(12) United States Patent
Anderberg et al.

(10) Patent No.: US 9,029,093 B2
(45) Date of Patent: May 12, 2015

(54) METHODS AND COMPOSITIONS FOR DIAGNOSIS AND PROGNOSIS OF RENAL INJURY AND RENAL FAILURE

(75) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US); James Patrick Kampf, San Diego, CA (US)

(73) Assignee: Astute Medical, Inc., San Diego, CA (US)

( * ) Notice: Subject to any disclaimer, the term of this patent is extended or adjusted under 35 U.S.C. 154(b) by 0 days.

(21) Appl. No.: 13/580,878

(22) PCT Filed: Feb. 26, 2011

(86) PCT No.: PCT/US2011/026384
§ 371 (c)(1),
(2), (4) Date: Oct. 23, 2012

(87) PCT Pub. No.: WO2011/106746
PCT Pub. Date: Sep. 1, 2011

(65) Prior Publication Data
US 2013/0210041 A1 Aug. 15, 2013

Related U.S. Application Data

(60) Provisional application No. 61/308,861, filed on Feb. 26, 2010.

(51) Int. Cl.
*G01N 33/53* (2006.01)
*G01N 33/536* (2006.01)
*G01N 33/68* (2006.01)

(52) U.S. Cl.
CPC ...... *G01N 33/6893* (2013.01); *G01N 2800/347* (2013.01); *G01N 2800/60* (2013.01)

(58) Field of Classification Search
CPC .............. G01R 33/302; C12Q 1/6895; G01N 2800/347; G01N 2800/56; G01N 2800/50; C07K 16/40
See application file for complete search history.

(56) References Cited

U.S. PATENT DOCUMENTS

| 6,218,122 B1 | 4/2001 | Friend et al. |
|---|---|---|
| 6,664,385 B1 | 12/2003 | Sanicola-Nadel et al. |
| 6,784,154 B2 | 8/2004 | Westenfelder |
| 6,861,404 B1 | 3/2005 | Cohen et al. |
| 6,941,172 B2 | 9/2005 | Nachum |
| 7,138,230 B2 | 11/2006 | Hu et al. |
| 7,141,382 B1 | 11/2006 | Parikh et al. |
| 7,235,358 B2 | 6/2007 | Wohlgemuth et al. |
| 7,608,413 B1 | 10/2009 | Joseloff et al. |
| 7,623,910 B2 * | 11/2009 | Couderc et al. ............ 600/509 |
| 7,662,578 B2 | 2/2010 | Devarajan |
| 7,833,699 B2 * | 11/2010 | Locht et al. .................. 435/4 |
| 7,981,684 B2 | 7/2011 | Levin et al. |
| 7,998,744 B2 | 8/2011 | Stevenson et al. |
| 8,008,008 B2 | 8/2011 | Parr et al. |
| 8,071,293 B2 | 12/2011 | High et al. |
| 8,080,394 B2 | 12/2011 | Levy et al. |
| 8,241,861 B1 | 8/2012 | Heinecke et al. |
| 8,252,905 B2 * | 8/2012 | Furusako et al. ........ 530/387.3 |
| 2003/0003588 A1 | 1/2003 | Comper |
| 2004/0053309 A1 | 3/2004 | Holt et al. |
| 2004/0106155 A1 | 6/2004 | Comper |
| 2005/0002934 A1 | 1/2005 | Reed |
| 2005/0048033 A1 | 3/2005 | Fraser et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2007/0031905 A1 | 2/2007 | Shariat |
| 2007/0087387 A1 | 4/2007 | Devarajan et al. |
| 2007/0093969 A1 | 4/2007 | Mendrick et al. |
| 2007/0105142 A1 | 5/2007 | Wilhelm |

(Continued)

FOREIGN PATENT DOCUMENTS

| CN | 1791797 A | 6/2006 |
|---|---|---|
| EP | 0828159 A1 | 3/1998 |
| EP | 1905846 A2 | 4/2008 |
| EP | 2261660 A1 | 12/2010 |
| EP | 2480882 A1 | 8/2012 |
| EP | 2513649 A1 | 10/2012 |
| JP | 2006038877 A | 2/2006 |
| RU | 2180965 C1 | 3/2002 |
| SU | 1429031 A1 | 10/1988 |
| WO | 9855508 A2 | 12/1998 |

(Continued)

OTHER PUBLICATIONS

Doumas et al., Infection and Immunity 2995;pp. 1271-1274.*
Shimano et al., Clinica Chimica Acta 225, 1994.*
Ohlsson et al., Mediators of inflammation 2001; vol. 10, 347-350.*
Ishii et al, 1990, Thromb Haemost. Apr. 12, 1990;63(2):157-62 Abstract only.*

(Continued)

*Primary Examiner* — Shafiqul Haq
*Assistant Examiner* — Carmencita M Belei
(74) *Attorney, Agent, or Firm* — Michael A. Whittaker; Acuity Law Group, P.C.

(57) ABSTRACT

The present invention relates to methods and compositions for monitoring, diagnosis, prognosis, and determination of treatment regimens in subjects suffering from or suspected of having a renal injury. In particular, the invention relates to using a plurality of assays configured to detect a kidney injury marker as diagnostic and prognostic biomarkers in renal injuries.

4 Claims, 2828 Drawing Sheets

(56) References Cited

U.S. PATENT DOCUMENTS

| | | | |
|---|---|---|---|
| 2007/0112327 A1 | 5/2007 | Yun et al. |
| 2007/0154897 A1 | 7/2007 | Yen et al. |
| 2007/0248989 A1 | 10/2007 | Devarajan |
| 2007/0249002 A1 | 10/2007 | Hu et al. |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0133141 A1 | 6/2008 | Frost |
| 2008/0153092 A1 | 6/2008 | Kienle et al. |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0148539 A1 | 6/2009 | Elias et al. |
| 2009/0176656 A1 | 7/2009 | Halloran |
| 2009/0178145 A1* | 7/2009 | Carr et al. ............ 800/3 |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0190156 A1* | 8/2011 | Whitfield et al. ............ 506/9 |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0190044 A1 | 7/2012 | Anderberg et al. |
| 2012/0190051 A1 | 7/2012 | Anderberg et al. |
| 2013/0035290 A1 | 2/2013 | Elias et al. |

FOREIGN PATENT DOCUMENTS

| | | |
|---|---|---|
| WO | 03054004 A2 | 7/2003 |
| WO | 03075016 A1 | 9/2003 |
| WO | 2004005934 A2 | 1/2004 |
| WO | 2005087264 A1 | 9/2005 |
| WO | 2006083986 A2 | 8/2006 |
| WO | 2007013919 A2 | 2/2007 |
| WO | 2007041623 A2 | 4/2007 |
| WO | 2008060607 A2 | 5/2008 |
| WO | 2008084331 A2 | 7/2008 |
| WO | 2008104804 A2 | 9/2008 |
| WO | 2008116867 A1 | 10/2008 |
| WO | 2008122670 A2 | 10/2008 |
| WO | 2008154238 A1 | 12/2008 |
| WO | 2009038742 A2 | 3/2009 |
| WO | 2010025424 A1 | 3/2010 |
| WO | 2010025434 A1 | 3/2010 |
| WO | 2010048346 A1 | 4/2010 |
| WO | 2010048347 A2 | 4/2010 |
| WO | 2010054389 A1 | 5/2010 |
| WO | 2010091236 A1 | 8/2010 |
| WO | 2010111746 A1 | 10/2010 |
| WO | 2010128158 A1 | 11/2010 |
| WO | 2011035323 A1 | 3/2011 |
| WO | 2011075744 A1 | 6/2011 |

OTHER PUBLICATIONS

Moreau et al, Biochimie 2008;vol. 90, pp. 284-295.*
Drannik et al., Zhurnal Akademii Med Nauk Ukraini 2007;vol. 13, issue 4, pp. 761-771, Abstract only.*
International Search Report and Written Opinion issued on Jun. 3, 2011 in PCT/US2011/026759.
International Search Report and Written Opinion issued on Sep. 7, 2012 in PCT/US2012/043279.
International Search Report and Written Opinion issued on Dec. 15, 2011 in PCT/US2011/001126.
International Search Report and Written Opinion issued on Nov. 25, 2011 in PCT/US2011/001127.
International Search Report and Written Opinion issued on Nov. 25, 2011 in PCT/US2011/001128.
International Search Report and Written Opinion issued on Nov. 25, 2011 in PCT/US2011/001125.
International Search Report and Written Opinion issued on Jun. 20, 2012 in PCT/US2012/020572.
International Search Report and Written Opinion issued on May 2, 2012 in PCT/US2012/022926.
International Search Report and Written Opinion issued on Sep. 21, 2012 in PCT/US2012/045583.
Non Final Office Action issued by the USPTO in U.S. Appl. No. 13/061,446 on Oct. 12, 2012.
Abd El Latif et al., Urinary epidermal growth factor excretion: A useful prognostic marker for progression of renal damage in children. J Med Sci Oct. 2007; 7(7): 1171-1176.
Abou-Shousha and Youssef, Interleukin-2 Regulatory Effect on P-Selectin and Interleukin-8 Production in Patients with Chronic Renal Failure. Egypt J Immunol. 2006;13(1):11-18.
Akcay et al., Mediators of Inflammation in Acute Kidney Injury. Mediators Inflamm. 2009;2009:137072 (12 pp).
Albright, Acute Renal Failure: A Practical Update. Mayo Clin. Proc. Jan. 2001;76(1):67-74.
Anders et al., Chemokines and chemokine receptors are involved in the resolution or progression of renal disease. Kidney Int. Feb. 2003;63(2):401-415.
Anilkumar et al., Trimeric assembly of the C-terminal region of Thrombospondin-1 or Thrombospondin-2 is necessary for cell spreading and fascin spike organisation. J Cell Sci. Jun. 1, 2002;115(Pt 11):2357-2366.
Arribas and Esselens, ADAM17 as a Therapeutic Target in Multiple Diseases. Curr Pharm Des. 2009;15(20):2319-2335.
Arrizabalaga et al., Tubular and Interstitial Expression of ICAM-1 as a Marker of Renal Injury in IgA Nephropathy. Am J Nephrol May-Jun. 2003;23(3):121-128.
Bagshaw et al., Urinary biomarkers in septic acute kidney injury. Intensive Care Med. Jul. 2007;33(7):1285-1296.
Bajwa et al., Immune Mechanisms and Novel Pharmacological Therapies of Acute Kidney Injury. Curr Drug Targets Dec. 2009;10(12):1196-1204.
Barrera-Chimal et al., Hsp72 is an early and sensitive biomarker to detect acute kidney injury. EMBO Mol Med. Jan. 2011;3(1):5-20.
Beushausen, NWG Biomarker Objectives. ILSI Health and Environmental Sciences Institute, ILSI-HESI Annual Meeting 2006:17 pp.
Bicik et al., Role of Transforming Growth Factor-.beta.2 in, and a Possible Transforming Growth Factor-beta2 Gene Polymorphism as a Marker of, Renal Dysfunction in Essential Hypertension: A Study in Turkish Patients, Current Therapeutic Research, 2005;44(4):266-278.
Biotrin International, Biotrin Biomarkers: How late do you want to detect preclinical kidney damage? Biotrin's acute kidney injury test (AKI Test). Biotrin's Preclinical Kidney Biomarkers: 8 pp.
Bonomini et al., Serum Levels of Soluble Adhesion Molecules in Chronic Renal Failure and Dialysis Patients. Nephron. Aug. 1998;79(4):399-407.
Bonventre and Zuk, Ischemic acute renal failure: An inflammatory disease? Kidney Int. Aug. 2004;66(2):480-485.
Bonventre, Dedifferentiation and Proliferation of Surviving Epithelial Cells in Acute Renal Failure. J Am Soc Nephrol Jun. 2003;14 Suppl 1:S55-S61.
Bonventre, Pathophysiology of Acute Kidney Injury: Roles of Potential Inhibitors of Inflammation. Contrib Nephrol. 2007; 156: 39-46.
Burne et al., IL-1 and TNF independent pathways mediate ICAM-1/VCAM-1 up-regulation in ischemia reperfusion injury. J Leukoc Biol. Aug. 2001;70(2):192-198.

(56) References Cited

OTHER PUBLICATIONS

Burne-Taney and Rabb, The role of adhesion molecules and T cells in ischemic renal injury. Curr Opin Nephrol Hypertens. Jan. 2003;12(1):85-90.
Canani et al., The Fatty Acid-Binding Protein-2 A54T Polymorphism Is Associated With Renal Disease in Patients With Type 2 Diabetes. Diabetes Nov. 2005;54(11):3326-3330.
Catania et al., Role of matrix metalloproteinases in renal pathophysiologies. Am J Physiol Renal Physiol Mar. 2007;292(3):F905-F911.
Coca et al., Biomarkers for the diagnosis and risk stratification of acute kidney injury: A systematic review. Kidney Int May 2008;73(9):1008-1016.
Cruz et al., North East Italian Prospective Hospital Renal Outcome Survey on Acute Kidney Injury (NEiPHROS-AKI): Targeting the Problem with the Rifle Criteria. Clin J Amer. Soc. Nephrol. May 2007;2(3):418-425.
Daha and Van Kooten, Is the proximal tubular cell a proinflammatory cell? Nephrol Dial Transplant 2000;15 Suppl 6:41-43.
De Sa et al., Leukocyte, platelet and endothelial activation in patients with acute renal failure treated by intermittent hemodialysis. Am J Nephrol. Jul.-Aug. 2001;21(4):264-273.
Devarajan and Williams, Proteomics for Biomarker Discovery in Acute Kidney Injury. Semin Nephrol. Nov. 2007;27(6):637-651.
Devarajan, Cellular and molecular derangements in acute tubular necrosis. Curr Opin Pediatr. Apr. 2005;17(2):193-199.
Devarajan, Novel biomarkers for the early prediction of acute kidney injury. Cancer Therapy Sep. 2005;3:477-488.
Devarajan, Update on Mechanisms of Ischemic Acute Kidney Injury. J Am Soc Nephrol. Jun. 2006;17(6):1503-1520.
Domanski et al., Purine and Cytokine Concentrations in the Renal Vein of the Allograft During Reperfusion. Transplant Proc. Jun. 2007;39(5):1319-1322.
FDA, European Medicines Agency to Consider Additional Test Results When Assessing New Drug Safety—Collaborative effort by FDA and EMEA expected to yield additional safety data. http://www.natap.org/2008/newsUpdates/071608_01.htm.
Ferguson et al., Biomarkers of nephrotoxic acute kidney injury. Toxicology Mar. 20, 2008;245(3):182-193.
Frangogiannis, Chemokines in ischemia and reperfusion. Thromb Haemost May 2007;97(5):738-747.
Furuichi et al., Chemokine/chemokine receptor-mediated inflammation regulates pathologic changes from acute kidney injury to chronic kidney disease. Clin Exp Nephrol Feb. 2009;13(1):9-14.
Furuichi et al., Roles of chemokines in renal ischemia/reperfusion injury. Front Biosci. May 1, 2008;13:4021-4028.
Galkina and Ley, Leukocyte Recruitment and Vascular Injury in Diabetic Nephropathy. J Am Soc Nephrol. Feb. 2006;17(2):368-377.
Garcia et al., Adenosine A2A receptor activation and macrophagemediated experimental glomerulonephritis. FASEB J. Feb. 2008;22(2):445-454.
Gbadegesin et al., Plasma and urinary soluble adhesion molecule expression is increased during first documented acute pyelonephritis. Arch Dis Child. Mar. 2002;86(3):218-221.
Goes et al., Effect of Recombinant Human Insulin-Like Growth Factor-1 on the Inflammatory Response to Acute Renal Injury. J Am Soc Nephrol. May 1996;7(5):710-720.
Office Action and Search Report issued by SIPO in Application No. 200980140805.3 dated Apr. 23, 2013—includes English Translation rec'd May 16, 2013.
Mishra et al., Neutrophil gelatinase-associated lipocalin (NGAL) as a biomarker for acute renal injury after cardiac surgery. Lancet. Apr. 2-8, 2005;365(9466):1231-1238.
International Preliminary Report on Patentability issued in PCT/US2011/055055 dated May 24, 2013.
Extended European Search Report and Written Opinion issued in EP 10838357 dated Jun. 3, 2013.
Stenvinkel et al., High Serum Hyaluronan Indicates Poor Survival in Renal Replacement Therapy. Am J Kidney Dis. Dec. 1999;34(6):1083-1088.

Non-Final Office Action issued by the United States Patent and Trade Office in U.S. Appl. No. 13/577,242 dated Jun. 20, 2013.
Extended European Search Report and Written Opinion issued in EP 10818036 dated Jun. 6, 2013.
Extended European Search Report and Written Opinion issued in EP 11740470 dated Jun. 18, 2013.
Tary-Lehmann et al., Enzyme-Linked Immunosorbent Assay Spot Detection of Interferon-Gamma and Interleukin 5-Producing Cells as a Predictive Marker for Renal Allograft Failure. Transplantation. Jul. 27, 1998;66(2):219-224.
Kimmel et al., Immunologic function and survival in hemodialysis patients. Kidney Int. Jul. 1998;54(1):236-244.
Simmons et al., Plasma cytokine levels predict mortality in patients with acute renal failure. Kidney Int. Apr. 2004;65(4):1357-1365.
Search Report issued by SIPO in Application No. 200980149555.X dated May 23, 2013—includes English translation.
Cai, Detection and Application for the biomarker of Rental Injury in Early Stage. Laboratory Med Clinic. Jun. 2005;2(3):124-127—incl Engl transl abstract only.
Office Action issued by SIPO in Application No. 200980149555.X dated Jul. 1, 2013—includes English translation.
Search Report issued by SIPO in Application No. 201080014932.1 dated Jun. 9, 2013—includes English translation.
Office Action issued by SIPO in Application No. 201080014932.1 dated Jun. 25, 2013—includes English translation.
Jung et al., Diagnostic significance of urinary enzymes in detecting acute rejection crises in renal transplant recipients depending on expression of results illustrated through the example of alanine aminopeptidase. Clin Biochem. Aug. 1985;18(4):257-260.
Search Report issued by SIPO in Application No. 200980149636.X dated Jun. 17, 2013—includes English translation.
Office Action issued by SIPO in Application No. 200980149636.X dated Jul. 1, 2013—includes English translation.
Extended European Search Report and Written Opinion issued in EP 11740468 dated Jun. 13, 2013.
Fried et al., Inflammatory and Prothrombotic Markers and the Progression of Renal Disease in Elderly Individuals. J Am Soc Nephrol. Dec. 2004;15(12):3184-3191.
Edelstein, Biomarkers of Acute Kidney Injury. Adv Chronic Kidney Dis.Jul. 2008;15(3)222-234.
Extended European Search Report and Written Opinion issued in EP 11740469 dated Jun. 13, 2013.
Fujisaki et al., Infusion of radiocontrast agents induces exaggerated release of urinary endothelin in patients with impaired renal function. Clin Exp Nephrol. Dec. 2003;7(4):279-283.
Hirai et al., Plasma endothelin-1(ET-1) is a useful marker for renal dysfunction. Atheroscler Suppl. Jun. 19, 2006;7(3):60[Mo-P1:65].
Cottone et al., Endothelin-1 and F2-isoprostane relate to and predict renal dysfunction in hypertensive patients. Nephrol Dial Transpl. Feb. 2009;24(2):497-503.
Schulz et al., Endothelin-1 as an early prognostic marker in acute renal failure (ARF) and sepsis. Kidney Blood Press Res. 2000;23(3-5):341-342.
Search Report issued by SIPO in Application No. 201080057014.7 dated Jul. 8, 2013—includes English translation.
Office Action issued by SIPO in Application No. 201080057014.7 dated Jul. 18, 2013—includes English translation.
Extended European Search Report and Written Opinion issued in EP 10812639 dated Jul. 16, 2013.
Song et al., Expression of TRAIL, DR4, and DR5 in kidney and serum from patients receiving renal transplantation. Transplant Proc. Jun. 2004;36(5):1340-1343.
Yuen et al., Ischemic and Nephrotoxic Acute Renal Failure are Distinguished by their Broad Transcriptomic Responses. Physiol Genomics. May 16, 2006;25(3):375-386.
Zager et al. Proximal tubular cytochrome c efflux: Determinant, and potential marker, of mitochondrial injury. Kidney Int. Jun. 2004;65(6):2123-2134.
International Preliminary Report on Patentability issued on Sep. 7, 2012 in PCT/US2011/026384.
Non-Final Office Action issued by the US Patent and Trademark Office on Nov. 16, 2012 in U.S. Appl. No. 13/389,351.

(56) References Cited

OTHER PUBLICATIONS

Non-Final Office Action issued by the US Patent and Trademark Office on Nov. 27, 2012 in U.S. Appl. No. 13/130,474.
Flynn et al., Urinary excretion of beta2-glycoprotein-1 (apolipoprotein H) and other markers of tubular malfunction in "non-tubular" renal disease J Clin Pathol. Jul. 1992;45(7):561-567.
Kasahara et al Clinical Significance of Serum Oxidized Low-Density Lipoprotein/beta2-Giycoprotein I Complexes in Patients with Chronic Renal Diseases. Nephron Clin Pract. 2004;98(1):15-24.
Lapsley et al., Beta 2-glycoprotein-1 (apolipoprotein H) excretion in chronic renal tubular disorders: Comparison with other protein markers of tubular malfunction. J Clin Pathol. Oct. 1991;44(10):812-816.
Matsuda et al., Beta 2-Glycoprotein I-Dependent and -Independent Anticardiolipin Antibody in Patients with End-Stage Renal Disease. Thromb Res. Oct. 15, 1993;72(2):109-117.
Ramirez et al., Prospective Study on Autoantibodies Against Apolipoprotein H (beta2GPI) in Several Clinical Parameters From Patients With Terminal Renal Failure and Functioning Renal Transplants. Transplant Proc. Jul.-Aug. 2009;41(6):2370-2.
Zheng et al., Antiphospholipid antibody profiles in lupus nephritis with glomerular microthrombosis: a prospective study of 124 cases. Arthritis Res Ther. 2009;11(3):1-9.
Extended European Search Report and Written Opinion issued in PCT/US2010044772 dated Dec. 3, 2012.
Voshol et al., Evaluation of Biomarker Discovery Approaches to Detect Protein Biomarkers of Acute Renal Allograft Rejection. J Proteome Res. Jul.-Aug. 2005;4(4):1192-1199.
Extended European Search Report and Written Opinion issued in PCT/US2010044708 dated Dec. 3, 2012.
Neziri et al., Cloning and molecular characterization of Dashurin encoded by C20orf116, a PCI-domain containing protein. Biochim Biophys Acta. Apr. 2010;1800(4):430-438.
Non Final Office Action issued by the US Patent and Trademark Office in U.S. Appl. No. 13/164,768 on Dec. 18, 2012.
Non Final Office Action issued by the US Patent and Trademark Office in U.S. Appl. No. 13/061,413 on Jan. 2, 2013.
Norman et al., Progressive Renal Disease: Fibroblasts, Extracellular Matrix, and Integrins. Exp Nephrol. Mar.-Apr. 1999;7(2):167-177.
International Search Report and Written Opinion issued in 200980154224.5 dated Nov. 23, 2012.
English Translation of International Search Report and Written Opinion issued in 200980154224.5 dated Nov. 23, 2012.
Zhu et al., Expression of Urinary Epidermal Growth Factor and Renal Function. J Clin Urol Dec. 31, 1998;13(8):374-379.
Zhu et al., Expression of Urinary Epidermal Growth Factor and Renal Function. J Clin Urol Dec. 31, 1998;13(8):374-379 (abstract English translation).
Sun et al., A Survey on the Relationship between the Epidermal Growth Factor and Renal Function. Int J Transpl Hemopurific Dec. 31, 2006;4(1):41-44.
Sun et al., A Survey on the Relationship between the Epidermal Growth Factor and Renal Function. Int J Transpl Hemopurific Dec. 31, 2006;4(1):41-44 (abstract English translation).
Non Final Office Action issued in 2009801542245 Dec. 17, 2012.
Non Final Office Action issued by the US Patent and Trademark Office in U.S. Appl. No. 13/125,360 on Jan. 24, 2013.
Caron et al. Ischemic injury alters endothelial cell properties of kidney cortex:stimulation of MMP-9. Exp Cell Res. Oct. 15, 2005;301(1):105-116.
Non Final Office Action issued by the US Patent and Trademark Office in U.S. Appl. No. 13/508,363 on Feb. 1, 2013.
Non Final Office Action issued by the US Patent and Trademark Office in U.S. Appl. No. 13/577,243 on Feb. 14, 2013.
Non Final Office Action issued in Japanese Patent Application No. 2011-525262 on Feb. 5, 2013.
Non Final Office Action issued in Japanese Patent Application No. 2011-525262 on Feb. 5, 2013 (English translation).
International Search Report and Written Opinion issued in PCT/US2012/066152 dated Mar. 15, 2013.
Extended European Search Report and Written Opinion issued in EP 10817878 dated Apr. 15, 2013.
Mezzano et al., Endothelial Cell Markers in Chronic Uremia: Relationship with Hemostatic Defects and Severity of Renal Failure. Thromb Res. Dec. 15, 1997;88(6):465-472.
Tan et al., The level of urinary secretory immunoglobulin A (sIgA) of patients with IgA nephropathy is elevated and associated with pathological phenotypes. Clin Exp Immunol. Apr. 2009;156(1):111-116.
Zhang et al., The level of serum secretory IgA of patients with IgA nephropathy is elevated and associated with pathological phenotypes. Nephrol Dial Transplant. Jan. 2008;23(1):207-212.
Search Report and Written Opinion issued by SIPO in 2009801406946 dated Apr. 15, 2013—includes English translation.
Office Action issued by SIPO in 2009801406946 dated May 29, 2013—includes English translation.
Search Report and Written Opinion issued in PCT/US2013/023479 dated May 15, 2013.
Choi et al., Expression of Vascular Endothelial Growth Factor-C and Its Receptor mRNA in the Rat Kidney With Ischemia-Reperfusion Injury. Clinical Kidney J. Jun. 2, 2011;4(Suppl 2):2 pages.
Cooper, Effect of Tobacco Smoking on Renal Function. Indian J Med Res Sep. 2006;124(3):261-268.
Extended European Search Report and Written Opinion issued in EP 10829198 dated May 21, 2013.
Senatorski et al., Urine activity of cathepsin B, collagenase and urine excretion of TGF-beta1 and fibronectin in membranous glomerulonephritis. Res Exp Med (Berl). Dec. 1998;198(4):199-206.
Schaefer et al., Urinary excretion of cathepsin B and cystatins as parameters of tubular damage. Kidney Int Suppl. Nov. 1994;47:S64-S67.
Kos et al., Cathepsins B,H and L and Their Inhibitors Stefin A and Cystatin C in Sera of Melanoma Patients. Clin Cancer Res. Oct. 1997;3(10):1815-1822.
Nambi et al., Down regulation of kidney neutral endopeptidase mRNA, protein and activity during acute renal failure: possible mechanism for ischemia-induced acute renal failure in rats? Mol Cell Biochem. Jul. 1999;197(1-2):53-59.
Li et al., Predictive value of RIFLE classification on prognosis of critically ill patients with acute kidney injury treated with continuous renal replacement therapy. Chin Med J (Engl). May 5, 2009;122(9):1020-1025.
Extended European Search Report and Written Opinion issued in EP 10829191 dated May 24, 2013.
Berahovich et al., Proteolytic activation of alternative CCR1 ligands in inflammation. J Immunol. Jun. 1, 2005;174(11):7341-7351.
Hatta et al., Cytokine Array Comparisons of Plasma from Cycling Fertile Women on Cycle Day 5 and Ovulation. Am J Reprod Immunol. Sep. 2009;62(3):158-164.
Grigoryev et al., The Local and Systemic Inflammatory Transcriptome after Acute Kidney Injury. J Am Soc Nephrol. Mar. 2008;19(3):547-558.
Gums et al., Serum Levels of Total Acid Phosphatase, Prostatic Acid Phosphatase, Total and Free Prostate-Specific Antigen in Patients Within Chronic Hemodialysis Program. Braz J Urol, Mar.-Apr. 2001;27(2):133-135.
Gupta et al., Role of Protein C in Renal Dysfunction after Polymicrobial Sepsis. J Am Soc Nephrol. Mar. 2007;18(3):860-867.
Han et al, Urinary biomarkers in the early diagnosis of acute kidney injury, Kidney Int. Apr. 2008;73(7):863-869.
Han et al., Upregulation of hyaluronan and its binding receptors in an experimental model of chronic cyclosporine nephropathy. Nephrology (Carlton). Mar. 2010;15(2):216-224.
Han, Biomarkers for Early Detection of Acute Kidney Injury. Nephrology Rounds Apr. 2008;6(4):6 pp.
Harris et al., Growth Factors and Cytokines in Acute Renal Failure. Adv Ren Replace Ther. Apr. 1997;4(2 Suppl):43-53.
He et al., Interleukin-18 binding protein transgenic mice are protected against ischemic acute kidney injury. Am J Physiol Renal Physiol. Nov. 2008;295(5):F1414-F1421.
Herget-Rosenthal et al., Early detection of acute renal failure by serum cystatin C. Kidney Int. Sep. 2004;66(3):1115-1122.

(56) References Cited

OTHER PUBLICATIONS

Hidaka et al., Urinary clusterin levels in the rat correlate with the severity of tubular damage and may help to differentiate between glomerular and tubular injuries. Cell Tissue Res. Dec. 2002;310(3):289-296.

Hirschberg et al. Factors Predicting Poor Outcome in Patients with Acute Renal Failure (ARF). J. Am. Soc. Nephrol. Sep. 1, 1996;7(9):1374.

Hoste et al., RIFLE criteria for acute kidney injury are associated with hospital mortality in critically ill patients: a cohort analysis. Crit Care, 2006;10(3):R73 (10 pages).

Hugo and Daniel, Thrombospondin in Renal Disease. Nephron Exp Nephrol. 2009;111(3):e61-e66.

Hugo et al. ,Thrombospondin 1 precedes and predicts the development of tubulointerstitial fibrosis in glomerular disease in the rat. Kidney Int. Feb. 1998;53(2):302-311.

Jang and Rabb, The innate immune response in ischemic acute kidney injury. Clin Immunol. Jan. 2009;130(1):41-50.

Jonsson, The role of fibroblast growth factor 23 in renal disease. Nephrol. Dial. Transplant Mar. 2005;20(3):479-482.

Julian et al., Sources of Urinary Proteins and their Analysis by Urinary Proteomics for the Detection of Biomarkers of Disease. Proteomics Clin Appl., 2009;3(9):1029-1043.

Kadiroglu et al., The Evaluation of Effects of Demographic Features, Biochemical Parameters, and Cytokines on Clinical Outcomes in Patients with Acute Renal Failure. Ren Fail. 2007;29(4):503-508.

Kalousova et al., Soluble Receptor for Advanced Glycation End Products in Patients With Decreased Renal Function. Am. J. Kidney Dis.Mar. 2006;47(3): 406-411.

Kamata et al., Up-regulation of glomerular extracellular matrix and transforming growth factor-beta expression in RF/J mice. Kidney Int. Mar. 1999;55(3):864-876.

Kehoe et al. Elevated Plasma Renin Activity Associated with Renal Dysfunction. Nephron 1986;44:51-57 (abstract only).

Kellum et al. Definition and Classification of Acute Kidney Injury. Nephron Clin Pract 2008;109(4):c182-c187.

Kellum., Acute kidney injury, Crit Care Med, 2008;36(4):S141-S145.

Keyes and Bagshaw, Early diagnosis of acute kidney injury in critically ill patients. Expert Rev Mol Diagn. Jul. 2008;8(4):455-464.

Khanna et al., Expression of TGF-beta and fibrogenic genes in transplant recipients with tacrolimus and cyclosporine nephrotoxicity. Kidney Int. Dec. 2002;62(6):2257-2263.

Kharasch et al., Gene Expression Profiling of Nephrotoxicity from the Sevoflurane Degradation Product Fluoromethyl-2,2-difluoro-1-(trifluoromethyl)vinyl Ether ("Compound A") in Rats. Toxicol Sci. Apr. 2006;90(2):419-431.

Kiley and Chevalier, Urinary biomarkers: The future looks promising. Kidney Int. Jul. 2009;76( 2): 133-134.

Kilis-Pstrusinska et al., [Levels of selected soluble adhesion molecules in blood serum of children with chronic glomerulonephritis]. Pol Merkur Lekarski. Apr. 2001;10(58):247-249.

Kilis-Pstrusinska et al., Serum levels of soluble adhesion molecules in children with glomerulonephritis (GN). Nephrol Dialysis Transplant. Jun. 2001;16(6):A62.

Kinsey et al., Inflammation in Acute Kidney Injury. Nephron Exp Nephrol. 2008; 109(4):e102-e107.

Koo et al., Cadaver versus living donor kidneys: Impact of donor factors on antigen induction before transplantation. Kidney Int. Oct. 1999;56(4):1551-1559.

Landray et al., Inflammation, Endothelial Dysfunction, and Platelet Activation in Patients With Chronic Kidney Disease: The Chronic Renal Impairment in Birmingham (CRIB) Study. Am J Kidney Dis. Feb. 2004;43(2):244-253.

Lang et al., Heat Shock Protein 60 Is Released in Immune-Mediated Glomerulonephritis and Aggravates Disease: In Vivo Evidence for an Immunologic Danger Signal. J Am Soc Nephrol. Feb. 2005;16(2):383-391.

Lapsley et al., Beta2-glycoprotein-1 (apolipoprotein H) excretion in chronic renal tubular disorders: Comparison with other protein markers of tubular malfunction. J Clin Pathol. Oct. 1991;44(10):812-816.

Larsson et al., Circulating concentration of FGF-23 increases as renal function declines in patients with chronic kidney disease, but does not change in response to variation in Phosphate intake in healthy voluntees. Kidney Int.Dec. 2003;64(6):2272-2279.

Liu et al., Predictive and pathogenetic value of plasma biomarkers for acute kidney injury in patients with acute lung injury. Crit Care Med Dec. 2007;35(12):2755-2761.

Liu et al., Serum Interleukin-6 and interleukin-8 are early biomarkers of acute kidney injury and predict prolonged mechanical ventilation in children undergoing cardiac surgery: a case-control study. Critical Care 2009;13(4):R104 (9 pp.).

Lopes-Virella et al., Urinary high density lipoprotein in minimal change glomerular disease and chronic glomerulopathies. Clin Chim Acta. May 16, 1979;94(1):73-81.

Lu et al., Increased Macrophage Infiltration and Fractalkine Expression in Cisplatin-Induced Acute Renal Failure in Mice. J Pharmacol Exp Ther. Jan. 2008;324(1):111-117.

Malyszko et al., Visfatin and apelin, new adipocytokines, and their relation to endothelial function in patients with chronic renal failure. Adv Med Sci. 2008;53(1):32-36.

Matousovic et al., IgA-containing immune complexes in the urine of IgA nephropathy patients. Nephrol Dial Transplant Sep. 2006;21(9):2478-2484.

Mattes, Experience With a Biomarker Consortium. CPath Predictive Safety Training Consortium, Critical Path Institute:48 pp.

Melnikov et al., Impaired IL-18 processing protects caspase-1-deficient mice from ischemic acute renal failure. J Clin Invest, May 2001;107(9):1145-1152.

Milford et al., Prognostic Markers in Diarrhoea-Associated Haemolytic-Uraemic Syndrome: Initial Neutrophil Count, Human Neutrophil Elastase and Von Willebrand Factor Antigen. Nephrol Dial Transplant 1991;6(4):232-237.

Montagna et al., Impairment of cellular redox status and membrane protein activities in kidneys from rats with ischemic acute renal failure. Biochim Biophys Acta Aug. 14, 1998;1407(2):99-108.

Musial et al., Soluble adhesion molecules in chronic renal failure (CRF) children treated conservatively. Nephrol Dialysis Transplant. 2002;17(Abstracts Suppl 1):232.

Nguyen et al., Heparin-Binding EGF-Like Growth Factor Is Up-Regulated in the Obstructed Kidney in a Cell- and Region-Specific Manner and Acts to Inhibit Apoptosis. Am J Pathol. Mar. 2000;156(3):889-898.

Nishiyama et al., Up-Regulation of Galectin-3 in Acute Renal Failure of the Rat. Am J Pathol. Sep. 2000;157(3):815-823.

Ohno et al., Prognostic significance of tenascin-C expression in clear cell renal cell carcinoma. Oncol Rep. 2008;20(3):511-516.

Ozer et al., A panel of urinary biomarkers to monitor reversibility of renal injury and a serum marker with improved potential to assess renal function. Nat Biotechnol. May 2010;28(5):486-494.

FDA, European Medicines Agency to Consider Additional Test Results When Assessing New Drug Safety—Collaborative effort by FDA and EMEA expected to yield additional safety data. http://www.natap.org/2008/newsUpdates/071608_01.htm dated Jun. 12, 2008.

Harpur et al., Biological Qualification of Biomarkers of Chemical-Induced Renal Toxicity in Two Strains of Male Rat. Toxicol Sci. Aug. 2011;122(2):235-252.

Final Office Action issued by the United States Patent and Trademark Office in U.S. Appl. No. 13/061,446 dated Jun. 7, 2013.

Non Final Office Action issued by the United States Patent and Trademark Office in U.S. Appl. No. 13/125,454 dated Mar. 5, 2013.

Thaker et al., Identification of thrombospondin 1 (TSP-1) as a novel mediator of cell injury in kidney ischemia. J Clin Invest Dec. 2005;115(12):3451-3458.

Restriction Requirement issued by the United States Patent and Trademark Office in U.S. Appl. No. 13/061,413 dated Sep. 5, 2012.

Response to Restriction Requirement in U.S. Appl. No. 13/061,413 dated Oct. 16, 2012.

Response to Non Final Office Action issued in U.S. Appl. No. 13/061,413 dated Jul. 2, 2013.

(56) References Cited

OTHER PUBLICATIONS

Final Office Action issued by the United States Patent and Trademark Office in U.S. Appl. No. 13/061,413 dated Aug. 23, 2013.
Restriction Requirement issued by the United States Patent and Trademark Office in U.S. Appl. No. 13/148,031 dated Mar. 20, 2013.
Mast et al., Clinical utility of the soluble transferrin receptor and comparison with serum ferritin in several populations. Clin Chem. Jan. 1998;44(1):45-51.
Non Final Office Action issued by the United States Patent and Trademark Office in U.S. Appl. No. 13/389,363 dated Apr. 18, 2013.
Iglesias et al., Thyroid Dysfunction and Kidney Disease (Revised version). Eur J Endocrinol. Dec. 18, 2008:32 pages retrieved from URL://www.eje.org/content!early/2008/12/18/EJE-08-0837.full.pdf.
Rajashekar et al., Systemic diseases with renal manifestations. Prim Care. Jun. 2008;35(2):297-328.abstract retrieved from URL:www.ncbi.nlm.nih.gov/pubmed/18486717.
Rini et al., Renal cell carcinoma. Lancet. Mar. 28, 2009;373(9669):1119-1132.
Non Final Office Action issued by the United States Patent and Trademark Office in U.S. Appl. No. 13/125,360 dated Aug. 27, 2013.
Sharma et al. Two-dimensional fluorescence difference gel electrophoresis analysis of the urine proteome in human diabetic nephropathy. Proteomics. Jul. 2005;5(10):2648-2655.
Non Final Office Action issued by the United States Patent and Trademark Office in U.S. Appl. No. 13/130,474 dated Nov. 27, 2012.
Non Final Office Action issued by the United States Patent and Trademark Office in U.S. Appl. No. 13/148,030 dated May 1, 2013.
Malm et al., Changes in the plasma levels of vitamin K-dependent proteins C and S and of C4b-binding protein during pregnancy and oral contraception. Br J Haematol. Apr. 1988;68(4):437-443.
Matsuzaka et al., Relationship between vitamin K dependent coagulation factors and anticoagulants (protein C and protein S) in neonatal vitamin K deficiency. Arch Dis Child. Mar. 1993;68(3 Spec No):297-302.
International Search Report and Written Opinion issued in PCT/US2013/028005 dated Jun. 18, 2013.
Maddens et al., Chitinase-like Proteins are Candidate Biomarkers for Sepsis-induced Acute Kidney Injury. Mol Cell Proteomics. Jan. 10, 2012;11(6):1-13.
Restriction Requirement issued by the United States Patent and Trademark Office in U.S. Appl. No. 13/517,244 dated Jul. 1, 2013.
Extended European Search Report and Written Opinion issued in EP 11751238 dated Aug. 13, 2013.
Haase et al., A comparison of the RIFLE and Acute Kidney Injury Network classifications for cardiac surgery-associated acute kidney injury: A prospective cohort study. J Thorac Cardiovasc Surg. Dec. 2009;138(6):1370-1376.
Zaffanello M et al., Early diagnosis of acute kidney injury with urinary biomarkers in the newborn. J Matern Fetal Neonatal Med. 2009;22 Suppl 3:62-66.
Extended European Search Report and Written Opinion issued in EP 11748210 dated Aug. 16, 2013.
Calabrese et al., Oxidative stress and cellular stress response in diabetic nephropathy. Database Biosis [Online]. Biosciences Information Service Jan. 2007; XP002705326. Database accession No. PREV200800097004 (abstract):3 pages & Cell Stress Chaperones. 2007 Winter;12(4):299-306.
Musial et al., The Heat Shock Protein Profile in Children with Chronic Kidney Disease. Perit Dial Int. Mar.-Apr. 2010;30(2):227-232.
Tao et al., Expression of 60-kDa and Inducible 70-kDa Stress Proteins in Gentamicin-Induced Acute Renal Failure. Clin Exp Nephrol. Jul. 1997;1:254-260.
Response dated May 16, 2012 to Extended European Search Report and Written Opinion in PCT/US2009/055449.
Extended European Search Report and Written Opinion issued on Feb. 23, 2012 in PCT/US2009/065419.
Extended European Search Report and Written Opinion issued on Jul. 27, 2012 in PCT/US2010/023294.
Extended European Search Report and Written Opinion issued on Oct. 24, 2011 in PCT/US2009/055449.
Extended European Search Report and Written Opinion issued on Feb. 22, 2012 in PCT/US2009/055460.
Extended European Search Report and Written Opinion issued on Jul. 9, 2012 in PCT/US2009/061561.
Extended European Search Report and Written Opinion issued on Aug. 23, 2012 in PCT/US2009/061562.
Extended European Search Report and Written Opinion issued on Jul. 9, 2012 in PCT/US2010/023292.
Extended European Search Report and Written Opinion issued on Aug. 23, 2012 in PCT/US2010/023297.
Extended European Search Report and Written Opinion issued on Jun. 8, 2012 in PCT/US2009/063906.
International Preliminary Report on Patentability issued on Oct. 21, 2011 in PCT/US2010/023297.
International Preliminary Report on Patentability issued on Mar. 29, 2011 in PCT/US2010/049234.
International Preliminary Report on Patentability issued on May 18, 2012 in PCT/US2010/055730.
International Preliminary Report on Patentability issued on Mar. 10, 2011 in PCT/US2009/055449.
International Preliminary Report on Patentability issued on Mar. 10, 2011 in PCT/US2009/055460.
International Preliminary Report on Patentability issued on Aug. 16, 2012 in PCT/US2011/023830.
International Preliminary Report on Patentability issued on Aug. 16, 2012 in PCT/US2011/023831.
International Preliminary Report on Patentability issued on Aug. 16, 2012 in PCT/US2011/023832.
International Preliminary Report on Patentability issued on Apr. 5, 2012 in PCT/US2010/049695.
International Preliminary Report on Patentability issued on May 5, 2011 in PCT/US2009/061561.
International Preliminary Report on Patentability issued on May 5, 2011 in PCT/US2009/061562.
International Preliminary Report on Patentability issued on Jun. 3, 2011 in PCT/US2009/065419.
International Preliminary Report on Patentability issued on Jul. 5, 2012 in PCT/US2010/061377.
International Preliminary Report on Patentability issued on Aug. 18, 2011 in PCT/US2010/023292.
International Preliminary Report on Patentability issued on Aug. 18, 2011 in PCT/US2010/023294.
International Preliminary Report on Patentability issued on May 10, 2011 in PCT/US2009/063906.
International Search Report and Written Opinion issued on Dec. 3, 2010 in PCT/US2010/049234.
International Search Report and Written Opinion issued on Feb. 8, 2011 in PCT/US2010/055730.
International Search Report and Written Opinion issued on Oct. 28, 2010 in PCT/US2010/044772.
International Search Report and Written Opinion issued on Oct. 8, 2010 in PCT/US2010/044708.
International Search Report and Written Opinion issued on Dec. 10, 2009 in PCT/US2009/055449.
International Search Report and Written Opinion issued on Dec. 31, 2009 in PCT/US2009/055460.
International Search Report and Written Opinion issued on Dec. 3, 2010 in PCT/US2010/049695.
International Search Report and Written Opinion issued on Jan. 20, 2010 in PCT/US2009/061561.
International Search Report and Written Opinion issued on Apr. 13, 2010 in PCT/US2009/061562.
International Search Report and Written Opinion issued on Mar. 30, 2010 in PCT/US2009/065419.
International Search Report and Written Opinion issued on Mar. 8, 2011 in PCT/US2010/061377.
International Search Report and Written Opinion issued on Apr. 30, 2010 in PCT/US2010/023292.
International Search Report and Written Opinion issued on Apr. 22, 2010 in PCT/US2010/023294.

(56) References Cited

OTHER PUBLICATIONS

International Search Report and Written Opinion issued on Jun. 3, 2010 in PCT/US2010/023297.
International Search Report and Written Opinion issued on Jan. 15, 2010 in PCT/US2009/063906.
International Search Report and Written Opinion issued on Nov. 18, 2010 in PCT/US2010/046910.
International Search Report and Written Opinion issued on Jan. 18, 2012 in PCT/US2011/053015.
International Search Report and Written Opinion issued on Feb. 24, 2012 in PCT/US2011/055055.
International Search Report and Written Opinion issued on Jan. 19, 2011 in PCT/US2010/055721.
International Search Report and Written Opinion issued on May 10, 2012 in PCT/US2012/020571.
International Search Report and Written Opinion issued on Apr. 27, 2011 in PCT/US2011/023830.
International Search Report and Written Opinion issued on Apr. 27, 2011 in PCT/US2011/023831.
International Search Report and Written Opinion issued on Apr. 29, 2011 in PCT/US2011/023832.
International Search Report and Written Opinion issued on May 17, 2011 in PCT/US2011/026384.
Office Action and Search Report issued by SIPO in Chinese application No. 201080062499.9 dated Jan. 24, 2014—includes English language translation.
Office Action and Search Report issued by SIPO in Chinese application No. 201080062499.9 dated Sep. 15, 2014—includes English language translation.
Office Action and Search Report issued by the JPO in Japanese application No. 2012-544950 dated Jun. 24, 2014—includes English language translation.
Fu and Tao, Study on the expression of VEGF,MMP-2 and TIMP-2 in the progression of IgA nephropathy, J Clin Exp Pathol. Oct. 2008;24(5):573-576—includes English language translation abstract only.
Humphreys and Bonventre, Mesenchymal Stein Cells in Acute Kidney Injury. Annu Rev Med. 2008;59:311-325.
Lu et al., Clinical Study of Plasma Thrombomodulin Detection. Zhongguo Shi Yan Xue Ye Xue Za Zhi. Feb. 2007;15(1):112-116.
Malyszko et al., Visfatin and apelin, new adipocytokines, and their relation to endothelial function in patients with chronic renal failure. Adv Med Sci. 2008;53(1):32-36.
U.S. Food and Drug Administration. "FDA Allows Marketing of the First Test to Assess Risk of Developing Acute Kidney Injury". Press Announcements. N.p., Sep. 5, 2014. Web. Oct. 22, 2014. <http://www.fda.gov/NewsEvents/Newsroom/PressAnnouncements/ucm412910.htm>.
Parikh et al., Kidney International, 70:199-203 2006.
Coca et al., Kidney International, 73:1008-1016 2008.
Parikh et al., cirt Care Med, 36(4Supplement):S159-S165 2008.
International Search Report and Written Opinion issued in PCT/US2011/026384 on May 17, 2011.
Parikh and Devarajan, New biomarkers of acute kidney injury. Crit Care Med 2008;36(4 Suppl):S159-S165.
Parikh et al., Urinary IL-18 is an early predictive biomarker of acute kidney injury after cardiac surgery. Kidney Int, 2006;70(1):199-203.
Perco et al., Protein biomarkers associated with acute renal failure and chronic kidney disease. Eur J Clin Invest. Nov. 2006;36(11):753-763.
Picard et al., Origin of renal myofibroblasts in the model of unilateral ureter obstruction in the rat. Histochem Cell Biol. Jul. 2008;130(1):141-155.
Price, Abrupt Changes in Prostate-Specific Antigen Concentration in Acute Renal Failure. Clin Chem. Jan. 1993;39(1):161-162.
Prozialeck and Edwards, Cell Adhesion Molecules in Chemically-Induced Renal Injury. Pharmacol Ther. Apr. 2007;114(1):74-93.
Radford et al. Predicting renal outcome in IgA nephropathy. J Am Soc Nephrol Feb. 1997;8(2):199-207.

Ramesh and Reeves, TNF-α mediates chemokine and cytokine expression and renal injury in cisplatin nephrotoxicity. J. Clin. Invest. Sep. 2002;110(6):835-842.
Ramesh et al., Endotoxin and cisplatin synergistically induce renal dysfunction and cytokine production in mice. Am J Physiol Renal Physiol. Jul. 2007;293(1):F325-F332.
Ramirez et al., Prospective Study on Autoantibodies Against Apolipoprotein H ( B2GPI) in Several Clinical Parameters From Patients With Terminal Renal Failure and Functioning Renal Transplants. Transplantation Proceedings Jul. 2009;41(6):2370-2372.
Ricci et al., The RIFLE criteria and mortality in acute kidney injury: A systematic review. Kidney Int Mar. 2008;73(5):538-546.
Rosenkranz et al., P-selectin deficiency exacerbates experimental glomerulonephritis: a protective role for endothelial P-selectin in inflammation. J Clin Invest Mar. 1999;103(5):649-659.
Rouschop et al., Pre-transplant plasma and cellular levels of CD44 correlate with acute renal allograft rejection Nephrol Dial Transplant Oct. 2005;20(10):2248-2254.
Rouschop et al., Renal expression of CD44 correlates with acute renal allograft rejection. Kidney Int. Sep. 2006;70(6):1127-1134.
Schena et al., EGF and MCP-1 Urinary Excretion Is a Suitable Prognostic Marker in Iga Nephropathy. J Am Soc of Nephrology; Meeting of the American Society of Nephrology. Sep. 1, 2002;13(Program and Abstracts Issue): 458A.
Schiffer et al., Activated Renal Macrophages Are Markers of Disease Onset and Disease Remission in Lupus Nephritis, J Immunol Feb. 1, 2008;180(3):1938-1947.
Schmaldienst et al., Angiogenin: a novel inhibitor of neutrophil-lactoferrin release during extracorporeal circulation. Kidney Blood Press Res. 2003;26(2):107-112.
Schmidt et al., Sexual hormone abnormalities in male patients with renal failure. Nephrol Dial Transplant. Mar. 2002;17(3):368-371.
Segawa et al., In situ expression and soluble form of P-selectin in human glomerulonephritis. Kidney Int Oct. 1997;52(4):1054-1063.
Segerer et al., Chemokines, Chemokine Receptors, and Renal Disease: From Basic Science to Pathophysiologic and Therapeutic Studies. J Am Soc Nephrol Jan. 2000;11(1):152-176.
Severini and Aliberti, Diagnostic significance of urinary enzymes: Development of a high performance liquid chromatographic method for the measurement of urinary lysozyme. Clin Chim Acta Feb. 27, 1987:163(1):97-103.
Shlipak et al., Elevations of Inflammatory and Procoagulant Biomarkers in Elderly Persons With Renal Insufficiency. Circulation Jan. 2003;107(1):87-92.
Shoji et al., Plasma angiopoietin-like protein 3 (ANGPTL3) concentration is associated with uremic dyslipidemia. Atherosclerosis. Dec. 2009;207(2):579-584.
Stafford-Smith et al., Acute Kidney Injury and Chronic Kidney Disease After Cardiac Surgery. Adv Chronic Kidney Dis. Jul. 2008;15(3):257-277.
Stasko et al., Soluble P-Selectin During a Single Hemodialysis Session in Patients With Chronic Renal Failure and Erythropoietin Treatment. Clin Appl Thromb Hemost. Oct. 2007;13(4):410-415.
Stuard et al., Soluble adhesion molecules in chronic renal failure patients. Nephrol Dialysis Transplant. 1997;12(9):A100.
Supavekin et al., Differential gene expression following early renal ischemia/reperfusion. Kidney Int. May 2003;63(5):1714-1724.
Sutton et al., Injury of the renal microvascular endothelium alters barrier function after ischemia. Am J Physiol Renal Physiol Aug. 2003;285(2):F191-F198.
Sutton et al., Microvascular endothelial injury and dysfunction during ischemic acute renal failure. Kidney Int. Nov. 2002;62(5):1539-1549.
Sutton, Alteration of microvascular permeability in acute kidney injury. Microvasc Res. Jan. 2009;77(1):4-7.
Symon et al., The endogenous insulin-like growth factor system in radiocontrast nephropathy. Am. J. Physiol. Renal Physiol. Mar. 1998;274(3 Pt 2):F490-497.
Takada et al., The Cytokine-adhesion Molecule Cascade in Ischemia/Reperfusion Injury of the Rat Kidney. Inhibition by a Soluble P-selectin Ligand. J. Clin. Invest. Jun. 1997; 99(11):2682-2690.

(56) References Cited

OTHER PUBLICATIONS

Taulan et al., Comprehensive analysis of the renal transcriptional response to acute uranyl nitrate exposure. BMC Genomics Jan. 11, 2006;7(2) 14 pages.
Teppo et al., Soluble Intercellular Adhesion Molecule-1 (Sicam-1) after Kidney Transplantation: The Origin and Role of Urinary Sicam-1? Transplantation Apr. 27, 2001;71(8):1113-1119.
Thorburn et al., CXC and CC chemokines induced in human renal epithelial cells by inflammatory cytokines. APMIS Jul. 2009;117(7):477-487.
Timoshanko et al., Interleukin-12 from Intrinsic Cells Is an Effector of Renal Injury in Crescentic Glomerulonephritis. J. Am. Soc. Nephrol. Mar. 2001;12(3):464-471.
Torres et al., The ratio of epidermal growth factor to monocyte chemotactic peptide-1 in the urine predicts renal prognosis in IgA nephropathy. Kidney Int. Feb. 2008;73(3):327-333.
Vaidya and Bonventre, Mechanistic biomarkers for cytotoxic acute kidney injury. Expert Opin Drug Metab Toxicol. Oct. 2006;2(5):697-713.
Vaidya et al., Biomarkers of Acute Kidney Injury. Annu Rev Pharmacol Toxicol. Feb. 2008;48:463-493.
Vanhoutte et al., Biomarker discovery with SELDI-TOF MS in human urine associated with early renal injury: evaluation with computational analytical tools. Nephrol Dial Transplant Oct. 2007;22(10):2932-2943.
Villanueva et al., Ischemic acute renal failure induces the expression of a wide range of nephrogenic proteins. Am J Physiol Regul Integr Comp Physiol Apr. 2006;290(4):R861-R870.
Vonderscher, Biomarker of Drug Induced Kidney Injury Qualification for Regulatory Decision Making (CRADA). IOM/FDA, Silver Spring, MD Apr. 23, 2007:31 pp.
Waikar et al., Diagnosis, Epidemiology and Outcomes of Acute Kidney Injury. Clin J Am Soc Nephrol. May 2008;3(3):844-861.
Wan et al., The pathogenesis of septic acute renal failure. Curr Opin Crit Care Dec. 2003;9(6):496-502.
Wang et al., Netrin-1 and kidney injury. I. Netrin-1 protects against ischemia-reperfusion injury of the kidney. Am J Physiol Renal Physiol. Apr. 2008;294(4):F739-F747.
Wang et al., Validation of putative genomic biomarkers of nephrotoxicity in rats. Toxicology Apr. 18, 2008;246(2-3):91-100.
Wilson and Hadley, Urinary lysozyme. J Pediatr. Feb. 1950;36(2):199-211.
Winchester et al., Sorbents in Acute Renal Failure and End-Stage Renal Disease: Middle Molecule and Cytokine Removal. Blood Purif. 2004;22(1):73-77.
Yang et al. Frequency of anti-bactericidal/permeability-increasing protein (BPI) and anti-azurocidin in patients with renal disease. Clin. Exp. Immunol. Jul. 1996;105(1):125-131.
Yu et al., Urinary biomarkers trefoil factor 3 and albumin enable early detection of kidney tubular injury. Nat Biotechnol May 2010;128(5):470-477.

\* cited by examiner

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.6E1 | 8.2E1 | 7.7E1 | 9.3E1 | 5.2E1 | 6.0E1 | 2.0E0 | 1.3E1 | 4.4E2 | 2.4E2 | 1475 | 37 | 252 | 37 | 0.58 |
| Ad | ug/mL | 3.4E-2 | 7.6E-2 | 6.8E-2 | 3.6E-1 | 8.7E-2 | 1.5E0 | 6.8E-4 | 4.3E-3 | 5.4E-1 | 8.5E0 | 421 | 33 | 165 | 33 | 0.65 |
| Af | ng/mL | 1.1E0 | 1.0E0 | 1.6E1 | 1.4E1 | 6.2E1 | 4.5E1 | 1.7E-3 | 1.7E-3 | 5.3E2 | 2.6E2 | 421 | 33 | 165 | 33 | 0.54 |
| Aj | ug/mL | 1.8E0 | 5.4E-1 | 2.7E0 | 2.1E0 | 2.5E0 | 2.6E0 | 1.5E-3 | 2.1E-3 | 6.1E0 | 6.1E0 | 421 | 33 | 165 | 33 | 0.43 |
| Al | mg/mL | 8.7E-5 | 9.5E-5 | 2.5E-4 | 2.6E-4 | 4.1E-4 | 3.4E-4 | 2.5E-6 | 7.6E-6 | 2.2E-3 | 1.3E-3 | 421 | 33 | 165 | 33 | 0.56 |
| An | U/mL | 4.9E1 | 8.8E1 | 1.6E2 | 5.1E2 | 4.5E2 | 1.4E3 | 9.8E-4 | 9.6E-1 | 5.5E3 | 7.8E3 | 421 | 33 | 165 | 33 | 0.63 |
| Ao | pg/mL | 8.6E1 | 1.1E2 | 5.4E2 | 3.2E2 | 3.6E3 | 7.9E2 | 1.5E0 | 5.4E0 | 3.9E4 | 4.5E3 | 421 | 33 | 165 | 33 | 0.58 |
| Ap | ng/mL | 2.9E1 | 4.5E1 | 4.5E1 | 5.8E1 | 5.0E1 | 5.3E1 | 8.4E-5 | 3.1E0 | 3.3E2 | 2.4E2 | 421 | 33 | 165 | 33 | 0.60 |
| Ar | ng/mL | 8.5E-1 | 2.6E0 | 1.3E1 | 5.8E0 | 2.0E2 | 9.6E0 | 3.4E-3 | 9.5E-2 | 4.1E3 | 5.1E1 | 421 | 33 | 165 | 33 | 0.68 |
| As | ng/mL | 8.7E-3 | 1.0E-2 | 1.3E-2 | 5.4E-2 | 1.7E-2 | 2.1E-1 | 1.7E-3 | 1.7E-3 | 1.3E-1 | 1.2E0 | 421 | 33 | 165 | 33 | 0.53 |
| Aw | pg/mL | 1.6E1 | 1.8E1 | 1.6E1 | 1.9E1 | 6.0E0 | 8.0E0 | 2.9E-2 | 1.1E1 | 4.8E1 | 5.1E1 | 421 | 33 | 165 | 33 | 0.60 |
| Ax | ng/mL | 2.0E0 | 8.7E0 | 1.3E1 | 5.3E1 | 5.3E1 | 1.3E2 | 1.9E-2 | 1.2E-2 | 7.7E2 | 6.2E2 | 421 | 33 | 165 | 33 | 0.67 |
| Ba | ng/mL | 5.7E1 | 2.2E2 | 4.1E2 | 1.3E3 | 1.1E3 | 2.9E3 | 2.7E-1 | 6.3E0 | 8.1E3 | 1.5E4 | 421 | 33 | 165 | 33 | 0.65 |
| Bb | ng/mL | 2.9E0 | 5.0E0 | 6.3E0 | 7.8E0 | 1.5E1 | 6.9E0 | 4.1E-3 | 2.6E-1 | 2.5E2 | 2.5E1 | 421 | 33 | 165 | 33 | 0.63 |
| Bc | ng/mL | 3.4E1 | 7.2E1 | 9.9E1 | 1.8E2 | 1.9E2 | 3.0E2 | 1.1E-1 | 8.0E0 | 1.2E3 | 1.2E3 | 421 | 33 | 165 | 33 | 0.66 |
| Bg | ng/mL | 7.4E-2 | 1.3E-1 | 4.5E0 | 1.3E1 | 2.1E1 | 6.9E1 | 5.3E-4 | 5.3E-4 | 2.5E2 | 4.0E2 | 421 | 33 | 165 | 33 | 0.61 |
| Bn | ng/mL | 5.6E-2 | 5.6E-2 | 1.2E0 | 3.1E0 | 2.0E0 | 1.0E1 | 5.6E-2 | 5.6E-2 | 9.7E0 | 5.8E1 | 421 | 33 | 165 | 33 | 0.53 |
| Bo | ng/mL | 1.2E1 | 2.0E1 | 1.4E1 | 1.9E1 | 1.9E1 | 1.5E1 | 1.6E-2 | 1.6E-2 | 2.8E2 | 5.3E1 | 421 | 33 | 165 | 33 | 0.60 |
| Ch | uIU/mL | 1.1E0 | 6.6E-1 | 1.9E1 | 3.8E1 | 1.1E2 | 2.1E2 | 3.4E-3 | 3.9E-2 | 1.8E3 | 1.2E3 | 421 | 33 | 165 | 33 | 0.40 |
| Co | pg/mL | 3.6E1 | 5.5E1 | 1.8E2 | 1.3E2 | 9.9E2 | 1.9E2 | 1.5E-1 | 1.5E-1 | 1.7E4 | 8.2E2 | 421 | 33 | 165 | 33 | 0.62 |
| Cp | ng/mL | 2.2E1 | 2.4E1 | 2.8E1 | 7.3E1 | 3.2E1 | 2.2E2 | 6.0E-1 | 6.0E-1 | 3.7E2 | 1.3E3 | 421 | 33 | 165 | 33 | 0.64 |
| Cq | ng/mL | 2.8E-2 | 3.2E-2 | 1.4E-1 | 1.6E0 | 8.8E-1 | 8.5E0 | 8.0E-4 | 8.0E-4 | 1.7E1 | 4.9E1 | 421 | 33 | 165 | 33 | 0.54 |
| Cs | ng/mL | 5.3E1 | 2.2E2 | 2.7E2 | 1.2E3 | 8.0E2 | 3.2E3 | 2.7E-2 | 2.7E0 | 1.1E4 | 1.8E4 | 421 | 33 | 165 | 33 | 0.65 |
| Ct | ng/mL | 8.6E-1 | 1.3E-1 | 3.5E1 | 4.6E1 | 1.0E2 | 1.3E2 | 1.1E-4 | 1.1E-4 | 6.2E2 | 4.7E2 | 421 | 33 | 165 | 33 | 0.40 |
| Cu | ng/mL | 2.3E-1 | 3.8E-1 | 4.1E-1 | 2.7E0 | 7.8E-1 | 1.1E1 | 9.0E-5 | 4.6E-2 | 9.2E0 | 6.6E1 | 421 | 33 | 165 | 33 | 0.67 |
| Cv | ng/mL | 4.7E0 | 8.9E0 | 2.2E1 | 6.0E1 | 6.0E1 | 1.3E2 | 1.4E-4 | 5.1E-2 | 5.3E2 | 5.2E2 | 421 | 33 | 165 | 33 | 0.55 |
| Cw | mIU/mL | 3.0E-2 | 3.9E-2 | 3.9E-2 | 2.5E-1 | 3.3E-2 | 1.2E0 | 8.9E-4 | 4.1E-3 | 2.4E-1 | 6.8E0 | 421 | 33 | 165 | 33 | 0.57 |
| Cx | ng/mL | 2.6E-1 | 2.6E-1 | 5.8E1 | 7.1E1 | 1.1E2 | 1.2E2 | 9.3E-5 | 9.3E-5 | 3.9E2 | 3.9E2 | 421 | 33 | 165 | 33 | 0.49 |
| Db | ug/mL | 7.5E0 | 8.2E0 | 9.1E0 | 8.4E0 | 8.7E0 | 6.5E0 | 4.5E-1 | 8.8E-1 | 1.0E2 | 2.3E1 | 421 | 33 | 165 | 33 | 0.50 |
| Dc | nmol/L | 1.8E-2 | 2.4E-2 | 5.5E-2 | 5.6E-1 | 1.3E-1 | 2.4E0 | 5.2E-6 | 1.0E-3 | 1.6E0 | 1.4E1 | 421 | 33 | 165 | 33 | 0.60 |
| Dd | ug/mL | 7.1E-2 | 7.2E-2 | 1.8E-1 | 2.6E-1 | 2.6E-1 | 6.3E-1 | 8.3E-5 | 3.3E-3 | 1.9E0 | 3.6E0 | 421 | 33 | 165 | 33 | 0.51 |
| De | ng/mL | 3.4E-3 | 3.4E-3 | 7.6E-2 | 1.1E-1 | 1.4E-1 | 2.1E-1 | 3.4E-3 | 3.4E-3 | 9.2E-1 | 9.0E-1 | 421 | 33 | 165 | 33 | 0.52 |
| Dg | ng/mL | 2.8E1 | 5.2E1 | 4.1E1 | 6.1E1 | 3.9E1 | 4.8E1 | 1.0E-1 | 2.3E0 | 1.9E2 | 1.9E2 | 421 | 33 | 165 | 33 | 0.62 |
| Di | pg/mL | 1.9E0 | 3.2E0 | 2.2E0 | 2.9E0 | 2.0E0 | 2.0E0 | 1.8E-1 | 1.8E-1 | 1.3E1 | 9.0E0 | 421 | 33 | 165 | 33 | 0.61 |
| Dk | uIU/mL | 1.6E-2 | 2.2E-2 | 9.0E-2 | 8.6E-2 | 5.3E-1 | 1.6E-1 | 1.1E-4 | 1.1E-4 | 8.9E0 | 6.3E-1 | 421 | 33 | 165 | 33 | 0.59 |
| Dl | ng/mL | 2.1E2 | 3.0E2 | 3.0E2 | 4.3E2 | 2.8E2 | 3.9E2 | 1.7E0 | 1.8E1 | 1.5E3 | 1.6E3 | 421 | 33 | 165 | 33 | 0.60 |
| Dp | ng/ml | 2.4E0 | 2.1E0 | 5.2E0 | 1.3E1 | 7.5E0 | 3.6E1 | 3.7E-3 | 3.7E-3 | 4.6E1 | 2.0E2 | 249 | 32 | 162 | 32 | 0.46 |
| Dr | pg/ml | 2.5E1 | 3.0E1 | 5.2E1 | 7.3E2 | 7.1E1 | 2.5E3 | 7.5E-1 | 7.5E-1 | 5.2E2 | 1.0E4 | 154 | 17 | 87 | 17 | 0.58 |
| Du | pg/ml | 6.9E1 | 1.8E2 | 8.0E2 | 2.5E3 | 2.9E3 | 6.2E3 | 1.2E0 | 1.2E0 | 2.6E4 | 2.4E4 | 95 | 15 | 74 | 15 | 0.55 |
| Ef | ng/ml | 1.3E-1 | 2.4E-1 | 8.3E-1 | 1.4E0 | 1.8E0 | 2.5E0 | 5.7E-4 | 1.1E-2 | 1.0E1 | 9.4E0 | 304 | 33 | 164 | 33 | 0.58 |
| Wm | % | 5.9E-1 | 1.9E0 | 2.0E1 | 1.2E2 | 1.5E2 | 3.0E2 | 5.4E-2 | 8.5E-2 | 2.4E3 | 1.0E3 | 341 | 36 | 184 | 36 | 0.59 |
| Ed | pg/ml | 5.2E-1 | 2.7E1 | 5.7E1 | 6.4E1 | 4.6E2 | 9.8E1 | 5.2E-1 | 5.2E-1 | 7.3E3 | 5.0E2 | 249 | 32 | 161 | 32 | 0.64 |
| Yf | ng/mL | 1.6E1 | 1.5E1 | 1.0E2 | 3.6E1 | 6.5E2 | 7.5E1 | 2.9E-1 | 2.9E-1 | 6.6E3 | 2.9E2 | 105 | 14 | 83 | 14 | 0.46 |
| Tj | pg/mL | 3.7E-1 | 3.7E-1 | 5.9E1 | 2.2E1 | 3.1E2 | 6.0E1 | 3.6E-1 | 3.6E-1 | 3.5E3 | 3.1E2 | 304 | 33 | 167 | 33 | 0.51 |
| Po | pg/ml | 4.8E-1 | 6.9E0 | 8.6E0 | 2.4E1 | 2.5E1 | 4.4E1 | 8.0E-3 | 2.6E-2 | 2.7E2 | 2.2E2 | 690 | 48 | 279 | 48 | 0.68 |
| Ti | ug/mL | 3.2E0 | 6.8E0 | 4.5E0 | 7.8E0 | 4.0E0 | 8.1E0 | 1.2E-1 | 8.7E-3 | 1.7E1 | 3.7E1 | 155 | 21 | 117 | 21 | 0.63 |
| Em | ng/ml | 2.9E-3 | 1.4E-2 | 5.5E-2 | 1.4E-1 | 1.1E-1 | 4.5E-1 | 1.9E-16 | 8.4E-4 | 6.0E-1 | 1.9E0 | 190 | 18 | 87 | 18 | 0.47 |
| Et | ng/ml | 1.3E3 | 3.0E3 | 1.5E3 | 2.7E3 | 1.1E3 | 1.3E3 | 7.5E1 | 1.1E2 | 5.0E3 | 5.0E3 | 689 | 48 | 279 | 48 | 0.76 |
| Eq | pg/ml | 1.6E2 | 8.2E1 | 3.3E2 | 2.7E2 | 4.0E2 | 4.0E2 | 1.0E0 | 1.0E0 | 1.8E3 | 1.3E3 | 95 | 15 | 74 | 15 | 0.44 |
| Th | ug/mL | 1.1E0 | 1.0E0 | 1.6E0 | 1.4E0 | 1.5E0 | 1.2E0 | 2.6E-3 | 2.6E-3 | 1.2E1 | 4.2E0 | 155 | 21 | 117 | 21 | 0.45 |
| Fa | ng/ml | 3.9E1 | 8.4E1 | 1.2E2 | 2.5E2 | 5.6E2 | 4.9E2 | 3.4E-2 | 6.0E-1 | 8.0E3 | 2.5E3 | 243 | 32 | 159 | 32 | 0.69 |
| Ez | ng/ml | 3.8E0 | 5.5E0 | 1.8E1 | 1.6E1 | 5.5E1 | 2.3E1 | 1.3E-2 | 5.8E-2 | 7.1E2 | 8.8E1 | 249 | 32 | 162 | 32 | 0.57 |
| Fb | ng/ml | 2.5E1 | 2.8E1 | 2.2E1 | 2.7E1 | 1.2E1 | 1.0E1 | 6.6E1 | 5.9E-1 | 5.7E1 | 4.3E1 | 244 | 32 | 159 | 32 | 0.62 |
| Ex | ng/ml | 7.4E-2 | 1.6E-1 | 2.4E-1 | 4.1E-1 | 7.2E-1 | 8.7E-1 | 3.5E-5 | 1.7E-4 | 8.9E0 | 4.1E0 | 224 | 23 | 113 | 23 | 0.64 |

Figure 1

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fc | pg/ml | 2.2E-1 | 2.2E-1 | 1.7E2 | 2.7E1 | 1.5E3 | 7.9E1 | 2.2E-1 | 2.2E-1 | 1.5E4 | 3.1E2 | 97 | 15 | 74 | 15 | 0.61 |
| Fd | pg/ml | 1.5E1 | 2.5E2 | 8.1E2 | 2.2E3 | 3.5E3 | 6.4E3 | 4.5E-1 | 9.8E-1 | 3.3E4 | 2.5E4 | 97 | 15 | 74 | 15 | 0.61 |
| Fi | pg/ml | 2.5E-1 | 2.5E-1 | 2.0E2 | 2.2E1 | 1.4E3 | 6.6E1 | 2.5E-1 | 2.5E-1 | 1.4E4 | 2.5E2 | 97 | 15 | 74 | 15 | 0.52 |
| Fn | ng/ml | 2.1E-1 | 2.1E-1 | 6.1E0 | 4.0E0 | 2.7E1 | 6.6E0 | 1.1E-14 | 2.1E-1 | 4.2E2 | 2.7E1 | 249 | 32 | 162 | 32 | 0.49 |
| Fp | ng/ml | 1.2E1 | 4.6E1 | 2.3E1 | 5.0E1 | 2.8E1 | 3.9E1 | 6.0E-3 | 9.7E-1 | 1.4E2 | 1.4E2 | 720 | 47 | 280 | 47 | 0.72 |
| Fr | ng/ml | 3.2E4 | 9.6E4 | 1.1E5 | 2.6E5 | 1.7E5 | 2.9E5 | 1.9E2 | 1.3E3 | 9.0E5 | 8.4E5 | 823 | 50 | 284 | 50 | 0.69 |
| Fw | pg/ml | 1.1E0 | 6.0E0 | 6.2E1 | 5.9E1 | 5.0E2 | 1.8E2 | 1.1E-14 | 1.2E-1 | 6.9E3 | 9.1E2 | 304 | 34 | 165 | 34 | 0.60 |
| Fy | ng/ml | 3.5E1 | 5.3E1 | 5.5E1 | 1.2E2 | 5.6E1 | 1.6E2 | 1.2E-1 | 5.3E0 | 3.3E2 | 6.5E2 | 246 | 31 | 161 | 31 | 0.63 |
| Gh | pg/ml | 3.9E0 | 3.9E0 | 7.6E1 | 1.3E1 | 2.7E2 | 2.2E1 | 2.9E-2 | 2.9E-2 | 1.8E3 | 8.0E1 | 95 | 15 | 74 | 15 | 0.47 |
| Gb | % | 4.0E1 | 3.7E1 | 4.6E1 | 6.1E1 | 3.8E1 | 7.0E1 | 2.2E0 | 2.1E1 | 2.3E2 | 3.0E2 | 97 | 15 | 73 | 15 | 0.58 |
| Gc | ng/ml | 9.9E1 | 1.3E2 | 1.5E2 | 1.6E2 | 1.7E2 | 1.3E2 | 6.4E0 | 2.9E1 | 1.2E3 | 4.7E2 | 166 | 17 | 90 | 17 | 0.57 |
| Gd | ng/ml | 3.0E1 | 2.4E1 | 3.2E1 | 3.2E1 | 1.7E1 | 2.3E1 | 3.0E0 | 7.6E0 | 8.1E1 | 8.0E1 | 188 | 17 | 83 | 17 | 0.45 |
| Gn | U/ml | 3.6E-1 | 1.5E-1 | 1.3E0 | 7.8E0 | 3.1E0 | 2.7E1 | 1.3E-3 | 5.6E-3 | 3.0E1 | 1.1E2 | 148 | 17 | 85 | 17 | 0.47 |
| Gl | pg/ml | 7.4E3 | 9.3E3 | 1.1E4 | 1.4E4 | 9.4E3 | 1.1E4 | 9.1E1 | 6.7E2 | 3.4E4 | 3.2E4 | 295 | 34 | 164 | 34 | 0.58 |
| Gp | U/ml | 1.7E0 | 5.2E-1 | 4.1E0 | 3.3E0 | 6.6E0 | 8.4E0 | 1.3E-3 | 1.5E-2 | 6.7E1 | 4.8E1 | 306 | 33 | 165 | 33 | 0.38 |
| Gz | ug/ml | 1.4E0 | 1.0E0 | 9.2E0 | 3.8E0 | 3.9E1 | 4.9E0 | 2.9E-16 | 1.0E-1 | 4.8E2 | 1.5E1 | 165 | 22 | 106 | 22 | 0.44 |
| Ha | ng/ml | 2.6E0 | 5.4E0 | 9.9E0 | 1.2E1 | 2.1E1 | 2.5E1 | 1.7E-2 | 6.4E-3 | 1.3E2 | 1.0E2 | 247 | 32 | 161 | 32 | 0.56 |
| Nm | pg/ml | 1.4E4 | 2.7E4 | 3.0E4 | 5.7E4 | 8.2E4 | 1.2E5 | 1.0E-9 | 1.0E-9 | 1.6E6 | 8.2E5 | 693 | 48 | 281 | 48 | 0.62 |
| Nn | pg/ml | 1.5E2 | 4.5E2 | 1.9E3 | 5.8E3 | 8.6E3 | 2.0E4 | 1.0E-9 | 1.0E-9 | 1.0E5 | 1.1E5 | 693 | 48 | 281 | 48 | 0.65 |
| No | pg/ml | 1.4E1 | 4.2E1 | 3.5E1 | 1.0E2 | 1.2E2 | 1.7E2 | 1.0E-9 | 1.0E-9 | 2.5E3 | 7.7E2 | 693 | 48 | 281 | 48 | 0.72 |
| Nq | pg/ml | 1.9E0 | 3.5E0 | 1.7E1 | 3.5E1 | 7.0E1 | 6.9E1 | 1.0E-9 | 1.0E-9 | 1.2E3 | 2.9E2 | 693 | 48 | 281 | 48 | 0.56 |
| Nr | pg/ml | 6.5E-1 | 6.1E0 | 3.1E1 | 6.7E1 | 2.0E2 | 2.2E2 | 1.0E-9 | 1.0E-9 | 4.1E3 | 1.4E3 | 693 | 48 | 281 | 48 | 0.66 |
| Ns | pg/ml | 1.0E-9 | 1.0E-9 | 9.7E0 | 1.7E0 | 5.6E1 | 1.1E1 | 1.0E-9 | 1.0E-9 | 1.1E3 | 7.9E1 | 693 | 48 | 281 | 48 | 0.47 |
| Nt | pg/ml | 1.0E2 | 1.6E2 | 1.3E2 | 2.1E2 | 1.1E2 | 2.0E2 | 1.0E-9 | 4.4E1 | 1.5E3 | 1.2E3 | 693 | 48 | 281 | 48 | 0.68 |
| Nu | pg/ml | 1.9E1 | 5.3E1 | 5.4E1 | 1.0E2 | 9.4E1 | 1.0E2 | 1.0E-9 | 1.0E-9 | 8.9E2 | 3.7E2 | 693 | 48 | 281 | 48 | 0.67 |
| Lu | pg/ml | 1.0E4 | 1.0E4 | 1.6E4 | 9.1E3 | 4.6E4 | 5.7E3 | 3.5E2 | 1.1E3 | 7.5E5 | 2.5E4 | 695 | 48 | 281 | 48 | 0.44 |
| Lv | pg/ml | 1.0E-9 | 1.7E1 | 1.1E1 | 3.3E1 | 2.1E1 | 4.6E1 | 1.0E-9 | 1.0E-9 | 2.4E2 | 1.8E2 | 695 | 48 | 281 | 48 | 0.64 |
| Lw | pg/ml | 1.0E-9 | 1.0E-9 | 3.7E-1 | 2.9E0 | 4.0E0 | 9.7E0 | 1.0E-9 | 1.0E-9 | 8.0E1 | 4.7E1 | 695 | 48 | 281 | 48 | 0.54 |
| Lx | pg/ml | 1.0E-9 | 1.7E2 | 1.3E2 | 5.4E2 | 4.2E2 | 9.0E2 | 1.0E-9 | 1.0E-9 | 6.2E3 | 4.5E3 | 695 | 48 | 281 | 48 | 0.73 |
| Ly | pg/ml | 1.0E-9 | 1.0E-9 | 1.0E1 | 1.3E1 | 2.0E1 | 2.0E1 | 1.0E-9 | 1.0E-9 | 1.6E2 | 7.2E1 | 695 | 48 | 281 | 48 | 0.52 |
| Lz | pg/ml | 1.0E-9 | 1.0E-9 | 4.9E0 | 5.0E0 | 3.4E1 | 1.5E1 | 1.0E-9 | 1.0E-9 | 6.0E2 | 6.2E1 | 695 | 48 | 281 | 48 | 0.52 |
| Ma | pg/ml | 2.7E2 | 6.5E2 | 1.4E3 | 3.2E3 | 3.8E3 | 8.6E3 | 1.0E-9 | 1.0E-9 | 6.5E4 | 5.2E4 | 695 | 48 | 281 | 48 | 0.63 |
| Mb | pg/ml | 2.5E1 | 3.5E1 | 3.1E1 | 3.6E1 | 1.6E1 | 1.7E1 | 5.4E0 | 4.1E0 | 2.1E2 | 7.1E1 | 695 | 48 | 281 | 48 | 0.57 |
| Mc | pg/ml | 1.0E-9 | 1.0E-9 | 3.6E-2 | 2.9E-2 | 5.3E-1 | 2.0E-1 | 1.0E-9 | 1.0E-9 | 1.3E1 | 1.4E0 | 695 | 48 | 281 | 48 | 0.50 |
| Md | pg/ml | 1.0E-9 | 1.0E-9 | 5.0E-1 | 8.5E-1 | 4.0E0 | 4.3E0 | 1.0E-9 | 1.0E-9 | 6.8E1 | 2.9E1 | 695 | 48 | 281 | 48 | 0.50 |
| Me | pg/ml | 3.2E1 | 2.4E1 | 3.1E1 | 2.5E1 | 2.0E1 | 2.9E1 | 1.0E-9 | 1.0E-9 | 3.2E2 | 1.8E2 | 695 | 48 | 281 | 48 | 0.36 |
| Mf | pg/ml | 1.0E-9 | 1.0E-9 | 5.0E-1 | 8.0E-1 | 2.9E0 | 1.9E0 | 1.0E-9 | 1.0E-9 | 5.6E1 | 9.1E0 | 695 | 48 | 281 | 48 | 0.56 |
| Mg | pg/ml | 1.7E0 | 2.4E0 | 7.3E0 | 9.5E0 | 1.2E1 | 1.5E1 | 1.0E-9 | 1.0E-9 | 9.2E1 | 6.6E1 | 695 | 48 | 281 | 48 | 0.55 |
| Mh | pg/ml | 1.0E-9 | 1.0E-9 | 1.5E0 | 2.3E0 | 1.1E1 | 6.9E0 | 1.0E-9 | 1.0E-9 | 1.6E2 | 4.2E1 | 695 | 48 | 281 | 48 | 0.59 |
| Mi | pg/ml | 1.0E-9 | 1.0E-9 | 4.9E-1 | 3.4E0 | 5.8E0 | 1.6E1 | 1.0E-9 | 1.0E-9 | 1.2E2 | 1.1E2 | 695 | 48 | 281 | 48 | 0.53 |
| Mj | pg/ml | 1.0E-9 | 1.0E-9 | 4.8E0 | 1.4E1 | 2.7E1 | 4.1E1 | 1.0E-9 | 1.0E-9 | 4.6E2 | 2.1E2 | 695 | 48 | 281 | 48 | 0.58 |
| Mk | pg/ml | 9.1E-1 | 2.9E0 | 1.5E1 | 1.7E1 | 9.7E1 | 7.2E1 | 1.0E-9 | 1.0E-9 | 1.7E3 | 5.0E2 | 695 | 48 | 281 | 48 | 0.53 |
| Ml | pg/ml | 1.0E-9 | 1.0E-9 | 5.8E0 | 2.3E1 | 8.2E1 | 8.9E1 | 1.0E-9 | 1.0E-9 | 2.1E3 | 5.1E2 | 695 | 48 | 281 | 48 | 0.55 |
| Mm | pg/ml | 5.4E2 | 8.8E2 | 9.2E2 | 1.7E3 | 1.1E3 | 2.2E3 | 1.0E-9 | 1.0E-9 | 7.3E3 | 1.2E4 | 695 | 48 | 281 | 48 | 0.62 |
| Mn | pg/ml | 5.3E0 | 8.3E0 | 1.0E1 | 1.3E1 | 2.4E1 | 2.0E1 | 1.0E-9 | 1.0E-9 | 3.5E2 | 1.3E2 | 695 | 48 | 281 | 48 | 0.61 |
| Mp | pg/ml | 1.0E-9 | 7.9E0 | 8.4E0 | 1.9E1 | 2.9E1 | 3.1E1 | 1.0E-9 | 1.0E-9 | 6.3E2 | 1.3E2 | 694 | 48 | 281 | 48 | 0.64 |
| Mq | pg/ml | 1.0E-9 | 1.0E-9 | 2.8E0 | 9.7E0 | 1.6E1 | 2.3E1 | 1.0E-9 | 1.0E-9 | 2.1E2 | 1.0E2 | 694 | 48 | 281 | 48 | 0.61 |
| Mr | pg/ml | 1.0E-9 | 3.2E0 | 1.6E1 | 1.5E2 | 7.9E1 | 5.6E2 | 1.0E-9 | 1.0E-9 | 1.4E3 | 3.4E3 | 694 | 48 | 281 | 48 | 0.61 |
| Ms | pg/ml | 4.1E2 | 3.1E2 | 5.6E2 | 3.7E2 | 6.4E2 | 3.4E2 | 1.0E-9 | 1.0E-9 | 5.6E3 | 1.4E3 | 694 | 48 | 281 | 48 | 0.43 |
| Mt | pg/ml | 1.0E-9 | 2.0E0 | 6.8E0 | 8.3E1 | 4.6E1 | 4.7E2 | 1.0E-9 | 1.0E-9 | 8.7E2 | 3.2E3 | 694 | 48 | 281 | 48 | 0.71 |
| Mu | pg/ml | 1.0E-9 | 1.0E-9 | 1.3E0 | 2.3E0 | 1.2E1 | 6.1E0 | 1.0E-9 | 1.0E-9 | 2.3E2 | 3.5E1 | 694 | 48 | 281 | 48 | 0.61 |
| Mv | pg/ml | 1.0E-9 | 1.0E-9 | 6.8E1 | 1.3E2 | 3.3E2 | 4.1E2 | 1.0E-9 | 1.0E-9 | 4.5E3 | 2.5E3 | 694 | 48 | 281 | 48 | 0.58 |
| Mw | pg/ml | 3.2E1 | 8.6E1 | 4.3E2 | 6.0E2 | 2.9E3 | 1.4E3 | 1.0E-9 | 1.0E-9 | 6.2E4 | 5.9E3 | 694 | 48 | 281 | 48 | 0.64 |
| Mx | pg/ml | 1.0E-9 | 1.0E-9 | 2.3E-1 | 8.3E-1 | 1.4E0 | 3.0E0 | 1.0E-9 | 1.0E-9 | 3.2E1 | 2.0E1 | 694 | 48 | 281 | 48 | 0.59 |
| My | pg/ml | 1.0E-9 | 1.0E-9 | 4.3E2 | 2.1E2 | 2.9E3 | 7.3E2 | 1.0E-9 | 1.0E-9 | 3.9E4 | 4.6E3 | 694 | 48 | 281 | 48 | 0.52 |
| Mz | pg/ml | 1.0E1 | 2.7E1 | 2.4E1 | 1.0E2 | 6.8E1 | 3.3E2 | 1.0E-9 | 1.0E-9 | 1.2E3 | 1.9E3 | 694 | 48 | 281 | 48 | 0.69 |
| Na | pg/ml | 1.0E-9 | 1.0E-9 | 7.7E-1 | 2.1E0 | 2.9E0 | 6.6E0 | 1.0E-9 | 1.0E-9 | 3.6E1 | 4.2E1 | 694 | 48 | 281 | 48 | 0.57 |

Figure 1 Continued

| Code | Units | Median | | Average | | Standard Deviation | | Minimum | | Maximum | | Number of Samples | | Number of Patients | | AUC |
|------|-------|--------|-----|---------|-----|------|------|---------|------|---------|------|--------|-----|----------|-----|-----|
|      |       | NonDis | Dis | NonDis  | Dis | NonDis | Dis | NonDis | Dis | NonDis | Dis | NonDis | Dis | NonDis | Dis |     |
| Nb | pg/ml | 1.9E0 | 3.1E0 | 4.0E0 | 1.1E1 | 1.3E1 | 3.3E1 | 1.0E-9 | 1.0E-9 | 2.3E2 | 2.1E2 | 694 | 48 | 281 | 48 | 0.63 |
| Nc | pg/ml | 3.8E2 | 2.7E2 | 6.2E2 | 3.7E2 | 7.7E2 | 3.6E2 | 1.0E-9 | 1.0E-9 | 9.2E3 | 1.1E3 | 694 | 48 | 281 | 48 | 0.44 |
| Nd | pg/ml | 2.9E1 | 6.5E0 | 2.7E1 | 1.6E1 | 5.0E1 | 2.0E1 | 1.0E-9 | 1.0E-9 | 1.2E3 | 9.4E1 | 694 | 48 | 281 | 48 | 0.37 |
| Ne | pg/ml | 4.7E2 | 3.5E2 | 6.0E2 | 3.8E2 | 5.9E2 | 3.3E2 | 1.0E-9 | 1.0E-9 | 7.0E3 | 1.7E3 | 694 | 48 | 281 | 48 | 0.39 |
| Nf | pg/ml | 1.0E-9 | 1.0E-9 | 3.2E0 | 7.2E0 | 1.0E1 | 2.5E1 | 1.0E-9 | 1.0E-9 | 1.6E2 | 1.3E2 | 694 | 48 | 281 | 48 | 0.51 |
| Ng | pg/ml | 2.1E1 | 1.0E1 | 1.3E2 | 8.0E1 | 2.6E2 | 1.8E2 | 1.0E-9 | 1.0E-9 | 2.3E3 | 1.2E3 | 694 | 48 | 281 | 48 | 0.47 |
| Nh | pg/ml | 7.1E1 | 4.0E1 | 9.4E1 | 5.0E1 | 8.6E1 | 3.7E1 | 1.0E-9 | 1.0E-9 | 5.6E2 | 1.5E2 | 694 | 48 | 281 | 48 | 0.34 |
| Ni | pg/ml | 1.0E-9 | 7.6E1 | 7.6E1 | 1.5E2 | 1.2E2 | 2.1E2 | 1.0E-9 | 1.0E-9 | 7.1E2 | 1.1E3 | 694 | 48 | 281 | 48 | 0.59 |
| Nj | pg/ml | 8.2E0 | 3.4E0 | 1.2E1 | 7.2E0 | 1.2E1 | 8.2E0 | 1.0E-9 | 1.0E-9 | 8.3E1 | 3.3E1 | 694 | 48 | 281 | 48 | 0.38 |
| Nk | pg/ml | 1.9E1 | 2.5E1 | 3.4E1 | 3.6E1 | 4.0E1 | 4.4E1 | 1.0E-9 | 1.0E-9 | 2.0E2 | 2.0E2 | 694 | 48 | 281 | 48 | 0.53 |
| Nl | pg/ml | 4.9E1 | 3.0E1 | 6.5E1 | 3.9E1 | 7.2E1 | 3.5E1 | 1.0E-9 | 1.0E-9 | 1.1E3 | 1.3E2 | 694 | 48 | 281 | 48 | 0.39 |
| Hl | pg/ml | 1.3E1 | 1.3E1 | 3.5E1 | 2.9E2 | 6.3E1 | 9.2E2 | 1.0E-9 | 1.0E-9 | 3.5E2 | 3.6E3 | 97 | 15 | 74 | 15 | 0.53 |
| Ho | pg/ml | 1.6E1 | 2.1E1 | 2.8E1 | 4.4E1 | 7.1E1 | 9.6E1 | 1.0E-9 | 2.0E0 | 7.0E2 | 3.9E2 | 97 | 15 | 74 | 15 | 0.58 |
| Hp | ng/ml | 1.6E0 | 3.9E0 | 1.2E2 | 2.4E2 | 3.0E2 | 4.0E2 | 1.0E-9 | 2.0E-1 | 8.9E2 | 8.9E2 | 97 | 15 | 74 | 15 | 0.64 |
| Tz | pg/ml | 5.2E3 | 7.5E3 | 1.3E4 | 2.0E4 | 6.4E4 | 6.5E4 | 1.0E-9 | 6.8E2 | 1.0E6 | 3.7E5 | 251 | 32 | 160 | 32 | 0.58 |
| Ua | pg/ml | 3.8E3 | 5.0E3 | 2.3E4 | 1.1E4 | 1.4E5 | 1.6E4 | 1.0E-9 | 9.4E2 | 2.1E6 | 6.6E4 | 251 | 32 | 160 | 32 | 0.55 |
| Ub | pg/ml | 5.7E2 | 4.8E2 | 8.6E2 | 8.1E2 | 1.0E3 | 9.2E2 | 1.0E-9 | 1.2E1 | 9.8E3 | 4.1E3 | 251 | 32 | 160 | 32 | 0.48 |
| Ue | pg/ml | 3.0E1 | 2.9E1 | 3.7E1 | 4.1E1 | 3.2E1 | 3.2E1 | 9.8E-2 | 5.9E0 | 3.5E2 | 1.4E2 | 251 | 32 | 160 | 32 | 0.54 |
| Uc | pg/ml | 8.6E2 | 1.4E3 | 1.6E3 | 3.8E3 | 2.7E3 | 1.0E4 | 1.0E-9 | 5.5E1 | 2.9E4 | 5.7E4 | 251 | 32 | 160 | 32 | 0.60 |
| Ud | pg/ml | 1.0E-9 | 1.0E-9 | 1.7E0 | 1.8E0 | 2.5E1 | 9.4E0 | 1.0E-9 | 1.0E-9 | 3.9E2 | 5.3E1 | 251 | 32 | 160 | 32 | 0.53 |
| Hq | pg/ml | 1.1E0 | 1.3E0 | 1.3E2 | 1.3E1 | 1.8E3 | 4.2E1 | 1.0E-9 | 1.0E-9 | 3.4E4 | 2.3E2 | 691 | 48 | 280 | 48 | 0.50 |
| Hr | pg/ml | 1.3E2 | 1.2E2 | 8.2E2 | 7.0E2 | 1.6E3 | 1.7E3 | 1.0E-9 | 1.0E-9 | 1.4E4 | 8.9E3 | 691 | 48 | 280 | 48 | 0.48 |
| Hu | pg/ml | 7.1E0 | 3.1E1 | 3.0E3 | 1.1E3 | 2.9E4 | 4.7E3 | 1.0E-9 | 1.0E-9 | 6.3E5 | 3.2E4 | 691 | 48 | 280 | 48 | 0.59 |
| Hv | pg/ml | 1.4E0 | 1.5E0 | 3.3E0 | 2.2E1 | 1.2E1 | 1.3E2 | 1.0E-9 | 1.0E-9 | 2.5E2 | 8.9E2 | 691 | 48 | 280 | 48 | 0.53 |
| Hw | pg/ml | 7.1E1 | 5.4E0 | 2.0E1 | 2.2E2 | 8.0E1 | 1.3E3 | 1.0E-9 | 1.0E-9 | 1.7E3 | 9.4E3 | 691 | 48 | 280 | 48 | 0.43 |
| Hx | pg/ml | 8.8E0 | 1.3E1 | 4.4E1 | 6.4E1 | 3.6E2 | 2.2E2 | 1.0E-9 | 1.0E-9 | 9.3E3 | 1.3E3 | 691 | 48 | 280 | 48 | 0.56 |
| Ib | ng/ml | 6.2E-2 | 4.4E-2 | 1.4E0 | 2.0E0 | 5.0E0 | 9.9E0 | 1.0E-9 | 1.0E-9 | 3.6E1 | 5.6E1 | 241 | 32 | 159 | 32 | 0.46 |
| Ic | U/ml | 2.2E2 | 2.2E2 | 7.3E2 | 2.0E2 | 6.1E3 | 1.3E2 | 2.4E0 | 2.1E1 | 9.3E4 | 4.2E2 | 241 | 32 | 159 | 32 | 0.53 |
| Id | U/ml | 6.4E-1 | 9.7E-1 | 1.2E0 | 1.6E1 | 2.0E0 | 7.6E1 | 1.0E-9 | 3.0E-1 | 2.3E1 | 4.3E2 | 241 | 32 | 159 | 32 | 0.67 |
| Tt | pg/ml | 1.6E2 | 1.7E2 | 1.7E2 | 1.8E2 | 5.1E1 | 7.3E1 | 4.3E1 | 1.0E2 | 3.6E2 | 4.4E2 | 231 | 28 | 153 | 28 | 0.54 |
| To | pg/ml | 1.6E0 | 1.6E0 | 1.9E0 | 1.8E0 | 2.4E0 | 2.5E0 | 1.0E-9 | 1.0E-9 | 2.3E1 | 1.2E1 | 242 | 30 | 157 | 30 | 0.48 |
| Tr | pg/ml | 2.8E0 | 5.2E0 | 5.8E0 | 1.1E1 | 2.0E1 | 1.7E1 | 1.0E-9 | 4.7E-2 | 3.1E2 | 7.6E1 | 238 | 29 | 156 | 29 | 0.64 |
| Tn | pg/ml | 2.6E1 | 4.7E1 | 8.0E1 | 2.1E2 | 2.2E2 | 5.3E2 | 2.4E0 | 6.6E0 | 1.8E3 | 2.3E3 | 242 | 30 | 157 | 30 | 0.64 |
| Tv | ng/ml | 1.2E1 | 1.3E1 | 1.9E1 | 2.7E2 | 3.7E1 | 1.3E3 | 1.0E-9 | 1.0E-9 | 4.9E2 | 7.1E3 | 242 | 30 | 157 | 30 | 0.50 |
| Ih | ng/ml | 6.9E1 | 1.8E2 | 2.1E2 | 3.7E2 | 3.7E2 | 5.0E2 | 1.0E-9 | 1.0E-9 | 2.6E3 | 2.8E3 | 694 | 48 | 280 | 48 | 0.62 |
| Ii | ng/ml | 9.0E1 | 1.1E2 | 2.6E2 | 3.7E2 | 7.4E2 | 8.1E2 | 7.3E-1 | 2.3E0 | 1.0E4 | 4.5E3 | 694 | 48 | 280 | 48 | 0.57 |
| Ij | ng/ml | 7.3E1 | 1.2E2 | 1.8E2 | 7.0E2 | 6.4E2 | 3.5E3 | 2.1E0 | 1.1E1 | 6.4E3 | 2.4E4 | 686 | 47 | 279 | 47 | 0.66 |
| Ik | ng/ml | 1.4E1 | 1.4E1 | 9.8E2 | 5.1E2 | 9.3E3 | 6.4E2 | 5.9E-1 | 2.3E0 | 1.2E5 | 2.5E3 | 690 | 48 | 279 | 48 | 0.66 |
| Il | ng/ml | 3.3E2 | 6.1E2 | 1.2E3 | 2.5E3 | 2.7E3 | 4.1E3 | 1.0E-9 | 1.0E-9 | 1.2E4 | 1.3E4 | 680 | 48 | 279 | 48 | 0.57 |
| Im | ng/ml | 1.9E2 | 6.5E2 | 3.4E2 | 8.6E2 | 5.0E2 | 1.2E3 | 1.3E1 | 4.7E1 | 6.0E3 | 6.2E3 | 689 | 48 | 279 | 48 | 0.69 |
| In | ng/ml | 3.9E0 | 3.2E0 | 2.5E1 | 1.0E2 | 1.7E2 | 6.5E2 | 1.0E-9 | 1.0E-9 | 3.9E3 | 4.5E3 | 694 | 48 | 280 | 48 | 0.45 |
| Hb | ng/ml | 2.4E1 | 3.3E1 | 3.2E1 | 4.9E1 | 2.9E1 | 4.6E1 | 4.8E-1 | 6.2E-1 | 1.5E2 | 1.9E2 | 248 | 32 | 160 | 32 | 0.62 |
| Hc | pg/ml | 6.7E2 | 6.4E2 | 3.7E3 | 2.9E3 | 1.3E4 | 9.0E3 | 1.0E-9 | 1.0E-9 | 1.0E5 | 5.0E4 | 248 | 32 | 160 | 32 | 0.46 |
| Hf | ng/ml | 1.5E2 | 2.0E2 | 3.8E2 | 3.2E2 | 5.3E2 | 3.9E2 | 1.0E-9 | 1.0E-9 | 2.5E3 | 1.8E3 | 248 | 32 | 160 | 32 | 0.50 |
| Io | ng/ml | 7.5E3 | 9.3E3 | 2.4E4 | 1.4E4 | 1.6E5 | 1.2E4 | 1.0E-9 | 1.8E2 | 4.0E6 | 5.4E4 | 687 | 48 | 280 | 48 | 0.54 |
| Ip | ng/ml | 8.7E0 | 3.0E1 | 1.9E1 | 2.8E1 | 2.4E1 | 2.2E1 | 1.0E-9 | 3.7E-2 | 2.6E2 | 8.8E1 | 687 | 48 | 280 | 48 | 0.62 |
| Iq | ug/ml | 9.5E-2 | 1.7E-1 | 4.0E1 | 6.3E0 | 7.3E2 | 3.2E1 | 1.0E-9 | 1.0E-9 | 1.4E4 | 2.2E2 | 687 | 48 | 280 | 48 | 0.56 |
| Ir | ug/ml | 3.3E-1 | 8.0E-1 | 3.8E0 | 1.5E1 | 2.8E1 | 5.8E1 | 1.0E-9 | 1.0E-9 | 5.1E2 | 3.7E2 | 686 | 48 | 280 | 48 | 0.67 |
| Is | ng/ml | 1.4E0 | 8.6E0 | 5.7E0 | 2.2E1 | 2.3E1 | 4.4E1 | 1.0E-9 | 5.3E-2 | 5.5E2 | 2.6E2 | 687 | 48 | 280 | 48 | 0.74 |
| It | ng/ml | 2.0E0 | 3.8E0 | 2.6E1 | 3.0E1 | 1.5E2 | 1.1E2 | 1.0E-9 | 1.0E-9 | 2.8E3 | 6.8E2 | 687 | 48 | 280 | 48 | 0.61 |
| Iu | ng/ml | 2.1E2 | 2.7E2 | 1.4E3 | 2.0E3 | 4.3E3 | 5.1E3 | 1.0E-9 | 1.0E-9 | 2.9E4 | 2.4E4 | 687 | 48 | 280 | 48 | 0.52 |
| Iv | ng/ml | 1.2E1 | 3.6E1 | 6.1E1 | 2.2E2 | 6.1E2 | 7.5E2 | 1.0E-9 | 1.0E-9 | 1.6E4 | 3.8E3 | 686 | 48 | 280 | 48 | 0.69 |
| Iz | ng/ml | 1.4E2 | 1.9E2 | 6.8E2 | 3.2E2 | 4.0E3 | 3.8E2 | 1.5E0 | 4.9E0 | 6.2E4 | 1.7E3 | 248 | 32 | 160 | 32 | 0.53 |
| Yg | pg/ml | 2.8E2 | 5.1E2 | 1.3E3 | 1.3E3 | 5.3E3 | 1.7E3 | 1.0E-9 | 1.1E0 | 5.0E4 | 5.0E3 | 95 | 14 | 73 | 14 | 0.60 |
| Yh | pg/ml | 2.1E2 | 6.6E2 | 5.2E2 | 6.4E2 | 9.2E2 | 6.5E2 | 1.0E-9 | 1.0E-9 | 7.8E3 | 2.3E3 | 95 | 14 | 73 | 14 | 0.58 |
| Yi | pg/ml | 2.6E2 | 6.9E2 | 5.2E2 | 2.8E3 | 8.6E2 | 6.8E3 | 1.0E-9 | 1.0E-9 | 7.6E3 | 2.6E4 | 95 | 14 | 73 | 14 | 0.70 |
| Yk | U/ml | 1.0E-9 | 1.0E-9 | 1.6E-1 | 4.0E-1 | 4.7E-1 | 1.5E0 | 1.0E-9 | 1.0E-9 | 3.0E0 | 5.6E0 | 95 | 14 | 73 | 14 | 0.44 |

Figure 1 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yj | pg/ml | 1.5E2 | 1.5E2 | 4.3E2 | 3.1E2 | 9.1E2 | 2.9E2 | 1.0E-9 | 1.7E1 | 7.0E3 | 8.5E2 | 95 | 14 | 73 | 14 | 0.53 |
| Yd | ng/ml | 2.0E-1 | 2.0E-1 | 3.3E-1 | 4.1E-1 | 3.6E-1 | 6.1E-1 | 6.6E-3 | 6.6E-3 | 1.8E0 | 2.3E0 | 100 | 15 | 77 | 15 | 0.49 |
| Wb | pg/ml | 3.1E4 | 3.8E4 | 3.5E4 | 4.8E4 | 2.1E4 | 3.3E4 | 2.2E3 | 1.4E4 | 1.6E5 | 1.5E5 | 99 | 15 | 77 | 15 | 0.64 |
| Vz | pg/ml | 3.2E0 | 2.8E0 | 4.7E0 | 5.0E0 | 6.0E0 | 5.4E0 | 1.0E-9 | 7.6E-2 | 4.0E1 | 2.2E1 | 99 | 15 | 77 | 15 | 0.55 |
| Si | ng/ml | 1.0E0 | 8.5E-1 | 2.0E0 | 1.9E0 | 2.7E0 | 1.8E0 | 8.6E-3 | 3.7E-2 | 1.3E1 | 5.6E0 | 97 | 15 | 74 | 15 | 0.53 |
| Sf | mIU/mL | 1.3E1 | 1.3E1 | 4.0E1 | 2.6E1 | 8.6E1 | 3.4E1 | 8.1E-2 | 9.4E-1 | 7.2E2 | 1.2E2 | 97 | 15 | 74 | 15 | 0.49 |
| Sh | mIU/mL | 1.3E1 | 7.7E0 | 4.8E1 | 3.6E1 | 1.0E2 | 7.6E1 | 2.9E-2 | 1.3E-1 | 5.9E2 | 2.9E2 | 97 | 15 | 74 | 15 | 0.44 |
| Sj | ng/ml | 4.0E-1 | 4.3E-1 | 4.1E-1 | 4.4E-1 | 1.0E-1 | 9.0E-2 | 1.1E-1 | 3.4E-1 | 6.6E-1 | 7.0E-1 | 97 | 15 | 74 | 15 | 0.57 |
| Rc | pg/ml | 5.5E3 | 7.7E3 | 7.3E3 | 7.4E3 | 6.0E3 | 4.0E3 | 1.9E2 | 1.3E3 | 3.9E4 | 1.7E4 | 248 | 32 | 160 | 32 | 0.56 |
| Rb | pg/ml | 7.9E-1 | 7.2E-1 | 2.6E0 | 3.9E0 | 4.4E0 | 1.0E1 | 1.0E-9 | 1.0E-9 | 4.3E1 | 5.6E1 | 248 | 32 | 160 | 32 | 0.52 |
| Zq | 2.6ng/ml | 2.3E2 | 3.9E2 | 3.0E2 | 5.0E2 | 2.6E2 | 3.3E2 | 8.3E0 | 1.8E1 | 9.7E2 | 9.7E2 | 97 | 15 | 74 | 15 | 0.69 |
| Zw | 2.5ng/ml | 5.7E0 | 4.7E0 | 1.1E1 | 1.6E1 | 1.4E1 | 2.1E1 | 6.3E-2 | 6.6E-1 | 5.9E1 | 6.3E1 | 100 | 15 | 77 | 15 | 0.58 |
| Zx | 2.3mU/ml | 1.3E-1 | 1.1E-1 | 3.7E-1 | 2.8E-1 | 1.2E0 | 4.7E-1 | 3.2E-2 | 6.1E-2 | 1.2E1 | 1.9E0 | 100 | 15 | 77 | 15 | 0.53 |
| Pz | ng/ml | 3.3E3 | 1.0E4 | 6.8E3 | 7.2E3 | 1.8E4 | 5.4E3 | 1.3E1 | 1.1E2 | 2.8E5 | 2.8E4 | 687 | 48 | 278 | 48 | 0.61 |
| Qa | ng/ml | 3.1E3 | 9.7E3 | 5.8E3 | 1.6E4 | 7.1E3 | 3.2E4 | 1.5E2 | 6.0E2 | 5.2E4 | 2.2E5 | 687 | 48 | 278 | 48 | 0.72 |
| Qb | ng/ml | 9.1E1 | 2.0E2 | 2.1E2 | 3.5E2 | 5.2E2 | 6.1E2 | 7.9E-1 | 6.2E0 | 8.3E3 | 4.1E3 | 687 | 48 | 278 | 48 | 0.64 |
| Qc | ng/ml | 2.1E2 | 4.9E2 | 4.4E2 | 6.4E2 | 7.6E2 | 7.8E2 | 1.0E-9 | 3.2E0 | 1.1E4 | 4.3E3 | 687 | 48 | 278 | 48 | 0.60 |
| Qd | ng/ml | 8.7E3 | 1.9E4 | 1.9E4 | 4.0E4 | 8.2E4 | 5.1E4 | 1.5E2 | 1.7E3 | 2.0E6 | 2.3E5 | 687 | 48 | 278 | 48 | 0.69 |
| Qe | ng/ml | 8.0E2 | 2.6E3 | 1.7E3 | 3.3E3 | 4.2E3 | 3.4E3 | 1.0E-9 | 1.5E2 | 9.7E4 | 1.8E4 | 687 | 48 | 278 | 48 | 0.73 |
| Jd | ng/ml | 9.2E-1 | 2.8E0 | 6.7E0 | 4.7E0 | 4.4E1 | 7.2E0 | 1.0E-9 | 1.0E-9 | 6.5E2 | 3.5E1 | 249 | 32 | 162 | 32 | 0.64 |
| Je | ng/ml | 1.0E-9 | 5.7E-1 | 2.3E0 | 2.2E0 | 8.0E0 | 3.1E0 | 1.0E-9 | 1.0E-9 | 8.8E1 | 1.1E1 | 249 | 32 | 162 | 32 | 0.55 |
| Jf | ng/ml | 1.0E-9 | 1.0E-9 | 1.1E0 | 1.1E0 | 2.3E0 | 1.8E0 | 1.0E-9 | 1.0E-9 | 1.2E1 | 7.7E0 | 249 | 32 | 162 | 32 | 0.54 |
| Jg | ng/ml | 4.4E2 | 1.1E3 | 7.3E2 | 1.4E3 | 9.6E2 | 1.4E3 | 1.0E-9 | 3.7E1 | 1.0E4 | 7.1E3 | 691 | 48 | 280 | 48 | 0.67 |
| Jh | ng/ml | 2.9E0 | 6.5E0 | 2.4E1 | 5.4E1 | 1.1E2 | 1.2E2 | 1.0E-9 | 1.0E-9 | 1.6E3 | 5.4E2 | 691 | 48 | 280 | 48 | 0.60 |
| Ji | ng/ml | 5.0E1 | 1.2E2 | 7.0E1 | 2.0E2 | 6.9E1 | 2.2E2 | 1.0E-9 | 1.3E1 | 5.3E2 | 1.3E3 | 691 | 48 | 280 | 48 | 0.78 |
| Sr | pg/mL | 3.4E2 | 1.2E3 | 8.1E2 | 2.2E3 | 1.3E3 | 3.7E3 | 1.0E-9 | 1.0E-9 | 9.8E3 | 2.1E4 | 239 | 32 | 157 | 32 | 0.70 |
| Ss | pg/mL | 9.2E4 | 1.1E5 | 1.5E5 | 1.5E5 | 1.9E5 | 1.5E5 | 2.7E3 | 1.3E4 | 1.8E6 | 5.7E5 | 239 | 32 | 157 | 32 | 0.51 |
| St | pg/mL | 2.2E7 | 8.4E7 | 4.9E7 | 1.4E8 | 9.0E7 | 3.0E8 | 1.0E-9 | 2.3E6 | 1.2E9 | 1.7E9 | 244 | 32 | 158 | 32 | 0.69 |
| Wc | ng/ml | 1.0E-9 | 1.0E-9 | 5.8E-2 | 1.2E-1 | 1.3E-1 | 4.6E-1 | 1.0E-9 | 1.0E-9 | 9.8E-1 | 1.8E0 | 100 | 15 | 77 | 15 | 0.38 |
| Wd | ng/ml | 9.4E0 | 1.2E1 | 3.6E1 | 1.3E2 | 1.0E2 | 3.1E2 | 1.0E-9 | 3.5E0 | 7.9E2 | 1.2E3 | 100 | 15 | 77 | 15 | 0.63 |
| We | ng/ml | 3.6E-1 | 4.7E-1 | 8.7E-1 | 4.9E0 | 1.4E0 | 9.0E0 | 1.0E-9 | 2.0E-3 | 9.7E0 | 2.3E1 | 100 | 15 | 77 | 15 | 0.54 |
| Wg | ng/ml | 1.0E-9 | 1.0E-9 | 1.6E-4 | 3.6E-2 | 1.6E-3 | 1.4E-1 | 1.0E-9 | 1.0E-9 | 1.6E-2 | 5.3E-1 | 100 | 15 | 77 | 15 | 0.53 |
| Wh | ng/ml | 1.0E-2 | 2.0E-2 | 7.0E-2 | 3.6E-1 | 2.6E-1 | 1.2E0 | 1.0E-9 | 3.7E-3 | 2.5E0 | 4.5E0 | 100 | 15 | 77 | 15 | 0.63 |
| Wf | ng/ml | 1.0E-9 | 1.0E-9 | 1.8E-1 | 2.8E-1 | 5.6E-1 | 6.0E-1 | 1.0E-9 | 1.0E-9 | 4.6E0 | 2.3E0 | 100 | 15 | 77 | 15 | 0.55 |
| Ra | pg/ml | 1.0E-9 | 1.0E-9 | 6.4E-1 | 2.7E0 | 1.3E0 | 1.1E1 | 1.0E-9 | 1.0E-9 | 7.3E0 | 6.4E1 | 248 | 32 | 160 | 32 | 0.53 |
| Qz | pg/ml | 1.1E1 | 1.2E1 | 6.1E1 | 5.0E1 | 1.0E2 | 7.5E1 | 1.0E-9 | 1.0E-9 | 7.1E2 | 2.3E2 | 248 | 32 | 160 | 32 | 0.51 |
| Qy | pg/ml | 4.3E-1 | 5.7E-1 | 1.0E1 | 5.9E0 | 5.7E1 | 1.9E1 | 1.0E-9 | 1.0E-9 | 6.5E2 | 9.7E1 | 248 | 32 | 160 | 32 | 0.55 |
| Qx | pg/ml | 1.0E-9 | 1.0E-9 | 6.8E0 | 6.1E0 | 5.2E1 | 2.0E1 | 1.0E-9 | 1.0E-9 | 5.8E2 | 1.1E2 | 248 | 32 | 160 | 32 | 0.52 |
| Qw | pg/ml | 1.0E-9 | 1.0E-9 | 2.5E0 | 1.5E0 | 1.1E1 | 4.1E0 | 1.0E-9 | 1.0E-9 | 1.2E2 | 2.3E1 | 248 | 32 | 160 | 32 | 0.50 |
| Qv | pg/ml | 2.4E4 | 2.1E4 | 3.4E4 | 2.1E4 | 5.7E4 | 1.8E4 | 1.0E-9 | 4.0E2 | 7.4E5 | 9.1E4 | 248 | 32 | 160 | 32 | 0.40 |
| Qu | pg/ml | 7.7E0 | 9.2E0 | 8.8E1 | 8.7E1 | 1.7E2 | 1.7E2 | 1.0E-9 | 1.0E-9 | 9.8E2 | 7.0E2 | 248 | 32 | 160 | 32 | 0.50 |
| Qt | pg/ml | 1.0E1 | 2.0E1 | 5.3E1 | 5.0E1 | 1.3E2 | 8.1E1 | 1.0E-9 | 1.0E-9 | 1.0E3 | 3.1E2 | 248 | 32 | 160 | 32 | 0.57 |
| Qh | ng/ml | 1.7E1 | 3.4E1 | 3.6E1 | 5.8E1 | 6.1E1 | 8.5E1 | 1.0E-9 | 3.8E0 | 6.4E2 | 4.6E2 | 248 | 32 | 160 | 32 | 0.63 |
| Qg | ng/ml | 8.5E0 | 4.9E0 | 2.1E1 | 1.4E1 | 7.1E1 | 2.7E1 | 5.1E-2 | 3.3E-1 | 1.0E3 | 1.4E2 | 248 | 32 | 160 | 32 | 0.41 |
| Jj | ng/ml | 6.7E2 | 2.8E2 | 1.9E3 | 5.3E2 | 1.4E4 | 6.1E2 | 2.3E0 | 1.2E1 | 3.4E5 | 3.3E3 | 691 | 48 | 280 | 48 | 0.33 |
| Jk | ng/ml | 3.0E0 | 3.9E0 | 2.2E1 | 2.8E1 | 4.7E1 | 5.1E1 | 1.0E-9 | 2.4E-1 | 3.9E2 | 2.4E2 | 691 | 48 | 280 | 48 | 0.56 |
| Jl | ng/ml | 3.9E-1 | 1.6E0 | 1.7E0 | 2.1E2 | 4.2E0 | 1.4E3 | 7.6E-4 | 1.5E-2 | 3.2E1 | 9.9E3 | 691 | 48 | 280 | 48 | 0.68 |
| Jm | ng/ml | 1.7E1 | 3.6E1 | 5.2E1 | 9.9E1 | 1.1E2 | 3.0E2 | 1.0E-9 | 2.5E-1 | 1.4E3 | 2.1E3 | 691 | 48 | 280 | 48 | 0.57 |
| Jn | pg/ml | 3.8E-1 | 8.9E-1 | 2.4E0 | 3.0E1 | 2.4E1 | 1.4E2 | 1.0E-9 | 1.0E-9 | 6.2E2 | 7.3E2 | 691 | 48 | 280 | 48 | 0.67 |
| Jo | pg/ml | 3.6E3 | 4.1E3 | 4.9E3 | 7.7E3 | 3.9E3 | 1.5E4 | 2.0E1 | 2.3E2 | 2.4E4 | 1.0E5 | 691 | 48 | 280 | 48 | 0.53 |
| Jp | pg/ml | 6.8E4 | 8.9E4 | 7.1E4 | 9.6E4 | 3.6E4 | 4.2E4 | 5.8E2 | 2.6E4 | 3.0E5 | 2.1E5 | 691 | 48 | 280 | 48 | 0.68 |
| Jq | pg/ml | 9.5E1 | 1.8E2 | 1.5E2 | 5.0E2 | 2.2E2 | 1.3E3 | 1.0E0 | 1.4E0 | 4.0E3 | 8.7E3 | 691 | 48 | 280 | 48 | 0.66 |
| Jr | pg/ml | 5.1E0 | 1.0E1 | 3.5E1 | 2.8E2 | 4.1E2 | 1.3E3 | 1.0E-9 | 1.0E-9 | 1.1E4 | 7.4E3 | 691 | 48 | 280 | 48 | 0.65 |
| Js | pg/ml | 1.3E1 | 1.8E1 | 5.2E1 | 1.5E2 | 4.0E2 | 5.9E2 | 1.0E-9 | 1.7E0 | 1.0E4 | 3.0E3 | 691 | 48 | 280 | 48 | 0.64 |
| Jt | pg/ml | 2.5E3 | 3.4E3 | 3.1E3 | 5.2E3 | 2.3E3 | 7.9E3 | 2.2E1 | 4.1E2 | 2.2E4 | 5.2E4 | 691 | 48 | 280 | 48 | 0.60 |
| Xa | pg/ml | 1.0E-9 | 8.7E0 | 9.0E0 | 1.0E2 | 1.7E1 | 3.1E2 | 1.0E-9 | 1.0E-9 | 9.6E1 | 1.2E3 | 99 | 15 | 77 | 15 | 0.72 |
| Ye | pg/ml | 1.0E-9 | 1.0E-9 | 5.2E0 | 1.2E0 | 1.3E1 | 4.6E0 | 1.0E-9 | 1.0E-9 | 6.9E1 | 1.8E1 | 99 | 15 | 77 | 15 | 0.39 |

Figure 1 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Tm | pg/ml | 1.0E-9 | 1.0E-9 | 3.5E0 | 1.1E0 | 6.8E0 | 2.9E0 | 1.0E-9 | 1.0E-9 | 4.6E1 | 8.4E0 | 99 | 15 | 77 | 15 | 0.41 |
| Tl | pg/ml | 1.3E-1 | 1.0E-9 | 3.1E-1 | 1.8E0 | 3.7E-1 | 6.3E0 | 1.0E-9 | 1.0E-9 | 1.8E0 | 2.5E1 | 99 | 15 | 77 | 15 | 0.38 |
| Ju | mIU/ml | 8.5E0 | 1.1E1 | 2.0E1 | 1.7E1 | 3.2E1 | 1.9E1 | 6.5E-2 | 1.9E-1 | 2.3E2 | 8.9E1 | 249 | 32 | 162 | 32 | 0.54 |
| Jv | mIU/ml | 1.1E1 | 1.2E1 | 3.5E1 | 2.9E1 | 6.3E1 | 4.0E1 | 1.0E-2 | 2.4E-2 | 4.4E2 | 1.9E2 | 249 | 32 | 162 | 32 | 0.52 |
| Jy | ng/ml | 1.6E-3 | 2.0E-3 | 2.2E-3 | 4.3E-3 | 4.3E-3 | 7.8E-3 | 1.0E-9 | 5.3E-4 | 5.2E-2 | 4.1E-2 | 249 | 32 | 162 | 32 | 0.62 |
| Kc | pg/ml | 2.3E1 | 3.2E1 | 4.1E1 | 5.0E1 | 4.3E1 | 6.0E1 | 1.0E-9 | 1.0E-9 | 1.9E2 | 2.7E2 | 249 | 32 | 160 | 32 | 0.55 |
| Kd | pg/ml | 1.0E-9 | 1.0E-9 | 1.6E2 | 1.7E3 | 5.4E2 | 6.8E3 | 1.0E-9 | 1.0E-9 | 4.8E3 | 3.8E4 | 249 | 32 | 160 | 32 | 0.57 |
| Ke | pg/ml | 1.2E4 | 1.9E4 | 1.4E4 | 3.5E4 | 1.1E4 | 5.7E4 | 3.4E2 | 1.8E3 | 7.0E4 | 3.2E5 | 249 | 32 | 160 | 32 | 0.68 |
| Kf | pg/mL | 6.4E0 | 7.3E0 | 6.8E0 | 1.1E1 | 5.6E0 | 1.5E1 | 1.0E-9 | 1.0E-9 | 2.6E1 | 7.8E1 | 249 | 32 | 160 | 32 | 0.57 |
| Kg | pg/mL | 1.1E3 | 1.1E3 | 1.9E3 | 2.3E3 | 2.6E3 | 4.8E3 | 7.3E1 | 1.3E1 | 2.2E4 | 2.7E4 | 249 | 32 | 160 | 32 | 0.47 |
| Ki | pg/ml | 6.1E1 | 7.6E1 | 7.0E1 | 8.4E1 | 5.2E1 | 6.2E1 | 1.0E-9 | 1.0E-9 | 3.8E2 | 2.5E2 | 248 | 32 | 160 | 32 | 0.57 |
| Kj | pg/ml | 1.0E3 | 7.7E2 | 1.6E3 | 1.7E3 | 1.6E3 | 2.8E3 | 1.4E1 | 3.3E1 | 1.0E4 | 1.5E4 | 249 | 32 | 160 | 32 | 0.42 |
| Kk | pg/ml | 6.9E0 | 1.0E1 | 1.1E1 | 1.7E1 | 1.5E1 | 1.8E1 | 1.0E-9 | 2.0E0 | 1.6E2 | 5.9E1 | 249 | 32 | 160 | 32 | 0.63 |
| Kl | pg/ml | 2.0E4 | 2.4E4 | 2.7E4 | 3.3E4 | 2.5E4 | 2.8E4 | 1.6E2 | 1.3E3 | 1.6E5 | 1.1E5 | 249 | 32 | 160 | 32 | 0.56 |
| Kn | pg/ml | 2.9E1 | 6.0E1 | 5.8E1 | 2.6E2 | 9.0E1 | 8.6E2 | 1.0E-9 | 1.0E-9 | 7.3E2 | 4.9E3 | 249 | 32 | 160 | 32 | 0.63 |
| Ko | pg/ml | 3.2E2 | 5.9E2 | 4.3E2 | 7.9E2 | 4.4E2 | 9.5E2 | 1.0E-9 | 1.0E-9 | 2.2E3 | 4.1E3 | 249 | 32 | 160 | 32 | 0.63 |
| Kp | pg/ml | 3.0E2 | 3.4E2 | 3.4E2 | 7.8E2 | 2.6E2 | 2.3E3 | 1.0E-9 | 3.7E1 | 1.7E3 | 1.3E4 | 249 | 32 | 160 | 32 | 0.56 |
| Kq | pg/ml | 3.0E2 | 5.6E2 | 4.8E2 | 6.0E3 | 8.7E2 | 2.8E4 | 1.6E0 | 4.8E1 | 9.8E3 | 1.6E5 | 240 | 32 | 154 | 32 | 0.71 |
| Kr | pg/ml | 3.8E-1 | 5.1E-1 | 2.2E0 | 1.5E1 | 4.2E0 | 7.3E1 | 1.0E-9 | 1.0E-9 | 3.5E1 | 4.2E2 | 240 | 32 | 154 | 32 | 0.53 |
| Ks | pg/ml | 1.4E4 | 1.7E4 | 2.0E4 | 2.0E4 | 1.8E4 | 1.7E4 | 5.1E1 | 9.9E2 | 1.1E5 | 5.1E4 | 240 | 32 | 154 | 32 | 0.51 |
| Ps | ng/ml | 1.6E2 | 4.7E2 | 4.8E2 | 7.7E2 | 1.3E3 | 9.3E2 | 4.1E-1 | 1.3E1 | 9.0E3 | 3.8E3 | 97 | 15 | 74 | 15 | 0.73 |
| Kx | ng/ml | 1.0E-9 | 5.8E-3 | 6.6E-3 | 1.4E-2 | 1.4E-2 | 2.0E-2 | 1.0E-9 | 1.0E-9 | 1.0E-1 | 6.5E-2 | 247 | 32 | 160 | 32 | 0.62 |
| Ky | ng/ml | 8.5E-2 | 2.8E-1 | 3.5E-1 | 6.2E-1 | 7.8E-1 | 7.5E-1 | 1.0E-9 | 1.0E-9 | 5.4E0 | 2.7E0 | 247 | 32 | 160 | 32 | 0.65 |
| Kz | ng/ml | 1.0E-9 | 1.0E-9 | 3.7E-3 | 5.5E-3 | 5.9E-3 | 6.9E-3 | 1.0E-9 | 1.0E-9 | 3.6E-2 | 1.8E-2 | 247 | 32 | 160 | 32 | 0.56 |
| Rz | ng/ml | 3.4E-1 | 3.3E-1 | 9.5E-1 | 1.5E0 | 1.4E0 | 2.0E0 | 3.6E-3 | 1.7E-2 | 6.7E0 | 5.9E0 | 97 | 15 | 74 | 15 | 0.57 |
| Ry | ng/ml | 1.6E-2 | 2.3E-2 | 2.2E-2 | 4.6E-2 | 2.2E-2 | 8.6E-2 | 1.0E-9 | 1.0E-9 | 1.2E-1 | 3.5E-1 | 97 | 15 | 74 | 15 | 0.59 |
| Rx | ng/ml | 1.0E-9 | 3.5E-5 | 1.7E-3 | 1.7E-3 | 3.2E-3 | 2.5E-3 | 1.0E-9 | 1.0E-9 | 2.0E-2 | 8.4E-3 | 97 | 15 | 74 | 15 | 0.56 |
| Ld | pg/ml | 1.0E-9 | 1.7E0 | 3.6E0 | 5.4E0 | 9.2E0 | 9.8E0 | 1.0E-9 | 1.0E-9 | 8.4E1 | 5.0E1 | 246 | 32 | 159 | 32 | 0.58 |
| Lh | pg/ml | 1.2E4 | 2.1E4 | 2.0E4 | 5.2E4 | 2.5E4 | 8.1E4 | 1.0E-9 | 6.7E2 | 2.6E5 | 4.1E5 | 691 | 48 | 281 | 48 | 0.68 |
| Li | pg/ml | 2.8E3 | 1.2E4 | 1.5E4 | 5.3E4 | 5.9E4 | 1.4E5 | 1.0E-9 | 3.4E1 | 1.3E6 | 9.2E5 | 691 | 48 | 281 | 48 | 0.71 |
| Lj | pg/ml | 2.3E3 | 7.7E3 | 2.1E4 | 4.4E4 | 6.5E4 | 8.5E4 | 1.0E-9 | 1.4E2 | 4.7E5 | 4.1E5 | 691 | 48 | 281 | 48 | 0.69 |
| Lp | pg/ml | 1.1E1 | 1.1E1 | 7.1E1 | 1.5E2 | 1.7E2 | 3.1E2 | 1.0E-9 | 1.0E-9 | 1.1E3 | 1.0E3 | 97 | 15 | 74 | 15 | 0.47 |
| Lt | pg/ml | 1.0E-9 | 1.0E-9 | 2.4E0 | 1.7E0 | 9.1E0 | 6.5E0 | 1.0E-9 | 1.0E-9 | 6.0E1 | 2.5E1 | 97 | 15 | 74 | 15 | 0.49 |
| Rv | ng/ml | 5.0E-4 | 8.0E-4 | 1.2E-3 | 2.3E-3 | 2.2E-3 | 3.7E-3 | 1.0E-9 | 1.0E-9 | 1.6E-2 | 1.2E-2 | 97 | 15 | 74 | 15 | 0.57 |
| Ru | ng/ml | 1.0E-9 | 1.0E-9 | 1.5E-2 | 5.0E-2 | 6.6E-2 | 1.2E-1 | 1.0E-9 | 1.0E-9 | 3.8E-1 | 3.5E-1 | 97 | 15 | 74 | 15 | 0.57 |
| Rt | ng/ml | 7.0E-2 | 3.6E-1 | 1.1E-1 | 5.8E-1 | 1.4E-1 | 1.9E0 | 1.0E-3 | 1.3E-3 | 6.3E-1 | 7.4E0 | 97 | 15 | 74 | 15 | 0.43 |
| Yl | pg/ml | 1.1E1 | 1.3E1 | 1.7E1 | 3.4E1 | 1.9E1 | 5.4E1 | 1.0E-9 | 1.0E-9 | 1.1E2 | 2.2E2 | 100 | 15 | 77 | 15 | 0.60 |
| Rm | ng/ml | 1.9E1 | 3.4E1 | 4.9E1 | 8.5E1 | 7.4E1 | 1.3E2 | 2.2E-1 | 3.9E-1 | 4.0E2 | 6.5E2 | 245 | 32 | 159 | 32 | 0.61 |
| Rh | ng/ml | 1.3E2 | 1.2E2 | 3.6E2 | 1.1E3 | 1.2E3 | 3.6E3 | 3.6E0 | 2.5E1 | 1.7E4 | 1.7E4 | 245 | 32 | 159 | 32 | 0.54 |
| Ri | ng/ml | 1.0E-9 | 1.0E-9 | 4.4E0 | 3.0E0 | 1.6E1 | 8.6E0 | 1.0E-9 | 1.0E-9 | 2.2E2 | 4.5E1 | 246 | 32 | 160 | 32 | 0.43 |
| Rg | ng/ml | 1.0E-9 | 1.0E-9 | 7.1E-2 | 4.8E-2 | 4.2E-1 | 1.5E-1 | 1.0E-9 | 1.0E-9 | 4.6E0 | 6.2E-1 | 245 | 32 | 159 | 32 | 0.51 |
| Rj | ng/ml | 1.0E-9 | 1.0E-9 | 1.6E0 | 8.9E0 | 6.0E0 | 4.8E1 | 1.0E-9 | 1.0E-9 | 8.0E1 | 2.7E2 | 246 | 32 | 160 | 32 | 0.47 |
| Rf | ng/ml | 3.7E-1 | 8.3E-1 | 9.8E-1 | 2.1E0 | 1.9E0 | 3.6E0 | 7.8E-3 | 1.8E-2 | 1.5E1 | 1.7E1 | 245 | 32 | 159 | 32 | 0.65 |
| Ql | pg/ml | 4.5E0 | 1.1E1 | 1.4E1 | 2.0E1 | 3.1E1 | 2.6E1 | 1.0E-9 | 1.0E-9 | 2.9E2 | 9.3E1 | 249 | 32 | 162 | 32 | 0.62 |
| Qm | pg/ml | 3.9E0 | 2.0E1 | 2.0E1 | 3.1E1 | 3.9E1 | 3.7E1 | 1.0E-9 | 1.0E-9 | 3.6E2 | 1.7E2 | 249 | 32 | 162 | 32 | 0.65 |
| Qn | pg/ml | 6.1E-1 | 6.1E-1 | 6.9E0 | 1.4E1 | 2.2E1 | 4.5E1 | 1.0E-9 | 1.0E-9 | 2.2E2 | 2.4E2 | 249 | 32 | 162 | 32 | 0.52 |
| Nv | pg/ml | 3.8E3 | 7.3E3 | 1.1E4 | 1.7E4 | 4.8E4 | 2.5E4 | 1.0E-9 | 1.5E2 | 1.1E6 | 1.1E5 | 696 | 48 | 281 | 48 | 0.65 |
| Nw | pg/ml | 8.1E3 | 1.7E4 | 1.2E4 | 3.0E4 | 1.7E4 | 4.2E4 | 8.6E0 | 1.7E3 | 2.1E5 | 2.2E5 | 696 | 48 | 281 | 48 | 0.75 |
| Nx | pg/ml | 2.0E2 | 2.7E2 | 3.8E2 | 7.1E2 | 6.6E2 | 8.6E2 | 1.0E-9 | 1.0E-9 | 7.4E3 | 4.1E3 | 696 | 48 | 281 | 48 | 0.65 |
| Ny | pg/ml | 5.5E0 | 1.7E1 | 6.2E1 | 1.1E2 | 9.6E2 | 4.1E2 | 1.0E-9 | 1.0E-9 | 2.5E4 | 2.8E3 | 696 | 48 | 281 | 48 | 0.68 |
| Oa | pg/ml | 1.6E2 | 4.6E2 | 4.0E2 | 9.0E2 | 6.9E2 | 1.0E3 | 1.0E-9 | 4.9E0 | 4.8E3 | 4.5E3 | 249 | 32 | 162 | 32 | 0.68 |
| Op | pg/ml | 4.2E5 | 4.4E5 | 4.1E5 | 4.1E5 | 1.6E5 | 2.0E5 | 3.3E4 | 6.7E4 | 7.3E5 | 7.5E5 | 97 | 15 | 74 | 15 | 0.50 |
| Wn | ng/ml | 1.3E1 | 2.2E1 | 5.8E1 | 3.1E2 | 2.1E2 | 7.7E2 | 8.9E-1 | 2.7E0 | 1.8E3 | 2.4E3 | 86 | 9 | 63 | 9 | 0.66 |
| Tk | ng/ml | 1.3E2 | 1.4E2 | 3.1E2 | 3.8E2 | 5.6E2 | 5.1E2 | 3.0E0 | 1.0E1 | 4.2E3 | 1.4E3 | 92 | 10 | 66 | 10 | 0.52 |
| Oe | pg/ml | 4.9E1 | 2.1E1 | 2.9E2 | 2.6E2 | 8.1E2 | 4.5E2 | 1.0E-9 | 1.0E-9 | 1.9E4 | 2.2E3 | 688 | 48 | 281 | 48 | 0.48 |
| Of | pg/ml | 1.8E2 | 9.8E1 | 6.4E3 | 6.0E3 | 3.1E4 | 2.0E4 | 1.0E-9 | 1.0E-9 | 6.2E5 | 1.1E5 | 695 | 48 | 281 | 48 | 0.47 |
| Og | pg/ml | 8.4E-2 | 5.8E-2 | 5.3E-1 | 2.2E-1 | 1.7E0 | 7.3E-1 | 1.0E-9 | 1.0E-9 | 2.0E1 | 5.0E0 | 695 | 48 | 281 | 48 | 0.43 |

Figure 1 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oh | pg/ml | 2.4E0 | 5.1E0 | 2.3E1 | 4.2E1 | 1.6E2 | 1.7E2 | 1.0E-9 | 1.4E-1 | 3.5E3 | 1.1E3 | 695 | 48 | 281 | 48 | 0.67 |
| Oi | pg/ml | 2.3E0 | 2.8E0 | 6.1E0 | 7.3E0 | 9.9E0 | 1.1E1 | 1.0E-9 | 1.0E-9 | 8.6E1 | 5.1E1 | 695 | 48 | 281 | 48 | 0.53 |
| Ok | pg/ml | 3.5E2 | 7.4E2 | 5.0E2 | 1.1E3 | 5.2E2 | 1.3E3 | 1.3E1 | 3.2E1 | 5.2E3 | 7.8E3 | 695 | 48 | 281 | 48 | 0.73 |
| Om | pg/ml | 3.8E2 | 6.5E2 | 8.5E2 | 2.4E3 | 2.3E3 | 7.4E3 | 1.0E-9 | 1.0E2 | 3.6E4 | 5.1E4 | 695 | 48 | 281 | 48 | 0.68 |
| On | pg/ml | 1.6E2 | 3.2E2 | 2.7E2 | 7.4E2 | 4.1E2 | 1.3E3 | 1.0E-9 | 1.5E1 | 4.5E3 | 8.5E3 | 695 | 48 | 281 | 48 | 0.71 |
| Or | pg/ml | 1.2E1 | 2.1E1 | 3.1E1 | 8.3E1 | 6.0E1 | 1.4E2 | 1.0E-9 | 1.0E-9 | 5.0E2 | 5.1E2 | 249 | 32 | 160 | 32 | 0.58 |
| Ow | pg/ml | 3.3E1 | 5.5E1 | 1.2E2 | 2.5E2 | 3.5E2 | 5.6E2 | 1.0E-9 | 1.0E-9 | 3.2E3 | 3.0E3 | 249 | 32 | 160 | 32 | 0.59 |
| Ou | pg/ml | 4.6E2 | 6.5E2 | 8.6E2 | 2.3E3 | 1.3E3 | 3.4E3 | 1.0E-9 | 1.0E-9 | 9.8E3 | 1.1E4 | 249 | 32 | 160 | 32 | 0.57 |
| Ul | ng/ml | 1.0E-9 | 1.0E-9 | 1.2E0 | 4.9E0 | 4.6E0 | 1.4E1 | 1.0E-9 | 1.0E-9 | 3.4E1 | 5.6E1 | 257 | 32 | 164 | 32 | 0.52 |
| Uo | ng/ml | 1.0E-9 | 1.0E-9 | 9.2E-2 | 5.1E-1 | 2.1E-1 | 1.4E-1 | 1.0E-9 | 1.0E-9 | 1.3E0 | 6.3E-1 | 257 | 32 | 164 | 32 | 0.46 |
| Uk | ng/ml | 1.0E-9 | 1.0E-9 | 7.8E-3 | 3.5E-3 | 2.7E-2 | 9.7E-3 | 1.0E-9 | 1.0E-9 | 3.2E-1 | 3.9E-2 | 257 | 32 | 164 | 32 | 0.37 |
| Um | ng/ml | 1.0E-9 | 1.0E-9 | 3.7E-1 | 2.0E-1 | 8.5E-1 | 4.7E-1 | 1.0E-9 | 1.0E-9 | 6.8E0 | 2.3E0 | 257 | 32 | 164 | 32 | 0.44 |
| Uf | ng/ml | 5.1E-2 | 1.1E-1 | 1.2E-1 | 3.6E-1 | 1.9E-1 | 9.8E-1 | 1.0E-3 | 9.8E-3 | 1.7E0 | 5.6E0 | 257 | 32 | 164 | 32 | 0.68 |
| Uh | ng/ml | 1.8E0 | 4.0E0 | 2.9E0 | 5.6E0 | 3.2E0 | 5.1E0 | 3.2E-2 | 9.5E-2 | 1.7E1 | 1.8E1 | 257 | 32 | 164 | 32 | 0.69 |
| Un | ng/ml | 1.8E0 | 2.5E0 | 2.1E0 | 3.7E0 | 1.3E0 | 4.2E0 | 2.0E-1 | 5.3E-1 | 8.0E0 | 2.5E1 | 257 | 32 | 164 | 32 | 0.70 |
| Ug | ng/ml | 1.4E1 | 1.3E1 | 2.7E1 | 2.5E1 | 2.8E1 | 3.3E1 | 6.9E-1 | 1.7E0 | 1.8E2 | 1.6E2 | 257 | 32 | 164 | 32 | 0.45 |
| Ur | ng/ml | 1.5E-1 | 4.5E-2 | 7.7E-1 | 7.4E-1 | 5.9E0 | 1.8E0 | 1.0E-9 | 1.0E-9 | 9.3E1 | 7.3E0 | 256 | 32 | 163 | 32 | 0.40 |
| Up | ng/ml | 1.0E-9 | 1.0E-9 | 5.4E-3 | 7.8E-2 | 2.5E-2 | 4.2E-1 | 1.0E-9 | 1.0E-9 | 3.3E-1 | 2.4E0 | 256 | 32 | 163 | 32 | 0.52 |
| Us | ng/ml | 3.2E-3 | 5.2E-5 | 1.8E-2 | 8.0E-2 | 4.4E-2 | 2.9E-1 | 1.0E-9 | 1.0E-9 | 4.0E-1 | 1.7E0 | 256 | 32 | 163 | 32 | 0.50 |
| Uv | ng/ml | 3.0E-3 | 3.2E-3 | 1.3E-2 | 2.6E-2 | 4.2E-2 | 8.0E-2 | 1.0E-9 | 1.0E-9 | 4.3E-1 | 4.1E-1 | 256 | 32 | 163 | 32 | 0.51 |
| Ut | ng/ml | 6.6E-1 | 1.1E0 | 2.9E0 | 5.3E0 | 9.1E0 | 1.3E1 | 1.0E-9 | 1.0E-9 | 7.8E1 | 6.5E1 | 256 | 32 | 163 | 32 | 0.62 |
| Uu | ng/ml | 7.0E0 | 5.4E0 | 7.7E0 | 8.7E0 | 5.0E0 | 9.1E0 | 4.5E-1 | 1.2E0 | 2.6E1 | 4.0E1 | 256 | 32 | 163 | 32 | 0.48 |
| Uw | ng/ml | 2.2E0 | 4.0E0 | 3.0E0 | 6.1E0 | 4.0E0 | 9.4E0 | 1.0E-9 | 9.9E-1 | 3.7E1 | 3.9E1 | 106 | 15 | 83 | 15 | 0.68 |
| Vb | ng/ml | 1.0E0 | 9.5E-1 | 1.0E0 | 1.3E0 | 4.3E-1 | 1.5E0 | 8.5E-2 | 2.6E-1 | 2.5E0 | 6.4E0 | 106 | 15 | 83 | 15 | 0.45 |
| Vc | ng/ml | 1.0E-9 | 1.0E-9 | 8.2E-3 | 1.0E-9 | 6.5E-2 | 0.0E0 | 1.0E-9 | 1.0E-9 | 6.5E-1 | 1.0E-9 | 106 | 15 | 83 | 15 | 0.47 |
| Uy | ng/ml | 1.2E0 | 1.4E0 | 4.5E0 | 1.1E1 | 1.2E1 | 2.1E1 | 3.1E-2 | 2.0E-2 | 9.9E1 | 6.4E1 | 106 | 15 | 83 | 15 | 0.53 |
| Uz | ng/ml | 1.0E-9 | 1.0E-9 | 4.2E-3 | 2.2E0 | 4.2E-2 | 8.5E0 | 1.0E-9 | 1.0E-9 | 4.4E-1 | 3.3E1 | 106 | 15 | 83 | 15 | 0.52 |
| Ux | ng/ml | 1.8E2 | 2.2E2 | 1.9E2 | 2.2E2 | 1.4E2 | 1.3E2 | 4.5E0 | 3.5E1 | 5.3E2 | 4.6E2 | 106 | 15 | 83 | 15 | 0.59 |
| Va | ng/ml | 1.9E1 | 4.9E1 | 2.7E1 | 1.7E1 | 2.7E1 | 2.6E1 | 1.2E-1 | 1.2E0 | 1.2E2 | 7.8E1 | 106 | 15 | 83 | 15 | 0.34 |
| Vh | ng/ml | 1.0E-3 | 1.4E-2 | 1.6E-2 | 7.4E-2 | 2.1E-2 | 2.2E-1 | 1.0E-9 | 2.2E-3 | 1.2E-1 | 8.6E-1 | 106 | 15 | 83 | 15 | 0.61 |
| Vj | ng/ml | 3.0E-3 | 1.1E-2 | 1.4E-1 | 1.4E-1 | 1.3E0 | 4.7E-1 | 1.0E-9 | 1.0E-9 | 1.4E1 | 1.8E0 | 106 | 15 | 83 | 15 | 0.67 |
| Vj | ng/ml | 2.6E1 | 6.2E1 | 2.1E2 | 7.0E1 | 9.6E2 | 5.6E1 | 1.4E0 | 5.4E0 | 8.4E3 | 1.7E2 | 106 | 13 | 83 | 13 | 0.60 |
| Vp | ng/ml | 1.0E-9 | 1.0E-9 | 4.0E-1 | 1.6E0 | 3.6E0 | 8.7E0 | 1.0E-9 | 1.0E-9 | 5.0E1 | 4.9E1 | 257 | 32 | 164 | 32 | 0.53 |
| Vt | ng/ml | 6.0E0 | 1.2E1 | 8.4E0 | 2.0E1 | 9.1E0 | 2.9E1 | 4.3E-1 | 1.8E0 | 8.6E1 | 1.6E2 | 257 | 32 | 164 | 32 | 0.69 |
| Vu | ng/ml | 1.0E-9 | 1.0E-9 | 2.3E0 | 2.5E0 | 5.6E0 | 5.0E0 | 1.0E-9 | 1.0E-9 | 5.1E1 | 2.2E1 | 253 | 30 | 164 | 30 | 0.53 |
| Vq | ng/ml | 1.6E2 | 6.6E2 | 4.1E3 | 1.8E3 | 4.8E4 | 3.2E3 | 2.0E-1 | 1.0E1 | 6.8E5 | 1.2E4 | 203 | 19 | 135 | 19 | 0.66 |
| Vo | ng/ml | 2.6E1 | 2.6E1 | 2.4E1 | 2.5E1 | 5.4E0 | 4.5E0 | 2.4E0 | 1.1E1 | 4.8E1 | 3.3E1 | 257 | 32 | 164 | 32 | 0.53 |
| Vs | ng/ml | 1.0E-9 | 1.0E-9 | 6.7E0 | 2.1E1 | 2.4E1 | 8.7E1 | 1.0E-9 | 1.0E-9 | 2.3E2 | 4.5E2 | 253 | 27 | 161 | 27 | 0.49 |
| Vv | ng/ml | 2.9E0 | 2.6E0 | 6.1E0 | 5.3E0 | 1.0E1 | 7.1E0 | 1.0E-9 | 1.0E-9 | 8.4E1 | 3.2E1 | 256 | 31 | 164 | 31 | 0.50 |
| Vw | ng/ml | 3.6E1 | 4.1E1 | 3.5E1 | 4.1E1 | 1.7E1 | 1.6E1 | 2.5E0 | 1.1E1 | 7.0E1 | 6.6E1 | 106 | 15 | 83 | 15 | 0.60 |
| Oy | pg/ml | 5.3E-1 | 4.0E1 | 6.6E0 | 2.9E0 | 3.2E1 | 8.6E0 | 1.0E-9 | 1.0E-9 | 4.0E2 | 4.9E1 | 694 | 48 | 280 | 48 | 0.45 |
| Oz | pg/ml | 1.3E-2 | 1.0E-9 | 3.4E-1 | 8.4E-1 | 1.5E0 | 4.0E0 | 1.0E-9 | 1.0E-9 | 2.9E1 | 2.8E1 | 694 | 48 | 280 | 48 | 0.49 |
| Pa | pg/ml | 3.8E-1 | 4.8E-1 | 1.5E0 | 6.0E0 | 5.5E0 | 3.3E1 | 1.0E-9 | 1.0E-9 | 8.6E1 | 2.3E2 | 694 | 48 | 280 | 48 | 0.55 |
| Pb | pg/ml | 1.0E-9 | 1.0E-9 | 9.3E-1 | 7.7E-1 | 1.9E1 | 4.6E0 | 1.0E-9 | 1.0E-9 | 4.9E2 | 3.2E1 | 694 | 48 | 280 | 48 | 0.43 |
| Pc | pg/ml | 4.7E-2 | 7.0E-2 | 3.7E-1 | 1.2E0 | 9.4E-1 | 5.4E0 | 1.0E-9 | 1.0E-9 | 1.6E1 | 3.8E1 | 694 | 48 | 280 | 48 | 0.52 |
| Pd | pg/ml | 1.7E0 | 3.4E0 | 5.1E0 | 9.0E0 | 3.3E1 | 1.9E1 | 1.0E-9 | 1.0E-9 | 8.4E2 | 1.2E2 | 694 | 48 | 280 | 48 | 0.61 |
| Pe | pg/ml | 2.0E1 | 6.0E1 | 1.0E2 | 6.6E2 | 3.5E2 | 2.4E3 | 1.0E-9 | 1.0E-9 | 4.7E3 | 1.5E4 | 694 | 48 | 280 | 48 | 0.69 |
| Pf | pg/ml | 1.4E0 | 6.5E0 | 1.1E1 | 3.4E1 | 6.4E1 | 8.3E1 | 1.0E-9 | 1.0E-9 | 1.5E3 | 4.3E2 | 694 | 48 | 280 | 48 | 0.71 |
| Pg | pg/ml | 3.0E0 | 1.0E1 | 4.7E1 | 7.7E1 | 3.8E2 | 2.2E2 | 1.0E-9 | 1.0E-9 | 7.7E3 | 1.2E3 | 694 | 48 | 280 | 48 | 0.66 |
| Ph | ng/ml | 1.7E-1 | 2.3E-1 | 3.2E-1 | 5.2E-1 | 4.5E-1 | 1.0E0 | 1.0E-9 | 1.0E-9 | 2.9E0 | 5.4E0 | 249 | 32 | 160 | 32 | 0.55 |
| Pi | ng/ml | 2.0E-1 | 3.0E-1 | 2.8E-1 | 2.9E0 | 3.6E-1 | 1.4E1 | 1.0E-9 | 1.0E-9 | 3.2E0 | 8.2E1 | 249 | 32 | 160 | 32 | 0.59 |
| Pj | ng/mL | 4.8E0 | 7.3E0 | 5.9E0 | 9.1E0 | 4.5E0 | 9.4E0 | 3.8E-2 | 1.4E0 | 3.1E1 | 5.5E1 | 249 | 32 | 160 | 32 | 0.65 |
| Pk | ng/ml | 8.9E-3 | 1.0E-2 | 1.4E-2 | 5.9E-2 | 2.2E-2 | 2.7E-1 | 1.0E-9 | 1.0E-9 | 2.5E-1 | 1.5E0 | 249 | 32 | 160 | 32 | 0.53 |
| aA | mg/dL | 8.0E-1 | 1.0E0 | 9.2E-1 | 1.3E0 | 4.7E-1 | 9.8E-1 | 2.0E-1 | 4.0E-1 | 4.2E0 | 4.7E0 | 2240 | 64 | 436 | 64 | 0.63 |
| aC | mg/mL | 2.9E0 | 2.2E0 | 3.2E0 | 2.4E0 | 1.4E0 | 1.0E0 | 8.5E-1 | 7.4E-1 | 8.9E0 | 5.5E0 | 437 | 33 | 174 | 33 | 0.34 |
| aD | ug/mL | 3.1E0 | 4.5E0 | 4.4E0 | 6.4E0 | 3.9E0 | 5.5E0 | 4.3E-1 | 7.7E-1 | 3.5E1 | 2.1E1 | 437 | 33 | 174 | 33 | 0.59 |
| aE | mg/mL | 5.6E-1 | 5.1E-1 | 5.8E-1 | 5.6E-1 | 1.5E-1 | 1.8E-1 | 2.1E-1 | 2.2E-1 | 1.1E0 | 1.2E0 | 437 | 33 | 174 | 33 | 0.43 |

Figure 1 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aF | ng/mL | 2.1E0 | 2.6E0 | 4.1E0 | 3.5E0 | 6.1E0 | 3.5E0 | 4.3E-3 | 3.7E-1 | 5.0E1 | 1.3E1 | 437 | 33 | 174 | 33 | 0.49 |
| aG | mg/mL | 1.4E-1 | 1.3E-1 | 1.6E-1 | 1.5E-1 | 9.1E-2 | 8.5E-2 | 1.7E-2 | 4.3E-2 | 5.4E-1 | 4.2E-1 | 437 | 33 | 174 | 33 | 0.47 |
| aH | ug/mL | 7.5E1 | 7.5E1 | 8.3E1 | 7.9E1 | 4.4E1 | 4.6E1 | 4.6E0 | 1.1E1 | 2.9E2 | 1.9E2 | 437 | 33 | 174 | 33 | 0.48 |
| aI | ug/mL | 1.9E2 | 1.6E2 | 1.9E2 | 1.6E2 | 6.0E1 | 5.7E1 | 2.8E1 | 7.5E1 | 3.7E2 | 2.9E2 | 437 | 33 | 174 | 33 | 0.34 |
| aJ | ug/mL | 2.4E0 | 3.3E0 | 2.9E0 | 4.6E0 | 2.1E0 | 4.2E0 | 7.6E-1 | 1.1E0 | 1.7E1 | 2.3E1 | 437 | 33 | 174 | 33 | 0.65 |
| aK | ng/mL | 1.6E0 | 1.3E0 | 2.5E0 | 1.8E0 | 2.7E0 | 1.5E0 | 2.9E-4 | 1.3E-1 | 1.8E1 | 5.5E0 | 437 | 33 | 174 | 33 | 0.45 |
| aL | mg/mL | 8.1E-1 | 7.8E-1 | 8.2E-1 | 7.8E-1 | 2.5E-1 | 2.7E-1 | 1.9E-1 | 2.7E-1 | 1.7E0 | 1.5E0 | 437 | 33 | 174 | 33 | 0.46 |
| aM | U/mL | 2.2E1 | 3.2E1 | 4.5E1 | 7.1E1 | 9.6E1 | 1.4E2 | 4.2E-2 | 4.2E-2 | 1.6E3 | 8.2E2 | 437 | 33 | 174 | 33 | 0.59 |
| aN | U/mL | 1.3E1 | 2.0E1 | 2.0E1 | 3.1E1 | 2.8E1 | 2.8E1 | 2.5E-3 | 2.5E-3 | 3.8E2 | 1.1E2 | 437 | 33 | 174 | 33 | 0.64 |
| aO | pg/mL | 3.1E1 | 4.1E1 | 3.2E2 | 4.1E2 | 8.3E2 | 6.8E2 | 6.0E-2 | 6.0E-2 | 6.6E3 | 2.4E3 | 437 | 33 | 174 | 33 | 0.55 |
| aP | ng/mL | 1.6E0 | 1.9E0 | 2.0E0 | 3.2E0 | 1.8E0 | 4.7E0 | 4.5E-1 | 6.3E-1 | 2.8E1 | 2.8E1 | 437 | 33 | 174 | 33 | 0.59 |
| aQ | ng/mL | 3.0E-1 | 2.6E-1 | 4.7E-1 | 3.4E-1 | 4.8E-1 | 2.7E-1 | 2.0E-4 | 5.1E-2 | 4.0E0 | 1.2E0 | 437 | 33 | 174 | 33 | 0.43 |
| aR | ng/mL | 1.7E0 | 2.3E0 | 2.7E0 | 2.8E0 | 3.3E0 | 2.9E0 | 1.8E-1 | 2.5E-1 | 3.4E1 | 1.7E1 | 437 | 33 | 174 | 33 | 0.54 |
| aS | ng/mL | 2.6E-1 | 3.6E-1 | 6.5E-1 | 6.3E-1 | 1.9E0 | 7.4E-1 | 4.2E-3 | 6.0E-2 | 3.3E1 | 2.8E0 | 437 | 33 | 174 | 33 | 0.55 |
| aU | pg/mL | 7.8E1 | 6.1E1 | 1.3E2 | 7.5E1 | 1.5E2 | 6.0E1 | 7.4E-2 | 9.6E0 | 1.3E3 | 2.3E2 | 437 | 33 | 174 | 33 | 0.40 |
| aV | ng/mL | 6.3E-1 | 4.2E-1 | 1.1E0 | 7.7E-1 | 2.0E0 | 9.8E-1 | 7.6E-4 | 9.1E-2 | 3.3E1 | 5.4E0 | 437 | 33 | 174 | 33 | 0.42 |
| aW | pg/mL | 1.9E1 | 1.7E1 | 2.0E1 | 2.9E1 | 2.0E1 | 7.0E1 | 7.2E-2 | 7.2E-2 | 2.4E2 | 4.2E2 | 437 | 33 | 174 | 33 | 0.49 |
| aX | ng/mL | 9.4E0 | 1.2E1 | 1.5E1 | 2.0E1 | 1.9E1 | 3.5E1 | 3.0E-1 | 1.6E0 | 2.2E2 | 1.7E2 | 437 | 33 | 174 | 33 | 0.50 |
| aY | pg/mL | 5.4E1 | 6.1E1 | 7.7E1 | 7.6E1 | 8.7E1 | 5.5E1 | 4.1E-1 | 4.1E-1 | 1.2E3 | 2.0E2 | 437 | 33 | 174 | 33 | 0.54 |
| aZ | pg/mL | 2.2E2 | 3.2E2 | 5.0E2 | 4.6E2 | 9.8E2 | 5.9E2 | 1.7E0 | 1.7E0 | 1.2E4 | 2.6E3 | 437 | 33 | 174 | 33 | 0.54 |
| bA | ng/mL | 8.0E0 | 2.2E1 | 3.0E1 | 1.7E2 | 7.8E1 | 3.6E2 | 3.0E-2 | 3.0E-2 | 9.4E2 | 1.5E3 | 437 | 33 | 174 | 33 | 0.69 |
| bB | ng/mL | 3.1E2 | 2.4E2 | 3.4E2 | 2.6E2 | 1.7E2 | 1.7E2 | 2.1E0 | 2.3E1 | 1.0E3 | 6.3E2 | 437 | 33 | 174 | 33 | 0.37 |
| bC | ng/mL | 3.3E2 | 3.4E2 | 5.6E2 | 8.3E2 | 7.4E2 | 1.1E3 | 9.8E1 | 5.0E1 | 4.7E3 | 4.7E3 | 437 | 33 | 174 | 33 | 0.58 |
| bE | mg/mL | 5.5E0 | 5.4E0 | 5.8E0 | 5.8E0 | 2.0E0 | 2.4E0 | 9.8E-1 | 1.3E0 | 1.3E1 | 1.2E1 | 437 | 33 | 174 | 33 | 0.48 |
| bF | pg/mL | 1.9E1 | 4.3E1 | 1.6E2 | 3.9E2 | 9.8E2 | 1.2E3 | 5.0E-2 | 7.7E0 | 1.1E4 | 6.3E3 | 437 | 33 | 174 | 33 | 0.68 |
| bG | ng/mL | 1.6E0 | 1.7E0 | 2.7E0 | 3.1E0 | 3.3E0 | 5.2E0 | 2.2E-2 | 1.1E-1 | 2.6E1 | 3.0E1 | 437 | 33 | 174 | 33 | 0.52 |
| bH | pg/mL | 5.7E-1 | 5.7E-1 | 4.9E0 | 4.8E0 | 1.6E1 | 6.3E0 | 5.7E-1 | 5.7E-1 | 2.8E2 | 2.2E1 | 437 | 33 | 174 | 33 | 0.54 |
| bI | ng/mL | 4.0E-3 | 4.0E-3 | 6.5E-2 | 8.5E-2 | 1.6E-1 | 2.1E-1 | 4.0E-3 | 4.0E-3 | 1.3E0 | 8.8E-1 | 437 | 33 | 174 | 33 | 0.51 |
| bJ | mg/mL | 2.4E0 | 1.9E0 | 2.7E0 | 2.4E0 | 2.1E0 | 1.8E0 | 2.5E-4 | 2.5E-4 | 1.3E1 | 7.0E0 | 437 | 33 | 174 | 33 | 0.46 |
| bL | pg/mL | 4.0E0 | 3.1E0 | 8.3E0 | 5.9E0 | 1.1E1 | 7.1E0 | 4.6E-2 | 4.6E-2 | 8.0E1 | 3.2E1 | 437 | 33 | 174 | 33 | 0.46 |
| bM | mg/mL | 1.7E0 | 2.3E0 | 2.0E0 | 2.7E0 | 1.4E0 | 1.6E0 | 9.2E-3 | 1.8E-2 | 8.8E0 | 8.4E0 | 437 | 33 | 174 | 33 | 0.64 |
| bN | ng/mL | 4.3E1 | 3.3E1 | 1.4E2 | 8.2E1 | 2.9E2 | 1.3E2 | 1.4E-1 | 5.9E-1 | 1.9E3 | 4.8E2 | 437 | 33 | 174 | 33 | 0.44 |
| bO | ng/mL | 4.0E-2 | 4.0E-2 | 1.0E1 | 9.7E0 | 2.3E1 | 1.9E1 | 4.0E-2 | 4.0E-2 | 1.9E2 | 6.6E1 | 437 | 33 | 174 | 33 | 0.48 |
| bP | mg/mL | 5.3E-1 | 6.8E-1 | 7.6E-1 | 8.4E-1 | 6.8E-1 | 7.4E-1 | 4.9E-2 | 1.4E-1 | 4.8E0 | 3.5E0 | 437 | 33 | 174 | 33 | 0.54 |
| bQ | pg/mL | 1.5E1 | 2.3E1 | 6.4E1 | 4.9E1 | 6.5E2 | 5.6E1 | 1.5E-1 | 1.5E-1 | 1.3E4 | 2.2E2 | 437 | 33 | 174 | 33 | 0.62 |
| bR | ng/mL | 1.2E-2 | 1.2E-2 | 1.4E-1 | 6.0E-2 | 4.6E-1 | 9.7E-2 | 1.2E-2 | 1.2E-2 | 8.7E0 | 3.9E-1 | 437 | 33 | 174 | 33 | 0.40 |
| bS | pg/mL | 9.4E-1 | 9.4E-1 | 7.2E0 | 3.8E0 | 2.9E1 | 1.2E1 | 9.4E-1 | 9.4E-1 | 3.9E2 | 6.7E1 | 437 | 33 | 174 | 33 | 0.46 |
| bU | ng/mL | 1.5E-1 | 1.3E-2 | 2.0E-1 | 1.2E-1 | 3.8E-1 | 1.5E-1 | 1.3E-2 | 1.3E-2 | 6.6E0 | 6.3E-1 | 437 | 33 | 174 | 33 | 0.41 |
| bV | pg/mL | 4.7E2 | 5.6E2 | 5.5E2 | 7.3E2 | 5.8E2 | 5.8E2 | 1.6E2 | 1.9E2 | 1.2E4 | 3.1E3 | 437 | 33 | 174 | 33 | 0.59 |
| bW | pg/mL | 3.2E2 | 3.2E2 | 4.9E2 | 1.4E3 | 4.8E2 | 4.3E3 | 8.4E1 | 1.2E2 | 4.8E3 | 2.5E4 | 437 | 33 | 174 | 33 | 0.55 |
| bX | ng/mL | 1.5E-3 | 2.5E-5 | 2.8E-3 | 2.0E-3 | 3.5E-3 | 2.5E-3 | 2.5E-5 | 2.5E-5 | 2.0E-2 | 7.1E-3 | 437 | 33 | 174 | 33 | 0.45 |
| bZ | pg/mL | 2.3E2 | 3.6E2 | 9.1E2 | 2.2E3 | 4.1E3 | 7.3E3 | 1.5E-1 | 1.5E-1 | 5.8E4 | 4.3E4 | 437 | 33 | 174 | 33 | 0.66 |
| cA | pg/mL | 6.0E-1 | 6.0E-1 | 2.8E0 | 1.0E0 | 1.8E1 | 2.5E0 | 6.0E-1 | 6.0E-1 | 3.7E2 | 1.5E1 | 437 | 33 | 174 | 33 | 0.45 |
| cB | ng/mL | 6.0E-2 | 4.2E-2 | 9.3E-2 | 6.5E-2 | 1.0E-1 | 8.5E-2 | 1.7E-3 | 1.7E-3 | 5.7E-1 | 4.0E-1 | 437 | 33 | 174 | 33 | 0.41 |
| cC | pg/mL | 4.6E1 | 4.6E1 | 4.8E1 | 3.8E1 | 4.0E1 | 2.6E1 | 1.0E0 | 1.0E0 | 4.5E2 | 7.3E1 | 437 | 33 | 174 | 33 | 0.44 |
| cD | pg/mL | 5.4E0 | 4.9E0 | 1.5E1 | 1.2E1 | 5.7E1 | 1.9E1 | 3.3E-1 | 3.3E-1 | 7.2E2 | 9.0E1 | 437 | 33 | 174 | 33 | 0.50 |
| cE | pg/mL | 3.2E1 | 8.5E1 | 1.5E2 | 2.3E2 | 4.6E2 | 3.4E2 | 1.2E-1 | 1.7E0 | 3.8E3 | 1.3E3 | 437 | 33 | 174 | 33 | 0.67 |
| cF | pg/mL | 1.3E1 | 5.3E-1 | 2.1E1 | 1.0E1 | 3.2E1 | 1.4E1 | 5.3E-1 | 5.3E-1 | 2.7E2 | 5.0E1 | 437 | 33 | 174 | 33 | 0.40 |
| cG | pg/mL | 4.3E1 | 8.1E1 | 1.1E2 | 1.2E2 | 5.2E2 | 1.2E2 | 7.8E0 | 6.4E0 | 1.0E4 | 4.9E2 | 437 | 33 | 174 | 33 | 0.70 |
| cH | uIU/mL | 3.1E0 | 2.2E0 | 6.5E0 | 6.3E0 | 1.2E1 | 1.1E1 | 8.6E-3 | 8.6E-3 | 1.6E2 | 5.3E1 | 437 | 33 | 174 | 33 | 0.41 |
| cI | ng/mL | 5.7E0 | 9.4E0 | 1.1E1 | 1.7E1 | 1.5E1 | 2.4E1 | 1.0E-3 | 1.0E-3 | 1.0E2 | 1.2E2 | 437 | 33 | 174 | 33 | 0.55 |
| cJ | ug/mL | 7.0E1 | 4.6E1 | 1.2E2 | 8.3E1 | 1.5E2 | 9.9E1 | 4.0E0 | 5.6E0 | 9.6E2 | 3.4E2 | 437 | 33 | 174 | 33 | 0.41 |
| cK | ng/mL | 3.8E-3 | 3.8E-3 | 5.5E-2 | 1.1E-2 | 1.9E-1 | 2.0E-2 | 3.8E-3 | 3.8E-3 | 1.7E0 | 8.2E-2 | 437 | 33 | 174 | 33 | 0.47 |
| cL | pg/mL | 1.9E2 | 2.0E2 | 3.6E2 | 2.9E2 | 1.3E3 | 2.5E2 | 1.6E1 | 4.8E1 | 2.4E4 | 1.4E3 | 437 | 33 | 174 | 33 | 0.58 |
| cM | pg/mL | 2.8E2 | 2.6E2 | 3.1E2 | 2.6E2 | 2.0E2 | 5.7E1 | 1.6E3 | 5.7E0 | 1.6E3 | 5.1E2 | 437 | 33 | 174 | 33 | 0.45 |
| cN | pg/mL | 1.2E2 | 1.3E2 | 1.3E2 | 1.4E2 | 6.4E1 | 5.5E1 | 3.8E1 | 7.4E1 | 1.1E3 | 2.9E2 | 437 | 33 | 174 | 33 | 0.61 |
| cO | pg/mL | 2.2E2 | 2.4E2 | 3.1E2 | 2.5E2 | 9.3E2 | 8.9E1 | 5.4E1 | 1.2E2 | 1.9E4 | 4.4E2 | 437 | 33 | 174 | 33 | 0.54 |

Figure 1 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cP | ng/mL | 2.5E3 | 2.4E3 | 2.6E3 | 2.8E3 | 9.2E2 | 1.1E3 | 6.2E2 | 1.3E3 | 5.7E3 | 5.6E3 | 437 | 33 | 174 | 33 | 0.52 |
| cQ | ng/mL | 4.3E-2 | 5.5E-2 | 1.3E-1 | 1.7E-1 | 2.4E-1 | 2.9E-1 | 2.0E-3 | 2.0E-3 | 2.2E0 | 1.2E0 | 437 | 33 | 174 | 33 | 0.52 |
| cR | ng/mL | 2.8E2 | 4.2E2 | 4.9E2 | 5.0E2 | 8.0E2 | 4.2E2 | 2.0E1 | 7.0E1 | 8.9E3 | 2.0E3 | 437 | 33 | 174 | 33 | 0.59 |
| cS | ng/mL | 2.6E2 | 3.2E2 | 3.8E2 | 6.9E2 | 3.8E2 | 1.3E3 | 4.1E1 | 4.8E1 | 2.7E3 | 7.1E3 | 437 | 33 | 174 | 33 | 0.56 |
| cT | ng/mL | 2.9E1 | 7.8E1 | 8.3E1 | 2.6E2 | 1.8E2 | 4.8E2 | 3.6E0 | 4.0E0 | 2.1E3 | 1.9E3 | 437 | 33 | 174 | 33 | 0.65 |
| cU | ng/mL | 5.4E1 | 6.4E1 | 7.5E1 | 9.8E1 | 9.9E1 | 9.3E1 | 6.2E0 | 1.6E1 | 1.6E3 | 4.2E2 | 437 | 33 | 174 | 33 | 0.58 |
| cV | ng/mL | 1.7E-1 | 2.4E-1 | 3.8E-1 | 4.1E-1 | 2.3E-1 | 4.7E-1 | 3.4E-4 | 3.6E-2 | 4.7E1 | 2.5E0 | 437 | 33 | 174 | 33 | 0.65 |
| cW | mIU/mL | 5.3E-2 | 4.2E-2 | 1.5E-1 | 8.1E-2 | 7.2E-1 | 8.5E-2 | 3.7E-4 | 1.4E-2 | 9.7E0 | 3.9E-1 | 437 | 33 | 174 | 33 | 0.50 |
| cX | ng/mL | 9.9E-2 | 1.2E-1 | 1.3E0 | 8.7E-1 | 4.2E0 | 1.6E0 | 2.3E-4 | 2.3E-4 | 2.8E1 | 5.4E0 | 437 | 33 | 174 | 33 | 0.49 |
| cY | ng/mL | 8.9E0 | 9.0E0 | 1.3E1 | 9.5E0 | 1.3E1 | 7.2E0 | 1.5E-1 | 9.3E-1 | 8.3E1 | 3.1E1 | 437 | 33 | 174 | 33 | 0.45 |
| cZ | ug/mL | 1.5E1 | 1.3E1 | 1.6E1 | 1.4E1 | 7.1E0 | 6.7E0 | 2.3E0 | 3.3E0 | 5.7E1 | 3.1E1 | 437 | 33 | 174 | 33 | 0.43 |
| dA | pg/mL | 3.3E2 | 3.6E2 | 3.8E2 | 3.8E2 | 3.1E2 | 2.0E2 | 9.0E1 | 1.5E2 | 5.8E3 | 1.1E3 | 437 | 33 | 174 | 33 | 0.51 |
| dB | ug/mL | 1.7E1 | 1.9E1 | 1.7E1 | 1.6E1 | 1.6E1 | 1.0E1 | 9.4E-1 | 2.2E0 | 2.5E2 | 3.0E1 | 437 | 33 | 174 | 33 | 0.53 |
| dC | nmol/L | 3.5E1 | 3.8E1 | 3.9E1 | 3.9E1 | 1.8E1 | 1.5E1 | 7.9E0 | 1.6E1 | 1.4E2 | 7.9E1 | 437 | 33 | 174 | 33 | 0.53 |
| dD | ug/mL | 3.7E1 | 3.0E1 | 3.8E1 | 3.4E1 | 1.1E1 | 1.2E1 | 1.3E1 | 1.4E1 | 7.6E1 | 6.4E1 | 437 | 33 | 174 | 33 | 0.37 |
| dE | ng/mL | 4.7E-1 | 2.3E-1 | 6.1E-1 | 4.6E-1 | 7.3E-1 | 6.5E-1 | 8.4E-3 | 8.4E-3 | 7.2E0 | 2.4E0 | 437 | 33 | 174 | 33 | 0.41 |
| dF | ng/mL | 2.2E2 | 2.8E2 | 2.6E2 | 4.3E2 | 1.8E2 | 3.2E2 | 7.5E1 | 8.4E1 | 1.3E3 | 1.2E3 | 437 | 33 | 174 | 33 | 0.69 |
| dG | ng/mL | 1.1E1 | 1.6E1 | 1.4E1 | 2.2E1 | 1.2E1 | 1.9E1 | 2.5E0 | 3.9E0 | 1.8E2 | 8.7E1 | 437 | 33 | 174 | 33 | 0.67 |
| dH | pg/mL | 7.5E0 | 1.1E1 | 1.3E1 | 1.4E1 | 4.0E1 | 1.4E1 | 4.0E-2 | 4.0E-2 | 6.7E2 | 7.6E1 | 437 | 33 | 174 | 33 | 0.61 |
| dI | pg/mL | 4.6E-1 | 4.6E-1 | 2.3E0 | 2.2E0 | 1.6E1 | 3.7E0 | 4.6E-1 | 4.6E-1 | 3.3E2 | 1.9E1 | 437 | 33 | 174 | 33 | 0.56 |
| dJ | ng/mL | 1.9E0 | 1.9E0 | 2.2E0 | 1.9E0 | 1.2E0 | 1.1E0 | 3.2E-2 | 3.2E-2 | 6.9E0 | 3.7E0 | 437 | 33 | 174 | 33 | 0.44 |
| dK | uIU/mL | 1.9E0 | 2.1E0 | 3.1E0 | 2.7E0 | 6.0E0 | 3.9E0 | 2.8E-4 | 1.4E-2 | 7.9E1 | 2.2E1 | 437 | 33 | 174 | 33 | 0.47 |
| dL | ng/mL | 8.7E2 | 1.2E3 | 1.0E3 | 1.3E3 | 4.9E2 | 9.1E2 | 3.4E2 | 4.1E2 | 3.4E3 | 4.8E3 | 437 | 33 | 174 | 33 | 0.61 |
| dM | pg/mL | 9.6E2 | 1.1E3 | 1.1E3 | 1.9E3 | 8.8E2 | 1.9E3 | 3.5E2 | 3.9E2 | 1.2E4 | 9.6E3 | 437 | 33 | 174 | 33 | 0.63 |
| dN | ug/mL | 9.3E1 | 1.1E2 | 9.9E1 | 1.3E2 | 3.6E1 | 6.4E1 | 2.5E1 | 3.4E1 | 2.8E2 | 3.3E2 | 437 | 33 | 174 | 33 | 0.62 |
| dR | pg/ml | 1.6E3 | 1.1E3 | 2.4E3 | 1.8E3 | 2.4E3 | 1.7E3 | 1.4E2 | 3.4E2 | 1.5E4 | 7.3E3 | 287 | 30 | 167 | 30 | 0.42 |
| dU | pg/ml | 9.7E3 | 1.6E4 | 1.3E4 | 1.6E4 | 1.2E4 | 1.2E4 | 6.9E2 | 3.1E3 | 5.3E4 | 3.8E4 | 46 | 12 | 43 | 12 | 0.57 |
| dX | ng/ml | 8.1E-2 | 5.2E-2 | 1.2E-1 | 1.2E-1 | 1.9E-1 | 1.5E-1 | 2.6E-3 | 2.6E-3 | 1.2E0 | 4.2E-1 | 121 | 9 | 43 | 9 | 0.49 |
| eF | ng/ml | 4.0E0 | 4.8E0 | 4.9E0 | 6.3E0 | 4.2E0 | 5.2E0 | 1.2E0 | 2.0E0 | 4.6E1 | 2.9E1 | 302 | 30 | 168 | 30 | 0.63 |
| eC | pg/ml | 3.1E2 | 2.6E2 | 3.6E2 | 3.5E2 | 2.2E2 | 4.2E2 | 9.9E0 | 1.9E1 | 1.4E3 | 2.0E3 | 231 | 27 | 159 | 27 | 0.37 |
| eD | pg/ml | 2.3E2 | 2.1E2 | 5.8E2 | 3.9E2 | 1.2E3 | 8.2E2 | 5.2E-1 | 5.2E-1 | 8.3E3 | 3.8E3 | 197 | 19 | 131 | 19 | 0.44 |
| eM | ng/ml | 3.2E0 | 2.5E0 | 4.9E0 | 4.8E0 | 5.5E0 | 6.3E0 | 3.3E-1 | 7.1E-1 | 3.9E1 | 2.6E1 | 155 | 18 | 67 | 18 | 0.42 |
| eP | ng/ml | 3.7E-3 | 4.5E-1 | 6.4E-1 | 3.5E0 | 1.6E0 | 9.1E0 | 3.7E-3 | 3.7E-3 | 1.2E1 | 2.8E1 | 121 | 9 | 43 | 9 | 0.61 |
| eT | ng/ml | 2.8E2 | 6.1E2 | 6.3E2 | 9.6E2 | 7.2E2 | 9.4E2 | 1.0E2 | 7.1E1 | 2.9E3 | 2.9E3 | 112 | 12 | 94 | 12 | 0.61 |
| eQ | pg/ml | 1.0E0 | 1.0E0 | 7.9E1 | 1.8E1 | 2.5E2 | 4.4E1 | 1.0E0 | 1.0E0 | 1.6E3 | 1.5E2 | 46 | 12 | 43 | 12 | 0.43 |
| fA | ng/ml | 2.0E2 | 1.1E2 | 4.0E2 | 3.6E2 | 4.4E2 | 4.2E2 | 2.6E1 | 6.2E1 | 1.5E3 | 1.2E3 | 46 | 12 | 43 | 12 | 0.45 |
| eZ | ng/ml | 5.1E1 | 6.0E1 | 5.8E1 | 6.6E1 | 2.5E1 | 2.5E1 | 1.8E1 | 3.2E1 | 1.2E2 | 1.1E2 | 112 | 12 | 94 | 12 | 0.61 |
| fB | ng/ml | 6.0E2 | 6.6E2 | 6.9E2 | 7.2E2 | 3.0E2 | 2.6E2 | 1.6E2 | 3.5E2 | 1.5E3 | 1.3E3 | 46 | 14 | 43 | 14 | 0.56 |
| fN | ng/ml | 2.1E-1 | 3.4E0 | 3.1E0 | 4.9E0 | 7.2E0 | 5.4E0 | 2.1E-1 | 2.1E-1 | 5.4E1 | 1.4E1 | 112 | 12 | 94 | 12 | 0.64 |
| fP | ng/ml | 2.4E2 | 2.8E2 | 2.8E2 | 3.3E2 | 1.7E2 | 2.1E2 | 1.8E0 | 1.6E1 | 1.0E3 | 8.6E2 | 276 | 29 | 162 | 29 | 0.57 |
| fR | ng/ml | 1.2E5 | 2.0E5 | 1.7E5 | 3.0E5 | 1.4E5 | 2.3E5 | 3.1E4 | 1.9E2 | 7.7E5 | 8.7E5 | 295 | 20 | 90 | 20 | 0.68 |
| fY | ng/ml | 2.7E2 | 2.5E2 | 2.6E2 | 2.6E2 | 1.1E2 | 1.0E2 | 3.6E1 | 1.2E2 | 4.8E2 | 4.3E2 | 112 | 12 | 94 | 12 | 0.47 |
| gC | ng/ml | 2.3E2 | 2.7E2 | 2.6E2 | 2.9E2 | 1.3E2 | 1.1E2 | 8.3E1 | 1.6E2 | 1.1E3 | 5.9E2 | 127 | 16 | 74 | 16 | 0.61 |
| gL | pg/ml | 6.3E4 | 6.7E4 | 7.0E4 | 8.0E4 | 3.1E4 | 4.2E4 | 1.4E4 | 4.1E4 | 2.0E5 | 2.2E5 | 287 | 30 | 167 | 30 | 0.56 |
| gP | U/ml | 2.8E2 | 2.5E2 | 2.9E2 | 2.8E2 | 1.1E2 | 1.0E2 | 1.2E1 | 9.6E1 | 1.1E3 | 5.2E2 | 298 | 30 | 168 | 30 | 0.47 |
| gW | ng/ml | 6.8E2 | 5.1E2 | 1.3E3 | 1.0E3 | 1.7E3 | 1.3E3 | 3.1E-1 | 1.5E2 | 9.5E3 | 4.3E3 | 252 | 19 | 157 | 19 | 0.48 |
| gV | ng/ml | 2.1E1 | 2.2E1 | 2.2E1 | 2.4E1 | 7.2E0 | 6.4E0 | 2.9E-3 | 1.7E1 | 3.9E1 | 3.4E1 | 109 | 7 | 27 | 7 | 0.63 |
| tF | pg/mL | 1.4E3 | 9.0E2 | 1.5E4 | 3.8E3 | 4.5E4 | 5.7E3 | 1.8E1 | 1.8E1 | 3.2E5 | 2.0E4 | 231 | 27 | 159 | 27 | 0.49 |
| gZ | ug/ml | 9.3E-1 | 9.3E-1 | 4.8E1 | 8.4E1 | 1.1E2 | 1.6E2 | 8.7E-2 | 1.1E-1 | 4.1E2 | 4.1E2 | 46 | 12 | 43 | 12 | 0.56 |
| hA | ng/ml | 2.0E0 | 3.6E0 | 9.2E0 | 6.8E0 | 3.7E1 | 6.9E0 | 1.7E-2 | 6.3E-2 | 3.5E2 | 2.5E1 | 197 | 21 | 131 | 21 | 0.65 |
| nM | pg/ml | 1.0E-9 | 1.0E-9 | 7.9E1 | 1.0E-9 | 9.0E2 | 0.0E0 | 1.0E-9 | 1.0E-9 | 1.0E4 | 1.0E-9 | 131 | 21 | 103 | 21 | 0.49 |
| nN | pg/ml | 1.2E3 | 2.1E3 | 5.1E3 | 3.7E3 | 2.5E4 | 4.5E3 | 1.1E2 | 2.8E2 | 2.7E5 | 2.1E4 | 131 | 21 | 103 | 21 | 0.65 |
| nO | pg/ml | 2.7E1 | 2.9E1 | 4.3E1 | 5.0E1 | 4.2E1 | 5.5E1 | 3.5E0 | 9.7E0 | 2.4E2 | 2.4E2 | 131 | 21 | 103 | 21 | 0.54 |
| nR | pg/ml | 1.3E1 | 2.0E1 | 3.8E1 | 7.7E1 | 8.7E1 | 1.7E2 | 1.0E-9 | 1.9E0 | 8.2E2 | 7.1E2 | 131 | 21 | 103 | 21 | 0.59 |
| nT | pg/ml | 8.5E1 | 8.8E1 | 2.2E2 | 1.0E2 | 8.0E2 | 6.6E1 | 1.0E-9 | 1.0E-9 | 6.6E3 | 3.4E2 | 131 | 21 | 103 | 21 | 0.53 |
| nU | pg/ml | 2.9E1 | 2.9E1 | 2.6E2 | 8.5E1 | 1.5E3 | 1.3E2 | 1.0E-9 | 1.0E-9 | 1.3E4 | 4.4E2 | 131 | 21 | 103 | 21 | 0.50 |
| lW | pg/ml | 1.0E-9 | 1.0E-9 | 1.3E1 | 5.3E0 | 4.7E1 | 1.1E1 | 1.0E-9 | 1.0E-9 | 3.9E2 | 4.4E1 | 131 | 21 | 103 | 21 | 0.49 |

Figure 1 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| lX | pg/ml | 1.0E3 | 7.5E2 | 1.1E3 | 7.6E2 | 5.6E2 | 3.9E2 | 1.2E2 | 1.9E2 | 2.6E3 | 1.6E3 | 131 | 21 | 103 | 21 | 0.33 |
| lY | pg/ml | 2.0E1 | 1.6E1 | 2.3E1 | 1.4E1 | 2.1E1 | 8.2E0 | 1.0E-9 | 5.7E-1 | 1.4E2 | 3.0E1 | 131 | 21 | 103 | 21 | 0.35 |
| mE | pg/ml | 1.0E-9 | 1.0E-9 | 2.9E0 | 1.5E0 | 8.3E0 | 2.8E0 | 1.0E-9 | 1.0E-9 | 5.8E1 | 9.2E0 | 131 | 21 | 103 | 21 | 0.48 |
| mF | pg/ml | 1.0E-9 | 2.7E-1 | 4.0E0 | 2.5E0 | 2.3E1 | 4.2E0 | 1.0E-9 | 1.0E-9 | 2.5E2 | 1.3E1 | 131 | 21 | 103 | 21 | 0.55 |
| mH | pg/ml | 3.6E0 | 2.6E0 | 5.1E0 | 4.3E0 | 6.7E0 | 4.6E0 | 2.3E-1 | 5.4E-1 | 5.3E1 | 1.9E1 | 131 | 21 | 103 | 21 | 0.44 |
| mI | pg/ml | 1.0E-9 | 2.6E0 | 1.2E1 | 1.5E1 | 2.7E1 | 2.3E1 | 1.0E-9 | 1.0E-9 | 1.8E2 | 7.8E1 | 131 | 21 | 103 | 21 | 0.55 |
| mM | pg/ml | 2.2E1 | 3.8E1 | 6.5E1 | 5.1E1 | 1.5E2 | 6.7E1 | 1.0E-9 | 1.0E-9 | 1.1E3 | 2.9E2 | 131 | 21 | 103 | 21 | 0.55 |
| mP | pg/ml | 1.4E1 | 1.5E1 | 1.8E1 | 1.4E1 | 2.3E1 | 7.9E0 | 1.0E-9 | 1.0E-9 | 1.9E2 | 3.2E1 | 130 | 21 | 102 | 21 | 0.48 |
| mS | pg/ml | 1.8E3 | 1.4E3 | 2.0E3 | 1.6E3 | 1.6E3 | 7.4E2 | 1.0E-9 | 1.0E-9 | 1.3E4 | 2.7E3 | 131 | 21 | 103 | 21 | 0.41 |
| mT | pg/ml | 4.8E1 | 5.6E1 | 1.2E2 | 6.5E1 | 2.1E2 | 3.6E1 | 9.7E0 | 1.2E1 | 1.4E3 | 1.4E2 | 130 | 21 | 102 | 21 | 0.52 |
| mU | pg/ml | 2.2E0 | 3.1E0 | 5.5E0 | 3.1E0 | 2.1E1 | 1.7E0 | 1.0E-9 | 6.0E-1 | 2.2E2 | 6.6E0 | 130 | 21 | 102 | 21 | 0.60 |
| mW | pg/ml | 2.3E3 | 2.2E3 | 2.6E3 | 2.7E3 | 1.4E3 | 2.4E3 | 3.1E2 | 1.7E2 | 1.0E4 | 1.1E4 | 130 | 21 | 102 | 21 | 0.48 |
| mY | pg/ml | 5.6E2 | 6.5E2 | 8.6E2 | 8.8E2 | 1.3E3 | 7.2E2 | 1.0E-9 | 1.0E-9 | 1.1E4 | 2.6E3 | 131 | 21 | 103 | 21 | 0.57 |
| mZ | pg/ml | 2.2E2 | 1.5E2 | 3.8E2 | 3.8E2 | 4.4E2 | 4.1E2 | 1.0E-9 | 1.1E1 | 3.1E3 | 1.4E3 | 130 | 21 | 102 | 21 | 0.44 |
| nA | pg/ml | 2.0E0 | 4.8E-1 | 1.1E1 | 4.9E0 | 4.4E1 | 1.2E1 | 1.0E-9 | 1.0E-9 | 4.4E2 | 5.5E1 | 130 | 21 | 102 | 21 | 0.40 |
| nB | pg/ml | 3.0E2 | 3.1E2 | 3.1E2 | 3.3E2 | 1.5E2 | 1.9E2 | 3.0E1 | 7.9E1 | 8.2E2 | 1.0E3 | 131 | 21 | 103 | 21 | 0.52 |
| nC | pg/ml | 1.0E-9 | 8.3E1 | 3.7E4 | 7.5E4 | 3.2E4 | 3.3E5 | 1.0E-9 | 1.0E-9 | 3.7E5 | 1.5E6 | 131 | 21 | 103 | 21 | 0.61 |
| nD | pg/ml | 8.5E0 | 5.1E0 | 3.5E1 | 1.4E1 | 2.0E2 | 2.8E1 | 1.0E-9 | 1.0E-9 | 1.7E3 | 1.3E2 | 130 | 21 | 102 | 21 | 0.46 |
| nF | pg/ml | 1.0E-9 | 1.0E-9 | 5.0E0 | 3.8E0 | 2.6E1 | 1.0E1 | 1.0E-9 | 1.0E-9 | 2.4E2 | 3.8E1 | 131 | 21 | 103 | 21 | 0.51 |
| nH | pg/ml | 3.8E-1 | 2.5E0 | 8.9E1 | 1.5E2 | 8.8E2 | 5.7E2 | 1.0E-9 | 1.0E-9 | 1.0E4 | 2.6E3 | 130 | 21 | 102 | 21 | 0.59 |
| nI | pg/ml | 4.6E1 | 1.0E-9 | 1.6E2 | 6.2E1 | 8.4E2 | 1.7E2 | 1.0E-9 | 1.0E-9 | 9.2E3 | 7.9E2 | 131 | 21 | 103 | 21 | 0.37 |
| nJ | pg/ml | 1.7E-1 | 1.7E-1 | 4.1E1 | 1.2E0 | 4.5E2 | 3.5E0 | 1.0E-9 | 1.0E-9 | 5.2E3 | 1.6E1 | 131 | 21 | 103 | 21 | 0.45 |
| nK | pg/ml | 1.0E-9 | 1.0E-9 | 5.8E1 | 2.0E1 | 3.4E2 | 5.0E1 | 1.0E-9 | 1.0E-9 | 3.2E3 | 2.3E2 | 130 | 21 | 102 | 21 | 0.52 |
| nL | pg/ml | 1.0E-9 | 3.4E0 | 3.9E2 | 3.3E2 | 3.9E3 | 1.1E3 | 1.0E-9 | 1.0E-9 | 4.5E4 | 5.2E3 | 131 | 21 | 103 | 21 | 0.60 |
| hL | pg/ml | 1.8E4 | 2.6E4 | 2.3E4 | 2.7E4 | 1.8E4 | 1.7E4 | 1.0E-9 | 1.0E-9 | 1.4E5 | 6.0E4 | 112 | 12 | 94 | 12 | 0.59 |
| hO | pg/ml | 1.6E4 | 1.5E4 | 1.7E4 | 1.6E4 | 3.2E3 | 4.5E3 | 1.1E4 | 1.1E4 | 2.8E4 | 2.7E4 | 112 | 12 | 94 | 12 | 0.41 |
| hP | ng/ml | 4.4E5 | 4.4E5 | 4.1E5 | 5.2E5 | 3.3E5 | 7.4E5 | 1.7E4 | 2.5E4 | 2.6E6 | 2.8E6 | 112 | 12 | 94 | 12 | 0.46 |
| wJ | pg/ml | 1.5E5 | 1.0E5 | 1.7E5 | 1.2E5 | 1.0E5 | 7.9E4 | 1.1E4 | 2.3E4 | 5.8E5 | 2.5E5 | 113 | 9 | 91 | 9 | 0.33 |
| wK | pg/ml | 3.5E4 | 3.5E4 | 4.8E4 | 4.0E4 | 5.4E4 | 3.3E4 | 3.7E3 | 1.1E4 | 5.0E5 | 1.2E5 | 113 | 9 | 91 | 9 | 0.44 |
| wL | pg/ml | 3.9E0 | 5.3E0 | 4.1E1 | 4.9E1 | 1.1E2 | 1.1E2 | 1.0E-9 | 1.0E-9 | 8.4E2 | 3.5E2 | 113 | 9 | 91 | 9 | 0.49 |
| wP | pg/ml | 2.6E4 | 7.0E4 | 4.2E4 | 8.7E4 | 4.6E4 | 8.1E4 | 1.1E3 | 1.8E4 | 3.0E5 | 2.6E5 | 113 | 9 | 91 | 9 | 0.73 |
| wQ | pg/ml | 3.7E1 | 2.9E1 | 6.1E1 | 4.0E1 | 8.1E1 | 4.9E1 | 1.0E-9 | 1.0E-9 | 5.1E2 | 1.6E2 | 113 | 9 | 91 | 9 | 0.45 |
| hR | pg/ml | 2.6E4 | 2.7E4 | 2.7E4 | 2.8E4 | 1.1E4 | 9.3E3 | 1.1E1 | 1.3E4 | 5.8E4 | 4.4E4 | 189 | 20 | 129 | 20 | 0.53 |
| hV | pg/ml | 4.4E2 | 3.6E2 | 4.7E2 | 5.0E2 | 2.4E2 | 5.3E2 | 6.8E1 | 9.5E1 | 1.5E3 | 2.5E3 | 189 | 20 | 129 | 20 | 0.42 |
| hW | pg/ml | 1.5E3 | 2.2E3 | 2.0E3 | 4.0E3 | 1.6E3 | 8.5E3 | 2.2E2 | 7.9E2 | 1.0E4 | 4.0E4 | 189 | 20 | 129 | 20 | 0.65 |
| hX | pg/ml | 9.0E2 | 1.2E3 | 1.0E3 | 1.2E3 | 7.8E2 | 5.7E2 | 1.3E2 | 3.1E2 | 8.6E3 | 2.9E3 | 189 | 20 | 129 | 20 | 0.60 |
| iA | pg/ml | 1.4E2 | 1.8E2 | 2.8E2 | 3.3E2 | 6.2E2 | 2.7E2 | 5.8E0 | 1.7E1 | 7.1E3 | 8.7E2 | 231 | 26 | 159 | 26 | 0.63 |
| iB | ng/ml | 4.8E0 | 7.7E0 | 6.0E0 | 9.0E0 | 4.9E0 | 6.0E0 | 3.3E-2 | 1.1E0 | 3.8E1 | 2.2E1 | 197 | 21 | 131 | 21 | 0.66 |
| iC | U/ml | 2.1E-1 | 6.7E-1 | 9.0E-1 | 1.3E0 | 4.6E0 | 2.6E0 | 1.0E-9 | 6.8E-2 | 5.5E1 | 1.2E1 | 197 | 21 | 131 | 21 | 0.69 |
| tQ | pg/ml | 1.1E3 | 1.3E3 | 1.2E3 | 1.5E3 | 5.5E2 | 8.8E2 | 2.8E2 | 6.3E2 | 2.5E3 | 3.3E3 | 108 | 8 | 88 | 8 | 0.55 |
| tT | pg/ml | 1.7E1 | 2.6E1 | 2.0E1 | 2.9E1 | 1.5E1 | 2.1E1 | 5.4E0 | 7.2E0 | 1.2E2 | 6.7E1 | 109 | 8 | 89 | 8 | 0.59 |
| tS | pg/ml | 1.1E0 | 1.1E0 | 1.3E0 | 1.5E0 | 1.3E0 | 2.2E0 | 1.0E-9 | 1.0E-9 | 8.5E0 | 7.0E0 | 109 | 9 | 89 | 9 | 0.47 |
| tX | pg/ml | 9.9E-1 | 1.2E0 | 1.2E0 | 2.3E0 | 9.8E-1 | 2.4E0 | 2.5E-2 | 9.3E-2 | 7.0E0 | 6.2E0 | 109 | 8 | 89 | 8 | 0.59 |
| tO | pg/ml | 4.4E0 | 3.9E0 | 5.1E0 | 4.5E0 | 3.3E0 | 2.7E0 | 1.0E-9 | 1.7E0 | 1.8E1 | 9.6E0 | 109 | 9 | 89 | 9 | 0.45 |
| tR | pg/ml | 2.1E-1 | 2.2E-1 | 2.9E-1 | 3.3E-1 | 2.9E-1 | 3.9E-1 | 1.0E-9 | 1.4E-2 | 1.6E0 | 1.3E0 | 108 | 9 | 88 | 9 | 0.51 |
| tU | pg/ml | 9.1E0 | 1.2E1 | 1.1E1 | 1.9E1 | 6.9E0 | 2.3E1 | 2.2E-1 | 5.0E0 | 4.4E1 | 8.0E1 | 111 | 9 | 90 | 9 | 0.61 |
| tN | pg/ml | 1.8E1 | 3.2E1 | 2.3E1 | 3.3E1 | 1.9E1 | 2.0E1 | 1.0E-9 | 6.1E0 | 1.5E2 | 6.5E1 | 109 | 8 | 88 | 8 | 0.66 |
| tV | ng/ml | 4.7E2 | 8.7E2 | 6.4E2 | 9.2E2 | 5.0E2 | 5.0E2 | 5.3E1 | 3.9E2 | 2.9E3 | 1.7E3 | 113 | 8 | 91 | 8 | 0.69 |
| iH | ng/ml | 1.6E5 | 1.5E5 | 1.5E5 | 1.5E5 | 4.7E4 | 4.7E4 | 5.1E4 | 5.1E4 | 2.7E5 | 2.4E5 | 231 | 26 | 159 | 26 | 0.48 |
| iJ | ng/ml | 5.4E4 | 4.6E4 | 5.5E4 | 5.2E4 | 2.9E4 | 3.2E4 | 5.5E3 | 1.1E4 | 2.5E5 | 1.8E5 | 231 | 26 | 159 | 26 | 0.44 |
| hB | ng/ml | 4.1E-1 | 5.6E-1 | 5.0E-1 | 8.4E-1 | 3.3E-1 | 7.5E-1 | 1.0E-9 | 1.2E-1 | 2.3E0 | 3.2E0 | 231 | 26 | 159 | 26 | 0.66 |
| hC | ng/ml | 3.9E3 | 7.6E3 | 6.8E3 | 1.1E4 | 1.0E4 | 1.4E4 | 1.0E-9 | 4.5E1 | 1.1E5 | 5.7E4 | 231 | 26 | 159 | 26 | 0.59 |
| hF | ng/ml | 1.0E-9 | 1.0E-9 | 2.1E1 | 3.7E-1 | 2.7E2 | 1.9E0 | 1.0E-9 | 1.0E-9 | 4.0E3 | 9.6E0 | 231 | 26 | 159 | 26 | 0.51 |
| hG | pg/ml | 6.9E3 | 6.8E3 | 7.4E3 | 8.2E3 | 3.2E3 | 4.3E3 | 2.8E1 | 3.6E3 | 1.9E4 | 2.0E4 | 231 | 26 | 159 | 26 | 0.52 |
| iO | ng/ml | 3.8E5 | 4.0E5 | 4.0E5 | 4.0E5 | 1.8E5 | 1.9E5 | 1.1E4 | 8.3E4 | 1.1E6 | 8.2E5 | 231 | 26 | 159 | 26 | 0.51 |
| iP | ng/ml | 5.0E4 | 5.9E4 | 5.5E4 | 7.0E4 | 5.2E4 | 1.0E5 | 1.0E-9 | 7.2E3 | 5.5E5 | 5.7E5 | 231 | 26 | 159 | 26 | 0.53 |
| iZ | ng/ml | 1.6E3 | 2.0E3 | 1.8E3 | 2.1E3 | 7.8E2 | 1.0E3 | 4.7E2 | 9.8E2 | 5.7E3 | 4.6E3 | 230 | 25 | 158 | 25 | 0.56 |

Figure 1 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| yH | pg/ml | 1.1E3 | 1.4E3 | 3.1E3 | 1.9E3 | 1.2E4 | 2.3E3 | 1.0E-9 | 3.0E2 | 1.2E5 | 7.7E3 | 113 | 9 | 92 | 9 | 0.54 |
| yK | U/ml | 2.2E1 | 2.8E1 | 4.5E1 | 3.3E1 | 6.9E1 | 3.2E1 | 1.0E-9 | 1.0E-9 | 3.8E2 | 1.0E2 | 113 | 9 | 92 | 9 | 0.49 |
| yJ | pg/ml | 3.3E4 | 4.0E4 | 4.5E4 | 4.6E4 | 3.3E4 | 2.9E4 | 1.7E3 | 2.7E3 | 1.6E5 | 8.5E4 | 113 | 9 | 92 | 9 | 0.53 |
| yD | ng/ml | 1.5E-2 | 1.5E-2 | 1.5E-2 | 1.6E-2 | 6.7E-3 | 7.5E-3 | 1.0E-9 | 6.3E-3 | 4.3E-2 | 3.0E-2 | 113 | 9 | 91 | 9 | 0.52 |
| jB | ng/ml | 2.6E5 | 2.1E5 | 2.6E5 | 2.8E5 | 9.3E4 | 1.7E5 | 5.7E4 | 1.2E5 | 4.7E5 | 6.2E5 | 46 | 12 | 43 | 12 | 0.46 |
| wB | pg/ml | 7.4E3 | 1.6E4 | 9.4E3 | 1.7E4 | 7.2E3 | 9.6E3 | 1.7E3 | 5.3E3 | 4.1E4 | 3.0E4 | 113 | 9 | 91 | 9 | 0.74 |
| pY | pg/ml | 5.9E0 | 6.8E0 | 8.6E0 | 6.9E0 | 1.9E1 | 3.7E0 | 2.1E0 | 2.6E0 | 2.0E2 | 1.7E1 | 112 | 12 | 94 | 12 | 0.53 |
| rC | pg/ml | 1.6E3 | 1.1E3 | 2.2E3 | 1.4E3 | 2.2E3 | 8.7E2 | 1.0E-9 | 7.0E1 | 1.5E4 | 3.4E3 | 189 | 18 | 128 | 18 | 0.41 |
| rB | pg/ml | 2.4E1 | 5.8E1 | 4.3E1 | 6.8E1 | 8.9E1 | 6.2E1 | 1.0E-9 | 1.0E-9 | 9.5E2 | 2.1E2 | 189 | 18 | 128 | 18 | 0.65 |
| zG | 2.5ng/ml | 2.0E-1 | 5.3E-1 | 4.5E-1 | 6.9E-1 | 8.0E-1 | 8.6E-1 | 1.0E-9 | 1.0E-9 | 4.8E0 | 2.7E0 | 113 | 9 | 92 | 9 | 0.60 |
| zH | 2.3mU/ml | 1.1E-1 | 9.0E-2 | 1.1E-1 | 9.3E-2 | 5.5E-2 | 2.5E-2 | 1.0E-2 | 4.4E-2 | 4.4E-1 | 1.4E-1 | 113 | 9 | 92 | 9 | 0.38 |
| zI | 2.6ng/ml | 2.0E0 | 4.5E0 | 3.8E0 | 6.3E0 | 4.5E0 | 5.9E0 | 5.4E-1 | 7.8E-1 | 2.7E1 | 1.6E1 | 113 | 9 | 92 | 9 | 0.63 |
| qA | ng/ml | 1.0E7 | 1.3E7 | 1.2E7 | 1.7E7 | 7.7E6 | 9.6E6 | 2.0E6 | 4.3E6 | 4.6E7 | 3.4E7 | 112 | 12 | 94 | 12 | 0.65 |
| qB | ng/ml | 6.4E5 | 6.7E5 | 8.2E5 | 1.1E6 | 5.6E5 | 1.0E6 | 2.1E5 | 2.4E5 | 2.9E6 | 3.8E6 | 112 | 12 | 94 | 12 | 0.55 |
| qC | ng/ml | 3.9E5 | 2.3E5 | 7.3E5 | 2.3E5 | 1.1E6 | 1.6E5 | 3.4E3 | 2.1E4 | 7.1E6 | 5.2E5 | 112 | 12 | 94 | 12 | 0.28 |
| qD | ng/ml | 1.6E7 | 1.2E7 | 1.8E7 | 1.3E7 | 8.8E6 | 4.8E6 | 1.2E6 | 8.4E6 | 5.2E7 | 2.6E7 | 112 | 12 | 94 | 12 | 0.32 |
| jD | ng/ml | 3.1E1 | 2.9E1 | 4.8E1 | 6.1E1 | 1.1E2 | 1.2E2 | 1.0E-9 | 1.0E-9 | 5.1E2 | 5.1E2 | 196 | 21 | 131 | 21 | 0.50 |
| jE | ng/ml | 1.0E-9 | 1.0E-9 | 7.1E0 | 1.3E1 | 1.7E1 | 1.9E1 | 1.0E-9 | 1.0E-9 | 1.2E2 | 5.6E1 | 196 | 21 | 131 | 21 | 0.60 |
| jF | ng/ml | 4.2E1 | 2.6E1 | 5.7E1 | 4.5E1 | 6.3E1 | 5.7E1 | 1.0E-9 | 1.0E-9 | 3.5E2 | 1.9E2 | 196 | 21 | 131 | 21 | 0.44 |
| jG | ng/ml | 4.6E3 | 4.2E3 | 4.7E3 | 4.4E3 | 2.0E3 | 2.0E3 | 7.6E2 | 6.0E2 | 1.1E4 | 7.9E3 | 197 | 21 | 131 | 21 | 0.47 |
| jH | ng/ml | 7.6E1 | 7.9E1 | 8.5E1 | 9.9E1 | 4.8E1 | 8.8E1 | 1.3E1 | 1.5E1 | 3.3E2 | 4.3E2 | 197 | 21 | 131 | 21 | 0.51 |
| jI | ng/ml | 6.8E1 | 9.4E1 | 7.3E1 | 1.1E2 | 3.3E1 | 9.0E1 | 1.9E1 | 4.4E1 | 2.5E2 | 4.4E2 | 197 | 21 | 131 | 21 | 0.66 |
| sK | pg/mL | 3.7E3 | 4.7E3 | 4.1E3 | 6.7E3 | 1.6E3 | 6.5E3 | 1.1E3 | 2.1E3 | 1.0E4 | 2.3E4 | 113 | 9 | 92 | 9 | 0.64 |
| sM | pg/mL | 7.6E4 | 9.2E4 | 7.9E4 | 1.0E5 | 2.6E4 | 4.3E4 | 3.3E4 | 5.1E4 | 1.6E5 | 2.0E5 | 113 | 9 | 92 | 9 | 0.67 |
| sO | pg/mL | 2.9E8 | 2.5E8 | 2.8E8 | 2.3E8 | 1.0E8 | 1.2E8 | 4.9E7 | 6.6E7 | 5.7E8 | 4.0E8 | 113 | 9 | 92 | 9 | 0.40 |
| wC | ng/ml | 1.5E0 | 1.7E0 | 1.9E0 | 1.7E0 | 1.7E0 | 8.4E-1 | 2.5E-1 | 3.1E-1 | 1.5E1 | 2.9E0 | 113 | 9 | 91 | 9 | 0.52 |
| wD | ng/ml | 1.7E1 | 4.0E1 | 4.8E1 | 8.9E1 | 2.0E2 | 9.2E1 | 2.1E0 | 1.2E1 | 2.1E3 | 2.9E2 | 113 | 9 | 91 | 9 | 0.79 |
| wE | ng/ml | 4.8E1 | 4.5E1 | 4.9E1 | 5.1E1 | 2.3E1 | 1.7E1 | 3.2E0 | 3.6E1 | 1.4E2 | 8.9E1 | 113 | 9 | 91 | 9 | 0.50 |
| wG | ng/ml | 6.4E-2 | 5.9E-2 | 1.0E-1 | 1.5E-1 | 1.3E-1 | 2.3E-1 | 1.0E-9 | 1.0E-9 | 7.1E-1 | 6.8E-1 | 113 | 9 | 91 | 9 | 0.51 |
| wH | ng/ml | 1.8E-2 | 5.9E-2 | 1.5E-1 | 7.4E-1 | 5.2E-1 | 1.8E0 | 1.0E-9 | 1.0E-9 | 4.2E0 | 5.6E0 | 113 | 9 | 91 | 9 | 0.66 |
| wF | ng/ml | 1.4E-1 | 8.1E-1 | 1.5E0 | 3.2E0 | 7.1E0 | 3.9E0 | 1.0E-9 | 1.0E-9 | 5.7E1 | 9.6E0 | 113 | 9 | 91 | 9 | 0.66 |
| rA | pg/ml | 2.6E1 | 2.6E1 | 3.1E1 | 3.2E1 | 2.5E1 | 2.2E1 | 1.0E-9 | 6.9E0 | 2.0E2 | 9.6E1 | 197 | 19 | 131 | 19 | 0.52 |
| qZ | pg/ml | 4.1E1 | 8.0E1 | 3.7E2 | 9.4E2 | 1.8E3 | 2.6E3 | 1.0E-9 | 6.5E-4 | 1.0E4 | 1.0E4 | 155 | 16 | 118 | 16 | 0.61 |
| qY | pg/ml | 2.6E1 | 1.1E1 | 5.1E1 | 2.1E1 | 6.6E1 | 2.4E1 | 8.7E-1 | 2.1E0 | 5.3E2 | 9.1E1 | 197 | 19 | 131 | 19 | 0.33 |
| qX | pg/ml | 5.9E1 | 7.5E1 | 6.5E1 | 8.5E1 | 4.2E1 | 5.4E1 | 1.0E-9 | 1.7E1 | 2.1E2 | 2.0E2 | 197 | 19 | 131 | 19 | 0.60 |
| qW | pg/ml | 9.2E0 | 7.4E0 | 1.4E1 | 1.1E1 | 1.6E1 | 1.1E1 | 1.0E-9 | 1.0E-9 | 1.2E2 | 3.9E1 | 197 | 19 | 131 | 19 | 0.45 |
| qV | pg/ml | 2.2E3 | 1.9E3 | 2.9E3 | 2.7E3 | 2.1E3 | 2.3E3 | 1.0E2 | 6.3E2 | 1.1E4 | 9.6E3 | 197 | 19 | 131 | 19 | 0.47 |
| qU | pg/ml | 6.1E1 | 1.1E2 | 1.6E2 | 1.7E2 | 2.8E2 | 2.0E2 | 1.0E-9 | 3.5E0 | 2.1E3 | 7.9E2 | 197 | 19 | 131 | 19 | 0.56 |
| qT | pg/ml | 4.0E1 | 6.0E1 | 6.8E1 | 8.0E1 | 9.8E1 | 7.6E1 | 1.0E-9 | 6.9E0 | 9.0E2 | 3.0E2 | 197 | 19 | 131 | 19 | 0.57 |
| qI | ng/ml | 6.5E4 | 6.2E4 | 6.4E4 | 6.3E4 | 3.0E4 | 2.7E4 | 5.4E3 | 2.7E4 | 1.6E5 | 1.2E5 | 112 | 10 | 94 | 10 | 0.48 |
| qH | ng/ml | 6.5E4 | 5.4E4 | 7.2E4 | 6.5E4 | 4.5E4 | 3.8E4 | 7.6E3 | 1.0E4 | 2.7E5 | 1.4E5 | 112 | 10 | 94 | 10 | 0.47 |
| qG | ng/ml | 1.9E5 | 1.9E5 | 2.0E5 | 1.8E5 | 7.1E4 | 5.8E4 | 1.7E4 | 9.9E4 | 4.2E5 | 2.7E5 | 112 | 10 | 94 | 10 | 0.43 |
| jK | ng/ml | 1.6E3 | 1.3E3 | 1.7E3 | 1.5E3 | 6.5E2 | 5.9E2 | 2.8E2 | 7.5E2 | 4.3E3 | 2.8E3 | 197 | 21 | 131 | 21 | 0.37 |
| jL | ng/ml | 1.9E2 | 2.6E2 | 2.8E2 | 3.6E2 | 2.5E2 | 3.4E2 | 3.6E1 | 1.2E2 | 2.1E3 | 1.7E3 | 197 | 21 | 131 | 21 | 0.62 |
| jM | ng/ml | 7.4E4 | 6.8E4 | 7.8E4 | 7.3E4 | 3.9E4 | 4.2E4 | 3.9E2 | 5.7E3 | 1.9E5 | 1.5E5 | 197 | 21 | 131 | 21 | 0.47 |
| jO | pg/ml | 2.1E5 | 2.0E5 | 2.6E5 | 2.5E5 | 1.5E5 | 1.2E5 | 5.2E4 | 9.8E4 | 1.1E6 | 5.2E5 | 197 | 21 | 131 | 21 | 0.50 |
| jP | pg/ml | 2.2E5 | 2.2E5 | 2.6E5 | 2.8E5 | 1.6E5 | 1.7E5 | 3.6E4 | 8.4E4 | 9.2E5 | 5.8E5 | 197 | 21 | 131 | 21 | 0.53 |
| jQ | pg/ml | 2.7E3 | 2.1E3 | 3.8E3 | 4.8E3 | 3.5E3 | 1.2E4 | 1.0E-9 | 4.9E2 | 1.8E4 | 5.6E4 | 197 | 21 | 131 | 21 | 0.42 |
| jR | pg/ml | 7.7E3 | 4.0E3 | 1.2E4 | 1.6E4 | 1.3E4 | 3.9E4 | 1.0E-9 | 3.0E1 | 9.0E4 | 1.8E5 | 197 | 21 | 131 | 21 | 0.42 |
| jT | pg/ml | 1.8E5 | 1.6E5 | 1.8E5 | 1.8E5 | 6.6E4 | 9.4E4 | 6.8E4 | 7.5E4 | 4.5E5 | 4.7E5 | 197 | 21 | 131 | 21 | 0.45 |
| xA | pg/ml | 3.9E0 | 7.3E0 | 1.4E1 | 1.9E1 | 4.2E1 | 3.4E1 | 1.0E-9 | 1.0E-9 | 3.9E2 | 1.1E2 | 113 | 9 | 92 | 9 | 0.58 |
| yE | pg/ml | 7.9E1 | 7.9E1 | 8.6E1 | 1.1E2 | 4.0E1 | 7.3E1 | 1.8E1 | 1.6E1 | 3.0E2 | 2.5E2 | 113 | 9 | 92 | 9 | 0.57 |
| tM | pg/ml | 3.9E1 | 4.4E1 | 4.0E1 | 5.1E1 | 1.8E1 | 3.1E1 | 1.0E-9 | 1.6E1 | 1.0E2 | 1.1E2 | 113 | 9 | 92 | 9 | 0.57 |
| tL | pg/ml | 1.0E-9 | 1.0E-9 | 3.5E0 | 3.0E0 | 2.5E1 | 8.7E0 | 1.0E-9 | 1.0E-9 | 2.6E2 | 2.6E1 | 113 | 9 | 92 | 9 | 0.54 |
| jU | mIU/ml | 4.6E0 | 2.3E0 | 1.1E1 | 8.5E0 | 1.7E1 | 1.3E1 | 6.2E-2 | 4.2E-2 | 1.1E2 | 5.3E1 | 197 | 21 | 131 | 21 | 0.44 |
| jV | mIU/ml | 1.5E0 | 1.1E0 | 3.8E0 | 2.5E0 | 6.4E0 | 3.0E0 | 1.7E-3 | 2.2E-3 | 3.5E1 | 1.0E1 | 197 | 21 | 131 | 21 | 0.46 |
| jY | ng/ml | 5.9E-4 | 3.9E-3 | 5.8E-3 | 6.0E-3 | 2.7E-3 | 6.6E-3 | 1.0E-9 | 1.0E-9 | 3.0E-1 | 2.4E-2 | 197 | 21 | 131 | 21 | 0.66 |

Figure 1 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| kC | pg/ml | 9.7E1 | 8.8E1 | 1.8E2 | 1.5E2 | 3.8E2 | 1.4E2 | 2.1E1 | 3.6E1 | 3.5E3 | 5.9E2 | 131 | 21 | 103 | 21 | 0.46 |
| kE | pg/ml | 1.3E5 | 1.3E5 | 1.3E5 | 1.4E5 | 3.8E4 | 4.9E4 | 1.2E4 | 5.1E4 | 2.3E5 | 2.7E5 | 131 | 21 | 103 | 21 | 0.48 |
| kF | pg/mL | 6.0E1 | 6.9E1 | 6.8E1 | 7.0E1 | 4.8E1 | 2.3E1 | 2.6E1 | 3.4E1 | 5.1E2 | 1.2E2 | 131 | 21 | 103 | 21 | 0.59 |
| kG | pg/mL | 9.2E3 | 9.2E3 | 1.2E4 | 1.3E4 | 1.4E4 | 1.1E4 | 7.5E2 | 1.1E3 | 1.2E5 | 5.0E4 | 131 | 21 | 103 | 21 | 0.55 |
| kI | pg/ml | 1.8E2 | 1.8E2 | 2.2E2 | 2.1E2 | 1.3E2 | 1.3E2 | 4.4E1 | 1.0E-9 | 8.7E2 | 6.2E2 | 131 | 21 | 103 | 21 | 0.49 |
| kK | pg/ml | 1.0E2 | 1.4E2 | 1.6E2 | 1.9E2 | 1.9E2 | 1.8E2 | 6.4E0 | 2.9E1 | 1.6E3 | 6.3E2 | 131 | 21 | 103 | 21 | 0.55 |
| kN | pg/ml | 9.5E2 | 1.0E3 | 2.0E3 | 1.7E3 | 5.2E3 | 2.1E3 | 7.6E1 | 3.8E2 | 5.5E4 | 8.7E3 | 131 | 21 | 103 | 21 | 0.53 |
| kO | pg/ml | 7.2E3 | 6.1E3 | 8.6E3 | 7.9E3 | 1.1E4 | 3.8E3 | 3.4E2 | 4.2E3 | 1.3E5 | 1.9E4 | 131 | 21 | 103 | 21 | 0.46 |
| kP | pg/ml | 6.3E3 | 4.5E3 | 7.5E3 | 5.7E3 | 6.2E3 | 4.0E3 | 8.6E2 | 1.4E3 | 4.8E4 | 1.7E4 | 131 | 21 | 103 | 21 | 0.39 |
| kQ | pg/ml | 4.1E3 | 4.3E3 | 4.9E3 | 5.2E3 | 3.0E3 | 4.1E3 | 5.6E2 | 1.4E3 | 2.5E4 | 2.2E4 | 231 | 26 | 159 | 26 | 0.50 |
| kR | pg/ml | 2.1E1 | 1.6E1 | 3.1E1 | 2.7E1 | 6.9E1 | 2.6E1 | 1.0E-9 | 5.5E0 | 1.0E3 | 1.1E2 | 231 | 26 | 159 | 26 | 0.44 |
| kS | pg/ml | 8.0E2 | 9.4E2 | 9.7E2 | 1.0E3 | 1.0E3 | 6.5E2 | 8.2E1 | 2.9E2 | 1.4E4 | 3.0E3 | 231 | 26 | 159 | 26 | 0.54 |
| pS | pg/ml | 1.9E5 | 1.4E5 | 2.2E5 | 1.6E5 | 1.1E5 | 9.2E4 | 7.5E4 | 6.0E4 | 8.3E5 | 3.6E5 | 113 | 9 | 92 | 9 | 0.31 |
| rZ | ng/ml | 1.0E-9 | 2.2E-3 | 5.4E-3 | 2.6E-2 | 1.5E-2 | 6.9E-2 | 1.0E-9 | 1.0E-9 | 1.1E-1 | 2.9E-1 | 190 | 17 | 126 | 17 | 0.61 |
| rY | ng/ml | 5.7E-2 | 6.9E-2 | 3.6E-1 | 8.8E-1 | 2.3E0 | 3.3E0 | 1.0E-9 | 1.0E-9 | 2.3E1 | 1.4E1 | 190 | 17 | 126 | 17 | 0.58 |
| rX | ng/ml | 1.0E-9 | 1.0E-9 | 6.9E-2 | 1.5E-1 | 4.2E-1 | 5.7E-1 | 1.0E-9 | 1.0E-9 | 3.7E0 | 2.3E0 | 190 | 17 | 126 | 17 | 0.64 |
| IK | pg/ml | 9.9E1 | 2.0E1 | 1.9E2 | 1.1E2 | 3.1E2 | 2.0E2 | 1.0E-9 | 1.0E-9 | 3.3E3 | 7.9E2 | 196 | 21 | 131 | 21 | 0.35 |
| IL | pg/ml | 1.6E3 | 1.7E3 | 2.6E3 | 2.1E3 | 3.7E3 | 1.7E3 | 1.5E1 | 1.9E2 | 4.2E4 | 6.3E3 | 197 | 21 | 131 | 21 | 0.49 |
| IM | pg/ml | 1.1E3 | 2.6E3 | 3.5E3 | 6.8E3 | 7.5E3 | 1.1E4 | 1.2E2 | 9.5E0 | 5.1E4 | 4.0E4 | 197 | 21 | 131 | 21 | 0.61 |
| IN | pg/ml | 1.0E-9 | 3.0E0 | 4.2E0 | 5.2E0 | 1.5E1 | 8.6E0 | 1.0E-9 | 1.0E-9 | 1.5E2 | 3.5E1 | 197 | 21 | 131 | 21 | 0.58 |
| IO | pg/ml | 1.0E-9 | 1.0E-9 | 1.6E0 | 8.2E0 | 1.1E1 | 3.1E1 | 1.0E-9 | 1.0E-9 | 1.3E2 | 1.4E2 | 196 | 21 | 131 | 21 | 0.53 |
| zA | ng/ml | 2.0E7 | 1.8E7 | 2.0E7 | 1.7E7 | 6.6E6 | 5.9E6 | 5.9E6 | 7.5E6 | 3.6E7 | 2.5E7 | 109 | 9 | 87 | 9 | 0.38 |
| rW | ng/ml | 1.5E-2 | 1.5E-2 | 3.5E-2 | 1.8E-2 | 5.1E-2 | 1.1E-2 | 1.0E-9 | 7.4E-3 | 3.2E-1 | 4.3E-2 | 112 | 9 | 93 | 9 | 0.51 |
| rV | ng/ml | 1.0E-9 | 1.0E-9 | 1.8E-2 | 1.2E-2 | 5.8E-2 | 2.1E-2 | 1.0E-9 | 1.0E-9 | 2.8E-1 | 5.6E-2 | 112 | 9 | 93 | 9 | 0.56 |
| rU | ng/ml | 8.2E-2 | 7.6E-2 | 2.7E-1 | 1.3E-1 | 6.5E-1 | 1.2E-1 | 1.0E-9 | 1.0E-9 | 4.4E0 | 4.0E-1 | 112 | 9 | 93 | 9 | 0.54 |
| rT | ng/ml | 5.4E0 | 6.9E0 | 5.9E0 | 7.8E0 | 3.8E0 | 4.3E0 | 8.9E-2 | 1.0E0 | 2.1E1 | 1.3E1 | 112 | 9 | 93 | 9 | 0.65 |
| rS | ng/ml | 3.7E0 | 5.2E0 | 5.3E0 | 1.4E1 | 5.1E0 | 1.9E1 | 3.9E-1 | 2.0E0 | 3.8E1 | 5.9E1 | 112 | 9 | 93 | 9 | 0.66 |
| sC | pg/mL | 8.0E3 | 6.2E3 | 1.3E4 | 9.1E3 | 1.4E4 | 7.7E3 | 1.7E3 | 3.4E3 | 8.0E4 | 2.8E4 | 113 | 9 | 92 | 9 | 0.47 |
| yL | pg/ml | 3.0E1 | 4.1E1 | 3.4E1 | 5.7E1 | 2.3E1 | 5.5E1 | 5.6E0 | 1.6E1 | 1.8E2 | 1.9E2 | 111 | 9 | 90 | 9 | 0.64 |
| rP | ng/ml | 1.0E2 | 7.4E1 | 2.8E2 | 2.5E2 | 9.3E2 | 2.4E2 | 1.0E-9 | 1.2E1 | 9.7E3 | 5.0E2 | 112 | 9 | 93 | 9 | 0.54 |
| rQ | ng/ml | 1.0E-9 | 1.0E-9 | 8.0E0 | 1.9E1 | 2.8E1 | 5.6E1 | 1.0E-9 | 1.0E-9 | 1.7E2 | 1.7E2 | 112 | 9 | 93 | 9 | 0.49 |
| rO | ng/ml | 3.0E-2 | 1.5E-2 | 6.4E-2 | 3.9E-2 | 1.0E-1 | 5.5E-2 | 1.0E-9 | 1.0E-9 | 4.9E-1 | 1.4E-1 | 112 | 9 | 93 | 9 | 0.43 |
| rR | ng/ml | 4.0E0 | 4.0E0 | 2.0E1 | 8.8E0 | 5.0E1 | 1.3E1 | 1.0E-9 | 1.0E-9 | 4.5E2 | 3.9E1 | 112 | 9 | 93 | 9 | 0.45 |
| rN | ng/ml | 6.0E-1 | 7.9E-1 | 7.3E-1 | 2.4E0 | 5.2E-1 | 4.1E0 | 5.1E-2 | 3.1E-1 | 3.0E0 | 1.3E1 | 112 | 9 | 93 | 9 | 0.63 |
| qO | pg/ml | 1.0E4 | 1.2E4 | 1.5E4 | 1.8E4 | 1.3E4 | 1.7E4 | 7.4E2 | 5.4E3 | 6.4E4 | 6.3E4 | 112 | 10 | 92 | 10 | 0.56 |
| qP | pg/ml | 3.6E2 | 3.5E2 | 5.0E2 | 5.9E2 | 3.9E2 | 6.8E2 | 1.0E-9 | 1.5E2 | 2.2E3 | 2.5E3 | 112 | 10 | 92 | 10 | 0.50 |
| qQ | pg/ml | 1.5E1 | 1.1E1 | 1.7E1 | 1.8E1 | 3.8E1 | 2.0E1 | 1.0E-9 | 1.0E-9 | 2.8E2 | 4.3E1 | 112 | 10 | 92 | 10 | 0.57 |
| nW | pg/ml | 1.1E5 | 1.1E5 | 1.1E5 | 1.1E5 | 2.5E4 | 3.5E4 | 5.8E4 | 3.6E4 | 1.8E5 | 2.1E5 | 231 | 26 | 159 | 26 | 0.48 |
| nY | pg/ml | 2.1E3 | 2.1E3 | 2.4E3 | 2.7E3 | 1.6E3 | 1.7E3 | 5.1E2 | 6.3E2 | 1.3E4 | 8.1E3 | 231 | 26 | 159 | 26 | 0.54 |
| oO | pg/ml | 7.8E4 | 1.0E5 | 1.1E5 | 1.2E5 | 9.7E4 | 7.8E4 | 1.5E4 | 3.3E3 | 6.2E5 | 3.4E5 | 123 | 20 | 97 | 20 | 0.60 |
| oP | pg/ml | 1.2E5 | 1.4E5 | 1.4E5 | 1.5E5 | 9.1E4 | 9.8E4 | 2.4E4 | 2.4E4 | 4.5E5 | 4.6E5 | 123 | 20 | 97 | 20 | 0.55 |
| oQ | pg/ml | 2.8E3 | 3.2E3 | 3.5E3 | 4.3E3 | 2.8E3 | 3.6E3 | 9.3E2 | 8.7E2 | 2.1E4 | 1.7E4 | 123 | 20 | 97 | 20 | 0.59 |
| oE | pg/ml | 1.3E2 | 6.2E2 | 3.6E2 | 8.8E2 | 5.4E2 | 9.1E2 | 1.0E-9 | 1.0E-9 | 4.7E3 | 3.4E3 | 231 | 26 | 159 | 26 | 0.67 |
| oF | pg/ml | 7.7E3 | 1.9E4 | 2.0E4 | 3.8E4 | 3.6E4 | 4.6E4 | 6.4E1 | 1.3E2 | 2.5E5 | 1.7E5 | 231 | 26 | 159 | 26 | 0.66 |
| oH | pg/ml | 4.4E1 | 3.8E1 | 9.3E1 | 5.2E1 | 1.4E2 | 4.7E1 | 4.2E0 | 7.3E0 | 9.9E2 | 1.8E2 | 231 | 26 | 159 | 26 | 0.42 |
| oK | pg/ml | 7.6E2 | 1.0E3 | 1.8E3 | 2.0E3 | 2.5E3 | 2.1E3 | 5.2E1 | 2.3E2 | 1.8E4 | 7.3E3 | 231 | 26 | 159 | 26 | 0.57 |
| oN | pg/ml | 5.0E2 | 5.0E2 | 7.5E2 | 6.3E2 | 1.4E3 | 4.1E2 | 1.5E2 | 1.1E2 | 1.8E4 | 1.8E3 | 231 | 26 | 159 | 26 | 0.51 |
| oW | pg/ml | 2.1E2 | 3.6E2 | 4.0E2 | 6.1E2 | 8.7E2 | 8.0E2 | 7.7E1 | 9.5E1 | 6.0E3 | 2.7E3 | 46 | 12 | 43 | 12 | 0.59 |
| oT | pg/ml | 3.3E2 | 3.4E2 | 3.7E2 | 3.4E2 | 1.9E2 | 1.2E2 | 9.9E1 | 1.4E2 | 7.9E2 | 5.4E2 | 46 | 12 | 43 | 12 | 0.48 |
| oV | pg/ml | 1.3E2 | 9.3E1 | 3.0E2 | 1.4E2 | 5.1E2 | 1.7E2 | 1.0E-9 | 1.1E1 | 2.4E3 | 6.3E2 | 46 | 12 | 43 | 12 | 0.41 |
| oD | pg/ml | 1.7E4 | 1.5E4 | 1.7E4 | 1.7E4 | 7.4E3 | 6.0E3 | 6.6E3 | 1.1E4 | 4.6E4 | 3.3E4 | 46 | 12 | 43 | 12 | 0.47 |
| uL | ng/ml | 3.8E1 | 4.3E1 | 5.5E1 | 4.5E1 | 7.0E1 | 2.4E1 | 1.0E-9 | 2.1E1 | 4.0E2 | 9.2E1 | 111 | 9 | 90 | 9 | 0.53 |
| uO | ng/ml | 3.6E-1 | 4.5E-1 | 8.7E-1 | 6.5E-1 | 1.3E0 | 7.4E-1 | 1.0E-9 | 1.0E-9 | 9.3E0 | 1.7E0 | 111 | 9 | 90 | 9 | 0.47 |
| uM | ng/ml | 5.9E-1 | 3.2E-1 | 9.1E-1 | 6.6E-1 | 1.6E0 | 8.6E-1 | 1.0E-9 | 1.0E-9 | 1.3E1 | 2.5E0 | 111 | 9 | 90 | 9 | 0.40 |
| uI | ng/ml | 7.4E-2 | 5.9E-2 | 1.2E-1 | 8.2E-2 | 1.6E-1 | 5.0E-2 | 1.6E-2 | 3.4E-2 | 1.1E0 | 1.8E-1 | 110 | 9 | 89 | 9 | 0.47 |
| uN | ng/ml | 1.5E1 | 1.9E1 | 1.7E1 | 2.0E1 | 6.8E0 | 8.2E0 | 6.3E0 | 9.2E0 | 4.1E1 | 3.3E1 | 111 | 9 | 90 | 9 | 0.63 |
| uG | ng/ml | 1.9E1 | 2.2E1 | 2.3E1 | 3.7E1 | 1.6E1 | 3.9E1 | 1.2E0 | 6.5E0 | 8.9E1 | 1.3E2 | 111 | 9 | 90 | 9 | 0.60 |

Figure 1 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| uR | ng/ml | 2.4E0 | 3.3E0 | 3.4E0 | 3.4E0 | 6.1E0 | 2.0E0 | 7.3E-1 | 1.3E0 | 6.4E1 | 6.6E0 | 113 | 9 | 92 | 9 | 0.57 |
| uP | ng/ml | 2.3E0 | 2.5E0 | 2.6E0 | 2.8E0 | 1.2E0 | 1.3E0 | 1.1E0 | 9.3E-1 | 9.1E0 | 4.8E0 | 113 | 9 | 92 | 9 | 0.58 |
| uV | ng/ml | 2.3E-3 | 1.3E-3 | 1.5E-2 | 4.1E-3 | 3.2E-2 | 5.9E-3 | 1.0E-9 | 1.0E-9 | 2.0E-1 | 1.8E-2 | 113 | 9 | 92 | 9 | 0.42 |
| uT | ng/ml | 6.3E1 | 1.1E2 | 8.3E1 | 1.5E2 | 8.1E1 | 1.2E2 | 8.7E0 | 4.7E1 | 5.8E2 | 4.1E2 | 113 | 9 | 92 | 9 | 0.74 |
| uU | ng/ml | 1.7E0 | 2.7E0 | 2.0E0 | 4.0E0 | 1.2E0 | 6.0E0 | 5.2E-1 | 5.4E-1 | 7.0E0 | 2.0E1 | 113 | 9 | 92 | 9 | 0.55 |
| uW | ng/ml | 7.4E0 | 8.1E0 | 7.9E0 | 8.0E0 | 2.7E0 | 2.4E0 | 3.5E0 | 3.1E0 | 2.2E1 | 1.2E1 | 111 | 9 | 90 | 9 | 0.59 |
| vB | ng/ml | 2.8E0 | 3.2E0 | 3.0E0 | 3.4E0 | 1.7E0 | 1.6E0 | 5.9E-1 | 1.3E0 | 1.0E1 | 6.6E0 | 111 | 9 | 90 | 9 | 0.57 |
| vC | ng/ml | 1.0E-9 | 1.0E-9 | 3.7E-3 | 1.0E-9 | 2.4E-2 | 0.0E0 | 1.0E-9 | 1.0E-9 | 2.0E-1 | 1.0E-9 | 111 | 9 | 90 | 9 | 0.48 |
| uY | ng/ml | 6.8E-1 | 7.5E-1 | 1.1E0 | 1.3E0 | 1.0E0 | 1.4E0 | 6.8E-2 | 1.8E-1 | 4.9E0 | 4.4E0 | 111 | 9 | 90 | 9 | 0.48 |
| uZ | ng/ml | 5.5E-1 | 5.9E-1 | 7.4E-1 | 7.9E-1 | 8.7E-1 | 6.9E-1 | 4.7E-2 | 1.0E-1 | 7.2E0 | 2.0E0 | 111 | 9 | 90 | 9 | 0.52 |
| uX | ng/ml | 1.2E1 | 1.7E1 | 1.3E1 | 3.0E1 | 7.1E0 | 2.9E1 | 3.6E0 | 4.0E0 | 4.0E1 | 7.8E1 | 111 | 9 | 90 | 9 | 0.63 |
| vA | ng/ml | 7.0E-2 | 7.3E-2 | 8.2E-2 | 1.0E-1 | 5.2E-2 | 1.2E-1 | 1.7E-2 | 2.5E-2 | 3.0E-1 | 4.2E-1 | 111 | 9 | 90 | 9 | 0.48 |
| vH | ng/ml | 1.2E-1 | 1.1E-1 | 1.6E-1 | 3.5E-1 | 1.5E-1 | 5.9E-1 | 9.9E-3 | 4.7E-2 | 9.6E-1 | 1.9E0 | 113 | 9 | 92 | 9 | 0.54 |
| vI | ng/ml | 1.6E0 | 2.9E0 | 2.0E0 | 3.0E0 | 1.8E0 | 3.1E0 | 4.2E-3 | 1.7E-3 | 1.0E1 | 1.0E1 | 113 | 9 | 92 | 9 | 0.60 |
| vP | ng/ml | 4.4E2 | 3.1E2 | 5.5E2 | 4.7E2 | 4.7E2 | 4.5E2 | 4.0E1 | 1.5E2 | 2.4E3 | 1.6E3 | 113 | 9 | 92 | 9 | 0.46 |
| vT | ng/ml | 7.9E1 | 7.7E1 | 1.0E2 | 8.9E1 | 9.4E1 | 4.1E1 | 2.4E1 | 4.6E1 | 6.9E2 | 1.6E2 | 113 | 9 | 92 | 9 | 0.50 |
| vU | ng/ml | 1.0E-9 | 1.0E-9 | 2.1E1 | 2.5E1 | 3.3E1 | 4.5E1 | 1.0E-9 | 1.0E-9 | 1.3E2 | 1.1E2 | 113 | 9 | 92 | 9 | 0.50 |
| vQ | ng/ml | 3.5E2 | 3.2E2 | 3.7E2 | 3.7E2 | 1.4E2 | 1.7E2 | 6.7E1 | 1.9E2 | 8.4E2 | 6.0E2 | 113 | 9 | 92 | 9 | 0.49 |
| vO | ng/ml | 1.8E3 | 2.0E3 | 1.8E3 | 2.1E3 | 4.3E2 | 6.9E2 | 1.0E3 | 1.0E3 | 3.0E3 | 3.2E3 | 113 | 9 | 92 | 9 | 0.61 |
| vS | ng/ml | 1.3E3 | 1.4E3 | 1.2E3 | 1.5E3 | 4.6E2 | 3.1E2 | 1.0E-9 | 1.1E3 | 2.1E3 | 1.9E3 | 113 | 9 | 92 | 9 | 0.72 |
| vV | ng/ml | 9.5E2 | 9.4E2 | 1.5E3 | 2.4E4 | 1.8E3 | 7.0E4 | 2.1E1 | 2.3E2 | 1.1E4 | 2.1E5 | 113 | 9 | 92 | 9 | 0.47 |
| vW | ng/ml | 1.3E2 | 1.6E2 | 1.7E2 | 2.7E2 | 1.2E2 | 2.3E2 | 4.3E1 | 6.0E1 | 6.7E2 | 7.7E2 | 113 | 9 | 92 | 9 | 0.61 |
| pF | pg/ml | 4.5E-1 | 5.6E-1 | 1.0E0 | 1.0E0 | 5.7E0 | 9.4E-1 | 1.0E-9 | 1.8E-1 | 8.7E1 | 4.4E0 | 231 | 26 | 159 | 26 | 0.64 |
| pH | ng/ml | 8.8E0 | 1.2E1 | 9.8E0 | 1.3E1 | 6.4E0 | 1.1E1 | 3.0E0 | 3.3E0 | 4.2E1 | 4.7E1 | 46 | 12 | 43 | 12 | 0.62 |
| pI | ng/ml | 7.0E1 | 6.3E1 | 7.6E1 | 6.6E1 | 3.8E1 | 2.8E1 | 2.6E1 | 2.5E1 | 2.0E2 | 1.2E2 | 46 | 12 | 43 | 12 | 0.44 |
| pK | ng/ml | 4.6E-1 | 3.9E-1 | 5.1E-1 | 5.2E-1 | 2.6E-1 | 3.3E-1 | 1.7E-1 | 1.6E-1 | 1.6E0 | 1.4E0 | 46 | 12 | 43 | 12 | 0.49 |

Analyte panel data:

Unconstrained panels with 3 analytes, where 1.0E-10 >= 'model p-value' > 0. Contains 13,737 panels of 36,050,556 total panels evaluated. :
Ji[Ms(aA Aj Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ng(aA Ba Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Et(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Nq(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Lv(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Md(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lw Lx Ly Lz Ma Mb Mc Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ml(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lx Ly Lz Ma Mb Mc Me Mf Mg Mh Mi Mj Mk Mm Mn Mp Mq Mr Mt Mu Mv Mw Mx My Mz Na Nb Nc Nd Ne Nf Nh Ni Nj Nk Nl Nm Nn No Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Mw(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lw Lx Ly Lz Ma Mb Mc Me Mf Mg Mh Mi Mj Mk Mm Mn Mp Mq Mr Mt Mu Mv Mx My Mz Na Nb Nc Nd Ne Nf Nh Ni Nj Nk Nl Nm Nn No Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) My(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lw Lx Ly Lz Ma Mb Mc Me Mf Mg Mh Mi Mj Mk Mm Mn Mp Mq Mr Mt Mu Mv Mx Mz Na Nb Nc Nd Ne Nf Nh Ni Nj Nk Nl Nm Nn No Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Nb(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lw Lx Ly Lz Ma Mb Mc Me Mf Mg Mh Mi Mj Mk Mm Mn Mp Mq Mr Mt Mu Mv Mx Mz Na Nc Nd Ne Nf Nh Ni Nj Nk Nl Nm Nn No Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ne(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lw Lx Ly Lz Ma Mb Mc Me Mf Mg Mh Mi Mj Mk Mm Mn Mp Mq Mr Mt Mu Mv Mx Mz Na Nc Nd Nf Nh Ni Nj Nk Nl Nm Nn No Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ni(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lw Lx Ly

Om On Oz Pa Pc Pd Pe Pg) Jq(aA Jr Js Jt Lh Li Nw Oe Og Oh Oi Ok Om On Oz Pa Pc Pd Pe Pg) Jr(aA Js Jt Lh Li Nw Oe Og Oh Oi Ok Om On Oz Pa Pc Pd Pe Pg) Js(aA Jt Lh Li Nw Oe Og Oh Oi Ok Om On Oz Pa Pc Pd Pe Pg) Jt(aA Lh Li Nw Oe Og Oh Oi Ok Om On Oz Pa Pc Pd Pe Pg) Lh(aA Li Nw Oe Og Oh Oi Ok Om On Oz Pa Pc Pd Pe Pg) Li(aA Nw Oe Og Oh Oi Ok Om On Oz Pa Pc Pd Pe Pg) Nw(aA Oe Og Oh Oi Ok Om On Oz Pa Pc Pd Pe Pg) Oe(aA Og Oh Oi Ok Om On Oz Pa Pc Pd Pe Pg) Og(aA Oh Oi Ok Om On Oz Pa Pc Pd Pe Pg) Oh(aA Oi Ok Om On Oz Pa Pc Pd Pe Pg) Oi(aA Ok Om On Oz Pa Pc Pd Pe Pg) Ok(aA Om On Oz Pa Pc Pd Pe Pg) Om(aA On Oz Pa Pc Pd Pe Pg) On(aA Oz Pa Pc Pd Pe Pg) Oz(aA Pa Pc Pd Pe Pg) Pa(aA Pc Pd Pe Pg) Pc(aA Pd Pe Pg) Pd(aA Pe Pg) Pe(aA Pg) WmgP PgaA} Et{Ng(aA Aj An Ar Aw Ax BA Bc Bo cI Cp Cs cT Di dM Ef Fp Fr Hq Hr Hu Hv Hw Hx Id Ih Ii Ij Ik Il Im In Io Ip Iq Ir Is It Iu Iv Jg Jh Jj Jk Jl Jm Jn Jo Jp Jq Jr Js Jt Jy Ke Kq Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Ni Nj Nk Nl Nm Nn No Nq Nr Ns Nt Nu Nv Nw Nx Ny Oa Oe Of Og Oh Oi Ok Om On Or Ou Oy Oz Pa Pb Pc Pd Pe Pf Pg Po Pz Qa Qb Qc Qd Qe Uk Wm) Ms(aA Aj Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) In(aA Aj Fp Fr Hq Hr Hu Hv Hw Hx Ih Ii Ij Ik Il Im Io Ip Iq Ir It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Lj(aA Aj Fp Fr Hq Hr Hu Hv Hw Hx Ih Ii Ij Ik Il Im Io Ip Iq Ir Is It Iu Iv Jg Jh Jj Jk Jl Jm Jn Jo Jp Jq Jr Js Jt Lh Li Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Is(aA Aj Fp Fr Hq Hr Hu Hv Hw Hx Ih Ii Ij Ik Il Im Io Ip Iq Ir It Iu Iv Jg Jh Jj Jk Jl Jm Jn Jo Jp Jq Jr Js Jt Lh Li Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Jj(aA Fp Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Li Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Fp(aA Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Li Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Lv(aA Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Li Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nd(aA Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Li Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nh(aA Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Li Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Qa(aA Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Li Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qb Qc Qd Qe) aA(Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Li Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qb Qc Qd Qe) Nw(Fr Hq Hr Hu Hv Hw Hx Ih Ii Ik Il Im Io Ip Iq Ir It Iu Iv Jg Jh Jk Jl Jm Jn Jo Jp Jq Jr Js Jt Lh Li Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qb Qc Qd Qe) Lu(Fr Hq Hr Hu Hv Hw Hx Ih Ii Ij Ik Il Im Io Iq Ir It Iv Jg Jh Jk Jl Jm Jn Jo Jp Jq Jr Js Jt Lh Li Lw Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qb Qc Qd Qe) Qe(Fr Hq Hr Hu Hv Hw Hx Ih Ii Ik Il Im Io Iq It Iu Iv Jg Jh Jk Jl Jm Jn Jo Jp Jq Jr Js Jt Lh Li Lw Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qb Qc Qd) Jk(Aj Fr Hq Hr Hu Hv Hw Hx Ih Ii Ik Il Im Io Iq It Iu Jg Jh Jk Jm Jn Jo Jq Jr Js Jt Lh Li Lw Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nj Nk Nl Nm Nq Nr Ns Nt Nu Nv Nx Ny Oe Of Og Oh Oi Ok Om On Oy Oz Pa Pb Pc Pd Pe Pf Pg Po Pz Qc Qd) Im(Aj Fr Hq Hr Hu Hv Hw Hx Ih Ii Ik Il Io Iq Iu Jh Jk Jm Jn Jo Jp Jq Jr Js Jt Lh Li Lw Lx Ly Ma Mb Md Me Mf Mg Mh Mi Mk Ml Mm Mn Mp Mq Mr Mt Mu Mv Mw Mx My Mz Na Nb Nc Ne Nf Ni Nj Nk Nl Nm Nn Nq Nr Ns Nt Nu Nv Nx Ny Oe Of Og Oh Oi Ok On Oy Oz Pa Pb Pc Pd Pe Pf Pg Po Pz Qc Qd) Ni(Fr Hq Hr Hu Hv Hw Ih Ii Ik Il Io Jg Jh Jm Jn Jo Jp Jq Jr Js Jt Lh Li Lw Lx Mb Md Me Mf Mg Mh Mi Ml Mm Mp Mq Mr Mt Mu Mw Mx My Mz Nb Nc Ne Nj Nk Nl Nn No Nq Nr Ns Nt Nu Nv Nx Oe Of Og Oh Oi Ok Om On Oy Oz Pa Pb Pc Pd Pe Pf Pg Po Qb Qc Qd) Me(Fr Hq Hr Hu Hv Hw Ih Ii Ik Il Io Jm Jn Jo Jp Jq Jr Js Jt Lh Li Lw Lx Ly Mb Md Mf Mg Mh Mm Mp Mq Mr Mt Mu Mw Mx My Mz Na Nb Nc Ne Nj Nl Nq Ns Nt Nu Nx Oe Of Og Oh Ok On Oy Pb Pc Pe Pf Po Qb Qc Qd) Mq(Fr Hq Hr Hu Hw Ih Ii Ik Il Io Jh Jk Jm Jn Jo Jq Jr Jt Lh Li Lw Lx Mb Md Mf Mg Mh Mk Ml Mm Mr Mt Mw Mx My Mz Nb Nc Ne Nj Nk Nl Nq Ns Nt Nv Nx Oe Of Og Oh Oi Ok Oy Oz Pa Pb Pc Pe Pf Pg Qd) Jr(Fr Hq Hr Hu Hv Hw Ih Ii Ik Il Io Iq Jk Jm Jn Jo Jq Jt Lh Li Lw Lx Mb Md Mf Mg Mh Mk Mr Mt Mu Mw Mx My Mz Nb Nc Ne Nj Nk Nl Nq Ns Nt Nu Nv Nx Oe Of Og Oh Oi Ok Oy Pa Pb Pc Pe Pf Pg Pf Qd) Mt(Hq Hr Hu Hv Hw Ih Ii Ik Il Io Jk Jm Jn Jo Jq Jt Lh Li Lw Lx Mb Md Mf Mg Mh Mk Mm Mr Mw My Mz Nb Nc Ne Nj Nk Nl Nq Ns Nt Nv Oe Of Og Oh Oi Ok Oy Oz Pa Pb Pc Pe Pf Qd) Jo(Fr Hq Hu Hv Hw Ik Il Io Jm Jn Jq Js Jt Lh Li Lx Mb Mf Mh Ml Mr Mu Mw Mx My Mz Nb Nc Ne Nj Nl Nr Ns Nt Nu Nx Oe Oh Ok Om On Oy Pb Pc Pd Pe Pf Po Qb Qd) Pb(Fr Hq Hu Hv Hw Ik Il Io Jm Jn Jq Lh Li Lx Mb Mf Mh Ml Mr Mu Mx My Mz Nb Nc Ne Nj Nl Nr Ns Nt Nu Nx Oe Og Oh Ok On Oy Pc Pd Pe Pf Pg Po Qd) Oy(Fr Hu Ik Il Io Jg Jm Jn Jq Lh Li Lx Mf Mh Mr Mu Mv Mw Mx Mz Nb Nc Ne Nj Nl Nn Nq Nt Nu Nx Oh Ok Om On Pc Pd Pe Pf Pg Po Qb Qd Wm) Oh(Hq Hr Hu Hw Ih Ii Ik Il Io Jm Jq Jt Lh Li Lx Mb Md Mg Mh Mr My Mz Nb Nc Ne Nj Nl Nq Ns Nt Oe Of Og Oi Pa Pe Pf Qd) My(Fr Hu Ik Il Io Jg Jh Jm Jq Lh Li Lx Mh Mr Mu Mv Mw Nb Nc Ne Nj Nl Nq Nt Ok Om On Pc Pe Pf Po Qd Wm) Nj(Fr Hq Hu Ii Il Io Jm Jn Jq Lh Li Lx Mg Mh Mr Mu Mz Nb Nk Ns Oe Of Og Ok On Pe Pe Pf Qd) Pf(Aj Ch Co Hq Ii Ik Il Io Jq Lh Mh Mr Nb Nc Ne Nl Nq Ns Oe Og Pa Qd) Jq(Hq Ii Ik Il Io Jm Jt Li Lx Mb Md Mh Nb Nc Ne Nl Ns Om Qd) Lh(Hq Ir Hw Ii Il Jt Mb Md Mg Mk Mw Nc Ne Nl Nq Ns Of Og) Nl(Fr Hq Ii Io Li

Figure 1 Continued

Lx Mh Mr Mz Nb Ne Nk Ns Oe Og Qd) Hq(Fr Ik Il Jm Li Lx Mh Mr Mz Nb Ne Ne Pe Po Qd) Qd(Hw Ii Ik Il Io Jt Mh Nb Nc Ne Nq Ns Oe Og)
Lx(Ii Ik Il Io Md Mr Ne Nq Ns Oe Of Pa Pg) Li(Ii Ik Il Io Jt Nc Ne Nq Ns Oe Og Pa) Mr(Hw Ii Ik Il Mb Mk Nc Ne Ns Of) Ik(Ii Mg Mh Mz Ns
Oe Of Og) Mh(Ii Il Nb Nc Ne Ns) Ns(Nb Nc Ne On) Nt(Ii Jt Oe) Nc(Io Nb Nk) On(Ii Mw Of) Aj(bA Mm) Po Li NbNe} Nw{Ms(aA Fp Fr Hq Hr
Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf
Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu
Nv Nx Ny Oe Of Og Oh Oi Ok Om On Oy Oz Pa Pb Pc Pd Pe Pf Pg Po Pz Qa Qb Qc Qd Qe Wm) Nd(aA Fp Fr Hq Hr Hu Hv Hw Hx Ih Ii Ij Ik
Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm
Mn Mp Mq Mr Mt Mu Mv Mw Mx My Mz Na Nb Nc Ne Nf Ng Nh Ni Nj Nk Nl Nm Nn No Nq Nr Ns Nt Nu Nv Nx Ny Oe Of Og Oh Oi Ok
Om On Oy Oz Pa Pb Pc Pd Pe Pf Pg Po Pz Qa Qb Qc Qd Qe) In(aA Fp Fr Hq Hr Hu Hv Hw Hx Ih Ii Ij Ik Il Im Io Ip Iq Ir Is It Iu Iv Jg Jh Jj Jk Jl
Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My
Mz Na Nb Nc Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po
Pz Qa Qb Qc Qd Qe) Is(aA Fp Fr Hq Hr Hu Hv Hw Hx Ih Ii Ij Ik Il Im Io Ip Iq Ir It Iu Iv Jg Jh Jj Jk Jl Jm Jn Jo Jp Jq Jr Js Jt Lh Li Lj Lu Lv Lw
Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Ng Nh Ni Nj Nk Nl
Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Oy(aA Fp Fr Hq Hr
Hu Hv Hw Hx Ih Ii Ij Ik Il Im Io Ip Iq Ir It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh
Mi Mj Mk Ml Mm Mn Mp Mq Mr Mt Mu Mv Mw Mx My Mz Na Nb Nc Ne Nf Ng Nh Ni Nj Nk Nl Nm Nn No Nq Nr Ns Nt Nu Nv Nx Ny Oe
Of Og Oh Oi Ok Om On Oz Pa Pb Pc Pd Pe Pf Pg Po Pz Qa Qb Qc Qd Qe) Pb(aA Fp Fr Hq Hr Hu Hv Hw Hx Ih Ii Ij Ik Il Im Io Ip Iq Ir It Iu Iv
Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv
Mw Mx My Mz Na Nb Nc Ne Nf Ng Nh Ni Nj Nk Nl Nm Nn No Nq Nr Ns Nt Nu Nv Nx Ny Oe Of Og Oh Oi Ok Om On Oz Pa Pc Pd Pe Pf Pg
Po Pz Qa Qb Qc Qd Qe) aA(Fp Fr Hq Hr Hu Hv Hw Hx Ih Ii Ij Ik Il Im Io Ip Iq Ir It Iu Iv Jg Jh Jj Jk Jl Jm Jn Jo Jp Jq Jr Js Jt Lh Li Lj Lu Lv Lw
Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Ng Nh Ni Nj Nk Nl
Nm Nn No Nq Nr Ns Nt Nu Nv Nx Ny Oe Of Og Oh Oi Ok Om On Oz Pa Pc Pd Pe Pf Pg Po Pz Qa Qb Qc Qd Qe) Fp(Fr Hq Hr Hu Hv Hw Hx
Ih Ii Ik Il Im Io Ip Iq Ir It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml
Mm Mn Mp Mq Mr Mt Mu Mv Mw Mx My Mz Na Nb Nc Ne Nf Ng Nh Ni Nj Nk Nl Nm Nn No Nq Nr Ns Nt Nu Nv Nx Ny Oe Of Og Oh Oi
Ok Om On Oz Pa Pc Pd Pe Pf Pg Po Pz Qa Qb Qc Qd Qe) Lv(Fr Hq Hr Hu Hv Hw Hx Ih Ii Ik Il Im Io Ip Iq Ir It Iu Iv Jg Jh Jj Jk Jl Jm Jn Jo Jp
Jq Jr Js Jt Lh Li Lj Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc
Ne Nf Ng Nh Ni Nj Nk Nl Nm Nn No Nq Nr Ns Nt Nu Nv Nx Ny Oe Of Og Oh Oi Ok Om On Oz Pa Pc Pd Pe Pf Pg Po Pz Qa Qb Qc Qd Qe)
Jj(Fr Hq Hr Hu Hv Hw Hx Ih Ii Ik Il Im Io Ip Iq Ir It Iu Iv Jg Jh Jk Jl Jm Jn Jo Jp Jq Jr Js Jt Lh Li Lj Lu Lv Ly Lz Ma Mb Mc Md Me Mf Mg
Mh Mi Mj Mk Ml Mm Mn Mp Mq Mr Mt Mu Mv Mw Mx My Mz Na Nb Nc Ne Nf Ng Nh Ni Nj Nk Nl Nm Nn Nq Nr Ns Nt Nu Nv Nx Ny Oe
Of Og Oh Oi Ok Om On Oz Pa Pc Pd Pe Pf Pg Po Pz Qa Qb Qc Qd Qe) Im(Fr Hq Hr Hu Hv Hw Hx Ih Ii Ik Il Io Iq It Iu Jg Jh Jk Jl Jm Jn Jo Jp
Jq Jr Js Jt Lh Li Lj Lu Lw Lx Ly Lz Ma Mb Mc Md Me Mf Mg Mh Mi Mj Mk Ml Mm Mq Mr Mt Mu Mv Mw My Mz Na Nb Nc Ne Ng Nh Ni
Nj Nk Nl Nm Nn Nq Ns Nt Nu Nv Nx Ny Oe Of Og Oh Oi Ok On Oz Pa Pc Pd Pe Pf Pg Po Pz Qa Qb Qc Qd Qe) My(Fr Hq Hr Hu Hv Hw Hx
Ih Ii Ij Ik Il Io Jg Jh Jk Jl Jm Jn Jo Jp Jq Jr Js Jt Lh Li Lj Lu Lw Lx Lz Ma Mb Md Me Mf Mh Mi Ml Mm Mp Mq Mr Mt Mu Mv Mw Na Nb Nc
Ne Ng Nh Ni Nj Nk Nl Nm Nn No Nq Ns Nt Nu Nx Oe Og Oh Oi Ok Om On Oy Oz Pa Pb Pc Pd Pe Pf Pg Po Pz Qa Qb Qc Qd Qe) Me(Fr Hq Hr Hu Hv
Hw Hx Ih Ii Ik Il Io Jh Jk Jl Jm Jn Jo Jp Jq Jr Li Lj Lu Lw Lx Lz Ma Mb Md Mf Mh Mk Ml Mm Mq Mt Mu Mv Mw Nb Nc Ne Ng Nh Ni Nj
Nk Nl Nq Ns Nt Nv Nx Ny Oe Of Og Oh Ok Pa Pc Pe Pf Pg Po Pz Qa Qd Qe) Ng(Fr Hq Hr Hu Hv Hw Hx Ii Ik Il Io Jg Jh Jk Jl Jm Jn Jo Jp Jq
Jr Jt Lh Li Lj Lu Lw Lx Lz Ma Md Mg Mm Mq Mr Mt Mu Mv Mw Nb Nc Ne Nh Ni Nj Nk Nl Ns Nt Nu Nx Oh Ok Om On Pa Pc Pd Pe Pf Po
Qa Qd Qe) Ni(Hq Hr Hu Hv Hw Hx Ii Ik Il Io Jh Jk Jl Jm Jn Jo Jp Jq Jr Li Lj Lu Lx Mb Md Mf Mh Mm Mq Mr Mt Mu Mw Nb Nc Ne Nh Nj
Nl Nq Ns Nt Nv Nx Ny Oe Of Og Oh Ok Pa Pc Pe Pf Pg Po Pz Qa Qd Qe) Mq(Hq Hr Hu Hw Hx Ih Ii Ik Io Jh Jk Jl Jm Jn Jo Jq Jr Lj Lu Md Mt
Mu Mw Nc Ne Nh Nj Nk Nl Nq Ns Nv Nx Ny Oe Of Og Oh Ok Pa Pf Pg Po Qa Qe) Nh(Hq Hr Hu Hv Hw Hx Ih Ii Ik Il Jm Jo Jq Jr Lh Lj Lu
Md Mw Nb Nc Ne Nk Ns Nv Oe Of Og Ok Pa Pf Pg Qa Qd Qe) Qa(Hq Hr Hw Hx Ih Ii Ik Il Io It Jk Jo Lj Lu Mb Md Mj Mt Mw Nj Nk Nq Ns
Nv Nx Ny Oe Of Og Pa Pf Pg Po Qb) Md(Hv Hw Ii Ik Io Jl Jm Jn Jo Jq Jr Jt Lh Lj Lu Mb Mt Nb Ne Nj Nl Ns Nt Ok Om On Pa Pf Qe) Nj(Hq
Hr Hw Ii Jl Jq Jr Lj Lu Mt Mw Nb Nk Ns Nv Og Ok Pa Pf Pg Qd Qe) Ii(Hv Hw Ik Jl Jm Jo Jq Jr Jt Lh Lj Lu Mt Nt Ok Pf Po Qd Qe) Jl(Hq Hr
Hx Ik Jk Lj Lu Mk Mw Nb Nk Ns Nv Of Og Pa Pg Po) Lu(Hq Hu Hx Jk Jr Lj Mw Ns Nv Of Og Ok Pa Pf Pg Qe) Ik(Hq Hu Jk Jo Jq Lj Mw Ns
Nv Of Og Pg Qe) Qe(Hq Ih Io Jk Mw Nk Nq Ns Nv Oe Og Pa) Lj(Hq Io Lz Mt Nk Ns Oe Ok Pa) Lh(Hx Mw Nv Of Pg) Ok(Hq Hr Ns Nv Pa)
Mt(Mw Ns Nv Pa) Ns(Hq Jr) Nk(Nc Nl) Pf(Hq Pa) MrHx MwOn JnJs JrNv} Is{Ms(aA Fp Fr Hq Hr Hu Hv Hw Hx Ih Ii Ij Ik Il Im In Io Ip Iq Ir
It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt
Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa
Pb Pc Pd Pe Pf Pg Po Pz Qa Qb Qc Qd Qe) In(aA Fp Fr Hq Hr Hu Hv Hw Hx Ih Ii Ij Ik Il Im Io Ip Iq Ir It Iu Iv Jg Jh Jj Jk Jl Jm Jn Jo Jp Jq Jr Js
Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd
Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc
Qd Qe) Jj(aA Fp Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Li Lj Lu Lv Lw Lx Ly Lz Ma
Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No
Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Nd(aA Fp Fr Hq Hr Hw Ih Ii Ij Ik
Il Im Io It Iu Jg Jk Jl Jm Jo Jp Jq Lh Li Lj Lu Lv Lw Lx Me Mi Mm Mp Mq Mr Mt Mw Mz Nb Nc Ne Ng Ni Nk Nl No Ns Oe Og Oh Oi Ok
Om On Oy Pa Pb Pc Pe Pf Po Qa Qd Qe) Fp(aA Fr Hq Hr Hw Ih Ii Ik Il Im Io Iq It Iu Jg Jk Jl Jm Jo Jp Jq Lh Lu Lv Lw Lx Lz Md Me Mj Mk
Mm Mq Mr Mt My Mz Nb Nc Ne Ng Nh Ni Nk Nl Nq Ns Nt Oe Og Oi Ok On Oy Pa Pb Pc Pf Qb) Ni(aA Fr Hq Hr Hw Ih Ii Ik Il Im Io It Iu Jg
Jk Jl Jo Jp Lh Li Lj Lu Lv Lw Lx Md Me Mm Mq Mr Mt My Mz Nb Nc Ne Ng Nh Nj Nl Ns Nt Nx Og Oh Ok On Oy Pb Pc Pf Po Qa Qe)
Ok(aA Fr Hq Hr Hu Hw Hx Ih Ii Ik Il Im Io Iq It Iu Jk Jl Jm Jo Jr Jt Lj Lu Lv Lx Mb Md Me Mg Mq Mt My Nb Ng Nh Nj Nk Nm Nq Ns Nv Oe
Of Og Oi Oy Pa Pb Pc Pf) Lv(aA Hq Hw Ih Ii Il Im Io It Jk Jl Jo Jp Li Lj Lu Lx Me Mm Mq Mt My Mz Nb Ng Nh Nk Ns Og Oy Pb Pf) Ng(aA
Fr Hu Ik Jg Jl Jp Lh Li Lu Lx Mm Mq Mt Nb Nk Nt Om On Pf) Oy(Fr Jg Jl Lh Li Lu Lx Mq Mt Om On Pc Pf) Ii(Fr Jl Lh Li Lx Mq Mt On Pf)
Pb(Fr Jl Lh Li Lu Lx Mq Mt Pf) Og(Jl Lh Lu Mq Mt Nh On Pf) Jk(Fr Lh Li Lx Mt On Pf) Hq(Fr Li Lx Mq Pf) Nk(Jl Lj Nc Nh) Mq(aA Hw Ns)
My(Fr Lh On) Lj(aA Ih Lu) Lx(aA Me) Mt(Ih Me) Lh(Hr Hx) MkJl NeNh] Jj{Fp(aA Fr Hq Hu Hv Hw Ii Ij Ik Il Im In Ip Ir Iu Jg Jh Jk Jl Jm Jn
Jo Jp Jq Jr Js Jt Lh Li Lu Lv Lw Lx Lz Ma Me Mf Mg Mi Mm Mn Mp Mq Mr Ms Mt Mu Mv Mw Mx Mz Na Nb Nc Nd Ne Ng Nh Ni Nj Nk
Nl Nm Nn No Ns Nt Nu Nv Nx Ny Of Oh Ok Om On Pa Pb Pc Pd Pe Pf Pg Po Pz Qa Qb Qc Qd Qe) Qe(aA Fr Hq Hu Hv Hx Ih Ik Il Im In Io
Jg Jl Jm Jn Jo Jp Jq Jr Jt Lh Li Lj Lu Lv Lw Lx Ly Lz Ma Mb Me Mf Mg Mm Mq Mr Ms Mt Mu Mw My Mz Nb Nc Nd Ne Ng Nh Ni Nj Nk Nl

Figure 1 Continued

Nq Ns Nt Nu Nx Oe Og Oh Ok Om On Oy Pa Pb Pc Pd Pe Pf Po Qa Qb) Ok(aA Fr Hq Hr Hu Hw Hx Ik Il Im In Io Ip Jl Jm Jn Jq Jr Js Lh Li Lj
Lu Lv Lx Mb Md Me Mf Mh Mq Mr Ms Mt Mu Mw Mx My Mz Nb Nc Nd Ne Ng Nh Ni Nj Nl Nn Nq Nr Ns Nt Nu Nx Oe Oh On Oy Pa Pb Pc
Pd Pe Pf Pg Po Qa Qb Qd) Jl(Fr Hq Hu Hx Ik Il Im In Io Jg Jm Jn Jp Jq Jr Jt Lh Li Lj Lu Lv Lw Lx Lz Mb Me Mf Mg Mk Mq Ms Mt My Mz
Nb Nc Nd Ne Ng Nh Ni Nj Nk Nl Nq Ns Nt Nu Nx Og Oh Om On Oy Pb Pd Pf Po Qa Qd) Qa(aA Fr Hq Hu Hx Ih Ik Il Im In Io Jg Jp Jq Jr Lh
Li Lj Lu Lv Lw Lx Mb Me Mf Mg Mm Mq Mr Ms Mt Mz Nb Nc Nd Ne Nh Ni Nj Nk Nl Nq Nt Nu Nx Oh Om On Pb Pc Pd Pf Po Qb) Im(aA
Fr Hq Hu Ik Ih Io Jg Jo Jp Jq Jr Jt Lh Li Lj Lu Lv Lw Lx Ly Me Mf Mh Mm Mq Mr Ms Mt Mu Mz Nb Nc Nd Ne Nh Ni Nj Nl Nt Nu Nx Oh
Om On Pb Pd Pe Pf Po Qd) On(Ik Il In Jm Jr Li Lj Lu Lv Lx Mb Md Me Mf Mh Mq Ms Mt My Nc Nd Ne Ng Nh Ni Nj Nl Nq Ns Nt Nx Oh Oy
Pb Pf Po Qd) Mt(Ik Il Jm Jq Jr Lh Li Lj Lv Lx Me Mq Ms Nd Nh Ni Nt Nx Oh Pf Po Qd) Lh(Ik In Jm Li Lj Lv Lx Mq Ms Nd Nh Ni Nj Nl Nt
Nx Oh Pb Pf Qd) Lv(Ik Jp Li Lj Lx Nh Nt Nx Oh Pf Po Qd) Nx(Li Lj Lx Mq Nh Nt Oh Pf Po Qd) Ik(Fr Jp Li Lj Lx Mz Oh Qd) Nd(Fr Jp Li Lx
Oh Po Qd) Mq(Li Lj Lx Nt Oh Qd) Nh(Li Lx Oh Po Qd) Nt(Li Lj Lx Oh) Li(In Ni) WmPf LxMs} Ok{Ms(aA Fp Fr Hq Hr Hu Hw Hx Ih Ii Ij Ik
Il Im In Io Iq Jg Jl Jm Jn Jo Jp Jq Jr Js Jt Lh Li Lj Lu Lv Lw Lx Md Me Mf Mg Mh Mi Mm Mp Mq Mr Mt Mu Mw Mx My Mz Na Nb Nc Nd
Ne Ng Nh Ni Nj Nk Nl Nm Nn No Nq Nr Ns Nt Nu Nx Oe Of Og Oh Oi Om On Oy Oz Pa Pb Pc Pe Pf Po Qa Qb Qc Qd Qe) In(aA Fp Fr Hq
Hu Hw Ih Ik Il Im Io Jl Jm Jn Jo Jq Jr Js Lh Li Lj Lu Lv Lw Lx Me Mf Mh Mq Mr Mt Mu Mw Mx My Mz Nb Nc Nd Ne Ng Nh Ni Nj Nl Nn
Nq Ns Nt Nu Nx Oe Of Og Oh Om On Oy Pb Pc Pd Pe Pf Po Qa Qb Qd Qe) Fp(aA Fr Hq Hr Hu Hw Ih Ii Im Io It Iu Jk Jl Jm Jn Jo Jp Jq Jr Jt
Lh Lu Lv Lw Lz Md Me Mj Mm Mq Mr Mt My Mz Nb Nc Nd Ne Ng Nh Ni Nj Nl Nq Ns Nv Oe Of Og Oh Oi On Oy Oz Pa Pb Pc Pf Qa Qe)
Ng(aA Fr Hu Ik Im Jg Jl Jr Lh Li Lu Lv Lx Me Mq Mt Mu Nb Nd Nh Ni On Pb Pf Qa Qe) Nd(aA Fr Im Jl Jo Lh Lj Lv Lx Mq Pb Qa Qe) Lv(aA
Hq Im Jl Jo Lj Lu Nh Oy Pb Qa) Jo(Ik Jl Lh Lu Me Mq Nh Ni Qa Qe) Jl(Ii Im Lu Me Mk Ni Oy Pb) aA(Im Jr Lj Lx Me Mq Pb Qe) Pb(Lj Lu
Mq Nh Pf Qa) Oy(Fr Lh Lx On Pf) Ni(Im Lj Qa Qe) Lu(Im Lj) Ii(Qa Qe) MyOn} On{Ms(aA Fp Fr Hq Hr Hu Hv Hw Hx Ih Ii Ij Ik Il Im In Io
Ip Iq Ir It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mp Mq Mr Mt
Mu Mv Mw Mx My Mz Na Nb Nc Nd Ne Nf Ng Nh Ni Nj Nk Nl Nm Nn No Nq Ns Nt Nu Nv Nx Oe Of Og Oh Oi Om On Oy Oz Pa Pb Pc Pd Pe
Pf Pg Po Pz Qa Qb Qd Qe) Oy(Fp Fr Hr Hu Hw Ij Ik Il Im In Io Jg Jl Jm Jn Jp Jr Lh Li Lj Lu Lv Lw Lx Mb Md Me Mf Mh Ml Mq Mt Mu Mw
My Mz Nb Nc Nd Ne Ng Nh Ni Nj Nk Nl Nq Ns Nt Nu Nx Oh Om Pa Pb Pc Pd Pf Po Qa Qd Qe Wm) Ng(Fp Fr Hq Hu Hw Hx Ii Ik Il Im In Io
Jg Jh Jl Jm Jp Jq Jr Lh Li Lj Lu Lv Lw Lx Mb Me Mh Mk Mq Mt Mu My Nb Nd Ne Nh Ni Nj Nk Ns Nt Nx Oh Om Pb Pc Pd Pf Po Qa Qd Qe
Wm) Fp(aA Hq Ii In Jk Jo Lv Md Mk Mw My Nd Ni Nk Nq Ns Oe Og Pb) My(Ik Im In Jh Lv Lx Mb Md Me Mq Mt Nd Nh Ni Nj Pb Qe)
Nd(Im In Jl Lj Lv Mw Pb Qa Qe) In(Im Lj Me Mq Nh Nj Qa Qe) Lj(Lv Ni)} In{Qa(aA Fp Fr Hq Hu Hw Ik Il Im Iq Jg Jl Jm Jp Jq Jr Jt Lh Li Lj
Lu Lv Lw Lx Me Mh Mm Mq Mr Ms Mt Mz Nb Nd Ne Ng Nh Ni Nj Nk Nl Nq Ns Nt Nu Nx Og Oh Om Oy Pb Pc Pd Pe Pf Po Qb Qe) Fp(aA
Fr Im Jg Jl Jn Jo Jp Jq Jt Lh Li Lv Lw Lx Me Mm Mq Mr Mt Mu Mw Mz Nh Ni Nj Nt Nv Nx Oh Om Pb Pc Pe Pf Po Qd Qe) Qe(aA Ik Il Im Jl
Jq Jr Lh Li Lv Lw Lx Me Mq Mr Ms Mt Mz Nb Nd Ng Nh Ni Nj Nl Nt Nu Nx Oh Om Pb Pe Pf) Jl(Ik Im Li Lj Lv Lx Me Ms Mt Nd Nh Nj Nx)
Li(aA Im Jq Lh Lv Me Mq Mt Nd Nh Ni Nj) Im(aA Lh Lv Mq Mr Mt Nd Nh Nt) Lj(aA Lh Lv Mq Mt Om) Lx(aA Lv Mq Nh) Lh(Mt Nd Nh)
Pf(Vt Wm) PoaA MqMt NgJg} Fp{aA(Fr Hq Ih Il Im Ip Jg Jl Jm Jn Jp Jq Jr Lh Li Lv Lw Lx Ma Md Me Mf Mm Mn Mq Ms Mt Mw Mz Nc Nd
Ne Ng Nh Ni Nj Nk Nl Nm Nq Ns Nt Nx Oe Oh Om Oy Oz Pb Pc Pf Po Pz Qa Qd Qe) Jp(Lv Ms Nd Ng Ni Nk Pb) Fr(Ms Nd Ng Oy Pb) Lv(Im
Jl Mm Mt) Ms(Jl Lh Mt Om) Oy(Jg Lh Lx Om) Pb(Jl Lh Mt) NgJg NkJl} Ng{Jg(Fr Ik Im Jl Lh Li Lj Lv Lx Mq Ms Mt Nd Nh Ni Nt Nx Oh Om
Pf Po Qa Qd Qe) Fr(Ik Im Nd Qa Qe) Lh(Im Mt) Pf(Ba Wm) QeOm} Nd{Jl(Im Jp Li Lv Lx Ms Mt Qa Qe) Lh(Im Jp Lj Pb Qa Qe) Fr(Im Lj Qa
Qe) Qe(aA Jp Lx) aA(Im Lx) LvLi} Ms{Mt(Im Jl Jq Lh Lv Qe) Lh(aA Im Lx Qa Qe) Qe(aA Ni Om) Lx(aA Jl) Im(aA Jl)} Oy{Lh(Fr Im Jg Mt)
Lx(Jg Mt) JlOm VtPf} Lv{aA(Im Li Lj Lx Qe)}

Unconstrained panels with 3 analytes, where 1.0E-9 >= 'model p-value' > 1.0E-10. Contains 9,600 panels of 36,050,556 total panels evaluated. :
Et{Ng(aC Ad AF aH aJ aK Al aM aN AO Ap As aU aW aX Bb bF Bg bH bJ bL BN bR bS bV bZ cA Ch cK cN Co Cq Ct Cu Cv CW Cx Db Dc
Dd DE Dg dI dJ Dk Dl Dp Ed Ez Fa Fb Fw Fy Gl GP Hb Hc Hf Ic Iz Kc Kd Kf Kg Ki Kj Kk Kl Kn Ko Kp Kr Ks Kx Ky Kz Ld Ow Ph Pi Pj Pk
Qh Ql Qm Qn Qt Qv Qw Ra Rc Rf Rh Ri Sr St Tn Tr Tz Ua Ub Uc Ud Ue Uf Uh Ul Um Un Uo Ur Us Ut Uu Uv Vp Vt Tj) Nt(Fr Hq Hr Hu Hv
Hw Hx Ih Ij Ik Il Io Iq Ir It Iu Iv Jg Jh Jk Jm Jn Jp Jq Js Lh Li Lw Lx Ly Lz Ma Mb Mc Md Mf Mg Mh Mi Mj Mk Ml Mm Mn Mp Mr Mu Mv
Mw Mx Mz Na Nb Nc Ne Nf Nj Nk Nl Nm Nn No Nq Nr Ns Nu Nv Nx Ny Of Og Oi Ok Om On Oz Pa Pc Pd Pe Pf Pg Po Pz Qb Qc Qd)
Mz(Fr Hr Hu Hv Hw Hx Ih Ii Il Io Iq It Iu Iv Jg Jh Jk Jm Jn Jp Jq Js Jt Lh Li Lw Lx Ly Lz Ma Mb Mc Md Mf Mg Mh Mi Mj Mk Ml Mm Mn
Mp Mr Mu Mv Mw Mx My Na Nb Nc Ne Nf Nk Nm Nn No Nq Nr Ns Nu Nv Nx Ny Oe Of Og Oi Ok Om On Oz Pa Pc Pd Pe Pf Pg Po Pz Qb
Qc Qd) Nb(Aj Fr Hr Hu Hv Hw Hx Ih Ii Ij Ik Il Io Ip Iq Ir It Iu Iv Jg Jh Jk Jm Jn Jp Js Jt Lh Li Lw Lx Ly Lz Ma Mb Mc Md Mf Mg Mi Mj Mk
Ml Mm Mn Mp Mr Mu Mv Mw Mx Na Nf Nk Nm Nn No Nq Nr Nu Nv Nx Ny Oe Of Og Oi Ok Om On Oz Pa Pc Pd Pe Pg Po Pz Qb Qc)
Nc(Fr Hr Hu Hv Hw Hx Ih Ii Ij Ik Il Ip Iq Ir It Iu Iv Jg Jh Jk Jm Jn Jp Js Jt Lw Lx Ly Lz Ma Mb Mc Md Mf Mg Mi Mj Mk Ml Mm Mn Mp Mu
Mv Mw Mx Na Ne Nf Nj Nl Nm Nn No Nq Nr Nu Nv Nx Ny Oe Of Og Oi Ok Om On Oz Pa Pc Pd Pe Pg Po Pz Qb Qc) Ns(Fr Hq Hr Hu Hv
Hw Hx Ih Ii Ij Il Io Ip Iq Ir It Iu Iv Jg Jh Jk Jm Jn Jp Js Jt Lw Ly Lz Ma Mb Mc Md Mf Mg Mi Mj Mk Ml Mm Mn Mp Mu Mv Mw Mx My Na
Nf Nk Nm Nn No Nq Nr Nu Nv Nx Ny Oe Of Og Oi Ok Om Oy Oz Pa Pc Pd Pe Pg Po Pz Qb Qc) Mh(Fr Hr Hu Hv Hw Hx Ih Ii Io Ip Iq Ir It Iu
Iv Jg Jh Jk Jm Jn Jp Js Jt Lh Li Lw Lx Ly Lz Ma Mb Mc Md Mf Mg Mi Mj Mk Ml Mm Mn Mp Mr Mu Mv Mw Mx Na Nf Nk Nm Nn No Nq
Nr Nu Nv Nx Ny Oe Of Og Oi Ok Om On Oz Pa Pc Pd Pe Pg Po Pz Qb Qc) Ne(Fr Hr Hu Hv Hw Hx Ih Ii Ij Ik Il Io Ip Iq Ir It Iu Iv Jg Jh Jk Jm
Jn Jp Js Jt Lw Ly Lz Ma Mb Mc Md Mf Mg Mi Mj Mk Ml Mm Mn Mp Mu Mv Mw Mx Na Nf Nj Nk Nm Nn No Nq Nr Nu Nv Nx Ny Oe Of
Og Oi Ok Om On Oz Pa Pc Pd Pe Pg Po Pz Qb Qc) Mr(Aj Fr Hr Hu Hv Hx Ih Ij Io Ip Iq Ir It Iu Iv Jg Jh Jk Jm Jn Jp Jq Js Jt Kg Lh Li Lw Ly Lz
Ma Mc Md Mf Mg Mi Mj Ml Mm Mn Mp Mu Mv Mw Mx Na Nf Nk Nm Nn No Nq Nr Nu Nv Nx Ny Oe Og Oi Ok Om On Oz Pa Pc Pd Pe Pg
Po Pz Qb Qc Qd) Pf(Ap Ct Fr Hr Hu Hv Hw Hx Ih Ij Ip Iq Ir It Iu Iv Iz Jg Jh Jk Jm Jn Jp Js Jt Kg Li Lw Lx Ly Lz Ma Mb Mc Md Mf Mg Mi Mj
Mk Ml Mm Mn Mp Mu Mv Mw Mx Na Nf Nk Nm Nn No Nr Nu Nv Nx Ny Of Oi Ok Om On Oz Pc Pd Pe Pg Po Pz Qb Qc Wm) Ik(Fr Hr Hu
Hv Hw Hx Ih Ij Il Io Ip Iq Ir It Iu Iv Jg Jh Jk Jm Jn Jp Js Jt Lh Lw Ly Lz Ma Mb Mc Md Mf Mi Mj Mk Ml Mm Mn Mp Mu Mv Mw Mx Na Nf
Nj Nk Nl Nm Nn No Nq Nr Nu Nv Nx Ny Oi Ok Om On Oz Pa Pc Pd Pe Pg Po Pz Qb Qc) Hq(Hr Hu Hv Hw Hx Ih Ii Ij Io Ip Iq Ir It Iu Iv Jg Jh
Jk Jn Jp Js Jt Lw Ly Lz Ma Mb Mc Md Mf Mg Mi Mj Mk Ml Mm Mn Mp Mu Mv Mw Mx My Na Nf Nk Nm Nn No Nq Nr Nu Nv Nx Ny Oe
Of Og Oi Ok Om On Oy Oz Pa Pc Pd Pg Pz Qb Qc) Li(Aj Fr Hr Hu Hv Hw Hx Ih Ij Ip Iq Ir It Iu Iv Jg Jh Jk Jm Jn Jp Js Lh Lw Lx Ly Lz Ma
Mb Mc Md Mf Mg Mi Mj Mk Ml Mm Mn Mp Mu Mv Mw Mx Na Nf Nk Nm Nn No Nr Nu Nv Nx Ny Of Oi Ok Om On Oz Pc Pd Pe Pg Po Pz
Qb Qc Qd Wm) Nl(Hr Hu Hv Hw Hx Ih Ij Il Ip Iq Ir It Iu Iv Jg Jh Jk Jm Jn Jp Js Jt Lw Ly Lz Ma Mb Mc Md Mf Mg Mi Mj Mk Ml Mm Mn Mp
Mu Mv Mw Mx Na Nf Nj Nm Nn No Nq Nr Nu Nv Nx Ny Of Oi Ok Om On Oz Pa Pc Pd Pe Pg Po Pz Qb Qc) Qd(Aj Fr Hr Hu Hv Hx Ih Ij Ip
Iq Ir It Iu Iv Jg Jh Jk Jm Jn Jp Js Lh Lw Lx Ly Lz Ma Mb Mc Md Mf Mg Mi Mj Mk Ml Mm Mn Mp Mu Mv Mw Mx Na Nf Nk Nm Nn No Nr
Nu Nv Nx Ny Of Oi Ok Om On Oz Pa Pc Pd Pe Pg Po Pz Qb Qc) Io(Fr Hr Hu Hv Hw Hx Ih Ii Il Ip Iq Ir It Iu Iv Jg Jh Jk Jm Jn Jp Js Jt Lh Lw Ly

Figure 1 Continued

Js Jt Lh Li Lw Lx Lz Ma Mb Mf Mh Mj Mk Ml Mm Mr Mu Mv Mz Na Nb Nc Ne Nk Nl Nq Nt Nu Nx Ny Oe Of Og Oh Oi Pa Pc Pe Pf Pg Po Pz Qd) Hq(Fr Hr Hu Hv Hw Hx Ih Il Io Ir It Jm Jn Jo Jq Jt Lh Li Lw Lx Lz Ma Mb Mf Mh Mi Mk Mm Mp Mr Mu Mv Mx Mz Na Nb Nc Ne Nk Nl Nq Nt Nu Nx Ny Oc Of Og Oh Oi On Oz Pa Pc Pd Pe Pg Po Qd) Mq(Fr Hv Ij Il Ip Iq Ir It Iu Iv Jg Jp Js Jt Lh Li Lw Lx Ly Lz Ma Mb Mc Mf Mg Mh Mi Mj Mk Ml Mm Mn Mp Mr Mv Mx Mz Na Nb Nf Nm Nn No Nr Nt Nu Oi Om On Oz Pc Pd Pe Pz Qb Qc Qd) Pa(Fr Hr Hu Hv Hw Hx Ih Il Io Jh Jk Jm Jn Jo Jp Jq Jt Lh Li Lw Lx Lz Ma Mb Mf Mh Mk Mm Mr Mu Mv Mz Na Nb Nc Ne Nk Nl Nq Nr Nt Nu Nx Ny Oe Of Og Oh Oi On Pc Pd Pe Pg Po Qd) Jq(Fr Hr Hu Hv Hw Hx Ih Il Io Iq It Jh Jk Jm Jo Jt Li Lx Lz Ma Mb Mf Mh Mk Ml Mm Mr Mu Mv Nb Nc Ne Nf Nk Nl Nq Nt Nu Nx Ny Oe Of Og Oh Oi Om Pc Pe Pf Pg Po Qd) Pf(Hr Hu Hv Hw Hx Ih Il Io Jh Jk Jm Jn Jo Jt Lh Li Lw Lx Lz Mb Mf Mh Mk Mm Mr Mu Mv Mz Na Nb Nc Ne Nk Nl Nq Nt Nu Nx Ny Oe Of Og Oh Oi Oz Pc Pe Pg Po Pz Qd) Hw(Hr Hu Hv Hx Ih Il Io It Jh Jk Jm Jn Jo Jt Lh Li Lx Lz Ma Mb Mf Mh Mk Mr Mu Mv Nb Nc Ne Nk Nl Nq Nt Nx Ny Oe Of Og Oh Om Pc Pe Pg Po Qd) Ni(Fr Ih Ij Ip Iq Ir It Iu Iv Jg Js Jt Lh Lw Ly Lz Ma Mc Mg Mi Mj Mk Ml Mn Mp Mv Mx Mz Na Nf Nk Nm Nn No Nr Nu Oi Om On Oz Pd Qb Qc) Nk(Fr Hr Hu Hv Hx Ih Il Io Jh Jk Jm Jn Jo Jt Lh Li Lw Lx Lz Ma Mh Mk Mm Mr Mu Nb Nc Ne Nk Nq Nt Nu Nx Ny Oe Of Og Oh Oi Oz Pc Pe Pg Po Pz Qd) Og(Fr Hr Hu Hv Hx Il Io Jg Jm Jn Jo Jt Lh Li Lw Lx Lz Mb Mf Mh Mr Mu Nb Nc Ne Ng Nk Nq Nt Nu Nx Ny Oe Oh Om On Pc Pd Pe Pg Po Qd) Ng(Ih Ij Ip Iq Ir It Iu Iv Js Ly Mb Mc Mf Mh Mi Mj Mk Ml Mn Mp Mx Mz Na Nf Nm Nn No Nq Nr Ny Oe Of Oi Oz Pg Pz Qb Qc Wm) Io(Hr Hu Hv Hx Il Jg Jh Jk Jm Jn Jo Jt Lh Li Lw Lx Mb Mf Mk Mr Mu Mv Na Nb Nc Ne Nq Nt Nx Ny Oe Of Oh Pe Pg Po Qd) Me(Ij Ip Iq Ir It Iu Iv Jg Js Jt Lh Ly Mc Mg Mi Mj Mn Mp Mr Mx Mz Na Nf Nm Nn No Nr Nu Oi Om On Oz Pd Qb Qc) Pg(Fr Hr Hu Hv Hx Il Jm Jn Jo Jt Li Lx Lz Ma Mb Mf Mh Mi Mr Mu Nb Nc Ne Nk Nq Nt Nx Oe Oh Oi On Pe Po Qd) Qd(Hr Hu Hv Hx Ih Il Jk Jm Jo Jt Lh Lw Lx Lz Mb Mf Mh Mk Mu Nb Nc Ne Nk Nq Nt Nx Ny Oe Of Oh Oi Pc) Ne(Hr Hu Hv Hx Ih Il Jk Jm Jn Jo Jt Lh Li Lw Lx Lz Mk Mr Nb Nc Nk Nt Nx Oe Of Oh Oi Pc Pe Pz) Of(Fr Hr Hu Hv Hx Il Jg Jm Jn Jo Jt Li Lx Lz Ma Mr Mu My Nb Nc Nk Nt Oe Oh On Pc Pe Po) Nb(Hr Hu Hv Hx Il Jk Jm Jn Lh Li Lx Mf Mk Mr Mu Mv Nc Nk Nq Nt Ny Oe Oh Pe) Oe(Hr Hu Hv Hx Il Jk Jm Jn Jo Jt Lh Li Lx Nc Nt Nu Nx Ny Oh Pe Po) Nt(Hr Hu Hv Hx Jk Jm Jn Jo Jt Mk Mu Mv Nk Nq Nx Ny Oh Oi Pz) My(Ip Iq Ir It Iu Iv Ly Mc Mg Mj Mk Mn Mx Mz Nf No Nr Ny Wm) Hv(Hr Hu Hv Il It Jk Jm Jo Lx Mb Mu Mv Nc Nk Nq Nx Ny Oh) Lh(Hr Hu Il Jk Jo Mb Mh Mk Mu Mv Nc Nk Nq Nx Ny Po) Hx(Hu Il Jm Jn Jo Jt Lx Mf Mh Mi Ml Nc Nq Oh Pe) Hr(Il Jm Jn Jo Jt Li Lx Mf Mh Mr Nc Nq Oh Pe) Jk(Fr Il Jm Jo Jt Li Lx Mr Mu Nc Oh On Pe) Hu(Fr Il Jm Li Lx Mf Nc Nk Oh On Pe) Im(Ij Ip Ir Iv Mn Mp Mx Nf No Nr Om) Jn(Il Jm Lx Mb Mf Mh Nc Nk Nq Nx Ny) Il(Fr Jm Jo Jt Li Lx Nk Oh Pe) Nq(Fr Jm Jo Jt Li Lx Oh Pe) Jm(Mb Mk Mu Mv Nc Nk Ny) Pc(Lx Lz Mh Mk Nk Ny Po) Jt(Jo Mb Nc Nx Ny) Oh(Ih Mb Mh Nk Oi) Mr(Mh Mk Ny Po) Mu(Fr On Pc) Mv(Fr On Pc) Nk(Li Lx Mh) Ij(Fp Jj Lv) Jo(Mb Nx Ny) Wm(In Ji) qC(Db Mh) NoJj LxIh LzLi MbMc MkOn MlNy} Is{Lv(Fr Hr Hu Hv Hx Ij Ik Ip Iq Ir Iu Iv Jg Jh Jm Jn Jq Jr Js Jt Lh Lw Ly Lz Ma Mb Mc Md Mf Mg Mh Mi Mj Mk Ml Mn Mp Mr Mu Mv Mw Mx Na Nc Ne Nf Nj Nl Nm Nn No Nq Nr Nt Nu Nv Nx Ny Oe Of Oh Oi Om On Oz Pa Pc Pd Pe Pg Po Pz Qa Qb Qc Qd Qe) aA(Fr Hq Hr Hu Hv Hw Hx Ih Ii Ik Il Im Io Iq It Iu Jk Ji Jo Jp Jq Jr Lh Li Lu Lw Ma Mb Md Me Mf Mh Mk Mm Mn Mt My Mz Nb Nc Ne Nh Nj Nk Nl Nq Nr Ns Nt Nu Nx Oe Og Oh Oi Om On Oy Pb Pc Pd Pf Po Qa Qd Qe) Mq(Fr Hr Hu Hx Ih Ik Il Im Io Iq It Iu Jg Jk Jl Jm Jn Jo Jp Jq Jr Lh Li Lj Lu Lw Lx Lz Mb Md Me Mh Mj Mk Mm Mr Mt Mw My Mz Nb Nc Ne Nh Nj Nk Nl Nq Nt Nu Nv Nx Oe Of Oh Oi On Pc Pd Pf Qa Qb Qd Qe) Ok(Hv Ij Ip Ir Iv Jg Jh Jn Jp Jq Js Lh Li Lw Ly Lz Ma Mc Mf Mh Mi Mj Mk Ml Mm Mn Mp Mr Mu Mv Mw Mx Mz Na Nc Ne Nf Nl Nn No Nr Nt Nu Nx Ny Oh Om On Oz Pd Pe Pg Po Pz Qa Qb Qc Qd Qe) Ni(Hu Hv Hx Ij Ip Iq Ir Iv Jh Jm Jn Jq Jr Js Jt Ly Lz Ma Mb Mc Mf Mg Mh Mi Mj Mk Ml Mn Mp Mu Mv Mw Mx Na Nf Nk Nm Nn No Nq It Nu Nv Ny Oe Of Oi Om Oz Pa Pd Pc Pg Pz Qb Qc Qd) Mt(Fr Hq Hr Hu Hv Hw Hx Ik Il Im Io Iq It Iu Jl Jm Jo Jp Jq Jr Lh Li Lj Lu Lw Lx Mb Md Mk Mm Mr Mw My Mz Nb Nc Ne Nh Nj Nk Nq Ns Nt Nx Oe Of Oh Oi On Pa Pc Pe Pf Qa Qb Qe) Fp(Hu Hv Hx Ij Ip Ir Iv Jh Jn Jr Js Jt Li Lj Ly Ma Mb Mc Mf Mg Mh Mi Ml Mn Mp Mu Mv Mw Mx Na Nf Nj Nm Nn No Nr Nu Nv Nx Ny Of Oh Om Oz Pd Pc Pg Po Pz Qa Qc Qd Qe) Pf(Ct Fr Hr Hu Hw Ih Ik Il Im Io Iq It Iu Jl Jm Jo Jp Jq Lh Li Lj Lu Lw Lx Lz Md Me Mk Mm Mr My Mz Nb Nc Ne Nh Nj Nk Nl Nq Ns Nt Nx Oe Oh Oi On Pa Pc Pe Pg Qb Qe) Ng(Hq Hr Hw Hx Ih Ii Il Im Io Iq It Iu Jh Jq Jr Js Jt Lj Lw Ma Mb Me Mg Mp Mr Mu Mv Mw Mz Nc Ne Nh Nj Nl Nn No Ns Nu Nx Og Oh Oy Pb Pc Pd Pe Pg Po Qa Qd Qe Wm) Lx(Fr Hr Hu Hv Hw Hx Ih Ik Il Im Io Iq It Iu Jl Jm Jo Jp Jq Lh Lj Lu Lw Mb Md Mh Mj Mk Mm Mr My Mz Nb Nc Ne Nh Nj Nk Nl Nq Ns Nt Nx Oe Og Oi Pa Pc Pe Pg Qb) Nd(Hu Hv Hx Ip Iq Ir Iv Jh Jn Jr Js Jt Ly Lz Ma Mb Mc Md Mf Mg Mh Mj Mk Ml Mn Mu Mv Mx My Na Nf Nh Nj Nm Nn Nq Nr Nt Nu Nv Nx Ny Of Oz Pd Pg Pz Qb Qc) Og(Fr Hq Hu Hw Ih fi Ik fl Im Io Iq It Iu Jg Jk Jp Jq Jr Li Lj Lw Mb Me Mm Mr Mu Mz Nb Nc Ne Nj Nk Nl Nq Ns Nt Nu Nx Oh Om Oy Pb Pc Pd Pe Po Qa Qd Qe) Me(Fr Hq Hr Hw Ih li Ik Il Im Io Iq It Iu Jg Jk Jl Jo Jp Lh Li Lj Lu Lw Md Mm Mr My Mz Nb Ne Nh Nj Nk Nl Ns Nt Nu Nx Oe Oh On Oy Pb Pc Qe) Pb(Hq Hu Hw Ih Ik Il Im Io Iq It Jg Jk Jp Jq Lj Lw Mb Mm Mr Mz Nb Ne Nh Nj Nk Nl Ns Nt Nu Nx Oh Om On Oy Pc Pd Pe Po Qa Qe) Nh(Fr Hq Hr Hw Ih li Il Im Io It Iu Jk Jl Jo Jp Jq Lh Li Lj Lu Lw Mm Mr My Mz Nb Nc Nl Ns Nt Oe Oh Oi On Oy Pc Pe Qe) Il(Fr Hq Hw Ih li Im Io It Iu Jg Jk Jl Jp Jq Lh Li Lj Lu Lw Mm Mr Mz Nb Ne Nk Ns Nt Nx Oe Oh On Oy Pe Po Qa Qd Qe) Lj(Fr Hq Hr Hw li Ik Im Io Iq It Iu Jg Jk Jl Jp Jq Lh Lw Lz Mm Mz Nb Nc Ne Nj Nl Ns Nt Nx Oe Oi Om On Oy Pc Qb) Lu(Fr Hq Hr Hw Ih li Im Io Iq It Jk Jl Jo Jp Jq Lh Li Lw Md Mm My Mz Nb Nj Nk Nl Nq Ns Nt Nx Oe Oh Oi On Qe) Oy(Hq Hu Hw Ih Ik Im Io Iq It Jh Jp Jq Lw Mm Mr Mu Mv Mz Nb Ne Nj Nk Nn Nt Nu Nx Oh Pd Pc Pg Po Qa Qe) Lh(Hq Hw Ih Ik Im Io Iq It Iu Jo Li Mb Md Mk Mm Mw Mz Nb Nj Nk Nl Nq Ns Nv Ny Oe Of Pg Po) Jl(Hq Hr Hw Hx Ih Ik Im Io Iq It Iu Jk Jo Jp Li Mb My Mz Nb Ne Nj Nq Ns Nt Nx Oe Pa) Fr(Hr Hu Hw Ih Ik Im Io Iq Jo Md Mk Mu Mv Mw Mz Nj Nk Nl Nq Ns Nt Nv Oe Of) Li(Hr Hw Ih Im Io Iq It Iu Jo Jq Lw Mk My Mz Nb Nj Nk Nq Ns Nt Oe Oi) Im(Hq Hw Ih Ii Io Iq It Jk Jp Lw Mm Mr Nb Nj Nk Ns Nt Nx Oe On) Nk(Hw Ih Ik Jp Mr Nb Ne Nj Nl Nt Nu Oh On Pc Po Qa Qe) Hq(Hw Ih Ik Io Jg Jp Mr Mz Nb Nj Ns Nt Oh On Po Qe) Ii(Hu Ik Jg Jp Mm Mr Mz Nb Nj Nt Nx Oh Om Po Qe) On(Hw Ih Io Iq Jo Md Mk Mw Nj Nq Ns Oe Of) Nt(Hw Ih Io It Jk Jo My Nq Ns Oe Oi) Jp(Hw Ih Ik Io Iq Jk My Nj Nq Ns Oe) In(Aj aN bR Ch Ct dE dJ dN Vt Wm) Hw(Ih Ik Io Mr Mz Nb Ns Oh Qe) Jk(Hu Ik Jg Nb Nj Oh Qa Qe) Ns(Ih Lw Mm Nb Nu Pc) My(Jg Jh Nb Om Pc) Ih(Ik Mz Nb Qa Qe) Wm(Ji Jj Ms) Nc(Ne Nj Nl) Io(Mm Mz Nb) Mr(Hx Mk) Nj(Mz Nb) It(Jq Qa) Qb(Qa Qe) Jo(Ik Nx) AjaN BaCt NeNl JjbR JnJs} Ok{aA(Fr Hq Hr Hu Hv Hw Hx Ih Ii Ij Ik Il Io Ip Iq It Iu Jg Jh Jk Jl Jm Jn Jo Jp Jq Js Jt Lh Li Lu Lw Lz Ma Mb Mc Md Mf Mg Mh Mk Ml Mm Mn Mp Mr Mt Mu Mv Mw Mx My Mz Na Nb Nc Ne Nf Nh Ni Nj Nk Nl Nm Nn Nq Nr Ns Nt Nu Nv Nx Oe Of Og Oh Oi Om On Oy Oz Pa Pc Pd Pe Pf Pg Po Qa Qb Qc Qd) Lv(Fr Hr Hu Hv Hw Hx Ih Ii Ij Ik Il Io Ip Iq Ir It Iu Iv Jg Jh Jk Jm Jn Jp Jq Jr Js Jt Lh Li Lw Lx Ma Mc Md Me Mg Mh Mk Mm Mp Mq Mr Mt Mu Mw Mx My Mz Na Nb Nc Ne Ni Nj Nk Nl Nm Nn Nq Ns Nt Nu Nv Nx Oe Of Og Oh Oi On Oz Pa Pc Pd Pe Pf Pg Po Pz Qb Qc Qd Qe) Ng(Hq Hr Hv Hw Hx Ih Ii Ij Il Io Ip Iq It Iv Jh Jk Jm Jn Jo Jp Jq Jt Lj Lw Lz Ma Mb Mf Mg Mh Mi Mm Mp Mr Mv Mw Mx Mz Nc Ne Nj Nk Nl Nn Nq Nr Ns Nt Nu Nx Oe Oh Oi Om Oy Pa Pc Pd Pe Pg Po Qb Qc Qd) Fp(Hv Hx Ij Ik Il Ip Iq Ir Iv Jg Jh Js Li Lj Lx Ly Ma Mb Mc Mf Mg Mh Mi Mk Ml Mn Mp Mu Mv Mw Mx Na Nf Nl Nm Nn No Nr Nt Nu Nx Ny Om Pd Pe Pg Po Pz Qb Qc Qd) Jl(Hq Hr Hw Hx Ih Ik Il Io It Iu Jk Jm Jq Jr Jt Li Lj Lw Lx Mb Md Mf Mh Mq Mt Mw My Nb Nc Ne Nh Nj Nk Nl Nq Nr Ns Nv Oe Of Og Oh Oi Pa Pc Pf Pg Qa Qe) Nd(Hq Hr Hw Ii Ij Il Io Jg Jm Jn Jp Jq Jr Li Lu Lw Me Mh Mi Mp Mr Mt Mu Mw Mz Nb Nh Ni Nn Ns Oe Of Og Oh Oi On Oy Oz Pa Pc Pe Pf Po Qb Qc Qd) In(Hr Hv Hx Ii Ij Ip Iq Ir It Iu Iv Jg Jh Jk Jp Jt Ly Lz Ma Mb Mc Md Mg Mi Mj Mk Ml Mm Mn Mp Mv Na Nf Nk Nm No Nr Nv Ny Oi Oz Pa Pg Pz Qc Wm) Im(Fr Hq Hr Hw Ih Ii Ik Il Io Jk Jo Jq Jr Jt Lh Lj Lw Lx Me Mh Mq Mr Mt My Nb Nc Ne Nh Nj

Figure 1 Continued

Figure 1 Continued

Po Qd) Lh(aA Fr Li Lx Mm Mt Mz Ng Oh Oy Pf Qd) Fr(Jq Li Lx Mq Mr Mz Oh Oy Pb Qd) Im(Jq Li Lx Mm Mp Mr Mt Mz Ni Pe) Lx(Jq Mq Mr Oy Pb Pe Qd) Li(aA Jq Mq Ni) aA(Lj Po)} Ng{Jg(aA Hu Ij Il Jn Jp Jq Jr Js Lu Lw Me Mg Mp Mr Mu Mw My Mz Nb Ne Nj Nk Nl Nr Ns Nu Nv Oy Pb Pd Pe Qb) Pf(Ad bA Bc bR dJ dM Ef Jy Ke Ko Kq Lh Pj Rg Uf Uh Un Ur) Fr(Jl Jr Lh Li Lx Mq Mt Nh Nj Nt Nx Om Qd) Om(Im Jl Lh Li Lx Mq Mt Qa Qd) Lh(Jp Li Lx Nh Qa Qe) Mt(Im Jl Mq Qe) Lx(aA Jl Mq) Ni(Im Li Qe) Im(aA Jl) Kq(Il Mg) lkJp QeaA} aA{Im(Hq Ih Il Jl Jq Jr Lh Li Lj Lu Lw Lx Me Mf Mm Mq Mt Nh Ni Nj Nk Nq Ns Nx Pb Pf Qe) Lx(Ik Jl Jq Lj Lw Me Mf Mq My Mz Nh Ni Nj Nq Ns Nx Oy Pb Qa Qe) Qe(Ih Ik Il Jq Lj Lw Me Mq Mt Nh Ni Nj Nk Nq Nx Pb Pf) Lj(Ik Jg Jl Jq Lh Lw Mm Mq Mt Nh Ni Nj Nk Nx Om Pb) Ni(Li Qa) PoPb} Ni{Im(Fr Jl Jp Lh Li Lj Lu Lx Mm Mr Mt Nh Nj Oh Pf Qa Qe) Qe(Jl Jp Jq Lh Li Lj Lx Mt Nc Nh Nj Nl Nx Pb Pf) Qa(Jl Jp Jq Lh Li Lx Mt Nj Nx Pb Pf) Jl(Li Lj Lx Mt Nj) Li(Mt Nh Nj Pb) Lx(Nh Nj Pb) Lj(Jp Lh Mt) NjJp} Oy{Pf(Ad As bA dM Id Im Jl Jy Kd Ke Kn Kq Lh Mt Or Qa Qe Tv Ul Un Ur Us) Lx(Fr Ik Im Jl Lh Mq Nh Nx Om Qa Qe) Lh(Ik Jl Jp Li Mv Nh Om Qa Qe) Fr(Ik Im Jl Mq Nh Om Qa Qe) Jl(Im Jg Li Mt) Qa(Jg Om) Qe(Jg Om)} Jl{Im(Hq Lu Lx Mt Nh Nk Nx Og Pb) Lx(Me Mk My Nh Nk Pa Pb) Mt(Lj Me Mk My Nk Ns Pb) Nk(Li Lj Nh Qa Qe) Mk(Om Qe) Li(Pa Pb) NeNh HxQa LjPa PbPf} Lh{Pb(Im Li Lj Lx Mt Nh Pf Qa Qe) Im(Hq Ii Mt Nh) Mt(Lj My) MyJh NhLj IiQe} Pb{Mq(Fr Li Lx Mt Pf Qa) Pf(Mt Qa)} Nh{Ne(Im Qa Qe) Nk(Qa Qe)} Ji{Pf(Aj Co Ct Ha) IlUk} Ad{Aj(bA Pf)} Nk{Qa(Nc Nj)} DrIlKg LiwPnW aMbAgV

Unconstrained panels with 3 analytes, where 1.0E-8 >= 'model p-value' > 1.0E-9. Contains 18,905 panels of 36,050,556 total panels evaluated. : Is{Mz(Hr Hu Hv Hx Ik Im Ip Iq Ir It Iu Iv Jg Jh Jk Jm Jn Jo Jp Jq Jr Js Jt Lw Ly Lz Ma Mb Mc Md Mf Mg Mh Mi Mj Mk Ml Mm Mn Mp Mr Mu Mv Mw Mx My Na Nb Nc Ne Nf Nk Nl Nm Nn No Nq Nr Ns Nt Nu Nv Nx Ny Oe Of Oh Oi Om On Oz Pa Pc Pd Pe Pg Po Pz Qa Qb Qd Qe) Nb(Ct Fr Hr Hu Hv Hx Ij Ik Ip Iq Ir It Iu Iv Jg Jh Jm Jn Jo Jp Jq Jr Js Jt Lw Ly Lz Ma Mb Mc Md Mf Mg Mh Mi Mj Mk Ml Mm Mn Mp Mr Mu Mv Mw Mx Na Nc Ne Nf Nl Nm Nn No Nq Nr Nt Nu Nv Nx Ny Oe Of Oh Oi Om On Oz Pa Pc Pd Pe Pg Po Pz Qa Qb Qc Qd Qe) Io(Hr Hu Hv Hx Ih Ii Ik Ip Iq Ir It Iu Iv Jg Jh Jk Jm Jn Jo Jq Jr Js Jt Lw Ly Lz Ma Mb Mc Md Mf Mg Mh Mi Mj Mk Ml Mn Mp Mr Mu Mv Mw Mx My Na Nc Ne Nf Nj Nk Nl Nm Nn No Nq Nr Ns Nu Nv Nx Ny Oe Of Oh Oi Om Oz Pa Pc Pd Pe Pg Po Pz Qa Qb Qc Qd Qe) Jk(Hq Hr Hv Hw Hx Ih Ii Ij Ip Iq Ir It Iu Iv Jh Jm Jn Jo Jq Jr Js Jt jV Lw Ly Lz Ma Mb Mc Md Mf Mg Mh Mi Mj Mk Ml Mm Mn Mp Mr Mu Mv Mw Mx My Na Nc Ne Nf Ng Nk Nl Nm Nn No Nq Nr Ns Nu Nv Nx Ny Oe Of Oi Om Oy Oz Pa Pc Pd Pe Pg Po Pz Qb Qc Qd) Nj(Hr Hu Hv Hw Hx Ih Ik Il Ip Iq It Iu Iv Jg Jh Jm Jn Jo Jq Jr Js Jt Lw Ly Lz Ma Mb Mc Md Mf Mg Mh Mi Mj Mk Ml Mm Mp Mr Mu Mv Mw Mx My Na Ne Nf Nh Nl Nm Nn No Nq Nr Ns Nt Nu Nv Nx Oe Of Oh Oi Om Oz Pa Pc Pd Pe Pg Po Pz Qa Qb Qc Qd Qe) Ih(aN Ct Hr Hu Hv Hx Ii Ij Ip Iq Ir It Iu Iv Jg Jh Jm Jn Jo Jq Jr Js Jt Lw Ly Lz Ma Mb Mc Md Mf Mg Mh Mi Mj Mk Ml Mm Mn Mp Mr Mu Mv Mw Mx My Na Nc Ne Nf Nl Nm Nn No Nq Nr Nu Nv Nx Ny Oe Of Oh Oi Om Oz Pa Pc Pd Pe Pg Po Pz Qb Qc Qd) Jp(Fr Hr Hu Hv Hx Ij Ip Ir It Iu Iv Jg Jh Jm Jn Jo Jq Jr Js Jt Lh Li Lw Ly Lz Ma Mb Mc Md Mf Mg Mh Mi Mj Mk Ml Mm Mn Mp Mr Mu Mv Mw Mx Na Nc Ne Nf Nl Nm Nn No Nr Nt Nu Nv Nx Ny Of Oh Oi Om On Oz Pa Pc Pd Pe Pg Po Pz Qa Qb Qc Qd Qe) Ns(Hr Hu Hv Hx Ii Ij Ik Ip Iq Ir It Iu Iv Jg Jh Jm Jn Jo Jq Jr Js Jt Ly Lz Ma Mb Mc Md Mf Mg Mh Mi Mj Mk Ml Mn Mp Mr Mu Mv Mw Mx My Na Nc Ne Nf Nk Nl Nm Nn No Nq Nr Nv Nx Ny Oe Of Oh Oi Om Oy Oz Pa Pd Pe Pg Po Pz Qa Qb Qc Qd Qe) Hw(Hr Hu Hv Hx Ii Ij Ip Iq Ir It Iu Iv Jg Jh Jm Jn Jo Jq Jr Js Jt Lw Ly Lz Ma Mb Mc Md Mf Mg Mh Mi Mj Mk Ml Mm Mn Mp Mu Mv Mw Mx My Na Nc Ne Nf Nl Nm Nn No Nq Nr Nu Nv Nx Ny Oe Of Oi Om Oz Pa Pc Pd Pe Pg Po Pz Qa Qb Qc Qd) On(Fr Hr Hu Hv Hx Ij Ik Ip Ir It Iu Iv Jg Jh Jl Jm Jn Jq Jr Js Jt Lh Li Lw Lx Ly Lz Ma Mb Mc Mf Mg Mh Mi Mj Ml Mm Mn Mp Mr Mu Mv Mx Na Nc Ne Nf Nl Nm Nn No Nr Nt Nu Nv Nx Ny Oh Oi Om Oz Pa Pc Pd Pe Pg Po Pz Qa Qb Qc Qd Qe) Hq(Hr Hu Hv Hx Ii Ij Ip Iq Ir It Iu Iv Jh Jm Jn Jo Jq Jr Js Jt Lw Ly Lz Ma Mb Mc Md Mf Mg Mh Mi Mj Mk Ml Mm Mn Mp Mu Mv Mw Mx My Na Nc Ne Nf Nk Nl Nm Nn No Nq Nr Nu Nv Nx Ny Oe Of Oi Om Oz Pa Pc Pd Pe Pg Pz Qa Qb Qc Qd) Nt(Hr Hu Hv Hx Ij Ik Ip Iq Ir Iu Iv Jg Jh Jm Jn Jq Jr Js Jt Lh Lw Ly Lz Ma Mb Mc Md Mf Mg Mh Mi Mj Mk Ml Mm Mn Mp Mr Mu Mv Mw Mx Na Nc Nc Nf Nl Nm Nn No Nr Nu Nv Nx Ny Of Oh Om Oz Pa Pc Pd Pe Pg Po Pz Qa Qb Qc Qd Qe) Im(Hr Hu Hv Hx Ij Ik Ip Ir Iu Iv Jg Jh Jm Jn Jo Jq Jr Js Jt Ly Lz Ma Mb Mc Md Mf Mg Mh Mi Mj Mk Ml Mn Mp Mu Mv Mw Mx My Na Nc Ne Nf Nl Nm Nn No Nq Nr Nu Nv Ny Of Oh Oi Om Oz Pa Pc Pd Pe Pg Po Pz Qa Qb Qc Qd Qe) Jj(aC AD AF Aj Al aM AN AO Ap Ar As AW Ax BA Bb Bc Bg bL bM BN Bo bS bU bV cA cF Ch cI cJ CO Cp CQ Cs CT Cu CV Cw Cx Db Dc Dd DE Dg dH Di dJ DK Dl dM Dp Oa Ou Qm Uk Us Vt) Ii(Hr Hv Hx Ip Iq Ir It Iu Iv Jh Jm Jn Jo Jq Jr Js Jt Lw Ly Lz Ma Mb Mc Md Mf Mg Mh Mi Mj Mk Ml Mn Mp Mu Mv Mw Mx My Na Nc Ne Nf Nk Nl Nm Nn No Nq Nr Nu Nv Ny Oe Of Oi Oy Oz Pa Pb Pc Pd Pe Pg Pz Qa Qb Qc Qd) Li(Fr Hu Hv Hx Ij Ik Ip Ir Iv Jg Jh Jm Jn Jr Js Jt Lj Lx Ly Lz Ma Mb Mc Md Mf Mg Mh Mi Mj Ml Mm Mn Mp Mr Mu Mv Mw Mx Na Nc Ne Nf Nl Nm Nn No Nr Nu Nv Nx Ny Of Oh Om Oz Pa Pc Pd Pe Pg Po Pz Qa Qb Qc Qd Qe) Nk(Ct Hr Hu Hv Hx Ij Ip Iq Ir It Iu Iv Jg Jh Jm Jn Jo Jq Jr Js Jt Lw Ly Lz Ma Mb Mc Md Mf Mg Mh Mi Mj Mk Ml Mm Mn Mp Mu Mv Mw Mx My Na Nf Nm Nn No Nq Nr Nv Nx Ny Oe Of Oi Om Oz Pa Pc Pd Pg Pz Qb Qc Qd) Jl(Ct Fr Hu Hv Ij Ip Ir Iv Jg Jh Jm Jn Jq Jr Js Jt Lh Lw Ly Lz Ma Mc Md Mf Mg Mh Mi Mj Ml Mm Mn Mp Mr Mu Mv Mw Mx Na Nc Nf Nl Nm Nn No Nr Nu Nv Ny Of Oh Oi Om Oz Pc Pd Pe Pg Po Pz Qa Qb Qc Qd Qe) Fr(Hv Hx Ij Ip Ir It Iu Iv Jg Jh Jm Jn Jq Jr Js Jt Lh Lw Ly Lz Ma Mb Mc Mf Mg Mh Mi Mj Ml Mm Mn Mp Mr Mx Na Nc Ne Nf Nm Nn No Nr Nu Nx Ny Oh Oi Om Oz Pa Pc Pd Pe Pg Po Pz Qa Qb Qc Qd Qe) Il(Ct Hr Hu Hv Hx Ij Ik Ip Iq Ir Iv Jh Jm Jn Jo Jr Js Jt Ly Lz Ma Mb Mc Md Mf Mg Mh Mi Mj Mk Ml Mn Mp Mu Mv Mw Mx My Na Nc Nf Nl Nm Nn No Nq Nr Nu Nv Ny Of Oi Om Oz Pa Pc Pd Pg Pz Qb Qc) Lu(Hu Hv Hx Ij Ik Ip Ir Iu Iv Jg Jh Jm Jn Jr Js Jt Ly Lz Ma Mb Mc Mf Mg Mh Mi Mj Mk Ml Mn Mp Mr Mu Mv Mw Mx Na Nc Nc Nf Nm Nn No Nr Nu Nv Ny Of Om Oz Pa Pc Pd Pe Pg Po Pz Qa Qb Qc Qd) Nh(Hu Hv Hx Ij Ik Ip Iq Ir Iv Jg Jh Jm Jn Jr Js Jt Ly Lz Ma Mb Mc Md Mf Mg Mh Mi Mj Mk Ml Mn Mp Mu Mv Mw Mx Na Nf Nm Nn No Nq Nr Nu Nv Nx Ny Of Om Oz Pa Pd Pg Po Pz Qa Qb Qc Qd) Ik(Hr Hu Hv Hx Iq It Iu Jg Jm Jn Jq Jr Js Jt Lw Lz Ma Mb Md Mf Mg Mh Mi Mj Mk Mm Mp Mr Mu Mw My Na Nc Ne Nl Nm No Nq Nu Nv Nx Oe Of Oh Oi Om Pa Pc Pd Pe Po Pz Qa Qb Qc Qd Qe) In(aC AD aI Al aM An Ao Ar As aW Ax bA bB BC bL bM bN bS bU bV bW cA cC cF cH cI cJ cN CO cQ Cs Cu CV Cw cZ Dc dD De dF Di Dk dL dM Id Iz Ke Ko Ou Ua Uh Uk Ul Un) Lj(Hu Hv Hx Ij Ip Ir Iv Jh Jm Jn Jo Jr Js Jt Ly Ma Mb Mc Md Mf Mg Mh Mi Mj Mk Ml Mn Mp Mr Mu Mv Mw Mx My Na Nf Nm Nn No Nq Nr Nu Nv Ny Of Oh Oz Pa Pd Pe Pg Po Pz Qa Qc Qd Qe) Me(Hu Hv Hx Ij Ip Ir Iv Jh Jm Jn Jq Jr Js Jt Ly Lz Ma Mb Mc Mf Mg Mh Mi Mj Mk Ml Mn Mp Mu Mv Mw Mx Na Nc Nf Nm Nn No Nq Nr Nv Ny Of Oi Om Oz Pa Pd Pe Pg Po Pz Qa Qb Qc Qd) Mm(Hr Hu Hv Hx Ij Iq It Iu Jg Jm Jn Jo Jq Jr Js Jt Lw Lz Ma Mb Md Mf Mg Mh Mi Mk Ml Mr Mu Mw My Na Nc Ne Nl No Nq Nu Nv Nx Oe Of Oh Oi Om Pa Pc Pd Pe Pg Po Qa Qb Qd Qe) Lh(Hu Hv Ij Ip Ir Iv Jg Jh Jm Jn Jq Jr Js Jt Lw Ly Lz Ma Mc Mf Mg Mh Mi Mj Ml Mn Mp Mr Mu Mv Mx Na Nc Nc Nf Nm Nn No Nr Nu Nx Oh Oi Om Oz Pa Pc Pd Pe Pz Qa Qb Qc Qd Qe) Pb(Hr Hv Hx Ij Ip Ir Iu Iv Jh Jm Jn Jo Jr Js Jt Ly Lz Ma Mc Md Mf Mg Mh Mi Mj Mk Ml Mn Mp Mu Mv Mw Mx My Na Nc Nf Nm Nn No Nq Nr Nv Ny Oe Of Oi Oz Pa Pg Pz Qb Qc Qd) Qe(Hr Hu Hv Hx Iq Ir It Iu Jg Jm Jn Jo Jq Jr Js Jt Lw Lx Ly Lz Ma Mb Md Mf Mh Mi Mj Mk Mr Mu Mw My Na Nc Ne Nl Nq Nu Nv Nx Oe Of Oh Oi Om Pa Pc Pd Pe Po Pz Qa Qd) Oy(bA Hr Hv Hx Ij Ip Ir Iu Iv Jm Jn Jo Jr Js Jt Ly Lz Ma Mb Mc Md Mf Mg Mh Mi Mj Mk Ml Mn Mp Mw Mx My Na Nc Nf Nl Nm No Nq Nr Nv Ny Oe Of Oi Oz Pa Pz Qb Qc Qd Wm) Iq(Hr Hu Hv Hx It Iu Jg Jm Jn Jo Jq Jr Js Jt Lw Ma Mb Md Mf Mh Mi Mk Mp Mr Mu Mw My Na Nc Ne Nl No Nq Nu Nx Oe Of Oh Oi Om Pa Pc Pd Pe Pg Po Pz Qa

Figure 1 Continued

Qb Qd) Ng(Ad aN Aw Ba Bo bR dF Di dJ dM Hv Ij Ip Ir Iv Jm Jn Jo Kq Ly Lz Mc Md Mf Mh Mi Mj Mk Ml Mn Mx My Na Nf Nm Nq Nr Nv Ny Oe Of Oi Oz Pa Pz Qb Qc Qg Uf) Pf(Aj aN Ch Hv Hx Ij Ip Ir Iv Jg Jh Jn Jr Js Jt Ly Ma Mb Mc Mf Mg Mh Mi Mj Ml Mn Mp Mu Mv Mw Mx Na Nf Nm Nn No Nr Nu Nv Ny Of Om Oz Pd Po Pz Qa Qc Qd) Og(Hr Hv Hx Ij Ip Ir Iv Jh Jm Jn Jo Js Jt Ly Lz Ma Mc Md Mf Mg Mh Mi Mj Mk Ml Mn Mp Mv Mw Mx My Na Nf Nm Nn No Nr Nv Ny Oe Of Oi Oz Pa Pg Pz Qb Qc) Lx(Ij Ip Ir Iv Jg Jh Jn Jr Js Jt Ly Lz Ma Mc Mf Mg Mi Ml Mn Mp Mu Mv Mw Mx Na Nf Nm Nn No Nr Nu Nv Ny Of Oh Om Oz Pd Po Pz Qa Qc Qd) It(Hr Hu Hv Hx Ij Iu Jg Jm Jn Jo Jr Jt Lw Ma Mb Md Mf Mh Mk Mr Mu Mw Mx My Na Nc Ne Nl No Nq Nu Nx Oe Of Oh Oi Om Pc Pd Pe Pg Po Qd) Mt(Ij Ip Ir Iv Jg Jh Jn Js Jt Ly Lz Ma Mc Mf Mg Mh Mi Mj Ml Mn Mp Mu Mv Mx Na Nf Nl Nm Nn No Nr Nu Nv Ny Om Oz Pd Pg Po Pz Qc Qd) Jq(Ct Hr Hu Hx Ir Iu Iv Jg Jm Jo Jr Js Lw Ma Mb Md Mf Mh Mk Mr Mu Mw My Nc Ne Nl No Nq Nu Nx Oe Of Oh Oi Om Pa Pc Pd Pe Po Qa Qd) Nx(Hr Hu Hv Hx Iu Jg Jm Jn Jr Jt Lw Ma Mb Md Mf Mg Mh Mk Mr Mu Mw My Nc Ne Nl No Nq Nu Oe Of Oh Oi Om Pa Pc Pd Pe Po Qa Qb Qd) Mr(aA Hr Hu Iu Jg Jm Jo Jr Lw Lz Ma Mb Md Mf Mh Mj Mw My Nc Ne Nl Nq Nr Nu Nv Ny Oe Of Oh Oi Om Pa Pc Pd Pg Po Qa Qd) aA(Ij Ip Ir Iv Jg Jh Jm Jn Js Jt Ly Lz Mc Mg Mi Mj Ml Mp Mu Mv Mw Mx Na Nf Nm Nn No Nv Ny Of Oz Pa Pe Pg Pz Qb Qc) Mq(Ct Hv Ij Ip Ir Iv Jh Js Jt Ly Ma Mc Mf Mg Mi Ml Mn Mp Mu Mv Mx Na Nf Nm Nn No Nr Ny Om Oz Pa Pc Pg Po Pz Qc) Oh(Hr Hu Hv Hx Iu Jg Jm Jo Jr Lw Lz Mb Md Mf Mh Mk Mu My Nc Ne Nl Nq Nu Oe Of Oi Om Pa Pc Pd Pe Po Qa Qb Qd) Oe(Hr Hu Hx Iu Jg Jm Jo Jr Js Jt Lw Ma Mb Md Mh Mk Mp Mu Mw My Nc Ne Nl No Nq Nu Om Pc Pd Pe Po Qa Qd) My(Hr Hu Hx Iu Jm Jo Jr Lw Ma Mb Mh Mi Ml Mp Mu Mv Mw Nc Ne Nl Nn No Nq Nu Oi Pd Pe Pg Po Qa Qd) Lw(Hr Hu Hx Iu Jg Jm Jo Jr Ma Mb Md Mh Mk Mu Nc Ne Nl Nq Nu Of Oi Om Pa Pc Pd Pe Po Qa Qd) Jg(Hr Hu Hx Iu Jm Jo Jr Jt Mb Md Mg Mh Mk Mu Mv Mw Nc Ne Nl Nq Nu Of Oi Pa Pc Pe Qa Qd) Jo(Hr Hu Hv Hx Iu Jr Jt Ma Mb Mf Mh Mu Nc Ne Nl Nm Nq Nu Oi Om Pc Pd Pe Pg Po Qa Qd) Nl(Hr Hu Iu Jm Jr Ma Mb Md Mh Mk Mp Mu No Nq Nu Oi Om Pa Pc Pd Pe Po Qa Qb Qd) Nq(Hr Hu Iu Jm Jr Ma Mb Mp Mu Mw Nc Ne No Nu Oi Om Pc Pd Pe Po Qa Qd) Ne(aN Ct Hr Hu Hx Iu Jm Jr Mb Md No Nu Oi Om Pc Pd Pe Po Qa Qb Qd) Hr(Hu Hv Iu Jr Jt Mb Mf Mh Mu Nc Nf Nu Oi Om Pc Pd Pe Po Qa Qd) Pc(Hu Hx Iu Jm Jr Mb Md Mh Mk Mu Mw Nc Nu Oi Pe Po Qa Qd) Pe(Hu Hx Iu Jr Lz Mb Md Mh Mj Mk Nc Nr Of Oi Pa Qa Qd) Mb(Hv Iu Jr Jt Mc Md Mk Mu Nc Nu Oi Om Po Qa Qd) Ct(Ad aN bA Bc bR cT dF dJ dM Hu Ji Kq Ms Ni) Iu(Hu Hx Jr Md Mf Mh Nc Nu Oi Om Pd Po Qa Qd) Oi(Hu Hx Jr Mu Nc Nu Om Pd Po Qa Qd) Et(Al aN Ao Ap Bg cI Co Iz Uk Wm) Om(Hu Jr Md Mh Mk Mw Nu Of Qa Qd) Aj(Ad Ba bR dF dJ dM Ji Ms Ni) Po(Hu Hx Jm Md Mk Nc Of Pa Qb) Nu(Jm Jr Lz Md Mk Nc Qa Qd) Nc(Hu Hx Jr Mh Pd Qa Qd) Qa(Hu Hx Jm Jr Md Mk) Qd(Hx Jm Jr Qb) aN(bR Ch Ji Ms) Hu(Md Mk Of) Jr(Jn Js Md) Ji(Dd Uk) WmHx PaPd} Nw{Iv(Fr Hq Hr Hu Hv Hw Hx Ih Il Io Ip Iq Ir It Iu Jg Jh Jk Jm Jn Jo Jp Jq Jr Js Jt Lh Li Lw Lx Ly Lz Ma Mb Mc Mf Mg Mh Mi Mj Mk Ml Mm Mn Mp Mr Mt Mu Mv Mx Mz Na Nb Nc Ne Nf Nk Nl Nm Nn No Nq Nr Nt Nu Nv Nx Ny Oe Of Og Oh Oi Ok Om On Oz Pa Pc Pd Pe Pf Pg Po Pz Qb Qc Qd) Nm(Fr Hq Hr Hu Hv Hw Hx Ih Il Io Ip Iq Ir It Iu Jg Jh Jk Jm Jn Jo Jp Jq Jr Js Jt Lh Li Lw Lx Ly Lz Ma Mb Mc Mf Mg Mh Mi Mj Mk Ml Mm Mn Mp Mr Mu Mv Mx Mz Na Nb Nc Ne Nf Nk Nl Nn No Nq Nr Nt Nu Nv Nx Ny Oe Of Og Oh Oi Om On Oz Pa Pc Pd Pe Pf Pg Po Pz Qb Qc Qd) Iq(Fr Hq Hr Hu Hv Hw Hx Ih Ij Il Io Ip Ir It Iu Jg Jh Jk Jm Jn Jo Jp Js Jt Lh Li Lw Lx Ly Lz Ma Mb Mc Mf Mg Mh Mi Mj Mk Ml Mm Mn Mp Mr Mu Mv Mw Mx Mz Na Nb Nc Ne Nf Nk Nl Nn No Nq Nr Nt Nu Nv Nx Ny Oe Of Og Oh Oi Om On Oz Pa Pc Pd Pe Pf Pg Po Pz Qb Qc Qd) Ir(Fr Hr Hu Hv Hw Hx Ih Il Io Ip It Iu Jg Jh Jk Jm Jn Jo Jp Jq Jr Js Jt Lh Li Lw Lx Ly Lz Ma Mb Mc Mf Mg Mh Mi Mj Mk Ml Mm Mn Mp Mr Mu Mv Mx Mz Na Nb Nc Ne Nf Nk Nl Nn No Nq Nr Nt Nu Nv Nx Ny Oe Of Og Oh Oi Ok Om On Oz Pa Pc Pd Pe Pf Pg Po Pz Qb Qc Qd) Qb(Fr Hq Hr Hu Hv Hw Hx Ih Ij Il Io Ip It Iu Jg Jh Jk Jm Jn Jo Jp Jq Jr Js Jt Lh Li Lw Lx Ly Lz Ma Mb Mc Mf Mg Mh Mi Mj Mk Ml Mm Mn Mp Mr Mu Mv Mx Mz Na Nb Nc Ne Nf Nk Nl Nn No Nq Nr Nt Nu Nx Ny Oe Of Og Oh Oi Om On Oz Pa Pc Pd Pe Pf Pg Po Pz Qc Qd) Qc(Fr Hq Hr Hu Hv Hw Hx Ih Ij Il Io Ip It Iu Jg Jh Jk Jm Jn Jo Jp Jq Jr Js Jt Lh Li Lw Lx Ly Lz Ma Mb Mc Mf Mg Mh Mi Mj Mk Ml Mm Mn Mp Mr Mu Mv Mx Mz Na Nb Nc Ne Nf Nk Nl Nn No Nq Nr Nt Nu Nx Ny Oe Of Og Oh Oi Om On Oz Pa Pc Pd Pe Pf Pg Po Pz Qd) Jp(Fr Hq Hr Hu Hv Hw Hx Ih Ij Il Io Ip It Iu Jg Jh Jk Jm Jn Jo Jq Jr Js Jt Lh Li Lw Lx Ly Lz Ma Mb Mc Mf Mg Mh Mi Mj Mk Ml Mm Mn Mp Mr Mu Mv Mx Mz Na Nb Nc Ne Nf Nk Nl Nn No Nq Nr Nt Nu Nx Ny Oe Of Og Oh Oi Om On Oz Pc Pd Pe Pf Pg Po Pz Qd) Nr(Fr Hq Hr Hu Hv Hw Hx Ih Ij Il Io Ip It Iu Jg Jh Jk Jm Jn Jo Jq Jr Js Jt Lh Li Lw Lx Lz Ma Mb Mc Mf Mg Mh Mi Mj Mk Ml Mm Mp Mr Mu Mv Mw Mx Mz Na Nb Nc Ne Nk Nl Nn No Nq Nt Nu Nv Nx Ny Oe Of Og Oh Oi Om On Oz Pc Pd Pe Pf Pg Po Pz Qd) Mi(Fr Hr Hu Hv Hw Ih Il Io Ip It Iu Jg Jh Jk Jm Jn Jo Jq Jr Js Jt Lh Li Lw Lx Ly Lz Ma Mb Mc Mf Mg Mh Mj Mk Ml Mm Mn Mp Mr Mu Mv Mx Mz Na Nb Nc Ne Nf Nk Nl Nn No Nq Nt Nu Nv Nx Ny Oe Of Og Oh Oi Ok Om On Oz Pa Pc Pd Pe Pf Po Pz Qd) Ml(Fr Hq Hr Hu Hv Hw Ih Ij Il Io Ip It Iu Jg Jh Jk Jm Jn Jo Js Jt Lh Li Lw Lx Ly Lz Ma Mb Mc Mf Mg Mh Mj Mk Mm Mn Mp Mr Mu Mv Mw Mx Mz Na Nb Nc Ne Nf Nk Nl Nn No Nq Nt Nu Nv Nx Oe Of Og Oh Oi Om On Oz Pa Pc Pd Pe Pf Pg Po Pz Qd) Mx(Fr Hr Hu Hv Hw Hx Ih Il Io Ip It Iu Jg Jh Jk Jm Jn Jo Jq Jr Js Jt Lh Li Lw Lx Ly Lz Ma Mb Mc Mf Mg Mh Mj Mk Mm Mn Mp Mr Mu Mv Mz Na Nb Nc Ne Nf Nk Nl Nn No Nq Nt Nu Nx Ny Oe Of Og Oh Oi Om On Oz Pa Pc Pd Pe Pf Pg Po Pz Qd) Js(Fr Hq Hr Hu Hv Hw Hx Ih Ij Il Io Ip It Iu Jg Jh Jk Jm Jo Jq Jt Lh Li Lw Lx Ly Lz Ma Mb Mc Mf Mg Mh Mj Mk Mm Mn Mp Mr Mu Mv Mz Na Nb Nc Ne Nf Nk Nl Nn No Nq Nt Nu Nx Ny Oe Of Og Oh Oi Om On Oz Pa Pc Pd Pe Pf Pg Po Pz Qd) Mc(Fr Hq Hr Hu Hv Hw Hx Ih Il Io Ip It Iu Jg Jh Jk Jm Jn Jo Jq Jr Jt Lh Li Lw Lx Ly Lz Ma Mf Mg Mh Mj Mk Mm Mp Mr Mu Mv Mw Mz Na Nb Nc Ne Nk Nl Nn Nq Nt Nu Nv Nx Ny Oe Of Og Oh Oi Om On Oz Pa Pc Pd Pe Pf Pg Po Pz Qd) Mp(Fr Hr Hu Hv Hw Hx Ih Il Io Ip It Iu Jg Jh Jk Jm Jn Jo Jq Jr Jt Lh Li Lw Lx Ly Lz Ma Mb Mf Mg Mh Mj Mk Mm Mn Mr Mu Mv Mz Na Nb Nc Ne Nk Nl Nn Nq Nt Nu Nv Nx Ny Oe Of Og Oh Oi Om On Oz Pa Pc Pd Pe Pf Pg Po Pz Qd) Ip(Fr Hq Hr Hu Hv Hw Hx Ih Il Io It Iu Jg Jh Jk Jm Jn Jo Jq Jr Jt Lh Li Lw Lx Lz Ma Mb Mf Mg Mh Mk Mm Mr Mu Mv Mw Mz Na Nb Nc Ne Nk Nl Nn Nq Nt Nu Nv Nx Ny Oe Of Og Oh Oi Ok Om On Oz Pa Pc Pd Pe Pf Pg Po Pz Qd) No(Fr Hq Hr Hu Hv Hw Hx Ih Ii Il Io It Jg Jh Jk Jm Jn Jo Jq Jr Jt Lh Li Lw Lx Lz Ma Mb Mf Mh Mk Mm Mr Mt Mu Mv Mw Mz Na Nb Nc Ne Nk Nl Nq Nt Nu Nv Nx Ny Oe Of Og Oh Oi Ok Om On Oz Pa Pc Pd Pe Pf Pg Po Pz Qd) Ly(Fr Hq Hr Hu Hv Hw Hx Ih Il Io It Iu Jg Jh Jk Jm Jn Jo Jq Jr Jt Lh Li Lw Lx Lz Ma Mb Mf Mh Mk Mm Mr Mt Mu Mv Mw Mz Na Nb Nc Ne Nk Nl Nq Nt Nu Nv Nx Ny Oe Of Og Oh Oi Ok Om On Oz Pa Pc Pd Pe Pf Pg Po Pz Qd) Mn(Fr Hq Hr Hu Hv Hw Hx Ih Ii Il Io It Jg Jh Jk Jm Jn Jo Jq Jr Jt Lh Li Lw Lx Lz Ma Mb Mf Mh Mk Mm Mr Mt Mu Mv Mw Mz Na Nb Nc Nc Nk Nl Nq Nt Nu Nv Nx Ny Oe Of Og Oh Oi Ok Om On Oz Pa Pc Pd Pe Pf Pg Po Pz Qd) Mg(Fr Hq Hr Hu Hv Hw Hx Ih Il Io It Iu Jg Jh Jk Jm Jn Jo Jq Jr Jt Lh Li Lw Lx Lz Ma Mb Mf Mh Mk Mm Mr Mu Mv Mw Mz Na Nb Nc Ne Nk Nl Nn Nq Nt Nu Nv Nx Ny Oe Of Og Oh Oi Om On Oz Pa Pc Pd Pe Pf Pg Po Pz Qd) Ij(Fr Hq Hr Hu Hv Hw Hx Ih Ii Il Io It Jg Jh Jk Jl Jm Jn Jo Jq Jr Jt Lh Li Lw Lx Lz Ma Mb Mf Mh Mk Mm Mr Mt Mu Mv Mz Na Nb Nc Ne Nk Nl Nq Nt Nu Nv Nx Ny Oe Of Og Oh Oi Ok On Oz Pa Pc Pd Pe Pf Pg Po Pz Qd) Nn(Fr Hq Hr Hu Hv Hw Hx Ih Il Io It Iu Jg Jh Jk Jm Jn Jo Jq Jr Jt Lh Li Lw Lx Lz Ma Mb Mf Mh Mk Mm Mr Mu Mv Mz Na Nb Nc Ne Nk Nl Nq Nt Nu Nv Nx Ny Oe Of Og Oh Oi Om On Oz Pa Pc Pd Pe Pf Pg Po Pz Qd) Mj(Fr Hq Hr Hu Hv Hw Hx Ih Ii Il Io It Jg Jh Jk Jm Jn Jo Jq Jt Lh Li Lw Lx Lz Ma Mb Mf Mh Mk Mm Mr Mu Mv Mw Mz Na Nb Nc Ne Nk Nl Nq Nt Nu Nv Nx Ny Oe Of Og Oh Oi Om On Oz Pa Pc Pd Pe Pf Pg Po Pz Qd) Nf(Fr Hq Hr Hu Hv Hw Hx Ih Il Io It Jg Jh Jk Jm Jn Jo Jr Jt Lh Li Lw Lx Lz Ma Mb Mf Mh Mk Mm Mr Mt Mu Mv Mw Mz Na Nb Nc Ne Nk Nl Nq Nt Nu Nv Nx Ny Oe Of Og Oh Oi Om On Oz Pa Pc Pd Pe Pf Pg Po Pz Qd) Iu(Fr Hq Hr Hu Hv Hw Hx Ih Il Io It Jg Jh Jk Jm Jn Jo Jq Jt Lh Li Lw Lx Lz Ma Mb Mf Mh Mk Mm Mr Mu Mv Mw Mz Na Nb Nc Ne Nk Nl Nq Nt Nu Nv Nx Ny Oe Of Og Oh Oi Om On Oz Pa Pc Pd Pe Pf Pg Po Pz Qd) Om(Fr Hq Hr Hu Hv Hx Ih Il Io It Jg Jh Jk

Figure 1 Continued

Jm Jn Jo Jr Jt Lh Li Lw Lx Lz Ma Mb Mf Mh Mk Mm Mr Mt Mu Mv Mz Na Nb Nc Ne Nk Nl Nq Nt Nu Nx Ny Oe Of Oh Oi On Oz Pa Pc Pd Pe Pf Pg Po Pz Qd) Jg(Fr Hq Hr Hu Hv Hw Hx Ih Il It Jh Jk Jm Jn Jo Jq Jr Jt Lh Li Lw Lx Lz Ma Mb Mf Mh Mk Mm Mr Mu Mv Mz Na Nb Nc Ne Nk Nl Nq Nt Nu Nx Ny Oe Of Oh Oi On Oz Pa Pc Pd Pe Pf Pg Po Pz Qd) Oz(Fr Hr Hu Hv Hw Hx Ih Il Io It Jh Jk Jm Jn Jo Jq Jr Jt Lh Li Lw Lx Lz Ma Mb Mf Mh Mk Mm Mr Mu Mv Mz Na Nb Nc Ne Nk Nq Nt Nu Nx Ny Oe Of Og Oh Oi On Pa Pc Pd Pe Pg Po Pz Qd) Pd(Fr Hr Hu Hv Hw Hx Ih Il Io It Jh Jk Jm Jn Jo Jq Jr Jt Lh Li Lw Lx Lz Ma Mb Mf Mh Mk Mm Mr Mu Mv Mz Na Nb Nc Ne Nk Nl Nq Nt Nu Nx Ny Oe Of Oh Oi On Pc Pe Pf Pg Po Pz Qd) Mz(Fr Hr Hu Hv Hw Hx Ih Il Io It Jh Jk Jm Jn Jo Jq Jt Lh Li Lw Lx Lz Ma Mb Mf Mh Mk Mm Mr Mu Mv Na Nb Nc Ne Nk Nl Nq Nt Nu Nx Ny Oe Of Og Oh Oi On Pc Pe Pg Po Pz Qd) Na(Fr Hr Hu Hv Hw Hx Ih Il It Jh Jk Jm Jn Jo Jq Jt Lh Li Lw Lx Lz Ma Mb Mf Mh Mk Mm Mr Mu Mv Nb Nc Ne Nk Nl Nq Nt Nu Nx Ny Oe Of Og Oh Oi On Pc Pe Pg Po Pz Qd) It(Fr Hr Hu Hx Ih Il Io Jh Jk Jm Jn Jo Jt Lh Li Lw Lx Lz Ma Mb Mf Mh Mk Mm Mr Mu Mv Nb Nc Ne Nk Nl Nq Nt Nu Nx Ny Oe Of Og Oh Oi On Pa Pc Pe Pf Pg Po Pz Qd) Pz(Fr Hq Hr Hu Hv Hw Hx Ih Il Io Jh Jk Jm Jn Jo Jq Jt Lh Li Lw Lx Lz Ma Mb Mf Mh Mk Mm Mr Mu Mv Nb Nc Nk Nq Nu Nx Ny Oe Of Og Oh Oi On Pa Pc Pe Pg Po Qd) Mm(Fr Hr Hu Hv Hw Hx Ih Il Io Jh Jk Jm Jn Jo Jt Lh Li Lw Lx Lz Ma Mb Mf Mh Mk Mr Mu Mv Nb Nc Ne Nk Nq Nt Nu Nx Ny Oe Of Og Oh Oi On Pc Pe Pg Po Qd) Nu(Fr Hr Hu Hv Hw Hx Ih Il Io Jh Jk Jm Jn Jo Jt Lh Li Lw Lx Lz Ma Mb Mf Mh Mk Mr Mu Mv Nb Nc Ne Nk Nl Nq Nt Nx Ny Of Oh Oi On Pc Pe Pg Po Qd) Jh(Fr Hq Hr Hu Hv Hx Ih Il Jk Jm Jn Jo Jt Lh Li Lw Lx Lz Ma Mb Mf Mh Mk Mr Mu Mv Nb Nc Ne Nk Nq Nt Nx Ny Oe Of Og Oh Oi On Pc Pe Pg Po Qd) Ma(Fr Hr Hu Hv Hx Ih Il Io Jk Jm Jn Jo Jt Lh Li Lw Lx Lz Mb Mf Mh Mk Mr Mu Mv Nb Nc Ne Nk Nq Nt Nx Ny Oe Og Oh Oi On Pc Pe Pf Po Qd) Lw(Fr Hr Hu Hv Hw Hx Ih Il Jk Jm Jn Jo Jq Jt Lh Li Lx Lz Mb Mf Mh Mk Mr Mu Mv Nb Nc Nk Nq Nt Nx Ny Oe Of Oh Oi On Pc Pe Pg Po) On(Fr Hr Hv Hw Hx Ih Il Io Jm Jn Jo Jq Jr Jt Lh Li Lx Lz Mb Mf Mh Mr Nb Nc Ne Nk Nl Nq Nt Nx Ny Oe Oh Oi Ok Pc Pe Pf Po Qd) Ih(Fr Hr Hu Hv Hx Il Io Jk Jm Jn Jo Jt Lh Li Lz Mb Mf Mh Mk Mr Mu Mv Nb Nc Nk Nq Nt Nx Ny Oe Of Og Oi Pc Pe Pg Po) Oi(Fr Hr Hu Hv Hw Hx Il Io Jk Jm Jn Jo Jt Lh Li Lx Lz Mb Mf Mh Mr Mu Mv Nb Nc Nk Nq Nx Ny Oe Of Og Pc Pe Po) Mv(Hr Hu Hx Il Jk Jn Jo Jt Li Lx Lz Mb Mf Mh Mk Mr Mu Nc Ne Nk Nl Nq Nv Nx Ny Oe Of Og Oh Pe Pg Po Qd) Fr(Hr Hv Hw Hx Io Jm Jn Jo Jt Lh Li Lx Lz Mb Mf Mh Mk Mr Nb Nc Ne Nk Nt Nx Ny Oe Oh Pc Pe Pf Po Qd) Pc(Hr Hv Hx Il Io Jk Jm Jn Jo Jt Lh Li Lx Lz Mb Mf Mh Mk Mr Nb Nc Nk Nq Nt Nx Ny Oe Oh Pe Pg Po) Lz(Hr Hu Hv Hx Il Io Jk Jm Jn Jo Jt Lh Lx Mb Mf Mh Mk Mr Mu Nb Nc Nk Nq Nt Nx Ny Oe Oh Po) Mk(Hr Hu Hv Hx Il Jk Jn Jo Jt Li Lx Mb Mf Mh Mu Mw Nc Nk Nq Nv Nx Ny Oe Of Og Oh Pg Po) Po(Hr Hu Hv Hx Il Jk Jm Jn Jo Jt Li Lx Mb Mf Mh Mu Nb Nc Ne Nk Nq Nt Nx Ny Oh Qd) Mf(Hv Il Jk Jm Jo Jt Lh Li Lx Mb Mh Mr Mu Nc Ne Nk Nl Nq Nt Nx Ny Oe Of Oh Pe) Mb(Hr Hu Hx Il Jk Li Lx Mh Mr Mu Nb Nc Ne Nk Nl Nq Nt Nx Ny Oe Of Pe) Mh(Hu Hv Il Io Jk Jm Jo Jt Li Lx Mu Nb Nc Ne Nq Nt Nx Ny Oe Of) Mr(Hu Hv Il Jm Jn Jo Jt Lh Li Lx Mu Nc Nk Nq Nt Nx Oe Oh Pe Qd) Mu(Hr Hu Hx Il Jn Jo Jt Li Lx Nc Ne Nk Nq Nx Ny Oe Oh Pe) Nx(Hr Hu Hx Il Jk Jm Li Lx Nb Nc Nk Nq Nv Ny Of Oh Pe) Ny(Hr Hu Hx Il Jk Li Lx Mw Nc Ne Nk Nq Nv Of Oh Pg) qC(aN aZ Ba Ch dB dE Gl Hu Lj Me oE qA Qy Wm) Li(Hv Hx Jm Jn Jo Jt Lh Lx Nc Nt Oh Pe Qd) Pe(Hu Hv Jm Jn Jo Jt Lh Nc Nt Oh Qd) Jk(Hq Hr Hu Hx Jn Nk Nq Of Og Pg) Jt(Hu Hv Jm Jn Lh Lx Nb Nk Oh) Nq(Hu Il Nc Ne Nk Nl Oe Of) Jo(Hu Jm Jn Lx Nb Nc Nk Oh) Lh(Hv Jm Jn Jq Lx Nt Oh) qD(Ba Ch Dk Ng Nv Qy Ua) Wm(bA Et Ij Mw Oy Pf) Jn(Hu Hv Jq Oh Qd) Lx(Jm Nc Nt Oh) Nk(Hr Hx Io Oe) Of(Mw Nv Og Pg) Et(Aj Ap Kg) Nc(Il Nt Oh) Ng(Ad Ba Kq) Hr(Hu Hx) Pf(Co Ct) Ntll JmOh OwfN OybA} Et{Aj(aD aE AF aG aH al aJ aK AL aM AN aO aP aQ AR AS aU aV AW aX aY aZ BB bC bE bF BG bH bI bJ bL bM BN BO bP bQ bR bS bU bV bW bX bZ cA cB cC cD cE cF cG cH cJ cK cL cM cN cO CP CQ cR cS Ct cU CV CW CX cY cZ dA DB DC DD DE dF DG dH DI dJ DK DL dN Dp Ed EF Fb Fr Fy Gl GP Hc Hq Hr Hv Hw Hx Ih Ii Ij Ik Io Ip Iq Ir It Iu Iv Iz Jd Jg Jh Jk Jn JO Jp Jr Js Jt Kd Ke Kg Kk Kl Kn Ko Kp Kr Kx Lh Lu Lw Ly Lz Ma Mb Mc Md Mf Mg Mh Mj Mk Ml Mn Mp Mu Mv Mw Mx Mz Na Nc Ne Nf Nh Nj Nk Nl Nm Nn Nq Nr Ns Nt Nu Nv Nx Ny Oe Of Og Oi Ok Om On Or Ow Pa Pc Pd Pg Pi Pk Po Pz Qb Qc Qh Qm Qn Qt Qv Qy Ra Ri Rm Sr Ss St Tn Tv Ua Uc Ud Uk Ul Un Up Ur Us Uu Vp Vt Wm Tj) Kg(Ad Af An AO Ap As Ax Bc Bn Ch cI Cq Cs cT Cu Cw Cx Dc De dM Dp Ed Hv Hw Id Ij Il Im Ji Jj Jl Jm Jn Jq Jr Jy Kd Ke Kn Ko Kp Kq Kr Lh Li Lv Lw Lx Me Mi Mj Ml Mm Ms Mw My Na Nd Ne Ni Nm No Oh Or Ou Oy Oz Pe Pi Pk Qa Qd Qe Ra Ri Sr Tv Uc Ud UK Ul Un Up Ur Us Vp Wm) Ng(aD aE aG al aL aP aQ aR aS aV aY aZ bB bC bE bG bl bM bO bP bQ bU bW bX cB cC cD cE cF cG cH cJ cL cM cO cP cQ cR cS cU cV cX cY cZ dA dB dG dH dK dL dN dR eC eF Fn fP gL gW Ha Ib Jd Je Jf Ju Jv oE pF Qg Qu Qx Qy Qz Rb Rg Rj Rm Ss To Tt Tv Ug Up Vo Vv) Mn(Fr Hr Hu Hv Hw Hx Ih Ii Ij Il Io Ip Iq Ir It Iu Iv Jg Jh Jk Jm Jn Jp Js Jt Lw Ly Lz Ma Mb Mc Md Mf Mg Mi Mj Mk Ml Mm Mp Mu Mv Mw Mx Na Nf Nk Nm Nn No Nq Nr Nu Nv Nx Ny Oe Of Og Oi Ok Om On Oz Pa Pc Pd Pe Pg Po Pz Qb Qc) Ij(Fr Hr Hu Hv Hw Hx Ih Ii Il Io Ip Iq Ir It Iu Iv Jg Jh Jk Jm Jn Jp Js Jt Lw Ly Lz Ma Mc Md Mf Mg Mi Mj Mk Ml Mm Mp Mu Mv Mw Mx Mz Na Nf Nk Nm Nn No Nq Nr Nu Nv Nx Ny Oe Of Og Oi Ok Om On Oz Pa Pc Pd Pe Pg Po Pz Qb Qc) Ip(Fr Hr Hu Hv Hw Hx Ih Ii Iq Ir It Iu Iv Jg Jh Jk Jm Jn Jp Js Jt Lw Ly Lz Ma Mb Mc Md Mf Mg Mi Mj Mk Ml Mm Mp Mu Mv Mw Mx Mz Na Nf Nk Nm Nn No Nq Nr Nt Nu Nv Nx Ny Oe Of Og Oi Ok Om On Oz Pa Pc Pd Pe Pg Po Pz Qb Qc) No(Ap Ch Ct Fr Hr Hu Hv Hw Hx Ih Ii Iq Ir It Iu Iv Jg Jh Jk Jn Jp Js Jt Lw Ly Lz Ma Mc Md Mf Mg Mi Mj Mk Ml Mm Mp Mu Mv Mw Mx Na Nf Nk Nm Nn Nq Nu Nv Nx Ny Of Og Oi Ok Om ON Oz Pa Pc Pd Pe Pg Po Pz Qb Qc Wm) Pz(Fr Hr Hu Hv Hw Hx Ih Ii Io Iq Ir It Iu Iv Jg Jh Jk Jn Jp Js Jt Lw Ly Lz Ma Mb Mc Md Mf Mg Mi Mj Mk Ml Mm Mp Mu Mv Mw Mx Na Nf Nk Nm Nn Nq Nr Nu Nv Nx Ny Oe Of Og Oi Ok Om On Oz Pa Pc Pd Pe Pg Po Qb Qc Wm) Mc(Fr Hr Hu Hv Hw Hx Ih Ii Il Iq Ir It Iu Iv Jg Jh Jk Jm Jn Jp Js Jt Lw Ly Lz Ma Md Mf Mg Mi Mj Mk Ml Mm Mp Mu Mv Mw Mx Na Nf Nk Nm Nn Nq Nr Nu Nv Nx Ny Oe Of Og Oi Ok Om On Oz Pa Pc Pd Pe Pg Po Qb Qc) Ir(Fr Hr Hu Hv Hw Hx Ih Ii Iq It Iu Iv Jg Jh Jk Jm Jn Jp Js Jt Lw Ly Lz Ma Mb Md Mf Mg Mi Mj Mk Ml Mm Mp Mu Mv Mw Mx Mz Na Nf Nk Nm Nn Nq Nr Nu Nv Nx Ny Of Og Oi Ok Om On Oz Pa Pc Pd Pe Pg Po Qb Qc) It(Fr Hr Hu Hv Hw Hx Ih Ii Iq Iu Iv Jg Jh Jk Jm Jn Jp Js Jt Lw Ly Lz Ma Mb Md Mf Mg Mi Mj Mk Ml Mm Mp Mu Mv Mw Mx Na Nf Nk Nm Nn Nq Nr Nu Nv Nx Ny Oe Of Og Oi Ok Om On Oz Pa Pc Pd Pe Pg Po Qb Qc) Iu(Fr Hr Hu Hv Hw Hx Ih Ii Iq Iv Jg Jh Jk Jm Jn Jp Js Jt Lw Ly Lz Ma Mb Md Mf Mg Mi Mj Mk Ml Mm Mp Mu Mv Mw Mx Na Nf Nk Nm Nn Nq Nr Nu Nv Nx Ny Oe Of Og Oi Ok Om On Oz Pa Pc Pd Pe Pg Po Qb Qc) Ny(Fr Hr Hu Hv Hw Hx Ih Ii Il Io Iq Iv Jg Jh Jk Jm Jn Jp Js Jt Lw Ly Lz Ma Mb Md Mf Mg Mi Mj Mk Mm Mp Mu Mv Mw Mx Na Nf Nk Nm Nn Nq Nr Nu Nv Nx Oe Of Og Oi Ok Om On Oz Pa Pc Pd Pg Po Qb Qc) Nm(Fr Hr Hu Hv Hw Hx Ih Ii Il Io Iq Iv Jg Jh Jk Jn Jp Js Jt Lw Ly Lz Ma Mb Md Mf Mg Mi Mj Mk Ml Mm Mp Mu Mv Mw Mx Na Nf Nk Nn Nq Nr Nu Nv Nx Oe Of Og Oi Om On Oz Pa Pc Pd Pg Po Qb Qc) Ly(Fr Hr Hu Hv Hw Hx Ih Ii Il Iq Iv Jg Jh Jk Jn Jp Js Jt Lw Lz Ma Mb Md Mf Mg Mi Mj Mk Ml Mm Mp Mu Mv Mw Mx Na Nf Nk Nn Nq Nr Nu Nv Nx Of Og Oi Ok Om On Oz Pa Pc Pd Pe Pg Po Qb Qc) In(aC Ad An AO Ar As bA Bb Bc Bg BN bV Co Cq CT Cu Cv Cw Db Dc DE Dg Dk dM Dp Ef Fa Fb Hc Id Iz Kd Ke Kj Kk Kl Kn Ko Kp Kq Kr Kx Or Ou Ow Pi Pk Qy Ra Rm Sr Uk Ul Un Us) Mj(Fr Hr Hu Hv Hw Hx Ih Ii Iq Iv Jg Jh Jk Jm Jn Jp Js Jt Lw Lz Ma Mb Md Mf Mg Mi Mk Ml Mm Mp Mu Mv Mw Mx Na Nf Nk Nn Nq Nr Nu Nv Nx Oe Of Og Oi Ok Om On Oz Pa Pc Pd Pg Po Qb Qc) Ix(Fr Hr Hu Hv Hw Ih Ii Il Io Iq Iv Jg Jh Jk Jn Jp Js Jt Lw Lz Ma Mb Md Mf Mg Mi Mk Mm Mp Mu Mv Mw Mx Na Nf Nk Nn Nq Nr Nu Nv Nx Of Og Oi Ok Om On Oz Pa Pc Pd Pg Po Qb Qc) Iv(Fr Hr Hu Hv Hw Ih Ii Iq Jg Jh Jk Jm Jn Jp Js Jt Lw Lz Ma Mb Md Mf Mg Mi Mk Ml Mm Mp Mu Mv Mw Mx Na Nf Nk Nn Nq Nr Nu Nv Nx Of Oi Ok Om On Oz Pa Pc Pd Pe Pg Po Qb Qc) Ma(Fr Hr Hu Hv Hw Ih Ii Iq Jg Jh Jk Jn Jp Js Jt Lw Lz Mb Md Mf Mg Mi Mk Ml Mm Mp Mu Mv Mw Mx Na Nf Nk Nn Nq Nr Nu Nv Nx Of Og Oi Ok Om On Oz Pa Pc Pd Pg Po Qb Qc) Mi(Ct Fr Hr Hu Hv Hw Ih Iq Jg Jh Jk Jn Jp Js Jt Lw Lz Md Mf

Nm Nn No Nq Nr Ns Nu Nv Ny Oe Of Og Oi Oy Oz Pa Pc Pd Pe Pg Pz Qb Qc Wm) Lx(Hq Hr Hu Hv Hw Hx Ih Ii Ij Io Ip Iq Ir It Iu Iv Jh Jk Jp
Js Lj Lw Ly Lz Ma Mb Mc Md Mf Mg Mh Mi Mj Mk Ml Mm Mn Mp Mu Mv Mw Mx My Na Nb Nc Nf Ng Nk Nm Nn No Nq Nr Ns Nu Nv
Ny Oe Of Og Oi Oy Oz Pa Pc Pg Po Pz Qb Qc Wm) Po(Fr Hr Hu Hv Hw Ij Il Io Ip Ir Jn Jo Jq Jr Js Jt Lj Lu Lw Ly Lz Ma Mb Md Me Mf Mg
Mm Mp Mr Mu Mw Mx My Na Nb Nc Ne Ng Nk Nl Nm Nn No Nr Ns Nu Nv Ny Of Og Oy Pa Pc Pd Pe Pg Pz Qb Qc) Nx(Hu Hv Hw Ih Ii Ij
Io Ip Ir It Jk Jn Jo Js Jt Lu Lw Ma Me Mf Mg Mh Mi Mj Mm Mp Mu Mv Mx Na Nb Nc Nd Ne Nf Nj Nl Nm Nn No Ns Nu Nv Pa Pb Pc Pd Pg
Pz Qb Qc) Oh(aA Hu Hw Ij Il Ip Ir Jm Jn Jo Jp Jq Jr Jt Lj Lu Lw Mf Mg Mm Mr Mu Mw Mz Nb Nc Ne Nl Nm Nr Nu Nv Pb Pd Pe Pg Pz Qb
Wm) Pf(aA bL bR CO Ct Lf Fj Il Ip Jg Jm Jn Jo Jp Jr Js Jt Lj Me Mr Mu Mw Nb Ne Ni Nj Nl Nr Nu Nv Oa Oy Pb Pz Qb Un Vt) Lv(Hu Ih Ii
Ij Ip Ir It Iv Jk Jo Jt Lu Lw Me Mg Mu Mx Nb Nc Nd Ne Ni Nj Nl Nm Nn No Nu Ny Pb Pc Pd Pe Pg Qb Qc Wm) Ik(aA Hv Hw Ih Ii Ij Il Ir Jk
Jo Jr Lw Me Mi Mj Mn Ms Mu Mx Na Nd Nf Nh Ni Nm Nn Nr Ns Nu Ny Pc Pd Pe Pg Qc) Nh(aA Ii Ij Il Ip Jn Jo Jr Js Jt Me Mg Mm Mp Mr
Mu Nb Ne Ni Nm Nn No Nr Nu Ny Pb Pd Pe Pg Pz Qb Qc) Lh(Hv Ii Ij Iq Ir It Iu Jh Jk Jo Ly Mc Mg Mi Mj Mk Ml Mn Mp Mv Nf Nm Nn No
Nv Ny Of Og Oi Oz Qc) Om(aA Fr Il Jg Jm Jn Jp Jr Js Lu Md Me Mf Mh Mr Mw My Mz Nb Nc Ne Ni Nj Nl Nr Ns Nu Oy Pb Pd Qb) Mt(Hq
Hr Hx Iq Iu Iv Jh Jk Ly Lz Ma Mb Mc Md Mi Mj Mk Ml Mn Mv Na Ny Oe Of Og Oi Oz Pa Wm) Mq(aA Ij Il Ip Ir Jn Jr Jt Mm Mp Mr Mw Nc
Nd Ne Nj Nl Nm No Nr Nu Nv Pb Pd Pg Pz Qb Qc) Jg(aA Fr Il Io Jm Jn Jq Jr Js Lu Me Mf Mh Mr Ms Mw Mz Nc Ne Ni Nj Nl Nr Nu Pb Pe
Qb) Fr(Il Jm Jn Jp Jq Jr Js Jt Me Mf Ms My Mz Nc Ne Ng Nj Nl Nu Oy Pb Pz Qb) Lj(Dp Hu Jh Jn Jo Jp Jq Jt Me Mg Mm Mr Mu Mw Mz Ni
Nj Nl Nv Ou Pz) Jp(Il Jm Jq Jr Lu Me Mf Mr Ms Ne Ni Nl Nr Nu Wm) Nd(Ij Il Jm Jn Jq Js Mm Mp Mr No Pe Pz Qb) Wm(Ih Jq Mw Mz No
On Pe Qc) Dp(Il Im Ji Jl Oa Qa Qe) Mz(aA Il Jm Jr Ne Nj Nl) Ji(Ao Ax cI Co Cs Oa) Jq(Il Ms Ne Nj Nl) Nv(Me Ms Ni Nj Nl) Vt(Im Jl nW Qa)
Ng(Ad Ba Kq) Jm(aA Ni Nj) No(oE oN) Il(Oa Un) Qa(bR cI) AdAj NraA MwNj NiQb VqoE} Lv{Qa(Fr Hr Hu Hv Hw Hx Ih Ii Ij Ik Io Ip Iq Ir
It Iu Iv Jg Jh Jk Jm Jn Jo Jp Jq Jr Js Jt Lh Lu Lw Lx Ly Lz Ma Mb Mc Md Me Mf Mg Mh Mi Mj Mk Ml Mm Mn Mp Mr Mu Mw Mx My Mz
Na Nb Nc Ne Nf Nj Nl Nm Nn No Nq Ns Nt Nu Nv Nx Ny Oe Of Og Oh Oi Om On Oz Pa Pc Pd Pe Pg Po Pz Qc Qd Qe) Li(Fr Hr Hu Hv Hw
Hx Ih Ii Ij Ik Ip Iq Ir It Iu Iv Jg Jh Jk Jm Jn Jo Jr Js Jt Lh Lj Lw Lx Ly Lz Ma Mb Mc Md Mf Mg Mh Mi Mj Mk Ml Mn Mp Mr Mu Mv Mw Mx
My Na Nb Nc Ne Nf Nj Nl Nm Nn No Nq Nr Nt Nu Nv Nx Ny Oe Of Og Oh Oi Om Oz Pa Pc Pd Pe Pf Pg Po Pz Qb Qc Qd) Im(Hr Hu Hv Hw
Hx Ih Ii Ik Ip Iq Ir It Iu Iv Jg Jh Jk Jm Jn Jo Jq Jr Js Jt Lw Ly Lz Ma Mb Mc Md Me Mf Mg Mh Mi Mj Mk Ml Mn Mp Mu Mv Mw Mx My Na
Nb Nc Ne Nf Nj Nk Nl Nm Nn No Nq Nr Ns Nt Nu Nv Ny Oe Of Og Oi Om Oy Oz Pa Pc Pd Pe Pg Po Pz Qb Qc) Mt(Fr Hq Hu Hw Ih Ii Ik Il
Io Ip It Iu Jg Jk Jm Jn Jo Jp Jq Jr Js Jt Lh Lu Lw Lx Md Me Mh Mk Mm Mp Mr Mu Mw Mx My Mz Nb Nc Nd Ne Nf Nh Ni Nj Nk Nl No Nq
Ns Nt Nu Nx Oe Of Og Oh Oi Om On Oz Pa Pc Pd Pe Pf Pg Po Qc) Qe(Fr Hr Hu Hw Ih Ii Ik Il Io Iq It Iu Jg Jk Jm Jn Jo Jp Jq Jr Jt Lh Lj Lu Lw
Lx Lz Md Me Mh Mj Mk Mm Mp Mr Mu Mw My Mz Na Nb Nc Ne Nj Nk Nl No Nq Ns Nt Nu Nx Oe Of Og Oh Oi Om On Oy Pa Pc Pd Pe Pf
Pg Po Qb Qd) aA(Fr Hq Hu Ih Ij Ik Il Io Ip Ir Jg Jm Jn Jq Jr Js Jt Lu Ma Md Me Mf Mh Mn Mp Mr Mu Mw Mx My Na Nb Nc Ne Ng Ni Nj Nk
Nl Nm Nn No Nq Nr Ns Nt Nu Nv Ny Og Om Oy Oz Pb Pc Pd Pe Pg Pz Qb Qc) Lx(Fr Hq Hr Hu Hw Ih Ii Ik Il Io Jg Jk Jm Jn Jo Jp Jq Jr Jt Lh
Lj Lu Lw Md Me Mk Mm Mp Mr Mu Mw My Mz Nb Nc Ne Nj Nk Nl No Nq Ns Nt Nu Nx Oe Of Og Oh Om On Pa Pc Pd Pe Pf Pg Qd) Lj(Hq
Hr Hu Hw Ih Ik Il Io Ip It Jh Jm Jn Jq Jr Jt Lu Lw Lz Me Mi Mk Mp Mr Ms Mu Mv Mw Mz Nb Nc Ne Ng Nj Nk Nl Nn No Nq Ns Nt Nu Nv
Nx Oh Oy Pa Pc Pd Pe Pf Po Pz Qd) Jl(Fr Hq Hr Hu Hw Ih Ii Ik Il Io Jg Jk Jn Jo Jp Jq Jr Lh Lu Lw Md Me Mk Mm Mq Mr Mw My Mz Nb Nc
Ne Ni Nj Nk Nl Nq Ns Nt Nx Oe Of Og Oh Om On Pb Pc Pf Pg Po Qd) On(Hq Hr Hu Hw Ik Il Io Jh Jm Jn Jo Jp Jq Jr Lh Lu Lw Md Me Mg
Mh Mk Mm Mq Mr Mu Mv Mw Mz Nb Nc Ne Ni Nj Nk Nl Nq Nt Nu Nv Nx Oe Og Oh Pa Pc Pf Pg Po Qd) Jp(Hq Ik Il Io Jq Jr Lh Lu Lw Me
Mm Mq Mr My Mz Nb Ne Ni Nj Nl Nq Ns Nt Nu Nx Oh Oy Pb Pe Pf Po Qd) Qd(Fr Hq Ik Il Io Jq Lh Lu Me Mm Mq Mr Ms Mz Nb Nd Ng Nh
Ni Nj Nk Nx Oh Om Oy Pb Pc Pf) Nh(Fr Jq Lh Mm Mp Mq Mr Mw Mz Ne No Oh Om Pb Pf Po) Oh(Fr Lh Me Mm Mq Mr Mz Nb Nd Ni Pb
Pf) Pf(Hq Jq Lh Mm Mq Mr Ms Mz Nd Ng Ni) Mq(Fr Jq Mm Ms Mz Nd Nt Nx Pb) Ms(Fr Jg Jq Mp Mz Nx Om Po) Nd(Lh Mm Mp Mr Mw
Mz Po) Lh(Mm My Mz Ng Pb) Pb(Fr Mr Om Po) Fr(My Mz) Jg(My Oy) PoHq MmMr OmOy} Ms{Ji(aC AD aE AF aG aH aI aJ aK AL aM
AN AO aP aQ AR AS aU aV AW AX aY aZ Ba BB BC bE bF BG bH bI bM BN BO bP bQ bR bS bU bV bW bX bZ cB cC cD cE cF cG cH cJ
cK cL cM cN cO CP CQ cR CS cT CU CV cW CX cY cZ dA DB DC dD dF DG dH DI DK DL dN Dp dR eC Ed EF Ez Fa Fb Fn fP gL Gp hA
Hb IB Ic Id Iz Jd JE JF jG jK jL jM jO jP jQ jR JU JV Jy Ke Kg Kj Kk Kn Ko Kp IL IN nW Oa oE oN Ou Ow Qg Qh Ql Qm Qn Qt Qu Qv Qw
Qx Qy Qz Ra Rb Rc Rf Rg Rh Rj Rm Sr Ss St Tn To Tr Tt Tv Tz Ua Ub Uc Ud Uf Ug Uh Um Un Uo Ut Uu Vo Vp Vt) Jl(Fr Hq Hr Hu Hv Hw
Hx Ih Ii Ij Il Io Ip Iq It Iu Jh Jk Jm Jn Jo Jr Js Jt Lj Lu Ly Lz Ma Mb Mc Mf Mh Mk Ml Mm Mp Mr Mu Mv Mw Mx My Na Nc Ne Nf Ng Nj Nl
Nm Nn No Nq Nr Ns Nt Nu Oe Og Oi Oy Pa Pc Pd Pe Pg Po Pz Qc Qd Wm) Mt(Hq Hu Hv Hw Ih Ij Ik Il Io Ip Ir Jh Jm Jn Jo Js Jt Lu Mf Mh
Mi Mm Mu Mw Mx My Na Nb Nc Nd Ne Nf Ng Nh Nj Nk Nm Nn No Nq Ns Nt Nu Nv Ny Oe Og Oi Oy Oz Pa Pd Pg Pz Qb Qc) Lh(Fr Hq Hr
Hu Hw Hx Ii Ik Il Io Iu Jg Jm Jn Jo Js Jt Lu Lw Me Mf Mm Mp Mr Mu Mw Mx My Na Nb Nc Ne Nj Nk Nl Nn No Nq Ns Nt Nu Oe Og Oy Pc
Pe Po Qb Wm) Qa(Hq Hu Hw Ih Ik Il Im Io It Jn Jr Jt Li Lu Lw Me Mm Mp Mr Mu Mw Nb Nc Ne Ng Nh Nj Nn No Nt Nu Og Oh Oy Pb Pc Pe
Pf Po Qb Qe Wm) Lx(Fr Hq Hu Hw Ik Il Io Jg Jn Jo Jp Jr Jt Li Lu Lw Me Mf Mi Mm Mp Mu Mw Nb Ne Ng Nj Nk Nl Nn No Ns Nt Nu Oy Pa
Pc Pe Pf) Qe(Hq Hu Ih Ik Il Io Jn Jo Jr Jt Li Lu Lw Me Mm Mp Mr Mu Mw Nb Ne Ng Nj Nl Nn No Nq Nt Nu Og Oh Oy Pb Pc Pe Pf Po)
Im(Hq Ik Il Jg Jq Jr Jt Li Lj Lu Lw Me Mi Mm Mp Mu Mz Nb Nd Ng Nj Nk Nn Nt Nu Pb Pc Pe Pf Po Qd) Om(Fr Jp Jr Li Lj Md Mp Mq Mr
Mz Nd Nh Ni Nt Nx Oy Pb Pf Po) Qd(aA Fr Ik Jg Jp Jq Li Mq Mz Nd Nh Ni Nx Oh Pf Wm) Jp(aA Ik Jq Jr Li Lj Me Mr Nh Ni Nj Nt Nx Oh
Po) Fr(aA Jq Jr Lj Mq Mz Nd Ng Nh Nt Nx Oh) Jq(aA Jg Li Mq Nh Nt Oh Pf Wm) Mq(aA Jg Li Lj Mz Nx Oh) Li(Mz Nd Nh Nt Nx Pb) Oh(Jg
Mz Nh Ni Nt Nx) aA(Ij Jg Lw Mz Nt Pf) Aj(Ad Kq) Wm(Ke Pf)} aA{Qe(Fr Hq Hr Hu Hv Hw Hx Ii Ij Io Ip Iq It Iu Jg Jh Jk Jl Jm Jn Jo Jp Jr Js
Jt Lh Li Lu Ly Lz Ma Mb Mc Md Mf Mg Mh Mi Mj Mk Ml Mm Mn Mp Mr Mu Mv Mw Mx My Mz Na Nb Nc Ne Nf Nl Nm Nn No Nr Ns Nt
Nu Nv Ny Oe Of Og Oh Oi Om On Oy Oz Pa Pc Pd Pe Pg Po Pz Qa Qb Qc Qd) Lx(Fr Hq Hr Hu Hv Hw Hx Ih Ii Ij Il Io Ip Iq Ir It Iu Jg Jh Jk
Jm Jn Jo Jp Jr Js Jt Lh Li Lu Ly Lz Ma Mb Mc Md Mg Mh Mi Mj Mk Ml Mm Mn Mp Mr Mt Mu Mv Mw Mx Na Nb Nc Ne Nf Nk Nl Nm Nn
No Nr Nt Nu Nv Ny Oe Of Og Oh Oi Om On Oz Pa Pc Pd Pe Pf Pg Po Pz Qb Qc Qd) Im(Fr Hr Hu Hv Hw Hx Ii Ij Ik Io Ip Iq Ir It Iu Iv Jg Jh Jk
Jm Jn Jo Jp Js Jt Ly Lz Ma Mb Mc Md Mg Mh Mi Mj Mk Ml Mn Mp Mr Mu Mv Mw Mx My Mz Na Nb Nc Ne Nf Nl Nm Nn No Nr Nt Nu Nv
Ny Oe Of Og Oh Oi Om On Oy Oz Pa Pc Pd Pe Pg Po Pz Qa Qb Qc Qd) Qa(Fr Hq Hr Hu Hv Hw Hx Ih Ii Ik Il Io It Jg Jk Jl Jp Jq Jr Lh Li Lj Lu
Lw Ma Mb Md Me Mf Mh Mm Mn Mq Mt My Mz Nb Nc Ne Ng Nh Nj Nk Nl Nq Ns Nt Nx Oe Og Oh Om On Oy Pb Pc Pd Pf Po Qb) Lj(Fr
Hq Hu Hv Hw Hx Ih Ij Il Io Ip Jh Jm Jn Jo Jp Jr Li Lu Lz Ma Mb Md Me Mf Mg Mh Mn Mp Mr Mu Mv Mw My Mz Nb Nc Ne Ng Nl Nm Nn
Nq Nr Ns Nt Nu Nv Oe Oh Oy Pa Pc Pd Pf Pg Po Pz Qd) Li(Hq Ik Il Io Jl Jq Jr Lh Lu Lw Me Mf Mm Mq Mt My Mz Nc Ng Nh Nj Nk Nq Ns
Nt Nx Oh On Oy Pb Pf Po Qd) Po(Hq Il Jl Jp Jq Jr Lh Lw Me Mf Mm Mq Mt My Mz Ng Nh Ni Nj Nk Nq Ns Nt Nx Oh On Oy Pf Qd) Mt(Jl Jq
Jr Lh Lw Me Mf Mm Mq My Mz Nd Ne Ng Nh Ni Nj Nq Ns Nx Oh On Oy Pb Pf Qd) Lh(Hx Ii Jl Jq Jr Lw Me Mm Mq My Mz Ng Nh Ni Nj
Nq Ns Nx Oh Oy Pb Pf Qd) Mq(Fr Jl Jp Jq Jr Lw Mm Mz Nd Nh Nj Nt Nx Oh Om On Pb Pf Qd) Jl(Jq Jr Lw Me Mf Mz Ng Nh Ni Nj Ns Nx
Oh On Pb Pf Qd) Pf(Aj Ct Jq Jr Lw Mz Nd Nh Ni Nj Nx On Oy Pb Qd Wm) Qd(Ik Il Lw Me Mm Mz Nd Nh Ni Nj Nq Nx Pb Pc) Nd(Fr Il Jp Jq
Lw Mm Mn Mp Mw Mz Oh Om) On(Jk Jr Lw Me Mf Mh Nh Ni Nj Nq Ns Pb) Nh(Jq Lw Mn Mz Ne Oh) Om(Ng Oy Pb) Lw(Nx Oh) FrNg

Figure 1 Continued

Figure 1 Continued

Wm(Ke Kq No) No(oE oN) Nq(bA Ke) Li(Mq Nh) Aj{Kq TrJh IlKe} Qa{Mq(Fr Hq Hr Hw Ih Ii Il It Jk Jp Jq Lh Li Lj Lu Lx Mt Mz Ne Nh Nj Nk Ns Nt Nx Og Pf Qb) Nk(Fr Ih Ik Il Jp Jq Jr Lh Li Lj Lu Lx Mr Mt Ne Nl Nt Nx Pb Pe Pf) Lh(Hq Hr Hw Hx Ih Ii Il Jk Jo Lj Mb Mt My Nh Nj Nq Of Og Pf Qb) Pb(Fr Hu Ik Il Jg Jp Jq Li Lu Lx Me Mr Mt Nh Nt Nx Om Pe Qb) Mt(Hq Ih Ii Il It Jk Jq Lj Me My Ne Nq Ns Oe Og Pf Qb) Jq(Fr Hq Hr Ih Ii Ik Il It Li Lx Md Nh Og Pf Qb) Fr(Hq Ii Il Jk Me My Nh Nj Nq Ns Og) Pf(Ct Hq Ih Jk Nh Pa Qb) Lx(Hq Ih Me Nh Qb) Li(Hq Ih Jk Me Nh) Om(Hq Ii Jk My Og) Jp(Jk Me Nh Nj) Nx(Ih Ii Og Qb) Ct(BA cT) My(Jg Jh) Ih(Ik Il) AdAj TiIi NcNh NeNj JgJk} Qe{Mt(Hq Ih Ii Il Io Jk Jq Lh Lj Lw Lx Me Mq Mr My Ne Nh Nj Nk Nq Ns Oe Og Oi Pb Pf Qb) Mq(Fr Hq Hr Hw Ih Ii Jp Jq Lh Li Lj Lu Lx Mz Nh Nj Nk Ns Nt Nx Og Pb Pf) Jq(Fr Hq Hr Ih Ii Ik Il It Lh Li Lu Lx Mb Md Nh Nj Nk Nt Nx Og Pb Pf) Lh(Hq Hr Hw Hx Ih Il Jk Jo Lj Mk Mw My Nh Nj Nk Ns Of Og Pf) Nh(Fr Ih Jp Li Lu Lx Me Mr Mz Nc Nl Nx Og Om Pb Pf) Pb(Fr Ik Li Lx Me Mr Nt Nx Om Pe Pf) Fr(Hq Il Jk Me My Nj Nq Og) Nk(Li Lx Nc Ne Nj Nl Pf) Om(Hq Ii Jk My Og) Hq(Li Lx Pf) Me(Li Lx) My(Jg Jh) Nx(Ii Og) AdAj CtbA NjJp IkOg PaPf} Lh{Nh(Fr Hq Hr Hx Ii Jk Jo Jp Jq Jr Li Lx Md Mk Mm Mq Mt My Mz Nc Ne Nk Ns Of Og Oh Pf Qd) Mt(Hq Hr Hx Ii Il Jk Jo Jq Jr Li Lx Md Me Mk Mq Mw Nj Nq Ns Of Og Pf Qd) Pb(Fr Hr Hx Ii Ik Jg Jp Jr Mb Mm Mq My Ne Nj Nl Nt Nx Oh Om Pd Po Qd) Lj(Fr Hq Hr Hx Ii Ik Jp Lu Mm Mq Nj Nk Nr Nx) My(Fr Jg Jp Li Lx Om Pf Wm) Lx(Hq Hr Ii Mq Nj Of) Ii(Li Pf Qd) Hq(Li Pf) Qd(Hr Hx) NcNk NjJp} Mq{Lx(Fr Hq Jn Jp Jq Lj Lu Me Mr Mt My Mz Nh Nj Nk Ns Nt Nx Pf Qd) Mt(Fr Jp Jq Li Lj Me Mr Mz Nh Ns Oh Pf Qd) Lj(Fr Jg Jp Jq Mm Nh Ns Nt Nx Om Pb) Nh(Fr Jp Jq Li Oh Pf Qd) Fr(Jq My Nj Ns Qd) Li(Hq Jq Lu Nj Ns) Qd(Jq Ns Pb Pf) Jp(Jq Nj Ns Pb) Pb(Oh Om) Pf(Ct Jq) AdAj MyJg} Nh{Lx(Fr Hq Jp Jq Me Mr Mz Nc Ne Nk Ns Pb Pe Qd) Fr(Jq Jr Li Lj Me My Mz Ne Pb Qd) Li(Jq Lu Me Mz Nc Ne Nk Pb) Lj(Jp Jq Mt Ne Nk Om) Jp(Jq Me Ne Nk) Qd(Jq Ne Nk) Jq(Mt Pf) PbPf} Mt{Lj(Fr Ih Jp Jq Lu Lw Me Mm Mr Nk Ns Om Pb) Pb(Fr Jq Li Lx Me Mr Oh Om Pe Po Qd) Me(Jp Li Lx Oh Pf Qd) Jq(Li Lx Md Ns Pf Qd) Qd(Il Nk Nq Ns) Lx(Hq My) AdAj FrMy NsLi} Pf{Ct(Ad BA Bc cT Ij Jp Jq Ke Kq Mk Pb) Pb(bA Fr Jq Ke Kn Lx Mr Nt Om Ur Vt) Aj(Bc bR Jg Jp Jq Ke Kq Mk Qd) Wm(Jq Lw My Oz) Vt(Ha Oz Ur) Ii(Ke Un)} No{oE(aF aO aP Bc bV Ch cK Ct DE Gl Jk Ne Nj Nk nW oN Vt) oN(Ar Ha Ib Nk Rg Ri Wm) gP(Ha Rg Ss Wm Tj) Wm(My oH) Ow(fN qD) Ou(fN uM) HagW dBqC} Ke{Wm(bA fP gP hG Ib iH iO My nW oE oF oH oK pF) Ch(eF gP iJ oE oH oN pF) DbqC IiOa gWhG wDnW} Pb{Fr(Ik Lj Lx Nj Nt Qd) Lx(Ik Jq Me Mr Pe) Aj(Ad Kq) Li(Jq Me) IkJp LjOm} Aj{Ad(aJ Ba bF cT dF Hu Il Lx Qd) Kq(Il My Oa)} Wm{My(Jp Om) Vt(oE oH) TjLx ThSt MdJq JrJs UhbA} Li{nW(tR tS tU) jT(sO vW) vS(jO Mz) MdJq NkNl} Fr{Qd(Il My Nj Nq) Lj(Ik Jq Me Nj)} Ct{Ba(As Dc Vt) Ad(bA cT) Kq(Dp Il)} Vt{qZ(dB nW) oE(cH Ne) MeqC nWvS} Lx{MdJq MeQd MyJg NkNl} Lj{Jp(Ik Nj) LuOm wPnW} Vq{Ed(Fi oE) NkoE} Ch{Kq(cI gP)} Mz{Rb(qC qD)} Il{DrOr FiIv} wDjYnW

Unconstrained panels with 3 analytes, where 2.0E-8 >= 'model p-value' > 1.0E-8. Contains 7,758 panels of 36,050,556 total panels evaluated.: Is{In(aE AF aG aJ aK aL aO AP aQ aS aU aV Aw aX aY aZ Ba Bb bF BG bH bI bJ Bn BO bP bQ bX bZ cB cE cG cK cL cM Cp Cq cR cS cT cU cW CX cY DB Dd DG dH dI Dl Dp Hc Kd Kk Kn Kp Kq Oa Ow Pj Qm Ur Us) Jj(aE aG aH al aJ aK aL aP aQ aR aS aU aV aX aY aZ bB bC bE bF bG bH bI bJ bO bP bQ bW bX bZ cB cC cD cE cG cH cK cL cM cN cP cR cS cU cW cX cY cZ dA dB dC dD dF dG dI dL dN Ed Jv Kp Qg Sr Ua Uh Ul) Ne(Aj dM Hv Ij Ip Ir Iv Jh Jn Js Jt Ly Lz Ma Mc Mf Mg Mh Mi Mj Mk Mp Mu Mv Mw Mx Na Nf Nm Nn Nr Nv Of Oz Pa Pg Pz Qc) Jg(Aj Ct Hv Ij Ip Ir Iv Jh Jn Js Ly Lz Ma Mc Mf Mi Mj Ml Mn Mp Mx Na Nf Nm Nn No Nr Nv Ny Om Oz Pd Pg Po Pz Qb Qc) Pe(Ct Hv Ij Ip Ir Iv Jm Jn Js Jt Ly Ma Mc Mf Mg Mi Ml Mp Mr Mu Mv Mw Na Nm Nn No Nv Ny Om Oz Pd Pg Po Pz Qb) Lw(Hv Ij Ip Ir Iv Jh Jn Js Jt Ly Lz Mc Mf Mg Mi Mj Ml Mn Mp Mv Mw Mx Na Nf Nm Nn No Nr Nv Ny Oz Pg Pz Qb Qc) Jo(aN Ip Ir Iv Jh Jm Jn Js Ly Lz Mc Md Mg Mi Mj Mk Ml Mn Mp Mv Mw Mx Na Nf Nn No Nr Nv Ny Of Oz Pa Pz Qb Qc) Nl(Hv Hx Ij Ip Ir Iv Jh Jn Js Jt Ly Lz Mc Mf Mg Mi Mj Ml Mn Mv Mw Mx Na Nf Nm Nn Nr Nv Ny Of Oz Pg Pz Qc) Nu(Hu Hv Hx Ij Ip Iv Jn Js Jt Ly Ma Mc Mf Mg Mh Mi Mj Mp Mu Mw Nm Nn No Nr Nv Of Oz Pa Pd Pg Po Pz Qb) Oe(Hv Ij Ip Ir Iv Jh Jn Ly Lz Mc Mf Mg Mi Mj Ml Mn Mv Mx Na Nf Nm Nn Nr Nv Ny Of Oi Oz Pa Pg Pz Qb Qc) Mb(Hu Hx Ij Ip Iv Jh Jm Jn Js Lz Ma Mf Mg Mh Mi Mj Mp Mw Na Nf Nm Nn No Nv Of Oz Pa Pd Pg Pz Qb Qc) Qa(Hv Ij Ip Ir Iv Jn Js Jt Ly Lz Ma Mf Mg Mh Mi Mj Mp Mu Mw Na Nm No Nr Nv Ny Of Pa Pd Pg Po Pz Qd) Oh(Ij Ip Ir Iv Jh Jn Js Jt Ly Ma Mc Mg Mi Mj Ml Mn Mp Mv Mw Mx Na Nf Nm Nn No Nr Nv Ny Oz Pg Pz Qc) My(Hv Ij Ip Ir Iv Jn Js Jt Ly Lz Mc Md Mf Mg Mj Mk Mn Mx Na Nf Nm Nr Nv Ny Of Oz Pa Pz Qb Qc Wm) Iu(Hv Ip Iv Jm Jn Js Jt Ly Lz Ma Mc Mi Mj Mk Mp Mu Mw Mx Na Nf Nm Nn No Nr Nv Of Oz Pa Pg Pz Qb) Hr(Hx Ij Ip Iv Jm Jn Js Ly Lz Ma Mc Md Mi Mk Ml Mp Mw Mx Na Nm Nn No Nr Nv Of Oz Pa Pg Qb Qc) Qd(Hu Hv Ij Ir Iv Jn Js Jt Ly Lz Ma Md Mf Mh Mi Mj Mk Mp Mu Mw Na Nn No Nv Of Pa Pd Pg Po Pz) Mr(Ct Hv Ij Ip Ir Iv Jh Jn Js Jt Ly Mc Mg Mi Ml Mn Mp Mu Mv Mx Na Nf Nm Nn No Oz Pz Qb Qc) Jq(Hv Ij Ip Jh Jn Jt Ly Lz Mc Mg Mi Mj Ml Mn Mp Mv Mx Na Nf Nm Nn Nr Nv Ny Oz Pg Pz Qb Qc) Jr(Hu Hv Hx Ip Iv Jm Jt Lz Ma Mf Mh Mi Mj Mk Mp Mu Mw Na Nm No Nv Of Pa Pd Pg Po Qb) Nx(Ij Ip Ir Iv Jh Js Ly Lz Mc Mi Mj Ml Mn Mp Mv Mx Na Nf Nm Nn Nr Nv Ny Oz Pg Pz Qc) Pc(Hv Jh Jn Js Jt Ly Lz Ma Mc Mf Mg Mi Mp Mv Mx Na Nm Nn No Nv Of Om Pa Pd Pg Pz Qb) It(Ip Ir Iv Jh Js Ly Lz Mc Mg Mi Mj Ml Mn Mp Mv Nf Nm Nn Nr Nv Ny Oz Pa Pz Qb Qc) Oi(Hv Jm Jn Js Jt Ly Lz Ma Md Mf Mh Mi Mk Mp Mw Mx Na Nm Nn No Nr Of Pa Pg Qb) Om(Ct Hv Hx Ij Jh Jm Jn Js Jt Lz Ma Mf Mg Mu Mv Na Nc No Nv Pa Pd Pg Po Pz Qb) Nq(Hv Hx Jh Jn Js Jt Lz Md Mf Mh Mi Mk Mv Mx Na Nm Nn Nr Of Pa Pg Pz Qb Qc) Hu(Hv Hx Ij Jm Jn Js Jt Lz Ma Mf Mg Mh Mi Mj Mu Mv Mw Na No Nv Pa Pd Qb) Po(Hv Ij Jn Js Jt Ly Lz Ma Mf Mg Mh Mj Mu Mv Mw Na No Nr Nv Pd Pg Pz) Iq(Ij Ip Ir Iv Jh Ly Lz Mc Mg Mj Ml Mn Mv Mx Nf Nm Nn Nr Nv Ny Oz Qc) Ct(aA As Aw bV Cu cV Fr Ij Im Jp Lv Lx Me Mt Mw Nj No Nw Ok On Pb) Nc(Hv Jm Jn Jt Ly Ma Md Mf Mi Mk Mp Mu Mw Mx Na No Nr Of Pa Pg Qb) Qe(Ij Ip Iv Jh Mc Mg Ml Mn Mp Mv Mx Nf Nm Nn No Nr Ny Oz Pg Qc) Mm(Ip Ir Iv Jh Ly Mc Mj Mn Mp Mv Mx Nf Nm Nn Nr Ny Oz Pz Qc) Mh(Hv Hx Jm Js Lz Ma Md Mj Mk Mp Mu Mw No Of Pa Pd Qb) Ik(Ij Ip Ir Iv Jh Ly Mc Ml Mn Mv Mx Nf Nn Nr Ny Oz Pg) Aj(aA aI bA bB bV cM cQ cV Jp Kq Mq Nb Nk) Ng(Ar bA Bc bF bV cV Dg dN Jy Ko Uh Uk Ur) Et(aC aO bA Cq Cw Dd De Dg Dk dM Kj Us) Md(Hv Hx Jm Jn Jt Ma Mf Mu No Pd Pg) Hx(Hv Jm Ma Mi Mk Ml Mu Mw No Pd) Mk(Jm Mf Mi Mp Mu Pa Pd) Mu(Jm Mf Mw Of Pa Pd) No(Jm Mf Nr Pa Pd) Jk(bA iB iC jK jU) aN(Ii Ni Nw Oy Wm) Nj(Ij Ir Mn Ny) Jm(Ma Mf Mw Pd) Mz(Ij jK Qc) Pd(Ma Of Qb) bR(Ii Ms Pf) Ij(Ii Io) CoPf WmjV MlNy TrOy IvJn JicI PaPg} Ok{Nb(Hv Ij Ip Iq Ir It Iu Iv Jg Jh Jp Js Ly Lz Ma Mc Mi Mj Mk Ml Mm Mn Mp Mv Mw Na Nf Nm Nn No Nr Nt Nu Nv Ny Om Oz Pd Pg Pz Qb Qc) Jq(Hv Ij Ip Ir Iu Iv Jg Jh Jk Jn Jp Js Lw Ly Lz Ma Mc Mi Mj Mk Ml Mm Mn Mp Mv Mw Na Nf Nn No Nr Nv Nx Ny Oz Pd Pg Pz Qb Qc) Nj(Hv Hx Ij Ip Iq Ir It Iu Iv Jg Jh Js Ly Lz Ma Mb Mc Mf Mj Mk Ml Mn Mv Na Nc Nf Nl No Nq Nr Nt Nu Nv Nx Ny Om Pd Pg Pz) Qd(Hv Ip Ir Iu Iv Jg Jh Jn Jp Js Ly Ma Mc Mi Mj Mk Ml Mn Mp Mv Mw Mx Na Nf Nn No Nr Nt Nu Nv Ny Om Oz Pd Pe Pg Po Qb Qc) Hq(Hr Hv Hw Ih Ij Ip Iq Ir It Iu Iv Jg Js Jt Lw Ma Md Mg Mi Ml Mm Mp Mv Mw Na Nk Nm No Nq Nr Nt Nx Of Om Pa Pd Pg Qc) Pf(Aj Ct Hv Ij Ip Ir It Iu Iv Jg Jh Js Ly Ma Mc Mi Mj Mk Ml Mn Mp Mv Mw Nf Nn No Nr Nu Nv Ny Om Pd Pz Qb Qc) Fr(Hv Hx Ih Iq Iu Jh Lh Li Lw Lz Ma Mk Mm Mr Mu Mv Mx Na Nk Nm Nt Nu Nv Nx On Oz Pc Pd Pe Pg Po Pz Qb Qc) Og(Hr Hx Ih Ii Jg Jn Jp Jt Lw Mb Md Mf Mi Mp Mw Mx My Mz Nk Nn Nq Nu Nx Oe Of Oi Om Oz Pa Pd Pe Pg Qb Qc) Ne(Hu Hx Ih Ij Ik Il Iq It Iu Jg Jk Jm Jn Jp Jt Lw Md Mg Mi Mu Mz Nc Nm Nn Nt Nx Of Om Oz Pa Pe Po Qc) Li(Hu Hv Hx Iq Jm Jn Jp Lw Lz Ma Mb Mf Mg Mh Mk Mm Mr Mu Mw Mx Mz Na Nm Nt Nu Nv Nx Oh On Oz Pe Po) Hw(Hr Hu Hv Ih Jp Jt Lw Mb Md Mf Mg Mi Mm Mp Mw Na Nk Nm Nn Nq Nr Nt Nu Nx Of Oi Om Oz Pa Pg Qb) Ik(Hv Ij Il Iq It Iu Iv Jh Js Md Mf Mi Mm Mp Mu Mw Mx Na Nc

Figure 1 Continued

Figure 1 Continued

Mq(Hu Ih Jk Lu Lw Mf Mg Ms Mu Nb Ni Nn Ns Ny Pc Pe Wm) Jg(Hw Ih Ij Ip Jo Jp Jt Mj Mx My Nb Nq Ns Oy Pd Wm) Lj(bA Ij Il Ip Jm Jr Jy Lu Mp Nb Ne Nm Nu Pb Pd Pg) Fr(aA Hu Ij Ip Ir Mm Mr Mw Mx Nb Nm Nr Nv Pd Pe) Wm(bA Ij Il Ip Jm Jt Lw Mr Nb Nm Nr Om Pg Pz) Nh(Hu Ir Jk Lu Lw Ma Mf Mj Mn Ms Nc Nf Nk Pc) Jp(aA Hu Jn Jo Jt Mh Mu Mx Mz Nb Pb Pd Pe Qb) Ji(Aj Ap bA Bb Ch Ct Cx Dd De Dk gP oE Uk) Om(Hq Hu Ih Ip Ir Jt Mb Mj Mx Of Pe Pz Qc) Mz(Jn Jq Jt Mr Ms Mu Nr Nv Pd Qb) Jq(aA Jm Lu Mw Nb Ni Nr Nu) Nv(aA Il Jm Jr Mf Ne Ng Pb) Mw(Jm Jr Ni Nl Vt) Ng(Cu Ef Ke Uf) Nj(Jt Mp Ni Pz) aA(Il Jr Nd Pz) Dp(Kq Nw Vt) Me(Jm Pz) Nd(Mu Nr) Qe(bA Vt) Jr(Jm Pz) Ou(Im Oa) NonW Mslj IlQm} Ji{Ng(aC Af Aj aM aN As aW Bb BN bV bZ cE cF Ch cN Co CV Cw Cx Db Dc dE dG Dk Dl dN Dp eF gP Ko Oa Qg Qt Qv Rc Rh Ri Sr Tt Ub Ue Ul Um Uo) Pf(AF Al An aO Ar AW Ax Bc bG Bn bQ bU cE cF cG cK cL Cp Cs CV Cx Dp Ef Gl Gp Kj oN Qg Qt Tv Ua Um Up Ut Uv) Uk(Ao Bn De Dk Ed GP Ic Id Jd Jy Kp Lx Md Mk Nd Ni Nj Nk Nr Nv Oh Ou Qg Qm Tn To Tv Ul Us Tj) Ii(Al aM aN Ap aW bF Bg bJ Bn Bo bV bZ cN Cq Ct cV Cx Db DE DG Di dJ Dl Dp Ed Fy Sr Uh) Ms(Fw gW Hc Hf iC iH jD jH jI jT jY Kc Kd Kf Ki Kl Kq Ky Ld lK lM lO oH Or Ph Pi Pj Pk Vv) Et(Af Ax bA Bb Bc Bg BN Cq Cs Cx Dg Ed Ib Iz Kj Oa Us Uv) Oy(Ad Af Aw Ax Bc cT Cu Dd dM Dp Ef gP Jy Tn Uc Uf Uo Ur Uu) Aj(aA bF bJ dF dM Gp Jg Jm Jp Lv Mq Mw Nd Pb Qd Qe) Pb(AF Ar bN bV CT Dd Ed Kp Oa Qg Qv Rb Uo Ur) Ne(aW bJ bN cA cN cT cV dE dJ dR eF gL oE) bA(aC Ao Ba Cs Cw dE Il Jo My Ni Nl Oz) Ct(cT dM Jm Jp Lv Nb Ni Qd) Lj(bF bJ bR cI cT Dd dE dM) Im(aC Co DE Dk Ha Us) cl(bN bR dJ Il Mw Nk Oz) Ur(Bn Dp Il Jm Oa Wm) Cs(Ha Jo Nd Ni Nj) Dd(Lv Nb Nd Ni Qe) Ch(fP Il oE oH) Tj(Il Li Lx Oa) Ni(Ao bN dM) gP(aW Li Oa) oE(bG cH No) Ax(Nd Nj) fN(Ou Ow) lN(Nh nW) BgMy WmjD HaLi MhqC MkTr MtbR NddM JpjO aNbN} Lv{Lx(Hv Hx Ij Ip Iq Ir It Iu Iv Jh Js Ly Lz Ma Mb Mc Mf Mg Mh Mi Mj Ml Mn Mv Mx Na Nf Nm Nn Nr Nv Ny Oi Oz Po Pz Qb Qc) Lj(Hv Hx Ii Ij Iq Ir Iu Iv Jk Jo Js Ly Ma Mb Mc Md Mf Mg Mh Mj Ml Mn Mx My Na Nf Nm Nr Ny Oe Of Og Oi Oz Pg Qb Qc Wm) On(Fr Hv Hx Ih Ij Ip Iq Ir It Iu Iv Jg Js Jt Lz Ma Mb Mc Mf Mj Ml Mn Mp Mx Na Nf Nm No Nr Ny Oi Om Oz Pc Pd Pz Qb Qc) Mt(Hr Hv Hx Ij Jq Ir Iv Jh Ly Lz Ma Mb Mc Mf Mg Mi Mj Ml Mn Mv Na Nm Nn Nr Nv Ny Pz Qb) Qe(Hv Hx Ij Ip Ir Jv Jh Js Ly Ma Mb Mc Mf Mg Mi Ml Mn Mv Mx Nf Nm Nn Nr Nv Ny Oz Pz Qc) aA(Hr Hv Hw Hx Ii Iq It Iu Iv Jh Jk Jo Ly Lz Mb Mc Mg Mi Mj Mk Ml Mv Nf Oe Of Oi Pa) Qd(Hu Hw It Jg Jn Jo Jr Lw Mp Mu Mw Nc Ne Nl Nq Ns Nt Nu Og Pe Po) Jp(Fr Hu Hw Jk Jm Jn Jo Md Mf Mh Mx Nc Nk Of Og Om Pa Pc) Oh(Hq Ik Il Io Jg Jn Jq Jr Lu Ng Nk Ns Nt Nx Om Oy Pe Po) Lh(Hq Hr Hx Ii Il Jo Jr Mq Ni Nx Of) Nh(Jg Jn Jr Jt Ms Nb Ni Nk Nx Pe) Pf(Fr Il Jn Jr Me Nb Nt Nx Om Pa) Fr(Hq Il Jq Jr Me Nj Nt Nx) Mm(Jr Me Ms Mz Nb Ng Ni Pb) Mq(Jg Jn Mr Ng Ns Om Oy Po) Nd(Jg Jn No Om Pe) Po(Mz Ng Ni Oy) Mr(Mz Nx Oy) Et(Ao Ap) Nt(Ms Pb) AdAj MsMw MyOm MzJr IjIm} Et{Aj(dR Ez Fa Fn Fw gL Ha Hb Hf Ic jD Je Jf Ju Jv Kc Kf Ki Kj Ks Ky Kz Ld Ph Ql Qw Qx Qz Rc Rf Rg Rh Rj To Tz Ub Ue Uf Ug Uh Um Uo Ut Uv Vo) Kg(aA Ar Co Cp Ct Cv Dd Iv Iz Js Jt Kf Kk Kx Mh Mq Mz Nb Nf Nj Nk Nr Oi Om Ow Pb Pd Pg Po Qc Qh Qm Qn Qv Rj Rm Ss St Uf Uu Uv) Wm(aC aO bH bN Ct gP Hu Hw Ih Il JD Jh Jk Jm Jt Lz Md Mk Mq Na Nd Ni nW Nx Ny Oe Og Oi oN Pa Pc Pg) Ch(Ap Ar Ax bN Ct eC fP hB iZ Jm Li Mq Mr Nd Nw oE Oh oN Or Oz Pe Qd Qh Ri Sr St tF) Ct(Ap As Bc Dc Ed Id Ij Iv Jr Jy Ke Kq Li Me Ml Mt Mw Nw Oh Ou Qd) Uk(Ao Cs Gl Il Iz Jm Jq Kd Ke Lw Or Oy Oz Qe Us Vt) Jo(An aO Bc Co Cp cT dM Fy Ke Kq Ou Ra Tv Un Us) Oy(Ap Ar As Ax Cp Cu Dc dM Ed Id Kd Oa Tv Un Ur) Ap(cI Cs dM Id Ii Jm Lx Mh Ni Oa Ou Oz Qd) bA(aF Aw bL Dk Gl Jk Jt Mk Mw Ne Pb) Co(cT Im Jy Li Mq Mr Nb Nw Ou Pe) Lj(aO bL bN bR bV Iz Ks Ur Us) cI(aA aC aO Ml Mm My Ni Oz Pf) Ms(aO bL dM Kj Kl Oa Qu Vt) Oa(Iz Jy Oi Ou Oz Ur Us) Pf(aC bL De Hc Kl Qu) Ii(Ax Cu Kd Vt) Cs(aA Ih Ni) Ed(Gl Mm Vt) Ao(Nb Nw) Ax(Jt Mm) Ng(nW Vq) TjLx NooE MmVt IzJy} Im{Ni(Hv Hx Ip Iq Ir Iv Jh Jm Js Ly Lz Ma Mc Md Mg Mj Mk Ml Mn Mv Na Nf Nk Nm Nq Nr Nv Ny Of Oi Pz Qb Qc) Nd(Hv Hw Ih Ij Io Ir It Iu Jk Jo Js Mh Mx Nf Nq Ns Nu Nv Oi Oy Pg Qc) Lh(Hu It Iu Jg Jn Jq Jt Mf Mg Mh Mv Nc Nu Nv Ny Oi Om Pa Pd Pg Po) Ms(Hu Hw Io Jn Jo Ly Mf Mw Na Ne Nl No Nq Ns Nv Oe Og Pa Pd Pg) On(Ih Ik Io Jn Li Lw Mb Mf Mr Mu Mv Mz Nb Nc Ne Nk Nt Nv Oh Pe) Mt(Hu Hv Iq Iu Jt Mf Mh Mi Mm Mp Nb Nc Ne Nq Nu Om Pa Pc Po) Qd(Hq Ih Il It Li Lx Me Mr Nj Nk Nx Oe Og Om Pf) Fr(Hu Hw Ih Jr Lw Lx Mf Mr Mw Mz Ne Nl Nt Pf) Mq(Hr Ih Ii Jn Jr Lw Me Mm Nb Nk Nl Oe Pc Pe) Nh(Hw Io It Jn Jt Mi Mp Nb Nl Nt Oy Pc Po) Qe(Il Jk Jp Li Lw Mm Mz Nt Oe Om Oy Pe Qb) Lx(Hw Ih Mh Mz Nj Nk Ns Nt Oe Og Pe Pg) Ng(Ad Ba Jr Me Mp Mv Mz Nb Oh Pc Po Wm) Pf(Ih Il Mr Mz Nj Nk Nt Nx Og Pa) Lu(Jr Me Nj Nk Ns Nt Oc Om Oy) Mr(Hw Hx Jp Me Mm Nj Nk Og) Nt(Jp Jq Li Me Oe Og Pb) Lj(Jp Jq Me Mm Nk Nx Om) Il(Jp Jq Li Me Pe) Nx(Jp Li Mz Og Pe) Hq(Jq Mz Pe Po) Nk(Li Pe) Jq(Li Og) Om(Og Pb) AjKq LwMe MzPb HwPe IkJp} Ng{Kq(Af Al An Ao Ap As bA Bb Bg Bn Bo cI Co Cp Cq Cs Ct Cu Cv Cw Cx Db Dc Dd Dk Dl Ed Ef Fn Fr Ha Hq Ic Ih Ip Iq Ir It Iu Jg Jk Jn Jq Js Ju Jv Kj Kk Kp Lw Mm Ms Mt Mv Ni Nk Nu Om On Or Oy Pd Pe Po Pz Qb Qd Qg Qh Ql Qn Qt Qv Ra Ri St Tn Tr Tv Ub Ue Um Un Us Tj) Pf(aA aE aF aG AJ aK aL Ao aR AS aU aX aY aZ bG bH bJ bM bN bO bP bQ bW bX bZ cB cC cG cH cI cL cN Co Cq cR cS Ct cW cY dB Dc dD dG dI DK dL Fb Fw Fy gP Jd Jp Kk Mq Nt Ql Qt Qv Rb Rf Rh St Tn Um Us) Fr(Hq Hw Ir It Iv Jo Js Lu Mb Mf Mg Mp Mx My Nr Ns Nu Ny Oy Pd Pe Qc) Qe(Ad Jt Ke Lu Lw Me Mg Mr Mv Nb Nj Pb Pc Wm) Ke(Ad Dp Ef gP Hx Jg Jp Oa Pb Qm Tr Uk Uu) Lh(Ii Jn Jq Jr Lw Mz Nb Nj Nl Oy Pc) Lx(Ad Ba Hu Jh Jt Li Me Pe Uf Wm) Om(Il Md Me Mm Mr Mz Ne Nl Nu Nx) Mt(Ad Ik Jh Jr Lw Me Mm Pb Pc) Li(Jh Lu Me Mm Mu Pb Qd Wm) Ba(Ct Id Ij On Sr St) Ad(Jp On Uh) Qd(aA bA Ik) Ij(Bc Vt) Il(Un Xa) Sr(Nw Uf) Jp(Cp Ni) qC(Nm Nw) WmJq HaPe NooE OnUf} On{Lj(Ip It Iu Jg Jh Jm Js Li Ly Ma Mc Mg Mh Mi Mj Mn Mp Mu Mx Na Nm Nn Nu Ny Oh Om Oz Pd Pe Pg Po Pz Qb Qc Qd Wm) Ni(Hx Ih Ij Io Jn Jp Jt Lh Lw Mf Mg Mk Mm Mr Mu Mv Mx Mz Nb Nt Nu Oi Pa Pc Pd Pe) Me(Ik Io Jh Jn Jq Lu Lw Mf Mg Mh Mk Mm Mu Mv Mz Nb Nc Ne Nq Nt Nv Nx) Nh(Fr Hr Ih Il Jn Jp Lw Mg Mr Mt Nb Nl Nq Nv Oh Oi Pa Pe Po) Mw(aA Fr Hq Hr Jp Jr Lh Lu Mb Md Mz Nb Nk Nt Og Om Pa Po) Mq(Il Io Jn Lw Mb Mf Mh Mk Mz Nb Nc Ne Nk Nl Oh Pg) Ns(Hu Hw Ik Jo Lu Mb Mh Nb Ne Nl Nq Nu Of Og Qd) Pb(Fr Hw Il Jk Mf Mx Mz Nb Nc Nt Nx Of Oh Pd Po) aA(Hq Hu Ii Ik Il Jq Mb Md Mz Nx Oe Of Og Oh Qd) Mt(Hq Hu Jq Jr Md Mv Nj Nq Oe Of Pf Qd Qe) Nj(Hq Hu Jo Jq Jr Li Lx Mh Mk Oe Pf Qd) Ii(Hu Jn Mb Mr Ne Nl Nq Nt Og Oh Pe) Og(Hq Io Jq Jr Li Lu Lx Ne Nl Nq) Jk(Fr Jq Jr Lu Mh Mr Nl Pe) Qe(Hw Ih Il Io Lu Nk Pf) Jq(Hq Li Lx Mb Of Pf) Pf(Ct Mk Nq Oe Of) Lx(Md Nq Oe Of) Mk(Hu Li Qd) Hq(Jr Po Qd) Oe(Li Qd) AjMs IkOf} Qe{Ms(Hr Hv Hw Iq It Iu Jh Jk Js Lj Ly Ma Mb Mf Mi Ml Mv Mx Na Nc Nf Ns Nv Oe Oi Pa Pd Pg Qb Qd Wm) Mt(Fr Hr Hu Hw Ik Iq Iu Jn Jp Jr Li Lu Md Mm Mz Nb Nc Nt Nx Oh Om Pa Pc Pe) Mq(Il Iq It Jg Jk Jn Jo Jr Lw Me Mm Mr My Nb Ne Nl Nq Oe Oh Om Pc Qb) Nd(Hx Jh Js Ly Lz Mb Mc Md Mf Mg Mk Ml Mn Mv Nj Nm Nr Ny Of Pg Pz Qc) Lh(Ik Iq Li Lu Lw Lx Mb Md Me Mm Mz Nb Ne Nl Nq Nv Nx Oe Pa Pg Qb) Jq(Hw Io Iq Jg Jk Jp Lj Me Mm Mr Mz Nb Ne Nl Nq Ns Oe Pa Pc Qb) Nh(Hq Il Io It Jg Jk Jr Lj Lw Mm Nb Ns Nt Oe Oh Pc Pe Qb) Ni(Hv Ij Ip Ir Iv Jh Js Ly Mc Mg Mj Ml Mv Nm Nr Ny) Nk(Ik Jr Lj Mr Nt Nx Og Pb Pe) Oy(Ik Jh Jp Mu Nt Nx Pc Pd Po) Me(Hq Jp Mm Nx Om Pf) Nj(Li Lx Ne Om Pb Pf) Fr(Ii Ik Lj Nl Ns) Pb(Jg Jp Lu Lw Mz) Li(Il Jk Lu Og) Om(Il Lj Md Ns) Aj(BA Pf) Lx(Ih Mh My) Nx(Hq Ih Oe) Ct(Ba Pf) Jg(Jk Og) aA(Ir Iv) NtOe MrHq NeNl IkJp OgPf} Lh{Ms(Hv Ih Ij Ip Iq Ir It Iv Jh Jk Ly Lz Ma Mb Mc Md Mg Mh Mi Mj Mk Ml Mn Mv Nf Nm Nr Nv Ny Of Oi Oz Pa Pd Pg Pz Qc) Nd(Hu Hw Ih Il Io Ip Ir It Iu Jt Lu Ly Ma Me Mg Ml Mn Mr Mu Mx Na Nc Nj Nl Nn Nr Nt Nu Nv Oi Oz Pd Pe Pz Qc) Mt(Hu Hw Ih Jp Lw Mb Mg Mm Mz Nb Nk Nl Nv Nx Ny Oe Oh Oi Pa Pc Pg) Lj(Hw Il Jg Jq Lw Lx Mb Me Mh Mz Nb Nc Nl Ns Nt Om Pc Pf Qd) Oy(Hq Hw Hx Ii Ij Jh Ma Mb Me Mp Mr Nk Nn Nq Nu Nv Pe Pg Qb) Nh(Hw Il It Jg Jn Lu Lw Me Mw Nb Nl Nv Nx Ny Pc Pg Po) aA(Hq Hr Ik Il Jm Md Mf Mh Mk Nb Nt Of Pc) Lx(Hx Jk Jo Jq Md Mc Mw Nk Nq Ns Pa Qd) Pb(Hu Hw Il Jq Lw Me Mz Nb Nc Pc Pe) Li(Hr Hx Il Jk Me Mq Nj Nk Ns Of) Qd(Hq Il Jo Mq My Nj Pf) Ni(Jp My Nc Nl Oh) Pf(Hr Hx Mq Of Pa) My(Ik Mq Nx) Ii(Jp Nx) FrJk MdJq MqHr MwJg NkNl} aA{Lj(Hr Ii Iq Ir It Iu Jk Js Jt Ly Mc Mi Mj Mk Ml Mx Na Nf No Ny Of Og Oi Oz Pe Qb Qc) Li(Hu

Figure 1 Continued

Hv Hw Hx Ih Ip Jk Jm Jn Jp Lz Ma Mb Md Mk Mn Mv Nb Ne Nl Nu Oe Og Om Pc Pd) Po(Hr Hu Hw Ih Ii Ik Jg Jk Jm Jn Mb Md Mk Mn Nb Nc Ne Nl Nu Oe Og Om Pc) Mt(Hu Ik Il Ip Jp Mh Mn Mr Nc Nk Nt Om Pc) Qd(Fr Jg Jq Jr Mf Mh Nk Ns Nt Oh Om Oy) Nx(Jq Jr Mm Mz Nd Nh Ni Oh Pb) Pf(Hq Ik Jp Mc Mm Ns Nt Oh Om) Ms(Ik Jn Jr Mm Nh Nr Nv) Mq(Il Jg Mf Mn Ns Pc) Mz(Ik Jq Jr Lw Mm Nt) Nd(Ij Jg Jn Jr No) Nh(Fr Jp Jr Mm Om) Oh(Ik Jq Me Nj Pb) Lw(Ik Jp Jr Nt) Mm(Ik Me Ni) Om(Md My Ns) Nt(Jq Pb) Nj(Fr Jp) AdAj NooN LxIv IkJq} Mt{Qd(Fr Hq Ih Ii Ik Io Jk Jr Li Lj Lu Lw Lx Mr My Ne Nh Nj Nx Oe Og Oi Pc Pf) Ms(Hr Hx Ii Iq It Iu Iv Jk Ly Lz Ma Mb Mc Md Mg Mj Mk Ml Mn Mv Nl Nr Of) Lj(Hq Ik Il Io Jg Jr Jt Lx Mz Nb Ne Nj Nt Nx Oe Pa Pc Pe Pf) Ni(Fr Jn Lw Me Mp Mz Nc Nd Nl Ns Nt Nx Om Oy Pc) Mq(Hu Jn Jr Lw My Nj Nk Nt Nx Og Pc Pe) Jq(Fr Jp Jr Me Mr Nt Oh Oy) Pb(Jp Jr Jt Mz Nd Nh Nt Nx) My(Jg Jh Jp Li Mr Om) Lx(Mr Nh Ns Pe Pg) Nd(Jt Lw Mm Mp Mz) Pf(Aj Ct Mr Ns Pa) Nh(Fr Li Mr Ne) Me(Fr Mm Mr) Jp(Nj Ns Oy) Li(Hq Nk Nq) PoHq NsJr} Lx{Ms(Hv Ih Ij Ip Ir Jh Jm Js Lj Lz Mb Ml Mv Mx My Na Nc Nf Nm Nq Nv Oe Og Oz Pd Pg Po Pz Qh Wm) Mq(Hr Hu Hw Ih Ii Ik Jg Jr Li Lw Md Nb Ne Nl Nq Oe Og Oh Pa Pc Pe) Nh(Hw Jn Jr Jt Li Lj Lu Lw Mm Nb Nd Nx Oe Og Oh Om Pa Pc Pf) Nd(Hv Hw Ij Jr Md Mi Mu Na Nb Ne Nk No Ns Nx Oz Pd) Ni(Fr Jm Jn Jt Lu Lw Mu My Mz Ns Om Pa) Oy(Jm Jn Jo Jr Lw Mm Ne Nk Nl Nu Pc) Pb(Li Mz Nj Nt Nx Om Qd) Jq(Hq Ik Nj Nt Qd) Me(Fr Jp Mr) Nj(Nk Qd Tj) Hq(Ik Nx Qd) My(Fr Jh) Nk(Nc Qd) EdFi} Pf{Oy(aF aM Ar aW Bb bV cF Ch cI cK cM dB Dd dH dN Ed Fa Fb Fn Gp Ib Jd Je Ju Jv Kg Ki Kx Ky Li Nx Oa OH oN Ow Ph Qg Qh Qm Qu Qv Rf Rg Ub Ud Uf Ug Uv) Ct(As bR Cu Dc dJ dM Lz Mw Nk Om Oz Qd Un) Pb(Aj bS dM Id Iz Jp Kd Nx Pe Qd Un) Aj(BA dJ dM Ij Nk Nw Un Vt) Mq(Jp Ms Mz Ni Ns) Nh(Fr Jp Mz Ne Qd) Ke(Ch Co Iz oN Oz) Nd(Li Mm Mr Mz) Vt(Ii Jo Uk Tj) Wm(Hq Lj Qd) Ch(Jp Kq) Ms(Jp Mz) Ni(Nj Oh) Oz(bS Ur) dM(bL bR) CoKq EdFi TjNw MkOr HqJy} Li{Ni(Hu Ih Ii Io Jg Jo Jt Lj Lz Mb Md Mf Mi Mp Mu Mw Nb Nf Nk Nn Oe Of Pa Pd Po Qb Qc) Nd(Hq Hw Ij Jg Jr Mu Nb Nh Nn No Ns Nt Nx Og Oi Oz Pa Po) Mq(Hr Hw Jp Lw Me Mz Nk Nq Nt Nx Og Qd) Nh(Hq Jp Lw Mm Mr Nl Ns Og Qd) Ms(Fr Ik Lw Me Mr Mu Nk Oh) Jq(Hq Ik Lu Me Nj Nt Oy) Pb(Fr Ik Lu Mr Nt) jT(rS vA vT wB wQ) vS(bB dB gP oN Tr) Me(Jp Lw Mm) Nk(Nc Ne Nj) Oy(Jg Mr) gP(uU uY) nW(wD yD) AdAj NwqC} Nw{Ij(Ip Ir Iu Iv Ly Mc Mg Mi Mj Mn Mp Mx Nf Nm Nn Nx Om Pb) CtbA NcNk OmPb} Lj{Ni(Ik Mu Nc Nt Oh Pb) Mc(Jg Jp Mm Om) Mq(Lu Mz Nj Nk) Wm(Jp Lw) Nh(Jg Mm) Jq(Ik Nt) qC(Lw Mz) LuJp HqOm JgOy} Jp{Mq(Lu Me Nt Oh Oy) Nh(Jr Mr Nc Ns Pb) Ni(Jr Oh Pb Po) NjNk IkJq} Nh{Pb(Mq Mr Om Po) Po(Ni Nk) Oh(Ne Ni) MqMz JgOy} Mq{Jq(Nt Oh Pb) Oh(Ni Ns) Pb(Nt Po)} Il{DrKj MzqC NiWf IvWc XaKg OmOy} Vt{oE(bN nW) DbqZ WmbA MeqD} Oy{Jg(Ni Oh) Om(Nt Oh) WmMr} Ba{Ct(aC Ad Jq)} Wm{TiSt LwbA} Ni{Nj(Oh Po)} qZ{DbHc KoOu} nW{AxwP PjwD} ChMzqC IbTruI Unconstrained panels with 2 analytes, where 1.0E-8 >= 'model p-value' > 0. Contains 595 panels of 193,455 total panels evaluated. : Et(aA Aj Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ji(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Nw(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Is(aA Fp Fr Hq Hr Hu Hv Hw Hx Ih Ii Ik Il Im In Io Iq It Iu Jg Jj Jk Jl Jm Jn Jo Jp Jq Jr Lh Li Lj Lu Lv Lw Lx Ma Mb Md Me Mf Mh Mk Mm Mq Mr Ms Mt Mu My Mz Nb Nc Nd Ne Ng Nh Ni Nj Nk Nl No Nq Ns Nt Nu Nx Oe Of Og Oh Oi Ok Om On Oy Pa Pb Pc Pd Pe Pf Po Qa Qb Qd Qe) Ok(aA Fp Fr Hq Hw Ii Ik Im In Io Ij Jl Jo Jq Jr Lh Li Lj Lu Lv Lx Me Mh Mq Mr Ms Mt My Nb Nc Nd Ne Ng Nh Ni Nj Nl Ns Oe Og Oh On Oy Pb Pc Pf Po Qa Qd Qe) Fp(aA Fr Im In Jg Jj Jl Jp Jq Lh Lv Lx Mm Mq Mt Nh Ni Om On Qa Qd Qe) Jj(Ik Im Jl Lh Li Lv Lx Mt Nt Nx Oh On Po Qa Qd Qe) Lv(aA Im Jl Jp Li Lj Lx Mt On Qa Qd Qe) Nd(Fr Im Jl Jp Lh On Qa Qe) In(Im Jl Li Lx Mt On Qa Qe) Ms(Jl Lh Lx Mt On Qa Qe) aA(Im Li Lj Lx Po Qa Qe) Ni(Im Li On Qa Qe) On(Lj My Ng Oy) Mt(Im Jl Qe) Ng(Jg Kq) Im(Jl Lh) LxJl MqQa Unconstrained panels with 2 analytes, where 1.0E-7 >= 'model p-value' > 1.0E-8. Contains 386 panels of 193,455 total panels evaluated. : Ok(Hr Hu Hv Hx Ih Ij Il Ip Iq Ir It Iu Iv Jg Jh Jk Jm Jn Jp Js Jt Lw Ly Lz Ma Mb Mc Md Mf Mg Mi Mj Mk Ml Mm Mn Mp Mu Mv Mw Mx Mz Na Nf Nk Nm Nn No Nq Nr Nt Nu Nv Nx Ny Of Oi Om Oz Pa Pd Pe Pg Pz Qb Qc) Qa(Fr Hq Hw Ih Ik Il Im Jg Jl Jp Jq Lh Li Lu Lw Lx Me Mm Mr Mt Mz Nb Ne Ng Nh Nj Nk Nt Nx Og Om On Oy Pb Pf Qb] Is(Aj aN Ct Ij Ip Ir Iv Jh Js Jt Ly Lz Mc Mg Mi Mj Ml Mn Mp Mv Mw Mx Na Nf Nm Nn Nr Nv Ny Oz Pg Pz Qc) Jl(aA Jp Jq Lh Li Lj Me Mq Mz Ng Nh Ni Nj Nk Ns Nt Nx Og Oh Om On Oy Pb Pf Qd Qe) On(aA Hq Ii Im Jk Jq Jr Li Lx Me Mh Mq Mt Mw Nh Nj Nl Ns Oe Of Og Pb Pf Qd Qe) Fp(Hq Jn Jt Li Lu Lw Me Mp Mr Ms Mu Mw Mz Nb Nd Nk Nt Nx Oh Pb Pc Pe Pf) Qe(Fr Im Jp Jq Li Lx Me Mq Mr Ng Nh Nj Nk Nt Nx Og Om Pb Pf) Ji(aC Af Aj Ao Ax bA bN eI Co Cs Ct Dd dM gP gW Uk Ur Us Tj) Mt(aA Jp Jq Jr Lh Li Lj Lx Me Mq Mr Nd Ng Ni Pb Pe Pf Qd) Im(Fr Jp Jq Li Lu Lx Me Mq Mr Ms Mz Ng Nh Nt Nx Pe Pf Qd) Lv(Fr Jg Lh Mm Mq Mz Nh Nt Oh Om Pf Po) Lx(Jq Lh Me Mq Mr Nd Ng Nh Ni Oy Pb Qd) Jj(Fr Jg Jp Jq Lj Mq Nh Nv Om Pf) Lh(aA In Li Lj Ng Nh Oy Pb Pf Qd) Et(Ap bA Ch cI Cs Ct Kg Oa Uk) aA(Fr Mq Nh Nt Nx Oh Om Pf Qd) In(Lj Mq Nt Om Po Qd Un Vt) Fr(Lj Mq Ng Nh Oy Qd) Li(Jq Me Mq Ms Nd Nh) Qd(Mq Ms Nd Nh Ni) Mq(Jp Lj Pf) Om(Lj Ms Ng) Aj(Ad Kq) Pf(Ct Wm) oE(No Vt) NgKe NhJp NwqC Unconstrained panels with 2 analytes, where 1.0E-6 >= 'model p-value' > 1.0E-7. Contains 1,021 panels of 193,455 total panels evaluated. : Ji(AD aE aF aG aH aI aJ aK AL aM AN aO AP aQ AR AS aU aV AW aX aY aZ Ba BB BC bE bF BG bH bI bJ bL bM Bn BO bP bQ bR bS bU bV bW bX bZ cA cB cC cD cE cF cG CH cJ cK cL cM cN cO CP CQ cR cS cT CU CV CW CX cY cZ dA DB DC dD DE dF DG dH DI dJ DK

Figure 1 Continued

DL dN Dp dR eC Ed EF Fa Fb Fn Fy GL Gp Ha Hc Hf Ib IC Id Iz JD JE JF jO jP Ju Jv Jy Kg Kj Kk Ko Kp Kq lK lN nW Oa oE oN Ou Ow qC Qg Qh Ql Qm Qn Qt Qu Qv Qw Qx Qy Qz Ra Rb Rc Rf Rg Rh Ri Rj Rm Sr Ss St Tn To Tr Tt Tv Tz Ua Ub Uc Ud Ue Uf Ug Uh Ul Um Un Uo Up Ut Uu Uv Vo Vp Vt) Qa(Aj bA Ct Hr Hu Hv Hx Ii Ij Io Ip Iq Ir It Iu Iv Jh Jk Jm Jn Jo Jr Js Jt Lj Ly Lz Ma Mb Mc Md Mf Mg Mh Mi Mj Mk Ml Mn Mp Mu Mv Mw Mx My Na Nc Ne Nf Nl Nm Nn No Nq Nr Ns Nu Nv Ny Oe Of Oh Oi Oz Pa Pc Pd Pe Pg Po Pz Qc Qd Qe Uk) Fp(Hr Hu Hv Hw Hx Ih Ii Ij Ik Il Io Ip Iq Ir It Iu Iv Jh Jk Jm Jo Jr Js Lj Ly Lz Ma Mb Mc Md Mf Mg Mh Mi Mj Mk Ml Mn Mv Mx My Na Nc Ne Nf Ng Nj Nl Nm Nn No Nq Nr Ns Nu Nv Ny Oe Of Og Oi Oy Oz Pa Pd Pg Po Pz Qb Qc) On(Fr Hr Hu Hv Hw Hx Ih Ij Ik Il Io Ip Iq Ir Iu Iv Jg Jh Jm Jn Jo Jp Js Jt Lh Lu Lw Ma Mb Md Mf Mg Mi Mj Mk Ml Mm Mr Mu Mv Mx Mz Na Nb Nc Ne Nf Nk No Nq Nt Nu Nv Nx Oh Oi Om Pa Pc Pd Pe Pg Po Pz Qc) Qe(Aj bA Hq Hr Hu Hv Hw Hx Ih Ii Ik Il Io Ip Iq It Iu Jg Jk Jm Jn Jo Jr Jt Lj Lu Lw Ly Ma Mb Mf Mh Mi Mm Mp Mu Mw Mx My Mz Na Nb Nc Ne Nl No Nq Ns Nu Oe Oh Oi Oy Pa Pc Pd Pe Pg Po Qb Qd) Jl(Fr Hq Hr Hu Hv Hw Hx Ih Ii Ik Il Io Ip Iq Jg Jk Jn Jo Jr Jt Lu Lw Ma Mb Mf Mh Mk Mm Mp Mr Mu Mw Mx My Na Nb Nc Ne Nl Nm No Nq Nu Oe Of Oi Pa Pc Pd Pe Po) Mt(Fr Hu Hv Hw Ik Il Io Ip Jg Jn Jo Js Jt Lu Lw Mb Mf Mh Mi Mm Mp Mu Mw Mx My Mz Na Nb Ne Nf Nh Nj Nk Nl No Ns Nt Nu Nx Oe Og Oh Oi Om Oy Pa Pc Pd Po) Im(Hq Hu Hv Hw Ih Ik Il Io Iq Jg Jk Jn Jo Jr Jt Lj Lw Ly Mb Mf Mh Mi Mm Mp Mu Mx Na Nb Nc Ne Nj Nk Nl No Ns Nu Oe Og Oh Om Oy Pa Pb Pc Pd Pg Po) Lx(Fr Hq Hu Hv Hw Ik Il Jg Jn Jo Jp Jr Jt Lt Lj Lu Lw Mb Mf Mm Mu Mx My Mz Nb Nc Ne Nj Nk Nl Ns Nt Nu Nx Oe Og Oh Om Pa Pc Pe Pf Tj) Li(Fr Hq Ik Il Jn Jp Jr Lu Lw Mm Mr Mz Nb Ne Ng Nj Nk Nl Ns Nt Nx Og Oh Om Oy Pb Pe Pf Qd rS sC tR uP uU uV vS vT wQ xA) Lh(Fr Hq Hr Hx Ii Ik Il Jg Jn Jp Jq Jr Lw Mb Md Me Mk Mm Mq Mw My Mz Nb Nc Ne Ni Nj Nl Nt Nx Of Og Oh Po) Pf(Aj bA bL bR bS cA Ch CO dM Dr In Jp Jq Ke Mz Nd Nh Ni Nt Om Oy Pb Qd Uk Un Ur Vt Tj) Lv(Hu Ij Ik In Jn Jq Jr Js Jt Lw Mp Mr Ms Mu Mw Nb Nd Ni Nl No Nr Nu Nv Nx Pb Pe Qb) Qd(Aj Ik Il Jg Jp Jq Jr Lj Lu Me Mm Mr Mz Nb Ne Ng Nj Nl Nt Nx Og Oh Om Pb Pc Pe Po) Et(aC An AO Ar Ax Bg bV Co Dc Dg Dl dM Ed Id Iz Kd Ke Kj Or Ou Ur Us Uu Vt) Jj(aA Cu Ij Jm Jn Jr Js Jt Ke Kq Mw Mz Nr Oa Pz Qb Un Vt Wm) aA(Ij Ik Il In Jg Jn Jp Jq Jr Lw Mf Mm Ms Mz Nd Ni Nj Nr) Ke(Aj Cp Ct gW Ib In Lj Ms Oa oE oN Oy Oz Pb Uk) Fr(Ik In Jq Jr Me Ms Mz Ni Nj Nl Nt Nx Oh Pb) Jp(Ik In Jq Jr Lj Me Mr Ms Ng Ni Nj Nl Po) Nh(In Jg Jq Lj Mq Mr Mz Oh Om Pe Po) In(Fy Id Ik Jg Jq Kq Mr Nx Oa Oh) Is(aC bR Ch dM iB iC jK jV Uk Ur) Lj(Ik Jg Jq Mm Mu Nd Ni Nt Nx Ou) Mq(Jg Jq Mz Nd Nt Nx Oh Om Po) No(eC nW oH oN pF qC qD) Ms(Jg Jq Nt Oh Po) Nd(Mr Oh Om Pe Po) Nw(fN hO oE qD Wm) Ni(Jg Oh Om Po) Ct(BA Kq) Ng(Ad Ba Uf) Oy(Jg Kq Om) Wm(bA Jq) Mz(jK qC) Pb(Om Po) qZ(dB Ou) ChKq NtJq UrVt VqoE aCbA

Unconstrained panels with 2 analytes, where 1.0E-5 >= 'model p-value' > 1.0E-6. Contains 1,877 panels of 193,455 total panels evaluated. :
Et(AD AF aG aH aJ aK AL aM aN aR As aU AW aX Ba Bb BC bH bl bL bM BN BO bP bQ bR bS bW bZ cA cE cF cG cH cK cL cN cO CP CQ cR cT CU CV CW Cx cY dA Db DD DE dF dH Dl dJ Dk dN Dp Ef Ez Fa Fb Fn Fw Fy Gl GP Ha Hb Hc Hf Ib Ic Jd Je Jf Ju Jv Jy Kc Kf Ki Kk Kl Kn Ko Kp Kq Kr Ks Kx Kz Ld nW oE oN Ow pF Ph Pi Pk Qh Ql Qm Qn Qt Qu Qv Qw Qx Qy Qz Ra Rc Rf Rh Ri Rj Rm Sr Ss St To Tv Tz Ua Ub Uc Ud Ue Uf Ug Uh Ul Um Un Uo Up Ut Uv Vo Vp Vv Tj) Li(Hr Hu Hv Hw Hx Ih Ii Ij Io Ip Iq Ir It Iu Iv Jg Jh Jk Jm Jo Js Jt Ke Lj Ly Lz Ma Mb Mc Md Mf Mg Mh Mi Mj Mk Ml Mn Mp Mu Mv Mw Mx My Na Nc Nf Nm Nn No Nq Nr Nu Nv Ny Oe Of Oi Oz Pa Pc Pd Pg Po pS Pz Qb QC rN rO rP rQ rR rT rU rV rW sK sM sO tO tS tU uG uI uL uM uN uO uR uT uW uX uY uZ vA vB vC vH vI vO vP vQ vU vV vW wB wC wD wE wF wG wH wJ wK wL wP yD yH yJ yK yL zA zG zH zI yE tM tL Wm) Is(AD aF aG al aJ aK Al aM An AO aQ Ar AS aU aV aW aX aZ bA bB BC bF bG bH bL bM BN bP bQ bS bU bV bW bZ cA cC cE cF cG cH cI cJ cK cL cM cN CO CQ cR Cs cT cU CV cW cY cZ Dc DD DE dF dG dH DI dJ Dk dL dN hA hR hW Id Iz jD jE jF jG jH jI jL jM jO jP jQ jR jT jU jY Ke Kg Kj lK lL lM lN lO oE Ou Qg qT qU Qv qW qX qY rA rB rC rX Ua Uh Ul Un Us Vt Wm Tj) Pf(aC AD aF al aJ aM AN AO aQ Ar As aV aW Ax aY bB Bc bF bM bN bQ bU bV bW bZ cC cE cF cG cH cI cK cL cM cQ cR Cs cT CU CV Cw dA Dc dE dH dI dJ dL dN Dp Ed Ef Fr Gd GP Ha Hb Hq Id Ik Iz Jg Jn Jr Jt Jy Kd Kg Kj Kk Kn Ko Kp Kq Ky Lj Lu Lw Me Mm Mr Ms Mu Mw Nb Ne Ng Nj Nl Nx Oa oE Oh oN Or Ou Pa Pe Pj Po Qg Qm Qv Qw Rg Sr St Tv Ua Uh UI Us Wb Wc Xa) Ke(Ao Ap Aw Ax Bb Bc Bn Ch cI Co Cs De Dk Dp eC Ed fN Fp GP Hc hL Hq Hx Id iH Ii Il Im Iz JD Ji Jk Jl JM Jo jQ jR Kg Kj Kk lM Lw Lx Md Mk Mw My Nb Nd Ne Nv NW OH Om Or Ou Ow Pa pF Pg pY QA qC Qd Qe Qm Qt qX To Tr Tt Uh Ur Us Ut Vt Wm Tj) Nw(aC AD aF al AJ aM AN Ao As aW Ax bA BB bH bJ bL bM bN bR bS bV bW cA cF Ch cI cK cN CO cQ Cs CT CU cV Cw Dc dE dF dJ Dk dL dM dN Dp Ed eT eZ fY gP gW hL hP Id Jd JE IN Oa oN Or Ou pY qA qB Rh rS Sr Ss Tv Uk Ul Un Ur Us Vt Tj) Qd(bA Ct Hq Hr Hu Hv Hw Hx Ih Ii Ij lo Ip Iq Ir It Iu Iv Jh Jk Jm Jn Jo Js Jt Lw Ly Lz Ma Mb Mc Md Mf Mg Mh Mi Mj Mk Ml Mn Mp Mu Mv Mw Mx My Na Nc Nf Nk Nm Nn No Nq Nr Ns Nu Nv Ny OE Of Oi Oy Oz Pa Pd Pg Pz Qb QC Uk Vt Wm) Ji(eD EZ fN fP Fw hA HB hC hF hG hO hP iA iB iH iJ iO iP iZ jG jH jI jK jL jM jQ jR jT jU jV jY Kc Kd Kf Ki Kl Kn kQ KR KS Kx Ky Kz Ld 1L lM lO nY oF oH oK Or pF Ph Pi Pj Pk qD qT qU qW qX qY rA vS Vv Ti Th tF) Lv(Hq Hr Hv Hw Hx Ih Ii Il Io Ip Iq Ir It Iu Iv Jh Jk Jm Jo Lu Ly Lz Ma Mb Mc Md Me Mf Mg Mh Mi Mj Mk Ml Mn Mv Mx My Na Nc Ne Nf Ng Nj Nk Nm Nn Nq Ns Ny Oe Of Og Oi Oy Oz Pa Pc Pd Pg Pz Qc) Lh(Hu Hv Hw Ih Ij Io Ip Iq Ir It Iu Iv Jh Jk Jm Jo Js Jt Lu Ly Lz Ma Mc Mf Mg Mh Mi Mj Ml Mn Mp Mr Mu Mv Mx Na Nf Nk Nm Nn No Nq Nr Ns Nu Nv Ny Oe Oi Om Oz Pa Pc Pd Pe Pg Pz Qb Qc) Lx(bR bS CO Fi Hr Hx Ih Ii Ij Io Ip Iq Ir It Iu Iv Jh Jk Jm Js Ly Lz Ma Mc Md Mg Mh Mi Mj Mk Ml Mn Mp Mv Mw Na Nf Nm Nn No Nr Ny Of Oi oN Oz Pd Pg Po Pz Qb Qc Uk Vt Wm) Jj(Ad Ar Ax BA Bc Cs Dc Dp Fa Fb Fy Hu Id Ii Il Ip Ir Jk Jo Kn Ko Kp Mg Mj Mm Mp Mr Mu Mx Nb Nd Ne Ni Nj Nl Nm Nn No Nu Ny oE Ou Pd Pe Pg Pj Qc Qh Qm Rm Sr St Tr Uc Uf Uh) Mz(eD hA hR hV hW hX iB iC Ik In jD jE jF JG jH jI jL jM jO JP JQ JR jT jU jV jY Lj lK lL lM lN lO Mr Ms Nd Nt Oh Om Po qD qX qY rC vS) Im(Aj Ct Dr Hr Hx Ii Ij Ip Ir It Iu Iv Jh Jm Js Lz Ma Mc Md Mg Mj Mk Ml Mn Mv Mw My Nf Nm Nn Nq Nr Nv Ny Of Oi Ou Oz Pz Qb Qc Uk Ur Vt Ye Wm) aA(Hu Ih Ip Ir Jm Jo Js Jt Lu Ma Mb Me Mg Mh Mj Ml Mn Mp Mr Mu Mw Mx Na Nb Nc Ne Ng Nk Nl Nm Nn No Ns Nu Nv Ny Og Pb Pc Pd Pe Pg Pz Qb Qc) Lj(bA bF bR bV bW cE dF dM dN Hu Jh Jo Jr Jt Jy Kq Lu Lw Me Mp Mr Ms Mw Nb Ne Nj Nk Nl Nv oE Oh Pb Pc Pe Po qC Uf Uh Un Vt We Wm) Mt(Aj bR Ct Hq Hr Hx Ih Ii Ij Iq Ir It Iu Iv Jh Jk Jm Ly Lz Ma Mc Md Mg Mj Mk Ml Mn Mv Nc Nm Nn Nq Nr Nv Ny Of Oz Pg Pz Qb Qc Ur Vt) No(aC bS cA eT eZ fN fP hB hC hF hG hL hO hP iA iH iJ iO iP iZ kQ kR kS Mq Nd Nh nY oF oK pY qA qB qH Tt uM vS Wm Tj Th tF) Mq(Hu Ij Ik Ir Jm Jn Jr Js Jt Lu Lw Me Mi Mm Mp Mr Ms Mu Mw Nb Nc Ne Ng Ni Nj Nl Nn Nr Ns Nu Nv Og Pb Pc Pd Pe Qb Vt) Jp(Aj Ct Fr Hu Hv Hw Il Io Jn Jo Jt Lu Lw Mb Mf Mh Mm Mu Mx Nb Nc Ne Nl Nq Ns Nu Nx Og Oh Om Oy Pb Pc Pd Pe Wm) Fr(Hq Hu Hv Hw Ih Il Ir Jg Jk Jn Js Jt Lw Mb Mf Mm Mr Mw Mx My Na Nb Nc Ne Nq Ns Nu Of Og Om Pe Po Qb) Qe(CT Id Ij Ir Iv Jh Js Lz Mc Md Mg Mj Mk Ml Mn Mv Nf Nm Nn Nr Nv Ny Of Ou Oz Pz Qc Uk Ur Vt Wm Th) Jl(Aj Ct Ij Ir It Iu Iv Jh Jm Js Ly Lz Mc Md Mg Mi Mj Ml Mn Mv Nf Nn Nr Nv Ny Oz Pg Pz Qb Qc Ur Vt) Nt(Jg Jn Jr Jt Lu Lw Me Mm Mp Mr Mu Mw Nb Nd Ng Nh Ni Nk Ns Nx Oe Og Oh Om Pb Pc Pe Po) In(Ad Ar Ax Cs Cu dN Fa Ij Jn Jr Js Jt Kd Kn Ko Mm Mu Mw Nv Ou Pe Pj Qb Sr St Uf Uh Wm) Om(Ct Hu Ik Il Jq Jr Lu Mb Md Me Mh Mr Mx My Nb Ne Nj Nl Ns Nu Nx Of Og Oh Pe Po) Po(Hq Il Jg Jq Jr Jt Lu Me Mm Mr Nb Ne Ng Nj Nk Nl Nx Og Oh Oy Pe) Nh(Ij Jn Jr Jt Lw Me Mi Mm Mp Ms Mu Mw Nb Ne Ni Nk Nv Nx Ny Pb Pc) Qa(aC bR Ch cI cT Cv dE dM Fi Gp Ou Qg Rt Uh Ur Vt Ye Wm Ti Th) Kq(Ao Bg cI Co De Dk Iz jD Jk Kg Kj Ms My Oa Pz Pb Uk Ur Vt) Vt(bA eC Ed Gp hB Il Ms Mw nW oH Ou Oz pF qC qD St Uk) bA(Ad al Aj Ar Ax bF bM Cs dF dJ fR Oa Oy Pb Pe Uh) On(Aj Ch Ct It Ly Lz Mc Mn Mp Nm Nn Nr Ny Oz Qh) Aj(Ba

Figure 1 Continued

Cu dF Ef Fy Id Ij Jg Ok St Uc Uf Un) Jq(Ik Jg Jr Mm Mr Nd Ne Ni Nj Nl Nx Oh Uk) Oh(Ik Jg Jr Jt Me Mm Mr Nb Nj Nx Pe) Id(Ng oE Ou Oz Pb qC qZ Uk Ur vS) qZ(Db dE Fb Ow Pj qA qB uM vS) Ct(Ad cT Cu dF Fy Ij Ok Pe) Ng(Cu Fy Nv St Tn Tr Uh Un) Nd(Ij Jg Jt Mm Mp Mw Nv) Wm(dF dM hB oE Ok Pe) Ni(Mm Nj Nl Nv Nx Qb) Jg(Jr Me Mr My Og Pe) Un(jD Ms Oz qC Uk Ur) II(Dr Sf Wc Yl Xa) aC(Cu dF dM fR) Lw(Oa Uh Ur) Mr(Ik Mm Nx) Ms(Mp Nv Nx) St(Ye Ti Th) Oa(Ou Ur) Vq(Ed Or) Pe(Ha Nx) qC(Kn Ny) nW(uX wD) DrNq MmJr IjWc KdoE OuUr aFdF cPeP cTfR

Unconstrained panels with 2 analytes, where 1.0E-4 >= 'model p-value' > 1.0E-5. Contains 4,188 panels of 193,455 total panels evaluated. :
Ke(aA aC AD aE AF aG aH al aJ aK AL aM AN aO aQ AR AS aU aV aW aX aY aZ BA bB bC bE bF BG bH bI bJ bL bM bN BO bP bQ bR bS bU bV bW bX bZ cA cB cC cD cE cF cG cH cJ cK cL cM cN cO cP CQ cR cS cT CU CV CW CX cY DB DC DD dE dF DG dH DI dJ dK DL dM dN dR eD EF eT EZ Fa Fb Fn fP Fr Fw FY GL HA HB hC HF hG hO hP Hr Hu HV HW iA iB IC Ih IJ Ik IO IP Iq Ir It Iu Iv iZ JE JF JG JH jI jK jL Jn jO JP Jq Jr Js JT JU JV JY Kc Kd Kf Ki Kl Kn Ko Kp KQ KR KS Kx Ky Kz Ld Lh lK IL lN IO Lu Lv Ly Lz Ma Mb Mc Me Mf Mg Mh Mi Mj Ml Mm Mn Mp Mq Mr Mt Mu Mv Mx Mz Na Nc Nf Nh Ni Nj Nk Nl Nm Nn No Nq Nr Ns Nt Nu Nx NY Oe OF Og Oi OK On Pc Pd Pe Ph Pi Pj Pk Po Pz QB Qc qD Qg Qh Ql Qn Qu Qv Qw Qx Qy QZ RA Rb Rc Rf Rg Rh Ri Rj Rm rO rP rS rW sC sO Sr Ss St Tn Tv Tz Ua Ub Uc Ud Ue Uf Ug uI UI UM UN UO Up Uu UV vA Vo Vp vS vV vW wD wP yD tF) Pf(aE Af aG aH aK AL AP aR aS aU Aw aX aZ Ba Bb bC bE BG bH bI bJ Bn BO bP bX cB cD cJ cN CP Cq cS cW CX cY cZ DB dC DD De dF DG Di DK DI dR Du eC eF Em Eq Ex Ez Fa Fb Fc Fd Fi Fn fP fR Fw Fy Gb Gc Gh GL Gn Gz hB HC Hf Hl Ho Hp Hr Hu Hv Hw Hx Ib Ic IH Ii Ij Il Io Ip Iq Ir It Iu Iv Jd Je Jf Jh Jk Jm Jo Js Ju Jv Kc Kf Ki Kl Kr Ks Kx Kz Ld Lp Lt Ly Lz Ma Mb Mc Md Mf Mg Mh Mi Mj Mk Ml Mn Mp Mv Mx My Na Nc Nf Nk Nm Nn No Nq Nr Ns Nu Nv nW Ny Oe Of Og oH Oi Op Ow Oz Pc Pd pF Pg Ph Pi Pk Ps Pz Qb Qc Qh Ql Qn Qt Qu Qx Qy Qz Ra Rb Rc Rf Rh Ri Rj Rm Rt Ru Rv Rx Ry Rz Sf Sh Si Sj Ss Tn To Tr Tz Ub Uc Ud Ue Uf Ug Um Uo Up Ut Uu Uv Uw Ux Uy Uz Va Vb Vc Vh Vi Vo Vp Vu Vv Vw Vz Wd We Wf Wg Wh Yd Yh Yk Yl Zq Zw Zx Ye Tm Tl Ti Th tF) Nw(aE Af aG aH aK AL aO AP aQ AR aS aU aV Aw aX aY aZ Ba BC bE bF BG bI Bn BO bP bQ bU bX bZ cB cC cD cE cG cH cJ cL cM CP Cq cR cS Cv cW CX cY cZ dA DB dC DD Dc DG dH DI dK DI dR eC eD EF Ez Fa Fb Fn fP Fw Fy GL Gp HA HB HC HF hG iA IB IC iH iJ iO iP Iz jD JF jG jH jI jK jL jM jO jP jQ jR jT JU JV JY Kc Kd Kf Kg Ki Kj Kk Kl Kn Ko Kp KQ KR KS Kx Ky Kz Ld lK IL IM IO nW nY oF oH oK Ow pF Ph Pi Pj Pk QG QH ql Ql Qm Qn qO qP qQ Qt Qu Qv Qw QX Qy Qz Ra Rb Rc Rf Rg Ri Rj Rm rO rT rU rW St Tn To Tr Tt Ua Ub Uc Ud Ue Uf Ug Uh Um Uo Up Us Uu Uv Vo Vp vT Vu Vv Th tF) Qa(AD aE aF aG aH aI aJ aK AL aM AN aO AP aQ AR AS aU aV AW AX aY aZ Ba BB BC bE bF BG bH bI bJ bL bM BN BO bP bQ bS bU bV bW bX bZ cA cB cC cD cE cF cG cH cJ cK cL cM cN CO CP CQ cR CS CT CU cV CW CX cY cZ dA DB DC DD De dF DG dH DI dJ DK DL dN Dp Dr Du eC Ed Eq Fa Fb fR Fy Gd gP Gz Ha Hb Hf Ib Ic Id Iz Jv Jy Kd Kg Ki Kj Kk Kn Ko Kp Kq Kr Ks Ky Ld Lp Oa oE oH Or Ow pF Pj Ps qC Qm Qn Qt Qu Qv Qw Rf Rh Ri Rm Sh Si Sj Sr Ss St Tn To Tt Tv Ua Ub Ue Uf Ug Ul Um Un Uo Up Us Uu Uv Uy Va Vb Vc Vi Vp Vw Vz Wb Wc Wd We Wh Yd YI Zq Zw Tm Tl Xa Tj) Kq(aA Ad AF aK AL aM An Ap AR As AW Ax BA Bb Bc bL BN Bo bR bS bV cA Cp Cq Cs Cu Cv CW Cx cY Db Dc Dd dE Dg Di Dl dM dN Dp Ed Ef Fa Fp Gl GP gW HA Hb Hc Hq Hu hV Hx Ib Ic Id Ih Ii Il Im Is Jd JE jF Jg Jh Jl JM JO JQ jR Jt jU JV Kd Kk Kl Kp Ks Li IN IO Lw Lx Md Mh Mk Mm Mq Mw Nb Nd Ne Ni Nj Nk No Nu Nv Nx Ny oE Of Oh Oi oN Or Ou Ow Pa Pc Pe Pg Pj Qb QC Qd Qe Ql Qm Qt Qu Qv QX Qy Qz Rc Rh Sr Ss St Tn Tv Ua Uh Ul Um Un Uo Us Ut Uu Wc Wm Tj Ti Th) Lj(aC AD aE al AJ aM aN aP aQ aU aX aZ Ba bB BC bL bN bS bU bZ cA cF cG cH cI cJ cK cL cM cN Cp cQ cR cS CT CU CV Cw Dc dD dE dG Dl dJ dL Dp Dr eC eF fP Fy gL GP Ha HB hC Hq Hr Hv Hw Hx Id Ih Ii IJ Il Io Ip Iq Ir It Iu Iv Jk Jm Jn Js Kd Kk Kn Ko Kp Ly Lz Ma Mb Mc Md Mf Mg Mh Mi Mj Mk Ml Mn Mv Mx My Na Nc Nf Ng Nm Nn No Nq Nr Ns Nu Ny Oc OF Og oH Oi Or Oy Oz Pa Pd pF Pg Pj Pz Qb Qc Qm Qv rS Sr Uk Ul Ur uX Vi vS wB Wd Wh wP zA Xa tF) Is(aE Af aH aL AP aR Aw aY Ba Bb bE Bg bI bJ Bn BO bX cB cD CP cS Cu Cw CX dA DB dC Dg dK Dl Dp Dr eC ED Ez Fa Fb Fn fR Fw Fy Gl GP Ha HB Hc Hf hV hX Ib Ic Id Je Jf Ju Jv Jy Kd Ki Kk Kn Ko Kp Kr Ks Kx Ky Kz Ld IX IY Oa oH Or Ow pF Pi Pj Pk qC Qh Ql Qm Qn Qt Qu qV Qw Qx Qy Qz Ra Rb Rc Rf Rg Rh Rj Rj Rm rZ Sr Ss St Tn To Tr Tt Tv Tz Ub Uc Ud Ue Uf Ug Um Uo Up Ut Uu Uv Va Vo Vp Vv Wc Ye Tl Ti Th) qZ(aC AD aG aH Aj aL aM aN aO aQ aR aW Ax aZ Bb BC bJ bL bM bQ bR bS bW bZ cA cB cC CH cL cO Cs CT cU cY dD dJ DL dM fN fP Gl Hc hG hL hP Ib iH iJ iO iP Ji Kn Ko Kr Kz Mz oE oN Or pS qC qO qP rO rQ rS rU rW sC sM sO tO tR tS tU uG ul uL uN u0 uV uW uX uY uZ vA vB vC vH vI vO vV wB wC wD wE wF wG wH wJ wK wL wP wQ yD yK yL zA zH tL xA Wm tF) Vt(aA AJ Ax Ba bF bH bL bN bR bV bZ Cs CT cV dF Di dM dN Dp cZ Fa fN Fp Fr Fy gP hC hF hG hO hP iA Ic Id iH IJ IO iP iZ jK Jm Jn Jo Jp Jq Jy Kg Kj Kk Kn Ko Kp kQ kR kS Lh Li Lv Lw Ma Mc Mm Mr Mt Nb Nd Ne Ng Ni Nk No Nq Nr NY Oa oF Oh OK ON Or Ow Oy Pb Pe Pg pY Qc Qg Qh Qm Qv qX Rc Rf Rh Ri Sr Tr Uf Ug Uh Ul Un Us vS Tk Wn Wm tF) bA(aA aD AF aJ Al aM AN Ao Ap aQ As aU AW Ba BB Bc Bg bL BN Bo bR bS bU bW bZ cA cH cC cE cF cG CH cI cJ cK cN Co Cp Cq cR cS CU CV Cw Cx cZ Db Dc DD DE DG Di Dk DL dM dN Dr dX eP Ex Fa Fp Fr Fw Gd Gf gW Hq Hu Id Im In Jk JI Jm Jp Jq Jr Jy Li Lx Mq Mt Mw Ng No Oz Pg Po Pz Qb Qc Qm Rf St Uf Uk Un Ur) Qe(aC AD Af al aM AN Ao Ap aQ Ar As aU AW AX Ba BB Bc bF Bg bH bL BN bR bS bV bW bZ cA cE cF Ch cI cK cN CO Cp CQ cR Cs Cu CV Cw Cx Db Dc DD dE dF DI dJ Dk dM dN Dp Dr Fy GP Iz Jy Kd Kg Kj Kk Kn Ko Kp Oa oE oH Or Ow Pj qC Qg Qm Qv Rh Sr Tv Ua Uf Uh Ul Um Un Us Va We Ye Tj Ti) Im(aC AD aI AN Ar As Ax bB bF bR bS bV bW cA Ch cl Cs Cu CV Cw Dc dD dE dF dJ dL dM dN Eq Fs Fi Fy Gc Gh Gn GP Gz Hb HI Id Iz Jy Kd Kg Ki Kj Kk Kn Ko Kp Ks Ld Lp Oa oE Op Or Ow Pi Pj Qv Sf Sh Si Sj Sr Tv Ua Uf Uh Ul Un Us Uw Uz Va Vi Vq Vz Wb Wc We Wg Yg Yh Yi Yk Yl Tm Tl Xa Ti Th) Un(Ax bN Ch cl Cs CT Dp eC Ed Fy GP gW Hx Ib Id Ih Ii Ij Il Iz jH jK Jl JM JO Jp Jq jV Jy Kd Kg Kj Kk Ko Kp Li IN IO Lv Lw Lx Ma Mm Mq Mw Nb Nd Ne Ni Nk No Nr Oa oE Oh Oi Or Ou Ow Oy Pb Pe pY Qc QD Qg Qh Qm Qv qX Rf Rh Sr St Uf Ug Uh Ul Um Uo Us Uu Wm Tj) Et(aE al aP aQ aS aV aY aZ bB bE bF bG bJ bU bX cB cC cD cJ cM cS cX cZ dB dC dG dK dL DR eC eF fP gL gW hB hC hF hG iA iB iH iJ iO iP iZ jD jI jO jP kQ kR kS Ky IN nY oF oH oK Pj qC Qg qY Rh Rg rX rZ Tn Tr TT uV Vq vS Vu vV Ti Th tF) No(Aj aU bR bV CT cV dE dJ dM dN eF Fr fY gP Gz iB iC Id Ik In Jg jK Jp Jq Jr IN Me Mr Ms Ne Ni Nj Nl Nt Nx Oa Oh Om Or Ou Po qG ql qO qP qQ qT qU qV qX qY rA rB rS rU rW sC tR Uf Uh Uk uO Ur uV uY uZ vA vB vV wB wE wH wL wP wQ yD yL zA xA Ti) Id(aA Ar Ax Bc bZ Ch Cs CT Cx dM Dp eC Ed eZ Fa fN Fp Fy Gp gW HB Ij Il jK Jl Jm Jp Jy Kj Kk Kp Li Lv Lw Lx Mm Mq Ms Mt Mw Nb Nd Ne Ni Nr nW Oa OH Oi Ok On Or Oy Pe pF Pj Qc QD Qh Qm Qv qX rC Rh Rj St Uf Uh uM wP tF) Jp(Ar Ax Ch Cs ED Hq Hr Hx Ih Ii Ij Ip Iq Ir It Iu Iv Iz jD Jg Jh JK Jm jO jR Js IN Ly Lz Ma Mc Md Mg Mi Mj Mk Ml Mn Mp Mv Mw My Na Nf Nk Nm Nn Nr Nv Ny Oa Oe Of Oi Oz Pa Pg Pz Qb Qc qX rA rB rX Sr Uk Ur) Pe(aC aD aF al AJ aM aN aQ aU aW aX bB bJ bL bN bQ bR bS bU bV bW cA cF cG Ch cI cK cM CO cQ cT CV dE dF dH dJ dM dN GP Hu Ik Jn Jq Jr Mm Mp Ms Mu Mw Mz Nb Ne Ni Nj Nl Nv oE Ou Oy Pb qC Uh Uk Ur Tj) Po(Fi Hr Hu Hv Hw Hx Ih Ii Ij Ik Io Ip Iq Ir It Iu Iv Jh Jk Jm Jn Jo Js Lw Ly Lz Ma Mb Mc Md Mf Mg Mh Mi Mj Mk Ml Mn Mp Mu Mv Mw Mx My Na Nc Nf Nm Nn Nq Nr Ns Nu Nv Ny Oe Of Oi Oz Pa Pc Pd Pg Pz Qb Qc Tj) Jj(Al An Ap As Aw Bb bR bV bZ Cp Cq cT Cv Cw dF Dg Dk Dl dM dN Ed Ef Ez Fw Gp HB Hv Hw Ih In Iv Jy Kd Kf Kk Kl Kr Ks Kx Ky Lu Lw Ma Me Mf Mh Mi Mv Nc Ng Of Or Pb Pc Pi Ql Qt Rf Tn Tv Tz Uk Ul Us Ut Vo) Mq(Aj Ar Ax Cs Ct dE dM dN Dr Fy Hq Hr Hv Hw Hx Ih Ii Il Io Ip Iq It Iu Jh Jk Jo Ly Lz Ma Mb Mc Md Mf Mg Mh Mj Mk

Figure 1 Continued

Ml Mn Mv Mx My Na Nf Nk Nm Nq Ny Oa Oe Of Oi Ou Oy Oz Pa Pg Pj Pz Qc Uh Uk We Wm) Nt(Hq Hr Hu Hv Hw Hx Ih Ii Ij Ik Il Io Ip Iq Ir It Iu Iv Jh Jk Jm Jo Js Ly Lz Ma Mb Mc Md Mf Mg Mh Mi Mj Mk Ml Mn Mv Mx My Na Nc Ne Nf Nj Nl Nm Nn Nq Nr Nu Nv Ny oE Of Oi Oy Oz Pa Pd Pg Pz Qb Qc) Nh(Hq Hr Hu Hv Hw Hx Ih Ii Ik Il Io Ip Iq Ir It Iu Iv Jh Jk Jm Jo Js Lu Ly Lz Ma Mb Mc Md Mf Mg Mh Mj Mk Ml Mn Mv Mx My Na Nc Nd Nf Ng Nj Nl Nm Nn Nq Nr Ns Nu Oe Of Og Oi Oy Oz Pa Pd Pg Pz Qb Qc) In(As Ba Bc bV Cp Cv Cw Dc dF dG dJ dL dM Dp Dr Fb Hu Ih Il Ip Ir Iv Jm Jo Jy Kf Kk Kp Kr Kx Lw Me Mj Mp Mx Nb Nc Nd Ne Ni Nj Nl Nn Nr Nu Ny Or Pd Pg Pi Pk Qh Ql Qm Rf Rm Tv Uc Ul Us Vq We Xa) Qd(aC AD aI AN Ar As Ax bB Bc bF bL bN bR bS bV cA Ch cI cK cN Cs cT Cu CV Cw Dc dD dE dF Di dM dN Dp GP iB iC Iz jE jK Jy Kd Kj lN Oa oH Ou qD Qv qY Rh Sr Ua Uf Uh Ul Ur Us Tj) Om(Aj Hq Hr Hv Hw Hx Ih Ii Ij Io Ip Iq Ir It Iu Iv Jg Jh Jk Jm Jn Jo Js Jt Lw Ly Lz Ma Mc Mf Mg Mi Mj Mk Ml Mm Mn Mp Mu Mv Mw Na Nc Nf Nk Nm Nn Nq Nr Nv Ny Oe Oi Oz Pa Pc Pd Pg Pz Qb Qc) Il(Du Eq Fc Fd Fi Gb Gh Gz Hl Ho Hp Jg Jq Lp Lt Nd Ni Nx Oh Op Ou Ps Rt Ru Rv Rx Ry Rz Sh Si Sj Uh Uk Ur Uw Uy Uz Va Vb Vc Vh Vi Vz Wb Wd We Wg Wh Yd Yh Yi Yk Zq Zw Zx Ye Tm Tl) Jq(Aj Ar Ax cI Cs Ct dM Ed Hu Ij Ip Ir Iv Jm Jn Js Jt Lu Lw Ma Mb Md Me Mf Mh Mj Mp Mu Mv Mw Mx Nb Nc Ng Nn Nr Ns Nu Nv Ny Oa oE Og Ou Pa Pb Pc Pd Pg Pz Qb Qc St Uf Uh Ur) Lx(aC AD Aj aN aV bL bQ bU bV bW cA cC cF cG Ch cI cK cL Cs CT Cv dA Dc dE dF dH dI dJ dM dN Dp Dr Fc Fy Gp Jy Kd Kk Kn Oa oE Or Ou Sr Uf Uh Ul Ur Us Wc Yk) Fr(aC Aj CT Dr Hr Hx Ii Ij Io Ip Iq It Iu Iv Jh Jm Jo Lu Ly Lz Ma Mc Md Mg Mh Mi Mj Mk Ml Mn Mp Mu Mv Nf Nk Nm Nn Nr Nv Ny Oe Oi Oz Pa Pc Pd Pg Pz Qc) Jg(Ct Hq Hu Hv Hw Ih Ij Ik Io Ip Ir Iv Jm Jn Jo Js Jt Lu Lw Mb Mf Mh Mi Mm Mp Mu Mw Mx Na Nb Nc Ne Nf Nj Nk Nl Nq Nr Ns Nu Nx Oe Of Oi Pa Pb Pc Pd Pg Qb) Oh(Hq Hu Hv Hw Ij Ip Ir Iv Jn Jo Kd Lu Lw Ma Mb Mf Mh Mi Mp Mu Mw Mx Na Nc Ne Ng Nk Nl Nm Ns Nu Nv Oe Og Ou Oy Pb Pc Pd Pg Pz Uh Uk Wm) Mz(eT eZ fN fY hL hO hP Hu Jn Jt Lu Lw Me Mm Mu Mx Nb Nc Ne Ni Nj Nl Nu Nv Nx pY qA qB qT qU qV qW rA rB rW rX rY rZ uX wB wP) Oa(bF bV cE cT dF dM dN Dr eC Fc Fi Fy Gp HB Ji Jy Kn Ko Lp Mw Nd Ng Ni Nk oE oH Ok On pF Pj qC Sr Uf Uh Uk We Ye Xa Ti Th) aA(aC Ad Ar Ax bF bM bR Cs Cu dF Hq Hr Hv Hw Hx Ii Io Iq It Iu Iv Jh Jk Ly Lz Mc Md Mi Mk Mv My Nf Nq Oe Of Oi Oy Oz Pa Uh) Ou(Aj Ar Ax Bc Ch Cs Ct Dr Fa Fp Fy Ij Jl Kd Kk Kn Ko Li Ms Mw Nd Ng Oy Oz Pb Pj qC qX Rf Sr St Uf Uh Uk uX Vq wD Wm Ti) dF(AD aJ aM AN aO Ar aU Ax Bb Bc bL bM bR bS bU bW cA cC cF CH cI cK cL cO Cs cT Dc dE dH dJ dM dN Fp Ng) Nx(Hu Hv Hw Ij Ik Jm Jn Jr Js Jt Lu Lw Me Mh Mi Mm Mp Mu Mw Mx Na Nb Nc Nd Ne Ng Nj Nl Nr Ns Nu Nv Og Pb Pc Qb) Wm(aC aI aJ bB bF bR bV bW bZ cE cN cT cV dD dL dN Jl Lh Lv Lw Mr Mt Mw Nb oH On pF qC rS Uh Ur uX We Xa Ti) Li(Aj Ct dM eZ fN fP gP hL hP Jy oE oH oN pF pY qA qB qD qG qH qI qO qP qQ qX Rg Sr tN tQ tT tV tX Uh Uk Ur) Uh(Ad Aj As Ax Ch Cs Ct Cu Cw Dc Ed Fp Fy Jl Jr Kd Kn Lv Mr Ms Mw Ni oE Or Oz Ra Sr Tv Uk Up Ur Us) Jl(aC aD AN Ar Ax bR bS bV cA Ch cI Cs cT dE dM dN Gp Gz Hb Iz Ko oE Pj qC Uf Uk Us Tj) Lw(Ed eZ Fa fN Fy Gp Hb hO hP iB iC Ik jQ Jr Kk Ko Kp IK lN Mr Nd qC qD Qm qY St Uf Uk) oE(Ar Bc cH Dr Ex Fy Gz hB kC Kk Kn Ko Lh mM Mr Mt Mw nD nI Nm Nr Nu Pj Sr St Uy We) Mr(Hu Jn Jr Jt Me Mf Mp Ms Mu Mw Nb Nc Ne Ni Nj Nl Nu Nv Oy Pb Pc Qb Ur) Ji(eT Ex fR fY hL hR hV hW hX pY qA qB qI qV rB rC rX rZ Va Vu vV Wc wP yL) Ni(Ar Ax Cs Hu Ih Ij Ik Jn Jr Js Jt Mp Mu Mw Mx Nc Ne Nr Pg St We Xa) Fp(aD bB bF bR bV bW cE cF cT dE dM dN Dr fR Uf Ur Uw Vi We Wh) Cs(aC aU Ba Bc bF cE cG cT dJ dM Gp Lv Mt Ok qC Ur vS wP zA) Uk(Ad Ax Cu Fy Ij Kd Kn Ko Lh Mw Nm Ok On Pj Sr St Tr Uf Ul) Ur(Ad Ax Bc Cu Dc Fy Ij Kd Kn Ko Lh Rm Sr St Tv Uf Us) Mt(Ar Ax bQ bS bU cA cF Ch cK cO Cv Dc dH dM oN Wc) aC(Ad aJ Ar Ax Ba Bc bF bW bZ cE cG cS cT Dc dG dN) St(Bc Ch Ct dM Dr Eq Ms Nk Sh Sr Tv Va Vi Wc Yk) Ng(Ar Ax Bg Cp Dg Ef Fa Jt Kn Ko Mu Sr Uc Xa) dM(Ad aI Ar aU Ax bF bR Cu dJ gW Ij Lv Qm rC) Mm(Hu Ij Ik Jn Js Jt Me Ms Mu Nb Ne Nj Nl) Jr(Ik Jt Me Mp Ms Mu Mw Nb Nd Ne Nj Nl Nv) Dr(aJ Ba cT fR Gp Jn Jy Lv Or Oz Pb Qb) Fy(bW Ch Dp Ed Gz Jo Kg Kj Or Oy Oz Pb) Ms(Ij Ik Jn Js Jt Kn Mu Mw Qb Uf) Nd(Aa Jn Js Mi Mu Nb Ny Pd Pg Qb) cT(Ad aI Aj Ar Ax Bc Cu Dc eP) Jt(Ik Lu Mb Mu Nb Ne Nj Nl Pb) Nv(Ik Me Ne Nj Nl Ns Og Oy Pb) Aj(Bc Dg Ko Lh Lv Sr Tn Tr) Ax(aU bF cE Gp Jy Lv qC vS) Ct(Ef Kn Lh Lv Mw Pg Sr Uf) aJ(Ad aI Ar bF bR cE dE dJ) qC(Dc Ih Ko Kp Nm Rm wD) Mw(Ik Kd Kk Ne Nj Nl) Kn(eC eD Oy Pb qD rB) Uf(Ed Kd Kj Oz qX Sr) Ik(Jn Js Mp Pb Qb) On(Ao Co Rt Wc Tl) Or(Pj We Zq Tl Xa) bF(aM Dc dJ dL dN) Ar(cE dJ Gp Lv) Jn(Me Nb Va Vq) Ny(fN hL qA qD) Vi(Kg Oz Pb Qb) Pj(Fa qX Sr wD) Ch(hB Ij Ok) Nj(Mp Mu Nb) Nl(Mp Nb Nk) We(Ld Pb Qb) Xa(Jy Oz Pb) fR(bR gP Ij) wD(dE Ri tF) vS(Ko Kp Sr) Ad(Gp Kj) Fa(Fi Th) Me(Js Mu) Oy(Tr Vs) Oz(Uw Wh) dJ(Cu dN) DcGp FiNr LvbV MyJh NcNk QbYe WcJy KdeC KgOk KowP OwuX bBqX bRdG cPdX dBrN hBoN

Unconstrained panels with 2 analytes, where 1.0E-3 >= 'model p-value' > 1.0E-4. Contains 11,496 panels of 193,455 total panels evaluated. :
Id(aC AD aE AF aI aJ aK Al aM AN Ao AP aQ aR AS aU aV AW aX aZ Ba BB bC bE bF BG bH bI bJ bL bM BN BO bP bQ bR bS bU bV bW bX cA cC cD cE cF cG cH cI cJ cK cL cM cN CO CP CQ cR cS CU CV CW cX cY cZ DB Dc DD DE dF DG dH DI dJ DK DL dN dR eD EF eT Ez Fb Fn fP Fr Fw fY GL gP HA HC HF hG hL hO hP Hq Hr Hu HV Hw Hx iA IB IC IH Ii iJ Ik IO IP Iq Ir It Iu Iv IZ JD JE JF JG JH jI Jk jL jM Jn JO JQ JR Js JT JU JV Kc Kd Kf Kg Ki Kl Kn Ko kQ KR KS Kx Ky Kz Ld Lh lL lM IN Lu Ly Lz Ma Mb Mc Md Me Mf Mg Mh Mi Mj Mk Ml Mn Mp Mr Mu Mv Mx My Mz Na Nc Nf Nh Nj Nk Nl Nm Nn Nq Ns Nt Nu Nv Nx NY Oe OF Og oK Om oN Ow Pa Pc Pd Pg Ph Pi Pk Po pS pY Pz qA QB QG qH qI Ql Qn qO qP qQ QT QU qV QW Qx QY Qz RA RB Rc Rf Rg Ri Rm rN rO rP rQ rR rS rT rU rV rW sC sK sM sO Sr Ss Tn To TR Tt Tv Tz Ua Ub Uc Ud Ue UG uI UL Um uN UO UP uR Us UT UU UV uW uX uY uZ vA vB vC vH vJ VO VP vQ vT vU vV vW wB wC wD wE wF wG wH wJ wK wL wQ yD yH yJ yK yL zA zG zH zI yE tM tL xA Wm Tj) Un(aA aC AD aE AF aG aH aI aJ aK AL aM AN AO aP aQ aR AS aU aV AW aX aY aZ Ba BB BC bE bF BG bH bI bJ bL bM Bn BO bP bQ bR bS bU bV bW bX bZ cA cB cC cD cE cF cG cH cI cK cL cM cN CO CP CQ cR cS CU CV CW CX cY cZ dA DB DC DD DE dF DG dH DI dJ DK DL dM dN dR eD EF eT EZ Fa Fb FN Fp Fr Fw fY GL Gz HA HB Hc Hf hL hO hP Hq HR Hu HV HW hX iA iB IC IK Ik Io Ip Iq Ir It Iu Iv Jd JE JF JG Jh jI Jk jL Jn jP jQ JR Js JT JU Jv jY Kc Kf Ki Kl Kn kQ Kr Ks Kx Ky Kz Ld Lh lK lL lM Lu Ly Lz Mb Mc Md Me Mf Mg Mh Mi Mj Mk Ml Mn Mp Mr Mt Mu Mv Mx My Mz Na Nc Nf Nh Nj Nl Nm Nn Nq Ns Nt Nu Nv nW Nx Ny Oe Of Og oH Ok Om ON Pa Pc Pd pF Pg Ph Pi Pj Pk Po Pz qA QB Ql Qn Qt QU qV Qw Qx QY QZ RA RB RC Rg Ri Rj Rm Ss Tn To Tr Tt Tv Tz Ua Ub Uc Ud Ue Up Ut Uv Va Vo Vp Vq vS Vv Wc Xa Ti Th tF) Fy(aA aC AD AF aI aJ aK AL aM AN AO aP AR AS aU AW AX aZ BA BB BC bF Bg bH bI bJ bL bM BN Bo bP bQ bR bS bU bV bZ cA cD cE cF cG cH cI cK cL cN CO Cp CQ CS cT CU CV CW CX cY Db Dc Dd DE dF Dg dH Di dJ Dk DL dM dN Dr eC Ef Ex Ez Fa Fb Fn Fp Fr Gl GP Ha HB Hc HF hG Hq Hr Hu Hv Hw Hx Ib Ic Ih Ii Ij Ik Il Io Ip Iq It Iz Jd Je Jf Jg Jh Jk Jl Jm Jn Jp Jq Jr Js Jt Jv Jy Kd Kf Ki Kk Kl Kn Ko Kp Kq Ks Kx Ky Kz Ld Lh Li Lu Lv Ly Lz Ma Mb Mc Md Me Mf Mg Mh Mi Mj Mk Ml Mm Mn Mp Mr Ms Mt Mu Mv MW Mx My Mz Na Nb Nc ND Ne Nf Nh Ni Nj Nk Nl Nm Nn No Nq Nr Ns Nt Nu Nv nW Nx Ny Oe Of Og OH Oi Ok Om ON Ow Pa Pc Pd Pe pF Pg Ph Pi Pj Pk Po Pz Qb Qc Qd Qg Qh Ql Qm Qn Qt Qu Qv qW QX Qy Qz Ra RB Rc Rf Rg Rh Ri Rj Rm Sr Ss St Tn To Tv Tz Ua Ub Uc Ud Ue Uf Ug Ul Um Uo Up Us Ut Uu Uv Vo Vp Vq vS Wc We Xa Wm Tj tF) No(AD aE aF aG aH aI aJ aK aL aM AN AO aP aQ AR AS aV aW AX aY aZ Ba BB BC bE bF bG bH bI bJ bL bM BN Bo bP bQ bR bS bU bV bW bX bZ cB cC cD cE cF cG cH cI cK cL cN CO cP cQ cR CS CU Cv CW cX cY cZ dA dB DC dD dF DG dH DI DK DL Dp DR ED Ex Fa Fb Fi Fn fR Gd Gh gL Gp gW HA Hb Hc hR Hu hV HW hX Ib Ic Ij Il Ip Ir Iz JD JE jF jG jH jl jL jM Jn JO jP jQ jR Js JT jU JV JY Kd Kf Kg Kj Kk Kn Ko Kp Kr Kx Ky Kz Ld lK lL lM lO Lu Lw Mb Mf Mm Mp Mu Mw Mx Mz Nb Nc Ng Ns Nu Nv Op Ow Pb Pc Pd Pe Pg Pi Pj Pk pS Qb Qg Qh Ql Qm Qn Qv qW Qx QZ Ra rC Rf Ri rN rO rP rQ rR rT rV rX

Ne Ng Nj Nk Nl Ns Nu Og Pb Pc Pd qT qU qV qW qX qY rA rB rC) bF(AD aF al Aj AN aO aP As aU bB Bc bL bM Bn bR bS bU bV bW cA
cC cF CH cl cK cL CO Cp Cq cS Ct CV Cw dE dG Dl fR Ml Ng qX) We(Aj aM bR cQ cS Cx Dp Ed Ex Fw Ir Iv Jo Kg Kj Kk Lz Mh Mi Ml
Nb Nc Nd Ng Nk Nl Nq Nr Nu Ow Oy Oz Ps Ql Qx Qz Ra Rm Rt Tz Va Vi Wc Ye) Ok(aC AD aJ An Ao Ap As bL bN bR bS bV bW cA cl Co
Cv Cw Dc dE Dp Ed Gp Iz jD jE jO Kj Kk lN Ow Qh Qm Qv qX rX rZ Tv Ul Us Uu vS Tj) Mm(Ed Hv Hw Ih Il Io Ip Ir Iv Jm Jo Kk Lu Ma
Mb Mf Mh Mi Mj Ml Mp Mv Mx Na Nc Nf Ng Nn Nr Ns Nu Ny Og Oy Pa Pb Pc Pd Pg Pz Qb Qc rX) Jt(Aj Ct Hq Hr Hu Hw Ih Ii Il Io Ip Ir It
Iv Jm Jo Ma Me Mf Mh Mi Mj Mp Mv Mx My Na Nc Nk Nn Nr Ns Nu Ny Oe Og Oy Pc Pd Pg Pz Qb Qc) Nb(aC AD al AJ bB Bc bR bV bW
Ct Cv Dc dE fR Hu Ik Ip Ir Jo Me Mi Mp Ms Mu Mx Nc Ne Nr Nu Ny Pb Pg Pj Pz Qb Wc Tm Tl Ti Th) Nd(bV dG Hu Hv Hw Ih Ik Ip Ir Jm Jo
Kk Ma Me Mh Mj Mn Ms Mv Mx Na Nf Nm Nn Nq Nr Nu Oz Pa Pb Pc Pz Qc Qm Tn Tr Tv Uw Vi Wb Zq) aJ(aD Aj aM An aQ As aU Ba BB
Bc bL bN bS bU bW bZ cA cB cC cF cG cH cJ cK cM Cp Ct CV Cw Dc dD eP Ex gP Ml Ne Ng Nr Vq) fR(Ad Aj aM AN aQ As aU AW Ba
bB Bc Bg bL bM Bo bS bU cB cF Ch cK Cp Cq cS cV Cw cY Db Dc dE dH dJ dR Il Iv Mi Nq Nr Po) Ik(Hu Hv Hw Ih Il Ip Ir Jm Jo Lu Ma Me
Mh Mi Mj Mn Mu Mx Na Nc Ne Nf Ng Nj Nk Nl Nm Nn Nr Ns Nu Ny Og Oy Pa Pc Pd Pg Pz Qc) Nw(Ex hR hV hW hX iZ qT qU qV qW qY
rA rB rC rN rP rQ rR rV sC sK sM tU Tz uG uM uN uT uU uV vB vH vS vV wB wL wP xA Ti) aC(al Al aM An Ao AP As Aw aX BB bC bE
Bg Bn bR bV cF cH cN Cp Cq cR cU CV Cw Dg dH dJ Dk DL Gp Ml Nr Om Po) Dc(Ad al Aj aM aU Ba bB Bc bM bR bW bZ cE cF cG cK
cS Ct cV dE DG dJ dL eC fN Hb hL hV jD jK jM jV Ng Pj qA qD vS) Oz(bV Fc Fd Fi Gb Gh Hl Ho Hp Jg Kk Lp Op Pj Ps Qm Rt Ru Rx Ry
Rz Sf Tr Ux Uz Va Vh Vq Vw Wb Wd Wg Yi Yl Zq Ye Tl Ti) Mu(Hu Hv Hw Ih Il Ip Ir Jv Jm Jo Lu Ma Mb Mf Mh Mi Mp Mx My Nc Ne Nk
Nl Nr Ns Nu Ny Og Oy Pb Pc Pd Pg Pz Qb Qc) Ny(Aj bV Ct eT eZ fY hO hP iB IC jE Jg jl jK Me Ms Ne Nj Nl Nu pY qB qO rN rS rW rZ tT
uM vS vV wP yD) Pb(bV Gn Hl Hu Kf Kk Mp Mx Ne Nj Nl Nr Pd Pg Ps Qb Qm Rt Ry Uw Uz Vh Vq Wd Wg Wh Yg Yi Yk Zq Tl) dG(AD al
Aj An aU BB Bc bL bM bN bS bU cA cB cC cE cF cH cl cK cO Ct dE dH dJ Ml Ng ul) Nr(aD al Aj aN bB bR bV bW Ct Cv dE Gd Kk Lp Me
Ms Nj Op Sh Uy Va Vi vS Wc Wh Ye Ti Th) Qb(Aj bV Ct eP Fi Hu Lu Me Mp Ne Nj Nk Nl Nu Og Uw Uz Va Vw Wb Wc Wd Wg Wh Yi Zq
Tl) cE(AD al Aj aM AN As Bc bL bM bR bW cA cF cH cl cK cL cS Ct dE dJ dL Ml Ng qX) Ad(al An aU Ba Bc bM bW bZ cG Ch cl cS Cv dJ
dL Ed Jo Kg Kk Ms Oy qX rB vS wP) Ml(al bB bN bR bV bW bZ cl cN cV dE dJ eC eP iC Jg pF Pj Ps Uw Vi Wb Wc Wh Zq) Il(Aj Ct Em Ex
Fb Gc Gn Hb Kk lX Me Pj Qm Qv Rf Tv Ux Vj Vq Vw Wf Yg Yj Ti Yf) Pf(eM gW hF hG iA iB iJ iO iP iZ kQ kR kS nY oF oK Tt ul Vj Vq
Vs Yg Yi Yj Yf) Jg(Ch Hr Hx li Iq It Iu Jh Jk Ly Lz Ma Mc Md Mg Mj Mk Mn Mv Nm Nn Pz Qc Uu) Bc(al An aU bL bR bZ cA cF cl cK Ct
dE dJ Dp dR Ed GP Kk Ng oF oH Rf) Aj(al Ap Bg bZ cG Cp dJ Dl Ez Fb Gp Kf Kl Nt Pd Pg Pj Po Pz Qh Uw Vi) Nq(Em Eq Gn Hl Ps Sh Sj
Uw Uy Uz Va Vc Vi Wb Wc Wg Yi Yk Yl Ye Tl Ti) Ng(Ap Aw Bb bV bZ Cw Dk Ez Fb Hu Kf Kk Kl Mp Pj Qh Qm Rf Uw Vi Vq Wd) Ld(bV
Fc Fi Uw Ux Va Vh Vi Vw Wb Wc Wd Wh Yd Yi Yk Yl Zq Ye Tl) Pj(bV Ed iB jD jl jK Kk lO Ms oH pF Qh qU Qv rA Tn Tv Ul Us vS)
Pg(bL hA iB iC jE jl jO jU lN Me Ms Ne Nj Nl qX rA rX rZ) Nm(Kk qG qH ql qO rN sC vA vS vV wB wH wP yL yE tM xA) Nl(Hu Hw Ip Ir Jo
Me Mi Ms Mx Nc Ne Nn Nu Pc Pd Pz) Ql(eP Fi Gd jD jK qX Ru Uw Uy Va Vi Wb Wc Wd Wh Ye) Gp(aM An As Bn Cp Cq Ct Cv Cw dJ eP
Fw Tv Us) Me(Hu Ih Ip Ir Mp Mx Nc Ne Nj Nn Nu Pc Pd Pz) Kr(qX rN rS uT uV vS vV wB wH wP zI yE tM xA) Mp(Hu iB Ir jK jO Lu Mb
Mh Mx Nc Ne Nu qY) Vi(bR cQ Dp Ed Kc Lz Mh Mi Nc Ow Pa Wc Tl) al(aM An As Ba bM bW bZ cF cl cN cS dJ qX) cG(An bL bR bU cA
cF cl cK dJ hA qX ul) Ct(Cp Dg Fb Hu Kf Nt Po Qh Tn Tr Uc) Ed(eP Fi Hb nD Om Tr Uw Wd Wh Zq Ti) Ne(bV Hu Ip Jo Mi Ms Mx Nk Nn
Pc Pz) qX(cJ cU cZ dJ dL Fb qD Qm Tr Tv wB) Wc(Ex Jh Mi Om Pi Po Qx Ra Rm Uw) bB(cF hA jD jG jl jM jV qY rA Rf) bV(Kk Mn Nk
Om Po Qc Qh Qm Rf Vq) bZ(aD An As bM bR cA dE dJ dL nD) vS(cH dL Kf Mj Qh Rm rN Tr Tv Us) Ba(aD An As Ch dJ dL dX cP Ti)
Ms(Hb Hu Ir Jo Mj Mx Nn Nu Pz) Nj(Hu Ip Ir Mi Mx Na Nk Nn Pz) eC(kl Kk Mj nD nl Tv Us Wn) Po(bL bR dE dX eP Fc) Tr(Co Gz Hq Mk
ul uN) lr(Fi Hu Nu oH pF Tv) Om(Ao Ch cl Co Ib Iz) bW(bR dJ Kk Qm Rf rN) wP(cH dJ eD nW Ow Tv) Ye(Of Ow Ps Rm Wh) rN(Db dE Mf
nW Ow) Ch(eF oF Tn wB) Qm(Kk Qv Tv Ul) bR(dL mW nD nl) dJ(An Cp Cv dL) nW(rS tU uT wB) Db(nl uT wB) Ti(Mh Ow Ul) Hu(Mx Nu
Pc) Qh(jV Nk Oy) Kf(sC uM vV) Ps(cQ Ul Vq) Rm(jK Lp Va) Rf(aM cV pF) nD(aZ gL iA) jl(iC lN qY) An(aU dL) Tv(Nk Uo) Qc(Cv lY)
Kg(Uw Yi) Vq(cV Qv) Oy(Cp Tn) dB(tV wB) nl(iA pF) rX(lp qY) rS(Fb Mh) AaLu BoeM ExFi NsNu MxPc UcKj IhqD HbUl WhQx KcUw
KkaM OwcP aUcU cFdL cHpF cPgV eDmH nRlK

Constrained panels with 3 analytes, where 1.0E-10 >= 'model p-value' > 0. Contains 3,297 panels of 36,050,556 total panels evaluated. :
Et{Ng(aA Aj Ar Ax BA Bc cl Cp Cs cT dM Ef Fp Fr Hu Id Ik Il Im In Io Is Jg Ji Jj Jl Jm Jq Jr Jy Ke Kq Lh Li Lj Lu Lv Lx Me Mq Mr Ms Mt
Mu Mv Mw Nb Nc Nd Ne Nh Ni Nj Nl Nt Nw Nx Oa Oh Ok Om On Or Ou Pb Pc Pf Po Qa Qd Qe Uk Wm) Ms(aA Aj Fp Fr Hq Ik Im In Io Is
Jj Jl Jm Jn Jo Jq Jr Lh Li Lj Lu Lv Lx Me Mp Mq Mr Mt Mu Mw Mz Nb Nc Nd Ne Nh Ni Nj Nl Nt Nw Nx Oh Ok On Pb Pc Pe Pf Po Qa Qb
Qd Qe Wm) Oy(aA Fp Fr Hu Ik Il Im In Io Is Jg Ji Jj Jl Jm Jq Jr Lh Li Lj Lu Lv Lx Me Mh Mq Mr Mt Mu Mv Mz Nb Nc Nd Ne Nh Ni Nj Nl Nn
Nt Nw Oh Om On Pc Pd Pe Pf Pg Po Qa Qd Qe Wm) My(aA Fp Fr Hu Ik Im Io Is Jg Jh Ji Jl Jm Jq Jr Lh Li Lj Lx Me Mh Mq Mr Mt Mu
Mv Mw Nb Nc Ne Nh Ni Nj Nl Nq Nt Nw Oh Ok Om On Pc Pe Pf Po Qa Qe Wm) In(aA Aj Fp Ih Ik Im Is Ji Jj Jl Jm Jn Jq Jr Lh Li Lj Lu Lv Lx
Me Mh Mq Mr Mt Mz Nb Nc Nd Ne Nh Ni Nj Nl Nt Nu Nw Nx Oh Ok Pb Pe Pf Po Qa Qb Qd Qe Wm) Jo(aA Fp Hu Hw Ik Il Im Is Ji Jl Jm Jn
Jq Jr Lh Li Lj Lu Lv Lx Me Mf Mh Mq Mr Mt Mu Mz Nb Nc Nd Ne Nh Ni Nj Nl Ns Nt Nw Nx Oh Ok Pb Pe Pf Po Qa Qd Qe) Pb(aA Fp Fr Hu
Ik Im Io Is Ji Jj Jl Jq Jr Lh Li Lj Lu Lv Lx Mb Me Mh Mq Mr Mt Mu Mz Nb Nc Nd Ne Nh Ni Nj Nl Nt Nw Oh Ok On Pe Pf Po Qa Qd Qe)
Jj(aA Fp Ik Il Im Io Is Ji Jl Jm Jq Jr Lh Li Lj Lu Lv Lx Me Mh Mq Mr Mt Nb Nc Nd Ne Nh Ni Nj Nl Nt Nu Nw Nx Oh Pf Po Qa Qd Qe
Wm) Hq(aA Fp Ik Im Is Ji Jl Jm Jq Jr Lh Li Lj Lu Lv Lx Me Mh Mq Mr Mt Mz Nb Nc Ne Nj Nl Nw Oh Pe Pf Po Qa Qd Qe) Im(aA Aj Hw
Ih Ii Il Io Ji Jl Jr Jt Lh Lj Lu Lv Me Mh Mq Mr Mt Nd Nh Ni Nj Nl Nq Ns Nw Oe Og Oh Pf Qd Qe) Lu(Fp Hu Is Ji Jl Jq Jr Li Lj Lv Me Mh Mq
Mt Nc Nd Ne Nh Ni Nj Nl Nq Ns Nw Of Og Oh Pf Qa Qd Qe) Nd(aA Fp Fr Is Ji Jl Jq Jr Lh Li Lj Lv Lx Me Mh Mp Mq Mr Mt Mz Ni Nw Oh
On Pe Pf Qa Qd Qe) Ns(aA Fp Ik Is Ji Jl Jq Jr Lh Li Lj Lv Lx Mh Mq Mr Mt Nb Nc Ne Nl Nw Oh On Pf Qa Qd Qe) Ni(aA Fp Ik Is Ji Jl Jm Jr
Li Lj Lv Lx Me Mh Mq Mr Mt Nc Ne Nh Nj Nl Nw Oh Pf Qa Qd Qe) Nj(aA Io Jl Jq Jr Lh Li Lj Lx Me Mh Mq Mr Mt Nb Nk Nw Oh Pf Qa Qd
Qe) li(Fp Ik Is Ji Jl Jr Lh Li Lj Lv Lx Mq Mr Mt Nt Nw Oh On Po Qa Qd Qe) Is(aA Aj Fp Hr Hw Ih Io Iq Ji Jk Jt Lj Lv Md Me Mg Nh Nq Oe
Of Og) Jl(Aj Hr Hw Io Jk Jr Jt Lj Lv Mb Me Mk Mt Nh Nq Nw Oe Og Oh Pa) Qa(aA Hr Hw Ih Io It Jk Jt Lj Lv Mb Me Mm Nh Nq Nw Oe Og
Qb) Ji(aA Fp Ih Io Jt Lj Md Mg Mm Mw Nh Nq Nv Nx Of Og Om Wm) Lv(aA Fp Io Lr Li Lj Me Mq Mr Mt Nb Nh Nw Oh Pf Qe) Me(aA Jr Li
Lj Lx Mq Mt Nc Nh Nl Nw Oh Pf Qd Qe) Nw(aA Ik Io Jr Lj Md Mq Mw Nh Nl Nv Of Pa Qe) Jq(Ik Io Li Lx Mb Md Mh Mq Mt Nc Nh Nl Pf)
Qe(aA Hw Ih Io Jk Jt Mm Mq Nh Nq Oe Og) Lh(Hr Hw Jt Mb Md Mg Mw Nh Nq Nv Of Og) Lj(aA Aj Ik Io Jt Mq Mt Nh Oe Pa Wm) Io(Jr Li
Lx Mt Nc Nl Oh Pf Qd) aA(Fp Jm Jr Md Mf Mh Mq Nh Nq) Mq(Hw Jr Mt Nh Oh Pf) Nl(Mh Nb Nk Oh Pf) Nq(Li Mt Oh Qd) Lx(Md Of Pa
Pg) Mr(Hw Mb Mk Of) Ik(Mg Mz Of Og) Pf(Aj Ch Co Pa) Mt(Jr Mg Mm) Nb(Nc Ne Qd) Nh(Jr Ne Oh) Jt(Li Nt Qd) Aj(bA Mm) Fp(Md Nk)
Oe(Nt Oh) On(Mw Of) NcNk HwQd} Nw{In(aA Fp Hw Ik Im Is Jj Jl Jm Jo Jq Jr Li Lj Lu Lv Lx Md Me Mq Ms Mt My Nb Nc Nd Ne Ng Nh
Ni Nj Nl Ns Nt Nx Oh Ok Oy Pb Pf Qa Qc) Oy(aA Fp Fr Ik Il Im Io Is Jg Jh Ji Jj Jl Jm Jr Lh Lu Lv Lx Me Mq Mr Mt Mu Mv Nb Nd Nh Ni Nj
Nt Ok On Pb Pc Pe Pf Qa Qe) Jj(aA Fp Ik Im Io Is Jl Jm Jr Lj Lu Lv Md Me Mf Mq Ms Mt My Nb Nd Ne Ng Nh Ni Nj Nl Ns Nt Nx Oh Ok Pb

Figure 1 Continued

Pf Qa Qd Qe) Pb(aA Fp Hw Ik Im Io Is Ji Jl Jo Jq Jr Lh Lj Lu Lv Md Me Mq Mr Ms Mt My Nb Nd Ne Ng Nh Ni Nj Nl Ok Pe Pf Qa Qe) Qa(Hq
Hr Hw Hx Ih Il Ik Im Io It Jk Lu Mb Md Me Ms Mw My Nd Ng Nh Ni Nj Nk Nq Ns Nv Ny Oe Of Og Pa Qb) Ni(aA Fp Ii Ik Im Is Jl Li Lj Lu
Lv Md Me Mq Ms Mt Mw My Nc Nd Ng Nh Nj Nl Ns Nv Of Oh Pf Pg Qe) Is(aA Fp Hq Hw Ih Ii Im Io Jk Lj Lu Lv Md Me Mq Ms Mw My
Nd Ng Nh Nj Nk Nq Ns Nv Of Og Pa) My(aA Fp Fr Ik Im Io Jg Jh Ji Jl Jr Lh Lu Lv Me Mq Mr Mt Nb Nd Nh Nj Nq Ok On Pc Qe) Ng(aA Fp
Fr Ik Im Jg Jl Jm Jr Lh Lu Lv Lx Me Mq Mt Mu Nb Nd Nh Nj Nt Ok Om On Pf Qe) Ii(Fp Hv Hw Ik Im Jl Jm Jo Jq Jr Jt Lh Lj Lu Lv Me Mq
Mt Nh Nj Nt Ok Pf Po Qd Qe) Md(aA Fp Hv Hw Ik Im Io Ji Jl Jq Jr Lh Lu Lv Me Mq Mt Nb Nd Nh Nj Nl Ok On Qe) Jl(Hq Hr Hx Im Jk Lj Lu
Me Mk Ms Mw Nb Nd Nj Nk Ns Nv Of Og Pa Pg Po) Mq(aA Fp Hq Hr Hu Im Lj Lu Lv Me Ms Mw Nd Nh Nj Ns Nv Nx Of Og Pg) Ms(aA Fp
Ik Im Io Jr Lh Lu Lv Me Mt Nd Nh Nj Oh On Pc Qe Wm) Me(aA Fp Hq Hr Im Lj Lu Lv Mt Mw Nd Nh Nj Ns Nv Of Pg) Lu(Fp Hq Im Lj Lv
Mw Nh Nj Ns Nv Of Og Ok Pg Qe) Nd(aA Fp Fr Im Ji Lh Lj Lv Mp Mr Ns Ok Pe Qe) Qe(Hq Ih Io Jk Mw Nj Nk Nq Ns Nv Oe Og Pa) Lj(aA
Hq Ik Io Lv Lz Mt Nh Nj Nk Ns Ok Pa) Im(aA Fp Hq Io Lv Mw Nh Nj Ns Nv Og Pa) Nv(aA Fp Ik Ji Jr Lh Lv Mt Nh Nj Ok) Fp(aA Hq Lv Mw
Nh Nk Ns Ok Pa) Ns(aA Ik Jr Lv Mt Nh Nj Ok) Mw(aA Ik Ji Lh Lv Mt Nh On) Ji(Hr Hx Nx Ny Of Om Pg) Lv(aA Hq Io Nh Of Pg) Ik(Hq Hu
Jk Of Og Pg) aA(Lw Mf Nh Nj Nq) Nk(Nc Nh Nj Nl) Ok(Hq Hr Nj Pa) Lh(Hx Of Pg) Pa(Mt Pf) MrHx NeNh HqPf JnJs} Ji{Oy(aA Fp Fr Ik Il
Im In Io Is Jg Jj Jl Lh Li Lu Lv Lx Mq Mr Mt Mv Nb Nd Ni Ok On Pc Pe Pf Qa Qc Wm) My(aA Fp Fr Ik Il Im In Io Is Jg Jh Jj Jl Jo Li Lu Lv
Lx Mq Mt Nb Nd Nh Ni Nq Ok On Pf Qa Qe Wm) Pb(aA Fp Fr Ii Ik Im In Io Is Jj Jl Jo Li Lj Lu Lx Md Mq Mr Ms Mt Nd Ng Nh Ni Ok Pf Qa
Qe Wm) Ii(aA Fp Fr Il Im In Is Jj Jl Jm Lh Li Lj Lu Lv Lx Mq Mr Ms Mt Nd Ni Ok Pe Pf Qa Qe Wm) Md(aA Fp Fr Ik Im Io Is Jj Jl Jo Li Lj Lu
Lv Lx Mq Ms Mt Nb Nd Nh Ni Ok Pf Qa Qe Wm) Jl(Hq Hr Hw Hx Ih Im In Io Jj Jk Jo Mk Ms Mw Nb Nd Ng Ni Nk Ns Nv Nx Of Og Pa Pg)
Nd(aA Fp Fr Im In Is Jj Jo Jp Li Lj Lu Lx Mq Mt Mw Ng Ni Nk Oh Ok Pf Qa Qe) Ng(aA Ba Fp Fr Il Im In Io Is Jg Jj Li Lu Mq Mt Nb Ni Ok
On Pf Qa Qe Wm) Is(Hq Hr Hw Hx Ih In Io Jj Jk Jo Jq Jt Lj Lu Ms Nh Ni Nk Ns Nv Nx Og) Qa(Hq Hr Hw Ih In Io It Jj Jk Jo Jt Ni Nk Nq Ns
Nv Nx Og Qb) Qe(Hq Hx Ih In Io Jj Jk Jo Jt Mw Ni Nk Nq Ns Nv Nx Og Pa Qb) Im(aA Fp Hq Ih In Io Jj Jo Jq Lj Lu Ms Mt Nh Ni Ns Og)
Wm(gP Hx In Jj Jo Lv Ml Ms Mw Nb Nk Nq Nv Nx Ny Pz) Fp(aA Hq Hr Hx Ih In Jj Jo Lu Mw Ni Nk Ns Nv Og) Lu(Hq In Jj Jo Lj Ms Mw Ni
Ns Nv Nx Of Og Pg) Jj(aA Ik Il In Jm Lj Lv Mq Ms Mt Nh Ni Pf) Fr(Hq Jk Mg Mu Mv Mw Nq Nv Nx Of Om) In(aA Jm Li Lj Me Mq Ms Nb
Nh Ni Pf) Jo(Li Lj Lv Mq Ms Mt Nh Ni Ok Pf) Nx(Ik Li Lv Lx Mq Mt Nh Ni Ok Pf) Lj(aA Hq Ih Io Lv Mt Ni Nk) Ok(Hr Io Jt Mw Ni Of Og
Om) Pf(Hq Ih Ni Ns Og Pa Pe Pg) Mq(Hq Hr Hw Hx Ih Ns) Ms(aA Aj Hq Io Ni Nk) Mw(Ik Jg Li Lx Mt On) Nk(Nc Ne Nh Nj Nl) Li(Hq Ih Ni
Nq Pa) Ns(aA Io Mt Nh) Lx(Of Pa Pg) Mr(Hx Mk Nb) Mt(Ih Io Of) Lv(Hq Io) Nh(Ne Og) Hx(Il Pe) Jk(Il On) aA(Ih Ni) MkPe IkOf IoOg QdJt
JnJs} Jj{Fp(aA Fr Ij Ik Il Im In Ip Is Jg Jl Jm Jn Jo Jp Jq Jt Lh Li Lv Lw Lx Mg Mm Mp Mq Mr Mt Mu Mw Mz Nd Nh Ni Nl Nm Nt Nv Nx Oh
Ok Om On Pb Pe Pf Po Pz Qa Qd Qe) Im(aA Fr Ik In Io Is Jl Jq Jr Lh Li Lj Lu Lv Lx Ly Me Mf Mq Mr Ms Mt Mz Nb Nd Nh Ni Nj Nl Nt Nu
Nx Oh Ok Om On Pd Pe Pf Po Qa Qd Qe) Ok(aA Fr Ik Il In Is Jl Jm Jr Lh Li Lj Lu Lv Lx Me Mq Ms Mt Nb Nc Nd Ne Ng Nh Ni Nj Nl Nt Nx
Oh Pb Pf Po Qa Qd Qe) On(Ik In Is Jl Jm Jr Li Lj Lu Lv Lx Me Mf Mh Mq Ms Mt My Nd Ne Ng Nh Ni Nj Nl Nq Ns Nt Nx Oh Oy Pb Pf Po Qa
Qd Qe) Jl(Ik In Is Jm Jp Jq Lh Li Lj Lu Lv Lx Mb Me Mf Mq Ms Mt Nb Nd Nh Ni Nj Nk Nl Ns Nt Nx Oh Pb Pf Qa Qe) Qe(aA Fr Ik In Is Jg Jq
Jr Lh Li Lu Lv Lx Me Mq Ms Mt Nb Nd Nh Ni Nj Nk Nl Nt Nu Nx Oh Om Pb Pf) Is(Fr Hq Ik In Io Lh Li Lj Lu Lv Lx Me Mq Ms Mt Mz Nb
Nd Nh Ni Nj Nl Nt Nu Nx Oh Pb Pf Po) Qa(Fr Hu Ik In Jg Jq Lh Li Lu Lv Lx Me Mq Ms Mt Mz Nb Nd Nh Ni Nj Nk Nt Nx Oh Om Pb Pf)
Mt(Ik Il Jm Jq Jr Lh Li Lj Lv Lx Me Mq Ms Nd Nh Ni Nt Nx Oh Pf Po Qd) Lh(Ik In Jm Li Lj Lv Lx Mq Ms Nd Nh Ni Nj Nl Nt Nx Oh Pb Pf
Qd) Lv(Ik Jp Li Lj Lx Nh Nt Nx Oh Pf Po Qd) Nx(Li Lj Lx Mq Nh Nt Oh Pf Po Qd) Ik(Fr Jp Li Lj Lx Mz Oh Qd) Nd(Fr Jp Li Lx Oh Po Qd)
Mq(Li Lj Lx Nt Oh Qd) Nh(Li Lx Oh Po Qd) Nt(Li Lj Lx Oh) Li(In Ni) LxMs} Is{Ms(aA Fp Fr Hq Hw Il In Io It Jg Jl Jp Lh Li Lu Lv Lw Lx
Me Mm Mq Mr Mt Mz Nb Nd Nh Ni Nk Nt Nx Oh Ok Om On Oy Pb Pc Pf Qe) Nd(aA Fp Fr Ih Im In It Jl Jo Jp Lh Li Lj Lu Lv Lx Mm Mp
Mq Mr Mt Mz Nb Ne Ng Ni Nk Og Oh Ok On Oy Pb Pe Pf Qe) Ni(aA Fp Fr Hq Hw Il Im In It Jl Jo Jp Lh Li Lj Lu Lv Lx Mm Mq Mt Nc Ng
Nh Nj Nl Og Oh Ok On Oy Pb Pf Qe) In(aA Fp Ik Il Jl Lh Li Lj Lu Lv Lx Me Mq Mr Mt Mz Nb Ng Nh Nj Nl Nq Nt Nu Nx Og Ok Oy Pb Pf Po
Qa Qe) Lv(aA Fp Hq Hw Ii Il Im Io It Jk Jo Li Lj Lu Lx Me Mq Mt My Nb Ng Nh Nk Ns Og Ok Oy Pb Pf) Fp(aA Fr Hq Hr Hw Ih Ii It Jk Jp Lu
Mj Mm Mq Mt Nc Ng Nk Ns Og Ok On Oy Pb Qb) Ok(aA Hq Hr Hw Ih Ii Io Jk Jo Jt Lj Lu Me Mq My Ng Nh Nq Ns Og Oi Oy Pb) Ng(aA Fr
Hu Ik Jg Jl Jp Lh Li Lu Lx Mm Mq Mt Nb Nk Nt Om On Pf) Oy(Fr Jg Jl Lh Li Lu Lx Mq Mt Om On Pc Pf) Ii(Fr Jl Lh Li Lx Mq Mt On Pf)
Pb(Fr Jl Lh Li Lu Lx Mq Mt Pf) Og(Jl Lh Lu Mq Mt Nh On Pf) Jk(Fr Lh Li Lx Mt On Pf) Hq(Fr Li Lx Mq Pf) Nk(Jl Lj Nc Nh) Mq(aA Hw Ns) My(Fr Lh On) Lj(aA Ih Lu) Lx(aA Me) Mt(Ih Me) Lh(Hr Hx) MkJl NeNh} In{Fp(aA Fr Im Jg Jl Jn Jo Jp Jq Jt Lh Li Lv Lw Lx Me Mm Mq Mr Mt Mu Mw Mz Nh Ni Nj Nt Nv Nx Oh Ok Om On Pb Pc Pe Pf Po Qa Qd Qe) Ok(aA Ik Im Jl Jm Jq Jr Lh Li Lj Lu Lv Lx Me Mh Mq Mr Ms Mt Nb Nc Nd Ne Ng Nh Ni Nj Nl Nt Nx Oh On Pb Pc Pf Po Qa Qb Qd Qe) Qa(aA Hu Ik Jl Jq Jr Lh Li Lj Lv Lw Lx Me Mm Mq Mr Ms Mt Mz Nb Nd Ng Nh Ni Nj Nk Nq Nt Nx Oh Om On Pb Pe Pf Qe) Qe(aA Ik Im Jl Jq Jr Lh Li Lv Lw Lx Me Mq Mr Ms Mt Mz Nb Nd Ng Nh Ni Nj Nl Nt Nu Nx Oh Om On Pb Pe Pf) Jl(Ik Im Li Lj Lv Lx Me Ms Mt Nd Nh Nj Nx) Li(aA Im Jq Lh Lv Me Mq Mt Nd Nh Ni Nj) On(Im Lj Me Mq Ms My Nd Ng Nh Nj Oy) Im(aA Lh Lv Mq Mr Mt Nd Nh Nt) Lj(aA Lh Lv Mq Mt Om) Lx(aA Lv Mq Nh) Lh(Mt Nd Nh) Pf(Vt Wm) PoaA MqMt NgJg} Ok{Ms(aA Fp Fr Hq Im Io Jl Jo Jq Jr Lh Lj Lu Lv Lx Me Mq Mt Mu Mz Nb Nd Ng Nh Ni Nn Oh On Oy Pb Pc Pf Qa Qe) Ng(aA Fp Fr Hu Ik Im Jg Jl Jr Lh Li Lu Lv Lx Me Mq Mt Mu Nb Nd Nh Ni On Pb Pf Qa Qe) Fp(aA Fr Hq Hr Hw Ih Ii Im Jl Jo Jq Lu Lv Md Me Mq Nd Ni Nk Ns Oy Pb Pc) Nd(aA Fr Im Jl Jo Lh Lj Lv Lx Mq Pb Qa Qe) Lv(aA Hq Im Jl Jo Lj Lu Nh Oy Pb Qa) Jo(Ik Jl Lh Lu Me Mq Nh Ni Qa Qe) Jl(Ii Im Lu Me Mk Ni Oy Pb) aA(Im Jr Lj Lx Me Mq Pb Qe) Pb(Lj Lu Mq Nh Pf Qa) Oy(Fr Lh Lx On Pf) Ni(Im Lj Qa Qe) Lu(Im Lj) Ii(Qa Qe) MyOn} On{Ng(Fp Fr Hu Ik Im Io Jg Jl Jp Jr Lh Li Lj Lu Lv Lx Me Mk Mq Ms Mt My Nb Nd Nh Ni Nj Nk Nt Nx Oh Om Oy Pb Pf Qa Qd Qe Wm) Oy(Fp Fr Hr Hu Ik Il Im Jg Jl Jm Jr Lh Li Lj Lu Lv Lx Mb Md Me Mq Ms Mt Mz Nb Nd Nh Ni Nj Nx Oh Om Pf Po Qa Qe Wm) Ms(aA Fp Hq Im Io Jk Jl Jr Lj Lv Lx Me Mq Mt My Mz Nd Nh Ni Nk Nq Ns Nx Oh Pb Qa Qe) Fp(aA Hq Ii Jk Jo Lv Md Mk Mw My Nd Ni Nk Nq Ns Oe Og Pb) My(Ik Im Jh Lv Lx Mb Md Me Mq Mt Nd Nh Ni Nj Pb Qe) Nd(Im Jl Lj Lv Mw Pb Qa Qe) Lj(Lv Ni)} Fp{aA(Fr Im Jl Jp Jq Lh Lv Lw Lx Mm Mq Ms Mt Mz Ni Nk Nx Oh Om Pb Pc Qe) Jp(Lv Ms Nd Ng Ni Nk Pb) Fr(Ms Nd Ng Oy Pb) Lv(Im Jl Mm Mt) Ms(Jl Lh Mt Om) Oy(Jg Lh Lx Om) Pb(Jl Lh Mt) NgJg NkJl} Ng{Jg(Fr Ik Im Jl Lh Li Lj Lv Lx Mq Ms Mt Nd Nh Ni Nt Nx Oh Om Pf Po Qa Qd Qe) Fr(Ik Im Nd Qa Qe) Lh(Im Mt) Pf(Ba Wm) QeOm} Nd{Jl(Im Jp Li Lv Lx Ms Mt Qa Qe) Lh(Im Jp Lj Pb Qa Qe) Fr(Im Lj Qa Qe) Qe(aA Jp Lx) aA(Im Lx) LvLi} Ms{Mt(Im Jl Jq Lh Lv Qe) Lh(aA Im Lx Qa Qe) Qe(aA Ni Om) Lx(aA Jl) Im(aA Jl)} Oy{Lh(Fr Im Jg Mt) Lx(Jg Mt) JlOm VtPf} Lv{aA(Im Li Lj Lx Qe)}

Constrained panels with 3 analytes, where 1.0E-9 >= 'model p-value' > 1.0E-10. Contains 2,637 panels of 36,050,556 total panels evaluated. : Is{Me(aA Fr Hq Hr Hw Ih Ii Il Im Iq It Jk Jl Jo Jp Lh Li Lj Lu Mm Mq Mz Ng Nh Nk Ns Nt Og On Oy Pb Pf) Nk(aA Fr Hw Ih Il Im Jp Lh Li Lu Lx Mq Mr Mt Nb Ne Nj Nl Nt Nu Og Oh On Oy Pb Pe Pf Qa Qe) Oy(aA Hu Hw Ih Ik Io It Jh Jp Lj Lw Mm Mr Mu Mv Mz Nb Nh Nj Nn Nt Nx Oh Pd Pe Pg Po Qe) Pb(aA Hu Hw Ih Ik Il Io Iq Jp Lj Mm Mr Mz Nb Ng Nh Nj Nl Nt Nx Og Oh Om On Pd Pe Po Qe) Hw(aA Fr Hq Ih Im Io Jl Jp Lh Li Lj Lu Lx Mr Mt Mz Nb Ng Nh Ns Nt Og On Pf Qe) Nh(aA Fr Hq Ih Ii Im It Jk Jl Jp Lh Li Lj Lu Lx Mq Mz Nb Nc Ng Nl On

Figure 1 Continued

Pf) Im(aA Fr Hq Ih Ii Il Io Iq Jk Jl Jp Lh Lu Mm Nb Ng Nj Ns Nt Nx Og On) Lj(Fr Hq Ii Il Io Iq It Jk Jl Jp Lh Mm Mq Mt Nb Nc Nj Ns Nt Og On Qb) Lu(Hq Ih Ii Il Jk Jl Jp Lh Li Lw Lx Mm Mq Mt My Mz Ns Nt On Pf) Ih(aA Fr Il Jl Jp Lh Li Lx Mq Mz Nb Ng Ns Nt Og On Pf Qa Qe) Ns(aA Fr Hq Jl Jp Lh Li Lw Lx Mm Mt Nb Nt Nu On Pc Pf) Hq(aA Io Jl Jp Lh Mr Mt Mz Nb Nj Nt Og Oh On Po Qe) Ii(Hu Ik Jg Jp Mm Mr Mz Nb Nj Nt Nx Oh Om Po Qe) Jl(Hr Hx Il Io Jk Jo Li Lx Mt My Nj Nq Oe Pa Pf) Lh(aA Il Iq It Jo Md Mk Mt Mw Nb Nj Nq Nv Of Pf) Fr(Hu Il Jo Md Mk Mq Mv Mw Nj Nl Nq Oe Of Og) My(aA Jg Jh Jp Li Lx Mq Mt Nb Nt Om Pc Pf) Io(aA Jp Li Lx Mm Mt Mz Nb Ng Nt Og On Pf) Jk(aA Hu Ik Jg Jp Mq Nb Nj Nt Oh Qa Qe) Og(aA Ik Jg Jp Li Lx Mz Nb Nj Nt Nx Qe) In(Aj aN bR Ch Ct dE dJ dN Vt Wm) Mq(Hr Il It Jo Li Lx Mt Nj Pf) Ng(It Jh Mu Mz Nx Pc Po Qe Wm) On(Il Jo Md Mk Mw Nj Nq Oe Of) aA(Li Lw Mt Mz Nc Nj Nq Pf Qe) Ii(It Jp Li Lx Nb Pf Qe) Nq(Jp Li Lx Mt Nt) Nj(Jp Li Mz Nb Nc) Nt(It Jo Oe Oi) Lx(Mh Oe Pg Qb) Ct(Ba Et Pf) Jo(Ik Li Nx) Et(Ch Kg) Mr(Hx Mk) Mt(Oi Pf) Nc(Ne Nl) Iq(Jp Li) It(Jq Qa) Qb(Qa Qe) AjaN WmMs NeNl JjbR JnJs PaPf} Ok{Pb(Fr Ik Im Io Jo Jq Jr Lh Li Lx Me Mh Mr Mt Mu Nb Nc Ne Ni Nj Nl Oh On Pc Pe Po Qd Qe) Im(Fr Hq Hr Hw Ih Ii Io Jk Jo Jr Jt Lh Lj Me Mq Mt Nh Nj Ns Nx Og Oy Pf Qa Qd Qe) Jo(aA Fr Jm Jq Jr Li Lj Lx Mf Mh Mr Mt Nb Ng Nj Nl Ns Nt Nw Nx On Pe Pf Po Qd) Me(Fr Hq Hr Hw Ii Jr Li Lj Li Lv Lx Mq Mt Nd Nh Ni Oh Oy Pc Pf Qa Qd Qe) Mq(Hq Hr Hw Ii Jq Jr Lj Lu Lv Lx Mt My Nh Ni Nj Ns Og Oy Pf Qa Qe) Qa(aA Hq Hr Hw Ih Io It Jk Jt Lu My Nh Nj Nk Nq Ns Oe Og Oy Qb) Lj(Fr Hq Hr Hw Ii Io Jl Jq Jt Mt Nb Ng Nh Nj Nk Ns Oe On Oy Pa) Qe(Hq Hr Hw Ih Io Jk Jq Jt Lu Lv My Nh Nj Nq Ns Oe Og Oy Pa) Ni(aA Jq Jr Li Lu Lv Lx Mt Nc Nd Nh Nj Nl Oh Oy Pc Pf Qd) Nd(Jp Jq Jr Li Lu Mp Mr Mt Nb Oh On Oy Pc Pe Pf Qd) Jl(aA Hq Hr Hw Hx Jk Jt Mt My Nh Nj Nk Nq Ns Og Pa) Oy(aA Ik Jr Li Lu Mr Mt Mu Nb Nh Pd Pe Po Qd) Lu(Jr Lx Mt My Nh Nj Ns Of Og Oh Pf Qd) Nh(aA Fr Ii Jq Jr Lh Lx Nb Ne Og Pf) Ng(Jh Mv Nj Nt Oh Om Pc Po Qd) Ii(Et Fr Jr Lh Lv Lx Mt Po Qd) Mt(Hq Jq Jr Lv My Ns Nw) Et(Hq Hr Io Jt Nb Ns) My(aA Fr Jh Lh Lv Lx) aA(Lw Mf Nj Ns Pf) Nw(Ik Mw Nx Of) Lv(Io Li Nb) Hq(Jr Lx Pf) WmIn NsJr MdJq NcNk QdJt PaPf} Jj{Lx(aA Fr In Jg Jm Jn Jo Jq Jr Jt Li Lu Me Mr Mz Ne Ni Nj Nl Oh Om Pb Pd Pe Pf Qd) Qd(aA Fr In Jg Jq Jr Li Lj Lu Me Mr Ms Mz Nb Ne Ni Nj Nl Nt Oh Om Pb Pf Po Wm) Ik(In Ip Jg Jm Jn Jq Js Jt Mm Mp Mq Mr Mw No Nt Nv Nx Om Pb Pf Po Pz Qb) Nt(Fr Il In Ip Jm Jn Jp Jq Jr Me Mp Ms Mw Mz Nh Ni Om Pb Pf Po Qb) Li(aA Fr Jm Jn Jp Jq Jr Lu Lz Me Ms Mz Nb Ne Nj Nl Oh Om Pb Pf Po) Lv(aA Fr Il Jg Jm Jn Jq Jr Js Mm Mp Mq Mr Mw Mz Nr Nv Om Pz) Lh(aA Hx Il Jg Jp Jr Lu Me My Mz Nb Nc Ne Ng Nu Oy Po Wm) Nx(aA Fr Il In Jg Jm Jp Jq Jr Mr Ms Mw Mz Ni Nr Om Pe) Po(aA Hq In Jg Jm Jp Mq Ms Mz Ni Nj Oh Om Pb Pf) Mt(aA Fr In Ip Jn Jo Jp Jt Mr Mz Nj Ns Om Pb Pe) Nh(Fr Jg Jm Jp Jq Lj Mq Mw Mz Nv Om Pf) Mq(Fr Jg Jm Jp Jq Js Mz Om Pf) Nd(Jg Jt Lj Mw Mz Nv Om Pf) Oh(Fr Jg Me Ms Ni Nj Om Pf) Om(In Lj Ms Ng Pf) Et(Aj Ap Dp Oa) Wm(Im Qa Qe) Lj(aA Fr Jg) Pf(Dp Jq Mz) Nj(Fr Jp) Vt(Il oE) NgJg} In{Im(Fr Ik Jn Jq Jr Jt Lj Lu Lw Lx Me Mm Ms Mz Nb Ng Ni Nj Nl Nu Nx Oh Om Pe Pf Po Qd Vt) On(aA Hu Ik Jl Jq Jr Li Lv Lx Mh Mt Mw Ne Ni Nl Nq Ns Nt Nx Og Oh Pb Pf Po Qd) Jl(aA Jn Jp Jq Jr Lh Lw Mq Mz Nb Ng Ni Nl Ns Nt Og Oh Om Oy Pb Pf Po Qd) Li(Ik Jo Jr Jt Lu Lw Lx Mm Mr Ms Mz Nb Nc Ne Ng Nl Nt Nx Oh Om Pb Qd) Mt(aA Jq Jr Jt Lv Lx Me Mr Ms Nd Nh Ni Nj Nt Nx Oh Om Pe Pf Po Qd) Lx(Ik Jq Jr Jt Lh Me Mr Ms Mz Nd Ni Nj Nt Nx Oh Om Pe Qd) Lh(aA Ik Jr Mq Ms Ng Nj Nx Oh Oy Pb Pf Po Qd) Ji(aM bA bN bR cI Cs dE dJ dM dN Dp Oa Vt) Mq(aA Jp Jq Lv Nh Nt Nx Oh Om Pf Po Qd) Qe(Hu Jn Jo Jt Lj Mm Ne Og Po Vt) Et(Ap Ax Ch eI Cs Ed Kg Oa Vt) Fp(Hw Il Jm Jr Js Mp Nb Nk Nl) Lj(Fr Ik Jg Jq Mm Nd Nh Nt Nx) Qd(aA Ik Lv Nd Nh Nj Nx Om) Po(Lv Nd Nh Nj Nt Nx) Nh(Jq Mr Oh Om Pf) Qa(Aj dE Vt Wm) Pf(dE dJ Lv Un) Wm(Jq Nw) Lv(aA Oh) Nd(Fr Jp) Om(Ms Ng) NtJq MwVt NxaA} Fp{Jl(Fr Hq Hr Ih Ii Im Jp Jq Lw Lx Mk Mm Mt Mz Nd Ne Ng Nh Ni Ns Nx Og Oh Om Oy Pa) Jq(Fr Hq Im Jg Jp Lh Lv Lx Md Mm Mq Ms Mt Mz Nh Ni Nk Nt On Pb Qa Qe) Fr(Hq Im Jk Jp Lv Lw Me Mm Mq Mt Mw My Mz Nh Ni Nj Nk Nq Ns Qa) Lv(Hq Jg Lh Li Lw Lx Mq Mr Ms Mz Nh Ni Nk Oh Om Pb Qa Qd Qe) Mm(Im Jp Lh Mq Mr Ms Mt Mz Nd Ng Nh Ni Nk Pb Qa Qe) Im(Hq Ih Jp Lh Lu Lw Mq Ms Mt Ng Nh Ni Nk On Pb) Jp(Hq Lh Lu Lw Me Mq Mt Nh Nq Ns On Oy Qa) Lh(Hq Hr Hx Ii Md Mt My Nd Ng Nh Ni Nk) Mt(Hq Ih Lw Mq Mr Ng Ni Nk Ns Oy) On(Hr Hw Ih Me Mq Nb Nh Nv Of Oi) Pb(Jg Lx Mq Mr Ni Om Pe Pf Qa Qe) Ms(Jg Lx Mq Mz Nx Oh Qa Qd Qe) Ni(Jg Lx Oh Qa Qd Qe) Nk(Nc Nh Qa Qd Qe) My(Jg Jh Om) Qa(Hq Ih Qb) LxMq NgOm} Nd{On(aA Hu Ii Jk Jo Jp Jq Lh Li Lx Md Me Mh Mk Mq Mr Mz Ne Ni Ns Oe Of Og Oh Oi Pe Pf Qd) Jl(aA Fr Jg Jn Jq Lh Lj Lw Mm Mp Mq Mw Mz Ne Ng Ni Nk Og Oh Om Pb Pf Po Qd) Qe(Im Jq Li Lv Lw Mm Mp Mq Mr Ms Mt Mz Ne Ni Nk Om Pb Pe Pf) Qa(aA Im Jp Jq Li Lv Lx Mm Mp Mq Mr Ms Ne Ni Nk Pb Pe Pf) Jp(Fr Im Jq Li Lj Lv Lx Mp Mq Mr Ms Oh Pb Pe Pf Po Qd) Lh(aA Fr Li Lx Mm Ms Mt Mz Ng Oh Oy Pf Qd) Fr(Jq Li Lv Lx Mq Mr Mz Oh Oy Pb Qd) Im(Jq Li Lv Lx Mm Mp Mr Mt Mz Ni Pe) Lx(Jq Lv Mq Mr Ms Oy Pb Pe Qd) Li(aA Jq Mq Ni) aA(Lj Lv Po) AjEt LvLj} Lv{Im(Fr Hq Il Io Jl Jp Lh Li Lj Lu Lx Mm Mq Mr Ms Mt Mz Ng Nh Ni Nx Oh On Pb Pf Qa Qd Qe) Li(Hq Il Io Jl Jp Jq Lu Me Mm Mq Ms Mt Mz Ng Nh Ni Nk Ns On Oy Pb Qa Qe) aA(Jl Jp Lh Lw Mm Mq Ms Mt Mz Nh Nx Oh On Pf Po Qa Qd) Qa(Hq Il Jl Lj Mq Ms Mt Ng Nh Ni Nk Oy Pb Pf Qb) Lj(Fr Jg Jl Jp Lh Mm Mq Mt Nh Ni Om Pb) Qe(Hq Jl Mq Ms Mt Ng Nh Ni Pb) Lx(Jl Mq Ms Ng Nh Ni Oy Pb) Mt(Jl Mq Ng Oy Pb Qd) On(Ii Jk Nh Ns Of Pb) Ms(Jl Jp Lh Oh) Ng(Fr Jl Jp Om) Oy(Fr Jl Lh Pf) Et(Aj Ch) Nh(Jl Jp) PbPf} Et{Aj(aA aC Ad Ao Ax Ba Bc cI Cs cT Cu dM Id Il Ji Jm Jq Jy Kq Li Lx Mi Mq Mr Mt My Nb Ni No Oa Ou Oy Oz Pe Qa Qd Qe) Ng(bL bN Ed Fy gP Kg Qh Qm Rh Ri Sr St Ur Uu) Ii(Fr Hu Il Jm Jn Mu Nx Pe Qb) On(Hu Jk Jt Md Mk Nq Nv Oe Og) Ns(Fr Io Jm Nt Nu Pc Pe) Kg(bA Fy Lj Mr Oa Pf Vt) Wm(aA Jo Li Mw Nv Pf) Mb(Hq Hw Jn Mz Pe) Mu(Hu Mg Nq Of Qz) Io(Jm Lh Mr Nb Nt) bA(Ch Co Ct Lj Oy) Fr(Hu Mg Nq Of) Pe(Hr Jt Mk Pa) Pf(Ap Ct Iz) Ch(cI Ou) Nt(Mg Mm) Hu(Mg Of) Jn(Hq Js) Og(Il Jm) ApJi AxJo CtJl MlNy MmLi MrJt} Ms{Mt(aA Fr Jg Jp Jr Li Lj Lw Lx Me Mp Mq Mr Mz Ni Nx Oh Om Pb Pc Pe Pf Po Qa Qd) Jl(aA Ik Jg Jp Jq Lh Li Lw Me Mq Mz Nb Nh Ni Nk Nx Oh Om Pb Pf Qa Qe) Lh(Jp Jq Jr Li Lj Mq Mz Ng Nh Ni Nx Oh Om Pb Pf Qd) Lx(Im Jq Mq Mr Mz Nh Ni Nx Oh Om Pb Qa Qd Qe) Qa(aA Fr Jg Jp Jq Mq Mz Ni Nk Nx Om) Im(Fr Jp Mq Mr Nh Ni Nx Oh Om Qe) Ji(bA bL cI Ct dE dJ Gl Ha Uk Tj) Qe(Fr Jg Jp Jq Mq Mz Nh Nk Nx) aA(Li Lj Nx Oh Om Po) Om(Ng Oh Qd) Wm(Jp On) MqJp NiLi} Nw{Hq(Io Jq Jr Lh Li Mi Mr Mt Nt Pc Qd) Pe(Hr Hx Mh Mk Nb Ny Pa Pf Pg Po) Mr(Mh Mk Mw Nb Nv Ny Pg Po) Lh(Hr Jk Mk Nb Nx Ny Po) Nv(Fr Io Jq Nb Nt On Wm) Mw(Fr Io Jg Jr Nb Pa) Ii(Li Lx Nl Nx Oh On) Hw(Hr Hx Mb Ny Of) Nq(Jl Li Mt Qd) Nt(Io Oc Of Pg) Jq(Hr Of Pa Pg) Og(Jm Jr Mt Pf) On(Jk Mk Mu Mv) Nb(Ns Of Pg) Jo(Hr Nx Of) Pa(Jr Lx Nl) Fr(Jk Mv) Mu(Lu Pc) Io(Pg Qd) qC(Db Mh) WmMy MlNy MtJl NeNl NeNk HrHv JrJs} Ng{Jg(aA Hu Il Jn Jp Jq Jr Lu Me Mg Mp Mr Mu Mw My Mz Nb Nk Nr Ns Oy Pb Pe Qb Wm) Pf(Ad bA Bc bR dJ dM Ef Jy Ke Ko Kq Lh Pj Rg Uf Uh Un Ur) Fr(Jl Jr Lh Li Lx Mq Mt Nh Nj Nt Nx Om Qd) Om(Im Jl Lh Li Lx Mq Mt Qa Qd) Lh(Jp Li Lx Nh Qa Qe) On(aA Md Mw Mz Pz) Mt(Im Jl Mq Qe) Lx(aA Jl Mq) Ni(Im Li Qe) Im(aA Jl) Jp(Ik Wm) Kq(Il Mg) QeaA} aA{Im(Hq Ih Il Jl Jq Jr Lh Li Lj Lu Lw Lx Me Mf Mm Mq Mt Nh Ni Nj Nk Nq Ns Nx Pb Pf Qe) Lx(Jl Jq Lj Lw Me Mf Mq My Mz Nh Ni Nj Nq Ns Nx Oy Pb Qa Qe) Lj(Ik Jg Jl Jq Lh Lw Mm Mq Mt Nh Ni Nj Nk Nx Om On Pb Qe) Qe(Ih Jq Lw Me Mq Mt Nh Ni Nj Nk Nq Nx Pb Pf) Ni(Li Qa) On(My Oy) PoPb} Ni{Im(Fr Jl Jp Lh Li Lj Lu Lx Mm Mr Mt Nh Nj Oh On Pf Qa Qe) Qe(Jl Jp Jq Lh Li Lj Lx Mt Nc Nh Nj Nl Nx On Pb Pf) Qa(Jl Jp Jq Lh Li Lx Mt Nj Nx On Pb Pf) Li(Jl Mt Nh Nj On Pb) Lx(Jl Nh Nj Pb) Lj(Jl Jp Lh Mt) Nj(Jl Jp On) On(Nh Pb) MtJl} Oy{Pf(Ad As bA dM Id Im Jl Jy Kd Ke Kn Kq Lh Mt Or Qa Qe Tv Ul Un Ur Us Wm) Lx(Fr Ik Im Jl Lh Mq Nh Nx Om Qa Qe Wm) Lh(Ik Jl Jp Li Mv Nh Om Qa Qe) Fr(Ik Im Jl Mq Nh Om Qa Qe) Jl(Im Jg Li Mt) Qa(Jg Om) Qe(Jg Om) WmPo} On{My(Ii Jk Jr Li Lj Lu Nb Nk Ns Nx Oh Pa Pf Qa Wm) Lj(Hq Ii Jk Lu Me Mq Mt Nh Nj Nk Ns Oe Pb) Ii(Im Jl Me Mq Qa Qe) Pb(Me Mq Nh Pf) Jk(Im Jl Qa) Mw(Im Mt) NsMq MkJl} Jl{Im(Hq Lu Lx Mt Nh Nk Nx Og Pb) Lx(Me Mk My Nh Nk Pa Pb) Mt(Lj Me Mk My Nk Ns Pb) Nk(Li Lj Nh Qa Qe) Mk(Om Qe) Li(Pa Pb) NeNh HxQa LjPa PbPf} Lh{Pb(Im Li Lj Lx Mt Nh Pf Qa Qe) Im(Hq Ii Mt Nh) Mt(Lj My) MyJh NhLj IiQe}

Figure 1 Continued

Ji{Wm(bA bN bR dM It Jd nW oE oH oN Qx Tj) Pf(Aj Co Ct Ha) IlUk} Pb{Mq(Fr Li Lx Mt Pf Qa) Pf(Mt Qa)} Nh{Ne(Im Qa Qe) Nk(Qa Qe)} Ad{Aj(bA Pf)} Wm{NooE KeoN} Nk{Qa(Nc Nj)} DrIlKg LiwPnW aMbAgV

Constrained panels with 3 analytes, where 1.0E-8 >= 'model p-value' > 1.0E-9. Contains 5,022 panels of 36,050,556 total panels evaluated. : In{Pf(aA aC AD aF Aj aM bA Bc bL bR bS bU bV cA cC cF Ch cK CO Ct dH dM Dp Id Ik Iz Jj Jq Jr Jt Kd Ke Kn Ko Kq Lj Lx Me Mr Mz Nd Nj Nt Nx Oa Oh Om Pj Po Qd Sr Ul Tj) Lj(aM bC bR bW cE dF dM dN Hu Jh Jj Jo Jp Jr Jt Jy Ke Kq Lw Lx Me Mr Mu Mw Mz Nb Ne Ni Nj Nl Nv Oh Ou Pe Po Qd Uf Un Vt Wm) Vt(BA Ed Fp Id Ij Il Jj Jl Ke Kn Kq Li Lx Mq Mt Nb Nd No Nr Oa oE Oh Ou Oz Pe Qd Qh St Uf Ul Un Ur Wm) Lh(Hr Hx Ih Ii Il Jg Jm Jn Jp Jq Js Lv Lw Me Mm Mr Mw My Mz Nb Nc Ne Ni Nl Nt Nu Of Om On Pd Qb Wm) Po(Hq Ik Il Jg Jn Jp Jq Jr Jt Li Lw Me Mm Mr Ms Mz Nb Nc Ne Ng Ni Nl Nu Oh Om Oy Pb Pe Qd) Et(aC AO bA bN bV Co CT dE Dg dM Dp Hc Id Iz Kd Ke Kn Ou Qy Ra Rm Sr Uk Ul Un Us) Qd(Fr Jg Jn Jo Jq Jr Lu Lw Me Mh Mm Mr Ms Mu Mz Nb Nc Ne Ng Ni Nl Nt Oh Pc Pe Wm) Mq(Fr Ih Ik Jg Jj Jn Jr Js Jt Mm Mr Mw Mz Nc Nd Nj Nl Nu Nv Pe Qb Un) Om(aA Hu Ih Ik Jr Lv Me Mh Mr My Mz Nd Ne Ni Nj Nl Nt Nx Oh Oy Pb) Nh(aA Fr Jg Jj Jn Jp Jr Jt Lv Mm Mp Mw Mz No Nt Nv Nx Pe Qb) Un(Ax Cs Dp Id Il Im Is Jj Jm Li Ms Mw Ng Oa Oz Pb Qa Qe Wm) Mt(Fr Hv Hw Ik Jn Jo Jp Js Lw Mh Mm Mz Nb Ng Ns Pb Pd Qb) Nt(aA Fr Jn Jp Jr Lv Me Mm Mr Mw Mz Ng Nx Oh Pb Pe Qb) Qa(bA bL bR Ch cI Ct dJ dN Dp Id Iz Ke Ou Ua Uh Uk Ul) Im(Hv Hw Il Jo Jp Ke Mf Mh Mi Nc Ne Og Pb Pc Pd Wm) Is(aC aD aM bV cV dL dM Id Iz Ke Ko Ou Ua Uh Uk Ul) Lv(Fr Ik Jg Jn Jp Jq Jr Js Jt Mm Mr Mw Mz Nx Pe) Lx(Hv Hw Jg Jn Jo Lw Mm Nb Nc Ne Ng Nl Oy Pb) Qe(Ad Aj As bA Ch cI Cs cT Cv dE Id Ke Kn Wm) Oh(aA Ik Jj Jq Jt Me Mr Ms Nd Ni Nj Nx Pe) Jl(Jg Js Jt Mb Mk Mr Mw Nc Ne Nq Qb Wm) On(Jk Jn Mf Mk Mr Mx Mz Nb Nc Nu Of Pe) Ik(aA Fr Jp Jq Js Jt Mm Mr Mz Pe Qb) Wm(bA dF Jj Ke Li Mw No Pe) Jq(aA Fr Jj Mr Ms Nd Nx) Nd(Jt Mr Mw Nv Pe) Ke(Ax Bc Mw Ng Oa) Li(Hw Jn Ns Oy Pe) Nx(Fr Jr Jt Mr Pe) Nj(aA Fr Jp Mz) No(eC oE oN) Ng(Fr Kq Uf) Jj(Jg Jm Nv) aA(Jr Lw Mz) Aj(Ad Kq) Mw(Id Kn) Ji(Fy Qm) ChKq FrJr MeJp VqoE PedE} Jj{Pf(aA bL bR CO Ct Fr Ij Il Ip Jg Jm Jn Jo Jp Jr Js Jt Lj Me Mr Mu Mw Nb Ne Ni Nj Nl Nr Nu Nv Oa Oy Pb Pz Qb Un Vt) Nh(aA Ii Ij Ik Il Ip Jn Jo Jr Js Jt Me Mg Mm Mp Mr Mu Nb Ne Ni Nm Nn No Nr Nu Ny Pb Pd Pe Pg Pz Qb Qc) Oh(aA Hu Ij Il Ip Jm Jn Jo Jp Jq Jr Jt Lj Lu Mf Mg Mr Mu Mw Mz Nb Nc Ne Nl Nr Nu Nv Pb Pd Pe Pg Pz Wm) Jg(aA Fr Il Io Jm Jn Jq Jr Js Li Lu Me Mf Mh Mr Ms Mw Mz Nc Ne Ni Nj Nl Nr Nt Nu Om Pb Pe Qb) Mq(aA Ij Il Ip Ir Jn Jr Jt Mm Mp Mr Mw Nc Nd Ne Nj Nl Nm No Nr Nu Nv Pb Pd Pg Pz Qb Qc) Lv(Hu Ih Ij Ip Ir Jt Mg Mu Nb Nc Nd Ne Nj Nl Nm Nn No Nu Ny Pb Pd Pe Pg Qb Qc Wm) Om(aA Fr Il Jm Jn Jp Jr Lu Md Me Mf Mh Mw My Mz Nb Nc Ne Ni Nj Nl Nr Nu Oy Pb Qb) Nx(Ij Ip Jn Jo Js Jt Lu Me Mf Mh Mu Mx Nb Nc Nd Ne Nj Nl No Nu Nv Pb Pd Pz Qb) Fr(Il Jm Jn Jp Jq Jr Js Jt Me Mf Ms My Mz Nc Ne Ng Ni Nl Nu Oy Pb Po Pz Qb) Ik(aA Hw Ij Il Ir Jo Jr Lw Mi Mj Ms Mu Ni Nm Nn Nr Nu Ny Pc Pd Pe Pg Qc) Lj(Dp Hu Jh Jn Jo Jp Jq Jt Lx Me Mg Mm Mr Mu Mw Mz Ni Nj Nl Nv Ou Po Pz) Et(AO Ax bA Ch cI Co Cs Ed Gl Hc Iz Jd Kg Or Ou Ow Rm Us Vt) Jp(Il Jm Jq Jr Lu Lx Me Mf Mr Ms Ne Ni Nl Nr Nu Wm) Nd(Ij Il Jm Jn Jq Js Mm Mp Mr No Nt Pe Pz Qb) Wm(Fp Ih Jq Lx Mt Mw Mz No Nw Ok On Pe Qc) Is(aN bA cI Ct dJ dM Dp Oa Ou Qm Uk Us Vt) Po(Ip Jn Jq Jt Me Mm Mw Nb Ne Nk Nl Pz) Dp(Il Im Ji Jl Oa Qa Qd Qe) Mz(aA Il Jm Jr Ne Nj Nl) Qd(Jm Lz Mm Mu Pc) Jq(Il Ms Ne Nj Nl) Nv(Me Ms Ni Nj Nl) Vt(Im Jl nW Qa) Ng(Ad Ba Kq) Jm(aA Ni Nj) No(oE oN) Lx(Ip Mf) Il(Oa Un) Qa(bR cI) Ji(cI Oa) aA(Nr Nt) AdAj MwNj NiQb VqoE} Im{Mt(Fr Hq Ih Ii Il Io Jk Jp Jq Jr Li Lj Lu Lw Lx Me Mq Mr My Mz Nh Nk Ns Nt Nx Oe Og Oh On Oy Pb Pe Pf Qa Qd Qe) Lh(Hr Hw Hx Ih Ik Il Jk Jl Jo Jp Li Lj Lu Lw Lx Me Mm Mq My Mz Ne Nj Nk Nl Ns Nx Oe Of Og Oh On Pf Qa Qd Qe) Jl(Fr Hr Hw Hx Ih Ii Ik Il Io Jk Jp Jq Li Lj Lw Me Mf Mk Mq My Mz Nj Ns Nt Oe Oh Om On Pa Pf Qa Qd Qe) Ms(Hq Ik Il Jg Jq Jr Jt Li Lj Lu Lw Me Mi Mm Mp Mu Mz Nb Nd Ng Nj Nk Nn Nt Nu Pb Pc Pe Pf Po Qa Qd) Nh(Fr Hq Ih Il Jp Jq Jr Li Lj Lu Lw Lx Me Mm Mq Mr Mz Nc Ng Nk Ns Nx Og Oh Om On Pb Pe Pf Qa Qd Qe) Mq(Fr Hq Hw Il Jp Jq Li Lj Lu Lx Mr Mz Nd Ng Ni Nj Ns Nt Nx Og Oh On Oy Pb Pf Qa Qd Qe) On(Hq Hu Hw Il Jq Jr Lj Lu Lx Md Me Mh Mk Nj Nl Nq Ns Nx Oe Of Og Pb Pf Qa Qd Qe) Ng(Hu Ik Jh Jp Jq Jt Ke Kq Li Lu Lw Lx Mm Mr Mu Nd Nt Nx Pe Pf Qa Qd Qe Uf) Lu(Fr Hq Il Jp Jq Li Lj Lw Lx Mm Mr Mz Nd Nx Og Oh Pb Pe Pf Qa Qd Qe) Fp(Hw Jg Jt Lx Mr Mz Nd Ns Nt Nx Oe Og Oh Om Oy Pe Qa Qd Qe) Fr(Hq Ii Il Jk Jq Lj Me My Nj Nq Ns Nx Oe Og Pb Qa Qd Qe) Nd(Jg Jn Jt Lj Lw Mi Nb Ne Nk Og Oh Om Pa Pb Pc Pf Po Qd) Ni(Hq Hw Il Jq Jr Lw Mp Mz Nc Ne Nl Nt Nx Og Pb Pc Pe Qd) Qa(aA Hq Ih It Jp Jq Lx Nk Nx Og Pb Pf Qb) Qe(Hq Ih Jq Lx Me Mr Nj Nk Nx Og Pb Pf) Lx(Hq Il Jq Me Mr My Nx Pb) Lv(Mp Nb Nt Om Oy Pe Po) Ji(Aj Ch cI Ct Dd gP Uk) Et(Ap Ch Ct Iz Kg Wm) Pf(Aj Ct Hq Jq Me Pb) Mr(Hq Il Nx Oy Pb) Li(Hq Me Oy Pb) Nk(Nc Nj Nl) Oy(Jg Om Pe) Me(Jp Mm) AdAj NjJp PbPe} Jl{Nh(aA Fr Jp Jq Lh Li Lj Lw Me Mk Mm Mq Mt Mz Nc Ng Ni Nl Ns Nx Og Oh Om On Oy Pb Pf Qa Qd Qe) Qe(aA Hq Hr Hw Hx Ih Ii Jk Jq Lu Me Mq Mt My Ne Ng Nj Nq Ns Nx Og Oy Pa Pb Pf) Lv(Hq Ii Il Jg Jn Jp Lh Me Mk Mq Mz Nb Ni Nk Ns Nx Og Oh Om On Pb Pf Qd) Qa(Hq Hr Hw Ih Ii Jk Jq Lu Me Mk My Ne Ng Nj Ns Nx Og Oy Pa Pb Pf Qb) aA(Jq Jr Lh Li Lw Me Mf Mq Mt Mz Ng Ni Nj Ns Nx Oh On Pb Pf Po Qd) Li(Hq Hr Ii Jk Jq Lu Lw Me Mk Mq Mt My Ng Nj Nq Nr Ns Nx Og) Ni(Jg Jp Jq Lh Mm Nc Ng Nl Nx Og Oh Om On Oy Pb Pf Po Qd) Lj(Fr Ik Jg Jp Jq Lh Lu Me Mm Mq Ms Ns Nx Om On Pb) Lx(Hq Hr Hw Ii Jk Jq Lu Mq Mt Nj Nq Ns Nx Oe Og) Pb(Fr Ik Jg Jp Jq Lh Me Mq Nt Nx Oh Om On Po Qd) Oy(Ik Jh Jp Jq Me Mq Mv Nb Nd Nx Oh Po Wm) Pf(Ct Hq Jq Me Mk Mq Mt Ng Nk Ns Nx Pa) Ms(Fr Hq Mw Ne Nj Ns Nt Pc Po Qd Wm) Ng(Ik Jp Jq Lh Mq Nb Nk Nt Nx Wm) On(Hq Me Nj Nk Nq Ns Oe Of Og Pa) Mk(Fr Ik Jg Jp Lh Nd Nx Oh Po) Mt(Ii Jk Jq Mq Ne Nq Og Pa) Nd(Hr Jr Mr Nb No Ns Nx Pc) Nk(Jp Nc Ne Nj Nl Oh Qd) Jq(Hr Hx Ik Mb Mq Og) Jp(Ik Me Mq Nj Ns) Om(Ii Jk My Ns Og) Lh(Hr Hx Ii My) Ct(Ba Is Ji) Et(Ch Kg Wm) Jk(Fp Fr Jg) Aj(Ad Ji) Ns(Mq Nx) Me(Hr Oh) My(Jg Jh) Og(Ik Nx) MlHx OhPa} Qa{Mq(aA Fp Fr Hq Hr Hw Ih Ii It Jp Jq Li Lj Lu Lx Mt Ne Ng Nh Ni Nj Nk Ns Nx Og On Oy Pf Qb) Mt(aA Hq Ih Ii It Jk Jq Lh Lj Me My Nd Ne Ng Nk Nq Ns Og Oy Pb Pf Qb) Nk(aA Fr Ih Jp Jq Jr Lh Li Lj Lu Lx Mr Ne Ng Nl Nt Nx On Pb Pe Pf) Ms(Hq Hu Ik Li Lw Me Mm Mp Mr Mu Nb Ne Nh Nt Oh Pb Pc Pe Pf Wm) Lh(aA Hq Hr Hw Hx Ih Ii Il Jk Jo Lj Mb My Nh Nj Nq Of Og Pf Qb) On(Hq Hr Hw Ih Jq Lv Mb Md Me Mk Mw Nh Nj Nq Ns Oe Og Pb Qb) Pb(aA Fr Hu Ik Jg Jp Jq Li Lu Lx Me Mr Nh Nt Nx Om Pe Qb) aA(Ih Jq Li Lj Lw Me Mm Mz Nc Ne Ng Nh Nj Nq Nx Oy Pf) Fp(Hr It Jg Lw Lx Mz Nd Ne Ng Nh Nx Oh Om Oy Pc) Jq(Fr Hq Hr Ih Ii Ik It Li Lx Md Ng Nh Og Pf Qb) Ni(Fr Hq Hw It Jg Lj Mm Mr Nc Ng Nh Om Oy Pc) Ng(BA Hu Ik Jp Li Lx Mm Nt Nx Pf Wm) Fr(Hq Ii It Jk Me My Nh Nj Nq Ns Og) Nd(Ih Jg Lj Lw Mz Og Oh Om Pc Qb Qe) Lv(Io Jp Lx Mm Mz Nb Nx) Pf(Ct Hq Ih Jk Nh Pa Qb) Li(Hq Ih Jk Me Nh Oy) Ct(BA cT Et Ji) Lx(Hq Ih Me Nh Qb) Jp(Jk Me Nh Nj Oy) Nx(Ih Ii Og Oy Qb) Om(Hq Ii Jk My Og) Et(Ap Ch Kg Uk) Is(Hr Ii Mb) Oy(Mr Mv Pc) My(Jg Jh) AdAj TiIi NcNh NeNj IhIk JgJk} Lh{Nh(aA Fr Hq Hr Hx Ii Jk Jo Jp Jq Jr Li Lv Lx Md Mk Mm Mq Mt My Mz Nc Ne Ni Nk Ns Of Og Oh On Pf Qd Qe) Oy(aA Hr Hu Il Jm Jn Jq Jr Lj Lu Lw Mm Mq Ms Mu Mw Mz Nb Ne Ni Nj Nl Nt Nx Oh Pb Pc Pd Po Qd Wm) Pb(aA Fr Hr Hx Ii Ik Jg Jp Jr Lv Mb Mm Mq My Ne Ng Ni Nj Nl Nt Nx Oh Om On Pd Po Qd) Mt(aA Hq Hr Hx Ii Jk Jo Jq Jr Li Lv Lx Md Me Mk Mq Mw Ni Nj Nq Ns Of Og Pf Qd Qe) Qe(aA Hq Hr Hw Hx Ih Il Jk Jo Jq Lj Lv Mk Mq Mw My Nj Nk Ns Of Og Pf) Ms(Fr Hq Hr Hx Ii Ik Jg Jn Lw Me Mm Mp Mr Mw My Nb Nn Nt Pc Po Wm) aA(Hx Ii Jq Jr Li Lw Lx Me Mm Mq My Mz Ng Ni Nj Nq Ns Nx Oh Pf Qd) Nd(Hq Hr Hx Ii Jn Jo Jq Jr Lv Lw Mp Mq Mw My Ni No Of Pc Po) Ng(Hr Hu Hx Ik Lj Lv Mm Mq Mu Mw Ni Nt Nx Oh Po Qd Wm) Lj(Fr Hq Hr Hx Ii Ik Jp Lu Mm Mq Nj Nk Nr Nx) Lx(Fp Hq Hr Ii Lv Mq My Ni Nj Of) Ok(Hq Hr Hw Hx Jt Md Nj Ns Of Og) My(Fr Jg Jp Li Lv Om Pf Wm) Lv(Jp Mm Mz Oh Pf Qd) Ni(Li Nj Pf Qd) Ii(Li On Pf Qd) Fp(Mq Mz Of) Hq(Li Pf) Qd(Hr Hx) On(Jk Of) EtKg NcNk NjJp} Et{Kg(Ad Aj aO Ap Ax Bc Ch cI Cs cT Cu Cw Dc dM Dp Id Ij Il Ji Jm Jq Jr Jy Kd Ke

Figure 1 Continued

Kn Ko Kp Kq Kr Li Lv Lw Lx Ml Mm Ms Na Ni No Nw Oh Or Ou Oz Pe Pi Qd Qe Ra Ri Sr Tv Ud Uk Un Us Wm) Ch(aA aC Cs cT dM Ed Fp Hu Id Il Ji Jo Jy Ke Kq Lj Lx Mm Ms Mt Nb Ni No Oa oH pF Qe Uk Ur Us) Ct(aA Ax Ba Cs cT Cu dM Fp Hu Il Ji Jm Jq Lj Lv Lx Mi Mm Mq Mr Ms Nb Ni No Oa Oz Pe Qe) Aj(bN bV Dp Ed Fb Fy jO Kd Ke Kn Or Ra Ri Sr St Tv Uk Ul Us Vt Wm) Wm(bA cl dM Ii Is Jq Lv Lw Mg ,Mh Mm Nq Of Oh Oz Pb Pz Qc Qd Qe) bA(aC AO Ap Ba Bg cl Cs Cw De Hq Ii Iz Jo Ms My Nd Oa) Jo(Ad Ao Ap As cl Cq Cs Cu Cw Dc Id Kd Kn Oa Vt) Lj(aC Ap cl Co cT dE Dg Dl dM gP Ha Jy Kj Ou Uk) Uk(Ap Ed Id Is Ji Mm Ms My Oa Ou Pf Ul) Ap(aA Ax Is Mm Mq Ms Nb No Nw Qe) Oy(cl Cs cT Jy Ke Kq Or Ou Vt) Is(Al aN Ao Bg cl Co Iz) Ji(Ao cl Co Cw Dk Gl) Pf(AO Bg Dg Ef Kj) Cs(li Jt Mm Ms) Ng(eC oE pF) Oa(li Kj Mm) Co(Lv Lx) Ms(cI Dg) Dcli NooN IzOu aAaO} Pf{Oy(aA aC Aj AN Bc bL Bn bR bS cA Cp CQ CT Cu Cw Dc dE dJ Dp Fp Fr Fy gP Ha Jg Jp Jq Ko Kp Kr Lx Mq Nh Nt Om Ou Pi Pk Qd Qx Ra Rb Rj Sr Tn Tr Uc Up Ut Vp Vs) Ng(An Ap Aw Bb bL Bo bS cO Cp cT Cu dE Dg Di Dp Ez Fr Gp Ha Hb Id Kd Kf Kn Kp Lv Mt Om Or Ou Qe Qg Qm Rc Ri Sr Tr Uc Ue Ul Uu Vt Tj) Ji(bL bR bS cA Ch cl cO Dd DE dM gP Ib Iz Kg Uk Ur Us Tj) Lv(Hq Jp Jq Lj Mm Mq Mr Ms Mt Mz Nd Nh Ni Oh On Qd Qe) Pb(aA bA Ct Fr Jq Ke Kn Lx Mr Nd Nh Ni Nt Om Qe Ur Vt) aA(Aj Ct Jq Jr Lw Mq Ms Mt Mz Nd Nh Ni Nj Nx On Qd) Ct(Ad BA Bc cT Ij Jp Jq Ke Kq Mk Mq Ni Nw) Aj(Bc bR Is Jg Jp Jq Ke Kq Mk Ni Qd) On(Hq Ii Jk Me Mq Mw Nh Ni Ns Og Pa) Jq(Fp Mq Ms Mt Nd Nh Ok Qe) Fp(Hq Ms Mz Nh Ni Nk) Qe(Hq Mq Ms Nh Nk Pa) Ok(Hr li My Nj Ns Og) Nd(Fr Lx Mq Mt Qd) Ni(Jp Lx Mt Nh Qd) Mq(Mt Nh Qd) Ms(Om Qd Wm) Vt(Ha Oz Ur) Ii(Ke Un) Is(aN Ch) CoNw WmMy MeMt} Qe{Mq(Fp Fr Hq Hr Hw Ih Ii Jp Jq Li Lj Lu Lx Mt Mz Ng Nh Ni Nj Nk Ns Nt Nx Og On Oy Pb) Jq(Fr Hq Hr Ih Ii Ik Il It Li Lu Lv Lx Mb Md Mt Ng Nh Nj Nk Nt Nx Og On Oy Pb) Ms(Hq Hu Ik Il Jr Li Lw Me Mm Mp Mr Mu Nb Nj Nt Nu Oh Pb Pc Pe Po) Nh(Fp Fr Ih Jp Li Lu Lx Me Mr Mt Mz Nc Ng Nl Nx Og Om On Oy Pb) Mt(Hq Ih Ii Jk Me Mr My Ne Nk Ns Oe Og Oy Pb Qb) Ng(BA Fp Hu Ik Jh Jp Li Lx Mm Mu Nd Nk Nt Nx) Lv(Il Io Jp Lj Lx Mm Mr Mz Nb Nk Ns Nx On Oy) Fp(Hq Ih Lw Mr Nd Ne Nx Og Om Oy Pc Qb) Ni(Fr Hq Hr Il Mm Mr Og Oh Om Oy Pc) On(Hq Jk Me Mk Mw Nj Nq Ns Oe Og Pb) Pb(Fr Ik Li Lx Me Mr Nt Nx Om Pe) aA(Hq Li Mf Mm Mz Nc Ne Ns Oy) Fr(Hq Il Jk Me My Nj Nq Og) Nd(Ih Jg Jn Lj Og Oh Pc) Nk(Li Lx Nc Ne Nj Nl) Is(Io Iq It Iu My Ns) Om(Hq li Jk My Og) Oy(Li Mr Mv Pe) Ct(bA Ji) Lx(Hq Me) My(Jg Jh) Li(Hq Me) Nx(Ii Og) AdAj NjJp IkOg JiUk} On{Mq(aA Hq Hr Hu Hw Jk Jo Jq Jr Li Lu Lv Lx Md Me Mt Mw Nh Ni Nj Nq Nv Of Og Qd) Ni(aA Hq Hu Hw Ii Jk Jo Jr Lv Lx Md Me Mh Mt Mw Nc Ne Nl Nq Ns Of Og Oh Qd) Pb(aA Ii Ik Io Jq Jr Li Lu Lx Mb Mh Mr Mt Mw Ne Nj Nl Nq Ns Oe Og Pe Qd) Me(aA Hq Hr Hu Hw Jk Jo Jr Li Lv Lx Md Mt Mw Nh Nj Ns Oe Of Og Qd) Nh(aA Hq Hu Ii Jk Jq Jr Li Lx Md Mk Mw Nc Ne Nk Ns Oe Of Og Qd) Lv(Hq Hu Il Io Jo Lx Md Mt Mw Nj Nq Nv Og Oh Qd) Lj(Hw Ih Ik Io Jq Md Mk Mw Nq Nt Nx Og Oi Pa) Ii(Ik Jq Jr Li Lx Mh Mt Nj Ns Nx Ok Po Qd) Mw(Ik Jg Li Lx Mk Nj Ns Nx Oh Ok Pc Qd) Ok(Hq Hr Hu Hw Jk Jt Md Mk Ns Of Og) Ns(aA Hq Jk Jq Jr Li Lx Mt Nj) aA(Jk Jr Lw Mf Mh Mt Nj Nq) Jk(Ik Li Lx Mt Nj Qd) Og(Ik Mt Nj Qd) Nk(Nc Nj Nl) Hq(Li Lx Mh) Nq(Li Qd) Mk(Lx Mt) Is(Mu Mv) MdJq NjOf} Fp{Nk(Il Jg Jn Jt Li Lw Lx Mq Mr Ms Mu Mz Ne Nj Nl Nt Nx Oh Om Pb Pc Pe) Pb(Jn Jo Jt Li Lw Mi Mp Ms Mu Mz Nb Nh Nt Nv Nx Oh Pc Pg Po Qd) Ni(Jt Li Lw Mp Mq Mr Ms Mu Mw Mz Nc Nh Nj Nl Nt Nx Om Pc Pe) Mr(Hq Hr Hx Jg Lw Lx Mk Mq Ms Mz Nd Nh Nx Oh Oy Pc Qd) Nh(Jg Jt 1J Lw Lx Mp Mq Ms Mz Nc Nx Oh Om Pc Pe Qd) Qd(Hq It Jg Jq Lu Lw Lx Mm Mq Mz Nd Ng Om Oy Pc) Ms(Jn Jt Li Lw Mp Mu Mw Nb Nn Nt Nv Pc Pe Pz) Lx(Hq Jg Lu Lw Me Mh Mm My Mz Nd Ng Pc Pg) Mq(Hq Jg Jn Lw Mz Ns Nt Nx Oh Om Oy Pc) Mz(Jg Lu Lw Nd Nt Nx Oh Pc Pe) Jg(Hq Lw Me Mw Nd Ns Og Oi) Oh(Hq Jq Lu Lw Me Mm Nd) Oy(Jh Mm Mu Mv Nt Pc Pe) Nd(Jq Jt Mp Om Pe) Jq(Hr It Nx Pc) Om(Hq Md Ns Og) Lw(Ns Nt Nx) Mm(Lu Me Ns) Ng(Jt Mu Nt) Jt(Hr It) HqLi NxPe} Ng{Fr(aA Hu Ij Jh Jm Jn Jp Jq Jt Lj Lw Me Mm Mr Ms Mu Mw Mz Nb Nc Ne Ni Nl Nv Oh Pb Po Pz Qb Wm) Ji(Ad bA Bc bF Bg bJ Bo bR cI cT dF Dg dJ dM Ef Gp Jy Kq Tn Tr Uc Uf Uh Uk Uu) Mt(aA Ba Jp Jq Jt Li Lj Lx Mr Ms Mu Ni Nt Nx Oh Pe Po Qd) Kq(Ba Dp Ij Is jE jF Ke Lx Mq Mw Nd Ne Nj Pb Uh Uo Ur Wm) Om(aA Hu Ik Jp Jr Lj Lu Mu Mw Nb Nd Nh Ni Nt Oh Pb Po Wm) Lx(Ik Jp Jq Mr Ms Mu Nd Nh Ni Nt Nx Qd) Is(Ad aN Aw Ba Bo bR dF Di dJ dM Qg Uf) Ba(Ad Jp Kc Nw Pe Qd Uh Un Vt) Li(aA Ik Jp Jq Mq Nd Nh Nt Nx) Ke(Bc fN Il Mg Mw oE Uf Wm) Jp(Mq Nd Nh Nt Po) Ad(Aj Nw Ur) Wm(Ij Ok Qd) Mq(Nt Qd) Uf(Ij Il) PoaA LvQd KovS NwqD} Lx{Oy(Ad Hu Ij Il Jh Jp Jq Jt Li Lu Me Mr Ms Mu Mw Mz Nb Ni Nj Nt Nv Oh Pb Pe Po Qd) Nd(Hq Hx Jg Jn Jt Li Lj Lw Me Mh Mm Mp Mt Mw My Mz Ni Ny Oh Om Pa Pc Pg) Ni(Ik Jg Jp Jq Jr Li Lj Me Mm Mq Mr Mt Nc Ne Nl Nt Nx Oh Pc Pe Qd) Ms(Fr Hq Ik Jg Jn Jp Jr Jt Li Lw Me Mp Mu Nb Nj Nk Nn Nt Pc Pe) Nh(Fr Hq Jp Jq Me Mq Mr Mz Nc Ne Nk Ns Pb Pe Qd) Mq(Hq Jn Jq Lj Lu Me Mr Mt Mz Nj Ns Qd) Lv(Hq Jp Jq Lj Me Mr Mt Mz Oh Pg Qd) Ok(Hr Jq Md Mh Nj Ns Of Pa Pg) Pb(Fr Ik Jq Me Mr Mt Pe) Mt(Hq Jq Me My) aA(Hq Jr Qd) AdAj WmTj MdJq MeQd MyJg NkNl} aA{Mt(Jq Jr Li Lw Me Mf Mm Mq My Mz Nd Ne Nh Ni Nj Nq Ns Nx Oh Oy Pb Po Qd) Mq(Fr Jp Jq Jr Li Lw Mm Ms Mz Nd Nh Nj Nt Nx Oh Om Pb Po Qd) Li(Hq Jq Jr Lw Me Mf Mm My Mz Nh Nj Nk Nq Ns Nx Oy Pb Qd) Po(Hq Jq Lj Lw Me Mm My Mz Nh Ni Nj Nk Ns Nx Oy Qd) Qd(Lj Lw Me Mm Ms Mz Nd Nh Ni Nj Nq Nx Pb Pc) Nd(Fr Il Jp Jq Lw Mm Mn Mp Mw Mz Oh Om) Lv(Il Jm Jn Jq Jr Mn Nr Nt Om Pb) Lj(Fr Jh Jp Jr Me Mf Mz Ns Nt Pc) Ms(Fr Ij Jg Jp Jq Lw Mz Nt) Nh(Jq Lw Mn Mz Ne Oh) Lw(Nx Oh) Om(Oy Pb) MmJr MzNj NiOh JgOy} Ok{Oy(Hu Il Jg Jq Mh Mi Mv Nc Ne Nj Nl Nn Ns Oh Om Pc Pg) Ii(Ik Il Jm Jq Li Mh Mr Mu Nb Nj Nt Nx Oh Pc Pe Qb) My(Ik Jg Li Mr Mu Mv Nb Nq Om Pc Po Qd) Fr(Hq Jk Mg Ni Nj Nl Nq Ns Of Og) Hr(Ik Jq Li Mr Mt Nx Oh Pe Po Qd) Qd(Hq Hw Io Mt Nb Nj Nq Ns Og) Jq(Hq Hw Ik Jt Mb Nb Nj Ns Og) Og(Ik Jm Li Mu Nj Oh Pc) Hq(Li Mh Mr Oh Pc Po) Ns(Li Nb Oh Pc) Nj(Jr Nb Nk Oh) Hw(Mh Mr Oh Po) Li(Io Jt Nq) Mu(Nq Of) Ni(Mh Ne) Ik(Mg Oi) WmMs NtJt NkNl JnJs OeOh PaPe} Lv{Qd(Fr Hq Il Io Jp Lu Me Mm Mq Mr Ms Mz Nb Nd Nh Ni Nx Oh Oy Pb) Jp(Hq Ik Io Jr Lu Me Mq Mr Mt Mz Ni Nj Ns Nt Nx Oh Oy Pb) Lj(Hq Ik Io Jq Lu Me Mr Ms Mu Mw Mz Nb Nk Nt Nx Oh) Nh(Fr Jq Mm Mp Mq Mr Mw Mz Ne No Oh Om Pb Po) Oh(Fr Me Mm Mq Mr Mt Mz Nb Nd Ni Pb) Mq(Fr Jq Mm Ms Mz Nd Nt Nx Pb) Ms(Fr Jg Jq Mp Mz Nx Om Po) Mt(Jq Me Mm Mr Mz Nd Ni Ns) Nd(Mm Mp Mr Mw Mz Po) Pb(Fr Mr Om Po) Fr(My Mz) Jg(My Oy) PoHq MmMr OmOy} Ms{Om(Fr Jp Jr Li Lj Md Mp Mq Mr Mz Nd Nh Ni Nt Nx Oy Pb Po) Jp(Ik Jq Jr Li Lj Me Mr Nh Ni Nj Nt Nx Oh Po Qd) Qd(Fr Ik Jg Jq Li Mq Mz Nd Nh Ni Nx Oh Wm) Mt(Jn Jt Mm Mu Nb Nd Nh Nk Nn No Ns Nt) Fr(Jq Jr Lj Mq Mz Nd Nh Nt Nx Oh) Ji(Dp eC Ju Kg Kj lN nW oE Ow) Li(Jq Mq Mz Nd Nh Nt Nx Pb) Oh(Jg Jq Mq Mz Nh Ni Nt Nx) Mq(Jg Jq Lj Mz Nx) Jq(Jg Nh Nt Wm) Aj(Ad Is Kq) Is(aN Ct) WmKe} Is{Ct(Ad aN bA Bc bR cT dF dJ dM Hu Ih Il Ji Jq Kq Mq Nb Ne Ni Nk) Jk(Io jV Mm Mr Mu Mz Nx Om Pe Po Qd) Aj(Ad Ba bR dF dJ dM Ji Ni) It(Hv Hw My Nb Ne Nl Qd) Jo(Jg Mm Mr Nj Om Pe Po) Hr(Hw Jq Lw Mr Pe) Ih(aN Mm Nj Nx Oh) Io(Jg My Nj Ns Nx) Jg(Mw Nq Ns Oe) Pc(Hx Ii Mk Pa) aN(bR Ch Ji Ne) My(Mm Mr Mu) Jq(Ii Mb Md) Wm(Hx Oy) Mz(Nb Ns) Ne(Nj Nu) Ji(Dd Uk) NqQd LwIi MdOm MrIq JrJs OybA} Nd{Fr(Hu Ih Jk Jn Jr Js Jt Lw Me Mm Mp Mt Mw My Na Ni No Ns Og Pe Po Qb) Li(Jn Jt Lu Lw Me Mi Mm Mp Mr Mt Mw Mz Nk Oh Om Oy Pb Pe Qd) Jp(Jn Jr Jt Lw Me Mh Mi Mm Mt Mw Mz Ni No Ns Om Pa Pc Pd) Qd(Jg Jq Lj Mm Mp Mq Mr Mt Mz Ni Oh Om Pc Pe) Lj(Jg Jq Mm Mp Mq Mr Mt Om) Mt(Jq Mq Mr Oh Pe Po) Mm(Mr Pe) Mq(Jq Oh) Ji(bA cI) MpMz MrOh} Ji{Ii(bA bN bR cI Cs cT Cu dF dM Oa Rh Uk) Uk(bN Dp Ib Jm Lj Mw Ne Oa Oy Pb) bA(Aj Ch cI Co Ct Lj Ne Oy Pb) Aj(Ad Ba Dg Il Mt Ni) Wm(Dk eC Ib lN Um Vp) Ct(Ba Il Mq Mt Mw) Ne(aC aJ bV cI dM) Oy(Ar Ba bF cI Tr) Pb(Ax cI Cs Gp Us) Lj(gP Ha qC Tj) Dd(Il Jm) Ha(Ax Oa) MeqC NicI IlUs JpjP RhgP jDnW} Mt{Lj(Fr Ih Jp Jq Lu Lw Me Mm Mq Mr Nh Nk Ns Om Oy Pb) Mq(Fr Jp Jq Li Me Mr Mz Nh Ni Ns Oh Oy Qd) Ni(Jp Jq Jr Mm Mr Nh Nj Oh Pb Pe Po Qd) Pb(Fr Jq Li Me Mr Oh Om Pe Po Qd) Oy(Fr Jg Li Mr Om Pe Po Qd) Qd(Jq Me Nk Nq Ns) Jq(Li Md Nh Ns) Me(Jp Li Oh) AdAj FrMy NsLi} Fr{Oy(Ij Il Jg Jq Jr Li Lj Me Mr Nj Nl Nt Nx Oh Pe Po Qd) Nh(Jq Jr Li Lj Me Mq My Mz Ne Ni Pb Qd) Qd(Il Mq My Ni Nj Nq Pb) Lj(Ik Jq Me Mq Ni Nj Pb) Mq(Jq My Nj Ns) Pb(Ik Nj Nt) NiNj}

Figure 1 Continued

Ni{Li(Hq Jp Jq Lu Lw Me Mm Mq Nc Ne Nl Nt Nx Oh Oy Qd) Lj(Jg Jq Mm Mq Nh Nj Nl Nx Om Qd) Qd(Jp Mq Nc Nh Nj Nl Oh) Jp(Ik Mq Nc Nh Nl) AdAj PoPb ThSt llWc} No{oE(aF aO aP Bc bV Ch cK Ct DE Gl Jk Ne Nj Nk nW oN Oy Vt) oN(Ar Ha Nk Oy Rg Ri Wm) Wm(gP My oH Oy) gP(Ha Rg Tj) Ou(fN uM) OwfN dBqC} Mq{Lj(Jg Jp Jq Mm Nh Ns Nt Nx Om Pb) Li(Hq Jq Lu Nh Nj Ns Oy) Jp(Jq Nh Nj Ns Pb) Qd(Jq Nh Ns Pb) Nh(Jq Oh) Jg(My Oy) Om(Oy Pb) AdAj OhPb} Nw{qC(aN aZ Ba Ch dB dE Gl Hu Lj Me oE qA Qy Wm) qD(Ba Ch Dk Nv Qy Ua) Wm(bA Mw Oy) OwfN OybA} Nh{Li(Jq Lu Me Mz Nc Ne Nk Oy Pb) Jp(Jq Lj Me Ne Nk) Lj(Jq Ne Nk Om) Qd(Jq Ne Nk) OmOy} Oy{Om(Li Lj Mr Pe Po Qd) Jg(Mr Pe Po Qd) Ke(Il Nq Wm) Kq(Aj Wm) NqbA TrJh} Aj{Ad(aJ Ba bF cT dF Hu Il Pb Qd) Kq(Il My Oa Pb)} Wm{Ke(bA gP Ib My oE) My(Jp Om) Vt(oE oH) MdJq JrJs UhbA} Li{Jq(Md Pb) jT(sO vW) vS(jO Mz) MePb NkNl tUnW} Ct{Ba(As Dc Vt) Ad(bA cT) Kq(Dp Il)} Vt{qZ(dB nW) oE(cH Ne) MeqC nWvS} Ke{Ch(oE oN) DbqC IiOa wDnW} Lj{Jp(Ik Nj) Om(Lu Pb) wPnW} Fi{EdVq IlIv} Mz{Rb(qC qD)} ChKqcI DrIlOr NkVqoE IkJpPb wDjYnW

Constrained panels with 3 analytes, where 1.0E-7 >= 'model p-value' > 1.0E-8. Contains 10,179 panels of 36,050,556 total panels evaluated. : In{Lj(AD aI As Aw BA bB Bc bF bU bV cF cG cN Cp Cu Cw dE dG dJ dL Dp Fy Hv Hw Id Ij Jn Js Kd Kf Kn Ko Lu Mi Mp Nc Nu Pb Pc Pd Pg Pj Qb Qm Sr Uc Uh Ul Us) Vt(aA Ad Ax bF bL bN bV bW Cs cT Cu cV dF dJ dM dN Dp eC Fa Fb Fy Gp Ih Jm Jn Jy Kk Ko Kp Lh Lw Mm Mr Mz Ni Nj Nm Nt Nw Ny Ok On Ow Pb Qb Qm Rh Rm Uh Uk Us) Oa(Ad aM bA BC bL bR bV bW cE cT dE dF dJ dM dN Dp Fy Id Ij Im Is Jj Jq Kd Kn Ko Kp Kq Lw Mm Mq Mr Mw Nm No Nw Ok On Ou Pj Sr Uf Uh Ul) Ke(aM Ao Ch Cp Cs Dp Ed Fp Ib Id Il Iz Jl Jm Kn Li Lw Lx Md Mq Ms Mt My Nd Nj Nr Nw Oh Ou Oy Oz Pb Pe Pj Qd Qm St Uf Uh Uk) Mq(Ax Bc Cs dE Hu Id Ij Il Ip Ir Iv Jm Jo Ko Lw Me Mp Ms Mu Mx Nb Ne Ng Ni Nn No Nr Ns Ny Pb Pc Pd Pg Pj Pz Qc Wm) Nx(Hv Hw Ih Ij Ik Il Jg Jm Jn Jo Jp Js Lw Me Mh Mi Mm Ms Mu Mw Mx Mz Na Nb Nc Nd Ne Ng Ni Nj Nl No Nu Nv Pb Qb) Pf(Ed Fr Fy Hv Hw Jg Jn Jo Jp Js Lw Mm Ms Mu Mw Mx Nb Nc Ne Ng Ni Nl Nu Nv Oy Pb Pe Qb Rg Tv Ua Uh Ur Us) Id(Ax Bc Dp Fy Il Im Jl Jm Kq Li Lx Mm Mt Mz Nb Nd Ng No Nr Nw Oh Ok Ou Oz Pb Pe Qb Qd Qh St Uf Uh Wm) Jq(Ax Hu Ij Il Iv Jg Jm Jn Jp Jr Jt Lu Me Mh Mm Mu Mw Mx Mz Nb Nc Ne Ni Nj Nl Nr Nu Nv Pc Pd Pe Qb) Nh(Hv Hw Ih Ij Ik Il Ip Ir Jm Jo Js Lw Me Mh Mi Mn Mu Mx Na Nb Ne Nf Ni Nn Nu Ny Pc Pd Pg Pz Qc) Oh(Fr Hu Hv Hw Ij Ir Iv Jg Jn Jo Jp Jr Lu Lw Mh Mm Mu Mx Mz Nb Nc Ne Nl Nm Nu Nv Pb Pd Pg Qb Wm) Nw(AD aM As Ax bA bR bV Cs Cu Cw dE dF dJ dM dN Dp Ed Fy Kd Kn Ko Kq Kr Ou Ra Rh Sr Ul Us) aA(Fr Ij Il Ip Ir Jg Jm Jn Jp Js Jt Me Mf Mh Mm Mn Mr Mw Nd Nl Nr Nu Nv Ny Pd Pe Pz Qb Qc Wm) Lv(Hu Ih Ij Il Ip Ir Jm Lw Me Mp Mu Mx Nb Nc Nd Ne Ni Nj Nl Nn No Nr Nu Nv Ny Pb Pd Pz Qb) Pe(AD aM bA Bc bL bR bV bW cF Co Cv dJ dM dN Ha Jg Jn Jp Jr Lh Mm Mz Nj Om Qb Ul Un) Kq(Ao Ax Co Cs Ct De Dk Dp Il Im Iz Jj Jk Jl Kj Li Lw Lx Mw My Oy Oz Pb Pj Uh Wm) Wm(bB bV cE cT cV dM dN Ih Jn Jp Jr Jt Lw Lx Mr Mt Nm Om On Pj Po Uh Ti) Im(aD Aj As bW Ch Ct Cv dE dN Dp Dr Kd Kk Kn Ko Ou Ow Pj Uf Uh Uk Ul Us) Qe(aC bN bR bV dF dJ dM dN Dp Fy Kd Ko Ou Pj Qm Ra Rh Sr Uh Uk Ul Us) Mw(Ax Cs Fa Fy Ik Iz Jj Kd Kk Ko Kp Kr Mr Nj Ou Pi Pj Pk Sr Ul) Uh(Ad As Ax bA Bc Cq Cs Cu Cw Dc Kd Kn Lw Mr Sr Tv Us) Fp(aD aM bA bB BC bV bW cE dE dF dJ dL dM dN Uf) Fr(Jj Jn Js Jt Me Mr Ms Mz Nc Ne Ni Nl Nu Oy Pb Qb) Nt(Ir Jg Js Jt Lw Mh Mp Ms Mu Na Nb Nf Ni Nj Ns Pc) Un(Aj aM bA bN cH dJ Fy Hx Lw Lx Nd Ne Nr Oy Rh Ul) Jl(aC Ad Aj Ar Ax bA Ch Cs Ct dE Iz Kd Kn Ko Pj) Mr(Jg Jj Jn Jp Jr Js Mm Mz Ne Nj Nl Nv Pb Qb) Fy(Aj Bc bW Ch Ct dJ Et Is Jj Lw Ng Pb Qa) Qd(Ad Aj bA Cs cT dE Dp Hu Jp Jt Nu Ou Ul) Om(Jn Js Jt Lu Md Mx Nb Nc Ns Nu Og Qb) No(bS cA dE dJ Ik Nd Nj Pj uM Tj Th) Jg(Jr Me Mh Ms My Mz Nd Ni Nj Oy Qb) Mt(Ad Aj As Ax Bc bR Ch Cs Cu Cv) Jj(Cu Ij Jn Jp Jr Js Jt Mz Nr Qb) Li(Ad Bc Dp Kd Kn Ko Ou Rg Ul) Nj(Jr Js Jt Mm Mp Ni Nv Qb) Jp(Jr Jt Mh Ms Ne Ni Nl Nu) Ax(Hu Kn Nb Ny Ou Uf Ul) Nd(Ij Jn Js Mm Mp Mz Qb) St(Ad Bc Ch Dr Lw Ng Ti) Lx(bR dN Dp Kd Kn Tj) Ik(Jn Jr Lw Mp Nv Pb) Jt(Jr Lh Mz Ne Nl Qb) Bc(Ed Kn Ko Ou Sr) Me(Jn Js Mm Nv Qb) Ng(Ad Ba Cu Nv Uc) Is(jU jV Qm Ur Us) Mz(jK Jr Ne Nl) Ji(eC jO jP oE) Kn(Il Lw Pb Uf) Aj(Cu Ok Uc) Po(dE Hw Jo) Et(aF bL Tv) Qa(gP Qg Qm) Jr(Mm Nv Qb) Js(Mm Nb Ni) Uf(Cs Kd Lw) Ch(Ok On) Dr(Hu Il) Vq(Ed Jn) CsOk CtCu FaLw MsNv NiQb SrPj} Et{Uk(AO Ax bA cI Co Cs Ct Cu Dc De dM Fp Gl Hc Il Im Iz JD Jl Jm JO Jq Jr Jy Kd Ke Kn Kq Lw Me Mi Ml Mq Mr Nd Ni No Nw Oi Or Oy Oz Qd Qe Qu qX Ra Sr Tv Ud Un Us Vt Wm) cI(aA aC aF AO Ap Ax bL bN cH Co Cs CT dM eC Ed Fp Hq Ii Im Iz Jl jO Jq Kj Lv Me Mg Mh Ml Mm Mq My Nb Nd Ne Ni No Nw Oa Oz Pb Pf Qa Qc Qd Qe qX) bA(aF aH aL Aw Ax bL bN cG Dg Dk Ed Ef Fp Gl Hc Hu Ib Is Jd Jg Ji Jk Jt Kj Mh Mk Ml Mm Mw Ne No Nv Nw Of Oz Pb Pf Pg Qa Qe Qu Ss Vt Vv) Ct(aC Ap bN bV Ch Cp Dc Dp Ed Fb Fy Id Jr Jy Kd Ke Kn Kq Li Me Ml Mt Mw Nw Oh Or Ou Pi Qd Qh qX Ra Ri Sr St Tv Ud Ul Un Us Vt Wm) Iz(aA Ax Bc Cs cT dM Ed Fp Fr Hu Id Il Ji Jl Jo Jq Jy Kd Ke Kq Lj Lv Lx Mm Mq Ms Mw Nb Ni No Nw Oa Or Oz Pe Qa Qd Qe Un Vt Wm) Co(aA aC Ar Ax Cs cT dM Ed Fp Hu Ii Im Jl Jq Jy Ke Kq Li Mh Ml Mm Mq Mr Ms Mu Nb Ni No Nw Oi On Ou Oy Oz Pe Po Qa Qd Qe Ur) Kj(Ad Ax Bc Cs Cu Dc Ed Id Il Im Is Ji Jl jO Jq Jy Kd Ke Kn Kq Kr Lw Mm Mr Ms Nb Ni No Or Ou Oz Qa Qd Qe Sr Un Us Vt Wm) Ao(aA aC cT dM Fp Ii Im Jh Jl Jq Jy Ke Kq Li Lv Lx Ml Mm Mq Mr Mt Mu Nb Ni No Nq Nw Oi Ou Oy Oz Pe Qa Qd Qe Ur Wm) Oa(aO Ap cT De Dl dM Ed Gl gP Ha Ih Is Ji Jt Jy Ks Lw Ms Nd Ne Ni Nk Nv nW Oe Oi Ou Oy Oz PF Qv Tv Ur Us Wm Tj) Oy(aC Ad aO Ap Ar As Ax bN bV Cp Cq Cu Dc dM Dp Ed Fa Fy Id Kd Kn Pi Qh Qv Ra Ri Sr Tn Tr Tv Un Ur Us Vp Vs) Pf(aC aF bL bN bR bS cA cG cO DE dH Dk Dl dM Ed Gl Ha Hc Ib Jd Kl Ks oN Ow Qt Qu Ss Ua Ur Us Uu Vt Vv Tj) Ed(aO Ap De Gl Id Ii Is jD Ji Jk jM Jo Jy Lj Lw Mm Ms My Ne Ni Nk Oi Ow Oz Pb Qu Ur Us Vt Wm Tj) Ch(Ap Ar Ax bF bH bL bN eC Fb Fy Gp jD Jm Kd Li Lu Mq Mr Nd Nw Oh Or Oz Pe Qd Qh Qv Ri St tF) Jo(aC aO bL bV Cp cT dM Dp Fy Jy Ke Kp Kq Kr Or Ou Pi Pk Ra Rj Sr Tv Uc Ud Ul Un Up Us Vp) Ap(bL bN Cs cT dM Fp Id Ii Jl Jm Jy Ke Li Lv Lx Mh Ne Ni Ou Oz Pe Qd Ri Ur Us Vq Vt Wm) Cs(aA aC aO bL bN cO cT Dg dH Dl dM Ha Ih jD Jy Lv My Nd Ni Nj Oi Ou Oz Pb Ur Us) Ms(aC aH aO bL cT dE Dl dM Gl Id Jy Kd Ke Kl Kn Ks Or Ou Ow Qu Ss Un Ur Uu Vt) Is(aC aO bN bR Cq Cw Dd De Dg dM Gl Hc Ib jO jP Ks Qu Tv Ua Ur Us Uu) Wm(aC aO bH bN JD Ks nW oE oH oN Ou qV qX Ur Us Vv Tj) Ax(aA aC Dg Dl Ha Ii Jt Lv Mm Nd Ni Oi Oz Pb Ur Us) aC(aA aK aL aX bE dM Fp Im Ji Jj My Ne No Oz Qa) Ii(Ad As Cu Cw Id Kd Ke Kn Ou Un Us Vt) aO(bV cT dM Fp hB Jl Lv Lx Mt No Nw Qa) Lj(bL eC Ks nW pF Qv Ri Tv Ur Us vS) Ou(Bg Hc Hq Mm My Ow Oz Pb Qu Ur Uu) Ji(bN dM gP Hc Ib Jd jO jP Ow Us) Dg(Im Jl Lv Lx Mq No Qa Qd Qe) Ke(Cp Dc Dk Ib Jt Mm My Oz Pb) dM(Fp jD Jj Mh Mm My Nd Ne Oz) qX(Aj cD cP cQ dE Fb Kg nW) Qa(Al Bg Cw Dl Ib Ur Us) Vt(Mm nW oE Oz Pb Ur Us) Aj(jD jP nW oE oN Vq) Jl(Bg De Dk Dl Ur Us) aA(aF Bg bL Cw De Ef) No(eC gP nW oE Tj) Mm(Id Jy Un Ur Us) My(Ar Bo cT Jy Kq) Jj(bL bN nW oE oN) Dk(Kq Lv Mu Nw) Id(De Jt Oz Pb) Im(Bg Dl Ow) Qe(Al Dl Us) Oz(Kd Ur Us) jD(aM cB Gl) Fp(dE Kg) Lv(Bg De) Lx(oN Tj) Jt(Dc Kd) Jy(Hc Hq) qZ(dB fP) BbNw LwUr MtoN NebV IbKq VqoE nWuN} Pf{Aj(BA BB bL bS bU cA cF cM CO cT Cu Cv Dc dE Dg dJ Dl dM Ef Gp Ha Hq Id Ij Il Jl Jt Jy Kd Kn Ko Lh Lv Lz Mq Mt Mw Nb Nd Nk No Nt Nw Ok Om On Ou Oz Pa Pb Pj Pz Qa Qc Rg Sr Uc Uf Uh Ul Un Vt Tj) Ct(As bL bR bS bU cA CO Cp Cu Cv Cw Dc dE dJ dM Dp Fy Gp Ha Hq Hw Id Il Iv Jg Jn Jr Jt Jy Kd Kn Ko Lh Lv Lw Lz Mr Mt Mw Na Nb Nd Nk No Ok Om On Ou Oz Pa Qd Qc Rg Sr Uh Ul Un Ur Vt Tj) Pb(aC aD aN bL bR bS bV cA Ch CO cT dE dM Ed Gp Ha Id Ik Iz Jg Jp Jr Jt Jy Kd Kk Ko Kp Kq Li Me Mm Ms Mz Nb Ne Nj Nl Nx Oh Ou Pe Pj Po Qd Qm Sr Tv Ua Uh Uk Ul Un Us Tj) Ni(aF bL bR bS Ch CO dM Fr Jg Jn Jq Jr Lj Mm Mq Mr Ms Mz Nc Nd Ne Ng Nj Nl Nt Nx Oh Om Oy Po Vt) Lh(Hr Hx Il Jk Jl Jo Jp Jq Jr Lj Me Mk Mm Mq Mw Mz Ne Nj Nl Ns Nx Of Og Oh Pa Pe Qd) Jj(aF bA bS cA cK dE dH dJ dM Fy Ha Ir Iz Lu Mg Mm Ms Nc Nm oE oN Pa Pe Pj Rg) Im(Ch Co Fr Hw Ih Il Io Jp Jr Lw Lx Mm Mr Mz Nj Nk Ns Nt Nx Og Om Pa Pe Qd) Ch(aA Ad bA bR dM Jp Jq Ke Kq Ky Mk Mt Nd Nw oH Ok On

Figure 1 Continued

Qa Qd Uh Un Ur) Co(aA bA Is Jl Jp Jq Jy Ke Kq Lv Lx Mq Mt Nb Oi Om On Ou Oy Uh Ur Vt) Nh(Fr Jp Jr Jt Lj Me Mm Mr Ms Mt Mz Nb Nc Ne Ng Nk Nt Nx Oh Om Pe Qd) Oz(aC bA bR bS cA cO dE dM Ha Id Iz Kd Ke Kn Pj Ua Uk Un Ur Us Th) Oy(Ik Jn Jr Jt Li Mm Mr Mu Mz Nd Nj Nl Nv Nx oE OH oN Pe Po) Qd(Hq Jl Jp Jq Lu Me Mr Mt Mz Nb Ng Nj Nk Nt Nx Og Om On Pa) Mq(Fr Hq Jg Jn Jp Jr Lj Mm Ms Mz Ng Nj Nl Ns Nt Nx Oh Om) Jq(Fr Hq Ik Jp Lj Lx Md Mm Mz Ng Nj Nt Nx Oh On Pa Uk Ur) Ke(Ao Cp De Ha Hq Ib Iz Jk Jo Kg Kj Mk My Nv oN Pa Uk Tj) Nd(bA dM Fp Jg Jn Jt Lj Lw Mm Mp Mr Mw Mz Oh Om Pe Po) Jl(Hr Ii Jk Jp Jr Lj Lu Lw My Mz Nj Nt Og Oh Om On Tj) Vt(aA Ed Gp Hq Ii Iz Jk Jo Kg Kj Mk Ms oE Pa Rg Uk Tj) Qa(Ha Hw It Lu Lx Me Mz Ne Nj Ns Nx Og On Pe Uk Ur) Qe(Ih Il Jk Jp Lu Me Mr Mz Nj Ns Nt Nx Og Om On Pe) aA(aO bL bR bS cO Hq Jn Jp Me Mf Mm Ng Ns Nt Oh Om) Mt(bR bS cO Hq Jp Jr Lw Mr My Mz Nk Ns On Pa Pe) Is(aC aD Al bA bL bR bS cA cO dH dJ dM Ha Uk Ur) dM(bL bR bS cA cO dH Hq Iz Jk Mk Ne Nk Nw Wm) Mk(aC bA bL bS Jy Kk On Or Ou Uk Un Ur) Nw(aC Ao bA bL bR bS cO Ha Iz oN Tj) On(Hu Hw Jo Jr Lu Md Nj Nl Nq Oe Of) Hq(aC bA bR gP Jp Jy Lx Or Ou Ur) Un(Ha Iz Jk Jo Kg Kj Ms Uk Ur Tj) Lv(Fr Il Jn Jr Nb Nt Nx Om) Ng(Fy Jp Li Lx Mu Nt Nx oE) Fp(Jn Lw Nx Oh Pa Pc Pe) Ms(Fr Jg Jp Mz Nt Nx Oh) Ji(Dp Gl Kj nW oE oN) Jp(Ik Iz Me Nj Nt Pa) Lx(Me Mz Nj Pa Tj) Ha(Id Lj Lw Oa) Uk(Id Lw Sr Ul) Ur(Dp Id Lw Ul) bA(bL Jk Lj Wm) bR(aC dE Lj My) No(bS oN Tj) Wm(Mw Nv) Fr(Me Nj) Nk(Nl oN) Ii(Kd Kn) Kg(Dr Pj) Kq(Iz Jk) bS(Ne Pa) EdFi TjLw MyOm MzNj JoKn JyoN} Jj{Wm(aA bA dF dM Fr Ij Il Io Ip Iq It Jg Jk Jm Jn Jr Js Jt Ke Lw Mi Mj Mm Mp Mq Mr Ms Nb Nd Ng Nm Nr Nt Nv Nx Ny oE Om Pb Pd Pg Po Pz Qb Uh Un Vt) Lj(Ad BA Bc bF bR cT Cu dF dM Ij Il Ip Jk Jm Jr Js Jy Ke Kq Lu Lw Mf Mp Nb Nc Ne Nk Nm Nu oE Pb Pc Pd Pe Pg Sr Uf Uh Un Vt) Il(aA Ad Ax bA Bc Cs Cu Fa Fb Id Jn Jr Js Jt Kd Ke Kn Ko Kp Kq Mm Mw Ni Nj Nm Nr Nu Nv Ou Pj Pz Qm Rm Sr Uf Uh Uk) Mz(Hu Ij Ip Ir Jk Jn Jo Jp Jq Js Jt Lu Me Mf Mg Mh Mm Mp Mr Ms Mu Mw Mx Nb Nc Ni Nr Nu Nv Pd Pe Pg Pz Qb) Jq(aA Hu Ij Ip Ir Jm Jn Jr Js Jt Lu Me Mf Mg Mh Mm Mr Mu Mw Nb Nc Ni Nr Nu Nv Pb Pc Pd Pe Pg Pz Qb) Mw(aA Dp Fr Hu Ip Jm Jn Jo Jp Jr Js Jt Lu Me Mf Mr Ms Nb Nc Ne Ni Nl Nr Nu Oa Pd Pe Pz Qb Vt) Jm(Cu Hu Ij Jn Jr Js Jt Kq Lu Me Mm Mp Mr Ms Mu Nb Ne Nl Nm Nr Nu Nv Ou Pd Pe Pz Un Vt) Oa(Ad bA Bc Fy Ij Im Jl Jp Jy Ke Ko Kp Kq Lw Nd No Nw Ou Pb Pj Qd Qe Qm Sr Uf Uh Un Vt) Dp(Ad Ax Cu Id Ij Jp Ke Ko Kq Lh Li Lx No Nr Nw Oh Ou Pe Pj Qm Sr St Uf Uh Un Vt) Jn(aA Hu Ij Ip Jo Jp Jr Jt Lu Me Mr Ms Mu Nb Ne Ni Nj Nl Nr Nu Nv Pd Pe Pg Pz Qb) Vt(bA eC Ed Ij Jy Kq Li Lx Mq Ms Nd No Nr Oh Ou Oz Pb Qc Qd Qe Qh Qm Rm St Us) Jr(aA Hu Ij Ip Jo Js Jt Mg Mm Mp Mr Mu Nd Ni Nj Nl Nm Nr Nu Nv Pd Pg Pz Qb) Pz(aA Hu Ij Js Jt Me Mf Mh Mr Ms Mu Nb Nc Ne Ni Nj Nl Nr Nu Pe Qb) Jp(aA Hu Ij Io Ip Jo Js Jt Lw Mh Mu Mx Nb Nc Ns Pb Pd Pe Qb) Nv(aA Fr Lu Mf Mh Mr My Nb Nc Nc Ng Nr Ns Nu Oy Pb) Nd(aA Cu Ii Ip Jk Jo Mj Mu Nm Nn Nr Ny Pd Pg Qc) Nj(aA Ij Ip Js Jt Mp Mr Mu Nb Ni Nm No Nr Pe Qb) Jl(aC Ad Ar Ax Bc bN bR cI Ke Kp Ou Pj Qm Uh Un) Fr(aA Hu Ij Ip Ir Mm Mr Mx Nb Nm Nr Ns Pd Pe) Mq(Hu Jk Lw Mf Mg Ms Mu Nb Ni Nn Ns Ny Pc Pe) Im(aC bA bR cJ Jy Ke Ko Kp Ou Ow Pj Ul Un Us) Js(aA Hu Ip Lu Me Mg Mm Ms Mu Nb Ni Nl Nu Pd) Qb(aA Hu Jt Mc Mg Mm Mr Ms Mu Nb Nl Nu Pd) Nl(Ij Ip Jt Mm Mp Mr Nb Ni Nk Nm No) Ji(bA bN bR dM Ed jO lN nW oE oN Ou) aA(Ij Ip Jt Lw Mf Mm Nm Nu Pd Qc) Nr(Ij Ip Jt Me Mm Mr Mu Ni Nm) Qe(bA bN bR cI Id Jy Ou Qm Us) Kq(Ao Ch Co De Dk Iz My Oy Pb) Fp(Ad bA Bc Cu dF dJ Ke Ou) Ng(Cu Ef Fy Ke Uc Uf Un) Ij(Mf Mm Ms Ne Ni Nu Pb) Nh(Hu Jk Lw Mn Nk Pc) Qa(bA gP Ou Qg Qm Uh) Jt(Hu Mb Me Ne Ni) Nw(Ao Ax bA oE Ou) Ni(Mm Mp Nc) Qd(bA gP Ou) Jg(My Nb Ns) Pb(Cu Ke Un) oE(Is Kc To) Ax(Mt Ou) Mr(Mm Nm) Ms(Mp Un) NonW NcNk IsjV} Ng{Uf(Ad Ba Dp Ef Fy Gp Hu Id Jg Jh Jl jO Jp Jq Jy Kd Kn Ko Lj Lv Lw Lx Ml Mq Mt Mw Nb Ni Nj No Nr Nw Oa Ok Om On Or Ou Pe Qa Qd Qe Ql Qm Sr St Uh Uk Ul Un Ur Us Vt Wm) Ba(Aj Ar Aw Cp Ct Fr Id Ij Il Im Jg Jh Jl Jq Jt Jy Ko Lh Li Lj Lv Lw Lx Mg Ml Mq Mw Nb No Oh Ok Om On Or Ou Pb Pg Pj Po Qb Qc Qh Qm Ri Sr St Tn Tr Ur Wm) Kc(Ad Bg Dp eC Ef Fr Fy GP Hv Hx Ii Ij Is Jg Ji Jl Jp jV Jy Ko Lj Lx Mq Ms Mt Mv Ne Nj Nr Oa Oh Ok oN Ou Oz Pb Pz Qa qD Qe Qm Rh Uk Uu Vt) Qa(Ad Aw Bc bF Bo bR cT dF Dg Gp Ih Jh Jy Lu Lw Me Mg Mr Mu Mv Mz Nb Nc Ne Nh Nj Oh Ou Pb Pc Po Qb Qg Qm Tr Uh Uk Ur Vt) Im(Ad al Aw Bc bF bR Cv dF Dg dM dN Il Jr Ko Lj Me Mg Mi Mp Mv Mz Nb Nj Nk Nn Nu Nv Oh Ou Pc Po Tr Uh Un Vt Wm) Jp(aA Ad An Ar Aw Ax Cp Cu Dp Hu Id Jq Jr Jy Ko Lj Lu Me Mr Ms Mu Ni Nj Nx Oh Ou Qd Qm Sr) Li(Ad Fp Hu Jh Jr Jt Jy Lj Lu Lw Lx Lz Me Mg Mm Mr Ms Mu Mv Mw Mz Nb Nj Nk Nv Oh Pb Qd Wm) Nw(Aw bA bF bR Cp Cu Cw dF Di dM dN Dp Ef Fy Jy Ko oE Ou qC Qm Qt Rh Sr Tn Tr Uc Uh Ul Uu) Qe(Ad Aw Bc bF Cp cT dF Ih Jr Jt Jy Lu Lw Me Mg Mr Mv Mz Nb Ne Nj Oh Pb Pc Pe Po Tr Wm) Mt(Ad Aw Cp Cu Hu Ij Ik Ip Jh Jo Jr Lw Me Mm Mp Mv Mw Mz Nb Nd Nh Ns Nv Pb Pc Wm) Lx(Ad Ef Hu Jh Jn Jo Jr Jt Lu Lw Me Mm Mv Mw Mz Nb Nj Nk Oh Pb Pc Pe Un Wm Tj) Is(Ar bA bB Bc bF bV cV Dg dN Gp Id Jy Kl Ko Ou Qm Qv Sr Tr Uh Uk Ul Un Ur Vt) Jl(Ad bA Hu Jh Jt Lj Lu Lw Mb Me Mm Mu Mw Mz Ne Nj Oh Pb Po Qd Uh) Ad(Ar bA dM Fr Hu Ij Il Mq Mw Nb Oh Ok Om On Pe Qd Uh Un) Ji(Dp eC Fa Fb Fy gP Kl Ko Kp Oa oE Ou qC qD Qg Qm Rh Ri) Qd(aA bA cT Ik Jh Jq Mm Mu Nb Nh Nj Nt Nx Oh Po Tr) Lh(Ii Jh Jn Jq Jr Lw Mv Mz Nb Ne Nj Nk Nl Pc Pz) Ij(Bc Bo Dg dM Id Jy Ou Tr Uh Uk Ul Un Ur Vt) Fp(Hu Jh Mg Mp Mv Mw Nn Nv Nx Po Pz) Lv(Jt Mm Mp Mq Mu Mw Nt Nv Nx Oh Po) On(Aw Bc Dp Id Jy Qt Rh Uh Uk Ur Vt) Nt(aA Jq Lj Mp Mu Mw Oh Po) Om(Bo Il Md Me Mm Mr Nu Nx) Kq(bA bF cI dE Fy gP hV) Mq(Jq Nh Nx Oh Po Tr) bA(Jg Pe Pz Uh Vt Wm) Wm(Jq Jt Mw No) Il(Id Un Vt Xa) Ko(Jy qC Uh Un) aA(Mm Nx Oh) qC(Mz Nm Uc) Po(Nh Ni) No(eC Th) Mw(Id Tr) Jg(Un Vt) Ok(Aw Jy) oE(Vq Vt) AjEf BcSt HaPe UcUr TnUh JhLj} Jl{Mz(Fr Hr Ik Jg Jq Jr Lh Li Lj Lu Lw Mb Me Mf Mk Mm Mq Nb Ne Ni Nj Nk Nl Ns Nt Nx Og Oh Oy Pa Pb) Mk(aA Hu Ij Jh Jn Jq Jr Lj Lu Lw Mb Mc Mf Mm Mq Mu Mv Mw Nb Ne Ni Nj Nk Nl Nt Pb Pc Qd) Mq(Fr Hq Hr Hw Hx Ii Jg Jr Lh Lu Lw Mb Me Mm Nb Ni Nj Nk Nt Nx Og Oh Om On Pa Po Qd) Ns(Fr Hu Ik Jg Jn Jq Jr Lh Lu Lw Mb Me Mm Mw Nb Ni Nj Nk Nl Nt Og Oh Pb Pc Po Qd) Nj(Fr Hr Ii Jg Jq Jr Lh Lj Lu Lw Me Mm Mp Mw Nb Nc Ne Nx Og Oh Om Oy Pb Po Qd) Nk(aA Fr Hu Ik Jg Jn Jq Jr Lh Lu Lw Mb Me Mf Mm Mw My Nb Nt Nx Og Om Oy Pb Po) Oy(aA Hu Ij Jn Jr Lj Lu Lw Mb Mf Mm Mp Mr Mu Mw Ne Nn Nt Nv Pc Pd Pe Qd) Jq(Ct Fr Hq Hw Ii Jg Jp Lh Lu Md Me Mf Mm Nb Nt Nx Oh On Pa Qd) Hr(Fr Hv Hw Ik Jg Jr Jt Lj Lw Mf Nh Ni Nx Oh Om On Pb Po Qd) Mb(Fr Hq Hw Jn Jp Jt Lh Lu Lw Mm Nb Ni Og Oh Om On Pb Qa) Me(Fr Hq Hw Hx Ii Jg Jn Lh Lw Mm Nb Ni Nt Nx Og Om Po Qd) Jp(aA Hq Ii Io Jk Jr Lu Lw Mf My Nq Nt Nx Og Oh Pa Qa) Pb(Hu Hw Ip Jn Jr Lu Lw Mf Mm Mr Nb Ne Nl Og Pd Pe) Om(aA Ct Hq Hw Hx Jo Lu Md Mw Nq Nv Of Oh Pa Qd) Nb(Hw Ii Jk Lh Lj Lw Mm My Nh Nl Nx Og Oh Qd) Fr(Hq Ii Ik Jr Lw My Ni Nl Nq Nt Og Pa Qd) Lh(Hq Hw Jk Jo Lu Md Mw Nq Nv Of Og Pa Pg) Jg(Aj Hq Ii Io Jr Lu Lw Mw Nq Oe Og Pa) Ik(aA Hw Ii Jk Jo Lw Mm My Ne Ni Oh) Ji(bN Co Dd DE Dk Ha Ib Ur Us Tj) Lj(Hq Hw Ih Ii Lw Lz Ne Nr Nt Og Oh) Qd(Hq Hw Hx Jk Lu Nq Nx Og Oh Pa) Ct(Ad bA cT Ij Im Kq Mt Qa Qe) Nt(aA Ii Jk Ne Ni Oe Og Oh Pa) On(Hw Hx Jo Jr Lu Md Mf Mw Nv) Po(Hq Hw Hx Ii Jk My Og Pa) Lw(Hw Ii Lu My Ni Nx Og Oh) Nx(Ii Jk Jo Lu My Oh Pa) Aj(Ba Im Is Ok Qe) Lu(Jk Mm My Og Oh) Ni(Hw Jn Jr Mp Mw) Oh(Hq Hw Jk Og) aA(Mm My Ne Nq) Nc(Ne Nl Qa) Jr(Mm Nh Pa) Li(Hw Qa Qe) My(Mv Wm) Ii(Jt Ke) Og(Hu Mw) TjLx NqQa MsNv NeNl HwHx JnJs UrVt} Im{Jp(Fr Hq Ih Ik Il Io Jk Jn Jq Jr Li Lj Lw Lx Mf Mh Mr My Mz Ne Nk Nl Nq Ns Nt Nu Nx Oe Og Oh On Oy Pb Pe Po Qd Qe) Og(Hq Hu Ik Il Jg Jn Jq Jr Jt Li Lj Lw Lx Me Mf Mm Mr Mu Mz Nb Nj Nl Nt Nu Nx Oh Om Pb Pc Pe Po Qd) Nx(Hq Hw Ii Il Io Jn Jq Jr Jt Li Lj Lw Me Mi Mm Mz Nb Nj Ns Nt Oe Oh Om Oy Pb Pc Pe Po Qd) Qd(Hq Hw Ih Ii Il Io It Jk Jq Li Lw Lx Me Mm Mr Nj Nk Nl Ns Nt Oe Oh Om Oy Pb Pc Pe) Nt(Fr Hq Ii Il Io Jq Li Lj Lu Lw Lx Me Mp Mr Mz Nk Ns Oe Oi Om Oy Pb Po Qa Qe) Mm(Hq Hw Ik Il Io Jn Jq Jr Li Lj Mh Mq Mr Mz Nb Ne Nj Nl Ns Oh Oy Pb Pe Qa Qe) Lw(Hq Hw Ik Il Io Jr Li Lj Lx Me Mr Mz Nb Nj Nl Ns Oh Oy Pb Qa Qe Uk Wm) Hq(Jn Jq Jr Jt Lj Me Mf Mh Mi Mp Mu Mz Nb Nj Nl Oe Oh Om Pc Pd Pe Po) Jq(Aj Ct Hw Ik Il Li Lj Mb Md Me Mr Nb Ne Nj Nl Ns Oh Oy Pb Pe Wm) Lj(Hw Ih Ik Il Io Jg Lx Me Mr Mu Mz Nb Nj Nk Ns Oe Om Pb Pc Pe) Pb(Hu Ik Il Jr Me Mh Mi Mu Mz Nb Ne Nj Nl Nu

Figure 1 Continued

Oh Om Pc Pd Po) Lx(Fr Hw Hx Ih Ii Ik Io Jk Jn Mh Mz Nj Nk Ns Oe Pe Pg Tj) Li(Fr Hw Ih Ii Il Io Jk Mr Mz Nj Nk Nl Ns Oe On Pe Qa Qe)
Oy(Ik Jh Ke Lu Mi Mu Mv Mz Nb Oh Pc Pd Pg Po Qa Qe Vt) Il(Jn Jr Jt Me Mi Mz Nb Nj Oh Om Pc Pe Po Qa Qe) Ji(aC aN bR dE Dp Gl Ha
Ib Iz Kg Kj Ou Ow Us Tj) Mc(Hw Jr Lu Mr Mz Nb Nj Oh Om Pc Pe Qa) Nj(Jn Jr Lu Mp Mr Mz Nb Oh Om Pe Qa) Aj(dF Is Ke Kq Ni Nw Ou
Uf Vt Wc) Pe(Hr Hw Hx Ii Io Jr Nk Ns Pa Qe) Om(Hu Hw Ii Jk My Ns Oe Qa Qe) Mr(Hw Hx Ii Jk Jr Nk Ns Qa) Mz(Fr Hw Ih Jk Jr Nb Nk Qe)
Ct(Ba Ke Kq Ni Nw Vt) Fr(Hu Ik Jr Ne Nl Oh) Ns(Jr Lu Nu Oh Pc Qe) Nk(Jr Lu Mq Ne Nu Oh) Qa(Hr Hw li Jk Mb Ne) On(Hr Ih Io Mu Mv
Nv) Qe(Ii Jk Oe Qb) Nl(Nb Nc Ne) Jn(Hw Js Mq) Oh(Hw Nb Oe) Vt(Ii Uk Ur) Ch(Kq Ou) My(Jg Jh) Ih(Jr Mq) Ke(Ii Uk) DrJt WmMs PoNh
LuJr} Ji{Aj(aA bF bJ bR cT dF dJ dM Dp Ef Fb Fy Gp Jg Jm Jp Kl Li Lv Mq Mw Nb Qa Qd Qe Tr Uc Uf Uh Uu) Oa(bA bJ cI Dd Dp eC GP
Hx Ih Jy Ne Ni Nk nW oE Oy Oz Pb Qg Ur Us Tj) Dp(Ct Dd Ib Ii Il Jo Kg Lj lN Mk Ne Ni Oy Oz Pb Qv Ur Us Tj) Il(aC bA cA Ch cI dE dM
Ha Ib Iz Kg Kj Ow Up Ur Wc Tj) Lj(bF bJ bR cT Dd dM eC Gp Jy nW oE Ou qD Qg Ri Ur Us) qC(AW Ax aZ bN cB Ch Gl Jn jO Li Mh Ms
Ou Ow Wm) oE(Af aW BG bN CH De Ne Nk No nW Ow To Uk Vt) Cs(bJ cT dH gP Ha Ih Jo Mj Mk Nd Nj Nk Nx oN Tj) Ct(bF bJ cT dF dM
Ef Fy Jm Jp Jy Kq Lv Nb Ni Rh) Mt(bJ bL bQ bR bS bU cA cF cG Ch cK cO dH Dk oN) cI(bN bR dJ eC Gp Is Jo Jy Mm Mw Nk Oz Qg Qv)
Tj(Ax Ed Fa Fp Is Jy Li Lx Mh Mr Mw No Tr) Oy(bR cT dF dM Ef Fa Fy Gp Jy Kq Ou Qv Ur) bA(aC dE Gl gP Ib Is jD Jo Kg My Ni Oz Qg)
jO(iC Is Jp Mc Mp Mz Na Nc Nh Nk Qg Ql Uk) Wm(Ao Gp Ha Je qB qD qX Qz Ur Us Ut Vv) lN(Ik JP Mc Na Nh Nj Nk Nt Og Uk tF) Ii(Ed
Fa Fb Fy Id Ou Ow Qm Sr Uf Uh) bF(aF Ao Ap Ch Co hA Hq Jo Mk My Nd) gP(aW cH Ed Hc Li Mh My No Qa Rb Uk) Oz(aC bN dM Gp Kp
Qm Qv Tr Ur Us) Pb(bN bV cT dM Fy Kp Ou Qv Rb Ur) Ax(bQ cO dH Mk Nj Nk Nx oN Rg) Ch(Ba cT dF eC Is Kq Mw oH qD) Co(cT dF Li
Lv Lx Mq Nb Tr) Jo(cT dF dM dN Fy Gp Uf Uh) bN(aN bR Dd dM jD jM jV Ni) Ha(Ed Fp Li Lx Mw Pe Qa) Jy(Ao Dk Ib Mk My Nv Ut)
Qv(Hx Ib Jm Md Mk My) Us(Is Jm Mw Nd Qa Qe) aC(aX bE bJ dM Is Mw) nW(Bc Ne No Rh Vt) Dd(Lv Nb Qe Ri) My(Bg Bo bR cT) Qg(De
Ed jD Md) Kg(Fy Mw Uf Uh) dM(bR Is Mm Nd) qD(cB Hc Me Ou) oN(dF Li Ne No) Ib(Mw Ne Ni) Kq(Ao Dc Dk) Ur(Bn Is Jm) bJ(aN bV
cV) fN(Ms Ou Ow) Ed(Hx Nk) No(cA dE) Tr(Hq Mk) bR(Is Qa) eC(cW Ne) AlJm AoNb DkNw FbqX FpdE FyUk MwIz NdcT NiRb NkbV
OwhP aFdF aHeZ} Qa{Oy(bA Hu Ih Ik Jh Jq Ke Lj Lu Lw Me Mi Mm Mu Mz Nb Ne Nh Nj Nk Nt Oh Pd Pe Pg Po Qe Uk Vt Wm) Ih(Aj bA
Ct Fr Hq Hu Hw Jg Jp Lj Lu Lw Me Mm Mr Mz Nb Ne Nh Nj Nt Og Oh Om Pb Uk) Lu(Hq Jg Jp Jq Li Lj Lw Lx Mm Mr Mz Ne Nh Nj Ns Nt
Nx Og Oh Om On Qb) Lx(Hr Hw Hx Ii It Jk Mb Mh Mr Mt My Nj Nq Ns Nx Oe Og On Pg Po Tj) Mc(Hq Hr Hw It Jg Jq Lh Lj Mm Mr Mz Nh
Nk Nt Nx Og Oh Om Pc Qb) Aj(BA bF bR cT dF Jq Ke Ms Ne Ni Nk Nw Ou Qg Uh) Mm(Hq Hu Hw Jq Jr Lj Mb Mr Nb Ne Nh Nj Ns Og Pb
Qe) Nx(Fr Hq Hr Hw It Jk Jo Jq Lh Mr Mt Nh Ns Oe On Qe) Mr(Hq Hr Hw Hx Ii Il Jk Mb Mk Mz Nh Nj Og Qb) Jp(Hq Hw Ii Ik Io It Jq Mb
Mt My Nq Ns Og Qb) Ct(Bc dF Hu Jq Kq Lv Mq Ms Ni Nk Nw Om Uh) Ne(bA Hq Ik Iq Jr Li Lj Nb Nc Nl Nq Nt Pb) Jg(Hq Hu Ii Io It Lj Mw
Nk Nq Ns Oe Og) Om(Hr Hw It Jo Lj Md Nh Nj Nq Ns Of Qb) Pb(Hw Lj Lw Mb Mz Nb Nj Oh Pc Pd Po Qe) Li(Hr Hw Ii It Mt My Nj Nq Ns
Og Qb) Nt(Ii Jk Jq Nc Nq Ns Oe Og Oi Qb) Hq(Hu Jr Lj Mz Nj Oh Pe Po Qe) Ik(Hr Ii It Jk Lj Ns Og Oh Qe) On(Hx Io It Jo Mv Nb Nv Of)
Nk(Hu Hw Nb Og Pc Qe Uk) Qb(Fr Lj Mz Nh Nj Oh Qe) Jk(bA Hu Mu Nb Oh Pc Th) Ii(bA Hu Ke Po Uh Vt) Jq(Hw Iq Jo Lh Mb Nj) Og(Hu
Lw Mz Nb Nh Nj) Uk(Ib Id Ke Ou Vt Th) Pe(Hr Hw Hx Il Mb Mk) Ns(Hu Lh Lw Nb Pc) It(Jn Jt Nh Qe Wm) Th(Mh Ni Nl Oz) Fr(Hu Lj Mw
Oe) Lw(Hr Hw Mb) Mz(Hw Nh Nj) Nc(Lj Nj Nl) Qe(Hr Il Mb) My(Pc Wm) Oe(Hu Oh) ChbA TiKg MwLh NbNj NhNl HwLj JnJs UrVt
VqoE} Qe{Oy(bA Hu Ih Ik Jh Jp Jr Jt Lu Lw Me Mi Mm Mu Mz Nb Ne Nj Nk Nn Nt Nu Nx Oh Pc Pd Pg Po) Pb(Hu Ih Il Jg Jp Jr Lj Lu Lw
Mm Mu Mz Nb Ne Nj Nk Nl Nu Og Oh Pc Pd Po) Hq(Hu Ik Jg Jp Jr Lj Lu Lw Ma Me Mm Mr Mz Nh Nj Nt Nx Og Oh Pc Pe Po) Ih(Ik Il Jg Jp
Jr Li Lj Lw Lx Mc Mm Mr Mz Nb Nj Nt Nx Og Oh Om On) Ns(Fr Ik Jg Jp Jq Jr Li Lu Lw Lx Mm Mr Nb Nh Nt Nu Nx Om Pc Pe) Nk(Fr Ik Jp
Jr Lj Lu Lw Me Mr Mz Nb Nt Nu Nx Og Oh Om On Pc Pe) Me(Hr Il Jg Jp Jq Lh Lj Lw Mm Mr Mz Nj Nt Nx Og Oh Om Pc) Lu(Jg Jp Jr Li Lj
Lw Lx Mm Mr Mz Nj Nx Og Oh Om On) Lx(Hr Ii Il Jk Mh Mr My Nj Nx Oe Og Pa Pg Po Tj) Mr(Hr Hw Hx Ii Ik Il Jp Mk Mm My Nj Nx Og
Pa) Og(Hu Jg Jp Li Lw Mm Mu Mz Nb Nj Nt Pc) Om(Hr Hu Hw Il Jo Lj Md Mw Nj Nq Oe Of) Ik(Ii Jk Jp Lj Lw Mm Mz Ne Oe Oi) Fr(Ii Jr Lj
Mw Ne Nl Nt Nx Oe) Jp(Il Io Jk Lj Lw My Nq Nt Oe) Jg(Ii Io Jk Lj Mw Nq Oe Oi) Li(Ii Il Io Jk Nj Nq Nt Nx) Mm(Jr Lj Mz Nb Nh Nj Nl)
On(Hw Io Md Mu Mv Nx Of) Aj(BA cT dF Jq Ni) Nt(Ii Io Jk Ne Oe Oi) Nb(Lh Lw Mz Nj Nl Oe) Ne(bA Il Nc Nj Nl) Nx(Jk Jo Lh Nj Oe)
Ct(Ba cT Jq Ni) Mz(Jr Nj Nl Oe) Uk(Id Jq Ke Vt) Pe(Hr Il Mk Pa) Lh(Mb Md Nq) bA(Ch Ii Wm) Lw(Hr Lj) Nc(Nj Nl) WmMs MuJk HwJq
IiKe IlQd JnJs OeOh UrVt} On{Md(aA Ik Jk Jn Jr Lh Lu Lx Mb Mh Mk Mr Mt Mw Mz Ne Nj Nl Nq Oe Of Pe Qd) Jq(aA Hq Hr Hu Hw Ik Jk
Jo Jr Li Lu Lx Mb Mh Mt Ne Nj Nl Nq Of Og Om Qd) Hu(aA Hq Hw Ii Ik Io Lh Li Lu Lx Mb Mf Mk Mt Nb Ne Nj Nl Ns Oe Og) Hq(aA Ik Jr
Lh Lu Mb Mf Mr Mt Ne Nj Nl Nq Oe Og Oh Pe Po Qd) Jk(Fr Io Jm Jp Jr Lu Mh Mk Mr Mu Nb Ne Nl Nt Nx Pb Pe Po) Of(Ii Ik Io Jr Li Lu Lx
Mb Mh Mr Mt Nb Ne Nl Nq Nt Pb Pe) Qd(aA Hw Io Jo Jt Lu Lx Mh Mk Mt Nj Nk Ns Nv Nx Oe) Ii(Jm Jn Lw Mb Mf Mr Mz Ne Nl Nq Nt Og
Oh Pe) Lx(Lu Mt Mu Mv Mz Nj Nq Nv Nx Oe Og Pa Pg) Mk(Ik Lh Li Mr Nj Nl Ns Nt Nx Oh Pe Po Wm) Mw(aA Fr Jp Jr Lh Mb Mz Nb Nt
Og Om Wm) Lh(Hr Hw Hx Jo Mb Nb Ne Nl Nq Nv Pg) Mt(Jr Li Mu Mv Mz Nj Nq Nv Oe Oh) Og(aA Io Jr Li Lu Mh Ne Nl Nq Ns) Oe(Ik Jr
Li Mh Ne Nj Nl Nt Oh) Ns(Ik Lu Mh Nb Ne Nl Nq Nu) Pb(Hw Mf Nb Nc Nt Oh Pd Po) Lu(Jr Li Lw Mz Nl Nq Oh) Mb(aA Hv Hw Jn Mc Mr
Pe) Nj(Jo Jr Li Mh Mz Nb) Nq(Jr Mh Nb Nt Oh) Jo(Ik Li Mf Nt Nx) Hw(Jr Li Mh Mr) Ct(Is Mq Ms) Ne(Nc Nk Nl) Ik(aA Mg Oi) Li(Io Mv Nk)
Nl(Nb Nc) Jr(Mh Nk) aA(Mz Nx) AjMs WmNv NtIo MrHx JnJs NwqD} Ms{Jp(Fr Hu Ij Io Jg Jn Js Jt Lu Lw Mf Mh Mm Mp Mu Mw Mx Mz
Nb Ne Nl Nn Ns Nu Pb Pc Pe Qb) Fr(Ij Ik Jg Jn Js Jt Li Lw Me Mp Mr Mw Mx Nb Ne Ni Nj Nl Nu Oy Pb Pe Po Qb) Qd(Hu Jn Jr Lj Lw Me
Mm Mp Mr Mu Mw Nb Ne Nj Nk Nl Nn Nq Nt Pb Pc Pe Po) Li(Hq Ik Jg Jn Jr Jt Lu Lw Me Mm Mp Mr Mu Mw Nb Nj Nk Oh Oy Pc Pe)
aA(Ik Il Ip Jn Jr Js Jt Mm Mn Mp Mw Nd Nh Nn No Nr Nu Nv Ny Pz Qb) Oh(Hu Ij Ik Jn Jr Jt Lw Me Mm Mp Mr Mu Mw Nb Nd Nk Nv Pb Pe
Po) Jq(Ij Ik Lj Mm Mp Mr Mu Mw Mz Nb Nd Ni Nu Nx Pc Pe Po) Nw(Aj bA bR dE dM dN Dp Jy oE Or Ou Uk Ul Un Ur Vt Tj) Nx(Jg Jr Jt Lj
Mp Mr Mu Mw Mz Nh Ni Nt Pe Po) Lv(Ij Jn Jr Js Jt Mm Mr Mu Mw Nh No Nt Nv) Is(bA bR bS cA Ch dE dJ dM dN Uk Ur Vt) Po(Fp Hq Jg
Mq Mr Mz Nd Nh Ni Nt Pb) Nh(Jg Jt Lj Mp Mq Mr Mw Mz No Nv) Om(Jn Me Mw Nb Ne No Ns Pe Qb Wm) Mz(Ik Jg Jr Lj Mp Mr Mu Nt)
Jg(Jr Lj Mr Nd Ni Nt Pe) Wm(Lw Lx Mt No Pe Un) Mq(Jn Js Mp Mw Nt Nv) Ke(Aj oE Oz Pb) Lj(Mm Mu Ni Nt) Fp(Ij No Nq) Nt(Mp Mw)
Nd(Mp Nv) Ur(Un Vt) AjOk CtKq NiNv VtoE} Lh{Ni(Fr Hq Hr Hx Ii Ik Jg Jn Jo Jp Jq Jr Lv Lw Md Mm Mq Mw My Mz Nb Nc Ne Nl Nt Nx
Of Oh Po) My(Hr Hu Ii Ik Jn Jq Jr Lu Lw Mb Me Mm Mq Mu Mv Mz Nb Nc Nj Nl Nq Nt Nx Oh Pc Po Qd) Jp(Hq Hr Hx Ii Ik Jk Jo Jq Jr Lu
Mb Md Me Mf Mq Mw Nb Ne Nl Nq Ns Nx Of Og Oh) Ii(Fr Hr Hu Ik Jg Jn Jq Jr Lv Lw Mm Mq Mz Nb Ne Nj Nl Nt Nx Oh Om Po) Hr(aA
Hx Ik Jq Jr Li Lv Lw Me Mm Mq Mz Ne Nj Nl Nt Nx Of Oh Po) Li(Hw Hx Il Jk Jo Jq Lu Md Me Mq Mw Nj Nk Nl Nq Ns Of Og Qd) Mq(Hq
Hx Jo Jq Jr Lv Mm Mz Nj Nl Ns Nt Nx Of Og Oh Qd) Hx(Ik Jq Jr Lv Lx Mm Mz Nb Nc Ne Nj Nl Nt Nx Oh) Nj(Fr Hq Jq Jr Mm Mz Nb Nk
Nx Of Oh Qd) Lx(Jk Jo Jq Lj Md Me Nq Ns Og Pa Qd) Pb(Hu Hw Il Jq Lw Mc Mz Nb Nc Pc Pe) Lv(Hq Il Jn Jo Jq Jr Mr Nb Nx Of) Qd(Hq
Hw Il Jk Jo Me Nk Nq Nx Og) Of(aA Fr Ik Jg Mm Nt Nx Oh Om) Ik(Jo Jq Mm Mz Og Oh) Lj(Hw Jg Jq Me Nt Om) Oh(Hq Il Mb Me Nl)
Mm(Jr Mb Me Nl) Mw(Fr Jg Om Wm) aA(Md Mk Nb) Mz(Ne Nl) Nk(Ne Nl) Jg(Jk Og) Jo(Nt Nx) Jq(Md Om) BaCt WmNv PoHq FiIl FrJk
MrNd IjOy NxOg} aA{Lw(Fr Ik Il Ip Jg Jn Jp Jq Jr Mb Me Mf Mh Mm Mn Mw Mz Ne Ni Nj Nl Nr Ns Nt Om Pb Pz) Mz(Fr Ik Jg Jm Jp Jq Jr
Mb Me Mf Mh Mm Ne Ni Nl Nr Nt Nu Nx Oh Om Pb Pc Pd) Nd(Ij Ip Jg Jm Jn Jr Js Jt Mr Ne Nn No Nr Nt Nv Nx Ny Pb Pc Pd Pe Pz Qb Qc)
Jq(Fr Ik Jg Jm Jp Jr Mb Md Me Mf Mh Mm Ni Nj Nr Ns Nt Nu Nx Oh Pb Pc Qd) Mm(Ik Il Jn Jp Mb Me Mf Mh Mr Nb Nh Ni Nj Nr Ns Nt Nx

Figure 1 Continued

Oh Om Pb) Nh(Fr Ip Jg Jn Jp Jr Me Mw Nc Ni Nk Nl No Ns Nt Nx Om Pb Pc) Fr(Ik Jr Me Mf My Ni Nj Nl Nq Ns Nt Nx Oh Oy Pb) Jr(Ik Il Jg
Jp Me Ni Nj Ns Nt Nx Oh Om Pb Qd) Nx(Jm Jp Me Mf Mh Ni Nj Ns Nt Oh Om Pb Pc) Oh(Ik Jg Jp Me Mf Nb Nj Ns Nt Om Pb Qd) Om(Hu
Md Me Mf Mh My Ni Nj Ns Nt Qd) Jp(Ik Me Mf Mh Ni Nj Ns Nt Pb) Mq(Il Jg Jm Jn Mf Mn Ns Pc) Pb(Ij Ik Il Jg Nr Nt Pd) Ni(Il Jg Mn Nj Nt)
Nk(Nc Nj Nl Qd) Ns(Ik Jg Nt) Me(Jg Jn Nt) Aj(Ad Is) Mn(Ik Nj) Il(Mf Nj) Ctls NtPc MyJg IkJn} Li{Pb(Fr Hw Ik Il Io Jo Jp Jr Jt Lu Lw Lx
Mm Mr Mu Mz Nb Ne Nj Nk Nl Nt Nx Oh Om Pe Po Qd) vS(aH al bB Ch CO cV DB DE dJ fP gP Hq Hu Ma My Nq nW oK oN Qy rB Ri sC
Ur Uu) Oy(Fp Ik Jg Jh Jp Jq Jy Lu Lw Me Mi Mr Mu Mz Nb Nj Nt Nx Pc Pd Pe Po Qd Wm) Mc(Fp Fr Hq Jp Jq Lu Lw Lx Mm Mq Mz Nj Nk
Ns Nt Nx Oh Pc Qd xA) Jq(Hq Hr Ii Ik Lu Lx Mb Mm Ne Nj Nk Nl Nq Ns Nt Nx Og Qd) Lu(Fp Jp Lw Lx Mm Mt Mz Nj Ns Nt Nx Qd) Qd(Hq
Il Io Mq Nh Nj Nk Nq Ns Nx Og) rS(dB dJ Hq jO jT kR nW oN rU uY) Jp(Hq Ik Io Mq My Nh Nj Nq Ns) Mt(Hq Lw Mr My Nh Nj Nk Nq)
Nt(Mq Nk Nq Ns Oe Og Oi) gP(tR uU uV uY vC vQ) jT(uX vA vT wB wQ zA) xA(dB dJ Mz Nm nW rB) Mq(Lw Mz Nk Nx Og) Nh(Hq Lw
Mm Mr Ns) Nj(Fr Hq Lx Mz Nk) uM(dB jO Mz Nw Ri) Ns(Fp Nx Om) My(Fr Jh Om) Nk(Lx Nc Ne) Hq(Fr Lx vT) Ip(sC wQ zA) Nw(fN qC
uU) dB(rU sC) wP(eF jO) uZ(oE Ur) AdAj WmLv FpLw NqrU MksC MzqC dEuV} Lj{Ni(Hu Ik Jh Jn Jr Jt Lu Lw Mi Mp Mr Mu Mw Mz Nc
Nd Ne Nn Nt Nv Oh Pb Pc Pe Po We) Nh(Jg Jh Jt Lu Lw Me Mm Mp Mr Mu Mw Mz Nb Nc Nl Nt Nx Oh Pb Pc Pe Qd) Nd(Jh Jt Lw Mi Mu
Mw Mz Nb Nk Nn Nq Nt Nv Nx Oh Pb Pc Pe Po) Jp(Fr Io Jq Jr Lu Lw Lx Me Mf Mm Mr Nk Ns Nt Nx Om Oy Pb) Fr(Hq Jr Lu Mm My Mz
Ne Nk Nl Nq Ns Nt Nx Om Pa Qd) Jq(bA Ik Jg Lu Lx Mm Mu Nj Nt Nx Pb qC Qd) Nk(Ik Jg Lx Mq Mu Nc Ne Nj Nl Nt Om Qd) Kc(eC gP Ha
Ii oE oN Oy Oz Pb qC Uk) Lx(Ik Lu Me Mh Mt Nj Nt Nx Pb Tj) Me(Jg Mm Mq Mu Nt Nx Om Pc Qd) qC(Id Kn Lw Mz No Ny rB Un Vt)
Jg(Io Lu Mr Nj Nx Oy Pb Qd) Om(Hq Hw Md Nj Ns Nt Og Pa) Mm(Hu Ik Lu Mr Nj Nt) Mq(Lu Mz Nj Oh Pc Qd) Pb(bA Ik Mr Mu Nt Nx)
Jy(bA bR bS cA cO) Kq(Aj Ch Ct Oy) Nx(Lu Mr Mt Nt) Ou(Ha Uk Ur) Aj(Ad Ba) Wm(bA Lv) No(eC oE) Lu(Nt Qd) Is(aN bR) qD(Lw Nw)
BaCt MtbR MyJh IkQd IlSf} Mt{Ns(Fr Jg Jp Jr Jt Lw Lx Me Mm Mr Mz Nd Nh Ni Nt Nx Oh Om Pb Pc Pe Po) Oy(Il Jh Jp Jq Jr Jt Lw Me Mi
Mm Mu Mv Mz Nb Nh Ni Nn Nt Nx Oh Pc Pd) Pb(Hv Hw Ik Ip Jg Jn Jo Jp Jr Jt Lw Mm Mz Nb Nd Nh Nj Nt Nx Pc Pd) Mr(Hq Hx Jp Jq Jr Lw
Lx Me Mk Mm My Mz Nh Nj Nk Nx Oh Qd) Nd(Jg Jn Jr Jt Lw Me Mi Mm Mp Mw Mz Na Nc No Om Pa Pc) Nh(Fr Jp Jr Jt Lw Me Mm Mz
Nc Ne Nk Nx Oh Om Pe Po Qd) Fr(Hq Hu Jk Jq Jr Me Mz Ni Nj Nq Nt Nx Og Oh) Pe(Hq Jp Jr Lx Mc Mk My Mz Nk Nx Oh Pa) Me(Jq Jr Lw
Mm Mz Ni Nt Nx Om Po) Jp(Io Jq Jr Lw My Nj Nq Nt Oh) Jr(Jq Lw Lx Mm Mq Mz Nk Oh) My(Jg Jh Jt Nb Om Po Qd) Nk(Nc Nj Nl Nt Oh
Po) Lx(Md Mh Nj Of Pg) Om(Hu Md Ni Of Og) Nt(Jq Mz Oe Oi) Po(Hq Ii Og) Ni(Lw Nx Pc) Nj(Mq Mz Oh) Wm(bR oN) Is(Aj bR) Qd(Io
Og) Jn(Js Mq) Jq(Ii Oh) LwOh MzNx NwoN VtoE} Lv{Mm(Fr Hu Ik Io Jn Jq Jr Lu Me Mz Nb Ni Ns Nt Nx Oy Pb Pe Po) Mr(Fr Ik Il Jg Jn Jq
Jr Mk Mp Mq Mw Mz Nb Ni Nt Nx Om Oy Po) Jg(Il Io Jq Jr Me Mq Mw Mz Nd Nh Ni Ns Nx Og Oh Pb Pe) Nx(Fr Jn Jq Jr Mw Mz Nb Nd Nh
Ni No Nt Oh Pb Pe Po) Om(Hq Hu Il Jo Jr Md Me Mq My Mz Nd Ni Ns Nt Of Og) Fr(Hq Hu Il Jk Jn Jq Jr Me Ne Ni Nj Nl Ns Nt) Mz(Ik Jn Jq
Jr Lu Nb Ne Nj Nl Nt Pb Pe Po) Nd(Ij Jn Jq Jr Js Jt Lw Mu No Nv Pb Pe Qb) Jq(Ik Jn Mw Nb Ni Nt Oh Pb Po Wm) Pb(Ik Jn Jr Mp Nb No Nt
Nv Pe) Po(Il Mq Nb Ni Nk Ns Nt Oy) Mq(Jn Jr Mw Nb Ns Nu Oy) Nh(Jn Jr Jt Nb Ni Nk Pe) Nt(Jn Mp Mw Ni Oh Oy) Oh(Hq Il Lu Ns Oy)
Ni(Jn Mp Mw No) Nb(Jn Mp Mw) Ct(Ba Is) Nk(Nc Nl) Jn(Me Pe) Oy(Nv Pe) AdAj MwJr MyJh IsaN} Is{Aj(aI bA bB Bc bV cM cQ cV dD
Dg Gp Hu Id Ih Il Jg Jp Jq jV Ko Kq Mq Nb Ne Nk Nw Ou Oy Qg Uh Uk Ul Ur) aN(bA bS bU bV cF cJ cV dJ Hw Ii Jk Jo Lx Mq Nb Ni Nl No
Nw Oi Oy Pb Uk Wm) Ct(bV Cu cV dN Fy Gp Id Jp jV Jy Ke Ko Nj Ou Qg Qm Sr Uk Ul Ur Us) Uk(bA Ch dJ dM Id Ii Il jF jV Kc Lw Mk My
Nk Ou Oy Pb Qg Ul Vt) Oy(Ad Ar As Aw bR bV cT dF dJ dM dN Jy Ke Kq Ou Tr Uh Us Vt) Ch(aC bA bR cV dF dM Kq Nb oH Ou Qg Ur)
Ne(aC aD bA bR bS bV bW cA cV dJ dM dN) Ii(aD Ar bA bR bV cV dF dJ dM dN Ke Vt) Wm(bA bR cV dM jV Mw My Nb Nv qX) jV(Jp Nc
Nh Nk Ou Qg Rb) Jk(bA dM iB iC jK jU) Jo(bA bR cV dF dM dN) Qg(jD jK jO jU) bR(dM Ni Nw) TjLx LwjQ MzjK IhdJ JvjO UrVt PbbA}
Lx{Pb(Hq Hu Hv Hw Jg Jn Jo Jp Jr Jt Lu Lw Mb Mu Mz Nb Nc Nj Nl Nt Nx Oh Om Pc Pd Pg Qd Tj) Oy(bA dE Jm Jn Jo Jr Ke Kq Lw Mi Mm
Ne Nk Nl Nu Ou Pc Tr Vt) Nj(Fr Hq Jn Jp Jq Jr Jt Lu Me Mr Mz Nb Nk Oh Om Pe Qd Tj) Hq(Fr Ik Jg Jp Jq Me Mr Mz Nt Nx Oh Om Pe Qd
vS) Mr(Hx Ii Ik Jq Lu Me Mk My Mz Nk Nx Pa Qd) Me(Fr Jg Jp Jq Lw Mm Mz Nt Nx Oh Pe) Tj(Il Mq Ne Ni Nw Or Qm Ur Vt) Jq(Fr Ik Lu
Mb Ns Nt Nx Pa Qd) Pe(Ik Jp Lu Mk Mz Nk Ns Nx Pa) Fr(Ik Jk Jr My Nl Nq Ns) Nd(Md Mi Ml Mu Nb Nh Nx) Qd(Io Lu Nk Nq Ns Pa Pg)
My(Jh Jp Mu Nx Om Wm) Nk(Jr Nc Ne Nt oN) Ik(Jn Jp Mz Ns Og) Lu(Jp Lw Mz Nx) Pg(Nh Ni Nt Nx) oN(Ne No Rg Wm) Ns(Jp Nt Om)
Ct(Ba Kq) EdFi NtOe MwJg MzNx JnJs} Mq{Nh(Jg Jn Jr Jt Lw Mm Mp Mr Mw Mz Nb Ne Ni Nk No Ns Nt Nx Og Om Pb Pc Pe Po) Jq(Hr Ik
Jg Jr Lu Md Mm Mw Mz Nb Ne Ni Nj Nl Ns Nt Nu Nx Oh Pb Pc Po) Fr(Hq Hu Jk Jn Jp Jr Me Mw Mz Nc Ne Ni Nl Nq Nt Nx Of Og Oh)
Oh(Hw Jg Jp Lu Mc Mr Mz Nb Ni Nj Ns Nt Nx Og Om Oy Qd) Jp(Ik Jr Lu Me Mf My Mz Nl Nq Nt Nx Og Oy Qd) Nd(Jg Jt Mm Mp Mr Mw
Mz No Nt Om Pe Po) Qd(Aj Hq Hr Hw It Lu Nj Nk Nt Nx Og Pc) Nt(Jn Mz Ni Ns Nx Og Oy Pb Pc) Pb(Jg Mr Mz Nx Pe Po) Ct(Ad Ba Cu Kq
Nw) Ni(Jg Nj Nx Po) Om(Md My Ns Og) Po(Hq Oy) Ns(Jg Nx) Mz(Nj Nx) Nk(Nc Nl) JgOg tUnW} Nw{qC(aG Ao aW Ax Bg bL Bo bQ cB
cL CO Cs dJ DK eD fN Hc Hq Ib iH Iz Jd Je jF Jn jP Kk Kz Mc My Mz Ne Nk Nq Nv nW Oa Ou Ow Qt RB Ua Uh Ur Vt Vv tF) qD(Aj Ao aZ
Bg bL cB CO DB dE Gl Hc Hq Hu Iz JD Je jF Jk Jn Mh My Mz Nq nW oE Ow Oy qA Qt Vv Wm) fN(dE DK hO jD Kp Mh Nk nW Ou)
Wm(bR cV dM gP nW oE oH oN Tj) oE(CH Ne No Oz Vq Vt) Oy(Ad Jy Kq Sr Tr) bA(Hq Jk Oz Pa Pb) nW(jE qA rS vH wD) Tj(Il Mr No Po)
oN(dF Jy No Rh) Il(Aj Ct Uk) hO(dB dE Nv) dM(Ne Oz) qA(bP Qc) qZ(DB) AdAj JyNv RhgP} No{oN(aI Aj Bc bJ cK Ct dA dD DE eC Hb Ii
Jk Jy Ke Ml Mw Mz Nc Ni Nj Nl Nr Oz Uh Ur Vp Vt Tj) oE(Aj dA dH gP Ha Hc hG Hq Ii Iz Ke Nv Ow Pb Rg Rh Tt Tj Th) eC(Aj Ch Ct DE
Gl Ha Jk Ne Nj Nk Nv Oy Ss Vt Wm) nW(Ar Bc Ha Ne Nk Nl Nr Oy qX Rg Vt wQ yD Tj) qC(aW aZ Ch Db dE Hu Ib jF Me Nq Ou rB Wm)
qD(Ch cO DB dE Hq Hu Jk jO Nq Nv Ou rB) gP(Hb Hc Hq Ke Oa Qm Ri Tt Uh Ur Vt) Nd(Fp Jq Mp Mr Pe) Wm(bA Mw Nv Th) oH(Ar Ch
De Rg) Th(Aj Ni Oz) uM(Ow rB xA) Nh(Jq Ni) AdAj BaCt FpNr NiNj NkfN iHrB} Kc{oE(Aj AO aW Bc BG cH Co Cp Ct De Dk Ex Hc Ib Iz
My Ne Oa oN Ow Oz Rh To Ut Vq Vt) Wm(cI cV Dk dM eC gW Hx Ii JD Mk Mw Nb Nv Ny qC Qx Ut Vp Tj) oN(Aj Ao Ax Bc Bg Co Cp Cs
Dk Hc Ib Iz Mh Ne Oa Oz Rh Ut Vt) Il(Aj Ch Cp Ct Ii Iz Jk Uk) Oy(Dp Jy Mw Oa Tr Uk Vt) qC(aW aZ Ch Me qA Qy) Oz(Aj Ao Cp Ct Ib)
Ch(fN hP qD tF) Ii(Ax Dp Pb Vt) Oa(Aj gP Ha Uk) nW(jQ jR Vt wP) Hc(eC gP qD) Pb(Cp Ib Ou) eF(jE jU jV) fN(Aj Ou Ow) Ct(Ba Dp)
Uk(Ao Ib) fP(jD jU) gW(To Tt) DpKg OwqA UtpF hGjM} Qd{Nh(Jg Jp Lu Me Mm Mr Mz Nb Nc Nl Nx Og Oh Om Oy Pb Pc) Ni(Aj Jg Jq Jr
Lu Mm Mr Ne Nt Nx Om Pb Pc Po) Om(Hq Hw Ii Jo Lu Md Me My Nj Nq Ns Og Pb) Fr(Hq Jk Jq Jr Me Ne Nl Ns Nt Nx Og) Ik(Jp Jq Mm Mr
Mz Nk Og Oy Pb Pc) Jq(Jp Lu Md Nb Nj Nt Nx Pb Pc) Nd(Lw Mi Mw Nb Nk Og Pb Po) Wm(bA gP Lw My Nv oE oH) Me(Jg Jp Mm Nx Oh
Pb Pc) Pb(Jp Mr Nt Nx Pe Po) Aj(BA cT dF Ou) Nj(Jp Mr Mz Nb Nk) Nx(Lu Mr Og Oy) Ct(BA cT) Nk(Nc Ne Nl) Jg(Il My Og) ChbA PoHq
LuJp MrIl MyJh} Fr{Oy(Hu Hw Ir Jm Jn Jo Jp Js Jt Lw Mf Ml Mx Mz Nb Nc Ne Ni Nu Nv Pb Pd Qb) Pb(Il Jp Jq Jr Jt Mb Me Mr Mx My Mz
Nc Ne Ni Nl Nu Nx Oh Om Pc Po) My(Ik Jh Jp Jq Jr Me Ni Nj Nl Nt Nx Om Wm) Jq(Ik Jr Mb Md Mz Ne Ni Nj Nl Nt Nx Oh) Nh(Hu Jk Jp Lw
Mr Nk Ns Nx Og Oh) Ni(Ik Jp Jr Nc Ne Nl Nt Nx Oh) Me(Jp Jr Mz Nj Nl Nt Nx Oh) Nj(Jk Jp Jr Mz Nk Oh) Nt(Jk Jr Nq Ns) Jr(Hq Mz Ns)
Nk(Nc Nl) MzNl IkJk} Jp{Ni(Jq Jr Lu Lw Mb Mc Mf Mh Mm Mr Mx Ne Ns Nt Nx Oh Om Pb Pc Pe Po) Nj(Io Jq Jr Lu Me Mh Mr Mz Nb Nc
Nk Ns Oh Pb Pe Po) Nh(Io Jr Lu Lw Mr Mz Nc Ns Nx Oh Oy Pb Pe Po) Me(Ik Jr Lw Mm Nt Nx Oh Pb Po) Oy(Ik Jg Mr Nt Om Pe Po Wm)
Ik(Jq Mr Ns Og Oh) Pb(Jq Mr Nt Pe Po) Wm(Lw Mw Nv) Jq(Mb Md Nt) Aj(Id Sr) Nk(Nd Nl) Ok(Hr Mb) CtbA PoHq NsNt MyJh} Fp{Oy(Il
Jo Jt Mi Mp Mw Nb Nn Nv Nx Oh Pd Pg Po Pz) Hq(Jn Jt Mi Mp Mu Mw Nn Nv Pc Pe Po) Nd(Jn Lw Mi Mu Mw Nn Nv Pc Po) Pc(Jn Jt Me Ns

Figure 1 Continued

Nt Nx Oh Pe) Il(Fi Rt Sf Va Wc Yk) Nk(Mp Mw Nn Pa Po) Hr(Hv Hw Jo Lw Pe) Jn(Ih Js Lu Me Nx) Oh(Jt Nb Nt Nx Pe) Lu(Lw Mp Mw)
My(Mv Nb Nq) Ns(Nn Nv) Mk(Mp Pe) Nx(Jt Og) NtOe LwMu MpPd NeNl HuJg PzOg JrJs} Nh{Jq(Jg Jr Md Mm Mp Mr Mw Mz Nb Ne Ni
Nk Nt Nx Og Oh Pb Pc Pe Po) Om(Jr Md Me Mr My Mz Ne Ni Ns Og Oh Pb) Mr(Jg Mm Mz Nc Ni Nk Nx Oh Pb Po) Oh(Me Mz Nb Ne Ni
Nk Pb Pe) Po(Hq Mz Ne Ni Nk Oy Pb) Mm(Jr Me Mz Ne Ni) Mz(Jr Ne Ni Pe) Ne(Jn Jr Pe) Ni(Jg Mp Mw) Nk(Jr Pe) Jg(My Oy) VtoE PbPe}
Vt{oE(Aj aW aY bG bN cM Ct dD dJ Gp Jo Jy Mm Nb Nk nW Ow Oz Qg Ql Rh To Uk Ur Vq) qZ(aW bL Db dE dJ Gl hP iH Kr Kz qC uM)
bA(Ii Ne Oy Oz Pb Ur Wm) qC(DB dE iH Mz rB) Ur(Ed Il Ou Oz Wm) nW(jK Ne Rh wP Wm) Oy(Il Kq Mw Nq) Aj(Ad Ba Kq) MeqD NeeC
IlUk jOvS} Kq{Aj(Ad Ao bJ bR Ch cf Co Dk Dp Fb Gp Ib Id Iz JD Je jF Md Mk Mw Nb Nv oN Ou Oz Pg Ut Tj) Ct(bA Id Jm Md Mw Oa Oh
Ou Ow Oy Oz Pb Wm) Ch(bA bN Gp Il oE oH oN Ou Oy Oz Ur Us) Wm(cI My Nv oN) Oy(cI Dp Il) Iz(Il Uk) OufN} Nd{Mr(Jg Jn Jq Jr Lw
Mp Mw Mz Nv Om Pb Po Qb) Oh(Jg Jq Jt Lw Mm Mw Mz Nb Ni Om Pb Pc Po) Po(Jq Jt Mm Mp Mz Ni Om Pb Pe) Pe(Jg Jq Mp Mw Mz Nv
Om Pb) Om(Mm Mp Mz Og Oy Pb) Jq(Jg Mm Mp Mw Mz) Mm(Ij Jr Mz) Jg(My Mz Oy) MpJt} Il{Dr(Ii Kj Me Nc Ni Pa Pb Rt Tz Wc Tl Wm)
Kg(Em HI Uw Uz Vi Wg Yi Xa) Ni(Fi Rt Vb Wf Yk Tl Xa) Sf(Iv Ld Oa Or Oz Qb) Fi(Ed Fa Ld Oa Or) Xa(Ap Dg Jo Jt Oy) Iv(Rt Wc Yk Tl)
Or(Rt Wc Zx Tl) Oy(Jg Om) ApPs BaCt MzqC YkOa} Ct{Ba(aC Ad Aj An Ax bA Bc Bn Cp Cq Cs Cu Cw dF dJ Fy Hv Hw Id Ij Iv Jn Jq Jr Kd
Kn Mr Oh Oz Pe Qb Tv Ul Un Us) bA(Bc bF Cu Dc dJ Pz Wm) cT(Bc Cu) MzqC} Ni{Oh(Ik Jg Jq Mm Mr Nc Nj Nl Nt Nx Om Pb Po) Po(Hq
Jg Jq Mm Nc Nj Nl Nt Nx Oy) Jg(Aj My Nc Nj Oy Pb) Om(Md My Nj Oy Pb) Nj(Mm Mp Mw) St(Vb Wc Ye) MmJr QbWe VqoE}
Wm{bA(Hb Jq Lw Oa Oy Oz Pb Pj St Un Ur) oE(Jq Kd Kn Lw Uh Vq) Jq(dM My Nv Ny) Uh(dM hB oH oN) Lw(cV dM oH) Mr(My Oy)
Kn(oH qC) Ou(qZ Ti) TjPo MyOk MzqC OyPe qZuM} Oy{Om(Ik Jg Jr Lu Md Me Mh Mi Mu Mz Nb Ne Nj Nl Nt Oh Pb Pc) Jg(Jq Jr Mc Mz
Nt Nx Oh Qb) Nq(Dr Kn Tr Tv Un) Pe(bA Ha) AdAj PoMr MzqC} Aj{Ad(Bc bZ cE cS dG dJ dM Dp Ef Fy Gp Id Jy Mw Nj Oa Oh Ou Oz Pe
Qm Uh Uk Ul Ur) BadJ MzqC IdUh VqoE} Vq{oE(aE As aZ bG bU cH cJ cR dJ Ip Jr Ki Ks Ld Mk MI Mm NI nW Or Oz Pb Qm Qv Qz Ri
Uu) EdRx} qC{Mz(aW aZ Ch Db Hq Iz Me Of Ou Ow Ua Uk) Kn(DB Me) Ny(Ch Ou Ow) Id(Ou Ow) ChUc MeUn KoOu} Pb{Mr(Ik Jg Nx
Oh Om Po) Po(Jq Nt Om Pe) Om(Nt Oh Pe) Ik(Jq Pe) Dbnl NtJq NxPe} nW{wD(dE hB Kp Pj qD qZ Ri uX tF) uX(dJ Mz uM) wP(Ax Cs)
IdvS} Ou{qZ(Dg dJ Ko Mf Mm Nm Ss Uf) Ko(fN ql rS wP) fN(Lw Ny)} Po{eP(Al Dd Hv) Nk(Nc NI) MyJg} vS{Mz(rA Rb Sr) ChUc LuId
UaKo} bA{aC(Ad Ar Bc) bRfR} qZ{Hc(DB) KoOw eDxA} Ok{MI(Hx Ny) HrQb} My{Jg(Jq Mr)} Ld{DueC WekR} Un{qD(Ch Hc)}
BaSsdX DpIjWc DrNqKg EdFiNr NtMdJq MzUbpS IbTruI IdOwfN Constrained panels with 2 analytes, where 1.0E-8 >= 'model p-value' > 0. Contains 288 panels of 193,455 total panels evaluated. : Et(aA Aj Fp
Hq Ik Im In Io Is Ji Jj Jl Jo Jq Jr Lh Li Lj Lu Lv Lx Me Mm Mq Mr Ms Mt My Nb Nc Nd Ne Ng Nh Ni Nj Nl Ns Nt Nw Oh Oy Pb Pf Qa Qd Qe
Wm) Is(aA Fp Fr Hq Hw Ih Ii Il Im In Io Ji Jj Jk Jl Jp Lh Li Lj Lu Lv Lx Me Mm Mq Ms Mt Mz Nb Nd Ng Nh Ni Nj Nk Ns Nt Nw Og Ok On
Oy Pb Pf Qe) Ok(aA Fp Fr Ii In Jo Jq Jr Lh Li Lj Lu Lv Lx Me Mh Mq Ms Mt Nb Nd Ng Nh Ni Nj Ns Nw Oh Oy Pb Pf Qa Qd Qe)
Nw(aA Fp Ii Ik Im In Jj Jl Jr Lj Lu Lv Md Me Mq Ms Mt Mw My Nd Ng Nh Ni Nj Nl Ns Oy Pa Pb Pf Qa Qe) Ji(aA Fp Hq Ii Im In Io Jj Jl Jo Lj
Lu Lv Md Mq Ms My Nd Ng Nh Ni Ns Nx Og Oy Pb Pf) Fp(aA Fr Im In Jg Jj Jl Jp Jq Lh Lv Lx Mm Mq Mt Nb Ni Om On Qa Qd Qe) Jj(Ik Im
Jl Lh Li Lv Lx Mt Nt Nx Oh On Po Qa Qd Qe) Lv(aA Im Jl Jp Li Lj Lx Mt On Qa Qd Qe) Nd(Fr Im Jl Jp Lh On Qa Qe) In(Im Jl Li Lx Mt On
Qa Qe) Ms(Jl Lh Lx Mt On Qa Qe) aA(Im Li Lj Lx Po Qa Qe) Ni(Im Li On Qa Qe) On(Lj My Ng Oy) Mt(Im Jl Qe) Ng(Jg Kq) Im(Jl Lh) LxJl
MqQa Constrained panels with 2 analytes, where 1.0E-7 >= 'model p-value' > 1.0E-8. Contains 273 panels of 193,455 total panels evaluated. : Qa(Fr
Hq Hw Ih Im Jg Jl Jp Jq Lh Li Lu Lw Lx Me Mm Mr Mt Mz Nb Ne Ng Nh Nj Nk Nt Nx Og Om On Oy Pb Pf Qb) Jl(aA Jp Jq Lh Li Lj Me Mq
Mz Ng Nh Ni Nj Nk Ns Nt Nx Og Oh Om On Oy Pb Pf Qd Qe) On(aA Hq Ii Im Jk Jq Jr Li Lx Me Mh Mq Mt Mw Nh Nj Nl Ns Oe Of Og Pb Pf
Qd Qe) Qe(Fr Im Jp Jq Lh Li Lx Me Mq Mr Ng Nh Nj Nk Nt Nx Og Om Pb Pf) Fp(Jn Jt Li Lw Mp Mr Ms Mu Mw Mz Nk Nt Nx Oh Pb Pc Pe
Pf) Mt(aA Jp Jq Jr Lh Li Lj Lx Me Mq Mr Nd Ng Ni Pb Pe Pf Qd) Im(Fr Jp Jq Li Lu Lx Me Mq Mr Ms Mz Ng Nh Nt Nx Pe Pf Qd) Lv(Fr Jg
Lh Mm Mq Mz Nh Nt Oh Om Pf Po) Lx(Jq Lh Me Mq Mr Nd Ng Nh Ni Oy Pb Qd) Ji(Aj bA bN cl Ct Dd dM Uk Ur Us) Jj(Fr Jg Jp Jq Lj Mq
Nh Nv Om Pf) Lh(aA In Li Lj Ng Nh Oy Pb Pf Qd) Et(Ap bA Ch cl Cs Ct Kg Oa Uk) aA(Fr Mq Nh Nt Nx Oh Om Pf Qd) In(Lj Mq Nt Om Po
Qd Un Vt) Fr(Lj Mq Ng Nh Oy Qd) Li(Jq Me Mq Ms Nd Nh) Qd(Mq Ms Nd Nh Ni) Aj(Ad Is Kq) Mq(Jp Lj Pf) Om(Lj Ms Ng) Ct(Is Pf) oE(No
Vt) NgKe NhJp IsaN NwqC Constrained panels with 2 analytes, where 1.0E-6 >= 'model p-value' > 1.0E-7. Contains 445 panels of 193,455 total panels evaluated. : Lh(Fr
Hq Hr Hx Ii Ik Il Jg Jn Jp Jq Jr Lw Mb Md Me Mk Mm Mq Mw My Mz Nb Nc Ne Ni Nj Nl Nt Nx Of Og Oh On Po) Pf(Aj bA bL bR bS cA Ch
CO dM Dr In Jp Jq Ke Lx Mz Nd Nh Ni Nt Om Oy Pb Qd Uk Un Ur Vt Tj) Lv(Hu Ij Ik In Jn Jq Jr Js Jt Lw Mp Mr Ms Mu Mw Nb Nd Ni Nl
No Nr Nu Nv Nx Pb Pe Qb) Qd(Aj Ik Jg Jp Jq Jr Li Lj Lu Me Mm Mr Mz Nb Ne Ng Nj Nl Nt Nx Og Oh Om Pb Pc Pe Po) Li(Fr Hq Ik Jp Jr Lu
Lw Lx Mm Mr Mz Nb Ne Ng Nj Nk Nl Ns Nt Nx Oh Om Oy Pb rS vS) Lx(Fr Hq Ik Jg Jn Jp Jr Jt Lj Lu Lw Mz Ne Nj Nl Ns Nt Nx Oh Om Pe
Tj) Et(aC AO Ax bV Co Dg dM Ed Id Iz Kd Ke Kj Or Ou Ur Us Uu Vt) Im(Hq Hw Ik Il Jn Jr Lj Lw Mm Nb Ne Nj Nl Ns Nu Og Oh Om Pb)
Qe(Aj bA Hq Ih Ik Il Jg Jr Lj Lu Lw Mm Mz Nb Nl Ns Oy Pe Qa) Jj(aA Cu Ij Jm Jn Jr Js Jt Ke Kq Mw Mz Nr Oa Pz Qb Un Vt Wm) aA(Ij Ik Il
In Jg Jn Jp Jq Jr Lw Mf Mm Ms Mz Nd Ni Nj Nr) Fr(Ik In Jl Jq Jr Me Ms Mt Mz Ni Nj Nl Nt Nx Oh Pb) Mt(Jn Jt Lw Mm Mz Nh Nj Ns Nt Nx
Oh Om Oy Po) Jl(Hu Hw Ik Jg Jr Lu Lw Mb Mf Mk Mm Mw Nb Po) Ke(Aj Cp Ct Ib In Lj Ms Oa oE oN Oy Oz Pb Uk) Jp(Ik In Jq Jr Lj Me Mr
Ms Ng Ni Nj Nt Po) Nh(In Jg Jq Lj Mq Mr Mz Oh Om Pe Po) In(Fy Id Ik Jg Jq Kq Mr Nx Oa Oh) Ji(Dp eC Fy Gp jO IN Oa oE oN qC) Lj(Ik Jg
Jq Mm Mu Nd Ni Nt Nx Ou) Mq(Jg Jq Mz Nd Nt Nx Oh Om Po) On(Hu Hw Ik Lu Mb Ne Nq Nt) Is(aC bR Ch dM jV Uk Ur) Ms(Jg Jq Nt Oh
Po) Nd(Mr Oh Om Pe Po) Ct(BA Kq Qa) No(eC oN qC qD) Ni(Jg Oh Om Po) Ng(Ad Ba Uf) Qa(Aj bA Uk) Nw(hO oE qD) Oy(Jg Kq Om)
Wm(bA Jq) Mz(jK qC) Pb(Om Po) qZ(dB Ou) ChKq NtJq UrVt VqoE aCbA Constrained panels with 2 analytes, where 1.0E-5 >= 'model p-value' > 1.0E-6. Contains 780 panels of 193,455 total panels evaluated. : Pf(aC aD
AN bV cF cK cL Cv dE dH dJ Dp Ed Fr Ha Hq Id Ik Iz Jg Jn Jr Jt Jy Kd Kg Kj Kk Kn Ko Kq Lj Lu Lw Me Mm Mr Ms Mu Mw Nb Ne Ng Nj
Nl Nx Oa oE Oh oN Ou Pa Pe Pj Po Rg Sr Ua Uh Ul Us Wb Wc) Jj(Ad Ar Ax BA Bc Cs Dc Dp Fa Fb Fy Hu Id Ii Il Ip Ir Jk Jo Kn Ko Kp Mg
Mj Mm Mp Mr Mu Mx Nb Nd Ne Ni Nj Nl Nm Nn No Nu Ny oE Ou Pd Pe Pg Pj Qc Qh Qm Rm Sr St Tr Uc Uf Uh) Lj(bA bF bR bV bW cE
dF dM dN Hu Jh Jo Jr Jt Jy Kq Lu Lw Me Mp Mr Ms Mw Mz Nb Ne Nj Nk Nl Nv oE Oh Pb Pc Pe Po qC Uf Uh Un Vt We) Ke(Ao Ax Ch cI
Co Dk Dp eC Ed fN Hc hL Hq Ii Il Im Is Iz jD Jk jM Kg Kj Lw Md My Nd Ne Nv Ou QA qC Qe qX Ur Us Ut Vt Wm) Mq(Hu Ik Ir Jn Jr Js Jt
Lu Lw Me Mm Mp Mr Ms Mu Mw Nb Nc Ne Ng Ni Nj Nl Nn No Ns Nu Nv Pb Pc Pe Qb Vt) In(Ad Ar Ax Cs Cu dN Fa Ij Jn Jr Js Jt Kd Kn Ko
Mm Mu Mw Mz Nv Ou Pe Pj Qb Sr St Uf Uh Wm) aA(Hu Ip Ir Jm Js Jt Ma Me Mh Mn Mr Mu Mw Mx Nb Ne Nl No Ns Nu Nv Ny Pb Pc Pd
Pe Pz Qb Qc) Jp(Aj Ct Fr Hw Io Jn Jt Lu Lw Mb Mf Mh Mm Mx Mz Nb Nc Ne Nl Ns Nu Nx Oh Om Oy Pb Pe Wm) Nw(aC aD Aj Ao bA bR

Figure 1 Continued bV Co Ct Dk dM dN Dp Ed Id Oa oN Or Ou Rh rS Uk Ul Ur Vt Tj) Om(Ct Fr Hu Jq Jr Lh Lu Md Me Mh Mr Mx My Mz Nb Ne Nj Nl Ns Nt Nx Of Og Oh Pe Po) Is(aD Al Ar bA bS bV cI cV dJ dN Id Iz Kg Kj oE Ou Qg Qv rX Ua Uh Ul Us Vt Tj) Po(Fr Hq Il Jg Jq Jr Jt Lu Me Mm Mr Mz Nb Ne Ng Nj Nk Nl Nt Nx Og Oh Oy Pe) Nh(Ij Jn Jr Jt Lw Me Mi Mm Mp Ms Mu Mw Nb Ne Ni Nk No Nt Nv Nx Ny Pb Pc) Vt(bA eC Ed Gp Il Im Jl Kq Lx Ms Mw nW oH Ou Oz pF Qa qC QD Qe St Uk) Fr(Hq Hu Il Jk Jn Js Jt Lw Mb Mf Mm Mr Mx My Nb Nc Ne Ns Nu Og Pe) Nt(Jg Jn Jr Lw Me Mm Mp Mr Mu Mw Mz Ng Ni Ns Nx Oh Pb Pc Pe) Aj(BA Cu dF Ef Fy Id Ij Im Jg Jl Mt Ok On St Uc Uf Un) Kq(Ao Bg cI Co De Dk Iz jD Jk Kg Kj Ms My Oa Oz Pb Uk Ur) Et(bL bN cT Fy Hc Jy Kl Ks nW oE oN Ow pF Qu Qv Un Vv) Qa(aC bR Ch cI cT Cv dE dM Fi Gp Ou Qg Rt Uh Ur Ye) bA(Ad al Ar Ax bF bM Cs dF dJ Oa Oy Pb Pe Qd Uh) Ct(Ad cT Cu dF Fy Ij Im Jl Mt Ok On Pe Qd Qe) Jq(Ik Jg Jr Mm Mr Mz Nd Ne Ni Nj Nl Nx Oh Uk) Mz(Ik Jg Jr Mr Ms Nd Oh qD qX qY rC vS) Id(Ng oE Ou Oz Pb qC Qe qZ Uk Ur vS) Oh(Ik Jg Jr Jt Me Mm Mr Nb Nj Nx Pe) qZ(Db dE Fb Ow Pj qA qB uM vS) No(aC bS cA Nd uM vS Tj Th) Ng(Cu Fy Nv St Tn Tr Uh Un) Wm(dF dM hB Im oE Ok Qd) Lx(bR bS CO Fi oN Uk) Nd(Ij Jg Jt Mm Mp Mw Nv) Ur(Im Jl Lw Oa Ou Qe Un) Ni(Mm Nj Nl Nv Nx Qb) Il(Dr Lv Sf Wc Yl Xa) Qd(Lw Mu Nk oE qC Uk) Jg(Jr Me Mr My Og Pe) Un(jD Ms Oz qC Uk) Im(Dr Ou Uk Ye) aC(Cu dF dM fR) Lv(Me Mx Ne) Mr(Ik Mm Nx) Ms(Mp Nv Nx) Qc(cT Ou Uk) Ji(qD qY vS) qC(Kn Li Ny) Lw(Oa Uh) Pe(Ha Nx) nW(uX wD) ChOn DrNq EdVq MmJr MtbR IjWc StYe KdoE OaOu aFdF cPeP Constrained panels with 2 analytes, where 1.0E-4 >= 'model p-value' > 1.0E-5. Contains 1,619 panels of 193,455 total panels evaluated. : In(As BA Bc bV Cp Cv Cw Dc dF dG dJ dL dM Dp Dr Fb Hu Ih Il Ip Ir Iv Jj Jm Jo Jy Kf Kk Kp Kr Kx Lw Me Mj Mp Mx Nb Nc Nd Ne Ni Nj Nl Nn No Nr Nu Ny Or Pd Pg Pi Pk Qh Ql Qm Rf Rm Tv Uc Ul Us Vq We Xa) Vt(aA Aj Ax Ba bF bH bN bV Cs CT cV dF dM Dp Fa Fr Fy Id Ij jK Jo Jp Jq Jy Kg Kk Ko Kp Li Lv Lw Mm Mt Nb Nd Ne Ng Ni No Nr Oa Oh Oy Pb Pe Qc Qh Qv qX Rf Rh Ri Uf Uh Ul vS Wm) Jj(Al Ap As Bb bR bV bZ Cp Cq cT Cw dF Dg Dl dM dN Ed Ef Ez Gp HB Hv Hw Ih Iv Jy Kd Kf Kk Kl Ks Lu Lw Ma Me Mf Mh Mi Mv Nc Ng Or Pc Pi Ql Rf Tn Tv Tz Ul Us Ut Vo) Id(aA bA bZ CT dM Dp eC Ed eZ Fa Fy Gp Hb Il Im jK Jl Jp Jy Kk Kp Kq Li Lj Lv Lw Lx Mq Ms Mt Mw Nb Nd No Oa Oh Or Oy pF Qa QD Qv qX rC Rj St Uf Uh uM Un wP) Lx(aC AD Aj aN aV bA bL bQ bU bV cA cC cF cG Ch cK cL Cs Ct Cv dA Dc dH dI dJ dM dN Dp Dr Fc Fy Gp Jy Kd Kk Kn Kq Oa oE Or Ou Sr Uh Ul Un Ur Wc Yk) Jq(Aj Ar Ax bA cI Cs Ct dM Ed Hu Ij Il Ir Jn Jt Lu Ma Mb Md Me Mh Mp Mu Mw Mx Nb Nc Ng No Nr Ns Nu Nv Oa oE Og Ou Pb Pc Pd Pe Pg Pz Qb St Uf Uh Un Ur) Lj(Ad al Aj aM Ba bB Bc cG cT Cu Cv Dc Di Dp Dr eC Fy Gp Ha HB Hw Ij Jn Kd Kk Kn Ko Kp Ma Mi Or pF Pj Qm Qv rS Sr Uk Ul Ur uX Vi vS wB Wd Wh wP Xa) Un(Ax bA bN cI Cs CT eC Ed Fy Gp Ii Il Im Iz Jl Jo Jy Kg Kj Kk Li Lw Mq Mw Nb Nd Ne Ni Oa oE Oh Ou Oy Pb Qa QD Qe Qv qX St Uf Uh Um Us Wm) Kq(Ax bA bL Cs Dp Ed gW Hc Hq hV Ib Ii Il Im Is Jd Je jF jM Jo lO Lw Md Mk Mw Nd Ne Nv oE oN Ou Ow Qa qC Qe Qt Qu qX Ss Ua Us Ut Uu Wc Tj) Uh(aA Ad Aj As Ax Ch Cs Ct Cu Cw Dc Ed Fp Fy Il Im Jl Jr Kd Kn Li Lv Mq Mr Ms Mw Ni No Oa oE Oh Or Ou Oz Pe Qd Qe Ra Sr Tv Uk Up Ur Us Wm) Oa(bF bV cE cT dF dM dN Dr eC Fc Fi Fy Gp HB Im Jl Jp Jy Kn Ko Lp Mq Mw Nd Ng Ni Nk No oE oH Ok On pF Pj qC Qd Sr Uf Uk We Ye Xa) Ou(Aj Ar Ax Bc Ch Cs Ct Dr Fa Fp Fy Ij Il Jl Kd Kk Kn Ko Li Mq Ms Mw Nd Ng No Oh Oy Oz Pb Pe Pj qC Qd qX Rf Sr St Uf Uk uX wD Wm Ti) bA(aD aJ aM aU bB Bc bL bR bS bW cE cF cK Dc dE dG dL dM dN Dr Fa Fp Fr Im Jl Jp Jr Jy Li Mq Mt Mw Ng No Oz Qc Qm Rf St Uf Uk Ur) Im(aC aD al aN Ar bB bR bS bV bW cA Ch cI Cs Cv dE dF dM dN Fy gP Iz Jy Kd Kj Kk Kn Ko oE Or Ow Pj Qv Sh Tv Uf Ul We) Pe(aC Aj bL bR bS bV cA Ch Co Cv dE dM dN Gp Hu Ik Jn Jr Mm Mp Ms Mu Mw Mz Nb Ne Ni Nj Nl Nv Op Pb qC Uk Ur Tj) Nx(Hv Hw Ij Ik Jg Jn Jr Js Jt Lu Lw Me Mh Mi Mm Mp Mu Mw Mx Mz Nb Nc Nd Ne Ng Nj Nl No Nu Nv Og Pb Pc Qb) Wm(aI aJ bB bF bR bV bZ cE cT cV dN Lv Lw Mq Mr Mt Mw Nb oH On pF qC qZ rS Ur uX We Xa Ti) Qd(aC An Ar bN bR bS bV Ch cI cT dE dF dM dN Dp GP Iz Jy Kj IN oH qD Qv qY Sr Ul Ur Us) Qe(aC bR bV Ch cI Cv dE dF dM Dr Fy Gp Jy Kd Kj Kk Kn oE oH Or qC Qg Qv Sr Ul Us Va We Ye) Jl(aC aD AN Ar Ax bR bS bV cA Ch cI Cs cT dE dM dN Gp Gz Hb Iz Ko oE Pj qC Uf Uk Us Tj) No(Aj aU bR bV CT cV dE dJ dM dN Ik jK Jr Me Mr Ms Ne Ni Nj Nl Or rB Uf Uk Ur xA) dF(aA AD aJ An aO Ar Ax bL bM bR bS bU cA cF Ch cI cK cO Cs Dc dE dH dJ dM Fp Ng) Mr(Hu Jn Jr Jt Lw Me Mf Mp Ms Mu Mw Nb Nc Ne Ni Nj Nl Nr Nu Nv oE Oy Pb Pc Qb Ur) Qa(bS Dp Dr eC Fy gP Ha Ib Iz Jy Kg Kj Kk oE oH pF Pj qC Qm Qv Tv Uf Um Us We Tj) Uk(Ad Ax Cu Fy Ij Il Jp Kd Kn Ko Lh Li Lw Mq Mw Nm Oh Ok On Pj Sr St Tr Uf Ul) Ni(Ar Ax Cs Hu Ih Ij Ik Il Jn Jr Js Jt Mp Mu Mw Mx Mz Nc Ne Nr Pg St We Xa) qZ(AD Aj aL aw aZ Bb Bc bL bW Ch dJ Dl fP Hc Ib iH Ke Kn Ko Kr Kz Or vV) Lw(Ed Fa Fy Gp Hb Ik Jg Jr Kk Ko Kp IN Mz Nd Oh Po qC qD Qm qY St Uf) Ur(Ad Ax Bc Cs Cu Dc Fp Fy Ij Il Jp Kd Kn Ko Lh Li Rm Sr St Tv Uf Us) oE(Ar Bc cH Dr Fy hB kC Kk Kn Ko Lh Li mM Mt Mw nD nl Pj Sr St Uy) Cs(aA aC aU Ba Bc bF cE cG cT dJ dM Gp Jp Lv Mq Mt Ok qC vS wP) Mz(Hu Jn Jt Lu Me Mm Mu Mx Nb Nc Ne Nj Nl Nu Nv uX wB wP) Dr(aJ Ba cT Et Fp FR Gp Is Jn Jy Lv Mq Or Oz Pb Qb St) aC(aA Ad aJ Ar Ax Ba Bc bF bW bZ cE cG cS cT Dc dG dN Fr) dM(Ad al Ar aU Ax bF bR Cu dJ Fp Ij Li Lv Mq Mt Qm rC St) Is(eC Ed Gp Jy Kk Ko lX lY oH qC Qm rZ Uf Va Wc Ye Tl) Fp(aD bB bF bR bV bW cE cF cT dE dN Uf Uw Vi We Wh) Fy(bW Ch Dp Ed Gz Jo Ke Kg Kj Mq Nw Or Oy Oz Pb Pf) Mt(Ar Ax bQ bS bU cA cF Ch cK cO Cv Dc dH oN Wc) Ng(Ar Ax Bg Cp Dg Ef Fa Jt Kn Ko Mu Oh Sr Uc Xa) Jg(Ct Io Jn Lu Mh Mx Nb Nc Ne Nj Nl Ns Nu Pb Qb) Aj(Bc cT Dg Fr Ko Lh Li Lv Mq Om Sr Tn Tr) Mm(Hu Ij Ik Jn Js Jt Mc Ms Mu Nb Nc Nj Nl) Jr(Ik Jt Me Mp Ms Mu Mw Nb Nd Ne Nj Nl Nv) Oh(Hu Hw Jn Kd Lu Mb Mu Ne Nl Ns Nu Nv Pb) Ax(aA aU bF cE cT Gp Jp Jy Lv Mq qC vS) Ct(Ef Fr Kn Lh Li Lv Mq Mw Pg Sr St Uf) Et(eC jD jO jP IN qC rX rZ tT uV vS vV) Ms(Ij Ik Jn Js Jt Kn Mu Mw Qb St Uf) Nd(Aa Il Jn Js Mi Mu Nb Ny Pd Pg Qb) St(Bc Ch Eq Nk Sh Sr Va Vi Wc Yk) Ar(aA aJ cE cT dJ Gp Jp Lv Mq) Ik(Jn Js Jt Mp Mw Nv Pb Po Qb) Jt(Lu Mb Mu Nb Ne Nj Nl Pb) Nv(Me Ne Nj Nl Ns Og Oy Pb) cT(Ad al Bc Cu Dc dN eP Fr) Jp(Ch Ed Iz qX rB rX Sr) aJ(Ad al bF bR cE dE dJ) qC(Dc Ih Ko Kp Nm Rm wD) Il(Eq Sh Va Yk Ye Tl) Uf(Ed Kd Kj Oz qX Sr) Pj(Fa Mq Or qX Sr wD) bF(aA aM Dc dJ dL dN) Mw(Kd Kk Ne Nj Nl) We(Ld Mq Or Pb Qb) Jn(Me Nb Po Va Vq) Kn(eC Oy Pb qD rB) Li(gP Jy qX Rg Sr) Nw(eC Iz qX rW vT) On(Ao Co Rt Wc Tl) Nh(Ip Js Nc Nn) Xa(Jy Or Oz Pb) Ke(hV rA uM uV) Vt(Kg Oz Pb Qb) aA(Ad bM bR Cu) Ch(hB Ij Ok) Po(Fi Ns Tj) Nj(Mp Mu Nb) Nl(Mp Nb Nk) Ji(vV Wc yL) Pf(eC Gz Yk) wD(dE Ri tF) vS(Ko Kp Sr) Ad(Gp Kj) Fa(Fi Th) Me(Js Mu) Mq(dE dN) Or(Zq Tl) Oy(Tr Vs) Oz(Uw Wh) bR(dG fR) dJ(Cu dN) DcGp FiNr LvbV MyJh NcNk QbYe WcJy KdeC KgOk KowP NyqA OwuX bBqX dBrN fRgP hBoN Constrained panels with 2 analytes, where 1.0E-3 >= 'model p-value' > 1.0E-4. Contains 3,604 panels of 193,455 total panels evaluated. : dM(aA aD AJ aK An aQ Ba BB Bc bL bM bU bZ cA cB cE cF cG cK Cp CT Cv Dc dD dE DG dN Dr Ed Fa FR Fy Gp Hb Il jK Jp Jr Jy Kd Kk Kn Ko Lh Lw Me Ml Mn Mr Ms Mw Mz Nb Nd Ne Ng Ni Nr Nx Ny Oh Ok Om On Or Ou Oz Pg Pj Po QC Qh qX Rf rX rY sC Sr Uf Uh ul Uk Ur vT vV wD zH) Ur(aA Ar As bV Cp Cq cT Cv Cw dF dN Dp Dr Ed Fa Fb Fr Hu Hv Hw Ih In Ip Ir It Iv Jg Jm Jn Jr Js Jt Jy Kf Kk Kp Kr Kx Lv Me Mj Ml Mm Mp Mq Ms Mt MW Mz Na Nb Nd Ng Nl Nm Nr Ny Oh Ok Om On Or Oz Pb Pd Pg Pi Pj Pk Po Pz Qb QC Qh Ql Qm Ra Rf Rj Tn Tr Uc Uk Ul Up uX vS We) Cs(AD al aJ aM An Ar As Aw BB bC bR bW bZ cF cL Cp Cv Dc dE DG dN Dp eD eF Fb fN FR Ha HB Hu Ij Il jV Jy Kd Kk Kn Ko Kp Ky Lh Lw Mc Mm Mr Ms Mw Nb Nd Ng Nj Nk No Nr oE OH Om ON Or Pj Qc Qg Qm qX rB rC Rg sC Sr Uf Uk Ul uM Vq wB We Wh Ti) Ax(AD al AJ aM AN As Aw Ba bB Bc bR bW bZ cF cG Cp Ct Cv Dc dE dG dJ dN Dp eC eD Fr Ha Hb Hu Ij Il jK Kd Kk Kn Ko Ky Lw Lx Mc Me Mm Mr Ms Mw Nb Nd Nk No oE oH Oi Ok Om On Or Oy Pb Pj qD qX rB rC Rg Sr Uf Ul uM wB We wL wP

Figure 1 Continued xA) Hq(Lx Nc Pf Po wB yJ) Og(Hu Jm Nc Nt Oh Pf) eP(Bb Dd Ed Kp Kz Po) tU(Gl jP Kz qY rC Tj) jE(dR gP hG iH iP oK) qH(bP iJ rC Ue Us Vo) xA(Ax cH jP Kr Pd Vt) uI(bP cH qY Us Uu Vo) dK(qQ uV uZ vQ wP) sK(cP Jn JP Kz) qX(aW Jf Ql Wm Tj) Vt(qP uU uX vW) Pf(Lz Oz Pe Pg) Mk(aA Jl On) Ou(qO qP uV) cH(qQ uT vU) iP(jV lN wP) yJ(Ao Hu Jd) wB(bO Gl Hu) uO(Kp Kr Vv) uU(Cs Ml Vv) vV(aK jQ jR) Dp(jK lN) Nb(Nc Oz) Jt(Nt Ok) Ow(ql qO) aA(Hw Pg) bP(uN uV) gW(Ti Th) rV(gP qY) qQ(jT Kp) uZ(Cs Kr) WmtL GluT WceM VowP Ozcl
aNwE aWrT dRjF hGjH rCuV jMkQ jPnY lKqP} Et{Ng(aA aC AD aE AF aG aH aI AJ aK AL aM AN AO AP aQ AR AS aU aV AW AX aY
aZ BA BB BC bE bF BG bH bI bJ bL bM BN BO bP bQ bR bS bU bV bW bX bZ cA cB cC cD cE cF cG CH cI cJ cK cL cM cN CO CP CQ cR
CS CT CU CV CW CX cY cZ dA DB DC DD DE dF DG dH DI dJ DK DL dM dN Dp dR eC Ed EF eT EZ Fa Fb FN FP Fr Fw FY GL GP gW
Gz Ha HB HC HF hG hL hO hP Hq Hr Hu Hv Hw Hx iA Ib Ic Id IH Ii IJ Ik Il Im In IO IP Iq Ir Is It Iu Iv IZ Jd Je Jf Jg Jh Jj Jk Jl Jm Jn Jo Jp Jq
Jr Js Jt Ju Jv Jy Kc Kd Ke Kf Kg Ki Kj Kk Kl Kn Ko Kp KQ KR KS Kx Ky Kz Ld Lh Lj Lu Lv Lw Lx Ly Lz Ma Mb Mc Md Me Mf Mg Mh
Mi Mj Mk Ml Mm Mn Mp Mq Mr Ms Mt Mu Mv Mw Mx My Mz Na Nb Nc Nd Ne Nf Nh Ni Nj Nk Nl Nm Nn No Nq Nr Ns Nt Nu Nv nW
Nx NY Oa OE OF Og OH Oi OK Om ON Or Ou Ow Oy Oz Pa Pb Pc Pd Pe PF Pg Ph Pi Pj Pk Po pS pY Pz QA QB QC QD Qe QG QH qI Ql
Qm Qn qO qP qQ Qt Qu Qv Qw Qx Qy Qz Ra Rb Rc Rf Rg Rh Ri Rj Rm rO rP rT rV rW sC sO Sr Ss St Tn TO TR tS TT tU Tv Tz Ua Ub Uc
Ud Ue Uf Ug Uh Uk UL UM Un UO UP UR Us UT UU UV uY VO VP VQ VS VT VU VV vW wB wC wD wE wF wG wH wJ wK wL wP
wQ yD yH yJ yK yL zA zG zH yE tM tL xA Wn Wm Tj tF) Aj(aA aC Ad AF aH aK AI aM aN AO Ap Ar As aW Ax BA Bb Bc bF Bg bH bI bJ
bL BN bR cC cD cG Ch cI cK cL cM CO CP CQ cT Cu CW Cx Dc DE dI dJ DK dM dR eF eP Fn Fp Fr Fy Gl GP gW HA Hb Hc Hf Hq Hr Hu
Hv Hw IC Id Ih Ii Ij Ik Il Im In Is Iu Iv Iz JD JE JF JG Jj Jl JM Jn JO JP Jq JR Jy Kc Kd Kg Ki Kj Kk Kl Kn Kp Kq Kr Ks Kx Ky Kz Ld Lh Lj
lL lM lN lO Lu Lv Lx Ma Mb Mc Md Mh Mi Mk Mm Mn Mq Mr Ms Mt Mw Mx My Nb Nc Nd Ne Nh Ni Nj Nk No Nr Nt Nv nW Ny Oa OE
Of Oh oK Om oN Ou Ow Oy Oz Pa Pb Pd Pe Pf Pg Pi Pj Pk Po Pz Qa QC QD Qe Qg Qh qI Qm Qn QT qU QV qW qX qY qZ rA RB rC Ri rS
rT rW Sr Ss St Tn To Tv Tz Ua Ub Uc Ud Ue Uf Ug Uh Uk Ul UM Un Uo Up Ur Us Ut Uu UV Vo Vp Vq vS wP zI Wm Tj) Jj(aA Ad Af Al
An AO Ap Ar As Aw Ax BA Bb Bc Bg BN Bo Ch cI Co Cp Cq Ct Cu Cv Cw Cx Db Dc Dd Dc Dg Di Dk Dl Dp Ed Ef Ez Fa Fb FN Fp Fr Gl
GP gW Hq Hr Hu Hv Hw Hx Ib Ic Ih Ii Ij Ik Il Im In Io Ip Iq Ir Is It Iu Iv Iz Je Jf Jg Jh Jk Jl Jm Jn Jo Jp Jq Jr Js Jt Ju Jv Jy Kc Kd Ke Ki Kj Kk
Kl Ko Kp Kq Kr Ks Kx Ld Lh Lj Lu Lv Lw Lx Ly Lz Ma Mb Mc Md Me Mf Mg Mh Mi Mj Mk Ml Mm Mn Mp Mq Mr Ms Mt Mu Mv Mw
Mx My Mz Na Nb Nc Nd Ne Nf Nh Ni Nj Nk Nl Nm Nn No Nq Nr Ns Nt Nu Nv Nx Ny Oa Oe Of Og Oh Oi Ok Om ON Or Ou Oy Oz Pa Pb
Pc Pd Pe Pf Pg Pi Pk Po Pz Qa Qb Qc Qd Qe Qg Qh Ql Qm Qn Qt Qu Qv Qw Qx Qy Ra Rb Rc Rf Rm Sr Ss St To Tz Ua Ub Uc Ud Uk Ul uM
Un Up Ur Us Ut Uu Uv Vo vS Vt Wm Tj) Lj(aA aC Ap bA bN bO bR cI Ct Cx De dI Dl dM eC Fp Fr gP Ha Hq Hr Hu Hv Hw Hx Ih Ii Ij Ik Il
Im In Io Ip Iq Ir Is It Iu Iv Jg Jh Jk Jl Jm Jn Jo Jp Jq Jr Js Jt Kg Lh Lu Lv Lw Lx Ly Lz Ma Mb Mc Md Me Mf Mg Mh Mi Mj Mk Ml Mm Mn
Mp Mq Mr Ms Mt Mu Mv Mw Mx My Mz Na Nb Nc Nd Ne Nf Nh Ni Nj Nk Nl Nm Nn No Nq Nr Ns Nt Nu Nv nW Nx Ny OE Of Og Oh Oi
Ok Om ON Ou Oy Oz Pa Pb Pc Pd Pe PF Pg Po pS Pz Qa Qb QC Qd Qe qG qH qI qO qP qQ Qv rO rP rQ rR rS rT rV rW sC sK sO tO tQ tR tS
tU uI Uk uM uN uO uP UR Us uT uU uV uW uY uZ vA vB vC vH vI vO vP vQ vS vT vU vV vW wB wC wE wG wH wJ wK wL wP wQ yD
yH yJ yK zA zG zH zI yE tM tL xA Wm) qX(aC AD aE AF aG aH aI aJ aK AL aM AN AO AP aQ AR AS aU aV AW AX aY aZ BA BB BC
bE bF BG bH bI bJ bL bM BN BO bP bQ bR bS bU bV bW bX bZ cA cB cC cD cE cF cG CH cI cJ cK cL cM cN CO CP CQ cR CS CT CU
CV CW CX cY cZ dA DB DC DD DE dF DG dH DI dJ DK DL dM dN Dp Ed EF Ez Fa Fb fP Fw Gl Gp Hb Hc Hf Ib Ic Id Iz Jd Je Jf Jy Kc Kd
Ke Kf Kg Ki Kj Kk Kl Kn Ko Kp Kq Kr Ks Kx Ky Kz Ld nW Oa oE oK Or Ou Ow Ph Pi Pj Pk qC QH Ql Qm Qn Qt Qw Qx Qy Qz Ra Rb Rc
Ri Rj Rm Sr St Ua Ub Uc Uk uM Us Ut vS Vt Vv Wm Tj tF) In(aA aC AF AI aM AO Ap Ar Ax BA Bc Bg bL bN Ch cI Co Cs Ct Cx Db Dc
DE Dg Dk Dl Dp Ed Ef Fa Fp Fr Gl Hb Hc Hq Hr Hu Hv Hw Hx Ic Id Ih Ii Ij Ik Il Im Io Ip Iq Ir Is It Iu Iv Iz Jd Jg Jh Jk Jl Jm Jn Jo Jp Jq Jr Js Jt
Jy Kd Ke Kk Kl Kn Kp Kq Kr Kx Lh Lu Lv Lw Lx Ly Lz Ma Mb Mc Md Me Mf Mg Mh Mi Mj Mk Ml Mm Mn Mp Mq Mr Ms Mt Mu Mv
Mw Mx My Mz Na Nb Nc Nd Ne Nf Nh Ni Nj Nk Nl Nm Nn No Nq Nr Ns Nt Nu Nv Nx Ny Oa Oe Of Og Oh Oi Ok Om On Or Oy Oz Pa Pb
Pc Pd Pe Pf Pg Pi Pk Po Pz Qa Qb Qc Qd Qe Qh Qn Qu Qv Qz Ra Rm Sr Ss St Ua Uc Uf Uk Ul Un Up Us Uu Uv Vt Vv Wm) Ms(aA aC Af aH
AO Ap Ar Aw Ax Ba Bg bL Bn Ch cI Co cR Ct CW Cx Db DE Dg Dk Fp Fr Gl Hc Hq Hr Hu Hv Hw Hx Ih Ii Ij Ik Il Im Io Ip Iq Ir Is It Iu Iv Iz
Jg Jh Jk Jl Jm Jn Jo Jp Jq Jr Js Jt Kg Kj Kl Lh Lu Lv Lw Lx Ly Lz Ma Mb Mc Md Me Mf Mg Mh Mi Mj Mk Ml Mm Mn Mp Mq Mr Mt Mu
Mv Mw Mx My Mz Na Nb Nc Nd Ne Nf Nh Ni Nj Nk Nl Nm Nn No Nq Nr Ns Nt Nu Nv Nx Ny Oa Oe Of Og Oh Oi Ok Om ON Or Oy Oz Pa
Pb Pc Pd Pe Pf Pg Po Pz Qa Qb Qc Qd Qe Qu Uk uO Ur Uu vS vV Wm) Oy(aA Ar Ax bA Ch cI Cs Ct dM Fa Fp Fr Hq Hr Hu Hv Hw Hx Ih Ii
Ij Ik Il Im Io Ip Iq Ir Is It Iu Iv Jg Jh Jk Jm Jn Jo Jp Jq Jr Js Jt Lh Lu Lv Lw Lx Ly Lz Ma Mb Mc Md Me Mf Mg Mh Mi Mj Mk Ml Mm Mn Mp
Mq Mr Mt Mu Mv Mw Mx My Mz Na Nb Nc Nd Ne Nf Nh Ni Nj Nk Nl Nm Nn No Nq Nr Ns Nt Nu Nv Nx Ny Oa Oe Of Og Oh Oi Ok Om
On Oz Pa Pb Pc Pd Pe Pf Pg Po Pz Qa Qb Qc Qe Qv Uk Vs wD Wm) Is(aA aN Ao Ch cI Ct Fp Fr Hq Hr Hu Hv Hw Hx Ih Ii Ij Ik Il Im Io Ip Iq
Ir It Iu Iv Jg Jh Jk Jl Jm Jn JO JP Jq Jr Js Jt Kg Lh Lu Lv Lw Lx Ly Lz Ma Mb Mc Md Me Mf Mg Mh Mi Mj Mk Ml Mm Mn Mp Mq Mr Mt
Mu Mv Mw Mx My Mz Na Nb Nc Nd Nc Nf Nh Ni Nj Nk Nl Nm Nn No Nq Nr Ns Nt Nu Nv Nx Ny Oe Of Og Oh Oi Ok Om On Oz Pa Pb Pc
Pd Pe Pf Pg Po Pz Qa Qb Qc Qd Qe Wm) Ch(aA aC bA bN cI dM dR eC eF eZ fP gL gP hB hC hF hG hO Hu iA iH Ii iJ Il Im iO iP iZ jD jG Jl
jM JO jP Jy kQ kR kS lL lM lN Lv Mm Nb Nd nW nY Oa oE oF oH oK oN Ou PF qB qC qD qG Qh qI qQ qT qU QV qY qZ rA rU Sr TN tO
tR tS Uk uM uP UR Us uT uV vO vP vQ vS vT vU vV vW wB wC wD wE wF wG wJ wK wL wP wQ yD yH yJ yL zA zG zH zI tM tL xA tF)
Nd(aA cI Ct Fp Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Lu Lv Lw Lx Ly Lz Ma Mb Mc
Md Me Mf Mg Mh Mi Mj Mk Ml Mm Mn Mp Mq Mr Mt Mu Mv Mw Mx My Mz Na Nb Nc Ne Nf Nh Ni Nj Nk Nl Nm Nn No Nq Nr Ns Nt
Nu Nv Nx Ny Oe Of Og Oh Oi Ok Om On Op Oz Pa Pb Pc Pd Pe Pf Pg Po Pz Qa Qb Qc Qd Qe Si wD Yd Wm) Im(aA cI Ct Fp Fr Hq Hr Hu
Hv Hw Hx Ih Ii Ij Ik Il Io Ip Iq Ir It Iu Iv Iz Jg Jh Jk Jl Jm Jn Jo Jp Jq Jr Js Jt Lh Lu Lv Lw Lx Ly Lz Ma Mb Mc Md Me Mf Mg Mh Mi Mj Mk
Ml Mm Mn Mp Mq Mr Mt Mu Mv Mw Mx My Mz Na Nb Nc Ne Nf Nh Ni Nj Nk Nl Nm Nn No Nq Nr Ns Nt Nu Nv Nx Ny Oe Of Og Oh Oi
Ok Om On Oz Pa Pb Pc Pd Pe Pf Pg Po Pz Qa Qb Qc Qd Qe Si Uk Zq Wm) Pb(aA cI Ct Ed Fp Fr Hq Hr Hu Hv Hw Hx Ih Ii Ij Ik Il Io Ip Iq Ir It
Iu Iv Jg Jh Jk Jl Jm Jn Jo Jp Jq Jr Js Jt Lh Lu Lv Lw Lx Ly Lz Ma Mb Mc Md Me Mf Mg Mh Mi Mj Mk Ml Mm Mn Mp Mq Mr Mt Mu Mv
Mw Mx My Mz Na Nb Nc Nc Nf Nh Ni Nj Nk Nl Nm Nn No Nq Nr Ns Nt Nu Nv Nx Ny Oa Oe Of Og Oh Oi Ok Om On Oz Pa Pc Pd Pe Pf Pg
Po Pz Qa Qb Qc Qd Qe Uk Vq Wm) Lv(aA Ao Ct Dk eP Fp Fr Hq Hr Hu Hv Hw Hx Ih Ii Ij Ik Il Io Ip Iq Ir It Iu Iv Iz Jg Jh Jk Jl Jm Jn Jo Jp Jq
Jr Js Jt Lh Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Ne Nf Nh
Ni Nj Nk Nl Nm Nn No Nq Nr Ns Nt Nu Nv Nx Ny Oe Of Og Oh Oi Ok Om On Oz Pa Pc Pd Pe Pf Pg Po Pz Qa Qb Qc Qd Qe Wm) Fp(aA cI
Ct eP Fr Hq Hr Hu Hv Hw Hx Ih Ii Ij Ik Il Io Ip Iq Ir It Iu Iv Jg Jh Jk Jl Jm Jn Jo Jp Jq Jr Js Jt Lh Lu Lw Lx Ly Lz Ma Mb Mc Md Me Mf Mg
Mh Mi Mj Mk Ml Mm Mn Mp Mq Mr Mt Mu Mv Mw Mx My Mz Na Nb Nc Ne Nf Nh Ni Nj Nk Nl Nm Nn No Nq Nr Ns Nt Nu Nv Nx Ny Oe
Of Og Oh Oi Ok Om On Oz Pa Pc Pd Pe Pf Pg Po Pz Qa Qb Qc Qd Qe vS Wm) Ni(aA cI Ct eP Fr Hq Hr Hu Hv Hw Hx Ih Ii Ij Ik Il Io Ip Iq Ir
It Iu Iv Jg Jh Jk Jl Jm Jn Jo Jp Jq Jr Js Jt Lh Lu Lw Lx Ly Lz Ma Mb Mc Md Me Mf Mg Mh Mi Mj Mk Ml Mm Mn Mp Mq Mr Mt Mu Mv Mw
Mx My Mz Na Nb Nc Nc Nf Nh Nj Nk Nl Nm Nn No Nq Nr Ns Nt Nu Nv Nx Ny Oe Of Og Oh Oi Ok Om On Oz Pa Pc Pd Pe Pf Pg Po Pz Qa

Figure 1 Continued

Vt Vu Vv Wm Tj) Jl(Al aQ aU aW Bb bS bW bX cA cB cF cN cP Cv dC Dd dM Ed Fr Gz Hb Hu Hv Ij Ik Il Iz Je Jj Jk Kf Kg Kj Kk Kl Kp Kz Ld Lz Mb Me Mh Ml Mq Mu My Nd Ow Oy Pi Pj Qg Qm Qt Qu Qw Qx Qz Rb Rc Rj Rm Sr Ss St Tz Ua Uh Ul Up Ur Uu Vp Vs) Ql(aD Af Aj aQ BB bL BN bP bZ cP CX dC dJ dL dN Ed Gd Gp Hb Ii Ij Il Im Ip Iq Ir Iu Je Jp Kj Kp Ky Kz Ly Md Me Mh Ml Mn Mq Nn Nq Nv Nx Oi Om Ow Oy Oz Pa Pb Pf Qa Qh Qd Qe Qh Qn Qz Rb Rf Ue Ur Vq Tj) Ed(BA Bo bR cF cP CT Cw dF dN Ef Fy Gl Hb Hw Ih Ii Il Jn Ki Kn Kq Kx Ky Ld Lx Mn Nr Of Oh Ok On Ou Ow Pe Qc Qm Qx Rf Rm Sr St Uh Uk Ul Vv) Qb(aA Al aQ BA BB bS cA cF cN cP cT Cv Dc Dd dF dL Em Gp Hv Il Ip Jk Ju Ly Lz Me Mg Mj Mq Nc Nd Ny Oh Pf Qm Rg Up) Lx(aA Al Ba Bb cN cP Cq Ct Cv Dc Dd De dM Ex Gd Gp Ik Ip Kp Kz Me Mq Nc Nd Ny Of Og Oy Pa Qm Qz Rg Sr St Ul Up Us) Ow(aA Ad bA Bb bF cN cP Cv Dd dK dM dN Em Gp Hf Ij Il Kp Kz Ly Me Mw Nm Qc Qm Qv Ra Rf Rg Rm St Ua Ul Us Vs) St(Aj aM Bb Bo cP Cx Dd dM Hq Hu Ib Jj Jo Kd Kg Kj Kp Kz Lv Ly Mq Nc Nl Ph Qt Qz Sr Up Ur Vq) Qa(aU BA Bb cN cP Cv cY Dd dF dM Em Gp Hv Jk Ju Kp Kr Kz Me Nc Nd Pa Qm Ul Up Vp) cP(aZ bB cE cG dF Fw Gp Hb Ij Im Ky Lz Ml Mp Mq Nq Oh Pe Pf Pg Qc Qd Qe Qm Rm Tz) Mq(aG aQ aZ BA cD cN CT dF dM Ik Il Lu Ma Oe Of Ok Qc) Sr(aH aQ aU Bb CV Gp Il Ip Iq Ky Kz Ly Md Nq Rb Ul Ur Us) bA(aM bB bL Ct Hb Ij Jj Ml Pf Pj Qc Qd Qe) Im(Bb cN Jk Kp Kz Me Nd Ul Up Us Vp) Gp(Af bM cX Fy Hr Oa Qe Rm Uv Vq) dF(aF bL CX Fp Me Oy Qc Qe) Bb(Fy Kq Ok On Pe Qd Qe Rf) Qe(Ba cN Ct Dd Of Ul) Kz(Kq Oh On Qm Rm Tz) Ur(cN dN Hw Nr Rm) Me(bZ Oh Ok On) cN(Ij Ml Pe Pj) Cv(Kx Oa Pe) Dd(Ih Pe Qd) Il(Hb Oa Or) Ky(Hr Uv Vq) On(dM Kj Kp) aJ(aQ aU cB) Ba(Qd Ss) Fy(Kg Qc) Ik(Hx Oy) Ir(Ko Us) Qt(Oh Qc) NnNd NqVq LyRm MvMy HfOh KpKq UsPf PbdL} Ok{In(aA Fp Fr Hq Hr Hu Hv Hw Hx Ih Ii Ij Ik Il Im Io Ip Iq Ir It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn Nq Nr Ns Nt Nu Nv Nx Ny Oe Of Og Oh Oi Om On Oy Oz Pa Pb Pc Pd Pe Pf Pg Po Pz Qa Qb Qc Qd Qe Vt Wm) Fp(aA Fr Hq Hr Hu Hv Hw Hx Ih Ii Ij Ik Il Im Io Ip Iq Ir It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn Nq Nr Ns Nt Nu Nv Nx Ny Oe Of Og Oh Oi Om On Oy Oz Pa Pb Pc Pd Pe Pf Pg Po Pz Qa Qb Qc Qd Qe) Jj(aA Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn Nq Nr Ns Nt Nu Nv Nx Ny Oe Of Og Oh Oi Om On Oy Oz Pa Pb Pc Pd Pe Pf Pg Po Pz Qa Qb Qc Qd Qe) Nd(Fr Hq Hr Hu Hv Hw Hx Ih Ii Ij Ik Il Im Io Ip Iq Ir It Iu Iv Jg Jh Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Ms Mt Mu Mv Mw Mx My Na Nb Nc Ne Nf Ng Nh Ni Nj Nk Nl Nm Nn Nq Nr Ns Nt Nu Nv Nx Ny Oe Of Og Oh Oi Om On Oy Oz Pa Pb Pc Pd Pe Pf Pg Po Pz Qa Qb Qc Qd Qe) Pb(Hq Hr Hu Hw Hx Ih Ii Ik Il Im Io Ip Iq Ir Iu Jg Jk Jl Jo Jq Jr Js Jt Lh Lj Lu Lv Lw Lx Ly Lz Mb Md Me Mf Mg Mh Mj Mk Ml Mn Mq Mr Ms Mt Mv Mw Mx My Nb Nc Ne Ng Nh Ni Nj Nk Nl Nm Nq Nr Ns Nt Nu Nx Oe Of Og Oh Om Oy Pc Pd Pe Pf Pg Po Qa Qb Qd Qe) Ms(aA Hq Hr Hu Hw Hx Ih Ii Ik Il Im Io Iu Jk Jn Jo Jr Js Jt Lh Lj Lu Lv Lw Lx Mb Md Me Mf Mg Ml Mp Mq Mt Mw Na Nb Nc Ne Ng Nh Ni Nj Nk Nl Nm Ns Nt Nu Nx Oe Of Og Oh Oi Oy Oz Pa Pd Pf Qa Qb Qc) Ng(Hq Hr Hu Hw Hx Ii Ik Il Im Io Jg Jh Jo Jr Lj Lu Lv Lx Mb Me Mq Mt Mv Mw Nb Nc Ne Nh Ni Nj Nl Oh On Oy Pa Pf Qa Qe Wm) Jo(Hq Hu Hx Ii Ik Il Im Io Jr Lj Lu Lv Mb Md Me Mf Mq Mt My Nb Nc Ne Nh Ni Nj Nl Nq Ns Nt Nu Nx Oy Pa Pf Qe) Ii(Hu Ik Il Im Jr Lh Lj Lu Lv Lx Mb Me Mq Mt Nh Ni Nj Oy Po Qa Qb Qe) Ni(Hw Ik Im Jt Lj Lv Mb Md Me Mq Nc Nh Nj Nl Nq Oy Qa Qb Qe) Oy(Hw Ik Im Jr Lj Lv Mb Mq Mt Mv Nh Nj Pd Pe Pf Qe) Jt(Hu Ik Im Lj Lv Mb Me Mq Mt Nb Nh Nj Qa Qe) Lj(Hw Ik Im Io Lu Lv Me Mq Nb Nh Nj Pa) Lv(Hq Hr Im Io Jk Md Mq Nh Nq Oe) Nh(Hq Hr Hw Im Io Lu Mq Ne Qc) Mq(Hr Hw Hx Nq Ns Oc) Im(Hq Hw Jk Nj) Ow(fN qC) cD(Ti Th) LuNj MeHr IhQa VqoE aZqC} wD{Tr(AN AW aY aZ Ba Bg bL bP bS cA cB cG Ch cK cL cN CO Cp Ct Cw dA DB DE dH dI DK Ef HA Hc Hq Hr Hw Ib iH Iz Jd jF Jh Jk jM jO jY Kr Kz Ma Md Me Mf Mg Mi Mk Mu Mv My Nc Ng Nk Nn Nq Nv oE Of oN Or Ou Ow Oy Pd pF Pg qH Qw Qy RB Ri Tn Ua Ub uI uM Uu vA Vp yL Tj) To(AW aZ Bg bL bN bR cO Cp Ct Cw DB DE Fb HA Hc Hq Hw iA Ib In Iv Iz jF Jj Jk jM jY Ki Kk Kn Kr Me Mg Mk Mv My Nc Ng Nk Nq Nv Of Ou Ow Oy Pj qC qD qH Qy RB Ri rW Ub uI uM uT uZ vT wP xA Tj) Pj(As aZ bL bN bR cB CH cO CS Cw DB De dN Fb hO Hu iH jF jO Js Ki Kk Ko Kz Ld Lj lK Lu Lz Me Mg Mt Mv My Ng Nk Ny Ou Ow qD qH Ql Qy Qz Rb Ri Rj rZ sC Sr Ub uM uX uY vA vT Vv vW) Lu(Aj An Ao Ar Aw aZ Bg bL bN Bo bS CH Cs Ct Cv Cx DB DE Dk dM Ef Ez Fb Fn Gp Ha Hc Hf iH Iz Jd Je Jf jM jO jY Kd Kg Ki Kk Kp Kr Kz Ld Ou Ow qC qH Ql rA Rb rC rW Tj) uM(AW Bg bL Bo bX Ch Cs Ct DB DE Dg Fw Hc Id iH jD jM jO Kc Kd Ki Ko Kr Kz qC qD Ql Qm Qx Qy RB rC Ri Tn Ua Uf Ur Vp Vt yH Wm Tj) Db(Ad aF Bb bL cH cP Cv dE dK Im Ip Iu jM jT Kc Kf Ko Kp My qC qD Qh Qm Qy rC Ri rZ Sr Tn Tv Ub Uf Uh uI uW uY uZ vA vI Vt zH tL) dB(aW cH cP Cs Dc Dg Fa JD Kc Kf Ko Kp Kr Lj Mh Mr Mt Pc qC qD Qh QY rC Ri Rm rW rX Tn Tv Uf Uh Ur Us uZ Vt zH) dE(Aw cP Cs CV De Hc iH Jd Ko Kp Kr Kz My qC qD Ql Qy Rb rC Ri rZ Sr Tn Tv Uf Ur Us uW uZ vA Tj tF) Ri(As bL bR cO cV cW De dJ Fb Hq iH jM jO Kr Lj Me oN Ou Ow qC Rb Tn Ub uY uZ) jO(Cs Id Ip Jf Js Kc Kn Ko Kp Ny Ou qC qD Qh Rf Rm Sr Tn Tv Ub Uf Un) iH(Ad aF cP dJ fN jM Kf Ko qC qD Qh Ql Qm qQ rC Sr Ss Ur uZ Vt tF) Ko(bL bN bR cO De Fb Hc Jd Ng Of Ou Ow qH RB Ub vW Tj) Tv(Aw Cp De Hq Hr Hw Hx jF Jk Me Of qH uI Tj) bL(Bb Cv Fb Kp Lj Ny Pg qD Ql Rb rC uY Vt zH) Tn(Aw bN bR De dK JK Kp Kr Me Of qH uI) Ou(Ad dJ fN Ip jM Nm Ss Tt Uc Ur Uu) qC(aW aZ De Ip Jd Me rZ Ur) jM(As Fb Js Kp Kr Ny Ow Qh) Ad(Aw bN Cw Hw Me qH vA) Nm(Ct Cw Ng Nk Ow Vv) Rb(Kp Me My Qh Qy uI) bR(bS cC lK Qy rC Ur) dJ(Kp Lj Ow qX Ub Vv) Cs(Hq jT uU uZ Tj) Tt(Aw Jk Kr Me uI) Qh(Aw cO Hq Jk rB) qD(Ch De Kr Me Qy) Kp(cV De eD rB) Lj(dC Ip jT rB) Hq(Ax Fa Pe) Sr(cO Mc rB) Ow(Ss Uc Uu) Ur(cF Cw hR) gP(Id Kx Mh) Dc(Ny Uc) Ng(Ss Uf) Ip(cB cO) Uu(qH uI) dC(aW Mh) AsMd BbjF CwKf TjPe FbrB MeQl JkUs UfqH VtvA} oE{Vq(aA aC AD aE AF aG aH aI AJ aK AL aM AN AO AP aQ AR AS aU aV AW aX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR cS CT CU CV CW CX cY cZ dA DB DC DD DE dF DG dH DI dJ DK DL dM dN Dp DR Ed EF Eq Ex Ez Fa Fb Fi Fn FP Fr Fw Fy Gc GL GP Gz Ha HB HC HF hG Hl Hp Hq Hr Hu Hv Hw Hx iA Ib Ic Id IH Ii IJ Ik Il Im In IO IP Iq Ir It Iu Iv IZ Jd Je Jf Jg Jh Jj Jk Jl Jm Jn Jo Jp Jq Jr Js Jt Ju Jv Jy KC Kd kE Kf Kg Ki Kj Kk Kl KN Ko KP KQ KR KS Ky Kz Ld Lh Lj Lp Lt Lu Lv Lw LX Ly Lz Ma Mb Mc Md ME Mf Mg MH Mi Mj Mk Ml MM Mn Mp Mq Mr MS Mt Mu Mv Mw Mx My mZ NA Nb Nc ND Ne Nf Ng Nh Nl NJ Nk Nl Nm Nn nO Nq NR Ns NT Nu Nv Nx NY Oa Oe OF Og OH Oi oK Om ON Op Or Ou Ow Oy Oz Pa Pb Pc Pd Pe PF Pg Ph Pi Pj Pk Po Ps Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sh Si Sr Ss St Tn To Tv Tz Ua Ub Uc Ud Ue Uf Ug Uh Uk Ul Um Un Uo Up Ur Us Ut Uu Uv Uw Va Vc Vo Vp Vs Vt Vu Vw Vz Wc Wd We Wf Wh Yg Yh Yk Yl Zx Tm Xa Wm Tj Ti Th tF Yf) Vt(aE aP aY bJ bL bM bV cH cI cM cQ cS cW dB dE Ex fP Gl GP Gz Hc IH Ii In Io Iu Jj Jk Ki Kk Kp Ld Lj Lu Mc Mj Mk MM Ms Mw Nb Ne Ng Nh Nk Nn Ny Oa oH oN Op Ou Ow Oy Pi Qg Rh Sr To Um Yd Yh xA Tk Wn Wm Tj Th tF) nI(Aj An Ao Ap Ar As Ax Ba Bb Bc BG Bn Bo Ch Co Cp Cq Cs Ct Cv Cw Cx Db Dc Dd Dg Dk Dl nD Ni Rb Rh To Up Wm) Op(Im kC Ld Lh Lj Lx Oa Oh On Qa Qb Qd Qe St Tz Un) mM(Hb Id Jq Kd Lh Mw Nb nD Ni Qt St To Uh Up Ur) bG(nD Ps Ux Uz Va Vc Vi Wf Wg Wh Yd Yh Yl Yf) Iv(Fi Ru Uy Vc Wd We Wh Yd Yi Yj Yl Yf) nD(Hu Im KR Mh Pf Rb Ri St Up) Yd(Bc Ld Lx Po Qa St Un) Dr(Gl kR Mm Rh To Th) Gz(Jl Lx Mt Uy Th) Ow(Id Im Pj Rf Un) Vi(Hu Im kC Ld Oa) Rh(Gc Hl kC Yl) Uw(cG Gl Kl Mm) Bc(Rt Rz Ux) To(Jj kC nA) Wh(Bg Dg Ss) Uy(bH cG Iq) yL(dB Sr Tr) Ld(Vj Zq) Lj(In uZ) BgWd DgWe YfcG GpRt IdqC OutX UpkC PdxA} qC{Id(aD aG aH Aj aK aL aM aN AP aQ aU aV AW AX aZ Ba BC Bg bL bN Bo bQ bR bS bV cB cF Ch

Figure 1 Continued

Tv) Wm(As hO Rf) Tj(Ax Nr Pe) Ch(Qh Uu) AnLu DbaF TtKr NyeD PeoK} uM{Ny(Aj bV Ch Fb hB Ib oF Ua Wm) Wm(dF Kn qX Ri Vs)
Ax(bW dE Ri) Ch(Kq Tn Uc) Uc(Aj Iz) Ib(Kq Kr) Kf(Db dE) DgVv LwyL UaKq JlrB dEhB} Db{wB(Ax It Kc Kf Na Pj Qy) nI(iA jB Mt Oa
Oz Pb) uT(aF Ax Hc Pj) Xa(Oz pK) Pb(nA nD) bA(yL xA) FdpK KfxA OznD cTyL hBuY} Ch{Rz(dU oD oV oW pH pI pK) Ny(eZ fN hO hP
pY qB) We(gL hB hG iZ) Xa(gL kR On) wB(Ad Ss Uc) SsuT KqgP} Oa{Mj(eQ jB oD oV pI) gP(Fi Gh Rt Si Vj) Op(hB iA oH pF) Gh(iP oF
oN) eC(Yh Yi Wn) We(oF oN) hB(Yh Yi) RieQ} mZ{Dr(bF bZ hG Jy Ma oF oH Yd) We(bZ hG iJ Jy Ni Vi) bZ(Gc Uy Tl) Xa(iJ oV) Rz(iJ Ni)
MaUy WhPb TloV} Bc{pI(Eq Fc Fd Fi Gc Lp Lt Op Ru Rv Ux Wf Yh Zx) Yh(dU pH) Oz(Rt Vj) eQ(Ri Ss) pK(Wd Tl)} qX{dJ(Js Kq Mr Ny
Pg Pj rC rW sC) Kq(De Md rB) Ny(Fb Pj Tj) Pj(Jy Ql) rB(Ad Fb) PgbL} Ly{hX(kC kI lY ml nC nD nH nL) lY(hV iB rY rZ) kC(hW rB rY)
nH(hV iB) nLiB} Qe{Nh(Ih Ms Ne Ni Pb) Mt(Ih Ms Oy Pb) Ms(Ik Nx) Ni(Ih Nj) WmTh TijD GlWe JgOy} On{Oy(Hu Ik Lv Mb Me Mt Mv
Nh Nj Nl) Ms(Ik Mt Nh Pb) EdFi MbMk NhPb} Aj{Ad(BA cT dF hP Ni Pb rS) Kq(fN jF jM) Ny(fN jD) BaaC KlrS} Jp{kl(hX rB rC rX rY rZ)
IW(IK rX rY rZ) IK(kK nB) MsMt IkPb} Wm{xA(As Kr Mt rS) dM(uW uZ vA) rS(As Rf Vv) QduP KqvA NyrB} yL{dM(Lu Ri Tv wL)
Vv(Dg Pj Ss) Hq(Ax Pd) Ny(bL dE) bA(Tn Tj)} Ed{Fi(Ij Jn Jy Mt Nr Uw Wh) Wh(gP Jn Ye) We(Jn Ye)} Fa{eC(Gd Op Yd Yh Yi Yl) dE(uU
vT) gP(Rt Yk) RieQ rBuY} Pb{nI(bR Gz Qm Rx) cQ(Ps Zq Xa) nF(Vi Yi) MsMt WhnT] Hq{Ax(uT vI wB zH) Pe(uU wK wQ zH) Pd(uT
wB)} nO{Lv(hA jE jO jP IK qT) Aa(iB jI) Me(hV iB)} jB{gL(Rt Uy Vb) DraD FiJm IjYk IqRt RukC UpPh UyhB} nF{Yk(Ij Nr Yi) hB(Dr Uy)
CxXa IjSh YioQ JmRt} xA{Pd(Ms Oy qA Ua) Ax(Mj Tj) eD(Kn Kr) TjPe} Ss{Kk(rW tR uG uW vV yD) wB(Qy Ua)} nD{Fy(Jt Up) eD(hV
mH) IjYk IrUp OzPi PaeC} jO{uX(Fb Ny qY) tV(dM Kr) TihB JluT cGuI} kR{Xa(iO Kj) IX(Wd Wh) lY(Rt Ry) GhfB IvWe} IK{nR(AA iB Jn
IO mT qU) MvkK} Kq{Ti(eD gW) fN(Ct Ib) AwuO ThgW TthP} Ad{wB(Aw Hc Of Oy) CtTk TieD} Mh{tU(dE jT Rb Ri) rS(Tn wJ)}
vV{jR(cU Mt Ny Qd Un) MtfY} Ni{We(iO Qb) XaiO OpOh UhmM}

Figure 1 Continued wC wL tM tL) uT(DB dE oK Ri) Ni(Jg Jp Qe We) zI(bL dJ Ug Ur) Nh(Fr Jp Pb) uZ(dM hB Lw) Aa(Rz Zq) gP(uX tM) iJ(qH rB) AstM DbnI ThgL HaPf IlSf IprR WeoN RieQ OphG OmPb dBrT dCzA dJqX dMuU fYqO jRvV} Il{Iv(Dr Fc Fi Gd Rt Sf Sh Vb Vc Wc Yk Tl) Fi(Ed jB Ld Mr mZ Ni Oa Or oV Qa) nD(Ed Kj Kp Kr Kz Or Qm Ss Up Ur) Dr(Ed jB Jo Jy Kg Kj mZ nF) Xa(Ap Ch Dg Ed Kg Kj Ni Oy) Yk(Ed Jo Ld Mq Ni Oa Or) Sf(Ed Ld Mq Oa oO Or Oz) Ni(Rt Vb Wc Wf Tl) Rt(Ld lY Oa Or) Sh(Ld Mq Oa) Kg(Hl Vi Yl) Ps(Ap Ch Dg) Oy(Lx Mt On) Ed(Wh Yf) Eq(Mq Oa) Wc(Or Un) Ye(bH Ql) nF(Vz Yl) lK(kK mS) ApUw GhjB MsQe ZxOr VbdA UymZ} Qa{Fi(bR cQ Ed Fc Gl Ih Kr Mm Ms Nc Ny Oz Pb Rh) gP(Ho Lp Op Rt Si Vi Wc We Yh Yi Tl) Th(Hf Jk Jy Kg Ne Nh Ni Nl Oz Uk) Ms(Hu Ik Lh Lv Mt Nh Ni Nx On Pb) Pb(Ih Ik Mt Nh Ni Pf Rt Yf) We(Gl Ii Kg Mm Nc Ye) Yc(Gl Mm Of St Ul) Kg(Vi Wh Xa Ti) Op(hB hG oH pK) Ih(Ct Mt Nh) Nj(Ni Nk) Jg(Jk Oy) Wh(Ed Qz) Kr(nD Rt) fN(Ou Ow) jT(vA vB) TiIi GlZq NkNl JtXa UfvA UpnD} Ou{fN(aJ aP bA cW dL dM dN Fa hB Id Jl Ko Kp Kq Lw Lx Mx Nx Ny On Ow Po Qd Qe Uc Ul Un uX Vs Vt) Nm(pS rN sC uN uV uX wH yE tM xA) uX(cV dJ jO Ko Lu Ss Uc Ur Uu) tM(Ad dJ Ko Tt Uc Ur) rS(Ad Dg Id Ko Uc Uf) uV(Ip Uc Uf Vt) Dg(rN tU uG) yE(Ko Uc Ur) pS(Tv Uc Us) Pj(qX wF) eD(Ow Ti) sC(Kf Vt) QdrR SsrN KoqI KqjM UfrV dJtX dMzH} St{Ye(Aj Ap bH bP bR cQ cZ dA Dg Ed Gl Iv Jn Jy Ld Me mZ Nb Nc Ni Nj Nk Nl Op Or Oz Pf Ql Um Vq Yk Wm) nD(Bo Cx Ii KR Nk Oz Ss Up) Ni(Fi Vb Wc Wf Yh Zw Th) Yk(Dl gP Iv Kg Nb nT Vq) Op(hB hG iO kR pF) jB(Fi Rt Ru Wc Yj) Va(Dg Dp gP hF) Wc(Iv Nb Nk) Nj(Eq Ti) Xa(Ap Dl) Vi(Kg mZ) nI(As Db) AjWh FdIv FimZ HlIi UsmW} Kp{uO(aW cH Db dE dJ eD Id Kr Me RB Vt) vA(bW dB dE Dg Id Ko Nm Ss Uf Vt Wm) sC(aZ DB dE Dg dM Id Pj rW Vt) dJ(qO rP tT uN vB vI vV yD tM) Ss(rW uI vV yL xA) eD(rS rW uV yD xA) jO(tV uX yD zA tM) Db(rN uV yD tM) fN(Aj Ch jE Ow) Ko(rP rS rT) dB(uV yL tM) rB(vI vV yD) Wm(rS xA) dE(uV yL) vV(jR Ri) LuyD IdrS PbPf cHwQ oKuV} Pb{Pf(bS Id Ik Iz Kk Lv Mt Ne Nh Nj Nl Nt Nu Nx Om Qd Qe Ua Ur Vt) Vq(dM kE lX mP mW nA nC nI nJ nO nT oF oP Vi) Qe(Ih Ik Ms Mt Nh Ni Nt Nu) nI(bR DB jB Qm Rx) Nh(Jp Lh Lx On Qd) Ms(Lx Mt On) Wh(Ed mZ nT) cQ(Ps Zq Xa) Db(nA nD) Ik(Jp On) nF(Vi Yi) AdAj DrkR LxMq MtQd KqcI RioV} Uf{rS(Aj cS Cw DB Fb iH Ma Ow qH Ql Rb uI yL) qH(Bo dB dE hL Lw Ql rO tU Vt) jO(rN tQ tT uN uT uX wB yL zI) uI(bR cH DB dE dM Ql Rb) vA(Cs Id Kd Kn Kr Ra Vt) Cs(sC uP uZ xA) cO(rN uT wH yL) dB(rN tQ wH yL) Aw(sK tU) Ow(fN uV) iH(tQ tT) yL(dE Vv) DbrN RbxA QyuT bNsM dMsC rBqX} xA{Vt(bL Db dE dJ hP iH jD jT Kr Kz Me Ny Qg RB rC Wm Tj tF) Id(dJ eD hP iH Ko Kz Me Qg Ss Ur) Wm(As Cs Ko Kr Mt Nm Qd rS Uc) Pd(Bg Db Jk Mf Ms Oy qA Ua) Nm(Aj Ch Ct Cw Ow wB) eD(Ax Cs Kn Kr) Db(bA Fa Kf) Ko(bR Fb Ib) Tj(Ax Pc) AjUc FbcH SrKr SsKk KfdB} Ow{fN(Ad bA bV Cp cW dL dM Fa hB Id Jl Kq Lw Ny On Qd Uc Vs) Nm(pS rN uN uX wB wF wH yE tM) uX(cV dJ Ko Lu Ss Uc Ur Uu) Ko(qI rS rT yD yE tM) Uc(pS rS yE tM) Dg(rN rS) Ny(jD qA) Ur(yE tM) IdrS TvpS VteC dJtX} Ms{Mt(Jl Jp Jr Lh Lv Lx Mp Mq Nh Nk Ns Nt Nx Oh Om On Pf Po Qd Qe) Qe(Hu Ik Jr Lh Lv Lx Nb Nh Ni Nj Nt Nx Oh Om On) On(Hq Jk Jr Lx Nh Ni Nq Nx Oy) Lx(Ik Nh Nt Nx) Nh(Jp Qd) AdAj IkJp} wB{Nm(Aj Aw Ch Ct Cw Db Hc Hu Ib Iz jO Ma Oy Qy Ua vA Vv) Db(aF Ax Cs It Kc Ko Mh Pj Qy) Ad(Aw Ch Hc Ib Iz Of Oy) Cs(dB dJ Ss Ug Ur) Uc(Ch Ct Hc) Ss(Ch Qy Ua) Ax(dB Hq) Mh(dB dE) jO(Jl Pj) HqPd KobR} Id{rS(Db iH jO Ko Kz Me Ny Or qY Rb uU Uv uY uZ vA Vv zH) vA(bR dM Fb jD jT Ko Kr Nm Pj Ri Ss) dM(sC uG uU uZ) jT(rW uN vB vV) iH(qY rB rC) bR(uU yL) uZ(Rb Ur) UvvT gPyL hPzH rCnY qYrW jOuT jRvV lKsC} Pf{Oy(As dE gP Ha Ko Lx Mt On Tv Un Vs We Wh Xa) Wb(Ap cQ Ed Kg Mg Mm) nD(Db Hf KR Pi Rg) Dr(Kg mZ nF) Yk(gP lY Tl) Wc(gP hG oH) lY(Fc Yg) nF(Vz Yl) kI(gZ jB) AdAj EqOe ThOz MgZq MkUk IiUn XaKg NxOg} Vq{Ed(aZ Dr Fc Fi Ho Lt Ps Rx Vi Wc We Yk Xa Th Yf) Oz(kE nJ Yk Xa) nT(Rt Sh Wc Yk) Rm(Wc Yk Zw) mM(aZ Gp oF) fB(nO Ri) mW(Kg Kj) ApPs YfnC WcJn ViOy eCmP eQoF nJiZ} Ko{bR(pS rN rT uT uX wH zI tM) Fb(rS sC uN uV vA wF) dM(sC uI uO uU vA yL) Jy(rS uO vA yD yL) rS(Cs Ny Rb Wm) Ib(rU rW) LwhO bNuX dBtT dEyL tNjO rBqX jRvV jTuN} Vt{vA(dE dM Fb jD jT Kq Kr Or Pj Qg rR uT tM) uT(Db dE Hq iH jO qH) jT(qH uN vB vW) dE(eZ uU zI) rB(iH sC tM) eZ(DB) zI(iH jO) vV(jR qP) NkuO IbvT jFsC} Lx{Oy(Ad Ef gP Ik Jm Me Mq Mt Nb Nx On Uc Wm) oN(Mw Ne Nk Nl Qg Qm) Hq(gP Lv Me yE) Fi(Ed Fc Mk) Wc(gP hG) bS(Mk Ne) ExcV LvNh LzHx MdJq NiQe YkgP JkOn} dB{hB(rC rO rU sC uL uO uY uZ vA vT vW wQ yL) Fa(rO rT rU sC uO) Mh(rS tU uT) yL(dM Ny Sr) Ax(rU uT) Cs(pS sC) Kf(sC vA) SrrN KqjD VseZ dMvI tVjO qYuX} mZ{Dr(bF bH bZ cV hG Jy Ma Nq oH Yd) We(bZ hG iJ Jy Kq Ld Ni Vi) Ni(Rz Vi Xa) Tl(bZ hG oV) Ma(Gh Uy) Xa(iJ oV) bZ(Gc Uy) YjoH YdLd KrVi RziJ} Qe{Mt(Ih Ii Jk My Ni Nk Ns Oy) Nh(Ih Lv Nc Ne Ni Nk Og) Th(Jy Nl Oz) Ni(Lv Nj On) Ih(Ik Nj Og) Oy(Jg Jh On) Gl(We Zq) NkNl KgVi OphB} Aj{Ad(BA cT dF fN Gp hP Hu jV Ni Oy rS Uk) gV(BA cG cP dF dM Gl) Kq(fN hP jF jM lN oN) Nm(sC vA) BaaC KlrS NyhP} On{Oy(Hu Ik Jm Lv Mb Me Mq Mt Nb Nh Ni Nj Nx Om) Ik(Ii Mk My) Wc(Ch Dp gP) Mb(Mk My) Nj(Ni Nk) ChXa EdFi NeNh HlKg} qX{Pj(bA dJ Jl Jy Kq Ny Qd Ql rW) dJ(bZ cU eZ Kq Mr rC Uh) Kq(De Hw Jk Md rB) Ny(bL Fb Tj) rB(Ad Fb) NmsC PgbL} Db{nI(cV iA Mt Oa Oz pH Ur) uT(aF Ax Cs Hc Pj Qy Wm) yL(bA cT Sr) hB(uL uY) pK(Fd Xa) OznD aCfR jTuX} Ed{Fi(Fy Ij Ir Jn Jy Lv Mt Nr Uw We Wh Xa) Wh(gP Jn Ri Ye) Wc(Ij Mt) We(Jn Ye) HuZq XagP} Cs{jT(pS rS rW uN uO uX wQ) Pj(sC vQ) dM(uU uZ) DgsC RbtU WneC UhoN bLvQ bWuZ rBzA jRvV yEuU} Wc{gL(jB lY mE mF mI nA nU) gP(Fa Ij Mt) Dp(Ij Mt) Jn(jB nA) kR(lY oQ) AaQc QbJy KrpH OmjB} gV{bA(Af aM Bn Ch CX De) cP(bB Ch cR cU Cx) Bo(aX cT dN Gd) Cx(cT cV) BacX CtcT} Ly{hX(kC kI lY mI nC nD nH nL) iB(lY nH nL) kC(hW rB rY) lYrZ nChR nDrX jQkK} yL{Sr(dE rB rS Tj) Vv(Dg Nm Pj Ss) bA(Hq Tn Tj) Kq(bL dE) Ny(bL dE) NmIb HqPd dMwL} kR{Xa(Ch iO Iv Kj lX lY Oa) We(Iv Ld Oa) Op(Ld Oa) lX(Wd Wh) lY(Rt Ry)} eC{Ld(Du Eq Op We Yl Yf) Wn(Bb bF cG Kx Oa Rf) nD(Kz Pa) FaYl} Bc{pI(Eq Fd Gc Lt Ss Ux Yj) eQ(Lt Ri Ss) Yh(dU pH) ZxpK RtOz} Ch{We(gL hB hG iZ) Xa(gL Nq oH) Ss(uT vI) Rz(dU pH) hP(Kq Ny) WhiO} jB{Rt(gL Iq) Uy(gL hB) DraD FiJm NrkI NbWe IhYh IjYk ZqKr RukC UpPh} Wm{rS(As jT Nk Rf Vv) dM(uZ wK) rB(cU Ny) KqvA gPtX jOuT} Sr{Me(rN sM tV uX) rB(iH Ny tM) rS(aW Kz) dMuU nDpF tVjO} dX{Ky(bA cP Dd Ju Jv) BaSs CqPo GdQl GpcP QbdN OeUr} nD{Fy(Jt Kg Kj Kr Oz Up) eD(hV mH) IjYk IrUp OzPi} Nm{Cw(rN uX wH) Fb(qH vA) Nk(uN uX) CtwF VveZ dMvA} nF{Cx(Zq Xa) Dr(bZ hB) Ij(Sh Yk) Yi(oQ Yk) JmRt UyhB} jO{uX(Fb Nk Ny qY) tV(dM Kr) uT(Jl Pj) TihB cGuI} lK{nR(iB Jn mT qU) Jp(kK lW nB) LvnO MvkK} vV{jR(cU Fy Mt Ny Pe Qd Un) MtfY NyrB} Kq{Aw(jF uO) fN(Ct Ib) DejE ThgW TthP} Oa{Op(hB pF) MjoV YipH RieQ VihG mMpI} nO{Lv(jE jL jP qT) Me(hV iB) eDmH} iO{Iv(We Yi Xa) Ni(We Xa) YkLd XabG} Fa{gP(Rt Rx Yk) HquU RieQ dEsC} Wn{Mw(Ct Uk Vv) Uh(Ii Vv) ApCt} uI{cG(bQ bR Rb) DgVv SsKk JyNy} Fb{dJ(tX uX) NyrB UnvA} Mh{tU(dE jT Rb Ri)} Na{iB(nC nH nL) hXkI} Ij{Yk(lY nA nT) fRgP} Kr{oW(Uw Wh) DrgZ TntN} Rm{cQ(Va Vb Ye) oKuT} sC{RbQd KfdE PgbL PjdM} Ax{HquT UhoN dEvT} Ct{AdbA BaaC UrzA} Ti{eD(Ad Jl Jy)} Fi{Fw(Mr Nr Oz)} Nk{SsuX JlfN PjwF} Qb{NiWe JyRt OphG} Jp{lW(rX rY rZ)} Ld{FckC OphB VikE} Ny{rB(cU qA) jTuN} Pe{ThOz HafN HqwQ} hX{Mx(kC kI) lYkC} uZ{UcIz RbQd aWdM} Dg{Vv(vA yD)} Uw{GliJ aIpI} pK{BgRz DiDr} FrIkOy NrgZkI LuLweZ MtIbfN NiUhmM HqPduT HrlYiB HwYepI IrRieQ YiYknT RbQdjV ZqOpoW SsKkyD JyPjrA UrgPnJ VbgLoT UycRdU PgbLwF aCbRfR bGnIpH Constrained panels with 3 analytes. where 1.0E-9 >= 'AUC p-value' > 1.0E-10. Contains 8,669 panels of 36,050,556 total panels evaluated. : Et{Kj(Ad aO Ax Bc cI Cu Cw Dc Fy Id Il Is Ji Jy Kd Ke Ko Kp Kq Kr Li Lv Mm My Nb Nd Ni No Oz Pb Pi Qa Qe Qh Ra Sr Tv Ud Wm) Kg(Ap bA dM Dp Fp Fy Id Il jD Jj Jm Kd Ke Kn Ko Kp Li Lv Lw Lx MM Mr No Nw Or Ou Oz Pe Qa Qd Ri Sr Un Us Vi Yi) Oy(Ad AO Ap As bV Co Cp Cq cT Cu Dc Dp Fy Id Jl Kd Ke Kn Kq oE Ou pF Pi qC Ra Ri Tn Tr Un Ur Us Vp Vt wP) Iz(aA Ax bA Bc Cs Ed Fa Fp Fr Hu Il Jy Kd Kq Mq Mw Nd Ni No Nw oE Ou Pe pF Qa Qe Qh Sr Ur Us Vt vV Wm) Ao(aA aC Ax bA bN dM Ed Fa Fp Fy Hu Jh Jm Jr Jy Lx Mh

Figure 1 Continued

Figure 1 Continued dE dJ iH Iz QI Ur) Ow(Kc Kp Lx On Pd Pg Po) Vt(Id Nf Ni Oa Oh uM yL) Rb(dM Kc Kq Pj Uk yL) Qd(bS cS dJ jF Ly Ua) vS(cH DI Mh Oa Rm Sr) Kp(aD fN jE rA uV) Kq(Bg Hu Ib iH jF) dE(Cu Fy Kk Mt yL) Ct(Ad Cu Jt Qe) Lw(aW Cs Kr Oa) Id(eZ Nb Uk vV) Dc(Hu iH Jk) DI(Ib Mg Vv) No(Gl Ra rX) Mh(Af Fb Nx) Pg(Bg Nq Oy) rB(Kd Rm Sr) Fa(Hc Hu) Hq(Mt Oh) Qe(Ba Mc) Ji(vV tL) Js(jU Qg) Ql(Uf yL) Uk(Ad Oa) CoLx FbqZ MrdJ UcHc IbTr IpvV JqaW KdKr KkPj PdbS rSyL} Ng{Pf(An Ap Bb cO Cp Cu Dg Di dM Ez Fy Gp Hb Ik Jh Jn Jy Kf Kn
Kp Lv Lw Me Mg Mv Mw Nb Nc Ni Nl Nt Nv oE OH Om oN Or Pa Pz Qa Qe Qm Rc Sr Uc Ul Wh) Uf(Ba Bc Dp Ef Fr Fy Id Jh Jp Jq Jy Kd
Kk Kn Ko Lh Lj Lx Mg Ml Mt Nd Ne Ni No Nr Oa Ok Om On Or Pg Qb Qc Qd Ql Ra Ul Un Us Uu Vt) Mt(Ar Bc Fr Hu Ik Ip Jq Jr Lh Lj Lv
Me Ms Mv Mw Mz Nb Nh Ns Nt Oh Om On Pc Qa Qd Tr Wm) Lx(Ba Bc Ef Fp Fr Hu Ik Jp Jq Lv Me Mz Nb Nd Nh Nj Nk Nt Nx Om On Qd
Qm Uc Un Wm) Qe(Ad Ba Fp Hu Ik Im Jp Jq Li Lu Lv Mv Mz Nb Nj Nk Nt Oh Om On Pb Qg Tr Uk Wh Wm) Kq(cI gP Ij Il Im Ji Ke Mw Nd
Ne qX uM Uo uZ vS Xa) Jg(Aj Ik Il Im Jp Jr Lh Li Lj Mp Nh Oh Qd Un yL) Ad(Ar Ba Ij Ji Jo Jp Li Mq Ok On Pe Qa wP Wn) Ji(Bg cI cT dJ
eC Kl Qg Qm Rh Ri Tn Uh yL) On(Ba Io Jr Lu Me Mq My Nb Nk Nt Nx Om Qd) Im(dE Dg Fp Ke Ko Lh Li Nh Nx Uh Wh) Ba(Id Ij Jp Ke Ok
Pe Pj Qa Un Ur) Dg(Ar Ij No qD qZ Sr tU uU Wn) Tr(Id jE Mq Oy Qa Qd qZ St Uh) Uc(Nw rO rX tV Ur vA tM) Qa(Fi Fp Ih Kc Nx Wh Wm)
Xa(Fw iO Jk Om Qd St Wh) Li(Fp gP Jp Nd Nh Nx Wm) wD(Bh dE Ez jT Kr qD Vo) Fr(Fp Hu Ik Nh Nx Wm) Ij(Ko Uh Uk Un Vq We)
Nw(gP Qt Rh Tn Tt Uu) vS(dJ Jt Ny Ss Vo Wm) No(fN Il Nh Vq wP) St(Bc Vi Wd Yi) Jp(Lj Lv Nd Nh) Tn(Pj Uh Vq) Ke(oE oN uM) Ok(Qm
Uk Ur) fN(Bb Id Jt) wB(Pj Ur Vo) Wm(Mw Qd) Fp(Nx Qd) Mz(rU zA) Nd(Jl Lh) Om(Nh Pb) Vq(Fb Jn) uT(Uu Vo) ApWn HaPe NrWh MsLh
IdoE IlPs KouP UnjK VtqZ PjqX} vS{Lj(aM bA bE bV cE Ch Cq Cu Cv Cw Dc dL jD jK Kd lM Mf Mx oE Pi Pk QX rB Rj rS Ul Up Uv Vp)
Pj(As Ax bE cG dF Fa Ha Hf hW Js jY Kn Lx Lz Mr Mx Na Nr Nx Ow Pe QD Qh Rb rX Us uT Vp wG) aW(Cq Dc Dl Fy Hv Hx Ij It Jq Kn Kr
Lw Mj Nx Ok Pi Qh qZ Ra Rb Rj Tn Ul Un Up Vp) Wm(Ad As bA Cv Dc dF jQ Js jT Lu Mj Mr nW Nx Pe Po qQ qX Rj Rm rW uI Un Vs vU)
Ke(Ao Ax Ba Bg Bo Co Dk hO Hq Hr Ib iH Mw My Nb Nv Om Oy Qt Qu Qx Ri Uh) Cs(Ad aV bE bW cG cJ cZ dR Hq iJ Kf Kp Mb Ny Qc
qP sC Us) Tr(aC aN aZ bS Co Db dJ Dl Ed Kk Lx Qd rA sM Un) Sr(Bg bN dB hR Iz jD Kc Kn Kp Mr My oE Qh) Lu(bA Cu Dc Fy Kd Kf Kk
Kn Ou Ul Us Vs) Uf(AN Ax Db hO Js Kx Oa Qd Rj uI Us) dJ(Ed hB Lh Mh Mj Mr Pe Pg Po Rm Tv) Kz(Ax bV Jt Kf Kn Kp Uc Un Ur) dB(Im
Kd Kr Mh Mt Ny Ok Ou Po) Mf(Dc Fa Fy Kd Kp Kr Pe Rm) Ad(bA Ct Ib Jh Lz nW Vv) Db(aF Kd Mt Ny Po uT wB) Nm(bA Cw Mg Nu qX
qZ) Kp(aH cH dE Dg Kr Qz) Us(Aj Aw Ct Kr Of Uk) wD(aZ Hc Nw qD rZ Ur) nW(Fr Jt Lh Pe rN Uc) Ri(Im Ny Oa Pe rX) Ou(cH Dl eD Kf
Qa) Ax(Hw Ji Kd wL) Tj(Ha Lh Lx Po) Uc(Hr Mv My qH) Tv(Aj dE Jk Uk) Qy(cG Kr Mx Un) Oa(dE jT rB wL) cH(Kr Kx Ow Pg) Ch(Kq Ok
Un) Qa(Ct Hc qD) Qh(dE jO wL) bL(Ha Nr Pf) eD(Jl Kd Vs) Fa(Hc Hu) Lx(bQ cL) Ua(Kq Qd) Ss(Kk Kn) Kr(Ny Vv) Kx(IL qD) Un(Aw De)
Ur(Of Uk) Uu(No qZ) Pe(Qc rB) cG(Bg hA) jO(Ok Vs) CtJt DlOw MdKq MtVo MxVv JluI KfcB NwvU NybV PgaZ} Im{Fi(aM Dr Fc Hv Hw
Hx Id Ij Jn Jq Jr Js Kd Kn Kq Kr Ld Lh Lx Mi Mj Ml Mr Mt Mz NA Nb Nf Ni Ny Om Pb Pe Pf Pi Pk Qt Qv Qx Qz Ra Rb Rc Rj Tv Uc Up Uw
Uz Vi Vp Vt We Wg Xa Tj) Mt(Hq Ih Il Jk Jp Jr Lh Li Lv Lw Lx Nd Nh Ni Ns Oe On Oy Pb Pf Qd Qe) Nh(Hq Ih Il Jl Jq Jr Lj Lu Lv Ne Ni Nk
Ns Og Om Ph Pf Po Qa Qd) Fp(Hq Hw Jg Jq Jt Lu Lx Ms Nd Ni Nk Ns Nt Oe Og Oh Oy Qa) Nx(Hq Il Jl Jp Jq Lh Li Lv Lw Mz Nb Og On Pb
Pc Po Qd) Wc(Ad Dp Ij Jy Mz Nb nF Ni Rb Ul Vi Vs We Xa) Lv(Il Jp Lx Mp Nd Oh On Qa Qd Qe) nA(Dc Hf Kr Ks oE Op Qu Up Yk) Qe(Ih
Jk Jq Li Ms Ni Og Pb) We(Aj Gz Kj Nd Or Ss Vb Wm) Lh(Hx Ik Ms Mz Ne Nj Nl Ok) On(Hq Lj Lx Ms My Ni Nj Nl) Kg(Dr Gn Hl Vh Tl Xa
Yf) Ye(cV Nc Qv Us Wm Yf) Ok(Hr Jl Ns Pf Qa Qd) Dr(cQ cV Gz Qy Us) Lx(Ih Mq Mz Ni Oy) Yk(Ar Mh Pf Us Wh) eP(aU bS Gp My Uh)
nJ(bR Hf Ri Ur Vq) Ms(Jp Li Mp Qa) Ji(cI Ha Si Uk) Lj(Ih Jl Nd Ni) Nw(cI gP Uk Tj) Ap(Wd Zq Tm) Yf(Ch Fa Ni) Nj(Jp Li Qd) Xa(Ii Ss Vb)
Yl(Ax Ih Wm) Uf(Aj Ct Iz) Pb(Hl Ke Qd) mM(bR Ks oE) nD(aZ Fy Qv) wP(aW Mf Ou) Dg(Lp Rz) Nd(Mp Qd) Ho(As Us) Qa(Ih Ni) Jl(Li
Mz) Jt(Gn Uw) Uk(dE Vt) kC(Db Ks) kO(Cq Dc) AjdE BaUx BbWd CtKq PoHq NcNk NlLi IkJp IzWh ZxOu TmQm KeoN OwdM UpmW
VbbA eCnF qZuM yEnW oKuT} Mz{uM(aF aJ aW Dg Dp Fa Fr iP Kc Kf lN Mf Mq Ny oE qY Sr Tz Uh yH zA) xA(Ad aJ aW bA cE cG Cs
hB Il Jf jY Nc Nm Ql Uc) wP(bN cH Id Lj Mf Ms Nk Ny Of Or uO vA Wm) Fp(Fr Lh Mm Mq Nd Ni Nk Nt Nx Oh Pc Qa) Pf(Hq Jr Lx Mc Mq
Ms Mt Ni Nj Oy Pa Qe) rO(aW bR cB Hw Jk Lw Ly Mq Nk Qc Ql) tM(aW dK Lj Ly Nk rV Sr Tr Vo vT) Nh(Fr Li Lj Lx Ms Pb Qa Qd uX)
qX(Dp Li Ms No uZ Vp Vs tL Wm) jK(Aj aQ cY eC Mp Rb Uf Uk Vv) Nd(Jg Lh Li Lx Mq Mt No Oh) Qe(Ih Lu Lv Me Nj Nl Ns Og) wD(Hw
Il jP Md Mf uY Vp zH) uX(aP cS hP Ne oK Or rU uY) wB(Hq Lj Ou vB Vv Tj) rC(Aj Co Ct hB Jf Vv) yL(bL cE Hw lM Qc Vp) uO(hB Kl lM
No Ri Uh) Qa(Hq Hw Ih Nj Oy) jD(Ar cY Kk Qg Uh) rA(Jy rU rV uT zH) Mt(Me Nj Ns Oy) yH(dF Il Ss Us) rB(Dp Rb rV Wm) qZ(Aj Je Jf
Tz) rU(AJ Jf Kk) Ch(oE zA zH) Lx(aA Mq Nj) Jy(hR jF jM) Ou(pS rN uV) eC(rN uG uU) qY(Mp zI yE) lN(Og uT tF) sC(Cs Kf Vt) Me(No
Nu) Mq(Hr Ns) Ua(wE zA) Jk(rV wE) Li(Ms Pb) tT(eD Rc) tU(dF Lj) yE(Or Wm) rW(Mg Nc) oE(Ow Rh) uL(Ib Tz) FawQ LyrS NifN NjOn
HqwH HwrV QdPb JfpS JgOy QyzA QwzH TlmZ OevV VprN PjwF hLnW iCjO jQvP} Qe{Pb(eP Hu Il Jg Jl Jp Jq Jr Lh Li Lj Lu Lv Lx Me
Mq Mr Nb Ne Nj Nk Nl Nx Og Oh Om On Pd Qa) Ih(Ct Hu Il Jg Jl Jq Jr Lh Li Lj Lw Lx Me Mq Nb Nl Nt Nu Nx Oh Om On Oy Pf Uk) Nh(Fr
Hq Jl Jp Jq Lh Li Lu Lx Me Mq Mt Nl Ns Nx Om On Oy Pf) Ni(Hq Hr Il Jl Jp Jq Lh Li Nc Nl Nx Og Oh Om Oy Pc Pf) Ms(aA Hq Jg Jp Jq Lw
Me Mm Mp Nk Nu Pc Pf Po Vt Wm) Oy(Fp Hu Ik Jp Lh Li Lu Lv Lx Mv Nb Nj Nt Nx Om Pf) Og(Fp Hu Ik Jg Li Lu Mt Nj Nk Nt Nx Om On
Pf) Fp(Hq Jq Lv Lw Mm Ne Nk Nx Om Pc Qb) Mt(Hq Jl Jq Lh Lv Me Mq Nc Oc Qb) Ii(Kn Lh Li Lx Nt Nx Om On Vt Ti) Nj(Li Lu Lx Nb Nc
Nk Nx On Pf) Lv(Hq Il Io Jq Li Lj Lx) Jk(Jg Li Lx Nt Nx Om Pf) Nd(Jn Lw Mr Op Pe) Ok(Jq My Ns Oe Pa) Th(Mh Ne No Uk) Hr(Jq Lh Me
Qa) Ye(Gl Mm Ul We) qZ(bL Fb Qy wQ) Xa(Dl Gl Kg) On(Hq My Nq) eP(Al Kz Me) Aj(Ad Wh) Fi(cQ Ed) Ne(Nk Nl) Kg(Wc Ti) Nw(cI gP)
nD(Kr Up) CtcT NooN NqLi NsJl LuLj MdJq MyJg NcNk NlOp IvWc NxPf dEyL qDrX nWuT} Qa{Ih(Hq Hu Hw Ik Jg Jl Jq Lh Li Lj Lu Lx
Me Nb Ne Nj Nk Nt Nx Og Oh Oy Pf Uk Wc Ye) Pb(Fd Hu Hw Jg Jl Jp Jq Lh Li Lj Lu Lv Lx Mb Nb Nj Nt Nx Om On Pd) Ni(Fi Fp Hq Hw It
Jg Jp Li Lj Lv Lx Mt Nc Nd Nh Nx On Pf Wc We) Fp(Fr Hq It Jg Jq Lv Lw Lx Nd Ne Nh Nk Nx Oh Om Oy Qb) Ms(Hq Jp Li Lx Mp Nb Ne
Nk Nt Oh Om Pf Vt Wm Th) Nd(Jq Lj Mm Mq Mr Ne Nk Og Oh Om Pc Qb Yc) Nh(It Jp Li Lv Lx Nc Ne Nk Og On Oy Pf) Fi(aZ Iq Iv Kg nF
Pa Qt Qv Qz Ul Wm) Mt(Hq Ii Jk Lj Lv My Nk Nq Ns Oy) Ok(Io It Mc Mq My Nk Ns Oe Og) Th(Fa Kz Me Mh Nc No Oy Pa) eP(bR Ed Ex Ik
Of Qz Vq) Lv(Hq Li Lj Lx Oy Qb) Ke(gP Ii oN We Zq Ye) Rt(bR Dp Mm Nc Oz Pa) Ii(Nx On Uh Wh) We(Aj Nl Oy Qz) Kg(Dr Uz Vh Wg)
gP(Ji Nw Uh Uk) Ye(bH bR Kr) On(Hx Mb Oy) qZ(bS Fb Gl) oE(nD Vi Yi) Lx(Hr Nj) Mm(Dr Ps) Nc(Nk Yi) Hu(Jk Oy) Wh(Jt Oz) Qg(Ct Uk)
bR(Si Wc) cI(Ne Nw) DbnI HrNx IlSf HfnD ZwKr JtUz RieQ OppF VbbH PjqX wPjO qDrS} Nw{Mr(Hq Mh Mw My Nb Nv Ny Pg Po wQ)
Jl(Hq Hr Hx Jk Mw Nb Nk Nv Of Po) Lh(Hq Jk Mw Nb Nv Nx Ny Of Pg Po) Oz(aC aN bA bV dM Kp Oa oN Uk Tj) Ms(Aj bR dE Dp oN rW
Un Ur Vt) Pf(aN bL Co Ct dM Ha Iz Uk Tj) Pb(aN Ax dN Ed Id Kc Kp Sr) sK(hP Hw Mf On Qg sC Tj tF) Pe(Hq Mh Nb Ny Pa Pg Po) wQ(Ad
bA cT gP Kk Nk Tv) jD(Jy Ko Ra Uc Ur wD Wm) rS(Ad cO Cs Je Ki Nk Nm) uT(Co Dk Hc Jd Nq Nv On) Of(Hw Jo Jq Nb Nt Ok) oE(Bc Ct
Kd Me Mt Uk) Wm(gP jK My Nv wP) Tj(bA Ed Il lO Lx) wB(Ba Hc Je My Nq) qX(Fb Id Js rO sC) Nv(Ed Fr Jq On) wP(Gl No qY Uu) wD(jP
Md qH qT) qZ(Je Ou Ow Ua) rU(Ch fN Kk Vv) rO(Ar Kz My Nq) oN(dF Jy Li Rh) Mw(Fr Ok On) Uc(jM sC uM) Lj(wL tM tL) gP(Li Mh Uk)
rB(Dp Ef Jy) jK(Ba Je Qy) Ax(wH wL) Ed(dM Ne) No(fN nW) Mu(On Pc) Hq(Jq Mi) Hw(Hx Ny) Ii(bA Sr) Il(cI Iz) Js(Jr lN) Ul(sC Uk)
aA(Lw Mq) tU(jF uY) jM(Id Us) xA(bW Oa) vT(fN sM) FrMv FweD MdvH NedM JkOn JoNx JpjO JqPg JylM KevW KkuO KqjF KzuU UfzA
VuhO OybA aNrV aVvV aWuV aYhA tFrX hVnW jRvP} wD{qD(Aw Bg cP eF Iz Jd Jk Kz Mh My Nm Ny Of Oy qH rB Ri rW rZ) dE(Ax bS
cO Fa Iu Ji jT lK Ly Mh Mr Nx Oa Ow pY qX rX) Ri(aP Cs dN jF Kp Kz Mh Mu Mv Nd Nq Ny oK qH Ur vV) bL(aW Cs Kr Lx Mh Nm Ou

Figure 1 Continued

Ow pY Qh qZ rW rX) Db(bP Fb jY Md Mh Rc uT wC wF wP tF) Hq(Dp Fy Ji Ke Kn Pd Pg qZ Uf uM Vs) dB(jE Kn Qg rN rR rY Ua wF wP
tL) uM(bS iA Mm Nx Ou Ow pY rR rZ wC) Ko(Hr li jD jM jT Md Me Mk uZ) De(Ad As Bb Ji Kq Nm Qh uZ) Pj(AW Bo Ic Iz rB Ur) uZ(aW
aZ Id Qu Qy Rb) Tj(Ax Ip Kr Qh Ql) Ke(cO Me Nb Nv Qu) bR(Ad Bg bH Co dl) Nm(Fb qH Ub vA) Ny(Hc Jk Ly rB) Ur(Ct Hr Kz Ub) iH(Kp
rR wF tL) jO(Fa Mh Mj qZ) Lu(oE Qn rS) Mf(bN dC Rb) Nk(Nc Ss Uu) Tn(An Kq Mt) Ip(Nd qH Qy) Ji(jD Me rB) Ou(cP jT Us) cO(Fb Pd rC)
dJ(cU Kk tF) Bb(Nq Qy) Md(Kp Uc) To(lu Ni) Tr(bQ Tt) Ss(Ct My) Ra(rB vA) Jk(Ad Ql) jT(Mh Oa) CsjM FbQy MeUf MtcC HrUs RbKy QhOy QgJs KruY OwcP VtrB aKcY aZrC eDqB tFqZ zHjF} qZ{Ko(aD aH Aj bQ bR cU hL Il Iz jF Ji Kg lK qA qX rA Sr) Bb(aH aL Cs Ct dE Ib iH Iz Nq Of Oy Rb Tt Ua) Hc(Ax fP Iu Ke Kq Kr Li lK Mg Sr Ss Ur Vo) dE(aD fP hL Hq Ke Ki Or Ou qB Ua) Hu(Bc Ke Kr Rb Ss Un Vo Wm) Uf(aI Dk Id Kz Mv Nn Ql Ua) Aj(Db dJ Iu Kr No Pj Ur) Ch(eD Ez Fb Mg Pd Ql Ur) Dl(aG aW aZ Ct Hr Nj Ra) fP(Ar Jl Mf Qd Rb rC Uu) uM(aW Dp Ji Kc Ss Uc vB) Bc(aH bL jF Kr Kz Mf) Lj(Co Ke Ql sC wH wL) oN(Ad Ar Cs Ke Oa Pg) Fb(aG bQ cH Ji Qd) Hq(bW Db Kq Kr qA) aL(bW Dg iH Ke Kq) aW(eD Ji Ny Ou Ow) bL(Db Nr Pc Pg qA) Ad(aZ Ef Nv rA) Qd(cO Ou Ow uO) Vt(Hr Hw Jo Tj) Ax(bS Hw sC) Wm(cC Nm Or) Lu(dL Ib oE) Sr(Kr Oy rB) Pd(bQ cL Qy) Pj(bW rB yL) iH(Hf Ji qB) qA(cO nW qD) sO(Ji Ke Uh) Ar(Gl jF) Ct(Jt Ss) Db(jD Mi) No(Ib Ld) Id(rB Vp) Jk(Ss Uu) Of(Tv Ur) Ou(cC cH) CssC TjyL GlKe NmQl LxaZ MfxA MhwH MmuY TrrQ IhRb OrbW OwcH UnaH UraD UuOy aGlK eDrS yKjF jOuX} Lx{Oy(aA bA bS cA Cp cT Cu cV Cw Dc dE Hu Id Ij Jg Jh Jn Jo Jr Jt Kp Li Lv Lw Mi Mr Ms Mw Nh Nu oE Oh oN Pc Pe Qm Tn Tr) Pb(aA Ik Jl Jn Jq Lh Lv Me Mr Mt Nb Ni Nj Nt Nx Om On Pc Pe Pf Qd) Nd(Hq Jg Jq Jt Lh Li Lj Me Mh Mi Mp Mr Mu Nh Ni Oh Om Pe Pf) Ms(aA Hq Jn Jp Jq Jr Lh Li Lv Mp Mq Ni Nj Nk Oh Om Qd) Fp(Jg Jl Jq Lh Lu Lw Me Mh Mm Mq My Pc Pg Qd) Mq(Hq Jq Lv Me Mt Nh Ni Nj Ns On) Nh(Jl Jp Me Nc Ne Ni Nk Ns Qd) oN(Bc Gp Ke Lj Oa oE Pf Wm) Lv(aA Jp Jq Lj Me Ni On) Ok(aA Hr Lu Md Me Ns Pa) My(bS Lz Mk Mt On Wm) Hq(aA dE Jl oE uM vT) Tj(gP hO Qm Vt) Mt(Jq Lj Me Nj) qD(aZ bL bQ hA) Ni(aA Lj Nj) Jl(Hw Jq Nj) Nx(aA Me Og) nW(rQ rS tU) Co(bS dE) Yk(iO Kg) Wc(Dp Th) qX(dJ Pj) ApXa DkIv EdYf FiSt GlWb MeJq MkdE NjNk TruI LjgP OfOn OwoE cOfN dBvV rSyL} Pf{Pb(aA Aj aN bL cA Ch Ct dE dM Ha Hu Jg Jp Jq Jr Jt Kd Kn Ko Kq Lh Lu Lw Me Mq Ms Nb Nc Ni Nv On Pj Uk Un Wb Tj) Oy(Ad aN bA bL bR cQ dJ dM Jr Jy Kn Kq Lh Mv Nd Nh Nj Nx oH Om Or Sr Tn Uc Ul Ur Us Vt Wm) Nd(bL dE Jg Jn Jq Jr Js Lv Mm Mq Mr Mu Mw Nk No Nv Nx Oh Om Pc Qd Uk) Nb(Fp Jp Jr Lh Lj Lv Ms Mt Nb Ne Ni Nk Nx On) Mt(Aj Ct Hq Jr Me My Ni Nk Ns Pa) Ct(Bc dE dJ Ji Jl Jp Kq Ni) Ok(Hq Lu Me Mq My Nj Ns Og) nD(aZ bR cJ Dp Ed Fc Qm Tl) dE(Aj Ji Jo oE oN Pa uI) Fp(Hq Jq Ms Ni Nx Rt) oN(Dr Gh Nk Uh Vt Wc) Wb(Gl Ih Qz Uf) Wc(Dp Iv Jn lY) Vt(Ha Ii nW Uk) eP(Gp Jl St Ul) Aj(bR cM dJ) Ch(Ha oH Xa) Dr(Ed nJ Rt) Db(uI xA) Fi(Ed Iv) Ms(Jr Nx) Ni(Nj Wf) Ii(Ke Kn) Xa(Ap Co) Tl(mM nT) dJ(qX xA) HaOa MdJq MmPs NjNk IzKq ZqKg JiUk KeoE OufN bLdM rNnW} oE{Ke(aF Aj Aw Co Cp Dk Ex Gl Hq Ib Iz Mh Mk My No Nv Oa Oy Pb) nD(aZ bI bR cI Fy iJ Il kC kI Lj Oa Pa Qb Rh) Ow(Ar Dc Kd Ko Lj Oa Oh Pe Qd Sr St Uh) mM(Fy Ir Ji Kk Li Lj nI Nk Oa Qd Qu Sr) nI(aF aO aS Gp Kr Lj Ms Qw Ri Ur Vt) Ji(Bg cI Lj My Nh Nk Ou uY Vt Wm) Op(Ir Jm kR Li Ml No Po Qx Uh Uy) Id(Aj Ch dE Lu Pb rB To uZ) Vt(Aj Ct dD De Jy Ri uM Ur) No(Aj bV Ct De Iz Nk uY) kC(bI Kr Ni Nl Qu Ri) kR(Hl Rt Uz Vi Wg Wh) Ch(Kn Kq Qh Sr St) Aj(Bc Ko Kq Wh) Un(Hc Lu Ne Ou) Uw(Bg Ss Yd Yg) Th(Lj Sr St) Hl(bH Gl Rt) bG(kI nA Uy) nW(sM vO wH) Ct(Bc Ko) Lu(Kd Kk) Tr(uN wH) Yh(aS Ub) St(Rz Ye) DgXa DrcI WmRf YfGp GlZw NiUy NkKd TonJ IhLj YdaF RbkI SsWd WhiO JnVi KlUx LirB OaPj hOyL} Fp{Ni(aA Fr Jl Jq Jt Lh Li Lv Mm Mp Mw Nh Nt Nx Oh Om Pb Qd) Jq(aA Fr Hq Hr It Jg Jl Lh Lv Mm Nd Nt Nx Oh Qd) Ms(Fr Jg Jn Jt Li Lv Lw Mw Nt Nv Oh Pb Pz) Nk(Jg Jp Lh Lv Mm Nl Nt Nx Om Pb Qd) Oy(Il Jh Lh Li Mu Mv Nt Nv Nx Oh Qd) Nd(Lh Mm Mp Mu No Nv Oh Om Qd We) Hq(Jg Jl Lh Li Mu Mw Nv Oh Po Qd) Pb(Jo Lw Mi Mp Mq Mr Pc Pe Pg Po) Jg(Hu Lv Lw Me Mw Ns Og Oi Qd) Om(aA Jl Lv Md My Ns Og Qd Wc) Fr(aA Jk Jp Lv Me My Nj Ns) Nh(Jt Lv Lw Mp Nx Oh Pc) Jl(aA Ih Jk Lv Lw Og Oh) Lh(aA Hx Ii Jp Lv) Oh(aA Lv Lw Nb Nx) Ns(Il Li Mm Nv) Qd(Lu Lv Lw) St(Du Yk Th) Wc(Uw We Wh) Jp(Lu Mm Mq) Mt(Mq Mr) Il(Hr Va) Nx(Lw Og) dE(Ji No) nW(zA yE) NtOe MmUw UfrB ViVq PcaA} No{Th(Aj Co cS Fa Ii Jk Kc Kz Lv Mh Mm Ne Nj Ou St Tj) oN(aI Aj cK dD Ji jK Ml Mt Ni Nj Qg Qv rS Ur Tj) Nd(Jq Jr Lh Mi Mm Mt Mu Mw Nb Nh Nn Nx Oh Pa) cC(aN Gl Jk Lj My nF Nj Nk Nr Nv Ou Ss) uY(bL cO hP Hu Ib Kr Nl Nn Nv uM) nW(Ar bL bS Hb hR Ne Nk Pg Uh) rB(Bg cU Fb Ha Jf Jy Tj) gP(Fw Ld Li Mt Uv Wc) fN(Aj cO Ct jO Vv) wQ(Aw cS Ne Or Vp) hO(Ch Nn Tz Ut) wP(Aw Ba vA xA) uZ(Co Hc Jf Vu) Ke(rS sC vW) Oy(Tn Wm Tj) Pb(Ik Ne Nl) eP(aW Ou Vq) qD(jU Ra rX) uO(Ha Kp Nl) Ed(Fi yL) Md(Jq uV) Ms(Ik Mt) Ii(bS Vt) Il(Fi Sf) Uf(vA vW) Pj(uM vT) cS(rS rW) wB(cO Nq) qX(Aj Dp) rU(Ct Hw) oH(Ch Wm) uW(bR dM) HajV NmqH NjNk UbuI YkjB JfrC WcWh JyrA dJpF hRiH hVsC jQvV uMvB} Lj{On(gP Ha Hq Hw Ih Ik Io Lu Lv Me Mq Mt My Nj Nk Nq Ns Og Ok Pa) Mt(Fr Jl Jq Lh Lu Lw Me Mq Nh Nk Ns Nx Om) rS(dE eD Fb fY Hq Id iO jR kR Pj zH Tj) Lv(aA Ik Jg Jp Mm Mw Nh Ni Nx Oh Pb) wB(bL gP Ha hP iH Ip Kr nW Qg Rb Ri) wP(bL cJ cS dJ fY gP Ip qD Uu) Nh(Jg Jl Lh Mu Ni Nx Om Qd) uT(bL cC gP jD jO Pj Qg) Nd(Lh Mp Mu Mw Nv Om) Ni(Nc Nl Nx Om Zq) gP(Kq pS tV zl yE) Jp(Ik Ms Ne Pb) Ok(Fr Hr Jl Jq) Pj(qX tU vQ xA) Ji(Ha nW Tj) cC(rR zH tM) As(rR tL) Ed(eP Wh) Qd(Pb qD) Jg(Oy Pb) Ke(pY wL) tU(Hq rB) wH(Kc nY) jT(rT tN) xA(Ss Vt) pS(nW Ri) AdAj FrIk HaKq NmvA MsOm XakR JyqX KruZ OphB UnqD bRfR dBrO dCwL dEvP dJtX dMsC tMnW rTnY} Ji{uM(lL Mh Nm Oe Ou Ow Qh Qx sC Ur) Wm(bN Jo lN Lv Md Ml Ny qB rS) eP(aP cS dL Ip Lz Ml Ow Pa Pe) eZ(aZ Bg bQ Ch Hu Mu My Ua) uY(Ba bN Ib Iz Jd Mu Of Om) Ne(aC bA dM eC nW oN Th) jP(hP Jp Og qD qY wP xA) lN(cB Ik Nj Nt Ql Tj tF) gP(aW Cs Ed Mh My Rh) Ax(dH eD oN Pb Tj) Ii(bR Ed Id Qm Uh) Uk(Ib Jm Oy Pb qX) dM(Pb sC uI vA yL) Ms(Ha Kj nW Ow) yL(De Ed Gl Rb) Cs(Ha rS Tj) Ow(eC qX rB) wP(Ou Qy Rb) rC(iH Jf Kg) qY(Hr Md yD) jO(Jl Na Uf) sC(aW Kp rW) vV(qD qP rB) Aj(Ad Dg) Nm(hO vA) Tr(Oy uI) Li(hP oN) cI(dJ Jo) eC(Ch Gl) rS(aW Uf) uT(oK Qy) ArOy AwuL EdFi GpPb HaOa NbWc HqwH IdqX KkqD OuuV UrhO aLjK cBrO cOzA dEfN dRjF eDxA nWvO} Ke{qA(aZ bL cS Cw jO Kz Mc Md Mu Ne Nv Ny Qc Sr Vv tF) qD(Aj Ao AW Bg cB Co Ct Dk Id Kg Mw My Nq) rS(Cs Cw Fb fN iH jP Kz oK Pk Ss uM) uV(aW Cw eD Io Jn Ko Ms rB sO Vv) sC(Bo cP Fb hO Kr qO Qu rO) oN(Dk dN Mh Oa Qm qV Rh Vt) uM(Je Of Ow Oy Ri uN vV) fN(Dc Jd Nb Qu Rh vV) hL(AW aZ cB Ms Vv) wP(eF jP Ms sO Wm) pY(aW Id jE jU Mu) vA(dM Fb Qu Ra) vV(aK Jp Ko Tn) eF(jF jM qX) sO(dM Fb Qt) uO(Ko Mf Mh) uY(Ao My Qt) Ny(jM qX) cP(Ba cP) yD(cO Vv) rP(aG Aw) MfvW MhwL HwyL TtgW IlOy LiwQ PcqX aWjD dJuN tFlN iAjE iHjR jMrW} nW{wP(aM aP bV cH Cp Cq Cu Cw hW jY Kr Ni Nr Nv Nx On Qb Qh Rj rN sK Ud uT Vp Vv) wB(aJ bW hC iA Ib It Kp Kq Mx Oa Pd vV) uT(aD aJ Ax bW Db Ny Oa sM vV yD) uN(bC dG Fb Kp qD tV Un) tU(Ax dF dG Oa Pe Wm) yD(bA dG Fy Kd Kr Vs) zA(aA aD An hW Kd Vv) sM(Bc cG dH Kp Kr) rN(bW DB dN Sr) Qd(jR qD uM tM) yL(aA dG Lw Mx) vO(bV dN hC Sr) vV(aP bV dN Un) Ko(rS tX wH) Vt(eC Gp Rh) hL(Jl Kq Ny) yE(Ad Kp Oa) tM(Bc Mq Ny) uG(Fb Mq Mw) Cs(tV vW) Un(rC rS) pS(Ad Kp) uM(Uf Vs) JgrZ SrvH KqjE PjqX aAwH bAuP eDtX hBrQ} Mt{Pb(Ip Jl Jp Jq Jr Lh Lv Me Mq Nb Nd Nh Nt Nx Oh Om On Pd Pe Po Wc) Ms(Aj Fr Jg Jn Jq Jt Lw Me Mm Mr Mu Nb Nd Ni Nn Pc Pe) Nd(Jg Jq Jr Li Me Mi Mq Mr Mw Ne Ns Oh Om Pe Po Qd) Oy(Jp Jq Li Me Nb Nx Om Pd Po Qd) Ni(Jp Li Nj On Qd) Nh(Jp Li Ne Qd) Ok(Hr Jq Jr Lu) On(Ii Jk My Nq) Ns(Li Me Qd) Nq(Li Qd) Lv(Jp Li) Pj(qX sC) vV(aV qP) AdAj ChdM DrmZ PoHq FiFw MdJq NjNk IduU XaKg} Ok{Oy(aA Fr Jg Jq Lh Lu Mh Mr Mu Oh Om Pc Po Qd) Jl(Jo Jt Lv Me Nh Ni Nj Nq Ns) Jq(Ik Jt Mb Md Mq Nh Ni Nj) Li(Hq Io Me My Nq Ns Og) Lu(Jr Me My Ns Og Oh) Ii(Fr Mr Mu Pc Pe Qd) Jo(aA Fr Lh On Pe Qd) Nj(aA Lh Og Oh Qd) Aj(Jg Ms Oz Pa) Kg(Hl Yi Xa Th) Fr(Ms Nh Pb) Mh(Hq Hw Ni) Jt(Lh On Qd) Ns(Jr Nb) Me(Jr Oh) Ms(Nn On) My(Ik Nb) Nk(Nc Nl) Hr(Ik Lh) PoHq FbqH NqQd NhaA NiOh JmOg PaPe} wP{Ko(cO Cs Cw dB eF Id iH Nk Ny Qy vW xA) Ad(Ch Cp Ct Jh Jk Nk Oy qH) Vt(DB dE Hr iH RB vT) Pg(aZ bL Db dE Hq oK) dB(aF cH Dc Mh Mr Pe) jO(Kf Kk Nx

Figure 1 Continued

Oh Pj Qy) Id(hG hP Hw Nh Tj) Tr(Jk Ma Ow ul Uk) Db(Ar lq Kn Qh) Ou(Ax cH Iu Uu) eD(Ax Js Kn Qh) Cs(Pj uM Ur) Wm(Js Ny Qh) dE(Mh Oa Sr) Cw(Jt Kf) Ny(Ch Rb) Ow(Ur Vo) AjNm AroK AxHq MhRf SrrB QhJk JoKr VvPj PecO dJqX} St{Ye(bL Il Kg Lv Mq Oa Oh Ow Pb Rb Sh Va) Yk(Aj iO Jt mZ Nc nF Nl Oz Uk) nD(bJ Db Dp eC Ed Kf Kj Oe Oy) Rt(Ad As Bn Cq Cu Cw Dc) Dr(Dl Ji mZ Nd Nj Wc) eP(Cv Hb Lz Nq Nx) Wc(Ex hG Jy mZ) Aj(Vi We Xa) Dl(Uz Vi Wg) Nd(Eq Op Tl) Ch(Vi Wh) Ed(Fi Th) Nj(Yl Tl) Yh(hF kR) Jy(Eq Th) Op(Nc Nl) ApWd BnmW BoTi DgXa MmVa SfmZ ShQz RzhG OujB VbcQ VqmS dEqD} uM{Uf(aF As cO Cq Cu Hv Jn Jr Js Mj Oa Sr Ud Un Ur Us) Vt(bW Ib iH Me Mm Ny Ow RB vA xA) Wm(aF cT dD hB Ip Mq Ou tX uT wB) Ny(Ax bA Dp Hc Kc Kf Ou) Id(Cv Jl Mx Nb Qh Rj) Ko(bW Rb Sr uX wF) Kf(Aj bW Ib Ow) Kq(Aj Hc Ou) bW(Dc Kr Nr) Lw(aW rC) Mm(bA Kn) Sr(Kc rB) Pg(bL Co) dE(Fa Kp) AdIb AxNi DpQh NmqX MfbA MxaF NkJl UcOf QgPe OuUn} qD{Un(bN cB cO Ib jD Jo Ny Ql Rb Ua Wm) Qd(Ct Id Iz jF Kr Ly Me Ny Rh Ua) Ch(Id Ih Kn Nm Pg Pj Uc Uf) Ny(aZ Ct Je Kd Oy Qy Sr Ua) Id(Aj cY Ib Ko Lw Nk Ra) Kq(Aj Aw aZ Bg Hq Iz Mv) Kd(aZ bL Ct Kz Oy) Db(Lw qX tV yL) Jl(bN My Ow Oy) Vt(Dp Kk Mc Wm) Lw(aW Hc Me) qX(Ko Pj Wm) Aj(Ko Uc) Kn(Kz Wm) Pe(Ct Of) CuaZ MhtU SrKz JydB} On{Nh(Hq Hu Ii Jk Jr Li Lv Md Mk Mq My Nc Ni Nk Ns Og) Pb(Li Mb Me Mq Nb Ne Ni Nj Nl Nq Ns) My(Ii Li Lv Me Mq Ms Nb Ni Nj) Ms(Io Lv Me Mq Nk Ns Oh) Oy(Hr Jg Lu Md Oh Po Wm) cP(Al cP Kf Pa Ph Vq) Ii(Li Lv Nj Nq Nx) Wc(Gl jB Nc Nd) Hq(Ik Mb Nj) Jk(Ik Lv Nj) Dr(Kg mZ) Ni(Nc Nl) ChoN GlTl NqMq MeHr NdOe IkOg} qX{Pj(aU bF cZ dR Ed Fb Fy Lv Lz Mh Ms Nk Pg rB sC Sr Uc Uk Ur Vt Wm) dJ(bF cE cG dF Fb Jy Lz Mh Mj Qh qY rR vV wB zH) Ny(Aj Ct dE hP Id Ql Rb Uk Wm) Kq(bL Nv Oy Qy Ua Tj) Vt(Hr jT kS rB sC) Li(fP Ql Ue) Fb(fY qP) Nm(Ct rW) Ql(Ko Uf) rB(Bb Kp) TjPg UcOy IdsC} Nd{Fr(Hu Jl Jq Js Lv Me Mm Mp Mr Ms Na Ni Ns Og Po Qb Qd) Jp(aA Jq Jr Lw Mh Mi Mm Mr Ni Nk Ns Om Pa Pc Pe) Lh(Hr Jl Li Lv Mm Ms Mw Oh Oy Pb) Jl(Lv Nb Nc Nk Og Oy Pb) Qd(Jg Li Lv Mp Pb) Li(Jq Mp Ms Mw) Ed(We Zq) Mp(Ij Mw) Jg(My Oh) LvOh MsOm XaPb RzOz} eP{Sr(aA bL Ij Kp Mn Of Qc) Ow(bE bL Hb Mv Qb Tz Ud) Ed(Ij Ir Lz Ml Oz Pb) Gp(aF Dd Fa Uu) Qb(Db Kz Ni Wm) Jl(Ii Ms Nj Pe) cP(Cv Em Mg Pj) Mq(Cv Em Ky) Qc(Cv Dd Me) Ql(aU De Kx) Pe(Al cS Us) dF(aO Db dJ) Kq(Oz Pb) BaaM NqUv LvIl McJn KycF LhdM RmVq bLcG cTdL} Tr{Oy(Jh Jl Po pS uX yD) uI(bA cE dH Fr tT uX) uN(Aw Jo Mf Nq Uk wB) Hq(tN wB yL zI) vV(aK cZ Ma Rb) Jk(pS uV wB) yD(Iz Nc uT) yL(Mx Nk Ua) uX(Aj Cw Jo) Ef(uV wB) Nq(uT wH) Mg(rY tV) Tt(qB rS) Ow(yH zI) tN(Kr Nk) MapS IzsK OfuT OuwH bRyH eDwF} Uf{rS(Aw aZ bS cL cO dE hO Ib jO Kz Ny Qy Tt Wm) qH(aM Fb Hq jD jR Rb uO wB) uI(As Bn Bo Nu Ny Ra rT Sr) vA(Ad Cu Dc dM Mj Ml Pi) wB(Ch cO Qy) Db(vI xA) sK(bN Me) vH(Aw Cw) CsuO WmrB IdvW IztU LdvV OurN cOrW dEtQ tFrX zGjO} Il{Wc(Ex hG Jy Nb nT Oa) Oy(Fr Kq Uw Vi Vt) nD(aZ bR Ri Us Yk) Dr(Ni nJ Oa Rt) Kj(Em Gn Hl Yk) Fi(Fa Kq Mq) Sf(Ar mZ Pa) Kg(Du Em Yi) Rt(Bc Hr Me) Sh(Oz Xa) Tl(nT Vu) Ps(Al Kc) AdAj ChKq DgUw LvLi YkaZ WhOz JoYl XaPb} Pb{Vq(bV Dr Jn Tn Tv Yk Xa) Li(Ik Ms Ne Nj Nl Qd) nI(aZ bH bI Rh Up Wc) Jp(Mq Ms Nj Nt Nu) Nh(Fr Om Po) Kq(Aj Ch Ct) Mq(Nx Om) Qd(Ik Wm) Jn(Lp Op) Uw(cQ nT) DbmP EdZq FynD HaPe NuJq MsOm YimZ WcUn WhnF XakR VicQ} wB{Db(Hc Ny Oa Pe qY Vt xA) dB(Hc Jl Kr Ms Nm Oa Qy) Ur(Ch Hc Mh Oa Ou Tt) Nm(cB Cs hG Nq) Ad(Jd Mg Ua) Ax(Ha iH Ri) Hc(Jg Ny Ss) Cs(hP Qg) Wm(jO Me) Ss(Bg Iz) Qy(Dg Pj) Vt(iH Me) ChPj MhgP UcJh HqPe KrjO} xA{Pd(bL bM CH Hq Id Qd Rb Wm) Ko(DB dE Jl rS Vt) Wm(An Ny qY Up Us) Id(Kr Nm Ny Uv Tj) Cs(aK Dg Kr Tj) Vt(bN eD jK Kp) Nm(Ib Uk) DbPe MfKr NyqA dBhB} Li{Nh(Fr Jl Jp Lh Lu Nc Ne Ni Nk Ns Qd) Lv(Hq Io Lu Me Mq Ms Ni Nk Ns) Ms(Jp Nx) Vv(uP uV) fN(Jr lL) rS(Ha Ph) vC(Hw Qg) AdAj WmOy MauZ JyjM WnbX UutR cYfY} Kp{vA(jT Kr Mf Pj qA Qd Ur) uO(aZ bS dB Ko Ly Mf) sC(aH fN jF qA rA) vV(eD Ko qP) dB(fN rN) pS(Lu Uu) zA(Mc qH) vB(cH jT) ChhP RbyD dEwH dMuZ eDyL rWoK} Kq{Ch(bN cI jD jM oH oN Uo) Aj(bJ jD lO Oy) jF(cF Ct Ed Kj) jD(De Nv Ow) jE(Aw Jk Nv) jM(De Ow Uk) Tt(fN gW) AwhV CtOz DrmZ HqyL WcgP QyuO QtjO KzvA cFlO} Ed{Wh(bR Dp Fc Fy Gz Ij Nc Nr Oh Oz Qb Qz We Zq) Vq(cV eC Fb nJ nY Ur) Fi(Mr Po Rm) Jn(Fc Wd Xa) We(cQ Nb) FynD NqZq XakR UwgP} Ou{fN(bV cT Cv dG Fr Jy Kf oF) Pj(qI tU uT) Ad(pS yE) Dg(uU vH) Dl(rR uT) Vt(rR zH) rS(bC Wm) oV(Jk Oa) NmyL QdjV SstX KrtM NyqA UwpI dBrN dJyE} Id{rS(aW eC Hr jF Nb rC Ri Wm) zH(bR Hw lN rB Ur) vA(cE Qg Ra) eZ(bQ dB) iJ(qH rB) uZ(Qg Tz) NkfN RivV NyuO UvsC bRuG dEyL dMuW} Db{uT(cH Hf Kc lL Mh Oa vV yL) nI(eC Ij Mw Up) Sr(rN vI) Kf(rS uY) Oa(kC kO) bA(uW uY) hB(rB rC) BogV IjnD KnsC PerS aFtM} Ow{fN(aA cT hW Jg Lh Nx Pg Po Sr Ul) qB(bA Qh Tv Us) sC(Kf Nm Vt) Ad(pS tM) rN(dB Ss) DgtU WmrS UspS VtuV dMzH jOuX} dB{tT(Bb Kr Mf Nm Ur) rN(cH dM jT Qg qY) sC(Ax dM Kn Vt) yL(cH Jy Lw) Cs(rU zI) rT(Ax Mh) FawQ SrwH KotN cHtV hBvV} Vt{vA(cE Iq Md Nf rS) sC(dM iH Nk Qg) eC(Ms Ne Nh) uT(cO hG oK) cZ(bL qH) vV(jQ jT) NihP dEsO dMuU iHtM iOvW} Wc{Ij(cQ Nb Ni Rb Vq) Iv(bZ Hu Oh Tn) Jn(gP Gz Nb Nc) Vq(Ex Nr Oz) NrhG NbWe RmcQ OmOy gLnD} Ko{Fb(tN yJ) Mr(fN rS) Ib(rO rS) wH(dE Hq) vV(jT Jy) ChcZ CwrW MhtU OfrT bNyD bRyL dMvB jOuX oKuT} Aj{Ad(aA aJ Bc bF cS dM Lv Mq Mw Oz rB Ul) Ba(bL dE dJ) BcbF DgrS XaJy} Ms{Lh(aA Hq Ik Jr Nb Nh Ni Nt Nx) Jp(Jr Lv Ne Nt Nx) Nh(Jl Om) HaPe IkQd} Sr{rB(rN wC Wm) dJ(tT yL) dM(sC uZ) AxoN TieD NmvA HryL YkjB RtgP NyuZ WneC jRvV jTuN oKuT} nD{Fy(aZ bH Na Pa) Oz(dD eC kR) Ij(Ss Up) Yk(Nr Yi) Kr(iA Qd) MwKf RboF RiUh OapF iBlK} Ny{qA(bL bN Qc Vv) dM(uO uZ) tT(dJ eD) jD(Rb Uk) rS(Ch Wm) HqyL QyzA RmrB RivV cYjK} Nm{Kk(sC uO yD) Ct(fN tV) Fb(sC uN) Nk(yD tM) VvtT bAvA dMsC jRvV jTuN} yL{dE(As Jq Lw Ur) As(dM Pj) Vv(dJ Ur) eD(dM rS) TjVs LwdJ UcHq SsKk} Jp{Lv(Ik Nh Ni Oy) Nh(Mq Ne Ni) Ik(Ni Og Oy) rB(kC mI) NiNj} Xa{iO(cG Kf Nl Oa Yk) ApVq BgoH ChJl NikC KgkR RjhF OzcQ aOhB} mZ{Dr(hB Hc We) Yd(Kr lY) Tl(lY oH) Ld(Vi Yf) NiRy WeJl JyUy PioV} uT{Ad(Of qH) Kr(jO Tt) Pj(bR oK) ChUu CsuO WmRi MhbL RbQy KcjO} Oa{hB(Rt Vi Th) nI(jB pF) EfRt GhhF IiUn WeYe OphG kEpI} bA{Ct(bU Cu Dc Dl Ef) aC(Ar Bc) vV(Lu Tn) HquY KruO} Oz{Jn(Lp Op) Rt(Dc Jr) DrVq HaPe YinF WhnT PscQ OphG} Cs{Qg(tU vQ) sC(Ip Ri) MmuZ HqvQ RbrS iJrB zAuU} Fa{Th(kQ kR) eC(Fc Yf) TieD YkiO WekR wQjT jRvV} Fb{rS(cH Mf Wm) rB(hB sM) JtqH VouN dMzH} Fi{Ir(Kg Rt) Jm(gZ nF) ExFw NrIv QbJy RmcQ} Kr{oV(Hl Uy) BcpI IbuY QyzA UhmW VwoW jRvV} Wn{eC(Pa Qh Uh) Ct(Jg Vs) HbbW JkVs} Vq{Mw(mW Yk) nT(Oy Wd) NrRt KgVi cRdU} dM{sC(Js Kn Lu) uI(Iu Uu) WmvT MfuZ} hB{Uy(hR cE cG Ni) BcUx YinF SjkR} Ti{eD(aD Hb Jg Qv) iA(jD jM)} Nh{Fr(Jk Ne Oy) Qd(Ne Ni) LhOy} Pj{wF(bN Kk Rb) jO(tN tX) NkuV} dJ{uX(hO Nk) ArbF BaCt MhtX VvtT} Wm{AsyE QdgP RirS UhoN cErB} We{Ch(nY oF) FwYe FyKg PzKj} aC{fR(aX Ba bC cT cV)} cG{uI(dE jD oK qY) jRvV} gV{BodF CxbV aFcT aXcX bMcP} nO{Lv(jF jY qU) MeqY QcjL} nI{gZ(bG Ik Pi) RbeC UrjB} lK{nR(Js Ly mU Na) LykK} Bc{CtoH LtpK RipI jRvV} Hu{oO(Hl Op Vi) FrOy} Iv{Yi(eC kC) WhiO VcbZ} Zq{DlJn GlOr LdmM UpjB} Kn{JlrB dEsC eDlN jRvV} uX{NkUu SsKk UhjO aGjT} Mm{lN(mS nB) YeRm} Ir{HoUs RioV UpmW} Qd{ArgP QguO jTvB} Jn{KgUw RieQ VabH} Un{jD(bN Uk) HchP} Oy{FrNb LvJg TnPd} Pe{Ha(jM Uk) wQjT} Pg{TjrA HqwH bLvV} jB{DrdD YibM RvgL} Ba{AsCt SsVi} Fy{Kg(Em Vi)} Mx{nHhX nLhR} Ij{SfmM UpmW} Ip{mSlN jQvV} Yk{YinA nTpH} Tl{aYdU lYkR} Ld{eQ(kC mM)} Oh{YghG WbOp} Uw{oH(Bg Ch)} Uy{NiiA lYkR} dE{KfvA tVjO} eC{HfkI YlnF} ArbFcA DgVvuV DpJlrB ThLhgW GzYeRm LwaHeZ MhtUnY MqHrJq HoJmnF YhVupH YjcRpK SsdFul JsJyrA RubGoV

Constrained panels with 3 analytes, where 1.0E-8 >= 'AUC p-value' > 1.0E-9. Contains 14,454 panels of 36,050,556 total panels evaluated. : Et{bA(aL Aw bL cG De Ed Ef Is Jd Jg Ji Kj Kl lO Mh Mk Ml Mw No Nv Nw Of oN Ow Pg Qa Qe Qt sO Ss Tt Ua Ur Uu Vt Tj) Ow(aA aO bH dM Fp Ii Il Is Jy Kj Li Lx Mh Mk Mq Nb Ni No Oh Oi Or Ou pF Qa Qe rN uM Ur Us wP tM Wm) Co(Ax bF Cs cT Fp Hu Ji Jr Jy Kd Ke Kq Lh Mh Mi Ml Mr Mu Ne oE On Or Ou Pe Qa Qe qZ Ri St Vt Wm) Ib(Ad As Cp Cq Cu Cw Dc Hw Id Im Is Ji Jn Jr Kd Ke Kp Ml Mr Mz Na

Figure 1 Continued

Om Pi Pk Tv Un Up Us Vp Vt wD) Ur(dM Dp Fp Hc Id Is Jl Jm Jy Kd Ke Kn Li Lw Lx Me mM Mr Nd Ni Or Ou Pe Qa Qd Ra Rm Sr Tv Ul Un) Kj(aA Ap cP Cs cT dM Ed Fp Ij Jl Jm Jn Jq Jr Kn Lw Mq Mr Na NW Oh oN Or Pe Qd Ul Un Vt) Us(cI dM Ef Id Ii Jk JM Kd Ke Kq Lw Lx mM Mr Nb Nw Oh oN Or Pe Qc Qd Sr St Tv Ul Un Vt) Gl(aA aC bH bN bV dM eC Fa Id Il Is Kd Ke Kq Ks Li Lv Me Nb Ne Nw Oh pF Qe qH Qm Un Wm) aO(aJ Ax cN dF dl Fa Hu iZ Jy Kk Li Lv Mm Mr My Nd NW Or Oz Qa Qe Qh Qv Ug Wm Ti) bN(aA aN bL bV cT Jl Jq Jr Jt Li Lv Lw Lx Ne No Nw oE Or Oz pF QA Qd Sr uN Vt) qC(aG bQ Db fP Hc Hf lh Iz Js Kf Ld Mr Ms Mv Of Pe Qa Qd Ql Qy Rb Ua Uk uN wD yL) Ao(bL cT eC Id Jq Kd Ke Kq Ml Mr Mu oE On Or Ou pF Qd Ri St Un vS Vt wH Wm) Hc(Bg dM eC Fa Fp Il Is Jl Jy Lx Mq Mw Nb Ne Ni Nw Or Ou Pe Qe vV wF Wm) oN(Bc cH cU dF Fw Fy Id In Jy Kd Ke Kk Me Ml Mr Ni Nw Oh pF Po Qd Qe Rh) uM(cD dE Im IZ Lx Lz Mf Mr Ms Mt Oe Ou Pe Qd QH Rm rN rZ tQ wF wG) Kg(Ad cT Cu Cw Dc Dr Hf Ij Jl Jq Jr Jy Lh Ml Na Ni Pi Ra rN Tv Ud Yj) Ks(Ap Ax Cs Dp Fp Il Is Jm Jy Kk Kl Li Mw My Ne No Nw Oh Qa Qe Uu Vt) Qu(aA Ax bV Cs cT dM Ed Jl Jy Kq Li Lx Nb Ni No Or Ou Qa Qh Qv wD) bL(aC Ap Ed Il Jl Jo Jr Li Lv Lx Me Mm Mr Mt No Nw Oh Oz Qa Qe yL) dM(Bg bR Ed Iz Ji Jk Jq Jr Kk Kl Lv Me Ml No Nw Or pY Qa Qe Ss) Jt(aF An As Cq Cw Kn Ko Kp Kr Or Ou Pi Pk Qh Ra Tv Uc Ul Up) Wm(aC Ap Bg Dg Dk Dl Id Jd Ke Kl mM nW Qt Qv Tv Um Vt Tj) jO(aA iB jD Jq Lh Li lK Lw Lx Mc Mh Ms Mt Nw Qa Qe Ra rZ) Id(Af Bn Ch cI Cp Dg Ed gP Iz Md Mm Oi Oz Pf Qv rB Ug) Jy(aF Ap Ax Cs Dc Dk Fp Hq Kl Li Pg Ss Ua Uu Vt Vv Tj) cT(aF aH Ax Ba Bg Dg Dk Ef Iz Mh Mm My Nd Oz Pb Vt Vv) Ou(Ap Ax Cs Dg Ef Hq Jk Kl My Nj Oz Pb rN Ss uN Uu) jM(Cu Dc dF dL Fw Kd Kk Kn Kp Kq Kr Or Qh Rm Sr Un) jP(aA Dc Jj Jp Js lN Mc Ng Qd Ra rT rX Un uX wH wK) Iz(bH eC Fb Fy Ji Jm Jq Kn Lw Lx Mr Oh Qd Ri Un) Qv(aF aL Il Is Jd Jm Kl Lw Mh mM Nd Qd Qy Ss Vt) De(Fy iB jI Ke Kn oE Or Ri Sr St uT uU Vs Vt) Qa(aC Al Bg dE Dg Dl Ef Ha nW Tv Ua Vv xA Tj) Ed(Ap dE eC Fc gP Jk Lw Ni Nk nW rX Vv We) Uu(Fp Il Is Jl Mq Nb Nd Ni No Or Qd Qe Sr) oE(bG cH cP In Jo Kd Mm Mt My Op Rh To Vv) Bg(eC Hu Il Lx Mt No Nw Pe Qh uT vV wH) Dg(bV Cs Il Im Kq Li Lx Mh Nd Oh Qe Ri) Vt(Ap cI eC gP Im My Ne Ni nW Pf rB xA) Is(bR Dd Ef Ha Jd Kl Qt Tv Ua Ut Tj) Kq(Ap Aw Cq Cw Dl Ef hA Jk Kl My Nv) tT(cB eD Hq jD Kz Mf Mh Mv Mz Qy rB) uV(An Ct Jj Kk Lz Ms Mt Nk RB vV) Ax(dH gP Jq Mc Me Ri Tv Vv wL tL) Jd(Fa Im Kk Lv Mq Nb Ni No Oi uT) Ss(aA Jl Mq Nb Ni No Or Pe Qd Sr) bV(aC aF Dl Ii Jo Mh Mm Nd Ni Oz) vV(bR Ji jQ Kr Lz Me qX qZ rB rS) Cs(bQ cO dH Dl eC Mc oH Ri Tv) Ne(Ap eC iZ Ke Or Sr Ul Un Th) Jl(aF dE Dl Ef gP Jk Kl Ua Tj) mM(Bo bQ cD cV Dr Gc Gp Kc Uk) Cw(Cu Ij jl Lh Me Ml Mr Pe) Dk(Dc Fa iZ Kd Ke Ml Mr Ny) Lx(aC aF bS cG cK cO dH gP) Kl(Li Mq Nb Nd Ni No Nw Qe) Or(Hq Jk Md Mk Ni Nj Oz Tj) wD(Ct Ef hO Jj rB Ri rS tF) qH(Bc cH iH Kz Mp Uf uX wP) vS(Aw cO Fw Hq Im Mj qV Tv) Ap(Jm Ke Pe Qd Rh Ri Uf) Oa(Fi Ji Lw qZ rS sC wP) Op(kR mZ Nc Nl Oh Pb Pf) aC(Ji Mm No Nw Oz Pe Qe) eC(In Jj Ms My No Oy Vv) Ef(Lv Mq Nb No Qh Sr) Fa(Hq Ih Jk Mk Nv Tj) Tv(Fp Ir Me Mw Oz Qe) Kd(cI Jk Md Mm Nv Oz) nW(Ar Bc jl Mh Pf Uk) pF(cl Ct Hq In Mm My) Ua(Il Lv Mw Qh wH) Ii(aJ Pk Ra Ul Up) Vv(Il Im Mm No qO) cO(vO wP yL yE tM) gP(Ji Li Nw Qd Qe) rS(cB DB Ny Ra) Wc(Dr Fp Nb Ni) Ke(cI Kf Md Nv) aF(Li Mt No Nw) dE(bH Me No Pe) rB(Ql Rb uN Up) yL(Jj Mf Ml tU) Aw(hW iB tU) Db(kC nD uX) Dl(Mr Qd Sr) Tj(Cu Mr Nw) Ha(Im Li Qe) Qy(Mq uX wB) Jo(Rj Ud Vq) Kr(mS mZ xA) Um(Ad Cu Dc) Oz(St Un Wh) bR(dI uX Yd) eP(Al Ij Nr) wP(Mf Ny Of) uN(eD Mf qD) Mm(Uw Xa) Im(Sh Sj) Jk(Sr tQ) Jm(An Ug) Kz(rT sM) Ul(Of Ug) aW(jI rW) eF(tX wB) hA(cG dA) qZ(bQ Ql) xA(jY Pd) lN(Js Ng) vP(jQ jR) AjWh AlQe AsnI BaUx BbNw ThMh FweD FyPb LzrT MesM MqQt MrlN MsqA MtrP MyuT MzqX NbJe HqKk HuwH TtjI HfnD QdqD StOi JjsO RynF RimS NyrW OyhB aAaH aLiB cPtU tFrX tQiH iZjD jYul} Pf{Oy(aC Aj An Bc Bn bS cA Cp Cq CT Cu Cw Dc Dp Fp Fy Id Ik In Ip Jg Jh Jn Jp Jq Kd Kp Kr Lv Ms Nb Nc Ne Nl Nt oE oN Ou Pb Pi Pk Qa Qd Qx Ra Rb Rj Up Ut Uw Vi Vp) In(aA aC aD aF Aj aM Bc bR bS cA cF cK cO Ct dH Dp Hv Hw Id Ih Ir Iz Jg Jo Jp Jt Ke Ko Kq Lh Lw Mm Mr Ms Mu Nb Nc Ni Nv Oa oE Oh Om oN Pa Pe Pj Ua Uh Wb) Ct(Ad As Ba bL bR bS cA Co Cu Cw Ha Hw Ij Im Iv Jj Jn Jr Jt Jy Ko Mk Mr Mw Na Nb Nd Nk No Ok Om On Oz Pa Qa Qe Ri Uf Ul Un Us) Pb(aC aD An bA bR bV cK CO Dr Gp Hv Hw Im Jl Jn Jo Jy Li Lj Mm Mr Mu oE Oh oN Ou Pc Pe Po Qm Qv Sr Uh Us) Ng(aA Aw bA Bo cT Dp eC Fr Gb Hu Ij Im Jl Jo Kd Li Lu Mm Mp Mq Mr Mu Nk Nu Ou Pc Pe Po Qd Rg Vq Wb Xa) Ni(Aj bL dE dJ Im Iz Jp Jq Jr Lh Lj Lv Lx Ms Nc Nd Ne Nl Nt Nx Oh Om ON Qb Qd Uk Vt Wc We Ti) Uk(aF Bc bL bS Ch Co dE dH dJ Dp Ha Hq Im Iz Ke Kn Mw My Nk Oa oN Oz Qa Qe Sr Ul Un Tj) Jj(aA aF bR bS cA cK cO dH Fr Fy Ij Ir Jo Jt Mm Mq Mr Nr nW oE Pe Po Qb Rg) Nd(aA Aj bS Ch cO dJ dM Fp Im Iz Jl Jt Lj Lw Ms Nb Nt oN Pe Po Ur Wc) Nw(aC aF Aj Ao bA bR bS cA Ch cO De dH Dk Dp Jd Kg nW Oa Qt Ua Ur) oN(aA Aj Bc dF Id Is Iz Jy Kd Kn Ko Kq Mk Mt Mw Ne On qZ Sj Un Ur) Ms(dE Hq Ik Im Jl Jn Jp Jq Js Lh Mp Mw Nb Nj No Nt Om Qd Un Vt) Mz(aA Ik Jl Jq Lh Li Lj Lu Lv Mr Nb Ne Nl Nt Nx Oh Pe Qa Qd) Nj(Fr Hq Im Jn Jp Jr Lh Lx Mp Mq Mu Nb No Nx Og On Qa Qd) Qe(bL Ha Hq Il Im Jl Jq Lh Lu Lv Me Nk Ns Nt Om On Pa Pe) Iz(Ha Im Is Ji Jl Jy Mk Mt Mw Ne oE oH Pa Qd Uf Uh Un) Jr(aA Hq Jp Lh Lj Lv Me Mq Nb Ne Nk Ns Nx On Pa Rt Wc) Ji(Aj bL bS cA Ch cI Co De dM Ib nW oE Rt Ur Us Tj) Mk(Aj bL bS cA dE dJ Ha Ke Kk On Uh Un Ur Vt Yk) Qa(bL Fi Ha Hq Hw Jk Lu Lv Mt Nk Ns Nx Og Pa Rt) dE(aA bA bR bS dM Hq Is Jk Kg Mq Ne No Oz Ur) Aj(Bc bL Dg Ha Is Jg Jp Kq Nk Pa Qg Un Xa) Lv(Hq Il Im Jp Jq Lh Lj Mq Mt Nx Oh Om Qd) Wc(Dr Im Je Kq Nb nD nT Ps Ql Qm Rb Un) Pa(bL bS cA Fp Jp Ke Lx Nx On Vt Wb) Ha(Fp Hq Id Im Is Lx Oz Pc Pe Un) Mt(Ch Co Jl Jp Jq Lh Lw Mq On Qd) Nh(Fr Jl Jq Me Mq Nc Nt Oh Om Qd) nD(bJ dB dI eC Gp Kp Kz Ou Up Zx) Oz(aN bS cA Ke Rt Un Ur Vt Wb) Ne(aC bL bS cA dM Nb Nk oE) Hq(gP Im Jp Lx Nx On uM vS) Yk(aZ Ed iO nT Ps Qb St Wb) Og(Ik Jn Lh Lw Nt Oh Om On) Is(Al bL bR bS cA Ch dJ) Nx(aA Lj Lx Me Mq Nb Ns) nW(Bc sM uG uM uN uU yH) Jo(Dr Kn Vt Wb Zq Xa) oE(bL Ch Hc mM Op To) Fp(Lw Nk Oh Pc Pe) Jk(bL Jg Kq On Vt) Jp(Ch Ik Lj My Nq) Kg(Ps Uw Vt Wh Ti) Dr(cQ cV gP kE) Im(Ih Il Lh On) Wb(bL Gz Mi Wm) vS(Db jO rB Ua) Co(Kq Ps Wh) Tj(No Un Vt) Fi(Fc Ps Ql) Lx(Me Nk Ns) My(bL On Wm) Ii(Jq Lh On) Xa(Dg Mg Qz) Ok(aA Hr Jq) Ur(Bc Un Vt) cO(fN uM uT) Ap(Ps Zq) Ed(Vc Yf) Eq(cV St) Me(Jn We) Mq(Jq Ns) Nk(Nc Nl) Tl(gP kE) Rt(Bc Qb) Op(oH St) qC(dB Ua) ChKq DbnI FcnF NqOn MmHp TvTk IlSf IvVc SjkR WemZ WhQz QhoD JlLj KroV RieQ VagP VtoH PjqX aNbS aWbL cIdJ jRvV} Ng{Qe(aA Ar bA Bb Bc bF Bg bR Cp dE dF Dg Di Fr Gp Id Jh Jl Jr Jt Jy Ke Ko Lh Lw Me Mg Mm Mq Mr Mu Ne Pc Pe Po Qm Uh Un Ur Vt We) Uh(Ar As Ax Cp Cs Cu Dl Ef Fa Fp Fr Id In Jg Jj Jl Jy Ko Lj Lx Mq Nb Ni No Nr Nw oE Ok On Pe Qa Qh Qm Qt Ra Sr Tv Un Us Wm) Lx(aA bS Cu Dg Ez Gp Id Im In Jh Jl Jr Jt Jy Kl Kp Lh Li Lu Mq Ms Mu Mv Mw Ni Oh Pb Pc Qa Qg Qt St Tr Vt Wh Xa) Qa(Bb Bc bF bR Cp dF Dg Di dM GP Hu Ik Im Jp Ko Lh Li Lu Lv Mz Nh Ni Nj Nk Nt Om On Pb Qb Qm Ue Uk Un Ur) Ad(Ap Ax bA dF Fp Fr Hu Im Jg Jl jV Ke Lh Lj Lv Mt Mw Nb No oE Oh Qd Qm rC Sr St Uk Un wD) Li(Ba Ef Fr Hu Ik Jh Jl Jq Jr Jt Lh Lj Lu Lw Lz Me Ms Mu Mv Mw Mz Nj Nt Oh Om Pb qC Qd sC) Jg(Bc Fr Hu In Jl Jn Jq Lv Me Mg Mq Mr Mw My Nb Ns Nt Om Oy Pb Pj Qb qC Qm vl Vt) Ba(aC Ax Bc Ct dE Hb Jl Jq Ko Ld Lh Lj Lv Mg Mw Nr Om Pg Qb Qc Qg Qh Qm Sr St) Mt(Aw Ax Bb Bo Cp Cu CV Dg Di Id Ij Jh Jl Jt Lw Mm Mp Mq Mr Ni Nv Pb Pc Qm) Jp(An Aw Ax Cp Cs Hu Il Im jO Jr Ko Ms Nb Nj Nt Nu Nx Om On Pb Po Qm Vq Xa) Ij(Ar bA BC Cp dE dM dN Fb Fi Id Ke Kl Kp Qm Ub Ul Vt Wh Yk) Im(Ar Bc Fr Id Ik Il Jt Lj Nd Nt Om Ow Pj Po Qd Uk Un Ur Vt Wm) Nw(Aw bA bF bR Cp dF dM Fy Gp Jy Ko Kp Qm Sr Ue Uk Ul wD) Is(Aw bB Bc bF bV dN Jy Ke Kl Kp qD Qv Rh Sr Ul Un Vt) Uf(aM An bA bR dF dJ Fa gP Jl Lw Mr oE oH Ou Tn Tr Wm) Xa(bZ Ed In Iz Jl Jn Mv My Mz No Nr Ou Pz Qu Tn Vq) Ok(bA Bo Cp dJ dM Gp Id Jy Ko Oa Qh Qt Rh Sr Un Uu) qC(Ap Bc Fb Js Kp Mm Mp Pd Pg Qh Ql Rm Ss St Ue wD) Ar(bA Bc bF cE dF dJ Ef Gp Il Jl Mw oE Qd Tr vS) Om(Dg dJ Fr Hu Ik In Jj Jr Lh Lj Ms Nd Nt Po Qd) Fp(Dg Hu Jl Jt Lh Mm Mp Mu Mv Mw Nt Nv Po Pz) Tr(Gp jK Lh Mp Mw Mz Nr Pe Qm rC Sr Uk Uo Ur) On(Bc Fr gP Id Jl Ko Lh Md Mk Mw Mz Oh Pz Ur) Un(Dg eC Gp Il Jj Ko Mw oE rC Ur vS) Ji(bF bJ bR Ef Gp Jy Ko Kp Uu zA) Kq(bA bF dE Dp Fy Mq Nj oE rC rY) Bc(Dg eC fN Ke Ko oH pF Tn Ur) Mw(Id

Figure 1 Continued

Ke Kn Ko Kp Qm Rh Tn Vt) St(Ap Dg Dr gP Ni Nk Tn Va Yj) Pe(bF bR dE Dg dJ gP qD Qg Uk) No(Ik Mz Nb Nx Pd Pg Wh Wm) Vt(eC Ef eZ Gp lN oH Tn) Pj(ln jD lN oE uT wP) qD(Ez Jl Nx Pd Qm Vo) wD(Ap dJ jO Kl Ny uM) Fr(Nb Nj Nl Nt Vq) Nh(Jl Lh Oh Po Qd) Uc(gW hV
qZ rR rU) Ke(gP Oz Pb Pz Qm) Dg(Fy Nb Qh vI) Wm(Jj Jl Nv Pg) Ez(qB qX uT wB) Id(eC Gp Il Tn) Qd(Ik In Lv Pb) Ko(jD rY Tn vV) vS(Jl
Qh Sr Us) Nt(In Lh Po) Ss(sK sO tX) Wh(Ed Fw Jn) Lj(dF Hu Nx) Vq(bZ cV Ma) fN(Kp Pg Qh) Nd(Nv Tn) Ik(Lh Oh) Il(Uw Wd) Nx(Oh Po)
Ur(vB zA) ApqZ BbrC EfJj FyUk NmvB NrdF LvLh NkTn InJt JnUw KlWn KnoE NyzA UuwP VozH} In{Im(aA aD aM Ar bC bW Cv dJ dL
dM dN Hl Hv Hw Jn Jo Jp Kn Ko Kq Lu Me Mf Mh Mi Mq Mr Mz Nc Ni Oa Og Ou Ow Pb Pc Pe Sr Uh Uk) Lj(AD aI bF Di Dp eC hB Hv Hw
Id IJ Jj Jo Jr Jy Kf Kp Lu Lw Mm Mr Nc Ni Nu Pb Pe pF Pg Qm Uc Ul Us vS wP) St(bV bW cI cT dM dN Dp Dr Hw Id Jt Kn Ko Kq Lh Li Me
Mw Na Nd Ni Nj Ou Tv Uc Uk Ul Up Us Vq Yd Yk Ti) Oa(Ba cT dN eC gP hB Id Ij Jj Jl Jt Ko Kp Li Lw Lx Mm Mt Ne Nk Nm OH On Ou Pe
qC Qd Sr Uh Us) Qd(aA aC Aj aM Ax bA Bc Ch Cs Dp Jn Jo Jp Jq Jt Kd Ke Lh Lu Lw Mm Mr Ow Pe Sr Uf Uh Us) Lx(Bc bL Co dE Dp Hv
Hw Jn Jo Jq Kq Lh Lw Mm Mr Mz Nc oE Oh oN Pb Pe Sr Uf Uh) On(aA Ax Ch Hc Hu Iz Jl Jn Jq Jr Lh Mf Mh Mk Mr Mw Mx Mz Nb Ni Of
Og Oh Pe Wm) Mt(Aj Ar Bc Fr Hv Hw Jl Jn Jo Lh Lw Mh Mm Mr Mz Ni Pb Pe Sr Wm) Nw(Ad As bR Cs Cu Cw dE dF dJ dL dN Fy Kd Ke
Ko Kq Kr Ra Up Us) Uh(Bc Bn Cp Cq Cs Cu Cw Dc Ih Jt Kd Ke Kn Li Lw Ml Mr Qb Ra Us) Nt(Fr Jg Jn Jq Jr Jt Lv Mh Mm Mq Mr Mu Na Nf
Nh Nj Oh Pc Pe) Ik(aA Ih Ir Jg Jn Jq Lw Mm Mq Mr Mw Mz Na Nb Nv Nx Pd Pe Pg) Po(bL Hw Jg Jn Jo Jq Jr Lh Lv Lw Me Mm Mr Nc Ne Ni
Nl Wm) No(Ad bA Bc Il Jn Kn Lv Mb Mf Mz Nb Ne Nl Pb Ql Sr wP Wm) Mz(aA Il Ir Jj Jn Js Mq Nj Nu Om Qb rU Sr Uf wD) Jl(dE Jj Jr Lv
Mb Me Nb Nc Ne Nl Nq Ns Pb Pj Wm) Pd(aC Ar Bc bL dE Ir Jj Js Lh Mw Nh Nu Oh Pj Qb) Sr(aM aN Ax Bc dJ Dp Il Jm Kn Kp Nd oE Ok
Uf) Li(aA aM dE Dp Hw Jn Jo Lu Mm Mr Oh Oy Pe Wn) Mw(Ax Bc Fa Iz Kd Ke Kq Nd Nu Pj Rm Uf Vq) Nh(Ij Jg Jj Jm Jr Js Jt Mp Nb Nv
Nx Oh) Jp(Jj Jr Lv Mf Mq Ms Nj Nl Nu Nx Qb Wm) Un(bA cH dJ Dp Fy Jj Mq Ne oE qC Ul) Qb(Ba Bc Jj Jt Lh Nj Om Pj Uf Wm) eC(Gn Ho
Id Is Ke Us Uw We Wg Yj) Qe(bV dM dN Fy gP Ou Qm Tv Ti) Js(Ip Jg Jj jU Nd Nj Nu Nx Om) Uf(Aj Ax Ch Ih Ij Iz Jj jO Ul) Ar(aA aC bA
dE dJ dM It oE) Pe(bA bR bW cF Co dM Pj qC) Ax(bL bN dE Ke Kq Ok Pj) Mq(Ih Ip Jg Jt Lh Om Pj) Bc(Dp Ed Id Kk Ko Rm) Is(Ke Ko Ou
qD Qm Us) Jg(Aj Jj Me Ms Nu Oy) Kq(Aj Ao Ct Dp gW Iz) Ok(bN Ct Dp Ed Iz qC) Om(Jj Jn Me Nd Og Pb) Id(bN fN Il oE Pb) Ih(dE Jn Ou
qC Wm) Lh(aA Jn Me Nj Nu) Oh(Me Nd Nj Nx Wb) Ad(Ch Ct Kj Uu) Il(Hl Ke Nu Sf) Qa(dN Fi Fy oH) Vq(bA bV cV dF) Pj(dM Fp Qh Ul)
Wm(aA Jj qD) Ms(Jt Ke Nv) Nd(Fa Jt Nv) Ji(Fy oE Qm) Rm(dJ Jj Ye) Nx(aA Jr Nu) Aj(Ij Uc) Dr(mZ Ul) Fp(aM bC) Nj(Fr Nv) Tr(gW qA)
Ke(Ch qA) Ko(gW hL) Vt(dN jK) EdNm NuJr MbJt MePg NbJn IjdE IvZq KdoE aWvS wPnW} Jj{Lj(bF dF Dp Fr Ip Jn Jq Jr Js Kq Lu Mg Mp
Nb Nc Ne Ni Nj Nl Nm Nu Nv Oh Ou Pd Pg Po Pz Qd Qm Tr Uc Uf Uh uM Un) Mw(aC Ad Hu Il Jg Jr Js Kd Kk Kn Ms Mz Nb Ne Nj Nl Nu
Oh Om Po Pz Qm Rm Tr Uf Uh Us) Dp(Ad Bc Dg dJ Fy Ij It Jg Jl Ko Kp Lh Lx Mz Nd Nm Oa oE Oh On Pb Qd St Uh Un Vt) Wm(fN Fr Fy
hP Ih It Jk Jq Kq Lv Mq Nb Nm No Nr Nv Nx Ny oE Om Pd Po Pz Qb St vS) Il(Ad Bc Fr Fy Jg Jn Js Ke Ko Kp Kq Lv Mm Nj Nm No Oa Om
Pd Pj Pz Ql Qm St Uf Uh) Jm(Cs dJ Ed Fr Hw Ij Jo Jq Jt Jy Kq Lw Mf Mg Mp Mr Nb Nc Nr oE Ou Pe Po Tr Uf Uk) Mz(Fr Ij Ir Jk Jn Jo Jq Jr
Js Jt Lu Me Mf Mg Mq Nb Nc Nm Nu Nv Qb Tr yL) Jg(Io Jn Li Lu Me Mf Mh Mq Mr Ms My Nb Nc Ne Nj Nl Nr Ns Nu Om Pe Qb Qd) Jp(Hu
Ij Io Ip Jn Jo Jq Js Jt Lh Lu Mh Mq Mr Nb Nc Ni Nr Ns Om Pd Pe Qb) oE(Ar Bb cI Dc Is kC Kk Ko Kp Kq Lx Mt Oa Ow Pe Pg Pj Qm Rf Rm
Sr Uh) Nd(Fy Ii Ip Jk Jn Jq Jr Jt Ma Mr Mu Nm Nn Nr Ny Oa Qc Tr Un Vt) Oh(Hu Ip Jn Jr Lu Me Mg Ms Nb Ni Nj Nu Nv Om Pd Pg Pz Us
Vt) Lv(Hu Ij Ir Jq Jr Mg Nb Nj Nl Nm Nr Nu Nv Om Pb Pg Qb Qc) Pb(Ad Cu Fa Id Kn Ko Mm Nr Oa Pz Qb Qh Rm Tr Uc Uh Vq) Nh(Ii Ij Js
Jt Mg Mn Mp Nk Nm Nn Nu Ny Pg Qb Qc) Oa(fN Im Ip Ji Kp Kq nW Ok Pj Qe Qm Uc Uf Uh Un) Vt(Ed Gp hP Ij Lx Ms Mt Nw Oz Qa Qh
Qm St Us uU) Po(Ip Jn Li Mm Ms Nb Ne Ni Nj Nk Nl Om Pz Qd) fN(Ad Bb Is Jl Kq Nx Qh Ql Ra Rm Tr Uf Un Vo) No(eC Ip Jn Lu Me Mf
Ms Nc Ne Nj Nl nW Th) Qd(gP Jq Jr Lh Lu Lz Me Mr Nb Ne Pc Qm Us) Jl(gP Jq Lh Lu Mb Me Mf Nb Nk Nl Nx) Kq(Ax Ch Co Ib Iz Md My
Nv Oy Oz Qt) Ik(Hw Jo Lw Mi Mj Mq Mr Ni Pc Pe) Im(aA bR dJ gP Jy Ke Mq Pj Tr Us) Uh(Ad Ax Bc Cs Fp Ms Oz Qa Rm Us) Nj(Fr Jn Jr Js
Nv Om Pd Pg Pz) Li(Fr Jq Jr Lh Mq Nb Ni Om oN) Nw(Ao Ax bA bR cI nW oN Ul Us) Nt(Fr Jn Jr Me Mp Mq Ni Qb) Lx(Fr Jo Jq Jt Mr oN
Pe) Ms(Jn Jq Nv Pg Pj Pz Un) Pz(Hu Jn Jr Js Me Nl) Qa(bR Fr Mq oN qC Qm) Qe(bA bR Id Jy nW Ou) Om(Jn Jr Md Me Nc Nl) Bc(Ko oH Qh
St Us) Fp(Ad dE dJ Uc Uf) Js(Hu Ip Me Ni Pd) Nm(uM vA vS yL) Tr(Ip It qA Rm) Is(hP nW Ou qD) Ji(bR dM nW oN) Jn(Me Pd Pg Vq)
Qm(qC Qh St Un) Nv(Me Mf Nl Oy) Ao(Fy Ok On) Mt(aA Ax Cs) Un(jD Oz Qh) Pd(Ip Jq Jr) qC(Dl Ih Rm) Aj(Ok Uc) Mm(Pg Qc) Kp(Oz St)
Ks(uV wD) Lh(aA Hx) Us(Fy Ok) Pj(qD qX) nW(uT wB) AdOy CoOn EdWh FbVq FrNl HuIp TowP JrPg KegW KorW RioT UfOz PedJ}
Im{Wc(bA bC Hl Il Is Iv Jh Ji Jq Lx Ml Mq Mr Mt Om Po Qa Qv Qw Qx St Tn Tv Un Uw Vh Vt Wd) Pb(Dr Gn Il Jl Jp Lh Li Lj Lv Lw Lx Ms
Nd Nj Nt Nu Om On Qa Uz Vi We Wg Yl Tl Xa) Fi(bA bC dF Is Ji Jy kC Lw mF Mq Nw On Ou Ow Pg Qw Rt Sr Tn Un Uv Vh Ye Tl) Lx(aA
Ik Io Jk Jl Jn Jp Lh Lj Lu Lw Me Mr Nk Nt Oe oN Pe Qa Qd Qe Yk Tj) Ms(Fr Ik Il Jl Jq Jr Ke Lj Lv Lw Nd Ni Nj Nt Nu Oh Om Po Qd Vt Yf)
On(Hu Hw Ih Ii Il Io Jk Jl Jq Jr Lh Li Lu Me Mk Mq Nq Oe Og Qa Qe) Il(Dr Eq Jp Jr Lh Li Lj Lu Nb Ni Nj Nt Og Po Qd Qe Sh Ye) Nx(aA Fr
Hw Ii Jn Lu Me Mi Mq Mr Ni Ns Nt Oe Oh Om Oy Pe) Mt(Ct Fr Ii Io Jl Lu Me Mq Mr My Mz Nk Nt Og Oh Pe Qa) Li(Hq Hw Ih Jk Jq Lh Lu
Lw Me Mz Ni Ns Oe Og Oy Qa Qd) Qe(Hq Jl Jp Lh Lu Lw Me Mr Mz Nk Ns Nt Oe Om Oy Qb) Lj(aA Fr Hq Hw Ik Jg Jp Jq Lh Lu Lw Nj Ns
Nt Oe Om) Nd(aA Jg Jq Jt Lu Lw Mm Mq Mr Mz Og Oh Om Pe Po) We(bS Ch Co cS Iz Jo Jv Kl Nl Qu Qv Qy Rc Sh) Vb(aM cT Cw dF Dr
Em Gn Hl Kd Kn Kp Kr Pi) Yf(Aa bC cS Gp Ib Me Mh Or Ow Ra Sh Yi) Nw(aC Aj aN Ao Ct dE Dk dM Iz oN Ow Ur) Qa(Hq Hw Jk Lh Lu
Nj Nk Nt Og Oy Qb) Th(Aj Ar dN Fa Kq Mp Oz St Uk Ye) Lv(Fr Hq Jl Mm Ni Om Op Po Zx) Nh(Lw Me Mm Mq Mr Mz Nc Oh Pe) vS(bE dJ
Kr Kx RB Tr Ua Uf) Ni(Dr Jp Lh Nc Ne Nj Nl Qd) Sh(aC aQ bR Jy Qv Ri Ul Us) Ji(aC Aj aN Ct Dd dE oN Ow) Fr(Ik Is Jk Nj Nl Ok Oy)
Qd(Hq Hw Ih Jk Nl Oe Og) Op(aG hG iP mF nY oH pF) Ye(bH dH Me Or Qm Ri) Lh(Hq Hr Ih Is My Oy) Ow(bW gP Ke pS Uh Uk) eP(aN Dd
Hb Hc Ny Qz) Ct(bA dE Ok Rb Xa) Ti(Aj Co Ii Kg Uk) Fp(Mm Mq Mr Mz Pe) Nj(Jr Mp Nb Nk Tm) Ho(Cq Cu Cw Dc Hl) Jp(Hq Jr Ne Nl
Nq) nJ(dI Kf Kr Rh Us) kC(bR Hf Kr oE Rh) Ch(eF Kq qC wP) Dr(aQ Nc Qv Wm) Ii(Gn Ke Un Vt) Is(aA Io Jl Mm) Yk(Ld lY Nq St) Jt(Ry
Vh Vi Tl) Rt(Aa An Kg Us) Uk(gP Ke Lw nA) Up(lX mP mT nI) mM(aZ cB Hb Ur) Aj(Jg Ok Wh) Db(nI uT wB) Iz(Kq Ok Un) Vw(Ba Bc
Cw) nA(bI bR Ri) nD(Dp Ha Us) wP(dB eD jO) Fc(Fa Gp) Nt(Ns Og) Nb(Ne Nl) Qz(Wd Wh) Jr(Hq Ih) Ke(gP Oy) Ps(Em Us) Vt(nW Ur)
aC(dM Tm) nI(bR oE) qX(Fb Pj) AnHp DcUz DgZq DlVh PoNl GpLt HaPe NodE MfrS NeNk HlIt IbXa ToeQ IkJl SjcR KgYl KlUw RhlX
OkaA OmOy VcbZ VagP bBrB nUoE wBnW} vS{Pj(Ad aN aW Ch CQ cT Cu dB Dc dD dM Ed Fy Hv Hw Jq Jy Kd Kf Kq Lh Mb Mh Mj Ml
Ou Pb Pi Qa qC qH Qy Ra rB Rj Tv Uc Un Up wB wF Wm) aW(aM An Bn Cp Cu Cw dL dM Hw Ih Ir Iv Jn Jo Jr Js Kd Kq Lh Ml Mq Mr Na
Nf Nr Ny Om Ou Pb Pe Ph Pk Qd Qx sM Ud Uf Uv Vo Vs) Lj(An aO bW cW dF Dp hB Hv HW Ij Ir Iv Jn Jq Jr Js kQ Ml Mr Na Nf Ni Pb Pe
pS qP qZ sK uX Vs) Wm(bE cT dD Fp hL Ir Jl Kd Kf kS Kx Ld Lh Lx Nr Ok Ou Ow Ph Pi Qa Ri Uc uM Ur uT wB wD wJ) Nm(Aw Ch Db Hc
Ib Iz Kx Lx Mh Nk Oa Of Qc qD QH Qy vA wD) Ny(aD Aj bA cH DE Hc Iz Jd Je Kz nW Oa rB uM Un Us) Tr(An bQ cI Dp Ez Fp Hf Ih Is iZ
jY Mk qX uN Vv tM) Ch(Ar bA Fa Fy Ij Jt Kf Kr Lh Nx Qa Qd St Tt Vo) dJ(Dc dF Fp Ha Is Kd Kf Kn Kx Lz Mx Oh Ok Uf Us) Uc(cB Db De
Hu Jd Jk Kk Lu Md Mf Nb Nk Ua Vv) dB(Ar dF Ed Ha Kc Kx Nx Ph Pi Qa Qd Uf Un wH) nW(aP Dc dF hW Kf Kn Ou Po sM Tv Uf Us Vs
wB) Pe(dE Hu iH Jd Je jO My qD Qy Rb Tn Ua Ur) Db(Cu dF Ha Jl Mh Ou Ph Pi Qa Us uX vJ) wD(Aw Bo cC Ct Iu jP Mf My Oa Qy rW tF)
Ke(bQ Ct jD jY Ma Ms Mu Mx Nq uV Vv) Kx(Ad bS bV Dc dE Fb jO Js Jt Kd qX) Uf(Bg bL Bo cO Hf Is Iz Na qX Ua uV) eD(dF Fp Kf Kk
Lh Mq qQ qX tX Un Us) Ad(cI Hc Kj Mf qC qH qZ rB yE) Lu(An dL Ha hB Ra Ud Up uX Vp) Lx(aZ Bg bL dE Mk Nd uI Ur wL) Qa(Aw iH

Figure 1 Continued jQ Ly Mf oK Qy Um vA) Kz(bA Cs Dc Kr Lh Mx Ok Tv Us) jO(Dc Fy Ha Mr Nx Po Qd qZ Rm) cH(Jl Js Mh Oa qD Qh Rb Rm) Mf(Fp Js Kf
Kn Lh Mr Ok) Tv(An bW cB Jo lL rB yL) Kr(Ax bA bL dE Mh Nd Oa) Un(Ct Fb hG iH Ou ul vA) qC(Ar dM Ih Kf Ok Qb St) Cs(bC dM Dp
Kd qZ wB) Ua(cG Jt Mx Ok Pg Us) Kp(jP Me Rb Ri Ur Uu) Kq(Hc Jh Mv My Qy Ut) Sr(Aw Hc iH Kk Rm) dE(Dc Fw hB Lh Mr) Qd(jT Ow Qc Vv) Jl(bE cO iP uM) Kf(Ow Qz Rb uM) bL(cG Mh Mt Po) Ax(Qc qD uM) Fa(aZ rB Ur) Hc(hW Jt Nx) Qy(Ar Fr Ok) Js(bW Dg Qg) Kn(iH oK sC) Ou(aZ bC Qe) Vv(Ap Dl Nr) Pg(Bg bS Co) Aj(Jt Tt) Dc(Hq iH) Po(Nq oN) Rb(Ar Ih) Qz(Oa Qh) Ok(iH qH) qD(Lh Oa) AwUr CoMt TjMr FpRi MxgW TnOf IsjQ QeOw JtqH KkUu NwsK aHqZ cGcL wLrN} qC{Wm(Af aJ An aZ Bb Ch cL Ct Cu dM Kr Ky Lw Md Nk Nx Oh Ok Ou Ow Qm qX Rb Rf Rm rS Uh Ur Ut) Pe(aW bN bS cC cO eD hA iH jE jM jU Ma Mh My Ni Nm Nq oN Ou Oz Pj qA Qw Uk uM Tj) Ou(Ad Ar Cu Dg Fa fN It Iu Kd Kn Kr Mp Mt Oa On Pd Pg Po Qc Rm St Tr Uf) Kq(aG aL aW Ba Ct De hV jD JE Jh jM Kr Ma Mu Mw My Nq Qt) Ch(Bc Cu dM Ef Fb Ii Ij Iu Lh Mh Mw Nx Om Ss Ue Ut wD) Ko(aA An bR dE dL Hf Jy Kj Kp Lx Mh Ni Of Oh Rm vV tL) Pj(An cB dM Ed jE Jl Ki Kp Ld Mc Me Ms Mt Ql qX Ra Rh) Ax(Aj aW Ct Cv Db dE dJ Hc Ip Is Jl Lw Mv Ow Oy Ur) dB(Ar bA Bc Cv Fr Ir Kr Mh Mj Mr Oh Ok On Qm rN Sr) Kp(Aj aW dE dJ Hc Hq jM Lw Ly Me Nm rW rX uM yD) Cs(aZ Db dE dJ Jl jU Kc Kn Kz Me Ql qX Rb Ur) Qd(aW bH Ct Jl Mc Mh Nm nW Ph qX Rh rX Ur wD) Ql(aZ Dc dM Jl Kd Kr Lx Mh Mp Nm Oa qA Qe) Db(Ar Fr Jq Mp Ok On Qe Qm St wB wP) Nm(aG Cw Hq Kj Me Mv qA Qw Rb Tt Ua) Is(aN bN Hc Kz Ne Ni Nk Ow Qw Qy rX) Aj(Bc Cu Ez Lh Nr Pd Qh Qm Tn Vo) Lx(bL bQ bS cL hA Mk Nq Oy pF Rb) Qa(aW dJ jF jM Mv Qg Qw Uk Ur yL) Kn(bQ Ct eD Hc Id jE Jl Ke nW rB) Ow(Cu Dc Dg Fr Ih It Kr Mm Nt Nv) Pg(Co Hc Hu Ib iH jE jU Ma Rb Ua) Ar(dM Hc Hq Ib Me qX Qy Ur Vv) Ny(Co jU Lw qX Rm uM vV wD yL) Oh(hP Ib Ne qA Ra Rb Ua Uk Ur) aZ(Bc dF hB Kc Kx Lh Mr Rm Uc) Mh(Cu Cx Ih Jq Jr rS uM wB) Qe(Fb Hc Iz Jk Of Oy qX rX) Ok(Hc jO Me Oy Qy Rb Ua Uk) Dc(aW Ct Hq Iz Kr Of Oy) Ih(bN Ib jF Ly Nk qA Ua) Jl(dJ Lw nW Qw Ue Vt Vv) Kc(dE Js Kr Nt Oa Qb Ra) Li(Ct dE fP Hq Jq Ly qX) Cu(Aw Hq iH Kz Oy Ua) Rb(aN Ed Js Mp Qm Rm) Jt(Hc Ib Kk Me Of Vv) Kd(bL bS Ct iH Kz Ur) Lj(jE qA qB qZ vH wB) Oa(dE dJ Ip Jq qB Ur) Un(Hf Hu Kk Ma rB Uk) Kr(Ib Jq Kz qX rB) Pd(cA Me Nd Oy rB) wD(bQ dJ eD Iu Mf) Ad(Iz Me Oy Ua) Dl(Kk Mt qZ Uk) Ur(Kk Mr qX rB) Fb(aN dJ rB) Js(Kz qA Uk) dE(Jy Lw Mp) dM(aD uI vV) yL(Id oE Sr) Ct(Nt Rm) Me(aA iZ) Ib(Bb Qc) Ke(jD vV) Kk(dJ qA) Lh(Hc Kz) aN(Nx Rm) FaMv FrQy LuLw MwVt UaQh UcIz HqSt SrqX JyaW LdUf qAqZ} Qa{Oy(cI eP Fr Ik Jh Jp Ke Lh Li Lu Lx Nb Ni Nj Nk Nt Nx Om qD Qe Qg Tr Uh Uk Vs Wh) Pb(aA cI Dr eP Fr Ho Ke Lw Me Mm Mq Mr Ne Nk Oh Pc Pe Po Ps Qb Uk Ur) Lx(aA Fi Hw Ii It Jk Jq Lu Mb Me Mq Mt Nk Nq Ns Nx Oe Og ON Qb) Ms(aA bR bS cI Ct dE Fr Jg Jl Jq Lw Me Mm Mq Mr Mu Pc Pe Uk Un) Ih(aA Aj bL bR bS cI dE Fr Jp Lw Mm Mq Mr Om On Rt Vt) Ii(Ar bA bR cI Hu Ik Is Jg Kn Lh Li Nt Om Un Vt Zq Ye) Nk(fN Hu Hw Is Jg Jr Li Lj Lu Lv Nb Ne Nt Nx Og On) Nj(aA Fr Hq Jl Jp Jq Li Lu Nb Nc Ne Og On Qb We) Fi(bA Dp Dr Fa Gp Gz Ib Jy Kc Ld Nr Or St Ye) Li(gP Hq Hr Hw Jk Jl Jq Lu Me Mt Nq Ns Og Qb) Nh(Fr Jl Jq Lh Lu Me Mm Mq Mr Nl Nx Om Qb) We(cQ Dl Ed Iq Jt Kf Kj Me Nd Rt Uk Up Wc) On(Hq Hr Hw Jk Lu Lv Me Mk My Nq Ns Og) Ni(cI Ct Fr Jl Jq Lh Mm Mr Om Pc Rt) Ye(aZ cQ Jt Kg Nc Ne Nl Pa Rt Wh Th) Nx(Hq Hw Jk Jo Lu Lv Mt Ns Og Qb Qe) Jg(Hq It Lj Lu Me Mw My Nq Ns Og) gP(Hx Id Kk Kn Ko No Ou Ow Qg Va) Mt(It Jp Jq Lh Me Mq Ne Og Qb) Ik(Hr It Jk Jp Lj Ns Og Oh Qe) Uk(bN Ha Hx Ib Mk Nw Qm Ul Vt) Lv(Il Io Jl Jp Mm Mq Mz Nb) Hq(Hu Jp Jq Jr Lh Lj Om Po) Rt(Gl Jy Kc Me Nd Sj Us Wm) Mb(Jl Jp Jq Lh Oh Qe) Nd(aA bA cI dM Lw Pe) Ne(aC bW dE dM eP Nl) Wc(Dp Dr Il Jn Us Wh) Lj(aA Hw It Lu Om Qb) vA(dE Fb Hx qD Qg Tr) Yf(Mm Oz Rh Vq Wm) Th(bA Ct oE Ur Us) Mz(eP Lu Me Og Qb) Jt(Dr Vh Vi Wg Zq) Nq(Jl Jp Nt Om) Wh(Aj Ch Dg Ke) Qg(Aj Ch cI uM) Jk(Jp Nb Nt Om) Og(Hu Jp Nt Om) Ct(Ba cT Uf) Fp(Mm Mq Pc) Ns(Hu Jl Nt) Hr(Jq Lh Me) nD(Db eC Ri) qD(Hc Me Ow) qX(Fb Ko Ql) nW(rS sM tM) Ha(Ar Pe) Nl(cI Nc) Hw(Jp Qe) Il(Eq Yk) It(Is Qe) Wd(Ke Qz) Jq(Iq Md) Xa(Dg Kf) Kr(mW Sj) Nw(oN Tj) Ok(aA Qb) eP(cA Hb) AdAj ChoH DrKe WmxA FbrB MkJl HxLh YhbH KfUw RhVc OwoE OuqZ UhoN VbcQ VihG dMrC nIjB jOuT} Qe{Oy(Ad Cp Fr Jr Lw Me Mi Mq Mr Mu Mz Ne Nk Nl Nn Nu Oh Pc Pd Pe Po Tr Uk Vs We Wm) Nk(Ik Jq Jr Lh Li Lj Lu Lv Lw Lx Me Nb Nt Nu Nx Oh Om On Pc Uk) Ns(Hu Ik Jg Jq Jr Li Lu Lv Lx Mq Nb Nl Nt Nu Nx Oh Om On) Lx(aA Hr Il Jq Lu Me Mh Mq Mr My Nx Oe Og Pa Pg Po Tj) Hq(aA Hu Ik Jg Jp Jq Jr Li Lj Lu Nj Nt Nx Og Oh Om Po) Pb(aA Dr Fr Ke Lw Mm Mu Mz Op Pc Pe Po Uw Vi We Wh Xa) Jq(Hw Ik Il It Jl Li Lu Mb Me Mq Nj Nt Nx Og On) Mm(Fi Hu Ih Ik Lv Nh Ni Nj Og Rt Uw Wh Zq) Lj(aA Fr Ik Jg Jp Lh Lw Me Mq Mu Nb Om Pc) Ne(aA Aj cI dM Ik Il Jr Nb Nc Nt Nu Uk) Me(Jg Jl Li Nj Nt Nx Og Oh Om On Pc) Mq(eP Fp Hr Hw Lv Ms Ni Nj Nx Og On) Mr(Fp Hr Hx Ih Lv Ms Mt Nh Ni Nj Og) aA(Ih Is Lv Mt Mz Nh Ni Nj Nq Nx Ok) Aj(Ba cT Dg Ih Jg Ms Nw Ok Qg We) Lu(Jg Jl Jp Jr Li Lw Nx Oh Om On) Lh(Hw Hx Lv Mb Mk My Nj Nq Nx Og) Uk(gP Ji Ke Ms Nw Qg Qm Tv Ul Vt) Ii(bA Hu Id Ik Jg Ke Po We Xa) Wh(Ap Dg Ed Gl Iq Kg Qz Wc Ye) Om(Hr Hu Hw Il Jo My Nj Nq Oc) eP(aQ aU aZ cF Em Kp Nc Ow Qm) Ct(BA Ji Ms Mt Ni Qg Tr) Jk(Fr Hu Ik Jp Mu Oh On Po) Jl(Hw Li Lv Ms Nj Nq Nx Og) Fi(Gl Iv Nd Ni Oz Rh Ul) On(Hw Io Lv Mk Nx Oc Of) Mz(Hr Ik Jr Lw Nb Oe) Wc(cQ gP Je Jn Ni Qv) We(Ed Iq Kj Nc Ni Nl) Jp(Ih Ik Lv Nj Nq Og) Jt(Dr Mb Uz Vi Wg Xa) Th(Ax Ky Kz Ms Ur) Fr(Ms Ni Nj Nl Nq) Hr(Hv Hw Jn Lw Pe) Jg(Hu Io Mw Nq Oe) Li(gP Il Io Nt Nx) My(Jh Mv Nq Wm) Ye(aZ bH Ih Of) Og(Lw Mu Nb Pc) qZ(aL cO Gl Ou) Ms(Mu Pe Un) Ik(Lw Oe Oi) Kg(Uw Uz Wg) Rt(Ni Oz Us) Nw(Co Dk Tj) Nx(Jo Lv Oe) Op(aZ hG Oh) gP(fR Ke No) Ba(Ux Vw) Nb(Lv Nl) Nc(Nj Nl) Pe(Ha Mk) cI(Nd Ni) nD(aZ bH) wB(jO Qy) DbnI FbrB GpVt NqMu NtIo IhdE IlSf KpsC OurR nOjL wPjO qDyL tMnW} Is{Ct(aA cV dF dN Gp Id Il Ji Jl Jq jU jV Jy Ko Lv oH On qD Qm Sr Tr Ul Us) Aj(BA Bc cV dD dF Dg dM Ih Jp Kl Mt Ne Ni Nk Oy qD Qm rC Uk Ur) Ch(bA bF bN bR cQ dF Di dM Gp hP Ih Ii Jp Ms Nb oE rC Uk Ur Xa tF) Ii(aD aI aM Ar bA bV Cu cV dF dM Id Kc Lw Mr Pe Qg Qm Uh Un Vt) Oy(aC Ad bA cI cV dF Dg Di dJ dN Ke Kq oE qD Qm Qv Uf Ur Vs) Qg(aN bA bV cI dM Ed Iz Jk Jo Kg Kj Lj Ms oE Ua) Uk(bA dM Id Il Ji Jk Ke My Ni Nk Pb rB Ur Us Vt) Jo(bA cV dF dJ Fr Jl Lh Mm Mr On Pe Po Uh We) My(aA Fr iB Io Jh jK Jl Lh Mm Mr Mu Om Pc) rB(Af aW cZ kO Kq Kr Mb Mp Ne Nw oH qD) Lh(Hw Il It Jk Lu Me Mk Mw Nb Nk Ns) rX(eD Ih It Iv Jk Md Ms Na Qb qY rC) Fr(Hq Hw Il Me Mq Nk Nl Oe Of Pb) aN(bV cV Iz Kj Lv Oa Oi Qm Qv Wm) Ne(aC bR bV bW cV dJ dN Nu oE) rA(Al bA cT dM Ib Jy Ou qY Uf) jK(Hq Iz Ko Mk nW Ow Qy Vv Wm) Jl(Hq Hr Hx Il Io Lu Me Nk) Rt(An Ms Nc nJ Oz Pb Ul We) Mr(Hq Hr Hw Hx Jk Mk Nk) aA(Hq Hw Li Mt Mz Ni Ns) dM(bR Jk Lj Ms Nd Pb qX) Io(Hq Hw Jg Mm Ns On) Ye(Gl Kg Nc Of Op Ul) Pc(Ha Hr Hx Jk Mk Nk) dJ(cV Jk Ni qD zI xA) qX(cZ Id It Ow qY Uf) oE(Jv mM nD Op Ow Wm) Lw(Hr jQ Lu Ns qY) Ms(bA dN Un Ur Vt) Kg(Dr Hl Uh Uw Zq) bR(fR Ih Jk Lj Nw) rC(Ib Ju Mk Ql Ua) It(Hv Hw Jq Qd) Wc(Je Nb Us We) Pb(Fi Ke Op Wh) nD(Dp Ed Rh Wm) jM(bA Jy Ke mI) nW(qU rN zA tM) Nk(Me Nu Oh) Ih(bS cV Ur) Nw(Dk gP Tj) lY(Na Nh Up) wP(cO Db Wm) jD(Jv Rb Vv) qZ(bL cO Qy) Ed(Zq Th) Ns(Mm Pc) Lx(Mh Pg) Md(Om On) Hq(iB qD) We(Nc Qz) Jk(bA dF) Js(Jn Jr) jO(bB Ql) kI(hX qW) oN(dF Ke) uM(Dp Uf) AlNb AxHa BcUr DrmZ ThFa FiFw LywD MeMm MwOn NdOp HrHw IlSf IzKq YknF JmlL JvqD OeiC OuoV PjqU aDjV mlIN jEjF jYkO} Pb{Nw(aC Ad Aj An Ao As bR bS Cs cT Cu Cw Dc dF Dp Gp hB Kd Kn Ko Kq Kr Oa Ou pF Pi Pk Ra Rh Tv Uk Ul Un Ur Vt) On(Hw Ii Io Jk Jl Jq Jr Lh Lu Lv Mh Mr My Nc Nt Oe Of Og Oh Pd Pe Po Qd Rt Wc) Lx(Fi Hq Hu Hv Jg Jo Jp Jr Jt Li Lj Lu Lw Mb Mu Mz Ne Nl Oh Oy Pd) Qd(Gz Hu Jg Jl Jp Jr Lh Lv Ms Nb Ne Ni Nj Nl Nt Nx Oh Om Pd Po) Li(aA Fr Il Io Jp Jq Jr Lh Lu Lw Me Mq Mu Nb Ni Nt Nx Oh Om Po) No(aN bS eC Ip Jq Lu Lv Mb Me Ms Nb Nc Nj Nu Nx oE Op Pd Vq) Lj(aA dF Fr Hu Ik Ke Kq Lh Mq Mu Mz Nd Ne Ni Nl Nt Nv Nx) Mt(aA Hw Ik Jg Jn Jo Jt Lw Mm Mr Mz Ni Nj Ns Pc Yk) nI(Aw bZ cP Hf Id Kr Oa oE Op Pi Ri Uk Uo) Jp(Hu Jr Lh Lv Mb Me Ne Ni Nl Om Pd Po) Vq(bA cV dF dG Ed Fa Gn Kk Lp oH Tr We) Nh(Jg Jr Jt Lv Mq Mu Nb Nt Nv Oh Pg) Ke(Ax Ed Gp Ib Ii Ne Oa oN Pe Qm Wm) Nt(Jq Jr Lh Mq Ms Mz Oh Om Po) Ji(bA bN Cs Kp Qv Rb Ur Us Wc) Wh(cQ Fw Jn Nb nC Or Ow Qb Ql) Xa(aM cS Fw iO Jn Mq Nb Ql Un) Nd(Jg

Figure 1 Continued

Mp Mq Mz Nv Oh Om Po) Om(Ik Lh Mb Mz Ns Og Oy) Mq(Ip Ir Jg Jq Mz Oh) Op(hB hG Il iZ oE St) Ms(Jl Lh Nv Po Un) Ok(Ed Kg Kj Ur Wm) Nu(Ir Jg Jr Mw) Ik(aA Fr Lh Nv) Il(Dr Id Sf Yk) Zq(Fw Ni Nj Oa) Jl(Lv Mb Nb Po) Jn(Fp Uw Va Vi) Pe(aN dE dM oE) Mz(Ir Lh Me) Wd(Ed mZ nT) Kq(Dk Id Iz) Vi(cS kR mZ) Ar(bV dM) Db(kC kO) Po(Hq Lv) Gz(Fa Oa) St(nD Yk) Wc(Ij lY) Rz(lv mZ) Lh(Jg Nl) Ur(Un Vt) Uw(Ed nF) FiNr LvOh NbWe IddM YeQl KnoE PsbV RmVa UyhB VtbA PinD mSlN} Lj{Ni(aA bF bR dF fN Fr Hu Ik Jh Jl Jq Lh Mm Mp Mu Mw Mz Nd Ne Nj Nt Nv Oh Po Qd Rz) Jp(aA Ha Hq Io Jg Jl Jq Jr Lu Lw Lx Me Mf Mq Mu Nj Nk Nl Ns Nt Nx Om Oy Pa) Jg(aA Ik Io Jl Lu Lx Me Ms My Mz Nb Ne Nk Nl Ns Nx Og Qd) Nd(aA dF dM Jh Jl Jq Mm Mq Mv Mz No Nq Nt Nx Oh Po Qd) Nh(aA Jh Jq Jt Lu Mm Mp Mq Ms Mw Nb Nc Ne Nk Nl Nt Oh) oE(aE Bb Bc cH cM Jq Jy kC Ko Lx Ne No Pj Qg Rh To Un) Lv(Fr Hq Io Jl Jq Lh Lu Me Mq Ms Mu Mz Nb Nk Nt Om) qD(Cv Id Jq Jy Kn Lx Ny rX tU Vt wB wF zI) Mz(aA Hu Ik Jl Ms Mu Ne Qd rV uM) Kq(Aj Ch cI Ct Ii Iz Oy Uk xA Tj) On(aA Jk Jl Jq Md Mw Nt Nx Oe Oi) Nw(bA bR dF dM Ha pF rR Uk Tj) rS(Ke Kr Ly Mj Mm Nm No sC Wm) Ms(Jl Lh Mp Mw Nt Nx Qd Un) Om(Hq Hw Lu Md Nk Ns Og Oy) wP(gW iA jF jQ Kp Ow rR) Lx(aA Ik Me Mq Nj Nk) Ji(bF eC Qg Uk tM tL) gP(Jl Jy Qd Uh Un Vt) wB(bR jD jO Ly Pj rB) qZ(bW iO Ld Ow Qy Rb) Tj(Iv No tU Un wD) Ha(dF Ke Ou Pe wD) uM(Cv Id Ip nY Uf) Fr(Ne Nj Nl Nq) Mt(aA Mm Mr Oy) Ik(aA Jl Mu Qd) We(bH Ed hG Ye) Jy(jV rB Rt Th) cJ(rU rV uY wF) qX(fY Ko Uc vP) uZ(dL Ul uX Vs) Zq(Ed Nj Or) Jl(Ih Nb Nx) dM(bR Qm vT) xA(aV eD Pd) uT(dJ lN uO) Th(hB pF) Tr(tU zI) Ii(Ke Un) Ip(zI tM) Nx(aA Lu) Ou(Ne Qg) Vt(nW oH) dF(oN Uk) jT(wG tL) pS(dB dE) rT(Ko rB) oV(Mj To) AjOk DbkC LytU MdJq RbwL KctL OppF VsOy PjuP jRrW nWvW} wD{uM(aZ cH dI hF iO Ip Iu Jk kR Ma Mf Nd Ni Nm Ny Og qX rX) Db(cT Fy iA jD jE Jk Kr Mk Ny Qg Qn rB rR rY wB tM) qD(aW Ba CO Cs Dk eD Hq Hu Ko Mf Nq Oa Qd Rb Ua) Ri(aH aW bN bP cC Iq lK Mf Oa Or rO vA Vv tL Wm) Kr(Fb Hq Jo jT jY Ou Qg rB Vv xA tF) dE(bH bN Ct Mf Nm Ou rB rY vI Vt yL) Mz(Hq Jk Mk Nc Nk Qn wC wF tM tL) Ji(eD hO Hr iA jP Md Or Qg uZ tF) bL(bH bS dB kR Mf qX rB rY yH tF) jT(aW bS eD Lu qX Qy rA Rb Ua Wm) Bb(Ao Aw Bg Co Hc Hq Jd Mv My) Tj(Ks Mr Mt Nr Ny Pg Rm Us uZ) Uf(aZ Ch cL De My Nq Ou Ow uI) Ad(Hx Kz Md Nb Of Ow Oy Ub) Ny(eD Hq Iz Jd Nv rW Ua tF) Ko(cP Jk Or uO Vv tL tF) dB(iA jM jY Ky Qu rO tM) iH(bP iA Kn rB rO rX tM) Md(jO rC Sr Tv Ue Ur) Me(bS Fb Id Kn Kx) Tv(Cw Nk Oy Vp Vu) Rb(aW bP dJ Hr Jk) Ke(cP hO Hr Jk pY) Kp(aZ cO Cw Hc Mf) Ur(Aw Hc Ii Of wC) zH(aZ Co My Nd Qy) Lu(bW cT iA tF) Ub(cO cP Js Us) Hq(Mt rC Us uZ) Tn(As Kn uT tL) Ip(aW aZ Hc jM) Ql(cH jD Nh Nv) bR(jY Qw Ua wF) qH(Fb Rc rY tF) jO(Kx Mr Vv wP) De(Bn Vt tL) Nm(Aw Kk Or) Tr(bF Pa yD) rC(cH hR jM) rB(Kx Ou rZ) jF(Fy jE rW) uZ(Bg dM Ua) Cs(rO rU) Ct(dJ Uc) Dg(cO Vv) Mf(Pj qB) Mt(jM oN) Nd(Pd Pg) Nk(dJ Nl) Iu(iA tF) Jk(Ks Uu) Nw(Je On) Us(Hw vA) aZ(jD qY) cP(bS kS) AsNf WmbN EzUa FbcH NbKn HrSr TorU HcbP JdKq SsVv QhOf KyOu OrVt PgjM cOtF cYjQ dCeD jRvP} Lx{Oy(Ba Bc Cq dJ Dp Fr Gp Jp Kd Ko Kr Lh Mm Mu Ne Ni Nj Nk Nl Nt Nv Om Ou Pi Po Sr Tv Uf Un Us Vp Vs) Hq(Fp Hw Jn Jq Jr Lh Mi Mr Mt Mu Mz Nx Ok oN Qd uL uZ vV yL) Ni(Ik Jg Jl Jp Jq Lh Li Mt Nc Ne Nl Nt Nx Oh On Pc Qd) Nj(aA Fr Jn Jp Jq Jr Lh Li Lu Me Nb oE Oh ON Qd Wc) oN(bG dE dF dJ Ij Ir jK Ko Kp Kq Mz Nb qZ Rg Uh Vt) Ns(aA Ik Jg Jp Jq Li Mt Nb Ne Nt Nx Om On Pe Qd) Nd(Hx Jn Lw Ml Mm My Nb Nx Ny Pa Pc Pg Qd Wb Wc) Nk(fN Ik Jr Li Mr Mz Nc Ne Nl Nt oE Pc Pe Qd Wc) Me(aA Jg Jl Jp Li Mr Ms Nt Oh On Pe Pg Qd) Ms(Fr Jg Jl Jt Lw Mr Mu Nb Nn Pc Pe Un) On(Hu Ii Lu Mk Mt Mz Nh Nq Nx Oe Og Pa) Mz(Jr Li Lu Lv Mr Nc Nl Pa Pg yH) Tj(dE Ji jO Mq Mw Ne oE Wm) Jp(Ik Io Jr Lu My Nl Nq Pa) Mt(Co Jl Jr Lh Lv Md Pg) aA(Jr Mf Mq My Nh Nq Qd) Wc(bS Jn Kq Nb Pi Un) Lv(Jl Lh Mr Oh Qd) My(Mr Mu Nb Ok Pg) Ne(cA cK dE Nl oE) Jq(Ik Mb Nh Ok Pa) Co(Gp Kq Nw uM) Nq(Jg Lh Mu Qd) Mq(bS Jn Mr Qd) Yk(hG lY nT St) qD(Bg cL Id Pg) oE(bG Ch dE Qm) Mk(cA Ny Qm) Nh(Fr Lh Pe) Wb(Ap Kg Mm) Nx(Jl Li Lu) Ok(Mh Of Pg) qZ(aL Gl Hc) Aj(Ad Jg) Ed(Fc Ho) Fi(Fw Oa) Fp(dJ Mr) Ii(Om Un) Ik(Fr Og) Jk(Jg Mu) Op(hG Oz) dE(bQ cG) gP(Oa Rg) AobS DgXa DrnF WmMw ExbR NoaN LzNy NcNl IoQd LifN WneC OgOm UkOz VtvA PghO cOzA dBrT eDwP nWvV} Mz{uM(Af Ax bV cJ Cs Kk Kl Mh Ms Ni Ou Ow Pk Qc rO uT Vt yL) Ms(fN Ik Jp Lh Mp Mw Nt Oh Om Po Qb Qd qY rX) Nd(aA Jl Jr Lv Mi Mr Mu Nn Nv Om Pe Pg Po Qd) Nh(Jg Jl Jp Jr Lh Lv Mq Mt Mu Nb Ne Oh Om Po) Li(Hq Ik jK Jl Lu Lv Me Mq Ne Nj Nl Ns Oy) yL(Co ED Hq Lw Mm Pj Ql rS rV Tr wP tF) rO(Cs Dg Jl Jy Ko Mm Nc Nt Nv Ow uX vB tM) jK(cI Ct dM hB Id Jf Mh Na Nw Ow Pj Vt) xA(Db Fr Jg Ji Ly Mf Mm Mq Mx uX) Mq(Jn Jq Jr Lw Me Mt Nj Nx) rC(aJ Ji Ke Qg qX Ri Wm Tj) Nc(qX rU uO wB wE wP zA) uY(aA aJ bA bW oE Tz Uk) wB(Nv Ow Pk Qc vV Wm) jD(aD cZ Jf Un Wm Tj) pS(aW Il Ly Nk Pj Uu) Mt(Jr Lv Lw Nt On) qX(Ha Ml Na rR tM) No(Mb Nr Ns oN) Me(Jn Jq Jr Nx) hV(bF eC Jy nW) zI(Nm Pk rU Uu) rA(bA bB cE eZ) jM(Ar bB cJ cZ) zA(Ct Il Iz Vv) vV(Ip jQ Qc yE) Nu(Jq Mw Ns) Nj(Fr Jp Qd) Tz(uO vT wE) Tr(Oy tU yD) Ik(Fr Jl Qd) Ko(rT vB wP) yH(bC sC Vv) zH(Jf Qn Ua) tM(Af Qn uL) uX(aW Hw Nk) Ct(oE uL) Fp(Mr Pe) Ib(vT wE) Jy(hA lO) Kg(Wh Xa) On(Ii Lu) eD(rN wH) rB(rU Uf) jT(rX rZ) yE(dK wE) rV(AJ) rS(hR oK) sC(Kn Pj) uO(Mf Mm) BotU DbvI DprW TjwL NmvA LvJp NarX NkvO NlQd HwrU JdqZ JhOy SteP WcVq JkuL KkoE KqjF RzmZ OwrN VptT VsqD PkwP bLwH bPvB bWuW fPlM tFrZ jRvP} Ji{uY(aN Ao Ct dJ hP Hw Kz Md Me Mv My Qt Qx rB Ua yL) yL(Hc hP Hr Jn Jy Md Nl Nm On Or Pj Qc rB rX) oE(Af aW bN cH Mm Ms nD Nj No Oa rC sC Uk) Wm(dM eC hP Hx Ib Nb Nk nW oH Ur Us wP) bA(Aj Co Ct dE fN gP Jo Ms Ni Oy uM vW) eC(Aj cI cW Hc Ii Iz Ms nW oN Oy Uk) eZ(aG Ao Aw Ba Co Cw Db De Hc Iz rB) rC(Ao Aw Ba Co Fb Gl Iz Jd Qx Qy) cI(bN Gp Il Mm Mw Nd Ni Oz Qm) rB(aW bF Cs Dp Fy Jy Ou Rb rW) uM(Ax Cs Dg dM Jl jT qD qX Ss) vV(aK bN cH dJ Jn Ri sC Ur vP) lN(Ct Dp eD hO jP Nh Og Vv) Gl(Qm rS sC Uw Wc XA) Aj(bJ dM Jg Mt Nb Ni) Uk(bN Il Mw Ne Oa oN) bF(Ch hA jM lM lO Oy) sC(bN Ch dE qX qY Rb) Cs(dH Mk Nd rU uZ) Ms(dJ Ju rW rX Tj) Ii(Fa Fy Ou Ow Uf) wP(Ko Mf Ny Ow vT) qZ(Ow Pk Tz Ua Ut) Ni(bN Ct fN jP) qY(Ik Nh Nj Of) vA(Fb Kp Tr Uf) Ax(bQ Mk Nx) De(Jl Kq Qg) Wc(Nd Oa Oe) Oy(Ba dM Ur) gP(cH Ow Rb) hA(bZ cG Tr) wB(eF jP Qy) nW(Bc No Oa) Ch(Kq oH) Ct(Ba dM) Fw(eD Fi) Ha(Fp Pe) Nm(qH xA) Nb(Ao Co) Jo(cT dN) aN(bJ rO) dE(uI wH) hO(Ko Vt) hP(Ih Pk) rU(Aw Mu) oN(Qg Qm) DkKq TjOa ThNo LueP MmdM NebV UbuV IlUr RaeD JylO KgVi KiqD KpfN RinD OnuT UfvW dBwH dJxA gWrW jTuN} Nw{Il(aN Ao bA bR bS Ch Co dE Dk dM dN Dp Jd Kg Oa Sf Ua Uk Us) Ii(Ad Ax bR bV Cu Cw Dc dF dN Ed Fy Id Kq Oa Rh Ul Un Us) oN(Ax Bc Cs Fy Ir Ke Ly Ml Mq Mt Nb Ne Oa Qm Uk Ul) Oz(Ao bR bS cA Ct Dk Gp Id Jd Je Qm Qx Rh Ur Us) cI(bR dF Hq Jy Kq Me Ml Mq Ni Pa Rh Ul Tj) bA(Ch Ha Hq Ib Ms Nd Ne Oa Pa Pg Uk Wm) Tj(Ax Cs Fp Kz Li Mq No Oa Po rA tQ) gP(aW Ed Hq Id Ir Kz My Qd Qm Vt) uT(Ao Bg Ch Je jF Ma My Pg wQ) Oa(dM Gp jK Ne Nv nW pF Uk) Oy(Sr Tn Tr Tv Ul Ur Us Vs) Uk(Ed Jm Me Sr Tv Us) wB(Ao Ar Bg Ch Co Dk) jD(AD aM Dc Kn Or) xA(Ad Cs dL Gl Mt qA) Ms(dM dN Jy Or Ul) sK(fN Je Qc Ql uY) Ed(bR Ha Hq Mk) Ne(aC bR bV dN) dM(Fp Nd Pa Wm) eC(Id Sr Vt Wn) rB(cU hB Rb Sr) jK(aL Ao bL Jd) Dk(Kq rO tU) jM(Cu Ke Or) vH(De Kz On) Ad(Aj wP) Ch(rO rT) Wm(Mw oH) Mq(dE eP) Nd(dF dN) Hq(bF pF) Ij(Ao Wc) Ra(lO rW) Jy(aF Nv) Kq(lO Nv) Pa(bV Cs) rC(fP Ri) AxHa FpbR GlWe MdId MeaN MvOn TzwL UarU IbuL IzrO QzwE QguV JpjP OpeM OuqX UflM UnvW VuqZ aFbF aWjI bNbV cHwP dRvP eDtQ fNrT wQhB} qZ{Bb(aD aO aW bM Hr jE Jk Kg Kz Mf oE qB qX) aL(aZ bL Ch Dl Hq Hu iO lL Mm qB rB rC) qA(cS dJ fP Hc Kz lK Ne oH oN uW wL) Sr(aN aW Ch Fb Gl lK Mv My Nq Qy) Bc(Ct De Hw Li Mc Nq oN rB Tn) Hc(Ap aW fN jF Jl Kn Ql rA) Uf(aO bL bS Co Ib My Of Tt) Vt(Hq Je jH Md Mx Of Ql Wm) Ad(bL Ct Cw Kg Lw Ra rB) Nq(Ar Ax bW dE dJ iH Vo) aW(Hu hV Il Mb Ua Un Uu) qB(aN bL eD fP Hq Ny Or) Ch(Ap iH Jt Uc Un tF) Fb(aN Jt Kr lL uY vA) Qy(Jt Li Mm Ss Un zA) aD(aH dJ eD gP jO Uu) sO(bL jT Kl Kr rC uM) Ax(cO Mi Nl Pg rB) Wm(cO Kn My Ny Qd) Hu(aH iH Ra Uu tF) fP(Ap cH Cs jF Ny) Aj(fN Ny Uc Vo) Ke(aZ Hq Tt Ut) Ow(cC dE lu rB) dJ(aH Ib Rb vB) jF(Id rW uM wL) jO(Kn Ou tV Un) Lw(dE Id oK) Ua(Jt Uc Uu) Tr(Il jR Ma) Jk(Dl Qh Uc) Pe(aZ hQ Tn) Gl(Lh Pd) Nm(Bg Ef) Mf(dE sC) Ib(Pj uY) Rb(Cs Oy) Qb(bL oN) Jl(cO uM) Jt(Kg Ph) Kn(aH Ss) Ko(aN Mb) Ou(cJ rB) Ur(Ct vV) aZ(lL Ql) cL(bW

Figure 1 Continued

Mm) hV(dE sC) iH(aG IL) DgvA DlHw TjxA NrbS UcOy HqaH IdrC TtcH TnOf lulz JswQ KqUt KrUk LibQ NybL OalK UnnW UuhL PdoE
eDuO} oE{Ke(aW bG cH cI Ct De Jd Je Jk Kg Ms Mv Mw Om Op Ou Oz Qt) Ow(Ax Bb Bc cH Ij Ir Js Kf Kk Kn Kq Kx Li Mw Op Qh Uf Us)
Id(Ar aW bN cH Ct kC Ne Nk Ou Rh rS uM Wm Th) Ch(Ar Bc Jl Jp Kd Ko Mr Mt Mw On Pj Uh Un) No(aO Bc dH Gl hG Jk Nv Rh Vj Wm
Tj) Op(aF bI hB Ij Jn Mt Oz Pk Ub Vu Xa) Kn(Aj De Hc Ii Jo Lu oN Wm) nD(aS Me Ml nN Pi Tz Ur Us) mM(Bc bG hB Of Om Pk) kC(aO Ms
Ne Nh Nk Qn) Aj(Ad Jg Tr Uc Uh) Ar(Kd Kk Rh Vt Th) Wh(aO dH iJ Iq mZ) Li(Kd Mk Ne Oy Th) Un(Iz Nk nW Oy Wm) Tr(tT wB wG zI)
Sr(Hc Kk Ne uZ) Oa(Bb Ne Rh To) Uh(Bc dE To Wm) Uw(aO kR Nl Rz) Uy(cQ Gp Jo mZ) IY(Qu Ri Ur Us) nA(Kr Ni Rb Ri) yL(dE Fb Kp
Lu) Ct(Kq Ny Uc) Mt(oN Oy Qm) Kd(aW bG cI) Pe(dB dE xA) kR(Fd Vh Yl) Dr(bH Gp) Wm(Hb Kk) Th(Fp Ld) Gl(Wd Yi) Mm(Hp Ry) We(mZ Qu) Vt(qY uZ) Oy(Mr Po) bG(Hl nJ) nI(Pi Pk) AdIz BcNe DgWd EdRx YfaO FbrX GnbH LuKq NiRu HpfP TzYd ToKk RbnJ QddE StVa RfOu WnVv UfrS UrmZ VqeQ PguM PjcH wBnW} No{Th(bA Ch Ha Iz Kg Kj Kl Mq Nk Oy Pa Rg Ul) Ms(Fp Jn Jr Lu Me Nb Nc Ne Ni Nj Nl Nu Nx) Nd(aA bS Jn Jt Lw Mq Mr Ni Nv Om Pe Po) Nh(Jg Jr Lu Lv Me Nb Nc Ne Ni Nk Ns Nx) eC(aF Aj Ar cI Ct Ha Kj Ml Oa Qu Vt Wm) Oy(bS eP Ik Il Jh Kp Mv Qm Uf Uh Uk) oN(Jk Ld Nr Oz Rg Rh Uf Ul uY uZ Vp) Tj(Hb jH Mw Ni nW Oa Qm Uh Wm) uO(aW dJ Kc Ko Mf Nc qX Uf) Wm(bS My Nv qB rB wP) Ii(bA cA Ke Kn Sr Un) gP(Qd Si Vq Vu Tl) wP(Ma Nq Qy Ua uY) nW(jU Nr Ri Ub Ul) vV(dJ Fw jT Kd sC) Ni(Lv Nc Nj Nl) rS(Aj aW Ly qD) Me(Jq Nb Pc) Yk(Aa Il nT) eP(Gp Nc Qc) fN(Hc Or Ra) oH(Ar Bc De) uY(dJ Hc Kz) Aj(Ad Jg) Nr(aN Fp) Ns(Ik Jq) Lu(Ik Nj) Mb(Lw Pc) Ne(bS Jd) Nl(bS Nk) Wc(Dp Vq) Op(hB kR) yD(Tr vT) qX(Md Vv) sC(Rb Vp) uI(cG dM) uZ(Pg St) pF(dA Hq) BchG ChMt FiFw NnvT NqMu MqdE HwyL IlSh IvrW YhjB RarB KohO KpwQ PdxA aKvP bOrC eDlN tFrX} Mt{Oy(As Cp Cs Dc Fr Ij Ip Jg Jr Jt Lh Lv Mq Mv Nh Nt Nv Oh Pe Pg Tr) Me(Ch Jl Jp Jq Jr Lh Li Lv Lw Nh Nx Oh Om On Po Qd) Nh(Fr Jl Jq Jr Lh Mq Nc Ni Nk Ns Nx Oh Om Po) On(Hq Hu Jr Li Lv Mk Mq Nj Ns Oe Of Og Qd) Ns(Jp Jq Jr Lv Mq Ni Nt Nx Oh Om Po) Lh(Hr Ii Jq Jr Li Lv Mk Mq Ni Nj Nq) Nd(aA Jl Jn Jt Lw Mm Na Pa Pc Wc) Li(Hq Jl Jq Lu Lw Mq Mr My Nj Nk) Jp(Aj Io Jr Mq My Nj Nq Nt Oh) Ni(Ct Jq Jr Lv Nx Oh Om Po) Qd(Io Jq Lv Mq My Nk Og Ok) Aj(Ba Bc Nb Tn Tr Wh Xa) Wc(bI Jn Jy Kg Oe Or Ql) Ch(bA bF Hu Nb Ne Tn) Nj(Fr Mp Mq Nb Ne Oh) Lv(aA Jq Mm Mq Oh) Nt(Jq Nk Oe Oi) Jr(Jq Mq Nk Oh) Wm(Ms rB rT) Ed(Fc Ho Yf) Po(Ii My Nk) Fr(Jk My Nq) Ap(uO Xa) Mq(Jq Oh) Ms(aA Vt) Jl(Jq Ok) Kg(Uw Wb) CtIj MuMy NkOh IdqD YkOz NxOg UfuO VbbH dBwP dJqX nIjB yDnW vPvV} nW{wP(aJ As cZ Dl Ed Hv Hw Ir Iv Jg Jn Jq Jr Kf Kx Lw Mh Mj Ml Mr Nf Om Ph Pi Pj Pk Po Qv QX Ra Rb Rm rX tU uG Up Us Ut Uv vH) Vt(bN cV dD Ed hR hW Mq Nb Ne Nk oH Qg Ul Ur Wm) uN(aP Ba Bc bV cT dF Fa Fr iA Kf Mm oF On Pj tX) wB(cH dB Ed Ko Mh Mw qX Rb Ss Un Up) sM(cH dF dG Jg Jl jT Mq qY Sr St Wm) Ny(hV jE jQ jR jU rN rS) uT(Ad aP Bc Lw Pj tS Un) vV(aA cG Fa Mx On Ou Uf) zA(bA hC Mx rB sK uU) rN(Ad Fr Ib Jg Ko Wm) Qd(jQ qU rC wF) Ko(pS uG yE tM) tU(dH oF Pg St) yD(dF Kn Tr Us) uU(Ap Fb Kl Mw) Wm(pS vH vW) Id(fN jK jU) Ke(fN jE qX) Un(hV qX sC) tT(Mw Po Tr) wH(bV Jt Lw) tM(Ax Oa Pd) rS(aJ dG Pe) uM(Fr Mx Pe) vO(aA Lw Mx) aP(vH yL) dN(hL xA) tS(Kr Oa) BcUh CssC MqrR JljK KqIO UlyL UutX VsuY PjwF cGuG dLrC} Kq{Ch(Aj bA Dk Dp eC Gp Ib Jp IO Md Ms Mw My Nd Nv Oa Oh Ou Oy Oz Uh Uk Um uO Ur Us Xa Tj tF) Aj(Ad Ao bR cI Co Dk Ib Id Il Iz Jd Md Mk Ms Mw My Nb Nv Oa Oz Pg Ut Vt Tj) qX(Aw Co Dk Hq HR Hu Ib Iz Jh Li Mu Ne Of Tt) Ct(bN Il JM Md Mw Oa Oh Oy Wm) cI(bL Co Hq Ii Iz Ne Oy Oz Wm) qD(dB Hu hV jD Kr Nq Qt Tt Ut) jD(aW Hq Ib Jk Ou Ua Uk) vA(Fb Jd Md Mh Qy Uf Ut) hV(aW De Md Qc Qy Rb) jM(Li Md Mh Nv Wm) Dk(Nd Oz Uk Ur) Th(Cs Fp Mh Oa) Vt(Ii Kg Ms Oy) dB(hA IO wH yL) Hc(hA IO uO) Iz(jE Uk uM) Wc(Il Jn Oe) Op(kR Oh oW) rB(Fb rA Wm) jF(Md Mh Uk) jO(cU Ua wP) Cw(fN gW) De(uM uO) Ed(Fi We) Tl(mZ Nd) Oy(Vs Wm) eP(Cv Mq) eZ(aH Tn) gP(Oa Uk) hA(cF Ql) jE(bL Of) lO(Ow Ua) AroN MdrA JdyL OuuV UtcW aLjK jRvV} Fp{Nk(Fr Il Jq Jt Li Lw Mp Mq Mr Ms Mu Mw Ne Nj Oh Pe Po) Mq(aA Fr Jg Jq Lh Lv Mm Ms Nh Ns Nt Nx Oh Om Qd) Lw(dE Fr Hr Li Lu Lv Mr Mu Nd Ni Ns Nt) Ms(Ij Mm Mr Mu Nb Ni Nn Nq Pc Pe Po) Mr(Hr Jg Lv Nd Nh Ni Nx Oh Qd) Mm(Fr Jl Lh Lu Me Oh Oy Qd) Wc(dF Hu Jg Jn Nb Nd Vq Wd) Pc(Hq Jq Ni Nt Nx Oh Qd) Th(gL Jy Uw Vi We Wh) Jl(Fr Ii Mk Nd Ns Pa) Jt(Hq Hr It Nd Nx Oh) Oy(Mp Mw Nb Po Pz Tr) Lu(Jn Li Mp Mw Oh) Ni(Mu Nc Nj Nl) Jn(Du Ih Me Nx) Pe(Hr Nh Nx Oh) My(Jh Lh Nq) Nd(Mw Po Rz) Il(Dr Ne Og) Ul(Du Vi Ye) Me(Li Oh) Wh(cV Ed) Lh(Md Of) dE(dF Jq) wP(eD rB) DudF FrMw GpeP NtOh MpHq NeNl ItQd PzOg XakR RtOn VaVq dBwB dHfR} St{Ye(aX bA cT Dp jB Je Mi Ml Mu NF Ou Qb Qg Qu Qx Qz Ud) nD(aZ Io Jt Lv Me Mh Ml mW Ni Nl Or Rh Ri Wm) Yk(Ar aZ bC Ct Iq Jo Kf kR Or Qz Up Wm) Fi(Ch Cs Cu Fw Gp gZ Iv Jy Nb Oa Or) Wc(As Cq dA gP hB Je Jn Lv Nj Or Qv) Sh(bR cQ Il Iv Jy Nb nF Oa) Ii(nI nJ Uz Vi Vt Wg Ti) Rt(An Ap Ax Cp Cs Nb Or) Va(dA Jn Jr Kc Nd Nk Wm) eP(aX dF Jk Kc Ne Qm Uu) Dr(Ed Kg kR Nc Nl) Ch(eF oH pF Xa) Dl(Ru Uw Yj Zq) Th(cT Fa Og Uk) Kg(Hl Uz Wg Xa) nI(Bn Bo Ct jB) Ap(Wh Zq Tl) Dg(Uw Vi Zq) Wm(qD Yl Yf) mW(Bo Nk Up) Aj(Uw Yl) Cs(Du Zw) Nb(Si Tl) Ux(Ba Bc) AxZw DbkO DuIv EdWh EqNy NcVi YdmZ SibR KewQ OwqD UkgP rBqX} On{Ns(Ii Ik Jk Li Lu Lv Mc Mq My Ne Ni Nj Nl Nq Nu Ok) Ni(Hq Hw Ii Jk Jr Li Lv Me Mq Ne Nq Of Og Qd) Ii(Ar eP Jm Jr Lh Mb Mc Mq Nc Nl Nt Po Qd) Nj(Hu Jo Jr Li Lv Md Me Mq Nb Of Og) Jk(Io Jm Jr Li Lu Me Mq Nb Ne Nl Ok) Lv(Hq Hu Li Me Mq Mw Nq Of Og) Nh(Jl Jq Lh Me Oe Of Qd) Hq(Jr Me Mq Ne Nl Og Ok) Oy(Ar eP Fr Jl Jr Lh Tr) Ik(Hu Jo Jq Mg Of Oi) Li(Lu Me Mk Mw Nq Og) Ok(Hr Hw Mk My Of Og) Wc(aO iO Jn oN Qz) Nq(Jr Mh Og Qd) Mq(Hr Hu Hw Og) Ms(aA Aj Ct Jl) eP(Cv Hc Kg Qn) Ch(oH qD Yk) Xa(Bg Co Dg) Mb(Jl Lh) Nl(Nk Og) Yk(Iv Oz) AjoN WmMy EdFc TieD FiFw NuMk MeHw NdaA YdQz TlmZ RtjB dEyL} qD{Ny(aG aL Ba Bg Co De Hu Jd Jl Kn Lw Mv My Nq Of qB qX rX) Un(Aj Ax Ba Bg Cp De eF Hu Id Ij Jd Mv Nk rB) Lw(Aw Ax cB Ch Cs Ct dE Jl Kz Lu Mu Oa) Kn(Ct eD Hc Hu JO Ke Me Oy qA Rb Tj) Qd(Ax Il Ke Li Mc Nx Oa qA qX uO yL) Ch(Bb Cp Dc Fr Jh Nx Pe Qh qX wP) Jl(Aj cO Ct dB Ne Ou Pj Ua Vt) Ke(Ax cY eF jD Ik Oa Of qB) Id(Dc jK Jy Kd Ki VV) dB(aA aJ Cu Pg qX tT wP) Kd(dJ Ib iH Jk Wm) Dc(Aj Kr Oy Wm) Of(Ad Cu Nm Sr) Pg(bL bQ Hq Oy) Kr(qU qX vV) Ax(uM Vt) Db(rX tT) Nm(Kk wF) Hc(Om Sr) Pe(aZ rB) AjJt CsVt CuOy TruN JyKz RivV UrqX dMyL} wP{dB(Ad Ax Bb Ch hO Kf Kn Nr Ny Pj Qh qY Sr Tv) jO(Fb Fr Ij Ir Ni Nm Nn Oa Ok Qd Qh Ql Qm Wm) Ny(aZ bL cH Cs Db dE dJ Ke rB uM Tj) Ko(An Aw Ch Hc Ms Of qH sC Sr) Ad(cS Db EF Mg Mh Ua Uk) Vt(Ct Me oK Ow qY sC uM) Sr(aW cO cS dJ Ne uI) Pe(DE dJ oN RB) Cs(cO dE Qg rO uW) Mh(bL dJ oH Ri Us) Id(eF Kz Or Ou Ow) Db(Bb cH Iu Lu) Rb(Ar Lu Pj Qy) Ow(cH Iu Jt Uc) Ou(Dl Kf Pj Vo) oK(Jl Js Kn Un) Ch(Bb Tn Tv) Wm(Cv Rj Tv) cO(Ar Pd Uf) eD(Fa Oa Rf) Lu(bA Kr) Uc(Aj Jk) Tr(Iz Tt) Kp(aW Me) AwNm DeOa MfhO JsdJ KeaG KkPj KndE NxaZ UnvA PgoN} Nd{Mp(Il Jg Jn Jq Jr Js Lh Lv Mq Ms Nb Ne Ni Nr Nv Nx Og Oh Om Po) Lh(aA Hq Hx Ii Jn Jo Jq Jr Lw Mq My Ni Of Pc Po Qd) Li(aA Jn Jt Lu Lw Me Mi Mm Mq Mr Ni Nk Oh Om Oy Pe) Oh(Jq Jr Mi Mq Mr Ms Mu Mw Nb Ne Ni Nv Om Po Qd) Lv(aA Jg Jn Jq Js Jt Mm Mw Nv Om Po) Mq(Jg Jl Jq Js Mm Mw Nx Om Po Qd) Qd(Jl Mm Ms Mw Nb Ni Om Pc Po) Jg(aA Jn Jq Js Mw Og Po) Fr(aA Ih Jt Lw Pe) Om(Jr Md Mw Og Oy) Wc(Fa Ij Po Zq) Jp(Jn Jt Me Pd) Jl(Lw Mr Ni) Oa(Rz We Ye) Po(Hq Oy) Il(Sh Tl) Oz(Uw Xa) ChTn EdRz MsNv ZqKc UkVt} uM{Uf(aA Bg Bn bV cT Cw Dc Fn Hw Hx Ib Ij Ir Iv Iz Kf Kn Ml Na Nm Pk Ra Rj rS sK Uc uI uN Up Vp) Ny(bW cH Ct dF dM Ed Iz Jl Ko Kp Ow Qv Ri Sr tR Uk uX vB) Wm(Ax cE dM Id Jq Kf Kk Kr Ow Pe Pg Po qY) Kp(bM bV dM jE IL Mx oK Sr uV) Ax(bC dB lM Lw Mf pS) Cs(dE iO nY pS uT wB) Vt(eC Lw Nk pS Qg qY) Jl(aF Ni Ou Ri xA) Ko(Cv lN Mr Ow tN) uX(dB jO Kr Ow) Kf(Ct Kg Uk) Pg(cH Hq Nq) Ch(Mr oF) Dp(Oa Pe) Mm(Cu Dc) Mx(Ni Ou) Id(Mh Uv) Pj(bA qX) bW(Ir Kn) AdAj PodE HaPe UcOy TrqX SrKz QtKe VsdB cOdG hBjO} Il{Oy(Cs Dr Hl Id Lh Om Pc Sr Un Uz Vh Yk Yl) Ps(Bb Dl Fi Gl Iq Me Mg Mm Nc Pa Qz) Sf(bR Jy Mr Nr Oe Ow Qb Qd Xa) Wc(Dr Jn Jr Ld Lh lY Mq oV Vu) Fi(Fw Ir Jy lY nF Pe Ql Un) Yk(Ar Fa iO Jl nT Oe Oz Pa) nD(Db Dp Pi Pk Rb Tz Uh Tl) Dr(Jt Me Mq Nm Or Pa) Xa(Aj Bb Jo Mg Pa) Vb(bA cQ hB hG Mi) eP(cP Jd Ou Rf Tz) Kg(Gn Ry Uz Wg) Kj(Uw Uz Vi Wg)

Figure 1 Continued

Figure 1 Continued rO) Mr(rT sC) tQ(Dg Kl) wH(cH Id) LweZ TvpS JlrO Jyul KrzI LhsC hBjO} Ou{fN(aA Bc cM Cp dF Jt Lh Ni Nm Qh Sr Ut Wm) uV(Ax Dl
Pj) vP(Ax Qd) AprS DgsK DlwH NmvA JttM KnjO KrpS UnsC UwoV dJvO} Cs{uO(eD jR Mf rB Rc zH) rS(eD iH iO Ri) sC(cJ dE Rb)
uZ(bM Dg Dp) tU(eD rC) DgrU HwvQ SroN QgvC UrtV PjvA bAuU cJyD cVzI} nD{Kr(Ij Ma oF Oh Uh) Fy(Me Ml Nt Ss) eC(Hu Me Mh Rb) Up(Jn Pi Qc) Ir(bR Ri) Pi(Mh Ml) DbMw MaSs IjRi gLnN lYhX nIpF} Ar{aC(aA aJ Ba Bc cE cT dF) dF(aF bL dJ oN) Ch(eF tF) dJ(bZ cE) oN(Sr Uh) DrGp ThhC MmPs JlbN RieQ UyoH bAbF} mZ{Dr(dF Fr Hq Lv Nr oV Rz) We(bF oV Vu) Tl(bF Ma Tn) Ye(dF Jl) Rz(hG Jy) oH(Hl Zw) FyUp UbVi YdPi ZqoV WhiJ} rB{Wm(bF Cv dF Fb Jy Kn Qd) Fb(Jl Qd Qh Sr Un) Qd(iJ Ql Rb vV) Ad(cU Uk) iH(Cu Pe) RbRm JlPj JyKn QlcU} vV{jR(Bb Js jY Kf Kk Pg Po Qh Ql Tv Wm) Nm(Ki Kk) Id(Me vP) Qd(jQ jT) AsaW RicJ aVbF cGuI cUvP dFdJ} Ni{Nj(Fr Lh Oh Qd) Qd(Lv Nc Nl) Oh(Fi Lv We) Qb(Wh Zq) iO(Wd Wh) FwWe NtLh JmRt LpoQ UnjD UyhG fRoW} Db{nI(bI Hb Jn kS Qd) rN(aF Hf jT) Ur(nA nJ) tV(Bb jO) uX(aF jO) IdvI KfsC bWoO cGuI hBuZ sMjT} rS{Wm(Cv Ip Kn Kr Qh Tv) Ad(Ch Ib Uk) Fb(aW oK Pj) Mh(bS dE Nq) AxRi MfRm NkUc IdQg PeiH} fR{bR(aM aN bA bF bX cS cV Jn Jr Nr Po Qb) aC(Aw bL cS) gP(Ld Pe) RmVb mFkR} Fi{Fw(eM Ij Ir Jy Rm We) Nr(Fc Kg Mq Tl) Ir(cV Gz pI) PoFc IvQb SrgP PheQ} Id{vA(bF cG Ql rC Us Vv) fN(bN dE Ha Hq Qg) HaeZ RbzH RiuO bAuU bNvB cIeC} Ch{oH(Bc Sr Wh) Qh(eZ tM) kR(We Wh) AdeZ BaaC HaPe MwpF UcuZ TnUh QmcF jTuX} Dr{pF(Gl Iv Kg kR) nF(Ij Nr Rm) Fa(eC iO) Kg(Fy Tn) hB(Gl Th) BaSs KroW} Kr{tN(Hq Jk) uO(Mf Ri) FbvA IbfN QdnI QytR OfrN VbhB VvuZ dEwH jOuX jTuN} Un{jD(bS Ib jK Ne Nk Qg) Ii(Ax Ij Pe) NeeC HceZ JmUk tVjO jFsC} Jn{Kg(Vi We Wh) Up(nI pH) BaVb DlWe GzVa SiOh TlgP eCnF lYiB mSlN} Pe{Ha(Co Hf Mk Mw oN Ul Tj) Ii(bA dE dJ) gP(Hq Tj) jTrW} Pj{Vv(eZ vA yD) jO(dF tV uX) Kk(sC uO) wF(cO Ld) WmjK RbuV JlvT} Rm{Va(bR Gz Ih Mm) Ye(aZ bH Kg) GzYh YkcQ YjjB KgUw VbhG} eC{Wn(Hq Nu Po Uk) nF(Ij Nl Tl) Rb(mP nT) nJ(Iv Wm) FaWe} Nm{vA(cE cT dF Uk) Nk(rN wH) qH(Mr zI) KisC UrtT VvwF} Lv{Mq(Jq Lh Nx Oh) Hq(Oh Po) MyJg IiLh QdOh NxaA nOlN} uI{Jy(cG hA jT lK) cG(rW Ss vT) MpdE TnbW SraE SscE} Ld{eQ(kE kQ Rt Ti) Gh(hF oT) We(nH oF) HuRt UwmM} aC{aA(Ad Bc Dg Dl) bA(Ad cE Cu) cT(Ad Bc) NeJl} kR{lX(Du Uw We Yi Tl) PoYh IvRz SjoQ WeKj WhfB} uX{jO(iH Kk Lu Ne rC Ri) Ur(Cw Fb) SraP QyjT} eD{mH(qY rX rY rZ) Ti(Kl Nn Uc) KnKz nOqY} jB{nI(Fa Fr Ij) MwYk NbRz YhZq YiKd LphB RtPh} lK{Js(kO nJ nL) LynT MvnB QckK nNnR nOlL iBkG} Nk{Ss(rN tT tV) Po(Nc Nl) LwtN NjJl KfsC} Ik{Og(Fr Jl Oh Om) Fr(Jk My) MdJq IhQd} jT{uN(Ad cH Mf Qd Vo) Wm(pS sM vH)} Sr{Kz(rO uZ) BceQ MrgP IiKn UpmW zHlN} Kg{Fy(Gn Hl Uw Yf) Vi(Bc Nr) QbUw} Wn{Mw(Ii Jk) Vv(bW cG) BoHw FrIi HbbC} gV{cE(bM Cx) cP(Bn cX) DlGd bBdN cXdF} hB{Yh(Pi Po) Uy(Iv Oe) FaOp GhnR dEuZ} Ir{Rt(Gz hG) mM(bR Ur) OphG UsmW} Lh{Nt(Ii Og) Hr(Me Mq) HqsC IiOm} Oh{Wb(Gl Mm Qz) Op(hG Jy oH)} Uh{Rh(mM mW) oN(Bc Mr) AaYk AxNj} Cw{Kf(rT rU rV sC uY)} hX{Ly(kK kO) Mx(nC nL) lYkF} Wm{Qd(Ih Ne) IpuV dCrW} Fa{Hq(sC vT) nI(gZ pF)} Fb{MxsC UrsM dJuN jOrN} Nr{TjwF MnoV YknA RtgP} Nj{Fr(Jk Nb) NbQd QbWe} Qc{kI(hV qU rX) OphG} Qh{jV(Jk Ne Ua) JkpS} nF{CxWe YibH JmYe UycR} Bc{GpbL SsoD QmeQ} Mq{Og(Ip Nx) HwJs} Na{lY(hV iB) nChR} Uc{Of(rC uO) HqtV} Yk{Yi(iO mP) IjiO} Zq{ApNb GlJl aIpI} Kn{SsvA JofN jFsC} tT{Rb(Lu Rc) MfUe} Dg{KkyD VvsC} Po{YhhF QzVi} Gh{bGpI tFgZ} Lw{JsqY aWhO} Ly{nCjK qYkK} Me{nO(jE qW)} Iv{WdiO WeiJ} Wb{BaQb aIpI} Ye{WePs JlUl} Ur{DipK HqtN} Uw{GlhC YhiJ} bA{MfuO KzdX} dE{QdgP RatV} dJ{VvwF bFdN} gW{AxTh ExbV} AahAiP AsaWyD FcJynA FrHuJk MxnHbV NeJsrA HlaYiA KkUupS KycTdX LpcRdU bGnIpF cGcOrW nCnJhR hLtVjO Constrained panels with 3 analytes, where 3.3E-8 >= 'AUC p-value' > 1.0E-8. Contains 10,899 panels of 36,050,556 total panels evaluated. : Ng{Uh(An Aw bA Bg Cq Cw Dc Dg dN Fy Il Jh Jn Jp Jr Jt Kd Kn Lh Li Lv Lw Mg Mr Mt Mv Nm Oa Oh Om Pd Qd Uc Uk Uu Vt) Im(aN BA Cp dF dM eF Fb Hu Jr Kn Kp Lv Lw Mm Mp Ms Nb Ni Nj Nu Nv Oh Uc Uw) Jp(Cu Fa Fr Id In Jn Lu Mb Me Mq Mw Mz Ne Ni Nl Oa Oh Pd Qd Rh St Tr Uk Un) Ba(Cp Cs dJ Fp Fr Jg Kn Mm Nb Nm No Ny Oa Oh Pb Po Rf Ri Tn We Xa Wm Ti) Ad(Bc bZ Cs Cu Di Gp Il Jd Jr Kj Ko Ml Ni Nr Nv Ny Om Po Rh uM wH) Tr(Bc Fr Hb In Iu Jg Jl Lj Nb Nd No Oa Om Pj Qb Qh Ql qX Tz Vt Xa) Lx(Ap bF Cp Cw dF dM Fy Jn Ke Ko Lw Mm Mr Pe Qh Ri Sr Tn Uk Tj) Qd(bA Bc bF Cp dF Dg Gp Hu Lj Mz Ni Nt Nx Oh Qg Qm Rh Tn Uk Uu) Ar(aI Ap bB Bg bR cG cT Cu cV dM eC Ko Lh oH Om Pg Pz Qh Uc) Mw(aN Bc Cu Fa Gp Kk Ld Lh Nh Nt Nx Oa oE Om Pj Sr St Uc Uk) Un(Fr Fy Kl Li Lj Ms Mt Nr Pe Pz Qg Qh Qm Rh St Tn Uc Uk) Qa(Aw bA Bg Id Jq Kl Kp Mv Nb Ne Oh Pj Po Um Uu Vt Tj) St(Bb Dl Id Jg Jy Ko Kp Qg Qm Uc Ue Uk Ur Vt Wc Wm) Qe(Aw Bo cT Cu dM Kk Kl Kp Pj Rh Tn Uc Ue Uu) On(aA Aw cI dE Gp oE qD Qm Rh Uk Vq Vt Wc Wh) No(cV Hu Ir Jn Jr Kl Lu Lv Mg Pc Pz Qm We) Li(aA Mg Mm Mq Mr Nb Ni Nk Nv oE oH Qm Tn) Mt(aA Cw dF dJ Dk dM Jo Mu Rh Tn Vt Xa) Lh(Dg Lj Nj Nx Oh Pb Po Tn Uk Ur Uu vS) Ok(Aw bN bR Dp Ef Fy Ke oE Or Vq Vt) Jl(Bb fN Hu Ik In Ke Lj Pb Pj Ur) Xa(Bg Dk Hc iJ Oh Or Qc Rm Uw Wm) Ij(bR bW cN Cv dF dG Jy Nh Ur) Jg(aA Id Ko Ms Ni Nr Pe Rh vS) Nw(Cu cV Cw Di dN Dp eC Ef pF) qC(Af Ax Bg Cp Ih Oa Qb Sr Uu) wD(DB Fb Ks Rb Ri Ue Ur uZ) Dg(Ih Lv Mg Ml Mq Mr Tn Vt) Po(Hu Ik Mz Nb Nd Oh Pb Wm) Ke(Fy In Ji Lj Nr Oa Wn Wm) Fr(bR Jr Ko Ne Pj Qm Vt) Om(Il Lu Lv Mq Ni Nx Oh) Bc(Gp Id Il In Jj Qm) Tn(Dl Lj Mz Qm Uk vS) Ko(Fy Mq Pb Pe qX) Uf(Aw cI cT cV dM) qD(Cu Dc Kd Kn Pg) oE(Bb Is Jt Kd Qh) Id(In Pb Pz Uc) Il(Ez Fb Mz Yk) Ji(dF Fa Fy Oa) Lj(bF bZ Nt We) Nv(Ik Jj Lv Nh) Nx(Jr Lv Nh Nt) Vt(Kl pF Rc Ur) Fp(dF Jh Mg) Sr(cV Mm Pj) Jt(Nd uM wB) Kr(qZ uT wB) Pe(Ap dF Uc) jK(Bb Pj Ql) vS(Kp Pf Tt) Dc(Jj Ur) Dl(fN rC) Hu(Mm Oh) Is(fN Gp) Qh(jD Jj) Kq(eC Th) Ps(Pf We) Vq(bQ In) AjEf AprS BbMq WmNb EtWd EzyL NmUr NtPb LvOh MzIk NhJq UceC QbWh SsuX KlwB RfcV NywP PguM dJqX} Pf{Ct(bA bU cO Cp cT Cv Dc Dp Hq Id Il Jg Jq Ke Kf Kn Kr Ky Lh Lv Lw Lz Mq Ou Pi Qd Qm Ra Sr Tr Tv Uc Up Vt Tj) Aj(bB bS bU cA cO Dl Ef Gp Id Im Jq Jy Kl Kn Ko Kp Nb oE Ok Ou Oz qC Qe Qm Uc Ue Uf Uh Tj) Uk(bR cO dM Id Jq Jy Kd Ko Kq Lw Me Nm oE Or Pj Qd Rg Tv Uh Ur Us) Ni(aC aF bR bS Ch Co dM Hq Ik Jg Jl Jn Lw Mm Mq Mw Oy Ur Xa Tj) oN(aI cM dN Ij Jk Jp Kk Mr Nb Nl oE Oz Pj Qd Qg Qm Rg St Va Tj) Ha(Ar Ax Bc Co Cs Dp Jk Ke Nd Or Pj Qd Ql Qm Sr Ua Uh Ur) bL(aA Bc bS Ch cO dJ Iz Lw Ms Mt Nk No Oz Qd Qm Un Ur Wc) Hq(aA aN dJ Ik Jq Jy Kq Me Mw Nb Ne Nl Om Po Un Ur Vt) Oy(aA Dr Im Js Lu Lw Me Mm Mp Nv Oh Po Ps Pz qC Uz Wg) Ch(aC bR bS cA cV dJ Gp In Jy Ky Ou Pa Qg Qm Uh vS) Iz(dJ Ij Jp Kk Nb Nk Ok On Or Ou Oz Qa Qe Qg Ur) Im(aN dE Eq Hw Jl Jp Jr Nk Og Om Ow Qa Qd) Wc(bR cV Jy Kd Mi No Ny On Or Qb St Ul Wh) Qa(aN gP It Jq Lh Lx Me Nc On Pe Qb Yk) Mk(aC aN dM Dp Hb Jy Lh oE oH Or Pe) Jr(Jl Jq Lu Lw Lx Mm Mr Nl Nt Oh Om) Pa(aC aN dJ dM Js Nb Ne Nl Oh Ua Ur) dE(bV cL CO dJ Gp Lj Me oH Qe Qm) Ms(bS Lv Lw Me Ne Nl Nu Oh Qb Wm) In(bU cC Co dM Fr Ij Rg Sr Ur Tj) Qe(aA aN Fi gP Jp Mq Mr Rt Tj) Lj(bR bS cA dM Jq Ne Nl Nt oE) On(Hw Lu Lv Me Mq Nl Ns Oe Of) Un(Co Ib Jk Jo Kg Kj My Ua Us) dJ(aA aK aN eP Jk Jo My Ne Qu) Pb(cT Cv Ed Fr Ij Rg Tv Ul) Ns(Ik Jn Jp Lh Nb Nt Nu) Nj(aA Jg Jq Me Mw Oh Om) Kg(Fd Hl Ji Ke Uz We Wg) Ur(aO CO Dp Nk Pc Wm) nD(aN cC Pk Ri Rj St Us) Lv(aA Jl Jn Mm Nb Nt) Jp(Me Mq Mz Nc Nl Nx) Lh(Hr Me Mq Ne Nl Nx) Eq(Ba Ed Jn We Xa) Nd(bA Bc bR Us Tj) Jq(Ik Jl Lx Me Nt) Kc(Co Ib Ne Nv Tj) Oz(dM Id Kk Ua Tj) oE(aO dB My nA Pj) Mt(aA Bg Mr Pe) Nb(Jn Me Nc Nl) Ii(As Id Kd Xa) Is(aC dM Qg Ua) Wb(aX cV Il Ul) Qd(gP Nq Nx Og) Rt(Ld Nr Oa Or) Nw(aO Ul Us Vv) qC(cO Db Ou Rb) Lx(Lu Pg Tj) My(bS cA dM) Mz(Om Tv uM) Nk(Ik Nt nW) Jj(bA dM Mu) Ql(qX Yh Yk) Og(Jg Mu Mw) Oh(Ik Me Mq) Vt(Gp Qg Us) aN(bR cA Jk) vS(dB Qy Ri) Bg(Kq oH) Dr(Iv Us) Ed(Fc Ti) Fi(Fw Jn) Fp(Jn Yk) No(bS Op) Mg(We Wh) Zq(Dg mM) Ji(cO Dd) Qu(Wh Xa) Nx(Jl Lu) BaUx CoKy DpVa EfKq EteC FrIk GleP GzbR LwNh MqOm MwUa NlcA HcoH VznT SfSt RbrB ZxkE WdQz JkUh PsUf QmnJ VbbH bSdM dInI nOjL wBnW} In{Uh(aM bA dN Fp Hw Ij Ir Iv Jj Jl Jn Jr Ko Kp Kq Kr Lh Me Mq Mw Na Ni Ok Pe Pi Pk Rj Rm St Tv Uc Up Vp Wm) Oa(Ad As bR Cu Cw Dg Dp iJ Il Jp Jy Kd

Figure 1 Continued

Figure 1 Continued

Figure 1 Continued nW(jD wH) oN(Li Lx) AlMt AxMj BaUx CqNb FiOa NogP MmWb MqdE HcfN IzQv JicI QmeP OweC PaPe bLwD wPoK rBsC} Lx{Wc(cV
Fi Hu Je Jy Kd Mq Ni Ny Ra St Wh Yk) Oy(bR Fy Jl Jq Ke Kn Kq Qd Uh Ul uM Up Ur) Kq(Ch Ct Dk Ii Iz Nv Pg Uk Ut Tj) oN(Ad Ch Lz Mk
Ni Oz Pj Qd Uf) Lu(Jg Jr Li Mq Nl Ns Om Qd) Mr(Hx Ii Ik Jq Mt Nh Ni Nj) Hq(Fr Ik Li Nb Pe Qm uY) Jq(aA Lh Li Nt Nx On Qd) uM(bS Ch
cL Ni Nq vV Wm) Tj(Ad Dp Ed Ij Ke Un) Ns(Jl Jr Mh Mu Nl Pc) Mk(Gp Kp Pe qD Uk Yk) Fr(Jk Me My Nl Nq) Ms(bL bR Ha Qm Wm)
Mt(Ao Ch Mh Of Pe) Ne(aV bU cG Nb Nc) Ni(Fi Jr Me Mm Pc) Jg(Hu Io Jr My Og) Lh(aA Hr Ii Me Mq) Nx(Hx Mh My Mz Pg) Om(Hu Md
Nj Of Pa) gP(bS cA cK Nd Pg) qD(cG Ch Js Qy Ua) Co(Hb Ji oE Qm) Yk(Ld nD nF Oz) Fi(Kg Oz Qz) Lw(aA Ik Me) Mq(aN cA Jl) Nd(dE Md
wD) Li(Lz Mh Pa) On(Md Mw Nv) Uk(Qm Sr Vt) bS(Fp Il Wm) Ao(cK Mp) My(cK Mv) Mz(Ik Pe) Nb(NI Pg) Nj(Jt Pe) Nk(Jn Oh) Ii(Ke Xa)
Jl(aA Nq) Pa(Pd Qd) cO(dE vV) dB(rO wB) dJ(vV wP) rS(jO Wm) DbwP EfJk ThKz GpVt NmqH NtOe MbJt MeMm MfJp MpdE TrhA IkJn IlSf JslN XaVs KgVi OuoE Uuul dMsC nWvH} oE{Ow(Ad Fy hB Iu Jl Jp Lh Mn Mt Nb Om On Or Pg Po) Li(bG Ch fP Id Iz Jq Kn Lw Nj Pj Qd Rh To Tt) Oa(cH Id Kd Kn Ko Lw nA Nd Nk Qd Un) Aj(Ar Bb Ef Kd Ok Pj Qh St Uf Un) Ch(Bb Hu Nr Ny Ok Pe Pg Qd Qm) Pj(Ar cI Ct Kk Ms Ne Nk Sr Wm) kC(aF Bc bR kR Me Nd Nj Pg Pk) Op(bH Dp Fa Hu Kq Lz Mv Uw) mM(aS Ij Kq Qb Tz Un Uw Uy) Bc(Id Jo Kd Kk nW Qd Yf) Ke(bN Lw Md oF pY Rh Uk) Ct(Ad Kd Mw Qh Qm St) Kn(aW bG cH dE Nj Nl) kR(Gn Ho Ry Wc We Xa) Wm(Ld Mz nA Qh St) Ne(Jl Kd Pc Qd Uh) Sr(Ar aW dE Kp Nk) Ou(Dc Kd Ko Mw Mz) Un(bN cH Qm Rh To) No(aF cK dA Rg) We(cG Gl Ki Mm) Pe(Mk oN Oy To) nA(bI Ed Kd Mh) Ar(cH Mt tF) Gn(bM Hu Rt) Tr(tN vV wF) Hc(Ij Ko Om) dB(Id rN wH) mZ(Kr Qu Vt) nI(Fp iJ Me) Bb(wD yL) Ed(nU Wh) Mh(wJ wK) Mt(aO Mz) Hl(aY Kg) Yj(Jo Rt) Qh(Iz Oy) Xa(aO Qu) Kq(Bg Ex) Qm(Kd Kk) cI(Ko Uh) nJ(Ni Ri) nW(Id uT) uM(Kp Ny) DgFd DrJd YfKi GlWh LuwB MkkI MzaD ToYl YhSt JibG WcOn RhmP VtsC eCnD wLyL} wD{Ri(Aw Ax Bg Ch Ct hP hR Id Ke Of Qn rB uI vW) Hq(aW bA Dc jT Ko Kp Kq Kx Ql Rb) Kr(eD Me Mk Of Or Ow Ua wC wF) Tj(bR Fy Js Kn Nx Oa Po Vt) eD(aW bN dM iH Ip Kn qX yL) uZ(Ao bS Ch Co Hc Jd Qd Ur) Ua(Bb Ip Nm Qh Ql Uf Ur) Vt(Hc iA Ii jY Md Me Ub) Ou(aV cH jD jP Mk qD) Uf(Bo hO iA Iz Ma Rb) tF(aW jF jO My Qy rW) Bb(Hu Iz Je Oy qX) Fb(aW dB Jk Jn Ur) Me(Dc Kq Pi rC Ud) Ji(Jk Ne Ql Qu rO) Kp(Aw Hr Hx jF Jk) bL(hF Kx Ly Mm Pc) rB(Id jO Mf Oa rC) jT(Bg Co Ow qA Qd) Db(cI Iq Mr Og) De(Fy qZ Us zH) Ko(dC hO Iq rS) qD(cC Iu qX Wm) jD(aW jO Lu Mf) jM(Ad aW Nk Ur) Nm(Hc Ly Rb) Ke(Of On Oy) Ql(dB Hw Mk) uM(cC Mh Mx) Ad(Hr Jh) As(Hc Or) Cs(Ha Kd) Md(Bn Us) Mz(rR Vv) Nb(Dc Kq) Ip(aN Wm) Rb(Ne Nh) Ss(Aj Ch) Qn(dB jO) Ur(pY tL) cO(Mt rX) cP(aZ bP) hO(bS cC) iH(jY wC) rC(dM tU) AwUs BgzH CtUu FyHc LujE MhdJ MrTn CbwL UcIi HrqZ IzQh RcQy QgjO KyOw NyuO bRbU cGhA jFtL qXrW} Kq{Iz(cW Dk Il Ji Md Mw Nd Oa Oz Uo Ur Vt Th) Uk(Ao Bg Co De hV Jm lN My Nd Oa Oy Vt) qX(Aj Ch Id Ii Jd lO Mw nW Qt uM Ut Wm) uM(Aw cH JD Je Jo Nq Of Ow Qy Uf) Oy(Dp Fp Ji Jm Li Mw Nd No Oa rA) Ct(bA cT Dp jD Ji Ms oN qD) Vt(De Dk Ed gP jF Jo nW Ur) cI(Dk Hc jF Jk Oa Ua Ut Tj) Aj(Dp Fb Gp Je Ou We Xa) qD(aL Ba Db Ib jE Kg Wm) Bg(gP UO Ur Th) Ch(Ex Id Ke qZ St) Wc(Dp Fp Mh No Nr) rB(cU cY hV iH Rm) jD(bL cY Gl Md Ql) jM(cF Dp Hq Ny Ql) De(Ow rA Uh Ur) Dk(Ar Ke Oi Uh) Wm(gP oH Ur xA) jE(Ba Ef My Vv) lO(cY Jh Ou Ql) Db(fN nI yL) Nv(Ax hV Uh) jF(Jg Qd Ql) qZ(dD Gl oN) Ao(Ji Ur) Co(Ur Th) Tj(No Oa) Il(Jk Tl) Jh(hA hV) Li(fN gP) dB(wP xA) lN(Ba Ef) uO(Kr Md) AxbL CwhV FbuI HaOa LuwP MhoN NerA UavA HqwH IiUh HcyL YiKg JdwB JnTl KjcW RzmZ VvjR cYjV dEfN eDxA qAnW sCvV} Ji{Aj(aA Ba bF dJ Gp Il Jl Jm Kl Lv Mw Tr Uc) Il(Ch dE Iz Op Rt Up Us Wc) bN(aN Dd dM eC Oz rC uM wP) Mw(aC Ct Ha Kg oN Us uY) Wc(Dp hG Ij Jn Nc Wh Yh) Tj(Ed Fa Li No Tr wH) Nk(cI eC lN oN qY rS) rB(Ax Ks Ly Ms Uf Vo) Cs(Ih Jo Mj Nx wP) Qv(cI Ib Mk Oy Oz) Oa(eC Ih Ne Oy Qg) yL(Fb Qn sC Vv tF) uM(aW dE Kp tT xA) Wm(Gp Nq Pz rC) Oz(aC dM Qm Ur) eC(Bg My No Ou) wP(Ch qY uW vA) wB(cO Gl Hc hG) Co(Lv Mq Tr) Dp(Ii Ms Uk) Mh(oN wQ xA) Mt(Ch Ct Dk) Ko(jD rS rT) Oy(cT Fy Gp) cI(bR Qg Ri) uY(aW De qH) Ed(Qg We) Gl(Vw Wb) Ne(aJ Ib) Tr(Kg Mk) Hc(hP rS) dM(aC Jo) fR(bR gP) rC(De sC) qZ(cS Ou) qY(lN Nc) rO(Cw dB) oN(Bc Pe) vV(aW jT) AaYk AflN AxNj BgMy BnUr ChbA CtLv DbnI DdNb DkJl FygP NmsC NdUs NiYh SsxA WhKg QmnW OphG UpnD aFbF aNrU eFzA gWhV qDrX jPvA} Oy{Li(aA Ef Hu Jl Jr Lw Mi Mq Ms Mu Nt Nx Oh Po Tn Vs) Fp(dF Ij Jl Jo Jt Mi Mq Mr Nn Pd Pe Pg) Tr(Aj Gp Hu Il Jq Lh Lw Nd Oh Pa Qb Uk) Om(Fr Hu Jr Lu Md Mz Nb Ni Nt Pe Po Qd) Ij(Ar dM dN Fr Jg Lh Tv Uf Uk Un Vs) Mt(aA Ad Cu Cw Jh Jo Mp Ni Tv Us) Fr(Ir Jg Jm Mq Mz Ne Nl Nx Vs) Po(Ik Jg Jp Mz Nt Uf Uh Wm) No(Bg cA Fy Gp Hb Ko Mi) Jp(Ar Il Mq Ne Nl Nt Pd) Mw(Id Ke Lh Un Vs Vt) Jg(Jr Mp Ne Nl Oz Pe) Ar(Ad bA dM Ok Ou) Il(Jq Kn Sf Vs Wg) Tn(Lh Pe Pg Uh) Jh(Ir Jn Nu Pg) Lh(Mq Ne Nl) Uh(Ad Tv Vs) Un(jD Qh qZ) Vq(nC nJ We) Pe(dE qD Uk) Mz(bA Mu) Qd(Ik Vs) Ke(hL Oz) On(aA Tv) Vt(oH pF) wP(Ko Qh) AdbA BcnW FyUk LvOh MqJs NdNv UcrC YinF WeJn JlOk KpfN OweP UrwB PaqD} qZ{Wm(Ch hV Jk Nk Ou Ow Ql Qy rB) Hc(aD bS Fr Hq Ok QB Ra Uu) Ua(Bc Dl Ez Iu Ny Ql Vo) vV(aU dE jR lK oK qP uM) Ad(jF Jo Kj Ma rS Uk) Kr(bS Ib Il jF Ny oN) Un(aL cO Fb Hw Jk Nq) aW(Aj fP Je qA rA Rb) Bc(Bg bS cO Nv Of) dJ(aZ dL Kz Qx yD) oN(iH jY Lh Mf uM) Bb(Bg bL Co Gl) Rb(Jk Mu Or Qy) Sr(aL Lu Mu Mw) Ra(aH Ax aZ qB) Ke(aG aH Ch jO) bW(fP hV lK Tn) qA(aN Fb Hu Qy) Id(hV Ou Ow) Ny(aD Ct Tt) Vt(jF Nm Tz) bL(aG fP hV) cO(eD Nr qB) Aj(dE Ez) Ch(aH Ef) Gl(Ok Pe) Mf(Or Ow) Hq(Kn Uf) Tr(Uk uN) Iu(aN Bg) Ko(cB Ib) Kz(lK rA) Of(Uc Vo) Us(Ct Jk) Uu(Ef Kn) aD(aZ fN) fP(aC Ur) wL(Oa yL) qB(Fb Ow) sO(iJ Qg) uM(bM Nq) ArbQ AxIq CsrB DcHw DlaH NmuO LuQl MmOr MzVu IldE QyJl aGiO aLjD aZrC bSiH cHvB tFyL rAsC} On{Ii(Hu Jl Jn Jq Lw Mf Mh Mr Of Og Oh Pe) Hq(Li Lu Mf Mh Nq Ns Oe Oh Po Qd) Mb(Hu Hv Hw Jn Jq Mc Md Mr Pe) My(Jh Jk Jr Lu Md Nk Nx Oh Pa) Mq(Jq Jr Li Lu Me Nv Of) Nl(Hu Lu Md Mk Nb Nc Ne) Wc(mZ Ni Qv Vq Yh Wm Th) Jk(eP Fr Mh Mk Mu Nt Po) Og(Io Jr Lu Me Ne Ns Qd) Lv(Il Io Jl Jo Md Oh) Nj(Jl Jq Mh Mk Oe Qd) Nq(Jl Lu Nb Of Oh) Ni(Hu Jl Md Mh Oh) Jr(Lu Me Nk Ns) Li(Hw Io Oe Of) Rt(Ch Co Di Oa) oN(Ar Cs Hc Mh) Mk(Mz Ne Ns) Mw(Ik Mt Nh) Kg(Gn Uz Wg) eP(Cq Up Uu) Ch(Fi Yf) Ed(Dr Fd) Md(Ik Ok) Me(Hu Of) Nc(Ne Nk) Nd(Aj Yk) Xa(Ap Dl) Vb(cQ dA) nW(wB yL) CtbA WmMs FiIv GlYe NsNb LuOf MtJq NeNk HrLh IkOe HcqD ShQz JoNx OppF OuuM} Mz{Nd(Jn Jq Jt Lw Ms Mx Nb Nt Nx Oz Pa Pc Qb) Me(Fr Jg Mu Mw Nb Oh Pg Qd) Mq(Jl Lh Ms Ni Oh Om Pc Pe) Ms(Ij Jg Jq Jr Lv Nv Nx) Jp(Ik Jr Mb Ne Nl Nu qX) Li(aA Fr Jr Lw Nk Nt Nx) Nj(Jg Jr Mu Nb Ni No) rN(DB dE Hw Nk uM) Mt(aA Fr Mr My Pe) Nh(Mp Ni Nk Nt Nx) Qd(Jr Lv Nb Ne Og) xA(dF Fa uM vB zI) Ik(Lh Og Oh Om) jK(No Qg Uh Wm) uO(aJ Fr uX yE) Hq(Po tT zA) cU(hA tU yH) wP(Cs Ua uW) wE(Ct Hw Vv) yL(rU Vv zH) uM(Bo Nk uG) vB(cA Ct Kc) Nt(Lh rU) Nu(Jn Nb) Mb(Fr Na) Ni(Jg Lh) Tz(yH zA) Kk(pS uY) bF(rA rB) wB(Ir Jn) rO(Jf Vt) qP(tT vV) vT(Ua vO) CspS WmtM NonW MyJg NchL NkqX HwyH ZqKg JlJq KnrC KorS NxaA cGhA cJvV dFjM dJuX hBrB yEuL} Vt{Gp(Aj Ax bA Cs dM Ed Fa Jo Jy Kg Mw Nd No Oa Wm) nW(Ar cM dF Fa Ij Jy Kj Li Ml Mw pF Qm Qv St Uh) Ms(cT Jl Jn Lh Mq Nd Nr Oh Qd St Uh Ur) eC(Ar bH dD Ed gP Lw Mr Mt Oz sC Uk) Mw(bA dM Ib Jo Kg Ni oH Oz Ri Ur) Uk(Jm lN Mq Mt Ni Oh Uf Uh Ul) uM(Cv dB jF Kc Kr Mf Ou qD) wP(bN cO De eD Ko Ny Or) pF(bN Ne Nk Oa oH Ow Qg) bA(gP Ne Nl oN Oz Qg) qX(bF Ii Ko Md Ql Uh) gP(Id Oa St Ur tM) xA(Mf Mh Pj Ql rU) oH(Aj Nd Oz Qg Qm) Ed(Oz rB Ur) sC(hR Ki rW) Kg(Ok Uh) eQ(oF Ri) eZ(aH jM) zI(hP Me) AdAj BaCt NijK IbrW IiUh IlUr StWc QywB XakR KojD KrrR KzrT NyrB OwzH OzdM fPuT tTjT iHtL rUvA} wP{nW(Bb Bn cW Fw Hx Ib It Js Kk Md Na Nb qA rS Ul uP Ur wB yK) jO(Ax Bb Ch dF Kr Mh Mt Po Rm Ua Vv wB) Ko(Aj Ct cX hG Ib Iz Kz uO VV) dB(Fy Js Kr Mj Nx Rb Rm Ua) Cs(hP Nm nY Qy Ri Wm) Lu(Ar Ch Fa Kd Kk Ou) eD(dM Fy Kr Mt Pg qX) Ad(Dk Hc Hw Kz rB) Mf(Ke Kp Rb Rm To) dJ(Fa Fp hO Oa Qy) Ch(dE Kr Nm Pj) Mh(Kj Rj Sr Uc) Db(Nx qD Ur) Wm(Ip qY Vv) Nm(cO qH Uk) Sr(bN Hr Qy) Ny(Aj Ow Qy) Pg(Bg Ua Tj) Ax(De uM) Dl(Ow Vv) Id(rB Ri) Tr(Bg Of) Rb(Rf uI) Qd(uK Ou) Ke(oN sC) Kp(aZ Mu) Kr(dE Qy) Vo(Aj Vv) ArdE AwUc NoeF NrHq IhaW QhrB RiOa OwPj PdxA PeiH} Aj{Jg(aM As Ax Cs Cu dN Ij Il Jl Li Lv Mt Mw Nb Ni Oa Oh Om Pe Pg) Mt(Ax bA Cs dF

Figure 1 Continued

Dg dM Ij Jq Kp Me Mg Ok Om Pe) Bc(aC bA cK Cu dF Ef GP Kl Ko St) Ok(Ba bJ bN Ef Gp Il Jm Nb Oa Qd) St(nI Rt Ru Tr Uf Wd Tl) Ad(Fb Jy IN qX wB xA) Ba(aM bR cA Cu Ip Qd) qD(Cu Dl Ih Kd Pj Ur) Uc(bJ Fy Ne Oa oH) bA(aI bL cF Dg dJ) Ms(Jp Lh Uf Un) Tr(Mw qX Un wB) Tn(qX rA Uh) Xa(Jn Rm Us) Uf(hO Oz uM) dJ(Cu dF Ef) Ss(uT wB) Wh(Nr Rm) Kl(Sr Wn) fN(Kr Li) DgaC FyOz GpUn NmqX MwKp IkeP ZqOa JthP KorO NyrS CuuT PdxA bCgV dEdF} Li{Jq(Hq Hr Ii Ik Jl Lu Mq Ne Nj Ns oN) gP(Hc Id Iz Jk Jy Kd Ke Kg Sr Uh Un) Ns(Jp Jr Lu Lw Nb Nt Nx Qd) Ne(Fr Hq Lu Lw Nb Ni Nl oN) Nj(aA Jr Lh Lw Me Mq Nb Nx) Jl(Hq Lu Lw Mk Mq Ni Nx Pa) Qd(Hq Io Lu Lz Me Nb oN) Ms(aA Fr Jg Mq Mu Nk) Og(Ik Lw Mq Nt Oh Om) Jp(Io Jr Lu My Nt) Fr(Ik Jk Me Nq) Ni(Lh Lu Nt Nx) Nl(Hq Lh Lw Nb) oN(Bc Nk Sr St) Me(Hq Lu Nx) qX(Js qD Uf) Nq(Mu Mw) My(Jh Wm) Hq(Ik Po) Ii(Lh Nx) Wn(cA dA) fN(jO Vv) hL(Ip Ny) ChoH CtMt EfWc FiIl NoNr LuNx LwhP MrNh NcNk JgJk JyrA KepY KyjD fPlM} No{Ni(dE Fi Ik Me Nb Ne Nx Wc wQ) Tj(dE dJ Jq oH Or Pe Uk Ur) Ms(Hu Ir Js Lv Lw Mf Qb Qm) Ii(Ad cT Dc dJ Kd Kp Pi Uc) Me(Ik Jn Jr Lv Nc Nj Nx) Wc(Cu Cw Dc Dr Jn Pi Us) Nj(Jr Lv Mu Nb Nx) Ns(Jr Mq Nb Nx) dE(Ar bS Oa Qm) Ha(Oa oN Qm) Lv(Ik Jq Nl) Mb(Ip Jn Mw) Nh(Jq Mq Pc) Il(bS Eq Og) Ap(Wh Zq) Fp(aU dJ) Ne(Nb Nk) Ik(Jr Og) Yk(iO Oz) Ye(We Wh) Ri(eQ nD) bL(pF Qm) eP(aQ Em) rC(aN dM) jK(fP Ql) rS(Ko yL) oH(Iz Vp) ArwB CtMt WmYf ThMl NcNk NdJl JpjO JqPc KgVi KjnW KkyD NxOg PgvT bJoN bSuY cEul eDfN jDyL rWsC vPvV} Nd{Oh(aA Jl Jn Jt Lu Lw Me Mm Na Nh Nk Nt Nx Pa Pc Pe Wb) Jg(Hu Ih Jl Jr Mj Ms Mx Na Ns Nt Qb) Po(aA Jt Mm Ms Mw Nk Nt Og Om Wb) Mp(Ih Ir Jl Jt Me Mu Nt Ny Pd Qb) Qd(bA Jq Lw Mi Mr Nk Og Pe) Fp(Jn Mi Nn Pc Pe Uw Wh) Lv(Jr Mq Mu Mx Nn Nx Pz) Mw(aA Jl Jq Jr Mr Ms Nv) Ld(Rz Wc We Zq Xa) Om(Hu Jn Jo Ni Ns) Ms(Jq Js Un) Il(Sf Wb Yl) Wc(Jn Un Uw) Jl(Ar Jn Ns) Nv(Jr Mq Og) Uk(Id Pe Sr) Oz(Wb Wh Zq) Mm(Ij Jr) Mr(Ij Lh) FiIr MqMu IpaA QceP TlVi LpOa UnUr PedM} St{eP(Ba cH Dc Gd Gp Hx Mi Ni Ny Oi Ud) Wc(aM Cs Cu Cw Dc eF Ij Js Op) Yk(cQ Ed Fa Fi jB Jy Nm Oa) Vb(Ad bA Cq Cu Cw dA hB) Fi(Ax Fa Gn Hr Nr) nD(bR Ma mZ Qv Us) Dr(Jo Jt Nm Ye) Ti(Kg Ms Na Nc) Th(bA Kz Lh Me) Nk(mM mS Op Sh) Rt(Fp Iv Jy Um) mW(Ch De eC Ii) Db(kC mM wB) Eq(Bg Qv Ye) Ho(Ad Cq Cu) Sh(cV Ld Qv) Yl(Dl Nl Ny) Va(bC cQ Vq) Bc(nW Vw) Ct(Ni Tr) Gn(jB Kg) Hl(kR Nm) Ii(Ke Xa) Kf(Uz Wg) Op(Oh Oz) AxVw BaRz BonF CqFd DgRu WmYh NcXa SiJn ZwLd WhKc JtUz KgUw KrqD wHnW} qD{Kd(aW bM jD Ly Mv Of qA Ql RB Ua) Qd(aG Ju Mb Nq Pj Qc Tt Tv Vv) Jl(aZ cL Id jM Nk nW Of Qy Rb) Ch(Bg Jp Nt Pd Qm tV uV) Kn(cB dJ dM Ib Id Ko Ur) Lw(aZ dJ iH Kc Ne Ur) Un(aW Kk Qt vA Vv) Dc(aZ Ct Jk Rb) dB(Cv Fy Pe yL) Id(Kk Uk yL) Ih(bM Qg Rb) Ke(Cp Jd Qt) Kr(Cv rX xA) Ny(Ao Aw Jk) Pj(Kk Ms wF) qX(Dl qA Ql) Db(Fy uX) Pe(bQ Hq) rB(Cs Sr) wF(bL nW) AxrS BaFr CuCw DgrX WmuM HcPg JyKo OwdM aAaZ dEyL sMnW} Il{Sf(Lh Lz Ml nT Pc Ql Qv Tz) Sh(aZ bR Io Jn Mt Nr Pa Ql) Eq(Bc bH Fa Jf Nr Ps Ql) Rt(Cs Hl Jr Jy nT Po Vu) Yk(bH Jf Nb Rf Tz Vu) Dr(An cQ Ii Lv Tl) Tl(Kg Kj lY Nb) Un(Jk Ms Uk Ur) nD(bl Fy hC Uu) Ar(bS cA dM) Wc(Ed Je Ql) Kj(nI Ry Yl) Va(bR Oe Pa) Po(Ms Ni) Fi(Lh Sr) Mg(Wh Yl) Yi(Jt Pa) Xa(Jt Ye) Ke(Ii Uk) Kg(Uw Vh) Oa(Fd Yf) Op(Qb Qd) Ur(Bc eP) Vb(dM Vu) ChMt EdFc TzSi IdUk TrwB YhQl VznT KpfN UpmZ ViPa} Ms{Jp(Ch Ij Io Jg Jq Lu Me Mf Mh Mp Mx Ns Qb) Po(Hq Jg Jr Lh Nb Ni Oh Om Qd) Nt(Fr Jr Js Mq Mu Mw Nh Nv Qb) Lv(Jg Mp Mw Nh Nv Nx Om) Ni(Jg Jl Mp Nv Oh Qd) Nx(aA Ij Jg Jr Mq Nh) Un(Hb Id Ke Pj Uk Wm) Oh(Hu Jn Jr Mp Mw) Om(Jn Me Mq Ns Qb) Nh(Jn Jr Js Qb) Ik(Fr Js Mw Nv) Lh(Fr Hr Mr Nn) Jg(Nb Ne Qb) Wm(Mw Ok) Mq(Js Mw) Mt(Ch Ct) Qd(Hu Lw) Jq(Mp Nu) NsJl PjwB} Mt{Ch(aN Ar dF Jl Jp Mq Mr Mw Ny Oh Sr) Ct(bA Bc Cs cT dM Mc Nb Pe Tr) Lh(Hq Hx Jk Md My Ns Og Qd) Ni(aA Fr Jl Mm Mq Pc Wc) Om(Hu Jk Md My Og) Me(Fr Mm Mq Nt) Nk(Nc Ne Nl Pe) Wc(Dr Mq Nr Oz) aA(Jr Nj Ns Nx) Jg(Jk My Ns) Jp(Jq Lw Pe) Fi(Oa Oz) Fr(Hq Jr) Jn(Mq Nj) Jq(Ii Oh) Xa(Cp Dg) Og(Ip Po) xA(eD Pj) ArdM FpdE NsPe LvJl MmJr MrQd NeNl HqfN IdvA YkgP KorT QmjU UfuM UhoN cJvV} wB{nW(aA Bc Ch Cv dG Fr hL hW Ip Jt Jy Lw Mp Pj Pz Uc vH) Ad(Bg Hu Jh jO Kz Nq qH) Db(cT Fa Jl Qh Qm Rm) Nm(Ao Hq Jh Kz qX sO) Qy(bR Jg jO Ny Sr) Oa(hP Hq iH jM Qg) Cs(iH Ny Pj uO) Wm(dC gP hP rB) Hc(Ax jO Jt Kr) Ch(Ez Qh Uu) Tr(Hu Tt yD) Ur(Ct Kz Of) Pj(fP uM Vv) dB(cH Jd qY) jO(Jd Lh Rb) Mh(rS Ug) Ua(Kr Qh) Ou(Dg Ip) BgPz UcKg HuSs IbKr IdhG TvJk KpaH RivV VvdJ} uM{Uf(Fp hW jO Kd Mr Mx Nf Nr Pe Qx uV) Jl(Ch dB dE Dp Ko Mf qH Wm) Cs(Jd Kc Mf Ny rB vQ) Pj(dF Kk Kp Lw Ny uT) Kf(Jk Jo Kz Mf Mm) Ch(Ad Cu Fr Mq) Mx(Kk Ow Qm yL) Ni(Dg Mh Ny Qh) Dp(Kn Kr Po) Kp(iP qB tM) Ny(Bg tT yL) Un(jO Ow vA) Pg(aZ Bg Ua) qX(cH eD Ur) Ax(Cv Mj) Wm(nW Vv) Nm(bW hB) Kn(bC dE) ApVv ArKe PoHq FrQy MjbC IdjK RbOk KodF LhdE QmbV OuhB VseD PerB dGjO uXvT} Ed{Fi(Hu Hx Jh Kn Lh Ni Oa Un Vi Zq) We(aM bS Db Jy Mq nF Nj Nl Oa Wm) Wh(aQ bA cV Jy Lv oH Yi Tl Yf) Vq(bA Hb Jn kC nO Qv Uh) Zq(Fc Mm Nb Oh Yi) Fc(Hu Ir Xa) Nq(Dr Rx Yk) Rz(gP Iv Oz) nD(Ir Mg Pi) Yf(Fy Ow) Hu(Yk Ye) Wd(eM Oh) Jn(Lp Yi) Uw(cQ Fn) Ux(Ld nF) gP(Id Ke) HaPe MgYe TrvV JkTm UfrB UrnA PjrC bRfR eCnF} Wc{Jn(aM cS Cw Dp hB hG Hu Jh Mq Mr Ne Ni Oa Rb Un We Zq) Fp(bQ Fy Jh Jy Lv Mv Vi Zq) Vq(Oa Pc Ql Ul Us Vu Yk) Iv(Ba Jg Nq Qc Qd Uh) Wh(Ex Nb Pe Qb Un) Ij(bA Kg Qb Wm) Oh(Dr Je Jy Ni) Oa(Ef We Zq) Bc(lW oH) Dr(nJ Pz) Mr(aZ iO) Tz(Je Ni) Sr(gP Us) Jy(Dp Nr) nF(hG Un) AaUh PoNb IrUr YigP PzJe QbUs JhPs lXkR} Qd{Ni(Jg Jp Jr Ne Nt Nx Oh) Lv(Hq Io Jp Nb Nx Wm) Nh(Jq Me Mm Mq Om Pc) Nj(Jp Jr Nk Nx Og Oh) gP(Kc Oa Pe Rh Uk) Wm(My Oe oH Oi) nW(hL hV jV rS) Ik(Jp Og Oh) Ar(bN oN) Nq(Jp Oh) Nk(Nc Nl) Kp(sC uO) Kr(mW mZ) dE(Fp yL) eP(bB Cv) jO(Jp uT) lN(Nx tF) ChoH NtOg NbNl HrOk IbrO IibA QgqX JyjF bRfR cUrB sMjT kIrX} eP{cP(cI cS Ct Db dJ Ef Jq Ok Sr Us) Qc(aJ aP Bb bZ Gp Jv Ni Qx Rf) Pe(aQ bV cV Gl Hv Ip Jk) Sr(aZ Ba cD Mv Ns Oz) Me(Gp Jp Lh Mn Rm) Jl(bR Mr Oh) Uh(Ba Kz Nq) Un(Ba dF Ij) dL(Mv Rm Tz) Gp(Ha Iv) Mq(Aa Rf) Ql(Lz Ou) Oh(Ik Rg) Us(Lh Vq) ExKp GlQb NnHc LyTz JpRm KyOw RfbB NxOk cAcG} Ke{Oz(Ao cI Dk dM Ib jR lM Oa Qm Uk Wm) oN(aW dF Hq Jk Lw Mr My oK Qt) Ii(Bc Fp Mw Pe Un Wm) hL(eF Iz Jh Mw Of qH) yD(jD Mu uI vW) Ax(pY uO xA) qA(cO hG Kf) qX(Hr Nm sC) Ny(rA rS) gP(bI Hc) jM(Jy Ql) vV(Bo Mv) ChtF TopF KpuO KruV WneC PcrA aKvP eFjR hVhG jTuN} Jp{Ni(Lh Mf Mq Ne Nt Nx Oh Om Qb) Ch(Dp Fp Sr Uk Ur tF) Lv(aA Io Jl Lh Mr Oh) Ik(Jn Lh Me Mh Mr Pe) Mq(Jr My Nx Og Oh) Mb(Jl Lh Nu Om) Nj(Fr Nx Oh Po) Jr(Me Ne Nl Ns) Ct(Fp Oz Pe) Nh(Jq Lw Pe) Ar(Iz My) Ns(Nt Nu) Og(Nt Om) NuMe NkNl HrOk OwfN nLrB tUnW} qX{dJ(aI Ar Gp Jq Kk pF rS Uk) Fb(Ko Mh Mj Pg rS rW Un) rB(Bc cG Cs Dc Qh) Js(bW dE Jy Uh) Ql(qY rC Sr Uh) Ny(nW Qn sC Uf) Pj(aM Lw Mr Pe) Nm(Ou Uk xA) Ko(dE rC rX) Ct(Uc Uf) Id(Uh zH) sC(Cs Ur) WmUh MfdM NeUf UcHr TreZ SrjD JyuI LhbL OufY qAjT jOuT rNnW} Fp{Hq(Jn Mq Mr Nn Pc) We(cQ Du Nj Rh Ye) Th(Ma Ou Rz Wd) Nk(Jl Jn Nn Pc) Hr(Hv Hw Jl Jo) Mk(Mp Mr Pe) Uw(cQ Du Gl) dE(bF bZ Lv) Ns(Nn Pc) Mp(Pd Pg) Mq(Lw Ni) Mr(Hx Mm) It(Ir Jr) Js(Jn Jr) Vi(cQ Kg) Vq(cV Xa) CtOk DbnI FiNr MvMy NeJl NiPe TooV JtPc YeOf LpUl dFdJ nOjF} nW{uT(Cv Fb iP Ko Ou rA Ul) sM(Dg eT hW iA lM oF) rS(Ad Fb Mh Mp vO zA) vH(bV dF dH Fr vW) rN(bA bV eD iP) yD(Jt Nr Po) Jl(hV jR) tT(jR Uc) tV(aA Rb) rC(dM Jt) sK(cG Dg) tM(hC Js) yL(dN Uf) AdrX LwfN MxrW IdhV TrvV RieQ PdzI bWuU cHtL cWvO jYpS zAuN} Tr{uN(aZ bP Ct eD Fb Md Ow) vV(aU bW Hq Id Jk Ri) yD(Ef Id Jk Ny rX) yL(bW Db Nc pS Rb) Ct(gW tU uV uX) tT(bS Me Mf Of) wH(aZ Me Mk) pS(Bg dB uI) uX(cL Mu Qy) Hq(wF yH) Jk(tV tM) zI(An Iz) uI(lM Lw) uT(Co Pg) EfyH MfwF TtsK KiqA OwtU} Oa{Fi(cQ cV Jn Mw Ni Nr Rb Rh Vq) Zq(Aa Dl Yk Wm) Rt(Ba Bg Jy pH) bH(Fc nI Ye Yf) eQ(Bc Qh Rg Rh) Ne(bW dM nJ) Dr(cV pF) Du(bR hB) eC(nI Yf) gP(Uh Tj) nA(Hv Ii) nD(Db Oz) rS(eD Uf) TiNa ThNq WeVq YeUl KgVi RisC VcbZ PjpF dBrO jTpS} Nh{Lh(Ij Jl Md Mq My Nc Nk Ns Og Oh) Jg(Mq My Nb Ni Nk Ns Og) Lv(Jq Mm Mp Mq Nb Ne) Oh(Fr Jr Mq Ni Nk Po) Mw(Jr Mq Nb Ni Nk) Om(Jr Md Mq Ni Ns) Ne(Jn Mp Nb Nv) Po(Mq Ns Og) Fr(Hu Jq Me) NiJq NkJr} Uf{uI(aA Cq cU Fb Mh Qh wG) vA(Cq Ir Pk Qx Tv Un) qH(aE cC hV iH yL) uN(bN Ou Ow rB uZ) rS(Iz Nq oN) uU(bN Ou Ow) Me(sM tT) Kp(uO uV) Ur(Oz yL) iH(rN sK) uX(Db Ou) ChoH FbzA JsrB XaVq KkuV KnsC LduO cSsK jOuG jRvV oKuT} Ch{Ar(bA eC oF oH) Uc(rV uT wC tL) Xa(Lv Oh Vi Wh) Uh(eF Jl oH Ou) Qh(eF jV zA) Qm(bA bF hB) Bc(pF tF) Mw(hB oH) Tn(bL zH)

Figure 1 Continued aC(Cu Ef) uT(DB) FatF GpUn NqZq MaoV IdeC SraN JoOk KorT KrxA PsgL VqoF nliA} Kp{fN(Bc dE fP Ib Iz Ly Ql Tt Wm) uV(aW Dg iH
jF) vA(bX jU rW Uu) hL(dB Ko rB) xA(Ax Mf Nm} sC(bL bX Un) rS(iO Rb) AdvQ AxwL CwmM FynD SruZ JyrY UrtR aKvV aWrP cVuX
dBqA dErN dMuU iHyD wFjM jPuO} Oz{Rt(Cu Cw Fy Ir) nI(bR cP Ur Wm) Bc(Ps Ur Vi) Ti(Jl Pz Wm) Wh(cQ iJ Nb) Ye(Hu Ql Rm) nD(Kr
Ow Tn) Ok(Uk Ur) Uw(Mm nT) Vq(nL oP) BaCt DbkC DrkR NjZq PzVa WdJn XaOw RxhG LhOp QmdM UkUn PjjK} yL{dB(Bc cT dF Ou
qY Un) dE(bA hB Kf Nm Nx rS) Ny(bR eD Ri Ss) dM(Db dJ jO rY) Tj(Nm Po Rb) Sr(Ha jD Rb) Nm(Ow Ur) Id(eD Hw) Ri(bA cT) Pj(Jy rS)
BbRb DbrS MxjT NiSs UcVv IbKo OubC} Ar{aC(aX bF cG Cu dG Fr Gp Jl) bF(aF aM Co dE dM Hq) bL(bZ dM eF Gp Pg) dF(bS cA Ct dE)
dJ(aA bA cG Gp) Gp(bA dE) Lw(hO oN) Yk(iO Rm) cA(cE cG) PooN ThhB SroH JlbS} Wm{xA(Ad aK hL Id Po) rB(Ad Di Mn Tn) rS(Cs iH
Kk qY) As(rN uX tM) gP(rN Un uX) Sr(aN oH) Uh(oH Tv) tX(iH jT) uT(oK Rj) YfQb HbbA YhpH JyhR QmUr OuvP UnjD VsvW dCuI
dMtL} Ko{rS(Ax bN Ct iH iO jT Mb Mq uO) Db(rN tN uT wH) rT(Aw cB Hc Kz) jD(Mr Ql Un) jO(uT zI tM) xA(cH Hq Pd) bN(vI tM) hL(Jy
Vv) CtfN MgrW SruZ RivV tNiH lNsC} Kg{Fy(Rt Uz Vh Wg Wh Yl Tl Xa) Vi(Hu Oh Ok Po Pz Rm Tz) Xa(Cw iO lr Oh) Dr(Ij Nq Ok)
Uw(Dp Nx) Vq(dF Yi) AdUh TiOh NrWe HIlj IrWh OkVc} Ny{rB(aD Bc dM Ow Pj rW Un) qA(Ct Kk My Nf Qy tF) jD(Id Kd Kj) dM(rC vT)
rA(Ct Tj) jO(uG tM) AxeD ThgW SrpY QyuT KkuO PjrS bLwF bZhA cZjM sMjT} nD{eC(bG Ir Pi Sr Tz Uh) Fy(bR kI Or Ri Tz) Ir(Kr pF Ur
Us) Ma(Kj Kz Up) Ly(iB qY) Me(hB Uh) Up(oF Uh) oW(bG Pi) HuKz IiSr Ijbl KrhB bRbZ dFiJ} uT{jO(Cs Kz Mh Ql Qy Rm) oK(Cs Db Kr
Ou Qy) Ad(Hc Iz Mg) Dg(cO Ou Qy) Ua(dB Ez Ss) Pj(dB Fb iH) Ax(bL Ou) Ss(Ow Qy) DbDc DlOw TnPe KrOu} Lh{Lv(Hr Jq My Ni Nx
Oh) Hr(Jq Nj Nl Nt Om) Mb(Jl Oh Om) Ni(Jg Nx Om) Ik(Ii Jo Og) Nj(aA Nk) Hx(Mq Nt) Jg(Ii My) TjrA OgOm VsmZ dEsC} Vq{aZ(Jn nC nJ
Yk) dF(Kj Mg Ss) mS(Jn Jr Ri) Rm(Fi Yj) Vb(hB Jn) cV(kE Ss) nT(Cv Ry) IX(cR Qv) mW(eC Up) nC(Kj Or) nJ(Gp Mw) Iini IHfB UhmM
tFgZ} dM{ul(Db Dg jO Kr Nm Sr) zH(bS dB Hq Id Lu) Ad(aC Ct vA) sC(aW Fb jO) Ba(aC Ct) rC(aD Ql) xA(Pd Pj) NePe IjbL KfvA bRfR
cMvV eDuZ} Ct{bA(aC aS Ax bB bR cK Cs dE Ij It Ok) Ba(bL cA dE Lv) cT(Bc Cu Dc Fr) Bc(bF gP) Uc(rC tN) AdNi DgtU WnUu}
Pe{Ha(bR Dp eC gW Id Kz Nk rA) Uk(gP Mk Ul) dE(Ih Lv Pa) bF(Co Hq) dJ(Ih xA) AsIi ThJy MmWb WeYe QgoN UhgP eDxA} Jl{Mb(Hq
Nb Nk Ns Og) Nj(Nb Ni Og) Lv(Nb Nx) Nk(hL Ok) Ik(Jq Oh) mZ(Rz Tl) TiNI GlYe IiNx Ijlz JsrB OpOh PjjO cOzH} Ou{f Lj(Im In Jg Jp Lv Nh Ni qC vS) Is(aA Aj Fr Io Jl Lh Mm Uk) Ok(aA Aj Fr Jl Jq Lh Oh Qd) Im(Il In Ms Nd Qd Ye) Ji(cI eP oE Uk uM) wD(bL dB dE Ko Pj) Nd(Lh Mp Oh Qd) Jp(Ik Lv Ms Nh) In(JI Nt Pd) Kq(Aj Ch Ng) Nw(Ed rW vT) Vt(eC qD vS) oE(Ke nD nI) Nh(Fr Qd) Id(qD qZ) qC(Jl Ny) BaCt EdWh HaPe MsLh NgJg TrvS QbeP QdPb StYe PjqX aCfR dEqZ nRlK

Constrained panels with 2 analytes, where 1.0E-6 >= 'AUC p-value' > 1.0E-7. Contains 464 panels of 193,455 total panels evaluated. : Pf(aA Aj aN bL bS cA Ch dJ Ha Hq Ik Im Iz Jp Jq Ke Lh Lj Lw Me Mq Mr Mu Mw Nb Ne Nl Nt Oh Om ON Pa Pe Po Qd Ur Vt Wc Tj) Jj(Ad Fy Ij Il Jn Jq Jr Js Kq Mm Mw Nd Nj Nv Oa oE Pd Pe Pg Pz Qc St Tr Uc Uf Uh Un Vt) Lj(aA cE dF Fr Hu Ik Jq Kq Lh Mu Mw Mz Nd Ne Nl Nt Nv Nx oE Oh Om Ou Pb Po Qd) Im(Dr Fr Hq Hw Ik Jp Jr Lh Lv Lw Nb Ne Ng Ni Nj Nl Nt Nu Og Om Pb Sh Uk We) Li(aA Fr gP Hq Ik Jp Jq Jr Lh Lu Lw Mq Mr Nb Ni Nk Nt Nx oE Oh Om On Qd) Qa(aA cI Ct dM Fr Jl Jq Lh Lw Me Mm Mq Mr Ne Om qC Rt Uk Ur We Ye) No(Jd Jn Jr Lu Lv Lw Mf Mq Mr Nb Nc Ne Ni Nl Nu Nx oE Pc Pe) Lx(aN bQ cA cK Fr Jg Jr Lh Lu Lw Ne Nl Oh oN Uk Wc Tj) Qd(Ik Jr Lv Ms Mz Nb Ne Ni Nj Nl Nt Og Oh On qC qD Wm) On(Hq Hu Hw Jl Jr Lh Lu Mh Ne Nl Nq Ns Nt Oe Of Og) Et(bV eC Id jO jP Kd Ke Kl pF qC uM Un uV Vt Vv) In(Ih Ik Jg Jn Jp Js Jt Kq Lh Nu Oa Om Qb Sr Uf) Mt(aA Aj Fr Jl Lv Lw Mz Nt Nx Oh Om Pe Wc) Nw(Ao bA bR bV dM Oa oN Rh rS Uk wD Tj) Ji(Aj bA bN Dd dM eC Gp qY Ur Us yL) Jp(Jr Mb Mq Ne Ng Ni Nj Nl Nt Nu Pb) Mz(Ik Ir Jr Nh Nj Nt Po uM wB wP) Lh(Hr Ik Lv Mb Mq Ng Nh Ni Nt Pb) Qe(Aj cI Ct Fr Mm Mr Pe Uk Ye) Om(Lv Mq Ms Nd Ng Nh Og Oy Pb) Is(bR Ch dJ dM qC Qg rX Ur) Po(Ms Nd Ng Nh Ni Nt Pb) Lv(Jg Jl Nd Nh Nu Nx Oh) Kq(cI Ct De Dk Iz Oy Uk) Vt(Gp Ms Mw nW oH Uk xA) Jl(Ik Mb Ms Nb Nj Pb) Un(Ms oE qC qD Uk Ur) qZ(dJ Fb iH Ko qA uM) Ar(aC bF cE dF oE) Jg(Aj Ms Nd Nh Oy) wD(Kr qC qD Rb rC) Fr(Ik Ng Nj Oy) Nu(Ir Jq Mw Pb) Pe(Fp Pb qC Uk) oE(Id Kk Oa Pj) Ed(eP We Zq) Mq(Jq Js Nx) Ng(Ad Ba Uh) Jn(Fp Me Wc) Ke(oN Pb uV) Nt(Ms Pb) Nd(Nv Pg) qC(Ih Ko) AjBa CtbA DbwB FpMr NhOh IdwP TrOy IjWc IkJq SrvS StnD bRfR cPcP Constrained panels with 2 analytes, where 1.0E-5 >= 'AUC p-value' > 1.0E-6. Contains 909 panels of 193,455 total panels evaluated. : Jj(Ar Bb Bc Cu Dc Dg Dp Fa Fr Hu Ii Ip Ir Iv Jt Ke Ko Kp Ks Me Mg Mp Mq Nb Nc Nl Nm Nn Nr Nu Ny Pj Qb Qh Qm Rm Sr Us) Mz(aA Fr Ij Im In Jg Jl Jn Jp Jq Lh Lv Lw Mb Mf Mi Mp Mr Ms Mu Mw Mx Nb Ni Nr Oh Om Pb Pd Pe Pg Qb uX) Kq(Ao Ax Bg bL Co Cs Hc Hq hV Im Is jD Jk jM lO Lx Md My Nd Nv Oa Oz Pb Pf Qa qC Qe Qt qX Ua Ur Ut Vt) Lj(bA bB bF bR bV cG dM dN eC Gp hB Ij Jh Jl Jr Jy Ke Lu Lw Ma Me Mm Mp Mq Ms Nb Nj Nk pF rS Uf Uk Un) Qd(aA Aj Ar bA bN cI Ct dM Fr GP Jg Jl Jp Jq Lh Lu Lw Me Mq Mu Ng Nk Nx Oa oE Om Pc Po Uk vS) Pf(aC aD An bA bR cF cK cL CO dH dM Dp Fr Gz Id Jg Jl Jt Jy Kj Kk Ko Lu Mm Oa oE Ua Uh Un Us) Po(aA Fr Hq Ik Il Jg Jl Jn Jp Jq Jr Lh Lv Me Mq Mr Nb Ne Nj Nk Nl Ns Nx Oh Om Oy Pe) Im(aA aC Aj Ct dE dM dN Jl Jn Jq Ke Lu Me Mm Mq Mr Ns Oh Ow Pe Uh Un Ur Vt Wm) Is(aC aD Al Ar bA bS bV cI cV dN eC Ed Gp Iz Kg lX lY nD oE Qm Qv Rt Uh Ye Tj) Jp(aA Aj Ar Ch Ct Fr Io Jl Jq Lh Lu Lw Me Mf Mh Mx Nb Nc Ns Nx Oh Om Oy Pe) Qa(aC Aj bA bR bS Ch dE cP gP Ha Ib Iz Ke Kk Qg Tv Uh Um Un vS Vt Tj) Jl(aC aN Ar cI eP Hw Jq Lh Lu Me Mq Ng Ni Nk Ns Nt Og Om Oy Uh Uk uM) Qe(aC bA bR Ch Cv dE dM cP Fi Gp Jy Kc Kj Kk qC Qg Qv Uh Ur Us Vt) Pc(aC bA bL bR bS cA Ct dE dM Jn Lv Lw Mq Nd Ns Nu Ny oE oN Oy Tj) Nh(Ij In Jn Jq Jr Js Mp Mq Ms Mu Mw Nb Ne Ni Nk Nt Nv Nx Ny Pb) Ar(aI aU bA cG dJ dM Gp Il In Lx Mt Ng No oH Ok On Ou Ps qC) Oh(Ik In Jr Lh Mb Me Mq Ms Nb Ng Ni Nj Nt Nu Nx qC Uk Wb) Nw(aC aD Aj Co Ct Dk dN Dp eC Fy Id Iz Or sK Ul Ur Vt) No(bA cA Ct dE dJ Fi Hu Ip Mu Mw Mx Qb Uh Uk Wc Ye) Nt(Fr Jg Jq Jr Lv Me Mp Mq Mu Mw Ng Ni Ns Nx Om qC) Lh(aA Ii Jg Jn Jq Jr Me Mk My Ne Nj Nl Nx Og Om Oy) Lx(aC aV bA bL bU cG Ch Co dA Ex Jt oE Ur Vt Xa) Un(Ax eC Ed Gp Ii Il jD Ng Ni Oa Oy Oz Pb Uh vS) Fr(aC Jk Jq Lv Mb Me Mq My Nb Nc Ne Nl Nu Pb) Nd(aA Fa Ij Ir Jn Jq Jr Js Jt Mm Mq Mu Mw Nn) qC(Ax Cs Js Kd Kn Li Nm Nx Oa Ok Pg Pj Rm Wm) qZ(Ad aL aW aZ Bb Bc Ch Dl fP Hc Kr Kz qB Wm) Ct(Ad cT Cu dF Fy Ij Ji Mt Ok On St Uf) In(Ax Bc Fa Id Ij Ir Ke Nv Nx Pg Pj Uh) Jg(Jr Me Mq My Nb Ne Ni Ns Nu Og Pb Qb) Uk(Ad Fy Id Ij Ke Mr Mw Ok Sr St Uf Uh) Lv(aA Ik Jn Jq Js Jt Me Mm Mp Nv Pb) Oa(bV cE dM Fi Ji Ke Mw pF vS Zq Ye) aC(aA aJ BA Bc bF cE cG Cu dF dM) oE(Bc Dc kC Kd Kn mM Qh Rf Sr St Uh) Aj(bA Bc Cu Dg Ij On St Uc Uf Xa) Nu(Il Jn Jr Me Mq Mu Nb Nx Ny Pg) Om(Jr Md Me My Nb Ne Ni Nj Ns Of) Ax(bA bZ cE cG dF Gp Ke Mt uM) Ed(Ke Ok Ps Rz Uf Uw Vq Vt Xa) Jq(Ij Il Ir Jn Md Ms On Pg) vS(cH Cs Kp Kr Ny Uf wD Wm) Et(eP Fy jD lN nW rS vV) Ng(Fa Ko Nv Nx St Tn Tr) Vt(bA cT Ni Oz pF sC Ur) Ir(Fi Lw Mq Pb Wc Ye) St(Ch eP Ni Sh Va Yk) Jr(aA Ij Nv Nx Ny Pg) Fp(cE dE dF Uh Uw) Ms(Ke Mp Mw Nv Nx) Jn(Mq Mt Mu Nb Nj) Pb(Id Nv Pg Uw Xa) bF(aM aN dJ dL dN) Ni(Nv Nx Qb Uh) Ik(aA Mp Mu Nv) Ji(lN oN vV Wc) Ke(eC hL Oz qA) Ok(Ch Kg Kj Ur) On(aA Mw Wc Wm) wD(Fb Kp Ri Uf) Mm(Li Mq Mt) Sr(aN eP oH) Nx(aA Me Og) Uh(Li Mq Oz) dB(rN tV wP) dF(aF bL Cs) dM(Ij rC sC) eC(Id Kd nI) qX(dJ Fb Ko) Bc(Gp Ur) Ch(Mw Tn) Nr(aN Va) Mt(Jt Mr) Tr(tT uN) Rm(Va Ye) Ow(eP Wb) Oz(Ps Uw) cE(aN Cs) cG(bL uI) nW(sM tX) uM(Uf Wm) DbuT DcUr FynD NmwB MePg MhrS MpqY MwOg JsiB XaOr KdqD KowP QleP NyqA PdxA aJdE Constrained panels with 2 analytes, where 1.0E-4 >= 'AUC p-value' > 1.0E-5. Contains 1,823 panels of 193,455 total panels evaluated. : Uh(Ad Aj As Ax bA Bc Ch Cq Cs CT Cu Cw Dc dM dN Ed Fa Hw Id Ij Il Iv Jn Jr Jy Kd Kg Kn Lh Lj Lv Lw Lx Me Ml Mr Ms Mt MW Na Nb ND Nm Oa Or Ou Oy Pb Pe Pi Pk Qd Qm qX Ra Sr Tv Uf Up Ur Us Vt Wm) Jj(aC aI Al Ap As Ax BA bF bR bZ cF Cp Cq Cs cV dF dJ Dl Ed Ef Ez Fb HB Id Ih In Jk Jo Jy Kd Kf Kk Kl Kn Lu Ma Mf Mh Mj Mr Mu Mv Mx Nc Ng Ni Or Ou pF Pi Ql Rf Tn Tv Tz Ul Ut Vo Vq) Vt(Aj Ax Ba bF bH bN bV Cs cV dF dM Dp Fa Fr Ij Il Is jK Jl Jo Jp Jy Ke Kg Kk Kp Li Lj Lv Mq Mt Nb Nd Ng No Nr Oa Oh Ou Oy Pb Pe Qd Qh Qv qX Rh Ri St Uf uM wP Wm) Oa(Aj aM bA bF bR bW dF dN eC Fc Gp hB Ij Im Jl Jp Jy Kk Ko Lp Lx Mm Ms Mt Nd Ne Ni Nk No OH Ok On Ou Oz Pe Pj Qg Rt Sr St Uf Uk Ur Vi We Xa Tj Yf) Sr(Ar Ax bA cI Ct dE Fa Gp Hb Ii Il Kp Lh Li Lj Lx Mt Mw Nb ND Nc Ng No Ok Oy Oz Pb PF Pj qC QD Qe Qm qX qZ rB St Wc wP Wm) Ar(aA AD aJ Ba bB Bc bW cF cH cT dG dL eC Ed Fr hB Ij Im Jq Lh Lv Lw Me Ml Mm Mq Ms Mw Nb Ni Oh Or Oy Oz Pb Qc Qh Uk Ur vS) oE(aD aW Ax Bb Ch cI Ct Dr Fa Hb Hl Ij Im In Ir Jl kI Ko Kp Kq Mt Mw Nb Ng Ni nJ Nk Ny Oh Ok Om On Ow Pg Qa Qe Qm To Uf Uy Th) Mw(aC Aj aN Ax Ct Ed Fa Gp Id Ij Ik In Ir Iz Jq Jr Kk Kq Lv Mb Me Mh Mq Mx Nb Ne Ng Ni Nj Nl Ns Pb Pe Pj Qb Ua Un Ye Wm) Fr(aA Aj bF bL bR cA cF cK Ct dE dJ Gp Hq Hu In Iz Jl Jn Jr Js Lh Lw Mf Mm Mr Ms Mx Ni Ns Nx Og Oh Om Pe qC Uk) qC(aD Bb Bc Ch Cu dB Dc Dl dM Fa Fb Ip It jL Jr Jt Kc Kk Kp Kr Ld Lx Mh Mp Mt On Ou Ow Pd Pf Qb Ql Qm Rb Uf) Ij(Ax bA bV cI dN Ed Fa Fi Hu Iz Jn Lv Lw Mm Mp Ms Nb Ne Ng Ni Nj Nl Ns Nu Nx Og Oy Pb Sh Uf Ur Vb Yk Wm) Kq(bA Dp Ed Ex Fi fN gW Ib Id Ii Il Jd Je jF Jo Kg Kj Lw Mk Ms Ne oN Ow Qu rA rB Ss Us Uu vS Vv Wc Tl Tj) Pe(aA Aj bV Ch Co dN eC eP Fi Gp Hr Ik Jg Jy Lj Mp Mu Nh Nk Nr Nt Nx OH Om Ou QD Uf Ur Wc Ye Xa) Ax(aA aC aI aU bB bF cT dG dM Il Jl Jp Jy Ky Lv Lx Nb Nd Ng Ni No oH Ok On Or Ou Pb Uk Ur vS tF) Nb(Ik Ip Ir Jq Jr Js Lh Lv Me Mp Mq Nd Ne Nj Nl Nr Nv Nx Ny Pb Pg Qb Un Ur Wc Zq Ye Tl Xa Ti) Lj(aI aM Ba bW cT Cu Di Ha Hw Jn Jo Jt Kk Ko Mi Mr Or Pc Pj Qg Qm tU Ur uT Vi wB We Wh wP Zq) Uk(Bc Cs Cu Dc dF Fa Fp Ir Jn Jp Jq Jr Kn Ko Lh Li Mt Mz Nm Nr Ny Om On Pg Pj Po Qh Tn Tr Uc) Qd(aC An bR bS bV Ch cT dE dF dN Dp eC eP Id Iz Jy Kj lN Mm Mr oH pF Qv qY Ul Un Ur Us Ye) Jr(bA bZ cV Hu Ik In Ip Ir Jl Jn Jq Js Lv Me Mm Mp Mq Ms Mu Nj Nk Nn Nr Ns Pb Pd Pz Qb) Lx(AD Aj An bR cL cO Cs Ct Cv Dc dH dl dJ dM dN Dp Fi Gp Jy Kd Kk Kn Ul Un Vc Yk) Uf(Ch Cs Fa Fp Im Is Iz Kj Kk Mq Ms Oi Oy Oz Pb Qa Qc Qm qX rB rS St Un Ur Us uV) Un(Aj bA bN Cs Ct Id Iz Jl Jo Jy Kg Kj Kk Li Mq Nd Ne Oh Qe Qv qX Um Us Wc Wm) Fa(Aj bL Ct eC Gp Gz Id Jp Kd Kk

Figure 1 Continued

Ne Ni Nk No Oh Or Oy Oz Pb Pj vS Tj Th) In(aA Ad BA Cs Cu Dl Fy Iv Jm Jq Kn Ko Mp Nl Nr Pz Qh Rf Rm Tr Vq Wm) Jn(aA Hu Ik Ir Jg Jp Lw Mi Mp Mr Ms Mx nD Ni Nr Nt Oh Pb Pc Pg Va Vq Ye) No(aA aC bR cT cV dM Gp Hb Iz Jo Jt Kd Kp Mm Or Qm rB rX Sh Ul Ur Yk) Ng(bA Bc Cu dF Dg Fb Fy Hu Id Ik Jd Jq Jt Ke Nn Pg Pj Qh Qm Uc Vq Xa) Im(aD al aN bB bR bV bW cl dF eP gP Id Iz Kk Kn Ko Or Pj Qv Tv vS) Aj(Ap cG cT dF Ef Fy Id Jd Jl Ke Kl Ko Lh Li Nt Ny Om Pz Tn Tr) Nd(Aa Ih Ip Ke Ma Mi Mn Mr Mx Nr Nx Ny Pd Pz Qb Qc St wD Zq Xa) Is(Fi Id Jy Ke Kj Kk Ko nC nL oH Ou qD rZ Ua Ul Us Va Wc We Tl) Qe(bV cT dF Dr Id Kd Kn lX nD oH Or Ou pF qD qY Rt Ul Va vS We) Jq(Jg Lu Ma Me Mh Mp Mu Mx Ni Nr Ns Nv Og Oh Om Pb Pc Pd Qb Wm) Ur(Ad Cu Id Jl Jp Kn Li Mt Nr Ny On Pg Pj Qm Rm St Tr Uc wB Wm) Ik(Js Jt Lw Mi Mm Mq Mr Ms Mx Na Ni Nu Nx Ny Og Pb Pc Pg Qb) Qa(cT Cv Dp Dr eC Gp Id Jy Kg Kj oH Ou pF Pj qD Qm Qv qY Us) vS(Ad aW Fy Jl Js Kf Kn Kx Lh Mt Nm Nx Ok Pg Pj Qh Tv Uc Us) Cs(aC aI aU bA bB bF bZ cG dM fN Gp Jp Mt Ok On uM wB wP) Ed(Bc fR Gc Id Jp Ko Lh Mt Mz nI Nr On Pf Pj Vi Wd Yi Ti) Wc(Et Ex Jy Li Mq Mr Ni Nr Ny Om Po Ps Rm St Tz Uw Yi Xa) Pb(bA Cu Iv Js Kn Mq Nx Ny Oh Pd Ps Qb Ry St Vi Vq Yi Zq) Jl(bA bR bS cA Ch Ct dM Hb Iz Lw Nh Nx qD Qg Qm Us Ye) bF(aA aD aI aJ An bA Bc bR cA cC cF Ch cT dE dG dM Fp) cG(bM bR bS bU cA cF cI cK cO CT dE dJ dM Fp hA qX) wD(aW bS cC dM eD iA jD jY Ly Ny Ou Ow pY rB rX Tj tF) Nu(aA Hu Ip Js Lw Mm Mp Na Ni Nn Nr Ns Nv Pc Pz) Oh(aA Ct Hu Jg Lu Lw Mr Mu Ne Nl Ns Nv Om Op Ye) Ni(Ir Js Jt Lv Mm Mp Nc Nj Nl Pg We Zq Xa Ti) St(Bc cI dM Eq Gp Jy Ms mW Nk Or Oy Oz Qv Wm) Ke(Ch Ib Ii Il jD jM Kg Ne Oy qX qZ rA Us Wm) aC(Ad aI AP aX Bb bE bZ cT DG Dl Mq Mt) Nr(aA bA bR Ch dM Fi Lp Lv Me Mp Mu Or Ye) Jg(aA Ct Io Lu Lw Mh Mr Mx Nc Nj Nl Nx Uu) Xa(aM Et iO Iv Jy Mr Nc Nl Oz Ql Rm Va Yc) Li(aD bR bS Ch Ct dM eC Jy Kd Kj Pj qY Tj) Me(Aa Ir Js Mm Mn Mp Mu Nh Nn Nv Ny Pz) Mz(bA cT Hu Hw Js Lu Mh Ne Nl Nv Pc pF) Jp(An Hc Hw Id Iz Jt lY Mm Mr qX rB Wm) Oz(Cu Id Kk Kn Pj Vi Wb Wd Wh Yi Zq Ti) Pg(bL hA Ir Mp Mx Nj Oy qD rX rZ uM Wm) dF(aD An aO bR cA Ch cI cK dE dJ nD oN) Fp(aI bA bB bR cF dM Du lX Vi We Wh) Ny(aA aN Hv iB Lw Mf Mi Mr Mx uM Ye) Pf(bV Cv Dr Kd Kg Kn Ou Pj Rg Ul Yk) Mq(dE Kn Ko Lv Mp Nj Nl Nv Qb Tr) Nx(Js Mh Mp Mu Ne Nj Nl Nv Om Qb) On(Ao bL Ch cI Co Dk Iz oN Rt Vb) wP(Ad Db dJ eD hO jO Kp nW Pj Wm) Ct(Bc EF Lh Nt Om Qh Tn Tr) Ir(Il Mi Mm Mp Ms Mu Mx Pz Rt) aA(Ip Js Mf Nh Nj Nt Om Pz qY) cE(aJ aM bA Bc bM bR cA dJ dN) qZ(bL bW Or Ql Qy Rb Rm Ua Vo) Lh(Hq Hx Kg Lw Md Mm Nc Of) Nv(Mb My Ne Nj Nl Ns Og Oy) Lv(Hu Mr Mu Mx Ne Nl Qb) Tr(Kj pS vV wH yD yL zI) Pj(dM jK Ms qD uV wB wF) bZ(Ad Bb bL cH dE dJ nD) Ch(Cu eF hB Jd oF Qm) Po(Jt Lu Lw Mm Og Tj) Et(Dr mM rX rZ tT Vc) Nh(Ip Jt Mm Nc Nn Pc) Js(iC jK Mm Ms Mu rZ) Om(Hu Lu Mh Mr Mx Nl) bA(Ad Bc bS Dc dE Oy) nD(bQ eC gL hB iA Pi) qD(Ih Jy Kn Lw Mp rX) Wm(Hb Mt Ok Ps rS) Id(eZ Gp Il qX rC) Iv(fR Hv Lw Mi Zq) aI(Bc cI cT dM dN) uT(dB jO nW oK Rb) Ad(Gp Jo Kj Oy) Nn(Ms Nj Ns Ye) Nt(Lw Mm Mr Pc) Mt(bR cI Cv Yk) Mu(Ne Nj Nl Pd) Il(Eq Sf Sh Yl) Qb(Mb Ms Nj Wh) Ok(cI Iz jO Qv) cV(nl nN Rf Vq) fR(aN cB dR gP) Ps(Mh Nc Ye) Oy(Fy Tn Uc) dB(nI wB wH) dG(bL bR dE) hB(dJ Uy Vb) qX(Nw Ql uM) Bc(aU oH) Cu(bL Gp) Ji(Dp Fy) Kp(fN uM) Vq(mS mW) aJ(bR cF) dM(uI zH) nI(Db pF) wB(Kr nW) rS(Fb Ko) BbbB DrFw GpeP NmxA MbJt MmHu MpNj MsPz NeNk TzVa WbLd QhjV YeOw KfuM KgUw LpRm QljK NwOu aMcT eCkI eDmH nWvW

Constrained panels with 2 analytes, where 1.0E-3 >= 'AUC p-value' > 1.0E-4. Contains 2,896 panels of 193,455 total panels evaluated. : Cs(aA AD aJ aM An Ar Aw Ba Bb BC bR bW cF cL Cp cT dE DG dJ dN eC eF FR Ha Hu Ij Il Im Jl Jq Jy Kk Ky Lh Lv Lw Mr Ms Mw Nb Nd Ng Ni Nk No Nr oE OH Om Or Ou Pj Qb Qg Qm qX sC Sr Ur Wh Zq Ti) dM(AD An aQ aU BB Bc bL bR bU bZ cB cE cF cK Ct Cu dE dF dJ eC Fa fN Fr Gp Hb Id In Jj jK Jq Jy Lh Mq Mr Mt Mw Mz Nb Nd Ni Nv Ny Oh Ok Om On Or Oz Pg Po Qb qD Qh Qm qX Rf rX rY Sr Uf Uk Ur vT vV) vS(aD bA bV cG CU cZ DB Dc dF DG dJ Dl Fp Fr Fw Ha hB Ih Is Jt jY Kd Kk Lx Mj Mq Mr Mx Nr Nt Nu Ou Pd Pe Pf Ph Pi Po qC qD qX qY qZ Ri Rm rN sM St Ur uT uX Vo Vv vW wB wJ) Uk(aA aI An BA BB bV bZ cE Cw dG Dk Dl dN Ed Fb Fw HB Ih Il Ip It Iv Jg Jm Js Jt Jy Kf Kk Kr Kx Mm Mp Mq Nb Nd Ni Nt Nv oE Or Pd pF Pz Qb qC Ql Qm qX Rf Rm Tz Up Wn Wm) aA(Ad aI aM aU BB Bc bM bR cE cF Cu Dc dE Dg dJ eC Fa Gp Hu Ij Il Jj Jm Jq Jt Lw Ma Me Mh Mm Mn Mq Ms Mw Nb Ne Ni Nl Ns Nv Oa Pb Pc Pd Pj Qb QC qD Qm rC Rf St Uf Uh Vt) qC(Ad Af aG aI AJ An As aZ cH Cv Cx cZ Db dE dF dG dL Ed Fp hB hW Ib jE Jj Jq Jy Kf Lh Lw Mq Mr Nb Ng Ni Nr Nv oF Om Po qA Qc Qh qX Ra rB rX sM St Tr Uc Up Ur uT wB) Pb(Aa aJ bV dF dG dN Dr Ed Ex Fb Fy hB Hl Hu Ih Ip Jt Kf Kk Ko Kp Kx lX lY Me Mm Mp Mr Mu Mx nA nC Nd Ne nI Nj NL Nm Nn Nr Ou Pj Pz Qh Qm Tn Tr Vh Wd Wh Yl Wm) Qm(AJ bA cI cT dE dF dG dN Ed Fa Fp Fr hB Il jK Jn Jr Jy Kd Kj Kk Lh Li Lw Mq Mr Ms Mt Mw Nb ND Nl Nk Nr Oa Oh Ou Oz pF Qh Qv qX Rf Ul Va Wm) bA(aD aI aM aU bB bL bM bR cF cK dF dG dJ Fa Fr Gp Hb Ib Id Ih Im jD Jp Jq Jy Ko Lh Li Mq Mr Mt Mw Nb Ni Oh Ok Om On Or Oz Pj qX Rf St Uf Ur Wc Wm) Nr(aC aD aI AJ bB Bc bV bW Ct dE dF dN Dr Hb Hu Jy Kd Kj Kk Lu Lw Mm Mr Ms Mw Mx Ne Ng Ni Nj Nl Ns Op Ou Pc Pg Pj Qv Rf Sh Ul Us Vc Vi Xa Wm) Ax(AD AJ aM AN As Aw Ba Bc bR bW cF Cp Ct dE dJ dN Dp eC Fr Ha Hb Hu Jq Kd Kk Kn Ko Lw Mc Mm Mq Mr Ms nI Nk Oi Om Oy Pj Uf Ul wB) Gp(aC Aj aM As bM cI cN Cp Ct Cv Dc dE dG dN Dr Fp Jj Jl Jt Kn Ko Kx Lh Li Mq Mr Mt Mz nD Ng nI Nm Nt Oh Om Pg Pj Po Qh Rf Tr Vq Wm) In(Aa aM Bb cE Cp cV Dc dE dF DG dL dN Dr eC Fb hB iC Ii Il Ip Jo Kf Kx Lv lY Me Mm Mq Nb Nd Ne Nj Nn Ny Pe Ps Qc Tn Uc Yi Zq Xa) Oa(Ad Bc CT Cv Dc Di Dp Dr eQ Ha Hb Id Il Jq Kd Kn Kp Lh Li Lt Lv Lw Mq Mr mZ Nb nD Ng nI nJ Nm Om Or pI Qv qX qZ Tr Ul uT wB wP) Ur(dN Ed Fa Fb Fp Fr Fy Ih Il Ip It Jg Js Jt Kd Ke Kf Ko Lh Mw Mz Nd Ni Nm Oh Om Ou Oz Pd Pi Po Pz Qb Qh qX Sr Tn Us Vq wP) Aj(aI aU Bb bF Bg cE Cp Dc dG Dl eF Fb Fp Hu Il Jn Jt Jy Kk Kn Kp Lj Nb No Nv Oh Pd Pg Pj Po Ps Qh qZ Rf Sr Vo Vq) Bc(Ad aJ An bL bR bZ cA cF cG cI cK cT dE dG Dp Fa fN Fp HB Il Jy Kj Kk Lj Lv Ms Mw Nb Nd Ni oF Or Ou Qv Rf Wc) Mw(AD aI An bR cI cT dE dF hB Hu Jl Jn Js Jy Kd Kn Ko Kp Lh Lu Lw lY Mf Mm Mu Nx Pc Pd pF Pg Qv Uf Us Wc Ti) St(bV cT dN Dr eC Id Jl Jp Jq Kd Kj Kn Ko Kp Li Lv Lw Mq mS mZ Nb Ne nI nJ No Oi Ou pF qD qX Uh Ul Un Us Vi) bZ(aD aI aJ aM An As aU bB bM bR bW cA cF cK cO Cp CT Cv Dc DL Dr Hl Id Ih Iv Kd Mz Ng nI Pj qX Us Yl) Nd(cG Cu dF Ed Fb Hb Hu Id Il Jo Kk Ko Kx Lw Me Mj Mv Nf Ni Nu oE Oz Pa Pc Pj Ps Qh Rf Rz Tn Tr Uf Uw Tl) Mq(Ad bR Ct Cv Dc dF Dr eC eP Fb Fy Hu Id Jt Kk Kp Me Ms Mu Nc Ne Ni Nn Pj Rf Sj Sr uM Vi Ye Xa Wm Ti) Ij(aC aD bR bW Ch Cv dE Dp Dr eC hB Il Jy Kg Kj Kk Lu lX Mb Me Mf Mu Mx My Nc Or Ou Ow Rt Si Us Va Ye) Qb(Ad An bR bV cV Di Hu Jt Jy Lu Lw Me Mm Mp Mu Mx Ne Ng Nl Ns Nu oE Og Pd Pe Qg Tr Uf Uw Vi Ye Xa Wm) Pg(aC Ad An bR bS cA cI Co CT dE Ed fN Hu Hw Lu Lw Mm Ms Nc Ne Nl oH oN Pj Qv Rf rW vV wD wP yD Tj) Uf(aM cI Dp eC Id Il jD Jl JO Jq Jy Kd Kg Kn Li Lv Lw Ml Nb Ne Ni No oH Or Ou Rf rX Sr Ul uN yL) Fp(Aa AD aM bV bW CT Cu Cv Dc dN eC Ha Jy Kd Kk Kn Ko Kp lY oE Or Ou Pj Sr Tr Vq Xa Wm Ti) Ny(aC Ad An As bR CT Dc dE dN Ed Hw jI Kd Lu Mh Ms Ne Ng Ni Nj Nl Pc Pd rS rW rX rZ wP Tl Wm) Mt(Aa bQ bS bU bV cA cK cT Dc dF dN eC Fi fN Id Jy Kd Kk Kn lN Or Pj Rf rX Tv Ul Us Vq Tl Xa) Nb(aC aI bR Ct Dr Hb Hu Ih Il Lw Mf Mh Mm Mr Mu Mx NC Ni Nn Pd Pe pF Pj Pz Qc Wb We Tm Wm) Ed(Ad Bb bF Dr Fb Fi Fr Hb Jd Jg Jn Jq Jt Kd Kk Kn Li Mm Mp nD Nm Oh Om Qh Rf Sr Tr Vh Yf) oE(Ad As bG cH Cu Cv dB dD dF dN Fy hB Ip Jq Jy Lh Lw Mr Ms Ne Ou pF Po Tv Us yL Wm Ti tF) Oh(An bL bR cN dE Dr fR Hb Hw Id Jl Jt Jy Kd Kk Kn Kp Mm Or qD Qv rS Sr Uh Um Us Va Vi) aC(aM An As Aw bB bC bR bV bW cF cN Cp cR cS CV Cw Dc dL dN Ih Jp Li Ni Ok On Po Ps) Ng(aI Ap Bb Bg cG Cp cV Cw Dk Dl Ef Ez Il Jy Kk Kl Mg Mm Mp Ps Pz Ql Qt Rf Uw Zq Wm) Xa(bI bR dN Gz iJ Il Ji Jn Kg Kk Kq kR Ld Li Lj Lv Mc Mh Nq Ow Po Qd Sh Sr Un Vt Wm) Mr(Ad aI aJ Ar bR bV cF cT Dc dF eC Ib Jq Jr Js Jt Ko Mp Mu Nh Nu Nv Nx Tr Yk Ye) bF(Ad aF As bL bM Bn bW cH cK CO Cp Cq cS Ct Cu Cv Cw Dc Dl fR Id Iv Jr Mz qX) Fa(Ad Ch Cv

Figure 1 Continued dN Dp Dr Fi Hq Il Jl Jq Jy Kn Ko Kp Lw Ms nI nW Ou Qg Ul We Yk Yf) Ye(aP Ba dF Fw Hp Hu Ih Il Jk Jy Nu Nv On Pz Qc Ql Rf Sr Tz Un Ut Uw Vq Vu Wh) qX(Ad Ar Bb cE cJ CU cZ Dc dF iC Jy Kp Kr Li Lx Ou qD Qh qY rW Tr Uc Ut Wm) Ne(dG hB Hu Il Ip Ir Jn Jq Jr Js Jt Kn Kx Mp Ni Nl Nn Nu Pd Pz Qc Qh Rf Vt) Pe(Cv Dr fN Hu Ip Jq Jr Js Jt Kd Kj Ko Me Ni Nj Nv Pa Pj Pz Ul uM We wP xA) Wc(dF Fy hG Iv Je Jh Jr Kk Ld Lh Mz Nq Nv Ok Pi Qd Tn Ut Vq Vu Wd Wh Zq) Jl(Aa aD cT dE Gz Hu Id Jg Jy Kd Kn Mf Mk Mm pF Pj Qv qY rX Sr Ua We Tj) Ct(Ap Bb Cp Dc DG Dl Hu Id Ih Jd Jt Ke Ko Ni Nv Nx oF Po Pz Uc Vt) Lj(Ad Cv Dc Dp Fy Hb iB Id Kd Kn Kp pS qD Qv rR Tn Tr rV Ul Uw WD) Rf(aI aM bB bV bW dJ dN eC eP Il Jp Ko Lw Ms Ou Oz pF Qc Qh Qv Vt Wm) On(bR bS dE dN Dp eP Eq Fi Hc jD Kd Kg Kj Kk lY nD Or Ow Ua Us Yk Tl) Uh(aD aM bV cI Cv Dp Fy hB Hv Jp Jq Jt Kj Kk Ko Kp Kr mM Ow Qh Rj Ul) Fr(AD An As aU bM Ch cI cT Dc dN Dp Jt Kd Kj Kk pF Pj qY rX Ua) Nj(hB Hu Ih Il Ip Ir Jq Js Jt Me Mj Mm Ms Mv Mx Nk Nu Pd Pz Qc Zq) Sr(aI bV Dp eC eQ eZ Fi hB jD Jp Jy Kj Kk Kn Ko Lw Mm Mp mW Ou Qc) Lh(AN bL bV Ch cI dE Ib Il Iz Jy Kj Kk lX lY nC nL Qv uM Us Tj) Ar(As cS Cu Cv Cw Dc dN Dp Jr Jy Kd Kk Kn Ko Kp Pj Ri Ul Us wP) Lx(bV cF Dr eC Fy hA hB Id Ko Kp Or Ou pF qY Rg rQ rS wD wP Yf) Ni(Aa Ad aI dF fN Hu Ih Ip Iv Jr Ko Nn Pd pF Pj Pz Qc Qh uM Uw) aJ(AD aI An As Bb bL bS bU cA cB cG cK dF Dr Jj Jr Mz Oz Vq) Nl(Hu Il Ip Ir Jn Jq Jr Js Jt Me Mm Mp Ms Nk Nn Nu Pd Ps Pz) Im(bS cA Ch Cv Gd hB Jy Kd Kj lX lY nA nD Ou rX Ul uT wB wP) Ke(Ao cI Co Cp Dk Dp Fy Hc Hq Iz Jk Kj Lw Md My Nv Ou Ut) nD(aZ bR cV Db dD Et hC hV Ji Jp jQ Kq Kz oK PF Qa Tz) Mz(aI bR cE cN dF dG hB Ib Jt Jy Nc Nx Tv Ul Us Tl Wm) Jj(bB bV cE cI cN cT Cw dG dN fN Hv Hw iA Lw Mi Pc Wn) Oy(cT Cu Dc dF Id Jd Jh Kd Kn Ko Mu Nn Pd Qh Ut Vs We) Ad(aI Ba cE cG Ch cT dF dG Hb Iz rB rS Us Uu wB yL) Mm(Ih Il jK Jn Jq Mb Mh Mj Mu Mx Ns Nv rX Vt wD Zq) Jp(bL bR cI cT Cv Dc Dp Jy Kd Kg Kj Kk Kn Or rX Ul) cV(An bM bR cA cK dE Dr Fb fR Ih Kk Nt Ps Un Wh Wm) wP(Bb CH dE Is Kn Kr Mf Mh Nt Qd Qh Ql qY Rb Vo) Cu(An aU cA cI cK cT dE dJ Hb Ii jD Jk Ms rB Tv) Jr(aI bR cE cN cT dE dF dG Jt Lu Lw Mi Mx Pc qY) Pj(cI eC hB Il jI Jy Kg No Or pF Qh Qv rS Tn uT) qD(Ch Cv DB Dc jL Jq Js Kc Nv Nx qA uN wF Wm) Dr(Ba dF fR Il iO Is Kq kR mZ No pF Qd Rm Uw) Mp(Hb Hu iB jK Lu Mb Mf Mh Mx Nc Ns Og Pd Wm) Id(Fy Hb jD jK Jy Kk Li Ms No Or Ou pF Qv Vt) Ko(bN cI dN eC hL jD Kj Li No Oz tN uM Vt vV) Ps(bR cQ Fi Gz Jh Kc Me Nq Pa Qv Ri Va Vt We) Vq(aZ cN cR fB lX nC nI nJ oF Oz pF Qv Va Yk) Ch(Ba Bg Fb Fy Hu Jg Ky Om Qh Tr UT) Lw(Js Lv Ma Nh Nn Nv Nx qY uM Un Vt yL) Ip(Hu Ih Iv Me Mh Mi Mx oF Og rX vV wD) Jn(aN Kk kP Lp Lu lX lY Nv Nx Pd We Wm) Jq(bN Hu Jt lN Mb nL Nx Pz qY rX Un Vt) Li(bV Cv dF dN Dp iB Kk Kn Or Ou Rg Ul) Ok(bL bN bR bV Dp eC Jy Kd Kk Or Ow rX) Oz(dF Fb Fy HB Jd Kd Kp oF Qh Qv Wm) cE(aD An As bL cF cI cK cT dE dL Ih rA) fR(aM An aQ aU AW cF Db dJ Me Nw Qc) Il(Aa Fb Hb Js Lv lX lY mS Va Yk Tl) Ir(aN Hu Lp Lu Pc Pd pF Tr Va We Tl) Qe(Aa eC Fy hB iB iC lY mS nA rX rZ) cG(aD An As aU cH Cv Dc dL rA vV yL) wD(iO jP Mf Nx Qd rR rY Vv wF tL Wm) No(An aU bV Dp jK lX Ou rZ Va We) Yi(aZ Fw Gz iO Iv Kg mZ nF Pa Pc) Un(cI cT Fy oH Ou pF rC sC uM Va) aI(aM An Ba Bb bL bM cF cN dG dJ) bR(aP bB dL Ex Ih nI nN Nv Po Zq) dE(aP Ba bB dN hB Ih Po uT wB wH) eC(Em Kk Kn Kp Kq Kx Ld Pf Uc Us) Ms(Aa Fb Hu Iv Jt Lv Mu Nu Tz) dF(bM bS bU cF cO Dc dH Hq rA) dG(An Bb bS bU cA cF cK cO dJ) hB(bL Lu nI nJ Nk nW oN uM Ti) wB(cH Hc Hq Hu Qh Qy Rb Ri Wm) Nv(bL cI Jt Lu Mf Mh Nc qY) Uw(Gl Gz iJ Kc Kj Ld Pa Qv) jK(Ez Fb Jd Pf Qh Rm Tr Wm) rX(Jg Js jT Ma Nw Qa Qd qY) yL(As dB Jy Nm Rb rS Uc Vs) Po(aN bL bS bU Kk oH oN) Me(Ik Jt Ma Mx Nm Pc Pd) Tl(Dk Jk Jy Or Ut Vi Vu) Nx(Hv Lu Mi Mx Nc Pc uM) Vt(bJ Fy mW Qc rC Ul zH) cT(aD An bM cF cH Dc eP) dN(aU BB dJ Hb Qc Qh) uT(bL Kz Ou Ow Ri vV Wm) Ba(aD aM bB cA cI Ti) Et(lX lY mT nC nL uX) Nk(iC Js Nc Qh Rm Tn) Qa(Aa Fy lX lY rC uM) Vi(iO Kg kR mZ Nw Pa) eP(dL Gl Ik Kq Qc Rm) qZ(aD Ib Kn Ou Ow vV) pF(aD cH dJ Ih Kd Ld) Nu(Jt Lu Mx Nc Pd) Hu(Js Mu Og Pz Va) Zq(Ap Fw Or Qv Va) Qd(Fy lX lY Ou rZ) Wh(Ex Fw Or Ow Va) nW(rN tV uG uN uU) Aa(Lu Lv Mb Nh) An(aM aU bB dD) Bb(aU cN dD dL) Wm(Ih Jg Om Qc) Nn(Mb Mi Mx Pd) Mh(Nm Pz tU Wb) Tr(Hb qA yH tM) Tn(bL Iz Jk Ua) Jy(cI Ql rA Rt) Kq(Ou Rt uM Vb) Og(Jt Mu Pd Pz) Pf(Fy lX lY xA) nI(aZ iA Kz Pi) pS(Fb Ou Ow Qh) uX(dB jO Kr uM) Db(kI rN vI) Ti(bH jI Or) Fi(Ex Fw Nw) Ji(lX nC nL) We(Fw mZ Va) Kn(rB sC Um) Pc(Ih Iv Js) aM(Hb Kk rC) bB(bM cF cI) iC(jO Ow qY) Fb(Or sM) Fy(Jo Rt) Nq(Eq Yk) Mb(Mu Na) Nc(Mu Pz) Hw(Ik Iv) Is(Lp Yh) Qh(aN rB) Kp(hL yD) Rm(rB Yk) dJ(Cp zI) dL(cF rC) nO(hX lK) lY(hX Qc) qY(jY rZ) BogV DgaD DlrC Malh MiNh MlWb MxPd UcKj HvIk PzVa JscN KfsC KkqA KrxA RzmZ RiwF OmbL UyhG aUcU bMdD dBvI eDlX nCiB tVjO jDoF sMjT jRvV

Figure 1 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.0E1 | 6.2E1 | 8.2E1 | 6.6E1 | 5.8E1 | 4.1E1 | 1.0E0 | 1.3E1 | 4.8E2 | 1.6E2 | 1777 | 12 | 298 | 12 | 0.43 |
| Ad | ug/mL | 3.8E-2 | 8.1E-2 | 9.1E-2 | 1.1E-1 | 3.8E-1 | 1.1E-1 | 2.7E-4 | 1.8E-2 | 8.5E0 | 3.5E-1 | 511 | 8 | 198 | 8 | 0.65 |
| Af | ng/mL | 1.2E0 | 1.3E0 | 1.8E1 | 4.6E0 | 6.6E1 | 6.7E0 | 1.7E-3 | 1.7E-3 | 5.3E2 | 1.8E1 | 511 | 8 | 198 | 8 | 0.47 |
| Aj | ug/mL | 1.5E0 | 4.0E0 | 2.6E0 | 3.3E0 | 2.5E0 | 2.7E0 | 1.5E-3 | 8.4E-2 | 6.1E0 | 5.8E0 | 511 | 8 | 198 | 8 | 0.57 |
| Al | mg/mL | 8.8E-5 | 6.9E-5 | 2.4E-4 | 2.9E-4 | 4.0E-4 | 4.2E-4 | 2.3E-6 | 2.2E-5 | 2.2E-3 | 1.1E-3 | 511 | 8 | 198 | 8 | 0.51 |
| An | U/mL | 5.0E1 | 8.0E1 | 1.9E2 | 1.4E2 | 5.6E2 | 1.4E2 | 9.8E-4 | 1.4E1 | 7.8E3 | 4.3E2 | 511 | 8 | 198 | 8 | 0.61 |
| Ao | pg/mL | 9.0E1 | 1.2E2 | 4.7E2 | 7.8E2 | 3.2E3 | 1.5E3 | 1.5E0 | 2.1E1 | 3.9E4 | 4.5E3 | 511 | 8 | 198 | 8 | 0.62 |
| Ap | ng/mL | 3.2E1 | 5.2E1 | 4.7E1 | 8.8E1 | 4.9E1 | 9.0E1 | 8.4E-5 | 1.4E1 | 3.3E2 | 2.4E2 | 511 | 8 | 198 | 8 | 0.65 |
| Ar | ng/mL | 9.8E-1 | 3.6E0 | 1.1E1 | 5.3E0 | 1.8E2 | 7.1E0 | 3.4E-3 | 1.0E-1 | 4.1E3 | 2.2E1 | 511 | 8 | 198 | 8 | 0.65 |
| As | ng/mL | 8.7E-3 | 6.3E-3 | 1.5E-2 | 1.6E-2 | 5.7E-2 | 2.4E-2 | 1.7E-3 | 1.7E-3 | 1.2E0 | 7.0E-2 | 511 | 8 | 198 | 8 | 0.47 |
| Aw | pg/mL | 1.6E1 | 2.2E1 | 1.6E1 | 2.1E1 | 6.3E0 | 6.5E0 | 2.9E-2 | 1.1E1 | 5.1E1 | 2.9E1 | 511 | 8 | 198 | 8 | 0.71 |
| Ax | ng/mL | 2.1E0 | 2.3E0 | 1.5E1 | 1.0E1 | 6.0E1 | 1.5E1 | 1.2E-2 | 1.3E-1 | 7.7E2 | 4.4E1 | 511 | 8 | 198 | 8 | 0.53 |
| Ba | ng/mL | 6.2E1 | 8.8E2 | 4.4E2 | 3.7E3 | 1.1E3 | 5.3E3 | 2.7E-1 | 8.5E0 | 8.1E3 | 1.5E4 | 511 | 8 | 198 | 8 | 0.73 |
| Bb | ng/mL | 3.2E0 | 4.2E0 | 6.6E0 | 9.2E0 | 1.4E1 | 8.8E0 | 4.1E-1 | 2.2E0 | 2.5E2 | 2.5E1 | 511 | 8 | 198 | 8 | 0.65 |
| Bc | ng/mL | 3.8E1 | 9.5E1 | 1.1E2 | 2.5E2 | 1.9E2 | 3.9E2 | 1.1E-1 | 2.0E1 | 1.2E3 | 1.2E3 | 511 | 8 | 198 | 8 | 0.71 |
| Bg | ng/mL | 8.1E-2 | 1.1E0 | 5.3E0 | 5.1E1 | 2.9E1 | 1.4E2 | 5.3E-4 | 2.0E-2 | 4.4E2 | 4.0E2 | 511 | 8 | 198 | 8 | 0.71 |
| Bn | ng/mL | 5.6E-2 | 5.6E-2 | 1.4E0 | 1.4E0 | 3.2E0 | 3.0E0 | 5.6E-2 | 5.6E-2 | 5.8E1 | 8.6E0 | 511 | 8 | 198 | 8 | 0.47 |
| Bo | ng/mL | 1.2E1 | 1.4E1 | 1.4E1 | 1.7E1 | 1.8E1 | 1.5E1 | 1.6E-2 | 1.6E-2 | 2.8E2 | 3.9E1 | 511 | 8 | 198 | 8 | 0.57 |
| Ch | uIU/mL | 9.8E-1 | 1.9E0 | 1.7E1 | 1.5E2 | 9.6E1 | 4.2E2 | 3.4E-3 | 2.8E-1 | 1.8E3 | 1.2E3 | 511 | 8 | 198 | 8 | 0.59 |
| Co | pg/mL | 3.7E1 | 8.3E1 | 1.7E2 | 4.3E2 | 9.1E2 | 6.9E2 | 1.5E-1 | 4.2E1 | 1.7E4 | 2.1E3 | 511 | 8 | 198 | 8 | 0.78 |
| Cp | ng/mL | 2.2E1 | 5.0E1 | 3.0E1 | 4.5E1 | 6.3E1 | 2.4E1 | 6.0E-1 | 7.5E0 | 1.3E3 | 7.2E1 | 511 | 8 | 198 | 8 | 0.74 |
| Cq | ng/mL | 3.0E-2 | 3.7E-2 | 2.3E-1 | 1.8E-1 | 2.3E0 | 3.9E-1 | 8.0E-4 | 8.0E-4 | 4.9E1 | 1.1E0 | 511 | 8 | 198 | 8 | 0.58 |
| Cs | ng/mL | 6.6E1 | 5.7E1 | 3.2E2 | 1.6E2 | 1.1E3 | 2.5E2 | 2.7E-2 | 2.7E0 | 1.8E4 | 7.5E2 | 511 | 8 | 198 | 8 | 0.47 |
| Ct | ng/mL | 6.0E-1 | 5.0E0 | 3.7E1 | 9.5E1 | 1.1E2 | 1.7E2 | 1.1E-4 | 5.6E-2 | 6.2E2 | 4.2E2 | 511 | 8 | 198 | 8 | 0.57 |
| Cu | ng/mL | 2.4E-1 | 9.0E-1 | 5.3E-1 | 1.0E0 | 3.0E0 | 7.3E-1 | 9.0E-5 | 1.4E-1 | 6.6E1 | 2.3E0 | 511 | 8 | 198 | 8 | 0.83 |
| Cv | ng/mL | 5.6E0 | 4.5E0 | 2.6E1 | 1.7E1 | 6.5E1 | 3.0E1 | 1.4E-4 | 1.5E-1 | 5.3E2 | 8.9E1 | 511 | 8 | 198 | 8 | 0.42 |
| Cw | mIU/mL | 3.0E-2 | 5.3E-2 | 5.1E-2 | 6.5E-2 | 3.0E-1 | 3.9E-2 | 1.5E-4 | 5.5E-3 | 6.8E0 | 1.2E-1 | 511 | 8 | 198 | 8 | 0.73 |
| Cx | ng/mL | 4.6E-1 | 3.7E-2 | 6.3E1 | 4.0E1 | 1.1E2 | 1.1E2 | 9.3E-5 | 9.3E-5 | 3.9E2 | 3.2E2 | 511 | 8 | 198 | 8 | 0.40 |
| Db | ug/mL | 7.4E0 | 8.3E0 | 9.2E0 | 8.5E0 | 1.0E1 | 5.3E0 | 4.5E-1 | 1.2E0 | 1.4E2 | 1.5E1 | 511 | 8 | 198 | 8 | 0.56 |
| Dc | nmol/L | 1.9E-2 | 1.8E-2 | 8.4E-2 | 6.6E-2 | 6.3E-1 | 9.5E-2 | 5.2E-6 | 5.9E-3 | 1.4E1 | 2.7E-1 | 511 | 8 | 198 | 8 | 0.56 |
| Dd | ug/mL | 7.5E-2 | 8.3E-2 | 1.8E-1 | 2.1E-1 | 2.9E-1 | 2.7E-1 | 8.3E-5 | 3.3E-3 | 3.6E0 | 7.3E-1 | 511 | 8 | 198 | 8 | 0.48 |
| De | ng/mL | 3.4E-3 | 6.2E-2 | 8.0E-2 | 2.3E-1 | 1.4E-1 | 3.8E-1 | 3.4E-3 | 3.4E-3 | 9.2E-1 | 1.1E0 | 511 | 8 | 198 | 8 | 0.62 |
| Dg | ng/mL | 3.2E1 | 5.9E1 | 4.5E1 | 6.0E1 | 4.1E1 | 3.9E1 | 1.0E-1 | 4.3E0 | 1.9E2 | 1.2E2 | 511 | 8 | 198 | 8 | 0.62 |
| Di | pg/mL | 1.8E0 | 4.1E0 | 2.2E0 | 3.5E0 | 2.1E0 | 1.7E0 | 1.8E-1 | 1.8E-1 | 1.3E1 | 5.4E0 | 511 | 8 | 198 | 8 | 0.72 |
| Dk | uIU/mL | 1.6E-2 | 1.8E-2 | 8.3E-2 | 6.2E-2 | 4.8E-1 | 1.1E-1 | 1.1E-4 | 1.1E-4 | 8.9E0 | 3.3E-1 | 511 | 8 | 198 | 8 | 0.52 |
| Dl | ng/mL | 2.4E2 | 2.0E2 | 3.2E2 | 3.5E2 | 3.0E2 | 3.1E2 | 1.7E0 | 7.4E1 | 1.6E3 | 8.5E2 | 511 | 8 | 198 | 8 | 0.55 |
| Ef | ng/ml | 1.3E-1 | 6.4E0 | 8.9E-1 | 4.7E0 | 1.9E0 | 4.4E0 | 5.7E-4 | 9.1E-2 | 1.0E1 | 9.9E0 | 379 | 7 | 195 | 7 | 0.78 |
| Wm | % | 7.0E-1 | 2.7E0 | 3.4E1 | 3.4E1 | 1.8E2 | 6.7E1 | 5.4E-2 | 8.5E-2 | 2.4E3 | 1.9E2 | 416 | 9 | 214 | 9 | 0.66 |
| Po | pg/mL | 6.9E-1 | 1.5E1 | 8.6E0 | 3.3E1 | 2.4E1 | 5.9E1 | 8.0E-3 | 2.6E-2 | 2.7E2 | 2.2E2 | 899 | 13 | 335 | 13 | 0.73 |
| Et | ng/ml | 1.4E3 | 2.0E3 | 1.7E3 | 2.7E3 | 1.2E3 | 1.5E3 | 7.5E1 | 1.1E3 | 5.0E3 | 5.0E3 | 898 | 13 | 335 | 13 | 0.72 |
| Fp | ng/ml | 1.4E1 | 3.1E1 | 2.5E1 | 3.7E1 | 2.9E1 | 2.7E1 | 6.0E-3 | 9.7E-1 | 1.4E2 | 7.9E1 | 931 | 13 | 336 | 13 | 0.65 |
| Fr | ng/ml | 3.7E4 | 5.5E5 | 1.2E5 | 4.8E5 | 1.8E5 | 3.5E5 | 1.9E2 | 5.9E3 | 9.0E5 | 8.9E5 | 1043 | 14 | 340 | 14 | 0.80 |
| Fw | pg/ml | 1.2E0 | 7.8E0 | 5.8E1 | 1.5E1 | 4.5E2 | 1.8E1 | 1.1E-14 | 1.2E-1 | 6.9E3 | 4.2E1 | 380 | 7 | 196 | 7 | 0.64 |
| Gl | pg/ml | 7.2E3 | 2.3E4 | 1.1E4 | 1.8E4 | 9.2E3 | 1.2E4 | 9.1E1 | 6.7E2 | 3.4E4 | 3.2E4 | 370 | 7 | 194 | 7 | 0.70 |
| Nm | pg/ml | 1.4E4 | 4.2E4 | 3.3E4 | 8.4E4 | 8.2E4 | 1.2E5 | 1.0E-9 | 1.0E-9 | 1.6E6 | 4.4E5 | 902 | 13 | 337 | 13 | 0.65 |
| Nn | pg/ml | 1.6E2 | 1.3E3 | 1.9E3 | 1.4E3 | 8.2E3 | 3.1E4 | 1.0E-9 | 1.0E-9 | 1.0E5 | 1.1E5 | 902 | 13 | 337 | 13 | 0.74 |
| No | pg/ml | 1.6E1 | 5.1E1 | 3.8E1 | 1.7E2 | 1.1E2 | 3.0E2 | 1.0E-9 | 1.0E-9 | 2.5E3 | 9.5E2 | 902 | 13 | 337 | 13 | 0.70 |
| Nq | pg/ml | 2.0E0 | 2.5E1 | 2.0E1 | 8.3E1 | 7.6E1 | 1.1E2 | 1.0E-9 | 1.0E-9 | 1.2E3 | 3.0E2 | 902 | 13 | 337 | 13 | 0.66 |
| Nr | pg/ml | 1.2E0 | 8.3E0 | 2.9E1 | 1.2E2 | 1.8E2 | 3.8E2 | 1.0E-9 | 1.0E-9 | 4.1E3 | 1.4E3 | 902 | 13 | 337 | 13 | 0.60 |
| Ns | pg/ml | 1.0E-9 | 1.0E-9 | 9.2E0 | 1.0E-9 | 5.2E1 | 0.0E0 | 1.0E-9 | 1.0E-9 | 1.1E3 | 1.0E-9 | 902 | 13 | 337 | 13 | 0.45 |
| Nt | pg/ml | 1.0E2 | 2.2E2 | 1.4E2 | 3.0E2 | 1.2E2 | 3.1E2 | 1.0E-9 | 5.2E1 | 1.7E3 | 1.2E3 | 902 | 13 | 337 | 13 | 0.74 |
| Nu | pg/ml | 2.0E1 | 1.2E2 | 5.5E1 | 1.2E2 | 9.0E1 | 8.8E1 | 1.0E-9 | 1.0E-9 | 8.9E2 | 2.9E2 | 902 | 13 | 337 | 13 | 0.76 |
| Lu | pg/ml | 1.0E4 | 8.1E3 | 1.8E4 | 1.2E4 | 6.2E4 | 1.6E4 | 3.5E2 | 1.3E3 | 1.3E6 | 6.1E4 | 905 | 13 | 337 | 13 | 0.40 |
| Lv | pg/ml | 1.0E-9 | 4.3E1 | 1.1E1 | 5.4E1 | 2.2E1 | 6.7E1 | 1.0E-9 | 1.0E-9 | 2.6E2 | 1.9E2 | 905 | 13 | 337 | 13 | 0.70 |

Figure 2

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Lw | pg/ml | 1.0E-9 | 1.0E-9 | 3.7E-1 | 7.3E0 | 3.8E0 | 1.5E1 | 1.0E-9 | 1.0E-9 | 8.0E1 | 4.7E1 | 905 | 13 | 337 | 13 | 0.61 |
| Lx | pg/ml | 1.0E-9 | 3.6E2 | 1.7E2 | 8.2E2 | 8.6E2 | 1.2E3 | 1.0E-9 | 1.0E-9 | 2.2E4 | 4.0E3 | 905 | 13 | 337 | 13 | 0.78 |
| Ly | pg/ml | 1.0E-9 | 1.0E-9 | 1.0E1 | 1.3E1 | 2.0E1 | 2.4E1 | 1.0E-9 | 1.0E-9 | 1.6E2 | 7.2E1 | 905 | 13 | 337 | 13 | 0.50 |
| Lz | pg/ml | 1.0E-9 | 1.0E-9 | 4.0E0 | 3.6E0 | 3.0E1 | 1.3E1 | 1.0E-9 | 1.0E-9 | 6.0E2 | 4.7E1 | 905 | 13 | 337 | 13 | 0.50 |
| Ma | pg/ml | 2.9E2 | 2.5E3 | 1.4E3 | 8.4E3 | 3.6E3 | 1.6E4 | 1.0E-9 | 1.8E1 | 6.5E4 | 5.2E4 | 905 | 13 | 337 | 13 | 0.66 |
| Mb | pg/ml | 2.5E1 | 2.5E1 | 3.1E1 | 3.2E1 | 1.5E1 | 1.6E1 | 4.1E0 | 1.3E1 | 2.1E2 | 5.8E1 | 905 | 13 | 337 | 13 | 0.46 |
| Mc | pg/ml | 1.0E-9 | 1.0E-9 | 3.8E-2 | 1.1E-1 | 5.7E-1 | 3.9E-1 | 1.0E-9 | 1.0E-9 | 1.3E1 | 1.4E0 | 905 | 13 | 337 | 13 | 0.53 |
| Md | pg/ml | 1.0E-9 | 1.0E-9 | 4.4E-1 | 1.0E-9 | 3.6E0 | 0.0E0 | 1.0E-9 | 1.0E-9 | 6.8E1 | 1.0E-9 | 905 | 13 | 337 | 13 | 0.46 |
| Me | pg/ml | 3.3E1 | 2.4E1 | 3.2E1 | 3.5E1 | 2.0E1 | 4.7E1 | 1.0E-9 | 1.5E0 | 3.2E2 | 1.8E2 | 905 | 13 | 337 | 13 | 0.41 |
| Mf | pg/ml | 1.0E-9 | 1.0E-9 | 5.4E-1 | 7.8E-1 | 2.9E0 | 1.8E0 | 1.0E-9 | 1.0E-9 | 5.6E1 | 5.0E0 | 905 | 13 | 337 | 13 | 0.55 |
| Mg | pg/ml | 1.6E0 | 1.5E1 | 7.4E0 | 2.5E1 | 1.2E1 | 4.0E1 | 1.0E-9 | 1.0E-9 | 9.2E1 | 1.5E2 | 905 | 13 | 337 | 13 | 0.70 |
| Mh | pg/ml | 1.0E-9 | 2.9E-2 | 1.3E0 | 1.7E0 | 9.6E0 | 5.0E0 | 1.0E-9 | 1.0E-9 | 1.6E2 | 1.8E1 | 905 | 13 | 337 | 13 | 0.62 |
| Mi | pg/ml | 1.0E-9 | 1.0E-9 | 9.0E-1 | 1.4E1 | 1.2E1 | 3.3E1 | 1.0E-9 | 1.0E-9 | 3.2E2 | 1.1E2 | 905 | 13 | 337 | 13 | 0.64 |
| Mj | pg/ml | 1.0E-9 | 2.9E0 | 4.5E0 | 2.1E1 | 2.5E1 | 5.6E1 | 1.0E-9 | 1.0E-9 | 4.6E2 | 2.1E2 | 905 | 13 | 337 | 13 | 0.67 |
| Mk | pg/ml | 1.0E0 | 4.3E0 | 1.3E1 | 4.4E1 | 8.5E1 | 1.4E2 | 1.0E-9 | 1.0E-9 | 1.7E3 | 5.0E2 | 905 | 13 | 337 | 13 | 0.58 |
| Ml | pg/ml | 1.0E-9 | 1.0E-9 | 5.6E0 | 8.4E0 | 7.5E1 | 2.4E0 | 1.0E-9 | 1.0E-9 | 2.1E3 | 8.6E0 | 905 | 13 | 337 | 13 | 0.49 |
| Mm | pg/ml | 6.1E2 | 1.5E3 | 1.1E3 | 2.1E3 | 1.5E3 | 2.2E3 | 1.0E-9 | 6.2E1 | 1.2E4 | 6.5E3 | 905 | 13 | 337 | 13 | 0.66 |
| Mn | pg/ml | 5.6E0 | 1.6E1 | 1.0E1 | 1.7E1 | 2.3E1 | 1.5E1 | 1.0E-9 | 1.0E-9 | 3.5E2 | 5.1E1 | 905 | 13 | 337 | 13 | 0.69 |
| Mp | pg/ml | 1.0E-9 | 1.4E1 | 1.0E1 | 5.8E1 | 3.4E1 | 8.6E1 | 1.0E-9 | 1.0E-9 | 6.3E2 | 2.7E2 | 904 | 13 | 337 | 13 | 0.73 |
| Mq | pg/ml | 1.0E-9 | 1.0E-9 | 2.9E0 | 1.8E1 | 1.7E1 | 4.1E1 | 1.0E-9 | 1.0E-9 | 2.4E2 | 1.4E2 | 904 | 13 | 337 | 13 | 0.62 |
| Mr | pg/ml | 1.0E-9 | 5.7E0 | 2.8E1 | 2.8E2 | 1.6E2 | 9.3E2 | 1.0E-9 | 1.0E-9 | 2.2E3 | 3.4E3 | 904 | 13 | 337 | 13 | 0.67 |
| Ms | pg/ml | 4.1E2 | 5.1E2 | 5.6E2 | 5.0E2 | 6.5E2 | 4.0E2 | 1.0E-9 | 2.1E1 | 5.9E3 | 1.4E3 | 904 | 13 | 337 | 13 | 0.53 |
| Mt | pg/ml | 2.5E-1 | 4.6E0 | 1.1E1 | 1.9E1 | 1.2E2 | 3.1E1 | 1.0E-9 | 1.0E-9 | 3.2E3 | 9.5E1 | 904 | 13 | 337 | 13 | 0.80 |
| Mu | pg/ml | 1.0E-9 | 3.4E0 | 1.3E0 | 9.0E0 | 1.0E1 | 1.5E1 | 1.0E-9 | 1.0E-9 | 2.3E2 | 4.8E1 | 904 | 13 | 337 | 13 | 0.76 |
| Mv | pg/ml | 1.0E-9 | 8.6E1 | 7.0E1 | 2.4E2 | 3.2E2 | 3.1E2 | 1.0E-9 | 1.0E-9 | 4.5E3 | 9.0E2 | 904 | 13 | 337 | 13 | 0.72 |
| Mw | pg/ml | 3.8E1 | 4.3E2 | 5.2E2 | 1.3E3 | 3.3E3 | 1.9E3 | 1.0E-9 | 1.0E-9 | 6.2E4 | 5.3E3 | 904 | 13 | 337 | 13 | 0.74 |
| Mx | pg/ml | 1.0E-9 | 1.0E-9 | 2.8E-1 | 2.7E-1 | 1.5E0 | 6.2E-1 | 1.0E-9 | 1.0E-9 | 3.2E1 | 2.2E0 | 904 | 13 | 337 | 13 | 0.57 |
| My | pg/ml | 1.0E-9 | 1.1E2 | 4.7E2 | 3.7E2 | 3.0E3 | 5.8E2 | 1.0E-9 | 1.0E-9 | 3.9E4 | 1.9E3 | 904 | 13 | 337 | 13 | 0.66 |
| Mz | pg/ml | 1.1E1 | 2.9E1 | 3.0E1 | 6.3E1 | 9.9E1 | 6.8E1 | 1.0E-9 | 2.8E0 | 1.9E3 | 2.0E2 | 904 | 13 | 337 | 13 | 0.72 |
| Na | pg/ml | 1.0E-9 | 1.0E-9 | 7.3E-1 | 1.2E0 | 3.0E0 | 2.4E0 | 1.0E-9 | 1.0E-9 | 4.2E1 | 6.6E0 | 904 | 13 | 337 | 13 | 0.60 |
| Nb | pg/ml | 2.0E0 | 4.0E0 | 3.9E0 | 2.2E1 | 1.2E1 | 5.6E1 | 1.0E-9 | 1.0E-9 | 2.3E2 | 2.1E2 | 904 | 13 | 337 | 13 | 0.74 |
| Nc | pg/ml | 3.4E2 | 4.6E2 | 5.6E2 | 3.8E2 | 7.3E2 | 3.6E2 | 1.0E-9 | 1.0E-9 | 9.2E3 | 8.8E2 | 904 | 13 | 337 | 13 | 0.45 |
| Nd | pg/ml | 2.9E1 | 2.9E1 | 2.9E1 | 2.9E1 | 8.3E1 | 2.9E1 | 1.0E-9 | 2.9E0 | 2.1E3 | 1.0E2 | 904 | 13 | 337 | 13 | 0.53 |
| Ne | pg/ml | 4.4E2 | 3.6E2 | 5.8E2 | 4.3E2 | 5.7E2 | 3.3E2 | 1.0E-9 | 1.0E-9 | 7.0E3 | 1.1E3 | 904 | 13 | 337 | 13 | 0.46 |
| Nf | pg/ml | 1.0E-9 | 1.0E-9 | 3.0E0 | 2.4E0 | 1.1E1 | 5.0E0 | 1.0E-9 | 1.0E-9 | 1.6E2 | 1.8E1 | 904 | 13 | 337 | 13 | 0.53 |
| Ng | pg/ml | 1.9E1 | 3.9E1 | 1.3E2 | 1.1E2 | 2.5E2 | 1.4E2 | 1.0E-9 | 1.0E-9 | 2.3E3 | 4.0E2 | 904 | 13 | 337 | 13 | 0.53 |
| Nh | pg/ml | 6.9E1 | 5.0E1 | 9.0E1 | 5.5E1 | 8.2E1 | 3.8E1 | 1.0E-9 | 1.0E-9 | 5.6E2 | 1.3E2 | 904 | 13 | 337 | 13 | 0.38 |
| Ni | pg/ml | 1.0E-9 | 3.4E1 | 7.3E1 | 1.5E2 | 1.2E2 | 1.9E2 | 1.0E-9 | 1.0E-9 | 1.1E3 | 5.5E2 | 904 | 13 | 337 | 13 | 0.62 |
| Nj | pg/ml | 7.3E0 | 6.6E0 | 1.1E1 | 8.4E0 | 1.2E1 | 7.8E0 | 1.0E-9 | 1.0E-9 | 1.1E2 | 2.9E1 | 904 | 13 | 337 | 13 | 0.47 |
| Nk | pg/ml | 1.7E1 | 2.5E1 | 3.3E1 | 3.2E1 | 4.0E1 | 2.7E1 | 1.0E-9 | 1.0E-9 | 2.0E2 | 1.0E2 | 904 | 13 | 337 | 13 | 0.56 |
| Nl | pg/ml | 4.6E1 | 4.2E1 | 6.1E1 | 4.9E1 | 6.8E1 | 3.8E1 | 1.0E-9 | 1.0E-9 | 1.1E3 | 1.1E2 | 904 | 13 | 337 | 13 | 0.48 |
| Hq | pg/ml | 1.1E0 | 1.3E0 | 1.0E2 | 2.1E1 | 1.6E3 | 5.1E1 | 1.0E-9 | 1.0E-9 | 3.4E4 | 1.8E2 | 900 | 13 | 336 | 13 | 0.56 |
| Hr | pg/ml | 1.2E2 | 9.3E1 | 7.9E2 | 4.4E2 | 1.6E3 | 9.5E2 | 1.0E-9 | 1.0E-9 | 1.7E4 | 3.4E3 | 900 | 13 | 336 | 13 | 0.43 |
| Hu | pg/ml | 5.6E0 | 2.5E1 | 3.0E3 | 8.1E2 | 2.6E4 | 1.7E3 | 1.0E-9 | 1.0E-9 | 6.3E5 | 5.9E3 | 900 | 13 | 336 | 13 | 0.61 |
| Hv | pg/ml | 1.4E0 | 3.2E0 | 4.1E0 | 7.3E0 | 3.2E1 | 9.6E0 | 1.0E-9 | 4.7E-1 | 8.9E2 | 2.9E1 | 900 | 13 | 336 | 13 | 0.70 |
| Hw | pg/ml | 6.5E0 | 3.4E0 | 2.9E1 | 4.7E1 | 3.2E2 | 1.4E2 | 1.0E-9 | 5.1E-1 | 9.4E3 | 5.0E2 | 900 | 13 | 336 | 13 | 0.42 |
| Hx | pg/ml | 8.8E0 | 1.1E1 | 3.9E1 | 1.1E2 | 3.2E2 | 3.5E2 | 1.0E-9 | 1.0E-9 | 9.3E3 | 1.3E3 | 900 | 13 | 336 | 13 | 0.57 |
| Ih | ng/ml | 7.2E1 | 1.8E2 | 2.4E2 | 3.1E2 | 4.3E2 | 3.8E2 | 1.0E-9 | 1.0E-9 | 3.6E3 | 1.5E3 | 904 | 13 | 336 | 13 | 0.63 |
| Ii | ng/ml | 9.4E1 | 8.8E1 | 2.5E2 | 5.4E2 | 6.8E2 | 1.2E3 | 1.0E-9 | 3.2E1 | 1.0E4 | 4.5E3 | 903 | 13 | 336 | 13 | 0.61 |
| Ij | ng/ml | 7.7E1 | 1.3E2 | 2.0E2 | 1.8E2 | 9.9E2 | 1.6E2 | 1.0E-9 | 2.4E1 | 2.4E4 | 6.1E2 | 891 | 13 | 334 | 13 | 0.66 |
| Ik | ng/ml | 1.3E1 | 1.7E2 | 8.1E2 | 3.9E2 | 8.2E3 | 5.3E2 | 5.9E-1 | 2.6E0 | 1.2E5 | 1.5E3 | 898 | 13 | 334 | 13 | 0.67 |
| Il | ng/ml | 3.4E2 | 3.2E2 | 1.3E3 | 3.1E3 | 2.8E3 | 5.1E3 | 1.0E-9 | 1.0E-9 | 1.3E4 | 1.2E4 | 881 | 13 | 334 | 13 | 0.54 |
| Im | ng/ml | 2.1E2 | 7.0E2 | 3.9E2 | 7.8E2 | 6.0E2 | 1.0E3 | 1.3E1 | 5.5E1 | 6.2E3 | 4.0E3 | 897 | 13 | 335 | 13 | 0.64 |
| In | ng/ml | 3.7E0 | 6.2E-1 | 2.7E0 | 8.6E0 | 2.1E2 | 1.7E1 | 1.0E-9 | 1.0E-9 | 4.5E3 | 5.7E1 | 904 | 13 | 336 | 13 | 0.35 |
| Io | ng/ml | 8.1E3 | 1.2E4 | 2.4E4 | 1.4E4 | 1.5E5 | 1.1E4 | 1.0E-9 | 6.6E2 | 4.0E6 | 3.3E4 | 896 | 13 | 336 | 13 | 0.54 |
| Ip | ng/ml | 9.7E0 | 3.0E1 | 1.9E1 | 3.5E1 | 2.4E1 | 2.9E1 | 1.0E-9 | 4.4E-2 | 2.6E2 | 1.0E2 | 896 | 13 | 336 | 13 | 0.66 |
| Iq | ug/ml | 1.0E-1 | 3.1E-1 | 3.2E1 | 2.5E0 | 6.4E2 | 6.0E0 | 1.0E-9 | 1.0E-9 | 1.4E4 | 2.1E1 | 896 | 13 | 336 | 13 | 0.55 |

Figure 2 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ir | ug/ml | 3.5E-1 | 1.2E0 | 3.9E0 | 3.3E1 | 2.8E1 | 7.1E1 | 1.0E-9 | 1.0E-9 | 5.1E2 | 2.4E2 | 895 | 13 | 336 | 13 | 0.71 |
| Is | ng/ml | 1.5E0 | 1.6E1 | 6.6E0 | 3.9E1 | 2.3E1 | 6.8E1 | 1.0E-9 | 1.0E0 | 5.5E2 | 2.6E2 | 896 | 13 | 336 | 13 | 0.82 |
| It | ng/ml | 2.0E0 | 3.8E0 | 2.4E1 | 6.4E0 | 1.4E2 | 8.4E0 | 1.0E-9 | 1.0E-9 | 2.8E3 | 2.4E1 | 896 | 13 | 336 | 13 | 0.56 |
| Iu | ng/ml | 2.2E2 | 1.5E2 | 1.4E3 | 4.7E3 | 4.2E3 | 9.2E3 | 1.0E-9 | 1.0E-9 | 2.9E4 | 2.4E4 | 896 | 13 | 336 | 13 | 0.49 |
| Iv | ng/ml | 1.3E1 | 5.7E1 | 6.1E1 | 3.8E2 | 5.5E2 | 1.0E3 | 1.0E-9 | 1.9E0 | 1.6E4 | 3.8E3 | 895 | 13 | 336 | 13 | 0.77 |
| Pz | ng/ml | 3.9E3 | 1.0E4 | 8.3E3 | 7.1E3 | 3.8E4 | 4.3E3 | 1.3E1 | 1.1E2 | 1.0E6 | 1.3E4 | 896 | 13 | 334 | 13 | 0.59 |
| Qa | ng/ml | 3.5E3 | 1.6E4 | 6.5E3 | 1.5E4 | 1.0E4 | 1.0E4 | 1.2E1 | 6.0E2 | 2.2E5 | 3.2E4 | 896 | 13 | 334 | 13 | 0.72 |
| Qb | ng/ml | 9.7E1 | 2.1E2 | 2.1E2 | 3.0E2 | 4.9E2 | 2.7E2 | 7.9E-1 | 1.4E1 | 8.3E3 | 7.6E2 | 896 | 13 | 334 | 13 | 0.63 |
| Qc | ng/ml | 2.3E2 | 6.3E2 | 6.3E2 | 6.5E2 | 5.6E3 | 5.0E2 | 1.0E-9 | 1.1E1 | 1.7E5 | 1.4E3 | 896 | 13 | 334 | 13 | 0.63 |
| Qd | ng/ml | 9.2E3 | 3.4E4 | 1.9E4 | 5.8E4 | 7.3E4 | 6.7E4 | 1.5E2 | 2.8E3 | 2.0E6 | 2.2E5 | 896 | 13 | 334 | 13 | 0.71 |
| Qe | ng/ml | 9.2E2 | 3.2E3 | 1.9E3 | 4.2E3 | 4.7E3 | 4.8E3 | 1.0E-9 | 1.9E2 | 9.7E4 | 1.8E4 | 896 | 13 | 334 | 13 | 0.72 |
| Jg | ng/ml | 5.0E2 | 1.6E3 | 8.3E2 | 2.1E3 | 1.0E3 | 2.1E3 | 1.0E-9 | 4.0E1 | 1.0E4 | 7.1E3 | 900 | 13 | 336 | 13 | 0.71 |
| Jh | ng/ml | 3.0E0 | 6.1E1 | 2.9E1 | 7.2E1 | 1.2E2 | 8.6E1 | 1.0E-9 | 1.9E-1 | 1.6E3 | 2.9E2 | 900 | 13 | 336 | 13 | 0.77 |
| Ji | ng/ml | 5.3E1 | 2.0E2 | 7.9E1 | 3.4E2 | 9.0E1 | 4.7E2 | 1.0E-9 | 1.7E1 | 1.3E3 | 1.8E3 | 900 | 13 | 336 | 13 | 0.82 |
| Jj | ng/ml | 6.1E2 | 1.9E2 | 1.6E3 | 2.7E2 | 1.2E4 | 2.6E2 | 1.5E0 | 2.0E1 | 3.4E5 | 9.7E2 | 900 | 13 | 336 | 13 | 0.22 |
| Jk | ng/ml | 3.0E0 | 1.5E1 | 2.1E1 | 5.2E1 | 4.7E1 | 7.1E1 | 1.0E-9 | 2.5E-1 | 3.9E2 | 2.4E2 | 900 | 13 | 336 | 13 | 0.67 |
| Jl | ng/ml | 4.1E-1 | 1.9E0 | 2.6E0 | 7.7E2 | 1.9E1 | 2.8E3 | 7.6E-4 | 1.3E-1 | 5.4E2 | 9.9E3 | 900 | 13 | 336 | 13 | 0.77 |
| Jm | ng/ml | 1.8E1 | 5.9E0 | 5.8E1 | 4.3E1 | 1.3E2 | 5.8E1 | 1.0E-9 | 2.5E-1 | 2.1E3 | 1.8E2 | 900 | 13 | 336 | 13 | 0.48 |
| Jn | pg/ml | 4.0E-1 | 1.7E0 | 3.7E0 | 6.3E0 | 3.8E1 | 1.1E1 | 1.0E-9 | 1.0E-9 | 7.3E2 | 3.7E1 | 899 | 13 | 336 | 13 | 0.77 |
| Jo | pg/ml | 3.6E3 | 6.3E3 | 4.9E3 | 8.2E3 | 5.0E3 | 9.7E3 | 2.0E1 | 6.6E2 | 1.0E5 | 3.6E4 | 900 | 13 | 336 | 13 | 0.57 |
| Jp | pg/ml | 7.0E4 | 9.1E4 | 7.3E4 | 1.1E5 | 3.8E4 | 3.7E4 | 5.8E2 | 6.0E4 | 3.8E5 | 1.9E5 | 900 | 13 | 336 | 13 | 0.76 |
| Jq | pg/ml | 9.6E1 | 1.9E2 | 1.6E2 | 4.6E2 | 3.6E2 | 9.7E2 | 1.0E0 | 1.4E1 | 8.7E3 | 3.7E3 | 900 | 13 | 336 | 13 | 0.69 |
| Jr | pg/ml | 5.3E0 | 3.1E1 | 4.4E1 | 8.2E1 | 4.7E2 | 1.4E2 | 1.0E-9 | 1.0E-9 | 1.1E4 | 5.0E2 | 900 | 13 | 336 | 13 | 0.75 |
| Js | pg/ml | 1.3E1 | 2.1E1 | 5.3E1 | 6.4E1 | 3.8E2 | 1.2E2 | 1.0E-9 | 7.6E0 | 1.0E4 | 4.4E2 | 900 | 13 | 336 | 13 | 0.69 |
| Jt | pg/ml | 2.6E3 | 4.2E3 | 3.2E3 | 6.2E3 | 2.8E3 | 6.7E3 | 2.2E1 | 1.0E3 | 5.2E4 | 2.5E4 | 900 | 13 | 336 | 13 | 0.64 |
| Lh | pg/ml | 1.3E4 | 3.7E4 | 2.2E4 | 6.9E4 | 3.2E4 | 1.1E5 | 1.0E-9 | 1.3E3 | 4.8E5 | 4.1E5 | 900 | 13 | 337 | 13 | 0.72 |
| Li | pg/ml | 3.3E3 | 1.8E4 | 1.7E4 | 7.5E4 | 6.2E4 | 1.2E5 | 1.0E-9 | 3.4E1 | 1.3E6 | 4.1E5 | 900 | 13 | 337 | 13 | 0.68 |
| Lj | pg/ml | 2.8E3 | 1.1E4 | 2.3E4 | 2.6E4 | 6.6E4 | 3.2E4 | 1.0E-9 | 2.2E2 | 5.2E5 | 1.0E5 | 900 | 13 | 337 | 13 | 0.62 |
| Nv | pg/ml | 4.0E3 | 1.2E4 | 1.1E4 | 2.5E4 | 4.3E4 | 3.9E4 | 1.0E-9 | 1.0E3 | 1.1E6 | 1.3E5 | 906 | 13 | 337 | 13 | 0.72 |
| Nw | pg/ml | 8.9E3 | 1.9E4 | 1.3E4 | 4.0E4 | 1.7E4 | 5.5E4 | 8.6E1 | 6.8E3 | 2.1E5 | 2.1E5 | 906 | 13 | 337 | 13 | 0.77 |
| Nx | pg/ml | 2.2E2 | 2.6E2 | 4.1E2 | 8.4E2 | 6.5E2 | 9.3E2 | 1.0E-9 | 1.0E-9 | 7.4E3 | 2.8E3 | 906 | 13 | 337 | 13 | 0.65 |
| Ny | pg/ml | 6.4E0 | 1.7E1 | 5.7E1 | 6.8E1 | 8.5E2 | 1.6E2 | 1.0E-9 | 1.0E-9 | 2.5E4 | 6.1E2 | 906 | 13 | 337 | 13 | 0.67 |
| Oe | pg/ml | 6.8E1 | 1.8E1 | 2.9E2 | 2.4E2 | 7.5E2 | 3.6E2 | 1.0E-9 | 1.0E-9 | 1.9E4 | 1.1E3 | 897 | 13 | 336 | 13 | 0.48 |
| Of | pg/ml | 1.7E2 | 1.9E2 | 6.1E3 | 3.4E3 | 2.8E4 | 7.2E3 | 1.0E-9 | 7.4E0 | 6.2E5 | 2.4E4 | 905 | 13 | 337 | 13 | 0.54 |
| Og | pg/ml | 8.2E-2 | 8.2E-2 | 4.8E-1 | 1.8E-1 | 1.6E0 | 3.3E-1 | 1.0E-9 | 1.0E-9 | 2.0E1 | 1.2E0 | 905 | 13 | 337 | 13 | 0.46 |
| Oh | pg/ml | 2.7E0 | 6.4E0 | 2.0E1 | 2.6E1 | 1.5E2 | 3.9E1 | 1.0E-9 | 9.7E-1 | 3.5E3 | 1.3E2 | 905 | 13 | 337 | 13 | 0.73 |
| Oi | pg/ml | 2.6E0 | 1.0E-9 | 6.3E0 | 5.7E0 | 9.8E0 | 8.5E0 | 1.0E-9 | 1.0E-9 | 8.6E1 | 2.9E1 | 905 | 13 | 337 | 13 | 0.46 |
| Ok | pg/ml | 3.9E2 | 9.8E2 | 5.6E2 | 6.6E3 | 6.0E2 | 1.9E4 | 1.3E1 | 2.0E2 | 7.8E3 | 7.0E4 | 905 | 13 | 337 | 13 | 0.75 |
| Om | pg/ml | 4.0E2 | 1.1E3 | 8.9E2 | 2.8E3 | 2.7E3 | 3.6E3 | 1.0E-9 | 2.4E2 | 5.1E4 | 1.3E4 | 905 | 13 | 337 | 13 | 0.81 |
| On | pg/ml | 1.8E2 | 5.3E2 | 3.0E2 | 1.9E3 | 4.2E2 | 3.2E3 | 1.0E-9 | 1.0E2 | 4.5E3 | 9.8E3 | 905 | 13 | 337 | 13 | 0.82 |
| Oy | pg/ml | 4.9E-1 | 6.3E-1 | 5.7E0 | 3.6E0 | 2.9E1 | 8.9E0 | 1.0E-9 | 1.0E-9 | 4.0E2 | 3.3E1 | 904 | 13 | 336 | 13 | 0.52 |
| Oz | pg/ml | 3.1E-3 | 1.0E-9 | 3.1E-1 | 2.3E0 | 1.3E0 | 7.7E0 | 1.0E-9 | 1.0E-9 | 2.9E1 | 2.8E1 | 904 | 13 | 336 | 13 | 0.45 |
| Pa | pg/ml | 3.9E-1 | 7.2E-1 | 1.6E0 | 1.9E1 | 6.1E0 | 6.2E1 | 1.0E-9 | 1.0E-9 | 1.0E2 | 2.3E2 | 904 | 13 | 336 | 13 | 0.56 |
| Pb | pg/ml | 1.0E-9 | 1.0E-9 | 8.0E-1 | 2.4E-1 | 1.6E1 | 5.5E-1 | 1.0E-9 | 1.0E-9 | 4.9E2 | 1.9E0 | 904 | 13 | 336 | 13 | 0.52 |
| Pc | pg/ml | 4.4E-2 | 1.5E-1 | 3.6E-1 | 3.4E0 | 8.8E-1 | 1.0E1 | 1.0E-9 | 1.0E-9 | 1.6E1 | 3.8E1 | 904 | 13 | 336 | 13 | 0.54 |
| Pd | pg/ml | 1.9E0 | 3.6E0 | 5.1E0 | 1.1E1 | 2.9E1 | 1.7E1 | 1.0E-9 | 2.2E-1 | 8.4E2 | 5.5E1 | 904 | 13 | 336 | 13 | 0.60 |
| Pe | pg/ml | 2.2E1 | 8.7E1 | 1.2E2 | 1.3E3 | 4.4E2 | 4.1E3 | 1.0E-9 | 2.0E0 | 6.7E3 | 1.5E4 | 904 | 13 | 336 | 13 | 0.67 |
| Pf | pg/ml | 1.6E0 | 1.4E1 | 1.1E1 | 2.6E1 | 6.0E1 | 4.7E1 | 1.0E-9 | 4.7E-1 | 1.5E3 | 1.5E2 | 904 | 13 | 336 | 13 | 0.76 |
| Pg | pg/ml | 3.4E0 | 1.0E1 | 4.3E1 | 8.4E1 | 3.4E2 | 2.2E2 | 1.0E-9 | 2.9E-1 | 7.7E3 | 8.1E2 | 904 | 13 | 336 | 13 | 0.63 |
| aA | mg/dL | 8.0E-1 | 1.4E0 | 9.4E-1 | 1.7E0 | 4.9E-1 | 1.2E0 | 2.0E-1 | 5.5E-1 | 4.2E0 | 4.7E0 | 2667 | 22 | 507 | 22 | 0.73 |
| aC | mg/mL | 2.8E0 | 2.5E0 | 3.1E0 | 3.1E0 | 1.4E0 | 1.4E0 | 7.7E-1 | 1.6E0 | 8.9E0 | 5.5E0 | 535 | 9 | 207 | 9 | 0.50 |
| aD | ug/mL | 3.2E0 | 3.8E0 | 4.5E0 | 7.0E0 | 3.8E0 | 6.5E0 | 4.3E-1 | 1.1E0 | 3.5E1 | 2.1E1 | 535 | 9 | 207 | 9 | 0.61 |
| aE | mg/mL | 5.6E-1 | 6.7E-1 | 5.7E-1 | 6.6E-1 | 1.5E-1 | 1.5E-1 | 1.8E-1 | 4.7E-1 | 1.1E0 | 1.0E0 | 535 | 9 | 207 | 9 | 0.68 |
| aF | ng/mL | 2.2E0 | 2.7E0 | 4.0E0 | 5.2E0 | 5.7E0 | 5.8E0 | 4.3E-3 | 4.3E-3 | 5.0E1 | 1.5E1 | 535 | 9 | 207 | 9 | 0.51 |
| aG | mg/mL | 1.4E-1 | 9.0E-2 | 1.6E-1 | 1.5E-1 | 8.7E-2 | 8.9E-2 | 1.7E-2 | 6.9E-2 | 5.4E-1 | 3.0E-1 | 535 | 9 | 207 | 9 | 0.46 |
| aH | ug/mL | 7.5E1 | 6.5E1 | 8.2E1 | 8.5E1 | 4.4E1 | 4.9E1 | 4.6E0 | 3.2E1 | 2.9E2 | 1.8E2 | 535 | 9 | 207 | 9 | 0.49 |
| aI | ug/mL | 1.9E2 | 1.5E2 | 1.9E2 | 1.5E2 | 6.0E1 | 5.5E1 | 2.8E1 | 7.5E1 | 3.7E2 | 2.5E2 | 535 | 9 | 207 | 9 | 0.30 |

Figure 2 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aJ | ug/mL | 2.5E0 | 4.3E0 | 3.1E0 | 7.3E0 | 2.2E0 | 7.1E0 | 7.3E-1 | 1.8E0 | 1.7E1 | 2.3E1 | 535 | 9 | 207 | 9 | 0.72 |
| aK | ng/mL | 1.6E0 | 1.0E0 | 2.4E0 | 1.6E0 | 2.6E0 | 1.5E0 | 2.9E-4 | 1.3E-1 | 1.8E1 | 5.0E0 | 535 | 9 | 207 | 9 | 0.42 |
| aL | mg/mL | 8.0E-1 | 8.1E-1 | 8.1E-1 | 7.9E-1 | 2.6E-1 | 2.7E-1 | 1.9E-1 | 4.5E-1 | 1.7E0 | 1.2E0 | 535 | 9 | 207 | 9 | 0.47 |
| aM | U/mL | 2.2E1 | 3.3E1 | 4.9E1 | 4.5E1 | 1.1E2 | 3.0E1 | 4.2E-2 | 5.2E0 | 1.6E3 | 8.6E1 | 535 | 9 | 207 | 9 | 0.61 |
| aN | U/mL | 1.4E1 | 2.5E1 | 2.2E1 | 2.8E1 | 3.1E1 | 2.9E1 | 2.5E-3 | 3.6E0 | 3.8E2 | 1.0E2 | 535 | 9 | 207 | 9 | 0.60 |
| aO | pg/mL | 3.1E1 | 1.2E2 | 3.0E2 | 8.1E2 | 7.8E2 | 1.2E3 | 6.0E-2 | 8.2E0 | 6.6E3 | 3.5E3 | 535 | 9 | 207 | 9 | 0.67 |
| aP | ng/mL | 1.7E0 | 2.8E0 | 2.1E0 | 5.8E0 | 1.8E0 | 8.5E0 | 4.5E-1 | 1.1E0 | 2.8E1 | 2.8E1 | 535 | 9 | 207 | 9 | 0.76 |
| aQ | ng/mL | 3.0E-1 | 4.1E-1 | 4.5E-1 | 3.9E-1 | 4.5E-1 | 3.1E-1 | 2.0E-4 | 5.2E-2 | 4.0E0 | 1.1E0 | 535 | 9 | 207 | 9 | 0.50 |
| aR | ng/mL | 1.7E0 | 3.4E0 | 2.8E0 | 3.0E0 | 3.3E0 | 2.0E0 | 1.8E-1 | 2.5E-1 | 3.4E1 | 5.4E0 | 535 | 9 | 207 | 9 | 0.58 |
| aS | ng/mL | 2.6E-1 | 3.9E-1 | 6.3E-1 | 7.9E-1 | 1.7E0 | 9.1E-1 | 4.2E-3 | 6.0E-2 | 3.3E1 | 2.8E0 | 535 | 9 | 207 | 9 | 0.57 |
| aU | pg/mL | 7.5E1 | 5.7E1 | 1.3E2 | 8.1E1 | 1.5E2 | 8.2E1 | 7.4E-1 | 7.4E-2 | 1.3E3 | 2.3E2 | 535 | 9 | 207 | 9 | 0.41 |
| aV | ng/mL | 6.2E-1 | 5.3E-1 | 1.1E0 | 6.8E-1 | 1.8E0 | 5.3E-1 | 7.6E-4 | 1.5E-1 | 3.3E1 | 1.6E0 | 535 | 9 | 207 | 9 | 0.45 |
| aW | pg/mL | 1.9E1 | 1.5E1 | 2.0E1 | 6.1E1 | 1.8E1 | 1.4E2 | 7.2E-2 | 7.2E-2 | 2.4E2 | 4.3E2 | 535 | 9 | 207 | 9 | 0.45 |
| aX | ng/mL | 9.5E0 | 1.5E1 | 1.5E1 | 5.2E1 | 1.8E1 | 6.6E1 | 3.0E-1 | 2.1E0 | 2.2E2 | 1.7E2 | 535 | 9 | 207 | 9 | 0.63 |
| aY | pg/mL | 5.7E1 | 8.6E1 | 7.5E1 | 1.1E2 | 8.1E1 | 6.6E1 | 4.1E-1 | 2.7E1 | 1.2E3 | 2.0E2 | 535 | 9 | 207 | 9 | 0.66 |
| aZ | pg/mL | 2.2E2 | 3.0E2 | 5.0E2 | 4.3E2 | 9.5E2 | 5.5E2 | 1.7E0 | 2.4E1 | 1.2E4 | 1.8E3 | 535 | 9 | 207 | 9 | 0.54 |
| bA | ng/mL | 8.8E0 | 8.0E1 | 3.5E1 | 4.1E2 | 9.7E1 | 5.8E2 | 3.0E-2 | 4.7E0 | 9.4E2 | 1.5E3 | 535 | 9 | 207 | 9 | 0.77 |
| bB | ng/mL | 3.0E2 | 2.5E2 | 3.2E2 | 3.0E2 | 1.7E2 | 2.4E2 | 2.1E0 | 6.6E1 | 1.0E3 | 7.8E2 | 535 | 9 | 207 | 9 | 0.42 |
| bC | ng/mL | 3.5E2 | 3.2E2 | 6.1E2 | 1.1E3 | 8.1E2 | 1.3E3 | 9.8E0 | 1.8E2 | 4.7E3 | 4.0E3 | 535 | 9 | 207 | 9 | 0.62 |
| bE | mg/mL | 5.5E0 | 8.3E0 | 5.8E0 | 7.6E0 | 2.1E0 | 3.0E0 | 9.8E-1 | 3.4E0 | 1.3E1 | 1.2E1 | 535 | 9 | 207 | 9 | 0.67 |
| bF | pg/mL | 2.1E1 | 2.6E1 | 1.6E2 | 7.3E2 | 8.9E2 | 2.1E3 | 5.0E-2 | 1.2E1 | 1.1E4 | 6.3E3 | 535 | 9 | 207 | 9 | 0.62 |
| bG | ng/mL | 1.6E0 | 1.7E0 | 2.7E0 | 4.7E0 | 3.2E0 | 9.4E0 | 2.2E-2 | 1.9E-1 | 2.6E1 | 3.0E1 | 535 | 9 | 207 | 9 | 0.47 |
| bH | pg/mL | 5.7E-1 | 5.0E0 | 4.8E0 | 7.6E0 | 1.4E1 | 8.1E0 | 5.7E-1 | 5.7E-1 | 2.8E2 | 2.2E1 | 535 | 9 | 207 | 9 | 0.63 |
| bI | ng/mL | 4.0E-3 | 4.0E-3 | 6.2E-2 | 8.8E-2 | 1.6E-1 | 1.3E-1 | 4.0E-3 | 4.0E-3 | 1.3E0 | 3.1E-1 | 535 | 9 | 207 | 9 | 0.58 |
| bJ | mg/mL | 2.3E0 | 2.3E0 | 2.7E0 | 3.2E0 | 2.1E0 | 2.4E0 | 2.5E-4 | 1.2E0 | 1.3E1 | 8.9E0 | 535 | 9 | 207 | 9 | 0.58 |
| bL | pg/mL | 3.7E0 | 6.5E0 | 8.1E0 | 9.9E0 | 1.0E1 | 8.5E0 | 4.6E-2 | 1.2E0 | 8.0E1 | 2.4E1 | 535 | 9 | 207 | 9 | 0.59 |
| bM | mg/mL | 1.7E0 | 2.2E0 | 2.1E0 | 2.5E0 | 1.5E0 | 9.7E-1 | 9.2E-3 | 1.2E0 | 8.9E0 | 3.8E0 | 535 | 9 | 207 | 9 | 0.65 |
| bN | ng/mL | 4.5E1 | 3.3E1 | 1.3E2 | 5.3E1 | 2.8E2 | 7.5E1 | 1.4E-1 | 5.2E0 | 1.9E3 | 2.5E2 | 535 | 9 | 207 | 9 | 0.40 |
| bO | ng/mL | 4.0E-2 | 4.0E-2 | 1.1E1 | 9.3E-1 | 2.5E1 | 2.7E0 | 4.0E-2 | 4.0E-2 | 2.0E2 | 8.0E0 | 535 | 9 | 207 | 9 | 0.36 |
| bP | mg/mL | 5.4E-1 | 7.7E-1 | 7.7E-1 | 9.7E-1 | 6.8E-1 | 7.6E-1 | 4.9E-2 | 1.4E-1 | 4.8E0 | 2.7E0 | 535 | 9 | 207 | 9 | 0.62 |
| bQ | pg/mL | 1.6E1 | 4.1E1 | 5.8E1 | 5.5E1 | 5.9E2 | 5.8E1 | 1.5E-1 | 1.5E1 | 1.3E4 | 1.6E2 | 535 | 9 | 207 | 9 | 0.61 |
| bR | ng/mL | 1.2E-2 | 1.2E-2 | 1.3E-1 | 4.2E-2 | 4.2E-1 | 8.9E-2 | 1.2E-2 | 1.2E-2 | 8.7E0 | 2.8E-1 | 535 | 9 | 207 | 9 | 0.37 |
| bS | pg/mL | 9.4E-1 | 9.4E-1 | 6.8E0 | 8.3E0 | 2.6E1 | 2.2E1 | 9.4E-1 | 9.4E-1 | 3.9E2 | 6.7E1 | 535 | 9 | 207 | 9 | 0.49 |
| bU | ng/mL | 1.2E-1 | 1.3E-2 | 1.9E-1 | 6.9E-2 | 3.5E-1 | 1.3E-1 | 1.3E-2 | 1.3E-2 | 6.6E0 | 4.1E-1 | 535 | 9 | 207 | 9 | 0.30 |
| bV | pg/mL | 4.7E2 | 9.6E2 | 5.6E2 | 8.0E2 | 5.6E2 | 3.6E2 | 1.5E2 | 3.0E2 | 1.2E4 | 1.3E3 | 535 | 9 | 207 | 9 | 0.71 |
| bW | pg/mL | 3.3E2 | 5.5E2 | 6.1E2 | 1.2E3 | 1.7E3 | 1.5E3 | 8.4E1 | 2.0E2 | 2.5E4 | 3.9E3 | 535 | 9 | 207 | 9 | 0.65 |
| bX | ng/mL | 1.4E-3 | 2.5E-5 | 2.8E-3 | 5.7E-4 | 3.4E-3 | 1.1E-3 | 2.5E-5 | 2.5E-5 | 2.0E-2 | 3.1E-3 | 535 | 9 | 207 | 9 | 0.32 |
| bZ | pg/mL | 2.4E2 | 1.6E3 | 8.3E2 | 6.3E3 | 3.7E3 | 1.4E4 | 1.5E-1 | 1.3E2 | 5.8E4 | 4.3E4 | 535 | 9 | 207 | 9 | 0.76 |
| cA | pg/mL | 6.0E-1 | 6.0E-1 | 2.6E0 | 6.0E-1 | 1.6E1 | 0.0E0 | 6.0E-1 | 6.0E-1 | 3.7E2 | 6.0E-1 | 535 | 9 | 207 | 9 | 0.44 |
| cB | ng/mL | 5.7E-2 | 4.0E-2 | 8.8E-2 | 5.7E-2 | 1.0E-1 | 6.7E-2 | 1.7E-3 | 1.7E-3 | 5.7E-1 | 2.1E-1 | 535 | 9 | 207 | 9 | 0.40 |
| cC | pg/mL | 4.6E1 | 3.5E1 | 4.7E1 | 3.0E1 | 3.9E1 | 2.2E1 | 1.0E0 | 1.0E0 | 4.5E2 | 6.7E1 | 535 | 9 | 207 | 9 | 0.35 |
| cD | pg/mL | 5.3E0 | 2.9E0 | 1.5E1 | 6.8E0 | 5.2E1 | 1.2E1 | 3.3E-1 | 3.3E-1 | 7.2E2 | 3.9E1 | 535 | 9 | 207 | 9 | 0.34 |
| cE | pg/mL | 3.8E1 | 5.7E1 | 1.6E2 | 2.4E2 | 4.6E2 | 4.0E2 | 1.2E-1 | 1.7E0 | 3.8E3 | 1.3E3 | 535 | 9 | 207 | 9 | 0.58 |
| cF | pg/mL | 1.2E1 | 5.3E-1 | 2.0E1 | 7.6E0 | 3.0E1 | 1.3E1 | 5.3E-1 | 5.3E-1 | 2.7E2 | 3.8E1 | 535 | 9 | 207 | 9 | 0.36 |
| cG | pg/mL | 4.6E1 | 1.2E2 | 1.0E2 | 1.7E2 | 4.8E2 | 1.7E2 | 6.4E0 | 1.9E1 | 1.0E4 | 4.9E2 | 535 | 9 | 207 | 9 | 0.66 |
| cH | uIU/mL | 2.8E0 | 6.0E0 | 6.0E0 | 1.2E1 | 1.2E1 | 1.7E1 | 8.6E-3 | 8.6E-3 | 1.6E2 | 5.3E1 | 535 | 9 | 207 | 9 | 0.58 |
| cI | ng/mL | 5.7E0 | 9.9E0 | 1.2E1 | 2.4E1 | 1.6E1 | 3.6E1 | 1.0E-3 | 1.7E0 | 1.2E2 | 1.2E2 | 535 | 9 | 207 | 9 | 0.67 |
| cJ | ug/mL | 6.2E1 | 5.0E1 | 1.1E2 | 9.1E1 | 1.4E2 | 1.1E2 | 4.0E0 | 5.6E0 | 9.6E2 | 3.4E2 | 535 | 9 | 207 | 9 | 0.45 |
| cK | ng/mL | 3.8E-3 | 3.8E-3 | 4.8E-2 | 8.7E-3 | 1.7E-1 | 1.5E-2 | 3.8E-3 | 3.8E-3 | 1.7E0 | 4.8E-2 | 535 | 9 | 207 | 9 | 0.47 |
| cL | pg/mL | 2.0E2 | 2.1E2 | 3.8E2 | 3.9E2 | 1.2E3 | 4.0E2 | 1.6E1 | 7.9E1 | 2.4E4 | 1.3E3 | 535 | 9 | 207 | 9 | 0.59 |
| cM | pg/mL | 2.7E2 | 2.0E2 | 2.9E2 | 2.2E2 | 1.9E2 | 7.2E1 | 8.7E0 | 1.3E2 | 1.6E3 | 3.5E2 | 535 | 9 | 207 | 9 | 0.37 |
| cN | pg/mL | 1.2E2 | 1.2E2 | 1.3E2 | 1.5E2 | 6.2E1 | 6.4E1 | 3.8E1 | 8.6E1 | 1.1E3 | 2.8E2 | 535 | 9 | 207 | 9 | 0.58 |
| cO | pg/mL | 2.2E2 | 3.1E2 | 3.0E2 | 4.2E2 | 8.5E2 | 4.1E2 | 5.4E1 | 1.7E2 | 1.9E4 | 1.5E3 | 535 | 9 | 207 | 9 | 0.67 |
| cP | ng/mL | 2.5E3 | 3.4E3 | 2.6E3 | 3.7E3 | 9.0E2 | 1.5E3 | 6.2E2 | 1.4E3 | 5.7E3 | 5.6E3 | 535 | 9 | 207 | 9 | 0.74 |
| cQ | ng/mL | 4.9E-2 | 9.1E-2 | 1.4E-1 | 2.3E-1 | 2.8E-1 | 2.5E-1 | 2.0E-3 | 2.0E-3 | 2.2E0 | 7.3E-1 | 535 | 9 | 207 | 9 | 0.65 |
| cR | ng/mL | 2.9E2 | 5.5E2 | 5.0E2 | 8.4E2 | 7.8E2 | 7.0E2 | 2.0E1 | 2.5E2 | 8.9E3 | 2.3E3 | 535 | 9 | 207 | 9 | 0.72 |
| cS | ng/mL | 2.6E2 | 8.8E2 | 3.8E2 | 1.6E3 | 3.8E2 | 2.1E3 | 4.1E1 | 1.7E2 | 2.7E3 | 7.1E3 | 535 | 9 | 207 | 9 | 0.83 |

Figure 2 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cT | ng/mL | 3.3E1 | 1.3E2 | 8.7E1 | 6.5E2 | 1.9E2 | 7.9E2 | 3.6E0 | 1.3E1 | 2.1E3 | 1.9E3 | 535 | 9 | 207 | 9 | 0.70 |
| cU | ng/mL | 5.4E1 | 9.3E1 | 7.5E1 | 1.3E2 | 9.4E1 | 1.1E2 | 5.4E0 | 2.9E1 | 1.6E3 | 3.5E2 | 535 | 9 | 207 | 9 | 0.65 |
| cV | ng/mL | 1.8E-1 | 1.9E-1 | 3.9E-1 | 4.7E-1 | 2.1E0 | 7.8E-1 | 3.4E-4 | 8.4E-2 | 4.7E1 | 2.5E0 | 535 | 9 | 207 | 9 | 0.57 |
| cW | mIU/mL | 5.2E-2 | 8.6E-2 | 1.3E-1 | 1.2E-1 | 6.5E-1 | 1.0E-1 | 3.7E-4 | 3.6E-2 | 9.7E0 | 2.9E-1 | 535 | 9 | 207 | 9 | 0.66 |
| cX | ng/mL | 1.1E-1 | 2.9E-2 | 1.3E0 | 2.0E-1 | 4.2E0 | 3.5E-1 | 2.3E-4 | 2.3E-4 | 2.8E1 | 1.1E0 | 535 | 9 | 207 | 9 | 0.39 |
| cY | ng/mL | 8.6E0 | 5.1E0 | 1.3E1 | 8.3E0 | 1.3E1 | 9.6E0 | 1.5E-1 | 6.0E-1 | 8.3E1 | 3.1E1 | 535 | 9 | 207 | 9 | 0.38 |
| cZ | ug/mL | 1.5E1 | 1.6E1 | 1.6E1 | 1.6E1 | 7.2E0 | 8.4E0 | 2.3E0 | 7.0E0 | 5.7E1 | 3.0E1 | 535 | 9 | 207 | 9 | 0.50 |
| dA | pg/mL | 3.3E2 | 4.6E2 | 3.7E2 | 4.4E2 | 2.9E2 | 1.9E2 | 9.0E1 | 1.7E2 | 5.8E3 | 6.6E2 | 535 | 9 | 207 | 9 | 0.64 |
| dB | ug/mL | 1.7E1 | 1.9E1 | 1.7E1 | 1.8E1 | 1.5E1 | 9.6E0 | 9.4E-1 | 2.4E0 | 2.5E2 | 2.8E1 | 535 | 9 | 207 | 9 | 0.57 |
| dC | nmol/L | 3.5E1 | 3.3E1 | 3.9E1 | 3.8E1 | 1.8E1 | 1.6E1 | 7.6E0 | 2.3E1 | 1.4E2 | 7.6E1 | 535 | 9 | 207 | 9 | 0.48 |
| dD | ug/mL | 3.6E1 | 3.2E1 | 3.7E1 | 3.5E1 | 1.1E1 | 1.4E1 | 1.3E1 | 1.6E1 | 7.6E1 | 6.4E1 | 535 | 9 | 207 | 9 | 0.42 |
| dE | ng/mL | 4.7E-1 | 5.4E-1 | 5.9E-1 | 9.4E-1 | 6.9E-1 | 1.1E0 | 8.4E-3 | 8.4E-3 | 7.2E0 | 3.3E0 | 535 | 9 | 207 | 9 | 0.56 |
| dF | ng/mL | 2.3E2 | 2.9E2 | 2.8E2 | 4.0E2 | 2.0E2 | 2.6E2 | 5.6E1 | 1.0E2 | 1.3E3 | 8.3E2 | 535 | 9 | 207 | 9 | 0.65 |
| dG | ng/mL | 1.1E1 | 1.5E1 | 1.5E1 | 2.2E1 | 1.3E1 | 1.8E1 | 2.2E0 | 7.5E0 | 1.8E2 | 6.5E1 | 535 | 9 | 207 | 9 | 0.66 |
| dH | pg/mL | 7.7E0 | 1.1E1 | 1.3E1 | 1.8E1 | 3.6E1 | 2.2E1 | 4.0E-2 | 5.8E0 | 6.7E2 | 7.6E1 | 535 | 9 | 207 | 9 | 0.66 |
| dI | pg/mL | 4.6E-1 | 4.6E-1 | 2.1E0 | 3.8E0 | 1.5E1 | 6.0E0 | 4.6E-1 | 4.6E-1 | 3.3E2 | 1.9E1 | 535 | 9 | 207 | 9 | 0.64 |
| dJ | ng/mL | 1.9E0 | 1.7E0 | 2.1E0 | 2.0E0 | 1.2E0 | 8.6E-1 | 3.2E-2 | 8.4E-1 | 6.9E0 | 3.2E0 | 535 | 9 | 207 | 9 | 0.48 |
| dK | uIU/mL | 1.9E0 | 6.8E-1 | 3.1E0 | 1.0E0 | 6.1E0 | 1.2E0 | 2.8E-4 | 1.4E-2 | 7.9E1 | 3.0E0 | 535 | 9 | 207 | 9 | 0.26 |
| dL | ng/mL | 8.8E2 | 1.3E3 | 1.0E3 | 1.3E3 | 5.7E2 | 5.1E2 | 2.6E2 | 5.8E2 | 4.8E3 | 2.3E3 | 535 | 9 | 207 | 9 | 0.69 |
| dM | pg/mL | 9.7E2 | 1.3E3 | 1.3E3 | 2.6E3 | 1.3E3 | 2.7E3 | 3.4E2 | 6.0E2 | 1.6E4 | 8.8E3 | 535 | 9 | 207 | 9 | 0.62 |
| dN | ug/mL | 9.3E1 | 1.6E2 | 1.0E2 | 1.5E2 | 4.0E1 | 3.8E1 | 1.6E1 | 8.6E1 | 3.3E2 | 2.0E2 | 535 | 9 | 207 | 9 | 0.82 |
| dR | pg/ml | 1.6E3 | 1.1E3 | 2.3E3 | 2.0E3 | 2.3E3 | 2.4E3 | 1.4E2 | 1.3E2 | 1.5E4 | 7.3E3 | 365 | 7 | 197 | 7 | 0.42 |
| eF | ng/ml | 4.1E0 | 7.5E0 | 5.0E0 | 1.1E1 | 4.0E0 | 8.7E0 | 1.2E0 | 4.8E0 | 4.6E1 | 2.9E1 | 380 | 7 | 198 | 7 | 0.84 |
| fP | ng/ml | 2.6E2 | 3.9E2 | 2.9E2 | 3.1E2 | 1.7E2 | 1.7E2 | 1.8E0 | 1.6E1 | 1.0E3 | 5.0E2 | 346 | 7 | 189 | 7 | 0.58 |
| fR | ng/ml | 1.4E5 | 2.9E5 | 1.9E5 | 3.4E5 | 1.5E5 | 2.9E5 | 2.9E4 | 1.9E2 | 8.3E5 | 8.7E5 | 359 | 7 | 109 | 7 | 0.69 |
| gL | pg/ml | 6.5E4 | 1.2E5 | 7.0E4 | 1.1E5 | 2.9E4 | 6.6E4 | 1.4E4 | 4.1E4 | 2.0E5 | 2.2E5 | 365 | 7 | 197 | 7 | 0.65 |
| gP | U/ml | 2.7E2 | 3.0E2 | 2.8E2 | 3.1E2 | 1.1E2 | 8.3E1 | 1.2E1 | 1.9E2 | 1.1E3 | 4.4E2 | 376 | 7 | 198 | 7 | 0.64 |

Analyte panel data:

Unconstrained panels with 3 analytes, where 1.0E-8 >= 'model p-value' > 0. Contains 17 panels of 939,239 total panels evaluated. : Jj{Fr(Is Iv Lv Ma Md Mg Ns) Ma(Is On) Md(Om On) Mg(Is Jl)} Md{Fr(Is Ji) MuHu} MxJiaA Unconstrained panels with 3 analytes, where 1.0E-7 >= 'model p-value' > 1.0E-8. Contains 332 panels of 939,239 total panels evaluated. : Jj{Fr(aA Fp Hq Hr Hu Hv Hw Hx Ii Ij Ik Il Im In Io Ip Iq Ir It Iu Jh Ji Jk Jl Jm Jn Jo Jp Jq Jr Js Jt Lh Li Lj Lu Lw Ly Lz Mb Mc Mf Mh Mi Mj Ml Mm Mn Mp Mq Mr Ms Mt Mu Mv Mw Mx My Mz Na Nb Nc Nd Nf Ng Nh Ni Nj Nk Nl Nm Nn No Nq Nt Nu Nv Nw Nx Ny Oe Of Og Oh Oi Ok Om On Oy Oz Pa Pb Pc Pd Pe Pf Pg Po Pz Qa Qc Qd Qe) On(Hr Hv Ij Ik Il In Is Iu Iv Lv Lw Mg Ml Mn Mt Mu Mx My Nh No Ns Nt Of Pc) Is(Hr Ih Ij Ik Il In It Jg Jh Ji Lv Lw Md Ml Mu Mx Nn Nt Nu Ok Pc Qb) Ma(Iv Jh Ji Jk Jl Mu Nt Ok Om) Mg(aA Iv Ji Lv Mu Oh Ok) Ji(Il Iu Jh Jq Md Mu) Lv(Jl Mu) Iv(Jh Mu) MxJl} Fr{Ji(Hr Ij In Jq Ma Ml Mt Mx My Nf Ng Nh No Ns Nv Nx Of Og Oy) Is(Hr Hu Ij In Jm Lv Lw Mt My Ng Ns Of Oi Oy Qb) Md(Hv Iv Jr Lv Lw Mc Mp Nw Ok Om On) Oy(Iv Jl Lw Mk Nb On Oz) Iv(Hr In Lv Ng Of) Lw(aA My Ng Ns) Lv(Hr Ns Of) Ng(Mg Nt) Hr(aA Ok)} Ji{Md(aA Hv Is Iv Jh Jl Lu Ma Mu Mv Ni Nn Nq Om On Pc) Jq(Hr In Ir Is Iv Jh Jl Lv Ma Mu Ni) Hr(In Is Iv Jl Ma Mu) Ma(In Ml Nf) Mx(Is Iv Jl) In(Iv Jl)} On{Md(Hr Hv In Is Iv Lv Ma Mc Mg Mn Ni Nn No Oe Oi Pc Pz) Hr(In Is Iv Lv Ma Ng No Ns Of Oi) Mg(Ng Of Oy) In(Is Iv) MaOf} Is{Hr(Mu Oi Ok) In(Lw Mg Nt) MdOm} cS{bA(bR bU) bNcP bRcT} bJ{bAbU cTdN} LwMaaA Unconstrained panels with 3 analytes, where 1.0E-6 >= 'model p-value' > 1.0E-7. Contains 3,219 panels of 939,239 total panels evaluated. : Fr{Lv(aA Et Fp Hq Hr Hu Hv Hw Hx Ih Ii Ij Ik Il Im In Io Ip Iq Ir It Iu Jg Jh Ji Jk Jl Jm Jn Jo Jp Jq Jr Js Jt Lh Li Lj Lu Lw Lx Ly Lz Ma Mb Mc Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nu Nv Nw Nx Ny Oe Og Oh Oi Ok Om On Oy Oz Pa Pb Pc Pd Pe Pf Pg Po Pz Qa Qb Qc Qd Qe) Iv(aA Et Fp Hq Hu Hv Hw Hx Ih Ii Ij Ik Il Im Io Ip Iq Ir Is It Iu Jg Jh Ji Jk Jl Jm Jn Jo Jp Jq Jr Js Jt Lh Li Lj Lu Lw Lx Ly Lz Ma Mb Mc Me Mf Mg Mh Mi Mj Mk Ml Mm Mn Mp Mq Mr Ms Mt Mu Mv Mw Mx My Mz Na Nb Nc Nd Ne Nf Nh Ni Nj Nk Nl Nm Nn No Nq Nr Ns Nt Nu Nv Nw Nx Ny Oe Og Oh Oi Ok Om On Oz Pa Pb Pc Pd Pe Pf Pg Po Pz Qa Qb Qc Qd Qe) Md(aA Et Fp Hq Hr Hu Hv Hw Hx Ih Ii Ij Ik Il Im In Io Ip Iq Ir It Iu Jg Jh Jk Jl Jm Jn Jo Jp Jq Js Jt Lh Li Lj Lu Lx Ly Lz Ma Mb Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Oy Oz Pa Pb Pc Pd Pe Pf Pg Po Pz Qa Qb Qc Qd Qe) Is(aA Et Fp Hq Hv Hw Hx Ih Ii Ik Il Im Io Ip Iq Ir It Iu Jg Jh Ji Jk Jl Jn Jo Jp Jq Jr Js Jt Lh Li Lj Lu Lx Ly Lz Ma Mb Mc Me Mf Mg Mh Mi Mj Mk Ml Mm Mn Mp Mq Mr Ms Mu Mv Mw Mx Mz Na Nb Nc Nd Ne Nf Nh Ni Nj Nk Nl Nm Nn No Nq Nr Nt Nu Nv Nw Nx Ny Oe Og Oh Ok Om On Oz Pa Pb Pc Pd Pe Pf Pg Po Pz Qa Qc Qd Qe) Lw(Fp Hq Hr Hu Hv Hw Hx Ih Ii Ij Ik Il Im In Io Ip Iq Ir It Iu Jg Jh Ji Jk Jl Jm Jn Jp Jr Js Li Lj Lu Ly Lz Ma Mb Mc Me Mf Mg Mh Mi Mj Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nu Nv Nw Nx Ny Oe Of Og Oh Oi Ok Om On Oz Pa Pb Pc Pd Pe Pf Pg Pz Qa Qd) Ji(aA Et Fp Hq Hu Hv Hw Hx Ih Ii Ik Il Im Io Ip Iq Ir It Iu Jg Jh Jk Jl Jm Jn Jo Jp Jq Jr Js Jt Lh Li Lj Lu Lx Ly Lz Mb Mc Me Mf Mg Mh Mi Mj Mk Mm Mn Mp Mq Mr Ms Mu Mv Mw Mz Na Nb Nc Nd Ne Ni Nj Nk Nl Nm Nn Nq Nr Nt Nu Nw Ny Oe Oh Oi Ok Om On Oz Pa Pb Pc Pd Pe Pf Pg Po Pz Qa Qb Qc Qd Qe) Ng(aA Fp Hq Hr Hu Hv Ii Ij Ik Il Im In Ip Iq Ir It Iu Jg Jh Jk Jl Jn Jo Jp Jq Jr Js Jt Lh Lj Ly Lz Ma Mb Mc Mh Mi Mj Ml Mm Mn Mp Mq Mr Ms Mt Mu Mv Mw Mx My Mz

Figure 2 Continued

Na Nb Nc Nd Nf Nh Ni Nj Nk Nl Nm Nn No Nq Ns Nu Nw Nx Of Oh Oi Ok Om On Oy Oz Pa Pc Pd Pe Pf Pg Qa Qc Qd Qe) Ns(aA Hq Hr Hu Hv Ij Ik Im In Iq Ir Iu Jh Jl Jm Jr Jt Li Ma Mc Mg Mh Mi Mj Ml Mn Mp Mq Ms Mt Mu Mx My Mz Na Nb Nc Nf Nh Ni Nj Nk Nn No Nq Nr Nt Nu Nw Ny Oe Of Oh Oi Ok Om On Oy Oz Pa Pc Pd Pe Pf Pg Qd) Hr(Fp Hq Hu Hv Ik Il In Ip Iq Ir Iu Jh Jl Jm Jn Jq Jr Js Jt Lh Lj Ly Ma Mc Mg Mh Mi Mj Mn Mq Mr Ms Mt Mu Mv Mw My Mz Na Nh Ni Nk Nl Nm No Nq Nr Nt Nu Nw Oe Of Oh Oi Om On Oy Oz Pa Pd Pe Pf Qa Qd Qe) Of(aA Hu Hv Hx Ij Ik Il Ir Iu Jh Jl Jo Jr Jt Lh Ly Ma Mc Mg Mi Mq Ms Mu Mz Na Nb Nh Ni No Nt Nu Nw Oi Ok Om On Oz Pa Pc Pd Pe Pf Qd) Oy(aA Hu Hv Ij Ik Il Ir Iu Jh Jn Jr Jt Lh Ly Ma Mc Mg Mi Mj Mq Mr Ms Mu Mz Na Nh Ni Nn No Nt Nu Nw Oi Ok Om Pa Pc Pd Pe Pf Qd) Hu(aA Hv Ik Il Im In Ir Jh Jl Jm Jr Ly Ma Mc Mg Mn Mq Ms Mt Mu Mz Na Nh Ni No Nt Nu Oi Ok Om On Pa Pc Pd Qd) My(aA Hv Ik In Ir Jh Jl Jr Ma Mc Mg Mn Mq Ms Mu Mz Na Nb Nh Ni No Nt Nu Nw Oi Ok Om On Pa Pc Pc Qd) Ok(aA Hv Ij In Iq Jh Jl Jr Ma Mc Mg Mn Mt Mx Nf Nh Ni No Nv Oe Og Oi Pa Pc Pz Qd) aA(In Jr Ma Mc Mg Mt Mx Mz Ne No Oe On Pa Pc) On(In Ma Mt Mw Nh Ni Nv Ny Oe Og Oi) Jl(Ij Ma Mk Mt Nh Ni Nk Ny Oe Oi) Jj(Et Ih Jg Lx Me Mk Ne Nr Qb) Oi(Hv Ir Jr Mg Nh Nt Pc Qd) Qd(Il Jm Mx No Nr Pz) Hv(In Jm Ma Mt Nr) Ir(In It Ma Ml Mx) Nt(In Nr Nv) Nh(Ma Ni Nk) Mi(Hq Mt) cP(aW cS) MaJr bQcR} Ji{Jj(aA Et Fp Hq Hr Hu Hv Hw Hx Ih Ii Ij Ik Im In Io Ip Iq Ir It Iv Jg Jk Jl Jm Jn Jo Jp Jr Js Jt Lh Li Lj Lu Lv Lw Lx Ly Lz Mb Mc Me Mf Mh Mi Mj Mk Ml Mm Mn Mp Mq Mr Ms Mt Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jq(aA Et Fp Hq Hu Hv Hw Hx Ih Ii Ij Ik Il Im Io Ip Iq It Iu Jg Jk Jm Jn Jo Jp Jr Js Jt Lh Li Lj Lu Lw Lx Ly Lz Mb Mc Md Me Mf Mg Mh Mi Mj Mk Ml Mm Mn Mp Mq Mr Ms Mt Mv Mw Mx My Mz Na Nb Nc Nd Ne Nf Ng Nh Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ma(aA Et Fp Hq Hu Hv Hw Hx Ih Ii Ij Ik Il Im Io Iq Ir Is It Iu Iv Jg Jh Jk Jl Jm Jn Jo Jp Jr Js Lh Li Lj Lu Lv Lw Ly Lz Mb Mc Me Mf Mg Mh Mi Mj Mm Mn Mp Mq Mr Ms Mt Mu Mv Mw Mx My Mz Na Nb Nc Nd Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd) In(aA Fp Hu Hv Ih Ij Ik Il Im Io Ir Is It Iu Jg Jh Jk Jn Jo Jr Js Jt Li Lj Lu Lv Lw Lz Mc Md Mg Mh Mi Mj Mk Ml Mn Mp Mr Ms Mt Mu Mv Mw Mx My Mz Na Nb Nc Nd Nf Nh Ni Nj Nk Nm Nn No Nq Nr Ns Nt Nu Of Og Oh Oi Ok Om On Oy Oz Pa Pb Pc Pd Pe Pf Po Pz Qb Wm) Md(Et Hq Hr Hu Hw Hx Ih Ii Ik Il Io Ir It Iu Jg Jk Jm Jn Jo Jp Jr Js Jt Lh Li Lv Lw Lx Mc Mg Mh Mi Mj Mk Ml Mn Mp Mr Ms Mt Mw Mx My Mz Na Nb Nc Nd Ng Nh Nk Nl Nm No Nr Ns Nt Nu Nv Nw Ny Oe Of Og Oh Oi Ok Oz Pa Pd Pc Pf Pg Po Pz Qa Qb Qd Qe) Hr(aA Hv Ih Ij Ik Il Io Ir It Iu Jh Jk Jr Li Lu Lv Mc Mg Mh Mi Mj Mk Ml Mn Mp Mr Ms Mt Mv Mw Mx Nb Nd Nf Nh Ni Nk Nm No Ns Nt Nu Oi Ok Om On Oz Pa Pc Pe Pf Po Qd) Jh(Hv Ih Ij Is It Iv Jl Jn Js Lv Ml Mu Mx My Nf Ng Nh Nm No Ns Nx Ny Of Og Oi On Oy Pb Pc Pz) Jl(Hw Hx Ii Ij It Jn Jr Js Lv Lz Mg Ml Ms Mu Mz Nf Nk No Ny Of Og Oi Oy Pb Pc Pe Qb) Mx(Hv Ir Iu Lu Lv Mi Mj Ml Mr Ms Mt Mu Mv Nf Ni Nt Og Oh On Oz Pa Pe Pf Qd) Ml(aA Hv Ir Is Iv Lu Lv Mc Mg Mi Mt Mu Mv Nb Nh Ni Nt Og On Pc Pe Pf) Mu(aA Ij Is It Jn Js Lv Ms My Nf Ng No Ns Nx Ny Of Og Oi Oy Pb) Nf(aA Hv Ir Is Iu Iv Lu Mg Mi Mt Mv Ni Nn Nt Om On Pc Pf) Is(Ih Ij It Jm Jn Jr Js Mg Mz No Ny Oi Pb Pc Qb) Pc(aA Ij Iv Lv Mi Ms Ns Oi On) On(Ns Nv Nx Ny Of Og Oy) Mg(aA Ij Lv Ng Oi) Iv(Ij It Jn Js Mz) Ir(It Jn Jr Js) aA(Jn Jr Js Mz) Ny(Nb Pa Pe) Mv(Ij Of) NiIj ItIu} Jj{Is(aA Et Fp Hq Hu Hv Hw Hx Ii Im Io Ip Iq Ir Iu Iv Jk Jl Jm Jn Jo Jp Jq Jr Js Jt Lh Li Lj Lu Lx Ly Lz Mb Mc Me Mf Mh Mi Mj Mk Mm Mn Mp Mq Mr Ms Mt Mv Mw My Mz Na Nb Nc Nd Ne Nf Ng Nh Ni Nj Nk Nl Nm No Nq Nr Ns Nv Nw Nx Ny Oe Of Og Oh Oi Om Oy Oz Pa Pb Pd Pe Pf Pg Po Pz Qa Qc Qd Qe) On(aA Et Fp Hq Hu Hw Hx Ih Ii Im Io Ip Iq Ir It Jg Jh Jk Jl Jm Jn Jo Jp Jq Jr Js Jt Lh Li Lj Lu Lx Ly Lz Mb Mc Me Mf Mh Mi Mj Mk Mm Mp Mq Mr Ms Mv Mw Mz Na Nb Nc Nd Ne Nf Ng Ni Nj Nk Nl Nm Nn Nq Nr Nu Nv Nw Nx Ny Oe Og Oh Oi Ok Om Oy Oz Pa Pb Pd Pe Pf Pg Po Pz Qa Qb Qc Qd Qe) Jl(Hr Hu Hv Hx Ih Ii Ij Ik Il Im In Ip It Iu Iv Jg Jh Jk Jo Jr Lh Lj Lw Ly Lz Md Mh Mi Mj Ml Mn Mp Mq Ms Mt Mu Mv Mw My Mz Na Nb Nf Nh Ni Nk Nm Nn No Ns Nt Nu Nx Of Oh Oi Ok Om Pc Pd Pe Pf Pg Po Qd) Mu(aA Et Hr Hu Hv Ii Ik Il In Ip Iu Jh Jk Jn Jo Jp Jr Js Jt Lh Li Lw Md Mh Mi Mj Ml Mm Mp Mr Ms Mt Mv Mw Mx My Mz Nh Nn Ns Nt Nu Nw Nx Oh Oi Ok Om Oz Pa Pc Pd Pe Pf Po Qa Qc Qd Qe) Mg(Hr Hu Hv Ii Il In Iu Jg Jh Jk Jn Jp Jr Js Lh Lw Ma Md Mh Mi Mj Mm Mp Mr Ms Mt Mv Mw My Mz Ng Nh Nn Nt Nu Nv Nw Nx Oi Om Oz Pa Pc Pe Pf Po Qa Qd Qe) Ma(aA Hv Ii Il Iu Jg Jp Jr Jt Lh Lv Lw Mi Mj Mp Mr Ms Mt Mv Mw Mz Nb Nh Nn Nu Nv Nw Nx Oh Oz Pa Pc Pd Pe Pf Po Qa Qd Qe) Iv(Hr Hv Il In It Iu Jg Jk Jp Js Lh Lv Lw Md Mi Ml Mm Mp Ms Mt Mv Mw Mx Mz Nd Nn Nq Ns Nt Nu Nw Of Oh Ok Om Pc Pf) Nt(Hr Hv Il In Iu Jh Jk Lv Lw Md Mi Mj Mp Ms Mt Mv Mw Mz Nd Nn Ns Oh Oi Ok Om Pc Pf) Jh(Hv Il Iu Jk Li Lv Lw Md Mi Mj Mp Mt Mz Ns Nu Oh Ok Om Pa Pc Pf Po Qd) Om(Hr Hu Hv Ij Il In Iu Lv Mi Mj Ml Mp Nh Ns Nu Of Oh Pc Pf) Ok(Hr Hv Il Iu Jk Lu Lv Md Mi Mp Mt Mv Nh Nn Pc) Lv(Il Iu Jg Jk Mt Mv Mw Nn Nu Oh Pc Pf) Mi(Ik Jk Pc) Md(Jk Lh) MtIl} On{Hr(aA Et Fp Hq Hu Hv Hw Hx Ih Ii Ij Ik Il Im Io Ip Iq Ir It Iu Jg Jh Jk Jl Jm Jn Jo Jp Jq Jr Js Jt Lh Li Lj Lu Lw Lx Ly Lz Mb Mc Me Mf Mg Mh Mi Mj Mk Ml Mm Mn Mp Mq Mr Ms Mt Mu Mv Mw Mx My Mz Na Nb Nc Nd Ne Nf Nh Ni Nj Nk Nl Nm Nn Nq Nr Nt Nu Nv Nw Nx Ny Oe Og Oh Ok Om Oy Oz Pa Pb Pc Pd Pe Pf Pg Po Pz Qa Qb Qc Qd Qe) Md(aA Et Fp Hq Hu Hw Hx Ih Ii Ij Ik Il Im Io Ip Iq Ir It Iu Jg Jh Jk Jl Jm Jn Jo Jp Jq Jr Js Jt Lh Li Lj Lu Lw Lx Ly Lz Mb Mc Mf Mh Mi Mj Mk Ml Mm Mp Mq Mr Ms Mt Mu Mv Mw Mx My Mz Na Nb Nc Nd Ne Nf Ng Nh Nj Nk Nl Nm Nq Nr Ns Nt Nu Nv Nw Nx Ny Of Og Oh Ok Om Oy Oz Pa Pb Pd Pe Pf Pg Po Qa Qb Qc Qd Qe) Of(aA Hv Ih Ik Il In Io Ir Is Iv Jh Jl Jo Lu Lv Lw Mi Mn Ms Mu Mv Mx Nb Nh Ni Nk Nm Nn No Nq Ns Nt Oe Og Oi Om Oz Pa Pc Pf Pz) Ma(aA Hq Hu Hv Ij In Is Iv Jh Jl Jm Lv Lw Mg Mn Ms Mt Mu My Mz Ng Nh Ni Nn No Nq Nr Ns Nv Ny Oe Og Oi Ok Oy Pc Pg Pz) Oy(Hv In Is Iv Jh Jl Lv Lw Mk Mn Mt Mu Mv Mx Nb Ni Nn No Ns Oi Om Oz Pa Pc) In(aA Hu Hv Ir Lv Lw Mg Mi Mn My Ng Nh Ni No Ns Oe Og Oi Pc) Is(Ih Ij Iq It Jh Jm Lw Mg Mx Ng Ni Ns Nv Ny Oe Og Oi Pc Qb) Ng(Iv Jh Lv Lw Mn Mu Mv Mx Nn No Ns Oi Pc) Ns(Iv Lv Lw Mn Mx Nn No Oi Pc) My(Lv Lw Mg Mn Mu Mx No Oi Pc) Mg(aA Hu Lv Nv Ny Og Oi) Og(Jh Lv Lw Mu No Pc) Nv(Iv Jh Lv Mu Om) Ny(Iv Jl Lv Ni) Oi(Hu Iv Pc) Lw(aA Nx) LvHu MsPc MxIv NiIj} Is{Hr(aA Hv Ih Ik In Io Iq It Iu Iv Jh Jl Jm Jp Lh Lv Lw Ma Md Mg Mi Ml Mn Mq Mr Mt Mv Mx Mz Ni Nk Ns Nt Nu Nw Om Pa Pf Qb) In(aA Hv Ih Im Iq Ir It Iv Jg Jh Jl Jm Jo Jt Lh Lv Ma Md Mi Ml Mq Mu Mv Mx Nb Ni Nn Ns Oi Ok Om Pa Pc Pe Qb) Md(aA Ih It Jg Jh Jm Lv Lw Ma Mg Mi Mp Mu Mv Ni Nn Nq Nw Oi Ok Pc) It(aA Ir Iv Jh Lv Lw Ma Mg Mi Mu Ni Nt Oi Ok Pc) Ok(aA Ih Ij Jh Jq Lu Ma Mg Ml Mu Mx Og Pc Qb) Pc(aA Jm Lv Ma Mg Mi Nk Ns Oi Qb) Ih(aA Iv Jl Lw Ma Mg Mi Nt) Ma(aA Jh Jm Lw Mu Oi) Mg(aA Jm Lv Ng Oi Qb) Mu(Jm Lv Mx Oi Qb) Mx(aA Jm Mi Ni) Jh(Jm Lv Oi) Lw(aA Qb) Ni(Ij Ml) LvQb} cS{cT(aA aD aE aF aG aI aN aW aY bE Bg bJ bN bO bQ bS bU bX bZ cA cB cC cD cE cF cH cI cK cN cP cR cX dE dF dG dH dK dM dN) cP(aA aF aW aX bA bE BG bJ bR bU bZ cD cF cI cM cR dK) bA(aF aW bJ bN bQ bS bX cB cD cI cK dG dH) aA(bR bU cI dG) bR(bN bZ cN) bU(aX bN)} Md{Om(aA Hr Hu Hv In Iv Jl Lh Lu Lv Lw Lx Ma Mc Mi Mp Ms My Mz Nb Ng Nh Ni Nn Ns Nw Oe Of Og Oi Ok Oy Pc Qa Qd) Ok(Hr Jh Jl Mg Mp Mu Nn Nq Pc) Nw(Jh Ma Mg Mi Mu Nn Nq Pc) Lv(Jh Mu) Mi(Jh Mu) aA(Lw Mg)} Hr{Ok(aA Hv In Iv Jh Jl Lu Lv Ma Mg Mi Mt Mu) Jl(Iv Jh Lv Lw Ma Mg Mu Nk Oi Om) Lv(aA Iv Jh Mg Mu) Iv(Jh Mu Nw Om) aA(Lw Mg Mu) MiMu} aA{Lw(Hv Hw Ij In It Jl Jn Lv Mg Ml Mu Mx Na Nf Pb) Mg(In Jr Lv Ok Pc) Ma(Jr Nw Ok Pc) Lv(Mu Pc) OkPc bJcT bUcX} Jl{Mg(In Lv Ng Of Oi Ok Oy) Ok(In Ma Mx Og Pc) Lv(Jh Mu) Lw(In Ma) Om(Of Oy) MuOy InIv} bA{bU(aE aW aX bE bZ cR dK) bJ(aD aF aW bR bZ dK) aF(bZ cR) bR(aE bZ) bNdK dGdN} cT{dN(aE aF aM aW bE bN bQ dF dG) aD(bE bJ bZ) aW(bE bJ) BgbJ aXbU} In{Iv(Jh Lw Mg Mu Ok Om Pc) OkPc} Ok{Pc(Iv Lu Ma Mg Mi) MgNg} Oy{Mv(Bc Cu) MuHu} MgNgJg MuMyHu aXbUcP

Figure 2 Continued

Unconstrained panels with 3 analytes, where 1.0E-5 >= 'model p-value' > 1.0E-6. Contains 17,145 panels of 939,239 total panels evaluated. :
Fr[Og(aA Et Fp Hq Hr Hu Hv Hw Hx Ih Ii Ij Ik Il Im In Io Ip Iq Ir It Iu Jg Jh Jk Jl Jm Jn Jo Jp Jq Jr Js Jt Lh Li Lj Lu Lx Ly Lz Ma Mb Mc Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oh Oi Om Oy Oz Pa Pb Pc Pd Pe Pf Pg Po Pz Qa Qb Qc Qd Qe) Mw(aA Et Fp Hq Hu Hv Hw Hx Ih Ii Ij Ik Il Im In Io Ip Iq Ir It Iu Jg Jh Jk Jl Jm Jn Jo Jp Jq Jr Js Jt Lh Li Lj Lu Lx Ly Lz Ma Mb Mc Me Mf Mg Mh Mi Mj Mk Ml Mm Mn Mp Mq Mr Ms Mt Mu Mv Mx My Mz Na Nb Nc Nd Ne Nf Nh Ni Nj Nk Nl Nm Nn No Nq Nr Ns Nt Nu Nv Nw Nx Ny Oe Of Oh Oi Ok Om Oy Oz Pa Pb Pc Pd Pe Pf Pg Po Pz Qa Qb Qc Qd Qe) Jm(aA Et Fp Hq Hw Hx Ih Ii Ij Ik Il Im In Io Ip Iq Ir It Iu Jg Jh Jk Jl Jn Jo Jp Jq Jr Js Jt Lh Li Lj Lu Lx Ly Lz Ma Mb Mc Me Mf Mg Mh Mi Mj Mk Ml Mm Mn Mp Mq Mr Ms Mt Mu Mv Mx My Mz Na Nb Nc Nd Ne Nf Ng Nh Ni Nj Nk Nl Nm Nn No Nq Nr Nt Nu Nv Nw Nx Ny Oe Of Oh Oi Ok Om On Oy Oz Pa Pb Pc Pd Pe Pf Pg Po Pz Qa Qb Qc Qe) Nu(aA Et Fp Hq Hv Hw Hx Ih Ii Ij Ik Il Im In Io Ip Iq Ir It Iu Jg Jh Jk Jl Jn Jo Jp Jq Jr Js Jt Lh Li Lj Lu Lx Ly Lz Ma Mb Mc Me Mf Mg Mh Mi Mj Mk Ml Mm Mn Mp Mq Mr Ms Mt Mu Mv Mx Mz Na Nb Nc Nd Ne Nf Nh Ni Nj Nk Nl Nm Nn No Nq Nr Nt Nv Nw Nx Ny Oe Oi Ok Om On Oz Pa Pb Pc Pd Pe Pf Pg Po Pz Qa Qb Qc Qd Qe Wm) Mi(aA Et Fp Hu Hv Hw Hx Ih Ii Ij Ik Il Im In Io Ip Iq Ir It Iu Jg Jh Jk Jl Jn Jo Jp Jq Jr Js Jt Lh Li Lj Lu Lx Ly Lz Ma Mb Mc Me Mf Mg Mh Mj Mk Ml Mm Mn Mp Mq Mr Ms Mu Mv Mx My Mz Na Nb Nc Nd Ne Nf Nh Ni Nj Nk Nl Nm Nn No Nq Nr Nt Nv Nw Nx Ny Oe Oh Oi Ok Om On Oz Pa Pb Pc Pd Pe Pf Pg Po Pz Qa Qb Qc Qd Qe Wm) Lj(aA Et Fp Hq Hu Hv Hw Hx Ih Ii Ij Ik Il Im In Io Ip Iq Ir It Iu Jh Jk Jl Jn Jo Jp Jq Jr Js Jt Lh Li Lu Lx Ly Lz Ma Mb Mc Me Mf Mg Mh Mj Ml Mm Mn Mp Mq Mr Ms Mt Mu Mv Mx My Mz Na Nb Nc Nd Ne Nf Nh Ni Nj Nk Nl Nm Nn No Nq Nr Ns Nt Nv Nw Nx Ny Oe Of Oh Oi Ok Om On Oy Oz Pa Pb Pc Pd Pe Pf Pg Po Pz Qa Qb Qd) Nw(aA Et Fp Hq Hu Hv Hw Hx Ih Ii Ij Ik Il Im In Io Ip Iq Ir It Iu Jg Jh Jk Jl Jn Jo Jp Jq Jr Js Jt Lh Li Lu Lx Ly Lz Ma Mb Mc Me Mf Mg Mh Mj Mk Ml Mm Mn Mp Mq Mr Ms Mt Mu Mv Mx Mz Na Nb Nc Nd Ne Nf Nh Ni Nj Nk Nl Nm Nn No Nq Nr Nt Nv Nx Ny Oe Oh Oi Ok Om On Oz Pa Pb Pc Pd Pe Pf Pg Po Pz Qa Qb Qc Qd Qe) Oe(Et Fp Hq Hu Hv Hw Hx Ih Ii Ij Ik Il Im In Io Ip Iq Ir It Iu Jg Jh Jk Jn Jo Jp Jq Jr Js Jt Lh Li Lu Lx Ly Lz Ma Mb Mc Me Mf Mg Mh Mj Mk Ml Mm Mn Mp Mq Mr Ms Mt Mu Mv Mx My Mz Na Nb Nc Nd Ne Nf Ng Nh Ni Nj Nk Nl Nm Nn No Nq Nr Nt Nv Nx Ny Of Oh Oi Om Oy Oz Pa Pb Pc Pd Pe Pf Pg Po Pz Qa Qb Qc Qd Qe) Mq(aA Et Fp Hq Hv Hw Hx Ih Ii Ij Ik Il Im In Io Ip Iq Ir It Iu Jg Jh Jk Jl Jn Jo Jp Jq Jr Js Jt Lh Li Lu Lx Ly Lz Ma Mb Mc Me Mf Mg Mh Mj Mk Ml Mm Mn Mp Mr Ms Mt Mu Mv Mx Mz Na Nb Nc Nd Ne Nf Nh Ni Nj Nk Nl Nm Nn No Nq Nr Nt Nv Nx Ny Oh Oi Ok Om On Oz Pa Pb Pc Pd Pe Pf Pg Po Pz Qa Qb Qc Qd Qe) Na(aA Et Fp Hq Hv Hw Hx Ih Ii Ij Ik Il Im In Io Ip Iq Ir It Iu Jg Jh Jk Jl Jn Jo Jp Jq Jr Js Jt Lh Li Lu Lx Ly Lz Ma Mb Mc Me Mf Mg Mh Mj Mk Ml Mm Mn Mp Mr Ms Mt Mu Mv Mx Mz Nb Nc Nd Ne Nf Nh Ni Nj Nk Nl Nm Nn No Nq Nr Nt Nv Nx Ny Oh Oi Ok Om On Oz Pa Pb Pc Pd Pe Pf Pg Po Pz Qa Qb Qc Qd Qe) Mz(Et Fp Hq Hv Hw Hx Ih Ii Ij Ik Il Im In Io Ip Iq Ir It Iu Jg Jh Jk Jl Jn Jo Jp Jq Jr Js Jt Lh Li Lu Lx Ly Lz Ma Mb Mc Me Mf Mg Mh Mj Mk Ml Mm Mn Mp Mr Ms Mt Mu Mv Nb Nc Nd Ne Nf Nh Ni Nj Nk Nl Nm Nn No Nq Nr Nt Nv Nx Ny Oh Oi Ok Om On Oz Pa Pb Pc Pd Pe Pf Pg Po Pz Qa Qb Qc Qd Qe) Jh(aA Et Fp Hq Hv Hw Hx Ih Ii Ij Ik Il Im In Io Ip Iq Ir It Iu Jg Jk Jl Jn Jo Jp Jq Jr Js Jt Lh Li Lu Lx Ly Lz Ma Mb Mc Me Mf Mg Mh Mj Mk Ml Mm Mn Mp Mr Ms Mt Mu Mv Mx Nb Nc Nd Ne Nf Nh Ni Nj Nk Nl Nm Nn No Nq Nr Nt Nv Nx Ny Oh Oi Om On Oz Pa Pb Pc Pd Pe Pf Pg Po Pz Qa Qb Qc Qd Qe) Mc(Et Fp Hq Hv Hw Hx Ih Ii Ij Ik Il Im In Io Ip Iq Ir It Iu Jg Jk Jl Jn Jo Jp Jq Jr Js Jt Lh Li Lu Lx Ly Lz Ma Mb Me Mf Mg Mh Mj Mk Ml Mm Mn Mp Mr Ms Mt Mu Mv Mx Nb Nc Nd Ne Nf Nh Ni Nj Nk Nl Nm Nn No Nq Nr Nt Nv Nx Ny Oh Oi Om On Oz Pa Pb Pc Pd Pe Pf Pg Po Pz Qa Qb Qc Qd Qe) Mg(Et Fp Hq Hv Hw Hx Ih Ii Ij Ik Il Im In Io Ip Iq Ir It Iu Jg Jk Jl Jn Jo Jp Jq Jr Js Jt Lh Li Lu Lx Ly Lz Ma Mb Me Mf Mh Mj Mk Ml Mm Mn Mp Mr Ms Mt Mu Mv Mx Nb Nc Nd Ne Nf Nh Ni Nj Nk Nl Nm Nn No Nq Nr Nt Nv Nx Ny Oh Om On Oz Pa Pb Pc Pd Pe Pf Pg Po Pz Qa Qb Qc Qd Qe Wm) Mt(Et Fp Hq Hw Hx Ih Ii Ij Ik Il Im In Io Ip Iq Ir It Iu Jg Jk Jn Jo Jp Jq Jr Js Jt Lh Li Lu Lx Ly Lz Ma Mb Me Mf Mh Mj Mk Ml Mm Mn Mp Mr Ms Mu Mv Mx My Nb Nc Nd Ne Nf Nh Ni Nj Nk Nl Nm Nn No Nq Nr Nt Nv Nx Ny Of Oh Oi Om Oy Oz Pa Pb Pc Pd Pe Pf Pg Po Pz Qa Qb Qc Qd Qe) Pc(Et Fp Hq Hr Hv Hw Hx Ih Ii Ij Ik Il Im In Io Ip Iq Ir It Iu Jg Jk Jl Jn Jo Jp Jq Jr Js Jt Lh Li Lu Lx Ly Lz Ma Mb Mc Mf Mh Mj Mk Ml Mm Mn Mp Mr Ms Mu Mv Mx Nb Nc Nd Ne Nf Nh Ni Nj Nk Nl Nm Nn No Nq Nr Nt Nv Nx Ny Oh Om On Oz Pa Pb Pd Pe Pf Pg Po Pz Qa Qb Qc Qd Qe) Nt(aA Et Fp Hq Hv Hw Hx Ih Ii Ij Ik Il Im Io Ip Iq Ir It Iu Jg Jk Jl Jn Jo Jp Jq Jr Js Jt Lh Li Lu Lx Ly Lz Ma Mb Me Mf Mh Mj Mk Ml Mm Mn Mp Mr Ms Mu Mv Mx Nb Nc Nd Ne Nf Nh Ni Nj Nk Nl Nm Nn No Nq Nx Ny Oh Ok Om On Oz Pa Pb Pd Pe Pf Pg Po Pz Qa Qb Qc Qd Qe Wm) Nr(aA Et Fp Hq Hu Hx Ih Ii Ij Ik Il Im In Ip Iq Ir It Iu Jk Jl Jn Jo Jp Jq Jr Js Jt Lh Li Lx Ly Lz Ma Mb Me Mf Mh Mj Ml Mm Mn Mp Mr Ms Mu Mv Mx My Nb Nc Nd Ne Nf Ng Nh Ni Nj Nk Nl Nm Nn No Nq Nv Nx Ny Of Oh Oi Ok Om On Oy Oz Pa Pb Pd Pe Pf Pg Po Pz Qa Qc Qe) Ni(aA Et Fp Hq Hv Hw Hx Ih Ii Ij Ik Il Im In Io Ip Iq Ir It Iu Jg Jk Jn Jo Jp Jq Jr Js Jt Lh Li Lu Lx Ly Lz Ma Mb Me Mf Mh Mj Mk Ml Mm Mn Mp Mr Ms Mu Mv Mx Nb Nc Nd Ne Nf Nj Nk Nl Nm Nn No Nq Nv Nx Ny Oh Oi Om Oz Pa Pb Pd Pe Pf Pg Po Pz Qa Qb Qc Qd Qe) Nk(aA Et Fp Hq Hu Hv Hw Hx Ih Ii Ij Ik Il Im In Io Ip Iq Ir It Jk Jn Jo Jp Jq Jr Js Jt Lh Li Ly Lz Ma Mb Me Mf Mh Mj Ml Mm Mn Mp Mr Ms Mu Mv Mx My Nb Nc Nd Ne Nf Nj Nl Nm Nn No Nq Nv Nx Ny Of Oh Oi Ok Om On Oy Oz Pa Pb Pd Pe Pf Pg Pz Qa Qc Qd Qe) Nh(aA Et Fp Hq Hv Hw Hx Ih Ii Ij Ik Il Im In Io Ip Iq Ir It Iu Jg Jk Jn Jo Jp Jq Jr Js Jt Lh Li Lu Lx Ly Lz Mb Me Mf Mh Mj Mk Ml Mm Mn Mp Mr Ms Mu Mv Mx Nb Nc Nd Ne Nf Nj Nl Nm Nn No Nq Nv Nx Ny Oh Om Oz Pa Pb Pd Pe Pf Pg Po Pz Qa Qb Qc Qd Qe Wm) Hv(aA Et Fp Hq Hw Hx Ih Ii Ij Ik Il Im Io Ip Iq Ir It Iu Jg Jk Jl Jn Jo Jp Jq Jr Js Jt Lh Li Lu Lx Ly Lz Mb Me Mf Mh Mj Mk Ml Mm Mn Mp Mr Ms Mu Mv Nb Nc Nd Ne Nf Nj Nl Nm Nn No Nq Nv Nx Ny Oh Om On Oz Pa Pb Pd Pe Pf Pg Po Pz Qa Qb Qc Qd Qe) In(Et Fp Hq Hw Hx Ih Ii Ij Ik Il Im Io Ip Iq It Iu Jk Jl Jn Jo Jp Jq Jr Js Jt Lh Li Lx Ly Lz Ma Mb Me Mf Mh Mj Ml Mm Mn Mp Mr Ms Mu Mv Mx Nb Nc Nd Ne Nf Nj Nl Nm Nn No Nq Nv Nx Ny Of Oh Oi Om Oy Oz Pa Pb Pd Pe Pf Pg Po Pz Qa Qb Qc Qd Qe Wm) Jr(Et Fp Hq Hw Hx Ih Ii Ij Ik Il Im Io Ip Iq Ir It Iu Jg Jk Jl Jn Jo Jp Jq Js Jt Lh Li Lu Lx Ly Lz Mb Me Mf Mh Mj Mk Ml Mm Mn Mp Mr Ms Mu Mv Mx Nb Nc Nd Ne Nf Nj Nl Nm Nn No Nq Nv Nx Ny Oh Om On Oz Pa Pb Pd Pe Pf Pg Po Pz Qa Qb Qc Qd Qe) Ma(Et Fp Hq Hw Hx Ih Ii Ij Ik Il Im Io Ip Iq It Iu Jg Jk Jn Jo Jp Jq Js Jt Lh Li Lu Lx Ly Lz Mb Me Mf Mh Mj Mk Ml Mm Mn Mp Mr Ms Mu Mv Mx Nb Nc Nd Ne Nf Nj Nl Nm Nn No Nq Nv Nx Ny Oh Oi Om Oz Pa Pb Pd Pe Pf Pg Po Pz Qa Qb Qc Qd Qe Wm) Ir(aA Et Fp Hq Hw Hx Ih Ii Ij Ik Il Im Io Ip Iq Iu Jg Jk Jl Jn Jo Jp Jq Js Jt Lh Li Lu Lx Ly Lz Mb Me Mf Mh Mj Mk Mm Mn Mp Mr Ms Mu Mv Nb Nc Nd Ne Nf Nj Nl Nm Nn No Nq Nv Nx Ny Oh Ok Om On Oz Pa Pb Pd Pe Pf Pg Po Pz Qa Qb Qc Qd Qe) Oi(aA Et Fp Hq Hw Hx Ih Ii Ij Ik Il Im Io Ip Iq It Iu Jg Jk Jn Jo Jp Jq Js Jt Lh Li Lu Lx Ly Lz Mb Me Mf Mh Mj Mk Ml Mm Mn Mp Mr Ms Mu Mv Mx Nb Nc Nd Ne Nf Nj Nl Nm Nn No Nq Nv Nx Ny Oh Om Oz Pa Pb Pd Pe Pf Pg Po Pz Qa Qb Qc Qe) On(Et Fp Hq Hw Hx Ih Ii Ij Ik Il Im Io Ip Iq It Iu Jg Jk Jl Jn Jo Jp Jq Js Jt Lh Li Lu Lx Ly Lz Mb Me Mf Mh Mj Mk Ml Mm Mn Mp Mr Ms Mu Mv Mx Nb Nc Nd Ne Nf Nj Nl Nm Nn No Nq Nx Oh Ok Om Oz Pa Pb Pd Pe Pf Pg Po Pz Qa Qb Qc Qd Qe) Jl(aA Et Fp Hq Hw Hx Ih Ij Ik Il Im Io Ip Iq It Iu Jg Jk Jn Jo Jp Jq Js Jt Lh Li Lx Ly Lz Mb Me Mf Mh Mj Ml Mm Mn Mp Mr Ms Mu Mv Mx Nb Nc Nd Ne Nf Nj Nl Nm Nn No Nq Nv Nx On Om Oz Pa Pb Pd Pe Pf Pg Po Pz Qa Qb Qc Qd Qe) Pe(aA Et Fp Hq Hu Hw Hx Ih Ii Ij Ik Il Im Io Ip Iq It Iu Jk Jn Jo Jp Jq Js Jt Lh Li Lx Ly Lz Mb Me Mf Mh Mj Mk Ml Mm Mn Mp Mr Ms Mu Mv Mx Nb Nc Nd Ne Nf Nj Nm Nn No Nq Nv Nx Ny Oh Ok Om Oz Pa Pb Pd Pf Pg Po Pz Qa Qd Qe) aA(cX Et Fp Hq Hw Hx Ih Ii Ij Ik Il Im Io Ip Iq It Iu Jg Jk Jn Jo Jp Jq Js Jt Lh Li Lu Lx Ly Lz Mb Me Mf Mh Mj Mk Ml Mm Mn Mp Mr Ms Mu Mv Nb Nc Nd Nf Nj Nl Nm Nn Nq Nv Nx Ny Oh Om Oz Pb Pd Pf Pg Po Pz Qa Qb Qc Qd Qe) Pa(Et Fp Hq

Figure 2 Continued

Hw Hx Ih Ii Ij Ik Il Im Io Ip Iq It Iu Jk Jn Jo Jp Jq Js Jt Lh Li Lx Ly Lz Mb Me Mf Mh Mj Mk Ml Mm Mn Mp Mr Ms Mu Mv Mx Nb Nc Nd Ne Nf Nj Nl Nm Nn No Nq Nv Nx Ny Oh Om Oz Pb Pd Pf Pg Po Pz Qa Qc Qd Qe) My(Et Fp Hq Hu Hw Hx Ih Ii Ij Il Im Io Ip Iq It Iu Jg Jk Jn Jo Jp Jq Js Jt Lh Li Lu Lx Ly Lz Mb Me Mf Mh Mj Mk Ml Mm Mp Mr Mv Mx Nc Nd Ne Nf Nj Nl Nm Nn Nq Nv Nx Ny Of Oh Oy Oz Pb Pd Pf Pg Po Pz Qa Qb Qc Qe) Qd(Et Fp Hq Hw Hx Ih Ii Ij Ik Im Io Ip Iq It Iu Jg Jk Jn Jo Jp Jq Js Jt Lh Li Lu Lx Ly Lz Mb Me Mf Mh Mj Mk Ml Mm Mn Mp Mr Ms Mu Mv Nb Nc Nd Ne Nf Nj Nl Nm Nn Nq Nv Nx Ny Oh Om Oz Pb Pd Pf Pg Po Qa Qb Qc Qe) Ok(Et Fp Hq Hw Hx Ih Ii Ik Il Im Io Ip It Iu Jg Jk Jn Jo Jp Jq Js Jt Lh Li Lu Lx Ly Lz Mb Me Mf Mh Mj Mk Ml Mm Mp Mr Ms Mu Mv Nb Nc Nd Ne Nj Nl Nm Nn Nq Nx Ny Oh Om Oz Pb Pd Pf Pg Po Qa Qb Qc Qe) Mn(Et Fp Hq Ih Ii Ij Ik Il Im Io Ip Iq It Iu Jk Jn Jo Jp Jq Js Jt Lh Li Ly Lz Mb Mf Mh Mj Ml Mm Mp Mr Ms Mu Mv Mx Nb Nc Nd Nf Nj Nl Nm Nn No Nq Nv Nx Ny Of Oh Om Oy Oz Pb Pd Pf Pg Pz Qa Qc Qe) Hu(Et Fp Hq Hw Hx Ih Ii Ij Io Ip Iq It Iu Jg Jk Jn Jo Jp Jq Js Jt Lh Li Lu Lx Lz Mb Me Mf Mh Mj Mk Ml Mm Mp Mr Mv Mx Nb Nc Nd Ne Nf Nj Nl Nm Nn Nq Nv Nx Ny Oh Oz Pb Pf Pg Po Pz Qa Qb Qc Qe) No(Et Fp Hq Ii Ij Ik Il Im Ip Iq It Iu Jk Jn Jo Jp Jq Js Jt Lh Li Lx Ly Lz Mb Mc Mf Mh Mj Ml Mm Mp Mr Ms Mu Mv Mx Nb Nc Nd Ne Nf Nj Nl Nm Nn Nq Nv Nx Ny Oh Om Oz Pb Pd Pf Pg Pz Qa Qc Qe) Ms(Et Fp Hq Hx Ih Ii Ij Ik Il Im Io Ip Iq It Iu Jk Jn Jo Jp Jq Js Jt Lh Li Ly Lz Mb Mf Mh Mj Ml Mm Mp Mr Mu Mv Mx Nb Nc Nd Nc Nf Nj Nl Nm Nn Nq Nv Nx Ny Oh Om Oz Pb Pd Pf Pg Pz Qa Qc) Il(Et Fp Hq Ih Ii Ij Ik Im Io Ip Iq It Iu Jk Jn Jo Jp Jq Js Jt Lh Li Ly Mb Mf Mh Mj Ml Mm Mp Mr Mu Mv Mx Nb Nc Nd Ne Nf Nj Nl Nm Nn Nq Ns Nv Nx Ny Oh Om Oz Pb Pd Pf Pg Pz Qa Qc Qe) Nq(Et Fp Hq Ih Ii Ij Ik Im Ip Iq It Iu Jk Jn Jo Jp Jq Js Jt Lh Li Ly Lz Mb Mh Mj Ml Mm Mp Mr Mu Mv Mx Nb Nc Nd Nf Nj Nl Nm Nn Nv Nx Ny Of Oh Om Oy Oz Pb Pd Pf Pg Pz Qa Qc Qe) Hq(Et Fp Ii Ij Ik Im Ip Iq It Iu Jk Jn Jo Jp Jq Js Jt Lh Li Lx Ly Mb Mf Mh Mj Ml Mm Mp Mr Mu Mv Mx Nb Nc Nd Nf Nj Nl Nm Nn Nv Nx Ny Of Oh Om Oy Oz Pb Pd Pf Pg Pz Qa Qc Qe) Jn(Fp Hw Hx Ih Ii Ij Ik Im Io Ip Iq It Iu Jk Jp Jq Js Jt Li Ly Lz Mb Mf Mh Mj Ml Mp Mr Mu Mv Mx Nb Nc Nd Ne Nf Nj Nl Nm Nn Ns Nv Ny Of Oh Om Oz Pb Pd Pf Pg Pz Qa Qb) Of(Et Fp Hw Ih Ii Im Io Ip Iq It Jg Jk Jp Jq Js Li Lu Lx Lz Mb Me Mf Mh Mj Mk Ml Mm Mp Mr Mv Mx Nc Nd Ne Nf Nj Nl Nm Nn Nv Nx Ny Oh Oy Pb Pg Po Pz Qa Qb Qc Qe Wm) Oy(Et Fp Hw Hx Ih Ii Im Io Ip Iq It Jg Jk Jo Jp Jq Js Li Lu Lx Lz Mb Me Mf Mh Ml Mm Mp Mv Mx Nc Nd Ne Nf Nj Nl Nm Nv Nx Ny Oh Pb Pg Po Pz Qa Qb Qc Qe Wm) Oz(Fp Hx Ih Ii Ij Ik Im Io Ip Iq It Iu Jk Jp Jq Js Jt Ly Lz Mb Mf Mh Mj Mk Ml Mp Mr Mu Mv Mx Nb Nd Nf Nj Nl Nm Nn Nv Nx Ny Oh Om Pb Pd Pf Pg Po Pz Qa Qe) Iu(Fp Hw Hx Ih Ii Ij Ik Im Io Ip Iq It Jk Jp Jq Js Jt Lx Ly Lz Mb Mf Mh Mj Ml Mp Mr Mu Mv Mx Nb Nd Nf Nj Nm Nn Nv Nx Ny Oh Om Pb Pd Pf Pg Pz Qa Qe) Mv(Fp Ih Ii Ij Ik Im Io Ip Iq It Jg Jp Jq Js Jt Lh Ly Lz Mb Mh Mj Ml Mp Mr Mu Mx Nb Nd Nf Nj Nl Nm Nn Ns Nv Nx Oh Om Pb Pd Pf Pg Pz Qa Qc Qe) cT(aE AF aH aL Ao aR aS aU aW AX aZ Bb bE Bg bH bI bJ bM bN Bo bQ bR bU bX bZ cC cD cE cF CH Cp Cq cR CS cU CX dF dG DK dM) Ij(Et Fp Hr Hx Ik Im Ip Iq Jk Jo Jp Jq Js Jt Lh Ly Mb Me Mh Mj Ml Mm Mp Mr Mu Mx Nb Nd Nf Nj Nl Nm Nn Nv Nx Oh Om Pd Pf Pg Pz Qa Qe) Iq(Et Fp Ii Ik Im Ip Jk Jo Jp Jq Js Jt Lh Li Ly Mh Mj Ml Mp Mr Mu Mx Nb Nd Nf Nj Nl Nm Nv Nx Ny Oh Om Pb Pd Pf Pg Pz Qa Qc Qe) Hr(Et Hw Hx Ih Ii Im Io It Jg Jk Jo Jp Li Lu Lx Lz Mb Me Mf Mk Ml Mm Mp Mx Nb Nc Nd Ne Nf Nj Nn Nv Nx Ny Pb Pg Po Pz Qb Qc) Ns(Et Fp Hw Hx Ih Ii Io Ip It Jg Jk Jo Jp Jq Js Lh Lu Lx Ly Lz Mb Me Mf Mk Mm Mr Nd Ne Nl Nm Nv Nx Pb Po Pz Qa Qb Qc Qe) Pf(Fp Ih Ii Ik Im Io Ip It Jk Jp Jq Jt Li Ly Lz Mb Mh Mj Ml Mp Mr Mu Mx Nb Nd Nf Nj Nm Nn Nv Ny Oh Om Pb Pg Pz Qa Qe) Om(Fp Hw Hx Ih Ii Ik Im Ip It Jg Jk Jt Ly Mb Mh Mj Ml Mp Mr Mu Mx Nd Nf Nj Nl Nm Nn Nv Nx Ny Oh Pb Pd Pg Pz Qa) Mh(Fp Ih Ii Ik Im Ip It Jk Jp Jq Js Jt Ly Lz Mj Ml Mp Mr Mu Mx Nd Nf Nj Nm Nv Ny Oh Pb Pd Pg Qa) Jt(Hw Ih Ii Ik Im Ip It Jk Jo Js Lw Ly Mb Mj Ml Mp Mr Mu Mx Nf Nj Nn Nv Ny Oh Pb Pd Pg Pz) Oh(Ih Ii Ik Im Ip It Jk Jq Ly Mb Mj Ml Mp Mr Mu Mx Nd Nf Nj Nm Nn Nv Ny Pb Pd Pg Pz) Nv(Fp Ik Im Ip Jp Jq Js Lh Ly Mj Ml Mp Mr Mu Mx Nb Ng Nj Nl Nm Nx Pd Qa Qe) Pb(Fp Hx Ik Im Ip Jo Jp Jq Js Lh Ly Mj Mp Mr Mu Mx Nb Ng Nj Nm Pd Qa Qe) Ml(Fp Hx Ik Ip Jo Jp Jq Js Lh Ly Mb Mj Mp Mr Mu Nb Nj Nm Pd Qa Qe) Nf(Fp Ik Im Ip Jo Jp Jq Js Lh Li Ly Mj Mp Mr Mu Nb Nl Nm Pd Qa Qe) Ik(Ih Ii Ip Jk Jp Jq Js Mj Mp Mr Mx Nd Nm Nn Ny Pg Pz Qa Qe) Qa(Hw Hx Ih Ii Im Ip It Jk Js Ly Mx Nj Nn Ny Pd Pg Pz Qb) cS(AP aW aZ bN Bo bQ bR bS bU cI cK cR cX DG dH dM) Ng(Et Hw Hx Ih Io Li Lu Lx Me Mf Mk Nc Ny Po Pz Qb Wm) Pg(Fp Im Ip Jq Js Lh Ly Mj Mp Mr Mu Mx Nb Nj Nl Nm Pd) Mr(Ih Ii Im Ip It Jk Jq Mp Mu Mx Nj Nm Ny Pz Wm) Jq(Ih Ii Im It Lw Ly Mp Mx Nj Nn Ny Pd Pz) Mj(Ih Ii Ip It Jk Mp Mu Mx Nj Nm Ny Pz) Lw(Et Jo Lh Lx Mk Po Qb Qc Qc Wm) bA(aW bJ bQ bR bU cR cX dG Dk dM) Mx(Fp Ip Js Ly Mp Mu Nm Pd Qe) Pz(Et Fp Ip Jp Js Nj Nm Pd Qe) cR(aW Ba bE Bo cA cP cX DK) Ny(Fp Hx Jo Js Lh Mu Nb Pd) aX(aW aZ bR bU cA cK cP cX) Ii(Js Lh Ly Mp Mu Nb Qe) Jk(Im Lh Ly Mp Mu Nb Pd) Nj(Im Ip Mp Mu Nd Nm) aW(aE Ba Bo DK) Wm(Ji Jj Lv Md) cP(aL aR bE Dk) Nn(Jp Js Qe) Mu(Ip Nm Pd) Dk(bE bU) Mp(Lx Nd) Im(Ih Nd) It(Fp Js) NmLy} Ji{Oz(aA Et Fp Hq Hu Hv Hw Hx Ih Ii Ij Ik Il Im Io Ip Iq Ir Is It Iu Iv Jg Jh Jk Jl Jm Jn Jo Jp Jr Js Jt Lh Li Lj Lu Lv Lw Lx Ly Lz Mb Mc Me Mf Mg Mh Mi Mj Mk Ml Mm Mn Mp Mq Mr Ms Mt Mu Mv Mw My Mz Na Nb Nc Nd Nc Nf Ng Nh Ni Nj Nk Nl Nm Nn No Nq Nr Ns Nt Nu Nv Nw Nx Ny Oe Of Og Oh Oi Ok Om On Oy Pa Pb Pc Pd Pe Pf Pg Po Pz Qa Qb Qc Qd Qe) Nh(aA Et Fp Hq Hu Hv Hw Hx Ih Ii Ij Ik Il Im Io Ip Iq Ir Is It Iu Iv Jg Jk Jl Jm Jn Jo Jp Jr Js Jt Lh Li Lj Lu Lv Lw Lx Ly Lz Mb Mc Mc Mf Mg Mh Mi Mj Mk Mm Mn Mp Mq Mr Ms Mt Mu Mv Mw Mx My Mz Na Nb Nc Nd Ne Nf Ng Ni Nj Nk Nl Nm Nn No Nq Nr Ns Nt Nu Nv Nw Nx Ny Oe Of Og Oh Oi Ok Om On Oy Pa Pb Pc Pd Pe Pf Pg Po Pz Qa Qb Qc Qd Qe) Pa(aA Et Fp Hq Hu Hv Hw Hx Ih Ii Ij Ik Il Im Io Ip Iq Ir Is It Iu Iv Jg Jh Jk Jl Jm Jn Jo Jp Jr Js Jt Lh Li Lj Lu Lv Lw Lx Ly Lz Mb Mc Me Mf Mg Mh Mi Mj Mk Ml Mm Mn Mp Mq Mr Ms Mt Mu Mv Mw My Mz Na Nb Nc Nd Ne Nf Ng Ni Nj Nk Nl Nm Nn No Nq Nr Ns Nt Nu Nv Nw Nx Oe Of Og Oh Oi Ok Om On Oy Pb Pc Pd Pe Pf Pg Po Pz Qa Qb Qc Qd Qe) Lu(aA Et Fp Hq Hu Hv Hw Hx Ih Ii Ij Ik Il Im Io Ip Iq Ir Is It Iu Iv Jg Jh Jk Jl Jm Jn Jo Jp Jr Js Jt Lh Li Lj Lv Lw Lx Ly Lz Mb Mc Me Mf Mg Mh Mi Mj Mk Mm Mn Mp Mq Mr Ms Mt Mu Mv Mw My Mz Na Nb Nc Nd Ne Ng Ni Nj Nk Nl Nm Nn No Nq Nr Ns Nt Nu Nv Nw Nx Ny Oe Of Og Oh Oi Ok Om On Oy Pb Pc Pd Pe Pf Pg Po Pz Qa Qb Qc Qd Qe) Pf(aA Et Fp Hq Hu Hv Hw Hx Ih Ii Ij Ik Il Im Io Ip Iq Ir Is It Iu Iv Jg Jh Jk Jl Jm Jn Jo Jp Jr Js Jt Lh Li Lj Lv Lw Lx Ly Lz Mb Mc Me Mf Mg Mh Mi Mj Mk Mm Mn Mp Mq Mr Ms Mt Mu Mv Mw My Mz Na Nb Nc Nd Ne Ng Ni Nj Nk Nl Nm Nn No Nq Nr Ns Nt Nu Nv Nw Nx Ny Oe Of Og Oh Oi Ok Om On Oy Pb Pc Pd Pe Pg Po Pz Qa Qb Qc Qd Qe) No(aA Et Fp Hq Hu Hv Hw Hx Ih Ii Ij Ik Il Im Io Ip Iq Ir It Iu Iv Jg Jk Jm Jn Jo Jp Jr Js Jt Lh Li Lj Lv Lw Lx Ly Lz Mb Mc Me Mf Mg Mh Mi Mj Mk Ml Mm Mn Mp Mq Mr Ms Mt Mv Mw Mx My Mz Na Nb Nc Nd Ne Nf Ng Ni Nj Nk Nl Nm Nn Nq Nr Ns Nt Nu Nv Nw Nx Ny Oe Of Og Oh Oi Ok Om On Oy Pb Pc Pd Pe Pg Po Pz Qa Qb Qc Qd Qe) Ns(aA Et Fp Hq Hu Hv Hw Hx Ih Ii Ij Ik Il Im Io Ip Iq Ir Is It Iu Iv Jg Jk Jl Jm Jn Jo Jp Jr Js Jt Lh Li Lj Lv Lw Lx Ly Lz Mb Mc Me Mf Mg Mh Mi Mj Mk Ml Mm Mn Mp Mq Mr Ms Mt Mv Mw Mx My Mz Na Nb Nc Nd Ne Nf Ng Ni Nj Nk Nl Nm Nn Nq Nr Nt Nu Nv Nw Nx Ny Oe Of Og Oh Oi Ok Om Oy Pb Pd Pc Pg Po Pz Qa Qb Qc Qd Qe) Mi(aA Et Fp Hq Hu Hv Hw Hx Ih Ii Ij Ik Il Im Io Ip Iq Ir Is It Iu Iv Jg Jh Jk Jl Jm Jn Jo Jp Jr Js Jt Lh Li Lj Lv Lw Lx Ly Lz Mb Mc Me Mf Mg Mh Mj Mk Mm Mn Mp Mq Mr Ms Mt Mu Mv Mw My Mz Na Nb Nc Nd Ne Ng Ni Nj Nk Nl Nm Nn Nq Nr Nt Nu Nv Nw Nx Ny Oe Of Og Oh Oi Ok Om On Oy Pb Pd Pe Pg Po Pz Qa Qb Qc Qd Qe) Hv(aA Et Fp Hq Hu Hw Hx Ih Ii Ij Ik Il Im Io Ip Iq Ir Is It Iu Iv Jg Jk Jl Jm Jn Jo Jp Jr Js Jt Lh Li Lj Lv Lw Lx Ly Lz Mb Mc Me Mf Mg Mh Mj Mk Mm Mn Mp Mq Mr Ms Mt Mu Mv Mw My Mz Na Nb Nc Nd Ne Ng Ni Nj Nk Nl Nm Nn Nq Nr Nt Nu Nv Nw Nx Ny Oe Of Og Oh Oi Ok Om On Oy Pb Pc Pd Pe Pg Po Pz Qa Qb Qc Qd Qe) Mv(aA Et Fp Hq Hu Hw Hx Ih Ii Ik Il Im Io Ip Iq Ir Is It Iu Iv Jg Jh Jk Jl Jm Jn Jo Jp Jr Js Jt Lh Li Lj Lv Lw Lx Ly Lz Mb Mc Me Mf Mg Mh Mj Mk Mm Mn Mp Mq Mr Ms Mt Mu Mw My Mz Na Nb Nc Nd Ne Ng Ni Nj Nk Nl Nm Nn Nq Nr Nt Nu Nv Nw Nx Ny Oe Og Oh Oi Ok Om On Oy Pb Pc Pd Pe Pg Po Pz Qa Qb Qc Qd Qe) Lv(aA Et Fp Hq Hu Hw Hx Ih Ii Ij Ik Il Im

Figure 2 Continued bU(aP aY dI) CsCu aPbR} cS{cP(aC aD aE aG aH aI aJ aK aL aM aN aO aP aQ AR aS aU aV aY aZ Ba BB BC bF bH bI bL bM BO bP bQ bS bV bW bX cA cB cC cE cG CH cI cK cL cN CO cQ Cs CU cV cW CX cY cZ dA dB dC dD DE dF dG dH dI dJ dL dM dN) bR(aD aE aF al aJ aN aP aV aW aX aY Ba bE bF bG bH bJ bM bO bP bU bV cH cI cK cQ cR cU cX dA dD dI dM dN) bU(aD aE aJ aM aN aP aV aW aY Ba bE bG bH bJ bM bO bV bZ cH cI cN cQ cR cU dA dI dM dN) bN(aD aJ aN aW Ba bE bO bS bX bZ cA cB cC cD cF cI cK cN cQ dH dK dN) cI(aD aJ aX bG bZ cF cM cN cQ dN eF) aX{bX cB cK) bZ(aW bQ dH) BaBo aIaW aJdG bEdD} Md{Om(Et Fp Hq Hw Hx Ih Ii Ij Ik Il Im Io Ip Iq Ir It Iu Jg Jh Jk Jm Jn Jo Jp Jq Jr Js Jt Li Lj Ly Lz Mb Me Mf Mg Mh Mj Mk Ml Mm Mn Mq Mr Mt Mu Mv Mw Mx Na Nc Nd Ne Nf Nj Nk Nl Nm No Nq Nr Nt Nu Nv Nx Ny Oh Oz Pa Pb Pd Pe Pf Pg Po Pz Qb Qc Qe) Nw(Hr Hv Ik In Ir Iv Jg Jk Jo Jp Jr Jt Lh Lu Lw Mc Mp Mt Mv Nb Nh Ni No Ns Nt Oi Pa Pe Pf Qa) Jh(Hv Iv Lh Lw Lx Mc Mp Mz No Pc Qa) Mi(Iv Jg Jp Lw Ma Mg Mt Nn Nt Pc) Mu(Hr Iv Lh Lw Lx Ma Mp Mz Pc) Mp(Iv Jg Jp Lh Mt Nb Nt) Iv(Jg Lw Mv Nn Nq Pc) Lx(Ma Mg) WmMw NqHu} Iv{In(Hr Hv Il Ir It Iu Jg Jp Jt Lh Ma Mi Ml Mp Mq Ms Mt Mv Mw Mz Nb Nd Nn Nq Nt Nw Oh Pf) Hr(Et Hv It Jg Jp Lh Lw Ma Mg Mi Mp Ms Mt Mv Mw Mz Nn Oi Pc Pf) Jh(Hu Hv Ij It Lw Ma Mg Mi Ml Mu Mx Ng Nn Ns Nw Of Og Oi Oy Pc) Mu(It Jm Js Lw Ma Mg Mi Ml Mx Ng Nk Ns Of Oi Oy Pc) Pc(It Jp Lw Ma Mg Mi Mv Nk Ns Nw Oi Om) Ma(Jg Jp Lw Mi Ml Ms Nn Nw Oi Om) Om(Ij It Ml Mx Of Oy) Nw(It Mg Ml Mx Oi) Lw(It Mg Mi Mx) Jg(Ng Of Oi) Mg(Ng Oi) NnOi MiMx IrIt} Mu{Hr(Et Hv Jh Jp Jr Lw Ma Mg Mh Mj Mr Mt Mz Ns Nt Nu Nw Oi Om Pa Pe Pf Qa Qd Qe) Oy(Ad Bc Bg Ch Co Ct Cu Lw Mi Nb Nw Om Oz Pa Pe) Lw(Hv In Jh Jm Ma Mi Ng Ns Nw Of Og Oi) Ma(Hu Hv Mi Mz Ng Ns Nw Of Oi Pa Pc) Mi(Hq In Jh Mt Ng Ns Of Pc) In(Jt Lh Nt Nw Pa Pe Qa) Ng(Jg Jh Mg Nw Om) Nw(My Ns Of Oi) Jh(Hu Ns Of) Om(Hu My Of) Oi(Nt Qd) CuHw NbOf} Mi{Jh(Hq Hr Hu Hv Ij Il In Jr Lw Ma Ml Mt Mx Mz Nf Ng Nh Nn Ns Nw Of Oi Oy Pc Pf) Pc(Hv Ik In Jp Lw Ma Mg Mq Mt Mz Ni Nk Ns Nt Nw Oi Om Qd) Om(Hr Ij In Ml Mt Nf Of Oy Pb) Hr(Jg Jp Lw Ma Mt Nw Qe) Ma(Hq Lw Nw) In(Lw Nt) Nw(Ml Mx) MgHq NgJg} Om{Of(Hr Hv In Jh Lh Lu Ma Mg Mp Mr Nb Ns Nt Oz Pa Pc Pe Pf) In(Hr Hu Lw Ma My Ng Ns Nt Pa Pc Pe Qa Wm) Hr(Hv Ma Mr Mt Ng Ns Oi Pf Qd Qe) Oy(Ma Mk Nb Oz Pa Pc) Ng(Jh Ma Mg) Hu(Jh Ma) NsPc} Nw{Ma(Hr Hv Ij In Ir Iu Jh Jr Lw Ml Ms Mt Mx My Nf Nh Ni No Ns Nt Ny Of Oi Oy Oz Pa Pb Pc Pe) Hr(Hv Jh Mg Mt Mv Ni Nt Oi) Mg(In My Ng Of Oi Oy) Jh(My Ng Ns Of Oy) NsPc NtIn NbNy} Oy{Mv(Ad Af Aj Al An Ao Ap Ar As Aw Ax Ba Bb Bg Bn Bo Ch Co Cp Cq Cs Ct Cv Cw Cx Db Dc Dd De Dg Di Dk Dl) Jh(Mk Nb Oz Pa Pe) Nq(Ba Bc Cu) Mg(Bg Nb Pe)} aX{cP(aW Bg bX bZ cD Ch cI Co Cx dK) bU(aE aJ aW Ba cI dK dN) cX(Ba Bg Ch Cu) BgaZ bRdK} Ma{Lw(Hv Jh Jp Ms Mt Nt Pa) Jh(Hu Hv Ng Pc) Pc(Hv Nt Qd) NtMs NgJg HrHv} bZ{Ba(aW bQ bR cC cE cR) cP(aF aJ aW bE bQ dK) aJ(bR dG)} Jh{Lw(Hv Ng Pa) Hr(Hv Mz Qd) Of(Hv Nb Pe) Ng(Mg Nt) QdPc} In{Nt(Hv Lw Pc Qa) Lw(Hv Lh Wm)} bE{eF(aF aW cE cI dK) aWgL cPdK} aJ{cP(bU cR dK) dGdN} cR{Ba(aW bQ) cPdK} Cu{CsEf McMx} NtOiPc LwHrHv

Unconstrained panels with 2 analytes, where 1.0E-7 >= 'model p-value' > 0. Contains 5 panels of 19,595 total panels evaluated. : Fr(aA Ji Jj) Jj(Is On)

Unconstrained panels with 2 analytes, where 1.0E-6 >= 'model p-value' > 1.0E-7. Contains 49 panels of 19,595 total panels evaluated. : Fr(Hr Hu Hv Is Iv Jr Lv Lw Ma Md My Ng Nh Ns Of Oi Ok On Oy) Ji(Hr In Is Jh Jj Jl Jq Ma Md Ml Mu Pc) On(Hr In Ma Md Ng Ns Of Oy) Jj(Iv Jl Mg Mu Nt Om) Is(Hr In) cS(cP cT)

Unconstrained panels with 2 analytes, where 1.0E-5 >= 'model p-value' > 1.0E-6. Contains 381 panels of 19,595 total panels evaluated. : Ji(aA Et Fp Hq Hu Hv Hw Hx Ih Ii Ij Ik Il Im Io Ip Iq Ir It Iu Iv Jg Jk Jm Jn Jo Jp Jr Js Jt Lh Li Lj Lu Lv Lw Lx Ly Lz Mb Mc Me Mf Mg Mh Mi Mj Mk Mm Mn Mp Mq Mr Ms Mt Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pd Pe Pf Pg Po Pz Qa Qb Qc Qd Qe) Fr(cS cT Et Fp Hq Hw Hx Ih Ii Ij Ik Il Im In Io Ip Iq Ir It Iu Jg Jh Jk Jl Jm Jn Jo Jp Jq Js Jt Lh Li Lj Lu Lx Ly Lz Mb Mc Me Mf Mg Mh Mi Mj Mk Ml Mm Mn Mp Mq Mr Ms Mt Mu Mv Mw Mx Mz Na Nb Nc Nd Ne Nf Ni Nj Nk Nl Nm Nn No Nq Nr Nt Nu Nv Nw Nx Ny Oe Og Oh Om Oz Pa Pb Pc Pd Pe Pf Pg Po Pz Qa Qb Qc Qd Qe) On(aA Hq Hu Hv Hw Hx Ih Ii Ij Il Io Ip Iq Ir Is It Iu Iv Jh Jk Jl Jm Jr Li Lj Lu Lv Lw Mc Mg Mh Mi Mj Ml Mn Mp Mq Mr Ms Mt Mu Mv Mw Mx My Mz Na Nd Nf Nh Ni Nk Nm Nn No Nq Nr Nt Nu Nv Nx Ny Oe Og Oh Oi Ok Oz Pa Pb Pc Pd Pe Pf Pg Pz Qb Qd) Is(aA Hv Ih Ij Iq It Jh Jl Jm Lv Lw Ma Md Mg Mi Ml Mu Mv Mx Ni Nk Nn Ns Nt Nw Og Oi Ok Om Pc Pf Qb) Jj(Jg Jh Jk Lh Lv Ma Mi Mt Mv Nw Oh Ok Pf Po Qd) Ok(aA Hr In Iv Jh Jl Lv Ma Md Mg Mi Mu Nn Pc) bA(aF aW bJ bR bU bZ cP cR cS dK) Jl(Hr Jh Lv Lw Ma Mg) aA(cS Lv Lw Ma Mg) Lv(Jh Mg Mu) cS(bN bR bU) Md(Nw Om) Mi(Jh Pc) cT(bJ dN) MaNw IvJh Unconstrained panels with 2 analytes, where 1.0E-4 >= 'model p-value' > 1.0E-5. Contains 688 panels of 19,595 total panels evaluated. : Ok(Et Hq Hu Hv Hw Hx Ih Ii Ij Ik Il Im Io Ip Iq Ir It Iu Jg Jk Jm Jn Jo Jp Jq Jr Js Jt Lh Li Lj Lu Lw Lx Lz Mc Me Mf Mh Mj Mk Ml Mn Mp Mq Mr Ms Mt Mv Mw Mx My Mz Na Nb Nc Nd Ne Nf Ng Nh Ni Nj Nk Nl Nm No Nq Nr Ns Nt Nu Nw Nx Ny Oe Of Og Oh Oi Om Oy Oz Pa Pb Pd Pe Pf Pg Po Pz Qa Qd Qe) Is(Et Fp Hq Hu Hw Hx Ii Ik Il Im Io Ip Ir Iu Iv Jg Jk Jn Jo Jp Jq Jr Js Jt Lh Li Lj Lu Lx Ly Lz Mb Mc Me Mf Mh Mj Mk Mm Mn Mp Mq Mr Ms Mt Mw My Mz Na Nb Nc Nd Ne Nf Ng Nh Nj Nl Nm No Nq Nr Nu Nv Nx Ny Oe Of Oh Oy Oz Pa Pb Pd Pe Pg Po Pz Qa Qc Qd Qe) bA(aA aC aD aE aG aH aI aJ aK aL aM aN aO aP aQ aR aS aU aV aX aY aZ bB bC bE bF BG bH bI bL bM bN bO bP bQ bS bV bW bX cA cB cC cD cE cF cG CH cI cJ cK cL cM cN CO cQ cT cU cV cW cX cY cZ dA dB dC dD dE dF dG dH dI dJ dL dM dN Fr) cS(aC aD aE aF aG aH aI aJ aK aL aM aN aO aP aS aU aV aW aX aY aZ Ba bE bF BG bH bI bJ bL bM bO bP bQ bS bV bX bZ cA cB cC cD cF cG cH cI cK cM cN cO cQ cR cU cW cX cY cZ dA dD dE dG dH dI dK dL dM dN) Jl(aA Hv Hw Ih Ii Ij Ik Il Im In Ip Ir It Iv Jg Jm Jp Jr Lz Mc Md Mi Ml Mp Mq Ms Mt Mu Mv Mx My Mz Nb Ni Nk Nm Nn No Nr Ns Nt Nu Nw Oe Of Og Oh Oi Om Oy Pc Pd Pf Qd) Jj(aA Et Hv Ii Ik Il Im Iu Jn Jo Jp Jq Jr Js Jt Lw Lx Mj Mm Mp Mq Mr Mw Mz Nb Nn Nq Nu Nv Nx Of Oz Pa Pc Pd Pe Pg Qa Qe) aA(aE aF aW bE bJ bM bR bU bX bZ cA cI cP cR cT cX dG dK Hr Iv Jg Jh Jr Mi Mn Mt Mu Mv Mz Nw Om Pc Pf Po) On(Et Fp Ik Im Jg Jn Jo Jp Jq Js Jt Lh Lx Ly Lz Mb Me Mf Mk Mm Nb Nc Ne Nj Nl Nw Om Po Qa Qc Qe) cT(aD aE aF aI aJ aP aW aX aY bE Bg bL bM bO bP bR bU bW bX bZ Ch cI CO cP cR cU DE dK dM) Mu(Cq Et Hr Hu Hv In Iv Jh Jp Jr Lw Ma Md Mg Mi Mt Mz Ng Ns Nt Nw Of Og Oi Om Pa Pc Pe Pf Qd) Lv(Et Hr Hv Iu Iv Jg Jp Lw Ma Mi Mp Mr Mt Mv Mw Mz Nb Nn Nt Nu Nw Oh Om Pa Pc Pe Pf Qd) Om(Hr Hu Hv In Iv Jh Lw Ma Mi Mt My Ng Ns Nt Nw Of Og Oi Oy Pa Pc Pf Qd) Nw(Hr Hv In Iv Jh Lw Mg Mi Ml Mp Mt Mv Nh Ni Ns Nt Oi Oz Pc Pf) Jh(Hr Hu Hv Lw Ma Mz Ng Ns Nt Oh Pa Pc Pe Pf Qd) Iv(Hr In It Jg Jp Lw Ma Mg Mi Mt Mv Nn Pc Pf) Fr(aE aW aX Ba bE bU cC cP cR cX DK Wm) Mi(Hr Jg Jp Lw Ma Md Mt Mv Nn Nt Wm) Ba(aW aX bZ cP cR) Ma(Hv Lw Mt Nt) Pc(Mt Nt Qd) aX(bU Co cP) aJ(bU cP) eF(bE cI) WmJi NtIn LwMt bZcP Unconstrained panels with 2 analytes, where 1.0E-3 >= 'model p-value' > 1.0E-4. Contains 1,676 panels of 19,595 total panels evaluated. : aA(aC aD aG aH aI aJ aK aL aM aN aO aP aQ aR aS aU aV aX aY aZ Ba bB bC bF BG bH bI bL bN bO bP bQ bS bV bW cB cC cD cE cF cG cH cJ cK cL cM cN CO cQ cU cV cW cY cZ dA dB dC dD dE dF dH dI dJ dL dM dN dR eF Et FP fR gL gP Hu Hv Ii Ij Ik Il Im In Ip Iq Ir It Iu Jk Jn Jp Jq Js Jt Lh Li Lj Lx Lz Mc Md Me Mf Mh Mj Ml Mm Mp Mq Mr Ms Mw Mx Na Nb Nd Ne Nf Nh Ni Nk Nl Nm Nn No Nq Ns Nt Nu

Figure 2 Continued

Nv Nx Ny Of Oh Oi Oz Pa Pd Pe Pg Qa Qc Qd Qe) Ba(aC AD aE AF aG aH al aJ aK AL aM AN AO aP aQ AR aS aU aV Aw Ax aY aZ bA BB BC bE bF BG bH bI bJ bL bM BN BO bP bQ bR bS bU bV bW bX cA cB cC cD cE cF cG CH cI cJ cK cL cM cN CO Cp CQ Cs CT CU CV CW CX cY cZ dA dB DC DD DE dF dG dH DI dJ DL dM dN Ef) Fr(Aa aC AD AF aG aH al AJ aK AL aM AN AO AP aQ AR AS aU aV Aw Ax aY aZ BB BC bF BG bH bI bJ bL bM BN BO bP bQ bR bS bV bW bX bZ cA cB cD cE cF cG CH cI cJ cK cL cM cN CO Cp CQ Cs Ct CU CV CW Cx cY cZ dA DB DC DD DE dF DG dH DI dJ DL dM dN Ef) Mi(Bg Et Fp Hq Hu Hv Hw Hx Ih Ii Ij Ik Il Im In Io Ip Iq Ir It Iu Jk Jm Jn Jo Jq Jr Js Jt Lh Li Lj Lu Lx Ly Lz Mb Mc Me Mf Mg Mh Mj Mk Ml Mm Mn Mp Mq Mr Ms Mw Mx My Mz Na Nb Nc Nd Ne Nf Ng Nh Ni Nj Nk Nl Nm No Nq Nr Ns Nu Nv Nx Ny Oe Of Og Oh Oi Oy Oz Pa Pb Pd Pe Pf Pg Po Pz Qa Qb Qc Qd Qe) Iv(Et Fp Hq Hu Hv Hw Hx Ih Ii Ij Ik Il Im Io Ip Iq Ir Iu Jk Jm Jn Jo Jq Jr Js Jt Lh Li Lj Lu Lx Ly Lz Mb Mc Md Me Mf Mh Mj Mk Ml Mm Mn Mp Mq Mr Ms Mw Mx My Mz Na Nb Nc Nd Ne Nf Ng Nh Ni Nj Nk Nl Nm No Nq Nr Ns Nt Nu Nv Nx Ny Oe Of Og Oh Oi Oy Oz Pa Pb Pd Pe Pg Po Pz Qa Qb Qc Qd Qe) Mu(Ao Bb Bg Co Dk Fp Hq Hw Hx Ih Ii Ij Ik Il Im Io Ip Iq Ir It Iu Jg Jk Jm Jn Jo Jq Js Jt Lh Li Lj Lu Lx Ly Lz Mb Mc Me Mf Mh Mj Mk Ml Mm Mn Mp Mq Mr Ms Mv Mw Mx My Na Nb Nc Nd Ne Nf Nh Ni Nj Nk Nl Nm Nn No Nq Nr Nu Nv Nx Ny Oe Oh Oy Oz Pb Pd Pg Po Pz Qa Qb Qc Qe) Nw(Et Fp Hq Hu Hw Hx Ih Ii Ij Ik Il Im Io Ip Iq Ir It Iu Jg Jk Jm Jn Jo Jp Jq Jr Js Jt Lh Li Lj Lu Lx Ly Lz Mb Mc Me Mf Mh Mj Mk Mm Mn Mq Mr Ms Mw Mx My Mz Na Nb Nc Nd Ne Nf Ng Nj Nk Nl Nm Nn No Nq Nr Nu Nv Nx Ny Oe Of Og Oh Oy Pa Pb Pd Pe Pg Po Pz Qa Qb Qc Qd Qe) Om(Et Fp Hq Hw Hx Ih Ii Ij Ik Il Im Io Ip Iq Ir It Iu Jg Jk Jm Jn Jo Jp Jq Jr Js Jt Lh Li Lj Lu Lx Ly Lz Mb Mc Me Mf Mg Mh Mj Mk Ml Mm Mn Mp Mq Mr Ms Mv Mw Mx Mz Na Nb Nc Nd Ne Nf Nh Ni Nj Nk Nl Nm Nn No Nq Nr Nu Nv Nx Ny Oe Oh Oz Pb Pd Pe Pg Po Pz Qa Qb Qc Qe Wm) cT(aC Ad Af aG aH Aj aK AL aM AN AO Ap aQ AR AS aU aV Aw Ax aZ BB BC bF bG bH bI BN Bo bQ bS bV cA cB cC cD cE cF cG cH cI cK cL cM cN Cp CQ Cs Ct Cu CV CW CX cY cZ dA DB DC DD dF DG dH DI dJ Dk DL eF) Lv(Fp Hq Hu Hw Hx Ih Ii Ij Ik Il Im In Io Ip Iq Ir It Jk Jm Jn Jo Jq Jr Js Jt Lh Li Lj Lu Lx Ly Lz Mb Mc Md Me Mf Mh Mj Mk Ml Mm Mn Mq Ms Mx My Na Nc Nd Ne Nf Ng Nh Ni Nj Nk Nl Nm No Nq Nr Ns Nv Nx Ny Oe Of Og Oi Oy Oz Pb Pd Pg Po Pz Qa Qb Qc Qe Wm) Jh(Et Fp Hq Ih Ij Ik Il Im In Io Ip Iq Ir It Iu Jg Jm Jn Jo Jp Jq Jr Js Jt Lh Li Lj Lu Lx Mc Md Mf Mg Mh Mj Mk Ml Mm Mn Mp Mq Mr Ms Mt Mv Mw Mx My Na Nb Nc Nd Ne Nh Ni Nj Nk Nl Nm Nn No Nq Nr Nu Nv Nx Ny Oe Of Og Oi Oy Oz Pb Pd Pg Po Pz Qa Qb Qc Qe) Ji(Et Fp Hq Hu Hx Io Iq Iu Jk Jn Jo Jq Js Jt Lh Li Lj Lu Lx Ly Mb Me Mf Mh Mj Mk Mm Mn Mr Mw Na Nc Nd Ne Nf Ng Nh Nj Nl Nq Nv Nx Ny Oz Pa Pb Pe Pg Po Pz Qa Qb Qc Qe Wm) Jj(Fp Hq Hr Hu Hw Ij In Io Ip Ir It Jm Li Lj Lu Ly Mc Md Mf Mh Mk Ml Mn Ms Mx My Na Nc Nd Ne Nf Ng Nh Ni Nj Nk Nl Nm No Nr Ns Ny Oi Oy Pz Qb Qc Wm) cS(Ad Af Aj Al An Ao Ap aQ AR As Aw Ax BB BC Bn Bo bW cE Ch cJ cL Co Cp Cq Cs Ct Cu CV Cw Cx DB DC Dd De dF Dg Di dJ Dk Dl eF gL) Mt(Et Hr Hv In Ir Iu Jg Jp Jq Jr Jt Lh Mc Md Mg Mh Mj Mp Mq Mr Ms Mv Mz Nb Nd Ni Nk Nn No Ns Nt Nu Oh Oi Oz Pa Pe Pf Po Qa Qd Qe Wm) Nt(Et Hr Hv Ir It Jg Jm Jp Jq Jr Lw Mc Md Mg Mh Mj Mp Mq Mr Ms Mv Mw Mz Nd Ng Ni Nk Nn Ns Of Oh Oi Pa Pe Pf Po Qa Qd Qe) bA(Ad Af Aj Al An Ao Ap Ar As Aw Ax Bb Bc Bn Bo Cp Cq Cs Ct Cu Cv Cw Cx Db Dc Dd De Dg Di Dk Dl dR eF gL gP) Ma(Et Hr Ir Iu Jg Jp Jq Jr Jt Lh Lx Mg Mj Mp Mq Mr Ms Mv Mw Mz Nb Nn Nu Nv Oh Oz Pa Pc Pe Pf Po Qa Qd Qe) Mg(Bg Hr Hv In Ir Jp Jr Lh Lw Lx Mh Mj Mq Mr Mv Mz Ng Nn No Oh Oi Oz Pa Pc Pe Pf Qa Qd Qe) aX(aE al aJ AO Ar AW Bg bM bO bR bX bZ cA cB cD Ch cI cK Cp Ct Cu Cx Dc dK dN) Lw(Et Hr Hv In Jg Jp Jr Lh Mj Mr Mv Mw Mz Nb Nu Oh Pa Pc Pe Pf Po Qa Qd Qe Wm) Jp(Hr Hv Jr Lh Md Mj Mp Mq Mr Mv Mz Ni Nn Ns Oh Oi Pa Pc Pe Pf Qd Wm) aJ(aE aF al aU aW bE bN bR bX bZ cB cC cD cF cI cK cR cX dG dK dN eF) Pf(Et Hr Hv In Jg Lh Md Mq Ms Mv Mz Nb Ni Nk Nn Ns Oi Pa Pc Pe Qd) dN(aE aF aM aW bE bN bR bU bX bZ cA cI cP cR dK dR eF gL gP) Mv(Ao Et Hr Hv In Jr Md Mz Ng Ns Oh Oi Pa Pc Pe Qd Qe) Jg(Hu Hv Md Mr My Mz Ng Ns Of Oh Oi Pa Pe Qa Qd Wm) Pc(Et Hv Jq Jr Lh Lx Mj Mq Mr Mz Oh Pa Pe Po Qa Qe) bZ(aD aF aP aW bE bQ bR bU bX cA cC cD cI dK) In(Cu Hv Jt Lh Mz Oh Po Qa Qd Qe) cP(aP aW bE Bg bU bV cR Cu dI dK) Hr(Et Hv Lh Mj Mz Po Qa Qd Qe) Qd(Hv Lh Mp Mz Nn Oi Pa Pe) Ok(Fp Ly Mb Mm Nv Qb Qc Wm) Cu(bE Cs Dc Ef Ii Mx) aP(aW bR bU bX cI dK) Nn(Hv Mq Mz Pa Pe) Md(Lh Lx Mp Nb) Mz(Hv Mq Pa Pe) bE(dK dR gL gP) eF(aF aW bQ dK) Wm(Is On) Mp(Hq Nd) gL(aF aW) AoNq CoOy CtEf EtHv cRdK Unconstrained panels with 2 analytes, where $1.0E-2 >=$ 'model p-value' $> 1.0E-3$. Contains 2,754 panels of 19,595 total panels evaluated. :
Mg(Ad Af Aj Al An Ao Ap Ar As Aw Ax Ba Bb Bc Bn Bo Ch Co Cp Cq Cs Ct Cu Cv Cw Cx Db Dc Dd De Dg Di Dk Dl Et Fp Hq Hu Hw Hx Ih Ii Ij Ik Il Im Io Ip Iq It Iu Jg Jk Jm Jn Jo Jq Js Jt Li Lj Lu Ly Lz Mb Mc Md Me Mf Mk Ml Mm Mn Mp Ms Mw Mx My Na Nb Nc Nd Ne Nf Nh Ni Nj Nk Nl Nm Nq Nr Ns Nu Nv Nx Ny Oe Of Og Oy Pb Pd Pg Po Pz Qb Qc Wm) cP(aC AD aE AF aG aH al Aj aK AL aM AN AO Ap aQ AR AS aU aV Aw Ax aY aZ BB BC bF bG bH bI bJ bL bM BN BO bP bS bV bW bX cA cB cC cD cE cF cG CH cI cJ cK cL cM cN CO Cp CQ Cs Ct cU CV CW CX cY cZ dA DB DC DD DE dF DG dH Di dJ Dk DL dM eF gL) Mv(Af Ap Aw Bb Bc Bg Bn Bo Co Cp Cq Ct Cu Dc Dd Dg Dk Fp Hq Hu Hw Hx Ih Ii Ij Ik Il Im Io Ip Iq Ir It Iu Jg Jk Jm Jn Jo Jq Js Jt Lh Li Lj Lu Lx Ly Lz Mb Mc Me Mf Mh Mj Mk Ml Mm Mn Mp Mq Mr Ms Mw Mx My Mz Na Nb Nc Nd Ne Nf Nh Ni Nj Nk Nl Nm Nn No Nq Nr Nu Nv Nx Ny Oe Of Og Oi Oy Oz Pb Pd Pg Po Pz Qa Qb Qc Wm) bZ(aC Ad aE Af aG aH al Aj aK AL aM AN AO Ap aQ AR AS aU aV Aw Ax aY aZ BB BC bF BG bH bI bJ bL bM BN BO bP bS bV bW cB cE cF cG CH cJ cK cL cM cN CO Cp CQ cR Cs Ct CU CV CW CX cY cZ dA DB DC DD DE dF DG dH DI dJ Dk DL dM eF) aX(aC AD AF aG aH Aj aK AL aM AN AP aQ aR AS aU Av Ax aY aZ BB BC bE bF bG bH bI bJ bL BN Bo bP bQ bS bV bW cC cE cF cG cH cI cL cM cN cO CQ cR Cs cU CV CW cX cY cZ dA DB DC DD dE dF DG dH DI dJ Dk DL dM dR eF fP gL gP) Ma(Aa Ad Af Al An Ba Bb Bc Bg Bo Ch Co Cp Cs Cu Cv Dc Dd De Di Dl Fp Hq Hu Hw Hx Ih Ii Ij Ik Il Im In Io Ip Iq It Jk Jm Jn Jo Js Li Lj Lu Ly Lz Mb Mc Md Me Mf Mh Mk Ml Mm Mn Mx My Na Nc Nd Ne Nf Ng Nh Ni Nj Nk Nl Nm No Nq Nr Ns Nx Ny Oe Of Og Oi Oy Oz Pb Pd Pg Po Pz Qb Qc Wm) Hv(Fp Hq Hu Hw Hx Ih Ii Ij Ik Il Im Io Ip Iq Ir It Iu Jk Jm Jn Jo Jq Jr Js Jt Lh Li Lj Lu Lx Ly Lz Mb Mc Md Me Mf Mh Mj Mk Ml Mm Mn Mp Mq Mr Ms Mw Mx My Na Nb Nc Nd Ne Nf Ng Nh Ni Nj Nk Nm No Nq Nr Ns Nu Nv Nx Ny Oe Of Og Oh Oi Oy Oz Pa Pb Pd Pe Pg Po Pz Qa Qb Qc Qe) Mz(Et Fp Hq Hu Hw Hx Ih Ii Ij Ik Il Im Io Ip Iq Ir It Iu Jk Jm Jn Jo Jq Jr Js Jt Lh Li Lj Lu Lx Ly Lz Mb Mc Md Me Mf Mh Mj Mk Ml Mm Mn Mp Mr Ms Mw Mx My Na Nb Nc Nd Ne Nf Ng Nh Ni Nj Nk Nl Nm No Nq Nr Ns Nu Nv Nx Ny Oe Of Og Oh Oi Oy Oz Pb Pd Pg Po Pz Qa Qb Qc Qe) Qd(Et Fp Hq Hu Hw Hx Ih Ii Ij Ik Il Im Io Ip Iq Ir It Iu Jk Jm Jn Jo Jq Jr Js Jt Li Lj Lu Lx Ly Lz Mb Mc Md Me Mf Mh Mj Mk Ml Mm Mn Mq Mr Ms Mw Mx My Na Nb Nc Nd Ne Nf Ng Nh Ni Nj Nk Nl Nm No Nq Nr Ns Nu Nv Nx Ny Oe Of Og Oh Oy Oz Pb Pd Pg Po Pz Qa Qb Qc Qe Wm) Mt(Af Al An Ao Ax Ba Bb Bc Bg Bn Bo Ch Cp Cq Cs Cu Cv Cx Dc Dd De Dg Di Dk Fp Hq Hu Hw Hx Ih Ii Ij Ik Il Im Io Ip Iq It Jk Jm Jn Jo Js Li Lj Lu Lx Ly Lz Mb Me Mf Mk Ml Mm Mn Mw Mx My Na Nc Ne Nf Ng Nh Nj Nl Nm Nq Nr Nv Nx Ny Oe Of Og Oy Pb Pd Pg Pz Qb Qc) aP(aC aD aE aF aG aH al aJ aK aL aM aN aO aQ aR aS aU aV aY aZ bB bC bE bF BG bH bI bJ bL bM bN bO bP bQ bS bV bW cA cB cC cD cE cF cG CH cJ cK cL cM cN CO Cp cQ cR CU cV cW cX cY cZ dA dB dC dD DE dF dG dH dI dJ dL dM dN eF gL) Jg(Et Fp Hq Hr Ih Ii Ij Ik Il Im In Io Ip Iq Ir It Iu Jk Jm Jn Jo Jp Jq Jr Js Jt Lh Li Lj Lu Ly Mb Mc Me Mf Mh Mj Mk Ml Mm Mn Mp Mq Ms Mw Mx Na Nb Nc Nd Ne Nf Nh Ni Nj Nk Nl Nm Nn No Nr Nu Nv Nx Ny Oe Og Oy Oz Pb Pc Pd Pg Po Pz Qb Qc Qe) Pf(Fp Hq Hu Hw Hx Ih Ii Ij Ik Il Im Io Ip Iq Ir It Iu Jk Jm Jn Jo Jq Jr Js Jt Li Lj Lu Lx Ly Lz Mb Mc Me Mf Mh Mj Mk Ml Mm Mn Mp Mr Mw Mx My Na Nc Nd Ne Nf Ng Nh Nj Nl Nm No Nq Nr Nu Nv Nx Ny Oe Of Og Oh Oy Oz Pb Pd Pg Po Pz Qa Qb Qc Qe Wm) Jp(Et Fp Hq Hu Hw

Figure 2 Continued

Hx Ih Ii Ij Ik Il Im In Io Ip Iq Ir It Iu Jk Jm Jn Jo Jq Js Jt Li Lj Lu Lx Ly Lz Mb Mc Me Mf Mh Mk Ml Mm Mn Ms Mw Mx My Na Nb Nc Nd Ne Nf Ng Nh Nj Nk Nl Nm No Nq Nr Nu Nv Nx Ny Oe Of Og Oy Oz Pb Pd Pg Po Pz Qa Qb Qc Qe) Lw(Fp Hq Hu Hw Hx Ih Ii Ij Ik Il Im Io Ip Iq Ir It Iu Jk Jm Jn Jo Jq Js Jt Li Lj Lu Lx Ly Lz Mb Mc Md Me Mf Mh Mk Ml Mm Mn Mp Mq Ms Mx My Na Nc Nd Ne Nf Ng Nh Ni Nj Nk Nl Nm Nn No Nq Nr Ns Nv Nx Ny Oe Of Og Oi Oy Oz Pb Pd Pg Pz Qb Qc) Cu(aA Ad aE AF aH aI aJ aM An Ao Ap As aU AW Ax aZ BC BG bH bJ BN bO bR bU bW bX cA cC CH cI cK CO Cp Cq cR Cv Cw CX cY Dd De Di DK Dl dN Fw Hr Hw Hx It Jj Js Mc Md Mi Mr Mu Nk Nv Ny Of Oy Pa Pb Pe Pg) eF(aC aD aE aG aH aI aK aL aM aN aO aQ aR aS aU aV aY aZ bB bC bF bG bH bI bJ bL bM bN bO bP bR bS bU bV bW bX cA cB cC cD cE cF cG cH cJ cK cL cM cN cO cQ cR cU cV cW cX cY cZ dA dB dC dD dE dF dG dH dI dJ dL dM dR gL gP) Qa(Et Hu Ih Ij Ik Il Im Io Ip Iq Ir It Iu Jk Jm Jn Jq Jr Js Jt Lh Li Lj Lu Lx Mc Md Mh Mj Mk Ml Mm Mn Mp Mq Mr Ms Mw Mx My Na Nb Nd Ne Nf Nh Ni Nk Nm Nn No Nq Nr Ns Nu Nv Nx Oe Of Og Oh Oi Oy Oz Pa Pb Pd Pe Pg Po Qb Qe) Lh(Et Hq Hu Ih Ij Ik Il Im Io Ip Ir It Iu Jk Jm Jn Jq Jr Js Jt Li Lu Lx Mc Mh Mj Mk Ml Mm Mn Mp Mq Mr Ms Mw My Na Nb Nd Nf Ng Nh Ni Nk Nm Nn No Nq Nr Ns Nt Nu Nv Nx Oe Of Og Oh Oi Oy Oz Pa Pb Pd Pe Pg Po Qe Wm) dN(aC aD aG aH aI aK aL aN aO aQ aR aS aU aV aY aZ bB bC bF BG bH bI bJ bL bM bO bP bQ bS bV bW cB cC cD cE cF cG cH cJ cK cL cM cN CO cQ cU cV cW cX cY cZ dA dB dC dD DE dF dG dH dI dJ dL dM fP) aJ(aC aD aG aH aK aL aM aN aO aQ aR aS aV aY aZ bB bC bF BG bH bI bJ bL bM bO bP bQ bS bV bW cA cE cG CH cJ cL cM cN CO cQ cU cV cW cY cZ dA dB dC dD DE dF dH dI dJ dL dM dR gL gP) Nt(Fp Hq Hu Hw Hx Ih Ii Ij Ik Il Im Io Ip Iq Iu Jk Jn Jo Js Jt Li Lj Lu Lx Ly Lz Mb Me Mf Mk Ml Mm Mn Mx My Na Nb Nc Ne Nf Nh Nj Nl Nm No Nq Nr Nu Nv Nx Ny Oe Og Oy Oz Pb Pd Pg Pz Qb Qc Wm) Pc(Fp Hr Hu Ii Ij Ik Il Im In Ip Ir Iu Jk Jn Jo Js Jt Li Lj Lu Mc Md Me Mh Mk Mm Mp Ms Mw Mx My Na Nb Nc Nd Ne Nh Ni Nj Nk Nl Nm Nn No Nq Nr Ns Nu Nv Nx Ny Of Og Oi Oy Oz Pd Pg Qb Qc) Et(Fp Hu Ik Il Im In Io Ip Ir Iu Jk Jn Jq Jr Js Jt Li Lu Lx Mc Md Mh Mj Mk Mn Mp Mq Mr Ms Mw My Na Nb Nd Ng Nh Ni Nk Nn No Nq Ns Nu Nv Nx Oc Of Og Oh Oi Oz Pa Pd Pe Pg Po Qe Wm) aA(Aa Ad Af Aj Al An Ao Ap Ar As Aw Ax Bb Bc Bn Bo Ch Cp Cq Cs Ct Cv Cw Cx Dc Dd De Dg Di Dl Hq Hw Hx Ih Io Jm Jo Lu Ly Mb Mk My Nc Ng Nj Nr Oe Og Oy Pb Pz Qb Wm) Oh(Hr Hu Ik Ip Ir It Iu Jk Jm Jn Jq Jr Jt Li Lj Lu Lx Mc Md Mh Mj Ml Mm Mp Mq Mr Ms Mw Na Nb Nd Nh Ni Nk Nm Nn No Nq Ns Nu Nv Nx Oe Og Oi Oz Pa Pd Pe Po Qe) Qe(Hu Ih Ik Ip Ir It Iu Jk Jm Jq Jr Jt Li Lu Lx Mc Md Mh Mj Mm Mp Mq Mr Ms Mw Na Nb Nd Nh Ni Nk Nn No Nq Ns Nu Nv Nx Oe Og Oi Oz Pa Pd Pe Po Qe) dK(aD aE aF aI aM aN aO Ar aW aY bC bF BG bH bJ bN bO bR bU bV bW bX cA cC cD cF cG cI cM cN CO cQ cU cW cX dE dF dG dH dI dM gL) Nn(Bg Fp Hr Ik Im In Ip Ir Iu Jk Jn Jq Jr Js Jt Li Lj Lx Md Mh Mj Mm Mp Mr Ms Mw My Na Nb Nh Ni Nk No Ns Nu Nv Nx Og Oi Oy Oz Pd Po) Pa(Hr Ik Im In Ip Ir Jk Jn Jq Jr Js Jt Li Lx Lz Mc Md Mj Mm Mp Mq Ms Mw Nb Nh Ni Nk Nq Ns Nu Nv Nx Oi Oy Pd Pe Po Wm) Pe(Hr Hu Ik Im In Ip Jk Jn Jq Jr Js Jt Li Lx Lz Mc Md Mj Mm Mp Mq Mr Ms Mw My Nb Nh Ni Nk Nq Ns Nu Nv Nx Oi Oy Pd Po) Po(Ip Ir It Iu Jm Jq Jr Jt Lu Lx Mc Md Mj Ml Mm Mp Mq Mr Ms Mw Nb Nd Nh Ni Nk No Nr Ns Nu Nv Of Og Oi Oy Oz) Ef(Ad Af Aj Al An Ao Ap Ar As Aw Ax Bb Bc Bg Bn Bo Ch Co Cp Cq Cs Cv Cw Cx Db Dc Dd De Dg Di Dk Dl Fw Gl) Mp(Hr Ik Il In Ip Ir Iu Jn Jq Jr Jt Li Lu Lx Mc Mh Mj Mq Mr Ms Mw Na Nb Nh Nj No Ns Nu Nv Oi Oz Pg Wm) In(Ad Aw Ba Bc Bg Ch Co Cp Cw De Ii Iu Jk Jn Jq Jr Js Li Lx Mj Mm Mq Mr Mw Nb Nu Nv Nx Oz Pd Wm) Mu(Ad Af Aj Al An Ap Ar As Aw Ax Ba Bc Bn Bo Ch Cp Cs Ct Cv Cw Cx Db Dc Dd De Dg Di Dl Wm) Mr(Af Ba Bg Ch Cs Cx Di Hr Ip Jk Jq Jr Jt Lx Mj Mm Mq Ms Mw Nb Ni Nk Nu Nv Wm) Mi(Ad Af An Ap Ar As Ax Ba Bb Bc Bn Ch Co Cp Cq Cs Ct Cv Cw Cx Dc Dd De Di) bE(aD aE aI aL aO Ar aW aY Bg bO bR bU bV bX cD Ch cM Co cR cW cY cZ dD dL) Nv(Hr Hu Ir Iu Jm Jr Md Mh Mj Mq Ms Mw My Ng Ni Nk Ns Nu Of Og Oi Oy Oz) Mj(Ip Ir It Iu Jm Jq Jr Jt Lx Md Mm Mq Ms Mw Nb Ni Nk Ns Nu Oi Oz) Lx(Hq Hr Ir Iu Jq Jr Jt Mq Ms Mw Nb Nd Ni No Ns Nu Oi Oz Wm) gL(aE aG aH aN bO bQ bR bU bW bX cA cC cD cI cT cX dI dM) Mq(Hr Ir Iu Jk Jq Jr Js Jt Mc Md Mm Ms Mw Nb No Ns Nu) Co(aE aI aW bC bU bV bW bX cA cC cR cX Dk Ii Jj Nk) Hr(Ii Ik Il Im Jk Jq Jr Js Jt Li Mm Mw Nb Nu Oz Pg) Nu(Ba Bg Ch Ir Jq Jr Mw Nb Ni Ns Oi Oz Wm) Jh(Bg Hw Hx Ii Jk Ly Lz Mb Me Nf Ny Wm) Jj(Ba Bg Ch Hx Ih Iq Lz Mb Me Oe Og Pb) Jr(Ip Iu Jk Jq Jt Mm Mw Nb Ni Ns Oz) Ba(Aj Ap As Db Dg Dl Fw Gl Mc Nk) Bg(bC bW cR Mc Nh Ni Nk Of Oy) Nb(Ml Mm Mw My Ny Of Oy Pb Wm) Jt(Hw Ij It Jn Js Md Ml Oi Pb) bU(aE aW aY bH bV cI cR dI dM) Mw(Ir Jq Mh Ni Ns Oi Oz) bX(aW bH bO bV cR dI dM) aW(aI aO bW cG cR) Wm(My Nd No Nw) Nq(Cq Dc Dk Md) Ni(Aa Jk Mm Oz) Md(Jq No Nx) cR(Aw Cp De) cS(dR fP gP) cT(dR fP gP) Fr(Fw Gl) Oz(Jq Ns) AaIs ChNk DcLv NoMl MsLi Irlt JkOi aIcI bAfP Constrained panels with 3 analytes, where 1.0E-8 >= 'model p-value' > 0. Contains 17 panels of 939,239 total panels evaluated. : Jj{Fr(Is Iv Lv Ma Md Mg Ns) Ma(Is On) Md(Om On) Mg(Is Jl)} Md{Fr(Is Ji) MuHu} MxJiaA Constrained panels with 3 analytes, where 1.0E-7 >= 'model p-value' > 1.0E-8. Contains 190 panels of 939,239 total panels evaluated. : Fr{Is(Hr Hu In Jm Lv Lw Mt My Ng Ns Of Oi Oy Qb) Ji(Hr In Jj Jq Ml Mt Mx My Nf Ng No Ns Of Oy) Md(Hv Iv Jr Lv Lw Mc Mp Nw Ok Om On) Oy(Iv Jl Lw Mk Nb On Oz) Iv(Hr In Lv Ng Of) Lw(Jj My Ng Ns) Lv(Hr Ns Of) Nt(Jj Ng) Hr(aA Ok) MgNg NhJj} Ji{Md(aA Hv Is Iv Jh Jj Jl Lu Ma Mu Mv Ni Nn Nq Om On Pc) Jq(Hr In Ir Is Iv Jh Jj Jl Lv Ma Mu Ni) Hr(In Is Iv Jl Ma Mu) Jj(Il Iu Jh Ma Mg Mu) Ma(In Ml Nf) Mx(Is Iv Jl) In(Iv Jl)} On{Md(Hr In Is Iv Lv Ma Mc Ni Nn No Oe Oi Pc Pz) Hr(In Is Iv Jj Lv Ma Ng No Ns Of Oi) Mg(Jj Ng Of Oy) Jj(Is Mx No) In(Is Iv) MaOf} Jj{Is(Hr Ih Jh Md Ml Mu Mx Nt Pc) Ma(Iv Jh Jk Jl Mu Nt Ok Om) Mg(aA Iv Lv Mu Oh Ok) Lv(Jl Mu) Iv(Jh Mu) MxJl} Is{Hr(Mu Oi Ok) In(Lw Mg Nt) MdOm} cS{bA(bR bU) bNcP bRcT} bJ{bAbU cTdN} LwMaaA Constrained panels with 3 analytes, where 1.0E-6 >= 'model p-value' > 1.0E-7. Contains 898 panels of 939,239 total panels evaluated. : Ji{Mx(Hr Hv In Ir Iu Jh Jj Lu Lv Ma Mi Mj Mt Mu Mv Ni Nt Og On Oz Pa Pe Pf Qd) Nf(aA Hr Hv Jn Jr Js Iv Jh Jl Lu Mg Mi Mu Mv Ni Nn Nt On Pc) Ml(aA Hr Hv In Ir Is Iv Jh Jj Jl Lu Lv Mc Mu Mv Ni Pc Pf) Ma(aA Hw Ij Is It Jl Jn Jr Js Me Mz Ny Om On Pb Pc) Jl(Hx Ii Ij It Jh Jj Jn Js Mg Mz Ny Of Pb Pc Pe) In(Ir Is Iu Jh Jo Jt Md Mg Mu Ni Nt On Pc Wm) Is(Ih Ij It Jn Jr Js Mg Mz Ny Pb Pc Qb) Md(Hr Ir Jg Jp Mc Mg Mi Mt Nb Nt Pf) Jh(Hr Ij It Jn Js Ny Of Pb) aA(Hr Jn Jq Jr Js Mg Mz Pc) Mu(Ij It Jn Js Ny Of Pb) Iv(Ij It Jj Jn Js Mz Pc) Mg(Hr Ij Lv Ng Oi) Ny(Fr Nb On Pa Pe) Mv(Hr Ij Jq Of) Ir(It Jn Jr Js) Hr(Jj Lu Pf) On(Nv Og Oy) Ij(Ni Pc) Jq(Hv Mi) FrMz NsPc Itlu} Jj{Ma(aA Hv Ii Il Iu Jg Jp Jr Jt Lh Lv Lw Mg Mi Mj Mp Mr Ms Mt Mv Mw Mz Nb Nh Nn Nu Nv Nw Nx Oh Oz Pa Pc Pd Pe Pf Po Qa Qd Qe) Mg(Hr Hv Il Jh Jk Jp Jr Lh Md Mi Mj Mt Mv Mw Mz Nh Nt Nu Nw Om Oz Pc Pf Po Qa Qd Qe) Jh(Hv Il Iu Jl Li Lv Lw Md Mi Mj Mp Mu Mz Ns Nt Nu Oh Ok Pc Pf Qd) Iv(Hr In Jg Jk Jl Lv Lw Md Ml Mt Mv Mw Mx Nn Nt Ok Om Pc) Lv(Il Iu Jg Jk Mt Mv Mw Nn Nt Nu Oh Ok Om Pc Pf) Mu(Hr Iu Jl Lw Md Ml Mj Ns Nt Nu Ok Pd Qd) Ok(Hr Il Jk Jl Lu Md Mt Mv Nn Nt Pc) Nt(Hv Jl Md Mi Nn Om Pc) Md(Jk Jl Lh) Mi(Ik Jk Pc) Hr(Jl Om) LwJl Mtll} Is{Md(aA Hr Ih In It Jg Jh Jm Lv Lw Ma Mg Mi Mp Mu Mv Ni Nn Nq Nw Oi Ok Pc) In(Hr Hv Ir It Iv Jh Jl Jt Lh Ma Mi Ml Mu Mx Nb Ni Ok Om Pa Pc Pe) It(Hr Ir Iv Jh Lv Lw Ma Mg Mu Ni Nt Oi Ok On Pc) On(Ih Ij Jm Ma Mg Ns Nv Ny Oe Og Oi Oy Qb) Hr(Ih Iv Jh Jl Jm Lv Lw Ma Mg Mi Ni Nt) Ok(Ih Ij Jh Jq Ma Mg Ml Mx Og Pc Qb) Pc(aA Jm Lv Ma Mg Mi Nk Ns Oi Qb) Mg(aA Ih Jm Lv Ng Oi Qb) Ma(aA Jh Jm Lw Mu Oi) Ih(aA Iv Jl Lw Mi Nt) Mu(Jm Lv Mx Oi Qb) Mx(aA Jm Mi Ni) Jh(Jm Lv Oi) Ni(Ij Ml) Qb(Lv Lw)} Fr{Hr(Hu Hv Jl Jr Lw Md Mq My Ng Nh Ni Ns Oi On Qd) Of(Hv Ir Jh Jl Jt Lw Mg Nb Ni Nt Ok Om On) Nt(Hu In Md My Nr Nv Oi Oy) Hv(Hu In Lw Ma My Ng Ns

Figure 2 Continued

Oy) Iv(Jm Lw Ma Mx My Ns Oi) Jl(Lw Ma Mk Mt Oe Oi) On(Ma My Nv Ny Oe Og) Hu(Jh Lv Lw Mg Om) Oy(Lv Mg Om Pa Pe) Md(Ir Ni Ns Oi) Ma(aA Lw Ok) My(Jh Jr Om) Ng(Ik Jh Om) Ir(In It Ml) Oi(Mg Nh Qd) Mi(Hq Mt) aA(Mg Mt) cP(aW cS) LvLw bQcR} On{Ma(aA Hu Hv In Iv Jh Lw Ms My Ng Ns Nv Ny Og Oy Pc) Oy(Hr In Jh Jl Lw Mt Mu Mv Mx No Om Oz Pc) In(Hu Ir Lv Lw Mg My Ng Ni Ns Of) Mg(aA Hu Lv My Nv Ny Og Oi) Pc(Ms My Ng Ns Of Og Oi) Nv(Iv Jh Lv Mu Om) No(My Ng Of Og) Mx(Iv My Ng Of) Ni(Hr Ij Ny Of) Lw(My Nx Og) Hr(Mn Mt My) Ny(Iv Jl Lv) Mu(Ng Og) Jh(Ng Og) Oi(Hu Iv) LvOf} Md{Om(aA Hr Hu Hv In Iv Jl Lv Mc Mi Mp Ng Ni Nn Nw Oe Of Og Oi Ok Oy Pc Qa) Ok(Hr Jh Jl Mg Mp Mu Nn Nq Pc) Nw(Jh Ma Mg Mi Mu Nn Nq Pc) Lv(Jh Mu) Mi(Jh Mu) aA(Lw Mg)} aA{Lw(Hr Hv Hw Ij In It Jn Lv Mg Ml Mu Mx Na Nf Pb) Mg(Hr In Jr Lv Ok Pc) Ma(Jr Nw Ok Pc) cS(bR bU cI dG) Lv(Hr Mu Pc) Hr(Mu Ok) OkPc bJcT bUcX} Hr{Ok(Hv In Iv Jh Jl Lu Lv Ma Mg Mi Mt Mu) Jl(Iv Jh Lv Lw Ma Mg Mu Nk Oi Om) Iv(Jh Lv Mu Nw Om) Lv(Jh Mg Mu) MiMu} cS{bA(aF aW bJ bN bQ cI cP dG dH) cT(aD aF aW Bg bJ bN bU cI cP) cP(aF bE Bg bR bU bZ cI) bR(bN bZ cN) bU(aX bN)} Jl{Mg(In Lv Ng Of Oi Ok Oy) Ok(In Ma Mx Og Pc) Lv(Jh Mu) Lw(In Ma) Om(Of Oy) MuOy InIv} bA{bU(aE aW aX bE bZ cR dK) bJ(aD aF aW bR bZ dK) aF(bZ cR) bR(aE bZ) bNdK dGdN} cT{dN(aE aF aM aW bE bN bQ dF dG) aD(bE bJ bZ) aW(bE bJ) BgbJ aXbU} In{Iv(Jh Lw Mg Mu Ok Om Pc) OkPc} Ok{Pc(Iv Lu Ma Mg Mi) MgNg} Oy{Mv(Bc Cu) MuHu} MgNgJg MuMyHu aXbUcP

Constrained panels with 3 analytes, where 1.0E-5 >= 'model p-value' > 1.0E-6. Contains 1,822 panels of 939,239 total panels evaluated. : Jj{Hv(Et Hr Ii Ik Il Ip Iu Jg Jp Jt Lh Lv Lw Md Mj Ml Mm Mp Mt Mv Mw Mz Nn Nu Nv Nw Nx Of Oh Pc Pd Pf Qd Qe) Iu(Ik Il Jg Jp Jr Lh Lw Mi Mj Mp Mt Mv Mw Mz Nn Nu Nv Nw Oh Pc Pf Po Qa Qd Qe) Pc(aA Ii Ik Il Jp Jt Lh Mj Mq Mr Mt Mw Mz Nu Nv Nw Oh Pe Pf Po Qa Qd Qe) Lw(aA Ik Il Jp Lv Mi Mj Mp Mt Mv Mw Mz Nu Nv Oh Pa Pf Po Qa Qd Qe) Il(aA Et Hr Ik Jg Jp Jq Jr Jt Mm Mp Mq Ms Mw Mz Nn Nu Nx Of Oh) Lv(aA Ii Ik Jp Jt Lh Mi Mm Mp Ms Mz Nh Nq Nw Oz Pa Po Qd) Nu(Ii Jg Jr Mi Mj Mp Mq Mv Mw Mz Nn Oh Pa Pe Pf Qa Qe) Md(Ii Jg Jo Jt Lx Mi Mp Mt Mv Nb Nn Nv Nw Oh Pf Po Qa) Nn(Ik Mi Mj Mq Mr Mt Mw Mz Pa Pe Pf Qa Qd Qe) Mp(Ii Ik Jg Jp Jt Lh Mj Mt Mv Mw Mz Qa Qd Qe) Mi(Hr Jg Lh Ml Mt Mv Mw Mz Nx Oh Pf Qe) Jg(aA Jr Mj Mr Mz Ns Oh Pf Qa Qd Qe) Hr(Ii Lh Mj Nv Pf Po Qa Qd Qe) Mz(Ii Ik Mj Mq Mv Pd Pf) Ik(Jp Mj Mw Nd Oh Qd) Ml(Jo Jt Mj Qa Qd) Mv(Lh Nw Oh Qd) Mw(Ii Mj Pa Pd) In(Jo Jt Lh) Ns(Mt Nv) Ma(Jq Wm) Ms(Pf Po) Qd(Mx Ok) aA(Mj Mn)} aA{Pc(In Iv Jh Jl Jr Lw Md Mi Mj Mq Mu Mz Nk Ns Nt Nw Om On Pf Po Qd) Om(Hr Hu Ij In Jn Jr Js Lw Ma Ml Mx Nf Ns Ny Of Ok Oy Pb) bZ(aF aW bE bJ bQ bR bU bX cA cC cE cI cP cT cX dG dH) Lw(Jg Jh Jo Jr Js Me Mv Mz Nw Ny Of Ok Pf) cX(aF aW bE bR bX cA cD cI cP cS cT dG Fr) Ma(Hr Iv Jg Jh Lv Md Mg Mi Mn Ms Mu Mz) Md(Jg Jr Lv Mi Mp Mu Nn Nw Ok Pf) cS(aF aP aW bN bS cA cB cK dH) Nw(Hr In Jh Lv Mg Mt Mu Mx) Ok(In Jh Jr Mu Mx Nf Nn Pf) aF(bA bE bR cI cP cR cT) bJ(aW bR bU bX cA cI cP) Lv(Jh Jr Me Mn Mx Nn) Hr(Iv Jh Jr Mi Pf Po) cT(aE aW bE bR bU cR) Mg(Hu Iv Jl Ng) Jr(In Jh Js Mx) bE(aW bR bU cP) cP(aW bU cI) Mx(Jl On) aX(bR bU) NsMu MtOn InIv} Iv{In(Hr Hv Il Ir Iu Jg Jt Lh Lv Ma Mi Ml Mp Ms Mt Mv Mw Mz Nb Nn Nq Nt Nw Oh) Hr(Et Hv It Jg Jp Lh Lw Ma Mg Mi Mp Ms Mt Mv Mw Mz Nn Oi Pf) Ma(Jg Jh Jl Jp Lv Lw Mi Ml Ms Mu Nn Nw Oi Ok Om Pc) Lv(It Jh Jp Lw Md Mg Ml Mu Mv Mx Nn Nw Ok Pc) Md(Jg Jh Jl Lw Mi Mp Mu Mv Nn Nq Nw Ok Pc) Pc(It Jh Jl Jp Mg Mi Mu Nk Nw Oi Om On) Ok(Ij It Jh Mg Ml Mu Mx Nf Nn Og Oi) Mu(It Jh Lw Mi Ml Mx Nk Of Oi) It(Ir Jh Jl Lw Nw Om On) Mx(Is Jl Lw Mi Nw Om) Jh(Lw Mi Ng Of Oi On) Ji(Hv Hw Jr Me Ny Pb) Mg(Lw Ng Nw Oi On) Oi(Jg Jl Nn Nw) Om(Ij Ml Of Oy) On(Ij Og Qb) Jg(Ng Of) Jl(Ih Nk) LwMi MlNw} Mu{Hr(Et Hv Jh Jr Lw Ma Mg Mr Mt Mz Ns Nt Nw Oi Om Pa Pe Pf Qa Qd Qe) Lw(Hv In Is Jh Jl Jm Lv Ma Md Mi Ng Ns Nw Og Oi On Oy) Ma(Hu Hv Jl Md Mi Mz Ng Ns Nw Of Oi Ok Pa Pc) In(Jl Jt Lh Mi Nt Nw Ok On Pa Pe Qa) Oy(Bc Co Cu Is Nb Nw Om Oz Pa Pe) Of(Is Jh Jl Lv Mi Nb Nw Ok Om) Ng(Is Jg Jh Mg Nw Ok Om) Ns(Is Jh Jl Mi Nw Ok) Md(Jl Lh Lx Mp Mz Pc) Ji(Hw Jr Mz Om) Oi(Jl Nt Nw Qd) Mi(Hq Pc) My(Nw Om) Hu(Jh Om) Jl(Mx Nk) On(Ny Oe) CuHw LvJh OgOk} Jl{Md(Hr In Is Jg Jh Jq Lv Lw Ma Mg Mi Mp Ni Nk Nn Nw Oi Pc) Lv(Hx Jp Lw Mt Mv Mw Mx Mz Nn Nw Om Pc) In(Hv Ir Jh Jt Ma Ns Nt Nw Om Pc Pf) Lw(Ih Is Jh Mg Mx Nk Ns Oi Ok On) Jh(Ma Ng Ns Nw Of Oi Ok Oy Pc) Om(Hu Ij Mt Mx My Ng Ns Ny Oi) On(Hx Ii Mg Nk Nv Og Pc Pg) Is(Hw Hx Lz Mx Nk Oy Qb) Pc(Ma Mg Mi Nk Ns Oi) Ns(Hr Jg Mg Nn) Mx(Ir Mi Nk Nw) Mg(Jm Nr Og) Jg(My Ng Of) Oi(Nn Pf) MaNw NkPf IrIt} cT{bE(aE aF aI aY Bg bO bR bU bZ cD Ch cP Cu cW dD dK Fr) bZ(aE aF aJ aW bJ bM bQ bR bX cE cP cR dF dK) dK(aD aF aJ aW aX aY bJ bR bU cF cP cR dN) bJ(aE aF aI aJ aN aY Ch cI Cu dL Fr) aE(aI aJ aX aY bR bU bX cP cR) aW(aI aJ aX Bg bW bX cP cR Fr) aX(aD Bg bR bX cD Ch cP) Fr(aL bQ cR cS Dk dM) aF(aJ aP aY cP cR) bU(aJ aP aY dI dN) Bg(bW cP cR dN) aJ(bR cP cR) dN(aH dL) ChcS CsCu aPbR} bA{bZ(aD aW bE bQ bX cC cD cE cF cG cI cP cR dF dH dK) bE(aD aF aI aW bO bR cD cP cS dD dK dN) cI(aD aI bJ bR bU bX cB cP cR dK dN eF) cR(aE aW Bg bN bQ bR bX cB cP dK Fr) bJ(aE Bg bO cB cD Ch cK cP dN Fr) aF(aE bR bX cP cU dK dN) Fr(aW bQ bU cX dG dM) cP(aE aW Bg bN bU dK) dN(aE aM bN bQ bU dF) bR(aW aX cO cU dK) aD(aM bN dG) bX(aE aX bN) bU(aY cO) BgcS aEcB bMbN bQcO cFdK} Is{Ni(Hv Hw Jn Jr Js Mz Nf Ny Of Pb Pc) Mx(Hv Ih Ir Lv Lw Nt Nw Om Pf Qb) Jh(Ih Lw Mi Ng Ns Of Oy Pc Qb) Jg(Ij My Ng Ns Of Og Oy) Nn(Jm Ns Og Oi Oy Qb) Nt(Jm Md Nk Nr Oi Qb) Ml(Ir Jm Lv Mi Om Pf) Lw(Hv Ij Jm Ns Oi) Om(Ij Ns Of Og Oy) Pf(Ih Md Nr Oi Qb) Lv(Ih Jm Oi) Md(Lx Mq Qb) Mg(Of Og Oy) Mv(Ns Of Oy) Ir(Jn Jr Js) Lz(Oz Pa) Mi(Hq Qb) Mp(Hq Nd) Mt(Nr Nw) NbNy IhPc QbNw LiLj OyOz} Ji{Mz(Hv Ir Jh Lu Mg Mt Mv Ni Nt Pa Pe Pf) Ny(Hv Iu Mg Mr Mt Mv Ni Nq Nt Om Oz Pc) Hv(Hw Ij Ir It Jn Jr Js Ni Nt Pb) Pb(Mg Mv Nb Ni Nt Oz Pc Pe) Js(Lu Mt Mv Ni Nt Pc Pf) Om(Ij Jh Mg Mv Nt Of Pa) Jn(Hr Lu Mv Ni Og Pc) Jr(Jh Lu Mv Ni Og Pc) Ij(Il Lv Mt Nb Nt) Nt(Hw It Me) Ni(Hw It Me) Jk(Ng Of Oy) Nq(My Of) Oy(Mk Oz) Pc(It Mt) NnNs NoOn MiHq NbOf NgJg HwJh IlJm} Lv{Pc(Hv Jh Jp Ma Md Mg Mi Mt Mz Nt Nw Om Pa Pe Pf Qd) Hr(Hv Jp Mi Mt Mv Mw Mz Nt Nw Om Pa Pf) Md(Jg Jt Lh Mi Mp Mt Nb Nn Nt Nw Ok) Mg(Hv In Jh Ng Nw Oi Ok Pa) Jh(Hu Hv Mi Of On Pa) Nn(Mi Ns Nt Ok Pa) Lw(Hv Ma Mt Pa) In(Jt Nt Ok Om) It(Ir Jt) Ok(Jq Lu) Om(Ij Of) NsJg MlJt MtPa NbNy OnPg} On{Ny(Hv In Ir Jh Lw Mt Nb Nt Og Pa Pc Pe Pf Qd) Nv(Hv Jp Mj Mn Mt Mv Nn No Nq Nt Nw Pf Qd) Jh(Hu Hv In Lw Mg My Ns Oe) Pc(Mg Mi Mt Mw Mz Ni Qd) Mt(In Lw Mi Ns Og) Ni(Ml Mx Nf Nx Pb) Mg(Ij Jm Oe Pz) In(Mz Nt Oh Om) Ir(It Ml Mx) Og(Hv Nn Om) No(Hu Ms) NqOy LwHv MiMx PaPf} Ok{In(Hv Jh Lu Ma Md Mg Mi Mt Nh Nn Nt Oh Pf Qa Qd) Md(Hv Lu Ma Mc Mi Mt Mv Nb Ni Nw Pf Qa) Nn(Jh Jq Ma Mg Ml Mx Nf Ns Of Oi) Jh(Hv Ma Mi Ng Of Og Pc) Ma(Hv Mi Ms Mt Nw) Mg(Hv Lu Of Og Oi) Of(Mv Nq Om) Pc(Mt Oi Qd) Hr(Nw Oi) NsLu MiMx OgOm} Om{Of(Hr Hv In Jh Lh Lu Ma Mi Mp Nb Nt Oz Pa Pe Pf) In(Hr Hu Lw Ma Mi My Ng Ns Nt Pa Pc Pe Qa) Hr(Hv Ma Mi Mr Mt Ng Ns Oi Pf Qd Qe) Mi(Ij Ml Mt Nf Oy Pb Pc) Oy(Ma Mk Nb Oz Pa Pc) Ng(Jh Ma Mg) Fr(Jh Mw) Hu(Jh Ma) NsPc} Fr{aX(aW aZ bR bU cA cK cP cX) cR(aW Ba bE Bo cP cX DK) cS(bN Bo bQ bR bU cI DG) In(Jt Lh Pa Pe Qa) aW(aE Ba Bo DK) cP(aL aR bE Dk) Qa(Ij It Ml) Dk(bE bU) Nt(Hq Pg) Mp(Hq Nd) Ny(Jt Nb) MtNw IuJm PaPf} Jh{Md(Hv Lh Lw Lx Mc Mp Mz No Pc Qa) Ma(Hu Hv Lw Mi Ng Nw Pc) Mi(Hq Hr Lw Ns Of Pc) Nw(Hr My Ng Ns Of Oy) Oy(Mk Nb Oz Pa Pe) Lw(Hv Ng Pa) Hr(Hv Mz Qd) Of(Hv Nb Pc) Ng(Mg Nt) QdPc} cS{cI(aD aI aX bN bR bU bZ cM cN cQ eF) bN(aD aJ aW Ba bX cB cD dN) bU(aJ aN aW Ba bZ cN cQ dA) bR(aJ aN aW aX Ba cQ dA) aX(bX cB cK) bZ(aW bQ dH) BaBo ChcP aJdG bEdD} Nw{Md(Hr Hv Lu Mc Mp Mt Mv Nb Ni Nt) Hr(Hv Ma Mg Mi Mt Mv Ni Nt Oi) Mg(In My Ng Of Oi Oy) Ma(Lw Ml Pc) Mi(Ml Mx Pc) NsPc NtIn NbNy} Mi{Md(Jg Jp Lw Ma Mg Mt Nn Nt Pc) Pc(In Jp Lw Ma Mt Nk Nt) Hr(Jg Jp Lw Ma Mt Qe) Lw(In Ma) Hq(Ma Mg) NtIn NgJg} aX{cP(aW Bg bX bZ cD Ch cI Co dK) bU(aE aJ aW Ba cI dK dN) cX(Ba Bg Ch Cu) BgaZ bRdK} bZ{Ba(aW bQ bR cC cE cR) cP(aF aJ aW bE bQ dK) aJ(bR dG)} Ma{Lw(Hv Jp Ms Mt Nt Pa) Pc(Hv Nt

Figure 2 Continued

Qd) NtMs LxMd NgJg HrHv} Md{Mp(Jg Jp Lh Mt Nb Nt) NqHu LxMg} bE{eF(aF aW cE cI dK) aWgL cPdK} In{Nt(Hv Lw Pc Qa) Lw(Hv Lh)} Oy{Nq(Ba Bc Cu) Mg(Bg Nb Pe)} aJ{cP(bU cR dK) dGdN} cR{Ba(aW bQ) cPdK} CuMcMx NtOiPc LwHrHv

Constrained panels with 3 analytes, where 1.0E-4 >= 'model p-value' > 1.0E-5. Contains 2,831 panels of 939,239 total panels evaluated. : Md{Jh(aA Et Hr Hu Jg Jp Jq Jr Js Jt Li Ma Mh Mj Mq Mr Mt Mu Nb Ni Nn Nt Nx Oh Oi Oz Pa Pe Pf Po Qd Qe) aA(Et Hv Iv Jp Jq Js Jt Lh Lx Mc Mh Mj Mn Mq Mt Mv Mz Nb Nm No Nq Nt Nv Nx Oh Pd Pe Po Qa Qd) Lx(Et Hr Hv In Iv Jg Jp Jt Lj Lv Lw Lz Mh Mi Mp Ms Mt Mv Mz Nb Ni Nn Nq Nt Pc Qa) Jg(Hv Jr Lh Lw Ma Mj Mq Mr Mt Mu Mz Nb Ni No Ns Nt Oh Oi Pa Pe Pf Po Qa Qd Qe) Mi(Et Hr Hv Ir Jr Jt Lh Mp Mq Mv Mw Mz Nb Ni No Nq Nu Nv Oh Pf Po Qa Qd Qe) Mp(Et Hr Hv In Ir Jr Jt Lw Ma Mj Mr Mv Mz Ni No Nu Nv Oz Pa Pc Pe Pf Po) Pc(Hv Jj Jp Jq Jt Lh Ma Mg Mj Mq Mr Mt Mv Mz Nb No Nt Nv Pf Qa Qd Qe) Mu(Et Hv Jp Jq Jr Jt Mc Mg Mt Nb No Nt Oi Pa Pe Pf Po Qa Qd) Lv(Hv Hx Jo Lw Mr Mv Mw No Nq Nu Nv Oz Pd Pe Pf Po Qa) Nt(Hr Hv Iv Jp Jq Lw Ma Mq Mt Mv Nb Nn No Oi Pf) Lh(Hr Hv Iv Jp Jq Lw Ma Mg Mt Mv Mz Ni Nn Nq Pf) Mt(Hv Iv Jq Jt Lw Mg Nb Nn No Pa Pe Pf) Iv(Et Hv Jp Mg Mq Mw Mz Nb No Oi Pf) Nn(Hv Jp Jq Jt Mz Nb No Pf Qd) Mg(Hv Jp Mz Nb No Pa Pc Pf Qa) Jj(Ij Jq Js No Nq Nx Pe Pg) Lw(Hv Jp Mv Nb Pf Qa) Ma(Jq Jt Nb No Qa) Nb(Jp Mv Mz Pf) Mz(Mv Pf)} In{Nt(aA Et Hr Hx Ir Iu Jh Jp Jq Jr Js Jt Lh Lx Ma Mg Mj Mp Mr Ms Mt Mv Mz Nb Nh Nn Ns Nu Oh Oi Pa Pe Pf Po Qd Qe) Mg(Bb Cu Hr Hv Jh Jq Jr Js Lh Lw Mi Mj Mr Mt Mu Mz Nb Ng Oh Oz Pa Pc Pe Pf Qa Qd Qe) Lh(aA Hr Hv Ir Jh Jr Lv Ma Mi Mp Mt Mv Mz Nh Ni Nn Nw Oh Ok Om Pc Pf Qa Qd) Lw(Iu Jh Jp Jr Lv Ma Mj Mr Mt Mv Mz Nb Nw Oh Pa Pe Pf Po Qa Qd Qe) Mi(Hv Il Ir Jg Jr Jt Mj Mq Mt Mz Nb Nn Nu Nw Nx Oh Pf Qa Qd Qe) aA(Hv Il Jg Jq Jt Lx Mj Mn Mt Mv Mz Nv Nx Oh Pe Pf Po Qa Qd Wm) Mu(Cq Hu Hv Hx Ir Iu Jo Jr Mh Mr Mt Mz Nb Ns Pc Pf Po Qd Qe) Jt(Hv Jh Lx Ma Mp Mr Mt Mv Ni Nn Nw Oh Oi Ok Om Pc Pf Qa) Lv(Hv Hx Ir Iu Jo Mr Ms Nb Oh Oz Pa Pe Po Qa Qe Wm) Qa(Hr Ir Iv Jg Jh Jo Ma Mr Nb Pa Pc Pe) Jh(Hv Ir Jr Mr Nb Oh Pa Pc Po Qe) Nw(Hv Ir Iu Jo Mr Nb Ok Pa Pc Pe) Om(Hv Hx Ir Iu Mr Nb Oy Qd) Pc(Hv Mj Mt Mz Pe Pf Qd Qe) Mt(Hr Hv Mr Nb Pa Pe) Ma(Hv Nb Pa Pe) Iv(Mr Pa Pe Qd) Nb(Hv Mz Qd) Jg(Hv Ns Qd) Cu(Dc Mx) Mv(Hv Mz) Hr(Po Qe) WmMr HxOk} Hr{Jh(Et Hu Jp Jr Lh Li Lw Ma Mg Mh Mj Mp Mq Mr Mt Ng Ns Nt Nu Oh Oi Oz Pa Pc Pf Po Qa Qe) Mt(aA Hv Jp Jr Lh Lw Ma Mg Mj Mq Mr Mv Mz Ni Ns Nt Oi Pa Pe Pf Po Qa Qd Qe) aA(Et Hv Jg Jj Jk Jp Lh Lx Mh Mj Mn Mq Mv Mw Mz Nt Nu Nv Oh Pe Qa Qd Qe) Ma(Et Jg Jp Jr Jt Lh Lv Lw Mr Ms Mv Mz Nb Nt Oh Pa Pe Pf Po Qa Qd Qe) Mg(Hv Jp Jr Lh Lw Mi Mj Mr Mz Ng Nt Oh Oi Oz Pa Pe Pf Po Qa Qd Qe) Lv(Et Iu Jg Jr Jt Lh Lw Lx Mj Mp Mr Nb Nu Oh Pe Po Qa Qd Qe) Nt(Hv Jp Lw Mi Mp Mq Ms Mv Mw Mz Nk Oi Pf Po Qa Qd Qe) Mi(Et Hq Hv Ik Jr Lh Mq Mv Mw Mz Nu Pf Po Qa Qd) Pf(Hv Jp Lh Lw Mq Mz Nb Ni Oi Pa Pe Qa Qd Qe) Lw(Jp Lh Mj Mr Mv Mz Pa Pe Po Qa Qd Qe) Mv(Hv Lh Mr Mz Pa Pe Qa Qd Qe) Hv(Et Jg Jp Lh Mz Po Qd Qe) Qd(Jg Jp Lh Mz Oi Pa Po) Jj(Jo Jr Js Mq Mr Nb Pe) Qa(Jp Nk Oi Pa) Po(Jp Oi) Om(Pa Pe) MjJp MqMz LhOi} Jj{Pc(Et Hu Im Ir Jn Jo Jq Jr Js Lw Lx Mm Mp Ms Nb Nh Nx Of Oz Pa Pd) Jr(Et Ik Ip Jo Jp Jt Lw Mm Mp Mr Ms Mw Nn Nq Of Oz Pa Pd Pe) Ms(Ik Ip Iu Jo Li Lw Mp Mr Nb Nh Nn Nq Oz Pa Pd Pe Pg) Nn(aA Et Jo Jp Jt Lw Lx Mm Mp Nh Ns Nx Of Oz Pd) Iu(aA Et Ip Jq Js Jt Lx Mm Mq Mr Nh Nq Nx Pd Pe) Lw(Et Im Lx Mm Mq Mr Nb Nq Nx Of Oz Pd Pe Pg) Nq(aA Ao Ip Jn Jq Mm Mr My Nh Ns Nx Oz) Mp(aA Et Jo Mr Nb Nh Ns Nx Of Pa Pd Pe) Jt(Hw Ij It Jn Js Mx Na Nf Ny Pb) Oz(Im Ip Jn Jq Js Lx Mm Mw Nu Nx) Pa(Et Ik Im Ip Jn Jp Jq Lx Mm Nx) Mr(Ik Mm Mw Nu Nx Of) Jo(Hw Ij It Nf Ny Pb) Mq(Jp Js Mm Ns Of) aA(Ii Lx Mw Nu Pd) Pe(Ik Lx Mm Nx) Bg(Mg Mi Mu) Ml(Ir Js No) Bb(Mg Mv) Ch(Mi Mu) Mm(Ik Nb) Hq(Lx Mi) AoMv CuMx DkMu WmLv NsLi NuOf NbNx NhJq IkJs JpLh} Jh{Of(Ir Jg Jp Jr Jt Lh Lw Ma Mc Mg Mj Mp Mr Mt Mz Nn Nt Oh Oz Pa Pc Pf Po Qa Qe) Oi(Hu Jp Jr Li Lj Ma Mg Mj Mr Mt Mu Mz Nn Nt Nu Nw Oh Om Pa Pc Pe Pf Qa Qd Qe) Ns(aA Hu Hv Jg Jp Jr Lw Ma Mc Mp Mq Mt Mz Nn Nt Oh Om Oz Pa Pc Pe Pf Qd) Ng(Hv Iu Jg Jp Jr Lh Mj Mp Mt Mz Nn Oh Pa Pc Pf Qd Qe) Pc(Hu Hv Jr Mg Mj Mr Mt Mu Mz Nt Nw Oh Oy Pa Pe Pf) Oy(Il Lh Mg Mj Mp Mr Mu Nn Om Pf Po) Ma(Jr Ms Mz Nt Oh Pa Pe Qd) Hu(Hv Li Mg Mt Nt Oh Pa Pf) Lw(Mf My Mz Nt Oh Pe Qd) Mu(Hv Jl My Mz Og Om Qd) My(Jg Nb Nn Om) Ml(Ir No Qa) Mp(Hq Nd Pg) aA(Iv Mz Pf) Nn(Nt Og) Ms(Li Nt) It(Ir Qa) LxHq NbNy IjQa} Pc{Ma(Et Ir Iu Jp Jq Jr Jt Lh Lw Mg Mj Mq Mr Ms Mt Mv Mz Nb Ns Oh Om Pa Pe Pf Qa Qe) Mg(Hv Ir Jp Jr Lh Mj Mr Mt Mz Ng Ni No Ns Nw Oh Oi Oy Oz Pa Pe Pf Qa Qd Qe) Ns(Hv Jp Lv Mj Mq Mt Mu Mv Mz Nt Pf Qd) Mu(Hv Mr Mz Ng Nt Of Oi Oy Pa Pe Qd) Hv(Et Jp Lw Mt Mz Nk Nt Om Pa Pf) Jp(Lw Mj Mq Mr Ni Nt Oi Pa Pe) Mz(Mq Mt Mv Nt Oi Pa Pe Pf) Nk(Mj Mr Nt Pa Pe Pf Qd) Om(Hu My Ng Nt Og Oi Qd) Nw(Jl My Ni Nt Oi Oy) Mt(Ni Oi Pa Pe Qd) Lv(Iu Mr Mv Mw) Ni(Mj Pa Pf) Oi(Mj Pf Qd) Lw(Mr Pf) NtQd MiHq NbOy} Jg{Ng(aA Hv Iu Jp Jr Lh Lv Lw Mj Mp Mr Mt Mv Mz Nk Ns Nt Nu Nw Oh Ok Om Pa Pf Qd) Ns(aA Hv Iv Jr Lw Ma Mi Mp Mr Mt Mz Ni Nt Oh Oi Oz Pf Qd) My(aA Hv Iv Lv Lw Ma Mi Mr Mt Mu Nb Nq Nw Om Pa Qd) Of(aA Hv Lh Lv Ma Mi Mu Nb Ni Nt Nw Ok Pa Pe Qd) Oy(Hv Iv Jl Lv Ma Mi Mk Nb Nw Oz Pa Pe Qd) Ma(Hu Hv Lv Lw Mi Ms Mz Oi Pa Pe Qd) Mi(aA Hu Iv Lv Mt) Oi(Jl Mt Nt Pf Qd) Hu(aA Hv Lv Mu) Iv(aA It Ml) Lw(Hv Qd) aA(Jr Qd) LvHv MwJl OgOk} aX{aW(aA aI aJ aO aZ Bg bR bX bZ cA cB cD cI cK dK dN) cI(aD aI aJ Bg bO bR bX bZ cB cD cT cW dK dN eF) bX(aA aC aD aE aI Bg bN bZ Ch De dK dN Fr) cA(aA aC bA Bg bZ Ch cP cS Cu dK dN) cK(aA aJ aP bA Bg bZ cD Cu dN) dK(aA aJ Bg bN bZ cB cD cF dN) bR(aE aJ aP Ba bZ Ch cP dN) bU(aP aY bH bZ Ch Co) Bg(aI bM cB cS Dk) aA(bV cB cD dA dH) cT(aF bM bZ cB Co) aZ(Ba Ch Co Cu) bA(bQ bV cB dH) Fr(Bo bQ Dk) Ba(bZ cB) cP(aF Cu) CoDg aJdG bScS} Mu{Of(Bg Cu Et Hv Jt Lh Mg Mr Mt Nt Pa Pe Pf) Oi(Hv Jp Mg Mt Mz Nu Oh Om Pa Pf) Oy(Et Lh Mg Mk Mp Mr Mt Nt Pf Po) Ns(Hu Hv Jp Mt Mz Nt Om Oz Pf) Nk(Ao Bb Co Dk Mh Mr Oz Pa Pe) Ng(Et Jp Mt Nt Pa Pf) Cq(Cu Lw Mc Mr Mt) Mx(Ao Bb Co Dk Ir) Hu(Ij Mg Mt Nt Pf) It(Ir Jt Qa Qd) Ao(Bg Mc Mq) Ml(Ir Jt Qa) Mp(Hq Nd Pg) Nb(My Ny Pb) Bg(Dk Jk) Co(Hx Mw) Cu(Nv Pg) Ij(Jt Qa) Jl(Mz Nw) Og(Mg Om) BcHw ChJk DdLw DkMc IrJs QeJm} Lw{Hv(Ij It Iv Jp Mg Mi Ml Mt Mv Mw Mx Mz Na Nf Nt Nw Om Pa Pb Pf) Ma(Iu Lh Mf Mr Mv Mz Nb Om Pe Qd Qe) Mg(Jp Mr Mt Mz Ng Oh Oi Pa Pe Pf Qd) Mv(Iv Lv Mz Ng Ns Nt Oy Pa Qd) Mi(Hq Jp Lv Ml Mt Nn Ns Nw) Ok(Hw Ij Jq Ml Nf Nm Pb) Jp(Io Iv Lv Ns Nt Pa) Ns(Mt Nt Nw Pf) Lv(Iu Mw Nn Pf) Nt(Ms Nn Oi) Nb(Ny Of Pb) Co(Ii Oy) Mp(Hq Nd) Mt(Oi Pa) Iv(Ml Nw) AoNq CuIi IjOm NwOi OyPa} Om{Ij(Hv Mh Ni Nt Ok Pa Pe Qa Qd) Ny(Iv Lh Mi Mr Nb Ni Pa Pe Qa) Oi(Iv Mg Mt Nn Nt Oh Pa Pf Qd) Oy(Hv Mg Mp Nn Nt Nw Pe Pf) Ml(Ir Mh Ni No Pe Qa Qd) Ng(Iv Mt Mv Nn Nt Pf) Pb(Nb Ni Oz Pa Pe Qa) Ns(Ma Mi Mp Nn Oz) My(Ma Nn Nq Nw Pa) Ir(It Jn Jr Js) Mp(Hq Nd Pg) Nf(Ni Ok Qa) Hu(Mg Mv Pf) Jl(Hw Hx Ii) Ma(Hv Mi) Qa(Hw It) Ok(Jq Lu) NnMs MiHq IiPa IvJs} aA{Mx(Iv Jq Mi Mj Mz Nn Oh Pf Po Qd) cR(Bg bQ bV bX cA cK Co dK) Ba(Bg bJ bR bU Ch cX) Nn(Iv Mq Mt Ns Nt Qd) dG(aJ bA bM dK dN Fr) Nc(Iv Mj Mp Mt Nt) aW(bR bU bX cA Co) cX(bA Bg Ch Co De) dK(bE bJ bN bZ cF) aF(bF bJ bU bX) Mp(Hq Nd Pg) bZ(cK dA dF) cU(bQ bR dH) Ns(Mq Mv) Nt(Nk Nl) Jr(Jn Mn) bH(bU cD) bJ(cB cK) BgcP CxcT WmMa FrdM LzPf ItIv aEbR bEcK bFbQ bUcI} cT{Cu(Ad An As aW Ax Bn Cp Cq Cv Cw Dc dN) cI(aD aI aP aY bR bW bX cW eF) aF(aD bL bW cU dE dH eF gL) dN(Ad An Ax Cq Cs Cw Dc) cD(aY bH bW cO dE dI) De(aL aW bE Cx Dk) bU(bH bL bP bW dE) Ch(aI aW cO cP) aD(aE aL aS cR) bQ(aP CO eF) bR(bW cO cU dI) Bg(bM DK) cC(bL bZ dE) Co(aW Dk) aI(aH aL) aY(bX cR) bW(aE bN) cP(cR cU) aQaU aWeF cSfP} Ma{Ms(Hv Ir Jp Jr Lh Li Lv Mi Mq Mr Mt Mz Nb Nn Oh Pa Pe Pf Qa Qd Qe) Nn(Hv Jp Lv Mi Mr Mz Nt Oi Pa Pe Qd) Lv(Hv Mi Mp Mr Mz Nb Oh Pa Pc) Hv(Iv Jp Mi Mt Mz Nt Pa) Pa(Et Jp Mt Mv Mz Qd) Pe(Jp Mg Mt Mv Mz) Nb(Ml Ny Of Oy) Mi(Jp Mt Mz) Jt(Ij It Ml) Oi(Mt Nt Qd) Mv(Iv Mz) NoMl NsMq NUp LxHq MzIv} Mg{Ng(Bg Hv Jk Jp Jr Lh Mj Mr Mt Mv Mw Mz Nb Nn Nt Nv Oh Oz Pa Pe Pf Qa Qd Qc) Oi(Hv Jp Jr Mj Mt Mz Nn Nt Oh Pa Pc Pf Qa Qd Qe Wm) Oy(Ba Ch Cu Mk Oz Pa Pf Po) Nw(Hu Ij Ml Og Pb) Mt(Hv Ns Pa Pe) Of(Bg Nb Pa Pe) Fr(Ap Bb Dg) Hv(Jp Mz Pf)

Figure 2 Continued

Cu(Hw Ii) Dc(Jl Lv) It(Iv Qa) LxHq MiJr MzPf IvJm} Iv{It(Hv Jp Jt Mi Mp Mt Mv Mw Mz Nd Nn Nt Pf Qa Qd) Oi(Et Jp Ml Mp Mt Mv Mz
Nt Oh Pf) Ml(Hv Ir Mi Mv Mz Nn Pf) Nk(Hv Jp Mp Mv Nt Pa Pf) Mx(Hv Ir Jp Mz Nn Qd) Ih(Jp Mz Nd Oh Pf Qd) Mp(Hq Jm Ms Nd) Nr(Mt
Pf) Ns(Mq Nn) Ir(Jn Js) MiHq MtNw LjPf} Ok{Lv(Hw Ij It Ml Nf Ny Pb) Qa(Hv Hw Ij It Jq Ml Mx) Ni(Hw Ij Jq Ml Nf Pb) Lu(Jp Mz Nw Oh
Qd) Hv(Ij It Jq Ml Nf) Ir(It Jn Jq Ml) Of(Jk Mp Nb Nt) Og(Il Iu Mv Nt) Qd(It Ml Mx) Ny(Mi Nb Nq) Mp(Hq Nd) Ng(Jk Mv) Oy(Mk Nb)
NqMy MiJq MtOi NfOh} cP{bE(al aP aW Bg bO bU cM cR Cu dD dN) Cu(Ad aW Ax bJ Bn Cp Cq Cs Dc) dK(aP BG bU bW cU dl dN) aP(aF
aW Bg bR bU cl) Ba(Ao aR aW bZ Dk) Bg(aJ aW cR dl) aF(aJ cR dN Fr) dN(bN bU cR) aJ(aW bR) bZ(cC cE) AoFr ChbA aWcR bUdl}
Ba{bZ(aF aZ bE bJ bU bX cG dF dH) Cu(aW bE bJ bQ Cq Cs Dc) bU(aW aY bE cR cU dN) al(aH aL aW bE bJ) cU(aZ bJ bR cC dH) aW(bR
Ch dN) Bg(aZ dN) Fr(bQ Dk) aY(bJ bR) cC(Ch cR) cH(aM bR) CtEf aFcR aZcS bNdN bQcO} Lv{Jt(Hv Hw Ij Jn Jr Js Me Mx Nf Ny Pb) Nn(Hv Iu Jp Mt Mz Oi Pe Pf) Ir(Jn Jr Js Ml Mx) Nb(Ml Mx Of Pb) Mp(Hq Nd Pg) Oz(Lz Ns Oy) Pa(Jp Mv Mw) Mi(Hq Jp) Ml(No Qa) Ms(Li Nt) MxPe NdIk ItQa} Nw{Oy(Jk Jl Mk Mv Nb Nn Oz Pa Pe) Ir(It Jn Jr Js Ml Mx) Mv(My Ng Ns Of) Jl(Hx Ml Mt Ny) Nn(My Nf Ns) Mi(Hq Mt Nf) Nb(My Of Pb) Nq(My Of) Nt(Of Oi) Ny(Pa Pe) Oz(Lz Pb) Pf(Lj Pa) MlHv MpHq MtOi MxQd} bZ{dK(aD aJ aW bE bR bU bX cA cC cD cR) aJ(aF aW bQ bU cC cE cI dF dH) aW(bE bR bU bX cA cC) cS(aD aF bS bX cD cE) aP(bR bU dH) bE(aD bR cA) Fr(bQ cE) bRdN} Mi{Hq(Hv Jl Jp Jr Mj Mp Mt Mv Mz Nn Nt Nu Oh Pf Po Qd) Ml(Hv Ir Jr Jt Mz Ni Qa Qd) Bg(Cq Nk Of Oy Pg) Mx(Ir Jt Nn Qd) Nn(Ns Nt) Ir(It Js) ItJt} Nt{Oi(Hv Jl Jp Mp Ms Mt Mv Mz Nn Oh Pf Qd) It(Hv Ir Jl Qa) Nn(Hv Ns) Nr(Jl Pf) Mp(Hq Nd) Mv(Ng Of) NsJp JlOf} bA{dG(aJ aP CU dL) Ch(aW bR bU cX) Cu(Cs Dc dM) aW(Bg Co De) BgDk CocR CqDe CxbU aHaI bQeF cDcO cSfP cUdH} cS{bE(aC aI cK cZ) cR(Bg bS cB cK) eF(bQ bR bU cV) Ar(Bg Ch) cN(cD dG) BgcI BocX ChbR aFcQ aPdG cBdA cUdH} Jl{Mp(Hq Lz Nd Pg) Oy(Mv Nn Nq Pf) Mx(Ni Ns Oi) Nn(Mt Of) Mv(My Of) Ir(Js Ml) Li(Lj Lz) NrPf NeNh IhQd} aJ{dK(aW bN bR bU cF cR dG dN) dN(aF aW bN bR bU cI) aW(bR bU cR) cI(aI bU) bRcH dGeF} bE{eF(aD aE aG aN bQ bU cD dF) gL(aD aF aN) Fr(Bo cD) aIaW aPbU bOdR dKdN} Mt{Oi(Hv Nn Pa Pe Pf Qd) Ns(Hv Mp Mq Nn Oz) Nb(Of Oy) NrPf MpHq IrIt} Fr{Dk(Bg cC cX Ef) Cu(Cs Nv) cC(aE dK) CoOy DgbC bRdI} Mv{Oy(Mk Nb Oz Pa Pe) Of(Bc Cu Nb) Ao(Jk Mr)} dN{eF(bQ cE cI cV) bN(bU bX dK) dK(bU cR) bQgL} Cu{Ef(Ax Ct Dc Dk) BgDk NqNv NkIi} Mp{Hq(Hv Jp Lh) Nd(Jp Lh) Pg(Lh Nb)} aP{bR(aW cH cI) bU(aW cI)} eF{aE(cC cV) cI(aF dK) bQdK} Nn{Ns(Jp Mq) NbOy QdOi} Nq{Ao(Mx Nk) MyIs} It{Ir(Qa Qd) HvJt} Oy{Bg(Co Pd) NbPf} PoLiOn NbIsOf

Constrained panels with 3 analytes, where 1.0E-3 >= 'model p-value' > 1.0E-4. Contains 3,509 panels of 939,239 total panels evaluated. : In{Pa(Et Hr Hv Ik Im Ip Jg Jk Jn Jq Jr Js Lx Mj Mm Mp Mq Mr Mv Mw Mz Ni Nn Nu Nv Nx Oh Pc Pf Po Qd Qe) Pe(Et Hr Hv Im Ip Ir Jg Jk Jq Jr Js Lx Lz Mj Mp Mq Mr Mv Mw Mz Nh Ni Nn Nq Nu Nv Nx Oh Pf Po Qd Qe) Nb(aA Et Hr Im Ir Jg Jn Jp Jq Jr Js Lx Md Mj Mm Mp Mq Mr Mv Mw Nh Ni Nu Of Oh Oy Pc Pf Po Qe) Pc(Et Ik Il Ir Iu Jg Jk Jn Jo Jq Jr Js Lw Lx Md Mp Mq Mr Mv Mw No Ns Nu Nv Nx Oh Oz Pd Po) Hv(Et Hr Hx Ip Ir Iu Jo Jq Lx Mm Mp Mq Mr Mw Mz Ni Nn Nq Nu Oh Pf Po Qa Qd Qe Wm) Ma(Bc Hx Ii Ir Iu Jk Jn Jq Js Li Mg Mj Mp Mq Mr Mw Nu Nv Oh Oz Pd Po Qe Wm) Mq(aA Et Hr Ir Jg Jr Js Jt Lw Lx Mg Mj Mt Mv Mw Mz Nn Ns Nu Oh Qa Qe Wm) Mz(Hr Hx Ik Ir Iu Jg Jo Jr Jt Mp Mr Mt Nn Nq Nu Oh Oz Pf Po Qa Qd Wm) Ir(aA Et Jg Jp Lw Lx Mg Mj Mp Mr Mt Mv Nv Oh Pf Po Qd Qe Wm) Nu(aA Ba Bc Co Cu De Jg Jh Jq Jr Lw Mg Mp Mr Mv Nn Qa Wm) Qd(Hx Il Iu Jo Jt Lx Ml Mp Mr Mt Mv Ni Nn Nq Oh Po Wm) Cu(Cq Cs Hw Hx Ii Md Mi Mv Nh Nk Nv Ny Of Oy Pb Pg) Jg(Hu Iu Jn Jq Jr Js Lw Mh Mj Mp Mr My Oh Oz Pf Qe) Jr(Et Ip Jk Jo Jt Mm Mp Mr Mt Mv Mw Nn Nv Oh Qe) Lw(Et Hx Ik Il Jk Jn Jo Js Jt Lx Mf Mp Mw Nv) Mr(Et Jp Jq Lx Mj Mp Mv Mw Nn Nv Oh Po Qe) Qa(Hx Iu Jp Lx Ml Mt Mv Ni Nn Nq Oz Pf Po) Mp(aA Et Hq Jq Mj Mt Mv Mw Nd Ns Qe) Jo(aA Jh Lx Mi Mt Mv Nn Oh Pf Qe Wm) Jt(Hr Hw Ij It Md Mj Ml Nh Nq Po Qe) Jq(Iu Jh Jp Mj Mv Mw Nn Oz Pf Wm) Mg(Hx Jn Jp Mh Nh Nn No Oi Po) Mv(Ao Hu Hx Iu Jn Ns Oh Qe) Nn(Ba Bc Iu Mj Oz Pf Qe) Wm(Jj Mn Ms Mw Nh Nx) Hr(Js Lx Mj Mw Nv Oh) Hx(Jh Lx Mt Oh Pf Po) aA(Ii Ip Jk Js Qe) Co(Iv Nh Nk Oy) Et(Mh Mj Oh Oz) Nq(Cq Dc Dk Hu) Mt(Cs Lx Ns Pf) Iu(Jh Jp Mj Pf) Ba(Mc Nh Nk) Mi(Bg Js Ni) Nv(Md Ns Oi) No(Md Ml) Nt(Bc Il) Nh(Bg De) Jh(Js Lx) Oh(Jp Ni) MjOz MsLi HwJj} Md{Nn(Et Hx Il Ir Iu Jg Jn Jo Jr Js Lw Ma Me Mg Mj Mq Mr Mv Mw Nh Ni Nu Nv Nx Oi Oz Pa Pe Pg Po Qa Qe) Mv(Cu Et Hv Ir Jp Jq Jr Jt Mg Mq Mr Mt Ni No Nu Nv Nx Oh Oi Pa Pe Pf Po Qa Qd Qe) Jq(Et Hv Jg Jp Jt Lu Mg Mj Mr Mz Nb Ni No Nq Nu Oh Oz Pa Pe Pf Pg Po Qa Qd Qe) Hv(Et Ip Jo Jp Jt Mm Mq Mw Mz Nh Ni Nk Nm No Nq Nv Nx Oh Pe Pf Po Qa Qe) Pc(Et Hu Ik Il Im Ir Jg Jk Jn Jo Jr Js Lw Mw Nh Ni Nq Nu Nx Oh Pd Pe Po) Lw(Hx Il Ir Iu Jk Jo Js Jt Mj Mq Mr Mz Ni No Nq Nv Oz Pe Pg Po Qe) Jp(Ik Jg Jr Jt Mc Mj Mq Mr Mt Mz Ni No Nq Nu Nx Oh Pa Pe Pf Po Qa) Nq(Cu Et Jr Jt Ma Mq Mz No Nt Nx Oh Pa Pe Pf Po Qa Qd Qe) Mz(Ik Jo Jr Jt Lu Mc Mq Mt No Nt Oh Oz Pa Pe Po Qa) Nb(Et Hr Jr Lh Mj Mw Ni Nk Nu Nv Oh Oi Po Qa Qd) No(Et Hr Jr Jt Mq Mw Ni Nk Nv Oh Pf Qa Qd Qe) Mg(Hx Jg Js Jt Mj Mq Mr Nt Nu Nv Oz Pg Po Qe) Qa(Et Jt Lh Mq Mt Ni Nk Nt Nv Nx Pc Pf Po) Ni(Jt Mj Mt Nt Nv Oh Pe Pf Po Qd Qe) Jt(Hr Jr Mc Mq Mr Nv Oh Oi Pf Po) Mt(Bg Jr Mc Mq Mr Oi Oz Po Qd) Et(Jr Lu Mc Mj Oh Pe Pf Po) Ma(Hx Mq Nv Nx Oz Pg Po) Cu(Ii Jj Mc Mi Nk Oi) Mq(Mw Nu Oh Pf Po Qd) Nt(It Lh Mc Nd Nu) Jj(Hw Hx Mk Nm Nr) Nv(Hr Mc Oi Pe Pf) Lh(Jr Nk Oi Qd) Po(Mc Nk Qd) Jg(Js Mc Nu) Mi(Bc Bg) McQd JkaA JnJs OiPf} Hr{Mp(Et Hq Hv Ik Jg Jp Jq Jr Jt Lw Lx Ma Mh Mj Mq Mr Mw Mz Nb Nd Ni Ns Nu Oi Pa Pe Qe) Mq(Et Hv Jg Jk Jp Jr Js Jt Lw Lx Ma Mg Mj Mr Mv Mw Nn Ns Nu Oh Pa Pe Qa Qd Qe) Pa(Et Hv Ik Ip Jg Jk Jp Jq Jr Js Li Lx Mj Mr Mw Mz Ni Nk Nn Nu Nv Oh Po Qe) Pc(Et Hv Ip Jg Jp Jq Jr Lx Mj Mr Mw Mz Ni Nn Nu Nv Oh Oi Pc Po Qa Qd Qe) Mr(Et Hv Ip Jg Jk Jp Jq Jr Jt Lh Lx Mj Mw Mz Nb Nn Nu Nv Oh Oi Qe) Jr(Et Ip Jg Jk Jp Jt Lw Lx Mj Mm Mv Mw Mz Nb Nn Nu Nv Oh) Et(Lh Lu Lw Mg Mh Mj Mv Mz Nb Nu Oh Oi Oz Qe) Ma(Ii Ir Iu Jk Jq Js Lx Mg Mj Mw No Nu Nv Oz) Lw(Ik Il Iu Jk Js Lx Mw Nb Nu Nv Oh Oz) Mz(Ik Jg Jp Lh Mj Nn Nu Oh Oi Po Qa Qe) Ni(Jg Jk Jp Lx Mg Mj Mv Mw Nv Oh Po Qe) Nb(Jp Lx Mg Mw Nu Ny Of Oh Oy Pb) Hv(Ip Lx Mj Mm Mw Nn Nu Nv Oh Qa) Oi(Jg Jk Jp Jt Lx Mj Mv Nv Oh Qe) Lh(Hq Jp Lx Ms Mw Nd Oh Qa Qe) Jt(Hw Ij It Jn Ml Nn Pb Pc) Nu(Jg Jp Jq Mg Mj Mw Nv) Mg(Js Lx Mh Mv No Nv) Jg(Js Mh Mj Oh Oz Qe) Cu(Mv Mx Nk No Pb) Jp(Ik Mh Mv Oh Qe) Mj(Mv Mw Nn) Ns(Mv Nv) Jj(Mk My) CsMt PoNk NnQd NoMl LxHq MsLi MvOh MwOz} Cu{Nk(Ad An As Bn Cp Cq Cs Cw Dc Dd Hv Hw Hx Ij It Jn Jo Jq Jr Js Mc Ml Na Nb Nc Nf Ny Of Oy Pb Pe) Dc(aZ bX cA cK cX dK Ir Is Jh Jj Jl Lv Ma Mg Mu Mv Nq Oi Oz Pb) Mv(Aw Cp Cq Ct Dk Hw Hx Ii Jg Jh Jk Nv Ny Om Pb Pg) Cq(bA Ef Ir Jh Jj Jl Mg Mi Mr Mt Nq Nu Oi) Mx(Aj Fr Ii Ji Ma Mi Mr Mu Ni Nu Oi Oy Pa) Jj(An Ax Cs Hw Hx Ij Js Ml Ny Pb Pe) cP(aM An As Bg bH cR Cv Cw cX DK) Mc(Ax Cs Js Lz Ml Nu Nv Pe Pg) Oy(Ba Bg Co Fr Jh Ma Mi Oi Om) Nv(Bg Jl Lu Ma Mg Mr Mt On) Pb(Hx Ii Mg Mi Ni Nq Oe Oi) Cs(aA aW aX aZ bE cA cR) Pg(Bg Fr Lv Ma Mi Nq Oi) Bg(aW bE cR dK Of) Mg(Dd Hx Jo Nm Of) Mu(Dd Hx Mt Pe Po) Nq(Hw Hx Ny Of) Ii(Fr Ir Nu Pa) aX(bR bV cI dH) cX(aJ bE bJ cR) Ef(Ad Cp Fw) Hw(Mi Qd) Oi(Of Pe) aW(aA cR) bE(aI Ch) bJ(cA dK) AxbA FrPe HxOz JiNy JrJs aJdG bQbZ cRdK} Oi{Nn(Et Hv Ik Iu Jg Jp Jr Jt Lh Lw Lx Mj Mp Mq Mr Mv Mz Nu Nv Oh Pa Pe Pf Po Qa Qe) Pc(Et Hu Ik Iu Jg Jk Jn Js Jt Lh Lw Lx Mp Mr Mv Mw Nb Nu Nv Oh Pa Pd Po Qa Qe) Jg(Et Hu Hv Iu Jp Jr Lj Lw Mg Mj Mr Mv My Mz Nu Of Oh Oy Pa Pe Qa Qe) Jp(Ik Iu Jr Lw Mj Mr Mt Mv Nu Oh Pa Pe Pf Qa Qd) Mg(Et Ir Js Lh Lj Lx Ma Mp Mr Mv No Nu Oz Po) Oh(Et Hv Ik Jt Ma Mq Mt Mv Mz Nb Nu Pa Pe Qd) Et(Jk Jr Lw Mj Mv Mz Nb Pa Pe Pf Qa) Mv(Jr Lh Mj Mz Nu Pa Pf Qa Qd Qe) Ma(Ii Jk Jt Lh Li Mp Nv Wm) Lw(Jk Lx Mp Nv Pf Po Qd) Mz(Ik Jk Mj Nu Pf Po) Jt(Hv Hw Ij It Ml Pb) Qd(Hv Ml Pf) Pa(Lx Mp Qa) Mt(Cq Ns) DkFr NuQa LxPe} Ns{Nn(Et Hv Il Iu Jq Jr Jt Lh Lw Lx Ma Mg Mj Mp Mr Mv Mw Mz Nb Ni Nu Nv Oz Pa Pc Pf Po Qa Qd Qe) Pc(Et Hu Ik Il Ir Jn Jq Jr Js Jt Lh Lw Lx Mp Mr Mw Nb Ni

Figure 2 Continued

No Nu Nv Oh Oz Po Qa Qe) Mq(Et Hv Jp Jr Lh Lw Lx Mg Mj Mp Mv Mw Mz Nt Nu Oh Oz Pa Pf Po Qa Qd Qe) Mp(Et Hv Jp Jr Lw Ma Mg Mj Ms Mv Mw Mz Nb Nt Nu Nv Oz Pf Qa Qe) Lw(Il Iu Jk Jr Li Mj Mw Nq Nu Nv Oh Oz Pa Pe Po) Mv(Et Hv Jp Jr Mt Mz Nt Nu Oh Oz Pa Pe Pf) Oz(Et Hv Jp Ma Mg Mz Nv Oh Pf Qa Qd) Jp(Hv Jr Mt Nu Oh Pf) Mt(Nt Pa Pe Pf) Nu(Ma Mg) Nv(Hv Ma) DkMu NtPf MkJj} Mg{Bg(Ao Bb Dc Dd Hw Ii Jg Jk Jm Mc My Nh Nj Nk Og Pz) Of(Ba Jg Jt Lh Mj Mr Mv Nt Nv Oz Po) Ng(Ba Et Il Lx Ma Mp No Nu Po) Bb(Ba Hw Jp Mr Mt Mu Nk) Dd(Fr Is Jl Jp Lv Lw Mt) Nb(Ij Ml My Ny Og Pb Pg) Oy(Il Jg Lh Mr Mv Nn Nv) Qa(Hw Ij Jm Jn Ml Pb) Ma(Aj Jr Mr Oh Oz) Jg(Ba Hu My Ni Og) Jp(Ap Dg Jr Pa Pe) Nn(Mr Oz Pa Pe) Lw(Jr Mf Mh Mj) Ap(Ba Mt Nk) Ct(Ba Fr Mv) Hu(Lh Mv Nv) Jl(Al Cq Dg) Jt(Ij It Ml) Ao(Fr Nq) Po(My Pb) Mc(Ax Cs) Mi(Aj Cq) Ni(Oz Pa) Hq(Lh Mp) Jm(Mj Qe) AfMr BaDg ChJj CoMu DcIs NoMl NtMs IrIt JrPa LhPg} Nb{Of(Et Hv Ip Iv Jk Jp Lh Lx Mi Mj Mp Mw Mz Nn Nq Nt Nu Nv Oh Pc Pf Po Qa Qd Qe) Oy(Et Hv Iv Jk Jp Lh Li Lw Lx Mi Mj Ml Mp Mw Mz Nq Nt Nu Nv Oh Po Qa Qd Qe) Ny(Et Hv Iv Jg Jp Jq Lx Mi Mp Mt Mv Mz Nn Nt Nv Oh Pc Pf Po Qa Qd) Pb(Hv Jh Jp Ma Mp Mt Mv Mz Nn Pc Pf) Ij(Jh Lw Ma Mt Mu Mv Mz Qa Qd) Ml(Hv Lw Mt Mv Mz Pf Qa Qd) My(Ma Mt Mv Nn Nq Pc) It(Hv Lw Qa Qd) Ma(Et Oh Pg) Mp(Hq Lw Nd) Pc(Lw Nk Pg) CoMu NnMs MvNg MwJg MxQd} Mv{Ng(Ao Co Db Et Iu Jp Lh Mp Mt Nn Nu Pa Pc) Of(Ir Jg Jq Jt Lh Mp Mr Ni Nn Nx Oz Pa Pe) Cp(Fr Ji Jj Mr Mt Mu Ni Nj Nu) Oy(Jg Lh Mp Mr Nn Nx Pc Po) Ao(Fr Mc Mt Nh Nk Nu Og) Bb(Fr Lw Mr Mt Nk Nu Og) Co(Ij Jk Mr Mu Og) Hu(Jg Lh Mt Nn Nt) Jt(Hw Ij It Ml Pb) Pc(Hv Mr Ni Pa Pe) Nk(Mr Oz Pa Pe) Cq(Jl Mi Mt) Ml(Ir No Qa) Mp(Hq Nd Pg) Af(Jj Mr) Dk(Jj Og) Lw(Dd Mf) Ni(Oh Pa) It(Ir Qa) Jk(Ap Bg) Bcli CUh DeMu NtMs LxHq LzOz IjQa QeJm} Lw{Pc(Iu Jr Lh Lu Lx Me Mj Mp Mq Mw Nj Nu Nv Oz Pa Pe Po Qe) Jg(Io Jm Mf Mj Mp Mr Og Pa Pe) Jm(Il Iu Jk Nv Oh Pf Po Qe) Lu(Et Mm Mp Ms Mw Nu Oh) Nn(Iu Me Mq Mr Ne Qd) Ml(Ir Jt Lh Ni No Qa) Lh(Ij It Nf Of Pb) Oy(Bg Mk Oz Pe Po) Ir(It Jn Jr Js) Qa(Hw Ij It Pb) Dc(Fr Lv Mu) Nq(Dd My Of) Mp(Mj Pd Pg) Oz(Hq Lz Pb) Po(Of Pb) Lx(Hq Nd) Mz(Pa Pf) Jk(Ng Og) Jt(Ij It) AnMa BbMu Bgli DdFr NuMq LzPa MfMw MsLi JpPf PbPe} Jt{It(aA Ir Jh Jp Jr Mj Mp Mr Mt Mz Ni Nn Oh Om Pc Pf Qa Qd) Ml(aA Hv Jh Jp Jq Jr Mp Mr Mt Mz Ni Nn No Oh Pc Pf Qa) Ma(Hw Jn Jo Jr Js Mx Nf Nn Ny Of Pb) Mi(Hv Hw Ij Jn Jr Js Nf Ny Pb) Ij(aA Hv Jh Mt Ni Nn Pc Pf) Pb(aA Hv Mp Mu Ni Nn Pc Pf) Of(Jg Mp Nn Nq Pc) Hv(Hw Jn Js Ni) Pc(Hw Jn Nf Ny) Nn(Jn Nf Ny) aA(Hw Mx Ny) Lv(Dc Na) NiHw} Nk{Pc(Iu Jr Js Lh Mp Nh Nl No Nv Oh Oz Po Qa Qe) Hv(Bg Iu Mp Mr Nt Oh Oz Pa Pe Pf Po Qa Qe) Pa(Jr Lx Mj Mt Nn Oh Pf Po Qa Qd Qe) Bg(Ij Li Mc Mp Mt Mu Nc Nh Nu Qd) Pe(Jr Lx Mt Nn Oh Pf Po Qa Qe) Ch(Li Mc Mi Mp Mu Nc Qd) Oz(Jg Jp Mt Qa Qd) Mr(Mt Nn Pf Qd) Ba(Ma Mc Qd) Cv(Fr Is Mt) Nt(Oh Pf) Mc(Co Di) Mi(Cq Nc) BbNq LvNc MlQa NhPf} Jg{Of(Il Iu Jo Jp Jr Mj Mp Mq Mr Mt Mz Nu Oh Oz Pf Po Qa Qe) Oy(Il Jp Jr Lh Mj Mp Mq Mr Mt Ni Nu Oh Pf Po Qa Qe) My(Jr Lh Mj Mq Mz Ni Nt Oh Pe Pf Po) Hu(Mj Mq Mr Mt Mz Ni Nt Oh Pa Pe Pf) Ni(Iu Mj Mp Mw Oh Oz Pa Pc Pf) Mw(Hv Lh Mj Mr Pa Pe) Qa(Ij It Jm Ml Pb) Og(Jq Mq Nu Qe) Mp(Hq Nd Pg) NoMl HvPf Irlt QeJm LhPg} bE{al(aE aH aJ aN aP aX aY Bg bO bU bZ cD Ch cI cQ dK dN) dK(aC aD aP aW aY BG bO bR bU cD cF cR cW) aW(aO aP bO bU cA cD cM dD dN) bO(aC aK aU bG bU cK cY) bU(aY bH bV bZ cW dN) cP(aF bG bV Ch cW) aA(Bg Ch Cx De) aX(aC aD cZ dD) bZ(cE cK cW) gL(cA cE cI) aL(cI dN) aP(bS cK) dR(bF cA) BgdN aEdD aJcK} Bg{Mt(Cq Dc Dk Jj Mu Nv Ny Of Oy) Mu(Co Dc Dc Hx Mk My Pz) Of(Ba Co Jh Mp Mr Nq Om) Dk(Ba Co cP dN Ef Mw) Mi(Jk Jm Mc Mx Nv Pb) Jj(Iu Mr Nh Nn Nu Qd) Oy(Ba Jh Mc Mp Om) aP(aW aZ bR bU cI) Ji(Dc Jq Mx Ny) aW(aA aJ cR dN) cP(bC bW dN) cR(aJ dK dN) aA(bJ Cx) dK(Ar dN) DcLi NqMy NuMc} Ir{It(aA Et Hv Jj Jp Jr Lh Lx Ma Mj Mq Mr Mz Nu Nv Oh Pc Pf Po Qe) Ml(aA Hv Ip Lh Ma Mj Mt Mz Nn No Nt Oh Pc Pf Qa Qd) Mx(aA Et Nn Pf Qd) Jn(aA Jh Mi Mu Pf) Jr(Iv Jh Mi Mu Pf) Js(Jh Nt Pf Qd) Mp(Hq Nd Pc) Cq(Mi Mt) CsMt DcLv DeMu NnMa} aP{bZ(aF bQ bS bX cA cC cD cE cI cK) cl(aF al bS bX cA cB cK dK dN) dK(aF aW bN bR bU cF cR dG) cA(aW aX bN cF cR dN) cK(aF aW bN cF cR dN) bR(aF bU Ch Co dN) dH(aX bN cF cU dN) bU(bH Ch Co dN) aW(bX cB Co) cP(bX Ch cR) CocR aFcD aXcB bNbX dGdN} Qa{It(aA Hv Ik Iu Jp Lh Ma Mi Mq Mt Mz Ni Nn Nu Pc Pe Pf) Ml(aA Jp Ma Mt Ni Nn No Nt Pc Pf) Ij(aA Jp Lv Ma Mi Mt Ni Nt Pc Pf) Hw(aA Jh Jl Lv Ma Mu Pc) Ph(Jh Ma Mu Pc) Om(Hv Jn Js) Pa(Ih Ma Pc) aA(Mx Ne) NnJm NrPf MiHq HxJl Ihlv JhJn} Oy{Oz(Jk Jp Ma Mi Mp Mt Nn Nq Nt Nv Pc Pf Po) Co(Ch Dg Hu Lu Ma Mi Mt Nu On Pf) Nn(Jp Lh Mk Mq Mt Nv Pa Pe Qe) Mt(Aw Cs Mk Pa Po) Ma(Aw Ba Cp Po) Mi(Ad Bc Ch Nd) Pe(Jk Nq Nv Pf) Pf(Mk Mp Pa) Jh(Mc Pd) Nv(Pa Pc) Om(Af Cx) BaDe ChPd PoPc NtMk} eF{aX(bG bQ bR bV cA cC cE cK cV dH) dK(aF aG aS aW bR cC cD cF cV) aE(aF bQ bR bU bX cD cT) aL(aF aW bR bU cD cT) bQ(aF aJ aW bR bZ) cV(aG aJ aN aW cT) cC(aG aW bH dI) aF(aG cP cS) bR(aG aH dI) cT(aS cE dF) dG(cS dN) bHcD bUdI bZcE dFdN} Ni{Pc(Iu Jr Lx Mp Mr Mw No Nu Nv Oh Oz Po Qe) Nn(Iu Jp Jr Mj Mp Mr Mt Oh Oz Pa Pf Qe) Pa(Jp Lx Mj Mp Mt Mw Nu Oh Pf Po Qe) Ml(Hv No Pf Qd) Mt(Cq Cs Dc) It(Hv Om Qd) Jp(Mp Oh Pf) CqNq MjMp} cP{aW(Bb Bc bU Ch Co De dI) aF(aO cO cU dH dI gL) Co(Ao aR bH bW Dk) cl(bU bW cG cM gL) bH(Bb bU bX cC cR) aE(aJ cG cM) cU(aU bR cY) Ch(aA aJ) Cx(aA bC) De(aR Dk) bV(bU bX) AfbW alcZ cCgL} Mu{Co(Dc Fr Ij It Jh Js Ma Mc Ml Mq Mr Mt Og Pz) Dc(Hq Hu Is Jl Lv) Ba(Hu Jh Ng) Bb(Ij Mc Mt) De(Fr Mq On) Ch(Nd Nu) Cs(Hq Hu) Dd(Is Jp) Dk(Fr Mq) Ml(Jq No) AoJj CpOn LxHq MjMx NfJq HuPb} aX{cK(aC aD aE al bN bO cZ dM) cD(aE al aJ bH bZ cA cX) cB(aD aE al bZ Ch dN) cA(aD aE al aJ bN) bZ(aD bQ cC cE) aC(bV dH) aF(aJ aO) bN(bM dN) ArCs BnCx CbcC aEal aJbS aZdN cSfP cUdH} Mp{Pg(Hv Jp Ma Mj Mr Mt Mz Nt Oz Pa Pc Pe Pf Po) Nd(Hv Lx Ma Mi Mj Mr Mt Mz Oz Pa Pc Pe Pf) Hq(Lx Ma Mj Mr Mz Nu Oz Pa Pc Pe Pf Po) Lz(Oz Pa Pe) MsaA} bZ{dN(aF aW bQ bU bX cA cE dH) aD(aF bJ bQ cC cE cI) aE(bR bU bX cC cM) bR(aF cE cA dI) aF(bX cD) al(aH cE) cl(cM cW) dM(cE cK) BccA CocC CxaA aWcD bHbX} Nq{Cq(Hu Ij Jh Jj Jl Mi Mr Mt Nd Nj) My(Ba Iv Jh Jp Mt Mz Qd) Ao(Ba Mc Nh) Of(Ba Iv Jp) Co(Hx Ij) Dk(Ij Jj) Qd(It Ml) Jl(Dc Mk) BaNv WmNo} aJ{dG(al aU bC bF bW cC cO cR cU cX) cl(aK aU cB cM) Co(aW bU cR) aE(al bR cB) cX(cD cF De) cR(aF cK) ChbU alaW bNcC cUdH} Nn{Ma(Et Jr Lh Mq Pf Qe) Mq(Hv Jh Jp Mz) Pe(Hv Jp Mt Mz) Lh(Nf Of Pg) Pa(Hv Jp Mz) ChJj NoMl NuJr MzHv QeJm OzPb} Mi{Cq(Fr Is Jh Jj Jl Jp Mr Mt Nd On) Nu(Hx Mh Ny Of Pb Pg) Ch(Jk Mc Mx Nu) AnJj BcPb LxHq LzOz MwMy} dK{cR(Ar aW bG bU bX cF Co) bU(bH bV cU dl dM) dl(bR bX cC cF) gL(aF cF cl) al(aW cl) bX(bH bV) bRcU cFdM} aA{Cx(bR bU cC Ch Co cR De) Mx(Js Nx Pe) Jq(Jn Ml Nf) De(aW bJ) Li(Lz Ms) ChaW CobQ LxHq ItJo NxOf aHal} Pc{Et(Jr Mr Pa Pe) Nu(Jr Mq Pa Pe) Mr(Hv Pa Pe) Lx(Hq Nd) Mj(Hv Pe) NoMl MqOh MsLi NdIk QeJm JpPf JrPa} Ma{Ba(Jj Mx Nh Nu) Nd(Ik Lx Nh) Jr(Et Mr Nu) Ml(Hx Jq) Mq(Mw Nu) Jl(Al Dc) Oz(Hq Lz) PoOf NgJk} Mt{Cs(Jj Mc Mr) Nw(Jp Pf Qd) Cq(Jl Lv) Nr(Nt Po) Ms(Li Nt) ChJj DcLv NoMl LxHq} gL{cl(cl(aF bW cC cT cX) aW(aF bQ cC cT) aE(aF cC) bQ(cS cT) aFdM cCdI cTdF} It{Hv(Iu Lh Mj Mq Qd Qe) Nt(Hq Jq Mz Qd) Qd(Lh Mq Wm) LvJo} Pf{Lj(Hv Jr Li Mz Qd) Lz(Oz Pa Pe) Ml(Jq Mc No) NtMs MzPa NfJq} Jj{Ch(Mr Nh Nu Qd) Hx(Mi Ny Pb) AfFr WmNh MeJo MlHw} Ba{De(Ao Bb Dk) cU(cA cG cL) Co(Bb Dk) NuMc cVcX} Lx{Hq(Hv Iv Jp Lv Ms Nt Om Pa) Nd(Jh Mh)} Li{Lj(Iv Jp Oh Qd) Ms(Jp Lh Nt) Lz(Oz Pa)} Fr{Mr(Af Bn Cq Dk) Is(Al Dc) CsLj CtEf} Ml{No(Hv Jp Mz Qd) NUq LvHx McQd MjJh} aW{cR(al bX Co) dl(bU bX)} dN{bH(bR bU bX) aEbX bNcA} Nt{Jq(Ij Nf) PoNr NeNh} Mx{Iv(Nd Oh) LvMj QdPe} My{Mw(Iv Wm) Jh(Mc Po)} Dk{Ef(Aj Ct) CocR} Nu{Mc(Ch Di) JrPa} Lz{Qd(Oz Pa) OhPa} Bc{CtEf cKcS} Lv{HxPb IjJo} bU{bHbV dIdM} CoCqJl MsLhOf NfNvNw IvJnJq Constrained panels with 2 analytes, where 1.0E-7 >= 'model p-value' > 0. Contains 5 panels of 19,595 total panels evaluated. : Fr(aA Ji Jj) Jj(Is On)

Figure 2 Continued

Constrained panels with 2 analytes, where 1.0E-6 >= 'model p-value' > 1.0E-7. Contains 44 panels of 19,595 total panels evaluated. : Fr(Hr Hu Hv Is Iv Lv Lw Md My Ng Ns Of Ok Oy) Ji(Hr In Is Jh Jj Jl Jq Ma Md Ml Mu Pc) On(Hr In Ma Md Ng Ns Of Oy) Jj(Iv Jl Mg Mu Nt Om) Is(Hr In) cS(cP cT)

Constrained panels with 2 analytes, where 1.0E-5 >= 'model p-value' > 1.0E-6. Contains 101 panels of 19,595 total panels evaluated. : Is(Ih It Jh Jm Lv Lw Ma Md Mg Mi Mu Oi Ok On Pc Qb) Jj(Jg Jh Jk Lh Lv Ma Mi Mt Mv Nw Oh Ok Pf Po Qd) Ok(aA Hr In Iv Jh Jl Lv Ma Md Mg Mi Mu Nn Pc) On(Hu Iv Jh Ji Lv Lw Mg Mt Mu My Ny Oe Og Oi) bA(aF aW bJ bR bU bZ cP cR cS dK) Jl(Hr Jh Lv Lw Ma Mg) aA(cS Ji Lv Lw Ma Mg) Ji(Jn Js Mx Nf) cS(bN bR bU Fr) Lv(Jh Mg Mu) cT(bJ dN Fr) Md(Nw Om) Mi(Jh Pc) MaNw IvJh Constrained panels with 2 analytes, where 1.0E-4 >= 'model p-value' > 1.0E-5. Contains 250 panels of 19,595 total panels evaluated. : Jj(aA Et Hv Ii Ik Il Im Iu Jn Jo Jp Jq Jr Js Jt Lw Lx Mj Mm Mp Mq Mr Mw Mz Nb Nn Nq Nu Nv Nx Of Oz Pa Pc Pd Pe Pg Qa Qe) aA(aF aW bE bJ bR bU bX bZ cI cP cR cT cX Hr Iv Jg Jh Jr Mi Mn Mt Mu Mv Mz Nw Om Pc Pf Po) Lv(Hr Hv Iu Iv Jg Jp Lw Ma Mi Mp Mr Mt Mv Mw Mz Nb Nn Nt Nu Nw Oh Om Pa Pc Pe Pf Qd) Mu(Cq Hr Hv In Iv Jh Jl Lw Ma Md Mi Mt Mz Ng Ns Nt Nw Oi Om Pa Pc Pf Qd) Iv(Hr In It Jg Jl Jp Lw Ma Mg Mi Mt Mv Nn Nw Om Pc Pf) Jh(Hr Hu Hv Lw Ma Mz Ng Ns Nt Nw Oh Om Pa Pc Pe Pf Qd) cT(aD aE aJ aP aW aX aY bE Bg bW bX bZ Ch cP cR dK) Om(Hr Hu In Jl Ma Mi My Ng Ns Of Oy Pc Qd) Mi(Hr Jg Jp Lw Ma Md Mt Mv Nn Nt Nw) Ba(aW aX bZ cP cR cS Fr) Ok(Hv Jp Lu Mt Nw Pf Qd) Fr(aW aX bA bE cP cR) Jl(In Md Nk Ns Oi Pc) Nw(Hr In Lw Mg Pc) bA(aE Bg bX Ch dN) cS(aW Bg cF cI dN) Ma(Hv Lw Mt Nt) Pc(Mt Nt Qd) aX(bU Co cP) aJ(bU cP) eF(bE cI) NtIn LwMt bZcP Constrained panels with 2 analytes, where 1.0E-3 >= 'model p-value' > 1.0E-4. Contains 327 panels of 19,595 total panels evaluated. : Ma(Et Hr Ir Jg Jp Jq Jr Jt Lh Lx Mg Mj Mp Mr Ms Mv Mw Mz Nb Nn Nu Nv Oh Oz Pa Pc Pe Pf Po Qa Qd Qe) Mg(Bg Hr Hv In Jp Jr Lh Lw Mj Mr Mt Mv Mz Ng Nn No Nt Oh Oi Oz Pa Pc Pe Pf Qa Qd Qe) Lw(Et Hr Hv In Jg Jp Jr Lh Mj Mr Mv Mw Mz Nb Nt Nu Oh Pa Pc Pe Pf Po Qa Qd Qe) Pc(Et Hv Jp Jq Jr Lh Lx Mj Mq Mr Mv Mz Oh Pa Pe Pf Po Qa Qe) Mv(Ao Et Hr Hv In Jp Jr Mz Ng Ns Nt Oh Oi Pa Pe Qd Qe) aX(aI aJ aW Bg bR bX bZ cA cB cD Ch cI cK Cp De dK dN) Jg(Hu Hv Md Mr My Mz Ng Ns Of Oh Oi Pa Pe Pf Qa Qd) Jp(Hr Hv Jh Jr Lh Mp Mq Ni Nn Ns Nt Pa Pe Pf Qd) Mt(Hr Hv In Jh Md Nn Ns Nt Oi Pa Pe Pf Qd) bZ(aD aF aJ aW bE bR bU bX cA cC dK dN) Mz(Hr Hv In Iv Mi Mq Nn Nt Pa Pc Pf) cP(aP aW bE Bg bU bV cR Cu dI dK dN) Hr(Et Hv Lh Mj Nt Pf Po Qa Qd Qe) In(Cu Hv Jt Lh Oh Pf Po Qa Qd Qe) aA(Bg Co Et Lh Lx Md Mj Nn Nt Qd) Jh(Jr Md Mj Mp Mr Of Oi Qa Qe) Nn(Hv Mq Nt Pa Pe Pf Qd) Cu(Ba bE Cs Dc Ii Mx) Jj(Ij Ip Li Ms Qb Wm) aJ(aF aW bR cR dK dN) aP(aW bR bU bX cI dK) Md(Lh Lx Mp Nb Nt) Hv(Et Mi Nt Pf Qd) dN(aW Ba bN bU dK) eF(aF aW bQ cT dK) Mu(Ao Bb Co Dk) Pf(Mi Ni Nt Qd) Oi(Iv Nt Qd) Mi(Bg Hq) Mp(Hq Nd) dK(bE cR) gL(aF aW) AoNq BaEf CoOy Constrained panels with 2 analytes, where 1.0E-2 >= 'model p-value' > 1.0E-3. Contains 340 panels of 19,595 total panels evaluated. : In(Ba Bc Bg Co De Et Ii Iu Jg Jk Jn Jq Jr Js Li Lx Mj Mm Mp Mq Mr Mw Nb Nu Nv Nx Oz Pa Pc Pd Pe Wm) Hr(Cu Ii Ik Il Im Jg Jk Jq Jr Js Jt Li Lx Mm Mp Mq Mr Mw Nb Nu Nv Oh Oz Pa Pe Pg) Cu(aW Ax bJ cR cX dK Fw Hw Hx It Jj Js Md Nk Nv Ny Of Oy Pb Pe Pg) Mp(Hv Ir Jg Jq Jr Jt Lw Mj Mq Mr Mw Nb Ni Nn Ns Nu Pa Pc Pe Pg Qe) Nn(Et Iu Jq Jr Jt Lh Lw Lx Md Mj Mr Ni Ns Nu Oi Oz Qa Qe) bE(aD aI aO Ar aW aY Bg bO bU bV bX Ch cM Co cW dD) Nu(Ba Bg Ch Hv Jq Jr Lh Mq Mr Mw Nb Pa Pc Pe) Pa(Et Hv Jq Jr Lx Mj Mw Ni Nv Oh Po Qa Qe) Pc(Ir Iu Jg Js Jt Md Mw Nb Ni No Ns Nv Oz) Bg(aJ aP bC bW cR dK dN) Jj Mc Mr Nk Oy) bU(aE aW aY bH bV cI cR dI dK dM) Nb(Et Jr Ml Mm Ny Of Oh Oy Pb) Jt(Hw Ij It Jn Js Md Ml Oi Pb) Pe(Et Hv Jr Lx Mj Mw Oh Po Qe) dK(Ar aW bW bX cF Co cU dM gL) Co(aJ aP cR dN Ii Jj Nk) Ni(Jg Jk Mm Mw Oh Oz Qe) Jr(Et Ip Jg Mm Mq Mr Mw) Oi(Et Jk Lx Mj Nv Oh Qe) Md(Jq No Nq Nv Nx Qa) aW(aI aO bW bX cG cR) Ch(aA aJ aP Jj Nk) Lw(Iu Lx Mq Nv Oz) Hv(Lh Mm Mw Oh Qe) bX(bH bO bV cR dI) Ba(Ij Ma Mc Nk) Mq(Lx Mw Ns Oh) Jg(Lh Mj Oy Qe) aP(aF cB cK De) Nq(Cq Dc Dk) Qa(Ij It Ml) De(aJ cR) Ns(Nv Oz) Lx(Hq Nd) Mr(Jq Mw) Ms(Lh Li) Oh(Et Lh) cI(aI gL) cF(aE cV) CpcR CqMi CsMt CxaA DcLv WmMa NoMl Irlt JqOz cPgL Unconstrained panels with 3 analytes, where 1.0E-8 >= 'AUC p-value' > 0. Contains 4,119 panels of 939,239 total panels evaluated. : Jj(Fr(aA Et Fp Hq Hr Hu Hv Hw Hx Ih Ii Ij Ik Il Im In Io Ip Iq Ir Is It Iu Iv Jg Jh Ji Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Jl(aA Et Fp Hq Hr Hu Hv Hw Hx Ih Ii Ij Ik Il Im In Io Ip Iq Ir Is It Iu Iv Jg Jh Ji Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Is(aA Et Fp Hq Hr Hu Hv Hw Hx Ih Ii Ij Ik Il Im In Io Ip Iq Ir It Iu Iv Jg Jh Ji Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Om(aA Et Fp Hq Hr Hu Hv Hw Hx Ih Ii Ij Ik Il Im In Io Ip Iq Ir It Iu Iv Jg Jh Ji Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) On(aA Et Fp Hq Hr Hu Hv Hw Hx Ih Ii Ij Ik Il Im In Io Ip Iq Ir It Iu Iv Jg Jh Ji Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Oy Oz Pa Pb Pc Pd Pe Pf Pg Po Pz Qa Qb Qc Qd Qe) Iv(Et Fp Hq Hr Hu Hv Hw Hx Ih Ii Ij Ik Il Im In Io Ip Iq Ir It Iu Jg Jh Ji Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Oy Oz Pa Pb Pc Pd Pe Pf Pg Po Pz Qa Qb Qc Qd Qe) Mu(aA Et Hq Hr Hu Hv Hx Ih Ii Ij Ik Il In Io Ip Ir It Iu Jh Ji Jk Jn Jo Jp Jq Jr Js Jt Lu Lv Lw Lx Ly Lz Ma Mb Mc Md Mg Mh Mj Mk Ml Mm Mn Ms Mt Mv Mw Mx My Mz Na Nc Nf Ng Nh Ni Nj Nk Nl No Nq Ns Nt Nu Nv Nw Nx Oe Of Og Oh Oi Ok Oy Pb Pd Pf Pg Po Qd Qe) Ji(Hq Hr Hu Hv Hx Ih Ij Ik Il Im In Io Ip Ir It Iu Jh Jk Jn Jo Jp Jr Js Jt Lh Li Lj Lu Lv Lx Ly Lz Ma Mc Md Mg Mh Mi Mj Mk Ml Mn Ms Mt Mv Mw My Mz Na Nc Nd Nf Ng Nh Ni Nj Nk Nn No Nq Ns Nt Nu Ny Of Og Oh Oi Ok Oy Pb Pc Pd Pf Pg Po Pz Qb Qd Qe) Ma(aA Et Hr Hu Hv Ii Ij Ik Il Ip Ir Iu Jh Jk Jm Jn Jo Jp Jq Jr Js Jt Lh Li Lj Lv Lw Lx Ly Mc Md Mg Mh Mj Mk Mm Mp Mr Ms Mt Mv Mw Mz Na Nc Nd Ne Ng Nh Nj Nk Nl Nm No Ns Nt Nu Nv Nw Nx Ny Of Oh Ok Pa Pc Pd Pe Pf Pg Po Qa Qb Qd Qe Wm) Jh(Et Hr Hu Hv Ii Ij Ik Il In Io Ip Ir Iu Jk Jn Jo Jp Jq Jr Js Jt Lh Lu Lv Lx Ly Mc Md Mg Mh Mj Mk Ml Mm Mp Mr Ms Mt Mv Mw My Mz Na Nc Nd Nh Ni Nk Nn Ns Nt Nu Nv Nw Nx Oh Oi Ok Pd Pf Pg Po Qa Qd Qe) Mt(Et Hv Ih Ij Ik Il Im In Io Ip Ir Iu Jk Jn Jo Jp Jq Jr Js Lh Li Lv Mc Md Mg Mi Mj Mk Ml Mm Mp Mq Ms Mv Mw Mz Na Nd Nf Nh Ni Nk Nn Nq Ns Nt Nu Nw Nx Of Oh Oi Pd Pf Po Qa Qd Qe) Pf(aA Et Hu Hv Ih Ik Il In Io Ip Jk Jo Jp Jq Jr Js Lj Lu Lv Ly Lz Mc Md Mg Mh Mj Mk Ml Mm Ms Mv Mw

MvOy bAbN cTdM} Om{Hr(Hu Hv Ih In Iv Mc Md Ng Ni Nk Nr Ns Oe Of Og Oi Oy Pz) Oi(Hu Ir Iu Iv Lu Md Ns Of Og Oh Oy Pf Wm) Ir(Ij In It Mc Md Ml Mx Nk Of Og Oy) Md(Hv In Iv Jh Jm Lu Of Og Oy) Oy(Iu Iv Jl Lu Mk Nb Oz Pa) Og(Hu Hv Iu Iv Nk Ns) In(Iv Oh Wm) Lu(Ns Of) WmNg NkHv} Ji{Hr(Hv Ih Il In Ir Iv Jh Lu Lv Mc Md Mh Mi Ml Mn Mr Ms Mt Mu Mw Mx Nh Ni Nj Nk No Ns Og Oi Pf) Ir(Hv In It Jn Jq Jr Js Md Ml Mx) Jh(Hv Ih In Mc No Ns Og Oi Pz Qb) In(Hv Iu Iv Md Nh Nt Wm) Md(Iu Mc Mv Ni Og) Iu(Ij It Mx) Iv(Oi Qb) WmOi MvIj} cD{bA(bF bL bN bO bR bZ cF cH CO cR cU cX De dK) cT(aM aX bH bL bN bO bZ cF cH CO cU cX dK) Ba(bB BG bL bN bZ cH Co cX De) aX(aE bN cP cW dK eF) eF(aF bH cH) bZcP} eF{aE(aL bE bR cC cH cV cX dF dG) bE(aD aF aG aN aW cE dF dK) dF(aD aN aP bZ cR cU d

Mw(Et Jo Jt Lh Lx Ly Na Ni Nv Nx Of Pd Po) Ik(Et Ip Jr Js Mj Mm Ms Nq Ns Nv Of Po) Et(In Jr Lu Md Mj Ni Nq Ns Oi) Po(In Ms Nh Ni Nk Nx Oi) Mj(Ip Mp Ni Nn Nq Of Pd) Cu(Ii Md Mx Nj Nk Pe) Mm(In Jr Lu Mi Mr) Js(In Md Ni Nn Nq) Nv(In Mr Ni Nk Ns) Jr(aA Nh Nq Of) aA(Iv Mn Nn) Wm(Is Om) Mr(Hr Of) Ni(Jt Lx) CoOy NoLh MiIp IuNx} Is{In(Et Fp Hq Hu Hw Hx Ij Il Im Io Ip Iq Iu Jg Jk Jn Jo Jp Jq Jr Js Jt Lh Li Lj Lu Lv Lx Ly Lz Ma Mc Me Mf Mh Mk Ml Mm Mq Ms Mv Mw My Na Nc Nd Nf Ng Nj Nk Nl Nm No Nq Nr Nu Nw Ny Oe Of Oh Ok Oy Oz Pb Pg Po Qa Qc Qd Qe) Jm(Et Fp Hq Hu Hw Ii Ik Io Ir It Iu Ji Jk Jl Jn Jo Jq Jr Js Jt Li Lj Lu Lx Ma Mb Mf Mg Mh Mi Mj Mk Ml Mm Mq Mu My Mz Na Nb Nd Ne Nf Ng Ni Nj Nk Nl Nm Nq Nr Nv Nw Nx Ny Oe Ok Oy Oz Pa Pb Pe Pg Po Qa Qc Qe) Oi(aA Et Hq Hu Hw Hx Ii Ij Ik Il Io Ip Iq It Jg Jn Jp Jq Jr Js Jt Li Lj Lu Lx Ly Lz Ma Mb Mc Me Mh Mi Mk Ml Mm Mn Mp Mq Mr Ms Mu Mw My Mz Na Nc Nd Nf Ng Nj Nk Nm No Nq Nw Ny Oe Of Og Oy Pb Pg Pz Qc Qe) Hr(Hq Hu Hw Hx Ii Ij Il Im Ip Ir Iu Jn Jp Jq Jr Js Jt Li Lj Lw Ly Lz Ma Mb Me Mf Mg Mh Ml Mp Mq Ms Mu Mw Mx My Mz Na Nc Nd Ng Nj Nl Nm Nn Nq Nt Nu Nw Nx Ny Oe Of Og Ok Oy Pb Pc Pd Pf Qc) aA(Hq Hv Hw Ii Ij Il Io Ir It Iu Iv Jg Jh Ji Jn Jo Jp Js Li Lz Ma Mf Mg Mi Mj Mn Mp Mu Mv Mw My Na Nd Nf Ng Nh Nj Nk Nm Ns Nt Nw Ny Oe Of Og Oy Pa Pb Pd Pf Pg Qc Qe) Qb(Et Hu Hw Ij Ik Il Io Iq It Jg Jp Li Lu Lx Lz Ma Mc Me Mg Mi Mk Ml Mp Mr Ms Mu Mv Mw Mx Mz Nd Ng Nj Nk Nq Ns Oe Of Og Oy Pd Pe Po Qa) Ih(Fr Hu Hx Ij Ik Io Iq It Ji Jl Jp Jr Li Lv Lw Mc Mi Mr Ms Mv Mw Mx My Mz Nc Nd Ng Ni Nj No Nu Oe Of Oh Om Oy Pa Pc Pd Pe Pz) Iq(Hv Ij It Iv Jg Ji Jp Li Lv Lw Ma Mc Md Mg Mh Mn Mp Ms Mt Mv Mw Mx Mz Nd Nh Nn Ns Nt Nu Of Og Oh Om Oy Pc Pd Pf) Mn(Hv Ij Io It Iv Jh Ji Jp Lw Mc Md Mi Mt Mv Mx Mz Nk Nn Ns Nt Oe Of Og Om Oy Pc Pf Pz) Nh(Hv Ij Io It Iv Jh Ji Lw Mc Md Mi Mv Mx Mz Ne Nk Nn No Ns Oe Of Og Om Oy Pc Pf Pz) Fr(Hq Hu Hv Hx Ij Io It Iu Iv Li Lx Ly Md Mx My Nf Ni Nk Nn Ns Oe Of Og Oy Po) Md(Hv Io It Iv Jh Ji Jp Lv Mi Mr Mt Mv Mz Ni Nk Nn Ns Nt Nu Oe Og Pc Pf Pz) Pz(Et Hv Ik It Iv Jg Ji Jp Lw Mc Mg Mi Mr Mu Mv Mz Nn Ns Nu Nw Og Ok Pc) Jh(Hv Ii Ij Im Io It Iu Iv Jk Mc Mx Nk Nm No Nq Nr Ns Nu Oe Of Og Oy Pc) Mc(Hv Ij Iv Ji Jp Lv Lz Mi Ms Mt Mx Nk Ns Nt Oe Of Og Om Oy Pf) Lv(Hv Ij Im Io Iv Jq Ms Mt Mx Mz Nd Nk No Nr Ns Of Og) Iv(Hv Ij Io Jp Lz Mv Mx Nk Nn Ns Oe Og Oy Pc) No(Hv It Ji Jp Mi Mt Mv Mz Ns Nt Og Om Pf) Mt(Hv Ij Io It Iu Mx Nr Ns Oe Of Og Oy) Nk(Hv Ji Lw Mh Mv Nc Nn Og Om Pf) Om(Ii Ij Jq Ms Nr Ns Of Og Oy) Og(Hv Lw Mv Mx Ns Nt Ok) Nr(Ji Mv Ni Nt Pf) Ns(Hv It Ji Nt Pf) Mx(Hv Ir Ji Ni) Ni(Ij It Of) Hv(Hx Ij It) Nt(Ij Of) Im(Mi Mv) Ir(Js Ml) Pf(Oy Pe) NbNy HxJl ItIu JiJq} Fr{cD(aC aD aE Af aI aJ Al aM AN Ao AP aQ aR aS Aw Ax aY BB BC bF Bg bL Bn bO bP bS bV bW bX cB cE cF cG cJ cK cL cM cN CO Cp Cq cR cS Ct cU cV CW cZ Dc DD DE dG dH DI dK DL dM) Oi(aA Hq Hw Hx Ii Ij Ik Im In Io Ip Iq Ir Jg Jk Jl Jm Jo Jq Js Jt Lh Li Lu Lx Lz Me Mi Mj Mk Ml Mm Mp Mt Mv Mw Mx My Nb Nc Nd Ni Nj Nm Nn No Nr Nv Nx Ny Oe Og Oz Pa Pe Pf Pg Pz Qb) Iv(Et Hx Ik Ip Ir Jl Jn Jo Jp Jq Jr Jt Lh Lu Lv Lx Ma Mb Me Mf Mi Mj Mk Mm Mp Mq Mr Mu Mv Mw Mz Na Nb Nc Nd Ne Ni Nj Nl Nn No Nt Nu Nx Oh Ok Pa Pd Pe Qc Qe) Hv(aA Hr Hw Ii Ik Il Jg Jh Ji Jp Js Lh Lj Lv Lw Lz Mb Me Mh Mk Mm Mn Ms Mt Mv Mw My Mz Na Nb Nd Nh Nu Nv Nw Ny Om Pa Pb Pc Pd Pg Po) cC(Af aG AL Ar AW Ax aZ bA Bc bE Bg bJ bM bO bP bR bU bW bZ cA cG CH Co Cp CQ cT cU cV Cw Cx DB Dc De dG dJ dM) dN(aC AD aL aN Ao aQ aR AS aV aY BB Bc bF bL Bn bO bS bX cB cF Ch cJ cN CO cQ Ct Cv cW Cx cZ dA Dd DE Di Dl) Ji(Et Fp Hx Ii Ij Io Jh Jk Jn Jo Jr Js Lh Li Lu Lv Ly Mb Mm Mn Mt Mw My Mz Nc Nd Ng Ni Nj Nu Nv Nx Ny Oe Om Po Qa Qc) Ng(Hx Io Iq It Jh Jm Jp Lj Lw Lz Md Mg Ml Ms Mx Na Nf Nh Ni Nr Ns Nu Nw Nx Oe Pc Pd Pz) Mc(Bc Hu Ij Il Io Iq Jk Jm Jn Jp Lw Md My Mz Nb Nf Nh Nk Nq Nr Ns Nw Og Om Oy Pc) cI(aA aF aH Aj aL aO aP Ax aY BA Bc bE bO bP bX cM Cq cR cV dF Dg dL dM) Dk(aF aH aI aO aW bA bC bL bN bO bP cA cB cF cH cK cP Cs cU cV dF dG dM) cP(Ad Af Aj Al aU aY BN bO cA cH cM CS cW cZ Db dE Dg Di dJ) dB(aH Aj AL Ap Ar aW AX Ba Bc bE bJ bU cA cR Cx Dc dF dG dM) Nq(aA Ih In Jm Jp Mj Ms Mt Mu Mz Nb Nk Nr Oe Of Og Oh Om Oy) Iq(Hu Jh Jp Js Md Mj Mr Ms Nh Nk Ns Nw Of Oh Ok Om Oy) bU(aE Aj Ar aZ bA Bg bJ CH cQ cR Cs dA Db dF dJ) No(Hu Il Jn Jp Lw Ms Mz Nh Ns Nw Of Ok Om Oy) Ih(Hu Io Lw Md Ms Nh Nk Ns Nw Oe Of Ok Om Oy) Om(aA Ij Io Jh Jk Ly My Nf Nk Ns Nv Pz) cX(Aj Ar bE bJ bR CH cQ cR Cs dE dF) Nr(Et Hq Jh Jp Mj Ms Mt Mz Na Pd) Ly(aA Hu Jp Md Mz Nk Ns Og Oy Pz) bQ(aF aG aQ aU BN cN cZ dK Dl) In(Hu Lw Ms Nk Ns Nw Oc Of Ok) aL(Aj aW aZ bO bP cM cT Db dE) bE(aC aZ bO bR cE Db Dg dM) aA(Hq Hx Li Mz Na Nk Pz) aH(aD Ar aZ Bc bJ Cs) Pz(Et Jp Js Nt Of) Jm(Lw Mr Nu Nw Nx) Cs(aZ dE dF Oy) Nw(Md Nh Oe Qb) Db(bJ bR cR) Dg(aW aZ dE) Oe(Ms Nk Nu) Bo(bH Nh) Nb(Of Oy) aW(Bc cR) bJ(Aj aZ) WmMr NhNk OyOz cEcR dGdL} Ji{Hr(Et Hq Hu Hw Hx Ii Ij Ik Im Io Ip Iq It Iu Jg Jm Jn Jo Jp Jr Js Jt Lh Li Lj Lw Ly Lz Ma Mb Me Mf Mg Mj Mk Mm Mp Mq Mv My Mz Na Nb Nc Nd Ne Ng Nl Nm Nn Nq Nr Nt Nu Nv Nw Nx Ny Oe Of Oh Ok Om Oy Oz Pa Pb Pc Pd Pe Pg Pz Qb Qc Qd) In(Fp Ij Il Ip Jp Jq Lu Mk Mn Ms Mt Mv Mw Mx Na Nc Nd Ni Nk Nl Nr Ns Nu Of Og Oh Oi Om Oy Pd Pf Pz) Jh(aA Et Hu Hx Ii Il Im Io Iq Ir Iv Jg Lh Lu Lv Mn Mr Ms Nd Ng Nh Ni Nk Nm Nn Nq Nr Nv Nx Oe Of Oy) Lu(Hv Ih Ir Iu Iv Mc Md Ms Mw Mx Nh Nk No Nr Ns Of Og Oi Pz Qb) Og(Hv Hw Ih Ij It Iu Iv Jn Jq Jr Js Mc Me Ml Mv Mw Mz No Pb) Iv(Ih Io Lv Ma Mc Md Ms Mx Nd Nh Ni Nk No Ns Pz) Mv(aA Hw Ih It Jq Mx Nf No Ny Oi Om Pb Pz Qb) Mc(aA Hv Ir Mn Ms Mw Nh Ni Nk Ns Oi Pf Wm) Md(Ih Jp Mh Ms Mt Mx Nk No Oh Oi Om Pf) Oi(Hv Il Ir Iu Jp Mt Mu Mw Ni Ns Pf) No(aA Hv Jp Mu Mw Mz Nh Ns Pf) Iu(Hw Jn Jr Js Ml Nk Ny Om Pb) Hv(Ih Lv Ms Nk Ns Qb) Qb(aA Jl Mt Mu Pf) Pz(Jp Mt Mu Pf) aA(Lv Mh Ne Nf) Pf(Ih Nr Pe) Wm(Fp Mr) Mx(Mw Oh) Ni(It Ml) Ir(Ij Nf) NsIh HxJl IlJq} cS{cP(aA aC AD aE AF aG aH aI aJ aK aL aM aO aP aQ Ar AS aU aV aW AX aY aZ bB bC bF bG bI bL bM bP bS bV bW bX cA cB cE cH cL cN cO Cp cR cT CU cV cW cX cY cZ dA dC dD DE dF dG dH dI dJ dM) bR(aC aD aF aK aM aO aP aR As aU aW BC bF bG bP bW bZ cB cO cU cV cW cX cY cZ DG dI eF) dN(aA aD aE aG aH aJ aK aM aN aP aR aU aW bA bB bC bJ bV bZ cC cG cN cU cV cZ dA dC dG dI dL) bU(aE aG aH aI Aj aN aP aQ aV aX aZ bH bI bJ bL bM bP bS bV bX cE cJ cK cO dC dK dM eF) cD(aI aJ aY bJ bM bO bX bZ cH cK cM cR cX dI dK) Bo(aA aX bN bP bS cK cR Cu cX dE) bQ(AJ aP Bg bO bZ cN cR dA gL) cQ(As bJ bO bX cA cB cC cK cX dK) bN(aJ aN bX bZ cF cM cR eF) aA(bJ bO bS bX cC cF) bA(aD bO bX cF dF dG) cI(aI aJ bS cF cM cR) bE(aC bO cK cZ) cT(aD aN bJ cC) Ar(bP cH cX) bS(dA dJ) dE(Aj Dg) bXcF bZcE dGeF} Om{Og(Hq Ih Ij In Io Ip Jh Jm Jo Jp Lu Lw Lz Mc Mg Mh Mi Ms Mt Mv Mx My Nd Nf Nh Ni Nr Of Oh Ok Oy Pz) Hr(Hq Ij Io Iq Ir It Jh Jm Jo Lu Lv Lw Mi Mj Ml Mn Mr Ms Mx My Mz Na Nd Nf Nh Nj Nm Nq Ny Pb) aA(Ii Ij Io Iu Iv Jh Jm Jo Lu Lw Lz Ma Mx My Nd Ne Nf Ng Nl Nn Ny Oe Of Oh Pc Pf Pz Qb Wm) Md(Hu Ih Ij Iu Jo Jp Jr Mc Mh Ms Mt Mw Nd Ng Nh Ni Nj Nk Nr Ns Oe Oh Pf Pz) Ir(Hu Hv Hw Ih Ii Io Iq Jn Jo Jq Lu Ms Mu Nf Ni Nr Ns Ny Oe Pb Pc Pz) Ns(Hu Hv In Iu Iv Jh Jm Jo Jp Mc Ms Mt Nk Of Oy Pz) Nk(Hu In Iu Iv Jo Lu Mc Ms Nc Of Oh Oi Oy Pc) Oi(Hv Ij Jh Jp Lw Mt Mv My Mz Na Nd Nw Pd) Oy(Hv In Jp Lh Mc Mr Mt Nd Oh Pe Pf Po Pz) Of(Hv In Iu Iv Jh Jp Jq Mc Mv Ni) Lu(Hu Hv In Iv Mc My Nr Pz) In(Hu Hv Iu Jn Jp Nh Nt) Hu(Hv Iu Iv Mv) Ms(Hv Iv Nd) Iu(Hv Oe) Iv(Jp Ma) CuMc WmMr IlJm PzJh} dN{dR(aE aF aG aH aI aJ aK aL aO aS aU aV aY aZ bC bI bJ bL bO bQ bR bS bU bV bW bZ cB cF cG cJ cL cN cO cU cV cW cX cY cZ dB dC dE dF dG dH) gP(aF aH aI aN aP aR aU bC bI bJ bM bP bR bS bW bX bZ cC cF cI cK cM cN cO cR cV cX cZ dA dD dE dH dJ dL gL) cR(aA aJ aK aL aO aQ aS aU aV aX Ba bF BG bH bN bU cA CH cK cM cP cW cX dD dM) cT(aA aF aG aJ aK aM aP aV aW aZ bC bI bV bW cJ cW cY dD dI dJ dM) bA(aC aU aX bH bL bS cA cD cN Co dA dC De dH dI) gL(aL aQ aS aU aY bG bM bV bW cB cD cM cW dA dE) Ba(aD aY bB bO cB cD cF cK Co cU dA DE dH) aX(aC bF bR bX cP cW cZ dK) bZ(bJ cA cK cM cW cX) cP(aU BG bH bN bU) aA(bJ bS cA cH cK) dK(aI bR bU bX) aP(bN bR bU) eF(aY cW) aJbR bHbX bUdI} aA{cX(aF aH aJ aM An aO aP aQ aR aS Ax aZ bB bC Bg bH bM Bo bV bW cB cE cG cL cN cO Cp dA dB dC dH dI dJ dL dM dR gL) Lv(Hq Hw Ii Ij Im Ip Iq Ir It Iu Jm Jp Li Lj Lz Ma Mb Mc Me Ml Mm Mn Mp Mt Mx Nf Nn Nq Nw Ny Oe Oy Pc Pd Pg) bU(aC aG aH aJ aK aL aM aO aQ aR aS aV aW bB bE bM bP bV cC cE Ch cJ cK cL Co cQ cT Cu cV Cx cZ dA dD dF dM)

Figure 2 Continued

In{Jr Li Ma Mm Mn Mz Nw Oh Wm) cD(aX bF bJ bO bR cH cR dR) Ma(Ih Iv Jr Lw Mz Nw Pc) Jr(Jh Mm Mn Mp Mu Pc) bJ(aY bN bO cI dD dK) bR(bF bO cO cR cU) cI(bF bN bO cO dK) Mc(Mp Mz Nq Pf) dK(aY bF bG cR) Mu(Ih Iv No) aF(cH dR gL) Co(Bo bQ) Nn(Jp Nk) Mz(Hr Mp) bN(bO cH) bZ(cE dG) eF(cV dG) CxcR NoMn aLdR bFcC} Cu{Mc(Aj Ar Bg Cw Db Hv Ii Ik In Iu Jg Jn Jt Lu Lw Ma Mf Mp Mq Mt Na Nb Ne Ng Nh Nj Nl Nm Nn Nq Nv Nw Og Ok Oz Pd Pe Qa Qc) In(An Ao Cp Cv Db Di Ij It Iu Jg Jq Js Lh Lw Lz Me Mf Mj Ml Mn Mu Mz Nb Nf Nj Nl Nn Ns Oh Ok Oz Pb Pd Pe Qc Qe) No(Al Cq Hr Hw Hx Jm Md Nk Nu Ny Of Oy) Dk(aK aW aY bA cF cK cL cQ cR) Nk(Al Hw Ih Md Mh Nu Pz) cT(bJ Bo cH cl) Ba(cD cX) Cs(Ef Fw) Ii(Bo Lw) Pz(Mu Nu) bA(bJ dM) DcOi NqOy HxIh aWcQ aXbU bJcP bQcR} bA{bU(aG aH aJ aK aO aQ AR aU aX aZ bE bM bP bQ bS bV bX cL cN cP cQ Cx dB dE dH Di dJ eF) cD(aD aU aX Bg bH bJ cB Ch cT dD eF) cI(aU bB bF bZ cG cH cX dD dK dR gP) bJ(aE aN Bg bO bR bZ Ch cU cX) bN(bM bO bR cF cR cU cX dK) cX(Af bO cF Co cR cU) cH(aF bC cA dK dL) cU(bO cA cF dK) aD(aF bR cO) dK(aI bG bR) aF(aI bG) ChcC CobQ aEcB bRcR} Iv{Ma(Hv Ih Ir It Jh Jm Jp Lw Md Ms Mt Mx Nd Nh Ns Nw Of Oh Pc Pf) Jp(Hr Ih In Io Jh Lv Lw Md Mi Mu Ng Nk Ns Oe Og Oi Pf Pz) In(Et Hr Hv Jn Mg Mm Mt Mu Mv Mz Nt Nw Ok Pf) Jh(Hr Hv Jl Lv Md Mt Mu Ng Ns Nu Oe Of Og Oy) Mu(Hr Hv Jm Lw Md Nk Ns Oi Oy) Lv(Hv Md Mp Ms Nd Nk Nw Oh) Hr(Jl Mt Nk Oi) Jl(Ih Mx Nk) NqMd MvNg NkPc NwOi} cT{cI(aM aU aX bC bF bJ bN cC CO cR cY Dc dK) cD(aU bB bC bF bG bJ bR cB cG Cp cR cY) bU(aF aL BB bF bI bR cO dJ) cU(aN bN Bo cF cM cX dK) cX(Af bO cF Co De) cH(aD aF bO cC) Co(aZ cC dB) bJ(aN Bg Ch) aD(aU aX) bE(Bg Ch) aFfP aIdK bZcP} Ba{bU(aI aW aY bB bO bR cD cO Cs Cx dB) cD(aD aI aX bR cB Ch cO cR Cs dM) cH(aL bJ Bo bS cA Ct DB dE dM) cI(Ad As bG bO cF Ch dA dM) Bo(aI bN cF cR cU) cX(bO cR Db dE) bJ(bG bZ cU) As(bO dM) aL(Bg Ch) bR(cU dB) CoOy MgIn aIaW bNcR cBdB} eF{dF(aI bN bO bR bU bW cC cD cF cH) aG(aL bC bJ bR bW cO cR cV) aE(aS bJ bN bS bU cA cR) aN(aL bN bR bU cH cR cV) aD(aF bJ bN cH cV cZ) aH(aI bN bR bU cR) bU(bE bF bN cH) bQ(bE cF cR) aF(cC cQ) cE(bZ cC) dK(aL cH) bEcD dGdL} In{Mt(Dc Dg Hu Hv Ij Jn Li Mb Mi Mp Ms My Nh Nm No Nu Ok Pc Wm) Mg(Ad An As Aw Bg Bn Ch Cs Cw Cx Db Dl Mi Oh Ok) Mi(Bc Jn Jr Lw) Mu(Bc Lw Nh Pd) Nt(Hv Qa Wm) Hv(Mv Oh) Jr(Mp Nm) Nw(Hr Iu) BcMa CvJt LwLi McJn} cP{Co(aE aF aU Ax aY aZ Bb bN bO bQ bR cA cC cD cF cM Cq Cs) bZ(aG aL aN aS aW aY bE bG bN bO bX cF cK cQ cX cZ dM) aX(Bg Ch cI) dK(bW cG cR) De(cH cI) aU(Bg Ch) bU(bH dI)} bU{aX(aN Ar aY Bc bO cD cW dA dK) aJ(aY bH bZ cU cX dG) aP(bN bR cH) dI(aD aE dC) bE(cW dK) bZ(dA dK)} Mt{Md(Hu Ih Jn Mc Nb Pz) Ns(Ih Jn Mc Pz) Nk(Af Ap Bo) Oi(Bc Lw Pf) Jn(Ih Mc) WmNg} Oi{Nw(Ir Iu Jh Mg Mv Pf) Pf(Hv Jh Lw Mg) Mg(Jp Oh) Jh(Oh Wm) HrQd} Co{Oy(Hu Hv Ir Iu Mc Mx Nd Nj Nk Pz) cQ(cX Dg)} Lx{Md(Ih Iq Mb Mc Nb Nr Oe Pc Pz) AfNk WmNi NdOg} bZ{cQ(aE aF bJ bQ cD cI dK) cE(cA cC cR) aPbR bQdK} Hv{Mv(Ng Nk Ns) Lv(Ir Oh) Mu(Hr Ir) Jh(Hr Mc) NiOh} bE{dR(aD aF aN cI) gL(aF cI dK)} aJ{bR(cR cU cX) cI(aI bN cR)} aX{cD(aP bO cR dD) Bo(cR cX)} Mu{Nu(Md Ns) LwPc IqIr PzOk} Mv{Pz(Bc Nw Ok) BcMc DdLw} Mr{Wm(Lv Lw) CqIr NnOy} Jh{Mc(Ir Jr Oh) PzNw} Lv{DdMg HrNw} Mi{DkJp WmNh} Nk{Jl(Hr Pc)} CpCsEf LwIlJm MpNiIr aPbNbR

Unconstrained panels with 3 analytes, where 1.0E-6 >= 'AUC p-value' > 1.0E-7. Contains 12,635 panels of 939,239 total panels evaluated.

Is{Lv(Et Fp Fr Hq Hu Hw Hx Ii Ik Il Ip Ir It Iu Jh Ji Jk Jl Jn Jo Jp Jr Js Jt Lh Li Lj Lu Lw Lx Ly Lz Ma Mb Me Mf Mg Mh Mi Mj Mk Ml Mm Mp Mq Mr Mv Mw My Na Nb Nc Ne Nf Ng Ni Nj Nl Nm Nn Nq Nt Nu Nv Nw Nx Ny Oe Oh Om On Oy Oz Pa Pb Pc Pd Pe Pf Pg Po Qa Qc Qd Qe) Og(Et Fp Hq Hu Hw Hx Ii Ij Ik Il Im Io Ip Ir It Iu Jg Jk Jl Jn Jo Jp Jq Jr Js Jt Li Lj Lu Lx Ly Lz Ma Mb Me Mf Mg Mh Mi Mk Ml Mm Mp Mq Mr Ms Mu Mw My Mz Na Nb Nc Nd Nf Ng Ni Nj Nm Nn Nq Nr Nu Nv Nw Nx Ny Oe Of Oh Oy Oz Pa Pb Pc Pd Pe Pf Pg Po Qa Qc Qe) Hv(Et Fp Hq Hu Hw Ii Ik Il Im Io Ip Ir Iu Jg Jk Jl Jn Jo Jp Jq Jr Js Jt Lh Li Lj Lu Lw Lz Ma Mb Me Mf Mg Mh Mi Mj Mk Ml Mm Mp Mq Mr Ms Mu Mv Mw My Mz Na Nb Nd Nf Ng Ni Nj Nm Nn Nq Nr Nt Nu Nv Nw Nx Ny Oe Of Oh Ok Om On Oy Pb Pc Pd Pf Pg Po Qa Qc Qe) Jh(Et Fp Fr Hq Hu Hw Hx Ik Il Ip Ir Jg Ji Jl Jn Jo Jp Jq Jr Js Jt Lh Li Lj Lu Lw Lx Ly Lz Ma Mb Me Mf Mg Mh Mi Mj Mk Ml Mm Mp Mq Mr Ms Mt Mu Mv Mw My Mz Na Nb Nc Nd Ne Nf Ng Ni Nj Nl Nn Nt Nv Nw Nx Ny Oh Ok Om On Oz Pa Pb Pd Pe Pf Pg Po Qa Qc Qe) Mc(Et Fp Hq Hu Hw Hx Ii Ik Il Im Io Ip Ir It Iu Jg Jk Jl Jn Jo Jq Jr Js Jt Lh Li Lj Lu Lw Lx Ly Ma Mb Me Mf Mg Mh Mk Ml Mm Mp Mq Mr Mu Mv Mw My Mz Na Nb Nc Nd Nf Ng Nj Nl Nm Nn No Nq Nr Nu Nv Nw Nx Ny Oh Ok On Oz Pa Pb Pc Pd Pe Pg Po Qa Qc Qe) Iv(Et Fp Hq Hu Hw Hx Ii Ik Il Im Ip Ir Iu Jg Ji Jk Jl Jn Jo Jq Jr Js Jt Lh Li Lj Lu Lw Lx Ly Ma Mb Me Mf Mg Mh Mi Mj Mk Ml Mm Mp Mr Ms Mt Mu Mw My Mz Na Nd Ne Nf Ng Ni Nj Nl Nm No Nq Nr Nt Nu Nv Nw Nx Ny Of Oh Ok Om On Pb Pd Pf Pg Qa Qc Qe) Md(Fp Hq Hu Hw Hx Ii Ij Ik Il Im Ip Ir Iu Jg Jk Jl Jn Jo Jq Jr Js Jt Lh Li Lj Lu Lw Lx Ly Lz Ma Mb Me Mf Mg Mh Mj Mk Ml Mm Mp Mq Ms Mu Mw Mx My Na Nb Nc Nd Ne Nf Ng Nj Nl Nm No Nq Nr Nv Nw Nx Ny Of Oh Ok Oy Oz Pa Pb Pd Pe Pg Po Qa Qc Qe) Nh(Fp Hq Hu Hw Hx Ii Ik Il Im Ip Ir Iu Jg Jk Jl Jn Jo Jp Jq Jr Js Jt Lh Li Lj Lu Lx Ly Lz Ma Mb Me Mf Mg Mh Mj Mk Ml Mm Mn Mp Mq Mr Ms Mt Mu Mw My Na Nb Nc Nd Nf Ng Ni Nj Nl Nm Nq Nr Nt Nu Nv Nw Nx Ny Oh Ok Oz Pa Pb Pd Pe Pg Po Qa Qc Qe) Mn(Et Fp Hq Hu Hw Hx Ii Ik Il Im Ip Ir Iu Jg Jk Jl Jn Jo Jq Jr Js Jt Li Lj Lu Lx Ly Lz Ma Mb Me Mf Mg Mh Mk Ml Mm Mp Mq Mr Ms Mu Mw My Na Nb Nc Nd Ne Nf Ng Ni Nj Nl Nm No Nq Nr Nu Nv Nw Nx Ny Oh Ok Oz Pa Pb Pd Pe Pg Po Qa Qc Qe) Ns(Hq Hu Hw Hx Ii Ij Ik Il Im Io Ip Iu Jg Jl Jn Jo Jp Jq Jr Js Jt Li Lj Lu Lw Ly Lz Ma Mb Me Mf Mg Mh Mi Ml Mm Mp Mq Mr Ms Mu Mv Mw Mx Mz Na Nb Nc Nd Nf Ng Ni Nj Nk Nm Nn Nq Nr Nu Nw Ny Oe Of Oh Ok On Oy Pb Pc Pd Pg Qa Qc Qe) Pz(Fp Hq Hu Hw Hx Ii Ij Il Io Ip Iq Jk Jl Jn Jo Jq Jr Js Jt Lh Li Lj Lu Lx Ly Lz Ma Mb Me Mf Mh Mj Mk Ml Mm Mp Mq Ms Mw Mx My Na Nb Nc Nd Nf Ng Ni Nj Nk Nl Nm No Nq Nr Nv Nx Ny Oe Of Oh Oy Oz Pa Pb Pd Pe Pg Po Qa Qb Qc Qd Qe) Mt(aA Fp Fr Hq Hu Hw Hx Ii Ik Il Im Ip Ir Ji Jk Jl Jn Jo Jp Jq Jr Js Jt Lh Li Lj Lu Lw Lx Ly Lz Ma Mb Me Mf Mh Mk Ml Mm Mp Ms Mw My Mz Na Nb Nd Nf Ng Ni Nj Nk Nl Nm Nt Nu Nv Nx Ny Oh Ok Om Pb Pc Pd Pf Pg Po Qa Qc Qe) Iq(Et Fp Hq Hu Hw Hx Ii Ik Il Im Io Ip Ir Iu Jk Jl Jn Jo Jq Jr Js Jt Lh Lj Lu Lx Ly Lz Mb Me Mf Mi Mj Mk Ml Mm Mq Mr Mu My Na Nb Nc Ne Nf Ng Ni Nj Nk Nl Nm No Nq Nr Nv Nw Nx Ny Oe Ok Oz Pa Pb Pe Pg Po Qa Qc Qd Qe) Fr(Et Fp Hr Hw Ii Ik Il Ip Ir Jg Ji Jl Jn Jo Jq Jr Js Jt Lh Lj Lu Lw Lz Ma Mb Me Mf Mg Mh Mi Mj Mk Ml Mm Mp Mq Mr Ms Mu Mv Mw Mz Na Nb Nc Nd Nj Nl Nm Nt Nu Nv Nw Nx Ny Oh Ok Om On Pa Pb Pc Pd Pe Pf Pg Qc Qe) It(Fp Hq Hu Hw Hx Ii Ij Ik Il Im Io Ip Jg Ji Jl Jp Jr Js Li Lj Lu Lw Ly Lz Ma Mb Mg Mh Mi Mk Ml Mm Mp Mr Ms Mv Mw Mx My Mz Na Nb Nc Nd Nf Ng Nj Nk Nl Nn Nq Nr Nt Nu Nw Ny Oe Of Om On Oy Pb Pc Pd Pf Qc) Ji(Et Fp Hq Hu Hx Ii Ij Ik Il Im Io Ip Iu Jn Jo Jp Js Jt Lh Li Lj Lu Lx Ly Lz Mb Mf Mh Mi Mk Mr Ms Mv Mw My Mz Nb Nd Nf Ng Ni Nj Nq Nt Nu Nv Nx Ny Oe Of Oy Pa Pb Pc Pd Pf Pg Qa Qc Qe) Ih(Et Fp Hq Hw Ii Il Im Ip Jg Jk Jn Jo Jq Js Jt Lh Lj Lu Lx Ly Lz Ma Mb Me Mf Mg Mj Mk Ml Mm Mp Mq Mu Na Nb Nc Nf Nk Nl Nm Nn Nq Nr Nv Nw Nx Ny Ok Oz Pb Pg Po Qa Qc Qd Qe) No(Et Hu Hw Ii Ij Ik Il Io Ip Iu Jg Jn Jo Jr Li Lu Lw Lx Ly Ma Mb Me Mg Mm Mp Mr Ms Mu Mw Mx My Nd Nf Ng Nk Nm Nn Nq Nr Nu Nw Ny Oe Of Oh Ok Oy Pb Pc Pd Qb Qc) Pf(Fp Hq Hu Hw Hx Ii Ij Il Im Io Ir Iu Jk Jo Jp Js Lj Lw Lz Mh Mi Ml Mp Mr Ms Mv Mw Mx My Mz Nd Nf Ng Ni Nm Nn Nq Nt Nu Nv Ny Oe Of Om Pa Pb Pc Pg Po Qa Qc) Qb(Aa Fp Hq Hx Ii Im Ip Ir Iu Jk Jn Jo Jq Jr Js Jt Lh Lj Ly Mb Mf Mh Mj Mm Mq My Na Nb Nc Ne Nf Ni Nl Nm Nr Nv Nx Ny Ok Oz Pa Pb Pg Qc Qd Qe) Om(Hq Hu Hw Hx Ik Il Im Io Iu Jk Jo Jp Js Jt Lj Lu Lz Mb Mh Mi Ml Mr Mv Mw Mx My Mz Nd Nf Ng Ni Nj Nm Nq Nt Nu Nv Nx Ny Oe Pa Pb Pc Pd Pg Qc) Nt(Hq Hu Hw Hx Ii Im Io Ir Iu Jk Jo Jp Js Jt Lu Lz Me Mh Mi Mr Ms Mw Mx My Mz Nd Nf Ng Ni Nk Nm Nn Nq Nv Nx Ny Oe Oy Pa Pc Pd Pg Qa Qc) Nk(Hu Hw Hx Ij Ik Il Im Io Iu Jg Jp Jr Js Li Ma Me Mg Mi Mk Mm Mp Ms Mu Mw Mx Mz Nd Nf Ng Ni Nj Nl Nq Nr Nu

Figure 2 Continued

Me Mf Mg Mh Mi Mj Mn Mp Mq Mr Mu Mv Mw Mz Nb Nc Nf Nk Nl Nm Nn No Nq Nt Nu Ny Oe Og Oi Ok Oz Pa Pb Pd Pe Pg Po Pz Qb Qc) Jp(aA Hu Hv Hw Ii Ij Ik Il Im Iq Ir It Iu Jg Jl Jm Jo Jt Lh Li Lj Lu Lz Mb Mc Me Mf Mg Mh Mj Mk Ml Mn Mp Mq Mr Ms Mt Mv Mx My Mz Nd Nf Nh Ni Nj Nm Nn No Nq Nt Nu Ny Of Oh Ok Pb Pc Pd Pg Po Qb Qc) Jh(Et Hq Hu Hw Ih Ii Ij Ik Il Io It Iu Jg Jm Jr Js Lh Lj Lu Lw Lx Lz Mc Mg Mh Mj Ml Mn Mp Mr Ms Mv Mw Mx My Mz Nd Nf Nh Ni Nk Nn Nq Nt Nw Ny Oh Ok Pb Pc Pd Pf Pg Pz Qb) Mu(Hq Hu Hw Ih Ij Il Io Ir It Iu Jk Lu Lz Mc Mg Mm Mn Mr Ms Mt Mx My Mz Nd Nf Ng Nh Nq Nt Nu Nw Oe Of Og Oh Pd Pf Pz Qb) Lv(Et Hx Ih Ij Io Ip Ir It Iu Jm Jt Lu Lw Lx Lz Mb Me Mg Mh Mk Ml Mt Mx Mz Nc Nf Nh Ns Nu Ny Oe Of Oi Ok Pc Pd Pf Pz) In(aA Il Ip Jg Jk Jr Jt Lh Li Lx Md Mk Mp Ms Mw Nc Nd Nh Nn Nq Ns Nu Nv Oe Pc Pd Pg Po Qa) Hr(aA Hv Ih It Jq Md Mi Mj Ml Mp Mr Ms Mz Nd Ni Ns Nw Nx Ok Pf Qd) Mv(aA Hu Hv Ih Ij Io It Iu Lw Md Mz Nk Ns Nw Oe Of Og Oy) Pf(Hv Ih Iu Lj Lz Md Mh Ms Mt Mz Nd Nh Nk Ns Oe Og Ok Pe) Oi(Et Jg Jl Lw Lx Mg Mt Mz Nn Nt Oh Ok Qd) Jl(It Iu Lz Md Ns Of Oy Pz Qb) Mt(Ih It Lw Md Nd Nk Ns Oy) Nw(Ih Lu Md Ni Og Qb) Lw(aA Lu Mw Nk Og) Nk(Hv Jg Nn) aA(Mn Nn Pc) Md(Lx Ok) CoOy NqMy Hvlh PzOk} aA{Lv(Et Fp Hx Ih In Io Jh Jl Jn Jo Jq Js Jt Lu Lx Ly Mf Mg Mi Mk Mq Mr Mu My Na Nc Ng Nh Ni Nj Nk Nm No Nr Nu Nv Nx Og Oi Pa Pb Pe Pf Pz Qa Qb Qe) cX(Ad Af Aj Ar As aV AW aX Bb bE Bn bX Cq Cs Cw cZ Db Dc Dd dE dF Dg eF gP) bR(aE aF aI aN aS aU aX aY aZ bC bG bH bI cA cB cC cF cK cL Cx dB dC dG dH) dN(aE aI aK aU aX aY bA bG bO cB cD cF Ch cI cN cO Cx cY dH dL) bJ(aC aD aE aI aM aN bG bI bS cA cB cF Ch cK cM cR cU gL) Ma(Hr Hv Hx Jp Ly Me Mh Mn Ms Mt Ng Ns Nu Of Oh Wm) cl(aK aM aU aX bG bX cA cB cF cG cH cM cY dR gL gP) Mc(Hr Jg Jh Jp Jr Lw Lx Mf Mg Mm Mt Mv Nw Oh Po) In(Et Hr Hv Ip Jg Jh Mf Mi Mt Mv Nq Pc Pd Pf Po) bN(aD aM aN aY bF bI bW cA cB cC cF cM cO cR cU) cD(aI aU aY bA bC bH bL cF cL Co cU cW Cx cY) Mz(Jh Jr Li Mf Mg Mm Mn Mu Mv No Nq Pc Pf) Mu(Hu Hv Hx Lw Md Mh Nk Nq Ns Of Oy) Jr(Et Hr Jg Jp Mg Mt Mv Nk Nq Nw Pf) dK(aD aI aN bO cA cB cF cU dG gL) Lw(Jp Mb Mt Mw Nk No Nq Oi Pf) Mn(Hx Ih Jh Md Mp Nn Ns Oh Pf) bU(Af Ba Bb Bg bQ bX cM Cp De) Nw(Hr Md Mh Mv Nn No Ns Pf) Nn(Hx Md Ni Ns Oi Pf) bZ(aE aH Bo cF cR dH) Nq(Md My Ns Of Oy) Pf(Hv Ne No Ns Oi) Cx(aI Bc Bo) Wm(Mi Mt Oz) No(Jp Mm Mp) aF(eF fP gP) cC(cH eF gL) Mp(Jp Ni) Hr(Jq Ni) cH(bO cM) cR(cA cF) dR(bQ dF) CoDk CudM NsMt MgOi NkPc aHal aLeF cUdG} dN{cR(aC aD aE aG aI aM aN aP aR aW bB bC bI bJ bL bO bP bR bS bW cB cF cG cI cJ cL cN CO Cp cQ CU cV cZ dA dB dC dE dH dI dJ dL) bZ(aF aH aI aL aM aN aO aP aQ aS aW aX aZ bB bC bF bG bI bL bO bW cC cF cG cH cI cJ cL cN cO cV cZ dB dC dF dG dH dI dJ dL dM) Ba(aE aK aM An Ao AP aU aV aW Ax bH bJ bP bS bX cA cI cM cN cO Cs Ct Cx dB dI dJ dK dL) gP(aD aE aI aL aO aQ aS aW aY aZ bB bL bO bU bV cB cE cG cJ cL cP cU cW dB dC dG) bA(aE aG aJ aK aN aP aR aW aZ bC bI bM bW bX cC cI cJ cL cY dB dE dJ dL dM) cP(aF aI aK aO aV bF bJ bO bR bX cA cD cF cH cI cK cM cO cT cU cX cY De) bX(aI aK aL aU aV bF bN bO bU cII cM cO cW cX cY dD) al(aE aL aU aV bF bN bU bV cA cH cI cK dM) cT(aC aH aL Ao aQ Ax bB bP Cs cZ dE dF) dK(aJ aY bF bG cF cH cK cQ Cu cX) aX(aE aL aS aY bO cA cD cH cK) Cu(Af aW aZ bN cX Dl) aJ(bF bG cH cX dG) bV(bF bU cA cK) aP(cH cK dG) bH(bN bR cA) bG(bN cQ) bJ(aL aS) bU(cO cY) cH(cM cW) dR(bB cD) aZgL} In{Cu(Ad Af Aj Ap Ar As Aw Ba Bb Bg Bn Bo Ch Cw Dd Dg Dl Et Fp Hq Hr Hu Hv Hw Ih Il Im Io Ip Iq Ir Jh Jn Jo Jp Jr Jt Li Lj Lu Ly Ma Mh Mm Mp Mq Mv My Na Ne Ng Ni Nm No Nr Nt Nw Oe Og Oi Pc Pf Po Qa Qb Qd) Mt(Ad Al An Ao Ax Bb Bo Cs Cv Cw Db Dd Di Dk Dl Fp Hq Hr Hw Ih Im Io Ip Ir It Jh Jm Jp Js Lj Ly Lz Mc Me Mg Mj Mk Ml Mm Mn Mq Mu Mv Mw Mx Na Nb Nc Nd Ne Nl Nn Nq Nt Nw Of Og Oh Oy Oz Pb Pd Pf Po Pz) Nw(Hv Ir Jh Jr Lu Ma Md Mg Mi Mn Mp Ms Mv Nh Nn Ns Nt Og Oh Pd Pf Pz) Mg(Cp Hv Ir Jl Jp Jr Mp Mr Mu Mw Mz Ns Pa Pc Pe Wm) Mp(Bc Hq Iu Jn Jp Js Lw Mi Nd No Nt Nu Ok Pe) Hv(Bc Cw Et Jg Jh Jl Jp Lh Li Mu Nx Ok Pf Qa) Nt(Bc Jh Jl Jp Jr Lx Mj Ms Mu Mz Nh Oh) Ok(Hr Ir Iu Jh Ma Md Nu Of Oh Pz) Bc(Cv Li Mk Mv Nn Nu Pd Qd) Jr(Jh Jp Ms Mu Mw Nn Nq Nu) Nu(Cw Di Jh Jn Li Qa) Nh(Cw Lx Mv Po Qa Wm) Jp(Li Lw Mi Mu Nn) Pd(Al Cv Dc Dd) Wm(Et Jh Mm) Lw(Ap Cv Oh) Mu(Jn Ly Nc) Nn(Jn Js) Md(Lx Nm) CoOy CwNc NsMw IqQa JhOh} Mt{Oi(An Ao Ba Bo Cq Dc Dg Dk Hr Hu Ir Jh Jp Jr Jt Md Mg Mi Mp Ms Mu Mv Nn Ns Nt Nu Nw Oh) Ns(Hr Hu Hv Ij Io Iq It Jh Jp Jr Lw Md Mi Mn Mp Mu Nb Ng Nn Nu Nw Ny Of Qb) Md(Hr Io Iq It Jh Jp Jq Jr Lw Lx Mi Mn Mp Mu Nl Nn Nu Nw Of Oz Pb Wm) Mc(Ba Cq Di Hr Hu Ij Jh Jr Lw Mi Mp Mu My Nb Ng Nn Nu Ny Of Qb) Nk(Ad Aj Al An Ba Bb Bc Cq Cs Ct Cu Cv Db Dc Dd Dk Dl Jl) Mu(Hu Hv Ih Il Io Iq Jk Jm Jn Lw My Ng Nq Of Oy Pz Qb) Jh(Hr Hv Ih Ir Jn Jr Ng Nu Of Oh Pz) Jn(Hr Hu Hw Ij It Lw Mx My Nq Oy) Ih(Ba Cu Hu Ir Jr Lh Lw Mi Ok) Ni(Hv Lw Mp Nw Oh Ok Wm) Hu(Ij Lw Mi Mx Nq Nu Pz) Oy(Bc Bg Cs Cu Pf) Pz(Ij Mi My Nw) Cu(Dc No Nv) Wm(Mi Nb Nd) Hr(Mr Nw Qd) Lv(Hv Nw) Ij(Mi Nu) Cslr NrPf LwOg MhHv MvNg NbHx} eF{aE(aC aD aF aH aI aN aR aX aZ bC bF bL bO bQ bV bW bZ cF cG cK cO cU cW dB dD dH dI dK dL) bU(aD aF aL aW aY bH bJ bL bQ bR cE cN cP cR cU cX dA dC dK dL) cD(aH aN aW bN bP bR bZ cA cF cK cN cT cV cX dG dI dK dM) dF(aC aG aK aL aQ aY bC bF bL bP bS cA cB cK cN cW cY dC) aG(aC aS aU bH bN cA cF cK cU cX cZ dG dI dK dR) aN(aD aF aH aS bF bJ bO bQ bS bW cU dG dK) bR(aF aL bE bF bJ bN bO bQ cC cE cH cU dK) aD(aL aS aY bB bF bO cC dC dG dK) bQ(bC bH bL bN bW cH cO cV) cC(aH bA bL bN cP cW dC dM) aF(aQ bF bN bO cE cH cR) aH(bB bE bL bZ cU dL) aL(aW bA bN cT cW) dK(bF cE cQ cR cV) bE(aY bO cW cX) bF(bN cU) cH(aW bO) aJdG cEcF} Ba{bU(Af aH An Ao aR bA bE Bg bI bM bZ cB cF cG cJ cK cM cN CQ Ct CW De dH Di dK dL) cH(aH Aj AN Ao aQ Ax Bc bF Bg bP cE Ch cK Cp Cq Cs Cw dA Dc dF DG dI dJ Dk) cD(aE aK aM AN Ap aR As aV Aw bJ bO cF cG cL cM cU cV Cx Db dE Di dK) cX(aD aE aI aN Ar Bc BN bR cB cC cF Co cU Cx De dM) Bo(aM aU aX bB bF bG bO cA cG cO Cu dM) bN(aD aI As bO bR cC Co Cp CU dB dE) cl(aM Aw bJ bS cA cG cR Cs Ct dE) Cu(aH aW bJ bR dB Dc dM Ih No) As(bR bS cA cK dE dG) dB(Bg bZ Ch Co De) dM(bO Cp cR dH) Bg(bE bJ) Mc(Mg Nh) al(bQ cC) bZ(aZ Dk) cR(aW bR) ChbJ CocT DbcB LwNi MgOi aLbG cCcU} bA{cD(aE aF aI aN aP aR aZ BB bC bG bI bM bS bV cA cG cI cK cL cW cY dA dB dC dE dG dH gP) bU(aC Ao aV Aw Ax Bc BG bI Bo cC cE Ch cJ cM Cq Cs cY cZ dA dF dL) cI(Ad aV aX bC bG bM bS cA cC cF cK cM cU cW cY dA De gL) cH(aL aS bB bJ bN bS cF cK cV cX dA dH dJ) bZ(aD aE aF aH bS bX cF cL cX dF dG dl) bJ(aC aI aY bF bG cB cF dC dK fP) Co(aD Aj aZ bN bR cC DB) bR(aE bH bL bO cB cC cF) cR(aD aE aF aN aY Bo cF) cX(aD aI aX Bb cB cC dK) bN(aB aN cB cC Cp) bO(aD cB cC cF dK) dK(bF cE cF cP) cU(aY cM dl) aF(bF gP) aH(al Cu) cC(aD Bg) BocO DedB aEal bBcF} Cu{Dk(AD AN aP aQ As aU aV bF bJ bL Bn bP bQ bS bZ cD cE cI cJ cM cO Cq cV Cw cY cZ dB Dc Dd dE dF dI dJ dL Jh) Mc(Af Ap Aw Bc Bo Ch Cs Dd Dl Il Im Iq Jp Lh Lx Me Mj Ml Mm Mn Nr Nx Pc Pf Pg Qd) No(Dd Ii Ij Jo Jq Js Mx Nd Nv Pg Pz) aW(aH Aj bN Bo bU cI cR cT cX) Nk(Bb Cq Ii Jm Nd Of Oi Oy) Ih(Cq Jm Ms Mx Nd Nv Ny Oy) Oi(Al Hx Jm Md Mx Nv Of) Nn(Cq Hx Md Ny Of) bQ(Af Aj aX cT Dl) Dc(Bo cA Cx Nu) aH(bN bR cT cX) cI(aZ cM cP cQ) Oy(Co Mu Nu) cP(aU Cs dK) cT(bN bR Cs) Aj(bJ dK) Bo(Af aX) Hx(Nd Nu) Pz(Mi Mv) Nv(Jl Lv) cQ(bN Cx) CtEf MrHr aXcX bZcE} Jh{Hv(Hu Ih Ir Iu Jl Jp Jr Lv Md Mh Mz Ng Nk Ns Nt Nu Nw Of Oh Oi Oy Pf) Mc(Hr Hu Jl Jn Jp Lx Md Mz Nc Ng Nh Ns Nt Nu Nw Ok Pf Qa Qe) Nw(Hr Ih Io Ir Iu Jr Lu Mn Nh Ni Nm No Ns Nu Oe Og) Oh(Hu Ih Jr Md Mr Ng Nh Ni Nk No Ns Nu Oe Of Oy) Jl(Hr Ir Md Nk Ns Nu Of Oi Oy Pz) Jr(Hr Ih Md Ms Mz Nd Nh Ns Nu Pf) Nu(Hr Hu Ir Ng Ns Oi Ok) Oi(Ir Jp Mg Mz Na Nt) Ok(Hr Ni No Ns Of Pz) Oy(Co Mk Nb Pa Pe Pf) Md(Jn Jp Lx Nt Pf) Ns(Ir Jp Nt Pf) Hr(Mr Mz Qa Qd) Wm(Mr Ng) Nh(Ir Mz) PzJp OfPf} cP{bZ(aC aD aF aI aJ aK aM An aO aP aQ aR aU aV AX aZ bC bF bH bL bM Bn bS bV bW cA cC cG cH cJ cL cN cO cR Cs cU cV cW cY dA DB dC dD DE dG dH dI dJ Dk dL) Co(aD Aj aK AL aM aN aO AR aS aV Aw aX bL Bn cE cK cL cN Cp cR Cw cY cZ DB Dc Dd De Dg dJ Dk Dl) dK(al aU aY bE bF BG bH bN bO cB cD CH cI cO cT cU Cx De dR gL) De(Af aR aW aY bO cA Ch Cs) bU(aJ aP bE cO) cO(cD Ch Cx) aF(aO gL) bE(Bg Ch) CxaU aXbR cGcI} cT{bN(aG aH aI aJ aK AO aP aQ Aw aX aZ bC bE bM bQ bV bW cA cC cG cK cN cV cW dB De dH dI dL) cD(aD aE aF aV aY Bg bI bV bW

Figure 2 Continued cA Ch cK cL cM cV cW) cI(aK aN aO aV bL bW cA cK cL cM Cp dD) bZ(aE aF aG aL aN bJ bR bX dF DK) cU(aD aE aH aY bJ bO cA cC cK dC) dK(aM bG bN bO bR cF cH cR cX) aD(aF bN bR CO cR cX) Co(aH Cs Dg Dk dM) bJ(aE aY bO bR) bN(bO cH Cp cX) cC(bF bG bL cX) aF(aI bF gP) cB(aE aH cX) Bo(Aw cO) Cp(cH Cs) bR(cR cX) BcCx aYcR bOcF} Mu{Hv(Ih Iu Jm Mc Md Mh Mv Ng Nk No Ns Oh Oy) Pz(Et Jn Jp Lw Mg Nm No Nt Nu Nw Pd) Nu(Hu Ij Jk Lw Mc My Ny Of Oy) Jn(Ih Ij Jm Md Ns Oy Pc Qb) Lw(Hx Ih Jm Mb Oi Pg) Mr(Hr My Ns Oy Pg Wm) Ih(Jp Jr Mg Nc Pd) Nq(Hr Ir Jp Oh) Oi(Mg Nt Nw Pf) Ly(Hr Md Pc) Mc(Jp Mp Oz) Jm(Mg Nc Pd) No(Jp Pc) Nk(Nc Nt) CoOy NhPc IqOh} Nw{Ni(Hv Ir Iu Md Nc Nh Nm Ns Og Oh Oi Pc Pf Pz) Hr(Hv Ih Ik Io Lu Ma Mc Md Mn Mr Nh Nk No Ns) Oi(Hv Lu Lv Ma Md Mi Mp Nn Ns Nt Oh Pd Wm) Lv(Hv Ir Iu Md Mn Nh Nk Ns Pz) Lu(Hv Ir Mc Md Nh No Ns) Mv(Md Nh Nk No Nr Ns) Ir(Io Ma Mc Ml Pz) Pz(Jl Ma Nt Pf) Md(Mc Og)} bU{aX(aG aI aJ aM aW Bb bL bX Co cQ cR cX cZ Db Dg dM) aJ(aD aE aI bE bF bG bJ bL bS cF cK cO dK) dI(aG aP aS aY cR cW cZ dA dK) aP(aY bH bZ cF cR cX dG) bZ(aE cE cQ) aY(bE dK) bEgP bHdA cIgL cRdK} Oi{Pf(Et Ir Jp Js Md Mm Mp Ms Mz Na Nk Nn Ns Nt Nu Of Oh Oy Wm) Nt(Hr Jp Mv Mz Oh) Mg(Af Dd Ir Jl Mv) Wm(Jt Mi Qd) Lw(Ir Jp Oh) Mv(Et Hv Ok) Hr(Hv Jl Ok) LxMd} Oy{Co(Af Bc Bo Ct Db Dd Dg Hq Hr Hx Ih Ij Jg Jl Lw Ly Md Mh Mi Mk Mr Ms Mv Mw Nc Nh Nq Ns Nt Nv Oh Pd) Mv(Ad Hv Mp Mr) BcMa MgNb} bZ{cE(aD aI aP aS bJ cX dK dL) dK(bR bX cC cD cI cR) bQ(aE bV bX cR cW) cQ(aH bX cA cC) aE(bJ bX cC) cI(bX cM) ArDk BocR aHaI aXcD cCcW} Hv{Mv(Hu Ih Ir It Jm Lj Lv Lw Mc Md Ml Ni Oe Of Og) Lv(It Iu Jp Md Ml Mp Ms Nk) Nk(Jg Jl Pf) Md(Lx Pf) NqIr LuLw MpNi HrJp} Jl{Nk(Ir Jm Lw Md Mg Mp Mv Nc Nn Ns Nt Of Oh Pf) Wm(It Jm Lw Mg Ml Mx Nb Of) MgPz} aX{cD(aD aM aS aY bR bX cZ) Bo(aI bR bX cZ dD) cI(aD aI bX gL) aD(bX dK) cX(Bc Cx) aEbR} Jn{Nq(Hu Ij Mc Md My Ns Pc) Mc(Md Mq Mw Nb Nu) Md(Lx Mv Nn) Ns(Mv Nn) Mi(Hr Hw) LwMw} Lv{Jp(Ir Md Nh Nk) Hr(Js Mp Mz) Wm(Mp Nu) Nh(Mz Oh) MdJs NkOh PzOk} bR{aP(bF bJ cF cK cR cU cX) aJ(bJ bN cD dK) dK(aY dH) cIgL} Mc{Lx(Mi Mp Nb Ns) Nn(Md Ns) Mp(Ir Mv) Jr(Mw Nq) CwMv MiJp HrQd} Ni{Oh(Jp Md Mp No Ns) Hr(Jp Jq Ok) Lx(Hq Md) Js(Mp Pc)} bE{gP(aD aY bO cE cM cW cX) gL(aN aW) BgdD aEdR} Wm{Nb(Md Mg Mi Ml Mx) Mr(Mp Nn Nq Pc) MiNd} aJ{bN(aD cD cH cR cX) cX(cD cI cR) cDcR} Mv{Of(Bc Nb Ok) Ng(Mg Nm) BcJk MpIj} dK{cR(aY bX cN) Ar(Bg Ch) aI(cI dA)} Lw{Dd(Co Ma Nq) Mw(Ih Og) CoIi} Md{Lx(Io Jm Nh Nu Og) NuJp} cI{gL(aI bO cC cX) aIaP} Bc{Ef(Cs Ct) Nq(Ao Pz)} Mr{Hr(Cx Di Jp) CsIu} Ir{Nu(Ml Nn) Nb(Ml Ns)} Co{AjcQ DgaP NcNk} Ih{Jr(Mw Nn Nq)} Pz{Mi(Jp Ok) NnOk} Ct{Ef(Bo Dk)} cR{BgDk CpcX} NsNuJp MgOgOk

Unconstrained panels with 3 analytes, where 9.4E-6 >= 'AUC p-value' > 1.0E-6. Contains 27,789 panels of 939,239 total panels evaluated. : Ji{Ma(Et Fp Hq Hu Hw Hx Ii Ij Ik Il Im Io Ip Is Iu Jg Jk Jl Jm Jn Jo Jp Jr Js Jt Lh Li Lj Lu Lv Lx Ly Lz Me Mf Mg Mh Mi Mj Mk Ml Mm Mp Mq Mr Ms Mt Mu Mv Mw My Mz Na Nb Nc Nd Ne Nf Ng Ni Nj Nk Nl Nm Nn Nq Nr Nt Nu Nv Nw Nx Ny Oe Of Oh Ok Om On Oy Oz Pa Pb Pc Pd Pe Pf Pg Po Qa Qb Qc Qd Qe Wm) Nu(aA Et Fp Hq Hu Hw Hx Ii Ij Ik Il Im Io Ip Iq Ir It Iu Jg Jk Jl Jm Jn Jo Jp Jq Js Jt Lh Li Lj Lv Lw Lx Ly Lz Mb Me Mf Mh Mi Mj Mk Ml Mm Mn Mp Mq Mr Mt Mu Mv Mw Mx My Mz Na Nb Nc Nd Ne Ng Nh Ni Nj Nl Nn Nq Nr Nt Nv Nw Nx Ny Oe Of Oh Ok Om On Oy Oz Pa Pb Pc Pd Pe Pf Pg Po Qa Qc Qe) Nj(aA Et Fp Hq Hu Hw Hx Ii Ij Ik Il Im Io Ip Iq Ir It Iu Jg Jk Jl Jm Jn Jo Jp Jq Jr Js Jt Lh Li Lj Lv Lw Lx Ly Lz Mb Me Mf Mh Mi Mj Mk Ml Mm Mn Mp Mq Mr Mt Mu Mv Mw My Mz Nb Nc Nd Ne Nf Ng Nh Ni Nk Nl Nm Nn Nq Nr Nt Nv Nw Nx Ny Oe Of Oh Ok Om On Oy Pa Pb Pc Pd Pf Pg Pz Qa Qc Qe) Lj(aA Et Fp Hq Hu Hw Hx Ii Ij Ik Il Im Io Ip Iq Ir It Iu Jg Jl Jm Jo Jp Jr Jt Lh Li Lv Lw Lz Mb Me Mf Mh Mi Mj Mk Mm Mn Mp Mq Mr Mt Mu Mv Mw Mx My Mz Na Nb Nc Nd Ne Ng Nh Ni Nk Nl Nm Nn Nq Nr Nt Nv Nw Nx Ny Oe Of Oh Ok Om On Oy Oz Pa Pb Pc Pd Pe Pf Pg Pz Qb Qc Qd Qe) Oe(aA Et Fp Hq Hu Hw Hx Ii Ij Ik Im Io Ip Iq Ir It Iu Jg Jk Jl Jm Jo Jp Jr Js Jt Lh Li Lv Lw Lx Lz Mb Md Me Mf Mh Mi Mj Mk Mm Mn Mp Mq Mr Ms Mu Mw My Mz Na Nb Nc Nd Ng Nh Nk Nl Nn Nq Nr Nt Nv Nw Nx Ny Of Og Oh Ok Om On Oy Oz Pa Pb Pc Pd Pe Pf Pg Pz Qa Qb Qc Qd Wm) Hx(Et Fp Hq Hu Hw Ih Ii Ij Ik Il Im Io Ip Iq Ir It Iu Jg Jk Jm Jo Jr Jt Li Lv Lw Lx Ly Lz Mb Md Me Mf Mh Mi Mj Mk Ml Mm Mn Mp Mq Mt Mu Mx My Mz Na Nb Nc Nd Ne Ng Nh Ni Nk Nl Nm Nn Nq Nr Ns Nt Nv Nw Nx Of Oh Ok Om On Oy Oz Pa Pc Pd Pe Pg Po Pz Qa Qb Qc Qd Qe) Nx(aA Et Fp Hq Hu Hw Ii Ij Ik Im Io Ip Iq It Iu Jg Jk Jl Jm Jn Jo Jp Jr Js Jt Lh Li Lw Lx Ly Lz Mf Mh Mi Mj Mk Ml Mm Mn Mp Mr Ms Mu Mv Mw Mx My Mz Na Nb Nc Nd Ne Ng Nh Nk Nl Nn Nq Nr Nt Nw Ny Of Og Oh Ok Om On Oy Oz Pa Pb Pc Pd Pe Pg Po Pz Qa Qb Qc Qd Qe) Ii(aA Ba Co Cu Et Fp Hq Hu Hw Ik Il Im Io Ip Iq It Jg Jk Jl Jo Jp Jr Jt Lh Li Lv Lw Lx Lz Mb Md Me Mf Mh Mi Mj Mk Mm Mn Mp Mr Ms Mu Mx My Mz Na Nb Nc Nd Ng Nh Ni Nk Nl Nn Nq Nr Ns Nt Nv Nw Ny Of Oh Ok Om On Oy Oz Pa Pc Pd Pe Pg Po Pz Qa Qb Qc Qd Qe) Ik(aA Et Fp Hq Hu Hw Ih Ij Il Im Io Ip Iq Ir It Iu Jg Jk Jl Jm Jn Jo Jp Js Jt Lh Li Lv Lw Lx Ly Lz Me Mf Mh Mi Mj Mk Ml Mm Mn Mp Mr Mt Mu Mv Mw My Nb Nc Nf Ng Nh Ni Nk Nl Nm Nn Nq Nr Nt Nv Nw Ny Of Oh Ok Om On Oy Pb Pc Pd Pe Pf Pg Po Qa Qc Qd Qe) Io(Et Fp Hq Hu Hw Ij Im Ip Iq It Iu Jg Jk Jl Jm Jo Jr Js Jt Lh Li Lw Lx Ly Lz Mb Me Mf Mg Mh Mi Mj Mk Ml Mm Mn Mp Mq Mr Mu Mx My Mz Na Nb Nc Nd Ne Ng Nh Nk Nl Nm Nn Nq Nr Nt Nv Nw Ny Of Oh Ok Om On Oy Oz Pa Pb Pc Pd Pe Pg Po Pz Qa Qb Qc Qd Qe) Fp(aA Et Hq Hu Hw Ij Il Im Ip Iq Ir It Iu Jg Jk Jl Jm Jo Jp Jr Jt Lh Li Lw Lz Mb Md Mf Mh Mi Mj Mk Mm Mn Mp Mq Mr Mt Mu Mv Mw Mx My Mz Na Nb Nc Nd Ng Nh Nk Nl Nm Nn Nq Nr Nt Nv Nw Ny Of Oh Ok Om On Oy Oz Pa Pb Pc Pd Pe Pg Pz Qb Qc Qd Qe) Hu(aA Et Hq Hw Il Im Ip Iq Ir It Iu Jg Jk Jl Jm Jn Jo Jp Jq Jr Js Jt Lh Li Lw Lz Mb Me Mf Mg Mh Mi Mj Mk Ml Mm Mn Mp Mq Mr Mu My Mz Na Nb Nc Nd Nf Ng Nh Nk Nl Nm Nn Nq Nr Nt Nv Nw Ny Of Oh Ok Om Oy Oz Pa Pb Pc Pd Pe Pf Pg Pz Qa Qc Qd) Mh(Et Hq Hw Ij Il Im Ip Iq It Jg Jk Jl Jm Jo Jq Jr Js Jt Lh Li Lv Lw Lx Ly Lz Mb Me Mf Mg Mi Mj Mk Mm Mp Mq Mu Mv My Mz Na Nb Nc Nd Ne Nf Ng Nl Nm Nn Nq Nr Nt Nv Nw Ny Of Oh Ok Om On Oy Pa Pb Pc Pd Pe Pf Pg Po Pz Qa Qc Qd Qe Wm) Mu(Et Hq Hw Ij Il Im Ip Ir Is It Iu Jg Jk Jl Jn Jo Jp Jr Js Jt Lh Li Lu Lv Lw Lx Ly Lz Mb Me Mf Mg Mi Mj Mk Ml Mm Mp Mq Mr Mt Mv Mw My Mz Na Nb Nc Nd Ng Ni Nl Nm Nt Nv Nw Ny Oh Ok Om On Oy Oz Pa Pb Pc Pd Pe Pf Pg Po Qa Qc Qe) Nr(aA Et Hq Hw Ij Im Ip Iq Ir It Iu Jg Jk Jm Jo Jr Jt Lh Li Lw Lx Ly Lz Mb Me Mf Mg Mi Mj Mk Ml Mm Mn Mp Mq Mr My Mz Na Nb Nc Nd Ne Ng Nh Nk Nl Nm Nn Nq Nt Nv Nw Ny Of Oh Ok Oy Oz Pa Pb Pc Pd Pe Pg Po Pz Qa Qb Qc Qd Qe Wm) Il(Et Hq Hw Ij Im Ip Ir It Iu Jg Jk Jl Jn Jo Jp Jr Js Jt Lh Li Lv Lw Lx Ly Lz Mb Me Mf Mg Mi Mj Mk Ml Mm Mp Mq Mr Mv Mw My Mz Na Nb Nc Nd Ne Ng Nl Nm Nn Nq Nt Nv Nw Ny Oh Ok Om On Oz Pb Pc Pd Pe Pf Pg Po Qa Qc Qd Qe Wm) Of(aA Et Hq Hw Ij Im Ip Iq It Jg Jk Jl Jm Jn Jo Jq Jr Js Jt Lh Li Lw Lx Ly Lz Mb Me Mf Mg Mi Mj Mk Mm Mn Mp Mq Mr My Mz Na Nb Nc Nd Ne Nf Ng Nh Nk Nl Nm Nn Nq Nt Nv Nw Ny Og Oh Ok Oy Oz Pa Pc Pd Pe Pg Po Pz Qa Qc Qd Qe) Ip(aA Et Hq Hw Ij Im Iq Ir It Iu Jk Jl Jm Jn Jo Jp Jq Jr Js Jt Lh Li Lv Lw Lz Mb Me Mi Mj Mk Ml Mm Mn Mr Ms Mt Mv Mw My Mz Na Nb Nd Nf Ng Nh Ni Nk Nl Nm Nn Nq Nt Nv Nw Ny Oh Ok Om On Oy Pa Pb Pc Pd Pf Pg Pz Qb Qc) Oy(aA Co Et Hq Hw Ij Im Iq It Jg Jl Jm Jn Jo Jq Jr Js Jt Lh Li Lw Lx Ly Lz Mb Me Mf Mg Mi Mj Ml Mm Mn Mp Mq Mr Mx My Mz Na Nc Nd Ne Ng Nk Nl Nm Nn Nq Nt Nv Nw Ny Oh Ok Oz Pa Pb Pc Pd Pe Pg Po Pz Qa Qc Qd Qe Wm) Nb(aA Et Hq Ij Im Iq Ir It Iu Jg Jk Jm Jn Jo Jp Jr Jt Lh Li Lx Ly Lz Mb Mf Mi Mj Mk Ml Mm Mn Mp Mq Mr Mt Mv Mw My Nc Nd Ne Ng Nh Nk Nl Nm Nn Nq Nt Nv Nw Oh Ok Om On Oz Pa Pb Pc Pd Pe Pf Pg Po Qb Qc Qd Qe) Nd(Et Hq Hw Ij Im It Jg Jk Jl Jm Jn Jo Jp Jq Jr Js Jt Lh Li Lw Lx Ly Lz Mb Me Mf Mg Mi Mj Mk Ml Mm Mq Mv Mw My Mz Na Nc Ne Nf Ng Nl Nm Nn Nq Nt Nv Nw Ny Oh Ok Om On Oz Pa Pb Pc Pd Pe Pg Po Qa Qc Qd Qe) Iq(aA Et Hq Ij Im It Iu Jg Jk Jl Jm Jo Jr Jt Lh Li Lw Lx Ly Lz Mb Me Mf Mg Mi Mj Mk Ml Mm Mp Mq Mr Mx My Mz Na Nc Ne Ng Nk Nl Nm Nn Nq Nt Nv Nw Ny Oh Ok Om On Oz Pa Pc Pd Pe Pg Po Pz Qa Qb Qc Qd Qe) Mn(aA Et Hq Hw Ij Im It Jg Jk Jl

Figure 2 Continued

Jm Jn Jo Js Jt Lh Li Lw Lx Ly Lz Mb Me Mf Mg Mi Mj Mk Ml Mm Mp Mq Mr Mx My Mz Na Nc Ne Ng Nh Nl Nm Nn Nq Nt Nv Nw Ny Oh Ok Oz Pa Pb Pc Pd Pe Pg Po Qa Qc Qd Qe Wm) Nq(Et Hq Hw Ij Im Ir It Iu Jk Jl Jm Jo Jp Jq Jt Lh Li Lv Lw Lx Lz Mb Me Mf Mi Mj Mk Ml Mm Mr Mt Mw Mx My Mz Na Nc Ng Nh Nk Nl Nm Nt Nv Nw Ny Oh Ok Om On Pa Pc Pd Pf Pg Po Pz Qa Qb Qc Qe Wm) Qc(aA Et Hq Hw Ij Im Ir It Iu Jg Jk Jl Jo Jp Jr Jt Lh Li Lw Lz Mb Md Me Mf Mi Mj Mk Mm Mr Ms Mv Mw Mx My Na Nc Ng Nh Ni Nk Nl Nn Ns Nt Nv Nw Oh Ok Om On Oz Pa Pb Pc Pd Pe Pg Pz Qb Qd Qe) Lv(Hq Hw Ij Im Jg Jk Jl Jm Jn Jo Jr Js Jt Lh Li Lw Lx Ly Lz Mb Me Mf Mg Mi Mj Mk Mm Mp Mq Mr Mx My Mz Na Nc Ne Nf Ng Nl Nm Nn Nt Nv Nw Ny Ok Om On Oz Pa Pb Pc Pd Pe Pg Po Qa Qd Qe) My(aA Et Hq Hw Ij Im Ir It Iu Jg Jk Jl Jm Jn Jo Jp Jr Jt Lh Li Lz Mb Md Mf Mi Mj Ml Mm Mr Mx Mz Nc Ng Nh Nk Nl Nm Nn Ns Nt Nv Nw Ny Oh Ok Om On Pb Pc Pd Pf Pg Po Pz Qb Qd Wm) Jp(aA Et Hq Im Jg Jk Jl Jm Jo Jt Lh Li Lw Lx Ly Lz Mb Me Mf Mg Mi Mj Mk Ml Mm Mp Mq Mr Mt Mv Mw Na Nc Ne Ng Nl Nm Nn Nt Nv Nw Oh Ok On Oz Pa Pc Pd Pe Pf Pg Po Qa Qd Qe Wm) Nh(Et Hq Hw Im Jg Jk Jl Jm Jn Jo Jr Js Jt Lh Li Lw Lx Ly Lz Mb Me Mf Mg Mi Mj Mk Ml Mm Mp Mq Mr Mz Na Nc Ne Nf Ng Nk Nl Nm Nn Nv Nw Ny Ok On Oz Pa Pb Pc Pd Pe Pg Po Qa Qd Qe) It(Et Hq Hv Hw Ij Im Jg Jh Jk Jm Jn Jr Js Lh Li Lw Ly Lz Mb Me Mf Mi Mj Mk Ml Mm Mp Mq Mr Mx Mz Na Nc Ne Nf Ng Nk Nl Nm Nn Nv Nw Ny Ok Om On Pa Pb Pc Pd Pe Pz Qa Wm) aA(Et Hq Hv Hw Ij Im Ir Jg Jk Jl Jm Jo Jt Lh Li Lw Lx Ly Mb Me Mf Mg Mi Mj Mk Ml Mm Mp Mq Mr Mt Mz Na Nc Ng Nl Nm Nt Nv Nw Ny Ok Om On Pa Pb Pd Pe Pg Po Qa Qd Qe) Pc(Et Hq Hw Ij Im Iu Jg Jk Jl Jn Jo Jq Jt Lh Li Lw Lx Ly Lz Mb Md Me Mf Mi Mj Mk Ml Mm Mr Mt Mv Mw Mx Na Nc Ne Ng Nl Nn Nt Nv Nw Ny Oh Ok Om On Pb Pd Pf Pg Po Pz) Ns(Et Hq Hw Im Jg Jk Jm Jn Jo Jq Js Jt Lh Li Lw Lx Ly Lz Mb Me Mf Mg Mi Mj Mk Mm Mp Mq Mz Nc Ne Nf Ng Nl Nm Nn Nv Nw Ny Ok Oz Pa Pb Pd Pe Pg Po Qa Qd Qe Wm) Pz(Et Hq Hw Ij Im Jg Jm Jn Jo Jr Js Jt Lh Li Lw Lx Ly Lz Mb Me Mf Mg Mi Mk Ml Mm Mp Mq Mx Mz Na Nc Ne Ng Nl Nm Nn Nt Nv Nw Ny Oz Pa Pb Pd Pe Pg Po Qa Qb Qe) Oh(Et Hq Im Ir Is Iu Jg Jk Jl Jm Jo Jt Lh Lw Lx Ly Lz Mb Me Mf Mj Mk Ml Mm Mp Mq Mr Mt Mv Mw Mz Na Nc Ne Ng Nl Nm Nn Nt Nv Nw Ok Om On Pd Pe Pf Pg Po Qa Qe) Om(Et Hq Hw Ij Im Is Iv Jm Jn Jo Jr Js Jt Lh Li Lw Lx Ly Lz Mb Me Mf Mg Mj Mk Ml Mm Mp Mq Mr Mz Na Nc Ne Nf Ng Nl Nm Nn Nv Nw Ny Oz Pb Pd Pf Pg Po Qa Qe) On(Et Hq Hw Im Is Iu Jg Jk Jl Jm Jo Jt Lh Li Lw Lx Lz Mb Me Mf Mi Mj Mk Ml Mm Mp Mq Mr Mt Mv Mw Na Nc Nl Nm Nt Nw Ok Oz Pa Pb Pd Pe Pf Pg Po Qa Qe) Lz(Et Hq Hw Ij Im Ir Iu Jk Jl Jn Jo Jq Jr Lh Li Mb Mi Mj Mk Ml Mr Mt Mv Mw Mx Na Nc Ng Ni Nk Nl Nn Nt Nv Nw Ny Ok Oz Pa Pb Pd Pe Pf Pg Qb Qd) Mv(Et Hq Jg Jk Jl Jo Jt Lh Li Lw Lx Ly Mb Me Mf Mg Mi Mj Mk Mm Mp Mq Mr Mt Mw Na Nc Ne Nl Nm Nt Nv Nw Ok Oz Pa Pd Pe Pf Pg Po Qa Qd Qe) Ng(Et Hq Hw Im Ir Iu Jk Jl Jo Jr Js Jt Lh Li Lw Mb Md Me Mf Mi Mj Mk Mm Mp Ms Mt Mx Mz Na Nc Nk Nl Nm Nn Nw Ny Og Ok Pd Pg Qb Qd Qe Wm) Ij(Et Hq Hv Jg Jh Jk Jl Jm Jn Jq Jr Js Lh Li Lw Ly Mb Me Mf Mg Mi Mk Mm Mp Mq Mr Mx Mz Nc Ne Nf Nk Nl Nm Nn Ny Ok Pa Pb Pd Pe Po Qb) Pf(Hq Hw Jg Jk Jl Jn Jo Jr Js Jt Lh Lw Lx Ly Mb Me Mf Mg Mi Mj Mk Ml Mm Mp Mq Mr Mt Mz Na Nc Ne Nl Nm Nt Nw Ok Oz Pb Pd Qa Qd Qe Wm) Mw(Et Hq Jl Jm Jo Jt Lh Li Lw Lx Ly Mb Me Mf Mg Mi Mj Mk Mm Mp Mq Na Nc Ne Nl Nm Nt Nv Nw Ok Oz Pa Pe Pg Po Qa Qd Qe Wm) Qb(Et Hq Hw Im Jg Jm Jn Jo Jq Js Jt Lh Li Lw Lx Ly Mb Me Mf Mg Mm Mp Mq Mz Nc Ne Nf Nl Nm Nt Nv Nw Ny Oz Pa Pb Pe Pg Po Wm) Ml(Et Hw Im Is Iv Jg Jk Jm Jn Jr Lh Li Lw Mb Me Mf Mi Mj Mk Mm Mp Ms Mt Mx Mz Na Nf Nl Nm Nn Nw Ny Ok Oz Pa Pb Pd Pe Pg Qd) Mt(Hq Hw Jg Jk Jm Jn Jo Jr Js Jt Li Lw Lx Ly Mb Me Mf Mi Mj Mk Mm Mp Mq Mz Nc Ne Nf Nl Nn Nt Nv Ok Oz Pd Pg Qa Qd Qe Wm) Nk(Et Hq Hw Im Jg Jk Jm Jo Js Jt Lh Lw Lx Ly Mb Me Mf Mg Mi Mj Mm Mp Mq Mz Na Ne Nm Nv Nw Ny Ok Pb Pd Pg Po Qa Qd Qe Wm) Iu(Et Hq Im Jg Jk Jl Jm Jt Lh Li Lw Lx Ly Mb Mf Mi Mj Mk Mm Mp Mq Mr Na Nc Ne Nl Nm Nn Nt Nv Nw Ok Pd Pe Pg Po Qa Qd Qe) Ms(Hq Hw Jg Jm Jo Jq Jr Jt Lh Li Lx Mb Mf Mg Mi Mk Mm Mp Mq Mx Mz Nc Ne Nf Nl Nm Nv Nw Ny Oz Pb Pe Pg Po Qa Qd Qe Wm) Mx(Et Hq Hw Im Jg Jm Jn Jo Jr Js Jt Lh Li Lw Lx Mf Mg Mk Mm Mp Mq Mz Ne Nf Nl Nm Nn Nt Nv Nw Ny Ok Oz Pb Pd Pg Po) Ir(Cs Et Hq Im Is Jg Jk Jm Lh Li Lw Lx Ly Mf Mg Mi Mj Mk Mm Mp Mq Mr Nc Ne Nl Nm Nn Nt Nv Nw Ok Oz Pa Pg Po Qd Qe) Mr(Et Im Jg Jk Jl Jt Lh Li Lw Lx Ly Mb Me Mf Mi Mj Mk Mm Mp Mq Nc Ne Ni Nl Nm Nn Nt Nv Nw Ny Oz Pd Pe Qd Qe) Na(Et Hq Ih Im Is Jg Jm Jo Jq Li Lx Ly Mb Mc Me Mf Mm Mp Nc Nf Ni Nl Nm Nn Nv Nw Ny Og Pg Po Qa Qe) Mi(Et Hq Hw Im Jk Jl Jo Lh Lw Ly Mb Me Mj Mk Mm Nc Ni Nl Nn Nt Nv Ny Ok Pa Pb Pd Pg Po Qe Wm) Et(Hq Im Jg Jk Jl Jq Jr Lh Li Lw Mb Me Mg Mj Mk Mp Nl Nn Nt Nv Nw Ny Ok Pa Pd Pe Pg Qd) Ni(Hq Im Jk Jl Jm Js Jt Lh Lx Ly Mb Mf Mg Mj Mk Mm Mp Mq Ne Nt Nv Nw Pa Pe Pg Po Qd Qe Wm) Jq(Im Iv Jg Jh Jl Jr Js Jt Lh Li Lx Mb Mc Md Mg Mj Mm Mz Nn Nv Nw Ny Oi Pg Qa Qe Wm) Pd(Hq Hw Im Jk Jl Jn Jo Jt Lh Li Mb Md Mg Mj Mk Nl Nm Nn Nt Nv Nw Ny Ok Pb Pg Qe) Mk(Hq Hw Im Jl Jm Jn Jo Jt Lh Li Lw Mb Me Mj Nc Nf Nl Nm Nv Ny Ok Pg Qa Qe) Is(Hv Hw Jg Jk Jl Jr Lw Me Mg Mj Mm Mp Mq Nc Ne Nl Nm Nn Nw Ok Oz Pe Po Qd) Pb(Hq Hv Hw It Iv Jr Js Li Lw Me Mf Mg Mm Mp Mz Nc Nl Nm Nn Ny Ok Po Qa) Ny(Hq Hv Hw Im Iv Jg Jh Jr Lh Li Mg Mj Mz Nc Nl Nn Ok Oz Pa Pe Po) Mj(Hq Im Jk Jm Jo Jt Lh Li Lu Mb Md Me Nc Nf Nl Nm Nn Nv Pg) Nl(Hq Ih Jk Jl Jm Jo Jr Li Lw Mb Nc Ne Nn Nt Nv Ok Pg) Jn(Hq Hv Hw Iv Jg Jh Jr Li Mb Md Me Mg Mm Nc Nv Nw Ok) Og(Jo Jt Lx Mm Mp Mq Ne Nm Nv Oz Pe Pg Po Qa Qd Qe Wm) Nf(Hv Jh Jk Jl Jr Js Jt Lh Li Mc Mg Nc Nw Oi Ok Po) Nt(Ih Im Jk Jl Jm Jo Lh Md Mf Nc Nm No Nv Pa Pg) Ih(Jm Jo Jr Lx Ly Me Mf Mg Mq Ne Oz Pa Pe Po) Jl(Hq Hw Im Jm Jo Md Nm Nv Ok Oz Pa Pe Pg Po) Hw(Hv Iv Jg Jh Jr Js Mg Mm Mz Nc Pa Pe) Im(Hq Jg Jk Jo Li Md Mp Mz Nn Nv Qd Qe) Ok(Hq Jo Js Ly Mb Mq Mz Nm Nn Nv Nw Pg) Jr(Hq Hv Iv Jh Jm Js Mc Me Mf Nc Nv) Lh(Jg Jk Jo Li Mb Nn Nv Nw Pg Qd Qe) Jk(Hq Jo Lu Mb Md Mf Nv Pg Po) Js(Hv Iv Jh Mb Mc Nc Nw Wm) Nn(Hq Jg Jo Ly Mb Nv Oz Qd Wm) Mc(Ba Jm Mq Mz Ne Qa) Md(Jo Jt Nv Pg Qa Qe) Hv(Iv Me Mg Ne Oz Pa) Jg(Hq Jo Ly Mb Nv Pg) Mz(Iv Jh Me Mg) Hq(Li Lx Ly Pg) Jm(Ly No Oi Qd) Jo(Jt Li Nw Pg) Wm(Fr Li Pa) Nv(Nw Po Qd) Nm(Lw Oi) No(Mg Ne) Me(Iv Jh) Pa(Oz Pe) Pg(Pe Po) FrQd MbJt NeIv} Is{Ma(Et Fp Hq Hu Hw Hx Ii Ik Il Io Ip Ir Iu Jg Jk Jl Jn Jo Jp Jq Jr Js Jt Lh Li Lj Lu Lw Lx Ly Lz Mb Me Mf Mg Mh Mi Mj Mk Ml Mm Mp Mq Mr Ms Mu Mv Mw Mx My Na Nb Nc Nd Ne Nf Ng Nj Nl Nm Nn Nq Nt Nu Nv Nw Nx Ny Oe Oh Ok Om On Oy Oz Pa Pb Pc Pd Pe Pf Pg Po Qa Qc Qe) Il(Fp Hq Hu Hw Hx Ii Ij Ik Im Io Ip Ir Iu Jg Jk Jl Jn Jo Jq Jr Js Jt Lh Li Lj Lu Lw Lx Ly Lz Mb Me Mf Mg Mh Mi Mj Mk Ml Mm Mp Mq Mr Ms Mu Mv Mx Mz Na Nb Nc Nd Ne Nf Ng Ni Nj Nl Nm Nn Nq Nr Nt Nu Nv Nw Nx Ny Oe Of Oh Ok On Oy Oz Pa Pb Pc Pd Pe Pg Po Qa Qc Qd Qe) Ip(Fp Hq Hu Hw Hx Ii Ij Ik Im Io Ir Iu Jg Jl Jn Jo Jp Jq Jr Js Jt Lh Li Lj Lu Lw Lx Ly Lz Mb Me Mf Mg Mh Mi Mj Mk Ml Mm Mp Mr Ms Mu Mv Mw Mx My Mz Na Nb Nc Nd Nf Ng Ni Nj Nk Nl Nm Nn Nq Nr Nt Nu Nv Nw Nx Ny Oe Of Oh Om On Oy Oz Pb Pc Pd Pe Pf Pg Qa Qc Qe) Mu(Et Fp Hq Hu Hw Hx Ii Ij Ik Io Ir It Iu Jg Jk Jl Jn Jo Jp Jq Jr Js Jt Lh Li Lj Lu Lv Lw Lx Ly Lz Mb Me Mf Mg Mh Mi Mj Mk Ml Mm Mp Mq Mr Ms Mt Mv Mw My Ma Nb Nc Nd Nf Ng Ni Nj Nk Nl Nm Nn Nt Nu Nv Nw Nx Ny Oe Ok Om On Oz Pa Pb Pc Pd Pe Pf Pg Po Qa Qc Qe) Qc(Fp Hq Hu Hw Hx Ii Ij Ik Im Io Ir Iu Jg Jk Jl Jn Jo Jp Jq Jr Js Jt Lh Li Lj Lu Lw Lx Ly Lz Mb Me Mf Mg Mh Mj Mk Ml Mm Mp Mq Mr Ms Mv Mw Mx My Mz Na Nb Nc Nd Nf Ng Ni Nj Nk Nm Nn Nq Nr Nu Nv Nw Nx Ny Oe Of Oh Ok On Oy Oz Pa Pb Pc Pd Pe Pg Po Qa Qe) Ml(Fp Hq Hu Hw Hx Ii Ij Ik Im Io Iu Jg Jk Jl Jn Jp Jq Jr Js Lh Li Lj Lu Lw Lx Ly Lz Mb Me Mf Mg Mi Mk Mm Mp Mq Mr Ms Mv Mw Mx My Mz Na Nb Nc Nd Ne Nf Ng Nj Nk Nl Nm Nn Nq Nr Nt Nu Nv Nw Nx Ny Of Oh On Oy Oz Pa Pb Pc Pd Pe Pg Po Qa Qd Qe Wm) Hq(Fp Hu Hw Hx Ii Ij Ik Im Io Ir Iu Jg Jk Jl Jn Jo Jq Jr Js Jt Lh Li Lj Lu Lw Lx Ly Lz Mb Me Mf Mg Mi Mk Mm Mp Mq Mr Ms Mx My Mz Na Nb Nc Nd Ne Nf Ng Nj Nk Nl Nm Nn No Nq Nr Nu Nv Nw Nx Ny Oe Of Oh Ok On Oy Oz Pa Pb Pc Pd Pe Pg Po Qa Qe) Li(Fp Hu Hw Hx Ii Ik Io Ir Iu Jg Jk Jl Jn Jo Jp Jq Jr Js Jt Lh Lj Lu Lw Lx Ly Mb Me Mf Mg Mh Mj Mk Mm Mp Mq Mr Ms Mv Mw My Mz Na Nb Nc Nd Ne Nf Ng Ni Nj Nl Nm Nn Nq Nt Nu Nv Nw Nx Ny Oe Oh Ok Om On Oz Pa Pb Pc Pd Pe Pf Pg Po Qa Qe) Lj(Fp Hu Hw Hx Ii Ij Ik Im Io Ir Iu Jg Jk Jl Jn Jo Jp Jq Js Jt Lu Lw Lx Ly

ItNy} Fr{aA(aL aW aZ bR cP dB Et Fp Hr Hw Ii Ij Ik Il Im Ir It Iu Jg Jh Jk Jl Jn Jo Jp Js Jt Lh Lj Lu Lx Lz Ma Mb Me Mg Mi Mj Mk Ml Mm Mp Mq Mr Mt Mw Mx My Nb Nc Nd Nf Nh Nj Nt Nv Nx Ny Og Oh Ok Pa Pd Pe Pf Pg Po Qb Qc Wm) Nw(Et Hq Hr Hw Ii Ik Il Im Ip Ir It Iu Jg Jh Jk Jl Jn Jo Jp Jq Jr Js Jt Lu Lv Lw Lx Lz Ma Mb Me Mg Mh Mi Mj Mk Ml Mm Mp Ms Mt Mu Mv Mw Mz Na Nb Nc Nd Ne Nj Nl Nt Nu Nx Ny Oh Ok Om Oz Pa Pb Pc Pd Pe Pf Pg Po Qc) Oe(Hq Hu Hw Ii Ij Il Im Ip Ir It Iu Jg Jk Jl Jn Jo Jq Jr Jt Lh Li Lu Lv Lx Lz Mb Me Mg Mh Mi Mj Mk Mm Mp Mq Mr Mt Mu Mv Mw Mx My Nb Nc Nd Ne Nj Nl Nm Nn Nv Ny Of Og Ok Oz Pa Pc Pd Pe Pf Pg Qb) Mr(Af An Ao Cq Cs Dd Et Fp Hq Hr Hw Hx Ik Im Ip Ir Jg Jo Jq Jr Lh Li Lj Lu Lw Lx Ly Lz Mb Me Mg Mh Mi Mj Mk Mm Mp Mu Mv Mw Mx Na Nb Nd Nh Nj Nk Nl Nm Nn Nu Nx Ny Of Oh Ok Oy Pd Pf Po Qb) aW(aC aF aG Al aM aN AO AP aR Aw Ax aY BA bC bF Bg bl bJ bL bM Bn bP bW bX cA cB cE cF cG CH cJ cK cM CO CQ CT CU cV CW Cx dA Dc DD DE dF dG dH dJ dK dL) Jm(Et Hq Hw Ih Ii Ij Ip Ir It Jg Jh Jk Jl Jo Jq Jr Jt Lh Li Lv Lx Lz Mb Me Mi Mj Mk Mm Mp Mq Mt Mv Mw Mx My Nc Ne Nf Nj Nl Nm Nn No Nv Ny Og Oh Ok Oy Oz Pa Pb Pc Pe Pf Pg Po Pz Qb Qc Wm) aH(aC aE aF aJ Al aM An AO AP aR AS aV Aw Ax aY BA BB bC bF BG bL bM bN bP bS bV bW bZ cE cG Ch cL cM cO CQ CT cU cV cW cZ dA Dc DD De dF dH Di dK dM) aL(aC aD aE Af aG al aJ aK aM AN AO aP aQ aR As aU aV Aw Bb bC bF Bg bL bM Bn bV bW bX cB cE cG Ch cJ cL cN CO Cp Ct Cu cV CW Cx cZ dA Dc Dd De dF dG dH Di dK DL) Nk(Bo Et Hq Hw Ii Im Ip It Jg Jk Jl Jn Jo Jq Jr Jt Lh Li Lu Lv Lx Lz Mb Me Mg Mh Mi Mj Mk Ml Mm Mn Mp Mq Mu Mv Mw Mx My Nb Nd Ne Ni Nl Nm Nn Nv Ny Ok Pa Pd Pe Pf Pg Qb) No(Aa Bc Cu Fp Hq Hr Hw Hx Ih Ii Ik In Ip Ir It Jg Jl Jo Jq Jt Lh Li Lu Lx Lz Mc Me Mi Mk Mm Mq Mt Mu Na Nc Nd Ne Nj Nl Nm Nn Nt Nu Nv Ny Og Oz Pa Pe Pf Pg Pz Qa Qb Qd Qe) Of(Et Hq Hu Hw Hx Ii Ik Ip Ir It Jn Jo Jq Jr Js Jt Lh Lj Lv Lw Lx Lz Mb Md Mg Mh Mi Mj Mk Ml Mm Mp Mu Mx Mz Nc Nd Nf Nj Nl Nn Nt Nv Ny Og Oh Ok Oy Oz Pa Pb Pd Pe Pf Po) Ih(Bc Cu Et Hq Hr Hw Hx Ii Ik Im In Ip It Iu Jg Jn Jo Jq Jt Lh Li Lu Lx Ma Me Mk Mn Mq Mt Mu Mw Na Nc Nd Ne Ni Nj Nm Nn Nr Nt Nu Nv Ny Pa Pb Pe Pf Pg Po Pz Qb Qe Wm) Io(Et Hq Hx Ii Ij Ik Il Ip Ir It Iu Jh Jk Jl Jn Jq Jr Js Jt Lv Lz Mc Mj Ml Mm Mp Ms Mt Mv Mw Mx My Nd Nf Ni Nl Nm Nn Nt Nv Ny Og Oh Ok Oz Pa Pc Pd Pe Pf Pz) Ly(Cq Et Fp Hw Hx Ik Im Ip Iu Jl Jn Jo Jr Jt Lh Li Lu Lx Lz Ma Mb Me Mf Mg Mi Mj Mm Mn Mp Mq Mv Mw Mx Na Nc Nd Ne Ni Nj Nl Nm Nn Nu Ny Pb Pd Pe Pf Po Qe Wm) Nu(Hq Hr Hu Ii Ij Il Ip Ir It Jg Jk Jo Jp Jq Jr Js Lw Lz Mc Mh Mk Ml Mn Ms Mt Mu Mw Mx My Mz Na Nb Nd Nf Ni Nl Nv Ny Oh Ok Om Pc Pd Pf Pg Po Qb Wm) bE(aE aF aG al Al aN AO Ap aR As aV Aw Ax aY BA Bb bF Bg bL bM Bn bS bV bW bX cF cH cJ cL CO Cp cQ Cs CT cV CW Cx cZ dA Dc dH Di dL) aZ(aD aE aF al Al AO Ap aQ aR As Aw bA BB Bc Bg bL bN bO bS bW bX cA cE cF cG Ch cK cL Cp Cq CT Cu cV CW dA Dc Dd DE dF dG dH dK) bU(aD aF al aJ aK aM AN Ao aQ aR aS aU aV BB bC bM Bn bS bV bW bX bZ cF cG cJ cK cL cM cN Co Cp Ct cU CW Cx cY cZ dC Dd DE dH Dl) Oy(An Bc Bo Cp Cq Cu Et Hq Hu Hx Ik Ip Ir It Jn Jq Jr Js Jt Li Lv Lw Lz Mb Md Mi Mj Ml Mm Mp Mx Mz Na Nf Nh Nj Ns Nt Og Oh Ok Pa Pd Pf) cX(Af al aK Al aM An Ao AP aQ aR aV Aw Ax Ba Bb bC bF bM Bn bS bV cB cE cG cJ cL cN CO Cq cS CT cU CW cZ Dd De dG Di dK Dl) In(Bc Cu Hq Hr Ii Ik Ip It Jg Jn Jq Js Jt Li Lu Lz Ma Mb Me Mf Mj Mk Mn Mq Mt Mu Mv Mw Mz Na Nd Ne Ni Nj Nm Nv Ny Pb Pf Pg Pz Wm) Nr(Fp Hr Hw Ii Im Ip It Iu Jg Jk Jo Li Lu Lv Lx Lz Ma Mb Me Mf Mh Mk Ml Mn Mq Mu Mv Mw Mx Nc Nl Nm Nn Nv Ny Pb Pg Po Qb Qd Qe) Nq(Fp Hw Hx Ik Im Iu Jn Jo Jr Jt Lh Li Lj Lu Lv Lx Mb Mf Mh Mk Mn Mq Mv Mw Nc Ne Nj Nl Nm Nv Ny Pa Pb Pe Pg Po Qb Qc Qd) Om(Et Hr Ik Im Ip Ir Iu Jl Jn Jq Jr Js Lh Lu Lx Lz Ma Mb Me Mf Mg Mh Mi Mj Mk Mm Mp Mu Mz Na Nc Ne Nj Nl Oh Oz Pa Pd Pe Pf) cR(aE aF aG Aj aK Al aM aO Ap AR aU aV Ax aY bA bF bJ bL bN bO bP bV cF cG cH cK Cp cQ Cs cV CW Cx DG dK dM dN) dE(aF Al An AO AP Aw AX aY Ba Bb Bc bN bO bP cA cE cH cL cN Co Cp CQ cS Ct cV Cw Cx dA Db Dc Dd De dG Di dM) Ns(Et Hu Hx Ij Ik Il Ip It Jk Jn Jq Jr Js Lv Lw Lz Mb Md Mg Mj Ml Mp Ms Mx My Mz Na Nd Nf Nj Nt Og Oh Ok Oz Pd Pf Po) Ni(Et Hq Hr Hu Ij Ir It Jg Jk Jq Jr Mc Mg Mj Ml Mm Mp Ms Mv Mw My Na Nb Nd Nf Nh Nj Nt Nx Og Oh Ok Oz Pc Pd Pf Pz Wm) Jh(Et Hu Hx Ij Il Ip Jg Jk Jn Jp Jq Js Lv Lw Md Mj Ml Mn My Mz Nb Nc Nd Ne Nf Nj Nl Nx Og Oh Ok Pd Pf Qa Qd Qe) Pz(Bc Hu Ij Ip Ir It Jk Jn Jo Jq Lh Lx Mc Md Ml Mm Mp Mv Mw My Na Nc Ne Nf Nj Nl Nm Og Pb Pd Pf Pg Po Qa Qb Qc Qd Qe) bJ(aE aF al Al aN AO Ap As Aw Bg bL bN bP bS bW bX cE cF cJ cK cL cM Co cQ Ct cU cV dA Dc dE dF dG dH Di dL) Mc(An Ao Ax Fp Hq Hr Hw Hx Ik Im Ip It Iu Jo Jt Lh Ma Mb Me Mf Mn Mq Na Ne Nj Nt Pb Pe Pf Qa Qd Qe) Mz(Hq Hu Hx Ij Ik Il It Jn Jr Li Lv Lw Mb Md Mg Ml Mt Mx My Na Nb Nd Nf Nj Nl Nt Nx Og Pa Pd Pf Qb) Nh(Et Hu Ij Ik Il Ir It Jg Jk Jn Jp Lv Lw Md Me Mh Mj Ml Ms My Nb Nf Nl Nt Nx Og Oh Ok Pa Pc Pf Po) Jp(Hq Hu Ij Ik Il It Jg Jk Jn Lw Lx Lz Mg Ml Mn Ms Mx My Na Nb Nd Nf Nv Nx Og Ok Pa Pc Pd Qb Wm) Md(Et Hq Hu Ik Ip Jn Jq Jr Js Lv Lw Mp Ms Na Nj Nt Nx Og Oh Ok Pd Pf) Ms(Hq Hu Ij Il Ip Jk Jn Jr Js Lv Mb Ml My Na Nd Nf Nt Og Ok Pa Qb) bR(aF Aj Ar aY bA Bg bN bO bP bX Ch cQ cS cV dA Dg dH dJ dK dL dM) Lw(Cq Dd Hq Hu Ij Ik Ip Jk Jn Lv Lx Mb Na Nf Nj Nn Pa Pc Po Qb) Db(aD aE aO aV aY bO cA cG cK cL cM cN cQ cS cV dA dH dJ dK) Na

Figure 2 Continued

Qb Qc Wm) Ik(aA Co Fp Hq Hw Hx Ih Io Iq It Jo Lz Mb Mc Mf Mh Mq Mr Mx Nb Nc Ne Nf Ng Nh Nj Nl No Nr Oe Og Oi Oy Oz Pa Pb Pe
Pz) Js(aA Fp Hq Hw Hx Iq Ir Jm Jq Lw Lz Mb Me Mn Mr Nb Nc Nd Ne Nf Nj Nl Nm Nr Ny Oe Og Oi Oy Oz Pa Pb Pc Pe Pg Pz Qb Qc)
Hu(aA Co Fp Hr In Ir It Iu Jm Jo Jq Li Lj Lw Mc Md Mf Mh Mk Ml Mn Mq My Na Nd Ng Nh Ni Nk Nm Ns Ny Pc Pg Pz Qb Qc) Mr(aA Et
Hq Hx Ih Io Iq It Jm Jo Lu Mb Mc Md Me Mh Mk Ml Mn Mz Na Nb Nc Nd Ne Ng Nj No Nr Ns Oe Oi Oy Pe Qe) Na(aA Fp Hq Hv In Ip Ir Iu
Jq Li Lj Lw Lz Md Mf Mk Ml Mn Mq My Nf Ng Nh Ni Nk Nm No Ns Ny Pc Pe Pg Pz Qc) Jq(aA Ip Ir Jg Jm Jo Li Ly Mc Mf Mh Ml Mq Mx
My Nc Nd Ne Nf Ng Nh Nj Nk Nl Ns Ny Oi Pc Pg Pz Qc) Iu(aA In Ip It Jg Jm Li Lw Ly Lz Mc Md Mf Ml Mn My Ng Nh Ni Nj Nk Nm Ns Ny
Oi Pc Pe Pg Qb Qc) Co(An Ao Ap Bb Bg Cq Fp Hv Hw Il Ir Lv Lz Mq Mx Nd Nf Nh Nj Ns Nu Nv Ny Oi Pb Pe Pg Pz) Ni(aA Fp Hr Ir Jm Jo
Li Lj Lw Md Mk Mn My Nc Nd Ng Nj Nm No Ns Ny Pa Pc Pe Pz Qb Qc Wm) Jo(aA Fp Hr Hw In Ip Ir Jg Li Lj Lu Md Mh Mk Ml Mq My Nb
Nd Nk Ns Oi Pb Pe Pg Qc Wm) Li(Hw In Io Ip Ir It Jg Lu Lw Ly Lz Mc Md Mk Ml Mx Nd Ng Nh Nk Nm No Ny Oi Pc Pg) Jg(aA Hr In Io Ip
Ir It Lu Lw Ly Mc Mk My Nh Nm Nv Ny Oi Pc Pg Qc) Et(Hq Hw Iq Lj Mb Me Mn Nb Nc Nj Nl Nm Nr Ny Oy Oz Pa Pe Pz Qb) Mz(Hq Hw Iq
Lj Me Mn Nb Nr Oe Og Oy Oz Pa Pb Pe Pz Qb Qc Wm) Nv(Fp Hq Hw Iq Jm Lj Mb Me Nc Ng Nl Nm Nr Oz Pa Pc Pe Qb Qc) Pg(aA Hr Ip Ir
Ly Mc Md Mk Mq My Nd Nh Ns Ny Oi Qc) Hv(Hq Hw Me Nb Ne Nf Nl No Oe Oy Oz Pa Pe Qb Wm) Ns(aA Fp Ip Ir Ly Mq My Ng Nh Nm
Ny Pe Pz Qc) Mg(Ar Ax Bn Cs Cv Dc Dg Di Dk Lj Mb Qb Wm) Ip(Fp In Ir Lu Md Mk Ml My Nd Ng Nk Ny Qc) aA(Hr In Lw Mc Md Mh Mq
Nd Ne Ny Pc Pe Qe) Mq(Hr Ir Lw Ly Mc Md Mk Nc Ng Nh Nk) Mw(Hq Iq Mb Me Nf Oe Og Oz Pa Pb Wm) Wm(Il Jk Mv Nb Nd Nu Oi Ok
Qd) Mt(Af An Ax Bb Bo Ch Cq Dc Dd) Nh(Fp Ir Md Ml Mn Nd Ny Pe Qc) Mk(In Lw My Nk Nm Ny Pe Qc) Md(Ir My Nb Nm Ny Pe Qc)
Mv(Aj An Ao Bo Db Dk Dl) Il(Lj Mb Mc Nf Og Oz Pa) In(Bc Cw Jm My Pe Qb Qc) Ma(Ad Aj Bo Cs Dd Dl) Mc(Fp My Ng Pe Qc) Nt(Af Bg
Ch Cx) Ir(Ly Ml My Nk) Nu(Ch Mb Qb) Qe(Nf Oz Pa) Jl(Al Ba Cx) Ly(My Pe) Hr(My Oh) Oz(Jp Nw) BcLv ChlvCsPf LuLw NkPe}
Mt{Oi(aA Ad Aj Al Ap Aw Bb Co Cp Cs Cu Cw Db Dg Dd De Di Dl Et Fp Hq Hv Hw Hx Ih Ii Ij In Io It Iu Jg Jk Jl Jm Jn Jo Jq Js Lh Li Lj Lu Lv
Lx Ly Lz Ma Mc Me Mh Mj Mk Ml Mm Mq Mr Mw Mx My Mz Na Nb Nc Nd Ne Nm No Nq Nr Nv Nx Ny Oe Of Og Ok Oy Oz Pa Pb Pc Pd
Pe Pg Po Pz Qa Qd Qe) Iv(aA Et Fp Hq Hu Hv Hw Hx Ii Ij Ik Il Im Io Ip Iq Ir Iu Jg Jl Jm Jn Jo Jr Js Jt Lh Li Lj Lu Lx Ly Lz Mb Mc Me Mf Mg
Mh Mi Mj Mk Ml Mm Mn Mp Mr Ms Mv Mw Mx My Mz Nb Nc Nf Ng Nh Ni Nl Nm Nn No Nq Nt Nu Nv Nx Ny Oe Of Og Oh Ok Pb Pc Pd
Pg Po Pz Qa Qb Qc Qd) Jh(aA Dk Fp Hq Hw Ii Ij Ik Il Io Ip Iq It Iu Jk Jm Jo Jp Jq Js Jt Lh Li Lj Lu Lv Lw Lx Lz Mb Mg Mh Mj Mk Ml Mn
Mp Mr Ms Mu Mv Mw Mx My Mz Na Nb Nc Nd Nh Ni Nj Nk Nl Nm Nn No Nq Nr Nt Nv Nw Nx Ny Oe Og Ok Oy Pb Pc Pd Pe Pf Pg Po Qa
Qb Qc Qd Qe) Mc(Ad Ao Aw Bb Bc Bg Co Cp Cs Cv Cw Dc Dd Dg Dk Fp Hq Hv Hw Hx Ih Ii Io Ir It Jl Jm Jp Lh Li Lx Ly Ma Mj Mk Ml Mq
Mr Ms Mv Mw Mx Mz Nc Ne Ng Nh Nl No Nq Nv Nw Nx Of Oy Oz Pa Pb Pc Pf Po Qa Qd Qe Wm) Jr(Fp Hq Hr Hu Hv Hw Hx Ii Ij Im Io Iq
It Jn Jp Js Lh Li Lj Lv Lw Lx Ly Lz Ma Mf Mh Mi Ml Mp Ms Mu Mv Mw Mx My Mz Nb Nc Nd Ne Nf Ni Nk Nl Nm Nn No Nq Nu Nv Ny Of
Og Oh Ok Oy Oz Pb Pc Pf Pz Qb Qc) Mu(aA Fp Hq Hv Hw Ii Ij Ip Ir Jl Jm Js Lh Li Lv Ly Lz Ma Mb Me Mh Mj Mk Ml Mq Mr Ms Mv Mw
Mx Mz Na Nc Nd Ne Ng Nh Ni Nj Nk No Nq Nr Nt Nv Ny Oe Og Oh Ok Oy Pa Pd Pf Po Qa Qe) Ih(aA Ao Bc Cq Cs Cv Dc Dg Di Dk Fp Hq
Hr Hv Hw Hx Ij Jg Jl Jp Js Li Lx Lz Ma Mb Mj Mn Mp Mq Mr Mv Mw My Nb Ng Nh Nm Nn No Nq Nu Nw Of Oh Oy Pb Pf Po Pz Qa Qb Qe
Wm) Ns(Fp Hq Hw Hx Ii Ir Jl Jm Jq Js Lh Li Lv Lx Ly Lz Ma Mb Me Mf Mh Mj Ml Mq Mr Ms Mv Mw Mx Mz Nc Nd Ne Nh Ni Nj Nk Nl No
Nq Nr Nt Nv Nx Og Oh Ok Oy Oz Pa Pc Pf Po) Nu(Cq Hq Hr Hv Hw Hx Ii Ip Iq Ir It Jm Jn Li Lj Lv Lw Lx Lz Mi Ml Mn Mp Mu Mv Mx My
Nb Ne Ng Nh Ni Nk Nl Nn Nu Nq Nr Nw Ny Of Og Oh Ok Oy Pb Pc Pf Qb Wm) In(Af Ap Ar As Aw Ba Bg Bn Ch Co Cp Et Hx Ii Ik Il Iq Iu
Jg Jl Jq Lh Lu Ma Mf Mr Mz Ng Ni Nj Nk Nr Nv Nx Ny Oe Pa Pe Pg Qa Qb Qc Qd Qe) Lw(Af Bn Dd Hr Hv Ii Ij Iq It Jl Jm Jo Jp Lu Lv Ly
Mb Mi Mp Mq Mv Mw My Nb Ne Nf Ng Nj Nk Nl Nm Nn Nr Ny Oh Ok Oz Pa Pc Pg Pz Qh Wm) Mu(aA Hq Hr Hw Hx Ii Ij Ik Jp Lz Mb Mh
Mk Mp Mr Mv Mw Mx Mz Na Nb Nc Nf Nh Ni Nj Nk Nl Nn Nr Nt Ny Og Oh Ok Oz Pa Pc Pd Pf Pg) Nk(AA Ar As Aw Ax Bg Bn Ch Co Cp
Cw Cx De Di Hr Hv Ir Jg Jp Lv Mh Mi Mr Mv Nb Nn No Nt Nw Oh Ok Oz Pa Pc Pe Pf Pz Wm) Oy(Af Aj Al An As Ax Ba Bb Bn Bo Ch Co
Cp Cq Ct Cx Dc Dd Dg Di Dk Hv Ii Ir Jl Jp Js Lh Mi Mp Mr Mv No Nw Oh Ok Pc Po Pz) Jn(Hq Hx Ii Im Js Lh Li Lj Lv Lx Ly Lz Ma Mb Mk
Ml Mn Mp Mq Mr Mv Mw Nb Nc Ne Nh Nl Nn No Ny Of Og Oz Pb Pc Pe Qb Qc) Hu(Hq Hr Hv Hw Hx Io Iq Ir It Jm Jp Js Li Lj Lv Lz Ma Mj
Ml Mp Mq Mv Mw Nb Nc Nh Ni Nl Nn No Oz Pc Pf Qb) Pz(Cs Cu Hq Hw Hx Ir It Jg Jl Jp Lh Li Lv Lz Ma Ml Mp Mq Mr Mv Mx Ng Nn No
Nq Of Oh Ok Pe Pf Qd) Mi(Hr Hv Hw Hx Ii Il Iu Jo Jp Lz Mh Mx My Mz Ne Nh No Nq Ny Oe Of Og Oh Ok Pa Pc Pg Qc) Ij(Hq Hw Iq Ir
Jp Jq Lz Mj Mn Mp Mr Mv Mw Mx My Nb Ne Nh Nn No Nq Nw Ok Oz Pa Pc Pe Pf Po) Hr(aA Cs Hv Jl Jo Jp Jq Lh Lv Ly Mj Ml Mp Ms Mz
Na Nb Ng Nh Ni Nj Nn Nr Nx Ok Pc Qe) Ir(Hv Io Iq It Iu Jl Jp Jq Lj Ml Mp Mz Nb Ng Nh Ni Nn Nx Of Ok Oz Pc Qb) aA(Et Hv Ip It Jl Jp Li
Mf Mh Mm Mn Mp Mx Mz Ne Nl No Nq Oe Oh Ok Pc) Ni(Al Bc Dg Ip Jl Jp Jq Jt Lj Mn Ms Mw Mz Nb Nd Nm Nn No Nt Pc Pf) Nw(Ii Il Iu
Iq It Iu Lj Lz Ml Mn Ms Mx My Ng No Nr Oe Of Og Qb) Mp(Hw Il Iq Jp Lu Lv Mh Mj Mv Mx My Nb Ng Nq Nr Og Pd Qb) Ok(Hv Io Iq Jm
Lv Mh Mv Mx My No Nr Nv Of Og Oh Pc Pf Qb) Pf(Hq Hv Io Iq Jm Jp Mn Ms Mz Nd Ng Nh No Of Og Oh Pg) Nb(Hq Hw Ii Il Io Jo Lz Ml
Mx My Nn Nq Nv Ny Of Pc) Wm(It Jl Jm Lv Mh Ml Mr Ms Mx Nh Nr Oe Of Oz) Mv(Ao Cq Hv Il Io Iq Jk Jm My Mz Nr Oe Of Pc) Lv(Al Jm
Jp Lu Mj Ms Mz Nh Nr Oe Of Oh) Cq(Bg Cu Dg Hx Jl Mh Mr Nd Nj No Nq) Of(Bg Cu Ii Jl Jp Lh Li Mj Mn No Po) Oh(Hv Io Iq It Jp Lh Lj
Ml Ng Nh No) My(Iq It Jp Lz Mx Ne Nn Nq Oz Qb) Ba(Bo Fp Io Mx Ng No Nq Nr Pb) Hv(Il Jg Jp Lh Mj Mq Ng Qd) Hx(Aj Bc Bo Cu Dc Dd
Dg Dk) Jl(Hw It Iu Jm Mx Nr Qb) Nn(Jp Mj Mx Ng Nq Nr) No(Bc Di Jp Lh Og Qb) Mr(Af Al Dc Dg Lz Pg) Ng(Io It Jp Mg Ml) Bc(Ii Nj Og
Oz) Bo(Ii Nj Nv Og) Nr(Jp Mw Nt Qd) Nh(Js Mz Ne Nl) Jm(Il Jp Mj Nq) Pc(Lh Lx Mj Po) Cs(Al Mh Nd) Cu(Dk Hw Ny) Dc(Nd Nj) Lx(Hq
Nd) Io(Jp Nq) Lh(Jo Qb) Pb(Af Al) BgNv DdMg DgNj NmOg LzPa MhMz Mxlq} cS{cC(aC aD aG aH al aK aL aM aO aP aQ AR aV aW AX
aZ Ba bB bC bE bF bG bI bJ bL bM Bo bP bQ bS bU bV bW bZ cA cB cE cF cH cJ cK Cq Cs Ct CU cV cW cZ DB DC DD dE dF DG dH dI
dJ dL dM) bO(aC aE aG aH al aJ aK aL aM aN aO aP aQ AR aU aV aW aX aY aZ bB bC bF bG bI bL bM bN Bo bP bV bW bZ cB cE cG cH
cJ cL cM cN cO cR cU cV cW cX cZ dA dB dC dE dF dG dH dI dJ dK dM eF) Bo(aC aD aF: aG aH aJ Al aM aN aO AP aQ As aV Aw Ax Bb
bC bF bH bI bM Bn bQ bV bW bZ cE cG cI cJ cL cM cO Cp Cq Cs Ct CV CW Cx cY cZ dA DB DC dD dF dI dJ Dk DL dN) bQ(aC aE Af aG aH
aK AL aM Ap aQ AR AS aU aV Ax aZ bB BC bH bI bL bM bN bP bS bV bW cA cB cE cF cH cI cJ cK cL Co Cs cV CW cY cZ dB DC dD dE
Di dJ Dl dN) bX(aC aF AJ aK aL aM aO aP aQ AR AS aU aV aW aX aZ bB bC bF bG bM bS bV bW bZ cA cB cE cG cJ cL cN cO Cs cV cW
cY cZ dB dC dD dE dF DG dH dI dL dM) cK(aC aE aG aH aI AJ aK aM aO aP aQ aR As aV aZ bB bC bF bG bI bL bM bN bP bW cA cB cE
cH cJ cL cN cO Cs cU cV cW cX cZ DB dC dD dE dF dG dH dI dJ dM eF) cI(aC aD aE aG Aj aL aN aQ aR aS aV aW aZ Ba bB BC bF bG bI
bJ bM bV bW cG cH cJ cL CO Ct CU cV cX cY cZ DB dC dD dF dH dJ dK dM) cT(aA aC aF al aL aM aQ Ar aS aV aW aZ bA bB bE bF bG
bI bL bM bS bV bZ cA cE cG cH cJ cL cM cN cQ cR cU cV cX cY cZ dA dB dC dD dF dG dH dI) aD(aC aE aG aH al aJ aK aM aN aO aP aQ
aU aV aX aY aZ bB bF bI bL bM bP bW cA cE cF cH cM cN cX cY cZ dA dB dD dH dI dJ dK dM eF) bE(aF aG aH al aJ aK aM aP aU aV aW
aZ bB bC bF bG bI bJ bL bM bP bV bW cB cE cG cH cI cN cR cU cV cW dA dB dC dG dH dM dN eF gP) cF(aC aE aH al aJ aO aP AR aS aY bB
bC bF bJ bL bP bV bW cB cG cH cJ cL cM cO cU cV cW cX cZ dB dC dE dF dG dH dI dJ dK dM) bA(aA aF aJ aK aM aO aP aQ aR aV aW
aX aZ bB bC bF bI bL bM bW bZ cI cL cM cN cO cU cV cW cY cZ dA dB dC dD dE dI dJ dM) Ar(aC Af aH al Aj aK An AP As aW bF bG bJ
bL bM Bn bW cA cE cM CQ cR Cs Cu Cw Cx Db Dd dF DG dH dJ DK) cM(aC aE aG aH al aJ aM aN aQ aV aY aZ bI bJ bL bP bS bZ cA cB

AjcM AxFw DlcC MrNy NdOf HqOg aXcD c

Figure 2 Continued

Unconstrained panels with 2 analytes, where 1.0E-7 >= 'AUC p-value' > 0. Contains 46 panels of 19,595 total panels evaluated. : Jj(Fr Is Iv Jh Ji Jk Jl Ma Mt Mu Mv Nt Ok Om On Pf Qd) On(In Iv Ni No Oe Of Oi Pz) dN(cS cT dR eF Fr gL) Fr(bQ cD Iv Oi) Is(Hr In Jm) aA(bU cX) cS(bR cP) CuMc HrJi bAbU cIeF Unconstrained panels with 2 analytes, where 1.0E-6 >= 'AUC p-value' > 1.0E-7. Contains 98 panels of 19,595 total panels evaluated. : On(aA Hv Ih Ii Ij Io Iq Jm Lv Mc Md Mi Mr Ms Ng Nh Nk Nn Nr Ns Nv Ny Og Oy Pa) Is(aA Fr Hv Ih Iq Iv Jh Lv Mc Md Mn Mt Nh Ns Og Oi Pz Qb) Ji(Fr Hv Ih In Iv Jh Lu Mc Md No Oi) Om(aA Hr In Ir Md Nk Ns Of Og Oi Oy) Fr(aA cC cI cP dB Hv Iq Mc Ng) Jj(Il Jp Lv Mg Nu Nw Oh Qa Qe) dN(bA bZ cR gP) In(Cu Mt) cD(bA cS) cP(bZ Co) BacH LvaA MaIv aEeF bUcS Unconstrained panels with 2 analytes, where 1.0E-5 >= 'AUC p-value' > 1.0E-6. Contains 364 panels of 19,595 total panels evaluated. : Is(Hq Hu Hw Hx Ii Ij Ik Il Im Io Ip It Iu Jg Ji Jn Jo Jp Jq Jr Js Li Lj Lu Lw Ly Lz Ma Mb Me Mg Mh Mi Ml Mm Mp Mr Ms Mu Mv Mw Mx My Mz Na Nb Nd Nf Ng Ni Nj Nk Nm Nn No Nq Nr Nt Nu Nw Ny Oe Of Oh Om On Oy Pb Pc Pd Pf Qa Qc Qe) On(Et Fp Hq Hr Hu Hw Hx Ik Il Im Ip Ir It Iu Jg Ji Jk Jl Jn Jo Jp Jq Jr Jt Lh Li Lu Lw Lx Ly Lz Ma Mb Mh Mj Mk Ml Mm Mn Mp Mq Mt Mu Mw Mx My Mz Na Nb Nc Nd Nf Nj Nl Nm Nq Nt Nu Nw Nx Oh Ok Oz Pb Pc Pd Pe Pf Pg Po Qb Qc) Ji(aA Et Fp Hq Hu Hx Ii Ij Ik Il Io Ip Iq Ir It Iu Jp Lj Lv Lz Ma Mh Mi Mk Ml Mn Mr Ms Mt Mu Mv Mw Mx My Na Nb Nd Ng Nh Ni Nj Nk Nl Nq Nr Ns Nu Nx Oe Of Og Oh Om Oy Pb Pc Pd Pf Pz Qb Qc) Om(Fr Hu Hv Ih Ij Iu Iv Jh Jm Jo Jp Jr Lu Mc Ms Mt Mu Mv My Nd Ng Ni Nr Oe Oh Pz) Jj(Et Hv Ii Ij Ik Im Jr Js Jt Lh Lx Mi Mj Mm Mp Mr Mw Mz Nn Nq Nv Nx Of Pd Po) Fr(aH aL aW aZ bE bU cX Ih In Jm Ly Mr Nk No Nq Nr Nw Oe Of) cS(aA aD Ar bA bE BO bQ bS bX cC cF cI cK cQ) Mt(Hu Ih Ij Iv Jh Jn Jr Mc Md Mu Ns Nu Oi Pz) Iv(Hr In Jh Jl Jp Lv Mu Mv Pf) eF(aD aG aH aN bR bU cD dF) aA(bJ bN bR cD cl dN Mu) Ba(bU cD cI dN) Nw(In Jh Ni Oi) cT(bU cD cI cU) dN(aI bX cP) Cu(Nk No) Mu(Jn Nu) Hv(Jh Mv) bA(cH cl) CoOy NqJn LxMc MwIn NiOh NkJl JhJr OiPf aJbU aXcD bZcE Unconstrained panels with 2 analytes, where 1.0E-4 >= 'AUC p-value' > 1.0E-5. Contains 686 panels of 19,595 total panels evaluated. : Om(Fp Hq Hw Hx Ii Ik Il Im Io Ip Iq It Jg Jk Jl Jn Jq Js Jt Lh Li Lj Lv Lw Lx Ly Lz Ma Mb Me Mf Mg Mh Mi Mj Mk Ml Mn Mp Mq Mr Mw Mx Mz Na Nb Nc Ne Nf Nh Nj Nl Nm Nn No Nq Nt Nu Nv Nw Nx Ny On Oz Pa Pb Pc Pd Pe Pf Pg Po Qb Qc Wm) Fr(aE aF bJ bN bR bX cH cQ cR Cs cV dE dF dM Et Hq Hu Hx Ij Ik Il Io Ip It Jh Jk Jn Jp Jq Jr Js Lv Lw Md Ml Ms My Mz Na Nb Nd Nf Nh Ni Nn Ns Nt Nu Nx Og Oh Ok On Oy Pc Pd Pf Pz) Mt(aA Hr Hv Hw Hx Ii Io Iq Ir It Jl Jm Jp Js Lh Li Lv Lw Lx Lz Mh Mi Mj Ml Mp Mq Mr Ms Mv Mw Mx My Mz Nb Nc Ne Ng Nh Ni Nk Nl Nn No Nq Nr Nw Ny Of Oh Ok Oy Oz Pa Pc Pf Po Qb Wm) cS(aC aE aG aI1 aI aJ aK aM aN aO aP As aV aW aY aZ bB bC bG bI bJ bL bM bN bP bV bW bZ cA cB cE cH cJ cM cN cR cT cU cW cX cZ dA DB dC dG dH dI dJ dK dM) Ji(Hw Im Jg Jk Jl Jm Jn Jo Jq Jr Js Jt Lh Li Lw Lx Ly Mb Mc Mf Mg Mj Mm Mp Mq Mz Nc Ne Nf Nm Nn Nt Nv Nw Ny Ok Oz Pa Pe Pg Po Qa Qd Qe Wm) Jj(aA Co Cu Fp Hu Ip Ir Iu Jg Jn Jo Jq Li Lw Ly Mc Md Mk Mq Ms My Na Ng Nh Ni Nj Nm No Ns Ny Pe Pg Pz Qb Qc) dN(aE aj aK aL aO aP aS aU aV aX aY bF bG bH bJ bN bO bR bU bV cA cF cG cH cK cM CO cQ Cu cW cX cY dD dK) Nw(aA Hr Hv Ih Io Ir Iu Iv Jl Jp Jr Lu Lv Ma Mc Md Mh Mi Mn Ms Mu Mv Mw Mx Nb Nk No Ns Nu Oe Og Pf Pz) Jh(aA Hr Hu In Ir Jl Jn Jp Js Lx Mc Md Mr Mz Nc Ng Nh Ns Nt Nu Of Oh Oi Ok On Pf Po Qa Qe) Is(Et Fp Ir Jk Jl Jt Lh Lx Mf Mj Mk Mq Nc Ne Nl Nv Nx Ok Oz Pa Pe Pg Po Qd) Cu(Af aH AI aW aZ BA Bc bJ bN bQ bR bU cA cI cQ cR CX Dc Dd Jm Oy) Iv(Et Hv Ih It Jg Lw Md Mp Ms Mw Mz Nd Nk Nn Ns Nt Nu Oh Oi Ok Pc) aA(bF bO bZ cF cH cR cU dK In Jl Jp Jr Lw Ma Mn Mp Mv Mz Nn Nq Pf) cF(aF aL aY bE bF bJ bN bO bQ cA cC cE cH cK cR cU cV cX dC dG dK) Mu(Hq Hv In Iq Jp Jr Js Lw Mg Mp Mr Nh Nq Ns Nt Oh Oz Pc Pd Pz) In(Cw Hv Jl Jn Jp Jr Js Mg Mp Nm Nu Oh Ok Pf Qa) Jl(Hr Hv Ir Md Mg Mv Ns Nu Of Oy Pf Wm) Jn(Lw Lx Ma Md Mi Mp Mv Mw Nn Ns Nu) bA(aD bJ bO bR cB cF Co cR cU cX dK) Nu(Ir Jr Lx Mn Mv Nb Nn Ns Pf) On(Js Lj Me Mf Mv Ne Qa Qd Qe) Pf(Hv Jr Mc Mz Nk Nr Ok Oy) Lv(Hv Jp Js Mp Mz Oh Ok) bZ(aE bX cD cI cQ cT dK) Jp(Hv Jr Mc Mi Mp Ni) Lx(Md Mr Nb Nd Ns) cT(aD cH Co cX dK) Ba(cR cU cX dE) bU(aP aX dI dK) Mv(Mp Nb Ok) Co(cQ cR) Nn(Mc Mr) Lw(Mw Nb) Ir(Mp Nb) Jr(Mw Nq) Oi(Nt Oh) Ok(Mi Ni) bR(aJ aP) cP(De dK) CpcR bEgP cIgL Unconstrained panels with 2 analytes, where 1.0E-3 >= 'AUC p-value' > 1.0E-4. Contains 1,565 panels of 19,595 total panels evaluated. : Cu(aA AD aE aF aI AJ aK aM AN AP aQ Ar AS aU aV Aw AX aY Bb Bg Bn BO bS bX cC cD cE cF Ch cJ cK cL cM CO CP Cq CS CT CV CW DB dC dF DG dH Dl dJ DK Dl Fr Fw Hq Hr Hw Hx Ih Ii Ij Jo Jq Js Md Mh Mr Ms Mt Mx Nd Ni Nj Ns Nu Nv Ny Of Og Oi Oz Pa Pb Pg Pz) Jl(AI Et Fp Fr Hq Hu Hw Hx Ih Ii Ij Ik Il Im Io Ip Iq It Iu Jg Jk Jm Jn Jo Jp Jq Jr Js Jt Lh Li Lj Lu Lv Lw Lx Ly Lz Ma Mb Mc Me Mf Mh Mi Mj Mk Ml Mm Mn Mp Mq Mr Ms Mu Mw Mx My Mz Na Nb Nc Nd Nf Ng Nh Ni Nj Nl Nm Nn No Nq Nr Nt Nv Nx Ny Oe Og Oh Oi Ok Oz Pa Pb Pc Pd Pe Pg Po Pz Qa Qb Qc Qd Qe) Jh(Et Fp Hq Hw Hx Ih Ii Ij Ik Il Im Io Ip Iq It Iu Jg Jk Jm Jo Jq Jt Lh Li Lj Lu Lv Lw Ly Lz Ma Mb Me Mf Mg Mh Mi Mj Mk Ml Mm Mn Mp Mq Ms Mu Mv Mw Mx My Na Nb Nd Ne Nf Ni Nj Nk Nl Nm Nn No Nq Nr Nv Nx Ny Oe Og Oy Oz Pa Pb Pc Pd Pe Pg Pz Qb Qc Qd Wm) Jp(Et Fp Hq Hr Hu Hw Hx Ih Ik Im Io Ip Iq Ir It Iu Jg Jm Jn Js Jt Lh Li Lj Lu Lw Lx Ly Lz Ma Md Mg Mh Mj Mk Ml Mm Mn Mq Mr Ms Mv Mw Mx My Mz Na Nb Nc Nd Ne Nf Ng Nh Nj Nk Nm Nn No Nq Ns Nt Nu Nx Oe Of Og Oh Oi Ok Oy Pb Pc Pd Pe Pf Pg Po Qa Qb Qc Qd Qe) Iv(aA Fp Hq Hu Hw Hx Ii Ij Ik Il Im Io Ip Iq Ir Iu Jk Jm Jn Jo Jq Jr Js Jt Lh Li Lj Lu Lx Ly Lz Mb Mc Me Mf Mg Mh Mi Mj Mk Ml Mm Mn Mq Mr Mx My Na Nb Nc Ne Nf Ng Nh Ni Nj Nl Nm No Nq Nr Nv Nx Ny Oe Of Og Oy Oz Pa Pb Pd Pe Pg Po Pz Qa Qb Qc Qd Qe) Nw(Et Fp Hq Hu Hw Hx Ii Ij Ik Il Im Ip Iq It Jg Jk Jm Jn Jo Jq Js Jt Lh Li Lj Lw Lx Ly Lz Mb Mc Mf Mg Mj Mk Ml Mm Mp Mq Mr Mx My Mz Na Nb Nc Nd Ne Nf Ng Nj Nl Nm Nn Nq Nr Nt Nv Nx Ny Of Oh Ok Oy Oz Pa Pb Pc Pd Pe Pg Po Qa Qb Qc Qd Qe Wm) Fr(aD aI aO Ax aY BC bL bM BO bP cA cE cF cK cM cO cU dA Db dG dJ DK dL Fp Hr Hw Ii Im Ir Iu Jg Jo Jt Lh Li Lu Lx Lz Ma Mb Me Mf Mg Mh Mi Mj Mk Mm Mn Mp Mq Mt Mu Mv Mw Mx Nc Ne Nj Nl Nm Nv Ny Oz Pa Pb Pe Pg Po Qa Qb Qc Qd Qe Wm) Pf(Fp Hq Hr Hu Hw Ih Ij Ik Im Io Ip Iq Ir It Jg Jm Jn Jq Js Jt Lh Li Lj Lv Lw Lx Ly Lz Ma Md Mg Mh Mi Mj Ml Mn Mp Mq Mr Ms Mu Mv Mw Mx Na Nb Nc Nd Nf Ng Nh Ni Nj Nl Nm Nn No Nq Ns Nt Nv Nx Ny Of Og Oh Oz Pb Pc Pg Po Pz Qa Qd Qe) Mt(Af Aj Al Ao Ba Bb Bc Bo Cq Cs Dc Dd Dg Di Dk Et Fp Hq Ik Il Im Ip Iu Jg Jk Jo Jq Jt Lj Lu Ly Ma Mb Me Mf Mg Mk Mm Mn Na Nd Nf Nj Nm Nt Nv Nx Oe Og Pb Pd Pe Pg Qa Qc Qd Qe) Ok(aA Hr Hv Ih Ij Ik Im Io Iq Ir Iu Jg Jm Jo Jr Lu Lw Lx Ma Mc Md Mg Mh Mk Mp Mq Mr Ms Mu Mw Mx Mz Na Nd Nh Nk Nm Nn No Nq Ns Nt Nu Ny Oe Of Og Oh Oi Om Oy Pc Pd Po Pz Qa) aA(aD aE aF al aK aN aO aU aX aY bC bG bH bI bM bS bX cA cB cC cK CO cW Cx cY dA dC dD dG dR Et fR Hr Hv Ip Jg Li Lx Mc Mf Mg Mh Mm Ni Nt Nu Nv Oh Pc Po Qa) Mu(Bc Et Hr Hw Ih Ij Io Ip Jk Jm Jo Jq Jt Li Lu Lx Lz Mb Mc Md Me Mh Mi Mj Mk Mm Mv Mw Mx My Mz Na Nb Nc Nf Ng Ni Nj Nk Nl Nm Nn Nx Ny Of Oi Oy Pa) dN(aC aD aF aG aH aM aN aQ aR aW aZ bB bC bE Bg bI bL bM bP bS bW cB cC cD cE Ch cI cJ cL cN cU cV cZ dA dB dC dE dF dG dH dl dJ dL dM) eF(al aK aO aP aQ aR aS aV aW bA bB bC bG bH bI bL bM bS bV bW bX bZ cB cF cG cJ cL cM cN cO cP cQ cS cT cW cY dA dB dD dH dJ dL gP) Lx(Hw Hx Ih Ii Ij In Iq Ir It Jr Li Lj Lv Lw Ly Lz Mi Ml Mn Mp Mq Mv Mw Nf Nh Ni Nk Nm Nn Nr Nt Nx Ny Oe Oi Oy Oz Pb Pc Pz) Nu(Co Hq Hv Hw Hx Ip It Jg Js Lh Lv Lw Lz Ma Mc Md Mi Mj Mp Mq Mw Mz Na Ni No Nq Nt Nv Ny Og Oh Oi Pa Pe Po Pz Qa Qe) Jj(Hq Hr Hw Hx Ih In Io Iq It Jm Lj Lu Lz Mb Me Mf Mh Ml Mn Mx Nb Nc Nd Ne Nf Nk Nl Nr Oe Og Oi Oy Oz Pa Pb Pc Wm) Nt(Hr Hv In Ip Ir It Jg Jr Js Lv Mc Md Mh Mj Mp Ms Mv Mw Mz Nd Ni Nk Nr Ns Oe Of Og Oh Oy Qa Qe) Jn(Hq Hr Hw It Jg Jr Lh Lv Lz Mb Mc Mf Mg Mj Ml Mn Mq Mr Nb Nk Nm No Nr Og Oh Oy Pb Pc Pe Po) Jr(Et Hr Ih Ij Iq Jg Lh Lv Lw Ma Mc Md Mg Mi Mn Mp Mq Mv Mz Nb Ni Nm Nn Ns Nv Oh Pc Po Qa) Oh(Hv Ih Ik Io Iq Jg Lh Lw Ma Mc Md Mg Mi Mj Ml Mp Mr Mv Mw Mz Na Nh Nk Nn Nq Ns Qd) cS(aF AL aQ aR aS aU aX Ba Bc bF bH cG cL CO Cq Cs cV cY Dc dD dE dF Dg dL) Mv(Bc Et Il In Ip Iq Jq Js Lw Ly Mj Mr Mz Ng Nh Nm Ns Nx Of Oi Oy) bZ(aF aH aP Ar bA Bc bl bJ BO bQ bR bU cA cC cM cR cW cX dL) Ba(AD al aN aW bG bJ bN bO bR cB cC cF Co Cp Cs dB dM Mr) Hv(Et Hr Ik Ip Jg Jq Lh Ma Mh Mj Mw Mz Ni Nq Nv Po Qa Qd Qe) In(Bc Co Di Et Jg Lh Mi Mj Mm Mr Mz Nn No Nq Nv Pd Po Qd Qe) Co(aW aZ Bc bJ bN bR bU bX cA cC cl cX dB Dd Fw Mr Nk) bA(aE al aM bB bC bF bH bL bM bN bS bX cA cC cK De) dK(aD aI aJ aO aP aY bE bR bX cD cF cH cI cN cR) Mc(Di Jg Lh Mp Mw Mz Nb No Nv Po Qa Qd Qe) Mr(Af Ao As Bg Ct Cv Cx Hr Ir Jg Mp No Wm) Mz(Hr Ik Ir Iu Ma Mg Mh Mi Mp Ni Nq Po) Nb(Hx Lz Md Ml Mn Mp Nn No Ns Pe Wm) cT(bJ bM bN bR bX cB cC cF Cp cR) Hr(Et Jq Lh Lv Mp Mw Qa Qd Qe) aP(aI bN bS cD cF cH cI cK cR) Nn(Ij Ir Lw Md My Ns Oy) Mp(Hw Ma Md Mj Ni Ns Wm) aJ(aD bN cD cH cI cR cX) Lv(Et Jt Nc Nh Qa Wm) Mw(Ih Ir Md Ni Ns Oi) aX(aD aE Bo bX cI cP) Ni(Bc Et Js No Nv) Om(Et Mm Qa Qd Qc) bV(bU cC cD cR cU) cP(aU bO bU cO cU) Ef(Bc Bo Cs Ct) Wm(Is Mi My On) Mg(Af Mj Oi On) Ir(Lh Lw Ml Nx) cR(aY Bg bX dM) Po(Md Nh Ns) Jg(Js Lw Nk) Nv(Md Nh Ns) Oi(Et Qa Qd) bE(bU cW dR) Cp(cX Fw) No(Mb Og) Is(Al Dd) Js(Ma Nq) On(Cq Dc) bH(bU bX) cI(aI cG) CtcH NmOg LhPc bXcO

Unconstrained panels with 2 analytes, where 1.0E-2 >= 'AUC p-value' > 1.0E-3. Contains 3,208 panels of 19,595 total panels evaluated. : aA(Aa aC Ad Af aG aH aJ aL aM Ao aP aQ aR aS aV aW aZ bA BB bE Bg bL Bo bP bQ bV bW cE cG Ch cJ cL cM cN CP cQ cT cV cZ dB DE dF dH dI dJ dL dM eF Fp gL gP Hq Hu Hw Hx Ih Ii Ij Ik Il Im Io Iq Ir It Iu Jk Jm Jn Jo Jq Js Jt Lh Lj Lu Ly Lz Mb Md Me Mi Mj Mk Ml Mq Mr Ms Mw Mx My Na Nb Nc Nd Ne Nf Ng Nh Nj Nk Nl Nm No Nr Ns Nx Ny Oe Of Og Oi Oy Oz Pb Pd Pe Pg Qc Qd Qe Wm) Co(aC AD aE AF aG aH aI AJ aK AL aM AN AO AP aQ AR aS aU aV Aw AX aY BB bC bE bF BG bI bL bM Bn BO bP bQ bS bV bZ cB cD cE cF cG CH cK cL cM cN cO Cp Cq Cs Ct Cv CW Cx cZ dA Db DC dD DE dF DG dH DI dJ DK DL dM Ef Fr Hq Hr Hv Hw Hx Ih Ii Ij Ir Iv Jk Jl Jm Lw Mc Md Mh Mi Mt Nc Nd Nh Ni Nj Nv Ny Of Oi On Pb Pg Pz) Cu(aC aG aL AO aR bB bC bE bF bG bH bI bL bM bP bV bW bZ cB cG cH cN cU cY cZ dA dD DE dL dM Ef Et Fp Gl Hu Hv Ik Il Im Io Ip Iq Ir Is It Iu Iv Jg Jh Jk Jl Jn Jp Jr Jt Lh Li Lj Lu Lv Lw Lx Ly Lz Ma Mb Me Mf Mg Mj Mk Ml Mm Mn Mp Mq Mu Mv Mw My Mz Na Nb Nc Ne Nf Ng Nh Nl Nm Nn Nq Nr Nt Nw Nx Oe Oh Ok Om On Pc Pd Pe Pf Po Qa Qb Qc Qd Qe) Qe(Et Fp Hq Hu Hw Hx Ih Ii Ij Ik Il Im Io Ip Iq Ir It Iu Jg Jk Jm Jn Jo Jq Jr Js Jt Lh Li Lj Lu Lv Lw Lx Ly Lz Ma Mb Md Me Mf Mg Mh Mi Mj Mk Ml Mm Mn Mp Mq Mr Ms Mu Mv Mw Mx My Mz Na Nb Nc Nd Ne Nf Ng Nh Ni Nj Nk Nl Nm Nn No Nq Nr Ns Nv Nx Ny Oe Of Og Oh Oi Ok Oy Oz Pa Pb Pc Pd Pe Pg Po Pz Qa Qb Qc Qd) Qa(Et Fp Hq Hu Hw Hx Ih Ii Ij Ik Il Im Io Ip Iq Ir It Iu Jg Jk Jm Jn Jo Jq Js Jt Lh Li Lj Lu Lw Lx Ly Lz Ma Mb Md Me Mf Mg Mh Mi Mj Mk Ml Mm Mn Mp Mq Mr Ms Mu Mv Mw Mx My Mz Na Nb Nc Nd Ne Nf Ng Nh Ni Nj Nk Nl Nm Nn No Nq Nr Ns Nv Nx Ny Oe Of Og Oh Oy Oz Pa Pb Pc Pd Pe Pg Po Pz Qb Qc Qd Wm) Nv(Et Fp Hq Hr Hu Hw Hx Ih Ii Ij Ik Il Im Io Ip Iq Ir It Iu Jg Jk Jm Jn Jo Jp Jq Js Jt Lh Li Lj Lu Lv Lw Lx Ly Lz Ma Mb Me Mg Mh Mi Mj Mk Ml Mm Mn Mp Mq Mr Ms Mu Mv Mw Mx My Mz Na Nb Nc Nd Ne Nf Ng Nj Nk Nl Nm Nn No Nq Nr Nt Nx Ny Oe Of Og Oh Oi Ok Oy Oz Pa Pb Pc Pd Pe Pg Po Pz Qb Qc Qd) Et(Ba Fp Hq Hu Hw Hx Ih Ii Ij Ik Il Im Io Ip Iq Ir It Iu Jg Jm Jn Jq Js Jt Lh Li Lj Lu Lw Lx Ly Lz Ma Mb Mc Md Me Mf Mg Mh Mi Mj Mk Ml Mm Mn Mp Mq Mr Ms Mw Mx My Mz Na Nb Nc Nd Ne Nf Ng Nh Nj Nk Nl Nm Nn No Nq Nr Ns Nt Nu Nx Ny Oe Of Og Oh Ok Oy Pb Pc Pd Pe Pf Pg Po Pz Qb Qc Qd Wm) Lh(Fp Hq Hu Hw Hx Ih Ii Ij Ik Im Io Ip Iq It Iu Jg Jm Jo Jq Js Jt Li Lj Lu Lv Lw Lx Ly Lz Ma Mb Md Me Mf Mg Mh Mi Mj Mk Ml Mn Mp Mq Mr Mu Mv Mw Mx My Mz Na Nb Nc Nd Ne Nf Ng Nh Ni Nj Nk Nl Nm Nn No Nq Nr Ns Nt Nx Ny Oe Of Og Oi Ok Oy Pa Pb Pd Pe Pg Po Pz Qb Qc Qd Wm) Po(Fp Hq Hr Hu Hw Hx Ih Ii Ij Ik Il Im Io Ip Iq Ir It Jg Jk Jm Jo Jq Js Jt Li Lj Lu Lv Lw Lx Ly Lz Ma Me Mf Mg Mh Mi Mj Mk Ml Mm Mn Mp Mq Mr Ms Mu Mv Mw Mx My Na Nb Nc Nd Ne Nf Ng Ni Nj Nk Nl Nm Nn Nq Nr Nt Nx Ny Oe Of Og Oh Oi Oy Oz Pa Pb Pc Pd Pg Pz Qb Qd Wm) Mz(Fp Hq Hu Hw Hx Ih Ii Ij Il Im Io Ip Iq It Jg Jk Jm Jn Jo Jq Js Jt Li Lj Lu Lw Lx Ly Lz Mb Md Mc Mf Mj Mk Ml Mm Mn Mq Mr Ms Mw Mx My Na Nb Nc Nd Ne Nf Ng Nh Nj Nk Nl Nm Nn No Nr Ns Nx Ny Oe Of Og Oi Oy Oz Pa Pb Pc Pd Pe Pg Pz Qb Qc Qd Wm) Mw(Fp Hq Hu Hw Hx Ij Ik Im Io Ip Iq It Iu Jg Jk Jm Jq Js Li Lj Lu Lv Ly Lz Ma Mb Me Mg Mh Mi Mj Mk Ml Mn Mp Mq Mr Mv Mx My Na Nb Nc Nd Ne Nf Ng Nh Nj Nk Nl Nm Nn No Nq Nr Nx Ny Oe Of Og Oy Oz Pa Pb Pc Pe Pg Pz Qb Qc Qd Wm) Nt(Af Ba Cx Fp Hq Hu Hw Hx Ih Ii Ij Ik Il Im Io Iq Iu Jk Jm Jn Jo Jq Jt Li Lj Lu Lw Ly Lz Ma Mb Me Mf Mg Mi Mk Ml Mm Mn Mq Mr Mx My Na Nb Nc Ne Nf Ng Nh Nj Nl Nm Nn No Nq Nx Ny Oz Pa Pb Pc Pd Pe Pg Pz Qb Qc Qd Wm) aP(aC aD aE aF aG aH aK aL aM aN aO aQ aR aS aU aV aW aX aY aZ bA bB bC bE bF BG bH bI bJ bL bM bO bP bQ bV bW bX cA cB cC cG Ch cJ cL cM cN cO cP cQ cT cU cV cW cX cY cZ dA dB dC dD dF dG dH dI dJ dL dM fP Fr) Qd(Hw Ih Ij Ik Io Ip Iq Ir It Iu Jg Jk Jm Jn Jq Jr Li Lv Lw Lx Ly Lz Ma Md Me Mg Mh Mi Mj Ml Mm Mn Mp Ms Mu Mv Mx My Nb Nc Nd Nf Ng Nh Ni Nj Nk Nl Nm Nn No Nq Nr Ns Nu Nx Oe Of Og Ok Oy Pc Pd Pg Pz Qc Wm) Jg(Fp Hq Hr Hu Hw Hx Ih Ii Ij Ik Io Ip Iq Ir It Iu Jo Jq Jt Li Lu Lv Lx Ly Ma Mb Md Mg Mi Mj Mk Mp Mq Ms Mu Mv My Na Nb Nc Nd Ne Nf Nh Ni Nj Nm Nn No Nq Nr Ns Nx Ny Of Og Oi Oy Oz Pa Pb Pd Pe Pg Pz Wm) cR(AD aE Af aI Aj aK Al AN AO Ap Ar As aV AW AX Bb Bc bE bH bI bL Bn BO bP bR bU bW cA cC cD cF cG Ch cI cM cN cP CQ Cs Ct CW Cx cY dA Db Dc Dd DE dF DG dH DI Dk DL) Oh(Cs Fp Hq Hr Hu Hw Hx Ii Ij Il Im Ip Ir It Iu Jk Jm Jo Jq Js Jt Li Lj Lu Lx Ly Lz Mb Me Mf Mh Mk Mm Mn Mq Ms Mx My Nb Nc Nd Ne Nf Ng Nj Nl Nm No Nr Nx Ny Oe Of Og Oy Oz Pa Pb Pc Pd Pe Pg Pz Qb Qc) Jr(Fp Hq Hu Hv Hw Hx Ii Ik Il Im Io Ip Ir It Iu Jk Jm Jo Jq Js Jt Li Lj Ly Lz Me Mf Mh Mj Mk Ml Mm Mr Ms Mx My Na Nc Nd Ne Nf Ng Nh Nj Nk Nl No Nr Nx Ny Oe Of Og Oi Oy Oz Pa Pb Pd Pe Pg Pz Qb Qc) Mv(Ao Ar Db Dd Dk Fp Hq Hr Hu Hw Ih Ii Ij Ik Io Ir Jm Jo Jt Li Lj Lu Lv Lz Mb Mc Md Mg Mh Mi Ml Mm Mn Mq Ms Mx My Na Nc Ne Nf Ni Nj Nk Nl Nn No Nr Ny Oe Og Oz Pa Pb Pc Pd Pe Pz Qb Qc Wm) Fr(aC Af aG AJ aK Al aM AN Ao Ap aQ aR aS aU aV Aw aX BA BB bF BG bI Bn bS bV bW bZ cB cG Ch cJ cL cN Cp Cq cS CT CW Cx cY cZ DC DD De dH DI DJ Fw Lj Qc) Mp(Fp Hq Hu Hv Ih Ij Ik Il Im Ip Iq It Iu Jm Jo Jq Js Lu Lw Ly Mb Me Mf Mg Mh Mi Mk Ml Mn Mq Mx My Na Nc Nd Ne Nf Ng Nh Nj Nl Nm Nn No Nq Nr Nx Ny Oe Og Oi Oz Pa Pc Pe Pg Pz Qb) Hv(Ba Fp Hu Hw Hx Ih Ii Il Im Iq Ir It Iu Jk Jn Jo Jt Li Lu Lw Lx Ly Lz Mb Mc Md Mf Mg Mi Mk Ml Mm Mn Mq Ms Mx My Na Nb Nd Nh Nj Nk Nm Nn No Ns Nx Ny Of Oi Oy Pc Pd Pg Qc Wm) bZ(aD aG aI aJ aK aL aM aN aO aQ aR aS aV aW aX aY Ba BB bC bE bF bG bL bM bN bP bS bV bW cB cF cG cH cJ cK cL cN cO Ct cV cZ dA DB dC dD dE dF DG dH dI dJ Dk dM gP) cP(aE aF aI aJ aK aM aN aO Ap aV AW aY bA Bb bC bE bF BG bH bI bJ bL bM bN bR bV bW bX cA cB cC cD cE cF cG CH cI cK cL cM Cp cT cV cW CX cY dD dE dF dH dI gL) Nu(Bc Di Fp Hr Hu Ih Ij Ik Il Im Io Iq Iu Jk Jm Jo Jq Jt Li Lj Lu Ly Mb Mf Mg Mh Mk Ml Mm Mr Ms Mx My Nd Ne Nf Ng Nh Nj Nk Nl Nm Nr Nx Oe Of Oy Oz Pb Pc Pg Qb Qc Wm) Ba(aE Af aL aM aO aR Aw aZ bB BC bE bM Bo bS bX cA cJ cK cM cO CQ Cw Cx Db De dG dH Di dJ dK DL In Is Ji Jl Jp Jt Mc Mg Mm Na Nh Ni Nk Oi Ok Om On Pb) Lv(Bc Fp Hq Hw Ii Ik In Ip Iq Ir Jk Jq Li Lj Lu Lw Ly Lz Mb Md Mf Mg Mj Mk Mm Mn Mr Ms Mu Na Nb Nd Ne Nk Nl Nm Nn No Ns Nx Ny Oe Of Og Oi Oy Oz Pa Pc Pd Pe) Mr(Ad Aj Al An Ap Ar Aw Ax Bb Bc Bn Bo Ch Cp Cq Cs Cw Db Dc Dd De Dg Di Dk Dl Hw Ii Ij Im Ip Jk Jq Li Lw Lz Ma Mj Mm Mn Nb Nd Nm Nq Nr Og Pa Pc Pe Qc) Jn(Fp Hu Hx Ih Ij Ik Il Im Io Ip Iq Iu Jk Jm Jo Jq Js Li Lj Lu Ly Me

Figure 2 Continued

Mh Mk Mm Ms Mx My Na Nc Nd Ne Nf Ng Ni Nj Nl Nx Ny Oe Of Oi Ok Oz Pa Pg Pz Qc) Lx(Cs Fp Hq Hr Hu Ik Il Im Io Ip Iu Jk Jm Jo Jq Js Jt Lu Ma Mb Mc Mf Mg Mh Mj Mk Mm Ms Mx My Na Nc Ne Ng Nj Nl No Nq Of Og Pa Pd Pe Pg Qb Qc Wm) dK(aE aK aM aN aQ Ar aV aX aZ bB BC bF BG bJ bM bN bO bV cA cB cC cE cG cK cM cO Cp cQ cU cV cW cX cY dA dF dG dH dI dJ dL dM gL) Ok(Fp Hq Hu Hw Hx Ii Il Ip It Jk Jq Js Jt Lj Ly Lz Mb Me Mf Mj Ml Mm Mn My Nb Nc Ne Nf Ng Nj Nl Nr Nx Oz Pa Pb Pe Pg Qb Qc Wm) Mg(Bg Bn Cx Dd Hr Hu Ih Ii Ij Ik Im Ip Iq Ir It Jq Js Lw Ma Mc Md Mh Mi Ml Mq Mx My Nb Nd Ng Ni Nn No Nq Ns Og Pa Pc Pz Wm) Js(Fp Hr Hu Hw Ik Im Io Ip Iq It Jk Jm Li Lw Mb Mc Md Mf Mh Mj Mk Mm Mn Mq My Nb Ng Nh Nj Nm Nn Ns Oe Og Oi Pc Pg) Nn(Cq Hq Hr Hu Hw Hx Ih Ik Io Iq Jq Ly Lz Me Mf Mh Mi Mj Ml Mn Mq Mx Na Ni Nk Nm No Nr Nx Ny Oi Pa Pb Pc Pe) bA(aC aF aL aN aO Ar aU Aw aX aY Bb bE BG bI bQ bV bW Ch cL cM cO cT Cx cY dA dC dD dG Dl dJ dL gP) In(Ad Ap Aw Bb Dl Fp Ih Ii Ij Ik Il Ip Ir Iu Jk Jq Jt Li Lj Lw Ma Mq My Na Nb Nl Nr Nx Pe Pg Qb Wm) Cp(aE aH aI aL aW aY aZ Bc bJ bO bU bX cA cC cD cH cI cK cM cO CS cW dB dN Hr Iu Jj Mt Nk Oy) Pf(Af Al Bc Bo Cq Cs Dc Dd Di Hx Ii Il Iu Jk Jo Lu Mb Me Mf Mk Mm My Ne Ny Pa Pd Pe Qb Qc Wm) dN(Ad Af Aj Al An Ao Ap Ar As Aw Ax Bb Bc Bn bQ Cq Cs Ct Cv Cw Cx Db Dc Dd De Dg Di Dl fP) bU(aD aE aI aO Aw aY Bc Bg bL bN bO bW bX cG cI cO cQ cU cW cX dA dE dF dG dH dL dM gL) cT(aE aF aI aL aM aN Aw aY BB bC bE bF bH bI bL bO bW cG cM cO Cx dC De dH Di dL gP) Mu(Ar Dd Fp Hu Hx Ii Il Ir It Iu Lj Mf Ml Mn Mq Ms Nd Ne No Nr Oe Og Pb Pe Pg Qb Wm) bV(aD aE aI aK aM aN bB bE bJ bL bM bN bO bR bW bX cA cB cF cG cH cI cM cO cX dL) Nq(Bc Dd Fp Hr Hu Hw Ik Ip Ir Jm Jq Jt Lw Ly Mc Me Mn Ms Nh Nm No Ns Nx Ny Pc) Mj(Hr Ik Ip Ir Jm Jt Li Lw Ma Mc Mh Mi Mm Mn Mq My Nb Nh Ni Nj Nm Ns Oe Pc Pd) aI(aE Af aH aJ An Ap Ar AW aY BB Bc bE Bo bX cC cQ Ct Cv Cx dA Di dM) bX(aE aJ aM aO aS aU aY bE Bg bL bO bW cG cI cM cQ cU cV cW dA De dF dM) cS(Ad Af An Ao Ap Aw Ax Bb Bg Bn Ch Ct Cw Cx Dd De Di Dk Dl dR fP gL gP) Jp(Af Al Cq Dc Dd Ii Ij Il Jk Jo Jq Mb Me Mf Nl Nr Ny Oz Pa Qb Qc Wm) Bc(aU AW aX bF Bg CH cO CX cY Di Jj Jl Ma Nj Nk Og Oi On) Ir(Ij Ik Ip Iq Jq Lz Mc Md Mi Mn Mq Na Ni Nk Nm Nr Ns Ny Oe Oi Pb) Ma(Ar Dd Ik Ip Iq Jo Jq Li Lw Ly Mc Mn Na Nb Nh Nm No Nx Ny Pc) aJ(aE aM aN aY bF bG bJ bO bS cA cB cC cF cK cM cO cU dD dG eF) Nb(Hq Hr Hw Io Ip Jo Mh Mi Mq Mx Na Nf Nk Nm Nr Nx Pa Pb) Ni(Aa Af Ar Ii Ip Jk Jq Jt Lj Lw Mm Mn Nx Pa Pc Pd Qb Wm) Bg(aW bE BO cC cD cI cO cX dB Dk dL Ef Jj Mc Mt Oy) On(Aa Ad Af Aj Al An Ao Ax Bn Cs Ct Cv Cx Dd Dg Di Dk) Mt(Ad An Ap Ar As Aw Ax Bn Ch Ct Cv Cw Cx Db De Dl) Jq(Ik Ip Iu Li Lw Mc Md Mi Na Nh Ns Oe Og Oi Pc) No(Hr Ih Ip Iq Md Mn Na Nk Ns Ny Oe Oi Oy Pc) Ar(aO aU aW aX bF bH cG cH cO cX cY dF) bE(aC aE aN aY bF bO bR Ch cI cZ dD gL) eF(aC aM aU aX aZ bP cZ dE dI dM dR gL) Mi(Hr Hw Ip Jt Lu Lw Mm Mn Nm Nx Og) aE(aO aU bC cG cO cY dF dH dI gL) cD(bH bO cG cO cW cY dG dI dM gL) cI(aO bR bW cO dF dG dH dI dL) Ef(Aj Ao Ax Ch Cq Db Di Dk) Mc(Aw Cw Fp Ij Jk Li Mn Pe) Nk(Af Cv Cw Cx Di Jk Li Pe) Oi(Ii Jk Jt Mm Nx Pd Pg Wm) Ip(Ik Lu Mq Ms Ne Nx Og) Is(Aa Af Bn Cq Cv Dc) Jl(Af Bn Cq Cv Dc Ne) bR(aX bW dG dH dI dL) Ns(Jk Li Mn Ny Pe) Lw(Ij Ik Im Lu My) Om(Af Al Cq Dc Dd) gL(aF aN bI bQ cC) Di(cO Ct Cw Jh) Wm(Li Mm Nd Nh) Md(Li Mn Ny Pe) Mq(Hr Hw Mn Nx) Jj(Ad Aj Ch Cx) cX(aO Aw Bb dI) Hr(Ik Jo Nx) aD(cL cY dI) aX(bO cW Db) aY(aU bW cO) dL(bF CH) Bo(cG cO) Ik(Nd Pc) Jk(Jm Nh) aO(aF bJ) bN(dG dH) cQ(cU De) dM(cB cU) AncO CsGl CtaW DdJi NmMb LuMm LzPe MhJt HwNy ImNx bOdI cCcW

Constrained panels with 3 analytes, where 1.0E-8 >= 'AUC p-value' > 0. Contains 813 panels of 939,239 total panels evaluated. : Jj{Ma(aA Fr Hv Ii Il Is Iu Iv Jh Ji Jk Jl Jp Jq Jr Jt Lh Lv Lw Mg Mj Mp Mr Ms Mt Mu Mv Mw Mz Nh Nt Nu Nv Nw Nx Oh Ok Om On Pa Pc Pd Pe Pf Po Qa Qd Qc Wm) Lv(aA Fr Hv Ii Ik Il Iu Iv Jh Jk Jl Jp Jt Lh Mg Mm Mp Ms Mt Mu Mv Mw Mz Nh Nt Nu Nw Oh Ok Om Pf Po Qd) Mg(Fr Hv Il Is Iv Jh Ji Jk Jl Jp Mj Mt Mu Mv Mw Mz Nu Oh Ok Om On Pf) Iv(Fr Hr In Jg Jh Ji Jk Jl Lw Md Ml Mt Mu Mv Mw Mx Nn Nt Ok Om Pc) Jh(Hv Il Is Iu Ji Jl Md Mj Mp Mu Mz Ns Nt Nu Oh Ok Pf Qd) Il(Et Hv Ik Ji Jp Mm Mp Mt Mw Mz Nn Nu Nx Of Oh Ok) Md(Fr Is Ji Jk Jl Mt Mu Mv Nt Nv Ok Om On Pf) Mu(Hr Is Iu Ji Jl Lw Mj Ns Nt Nu Ok Pd Qd) Hv(Ik Mt Mv Mw Nt Nu Of Oh Pf Qd) Is(Fr Hr Ih Ml Mx Nt On Pc) Mv(Lw Mz Nu Nw Oh Ok Qd) Mw(Ik Jr Lw Mj Mr Nu) Jl(Hr Ji Lw Mx Nt Ok) Fr(Ji Lw Nh Ns Nt) Mt(Iu Mi Mp Nn Ns) Ik(Jp Mz Nd Oh Qd) Hr(Ji Om On Qd) Pf(Ms Mz Nn Nu) Ok(Jk Lu Nn) Nu(Jr Mz) Ji(Iu Ml) On(Mx No) CuHx NtOm} Is{In(Fr Hr Hv Ir It Iv Jh Ji Jl Lw Md Mg Mi Mx Nb Ni Nt Om Pa Pc Pe) Qb(Fr Jh Ji Jl Lv Lw Md Nn Nt Nw On Pc Pf) Oi(Fr Hr Jh Lv Lw Md Mg Nn Nt On Pc Pf) Jm(Fr Hr Jh Lv Lw Md Mx Nn Nt On Pc) Hr(Ih It Iv Jh Ji Lv Md Mi Ni) Ih(aA Iv Jh Md Nt Pf) Md(aA Om On) It(Ir Iv) Pc(aA Nk) FrNg MxaA OgOn} On{In(Hu Iv Lv Lw Md Mg My Ng Ni Ns Nt Ny Of Oy) No(Hr Hu Ji Md Ms My Ng Nv Of Og Oy) Iv(Ij It Md Mx Nv Ny Og Oi Qb) Oy(Jl Ma Mg Mt Mu Mv Nq Om Oz) Md(Ji Lv Mc Ni Oe Oi Pz) Ni(Ij Mx Nf Ny Of) Nv(Hv Mt Mu Om) Oi(Hr Hu Mg Pc) Mx(Ng Of) LvOf MgPz NgJh HvNy OgOm} Fr{Iv(Hr In Jm Lw Md Mx My Ng Ns Of Oi Oy) Ji(Hr In Jq Md Mx Nf No Ns Of Oy) Hv(Hu In Md Ng Ns Of Oy) bQ(aX BA bZ cR cS cT) Bo(aW aX bE cR cS) Dk(bE bU cC cR cX) Om(Hu Md Ng Of Oy) Oi(Md Mg Nh Nt) cP(aF aL aW bE) cC(aE dK) NrNt aAcX bEcD} aA{cX(bR bU bZ cA cD Ch cI Co cS De dG) bZ(aF bJ bQ bR bU cC cI dF) Om(Hr Hu In Jr Md Ns Oy) bU(aF aX bH bJ cI cS) Lv(Hr Jr Lw Md) cS(bN bR cI dG) Ji(Hr Md Mx) MgIn aFbF bJbR bNdK dGdN} In{Cu(Cq Dc Hx Ii Md Mg Mx Nh Nk Nu Nv Ny Of Oy Pg) Ji(Hr Ir Iu Iv Jh Md Nt Wm) Iv(Jh Jl Lw Oh Om) Mt(Jr Lw Ns) Om(Hr Ir Md) Mg(Bb Nb) NtJs LwMw LxNd MdMp HrHv} cS{bR(aJ aN bA bN cI cN cP cQ cT dA) bU(aJ bA bN bZ cI cN cP cQ cT dA) cP(bA bE Bg bN bZ Ch cI) bN(bA cD cI cT dN) cI(bA cQ cT eF) bA(bJ bQ) BaBo bQeF cDcN} eF{bE(aD aE aF aG aN aW cE cI dF dK) cI(aF aX bA cT dK dN) dN(bQ cE cV dF dG) cC(aE aG aW dK) aF(aG bQ cP) aE(bR cV) bQ(bZ dK) bHcD bZdF} bA{bU(aE aY bJ bZ cI cO cR dK dN) cI(aD aI bJ bR cB cR) bZ(bQ bR cC cD cE) dN(bJ bN dG) aD(bJ bN) cU(bR dG) cDcO cRdK} cT{dN(aE Bg bJ bN bU dG dK dL) bU(aE aY bH bL dK) aD(bJ bZ cI dK) bZ(bQ cC cE) cD(aX bH cO) bR(cI cU) CobQ aIcI} Om{Md(Hr Hv Iv Of Og Oi Oy) Hr(Hv Iv Ng Ns Of Oi) Oy(Iv Jl Mk Nb Oz Pa) Ir(It Ml Mx) Oi(Iv Oh Pf) LuOf} Ji{Ir(Hv It Jn Jq Jr Js Md Ml Mx) Hr(Iv Jh Lu Md Ml Mu Mx Pf) Md(Mc Mv Ni) Iu(It Mx) MvIj} dN{bU(aJ aX Ba bH bZ) bN(aJ aX Ba dK) bZ(bX cE) dK(cP cR) BaBg bQgL} cP{bZ(aF bQ cC cE dK) Co(Ao aW) Cu(aW cX) aX(bU cD) bUdK} Ba{aI(aH bJ) bQ(bZ Cu) bU(cR cU) cC(bZ Ch) bRcH} Cu{Mc(Js Lz Md Mx Nk Nu) DcNk MvOy} Hr{Lv(Hv Iv) Nw(Ni Oi) MaIv} Oy{Bc(Mv Nq) Mg(Bg Ch) CoNu} aP{bR(cH cI) bU(aX cI) bQbZ} Oi{Iv(Jh Mv Pf) WmMg} aX{aE(bU cD) bUcI cDdK} Mr{Ir(Ax Cs)} aJ{bRcH bUcI}

Constrained panels with 3 analytes, where 1.0E-7 >= 'AUC p-value' > 1.0E-8. Contains 610 panels of 939,239 total panels evaluated. : Jj{Hv(Et Hr Iu Jg Jp Jt Lh Md Mj Mm Mz Nv Nw Nx Pd Qe) Mi(Jh Jk Lv Ma Mu Mv Mz Nt Nu Oh Pf) Mg(aA Ch Jr Lh Md Nt Nw Qa Qd Qe) Nn(aA Jp Lv Ma Mj Mz Nt Nu Qd) Nu(Iu Mj Mp Mq Of Oh Qa Qe) Il(Hr Iu Jq Jr Jt Lw Mq Ms) Qd(Iu Jg Lw Ml Mp Mx Ok Pc) Jr(Et Ik Jp Mm Nq Of) Pc(Jh Lv Mt Nt Ok Pf) Md(Cu Js Nw Oh Qa) Lv(Jg Lw Nq Wm) Mp(Jp Mj Mv Mz) Hr(Mr Ok Pf Qe) Ik(Js Mj Mm Ms) Iu(Mz Nw Nx Pf) Lw(Jh Mt Pf) Ma(Jg Nb Oz) Cu(Mx Pe) Mr(Mm Of) Mz(Mj Pd) Ok(Mt Nt) PoMs NsNv MlQa MnaA MqJp MvLh MwPd MxJi JgPf JhLi} Is{Md(Fr It Jh Ji Lv Mi Mv Ni Nn Nt Pc Pf) Mx(Hv Ih Ir Iv Ji Lv Ni Qb) Ih(Ji Jl Lv Lw Mi On Pc) Hr(Lw Ma Mg Mu Nt Ok) In(Jt Lh Ma Ml Ok On) Fr(Hu My Ns Of Oy) Jh(It Ns Of Oy Pc) Om(Ij Ns Of Og Oy) Jm(Ma Mg Ml Mu) Nr(Mt Nt Pf) Ni(Ij It Of) Qb(Mg Mi Mu) Oi(It Ma Mu) On(Nv Ny Oy) Ir(Js Ml) aA(Ma Mg) NbNy HxJl JiJq OgOk} Iv{Ma(aA Fr Hv Jh Jp Lw Ms Nw Om On Pc) In(Hr Hv Mg Mt Mu Mv Mz Nt Nw Ok) Hr(Jh Jl Jp Mt Mu Oi On) Md(Jh Ji Jp Lv Mu Nq) Jh(Lv Mu Ng Of On) Jp(Ih Lv Lw Nk Oi) Mu(Lw Nk Oi) Jl(Ih Mx Nk) Lv(Fr Nw) MxJi NkPc NwOi OfOm} On{Ji(In Mx Nf Nv Og Oy) Pc(aA Md Ng Ni Of Oy) Ma(Md Ng Ns Nv Of) Ny(Ir Jl Lv Mt Nb) Lw(Hv Nx Og

Figure 2 Continued

Oy) Ni(Hr Ml Nx Pb) In(Hr Ir Mt Om) Mg(Ng Of Og) Oy(Fr Jh Mx) Md(Fr Nn) Ng(Hr Mu) Jl(Hx Ii) Nv(Lv Mn) NsMt MxaA HrOf HvOg PaPf} aA{Om(Ij Lw Ma Mx Nf Ny Of Pc) Lv(Ma Me Mn Mx Nn Nw Pc) In(Jr Mn Mz Nw Oh Wm) Ma(Jr Lw Mz Nw Pc) bU(aW bE cT Cx) Jr(Jh Mn Pc) bJ(cl dK) bZ(cE dG) cR(Cx dK) cX(aF Bg) CobQ MzHr NfJi aXcD bRcU bScS} Ji{Mv(Hr Jq Mx Nf Ny Om Pb) Fr(Mt My Mz Ng Ny) Md(Jp Lu Mt Om Pf) Ni(In It Ml) Hr(Jn Ma Mg) Mx(In Lu) Og(Jn Jr) Nflr HxJl InJq luNy JhOf} Om{ln(Hu Hv lu Ns Nt Of Oy) Md(Hu Mc Ng Ni Oe) Jh(Fr Ns Of Oi) Hr(Lv Mi Mr) Oy(Hv Pe Pf) FrMy MtOi MvHu HvOf IrJn OgOk} cS{bZ(bQ bR cD cE) bE(aC cK cZ) bU(aN aX eF) cP(aF cT Fr) bN(aJ bX) bR(aW eF) cl(al cM) cT(aD bJ) dG(bA eF) BocX bQgL} bA{bJ(aE Bg bO bR bZ cD Ch) bU(aX bE cP Cx Fr) bN(bM cR dK) bR(cR dK) cl(bZ dK) CudM aEcB} In{Mt(Hv Mi Mp Ok Pc) Mg(Mi Oh Ok) Hv(Mv Nt Oh) Lw(Mi Mu) Jr(Mi Mp) BcMa CuPb NtQa luNw} Fr{Ng(Jh Lw Mg) Hv(Hr Lw My) Dk(aW cP) Md(Mc Nw) Nb(Of Oy) cR(aW cX) JlOi OyOz aLcT} dN{cP(Bg bN bU cR) aX(bR bX dK) cT(aF aM aW) aP(bR bU) BgcR aJbR bHbX bUdK bZcA} bU{bE(cW dK eF) Ba(aW aY) aX(aY dK) bZ(aJ dK) cP(bH dl) aEeF aPbR} Cu{Mc(Nj Nv Pe) Nk(Hw Md Nu) bJ(cP cT) DcOi NoHr NqOy LwIi} Oi{Mg(Jp Nw Oh Pf) Jh(Nw Oh Pf) Lw(Mt Pf) MtPf HrQd} cT{bJ(aN Bg Ch cI) aX(aD cI) bE(Bg Ch) bZcP} cP{aX(Bg Ch cI) bZ(aW bE) dK(bW cR)} eF{aG(bR cV) bE(bQ cD) aHbR aNcV bZcE} Ba{bJ(bZ cU) aIaW bRcU} Md{Lx(Nb Pc) Mt(Mc Nb)} Hr{Hv(Jh Mu) LvNw NkJl} Dd{LvMg LwMv} Nk{AfLx JlPc} bE{gL(aF cI)} CoHuOy CqMrIr NsMvHv LwIlJm aIaJcI aPbRbZ Constrained panels with 3 analytes, where 1.0E-6 >= 'AUC p-value' > 1.0E-7. Contains 1,117 panels of 939,239 total panels evaluated. : Jj{Mp(aA Et Hv Ii Ik Jr Jt Lh Md Mr Ms Mw Nh Ns Nx Of Pd Qa Qe) Iu(Et Ik Jp Jq Jr Js Jt Lh Mj Mm Mr Ms Mv Mw Nv Oh Pd Qa Qe) Nn(Et Hv Ik Jr Jt Lx Md Mm Mr Ms Mw Nh Ns Nx Of Pd Qa Qe) Cu(An Bn Cp Cq Cs Dc Dd Hw Ij Js Ml Nu Ny Oy Pb) Pc(Et Hv Ik Il Jp Mg Mj Mr Mw Mz Nu Nw Oh Qa Qe) Nq(aA Ip Jn Jq Md Mm Mr Ms My Nh Ns Nx) Jg(Il Jr Md Mj Mr Mz Ns Nu Oh Qa Qe) Lw(Et Hv Ik Jp Mz Nu Nv Oh Qa Qe) Md(Ii Ij Jq Jt Lh Lx Po) Nu(aA Ii Mr Oz Pa Pe) Mg(Bg Hr Mi Nh Oz Po) Mi(Ik Lh Mw Nx Qe) Ms(Ip Jo Jr Li Pd) Hr(Js Lh Mj Nv Qa) Mq(Js Mm Mz Of) Jr(Ip Jo Jt Pd) aA(Il Lx Mw Pd) Hv(Ii Ip Ml) Lv(Oz Pa) Ii(Mw Mz) Jp(Lh Pa) CsMt WmIn NsLi MlJs JiJq} In{Nt(Bc Fr Jh Jl Jp Jr Lx Mj Mp Ms Mt Mu Mz Nh Nw Oh) Mg(Hv Ir Ji Jl Jp Jr Mr Mt Mu Mz Nw Pa Pc Pe) Iv(aA Il Jg Jt Lh Ma Mp Ms Mw Nn Nq Pc Qa) Om(Hx Jl Lh Lw Mi Mr My Nb Ng Pa Pc Pe Qa) Hv(aA Et Jg Jh Jl Lh Mu Nw Ok Pf Qa) Mp(Hq Iu Jn Js Lw Nd Nu Pe) Mt(aA Cs Hr Ir Mq Mu Nb Pf) Ji(Jl Jo Jt Ma Ml Mu Nf Pc) aA(Ip Jg Mv Pc Pf Po) Nu(Bc Jh Jn Jr Qa) Ok(Hr Jh Ma Md Oh) On(Jh Ma Mu Mz Oh) Nn(Bc Jn Jr Js) Jr(Jh Mu Mw) Cu(Hw Mv) Lw(Jp Oh) Md(Lx Nm) Nw(Ir Mi) CoOy WmNh MuIs JhOh} Is{Md(Jg Jl Lw Lx Ma Mg Mp Mq Mu Nq Nw Ok) Ni(Hv Hw Jn Jr Js Ml Mz Nf Ny Pb Pc) Ji(Ij It Jn Js Mz Nf Ny Pb Pc) Mx(Jl Lw Mi Mu Nt Nw Om Pf) Ns(Jg Lw Mu Mv Nn On Pc) Mg(Ih It Lv Ng Of Og Oy) It(Lv Lw Ma Nt On Pc) Jh(Lv Lw Ma Mi Ng Ok) Oy(Jg Jl Mu Mv Nn Oz) Fr(Hr Lv Lw Mt) Of(Jg Mu Mv Nb) Ml(Lv Om Pf) Ij(Jg Lw On) Hr(Jl On) Ir(Jn Jr) Og(Jg Nn) Ok(Ih Qb) Pc(Lv Mi) NqMy NtNk LwHv LzJl OeOn} Ji{Mx(Hv Jh Jl Ma Mi Mj Mt Mu Ni Og Pa Pe Pf) Ni(Hv Hw Ij Jn Jq Jr Me Mz Nf Ny Pb) Md(Hv Jg Jh Ma Mg Mi Mu Nb Nn Nq) Ml(Fr Hv Jh Lv Mc Mv) aA(Jn Jq Jr Js Ma Pc) Lu(Jn Jr Js Mz Nf) Mv(Jn Jr Js Mz Of) Iv(Ij It Nf Pc) Mu(Jq Nf Of) Hr(Jl Jq Nf) Ny(Mt Nb On) Oy(Jk Mk) NsPc MaJq MgOi MtIj MzIr IlJm JhJl OfOm} Om{Of(Jl Lh Lv Ma Mi Mu Nb Ok Oz Pa Pe Pf) Md(Jl Lv Mi Mp Nn Nw Ok Pc Qa) Oy(Ba Jh Mi Mp Mu Nn Nw Pc) Oi(Jl Mg Nn Nt Pa Pc Qd) Ns(Jl Ma Mi Mu Nn Pc) Iv(Ij It Ml Mx Ng Ny) Hr(Jl Ma Mt Mu Pa) aA(Jn Js Ml Ok Pb) Ng(Jh Mt Mu Mv) Hu(Jh Ma Mu Pf) Ni(Ij Nf) Ir(Jr Js) Jl(Hw Hx) Og(Mu Pc) FrMw MyJh NbNy HvIj} Jh{Ns(Hv Jl Jp Jr Mc Mt Nt Nw Oh Pf) Md(Hv Jl Jp Jr Lx Mc Mt Nt Oh Pf) Hr(Jl Jr Mr Mt Mz Nu Nw Ok Qa Qd) Of(Fr Hv Jl Mt Oh Ok Pf) Oi(Jl Jp Mg Mt Mz Nt Nu) Oy(Jl Mk Nb Pa Pe Pf) Hu(Hv Mt Oh On) Iv(It Lw Ok Pc) Ng(Hv Mt Oh) On(Hv Nv Ny) Lv(aA Hv) MzaA} Iv{Oi(Et Jg Jl Ma Mg Mt Mz Nn Nt Oh Ok) Hr(aA Hv It Mi Mp Ms Mz Nw Ok Pf) Lv(It Lw Mg Ml Mx Ok Pc) Ma(Jg Mi Mu Mv Mz Nn Ok) Md(Jl Lx Mt Mv Nw Ok Pf) It(Jl Jp Mt Mu Mv) Nk(Hv Mv Pf) Mu(Mx Of) Jp(Mx Pc) Pf(Ih Lj) aA(Nn Pc) NqMy LwMv} aA{cS(aF aP cA cB cK dH) Ma(Hr Mn Ms On Wm) Md(Mn Mu Nn Nq Nw) bR(aE aF aX Cx) Mu(Lv Lw Ns) Jr(Hr Jg Mg) bJ(cA cB cK) cX(aW bE bX) Pc(Mz Nk) dK(cF dG) BabU WmOz FrdM NnNs LvMg LwPf HrNw aHaI bHcD bZdH cAcR} Mt{Md(Jp Jq Jr Lw Lx Mi Mp Mu Nn Nw Oi Oz) Oi(Cq Hr Jp Mg Mu Nn Ns Nt Nw Oh) Ns(Hr Hv Jp Lw Mp Mu Nn) Mu(Hu Ng Of Oy) Hr(Mr Nw Qd) On(Lw Mi Og) Cs(Ir Oy) BgOy CuNv CvNk NrPf MvNg} On{My(Hr Lw Ma Mg Mx Pc) Ny(Lw Mu Og Pa Pc Pe) Hr(Lv Md Mn Ns Oy) Nv(Fr Jl Mj Nq Nw) Ir(It Ml Mx) Pc(Mi Ms Ns) Fr(Oe Of) Mg(Hu Jm) Jl(Og Pg) CoOy LvPg LwMu MaHu MiMx} cT{bZ(aE aF bJ bR bX dF dK) bU(aJ aP aX bE bW dI) dK(bR cF cP cR) dN(aH Ax Cs dF) aY(bJ cD cR) Cu(aW Cs) Dk(Co Fr) aD(aF cR) bJ(aE Fr) bW(cD cI) aLeF bLcC} Oi{Nt(Hr Jp Mu Mv Mz Nw Oh Pf) Pf(Et Jp Md Mu Mz Nn) Cu(Hx Md Mx Of) Mg(Ir Jl Mu Mv) Hr(Fr Jl Ok) Lw(Jp Mu) EtMv FrQd MuNw} bZ{bA(aD aF bX cF dF) dK(bR bX cC cD cR) aE(bU bX cC) cE(aD aI aP) dN(aF aW dH) Ba(aZ bU) aX(cD cP) cI(cM cS) aHaI aJcP aPbU} cP{dK(bA bE BG CU) Co(aR aX Dk) De(Af aR aW) Fr(Ao aX cR) aF(aO dN gL) bE(Bg bU Ch) bU(aJ aP) CsCu aXbR cGcI} Fr{Oy(Co Jl Mk Pe) bA(bJ cX dM) Dk(aX Mr) Ng(Ik Nt) Ni(Md Of) bU(aX cS) MaHv JlOf aEaW bEcR cIcS} Cu{Nk(Cq Ii Of Oy) Ba(aW bJ Dc) Mc(Cs Ml Pg) Oy(Co Mu Nu) CtEf DccA JlNv aWcR aXcX} Md{Nw(Hr Lu Lv Mc Mv Ni) Hv(Lv Lx Mu Mv Pf) Ni(Lx Oh) Jn(Nn Nq) NuJp NkJl} dK{eF(aG bR cD cV) aJ(bR bU dN) bA(bJ cF) bU(cR dI) ArBg aIcI bRdH bXcR} cS{Ar(Bg Ch) bA(bE dH) bU(aW Ba) cI(aX cN) cR(bS cK) aDbN aJdG bEdD} aX{bU(aJ aW Co) cI(aD aI bX) dN(cA cK) aDbX aEbR} Oy{Co(Dg Lw Mi Mu) Mr(Mu Mv) BcMa MgNb MpMv} Hr{Jp(Hv Mr Ni) Lv(Mp Mz) Nw(Hv Ma) MrMu} bA{aE(bR cR dN) ChbU aFcR aHaI bJcB cIdN} eF{aL(aW bR bU) aE(aF bQ) aJdG bQbR} Lw{Co(Dd Ii) DdNq MuJm MvHv NkJl} dN{aP(cK dG) BaaW aJdG bHbR bNbX} Mv{Of(Bc Nb Ok) NsNw MgNg} Ba{McNh aWcR bEbU cCcU} gL{bE(aN aW) cI(cC cX)} Ml{Ir(Nb Nu Nw)} Ni{LxHq JpOh NwPc} Nk{Pf(Hv Jl) CoNc} Ct{Ef(Bc Dk)} Ns{NuJp MuHv} aP{aIcI bHbU} cR{BgDk CpcX} MgOgOk aJcDcX aYbEbU Constrained panels with 3 analytes, where 1.0E-5 >= 'AUC p-value' > 1.0E-6. Contains 1,654 panels of 939,239 total panels evaluated. : In{Lw(aA Il Ir Iu Jg Jh Jl Jn Jr Js Mg Mq Mv Nb Nw Pf) Hv(Ip Ir Jq Jt Ma Mm Mp Mw Mz Nn Nu Pc Po Qd Qe Wm) Nt(aA Et Il Ir Lh Ma Mv Nn Ns Nu Ok Pf Po Qd Qe) Jr(Et Iu Jg Lx Mm Mq Mr Mv Mz Nv Oh Pc Pd) Mg(Hx Jh Jn Js Lh Mj Mq Nn No Nu Oz Pf) Mp(aA Lx Mj Mq Ms Mw Mz Nx Oz Pa Pc) Mz(Hr Iu Mi Mt Mu Mv Nn Oh Pf Qa) Iv(Ir Iu Lv Mi Ml Mr Nb Pa Pe Qd) Nu(aA Ir Js Mi Mq Mr Mv Nn Wm) Ok(aA Lv Mi Mu Nh Nn Nw Pc Pf) Mt(Hx Jt Lh Mr Pa Pe Qa Qd) Js(aA Hr Jg Jh Ma Mq Nq Pc) Oh(Et Jg Jp Ma Mi Ni Qd) Mw(Ir Mr Nn Oz Pc Pe) Jl(Ir Jh Jt Md Ns Pf) Nw(Lh Mr Mu Nb Pc) Qa(aA Jh Jp Pf) Jt(Fr Jj Mu Om) Wm(Jo Mr Qd) Ir(Jh Mi Mr) Jn(Ma Mv Pc) Om(Lv Ma Qd) Nn(Mj Mr) Lx(aA Hq) Iu(Jh Jp) Jj(Jo Lh) BcDi CoNh CsCu NsMu MiNx QcJh NvaA} Jj{Pc(aA Hu Ii Im Iu Jn Jq Jr Js Jt Lh Lx Mi Mm Mp Ms Nv Nx Of Pd Po) Cu(Ad Af As Ax Cw Hr Hv It Iv Jn Jq Jr Mj Mr Mz Nb Nf Nv Of Om) Lw(aA Im Iu Jr Lx Mi Mj Mm Mp Mq Ms Nn Nq Nx Of Pd Po) Iu(aA Ip Jg Lx Mi Mp Nh Nn Nq Pe Po) Pa(Et Ik Im Jr Lx Mm Mp Mw Nn Nx) Jo(Hr Hw Ij Md Ml Mp Nn Ny Pb) Oz(Im Jr Js Lx Mm Mw Nn Nq Nx) Jt(Hw Ij It Ml Mx Nf Ny Pb) Pe(Ik Jr Lx Md Mm Mp Nn Nx) Hr(aA Ii Jr Mi Mq My Po) Md(Mi Nb Nm No Nx Pg) Mr(Ik Jr Ms Nx) Nb(Mm Mp Ms Nx) Mi(Jg Ml Nn) aA(Ii Jg Mj) Ch(Mt Nu) Ml(Ir Mj) Mp(Jg Nn) Ms(Nh Pg) Mv(Ao Dk) AfOn CoNu CxJl NsMq NhJq} Md{Jp(aA Hv Ik Jr Lx Mc Mg Mi Mp Mr Mu Mv Ni Nn Nq Nt Oh Pf Po Qa) Mt(aA Hv Lh Lv Mq Mr Mv Mz Ni No Nt Ok Pa Pe Pf Po Qa) Jh(aA Hr Hu Js Lh Mh Mr Mz Nw Oi Ok Qa Qd Qe) Iv(Et Hv Jg Lh Lw Mg Mp Mw Mz Nn Nt Pc) Mp(aA Fr Ir Jl Jr Lx Mu Mv Nu) Nw(Hv Ma Mi Mu Nb Nn Nq) Ok(Fr Lu Lv Mc Mi Mv Ni) aA(Jr Lx Ma Mv Mz Pf Qa) Fr(Jr Lv Lw Ns Nt) Mu(Jr Lw Mc Mg Nt) Nb(Hv Lw

Figure 2 Continued

Figure 2 Continued bE bH Cp cR Cv Cw) Bg(aW cR Dk Nv Of Oy Pg) Nv(Ba Co Js Lu Ma Pb) Of(Ba Jh Ma Mu Mv Nq) Pa(Ii Ij Jj Js Ny Pe) Cs(aW aZ cR Fr Nu)
Hx(Ir Mu Mv Nq Pb) Pg(Jj Lv Mr Mt Nu) cT(Ad An As Cp Cw) Hw(Mg Mv Nq Nu) Jm(Js Ml Pb Pe) cA(Ad An aP Cw) Ba(bE Oy Pb) Ef(Ax
Dk Fw) Mx(Aj Fr Mu) Ij(Jh Mv Oz) Pe(Mr Mt Nu) aZ(Ad aP aX) Dd(Lw Mg) Ny(Jh Oz) Oy(De Om) bR(cO dI) dG(aA aJ) dK(bJ cR) MvJk
IrIt JjOk JrJs aPcK bHbU} Oi{Nn(Bc Hv Jl Jn Jr Js Jt Lh Lw Lx Mg Mj Mp Mr Mw Mz No Nv Po Qe) Mg(Et Hv Jr Js Lh Lj Lv Lw No Nu Oz
Pa Pc Pe Po Qa Qd Qe) Et(Jg Jr Lw Mj Mz Nb Pc Pe Qa) Nu(Ba Jk Jt Mp Mv Mw Oh Qa) Jg(Hv Iu Jp Lw Mz Nt Oh Qd) Jp(Jr Mj Mr Pc Pe Qa
Qd) Mv(Jr Lh Mj Qa Qd Qe) Jh(Lj Ma Mj Pa Pc) Oh(Mq Nb Pc Pe) Ma(Mp Nt Wm) Mu(Jl Pc Qd) Hv(Ik Jk Wm) Lw(Lx Nv) Ml(Iv Qa) Pc(Ok
Po) DkFr NtQd LxNb MwIu MxJl MzIk} Pc{Jh(Hu Mj Mr Mz Ng Ns Nt Of Oh Ok Oy Pf Qd) Nk(Hv Jr Mj Nv Oh Po Qa Qd Qe) Mt(Hv Lv
Ma Mg Mz Pa Pe Qd) Jp(Lw Ma Mg Mj Mq Ns Nt Pf) Jj(Ir Jo Lw Mq Nb Nh Pe) Ni(Mj Mw No Nu Nv Pf) Ok(aA Iv Lu Ma Mg Mi) Ns(aA Jl
Nt Nw Pf) Mu(Mi Ng Nt Pa Pe) Ma(Jr Lw Nw Om) aA(Lw Mj Mq Po) Nt(Hv Nw Om) Mg(Iv Jl On) Mv(Mr Mz Ng) Ji(Jr Js Nf) Lv(Mz Om)
Mi(Jl Nw) On(Jl Og) LwMw LxNd MjHv MzPf NwOy} Lw{aA(Hw Ij It Jg Jn Mg Ml Mx Nf Ny Ok) Ns(Jg Jp Jr Mv Nn Nu Nw Oh Pf) Jh(Ma
Mi Mu Mz Ng Nt Of On Qd) Jl(Fr Ih Lv Ma Mg Mu Mx Ok On) Ma(Fr Jp Mt Nb Nw Om) Mu(Dd Lv Mi Ng Nw Og) Jj(Mr Nb Oz Pa Pe Pg)
Lu(Et Mp Nu Oh) Jp(Io Mg Nt Pf) Hv(Jg Nt Nw) Iv(Mg Ml Nw) Pf(Jm Lv Mz) Ni(An Cv) Ii(Ba Bg) FrMy NnMr LvMw LxNd MiNw MlNb
MvMz IrIt JgOg} Jh{Of(Jg Jt Lv Ma Mg Mi Mj Mp Mr Mu Nb Oz Pa Pe Po) Ns(Jg Ma Mi Mp Mq Nn Oz Pa Pe) Ma(Hu Jl Mz Ng Nt Ok On)
Ng(Mg Mj Mp Nn Pa Qe) Mu(Hu Lv My Og Qd) Qa(Hw Ij It Ml Pb) Lv(Hu Mg On) Nb(Ij My Pb) Ir(Jn Jr Js) Oy(Il Mj Mp) Nn(Nt Ok) Lx(Hq
Nd) Hu(Li Pa) NtMs OkaA} bE{dK(aA aC aI aP aY Bg bO cF Ch cT cW dN) bO(aY bA Bg Ch dD dR) aI(aE aW bU cI dN) bR(aE aY bA bZ
cT) bU(Ch cR cZ dI) cD(aY bV cT cW) cP(aF bG cM dD) bX(cM cW dD) cT(aE aF aY) Ar(bG Ch) Bg(dL dN) aA(bZ Cx) aD(bA gL) cW(bZ
cK) dD(aN aW) aCcR aEcM aFbA aLdN cEgL} Oy{Nw(Jg Jk Jl Mg Mk Nb Nn Oz Pa Pe) Nn(Jl Jp Mj Mq Mt Nb Po) Mu(Et Lh Mk Nb Pa Pe
Pf) Jg(Hv Jl Jp Mt Nu Oz Pf) Mt(Aw Mk Nb Oz Pa) Mv(Lh Mk Nx Pa Po) Pf(Cs Mp Oz Pa Pe) Nb(Iv Jp Mp Oh) Bg(Mc Mr Nu) Po(Mg Mw
Nk) Om(Cx Mg) AdMi BaDe ChPd MkJp} Ok{Lv(Hw Ij It Jq Lu Mg Ml Nf Nn Ny Pb) Ma(Fr Hv Jl Mi Mt Nw) Mg(aA Hv Iv Jl Lu Of) Ni(Hw
Ij Jq Ml Nf Pb) Iv(Ij It Ml Nf Nn) Of(Jg Mp Mu Nn Nt) Mi(Jq Mx Ny) Ns(Mu Nn) Lu(Jp Nw) Ml(Hv Ir) Mx(aA Jl) It(Hv Ir) Og(Iu Mv) NqMy
MuNg NbNy JraA} Mg{Ng(aA Ji Jp Mw Oh Om) Bg(Dc Dd Jm Mc Og) Jl(Cq Ji Jm Lv On) Hv(Jp Mt Mz Pf) Iv(aA It Jm Nw) On(aA Lv Nv
Ny) Bb(Jj Mr Mt) Hu(aA Mv Nw) Of(Mj Mv Nw) Dd(Fr Is) Jg(Ni Og) Jm(Il Mj) DcNq NsMt MzPf IjNw IrIt JpJr} Mp{Hq(aA Fr Iv Jl Jp Mj
Mt Mu Mv Om) Ns(Lx Ma Mj Nb Ni Nn Nt Oh Pf) Nd(Fr Iv Jl Jp Mj Mt Mu Om) Pg(aA Jl Jp Mj Mt Mu Mv Om) Ni(Lx Mj Mw) Jm(Il Iv Mj)
aA(Ms Ne) LvMa LzJl MvNg NkIv} Jj{Bg(Iu Mi Mr Mt Mu Nn Nu) Ch(Iu Mi Mr Mu Nn) Oz(Ip Jn Jq Ms) Pa(Ip Jn Jq Ms) Af(Fr Mv Om)
Nq(Ao Cq Dk) Jo(It Me Nf) Jt(Jn Js Na) Co(Ii Mv) Mq(Iu Nn) Mu(Ao Dk) Hq(Lx Mi) BaMa CpMv WmNh NoMl NsMk MsPe IrIt} aX{bX(aC
aW bN bZ cT dK Fr) dK(aA bN bR bZ cF cI) aA(cA cB cK dH) aD(bZ cA cB cK) Fr(aW aZ cX) bA(bR cA cK) cS(cA cB cK) Co(aZ Dg)
aE(cB cT) aW(aI cP) bQ(bZ eF) cC(Ch eF) cI(aJ bZ) BacX aPbR bHcD cPcT} Mt{Cq(Ir Lv Mi Mu Ni) Nn(aA Jl Lv Pe) Ma(Hv Mi Ms Pa)
Ni(Af An Cs Pa) Nw(aA Is Mi Pf) Bg(Dc Dk Pz) Qa(Ij It Ml) Jl(Dc Lv Om) Ax(Ir Mc) Nr(Iv Po) Ns(Jg Pe) DcNq NoMl LvPa MiHq NbPb
JgOf} cR{Bg(aA aJ aW bC cP cS cT dK) aW(aJ Aw bX CT) aF(aJ aO Ba cT) aP(cA cK Co dK) bU(aY bH dM) cT(aA bZ Fr) Co(aJ dK) bA(bQ
cP) bV(aA cA) bX(bH dI) BaFr aIcI bGdK cBcS} Hv{It(Ir Lh Mj Ni Nt Qa Qd) Jg(Hu Lv Ma My Ns Of Pf) Ma(Jp Lv Mi Mu Nt) Ml(Ir Iv Ni
Nw Qa) Nk(Mj Po Qe) Ji(Jq Mz Nt) Nn(Lv Nt) Nq(My Of) Qa(Ij Om) NsNv LxNd} Jl{Ji(It Jn Js Ml Mz Ny Pb) Nw(Hx Ma Mu Mx Ny) Of(Ba
Jg Mu Nn) Ns(Jg Mu Nn) Lv(Jp Mx Om) Ir(Cs Dc Js) Ba(Cq Nv) Nt(It Nr) Mx(Mu Ni) CoNv FrMk MiHq MvMy} Nk{Co(Ao Bb Mc Nh Of)
Nc(Ba Bg Ch De Ma) Pe(Jr Mu Nn Pf) Nu(Ba Bg Ch) Pf(Mr Nh Pa) Ao(Mv Nq) Cv(Jp On) Mu(Mh Oz) AfOn BaNh DiMc NtaA MrMv IvPa
JgOz} bZ{aW(aA bA bU bX cC cD cT dK) aD(bJ cC cS dK) aF(aP bX cD cS) Ba(bR cP dF) aJ(dF dG dK) aP(bS cC cK) Bc(cA cK) aA(Cx
dA) cS(bS dH) bAcP bHbX} Nt{Ji(Hw Ij It Js Mc Mz Nf Ny Om Pb) Mv(Hu Ng Ns Of) Fr(Hq Nv Pg) It(Ir Mz Qa) Ns(Jg Pf) Ng(Mu Om)
Ij(Om Qa) MaJp MlIr NeNh NwOf} Ml{Ir(Fr Jp Jq Jr Lv Lx Mr Mu Mw Nn Pf) Nb(Lx Ns Nu) Iv(Jg Mz Nn) Om(No Pe Qa) Mc(Oh Pf)
Nw(Ma Mi) WmaA LuJi LxNd NiPf QaJp} cP{cI(aA aP bA bU bW cM) aF(aA aJ aP cT dI) bR(aJ aP cU dI) aA(bJ Cx) aW(Ba Bb) bH(bX cC)
bW(Af Co) cU(aU cT) BgbC aEcG bAbN bUbV} Iv{It(aA Jg Jt Mi Mw Nn Qa Qd) Mx(Ir Mi Nn Qd) Jg(Mi My Ng Of) Ir(Jn Jr Js) Nb(Ny Of)
Hq(Lx Mi) NsMq MwMy} Pf{Ns(Jg Mq Mv Nn) Mu(Hu Ng Of) Ni(Jg Nn Pa) Qa(Ij It Nr) Lj(Jr Mz Nw) Cs(Ir Mc) Lz(Pa Pe) Of(Jg Nb) FrPa
LxHq IrIt} Jp{Mi(Cq Hq Ma) Of(Jg Nb Nq) Nn(Lv Mq) Lx(Hq Nd) Ms(Li Ma) It(Ir Qa) Pa(Lv Ni) DcIs NqMy NsMq NbNy IjQa} aA{Qa(Hw
Ij It Ne) Cx(Bg cC Co) De(aW bJ) Nn(Mq Qd) Ma(Jg Mi) Mx(Oh Po) Jr(Jn Js) BgbJ FrdG LzLi MiJg} aP{cI(bX cA cB cK dK dN) bR(aF aW
Bg Ch cT) cF(cA cK dH dK) aW(Bg bU Ch) BgcC bAdG bNcK} cT{aE(aD bW eF) aW(aI bJ De) bJ(aF dL) bR(bW cO) bU(bP dE) eF(bQ cV)
AddN aDaL aYbX cDdI cSfP} dK{bR(bH bV cU) bX(bH bV dI) cF(aJ dI) cI(cG gL) eF(aF aW) ArcX BgdN aEaI bGcC bUcU} Nu{Co(Cq Ii
Of) Ns(Ma Mq Mw) Qa(Ij Pb) Jr(Ma Pa) AoMv NnNi NqMy NbPb IrIt JgOg} Ji{Af(Ba Dd Ii) Jq(Bg Lv Mi) Mz(Pa Pe) Nf(Mi Nn) Pb(Oz Pe)
MaIt MxQd NgJg OmPa} Mv{Of(Jq Nx Pa Pe) Ns(Et Jr Oh) Mr(Af Co) Nb(My Ng) AoNh DdIs EtNg NiOh} Om{Pb(Mi Nb Oz Pa Pe Qa)
Qa(Hw Jn Ny) Jg(My Ng) Ny(Lh Mr) MaMi IjQd} aE{aI(aJ bJ bU cI) bX(bA cG cO eF) bU(bV cG) CoaW aFbA bRcG cCgL} Is{Al(Ba Bg Fr
Hx Ma Mx) Dc(Bc Co On Qb) Dd(Hx Mu) BgJm} Fr{dG(bA cS) BgDk BnMr MiHq MyJr NbNy IrIt IuJm OgOn bRdI} Mu{Nw(Ma My Ng)
Of(Et Jt Mr) EtNg NsMz MyNb NfJq OgOn} aJ{Ch(bU cC) cI(aU cM) dN(aF aW) eF(bQ cV) aIdG bNcC cUdH} Lx{Nd(Ma Mh Mz Nn Oh
Pb) Ns(Mq Nn) MzHq NbPg} On{Cq(Lv Mi) Qd(Nv Ny) Og(Ma Nn) AnNi AxMc BgOf} bA{aF(bJ bX) CoaW CqDe aDaM bNbX bQeF cSfP
dGdL} Nw{Nn(My Nf) Mi(Mx Nf) Jg(My Of) LzOz NbNy} Bg{Bc(aW Jm) ArbC DkdN McOf cCcO cIcS} Jr{Ns(Jg Mq) CoJs NnNi NqMy
MaMs NbNy} bU{bH(aY bO dM) dI(aW dM) aVdA cGcI} Ba{cU(cA cG cL dH) aMcH cVcX} Mr{Co(Cq Ii Nv) CwIi DkNq IrIt} Nb{Ny(Js
Oh) NsLi MaMy IrJn} It{Ir(Jq Mw Qa Qd) NiJs} Oh{Ni(Jg Pa) NsJg LvMa} aW{BcCh CodN bNcS bXcO} cC{eF(bH dI) ChcO aNgL}
cI{cM(aO bV) aIbX bRcG} Nn{Mj(Ni Ns) IlJm} Lv{MaMz NdIk} My{NqMz MjMw} aF{aObX cSeF} bV{aIbJ bHcD} AdMiHw BccKcS
MaNdIk NeNhLh bQdMgL bRdIcF

Constrained panels with 3 analytes, where 1.0E-3 >= 'AUC p-value' > 1.0E-4. Contains 2,678 panels of 939,239 total panels evaluated. :
In{Hx(Hv Jg Jh Jn Jp Jr Js Lw Ma Mp Mr Mu Mv Mw Nn Nq Nu Oh Ok Pf Po Qa Qd) Ir(Ik It Jo Jr Lh Li Lv Lx Ma Mj Ml Mv Nb Nh Ni Nv
Nx Oh Pe Po Qe Wm) Mr(Et Hv Iu Jp Ma Mj Mm Mq Ms Mv Mz Nq Nv Nx Pc Po Qd Qe) Jt(aA Hr Hw Ij It Ma Ml Mp Mq Mz Nh Nn Nq Ok
Pb Po Qd Qe) Pa(Et Fr Hv Ip Jg Js Lw Lx Mj Mm Mv Mz Nn Nx Po Qa Qd Qe) Pe(Et Fr Hr Hv Ip Jg Js Ma Mj Mv Mz Ni Nv Nx Po Qa Qd
Qe) Nb(Et Hr Jp Lv Lx Md Mj Mq Mz Nh Ni Ny Oh Po Qa Qd Qe) Pc(Ik Il Jg Jl Jq Lw Mi Mj Mq Mv No Nx Pd Qa) Mq(Et Hr Jg Md Mj Mv
Nn Nq Ns Qa Qe Wm) Jo(Jp Jr Js Mi Mj Mp Mv Mz Nu Pf Po Qe) Qd(Iu Jg Lh Lx Mi Ml Mu Ni Nn Nq Po) Jq(Jg Jr Ma Md Mg Mp Mw Nn Nt
Nu Pd) Hr(Ii Ij Ik Ip Lh Lx Nu Nx Pd Po) Oz(Et Ip Jg Li Mm Mz Nn Nx) Ma(Ii Li Pd Po Qa Qe Wm) Mi(Cu Il Jg Lh Mj Qa Qe) Iu(Ip Jg Li Mv
Nn No Pd) Lv(Lh Lw Po Qe Wm) Lx(Il Jh Mj Nv Qe) Mh(Et Mg Mu Mw Nv) Jk(Et Lw Mp Ns Oi) Mu(Lh Po Qa Qe) Ik(Jn Lw Mj Ms) Jg(Hu
My Qa Qe) Wm(Im Mn Mw) Mv(Hu Lh Qe) Nh(Bg Nd Nn) Ns(Ii Ij) Lw(Hv Mj) Md(Nx Pg) Ip(Il Nn) Qa(Ml Nq) Li(Mp Ms) AjHv AwOy
BaNk BcBg CoIv CqPd DeNu MgNg MjaA MmNi HwJj IiJr NvOi} Md{Nn(Et Hv Ir Jq Js Lh Lv Lw Mi Mq Mv Mw Mz Ni No Nt Nv Oi Pa
Pe Pf Po Qa Qe) Jg(Jq Lh Lv Lw Mg Mi Mj Mp Mu Mz Nb Ni No Ns Oh Oi Pc Po Qa Qd Qe) Ni(Ba Et Ii Jn Jr Jt Lh Lw Mm Mv Mw Nx Pd

Figure 2 Continued

Figure 2 Continued dI{bR(aI Bc bZ cU) cC(bO cP cW dK) bU(Co De) bX(bO cP) cD(aI dK) eF(cA cK)} Dc{Is(Fr Jh Jl Lz Mc Mi Mr Mx Om) Jl(Co Jp Mr) Lv(Mt On) QdJp} bH{cC(bO Co cW gL) cD(aI aO bO dK) Co(bU bX) BbcP bRdH bVbX} It{Iu(Hv Js Mz Nu) Nt(Jq Qd) Nu(Jq Qe) Mq(Hv Js) WmQd HvQe} aP{bN(bX cA dH) Ch(bU cC) aF(cD cK) bZ(cA dH) bXcP cUdH dGdK} Bc{cO(bR bU cA cF cK) cX(bX cV dK) bJ(aU cY) IiQd} Mi{Hq(Jh Lx Mz Nu Nw Oh Pf) Cq(Fr Pf) FrMt LvJh} Li{Lj(Iv Jl Jp Lx Oh Pf) Lz(Jl Pe) Ms(Jh Mt) PoOn} Mc{Co(Lz Nj) Cs(Cw Lx) Di(Lz Nj) Lu(Ad Bb) AxPf CwMx} aF{bZ(aD aJ bR) cP(cO cU dH) aO(aY dK) bAdK} Ch{Jj(Nh Qd) bA(bR cX) JiJq aJbR bJdL bXcO} Lv{Jl(Jh Mw Mz) Pa(Jh Mw) NtMs LxHq LzOz} Nw{Mt(Iv Jl Jp) Ny(Pa Pe) MxQd NfNv OzPb} Ok{Hv(Ij Jq Nf) Lu(Mz Oh) Jk(Ng Of) NfOh} dK{bJ(aD dL) cF(dM gL) aJdG bGcD bUbW} Co{Jh(Ii Of) Pb(Mr Nu) HwQd bZcC} Ne{Nh(Hv Iu Mj Mr Pa Pe)} Lx{Mw(My Nd) Hq(Hv Nt) LzOz} aI{aH(De gL) AfbW cCdA cPcZ} aJ{dG(bC cC cO) DecX bZdH} Is{Cv(Jh Nj Qb) CsJj} Of{Lh(Nd Nv) AfOm PoLz} Pf{Oz(Lz Pb) NtMs NfJq} bA{bQ(cO dN) bZ(cG dH)} bJ{bV(cA cK) ArbG aDaO} bW{bN(bO bU bX) bQgL} Nu{CwIi MwMy NgJk} cP{DeDk bVbX cCgL} Ef{AjDk CtFr} Po{NrNt MyJh} Ms{NtMt LuIp} Nd{Ik(Et Jr)} Hx{Jj(Ny Pb)} Jl{DiMx IhQd} Lj{CsFr MhOh} Pa{AfOn LzOh} bZ{aDbQ cKdM} BoCwIi NgJkJp IvJnJq bXcQcX cScUdH

Constrained panels with 2 analytes, where 1.0E-7 >= 'AUC p-value' > 0. Contains 35 panels of 19,595 total panels evaluated. : Jj(Fr Is Iv Jh Ji Jk Jl Ma Mt Mu Mv Nt Ok Om On Pf Qd) On(In Iv Oe Of Oi) Is(Hr In Jm) cS(bR cP dN) aA(bU cX) FrIv HrJi bAbU cIeF cTdN Constrained panels with 2 analytes, where 1.0E-6 >= 'AUC p-value' > 1.0E-7. Contains 47 panels of 19,595 total panels evaluated. : Jj(Il Jp Lv Mg Nu Nw Oh Qa Qe) Is(Fr Ih Jh Lv Md Oi Qb) Om(aA Hr In Md Ns Of Oy) On(Lv Md Ng Ns Ny Og Oy) Fr(aA cP Hv Ji Ng) In(Cu Ji Mt) Ji(Jh Md) bZ(cP dN) LvaA MaIv aEeF bAdN bUcS Constrained panels with 2 analytes, where 1.0E-5 >= 'AUC p-value' > 1.0E-6. Contains 94 panels of 19,595 total panels evaluated. : Jj(Et Hv Ii Ij Ik Im Jr Js Jt Lh Lx Mi Mj Mm Mp Mr Mw Mz Nn Nq Nv Nx Of Pd Po) Iv(Hr In Jh Jl Jp Lv Mt Mu Mv Om Pf) Is(It Ji Lw Ma Mg Mi Mu On Pc) On(Hr Hu Ji Lw Ma Mt Mu My) Ji(aA Ma Ml Mu Mx Pc) Mt(Jh Md Mu Ns Oi) Om(Hu Jh Mu My Ng) aA(bJ bR cI cS Mu) Fr(aW bE Of) Jh(Hv Jr Nw) cS(bA cF cI) Nk(Cu Jl) In(Mw Nw) dN(Ba cP) CoOy MvHv NiOh aJbU aXcD Constrained panels with 2 analytes, where 1.0E-4 >= 'AUC p-value' > 1.0E-5. Contains 182 panels of 19,595 total panels evaluated. : Jh(aA Hr Hu Jl Jp Md Mr Mz Ng Ns Nt Of Oh Oi Ok On Pf Qa Qe) Jj(aA Co Cu Ip Iu Jg Jn Jo Jq Li Lw Mq Ms Pe Pg Qb) In(Hv Jl Jn Jr Js Mg Mp Mu Nu Oh Ok Pf Qa) aA(bZ cR Jr Lw Ma Mn Mt Mv Mz Nn Nw Pf) Lv(Fr Hv Jp Mp Mt Mz Nw Oh Ok Om) Mt(Hr Hv Lw Mi Nn Ok Pa Pc Pf) Iv(It Jg Lw Mz Nn Nw Oi Ok Pc) Fr(cR Hu Lw Md My Ns Ok Oy) Cu(aW Ba bJ cR cX Dc Oy) dK(bA bU bZ cP cT dN eF) Mu(Hv Lw Ns Nt Nw Pc) Jl(Hr Ji Md Mg Ns Om) Jp(Hv Jr Mi Mp Ni) dN(aJ aX bN bU Co) Ji(Jn Jq Js Nf) Nw(Hr Ma Md Mi) cR(BA Co Cp) eF(aF bE bQ cV) Nu(Jr Nb Nn) Ok(Is Mi Pf) Om(Ma Mi Pc) bR(aJ aP bA) bU(aP aX dI) cS(aW bN cT) Lw(Mw Nb) Lx(Md Nd) Oi(Nt Oh) Pf(Hv Mz) bZ(bX cT) NnMr MpIr MwJr aDcT bAbJ cIgL Constrained panels with 2 analytes, where 1.0E-3 >= 'AUC p-value' > 1.0E-4. Contains 267 panels of 19,595 total panels evaluated. : Hr(aA Cu Et Fr Hv Jn Jp Jq Jr Lh Lv Mp Mr Mu Mw Mz Nt Ok Pf Qa Qd Qe) In(Bc Co Et Jg Lh Lx Mj Mm Mr Mv Mz No Nt Nv Pd Po Qd Qe) Cu(Ax cP Cs dK Fw Hw Hx Ii Js Md Mx Nv Ny Of Pb Pg) Jp(Lh Lw Ma Mg Mq Mv Nn Ns Nt Ok Pc Pe Pf Qd) aA(aF bX Co Cx Et Iv Jg Lx Mg Nt Ok Pc Po) Hv(Et Jg Lh Ma Mw Mz Nt Nu Oh Ok Qd Qe) Pf(Jg Lv Lw Ma Mg Mi Mu Ni Nn Nt Pc Qd) Jh(Lv Lw Ma Mi Mj Mp Mu Pa Pc Pe Qd) Jr(Et Jg Lw Ma Mg Mp Mq Mv Nb Nn Pc) Nu(Lh Lv Lw Ma Mp Mq Mw Pa Pe) Mg(Iv Mj Mt Mz Nw Oh Oi Ok On) Mu(Jl Md Mi Mz Ng Oi Ok Pa) Mv(Et Lw Mz Ng Ns Nt Oh Oi) Mp(Ma Md Mj Mr Nb Ni Ns) Ok(Jl Lu Ma Md Nn Nw Pc) Lw(Jg Jl Lx Nn Nw Oh) bX(aX bA bH cR cT dK) bZ(aF bA bR bU cA cC) Mt(Cs Ma Nt Pe Qd) Jj(Nb Oz Pa Pc Wm) cR(aJ Bg cT dK dM) Lx(Mq Nn Oi Pc) Md(Nb Nn Nt Nv) Jl(Lv Ma Oi Pc) bU(bE bH bV cP) cI(aI aP aX cG) dK(aJ aP bE cF) Mz(Ma Mi Nt) Oh(Jg Lh Ma) aW(Ba dN eF) Bg(dN Mr) Ns(Nn Nv) Ml(Ir Nb) Ni(Mw No) Qd(Oi Om) Pc(Lh Nw) cT(bJ eF) BacS CoNk EtOi NtLv MiIv MrJg aEbA aPcK aXcP bEcW Constrained panels with 2 analytes, where 1.0E-2 >= 'AUC p-value' > 1.0E-3. Contains 333 panels of 19,595 total panels evaluated. : Pc(Et Hv Jq Js Lv Ma Mg Mj Mp Mr Mv Mw Mz Ni No Nt Nu Nv Oh Po Qa Qd Qe) Jg(Hr Hu Lh Lv Ma Md Mi Mj Mp My Mz Ni Ns Of Oi Oy Pa Pe Qa Qd Qe) Nn(Et Hv Jq Lh Lv Mg Mi Mj Mp Mq Mz Ni Nt Oi Pa Pe Qa Qd Qe) In(Ba Ii Ik Il Ip Ir Iu Jk Jq Jt Li Lw Mq Nb Nx Pe Pg Qb Wm) Lw(Et Hv Lh Lv Ma Mg Mi Mj Mp Mr Mz Nt Nv Po Qa Qd Qe) Ma(Et Jq Lh Lx Mg Mj Mr Mw Nb Nt Nv Po Qa Qd Qe) Hr(Ik Js Lx Mg Mi Mj Mq Mv Nb No Nu Nv Nx Oh Po) Pa(Jp Jr Lv Lx Mg Mp Mv Mw Mz Ni Nv Oh Po Qa Qe) bE(aA aI aY Bg bO bV bX bZ Ch Co cP cT Cu dD) Bg(aA aP bA Bc cP cS dK Jj Mc Mg Oy) Pe(Cu Et Jr Lv Lx Mp Mv Mw Mz Oh Qe) Mg(Hv Lh Lv Mv Ng No Nt Qa Qd Qe) cP(aA aJ aP aW bA bV cR cT dI gL) Co(aJ aP aX dK Ii Mc Of Pb) Mp(Hq Hv Jq Mq Mw Nd Pg Qe) aA(aW Ch cT Lh Md Mi Mj Qd) Oi(Ba Ii Jk Jt Nv Qe Wm) Lv(Mr Mu Mv Mw Nb Qd) aP(aF aW bX cB Ch cT) Fr(aX BA cS cT) bR(aX bV cI dH dI) bU(aE aY cI cR dM) bZ(aD aJ aW aX Ba) dK(Ar aX cU dM gL) Md(Jq Lh No Qa) Mr(Jq Jr Mw Nu) Mv(Ao Mi Qd Qe) Mm(Hv Jr Ni) Mq(Mw Mz Oh) Nb(Et Oh Pb) Qa(Ij It Ml) aE(aI cG cT) aF(aO bA gL) aW(aI Cp cR) Ba(Mc Nk) Ch(bA Jj) Mi(Hv Nt) Ni(Jk Qe) Ip(Jr Ms) Qd(Mu Ok) bV(bX cA) bW(cI cT) cD(cO dI) cR(aO De) AfOm BccX CpOy CuIt DcIs EtOh NsJk NuJq LxHq NdIk aYcT bObX

Figure 2 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.5E1 | 8.8E1 | 7.6E1 | 9.9E1 | 5.2E1 | 6.2E1 | 2.0E0 | 1.4E1 | 4.0E2 | 2.4E2 | 1392 | 30 | 230 | 30 | 0.61 |
| Ad | ug/mL | 3.4E-2 | 7.6E-2 | 6.5E-2 | 3.9E-1 | 8.4E-2 | 1.6E0 | 6.8E-4 | 4.3E-3 | 5.4E-1 | 8.5E0 | 357 | 29 | 135 | 29 | 0.66 |
| Af | ng/mL | 1.0E0 | 1.0E0 | 1.4E1 | 1.5E1 | 6.0E1 | 4.7E1 | 1.7E-3 | 1.7E-3 | 5.3E2 | 2.6E2 | 357 | 29 | 135 | 29 | 0.52 |
| Aj | ug/mL | 1.8E0 | 7.2E1 | 2.7E0 | 1.9E0 | 2.5E0 | 2.4E0 | 1.5E-3 | 2.1E-3 | 6.1E0 | 6.1E0 | 357 | 29 | 135 | 29 | 0.41 |
| Al | mg/mL | 8.7E-5 | 9.5E-5 | 2.5E-4 | 2.3E-4 | 4.1E-4 | 3.1E-4 | 2.5E-6 | 7.6E-6 | 1.9E-3 | 1.3E-3 | 357 | 29 | 135 | 29 | 0.55 |
| An | U/mL | 4.9E1 | 7.7E1 | 1.6E2 | 5.6E2 | 4.6E2 | 1.5E3 | 9.8E-4 | 9.6E-1 | 5.5E3 | 7.8E3 | 357 | 29 | 135 | 29 | 0.63 |
| Ao | pg/mL | 8.5E1 | 9.8E1 | 6.0E2 | 1.8E2 | 3.9E2 | 2.5E2 | 2.8E0 | 5.4E0 | 3.9E4 | 1.3E3 | 357 | 29 | 135 | 29 | 0.57 |
| Ap | ng/mL | 3.1E1 | 4.6E1 | 4.2E1 | 5.7E1 | 4.3E1 | 4.8E1 | 8.4E-5 | 3.1E0 | 2.9E2 | 1.7E2 | 357 | 29 | 135 | 29 | 0.60 |
| Ar | ng/mL | 8.5E-1 | 2.6E0 | 1.5E1 | 5.5E0 | 2.2E2 | 9.7E0 | 3.4E-3 | 3.4E-3 | 4.1E3 | 5.1E1 | 357 | 29 | 135 | 29 | 0.67 |
| As | ng/mL | 9.5E-3 | 1.0E-2 | 1.3E-2 | 5.8E-2 | 1.8E-2 | 2.3E-1 | 1.7E-3 | 1.7E-3 | 1.3E-1 | 1.2E0 | 357 | 29 | 135 | 29 | 0.53 |
| Aw | pg/mL | 1.6E1 | 1.7E1 | 1.6E1 | 1.9E1 | 5.9E0 | 8.2E0 | 2.9E-2 | 1.1E1 | 4.8E1 | 5.1E1 | 357 | 29 | 135 | 29 | 0.58 |
| Ax | ng/mL | 2.2E0 | 8.7E0 | 1.4E1 | 5.9E1 | 5.8E1 | 1.4E2 | 1.3E-2 | 1.2E-2 | 7.7E2 | 6.2E2 | 357 | 29 | 135 | 29 | 0.67 |
| Ba | ng/mL | 6.2E1 | 2.5E2 | 4.2E2 | 6.9E2 | 1.2E3 | 1.1E3 | 3.7E-1 | 6.3E0 | 8.1E3 | 4.4E3 | 357 | 29 | 135 | 29 | 0.65 |
| Bb | ng/mL | 2.8E0 | 5.0E0 | 6.1E0 | 7.5E0 | 1.5E1 | 6.5E0 | 4.1E-3 | 2.6E-1 | 2.5E2 | 1.9E1 | 357 | 29 | 135 | 29 | 0.63 |
| Bc | ng/mL | 3.4E1 | 7.2E1 | 1.0E2 | 1.8E2 | 1.9E2 | 3.0E2 | 1.1E-1 | 8.0E0 | 1.2E3 | 1.0E3 | 357 | 29 | 135 | 29 | 0.64 |
| Bg | ng/mL | 7.7E-2 | 1.3E-1 | 4.0E0 | 9.5E-1 | 1.9E1 | 1.3E0 | 5.3E-4 | 5.3E-4 | 2.5E2 | 4.8E0 | 357 | 29 | 135 | 29 | 0.61 |
| Bn | ng/mL | 5.6E-2 | 5.6E-2 | 1.1E0 | 3.2E0 | 1.9E0 | 1.1E1 | 5.6E-2 | 5.6E-2 | 9.7E0 | 5.8E1 | 357 | 29 | 135 | 29 | 0.51 |
| Bo | ng/mL | 1.2E1 | 2.0E1 | 1.4E1 | 1.9E1 | 2.0E1 | 1.5E1 | 1.6E-2 | 1.6E-2 | 2.8E2 | 5.3E1 | 357 | 29 | 135 | 29 | 0.62 |
| Ch | uIU/mL | 1.2E0 | 6.6E-1 | 2.1E1 | 5.6E0 | 1.1E2 | 1.9E1 | 3.4E-3 | 3.9E-2 | 1.8E3 | 1.1E2 | 357 | 29 | 135 | 29 | 0.37 |
| Co | pg/mL | 3.8E1 | 5.0E1 | 1.8E2 | 1.1E2 | 1.1E3 | 1.7E2 | 1.5E-1 | 1.5E-1 | 1.7E4 | 8.2E2 | 357 | 29 | 135 | 29 | 0.59 |
| Cp | ng/mL | 2.2E1 | 2.2E1 | 2.8E1 | 7.5E1 | 3.3E1 | 2.3E2 | 6.0E-1 | 6.0E-1 | 3.7E2 | 1.3E3 | 357 | 29 | 135 | 29 | 0.59 |
| Cq | ng/mL | 2.8E-2 | 3.1E-2 | 1.5E-2 | 1.7E0 | 9.5E-1 | 9.1E0 | 8.0E-4 | 8.0E-4 | 1.7E1 | 4.9E1 | 357 | 29 | 135 | 29 | 0.53 |
| Cs | ng/mL | 6.6E1 | 2.6E2 | 3.0E2 | 1.3E3 | 8.6E2 | 3.4E3 | 2.7E-2 | 5.2E0 | 1.1E4 | 1.8E4 | 357 | 29 | 135 | 29 | 0.67 |
| Ct | ng/mL | 8.9E-1 | 1.3E-1 | 4.0E1 | 3.7E1 | 1.1E2 | 1.2E2 | 1.1E-4 | 1.1E-4 | 6.2E2 | 4.7E2 | 357 | 29 | 135 | 29 | 0.38 |
| Cu | ng/mL | 2.4E-1 | 3.7E-1 | 4.0E-1 | 2.9E0 | 7.0E-1 | 1.2E1 | 9.6E-3 | 4.6E-2 | 9.2E0 | 6.6E1 | 357 | 29 | 135 | 29 | 0.65 |
| Cv | ng/mL | 4.1E0 | 7.0E0 | 1.8E1 | 6.4E1 | 4.9E1 | 1.4E2 | 1.4E-4 | 5.1E-2 | 5.3E2 | 5.2E2 | 357 | 29 | 135 | 29 | 0.55 |
| Cw | mIU/mL | 3.0E-2 | 3.4E-2 | 3.8E-2 | 2.8E-1 | 3.2E-2 | 1.2E0 | 8.9E-4 | 4.1E-3 | 2.4E-1 | 6.8E0 | 357 | 29 | 135 | 29 | 0.56 |
| Cx | ng/mL | 1.5E-1 | 1.1E0 | 5.1E1 | 7.0E1 | 9.9E1 | 1.2E2 | 9.3E-5 | 9.3E-5 | 3.9E2 | 3.9E2 | 357 | 29 | 135 | 29 | 0.50 |
| Db | ug/mL | 7.2E0 | 8.2E0 | 8.6E0 | 8.8E0 | 7.3E0 | 6.6E0 | 4.5E-1 | 8.8E-1 | 5.9E1 | 2.3E1 | 357 | 29 | 135 | 29 | 0.53 |
| Dc | nmol/L | 1.9E-2 | 2.4E-2 | 5.7E-2 | 6.2E-1 | 1.4E-1 | 2.6E0 | 5.2E-6 | 1.0E-3 | 1.6E0 | 1.4E1 | 357 | 29 | 135 | 29 | 0.59 |
| Dd | ug/mL | 6.9E-2 | 4.3E-2 | 1.8E-1 | 2.5E-1 | 2.7E-1 | 6.6E-1 | 1.9E-4 | 3.4E-3 | 1.9E0 | 3.6E0 | 357 | 29 | 135 | 29 | 0.49 |
| De | ng/mL | 3.4E-3 | 3.4E-3 | 7.8E-2 | 9.6E-2 | 1.4E-1 | 2.2E-1 | 3.4E-3 | 3.4E-3 | 9.2E-1 | 9.0E-1 | 357 | 29 | 135 | 29 | 0.49 |
| Dg | ng/mL | 2.9E1 | 5.2E1 | 4.2E1 | 6.3E1 | 3.8E1 | 5.0E1 | 1.0E-1 | 2.3E0 | 1.9E2 | 1.9E2 | 357 | 29 | 135 | 29 | 0.62 |
| Di | pg/mL | 2.0E0 | 2.8E0 | 2.2E0 | 2.8E0 | 2.0E0 | 2.1E0 | 1.8E-1 | 1.8E-1 | 1.3E1 | 9.0E0 | 357 | 29 | 135 | 29 | 0.60 |
| Dk | uIU/mL | 1.7E-2 | 2.5E-2 | 9.6E-1 | 8.4E-1 | 5.7E-1 | 1.6E-1 | 1.1E-4 | 1.1E-4 | 8.9E0 | 6.3E-1 | 357 | 29 | 135 | 29 | 0.59 |
| Dl | ng/mL | 2.3E2 | 3.7E2 | 3.1E2 | 4.5E2 | 2.8E2 | 4.1E2 | 1.7E0 | 1.8E1 | 1.5E3 | 1.6E3 | 357 | 29 | 135 | 29 | 0.60 |
| Dp | ng/ml | 2.3E0 | 1.7E0 | 5.1E0 | 1.4E1 | 7.9E0 | 3.8E1 | 3.7E-3 | 3.7E-3 | 4.6E1 | 2.0E2 | 217 | 29 | 135 | 29 | 0.46 |
| Dr | pg/ml | 2.1E1 | 3.0E1 | 4.7E1 | 8.2E2 | 7.1E1 | 2.7E3 | 7.5E-1 | 7.5E-1 | 5.2E2 | 1.0E4 | 125 | 15 | 71 | 15 | 0.61 |
| Du | pg/ml | 6.1E1 | 2.4E2 | 8.9E2 | 2.7E3 | 3.1E3 | 6.4E3 | 1.2E0 | 1.2E0 | 2.6E4 | 2.4E4 | 80 | 14 | 62 | 14 | 0.58 |
| Ef | ng/ml | 1.5E-1 | 2.4E-1 | 8.1E-1 | 8.7E-1 | 1.6E0 | 1.7E0 | 5.7E-4 | 1.1E-2 | 9.5E0 | 7.0E0 | 261 | 29 | 134 | 29 | 0.55 |
| Wm | % | 4.9E-1 | 1.8E0 | 2.3E1 | 1.3E2 | 1.6E2 | 3.1E2 | 5.4E-2 | 8.5E-2 | 2.4E3 | 1.0E3 | 283 | 33 | 151 | 33 | 0.60 |
| Ed | ng/mL | 5.2E-1 | 2.9E1 | 6.3E1 | 6.6E1 | 5.0E2 | 1.0E2 | 5.2E-1 | 5.2E-1 | 7.3E3 | 5.0E2 | 217 | 29 | 134 | 29 | 0.63 |
| Yf | ng/mL | 1.6E1 | 1.5E1 | 1.1E2 | 3.7E1 | 7.0E2 | 7.8E1 | 2.9E-1 | 2.9E-1 | 6.6E3 | 2.9E2 | 89 | 13 | 69 | 13 | 0.45 |
| Tj | pg/mL | 3.7E-1 | 3.7E-1 | 6.8E1 | 2.3E1 | 3.3E2 | 6.3E1 | 3.6E-1 | 3.7E-1 | 3.5E3 | 3.1E2 | 258 | 30 | 136 | 30 | 0.51 |
| Po | pg/mL | 6.7E-1 | 7.0E0 | 9.1E0 | 2.5E1 | 2.5E1 | 4.6E1 | 8.0E-3 | 2.6E-2 | 2.7E2 | 2.2E2 | 580 | 43 | 207 | 43 | 0.68 |
| Ti | ug/mL | 3.1E0 | 5.2E0 | 4.4E0 | 6.6E0 | 3.9E0 | 4.7E0 | 8.7E-3 | 8.0E-1 | 1.7E1 | 1.8E1 | 132 | 19 | 99 | 19 | 0.66 |
| Em | ng/ml | 9.2E-3 | 2.9E-3 | 6.7E-2 | 1.5E-1 | 1.2E-1 | 4.8E-1 | 1.9E-16 | 8.4E-4 | 6.0E-1 | 1.9E0 | 149 | 16 | 71 | 16 | 0.42 |
| Et | ng/ml | 1.3E3 | 3.0E3 | 1.6E3 | 2.8E3 | 1.1E3 | 1.2E3 | 7.7E1 | 1.1E2 | 5.0E3 | 5.0E3 | 579 | 43 | 207 | 43 | 0.77 |
| Eq | pg/ml | 1.9E2 | 5.8E1 | 3.5E2 | 2.3E2 | 4.0E2 | 3.6E2 | 1.0E0 | 1.0E0 | 1.8E3 | 1.3E3 | 80 | 14 | 62 | 14 | 0.37 |
| Th | ug/mL | 1.1E0 | 8.5E-1 | 1.7E0 | 1.2E0 | 1.6E0 | 1.2E0 | 2.6E-3 | 2.6E-3 | 1.2E1 | 4.2E0 | 132 | 19 | 99 | 19 | 0.39 |
| Fa | ng/ml | 4.0E1 | 1.1E2 | 1.3E2 | 2.8E2 | 6.0E2 | 5.1E2 | 3.4E-2 | 6.0E-1 | 8.0E3 | 2.5E3 | 212 | 29 | 133 | 29 | 0.72 |
| Ez | ng/ml | 5.0E0 | 5.0E0 | 2.0E1 | 1.3E1 | 5.9E1 | 2.0E1 | 1.3E-2 | 5.8E-2 | 7.1E2 | 8.8E1 | 217 | 29 | 135 | 29 | 0.52 |
| Fb | ng/ml | 2.5E1 | 2.8E1 | 2.3E1 | 2.8E1 | 1.1E1 | 9.5E0 | 6.6E-1 | 5.9E-1 | 5.7E1 | 4.3E1 | 213 | 29 | 133 | 29 | 0.61 |
| Ex | ng/ml | 7.8E-2 | 1.7E-1 | 2.5E-1 | 2.5E-1 | 7.6E-1 | 3.2E-1 | 3.5E-5 | 1.7E-4 | 8.9E0 | 1.2E0 | 190 | 21 | 89 | 21 | 0.59 |

Figure 3

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fc | pg/ml | 2.2E-1 | 2.2E-1 | 1.9E2 | 2.9E1 | 1.6E3 | 8.2E1 | 2.2E-1 | 2.2E-1 | 1.5E4 | 3.1E2 | 82 | 14 | 62 | 14 | 0.58 |
| Fd | pg/ml | 9.8E-1 | 2.2E2 | 8.8E2 | 2.4E3 | 3.8E3 | 6.6E3 | 4.5E-1 | 9.8E-1 | 3.3E4 | 2.5E4 | 82 | 14 | 62 | 14 | 0.60 |
| Fi | pg/ml | 2.5E-1 | 2.5E-1 | 2.2E2 | 2.3E1 | 1.6E3 | 6.8E1 | 2.5E-1 | 2.5E-1 | 1.4E4 | 2.5E2 | 82 | 14 | 62 | 14 | 0.51 |
| Fn | ng/ml | 2.1E-1 | 2.1E-1 | 6.3E0 | 4.3E0 | 2.9E1 | 6.9E0 | 1.1E-14 | 2.1E-1 | 4.2E2 | 2.7E1 | 217 | 29 | 135 | 29 | 0.49 |
| Fp | ng/ml | 1.2E1 | 4.6E1 | 2.4E1 | 5.2E1 | 2.8E1 | 4.0E1 | 6.0E-3 | 2.1E0 | 1.4E2 | 1.4E2 | 606 | 42 | 209 | 42 | 0.73 |
| Fr | ng/ml | 3.3E4 | 9.9E4 | 1.1E5 | 2.4E5 | 1.7E5 | 2.6E5 | 1.9E2 | 1.3E3 | 9.0E5 | 8.4E5 | 686 | 44 | 210 | 44 | 0.68 |
| Fw | pg/ml | 8.5E-1 | 2.9E0 | 7.0E1 | 6.4E1 | 5.4E2 | 1.9E2 | 1.1E-14 | 1.2E-1 | 6.9E3 | 9.1E2 | 259 | 30 | 135 | 30 | 0.59 |
| Fy | ng/ml | 3.5E1 | 5.1E1 | 5.5E1 | 1.2E2 | 5.7E1 | 1.7E2 | 1.2E-1 | 5.3E0 | 3.3E2 | 6.5E2 | 216 | 28 | 134 | 28 | 0.61 |
| Gh | pg/ml | 3.7E0 | 3.7E0 | 8.1E1 | 8.0E0 | 2.9E2 | 1.3E1 | 2.9E-2 | 2.9E-2 | 1.8E3 | 4.6E1 | 80 | 14 | 62 | 14 | 0.46 |
| Gb | % | 4.2E1 | 3.9E1 | 4.4E1 | 6.6E1 | 3.3E1 | 7.2E1 | 2.2E0 | 2.1E1 | 1.9E2 | 3.0E2 | 82 | 14 | 61 | 14 | 0.60 |
| Gc | ng/ml | 9.2E1 | 1.5E2 | 1.4E2 | 1.8E2 | 1.7E2 | 1.3E2 | 6.4E0 | 2.9E1 | 1.2E3 | 4.7E2 | 134 | 15 | 72 | 15 | 0.66 |
| Gd | ng/ml | 3.1E1 | 2.9E1 | 3.3E1 | 3.4E1 | 1.7E1 | 2.3E1 | 3.0E0 | 7.6E0 | 8.1E1 | 8.0E1 | 149 | 15 | 68 | 15 | 0.49 |
| Gn | U/ml | 3.6E-1 | 1.5E-1 | 1.3E0 | 8.7E0 | 3.3E0 | 2.9E1 | 1.3E-3 | 5.6E-3 | 3.0E1 | 1.1E2 | 119 | 15 | 69 | 15 | 0.47 |
| Gl | pg/ml | 7.8E3 | 9.7E3 | 1.1E4 | 1.4E4 | 9.4E3 | 1.1E4 | 9.1E1 | 7.7E2 | 3.3E4 | 3.1E4 | 252 | 30 | 135 | 30 | 0.59 |
| Gp | U/ml | 1.5E0 | 6.3E-1 | 4.0E0 | 3.3E0 | 6.8E0 | 8.7E0 | 1.3E-3 | 1.5E-2 | 6.7E1 | 4.8E1 | 261 | 30 | 135 | 30 | 0.38 |
| Gz | ug/ml | 1.4E0 | 1.0E0 | 9.7E0 | 4.0E0 | 4.2E1 | 5.0E0 | 2.9E-16 | 1.0E0 | 4.8E2 | 1.5E1 | 143 | 21 | 86 | 21 | 0.46 |
| Ha | pg/ml | 2.7E0 | 4.9E0 | 9.9E0 | 1.3E1 | 2.1E1 | 2.6E1 | 1.7E-2 | 6.4E-3 | 1.3E2 | 1.0E2 | 215 | 29 | 134 | 29 | 0.57 |
| Nm | pg/ml | 1.6E4 | 2.8E4 | 3.2E4 | 6.1E4 | 8.8E4 | 1.3E5 | 1.0E-9 | 1.0E-9 | 1.6E6 | 8.2E5 | 583 | 43 | 209 | 43 | 0.62 |
| Nn | pg/ml | 1.5E2 | 4.1E2 | 2.2E3 | 6.2E3 | 9.4E3 | 2.1E4 | 1.0E-9 | 1.0E-9 | 1.0E5 | 1.1E5 | 583 | 43 | 209 | 43 | 0.63 |
| No | pg/ml | 1.5E1 | 4.1E1 | 3.7E1 | 1.1E2 | 1.3E2 | 1.8E2 | 1.0E-9 | 1.7E0 | 2.5E3 | 7.7E2 | 583 | 43 | 209 | 43 | 0.71 |
| Nq | pg/ml | 2.0E0 | 4.0E0 | 1.9E1 | 3.1E1 | 7.6E1 | 6.4E1 | 1.0E-9 | 1.0E-9 | 1.2E3 | 2.9E2 | 583 | 43 | 209 | 43 | 0.55 |
| Nr | pg/ml | 8.8E-1 | 6.1E0 | 3.3E1 | 7.3E1 | 2.1E2 | 2.3E2 | 1.0E-9 | 1.0E-9 | 4.1E3 | 1.4E3 | 583 | 43 | 209 | 43 | 0.66 |
| Ns | pg/ml | 1.0E-9 | 1.0E-9 | 1.1E1 | 1.9E0 | 6.1E1 | 1.2E1 | 1.0E-9 | 1.0E-9 | 1.1E3 | 7.9E1 | 583 | 43 | 209 | 43 | 0.47 |
| Nt | pg/ml | 1.0E2 | 1.6E2 | 1.4E2 | 2.1E2 | 1.1E2 | 2.0E2 | 1.0E-9 | 4.4E1 | 1.5E3 | 1.2E3 | 583 | 43 | 209 | 43 | 0.66 |
| Nu | pg/ml | 2.3E1 | 5.2E1 | 5.7E1 | 9.8E1 | 9.5E1 | 1.1E2 | 1.0E-9 | 1.0E-9 | 8.9E2 | 3.7E2 | 583 | 43 | 209 | 43 | 0.63 |
| Lu | pg/ml | 1.0E4 | 1.0E4 | 1.7E4 | 9.3E3 | 4.7E4 | 5.8E3 | 3.5E2 | 1.1E3 | 7.5E5 | 2.5E4 | 585 | 43 | 209 | 43 | 0.45 |
| Lv | pg/ml | 1.0E-9 | 2.0E1 | 1.1E1 | 3.1E1 | 2.1E1 | 4.0E1 | 1.0E-9 | 1.0E-9 | 2.4E2 | 1.6E2 | 585 | 43 | 209 | 43 | 0.65 |
| Lw | pg/ml | 1.0E-9 | 1.0E-9 | 4.0E-1 | 2.1E0 | 4.3E0 | 7.6E0 | 1.0E-9 | 1.0E-9 | 8.0E1 | 4.0E1 | 585 | 43 | 209 | 43 | 0.54 |
| Lx | pg/ml | 1.0E-9 | 1.6E2 | 1.5E2 | 5.6E2 | 4.5E2 | 9.4E2 | 1.0E-9 | 1.0E-9 | 6.2E3 | 4.5E3 | 585 | 43 | 209 | 43 | 0.73 |
| Ly | pg/ml | 1.0E-9 | 1.0E-9 | 1.0E1 | 1.1E1 | 2.0E1 | 1.7E1 | 1.0E-9 | 1.0E-9 | 1.6E2 | 6.3E1 | 585 | 43 | 209 | 43 | 0.51 |
| Lz | pg/ml | 1.0E-9 | 1.0E-9 | 4.9E0 | 5.6E0 | 3.6E1 | 1.6E1 | 1.0E-9 | 1.0E-9 | 6.0E2 | 6.2E1 | 585 | 43 | 209 | 43 | 0.53 |
| Ma | pg/ml | 3.1E2 | 7.4E2 | 1.3E3 | 2.4E3 | 3.8E3 | 5.1E3 | 1.0E-9 | 1.0E-9 | 6.5E4 | 3.1E4 | 585 | 43 | 209 | 43 | 0.65 |
| Mb | pg/ml | 2.5E1 | 3.7E1 | 3.1E1 | 3.7E1 | 1.6E1 | 1.7E1 | 5.4E0 | 4.1E0 | 2.1E2 | 7.1E1 | 585 | 43 | 209 | 43 | 0.59 |
| Mc | pg/ml | 1.0E-9 | 1.0E-9 | 4.2E-2 | 1.0E-9 | 5.8E-1 | 0.0E0 | 1.0E-9 | 1.0E-9 | 1.3E1 | 1.0E-9 | 585 | 43 | 209 | 43 | 0.49 |
| Md | pg/ml | 1.0E-9 | 1.0E-9 | 4.8E-1 | 9.5E-1 | 3.3E0 | 4.6E0 | 1.0E-9 | 1.0E-9 | 6.5E1 | 2.9E1 | 585 | 43 | 209 | 43 | 0.50 |
| Me | pg/ml | 3.2E1 | 2.3E1 | 3.1E1 | 2.5E1 | 2.0E1 | 3.0E1 | 1.0E-9 | 1.0E-9 | 3.2E2 | 1.8E2 | 585 | 43 | 209 | 43 | 0.35 |
| Mf | pg/ml | 1.0E-9 | 1.0E-9 | 5.2E-1 | 7.8E-1 | 3.1E0 | 1.9E0 | 1.0E-9 | 1.0E-9 | 5.6E1 | 9.1E0 | 585 | 43 | 209 | 43 | 0.57 |
| Mg | pg/ml | 2.0E0 | 2.3E0 | 7.7E0 | 8.6E0 | 1.3E1 | 1.3E1 | 1.0E-9 | 1.0E-9 | 9.2E1 | 5.9E1 | 585 | 43 | 209 | 43 | 0.53 |
| Mh | pg/ml | 1.0E-9 | 1.0E-9 | 1.5E0 | 2.6E0 | 1.1E1 | 7.3E0 | 1.0E-9 | 1.0E-9 | 1.6E2 | 4.2E1 | 585 | 43 | 209 | 43 | 0.59 |
| Mi | pg/ml | 1.0E-9 | 1.0E-9 | 5.9E-1 | 3.6E0 | 6.3E0 | 1.7E1 | 1.0E-9 | 1.0E-9 | 1.2E2 | 1.1E2 | 585 | 43 | 209 | 43 | 0.52 |
| Mj | pg/ml | 1.0E-9 | 1.0E-9 | 4.8E0 | 1.5E1 | 2.7E1 | 4.4E1 | 1.0E-9 | 1.0E-9 | 4.6E2 | 2.1E2 | 585 | 43 | 209 | 43 | 0.55 |
| Mk | pg/ml | 5.3E-1 | 2.0E0 | 1.8E1 | 1.8E1 | 1.1E2 | 7.6E1 | 1.0E-9 | 1.0E-9 | 1.7E3 | 5.0E2 | 585 | 43 | 209 | 43 | 0.53 |
| Ml | pg/ml | 1.0E-9 | 1.0E-9 | 6.3E0 | 2.5E1 | 9.0E1 | 9.3E1 | 1.0E-9 | 1.0E-9 | 2.1E3 | 5.1E2 | 585 | 43 | 209 | 43 | 0.58 |
| Mm | pg/ml | 5.9E2 | 8.8E2 | 9.8E2 | 1.8E3 | 1.1E3 | 2.3E3 | 1.0E-9 | 1.0E-9 | 7.3E3 | 1.2E4 | 585 | 43 | 209 | 43 | 0.61 |
| Mn | pg/ml | 5.4E0 | 9.3E0 | 1.1E1 | 1.4E1 | 2.6E1 | 2.0E1 | 1.0E-9 | 4.2E-1 | 3.5E2 | 1.3E2 | 585 | 43 | 209 | 43 | 0.62 |
| Mp | pg/ml | 1.0E-9 | 7.4E0 | 9.2E0 | 2.0E1 | 3.2E1 | 3.2E1 | 1.0E-9 | 1.0E-9 | 6.3E2 | 1.3E2 | 584 | 43 | 209 | 43 | 0.63 |
| Mq | pg/ml | 1.0E-9 | 1.0E-9 | 2.9E0 | 1.1E1 | 1.7E1 | 2.4E1 | 1.0E-9 | 1.0E-9 | 2.1E2 | 1.0E2 | 584 | 43 | 209 | 43 | 0.62 |
| Mr | pg/ml | 1.0E-9 | 1.0E-9 | 1.9E1 | 1.7E2 | 8.5E1 | 5.9E2 | 1.0E-9 | 1.0E-9 | 1.4E3 | 3.4E3 | 584 | 43 | 209 | 43 | 0.59 |
| Ms | pg/ml | 4.1E2 | 2.6E2 | 5.6E2 | 3.7E2 | 6.5E2 | 3.9E2 | 1.0E-9 | 1.0E-9 | 5.6E3 | 1.9E3 | 584 | 43 | 209 | 43 | 0.41 |
| Mt | pg/ml | 2.2E-1 | 2.0E0 | 7.4E2 | 9.2E1 | 5.0E1 | 4.9E2 | 1.0E-9 | 1.0E-9 | 8.7E2 | 3.2E3 | 584 | 43 | 209 | 43 | 0.71 |
| Mu | pg/ml | 1.0E-9 | 1.0E-9 | 1.6E0 | 2.1E0 | 1.3E1 | 6.3E0 | 1.0E-9 | 1.0E-9 | 2.3E2 | 3.5E1 | 584 | 43 | 209 | 43 | 0.59 |
| Mv | pg/ml | 1.0E-9 | 1.0E-9 | 7.6E1 | 1.2E2 | 3.6E2 | 4.2E2 | 1.0E-9 | 1.0E-9 | 4.5E3 | 2.5E3 | 584 | 43 | 209 | 43 | 0.56 |
| Mw | pg/ml | 3.4E1 | 8.6E1 | 4.8E2 | 6.1E2 | 3.1E3 | 1.5E3 | 1.0E-9 | 1.0E-9 | 6.2E4 | 5.9E3 | 584 | 43 | 209 | 43 | 0.64 |
| Mx | pg/ml | 1.0E-9 | 1.0E-9 | 2.5E-1 | 9.2E-1 | 1.5E0 | 3.1E0 | 1.0E-9 | 1.0E-9 | 3.2E1 | 2.0E1 | 584 | 43 | 209 | 43 | 0.59 |
| My | pg/ml | 1.0E-9 | 1.0E-9 | 4.7E2 | 2.0E2 | 3.1E3 | 7.5E2 | 1.0E-9 | 1.0E-9 | 3.9E4 | 4.6E3 | 584 | 43 | 209 | 43 | 0.51 |
| Mz | pg/ml | 1.0E1 | 2.6E1 | 2.5E1 | 1.1E2 | 7.2E1 | 3.5E2 | 1.0E-9 | 1.0E-9 | 1.2E3 | 1.9E3 | 584 | 43 | 209 | 43 | 0.69 |
| Na | pg/ml | 1.0E-9 | 1.0E-9 | 7.4E-1 | 2.2E0 | 3.0E0 | 6.9E0 | 1.0E-9 | 1.0E-9 | 3.6E1 | 4.2E1 | 584 | 43 | 209 | 43 | 0.55 |

Figure 3 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nb | pg/ml | 1.9E0 | 2.5E0 | 4.2E0 | 1.1E1 | 1.4E1 | 3.5E1 | 1.0E-9 | 1.0E-9 | 2.3E2 | 2.1E2 | 584 | 43 | 209 | 43 | 0.60 |
| Nc | pg/ml | 4.0E2 | 2.3E2 | 6.3E2 | 3.3E2 | 7.9E2 | 3.5E2 | 1.0E-9 | 1.0E-9 | 9.2E3 | 1.1E3 | 584 | 43 | 209 | 43 | 0.41 |
| Nd | pg/ml | 2.9E1 | 6.5E0 | 2.7E1 | 1.6E1 | 5.4E1 | 2.0E1 | 1.0E-9 | 1.0E-9 | 1.2E3 | 9.4E1 | 584 | 43 | 209 | 43 | 0.37 |
| Ne | pg/ml | 4.7E2 | 2.9E2 | 6.1E2 | 3.6E2 | 6.0E2 | 3.2E2 | 1.0E-9 | 1.0E-9 | 7.0E3 | 1.7E3 | 584 | 43 | 209 | 43 | 0.37 |
| Nf | pg/ml | 1.0E-9 | 1.0E-9 | 3.0E0 | 7.8E0 | 1.1E1 | 2.7E1 | 1.0E-9 | 1.0E-9 | 1.6E2 | 1.3E2 | 584 | 43 | 209 | 43 | 0.52 |
| Ng | pg/ml | 3.6E1 | 1.0E1 | 1.4E2 | 7.9E1 | 2.6E2 | 1.9E2 | 1.0E-9 | 1.0E-9 | 2.3E3 | 1.2E3 | 584 | 43 | 209 | 43 | 0.44 |
| Nh | pg/ml | 7.1E1 | 3.7E1 | 9.5E1 | 5.6E1 | 8.8E1 | 6.8E1 | 1.0E-9 | 4.1E0 | 5.6E2 | 4.3E2 | 584 | 43 | 209 | 43 | 0.34 |
| Ni | pg/ml | 1.0E-9 | 1.4E1 | 7.8E1 | 1.4E2 | 1.2E2 | 2.1E2 | 1.0E-9 | 1.0E-9 | 7.1E2 | 1.1E3 | 584 | 43 | 209 | 43 | 0.57 |
| Nj | pg/ml | 7.9E0 | 2.8E0 | 1.1E1 | 6.4E0 | 1.2E1 | 7.9E0 | 1.0E-9 | 1.0E-9 | 8.3E1 | 3.3E1 | 584 | 43 | 209 | 43 | 0.36 |
| Nk | pg/ml | 2.0E1 | 1.7E1 | 3.5E1 | 3.4E1 | 4.0E1 | 4.5E1 | 1.0E-9 | 1.0E-9 | 2.0E2 | 2.0E2 | 584 | 43 | 209 | 43 | 0.50 |
| Nl | pg/ml | 4.9E1 | 2.4E1 | 6.6E1 | 3.5E1 | 7.4E1 | 3.3E1 | 1.0E-9 | 1.0E-9 | 1.1E3 | 1.3E2 | 584 | 43 | 209 | 43 | 0.36 |
| Hl | pg/ml | 1.8E1 | 1.8E1 | 4.0E1 | 3.1E2 | 6.7E1 | 9.5E2 | 1.0E-9 | 1.0E-9 | 3.5E2 | 3.6E3 | 82 | 14 | 62 | 14 | 0.53 |
| Ho | pg/ml | 1.7E1 | 2.0E1 | 2.9E1 | 4.6E1 | 7.7E1 | 9.9E1 | 1.0E-9 | 7.6E0 | 7.0E2 | 3.9E2 | 82 | 14 | 62 | 14 | 0.59 |
| Hp | ng/ml | 1.6E0 | 3.8E0 | 1.2E2 | 2.6E2 | 3.0E2 | 4.1E2 | 1.0E-9 | 2.0E-1 | 8.9E2 | 8.9E2 | 82 | 14 | 62 | 14 | 0.62 |
| Tz | ng/ml | 5.3E3 | 6.9E3 | 1.4E4 | 2.0E4 | 6.9E4 | 6.8E4 | 1.0E-9 | 6.8E2 | 1.0E6 | 3.7E5 | 219 | 29 | 133 | 29 | 0.55 |
| Ua | pg/ml | 3.9E3 | 5.1E3 | 1.6E4 | 8.7E3 | 2.9E4 | 1.2E4 | 1.0E-9 | 9.4E2 | 1.9E5 | 6.6E4 | 219 | 29 | 133 | 29 | 0.52 |
| Ub | pg/ml | 5.7E2 | 4.8E2 | 8.5E2 | 8.1E2 | 1.1E3 | 9.4E2 | 1.0E-9 | 1.2E1 | 9.8E3 | 4.1E3 | 219 | 29 | 133 | 29 | 0.48 |
| Ue | pg/ml | 2.9E1 | 2.7E1 | 3.6E1 | 4.2E1 | 3.2E1 | 3.5E1 | 9.8E-2 | 5.9E0 | 3.5E2 | 1.4E2 | 219 | 29 | 133 | 29 | 0.53 |
| Uc | pg/ml | 9.2E2 | 1.4E3 | 1.7E3 | 3.9E3 | 2.9E3 | 1.0E4 | 1.0E-9 | 5.5E1 | 2.9E4 | 5.7E4 | 219 | 29 | 133 | 29 | 0.59 |
| Ud | pg/ml | 1.0E-9 | 1.0E-9 | 1.9E0 | 1.8E0 | 2.6E1 | 9.9E0 | 1.0E-9 | 1.0E-9 | 3.9E2 | 5.3E1 | 219 | 29 | 133 | 29 | 0.51 |
| Hq | pg/ml | 1.1E0 | 1.3E0 | 1.5E2 | 1.3E1 | 2.0E3 | 4.4E1 | 1.0E-9 | 1.0E-9 | 3.4E4 | 2.3E2 | 581 | 43 | 208 | 43 | 0.51 |
| Hr | pg/ml | 1.3E2 | 1.2E2 | 8.0E2 | 7.4E2 | 1.6E3 | 1.7E3 | 1.0E-9 | 1.0E-9 | 1.4E4 | 8.9E3 | 581 | 43 | 208 | 43 | 0.49 |
| Hu | pg/ml | 1.1E1 | 3.4E1 | 3.2E3 | 1.1E3 | 3.1E4 | 5.0E3 | 1.0E-9 | 1.0E-9 | 6.3E5 | 3.2E4 | 581 | 43 | 208 | 43 | 0.59 |
| Hv | pg/ml | 1.5E0 | 1.5E0 | 3.4E0 | 2.4E1 | 1.2E1 | 1.4E2 | 1.0E-9 | 1.0E-9 | 2.5E2 | 8.9E2 | 581 | 43 | 208 | 43 | 0.50 |
| Hw | pg/ml | 7.0E0 | 5.0E0 | 2.2E1 | 2.4E2 | 8.6E1 | 1.4E3 | 1.0E-9 | 1.0E-9 | 1.7E3 | 9.4E3 | 581 | 43 | 208 | 43 | 0.42 |
| Hx | pg/ml | 9.6E0 | 1.4E1 | 4.7E1 | 7.1E1 | 4.0E2 | 2.3E2 | 1.0E-9 | 1.0E-9 | 9.3E3 | 1.3E3 | 581 | 43 | 208 | 43 | 0.56 |
| Ib | ng/ml | 6.7E-2 | 4.0E-2 | 2.3E0 | 2.2E0 | 7.8E0 | 1.0E1 | 1.0E-9 | 1.0E-9 | 5.3E1 | 5.6E1 | 210 | 29 | 132 | 29 | 0.44 |
| Ic | U/ml | 2.2E2 | 2.2E2 | 8.1E2 | 2.3E2 | 6.5E3 | 1.4E2 | 2.4E0 | 2.1E1 | 9.3E4 | 5.4E2 | 210 | 29 | 132 | 29 | 0.57 |
| Id | U/ml | 6.5E-1 | 9.9E-1 | 1.2E0 | 1.8E1 | 2.0E0 | 8.0E1 | 1.0E-9 | 2.4E-1 | 2.3E1 | 4.3E2 | 210 | 29 | 132 | 29 | 0.65 |
| Tt | pg/ml | 1.7E2 | 1.7E2 | 1.7E2 | 1.8E2 | 5.1E1 | 7.3E1 | 4.3E1 | 1.0E2 | 3.6E2 | 4.4E2 | 202 | 26 | 127 | 26 | 0.52 |
| To | pg/ml | 1.6E0 | 1.8E0 | 1.9E0 | 1.9E0 | 2.0E0 | 2.5E0 | 1.0E-9 | 1.0E-9 | 1.0E1 | 1.2E1 | 211 | 27 | 130 | 27 | 0.49 |
| Tr | pg/ml | 3.0E0 | 5.2E0 | 6.2E0 | 1.1E1 | 2.2E1 | 1.6E1 | 1.0E-9 | 4.7E-2 | 3.1E2 | 7.6E1 | 207 | 26 | 129 | 26 | 0.64 |
| Tn | pg/ml | 2.9E1 | 5.2E1 | 7.5E1 | 1.6E2 | 2.0E2 | 4.4E2 | 2.4E0 | 6.6E0 | 1.8E3 | 2.3E3 | 211 | 27 | 130 | 27 | 0.65 |
| Tv | ng/ml | 1.2E1 | 1.0E1 | 2.0E1 | 3.0E2 | 3.9E1 | 1.4E3 | 1.0E-9 | 1.0E-9 | 4.9E2 | 7.1E3 | 211 | 27 | 130 | 27 | 0.46 |
| Ih | ng/ml | 7.5E1 | 1.9E2 | 2.1E2 | 3.9E2 | 3.6E2 | 5.2E2 | 1.0E-9 | 1.0E-9 | 2.6E3 | 2.8E3 | 584 | 43 | 208 | 43 | 0.63 |
| Ii | ng/ml | 9.8E1 | 1.1E2 | 2.7E2 | 3.9E2 | 7.6E2 | 8.6E2 | 7.3E-1 | 2.3E0 | 1.0E4 | 4.5E3 | 584 | 43 | 208 | 43 | 0.55 |
| Ij | ng/ml | 7.6E1 | 1.3E2 | 1.9E2 | 7.7E2 | 6.3E2 | 3.7E3 | 2.1E0 | 1.1E1 | 6.4E3 | 2.4E4 | 579 | 42 | 207 | 42 | 0.67 |
| Ik | ng/ml | 1.4E1 | 2.5E2 | 1.1E3 | 5.5E2 | 1.0E4 | 6.7E2 | 5.9E-1 | 2.3E0 | 1.2E5 | 2.5E3 | 581 | 43 | 207 | 43 | 0.66 |
| Il | ng/ml | 3.4E2 | 6.0E2 | 1.3E3 | 2.2E3 | 2.7E3 | 3.7E3 | 1.0E-9 | 1.0E-9 | 1.2E4 | 1.3E4 | 574 | 43 | 207 | 43 | 0.57 |
| Im | ng/ml | 2.0E2 | 6.0E2 | 3.5E2 | 9.0E2 | 5.2E2 | 1.3E3 | 1.3E1 | 4.7E1 | 6.0E3 | 6.2E3 | 581 | 43 | 207 | 43 | 0.72 |
| In | ng/ml | 3.9E0 | 3.4E0 | 2.5E1 | 1.1E2 | 1.8E2 | 6.8E2 | 1.0E-9 | 1.0E-9 | 3.9E3 | 4.5E3 | 584 | 43 | 208 | 43 | 0.47 |
| Hb | ng/ml | 2.4E1 | 3.5E1 | 3.2E1 | 5.2E1 | 2.9E1 | 4.9E1 | 4.8E-1 | 6.2E-1 | 1.4E2 | 1.9E2 | 217 | 29 | 134 | 29 | 0.62 |
| Hc | pg/ml | 7.6E2 | 5.9E2 | 4.0E3 | 1.5E3 | 1.4E4 | 2.9E3 | 1.0E-9 | 1.0E-9 | 1.0E5 | 1.4E4 | 217 | 29 | 134 | 29 | 0.42 |
| Hf | ng/ml | 1.5E2 | 2.1E2 | 4.1E2 | 2.9E2 | 5.8E2 | 2.9E2 | 1.0E-9 | 1.0E-9 | 3.2E3 | 9.9E2 | 217 | 29 | 134 | 29 | 0.50 |
| Io | ng/ml | 8.4E3 | 1.5E4 | 2.7E4 | 1.5E4 | 1.8E5 | 1.3E4 | 1.0E-9 | 1.8E2 | 4.0E6 | 5.4E4 | 578 | 43 | 208 | 43 | 0.55 |
| Ip | ng/ml | 1.0E1 | 3.0E1 | 1.9E1 | 3.0E1 | 2.4E1 | 2.4E1 | 1.0E-9 | 3.7E-2 | 2.6E2 | 8.8E1 | 578 | 43 | 208 | 43 | 0.65 |
| Iq | ug/ml | 9.8E-2 | 1.9E-1 | 2.4E1 | 7.0E0 | 5.7E2 | 3.4E1 | 1.0E-9 | 1.0E-9 | 1.4E4 | 2.2E2 | 578 | 43 | 208 | 43 | 0.57 |
| Ir | ug/ml | 3.4E-1 | 8.3E-1 | 2.7E0 | 1.6E1 | 1.7E1 | 6.1E1 | 1.0E-9 | 1.0E-9 | 2.4E2 | 3.7E2 | 577 | 43 | 208 | 43 | 0.68 |
| Is | ng/ml | 1.5E0 | 6.5E0 | 5.4E0 | 2.1E1 | 1.1E1 | 4.6E1 | 1.0E-9 | 5.3E-2 | 8.8E1 | 2.6E2 | 578 | 43 | 208 | 43 | 0.71 |
| It | ng/ml | 1.9E0 | 4.2E0 | 2.2E1 | 3.3E1 | 1.5E2 | 1.1E2 | 1.0E-9 | 1.0E-9 | 2.8E3 | 6.8E2 | 578 | 43 | 208 | 43 | 0.64 |
| Iu | ng/ml | 2.2E2 | 3.1E2 | 1.3E3 | 2.2E3 | 4.0E3 | 5.3E3 | 1.0E-9 | 1.0E-9 | 2.9E4 | 2.4E4 | 578 | 43 | 208 | 43 | 0.53 |
| Iv | ng/ml | 1.4E1 | 3.2E1 | 4.1E1 | 2.4E2 | 1.0E1 | 7.9E2 | 1.0E-9 | 1.0E-9 | 1.6E3 | 3.8E3 | 577 | 43 | 208 | 43 | 0.67 |
| Iz | ng/ml | 1.5E2 | 1.9E2 | 7.3E2 | 2.6E2 | 4.3E3 | 2.7E2 | 1.5E0 | 4.9E0 | 6.2E4 | 1.0E3 | 217 | 29 | 134 | 29 | 0.50 |
| Yg | pg/ml | 2.8E2 | 3.8E2 | 1.3E3 | 8.4E2 | 5.6E3 | 1.4E3 | 1.0E-9 | 1.1E0 | 5.0E4 | 5.0E3 | 82 | 13 | 62 | 13 | 0.55 |
| Yh | pg/ml | 2.1E2 | 3.6E2 | 4.8E2 | 5.6E2 | 9.4E2 | 6.9E2 | 1.0E-9 | 1.0E-9 | 7.8E3 | 2.3E3 | 82 | 13 | 62 | 13 | 0.52 |
| Yi | pg/ml | 2.4E2 | 4.3E2 | 5.2E2 | 2.8E3 | 9.2E2 | 7.1E3 | 1.0E-9 | 1.0E-9 | 7.6E3 | 2.6E4 | 82 | 13 | 62 | 13 | 0.62 |
| Yk | U/ml | 1.0E-9 | 1.0E-9 | 1.6E-1 | 4.3E-1 | 4.6E-1 | 1.6E0 | 1.0E-9 | 1.0E-9 | 3.0E0 | 5.6E0 | 82 | 13 | 62 | 13 | 0.44 |

Figure 3 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yj | pg/ml | 1.4E2 | 1.7E2 | 4.3E2 | 3.1E2 | 9.6E2 | 3.0E2 | 1.0E-9 | 1.0E-9 | 7.0E3 | 8.5E2 | 82 | 13 | 62 | 13 | 0.52 |
| Yd | ng/ml | 2.0E-1 | 1.9E-1 | 3.2E-1 | 3.2E-1 | 3.7E-1 | 3.4E-1 | 6.6E-3 | 6.6E-3 | 1.8E0 | 1.1E0 | 85 | 14 | 65 | 14 | 0.49 |
| Wb | pg/ml | 3.0E4 | 3.4E4 | 3.6E4 | 4.6E4 | 2.4E4 | 3.4E4 | 2.2E3 | 1.4E4 | 1.6E5 | 1.5E5 | 84 | 14 | 65 | 14 | 0.60 |
| Vz | pg/ml | 3.0E0 | 2.6E0 | 4.1E0 | 4.9E0 | 4.8E0 | 5.6E0 | 1.0E-9 | 7.6E-2 | 2.9E1 | 2.2E1 | 84 | 14 | 65 | 14 | 0.55 |
| Si | ng/ml | 1.0E0 | 1.4E0 | 2.0E0 | 2.1E0 | 2.8E0 | 1.8E0 | 8.6E-3 | 3.7E-2 | 1.3E1 | 5.6E0 | 82 | 14 | 62 | 14 | 0.60 |
| Sf | mIU/mL | 1.4E1 | 1.4E1 | 4.5E1 | 2.6E1 | 9.3E1 | 3.5E1 | 8.1E-2 | 1.1E0 | 7.2E2 | 1.2E2 | 82 | 14 | 62 | 14 | 0.49 |
| Sh | mIU/mL | 1.4E1 | 8.3E0 | 5.3E1 | 3.7E1 | 1.1E2 | 7.8E1 | 2.9E-2 | 1.3E-1 | 5.9E2 | 2.9E2 | 82 | 14 | 62 | 14 | 0.44 |
| Sj | ng/ml | 4.2E-1 | 4.1E-1 | 4.2E-1 | 4.3E-1 | 9.9E-2 | 9.7E-2 | 1.1E-1 | 3.2E-1 | 6.2E-1 | 7.0E-1 | 82 | 14 | 62 | 14 | 0.50 |
| Rc | pg/ml | 5.7E3 | 7.6E3 | 7.2E3 | 7.2E3 | 5.4E3 | 3.8E3 | 1.9E2 | 2.1E3 | 2.3E4 | 1.7E4 | 216 | 29 | 133 | 29 | 0.56 |
| Rb | pg/ml | 7.6E-1 | 5.6E-1 | 2.7E0 | 3.7E0 | 4.5E0 | 1.0E1 | 1.0E-9 | 1.0E-9 | 4.3E1 | 5.6E1 | 216 | 29 | 133 | 29 | 0.48 |
| Zq | 2.6ng/ml | 2.2E2 | 4.6E2 | 2.8E2 | 5.2E2 | 2.3E2 | 3.3E2 | 8.3E0 | 1.8E1 | 9.7E2 | 9.7E2 | 82 | 14 | 62 | 14 | 0.72 |
| Zw | 2.5ng/ml | 5.6E0 | 4.6E0 | 1.1E1 | 1.6E1 | 1.4E1 | 2.2E1 | 6.3E-2 | 7.3E-2 | 5.9E1 | 6.3E1 | 85 | 14 | 65 | 14 | 0.55 |
| Zx | 2.3mU/ml | 1.2E-1 | 1.0E-1 | 2.6E-1 | 1.6E-1 | 5.0E-1 | 1.6E-1 | 3.2E-2 | 6.1E-2 | 3.0E0 | 6.7E-1 | 85 | 14 | 65 | 14 | 0.48 |
| Pz | ng/ml | 3.7E3 | 1.0E4 | 7.4E3 | 7.4E3 | 1.9E4 | 5.5E3 | 1.3E1 | 4.6E2 | 2.8E5 | 2.8E4 | 577 | 43 | 206 | 43 | 0.61 |
| Qa | ng/ml | 3.2E3 | 9.4E3 | 6.1E3 | 1.6E4 | 7.4E3 | 3.3E4 | 1.5E2 | 6.8E2 | 5.2E4 | 2.2E5 | 577 | 43 | 206 | 43 | 0.72 |
| Qb | ng/ml | 9.9E1 | 2.0E2 | 2.2E2 | 3.6E2 | 5.2E2 | 6.3E2 | 7.9E-1 | 6.2E0 | 8.3E3 | 4.1E3 | 577 | 43 | 206 | 43 | 0.65 |
| Qc | ng/ml | 2.5E2 | 4.8E2 | 4.7E2 | 6.6E2 | 8.0E2 | 8.1E2 | 1.0E-9 | 3.2E0 | 1.1E4 | 4.3E3 | 577 | 43 | 206 | 43 | 0.60 |
| Qd | ng/ml | 1.0E4 | 1.9E4 | 2.3E4 | 3.9E4 | 9.4E4 | 5.2E4 | 2.4E2 | 1.7E3 | 2.0E6 | 2.3E5 | 577 | 43 | 206 | 43 | 0.66 |
| Qe | ng/ml | 8.8E2 | 2.6E3 | 1.9E3 | 3.4E3 | 4.6E3 | 3.5E3 | 7.6E0 | 1.5E2 | 9.7E4 | 1.8E4 | 577 | 43 | 206 | 43 | 0.72 |
| Jd | ng/ml | 9.6E-1 | 2.5E0 | 7.2E0 | 4.1E0 | 4.7E1 | 7.2E0 | 1.0E-9 | 1.0E-9 | 6.5E2 | 3.5E1 | 217 | 29 | 135 | 29 | 0.60 |
| Je | ng/ml | 1.0E-9 | 5.7E-1 | 2.5E0 | 2.1E0 | 8.5E0 | 2.9E0 | 1.0E-9 | 1.0E-9 | 8.8E1 | 1.1E1 | 217 | 29 | 135 | 29 | 0.55 |
| Jf | ng/ml | 1.0E-9 | 1.0E-9 | 1.2E0 | 1.0E0 | 2.4E0 | 1.7E0 | 1.0E-9 | 1.0E-9 | 1.2E1 | 7.7E0 | 217 | 29 | 135 | 29 | 0.52 |
| Jg | ng/ml | 4.7E2 | 1.1E3 | 7.6E2 | 1.5E3 | 9.6E2 | 1.5E3 | 1.0E-9 | 3.7E1 | 1.0E4 | 7.1E3 | 581 | 43 | 208 | 43 | 0.68 |
| Jh | ng/ml | 3.1E0 | 6.6E0 | 2.6E1 | 5.6E1 | 1.1E2 | 1.3E2 | 1.0E-9 | 1.0E-9 | 1.6E3 | 5.4E2 | 581 | 43 | 208 | 43 | 0.59 |
| Ji | ng/ml | 5.0E1 | 1.2E2 | 7.1E1 | 2.0E2 | 7.0E1 | 2.3E2 | 1.0E-9 | 1.3E1 | 5.3E2 | 1.3E3 | 581 | 43 | 208 | 43 | 0.77 |
| Sr | pg/mL | 3.5E2 | 1.2E3 | 8.5E2 | 2.3E3 | 1.3E3 | 3.9E3 | 1.0E-9 | 1.0E-9 | 9.8E3 | 2.1E4 | 207 | 29 | 130 | 29 | 0.71 |
| Ss | pg/mL | 1.2E5 | 1.1E5 | 1.6E5 | 1.7E5 | 2.0E5 | 1.9E5 | 2.7E3 | 1.3E4 | 1.8E6 | 7.7E5 | 207 | 29 | 130 | 29 | 0.50 |
| St | pg/mL | 2.5E7 | 1.0E8 | 5.5E7 | 1.5E8 | 9.9E7 | 3.1E8 | 1.0E-9 | 2.3E6 | 1.2E9 | 1.7E9 | 212 | 29 | 131 | 29 | 0.69 |
| Wc | ng/ml | 1.0E-9 | 1.0E-9 | 5.3E-2 | 1.3E-1 | 1.3E-1 | 4.8E-1 | 1.0E-9 | 1.0E-9 | 9.8E-1 | 1.8E0 | 85 | 14 | 65 | 14 | 0.39 |
| Wd | ng/ml | 9.7E0 | 1.2E1 | 2.9E1 | 1.2E2 | 9.2E1 | 3.2E2 | 1.0E-9 | 3.5E0 | 7.9E2 | 1.2E3 | 85 | 14 | 65 | 14 | 0.60 |
| We | ng/ml | 4.7E-1 | 3.8E-1 | 8.3E-1 | 5.1E0 | 1.1E0 | 9.3E0 | 1.0E-9 | 2.0E-3 | 5.5E0 | 2.3E1 | 85 | 14 | 65 | 14 | 0.52 |
| Wg | ng/ml | 1.0E-9 | 1.0E-9 | 1.0E-9 | 3.8E-2 | 0.0E0 | 1.4E-1 | 1.0E-9 | 1.0E-9 | 1.0E-9 | 5.3E-1 | 85 | 14 | 65 | 14 | 0.54 |
| Wh | ng/ml | 1.1E-2 | 9.3E-3 | 6.7E-2 | 3.7E-1 | 2.8E-1 | 1.2E0 | 1.0E-9 | 3.7E-3 | 2.5E0 | 4.5E0 | 85 | 14 | 65 | 14 | 0.60 |
| Wf | ng/ml | 1.0E-9 | 1.0E-9 | 1.6E-1 | 2.3E-1 | 3.6E-1 | 6.2E-1 | 1.0E-9 | 1.0E-9 | 2.4E0 | 2.3E0 | 85 | 14 | 65 | 14 | 0.47 |
| Ra | pg/ml | 1.0E-9 | 1.0E-9 | 6.4E-1 | 2.8E0 | 1.3E0 | 1.2E1 | 1.0E-9 | 1.0E-9 | 7.3E0 | 6.4E1 | 216 | 29 | 133 | 29 | 0.51 |
| Qz | pg/ml | 1.0E1 | 1.1E1 | 6.0E1 | 5.3E1 | 1.0E2 | 7.8E1 | 1.0E-9 | 1.0E-9 | 7.1E2 | 2.3E2 | 216 | 29 | 133 | 29 | 0.53 |
| Qy | pg/ml | 4.6E-1 | 4.8E-1 | 1.5E1 | 4.4E0 | 7.2E1 | 1.8E1 | 1.0E-9 | 1.0E-9 | 6.5E2 | 9.7E1 | 216 | 29 | 133 | 29 | 0.49 |
| Qx | pg/ml | 1.0E-9 | 1.0E-9 | 7.6E0 | 6.0E0 | 5.5E1 | 2.1E1 | 1.0E-9 | 1.0E-9 | 5.8E2 | 1.1E2 | 216 | 29 | 133 | 29 | 0.50 |
| Qw | pg/ml | 4.5E-2 | 1.0E-9 | 2.2E0 | 7.2E-1 | 8.8E0 | 1.3E0 | 1.0E-9 | 1.0E-9 | 8.6E1 | 5.6E0 | 216 | 29 | 133 | 29 | 0.46 |
| Qv | pg/ml | 2.2E4 | 1.7E4 | 3.5E4 | 1.9E4 | 6.4E4 | 1.4E4 | 1.0E-9 | 4.0E2 | 7.4E5 | 5.0E4 | 216 | 29 | 133 | 29 | 0.39 |
| Qu | pg/ml | 1.2E1 | 1.2E1 | 8.9E1 | 6.8E1 | 1.7E2 | 1.4E2 | 1.0E-9 | 1.0E-9 | 9.8E2 | 7.0E2 | 216 | 29 | 133 | 29 | 0.48 |
| Qt | pg/ml | 1.2E1 | 2.1E1 | 5.7E1 | 4.0E1 | 1.4E2 | 6.4E1 | 1.0E-9 | 1.0E-9 | 1.0E3 | 2.7E2 | 216 | 29 | 133 | 29 | 0.54 |
| Qh | ng/ml | 1.7E1 | 3.6E1 | 3.7E1 | 5.8E1 | 6.3E1 | 8.7E1 | 1.0E-9 | 3.8E0 | 6.4E2 | 4.6E2 | 216 | 29 | 133 | 29 | 0.63 |
| Qg | ng/ml | 7.9E0 | 4.9E0 | 2.0E1 | 1.0E1 | 7.5E1 | 1.6E1 | 5.1E-2 | 3.3E-1 | 1.0E3 | 8.1E1 | 216 | 29 | 133 | 29 | 0.40 |
| Jj | ng/ml | 7.5E2 | 2.9E2 | 2.2E3 | 5.4E2 | 1.5E4 | 6.3E2 | 1.7E1 | 1.2E1 | 3.4E5 | 3.3E3 | 581 | 43 | 208 | 43 | 0.32 |
| Jk | ng/ml | 3.3E0 | 3.2E0 | 2.4E1 | 2.6E1 | 4.9E1 | 5.2E1 | 1.0E-9 | 2.2E-1 | 3.9E2 | 2.4E2 | 581 | 43 | 208 | 43 | 0.53 |
| Jl | ng/ml | 4.4E-1 | 1.6E0 | 1.8E0 | 2.4E2 | 4.3E0 | 1.5E3 | 7.6E-4 | 1.5E-2 | 3.2E1 | 9.9E3 | 581 | 43 | 208 | 43 | 0.66 |
| Jm | ng/ml | 1.9E1 | 3.7E1 | 5.2E1 | 1.0E2 | 9.7E1 | 3.2E2 | 1.0E-9 | 4.1E-1 | 1.0E3 | 2.1E3 | 581 | 43 | 208 | 43 | 0.57 |
| Jn | pg/ml | 4.0E-1 | 8.4E-1 | 1.7E0 | 3.3E1 | 5.8E0 | 1.4E2 | 1.0E-9 | 1.0E-9 | 6.2E1 | 7.3E2 | 581 | 43 | 208 | 43 | 0.65 |
| Jo | pg/ml | 4.0E3 | 3.7E3 | 5.1E3 | 7.7E3 | 3.9E3 | 1.6E4 | 4.2E1 | 2.3E2 | 2.4E4 | 1.0E5 | 581 | 43 | 208 | 43 | 0.49 |
| Jp | pg/ml | 7.0E4 | 8.9E4 | 7.3E4 | 9.4E4 | 3.4E4 | 4.1E4 | 2.1E3 | 2.6E4 | 2.1E5 | 2.1E5 | 581 | 43 | 208 | 43 | 0.66 |
| Jq | pg/ml | 9.5E1 | 1.6E2 | 1.5E2 | 5.3E2 | 2.2E2 | 1.4E3 | 2.6E0 | 1.4E0 | 4.0E3 | 8.7E3 | 581 | 43 | 208 | 43 | 0.64 |
| Jr | pg/ml | 5.2E0 | 1.0E1 | 2.2E1 | 3.1E2 | 1.0E2 | 1.4E3 | 1.0E-9 | 1.0E-9 | 1.9E3 | 7.4E3 | 581 | 43 | 208 | 43 | 0.64 |
| Js | pg/ml | 1.3E1 | 1.8E1 | 4.2E1 | 1.7E2 | 1.5E2 | 6.3E2 | 1.0E-9 | 1.7E0 | 2.0E3 | 3.0E3 | 581 | 43 | 208 | 43 | 0.62 |
| Jt | pg/ml | 2.7E3 | 3.4E3 | 3.2E3 | 5.1E3 | 2.2E3 | 8.3E3 | 1.5E2 | 4.1E2 | 1.3E4 | 5.2E4 | 581 | 43 | 208 | 43 | 0.57 |
| Xa | pg/ml | 6.1E-1 | 7.9E0 | 1.0E1 | 1.1E2 | 2.0E1 | 3.2E2 | 1.0E-9 | 1.0E-9 | 9.9E1 | 1.2E3 | 84 | 14 | 65 | 14 | 0.67 |
| Ye | pg/ml | 1.0E-9 | 1.0E-9 | 9.2E0 | 1.3E0 | 4.0E1 | 4.8E0 | 1.0E-9 | 1.0E-9 | 3.5E2 | 1.8E1 | 84 | 14 | 65 | 14 | 0.37 |

Figure 3 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Tm | pg/ml | 1.0E-9 | 1.0E-9 | 4.7E0 | 1.2E0 | 1.0E1 | 3.0E0 | 1.0E-9 | 1.0E-9 | 6.8E1 | 8.4E0 | 84 | 14 | 65 | 14 | 0.39 |
| Tl | pg/ml | 1.3E-1 | 1.0E-9 | 3.3E-1 | 1.9E0 | 3.8E-1 | 6.6E0 | 1.0E-9 | 1.0E-9 | 1.8E0 | 2.5E1 | 84 | 14 | 65 | 14 | 0.37 |
| Ju | mIU/ml | 9.0E0 | 1.1E1 | 2.1E1 | 1.7E1 | 3.3E1 | 2.0E1 | 6.5E-2 | 1.9E-1 | 2.3E2 | 8.9E1 | 217 | 29 | 135 | 29 | 0.56 |
| Jv | mIU/ml | 1.2E1 | 1.0E1 | 3.7E1 | 2.9E1 | 6.6E1 | 4.1E1 | 1.0E-2 | 8.2E-2 | 4.4E2 | 1.9E2 | 217 | 29 | 135 | 29 | 0.52 |
| Jy | ng/ml | 1.6E-3 | 2.0E-3 | 2.3E-3 | 3.7E-3 | 4.6E-3 | 7.4E-3 | 1.7E-4 | 5.3E-4 | 5.2E-2 | 4.1E-2 | 217 | 29 | 135 | 29 | 0.61 |
| Kc | pg/ml | 2.3E1 | 3.4E1 | 4.0E1 | 5.2E1 | 4.3E1 | 6.3E1 | 1.0E-9 | 1.0E-9 | 1.9E2 | 2.7E2 | 218 | 29 | 134 | 29 | 0.53 |
| Kd | pg/ml | 1.0E-9 | 1.0E-9 | 2.0E2 | 1.9E3 | 6.0E2 | 7.1E3 | 1.0E-9 | 1.0E-9 | 4.8E3 | 3.8E4 | 218 | 29 | 134 | 29 | 0.58 |
| Ke | pg/ml | 1.3E4 | 2.0E4 | 1.4E4 | 3.7E4 | 1.1E4 | 6.0E4 | 3.4E2 | 1.8E3 | 7.0E4 | 3.2E5 | 218 | 29 | 134 | 29 | 0.69 |
| Kf | pg/mL | 6.7E0 | 7.3E0 | 7.3E0 | 1.1E1 | 5.9E0 | 1.5E1 | 1.0E-9 | 1.0E-9 | 2.7E1 | 7.8E1 | 218 | 29 | 134 | 29 | 0.57 |
| Kg | pg/mL | 1.2E3 | 8.2E2 | 2.0E3 | 2.3E3 | 2.4E3 | 5.1E3 | 7.3E1 | 1.3E2 | 1.7E4 | 2.7E4 | 218 | 29 | 134 | 29 | 0.43 |
| Ki | pg/ml | 5.9E1 | 6.4E1 | 7.0E1 | 7.8E1 | 5.5E1 | 6.1E1 | 1.0E-9 | 1.0E-9 | 3.8E2 | 2.5E2 | 217 | 29 | 134 | 29 | 0.55 |
| Kj | pg/ml | 1.1E3 | 7.7E2 | 1.7E3 | 1.7E3 | 1.7E3 | 2.9E3 | 1.4E1 | 3.3E1 | 1.0E4 | 1.5E4 | 218 | 29 | 134 | 29 | 0.40 |
| Kk | pg/ml | 6.8E0 | 1.0E1 | 1.1E1 | 1.8E1 | 1.6E1 | 1.9E1 | 1.0E-9 | 2.0E0 | 1.6E2 | 5.9E1 | 218 | 29 | 134 | 29 | 0.63 |
| Kl | pg/ml | 2.1E4 | 2.3E4 | 2.9E4 | 3.3E4 | 2.6E4 | 2.9E4 | 1.6E2 | 1.3E3 | 1.6E5 | 1.1E5 | 218 | 29 | 134 | 29 | 0.54 |
| Kn | pg/ml | 3.0E1 | 5.7E1 | 6.2E1 | 2.7E2 | 9.5E1 | 9.0E2 | 1.0E-9 | 1.0E-9 | 7.3E2 | 4.9E3 | 218 | 29 | 134 | 29 | 0.60 |
| Ko | pg/ml | 3.4E2 | 6.2E2 | 4.6E2 | 8.7E2 | 4.5E2 | 9.8E2 | 1.0E-9 | 1.0E-9 | 2.2E3 | 4.1E3 | 218 | 29 | 134 | 29 | 0.65 |
| Kp | pg/ml | 3.4E2 | 3.6E2 | 3.5E2 | 8.3E2 | 2.7E2 | 2.4E3 | 1.0E-9 | 3.7E1 | 1.7E3 | 1.3E4 | 218 | 29 | 134 | 29 | 0.55 |
| Kq | pg/ml | 3.2E2 | 5.7E2 | 5.1E2 | 6.4E3 | 9.1E2 | 2.9E4 | 1.6E0 | 4.8E1 | 9.8E3 | 1.6E5 | 209 | 29 | 128 | 29 | 0.69 |
| Kr | pg/ml | 5.6E-1 | 1.0E-9 | 2.7E0 | 1.7E1 | 5.2E0 | 7.7E1 | 1.0E-9 | 1.0E-9 | 3.9E1 | 4.2E2 | 209 | 29 | 128 | 29 | 0.47 |
| Ks | pg/ml | 1.4E4 | 1.7E4 | 2.1E4 | 2.0E4 | 1.9E4 | 1.7E4 | 5.1E1 | 9.9E2 | 1.1E5 | 5.1E4 | 209 | 29 | 128 | 29 | 0.50 |
| Ps | ng/ml | 1.7E2 | 4.2E2 | 4.3E2 | 7.5E2 | 1.0E3 | 9.6E2 | 4.1E-1 | 1.3E1 | 8.3E3 | 3.8E3 | 82 | 14 | 62 | 14 | 0.70 |
| Kx | ng/ml | 1.0E-9 | 8.3E-3 | 7.1E-3 | 1.5E-2 | 1.4E-2 | 2.0E-2 | 1.0E-9 | 1.0E-9 | 1.0E-1 | 6.5E-2 | 214 | 29 | 133 | 29 | 0.63 |
| Ky | ng/ml | 1.0E-1 | 2.2E-1 | 3.8E-1 | 7.5E-1 | 8.3E-1 | 1.1E0 | 1.0E-9 | 1.0E-9 | 5.4E0 | 5.0E0 | 214 | 29 | 133 | 29 | 0.64 |
| Kz | ng/ml | 1.0E-9 | 1.0E-9 | 3.4E-3 | 5.6E-3 | 5.7E-3 | 6.9E-3 | 1.0E-9 | 1.0E-9 | 3.6E-2 | 1.8E-2 | 214 | 29 | 133 | 29 | 0.58 |
| Rz | ng/ml | 3.3E-1 | 3.1E-1 | 8.0E-1 | 1.5E0 | 1.3E0 | 2.0E0 | 3.6E-3 | 1.7E-2 | 6.5E0 | 5.9E0 | 82 | 14 | 62 | 14 | 0.56 |
| Ry | ng/ml | 1.6E-2 | 2.0E-2 | 2.1E-2 | 4.7E-2 | 2.3E-2 | 8.9E-2 | 1.0E-9 | 1.0E-9 | 1.2E-1 | 3.5E-1 | 82 | 14 | 62 | 14 | 0.59 |
| Rx | ng/ml | 1.0E-9 | 3.5E-5 | 1.9E-3 | 1.3E-3 | 3.5E-3 | 1.9E-3 | 1.0E-9 | 1.0E-9 | 2.0E-2 | 4.7E-3 | 82 | 14 | 62 | 14 | 0.53 |
| Ld | ng/ml | 1.0E-9 | 7.5E-1 | 3.7E0 | 5.7E0 | 9.6E0 | 1.0E1 | 1.0E-9 | 1.0E-9 | 8.4E1 | 5.0E1 | 216 | 29 | 133 | 29 | 0.58 |
| Lh | pg/ml | 1.3E4 | 2.2E4 | 2.1E4 | 5.4E4 | 2.7E4 | 8.4E4 | 1.0E-9 | 6.7E2 | 2.6E5 | 4.1E5 | 580 | 43 | 209 | 43 | 0.68 |
| Li | pg/ml | 3.1E3 | 1.2E4 | 1.5E4 | 5.7E4 | 3.9E4 | 1.5E5 | 1.0E-9 | 3.6E1 | 3.6E5 | 9.2E5 | 580 | 43 | 209 | 43 | 0.72 |
| Lj | pg/ml | 2.4E3 | 9.5E3 | 2.1E4 | 4.8E4 | 6.5E4 | 8.9E4 | 1.0E-9 | 1.0E2 | 4.7E5 | 4.1E5 | 580 | 43 | 209 | 43 | 0.71 |
| Lp | pg/ml | 1.1E1 | 6.2E0 | 6.4E1 | 1.6E2 | 1.4E2 | 3.2E2 | 1.0E-9 | 1.0E-9 | 7.7E2 | 1.0E3 | 82 | 14 | 62 | 14 | 0.46 |
| Lt | pg/ml | 1.0E-9 | 1.0E-9 | 2.6E0 | 1.8E0 | 9.7E0 | 6.7E0 | 1.0E-9 | 1.0E-9 | 6.0E1 | 2.5E1 | 82 | 14 | 62 | 14 | 0.49 |
| Rv | ng/ml | 5.0E-4 | 6.9E-4 | 1.1E-3 | 2.4E-3 | 2.1E-3 | 3.8E-3 | 1.0E-9 | 1.0E-9 | 1.6E-2 | 1.2E-2 | 82 | 14 | 62 | 14 | 0.57 |
| Ru | ng/ml | 1.0E-9 | 1.0E-9 | 1.8E-2 | 5.4E-2 | 7.1E-2 | 1.2E-1 | 1.0E-9 | 1.0E-9 | 3.8E-1 | 3.5E-1 | 82 | 14 | 62 | 14 | 0.57 |
| Rt | ng/ml | 6.9E-2 | 3.4E-2 | 1.1E-1 | 5.9E-1 | 1.3E-1 | 2.0E0 | 1.0E-3 | 1.3E-3 | 5.8E-1 | 7.4E0 | 82 | 14 | 62 | 14 | 0.39 |
| Yl | pg/ml | 1.1E1 | 1.2E1 | 1.6E1 | 3.4E1 | 1.8E1 | 5.6E1 | 1.0E-9 | 1.0E-9 | 1.1E2 | 2.2E2 | 85 | 14 | 65 | 14 | 0.58 |
| Rm | ng/ml | 1.9E1 | 4.0E1 | 5.1E1 | 8.8E1 | 7.7E1 | 1.3E2 | 2.2E-1 | 3.9E-1 | 4.0E2 | 6.5E2 | 213 | 29 | 132 | 29 | 0.59 |
| Rh | ng/ml | 1.3E2 | 1.7E2 | 2.8E2 | 1.2E3 | 5.0E2 | 3.7E3 | 4.7E0 | 2.5E1 | 3.8E3 | 1.7E4 | 213 | 29 | 132 | 29 | 0.59 |
| Ri | ng/ml | 1.0E-9 | 1.0E-9 | 4.3E0 | 1.4E0 | 1.7E1 | 3.3E0 | 1.0E-9 | 1.0E-9 | 2.2E2 | 1.6E1 | 214 | 29 | 133 | 29 | 0.42 |
| Rg | ng/ml | 1.0E-9 | 1.0E-9 | 6.8E-2 | 5.1E-2 | 3.9E-1 | 1.6E-1 | 1.0E-9 | 1.0E-9 | 3.3E0 | 6.2E-1 | 213 | 29 | 132 | 29 | 0.49 |
| Rj | ng/ml | 1.0E-9 | 1.0E-9 | 1.6E0 | 9.8E0 | 6.3E0 | 5.0E1 | 1.0E-9 | 1.0E-9 | 8.0E1 | 2.7E2 | 214 | 29 | 133 | 29 | 0.49 |
| Rf | ng/ml | 3.7E-1 | 9.7E-1 | 1.0E0 | 2.2E0 | 1.9E0 | 3.8E0 | 7.8E-3 | 1.4E-2 | 1.5E1 | 1.7E1 | 213 | 29 | 132 | 29 | 0.67 |
| Ql | pg/ml | 5.5E0 | 1.1E1 | 1.5E1 | 1.9E1 | 3.2E1 | 2.6E1 | 1.0E-9 | 1.0E-9 | 2.9E2 | 9.3E1 | 217 | 29 | 135 | 29 | 0.59 |
| Qm | pg/ml | 4.4E0 | 1.6E1 | 2.0E1 | 3.0E1 | 4.0E1 | 3.9E1 | 1.0E-9 | 1.0E-9 | 3.6E2 | 1.7E2 | 217 | 29 | 135 | 29 | 0.63 |
| Qn | pg/ml | 6.1E-1 | 6.1E-1 | 5.8E0 | 1.4E1 | 1.9E1 | 4.7E1 | 1.0E-9 | 1.0E-9 | 2.2E2 | 2.4E2 | 217 | 29 | 135 | 29 | 0.53 |
| Nv | pg/ml | 4.0E3 | 7.0E3 | 1.2E4 | 1.8E4 | 5.2E4 | 2.6E4 | 1.0E-9 | 1.5E2 | 1.1E6 | 1.1E5 | 585 | 43 | 209 | 43 | 0.64 |
| Nw | pg/ml | 8.5E3 | 1.7E4 | 1.3E4 | 3.0E4 | 1.8E4 | 4.4E4 | 8.6E1 | 1.7E3 | 2.1E5 | 2.2E5 | 585 | 43 | 209 | 43 | 0.73 |
| Nx | pg/ml | 2.2E2 | 2.6E2 | 4.1E2 | 6.7E2 | 6.9E2 | 8.6E2 | 1.0E-9 | 1.0E-9 | 7.4E3 | 4.1E3 | 585 | 43 | 209 | 43 | 0.61 |
| Ny | pg/ml | 5.7E0 | 1.6E1 | 7.2E1 | 1.3E2 | 1.0E3 | 4.3E2 | 1.0E-9 | 1.0E-9 | 2.5E4 | 2.8E3 | 585 | 43 | 209 | 43 | 0.67 |
| Oa | pg/ml | 1.6E2 | 4.1E2 | 4.1E2 | 9.5E2 | 7.0E2 | 1.1E3 | 1.0E-9 | 4.9E0 | 4.8E3 | 4.5E3 | 217 | 29 | 135 | 29 | 0.69 |
| Op | pg/ml | 4.1E5 | 4.1E5 | 4.0E5 | 3.8E5 | 1.5E5 | 1.8E5 | 3.3E4 | 6.7E4 | 7.3E5 | 6.6E5 | 82 | 14 | 62 | 14 | 0.48 |
| Wn | ng/ml | 1.4E1 | 2.7E1 | 6.5E1 | 9.3E1 | 2.3E2 | 1.3E2 | 1.2E0 | 2.7E0 | 1.8E3 | 3.4E2 | 71 | 8 | 53 | 8 | 0.67 |
| Tk | ng/ml | 1.9E2 | 1.5E2 | 3.9E2 | 4.1E2 | 6.5E2 | 5.4E2 | 3.0E0 | 1.0E1 | 4.2E3 | 1.4E3 | 79 | 9 | 58 | 9 | 0.48 |
| Oe | pg/ml | 9.1E1 | 9.4E0 | 3.1E2 | 2.7E2 | 8.7E2 | 4.7E2 | 1.0E-9 | 1.0E-9 | 1.9E4 | 2.2E3 | 580 | 43 | 209 | 43 | 0.45 |
| Of | pg/ml | 2.3E2 | 1.0E2 | 7.1E3 | 6.3E3 | 3.3E4 | 2.1E4 | 1.0E-9 | 1.0E-9 | 6.2E5 | 1.1E5 | 585 | 43 | 209 | 43 | 0.44 |
| Og | pg/ml | 9.2E-2 | 5.9E-2 | 9.9E-1 | 2.4E-1 | 5.8E0 | 7.7E-1 | 1.0E-9 | 1.0E-9 | 8.3E1 | 5.0E0 | 585 | 43 | 209 | 43 | 0.42 |

Figure 3 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oh | pg/ml | 2.4E0 | 5.5E0 | 2.5E1 | 4.6E1 | 1.7E2 | 1.8E2 | 1.0E-9 | 1.0E-9 | 3.5E3 | 1.1E3 | 585 | 43 | 209 | 43 | 0.65 |
| Oi | pg/ml | 2.8E0 | 3.0E0 | 6.5E0 | 7.3E0 | 1.0E1 | 1.0E1 | 1.0E-9 | 1.0E-9 | 8.6E1 | 5.1E1 | 585 | 43 | 209 | 43 | 0.52 |
| Ok | pg/ml | 3.9E2 | 6.5E2 | 5.2E2 | 1.2E3 | 5.0E2 | 1.4E3 | 1.3E1 | 3.2E1 | 5.2E3 | 7.8E3 | 585 | 43 | 209 | 43 | 0.72 |
| Om | pg/ml | 3.8E2 | 5.7E2 | 9.0E2 | 2.5E3 | 2.5E3 | 7.8E3 | 1.0E-9 | 1.0E2 | 3.6E4 | 5.1E4 | 585 | 43 | 209 | 43 | 0.63 |
| On | pg/ml | 1.8E2 | 2.9E2 | 2.9E2 | 7.5E2 | 4.3E2 | 1.4E3 | 8.4E-1 | 1.5E1 | 4.5E3 | 8.5E3 | 585 | 43 | 209 | 43 | 0.67 |
| Or | pg/ml | 1.4E1 | 1.9E1 | 3.4E1 | 7.9E1 | 6.3E1 | 1.4E2 | 1.0E-9 | 1.0E-9 | 5.0E2 | 5.1E2 | 218 | 29 | 134 | 29 | 0.55 |
| Ow | pg/ml | 3.3E1 | 6.1E1 | 1.1E2 | 2.7E2 | 3.1E2 | 5.8E2 | 1.0E-9 | 1.0E-9 | 2.7E3 | 3.0E3 | 218 | 29 | 134 | 29 | 0.62 |
| Ou | pg/ml | 4.7E2 | 6.8E2 | 8.8E2 | 2.0E3 | 1.3E3 | 3.0E3 | 1.0E-9 | 1.0E-9 | 9.8E3 | 9.6E3 | 218 | 29 | 134 | 29 | 0.57 |
| Ul | ng/ml | 1.0E-9 | 1.0E-9 | 1.4E0 | 5.4E0 | 4.7E0 | 1.5E1 | 1.0E-9 | 1.0E-9 | 3.4E1 | 5.6E1 | 224 | 29 | 137 | 29 | 0.52 |
| Uo | ng/ml | 1.0E-9 | 1.0E-9 | 1.1E-1 | 5.4E-2 | 2.7E-1 | 1.5E-1 | 1.0E-9 | 1.0E-9 | 2.6E0 | 6.3E-1 | 224 | 29 | 137 | 29 | 0.46 |
| Uk | ng/ml | 1.0E-9 | 1.0E-9 | 8.7E-3 | 3.9E-3 | 2.9E-2 | 1.0E-2 | 1.0E-9 | 1.0E-9 | 3.2E-1 | 3.9E-2 | 224 | 29 | 137 | 29 | 0.38 |
| Um | ng/ml | 1.0E-9 | 1.0E-9 | 4.2E-1 | 2.2E-1 | 1.0E0 | 4.9E-1 | 1.0E-9 | 1.0E-9 | 7.2E0 | 2.3E0 | 224 | 29 | 137 | 29 | 0.45 |
| Uf | ng/ml | 5.3E-2 | 9.8E-2 | 1.5E-1 | 3.6E-1 | 2.7E-1 | 1.0E0 | 1.0E-3 | 9.8E-3 | 2.1E0 | 5.6E0 | 224 | 29 | 137 | 29 | 0.66 |
| Uh | ng/ml | 1.9E0 | 4.5E0 | 2.9E0 | 6.1E0 | 3.1E0 | 5.1E0 | 3.2E-2 | 9.5E-1 | 1.7E1 | 1.8E1 | 224 | 29 | 137 | 29 | 0.72 |
| Un | ng/ml | 1.9E0 | 2.5E0 | 2.1E0 | 3.7E0 | 1.3E0 | 4.4E0 | 2.0E-1 | 5.3E-1 | 8.0E0 | 2.5E1 | 224 | 29 | 137 | 29 | 0.67 |
| Ug | ng/ml | 1.4E1 | 1.1E1 | 2.8E1 | 2.5E1 | 2.9E1 | 3.5E1 | 6.9E-1 | 1.7E0 | 1.8E2 | 1.6E2 | 224 | 29 | 137 | 29 | 0.42 |
| Ur | ng/ml | 1.5E-1 | 8.5E-3 | 8.5E-1 | 7.9E-1 | 6.3E0 | 1.9E0 | 1.0E-9 | 1.0E-9 | 9.3E1 | 7.3E0 | 223 | 29 | 136 | 29 | 0.39 |
| Up | ng/ml | 1.0E-9 | 1.0E-9 | 6.0E-3 | 8.5E-2 | 2.6E-2 | 4.4E-1 | 1.0E-9 | 1.0E-9 | 3.3E-1 | 2.4E0 | 223 | 29 | 136 | 29 | 0.50 |
| Us | ng/ml | 4.3E-3 | 1.0E-4 | 1.9E-2 | 8.7E-2 | 4.6E-2 | 3.1E-1 | 1.0E-9 | 1.0E-9 | 4.0E-1 | 1.7E0 | 223 | 29 | 136 | 29 | 0.50 |
| Uv | ng/ml | 3.2E-3 | 2.6E-3 | 1.3E-2 | 2.6E-2 | 3.9E-2 | 8.4E-2 | 1.0E-9 | 1.0E-9 | 4.3E-1 | 4.1E-1 | 223 | 29 | 136 | 29 | 0.46 |
| Ut | ng/ml | 7.6E-1 | 1.2E0 | 3.2E0 | 5.0E0 | 9.7E0 | 1.3E1 | 1.0E-9 | 1.0E-9 | 7.8E1 | 6.5E1 | 223 | 29 | 136 | 29 | 0.59 |
| Uu | ng/ml | 7.2E0 | 5.7E0 | 7.8E0 | 9.0E0 | 4.8E0 | 9.4E0 | 5.7E-1 | 1.2E0 | 2.6E1 | 4.0E1 | 223 | 29 | 136 | 29 | 0.47 |
| Uw | ng/ml | 2.2E0 | 3.1E0 | 2.9E0 | 5.8E0 | 4.2E0 | 9.8E0 | 1.0E-9 | 9.9E-1 | 3.7E1 | 3.9E1 | 90 | 14 | 70 | 14 | 0.65 |
| Vb | ng/ml | 1.0E0 | 9.2E-1 | 1.0E0 | 1.3E0 | 4.3E-1 | 1.6E0 | 8.5E-2 | 2.6E-1 | 2.5E0 | 6.4E0 | 90 | 14 | 70 | 14 | 0.46 |
| Vc | ng/ml | 1.0E-9 | 1.0E-9 | 1.6E-3 | 1.0E-9 | 1.2E-2 | 0.0E0 | 1.0E-9 | 1.0E-9 | 1.1E-1 | 1.0E-9 | 90 | 14 | 70 | 14 | 0.48 |
| Uy | ng/ml | 1.0E0 | 1.4E0 | 4.1E0 | 1.2E1 | 1.2E1 | 2.2E1 | 3.1E-2 | 2.0E-2 | 9.9E1 | 6.4E1 | 90 | 14 | 70 | 14 | 0.58 |
| Uz | ng/ml | 1.0E-9 | 1.0E-9 | 4.9E-3 | 2.4E0 | 4.6E-2 | 8.8E0 | 1.0E-9 | 1.0E-9 | 4.4E-1 | 3.3E1 | 90 | 14 | 70 | 14 | 0.53 |
| Ux | ng/ml | 1.7E2 | 2.0E2 | 1.9E2 | 2.2E2 | 1.3E2 | 1.3E2 | 4.5E0 | 3.5E1 | 5.3E2 | 4.6E2 | 90 | 14 | 70 | 14 | 0.58 |
| Va | ng/ml | 1.8E1 | 5.6E0 | 2.6E1 | 1.9E1 | 2.8E1 | 2.6E1 | 3.1E-1 | 1.2E0 | 1.2E2 | 7.8E1 | 90 | 14 | 70 | 14 | 0.39 |
| Vh | ng/ml | 1.0E-2 | 1.4E-2 | 1.6E-2 | 7.7E-2 | 2.1E-2 | 2.3E-1 | 1.0E-9 | 2.2E-3 | 1.2E-1 | 8.6E-1 | 90 | 14 | 70 | 14 | 0.62 |
| Vi | ng/ml | 3.0E-3 | 9.8E-3 | 1.6E-1 | 1.4E-1 | 1.4E0 | 4.8E-1 | 1.0E-9 | 1.0E-9 | 1.4E1 | 1.8E0 | 90 | 14 | 70 | 14 | 0.68 |
| Vj | ng/ml | 2.7E1 | 6.7E1 | 2.3E2 | 7.6E1 | 1.0E3 | 6.2E1 | 1.4E0 | 5.4E0 | 8.4E3 | 1.7E2 | 90 | 12 | 70 | 12 | 0.59 |
| Vp | ng/ml | 1.0E-9 | 1.0E-9 | 4.6E-1 | 1.7E0 | 3.8E0 | 9.1E0 | 1.0E-9 | 1.0E-9 | 5.0E1 | 4.9E1 | 224 | 29 | 137 | 29 | 0.51 |
| Vt | ng/ml | 6.1E0 | 1.2E1 | 8.3E0 | 2.0E1 | 9.3E0 | 2.9E1 | 4.3E-1 | 1.4E0 | 8.6E1 | 1.6E2 | 224 | 29 | 137 | 29 | 0.71 |
| Vu | ng/ml | 1.0E-9 | 1.0E-9 | 2.9E0 | 2.0E0 | 7.5E0 | 4.4E0 | 1.0E-9 | 1.0E-9 | 7.1E1 | 2.2E1 | 219 | 27 | 137 | 27 | 0.51 |
| Vq | ng/ml | 1.5E2 | 6.4E2 | 6.3E2 | 1.5E3 | 1.4E3 | 3.0E3 | 2.0E-1 | 1.0E1 | 1.1E4 | 1.2E4 | 175 | 18 | 115 | 18 | 0.65 |
| Vo | ng/ml | 2.6E1 | 2.5E1 | 2.5E1 | 2.5E1 | 5.1E0 | 4.6E0 | 2.5E0 | 1.1E1 | 4.8E1 | 3.3E1 | 224 | 29 | 137 | 29 | 0.48 |
| Vs | ng/ml | 2.6E-1 | 1.0E-9 | 7.3E0 | 2.3E1 | 2.6E1 | 9.3E1 | 1.0E-9 | 1.0E-9 | 2.3E2 | 4.5E2 | 218 | 24 | 135 | 24 | 0.45 |
| Vv | ng/ml | 3.3E0 | 2.5E0 | 6.3E0 | 4.5E0 | 1.0E1 | 6.4E0 | 1.0E-9 | 1.0E-9 | 8.4E1 | 3.2E1 | 223 | 28 | 137 | 28 | 0.46 |
| Vw | ng/ml | 3.6E1 | 4.0E1 | 3.4E1 | 4.0E1 | 1.7E1 | 1.6E1 | 2.5E0 | 1.1E1 | 7.0E1 | 6.6E1 | 90 | 14 | 70 | 14 | 0.59 |
| Oy | pg/ml | 5.5E-1 | 4.8E-1 | 7.3E0 | 3.1E0 | 3.5E1 | 9.1E0 | 1.0E-9 | 1.0E-9 | 4.0E2 | 4.9E1 | 584 | 43 | 208 | 43 | 0.45 |
| Oz | pg/ml | 1.3E-2 | 1.4E-2 | 3.5E-1 | 9.4E-1 | 1.6E0 | 4.3E0 | 1.0E-9 | 1.0E-9 | 2.9E1 | 2.8E1 | 584 | 43 | 208 | 43 | 0.51 |
| Pa | pg/ml | 3.9E-1 | 5.7E-1 | 1.5E0 | 6.6E0 | 5.8E0 | 3.4E1 | 1.0E-9 | 1.0E-9 | 8.6E1 | 2.3E2 | 584 | 43 | 208 | 43 | 0.57 |
| Pb | pg/ml | 1.0E-9 | 1.0E-9 | 1.1E0 | 8.5E-1 | 2.0E1 | 4.8E0 | 1.0E-9 | 1.0E-9 | 4.9E2 | 3.2E1 | 584 | 43 | 208 | 43 | 0.45 |
| Pc | pg/ml | 4.9E-2 | 1.6E-1 | 3.8E-1 | 1.3E0 | 1.0E0 | 5.7E0 | 1.0E-9 | 1.0E-9 | 1.6E1 | 3.8E1 | 584 | 43 | 208 | 43 | 0.54 |
| Pd | pg/ml | 1.8E0 | 4.1E0 | 5.5E0 | 9.6E0 | 3.6E1 | 2.0E1 | 1.0E-9 | 1.0E-9 | 8.4E2 | 1.2E2 | 584 | 43 | 208 | 43 | 0.63 |
| Pe | pg/ml | 2.1E1 | 6.1E1 | 1.1E2 | 7.3E2 | 3.7E2 | 2.5E3 | 1.0E-9 | 1.0E-9 | 4.7E3 | 1.5E4 | 584 | 43 | 208 | 43 | 0.71 |
| Pf | pg/ml | 1.5E0 | 6.6E0 | 1.1E1 | 3.6E1 | 6.6E1 | 8.7E1 | 1.0E-9 | 1.0E-9 | 1.5E3 | 4.3E2 | 584 | 43 | 208 | 43 | 0.71 |
| Pg | pg/ml | 3.3E0 | 9.7E0 | 5.4E1 | 8.2E1 | 4.2E2 | 2.3E2 | 1.0E-9 | 1.0E-9 | 7.7E3 | 1.2E3 | 584 | 43 | 208 | 43 | 0.66 |
| Ph | ng/ml | 1.6E-1 | 2.2E-1 | 3.3E-1 | 5.2E-1 | 4.9E-1 | 1.1E0 | 1.0E-9 | 1.0E-9 | 3.1E0 | 5.4E0 | 218 | 29 | 134 | 29 | 0.54 |
| Pi | ng/ml | 1.9E-1 | 2.7E-1 | 2.8E-1 | 3.1E-1 | 3.7E-1 | 1.5E1 | 1.0E-9 | 1.0E-9 | 3.2E0 | 8.2E1 | 218 | 29 | 134 | 29 | 0.61 |
| Pj | ng/mL | 5.2E0 | 7.4E0 | 6.1E0 | 7.9E0 | 4.7E0 | 4.3E0 | 3.8E-2 | 1.4E0 | 3.1E1 | 2.0E1 | 218 | 29 | 134 | 29 | 0.65 |
| Pk | ng/ml | 8.9E-3 | 1.0E-2 | 1.4E-2 | 6.3E-2 | 2.2E-2 | 2.8E-1 | 1.0E-9 | 1.0E-9 | 2.5E-1 | 1.5E0 | 218 | 29 | 134 | 29 | 0.52 |
| aA | mg/dL | 8.0E-1 | 1.0E0 | 9.1E-1 | 1.3E0 | 4.4E-1 | 9.8E-1 | 2.0E-1 | 4.0E-1 | 4.2E0 | 4.7E0 | 1815 | 54 | 323 | 54 | 0.63 |
| aC | mg/mL | 2.8E0 | 2.1E0 | 3.1E0 | 2.3E0 | 1.3E0 | 9.4E-1 | 8.5E-1 | 7.4E-1 | 8.2E0 | 5.5E0 | 363 | 31 | 141 | 31 | 0.32 |
| aD | ug/mL | 3.1E-1 | 4.5E0 | 4.3E0 | 6.0E0 | 3.5E0 | 4.8E0 | 8.5E-1 | 7.7E-1 | 3.1E1 | 2.1E1 | 363 | 31 | 141 | 31 | 0.60 |
| aE | mg/mL | 5.7E-1 | 5.0E-1 | 5.8E-1 | 5.4E-1 | 1.5E-1 | 1.8E-1 | 2.1E-1 | 2.2E-1 | 1.1E0 | 1.2E0 | 363 | 31 | 141 | 31 | 0.40 |

Figure 3 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aF | ng/mL | 2.1E0 | 2.6E0 | 4.1E0 | 4.2E0 | 6.1E0 | 4.7E0 | 4.3E-3 | 3.7E-1 | 5.0E1 | 1.8E1 | 363 | 31 | 141 | 31 | 0.50 |
| aG | mg/mL | 1.4E-1 | 1.3E-1 | 1.6E-1 | 1.5E-1 | 8.4E-2 | 8.5E-2 | 5.0E-2 | 4.3E-2 | 5.0E-1 | 4.2E-1 | 363 | 31 | 141 | 31 | 0.45 |
| aH | ug/mL | 7.5E1 | 7.1E1 | 8.1E1 | 7.7E1 | 4.2E1 | 4.4E1 | 9.6E0 | 1.1E1 | 2.9E2 | 1.9E2 | 363 | 31 | 141 | 31 | 0.47 |
| aI | ng/mL | 1.9E2 | 1.6E2 | 1.9E2 | 1.6E2 | 6.0E1 | 5.6E1 | 4.7E1 | 7.6E1 | 3.7E2 | 2.9E2 | 363 | 31 | 141 | 31 | 0.36 |
| aJ | ug/mL | 2.4E0 | 3.3E0 | 3.0E0 | 4.2E0 | 2.2E0 | 2.8E0 | 9.0E-1 | 1.1E0 | 1.7E1 | 1.2E1 | 363 | 31 | 141 | 31 | 0.65 |
| aK | ng/mL | 1.6E0 | 1.4E0 | 2.5E0 | 1.9E0 | 2.7E0 | 1.7E0 | 2.9E-4 | 1.3E-1 | 1.8E1 | 6.5E0 | 363 | 31 | 141 | 31 | 0.47 |
| aL | mg/mL | 7.9E-1 | 7.6E-1 | 8.0E-1 | 7.6E-1 | 2.4E-1 | 2.5E-1 | 2.2E-1 | 2.7E-1 | 1.7E0 | 1.5E0 | 363 | 31 | 141 | 31 | 0.45 |
| aM | U/mL | 2.2E1 | 3.2E1 | 4.4E1 | 8.4E1 | 1.0E2 | 1.5E2 | 4.2E-2 | 4.2E-2 | 1.6E3 | 8.2E2 | 363 | 31 | 141 | 31 | 0.62 |
| aN | U/mL | 1.4E1 | 2.0E1 | 2.1E1 | 3.2E1 | 3.0E1 | 2.9E1 | 2.5E-3 | 2.5E-3 | 3.8E2 | 1.1E2 | 363 | 31 | 141 | 31 | 0.63 |
| aO | pg/mL | 3.5E1 | 4.3E1 | 3.4E2 | 4.7E2 | 8.8E2 | 7.8E2 | 6.0E-2 | 6.0E-2 | 6.6E3 | 2.5E3 | 363 | 31 | 141 | 31 | 0.54 |
| aP | ng/mL | 1.6E0 | 1.9E0 | 2.0E0 | 2.5E0 | 1.2E0 | 1.6E0 | 5.4E-1 | 6.3E-1 | 7.0E0 | 6.5E0 | 363 | 31 | 141 | 31 | 0.59 |
| aQ | ng/mL | 3.0E-1 | 2.6E-1 | 4.6E-1 | 3.2E-1 | 4.9E-1 | 2.6E-1 | 2.0E-4 | 5.1E-2 | 4.0E0 | 1.2E0 | 363 | 31 | 141 | 31 | 0.43 |
| aR | ng/mL | 1.8E0 | 2.3E0 | 2.9E0 | 2.9E0 | 3.5E0 | 3.0E0 | 1.8E-1 | 7.1E-1 | 3.4E1 | 1.7E1 | 363 | 31 | 141 | 31 | 0.54 |
| aS | ng/mL | 2.7E-1 | 4.0E-1 | 7.2E-1 | 6.3E-1 | 2.0E0 | 7.3E-1 | 4.2E-3 | 6.0E-2 | 3.3E1 | 2.8E0 | 363 | 31 | 141 | 31 | 0.55 |
| aU | pg/mL | 7.8E1 | 6.5E1 | 1.3E2 | 8.8E1 | 1.5E2 | 9.6E1 | 7.4E-2 | 9.6E0 | 1.3E3 | 5.1E2 | 363 | 31 | 141 | 31 | 0.42 |
| aV | ng/mL | 6.3E-1 | 4.2E-1 | 1.1E0 | 8.2E-1 | 2.1E0 | 1.0E0 | 7.6E-4 | 9.1E-2 | 3.3E1 | 5.4E0 | 363 | 31 | 141 | 31 | 0.42 |
| aW | pg/mL | 1.9E1 | 2.0E1 | 2.0E1 | 3.2E1 | 2.1E1 | 7.2E1 | 7.2E-2 | 7.2E-2 | 2.4E2 | 4.2E2 | 363 | 31 | 141 | 31 | 0.52 |
| aX | ng/mL | 9.5E0 | 1.2E1 | 1.4E1 | 1.2E1 | 1.4E1 | 9.7E0 | 3.0E-1 | 1.6E0 | 8.0E1 | 3.1E1 | 363 | 31 | 141 | 31 | 0.47 |
| aY | pg/mL | 6.0E1 | 6.1E1 | 8.0E1 | 6.7E1 | 9.2E1 | 4.8E1 | 4.1E-1 | 4.1E-1 | 1.2E3 | 2.0E2 | 363 | 31 | 141 | 31 | 0.48 |
| aZ | pg/mL | 2.2E2 | 2.9E2 | 5.2E2 | 5.0E2 | 1.0E3 | 6.3E2 | 1.7E0 | 1.7E0 | 1.2E4 | 2.6E3 | 363 | 31 | 141 | 31 | 0.54 |
| bA | ng/mL | 8.5E0 | 3.0E1 | 3.0E1 | 9.5E1 | 7.7E1 | 1.8E2 | 3.0E-2 | 3.0E-2 | 9.4E2 | 9.4E2 | 363 | 31 | 141 | 31 | 0.69 |
| bB | ng/mL | 3.0E2 | 2.4E2 | 3.2E2 | 2.5E2 | 1.6E2 | 1.7E2 | 1.6E1 | 2.3E1 | 1.0E3 | 6.3E2 | 363 | 31 | 141 | 31 | 0.38 |
| bC | ng/mL | 3.3E2 | 3.3E2 | 5.7E2 | 7.6E2 | 7.3E2 | 1.1E3 | 2.7E1 | 5.0E1 | 4.7E3 | 4.7E3 | 363 | 31 | 141 | 31 | 0.55 |
| bE | mg/mL | 5.4E0 | 5.3E0 | 5.7E0 | 5.3E0 | 1.9E0 | 2.0E0 | 1.4E0 | 1.3E0 | 1.3E1 | 1.1E1 | 363 | 31 | 141 | 31 | 0.44 |
| bF | pg/mL | 2.0E1 | 4.8E1 | 1.8E2 | 2.1E2 | 1.1E3 | 5.0E2 | 5.0E-2 | 7.7E0 | 1.1E4 | 2.2E3 | 363 | 31 | 141 | 31 | 0.69 |
| bG | ng/mL | 1.6E0 | 1.8E0 | 2.8E0 | 3.0E0 | 3.4E0 | 3.5E0 | 2.2E-2 | 1.1E-1 | 2.6E1 | 1.5E1 | 363 | 31 | 141 | 31 | 0.51 |
| bH | pg/mL | 5.7E-1 | 5.7E-1 | 5.2E0 | 4.0E0 | 1.7E1 | 5.4E0 | 5.7E-1 | 5.7E-1 | 2.8E2 | 2.0E1 | 363 | 31 | 141 | 31 | 0.51 |
| bI | ng/mL | 4.0E-3 | 4.0E-3 | 7.0E-2 | 7.9E-2 | 1.7E-1 | 2.1E-1 | 4.0E-3 | 4.0E-3 | 1.3E0 | 8.8E-1 | 363 | 31 | 141 | 31 | 0.49 |
| bJ | mg/mL | 2.2E0 | 2.2E0 | 2.5E0 | 2.5E0 | 1.9E0 | 1.8E0 | 2.5E-4 | 2.5E-4 | 1.3E1 | 7.0E0 | 363 | 31 | 141 | 31 | 0.49 |
| bL | pg/mL | 4.1E0 | 3.1E0 | 8.4E0 | 5.9E0 | 1.0E1 | 6.8E0 | 4.6E-2 | 4.6E-2 | 4.9E1 | 3.2E1 | 363 | 31 | 141 | 31 | 0.46 |
| bM | mg/mL | 1.7E0 | 2.3E0 | 2.1E0 | 2.6E0 | 1.4E0 | 1.7E0 | 9.2E-3 | 1.8E-2 | 7.9E0 | 8.4E0 | 363 | 31 | 141 | 31 | 0.61 |
| bN | ng/mL | 4.7E1 | 3.1E1 | 1.3E2 | 7.8E1 | 2.7E2 | 1.3E2 | 1.4E-1 | 5.9E-1 | 1.9E3 | 4.8E2 | 363 | 31 | 141 | 31 | 0.41 |
| bO | ng/mL | 4.0E-2 | 4.0E-2 | 9.2E0 | 1.0E1 | 2.1E1 | 1.9E1 | 4.0E-2 | 4.0E-2 | 1.9E2 | 6.6E1 | 363 | 31 | 141 | 31 | 0.49 |
| bP | mg/mL | 5.1E-1 | 6.1E-1 | 7.3E-1 | 8.1E-1 | 6.6E-1 | 7.5E-1 | 8.2E-2 | 1.4E-1 | 4.8E0 | 3.5E0 | 363 | 31 | 141 | 31 | 0.54 |
| bQ | pg/mL | 1.5E1 | 2.3E1 | 7.0E1 | 4.7E1 | 7.1E2 | 5.4E1 | 1.5E-1 | 1.5E-1 | 1.3E4 | 2.2E2 | 363 | 31 | 141 | 31 | 0.65 |
| bR | ng/mL | 1.2E-2 | 1.2E-2 | 1.4E-1 | 5.4E-2 | 5.0E-1 | 9.2E-2 | 1.2E-2 | 1.2E-2 | 8.7E0 | 3.9E-1 | 363 | 31 | 141 | 31 | 0.39 |
| bS | pg/mL | 9.4E-1 | 9.4E-1 | 7.8E0 | 2.6E0 | 3.1E1 | 6.4E0 | 9.4E-1 | 9.4E-1 | 3.9E2 | 2.9E1 | 363 | 31 | 141 | 31 | 0.46 |
| bU | ng/mL | 1.3E-1 | 5.5E-2 | 2.1E-1 | 1.2E-1 | 4.1E-1 | 1.5E-1 | 1.3E-2 | 1.3E-2 | 6.6E0 | 6.3E-1 | 363 | 31 | 141 | 31 | 0.42 |
| bV | pg/mL | 4.7E2 | 5.6E2 | 5.3E2 | 7.1E2 | 2.4E2 | 5.8E2 | 1.7E2 | 1.9E2 | 1.6E3 | 3.1E3 | 363 | 31 | 141 | 31 | 0.59 |
| bW | pg/mL | 3.4E2 | 3.3E2 | 4.9E2 | 1.3E3 | 5.0E2 | 4.4E3 | 8.4E1 | 1.2E2 | 4.8E3 | 2.5E4 | 363 | 31 | 141 | 31 | 0.53 |
| bX | ng/mL | 1.5E-3 | 2.5E-5 | 2.8E-3 | 2.3E-3 | 3.4E-3 | 2.6E-3 | 2.5E-5 | 2.5E-5 | 2.0E-2 | 7.1E-3 | 363 | 31 | 141 | 31 | 0.47 |
| bZ | pg/mL | 2.4E2 | 3.1E2 | 9.1E2 | 1.0E3 | 4.3E3 | 1.5E3 | 1.5E-1 | 1.5E1 | 5.8E4 | 5.6E3 | 363 | 31 | 141 | 31 | 0.65 |
| cA | pg/mL | 6.0E-1 | 6.0E-1 | 3.0E0 | 1.1E0 | 2.0E1 | 2.6E0 | 6.0E-1 | 6.0E-1 | 3.7E2 | 1.5E1 | 363 | 31 | 141 | 31 | 0.45 |
| cB | ng/mL | 5.4E-2 | 4.1E-2 | 8.6E-2 | 6.0E-2 | 1.0E-1 | 8.3E-2 | 1.7E-3 | 1.7E-3 | 5.7E-1 | 4.0E-1 | 363 | 31 | 141 | 31 | 0.41 |
| cC | pg/mL | 4.6E1 | 4.9E1 | 4.9E1 | 3.9E1 | 4.2E1 | 2.6E1 | 1.0E0 | 1.0E0 | 4.5E2 | 7.3E1 | 363 | 31 | 141 | 31 | 0.45 |
| cD | pg/mL | 5.2E0 | 4.9E0 | 1.3E1 | 1.2E1 | 3.9E1 | 1.9E1 | 3.3E-1 | 3.3E-1 | 4.8E2 | 9.0E1 | 363 | 31 | 141 | 31 | 0.51 |
| cE | pg/mL | 3.2E1 | 9.6E1 | 1.5E2 | 2.1E2 | 4.8E2 | 3.0E2 | 1.2E-1 | 3.6E0 | 3.8E3 | 1.3E3 | 363 | 31 | 141 | 31 | 0.69 |
| cF | pg/mL | 1.2E1 | 5.3E-1 | 2.1E1 | 9.0E0 | 3.4E1 | 1.3E1 | 5.3E-1 | 5.3E-1 | 2.7E2 | 5.0E1 | 363 | 31 | 141 | 31 | 0.39 |
| cG | pg/mL | 4.3E1 | 8.4E1 | 1.1E2 | 1.1E2 | 5.7E2 | 9.5E1 | 7.8E0 | 6.4E0 | 1.0E4 | 4.1E2 | 363 | 31 | 141 | 31 | 0.71 |
| cH | uIU/mL | 3.1E0 | 2.1E0 | 6.7E0 | 4.3E0 | 1.3E1 | 7.8E0 | 8.6E-3 | 8.6E-3 | 1.6E2 | 3.9E1 | 363 | 31 | 141 | 31 | 0.37 |
| cI | ng/mL | 5.6E0 | 5.7E0 | 1.1E1 | 1.6E1 | 1.5E1 | 2.5E1 | 1.0E-3 | 1.0E-3 | 9.4E1 | 1.2E2 | 363 | 31 | 141 | 31 | 0.51 |
| cJ | ug/mL | 6.5E1 | 4.8E1 | 1.2E2 | 8.1E1 | 1.5E2 | 9.1E1 | 4.0E0 | 7.2E0 | 9.6E2 | 3.4E2 | 363 | 31 | 141 | 31 | 0.43 |
| cK | ng/mL | 3.8E-3 | 3.8E-3 | 5.9E-2 | 1.6E-2 | 2.0E-1 | 4.1E-2 | 3.8E-3 | 3.8E-3 | 1.7E0 | 2.1E-1 | 363 | 31 | 141 | 31 | 0.48 |
| cL | pg/mL | 1.9E2 | 2.0E2 | 4.0E2 | 2.8E2 | 1.5E3 | 2.4E2 | 1.6E1 | 4.8E1 | 2.4E4 | 1.4E3 | 363 | 31 | 141 | 31 | 0.56 |
| cM | pg/mL | 2.8E2 | 2.6E2 | 3.1E2 | 2.6E2 | 2.1E2 | 1.2E2 | 8.7E0 | 5.7E1 | 1.6E3 | 5.1E2 | 363 | 31 | 141 | 31 | 0.45 |
| cN | pg/mL | 1.2E2 | 1.3E2 | 1.3E2 | 1.4E2 | 7.0E1 | 5.0E1 | 3.8E1 | 7.4E1 | 1.1E3 | 2.9E2 | 363 | 31 | 141 | 31 | 0.60 |
| cO | pg/mL | 2.2E2 | 2.4E2 | 3.3E2 | 2.5E2 | 1.0E3 | 9.7E1 | 5.4E1 | 1.2E2 | 1.9E4 | 5.0E2 | 363 | 31 | 141 | 31 | 0.52 |

Figure 3 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cP | ng/mL | 2.6E3 | 2.3E3 | 2.6E3 | 2.7E3 | 9.4E2 | 1.1E3 | 6.2E2 | 1.3E3 | 5.7E3 | 5.9E3 | 363 | 31 | 141 | 31 | 0.48 |
| cQ | ng/mL | 4.9E-2 | 4.5E-2 | 1.2E-1 | 1.5E-1 | 2.3E-1 | 2.8E-1 | 2.0E-3 | 2.0E-3 | 2.2E0 | 1.2E0 | 363 | 31 | 141 | 31 | 0.49 |
| cR | ng/mL | 2.8E2 | 3.8E2 | 4.3E2 | 5.1E2 | 6.0E2 | 5.0E2 | 2.0E1 | 7.0E1 | 7.7E3 | 2.2E3 | 363 | 31 | 141 | 31 | 0.58 |
| cS | ng/mL | 2.6E2 | 3.0E2 | 3.7E2 | 5.1E2 | 3.7E2 | 6.4E2 | 4.7E1 | 4.8E1 | 2.7E3 | 2.6E3 | 363 | 31 | 141 | 31 | 0.52 |
| cT | ng/mL | 3.1E1 | 8.4E1 | 8.6E1 | 1.7E2 | 1.9E2 | 3.1E2 | 4.6E0 | 4.0E0 | 2.1E3 | 1.4E3 | 363 | 31 | 141 | 31 | 0.65 |
| cU | ng/mL | 5.3E1 | 6.6E1 | 7.7E1 | 9.5E1 | 1.1E2 | 8.5E1 | 6.2E0 | 1.6E1 | 1.6E3 | 4.2E2 | 363 | 31 | 141 | 31 | 0.59 |
| cV | ng/mL | 1.7E-1 | 2.8E-1 | 4.2E-1 | 4.8E-1 | 2.5E0 | 7.5E-1 | 3.4E-4 | 3.6E-2 | 4.7E1 | 4.2E0 | 363 | 31 | 141 | 31 | 0.67 |
| cW | mIU/mL | 5.3E-2 | 4.2E-2 | 1.6E-1 | 8.3E-2 | 7.9E-1 | 8.7E-2 | 3.7E-4 | 1.4E-2 | 9.7E0 | 3.9E-1 | 363 | 31 | 141 | 31 | 0.50 |
| cX | ng/mL | 1.0E-1 | 1.2E-1 | 1.4E0 | 1.8E0 | 4.5E0 | 5.1E0 | 2.3E-4 | 2.3E-4 | 2.8E1 | 2.8E1 | 363 | 31 | 141 | 31 | 0.50 |
| cY | ng/mL | 8.8E0 | 9.0E0 | 1.3E1 | 1.0E1 | 1.4E1 | 7.8E0 | 1.5E-1 | 9.3E-1 | 8.3E1 | 3.6E1 | 363 | 31 | 141 | 31 | 0.47 |
| cZ | ug/mL | 1.4E1 | 1.3E1 | 1.5E1 | 1.4E1 | 6.1E0 | 6.3E0 | 2.7E0 | 3.3E0 | 3.9E1 | 3.1E1 | 363 | 31 | 141 | 31 | 0.43 |
| dA | pg/mL | 3.3E2 | 3.5E2 | 3.7E2 | 3.7E2 | 3.3E2 | 2.0E2 | 9.0E1 | 1.5E2 | 5.8E3 | 1.1E3 | 363 | 31 | 141 | 31 | 0.50 |
| dB | ug/mL | 1.7E1 | 2.1E1 | 1.8E1 | 1.7E1 | 1.8E1 | 1.0E1 | 9.4E-1 | 2.2E0 | 2.5E2 | 3.0E1 | 363 | 31 | 141 | 31 | 0.56 |
| dC | nmol/L | 3.5E1 | 3.8E1 | 4.0E1 | 3.9E1 | 1.9E1 | 1.5E1 | 9.1E0 | 1.6E1 | 1.4E2 | 7.9E1 | 363 | 31 | 141 | 31 | 0.51 |
| dD | ug/mL | 3.6E1 | 2.9E1 | 3.7E1 | 3.2E1 | 1.1E1 | 1.1E1 | 1.3E1 | 1.4E1 | 7.6E1 | 5.7E1 | 363 | 31 | 141 | 31 | 0.34 |
| dE | ng/mL | 4.7E-1 | 3.0E-1 | 6.1E-1 | 4.5E-1 | 7.4E-1 | 5.6E-1 | 8.4E-3 | 8.4E-3 | 7.2E0 | 2.4E0 | 363 | 31 | 141 | 31 | 0.43 |
| dF | ng/mL | 2.2E2 | 2.8E2 | 2.7E2 | 4.4E2 | 1.8E2 | 3.2E2 | 7.5E1 | 8.4E1 | 1.3E3 | 1.2E3 | 363 | 31 | 141 | 31 | 0.70 |
| dG | ng/mL | 1.1E1 | 1.6E1 | 1.4E1 | 2.1E1 | 1.3E1 | 1.8E1 | 3.1E0 | 3.9E0 | 1.8E2 | 8.7E1 | 363 | 31 | 141 | 31 | 0.67 |
| dH | pg/mL | 7.5E0 | 1.0E1 | 1.3E1 | 1.2E1 | 4.1E1 | 9.6E0 | 4.0E-2 | 4.0E-2 | 6.7E2 | 4.9E1 | 363 | 31 | 141 | 31 | 0.60 |
| dI | pg/mL | 4.6E-1 | 4.6E-1 | 2.5E0 | 1.6E0 | 1.8E1 | 2.1E0 | 4.6E-1 | 4.6E-1 | 3.3E2 | 7.5E0 | 363 | 31 | 141 | 31 | 0.53 |
| dJ | ng/mL | 1.9E0 | 1.9E0 | 2.2E0 | 1.8E0 | 1.2E0 | 1.2E0 | 3.2E-1 | 3.2E-2 | 6.9E0 | 4.0E0 | 363 | 31 | 141 | 31 | 0.44 |
| dK | uIU/mL | 1.9E0 | 1.3E0 | 3.2E0 | 2.7E0 | 6.5E0 | 4.0E0 | 2.8E-4 | 2.9E-2 | 7.9E1 | 2.2E1 | 363 | 31 | 141 | 31 | 0.46 |
| dL | ng/mL | 8.8E2 | 1.2E3 | 1.0E3 | 1.3E3 | 4.9E2 | 9.2E2 | 3.4E2 | 4.1E2 | 3.4E3 | 4.8E3 | 363 | 31 | 141 | 31 | 0.59 |
| dM | pg/mL | 9.7E2 | 1.1E3 | 1.2E3 | 2.0E3 | 9.3E2 | 2.0E3 | 3.9E2 | 3.9E2 | 1.2E4 | 9.6E3 | 363 | 31 | 141 | 31 | 0.65 |
| dN | ug/ml | 9.4E1 | 1.0E2 | 9.9E1 | 1.2E2 | 3.4E1 | 6.5E1 | 2.5E1 | 3.4E1 | 2.4E2 | 3.3E2 | 363 | 31 | 141 | 31 | 0.59 |
| dR | pg/ml | 1.6E3 | 1.1E3 | 2.4E3 | 1.6E3 | 2.5E3 | 1.5E3 | 1.4E2 | 3.4E2 | 1.5E4 | 5.3E3 | 245 | 28 | 138 | 28 | 0.42 |
| dU | pg/ml | 9.7E3 | 1.4E4 | 1.4E4 | 1.6E4 | 1.2E4 | 1.2E4 | 6.9E2 | 3.1E3 | 5.3E4 | 3.8E4 | 40 | 13 | 37 | 13 | 0.56 |
| dX | ng/ml | 3.4E-2 | 8.2E-2 | 1.2E-1 | 1.6E-1 | 2.0E-1 | 1.6E-1 | 2.6E-3 | 2.6E-3 | 1.2E0 | 4.2E-1 | 92 | 7 | 30 | 7 | 0.63 |
| eF | ng/ml | 4.1E0 | 4.7E0 | 4.6E0 | 5.6E0 | 2.2E0 | 2.8E0 | 1.4E0 | 2.0E0 | 1.8E1 | 1.5E1 | 257 | 28 | 138 | 28 | 0.62 |
| eC | pg/ml | 3.1E2 | 2.4E2 | 3.7E2 | 3.3E2 | 2.2E2 | 4.2E2 | 4.5E1 | 1.9E1 | 1.4E3 | 2.0E3 | 203 | 27 | 135 | 27 | 0.33 |
| eD | pg/ml | 2.1E2 | 1.8E2 | 5.9E2 | 4.4E2 | 1.2E3 | 8.9E2 | 5.2E-1 | 5.2E-1 | 7.0E3 | 3.8E3 | 173 | 16 | 111 | 16 | 0.47 |
| eM | ng/ml | 3.5E0 | 2.5E0 | 4.7E0 | 4.6E0 | 4.4E0 | 6.3E0 | 7.6E-1 | 7.1E-1 | 2.4E1 | 2.6E1 | 122 | 17 | 50 | 17 | 0.39 |
| eP | ng/ml | 3.7E-3 | 3.7E-3 | 7.3E-1 | 4.4E0 | 1.8E0 | 1.0E1 | 3.7E-3 | 3.7E-3 | 1.2E1 | 2.8E1 | 92 | 7 | 30 | 7 | 0.55 |
| eT | ng/ml | 2.9E2 | 6.1E2 | 6.4E2 | 1.0E3 | 7.2E2 | 1.0E3 | 1.0E2 | 7.1E1 | 2.9E3 | 2.9E3 | 100 | 10 | 81 | 10 | 0.59 |
| eQ | pg/ml | 1.0E0 | 1.0E0 | 8.6E1 | 1.7E1 | 2.7E2 | 4.3E1 | 1.0E0 | 1.0E0 | 1.6E3 | 1.5E2 | 40 | 13 | 37 | 13 | 0.41 |
| fA | ng/ml | 1.9E2 | 1.1E2 | 3.8E2 | 3.4E2 | 4.4E2 | 4.1E2 | 2.6E1 | 6.2E1 | 1.5E3 | 1.2E3 | 40 | 13 | 37 | 13 | 0.46 |
| eZ | ng/ml | 5.2E1 | 6.0E1 | 6.0E1 | 6.6E1 | 2.6E1 | 2.6E1 | 1.8E1 | 3.2E1 | 1.2E2 | 1.1E2 | 100 | 10 | 81 | 10 | 0.59 |
| fB | ng/ml | 6.1E2 | 6.8E2 | 6.9E2 | 7.2E2 | 3.1E2 | 2.6E2 | 1.6E2 | 3.5E2 | 1.5E3 | 1.3E3 | 40 | 14 | 37 | 14 | 0.55 |
| fN | ng/ml | 2.1E-1 | 2.3E0 | 2.6E0 | 5.2E0 | 5.2E0 | 5.9E0 | 2.1E-1 | 2.1E-1 | 3.2E1 | 1.4E1 | 100 | 10 | 81 | 10 | 0.62 |
| fP | ng/ml | 2.5E2 | 3.1E2 | 2.9E2 | 3.5E2 | 1.7E2 | 2.2E2 | 1.8E0 | 3.3E1 | 1.0E3 | 8.6E2 | 240 | 28 | 137 | 28 | 0.58 |
| fR | ng/ml | 1.2E5 | 2.0E5 | 1.7E5 | 2.6E5 | 1.4E5 | 1.9E5 | 3.1E4 | 1.9E2 | 7.2E5 | 6.8E5 | 236 | 19 | 68 | 19 | 0.67 |
| fY | ng/ml | 2.6E2 | 2.2E2 | 2.5E2 | 2.4E2 | 1.0E2 | 1.1E2 | 3.6E1 | 1.2E1 | 4.8E2 | 4.3E2 | 100 | 10 | 81 | 10 | 0.46 |
| gC | ng/ml | 2.3E2 | 2.4E2 | 2.5E2 | 2.6E2 | 1.0E2 | 8.4E1 | 8.3E1 | 1.6E2 | 6.4E2 | 4.5E2 | 103 | 15 | 58 | 15 | 0.58 |
| gL | pg/ml | 6.3E4 | 6.7E4 | 6.9E4 | 7.6E4 | 2.8E4 | 3.4E4 | 1.1E4 | 4.4E4 | 1.8E5 | 1.7E5 | 245 | 28 | 138 | 28 | 0.56 |
| gP | U/ml | 2.8E2 | 2.5E2 | 2.8E2 | 2.7E2 | 1.1E2 | 9.4E1 | 1.2E1 | 9.6E1 | 1.1E3 | 5.2E2 | 253 | 28 | 138 | 28 | 0.47 |
| gW | ng/ml | 5.7E2 | 3.7E2 | 1.2E3 | 9.0E2 | 1.7E3 | 1.2E3 | 3.1E-1 | 1.5E2 | 9.5E3 | 4.3E3 | 213 | 16 | 129 | 16 | 0.47 |
| tF | pg/mL | 1.5E3 | 1.1E3 | 1.6E4 | 4.2E3 | 4.7E4 | 5.7E3 | 1.2E1 | 1.8E1 | 3.2E5 | 2.0E4 | 203 | 27 | 135 | 27 | 0.50 |
| gZ | ug/ml | 8.5E-1 | 6.3E-1 | 4.2E1 | 7.7E1 | 1.1E2 | 1.5E2 | 8.7E-2 | 1.1E-1 | 4.1E2 | 4.1E2 | 40 | 13 | 37 | 13 | 0.54 |
| hA | ng/ml | 2.2E0 | 4.8E0 | 1.0E1 | 7.4E0 | 3.9E1 | 6.8E0 | 1.7E-2 | 6.3E-2 | 3.5E2 | 2.5E1 | 173 | 18 | 111 | 18 | 0.68 |
| nM | pg/ml | 1.0E-9 | 1.0E-9 | 9.1E1 | 1.0E-9 | 9.6E2 | 0.0E0 | 1.0E-9 | 1.0E-9 | 1.0E4 | 1.0E-9 | 113 | 21 | 88 | 21 | 0.49 |
| nN | pg/ml | 1.4E3 | 2.0E3 | 5.8E3 | 3.4E3 | 2.7E4 | 4.6E3 | 1.1E2 | 2.6E2 | 2.7E5 | 2.1E4 | 113 | 21 | 88 | 21 | 0.58 |
| nO | pg/ml | 2.6E1 | 2.9E1 | 4.1E1 | 4.5E1 | 4.3E1 | 5.1E1 | 3.5E0 | 8.1E0 | 2.4E2 | 2.4E2 | 113 | 21 | 88 | 21 | 0.55 |
| nR | pg/ml | 1.5E1 | 2.2E1 | 4.3E1 | 5.8E1 | 9.3E1 | 9.6E1 | 1.0E-9 | 1.9E0 | 8.2E2 | 4.2E2 | 113 | 21 | 88 | 21 | 0.59 |
| nT | pg/ml | 7.3E1 | 9.0E1 | 2.2E2 | 9.2E1 | 8.5E2 | 3.5E1 | 1.0E-9 | 1.4E1 | 6.6E3 | 1.8E2 | 113 | 21 | 88 | 21 | 0.55 |
| nU | pg/ml | 3.9E1 | 4.4E1 | 3.0E2 | 6.1E1 | 1.6E3 | 6.5E1 | 1.0E-9 | 1.0E-9 | 1.3E4 | 2.2E2 | 113 | 21 | 88 | 21 | 0.51 |
| lW | pg/ml | 1.0E-9 | 1.0E-9 | 1.5E1 | 5.6E0 | 5.1E1 | 1.1E1 | 1.0E-9 | 1.0E-9 | 3.9E2 | 4.4E1 | 113 | 21 | 88 | 21 | 0.50 |
| lX | pg/ml | 9.4E2 | 5.3E2 | 9.9E2 | 8.1E2 | 5.3E2 | 5.5E2 | 1.2E2 | 1.9E2 | 2.5E3 | 2.5E3 | 113 | 21 | 88 | 21 | 0.38 |

Figure 3 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| lY | pg/ml | 1.9E1 | 1.7E1 | 2.3E1 | 1.6E1 | 2.2E1 | 1.1E1 | 1.0E-9 | 5.7E-1 | 1.4E2 | 4.5E1 | 113 | 21 | 88 | 21 | 0.41 |
| mE | pg/ml | 1.0E-9 | 1.0E-9 | 2.9E0 | 1.7E0 | 8.8E0 | 3.4E0 | 1.0E-9 | 1.0E-9 | 5.8E1 | 1.3E1 | 113 | 21 | 88 | 21 | 0.50 |
| mF | pg/ml | 1.0E-9 | 2.7E-1 | 4.3E0 | 2.0E0 | 2.5E1 | 4.0E0 | 1.0E-9 | 1.0E-9 | 2.5E2 | 1.3E1 | 113 | 21 | 88 | 21 | 0.56 |
| mH | pg/ml | 3.2E0 | 2.7E0 | 4.8E0 | 4.6E0 | 6.6E0 | 4.5E0 | 2.3E-1 | 9.0E-1 | 5.3E1 | 1.9E1 | 113 | 21 | 88 | 21 | 0.50 |
| mI | pg/ml | 1.0E-9 | 1.0E-9 | 1.3E1 | 1.4E1 | 2.9E1 | 2.3E1 | 1.0E-9 | 1.0E-9 | 1.8E2 | 7.8E1 | 113 | 21 | 88 | 21 | 0.53 |
| mM | pg/ml | 2.8E1 | 4.0E1 | 8.0E1 | 7.5E1 | 1.6E2 | 1.1E2 | 1.0E-9 | 1.0E-9 | 1.1E3 | 4.7E2 | 113 | 21 | 88 | 21 | 0.55 |
| mP | pg/ml | 1.4E1 | 1.5E1 | 2.0E1 | 1.4E1 | 2.6E1 | 6.8E0 | 1.0E-9 | 1.0E-9 | 1.9E2 | 2.4E1 | 112 | 21 | 87 | 21 | 0.48 |
| mS | pg/ml | 1.8E3 | 1.7E3 | 2.0E3 | 1.6E3 | 1.7E3 | 8.0E2 | 1.0E-9 | 1.0E-9 | 1.3E4 | 3.2E3 | 113 | 21 | 88 | 21 | 0.42 |
| mT | pg/ml | 5.4E1 | 5.9E1 | 1.2E2 | 6.4E1 | 1.9E2 | 3.3E1 | 1.0E1 | 1.2E1 | 1.4E3 | 1.4E2 | 112 | 21 | 87 | 21 | 0.49 |
| mU | pg/ml | 2.3E0 | 3.1E0 | 6.3E0 | 3.1E0 | 2.2E1 | 1.4E0 | 1.0E-9 | 6.0E-1 | 2.2E2 | 6.6E0 | 112 | 21 | 87 | 21 | 0.59 |
| mW | pg/ml | 2.5E2 | 2.2E3 | 2.8E3 | 2.4E3 | 1.6E3 | 1.5E3 | 4.3E2 | 1.7E2 | 1.0E4 | 6.2E3 | 112 | 21 | 87 | 21 | 0.44 |
| mY | pg/ml | 6.2E2 | 8.8E2 | 9.1E2 | 8.9E2 | 1.4E3 | 6.6E2 | 1.0E-9 | 1.0E-9 | 1.1E4 | 2.6E3 | 113 | 21 | 88 | 21 | 0.58 |
| mZ | pg/ml | 2.4E2 | 9.7E1 | 4.0E2 | 3.7E2 | 4.6E2 | 6.2E2 | 2.1E0 | 1.1E1 | 3.1E3 | 2.8E3 | 112 | 21 | 87 | 21 | 0.36 |
| nA | pg/ml | 1.6E0 | 4.8E-1 | 1.2E1 | 2.6E0 | 4.7E1 | 3.7E0 | 1.0E-9 | 1.0E-9 | 4.4E2 | 1.4E1 | 112 | 21 | 87 | 21 | 0.41 |
| nB | pg/ml | 3.1E2 | 3.2E2 | 3.3E2 | 3.4E2 | 1.5E2 | 1.9E2 | 3.0E1 | 7.9E1 | 8.2E2 | 1.0E3 | 113 | 21 | 88 | 21 | 0.52 |
| nC | pg/ml | 1.0E-9 | 7.5E1 | 4.3E3 | 7.4E4 | 3.4E4 | 3.3E5 | 1.0E-9 | 1.0E-9 | 3.7E5 | 1.5E6 | 113 | 21 | 88 | 21 | 0.58 |
| nD | pg/ml | 7.9E0 | 3.8E0 | 3.8E1 | 9.0E0 | 2.2E2 | 1.0E1 | 1.0E-9 | 1.0E-9 | 1.7E3 | 2.9E1 | 112 | 21 | 87 | 21 | 0.44 |
| nF | pg/ml | 1.0E-9 | 1.0E-9 | 5.0E0 | 2.0E0 | 2.8E1 | 6.2E0 | 1.0E-9 | 1.0E-9 | 2.4E2 | 2.1E1 | 113 | 21 | 88 | 21 | 0.50 |
| nH | pg/ml | 3.8E-1 | 2.0E0 | 1.0E2 | 1.4E2 | 9.5E2 | 5.7E2 | 1.0E-9 | 1.0E-9 | 1.0E4 | 2.6E3 | 112 | 21 | 87 | 21 | 0.57 |
| nI | pg/ml | 2.8E0 | 1.0E-9 | 1.7E2 | 2.6E1 | 9.0E2 | 4.2E1 | 1.0E-9 | 1.0E-9 | 9.2E3 | 1.3E2 | 113 | 21 | 88 | 21 | 0.37 |
| nJ | pg/ml | 1.7E-1 | 4.0E-1 | 4.8E1 | 6.5E-1 | 4.8E2 | 8.0E-1 | 1.0E-9 | 1.0E-9 | 5.2E3 | 2.4E0 | 113 | 21 | 88 | 21 | 0.48 |
| nK | pg/ml | 1.0E-9 | 1.0E-9 | 6.2E1 | 1.0E1 | 3.7E2 | 1.4E1 | 1.0E-9 | 1.0E-9 | 3.2E3 | 4.2E1 | 112 | 21 | 87 | 21 | 0.52 |
| nL | pg/ml | 1.0E-9 | 1.4E0 | 4.5E2 | 3.0E2 | 4.2E3 | 1.1E3 | 1.0E-9 | 1.0E-9 | 4.5E4 | 5.2E3 | 113 | 21 | 88 | 21 | 0.59 |
| hL | pg/ml | 1.9E4 | 2.6E4 | 2.3E4 | 2.9E4 | 1.8E4 | 1.7E4 | 2.6E3 | 7.9E3 | 1.4E5 | 6.0E4 | 100 | 10 | 81 | 10 | 0.63 |
| hO | pg/ml | 1.6E4 | 1.5E4 | 1.7E4 | 1.5E4 | 3.2E3 | 3.3E3 | 1.1E4 | 1.1E4 | 2.8E4 | 2.3E4 | 100 | 10 | 81 | 10 | 0.38 |
| hP | ng/ml | 4.4E5 | 4.4E5 | 4.3E5 | 6.1E5 | 3.4E5 | 7.9E5 | 1.7E4 | 3.4E4 | 2.6E6 | 2.8E6 | 100 | 10 | 81 | 10 | 0.52 |
| wJ | pg/ml | 1.5E5 | 1.0E5 | 1.8E5 | 1.2E5 | 1.1E5 | 7.9E4 | 1.1E4 | 2.3E4 | 5.8E5 | 2.5E5 | 99 | 9 | 76 | 9 | 0.34 |
| wK | pg/ml | 3.5E4 | 3.5E4 | 4.9E4 | 4.0E4 | 5.6E4 | 3.3E4 | 3.7E3 | 1.1E4 | 5.0E5 | 1.2E5 | 99 | 9 | 76 | 9 | 0.44 |
| wL | pg/ml | 4.0E0 | 5.3E0 | 4.6E1 | 4.9E1 | 1.1E2 | 1.1E2 | 1.0E-9 | 1.0E-9 | 8.4E2 | 3.5E2 | 99 | 9 | 76 | 9 | 0.47 |
| wP | pg/ml | 2.9E4 | 7.0E4 | 4.4E4 | 8.7E4 | 4.8E4 | 8.1E4 | 1.3E3 | 1.8E4 | 3.0E5 | 2.6E5 | 99 | 9 | 76 | 9 | 0.71 |
| wQ | pg/ml | 3.8E1 | 2.9E1 | 6.2E1 | 4.0E1 | 8.3E1 | 4.9E1 | 1.0E-9 | 1.0E-9 | 5.1E2 | 1.6E2 | 99 | 9 | 76 | 9 | 0.44 |
| hR | pg/ml | 2.6E4 | 2.9E4 | 2.7E4 | 2.9E4 | 1.1E4 | 9.4E3 | 1.1E1 | 1.3E4 | 5.8E4 | 4.4E4 | 165 | 17 | 109 | 17 | 0.56 |
| hV | pg/ml | 4.3E2 | 3.6E2 | 4.5E2 | 4.3E2 | 2.4E2 | 2.5E2 | 6.8E1 | 9.5E1 | 1.5E3 | 9.6E2 | 165 | 17 | 109 | 17 | 0.46 |
| hW | pg/ml | 1.6E3 | 2.4E3 | 2.1E3 | 4.9E3 | 1.7E3 | 9.1E3 | 2.2E2 | 1.2E3 | 1.0E4 | 4.0E4 | 165 | 17 | 109 | 17 | 0.72 |
| hX | pg/ml | 9.0E2 | 1.2E3 | 1.0E3 | 1.4E3 | 8.2E2 | 1.4E3 | 1.3E2 | 3.1E2 | 8.6E3 | 6.6E3 | 165 | 17 | 109 | 17 | 0.63 |
| iA | pg/ml | 1.5E2 | 2.0E2 | 3.0E2 | 3.4E2 | 6.6E2 | 2.6E2 | 1.1E1 | 7.0E1 | 7.1E3 | 8.7E2 | 203 | 26 | 135 | 26 | 0.65 |
| iB | ng/ml | 5.0E0 | 7.7E0 | 6.3E0 | 8.8E0 | 5.0E0 | 6.4E0 | 3.3E-2 | 1.1E0 | 3.8E1 | 2.2E1 | 173 | 18 | 111 | 18 | 0.61 |
| iC | U/ml | 2.3E-1 | 6.1E-1 | 1.0E0 | 1.5E0 | 4.9E0 | 2.8E0 | 1.0E-9 | 6.8E-2 | 5.5E1 | 1.2E1 | 173 | 18 | 111 | 18 | 0.68 |
| tQ | pg/ml | 1.1E3 | 1.3E3 | 1.2E3 | 1.5E3 | 5.7E2 | 8.8E2 | 2.8E2 | 6.3E2 | 2.5E3 | 3.3E3 | 94 | 8 | 73 | 8 | 0.55 |
| tT | pg/ml | 1.7E1 | 2.6E1 | 2.0E1 | 2.9E1 | 1.5E1 | 2.1E1 | 5.4E0 | 7.2E0 | 1.2E2 | 6.7E1 | 95 | 8 | 74 | 8 | 0.60 |
| tS | pg/ml | 1.0E0 | 1.1E0 | 1.1E0 | 1.5E0 | 1.0E0 | 2.2E0 | 1.0E-9 | 5.5E0 | 7.0E0 | 95 | 9 | 74 | 9 | 0.49 |
| tX | pg/ml | 9.9E-1 | 1.2E0 | 1.1E0 | 2.3E0 | 9.4E-1 | 2.4E0 | 2.5E-2 | 9.3E-2 | 7.0E0 | 6.2E0 | 95 | 8 | 74 | 8 | 0.61 |
| tO | pg/ml | 4.4E0 | 3.9E0 | 4.9E0 | 4.5E0 | 3.2E0 | 2.7E0 | 1.0E-9 | 1.7E0 | 1.8E1 | 9.6E0 | 95 | 9 | 74 | 9 | 0.46 |
| tR | pg/ml | 1.9E-1 | 2.2E-1 | 2.7E-1 | 3.3E-1 | 2.7E-1 | 3.9E-1 | 1.0E-9 | 1.4E-2 | 1.6E0 | 1.3E0 | 94 | 9 | 73 | 9 | 0.52 |
| tU | pg/ml | 9.1E0 | 1.2E1 | 1.1E1 | 1.9E1 | 6.9E0 | 2.3E1 | 2.2E-1 | 5.0E0 | 4.4E1 | 8.0E1 | 97 | 9 | 75 | 9 | 0.62 |
| tN | pg/ml | 1.8E1 | 3.2E1 | 2.2E1 | 3.3E1 | 1.9E1 | 2.0E1 | 1.0E-9 | 6.1E0 | 1.5E2 | 6.5E1 | 95 | 8 | 73 | 8 | 0.68 |
| tV | ng/ml | 4.8E2 | 8.7E2 | 6.3E2 | 9.2E2 | 4.7E2 | 5.0E2 | 5.3E1 | 3.9E2 | 2.6E3 | 1.7E3 | 99 | 8 | 76 | 8 | 0.70 |
| iH | ng/ml | 1.6E5 | 1.5E5 | 1.5E5 | 1.5E5 | 4.7E4 | 4.7E4 | 5.1E4 | 5.1E4 | 2.7E5 | 2.4E5 | 203 | 26 | 135 | 26 | 0.49 |
| iJ | ng/ml | 5.3E4 | 4.6E4 | 5.5E4 | 5.1E4 | 3.0E4 | 3.2E4 | 7.7E3 | 1.1E4 | 2.5E5 | 1.8E5 | 203 | 26 | 135 | 26 | 0.43 |
| hB | pg/ml | 4.3E-1 | 5.6E-1 | 5.4E-1 | 8.8E-1 | 4.1E-1 | 7.6E-1 | 1.2E-1 | 1.6E-1 | 3.0E0 | 3.2E0 | 203 | 26 | 135 | 26 | 0.65 |
| hC | pg/ml | 4.1E3 | 7.6E3 | 7.1E3 | 1.2E4 | 1.0E4 | 1.4E4 | 1.0E-9 | 4.5E1 | 1.1E5 | 5.7E4 | 203 | 26 | 135 | 26 | 0.59 |
| hF | ng/ml | 1.0E-9 | 1.0E-9 | 2.4E1 | 3.7E-1 | 2.9E2 | 1.9E0 | 1.0E-9 | 1.0E-9 | 4.0E3 | 9.6E0 | 203 | 26 | 135 | 26 | 0.51 |
| hG | pg/ml | 7.0E3 | 7.4E3 | 7.7E3 | 8.5E3 | 3.3E3 | 4.2E3 | 1.7E3 | 3.6E3 | 2.0E4 | 2.0E4 | 203 | 26 | 135 | 26 | 0.53 |
| iO | ng/ml | 3.8E5 | 3.7E5 | 4.0E5 | 4.0E5 | 1.8E5 | 1.9E5 | 8.3E4 | 8.3E4 | 1.1E6 | 8.2E5 | 203 | 26 | 135 | 26 | 0.50 |
| iP | ng/ml | 5.1E4 | 7.0E4 | 5.7E4 | 7.2E4 | 5.5E4 | 1.0E5 | 2.4E3 | 7.2E3 | 5.5E5 | 5.7E5 | 203 | 26 | 135 | 26 | 0.54 |
| iZ | ng/ml | 1.6E3 | 2.0E3 | 1.8E3 | 2.1E3 | 7.6E2 | 1.0E3 | 4.7E2 | 9.8E2 | 5.7E3 | 4.6E3 | 201 | 25 | 133 | 25 | 0.55 |
| yH | pg/ml | 1.1E3 | 1.4E3 | 3.4E3 | 1.9E3 | 1.3E4 | 2.3E3 | 1.0E-9 | 3.0E2 | 1.2E5 | 7.7E3 | 99 | 9 | 77 | 9 | 0.54 |

Figure 3 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| yK | U/ml | 2.1E1 | 2.8E1 | 4.5E1 | 3.3E1 | 7.1E1 | 3.2E1 | 1.0E-9 | 1.0E-9 | 3.8E2 | 1.0E2 | 99 | 9 | 77 | 9 | 0.50 |
| yJ | pg/ml | 3.3E4 | 4.0E4 | 4.4E4 | 4.6E4 | 3.4E4 | 2.9E4 | 1.7E3 | 2.7E3 | 1.6E5 | 8.5E4 | 99 | 9 | 77 | 9 | 0.54 |
| yD | ng/ml | 1.5E-2 | 1.5E-2 | 1.5E-2 | 1.6E-2 | 6.3E-3 | 7.5E-3 | 1.0E-9 | 6.3E-3 | 3.2E-2 | 3.0E-2 | 99 | 9 | 76 | 9 | 0.53 |
| jB | | 2.5E5 | 1.9E5 | 2.5E5 | 2.7E5 | 9.0E4 | 1.6E5 | 5.7E4 | 1.2E5 | 4.1E5 | 6.2E5 | 40 | 13 | 37 | 13 | 0.46 |
| wB | pg/ml | 8.3E3 | 1.6E4 | 9.6E3 | 1.7E4 | 7.4E3 | 9.6E3 | 1.7E3 | 5.3E3 | 4.1E4 | 3.0E4 | 99 | 9 | 76 | 9 | 0.73 |
| pY | pg/ml | 6.2E0 | 7.3E0 | 9.0E0 | 7.7E0 | 2.0E1 | 3.5E0 | 2.1E0 | 4.7E0 | 2.0E2 | 1.7E1 | 100 | 10 | 81 | 10 | 0.59 |
| rC | pg/ml | 1.5E3 | 1.4E3 | 2.2E3 | 1.6E3 | 2.3E3 | 9.6E2 | 1.0E-9 | 7.0E1 | 1.5E4 | 3.4E3 | 163 | 16 | 105 | 16 | 0.45 |
| rB | pg/ml | 2.4E1 | 5.3E1 | 4.7E1 | 6.4E1 | 9.5E1 | 6.4E1 | 1.0E-9 | 1.0E-9 | 9.5E2 | 2.1E2 | 163 | 16 | 105 | 16 | 0.60 |
| zG | 2.5ng/ml | 2.2E-1 | 5.3E-1 | 4.6E-1 | 6.9E-1 | 8.4E-1 | 8.6E-1 | 1.0E-9 | 1.0E-9 | 4.8E0 | 2.7E0 | 99 | 9 | 77 | 9 | 0.60 |
| zH | 2.3mU/ml | 1.1E-1 | 9.0E-2 | 1.1E-1 | 9.3E-2 | 5.4E-2 | 2.5E-2 | 1.0E-2 | 4.4E-2 | 4.4E-1 | 1.4E-1 | 99 | 9 | 77 | 9 | 0.39 |
| zI | 2.6ng/ml | 2.1E0 | 4.5E0 | 3.9E0 | 6.3E0 | 4.5E0 | 5.9E0 | 5.4E-1 | 7.8E-1 | 2.7E1 | 1.6E1 | 99 | 9 | 77 | 9 | 0.62 |
| qA | ng/ml | 9.9E6 | 1.3E7 | 1.2E7 | 1.6E7 | 7.9E6 | 8.7E6 | 2.0E6 | 4.3E6 | 4.6E7 | 3.0E7 | 100 | 10 | 81 | 10 | 0.65 |
| qB | ng/ml | 6.4E5 | 6.7E5 | 8.1E5 | 1.1E6 | 5.5E5 | 1.1E6 | 2.1E5 | 2.4E5 | 2.9E6 | 3.8E6 | 100 | 10 | 81 | 10 | 0.53 |
| qC | ng/ml | 3.8E5 | 2.3E5 | 7.0E5 | 2.4E5 | 1.0E6 | 1.7E5 | 3.4E3 | 2.1E4 | 7.1E6 | 5.2E5 | 100 | 10 | 81 | 10 | 0.29 |
| qD | ng/ml | 1.6E7 | 1.2E7 | 1.8E7 | 1.4E7 | 8.5E6 | 4.9E6 | 4.9E6 | 1.0E7 | 5.2E7 | 2.6E7 | 100 | 10 | 81 | 10 | 0.33 |
| jD | ng/ml | 3.6E1 | 4.0E1 | 5.2E1 | 5.0E1 | 6.3E1 | 5.0E1 | 1.0E-9 | 4.2E0 | 5.1E2 | 1.8E2 | 172 | 18 | 111 | 18 | 0.51 |
| jE | ng/ml | 1.0E-9 | 1.0E-9 | 6.2E0 | 1.1E1 | 1.6E1 | 1.7E1 | 1.0E-9 | 1.0E-9 | 1.2E2 | 5.6E1 | 172 | 18 | 111 | 18 | 0.59 |
| jF | ng/ml | 3.1E1 | 3.1E1 | 5.0E1 | 4.0E1 | 6.1E1 | 4.5E1 | 1.0E-9 | 1.0E-9 | 3.5E2 | 1.3E2 | 172 | 18 | 111 | 18 | 0.46 |
| jG | ng/ml | 4.4E3 | 4.4E3 | 4.5E3 | 4.4E3 | 1.9E3 | 2.0E3 | 7.6E2 | 6.0E2 | 9.6E3 | 7.9E3 | 173 | 18 | 111 | 18 | 0.48 |
| jH | ng/ml | 7.7E1 | 7.6E1 | 8.6E1 | 9.8E1 | 4.8E1 | 8.7E1 | 1.3E1 | 3.3E1 | 3.3E2 | 4.3E2 | 173 | 18 | 111 | 18 | 0.50 |
| jI | ng/ml | 7.3E1 | 9.8E1 | 7.7E1 | 1.2E2 | 3.3E1 | 9.3E1 | 2.8E1 | 4.4E1 | 2.5E2 | 4.4E2 | 173 | 18 | 111 | 18 | 0.65 |
| sK | pg/mL | 4.0E3 | 4.7E3 | 4.1E3 | 6.7E3 | 1.7E3 | 6.5E3 | 1.1E3 | 2.1E3 | 1.0E4 | 2.3E4 | 100 | 9 | 78 | 9 | 0.62 |
| sM | pg/mL | 8.1E4 | 9.2E4 | 8.1E4 | 1.0E5 | 2.7E4 | 4.3E4 | 3.3E4 | 5.1E4 | 1.6E5 | 2.0E5 | 100 | 9 | 78 | 9 | 0.65 |
| sO | pg/mL | 2.7E8 | 2.5E8 | 2.7E8 | 2.3E8 | 9.9E7 | 1.2E8 | 4.9E7 | 6.6E7 | 5.0E8 | 4.0E8 | 100 | 9 | 78 | 9 | 0.42 |
| wC | ng/ml | 1.5E0 | 1.7E0 | 1.9E0 | 1.7E0 | 1.7E0 | 8.4E-1 | 2.5E-1 | 3.1E-1 | 1.5E1 | 2.9E0 | 99 | 9 | 76 | 9 | 0.52 |
| wD | ng/ml | 2.0E1 | 4.0E1 | 5.3E1 | 8.9E1 | 2.2E2 | 9.2E1 | 2.8E0 | 1.2E1 | 2.1E3 | 2.9E2 | 99 | 9 | 76 | 9 | 0.78 |
| wE | ng/ml | 4.8E1 | 4.5E1 | 5.0E1 | 5.1E1 | 2.3E1 | 1.7E1 | 3.2E0 | 3.6E1 | 1.4E2 | 8.9E1 | 99 | 9 | 76 | 9 | 0.50 |
| wG | ng/ml | 4.9E-2 | 5.9E-2 | 9.5E-2 | 1.5E-1 | 1.1E-1 | 2.3E-1 | 1.0E-9 | 1.0E-9 | 4.8E-1 | 6.8E-1 | 99 | 9 | 76 | 9 | 0.52 |
| wH | ng/ml | 2.0E-2 | 5.9E-2 | 1.8E-1 | 7.4E-1 | 5.7E-1 | 1.8E0 | 1.0E-9 | 1.0E-9 | 4.2E0 | 5.6E0 | 99 | 9 | 76 | 9 | 0.63 |
| wF | ng/ml | 1.8E-1 | 8.1E-1 | 1.8E0 | 3.2E0 | 7.6E0 | 3.9E0 | 1.0E-9 | 1.0E-9 | 5.7E1 | 9.6E0 | 99 | 9 | 76 | 9 | 0.64 |
| rA | pg/ml | 2.5E1 | 2.4E1 | 3.0E1 | 3.0E1 | 2.3E1 | 1.9E1 | 1.0E-9 | 6.9E0 | 1.2E2 | 6.8E1 | 171 | 17 | 108 | 17 | 0.52 |
| qZ | pg/ml | 4.3E1 | 9.9E1 | 4.3E2 | 1.2E3 | 1.9E3 | 2.8E3 | 1.0E-9 | 1.5E-3 | 1.0E4 | 1.0E4 | 132 | 13 | 96 | 13 | 0.67 |
| qY | pg/ml | 2.3E1 | 1.1E1 | 5.3E1 | 1.9E1 | 7.1E1 | 1.8E1 | 8.7E-1 | 2.1E0 | 5.3E2 | 7.8E1 | 171 | 17 | 108 | 17 | 0.33 |
| qX | pg/ml | 5.3E1 | 6.8E1 | 6.3E1 | 8.5E1 | 4.2E1 | 6.3E1 | 1.0E-9 | 1.7E1 | 2.1E2 | 2.1E2 | 171 | 17 | 108 | 17 | 0.58 |
| qW | pg/ml | 8.6E0 | 6.0E0 | 1.2E1 | 1.0E1 | 1.2E1 | 1.0E1 | 1.0E-9 | 1.0E-9 | 7.1E1 | 3.1E1 | 171 | 17 | 108 | 17 | 0.45 |
| qV | pg/ml | 2.1E3 | 1.7E3 | 2.8E3 | 2.5E3 | 2.1E3 | 2.3E3 | 1.0E2 | 6.3E2 | 1.1E4 | 9.6E3 | 171 | 17 | 108 | 17 | 0.45 |
| qU | pg/ml | 5.6E1 | 1.2E2 | 1.6E2 | 2.3E2 | 2.8E2 | 3.1E2 | 1.0E-9 | 3.5E0 | 2.1E3 | 1.1E3 | 171 | 17 | 108 | 17 | 0.57 |
| qT | pg/ml | 4.1E1 | 4.1E1 | 6.9E1 | 8.8E1 | 1.0E2 | 8.2E1 | 1.0E-9 | 6.9E0 | 9.0E2 | 3.0E2 | 171 | 17 | 108 | 17 | 0.59 |
| qI | ng/ml | 6.9E4 | 5.9E4 | 6.8E4 | 5.7E4 | 3.1E4 | 2.0E4 | 5.4E3 | 1.0E4 | 1.6E5 | 9.2E4 | 98 | 9 | 79 | 9 | 0.39 |
| qH | ng/ml | 6.2E4 | 5.5E4 | 6.9E4 | 7.1E4 | 4.1E4 | 3.5E4 | 7.6E3 | 3.5E4 | 1.8E5 | 1.4E5 | 98 | 9 | 79 | 9 | 0.54 |
| qG | ng/ml | 1.9E5 | 1.7E5 | 2.0E5 | 1.8E5 | 7.3E4 | 6.1E4 | 1.7E4 | 9.9E4 | 4.2E5 | 2.7E5 | 98 | 9 | 79 | 9 | 0.41 |
| jK | ng/ml | 1.6E3 | 1.3E3 | 1.7E3 | 1.5E3 | 6.6E2 | 6.3E2 | 2.8E2 | 7.5E2 | 4.3E3 | 2.9E3 | 173 | 18 | 111 | 18 | 0.37 |
| jL | ng/ml | 2.0E2 | 2.5E2 | 3.0E2 | 3.7E2 | 2.6E2 | 3.7E2 | 3.6E1 | 1.2E2 | 2.1E3 | 1.7E3 | 173 | 18 | 111 | 18 | 0.60 |
| jM | ng/ml | 7.0E4 | 6.2E4 | 7.3E4 | 7.0E4 | 3.7E4 | 4.3E4 | 3.9E2 | 5.7E3 | 1.7E5 | 1.4E5 | 173 | 18 | 111 | 18 | 0.47 |
| jO | pg/ml | 2.2E5 | 2.3E5 | 2.7E5 | 2.4E5 | 1.5E5 | 1.1E5 | 5.2E4 | 9.8E4 | 8.0E5 | 5.2E5 | 173 | 18 | 111 | 18 | 0.48 |
| jP | pg/ml | 2.4E5 | 2.6E5 | 2.7E5 | 3.4E5 | 1.6E5 | 2.7E5 | 5.8E4 | 8.4E4 | 9.2E5 | 1.2E6 | 173 | 18 | 111 | 18 | 0.56 |
| jQ | pg/ml | 2.5E3 | 1.9E3 | 3.4E3 | 2.5E3 | 3.4E3 | 2.3E3 | 1.0E-9 | 4.6E2 | 1.8E4 | 9.2E3 | 173 | 18 | 111 | 18 | 0.43 |
| jR | pg/ml | 5.9E3 | 3.5E3 | 1.0E4 | 8.9E3 | 1.2E4 | 1.2E4 | 1.0E-9 | 3.0E1 | 9.0E4 | 4.6E4 | 173 | 18 | 111 | 18 | 0.42 |
| jT | pg/ml | 1.7E5 | 1.6E5 | 1.8E5 | 1.5E5 | 6.8E4 | 5.4E4 | 6.8E4 | 7.5E4 | 4.5E5 | 2.8E5 | 173 | 18 | 111 | 18 | 0.39 |
| xA | pg/ml | 4.7E0 | 7.3E0 | 1.5E1 | 1.9E1 | 4.5E1 | 3.4E1 | 1.0E-9 | 1.0E-9 | 3.9E2 | 1.1E2 | 99 | 9 | 77 | 9 | 0.58 |
| yE | pg/ml | 7.8E1 | 7.9E1 | 8.5E1 | 1.1E2 | 4.3E1 | 7.3E1 | 6.4E0 | 1.6E1 | 3.0E2 | 2.5E2 | 99 | 9 | 77 | 9 | 0.58 |
| tM | pg/ml | 4.0E1 | 4.4E1 | 4.1E1 | 5.1E1 | 1.8E1 | 3.1E1 | 1.0E-9 | 1.6E1 | 1.0E2 | 1.1E2 | 99 | 9 | 77 | 9 | 0.56 |
| tL | pg/ml | 1.0E-9 | 1.0E-9 | 4.0E0 | 3.0E0 | 2.7E1 | 8.7E0 | 1.0E-9 | 1.0E-9 | 2.6E2 | 2.6E1 | 99 | 9 | 77 | 9 | 0.53 |
| jU | mIU/ml | 4.6E0 | 4.8E0 | 1.0E1 | 1.0E1 | 1.7E1 | 1.3E1 | 6.2E-2 | 4.2E-2 | 1.1E2 | 5.3E1 | 173 | 18 | 111 | 18 | 0.51 |
| jV | mIU/ml | 1.5E0 | 1.1E0 | 3.4E0 | 2.4E0 | 5.8E0 | 2.8E0 | 1.7E-3 | 7.6E-2 | 3.3E1 | 1.0E1 | 173 | 18 | 111 | 18 | 0.48 |
| jY | ng/ml | 7.4E-4 | 4.0E-3 | 6.5E-3 | 7.5E-3 | 2.9E-2 | 8.3E-3 | 1.0E-9 | 1.0E-9 | 3.0E-1 | 2.6E-2 | 173 | 18 | 111 | 18 | 0.65 |
| kC | pg/ml | 9.6E1 | 9.7E1 | 1.9E2 | 1.4E2 | 4.1E2 | 1.4E2 | 2.1E1 | 3.6E1 | 3.5E3 | 5.9E2 | 113 | 21 | 88 | 21 | 0.48 |

Figure 3 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| kE | pg/ml | 1.4E5 | 1.4E5 | 1.4E5 | 1.4E5 | 3.9E4 | 5.0E4 | 1.2E4 | 5.1E4 | 2.3E5 | 2.7E5 | 113 | 21 | 88 | 21 | 0.49 |
| kF | pg/mL | 6.3E1 | 6.5E1 | 7.2E1 | 7.0E1 | 5.2E1 | 2.3E1 | 2.6E1 | 3.4E1 | 5.1E2 | 1.2E2 | 113 | 21 | 88 | 21 | 0.55 |
| kG | pg/mL | 9.2E3 | 9.2E3 | 1.4E4 | 1.4E4 | 1.7E4 | 1.2E4 | 7.5E2 | 1.1E3 | 1.2E5 | 5.0E4 | 113 | 21 | 88 | 21 | 0.54 |
| kI | pg/ml | 2.0E2 | 1.8E2 | 2.2E2 | 2.0E2 | 1.3E2 | 1.2E2 | 4.4E1 | 1.0E-9 | 8.7E2 | 6.2E2 | 113 | 21 | 88 | 21 | 0.45 |
| kK | pg/ml | 1.0E2 | 1.4E2 | 1.8E2 | 1.9E2 | 2.3E2 | 1.6E2 | 2.1E1 | 2.9E1 | 1.6E3 | 6.2E2 | 113 | 21 | 88 | 21 | 0.56 |
| kN | pg/ml | 1.0E3 | 8.9E2 | 2.1E3 | 3.2E3 | 5.6E3 | 8.4E3 | 7.6E1 | 3.8E2 | 5.5E4 | 3.9E4 | 113 | 21 | 88 | 21 | 0.51 |
| kO | pg/ml | 7.1E3 | 7.1E3 | 8.7E3 | 7.9E3 | 1.2E4 | 3.4E3 | 3.4E3 | 4.2E3 | 1.3E5 | 1.9E4 | 113 | 21 | 88 | 21 | 0.50 |
| kP | pg/ml | 6.4E3 | 5.4E3 | 7.5E3 | 6.5E3 | 6.3E3 | 4.3E3 | 8.6E2 | 1.4E3 | 4.8E4 | 1.7E4 | 113 | 21 | 88 | 21 | 0.45 |
| kQ | pg/ml | 4.3E3 | 4.3E3 | 5.0E3 | 5.4E3 | 2.9E3 | 4.0E3 | 5.6E2 | 1.4E3 | 2.5E4 | 2.2E4 | 203 | 26 | 135 | 26 | 0.51 |
| kR | pg/ml | 2.3E1 | 1.8E1 | 3.3E1 | 2.7E1 | 7.3E1 | 2.6E1 | 1.0E-9 | 5.5E0 | 1.0E3 | 1.1E2 | 203 | 26 | 135 | 26 | 0.43 |
| kS | pg/ml | 8.0E2 | 9.0E2 | 9.6E2 | 9.9E2 | 1.1E3 | 6.6E2 | 8.2E1 | 2.9E2 | 1.4E4 | 3.0E3 | 203 | 26 | 135 | 26 | 0.53 |
| pS | pg/ml | 1.9E5 | 1.4E5 | 2.2E5 | 1.6E5 | 1.1E5 | 9.2E4 | 7.5E4 | 6.0E4 | 8.3E5 | 3.6E5 | 100 | 9 | 78 | 9 | 0.30 |
| rZ | ng/ml | 6.0E-4 | 4.0E-3 | 6.3E-3 | 1.6E-2 | 1.6E-2 | 2.8E-2 | 1.0E-9 | 1.0E-9 | 1.1E-1 | 1.1E-1 | 165 | 16 | 104 | 16 | 0.59 |
| rY | ng/ml | 6.1E-2 | 6.5E-2 | 4.1E-1 | 7.9E-2 | 2.4E0 | 5.3E-2 | 1.0E-9 | 1.0E-9 | 2.3E1 | 2.1E-1 | 165 | 16 | 104 | 16 | 0.54 |
| rX | ng/ml | 1.0E-9 | 1.0E-9 | 7.9E-2 | 1.4E-2 | 4.5E-1 | 3.2E-2 | 1.0E-9 | 1.0E-9 | 3.7E0 | 1.2E-1 | 165 | 16 | 104 | 16 | 0.60 |
| lK | pg/ml | 8.1E1 | 5.2E1 | 1.8E2 | 1.2E2 | 3.2E2 | 1.7E2 | 1.0E-9 | 2.3E0 | 3.3E3 | 5.6E2 | 172 | 18 | 111 | 18 | 0.44 |
| lL | pg/ml | 1.6E3 | 1.8E3 | 2.7E3 | 2.3E3 | 4.0E3 | 1.9E3 | 1.5E1 | 1.9E2 | 4.2E4 | 6.8E3 | 173 | 18 | 111 | 18 | 0.52 |
| lM | pg/ml | 1.1E3 | 2.9E3 | 4.1E3 | 7.6E3 | 8.6E3 | 1.2E4 | 3.9E1 | 2.4E1 | 5.1E4 | 4.0E4 | 173 | 18 | 111 | 18 | 0.62 |
| lN | pg/ml | 1.0E-9 | 3.8E0 | 4.5E0 | 5.4E0 | 1.6E1 | 9.0E0 | 1.0E-9 | 1.0E-9 | 1.5E2 | 3.5E1 | 173 | 18 | 111 | 18 | 0.60 |
| lO | pg/ml | 1.0E-9 | 1.0E-9 | 1.8E0 | 9.5E0 | 1.2E1 | 3.3E1 | 1.0E-9 | 1.0E-9 | 1.3E2 | 1.4E2 | 172 | 18 | 111 | 18 | 0.54 |
| zA | ng/ml | 1.9E7 | 1.8E7 | 2.0E7 | 1.7E7 | 6.6E6 | 5.9E6 | 5.9E6 | 7.5E6 | 3.6E7 | 2.5E7 | 95 | 9 | 72 | 9 | 0.38 |
| rW | ng/ml | 1.3E-2 | 1.5E-2 | 3.5E-2 | 1.8E-2 | 5.4E-2 | 1.1E-2 | 1.0E-9 | 7.4E-3 | 3.2E-1 | 4.3E-2 | 98 | 9 | 78 | 9 | 0.54 |
| rV | ng/ml | 1.0E-9 | 1.0E-9 | 1.8E-2 | 1.2E-2 | 6.1E-2 | 2.1E-2 | 1.0E-9 | 1.0E-9 | 2.8E-1 | 5.6E-2 | 98 | 9 | 78 | 9 | 0.57 |
| rU | ng/ml | 7.6E-2 | 7.6E-2 | 2.7E-1 | 1.3E-1 | 6.8E-1 | 1.2E-1 | 1.0E-9 | 1.0E-9 | 4.4E0 | 4.0E-1 | 98 | 9 | 78 | 9 | 0.56 |
| rT | ng/ml | 5.4E0 | 6.9E0 | 6.1E0 | 7.8E0 | 4.0E0 | 4.3E0 | 8.9E-2 | 1.0E0 | 2.1E1 | 1.3E1 | 98 | 9 | 78 | 9 | 0.64 |
| rS | ng/ml | 3.6E0 | 5.2E0 | 5.3E0 | 1.4E1 | 5.3E0 | 1.9E1 | 3.9E-1 | 2.0E0 | 3.8E1 | 5.9E1 | 98 | 9 | 78 | 9 | 0.66 |
| sC | pg/mL | 7.4E3 | 6.2E3 | 1.3E4 | 9.1E3 | 1.5E4 | 7.7E3 | 1.7E3 | 3.4E3 | 8.0E4 | 2.8E4 | 100 | 9 | 78 | 9 | 0.48 |
| yL | ng/ml | 3.1E1 | 4.1E1 | 3.5E1 | 5.7E1 | 2.4E1 | 5.5E1 | 5.6E0 | 1.6E1 | 1.8E2 | 1.9E2 | 98 | 9 | 76 | 9 | 0.63 |
| rP | ng/ml | 1.1E2 | 7.4E1 | 3.1E2 | 2.5E2 | 9.9E2 | 2.4E2 | 1.0E-9 | 1.2E1 | 9.7E3 | 5.0E2 | 98 | 9 | 78 | 9 | 0.52 |
| rQ | ng/ml | 1.0E-9 | 1.0E-9 | 7.5E0 | 1.9E1 | 2.9E1 | 5.6E1 | 1.0E-9 | 1.0E-9 | 1.7E2 | 1.7E2 | 98 | 9 | 78 | 9 | 0.50 |
| rO | ng/ml | 3.0E-2 | 1.5E-2 | 6.2E-2 | 3.9E-2 | 1.0E-1 | 5.5E-2 | 1.0E-9 | 1.0E-9 | 4.9E-1 | 1.4E-1 | 98 | 9 | 78 | 9 | 0.43 |
| rR | ng/ml | 3.9E0 | 4.0E0 | 1.8E1 | 8.8E0 | 4.9E1 | 1.3E1 | 1.0E-9 | 1.0E-9 | 4.5E2 | 3.9E1 | 98 | 9 | 78 | 9 | 0.47 |
| rN | ng/ml | 6.0E-1 | 7.9E-1 | 7.2E-1 | 2.4E0 | 5.1E-1 | 4.1E0 | 5.1E-2 | 3.1E-1 | 3.0E0 | 1.3E1 | 98 | 9 | 78 | 9 | 0.63 |
| qO | pg/ml | 1.0E4 | 1.1E4 | 1.4E4 | 1.2E4 | 1.2E4 | 6.2E3 | 7.4E2 | 5.4E3 | 6.4E4 | 2.3E4 | 100 | 9 | 79 | 9 | 0.53 |
| qP | pg/ml | 3.6E2 | 3.2E2 | 4.7E2 | 3.9E2 | 3.8E2 | 2.0E2 | 1.0E-9 | 1.5E2 | 2.2E3 | 7.5E2 | 100 | 9 | 79 | 9 | 0.47 |
| qQ | pg/ml | 1.5E1 | 1.5E1 | 1.7E1 | 2.1E1 | 3.9E1 | 2.0E1 | 1.0E-9 | 1.0E-9 | 2.8E2 | 4.3E1 | 100 | 9 | 79 | 9 | 0.61 |
| nW | pg/ml | 1.1E5 | 1.1E5 | 1.1E5 | 1.1E5 | 2.5E4 | 3.4E4 | 5.8E4 | 3.6E4 | 1.8E5 | 1.9E5 | 203 | 26 | 135 | 26 | 0.47 |
| nY | pg/ml | 2.1E3 | 2.1E3 | 2.4E3 | 2.7E3 | 1.6E3 | 1.7E3 | 5.1E2 | 6.3E2 | 1.3E4 | 8.1E3 | 203 | 26 | 135 | 26 | 0.54 |
| oO | pg/ml | 8.6E4 | 9.6E4 | 1.2E5 | 1.0E5 | 1.0E5 | 5.2E4 | 2.6E4 | 3.3E3 | 6.2E5 | 2.1E5 | 105 | 20 | 82 | 20 | 0.55 |
| oP | pg/ml | 1.4E5 | 1.4E5 | 1.5E5 | 1.5E5 | 9.3E4 | 9.3E4 | 4.2E4 | 2.4E4 | 4.5E5 | 4.6E5 | 105 | 20 | 82 | 20 | 0.51 |
| oQ | pg/ml | 3.0E3 | 3.2E3 | 3.9E3 | 4.0E3 | 3.0E3 | 2.4E3 | 1.1E3 | 8.7E2 | 2.1E4 | 9.6E3 | 105 | 20 | 82 | 20 | 0.54 |
| oE | pg/ml | 1.5E2 | 6.2E2 | 3.8E2 | 9.0E2 | 5.5E2 | 9.0E2 | 1.0E-9 | 1.0E-9 | 4.7E3 | 3.4E3 | 203 | 26 | 135 | 26 | 0.69 |
| oF | pg/ml | 8.5E3 | 1.9E4 | 2.2E4 | 4.4E4 | 3.6E4 | 5.4E4 | 6.4E1 | 1.3E2 | 2.5E5 | 1.8E5 | 203 | 26 | 135 | 26 | 0.66 |
| oH | pg/ml | 4.1E1 | 3.5E1 | 9.4E1 | 4.9E1 | 1.4E2 | 4.8E1 | 4.2E0 | 7.3E0 | 9.9E2 | 1.8E2 | 203 | 26 | 135 | 26 | 0.40 |
| oK | pg/ml | 7.6E2 | 1.1E3 | 1.9E3 | 3.7E3 | 2.6E3 | 1.0E4 | 5.2E1 | 2.3E2 | 1.8E4 | 5.3E4 | 203 | 26 | 135 | 26 | 0.58 |
| oN | pg/ml | 5.1E2 | 5.1E2 | 7.9E2 | 8.0E2 | 1.5E3 | 9.5E2 | 1.5E2 | 1.1E2 | 1.8E4 | 5.0E3 | 203 | 26 | 135 | 26 | 0.53 |
| oW | pg/ml | 2.1E2 | 3.5E2 | 4.2E2 | 5.7E2 | 9.3E2 | 7.8E2 | 7.7E1 | 9.5E1 | 6.0E3 | 2.7E3 | 40 | 13 | 37 | 13 | 0.55 |
| oT | pg/ml | 3.2E2 | 3.0E2 | 3.7E2 | 3.4E2 | 2.0E2 | 1.2E2 | 9.9E1 | 1.4E2 | 7.9E2 | 5.4E2 | 40 | 13 | 37 | 13 | 0.49 |
| oV | pg/ml | 1.2E2 | 8.1E1 | 2.7E2 | 1.4E2 | 4.3E2 | 1.6E2 | 1.0E-9 | 1.1E1 | 2.2E3 | 6.3E2 | 40 | 13 | 37 | 13 | 0.41 |
| oD | pg/ml | 1.6E4 | 1.6E4 | 1.7E4 | 1.7E4 | 7.5E3 | 5.8E3 | 6.6E3 | 1.1E4 | 4.6E4 | 3.3E4 | 40 | 13 | 37 | 13 | 0.49 |
| uL | ng/ml | 3.8E1 | 4.3E1 | 5.5E1 | 4.5E1 | 7.2E1 | 2.4E1 | 1.0E-9 | 2.1E1 | 4.0E2 | 9.2E1 | 99 | 9 | 77 | 9 | 0.54 |
| uO | ng/ml | 4.0E-1 | 4.5E-1 | 9.0E-1 | 6.5E-1 | 1.4E0 | 7.4E-1 | 1.0E-9 | 1.0E-9 | 9.3E0 | 1.7E0 | 99 | 9 | 77 | 9 | 0.46 |
| uM | ng/ml | 5.9E-1 | 3.2E-1 | 9.4E-1 | 6.6E-1 | 1.7E0 | 8.6E-1 | 1.0E-9 | 1.0E-9 | 1.3E1 | 2.5E0 | 99 | 9 | 77 | 9 | 0.40 |
| uI | ng/ml | 7.3E-2 | 5.9E-2 | 1.2E-1 | 8.2E-2 | 1.6E-1 | 5.0E-2 | 1.6E-2 | 3.4E-2 | 1.1E0 | 1.8E-1 | 98 | 9 | 76 | 9 | 0.47 |
| uN | ng/ml | 1.5E1 | 1.9E1 | 1.7E1 | 2.0E1 | 6.9E0 | 8.2E0 | 6.3E0 | 9.2E0 | 4.1E1 | 3.3E1 | 99 | 9 | 77 | 9 | 0.63 |
| uG | ng/ml | 1.9E1 | 2.2E1 | 2.4E1 | 3.7E1 | 1.6E1 | 3.9E1 | 1.2E0 | 6.5E0 | 8.9E1 | 1.3E2 | 99 | 9 | 77 | 9 | 0.59 |
| uR | ng/ml | 2.5E0 | 3.3E0 | 3.6E0 | 3.4E0 | 6.5E0 | 2.0E0 | 7.3E-1 | 1.3E0 | 6.4E1 | 6.6E0 | 99 | 9 | 77 | 9 | 0.55 |

Figure 3 Continued

| Code | Units | Median | | Average | | Standard Deviation | | Minimum | | Maximum | | Number of Samples | | Number of Patients | | AUC |
|------|-------|--------|------|---------|------|-------|-------|--------|-------|--------|-------|--------|-----|---------|-----|------|
|      |       | NonDis | Dis  | NonDis  | Dis  | NonDis| Dis   | NonDis | Dis   | NonDis | Dis   | NonDis | Dis | NonDis  | Dis |      |
| uP   | ng/ml | 2.2E0  | 2.5E0| 2.6E0   | 2.8E0| 1.3E0 | 1.3E0 | 1.1E0  | 9.3E-1| 9.1E0  | 4.8E0 | 99     | 9   | 77      | 9   | 0.59 |
| uV   | ng/ml | 1.1E-3 | 1.3E-3| 1.3E-2 | 4.1E-3| 2.6E-2| 5.9E-3| 1.0E-9 | 1.0E-9| 2.0E-1 | 1.8E-2| 99     | 9   | 77      | 9   | 0.44 |
| uT   | ng/ml | 6.4E1  | 1.1E2| 8.8E1   | 1.5E2| 8.4E1 | 1.2E2 | 1.2E1  | 4.7E1 | 5.8E2  | 4.1E2 | 99     | 9   | 77      | 9   | 0.71 |
| uU   | ng/ml | 1.7E0  | 2.7E0| 2.0E0   | 4.0E0| 1.2E0 | 6.0E0 | 5.9E-1 | 5.4E-1| 7.0E0  | 2.0E1 | 99     | 9   | 77      | 9   | 0.55 |
| uW   | ng/ml | 7.6E0  | 8.1E0| 8.1E0   | 8.0E0| 2.9E0 | 2.4E0 | 3.5E0  | 3.1E0 | 2.2E1  | 1.2E1 | 99     | 9   | 77      | 9   | 0.56 |
| vB   | ng/ml | 2.9E0  | 3.2E0| 3.1E0   | 3.4E0| 1.7E0 | 1.6E0 | 5.9E-1 | 1.3E0 | 1.0E1  | 6.6E0 | 99     | 9   | 77      | 9   | 0.55 |
| vC   | ng/ml | 1.0E-9 | 1.0E-9| 4.1E-3 | 1.0E0| 2.5E-2| 0.0E0 | 1.0E-9 | 1.0E-9| 2.0E-1 | 1.0E-9| 99     | 9   | 77      | 9   | 0.47 |
| uY   | ng/ml | 6.9E-1 | 7.5E-1| 1.2E0  | 1.3E0| 1.0E0 | 1.4E0 | 6.8E-2 | 1.8E-1| 4.9E0  | 4.4E0 | 99     | 9   | 77      | 9   | 0.47 |
| uZ   | ng/ml | 5.4E-1 | 5.9E-1| 7.6E-1 | 7.9E-1| 9.1E-1| 6.9E-1| 1.0E-1 | 1.0E-1| 7.2E0  | 2.0E0 | 99     | 9   | 77      | 9   | 0.52 |
| uX   | ng/ml | 1.2E1  | 1.7E1| 1.3E1   | 3.0E1| 7.6E0 | 2.9E1 | 3.6E0  | 4.0E0 | 4.4E1  | 7.8E1 | 99     | 9   | 77      | 9   | 0.63 |
| vA   | ng/ml | 7.2E-2 | 7.3E-2| 8.5E-2 | 1.0E-1| 5.4E-2| 1.2E-1| 1.7E-2 | 2.5E-2| 3.0E-1 | 4.2E-1| 99     | 9   | 77      | 9   | 0.47 |
| vH   | ng/ml | 1.2E-1 | 1.1E-1| 1.7E-1 | 3.5E-1| 1.6E-1| 5.9E-1| 9.9E-3 | 4.7E-2| 9.6E-1 | 1.9E0 | 100    | 9   | 78      | 9   | 0.53 |
| vI   | ng/ml | 1.7E0  | 2.9E0| 2.1E0   | 3.0E0| 1.9E0 | 3.1E0 | 4.2E-3 | 1.7E-3| 1.0E1  | 1.0E1 | 100    | 9   | 78      | 9   | 0.59 |
| vP   | ng/ml | 4.2E2  | 3.1E2| 5.1E2   | 4.7E2| 4.5E2 | 4.5E2 | 4.0E1  | 1.5E2 | 2.4E3  | 1.6E3 | 99     | 9   | 77      | 9   | 0.49 |
| vT   | ng/ml | 8.2E1  | 7.7E1| 1.1E2   | 8.9E1| 1.0E2 | 4.1E1 | 2.4E1  | 4.6E1 | 6.9E2  | 1.6E2 | 99     | 9   | 77      | 9   | 0.49 |
| vU   | ng/ml | 1.0E-9 | 1.0E-9| 2.1E1  | 2.5E1| 3.1E1 | 4.5E1 | 1.0E-9 | 1.0E-9| 1.2E2  | 1.1E2 | 99     | 9   | 77      | 9   | 0.49 |
| vQ   | ng/ml | 3.5E2  | 3.2E2| 3.7E2   | 3.7E2| 1.4E2 | 1.7E2 | 6.7E1  | 1.9E2 | 8.4E2  | 6.0E2 | 99     | 9   | 77      | 9   | 0.50 |
| vO   | ng/ml | 1.8E3  | 2.0E3| 1.8E3   | 2.1E3| 4.4E2 | 6.9E2 | 1.0E3  | 1.0E3 | 3.0E3  | 3.2E3 | 99     | 9   | 77      | 9   | 0.61 |
| vS   | ng/ml | 1.3E3  | 1.4E3| 1.2E3   | 1.5E3| 4.7E2 | 3.1E2 | 1.0E-9 | 1.1E3 | 2.1E3  | 1.9E3 | 99     | 9   | 77      | 9   | 0.70 |
| vV   | ng/ml | 9.0E2  | 9.4E2| 1.4E2   | 2.4E4| 1.7E3 | 7.0E4 | 2.1E1  | 2.3E2 | 1.1E4  | 2.1E5 | 99     | 9   | 77      | 9   | 0.50 |
| vW   | ng/ml | 1.4E2  | 1.6E2| 1.7E2   | 2.7E2| 1.2E2 | 2.3E2 | 4.3E1  | 6.0E1 | 6.7E2  | 7.7E2 | 99     | 9   | 77      | 9   | 0.60 |
| pF   | pg/ml | 4.8E-1 | 7.5E-1| 1.1E0  | 1.1E0| 6.1E0 | 9.4E-1| 1.0E-9 | 1.8E-1| 8.7E1  | 4.4E0 | 203    | 26  | 135     | 26  | 0.66 |
| pH   | ng/ml | 7.9E0  | 1.2E1| 9.5E0   | 1.3E1| 6.6E0 | 1.1E1 | 3.0E0  | 3.3E0 | 4.2E1  | 4.7E1 | 40     | 13  | 37      | 13  | 0.62 |
| pI   | ng/ml | 7.0E1  | 6.0E1| 7.6E1   | 6.6E1| 4.1E1 | 2.7E1 | 2.6E1  | 2.5E1 | 2.0E2  | 1.2E2 | 40     | 13  | 37      | 13  | 0.44 |
| pK   | ng/ml | 4.9E-1 | 4.2E-1| 5.3E-1 | 5.3E-1| 2.7E-1| 3.2E-1| 1.7E-1 | 1.6E-1| 1.6E0  | 1.4E0 | 40     | 13  | 37      | 13  | 0.48 |

Analyte panel data:

Unconstrained panels with 3 analytes, where 1.0E-10 >= 'model p-value' > 0. Contains 4,594 panels of 35,857,239 total panels evaluated. :
Ji{Ms(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) My(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ng(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) In(aA Et Fp Fr Hq Hr Hu Hv Hw Hx Ih Ii Ij Ik Il Im Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Jj(aA Et Fp Fr Hq Hr Hu Hv Hw Hx Ih Ii Ij Ik Il Im Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Nx(aA Et Fp Fr Hq Hr Hu Hv Hw Hx Ih Ii Ij Ik Il Im Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nn No Nq Nr Ns Nt Nu Nv Nw Ny Oe Of Og Oh Oi Ok Om On Oy Oz Pa Pb Pc Pd Pe Pf Pg Po Pz Qa Qb Qc Qd Qe Wm) Oy(aA Et Fp Fr Hq Hr Hu Hv Hw Hx Ih Ii Ij Ik Il Im Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nn No Nq Nr Ns Nt Nu Nv Nw Ny Oe Of Og Oh Oi Ok Om On Oz Pa Pb Pc Pd Pe Pf Pg Po Pz Qa Qb Qc Qd Qe Wm) Et(aA Fp Fr Hq Hr Hu Hv Hw Hx Ih Ii Ij Ik Il Im Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nn No Nq Nr Ns Nt Nu Nv Nw Ny Oe Of Og Oh Oi Ok Om On Oz Pa Pb Pc Pd Pe Pf Pg Po Pz Qa Qb Qc Qd Qe) Fp(aA Fr Hq Hr Hu Hv Hw Hx Ih Ii Ij Ik Il Im Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nn No Nq Nr Ns Nt Nu Nv Nw Ny Oe Of Og Oh Oi Ok Om On Oz Pa Pb Pc Pd Pe Pf Pg Po Pz Qa Qb Qc Qd Qe) Lu(aA Fr Hq Hr Hu Hv Hw Hx Ih Ii Ij Ik Il Im Io Ip Iq Ir Is It Iu Iv Jg Jh Jk Jl Jm Jn Jo Jp Jq Jr Js Jt Lh Li Lj Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nn No Nq Nr Ns Nt Nu Nv Nw Ny Oe Of Og Oh Oi Ok Om On Oz Pa Pb Pc Pd Pe Pf Pg Po Pz Qa Qb Qc Qd Qe) Nd(aA Fr Hq Hr Hu Hv Hw Hx Ih Ii Ij Ik Il Im Io Ip Iq Ir Is It Iu Iv Jg Jh Jk Jl Jm Jn Jo Jp Jq Jr Js Jt Lh Li Lj Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Ne Nf Nh Ni Nj Nk Nl Nm Nn No Nq Nr Ns Nt Nu Nv Nw Ny Oe Of Og Oh Oi Ok Om On Oz Pa Pb Pc Pd Pe Pf Pg Po Pz Qa Qb Qc Qd Qe) Ii(aA Fr Hq Hr Hu Hv Hw Hx Ih Ij Ik Il Im Io Ip Iq Ir Is It Iu Iv Jg Jh Jk Jl Jm Jn Jo Jp Jq Jr Js Jt Lh Li Lj Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Ne Nf Nh Ni Nj Nk Nl Nm Nn No Nq Nr Ns Nt Nu Nv Nw

Lx Mq Mt No Nw On Qe Wm) Mq(li In Jn Jq Lu Lx Mg Ml Nc Ne Ns Oe Pb) In(Ik Iv Jl Li Lv Lx Mh Mt Nc Ne No Qe) No(Aj Ch Ii Ik Lu Lv Ne Ne Oe) Qe(Hq Ii Jk Lu Nc Ns Oe Pb) Lu(Li Lv Lx Nc Ne Pb) Oe(Ik Li Lx Mt Nc Ne) Ii(Jl Lh Li Lx Mt) Pf(Aj Ch Co Kg) Pb(Ik Lx Ne) Aj(Mm Oa) Mg(Ik Mt) Nc(Ni Nk) ChHu NsMt LxHq MdJq MkJl NiLi KgVt} Jj{Fp(aA Fr Hq Hu Hv Hw Ih Ii Ij Ik Il Im In Ip Ir Is It Iu Iv Jg Jk Jl Jm Jn Jo Jp Jq Jr Js Jt Lh Li Lj Lu Lv Lw Lx Lz Ma Mc Md Me Mf Mg Mi Mm Mn Mp Mq Mr Ms Mt Mu Mw Mx My Mz Na Nb Nc Nd Ne Nf Ng Nh Ni Nj Nk Nl Nm Nn No Nr Ns Nt Nv Nw Nx Ny Oe Of Oh Ok Om On Oy Oz Pa Pb Pc Pd Pe Pf Pg Po Pz Qa Qb Qc Qd Qe) Im(aA Fr Hq Hu Hv Hw Hx Ih Ik In Io Ip Ir Is It Iv Jg Jh Jk Jl Jm Jn Jo Jq Jr Js Jt Lh Li Lj Lu Lv Lw Lx Ly Mb Mc Me Mf Mg Mh Mi Mj Ml Mm Mn Mp Mq Mr Ms Mt Mu Mw Mx My Mz Nb Nc Nd Ne Nf Ng Nh Ni Nj Nl Nn No Nq Nr Ns Nt Nu Nw Nx Oe Og Oh Ok Om On Oy Oz Pa Pb Pc Pd Pe Pf Pg Po Pz Qa Qc Qd Qe) Is(Ik Jg Lh Li Lj Lu Lv Lx Me Mq Ms Mt Nb Nc Nd Ne Nj Nl No Nt Nw Ok Pf Qe) Qa(Ik Lh Li Lv Lx Me Mq Ms Nd Nj Nl Nw Ok) Ik(Ip Jl Lh Li Lj Lx No Nw Ok Qe) Mq(Lh Li Lj Lx Mt No Nw Ok Qe) Nd(Jl Lh Li Lx No Nw Ok On Qe) Nj(Li Lx No Nw Ok Qe) Ms(Lh Lx Nw Ok Qe) Nl(Lh No Nw Qe) Lv(Li Lx No) Me(Li Lx Nw) Lj(Lh Mt) LxJl NgJg} Nw{Ms(aA Fp Hq Hu Hv Hw Ik Il Im In Io Ip Ir Is Iv Jg Jl Jm Jn Jo Jq Jr Jt Lh Li Lj Lu Lv Lx Lz Mc Md Me Mf Ml Mn Mq Mr Mt Mw My Nb Nc Nd Ne Ng Nh Ni Nj Nl Nn No Ns Nt Oe Ok On Oy Pa Pb Pc Pe Pf Po Qa Qh Qe) Fp(lm In Md Mj My Ng Oe Oy Pb) Ng(Ik Im Is Jg Mq) My(Jg Jh) Nd(Im No) Jk(Im Qa) MqOy} Ng{Jg(aA Fp Fr Hu Ik Im In Ip Ir Is Jl Jn Jq Jr Lh Li Lj Lu Lv Lx Mc Me Mq Mr Ms Mt Mw My Mz Nc Nd Ne Nh Ni Nj Nl No Nr Nt Nx Oh Ok Om On Oy Pe Pf Po Qa Qb Qd Qe) On(Fp Im Lx) Ok(Fp Im)} Fp{In(Im Is Jl Jq Mm Ok Qa) Ms(Is Ok On) On(My Oy) JgOy JoOk} No{Nd(In Is Lv) NjIn} Ms{Ok(Im Is Lx) LxIs} IsJgOy WeLdmZ

Unconstrained panels with 3 analytes, where 1.0E-9 >= 'model p-value' > 1.0E-10. Contains 7,604 panels of 35,857,239 total panels evaluated. : Ji{Qc(Fr Hq Hr Hu Hv Hw Hx Ih Ij Ik Il Io Ip Iq Ir Is It Iu Iv Jg Jh Jk Jl Jm Jn Jp Jq Jr Js Jt Lh Li Lv Lw Lx Ly Lz Ma Mb Mc Me Mf Mg Mh Mi Mj Mk Ml Mm Mn Mp Mr Mt Mu Mv Mw Mx Mz Na Nb Nc Ne Nf Nh Ni Nj Nk Nl Nm Nn No Nq Nr Ns Nt Nu Nv Nw Ny Oe Of Oh Oi Ok Om On Oz Pa Pb Pc Pd Pe Pf Pg Po Pz Qa Qb Qd Qe) Nt(Fr Hq Hr Hu Hv Hw Hx Ih Ij Ik Il Io Ip Iq Ir Is It Iu Iv Jg Jh Jl Jm Jn Jp Jq Jr Js Lh Li Lv Lw Lx Ly Lz Ma Mb Mc Me Mf Mg Mh Mi Mj Mk Ml Mm Mn Mp Mq Mr Mt Mu Mv Mw Mx Mz Na Nb Nc Ne Nf Nh Ni Nj Nk Nl Nm Nn No Nq Nr Ns Nu Nv Nw Ny Of Oi Ok Om On Oz Pa Pc Pd Pe Pf Pg Po Pz Qa Qb Qd Qe) Ip(Fr Hq Hr Hu Hv Hw Hx Ih Ij Ik Il Io Iq Ir Is It Iu Iv Jg Jh Jk Jl Jm Jn Jp Jq Jr Js Lh Li Lv Lw Lx Ly Lz Ma Mb Mc Me Mf Mg Mh Mi Mj Mk Ml Mm Mn Mp Mg Mr Mt Mu Mv Mw Mx Mz Na Nb Nc Ne Nf Nh Ni Nj Nk Nm Nn No Nq Nr Ns Nu Nv Nw Ny Oe Of Oh Oi Ok Om On Oz Pa Pc Pd Pe Pf Pg Po Pz Qa Qb Qd Qe) Ir(aA Fr Hq Hr Hu Hv Hw Hx Ih Ij Ik Il Io Iq Is It Iu Iv Jg Jl Jm Jn Jp Jr Js Lh Li Lv Lw Lx Ly Lz Ma Mb Mc Me Mf Mg Mh Mi Mj Mk Ml Mm Mn Mp Mq Mr Mt Mu Mv Mw Mx Mz Na Nb Nc Ne Nf Nh Ni Nj Nk Nl Nm Nn No Nq Nr Ns Nu Nv Nw Ny Oe Of Oh Oi Ok Om On Oz Pa Pc Pd Pe Pf Pg Po Pz Qa Qb Qd Qe) Iu(Fr Hq Hr Hu Hv Hw Hx Ih Ij Ik Il Io Iq Is It Iv Jg Jh Jk Jl Jm Jn Jp Jq Jr Js Jt Lh Li Lv Lw Lx Ly Lz Ma Mb Mc Me Mf Mg Mh Mi Mj Mk Ml Mm Mn Mp Mr Mt Mu Mv Mw Mx Mz Na Nb Nc Ne Nf Nh Nj Nk Nl Nm Nn No Nq Nr Ns Nu Nv Nw Ny Oe Of Og Oh Oi Ok Om On Oz Pa Pc Pd Pe Pf Pg Po Pz Qa Qb Qd Qe) Nm(Fr Hq Hr Hu Hv Hw Hx Ih Ij Ik Il Io Iq Is It Iv Jg Jh Jk Jl Jm Jn Jp Jq Jr Js Jt Lh Lv Lw Lx Ly Lz Ma Mb Mc Me Mf Mg Mh Mi Mj Mk Ml Mm Mn Mp Mr Mt Mu Mv Mw Mx Mz Na Nb Nc Ne Nf Nh Nj Nk Nl Nn No Nq Nr Ns Nu Nv Nw Ny Oe Of Oh Oi Ok Om On Oz Pa Pc Pd Pe Pf Pg Po Pz Qb Qd Qe) Ly(Fr Hq Hr Hu Hv Hw Hx Ih Ij Ik Il Io Iq Is It Iv Jg Jh Jk Jl Jm Jn Jp Jr Js Jt Lh Li Lv Lw Lx Lz Ma Mb Mc Me Mf Mg Mh Mi Mj Mk Ml Mm Mn Mp Mr Mt Mu Mv Mw Mx Mz Na Nb Nc Ne Nf Nh Nj Nk Nn No Nq Nr Ns Nu Nv Nw Ny Oe Of Oh Oi Ok Om On Oz Pa Pc Pd Pe Pf Pg Po Pz Qa Qb Qd Qe) Mf(Fr Hq Hr Hu Hv Hw Hx Ih Ij Ik Il Io Iq Is It Iv Jh Jk Jl Jm Jn Jq Jr Js Jt Lh Li Lv Lw Lx Lz Ma Mb Mc Me Mg Mh Mi Mj Mk Ml Mm Mn Mp Mq Mr Mt Mu Mv Mw Mx Mz Na Nb Nc Ne Nh Ni Nj Nk Nl No Nq Nr Ns Nu Nv Nw Ny Oe Of Og Oi Ok Om On Oz Pa Pc Pd Pe Pf Pg Po Pz Qa Qb Qd Qe) Qb(Fr Hq Hr Hu Hv Hw Hx Ih Ij Ik Il Io Iq Is It Iv Jg Jh Jl Jm Jn Jp Jq Jr Js Jt Lh Li Lv Lw Lz Ma Mb Mc Me Mg Mh Mi Mj Mk Ml Mm Mn Mp Mr Mt Mu Mv Mw Mx Mz Na Nb Nc Ne Nf Nh Ni Nj Nk Nl Nn No Nq Nr Ns Nu Nv Nw Ny Oe Of Oh Oi Ok Om On Oz Pa Pb Pc Pd Pe Pf Pg Po Pz Qd) Nw(aA Fr Hq Hr Hu Hv Hw Hx Ih Ij Ik Il Io Iq Is It Iv Jg Jh Jk Jl Jm Jn Jp Jq Jr Js Jt Lh Li Lv Lw Lx Lz Ma Mb Mc Me Mg Mh Mi Mj Mk Ml Mm Mn Mp Mr Mt Mu Mv Mx Mz Na Nb Nc Ne Nf Nh Ni Nk Nn No Nq Nr Ns Nu Nv Nw Ny Oe Og Oh Oi Ok Om On Oz Pa Pc Pd Pe Pf Pg Po Pz Qa Qd Qe) Mz(Fr Hq Hr Hu Hv Hw Hx Ih Ij Ik Il Io Iq Is It Iv Jg Jh Jk Jl Jm Jn Jq Jr Js Jt Lh Li Lv Lw Lz Ma Mb Mc Me Mg Mh Mi Mj Mk Ml Mm Mn Mp Mr Mt Mu Mv Mw Mx Na Nb Nc Ne Nf Nh Ni Nk Nn No Nq Nr Ns Nu Nv Ny Oe Of Og Oi Ok Om On Oz Pa Pc Pd Pe Pf Pg Po Pz Qa Qd Qe) Il(Fr Hq Hr Hu Hv Hw Hx Ih Ij Ik Io Iq Is It Iv Jg Jh Jk Jl Jm Jn Jp Jq Jr Js Jt Lh Li Lv Lw Lx Lz Ma Mb Mc Me Mg Mh Mi Mj Mk Ml Mm Mn Mr Mt Mu Mv Mw Mx Na Nb Nc Ne Nh Ni Nj Nk Nl Nn No Nq Nr Ns Nu Nv Ny Oe Of Oi Ok Om On Oz Pa Pc Pd Pe Pf Pg Po Pz Qd Qe) Qd(Fr Hq Hr Hu Hv Hw Hx Ih Ij Ik Io Iq Is It Iv Jg Jh Jl Jm Jn Jp Jq Jr Js Lh Li Lv Lw Lx Lz Ma Mb Mc Me Mg Mh Mi Mj Mk Ml Mm Mn Mp Mr Mt Mu Mv Mw Mx Na Nb Nc Ne Nf Nh Nj Nk Nl Nn No Nq Nr Ns Nu Nv Ny Of Oh Oi Ok Om On Oz Pa Pc Pd Pe Pf Pg Po Pz Qa Qe) Jh(Fr Hq Hr Hu Hv Hw Hx Ih Ij Ik Io Iq It Iv Jg Jk Jl Jm Jn Jp Jq Jr Js Jt Lh Lv Lw Lz Ma Mb Mc Me Mg Mh Mi Mj Mk Ml Mm Mn Mp Mr Mt Mu Mv Mw Mx Na Nb Nc Ne Nf Nh Nj Nk Nl Nn No Nq Nr Ns Nu Nv Ny Oe Of Og Oh Oi Ok Om On Oz Pa Pc Pd Pe Pf Pg Po Pz Qe) Fr(aA Hq Hr Hu Hv Hw Hx Ih Ij Ik Io Iq Is It Iv Jl Jn Jm Jn Jp Jq Jr Js Lh Li Lv Lx Lz Ma Mb Mc Me Mg Mh Mi Mj Mk Ml Mm Mn Mp Mq Mr Mt Mu Mv Mx Na Nb Nc Ne Nf Nh Ni Nk Nl Nn No Nq Nr Ns Nu Nv Ny Oe Of Oi Ok Om On Oz Pa Pc Pd Pe Pf Pg Po Pz Qa Qe) Nk(Hq Hr Hu Hv Hw Hx Ih Ij Ik Io Iq Is It Iv Jg Jk Jl Jm Jn Jp Jq Jr Js Jt Lh Li Lv Lw Lz Ma Mb Mc Me Mg Mh Mi Mj Mk Ml Mm Mn Mp Mr Mt Mu Mv Mw Mx Na Nb Nf Nh Nl Nn No Nq Nr Ns Nu Nv Ny Oe Of Og Oh Oi Ok Om On Oz Pa Pc Pd Pe Pf Pg Po Pz Qe) Oz(aA Hq Hr Hu Hv Hw Hx Ih Ij Ik Io Iq Is Iv Jk Jl Jm Jn Jp Jq Jr Js Jt Li Lv Lx Lz Mb Mc Me Mg Mh Mi Mj Mk Ml Mm Mn Mp Mq Mr Mt Mu Mv Mw Mx Na Nb Nc Ne Nh Ni Nj Nl Nn No Nq Nr Ns Nu Nv Ny Oe Of Og Oi Ok Om On Pa Pc Pd Pe Pf Pg Po Pz Qa Qe) Ml(Hq Hr Hu Hv Hw Hx Ih Ij Ik Io Iq Is It Iv Jg Jk Jl Jm Jn Jp Jq Jr Js Jt Lh Lv Lw Lz Ma Mb Mc Me Mg Mh Mi Mj Mk Mm Mn Mp Mr Mu Mv Mw Mx Na Nb Nc Ne Nf Nh Nj Nn No Nq Nr Ns Nu Nv Ny Oe Of Oh Oi Ok Om On Pa Pc Pd Pe Pf Pg Po Pz Qe) Js(Hq Hr Hu Hv Hw Hx Ih Ij Ik Io Iq Is It Iv Jg Jk Jl Jm Jp Jq Jr Jt Lh Lv Lw Lz Ma Mb Mc Me Mg Mh Mi Mj Mk Mm Mn Mp Mr Mt Mu Mv Mw Mx Na Nb Nc Ne Nf Nh Ni Nj Nn Nq Nr Ns Nu Nv Ny Oe Of Oh Oi Ok Om On Pa Pc Pd Pe Pf Pg Po Pz Qe) Jn(aA Hq Hr Hu Hv Hw Hx Ih Ij Ik Io Iq Is It Iv Jg Jl Jm Jp Jr Lh Li Lv Lw Lz Ma Mb Mc Me Mg Mh Mi Mj Mk Mm Mn Mp Mr Mt Mu Mv Mw Mx Na Nb Nc Ne Nf Nh Nj Nn No Nq Nr Nu Nv Ny Oe Of Oh Oi Ok Om On Pa Pc Pd Pe Pf Pg Po Pz Qa Qe) Oi(Hq Hr Hu Hv Hw Hx Ih Ij Ik Io Iq Is It Iv Jg Jk Jl Jm Jp Jr Jt Lh Lv Lw Lz Ma Mb Mc Me Mg Mh Mi Mj Mk Mm Mn Mp Mr Mt Mu Mv Mw Mx Na Nb Nc Ne Nf Nh Nj Nn No Nq Nr Ns Nu Nv Ny Oe Of Og Oh Ok Om On Pa Pc Pd Pe Pf Pg Po Pz) Na(aA Hq Hr Hu Hv Hw Hx Ih Ij Ik Io Iq Is It Iv Jk Jl Jm Jq Jr Jt Li Lv Lx Lz Mb Mc Me Mg Mh Mi Mj Mk Mm Mn Mq Mr Mt Mu Mv Mw Nb Nc Ne Nh Ni Nj Nl No Nq Nr Ns Nu Nv Ny Oe Of Og Ok Om On Pa Pb Pc Pe Pf Pg Po Pz Qa Qe) Mx(aA Hq Hr Hu Hv Hw Hx Ih Ij Ik Io Iq Is Iv Jk Jl Jm Jq Jr Jt Li Lv Lx Lz Mb Mc Me Mg Mh Mi Mj Mk Mm Mn Mq Mr Mt Mu Mv Mw Nb Nc Ne Nh Ni Nj Nl No Nq Nr Ns Nu Nv Ny Oe Of Og Ok Om On Pa Pb Pc Pe Pf Pg Po Pz Qa Qe) Ij(aA Hq Hr Hu Hv Hw Hx Ih Io Iq It Iv Jg Jk Jl Jm Jp Jq Jr Jt Lh Lv Lw Lz Ma Mb Mc Me Mg Mh Mi Mj Mk Mm Mn Mp Mr Mu Mv Mw Nb Nc Nf Nh Nn No Nq Nr Ns Nu Nv Ny Oe Of Og Oh Ok Om On Pa Pb Pc Pd Pe Pf Pg Po Pz Qe) Iq(aA Hq Hr Hu Hv Hw Hx Ih Ik Io Is Iv Jk Jl Jm Jq Jr Jt Lh Li Lv Lx Mb Mc Md Mc Mg Mh Mi Mj

Figure 3 Continued

Pd Pg Pz Qc Wm) On(Ik Is Li Lj Mq Ms Mt Nd Ok Qa Qe Wm) Ok(Ik Is Li Lu Lx Mq Ms Mt Qa Qe) Im(Fr Is Lh Li Lv Lx Mm Mq Mt) Is(In Li Lx Mq Mt No) No(Ik Nd Wm) Lx(Lh Mq) WmPf} Ms{Ok(aA In Jl Jo Jr Jt Lh Li Lj Lu Lv Me Mq Mt Nc Nd Nj Nl No On Pc Qa Qe) Is(Im In Jg Lh Li Lj Lv Mm Mq Mt Nd Ni No On) Lx(aA Im Iv Jg Jl Jq Lh Lv Mq Mr Mt On) Im(aA Jl Lh Lv Mt No On) No(Lv Nd Nj Wm) Mt(Lh On) LjOn} Nd{No(aA Im Ip Iv Jg Jl Jn Jp Jq Jr Lh Lx Mm Mp Mq Mr Nc Oe Ok On Pb Pc Pe Qa Qe) Im(aA Is Iv Jl Lh Lv Lx Mm Mr Ok On Pe Pf) Is(In Lj Lx Mm Ok) Ok(Jl Jo Lj Lx) On(Lj My Oy) LxJl InQa LhLj} Ok{Jo(Ik Im Is Jl Lh Lv Me Mq Nj Qa) In(Im Is Lj Lx Me Mq Nj Qa) Im(Ii Jk Jt Nj Oe) Is(Ii Jk) QaJk} Im{Jk(aA Is Jl Lh Li On Qa) Nj(In No) Lh(Ii Oy) On(My Oy) aA(Lv Oe) MqIn NkNl} In{Is(Li Lj Lv Lx Me Mq Nj No) No(Ik Wm) Mq(Lx Qa) NjQa} Oy{Jg(Jl Lh Lx Mq Mr On Pe Qa) On(Ik Is Li Lx Mt)} No{Nj(Lv Mq Ni Nk) WmMy} Jk{Is(Li Lx) QaJg} Wm{Ke(Nb Ut)} AdAjdF LiwPnW

Unconstrained panels with 3 analytes, where 1.0E-8 >= 'model p-value' > 1.0E-9. Contains 9,396 panels of 35,857,239 total panels evaluated. : Et{Aj(aC Af Al aM aO Ap Ar As AW bA Bb bF bL Bn BO bV cI cK cM cO CP Cq CT Cv Cw Cx Db Dd De dF Dg Di dJ Dl dM Dp Ed Ef Ez Fa Fn Fp Fr Fw Fy Gl Gp Ha Hb Hf Hr Hw Hx Ib Ic Ih Ii Io Ip Iq Ir It Iu Iv Iz Jd Je Jf Jg Jh Jk Jn jO Jp Js Jt Ju Jv Jy Kc Kd Ke Kf Ki Kj Kk Kl Kn Ko Kp Kq Ks Kx Ky Kz Ld Lh Lu Lw Ly Lz Ma Mb Mc Md Mf Mg Mh Mi Mj Mn Mp Mu Mw Mx Mz Na Nf Nh Nj Nk Nl Nm Nn Nq Ns Nt Nu Nv Nw Nx Ny Oe Of Og Oh Oi Ok Om On Or Ou Ow Oz Pa Pb Pc Pg Ph Pi Pj Pk Po Pz Qb Qc Qg Qh Ql Qm Qn Qt Qu Qv Qw Qx Qy Qz Ra Rb Rc Rf Rg Rj Rm Sr Ss St Tn To Tv Tz Ua Ub Uc Ud Ue Uf Ug Uh Uk Um Un Uo Up Ur Us Ut Uu Uv Vp Tj) Kg(aA Al An AO Ap Ar Aw BA Bb bN Bo cl Co CP Ct Cv Db Dd Dg Di DK Dl dM Ed Ez Fa Fb Fn Fp Fr Fw Gl Gp Ha Hb Hc Hf Hq Hr Hu Hv Hw Hx Ib Ic Ih Ii Ik Il In Io Ip Iq Ir It Iu Iv Iz Jd Je Jf Jg Jh Jj Jk Jl Jn Jo Jp Jr Js Jt Ju Jv Jy Kc Ki Kj Kk Kl Ks Kx Kz Ld Lu Lv Lw Lx Ly Lz Ma Mb Mc Md Mf Mg Mh Mi Mj Mk Mn Mp Mq Mt Mu Mv Mw Mx My Mz Na Nb Nc Nd Nf Nh Ni Nj Nk Nl Nn Nq Nr Ns Nt Nu Nv Nw Nx Ny Oe Of Og Oh Oi Ok Om On Or Ou Ow Oy Oz Pa Pb Pc Pd Pg Ph Pj Pk Po Pz Qb Qc Qd Qg Ql Qm Qn Qt Qu Qv Qw Qx Qy Qz Rb Rc Rf Rg Rj Rm Ss St To Tz Ua Ub Uc Ud Ue Uf Ug Uh Uk Ul Um Uo Up Ur Ut Uu Uv Vo Vp Vq Vv Tj) Ch(aC Ad Af Al An Ao Ap Ar As AW Ax aZ Ba Bb Bc bF Bg bH bJ Bn BO cC cD Co CP Cq CT Cu Cv Cw Cx Db Dc DD De dF Dg Dk Dl Dp Ed Fa Fb Fp Fr Fw Gp Hb Hc Hf Hq Hr Hv Hw Hx Ic Id Ih Ii Ij Ik Il Io Ip Iq Ir It Iu Iv Iz Jg Jh Jk Jl Jn Jp Jq Js Ju Jv Jy Kc Kd Ke Kf Kj Kk Kn Ko Kp Kq Ks Kx Ky Kz Lh Li Lu Lw Ly Lz Ma Mb Mc Md Mf Mg Mh Mi Mj Mk Ml Mn Mp Mr Mu Mv Mw Mx My Mz Na Nc Nf Nh Ni Nj Nk Nl Nm Nn Nq Ns Nt Nu Nv Nw Nx Ny Oe Of Og Oh Oi Ok Om On Or Ou Ow Oy Oz Pa Pb Pc Pd Pg Pi Pj Pk Po Pz Qb Qc Qd Qh Qm Qt Qv Ra Rb Sr St Tn Tv Ug Uh Ul Ur Us Uv Vt Wm Tj) Ng(aD aE aF aG aH aI aJ aK aL aN aP aQ aR aS aU aV aX aY bB bC bE bH bI bL bM bP bQ bR bS bU bV bW bX bZ cA cB cC cE cF cG cH cJ cM cN cO cQ cR cS cU cV cW cX cY cZ dA dB dC dG dH dI dK dL dN eC eF Ez Fn Fy gL gP Ha Hc Ib Ic Iz Jd Je Jf Ju Jv Ky Kz pF Qg Ql Qn Qu Qw Qx Qy Qz Ra Rb Rc Rf Rg Rj Rm Ss To Tr Tt Tv Tz Ua Ub Uc Ud Ue Uf Ug Um Un Uo Up Ut Vo Vp Tj) Qd(Fr Hq Hr Hu Hv Hw Hx Ih Ii Ij Il Io Ip Iq Ir It Iv Jg Jh Jk Jl Jm Jn Jp Jq Js Lh Li Lw Lx Ly Lz Ma Mb Mc Md Mf Mg Mh Mi Mj Mk Ml Mm Mn Mp Mr Mu Mv Mw Mx My Mz Na Nb Nf Nh Ni Nk Nm Nn No Nq Nr Ns Nt Nu Nv Nw Nx Of Og Oh Oi Ok On Oy Oz Pa Pb Pc Pd Pe Pf Pg Po Pz Qb Qc Wm) Mx(Fr Hq Hr Hu Hv Hw Hx Ih Ii Ij Il Io Ip Iq Ir It Iu Iv Jg Jh Jk Jl Jm Jn Jp Jq Js Lh Lw Ly Lz Ma Mb Mc Md Mf Mg Mh Mi Mj Mk Ml Mm Mn Mp Mr Mu Mv Mw My Mz Na Nb Nf Nh Ni Nk Nm Nn Nq Nr Ns Nt Nu Nv Nw Nx Ny Of Og Oh Oi Ok Om On Oz Pa Pb Pc Pd Pe Pf Pg Po Pz Qb Qc) Po(Bg Co Fr Hr Hu Hv Hw Hx Ih Ij Ik Il Io Ip Iq Ir It Iu Iv Jg Jh Jk Jl Jm Jn Jp Jq Js Lh Li Lw Lx Ly Lz Ma Mb Mc Md Mf Mh Mi Mj Mk Ml Mm Mn Mp Mr Mu Mv Mw Mz Na Nb Nf Nh Nk Nm Nn No Nq Nr Nt Nu Nv Nw Nx Ny Of Og Oh Oi Ok Om On Oz Pa Pc Pd Pe Pf Pg Pz Qb Qc) Qb(Fr Hr Hu Hv Hw Hx Ih Il Io Ip Iq Ir It Iu Iv Jg Jh Jk Jl Jm Jn Jp Jq Js Lh Li Lv Lw Lx Ly Lz Ma Mb Mc Md Mf Mg Mh Mi Mj Mk Ml Mm Mn Mp Mr Mt Mu Mv Mw Mz Na Nb Nf Nh Ni Nk Nm No Nq Nr Ns Nt Nu Nv Nw Nx Ny Of Og Oh Oi Ok On Oz Pa Pb Pc Pd Pe Pf Pg Pz Qc) Ir(Fr Hq Hr Hu Hv Hw Hx Ih Ii Il Io Ip Iq It Iu Iv Jg Jh Jk Jl Jm Jn Jp Jq Js Lh Lw Ly Lz Ma Mc Md Mf Mg Mh Mi Mj Mk Ml Mm Mn Mp Mr Mu Mv Mw My Mz Nb Nf Nh Ni Nk Nm Nn No Nq Nr Ns Nt Nu Nv Nw Nx Ny Of Og Oh Oi Ok Om On Oz Pa Pb Pc Pd Pe Pf Pg Pz Qc) Mf(Fr Hq Hr Hu Hv Hw Hx Ih Ii Ij Ik Il Io Ip Iq It Iu Iv Jg Jh Jk Jm Jn Jp Js Lh Lw Ly Lz Ma Mb Mc Md Mg Mh Mi Mj Mk Ml Mm Mn Mp Mr Mu Mv Mw Mz Na Nb Nf Nh Ni Nk Nm Nn Nq Nr Ns Nt Nu Nv Nx Ny Of Og Oh Oi Ok Om On Oz Pa Pb Pc Pd Pe Pf Pg Pz Qc) Hu(Bg Fr Hq Hr Hv Hw Hx Ih Ij Il Io Ip Iq It Iu Iv Iz Jg Jh Jk Jm Jn Jp Jq Js Lh Lw Ly Lz Ma Mb Mc Md Mf Mi Mj Mk Ml Mm Mn Mp Mr Mu Mv Mw Mz Na Nb Nf Nh Ni Nk Nm Nn Nq Nr Nt Nu Nv Nx Ny Of Og Oh Oi Ok Om On Oz Pa Pc Pd Pe Pf Pg Pz Qc Wm) Nt(Fr Hq Hr Hv Hw Hx Ih Ij Ik Il Io Ip Iq It Iu Iv Jg Jh Jk Jl Jm Jn Jp Jq Js Lh Lw Ly Lz Ma Mb Mc Md Mi Mj Mk Ml Mm Mn Mp Mr Mu Mv Mw Mz Na Nb Nf Nh Ni Nk Nm Nn Nq Nr Nu Nv Nw Nx Ny Of Og Oh Oi Ok Om On Oz Pa Pc Pd Pe Pf Pg Pz Qc) Ih(Fr Hq Hr Hv Hw Hx Il Io Ip Iq It Iv Jg Jh Jk Jl Jm Jn Jp Jq Js Lh Lw Ly Lz Ma Mb Mc Md Mg Mh Mi Mj Mk Ml Mm Mn Mp Mr Mu Mv Mw My Mz Na Nb Nf Nh Nk Nm Nq Nr Ns Nu Nv Nw Nx Of Og Oh Oi Ok Om On Pa Pb Pc Pd Pe Pf Pg Pz Qc) Pc(Fr Hq Hr Hv Hw Hx Ii Ij Il Io Ip Iq It Iv Jg Jh Jk Jl Jm Jn Jp Js Lh Lw Ly Lz Ma Mb Mc Md Mg Mh Mi Mj Mk Mm Mn Mp Mr Mu Mv Mw Mz Na Nb Nf Nh Nk Nm Nn Nq Nr Nu Nv Nw Nx Of Og Oh Oi Ok Om On Oz Pa Pb Pd Pe Pf Pg Pz Qc) Og(Fr Hq Hr Hv Hw Hx Ii Ij Il Io Ip Iq It Iu Jg Jh Jk Jp Js Jt Lw Ly Lz Ma Mb Mc Md Mg Mi Mj Mk Mm Mn Mp Mr Mu Mv Mw My Mz Na Nb Nf Ni Nk Nm Nn Nq Nr Ns Nu Nv Nx Ny Of Oh Oi Ok Om On Oy Oz Pa Pb Pd Pe Pf Pg Pz Qc) Pe(Bg Co Ct Fr Hr Hv Hx Ij Io Ip Iq It Iu Iv Jg Jh Jk Jl Jm Jn Jp Jq Js Lh Lw Ly Lz Ma Mc Md Mg Mh Mi Mj Ml Mm Mn Mp Mr Mu Mv Mw Mz Na Nb Nf Nk Nm Nn Nq Nr Nu Nv Nw Nx Ny Of Oh Oi Ok Om On Oz Pd Pf Pg Pz Qc Wm) Ii(Cs Fr Hq Hr Hv Hw Hx Ij Il In Io Ip Iq It Iu Jg Jh Jk Jp Js Jt Lw Ly Lz Ma Mb Mc Md Mg Mi Mj Mk Mm Mn Mp Mu Mv Mw My Na Nb Nf Nk Nm Nn Nq Nr Ns Nu Nv Nx Ny Oa Of Oh Oi Ok Om On Oy Oz Pa Pb Pd Pg Pz Qc Wm) Il(Fr Hq Hr Hv Hw Hx Ij Io Ip Iq It Iu Jg Jh Jk Jp Js Lh Lw Ly Lz Ma Mb Mc Md Mg Mi Mj Mk Mm Mn Mp Mu Mv Mw Mz Na Nb Nf Nh Ni Nk Nm Nn Nq Nr Ns Nu Nv Nx Ny Of Oh Oi Ok Om On Oz Pa Pb Pd Pf Pg Pz Qc) Of(Fr Hq Hr Hv Hw Hx Ij Io Ip Iq It Jg Jh Jk Jm Jp Js Jt Lw Ly Lz Ma Mb Mc Md Mg Mi Mj Mk Mm Mn Mp Mu Mv Mw My Mz Na Nb Nf Nk Nm Nn Nq Nr Ns Nu Nv Nx Ny Oh Oi Ok Om On Oy Oz Pa Pb Pd Pf Pg Pz Qc) Mc(Fr Hq Hr Hv Hw Hx Ij Io Ip Iq It Iu Jg Jh Jk Jm Jp Js Lh Lw Ly Lz Ma Md Mg Mi Mj Mk Mm Mn Mp Mu Mv Mw Mz Na Nb Nf Ni Nk Nm Nn Nq Nr Ns Nu Nv Nx Ny Oh Oi Ok Om On Oz Pa Pb Pd Pf Pg Pz Qc) Mz(Fr Hr Hv Hw Hx Ij Io Ip Iq It Iu Iv Jg Jh Jk Jn Jp Jq Js Lh Lw Ly Lz Ma Mg Mi Mj Mk Mm Mn Mp Mr Mu Mv Mw Na Nb Nf Ni Nk Nm Nn Nq Nr Nu Nv Nw Nx Ny Oh Oi Ok Om On Oz Pa Pd Pf Pg Pz Qc) Nb(Fr Hq Hr Hv Hw Hx Ij Io Ip Iq It Iu Jg Jh Jk Jm Jp Js Lh Lw Ly Lz Ma Mb Md Mg Mi Mj Mk Mm Mn Mp Mr Mu Mv Mw Na Nf Ni Nk Nm Nn Nq Nr Nu Nv Nx Ny Oh Oi Ok Om On Oz Pa Pd Pf Pg Pz Qc) Hq(Fr Hr Hv Hw Hx Ij Io Ip Iq It Iu Jg Jh Jk Jp Js Lw Ly Lz Ma Md Mg Mi Mj Mk Mm Mn Mp Mu Mv Mw My Na Nf Ni Nk Nm Nn Nq Nr Ns Nu Nv Nx Ny Oh Oi Ok Om On Oy Oz Pa Pb Pd Pg Pz Qc Wm) Pf(Ao De Ef Fr Hc Hr Hv Hw Hx Ij Ip Iq It Iu Jg Jh Jk Jm Jp Js Kj Lh Lw Ly Lz Ma Md Mi Mj Mk Mm Mn Mp Mr Mu Mv Mw Na Nf Nk Nm Nn Nq Nr Nu Nv Nw Nx Ny Oh Oi Ok Om On Oz Pd Pg Pz Qc) Mg(Fr Hr Hv Hw Hx Ij Io Ip Iq It Iu Jg Jh Jk Jp Js Jt Lw Ly Lz Ma Md Mi Mj Mk Mm Mn Mp Mu Mv Mw My Na Nf Nk Nm Nn Nq Nr Ns Nu Nv Nx Ny Oh Oi Ok Om On Oy Oz Pa Pb Pd Pg Pz Qc) Hw(Fr Hr Hv Hx Ij Io Ip Iq It Jg Jh Jk Jm Jp Js Lw Ly Lz Ma Md Mi Mj Mk Mm Mn Mp Mu Mv Mw My Na Nf Nh Ni Nk Nm Nn Nq Nr Ns Nu Nv Nx Ny Oh Oi Ok Om On Oz Pa Pb Pd Pg Pz Qc) Lh(Fr Hv Hx Ij Io Ip Iq It Iu Iv Jg Jh Jl Jm Jn Jp Jq Js Lw Ly Lz Ma Mh Mi Mj Mk Ml Mm Mn Mp Mr Mu Mv Na Nf Ni Nk Nm Nn Nq Nr Nu Nw Ny Oh Oi Ok

Figure 3 Continued

Om On Oz Pa Pd Pg Pz Qc) Mm(Ax Bg Cs Ct Fr Hr Hv In Io Ip It Iv Iz Jg Jm Jn Jq Js Jt Lw Mb Md Mh Mk Ml Mp Mr Mu Mv Mw My Nf Nh Ni Nn Nq Nr Ns Nu Nv Nx Oa Oh Ok On Oy Pa Pb Pd Pg Qc Uk Vt) Mr(Co Fr Hv Hx Ij Ip Iq It Iu Iv Jg Jh Jl Jn Jp Js Lw Ly Lz Ma Mh Mi Mj Mn Mp Mu Mv Mw Na Nf Nk Nm Nn Nq Nr Nu Nv Nw Nx Ny Oh Oi Ok Om On Oz Pa Pd Pg Pz Qc Wm) Pb(Fr Hr Hv Hx Ij Ip Iq It Iu Jg Jh Jk Jp Js Lw Ly Lz Ma Md Mi Mj Mk Mn Mp Mu Mv Mw Na Nf Nk Nm Nn Nq Nr Ns Nu Nv Nx Ny Oh Oi Ok Om On Oy Oz Pa Pd Pg Pz Qc Wm) Io(Fr Hr Hv Hx Ij Ip Iq It Iu Jg Jh Jk Jp Js Jt Lw Ly Lz Ma Md Mi Mj Mk Mn Mp Mu Mv Mw Na Nf Ni Nk Nm Nn Nq Nr Nu Nv Nx Ny Oh Oi Ok Om On Oz Pa Pd Pg Pz Qc) Jm(Ct Fr Hr Hv Hx Ij Ip Iq It Iu Jg Jh Jk Jp Js Lw Ly Lz Ma Md Mi Mj Mk Mn Mp Mu Mv Mw Na Nf Nk Nm Nn Nq Nr Nu Nv Nx Ny Oh Oi Ok Om On Oz Pa Pd Pg Pz Qc Wm) Ns(Fr Hr Hv Hx Ij Ip Iq It Iu Jg Jh Jk Jp Js Lw Ly Lz Ma Md Mi Mj Mk Mn Mp Mu Mv Mw Na Nf Nk Nm Nn Nq Nr Nu Nv Nx Ny Oh Oi Ok Om On Oz Pa Pd Pg Pz Qc) Mb(Fr Hr Hx Ij Ip Iq It Iu Jg Jh Jk Jp Js Lw Ly Lz Ma Md Mi Mj Mk Mn Mp Mu Mv Mw Na Nf Nh Nk Nm Nn Nq Nr Nu Nv Nx Ny Oh Oi Ok Om On Oz Pa Pd Pg Pz Qc) Jn(Fr Hv Hx Ij Ip Iq It Iu Iv Jg Jh Jk Jp Jq Lw Ly Lz Ma Mi Mj Mk Mn Mp Mu Mv Mw Na Nf Nk Nm Nn Nq Nr Nu Nv Nx Ny Oh Oi Ok Om On Oz Pa Pd Pg Pz Qc Wm) Mh(Fr Hr Hv Hx Ij Ip Iq It Iu Jg Jh Jk Jp Js Lw Ly Lz Ma Mi Mk Mn Mp Mu Mv Mw Na Nf Nk Nm Nn Nq Nr Nu Nv Nx Ny Oh Oi Ok Om On Oz Pa Pd Pg Pz Qc Wm) Nh(Fr Hr Hv Hx Ij Ip Iq It Iu Jg Jh Jk Jp Js Lw Ly Lz Ma Mi Mj Mk Mn Mp Mu Mv Mw Na Nf Nk Nm Nn Nq Nr Nu Nv Nx Ny Oh Oi Ok Om On Oz Pa Pd Pg Pz Qc) Ni(Fr Hr Hv Hx Ij Ip Iq It Iu Jg Jh Jk Jp Js Lw Ly Lz Ma Mi Mj Mk Mn Mp Mu Mv Mw Na Nf Nk Nm Nn Nq Nr Nu Nv Nx Ny Oh Oi Ok Om On Oz Pa Pd Pg Pz Qc) Ml(Fr Hv Hx Ij Ip Iq It Iu Jg Jh Jk Jp Js Lw Ly Lz Ma Mi Mj Mn Mp Mu Mv Mw Na Nf Nk Nm Nn Nq Nr Nu Nv Nx Ny Oh Oi Ok Om On Oz Pd Pg Pz Qc) Iv(Fr Hv Ij Ip Iq It Iu Jg Jh Jl Jp Js Lw Ly Lz Ma Mi Mj Mn Mp Mu Mv Mw Na Nf Nk Nm Nn Nq Nr Nu Nv Nx Ny Oh Oi Ok Om On Oz Pa Pd Pg Pz Qc) Jq(Fr Hv Hx Ij Ip Iq It Iu Jg Jh Jk Jp Js Lw Ly Lz Ma Mi Mj Mk Mn Mp Mu Mv Mw Na Nf Nk Nm Nn Nr Nu Nv Ny Oh Oi Ok On Oz Pa Pd Pg Pz Qc Wm) Md(Fr Hr Hv Hx Ij In Ip It Jg Jk Js Jt Lw Ly Lz Ma Mi Mk Mn Mp Mu Mv Mw My Na Nf Nn Nq Nr Nu Nx Oh Oi Ok Om On Oy Oz Pa Pd Pg Pz Qc Wm) Jt(Bg Dc Fr Hr Hx Id Ij Ip Iq Iu Jh Jk Jp Lw Ly Lz Ma Mi Mj Mk Mn Mp Mu Mv Na Nf Nk Nm Nn Nq Nv Nx Ny Oi Om Oz Pa Pd Pg Pz Qc Vt Wm) Jo(aC Af Al An AO Ap Ar As BA Bb Bc BN Bo cI Co CP Cq Ct Cv Cx Db Dc Dd De Dg Di Dk dM Dp Fy Hc Iz Ke Kn Ko Kq Pi Rh) No(Ao Ap Bg Ct De Dg Dk Dl Ef Fr Hc Ij Iu Jg Jh Js Kj Kl Kr Lw Ly Mi Mn Mp Na Nf Nk Nm Nn Nu Oh Oi Ok Om Oz Pd Pz Qc Tj) My(Hr Hv Hx Ij Ip Iq It Iu Jk Jp Js Lw Ly Lz Ma Mi Mj Mk Mn Mp Na Nf Nk Nm Nq Nr Nu Nv Nx Ny Oi Om Oz Pa Pd Pg Pz Qc Uk) In(Ax Bg Cs Fr Hr Hx Ij Ip Iq Iu Jg Jh Jk Jp Lw Ly Lz Ma Mi Mj Mk Mn Mp Mv Na Nk Nm Nn Nv Nx Ny Oa Oi Om Oz Pa Pg Pz Qc) Nw(Bg Fr Hr Hx Ij Ip Iq It Iu Jg Jh Jp Js Lw Ly Lz Ma Mi Mj Mk Mn Mp Na Nf Nk Nm Nn Nr Nu Ny Oh Oi Ok Om On Oz Pd Pz Qc) Wm(aA aC Bg bN cP Ct dM Fp Hc Im Is Iz Jh Jk Jr Li Lv Lw Lx Ly Lz Me Mk Mq Mv Ne Nq Nx Ny Oe Oz Pg Pz Qa Qc Qe Vv) Oy(bA cl Cs Hr Hv Hx Ip Iq It Iu Jk Jp Js Lw Ly Lz Ma Mi Mj Mk Mn Na Nf Nk Nm Nq Nu Nv Nx Ny Oi Om Oz Pa Pz Qc Vt) Jl(Fr Ij Ip Iq It Iu Jg Jh Jp Js Lw Ly Lz Ma Mi Mn Mp Mv Na Nf Nk Nm Nn Nr Nu Ny Oh Oi Ok Om On Oz Pd Pg Pz Qc) Oe(Fr Hx Ij Ip Iq Iu Jh Jk Jp Lw Ly Lz Ma Mi Mj Mk Mn Mp Mv Na Nf Nk Nm Nn Nq Nv Nx Ny Oi Om Oz Pd Pz Qc) Oh(Hr Hv Hx Ip It Jg Jh Jk Js Li Lw Lz Ma Mj Mk Mu Mv Mw Na Nf Nm Nq Nr Nu Nv Nx Oi Ok On Pa Pd Pg Qc) Lv(Bg Fr Hx Ij Ip Iq Iu Jg Jp Js Lw Ly Lz Ma Mi Mn Mp Na Nf Nk Nm Nn Nr Ny Oi Ok Om On Oz Pd Pz Qc) Ik(Fr Hx Ij Ip Iq It Iu Jg Jp Lw Ly Lz Ma Mi Mj Mn Mp Na Nf Nk Nm Nn Nr Nu Ny Om On Oz Pa Pd Pz) It(Fr Hr Hv Hx Ip Iq Jg Jk Js Lw Ma Mk Mp Mu Mv Mw Na Nf Nq Nr Nu Nv Nx Oi Ok On Pa Pd Pg Qc) Hv(Hr Hx Ip Jg Jh Jk Js Mk Mp Mu Mv Mw Na Nf Nm Nq Nr Nu Nv Nx Ok On Pa Pd Pg Qc) Ok(Hr Hx Ip Jg Jh Jk Js Li Ma Mk Mp Mu Mv Mw Nm Nq Nr Nu Nv Nx Pa Pd Pg Qc) Jj(aC Af aO Ap Ax Ba Bb bN Bo cI Cs Ct De Dk Dp Ed Iz Jd Kr Qt Qy Rh Vt) Lx(Bg Co Ij Ip Iq Iu Jg Lw Ly Mi Mn Mp Na Nm Nn Nr Ny Om Oz Pd Pz Qc) Mw(Fr Hr Hx Ip Jg Jh Jk Js Ma Mk Mu Mv Nn Nq Nr Nu Nv Nx Pa Pd Pg) Bg(aA aC bA bN Im Is Jh Ji Jr Jy Ke Lj Mq Mt Ne Qe Ri Uk Ur) Li(Ij Ip Iu Jg Js Lw Ly Mi Mn Mp Na Nf Nn Nu Om Oz Pd Pz Qc) Nq(Fr Hr Ij Ip Jg Js Mp Mu Mv Nf Nr Nu On Pa Pd Pg Qc) Mt(Fr Ij Iu Jg Jp Ly Mi Mn Mp Na Nk Nn Nr Ny Om Pd) Mu(Fr Hr Jg Jh Jk Js Mk Mv Nn Nr Nu Nv Nx On Pa Pg) Ct(aA Ax bA bN Cs dM Im Ji Jr Lj Mq Oa Qa Rh Ri) Js(Hr Hx Ip Jg Jk Lz Mk Mv Nr Nu Nv Pa Pd) Lu(Fr Ij Iq Iu Jp Ly Mi Nm Nn Ny Om On) Oa(Af De Dg Dl Iz Kj Kl Kr Ks Ne Ri Uk) Pa(Fr Ip Jg Mk Nf Nr Nu On Pd Pg Qc) Iz(Im Is Ke Kr Lj Ne Ri Uk Vt) Co(bA Cs Im Is Ji Lj Mq Ne) Nu(Hr Ip Jk Lz Mk Nv Nx Oi) On(Hr Jh Jk Mk Mv Nv Nx Pg) Lj(Dg Dl Kj Kl Ks Ri Uk) Jk(Fr Ij Ip Jg Nr Pd) Hr(Ip Lw Nf Nr Pd) Cs(Dl Kj Kr Ne) Mv(Fr Jg Nn Nr) Qe(Ij Ip Ly Om) Ax(Dg Dl Kj) Mk(Jg Mp Nr) Hc(Jh Ke Uk) Jg(Jh Nv) Uk(AO) DeaA DkKe NrNv MpPg NcIj NeNy KjVt dMjO} Nw{Me(Fr Hq Hr Hu Hv Hw Hx Ih Ik Il Io Ip Iq Ir It Iu Iv Jg Jh Jk Jl Jm Jn Jo Jp Jq Jr Js Jt Lh Li Lu Lv Lw Ly Lz Ma Mb Mc Mf Mg Mh Mi Mj Mk Ml Mm Mn Mp Mr Mt Mu Mv Mx Mz Na Nb Ne Nf Nh Ni Nk Nn No Nq Nr Ns Nt Nu Nv Nx Ny Oe Of Og Oh Oi Ok Om On Oz Pa Pc Pd Pe Pf Pg Po Pz Qa Qb Qc Qd Qe) Im(Fr Hr Hu Hv Hw Hx Ih Ik Il Io Ip Iq Ir Is It Iu Iv Jg Jh Jl Jm Jn Jo Jp Jq Jr Js Jt Lh Li Lw Lx Ly Lz Ma Mb Mc Mf Mg Mh Mi Mj Mk Ml Mm Mn Mp Mr Mt Mu Mv Mw Mx Mz Na Nb Nc Ne Nf Nh Nk Nm Nn No Nq Nr Nt Nu Nv Nx Ny Of Oh Oi Ok Om On Oz Pa Pc Pd Pe Pf Pg Po Pz Qa Qb Qc Qd Qe) My(aA Fr Hq Hr Hu Hv Hw Hx Ih Ii Ij Il In Io Ip Ir It Jk Jl Jm Jn Jo Jp Jq Js Jt Li Lj Lw Lx Lz Mb Mc Md Mf Mh Mi Mj Mk Ml Mm Mn Mp Mr Mt Mu Mv Mw Mx Mz Na Nb Nc Ne Nf Ng Nh Ni Nl Nn No Nq Nr Ns Nt Oe Og Oi Om Oy Oz Pa Pb Pc Pd Pe Pf Pg Po Pz Qb Qc Qd Wm) Nj(Fr Hq Hr Hu Hv Hw Hx Ii Ik Il Io Ip Iq Ir It Iu Iv Jg Jh Jk Jl Jm Jn Jo Jp Jq Jr Js Jt Lh Li Lu Lv Lx Ly Lz Mc Mg Mh Mj Mk Ml Mm Mn Mr Mt Mu Mv Mw Mx Mz Na Nb Nc Nd Ne Nf Nh Nk Nl Nq Ns Nv Nx Ny Oe Of Og Oi Ok On Oz Pa Pc Pd Pe Pf Pg Po Pz Qb Qc Qd Qe) Ng(Fr Hq Hr Hu Hv Hw Hx Ih Ii Ij Il In Io Ip Iq Ir It Iu Iv Jh Jk Jl Jn Jo Jp Jq Js Jt Lj Lw Lz Mb Mc Md Mf Mg Mh Mi Mj Ml Mm Mn Mp Mr Mu Mv Mw Mx Mz Na Nb Nc Ne Nf Nh Ni Nm Nn No Nr Ns Nv Nx Oe Og Oh Om Oy Oz Pa Pb Pc Pd Pe Pf Pg Po Pz Qb Qc Qd) Nd(Fr Hq Hr Hu Hx Ih Ii Ij Ik Il Io Ip Iq Ir It Iu Jg Jh Jk Jm Jp Js Jt Lu Lw Lz Ma Mb Mc Mf Mg Mh Mi Mj Mk Ml Mm Mn Mt Mu Mv Mw Mx Mz Na Nb Nc Nf Nh Ni Nk Nl Nm Nn Nq Nr Ns Nt Nu Nv Nx Ny Of Og Oh Oi Om On Oz Pa Pc Pd Pg Po Pz Qb Qc Qd) Oy(Fr Hq Hr Hu Hv Hw Hx Ih Ii Ij Il In Io Ip Iq Ir It Jh Jk Jm Jn Jo Jp Jq Js Jt Lj Lw Lz Mb Mc Md Mf Mh Mi Mj Mk Ml Mm Mn Mp Mu Mv Mw Mx Mz Na Nb Nc Ne Nf Nh Ni Nn No Nr Ns Nt Nu Nv Oe Og Oh Ok Om Oz Pa Pb Pc Pd Pf Pg Po Pz Qb Qc Qd) Jj(Fr Hq Hr Hu Hx Ih Ii Ij In Io Iq Ir It Iu Jg Jh Jk Jo Jp Js Jt Lw Ly Lz Ma Mb Mg Mh Mi Mj Mk Ml Mm Mn Mp Mr Mu Mv Mw Mx Mz Na Nf Nk Nm Nn Nq Nr Ns Nu Nv Nx Ny Of Og Oh Oi Om On Oz Pa Pc Pd Pe Pf Pg Pz Qb Qc Qd Wm) Mq(aA Hq Hr Hu Hv Hw Hx Ih Ik Io Ir Is Iv Jg Jh Jk Jl Jm Jn Jq Jr Js Jt Li Lu Lv Lx Lz Mb Mc Mf Mg Mh Mj Mk Ml Mm Mr Mt Mu Mv Mz Nb Nc Ne Nh Ni Nl No Nq Nt Ny Oe Of Og Ok Pa Pc Pe Pf Pg Po Pz Qa Qe) Lj(Hq Hr Hu Hv Hw Hx Ih Ii Il Io Ip Ir Is Iv Jg Jh Jk Jl Jm Jn Jo Jq Jr Js Jt Lh Lx Lz Mb Mc Md Mf Mh Mj Mk Mm Mr Mt Mw Nb Nc Ne Nh Nk Nl Nq Nr Ns Nt Nv Og Oi Ok On Pa Pc Pe Pf Qa Qe) Is(aA Hq Hr Hu Hv Hw Hx Ih Ik Il Io Iv Jh Jl Jn Jo Jq Jr Jt Li Lu Lv Lx Mc Md Mj Mk Mt Mu Mv Mw Nc Ne Ni Nl No Nq Ns Nv Nx Oe Of Og Ok Pa Pf Pg Qa) aA(Hq Hu Hv Hx Ii Ik In Ip Jh Jk Jm Jo Jq Jr Jt Li Lu Lv Lw Lx Mb Mc Mf Mj Mk Mm Mt Mu Mv Mw Nc Ne Ni Nl Nq Ns Nv Oe Of Og Oh Pa Pb Pc Pf Pg Qa Qe) Lv(Hq Hu Hv Ii Ik In Io Iv Jk Jl Jm Jn Jo Jq Jr Lu Lx Mc Md Mt Mu Mw Nc Ne Ni Nl No Ns Nv Nx Oe Of Og Ok Pa Pb Pf Pg Qa Qe) Nl(Hq Hu Hv Hw Ii In Iv Jk Jl Jm Jn Jo Jq Jr Li Lu Lx Mc Md Mm Mt Mw Nb Nc Ni Nk No Ns Nv Nx Oe Og Ok Pa Pb Pc Pg Qa Qe) Qa(Hq Hr Hv Hw Hx Ih Ik Il Io It Jo Jq Jr Jt Lu Lx Mb Mc Mj Mk Mu Mv Mw Nc Ne Ni Nq Ns Nv Nx Ny Of Og Ok Pa Pb Pg Qb) Pb(Hv Hw Ii In Io Iv Jl Jn Jo Jq Jr Lh Li Lu Lx Mb Mc Md Mf Mh Ml Mr Mt Nb Nc Ne Nh Ni No Ns Oe Ok Pc Pe Pf Po Qe) Fp(Fr Ij Il Ip Iq Iu Jp Li Ma Mb Mf Mg Mi Ml Mn Mp Mx Mz Na Nf Nh Nn Nr Nt Nu Oh Om On Oz Pd Qc Qd) Md(Hv Hw Ii Ik In Iv Jl Jm Jo Jr Jt Lh Li Lu Lx Mt Nb Nc Ne Ni No Oe Ok Om Pe Pf Qe) Ii(Hv

Figure 3 Continued

Hw Ik Iv Jl Jm Jn Jo Jq Jr Jt Lh Li Lx Lx Mt Nc Ne No Ok Pe Po Qe) In(Hv Hw Iv Jl Jm Jn Jq Jr Li Lu Lx Mt Nb Nc Ne No Nt Oe Ok Pe Qe)
Ik(Hq Hu Hw Iv Jk Jn Jo Jq Jr Lx Mw No Ns Nv Oe Of Og Ok Pg Qe) Oe(Hq Hv Iv Jl Jn Jq Jr Li Lu Lx Mt Mw Nc Ne No Nt Ok Qe) Ok(Hq
Hr Hv Jk Jo Jr Jt Lu Lx Mt Mw Nc Ne Nv Nx) Lu(Hq Hv Jk Jr Lt Lx Mw Nc No Ns Nv Pg Qe) Mw(Iv Jg Jl Jn Jq Jr Lh Lx Mt On Qe) Jk(Iv Jl
Jr Lh Li Lx Mt Nc Ne On) Qe(Hq Hv Jo Mj Ni Ns Nv Og Pa) Lx(Hq Hv Iv Jn Jq Ni Ns Pa) Nc(Hv Jn Jq Ne Ni Nk Ns) Ne(Hv Jn Jq Jr Ni Ns)
Iv(Jo Jt Nb Nv Nx Ny) Li(hP Hq Hv Jo Ni Ns) Jr(Hv Ni Ns Nv) Jl(Ns Nv Pa) Jq(Nv Nx Om) Pe(Hq Mk) WmJi NsMt MuPc JnJs LhNv PaPf} Fp{aA(Fr Hq Hr Hu Hv Hw Hx Ih Ii Ij Ik Il Io Ip Ir It Iv Jg Jh Jk Jl Jm Jn Jo Jp Jr Jt Lh Li Lj Lu Lw Ly Lz Ma Mb Mc Md Me Mf Mg Mh Mi Mj Mk Ml Mn Mp Mr Mt Mu Mv Mw My Mz Na Nb Nc Nd Ne Nf Ng Nh Ni Nj Nk Nl Nm Nn No Nq Nr Ns Nt Nu Nv Nx Ny Oe Of Og Oh Oi Om On Oy Oz Pa Pc Pd Pe Pf Pg Po Pz Qa Qb Qc Qd Qe) Mm(Fr Hq Hr Hu Hv Hw Hx Ih Ii Ij Ik Il Io Ip Iq Ir It Iu Jg Jh Jk Jl Jm Jo Jp Js Jt Li Lj Lu Lw Lx Ly Lz Ma Mb Mc Md Me Mf Mg Mh Mi Mj Mk Ml Mn Mp Mq Mt Mu Mv Mw Mx My Mz Na Nb Nc Nd Ne Nf Nh Nj Nk Nl Nm Nn No Nq Nr Ns Nt Nu Nv Nx Oe Of Og Oh Oi Om On Oy Oz Pa Pc Pd Pe Pf Pg Po Pz Qa Qc Qd Qe) Jq(Fr Hq Hr Hu Hv Hw Hx Ih Ii Ik Il Io Ip Iq Ir It Iu Iv Jg Jk Jm Jn Jo Jp Jr Jt Lh Li Lj Lu Lv Lw Ly Lz Ma Mb Mc Me Mf Mh Mi Mj Mk Ml Mn Mp Mr Mu Mv Mw Mx My Mz Na Nb Nc Nd Ne Nf Ng Nh Ni Nj Nk Nl Nm Nn No Nq Nr Ns Nt Nv Nx Ny Oe Of Og Oh Oi Om On Oy Oz Pa Pb Pc Pd Pe Pf Pg Po Pz Qa Qc Qd Qe) Im(Fr Hr Hu Hv Hw Hx Ii Ik Il Io Ip Iq Ir It Iu Iv Jg Jh Jm Jo Jp Js Jt Li Lj Lu Lw Lx Ly Lz Ma Mb Mc Md Me Mf Mg Mh Mi Mj Mk Ml Mn Mp Mr Mt Mu Mv Mw Mx My Mz Na Nb Nc Nd Nf Nh Nj Nk Nl Nm Nn No Nq Nr Ns Nt Nu Nv Nx Ny Of Og Oh Oi Om On Oy Oz Pa Pb Pc Pd Pe Pf Pg Po Pz Qa Qb Qc Qd Qe) Is(Fr Hr Hu Hw Hx Ij Ik Il Io Ip Iq Ir It Iu Iv Jg Jh Jl Jm Jn Jp Jr Js Jt Lh Li Lj Lu Lw Ly Lz Ma Mb Mc Md Me Mf Mg Mh Mi Mk Ml Mn Mp Mr Mt Mu Mv Mw Mx My Mz Na Nb Nc Nf Nh Nj Nk Nl Nm Nn Nq Nr Nt Nu Nv Nx Ny Of Oh Oi Om On Oz Pa Pc Pd Pe Pf Pg Po Pz Qa Qb Qc Qd Qe) In(Hq Hu Hv Hw Ih Ii Ij Ik Il Ip Ir It Iu Jh Jm Jo Jp Js Jt Lj Lu Lw Lz Mc Me Mf Mh Mi Mn Mp Ms Mu Mv Mw Mx My Mz Na Nb Nc Nd Ne Nf Ng Nh Ni Nj Nk Nl Nm Nn Ns Nv Nx Ny Oe Og Oh Om Oy Oz Pa Pb Pc Pd Pf Pg Po Pz Qb Qc Qd) Ok(Fr Hx Ij Ik Il Io Ip Iq Ir It Iu Iv Jg Jh Jp Js Lh Li Lj Lw Ly Lz Ma Mb Mf Mg Mh Mi Mk Ml Mn Mp Mr Mu Mv Mw Mx Mz Na Nb Nf Nh Nk Nm Nn Nq Nr Nt Nu Nv Ny Of Oh Oi Om On Oz Pa Pd Pe Pf Pg Po Pz Qa Qb Qc Qd Qe) Mt(Fr Hq Hu Hv Hw Ih Ii Ip Ir Iv Jg Jk Jl Jn Jo Jp Jr Jt Lh Li Lu Lv Lw Lx Mc Md Me Mj Mn Mq Mr My Mz Nd Ne Ng Ni Nj Nk Nm No Nq Nr Ns Oe Og Oi On Oy Pb Pc Pe Pf Qa Qe) Lx(Hq Hv Hw Ih Ii Ir Iv Jg Jk Jl Jn Jo Jp Jr Jt Lh Li Lu Lv Lw Mc Md Me Mj Mq Mr My Mz Nc Nd Ne Nh Ni Nj Nk Nl No Ns Oe Og On Pa Pb Pc Pe Qa) Lv(Fr Hq Hv Ip Ir Iv Jg Jl Jm Jn Jo Jp Jr Lh Li Lj Lu Lw Me Mj Mn Mq Mr Ms Mw My Mz Nb Nc Nd Ne Ng Ni Nl Ns Oe On Oy Pb Pc Pe Pf Qa Qe) Mq(Fr Hq Hr Hv Hw Iv Jg Jl Jm Jn Jo Jp Jr Lh Li Lu Lw Mj Mn Mr Ms My Mz Nc Nd Ne Ng Ni Nj Nl Nn No Ns Oe Og On Oy Pb Pc Pe Pf Qa Qe) Lh(Hq Hr Hv Hw Hx Ii Jg Jk Jm Jn Jp Jr Li Lj Lw Md Mj Mk Mw My Mz Nb Nc Nd Ne Nh Ni Nj Nk Nl No Ns Nv Nx Ny Oe Of Og Pc Pg Qa Qe) Jl(Hq Hr Hv Hw Hx Ii Jg Jk Jn Jo Jp Jr Li Lu Lw Me Mj Mk Mn My Mz Nc Nd Ne Ng Ni Nj Nk Nl No Nr Ns Oe Og On Oy Pa Pb Pc Qa Qe) No(Hq Hv Hw Ih Ii Ik Io Ip Iv Jg Jk Jn Jo Jr Lu Lw Mc Me Mj Mr My Nc Ne Ng Nh Ni Nj Nk Nl Nq Nr Ns Oe On Oy Pb Pc Pe Qa) On(Hq Hr Hu Hv Ii Jn Jo Jr Lj Md Mc Mj Mk Mu Mv Mz Nb Nc Nd Ne Ni Nj Nk Nl Ns Nv Oe Of Og Pg Qa) Qa(Hq Hv Ih Ii It Jg Jk Jn Jo Mj Mr Ms Nd Ne Ng Ni Nk Oe Og Oy Pb Pc Qb) Ms(Fr Ip Iv Jn Jr Jt Li Lw Mn Mp Mr Mw Mz Nb Ni Nn Om Pc Pe Qe) Jg(Iv Jk Jn Jo Jr Md Me Mr Mu Mv Ne Ni Ns Oe Og Pb Pe) Jp(Hq Hv Iv Jn Lu Mc Nd Nc Ng Ni Nj Nl Ns Oe Oy Pb) Qe(Hq Jk Jn Ne Ng Ni Oe Pb) Fr(Jk My Nd Nj Oe Oy Pb) Mr(Jo Nd Ng Oy Pb Pc) Pb(Iv Jn Jr Li Pe) Li(Ng Ni Oe) Oy(Om Pc Pe) Wm(Ji Jj) Nl(Ne Nk) Iv(Jo Pc) MpNd NgOm JnJs} Jj{No(aA Fr Hq Hr Hu Hv Hw Hx Ih Ii Ij Il In Io Iq Ir It Iu Iv Iz Jh Jk Jn Jo Jp Jq Js Jt Lj Lw Ly Lz Ma Mb Mc Md Mg Mh Mi Mj Mk Ml Mm Mn Mp Mr Mu Mv Mw Mx My Mz Na Nb Nf Ng Ni Nk Nm Nn Nq Nr Ns Nu Nv Ny Oe Of Og Oh Oi Om On Oy Oz Pa Pb Pc Pd Pe Pf Pg Po Pz Qb Qc Qd) Mt(aA Fr Hq Hr Hu Hv Hw Hx Ih Ii Ij Il In Io Iq Ir It Iu Jg Jh Jk Jn Jo Jp Js Jt Lu Lw Ly Lz Ma Mb Mc Md Mf Mg Mh Mi Mj Mk Ml Mm Mn Mp Mu Mv Mw Mx My Mz Na Nb Nc Ne Nf Ng Nh Ni Nk Nm Nn Nq Nr Ns Nt Nu Nv Nx Ny Oe Of Og Oh Oi Om On Oy Oz Pa Pb Pc Pd Pg Pz Qb Qc Qd) Ok(Fr Hq Hr Hu Hv Hw Hx Ih Ii Ij In Io Ip Iq Ir It Iu Iv Jg Jh Jk Jn Jo Jp Jq Js Jt Lw Ly Lz Ma Mb Mc Md Mf Mg Mh Mi Mj Mk Ml Mm Mn Mp Mr Mu Mv Mw Mx My Mz Na Nf Ni Nk Nm Nn Nq Nr Ns Nt Nu Nv Nx Ny Oe Of Og Oh Oi Om On Oy Oz Pa Pb Pc Pd Pe Pf Pg Pz Qb Qc Qd) Lh(Fr Hq Hr Hu Hw Hx Ih Ii Ij In Io Iq Ir It Iu Iv Jg Jh Jk Jn Jo Jp Js Jt Lw Ly Lz Ma Mb Md Mf Mg Mh Mi Mj Mk Ml Mm Mn Mp Mr Mu Mv Mw Mx Mz Na Nf Nk Nm Nn Nq Nr Ns Nu Nv Nx Ny Of Og Oh Oi Om On Oz Pa Pc Pd Pe Pg Pz Qb Qc Qd Wm) Jl(Fr Hq Hu Hv Hw Hx Ih Ii Ij Il In Io Ip Ir It Iv Jk Jm Jn Jo Jp Jq Jr Jt Lu Lw Lz Mb Mc Mf Mg Mh Mk Ml Mm Mn Mr Mw My Mz Nb Nc Ne Nf Ng Nh Ni Nk Nm Nn Nq Nr Ns Nt Nu Nx Oe Og Oh Om On Oy Pa Pb Pc Pd Pe Pf Pg Pz Qb Qc Qd Wm) Qe(aA Fr Hq Hr Hw Hx Ih Ii Ij Io Iq Ir It Iu Jh Jk Jo Jp Js Jt Lw Ly Lz Ma Mb Md Mg Mh Mi Mj Mk Ml Mm Mn Mp Mu Mv Mw Mx My Na Nf Nk Nm Nn Nq Nr Ns Nu Nv Ny Of Og Oh Oi Om Oy Oz Pa Pd Pg Pz Qb Qc Qd Wm) Li(Fr Hq Hr Hu Hw Hx Ih Ii Ij Io Iq Iu Jh Jk Jo Jp Js Jt Lj Lw Ly Ma Mb Md Mf Mg Mh Mi Mj Mk Ml Mn Mp Mu Mv Mx My Na Nf Nk Nm Nn Nq Nr Ns Nu Nv Ny Oe Of Og Oh Oi Om Oy Oz Pa Pc Pd Pe Pf Pg Qb Qc Qd Wm) Lx(Fr Hq Hr Hu Hx Ih Ii Ij In Io Iq Iu Jh Jk Jp Js Lw Ly Lz Ma Mb Md Mg Mh Mi Mj Mk Ml Mm Mn Mp Mu Mv Mx My Na Nf Nk Nm Nn Nq Nr Ns Nu Nv Ny Oe Of Og Oh Oi Om Oy Oz Pc Pd Pf Pg Po Qb Qc Qd Wm) Ik(Hq Hu Hv Hw Hx Ih Ii Ij Il In Io Iq It Iu Jk Jo Lu Lw Lz Ma Mb Mc Me Mf Mg Mh Mi Mj Ml Mp Ms Mu Mx My Na Nb Nc Nd Ne Nf Ng Nh Ni Nj Nk Nl Nm Nr Ns Nt Nu Nx Ny Of Og Om Oy Oz Pa Pc Pd Pg Qc) Po(aA Hq Hu Hv Hw Ij Il In Ip Ir It Iv Jg Jn Jp Jq Jr Jt Lj Lu Mc Me Mf Mm Mn Mr Ms Mw My Mz Nb Nc Ne Ng Nh Ni Nm Nn Nr Ns Nt Nx Oh Om On Oy Pa Pb Pc Pd Pe Pf Pz Qb Qd) Lj(aA Fr Hu Hv Hw Ii Ij Il In Ir It Iu Iv Jh Jm Jn Jo Jp Jr Jt Lu Lw Lz Mc Mf Mg Mm Mn Mr Ms Mu Mw Mz Nb Nc Ne Nh Ni Nm Nv Nx Oh Om Pb Pc Pd Pe Pf Pg Pz Qb Qd Wm) Mq(aA Fr Hu Ih Ii Ij Il In It Iv Jn Jp Jr Js Jt Lu Lw Me Mf Mg Ml Mm Mn Mp Mr Ms Nb Ne Ng Nh Nm Nn Nr Ns Nu Nv Nx Ny Of Oh Om Pb Pc Pd Pe Pg Qb Qc Wm) Jg(aA Hw Il Ip Ir It Iv Jm Jn Jq Jr Lu Mf Mh Mr Ms Mw Mx My Mz Nb Nc Ne Nh Ni Nj Nr Ns Nt Nx Oe On Oy Pb Pe Pf Qb) Lv(aA Fr Ij Il Ip Ir Jn Jp Jr Mm Mr Mw Mz Nc Nd Nh Nj Nl Nm Nn Nr Nt Nv Nx Oh Om On Pf Pz Qb Qd) On(Hv Ip Iv Jm Jq Jr Lu Mb Mc Mf Mh Mw Nb Nc Ne Ng Nh Ni Nt Oe Oy Pb Pf) Nl(Fr Ij Jm Jn Jp Jq Jr Mn Mr Mw Mz Nk Nm Nn Nt Nv Nx Om Pf Pz Qb Qd) Nd(Fr Ij Ip Iv Jm Jp Jq Jt Mr Mw Mz Nv Om Pe Pf Pz Qb Qd) Nt(Fr Ij Ip Ir Jm Jn Jq Jr Me Mn Ms Mw Mz Nc Nj Pf Qb) Nj(Fr Ij Ip Jm Jp Jr Mw Mz Nv Om Pf Pz Qb Qd) Qa(aA Ij Jp Js Ma Mp Mv Nv Ny Of Oi Qc) Wm(Ih Is It Jq Mw Pe Qd) Ip(aA Jr Mc Mw Nc Ne Nh) Jm(Jq Jr Me Ne Nh) Dp(Im Oa Pf) Mc(Fr Nv Pz) Ne(Ij Jq Mz) Jr(Fr Pf Pz) Is(aA Bg) oE(Vq Vt) BaNg MsIj JqPf} Im{Ok(aA Hq Hr Hu Hv Hw Hx Ih Ik Il Io Iq Is Iu Jl Jn Jq Jr Li Lj Lu Lv Lx Mb Mc Md Me Mf Mg Mh Mj Ml Mm Mq Mt My Nb Nc Ne Nh Ni Nl No Nq Ns Of Og Oy Pb Pc Pf Qa) Lv(Hq Ii Il In Io Is Iv Jk Jl Jn Jo Jq Jr Lh Li Lj Lu Lx Me Mm Mq Mr Mt Mz Nb Ne Ni Nj Nl No Ns Oe Og Oy Pb Pc Pf Qa) Ng(aA Ba Hu Ik In Iv Jh Jl Jn Jp Jq Jr Ke Ko Lj Lu Lw Me Mr Ms Mu Mv Mz Nb Nd Ni Nj Nl No Nt Oe Om Pc Pe Pf Po Qa Qe) In(aA Ik Is Iv Jl Jn Jq Jr Lh Li Lj Lu Lx Me Mm Mr Ms Mt Mz Nc Nd Ne Ni Nl No Nt Oe On Pe Pf Qa Qe) aA(Hq Ih Ik Jq Jr Lh Li Lj Lu Lw Lx Mb Me Mf Ml Mm Mq Mt Nc Ne Ni Nj Nl No Nq Ns Og Oy Pb Pc Pf) Ms(Fr Iv Jg Jn Jq Jr Li Lj Lu Lw Me Ml Mm Mp Mq Mr Mz Nb Nd Ni Nj Nl Nt Oe Pc Pe Pf Po Qa Qe) Mq(Hq Hw Ii Is Jk Jn Jo Jq Jr Lh Li Lj Lu Lx Me Mm Mt Mz Nd Ni Nj Nl No Ns Oe Og Oy Pb) Nd(Fr Jg Jk Jn Jp Jq Jr Li Lj Lw Mi Mj Mp Mt Mz Nb Ne Ni Oe Og Pa Pc Pd Po Qa Qe) Nj(Fr Is Iv Jk Jl Jn Jp Jq Jr Lh Li Lj Lx Mm Mr Mt Mz Ni Nk On Pe) Lx(Hq Ii Is Iv Jk Jl Jn Jq Jr Lh Lu Me Mr Ni Nl Oe Oy Pb Pc) Oe(Is Iv Jl Lh Li Lj Lu Mm Mr Mt Ni Nl No Nt On Pe Qa Qe) Jk(Fr Iv Jg Jn Jr Ke Mr Mt Mz Nl No Nt Pe Pf Qe) Ni(Is Jl Lh Li Lj Mm Mr Mt Nc Nl No On Pe Pf) Lh(Hq Hr Hw Hx Il Jo Jt Lj Me My Nl Og Pb) Me(Is Jl Li Lj Mm Mt Nl No) Oy(Jg Jl

Figure 3 Continued

Li Mr Mt Pe Pf) Lu(Is Jl Li Lj Mm No) Lj(Is Jq Mm Mt On) No(Hq Ii Is Nl) Jl(Ii Mk Mt Og) Li(Hq Ii Jq Og) On(Ii Mw Og) WmJi Mtlv MyJg NcNk NeNl IsOg} Is{Ms(aA Fr Hq Hu Hv Hw Ih Ii Ik Il Io Ip Iq It Iu Iv Jh Jk Jl Jn Jo Jp Jq Jr Jt Lu Lw Mb Mc Mf Mh Ml Mn Mp Mr Mu Mw Mz Nb Nc Ne Ng Nh Nj Nk Nl Nn Ns Nt Nu Nx Oe Og Oh Om Oy Pa Pb Pc Pd Pe Pf Pg Po Qa Qe) In(Ik Il Iv Jg Jk Jl Jn Jq Jr Lh Lu Mh Mm Mr Mt Mz Nb Nc Ne Nh Ni Nl Nl Nt Oe Og On Oy Pe Pf Po Qa Qe) Lj(aA Hq Hv Hw Ih Ii Ik Io Jg Jk Jq Lh Lu Lv Lx Me Mj Mm Mq Mt Ne Ng Ni Nj Nl Oe Og Ok On Oy Pb) Lx(aA Hq Hv Ii Il Jl Jn Jo Jq Jr Lu Lv Me Mj Mq My Ne Ni Nj Nl Nq Ns Oe Og Ok Oy Pa Pb) No(Hq Hw Ii Ik Il Io Jk Jo Jt Lu Lv Me Mj Mq My Ne Ni Nj Nl Nq Ns Oe Og Ok Oy Pb) Nd(aA Fr Iv Jk Jl Jo Jp Jq Lh Li Lv Mq Mr Mt Ne Ng Oe Og On Pb Pe Pf Qa Qe) Ng(Fr Hu Ik Jh Jl Jp Lh Lu Lv Me Mm Nb Ni Nj Nl Nt Om Pc Pf Po Qe) Ok(Hq Hr Hv Hw Jt Lu Lv Md Me Mq Mt My Nc Ni Nj Nl Oe Of Og Oy Pb) Jk(Fr Jg Lh Lv Me Mq Mt Nj Nl Nt On Pf Qa Qe) Mq(Ii Jo Li Lv Mt Nj Nl Ns Oe Og Oy Pb) Lv(Jo Li Me Mt Og Oy Pb) Li(Ii Jo Me Ni Og Oy) Me(Mm Mt Og) Nl(Ne Ni Nk) Lh(Ii Jo Oy) My(Jg On) Oy(Mt Pf) MwJg NcNk NiNj IkOg} Ok{Ms(Fr Hq Hr Hu Hv Hw Hx Ih Ii Ij Ik Il Io Ip Iq Ir It Iu Iv Jg Jh Jk Jm Jn Jp Jq Js Lw Ly Lz Ma Mb Mc Md Mf Mg Mh Mi Mj Mk Ml Mm Mn Mp Mr Mu Mv Mw Mx My Mz Na Nb Ne Nf Nh Ni Nk Nm Nn Nq Nr Ns Nt Nu Nx Oe Of Og Oh Oi Om Oy Oz Pa Pb Pd Pe Pf Pg Po Pz Qb Qc Qd) Jo(aA In Ip Iv Jg Jm Jn Jq Jr Li Lj Lu Lx Mf Mh Ml Mr Mt Nb Nc Ne Ng Nh Ni Nl No Nt Oe On Pc Pe Pf Po Qe) Ng(aA Fr Hu In Iv Jh Jl Jm Jq Jr Lh Lj Lv Me Mu Mv Nb Nc Nd Ne Nj Nl No Nt Oe Pc Pf Po) Lj(aA Hr Hv Ii Ik Jg Jq Jt Lu Lv Lx Me Mq Mt Nc Ne Ni Nj Nl Oe Oy Pb Pc) Lx(aA Hq Hr Hv Ii Jk Jt Lu Lv Md Me Mq My Nj Nl Oe Oy Pa Pb) In(aA Ik Jl Jr Li Lu Lv Mh Mt Nb Nc Nd Ne Nl No Po Qe) Nd(aA Iv Jq Jr Lh Li Lv Mp Mq Mr Mt Pe Pf Qa Qe) Me(aA Jl Jr Li Lv Mt Nc Nj Nl No Qa) aA(Ik Jt Lv Mq Nj Nl Oe Pb) Qa(Hr Ii Jt Nj Oe Oy Pb) Mq(Ii Jt Nj Ns Oy Pb) No(Ik Jt Lv Nj Nl) Qe(Ii Jk Nj Oe) Oy(Jg Mt On Pf) Jl(Ii Jt Nj) My(Jg Mt) NjJr} Ji{Wm(bN cV Fr Hq Hr Hu Hw Ih Ij Ik Il Ip It Jg Jh Jl Jm Jn Jp Jq Jr Js Jt Lh Li Lu Lv Lw Lx Ly Lz Ma Mb Mc Me Mf Mg Mh Mi Mk Ml Mm Mn Mp Mq Mr Mt Mu Mv Mx Mz Na Nb Nc Nd Nf Nh Ni Nj Nk Nl Nm Nn No Nr Ns Nt Nu Oe Of Og OH Oi Om On Oz Pa Pc Pd Pe Pg Po Pz Qa Qb Qc Qd Qe Qx) Oh(Fr Il Iq It Jg Jp Lh Lw Lz Ma Mf Mn Mp Mx Mz Na Nf Nn Nr Nu On Oz Pd) Nf(Il Iq It Jp Lh Lw Lz Ma Mf Mn Mp Mx Na Nn Nr Nu On Oz Pd) Jg(Fr Iq It Jp Lh Lw Lz Ma Mf Mn Mp Mx Na Nn Nr Nu Oz Pd) Jp(Iq It Lh Lw Lz Ma Mf Mn Mp Mx Mz Na Nn Nr Nu Oz Pd) Lw(Fr Iq It Lh Lz Ma Mn Mp Mx Na Nn Nr Nu Oz Pd) Nn(Iq It Lh Lz Ma Mf Mn Mp Mx Na Nr Nu Pd) Ma(Iq It Lh Lz Mn Mp Mx Na Nr Nu Oz Pd) Mp(Il Iq It Lh Lz Mn Mx Na Nu On Pd) Pd(Iq It Lh Lz Mn Mx Na Nu) It(Iq Lz Mn Mx Nu Oz) Nu(Iq Lh Lz Mn) Lh(Mx Na Oz) Ms(Aj Ch) LzIq MxNa NgRh} No{Nd(Aj Fr Hq Hr Hu Hv Hw Hx Ih Ii Ij Ik Il Io Iq Ir It Iu Jh Jk Jm Jo Js Jt Li Lj Lu Lw Ly Lz Ma Mb Mc Md Me Mf Mg Mh Mi Mj Mk Ml Mn Mt Mu Mv Mw Mx My Mz Na Nb Nc Nf Nh Ni Nj Nk Nl Nm Nn Nq Nr Ns Nt Nu Nv Nx Ny Of Og Oh Oi Om Oy Oz Pa Pd Pf Pg Po Pz Qb Qc Qd) Nj(aA Hq Hv Ii Ik Io Ip Iv Jg Jk Jl Jn Jp Jq Jr Lh Li Lj Lu Lx Mc Me Mj Mm Mt Nb Ne Ng Nr Ns Oe On Oy Pb Pc Pf Qa Qe) Lv(aA Hq Ii Ik In Io Jk Jo Li Lj Lu Lx Md Me Mj Mm Mq Mt My Nc Ne Ng Nh Ni Nl Nq Ns Oe Oy Pb Qa) Ms(aA Ik In Ip Jg Jl Jq Jr Lh Lx Me Mq Mt Ne Nh Ni Nl Nx On Pc Qa Qe) In(Lx Me Mq Mt Nc Ne Nh Nl Qa Qe) Ng(Ba Ke Lh Lx Mq Mt On Qe Ri) Nl(Me Mq Ne Ni Nk) Wm(Mw Nv oE Oy) Ik(Jk Oe Pb) Mq(Ns Pb) Nc(Ni Nk) Jg(My Oy) Ri(Ch Iz) Ou(fN uM) AdAj QaJk OnOy} Lx{Ms(Hq Hv Ik In Ip Ir Jn Jr Jt Li Me Mf Ml Mm Mn Mw Mz Nb Nc Nd Ne Ng Nh Ni Nj Nl Nn Nt Nx Oe Om Oy Pa Pb Pc Pe Qa Qe) Nd(aA In Iv Jn Jp Jq Jr Lh Li Lj Lv Mm Mq Mr Mz Ng On Pb Pe Pf Qa Qe) Ng(aA Fr Ik In Iv Jh Jl Jn Jq Li Lv Me Mr Mt Nj Nl Nt Om Pe Qa Qe) aA(Hq Hv Ik In Jk Jq Lj Lv Mc Mq My Ni Nj Nl Nq Ns Oe Oy Pa Pb) Mq(Hq Hv Ii Jn Jo Jq Jr Lj Lv Me My Nj Nl Ns Oe Oy Pb) In(Ik Iv Jl Jn Jq Jr Lh Lv Me Mr Mt Nj Nl Pe Qa Qe) Jl(Ii Jk Jq Lv Me Mk My Ni Nj Oe Oy Pb) Lv(Hq Jn Jq Jr Lj Me Nj Oe Oy Pb) Oy(Ik Lh Mr Mt Pe Qa Qe Wm) Nj(Iv Jn Jq Jr Ni) Nl(Jq Ne Ni Nk) Pb(Iv Lh Mr Pe) My(Jg On) Jk(On Qa) MdJq IiLh} Ng{On(Fr Hu In Ip Jm Jp Jr Lh Lv Mb Mc Me Mk Mm Mw My Nc Ne Nh Ni Nj Nl Nt Nx Om Oy Pb Pf Po Pz) Li(aA Ik In Jh Jq Lh Lv Me Mm Mq Mt Ni Qa Qe) Pf(Ad Ba cO dJ dM Ke Ko Kq Pj Uh Ur Tj) Ba(Ke Pe Qa Qe Uh Ur Vt) Lh(aA Mq Ms Mt Qa Qe Wm) Ke(Dp eC Ne Rh Ri Wm) Qe(Fr Jq Mq Mt Om) Qa(Fr In Mq Om) Fr(Ik Mq) MqMt UcUr IkJp JhLj KovS} Li{In(aA Jl Jq Lv Me Mq Mt Nd Nj Nl Qa Qe) Ms(aA Jl Jq Lh Lv Mq Mt Ni On Qa Qe) Mq(aA Jo Jq Lv Nd Nj Ns Oy Pb) Nd(aA Iv Jl Jq Lh Lv Mm On) Lv(aA Jo Me Oy Pb) vS(cV dB jO Mz) Ni(Nc Nj Nl) Jk(Lh On Qa) jT(qH vA vW) nW(tR tS tU) Oy(Jg Lh) dB(qP sC) MdJq MyOn dEuM gPtR rBqD} Lj{Lv(aA In Jg Jl Jq Lh Lu Mm Mq Mt Nd On) Mq(aA In Jg Jq Mm Ms Mt Nd Nj Ns On) In(aA Ik Jg Jl Lh Mt Nj On Qa) Nd(aA Fr Jg Jl Jp Jq Mm Mp) Jg(aA Jq Me Ms Ni Nj Oy) On(Jk Me Mt My Ni Nj Oy) Mt(aA Jq Lh Me Ms) aA(Ik Jq Mm Nj) Lh(Ms Nj Pb) MeMm NiNj wPnW rBqC} Qa{In(Hu Ik Il Iv Jg Jk Jl Jn Jq Jr Lh Lv Me Mm Mr Ms Mt Nb Ne Ni Nl Nt Oe On Pe Pf) Nd(Jl Jp Jq Lh Lv Mm Mq Mr Ne On) Ms(Jg Jq Lh Lv Mq Mt On) Jk(Lh Lv Mq On Pf) Nk(Nc Nj Nl) My(Jg On) Ne(Nj Nl) Lh(Ii Oy) OnOy} Ms{Mt(aA Iv Jg Jl Jq Jr Lv Mq Mr Pe Qe) Lh(aA Jg Jl Jo Jr Lv Mq Nd On Qe Wm) On(Jr Lv Me Mq My Nd Nj Oy Qe) Qe(In Jg Jl Jq Lv Mq) WmKe JgJl} Oy{On(Hu Ij In Jm Jr Lv Mb Md Me Mq Nc Ne Nh Nj Nl Pf Po Qc Wm) Jg(aA Iv Jq Lv Me Mt Po Qe) Wm(Ke Pf Po) Pf(Ke Vt) MtLh} Ke{Wm(bN eC gP Hc Ib Jd Mw My Nv nW oE oH oN) Pf(Hq Jk) Cp(Ne Rh) nW(fN wD) DpKg HcRh} Qe{In(Ik Jq Me Mq Nd Nj Nl) Nd(Jl Jq Lh Mq Mr) Nl(Ne Nk) MyJg} Ad{Aj(aA aC BA Bc bN cE Dd dJ dM Pf)} My{On(Ik In Jg Jh Me Mq Mt Nj Wm) MqJg} Nd{Jl(In Jp Mm Mt) Lh(Mm Pb) MqJp} In{Mt(Jl Mq) WmPf NjJl} BaCtaC WmMdJq MzRbqD JgJkJl VtnWvS Unconstrained panels with 3 analytes, where 1.0E-7 >= 'model p-value' > 1.0E-8. Contains 20,082 panels of 35,857,239 total panels evaluated. : Et{Bg(Ad Af Al An AO Ap Ar As AW Ax Ba Bb Bc bF Bn BO cI Co Cp Cq Cs CT Cu Cv Cw Cx Db Dc DD De dF Dg Di Dk Dl dM Dp Ed Fa Fb Fp Fr Gl Gp Hb Hf Hq Hr Hv Hw Hx Ib Ic Id Ih Ii Ij Ik Il Io Ip It Iv Iz Je Jf Jg Jk Jl Jm Jn Jp Jq Js Kc Kd Kj Kk Kl Ko Kq Kr Ks Kx Lh Li Lu Lw Ly Lz Ma Mb Mc Md Me Mf Mg Mh Mi Mj Mk Ml Mn Mp Mr Ms Mu Mv Mw Mx My Mz Na Nb Nc Nd Nf Nh Ni Nj Nk Nl Nm Nn Nq Nr Ns Nt Nu Nv Nx Ny Oa Oe Of Og Oh Oi Ok Om On Or Ou Ow Oy Oz Pa Pb Pc Pd Pg Pj Pz Qa Qb Qc Qd Qh Qv Rh St Tv Ug Uh Us Uu Uv Vo Vt) Jo(aD aF aG aH aJ aK aL aM aN aQ aR aS aU AW aZ bC bF bG bH bI bJ bL bM bO bP bR bS bV bW bX cA cB cD cF cH cK cL cM cN cO cQ cR cS cT cU cV cW cY cZ dA dD dE dF dG dI dJ dK DL dN Ed Ef Ez Fa Fb Fn Fw Gl Gp Hb Hf Ib Ic Jd Je Jf Ju Jv Jy Kc Kf Ki Kj Kk Kl Kp Kr Ks Kx Kz Ld Or Ou Ow Ph Pj Pk Qh Qm Qn Qt Qu Qv Qw Qx Qy Qz Ra Rb Rf Ri Rj Rm Sr Ss St Tz Ua Ub Uc Ud Ue Uf Uh Uk Ul Un Up Ur Us Uv Vp Vv Tj) Ct(aC Ad Af An Ao Ap As Ba Bc Bn cI Co Cp Cq cT Cu Cv Cw Cx Dc De dF Dg Dk Dl Dp Ed Fb Fp Fr Hc Hf Hq Hu Hv Hw Id Ih Ii Ij Ik Il In Ir It Iv Iz Jl Jn Jq Js Jt Jy Kc Kd Kc Kj Kn Ko Kq Kr Lh Li Lu Lv Lw Lx Ly Lz Mc Md Me Mg Mh Mi Mj Mk Ml Mn Mr Ms Mt Mv Mw Mx My Mz Na Nb Nc Nd Ne Nf Ni Nj Nl Nm Nr Nw Ny Oe Om Ou Oy Oz Ph Pd Pg Po Qb Qc Qd Qe Qh Ra Sr St Uk Ul Us Vt) Wm(aJ aK aM aN AO aR aU aW aZ bA bB bF bH bI bL bO bS bV bX cC cD cH cI cM CO cQ cV cX cY dD dE dF dI DK dN Fr gP Hr Hv Hw Hx Ih Ij Ik Il Io Ip Iq Ir It Iu Iv JD Je Jg Jl Jp Js Kj Kl Kr Ks Lh Lu Ma Mb Mc Mf Mi Mj Ml Mn Mp Mt Mu Mx Mz Na Nb Nc Nd Nf Nh Ni Nj Nk Nl Nm Nn Nr Ns Nt Nu NW Oa oE Og OH Oi Ok Om On Pa Pc Pd pF Po Qb Qt Qx Uk Ur Us Tj Th) Ch(aD aE aF aG aH aI aJ aK aL aM aN aO aP aQ aR aS aU aV aX aY bB bC bE bG bI bL bM bP bQ bR bS bU bV bW bX bZ cA cB cE cF cG cH cJ cK cL cM cN cO cQ cR cS cU cV cW cX cY cZ dA dB dC dE dG dH dI dJ dK dL dN dR EF Ez Fn Fy GL gP Ha Ib Jd Je Jf Ki Kl Ld pF Ph Qg Ql Qn Qu Qw Qx Qy Qz Rc Rf Rg Rj Rm Ss To Tr Tt Tz Ua Ub Uc Ud Ue Uf Um Un Uo Up Ut Uu Vo Vp Vv) Iz(aA Ad Af An Ap As Ax BA Bc BN Bo cI Cp Cq Cs Cu Cv Cw Cx Db Dc De Dg Di Dl dM Dp Ed Fa Fb Fn Fp Fr Hb Hf Hw Ic Id Ij Il In Iv Jh Ji Jl Jm Jn Jq Jr Jt Jy Kc Kd Kj Kk Kl Kn Ko Kp Kq Ks Kx Lh Li Lv Lw Lx Ly Me Mg Mh Ml Mp Mq Mr Ms Mt Mv Mw Na Nb Ni Nj Nq Nr Nw Ny Om Or Ou Ow Oz

Figure 3 Continued

Pd Pe Pg Pi Po Qa Qc Qd Qe Qh Qt Qv Ra Rh Sr St Tn Tv Ug Uh Ul Un Ur Us Uv) Jj(Ad aH AL An Ar As Aw bA Bc bF bI bL Bn bO bQ bR bV cG cH cK cO CP Cq Cu Cv CW Cx Db Dc Dd Dg Di dJ Dl dM Ef Ez Fa Fb Fn Fw Gl Gp Hb Hf Ib Ic Id Je Jf Ju Jv Jy Kc Kd Ke Kf Ki Kj Kk Kl Kn Ko Kp Kq Ks Kx Kz Ld Or Ou Ow Pi Pk Qg Qh Ql Qm Qn Qu Qv Qw Qx Qz Ra Rb Rc Rg Ri Rj Rm Sr Ss St To Tv Tz Ua Ub Uc Ud Uc Uh Uk Ul Un Uo Up Ur Us Ut Uu Uv Vp Tj) Kg(aC aD aE aF aG aH al aJ aK aL aM aN aP aQ aR aS aU aV aW aX aY aZ bB bC bE bF bG bH bI bJ bL bM bO bP bQ bR bS bU bV bW bX bZ cA cB cC cD cE cF cG cH cJ cK cL cM cN cO cQ cR cS cT cU cV cW cX cY cZ dA dB dC dD dE dF dG dH dI dJ dL dN Dr eC Ef gP jD jO jP Ky Tn Tr Tt Vs Vu) Oa(Ad Al An AO Ap Ar As Aw Ax Bc BN BO cl Co Cp Cq Cs Cu Cv Cw Cx Db Dc Dd Di Dk dM Dp Ed Ef Ez Gl Gp Ha Hb Hc Hf Hv Ib Ih Ji Jk Jy Kc Kd Ke Kk Kp Ly Me Mg Mj Mn Ms Na Nh Nj Nm No Nv Oe Oi Ok On Ou Ow Oy Oz Pf Ph Qu Qv Rh Ss Tv Ua Ug Ur Us Uu Uv Vt Vv) Lj(aC Ad Af Al aM AN AO Ap Ar As AW Ax aZ BA Bb Bc bL BN BO bS bW cl cO CP Cq Cs cT Cu Cv Cw Cx Db Dc DD DE dH Di Dk dM Dp Ed Ef Gl GP Ha Hc Hf Ib Id Jd Jy Kc Kd Ke Kk Kp Ou Ow Ph Pj Qu Qv Rh Ss Tv Ua Ug Ur Us Uu vS Vt Vv Tj) Uk(Af Ap Ax Ba bN Co cP Cs Cu Cv Dc De Dg Dk Dl Dp Ed Gl Hq Hu Ib Id Ii Il Im In Is Jd Je Ji Jk Jm jO Jq Jr Jt Kc Kd Ke Kj Kl Kn Kp Kr Kx Lw Lx Me Mk Ml Mq Ms Mv Mw Ne No Or Ou Oy Oz Pe Pf Pi Qa Qe Qh Qt Qu Qv Qy Ra Rh Ri Sr Tv Ua Ul Us Vt Vv) Aj(aD aE aF aG aH al aJ aK aL aN aP aQ aR aS aU aV aX aY aZ bB bC bE bG bH bI bJ bM bP bQ bR bS bU bW bX bZ cA cB cC cD cE cF cG cH cJ cL cN cQ cR cS cU cV cW cX cY cZ dA dB dC dD dE dG dH dI dK dL dN eF gP gW jD jP Tr Tt Vo Vq Vu Vv) Hc(aA Ad Af An As Ax bA Bc Bo cl Cp Cq Cs Cu Cw Dc De Dg Dl dM Dp Ed Fa Hu Id Ij Im In Is Iv Ji Jm Jq Jr Jt Jy Kd Kj Kk Kl Kn Ko Kq Kr Ks Lh Lv Lw Lx Ly Me Mg Ml Mm Mq Mr Ms Ne Ni Nw Ny Om Ou Oz Pe Pi Qa Qe Qv Ra Rh Ri Ug Un Ur Us Vt) Cs(aA aC Ad Af AO Ap BN Cq Cw Cx De Dg dH Dk Gp Ha Hf Hq Hr Hu Hv Hw Ib Ih Im Is jD Ji Jk Jm Jq Jr Js Kl Ks Lv Ly Ma Mc Md Mc Mg Mj Mk Mn Mq Ms Mv My Na Nd Nh Ni Nj Nk Nm No Nq Nv Nx Oe Of Oi Ok On Oz Pa Pf Rh Ri Ur Us Tj) Mm(aC Ad Af An Ao Ap As Aw Ba Bb Bc Bn Bo cl Co Cq Cu Cv Cw Cx Dc De Dg Di Dk Dl dM Ed Ef Hx Ib Id Ij Iq Iu Jh Jk Jp Kd Ke Kj Kk Kl Kp Kr Ks Kx Ly Lz Ma Mi Mj Mn Na Nk Nm Ny Oi Om Oz Pz Qu Qv Rh Ri Sr Tv Ua Ug Ur Us Vv) Kj(Ad Af An AO As Bc Bn cl Co cP Cq Cu Cv Cw Dc De Dk Dp Ed Hf Hq Id Ij Il Im In Is Ji Jm jO Jq Jr Kd Ke Kf Kk Kn Ko Kp Kq Kr Ks Li Lw Lx Ly Me Mk Ml Mq Mr Ms My Ne Nr Oy Pe Pi Qa Qd Qe Qh Rh Ri Sr Tv Ul Un Us) Ao(aA aC Ax bA bN Bo cl Dg Dl dM Ed Fa Hu Id Ii Im In Is Jh Ji Jm Jq Jr Jt Jy Ke Kl Kr Ks Li Lv Lx Me Mg Mh Ml Mq Mr Ms Mt Nb Nd Nc Nw Oe Oy Pe Po Qa Qe Qv Rh Ri Ug Ur Us Vt) Co(aA aC Ax bN Bo cl cT Cu Dg Dl dM Ed Fa Fp Hu Id Ii Ij In Jh Jl Jm Jq Jr Jt Jy Ke Kl Kr Li Lv Lz Me Mg Mh Ml Ms Nb Nd Nw Oe Oy Pd Pg Qa Qc Qd Qe Qv Rh Ri Ug Ur Us Vt) Iu(Fr Hr Hv Hw Hx Ih Ij Ip Iq It Jg Jh Jk Jp Js Lw Ly Lz Ma Md Mi Mj Mk Mn Mp Mu Mv Mw Na Nf Nk Nm Nn Nq Nr Nu Nv Nx Ny Of Oh Oi Ok Om On Oz Pa Pc Pd Pg Pz Qc Qd) Ny(Fr Hr Hv Hx Ih Ij Ip Iq It Jg Jh Jk Jp Js Lw Ly Lz Ma Md Mi Mj Mk Mn Mp Mu Mv Mw Na Nf Nk Nm Nn Nq Nr Nu Nv Nx Oh Oi Ok Om On Oz Pa Pc Pd Pg Pz Qc Qd) Om(Fr Hr Hv Hx Ij Ip Iq It Jg Jh Jk Jp Js Ke Lw Ly Lz Ma Mi Mj Mk Mn Mp Mu Mv Mw Na Nf Nk Nm Nn Nq Nr Nu Nv Nx Oh Oi Ok On Oz Pa Pd Pg Pz Qb Qc Qd) Oz(cl Fr Hr Hv Hx Ih Ij Ip Iq It Jg Jh Jk Jp Js Lw Ly Lz Ma Mi Mj Mk Mn Mp Mu Mv Mw Na Nf Nk Nm Nn Nq Nr Nu Nv Nx Oh Oi Ok On Pa Pd Pg Pz Qc Vt) No(aC Ad Af Al An aO Ar As Aw Ax Ba Bb BN Bo bS cl Cp Cq Cu Cv Cw Cx Dc Dd Di Gl Ha Hf Ib Jd Je Kc Ks Qt Qu Qy Rh Ri Ss Ua Ur Us Uu Vt Vv) Ly(Fr Hr Hv Hx Ij Ip Iq It Jg Jh Jk Jp Js Lw Lz Ma Mi Mj Mk Mn Mp Mu Mv Mw Na Nf Nk Nm Nn Nq Nr Nu Nv Nx Oh Oi Ok On Pa Pd Pg Pz Qc Vt) Nk(Fr Hr Hv Hx Ij Ip Iq It Jg Jh Jk Jp Js Lw Lz Ma Md Mi Mj Mk Mn Mp Mu Mv Mw Na Nf Nm Nn Nq Nr Nu Nv Nx Oh Oi Ok On Pa Pd Pg Pz Qc) Oy(aC Ad Af An aO Ap As Ax Bc BN Cp Cq cT Cu Cv Cw Cx Dc Dg Di Dl dM Dp Ed Fa Id Jy Kd Ke Kl Kn Kq Kr Or Ou Qh Qv Rh Ri Tv Un Ur) Ij(Fr Hr Hv Hx Ih Ip Iq Ir It Jg Jh Jp Js Lw Lz Ma Mi Mj Mk Mn Mp Mu Mv Mw Na Nf Nm Nn Nr Nu Nv Nx Oh Oi Ok On Pa Pd Pg Pz Qb Qc) Jp(Fr Hr Hv Hx Ip Iq It Jg Jh Jk Js Lw Lz Ma Md Mi Mj Mk Mn Mp Mu Mv Mw Na Nf Nm Nn Nq Nr Nu Nv Nx Oh Oi Ok On Pa Pd Pg Pz Qc) Mi(Fr Hr Hv Hx Ip Iq It Jg Jh Jk Js Lw Lz Ma Mj Mk Mn Mp Mu Mv Mw Na Nf Nm Nn Nq Nr Nu Nv Nx Oh Oi Ok On Pa Pd Pg Pz Qc) Mj(Fr Hr Hv Hx Ip Iq It Jg Jh Jk Js Lw Lz Ma Md Mk Mn Mp Mu Mv Mw Na Nf Nm Nn Nq Nr Nu Nv Nx Oi Ok On Pa Pd Pg Pz Qc) Mn(Fr Hr Hv Hx Ip Iq It Jg Jh Jk Js Lw Lz Ma Mk Mp Mu Mv Mw Na Nf Nm Nn Nq Nr Nu Nv Nx Oh Oi Ok On Pa Pd Pg Pz Qc) Iq(Fr Hr Hv Hx Ip Jg Jh Jk Js Lw Lz Ma Md Mk Mp Mu Mv Mw Na Nf Nm Nn Nq Nr Nu Nv Nx Oh Oi Ok On Pa Pd Pg Pz Qc) Pz(Fr Hr Hv Hx Ip It Jg Jh Jk Js Lw Lz Ma Mk Mp Mu Mv Mw Na Nf Nm Nn Nq Nr Nu Nv Nx Oh Oi Ok On Pa Pd Pg Pz Qc) Nn(Fr Hr Hv Hx Ih Ip It Jg Jh Jk Js Lw Lz Ma Mk Mp Mu Mv Mw Na Nf Nm Nq Nr Nu Nv Nx Oh Oi Ok On Pa Pd Pg Qc) Nm(Fr Hr Hv Hx Ip It Jg Jh Jk Js Lw Lz Ma Md Mk Mp Mu Mv Mw Na Nf Nq Nr Nu Nv Nx Oi On Pa Pd Pg Qc) Ax(aA aC Af Ap bN De Hq Ib Ii Ji Jk Kl Kr Ks Mc Me Mg Ms My Nd Ne Nv Oe Ok Rh Ri Ur Us Uu Vv) Na(Fr Hr Hx Ip Ir Jg Jh Jk Js Lw Lz Ma Mk Mp Mu Mv Mw Nf Nq Nr Nu Nv Nx Oi Ok On Pa Pd Pg Qc) Jt(aC Ad An aO As bA Bc bN cl CP Cq Cu Cv Cw De Dk dM Ed Kd Ke Kn Ko Kq Pi Sr Tv Un Us) Lw(Fr Hv Hx Ip Jg Jh Jk Js Lz Ma Mk Mp Mu Mv Mw Nf Nq Nr Nu Nv Nx Oi Ok On Pa Pd Pg Qc) Lz(Fr Hr Hv Hx Ip Jt Jg Jh Jk Js Ma Mk Mp Mu Mv Mw Nf Nq Nr Nv Nx Ok On Pa Pd Pg Qc) Oi(Fr Hr Hv Hx Ip Jg Jh Jk Js Ma Mk Mp Mu Mv Mw Nf Nq Nr Nv Nx Ok On Pa Pd Pg Qc) Pf(aC Af aO Ap Aw Ba Bb bL bN cO Cp Cw Dg Dk Dl Ed Ib Jd Kl Kr Qt Qu Ua Us Vv Tj) De(aC bA dM Ed Fa Id Im In Is Ji Jq Jr Kd Ke Kr Lx Me Mq Ms My Nd Pe Ur Vt) Ma(Fr Hr Hv Hx Ip Jg Jh Jk Js Mk Mp Mu Mv Nf Nq Nr Nu Nv Nx On Pa Pd Pg Qc) Jk(aC bA cl De dM Ed Hr Hx Jh Kd Ke Mk Mp Mv Nf Nq Nv Nx Pa Pg Qc Qh Vt) My(aC Af An bA Bc bN Bo cl Cu Dc Dg Dl dM Ed Jy Ke Kr Rh Ri Ur Vt) Fr(Hr Hv Hx Ip Jg Jh Js Mk Mp Nf Nr Nu Nv Nx Oh Ok On Pd Pg Qc) aC(aA Af aK aL aO aU BN bV cl cP cY Dk dM Hq Im In Is Ms Ne) Mp(Hr Hx Ip Jg Jh Js Mu Mv Mw Nf Nr Nu Nv Nx Oh On Pa Pd Qc) Dk(aA bA Im In Is Ji Jq Kq Lv Lx Ml Mq Ms Mt Nw Pe Ri Vt) Nf(Hx Ip Jh Js Mk Mu Mv Mw Nr Nu Nv Nx Ok On Pd Pg Qc) Hx(Hr Ip Jg Jh Mk Mu Mv Nq Nr Nu Nv Nx On Pa Pd Pg Qc) Qe(Hr Ip Jg Jh Js Mk Mu Mv Mw Nr Nu Nv Nx On Pd Pg) Ji(Af Ap Aw Bb BN cl Cp Cw Dd Dg Dl Ib Kr Rh Ut) Ms(Af aO Ap bN cl Dg Dl dM Ed Ib Ke Kl Qu Ur Vt) Ng(dR fP gW hB iA iZ kQ nW oE oF oH oK Vq Vu Vv) Jh(Hr Ip It Js Md Mk Mv Nq Nr Nu Nv Nx Pa Pd Pg) Ke(Aw Cp Hq Ib Ii Jd Kr Mw Nb Nc Nv Rh Ut) Vt(bN Ed Hq Ib Ii In Kr Ne Ok Qv Rh Ri Ur Us) cI(aA aO bN cH cP Hq Ii In Me Mg Ml Mv Nd Ne) Is(Ad Al aN aO Ap bN Cp Cq Dd Dg Dl Ua) Kr(Ed Hq Ib Id In Lx Mg mM Ne Qa Qu Ur) Nx(Hr Ip Jg Js Mk Mv Nq Nr Nv Pa Pd Pg) bN(aA aO bV cP dM Hq Ii In Mg Ml Ne) Ed(Gl Hq Ii In Ne Rh Ri Ur Us Tj) Pd(Ip Jg Mk Mu Mv Nr Nu Nv On Pg) Dg(aA Hq Im In Nd Ne Qa Qe Rh) Pg(Hr Ip Jg Js Mk Mv Nr Nu Nv) aA(Af Ap Aw Bn Cp Cw Cx Dl) Ip(Jg Mk Mu Mv Nr Nv On) aO(bA bV dF dM Lx Mt Ur) Ap(Im In Mq Ne Qe Ur) Rh(In Kl Ks Mg Qu Vv) Nv(Hr Md Mk Mv Nq Pa) Dl(Hq Im Nd Qa Qe) Id(Af Cp Ii In Ne) Kd(Cp Ib Ii In Ne) On(Jg Js Nr Nu Ok) dM(gW hA jD Nd Ne) Mv(Hr Mk Nu Pa) bA(Ba Hq Ii Nd) Hr(Jg Mk Pa) Im(Ef Kl Ks) jD(cB Fb iZ) Cu(Ii In) Nr(Jg Nu) DcIi TjLx ThMh FaHq NqMk NuJg MtbF hBjO] Nw[Li(fN Fr hO Hr Hu Hw Hx Ih Ik Il Io Ip Iq Ir It Iu Iv Jg Jh Jl Jm Jn Jp Jq Jr Js Jt Lh Lj Lw Lx Ly Lz Ma Mh Mc Mf Mg Mh Mi Mj Mk Ml Mm Mn Mp Mr Mt Mu Mv Mw Mx Mz Na Nb Nc Ne Nf Nh Nk Nm Nn No Nq Nr Nt Nu Nv Nx Ny Of Og Oh Oi Ok Om On Oz Pa Pc Pd Pe Pf Pg Po Pz Qa Qb QC QD Qe wQ) Jn(aA Fr hO Hq Hr Hu Hv Hw Hx Ih Ij Il Io Ip Iq Ir It Iu Iv Jg Jh Jk Jl Jm Jo Jp Jq Jr Jt Lh Lu Lw Ly Lz Ma Mb Mc Mf Mg Mh Mi Mj Mk Ml Mm Mn Mp Mr Mt Mu Mv Mx Mz Na Nb Nf Nh Ni Nk Nm Nn No Nq Nr Ns Nt Nu Nv Nx Ny Of Og Oh Oi Ok Om On Oz Pa Pc Pd Pe Pf Pg Po Pz Qa Qh Qc Qd Qe) Mt(Fr Hq Hr Hu Hv Hw Hx Ih Ik Il Io Ip Iq Ir It Iu Iv Jg Jh Jl Jm Jo Jp Jq Jr Js Jt Lh Lu Lw Lx Ly Lz Ma Mb Mc Mf Mg Mh Mi Mj Mk Ml Mm Mn Mp Mr Mu Mv Mx Mz Na Nb Nc Ne Nf Nh Ni Nk Nm Nn No Nq Nr Nt Nu Nv Nx Ny Of Og Oh Oi Om On Oz Pa Pc Pd Pe Pf Pg Po Pz Qa Qb Qc Qd Qe) Ns(Fr Hq Hr Hu Hv Hw Hx Ih Ii Ij Il In Io Ip Iq Ir It Iu Iv Jg Jh Jk Jm Jo Jp Jq Js Jt Lh Lw Ly Lz Ma Mb Mc Md Mf Mg

Figure 3 Continued

My Mz Na Nb Nf Nh Nk Nm Nn Nr Nt Nu Nv Nx Ny Of Oh Oi Om On Oz Pa Pd Pe Pg Po Pz Qa Qb Qc Qd Qe) Ms(Hq Hr Hu Hv Hw Hx Ih Ii
Ij Ik Il Io Ip Iq Ir It Iu Jh Jk Jm Jo Jp Js Jt Ly Lz Ma Mb Mc Md Mf Mg Mh Mi Mj Mk Mn Mu Mv Mw Mx My Na Nc Ne Nf Nh Nk Nm Nn Nq
Nr Ns Nu Nv Nx Ny Of Og Oh Oi Om Oy Oz Pa Pb Pd Pg Pz Qb Qc Qd) Ni(Fr Hq Hr Hu Hv Hw Ih Ii Ik Il Io Ip Ir It Iu Iv Jg Jh Jk Jn Jo Jp Jq
Jr Js Jt Lu Lw Lz Mb Mc Md Me Mf Mg Mh Mi Mj Ml Mn Mp Mu Mw Mx My Mz Nb Ne Nh Nn Nq Ns Nt Nu Nx Of Og Oh Oi Om Oy Oz
Pa Pb Pc Pd Pg Po Qa Qc Qd Qe) Lv(Fr Hr Hu Hv Hw Hx Ih Ij Ik Ip Iq Ir It Iu Jg Jh Jm Jp Js Jt Lw Ly Lz Ma Mb Mc Md Mf Mg Mh Mi Mj
Mk Ml Mn Mp Mu Mv Mw Mx My Na Nc Nf Nh Nk Nm Nn Nq Nr Nt Nu Nv Nx Ny Of Oh Oi Om On Oz Pa Pc Pd Pg Po Pz Qb Qc Qd Qe)
Nd(Hq Hr Hu Hv Hw Hx Ih Ii Ij Ik Il Io Ip Iq Ir It Iu Jh Jm Jo Js Jt Lu Ly Lz Ma Mb Mc Md Me Mf Mg Mh Mk Ml Mn Mu Mv Mw Mx My Na
Nc Nf Nh Nj Nk Nl Nm Nn Nq Nr Ns Nt Nu Nv Nx Ny Of Oh Oi Om Oy Oz Pb Pg Pz Qb Qc Qd) Is(Fr Hq Hr Hu Hv Hw Hx Ih Ii Ik Il Io Ip Iq
Ir It Iu Iv Jg Jh Jm Jn Jo Jp Jq Jr Js Jt Lw Mb Mc Md Mf Mg Mh Mj Mk Ml Mm Mr Mw My Mz Nb Nc Ne Nh Nk Nl Nq Ns Nt Nu Nx Of Oi
On Oy Pb Pc Pd Pe Pf Po Qa Qb Qe) Nj(Hq Hr Hu Hv Hw Ih Ii Ij Ik Il Io Ip Ir Iu Jg Jh Jo Js Jt Lu Lw Mc Me Mf Mg Mh Mi Mj Ml Mn Mp Mu
Mw Mx My Na Nb Nc Ne Nf Nh Nl Nn Ns Nt Nx Oe Of Og Oi Om Oy Oz Pa Pb Pc Pd Pf Pg Po Qa Qd Qe) Me(Fr Hq Hr Hw Ih Ii Ik Il Io Ip Iq
Iu Iv Jg Jk Jn Jo Jp Jq Jr Lu Lw Mb Mc Mf Mh Mi Ml Mn Mp Mr Mx My Mz Nb Nc Ne Nh Nn Ns Nt Nu Nx Oe Og Om On Oy Oz Pa Pb Pc
Pd Pe Pf Pg Po Qa Qe) Oe(Fr Hq Hu Hv Hw Ih Ik Il Io Ip Ir Jg Jk Jn Jo Jp Jq Jr Js Jt Lw Mb Mc Mf Mh Mi Mj Ml Mn Mp Mu Mw Mx My Mz
Na Nb Nc Ne Nf Nh Nn Ns Nu Nx Og Oh Om Oy Oz Pa Pb Pc Pd Pf Pg Po Qd) In(Fr Hq Hu Hv Hw Ij Il Io Ip Iq Ir Jg Jk Jo Jp Js Jt Lw Mb Mc
Mf Mh Mi Mj Ml Mn Mp Mu Mw Mx My Na Nb Nf Nh Nm Nn Ns Nu Nx Of Og Oh Om Oy Oz Pa Pb Pc Pd Pg Po Qd Vt Wm) Lj(Fr Hq Hu
Hv Hw Ih Ii Ik Il Io Ip Iq Ir Iv Jg Jh Jk Jn Jo Jp Jr Lw Mb Mc Mf Mh Mj Ml Mp Mr Mu My Mz Nb Nc Ne Nh Nk Nl Nn Ns Nt Og Om Oy Pa Pb
Pc Pe Pf Qa Qe) Ok(Fr Ij Ip Ir It Iv Jg Jh Jm Jp Js Lw Ly Lz Ma Mi Mk Mn Mp Mr Mu Mv Mw Mx Mz Na Nf Nk Nm Nn Nr Nt Nu Nv Nx Ny
Oh Oi Om On Oz Pa Pd Pe Pg Po Pz Qb Qc Qd Qe) Iv(Fr Hq Hr Hv Hw Hx Ih Ii Ik Il Io Ip Iq It Iu Jg Jn Jo Jq Jr Jt Lu Lw Mb Mc Mf Mh Mj
Mk Ml Mm My Mz Nb Nc Ne Nh Nk Nl Ns Nt Of Og Oy Pb Pc Pf Qa Qe) Mr(Hq Hr Hv Hw Hx Ih Ii Ik Il Io Iq Iu Jg Jn Jo Jq Jr Jt Lu Lw Mb
Mc Mf Mh Mj Mk Ml Mm My Mz Nb Nc Ne Nh Nk Nl Nq Nr Ns Nt Of Og Pa Pb Pc Pf Qa Qe) Pe(Hq Hr Hv Hw Hx Ih Ii Ik Il Io Iq Iu Jg Jn Jo
Jq Jr Jt Lu Lw Mc Mf Mh Mj Mk Ml Mm My Mz Nb Nc Ne Nh Nk Nl Nr Ns Nt Of Og Pa Pb Pc Pf Qa Qe) Nl(Fr Hq Hv Hw Ih Ii Il Io Ip Ir Iu
Jg Jn Jo Jp Jq Jr Js Jt Lu Lw Mc Mh Mi Ml Mm Mn Mp Mz Nb Nc Nf Nh Ns Og On Oy Pa Pb Pc Pf Po Qa Qe) Lu(Fr Hq Hv Hw Ii Il Io Ip Ir Jg
Jk Jn Jo Jp Jq Jr Js Jt Lw Mf Mh Ml Mn My Mz Nb Nc Ne Nh Ns Nt Nx Og On Oy Pa Pb Pc Pf Qa Qe) Jn(Fr Hq Hr Hw Ih Ii Ik Il Io Iq Jg Jo Jr
Js Jt Lw Mb Md Mf Mh Ml Mm My Nb Nc Ne Nh Ns Nt Og On Oy Pa Pb Pc Pf Qa Qe) Jq(Aj Fr Hq Hr Hw Ih Ii Ik Il Io Jg Jk Jo Jr Jt Mb Md
Mf Mh Ml Mm Nb Nc Ne Nh Ns Nt Og Om On Oy Pb Pc Pf Qa Qe Wm) Jr(Fr Hq Hr Hw Ih Ii Ik Il Io Iq Jg Jn Jt Lw Mb Md Mf Ml Mm My
Mz Nb Nc Ne Nh Ns Nt Og On Oy Pb Pc Pf Qa Qe) Mm(Hq Hu Hv Hw Ii Ik Il Io Ir Jk Jo Js Jt Mb Mf Mg Mh Ml My Mz Nb Nc Ne Nh Ns Nt
Og On Oy Pb Pf Qa Qe) Jk(Hu Hv Hw Ik Ip Ir Jp Js Jt Lw Mf Mi Ml Mp Mu Mw Nb Nc Ne Nh Nn Nu Nv Nx Og Om Pa Pc Pd Pg Po Qd)
On(Hq Hr Hu Hw Ik Il Io Jo Jt Lw Mb Md Mf Mg Mh Mk Ml Mu Mv Mz Nc Ne Nh Nq Ns Nv Of Pb Pf Qa) Mz(Hq Hw Ih Ii Ik Il Io Jo Jt Lw
Mb Md Mf My Nb Nc Ne Nh Ns Nt Og Oy Pb Pc Pf Qa Qe) Pf(Aj Ch Co Ct Hq Hw Ih Ii Il Io Jo Lw Ml My Nc Ne Nh Ns Nt Og Pa Pb Pc Qa)
Qa(Hq Hw Ih Ii Il Io It Jo Mb Mj Ml My Ne Ns Og Oy Pb Pc Qb) Ke(Aj Bg Ch Cp Ct De Dk Hc Hq Ib Ii Iz Jj Jo Kg Oy Ua Ut) Og(Fr Hu Ik Io
Ip Jg Lw Mf Ml Nb Nc Ne Nh Nt Om Pc Po Qe) Jj(aC Aj Ao Ax Bg Ch Co Cs Cv De dJ Hc Iz Ko Rh Vt) Ne(Fr Hq Jg Lw Nb Nc Nh Nk Ns Pb
Pc Qe) Ji(Aj Bg Ch Ct Iz Kg Rh Uk) Oy(Fr Mi Nb Pc Pd Po Qe) Aj(Ad Ba Ko Uh Vt) Ii(Fr Jg Nt Po Qe) Ns(Jg Lw Nh Pc) My(Fr Jh Nb Pc)
Hq(Fr Ml Po Qe) Ch(dF Uh We) Ik(Jo Pb) Il(Ml Qe) BaCt FrPb NtJo MwJg IhQe} Ok{aA(Fr Hq Hr Hu Hv Hw Hx Ih Ii Ij Il Io Ip Iq Ir Is It Iu
Iv Jg Jh Jk Jl Jm Jn Jp Jq Jr Js Lh Li Lu Lw Ly Lz Ma Mb Mc Md Mf Mg Mh Mi Mj Mk Ml Mm Mn Mp Mr Mt Mu Mv Mw Mx My Mz Na Nb
Nc Ne Nf Nh Ni Nk Nn No Nq Nr Ns Nt Nu Nv Nx Ny Of Og Oh Oi Om On Oy Oz Pa Pc Pd Pe Pf Pg Po Qa Qb Qc Qe) Lx(Fr Hu Hw Hx Ih Ij
Ik Il Io Ip Iq Ir It Iu Iv Jg Jh Jl Jm Jn Jp Jq Jr Js Lh Li Lw Ly Lz Ma Mb Mc Mf Mg Mh Mi Mj Mk Ml Mm Mn Mp Mr Mt Mu Mv Mw Mx Mz
Na Nb Nc Ne Nf Nh Ni Nk Nm Nn No Nq Nr Ns Nt Nu Nv Nx Ny Of Og Oh Oi Om On Oz Pa Pc Pd Pe Pf Pg Po Pz Qa Qb Qc Qd Qe) Lj(Fr Hq
Hu Hv Hx Ih Ij Il Io Ip Iq Ir It Iu Iv Jh Jk Jl Jm Jn Jp Jr Js Lh Li Lw Ly Lz Ma Mb Mc Md Mf Mg Mh Mi Mj Mk Ml Mm Mn Mp Mr Mu Mv
Mw Mx My Mz Na Nb Nf Nh Nk Nm Nn No Nq Nr Ns Nt Nu Nv Nx Ny Of Og Oh Oi Om On Oz Pa Pd Pe Pf Pg Po Pz Qa Qb Qc Qd Qe)
Is(Fr Hu Hx Ih Ij Ik Il Io Ip Iq Ir It Iu Iv Jg Jh Jl Jm Jn Jp Jq Jr Js Lh Li Lw Ly Lz Ma Mb Mc Mf Mg Mh Mi Mj Mk Ml Mm Mn Mp Mr Mu Mv
Mw Mx Mz Na Nb Nc Nf Nh Nk Nm Nn Nq Nr Ns Nt Nu Nv Nx Ny Oh Oi Om On Oz Pa Pc Pd Pe Pf Pg Po Pz Qa Qb Qc Qd Qe) Mq(Fr Hq
Hr Hu Hv Hw Hx Ih Ik Il Io Ip Ir It Iu Iv Jg Jh Jk Jl Jm Jn Jp Jq Jr Js Lh Li Lu Lv Lw Ly Lz Mb Mc Md Me Mf Mg Mh Mj Mk Ml Mm Mr Mt
Mw Mx My Mz Nb Nc Ne Nh Ni Nl Nn No Nq Nt Nv Nx Oe Of Og Oi On Pa Pc Pe Pf Pg Po Pz Qa Qd Qe) Nd(Fr Hq Hr Hu Hv Hw Hx Ih Ii Ij
Ik Il Io Ip Iq Ir It Iu Jg Jh Jk Jm Jn Jp Js Jt Lu Lw Ly Lz Mc Md Me Mg Mh Mi Mj Ml Mm Mn Mu Mw Mx My Mz Na Nb Nc Ne Nf Ni Nj Nl
Nm Nn Nr Ns Oe Of Og Oh Oi Om On Oy Oz Pa Pb Pc Pd Pg Po Pz Qb Qc Qd) Ng(Hq Hr Hv Hw Hx Ih Ii Ij Il Io Ip Iq Ir It Iu Jk Jn Jp Js Jt Lw
Ly Lz Ma Mb Mc Md Mf Mg Mh Mi Mj Mk Ml Mm Mn Mp Mr Mw Mx My Mz Na Nf Nh Ni Nk Nm Nn Nq Nr Ns Nu Nv Nx Ny Of Og Oh
Oi Om Oy Oz Pa Pb Pd Pe Pg Pz Qb Qc Qd Wm) Me(Fr Hq Hr Hu Hv Hw Hx Ih Ii Ik Il Io Ip Iq Ir It Iu Iv Jg Jh Jk Jm Jn Jp Jq Js Jt Lh Lu Lw
Mb Mc Md Mf Mg Mh Mj Ml Mm Mn Mp Mr Mu Mw Mx My Mz Nb Ne Nh Ni Nn Ns Nt Oe Of Og Oh On Oy Pa Pb Pc Pd Pe Pf Pg Po Qb
Qc Qd Qe) In(Fr Hq Hr Hu Hv Hw Hx Ih Ii Ij Il Io Ip Iq Ir It Iv Jg Jh Jk Jm Jn Jq Js Jt Lh Lw Mb Mc Md Mf Mg Mi Ml Mm Mp Mr Mu Mw
Mx My Mz Na Nf Nh Ni Nn Nq Nr Ns Nt Nu Nx Oe Of Og Oh Oi Om On Oy Oz Pa Pb Pc Pd Pe Pf Pg Qb Qd) Qa(Hq Hu Hv Hw Hx Ih Ik Il Io
Ip Iq It Iu Iv Jg Jh Jl Jm Jn Jq Jr Js Lh Li Lu Lv Lw Lz Mb Mc Md Mf Mg Mh Mj Mk Ml Mm Mn Mr Mt Mv Mw My Mz Nb Nc Ne Nh Ni Nk
Nl Nm No Nq Ns Nv Nx Of Og Oi Om On Pa Pc Pe Pf Pg Pz Qb Qd) Jo(Fr Hq Hr Hu Hv Hw Hx Ih Ii Ij Il Io Iq Ir It Iu Jh Jk Jp Js Jt Lw Ly Lz
Ma Mb Mc Md Mg Mi Mj Mk Mm Mn Mp Mu Mv Mw Mx My Mz Na Nf Nk Nm Nn Nq Nr Ns Nu Nv Nx Ny Of Og Oh Oi Om Oy Oz Pa Pb
Pd Pg Pz Qb Qc Qd) Nj(Fr Hq Hr Hu Hv Hw Ii Io Ip Iq Ir Iu Iv Jg Jh Jk Jm Jn Jp Jq Js Jt Lh Li Lu Lv Ly Mc Md Mg Mh Mk Ml Mm Mn Mr Mt
Mw Mx My Mz Nb Nc Ne Nf Ni Nk Nl Nn Ns Oe Of Og Oi On Oy Pa Pb Pe Pf Po Pz Qb Qc Qd) Lv(Hq Hr Hu Hv Hw Ih Ii Ik Io Ip Ir It Iu
Iv Jg Jh Jk Jl Jm Jn Jq Jr Jt Lh Li Lu Ly Mb Mc Md Mg Mh Mj Mk Ml Mm Mr Mt Mw Mx My Mz Nb Nc Ne Nh Ni Nl Nq Ns Nx Oe Of Og
Oy Pa Pb Pc Pe Pf Pg Po Qd Qe) Mt(Hq Hr Hu Hv Hw Ih Ii Ik Io Ip Iv Jh Jk Jl Jm Jn Jq Jr Jt Lh Li Lu Mb Mc Md Mg Mh Mj Mk Ml Mm Mr
Mw Mz Nb Nc Ne Nh Ni Nl No Nq Ns Nv Nx Oe Of Og Pa Pb Pc Pe Pf Po Qe) No(Aj Hq Hr Hv Hw Hx Ii Il Io Ip Jk Jl Jm Jn Jq Jr Li Lu Mb
Mc Md Mf Mj Ml Mw My Nb Nc Ne Nh Ni Nq Nr Ns Oe Of Og Oy Pa Pb Pc Pf Qe) Nl(Fr Hq Hr Hv Hw Ii Io Ip Iv Jg Jk Jl Jm Jn Jq Jr Jt Lh Li
Lu Mc Md Mg Mh Mr My Mz Nb Nc Ne Ni Nk Ns Oe Of Og On Oy Pb Pc Pe Pf Po Qe) Jr(Hq Hr Hv Hw Ii Ik Io Iv Jk Jl Jn Jq Jt Lh Li Lu Mc Md
Mg Mh Mj Mm Mr My Mz Nb Nc Ne Nh Ni Nq Ns Oe Of Og Oy Pb Pc Pe Pf Qe) Li(Hq Hr Hu Hv Hw Ii Ik Io Iv Jk Jl Jm Jn Jq Jt Lu Mb Mc
Md Mg Mj Mk Mm Mw My Mz Nc Ne Nh Ni Nq Ns Oe Of Og Oy Pa Pb Pc Qe) Jt(Hq Hr Hv Hw Hx Ik Io Jk Jn Jq Lu Mb Mc Md Mf Mg Mj
Mk My Nb Nc Ne Nh Ni Nq Ns Oe Of Og Oy Pa Pb Pc Pf Qe) Qe(Hq Hr Hv Hw Ih Ik Io Iv Jn Jq Jt Lu Mb Md Mj Ml My Nb Nc Ne Nh Ni Nq
Ns Of Og Oy Pa Pb Pc Pf) Lu(Hq Hr Hv Hw Ii Iv Jk Jm Jn Jq Jt Md Mg Mh Ml My Nb Nc Ne Nh Ns Oe Of Og Oy Pb Pc Pf Po) Nc(Hr Hv Ii Io
Iv Jk Jn Jq Jt Lh Mh Nb Ne Ni Nk Ns Oe Og Oy Pb Pc Pf) Jt(Ik Iv Jg Jn Jq Lh Mr Ne Nt Oe On Pb Pc Pe Pf Po) Jq(Ii Ik Mb Md Mh Ne Nh
Oe Og Om Oy Pb Pc Pf) Ne(Hr Ii Jk Jn Nb Ni Oe Og Oy Pb Pc) Ik(Hr Ii Jk Jn Mg My Oe Og Oy Pb) Oe(Iv Lh My Nb Nh Pb Pf Po Qb) Po(Hq

Ko Kq Mk Mq Mt Nd Vt) Ba(aC Ct dJ Id Vt) Uh(Id Tv) MqJg dFdJ} Nd{Lh(aA Fr Hr Hx Ii In Jg Jl Jn Jo Jp Jq Jr Lv Mn Mp Mq Mt Mw My Mz Ne Of Og On Pc Pf Po) Jl(aA Fr Ij Ip Jg Jn Jq Jr Lv Me Mk Mn Mp Mq Mw Mz Ne Ns Oe Og On Pb Pc Pf Po) On(aA In Iv Jk Jo Jp Jq Lv Me Mk Mq Mr Mt Mw Ne Og Pb Pe Pf) Mq(aA Fr Jg Jq Lv Mm Mp Mr Mt Mz Pf) Jp(Iv Jq Lv Mm Mp Mr Mt Pe Pf Po) Mm(aA Iv Jq Lv Mr Pe Pf) Mt(aA Iv Jq Lv Mr Pe Pf) aA(Jg Jq Lv Po) Jg(My Pf) PoIn LvPf} Mt{Mq(aA Iv Jl Jn Jq Jr Lh Lv Me Mr My Mz Ne Nj Nl Ns Oe Og Pb Pf) Lv(aA In Iv Jl Jn Jq Jr Lh Me Mm Mr Mz Ne Ns Oe Pb Pe Pf) In(aA Iv Jn Jq Jr Lh Me Mr Mz Nj Nt On Pe Pf Po) Jl(Ii Jk Jq Me Mk My Ne Ni Nj Ns Oe Pb) Lh(Ii Jk Jo Me My Nj Of Pb) aA(Ip Jq Me Mm Nj Ns Pb) Jq(Md Me Nj Pb Pf) Pb(Iv Mr Pe Pf) Me(Mm Pf) On(Jk Mw) ChWe MyJg NeNl} Mq{In(aA Ir Jg Jl Jn Jq Jr Lh Lv Mr Mz Nc Ne Nh Nj Nl Nt On Pf Po Qd) aA(Ik Ip Jg Jq Jr Lh Lv Mm Mz Nc Ne Nj Nl Ns Pb Pc Pf Po) Jq(Jg Lv Md Ne Nh Nj Nl Ns Pb Pf) Nj(Fr Jn Jp Jr Lh Mz On) Jg(Jo Mw Ns Og Pb) Lh(Ii Jo Pb) Ct(Ba Pf) Ns(Lv On) Nk(Nc Nl) LvJn NeNl PbPf tUnW} My{On(Fr Hq Hr Hu Hv Hw Ii Ij Io Ip Ir Jk Jm Jn Jo Jp Jq Jr Jt Lh Lu Lv Mb Mc Md Mf Mi Mk Ml Mm Mw Mz Nb Nc Ne Nh Ni Nl Ns Nt Nx Oe Og Om Pa Pb Pc Pf Po) Jg(aA Iv Jl Jq Jr Lh Lv Me Mr Ni Nl Pe Po Wm) Wm(Jp Jq Lh Ny Om Pf Uh) Jh(Jl Lh)} aA{Lv(Ik In Ip Jg Jq Jr Lh Me Mm Mz Nj Nl Pb Pf Po) Lh(Ii In Jk Jo Me Nj Nl Oe Pb) Nj(Jq Mm Mz Po) Ik(In Jq Mm) Po(In Pb) Nl(Ne Nk) Jg(Jk Mw) MdJq MeMm} Wm{Uh(bA bN bV dF dM hB nW oE oH Vv) In(bA dF Jq Mw Pe) Pf(Hq Jq Ne Pb) Vt(oE oH Ur) Jq(Nv Ny) TjPo ThSt HbdM UrbA qZuM} Pf{Vt(Hq In Jk Jo Kg Ur Tj) Ct(Ad Ba Jq Mk Ni) Hq(aC bN Kq) Bg(In Ur) Co(Ij Uh) Iz(Ko Mw) ChUh JkdM KgKo LhPb} In{JI(Ik Jq Jr Lh Lv Me Nl Po) Lh(Ik Jr Nj Nl) Po(Lv Nj Nl) Me(Jg On) NjOn IkJq VqoE} Ct{Ba(Ad As Bn Ch Cp Cq Cs Cu Cw Dc dF dJ dM) dF(aC Ad dH dJ) Ad(bA cT)} Lh{Jo(Ik Jg Jl Lv Nl) Nl(Ne Nk Pb) Jg(Jk Mw) Pb(Ik Nj) NcNk IiJl} oE{Vq(cV Ed Gz Ip Nk Or Qv) Vt(bN cH Ne Op)} nW{wD(jY Pj qD uX) wP(Ax Cs) MzuX IdvS VtqZ hBjI} Jl{Lv(Jk Mk) Ne(Nj Nl) Nk(Nc Nl) Jg(Mk Mw) MlHx} Uh{Tv(Ch Jo Kg) Ad(Jo Kg) ChTn IdKg} qZ{Vt(bL dB dE uM) ChUu DbHc KobR} Mz{Rb(qC vS tM) IlqC VvrW rAvS} Jg{Mw(Me Mr On) MdJq JkPe} vS{ChUc Luld UaKo dBhB} Nk{Po(Nc Nl) NlJq} aC{dM(Ad bR) ChdF} Bc{Wc(eQ pK)} Ne{NlOn VteC} Nj{Jp(Lv Ni)} DrllKg DuLdeC EdFiVq MdJqOn IbTruI OarBqC dMrCjO Unconstrained panels with 2 analytes, where 1.0E-8 >= 'model p-value' > 0. Contains 311 panels of 192,797 total panels evaluated. : Et(aA Aj Ch Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Kg Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ji(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Jj(Fp Ik Im Is Jg Jl Lh Li Lj Lx Mq Mt No Nw Ok On Po Qa Qe) Nw(aA Fp Im Is Lj Lv Md Me Mq Ms My Nd Ng Nj Nl Oy Pb Qa) Fp(aA Im In Is Jl Jq Lh Lv Lx Mm Mq Mt No Ok On Qa) No(Lv Nd Nj) Ms(Is Lx Ok) Im(aA Lv Ok) Is(In Lx) AdAj NgJg JoOk Unconstrained panels with 2 analytes, where 1.0E-7 >= 'model p-value' > 1.0E-8. Contains 249 panels of 192,797 total panels evaluated. : Nw(Hq Ilr Hu Hv Hw Hx Ii Ik Il In Io Ip Ir It Iv Jg Jh Jk Jl Jm Jn Jo Jq Jr Jt Lh Li Lu Lx Mb Mc Mf Mh Mk Ml Mm Mr Mt Mu Mv Mw Nb Nc Ne Nh Ni No Nq Ns Nt Nv Oe Of Og Ok Pa Pc Pe Pf Pg Po Pz Qd Qe) Fp(Fr Hw Ip Ir Iv Jg Jm Jn Jp Jr Jt Li Lu Lw Me Mn Mr Ms Mw Mz Nb Nc Ne Ng Nh Ni Nj Nk Nl Nm Nn Ns Nt Oe Og Om Oy Pb Pc Pe Pf Pz Qd Qe) Im(In Is Iv Jk Jl Jn Jq Jr Lh Li Lj Lu Lx Me Mm Mq Mr Ms Mt Mz Nd Ng Ni Nj Nl No Oe Og On Pc Pf Qa) Ok(aA In Is Jl Jr Li Lj Lu Lv Lx Me Mq Mt Nc Nd Ng Nj Nl No Qa Qe) Lx(aA In Iv Jl Jn Jq Lh Lv Me Mq Mr Nd Ng Nj Nl Qa) Is(Jk Li Lj Lv Me Mq Mt Nd Ng Ni Nj Nl No Oe Og) No(Aj Ik In Me Mq Ms Mt Ne Nl Qa Wm) Jj(Ij Ip Jm Lv Nl Nt Pf Qb Wm) Et(Bg Co Cs Ct Iz Kj Oa Uk) Li(aA In Jq Lv Me Mq Ng Ni) Lj(aA Jg Lh Lv Mq Mt On) Qa(In Jk Lv Mq Ms Nd) Ms(Lh Mt On Qc) On(My Ng Oy) NgKc Unconstrained panels with 2 analytes, where 1.0E-6 >= 'model p-value' > 1.0E-7. Contains 653 panels of 192,797 total panels evaluated. : Is(aA Ct Fr Hq Hr Hu Hv Hw Hx Ih Ii Ik Il Io Ip Iq Ir Iu Iv Jg Jl Jm Jn Jo Jp Jq Jr Jt Lh Lu Lw Mb Mc Md Mf Mh Mj Mk Ml Mm Mr Mx My Mz Nb Nc Ne Nh Nk Nq Ns Nt Nu Of Oi On Oy Pb Pc Pd Pe Pf Po Qa Qe) Ok(Fr Hq Hr Hu Hv Hw Hx Ih Ii Ij Ik Il Io Ip Ir It Iv Jg Jk Jm Jn Jq Js Jt Lh Lw Mb Mc Md Mf Mg Mh Ml Mm Mr Mu Mw Mx My Mz Nb Ne Nh Ni Nn Nq Nr Ns Nt Oe Of Og Oi On Oy Pa Pb Pc Pd Pe Pf Pg Po Qb Qd) Im(Fr Hq Hu Hv Hw Hx Ih Ii Ij Ik Il Io Ip Iq Ir Iu Jg Jo Jp Js Jt Lw Mb Mc Mf Mg Mh Mi Mj Ml Mn Mp Mu Mw Mx My Na Nb Nc Ne Nf Nh Nk Nm Nn Nq Ns Nt Nu Nx Of Oh Oi Om Oy Oz Pa Pb Pc Pd Pg Po Qd Qe) No(aA aC Bg bS Ch Ct eC Hc Hq Hu Hv Hw Ii Il Io Ip Ir Iv Iz Jg Jl Jn Jq Jr Kj Lh Li Lj Lu Lx Mb Mc Mf Ml Mm Mr My Nb Nc Ng Nh Ni Nq Ns Nt Nx OE On Oy Pb Pc Pe Pf Qe Rh Ua Ur Vt Tj) Fp(Hq Hr Hu Hv Hv Hx Ih Ii Ij Ik Il Io Iq It Iu Jh Jk Jo Js Lj Ly Lz Ma Mb Mc Md Mf Mg Mh Mi Mj Mk Ml Mp Mu Mv Mx My Na Nd Nf Nq Nr Nu Nv Nx Ny Of Oh Oi Oz Pa Pd Pg Po Qb Qc) Li(fN Hq Ik Iv Jk Jl Jn Jr Lh Lu Lx Mm Mr Ms Mt Mz Nc Nd Ne Nh Nj Nl Ns Nt Oe Og On Oy Pb Pe Qa Qe tR uP uU uV vQ vS wC wD wF wH wL wP wQ yD xA) Lx(Hq Hv Hw Ii Ik Ip Ir Jg Jk Jo Jp Jr Js Jt Lj Lu Lw Mb Mf Mh Ml Mm Mt Mx My Mz Nb Nc Ne Nh Ni Ns Nt Oe Og On Oy Pa Pb Pc Pe Pf Qd Qe) Qa(aA Hq Hv Hw Ih Ii Ik Il Iv Jg Jl Jn Jo Jq Jr Lh Lj Lu Mb Mc Mm Mr Mt Mz Nb Ne Ng Nh Ni Nj Nk Nl Ns Nt Oe Og On Oy Pb Pc Pe Pf Qb) Nw(Fr hO Ih Ij Iq Iu Jp Js Lw Ly Lz Ma Mg Mi Mj Mn Mp Mx Mz Na Nf Nk Nm Nn Nr Nu Nx Ny Oh Oi Om On Oz Pd Qb QC) Jj(aA Fr Ir Iv Jn Jp Jq Jr Js Jt Mr Mw Mz Nc Nd Ne Nh Nj Nm Nn Nr Nv Nx Oa Oh Om Pe Pz Qd Vt) Et(aC Af An AO Ap Ax Bb bN cI Dc De Dg Dk Dl dM Ed Hc Id Ke Kl Kr Rh Ur Us Vt) Ke(Aj Ao Bg Ch Co Cp De Dk eC Hc Hq Ib Iz Jk Kg Lj Ms Oa oE Oy Rh Uk Ut) Qe(aA In Jl Jn Jq Lh Lj Lv Me Mq Mt Nd Ng Ni Nj Nl Oe) Mt(aA In Iv Jl Jn Jq Jr Lh Lv Me Mq Mr Ng Pe Pf) Lj(Fr Ik In Iv Jl Jq Me Mm Nd Ni Nj Nl Om) Mq(aA In Jg Jq Lh Lv Nj Nl On Pf) Ji(Aj Bg bN Ch Ct Rh Uk Ur) Lh(aA Nd Ng Nj Nl Oy) Jl(In Lv Ms Nd) Pf(Aj Bg Ct Wm) Jg(Lv My Oy) aA(Jq Lv Po) Ba(Ct Ng) Nd(Jp On) Kq(Aj Ng) oE(Vq Vt) WmJq aCdM Unconstrained panels with 2 analytes, where 1.0E-5 >= 'model p-value' > 1.0E-6. Contains 1,419 panels of 192,797 total panels evaluated. : No(AD Af Al aM AN Ao Ap aQ Ar As aU Ax Ba BB Bc bL BN BO bR cA cH cK CO Cp Cq Cs Cu CV Cw Cx Dc DE dF Dg Di dJ Dk Dl dM Dp Ed Ef Ez Fa fN fP Fr Fw GP Ha Hb Hf hO hP Hr Hx Ib Ic Id Ih Ij Iq It Iu Jd Je Jh Jk Jm Jo Jp Js Jt Ju Jv Kc Kd Ke Kg Kk Kl Kn Ko Kp Kr Ks Kx Ky Ld Lw Ly Lz Ma Md Mg Mh Mi Mj Mk Mn Mp Mu Mv Mw Mx Mz Na Nf Nk Nm Nn Nr Nu Nv nW Ny Oa Of Og OH Oi oK Om oN Or Ou Ow Oz Pa Pd pF Pg Ph Pi Pj Pk Po Pz Qb QC QD Qg Qn Qt Qu Qv Qw Qx Qy Ri Sr Ss Tv Ub Uh Uk Ul uM Un Us Ut Uu Vp vS Vv Th tF) Et(AD aF aG aJ aK AL aM aN aQ AR As aU AW aZ BA Bc bF bH bI bL bM Bn BO bP bQ bR bS bV bW bX cA cB cD cE cF cG cH cK cL cN cO CP CQ cR cT CU CV CW CX cY Db DD dE dF dH Dl dJ Dp Ef Ez Fa Fb Fn Fw Gl Gp Hb Hf Ib Ic Jd Je Ju Jv Jy Kc Kd Kf Ki Kk Kn Ko Kp Kq Ks Kx Ky Kz oE Or Ou Ow Ph Pi Pk Qh Qm Qn Qt Qu Qv Qw Qx Qy Qz Ra Rb Rc Rf Ri Rj Sr Ss St To Tv Ua Ug Uh Ul Um Un Uo Up Ut Uu Uv Vo Vv Tj) Ji(aC Ad Af Al aM AN Ao Ap Ar As AW Ax aY BA Bb Bc bF bJ bL Bn BO bR bS bV cA cF cH cl cK Co Cp Cq CS cT Cu CV Cw Cx Db Dc Dd DE dF Dg Di dJ Dk Dl dM Dp eC Ed Ef Fa GP gW Ha Hc Hf Ib Id Iz Jd jO Ju Kg Kj Kk Ko Kp Kr IN

Figure 3 Continued

Oa oE qC Qg Qm Qt Qu Qv Qw Qx Qy Qz Rb Rf Rg Ri Sr Ss St Tn To Tr Tv Tz Ua Ub Uc Uf Ug Uh Ul Um Uo Up Us Ut Uv Vp vS Vt Tj) Li(Fr hP Hr Hu Hv Hw Hx Ih It Ij Il Io Ip Iq Ir It Iu Jg Jh Jm Jo Jp Js Jt Lj Lw Ly Lz Ma Mb Mc Md Mf Mg Mh Mi Mj Mk Ml Mn Mp Mu Mv Mw Mx My Na Nb Nf Nk Nm Nn Nq Nr Nu Nv Nx Ny Of Oh Oi Om Oz Pa Pc Pd Pf Pg Po Pz Qb QC Qd rS tO tS tU tV uM uR uT vO vP vT vU vV vW wB wE wG wJ wK yH yJ yK yL zA zG zH zI yE tM tL) Ke(Af As Aw Ax Ba Bb BN Bo Cq Cs Ct Dc Dd Dp Ed Ef fN Fp gP gW hO hP Hv Hx Ii Il Im In JD Je Jh Jj JM JO Jt Kj Kk Kr IM IN Lx Ly Md Mk Mq Mu Mv Mw My Nb Ne Nh Nv Nx Om Oz Pb PF Pg QA qC Qe Qt Qu Qv Qy Rb Ri Tn To Tr Tt Tv Ua Uh Ur Us Vt Wm Tj) Qe(Aj Fr Hq Hr Hu Hv Hw Ih Ii Ij Ik Il Io Ip Iq Ir Iv Jg Jk Jm Jo Jp Jr Js Jt Lu Lw Ma Mb Mc Mf Mh Mi Mj Ml Mm Mn Mr Mw Mx My Mz Na Nb Nc Ne Nh Nk Nq Ns Nt Nu Nx Of Og Oi Om On Oy Pa Pb Pc Pd Pe Pf Po Qa) Qa(Aj Ch Ct Fr Hr Hu Hx Ij Io Ip Iq Ir It Iu Jh Jm Jp Js Jt Lw Ly Lz Ma Mc Md Mf Mg Mh Mi Mj Mk Ml Mn Mp Mu Mv Mw Mx My Na Nc Nf Nm Nn Nq Nr Nu Nv Nx Ny Of Oh Oi Om Oz Pa Pd Pg Po Pz Qc Qd Uh Ur) Mt(Fr Hu Hv Hw Ih Ij Ik Il Io Ip Ir Jg Jk Jo Jp Js Jt Lu Lw Mb Mf Mh Mi Ml Mm Mn Mp Mw Mx My Mz Na Nb Nc Nd Ne Nf Nh Ni Nj Nl Nm Nn Ns Nt Nx Oe Og Om On Oy Pa Pb Pc Pd Pg Po Qb Qc Qd) Lx(Fr Hr Hu Hx Ih Ij Il Io Iq It Iu Jh Jm Ly Lz Ma Mc Md Mg Mi Mj Mk Mn Mp Mu Mv Mw Na Nf Nk Nm Nn Nq Nr Nu Nv Nx Ny Of Oh Oi Om Oz Pd Pg Po Pz Qb Qc Vt Wm Tj) Jj(Ad Ax BA Cs Cu Dp Fa Fy Hu Hv Hw Id Ih Ii Il It Jk Jo Ko Kp Kq Lu Lw Me Mf Mg Ml Mm Mn Mp Mu Mv Mx Nb Ng Ni Nu Ny oE Pc Pd Pg Pj Qc Qh Rm Sr St Uc Uh Un) Lj(dF Hu Hv Hw Ij Ip Ir Jh Jn Jo Jp Jr Jt Lu Lw Mf Mi Mn Mp Mr Ms Mu Mw Mz Nb Nc Ne Ng Nh Nn Ns Nt Nv Nx Oe Oy Pb Pc Pe Pf Po Pz qC Qd Uh Ur Wm) Mq(Aj Ct Fr fj Ik Ip Ir Iv Jl Jn Jp Jr Js Me Ml Mm Mn Mr Ms Mw Mz Nc Nd Ne Ng Nh Nn Ns Nt Nx Og Oh Om Pb Pc Pe Po Qd Vt) Is(Aj aN Ch eC iC Ij It Jh jK jQ Js Ly Lz Ma Mg Mi Mn Mp Mu Mv Mw Na Nf Nm Nn Nr Nv Nx Ny Oh Om Oz Pa Pg Pz Qb Qc Qd Ur) Lh(Hq Hr Hx Ii Ik In Ir Iv Jg Jk Jl Jn Jo Jp Jq Jr Lv Mb Me Mm My Mz Nb Nc Ne Nh Ni Nt Oe Of Og Pb Pf Po Qd) aA(aC Fr Ij Ik In Ip Ir Jg Jl Jn Jp Jr Lw Me Mf Ml Mm Ms Mw Mz Nc Nd Ne Nh Nj Nl Nr Nt Nx Om On Pc Pf Qd) Jl(Fr Ik Ir Jg Jk Jn Jp Jq Jr Mb Me Mf Mk Mm Mz Nb Nc Ne Ng Nh Ni Nj Nl Ns Nt Oe Og On Oy Pb Pf Po) Pf(aC bL bN bR bS cA Ch cL CO dH dJ dM Dr Iv Iz Jq Kg Lv Me Nd Nj Nl oE Oy Ua Uh Uk Ur Vt Tj) Lv(Fr In Ip Ir Iv Jn Jp Jq Jr Me Mm Mr Mw Mz Nb Nc Nd Ne Nh Nj Nl Nt Om On Pe Po Qd) Ok(Iq Iu Jh Jp Ly Lz Ma Mi Mj Mk Mn Mp Mv Na Nf Nk Nm Nu Nv Nx Ny Oh Om Oz Pz Qc) Im(aC Aj Ch Ct Hr It Jh Jm Ly Lz Ma Md Mk Mv Nr Nv Ny Pz Qb Qc Uh Uk Ur Vt Wm) Jg(Aj In Iv Jn Jq Jr Me Mr Ms Mw Nd Ne Ni Nj Nl Og Pc Po) On(Ii In Jk Jq Jr Me Mw Nc Ne Ni Nj Nl Ns Oe Og) aC(Ad Ax Ba Bc cE Cs Cu Cv Dc dF Dg Fr) Po(In Jq Me Ms Nd Ng Ni Nj Nl Pb Tj) Vt(bN eC In Mw Ne Ng Qv Rh Uk Ur) Jq(Fr Ik Mm Nd Ne Nh Nj Nl Nt) Uh(Aj Ax Ch Cs Id Ng Oa Tv Wm) Nw(fN hP oE qA qB qD Rh Wm) Fr(Jr Me Ms Nd Ng Nj Nl) qZ(aZ bL DB dE Ko Ou) Wm(bA dF dM oE Pe Ur) Aj(Ba Cu Ij Pe Uc) Ct(Ad bA dF Kq Pe) Ng(Ad Ko Om Tn Uf) Mm(Jr Me Nd Nl) Mz(jK qC vS) Nd(Iv Mr Pe) Id(eC qC vS) Jp(Me Nj Nl) dM(jO rC rY) Kq(Ch Iz) Ur(Ax Oa) Ntln MsOm bRfR hBjO nWuX Unconstrained panels with 2 analytes, where 1.0E-4 >= 'model p-value' > 1.0E-5. Contains 3,009 panels of 192,797 total panels evaluated. :
Ke(aA aC AD aE aF al aJ aK AL aM AN aO Ap aQ AR aS aU aW aY aZ bA bB BC bF bG bH bI bJ bL bM bO bP bQ bR bS bU bV bW bX bZ cA cB cC cD cE cF cG cH cI cJ cK cL cM cN cO cP cQ cR cS cT CU CV CW CX cY Db dD dE dF Dg dH Dl dJ dK DL dM dN dR eD eF eT EZ Fa Fb Fn fP Fr Fw FY GL Gp HA HB hC HF hG hL Hr Hu Hw hX iA iB IC Id IH IJ Ik IO IP Iq Ir Is It Iu Iv jE JF JG jH JJ jK JL Jn JP JQ JR Js jT JU JV JY Kc Kd Kf Ki Kl Kn Ko Kp KQ kR KS Kx Ky Kz Ld Lh Li lK IL IO Lu Lv Lw Lz Ma Mb Mc Me Mf Mg Mh Mi Mj Ml Mm Mn Mp Mr Mt Mx Mz Na Nc Nd Nf Ni Nj Nk Nl Nm Nn Nq Nr Ns Nt Nu NW NY Oe OF Og OH Oi OK ON Or Ou Ow Pa Pc Pd Pe Ph Pi Pj Pk Po pY Pz QB Qc QD Qg QH QI Qm Qn Qw Qx QZ Ra Rc Rf Rg Rj Rm rP rS sC sO Sr Ss St Tz Ub Uc Ud Ue Uf Ug Ul UM Un UO Up Uu UV Vo Vp vS VV vW wP yD tF) Pf(AD aF al aJ aK Al aM AN AO aQ Ar As aU aV aW AX aY aZ bA bB Bc bF bG bH bI bJ bM Bn bO bP bQ bU bV bW bZ cC cD cE cF cG cH cI cJ cK cM cN CP CQ cR CS cT CU CV CW cX cY cZ dA Dc dD DE dF dG DI DK dL dN Dp eC Ed EF Em Eq Ez Fa Fr Fy Gc Gd Gh GP Ha Hb Hc Hq Hw Ib Id Ij Ik In Ip Ir Jg Jn Jp Jr Jt Kd Kj Kk Kn Ko Kp Kq Kr Kx Ky Kz Lu Lw Mm Mn Mr Ms Mw Mx Mz Nb Nc Ne Ng Nh Ni Nt nW Nx Oa Og oH Om ON Op Or Ou Pb Pc Pe Ph Pi Pj Pk Po Qb Qd Qg Qm Qn Qt Qu Qv Qw Qy Ra Rf Rg Rh Ri Rt Sf Sh Sr St Tv Ul Um Un Up Us Vp Vu Vv Wb Wc We YI Zq Zx Ye) No(aE aF aG aH aI aJ aK aL aO aP aR aS aV AW aX aY aZ bA bC bE bF bG bH bI bJ bL bM bP bQ bU bV bW bX bZ cB cC cD cE cF cG cI cJ cL cM cN cP cQ cR cS cT cU cW cX cY cZ dA DB dC DD dG dH dl dK dN dR eF eT eZ Fb Fn FY GL gW hB hC hF hG hL hR hX iA iB iC iH iJ iO iP iZ jD jE Jf jI jK jO jQ jR jT jV Jy Kf Ki KQ kR kS Kz lK IL IN nY oF pY qA qB QH QI Qm qP qY Qz Ra Rb Rc Rf Rg Rj Rm rS rU rW sC St Tn To TR Tt tU Tz Uc Ud Ue Uf Ug Um UO Up Uv uY uZ vA Vo Vu vV wB wE wL wP wQ yD xA) Ji(aD aE aF aG aH aI aJ aK aL aO aP aQ aR aS aU aV aX aZ bB bC bE bG bH bI bM bP bQ bU bW bX bZ cB cC cD cE cG cJ cL cM cN cO cP cQ cR cU cW cX cY cZ dA dB dC dD dG dH dI dK dL dN dR cF Ex EZ Fb FN fP Fw Fy GL hA HB hC hF hG hO hP hX iA iB IC iH iJ iO iP jD JE JF jG jH jI jK jL jM jP jQ jR jT jU JV JY Kc Kd Kf Ki Kl Kn KQ kR KS Kx Ky Kz Ld lK lL lM lO nW nY oF oH oK oN Or Ou Ow pF Ph Pi Pj Pk qD Qh QI Qn qY Ra Rc Rj Rm Tt Uc Ud Un Uu Vo VV Wc yL Ti Th tF) Uh(aA Ad An Ao As bA Bc Bg BN bV Co Cq Ct Cu Cv Cw Dc De dM Dp eC Ed Fa Fp Fy Hc Hq Hv Hw Ij Il In Ir Is Iv Iz Jl Jn Jo Jq Jr Kd Kg Kj Kk Kn Ko Kp Kq Kr Lh Li Lw Ly Me Ml Mm Mq Mr Ms Mw My Na Ne Nf Ni Nm Nw oE Or Oy Oz Pb Pe Pi Pk Qd Qe Qh Qt Qv Qy Ra Rh Ri Rj Sr St Tr Uk Ul Un Up Ur Us Vt Vv) Lj(aC Ad Aj aM BA bB bF bR bV bW cE cT Cv Dc Di dM dN Dp eC Fy Gp Hb Hq Hr Hx Id Ih Ii Il Io Iq It Iu Jk Jm Js Jy Kd Ko Kq Ly Lz Ma Mb Mc Md Mg Mh Mj Mk Ml Mv Mx My Na Nf Nk Nm Nq Nr Nu Ny oE Of Og Oh Oi Ou Oz Pa Pd pF Pg Qb Qc Qv Rh Ri rS Sr tU Uf Uk Ul Un vS Vt wB We wL wP zA Zq) Vt(aA aC Aj Ax bA bB bF bL bV Cs CT cV dD dF dJ dM Dp Ed Fa Fp Fr Gp HB Hv iA Ib Id Ij Il Is Iz Jk Jl Jn Jo Jq Jr Jy Kg Kj Kk Ko Kp Kq Kr Kz Li Lw Ly Mm Mn Ms Mt Nd Nr NW Oa oF oH oK Ou Ow Oy Oz Pb Pe pF Qa QC QD Qe Qg Qh Rf Ri Sr St Uf Ug Ul Us vS We Zx Wm) qZ(AD aG aH aI Aj aK aL aN aR aW BB bM bQ bR bS bW cA cB cC CH cK cO cR Cs cV Cw dD Dg dJ dL dM eC Fb fN fP Hc hP Ib Id iH iO iP KR Kz nW oE oH oK oN Ow Ph Pj qA qB qC qH rS sC sO tO tR tS tU uM uV uY vA vS vV wB wC wD wE wF wG wH wJ wK wL wP wQ yD yL zA xA Wm) Jj(aC Al Ap Ar As Aw Bb Bc bE bV cH Cp Cq cT Cv Cw Dc dF Dg dJ Dk DI dM eC Ef Fb Hb Hq Hr Hx In Io Iq Iu Jh Jy Kd Kf Kk Kn Kr Ks Kx Kz Ly Lz Ma Mb Mc Md Mh Mi Mj Mk Ms My Na Nf Nk Nq Ns Oe Of Og Oi Or Ou Oy Oz Pa Pb Pi Ql Qm Rf Rh Tn Tr Tv Uf Ul Ur Us Uu) aA(AD aI aM bB bF bM bN bR cE cF cH dD dF dJ dM eC Hq Hu Hv Hw Hx Ih Ii Il Io It Iu Iv Jh Jk Jm Jo Js Jt Lu Ly Lz Ma Mb Mc Md Mg Mh Mi Mj Mk Mn Mp Mr Mu Mv Mx My Na Nb Nf Ng Ni Nk Nm Nn Nq Ns Nu Nv Ny Oe Of Og Oh Oi Oy Oz Pa Pb Pd Pe Pg Pz Qb Qc) Jl(Aj Ct Hq Hr Hu Hv Hw Hx Ih Ii Ij Il Io Ip Iq It Iu Iv Jh Jm Jo Js Jt Lu Lw Ly Lz Ma Mc Md Mg Mh Mi Mj Ml Mn Mp Mr Mu Mv Mw Mx My Na Nf Nk Nm Nn Nq Nr Nu Nv Nx Ny oE Of Oh Oi Om Oz Pa Pc Pd Pe Pg Pz QB QC QD Ur) Mq(Ax Bg Ch Cs Dc dM Dr Hq Hr Hu Hv Hw Hx Id Ih Ii Il Io Iq It Iu Jh Jk Jm Jo Jt Ko Lu Lw Ly Lz Ma Mb Mc Md Mf Mg Mh Mi Mj Mk Mp Mu Mv Mx My Na Nb Nf Ni Nk Nm Nq Nr Nu Nv Ny Oe Of Oi Oy Oz Pa Pd Pg Pz Qb Qc Ur Wf Wm) Et(aE aH aI aP aS aV aX aY bB bC bE bG bJ bU bZ cC cJ cM cS cZ dA dB dC dG dK dL dN DR eC eF fP fR Fy gL gP gW Ha hB iZ Jf jl jO Ld nW oH oN Op pF Pj Qg QI Rg Rm Tn Tr TT Tz Ub Uc Ud Ue Uf Vp Vq Vu Yh Th) Lh(Aj Ch Ct eC Fr Hu Hv Hw Ih Ij Il Io Ip Iq It Iu Jh Jm Js Jt Kg Lu Lw Ly Lz Ma Mc Md Mf Mg Mh Mi Mj Mk Ml Mn Mp Mr Mu Mv Mw Mx Na Nf Nk Nm Nn Nq Nr Nu Nv Ny Oe Of Oi Oy Oz Pa Pd Pg Pz Qb Qc Ur Wm) Lv(Hq Hr Hu Hv Hw Ih Ij Ik Il Io Iq It Iu Jh Jm Jo Js Jt Lu Lw Lz

Figure 3 Continued

Ma Mc Mf Mh Mi Mj Ml Mn Mp Ms Mu Mv Mx My Na Nf Ng Ni Nm Nn Nr Ns Nu Nv Nx Ny Oe Of Og Oh Oy Oz Pa Pb Pc Pd Pg Pz Qb Qc Wm) Mz(eD eT eZ fN Fr hA hO hP hR hV hW hX iB iC lK lv jD jE jF JG jH jI jL jM jO jP JQ JR jT jU jV jY lK IL IM IN lO Me Mm Mr Ms Nc Nd Ne Nh Nj Nl Nt On Pe Po qA qB qD qX qY rW uX wB) Nw(aC AD Aj aM AN Ao As Ax bB Bg bL bN bR bS bV CH Co Cs Ct Cu cV Cw Dc dF dJ Dk dM Dp eC Ed eT eZ fY gW hL iC Id Iz jD jE jI jK jO Kr IN Oa pF pY Qv Ri rS rW Sr Uk Ul Ur vT Tj) Is(aC aD Al aM An aW bA bB Bg bL bN bR bS bV cA cH Co Cs cV dD dF dJ dM dN hA hR hW hX iB Iz jD jE jF jG jH jI jL jM jO jP jR jT jU jV jY Kg lK IL IM IN IO oE qU Qv qY Rh Ua Uk Wm) Im(Ad al AN As Ax bB Bg bN bS bV bW cA Co Cs Cu CV Cw Dc dE dF dJ dM dN Dr eC Fa GP Hb Hc Id Iz Kd Kg Kj Kk Kn Ko Kp Kq Ks Oa oE Or Ou pF Qv Qw Rh Ri Tv Ua Ul Un Ye Th) On(Aj Ch Ct Fr Hq Hr Hu Hv Hw Ih Ij Ik Il Io Ip Ir It Iv Jg Jm Jn Jo Jp Js Jt Lu Lw Mb Mc Md Mf Mg Mh Mk Ml Mm Mr Mu Mv Mx Na Nb Nh Nq Nt Nu Of Oi Pb Pc Pd Pe Po Qb Qd) dM(Ad aQ bB bF bR cE cH dD dF dJ eC eD Gp gW hA hR hV hW hX iB iC Ij jD jE jF jG jH jI jK jL jM jP JQ jR jT jU jV jY Li lK IL IM IN IO Lx MI Oa Pe qX qY rB rX rZ Ur) Li(aC Aj bL bN bS Ch Ct eC eT eZ fY hL hO oE pS pY qA qB qD qH ql rN rO rP rQ rR rU rV rW sC sK sM sO tN tQ tT tX uG ul uL uN uO Ur uW uX uY uZ vA vB vC vH vl Wm) Lx(Aa aC AD Aj Ax Bg bL bN bR bS CH CO Cs Ct Cu Cv Cw Dc dF Dp eC Fi Fy Gp Hc Id Iz Kd Kg Kk Ko Kq Kr Oa oE Qv Rh Ri Sr Ua Uk Ul Un Ur Us Vv) Jg(Ch Fr Hq Hu Hv Hw Ih Ij Ik Il Io Ip Ir Jh Jk Jo Jp Js Jt Lu Lw Mb Mf Mg Mh Ml Mm Mu Mv Mx Na Nb Nc Nf Nh Ns Nt Nu Oe Of Oh Oi Pa Pb Qb Qd) aC(AJ Al aM An Ao Ap Ar As Aw bA BB bF Bg Bn Bo bV cF cG CH Co Cp Cq Ct Cw Cx Db Dd De dG Di Dk Dl dN Dr fR Ij Jq Mw Pe Qa Qd Qe Wm) Po(Fr Hq Hu Hv Hw Ii Ik Il Ip Ir Iv Jk Jm Jn Jo Jp Jr Js Jt Lu Lw Mb Mf Ml Mm Mn Mr Mw Mx My Nb Nc Ne Nh Ns Nt Nx Oe Og Oh Om Oy Pe Pe Qd) Qe(bA Bg bN Ch Cs CT Cv dF Hx Id It Iu Jh Kg Ly Lz Md Mg Mk Mp Mu Mv Nf Nm Nn Nr Nv Ny oE Oh Oz Pg Pz Qb Qc Qd Qv Rh Ua Uk Ur Wm Th) Jq(Aj Ax Cs Ct eC Hu Ij In Ip Ir Iv Jm Jn Jp Jr Lu Mb Md Me Mh Ml Mn Mr Ms Mw Mx Nb Nc Nn Nr Nu Nx Oa oE Og Oh Pc Pe Pz Qb Qd Rh Uk Ur) Pe(Bg bL bN bR bS Ch CO Cv eC Fr Ha Ik In Ir Iz Jp Jr Kg Kj Me Mm Ms Nc Ne Nh Nj Nl Nt Nx oE Pb Qd Rh Ua Uk Ur Tj) Mt(Aj Bg bR bS Ch eC Hq Hr Hx Ii Iq It Iu Jh Jm Ly Lz Ma Mc Md Mg Mj Mk Mu Mv Nk Nq Nr Nu Nv Ny oE Of Oh Oi Oz Pz) dF(AD aF Aj aM aO Ax Bg bL bM bN bR bS bZ cA cF CH cl cK cL cO Cs Cv Dc dE dH dJ Fp hA In jO Nd Ng Qa) Ur(Ad bA Bc Cs Cu Cw Dc Dp Fa Fp Fy Id Ij Ip It Kd Kf Kn Ko Kq Lw Mr Mw Nr Ou Qd Qh Rm Sr St Tv Un Us) Qa(bA Bg bN bR bS cT Cv eC Gp Id Iz Kg Kj Kr oE oH pF qC Qg Qv Rh Rt Tv Ua Uk Wm Th) Qd(Aj bA Ik In Iv Jn Jr Me Mm Mr Ms Nc Nd Ne Ng Nh Ni Nj Nl Nt OE Om qC qD Wm) Wm(al bB bF bN bV cE cM cT cV dD eC hB In Jp Lw Mw Ng oF oH Ok pF rB Ti Th) In(Ax Cs Fa Fr Fy Id Ij Ik Ir Iv Jr Ko Kq Mr Nj Nl Oa Om Qb Sr St Un) Nt(Fr Ij ip Ir Iv Jn Jp Jr Me Mm Mr Ms Mw Ng Ni Nj Nl Oe Om Pc) Nl(Ij Ip Ir Iv Jn Jr Jt Me Mn Mp Mr Mw Nb Nc Ni Nk Nn Nv Om) Id(Aj Ch Ct eZ fN Hb hP Kp Mw Ne Ng Oa oE qD Qv Rh Uk uM wP) eC(Cu Dc Fy Ij Kd Kn Ko Kp Kq Mj Ml Mr Oa Pi Sr Tv Uc Un Us) Fr(Aj Ch Ct Ik Ir Iv Jn Mm Mr Mx Nc Ne Nh Ni Oe Og Oy Pb) Kq(Ao Bg Co De Dk Hc jD Jk Jo Kg Kj Ne Oa oE Oy Ua Uk) Ng(Ap Ax Cu Dg Fa Fy Ij Jp Nv Oa oE Sr St Tr Uc Un) Aj(Ap bA Dg Fa Fy Jp Ko Mw Oa Ok Sr St Tn Uf Un) Mm(Hu Ij Ik Ir Iv Jn Jp Ml Mr Ms Nc Ne Nh Ni Nj) oE(Bc cH Dr Fy Gz Ip Kd Ko Mw Nr Oa Sr St Uy) Ne(Fa Iv Jn Jp Jr Mn Mr Nh Oa Om Sr St Un) Ch(Ad BA Fy Ij Jp Mw Ok St Tn We Zq) Nd(Aa Ij Ir Jn Jr Jt Mp Mw Nv Om Qb) Nj(Ir Iv Jn Jr Jt Mp Mr Mw Ni Nv Om) Jp(Ik Ir Iv Jn Jr Mf Mr Ms Nc Nh Ni) Oa(bA Hb Ko Lp Lw Mw pF qC Rh Uk Zq) Cs(bA bF cE Cv dJ Gp qC vS wP) Iv(Ik Ir Jr Mb Ms Mw Nc Nh Om) Ko(bN Cs In Kg Kj qC Rh Uk vS) Mr(Ik Ir Jr Me Ms Nc Nh Pb) Ij(Bg Ct fR Hc Iz Ms Wc) St(Ct Dr Jk Qv Uk Ye Th) qC(Ax Dc Fb Kn Kp Ny Un) Jr(Ik Ir Jn Me Nh Om) Ax(bA cE Gp Hb vS) Fa(Fi Hq Iz Uk Th) Il(Dr Eq Sf Yl Ye) wD(dE nW Ou Pj Ri) Fy(Ct Jo Kg Uk) Me(Nh Nn Nv Om) Ms(Ir Nv Qb Un) aM(bA bF cE fR) Dr(cV mZ Qb) Nh(Jn Mn Om) We(Lz Ml Ye) Uk(Mw Sr Un) bA(Ad bB Oy) hB(dJ jD jl) Ct(cT Cu) Nc(Ni Nk) Kp(fN vS) Om(Og Oy) Un(Rh Wc) Vq(Ed Or) AdKj Mwlz IkJn HcJh OuuX aDcE cGhA dBrN Unconstrained panels with 2 analytes, where 1.0E-3 >= 'model p-value' > 1.0E-4. Contains 8,554 panels of 192,797 total panels evaluated.

Dl Ef Fb Fp Gp Hb Ih Ip It Jt Kd Kf Kk Kl Kn Lv Mn Nr Nv Ou Pd Pg Pj Pz Qh Rf Tr Tv Us Vq We Zq) Ng(Ar Aw bB Bc bF bV cE Cp cT Cw Dc dG Dk Ef Fb HB Hu Ik Ir Jt Kd Kf Kk Kn Mm Mu Nh Nn Or Ou pF Pj Qb Qh Qm Rf Rh Ul Uu Vq We) wD(aW bL bS cC DB dC eD Fb iA iO jD jP jY Kk Kr Nm Ny Ow pY qC qD Ql Qn RB rC rK rS rX rY To Tr Tv Ub Uf uM uX vS tL Tj tF) Fp(Aa aD aM aU bB bF bN bR bS bV bW cE cF cG cH cM cT CV Dc dE dJ dN Hb Kd lX Ou qY Rh Rt Rz Sr Uf Uk Ul Uw Uy We Wh Zq Th) Nh(Hu Hv Hw Ih Ik Ip Ir Jm Jo Js Jt Lu Lw Mi Mp Ms Mu Mx Na Nb Nf Ni Nj Nn Nr Ns Nv Nx Ny Og Oh Pa Pb Pc Pd Pg Pz Qb Qc) hB(bL bN cH cO eD fN hA hO hP hR hW hX iB iC jE jF jG jH jK jL jM jP jQ jR jT jU jV jY lK IL lM lN lO oH qC qY rB vS vV) Mm(Hv Hw Ih Ip Jm Jo Js Jt Kd Lu Mb Mf Mh Mn Mp Mu Mx Na Nb Nf Nn Nr Ns Nu Nv Nx Oe Og Oh Pa Pb Pc Pd Pg Qb Qc Sr Uk) Ir(Hu Hv Hw Ik Ip Jn Js Jt Lu Lw Mb Me Mf Ml Mn Mp Mu Mx Nb Nc Ni Nn Ns Nu Nv Nx Oe Og OH Pb Pc Pd pF Pg Pz Qb Tv) Ml(aI aJ bB bF Bg bN bR bV bW cE cH cl cT cV dD dE dJ dN Gh iC Jn jT Nv pF Qb qY Rz Wb Wc Wh Zq Zx Ye Tl) Jg(Bg Ct Hr Hx Ii Iq It Iu Iz Jm Ly Lz Ma Mc Md Mi Mj Mk Mn Mp Nk Nm Nn Nq Nr Nv Nx Ny Oz Pc Pd Pg Pz Qc) Ld(Fc Fd Fi Gb Gc Gh Gn Hl Ho Hp Lp Rt Ru Rv Rx Ry Rz Sf Si Uw Ux Vh Vw Wb Wc We Wh Yk Yl Zq Ye Tm Tl Xa) uX(aW bL bN cH cL cO DB dE dJ eD Fb hO hP hR iH jO jP jT Kr Lu Mf Nk Nm Ny Ow qC qD QY rB uM vS vV) Jn(Hu Ip Jm Jt Lp Lw Mb Me Mf Mn Mp Ms Mu Mx Nb Nc Ni Nn Nr Nu Nv Nx Ny Oh Pa Pc Pd Pg Pz Qb Vq We Zq) Nj(Hu Hv Hw Ih Ik Ip Jo Js Lw Ma Me Mn Ms Mu Mx Na Nb Nf Nk Nn Nr Nx Ny Og Oh Pa Pc Pg Pz Qb Qc Zq) On(Ao Bg Co Hc Hx Iq Iu Iz Jh Ly Lz Ma Mi Mj Mn Mp Nf Nk Nm Nn Nr Nv Nx Ny Oh Oz Pa Pg Pz Qc Rt Wc) Uk(Ad aM bB Cu Dc Hb Ip It Jt Kd Kf Kk Kn Kx Lh Lw Nm Nr Ok Or Ou pF Pg Pj Qh Qm Rf Tr Tv Uf Ul Us) Ik(Hv Hw Ih Ip Js Jt Lw Me Mj Mn Mp Ms Mx Na Nc Nf Ni Nn Nr Ns Nv Ny Og Oh Pa Pb Pc Pz Qb) Lw(Dp eZ fN Gp gW Hb hO hP hW hX iC jD jK jO jQ jT Kk IN Me Nd Qb qC qD qY Rh uM yL) Sr(bN Ch Ct Dp Gp Hb Hc hP Iz jD Jk Jo Kg Kj Kk Mn Oy pF Pj qC qD Qv Rh Ri Rt Uf vS) cE(Ad aJ AN bB Bg bL bM bN bR bS bV cA cF CH cL cO Ct Cu Dc dD dE dJ dL dN jl) Nd(Cu Ih Ip Js Me Mi Mn Mu Mx Na Nb Nf Nn Nr Nx Ny Oh Oz Pa Pc Pd Pg Pz Qc We Zq) Ad(aJ aM aU bB bF Bg bN bV bW bZ cH cT cV DD dJ Gp Hb Jo Kg Oy qC vS wP) Ny(eT eZ fN fY hL hO hP jI Me Nc pY qA qB qD rN rS rW tR tT uM uO vS vV wP) Dc(aI aU Ba bB bF bN bW CT Dg dJ eZ fN Gp Hb hO hP jD qA qB qD Rh vS) Ou(Bg Ch Ct gW hA Hb jD jI jO Kk IL pS qX qY rA rB Rf Rh rN rS uT wP) Me(Aa Hu Ih Ip Js Jt Mn Mp Mu Mx Nb Nc Nm Nr Nx Oh Pa Pc Pg Pz Qb) Cu(aD aU bB bF bL bN bS CH cT Cv dJ Gp Hb Jk Jo Kj oH Oy qC) We(aM Bc De Dp Ed Eq Kj Mh mZ Ni Nr Ow Oy Pb Qb Qx Ra Rh Rt Wc) Ct(Bc bF Cw Dg dJ EF Kd Kf Kn Lv Nr Nv Ok Pd Pg Qh Tn Uf) qC(cH Cv Ih Js Kc Kd Kf Kk Kr Lh Nm Nx Oh Ok Pg Rb Rm Uc Uf) bF(aD aJ bB Bg bL bM bR bV cA cF CH cO Cv dJ dL dN jI) Ms(Hb hW Ip Js Jt Kd Mn Mp Mu Mx Nb Nn Nr Nx Oh Pj) Zq(bR De Ed Gl Lz Mh mZ Nr Or Ow Oz Pb Qb Qx Rh Ye) Gp(aM Ar As Bc Bn Ch Cp Cq Cv Cw dJ dX eP Kd Tv) Kr(nD rN tV uM uO uT vS vV wB wH wP zI yE tM xA) Lh(Bg bN Hc Iz jI jO Kj lN oH pF Qv qY Rh Ua Tj) bB(aJ aM Bb Bc bR cF cl cT Cv dJ dN fR gW jl qX) Kn(bN eD fN Hb hP hX jD JO pF qD Rh sC vS) Uf(Ch Ed hO Iz jI Jo Kd Kg Kj rS uM uV vS yL) Nm(qH rN uM vA vS vV wB wH yL yE tM xA) Qb(Hu Jt Nb Nc Ni Oe Og Rz Wh Zx Ye Xa) Nr(Ch Fi Kd Kk Qv Rh Rt Wc Yl Ye Tl) Lv(Hx Ii Jk Ly Mb Md Mg Mk Nk Nq Oi) aJ(al bL bN bR cF cH cT dD dE dJ qY) jl(bW cU Dp Fb Ip jT nW Pg Pj Qh qY) Hb(Ch Cw Ed Kd Kk Qv Rh Tv Ul Us) cT(aD aI aM Bc CH Cv Dg dN fR) dJ(aM An Ba Bc bV cG Cv dG dN pF) Nc(Ip Jt Mn Mp Nb Nn Nv Nx Pz) Kd(bN Kk pF Pj qD Rh vS Wc Tl) Pg(Bg Ch hA hX iC jD jE jO lN) Nv(Mh My Ni Ns Oe Og Oy Pb) Ip(bV hW jQ Jt Mx Nb rX) Ok(Bg bN Ed jO Kg Qv Rh) Pj(Ed Kg Kk Or Qv Rh vS) cH(aM Ba bV cG dN pF wP) nW(rN rS tU uT vW wB wP) Js(iC jK jQ lN Ni qY) Jt(Lu Mb Mx Nb Nx Og) bR(bV cG dG dN nD nl) mZ(Gd Ry Rz Wh Tl Xa) vS(Kf Qh Rm Tr Tv Us) aM(al bV cF cV qY) nD(Ed gL oK Pi Up) Ni(Ih Mn Nn Nx) Tn(Bg Iz Jk Oy) Kf(Kg Kj sC uM) Kk(bN Qv Rh Vq) cF(bV cG dD dG) rN(Db dE Mf Rb) Ch(Dg Qh Wh) Tr(Mk Oy uN) Tv(pF rB Uo) Ye(Of Ow Ql) dG(bL bN cA) wB(DB Rb) Ba(aD Bg) Bc(Lt oH) Fb(hW rS) Mx(Mn Pc) Xa(kR Pb) Vq(bV cV) Oz(Uw Wh) dD(bV dN) tV(dB dE) BoeM CwRt DbuT TiUl ThMh MyJh WcQx QhJk RhOr VsOy PdhX aDfR bNdN cAcG cPeP jDoF qYqX

Constrained panels with 3 analytes, where 1.0E-10 >= 'model p-value' > 0. Contains 1,345 panels of 35,857,239 total panels evaluated. :
Et{Ng(aA Aj Ax BA Bc bN cl Fp Fr Hf Hu Ij Ik Im In Is Jg Ji Jj Jl Jm Jo Jq Jr Kg Kr Lh Li Lj Lu Lv Lx Mb Me Ml Mq Mr Ms Mt Mu Mw Nb Nc Nd Ne Nh Ni Nj Nl No Nt Nw Oe On Pc Pf Po Qa Qb Qe Rh Ri Wm) Jo(aA Fp Hu Hv Hw Ik Im Ip Is It Iv Ji Jj Jl Jm Jn Jq Jr Lh Li Lj Lu Lv Lx Mb Me Mf Mh Ml Mq Mr Ms Mt Mz Nc Nd Ne Nh Ni Nj Nl No Nt Oe Ok Pe Pf Po Qa Qe Wm) Ms(aA Aj Fp Ik lm Io Is Iv Ji Jj Jl Jm Jn Jq Jr Lh Li Lj Lu Lv Lx Me Mh Ml Mm Mq Mr Mt Nc Nd Ne Nj Nl No Nw Oh On Pc Pe Po Qa Qb Qe Wm) Jj(aA Fp Ik Im Io Is It Iv Ji Jl Jm Jq Jr Lh Li Lj Lu Lv Lx Me Mh Ml Mq Mr Mt Nc Nd Ne Nh Nj Nl No Nt Po Qa Qb Qe Wm) Nd(aA Fp Im In Is Iv Ji Jl Jn Jq Jr Lh Li Lj Lu Lv Lx Me Mg Mh Mp Mq Mr Mt Mz No Nw Oe Oy Pb Pe Pf Qa Qe) Im(aA Aj Ch Hq Hw Ii Il In Io Ji Jk Jr Jt Lu Lv Me Mg Ml Mq My Nc Ne Ni Nj Nl Ns Oe Of Og Oy Qe) Jt(aA Ax Fp Ik Is Iv Ji Jl Jn Jq Jr Lh Li Lj Lv Lx Me Mq Mr Mt Nc Ne Nj Nl No Nt Nw Qa Qe) Oy(aA Fp Ik Is Jg Ji Jl Jr Lh Li Lj Lu Lv Lx Me Mq Mr Mt Nc Ne Nj Nl Nw On Pf Po Qa Qe Wm) Is(aA Ch Fp Hq Hw Ii In Io Jk Lj Lu Md Me Mg Mq My Nc Ni Nj Nl Nq Ns Oe Of Og Pb) Ji(aA Fp Hq Ii In Jk Lj Lu Mb Md Mc Mg Mm Mw My Nj Nl Nq Ns Nv Nx Oe Of Om Pb) Me(aA Fp Hq In Jl Jr Li Lj Lu Lv Lx Mq Mt My Nc Ne Nj Nl No Nw Pb Qa Qe) My(aA Fp Ik Jg Jh Jr Lh Li Lu Lv Lx Mq Mt Nj Nl No Nw On Qa Qe Wm) Nj(aA Fp In Jn Jq Jr Li Lj Lu Lx Mg Mh Mq Ni No Nw Oe Pb Qa Qe) In(aA Fp Ik Iv Jl Jr Li Lj Lv Lx Mh Mq Mt Nc Ne Nl No Qa Qe) Lj(aA Aj Hq Ii Ik Io Jr Kg Lu Lv Mq Mt Nc Ne Ni Nl Oe Wm) Mq(aA Ii Jn Jq Jr Lu Lx Mg Ml Nc Ne Nl Ns Oe Pb) Qa(Hq Hw Ii Io Jk Lu Mj Ni Nl Nq Ns Nv Oe Pb) Nl(aA Jq Jr Lu Lx Nc Ni Nk No Oe Pb Qe) Oe(aA Fp Ik Jr Li Lx Mt Nc Ne No Qc) Lu(Fp Jr Li Lv Lx Nc Ne No Pb Qe) aA(Fp Ik Jk Jr Lv Mb Md Nq Ns Pb) li(Fp Jl Jr Lh Li Lx Mt No Qe) No(Aj Ch Ik Lv Nc Ne) Jr(Hq Mt Nc Ne Ns Pb) Qe(Hq Jk Nc Ns Pb) Fp(Hq Mj Ns Pb) Pf(Aj Ch Co Kg) Pb(Ik Lx Ne) Aj(Mm Oa) Mg(Ik Mt) Nc(Ni Nk) ChHu NsMt LxHq MdJq MkJl NiLi KgVt} Ji{Oy(aA Fp Fr Hu Ik Il Im In Is Jg Jl Jm Jo Jq Li Lj Lu Lx Mq Mr Mt Nd Ni Nl No Nw On Pc Pe Pf Qa Qe Wm) Im(aA Fp Hq Ii In Io Jj Jk Jo Jq Jt Lj Lu Md Mj Mq Ms Mw My Nd Ng Ni Nj Nl Nx Oe Og Pb) Md(aA Fp Ik Io Is Jj Jl Li Lj Lu Lx Mq Mt Nd Ne Ni Nj Nl No Nw Nx Oe Pf Qa Qe) Mq(Hr Hv Ii In Jj Jk Jo Jq Jt Lj Lx Mw My Nd Ng Nj Nl Ns Nv Nx Of Og Om Pb) Li(Hq Hv Ii In Jj Jk Jo Jt Me Mj Mk Mv Mw My Nd Ng Ni Nj Nq Ns Nv Oe Og Pb) Qa(Hq Hv Hx Ih Ii In Jk Jo Jt Mj Mk Mw My Nd Ne Ng Nv Nx Oe Of Og Pb Qb) Lu(Hv Ii In Jj Jk Jo Jq Lj Ms Mw My Ng Nq Ns Nv Nx Of Og Om Pb Pg) Is(Hq Hv Ii In Jk Jo Jq Jt Mj Mk Mv Mw My Nd Ng Nj Nl Nx Oe Of Pa Pb) No(Hq Hv Ii Ik Jk Jt Mj Mw My Nd Ne Nj Nl Nq Ns Nv Nx Oe) Ng(aA Fp Fr Hu Ik In Jg Jj Jo Jq Lj Mt Nd Ni On Pf Qe Wm) My(aA Fp Ik In Jg Jh Jj Jl Jo Jq Mt Nd Ni No Nw On Qe Wm) Pb(aA Fp Ik Io Jj Jl Jq Lj Mb Ms Mt Nd Ni Nj Nl Oe Pf) Jo(aA Fp Ik Iv Jl Jm Lj Me Mr Ms Nd Ni Nl Ok Pe Qe) Nx(Fp Ik Iv Jl Lj Mr Mt Nd Ne Ni Nl Nw Ok Pf Qe Wm) In(aA Fp Ii Ik Jj Jl Lj Me Ms Nc Nd Nj Nl Qe Wm) Jk(aA Fp Ik Jg Jl Jm Mr Mt Ne Nl On Pe Pf Qe) Ii(aA Fp Iv Jj Jl Jm Lj Mr Ms Ni Pe Qe) Lj(aA Hv Io Jj Jq Jt Mj Nd Ni Nj Oe) Qe(Hq Ih Jt Mj Mv Mw Nd Nv Oe Of) Jl(Hx Jt Mi Mj Mk Mw Nb Nd Nv Pa) Ms(aA Fp Hq Io Jj Jt Ni Wm) Ik(Jj Mg Mk Mv Mw Of Og Om) Ne(Nc Nd Nh Nj Nk Nl Wm) aA(Fp Hv Jq Jt Nd Ns Oe) Jj(Fp Hv Jm Nd Nl Wm) Mt(Mv Mw Ns Of Og) Wm(Mw Nq Nv Ny) Fp(Mj Mk Mw Nd) Ni(Jq Nc Nj Nl) Iv(Hx Jt Mk Nb) Pf(Hq Of Pa Pg) Mr(Hx Mk Nb) Nk(Nc Nj Nl) Ok(Jt Me Om) Pe(Hq Hx Mk) Mw(Jg Nw) Jq(Jr Me) MhMj MuPc NlOe JnJs NvNw} Jj{lm(Fp Ik Ip Is Iv Jl Jr Lh Li Lj Lu Lv Lx Me Mf Mq Mr Ms Mt Nc Nd Ne Nh Ni Nj Nl No Nt Nw Oe Ok On Pe Qa Qe) Fp(aA Fr Ik Ip Is Iv Jg Jl Jm Jq Lh Li Lj Lu Lv Lx Mm Mn Mq Mr Mt Mw Mz Nc Nl No Nt Nw Ok On Pz Qa Qe) Is(Ik Jg Lh Li Lj Lu Lv Lx Me Mq Ms Mt

Figure 3 Continued

Nb Nc Nd Ne Nj Ni No Nt Nw Ok Pf Qe) Qa(Ik Lh Li Lv Lx Me Mq Ms Nd Nj Nl Nw Ok) Ik(Ip Jl Lh Li Lj Lx No Nw Ok Qe) Mq(Lh Li Lj Lx Mt No Nw Ok Qe) Nd(Jl Lh Li Lx No Nw Ok On Qe) Nj(Li Lx No Nw Ok Qe) Ms(Lh Lx Nw Ok Qe) Nl(Lh No Nw Qe) Lv(Li Lx No) Me(Li Lx Nw) Lj(Lh Mt) LxJl NgJg} Ng{Jg(aA Fp Fr Hu Ik Im In Ip Ir Is Jl Jn Jq Jr Lh Li Lj Lu Lv Lx Mc Me Mq Ms Mt Mw My Mz Nc Nd Ne Nh Ni Nj Nl No Nr Nt Nw Nx Oh Ok On Oy Pe Pf Po Qa Qb Qd Qe) Nw(Fp Ik Im Is Mq) On(Fp Im Lx) Ok(Fp Im)} Nw{Ms(aA Fp Ik Im Is Iv Jr Lu Lv Lx Mc Mq Mt Nd Ni Nj Nl Ok Pb Pc Qa Qe) Fp(Im In Md Mj My Oe Oy Pb) My(Jg Jh) Nd(Im No) Jk(Im Qa) MqOy} Fp{In(Im Is Jl Jq Mm Ok Qa) Ms(Is Ok On) On(My Oy) JgOy JoOk} No{Nd(In Is Lv) NjIn} Ms{Ok(Im Is Lx) LxIs} IsJgOy WeLdmZ

Constrained panels with 3 analytes, where 1.0E-9 >= 'model p-value' > 1.0E-10. Contains 1,230 panels of 35,857,239 total panels evaluated. :
Et{Kg(Ad Af Aj Ax Bc Bg Ch Cs Cu Cw Dc De Dp Fy Id Ij Im Is Ji Jm Jq Kd Ke Kf Kn Ko Kp Kq Kr Lh Li Me Ml Mm Mr Ms Nc Nm No Oa Pe Pi Qa Qe Qh Ra Rh Ri Sr Tv Un Us Wm) Aj(aA Ao Ax Bc Bg bN Ch Co Cs Fb Hc Id Il Is Ji Jm Jq Jr Kr Mq My Nd Ne Oy Pe Qa Qe Rh Ri Ul Vt Wm) Ch(aA bA bN cl dM In Ji Jj Jm Jo Jr Jt Kr Lj Lv Lx Me Mm Mq Ms Nd Ne Oa Pe Qa Qe Rh Ri Uk) Pb(Hu Io Iv Jl Jn Jq Lh Li Lv Mb Mh Ml Mr Mt Mz Nb Nc Nh Ni No Nw Oe Pe Pf Po) My(Hu Io Iv Jl Jm Jn Jq Mb Mh Ml Mr Mz Nb Nc Ne Nh Ni Nt Oe Pc Pe Pf Po) Oy(Fr Hu Ij In Io Iv Jm Jn Jq Jt Mh Ml Mu Nb Nh No Nt Oe Pc Pd Pe Pg Qb) In(Ih Jm Jn Jq Lh Lu Mb Ml Mr Mz Nb Nh Nt Nw Oe Pe Pf Po Qb Wm) Jt(Cs Hv Hw Ih Ir It Jg Jm Lu Mh Ml Mz Nh Oa Ok Pe Pf Po Qd) Ns(Ik Jl Jm Lh Li Lu Lv Lx Mh Ml Nc No Nw Pc Pe Pf) Hq(Jl Jm Lh Li Lu Lv Mh Ml Mq Mr No Nw Pe Pf Po Qb) Ii(Hu Ih Ik Iv Jm Jq Lv Mh Mr Nt Nw Pe Pf Po Qb) Ng(aC aW cT dM Id Jy Ke Ko Oa Qh Uk Ur Uu Vt) Mb(Hv Hw Iv Jl Jn Jq Lh Mc Mr Mz Ni No Pe) Jo(Ad Ax Bg Cs Cu Cw Id Kd Oa Tv Vt) Oe(Iv Jl Jq Lu Lv Mh Ml Mm Nh Nt Nw) Lu(Jl Jq Md Mg Mh Ml Mt Nw Of) Lx(Jn Jq Lv Mg Nc Ne Ni Pa Pg) Lh(Hr Jk Md Mg Mw Nv Nx Of) Wm(Ji Mg Mm Mw Nv Of Pf) Ni(Jl Jm Mh Ne No Pf Qe) Ik(Jn Jq Mh Mz Nw Of Og) Li(Io Jk Jq Lv Mq Nc Ne) Lv(Io Mm Mt Nc Of) Jj(Ao Bg Co Hc Oa) Nw(Md Mw Nv Of Pg) No(Co Io Iz Nq) Mg(Hu Jm Nt Po) Ne(Jq Nc Nh Qe) Jl(Jk Mm Og Pa) Pf(Bg Ct Iz Pa) Io(Iv Nc Qe) Jq(Mh Ml Om) Md(Jn Mz) Mk(Mr Pe) Og(Jm Qe) CtIs McMl MhNc MmMq MrOf MtJk MwOn KrLj PaPe aAaO} Jj{Ik(aA Fr Ir Iv Jg Jm Jn Jp Jq Jr Js Jt Lv Mm Mn Mq Mr Mt Mw Mz Nn Nv Oh On Pb Pe Pf Po Pz Qb Qd) Lx(aA Hv Ip Iv Jg Jm Jn Jq Jr Lh Li Lj Mr Mt Nc Ne Nh Ni Nl No Nt Nw Ok On Pb Pe Qe) Mt(Ip Iv Jl Jm Jq Jr Lh Li Lv Me Mr Ms Nd Nj Nl No Nw Ok Pe Pf Po Qa Qe) No(Dp Ip Jg Jl Jm Jr Lh Lu Me Mf Ms Nc Ne Nh Nt Nw Nx Ok Qa Qe) Mq(Ip Ir Jg Jl Jm Jq Lv Mw Mz Nc Nd Nj Nl Nt On Pf Po Pz Qd) Qe(Jg Jl Jm Jq Jr Lh Li Lj Lu Lv Me Nc Ne Nh Ni Nt Nw Ok Po) Li(aA Hv Ip Iv Jl Jm Jq Lh Lu Ms Nc Ne Nh Ni Nl Nt Nw Ok) Nw(aA Iv Jl Jm Jr Lj Lu Lv Md My Nc Ne Ng Nt Oy Pb Po) Lh(aA Jl Jm Jr Lu Lv Me Nc Ne Ng Nh Nj Nt Pb Po) Ok(aA Jl Jm Jr Lj Lu Lv Me Nb Nc Ne Ng Nh Nl Po) Lj(Ip Jg Jl Jq Lv Me Nd Nj Nl Nt On Qa) Qa(Hv Ip Is Jg Jl Jq Lu Nb Nt Wm) Jl(Is Jg Lv Mc Ms Nj Nl Po) Po(Is Jm Lv Nd Nj Nl) On(Me Ms My Nj Nl) Jg(Lv Me Nd Nl) Wm(Im Ip Pf) Is(Hv Nh Ni) LvJm NlIp} Nw{Nd(aA Fp In Is Iv Jl Jn Jq Jr Li Lj Lv Lx Ly Md Me Mp Mq Mr My Ne Ng Oe Ok Oy Pb Pe Qa Qc) Oy(aA Ik Im Is Iv Jg Jl Jr Lh Li Lu Lv Lx Me Mr Mt Nj Nl On Pe Qa Qe) Im(aA Hq Ii In Lj Lu Lv Md Me Mq My Ni Nj Nl Ns Oe Og Pb) Fp(aA Hq Hv Ii Is Jk Jo Jq Lv Me Mm Mq Mw Nj Ns Nv Ok) Ng(aA Jm Jr Lh Li Lu Lv Lx Me Mt Nj Nl Ok On Qa Qe) Me(aA Ii In Is Lj Lx Md Mq Mw My Nc Nj Nl Pb) My(Ik Is Iv Jr Lh Lu Lv Mq Nj Ok On Qa Qe) Mq(Ii In Jo Lj Md Mw Nj Ns Nv Nx Pb) Nj(aA In Is Lj Md Ni No Pb Qa) Lj(aA Ik In Lu Lv Ni Oc Pb) Md(aA Jn Jq Qa) Is(Ii In Jk Pb) Qa(Ii In Oe) Ik(In Pb) WmMs MkJl NeNl HxIv QeJk JiPg} Fp{Is(aA Hq Ii Im Jk Jo Jq Lv Lx Mj Mm Mq Nd Ne Ng Ni Oe Og Ok Oy Pb) Im(aA Hq Ih Jk Jl Jn Jq Jr Lh Lv Mm Mq Ms Ne Ng Ni Oe Ok) In(aA Fr Iv Jg Jn Jr Lh Li Lv Lx Mq Mr Mt No Nt On Pe Qe) Ok(aA Hq Hr Ii Jk Jq Jt Lu Lv Md Mj Mm My Oe Oy Pb) Mm(aA Iv Jn Jq Jr Lh Lv Mr Ms Ng Ni Pb) Ms(aA Jg Jl Jp Jq Lh Lx Mt No) Jq(aA Jl Lx Md Mq Mt) Lh(Jo Ng Oy Pb) aA(Lv Lx Mq Pb) On(Jk Mw Pb) No(Lv Nd) Lx(Ng Oy) My(Jg Jh) FrNg MwJg NcNk} Ok{Ms(aA In Jl Jo Jr Jt Lh Li Lj Lu Lv Me Mq Mt Nc Nd Ng Nj Nl No On Pc Qa Qe) Jo(Ik Im Is Jl Lh Lv Me Mq Nd Nj Qa) Ng(Ik Is Li Lu Lx Mq Mt On Qa Qc) In(Im Is Lj Lx Me Mq Nj Qa) Nd(Im Is Jl Lj Lx No) Im(Ii Jk Jt Nj Oc) Is(Ii Jk) QaJk} Nd{No(aA Im Ip Iv Jg Jl Jn Jp Jq Lh Lx Mm Mp Mq Mr Ms Ne Oe On Pb Pc Pe Qa Qe) Im(aA Is Iv Jl Lh Lv Lx Mm Mr On Pe Pf) Is(In Lj Lx Mm Ms) On(Lj My Ng Oy) LxJl InQa LhLj} Ms{Is(Im In Jg Lh Li Lj Lv Mm Mq Mt Ni No On) Lx(aA Im Iv Jg Jl Jq Lh Lv Mq Mr Mt On) Im(aA Jl Lh Lv Mt No On) No(Lv Nj Wm) On(Lj Mt Ng) MtLh} Ng{Im(Fr Is Lh Li Lv Lx Mm Mq Mt) On(Ik Is Li Lj Mq Mt Qa Qe Wm) Is(In Li Lx Mq Mt No) Wm(Jg Pf) Lx(Lh Mq) BaJi NoIk} Im{Jk(aA Is Jl Lh Li On Qa) Nj(In No) Lh(Ii Oy) On(My Oy) aA(Lv Oe) MqIn NkNl} Oy{Jg(Jl Lh Lx Mq Mr On Pe Qa) On(Ik Is Li Lx Mt)} In{Is(Li Lj Lv Lx Me Mq Nj No) Mq(Lx Qa) NoIk NjQa} Wm{Ji(Hv Hx Ii Jk Jo Md Mj Pb) Ke(Nb Ut) NoMy} No{Nj(Lv Mq Ni Nk)} Jk{Is(Li Lx) QaJg} AdAjdF LiwPnW Constrained panels with 3 analytes, where 1.0E-8 >= 'model p-value' > 1.0E-9. Contains 2,651 panels of 35,857,239 total panels evaluated. : Im{Ng(aA Ba Hu Ik In Iv Jh Jl Jn Jp Jq Jr Ke Ko Lj Lu Lw Me Mr Ms Mu Mv Mz Nb Nd Ni Nj Nl No Nt Oe Om Pc Pe Pf Po Qa Qe) In(aA Ik Is Iv Jl Jn Jq Jr Lh Li Lj Lu Lv Lx Me Mm Mr Ms Mt Mz Nc Nd Ne Ni Nl No Nt Oe On Pe Pf Qa Qe) Mq(aA Hq Hw Ii Is Jk Jn Jo Jq Jr Lh Li Lj Lu Lv Lx Me Mm Ms Mt Mz Nd Ni Nj Nl No Ns Oe Og Ok Oy Pb) Lv(Hq Ii Il Io Is Iv Jk Jl Jn Jo Jr Li Lj Lu Lx Me Mm Mr Mt Mz Ni Nj Nl No Oe Og Ok Oy Qa) Ms(Fr Iv Jg Jn Jq Jr Li Lj Lu Lw Me Ml Mm Mp Mr Mz Nb Nd Ni Nj Nl Nt Oc Pc Pe Pf Po Qa Qe) Nd(Fr Jg Jk Jn Jp Jq Jr Li Lj Lw Mi Mj Mp Mt Mz Nb Ne Ni Oe Og Pa Pc Po Qa Qe) Nj(aA Fr Is Iv Jk Jl Jn Jp Jq Jr Lh Li Lj Lx Mm Mr Mt Mz Ni Nk On Pe) Lx(aA Hq Ii Iv Jk Jl Jn Jq Jr Lh Lu Me Mr Ni Nl Oe Ok Oy Pb Pe) Oe(Is Iv Jl Lh Li Lj Lu Mm Mr Mt Ni Nl No Nt On Pe Qa Qe) Ok(aA Hq Hr Hw Is Jl Jr Lj Lu Me Mt My Ni Nl Nw Og Oy Pb) Ni(aA Is Jl Lh Li Lj Mm Mr Mt Nc Nl No On Pe Pf) Jk(Fr Iv Jg Jn Jr Ke Mr Mt Mz Nl No Nt Pe Pf Qe) Lh(Hq Hr Hw Hx Il Jo Jt Lj Me My Nl Og Pb) Me(aA Is Jl Li Lj Mm Mt Nl No) Nw(Ik Is Iv Jn Jt Nc Ne Nv Qa) Fp(Iv Lu Mj Mr Og On Pb) Li(aA Hq Ii Jq Lu Og Oy) Jl(Ii Lu Mk Mt Og Oy) Lj(aA Jq Lu Mm Mt On) Et(Bg Co Ct Iz Wm) Oy(Jg Mr Mt Pe Pf) No(Hq Ii Lu Nl) aA(Jq Mm Mt Nl) On(Ii Mw Og) Lu(Is Mm) DpJj MtIv MyJg NcNk NeNl IsOg} Nw{Ii(Hv Hw Ik Iv Jl Jm Jn Jo Jq Jr Jt Lh Li Lj Lu Lv Lx Mt Nc Ne Nj Nl No Ok Pe Po Qe) Pb(aA Hw Iv Jl Jn Jq Jr Lh Li Lu Lv Lx Md Mr Mt Nc Ne Ng Ni Nl Oe Ok Pe Pf Qa Qe) Oe(aA Ik Is Iv Jl Jr Li Lu Lv Lx Md Mq Mt Mw My Nc Ne Nj Nl No Nt Ok Oy Qe) Qa(Hq Hr Hv Hx Ik Jo Jt Lu Lv Mb Me Mj Mw Ne Ni Nq Ns Nv Nx Of Og Pa Qb) Ok(Hq Hr Hv Ik In Jk Jo Jr Jt Lj Lu Lx Md Mt Mw Nc Ne Nj Nl Nv Nx Oy) In(aA Hw Iv Jl Jn Jq Jr Li Lu Lv Lx Mt Nb Nc Ne Nl No Nt Pe Qe) Lu(Hq Is Jk Jr Li Lv Lx Md Mq Mw Nc Nj Nl No Ns Nv Pg) Lv(aA Is Jo Li Lx Md Me Mq Mw Nc Nj Nl No Ns Nv Nx) Md(Hv Hw Ik Is Iv Jr Lh Li Lx Mt Nc Ne Ni Nl Qe) Ik(aA Hq Iv Jk Jn Jo Jq Jr Mw No Ns Nv Of Og) Is(Hq Hv Hx Jo Lj Mq Mw Nc Ni Nl Ns Nv Nx Og) Lx(aA Hq Hv Iv Jk Jn Jq Mw My Ni Nj Ns Pa) Jk(aA Iv Jl Jr Lh Li Mq Mt Nc Ne Nl On) Qe(Hq Hv Jo Mj Mw Ni Nj Ns Nv Og Pa) Nl(aA Hv Jq Lj Mq My Ni Nk No Ns) Mw(Iv Jg Jl Jn Jq Jr Lh Mt On) Nc(Hv Mq My Ne Ng Ni Nk Ns Oy) Ns(aA Jl Jr Li Me Mt Ne) Iv(Jo Jt Nb Ng Nv Nx Ny) My(aA Mr Mt Ni Pc Wm) Ne(Hv Jq Ng Ni Nj Oy) Li(hP Hq Hv Jo Me Ni) Lj(Hv Jq Mj Oy Pa) Nv(Jl Jq Jr Lh Me) Mq(aA Hq Hv Og) Oy(Jm Nb Ni Pc) Ng(Fr Nb Nt) Jr(Hv Ni Nj) Me(Jo Mt) Jn(Js Nj) Jq(Nx Om) Pa(Jl Pf) Pe(Hq Mk) BgEt WmJj MuPc HvaA} Jj{Lj(aA Fr Hu Ij Ir Iv Jh Jm Jn Jo Jr Jt Lu Mg Mm Mr Mu Mw Mz Nb Nc Ne Nh Ni No Nv Nx Om Pe Po Pz Wm) Lv(aA Fr Ij Il Ip Ir Jn Jp Jr Mm Mr Mw Mz Nc Nd Nh Nj Nl Nm Nn Nr Nt Nv Nx Oh Om On Pf Pz Qb Qd) Jl(Fr Hv Ip Ir Jm Jp Jq Jr Mb Mf Mw Mz Nb Nc Ne Nh Nm Nn Nt Nx Oh On Pz Qb Qd Wm) Mq(aA Fr Ij Jn Jp Jr Js Mf Mn Mr Ne Nh Nm Nn Nr Ns Nv Nx Oh Om Pb Pc Qb Qc Wm) Jg(aA Ip Ir Iv Jm Jn Jq Jr Lu Mr Ms Mt My Nc Ne Nh Ni Nj Nt Oy Pe Pf Po Qb) Nt(Fr Ij Ik Ip Ir Jm Jn Jq Jr Me Mn Ms Mt Mw Mz Nc Nj Nl On Pf Po Qb) Nl(Fr Ij Jm Jn Jp Jq Jr

Figure 3 Continued

Jl Jp Jq Jr Jt Lj Lv Me Mm Mr Ms Om Pe Po) Lx(Ad Hu Hv Ij Ip Jp Jr Jt Kq Lu Mm Mu Mw Mz Ne Nh Ni Pb Pc Wm) Ji(Ad Ap bA bF bN cT dF Dg dM eC Ko Qg Ri Uf Uh Uk Ur Uu) Fp(Ip Jh Jt Lv Mg Mn Mu Mw Nn Nt Nv Pc Pe Po Pz) Mq(aA Ad Dg Jl Jp Jq Ko Lj Lv Nt Om Po Uh Wm) Wm(dF Fr Ij Is Jl Jp Jq Mw Nw Ok Qd Uh) Fr(Jl Jq Jr Lj Lv Me Nd Nj Nl Nl Om) Uh(Ad Id Ij Jg Ko Kq Mw Rh Tn Tv) Jg(bA bF dF eC Ko Rh Ur) Ij(Dg dM Rh Uf Ur Vt) Is(aA aN Ap Dg Ku Ne) Kq(Il Mg Mw Ne Rh Ur) Jl(Ik Lv Nd Om) Jp(Lv Nd Nj Nt) On(Lu Nr Oe) Ad(Aj Ur) Po(aA Lv) Uc(eC qC) Ko(Mw Rh) LjOm} Lx{Pb(Hw Ik In Ir Jg Jn Jq Jr Lj Lu Me Mt Mz Nc Ne Nh Ni Nj Nl Oe On Pf Qa Qe) Oy(Ij Ip Ir Iv Jh Jn Jq Jr Lj Me Mz Nb Nd Ne Nh Ni Nj Nl Nt Om Pc Pf Po) Lj(Hq Hv Ik In Iv Jg Jl Jq Lh Lu Me Mm Mr Mt Nh Ni Nj Nl Oe On) Mr(Hq Hv Ii Jk Jo Lv Me Mk Mt My Ne Nh Ni Nj Nl Oe Pa) Mt(Hq Hv Iv Jk Jn Jq Jr Lv Me My Nd Ni Nj Ns Oe Pe) Nd(Fr Hq Hx Ir Jg Me Mh Mp My Ne Ny Oe Pa Pc) Hv(In Iv Jl Jn Jr Lh Me Mz Nh Nl On Pe Qa Qe) Ni(Ik In Jg Jr Lh Mm Nc Ne Nh On Pe Qa Qe) Hq(Iv Jl Jn Jq Jr Lh Me On Pe Qa Qe vS) Oe(Ik Iv Jg Lh Ne Nh Nl Nt On Pe Qa Qe) Me(Iv Jg Jq Lh Mm Nh Nj Nl On Qa) Ne(In Jl Jn Jq Jr Lh Nh Nj Qa Tj) Pe(Ii Jk Jo Mk My Nh Nj Nl Ns Pa) In(Hw Ir Jg Jt Mz Nc Nh Nt On) Iv(Hx Ik Jk Jo Lv Mb My Nl Pa) Qa(Ii Jo Jq Mb Mj My Nj Nl) Jn(Ik Jl Js Mb My Nh Nl Pa) Lh(Jk Jo My Nh Nj Nl Of Pa) On(Ii Mk Mv Mw Nj Nl Ns) Jl(Jo Jr Nl Ns Og Pa) Qe(Ii Jk Jq My Nj) Ik(Jo Jq Jr Mz) Nj(Jp Mz Nk) Jg(Jk Mv Mw) Jq(Mb Nh Pa) Jr(Nh Nl Pa) Wm(Ms Tj) Fp(Mh Pg) Pf(Co Pa) AdAj LvNl MbIs MqMz MyJh NcNk} Is{Oy(aA Fr Hu Ik Iv Jh Jl Jp Jq Lu Me Mm Mr Nb Nc Ne Nh Ni Nj Nl Nt Oe Om Pc Pd Pe Po Qa Qe Wm) Nj(aA Hq Jl Jn Jo Jp Jq Jr Lh Me Mm Mt Mz Nb Ne Nk Oe Og Pb Pf Qa Qe) Mm(aA Ii Jk Jn Jo Jq Jr Lh Lu Lv Ml Nc Ne Ni Nl Ns Oe Og Pb Pf) Lh(aA Hq Hr Hx Md Mk Mw My Nb Nc Ne Nl Ns Oe Of Og Pb Pf) Jk(aA Hu Ik Jl Jp Jq Jr Lu Mr Mz Nb Nc Ne Nh Ni Pe Po) Jo(Ik Iv Jg Jl Jn Jq Me Mr Mt Ne Ni Nl Nt Pe Pf Po Qe) Oe(aA Jg Jl Lv Mt Mz Nb Nc Ne Ni Nl Nt Og Pb Pf Qa Qe) Jq(aA Ii Ik Jl Lu Mb Md Mq Mt Ne Ni Nl Og Pb Pf Qe) Pb(aA Ik Jg Jl Lu Me Mr Mt Ne Ni Nl Pe Pf Po) Og(aA Jg Jl Lu Mt Nb Nc Ne Ni Nl Pf Qe) Ii(Fr Jg Jl Lv Mt Nl On Pf Po Qa Qe) Ni(aA Jg Jl Lv Mt Nc Nd Ne Pf Qe) Hq(Jg Jl Lv Me Mq Mt Nl Pf Po Qe) Me(aA Jg Jl Mq Nc Nd Nl Pf) Nc(aA Aj Mt Mz Nb Nc Nh Qa) Mq(aA Aj Ct Hr Hw Hx My) Nd(Jg Jn Jr Mn Mp Mw Mz) Nl(aA Lv Mz Nb Nc Pf) My(Jh Jl Mt Pc Pf) Aj(Ad aN Jg Pf) Ns(Jg Jl Mt On) aA(In Lv Mt Ok) Mk(Jl On Pe) Ch(aN Ji) Ct(Ba Pf) Jg(Mu Mv) WmMs LuPf MwOn QaQb} Lj{Jq(Fr Ik In Jl Lh Lu Mb Md Me Mm Ms Ne Nh Ni Nj Nl Nt On Pb Pc Qa Qe) Mm(Hu Ik In Iv Jg Jl Jn Jr Lh Lu Mr Ms Mt Ne Nh Ni Nj Nl On Qa) Jg(Io Iv Jk Jl Jn Jt Lh Lu Mt Mw My Ne Nh Nl Ns Oe Og Pb Qa) Lh(aA Hq Hv Hx Ii Ik Jo Lu Me Mj Mq Ne Nh Ni Nl Nr Oe Oy) In(Iv Jh Jn Jr Me Mr Nc Nd Ne Nh Ni Nl Nt Om Pe Qe Wm) On(aA Hq Hv Ii Ik Lu Md Mk Mw Ne Nh Nl Ns Oe Og Pb) Nd(Iv Jh Jn Jr Lw Mi Mr Mt Mw Nb Om Pc Pe Qa Qe) Jl(Ik Lu Me Ms Mt Ne Ni Nj Nk Oe Ok Pa Pb) Mq(Fr Jn Jr Lu Me Mj Ni Nl Pb Pc Qa Qc) Lv(Fr Ik Io Me Ms Nb Ni Nj Nl Pb Qa) Mt(Hv Iv Jn Lu Mr Ne Ni Nj Ns Oe Pb) Ke(Aj De eC Ii Jk Kg Kr Mj Ne qC Rh) Qa(Hv Jk Lu Me Mj Ms Ne Ni Nj Oe) aA(Hv Ip Lw Me Ms Ni Nl Oe Pb Pc) Nj(Fr Iv Jh Jn Jp Mr Nk Qe) Me(Fr Jp Nl Pc Qe) Ni(Ik Nc Ne Nl Qe) Ik(Fr Iv Jn Jp) Nl(Fr Ne Nk) Ji(Ha qC Rh) Aj(Ad Ba) Ms(Om Qe) qC(Mz Nw) MyJh NcNk NeNh QeOe} Ok{Jt(Ik Iv Jg Jn Jq Jr Lh Lu Lv Me Mr Mt Nb Nc Nl Nt Oe On Pb Pc Pe Pf Po Qe) Pb(Ik Iv Jl Jq Jr Lh Lu Lv Me Mr Mt Nb Nc Nd Ne Nj Nl Oe Pe Pf Po Qe) Oy(aA Fr Ik Iv Jl Jq Jr Lh Lu Lv Mr Nc Ne Nj Nl Pc Pe Po Qe) Lu(Hr Jl Jq Jr Lv Me Mq Mt My Nc Nd Ne Nj Nl Oe Qa Qe) In(Hr Iv Jg Jm Jn Jq Lh Mb Ml Mr Mw Nr Oe Pc Pe Pf Qb) My(Ik Jh Jl Lh Lv Mq Nd On Pf Po Qa Qe Wm) Hr(Ik Jl Jr Mq Mt Nc Nd Ne Nj Nl Pf Po Qe) Jq(Ii Ik Mb Md Mq Mt Nc Ne Nj Nl Oe Pf Qe) Nd(Fr Jn Jp Ly Me Mm Mw Oe On Pc Po) Jl(Jk Jr Lv Mb Mk Mt Nc Nl Ns Oe Og) Ii(Ik Iv Jr Lh Lv Me Mt Pf Po Qb) Mq(Jr Lv Me Mt Nc Nl Og Qa Qe) Oe(Jr Lv Mt Nc Ne Nj Nl Pf Po) Nl(Jr Lv Nb Ne Ni Nk Qe) Qa(Hq Hv Hw Lv Mj Ne Og) Mt(Jk Jr Lv Md Nj Qe) Nc(Jr Lv Ne Ni Nk Qe) Jk(aA Ik Jr Pf Po) Qe(Hq Me Ni Og) Nj(Lv Nb Ni) Ik(Jn Mg Og) Pf(Hq Me Pa) Jg(Mg Mw) Jr(aA Lv) WmMs PoHq Mblv MePc NbNe} Ke{Wm(aC Ao Bg CP cV Dk hO hP Hq Hx Ii In Iz jD Je Jk lM Mk Nq Nx Ny pF Qx Vp Tj) Rh(Aj Ao Aw Bg Ch Co Ct De Dk Dp Hq Ib Ii Iz Jk Jo Kg Mw My Nb Oa oE Oy Qt Tn Ut) Ne(Aj Ao Bg Ch Co Dk eC Hc Hq Ib Iz Jo Kg My Nb Oa oE Oy Ut) Pf(Aj Bg Ch Co Cp Ct De Dk Hc Ib Ii Jo Kg Mw Ua Ut) eC(Ao Bg Ch cl Cp Hc Ib Iz Kg Mw Ma My Oa Qt Tn Ut) Dp(Aj Bg Ch Cp De Dk Hc Hq Ib Ii Iz Jk Jo Oy Ut) fN(Aj bR cB Cw Db De Fb Gl Hc Kg Md Om Ou) Cp(Il Kr Kz Ly Mq Ms Oa oE Oz Ri Uk) Ms(Aj De Dk Hc Hq Iz Jk Kg oE Ut) Hc(hP Hu Jh Kr Mq oE qD Ri Uk) Iz(Ba Il Kr Mq Mw Oa Ri Uk Uu) Oa(Aj De Ii In Jk Kr Mj Nv) Ch(hP Kr Mw qD Ri Uh Uk) Aj(Ib Il Uh Ut Uu) Bg(Kr oE Ri Uk Ur) Jk(Ax Il Jm Mw Qa) Kg(Hx Kr Ri Uh) Uk(De Ib My Ut) Kr(Ib My Ut) cB(IN qC qD) oE(cH De Ib) Ax(Ii Ut) Hq(Mh Mq) qC(Db nW) DeUt DkRi qAnW} Qa{Jk(aA Fr Hu Ik Jl Jp Jq Jr Me Mm Mr Ms Mt Nd Ne Ni Nj Nl Nl Nt Nx Oe Om Pc Pe Po Uh) Nj(aA Jg Jl Jn Jp Jq Jr Lh Lv Me Mm Mq Mr Ms Mt Mz Ni Oe Og On Pb) Ms(aA Iv Jl Jr Me Mm Mr Mz Nd Ne Ni Nx Oe Om Pb Pc Pe Pf Wm) Jq(aA Hq Ii Ik Jo Lv Mb Md Me Mm Mq Mt Ne Ni Nl Oe Og Oy Pb) Nd(aA Fr Iv Jg Jn Jr Mn Mp Mt Ni Oe Og Pb Pc Pe Pf) Mq(aA Hr Hv Hw Ii Jo Lv Mj Mt Ne Ns Oe Og Oy Pb) Lv(aA Ii Jo Me Mj Mm Mt Ne Ni Oe Oy Pb Qb) Oe(aA Jg Jl Lh Mm Mt Ne Ni Nt On Pb) Lh(Hq Hr Hx Jo Mj My Ni Og Pb) Jl(Ii Me Mk Ne Ni Og Oy Pb) Mt(Ii Me My Ne Ni Oy Pb) Jg(Ii Jo Me Mw Ni Og Pb) Oy(Mr Om Pc Pe Pf) Pb(Ik Mr Ni On Pf) aA(Ik In Me Mm) Ne(Ik Nc Nh) Ni(Mm Nc Nl) On(Ii Mw Og) Ba(Aj Ct) CtcT WmIn MeMm MyJh IkOg} Qe{Ms(aA Fr Ik Iv Jn Jp Jr Lw Me Ml Mm Mr Mz Nd Ne Nh Ni Nj Nl Nt Nx Oe Om Pc Pe Pf Po) In(aA Ir Iv Jg Jl Jn Jr Lh Lv Mm Mr Mt Mz Nb Nc Ne Nh Ni Nt Oe Og On Pe Pf Po) Nd(aA Fr Iv Jg Jk Jn Jp Jr Lv Lw Mm Mp Mt Mz Ne Ni Oe Og On Pb Pc Pe Pf Po) Jq(aA Ii Ik Jk Jl Jo Lv Mb Md Me Mm Mq Mt Ne Nh Nj Nl Nw Oe Og Oy Pb) Mq(aA Hr Ii Jk Jn Jo Jr Lv Me Mj Mt Mz Nj Nl Ns Oe Og Oy Pb) Lv(aA Jk Jl Jn Jo Me Mm Mt Ni Nj Nl Oe Oy Pb) Nj(aA Jk Jl Jn Jp Jr Lh Mt Ne Ni Nk) Jk(aA Ik Jg Jl Lh Mt Nl On Pf) Lh(Ii Jo My Nl Oe Oy Pb) Mt(Me My Ni Oe Oy Pb) aA(Ik Me Mm Nl Oe) Me(Jl Mm Nl) Aj(Ad Ba) Fp(Jr Mj) My(Jh On) Nc(Ni Nk) Jl(Mk Oy) MwJg NeNh NiNl OyPf} Mt{Ms(Ij In Ip Jn Jp Jt Lw Me Mm Mn Mp Mz Nb Ne Ni Nn Om Pb Pc Pf Po Qd) Lv(aA In Iv Jl Jn Jq Jr Lh Me Mm Mq Mr Mz Nd Ne Ns Oe Og Pb Pe Pf) In(aA Iv Jn Jq Jr Lh Me Mr Mz Nj Nt On Pe Pf Po) Mq(aA Jl Jn Jq Jr Lh Me Mz Nd Nj Ns Oy Pb Pf) Jl(Ii Jk Jq Me Mk My Ne Ni Nj Ns Oe Oy Pb) Nd(aA Iv Jp Jq Lh Mr On Pe Pf) Lh(Ii Jk Jo Me My Nj Of Pb) aA(Ip Jq Me Mm Nj Ns Pb) Jq(Md Me Nj Pb Pf) Oy(Iv Mr Pe Pf) Pb(Iv Mr Pe Pf) Nw(Iv Ni Nv) Mc(Mm Pf) On(Jk Mw) AjPf BgJi ChWe MyJg NcNl} Pf{Oy(aA aC Ad Aj As bA bL Bn bS cO Cp Cq Cu Cw Dc dE dJ dM Dp Fp Id Jg Jl Jq Kd Kn Ko Kq Lh Lv oH Or Pi Pk Ra Sr Tn Tr Tv Uh Ul Un Ur Us Vp) Aj(Ba Co Hq Id Ij Jg Ji Jq Ko Kq Mk Mq Nd Vt) Ji(Bg bN Ch Co Ct De Iz Kg Ua Tj) Nd(Fp Jg Jl Jp Lh Lv Mm Mq On) Vt(Hq In Jk Jo Kg Ur Tj) Ct(Ad Ba Jq Mk Mq Ni) Hq(aC bN Fp Kq Nw) Mq(aA In Jq Pb) Ms(Jl Lh On Wm) Co(Ij Nw Uh) Bg(In Ur) My(On Wm) Iz(Ko Mw) Jk(dM Nw) Pb(Fp Lh) ChUh LvaA KgKo} Nw{Mr(Hq Hx Ii Jk Mk Mw Nb Nv Ny Of Pg Po) Jo(Hv Hw Ir Jl Jn Jq Jt Lh Nt Nx Pe) qC(aN aZ Ba DB dE Mh oE Qy Ur Wm) Pe(Hx Jk Nb Nv Of Pa Pg Po) Lh(Hq Hx Nb Nx Ny Of Pg) Mb(Hv Hw Iv Jn Jq Mc) Jl(Hq Hv Hx Nb Og Pg) Lu(Mu Mv Nc Of Og) Iv(Hv Mk Ns Of Pg) nW(eT fN rS vH wD) Ni(Ii Ik Mw Nv) Jg(Jk It Mu Mv) Jn(hO Hv Nv Nx) Wm(Mw Nv qB) Nt(Ii Jk Nv) Hw(Hv Nx Of) hO(dJ fN Ko) qD(Ba Ch Qy) Jk(Jm Po) MlNy MwPc NeNh HvNx KpfN} Nd{Lh(aA Fr Hr Hx Ii In Jg Jl Jn Jo Jp Jq Jr Lv Mn Mp Mq Mw My Mz Ne Of Og On Oy Pc Po) Jl(aA Fr Ip Jg Jn Jq Jr Lv Me Mk Mn Mp Mq Ms Mw Mz Nc Ns Oc Og On Pb Pc Po) On(aA In Iv Jk Jo Jp Jq Lv Me Mk Mq Mr Mw Ne Og Ph Pe) Mq(aA Fr Jg Jq Lv Mm Mp Mr Mz) Jp(Iv Jq Lv Mm Mp Mr Ms Pc Po) Mm(aA Iv Jq Lv Mr Pe) aA(Jg Jq Lv Pc Po) Jg(My Oy) PoIn FpPe} Ms{Om(aA Ik In Jg Jk Jl Jp Jq Ml Mw Mz Ne Ni Nl Nx Oe Pb Qd Wm) Lh(In Iv Jp Jq Me Mm Mw Ne Ni Nj Nl Nx Oe Pb Pc) Jl(Ik In Jp Jq Lv Me Ml Mq Mz Nj Om Po) Ji(bN cl Ct eC Ib Kg Kj Rh Ri Uk Ur) Jg(aA Jq Jr Lv Me Mq Mz Oy Po) Wm(Jp Jq Pe Uh) Mq(aA Fr Jp Jq) Fp(Ij Pb Pz) aA(Jq Lv Po) AdAj LvJp UrVt} Mq{In(aA Ir Jg Jl Jn Jq Jr Lh Lv Mr Mz Nc Ne Nh Nj Nl Nt On Po Qd) aA(Ip Jg Jq Jr Lh Lv Mm Mz Nc Ne Nj Nl Ns Pb Pc Po) Jq(Jg Lv Md Ne Nh Nj Nl Ns Pb) Nj(Fr Jn Jp Jr Lh Mz On) Jg(Aj Jo Mw Ns Og Pb) Ji(Aj Bg Ch Ct) Lh(Ii Jo Oy Pb) Ns(Lv On) Nk(Nc

Figure 3 Continued

Nl) AdAj BaCt FrOy LvJn NeNl tUnW} Ji{Rh(Aj Bg Ch Ct De Dp Hc Ii In Jk Jo Kg Mj Mk Ne Oy Qx Uh Uk) Ne(Aj Bg bN Ch dM eC Hc Kg Kr Oa Ri Uk Ur Ut) Wm(Bg Dk eC Hc Ib Jd nW oE Ur Ut Tj Th) In(Aj Bg bN Ch Cs Kr Oa) Aj(Ad Ba Jg) Oa(eC Ha Mj) Uk(bN Ib Jm) Ba(Ch Ct) Bg(bN Qg) Uh(Ch Kg) DeQg OufN} Fp{Pb(Ip Ir Jt Lw Mn Mz Ni Nl Om Pc) Oe(Jt Mn Mr Mz Nt Om Pe Qd) Oy(Iv Jh Mi Mp Mv Nb Nn Po) Pc(Jn Jr My Mz Ni Ns Pe) Ne(Nc Nh Nj Nk Nt) Jo(Ip Jt Om Pe Pz) Ni(Mn Nc Nj Nl) Hq(Fr Mi Mp Po) My(Mv Nb Om) Fr(Jn Nl) Ns(Lw Nn) Om(Md Og) MjJp MkMp MnNl NjNk HuJg HxIv} Jg{Oy(Hu Ij Ik Il In Ir Jn Jr Lu Mi Ml Mx Mz Nc Ne Nf Nh Ni Nj Nl Oz Pa Qb Qd) My(aA Iv Jl Jq Jr Lh Lv Me Mr Ni Nl Pe Po Wm) Mw(aA Jl Lh Me Mr On) Jk(aA Lh Pe) LvaA MdJq MeIn MkJl JoLh} Lh{Oy(aA Fr Ik Jl Lv Mm Nj Nl Om On Po Wm) aA(Ii In Jk Jo Lv Me Nj Nl Oe Pb) Nl(In Jo Ne Nk Pb) In(Ik Jl Jr Nj) Jo(Ik Jl Lv) My(Jh Wm) Pb(Ik Nj) NcNk IiJl} Wm{Uh(bA bN bV dF dM My nW oE oH Vv) In(bA dF Jq Mw Pe) My(Jp Jq Ny Om) Vt(oE oH Ur) Jq(Nv Ny) TjPo ThSt HbdM UrbA OyPe qZuM} aA{Lv(Ik In Ip Jq Jr Me Mm Mz Nj Nl Pb Po) Po(In Nj Oy Pb) Mm(Ik Me Nj) Jq(Ik Md Nj) Nl(Ne Nk) MzNj IkIn} Ct{Ba(Ad Aj As Bn Ch Cp Cq Cs Cu Cw Dc dF dJ dM) dF(aC Ad dH dJ) Ad(bA cT)} Jl{In(Ik Jq Jr Lv Me Nl Po) Lv(Jk Mk Oy) Ne(Nj Nl) Nk(Nc Nl) MlHx MyJh} On{My(Jk Jr Lv Mb Md Nc Ne Nh Ni Nl Ns) In(Me Nj) LuOy MdJq NeNl} Aj{Ad(aM bF cT Gp Hu Ne Pe Uh) Ba(aC dJ Id Vt) Uh(Id Tv) dFdJ} Vt{qZ(bL dB dE nW uM) oE(bN cH Ne Op) NeeC} nW{wD(jY Pj qD uX) wP(Ax Cs) MzuX IdvS hBjl} Uh{Tv(Ch Jo Kg) Ad(Jo Kg) ChTn IdKg} Vq{oE(cV In Ip Nk Or Qv) EdFi} Po{In(Lv Nj Nl) Nk(Nc Nl) HaOy} Mz{Rb(qC vS tM) IlqC VvrW rAvS} vS{ChUc LuId UaKo dBhB} aC{dM(Ad bR) ChdF} qZ{ChUu DbHc KobR} Bc{Wc(cQ pK)} Nj{Jp(Lv Ni)} Jq{NkNl IkIn} DrIlKg DuLdeC IbTruI OarBqC dMrCjO

Constrained panels with 2 analytes, where 1.0E-8 >= 'model p-value' > 0. Contains 145 panels of 192,797 total panels evaluated. : Et(aA Aj Ch Fp Ik Im In Is Iv Ji Jj Jl Jn Jo Jq Jr Jt Kg Li Lj Lu Lv Lx Mb Me Mh Ml Mq Mr Ms Mt My Nc Nd Ne Ng Nh Ni Nj Nl No Ns Nw Oe Oy Qa Qe Wm) Ji(aA Fp Ii Ik Im In Jj Jo Jq Jt Li Lj Lu Lx Md Mq Ms Mt My Nd Ng Ni Nj Nl Nx Oe Og Oy Pb Wm) Jj(Fp Ik Im Is Jg Jl Lh Li Lj Lx Mq Mt No Nw Ok On Po Qa Qe) Nw(aA Fp Im Is Lj Lv Md Me Mq Ms My Nd Ng Nj Nl Oy Pb Qa) Fp(aA Im In Is Jl Jq Lh Lv Lx Mm Mq Mt No Ok On Qa) No(Lv Nd Nj) Ms(Is Lx Ok) Im(aA Lv Ok) Is(In Lx) AdAj NgJg JoOk Constrained panels with 2 analytes, where 1.0E-7 >= 'model p-value' > 1.0E-8. Contains 177 panels of 192,797 total panels evaluated. : Im(In Is Iv Jk Jl Jn Jq Jr Lh Li Lj Lu Lx Me Mm Mq Mr Ms Mt Mz Nd Ng Ni Nj Nl No Oe Og On Pe Pf Qa) Ok(aA In Is Jl Jr Li Lj Lu Lv Lx Me Mq Mt Nc Nd Ng Nj Nl No Nw Qa Qe) Nw(Ii Ik In Iv Jn Jq Jr Li Lu Lx Mt Mw Nc Ne Ni No Ns Oe Qe) Fp(Fr Iv Jg Jn Jp Jr Li Lw Mr Ms Mz Ni Oe Pb Pc Pe Qe) Lx(aA In Iv Jl Jn Jq Lh Lv Me Mq Mr Nd Ng Nj Nl Qa) Is(Jk Li Lj Lv Me Mq Mt Nd Ng Ni Nj Nl No Oe Og) No(Aj Ik In Me Mq Ms Mt Ne Nl Qa) Jj(Ij Ip Jm Lv Nl Nt Pf Qb Wm) Et(Bg Co Cs Ct Iz Kj Oa Uk) Li(aA In Jq Lv Me Mq Ng Ni) Lj(aA Jg Lh Lv Mq Mt On) Qa(In Jk Lv Mq Ms Nd) Ms(Lh Mt On Qe) On(My Ng Oy) NgKe Constrained panels with 2 analytes, where 1.0E-6 >= 'model p-value' > 1.0E-7. Contains 309 panels of 192,797 total panels evaluated. : No(aA aC Bg bS Ch Ct eC Hc Ip Iv Iz Jg Jl Jn Jq Jr Kj Lh Li Lu Lx Mb Mf Mm Nc Ng Nh Ni Nq Ns OE Pb Pc Qe Rh Ua Ur Vt Tj) Jj(aA Fr Ir Iv Jn Jp Jq Jr Js Jt Mr Mw Mz Nc Nd Ne Nh Nj Nm Nn Nr Nv Nx Oa Oh Om Pe Pz Qd Vt) Li(fN Iv Jk Jl Jn Jr Lh Lu Lx Mm Mr Ms Mt Mz Nc Nd Ne Nh Nj Nl Ns Nt Oe Og On Oy Pb Qa Qe vS) Ke(Aj Ao Bg Ch Co Cp De Dk eC Et Hc Hq Ib Iz Jk Kg Lj Ms Oa oE Oy Rh Uk Ut) Qa(aA Is Jg Jl Jq Lh Lj Me Mm Mr Mt Ne Ng Ni Nj Nl Oe Og On Oy Pb Pf) Qe(aA Im In Is Jl Jn Jq Lh Lj Lv Lx Me Mq Mt Nd Ng Ni Nj Nl Oc) Et(aC AO Ap Ax bN cI De Dg dM Ed Hc Id Kl Kr Rh Ur Us Vt) Is(aA Ct Jg Jl Jn Jo Jq Lh Lu Mm Nb Nc Ne Nh Nt Oy Pb Pf) Lx(Ik Ir Jg Jr Lj Mt Mz Nc Ne Nh Ni Oe On Oy Pb Pe) Mt(aA In Iv Jl Jn Jq Jr Lh Lv Me Mq Mr Ng Pe Pf) Lj(Fr Ik In Iv Jl Jq Me Mm Nd Ni Nj Nl Om) Mq(aA In Jg Jq Lh Lv Nj Nl On Pf) Ji(Aj Bg bN Ch Ct Rh Uk Ur) Ok(Hr Ik Jq Jt Ne Oe Pb Pf) Lh(aA Nd Ng Nj Nl Oy) Im(Ml Nc Ne Nh Nt) Jl(In Lv Ms Nd) Jg(Lv My Oy) Pf(Aj Bg Ct) aA(Jq Lv Po) Ba(Ct Ng) Nd(Jp On) Kq(Aj Ng) Nw(hO qC) oE(Vq Vt) WmJq aCdM Constrained panels with 2 analytes, where 1.0E-5 >= 'model p-value' > 1.0E-6. Contains 581 panels of 192,797 total panels evaluated. : Jj(Ad Ax BA Cs Cu Dp Fa Fy Hu Hv Hw Id Ih Ii Il It Jk Jo Ke Ko Kp Kq Lu Lw Me Mf Mg Ml Mm Mn Mp Mu Mv Mx Nb Ng Ni Nu Ny oE Pc Pd Pg Pj Qc Qh Rm Sr St Uc Uh Un) Ke(Aw Ax bN Cs Ct Dp fN hO Ii Im In JD Jo Kj Kr Lx Md Mk Mv Mw My Nb Ne No Nv Om Oz Pb PF Qt Qy Ua Ur Us Vt Wm) Pf(aA aC bL bN bR bS cA Ch cL CO dH dJ dM Dr Iv Iz Jl Jq Kg Lh Lj Lv Me Nd Nj Nl oE Oy Qe Ua Uh Uk Ur Vt Tj) Mq(Aj Ct Fr Ik Ip Ir Iv Jl Jn Jp Jr Js Me Ml Mm Mn Mr Ms Mw Mz Nc Nd Ne Ng Nh Ns Nt Om Pb Pc Pe Po Qd Vt) Jl(aA Fr Ik Ir Jg Jk Jn Jp Jq Jr Lh Mb Me Mf Mk Mm Mz Nb Nc Ne Ng Nh Ni Nj Nl Ns Nt Oe Og On Oy Pb Po) Lh(Hq Hr Hx Ii Ik In Ir Iv Jg Jk Jn Jo Jp Jq Jr Lv Mb Me Mm My Mz Nc Ne Nh Ni Nt Oe Of Og Pb Po Qd) aA(aC Fr Ij Ik In Ip Ir Jg Jn Jp Jr Lw Me Mf Ml Mm Ms Mw Mz Nc Nd Ne Nh Nj Nl Nr Nt Nx Om On Pc Qd) Lj(dF Hu Ip Ir Jh Jn Jp Jr Jt Lu Lw Mr Ms Mu Mw Mz Nb Nc Ne Nh Nt Pb Pc Pe Po qC Uh Ur) Lv(Fr In Ip Ir Iv Jn Jp Jq Jr Me Mm Mr Mw Mz Nb Nc Nd Ne Nh Nj Nl Nt Om On Pe Po Qd) No(aD bN cA De dM Dp Gp Ha Ib Kg Kr qC qD Qt Qv Qw Ri Tv Uh Uk uM vS Vv Th) Jg(Aj In Iv Jn Jq Jr Me Mr Ms Mt Mw Nd Ne Ni Nj Nl Og Pe Po Qe) Ji(aC cI cV dM Dp eC Hc Ib Iz Kg Kr Oa oE qC Rb Ri Uh vS) Et(bA bV cP Ef Ib Jd Kd Ks oE Qt Qu Qv Qy Ri Ua Ug Vv) Qe(Aj Ik Iv Jk Jr Mm Mr Mz Nc Ne Nh Nt Og On Oy Pb Pe) Mt(Ip Jp Mm Mz Nd Ne Ni Nj Nl Ns Oe On Oy Pb Po Qd) On(Ii In Jk Jq Jr Me Mw Nc Ne Ni Nj Nl Ns Oe Og) aC(Ad Ax Ba Bc cE Cs Cu Cv Dc dF Dg Fr Im) Vt(bN eC Im In Lx Mw Ne Ng Qv Rh Uk Ur) Po(In Jq Me Ms Nd Ng Ni Nj Nl Pb Tj) Uh(Aj Ax Ch Cs Id Im Ng Oa Qa Tv Wm) Jq(Fr Ik Mm Nd Ne Nh Nj Nl Nt) Aj(Ba Cu Ij Im Is Pe Qa Uc) Ct(Ad bA dF Im Kq Pe Qa) Fr(Jr Me Ms Nd Ng Nj Nl) qZ(aZ bL DB dE Ko Ou) Wm(bA dF dM Im oE Ur) Ng(Ad Ko Om Tn Uf) Is(aN Ch eC jQ Ur) Mm(Jr Me Nd Nl) Ur(Ax Im Oa Qa) Ch(Im Kq Qa) Mz(jK qC vS) Nd(Iv Mr Pe) Id(eC qC vS) Jp(Me Nj Nl) Li(qC rS uM) Nw(oE qD Rh) dM(jO rC rY) TjLx NtIn MsOm ImUk IzKq bRfR hBjO nWuX Constrained panels with 2 analytes, where 1.0E-4 >= 'model p-value' > 1.0E-5. Contains 1,283 panels of 192,797 total panels evaluated. : Uh(aA Ad Ao As bA Bg bN bV Co Cq Ct Cu Cw Dc dM Dp eC Ed Fa Fp Fy Hc Hv Hw Ij In Is Iv Iz Jl Jn Jo Jq Jr Kd Kg Kj Kk Kn Ko Kp Kq Kr Li Lw Lx Me Ml Mm Mq Mr Ms Mw My Na Ne Nm Nw oE Or Pe Pi Pk Qd Qe Qv Ra Rh Rj Sr St Uk Ul Un Up Ur Us Vt Vv) Pf(aD bA cH cK Dp eC Ed Eq Ez Fr Hb Hc Ib Id Ik In Ip Ir Jg Jn Jp Jr Jt Kd Kj Kk Ko Kr Mm Mr Ms Mz Nb Nc Ne Ng Nh Ni Nt Oa Og oH Om ON Pb Pe Pj Po Qd Qt Qu Qv Qw Rg Rh Sr Ul Un Vv Wc) Vt(aA aC Aj Ax bA bB bF Cs CT cV dD dF dM Dp Ed Fa Gp Id Ij Is Jo Jq Kg Kj Kk Ko Li Lj Ly Mn Ms Nr Nw Oa oH oK Ou Oy Oz Pe pF Qa qC qD Qe Qg Ri St Ul vS We Zx Wm) Lj(aC Ad Aj aM BA bB bF bR bV bW cE cT Cv Dc Di dM dN Dp eC Fy Gp Hb Id Jy Kd Ko Kq oE Ou pF Qv Rh Ri rS Sr tU Uf Uk Ul Un vS wB We wL wP Zq) Pe(aA aC Bg bL bN bR bS Ch CO dM eC Fr Ha Ik In Ir Iz Jp Jq Jr Kg Kj Lh Me Mm Ms Mz Nc Ne Nh Nj Nl Nt Nx oE On Pb Po Qd Rh Ua Uk Ur Tj) Lx(Aa aC aD Aj Bg bL bN bR bS CH CO Cs Ct Cv Dc dF dM Dp eC Fi Fy Gp Hc Id Iz Kd Kg Kk Ko Kr Oa oE Qv Rh Ri Ua Uk Ul Un Ur Vv) Jq(aC Aj Ax Cs Ct dM eC Hu Ij In Ip Ir Iv Jn Jp Jr Mb Md Me Mh Ml Mr Ms Mw Mx Mz Nb Nc Nn Nr Nx Oa oE Oh Pc Pz Qb Qd Rh Uk Ur) Ur(Ad bA Bc Cs Cu Cw Dc dM Dp Fa Fp Fy Id Ij Ip It Jl Kd Kf Kn Ko Kq Lh Li Lw Mq Mr Mw Nr Nw Ou Qd Qe Qh Rm Sr St Tv Un Us) Im(aI bB bS bV bW cA Cs CV dE dF dJ dM dN Dr eC Fa gP Hb Hc Id Iz Kd Kg Kj Kk Ko oE Ou pF Qv Qw Rh Tv Ua Ul Un Ye Th) Jj(aC Al Ap Ar Bb Bc bV cH cT

Figure 3 Continued

Cw Dc dF Dg dJ Dl dM eC Fb Hb Kd Kf Kk Kn Ks Kz Ma Or Ou Pi Qm Rf Rh Tn Tr Tv Uf Ul Us) dF(aA AD aF Aj aM aO Ax Bg bL bN bR bS bZ cA cF CH cL cO Cs Cv Dc dE dH dJ dM Fp hA In Is jO Nd Ng Nw Qa Qe) Qd(aC Aj bA Ik In Iv Jg Jl Jn Jr Me Mm Mr Ms Nc Nd Ne Ng Nh Ni Nj Nl Nt OE Om On qC qD Wm) Nw(aC aD Aj Ao bB Bg bN Ch Co Cs Ct cV dM Dp eC Ed Id Iz jI Kr Oa pF Qv Ri rS rW Uk Ul vT Tj) Qa(aC bA Bg bN bR bS cT Cv eC Gp Id Iz Kg Kj Kr oE oH pF qC Qg Qv Rh Rt Tv Ua Uk Th) Wm(aC al bB bF bN bV cE cT cV dD eC hB In Jp Lh Lv Lw Mq Mw Ng oH Ok pF qZ rB Ti) eC(aA Cu Dc dM Et Fy Ij Kd Kn Ko Kp Kq Lh Li Mj Ml Mr Mt Oa Pi Sr Tv Uc Un Us) Aj(Ap bA Dg Fa Fr Fy Id Jl Jp Ko Lh Li Mt Mw Oa Ok On Sr St Tn Uf Un) Ch(Ad BA Fr Fy Id Ij Jg Jp Lh Li Mq Mt Mw Ok On Qe qZ St Tn We Zq) Nt(Fr Ip Ir Iv Jn Jp Jr Me Mm Mr Ms Mw Mz Ng Ni Nj Nl Oe Om On Pc Po) In(Ax Cs Fa Fr Fy Id Ij Ik Ir Iv Jr Ko Kq Mr Nj Nl Oa Om Qb Sr St Un) Mz(Fr Ik Iv Jg Jr Me Mm Mr Ms Nc Nd Ne Nh Nj Nl Po qD qY rW uX wB) Is(aC Al bB Bg bN bR bS bV cA Cs cV dJ dM Iz Kg oE Qv qY Rh Ua Uk) Ne(Fa Fr Id Iv Jn Jp Jr Kq Mm Mn Mr Nh Nl Oa Om Po Sr St Un) On(Ct Fr Ik Iv Jg Jn Jo Jp Mb Mh Mk Ml Mr Mu Mv Nh Of Pb Po) aA(AD aI aM bB bF bM bN bR cE cF cH dD dJ dM Ni Ns Pz Qb) oE(Bc cH Dr Fy Id Ip Jl Kd Ko Kq Li Mt Mw Ng Oa Qc Sr St Uy) Nl(Ij Ip Ir Iv Jn Jr Jt Me Mn Mp Mr Mw Nb Ni Nk Nn Nv Om) aC(aJ aM Ap bA bB bF bV cF cG cH dG dN Dr fR Ij Li Mw Qe) qZ(aH aW bS Dg dJ Fb Id iH Ke oK Ow Pj qA qB uM vS vV) Mm(Fr Hu Ij Ik Ir Iv Jn Jp Ml Mr Ms Nc Nh Ni Nj Po) Ng(Ap Ax Cu Dg Fa Fy Id Ij Jp Nv Oa Sr St Tr Uc Un) dM(Ad aQ bB bF bR cE cH dD dJ Gp Ij Li Ml Mq Oa rX) Kq(Ao Bg Co De Dk Hc jD Jk Jo Kg Kj Oa Oy Ua Uk) Fr(Ct Ik Ir Iv Jn Mr Mx Nc Nh Ni Oe Og Oy Pb) Qe(bA Bg bN Cs CT Cv Id Kg Qv Rh Ua Uk Th) Mr(Ik Ir Jp Jr Lh Me Ms Nc Nh Nj Pb Po) Iv(Ik Ir Jp Jr Mb Ms Mw Nc Nh Nj Om Po) Jg(Ir Jo Mh Mu Mv Mx Nc Nh Ns Oe Pb Qb) Oa(bA Hb Id Ko Lp Lw Mw pF qC Rh Uk Zq) Lv(Ih Ij Ik Mn Mp Ms Nn Nr Oh Pb Qb) Nd(Aa Ij Ir Jn Jr Jt Mp Mw Nv Om Qb) Cs(bA bF cE Cv dJ Gp Mq qC vS wP) Ct(cT Cu Fy Id Ij Jl Ko Lh Li St) Jp(Ik Ir Jn Jr Mf Ms Nc Nh Ni Po) Nj(Ir Jn Jr Jt Mp Mw Ni Nv Om) Id(Hb hP Kp Mq Mw Qv Rh Uk uM) Ko(bN Jo Kg Kj Mq qC Rh Uk vS) Po(Hq Jn Jr Nc Nh Oe Og Oy) qC(Ax Dc Fb Jl Kn Kp Ny Un) Dr(cV Et Il Mq mZ Qb St) Ji(hP pF qD qY vV Wc yL) Ax(bA cE Gp Hb Mq vS) Et(jO nW pF tT Yh Th) Jl(Ip Ml Mw Nx Om qD) Jr(Ik Ir Jn Me Nh Om) Uk(Fa Fy Mw Sr St Un) No(jK qY uO Vu xA) Ms(Ij Ir Nv Qb Un) aM(bA bF cE fR Ke) wD(dE nW Ou Pj Ri) Fa(Fi Hq Iz Th) Me(Nh Nn Nv Om) Ij(Bg Hc Iz Wc) Il(Eq Sf Yl Ye) St(Jk Qv Ye Th) Mq(Bg Dc Wf) Mt(Bg bR bS) Nh(Jn Mn Om) We(Lz Ml Ye) Ke(rS uM uV) Li(bL bN bS) bA(Ad bB Oy) hB(dJ jD jI) Fy(Jo Kg) Nc(Ni Nk) Kp(fN vS) Om(Og Oy) Un(Rh Wc) AdKj EdVq MwIz IkJn HcJh KgLh OuuX aDcE cGhA dBrN

Constrained panels with 2 analytes, where 1.0E-3 >= 'model p-value' > 1.0E-4. Contains 2,695 panels of 192,797 total panels evaluated. : eC(Ad aM As Ax bA bF cE cH cI Cp Cq Cs cV Cw dF dJ dL dN Dr Ed Fa Fp Fr Fw HB Hv Hw In Ip Ir Iv jI Jl Jn Jr Js Jt Jy Kf kI Kk Kr Lv Lw Me Mq Mw Mz Na nD Ne Nf Ng Ni Nr Ny oE Ok Om Or Ou Pb Pg Pk Po Qd Qe Qh Qv Ra Rf Rj Rm St Tn Tr Uk Ul Up Ur Vp) dM(aD aI aM An aU Ax BA bL bN cA cF cK cM Cs CT Cu Cv Dc DG dN Dp Fa fN Fp Fr Fy Hb Id In It Iz Jr Kd Kf Kk Kn Ko Kq Kx Lh Lv Me Mn Mt Mw Mz Nb Nd Ne Ng Ni Nj Nr Ok Or Ou Pj Po Qa qC QD Qe Qh Qm Qv Rf Rh sC Sr St uI Uk Un wD zH) Ur(aM As Ch Cp Cq Cv dF Dr Ed Fb Fr Hv Hw Ih Il Ir Iv Jg Jm Jn Jr Jt Jy Kk Kp Kr Kx Me Mj Ml Mp Mt Na Nb Nd Ne Nf Ng Nm oE Ok Om Or Pb Pd Pg Pi Pj Pk Po Pz Qb qC Qm Ra Rf Rh Rj Tn Tr Uc Uf Uk Ul Up uX Wc) Ax(aA AD Aj aM An aU Ba bB bF bN bR bV bW cF cG cH CT Cv Dc dJ Dp eD Id jI Jp Kd Kj Kk Ko Kq Kr Lv Mc Me Mm Mt Mw Nd Ne Ni oE oH Ou pF qD Qg Qv rB Rg Rh Ri Sr Uk Ul uM Un wB We wL wP Th) Wm(AA Dr Fp Fr Gp Hb hW Ih Ij Ip Iq Ir Iv Jg jI Jn Jr Js Jt Kd Ko Lz Me Mj Mm Mn Mr Ms Mt My Mz Na Nb Ne Nm Nr On Pg Pj QC qX qY rN rS rT Sr St tU tX Uk uM Un uT uX vS wB wD We wP Zq yE) Cs(aA AD aE aM aU Ba bB Bc bN bR bW cF cG cH cM cT Dc Dg Dp eD cF fN Fy Hb Id Ij Jp Kd Kk Ko Kq Lv Mc Mm Mt Mw Nd Ne Ng Ni oE oH Ok Ou Pj Qg rB Rg Rh Ri sC Sr Uk Ul uM Un wB We Th) Dr(aG aJ aM aQ Ar Ba bB Bc bR dD dF Ed Fa Fp fR Fw Gp Hb Ij In Is Iv Ji Jj Jn Kd Kg kR Ky Ld Li Lj Lp Lx Lz Me Mh Ml Mt Mw Nd No Nq Oa Pb pF Qa Qe Qx Rh Rt Rz Tz Un Vt Wc We Zq Ye Tl) Mw(bA bB Bg bN bV cH cI Ct Cv Dc dE dF Ed Fa Fy Gp Hb Hc Ib Ik In Ip Ir Jn Jr Jt Kd Kg Kj Kk Ko Kp Kq Me Ml Mm Mr Ms Mx Mz Nb Nc Ne Ng Nh Ni oH Ou Pe pF Qv Qw Rh Sr Ua Ul Un) oE(aA Ad aW Bb bN cM Cu Cv Dc dD dF dJ Ed Fa Fp Fr Fw HB Ij In Ir Jy kC Kf kI Kk Kn Lh Lw Me Ml mM Mq Mr Ms Mz nD Ne nI Ok Or Ou pF Pg Pj Po Qh Qv Rh Tv Uc Uk Un Us) In(aC Ad Ar BA bV Cu Dc Dp Hu Ih Ip Jn Jp Js Jt Kd Kf Kk Kn Kp Kr Me Mm Mu Mx Mz Nb Nc Nd Ne Nh Nn Nr Nv Nx Oh Ou Pg Pi Pj Qh Qm Rf Rh Rm Uc Uf Ul Us Vq We) Oa(aM bB bF bN bV cE cG Ch CT dF Dp eF Fa Fc Fi Fy Gp Ha hB Hq Ij Is Jy Kd Kk Kp Mm Mq Ms Ni oH Ok On Ou Pj Qg Qv Ri Rt Sr Uf Ul Un vS wB We wP Ye Tj Th) Aj(bB Bc bF cE cT Cv Cw Dc dG dJ Dl Ef Fb Fp Gp Hb Ih Ip It Jt Kd Kf Kk Kl Kn Kp Lv Mn Mr Nr Nv Om Ou Pd Pg Pj Po Pz Qh Rf Tr Tv Us Vq We Zq) Ng(Ar Aw bA bB Bc bF bV cE Cp cT Cw Dc dG Dk Ef Fb HB Hu Ik Ir Jt Kd Kf Kk Kn Kp Mm Mr Mu Nn Or Ou Pe pF Pj Qb Qh Qm Rf Rh Ul Uu Vq We) Ij(aM bL bN bS bV bW Co Cv dF Dp Ib Ik Jn Jp Jr Kg Kj Kk Me Mr Mx My Mz Nc Ne Nh Ni Nj Ns Og Oy Pb pF Qt Qv Qy Rh Rt Tv Ua Uk Vb Wf Ye Th) Ko(aA Bg Ch dF Dp Ed Fa Fp Fy Gp Hb Hc hX Id Is Iz Jq Jr Kk Kr Li Lw Ly Ms Ne Nr Nw Ou Oy Pe pF Qa Qe Qv Rf rS St uM Un uX vV wD wP) Uk(Ad aM bA bB Cu Dc dF Fp Hb Il Ip It Jl Jt Kd Kf Kk Kn Kp Kx Lh Li Lw Mm Mq Nm Nr Ok Or Ou pF Pg Pj Po Qd Qh Qm Rf Tr Tv Uf Ul Us) Pe(Dp Gp Hb Hc hP Hu Ib Id Ip Iv Jn Jt Kr Mb Mk Mn Nb Ni Nn Nv OH Om Oy Pa Pc Qb qC Qg Qv qY Ri Rt Tv Ul uM vS Vu Vv We) Fa(bA Bg bL bN bS Ch Ct Dc dJ Dp Fc fN Fy Gp Hc Hv Id Is Jk Jq Kd Kk Lw Ly Ms My nW oH Oy pF Pj qC Qg Rh Ri Sr Ua Un Tj) Ne(aC bV dF Fy HB Hw Ik Ip Ir Js Jt Kd Lw Me Mp Ms Mx Nb Ni Nj Nn Nt Nv Nx Ny Oh Or Ou Pc Pg Pz Qb Qh Rf Uf Ul Us uX) Id(aC bA bB bN bV cV dF Dp Ed Fp Fy Gp hX Is It Iz jK Jl Kj Kk Kq Kr Li Ms Mt Nb oH Oz pF Qd Qh qX qY rC Rj St Uf) Un(bA bN Ch Ct cV dF Ed Gp Hb Hc Ii Iz jD Jk Jo Kg Kj Kk Li Mq Nr oH Oy pF qD Qe Qv Ri Rt St Uo Us vS We Ye Tl) wD(aW bL bS cC DB eD Et Fb iA iO jD jP jY Kp Kr Mz Nw Ny pY qC qD Ql RB rC rR rS rX rY Uf uM vS tL Tj tF) Mz(Hu Hw Ip Ir Jn Jp Js Jt Lu Lw Mb Mf Mh Ml Mn Mu Mx Nb Ni Nn Nr Nv Nx Oh Om Pc pF Pg pS Qb Qd rO uM wP) St(bA Bg bN cV dF Eq Iz Jq Kd Kg Kj Kk Kr Lw Me Ml Mq Ms mW nD Ni oH Ou pF qC Rh Rt Sr Ua Ul Us Va Yh Yk) Mt(aC aV aY bF bL bN bQ bU bV bZ cA cF cG cK cL cO Ct CV dA Dc dF dH dI dJ fN hA hX qC Rh uX vS Wc) Li(aD aM Bg cA Cv Dc dF dJ Dp Ed Fy Hb Hc Ib Iz jI Kd Kg Kj Kk Kr oH oK Ou pF Qv qY Rh Sr Tv Ua Ul Th) Jn(Hu Ip Ir Iv Jm Jt Lp Mb Me Mf Mn Mp Mr Ms Mu Mx Nb Nc Ni Nn Nr Nv Nx Ny Oh Om Pc Pg Pz Qb We Zq) Kq(aM bL bN cI Dp Ed Hq Ib Jd Jc Kk Kr lN lO Md Mk Ms Mu My Nv Oz Pb pF qC Qt Qv Rh Rt uM Us Ut Tj) Ct(aA Bc bF cE Cw Dc Dg dJ EF Jg Jp Kd Kf Kn Lv Mr Nr Nv Ok Om Ou Pd Pg Po Qd Qh Sr Tn Uf) We(aM Bc De Dp Ed Eq Fp Im Is Iv Kj Ld Mh Mq mZ Nd Ni No Nr Ow Oy Pb Qa Qb Qe Qx Ra Rh Rt Wc) Me(Aa dF Hu Ih Ik Ip Ir Iv Js Jt Lw Mn Mp Mu Mx Nb Nc Nd Nj Nm Nr Nx Ny Oh Pa Pc Pg Pz Qb) Hb(aA Ad Ch Cu Cw Dc dF Ed Fp Fy Is Jl Jq Kd Kk Kn Lw Mq Mr Ms Ou Qa Qe Qv Rh Sr Tv Ul Us) Qd(An bB Bg bL bN bS Ch cT cV dF Fr Ip Iz Jp jQ Kj Kr Mh Ml Nb Og oH Pc pF Qv qY Rh Sr Ua) aC(aP bR bW bZ cR cT cU cV dJ Fp Gc Gp Ip Jg Jl Jp Lh Ml Mm Mq Mr Nr Ok On Pd Pg Po Zq) qC(aA Ad cH Cu Cv hB Ih Is Jq Js Kc Kd Kf Kk Kr Lh Lx Mr Nm Nx Oh Ok Pg Qe Rb Rm Sr Uc) bA(aA aD aI bM bR cA cE cF cH Cv Dc dJ dN Dp Fp Fr Hq Ib jI Jk Jl Jq Ml Pb Qc qX Rh) uX(aW bL bN cO DB dE dJ eD Et Fb iH jO Kr Lj Lu Mf Nk Nm Ny Ow QY rB uM vS vV) Fy(Bg bN bW cV dJ Dp Ed Hc hF Hq Ib Iz Jk Kj Kk Mm Mq Nw Oy pF Qe Qv Tv Ua vS Vt) Sr(bN Ch Dp Fp Gp Hc Iz jD Jk Jo Kg Kj Kk Kp Mm Mn Oy pF Pj Qe Qv Rh Ri Rt Uf vS) Jr(dF Hu Ip Jt Lu Lw Mb Mf Mn Mp Ms Mu Mx Nb Nc Ni Nn Nr Nv Nx Ny Oh Pc Pg Pz Qb) cE(Ad aJ An bB Bg bL bM bN bR bS bV cA cF CH cL Cu Dc dD dJ dN Fp Fr jI Jj Ml) Nd(Cu Ih Ip Js Lw Mi Mn Mu Mx Na Nb Nf Nn Nr Nx Ny Oh Oz Pa Pc Pd Pg Pz Qc Zq) Nj(Hu Hv Hw Ih Ip Js Lw Mn Ms

Figure 3 Continued

Mu Mx Na Nb Nf Nn Nr Nx Ny Oh Pa Pc Pg Pz Qb Zq) Fr(AD aM bB Bg bL bN bR bS bV cF cH cT Cv Dc dE dJ Gp Iz Ml Nb Ns Rh Ua)
Lx(aV bF bQ bU bZ cA cF cG cK cL dA dH dI Ex Fc hX jI oH pF qY Wc Yk Th Yf) Mq(bL bV dF dJ Dp Gp Hc Iz Kd Kk Kp Ky Pj Qt Qv Rf
Rh Ri Rt Ua Wc Ye Th) Ik(Hv Hw Ih Ip Ir Js Jt Lw Mn Mp Ms Mx Na Nc Ni Nn Nv Og Oh Om Pb Pc Qb) Zq(bR Dc Ed Fp Gl Iv Ld Lz Mh MI
mZ Nr Or Ow Oz Pb Qa Qb Qx Rh Vt Ye) Lj(bN dD hB jK Kk Kr oH oK pS qD Qg qY rR Rz uM uT Wd Wh tM tL Xa Th) bF(AD aJ bB Bg
bL bM bR bV cA cF CH cO Cu Cv Dc dJ dL dN jI Ml) vS(Ad Dc Et hB Im Jl Kd Kf Kn Kr Mr Nm Nw Ny Pj Qa Qh Rm Tr Tv Uf Us) Gp(Ad
aM Ar As Bc Bn Ch Cp Cq Cu Cv Cw Dc dF dJ dX eP Kd Lw Qe Tv) Fp(Aa aM bB bN bR bW cT CV Dc dJ Kd IX Ou qY Rh Rz Uf Ul Th)
Qb(Hu Ir Iv Jp Jt Lw Ml Mm Mr Nb Nc Nh Ni Nl Oe Og Wh Zx Ye Xa) Qe(bL bS bV cV Iz jO Kd Kj Kk Kr oH Ou pF Qg qY Rt Tv Um Vv
Ye) Jq(Ar bN bV Ch cl cV dF dJ Dp Ed Hc Iz Kk lN Ou pF Pj qD Qv Uf) Om(Bg Ch Hc Ib Ir Jo Jp Md Mh Ml Mm Mr Mx My Nc Ni Ns Oe
Pb) Ad(aJ aM aU bB Bg bN bV bZ cH cT CV Dd dJ Jo Kg Oy wP) Ms(dF hW Ip Js Jt Kd Mn Mp Mu Mx Nb Nh Nl Nn Nr Nx Oh Pj) Qa(Aa
bL cV Dp Hc Ib jQ jT Kk nD Pj Qw qY Um Vs Vv Ye Tj) Cu(aA aD aU bB bL bN bS CH cT Cv dJ Jk Jo Kj oH Oy) Is(Hc Ib Kj Kk Kr nD oH
pF Qg Qw rB Rt rX Tv Vv Wc Ye) Nh(Hw Ip Ir Js Jt Lw Mp Mx Nb Nf Ni Nn Nv Ny Oh Pc) bB(aJ aM Bb Bc bR cF cl cT Cv Dc dJ dN fR jl Jj
qX) Mr(Hu Ip Lw Mb Mf Mn Nb Ni Nn Nr Nv Nx Oh Oy Pc) Jp(Bg Hw Ip Iz jO Lu Lw Mb Mh Ml Mx Ns Oy Pb qY) Mm(Hv Hw Ih Js Jt Kd
Lu Mb Mh Mx Na Nb Nr Nx) dF(Hq Iz Jk Jo Kk Ml Nb oH oN Oy Pj qX Rh Uh) jl(bW cU Dp Fb Ip jT nW Ny Pg Pj Qh qY Uf Uh) Iv(Hu Ip
Mf Mn Mp Nb Nn Nr Nv Nx Oh Pb Pc) Jl(Bg bN bS Ch fN Iz jQ Qv qY rB Rh Ua uM) Lh(Bg bN Hc Iz jO Kj oH pF Qv qY Rh Ua Tj) aA(aQ
Ar Bc bS Cv Dc Dg Dl jK jT pF Pj qY) dJ(aJ aM An Ba Bc bV cG Cv Dc dG dN Ml pF) Ir(Hu Jt Lw Mn Mx Nb Nc Ni oH Pc pF Tv) Ou(Bg Ch
Kk pS qX rB Rf Rh rN rS uT wP) Uf(Ch Ed hO Iz Jo Kd Kg Kj rS uM uV yL) cT(aD al aJ aM Bc CH Cv Dc Dg dN fR) Ml(Bg bN bV bW cV
iC jT Nv pF qY Rz) Lw(Dp hP Kk Kp Nl qD qY Rh uM yL) Nc(lp Jt Mn Mp Nb Nn Nv Nx Ny Pz) bN(aJ Dc dG dN hB Jj Kd Kk Kn Ok)
Et(hX qH qY rN rS rX uM uV vV) Nm(qH uM vA vV wB yL yE tM xA) cH(aJ aM Ba bV cG dN hB pF wP) nD(bR Ed gL Im Kr oK Pf Pi Up)
Nr(Ch Fi Kd Kk Qv Rh Rt Wc) Nl(Hw Js Nx Ny Oh Pc Pg Pz) Nv(Mh My Ni Ns Oe Og Oy Pb) Nw(Hc Kg qY sK Ua uM Vu Vv) Vt(jK sC uM
wP Yi Tl XA) Bg(Ba Jg Ok On Pg Po Tn) Dc(al aU Ba bW Dg jD Rh) Ip(bV hW jQ Jt Mx Nb rX) Kd(Kk pF Pj qD Rh Wc Tl) aJ(al bL bR cF
dD dE qY) aM(al bV cF cV Jj qY Uh) hB(bL cO Jj oH qY rB vV) nW(rN rS tU uT vW wB wP) Po(Fc Fd Fi Ho Rt Wc) Im(Ib lX nA oH Vs Vv)
Jt(Lu Mb Mx Nb Nx Og) Kn(hX Jo pF qD Rh sC) Ny(rS rW tT uM vV wP) On(Ao Co Hc Iz Rt Wc) Pj(Ed Kg Kk Or Qv Rh) Ni(Ih Js Mn Nn
Nx) Kr(tV uM uT wB xA) Ld(Fc Fi Ho Rt Ye) Ok(Ed jO Kg Qv Rh) Uh(aD Ib jO mM pF) bR(bV cG dG dN nl) mZ(Ry Rz Wh Tl Xa) Ch(Dg
Pg Qh Wh) Ji(Gh Rt uM Zx) Jj(cV iA pF Vq) Kf(Kg Kj sC uM) cF(bV cG dD dG) rN(Db dE Mf Rb) Tr(Mk Oy uN) Tn(Iz Jk Oy) Tv(pF rB Uo)
Ye(Of Ow Ql) Kk(Qv Rh Vq) wB(DB Rb) qZ(Ql Qy Ua) Bc(Lt oH) Fb(hW rS) Mn(Mx Nt) Il(Wc Yk) Js(iC qY) Xa(kR Pb) Ke(rB Vu) Kp(uM
vA) Vq(bV cV) Oz(Uw Wh) Pg(hA hX) aD(Ba fR) cA(cG dG) dD(bV dN) tV(dB dE) CwRt DbuT TiUl ThMh NorB MxPc MyJh IzJg WcQx
QhJk RhOr VsOy PdhX bLdG jDoF qYqX

Unconstrained panels with 3 analytes, where 7.5E-11 >= 'AUC p-value' > 0. Contains 50,000 panels of 35,857,239 total panels evaluated. :
Li{lN(aA aC AD aE AF aG aH al AJ aK aL aM AN AO AP aQ AR AS aU aV AW AX aY aZ BA BB BC bE bF BG bH bI bJ bL bM BN BO
bP bQ bR bS bU bV bW bX bZ cA cB cC cD cE cF cG CH cl cJ cK cL cM cN CO CP CQ cR CS CT CU CV CW CX cY cZ dA DB DC DD
DE dF DG dH Dl dJ DK DL dM dN Dp dR eC ED EF ET EZ Fa Fb Fn FP Fr Fw FY GL GP gW HA HB HC HF hG hL hO hP Hq HR Hu HV
HW HX iA IB IC Id IH Ii IJ Ik Il Im In IO IP Iq Ir Is It Iu Iv IZ JD JE JF JG JH JI Jj JK JL JM Jn JO JP JQ JR Js JT JU JV JY Kc Kd Ke Kf Kg
Ki Kj Kk Kl Kn Ko Kp KQ KR KS Kx Ky Kz Ld Lh Lj IK IL IM IN IO Lu Lv Lw Lx Ly Lz Ma Mb Mc Md Me Mf Mg Mh Mi Mj Mk Ml Mm
Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE
OF Og OH Oi OK Om ON Or Ou Ow Oy Oz Pa Pb Pc Pd Pe PF Pg Ph Pi Pj Pk Po pS pY Pz QA QB QC QD Qe QG QH ql Ql Qm Qn qO qP
qQ QT QU QV QW QX QY QZ RA RB RC Rf Rg Rh Ri Rj Rm rN rO rP rQ rR rS rT rU rV rW rX rY rZ sC sK sM sO Sr Ss St TN TO tQ TR
tS TT tU TV tX Tz Ua Ub Uc Ud Ue Uf UG Uh ul Uk UL UM UN UO UP UR Us UT UU UV uW uX uY uZ vA vB vC vH vI VO VP vQ vS
VT VU VV vW wB wC wD wE wF wG wH wJ wK wL wP wQ yD yH yJ yK yL zA zG zH zI yE tM tL xA Wm Tj tF) vS(aA aC AD aE AF aG
aH al AJ aK aL aM AN AO AP aQ AR AS aU aV AW AX aY aZ BA BB BC bE bF BG bH bI bJ bL bM BN BO bP bQ bR bS bU bV bW bX
bZ cA cB cC cD cE cF cG CH cl cJ cK cL cM cN CO CP CQ cR CS CT CU CV CW CX cY cZ dA DB DC DD DE dF DG dH Dl dJ DK DL
dM dN Dp dR eC ED EF ET EZ Fa Fb Fn FP Fr Fw FY GL GP gW HA HB HC HF hG hL hO hP Hq HR Hu HV HW HX iA IB IC Id IH Ii IJ
Ik Il Im In IO IP Iq Ir Is It Iu Iv IZ JD JE JF JG JH JI Jj JK JL JM Jn JO JP JQ JR Js JT JU JV JY Kc Kd Ke Kf Kg Ki Kj Kk Kl Kn Ko Kp KQ
KR KS Kx Ky Kz Ld Lh Lj IK IL IM IN IO Lu Lv Lw Lx Ly Lz Ma Mb Mc Md Me Mf Mg Mh Mi Mj Mk Ml Mm Mn Mp Mq Mr Ms Mt Mu
Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON
Or Ou Ow Oy Oz Pa Pb Pc Pd Pe PF Pg Ph Pi Pj Pk Po pS pY Pz QA QB QC QD Qe QG QH ql Ql Qm Qn qO qP qQ QT QU QV QW QX QY
QZ RA RB RC Rf Rg Rh Ri Rj rN rO rP rQ rR rS rT rU rV rW rX rY rZ sC sK sM sO Sr Ss St TN TO tQ TR tS TT tU TV tX Tz Ua Ub Uc Ud
Ue Uf UG Uh ul Uk UL UM UN UO UP UR Us UT UU UV uW uX uY uZ vA vB vC vH vI VO VP vQ VT vU VV vW wB wC wD wE wF
wG wH wJ wK wL wP wQ yD yH yJ yK yL zA zG zH zI yE tM tL xA Wm Tj tF) uM(aA aC AD aE AF aG aH al aJ aK aL aM AN AO AP
aQ AR AS aU aV AW AX aY aZ BA BB BC bE bF BG bH bI bJ bL bM BN BO bP bQ bR bS bU bV bW bX bZ cA cB cC cD cE cF cG CH cl
cJ cK cL cM cN CO CP CQ cR CS CT CU CV CW CX cY cZ dA DB DC DD DE dF DG dH Dl dJ DK DL dM dN Dp dR eC ED EF ET EZ Fa
Fb Fn FP Fr Fw FY GL GP gW HA HB HC HF hG hL hO hP Hq HR Hu hV hW HX iA IB IC Id IH Ii IJ Ik Il Im In IO IP Iq Ir Is It Iu Iv IZ JD
JE JF JG JH JI Jj JK JL JM JO JP JQ JR Js JT JU JV JY Kc Kd Ke Kf Kg Ki Kj Kk Kl Kn Ko Kp KQ KR KS Kx Ky Kz Ld Lh Lj IK IL IM IN
IO Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf
Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph
Pi Pj Pk Po pS pY Pz QA QB qC QD Qe QG QH ql Ql Qm Qn qO qP qQ QT QU QV QW QX QY QZ RA RB RC Rf Rg Rh Ri Rj Rm rN rO rP
rQ rR rS rT rU rV rW rX rY rZ sC sK sM sO Sr Ss St TN TO tQ TR tS TT tU tV tX Tz Ua Ub Uc Ud Ue Uf UG Uh ul UK UL Um UN UO UP
UR Us UT UU UV uW uX uY uZ vA vB vC vH vI VO VP vQ Vs VT VU VV vW wB wC wD wE wF wG wH wJ wK wL wP wQ yD yH yJ yK
yL zA zG zH zI yE tM tL xA Wm Tj tF) uU(aA aC AD aE AF aG aH al aJ aK aL aM AN AO AP aQ AR As aU aV AW AX aY aZ BA BB BC
bE bF BG bH bI bJ bL bM BN BO bP bQ bR bS bU bV bW bX bZ cA cB cC cD cE cF cG CH cl cJ cK cL cM cN CO CP CQ cR CS CT CU
CV CW CX cY cZ dA DB DC DD DE dF DG dH Dl dJ DK DL dM dN Dp dR eC ED eF ET EZ Fa Fb Fn FP Fr Fw FY GL GP gW HA HB HC HF
hG hL hO hP Hq HR Hu HV HW HX iA Ib IC Id IH Ii IJ Ik Il Im In Io IP Iq Ir Is It Iu Iv iZ JD Je JF JG JH JI Jj JK JL JM Jn JO JP JQ JR Js JT
JU JV JY Kc Kd Ke Kf Kg Ki Kk Kl Kn Ko Kp KQ Kr kS Kx Ky Kz Ld Lh Lj IK IL IM IN IO Lu Lv Lw Lx Ly Lz Ma Mb Mc Md Me Mf Mg
Mh Mi Mj Mk Ml Mm Mp Mq Mr Ms Mt Mu Mv Mw Mx My Mz Na Nb Nc Nd Ne Nf Ng Nh Nj Nk Nl Nm Nn No Nq Nr Ns Nu Nv NW
Nx NY Oa OE Of Og OH OK Om ON Or Ou Ow Oy Oz Pa Pb Pc Pd Pe PF Pg Ph Pi Pj Pk Po pS pY Pz QA QB QC QD Qe QG QH ql Ql Qm
Qn qO qP qQ QT QU QV QW QX QY QZ RA RB RC Rf Rg Rh Ri Rj Rm rN rO rP rQ rR rS rT rU rV rW rX rY rZ sC sK sM sO Sr Ss St TN

Figure 3 Continued kQ kS rN tN tT tV tX uX wH zI yE tM tF) Rc(rN rQ tR tV uO uT vB vU vV vW wH wL yL zI) jO(cU dF hB Is kS oF Pg tV tX Uh uT uX yE tM) kQ(hX iB jE jG jL jM jP jQ jU jY IK IO rX) pS(bP bR Fb Kp oK Or Ow Qc Ra Sr Tn Us uY) hB(hV jE jH jK jM jY IK IN IO qY uY wQ) uX(aM bN bP dE dN Fb Kp Ou Ow qT qY rB) kS(hX iB jE jG jM jQ jR jY IM IN rX) tF(hX iB jE jG jL jM jQ IM IN rX) yE(Db dE Fb Il Jf IN oK Ou Ow Vo) yL(bW Db dE iP jU Sr Uh Ul Vo Tj) bP(rN tN tR tS tT tX vV wH zI) oK(rR sO tX uT uV wH zI tM tL) Tr(rP rT tO wF wG wH yJ zI) Jj(Fp Ik Im Is Jm Lx Ok Qa) uO(aW bA cT Kp Kr Ms Oe Vv) tM(bN Db dE iH Kr Ou Ow) rR(aW aZ bR bW cH Kr Vo) qP(aQ Fb Jk Lj IN Ou qX) zI(aM Bb bN jP To Vo) jM(Ef gL iP iZ kR oF) rX(fP gP iH iJ iO nY) uY(cE dF Kp No qX Vs) vB(As cE Kp qY Uh) Fb(qI uG vU yJ) Il(qH rP uR vV) hX(dR hG iH iO) iB(hF iH kR oH) iP(hV jE jH jU) jK(Dp hG nY oF) jQ(aQ cU cY Is) Kp(rT wQ yD) Vp(rN tX wH) Vo(uT wF tL) hC(jE jH IK) jU(eF gW iJ) vW(Id No Uh) Bo(Tk Wn) Ef(jE IN) Fp(Jg Ms) Ng(Jg Pf) Kr(rN rT) Ou(qI uG) aW(rP rT) cH(qO qQ) dE(wF wH) qY(iZ vI) jR(kR vV) uU(Id Sr) uZ(bC bW) WmtL EdtT TjwH LxMc IsjV WemZ RivV TkVt Owql PhqX bAwQ bRsO dHuI eFlK gPjY wLIN hViH} Nw{qC(aA aC AD aE AF aG aH aI aJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp dR eC ED EF eT EZ Fa Fb FN FP Fr Fw FY GL GP gW HA HB HC HF hG hL hO hP Hq HR Hu HV HW HX iA IB IC Id IH Ii IJ Ik Il Im In IO IP Iq Ir Is It Iu Iv IZ JD JE JF JG JH JI Jj JK JL JM Jn JO JP JQ JR Js JT JU JV JY Kc Kd Ke Kf Kg Ki Kj Kk Kl Kn Ko Kp KQ KR KS Kx Ky Kz Ld Lh Lj IK IL IM IN IO Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv nW Nx NY Oa OE OF Og OH Oi OK Om ON Or Ou Ow Oy Oz Pa Pb Pc Pd Pe PF Pg Ph Pi Pj Pk Po pY Pz QA QB Qc QD Qe QG QH qI QI Qm Qn qQ QT Qu Qv QW QX QY Qz RA RB RC Rf Rg Rh Ri Rj Rm rO rS rW rX sC sO Sr Ss St Tn To Tr Tt Tv Tz Ua Ub Uc Ud Ue Uf Ug Uh uI Uk Ul UM Un Uo Up Ur Us Ut Uu UV vA Vo Vp vS VT Vu Vv vW wD wF wK wL wP wQ yL tL Wm Tj tF) qD(aA aC AD aE AF aG aH aI aJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp dR eC ED EF eT EZ Fa Fb FN FP Fr Fw FY GL GP gW HA HB HC HF hG hL hP Hq HR Hu HV HW HX iA IB IC Id IH Ii IJ Ik Il Im In IO IP Iq Ir Is It Iu Iv IZ JD JE JF JG JH JI Jj JK JL JM Jn JO JP JQ JR Js JT JU JV JY Kc Kd Ke Kf Kg Ki Kj Kk Kl Kn Ko Kp KQ KR KS Kx Ky Kz Ld Lh Lj IK IL IM IN IO Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv nW Nx NY Oa OE OF Og OH Oi OK Om ON Or Ou Ow Oy Oz Pa Pb Pc Pd Pe PF Pg Ph Pi Pj Pk Po pS pY Pz QA QB Qc Qd Qe Qg QH QI Qm Qn qP QT QU Qv QW QX QY QZ RA RB Rc Rf Rg Rh Ri Rj Rm rO rS rU rW rX sC sO Sr Ss St Tn To Tr Tt tU Tv Tz Ua Ub Uc Ud Ue Uf Ug Uh uI Uk UL UM Un Uo Up Ur Us Ut Uu UV vH Vo Vp vS VT Vu VV wD wQ yD yE Wm Tj tF) hO(aA aC AD aE AF aG aH aI aJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp dR eC ED EF eT EZ Fa Fb FN FP Fr Fw FY GL GP gW HA HB HC HF hG hL hP Hq HR Hu HV HW HX iA IB IC Id IH Ii IJ Ik Il Im In IO IP Iq Ir Is It Iu Iv IZ JD JE JF JG JH JI Jj JK JL JM Jn JO JP JQ JR Js JT JU JV JY Kc Kd Ke Kf Kg Ki Kj Kk Kl Kn Ko Kp KQ KR KS Kx Ky Kz Ld Lh Lj IK IL IM IN IO Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv nW Nx NY Oa OE OF Og OH Oi OK Om ON Or Ou Ow Oy Oz Pa Pb Pc Pd Pe PF Pg Ph Pi Pj Pk Po pY Pz QA QB Qc Qd Qe Qg QH QI Qm Qn qO qP qQ QT Qu Qv Qw Qx QY Qz RA RB RC Rf Rg Rh Ri Rj Rm rS rU rW sC Sr Ss St Tn To Tr Tt Tv Tz Ua Ub Uc Ud Ue Uf Ug Uh uI Uk UL UM Un Uo Up Ur Us Ut Uu Uv Vo Vp vS VT Vv wD wL wQ zH tM Wm Tj tF) fN(aA aC AD aE AF aG aH aI aJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF dG dH DI dJ DK DL dM Dp dR eC ED EF eT EZ Fa Fb Fn FP Fr Fw FY GL GP gW HA HB HC HF hG hL hP Hq HR Hu HV HW HX iA Ib Ic Id IH Ii IJ Ik Il Im In IO IP Iq Ir Is It Iu Iv IZ JD JE JF JG JH JI Jj JK Jl Jm Jn JO JP JQ JR Js JT JU JV JY Kc Kd Ke Kf Kg Ki Kj Kn Ko Kp KQ Kr KS Kx Ky Kz Ld Lh Lj IK IL IM IN IO Lu Lv Lw Lx Lz Ma Mb Mc Md Me Mf Mh Mi Mj Mk Ml Mm Mn Mp Mq Mr Ms Mt Mv Mw Mx My Na Nb Nc Nd Ne Nf Ng Nh Ni Nj Nk Nl Nm Nn No Nq Nr Ns Nt Nu Nv nW Ny Oa OE OF Og OH Oi OK Om ON Or Ou Ow Oy Oz Pa Pb Pc Pd Pe PF Pg Ph Pi Pj Pk Po pY Pz QA QB Qc Qd Qe QG QH qI QI Qm Qn qO qP qQ QT QU QV QW QX QY QZ RA RB rC RE Rf Rh Ri Rj Rm rN rO rP rQ rR rS rT rU rW rZ sC Sr Ss St Tn To Tr Tt Tv Tz Ua Uf Ug Uh uI UK uI Ul Um Un Uo Up Ur Us Ut Uu Uv Vo Vp VT Vu Vv wJ wL wQ yH Wm Tj tF) hP(aA aC AD aE AF aG aH aI aJ aK aL aM AN AO AP aQ AR AS aU aV aW AX aZ BA BB BC bE bF BG bH bJ bL bM BN BO bP bQ bR bS bU bV bW bX bZ cA cB cC cD cE cF cG CH cI cJ cK cL cM CO CP CQ cR CS CT CU CV CW CX cY cZ dA DB DC DD DE dF DG dH DI dJ DK DL dM dN Dp dR eC ED EF eT EZ Fa Fb Fn FP Fr Fw fY GL GP gW HA HB HC Hf hL Hq hR Hu HV HW HX iA Ib IC Id IH IJ Ik Il Im In IO IP Iq Ir Is It Iu Iv Iz JD JE JF JG JH JI Jj JK JL JM Jn JO JP JQ JR Js JT Ju JV JY Kc Kd Ke Kf Kg Ki Kj Kk Kn Ko Kp KQ KR KS Kx Kz Ld Lh Lj IK IL IM IN IO Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv nW Nx NY Oa OE OF Og OH Oi OK Om ON Or Ou Ow Oy Oz Pa Pb Pc Pd Pe PF Pg Ph Pi Pj Pk Po pY Pz QA QB Qc Qd Qe Qg Qh QI Qm Qn Qt Qu Qv Qw QX QY Qz Ra RB Rc Rf Rg Rh Ri Rj Rm rW Sr Ss St Tn To Tr Tt Tv Tz Ua Ub Uc Ud Ue Uf Ug Uh Uk Ul Um Un Up Ur Us Ut Uu Uv Vo Vp Vt Vu Vv wL wQ Wm Tj tF) uM(aA AD aE AF aG aH aK aL AN Ao Ar As aV aW AX aZ BA BB BC bE bF BG bH bL Bn Bo bP bR bS bV bW cA cC cD cF cG CH cL cM CO CP CQ Cs cT Cu CW cZ dA dB Dc Dd dE dF dG dH dJ dK DL dM eC eD Ez Fb Fp Hc hL Hq Hr Hu Hv HW Hx Id Ih Ii Ij Il Im In Io Ip Iq Ir Is It Iu Iv Iz JD JE Jg JH JI Jj Jk JL Jn JO JP Jq Jr Js JT Jv Jy Kd Ke Kf Ki Kj Kn Ko Kp KQ Kr Ks Kx Lh Lj IK IL IM IO Lv Lw Lx Ly Ma Mb Md Me Mf Mg Mh Mi Mj Mk Ml Mm Mr Ms Mt Mu Mw Mx My Na Nb Nc Nd Ne Nf Ng Ni Nj Nk Nl Nm Nn No Nq Nr Nt Nu nW NY Oa OE Of Ok Om oN Or Ou Ow Oy Oz Pb Pc Pe Pf Pg Ph Pi Po pS Qa Qb Qc Qd Qe QH QI Qn QT qW qX QY qZ Ra RB rC Rf Rg Rh Ri Rj Rm rN rO rS rU rV rW sK Sr Ss Tr Ud Uf Uh UI Um Un Up Ur Us uT Uu Uv Vo Vp VT Vu Vv wB wD wQ Wm) Ms(aA eT cZ Fp Fr fY hL Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Lj Lu Lv Lw Lx Ly Lz Ma Mb Mc Md Me

SrvA WemZ KrtN zljO} qC{Lj(Af aZ Bn bX CH Cv Cx Di dJ dM eD Fb fN hP In Ip Jl Jq jT jU Jy Kc Kf Kk Ko Kp Ky Lw Md Mu Ng Ni Nm Nx Ny Oh Pc Pg Pj Qc Qd Ql RB Ri rS Ss tO tR tU uM Un uP Ur Ut uV vP vQ Vt wE wP wQ zI) Ko(Aj aN Ax aZ bN bR cB CH Cs Ct Db dH dM Fb Hc Hq Ib Iz Jl Jy Kp Kz lN Me Mg Mr Ng Oa Ou Ow Oy Rb Rh Ua Vt Wm) Vt(aZ bN bR bS cO Ct Cw DB dE dJ dM Fb hP Ib iH jF Jk jO Kr Kz lN Me Ny Of Ou Ql RB ul vA xA) dM(aZ bH Cs DB dE dJ eD Fb lh Jl Kp Kz Lu Mf Mh Nm Ou Pj Ql Rb yL Wm) Fb(Ad aN Ax cH dJ Kq Kr Mh Nm Ny Oa Ok QA Qd Qe Rb Uc Un Ur) Ny(Aj aZ CH Cs dJ Ib jO Me Ng Oa Ou qA RB Ri uM Wm) Kp(aZ CH DB Dg dJ fN Hc Ly Me rA RB Ur Wm) Cs(cH dJ eD fN hP In Kc Nm Pj Qg RB Ur) Qd(bN DB dE Hq Ib lN Ou Ow rB yL Wm) Jl(aN bN CH cO dB dJ fN jO Me rB Ur) Ng(Ad Dg Dl Jg Kl Kq Nm Pj Qe Uc Uf) Ch(Fa Is Kq Mw Qe Qh Sr Uc Uf Un) dB(Ax cH Cu Dc Kc Kf Kn Kq Lx Pg) rB(Ax Fp Ih Is Oa Pe Qa Qb Qe Wm) Db(Cu Dc Kc Kd Kn Kq Pg Un uX) Nm(Aj Ct Ib Kk Mg Mt Ou Ow Vv) Wm(Ip Is Ld Mt Rf Ri uM) Me(Ax Dc Ih Pe Qa Sr Un) Uc(Aj Ct Hc Of Ou Ow Oy) Qe(bN Ib In Ou Ow Rb yL) Pg(aZ bL Co dE Hq Nq) dJ(Ih Is Mt Oa Pe qX) Ur(Ct Fa Oa Oh yL) aZ(Cu Dc Fa Ok Pe) Ax(eD fN Ri uM) Kf(cB Cw iH Ou) cH(aN Oa Ou Ql) Rb(Ih Pe Qa) Kq(Aw Hc Qy) hP(Is Oh Pe) Ad(Aj Ib) Dg(Kk Vv) Qa(bN Ou) Qg(Is Js) Oa(fN Ri) Un(bN Hq) DcdE FaHc LxcO MhtU IpOu SrKz SsKk} mZ{Dr(aD aG Ba Bc bF bH bM bZ cA cI cV dD dF Em Gz Hc hG Hu Hw iA Ij Ik Il Jd Jh Kd Ki Kr Ld lY Ma mE Mg Mh Mq Mr Mt Nq OE Of oH Om oV Pa Pb Pf Ph Qt Rv Rz St Uh Ul Ur Us Vs Wd We Wh Yd Zq Tl Xa Yf) St(Du Eq Fc Fd Fi Gb Gc Gd Gh Gn Hl Ho Hp Lp Lt Op Ps Rt Ru Rv Rx Ry Rz Sf Sh Si Sj Uw Ux Uy Uz Va Vb Vc Vh Vi Vj Vw Vz Wc Wd We Wf Wg Wh Yd Yg Yh Yi Yj Yk Yl Zq Zw Zx Ye Tm Tl Xa Ti Th Yf) Ld(Du Em Eq Fc Fd Fi Gb Gc Gd Gh Gn Hl Ho Hp Lp Lt Op Ps Rt Ru Rv Rx Ry Rz Sf Sh Si Sj Uw Ux Uy Uz Va Vb Vc Vh Vi Vj Vw Vz Wb Wc Wd Wf Wg Wh Yd Yg Yh Yi Yj Yk Yl Zq Zw Zx Ye Tm Tl Xa Yf) We(aY aZ bG bR bZ cG Ch cZ dN Dp Fa Fn Gd hG iJ Iv Ju Jy Kc Kf kG Kj Kk Kr Lp lY Mq Mr Ni Oa oV Ow Oy Pb Pi Qt Qv Qx Ra Rf Rh Ru Sf Tt Ub Up Ur Uv Uy Va Vi Vp Vq Vt Ye Wm Tj Yf) Rz(bG bS cE cG Ch cL Dp fB Hq iJ Iv Jt Ju Jv Kc Kg Kj Kr lW lY mE Mq Mr mU Nd Ni Oa Oy Oz Pa Pb Pg Pi Qv Sf Sh Tt Ye Tj) Kr(Du Em Fd Gb Gc Gh Lp Ps Rt Ru Rv Ry Si Uw Uy Va Vh Vi Vw Vz Wh Yi Yl Zq Zx Tl Xa Ti Th) Xa(BG Dp gP Hl Ib iJ Jk lY Ng oV Qw Uy Vt) Wh(bG Dp Ef Ib Iz Kc Oy Pb Pi Qw) Tl(bR cG Gz lY nA oV Po Qt) Pi(Fi Gc Gd oV Yh Yl Ye) Zq(bG Dp Iv lY Tj) Uy(bZ Ma Mq Mt Pf) Gh(Ma Pa Po) Ry(lY Ni Vq) bZ(Gc Gd Yf) Ik(fB oV) Wc(hG lY) YfMh FiPb GdVw MqYe IjSf YhoH ZxUn RtlY} Kp{fN(aE AJ aO Ap aQ Ax aZ BC bF bL bR bW bX cB cD CH cN Co cR Cs Cv Cw DB Dc Dd dE DG dM Dp eD Fa Fb Fr Fw Gl HB Hc Hq hR Hu iA Ib iH Ii iJ Il iO iP jD jE jF Jl JO jT JY Kg Kj Kk Kr Lj lL lM lN Lv Lw Lx Ly Ma Mb Md Me Mh Mk Mm Mp Mq Mr Ms Mv Mx Ne Nf Ng Nq Nu NY Oa oF oK Ou Ow Pc Pf Pg Pk pY qA Qc qD Qh Ql qX Qy Rb Rc rT rW rX rY sC Sr Ss Tt Tv Tz Ua Ub Uf Uo Up Uu uV vA Vt VV Wm Tj tF) Db(pS rN rO rR rS rW sC sM tN tO tQ tR tS tT tU tV tX uM uO uP uR uT uV uW vA vI vO vP vQ vT vV vW wB wC wE wF wG wH wJ wK wL wP wQ yD yH yJ yK yL zA zG zH zI yE tM tL xA) dJ(hO pS qA qO rP rW sC sO tO tR tS tT uM uN uO uV uX vA vB vI vP vQ vV wK wP yD yJ yE tM xA) Ss(qB rW tR tS tU uI uM uO uV uW vA vP vQ vV wB wG wJ wK wL wP wQ yD yH yL zG zI yE xA) jO(pS qA qB sC tR tS tU tV tX uG uM uO uV uX vB vC wP yD zA zI yE tM) dB(rN rR rS rW sC tV uV vA wB wP yL tM) eD(rP rS rW tT tU uM uO uV wK wP yD xA) Wm(hP rP rS tU uM vA vQ vU vW wP xA) rB(qA rW uN uO uV vB vI vV wF yD) Ko(hP rP rS tU uM uV vA xA) sC(aZ dE Dg jM Pj rW Vt) uM(bW Ch dE Dg Mf Mm) hP(bW Ch iO Sr Uf) Rb(uV wG wQ yD) dE(rW uV wB yL) vA(bW Dg Nm Uf) wQ(cH Kr Me) tU(Dg Nm Pk) Lu(wP yD) DgqH ImnD VtqD VqoE cVwP qAjT jRvV oKuV} oE{Vq(aA aC aE Af aG aH aI aK aL aN aQ aR As aU aV aW aY aZ bA bB bF bG bI bL bM bN bQ bS bU bZ cA cC cE cF cG cI cJ cK cM cO cQ cR Cu cV cX cY cZ DB dC dD DE dF dH dJ dN Dp DR Ed eF Eq Ex Ez Fa Fb Fi Fn Fr Fw Gc GL GP Gz HB hF Ho Hp Hq Hr Hu Ib Ic Ih Ij Il Im In Io IP Iq Ir Is It Iu Iv IZ Jd Jg Jh Jl Jn Jo Jp Jq Jr Jt Ju Jv Jy KC Kd Kf Kg Ki Kk Kn Ko KQ kR KS Ky Kz Ld Lh Lp Lt Lv Lx Ly Ma Mb Mg Mh Mk Mm Mn Mr Mt Mv Mw My Na Nd Ne Ng Nh Ni Nj Nk Nl Nm Nn Nq Nr Ns Nt Nv Oa Oe oF Og oH Oi OK On Op Or Ou Oz Pb PF Pg Ph Pi Pk Po Ps Pz Qa Qb Qd Qe Qg Qh Ql Qm Qt Qv Qw Qy Qz Ri Rm Rt Rv Rx Ry Rz Sh Si Sj Sr Ss St Tn To Tv Tz Ua Ub Ue Uf Ug Uh Uk Ul Um Un Up Ur Ut Uu Uw Va Vc Vs Vt Vu Vz Wc Wd We Wh Yd Yg Yh Yj Yk Yl Zq Zw Zx Ye Tl Wm Ti Th tF Yf) Vt(aE aY bL cH Ex Ib Ii Io Kk Mm Nk oK Op Ow Rh Ri Rt Vi Yd Yh Yi Zq Zx xA Tk Th) Bc(Op Rt Rx Rz Ux Vb Vi Vj Vw Wc Yd Yh) Op(Im Lh Oa Qa Qb St Un) bG(Ps Vb Vh We Wh Yl Yf) Gz(Jl Lx Mt) Yh(aS Hr Ub) Rt(Gp Hr Ld) Vi(Hu Im Ld) nD(Kr St Up) Dr(kR Rh) Uh(mM Wm) AjWh ChWd NgKo WcUn LjuZ WnVv OutX UfqH UpmH UwfP PdxA} Lj{jT(eT pS qH rN rS rW sC sK sM sO tN tR tS tT tU tV tX uG uI uL uM uN uO uT uU uW uX uY uZ vA vB vC vH wB wF wL wP wQ yK zA zI xA) cJ(fN rR rS tU uI uM uP uV uW uZ vP vQ vT vU vW wC wH wL wQ yH yJ yK zA zG zH tM tL xA) nY(rQ rR rS tU uL uN uO uP uV vC vH vO vP vQ vU wB wC wH wK wL wP wQ zA zH tM tL) rS(bF cC dB dE dJ eD Fb Hq hR Ip jD Ko kR Qc qD Rb Ri rV Tt Tv Ub Uf zH) wP(bL bP dB dE eD jD jO Ou qD RB Ri rO Tn To Tt Tv Ue uW vT xA) tU(bL cC dB dE Dg Di eD Fb Hq Ip jD Ko Pj qD RB Ri Uf Tj) wB(DB dC gP hP Ip jD Nm Rb Ss Ur) xA(aU dE dM iJ Ip Jg Nm Rb Uf) cC(rR uP uT vP vQ vT zA tM) dC(rR vP wL zA tM tL) gP(pS tV zA zI yE tM) uP(dE Ip Rb Uf Vs Vt) In(Im Is Jg Qa Qe) Zq(Gl Iq Op Rh Vq) uT(DB dE jD Tt) Lw(hP uM uU uZ) Ok(Jo Jt Nd Ng) qD(Jy rB wF wQ) As(vQ zA tM) Ip(rR vQ wQ) Kc(vT wH wQ) hP(Cv Jq Vs) zI(bL dJ Ur) uU(dM Ul Vs) Is(Jk Tk) Jg(Nd Ng) Ri(rP vQ) dB(rT tV) dE(qP rT) fN(Jq Jy) tR(Ue Ur) uM(Ni Uf) LvIm TvpS KfvA WneC dJtX dMuZ rBzA jRvV} Ng{Uf(eD eT eZ fN hO hP Im jG jO Pf pY qA qB qD rS tO tR tS tU Uh uM uP uV vT vV wB wC wE wF wG wJ wK wL wP wQ yD tM xA Tk) Jg(Aj Fp Hu Ik Il Im In Ir Is Jr Js Lh Lv Lx Mb Me Ml Mq Mt Mv Mw Nd Nh Nj Nl Nn Nx Oh Ok Pb Pd Pf Pg Po Qa Qe Wm) Nm(eZ hL qB qD qH sC sK tN tO tR tS tU tV tX uM uT vA wB wC wE wF wG wP wQ yL zA xA) Uc(eC eZ fN hL hO hP qD rC rV uM Ur uY uZ vB vT wB wC zA zH tL) Pf(Ba dE dJ Is Jq Jr Ko Lh Lv Lx Mt Nj Nl Nx Oi Ok Pb Qg Uh Wm) Ko(eT eZ fN fY hL hO hP Im pY qA qB qD rO rW uM uO wP xA) Ok(Fp Hu Ik Im In Is Lx Mq Nd Nj Nl Pb Qe) Dg(hO hW Im Is qD sK tU uT uU wB wG) Lx(Ba Fp Ik Im Is Lv Me Nd Nj Qc Wm) Kq(fN jD jF jO jT lN qD) Is(aN Fp Ik In Qg Tk) Uh(Ad Ba Bc Cs Im Tn) fN(Ad Fa Ny Pg Qh) wB(Ad Pj Ss Uu Vo) qD(Jt Kf Pj Qd Vt) Ba(Aj Qc Ur Vt) On(Fp Ik Im Nd) Wm(Ij Lh uM) Zq(Bc Ch Iv) Ss(uT vI wJ) Ad(Aj Ur) Fp(Im Mt) Qe(In Nd) Qh(jT jV) Vq(dF Fb) ImLh IvRz JthP NyuM WnVs VowP PdxA cGjO} Vt{qD(Aw aZ bL bN bR Ch cO Cp Ct Cw DB DE Fb Ha Hc Hf hG hP Hq Hr Ib iH Iv Iz jD Jk JO jT Jy Kc Kg Kr Kz lN Me Mv Nk Ny Of Ou Ow Oy Qg qH Qt RB rS sC uI uO vA vW xA Tj) Tk(bL Bo cH Cs Ct cV cC Fp gP Hc hG iA Ii Il Is It Jn Jr Kn Ko kQ kR kS Ld Ms Mw Nd Pf Qa Qc Qd Qe Qh Ra Sr Tv Ug Vv) vA(DB dE eZ Fb gP hX iH iJ jD jF jK jT jU Ko lK lN Ny oF Ou Pg Qg Ql qX qY Rb rC Uf uT wP) xA(bL Db dE hP Hr iH jD Kr Kz Me Qg RB rS uM Tj tF) dE(eT eZ fN hP qB qP sC sO uI uM uP uT vT wB zI) rB(hO sC sK tU uG uL uN vC vT vV vW tM) uM(bW cJ Dp Fb In jT lN Ny Qc qX Uf) hP(Ct DB Fb In Kz Lx Ny Ou qX) Ou(fN fY qP rS sC uO uP vH) Fb(eT eZ fN pY sC) uT(Db hG Hr iH jO) jT(qH uN vB zA) Wn(eC Ii Vv) eZ(DB iH) gW(Ti Th) wB(Db hG) lN(qH vT) vV(jQ jR) GlZq IbvT ImZx XakR OwuP eTiH wPjO jFsC} Ch{St(Dr Du Fi Gb Gc Gh Gn Hl Ho Hp Lp Lt Op Ps Rt Ru Rv Rx Ry Rz Sf Sh Si Sj Uw Uy Uz Vb Vc Vh Vi Vw Vz Wb Wc Wd We Wf Wg Wh Yd Yh Yi Yj Yk Yl Zq Zw Zx Ye Tm Tl Xa Ti Th Yf) Zq(aC aY Bc bE bL bR cI cQ cV Dl Em Gl Hu Ih Im Iv Jo Jr Jt Kf Kn Kr Ld Lt Lv Ma Mk Mm Mq Mt Nb Nd Nm Oa Op Oz Pf Qa Qv Rh Ri Rj Rt Vq Vv Wc Wd We Wh Yd Yh Th) Rz(dU eQ gZ Im Is Iv jB Jd kC kF kG kI kK kN kO Ld lW lY mE mF mI mM Mq mS MT mU mY nA nB nC nF nH nI nJ nK nL nO nT nU oD oQ oT oV oW Oz pH pI pK) We(Ad Ba Bc Co eC Ef Fb Gc gL Hb hG Ij Im Is It Jd Jn Kq kR Lh Mq Mt On Ps Qa Qe Ql Qm Vq) uM(Kq Ny Pg Qh Tn Uc Uf) qD(Ko Kq Ny tV Uc uV) hP(Is Kq Ny Qh Tn) Im(Lp Wh Th Yf) Uf(qH tU uI vT) Mt(Lt Wd Wh) wB(Nm Pj Ss) kR(Wh Xa) AdAj EfWc NmxA IsTk QhwP UuuT} Ou{Uc(fN pS qA qB qG qH qI qP qQ rN rP rQ rR rS sC sM tR tS

Figure 3 Continued

Figure 3 Continued

UryE dJuX} jB{Rz(aY Nb Ru Us Yh) Dr(aD Kd) Ij(Up Yk) FiJm Nrkl YhZq YiKd UpPh} Wm{xA(As Mt rS) Rf(rS tU) rB(bA cU) AsrS MtrP TvUh KqvA qHjT jRqO} Ny{rB(uO vO vV) wB(bR Rb) jR(vP vV) yL(bL dE) ThgW bWhO eDtT qAjT} Ij{Yk(lY mM nA nD nF nT) Up(fB nD pH) DrKg ShnF} gW{Th(Ax Kq Oh Pe Qa) Ti(Mp Oh Qa) Ky(Ex Gz)} kR{We(Iv Kj lY) Xa(Kg Kj) lX(Wd Wh) GhfB YhpH RylY} xA{Pd(Ms Oy qA Ua) Ax(Mj Tj) TjPe KneD dJqX} Rb{Mh(tU wL) fN(Ed Kk) tT(Lu Rc) QdeZ cGul} Kq{To(dU eQ oV pl pK) AwuO TthP OppK} Uh{Wn(De gP li) Up(nD nF) AdKg NimM RinD} dE{Mh(tU wB) Kf(sC vA) AxwB QdeZ RatV JlvT} Il{Dr(Kg Rt) Fi(Iv oV) IvYj KjnD RtlY} Pg{bL(jD jE jT IK IN qX sC)} Yh{pH(aY cZ Dr iH nO Vu)} Zq{Gl(Lh Pe) Iv(Bg Dk) DlbR OpoW} Up{Pi(eQ nD pI) Ph(eQ fA) IrnD} wB{Ad(Aw Hc Of) Uc(Ct Hc Hr)} vV{Mt(aV fY) jR(Qd Un) TnbA aVbF} Qa{Jg(Jk Oy) ThVp RtgP qHjT} Ct{Tk(Tn Uu) BaaC UrzA} Mw{Wn(Ii Uk) HcTk KfnD} Qc{jL(nC nO) mWiB qUkl} Cw{Kf(rU rW) RtOz} Dr{aY(dU pF) KdnF} Nd{Jg(Oy Qe) OnOy} Jl{NkfN QghO dJvT} Pe{Tj(tU uU) TooV} Ph{AahA FieQ IioV} Pi{pI(Fi Lt) MjoO} Dg{MtuO KkuV} Ed{WeYe WhRh} Nf{mFqW qYkK} Uc{IzuZ OfvA} Ir{GzRt RieQ} Pj{NkwF bRuT} cG{hA(bN hP)} tU{MhqX QhJk} jT{MtqA aDqH} AdRtOz BgRzpK TnbAyL QeJgOy WhnHoT RjeDtT UycRdU aCbRfR bGcVoW dJqXrW mlhXrY Unconstrained panels with 2 analytes, where 1.0E-8 >= 'AUC p-value' > 0. Contains 440 panels of 192,797 total panels evaluated. : Et(aA aC Af Aj AO Ax Bg bN Ch cI Co Cs Ct De Dg Dk Dl Ef Fp Fr Gl Hc Hq Hr Hu Hv Hw Hx Ih Ii Ij Ik Il Im In Io Ip Iq Ir Is It Iu Iv Iz Jg Jh Ji Jj Jk Jl Jm Jn Jo Jp Jq Jr Js Jt Kg Kj Kr Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Oy Oz Pa Pb Pc Pd Pe Pf Pg Po Pz Qa Qb Qc Qd Qe Qv Uk Wm) Ji(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb QC Qd Qe vS) Nw(eZ fN Fp fY hO hP Hv Ik Im In Is Jj Jr Li Lj Lu Lv Lx Mb Me Mq Ms Mt Nc Nd Ne Ng Nh Nj Nl Oy Pb pY QA qC qD Qe uM vS vT) Fp(Im In Is Jg Jj Jl Jp Jq Li Lv Lw Lx Mm Mt Mz Nl No Ok On Pb Qa Qe) Li(fN Jj rS tU uM uP uU vS vT vU vW wG zI xA) Lx(Hq Hv Im Is Jj Lj Lv Me Ms Nd Nj Of Oy) Mz(eT fN fY hL pY qA qB qC qD rU rV rW vS) Jj(Ik Im Is Jm Lh Mt No Ok Qa Qe) No(hO Nd Nh Nj qC qD uM vS) Is(In Lj Ms Nd Ng Og) Ok(In Jo Jt Nd Ng) Id(qC rS uM vS) Qe(In Ms Nd Nj) dM(eD hR rB rC) wD(Db nW Tr uM) qZ(DB dJ Ko) Ke(fN qC uM) vS(Ko Lj Vt) Ng(Jg Pf) Im(Nj Op) Qa(In Ms) oE(Vq Vt) AdAj ChZq MtLj KpfN nWuX Unconstrained panels with 2 analytes, where 1.0E-7 >= 'AUC p-value' > 1.0E-8. Contains 433 panels of 192,797 total panels evaluated. : Fp(aA Fr Hq Hr Hu Ik Il Io Ip Ir It Iu Iv Jh Jk Jm Jo Jt Lh Lj Lu Ma Mc Md Me Mf Mj Mk Mn Mp Mq Ms Mu Mw Mx My Na Nb Nc Nd Ne Ng Nh Ni Nj Nk Nm Nn Nq Ns Nt Nu Nv Nx Ny Oe Og Oh Oi Om Oy Oz Pc Pd Pf Pg Po Pz Qb Qc Qd) Nw(aA eT hL Hq Hr Hu Hw Hx Ih Ii Il Io Ip Iq It Iu Iv Jg Jk Jm Jn Jp Jq Js Jt Lh Lz Ma Mc Md Mf Mh Mj Mk Ml Mn Mw My Mz Na Nb Nf Ni Nm No Nr Ns Nt Nu Nv OE Og Ok Om On Pa Pc Pd Pe Pf Pg Po Pz QB Qc Qd rW wQ zH) Et(Ad aK Al An Ap Ar As AW BA Bb Bc bL Bn BO bR cH Cp Cq Cu Cv Cw Cx Db Dc Dd dE Di dM Ed Ez Fa Fb Gp Hf Ic Jd Kk Kl Kp Ks oE Ow Qt Qu Qw Qy Rh Ri Ss To Ua Ug Uh Ur Us Uu Uv Vo Vt Vv Tj) Lx(aA Hr Hx Ij Ik In Ip Iq Ir It Iv Jg Jn Jq Js Li Mb Mc Mq Mt My Mz Ne Nf Ng Nh Ni Nl No Nq Nr Ns Ny Oe Og Ok Om Pb Pd Pe Pg Po Qa Qe Wm) No(eC fN Hc hP Ik Im In Is Iz Lj Lv Mb Ms Mt Nc Ne Ng Nl Nq uZ vA xA Wm Th) Li(hP Im In Is Lv Me Ms Mt Nd Ng Nh Nj Nl Og Pb qC uV uW vP vQ wH wP wQ tL) Ok(Ii Ik Im Is Jr Lj Lv Mb Me Mq Ms Nc Ne Nh Nj Nl Oe Pb Qa Qe) Im(Hw Il In Is Jk Lh Lj Lv Ms Mt Nd Ne Ng Nh Nl Oe Qa Qe) Mz(eZ hO hP Is Me Mq oE Pf Qa qY rO tU wD wE) Qa(Ih Jg Jk Lj Lv Mb Mj Nd Ng Nj Nl Pb) Qe(lk Jg Jk Lj Lv Mt Ng Nh Nl Og Oy Pb) Is(Jk Lv Mb Mt Nj Nl Oe Oy Pf Tk) Jj(Jg Lj Nt Nx On Pf Po Pz Wm) Lj(Jg Lv Ne Nh Nl On qC) Mt(Me Ms Nd Ng Nj) Ke(hO hP oE qD sC) Ji(qD uM Wm) Pf(Lv Nj Og) wD(iH Pj To) qZ(dE nW Pj) Aj(Ba Jg) Id(hP qD) Uf(Ng qH) mZ(Dr Rz) NdOn IvZq Unconstrained panels with 2 analytes, where 1.0E-6 >= 'AUC p-value' > 1.0E-7. Contains 912 panels of 192,797 total panels evaluated. : Et(aD aE aF aG aH aI aJ aL aM aN aP aQ aR aS aU aV aX aY aZ bB bC bE bF bG bH bI bJ bM bP bQ bS bU bV bW bX bZ cA cB cC cD cE cF cG cJ cK cL cM cN cO cP cQ cR cS cT cU cV cW cX cY cZ dA dB dC dD dI dJ dK dL dN Dp eC eF Fn Fw gP Ha Hb Ib Id Je Jf jO Ju Jv Jy Kc Kd Ke Kf Ki Kn Ko Kq Kx Ky Kz Ld oN Op Or Ou pF Ph Pi Pj Pk Qg QH Ql Qm Qn Qx Qz Ra Rb Rc Rf Rj Rm Sr St Tn Tr Tt Tv Tz Ub Uc Ud Ue Uf Ul UM Un Uo Up Ut uV Vp vS Vu wD Yd Yh) Qe(Aj Hq Hr Hu Hv Hx Ih Ii Il Io Ip Iq Is It Iu Iv Jh Jl Jm Jn Jo Jq Jr Lh Li Lu Lw Ly Lz Ma Mb Mc Md Me Mf Mg Mj Mk Ml Mm Mq Mu Mv Mw Mx Mz Na Nb Nc Ne Nf Ni Nk Nm Nn Nq Nr Ns Nt Nu Nx Ny Oe Of Oh Om On Oz Pa Pc Pd Pe Pf Po Pz Qa Qb QC Qd) Li(aA Hq Hr Hu Hv Hx Ih Ii Ik Il Io Ip Jh Jk Jl Jo Jq Jr Lj Lu Lw Lz Mb Mc Mg Mh Mj Mk Mq Mw My Mz Na Nb Nc Ne Ni No Nq Ns Of Ok Oy Pa Po Qa Qd rU rW sC tO uI uO uR uY uZ vA vC wB wD wF wJ wK yD yH yK zG zH tM) Im(aC Aj Fr Hq Hu Ih Ik Il Ip Iv Jg Jl Jp Jq Ke Lu Lw Mb Mc Me Mf Mg Ml Mm Mn Mp Mq Mw Mx My Mz Nb Nc Ni Nq Ns Nt Nu Nx oE Og On Oy Pb Pd Pf Pg Po Qd Sf Uh Ur Wc Zx Ye Wm Th) Lx(aN bS Ch Hc hP Hu Ih Ii Iu Jk Jl Jm Jp Jr Lh Lu Lw Ly Lz Ma Md Mf Mg Mh Mi Mj Mk Ml Mn Mp Mr Mu Mv Mw Mx Na Nb Nc Nk Nm Nn Nt Nu Nv Nx On Oz Pa Pc Pf Pz Qb Qc Qd uM) No(Aj Bg Ch Ct De gP gW Hb Hu Hw Hx Ib Ii Il Ip Ir Jg Jk Jr Jt Kg Kr Lu Md Me Ml Mz Nb Ni Ns OE Ok Pb Pf Po pY Qa qH Qt Qw Ri rW Ua Uh Uk uO Ur VT Tj) Qa(Hq Hr Hu Hv Hw Hx Ii Ik Il Ip Iq Is It Iu Jm Jo Jq Jr Lh Lu Lz Mc Md Me Mk Ml Mn Mq Mt Mw My Nb Nc Ne Nh Ni Nk Nq Ns Nt Nu Nx Oe Og On Oy Pa Pf Po Qb) Is(aN Ct Fr Hq Hr Hu Hv Hw Hx iC Ih Ii Ik Il Ip Iq Jg Jo Jp JQ Lh Lu Mc Me Mg Mj Mk Mm Mq My Nb Nc Ne Nh Ni Nq Ns Nt Nx Of Pb Pd Pg Po qY) Nw(Fr Ij Ir Jh Jl Jo Lw Ly Mg Mi Mm Mp Mr Mu Mv Mx Nk Nn Nq Nx Ny Of Oh Oi Oz qH ql qO qP rO rS rU tU uL uV uY wC wD wE wL tM tL Wm) Ok(Hq Hr Hu Hv Hw Hx Ij Il Io Ip Ir It Jg Jk Lh Lu Mc Md Mf Mg Mh Ml Mt Mw My Nb Ni Nq Ns Nt Nx Of Og Oy Pa Pf Qb) Lj(aA dF Fr Hu Ik In Jh Jl Jp Jq Lh Lu Lw Me Mm Mq Mu Mw Mz Nb Nc Nd Ng Ni Nj Nt Nv Nx Om Pb Pf Po) Jj(Ad Dp Fr Ip Ir Jl Jn Jp Jr Lv Mw Mz Nd Ne Nh Nj Nl Nm Nn Nr Nv Oa oE Pd Pg Qb Qc Qd St Uh Vt) Mz(eD hR iB Ir jD jK jM jO jQ jR jT IK IN Mt Nj qO qP qQ rS uL uM vT wB yH zA zH yE) Fp(Hv Hw Hx Ih Ii Ij Iq Jn Jr Js Ly Lz Mb Mg Mh Mi Ml Mr Mv Nf Nr Of Pa Pe Uh) Mt(Ch Ik In Ip Jk Jr Lh Lv Mb Mq My Nh Ns Oe Of Og Oy Pb Pf Po Qd) Pf(Aj In Ip Iz Jk Jr Mb Me Mk Mq Ms Nd Ne Nh Ni Nl Oe Pb) Ji(Aj Ao Bg BN Ch De Dk eC eZ fN hO hP Kg oE Uk yL) Ke(eC eT hL pY qA qB sO uV vS) dM(aC hW hX jD jK jO jQ qC qY) qZ(Ad aH aZ Dg Id iH oK Tr wL) Vt(eC In qC qD Uh vA xA Tk) Ng(Ba Kq Lh Ma Po Tn Uh) Id(fN oE uU vA vT vW wP) wD(bL dB dE Ko Kr qD Rb) Pe(Mj Mq qC Wm Tj) aC(Ax Ba cE Dg Fr) Nd(Fr Jp Lh Mp) In(Nt Pd Po St) qC(Cs Ko Kp Ny) St(Ch nD Ye) Uh(Mq oE Wm) Jg(Lv Oy) bF(aM aN) cG(hA jO) AjKq BaCt DbwB EdWh Mqlp MsLh TrvS ZqOa WemZ KkoE bRfR dBtV dFjO Unconstrained panels with 2 analytes, where 1.0E-5 >= 'AUC p-value' > 1.0E-6. Contains 1,643 panels of 192,797 total panels evaluated. : No(aA aC Ad Af Al AN Ao Ap Ar As Aw Ax Ba BB Bc bL BN BO bS cA cF cK CO Cp Cq Cs Cu CV Cw Cx Db Dc Dd dE Dg Di dJ Dk Dl Dp Ed Ef eT EZ Fa Fb Fr fY Gp Ha Hf hL Hq Hr Hv hX Id Ih Ij Io Iq It Iu Iv Jd Je Jh Jl Jm Jn JO Jp Jq Js jT Ju Jv Kc Kd Ke Kf Ki Kj Kk Kl Kn Ko Kp Ks Ky Kz Ld Lh lN Lw Ly Lz Ma Mc Mf Mg Mh Mi Mj Mk Mm Mn Mp Mq Mr Mu Mv Mw Mx My Na Nf Nk Nm Nn Nr Nt Nu

Figure 3 Continued

Nv nW Nx Ny Oa Of Og OH Oi Om ON Or Ou Ow Oy Oz Pa Pc Pd Pe pF Pg Ph Pj Pz qA QB Qc Qd Qm Qn qP Qu Qv Qx Qy Rc Rh Sr Ss tR tU Tv Ub Ue Uo Us UV uY Vo Vp Vv vW wE wH wP wQ yD zA) Pf(aA aC aN Bg bL bN bO bS cA Ch Ct dE dJ gP Hc Hq Hr Hv Hw Hx Ih Ii Ij Ik Il Io Iq Ir Iu Iv Jg Jh Jl Jm Jn Jq Js Lh Li Lu Lw Ly Lz Ma Mc Md Mg Mi Mj Mn Mp Mu Mv Mw My Na Nb Nc Nf Nk Nm Nn Nq Ns Nt Nu nW Nx oE Of oH Oi oN Oy Pa Pc Pd Pe Pg Po Qb Qt Rt Ua Uh Uk Ur Vt Wb Wm Tj Th) Li(dJ Fr gP Hw Ij Iq Ir It Iu Iv Jg Jm Jn Jp Js Jt Lh Ly Ma Md Mf Mi Ml Mm Mn Mp Mr Mu Mv Mx Nf Nk Nm Nn Nr Nt Nu Nv Nx Ny OE Oh Oi Om ON Oz Pc Pd Pe Pg Pz Qb Qc qH qI qP qQ qY rO rP rQ rR rT rV sK sM sO tQ uL uT vB vH vO vV wC wE wL yJ yL zA) Lj(dM eC Hq Hr Hv Hw Hx Ih Ii Ij Il Io Ip Iq Ir It Iu Iv Jk Jm Jn Jr Js Jt Ke Ly Lz Ma Mb Mc Md Mf Mg Mh Mi Mj Mk Ml Mn Mp Mr Ms Mv Mx Na Nf Nk Nm Nn Nq Nr Ns Nu Ny OE Of Og Oh Oi Ou Oy Oz Pa Pc Pd Pe Pg Pz Qb Qc Qd rS tU Uh Ur Vt Zq Wm) Im(aA Ax Ch Ct dM Fa Fi Gh Gn gP Gz Hl Hr Hv Hx Ih Ii Ij Io Iq Ir It Iu Iz Jh Jm Jn Jo Jr Js Jt Kk Lp Ly Lz Ma Md Mh Mi Mj Mk Mr Mu Mv Na Nf Nk Nm Nn Nr Nv Ny Of Oh Oi Om Oz Pa Pc Pe Pz Qb Qc Qv Rz Si Sj Tv Uk Vt Vz Wb We Yk Zq Tm) Is(aA Aj Ch cV dJ eC hW iB Ij Io Ir It Iu Iv jD jE Jh jI jK Jl Jm Jn jO JR Js JT jU jV IK IN Lw Ly Lz Ma Md Mf Mh Mi Ml Mn Mp Mr Mu Mv Mw Mx Na Nf Nk Nm Nn Nr Nu Nv Ny oE Oh Oi Om On Oz Pa Pc Pe Pz Qb QC Qd Qg rB Uk Ur) Mz(hA hV hW hX iC Ih Ij Iv jE jF jG jH JL jP Jr jU jV jY IL IM IO Lv Mf Nh Nl Ns Nu Ok Pd Pc Pg Po pS qG qH qI qX rA rC rN rP rR rT sC sK sO tX uI uN uO uR uU uV uX vA vB vC vH vU vV vW wH wJ wP yK yL zI tM xA) Mt(aA Aj Fr Hq Hr Hu Hx Ih Ii Ij Il Iq It Iv Jg Jh Jl Jm Jp Jq Js Lu Lw Ly Ma Mc Md Mf Mh Mi Mk Ml Mm Mn Mp Mv Mw Mx Na Nb Nc Nf Ni Nk Nl Nm Nn Nq Nr Nt Nu Nv Nx Ny oE Oi On Oz Pa Pc Pd Pe Pg Pz Qb Qc Wc) Qa(aA Aj bN Ct eC Fr Ij Io Ir Iv Jh Jl Jn Jp Js Jt Lw Ly Ma Mf Mg Mh Mi Mm Mp Mr Mu Mv Mx Na Nf Nm Nn Nr Nv Ny Of Oh Oi Om Oz Pc Pd Pe Pg Pz QC Qd Qg Uh Uk Ur Vt Wm Th) Uh(Ad Aj AN Ao As Ax Bg Bn Ch Cp Cq Cs Cu Cw Dc De dM Ed Fa gP Hc Hq Id Iv Iz Ji Jk Jo Jy Kg Lx Md Me Ml Ne Nf Ni Nm Oa Pe Qe Qv Ra Rh Ri Sr Tn Tr Tv Uc Uk Un Us Vv) Ok(aA Aj Fr Ih Iq Iu Iv Jh Jl Jm Jn Jp Jq Js Kg Lw Ly Lz Ma Mi Mj Mk Mm Mn Mp Mr Mu Mv Mx Na Nf Nk Nm Nn Nr Nu Nv Ny Oh Oi Om On Oz Pc Pd Pe Pg Po Pz QC Qd) Nw(Ax bA Bg bN eC Ed Fa jQ Kr Oa pF qG qQ qY Rh rN rP rQ rR rT rV sC sK tO uI Uk uO uP uT uU uZ vH vP vQ vV wB wF wG wH wJ wK wP yH yJ yK yL zA zG zI yE xA) Lx(aC aF Aj An AX bA bL BO cA cH cK Co Cs Ct cV Fr Gh Gp Hw Ib Il Io Jh Jo Jt Kc Kj Kr Mm oE OH Oi Pi qC Qg Rh Ri Sr St Uk Ur Uv Vt Wc Tj Th) Jj(aC Ax Bc Dc Dg dJ Fa Hu Ih Ii Ij Il It Jq Js Ke Kf Ko Kp Kq Ma Me Mg Mn Mp Mq Nb Nc Ng Ny Oh Om Pb Pj Qh Qm Rm Sr Tr Uc Uf Un Us Vq) Ji(aC Af aN Ar AW Ax bA bL Bo bS cA cl Co Cp Cq Cs Cx Dl dM gP Hc Ib Iz jO Kr Qg qY Rh Ri Ua Up Ur Ut Uv uY wD wE Tj Th) Et(DR Eq fN fP Fy gL gW hB hC hF hG iA iH iJ iO iP iZ jD jK jP kQ kR nW nY oF oH oK qA qC Rg uN Vq Vs vV Wc yL Ye Th) Pe(aN Bg bL Ch Ct dJ dM gP Ha Hc Hq Hw Iv Iz Kg Lv Lw Lz Mc Md Mi Mr Ns oE Of Oy Pb Po Qg Qt Ua Uk Ur vS Th) Ke(Aj Ax De eD eZ gP jG jO Kg Kr Ms Ne Ng Oa oN Pb Qe qH qI tU uI uO uY uZ vA vW wD wL wQ yD yL zH zI Wm) Vt(Ax bA bN cT dF Fa Fp Gp hP iA Ms Mw Ne Ng Nr nW Oa oF oH pF qB Qc Qv Rh Uk Ur) dM(gW hA hO hV iB iC Ij jF jH jI jL jM jP jR jT jU IK IL IO Oa qD rX rY rZ uW) Qe(aA Bg bN Ch Ct Fr Hw Ij Ir Jp Js Jt Mh Mi Mn Mp Mr Nv Oi Pg Uk Ur Wm Th) wD(aZ Bb cV De dJ Fb Id jF jM jO Kp Ks Kz qC Qh Ql rC Ri Tn Tv Ub Uf Uu) oE(bF cG Fb Ij Ip It Kd Kn Ko Kq Mw nD Oa Pg Pj Qd Qh Rt Sr St Uf Un Wc) Jg(In Ir Jr Lh Me Ml Mq Ms My Nc Nd Ne Nh Ni Nj Nl Og Pb Po Qb Qd) Lv(Fr Ik Jl Jp Jq Lh Me Mm Mw Nd Nh Nu Nv Ny Om On Pb Po Pz Qd) Fa(dJ eC Gp Hc hP Hq In Iz Ne Ng Oy Rh Uk Tj Th) Ir(Hq Ik Il In Jl Jr Mq Ms Nd Ng Nh Nj Og Pb Rt) On(Ik In Jr Mb Me Mq Ms Ne Ng Nh Nj Nl Oy) aC(aA Ad Ap Ar Bb Bc bF cG Cs Cu dF fR Mw) Id(eC hO qB qH rP sC tU uG uP uZ zH xA) Ij(Aj Hc In Iz Jl Jr Ne Ng Nh Ur Wc Th) Po(Hq Me Mq Ms Nd Ne Nh Nj Nl Nt Pb) Lh(aA Ik Jo Jr Kg Mb Mq Nh Ni Nj Nt) Fr(Ik Jr Mb Me Mq Ng Nh Nj Nl Pb) Jl(hP Ik In Jq Ms Nd Nj qD uM vT) Ng(Ad Jp Ko Mw Nn Nt Pg St Tr) Qd(Ik In Ms Nd Nh Nj qC qD Wm) vS(cH Kp Kr Ny Oa Sr Uf Un Wm) Jp(Ik Jr Mb Ms Ne Nh Nj Nl) Pg(eD jO Mb Me Nd Nj qC qD) dF(Ax CH Cs Ct dJ dX eP) qZ(Bb bL Cs cV Ss uM uY Wm) Mq(Hw Js Ma Nd Nj Nr Th) Oa(In Lp Ne pF qC Ur Th) Nh(Jr Mn Ne Nn Qb) Sr(hP In Jk qC Qw) Kq(Bg Ch Dk qD Th) cG(aN cA cL gW hP) Aj(Ko St Tn Uc) Mw(Ch Hc Ib Iz) qC(cH Fb Oh Pj) uM(cAx Ny Uf Wm) Cs(bA Gp uP) Ct(Ad bA cT) Nd(aA Nn Nv) Tr(Oy wB wH) Ik(aA In Jq) Ow(Gh Sf Zx) Ur(Ax St Wm) cE(aM aN dJ) mZ(Uy Tl Xa) Th(Fp St) Ms(Nt Qb) Zq(Bg Ed) Kp(qB vA) Uf(hO uI) bF(cV dJ) dB(rN wP) nD(oF Qc) wB(Kr Nm) qD(Jy Ny) AxxA ChTn DbuT WmrB MhrS NjQb Hwlv lhln IpJr OhhP aAdJ tXnW hBjO Unconstrained panels with 2 analytes, where 1.0E-4 >= 'AUC p-value' > 1.0E-5. Contains 4,211 panels of 192,797 total panels evaluated. :
Ji(AD aE aF aG aH al aJ aK AL aM An aO AP aQ aR As aU aV aX aY aZ Ba Bb BC bE bF bG bH bI bJ bM bO bP bQ bR bU bV bW bX bZ cB cC cD cE cF cG cH cI cK cL cM cN cO cP cQ cR CT CU CV CW cX cY cZ DB DC Dd dE dF DG dH DI dJ dK dL dN dR Ed EF eT Ez Fa Fw fY Gl Gp gW HA Hb HF hL hX Ic JD JE jG jK jL jP jQ jT Ju jV jY Kd Kj Kk KS IK IM nW Oa oN Or Ou pF Ph Pi pY qA qB QH Ql Qm Qt Qu Qv Qw Qx Qy Qz Rb Rc Rf Rj Rm rO rS Rt rW sC Sr Ss St Tn Tr Tt Tv Tz Ub Ud Uf Ug UL Um UO Us Uu uV vA Vo Vp VT vU vV wB Wc wG wK wP wQ yD yH yJ yK yL zA zH tM) No(aD aE aF aG aH al aJ aK aL aM aO aP aQ aR aS aU aV aW aX aY aZ bA bC bE bF bG bH bI bJ bM bP bQ bR bU bV bW bX bZ cB cC cD cE cG cH cI cJ cL cM cN cP cQ cR cS cT cU cW cX cY cZ dA dB dC dD dF dG dH dI dK dL dM dN dR eD eF Fn fP Fw Fy GL hA hB hC hF hG iA iB IC iH iJ iO iP iZ jD jE JF jH jI jK jP jQ jR jV JY KQ kR kS Kx IK IL IM IO nY oF oK Pi Pk QG Qh ql Ql qO qQ qY Qz Ra Rb Rf Rg Rj Rm rO rP rQ rR rS rU rV sC sK St Tn TO Tr tS Tt tV Tz Uc Ud Uf UG ul UL Um Un UP UT UU uW vB vC vH vP vQ VU vV wB wC wD wF wG wJ wK wL yH yJ yK yL zH tM tL Ti tF) Pe(aC AD aE aG al AJ aK AL aM An Ao AP aQ AR As aU aV AW AX aY aZ BA BB bC bF bG bJ bM bN BO bP bQ bR bS bU bV bW bX bZ cA cD cE cF cG cH cI cJ cK cL cM cN CO Cp Cq cR CS cT CU CV CW cY dA DB DC Dd DE dF DG dH DI DK Dl Dp dR eC EF Ez Fa Fb FN fP Fw Gp Hh Hf hP Hr Ib Ic Id iH Ir Iu Jd Je Jg Jh JJ jQ jT Ju Jy Kc Ke Ki Kj Kk Kp Kq Kr Ky Kz Ma Mf Mh Ml Mu Mx My Na Nd Nf Nr Ny Oa oF Og oH oN Or Ou pF Ph qD Qh Qn Qu Qv Qw Qx QY Rc Rg Rh Ri Rt Sr Ss Tn To Tr Tv Tz Ub Ud Ue Uf Ug Ul Um Uo Ut Uv Vo Vp Vt Vu Vv Wh Zq) Uh(aD aE Al aM aO Ap Ar AW BA Bb Bc bL Bo bV cH cl cL cM Co cQ CT CV Cx Db Dd dE DG Di dJ Dk Dl dN eC eF Ez Fb Fr hB hC HF hG Hr Hu Hv Hw Hx Ib Ih Ii Ij Ik Il In Io Ip Iq Ir Is It Iu Jd Jg Jl Jn Jp Jq Jr Js Jt Jv Kd Ke Kj Kk Kn Ko Kp KQ Kr Kx Ky Kz Lh Li Lv Lw Ly Mc Mf Mi Mj Mk Mm Mr Ms Mt Mu Mv Mw Mx My Mz Na Nb ND Nh Nj Nk Nl Nn Nr Nt Nu Nv Nw OF Og oH OK Om oN Or Ou Ow Oy Pb Pd pF Pg Ph Pi Pj Pk Po Pz Qb Qd Qg Qh Qm Qn Qw Qy Rb Rc Rf Rg Rj Rm To Tt Tz Ua Ud Ue Uf Ul Uo Up Ur Uu Uv Vp Vu wD Wn Tj) Vt(aC Aj aK aM aN aS aZ bB bF Bg bH bJ bL b0 bP bQ bS bV bZ cA cD Ch cL CS cV dD dE dJ dM Dp dR Ed Ef eT eZ fN Fr fY gL gP hB HC HF hG hL hO Hq Hr Hv Ic IH Ii IJ Il iO iP Is It Iv Iz Jg Jh Jk Jn Jo Jr Kc Ke Kg Kj Kk Kp KQ KR kS Kz Li Ly Lz Ma Mb Md Mj Mk Ml Mm Mq Mt My Mz Na Nd Nh Nl Nn Nq Nw Nx nY Oh OK oN Ou Ow Oy Oz Pa Pb Pd Pj pY Pz Qc Qd Qg Qh Qm qZ Rc Rf Ri sC Sr Ss St Uf ul Ul UM UO uP Us uT uU Uv vT vW wD wP Zq Tl Wm Tj Ti tF) Lx(Aa AD aE Af al aK AL aM AO Ap aQ AR aS aU aV aY aZ Ba Bb BC bE BG bH bI bJ bM bN bP bQ bU bW bX cB cC cD cE cG cl cN cP CQ cR cT Cu Cv CW CX cY cZ dA Db DC DD DE dF Dg Dl dJ Dk Dl dM Dp eC Ed Ef Eq EZ Fa Fb fN fP fR Gl gP gW Ha Hb Hp Ic Id Iz jO Jy Kd Ke Kg Ki Kk Kl Kq Ks Kx Ky Kz Ld Oa Ow pF Ph Pj Qh Qm Qt Qu Qv Qw Qx QY Qz Rb Rc Rf Rg Ss Tz Ua Ue Uf Ug Ul Um Un UO Us Ut Uu Vo Vu Vv Wb Yk Zx) Im(aE aI aJ Al aN Ao aQ Ar aU aW bB BC bF Bg bL bM bN bR bS bU bV bW bZ cE cF cG cH cI cJ cK cM cN Co cR Cs CV Db dD dE dF DG Di dJ dL dN DR Du eC eF Eq Fb Fc Fd Gb Gc Gp HB HC Hf Ho Hp iA Id iH iP Jf Ju Jv Kc Kd Kg Ki Kj Ko Kp Ks Ky Lt mT nA nD nW nY Oa oF oH Or Ou Ow pF Pj Ps qC Qg Qt Qu Qw Qy

Nu Nx Ok Pj Qh Us) Nt(Ip Jo Jq Nb Ne Nl Ns Oe Og Pb Qb) Uf(Ch Ed fN In rS tU Uk uV Vv wB wF) Ms(Jn Jq Js Mp Nn Nr Nv Oh Om Un)
Nl(aA Ip Ma Mn Nb Ne Ni Nk Nv Qb) Iv(Jh Jn Jq Ma Na Nx Of Oh Oy Rz) Zq(Ar Bc bR Dg Dl Gl Ld Op Vo Wc) Ko(bN Ed hP Kj qD rS sC
Uk wP xA) In(Js Ma Nu Nv Om Qb Un Vq Wm) Ar(Gp Hq It Mk My Ne Ps Th) Tr(eZ Kj pS qA tN tT uN uT) Ip(aA jQ Mx Nb Ne Nu Og Qb)
Js(jE jO jQ jT jV IN qX qY) Ch(Ad Ba Nr Ok Qh Qm We) nD(bQ gL hB Jn oK oN Pi) Ed(Ok Pj Rz Vq We Xa) Kr(oO tR uO uT yD zI) Uk(Ad
Fy It Ok Pj Un) Ma(Ih Jq Mx Ne Nu) Om(Mb Ml Ne Og Pb) dJ(bQ bZ hB pF qX) wB(dB nW Pj Rb uM) Ad(bZ Gp Jo Kj) Wm(Hb Jq Rf rS)
Tn(Bg Ct Iz Oy) Wc(Fp Jn Ow Un) Jy(eZ fN jD lK) uM(Kf Mp Mx qX) Fb(fN pS rS) Ne(Mn Nb Qb) Og(Ih Nn Oh) Ok(Ct jO Kj) Ow(Fi Rt
Ye) Un(Jk qD Th) Pd(hX Jq xA) cU(jO jQ rB) cV(bN Dr nN) Bc(Gp Tl) Db(tV wP) Fp(Aa lX) Nr(aN Ky) Mb(Nv Qb) Vq(Ps Ye) Pb(Nu Nv)
Pj(Qv wF) aA(cH qY) hX(kP ml) nW(sM uT) CubL CwRt DrpF GpdX NmOf MmHu UcvA IhJq QhrB TlKd KkfN WnVv aJbR aMcT bZcH dBuX dEtV hWjT qDrX jDoF

Unconstrained panels with 2 analytes, where 1.0E-3 >= 'AUC p-value' > 1.0E-4. Contains 10,813 panels of 192,797 total panels evaluated. : Oa(aA AD Af aG aH aI aJ aK Al aM AN AP AR aW Ax aZ BA BB BC BG bH bL bN BO bP bQ bR bS bU bV bW cA cD cE cF CH cI cJ cM cN CO cP cR CS CT CU CV Cw CX Db Dc DE DG dH Di Dk DL dN Dp DR Ed Ef EQ Ex Ez Fb Fc FN FP Fr Fw Gb Gc Gd GL Gn GP Gz Hb HC HF hG Hl Ho Hp Hq Hr Hu Hv Hw Hx Ib Ic Id IH Ii IJ Ik Il IO IP Iq Ir Is It Iu IZ Jd Je Jf Jg Jh Jk Jl Jo Jp Jq Jr Ju Jv Jy Kc Kd Kf Kg Ki Kj Kk Kl Kn Kp kQ KR KS Kx Kz Lh Li Lj Lu Lv Lw Ly Ma Mb Mc Md Me Mf Mg Mi Mk Ml Mn Mp Mq Mt Mu Mx My MZ Na Nb Nc ND Nh Ni Nj Nk Nl Nm Nn Nq Nr Ns Nt Nu Nv NY Oe Of Og Oh Oi OK Om ON Op Or Ow Oy Oz Pa Pb Pc Pd Pg Ph Pl Pk Po Pz Qb Qc Qd Qh Ql Qm Qn Qt Qu Qw Qx Qy QZ Rb Rc Rf Rg Rh Ri Rm rP Rv Rx sC Sf Sh Si Sj Sr Ss St Tn Tr tU Tv Tz Ua Ub Uc Ue Uf Ug Ul Um Uo Us UT Uu Uv Uw Ux Uz Va Vb Vc Vh Vi Vj Vo Vu Vv Vw Vz WB Wc Wd We Wf Wg wP Yd Yj Yk Yl Zw Zx XA Wm tF Yf) Kq(Ad aE Af aK Al aM AN Ap aR As aU aV AW aY aZ BA Bb Bc bF bG bI bJ BN Bo bP bS bU bZ cA cE cK cL cN cO Cp CQ cT Cu Cv CW Cx cY dA Db Dc Dd dE Dg dH Dl dJ dK Dl Dp dR ED EF eT Ex EZ Fa Fb Fi FN Fr Fw fY Gh GL Gp gW HA Hb hC HF hG HR hV HW HX iA IB IC Id IH Ii IJ Ik Il Im Io IP Iq Ir Is It Iu Iv iZ Jd JE JF jG JH JI jK JL JM Jn Jo JP jQ JR Js Jt JU JV JY Kc Kd Kf Kg Ki Kk Kl Kn Ko Kp kQ KR kS Kx Ky Kz Ld Lh Li lK lL lM lN Lu Lv Lw Ly Lz Mb Mc Md Me Mf Mg Mi Mj Mk Ml Mp Mq Mr Ms Mt Mv Mw Mx My Mz Na Nb ND Nf Nh Ni Nj Nk Nn Nr Nt Nu Nv NW Nx Ny Oe OF Og Oi Ok Om ON Op Or Ow Oz Pb Pc Pd Pg Pi Pj pY Pz QA Qb Qc Qd Qe Qg QH Ql Qm Qn Qt Qu Qw Qx QY qZ Ra RB Rc Rf Rg Rh Ri Rj Rm Ry sC Sr Ss St Tn To Tr Tv Tz Ub Uc Ud Ug uI Um uO Up Us Uv uZ Vo Vp Vv wB Wc wD yL Ye Tm Wm Tj) Ij(aA aC AD aE AF aG aH aI aK AL aM An Ao AP aQ AR AS aU aV AW AX aY aZ Ba BB BC bE bF bG bH bI bJ bM Bn BO bP bQ bR bU bX bZ cB cC cD cE cF cG cJ cK cL cN CO CP CQ cR CS cT CU CV CW CX cZ dA DB DC DD DE dF Dg dH Dl DK DL Dp dR Ed EF Ez Fb Fc Fi Fn fP fR Fw Gc Gh GL Gp Hb hC HF hG Hl Hp Hr Hv Hx iA Ib Ic Id IH Ii iJ Il iO Iq It Iu Jd Je Jf Jh Jk Jm Jn Jo Js Jy Ke Kg Ki Ko Kp kQ kR kS Ky Lu Ly Lz Ma Mb Mc Md Mf Mg Mi Mj Mk Ml Mn Mp Mr Mu Mv My Nc Nf Ni Nk Nn Nr Nt Nv nW Nx NY Oe Of OH Oi oK Om ON Op Or Ou Oz Pa Pb Pc Pd Pe Pj Pz Qb Qc Qg Qh Ql Qm Qu Qx Rb Rc Rf Rg Rh Ri Rm Rt Ry Rz Si Sr Ss St Tn Tr Tt Tv Tz Ub Uc Ud Ue Uf Ug Ul Um Un Uo Up Ut Uu Uv Vc Vo Vp Vv Vz Wb Wf Wh Yd Yk Yl Zq Zx Ye Tm Tl Xa Tj Ti) Qa(Aa AD aE AF aG aH aI aJ aK aL aM AO AP aQ aR AS aU aV Aw aX aZ Ba BB BC bE bG bH bI bJ bM Bn bP bQ bU bV bW bX bZ cB cC cD cE cF cG cJ cK cL cM cN Co CP CQ cR cS CU Cv CW CX cY cZ dA DB DC DD De dF DG dH dI DK DL dN Dp DR Ed EF Eq Ez Fb Fc Fn fP fR Fw Gb Gc Gh GL Gz Ha HB hF hG Hl hP iA iB Ic Id iH iJ iO iP JD JE JF jK jM jP jQ jR JU JV JY Kc Kf Ki Kl Kn Ko Kp kQ kR Ks Kx Ky Kz Ld lK lL lM Lp lX lY mM mU mW nA nI nT nY oF oK oN Op Or Ow Ph Pi Pj Pk qD Qh Ql Qm Qn Qu qV QX Qy Qz Ra Rb Rc Rf Rg Ri Rj Rm Ru Rv Rx Ry Rz Sf Sh Si Sj Sr Ss St Tn To Tr Tz Ub Uc Ud Ue Uf Ug Ul Un Uo Up Us Ut Uu Uv Uw Uz Vb Vc Vh Vi Vo Vp Vs vT Vu Vv Vz Wb Wc Wd We Wg Wh Yh Yj Zq Zw Zx Tm Tl Xa tF) Vt(aA AD aE AF aG aH aI aJ AL An AO AP aQ AR As aU aV AW aX aY Ba Bb BC bE bG bI bM Bn Bo bR bU bW bX cB cC cE cF cG cH cI cJ cK cM cN CO CP CQ cR Ct CU Cv CW CX cY cZ dA DB DC Dd Dc DG dH DI DK DL dN eF Ex Ez Fb Fn fP Fw Fy Gh Gl gW Gz Ha Hb Hu Hw HX Ib Id Ik Io Ip Iq Ir Iu iZ Jd Je Jf Jl Jm jO Jp Jq Js JT Ju Jv Jy Kd Kf Ki Kl Kn Ko Ks Kx Ky Ld Lh Lu Lv Lw Mc Me Mf Mg Mh Mi Mm Mp Mr Mu Mv Mx Nb Nc Nf Ni Nj Nk Nm Ns Nt Nu Nv Ny Oc Of Og Oi Om On Or Pc Pg Ph Pi Pk Po Ps qA Qb qH Ql Qn qO qP Qt Qu Qw QX Qy Qz Ra Rb Rg Rj Rm rQ rR rS RT rU rV rW sK sO Tn To Tr Tt tU Tv Tz Ua Ub Uc Ud Ue UG uL Un Up Ut Uu uV uW uY uZ vC vH Vo Vp vQ vU VV wB Wc wE Wh wQ yH yJ yK yL zH zI Ye tM tL Xa Wn Th) St(aC AD Af aM AN aO Ap Ar As AW BA BB BN bO bS cA cF cH cI cL cM Co CP Cq cT Cu CV Cw Cx Db Dc Dd dE Dg dH Di dJ Dk Dl DR Ed EF Eq Ez Fa Fb Fi Fn Fp Fr Gc Gh gL Gn Gp Ha Hb HC HF Hp hR Hv iA Ic Id IH Ik Im Io Ip Ir Is It Iu Iv Jd Je Jf Jg Jh jK Jl Jn JO Jp Jr Ju Jv Jy Kc Kd Kg Ki Kj Kk Kl Ko Kp Kr KS Kx Ky Kz Ld Lh Li Lv Lw Ly Lz Mb Mc Md Me Mg Mh Mi Mj Mk Ml mM Mn Mp Mq mS Mt Mu Mv MW Mx My Mz Nb Nd Nf Nh Ni Nj Nk Nl Nm Nn Nq Nr Ns Nt Nv Nx Ny Oe Of Og oH Oi Ok oN Op Or Ow Oz Pc Pd Pe Pg Ph Pj Pz Qb qC QD Qe Qg Qh Ql Qm Qn Qt Qu Qw Qx Qy qZ Ra rB Rg Rh Ri Rm Rz Sh Si Sr Ss Tn To Tr Tt Ud Ue Uf Ug Uh Um Un Uo Ut Uu Uv Ux Va Vi Vo vS Vu Vv Wc wD Yh Zx Tm Tj) Ke(aA aC Ad aJ Al aM AN aO Ar As AW aY aZ bA Bb Bc bG bI bJ BO bP bS bV bZ cD cH cI Cq CT Cu CV Cx Db Dc dF Dg dH Di dJ Dl dN Dp dR EF Fb Fn fP Fy gL gW HA HB hC hF HR Hw HX iA IC Id IH Ik Il IO IP Is It Iu Iv Iz JD JE JF jH JI jK JL Jm Jn jP JQ JR Js jT JU JV JY Kc Kd Kf Ki Kk Kn Ko Kp kR kS Kx Ky Ld Li lK lL lN lO Lu Lz Ma Mb Mc Md Me Mh Mi Mj Mk Ml Mm Mn Mp Mq Mt Mu Mv Mw Mx My Mz Nb Nd Nh Ni Nj Nk Nl Nm Nn Nr Ns Nu Nv NW Nx Ny Of Og Oh oK Om On Or Ow Oy Pa Pc Pd Pg Ph Pi Pj Pk Po Pz Qb Qc Qd Qh Qn qO qQ Qt Qu Qw Qx QY Qz RA Rc Rf Rg Rj Rm rN Sr Ss TN TO tQ Tr Tt TV Tz Ua Ub Ud Uf uG Ul Um Un Uo Ur uU vH Vo yJ Tj) Fa(aA aC AD aE aF aG aH aI aJ aK AL aM AN aO AP aQ AR AS aU aV AW AX aZ BA BB BC bE bF bG bH bI bJ bM bN BO bP bQ bR bU bV bW bX bZ cA cB cC cD cE cF cG cH cI cJ cK cL cM cN cO CP Cq cR CS cT CU Cv CW CX cY cZ dA DB DC DD dE dF DG DI DK Dl dM dR eD eF fP Fr fY GL gW hB hC hF hG Hr Hu Hw iA Ih iJ Ik iO iP Iq Ir Iu Iv jD Jf Jh Jl Jn Jr Js Jt Jv Jy Kl Kn kQ kR kS Kx Kz Ld Li Lv Lw Lz Ma Mb Md Mf Mg Mh Mi Ml Mp Mq Mr Mx Nc Nf Nk Nm Nn Nr Ns nW NY OF OH Om ON Ou Ow Pa Pd Ph Pi Pk Po Pz Qb Qc QD Ql Qn Qu Qz Ra Rb Rc Rg Rj Rm rO Ry Ss Tn To Tr Tv Tz Ub Uc Ud Un UP Ut Uu Uv uZ vA Vo Vq Vu Vv Wc wD Wh yL zH Zq Ye xA Tk Ti) Sr(aE Aj Al Ap aQ aR As aV aY BA Bb Bc bE bH bI bL bM bN BO bQ bR bS bU bZ cA cF cG cH cJ cL cP cQ cR Cs Ct Cu Cv CW CX cY DC dE dF DG dI dJ dM Dp Ed EF eT EZ Fb Fn FP Fr Fw fY Gl Gp gW HA hB hG hL hO Hr Hu Hw iA Ic iJ Ik Il IO iP Iq Ir Is It Iu Iv Je Jf JG Jh jK jM Jn JO Jp jQ JT Ju Kc Kd Kg Kj Kk Kl Ko Kp Kr Ky Kz Lh Li lN Lu Lw Lz Ma Mb Mc Me Mf Mh Mi Ml Mm Mn Mr Ms Mt Mu Na ND Nf Nh Ni Nj Nk Nl Nm Nn Nq Nr Ns Nu Nv nW Nx NY Oe oF Og OK On Ow Oy Pb Pc Pf Pg Ph Pi Pj Pk Po pS pY Pz qB Qd Qe Ql Qm Qn Qu Qv Qx qY RB Rc Rf Rg Ri Rj rS sC Ss tQ Tr tU Tv Uc Ud Ue Uf Ug Um Un Uo uP Us uT Uu uV vA Vo Vu wB Wc wE wH wJ yL zH zI Ye tM xA Tk Tj Th) wD(aC aE AF aG aH Aj aK AL AN AO Ap aQ AR aS aU aV AX aY bA BC bE bG bI bJ bM Bn bO bQ bR bU bW bX bZ cA cB cD cE cG Ch cI cJ cK cL cM cN Co Cp CQ cR cS CT CU Cv Cw CX cY cZ dA DC DD dH DI DK Dl dM dR eC Ef eT eZ Fn Fw FY GL Gp HA Hb hC hF hG hL hP Hq Hu hV hW hX iA Ic iJ Im iO Ip Iu Iz JE Jf jG jH jK Jm jP jQ jR Js Ju jV JY Kc Kf Kg Ki Kj Kk Kl Kn kQ kR Lj lL lM lN lO Lu Lx Lz Mf Mm Mt Mv Ng Nm Nq Nt Nx nY oE OF oH Or Pe pF Pg Ph Pi Pk qB QG qI Qm Qn qP qQ QT Qu QV QW QX Qz Ra Rf Rg Rh Rj Rm rO rP rR rS rT rU rV rX rY sC Tz Ua Uc Ud Ug uI

Figure 3 Continued

Figure 3 Continued

Figure 3 Continued ql qO qQ Qv qY rN rO sM tN tO tQ tR tS tV uN Ur vB vH vO vP wC wE wG wH yD yH zA zI yE) Ir(aA aN Fi gP Hu Hv Hw iA iH li Io Iu Jm
Jn Js Jt Lp Lu lX lY Lz Md Mh Mi Mj mM Mn mP Mr mS mT Mu Mv Nc Nf Nq Nv nW Nx nY Oe oH Oi Om Oz Pa pF Qc To Tr Tt Uk Wb
Wc Zw Ye Wm Th) lp(Aj aN cH Ed Hu Hv hW hX iC Ih Il In Iv Jh jK Jn Jq jR lX Lz Ma Mb Mf Mh Mi Mj Ml Mn Mp Ms Mv Na Nc Ni Nm
Nn Ns Nv Nx OF OH Om Oy Pa Pb Pc Pd pF qD qY Rh rX Tr Uk Wm) aA(Ad aE aI aJ aK aM aN Ap aQ aU aV bE bL bM bN bR bU cA cB
cF Ch cQ cV dD dE DG Gp Hu In Jn Jq Js jT Ma Mb Me Mf Mm Ms Nb Nc Ne Ng Nh Nm Nn Nu Nv Nx Om Pb Pd Pz Qb Qc Uk) Nh(Hq Hr
Hu Hv Hw Hx Ii Il In Io Iq It Iu Jh Jk Jm Jn Js Jt Lu Lw Ly Lz Mb Mc Md Mf Mg Mh Mi Mj Mk Ml Mm Mr Mv Mx My Nd Nf Ni Nj Nk Nm
Nq Ns Nx Oe Of Oi Oy Oz Pa Pc) Uk(aI aM An aZ bB Bc bN bQ bV bZ cH cT Cu cV Dc dD dG Ed hB iA Ih Iv Jg Jn Jq Js Kf Kk Kn Kx Ma
Me Mm Mn Mr Nm Nn Nv Og Oh Pd pF Pi Po Pz Qb Qh Qm Rf Tn Tr Uc Wn Wm) Ko(Bg Ch Ct eT eZ fN fY Gp hL hO hX In Iz Jo Jr Kg Kr
Kz Ms Ne Oy Pb pY qA qB qH Qv Rf Rh rP rT rW sK tN tU uM uN UO Ur Us uT vA vB vI vV wB wF yD yL zI) No(Eq Ex Fi Gz hR hV hW
jG jL jM jU Op pS qT qU qV qW qX rA rB rN RT Ry rZ Sf Sh sM sO tN tQ tT tX uN uR uX vI vO Vq Vs Wb Wc Wh Yk zG zl YE Tm Tl)
Qb(Ba cT Dg Gh Hq Hr Hu Ih Il Iq It Iv Jk Jq Lu Lw Ma Mc Me Mf Mm Mn Mu Mx My Nb Nc Ng Ni Nm Nn Nq Ns Nv Nx Oe Og Om Op
Oy Pb Pd Pz qC Qg qY Ur Wh Ye Wm) Ch(Bb Bc Bg bQ bZ cT Cu Cw dD Dg Ef Fb Fy HB Hu iA Ih It Jd Jh Jn Jr Kx Ma Mn Nb Nn Nv oF
Oh Om pF Pj Po Ps qC qD Qt Rf Rz Tr Uc uT Wh wP Xa) vS(aW bV cU cZ DB Dc dG dJ Dl Fy Ha hB Hf Jt Kd Kk Kx Mr Mx Oh Ou Pd Ph
Pi Po qD qQ qX Rb Rf Rm rN Tn Tv Uc Ur uT uX Vo Vv wB wJ wL) Lv(Aa Hq Hr Hv Hx Ii Il In Iq Jh Jm Jo Jt Lu Lw Ly Mb Mc Md Mf Mh
Mi Mj Mk Mr Mu Mv My Na Nf Nk Nm Nq Ns Oe Oi Oz Pa Pc Qc Ur Wm) Iv(bS fR Hr Hu Ih In Iq It Iu Jm Lw Ly Mc Md Mf Mi Ml Mm Mn
Mp Mu Mx My Ne Ng Nl Nm Ns Nu Nv Og Oz Pa Pb Pc Pd Wc We Ye Tl Ti Th) cV(AD Aj aM aN aX bM bQ bR bZ cA cH cl dD Ex fR gC
gL hB Ih Jy kI Kj Kk Me mH Ml mS mtU mZ Nl nK oW Qh Rf Tn Ur Vi Vq Yl Wm) Nj(Aa Hu Hv Hw Il In Io It Jh Jn Jr Js Jt Lw Lz Me Mf
Mh Mi Mj Ml Mm Mr Ms Mu Mv Mx Na Nd Ne Nf Ng Nk Nl Nm Nq Nu Nx Og Pb Qc) mZ(bR Du Em Eq Fc Gb Gn Hl Hp Kr Lt Op Pi Po Ps
Rb Rt Rv Sf Sh Si Sj Uw Ux Uz Va Vb Vc Vh Vw Vz Wb Wc Wg Yh Yk Zw Tm Ti Th Yf) qC(Ad AN aZ Bb Cq Cu dB DG dH Dl Ed hB Iu
jL Jt Kd Kf Kk Kr Mh Mp Ng Nv oF Pd Po qA Qc Qh Ql qX Rb Rf Ri rX Uc Ur uT wB) Jr(Aj aN bZ Ct Hq Hr Hu Iq It Jh Jm Js Lu Mf Mh Ml
Mn Mp Mu Mv Mx Na Nb Nc Nd Ni Nk Nm Ns Oh Oi Oy Pb Pc Pz Qc Qg Rf Tk) Ur(AI Bb cT Cu Cw Dc Dg dJ Dl Ed eM Fb Fw Fy hB Jg Kd
Kf Kn lX Me mW Ng Nm Nv Ou Pd Pi Po Pz Qm Rf Tn Tr Us Vq wB wP) Js(hA hR hW hX iB iC jD jF JG jH jI jK jL jM jP Jq jR jU jY lK lL
lM lO Ma Mb Me Mu Ng qT qU qV qW rA rB rC zA) Jy(eT fY hA hO hP hR hV hW hX iB iC jG jH jK jL jM jQ jR jT jU jV jY lL lM lN lO
pF pY qA qB qY rC sC uI uM yL zH) Ok(aM aN Ao Bg bL bN cH cI De dJ Dl eD fN Gp Hb Hc hX Iz jK jQ Kr qD qH Qv Tv Ua Ug UM uO
Uv Wc Wm Tj Th) Nl(Hu Ih In It Jq Jt Mb Me Mf Mh Ml Mm Mp Ms Mu Mv Mx Na Nc Nd Ng Nm Nn Ns Nu Nx Oe Og Oh Om Pb Pd Pz
Qc) pF(aD aE al Bc bN cH cM dD Ih It iZ Kd Kk Kx Ld Me nD Ne Ng Ni oF oH Or Pj Po Qh Qm Qv Rf Ri Tn Tr Vq Wm) Bc(al aU bB bL CT
eF EQ Fc Gh hB iA In Kj Lp Lt Ng nW oD oF oH pl Ps Qv Rt Vi Vj Zx Ye Xa Th) Nd(dG Hu Ii Il Io Iq It Jh Jn Lw Ly Me Mf Mh Mi Mj Ml
Ms Mu Mv Nb Nf Ng Ni Nq Nu Nx Og Pa Pb Pc Qc) lh(aE Aj aN cJ Ct dJ Gz Hb Hq Hr Jk Mb Mc Mm Mn Ms Mx Na Nb Ne Ng Nm Nn Nu
Nv Nx Oh Pb qD Qg Ye Wm) Jg(Bg Ed Hr Hv Hw Hx Iq Iu Iz Jm Jn Jt Lw Ly Md Mi Mj Mm Mu Mv Na Nf Nq Nx Oh Om Oz Pa Pc Qu Uu
Wm) Pj(Aj eT Gp hL hO In jK Jo Kg Kj Kr Kz Ly Ms oF Or Oz pS qD Qh qX Ri rS tU Ug uN uT uV Vv wG wP zI) Ne(aJ hB Hu In It Jq Me
Mf Mh Ml Mm Mp Ms Mu Mx Ng Ni Nn Nu Nv Nx Og Oh Pb Pd Pz Qc Qh Rf Tn) Tr(Ct Ed eT Gp hL In Kg Or qB qD qH rP rW sC tR uO uU
uV uX vA vU vV wF wK wP yD yL zl tM xA) Po(Aj bS Ct Eq fR Gb hP Hv Hw Iq Iz Jt Lw Mi Mk Mu Mv Nf oH Oi Pa Qv Wb Wc Yd Yh Ye
Wm Th) Ma(Aj Hx Il It Iu Jn Lw Ly Mb Mc Mf Mi Mj Ml Mp Ms Mu My Nb Nc Nm Ns Oe Of Og Oi Oy Oz Pb) Kr(mW nD nl oP oQ pS rN
sC tN tO tS tT tU tV tX uM uV uX vV wE wF wK wP wQ yL zA yE tM xA) dG(aI aN aY Bb bL bN bR bS bU cA cF cH cl cL cO cQ CT dE
dH dJ dK eD Gp hO hP jO uM) Jq(bN Hr Hu Hw Il Iq Iu Jm Jn Mb Md Mf Mh Ml Mm Mx Nb Ng Nm Nn Ns Nu Nv Og Oh Oi Pb Pc Pz) Qh(Bg bL
Ct ED fN fY Gp gW hP In Iz jD JK jQ jT jV Oy qA qB Qg tU Ua uM wB wP) nD(aJ aM aZ bZ cT cU Db dD Ed eF Fy Gp hC iA iZ Jm kR Kz
nW nY Ow Pk Rb Rm rY Tn Tz) Ad(al aJ aM aU bB Bg bL bN cH cT DD De Ef In Iz Kg oF Oy qA Qg uT wB wP yL zl) Nv(Aj Bg bL Ct Hq
Hu Hx Ii It Jk jO Mf Ml Mx My Nb Nc Ni Nq Ns Nu Oe Og Oy qD Wm) Ow(AN Fc Gn Hp It Op PS Ry Ux Uz Vc Vw Wb Wd Wg Wh Yg Zw
Tm Tl Xa Th Yf) Me(Gc Hx In It Jh Lw Mf Mk Mp Mu Mx Nb Nc Ng Nm Nq Ns Og Om Oz Pa Pc Pd Pz) Vq(Aj aZ bB Eq Fc Gp Kj Kk lX
mF mS mW oF Qv Rt Ry Va Vi Wc We Yk Yl Tm Tl) Fb(Aj ED hO hP hR hW jD jQ Ng Oz qA qD qX rB rX sM tU uT uX vH wB) Rf(Aj aM
Bg bV dJ Ed Gp lIb Hq In Iz Jn Kg Ky Ms Nn Qc Qt Qv Ri Ua Uv) Pd(Ct fN fY hP hV hW Mb Ml Mp Ms Mx Ng Nx Og Oh Oy Pb qA qB rB
sC yD) fR(aD aM aN aQ aZ bB bP bS bU cA cB cF cJ cX Db dC dD dE dH dN dR gP) cT(al AJ An Ap Bb Bg bL bR bU cF cH Cu Dg dJ Dk
eD IIb hW Ng Oy) Ng(Bb bQ Cu Cw DI Ef Fy hB Jt Kk Kx Mm Mn Nm Nu Nv Xa Wn Wm) It(Aj Bo bR bS cH Ct Jn Ky Lw Mp Mu Mx Nb
Og Qg Qm Ye Th) Oh(fN Hu II Jk Mb Mc Mu Na Nb Ni Ns Nu Nx Of Oy Pb qD rS) wP(aW aZ cH dE dJ eD hO jO Mf Mh Nm nW qD QI Qm
Rb Vo Wm) hB(aE Bb bG bI bL bN cH cP dA Hb hR In jK jT nW Pb qY uM) Ed(Dr Gb Gc Hb Jn kO Ps Rh Ry Tn Uw Ux Vh Wd Ye Ti Th)
wB(aN bR cH dE Dg dJ Hq iH Kc Kz Qy Ss Uc Uu Vo Wm) uT(aZ dB Dg iH jO Kz Nm oK Ou Rb rW To Tt uM Vo Wm) Aj(aU Bb Bg Fy Jn
Kf Kk Kl Kn Mg Om Pz Qm Tt Uw) bZ(aD al aM AN Bb bL bR bU cA cB dE Dl dX Kd) qD(cH Cu Cv Dc Kc Kd Kf Kn Lw Mp Nm qX uN
uX wF) Gp(aM Bb Ct Dg Di Dl dN Dr eF eP IY mM Nm Wm) hW(cB cU Dp eD hA Hc jO jP IK lN nW Rb Ri uM) Ba(aD aM Bg bL bN cH dE
dJ Hb In Iz Ti) Wm(bQ hP Iq oH Ps Qc qH qY rC rW Tn xA) Nm(aN Kj Ml Nu qH qQ tN tV wF yL zI xA) Mp(hX jK Jn jO IN Mb Ml Nc Ni
Og qY Th) II(Dr Eq Hp Lp Nu Ps Sf Vz Yh Yl Ye Tm) aJ(aE aN bL bN bU cA cF cJ dD dE dJ eP) Cu(aU bN cH Ct dE dJ Hr Jk Oz Pb Qg)
Ye(aM aP Hu Jn Ld Oz Ps Rm Uw Wh Xa) bR(al aM aN bB bQ cN dD dL nl oO tV) cU(dJ eD iC jT IL qW qX qY rA rX) Db(kC kl nl oO rN
tX uX vI zA) Dg(aD bB bL bN Ct hO qH sK wG) Nu(Mb Mm Mn Ms Nb Nn Nx Og Pz) Tn(bL Ef Hb He Hq Jk Kj Qt Ua) Jn(Lp Lw Md Mf
Mx nl Ns Oe Of) aM(aI bQ cF dD cP Hb Kk qY Xa) cH(An bN fN Hu iA kR oF uM xA) Mb(Aa Jt Mm Mn Mu Na Nn Nx) In(Dl Fy Jm Jt Nn
Pz Rm Uc) Ld(Eq Ps Rt Ry Ux Wb Wc Th) Om(Jk Jo Nb Nc Ni Ns Oe Oy) Oz(Gc Kk Ps Uw Ux Vi Ti Th) dD(aD aN bM cF dE Dr dX eP)
oF(Bb bG cP Ct dJ jK jO Pb) uM(Kn lM Lw Nx rN tV Us uX) Og(Jh Mf Mm Mn Mx Nx Pz) aI(aN bN cA cF cI dN dR) nW(jl rN tV uG uN uU
vW) Ct(Ap bQ DI EF Fy) Ms(Hu Ky Mn Nx Pz Tz) Nc(Mn Nb Ni Nk Nx Pz) dB(tN tQ tT tX vI wH) jT(aD jI Or Ou uN uX) yL(As Cv Lw Rb
Uc Ul) Dr(Fw Kg kR Rt Th) Ml(Aa Mm Nx Pz Qg) Xa(Bg Ib iO kR Pb) bB(Bb bN cF dN eP) iA(bN dJ jK jO Th) qY(Mx Nn qA qX rZ)
Wc(hG Mr Nb Rm) Kg(Fy Uw Vh Yi) Pb(Nn Ps Uw Vi) qX(hP Ou rW zH) Bo(aN eM Ti) Th(gL Kx Kz) Mm(Mv Nb Ni) Uc(Hc Kj Oy) Kk(bN
Kz Qv) Kn(eD fN sC) Ri(eQ Ky wF) Pi(mS nT oO) aD(Ap bQ gW) dX(cP Dd dL) Bb(eF zl) Ti(gW Kx) Fy(Jo Rt) Nn(Jk Ns) Mh(Ps tU)
Mn(Hu Ns) Mx(aN xA) Hb(bV dN) Rb(tV wH) Rm(jK rB) Ql(Ry Uy) Qm(Oy Qv) Ou(IL pS) Us(IY mW) Vi(Gz kR) bN(Cv iC) bQ(aN cA)
dH(ul zH) eP(cP dL) fN(An Vv) hA(oH tF) IW(hX jI) tX(eD Ss) jO(tV uX) AwPs EqRz FiFw LweZ NkiC YhpH PzOe QclY JhOf KcwG KdOy
KfsC KycI RtUw UpmW aEcF aWrT dEwH dJzl eFgC nOhX nTnI jRvP Constrained panels with 3 analytes, where 1.0E-10 >= 'AUC p-value' > 0. Contains 12,351 panels of 35,857,239 total panels evaluated. :
Et[Jo(aA aC Ad AO As Ax bA Bc Bg bN Ch cI Co cP Cq Cs Cu Cw Dc dM Dp Ed Fp Fy Hc Hu Id Ik Im Ip Is It Iv Iz Ji Jj Jm Jn Jq Jr Kd Ke
Kn Kq Kr Kx Lh Li Lj Lu Lv Lx Mb Me Mf Mh Ml Mq Mr Ms Mt Mz Nc Nd Ne Ng Nh Ni Nj Nl No Nt Oa Oe Ok Pe Pf Pi Po Qa Qe Rh Sr Tv

Ur) Cs(cH dJ eD fN hP In Kc Nm Pj Qg RB Ur) Qd(bN DB dE Hq Ib IN nW Ou Ow rB yL Wm) Nm(Aj Ct Ib Jj Kk Mg Mt Ng Of Ou Ow Vv)
Qe(bN Ch Ib In Ng nW Ou Ow RB yL) dB(Ax cH Cu Dc Kc Kf Kn Kq Lx Pg uX) rB(Ax Fp Ih Is Oa Pe Qa Qb Sr Wm) Ch(Fa Is Kq Mw Qh Sr
Uc Uf Un) Db(Cu Dc Kc Kd Kn Kq Pg Un uX) Ng(Ad Dg Dl Jg Kl Kq Pj Uc) Wm(Ip Is Ld Mt Rf Ri uM) Me(Ax Dc Ih Pe Qa Sr Un) Uc(Aj Ct
Hc Of Ou Ow Oy) Pg(aZ bL Co dE Hq Nq) dJ(Ih Is Mt Oa Pe qX) nW(dG Kq Ok Qa Sr Un) Ur(Ct Fa Oa Oh yL) aZ(Cu Dc Fa Ok Pe) Ax(eD
fN Ri uM) Qa(bN Ou Rb uM) Kf(cB Cw iH Ou) cH(aN Oa Ou Ql) hP(Is Oh Pe) Ad(Aj Ib) Rb(Ih Pe) Kq(Aw Qy) Oa(fN Ri) Un(bN Hq) DcdE
DgKk FaHc MhtU TrOy IpOu SrKz QgJs KruO bLdH} Li{rS(aL AW aZ Bg bL bQ bS cA Ch cK CO cS Cw DB dJ Fb fN fP Gl hB hG Hq Id iH jF jO jT Ko kR Ly Ma Mb Me Nm nW oK oN Ou Ow Oz qD Ql Qx Qz Rb sC Tz Ue uM uO Uu uW uY vA Vv Wm) uM(Ao Bg bL bQ bR bS cA cK CO Cv dB dE dJ dM fN Ib Id jD jO Jq Ko lN Lw Ma Ml Ms Mu Ni Nj Nm No Nq nW Ny oE Ou Oz qD QY rB Ri Tz Uc Ug Ul uP Ur vQ Vs VT Vv wQ xA Wm) fN(aA Aj Ct cV Dc dM eD Fb Fw gP Ha iB In jD Jj jM JO Jq jT Jy Kg Kk Kp Kq kR Lw Ly Mg Mk Mu Ng Ni Nk No nW Ny Ou Qd Rb Ri sC Tv uP uZ vA Vv xA Tj tF) hP(aA cH Cv Dc Fb gL Id In Ip Jq Jy Kc Kn Kq Lw Lx Mu Ng No Ny Qd qV Rb sC Sr St Un uZ vQ Vv xA) xA(bQ cP cV DB DE dJ eD fP hG Ip jM Ly Me Mk Ml Nm nW rB Ss Ug Ur UU Wm) uP(aI aL bL bS Cu dM Fb Hq Hu jG jM Kd Mj Nl Nv oN Pg Pj rU tS Ub Vv) sC(bL bS cA cK dB dE dM hR jD jF jM Nm Rb tR Ug Ur uU) vA(Ad bL dE dM eD Id jM jT Kp Nm qD Us Vt wP) Jj(Fp Ik Im Is Lx Mt Nc Nd Nj Nl Ok Qa Qe) uW(bR Db dE dM jD Ng oE rB Ri Ss Ug wP) uZ(cA cK dB dE dM jD jO lN Ms oE Tz wQ) wP(cO De eF jO nW oK oN Qy) wQ(hR Ip jM jT Ly Ml rU) tR(bO Fa gP jD Nq qB vW) rP(dJ Ko Ql Rb Ue Ug Ur) uU(aI bA dM fP gP Ma Nl) uY(bL bO cC dM lN oE Ur) jT(qH sO uX vT vW wB) uV(Ao Co dE jD lN Md) dB(qP rT rU tU uO) vT(cC dM Fb Hq Ip) Ng(Im Is Jg Nl) Ur(uO wC wH wL) jO(rR rU uT tM) nW(rN tU uX vH) vQ(gP jG Or Ub) vW(bS bX iO jD) Nd(Im Ok Qe) Wn(eC Ks Vv) qH(cH iJ Nm) qP(dE jF vV) uO(dJ Ms Nm) Fp(In Pb) Jk(Im Is) dM(uI uX) tU(De hG) rU(jD lN) vV(aK jR) ThgW IpzA SsuI cVtV cYfY gPqI rBqD tMoN oEuX} No{uM(aZ Ch cO DB dE dJ eD Fb Hq Hu Hw Ib In Iv Jj jO Ko Kp Ly Mf Mj Ne Ni Nk Nl Nq Nv nW Ny Ou Ow Qg Qx RB Ri St Ub Uf Ur uV vA Vv wQ yL xA Wm Tj) qD(Aj AW aZ Ba bL bR cB Ch cO Ct Cw DB dJ Fb fN Hc hP Hq Hu Ib In Iz jF Jk jO Lj Ng Nn Nq Nv Of qA qH qX Qy rB rX Ua Ur Vv wQ Tj) uZ(Aj aW aZ Bg bL Ch cO Ct DB dE Dk dM Ha Hq Hu Ib Iz jF Jk Lj Nc Nk Nl Nq Nv oE Qg qH qX rA Rb rW Tz Ua Ut Vv Tj) xA(bL Ch DB dE dJ dM eD jF jO Kz Ma Mf Nc Nv Pj Qc Rb yD Wm Tj) Th(Bg Ch Db Dp gW Hf Hv Iv Iz Jk Kg Kr Mh Mk Nh oE Rh Vp Wm) Nd(Fp Im In Ip Is Jg Jj Jp Lv Lx Mp Ms Ne Oe Ok Pb Qa Qe wP) fN(bR Ct Cw Fb hO In Jj Kp Ng Nk nW Or Ou Ow Qc Rb Ub Vv) uY(bL bN cO Cw DB dE dM gP Hq iH jO Nq Nv nW rB rS Ua) hO(bS cH Co dJ eC Ha Ib jF Mf Nc Qg Tz Ub Uf Vp Tj) Jj(Dp Fp Ik Im Ip Is Lh Mt Nj Nl Nq Ok Qa Qe) wP(aZ Ch cO eD hR iH jF jO Ko oN uW vA Vv) Ng(Ba eC Fp Ik Jg Nh Nl Ri rU Uh uV) Fp(Hq In Lv Mj Ms Nj Nq Oe Pb) wQ(dB Fb hR jT Ly Ne Nl nW Ri) uO(dB Kr Nk Nl Ri uV Vv Tj) nW(hR jD jI jK uX vV yD) Ne(eC Iz Nh qH vA vT) rS(Cw iH Nk Ou Ow Vv) In(eC Ik Nj Nl Vt) wB(Db Hc hG Hu Tn) sC(dB hV iH jF Ou) yL(dE eD Hq Vv Tj) vT(bL Fb Hq Nl Nv) hP(Hc Kr Qc Ra) qH(aE iJ jT Nl) vA(Ed Fb Kp Tj) Ms(Is Nh Wm) Nj(Im Ni Nk) Jk(eC Im Is) tU(bR hG jF) jT(oK qA rW) vV(aK gW jR) Ch(Ri We) Iz(Mw Ri) cO(rW uT) dB(rO rU) dM(uU uW) eC(dE Oy) gP(Hb Wc) jF(rW wH) WmqB TjHc FbuV NqIs NhPb NkyD UbuU IpKg JtOk NvrU OuqP aKvP bRuW} nW{wP(AD An Ar Ax Bc Cs Dc dL dM dN Fa Fp Fr hC Id Ih Ij Im Is jI Jl Kd Ko Kp Kq Lh Lj Lx Mq Mt Mw Ny Oa Ok Pd Pe Qa Qd Qe sM Sr Uc UN uU Vt Wm) uX(Ad An aW Ax bA bN bS cH Cs DB dE dJ Fa Fb Fy Id iH Im jO Ko Kp Lj Mq Ms Mw Ne Nm Ny Ou qU qY Sr Ss Tz Uc Ue uM Ur uY Vt vV Wm) wB(Ad Ax Db dL dM dN Jl Lj Mq Nm Ny QA Qd Qe Sr St Uf uN Vt Wm) Vt(eT eZ hX oE pS qD rS sO tS uM uN uT uY vH wH yD zI tM) yD(Ad Ax Cs Cu Fa hW Id Ko Kp Kq Lh Ny Pe Sr Tv Uc Un) tU(aJ dG dH dL Fr Jl Lj Mh Mq Pf Qa Qd Qe Uf Wm) dM(fN hW jI rC rN sC sM tO tV uT vV wL zH) uT(dL hC Il Jl Mq QA Sr Uf uN vI Wm) vV(aJ aP bA dF dG hB Kq Ok Qd tX Vs) Uf(jI rN rS sM tT uG uN uU vH wG) rS(Cs Fa Fr Id Is Jl Lj Mq Wm) uN(Ad bA cG hB Kq Nm Ny Tr Uc) Kq(fN hX jI qD uM vO xA) Id(fN hX rO tS uM zA) qA(aA cG dF Fr Kp Ny) Ad(tN tR wF wH tM) Mq(rN uM vH wL yH) Sr(fN hP pS tS tM) Jl(fN qD uM vH wL) zA(Ax Cs Kp Oa Qa) Qd(qD rN tT wH) dL(rN vI wH yL) tS(Ax Cs Kd Kp) Ko(tN vI wF) aJ(qD tO vH) tX(dB Lj Wm) hB(jI jO vH) hC(rN wH yL) Fa(uV wQ) Qe(sM wH) Ny(sM uU) qD(iZ Un) jI(Lx Ou) yL(Lw Vs) uM(dG dN) AxyE CstV FbhW FrfN MwrN KptM RiwF dFjO} Jj{Im(dJ Dp Fp Hc Ik Ip Is Iv Iz Jl Jr Lh Lj Lu Lv Lx Me Mf Mr Ms Mt Nc Nd Ne Nh Ni Nj Nl Nt Oe Ok On Pe Qa Qe Wm) Is(aN Bg De dJ Fp Hc hP Hv Ik Jg Lh Lj Lu Lv Lx Me Mq Ms Mt Nb Nc Nd Ne Nh Ni Nj Nl Nt Ok Pf Po Qa Qe Wm) Ik(Fp Ip Ir Jg Jm Jp Js Lh Lj Lv Lx Mn Mt Mw Nn Ok On Pb Pf Po Pz Qa Qb Qc Qd Qe) Fp(Fr Ip Iv Jg Jl Jm Jq Lh Lv Lx Mm Mn Mq Mr Mt Mw Nc Nl Nt Ok On Pz Qa Qe) Qe(Jg Jm Jq Jr Lh Lj Lu Lv Lx Me Ms Mt Nc Nd Ne Nh Ni Nj Nl Nt Ok Po Wm) Ok(Jm Jr Lj Lu Lv Lx Me Ms Mt Nb Nc Nd Ne Ng Nh Nj Nl Qa) Lx(Hv Ip Lj Lv Me Mq Ms Mt Nc Nd Ne Nj Nl Pb Qa) Qa(Hv Ip Jg Lh Lj Lv Me Mt Nd Nj Nl Wm) Lh(Jm Lj Me Ms Mt Nd Nj Nl Pb Wm) oE(Oa Qh To Tr Tv Uh Us Vq Vt) uM(Ax Dg Id Kf Ny Qh Uf Vt Wm) Lj(Hu Jg Jm Lv Mt Nd Nl Wm) Tr(fN hP rW uI uN yD yL) Mt(Ip Jm Lv Ms Nd Nj) Jm(Lv Nd Nj Nl Pz) Wm(Ip Mw Pf Uh) Nm(qH vA xA) fN(Cs Kp Rb) Nd(Mw On) Ng(Ad Ba) Pf(Nj Pb) LvPz KohO KruW OaUh UryL} Ng{Jg(Aj Fp Hu Ik Im In Ir Is Jr Lh Lj Lv Lx Me Mq Mt Mw Nd Ne Nh Nj Nl Nx Oh Ok Pf Po Qa Qb Qe Wm) Pf(Ba dE dJ Ik Is Jq Jr Ko Lh Lv Mt Nh Nj Nl Nx Ok Pb Qg Uf Uh Zq Wm) Ok(Fp Hu Ik Im In Is Jo Lj Lv Lx Mq Nc Nd Nj Nl Qa Qe) Uc(eC hO qD rC rV uM Ur uY uZ vB wC zH tL) Im(Dg Fp Fr Ko Lh Lx Mt Nl On Tr Uf Uh Ur) Lx(Ba Fp Ik Is Lv Me Nd Nj Nl Qe Wm) Tr(Ij qD sC Uh uN uV vV yD yL tM) Ba(Aj Id Is Ko Pe Qe Uh Ur Vt) Is(aN Dg Fp Ik In Nd Nl Qg) qD(Jt Kf Ko Kq Ny Pj Qd Vt) wB(Ad Dg Nm Pj Ss Uu Vo) Uf(Ij jO Ne tU Uh uM) fN(Ad Fa Kp Ny Pg Qh) Dg(hW sK tU uU wG) Nm(eZ qH uM yL xA) Ko(oE rW uO wP xA) Uh(Ad Bc Cs Tn Wm) Wm(Ij Lh uM) Ss(uT vI wJ) On(Fp Ik Nd) Vq(dF Fb oE) Ad(Aj Ur) In(Qa Qe) Qh(jT jV) Vo(uT wP) hP(Id Jt) xA(Pd Vt) uM(Kq Ny) AphO ChZq FpMt NdQe IvRz XamZ UuuT cGjO} uM{Uf(As Ax Ch Cq Cs Cu Cw Ed Hv Hw Hx Id Ij In Iv Jn Jq Jr Kk Kq Kr Lj Lw Ml Na Ni Ny Oa Ou Ow Pk qH qX Qy Rj rX Sr tQ tT Ud Up Us Vp Vt Vv) Ny(AJ Ax bA bV bW Ch cZ dF dG Dp Fb hB Ib Id iO Kf lM oF Ou qA Qv qX rB rN Sr Tz Ua uX Vt Wm) Id(aF bA bR cH cT dH dM In Kc Ko Kp Kz lK lN Lw Ou Ow pS qD Qg qX qY rB Ri Ur vA xA) Wm(aO bA bB dD dF dM Kn Kp Lw Mr Ou qD qX Ri tX uT Vs wB) Kp(bW Ch dE Dg eD Ko Mf Mm Ss) Vt(bW dE Dp In lN Mm qX Rb xA) Ax(bW dE Dp Fb Mm Ri) Kr(bC bW Ib Mm tV tM) Ch(Kq Pg Qh Tn Uc) Kf(bW DB dE Ou) dB(Fa hB Lx Vs) Mm(bA Dc Kd) Uc(Aj Iz Ou) Kq(Ib Ou Ua) Lj(cJ Lw Ni) dE(Fa hB Lx) rB(Jl Pf Sr) Dg(Kk Vv) Nm(Aj Ct) Ko(Jy wP) bW(Dc Mj) CsDp FbpS LwyL LxcO MxqD OuuX PjdF dJqX} mZ{Dr(aD Bc bZ cV dD dF hG Hu Ij Ik Il Kd Ki Kr lY Ma mE Mt Nq OE Of oH oV Pa Pf Qt Rz St Ul Us Wd We Wh Zq Xa Yf) We(bG Ch dN Dp Fa Gd hG iJ Iv Kc kG Kj Kr lY Mq Mr Ni Oa oV Oy Pb Pi Qv Qx Rh Sh Tt Ub Uy Vq Vt Ye Wm Tj) Rz(bG bS cE cG Ch cL Dp Hq iJ Iv Jv Kc Kj Kr Ld lW lY mE Mq Mr mU Nd Ni Oa Oy Oz Pa Pb Qv Sh Tt Ye Tj) Wh(bG Dp Ef Ib Iz Kc Kr Kz Oy Pb Pi Qw) Xa(BG Dp Ib iJ Jk Kr lY oV Qw Uy Vt) Kr(Fd Gc Ps Vh Vw Yi Zq Tl) St(Gd Sf Sh Uy Yh Ye) Tl(cG lY nA oV Po Qt) Zq(bG Dp Iv lY Tj) Gh(Ma Pa Po) Ry(lY Ni Vq) Uy(bZ Ma Mt) Yf(Ld Mh) Gd(bZ Vw) Mq(Zx Ye) oV(Ik Pi) FiPb GcbZ IjSf YhoH ZxUn} Lj{jT(eT pS rN rS rW sK sM tN tT tU tV tX uG uN uT uU uX vH wB wL wP wQ yK zI) wP(bL bP dB dE eD jD jO jR nY Ou qD RB Ri rO Ue uW vT xA) rS(dB dE dJ eD Fb Hq hR Id Ip jD Ko kR qD Rb Ri rV Uf zH Tj) tU(bL dB dE eD Fb Hq Ip jD Ko Pj qD RB Uf Tj) wB(DB dC gP hP Ip jD nY Rb Ss Ur) cJ(fN rR uZ wC wH wL zH tM tL) In(Im Is Jg Mt Qa Qc) xA(aU dM iJ Jg Nm Uf) nY(rR wC wH wL tM tL) uT(cC DB dE jD Ri) Nd(Fr Im Jg Ok On) gP(pS tV zI yE tM) Lw(hP qD uZ) Zq(Gl Op Rh) Ok(Jo Jt Lu) dB(rO rT tV) zI(bL dJ Ur) tM(As cC Tr) Lv(Im Lx) Ip(rR wQ) dC(wL zA) dM(uU uZ) qD(Jy rB) jR(qO vV) NjIm IsJk KpfN VshP cCrR dErT dJtX fYqX oEuZ} Kp{fN(Aj Ax aZ bA bR bW Ch Co Cs Cw DB dE Dg

Figure 3 Continued

Figure 3 Continued

Qe{Nh(Ms Ne) JgOy} Ld{eQ(kQ mM) OppF} Uh{AdKg NimM UpnF} hA{cG(bN hP) AaPh} qX{MhtU PgbL dJzH} Fa{Hc(fN hP)} Mt{DguO qAjT} Nf{mFqW qYkK} Uc{IzuZ OfvA} Wh{EdRh nHoT} Kk{SsyD cDlN} bR{PjuT aCfR} oV{ToPe IiPh} BgRzpK CwKfrU TnbAyL IrRieQ QhJktU QgJlhO RjeDtT UycRdU PgbLsC aDqHjT mIhXrY

Constrained panels with 3 analytes, where 1.0E-9 >= 'AUC p-value' > 1.0E-10. Contains 6,346 panels of 35,857,239 total panels evaluated. : Et{Vt(Af Ao Aw cI Cp Ct Dg Dk Dl Ed Ef Hq Jk Kc Kl Ks Ly Md Mg My Ne Nm No Nx oE Ok On qC qD qH Rh Ri Ug Ur Us Yd) Wm(aC Af AO bO Co Dg Dk Dl dM Ed Jd Kr oE oH pF qC Qu qV qX Qy qZ Rh Ri rT Tv Ug Us UV Vv wP Tj Th) aO(aW Ax bV bZ Cs cT dF Ed Fp Hc Im Is Kr Li Lx Me Mg Mm Mq Ms My Nd No Op Pe pF Qv Ri Rt Wc Yd Th) Jt(aC An As bN cI cP Cq Ed Hv Hw Ir Jn Kn Kp Kq Kr Kx Lh Mr Pe Pi Pk Qd Qh Qv Rh Uc Ul Un Us) vS(aG aZ cI Ct dE Ed Ef Hc Hu iH Iz jD Jl Kk Kx Ma Mf Ms My oE Of Ou Ow Oy Rm Us yL) Hc(aA aC Dp Hu Id Is Ji Jq Kd Ke Kq Ks Mr Ni oE Ou pF Qa qX Ra Un uT uU wB wG) Kr(cI Dk Ed Fp Ib Id Im Is Je Ji Kd Kk Kl Ko Li Lx Ml Oz Qa Qd Qe qH Qy Ri Uu) Rh(cI Dl dM Dr Ef Ez Hq Ii Jd Jk Ks Mv Ne No oE Of Oz Qu Qv Qy Ri Tv Ur Yl Th) Ao(bA cP dM Ed Hb Hu Id Jh Ji Kd Ke Ks Lx Me Ml Mr Nw Qa Qe Ri St Uh Vv yL) Qv(Af Aw cI cP dM Dp Jd Je Jk Jm Kl mM Mv Mw Of Qe Qt Qu Qy Ri Ua Vv) bN(aJ aN bV dM Fp Im Is Jk Jr Kj Lx Me Mm Ms Nd Ne No Pe Qa qC Qe qV) Co(aA cT dM Dp Ed Fa Fp Hu Ij Mh Mr Ms Nd pF Po Qa Qe Qh Ri Uh Us) Dk(bA Dc dM Fa Ji Jl Kd Ke Kq Lx Ml Mq Mt Nb Nw Ny Oe Qa Qe Ri Ug) Ib(Ad Af Cq Cs Cu Cw Dc hO Id Ij Im Kd Mm Ms Ne No Pf Pi Qa Us uV) De(aW bA cI cT Ji Jq Ke Kq Kx Lv Mh Nw oE Qa Ri St Ul Un Vs Vv) Ii(Ad aM As Cq cT Cw dM Dp Ed Id Kn Kp Kx Mr Or Pi Rm St Tv Un) No(aC dM eC Gl Je jO Ks My oE oN Qy Ri Ss Tv Ur Us Ut Vv) Pf(Ba bS dH dM Ed Ez Ha Ks oN Qu Qy Ss Tv Us Vu Vv Tj Th) Mm(aC dM Ed Id Iv Jl Jn Jq Kd Kl Ks Lh Mr Pe Ri Vv Yh) Ne(aJ Ap aW bV bW eC Id Kd Ke oE Or pF Ri Us Vv Yh Th) Oy(aM bV Cu Dc Dp Fy Id Jy Kd oE Or pF Ri Tv Ur Us uV) Ct(bV Cu dF Dp Fy Id Jl Jl Jq Ke lO oE qZ Ul uV) Kl(Id Is Jd Jm Kd Ke Ks Li Ly Mq Mv Qa Qe Qt Qy Ri) cI(aA Ax cP Cs Is Jd Ji Ks Me Ml Mq Ms Qa Qt Qy Ua) uM(bW dH iZ jD Kd Kp Oe Ou qC Qh Qy rZ sM tQ Tz uX) Hq(bA dM Ed Fa Jm Kk Lh Lx Mh Mr Pe pF Ug Ur Us) Kj(cP dK dM Ed Fp Fy Id In Ji Jq Kn Ko Ri Ul Un) Uk(aC bF cP eC Id Ji Jq Ke oE pF Qa qX rA Vv Th) My(bA dM Ed Jn Ks Lh Mz On pF Ri Ug Ur VV) Dg(bA cP Fb Fp Id Jd Jk Lx Mv Qa Qd Qe Qy) Ef(Fa Fb Ij Is Jm Li Lx Qa Qd Qe Qh Ri Tv) Fa(Aw Bn Cp Jk Mk Mv Nh Nv Ok On Qt Tj) mM(Bo bQ bR Cx Kc oF Op pF Pj Rb Ur Yd) Im(Ap dM Gl Jd Qt Qu Qy Ug Us Uu Vv) Oa(bA cP gP Ha jM nW oH Op Vu xA Th) Ax(dH dM hX jM Ks Mc Qu sC Tv Vu) Cs(bO cO dH dM Ha Hf Ks Tv Vv tM) Ed(Fi Gl In Jk Kc Mj qH Ur Us Tj) jO(aA Jl Lj lK Mh Mp Of Qc Qd Tv) Dl(bA cP Jd Je Ko Mv Qa Qe Qy) Jo(Hv Hw Jl Ko Pk Ra Ri Ul Un) Iz(aW cP jI Jq Ko oE Ou pF) Jk(aC bA dM Jl Kk Lh On Qh) Ke(Af Aw Bg Bn jD jM Ms Nx) Pe(Ap Ha Ns Pa qC Qt Ua Tj) qH(dB dE JY Ny ql tT Uf) nW(Jj Kg qV rN uG yL yE tM) Is(aC aN Ap jQ Qt Ur Uv) bA(Ba eT In lO Nd Nx Ok) Ly(Gl Kk Qt Qu Ur Vv) Qy(In qZ vV wP yD tM) Kg(Dr Hl pF rN Yi Th) Lh(Hr Md Mw Ns Nx Of) dM(bL eC Fp Jr Nv Nx) tT(cO cP fN jM Lj oK) qC(aW dB jP Me qA Qd) wD(cP Gl Hr Jh Mf Nk) Aw(hW Lv Qh qX uU) Bg(Jq oE Ou qX Th) Lx(bO Pg Ua Uv Tj) Yh(Dr Ma mZ Pb Wc) Op(bG bR Dr Ld oE) rS(aW Fb jP Ou yL) Af(Id Kd Li Mq) Ms(Kd Ks Qu Vv) Ua(Fp jI Mq Ug) In(aC aM Dp Kd) Rb(Gl nD uV Vv) Jl(fN Ni Og Pa) Kk(Mk Mv Nv Oz) Nw(Mw Nv Of Pg) Ur(Ap Dp Oz Qt) eC(Aj Ch Jj nF) jM(cH cT pF Qh) vV(aV dB Mf Ny) Bn(aA Id Tv) Fb(qX qZ rB) Yd(aY Jd Nh) Lj(Jy Vu wF) aC(aA cP cY) qA(jD oK Ow) qI(Aj bR dB) Bc(Rt Uu) Ch(oH rT) Cp(Id Kd) Dr(Gl Jd) Th(Ni Oz) Fp(Qt Tj) Ns(Jm Pc) Mh(Jq Ni) Mk(Mr Ug) Mq(aA Qt) Uv(Jr Qu) aW(bL tU) cD(lN qX) hX(cP Id) rN(dE fP) ApQe LwyL MgHf MlNy MrOf MwJg JqOm JylN KpsO RinD WnVv OuwP PhqX aUjQ bMhO bRjI cBwH cHoE cOtX cUrB dAhA dBtM dFeT dJqZ hRiZ jDuV wGjP jRvP} Nw{Lu(Hq Ii In Jk Jr Li Lx Md Mq My Nc Ne Ng Nl No Ns Oe Og Pg) Qa(Hq Hv Ik Im Lv Md Mw My Ne Ni Nq Ns Nv Oe Og Oy Pa Qb) Md(aA Ik Im Is Jq Lx Mq Mt Nc Nc Ni Pb Qe sK vH wD) Pb(aA Hw Iv Jl Jn Jq Jr Lh Mr Ng Ni Oe Ok Pe Pf) Mq(Hq Hv Ii Is Jj Jk Me My Nc Ng Nl Oe Og Oy) rO(Ao Co Hc Hq Hu iH Jd Je My Nq oE Qw qX Qz) Nc(Hv Ii In Is Jk Lv Me My Ne Ng Ni Ns Oy) Nl(aA Hv Ii Is Jk Lv Me My Ni Nk No Ns Oy) Lx(Hq Ii In Jk Me My Ni Ns Oe Oy Pa) Ik(Hq Iv Jn Jo Jq Jr Ni No Nv Oe Ok) Mt(Ii In Jk Me My Ni Ns Oe Oy uO) Li(Hv Ii In Jk Lv Me Mj Ng Ns Oy) Lj(aA Is Mj Ni Oe Pa rS wL tM tL) oE(Bg bN cH dJ Im Iz Kd Kr Ng Oa) Jr(Ii In Jj My Nd Ng Nj Ns Oy) No(Ii In Jj Jk Lv Ne Nq wP) Is(Hq Jo Lv My Ni Ns Nv Oe) Qe(Hq Mw My Ns Nv Oe Og Pa) Nc(Hv Ii In Jk Ng Ns Oy) uT(Co Dk Hc Jd Nq Nv On) Lv(Mw My Ns Nv Nx Oe) Nd(aA Iv Jn Jq Mr Pe) Im(Iv Jn My Ni Nv Ok) wB(Ba Gl Hc Je Nq qH) qZ(aG bR cO Qy Tz Wm) rS(bL cO Ko Nk Nm Ss) uL(Ao Ba Bg Hu Iz Ng) Mb(Hv Hw Iv Jn Jq) Me(Jo My Ng Ns Oy) Nt(Ii In Jj Ng) Nj(aA Jn Oe Ok) wP(hO iP qY Vo) wD(jD On qH vS) Jj(Iv Ng Wm) mZ(We Zq Xa) tU(Dk jF Qg) qI(bW Dg Jy) rW(Ng Tz Vv) vW(Ke Kf Us) Ii(Lh Ok) Jg(Jk Mw) Ri(eQ jD) wQ(Ad gP) sK(Kz Qc) sM(uM vT) qX(bL hO) jO(Jf Ou) jQ(qO vP) xA(Oa Wm) rU(aN Qz) sC(Uc Ul) uO(Kp Mz) uV(Nk Ow) vA(Kq Vv) DbrN TjwG PoJk MyJh UduY InOk JiNv UfzA aAvT dMuI dRvV fNqT hRoK hBjD} Ng{Pf(aC Ad bL bN bO Dg Fp Im In Ip Iv Jh Jn Jt Ke Kq Lw Me Mq Mw Nb Nc Nd Ne Ni Nt oH On Pe Pj Pz Qe Ri Tr Ue Ur Uu Tj) No(Ad Ap dJ Gp Hb Im Is Ko Li Lv Lx Mt Nc Nc Nj oE Ok Rh Uf Ur uY Vt wP Tj Th) Lx(Hu Hv Ij Ip Iv Jp Jq Kq Lh Li Lu Mq Ms Mt Mw Ne Nh Nt Om On Qa Qg Ri Uf) Is(Ap Di dJ Hu Im Jh Jp Lh Lj Lu Lv Mq Ms Mt Ne Nj Nt On Po Qe Uh Ur Wm) Im(Ap dF Ik In Jp Jq Lj Lv Mm Nd Ne Nh Nj Nx oE Po Qe Qg We Wm) Jg(Fr Ip Jj Jl Jn Jq Mc Ms My Nc Ni Nr Nt On Oy Pe Qd Uf yL) Uh(Ax Dg Dl Fa Ij Ko Kq Lj Mq Nm oE Pe Qa Rh Tv Uc Us) Ba(aC Ar Ct dJ Hb Ij In Jp Li Lj Mt Ne Qa Qc Qd Rf) Ji(Ad Ap aW bA cT Dg dM Kr oE Rh Ri Tr Uf yL) qC(dM Fb Id Jl Jt Kp Nr Ok Sr Ss Un Ur Uu wD) Fp(Fr Ip Jp Lh Li Mm Mw Om Pz Qa Qe) Li(Ik Lv Mt Nd Nj Ok Pb Qe rS Wm) Ok(Jh Jr Mc Ms Mt Nb Ne Po Wm) Uf(Hb In Jj oE Pe Rh Ri St Ur) Uc(jE Jj oE rO tV vA tM) Qe(Ik Lj Lv Mt Nj Nl Wm) Ij(Dg dJ dM Ko Qg Ri) Mt(Jp Lj Lv Me Po) Mw(Ko Kp oE Tn Wm) fN(Jt Kl Ql Sr Vo) Tn(Dg eC Ko Pj) Ke(eC oE Ri uM) wD(Bb Kl Kr uM) Wm(Jj rB vS) Ik(Fr Jp Qa) Ko(eC Mq uP) qD(Bb Dl Un) Ad(In rB) Dg(rS tX) Id(eC oE) Tr(iC Mq) Qa(Lv Qg) St(Jj jT) On(Mb Nl) zA(Mz Rb) BceQ FrNd MaVq SstX QhrB JjLh XakR KfuM KquO NyvS VtoE VozH dFjO dMrC} vS{Lj(An bE bV Cq Cu Cw Dc dL hB Hv Hw Ir Is jD Jn Jq Jr Js Kn Ml oE Pb Pi Pk pS Qa qX Ra Rj rS Ud Ul Up Vp) Db(aF cH Is Jl Kd Kx Mt Nm Ny Ok Ou Ph Po Qh Rm Uf Un uT uX) Wm(Ad aF Ax dF Fa hO jR Js jT Kk Lu Oa qX qZ Rj Sr uI uM wJ) Ke(aL Ao Ba Bg Co cP Dk Hq Hr Iz Jh Kx My Nv Of Om Qt Qx Uh) Pj(Ax bA bE cG cZ Fa hO Jj jY Kx Lx Nr Nx Oa Qd qX Rb Us) Sr(Ax cP Cs Hf jO Kp Mh Ms Mx Oa qZ Ri Tv Ua Uf Ur yL) Cs(Ad bA bL Hq iJ jO Kp Mb nW Ny vQ Tj) Ax(aW iH Ji Kd Mj nW qC Ri wL Tj) dB(Fy Im Kd Kr Mh Mt Nx Ny Ph Po) Tr(aD Fr hA Lx Nc Nq Ow Pg Qd) Kp(aH dE Kr Kz Mf nW oK qC Qz) Ad(Iz Lz Mg Mt nW Ou Ow yE) Nm(bA Cw Mg Nu Oa Of qX qZ) Vv(Ap dJ iO Kr Lu Mw Nr Qd) jO(Fa hB Kn Ok Ou Pe Tv Vs) dJ(Fp Kk Lx Mq Qa Qd Qh) aW(Cq Lw Nx Pi Un Ur) nW(bV dL dN Kq Mx Pe) Lu(Kd Kk Kn Ou Qh) Kr(bA cH fN Ny Us) Uf(aN Js Oa Ow Qd) wD(eD iH Kz qC wL) Jl(cO qC Ri Ua) Ch(Ok qD Rm) Qa(oH Ou Rb) Jt(Ct Kz Ou) Ny(bV qA Qy) Un(Aw Kz qD) Us(Aj Aw Ct) Vo(cI Lz Mt) Pg(Hq Nq oN) eD(hB rN Vs) Mf(Dc Kd) Ss(Kk Kn) Kf(Kz Ou) Kq(De Md) Pe(bL qC) AjTv CoKo CpUc DgKk TjLx FaHu FprB MxRj IhRb HcLh QcQd QhwL KxqC OadE PfbL cGhA} qC{Fb(aD Ch Cs cZ DB Dc Dl Fa hW Ih Is It Jl Jt Kd Kf Kn Kp Lh Mp Mr Mx Nb Nr Nx Pj wD Wm) Ny(aW Ax DB Hc hP Hu Iz Jk Ko Nq Ow Qy rX Sr Ua Ur) Lj(aA aJ Dc iO Is iZ Jj Kd Kn Kq lM Qe qZ rX Sr St) Ko(aA An cX iA jD Jj Kd Kk Ms Of Ql rS Sr wD) Jl(Aj aW aZ cL hP Id iH Jk Nk Ow Oy Qy Ua) Ax(aZ cH dJ Ip Kp Ou Pj Qd Rb Uh Ur Tj) Pe(bL Ch dB Ha jF Jk nW Oy Ua Ur Wm Tj) Kp(bS cB dE jO nW qA qB Qe rW rX uV) Ch(Bg Dc dM Ih Lx Nm Nr Nt Qa Tn) Cs(aZ Dg Fp jT Jy Ni Ri rX uM Tj) Vt(aW bL Hq Hr Ly Nk Ow uM yL Wm) Id(cF Ct jK Kc Ou qY vA vV yL) Rb(Ed Im Kc Lx Mh Pj Qd wD yL) cH(bR cB Mh Ow Qm Ri Sr

Figure 3 Continued

Figure 3 Continued

Figure 3 Continued bLuT} bA{Ad(Ct qH) TjyL LuvV} dX{cV(cP Dd) BbGp bRdL} Ld{Il(Sf Yk) OpkR} Wn{FrIi MwHq JkVs} Up{IrmW JnnD PinI} Oy{On(Ik Mb) LvJg} dE{LwyL KnsC eDtV} jR{vV(cG Pe) QlvP} Qc{nDjL qTkI} aY{HliA YkpH} bL{JlvT PgwF} bR{fR(aD aM)} AdOfuT BaZxQb CtDgtU CwKfrV ThKgUn GhbGpI NrgZkI MeInPd HuOpoO IrJgJk RzlYkR RiPboV PjqXsC aCnDhB bNeDuX cAcGhA Constrained panels with 3 analytes, where 1.0E-8 >= 'AUC p-value' > 1.0E-9. Contains 10,291 panels of 35,857,239 total panels evaluated. :
Et{Ri(Ap Aw bN cI dM Ed Fp Hq Im In Is Jd Jk Jr Jt Ke Kk Lx Ly Mg Mh Mk Ms Mv Of pF qH Qt Qu Qy Ua Ug uM Ur wD Yd) Ib(aO As bA bN cI Cp Fp Hw Is Iv Ji Jn Jq Jr Ke Kn Kq Lw Ml Mr Mz Nr Om Oz Pb Pc Pk Qc Ra Rh Tv Un Up Vp vS) dM(Ap cP Dg Ed Hf In Is Jd Je Ji Jt Kl Kr Me Mg Mh Mk Ml Ms Mv Mw Of Oz Qt Ss Ua Ur Vt Vv) Kd(aO Aw Bn cI Co Dd Ef Hq Jk Ks Md Mk My Nb Nh Nv Nx oE Ok Om Oz sC Tn Ur Us Ut vS) Ks(aO bN Co Dk Dp Ed Fp Hq Is Jd Jm Kk Lx Mv Of Oz Pe Qa Qe Qt Qu Qy St Ua Uu Wm) Id(Aw bN cI Co Dk Dl Ed Ef Hq In Jk Md Ms My Nx Ok On Qv Rh Ua Ur Us) uM(aJ Bg bR cD dE dF dL Fp Is jL jO Lx Mf Mr Ms Mt Rm rN Sr Vv wG yJ) pF(Ao bL bN cH cI cO Ct De dJ Im Jd Jk Jo Mg Mk Mm Mv No oE Qv Rh Vt) Ua(bN Ed Fa Hu In Is Jm Jr Ly Me Mw Oz Qa Qd Qe Qh Vt vV wH Wm) Ke(aO Co Cp Ef Hq Jk Ly Mk My Nh Nv Ok On Oy Qv Rb Rh Us Ut Wm) Vv(aO bA bN cI eC Ed hX In Jm Jr Lx oE Oz Pe Qa Qe St Uh Us Vt) cP(aW Co Cs Fp Im jI Jr Kl Kr Me Mh Mm Mq Nb Nd oE Rh tU Us Vo) Tv(Aw Cp De eC Fp Gp Ir Is Jk Jt Mh mM Nx Oz Pe Qa Qe St vS) bA(Aw cG Cw Gl Kj Kl Mg Mk Mm Mv Mw Nb Nv On Pb Qu sO vV Tj) aO(aJ cV Dr gL hB Ji Jq Jy Kk Ml Mr Nw oE Qa Rh St Vt Yh) Th(Cs Ed Fa Fp Hf Ir Iz Jk Jo Jy Lj Me Mm Mq Nj Ow St) bN(aA Dp Ed Jl Jq Kk Kr Ml Mt oE Qt Qu Qy Rh Ur Uv) Jd(Fa Is Jr Jt Kk Lx Me Mq Pe Qa Qe Ug Ur vS Vt) eC(Ax Bg cI Cs Ed IZ Kg Mm My Op Oy Rh Vt Wm) jO(Ip Jl Jj Lh Li Lu Lx Ml Mt Ng Nw Qa Qc ql) oE(Ao cI Co Im Ip Is Jo Mg Mm Mt My Pf Qv wD yL) St(Af Co Dg Dk Dl Ef Jk Jt Kl Kr Ne Nv On Qv) vS(An Ao Ba Dc Js Kn Kp Mr Mv Nr Pe qA Qh Rb) Me(bL bO Co De Dk Ef Qt Qv Rh tT Ug Ur Uv) Yh(aK aM bI bR cG dB Dp Fp Im nF Ng Oa Tl) Qy(Fa Is Jr Jt Kk Lx Ly Mq Pe Qa Qe Ug Ur) Vt(Co Dp Ha Mv Nv Of Op Oz Pf Qt Uu xA Wm) qH(aM aZ bW dL iO Ji Kp Lx Mt Nm qA rN uX) Jk(aJ aW bV Cu Dc Dp Jy Kq Rm Sr Ug Us) qC(Db dJ fP Ih iZ Kz Oh Qa Qe Ql qX Rb) De(aJ bV Cu Dc dF hW Ml Mr Po Ra uU) Jy(Ao Aw Co Dk Hq hR Mk Mv My Nv yL) Us(Ef Fp Ii Is Ji Jl Li Lx Mq Oz Qe) Tj(Fw Jl Li Mh Ml Mq Mr Mt Po wD) Qv(aL aM bF bO Is Lx Ly Oz Qa Ul) cT(Ao Ba Dk Hc Hq Iz mM My Oy qA) vV(aK Hc Iz jQ Kr Lz Mt Mv Qz uV) Cp(Cu Dc Kn Kq Kx Pi Qh Sr Un) Jq(Af Ao Bn cI Dg Dk Dl Ef Kl) Op(Il Jm Kg kR Mh Ow Oz Pb Qb) wD(Ct Ef Fb hO Mk Ow pY rS tF) Co(Jh Ji Jm Kx Ml Nw Ou Pg) Qa(Ap bL bO gP Qt Rh Ur Uv) Qu(cI Ed Fa Fp Jm Li Pe Ug) Kq(Aw Bn Ef Hq Ii Nv Oy Ut) Wm(Ap Hf Je mM Qx Um Vs) Oy(Ou Ra Tn Tr Un Vs wP) No(bL bO bS Ha Uu Vu) Lx(Ap bS dH Kl Qt Rh) Jt(Fy Qt Ra Rj Up Vp) Ug(bO Dp Jm Mv Oz Qt) mM(aY Bn cG cV Gc Rg) tT(cB eD Kz Mf Mh Mv) qX(aM bO Ct dE Kc Kj) jP(hX qI uU uX wB wK) uN(dJ Hc jD jT rB Tr) uV(Jh Jj Mt Nk Oa rB) Dc(Ef Hr Nx Tn Ut) Ed(cI Ms Nh Nv Wh) Ii(aJ bV Pk Ul Up) Ji(Dl Gl Kl Rh Uv) Kg(nD Vi Wg Wh Xa) Ur(aL Jm Mg Mr Mv) Vu(Cs Fp Im Li Pe) qA(cI Jj jT Kp Nk) Ap(Jm Jr Mq qV) Aw(Kn Sr tU Ul) Ax(bQ bZ cO wL) Dp(Hq Mk My Uv) Ef(aA Ko Ml Ra) Fa(bO Je Mw Nx) Is(Dd Ez Rh Ut) Yd(dH In Nj Qz) Qd(Dl Kl qD xA) Qe(bL Gl hO Qt) Kr(aA aC aM xA) Up(mT mW mZ nF) Pe(bF bL Je Tn) Pf(bF Eq Je Rt) qZ(Aj Kz Ou Ow) yL(eD Hq Jj tU) Cu(Hr Nx Ut) Mm(bS Rh Rx) Mq(Ba bL Gl) Ms(aM jD rX) Hc(Fy tU wH) Wh(Bg dH Eq) Ny(rW vP yD) Or(jM Mk Nh) Ul(Bn In Of) fN(cI Nk Qh) wP(An Of Ow) iZ(hO Ne qY) rS(Db Mf Ow) rN(Ch Hq Ou) nW(hW Im Uk) Af(Kx Vs) Cs(bQ rB) Dk(Fy Mr) Dr(Ch Wc) Mh(aW bO) Nd(aM Wc) Il(Eq Sf) Iv(Fi We) Qt(Jr Uh) Jj(hO rW) Kl(Fb lN) Kp(sC yD) Li(bL bO) Rt(Ld Oa) aA(Kj Rh) bR(hX uX) bV(aC In) jI(cD Cw) jY(uI xA) AowH BgoH DbuX DlSr FpHa FweD GlWe LwUt MaRy MtbF MwOn MyUh NgWd HqJl TtHf RarB JmUu KnNx KosC LhNv OaVs OutM aKaQ bWjG cBqD dAhX dFjM tQiH} Ng{Uh(As Aw bA Bn Cp Cq cT Cu Cw Dc dM Ef Fp Fr Hw Id Iv Jg Ji Jj Jn Jt Jy Kd Ke Kf Kn Li Lx Me Mg Ml Mr Mw Na Ne Nf Ni Nr Oa Ok Om Pd Pz Qe Qh Qm Qt Ra Ri Sr Un Up Uu Vt) Im(aC Ad Ba cE dE dJ dM eC eF Fa gP Hb Hu Id iJ Iv Jh Jl Jr Jt Kk Kp Kq Lu Lw Me Mq Ms Mv Mz Nb Ni Nt Oe Om Pc pF Qa Ri Rz Tn Uc Uk Vt Th) Lx(aA Ad Ap Bc bN Cu Dg dJ eC Ef Fr Gp Hb Hf Id In Jh Jl Jn Jt Jy Ko Kp Mm Mu Mz Ni oE Pb Pc Pe qC Qh Qm Qt Rh Sr Tn Uc Ur Vt) Pf(aA An bB Bc bR bS cA cO cV dM eC Hb Hu Ij Ir Jl Jp Jy Lj Lu Mm Mn Mr Ms No Nv oE Om Oy Pc Po Qa Qb Qd Rh Ul Un Vq vS Vt) Uf(Ad Ax Bc Fa Gp Hu Id Il Is jI Kd Kk Ko Lj Ml Mn Mq Mt Mw Nj Nr Nw Oa oH Om Pg Qa Qe Qm qZ Sr Tn Uk Ul Un Us uW Vt) Ba(Ad Ax bN Cs Fa Fp Fr Jg Jq Jr Kq Lh Lv Ml Mw Nb Nr Oa Ok Pg Pj Qb Qh Qm Rh Ri Sr St Wm) Qe(Ad Ap cT Dg Di Hu Jh Jq Jr Ko Lh Me Mg Ms Mv Nb Ne Nh Ni No Nt Nx Om On Pc Po Qg Tr Ur) Li(Ad dF dJ In Jh Jl Jp Jq Jr Ko Lh Lu Me Mm Mq Ms Mw Mz Nb Nh Nt oK Om On Qa qC) No(aC Bc bR bS cV dF Dp Hu In Ip Jr Ke Lh Mb Me Ni Nx pF Qa Uh Ul Vq) Mt(Hu Ij Ik In Ip Iv Jq Jr Lh Mn Mq Ms Mw Nb Nj Nt On Pc Qa Wm) Mw(aC Ad Fa Id Ke Kk Kq Lj Oa oH pF Qm Qn Rh Ri Tr Ur Vt) Ij(Ad Ap bA dF dG eC Fa Id Ke Kq oE Rh Uk Ur Vq Vt Th) Is(Ad bR cV fN Fr Jl Ko Mc Mm Nb Ni Om Pc Qa Tr Uk) Jg(aA bA bF Cs cT dF eC Fa Ko Lu oE Rf Rh Ur wB) Ok(aA Jl Jq Kr Lh Lu Nt Nw Oe On Pc Rh Ri Tn Ur) Qa(Ap Dg Hu Ko Lh Ms Nd Nj Nx Po qC Tr Ur Wm) Kq(Ap eC gP hP Ji Jj Ko Ne oE Rh Ur Uu vS Wm) Fp(Dg Jh Jl Jq Jt Lw Mg Mn Mu Nt Nv Pc Po) Tn(Ap cV Hb Id Ip Lh Nd Ne Nw oE rB St Uo) Pe(Ad Ap Dg dJ hP Ko qC Qg Rh Tr Uk Uu Tj) Ji(bF bN cV dF eF Hf Ko pF Qg Uc Uk zA) qC(Ap Bb Bg Cs Ez Kf Nt Oh Pg Qd Vt Wm) Ko(Fa Fy jD Jn Kr lN Rh St uY Wm) Dg(dF jI Jr Lv Ml Qh Sr St vS) Nw(aA Fr Iv Jm Kr Lh Nb On Rh) Vq(bA cV eF Fa Fr Jj Jn Ur) vS(Ar dJ Jl Lh Qh Sr Un Ur) Ad(dF eC Jo jT oE wD wP) Ke(gP Hv Kr Ne Pz Rh Wm) St(Ap Bc In Tr Ur Th) Lj(dF Hu Ik Jh On Pz) fN(Bb Bc Ez Id Jl Rb) Wm(Fr Jp Pg Qd Zq) Lh(Ik Ms Nd Rh Ur) wD(Ap Ez Ny Rb Ue) Zq(bR Nj Rh Wh) Sr(Ap hP jT lN) On(Hu Ne Nh Nj) wB(Ez Jt Kl Kr) oE(Bc Qh Tr Wd) Jp(Lv Nd Nj) eC(Fa Un Vt) qD(Id Jl Kc) Ap(sK wG) Uc(jD rR) Jj(Fy Tr) Ny(hP zA) Uu(iC tX) cG(hA hP) uT(Kr Pj) BbqZ ChWe FrHu NrUr MaNh MqIp NdJl IdjT IlWd SswG QhjD XacV VtdF VozI dMjQ} Jj{oE(aW Bc Dc Dp Fb Ij Ip Is It Jl Kf Kn Ko Kp Kq Lh Li Lj mM Mt Mw Pf Pg Pj Qa Qd Qe Rh Rm Sr St Uc) Pf(aC Bg bL bN bS cO De Hc Ir It Iz Jg Jn Me Ms Mw Nb Nc Ne Nh Nm Nt Oa ON Pz Qb Qt Rh Vt) Nl(Fr Ir Jl Jn Jp Jr Js Lv Me Mn Mq Nb Ne Nk Nm Nn Nt Nv Nx Ny Pd Pg Qb Qc Qd) Dp(Ad Dg Ij Il Ip Jg Kf Ko Kp Kq Lh Ne Nm Nr Nw Pe Pz Qh St Tn Tr Uf Vt Wm) Mw(aC Bg bN dJ Hc Hu Ip Ir Jr Ko Me Mz Nc Nh Nr Nt Nx Pz Qm Rh Rm Uh Us Vt) Lv(Hu Il Ip Ir It Jn Jp Jr Js Mp Nc Ne Nj Nm Nr Nt Ny On Pd Po Qb Qd Wm) Nj(Fr Ii Il Ir Jn Jp Js Ma Mn Mp Nb Nm Nn Nt Nv Nx Ny Om Pd Pg Qc Qd) Mz(Fr Hu Il Ir Jp Jr Me Ms Nc Nh Nn Nr Nt Nx Pd Pg Po Pz Qb Qd yL) Wm(hP Ih Ij Io Jl Jn Jp Jq Li Mn Mq Ms Nm Nr On Pd Po Pz Qc St) Ip(Hu Il Jg Jr Js Me Mq Nb Nc Nh Nn Nr On Po Pz Qb Qd St Uh Vt) Nd(Fr Ii Ij Il Ir It Jn Jr Js Mn Mp Mq Nm Nn Nr Om Pg Qc Qd) Jm(dJ Ij Ir Iv Jg Jn Jq Jt Mf Mm Mr Nb Ni No Nu On Pe Po Qm) Uh(Ad Ao Bg Ch Cs Cu Cw Dc Is It Ne Pd Qa Qe Qh Rh Rm Tv Vt) Lj(dF dJ Fr Ij Jh Jo Jq Jr Jt Kf Mm Mq Nb Ni Om Po) Ne(Jr Nb Nh Nm Nn Nx Oa On Po Pz Qh Rm St Uc Vt) No(aC Bg bN Ch eC Jr Lu Ms Nb Ni Nt Rh Ua Vt) Oa(dJ eC fN Ij Is It Kf Ko Kp nW pF Rh Us) Qa(Bg bO dJ Hc Iz Jl Mq oH Qg Qm Rh Vt) Qe(aC bA bL bO dJ Hc Iz nW qC Qm Us Vt) Jg(Ir Iv Jl Lu Mq Mr My Nc Nh Nt Oy Pe) On(Jr Lu Mc Mf Ms Mt Nc Nh Nt Oy Po) Pz(Hu Ir Jr Js Ms Nc Nh Nr Nx Qb) Im(bN bS cI dM eC nW nY Us Th) Li(dJ hP Iv Jl Jq Mq Ni Nt) fN(Dc dM Fa Is Js Ny Ra Uf) Mt(Iv Jl Jn Jq Mq Mr Pe) Vt(dJ eC Is Ms pF Qh Rh) uM(Ad Cs Jl Ko Rm Uc Vo) Bg(Ad Ij Kq Nw Ok Qh) Nt(Ir Jr Me Ms Po Qb) Ji(bN Ch cI Hc Iz Rh) Nx(Ir Jr Me Ms Nc Pd) dJ(Ij Lx Nw Pc Rm yL) qC(Cs Dg Pj Rb Uc) Po(Ms Nc Nh Pb) Lx(aA bN bO Jl) Ik(aA Hw Ij Mq) Is(cV Kr nW Qx) Nw(aA Jl Kr Rh) Ad(bN De hP) St(Ch Kr nW) Jr(Pd Pg Vq) vS(Nm Tv Us) Uc(eC Iz) Hu(Qb Qd) Jl(Lh Ok) Jn(Me Vq) dM(jO uW) hO(Dg Uf) hP(Sr Tv) qZ(Tr Uu) rN(nW Ur) DeFy FpKo NmNr IjIz ItUs KruO KswD LhaA RioT VqpF PbPg} Im{In(aA aC Aj bW dM eC Fa Hw Id Ir Iv Jg Jn Js Kk Ko Lu Lw Mh Ml Mm Mr Mz Ni Oa oE Op Pe Po Rh Ul

In Iq Ke Kp Kq Mm Mr My oH Om Pj Qh Qm Us vS Vt) Oa(Ad BA Bc dF dM eF Il Ji Jm Ke Mj Nm oH Ou Pd Pg Pj Qe Tr uM Vt Th) Me(Fr Ii Ir Jl Jp Js Lv Ma Mg Nj Nm Nn Nr Nv Om Pd Pg Po Qb Qc Qd) Mz(aA dM It Jn Jo Jt Lu Mf Mg Ml Mn Mq Mr Nb Nu Oh Om Pe pF rV uY) It(aC Ad Ax Cs dM Fa Fr Hu Jp Ke Kk Ko Nj Nl Nn Om Rh Rm Sr Vt) Pz(aA aC Hw Il Iv Jn Jo Jq Lu Mf Mh Ml Mq Mr Nb Ni Nu Oh Om Pe) Jm(aA aC Ad Bg CH dM Fa Fr Jl Nv Qb Qd Rh St Uc Uf Un Us Vt) fN(Ad Ax Bb Ez hO Id Ih Jl Jy Kn Kr Ks Mt Nm Pg Qa Qd Ql Sr Vo) Nd(Ad Ax Hu Ih Iv Jk Jo Jq Jt Ma Mg Mi Mm Mr Ny Oh Pd Pe) oE(Ad Bb cH Cu dF Fw Fy Ir Iu Jg kC Mr Pd Po Ur Uu Th) Nr(aC Hu Ir Jp Ko Mn Mq Ms Nb Nj Nl Nn Nv Qb Qd Vt) Lv(Fr Ih Iv Jl Jq Jt Mm Mn Mq Nb Nn Nv Oh Om Pe) Ad(aC bA Ch Hc Il Iz jD Lx My Qb qC qH Qt Rh) Nj(Bc Hu Ih Iv Jo Jq Jt Mg Mm Mq Mr Ni Oh Pe) Lx(aC Ax bL cH Ko Kp Kz Qh Qm Rh Rm Us Vt) Ms(Ii Ir Jl Jn Jp Js Ko Nm Nn Nv Oh Pg Qb) Ng(Ap Bc Dg Ef Fa Ko Nv On Pj Qh Tn Un Vt) eC(dM Id Is Ji Kd Qa Qe Qh Rm Tr Tv Un Ur) Nl(Ii Il Iv Jo Jq Jt Mp Nf Ni Oh Om Pe) Uc(Aj Bg De Fp Hc hO Ib My Qt Rh rW vS) Us(Bc Fp Fy hP Is Kp Nw Ok Qm St Vt yL) Vq(aZ cV dF Ed Fp Kf Ko Rm Sr St Ul Uu) Hu(Ir Jn Jp Js Mm Mn Nm Nn Pd Pg Qc) Rh(Fa Fy Ko Lh Ok Pe Qh Sr St Tr Un) qC(Ax cH Dl dM Is Jl Ks Oh Pe Qa Rm) Ir(Fr Jn Lu Mf Mn Mq Nb Nn Pd Tr) Jl(Bg Hv Mb Mf Nb No Nt On Po) Kr(Ke Ko Ok Pj Qa Qe vA wD yL) Nw(aC Ao Ax bA bR Ch Hc pF Ul) Pd(Il Jn Jp Js Nm Nn Qb Qc xA) Jg(aA Aj Bg Ch Cs Jn Jq Ni) Qh(Ax Ch Iz Ko Kp Nm Pj Qm) Vt(bA bL dF Il Kz Rm St uU) Qb(Bg Fr Hv Mg Mm Ni Om) Kq(Ao Ch Co De Dk Hc Iz) Ok(aC Aj Ao bL Ch Hc Iz) Pe(Bg bL CO Hc hP Iz) Fa(De Hc Iz Ko Pj Th) Fp(dF Dg Kp Pj Qm Uf) Mq(Jp Js No Nt On Po) Qa(bA bL bR cI cP Fy) Ke(Ax De Dk Pb pF Qe) aC(Ba Bc Cs Dg Li Qd) uM(Jt Kl Pj Qm Ur wD) Nm(Il Lu Pg uO wH) St(Il Ko Kp pF Qm) Jn(Il Nb Nt Pg Qd) Lh(Bg bL Ch Hc Iz) Rm(Bc hP Pj Qm rB) yL(Ji Rb Ss Ug Uu) Mf(Jp Nv Pg Qc) Mt(aA Ax Ch Cs) Qe(cI Id oH qD) Ko(Fy Is rW uO) Li(aA bL oK Th) nW(No uT wB wH) Bg(On Pg Tn) Et(qH wD Th) Fr(Nb Nt Pb) Qd(Lu Nb Om) pF(Kd Tr Un) Aj(Ba Ef) Ax(bL Fb) Ed(Tr Zq) Po(Iv Jq) No(bO bS) Nt(Jq Mn) Il(Jp Nn) Qc(Mg Nb) Ji(dM hO) Ks(uV vS) On(Ch My) wD(dB Rb) oH(Bc Is) AoFy DbrN MhJp TowP NyrW OmPb UfOz PjhO aHqZ dFoN hBjO} Ng{Uh(aM Ap bV cV Dd dF dG dJ dN eC eF Ez Fb Fy Hv Il In Ip Jh jI Jl Jp Jq Jr Kk Kp Kr Lh lO Lv Lw Mn Mt Nw On Or Pb pF Pg Pi Pk Po Qd Qv Rf Rj St Ul Ur Vp Vq) Dg(aA aC Ar bA Bc Cs Fa Fr Fy Hu Ih Iv Jl Jp Jq Ke Lh Li Lj Me Mq Mt Mv Mw Nb Nw Oa oE On Pg Po Qb Qc Qd qH Rf Rh Ri rN Ut Vt Wn) Qe(aA aC Aw bA Bb Bc bF bN dF dJ dM eC Fr Gp Hb Id Iv Jl Jn Jp Jt Kk Lw Mm Mq Mr Mu Oe oH Pc pF Pj qD Qm Qv Rh Ri Tn Uk Uu Vt Th) Mw(Ax bA Bc bF bR cT Cu cV dF dJ dM eC Fy Gp Hb Ik Ir Jy Kd Kf Kl Kn Lh Lv Nh Nl Ow Po qC Qh Sr St Uc Uk Ul Un Us Uu) Ko(Ax Bc bJ bN bZ dF Fp Fr Hu Il In Ip Jp Jr jT Kf Lh Lj Ml Mt Ne Nr Nw Oa Pz Qh Qm Rf Ri rY Sr Uk Ul Uo Ur Vq Vt Wn) Qa(aC Ad Bc bF bN cT dF dJ eC Fr Hb Id Jh Jl Jp Jq Lu Me Mm Mq Nb Ne Ni Nt Oe oH Om On Pc pF Pj Rh Rz Uk vS Vt Th) Ad(Ap bA bN Bo Di dM Fr Gp Hu Jp Jr Kj Lh Lj Mq Mt Nb Ne Nw Ok On Po Qd qZ Rh Ri rS St Tn Uk uM wH zI) Im(aA aU AW bA Bc bF bR bW cG cT CV dD dG Jn Jy Lp Mr Mu Nn oH Pe Qv Rh Ul Un Uu Wh Zq Xa) Lx(aC Aw bA bF Bo bR cE cH Cw dF Di dM eF Fy Jr Kd Ke Kf Kl Mr pF Tr Uk Ul Un Us Uu Vq Wn Tj) Tn(Bc bL Ch Dl Fr Jg jK Jq Li Mm Mq Mt Nj Nk Nr Oy Pz Qd Qg Qm Rh Ri Uk Ur Vp Vq vS Vt Wm) Ij(aM aW BC bF Bo bR bS bW Cv Fb Hc Jr Kl Kp Lj Mm Ne Nh Nl pF Po Qm Ul Un Uu Wc Yk) Vt(bF cT eZ Fa Fr Gp hP In Is Jg Kq Li Nr oF oH Pe pF Qg qZ Rh Ri St Uk Ur uT Xa) Uf(aM bA bN bS cV dF dJ dM Dp eC Fr Fy Jh Jq Kn Lw Ok On Or pF Po qY rB Uu Wm) Mt(aA Ap Aw Ax Bc Bo dJ dM Fr Jh Jl Jn Jt Lw Mm Mr Mz Ne Ni Nv Om Pe Qd Tr) Is(aA aC bF bN Bo bS cE dD dF dM eC Fa hP Id Kk Kl oE pF qD Qm Qv Rh Rz Uc) St(Cw Dl Gb Gc Hf Id Ip Jg jO Kp Lh Li Ne oE pF Qg Qv Ri Uc Uk Uw Wh Yk Wm) Ba(aM bL Dp eC Fy Ih Jh Jl Kk Kx Me Mg Mm Mq Nm oE oH Om On Or Po Tr Un) Lh(aA Fa Hu Jh Jr Lj Lv Mb Mq Mv Nb Nh Nj Nl Nt oE Om On Po qC Ri Uk Uu) Ap(Cs dF Fa Fp Fy hW Ih Jp Ke Li Lj Ml Nr Nw Oa Qd Qh Rf Tr tU uT Wn) Fr(bR dJ eC Jr Li Lj Me Nb Nc Nh Nj Nl No Nx oE Ok Pb PF Pj Qm Rh) Po(Hq Hu Ik In Jp Lj Lv Mq Mz Nc Nd Ne Nh Nj Nl Nt On Pb Pz Wm) Jg(aC bR bV Ch Cu dJ dM fN Fy Id Kc Pj Qh Qm Sr Un uT vS wD xA) Li(aA bA bF bR bS eC Id Ip Iv Ni oE oH pF Pj Qm Rh Ri Ue Ur Th) No(bB bF bN cA cE dM Jh Jl Jq Lu Mm Mq Nb Nt oH Om On Pc) Ok(Aw bA bN Bo dJ Fa Gp Mu Oa oE Qh Qm Qv Sr Uk Uu Vq vS) Pe(aC bF bR dF eC fN Fp Ha Iv oE oH Pj qD Ri Uc Ue Ur Vq) Kq(bN dF dM Gp Il In Kr Mg oH pF qX qY rC Ri Uo wD) Lj(Ip Jp Jt Mg Mm Mq Mu Mv Nt Nv Nx Om Qd Ur Wm) Vq(bB bQ bZ cT dM gL Gp In Jr Kf Kk oF oH Sr We) Ik(dF In Ir Jl Jq Ma Mm Mn Nn Nv Nx Om Pg Qd) Nw(bA bR cT Cw dF eC Ef pF Qm Ri Sr Uc Ur Uu) wD(bP DB dJ Fb fN Ji jO jT Ks Ql Rc Ri uZ) On(Jr Lu Lv Me Ms Nc Nr Nt Nx oE Oy Pz Wm) Ur(Bc Dc Ip It Ji Nm Pz Qh Tr wB zA Wm) oE(Ef Hb Ip Kd Kn Mz Pg Pj Qd Un Uu Wm) Fa(Gp Id Ji Mg Mm Ne Pj Qg Rh) Tr(eC Gp Ip Nr Oy pF Qd rB Un) qC(Ar Ax Kc Mm Pd Pf Qc Qh Vo) Wm(cV dF Ip Jq Nm Nr Nv Om) Jp(Ax Hu Jr Mb Nc Nh Nl Nt) vS(cG Kf Kl Kr Qd Ss Tt Us) Ma(Jr Me Ne Nj Nl Nu Pd) Uc(jM jY oH pF qX rU rX) Ji(bJ Fb Gp Oa Qm Uu Wh) Pg(Jr Mc Mz Nd Nh Nj qD) Pj(dF Qh Ri rT Sr wF wP) Lv(Jl Jq Nv Om Pz Qd) Ke(Bc Nr pF Qm Uk Uu) Pf(bA Bb Dp Ha Mu Rg) dF(Ax Fp Id Nr Oa) Bc(oD oF oH pF) Nn(Fp Nd Nh Nj) Uu(eT hW jK wP) cV(Fy Rf Sr Wh) eC(Kd Qh Sr Us) qD(Dc Jy rX wF) uT(DB Ez Jt) Nd(Mp Nv Zq) Ir(Mz Pz Rz) Ss(qZ sO wQ) dM(jK jO zH) Et(Dr We) Ez(hW yL) Fp(Mq Mr) Nt(In Ip) Nh(Mn Oh) Nj(Jl Nv) Il(Wh Zq) Jt(uM wP) fN(Cs Fb) wB(dB Rb) jT(Cu Un) ChWh DlqZ EfrB NmvB MmHu NlJl InPd ZqRi QdbF SrzH QhQm QgOa JnRz XaaM KphP KrtV NywP VoyL hBjO} Im{Aj(aN As Bc cM cT Cu Cv dF eF Fa Fb Id Ji Jq jT Kk Kl Kq Li Lw Mm Ms Mt Nd Ne No Pf Qe Qv Rh Tn Uc Ul Zq Wm) Jk(bV cE Cv Dc dF dG Dr Fa hB Hl Hu Id Ir Jn Jr Js Jt Kd Kk Ko Kq Me Mf Ml Mr Ni oE Or Qv Ry Sr Tr Un We) Ur(Cv dM Dp gP Hc Id In Ip Kd Kn Ko Kq Lj Lw Me mM Mr Ms nD Ne Nm Oa Op Ou Pe Pf Qa Qv Uk Ul Un Vt Th) Fi(Ad Cq Dc Ed Em Fa Gp Hl Hv Hw In Kd Kq Ld Lh Lw lY Mi Mr Mz nD Nr Pi Qa Qw Ra Ul Un Vt Xa) Ch(bA dD Di dM Fb Gp In Jg Ji Ke Ko Kq Ky Lh Mt Mw No Nw oE oH Ok pF Qv Ri Tn Tr Uk Wd wP) Iz(Bc bF cE cG dF eF Id Ij Ip Jg Jq Jy Kk Li Mw Ne oH On pF Qg Qv Rh Ri Tn Uw Zq Xa) Ke(bS Ct De eC Ha Jd Kj Kr Md Mk Mu Mv Mw My Nh Om On pF Qu Qv Qy Ri Tv Ua Vv Wm Tj) Uk(aC hN Ct dF In Jq Ko Lw mM Ne Nm No Nw PF Pj Qt Qu Qv Sr Tr Tv Ua Ul Us Vt Wm) Th(Ct cV dN hB Ib Ko Kq Kz Ld Li Lj Lp Lx Mm Oa oE Qa Qw St Uf Ul Un Vp Vu) Me(Dr Fr Hq Is Jg Jl Lh Lp Lu Lv Mm Ms Nc Ne No Oe Og On Pf Qa Qe Rt We Ye) Uh(Ao Co Ct De dM Hc Hq Ii Jo Kk Ko Mj Mm My nW Oa Ou Oy Qt Qv Qy Rh Ri Wm) dM(aQ Bg bL bR bS dJ eC Hb Hc Jo jQ Kk Ne Nw Oy Pf Qt Qv Qw Rh Ua Wm) oE(aW bN cH cM dE Ib Id Ip Ji kC Kd Ko mM Mt Mw nA Ne Nk nW Ua Wm) Rt(Ad aM As Bn Cp CQ Cu Cw Dc Gn Hr Iv Ji Kg Lx Pi Po Us Uv) Oy(dF Fa Hu Ik Is Jh Jl Jp Ko Li Lu Lw Mm Mq Om Pd Pf Pg Po Vs) In(Ad aM As bA bV cE Cs Ct Cv dF dJ dL dN Kd Kn Ou Qv Ua Us) We(Co Cp cQ Ef Eq Gl gP Ii Iq Kj Qu Rh Tt Vp Wc Yg Yk Wm) Ct(Ba dJ Fb Id Ji Ko Kq Lv Mt Nw Pf Qv Ri Tr Uf Ul Wm) Ms(Jn Lw Mf Ml Mq Mr Mz Nb Ni Nn Om Pa Pc Pe Po Vt Wm) Jr(Hw Il Is Iv Jn Jq Li Lj Lv Mr Mt Mz Ne Nh Ni Nl Pe) Jo(dE Fa Id Ik Ip Jq Kk Kn Ko Nt Nx On Po Tr Uf Vt) Ji(cI Dd De Dk Hc Ib Kg Kj Qt Qw Rm Tv Ua Ut Zx) Pf(aN gP Hc Ii Is Jq Lu Mm Mz Ni Og Pb Qt Qu Ua) No(gP Hq Io Jl Jn Jq Kg Mf Mq My Qe Qu Tv Ua) Nw(aC Ao dE gP Hc Ib Kg Kr Qt Qv Rh Tv Ua Vp) Mm(aC Hq Jq Lh Li Lu Ml Nc Ne Nh Ni Ns Oe) Nc(bW Jn Kk Ko Mr Mz On Or Pe Qa Qv Uf) Iv(Hw Hx Il Is Li Lj Lv Mb Ni Nl Oe Og) Jn(Hw Il Is Li Lj Lv Mt Nd Nh Nl Oe) Og(Fr Jl Lw Mf Ml Mq Mz Ni Nt Pc Pe) Lx(aC Bg Kg Kj Ks Pg Qt Qv Yk Tj) Hq(Fa Fr Jg Jl Jq Lh Mf Mz Nc On) Ii(Fr Id Jg Jq Ko Nt Nx On Qa Xa) vS(bE dJ Dp Et Kx Pj qC rB Tr Uf) Ni(aA Jl Lp Lu Mq Mz Nd On Pc) Il(Fr Is Jg Ml Mr On Pe Yg Ye) mM(Cq eC Gp Kc Or pF Qv Qw Rh) Wc(Ij Kq Lv Lw Mi Ra Uz Wg) Pb(Fr Ik Jg Jl Mq On Pc Pd) nA(bR Cq eC Hf Kg Or Rb Ri) Mr(Hw Lj Lv Mt Nh Nl Oe) Jq(Ik Jl Lu Mb Mq Qa Wm) Vt(gP Kg Kj Mj nW Qv Tv) rB(bA bF cG cU dF pS wP) Ns(Fr Jg Lw Nb Nu On) Mz(Hw Ik Mq Mt Nl Oe) Zq(Co De Dg Kr Qu Wm) Ye(Bc cV gP Gz Kr Qh) Ko(Jt Kg Kj Qv Qw Tv) Pe(Hw Lj Mt Nh Nl Oe) aA(Li Lv Mt Nl Oe Ok) nD(Af Gp Ha Ks Rh Tv) Dr(cV Dc Qw Rh Vp) Lu(Jl Lh Lw On Qa) Is(Hw Jl Mb Mq Mt) Lp(bC Dp Mb Qu Ul) Wm(Lw Oe oH Yl) Mu(Gn Hl On Xa) Mw(aC Jg On

Qe(cB Ct Kk Of Ql rX Ua uM Vv) aZ(cG dF hB Kd Mp Nx Pd Po Qc) Ad(Ct Hc Iz Kk Kz Mc Ow Uk) Db(aJ Fr hB Sr St vI wH yL) Uc(Bg cB Hr Jo Kz Mv Qt Ua) Jl(Ax bH bL Ct Kk Kp Ou Vv) wD(bH bQ cC cL eD Iu qX rA) Oh(bL cL Ib Ih Ow Uk Vt) Me(bV dG Lh Mp Ok uX) Sr(aW bN iH Kk rX yL) Ny(Bg Ct Kd Kn qX Vv) Ou(Dg iA Nx On Pd Po) Ih(bN iH Lx Tz uM) Js(Dg Ib Nc qA yL) Kf(dE jO Kg Kz Nk) Ok(bN cB jD Of Oy) rX(Ip Nr Qb Qd Ql) Ax(aW Jy Ni Vt) Kp(Cw Ib iO qX) Tr(bM Ed Ql) Qd(fN jF Ly) Kd(iH Kr uM) Kn(Hc iH Ss) Lh(cB Kz Ow) Vv(Ji Lx Nr) Pd(bS Ib Oy) cG(bL bS Hq) Cu(cB iH) Nn(bL Vt) Mt(fN Hq) Nc(Nk Rm) Qc(Ib Ow) Jt(Mg Ow) Kr(Jo Lw) aW(An Cx) yL(As oE) uM(Mq uX) CtNt FpfN LxMs UaQh IdKk QbQg StjO JydE KeuO NxaN OncB UfcL cOdG qAqY} Is{Uk(Aj aM aN Bg bN bS Ch Ct dJ eC Hc Hq In Iz Jk Lx Mk Ms Ne oE Oy Qg Qm Qv Ua Ul Ur Vt) Jo(Ad Bg dF Dg dJ Id Iv Jl Jn Jq Jr Lu Mm Mr Nb Nc Ne Nh Ni Nt On Pe Po Qa Qe Qg) Ne(aC Aj Ch Co cV dM eC Ik Iz Jq Kg Lh Li Lu Ni Nk Nt oE Pb Qa Qg Qv Ur) Oy(cV dF dJ dM hP Iv Jl Jq Lh Mm Ni Nl oE Om Pc Pe pF Po Qg Qv Tr Ur) Ct(aC Ad bN bS bV Ch cT cV dM fN hP jV Lx Mq Ms Ni Nj oH Pe Qv Rh) aN(aC bB Bg bN bS cA cH cV dF dJ eC Ii Iz Ji Kg Lx Mq Ms Nw Qv Ur) Jk(aA Aj BA bN bR cT cV dF dJ dM hW Jl Mr On Pe Qv St Ur Th) Aj(bN bR cM cV dF Dg dJ hP Id Jg Kl Ko Lx Ms Qn Ur) In(aC Bg bN bR bS cV dE dF eC Iz jV Kk Mr Oa Qv Ua) Ii(bN bR cV dF dJ Fr Iv Jl Jq Ke Mm Mq On Po Qa) Pb(Fr Jl Jq Lh Lu Me Mm Nb Nc Ni Nt Oc Po Qa) Kg(dJ Dr Gh Hl Id Ji Ko Lh Ok Op Uz Wg Ti) Hq(dF fN Jg Jr Lu Me Mq Nc Po Qa qY) rB(bA cU dF jQ oK Ou Qg rC sC uM wP) Jg(Ch Hu Jh Me Mg Mu Mv Ni Ns Oe) Jq(Ik Li Lu Md Mq Mt Nh Nj Nl Qe) Mm(Jr Lu Lv Me Nd Ni Nj Nl Oe) My(Fr Lh Lu Mq Nb Ok On Po Qe) eC(bN dM Kk Lx nF Nw Qg Vt Wm) Ch(bN Ji Jp Lx Mt qD Rc Rt) Lh(Hr Hx Mk Nc Nj Nl Oc Of) fN(cT dM Hc Ib Nk Of Ow) jO(hB hW jV Ke oF tV uT) Mc(Jl Mq Nc Nj Nl) Mk(hW Ik Jl On Qv) Iz(Fa jT Mw oE Ur) Qg(Cs Kj Qv Ua xA) aA(Lv Nd Nj Nl Og) cV(bN dJ Dr Ms Rt) nD(Ly oK qW qY Rt) Ns(Jl Lu Nb Qe) Qa(Hx Mb Oe Qb) Ur(Hc Ms Ua Wm) hP(Ni Ny Pj Vt) jQ(aU hX Ni Nk) jV(hX Ml Nt Ph) uM(cZ Dg Uf wD) Mq(Hr Hx Li) Nc(Nb Nl Oe) Nj(Jl Jn Jr) Kr(mM mS mZ) qY(iC kK qU) nW(hW iC uT) oE(bN Kd Op) Th(Qv St) Mb(Iv Jn) Mz(Jr Wn) Rb(rS tM) Jv(hR sC) Oe(Nb Qc) bL(jK wD) dJ(pF tT) dM(qD vA) wP(eD oK) lM(Aw kK) WmMs EdWe FrNq LxHc MdOk MgjT NdwD NiLi UahW HxIv YeUl KjKo TkbE OfOn OurS UpmP bNtM cOqZ dFoN nCjL iJqH} Ji{Kg(Ad Ax bA cI dK dM Fy Hf Id Ij Ip Ke Kf Lx Nm Pj Qa Qe Vt Wh Wm) Ch(aA aC Ba cI cT cV dF Gp Ij Jg Na Rb Rh Ri Rz sC Ur wP) De(aA bA Cs cT dM jT Kr lN Lx Oa Pe pF Rb Rh Uo Ur uY) Aj(aA bA cT dJ dM Gp Ij Ik Ko Lx Mq Mt Mw Qe St Uc) Qg(Af Bn Hc hX Ib Iz jD Jk Kr Nx Oa Oy Ua uM wD yL) Bg(aC Ba Bo cT dM eC Kr Lx Mq Pe Rh sC Uk Ur) Oy(BA bF bN cI dM Hf Kr pF Rh Ri Tr Uo Th) uM(Ad aW bA bN Cs Jl jT Kp lN Oa Tr tT xA) Kr(Ct Gl Hc Ib Iz Jo Kj Lx Ms mW Uk Ur) Ri(Ao bN Dk eZ Hc Ib Iz Jk Ms nD Ua vV) wD(Hc hO Hr iA Jk Ne Of Ql qT Qu rO) yL(Fb Hr Md Or Pj sC Tz Vv wL zH tF) bN(aN cI cV Jk Ko Lx Ms My Nd tM) vV(aK aW cH dJ Jn Qc sC Tz Ur vP) Cs(Co dH Ha Jo Mk Nd rU uZ Tj) Wm(Ib Of oH Qt rB Rt Up Ur wP) Iz(Ba dM cZ Fa Ij Li Mw qY Rh) eC(cI jl Ms My Oa oH Ou Pi Rh) oE(Af aW cH dJ Mm Oa sC Uk Yh) bA(Co Ct Dk Hq In Jk Jo vW) Ax(dH hP Jk Mc Mk Nx Ur) Th(Dk Dr Ed Hf Jk Mh Rb) Hc(eZ Ij Lx qY Rh Ur wB) wP(Ko Mf Mu Ny Ow uW vA) uY(Ao aW Mh My qH Qt Ur) In(aC cI dM Ed Uk Vt) xA(dJ Gl Mh Mz Nm Ss) Ii(dJ Fa Id Qm Tv) Jo(Ad cI Dg dM Rh) Rt(Il Iv Mk Pb Vq) jO(Ip Jl Na Uf Vs) sC(dE Mu Nm QX) Dk(Mq Mt Nw Pe) Gl(qP Rz Vw Zq) Ms(cI Ib Ju rB) Ne(aC cV Dd Ou) Wc(Bc kR Oa Yh) Rh(Jk Mj Uk Ur) eZ(Aw Ba Db eF) wB(hG Hq Jd On) vA(jP Kp Tr Uf) Ct(Ba dM Mm) Oa(Ha Uk Tj) dJ(cI pF tT) qY(fN Ma Mk) lN(Jy nW Vv) zA(Aw eF On) rO(aN Aw cB) Ub(fN uV) Op(aY Nd) Uk(Mw My) dE(uI wH) hO(Kc Ur) hP(bC cD) rB(Fb rW) qX(bL qD) vP(jQ jR) AoMq EdFi TjLx FaMj GhmZ NmqH MhwQ MkWh TzqZ UarC JnuO JylO KjVq KorS UfvW VvrW aOlM aYpF bRfR jTuN} Qa{Ne(aC Aj Ct dM Hc Ib Iz Jg Jq Jr Kg Lh Li Lv Me Mm Mq Ni Nk nW OE Og Oy Pb pF Qt Qv Qw Tv Uk Vt Th) In(aC bA bL bO bR bS Ch cT dJ Dp gP Id Ke Ko Kr oH pF Rh Ua Ul Ur) Jk(Ba bF bN jT Ke Kr Mm Mq Mr Oe On Pc Pe Ur Vt Wm) Jq(Hq Ii Ik Li Lv Mb Md Me Mt Ni Nj Nl Oe Og Pb) Oy(Fr Iv Jl Jp Li Lu Lx Mv Nb oH Ok Om Qg Tr We) Th(Ch Hf Ii Jy Kr Mj oE Oz Pa Qg Rh Ur Ye Wm) Lh(Hq Hr Hw Hx Jo Mb Me My Ni Nj Nl Nq Og) Kg(Ko Nw Qg Rh Uz Vi Vt Wc Wg Wh Xa Ti) Pb(aA Iv Jl Lu Mc Mm Mq Mr Oe On Pe Qc) Mb(Iv Jl Jn Jr Mc Mm Mr Mt On Pe Qe) Nj(aA Jl Jn Jp Jr Me Mm Mq Mr Oe On) Ii(bA bN Fr Hu Li Mz Nt Nx On Po Vt) nW(fN hW iC oH qD Qv rN sM Uk yE tM) Mt(Hv Jl Me Mq Nd Ni Ns Oe Og) nD(Db Kf kR Nu oE oK pF Rb Us) Nl(Jg Jl Me Nc Nh Ni Oe On) Li(Hq Hv Jo Me Mq My Ni Oe) Ur(Aj Bg Ch Hc Iz Kr Rh Ua) jT(bN Ib Iz Ms oK Qt rW Ua) Mj(cI Jl Ml Mq Mr Oa Pe) Nd(Aj bA dM Jn Jr Mr Pe) Qg(De gP Hc Kj Kr Ua Uk) Ct(BA bN dF Ih oH) Jg(Aj Mu Mv Nq Ns Oe) Rt(aC Dp Iv Ld Qd Vp) Uk(eC Hc Ib Iz Mk Vt) Mq(Hr Hw Lv Ns Og) Ms(aA Mm Mr Oe Vt) Jl(Hw Mk Ns Og Pa) On(Hw Mk My Nq Og) Up(Ke mM mU mW nT) bN(Ch eC jD oE pF) vA(dE Fb Hx Kp Tr) Aj(Ad Ko oH Rh) Fi(Ch Kd Qw Rh) Yh(eC gP oE pF) Jo(Hu Lx Nt Nx) Kr(Yj Zq Zw Tm) Lv(aA Mm Oe) Iv(Hr Hw Hx) Jr(Hq Hv Mm) Ye(aY Of Ul) Ou(qP uM wP) gP(Vt We Zw) oH(Ch Vt Wm) Bc(Lt Zx) Mc(Og Pc) Nh(Kc Nk) Ni(Nc Oc) Iz(Kc Mw) Wh(Ed Mk) Nw(cC Of) Op(hG pK) aA(Ik Nq) cT(jD jM) dM(jO uW) qD(rX uM) uT(jO oK) ChRh DbwB WmxA PoHq LxHc UbwD HrOk HvOg QchP QheQ TlKd KkeC OwfN bAjD bCuM dBwP dJpF} wD{Ri(aH AW Ax bN bP cC Ct fN hP hR Id Iq Ke lK Mf Oa Or rB rO Vv vW) bL(bH bS cF dB eD hF kR Kx Lh Lx Mf Mh Pe qX rB rW rY) De(bP Dc Fa Fy Jq JT Kn Mt Nx Om Ra Rc Un zH) Tj(bR Db Fy Kn Lx Lz Mr Nm Nx Oa Pg Rb Rm Vs) Uf(Aw Ba Bg dJ hO iA Iz Mv Nd Of Oy Qt rB Ua) Ko(dC hO Hq In Iq jP Nf Or rO rS Ua tL tF) Me(bS Dc Kn Kq Kr Kx Pi Pk Ud Up Vt) Hq(bF cU Dc Kp Kq Mz Nx qD Ql Ub Vt) jM(aW bH bS iO Ip Nk Nx Pg Qd rC Ur) Rb(iA Kk Nf Nh Nk Ns Ow Qn tM Wm) Kr(Il In Iq jD Mf Mk Ow rO wC tL) Ql(Ch Hr Js Mh Mk Ne Ow Ua Vv wF) bP(Aw Ch cP dB Hc Jd Kx Ky Mt Oa) eD(aW dC Fb iH Ip Kn Qh qX Ub yL) qD(aN cO Cw Iu Mf Ou Ow qX Vv Wm) uM(cC hB jP Lw Mh Mr Ok Qd sM uX) uZ(Bg Ch dM Jd Qd Qy rA rB rZ Ua) Kp(Aw Cw Hc Hr Hx jF Jk jP Mf) jD(bH bS jO Lu Mf Ny Ou Ub) Bb(Aw Hu Iz oE Qt qX Ua) Md(Bn Cs Qh Sr Ur Us Vt) tF(aW cO Iu jO Kz qH rW) jT(aW Lu qA Qy rA Ua Wm) Mz(In Nc rR Vv wC wF) Ip(aW aZ Ct Ow Qy Wm) rB(aZ dE iH jO Mf Ou) Db(cT Il Mr rV Vv) Ua(bR Ez Nm Ny Qh) dB(iA Ns qI Qn Qu) Aj(Dg Kl Ur Uu) Cs(Ha Kd rO rU) Nd(Lh Mt Ny Pg) Ub(Ch Nc Us wL) Vt(Hx iA Ii jY) Vv(Ap Ks Uc Vo) dE(hB jF vI yL) iH(jY Kn lM rX) tL(aZ jF Kz Ly) Ad(Ct Jh Oy) Fb(Ny qH rS) Nm(Ch Kz Ly) Hr(As Id Kn) Tv(Cw Nk Oy) Rc(Ba bR Qy) Qh(Iz Nv Vp) Of(Ke Ur Us) Ou(aV jP Qd) jO(Mj Mr wP) Mf(qB uO) My(Ss zH) Nh(Id Sr) Tn(bA Mr) Jk(Nw Uu) Kl(Mg Ow) Ny(Hu Nv) Ur(Ii wC) Us(Aw Kz) aZ(cP rX) bS(cP hO) cO(Dg rC) dC(Mh Wm) wL(Nw rS) hR(pY rC) iA(Iu Lu) qH(Mm zA) ChSs CozH CtdJ MtoN NkfN TrbF JylK KeOy KnbR cGhA jFrW jRvP} Qe{Ne(aC Bg Ch Ct eC Hc Iz Jg Jl Jq Kg Lh Li Me Mf Ml Mz Ni Nk Nt Oa oE Og Oy pF Tv Ua Uk Vt Th) In(aC bA cT dE dF dJ Dp eC Id Kd Ke Kn Ko Oa Qv Sr Ua Uk Ul Ur Us) Oy(Fr Hu Iv Jl Jp Li Lw Mi Mq Mr Mz Nb Nc Nl Nt Om Pc Pe Po Tr Vt) Pb(aA Fr Iv Jn Jr Lh Ml Mm Mq Mr Mz Nc Oe Om On Pc Pe Po) Jk(aA Iv Jl Jn Jp Ke Lh Mm Mq Mr Mz Nx On Pe Po Vt Th) Ch(Ba bN cT dF Di Gp Jg Lx Mt oH qD Qg Rz Ur Wh Th) Og(Iv Jl Jn Jq Jr Lh Me Mm Mq Mr Mz Nc Om On Pc Pe) Nl(aA Iv Jl Jn Jq Jr Lh Me Mm Mq Nc Oe On) Jg(Hq Hu Iv Jn Jo Jr Mr Mu Mv Nq Ns Oc Pe) Kg(Dr Hl Id Kc Ko Nw Tr Uz Vi We Wg Xa Th) Jq(Ii Ik Li Mb Me Mq Mt Nh Ni Oe Ok) Rt(Ad As Ba Cp Cq Cu Cw Dc lY Op Us) Ur(Ad Aj Bg Dc Dp Iz Rh Ua Us Vt Wm) Nh(Iv Jn Jr Lh Me Mm Oe Pe Th) Aj(Bc bN cT Dg jO Ko Ms Tr) Ct(BA bN dF Ni oH Qg Rh) Mb(Hv Hw Ir Iv Jn Jr Jt Pe) Mj(Ax Cs Ke Lh Mq Mx Oa Vt) Mt(Iv Jl Jn Jr Lh Mq Mr Ok) Oe(Ik Li Lv Mq Ms Mz Ni Nj) Vt(Jo Kj Kr Mm Qv Rh Uk) Me(Jl Lh Mm Nc On Pc) Ms(aA Fr Jp jT Mr Pe) Ni(Jl Jr Lh Mm Nc Pc) Ik(aA Iv Jn Jr Mm Mz) jO(bZ Nw Ua Vv wB wP) Lv(aA Jl Jn Jr Mm) My(Jh Lh Ok On Wm) Hr(Hw Iv Lh Mq Pe) Ii(bA Nx Om On Po) Th(Ax Iv Oz Uk) Ns(Jl Jr Li Mq) Nj(Fr Lh Mr Pe) nW(qY uU yL tM) Fb(fN hO rB) Lx(Pa Pg Tj) Mk(Jl On Pe) Nw(Bg bN Kr) jT(bL Iz Vv) Hq(Li Po) Hx(Iv Lh) Op(hB pF) Ou(rR vP) Uk(bN Ul) oH(Bc Wm) AaNd NtJo MmJr MzNc HvLi IzQg QchO WeYe QywB JlPa JylK KeKr KjKo OwqD bAjD dFoN dJpF eCnF nOjL} Lx{Oy(bA bS Cq cT Cu

Ir Jl Jp Jq Jr Lh Lv Me Qb Qd) Nj(Fr Ih Ir Jp Jr Lh Mq Mz Nv Qb Qd) eC(Id Ke Kq Qh Sr Uc Un Wc Yl Tl) Wm(bA Ih Jl Mq Ok Qb qD) Lv(Jl Jp Lh Nv On Pz Qb) Me(Jl Jn Js Jt Lh On Qd) Vq(bA bV cV Fa Kk Kz Rt) Mq(Ih Ir Lh Nl Qb Qd) Pe(aM bL dJ Iv Vp Tj) Aj(Ba Ij Ku Kq Ok) Mz(Jr Nl Pd uX) Ax(fN tU wB) Jl(fN Mb Ms) On(Ms Nl Qb) dM(Ij jQ qD) Dr(mZ Ul) Nd(Jp Lh) Nh(Qb Qd) Sr(Dp It) Ko(bN vl) Kq(Bg Dk) Uf(hO vA) DbrN NrOk NhPd NlJp TruN ljlz lvZq XaiO KeKr wPnW} qD{Ny(aJ Ao Ba Bg cB Co Hu Kg Kz Mg My Nq Of Oy Qd qX rA rS rW vV wK) Jy(Bg cK cO dJ Fb fN jM Kr Mk My Of Oh Ou Oy Qy Ri Ua) Un(cB cH dJ lb Iz jD Jo Kg Kz Me Ow Oy Ql Qy Rb vA) Ko(aJ cB Ct lz Kg Kk Of Qd qH qX rB rX Sr uN wF) dM(aZ dB dJ Jl Jq Kd Kk Lu Ou Qd RB sC Sr ul) Pg(bF bQ cH cO Cs Iz Jd Je Ma Mk Mv My Of Qy) Kd(aZ bL bM Ct dJ Fb Id Kr Kz nW Pj Rb) Qd(Cs jF Jl Kp Ly Oa tT Ua uO Ur yL) Kq(aH Ao Ct Db Dk jD Kr Me My Nb Nq) Dc(bR Cw Hu Id iH Kr Kz Of Wm) Jl(aW Bg Fb hR Id Ou Qy Wm) Pe(aZ cH Co Ct Hc jD Oy wQ) rX(bL Cv Ke Kp Lw Pj Ri Ur) rB(Ed Fa Ih Kr Pd qA Rm) Db(aJ Lw qX rW uT wH) Wm(Cv Jq Kn Lw Ri) Hc(Fa Lw Mw Om Uc) Pj(Aj Ed Ms qX wF) dB(aA Lw qX rQ wP) Id(Aj cF Kk Mg) Ih(bM Qg Rb Ri) Kc(aZ Cs Rb vV) St(Kr Rb wQ) wF(bL nW Ua) uN(dJ Nm Tr) Cs(pS uO) Fb(aA Lw) Mh(Cv rS) Kn(Kz qA) Of(Nm Tn) Oy(Kf Uc) cH(Ql qX) dE(rN tT) nW(Lw sM) BaFr CoFa CtCu DlKk LuaJ lpvV SrfN KpqB KrqU RiOa UrqX bLdIl qAqY} Ke{Kr(Aw Ax Bg Co Cs De Dk eC Ef Hc Jk Kj Ko Ms Mu Mw My nD Oa Oy Pb Ua Uk Ut Wm) eC(Ao Aw Bg bN cl Co Cp De Dk Hq Jd Kj Mv Mw My Nb Nv Om On Oy Qt Qy Rb Uk) Ne(Aj Ao Bg Co Cp dM Ed Hc Hq Ib Jo Kg Ms Nb Oz pF Rh Ri Uk) Ax(bN De Hq Jk Jo Kg Md Mj Mk Nv Oy Pb Ri uO Ut vW wH Tj) Ms(Aj De Ii jM Jo Kg Oa Oz Pb rY vV Wm) pF(bL bW wJ Hq Jk Jo Kg Mu Oa Oy Wm) Ii(Fa Fp Ih Mw Nr Pb Pe Rh Rm Wn) Wm(bN Hq Jk jM Kg Mk RB Ur) Oa(Aj De hO Jo Kg Mj Nv oH Ri) Mw(Bg Hc Hq Ib Jk Jo Oy) lM(cD dM Fb hB Md Nv Ri) Ri(Aj Bg Co Cp Dk) vV(Bo Mv qP Qu Tz) Hv(Jo Kg Kj Pb) Oz(Ao Bg Co Dk) dM(Pb qH ul vW) wP(aG Mf oN sC) hX(aW cB Dp jO) rS(Cw hO Kl Mf) oK(jD jM oN rB) uV(aN Me Mh Pk) Aj(Ba Jg St) Kg(De jV Na) Rh(Cp De Hc) yD(Mu ul vW) qA(Ou Ow qH) sO(bN hO Mh) uN(jT Ko uZ) vA(Je Kp Mh) vP(aK aV qP) Dp(jM lN) Fb(jD jO) Fp(Jk Mj) Jl(eT qH) hP(jD Mg) yL(Qu wL) Balz BgGp CsoN FaHq MeqH MuuX llOy OwqI UkbN bWuI cUjO cYjQ tFlN} Aj{Ba(aD aM AS Ax BN cH Cu Cv Cw Dc dF Dp Fa Fp Fr Hb Id Ih Ij It lz Ko Kp Kq Lv Me Mq Mr Mw Nd Ok Oy Pd Pe Rf Sr St Tv Us) Jg(aC As bA Bn bR cT Cw Dc dM Fa Id lj jD Jl Jq Jr Kn Ko Kx Lh Ml Mt Mw My Ni Nr Oa Po Qd Ri St Tv Ur Us Wm) Kq(Bg bN Dk eC Hc Hq Id ll Jk Ko Md Mw My Oa Oy Rh Ur Ut Th) Ko(Bc bN eC Fa Gp lj Jr Kr Ms Oa Qh rW Sr Tn Uf Uo wP) Ad(Dp eC Fb Hb jD Kg Kk Li lN oH pF St wB wP xA) Tn(Bg eC Hq Id Ip Jk Mt Oa Oy Pj rB) St(Bc Dl Id Kp Ne Qg Tv Uc Ue Ur We) Dg(An bA Bc hO Ij Me Oa sK wG) Ij(Hc Id Kl Mt Nd Oy Ri Tr) Mw(aC Id jD Pd Sr Tr Uc) Zq(Bc bR Hu Jn Mq Wh) Tr(hW Kz Mt wB zl) aC(Ap Bc dF Dl Fr) Uc(bN Ne Oa pF) Ok(bN Ms Nd Ne) Pe(Ha Mt Nd Tj) dJ(bA bF dF Fr) Lh(Nd Uu Vq) Oa(Qg Rz Wh) Mt(Ax Ms) Mz(qX rC) Vq(eF Ma) bA(Ap Dl) eC(Id Us) jO(dF Uf) uT(Ss Uu) AsfN NrjT IvRz WhcV QhjQ KlvH LihP NyrS UrwB} nW{wP(aG aJ Bn Dl Fw Hv Hw Hx Ib Iv Jg Jn Jq Jr Js jY Kk Md Me Mh Na Nb Nf Pb Ph Pj Pk qA Qv QX Rb rX tU uG Ul Ur vH yK) wB(aA aM Bc dB dE dG Fp iZ Jg Jt Ko Lw Mh Mp Mx Pd Ql qX Uc Up vH) rN(Ad bA dE iP Jg Kl Ko Lw Ny Ou Ql rA Rb Ss vH Wm) uN(Ba Bc Cp cT eF Fb Jt lM Lw Mm Mp Pj Qh vW zA) jl(Cs iA iC Lh Li Mh Mq Mw Nr oF On Qd St Uc) sM(cG cH cU dF Dg lM Pd qA St uT) uT(aD Ax Bc bW Lw Mw Pj Qd) yD(Fr Jt Mt Nr Pg Po Tr) tM(An Fp Ko Oa Pd Pe rB) rS(aJ Fb hB Mh Mp Qd vO) tU(iZ Jp Mp Nn Pd Qh) qA(Cp cT hW Om Tn Tr) wH(bV Jt Lw Rb St Tr) uU(Ap bM Kl lM Mp Mw) tX(aD Ar aZ It St) vV(cG Fa Po Tr Uf) hW(Fr St Uf zA) tV(aA dB dE Oa) vO(Lw Rb Ul Vv) Ko(hX uG yE) fN(bA dL Fa) zA(iZ Mx rB) Jl(hR qY} Uf(yL xA) dN(yL xA) hX(Oh Sr) tT(jR Uc) qB(bA dF) yE(th Ny) pS(Fb jY) rW(Mx qX) vH(aP Mp) CsuO CutS DgsK ldqY StjK QhiC RieQ PdzI aAhA dGyH wLiA tOiZ} Li{Oy(Fr Ik Iv Jl Jq Jr Lh Lu Mi Mq Mr Ms Mt Mz Nb Nc Ne Nh Ok Om Pe) Jk(aA Fr Ir Iv Jl Jr Lu Mq Mw Mz Ne Nh Nt Ok Om On Pe Qb) Ms(aA Ip Iv Jg Jl Jn Lh Mm Mq Ni Nt Om On Pe) Mt(aA Iv Jl Jn Jq Lh Mq Ne Ni Oe Ok oN) Nj(aA Iv Jl Jn Jp Jq Jr Lh Mm Nk On) Ne(dM eC Ik Iv Jq Lh Nc Ni Nk On) Nl(aA Iv Jl Jn Jq Lh Mm Nk On) Jr(Hq Lu Mm Mz Nd Nh Ni Ns Pb) Og(Ip Iv Jg Jl Jn Lh Mm Nt On) Me(aA Hq Jl Lh Mm Mq Ni Th) Pb(Ir Iv Jn Lh Mm Mr On Pe) Jq(Hq Jo Lv Mq Nh Ns Om) Mz(aA Jo Lu Lv Nc Oe) Nd(dM Jn Mr Ni Oe Pe) Ns(aA Jg Jl Lu Nt) sC(Dc Kn Kq Kr Ml) Lv(Hq Jl Mm Oe) dM(bL dJ eC jO) uW(Bg bW Fw iP) Mk(On Pe Ye) Jo(lk Jg Nt) Ok(Lu Mq Ni) rN(hG Hq Hu) oK(jD jO oN) Nq(Jl On) Mb(Iv Mc) My(Jg Jh) Nc(Lu Nk) Hv(aA Mq) Ii(Lh On) Wn(Hu Vp) oN(dF ql) uO(Ko Mf) BguZ DpTh DrRt PoHq GlZq TzvC HcJh IpjO YkjB JlPa JylK KdeC UvvA bSjD dJpF dLuY eDhX hGuG} Mz{Me(Ip Ir Iv Jg Jn Jq Jr Lh Lv Mn Mu Mx Nj Nx Pe) Nj(Fr Ip Ir Jg Jl Jp Jr Ms Mt Mw Nb On Po Qd) Nd(Iv Jg Jr Lh Lv Mq Mr Mt Pg Po) Ms(Ir Lh Lv Nh Po Qb Qd qX Wn) Mq(Iv Jl Jn Jr Lv Mt Nl Pb) wP(Cs Ko Nc Pk Ua uW Vv yL) qX(Ct Fb Id Kc Ou Ri Vs Vv) uY(aA aP Dp ll Jf Kk yE) vV(aK cJ jQ Mf Qc qP yE) Mt(Lv Nl Ns Oe Oy Pb) xA(Fa Fr Jl uX vB zl) pS(Cs Kk Nv Pj Uu) rN(DB Nk Nl Qc) uO(aJ cI Fr Ko yE) Uk(hR jK qY vT) uX(dJ Dk jP Nk) Nh(Ip Jg On) Tz(wE yH zA) Hq(tN tT wE) Ik(Jl Jp On) wB(Jn Mf Nc) rC(Co Jf Qg) jK(Na Rb Ua) tM(Af Qn Wm) yL(Mm rS rU) vB(aV cA Qw) vT(Ib Jk vO) Ct(wE zA) Ne(Jg Nl) Tr(tU uG) Jr(Ip Jg) Ko(rS rT) Kr(mZ nD) Nv(rU rV) cE(hR uG) cU(tU yH) eC(dM ld) rB(bF Rb) zH(Qn Ua) zl(Nm Pk) qH(iJ lN) jM(bB cG) rY(Qy Vv) pF(Rh Wn) CovI DpqY MbOk NczA NlJp lzlM JkwH RtVq QljD OerO VsjO cDyH dFhR tTqP rAql jQqO yEuL} dM{jO(cE eS dD fN Gp gW Id Js Kk Kq Mf Mj Mn Mp Ny oF Pe Ph Pj Qb Qh St Uf Ut Vv wB) Ij(bL bS Ct eC Hq Ii Jo Mv My Nd Oa Qt Qw Ua Vv) fN(Fa hO ld Kn Kr IL Lu Mt Ni Pg Qh Ql Wm) Pe(bL dJ eC eD Hq Jk Mj Nd Ne Oy Pb Tj) zH(bL bS dB Kr Lu Nq Ow Qy Ua uW yL) aC(aA cA cF cH cR Ct dF dJ Mw Ne) sC(cH Cs Kr Mh Ny Ou Qh qX ul Ur) jQ(Ct Fb Id Ih Ko Oa Pj Rm rY) rY(aW bS Fb Ko Mf Ne Ni Rb) eD(Ax Cs Kn Ou Rm Tv uZ) Mw(eC Hc jD Nd Oa Ua) rC(Id Ih Ko Ou Rm ul) Sr(eC ul uW vA yL) Cs(Gp qP rB uY} jK(Hc Oy Qy Ua) ul{Db Dg Id Vo) Lu(sK tO tV) Oa(bL Mj Ne) eC(Id Pi Us) rB(Jl Nr Pd) yL(Db Pj Uf) vA(Js Jt Kf) vT(Ad Ny Pj) Ct(Ad Ba) Kr(rW uO) dJ(dF qX) hA(bB cU) wL(Ow uZ) hR(pF qX) iO(qH uW) IdeZ TrzI QbjD JsuY OzqY PdxA aDjT aWrX bRfR cMvV dBwH} Nd{Jg(aA Fr Hu Ih Jk Jl Jq Lh Lv Mj Mm Mn Mp Ms Mu Mv Mx Na Ns Og On Pb Pd Po Qb Qd) Mp(Fr Ih Ir Iv Jn Jq Js Lv Mn Mq Mr Ms Mw Ne Nr Nv Og On Pb Pd Pe Po Qd) Lh(aA Fr Hr Hx Ii Iv Jl Jn Jo Jr Lw Mm Mn Mq Mw My Ne Og On Oy Pc Po) On(Hu Ip Iv Jl Jn Jq Jr Me Mh Mm Mn Mr Mu Mv Mw Oe Pe Po Qd) Mt(aA Jn Jq Jr Jt Lw Mm Mn Mr Mw Oe Pa Pc Pd Pe Qd) Fr(aA Ih Ip Ir Iv Jl Jq Mm Mn Ms Na Ne Po Qb Qd) Jp(aA Ip Iv Jq Lw Me Mm Mr Ni Pa Pc Pd Pe Qb) Lv(aA Ij Jq Mm Mq Nv Om Po Pz Qd) Mq(Ip Ir Jl Jq Mm Mn Mw Pb Po) Jl(Jk Ms Ne Og Pb Po) Po(Ms Mw Oy Pb) Zq(Ed Kr Ld mZ) Mm(Ij Ir Jr) Fp(Mr Pe) Oa(Lp Rz) dF(Ax jO) BcTI CtPe CwRt DboO MwIr IpaA WhmZ WnVv cGjO} wB{Ad(Ao cB Cp Cw dE Hq Hr Hu iH Jh Jk jO Mv Nq qH Rb rS) Pj(aZ bR cO Cs Fb Hc Hf hG Jy Kg Mh Ms Ou) Nm(Bg Cp Dk Hf Jd Mc Mg oK Qt sO Tn Wm) Rb(cB dE fN Hq jD Je jO Kz Lu Md oK Qy) dB(cH Cu Fp Fw jD Lh Nr Ra Ur Us yL Wm) Ny(aZ cB Cs Hq Hu jM jP Oa Qy rW Wm) Ss(Ct Jd Js Mv My Oa qH Qt Vv) Kr(aZ fN hP Mh Ou uV vV wQ Wm) dE(Hc Jl Kd Mj My Qh Qy St Uf) jO(Cs Hc Jd Je Kc Kf Ko Oa Qd) Db(aG cT Fp oF Ou Pb St Vs) Tr(Aw Ef Hu Kg Of Ow Ti yD) Cs(Hq iH Kz uO Uu) Oa(hP Hq iH jM rB) Mh(bL cC Ri rS) Hc(Jt Kq Ur Vo) Ax(hG Kz Ou) Wm(hP rB Ri) Uc(Aw Hu Oy) Ur(Kz Of vV) Dg(cO Ou) Jg(Ad Qy) Sr(Kz Qy) Qh(Oy Ua) Uf(Ma Nq) MgUu HuPd TvJk JlfN JyiH KooK KpaH RivV} Mt{Pb(aA Ik Ir Iv Jg Jp Jq Jr Lh Me Mr Nl Ns Oe On Pc Po Qd) Oy(Fr Ij Iv Jh Jq Jr Lh Lv Mq Nb Nt Pe Pg Po) Ms(aA Jn Jq Jt Lw Mm Mr Nb Ni Nn Om Pe Wm) Nj(Iv Jg Jn Jp Jq Jr Lh Ni On Pe Po Qd) Me(Jg Jl Jp Jq Jr Lh Lv Mm Mq Pe Po) Jk(Fr Iv Jg Jp Lh Om On Pe Po Qd) Ns(Ip Iv Jq Jr Lh Lv Mq Nl Po) Jr(Ip Lh Lv Mm Ne Ni Oe Ok) Po(Hq Ii My Ni Nl Oe) Lv(Jq Lh Mm Mq Na Ne Pe) Ni(Jg Jp Nc Nl On) Yk(Kg Mk Oz Vq Wc) Oe(Ip Ir Jg Nt Qd) Ok(Hr Jl Jq Md My) Nl(Ip Jg Jp Nk) Ct(bA cT Pe) eD(IN wP xA) uO(Nm Pj Uf) Wm(tU Th) Ed(Fi Yf) Mq(Jq Lh) My(Jg Jl) Zq(Dg Gl) Wc(Kg Vq) Rt(Bc Mk) hP(Mm Sr) zl(dJ Ur) ArTh CosC EqVq MgJg NcNk IdvA liOn IkOg KrnD wPjO vPvV} wP{jO(Bb Ed Fb Fp Ij Kc Mf

UnbN mMhB} Mq{Lh(Hx Ii Jr Lv Nc Nj Nl Oy) Lv(Ir Jp Mm Mw On Po) Nl(Ip Jp Mw Ne Pb Po) Th(Bg It Mw Ne Un) Fp(aA Jl Jn Jr Pc) Ip(Hc Me Nc Nj Pb) Nj(Jp On Po) Wc(Dp gP Kd) Pb(Fr Ir Nh) Mw(Hc Iz) Nc(Jp Nk) Jq(Hr Ir) DbvI DedF FiKd NmqH MkRt MlMm NeNh TnOy IlYk YeOf dEuI} Ms{Nh(Fr Jn Jp Jq Lv Mn Mp Mw Nc Nn Nv Oh Om Po Qb Qd) Lh(Iv Jl Jo Kg Me Mw Ni Oe On Pc Ur) Lv(Jl Jn Jp Mw Oh On Po Pz) On(Ik Jk Jr Nj Nl Oy Pb) Jp(Jr Ne Nj Nl) Po(Nj Nl Pb) Fr(Ik Nl) Ip(rX Ur) Jl(Nj rB) MpIk MwIr RmrB PdhX cGhA dBuT} Kq{hP(Aw bR Cs Cw Db De Ib Mv Qy Sr Vv) uO(aW Bg Hc Jh Kz Mv Of Ut) Ur(Ao Bg Dc Dk Hc) vA(Jd Mh Qy Ua Ut) Th(Ax Bg Dk Mu) jD(Fb Ib Jk Nv) Iz(Mw Uk Uo) qX(De Jk Om) Dk(Fi oH) Fb(rB uI) Wc(gP kR) hO(bM Ib) wH(dB Hq) BgoH CtRh EdFi HclK NvlN OpiO qAjT sCvV} Ou{rN(Ad bC cJ dJ Dl Kl Ur Vo) uV(Ad Ax bC Dg Dl Jt Kf Pj) yE(Dl Ip Kj Ss Tt Ug) rS(Ap Dl Kc Oh) Ad(uT uX vQ) Ax(pS uT vP) Dg(sM tQ wG) Ip(hW pS qA) Dl(wH tM) Qd(qP vP) Jt(qI tM) Uu(pS tX) Vs(qP sC) NmrW SsuG OweD UnsC UrtS PjqI aWtU bCvI cGhA oKuT} Fb{rS(Ad Db Lu Mm Nx Qd qX Rb rX Vo) pS(Ad Cq Db dJ Lu Vo) jD(cH Id Or Sr Un) rB(Pd Rm Sr uU) qH(Dl Jt Kf Nt) uX(dE Lu Me vT) tU(Cs Dg Pg) dB(tQ tV) dJ(rN uU) hP(bV Vv) qX(fY yK) jQ(cY rW) DbsM DgwG MmhO MxsC QdvT KfvA RihW aKrW bCuI cHxA dEtV} Sr{hP(Ax Cs dB Fa hB Ib Jl Jy Kn Mh Pj Qd Rb) Kz(eZ rO rR uT uZ tM tL) Mw(Hc Iz Jk Ua) jD(bA eZ oH Uk) Rt(Ba hF lY) uI(aE dE rS) pF(dJ nD Op) Db(cZ tM) Ii(bA Lh) bN(pS zH) rB(Dp hB) AwzA ThhF NmxA YkeQ KctM UpmW cOuT dEwH nDoK lNoH} Ct{Ba(aD aM An Ax bA bL BN bS cA cH Cp Cq Cs Cu Cw Dc Dr) bA(Ap Ax Bc cF cH Cu Dc dF Dg Dl Ef Fr It) cT(Bc Dg dJ Ef Fr Mw Pz) Ad(bZ gL hP) dF(Bc bN oN) dX(aM cP) DgrS UcuO SsuT XakR NyhP} Ne{Nh(Fr Ip Ir Jp Jq Jr Lh Lv Mn Mw Nn Nv Oh Om Po Qb Qd) Fa(Gz Hc Hq Iz Mm Mw Ul Th) Nl(Fr Jl Jp Jr Nk On Po) Mw(Hc Ib Iz Kg) Nj(Jl Jr On) Fr(Iz Pb) Jp(Lv Pb) Pi(mS nD) AxUr HcOn JlqH KgLh RipH} nD{Pi(Gp Hv Ii Mh Ml oK Oy Oz) Up(Gp hC Il Js Ma Oz Pb) oK(aZ kI Kz Ml Rb Ur) Db(Ky Mw Oz Pb Us) oN(Mh Oz Pb Rb) bR(bQ cU gL) Mh(aZ Gp) Rb(bQ Lh) Ri(Jn pH) Us(Ip Ma) kR(oF Xa) FyKg NrYk MleF IlKz IrUr OzoF} dB{tT(Dg dJ hR Ip Ny qY Uc) tQ(Ap Bb eD Mf Mm Rc) uT(Md Pj Qh Rb Tv) tX(cH dJ eD Pj) tV(dJ eD rS) rT(Kn Lh rN) vI(dL Jl Rb) Ax(rO uY) Vs(sC vW) cH(wH zI) pS(Mh Us) rN(Id Ql) uX(cL uY) DcvA MjsC KcuU aJhO bArW} Rt{Ir(cV Dp hG Il Kk Oz Pa Pb Uv) Ld(As Jn Kd Lp Mw Nr Qb Ul) Il(Cs dN Hl Ni nT Un Uv) Bc(Dr Fy Ih Pc Pi Po) Oz(Cu Dc Jr Po Un) Nr(Dp Dr oV) Qb(Ar Ba Bn) Fp(Kd We) CwDp DrPo JmlY kRpH} Cs{rS(iH iO kR Mb Ri) eD(Ip jT lN Tv) tU(Ha Mf rC Ss) sC(Db Nm RB) tM(bN Lu Rb) uO(Rc Ri Tj) uT(cO oK oN) aK(rW vV) tV(dE Ur) qH(Ap zA) DpuZ GpaM MmhP QgvC VpvQ PjvA aJuU bNpS cEdJ cJuY qXqP jToK} Fp{Th(Bc gL Il Mh Mm On Ow Oz Ul Ur Tm) Pc(Iv Jn Jr Mr My Ni Ns Oy) Oy(dF Iv Mi Mr Nb Nn) We(aY Va Wc) Jo(Ad Iv Mr) dF(dE Hq Yh) My(Mv Nb) Jn(Jl Js) NnNs MiHq MkMp MrOe WhcV cGhA} vV{jR(Ad Dc Js Kf Kk Mr Mx Nx Oh Pg Po Rb Tv Uc) jQ(cG Id Ip Jl Ny Un) Ri(cH cJ Jy uT) cU(aK aV dJ vP) Ip(aW Id Vv) Pj(Kk Vv) cG(uI vP) AsaW PoHq LzaV QdjT QhaK UrbF oKuT} Ny{hO(aJ bV Ib lM Mm qA rB tM) hP(Ib iO qX Ua Vv) uT(aZ Gl Hc Hq Qy) qA(bP Pj uZ Vv) dJ(qX tR uO) cG(hA uI) qH(cH Dg) sC(qX rW) uO(Mf Nv) DbrN TjtT RbrS QyzA bRuX tUjP jQvP} Bc{Tl(Il Iv Nb Ow Yh) Lt(Il kI Pb Qb) Gp(bL Dr mM) Kc(eQ pI pK) Lp(Ed Qb Rm) Il(Ux Vb) Wc(Jn mF) We(Kj Oy) eQ(Pk Rf) pI(Hf To) DrpK EdFc ThKz YdoH WfnI YeQl VbhB VidU aYpH} Ed{Wh(bR cQ Dp Fc Fi Fn Gc Gz Hb Hq Ic mE Mw oV Qb Un Vp Tj) Rz(Iv Jn Rh Ye) Fi(On Un Uw) We(Gc nF Vp) Wd(Jn My) Xa(kR Ye) YfIl GcRh HuTm} Id{Mw(Iz Jk Jo Kg) eZ(Qc qH Ss Vv) zH(Hq jF rW) sC(Cv jF Kc) Tj(vA wH) hX(Dp Rb) jD(bA oF) uG(Tz Vv) uZ(bM Cv) MfxA MxvA HqwH RiuO bNvB cBjT cHqH hPhB rBoK qBqX jKrS} Wc{Un(eM Gl Kd Kg Oz pF Ul) hG(aX bR dE Il Jn Lv mM) Il(Dr Ld Ni nT) Jn(gP nA Vp) Ow(Je OH) Po(Ex oH) Pi(pF pI) kR(lX nH) AroH DbpK NjpH OnhF bCoD} Db{uT(Fw Ma Mx qX rN) tV(Dc dE Qh Qn) Pj(tX vI wF) rN(aF Qg Rc) Ur(kO mW) uX(Bb bN) DrcV NmxA LweZ MjoO HfvI RctQ WeYe KnrS UpnI VsuY bAuI dFeP hBqY sMjT} Lv{Jp(Ik Jo Jr Me My Nh Ni Nj Nl Pb) Pb(Fr Ir Jl Mx Nh Po) On(Ii Jk Mk My) Jo(Lh Nv Pz) Oy(Fr Lh Nv) Nj(Jl Qd) Jq(Md Me) PoHq IiLh JkJl} Nm{vA(cG cU dF Ki Ow qX Uk) tT(hR Rb Ub Tj) zI(aW bR Cw Hc) qH(bA Ki lM Mr) xA(Aw Kj Mg Nk) Ki(rN sC) Vv(rS Wn) tN(Jk Tn) TjtX PhqX bAuO} jT{uN(AD cH Pj Qd Vo wL) uX(aZ cL eF jF Mu Qy) qA(Dc Pg qX) Ad(Kj qH) Rb(rN tT) Qd(oK Ua) QhJk JlwL UnvA aDrS aZrN} dJ{bF(aA aJ aN Bg bR) hO(aJ Fr lM) qX(rS uT uX) Fa(Rh rS) Vv(rW wF) bR(tV uX) zI(cU Qh) RbtT JlxA KkuX aApF dEtV hBqY} On{Nj(Ii Jk Jr Ni Nk Pb) Ik(Ii Jk Mk Of Og Pb) Me(Hr Mk My) Nh(Jk Mk Pb) Oy(Jr Nc Po) MbMy NlJk HlKg} cG{hA(Aa cH cT cU dA Js Mh Pg Qh qX qY Rm xA) hP(bL bZ Hq Oy Ua) qH(Ad Pj) uI(Jy vT) HqxA YhpH} Dg{qH(bA cH Cu dF Kn Mr Ni Ra Tv) Ow(sK uG wG) dE(tQ tT) wG(Ib Md) MgsK MhtU NihO NkrN QyuT cOtX} Th{Fa(aY Dp Fi Ic Mh Oz Rh Vp) Ar(aA It Ow) Un(Ax Ow Rh) Po(Oz Ye) Ld(gL pH) AxKz NngW YeQl cRdU} eD{xA(Cu Dc dF hB Kf Mr Qd) dF(cY hV jR) tX(iH lN qY) bA(Qx Qy) AxIp FaHu KnrT QntT dEtQ dHuI iHrN} Vv{Wn(aJ bF cJ cU eF Fa hB iP Lh Po) Qh(hP jV) Pj(wF wH) ApyD TigW MezA UcrW SsvI JlrS bWhP} Ad{rS(aW Ib Kk) Jo(bA dF) Ur(Kj Ul) tV(dE Hq) qH(cT oF) uT(Kz oK) CwtX MgtU IzUk JktT OwtM OytN bRpS} Oy{Fr(Hu Ir Mb Nj) Tn(Ip Lh Mw) Qh(lO tU uT) Pg(Jh Tv Vs) Jp(Nh Nj) PoUk FwWe MwbA IrJh} Kg{Dr(Hu kR Po Uw) Qb(Uw Vh Yi Xa) Xa(Gc Pj Un) Hl(Il Jn) GbIl MwnF WhUn JnVh LhRh} Ur{Ax(dF Ip Oz) Hq(tN tT tV) Ir(mW nF) Pg(Bg Co) tT(Mf wL) DipK FasC NrIp aOdF aWzI} Pb{Nh(Fr Jp Lh Mn Nv) Fr(Ik Nj Nl) Po(Nj Nl) Jp(Mb Nj) aA(Ik Lh) IvRz YhkR} aM{bF(bL bR cA cF cK cL cO cV hA) eP(aQ Aw cB cE cV Fw) cAcE} Rb{Pj(eZ uT uV wH) tV(Hc Hq Qy) uT(aZ Kz Md) AxwL LutX MwnI OhrS aWtU} Mf{Ax(tU uZ xA) uO(bA cT Mr) Jl(hP xA) MhrS UetT KdvA PieQ bNuX dEtQ} Ld{We(aW kE nH Ye) Fc(Il kC) oT(Du Gh) MkYe HlmM IlYj TlKd PjwF eQkC} Jk{Qh(fY jI jQ uT) Fr(Hu Ik) Mw(Tn Us) DrIl UcqH TnqX TvuT IkJp} Rz{jB(bJ De Dr Gl nI Nk nR Ri Va) Iv(Eq Oz) gZnR kRoQ} Lh{Ii(Jr Nt Po Qb) Nj(aA Jo) MeHr NlaA IkJo RieQ OppF bLqX dEsC} Mh{tU(aZ Ez Jy rS tF) DrcV JylK UpmW bSrT cJwL iJqH kRrS} Jl{aW(rS tU) qH(iJ Pj) MeJq NbNj QghR RjrB OppI bLuT dEuI hPwL} sC{Kf(aZ bR iH Nk) Un(hV jF Ow) Fa(Co My) BbqX QgJs KnaZ} Ye{Mk(Ow Ql Xa) We(aY Iv) Wh(Oz Qb) PoaY MwbR IlPa ItUl} Pd{xA(bA bW Co Iz Ma Of rA yD) Hq(tV vQ) cOzI} Uc{Nk(qH rS yD) Iz(rO rV) qH(cH Ib) MgrW HqtN HcuT} Pi{kI(Mj Yh) oV(Ru To) pI(Uw Wf) RieQ OpoW UpmW gZnI} cV{Dr(Il Lz Me Qb) bJ(nI nN) mM(hB Ir) EqIl WhiO} dE{hB(qY uZ yK) tV(qY wL) wH(Pj Ql) AptQ FauO TvuT} Mw{Iz(Fa Fr Kd Kk) nF(Af Kf) NkNl RhmW UkjD} Jp{Ik(Jo My Ni Ns Og) Ni(Nc Nl) Nj(Jr Nk)} bR{fR(bF bV cS Iv Jr Qb) TvpS IrmM aNcE} eP{Dd(dL Fw) dF(Al An) EmcP FwGp aJaQ aYdD bBcB} kR{We(Qv Va) Xa(iO nA) Uw(lX lY) FaYh FdlY OpPk} pH{Yh(Hl Ni Of Op Rh) NhRi YknT KdnF OpaY} Ow{Ss(rN tX) Pj(uT uV) rS(Ap Nx) MkXa VoyE} eQ{Ri(Ar bG oF Ph Un) Nr(Qh Qw) NbQw} rB{Rm(bA cU dF) Qh(sM Ua) AxwL QdxA VsuY} Po{Nj(Hq Ni Nk) Hq(uY vT) FcFi NcNk} Ar{DrGp FcnF TooV IlSf QtPs UyoH} Ax{bL(dF uT) RirS bNdF qHzA oKuT} Un{nF(Fc Ru Ry) Il(Sf Yk) GlTl} Fa{Gp(Bg Hq Iz) AaDe mMpI} Fr{Nj(Jr Nb) Ik(My Og) NlJr} Pg{HqwH HctU bLrT bSjD bWhO} Pj{hO(bM dH) UlUk aZuT cOwF} bA{Lu(rW tT) MduY JsjM RmjD} dX{Dd(aN cT dD) GpdD cOdF} hP{Lw(aW Lu Oh) MbQd NiQh} Kd{Tl(cR hF lY) DrmF} Uu{uT(Iz Mg) KkpS hBjK} aY{pF(Uy Yk) ZxdU OpiA} jB{FykI IhYj WhbQ LpfR} Nf{mWjI nClM qWkK} Ua{Qh(jK jQ tU)} Qd{uO(jQ Qg) DplN} Js{TjtX QgtU qHzA} hX{mI(nI nK) lWnJ} oV{AnRu ToIt RiPh} uI{Jy(hA lK) SstX} We{BgPs PzKj} Jn{UpmW nRlK} Jq{MdNh IkOg} Xa{RjhF cMiO} Kf{CwrO KzxA} Lp{nF(Jm oQ)} aW{AsyD SstT} gW{ExbP MxxA} gZ{FykI GhtF} nB{YhhB QcqU} jD{AnzA QloF} AaiPjI MkMlWd MpqVkN TvTkPa IiPhfA IrUpmT YgOhfR QbOphG RmiJqH UslXpF UycRpI aNbFcF bLdHhO

Constrained panels with 2 analytes, where 1.0E-8 >= 'AUC p-value' > 0. Contains 231 panels of 192,797 total panels evaluated. : Et(aA aC Aj AO Ax Bg bN Ch cI Co Cs Ct De Dg Ef Fp Hc Ik Im In Is Iv Iz Ji Jj Jl Jn Jo Jq Jr Jt Kg Kj Kr Li Lj Lu Lv Lx Mb Me Mh Ml Mq Mr Ms Mt My

Figure 3 Continued

Nc Nd Ne Ng Nh Ni Nj Nl No Ns Nw Oa Oc Oy Qa Qe Qv Uk Wm) Nw(Fp hO Ik Im In Is Jj Jr Li Lj Lu Lv Lx Me Mq Ms Mt Nc Nd Ne Ng Nj Nl Oy Pb Qa qC qD Qe uM vS vT) Ji(aA Fp Ii Ik Im In Jj Jo Jq Jt Li Lj Lu Lx Md Mq Ms Mt My Nd Ng Ni Nj Nl Nx Oe Og Oy Pb qC vS) Fp(Im In Is Jg Jj Jl Jp Jq Li Lv Lw Lx Mm Mt Mz No Ok On Pb Qa Qe) Jj(Ik Im Is Jm Lh Li Lx Mt No Ok Qa Qe) Lx(Im Is Lj Lv Me Ms Nd Nj Oy) No(Nd Nh Nj qC qD uM vS) Is(In Lj Ms Nd Ng Og) vS(Id Ko Li Lj Mz Vt) Ok(In Jo Jt Nd Ng) Qc(In Ms Nd Nj) qZ(DB dJ Ko) uM(Id Ke Li wD) Mz(qC qD rW) fN(Ke Kp Li) Ng(Jg Pf) Qa(In Ms) wD(Db nW) oE(Vq Vt) AdAj ChZq MtLj NjIm IdqC LirS dMrC nWuX

Constrained panels with 2 analytes, where 1.0E-7 >= 'AUC p-value' > 1.0E-8. Contains 210 panels of 192,797 total panels evaluated. : Lx(aA Ik In Ir Iv Jg Jn Jq Li Mq Mt Mz Ne Ng Nh Ni Nl No Oe Ok Pb Pe Qa Qe) Et(Ap bA dM Ed Jd Kl Ks oE Qt Qu Qy Rh Ri Ua Ug Ur Us Vt Vv) No(eC Hc Ik Im In Is Iz Lv Mb Ms Mt Nc Ne Ng Nl Nq Nw xA Th) Im(In Is Jk Lh Li Lj Lv Ms Mt Nd Nc Ng Nh Nl Oc Ok Qa Qe) Ok(Ik Is Jr Lj Lv Me Mq Ms Nc Ne Nj Nl Nw Oe Pb Qa Qe) Li(In Is Lv Me Ms Mt Nd Ng Nh Nj Nl Og Pb qC) Nw(aA Ii Iv Jn Jq Md Mw My Ni Ns OE rW) Qe(Ik Jg Jk Lj Lv Mt Ng Nh Nl Og Oy Pb) Fp(aA Fr Iv Lh Mq Ms Ni Oe Pc) Qa(Jg Jk Lj Lv Nd Ng Nj Nl Pb) Jj(Jg Lj Nt Nx On Pf Po Pz Wm) Is(Jk Lv Mt Nj Nl Oe Oy Pf) Mz(Me Mq oE Pf qY rO wD) Lj(Jg Lv Ne Nh Nl On qC) Mt(Me Ms Nd Ng Nj) Ji(qD uM Wm) Pf(Lv Nj Og) Aj(Ba Jg) Ke(hO oE) Uf(Ng qH) Pj(qZ wD) mZ(Dr Rz) NdOn IdhP IvZq dE

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.4E1 | 6.4E1 | 7.5E1 | 8.0E1 | 5.1E1 | 5.6E1 | 2.0E0 | 2.0E0 | 4.4E2 | 2.6E2 | 965 | 67 | 171 | 67 | 0.52 |
| Ad | ug/mL | 2.5E-2 | 6.9E-2 | 5.8E-2 | 2.4E-1 | 7.7E-2 | 1.1E0 | 6.8E-4 | 2.6E-3 | 3.7E-1 | 8.5E0 | 255 | 57 | 103 | 57 | 0.67 |
| Af | ng/mL | 9.2E-1 | 1.6E0 | 1.8E1 | 1.9E1 | 7.2E1 | 5.1E1 | 1.7E-3 | 1.7E-3 | 5.3E2 | 2.6E2 | 255 | 57 | 103 | 57 | 0.59 |
| Aj | ug/mL | 1.4E0 | 2.6E0 | 2.6E0 | 2.8E0 | 2.4E0 | 2.5E0 | 1.5E-3 | 2.1E-3 | 6.1E0 | 6.1E0 | 255 | 57 | 103 | 57 | 0.51 |
| Al | mg/mL | 9.0E-5 | 7.0E-5 | 2.5E-4 | 2.5E-4 | 4.2E-4 | 3.9E-4 | 2.5E-6 | 6.6E-6 | 1.9E-3 | 1.7E-3 | 255 | 57 | 103 | 57 | 0.51 |
| An | U/mL | 4.0E1 | 6.5E1 | 1.5E2 | 3.4E2 | 4.7E2 | 1.1E3 | 9.8E-4 | 9.0E-1 | 5.5E3 | 7.8E3 | 255 | 57 | 103 | 57 | 0.61 |
| Ao | pg/mL | 8.5E1 | 1.1E2 | 2.1E2 | 9.8E2 | 1.0E3 | 5.1E3 | 1.5E0 | 4.1E0 | 1.6E4 | 3.8E4 | 255 | 57 | 103 | 57 | 0.56 |
| Ap | ng/mL | 2.7E1 | 4.3E1 | 4.3E1 | 6.0E1 | 5.0E1 | 6.2E1 | 9.9E-1 | 2.7E0 | 3.3E2 | 2.9E2 | 255 | 57 | 103 | 57 | 0.61 |
| Ar | ng/mL | 6.5E-1 | 1.3E0 | 2.0E0 | 5.0E0 | 4.1E0 | 1.1E1 | 3.4E-3 | 4.1E-2 | 4.3E1 | 5.4E1 | 255 | 57 | 103 | 57 | 0.62 |
| As | ng/mL | 8.7E-3 | 1.1E-2 | 1.2E-2 | 3.4E-2 | 1.6E-2 | 1.6E-1 | 1.7E-3 | 1.7E-3 | 1.1E-1 | 1.2E0 | 255 | 57 | 103 | 57 | 0.56 |
| Aw | pg/mL | 1.6E1 | 1.8E1 | 1.6E1 | 2.0E1 | 5.4E0 | 7.9E0 | 3.5E0 | 1.1E1 | 3.3E1 | 5.1E1 | 255 | 57 | 103 | 57 | 0.66 |
| Ax | ng/mL | 2.1E0 | 2.6E0 | 8.2E0 | 2.6E1 | 1.8E1 | 1.1E2 | 1.9E-2 | 4.1E-2 | 1.5E2 | 7.7E2 | 255 | 57 | 103 | 57 | 0.53 |
| Ba | ng/mL | 3.7E1 | 1.4E2 | 2.8E2 | 9.8E2 | 7.3E2 | 2.5E3 | 3.7E-1 | 1.1E0 | 8.1E3 | 1.5E4 | 255 | 57 | 103 | 57 | 0.64 |
| Bb | ng/mL | 2.6E0 | 5.1E0 | 5.3E0 | 8.7E0 | 8.5E0 | 1.1E1 | 4.1E-3 | 4.1E-3 | 6.6E1 | 6.4E1 | 255 | 57 | 103 | 57 | 0.65 |
| Bc | ng/mL | 3.3E1 | 5.0E1 | 9.7E1 | 1.7E2 | 1.8E2 | 2.9E2 | 1.1E-1 | 2.9E-1 | 1.0E3 | 1.2E3 | 255 | 57 | 103 | 57 | 0.58 |
| Bg | ng/mL | 6.4E-2 | 2.1E-1 | 4.4E0 | 7.8E0 | 2.2E1 | 2.7E1 | 5.3E-4 | 5.3E-4 | 2.5E2 | 1.5E2 | 255 | 57 | 103 | 57 | 0.62 |
| Bn | ng/mL | 5.6E-2 | 5.6E-2 | 8.5E-1 | 2.9E0 | 1.6E0 | 7.9E0 | 5.6E-2 | 5.6E-2 | 8.5E0 | 5.8E1 | 255 | 57 | 103 | 57 | 0.59 |
| Bo | ng/mL | 1.1E1 | 1.5E1 | 1.3E1 | 2.2E1 | 9.6E0 | 3.7E1 | 1.6E-2 | 1.6E-2 | 7.4E1 | 2.8E2 | 255 | 57 | 103 | 57 | 0.60 |
| Ch | uIU/mL | 9.0E-1 | 1.4E0 | 6.5E0 | 3.3E1 | 2.1E1 | 1.0E2 | 3.4E-3 | 3.9E-2 | 2.3E2 | 5.3E2 | 255 | 57 | 103 | 57 | 0.61 |
| Co | ng/mL | 3.1E1 | 4.9E1 | 9.1E1 | 1.8E2 | 2.1E2 | 5.9E2 | 3.9E0 | 1.5E-1 | 1.9E3 | 4.4E3 | 255 | 57 | 103 | 57 | 0.63 |
| Cp | ng/mL | 1.9E1 | 2.6E1 | 2.5E1 | 6.3E1 | 2.5E1 | 1.7E2 | 6.0E-1 | 6.0E-1 | 2.9E2 | 1.3E3 | 255 | 57 | 103 | 57 | 0.68 |
| Cq | ng/mL | 2.4E-2 | 3.4E-2 | 1.6E-1 | 9.5E-1 | 1.1E0 | 6.5E0 | 8.0E-4 | 8.0E-4 | 1.7E1 | 4.9E1 | 255 | 57 | 103 | 57 | 0.56 |
| Cs | ng/mL | 4.5E1 | 9.6E1 | 2.1E2 | 4.7E2 | 4.0E2 | 1.5E3 | 2.7E-2 | 8.9E-1 | 2.9E3 | 1.1E4 | 255 | 57 | 103 | 57 | 0.57 |
| Ct | ng/mL | 1.2E0 | 4.3E-1 | 2.6E1 | 6.3E1 | 8.2E1 | 1.4E2 | 1.1E-4 | 2.8E-2 | 6.2E2 | 6.2E2 | 255 | 57 | 103 | 57 | 0.49 |
| Cu | ng/mL | 2.1E-1 | 3.4E-1 | 4.2E-1 | 1.6E0 | 9.2E-1 | 8.7E0 | 9.6E-3 | 1.5E-2 | 9.2E0 | 6.6E1 | 255 | 57 | 103 | 57 | 0.63 |
| Cv | ng/mL | 4.6E0 | 8.0E0 | 2.4E1 | 4.2E1 | 7.0E1 | 1.0E2 | 5.6E-3 | 2.4E-2 | 5.3E2 | 5.2E2 | 255 | 57 | 103 | 57 | 0.54 |
| Cw | mIU/mL | 2.8E-2 | 4.3E-2 | 3.8E-2 | 1.7E-1 | 3.0E-2 | 8.9E-1 | 2.3E-3 | 4.7E-3 | 1.9E-1 | 6.8E0 | 255 | 57 | 103 | 57 | 0.61 |
| Cx | ng/mL | 1.8E-1 | 2.0E0 | 5.4E1 | 8.4E1 | 1.0E2 | 1.3E2 | 9.3E-5 | 9.3E-5 | 3.9E2 | 3.9E2 | 255 | 57 | 103 | 57 | 0.55 |
| Db | ug/mL | 8.2E0 | 7.5E0 | 9.4E0 | 9.4E0 | 8.8E0 | 7.9E0 | 5.3E-1 | 8.7E-1 | 1.0E2 | 4.1E1 | 255 | 57 | 103 | 57 | 0.49 |
| Dc | nmol/L | 1.8E-2 | 2.5E-2 | 5.7E-2 | 3.3E-1 | 1.3E-1 | 1.9E0 | 5.2E-6 | 3.6E-4 | 1.2E0 | 1.4E1 | 255 | 57 | 103 | 57 | 0.56 |
| Dd | ug/mL | 6.9E-2 | 1.1E-1 | 1.8E-1 | 2.5E-1 | 2.6E-1 | 5.1E-1 | 1.9E-4 | 1.6E-4 | 1.6E0 | 3.6E0 | 255 | 57 | 103 | 57 | 0.52 |
| De | ng/mL | 3.4E-3 | 3.4E-3 | 5.6E-2 | 1.4E-1 | 1.1E-1 | 2.0E-1 | 3.4E-3 | 3.4E-3 | 5.9E-1 | 9.0E-1 | 255 | 57 | 103 | 57 | 0.62 |
| Dg | ng/mL | 2.5E1 | 4.6E1 | 3.9E1 | 5.6E1 | 3.8E1 | 4.2E1 | 2.8E-1 | 7.8E-1 | 1.9E2 | 1.9E2 | 255 | 57 | 103 | 57 | 0.63 |
| Di | pg/mL | 1.6E0 | 3.1E0 | 2.0E0 | 3.1E0 | 1.8E0 | 2.2E0 | 1.8E-1 | 1.8E-1 | 1.3E1 | 9.3E0 | 255 | 57 | 103 | 57 | 0.66 |
| Dk | uIU/mL | 1.4E-2 | 1.9E-2 | 9.3E-2 | 1.1E-1 | 6.3E-1 | 3.2E-1 | 1.1E-4 | 1.1E-4 | 8.9E0 | 2.3E0 | 255 | 57 | 103 | 57 | 0.60 |
| Dl | ng/mL | 2.0E2 | 2.8E2 | 2.7E2 | 4.2E2 | 2.4E2 | 3.6E2 | 3.1E0 | 4.7E0 | 1.4E3 | 1.6E3 | 255 | 57 | 103 | 57 | 0.63 |
| Dp | ng/ml | 2.5E0 | 2.2E0 | 4.9E0 | 9.3E0 | 6.8E0 | 2.9E1 | 3.7E-3 | 3.7E-3 | 4.3E1 | 2.0E2 | 122 | 51 | 99 | 51 | 0.47 |
| Dr | pg/ml | 3.4E1 | 3.4E1 | 5.7E1 | 6.0E2 | 6.6E1 | 2.3E3 | 7.5E-1 | 7.5E-1 | 2.9E2 | 1.0E4 | 99 | 21 | 50 | 21 | 0.56 |
| Du | pg/ml | 4.2E1 | 1.9E2 | 5.0E2 | 1.8E3 | 1.3E3 | 5.5E3 | 1.2E0 | 1.2E0 | 7.0E3 | 2.4E4 | 53 | 18 | 42 | 18 | 0.60 |
| Dw | ng/ml | 2.6E-2 | 9.2E-3 | 7.8E-2 | 2.2E-2 | 1.4E-1 | 1.7E-2 | 9.2E-3 | 9.2E-3 | 6.7E-1 | 4.9E-2 | 35 | 7 | 7 | 7 | 0.37 |
| Ef | ng/ml | 9.5E-2 | 2.3E-1 | 6.9E-1 | 1.4E0 | 1.7E0 | 2.5E0 | 5.7E-4 | 5.7E-3 | 1.0E1 | 9.5E0 | 165 | 53 | 102 | 53 | 0.61 |
| Wm | % | 8.2E-1 | 4.9E-1 | 3.0E1 | 2.5E1 | 1.9E2 | 1.2E2 | 5.4E-2 | 8.5E-2 | 2.4E3 | 8.7E2 | 204 | 56 | 119 | 56 | 0.50 |
| Ed | pg/ml | 5.2E-1 | 5.2E-1 | 9.3E1 | 2.8E1 | 6.6E2 | 4.0E1 | 5.2E-1 | 5.2E-1 | 7.3E3 | 1.5E2 | 122 | 51 | 98 | 51 | 0.49 |
| Eo | ng/ml | 2.3E0 | 1.8E0 | 4.7E0 | 3.0E0 | 5.2E0 | 3.5E0 | 1.3E-1 | 3.6E-1 | 1.7E1 | 9.2E0 | 35 | 7 | 7 | 7 | 0.43 |
| Yf | ng/mL | 1.6E1 | 1.5E1 | 1.4E2 | 3.0E1 | 8.4E2 | 4.6E1 | 2.9E-1 | 2.9E-1 | 6.6E3 | 1.7E2 | 61 | 18 | 50 | 18 | 0.42 |
| Tj | pg/mL | 3.7E-1 | 3.7E-1 | 7.6E1 | 9.0E0 | 3.7E2 | 2.3E1 | 3.6E-1 | 3.7E-1 | 3.5E3 | 1.4E2 | 165 | 52 | 103 | 52 | 0.47 |
| Po | pg/ml | 1.3E-1 | 3.6E0 | 8.0E0 | 1.2E1 | 2.7E1 | 3.1E1 | 8.0E-3 | 2.6E-2 | 2.7E2 | 2.2E2 | 359 | 90 | 189 | 90 | 0.61 |
| Ti | ug/mL | 2.8E0 | 4.4E0 | 4.1E0 | 6.7E0 | 3.7E0 | 7.7E0 | 1.2E-1 | 8.4E-1 | 1.6E1 | 3.7E1 | 86 | 24 | 69 | 24 | 0.62 |
| Em | ng/ml | 2.9E-3 | 1.3E-2 | 5.3E-2 | 1.2E-1 | 1.1E-1 | 3.8E-1 | 2.8E-16 | 2.8E-16 | 5.4E-1 | 1.9E0 | 123 | 27 | 51 | 27 | 0.52 |
| Et | ng/ml | 1.0E3 | 2.0E3 | 1.3E3 | 2.1E3 | 1.0E3 | 1.3E3 | 7.5E1 | 7.9E1 | 4.9E3 | 5.0E3 | 359 | 90 | 189 | 90 | 0.68 |
| Eq | pg/ml | 1.3E2 | 4.3E2 | 2.7E2 | 4.3E2 | 3.8E2 | 4.2E2 | 1.0E0 | 1.0E0 | 1.8E3 | 1.3E3 | 53 | 18 | 42 | 18 | 0.60 |
| Ew | U/ml | 1.7E0 | 1.9E0 | 1.8E0 | 2.0E0 | 8.2E-1 | 8.5E-1 | 6.5E-1 | 1.3E0 | 4.0E0 | 4.0E0 | 35 | 7 | 7 | 7 | 0.58 |
| Th | ug/mL | 1.1E0 | 1.1E0 | 1.5E0 | 1.9E0 | 1.6E0 | 1.8E0 | 2.6E-3 | 2.9E-1 | 1.2E1 | 7.5E0 | 86 | 24 | 69 | 24 | 0.57 |
| Fa | ng/ml | 3.9E1 | 4.0E1 | 1.2E2 | 1.6E2 | 7.3E2 | 3.4E2 | 3.4E-2 | 6.0E-1 | 8.0E3 | 2.1E3 | 120 | 51 | 98 | 51 | 0.60 |

Figure 4

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ez | ng/ml | 3.7E0 | 5.0E0 | 1.6E1 | 2.1E1 | 3.9E1 | 6.3E1 | 1.3E-2 | 1.3E-2 | 3.0E2 | 4.5E2 | 122 | 51 | 99 | 51 | 0.56 |
| Fb | ng/ml | 2.3E1 | 2.8E1 | 2.1E1 | 2.7E1 | 1.2E1 | 9.1E0 | 1.0E0 | 6.6E-1 | 5.7E1 | 4.3E1 | 120 | 52 | 98 | 52 | 0.66 |
| Ex | ng/ml | 6.0E-2 | 9.7E-2 | 2.4E-1 | 3.1E-1 | 8.4E-1 | 6.6E-1 | 3.5E-5 | 1.7E-4 | 8.9E0 | 4.1E0 | 126 | 43 | 69 | 43 | 0.63 |
| Fc | pg/ml | 2.2E-1 | 2.2E-1 | 2.9E2 | 1.9E1 | 2.0E3 | 7.1E1 | 2.2E-1 | 2.2E-1 | 1.5E4 | 3.1E2 | 53 | 19 | 42 | 19 | 0.51 |
| Fd | pg/ml | 2.9E1 | 7.3E1 | 9.7E2 | 1.5E3 | 4.6E3 | 5.7E3 | 9.8E-1 | 9.8E-1 | 3.3E4 | 2.5E4 | 53 | 19 | 42 | 19 | 0.51 |
| Fi | pg/ml | 2.5E-1 | 2.5E-1 | 3.3E2 | 2.1E1 | 1.9E3 | 6.2E1 | 2.5E-1 | 2.5E-1 | 1.4E4 | 2.5E2 | 53 | 19 | 42 | 19 | 0.47 |
| Fn | ng/ml | 2.1E-1 | 2.1E-1 | 8.5E0 | 2.9E0 | 3.8E1 | 5.5E0 | 1.1E-14 | 1.1E-14 | 4.2E2 | 2.7E1 | 122 | 51 | 99 | 51 | 0.46 |
| Fp | ng/ml | 9.4E0 | 2.1E1 | 2.0E1 | 3.1E1 | 2.6E1 | 3.3E1 | 6.0E-3 | 5.8E-2 | 1.4E2 | 1.3E2 | 380 | 90 | 189 | 90 | 0.60 |
| Fr | ng/ml | 2.5E3 | 5.5E4 | 9.9E4 | 1.8E5 | 1.7E5 | 2.4E5 | 6.4E2 | 1.3E3 | 8.4E5 | 8.4E5 | 464 | 95 | 193 | 95 | 0.62 |
| Fw | pg/ml | 7.1E-1 | 2.9E0 | 1.0E2 | 2.0E1 | 6.7E2 | 4.9E1 | 1.1E-14 | 1.7E-14 | 6.9E3 | 3.3E2 | 167 | 55 | 103 | 55 | 0.54 |
| Fy | ng/ml | 3.1E1 | 4.2E1 | 4.9E1 | 7.2E1 | 5.5E1 | 1.0E2 | 1.2E-1 | 1.2E-1 | 3.3E2 | 6.5E2 | 121 | 49 | 98 | 49 | 0.57 |
| Gh | pg/ml | 2.3E0 | 2.0E0 | 2.5E1 | 8.8E1 | 5.0E1 | 3.5E2 | 2.9E-2 | 2.9E-2 | 2.7E2 | 1.5E3 | 53 | 18 | 42 | 18 | 0.44 |
| Gb | % | 3.2E1 | 5.7E1 | 4.3E1 | 6.2E1 | 3.9E1 | 6.4E1 | 2.7E0 | 2.2E0 | 2.3E2 | 3.0E2 | 53 | 19 | 41 | 19 | 0.64 |
| Gc | ng/ml | 9.9E1 | 1.3E2 | 1.4E2 | 1.8E2 | 1.4E2 | 1.7E2 | 6.4E0 | 2.7E1 | 7.9E2 | 6.3E2 | 104 | 21 | 52 | 21 | 0.58 |
| Gd | ng/ml | 2.9E1 | 3.8E1 | 3.0E1 | 3.7E1 | 1.6E2 | 2.3E1 | 5.4E0 | 3.0E0 | 8.1E1 | 8.0E1 | 119 | 25 | 50 | 25 | 0.58 |
| Gn | U/ml | 5.0E-1 | 2.2E-1 | 1.7E0 | 5.8E0 | 3.7E0 | 2.5E1 | 1.3E-3 | 5.6E-3 | 3.0E1 | 1.1E2 | 95 | 21 | 50 | 21 | 0.42 |
| Gl | pg/ml | 6.1E3 | 1.1E4 | 9.8E3 | 1.3E4 | 9.0E3 | 9.8E3 | 2.3E2 | 5.3E2 | 3.4E4 | 3.2E4 | 162 | 55 | 102 | 55 | 0.61 |
| Gp | U/ml | 1.8E0 | 1.1E0 | 4.4E0 | 2.8E0 | 7.6E0 | 4.1E0 | 1.3E-3 | 1.5E-2 | 6.7E1 | 2.0E1 | 167 | 53 | 103 | 53 | 0.42 |
| Gz | ug/ml | 1.2E0 | 3.0E0 | 1.1E1 | 8.7E0 | 5.3E1 | 2.2E1 | 2.9E-16 | 4.2E-2 | 4.8E2 | 1.5E2 | 81 | 42 | 64 | 42 | 0.52 |
| Ha | ng/ml | 2.7E0 | 2.7E0 | 8.4E0 | 1.1E1 | 1.9E1 | 2.1E1 | 1.7E-2 | 1.4E-3 | 1.0E2 | 1.1E2 | 120 | 51 | 98 | 51 | 0.52 |
| Nm | pg/ml | 1.2E4 | 2.0E4 | 2.4E4 | 5.3E4 | 4.9E4 | 1.3E5 | 1.0E-9 | 1.0E-9 | 7.8E5 | 9.6E5 | 358 | 92 | 190 | 92 | 0.58 |
| Nn | pg/ml | 1.3E2 | 2.4E2 | 2.5E3 | 3.1E3 | 1.1E4 | 1.4E4 | 1.0E-9 | 1.0E-9 | 1.0E5 | 1.1E5 | 358 | 92 | 190 | 92 | 0.59 |
| No | pg/ml | 1.3E1 | 1.9E1 | 2.7E1 | 5.7E1 | 5.9E1 | 1.3E2 | 1.0E-9 | 1.0E-9 | 5.9E2 | 7.7E2 | 358 | 92 | 190 | 92 | 0.59 |
| Nq | pg/ml | 2.2E0 | 2.4E0 | 2.1E1 | 1.8E1 | 8.4E1 | 4.5E1 | 1.0E-9 | 1.0E-9 | 1.2E3 | 2.9E2 | 358 | 92 | 190 | 92 | 0.52 |
| Nr | pg/ml | 4.7E-1 | 2.5E0 | 1.6E1 | 3.7E1 | 7.0E1 | 1.6E2 | 1.0E-9 | 1.0E-9 | 9.8E2 | 1.4E3 | 358 | 92 | 190 | 92 | 0.61 |
| Ns | pg/ml | 1.0E-9 | 1.0E-9 | 8.9E0 | 7.0E0 | 4.5E1 | 3.4E1 | 1.0E-9 | 1.0E-9 | 6.8E2 | 2.4E2 | 358 | 92 | 190 | 92 | 0.48 |
| Nt | pg/ml | 9.4E1 | 1.3E2 | 1.2E2 | 1.7E2 | 9.2E1 | 1.6E2 | 1.0E-9 | 1.2E1 | 5.9E2 | 1.2E3 | 358 | 92 | 190 | 92 | 0.61 |
| Nu | pg/ml | 1.7E1 | 3.2E1 | 4.9E1 | 7.2E1 | 8.8E1 | 1.0E2 | 1.0E-9 | 1.0E-9 | 8.9E2 | 6.3E2 | 358 | 92 | 190 | 92 | 0.58 |
| Lu | pg/ml | 1.0E4 | 1.0E4 | 1.5E4 | 1.2E4 | 3.2E4 | 1.2E4 | 6.7E2 | 1.1E3 | 3.9E5 | 7.5E4 | 360 | 92 | 190 | 92 | 0.47 |
| Lv | pg/ml | 1.0E-9 | 6.9E-1 | 1.1E1 | 2.2E1 | 2.2E1 | 3.4E1 | 1.0E-9 | 1.0E-9 | 2.4E2 | 1.9E2 | 360 | 92 | 190 | 92 | 0.59 |
| Lw | pg/ml | 1.0E-9 | 1.0E-9 | 1.4E-1 | 2.4E0 | 1.8E0 | 1.1E1 | 1.0E-9 | 1.0E-9 | 3.2E1 | 8.0E1 | 360 | 92 | 190 | 92 | 0.53 |
| Lx | pg/ml | 1.0E-9 | 4.7E1 | 1.1E2 | 2.7E2 | 4.2E2 | 5.4E2 | 1.0E-9 | 1.0E-9 | 6.2E3 | 2.8E3 | 360 | 92 | 190 | 92 | 0.63 |
| Ly | pg/ml | 1.0E-9 | 1.0E-9 | 9.1E0 | 1.3E1 | 1.8E1 | 2.2E1 | 1.0E-9 | 1.0E-9 | 1.2E2 | 9.6E1 | 360 | 92 | 190 | 92 | 0.53 |
| Lz | pg/ml | 1.0E-9 | 1.0E-9 | 2.9E0 | 5.5E0 | 2.4E1 | 3.0E1 | 1.0E-9 | 1.0E-9 | 4.3E2 | 2.6E2 | 360 | 92 | 190 | 92 | 0.51 |
| Ma | pg/ml | 2.4E2 | 4.7E2 | 1.5E3 | 1.8E3 | 4.7E3 | 3.4E3 | 1.0E-9 | 1.0E-9 | 6.5E4 | 2.2E4 | 360 | 92 | 190 | 92 | 0.60 |
| Mb | pg/ml | 2.5E1 | 3.2E1 | 3.1E1 | 3.7E1 | 1.4E1 | 2.4E1 | 5.4E0 | 4.1E0 | 9.3E1 | 2.1E2 | 360 | 92 | 190 | 92 | 0.56 |
| Mc | pg/ml | 1.0E-9 | 1.0E-9 | 1.7E-2 | 1.7E-1 | 2.3E-1 | 1.4E0 | 1.0E-9 | 1.0E-9 | 4.0E0 | 1.3E1 | 360 | 92 | 190 | 92 | 0.51 |
| Md | pg/ml | 1.0E-9 | 1.0E-9 | 6.2E-1 | 7.2E-1 | 5.2E0 | 3.7E0 | 1.0E-9 | 1.0E-9 | 6.8E1 | 2.9E1 | 360 | 92 | 190 | 92 | 0.53 |
| Me | pg/ml | 3.2E1 | 2.8E1 | 2.9E1 | 3.1E1 | 1.6E1 | 3.8E1 | 1.0E-9 | 1.0E-9 | 1.2E2 | 3.2E2 | 360 | 92 | 190 | 92 | 0.44 |
| Mf | pg/ml | 1.0E-9 | 1.0E-9 | 3.7E-1 | 1.1E0 | 1.6E0 | 6.0E0 | 1.0E-9 | 1.0E-9 | 2.0E1 | 5.6E1 | 360 | 92 | 190 | 92 | 0.54 |
| Mg | pg/ml | 1.9E0 | 1.7E0 | 6.4E0 | 1.0E1 | 1.1E1 | 1.6E1 | 1.0E-9 | 1.0E-9 | 8.8E1 | 9.2E1 | 360 | 92 | 190 | 92 | 0.55 |
| Mh | pg/ml | 1.0E-9 | 1.0E-9 | 1.1E0 | 8.8E-1 | 8.4E0 | 3.1E0 | 1.0E-9 | 1.0E-9 | 1.1E2 | 1.8E1 | 360 | 92 | 190 | 92 | 0.53 |
| Mi | pg/ml | 1.0E-9 | 1.0E-9 | 6.9E-1 | 1.8E0 | 7.1E0 | 1.2E1 | 1.0E-9 | 1.0E-9 | 1.2E2 | 1.1E2 | 360 | 92 | 190 | 92 | 0.51 |
| Mj | pg/ml | 1.0E-9 | 1.0E-9 | 5.2E0 | 7.4E0 | 3.1E1 | 2.9E1 | 1.0E-9 | 1.0E-9 | 4.6E2 | 2.1E2 | 360 | 92 | 190 | 92 | 0.52 |
| Mk | pg/ml | 6.5E-1 | 1.5E0 | 1.6E1 | 1.3E1 | 9.9E1 | 5.4E1 | 1.0E-9 | 1.0E-9 | 1.7E3 | 5.0E2 | 360 | 92 | 190 | 92 | 0.50 |
| Ml | pg/ml | 1.0E-9 | 1.0E-9 | 9.1E0 | 9.4E0 | 1.1E2 | 5.5E1 | 1.0E-9 | 1.0E-9 | 2.1E3 | 5.1E2 | 360 | 92 | 190 | 92 | 0.55 |
| Mm | pg/ml | 4.0E2 | 8.3E2 | 8.0E2 | 1.5E3 | 9.7E2 | 1.9E3 | 1.0E-9 | 1.0E-9 | 6.0E3 | 1.2E4 | 360 | 92 | 190 | 92 | 0.60 |
| Mn | pg/ml | 4.8E0 | 7.3E0 | 1.0E1 | 1.2E1 | 2.5E1 | 1.3E1 | 1.0E-9 | 1.0E-9 | 3.5E2 | 7.8E1 | 360 | 92 | 190 | 92 | 0.62 |
| Mp | pg/ml | 1.0E-9 | 2.7E0 | 9.7E0 | 1.2E1 | 2.2E1 | 2.3E1 | 1.0E-9 | 1.0E-9 | 1.8E2 | 1.3E2 | 360 | 92 | 190 | 92 | 0.57 |
| Mq | pg/ml | 1.0E-9 | 1.0E-9 | 2.8E0 | 5.7E0 | 1.7E1 | 1.9E1 | 1.0E-9 | 1.0E-9 | 2.1E2 | 1.0E2 | 360 | 92 | 190 | 92 | 0.54 |
| Mr | pg/ml | 1.0E-9 | 1.0E-9 | 1.4E1 | 7.0E1 | 8.7E1 | 3.8E2 | 1.0E-9 | 1.0E-9 | 1.4E3 | 3.4E3 | 360 | 92 | 190 | 92 | 0.56 |
| Ms | pg/ml | 3.8E2 | 3.8E2 | 5.6E2 | 4.7E2 | 7.1E2 | 4.3E2 | 1.0E-9 | 1.0E-9 | 5.6E3 | 2.0E3 | 360 | 92 | 190 | 92 | 0.49 |
| Mt | pg/ml | 1.0E-9 | 7.6E-1 | 1.1E1 | 4.2E1 | 6.3E1 | 3.4E2 | 1.0E-9 | 1.0E-9 | 8.7E2 | 3.2E3 | 360 | 92 | 190 | 92 | 0.59 |
| Mu | pg/ml | 1.0E-9 | 1.0E-9 | 1.5E0 | 1.1E0 | 1.0E1 | 4.4E0 | 1.0E-9 | 1.0E-9 | 9.9E1 | 3.5E1 | 360 | 92 | 190 | 92 | 0.55 |
| Mv | pg/ml | 1.0E-9 | 1.0E-9 | 8.2E1 | 7.7E1 | 4.2E2 | 1.8E2 | 1.0E-9 | 1.0E-9 | 4.5E3 | 9.2E2 | 360 | 92 | 190 | 92 | 0.55 |
| Mw | pg/ml | 2.5E1 | 3.8E1 | 5.8E2 | 4.1E2 | 3.9E3 | 1.2E3 | 1.0E-9 | 1.0E-9 | 6.2E4 | 7.9E3 | 360 | 92 | 190 | 92 | 0.55 |
| Mx | pg/ml | 1.0E-9 | 1.0E-9 | 1.8E-1 | 5.0E-1 | 8.2E-1 | 2.2E0 | 1.0E-9 | 1.0E-9 | 9.2E0 | 2.0E1 | 360 | 92 | 190 | 92 | 0.55 |

Figure 4 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| My | pg/ml | 1.0E-9 | 1.0E-9 | 5.6E2 | 3.2E2 | 3.5E3 | 1.4E3 | 1.0E-9 | 1.0E-9 | 3.9E4 | 1.1E4 | 360 | 92 | 190 | 92 | 0.50 |
| Mz | pg/ml | 8.5E0 | 1.3E1 | 2.1E1 | 6.3E1 | 5.9E1 | 2.4E2 | 1.0E-9 | 1.0E-9 | 8.4E2 | 1.9E3 | 360 | 92 | 190 | 92 | 0.61 |
| Na | pg/ml | 1.0E-9 | 1.0E-9 | 5.7E-1 | 1.2E0 | 1.8E0 | 4.7E0 | 1.0E-9 | 1.0E-9 | 7.8E0 | 4.2E1 | 360 | 92 | 190 | 92 | 0.52 |
| Nb | pg/ml | 1.8E0 | 2.4E0 | 4.6E0 | 6.9E0 | 1.6E1 | 2.5E1 | 1.0E-9 | 1.0E-9 | 2.3E2 | 2.1E2 | 360 | 92 | 190 | 92 | 0.55 |
| Nc | pg/ml | 4.5E2 | 2.2E2 | 6.7E2 | 3.7E2 | 8.4E2 | 4.4E2 | 1.0E-9 | 1.0E-9 | 9.2E3 | 1.8E3 | 360 | 92 | 190 | 92 | 0.39 |
| Nd | pg/ml | 3.1E1 | 6.7E0 | 2.6E1 | 1.6E1 | 2.0E1 | 1.7E1 | 1.0E-9 | 1.0E-9 | 8.4E1 | 5.8E1 | 360 | 92 | 190 | 92 | 0.36 |
| Ne | pg/ml | 4.9E2 | 3.2E2 | 6.3E2 | 4.2E2 | 6.4E2 | 4.1E2 | 1.0E-9 | 1.0E-9 | 7.0E3 | 1.8E3 | 360 | 92 | 190 | 92 | 0.39 |
| Nf | pg/ml | 1.0E-9 | 1.0E-9 | 2.9E0 | 3.6E0 | 8.8E0 | 1.8E1 | 1.0E-9 | 1.0E-9 | 8.2E1 | 1.3E2 | 360 | 92 | 190 | 92 | 0.46 |
| Ng | pg/ml | 2.1E1 | 2.9E1 | 1.1E2 | 1.3E2 | 2.3E2 | 2.3E2 | 1.0E-9 | 1.0E-9 | 1.6E3 | 1.2E3 | 360 | 92 | 190 | 92 | 0.50 |
| Nh | pg/ml | 7.7E1 | 4.7E1 | 9.8E1 | 7.0E1 | 8.7E1 | 7.3E1 | 1.0E-9 | 3.1E0 | 5.6E2 | 3.5E2 | 360 | 92 | 190 | 92 | 0.38 |
| Ni | pg/ml | 4.5E0 | 1.4E1 | 7.4E1 | 1.1E2 | 1.1E2 | 1.7E2 | 1.0E-9 | 1.0E-9 | 7.1E2 | 1.1E3 | 360 | 92 | 190 | 92 | 0.54 |
| Nj | pg/ml | 9.0E0 | 3.8E0 | 1.2E1 | 7.6E0 | 1.2E1 | 9.6E0 | 1.0E-9 | 1.0E-9 | 8.3E1 | 5.8E1 | 360 | 92 | 190 | 92 | 0.37 |
| Nk | pg/ml | 2.2E1 | 1.4E1 | 3.6E1 | 2.5E1 | 4.0E1 | 3.2E1 | 1.0E-9 | 1.0E-9 | 1.8E2 | 1.5E2 | 360 | 92 | 190 | 92 | 0.43 |
| Nl | pg/ml | 5.2E1 | 2.7E1 | 7.0E1 | 4.0E1 | 8.2E1 | 4.1E1 | 1.0E-9 | 1.0E-9 | 1.1E3 | 1.6E2 | 360 | 92 | 190 | 92 | 0.37 |
| Hl | pg/ml | 1.3E1 | 1.4E1 | 4.5E1 | 2.1E2 | 7.9E1 | 8.2E2 | 1.0E-9 | 1.0E-9 | 3.5E2 | 3.6E3 | 53 | 19 | 42 | 19 | 0.46 |
| Ho | pg/ml | 1.5E1 | 1.9E1 | 3.2E1 | 3.8E1 | 9.6E1 | 8.6E1 | 1.0E-9 | 6.7E0 | 7.0E2 | 3.9E2 | 53 | 19 | 42 | 19 | 0.62 |
| Hp | ng/ml | 1.7E0 | 1.6E0 | 7.2E1 | 2.4E2 | 2.4E2 | 4.0E2 | 1.0E-9 | 1.0E-9 | 8.9E2 | 8.9E2 | 53 | 19 | 42 | 19 | 0.53 |
| Tz | pg/ml | 3.7E3 | 7.4E3 | 7.5E3 | 1.1E4 | 1.1E4 | 1.2E4 | 7.4E1 | 9.8E1 | 8.8E4 | 6.7E4 | 124 | 50 | 98 | 50 | 0.62 |
| Ua | pg/ml | 3.5E3 | 5.1E3 | 3.0E4 | 1.6E4 | 1.9E5 | 2.8E4 | 3.5E2 | 2.7E2 | 2.1E6 | 1.3E5 | 124 | 50 | 98 | 50 | 0.58 |
| Ub | pg/ml | 5.8E2 | 4.0E2 | 8.7E2 | 6.5E2 | 1.2E3 | 8.1E2 | 1.0E-9 | 1.2E1 | 9.8E3 | 4.4E3 | 124 | 50 | 98 | 50 | 0.43 |
| Ue | pg/ml | 3.1E1 | 2.7E1 | 3.5E1 | 4.6E1 | 2.4E1 | 4.7E1 | 4.2E0 | 1.0E-9 | 1.2E2 | 2.7E2 | 124 | 50 | 98 | 50 | 0.52 |
| Uc | pg/ml | 7.8E2 | 1.1E3 | 1.6E3 | 2.9E3 | 3.3E3 | 8.2E3 | 3.3E1 | 1.5E1 | 2.9E4 | 5.7E4 | 124 | 50 | 98 | 50 | 0.57 |
| Ud | pg/ml | 1.0E-9 | 1.0E-9 | 3.4E0 | 1.1E0 | 3.5E1 | 7.5E0 | 1.0E-9 | 1.0E-9 | 3.9E2 | 5.3E1 | 124 | 50 | 98 | 50 | 0.50 |
| Hq | pg/ml | 1.1E0 | 1.8E0 | 1.1E1 | 1.3E1 | 5.9E1 | 4.3E1 | 1.0E-9 | 1.0E-9 | 9.5E2 | 3.4E2 | 360 | 90 | 190 | 90 | 0.58 |
| Hr | pg/ml | 1.3E2 | 8.8E1 | 8.3E2 | 7.6E2 | 1.6E3 | 1.9E3 | 1.0E-9 | 1.0E-9 | 1.2E4 | 1.4E4 | 360 | 90 | 190 | 90 | 0.46 |
| Hu | pg/ml | 7.9E0 | 2.1E1 | 3.5E3 | 1.5E3 | 3.5E4 | 5.3E3 | 1.0E-9 | 1.0E-9 | 6.3E5 | 3.5E4 | 360 | 90 | 190 | 90 | 0.54 |
| Hv | pg/ml | 1.3E0 | 1.6E0 | 3.4E0 | 1.3E1 | 1.5E1 | 9.4E1 | 1.0E-9 | 1.0E-9 | 2.5E2 | 8.9E2 | 360 | 90 | 190 | 90 | 0.56 |
| Hw | pg/ml | 7.2E0 | 6.5E0 | 2.5E1 | 1.2E2 | 1.1E2 | 9.9E2 | 1.0E-9 | 1.0E-9 | 1.7E3 | 9.4E3 | 360 | 90 | 190 | 90 | 0.47 |
| Hx | pg/ml | 7.2E0 | 1.3E1 | 6.0E1 | 4.9E1 | 5.0E2 | 1.6E2 | 1.0E-9 | 1.0E-9 | 9.3E3 | 1.3E3 | 360 | 90 | 190 | 90 | 0.56 |
| Ib | ng/ml | 6.9E-2 | 4.4E-2 | 6.9E-1 | 3.2E0 | 3.0E0 | 1.0E1 | 1.0E-9 | 1.0E-9 | 3.0E1 | 5.6E1 | 122 | 51 | 99 | 51 | 0.48 |
| Ic | U/ml | 2.2E2 | 2.2E2 | 3.1E2 | 2.1E3 | 1.4E3 | 9.5E3 | 2.9E0 | 6.6E0 | 1.5E4 | 6.5E4 | 122 | 51 | 99 | 51 | 0.63 |
| Id | U/ml | 6.2E-1 | 6.9E-1 | 1.0E0 | 1.0E1 | 1.2E0 | 6.0E1 | 1.0E-9 | 2.2E-1 | 6.9E0 | 4.3E2 | 122 | 51 | 99 | 51 | 0.57 |
| Tt | pg/ml | 1.6E2 | 1.9E2 | 1.6E2 | 2.0E2 | 4.4E1 | 6.7E1 | 8.0E1 | 7.6E1 | 3.0E2 | 4.4E2 | 114 | 43 | 92 | 43 | 0.67 |
| To | pg/ml | 1.6E0 | 1.8E0 | 1.9E0 | 2.1E0 | 2.6E0 | 2.7E0 | 1.0E-9 | 1.0E-9 | 2.3E1 | 1.2E1 | 119 | 47 | 95 | 47 | 0.49 |
| Tr | pg/ml | 2.8E0 | 4.1E0 | 4.1E0 | 7.1E0 | 4.7E0 | 1.1E1 | 3.5E-2 | 1.0E-9 | 2.9E1 | 7.6E1 | 118 | 46 | 94 | 46 | 0.61 |
| Tn | pg/ml | 2.1E1 | 4.4E1 | 5.9E1 | 1.4E2 | 1.5E2 | 3.8E2 | 2.6E0 | 6.6E0 | 1.5E3 | 2.3E3 | 119 | 47 | 95 | 47 | 0.67 |
| Tv | ng/ml | 1.2E1 | 1.2E1 | 2.0E1 | 1.7E2 | 4.8E1 | 1.0E3 | 1.0E-9 | 1.0E-9 | 4.9E2 | 7.1E3 | 119 | 47 | 95 | 47 | 0.54 |
| Ih | ng/ml | 5.7E1 | 7.5E1 | 2.0E2 | 2.9E2 | 3.6E2 | 5.0E2 | 1.0E-9 | 1.0E-9 | 2.5E3 | 2.8E3 | 360 | 92 | 190 | 92 | 0.54 |
| Ii | ng/ml | 7.0E1 | 9.5E1 | 2.7E2 | 2.6E2 | 8.1E2 | 6.2E2 | 7.5E-1 | 1.3E0 | 8.4E3 | 4.5E3 | 360 | 92 | 190 | 92 | 0.53 |
| Ij | ng/ml | 7.0E1 | 7.1E1 | 2.0E2 | 3.9E2 | 7.3E2 | 2.6E3 | 2.1E0 | 9.3E0 | 6.4E3 | 2.4E4 | 358 | 89 | 190 | 89 | 0.53 |
| Ik | ng/ml | 1.2E1 | 6.1E1 | 9.2E2 | 1.7E3 | 9.2E3 | 1.3E4 | 5.9E-1 | 1.7E0 | 1.2E5 | 1.2E5 | 358 | 91 | 190 | 91 | 0.58 |
| Il | ng/ml | 3.3E2 | 2.6E2 | 1.4E3 | 1.1E3 | 3.0E3 | 2.6E3 | 1.0E-9 | 1.0E-9 | 1.2E4 | 1.3E4 | 354 | 89 | 190 | 89 | 0.46 |
| Im | ng/ml | 1.9E2 | 2.3E2 | 3.0E2 | 4.8E2 | 3.4E2 | 9.3E2 | 1.3E1 | 2.0E1 | 3.1E3 | 6.2E3 | 357 | 90 | 190 | 90 | 0.56 |
| In | ng/ml | 4.2E0 | 3.0E0 | 3.6E1 | 5.6E1 | 2.3E2 | 4.7E2 | 1.0E-9 | 1.0E-9 | 3.9E3 | 4.5E3 | 360 | 92 | 190 | 92 | 0.45 |
| Hb | ng/ml | 2.0E1 | 2.9E1 | 2.7E1 | 3.7E1 | 2.6E1 | 3.4E1 | 1.1E0 | 4.8E-1 | 1.5E2 | 2.0E2 | 120 | 53 | 98 | 53 | 0.62 |
| Hc | pg/ml | 6.1E2 | 5.8E2 | 2.2E3 | 4.3E3 | 4.9E3 | 1.4E4 | 1.0E-9 | 1.0E-9 | 3.6E4 | 1.0E5 | 120 | 53 | 98 | 53 | 0.55 |
| Hf | ng/ml | 1.2E2 | 1.5E2 | 3.6E2 | 2.5E2 | 5.3E2 | 3.2E2 | 1.0E-9 | 1.0E-9 | 2.5E3 | 1.8E3 | 120 | 53 | 98 | 53 | 0.51 |
| Io | ng/ml | 6.9E3 | 8.2E3 | 1.7E4 | 1.7E4 | 5.1E4 | 2.4E4 | 6.6E1 | 6.6E1 | 8.8E5 | 1.1E5 | 357 | 90 | 189 | 90 | 0.53 |
| Ip | ng/ml | 8.1E0 | 1.9E1 | 1.8E1 | 2.6E1 | 2.7E1 | 3.0E1 | 1.0E-9 | 4.9E-3 | 2.6E2 | 1.6E2 | 357 | 90 | 189 | 90 | 0.55 |
| Iq | ug/ml | 9.1E-2 | 1.1E-1 | 3.9E1 | 3.7E1 | 7.2E2 | 2.3E1 | 1.0E-9 | 1.0E-9 | 1.4E4 | 2.2E2 | 357 | 90 | 189 | 90 | 0.52 |
| Ir | ug/ml | 2.9E-1 | 5.5E-1 | 4.4E0 | 8.1E0 | 3.3E1 | 4.3E1 | 1.0E-9 | 1.0E-9 | 5.1E2 | 3.7E2 | 356 | 90 | 189 | 90 | 0.60 |
| Is | ng/ml | 1.3E0 | 3.1E0 | 6.4E0 | 1.2E1 | 3.1E1 | 3.3E1 | 1.0E-9 | 2.2E-3 | 5.5E2 | 2.6E2 | 357 | 90 | 189 | 90 | 0.62 |
| It | ng/ml | 1.9E0 | 2.5E0 | 2.6E1 | 6.1E1 | 1.3E2 | 7.5E1 | 1.0E-9 | 1.0E-9 | 1.2E3 | 6.8E2 | 357 | 90 | 189 | 90 | 0.57 |
| Iu | ng/ml | 1.9E2 | 2.4E2 | 1.6E3 | 1.5E3 | 5.0E3 | 3.8E3 | 1.0E-9 | 1.0E-9 | 2.9E4 | 2.4E4 | 357 | 90 | 189 | 90 | 0.52 |
| Iv | ng/ml | 1.1E1 | 2.3E1 | 8.5E1 | 1.3E2 | 8.5E2 | 5.5E2 | 1.0E-9 | 1.0E-9 | 1.6E4 | 3.8E3 | 357 | 90 | 189 | 90 | 0.63 |
| Iz | ng/ml | 1.2E2 | 1.7E2 | 4.2E2 | 1.5E3 | 9.7E2 | 8.5E3 | 1.5E0 | 4.1E0 | 8.4E3 | 6.2E4 | 120 | 53 | 98 | 53 | 0.58 |
| Yg | pg/ml | 2.5E2 | 3.5E2 | 5.7E2 | 4.0E3 | 8.6E2 | 1.2E4 | 1.0E-9 | 1.0E-9 | 4.2E3 | 5.0E4 | 51 | 18 | 41 | 18 | 0.58 |

Figure 4 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yh | pg/ml | 2.6E2 | 3.1E2 | 5.6E2 | 5.5E2 | 1.1E3 | 7.5E2 | 1.0E-9 | 1.0E-9 | 7.8E3 | 3.0E3 | 51 | 18 | 41 | 18 | 0.50 |
| Yi | pg/ml | 2.7E2 | 5.0E2 | 5.7E2 | 7.6E2 | 1.1E3 | 1.1E3 | 1.0E-9 | 1.0E-9 | 7.6E3 | 4.6E3 | 51 | 18 | 41 | 18 | 0.57 |
| Yk | U/ml | 1.0E-9 | 1.0E-9 | 9.9E-2 | 6.4E-1 | 2.9E-1 | 1.5E0 | 1.0E-9 | 1.0E-9 | 1.5E0 | 5.6E0 | 51 | 18 | 41 | 18 | 0.57 |
| Yj | pg/ml | 1.9E2 | 1.4E2 | 4.2E2 | 6.2E2 | 5.7E2 | 1.6E3 | 9.7E0 | 3.9E1 | 3.2E3 | 7.0E3 | 51 | 18 | 41 | 18 | 0.41 |
| Yd | ng/ml | 2.0E-1 | 2.7E-1 | 3.2E-1 | 3.5E-1 | 3.8E-1 | 3.8E-1 | 6.6E-3 | 1.7E-2 | 1.8E0 | 1.5E0 | 55 | 19 | 44 | 19 | 0.54 |
| Wb | pg/ml | 3.1E4 | 3.4E4 | 3.4E4 | 4.2E4 | 1.8E4 | 3.2E4 | 2.2E3 | 7.5E3 | 8.5E4 | 1.5E5 | 55 | 19 | 44 | 19 | 0.56 |
| Vz | pg/ml | 3.6E0 | 2.7E0 | 5.6E0 | 4.4E0 | 6.6E0 | 4.8E0 | 1.0E-9 | 7.3E-1 | 4.0E1 | 2.2E1 | 55 | 19 | 44 | 19 | 0.44 |
| Si | ng/ml | 9.1E-1 | 1.2E0 | 1.7E0 | 2.0E0 | 2.2E0 | 2.4E0 | 2.0E-2 | 8.6E-3 | 1.0E1 | 1.0E1 | 53 | 19 | 42 | 19 | 0.57 |
| Sf | mIU/mL | 1.1E1 | 1.9E1 | 4.8E1 | 3.3E1 | 1.1E2 | 4.3E1 | 8.1E-2 | 2.5E0 | 7.2E2 | 1.7E2 | 53 | 19 | 42 | 19 | 0.58 |
| Sh | mIU/mL | 7.7E0 | 1.7E1 | 4.1E1 | 6.3E1 | 1.1E2 | 1.1E2 | 2.9E-2 | 7.8E-2 | 5.9E2 | 3.7E2 | 53 | 19 | 42 | 19 | 0.60 |
| Sj | ng/ml | 4.0E-1 | 4.0E-1 | 4.0E-1 | 4.3E-1 | 9.0E-2 | 1.1E-1 | 1.9E-1 | 2.5E-1 | 5.7E-1 | 6.6E-1 | 53 | 19 | 42 | 19 | 0.56 |
| Rc | pg/ml | 5.0E3 | 7.6E3 | 6.4E3 | 8.6E3 | 5.0E3 | 7.2E3 | 1.9E2 | 2.4E2 | 3.0E4 | 3.9E4 | 122 | 50 | 98 | 50 | 0.60 |
| Rb | pg/ml | 7.5E-1 | 6.1E-1 | 2.4E0 | 3.1E0 | 3.6E0 | 8.4E0 | 1.0E-9 | 1.0E-9 | 1.6E1 | 5.6E1 | 122 | 50 | 98 | 50 | 0.50 |
| Zq | 2.6ng/ml | 1.6E2 | 3.9E2 | 2.5E2 | 4.2E2 | 2.5E2 | 3.0E2 | 8.3E0 | 1.7E1 | 9.7E2 | 9.7E2 | 52 | 19 | 41 | 19 | 0.69 |
| Zw | 2.5ng/ml | 4.3E0 | 6.7E0 | 1.0E1 | 1.3E1 | 1.4E1 | 1.8E1 | 6.3E-2 | 2.4E-1 | 5.9E1 | 5.9E1 | 55 | 19 | 44 | 19 | 0.51 |
| Zx | 2.3mU/ml | 1.1E-1 | 1.4E-1 | 4.0E-1 | 2.8E-1 | 1.6E0 | 6.3E-1 | 4.1E-2 | 3.2E-2 | 1.2E1 | 2.9E0 | 55 | 19 | 44 | 19 | 0.52 |
| Pz | ng/ml | 3.1E3 | 4.2E3 | 6.1E3 | 6.6E3 | 9.7E3 | 8.8E3 | 1.3E1 | 4.7E1 | 9.5E4 | 7.0E4 | 358 | 89 | 189 | 89 | 0.54 |
| Qa | ng/ml | 2.7E3 | 5.2E3 | 5.9E3 | 9.9E3 | 8.0E3 | 2.4E4 | 1.5E2 | 2.3E2 | 5.2E4 | 2.2E5 | 358 | 89 | 189 | 89 | 0.62 |
| Qb | ng/ml | 8.3E1 | 1.2E2 | 2.5E2 | 2.0E2 | 7.0E2 | 2.1E2 | 7.9E-1 | 4.4E0 | 8.3E3 | 1.1E3 | 358 | 89 | 189 | 89 | 0.57 |
| Qc | ng/ml | 1.9E2 | 2.9E2 | 4.7E2 | 4.6E2 | 9.5E2 | 5.2E2 | 8.1E-1 | 3.0E0 | 1.1E4 | 2.8E3 | 358 | 89 | 189 | 89 | 0.55 |
| Qd | ng/ml | 7.9E3 | 1.1E4 | 2.2E4 | 2.7E4 | 1.1E5 | 4.1E4 | 1.5E2 | 6.9E2 | 2.0E6 | 2.3E5 | 358 | 89 | 189 | 89 | 0.60 |
| Qe | ng/ml | 6.9E2 | 1.5E3 | 1.9E3 | 2.2E3 | 5.6E3 | 2.7E3 | 1.0E-9 | 4.7E1 | 9.7E4 | 1.8E4 | 358 | 89 | 189 | 89 | 0.61 |
| Jd | ng/ml | 4.3E-1 | 1.7E0 | 7.5E0 | 5.3E0 | 5.9E1 | 1.4E1 | 1.0E-9 | 1.0E-9 | 6.5E2 | 9.1E1 | 122 | 51 | 99 | 51 | 0.71 |
| Je | ng/ml | 1.0E-9 | 7.3E-1 | 1.4E0 | 3.0E0 | 5.4E0 | 6.6E0 | 1.0E-9 | 1.0E-9 | 5.6E1 | 4.5E1 | 122 | 51 | 99 | 51 | 0.63 |
| Jf | ng/ml | 1.0E-9 | 1.0E-9 | 7.4E-1 | 1.3E0 | 1.9E0 | 2.5E0 | 1.0E-9 | 1.0E-9 | 1.2E1 | 1.0E1 | 122 | 51 | 99 | 51 | 0.54 |
| Jg | ng/ml | 3.7E2 | 7.5E2 | 6.8E2 | 1.1E3 | 1.0E3 | 1.2E3 | 5.8E0 | 1.3E1 | 1.0E4 | 7.1E3 | 360 | 90 | 190 | 90 | 0.63 |
| Jh | ng/ml | 2.3E0 | 4.4E0 | 2.4E1 | 4.6E1 | 9.5E1 | 1.4E2 | 1.0E-9 | 1.0E-9 | 1.2E3 | 1.1E3 | 360 | 90 | 190 | 90 | 0.58 |
| Ji | ng/ml | 4.6E1 | 7.3E1 | 6.6E1 | 1.3E2 | 7.0E1 | 1.8E2 | 1.1E0 | 5.2E0 | 5.3E2 | 1.3E3 | 360 | 90 | 190 | 90 | 0.65 |
| Sr | pg/mL | 3.2E2 | 4.8E2 | 7.5E2 | 1.4E3 | 1.3E3 | 3.1E3 | 1.0E-9 | 1.0E-9 | 9.8E3 | 2.1E4 | 121 | 50 | 98 | 50 | 0.57 |
| Ss | pg/mL | 6.2E4 | 1.6E5 | 1.2E5 | 1.7E5 | 1.4E5 | 1.7E5 | 9.5E3 | 7.1E3 | 7.1E5 | 8.5E5 | 121 | 50 | 98 | 50 | 0.60 |
| St | pg/mL | 1.7E7 | 4.2E7 | 4.0E7 | 9.1E7 | 5.3E7 | 2.4E8 | 7.8E5 | 1.0E-9 | 4.1E8 | 1.7E9 | 119 | 49 | 96 | 49 | 0.61 |
| Wc | ng/ml | 1.0E-9 | 1.9E-2 | 6.2E-2 | 1.3E-1 | 1.6E-1 | 4.0E-1 | 1.0E-9 | 1.0E-9 | 9.8E-1 | 1.8E0 | 55 | 19 | 43 | 19 | 0.56 |
| Wd | ng/ml | 8.8E0 | 1.2E1 | 2.5E1 | 1.2E2 | 7.8E1 | 2.8E2 | 1.0E-9 | 1.5E0 | 5.4E2 | 1.2E3 | 55 | 19 | 43 | 19 | 0.63 |
| We | ng/ml | 2.6E-1 | 7.7E-1 | 6.0E-1 | 3.6E0 | 9.0E-1 | 6.8E0 | 1.0E-9 | 1.0E-9 | 3.9E0 | 2.3E1 | 55 | 19 | 43 | 19 | 0.67 |
| Wg | ng/ml | 1.0E-9 | 1.0E-9 | 2.9E-4 | 2.8E-2 | 2.2E-3 | 1.2E-1 | 1.0E-9 | 1.0E-9 | 1.6E-2 | 5.3E-1 | 55 | 19 | 43 | 19 | 0.52 |
| Wh | ng/ml | 8.7E-3 | 1.6E-2 | 3.4E-2 | 3.3E-1 | 1.1E-1 | 1.0E0 | 1.0E-9 | 1.0E-9 | 7.6E-1 | 4.5E0 | 55 | 19 | 43 | 19 | 0.67 |
| Wf | ng/ml | 1.0E-9 | 1.7E-1 | 2.0E-1 | 2.6E-1 | 6.5E-1 | 5.8E-1 | 1.0E-9 | 1.0E-9 | 4.6E0 | 2.3E0 | 55 | 19 | 43 | 19 | 0.58 |
| Ra | pg/ml | 1.0E-9 | 1.0E-9 | 6.8E-1 | 1.8E0 | 1.3E0 | 9.0E0 | 1.0E-9 | 1.0E-9 | 7.3E0 | 6.4E1 | 122 | 50 | 98 | 50 | 0.49 |
| Qz | pg/ml | 1.1E1 | 9.4E0 | 7.1E1 | 3.5E1 | 1.1E2 | 5.8E1 | 1.0E-9 | 1.0E-9 | 7.1E2 | 2.6E2 | 122 | 50 | 98 | 50 | 0.41 |
| Qy | pg/ml | 3.9E-1 | 6.4E-1 | 3.6E0 | 1.2E1 | 1.6E1 | 4.8E1 | 1.0E-9 | 1.0E-9 | 1.6E2 | 3.2E2 | 122 | 50 | 98 | 50 | 0.58 |
| Qx | pg/ml | 1.0E-9 | 1.0E-9 | 5.6E0 | 3.8E0 | 4.9E1 | 1.6E1 | 1.0E-9 | 1.0E-9 | 5.4E2 | 1.1E2 | 122 | 50 | 98 | 50 | 0.52 |
| Qw | pg/ml | 9.0E-2 | 1.0E-9 | 2.2E0 | 2.9E0 | 1.1E1 | 1.1E1 | 1.0E-9 | 1.0E-9 | 1.2E2 | 5.6E1 | 122 | 50 | 98 | 50 | 0.43 |
| Qv | pg/ml | 2.8E4 | 1.5E4 | 3.9E4 | 2.5E4 | 7.4E4 | 2.5E4 | 1.2E3 | 4.0E2 | 7.4E5 | 1.2E5 | 122 | 50 | 98 | 50 | 0.38 |
| Qu | pg/ml | 1.7E0 | 2.1E1 | 8.6E1 | 7.5E1 | 1.8E2 | 1.4E2 | 1.0E-9 | 1.0E-9 | 8.0E2 | 7.0E2 | 122 | 50 | 98 | 50 | 0.56 |
| Qt | pg/ml | 9.9E0 | 1.5E1 | 3.6E1 | 6.3E1 | 7.7E1 | 1.6E2 | 1.0E-9 | 1.0E-9 | 4.1E2 | 1.0E3 | 122 | 50 | 98 | 50 | 0.57 |
| Qh | ng/ml | 1.3E1 | 2.2E1 | 3.5E1 | 3.9E1 | 7.0E1 | 5.5E1 | 1.2E-1 | 7.8E-1 | 6.4E2 | 3.4E2 | 122 | 50 | 98 | 50 | 0.59 |
| Qg | ng/ml | 9.0E0 | 6.0E0 | 1.7E1 | 1.5E1 | 2.5E1 | 3.1E1 | 1.5E-1 | 3.3E-1 | 1.8E2 | 2.0E2 | 122 | 50 | 98 | 50 | 0.41 |
| Jj | ng/ml | 7.1E2 | 4.2E2 | 2.7E3 | 1.0E3 | 1.9E4 | 1.9E3 | 2.3E0 | 1.2E1 | 3.4E5 | 1.2E4 | 360 | 90 | 190 | 90 | 0.40 |
| Jk | ng/ml | 3.0E0 | 3.2E0 | 2.1E1 | 2.5E1 | 4.6E1 | 4.7E1 | 1.0E-9 | 4.3E-2 | 2.8E2 | 2.4E2 | 360 | 90 | 190 | 90 | 0.54 |
| Jl | ng/ml | 3.4E-1 | 5.8E-1 | 1.9E0 | 1.1E2 | 4.7E0 | 1.0E3 | 7.6E-4 | 1.9E-3 | 3.2E1 | 9.9E3 | 360 | 90 | 190 | 90 | 0.59 |
| Jm | ng/ml | 1.5E1 | 2.3E1 | 5.3E1 | 5.7E1 | 1.2E2 | 1.0E2 | 1.0E-9 | 2.3E-1 | 1.4E3 | 6.1E2 | 360 | 90 | 190 | 90 | 0.54 |
| Jn | pg/ml | 3.2E-1 | 5.5E-1 | 3.2E0 | 1.6E1 | 3.3E1 | 1.0E2 | 1.0E-9 | 1.0E-9 | 6.2E2 | 7.3E2 | 360 | 90 | 190 | 90 | 0.57 |
| Jo | pg/ml | 3.5E3 | 3.9E3 | 4.8E3 | 6.5E3 | 3.9E3 | 1.1E4 | 2.0E1 | 2.3E2 | 2.0E4 | 1.0E5 | 360 | 90 | 190 | 90 | 0.54 |
| Jp | pg/ml | 6.3E4 | 8.1E4 | 6.6E4 | 7.9E4 | 3.7E4 | 3.4E4 | 5.8E2 | 3.1E3 | 3.0E5 | 2.1E5 | 360 | 90 | 190 | 90 | 0.64 |
| Jq | pg/ml | 9.1E1 | 1.2E2 | 1.4E2 | 3.3E2 | 1.8E2 | 9.9E2 | 1.0E0 | 7.4E0 | 2.0E3 | 8.7E3 | 360 | 90 | 190 | 90 | 0.58 |
| Jr | pg/ml | 3.3E0 | 6.7E0 | 4.5E1 | 1.6E2 | 5.6E2 | 9.4E2 | 1.0E-9 | 1.0E-9 | 1.1E4 | 7.4E3 | 360 | 90 | 190 | 90 | 0.58 |
| Js | pg/ml | 1.2E1 | 1.4E1 | 6.5E1 | 9.5E1 | 5.4E2 | 4.4E2 | 1.0E-9 | 4.5E-1 | 1.0E4 | 3.0E3 | 360 | 90 | 190 | 90 | 0.55 |

Figure 4 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jt | pg/ml | 2.2E3 | 2.9E3 | 2.8E3 | 4.3E3 | 2.2E3 | 6.1E3 | 2.2E1 | 1.9E2 | 2.2E4 | 5.2E4 | 360 | 90 | 190 | 90 | 0.60 |
| Xa | pg/ml | 1.0E-9 | 8.7E0 | 7.0E0 | 8.2E1 | 1.5E1 | 2.8E2 | 1.0E-9 | 7.6E1 | 6.9E1 | 1.2E3 | 55 | 19 | 44 | 19 | 0.69 |
| Ye | pg/ml | 1.0E-9 | 1.0E-9 | 3.9E0 | 7.7E0 | 1.3E1 | 1.6E1 | 1.0E-9 | 1.0E-9 | 6.9E1 | 6.1E1 | 55 | 19 | 44 | 19 | 0.56 |
| Tm | pg/ml | 1.0E-9 | 1.0E-9 | 2.4E0 | 3.5E0 | 4.8E0 | 6.3E0 | 1.0E-9 | 1.0E-9 | 1.8E1 | 2.5E1 | 55 | 19 | 44 | 19 | 0.54 |
| Tl | pg/ml | 1.1E-1 | 4.7E-1 | 2.3E-1 | 1.6E0 | 3.6E-1 | 5.6E0 | 1.0E-9 | 1.0E-9 | 1.8E0 | 2.5E1 | 55 | 19 | 44 | 19 | 0.63 |
| Ju | mIU/ml | 7.2E0 | 1.0E1 | 2.0E1 | 1.5E1 | 3.4E1 | 1.9E1 | 6.5E-2 | 1.9E-1 | 2.3E2 | 9.3E1 | 122 | 51 | 99 | 51 | 0.55 |
| Jv | mIU/ml | 9.3E0 | 1.5E1 | 3.1E1 | 3.1E1 | 6.1E1 | 4.7E1 | 1.0E-2 | 2.4E-2 | 4.4E2 | 2.2E2 | 122 | 51 | 99 | 51 | 0.55 |
| Jy | ng/ml | 1.7E-3 | 1.6E-3 | 2.3E-3 | 2.8E-3 | 4.7E-3 | 5.7E-3 | 1.0E-9 | 4.5E-4 | 5.2E-2 | 4.1E-2 | 122 | 51 | 99 | 51 | 0.51 |
| Kc | pg/ml | 2.1E1 | 3.4E1 | 3.9E1 | 5.4E1 | 4.4E1 | 5.0E1 | 1.0E-9 | 1.0E-9 | 1.7E2 | 1.8E2 | 121 | 53 | 98 | 53 | 0.64 |
| Kd | pg/ml | 1.0E-9 | 1.0E-9 | 1.9E2 | 9.6E2 | 6.7E2 | 5.3E3 | 1.0E-9 | 1.0E-9 | 4.8E3 | 3.8E4 | 121 | 53 | 98 | 53 | 0.52 |
| Ke | pg/ml | 9.5E3 | 1.4E4 | 1.3E4 | 2.5E4 | 9.6E3 | 4.6E4 | 3.4E2 | 6.7E2 | 5.9E4 | 3.2E5 | 121 | 53 | 98 | 53 | 0.63 |
| Kf | pg/mL | 5.5E0 | 8.9E0 | 6.3E0 | 1.0E1 | 5.7E0 | 1.1E1 | 1.0E-9 | 1.0E-9 | 2.6E1 | 7.8E1 | 121 | 53 | 98 | 53 | 0.64 |
| Kg | pg/mL | 9.9E2 | 1.4E3 | 1.7E3 | 2.7E3 | 2.4E3 | 4.5E3 | 7.7E1 | 1.3E2 | 2.2E4 | 2.7E4 | 121 | 53 | 98 | 53 | 0.57 |
| Ki | pg/ml | 6.5E1 | 4.9E1 | 7.2E1 | 6.1E1 | 5.2E1 | 4.5E1 | 1.0E-9 | 1.0E-9 | 2.9E2 | 2.1E2 | 121 | 53 | 98 | 53 | 0.41 |
| Kj | pg/ml | 9.3E2 | 1.3E3 | 1.5E3 | 2.0E3 | 1.6E3 | 2.5E3 | 6.6E1 | 1.2E2 | 1.0E4 | 1.5E4 | 121 | 53 | 98 | 53 | 0.56 |
| Kk | pg/ml | 6.8E0 | 7.8E0 | 1.2E1 | 1.4E1 | 1.8E1 | 1.6E1 | 1.0E-9 | 1.0E-9 | 1.6E2 | 6.1E1 | 121 | 53 | 98 | 53 | 0.54 |
| Kl | pg/ml | 1.7E4 | 2.8E4 | 2.4E4 | 3.2E4 | 2.3E4 | 2.7E4 | 3.5E2 | 2.4E2 | 1.1E5 | 1.3E5 | 121 | 53 | 98 | 53 | 0.60 |
| Kn | pg/ml | 1.5E1 | 3.0E1 | 5.4E1 | 1.6E2 | 1.1E2 | 6.7E2 | 1.0E-9 | 1.0E-9 | 7.3E2 | 4.9E3 | 121 | 53 | 98 | 53 | 0.61 |
| Ko | pg/ml | 3.0E2 | 5.0E2 | 3.9E2 | 7.4E2 | 4.0E2 | 8.2E2 | 1.0E-9 | 1.0E-9 | 1.8E3 | 4.1E3 | 121 | 53 | 98 | 53 | 0.65 |
| Kp | pg/ml | 2.7E2 | 3.5E2 | 3.2E2 | 6.4E2 | 2.9E2 | 1.8E3 | 1.0E-9 | 1.0E-9 | 1.7E3 | 1.3E4 | 121 | 53 | 98 | 53 | 0.61 |
| Kq | pg/ml | 2.8E2 | 4.7E2 | 4.2E2 | 3.7E3 | 9.3E2 | 2.2E4 | 5.1E0 | 1.6E0 | 9.8E3 | 1.6E5 | 117 | 53 | 95 | 53 | 0.67 |
| Kr | pg/ml | 3.6E-1 | 2.9E-1 | 2.4E0 | 1.0E1 | 4.8E0 | 5.7E1 | 1.0E-9 | 1.0E-9 | 3.5E1 | 4.2E2 | 117 | 53 | 95 | 53 | 0.52 |
| Ks | pg/ml | 1.5E4 | 1.7E4 | 2.0E4 | 2.0E4 | 1.9E4 | 1.7E4 | 3.8E2 | 5.1E1 | 1.1E5 | 6.3E4 | 117 | 53 | 95 | 53 | 0.50 |
| Ps | ng/ml | 1.4E2 | 2.9E2 | 5.2E2 | 6.6E2 | 1.6E3 | 9.2E2 | 1.6E0 | 5.5E0 | 9.0E3 | 3.8E3 | 53 | 19 | 41 | 19 | 0.68 |
| Kx | ng/ml | 1.0E-9 | 3.3E-3 | 4.4E-3 | 9.9E-3 | 8.5E-3 | 1.8E-2 | 1.0E-9 | 1.0E-9 | 5.1E-2 | 9.5E-2 | 120 | 53 | 98 | 53 | 0.60 |
| Ky | ng/ml | 7.7E-2 | 1.8E-1 | 3.2E-1 | 4.3E-1 | 6.9E-1 | 7.1E-1 | 1.0E-9 | 1.0E-9 | 5.1E0 | 3.7E0 | 120 | 53 | 98 | 53 | 0.61 |
| Kz | ng/ml | 1.0E-9 | 1.0E-9 | 4.7E-3 | 4.1E-3 | 6.8E-3 | 5.8E-3 | 1.0E-9 | 1.0E-9 | 3.6E-2 | 1.8E-2 | 120 | 53 | 98 | 53 | 0.50 |
| Rz | ng/ml | 1.4E-1 | 3.3E-1 | 8.8E-1 | 1.1E0 | 1.5E0 | 1.9E0 | 3.6E-3 | 4.6E-3 | 6.7E0 | 6.5E0 | 53 | 19 | 42 | 19 | 0.61 |
| Ry | ng/ml | 1.6E-2 | 2.7E-2 | 1.9E-2 | 4.5E-2 | 1.8E-2 | 7.9E-2 | 1.0E-9 | 1.0E-9 | 1.0E-1 | 3.5E-1 | 53 | 19 | 42 | 19 | 0.60 |
| Rx | ng/ml | 3.5E-5 | 1.0E-9 | 2.1E-3 | 8.9E-4 | 3.8E-3 | 1.8E-3 | 1.0E-9 | 1.0E-9 | 2.0E-2 | 6.1E-3 | 53 | 19 | 42 | 19 | 0.41 |
| Ld | pg/ml | 1.0E-9 | 7.5E-1 | 3.6E0 | 3.5E0 | 9.5E0 | 5.6E0 | 1.0E-9 | 1.0E-9 | 6.9E1 | 2.3E1 | 119 | 53 | 97 | 53 | 0.56 |
| Lh | pg/ml | 1.0E4 | 1.6E4 | 1.8E4 | 3.3E4 | 2.6E4 | 5.9E4 | 1.0E-9 | 1.0E-9 | 2.6E5 | 4.1E5 | 359 | 90 | 190 | 90 | 0.62 |
| Li | pg/ml | 2.5E3 | 5.0E3 | 1.3E4 | 2.3E4 | 7.2E4 | 5.1E4 | 1.0E-9 | 1.3E1 | 1.3E6 | 3.1E5 | 359 | 90 | 190 | 90 | 0.62 |
| Lj | pg/ml | 1.7E3 | 4.5E3 | 1.4E4 | 2.3E4 | 5.1E4 | 6.1E4 | 1.0E-9 | 3.4E1 | 4.4E5 | 3.9E5 | 359 | 90 | 190 | 90 | 0.59 |
| Lp | pg/ml | 9.4E0 | 1.4E1 | 5.6E1 | 1.6E2 | 1.6E2 | 2.8E2 | 1.0E-9 | 1.0E-9 | 1.1E3 | 1.0E3 | 53 | 19 | 42 | 19 | 0.53 |
| Lt | pg/ml | 1.0E-9 | 1.0E-9 | 2.6E0 | 1.0E-9 | 9.6E0 | 0.0E0 | 1.0E-9 | 1.0E-9 | 6.0E1 | 1.0E-9 | 53 | 19 | 42 | 19 | 0.45 |
| Rv | ng/ml | 2.2E-4 | 1.1E-3 | 1.1E-3 | 2.6E-3 | 1.8E-3 | 4.4E-3 | 1.0E-9 | 1.0E-9 | 9.2E-3 | 1.6E-2 | 53 | 19 | 41 | 19 | 0.62 |
| Ru | ng/ml | 1.0E-9 | 1.0E-9 | 8.1E-3 | 3.7E-2 | 4.5E-2 | 1.1E-1 | 1.0E-9 | 1.0E-9 | 3.1E-1 | 3.6E-1 | 53 | 19 | 41 | 19 | 0.54 |
| Rt | ng/ml | 6.2E-2 | 1.0E-1 | 9.3E-2 | 5.3E-1 | 1.1E-1 | 1.7E0 | 1.6E-3 | 2.2E-3 | 4.5E-1 | 7.4E0 | 53 | 19 | 41 | 19 | 0.63 |
| Yl | pg/ml | 1.4E1 | 1.3E1 | 1.9E1 | 3.0E1 | 1.7E1 | 4.9E1 | 1.0E-9 | 2.1E0 | 6.5E1 | 2.2E2 | 55 | 19 | 44 | 19 | 0.53 |
| Rm | ng/ml | 1.6E1 | 2.5E1 | 5.2E1 | 5.4E1 | 8.3E1 | 6.8E1 | 2.2E-1 | 3.9E-1 | 4.0E2 | 3.2E2 | 121 | 49 | 97 | 49 | 0.56 |
| Rh | ng/ml | 1.3E2 | 1.7E2 | 4.7E2 | 2.8E2 | 1.6E3 | 4.6E2 | 4.7E0 | 7.6E0 | 1.7E4 | 3.0E3 | 121 | 49 | 97 | 49 | 0.53 |
| Ri | ng/ml | 1.0E-9 | 1.0E-9 | 4.3E0 | 2.8E0 | 1.0E1 | 7.7E0 | 1.0E-9 | 1.0E-9 | 7.4E1 | 4.5E1 | 122 | 49 | 98 | 49 | 0.45 |
| Rg | ng/ml | 1.0E-9 | 1.0E-9 | 3.2E-2 | 9.8E-2 | 2.6E-1 | 4.4E-1 | 1.0E-9 | 1.0E-9 | 2.7E0 | 3.0E0 | 121 | 49 | 97 | 49 | 0.54 |
| Rj | ng/ml | 1.0E-9 | 1.0E-9 | 1.8E0 | 6.3E0 | 7.6E0 | 3.8E1 | 1.0E-9 | 1.0E-9 | 8.0E1 | 2.7E2 | 122 | 49 | 98 | 49 | 0.50 |
| Rf | ng/ml | 3.4E-1 | 3.9E-1 | 8.0E-1 | 9.6E-1 | 1.5E0 | 2.0E0 | 7.8E-3 | 3.5E-2 | 1.4E1 | 1.4E1 | 121 | 49 | 97 | 49 | 0.54 |
| Ql | pg/ml | 5.0E0 | 4.5E0 | 1.1E1 | 1.5E1 | 1.7E1 | 3.2E1 | 1.0E-9 | 1.0E-9 | 1.2E2 | 1.8E2 | 122 | 51 | 99 | 51 | 0.47 |
| Qm | pg/ml | 1.7E0 | 1.5E1 | 2.0E1 | 2.7E1 | 4.4E1 | 3.3E1 | 1.0E-9 | 1.0E-9 | 3.6E2 | 1.3E2 | 122 | 51 | 99 | 51 | 0.62 |
| Qn | pg/ml | 6.1E-1 | 1.0E0 | 7.2E0 | 1.0E1 | 2.4E1 | 2.9E1 | 1.0E-9 | 1.0E-9 | 2.2E2 | 2.0E2 | 122 | 51 | 99 | 51 | 0.52 |
| Nv | pg/ml | 3.0E3 | 4.7E3 | 1.1E4 | 1.4E4 | 5.8E4 | 2.5E4 | 1.0E-9 | 1.9E1 | 1.1E6 | 1.6E5 | 362 | 92 | 190 | 92 | 0.61 |
| Nw | pg/ml | 7.1E3 | 1.2E4 | 1.2E4 | 1.9E4 | 2.1E4 | 3.2E4 | 8.6E1 | 1.9E2 | 2.1E5 | 2.2E5 | 362 | 92 | 190 | 92 | 0.66 |
| Nx | pg/ml | 1.2E2 | 2.3E2 | 3.6E2 | 5.3E2 | 6.8E2 | 7.5E2 | 1.0E-9 | 1.0E-9 | 7.4E3 | 4.1E3 | 362 | 92 | 190 | 92 | 0.62 |
| Ny | pg/ml | 5.2E0 | 1.0E1 | 9.8E1 | 7.9E1 | 1.3E3 | 3.2E2 | 1.0E-9 | 1.0E-9 | 2.5E4 | 2.8E3 | 362 | 92 | 190 | 92 | 0.59 |
| Oa | pg/ml | 1.6E2 | 2.5E2 | 4.0E2 | 4.9E2 | 7.6E2 | 6.2E2 | 1.0E-9 | 1.0E-9 | 4.8E3 | 2.4E3 | 122 | 51 | 99 | 51 | 0.57 |
| Op | pg/ml | 4.1E5 | 4.5E5 | 3.9E5 | 4.3E5 | 1.6E5 | 1.6E5 | 3.3E4 | 9.4E4 | 7.3E5 | 6.8E5 | 53 | 19 | 42 | 19 | 0.58 |
| Wn | ng/ml | 1.2E1 | 1.4E1 | 9.2E1 | 1.8E2 | 3.0E2 | 6.0E2 | 2.2E0 | 1.5E0 | 1.8E3 | 2.4E3 | 35 | 15 | 29 | 15 | 0.52 |
| Tk | ng/ml | 1.3E2 | 9.5E1 | 3.8E2 | 2.7E2 | 7.3E2 | 4.5E2 | 1.9E1 | 1.0E1 | 4.2E3 | 1.4E3 | 37 | 17 | 30 | 17 | 0.42 |

Figure 4 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oe | pg/ml | 1.1E1 | 5.6E1 | 2.3E2 | 2.8E2 | 3.7E2 | 4.8E2 | 1.0E-9 | 1.0E-9 | 2.7E3 | 2.3E3 | 357 | 92 | 190 | 92 | 0.52 |
| Of | pg/ml | 1.6E2 | 1.9E2 | 4.0E3 | 8.8E3 | 1.5E4 | 2.5E4 | 1.0E-9 | 1.0E-9 | 1.8E5 | 1.7E5 | 360 | 92 | 190 | 92 | 0.51 |
| Og | pg/ml | 8.4E-2 | 7.0E-2 | 5.8E-1 | 2.8E-1 | 1.9E0 | 6.4E-1 | 1.0E-9 | 1.0E-9 | 2.0E1 | 3.5E0 | 360 | 92 | 190 | 92 | 0.44 |
| Oh | pg/ml | 1.9E0 | 3.6E0 | 2.2E1 | 2.3E1 | 1.2E2 | 1.2E2 | 1.0E-9 | 1.0E-9 | 1.4E3 | 1.1E3 | 360 | 92 | 190 | 92 | 0.63 |
| Oi | pg/ml | 2.0E0 | 2.9E0 | 6.3E0 | 6.8E0 | 1.1E1 | 8.8E0 | 1.0E-9 | 1.0E-9 | 8.6E1 | 4.8E1 | 360 | 92 | 190 | 92 | 0.54 |
| Ok | pg/ml | 2.9E2 | 5.6E2 | 3.9E2 | 8.9E2 | 3.7E2 | 1.2E3 | 1.3E1 | 1.5E1 | 2.8E3 | 7.8E3 | 360 | 92 | 190 | 92 | 0.68 |
| Om | pg/ml | 3.6E2 | 5.6E2 | 7.4E2 | 1.8E3 | 2.0E3 | 5.7E3 | 1.0E-9 | 1.0E-9 | 3.0E4 | 5.1E4 | 360 | 92 | 190 | 92 | 0.61 |
| On | pg/ml | 1.3E2 | 2.6E2 | 2.5E2 | 5.1E2 | 4.5E2 | 1.0E3 | 1.0E-9 | 7.6E0 | 4.5E3 | 8.5E3 | 360 | 92 | 190 | 92 | 0.64 |
| Or | pg/ml | 1.0E1 | 2.1E1 | 2.9E1 | 4.3E1 | 6.1E1 | 8.3E1 | 1.0E-9 | 1.0E-9 | 5.0E2 | 5.1E2 | 120 | 54 | 98 | 54 | 0.54 |
| Ow | pg/ml | 2.7E1 | 5.3E1 | 9.9E1 | 1.9E2 | 2.9E2 | 6.4E2 | 1.0E-9 | 1.0E-9 | 2.3E3 | 4.7E3 | 120 | 54 | 98 | 54 | 0.62 |
| Ou | pg/ml | 5.0E2 | 6.0E2 | 8.2E2 | 1.3E3 | 1.2E3 | 1.9E3 | 3.5E1 | 1.0E-9 | 9.4E3 | 8.8E3 | 120 | 54 | 98 | 54 | 0.58 |
| Ul | ng/ml | 1.0E-9 | 1.0E-9 | 1.2E0 | 2.2E0 | 4.3E0 | 9.2E0 | 1.0E-9 | 1.0E-9 | 2.9E1 | 5.6E1 | 131 | 50 | 102 | 50 | 0.50 |
| Uo | ng/ml | 1.0E-9 | 1.0E-9 | 1.0E-1 | 7.1E-2 | 2.3E-1 | 1.7E-1 | 1.0E-9 | 1.0E-9 | 1.3E0 | 6.8E-1 | 131 | 50 | 102 | 50 | 0.48 |
| Uk | ng/ml | 1.0E-9 | 1.0E-9 | 4.7E-3 | 7.9E-3 | 1.1E-2 | 2.3E-2 | 1.0E-9 | 1.0E-9 | 9.9E-2 | 1.4E-1 | 131 | 50 | 102 | 50 | 0.46 |
| Um | ng/ml | 1.0E-9 | 1.0E-9 | 4.0E-1 | 3.9E-1 | 9.8E-1 | 7.6E-1 | 1.0E-9 | 1.0E-9 | 6.8E0 | 2.7E0 | 131 | 50 | 102 | 50 | 0.50 |
| Uf | ng/ml | 4.1E-2 | 1.0E-1 | 1.0E-1 | 3.3E-1 | 1.4E-1 | 8.4E-1 | 2.7E-3 | 1.0E-3 | 7.0E-1 | 5.6E0 | 131 | 50 | 102 | 50 | 0.66 |
| Uh | ng/ml | 1.6E0 | 2.9E0 | 2.7E0 | 3.9E0 | 2.7E0 | 4.0E0 | 3.2E-2 | 4.7E-2 | 1.5E1 | 1.7E1 | 131 | 50 | 102 | 50 | 0.60 |
| Un | ng/ml | 1.7E0 | 2.3E0 | 2.0E0 | 3.0E0 | 1.3E0 | 3.5E0 | 2.0E-1 | 3.4E-1 | 7.0E0 | 2.5E1 | 131 | 50 | 102 | 50 | 0.64 |
| Ug | ng/ml | 1.5E1 | 1.2E1 | 2.7E1 | 2.8E1 | 2.7E1 | 3.7E1 | 6.9E-1 | 8.8E-1 | 1.3E2 | 1.6E2 | 131 | 50 | 102 | 50 | 0.44 |
| Ur | ng/ml | 1.7E-1 | 9.6E-2 | 1.2E0 | 6.6E-1 | 8.2E0 | 1.5E0 | 1.0E-9 | 1.0E-9 | 9.3E1 | 7.3E0 | 131 | 50 | 102 | 50 | 0.44 |
| Up | ng/ml | 1.0E-9 | 1.0E-9 | 6.9E-3 | 5.0E-2 | 3.2E-2 | 3.4E-1 | 1.0E-9 | 1.0E-9 | 3.3E-1 | 2.4E0 | 131 | 50 | 102 | 50 | 0.50 |
| Us | ng/ml | 2.6E-3 | 1.8E-3 | 2.0E-2 | 4.6E-2 | 5.4E-2 | 2.3E-1 | 1.0E-9 | 1.0E-9 | 4.0E-1 | 1.7E0 | 131 | 50 | 102 | 50 | 0.48 |
| Uv | ng/ml | 3.5E-3 | 2.7E-3 | 1.3E-2 | 1.4E-2 | 4.0E-2 | 5.8E-2 | 1.0E-9 | 1.0E-9 | 3.5E-1 | 4.1E-1 | 131 | 50 | 102 | 50 | 0.46 |
| Ut | ng/ml | 5.0E-1 | 1.2E0 | 2.3E0 | 5.0E0 | 8.5E0 | 1.2E1 | 1.0E-9 | 1.0E-9 | 7.2E1 | 6.5E1 | 131 | 50 | 102 | 50 | 0.63 |
| Uu | ng/ml | 6.3E0 | 7.9E0 | 7.3E0 | 9.0E0 | 4.7E0 | 7.1E0 | 8.1E-1 | 1.0E0 | 2.4E1 | 4.0E1 | 131 | 50 | 102 | 50 | 0.57 |
| Uw | ng/ml | 2.0E0 | 2.2E0 | 3.1E0 | 5.0E0 | 5.0E0 | 8.7E0 | 1.0E-9 | 1.0E-9 | 3.7E1 | 3.9E1 | 62 | 19 | 50 | 19 | 0.59 |
| Vb | ng/ml | 1.1E0 | 1.1E0 | 1.1E0 | 1.2E0 | 4.3E-1 | 1.3E0 | 2.5E-1 | 8.5E-2 | 2.5E0 | 6.4E0 | 62 | 19 | 50 | 19 | 0.47 |
| Vc | ng/ml | 1.0E-9 | 1.0E-9 | 1.4E-2 | 1.0E-9 | 8.4E-2 | 0.0E0 | 1.0E-9 | 1.0E-9 | 6.5E-1 | 1.0E-9 | 62 | 19 | 50 | 19 | 0.47 |
| Uy | ng/ml | 1.3E0 | 1.0E0 | 4.1E0 | 5.5E0 | 9.0E0 | 1.3E1 | 5.3E-2 | 9.0E-2 | 5.1E1 | 4.6E1 | 62 | 19 | 50 | 19 | 0.47 |
| Uz | ng/ml | 1.0E-9 | 1.0E-9 | 7.1E-3 | 1.7E0 | 5.5E-2 | 7.6E0 | 1.0E-9 | 1.0E-9 | 4.4E-1 | 3.3E1 | 62 | 19 | 50 | 19 | 0.51 |
| Ux | ng/ml | 1.2E2 | 1.7E2 | 1.7E2 | 2.0E2 | 1.4E2 | 1.2E2 | 5.8E0 | 4.5E1 | 4.8E2 | 4.7E2 | 62 | 19 | 50 | 19 | 0.58 |
| Va | ng/ml | 1.8E1 | 2.6E1 | 2.5E1 | 2.9E1 | 2.6E1 | 2.4E1 | 1.2E-1 | 3.6E-1 | 1.2E2 | 7.8E1 | 62 | 19 | 50 | 19 | 0.56 |
| Vh | ng/ml | 5.2E-3 | 1.7E-2 | 1.3E-2 | 7.1E-2 | 1.8E-2 | 1.9E-1 | 1.0E-9 | 2.2E-3 | 1.2E-1 | 8.6E-1 | 62 | 19 | 50 | 19 | 0.73 |
| Vi | ng/ml | 2.5E-3 | 5.3E-3 | 2.3E-1 | 1.1E-1 | 1.7E0 | 4.2E-1 | 1.0E-9 | 2.8E-4 | 1.4E1 | 1.8E0 | 62 | 19 | 50 | 19 | 0.63 |
| Vj | ng/ml | 1.9E1 | 5.7E1 | 1.6E2 | 1.1E2 | 6.8E2 | 1.5E2 | 3.2E0 | 1.4E0 | 5.2E3 | 6.5E2 | 62 | 19 | 50 | 19 | 0.68 |
| Vp | ng/ml | 1.0E-9 | 1.0E-9 | 6.8E-1 | 1.0E0 | 5.0E0 | 6.9E0 | 1.0E-9 | 1.0E-9 | 5.0E1 | 4.9E1 | 131 | 50 | 102 | 50 | 0.50 |
| Vt | ng/ml | 6.1E0 | 6.7E0 | 8.2E0 | 1.3E1 | 6.9E0 | 2.4E1 | 6.0E-1 | 4.3E-1 | 3.2E1 | 1.6E2 | 131 | 50 | 102 | 50 | 0.55 |
| Vu | ng/ml | 1.0E-9 | 1.0E-9 | 1.9E0 | 2.3E0 | 5.4E0 | 4.5E0 | 1.0E-9 | 1.0E-9 | 5.1E1 | 2.4E1 | 130 | 48 | 102 | 48 | 0.55 |
| Vq | ng/ml | 1.5E2 | 2.4E2 | 7.5E3 | 4.2E2 | 6.7E4 | 4.7E2 | 2.0E-1 | 3.6E0 | 6.8E5 | 1.5E3 | 102 | 36 | 82 | 36 | 0.53 |
| Vo | ng/ml | 2.6E1 | 2.5E1 | 2.5E1 | 2.5E1 | 4.3E0 | 5.6E0 | 1.1E1 | 4.7E0 | 3.5E1 | 3.5E1 | 131 | 50 | 102 | 50 | 0.48 |
| Vs | ng/ml | 1.0E-9 | 1.0E-9 | 6.0E0 | 1.5E1 | 2.6E1 | 6.7E1 | 1.0E-9 | 1.0E-9 | 2.3E2 | 4.5E2 | 127 | 46 | 99 | 46 | 0.54 |
| Vv | ng/ml | 2.2E0 | 4.7E0 | 5.7E0 | 7.1E0 | 1.0E1 | 8.2E0 | 1.0E-9 | 1.0E-9 | 8.1E1 | 3.5E1 | 130 | 49 | 102 | 49 | 0.60 |
| Vw | ng/ml | 3.4E1 | 3.9E1 | 3.3E1 | 3.8E1 | 1.7E1 | 1.6E1 | 3.1E0 | 3.1E0 | 6.7E1 | 6.4E1 | 62 | 19 | 50 | 19 | 0.58 |
| Oy | pg/ml | 5.4E-1 | 8.7E-1 | 7.9E0 | 4.5E0 | 3.9E1 | 1.0E1 | 1.0E-9 | 1.0E-9 | 4.0E2 | 6.5E1 | 360 | 92 | 190 | 92 | 0.55 |
| Oz | pg/ml | 1.4E-3 | 1.6E-1 | 2.3E-1 | 6.1E-1 | 3.8E-1 | 2.9E0 | 1.0E-9 | 1.0E-9 | 2.6E0 | 2.8E1 | 360 | 92 | 190 | 92 | 0.57 |
| Pa | pg/ml | 3.3E-1 | 4.4E-1 | 1.3E0 | 3.6E0 | 5.6E0 | 2.4E1 | 1.0E-9 | 1.0E-9 | 8.6E1 | 2.3E2 | 360 | 92 | 190 | 92 | 0.59 |
| Pb | pg/ml | 1.0E-9 | 1.0E-9 | 1.6E0 | 7.6E-1 | 2.6E1 | 4.4E0 | 1.0E-9 | 1.0E-9 | 4.9E2 | 3.2E1 | 360 | 92 | 190 | 92 | 0.52 |
| Pc | pg/ml | 2.4E-2 | 2.4E-1 | 4.2E-1 | 8.4E-1 | 1.2E0 | 3.9E0 | 1.0E-9 | 1.0E-9 | 1.6E1 | 3.8E1 | 360 | 92 | 190 | 92 | 0.56 |
| Pd | pg/ml | 1.7E0 | 2.9E0 | 3.7E0 | 6.9E0 | 8.5E0 | 1.5E1 | 1.0E-9 | 1.0E-9 | 9.4E1 | 1.2E2 | 360 | 92 | 190 | 92 | 0.60 |
| Pe | pg/ml | 1.7E1 | 3.1E1 | 8.8E1 | 3.5E2 | 3.4E2 | 1.7E3 | 1.0E-9 | 1.0E-9 | 4.7E3 | 1.5E4 | 360 | 92 | 190 | 92 | 0.59 |
| Pf | pg/ml | 1.2E0 | 2.8E0 | 8.1E0 | 1.7E1 | 3.9E1 | 5.3E1 | 1.0E-9 | 1.0E-9 | 4.8E2 | 4.3E2 | 360 | 92 | 190 | 92 | 0.61 |
| Pg | pg/ml | 2.9E0 | 4.5E0 | 3.5E1 | 4.7E1 | 1.9E2 | 1.6E2 | 1.0E-9 | 1.0E-9 | 3.2E3 | 1.2E3 | 360 | 92 | 190 | 92 | 0.57 |
| Ph | ng/ml | 1.5E-1 | 2.4E-1 | 2.6E-1 | 4.5E-1 | 3.0E-1 | 8.1E-1 | 1.0E-9 | 1.0E-9 | 1.6E0 | 5.4E0 | 120 | 54 | 98 | 54 | 0.56 |
| Pi | ng/ml | 2.0E-1 | 2.4E-1 | 2.7E-1 | 1.8E0 | 4.1E-1 | 1.1E1 | 1.0E-9 | 1.0E-9 | 3.2E0 | 8.2E1 | 120 | 54 | 98 | 54 | 0.57 |
| Pj | ng/mL | 4.5E0 | 6.2E0 | 5.1E0 | 8.1E0 | 3.3E0 | 8.4E0 | 3.8E-2 | 4.0E-1 | 1.6E1 | 5.5E1 | 120 | 54 | 98 | 54 | 0.63 |
| Pk | ng/ml | 8.1E-3 | 1.1E-2 | 1.2E-2 | 4.8E-2 | 1.2E-2 | 2.1E-1 | 1.0E-9 | 1.0E-9 | 5.9E-2 | 1.5E0 | 120 | 54 | 98 | 54 | 0.58 |
| aA | mg/dL | 8.0E-1 | 9.9E-1 | 9.1E-1 | 1.2E0 | 4.4E-1 | 8.4E-1 | 3.0E-1 | 3.0E-1 | 4.1E0 | 4.7E0 | 1529 | 119 | 315 | 119 | 0.59 |

Figure 4 Continued

| Code | Units | Median | | Average | | Standard Deviation | | Minimum | | Maximum | | Number of Samples | | Number of Patients | | AUC |
|------|-------|--------|------|---------|------|--------|------|---------|------|---------|------|--------|------|--------|------|------|
| | | NonDis | Dis | NonDis | Dis | NonDis | Dis | NonDis | Dis | NonDis | Dis | NonDis | Dis | NonDis | Dis | |
| aC | mg/mL | 3.2E0 | 2.2E0 | 3.4E0 | 2.4E0 | 1.5E0 | 9.7E-1 | 1.1E0 | 8.5E-1 | 8.9E0 | 5.6E0 | 262 | 56 | 110 | 56 | 0.29 |
| aD | ug/mL | 3.1E0 | 3.5E0 | 4.5E0 | 5.1E0 | 4.0E0 | 4.4E0 | 4.3E-1 | 7.7E-1 | 3.5E1 | 2.1E1 | 262 | 56 | 110 | 56 | 0.53 |
| aE | mg/mL | 5.8E-1 | 5.5E-1 | 5.8E-1 | 5.8E-1 | 1.4E-1 | 1.5E-1 | 2.1E-1 | 3.4E-1 | 1.1E0 | 1.2E0 | 262 | 56 | 110 | 56 | 0.47 |
| aF | ng/mL | 2.0E0 | 2.2E0 | 4.1E0 | 4.1E0 | 6.5E0 | 4.9E0 | 4.3E-3 | 3.7E-1 | 5.0E1 | 2.4E1 | 262 | 56 | 110 | 56 | 0.52 |
| aG | mg/mL | 1.3E-1 | 1.3E-1 | 1.6E-1 | 1.5E-1 | 9.4E-2 | 7.6E-2 | 1.7E-2 | 5.0E-2 | 5.4E-1 | 3.7E-1 | 262 | 56 | 110 | 56 | 0.48 |
| aH | ug/mL | 7.0E1 | 7.5E1 | 7.8E1 | 8.1E1 | 3.8E1 | 5.1E1 | 4.6E0 | 1.1E1 | 2.7E2 | 2.9E2 | 262 | 56 | 110 | 56 | 0.50 |
| aI | ng/mL | 1.9E2 | 1.7E2 | 1.9E2 | 1.7E2 | 6.0E1 | 5.4E1 | 2.8E1 | 4.7E1 | 3.7E2 | 2.6E2 | 262 | 56 | 110 | 56 | 0.41 |
| aJ | ug/mL | 2.4E0 | 2.4E0 | 2.9E0 | 3.9E0 | 1.9E0 | 3.8E0 | 8.5E-1 | 1.1E0 | 1.2E1 | 2.3E1 | 262 | 56 | 110 | 56 | 0.55 |
| aK | ng/mL | 1.8E0 | 1.2E0 | 2.7E0 | 2.3E0 | 2.8E0 | 3.1E0 | 2.8E-2 | 2.9E-4 | 1.8E1 | 1.8E1 | 262 | 56 | 110 | 56 | 0.41 |
| aL | mg/mL | 8.3E-1 | 7.8E-1 | 8.4E-1 | 7.8E-1 | 2.7E-1 | 2.3E-1 | 1.9E-1 | 2.7E-1 | 1.7E0 | 1.6E0 | 262 | 56 | 110 | 56 | 0.43 |
| aM | U/mL | 1.9E1 | 2.6E1 | 4.2E1 | 5.3E1 | 1.1E2 | 1.1E2 | 4.2E-2 | 4.2E-2 | 1.6E3 | 8.2E2 | 262 | 56 | 110 | 56 | 0.57 |
| aN | U/mL | 9.3E0 | 1.7E1 | 1.4E1 | 2.6E1 | 1.5E1 | 2.8E1 | 2.5E-3 | 2.5E-3 | 9.8E1 | 1.1E2 | 262 | 56 | 110 | 56 | 0.67 |
| aO | pg/mL | 2.9E1 | 5.4E1 | 3.0E2 | 3.7E2 | 8.5E2 | 7.9E2 | 6.0E-2 | 6.0E-2 | 6.6E3 | 3.9E3 | 262 | 56 | 110 | 56 | 0.57 |
| aP | ng/mL | 1.7E0 | 1.7E0 | 2.1E0 | 2.7E0 | 2.1E0 | 3.8E0 | 4.5E-1 | 8.0E-1 | 2.8E1 | 2.8E1 | 262 | 56 | 110 | 56 | 0.54 |
| aQ | ng/mL | 3.2E-1 | 2.9E-1 | 4.9E-1 | 3.6E-1 | 5.0E-1 | 3.7E-1 | 1.9E-2 | 2.0E-4 | 4.0E0 | 2.5E0 | 262 | 56 | 110 | 56 | 0.42 |
| aR | ng/mL | 1.7E0 | 2.4E0 | 2.3E0 | 3.9E0 | 2.3E0 | 5.4E0 | 1.8E-1 | 4.5E-1 | 2.1E1 | 3.4E1 | 262 | 56 | 110 | 56 | 0.62 |
| aS | ng/mL | 2.4E-1 | 3.0E-1 | 6.5E-1 | 6.3E-1 | 2.3E0 | 7.3E-1 | 4.2E-3 | 2.8E-2 | 3.3E1 | 3.1E0 | 262 | 56 | 110 | 56 | 0.59 |
| aU | pg/mL | 8.7E1 | 5.7E1 | 1.4E2 | 9.6E1 | 1.6E2 | 1.2E2 | 7.4E-2 | 7.4E-2 | 1.3E3 | 8.5E2 | 262 | 56 | 110 | 56 | 0.39 |
| aV | ng/mL | 7.0E-1 | 4.9E-1 | 1.1E0 | 9.0E-1 | 1.2E0 | 1.8E0 | 2.2E-2 | 7.6E-4 | 8.7E0 | 1.3E1 | 262 | 56 | 110 | 56 | 0.38 |
| aW | pg/mL | 1.7E1 | 2.3E1 | 1.9E1 | 2.9E1 | 2.4E1 | 5.3E1 | 7.2E-2 | 7.2E-2 | 2.4E2 | 4.2E2 | 262 | 56 | 110 | 56 | 0.66 |
| aX | ng/mL | 1.0E1 | 8.5E0 | 1.6E1 | 1.7E1 | 2.2E1 | 2.6E1 | 3.0E-1 | 6.2E-1 | 2.2E2 | 1.3E2 | 262 | 56 | 110 | 56 | 0.49 |
| aY | pg/mL | 5.3E1 | 6.5E1 | 7.3E1 | 7.7E1 | 7.0E1 | 5.7E1 | 4.1E-1 | 4.1E-1 | 4.4E2 | 3.4E2 | 262 | 56 | 110 | 56 | 0.56 |
| aZ | pg/mL | 2.3E2 | 2.3E2 | 4.4E2 | 5.2E2 | 5.6E2 | 1.2E3 | 1.7E0 | 1.7E0 | 3.4E3 | 8.3E3 | 262 | 56 | 110 | 56 | 0.50 |
| bA | ng/mL | 6.8E0 | 1.2E1 | 2.4E1 | 8.3E1 | 6.9E1 | 2.3E2 | 3.0E-2 | 3.0E-2 | 7.1E2 | 1.5E3 | 262 | 56 | 110 | 56 | 0.65 |
| bB | ng/mL | 3.1E2 | 2.8E2 | 3.4E2 | 2.8E2 | 1.6E2 | 1.6E2 | 2.1E0 | 1.2E1 | 7.4E2 | 7.2E2 | 262 | 56 | 110 | 56 | 0.40 |
| bC | ng/mL | 3.4E2 | 4.0E2 | 5.2E2 | 8.8E2 | 6.0E2 | 1.1E3 | 2.7E1 | 1.3E1 | 4.0E3 | 4.7E3 | 262 | 56 | 110 | 56 | 0.58 |
| bE | mg/mL | 5.8E0 | 5.5E0 | 6.1E0 | 5.6E0 | 2.0E0 | 2.1E0 | 9.8E-1 | 1.3E0 | 1.2E1 | 1.1E1 | 262 | 56 | 110 | 56 | 0.42 |
| bF | pg/mL | 1.9E1 | 3.0E1 | 5.7E1 | 2.5E2 | 2.6E2 | 6.4E2 | 5.0E-2 | 6.1E0 | 3.3E3 | 3.3E3 | 262 | 56 | 110 | 56 | 0.64 |
| bG | ng/mL | 1.7E0 | 2.0E0 | 2.9E0 | 3.0E0 | 3.3E0 | 3.9E0 | 2.2E-2 | 1.1E-1 | 2.3E1 | 2.6E1 | 262 | 56 | 110 | 56 | 0.52 |
| bH | pg/mL | 5.7E-1 | 5.7E-1 | 5.1E0 | 4.5E0 | 1.8E1 | 6.3E0 | 5.7E-1 | 5.7E-1 | 2.8E2 | 2.7E1 | 262 | 56 | 110 | 56 | 0.52 |
| bI | ng/mL | 4.0E-3 | 4.0E-3 | 6.0E-2 | 8.7E-2 | 1.5E-1 | 1.9E-1 | 4.0E-3 | 4.0E-3 | 1.3E0 | 8.8E-1 | 262 | 56 | 110 | 56 | 0.53 |
| bJ | mg/mL | 2.6E0 | 2.1E0 | 3.0E0 | 2.4E0 | 2.2E0 | 1.9E0 | 2.5E-4 | 2.5E-4 | 1.3E1 | 8.5E0 | 262 | 56 | 110 | 56 | 0.43 |
| bL | pg/mL | 4.1E0 | 3.3E0 | 8.5E0 | 8.4E0 | 1.1E1 | 9.4E0 | 4.6E-2 | 4.6E-2 | 8.0E1 | 3.2E1 | 262 | 56 | 110 | 56 | 0.49 |
| bM | mg/mL | 1.5E0 | 2.1E0 | 1.9E0 | 2.5E0 | 1.3E0 | 1.6E0 | 9.2E-3 | 1.8E-2 | 8.8E0 | 8.4E0 | 262 | 56 | 110 | 56 | 0.63 |
| bN | ng/mL | 3.1E1 | 5.9E1 | 1.3E2 | 1.1E2 | 3.1E2 | 1.4E2 | 1.4E-1 | 5.9E-1 | 1.9E3 | 7.5E2 | 262 | 56 | 110 | 56 | 0.57 |
| bO | ng/mL | 4.0E-2 | 4.0E-2 | 1.1E1 | 1.3E1 | 2.4E1 | 2.4E1 | 4.0E-2 | 4.0E-2 | 1.9E2 | 1.2E2 | 262 | 56 | 110 | 56 | 0.49 |
| bP | mg/mL | 6.3E-1 | 5.0E-1 | 8.5E-1 | 7.6E-1 | 7.0E-1 | 7.4E-1 | 4.9E-2 | 9.7E-2 | 3.8E0 | 3.5E0 | 262 | 56 | 110 | 56 | 0.44 |
| bQ | pg/mL | 1.5E1 | 2.1E1 | 2.7E1 | 9.0E1 | 5.0E1 | 3.3E2 | 1.5E-1 | 1.5E-1 | 4.8E2 | 2.4E3 | 262 | 56 | 110 | 56 | 0.60 |
| bR | ng/mL | 1.2E-2 | 1.2E-2 | 1.3E-1 | 6.2E-2 | 2.5E-1 | 1.1E-1 | 1.2E-2 | 1.2E-2 | 3.4E0 | 4.8E-1 | 262 | 56 | 110 | 56 | 0.40 |
| bS | pg/mL | 9.4E-1 | 9.4E-1 | 7.8E0 | 6.7E0 | 2.7E1 | 1.5E1 | 9.4E-1 | 9.4E-1 | 3.4E2 | 6.7E1 | 262 | 56 | 110 | 56 | 0.50 |
| bU | ng/mL | 1.6E-1 | 3.4E-2 | 2.1E-1 | 1.2E-1 | 2.3E-1 | 1.4E-1 | 1.3E-2 | 1.3E-2 | 1.8E0 | 6.2E-1 | 262 | 56 | 110 | 56 | 0.36 |
| bV | pg/mL | 4.7E2 | 5.1E2 | 5.7E2 | 6.3E2 | 7.2E2 | 4.1E2 | 1.6E2 | 2.2E2 | 1.2E4 | 2.0E3 | 262 | 56 | 110 | 56 | 0.54 |
| bW | pg/mL | 3.5E2 | 3.4E2 | 5.2E2 | 1.0E3 | 4.8E2 | 3.3E3 | 1.1E2 | 1.1E2 | 3.4E3 | 2.5E4 | 262 | 56 | 110 | 56 | 0.53 |
| bX | ng/mL | 1.8E-3 | 2.5E-5 | 3.0E-3 | 2.3E-3 | 3.7E-3 | 2.8E-3 | 2.5E-5 | 2.5E-5 | 2.0E-2 | 8.5E-3 | 262 | 56 | 110 | 56 | 0.46 |
| bZ | pg/mL | 2.5E2 | 2.7E2 | 8.0E2 | 1.0E3 | 3.3E3 | 4.1E3 | 1.5E-1 | 3.5E1 | 4.4E4 | 3.1E4 | 262 | 56 | 110 | 56 | 0.52 |
| cA | pg/mL | 6.0E-1 | 6.0E-1 | 2.0E0 | 2.8E0 | 3.5E0 | 5.3E0 | 6.0E-1 | 6.0E-1 | 1.5E1 | 2.2E1 | 262 | 56 | 110 | 56 | 0.52 |
| cB | ng/mL | 6.7E-2 | 3.4E-2 | 9.8E-2 | 4.3E-2 | 1.0E-1 | 4.5E-2 | 1.7E-3 | 1.7E-3 | 5.4E-1 | 2.1E-1 | 262 | 56 | 110 | 56 | 0.32 |
| cC | pg/mL | 4.6E1 | 4.1E1 | 4.9E1 | 4.3E1 | 3.6E1 | 2.7E1 | 1.0E0 | 1.0E0 | 3.7E2 | 9.4E1 | 262 | 56 | 110 | 56 | 0.45 |
| cD | pg/mL | 6.1E0 | 4.5E0 | 1.3E1 | 2.1E1 | 5.9E1 | 5.2E1 | 3.3E-1 | 3.3E-1 | 7.2E2 | 2.9E2 | 262 | 56 | 110 | 56 | 0.44 |
| cE | pg/mL | 3.1E1 | 7.2E1 | 1.1E2 | 2.6E2 | 2.8E2 | 5.5E2 | 1.2E-1 | 1.2E-1 | 3.1E3 | 3.1E3 | 262 | 56 | 110 | 56 | 0.61 |
| cF | pg/mL | 1.4E1 | 5.3E-1 | 2.3E1 | 9.6E0 | 3.2E1 | 2.0E1 | 5.3E-1 | 5.3E-1 | 2.2E2 | 1.3E2 | 262 | 56 | 110 | 56 | 0.34 |
| cG | pg/mL | 4.2E1 | 5.5E1 | 6.7E1 | 1.3E2 | 9.1E1 | 1.9E2 | 9.6E0 | 1.8E1 | 1.1E3 | 1.2E3 | 262 | 56 | 110 | 56 | 0.61 |
| cH | uIU/mL | 2.8E0 | 2.5E0 | 5.6E0 | 5.8E0 | 8.3E0 | 7.3E0 | 8.6E-3 | 8.6E-3 | 8.7E1 | 3.9E1 | 262 | 56 | 110 | 56 | 0.50 |
| cI | ng/mL | 5.5E0 | 4.5E0 | 1.1E1 | 1.2E1 | 1.4E1 | 1.9E1 | 1.0E-3 | 1.0E-3 | 1.0E2 | 1.2E2 | 262 | 56 | 110 | 56 | 0.45 |
| cJ | ug/mL | 7.0E1 | 5.7E1 | 1.2E2 | 9.0E1 | 1.4E2 | 1.1E2 | 4.0E0 | 5.6E0 | 9.6E2 | 6.3E2 | 262 | 56 | 110 | 56 | 0.44 |
| cK | ng/mL | 3.8E-3 | 3.8E-3 | 6.9E-2 | 1.0E-2 | 2.1E-1 | 1.8E-2 | 3.8E-3 | 3.8E-3 | 1.7E0 | 8.2E-2 | 262 | 56 | 110 | 56 | 0.45 |
| cL | pg/mL | 1.9E2 | 2.5E2 | 2.7E2 | 4.1E2 | 4.7E2 | 8.1E2 | 2.5E1 | 3.7E1 | 7.1E3 | 5.9E3 | 262 | 56 | 110 | 56 | 0.56 |

Figure 4 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cM | pg/mL | 2.8E2 | 2.6E2 | 3.1E2 | 2.8E2 | 1.8E2 | 2.0E2 | 2.5E1 | 4.7E1 | 1.2E3 | 1.4E3 | 262 | 56 | 110 | 56 | 0.43 |
| cN | pg/mL | 1.2E2 | 1.2E2 | 1.2E2 | 1.4E2 | 4.2E1 | 5.7E1 | 3.8E1 | 6.5E1 | 3.0E2 | 3.2E2 | 262 | 56 | 110 | 56 | 0.60 |
| cO | pg/mL | 2.3E2 | 2.4E2 | 2.9E2 | 2.9E2 | 2.0E2 | 3.1E2 | 5.4E1 | 9.9E1 | 1.7E3 | 2.4E3 | 262 | 56 | 110 | 56 | 0.48 |
| cP | ng/mL | 2.4E3 | 2.8E3 | 2.5E3 | 2.7E3 | 8.7E2 | 1.0E3 | 6.2E2 | 1.3E3 | 5.7E3 | 5.6E3 | 262 | 56 | 110 | 56 | 0.57 |
| cQ | ng/mL | 3.9E-2 | 5.4E-2 | 1.2E-1 | 1.4E-1 | 2.1E-1 | 3.1E-1 | 2.0E-3 | 2.0E-3 | 1.5E0 | 2.1E0 | 262 | 56 | 110 | 56 | 0.55 |
| cR | ng/mL | 3.2E2 | 3.5E2 | 5.4E2 | 6.2E2 | 8.7E2 | 1.1E3 | 2.3E1 | 2.0E1 | 8.9E3 | 7.7E3 | 262 | 56 | 110 | 56 | 0.51 |
| cS | ng/mL | 2.5E2 | 3.2E2 | 4.2E2 | 5.3E2 | 4.6E2 | 9.4E2 | 4.1E1 | 4.8E1 | 2.7E3 | 7.1E3 | 262 | 56 | 110 | 56 | 0.56 |
| cT | ng/mL | 2.7E1 | 4.0E1 | 6.4E1 | 1.6E2 | 1.3E2 | 3.0E2 | 4.6E0 | 4.4E0 | 1.7E3 | 1.5E3 | 262 | 56 | 110 | 56 | 0.64 |
| cU | ng/mL | 5.6E1 | 4.4E1 | 7.3E1 | 7.2E1 | 6.8E1 | 6.9E1 | 9.2E0 | 1.4E1 | 7.7E2 | 3.5E2 | 262 | 56 | 110 | 56 | 0.47 |
| cV | ng/mL | 1.6E-1 | 2.2E-1 | 4.4E-1 | 5.1E-1 | 2.9E0 | 1.3E0 | 2.5E-2 | 3.4E-2 | 4.7E1 | 8.7E0 | 262 | 56 | 110 | 56 | 0.54 |
| cW | mIU/mL | 5.1E-2 | 6.0E-2 | 2.0E-1 | 8.2E-2 | 9.3E-1 | 7.3E-2 | 3.7E-4 | 1.6E-2 | 9.7E0 | 3.9E-1 | 262 | 56 | 110 | 56 | 0.56 |
| cX | ng/mL | 9.7E-2 | 2.0E-1 | 1.3E0 | 1.4E0 | 4.3E0 | 4.3E0 | 2.3E-4 | 2.3E-4 | 2.8E1 | 2.8E1 | 262 | 56 | 110 | 56 | 0.55 |
| cY | ng/mL | 9.9E0 | 6.8E0 | 1.4E1 | 1.0E1 | 1.3E1 | 1.2E1 | 2.5E-1 | 1.7E-1 | 8.3E1 | 7.5E1 | 262 | 56 | 110 | 56 | 0.39 |
| cZ | ug/mL | 1.5E1 | 1.5E1 | 1.6E1 | 1.5E1 | 7.5E0 | 7.0E0 | 2.3E0 | 2.8E0 | 5.7E1 | 3.4E1 | 262 | 56 | 110 | 56 | 0.49 |
| dA | pg/mL | 3.3E2 | 3.2E2 | 3.6E2 | 3.6E2 | 1.8E2 | 1.8E2 | 9.0E1 | 1.4E2 | 1.3E3 | 1.1E3 | 262 | 56 | 110 | 56 | 0.48 |
| dB | ug/mL | 1.7E1 | 2.1E1 | 1.9E1 | 1.9E1 | 2.0E1 | 9.0E0 | 2.1E0 | 2.2E0 | 2.5E2 | 4.0E1 | 262 | 56 | 110 | 56 | 0.63 |
| dC | nmol/L | 3.5E1 | 3.6E1 | 4.0E1 | 3.8E1 | 1.9E1 | 1.6E1 | 7.9E0 | 1.5E1 | 1.4E2 | 9.2E1 | 262 | 56 | 110 | 56 | 0.49 |
| dD | ug/mL | 3.8E1 | 3.3E1 | 3.9E1 | 3.5E1 | 1.1E1 | 9.7E0 | 1.3E1 | 1.4E1 | 7.6E1 | 5.6E1 | 262 | 56 | 110 | 56 | 0.38 |
| dE | ng/mL | 5.1E-1 | 4.6E-1 | 6.9E-1 | 5.6E-1 | 8.1E-1 | 5.8E-1 | 8.4E-3 | 8.4E-3 | 7.2E0 | 2.4E0 | 262 | 56 | 110 | 56 | 0.46 |
| dF | ng/mL | 2.1E2 | 2.4E2 | 2.6E2 | 3.5E2 | 1.8E2 | 2.4E2 | 7.5E1 | 1.0E2 | 1.2E3 | 1.2E3 | 262 | 56 | 110 | 56 | 0.61 |
| dG | ng/mL | 1.1E1 | 1.2E1 | 1.4E1 | 1.8E1 | 1.0E1 | 1.6E1 | 2.5E0 | 5.5E0 | 8.1E1 | 8.7E1 | 262 | 56 | 110 | 56 | 0.58 |
| dH | pg/mL | 7.5E0 | 8.4E0 | 1.2E1 | 1.6E1 | 2.8E1 | 2.9E1 | 4.0E-2 | 4.0E-2 | 3.1E2 | 2.0E2 | 262 | 56 | 110 | 56 | 0.54 |
| dI | ng/mL | 4.6E-1 | 4.6E-1 | 1.9E0 | 2.3E0 | 4.8E0 | 4.5E0 | 4.6E-1 | 4.6E-1 | 4.2E1 | 2.3E1 | 262 | 56 | 110 | 56 | 0.52 |
| dJ | ng/mL | 1.9E0 | 2.0E0 | 2.2E0 | 2.3E0 | 1.1E0 | 1.6E0 | 3.2E-2 | 3.2E-2 | 5.9E0 | 6.9E0 | 262 | 56 | 110 | 56 | 0.50 |
| dK | uIU/mL | 2.0E0 | 1.5E0 | 2.6E0 | 2.6E0 | 2.6E0 | 3.5E0 | 2.8E-4 | 1.4E-2 | 1.6E1 | 2.2E1 | 262 | 56 | 110 | 56 | 0.48 |
| dL | ng/mL | 8.9E2 | 9.1E2 | 1.0E3 | 1.2E3 | 5.0E2 | 8.1E2 | 3.4E2 | 4.5E2 | 3.4E3 | 4.8E3 | 262 | 56 | 110 | 56 | 0.54 |
| dM | pg/mL | 9.7E2 | 9.1E2 | 1.2E3 | 1.5E3 | 1.0E3 | 1.5E3 | 3.5E2 | 4.1E2 | 1.2E4 | 9.6E3 | 262 | 56 | 110 | 56 | 0.51 |
| dN | ug/mL | 9.0E1 | 1.1E2 | 9.9E1 | 1.2E2 | 3.7E1 | 5.0E1 | 2.5E1 | 4.1E1 | 2.8E2 | 3.3E2 | 262 | 56 | 110 | 56 | 0.63 |
| dR | pg/mL | 1.8E3 | 1.2E3 | 2.5E3 | 2.2E3 | 2.4E3 | 2.6E3 | 1.9E2 | 1.4E2 | 1.5E4 | 9.4E3 | 150 | 51 | 104 | 51 | 0.41 |
| dU | pg/ml | 9.1E3 | 1.7E4 | 1.2E4 | 1.6E4 | 1.1E4 | 1.4E4 | 2.5E3 | 6.9E2 | 5.3E4 | 4.6E4 | 27 | 13 | 26 | 13 | 0.56 |
| dX | ng/ml | 5.2E-2 | 3.4E-2 | 1.1E-1 | 1.6E-1 | 1.5E-1 | 2.6E-1 | 2.6E-3 | 2.6E-3 | 7.4E-1 | 8.1E-1 | 89 | 13 | 31 | 13 | 0.47 |
| dW | ng/ml | 1.7E-1 | 2.7E-1 | 2.1E-1 | 3.3E-1 | 1.5E-1 | 2.7E-1 | 5.0E-2 | 6.8E-2 | 5.8E-1 | 8.0E-1 | 36 | 7 | 7 | 7 | 0.61 |
| eF | ng/ml | 4.0E0 | 4.4E0 | 5.2E0 | 5.6E0 | 5.6E0 | 4.2E0 | 1.2E0 | 2.1E0 | 4.6E1 | 2.9E1 | 158 | 51 | 105 | 51 | 0.60 |
| eC | pg/mL | 3.0E2 | 2.6E2 | 3.7E2 | 3.6E2 | 2.5E2 | 3.5E2 | 9.9E0 | 7.1E1 | 1.4E3 | 2.0E3 | 105 | 51 | 97 | 51 | 0.44 |
| eD | pg/mL | 2.3E2 | 1.7E2 | 7.6E2 | 2.5E2 | 1.5E3 | 2.7E2 | 5.2E-1 | 5.2E-1 | 8.3E3 | 1.5E3 | 81 | 44 | 74 | 44 | 0.38 |
| eO | ng/ml | 5.8E1 | 6.1E1 | 3.8E2 | 1.2E2 | 4.1E2 | 1.1E2 | 2.0E1 | 4.1E1 | 1.2E3 | 3.3E2 | 36 | 7 | 7 | 7 | 0.46 |
| eM | ng/ml | 3.2E0 | 2.2E0 | 4.3E0 | 6.4E0 | 4.2E0 | 9.4E0 | 7.6E-1 | 3.3E-1 | 2.7E1 | 3.9E1 | 110 | 22 | 44 | 22 | 0.46 |
| eP | ng/ml | 3.7E-3 | 5.9E-1 | 8.1E-1 | 2.8E0 | 1.9E0 | 7.5E0 | 3.7E-3 | 3.7E-3 | 1.2E1 | 2.8E1 | 89 | 13 | 31 | 13 | 0.61 |
| eT | ng/ml | 2.8E2 | 3.0E2 | 6.0E2 | 7.0E2 | 6.5E2 | 8.4E2 | 1.0E2 | 7.1E1 | 2.5E3 | 2.9E3 | 55 | 24 | 54 | 24 | 0.52 |
| eQ | pg/ml | 1.0E0 | 1.0E0 | 1.2E2 | 3.6E1 | 3.3E2 | 7.1E1 | 1.0E0 | 1.0E0 | 1.6E3 | 2.2E2 | 27 | 13 | 26 | 13 | 0.47 |
| eW | U/ml | 6.7E-3 | 6.7E-3 | 8.2E-2 | 2.6E-1 | 1.5E-1 | 5.8E-1 | 6.7E-3 | 6.7E-3 | 6.6E-1 | 1.6E0 | 36 | 7 | 7 | 7 | 0.53 |
| fA | ng/ml | 2.0E2 | 1.8E2 | 4.4E2 | 4.0E2 | 4.9E2 | 4.3E2 | 2.6E1 | 4.0E1 | 1.5E3 | 1.4E3 | 27 | 14 | 26 | 14 | 0.51 |
| eZ | ng/ml | 5.4E1 | 5.5E1 | 6.2E1 | 5.8E1 | 2.5E1 | 2.4E1 | 2.3E1 | 1.8E1 | 1.2E2 | 1.2E2 | 55 | 24 | 54 | 24 | 0.47 |
| fB | ng/ml | 6.0E2 | 5.4E2 | 6.8E2 | 5.8E2 | 2.9E2 | 2.2E2 | 1.6E2 | 2.6E2 | 1.3E3 | 1.0E3 | 28 | 14 | 27 | 14 | 0.40 |
| fN | ng/ml | 2.1E-1 | 2.1E-1 | 3.9E0 | 1.7E1 | 9.2E0 | 6.4E1 | 2.1E-1 | 2.1E-1 | 5.4E1 | 3.2E2 | 55 | 24 | 54 | 24 | 0.55 |
| fP | ng/ml | 2.3E2 | 3.6E2 | 2.5E2 | 3.4E2 | 1.4E2 | 1.8E2 | 8.4E0 | 1.8E0 | 1.0E3 | 8.2E2 | 140 | 51 | 100 | 51 | 0.67 |
| fR | ng/ml | 1.2E5 | 1.7E5 | 1.7E5 | 2.9E5 | 1.3E5 | 2.3E5 | 3.1E4 | 1.9E2 | 7.7E5 | 8.7E5 | 202 | 32 | 60 | 32 | 0.64 |
| fY | ng/ml | 2.6E2 | 2.6E2 | 2.5E2 | 2.6E2 | 9.4E1 | 1.0E2 | 6.5E1 | 3.6E1 | 4.7E2 | 4.7E2 | 55 | 24 | 54 | 24 | 0.53 |
| gC | ng/ml | 2.3E2 | 2.0E2 | 2.7E2 | 2.4E2 | 1.4E2 | 1.3E2 | 1.2E2 | 8.3E1 | 1.1E3 | 5.9E2 | 84 | 15 | 49 | 15 | 0.41 |
| gL | pg/ml | 6.3E4 | 6.6E4 | 7.0E4 | 7.5E4 | 3.5E4 | 3.6E4 | 1.4E4 | 2.7E4 | 2.0E5 | 2.2E5 | 150 | 51 | 104 | 51 | 0.56 |
| gP | U/ml | 2.7E2 | 2.8E2 | 2.8E2 | 2.9E2 | 9.5E1 | 1.5E2 | 8.5E1 | 1.2E1 | 8.0E2 | 1.1E3 | 157 | 51 | 105 | 51 | 0.53 |
| gW | ng/ml | 8.5E2 | 5.1E2 | 1.5E3 | 1.0E3 | 1.9E3 | 1.4E3 | 3.7E1 | 3.1E-1 | 9.5E3 | 5.4E3 | 130 | 39 | 96 | 39 | 0.39 |
| gV | ng/ml | 2.1E1 | 1.7E1 | 2.2E1 | 1.9E1 | 7.5E0 | 9.9E0 | 2.9E-3 | 8.1E-2 | 3.9E1 | 3.4E1 | 77 | 10 | 19 | 10 | 0.42 |
| tF | pg/mL | 1.6E3 | 1.1E3 | 2.0E4 | 6.7E3 | 5.4E4 | 1.9E4 | 1.2E1 | 1.8E1 | 3.2E5 | 1.2E5 | 105 | 50 | 97 | 50 | 0.43 |
| gZ | ug/ml | 8.0E-1 | 8.8E-1 | 5.4E1 | 5.4E1 | 1.2E2 | 1.2E2 | 8.7E-2 | 1.1E-1 | 4.1E2 | 4.0E2 | 27 | 13 | 26 | 13 | 0.55 |
| hA | ng/ml | 2.1E0 | 2.2E0 | 7.1E0 | 6.1E0 | 2.4E1 | 1.1E1 | 1.7E-2 | 1.7E-2 | 1.6E2 | 6.1E1 | 81 | 45 | 74 | 45 | 0.52 |
| nM | pg/ml | 1.0E-9 | 1.0E-9 | 1.9E2 | 1.0E-9 | 1.4E3 | 0.0E0 | 1.0E-9 | 1.0E-9 | 1.0E4 | 1.0E-9 | 53 | 34 | 51 | 34 | 0.48 |

Figure 4 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nN | pg/ml | 1.0E3 | 2.6E3 | 1.8E3 | 1.1E4 | 2.6E3 | 4.5E4 | 1.1E2 | 2.3E2 | 1.7E4 | 2.7E5 | 53 | 34 | 51 | 34 | 0.74 |
| nO | pg/ml | 3.2E1 | 3.6E1 | 4.9E1 | 5.1E1 | 4.9E1 | 6.2E1 | 5.5E0 | 4.0E0 | 2.4E2 | 3.1E2 | 53 | 34 | 51 | 34 | 0.48 |
| nR | pg/ml | 1.3E1 | 2.0E1 | 2.9E1 | 7.0E1 | 4.6E1 | 1.8E2 | 1.0E-9 | 1.0E0 | 2.6E2 | 1.1E3 | 53 | 34 | 51 | 34 | 0.61 |
| nT | pg/ml | 1.1E2 | 7.3E1 | 3.7E2 | 1.1E2 | 1.2E3 | 1.3E2 | 1.0E-9 | 1.0E-9 | 6.6E3 | 6.9E2 | 53 | 34 | 51 | 34 | 0.45 |
| nU | pg/ml | 1.4E1 | 4.5E1 | 5.3E2 | 8.3E1 | 2.3E3 | 1.0E2 | 1.0E-9 | 1.0E-9 | 1.3E4 | 4.3E2 | 53 | 34 | 51 | 34 | 0.57 |
| lW | pg/ml | 1.0E-9 | 1.0E-9 | 1.5E1 | 1.8E1 | 5.5E1 | 5.6E1 | 1.0E-9 | 1.0E-9 | 3.9E2 | 2.9E2 | 53 | 34 | 51 | 34 | 0.51 |
| lX | pg/ml | 1.1E3 | 7.5E2 | 1.1E3 | 8.9E2 | 5.5E2 | 5.5E2 | 2.3E2 | 1.3E2 | 2.6E3 | 2.5E3 | 53 | 34 | 51 | 34 | 0.38 |
| lY | pg/ml | 1.8E1 | 1.9E1 | 2.2E1 | 2.0E1 | 2.3E1 | 1.5E1 | 1.0E-9 | 1.0E-9 | 1.4E2 | 5.9E1 | 53 | 34 | 51 | 34 | 0.51 |
| mE | pg/ml | 1.0E-9 | 1.0E-9 | 3.6E0 | 1.5E0 | 1.0E1 | 3.0E0 | 1.0E-9 | 1.0E-9 | 5.8E1 | 1.6E1 | 53 | 34 | 51 | 34 | 0.52 |
| mF | pg/ml | 1.0E-9 | 9.3E-2 | 1.8E0 | 9.0E0 | 3.3E0 | 4.2E1 | 1.0E-9 | 1.0E-9 | 1.5E1 | 2.5E2 | 53 | 34 | 51 | 34 | 0.53 |
| mH | pg/ml | 4.4E0 | 3.2E0 | 5.6E0 | 4.4E0 | 5.2E0 | 5.6E0 | 2.3E-1 | 4.0E-1 | 3.2E1 | 3.2E1 | 53 | 34 | 51 | 34 | 0.39 |
| ml | pg/ml | 1.0E-9 | 3.7E0 | 1.4E1 | 1.2E1 | 3.1E1 | 1.6E1 | 1.0E-9 | 1.0E-9 | 1.6E2 | 6.1E1 | 53 | 34 | 51 | 34 | 0.55 |
| mM | pg/ml | 1.8E1 | 3.5E1 | 4.3E1 | 1.0E2 | 5.9E1 | 1.9E2 | 1.0E-9 | 1.0E-9 | 2.3E2 | 9.8E2 | 53 | 34 | 51 | 34 | 0.59 |
| mP | pg/ml | 1.4E1 | 1.5E1 | 1.8E1 | 2.1E1 | 2.2E1 | 3.0E1 | 1.0E-9 | 1.6E0 | 1.5E2 | 1.9E2 | 52 | 34 | 50 | 34 | 0.56 |
| mS | pg/ml | 1.8E3 | 1.5E3 | 2.1E3 | 1.8E3 | 2.3E3 | 9.8E2 | 1.0E-9 | 1.0E-9 | 1.3E4 | 4.2E3 | 53 | 34 | 51 | 34 | 0.47 |
| mT | pg/ml | 5.3E1 | 7.3E1 | 1.5E2 | 9.6E1 | 2.8E2 | 1.2E2 | 9.7E0 | 1.2E1 | 1.4E3 | 6.8E2 | 52 | 34 | 50 | 34 | 0.51 |
| mU | pg/ml | 2.5E0 | 2.6E0 | 4.1E0 | 5.1E0 | 8.7E0 | 1.2E1 | 1.0E-9 | 5.5E-1 | 5.8E1 | 6.8E1 | 52 | 34 | 50 | 34 | 0.55 |
| mW | pg/ml | 2.0E3 | 2.1E3 | 2.6E3 | 2.6E3 | 1.7E3 | 2.0E3 | 3.1E2 | 1.0E-9 | 1.0E4 | 1.1E4 | 52 | 34 | 50 | 34 | 0.50 |
| mY | pg/ml | 4.8E2 | 6.6E2 | 9.9E2 | 8.7E2 | 1.8E3 | 1.0E3 | 1.0E-9 | 1.0E-9 | 1.1E4 | 5.6E3 | 53 | 34 | 51 | 34 | 0.57 |
| mZ | pg/ml | 1.8E2 | 2.8E2 | 3.1E2 | 5.0E2 | 2.9E2 | 5.4E2 | 1.0E-9 | 5.2E1 | 1.2E3 | 2.6E3 | 52 | 34 | 50 | 34 | 0.61 |
| nA | pg/ml | 1.3E0 | 2.6E0 | 1.6E1 | 8.7E0 | 6.7E1 | 1.5E1 | 1.0E-9 | 1.0E-9 | 4.4E2 | 5.5E1 | 52 | 34 | 50 | 34 | 0.57 |
| nB | pg/ml | 2.9E2 | 3.0E2 | 3.0E2 | 3.0E2 | 1.6E2 | 1.4E2 | 3.0E1 | 3.7E1 | 7.0E2 | 6.4E2 | 53 | 34 | 51 | 34 | 0.52 |
| nC | pg/ml | 1.0E-9 | 6.1E1 | 8.3E3 | 1.3E4 | 5.0E4 | 6.6E4 | 1.0E-9 | 1.0E-9 | 3.7E5 | 3.8E5 | 53 | 34 | 51 | 34 | 0.55 |
| nD | pg/ml | 6.7E0 | 8.2E0 | 7.2E1 | 1.4E1 | 3.2E2 | 2.3E1 | 1.0E-9 | 1.0E-9 | 1.7E3 | 1.3E2 | 52 | 34 | 50 | 34 | 0.51 |
| nF | pg/ml | 1.0E-9 | 1.0E-9 | 7.7E0 | 3.6E0 | 3.9E1 | 1.0E1 | 1.0E-9 | 1.0E-9 | 2.4E2 | 3.8E1 | 53 | 34 | 51 | 34 | 0.53 |
| nH | pg/ml | 3.8E-1 | 3.5E0 | 2.1E2 | 1.0E2 | 1.4E3 | 4.5E2 | 1.0E-9 | 1.0E-9 | 1.0E4 | 2.6E3 | 52 | 34 | 50 | 34 | 0.58 |
| nI | pg/ml | 4.6E1 | 4.6E1 | 2.9E2 | 8.7E1 | 1.3E3 | 1.6E2 | 1.0E-9 | 1.0E-9 | 9.2E3 | 7.9E2 | 53 | 34 | 51 | 34 | 0.47 |
| nJ | pg/ml | 1.0E-9 | 5.1E-1 | 1.0E2 | 1.4E0 | 7.1E2 | 3.0E0 | 1.0E-9 | 1.0E-9 | 5.2E3 | 1.6E1 | 53 | 34 | 51 | 34 | 0.58 |
| nK | pg/ml | 1.0E-9 | 1.0E-9 | 1.2E2 | 2.2E1 | 5.4E2 | 4.8E1 | 1.0E-9 | 1.0E-9 | 3.2E3 | 2.3E2 | 52 | 34 | 50 | 34 | 0.54 |
| nL | pg/ml | 1.0E-9 | 2.6E0 | 9.2E2 | 2.1E2 | 6.1E3 | 7.6E2 | 1.0E-9 | 1.0E-9 | 4.5E4 | 4.3E3 | 53 | 34 | 51 | 34 | 0.57 |
| hL | pg/ml | 1.8E4 | 1.7E4 | 2.4E4 | 2.0E4 | 2.2E4 | 1.4E4 | 1.0E-9 | 1.0E-9 | 1.4E5 | 6.0E4 | 55 | 24 | 54 | 24 | 0.48 |
| hO | pg/ml | 1.6E4 | 1.6E4 | 1.7E4 | 1.6E4 | 3.2E3 | 3.7E3 | 1.1E4 | 1.1E4 | 2.8E4 | 2.7E4 | 55 | 24 | 54 | 24 | 0.41 |
| hP | ng/ml | 4.4E5 | 4.4E5 | 3.5E5 | 4.2E5 | 1.8E5 | 5.3E5 | 2.3E4 | 2.5E4 | 9.0E5 | 2.8E6 | 55 | 24 | 54 | 24 | 0.48 |
| wJ | pg/ml | 1.5E5 | 1.0E5 | 1.6E5 | 1.5E5 | 6.9E4 | 1.0E5 | 3.2E4 | 3.6E4 | 3.1E5 | 4.7E5 | 54 | 24 | 53 | 24 | 0.42 |
| wK | pg/ml | 3.4E4 | 3.9E4 | 4.2E4 | 4.7E4 | 2.5E4 | 4.1E4 | 5.2E3 | 8.1E3 | 1.1E5 | 2.0E5 | 54 | 24 | 53 | 24 | 0.50 |
| wL | pg/ml | 5.8E0 | 1.6E0 | 5.6E1 | 7.5E0 | 1.3E2 | 1.0E1 | 1.0E-9 | 1.0E-9 | 8.4E2 | 3.1E1 | 54 | 24 | 53 | 24 | 0.38 |
| wP | pg/ml | 2.8E4 | 2.9E4 | 4.2E4 | 6.7E4 | 4.0E4 | 8.4E4 | 1.1E3 | 4.5E3 | 1.6E5 | 3.0E5 | 54 | 24 | 53 | 24 | 0.54 |
| wQ | pg/ml | 3.5E1 | 3.5E1 | 6.3E1 | 5.2E1 | 7.8E1 | 6.1E1 | 1.0E-9 | 1.0E-9 | 3.7E2 | 2.4E2 | 54 | 24 | 53 | 24 | 0.47 |
| hR | pg/ml | 2.9E4 | 2.6E4 | 3.0E4 | 2.5E4 | 1.2E4 | 1.0E4 | 1.8E3 | 1.0E-9 | 5.8E4 | 4.5E4 | 79 | 41 | 72 | 41 | 0.40 |
| hV | pg/ml | 4.7E2 | 3.8E2 | 5.1E2 | 4.6E2 | 2.5E2 | 4.1E2 | 1.3E2 | 1.0E-9 | 1.5E3 | 2.5E3 | 79 | 41 | 72 | 41 | 0.39 |
| hW | pg/ml | 1.5E3 | 1.7E3 | 1.8E3 | 3.0E3 | 9.5E2 | 6.1E3 | 5.7E2 | 1.0E-9 | 4.8E3 | 4.0E4 | 79 | 41 | 72 | 41 | 0.56 |
| hX | pg/ml | 9.3E2 | 8.1E2 | 1.1E3 | 9.4E2 | 1.0E3 | 4.6E2 | 3.6E2 | 2.5E0 | 8.6E3 | 2.6E3 | 79 | 41 | 72 | 41 | 0.42 |
| iA | pg/ml | 1.4E2 | 1.8E2 | 4.0E2 | 2.3E2 | 9.0E2 | 2.0E2 | 1.1E1 | 1.1E1 | 7.1E3 | 7.8E2 | 105 | 49 | 97 | 49 | 0.52 |
| iB | ng/ml | 4.9E0 | 6.1E0 | 6.3E0 | 7.5E0 | 4.7E0 | 5.9E0 | 3.7E-2 | 8.8E-2 | 1.9E1 | 2.4E1 | 81 | 45 | 74 | 45 | 0.57 |
| iC | U/ml | 2.2E-1 | 4.6E-1 | 4.4E-1 | 1.6E0 | 8.3E-1 | 5.0E0 | 1.0E-9 | 1.0E-9 | 6.4E0 | 3.2E1 | 81 | 45 | 74 | 45 | 0.66 |
| tQ | pg/ml | 1.1E3 | 1.6E3 | 1.2E3 | 1.5E3 | 5.3E2 | 6.9E2 | 2.8E2 | 5.3E2 | 2.5E3 | 3.3E3 | 53 | 23 | 52 | 23 | 0.59 |
| tT | pg/ml | 1.7E1 | 2.3E1 | 1.8E1 | 3.2E1 | 9.7E0 | 2.8E1 | 7.4E0 | 6.7E0 | 6.9E1 | 1.2E2 | 53 | 23 | 52 | 23 | 0.67 |
| tS | pg/ml | 1.1E0 | 1.1E0 | 1.4E0 | 2.3E0 | 1.4E0 | 3.0E0 | 1.0E-9 | 1.0E-9 | 8.5E0 | 1.0E1 | 53 | 23 | 52 | 23 | 0.54 |
| tX | pg/ml | 8.6E-1 | 1.2E0 | 1.1E0 | 2.4E0 | 8.6E-1 | 2.7E0 | 2.5E-2 | 3.7E-1 | 4.4E0 | 1.0E1 | 53 | 23 | 52 | 23 | 0.65 |
| tO | pg/ml | 3.9E0 | 4.4E0 | 4.7E0 | 6.3E0 | 3.1E0 | 5.0E0 | 1.0E-9 | 1.6E0 | 1.4E1 | 1.9E1 | 53 | 23 | 52 | 23 | 0.55 |
| tR | pg/ml | 2.2E-1 | 2.3E-1 | 2.9E-1 | 5.1E-1 | 2.9E-1 | 6.8E-1 | 1.0E-9 | 1.0E-9 | 1.5E0 | 2.5E0 | 53 | 23 | 52 | 23 | 0.55 |
| tU | pg/ml | 8.7E0 | 1.1E1 | 1.1E1 | 1.5E1 | 7.1E0 | 1.6E1 | 1.6E0 | 1.5E0 | 3.1E1 | 8.0E1 | 53 | 24 | 52 | 24 | 0.57 |
| tN | pg/ml | 1.7E1 | 1.9E1 | 2.1E1 | 4.0E1 | 1.4E1 | 3.9E1 | 1.0E-9 | 9.4E0 | 8.0E1 | 1.6E2 | 53 | 22 | 52 | 22 | 0.61 |
| tV | ng/ml | 4.2E2 | 9.0E2 | 5.3E2 | 9.3E2 | 5.0E2 | 6.5E2 | 1.5E2 | 2.2E2 | 2.9E3 | 3.1E3 | 54 | 24 | 53 | 24 | 0.71 |
| iH | ng/ml | 1.5E5 | 1.8E5 | 1.5E5 | 1.8E5 | 4.4E4 | 4.3E4 | 7.1E4 | 6.7E4 | 2.4E5 | 2.5E5 | 105 | 49 | 97 | 49 | 0.67 |
| iJ | ng/ml | 5.1E4 | 4.4E4 | 5.2E4 | 5.0E4 | 2.2E4 | 3.6E4 | 5.5E3 | 7.7E3 | 1.0E5 | 2.5E5 | 105 | 49 | 97 | 49 | 0.44 |
| hB | ng/ml | 4.4E-1 | 5.5E-1 | 5.0E-1 | 7.4E-1 | 3.2E-1 | 6.4E-1 | 1.0E-9 | 1.2E-1 | 1.7E0 | 3.0E0 | 105 | 49 | 97 | 49 | 0.60 |

Figure 4 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| hC | pg/ml | 3.7E3 | 4.8E3 | 5.7E3 | 8.8E3 | 7.5E3 | 1.1E4 | 1.0E-9 | 4.5E1 | 5.5E4 | 5.7E4 | 105 | 49 | 97 | 49 | 0.59 |
| hF | ng/ml | 1.0E-9 | 1.0E-9 | 4.7E1 | 1.0E-9 | 4.0E2 | 0.0E0 | 1.0E-9 | 1.0E-9 | 4.0E3 | 1.0E-9 | 105 | 49 | 97 | 49 | 0.48 |
| hG | pg/ml | 7.0E3 | 7.6E3 | 7.3E3 | 8.3E3 | 3.1E3 | 3.8E3 | 2.8E1 | 3.3E3 | 1.8E4 | 2.0E4 | 105 | 49 | 97 | 49 | 0.56 |
| iO | ng/ml | 3.8E5 | 3.7E5 | 4.1E5 | 3.9E5 | 1.9E5 | 1.8E5 | 1.1E4 | 8.3E4 | 1.1E6 | 9.2E5 | 105 | 49 | 97 | 49 | 0.48 |
| iP | ng/ml | 6.0E4 | 4.1E4 | 5.5E4 | 7.5E4 | 3.2E4 | 1.2E5 | 1.0E-9 | 3.8E3 | 2.5E5 | 5.7E5 | 105 | 49 | 97 | 49 | 0.45 |
| iZ | ng/ml | 1.6E3 | 1.6E3 | 1.8E3 | 2.0E3 | 7.5E2 | 1.0E3 | 4.7E2 | 7.5E2 | 5.1E3 | 5.7E3 | 105 | 49 | 97 | 49 | 0.54 |
| yH | pg/ml | 1.1E3 | 1.2E3 | 1.9E3 | 3.1E3 | 2.9E3 | 5.1E3 | 1.0E-9 | 2.4E2 | 1.5E4 | 2.5E4 | 54 | 24 | 53 | 24 | 0.59 |
| yK | U/ml | 1.9E1 | 2.9E1 | 4.8E1 | 5.3E1 | 8.2E1 | 6.4E1 | 1.0E-9 | 1.0E-9 | 3.8E2 | 3.0E2 | 54 | 24 | 53 | 24 | 0.62 |
| yJ | pg/ml | 3.4E4 | 3.8E4 | 4.6E4 | 4.5E4 | 3.4E4 | 3.4E4 | 1.7E3 | 2.7E3 | 1.6E5 | 1.3E5 | 54 | 24 | 53 | 24 | 0.49 |
| yD | ng/ml | 1.5E-2 | 1.6E-2 | 1.5E-2 | 1.7E-2 | 6.9E-3 | 8.0E-3 | 1.0E-9 | 4.3E-2 | 3.0E-2 | | 54 | 24 | 53 | 24 | 0.56 |
| jB | ng/ml | 2.8E5 | 2.3E5 | 2.8E5 | 2.3E5 | 9.6E4 | 8.7E4 | 5.7E4 | 9.9E4 | 4.7E5 | 3.9E5 | 27 | 13 | 26 | 13 | 0.34 |
| wB | pg/ml | 8.1E3 | 1.1E4 | 9.5E3 | 1.4E4 | 7.2E3 | 1.0E4 | 1.7E3 | 3.1E3 | 4.1E4 | 4.2E4 | 54 | 24 | 53 | 24 | 0.62 |
| pY | pg/ml | 6.0E0 | 6.2E0 | 1.1E1 | 6.9E0 | 2.6E1 | 3.1E0 | 2.1E0 | 2.6E0 | 2.0E2 | 1.7E1 | 55 | 24 | 54 | 24 | 0.53 |
| sI | ng/ml | 5.2E-2 | 5.6E-2 | 5.9E-2 | 6.0E-2 | 4.5E-2 | 2.3E-2 | 1.6E-2 | 2.5E-2 | 2.5E-1 | 1.2E-1 | 28 | 14 | 28 | 14 | 0.58 |
| sF | mIU/mL | 5.8E0 | 5.2E0 | 1.4E1 | 1.1E1 | 2.0E1 | 1.4E1 | 1.4E-1 | 9.3E-2 | 8.1E1 | 4.5E1 | 28 | 14 | 28 | 14 | 0.48 |
| sH | mIU/mL | 2.5E0 | 3.8E0 | 5.1E0 | 4.1E0 | 7.7E0 | 4.4E0 | 1.0E-9 | 1.0E-9 | 3.2E1 | 1.7E1 | 28 | 14 | 28 | 14 | 0.53 |
| sJ | ng/ml | 1.5E-1 | 1.5E-1 | 5.7E-1 | 1.3E-1 | 1.3E0 | 9.6E-2 | 1.0E-9 | 1.0E-9 | 5.9E0 | 3.2E-1 | 28 | 14 | 28 | 14 | 0.47 |
| rC | pg/ml | 1.9E3 | 1.1E3 | 2.3E3 | 1.6E3 | 2.2E3 | 1.5E3 | 9.3E1 | 1.9E2 | 1.5E4 | 7.3E3 | 78 | 41 | 72 | 41 | 0.39 |
| rB | pg/ml | 2.2E1 | 2.6E1 | 4.6E1 | 4.8E1 | 1.2E2 | 6.1E1 | 1.0E-9 | 1.0E-9 | 9.5E2 | 2.8E2 | 78 | 41 | 72 | 41 | 0.58 |
| zG | 2.5ng/ml | 2.2E-1 | 1.9E-1 | 4.8E-1 | 4.8E-1 | 7.5E-1 | 7.7E-1 | 1.0E-9 | 1.0E-9 | 4.4E0 | 2.7E0 | 54 | 24 | 53 | 24 | 0.47 |
| zH | 2.3mU/ml | 1.1E-1 | 8.8E-2 | 1.2E-1 | 8.8E-2 | 6.9E-2 | 3.1E-2 | 1.0E-2 | 1.9E-2 | 4.4E-1 | 1.4E-1 | 54 | 24 | 53 | 24 | 0.34 |
| zI | 2.6ng/ml | 1.9E0 | 2.2E0 | 3.4E0 | 5.7E0 | 3.6E0 | 7.3E0 | 6.3E-1 | 4.3E-1 | 1.6E1 | 2.7E1 | 54 | 24 | 53 | 24 | 0.58 |
| qA | ng/ml | 1.1E7 | 9.9E6 | 1.3E7 | 1.5E7 | 7.4E6 | 1.1E7 | 3.7E6 | 3.4E6 | 3.7E7 | 4.6E7 | 55 | 24 | 54 | 24 | 0.53 |
| qB | ng/ml | 6.1E5 | 5.3E5 | 8.3E5 | 9.2E5 | 5.9E5 | 8.4E5 | 2.1E5 | 1.9E5 | 2.9E6 | 3.8E6 | 55 | 24 | 54 | 24 | 0.48 |
| qC | ng/ml | 4.5E5 | 3.1E5 | 9.1E5 | 3.8E5 | 1.3E6 | 3.3E5 | 2.0E4 | 2.1E4 | 7.1E6 | 1.5E6 | 55 | 24 | 54 | 24 | 0.38 |
| qD | ng/ml | 1.6E7 | 1.5E7 | 2.0E7 | 1.6E7 | 1.0E7 | 5.8E6 | 1.2E6 | 4.9E6 | 5.2E7 | 2.9E7 | 55 | 24 | 54 | 24 | 0.38 |
| jD | ng/ml | 2.0E1 | 3.0E1 | 4.1E1 | 5.8E1 | 7.0E1 | 8.1E1 | 1.0E-9 | 1.0E-9 | 5.1E2 | 5.1E2 | 81 | 45 | 74 | 45 | 0.62 |
| jE | ng/ml | 1.0E-9 | 1.0E-9 | 8.5E0 | 7.8E0 | 2.1E1 | 1.5E1 | 1.0E-9 | 1.0E-9 | 1.2E2 | 5.1E1 | 81 | 45 | 74 | 45 | 0.51 |
| jF | ng/ml | 4.9E1 | 2.8E1 | 5.8E1 | 5.3E1 | 5.8E1 | 7.0E1 | 1.0E-9 | 1.0E-9 | 2.5E2 | 3.5E2 | 81 | 45 | 74 | 45 | 0.44 |
| jG | ng/ml | 4.4E3 | 4.3E3 | 4.4E3 | 4.7E3 | 1.9E3 | 2.1E3 | 7.6E2 | 6.7E2 | 8.9E3 | 1.1E4 | 81 | 45 | 74 | 45 | 0.53 |
| jH | ng/ml | 7.6E1 | 7.9E1 | 8.6E1 | 9.8E1 | 4.9E1 | 6.5E1 | 1.9E1 | 3.0E1 | 2.8E2 | 4.3E2 | 81 | 45 | 74 | 45 | 0.56 |
| jI | ng/ml | 6.3E1 | 8.2E1 | 6.9E1 | 9.4E1 | 3.5E1 | 6.8E1 | 1.9E1 | 3.1E1 | 2.5E2 | 4.4E2 | 81 | 45 | 74 | 45 | 0.65 |
| sK | pg/mL | 3.7E3 | 3.4E3 | 4.0E3 | 4.5E3 | 1.3E3 | 4.3E3 | 1.7E3 | 2.1E3 | 8.0E3 | 2.3E4 | 54 | 24 | 53 | 24 | 0.45 |
| sM | pg/mL | 7.3E4 | 8.4E4 | 7.5E4 | 9.0E4 | 2.1E4 | 4.0E4 | 3.3E4 | 4.5E4 | 1.5E5 | 2.0E5 | 54 | 24 | 53 | 24 | 0.61 |
| sO | pg/mL | 3.0E8 | 2.3E8 | 3.0E8 | 2.3E8 | 9.2E7 | 8.9E7 | 7.9E7 | 6.6E7 | 4.9E8 | 4.4E8 | 54 | 24 | 53 | 24 | 0.30 |
| wC | ng/ml | 1.6E0 | 1.4E0 | 2.2E0 | 1.7E0 | 2.3E0 | 1.1E0 | 2.5E-1 | 6.1E-2 | 1.5E1 | 4.8E0 | 54 | 24 | 53 | 24 | 0.48 |
| wD | ng/ml | 1.6E1 | 2.3E1 | 7.3E1 | 5.2E1 | 2.9E2 | 6.5E1 | 2.1E0 | 5.0E0 | 2.1E3 | 2.9E2 | 54 | 24 | 53 | 24 | 0.69 |
| wE | ng/ml | 4.9E1 | 5.0E1 | 5.3E1 | 4.7E1 | 2.5E1 | 1.8E1 | 7.0E0 | 3.2E0 | 1.4E2 | 8.4E1 | 54 | 24 | 53 | 24 | 0.44 |
| wG | ng/ml | 8.2E-2 | 3.0E-2 | 1.2E-1 | 7.2E-2 | 1.5E-1 | 1.4E-1 | 1.0E-9 | 1.0E-9 | 7.1E-1 | 6.8E-1 | 54 | 24 | 53 | 24 | 0.37 |
| wH | ng/ml | 1.9E-2 | 2.2E-2 | 1.6E-1 | 2.0E-1 | 4.9E-1 | 4.5E-1 | 1.0E-9 | 1.0E-9 | 2.9E0 | 1.9E0 | 54 | 24 | 53 | 24 | 0.53 |
| wF | ng/ml | 1.7E-1 | 1.3E-1 | 2.5E0 | 1.2E0 | 9.9E0 | 2.3E0 | 1.0E-9 | 1.0E-9 | 5.7E1 | 9.6E0 | 54 | 24 | 53 | 24 | 0.52 |
| rA | pg/ml | 2.4E1 | 2.6E1 | 3.0E1 | 3.2E1 | 2.7E1 | 2.2E1 | 1.0E-9 | 1.0E-9 | 2.0E2 | 9.6E1 | 80 | 45 | 74 | 45 | 0.53 |
| qZ | pg/ml | 4.3E1 | 4.5E1 | 1.9E2 | 7.0E2 | 1.2E3 | 2.4E3 | 2.8E-4 | 5.9E-4 | 1.0E4 | 1.0E4 | 71 | 36 | 68 | 36 | 0.53 |
| qY | pg/ml | 2.9E1 | 3.0E1 | 5.1E1 | 5.3E1 | 7.4E1 | 5.8E1 | 8.7E-1 | 2.1E0 | 5.3E2 | 2.8E2 | 80 | 45 | 74 | 45 | 0.53 |
| qX | pg/ml | 5.4E1 | 6.8E1 | 6.0E1 | 7.8E1 | 3.8E1 | 5.4E1 | 1.0E-9 | 1.0E-9 | 1.8E2 | 2.0E2 | 80 | 45 | 74 | 45 | 0.57 |
| qW | pg/ml | 9.7E0 | 7.3E0 | 1.5E1 | 1.1E1 | 2.0E1 | 1.1E1 | 1.0E-9 | 1.0E-9 | 1.2E2 | 3.9E1 | 80 | 45 | 74 | 45 | 0.43 |
| qV | pg/ml | 2.2E3 | 1.9E3 | 2.8E3 | 2.7E3 | 2.0E3 | 2.1E3 | 2.3E2 | 3.5E2 | 8.5E3 | 1.1E4 | 80 | 45 | 74 | 45 | 0.47 |
| qU | pg/ml | 5.5E1 | 5.6E1 | 1.7E2 | 1.3E2 | 2.6E2 | 1.8E2 | 2.6E2 | 1.8E2 | 1.4E3 | 8.0E2 | 80 | 45 | 74 | 45 | 0.50 |
| qT | pg/ml | 3.7E1 | 4.3E1 | 6.5E1 | 7.1E1 | 1.2E2 | 7.1E1 | 1.0E-9 | 1.0E-9 | 9.0E2 | 3.1E2 | 80 | 45 | 74 | 45 | 0.59 |
| qI | ng/ml | 5.4E4 | 6.5E4 | 6.2E4 | 7.0E4 | 3.1E4 | 3.4E4 | 1.1E4 | 2.5E4 | 1.6E5 | 1.6E5 | 54 | 24 | 54 | 24 | 0.58 |
| qH | ng/ml | 6.6E4 | 5.4E4 | 7.2E4 | 5.5E4 | 3.8E4 | 3.3E4 | 1.5E4 | 1.0E4 | 1.8E5 | 1.6E5 | 54 | 24 | 54 | 24 | 0.36 |
| qG | ng/ml | 1.8E5 | 1.9E5 | 1.9E5 | 1.9E5 | 5.9E4 | 5.3E4 | 5.8E4 | 1.0E5 | 3.3E5 | 2.9E5 | 54 | 24 | 54 | 24 | 0.49 |
| jK | ng/ml | 1.6E3 | 1.5E3 | 1.7E3 | 1.6E3 | 5.3E2 | 5.2E2 | 5.5E2 | 7.5E2 | 3.5E3 | 3.1E3 | 81 | 45 | 74 | 45 | 0.46 |
| jL | ng/ml | 1.7E2 | 2.1E2 | 2.5E2 | 3.4E2 | 1.9E2 | 3.3E2 | 3.6E1 | 3.7E1 | 9.6E2 | 1.7E3 | 81 | 45 | 74 | 45 | 0.58 |
| jM | ng/ml | 7.1E4 | 8.2E4 | 7.3E4 | 7.8E4 | 4.0E4 | 3.7E4 | 3.9E2 | 1.1E4 | 1.9E5 | 1.7E5 | 81 | 45 | 74 | 45 | 0.55 |
| jO | pg/ml | 2.1E5 | 2.3E5 | 2.7E5 | 2.6E5 | 1.7E5 | 1.3E5 | 5.2E4 | 9.6E4 | 1.1E6 | 5.9E5 | 81 | 45 | 74 | 45 | 0.52 |
| jP | pg/ml | 2.2E5 | 2.6E5 | 2.5E5 | 2.8E5 | 1.5E5 | 1.5E5 | 3.6E4 | 5.8E4 | 9.1E5 | 7.0E5 | 81 | 45 | 74 | 45 | 0.57 |

Figure 4 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jQ | pg/ml | 2.8E3 | 2.5E3 | 3.7E3 | 4.8E3 | 3.1E3 | 8.9E3 | 4.2E1 | 1.0E-9 | 1.3E4 | 5.6E4 | 81 | 45 | 74 | 45 | 0.45 |
| jR | pg/ml | 8.6E3 | 5.1E3 | 1.3E4 | 1.4E4 | 1.3E4 | 3.0E4 | 1.0E-9 | 1.0E-9 | 6.8E4 | 1.8E5 | 81 | 45 | 74 | 45 | 0.43 |
| jT | pg/ml | 1.7E5 | 1.7E5 | 1.7E5 | 1.8E5 | 6.3E4 | 7.7E4 | 6.8E4 | 8.8E4 | 3.9E5 | 4.7E5 | 81 | 45 | 74 | 45 | 0.51 |
| xA | pg/ml | 3.9E0 | 5.2E0 | 1.5E1 | 1.2E1 | 5.4E1 | 2.4E1 | 1.0E-9 | 1.0E-9 | 3.9E2 | 1.2E2 | 54 | 24 | 53 | 24 | 0.55 |
| yE | pg/ml | 7.9E1 | 7.7E1 | 8.3E1 | 8.8E1 | 4.4E1 | 4.7E1 | 1.8E1 | 1.4E1 | 3.0E2 | 2.5E2 | 54 | 24 | 53 | 24 | 0.52 |
| tM | pg/ml | 3.9E1 | 3.8E1 | 4.2E1 | 3.9E1 | 2.1E1 | 2.3E1 | 1.0E-9 | 1.0E-9 | 1.0E2 | 1.1E2 | 54 | 24 | 53 | 24 | 0.45 |
| tL | pg/ml | 1.0E-9 | 1.0E-9 | 6.9E0 | 1.3E-1 | 3.6E1 | 3.9E-1 | 1.0E-9 | 1.0E-9 | 2.6E2 | 1.8E0 | 54 | 24 | 53 | 24 | 0.45 |
| jU | mIU/ml | 3.5E0 | 4.3E0 | 1.0E1 | 5.8E0 | 1.8E1 | 5.2E0 | 8.9E-2 | 4.2E-2 | 8.1E1 | 1.8E1 | 81 | 45 | 74 | 45 | 0.50 |
| jV | mIU/ml | 1.5E0 | 1.4E0 | 3.4E0 | 3.3E0 | 5.5E0 | 5.7E0 | 3.4E-2 | 1.7E-3 | 3.1E1 | 3.5E1 | 81 | 45 | 74 | 45 | 0.48 |
| jY | ng/ml | 7.4E-4 | 1.0E-9 | 9.8E-3 | 2.9E-3 | 4.1E-2 | 4.9E-3 | 1.0E-9 | 1.0E-9 | 3.0E-1 | 2.1E-2 | 81 | 45 | 74 | 45 | 0.46 |
| kC | pg/ml | 9.7E1 | 1.2E2 | 2.3E2 | 1.8E2 | 5.6E2 | 2.0E2 | 2.9E1 | 2.1E1 | 3.5E3 | 1.1E3 | 53 | 34 | 51 | 34 | 0.57 |
| kE | pg/ml | 1.2E5 | 1.4E5 | 1.3E5 | 1.4E5 | 3.2E4 | 4.4E4 | 4.1E4 | 1.2E4 | 2.0E5 | 2.2E5 | 53 | 34 | 51 | 34 | 0.59 |
| kF | pg/mL | 6.0E1 | 6.6E1 | 7.4E1 | 6.9E1 | 7.1E1 | 2.0E1 | 2.7E1 | 2.6E1 | 5.1E2 | 1.2E2 | 53 | 34 | 51 | 34 | 0.59 |
| kG | pg/mL | 8.5E3 | 9.9E3 | 9.4E3 | 1.2E4 | 7.8E3 | 1.1E4 | 7.5E2 | 1.1E3 | 4.3E4 | 5.8E4 | 53 | 34 | 51 | 34 | 0.60 |
| kI | pg/ml | 2.0E2 | 2.0E2 | 2.4E2 | 2.2E2 | 1.5E2 | 1.3E2 | 7.9E1 | 7.6E1 | 8.7E2 | 6.7E2 | 53 | 34 | 51 | 34 | 0.44 |
| kK | pg/ml | 1.0E2 | 1.4E2 | 1.6E2 | 2.4E2 | 1.9E2 | 3.5E2 | 6.4E0 | 2.1E1 | 1.2E3 | 1.9E3 | 53 | 34 | 51 | 34 | 0.58 |
| kN | pg/ml | 9.2E2 | 1.1E3 | 1.4E3 | 1.9E3 | 1.9E3 | 3.3E3 | 2.4E2 | 7.3E1 | 1.3E4 | 1.7E4 | 53 | 34 | 51 | 34 | 0.52 |
| kO | pg/ml | 7.7E3 | 7.8E3 | 1.0E4 | 8.7E3 | 1.8E4 | 4.3E3 | 3.7E3 | 3.7E3 | 1.3E5 | 2.5E4 | 53 | 34 | 51 | 34 | 0.52 |
| kP | pg/ml | 4.8E3 | 5.9E3 | 6.8E3 | 7.1E3 | 6.1E3 | 4.8E3 | 8.6E2 | 1.5E3 | 3.3E4 | 2.0E4 | 53 | 34 | 51 | 34 | 0.55 |
| kQ | pg/ml | 4.2E3 | 4.5E3 | 4.9E3 | 5.9E3 | 2.6E3 | 4.7E3 | 5.6E2 | 2.0E3 | 1.4E4 | 2.5E4 | 105 | 49 | 97 | 49 | 0.54 |
| kR | pg/ml | 2.0E1 | 2.0E1 | 3.6E1 | 2.8E1 | 1.0E2 | 2.3E1 | 1.0E-9 | 4.8E0 | 1.0E3 | 1.1E2 | 105 | 49 | 97 | 49 | 0.50 |
| kS | pg/ml | 7.6E2 | 8.8E2 | 8.9E2 | 9.2E2 | 5.2E2 | 4.9E2 | 1.3E2 | 2.6E2 | 3.2E3 | 2.5E3 | 105 | 49 | 97 | 49 | 0.53 |
| pS | ng/ml | 1.8E5 | 1.3E5 | 2.1E5 | 1.9E5 | 9.0E4 | 1.6E5 | 9.7E4 | 6.0E4 | 5.0E5 | 8.3E5 | 54 | 24 | 53 | 24 | 0.32 |
| rZ | ng/ml | 1.0E-9 | 2.4E-3 | 7.1E-3 | 1.3E-2 | 2.0E-2 | 4.5E-2 | 1.0E-9 | 1.0E-9 | 1.1E-1 | 2.9E-1 | 78 | 41 | 71 | 41 | 0.62 |
| rY | ng/ml | 5.3E-2 | 6.1E-2 | 2.2E-1 | 4.1E-1 | 8.1E-1 | 2.1E0 | 1.0E-9 | 1.0E-9 | 6.3E0 | 1.4E1 | 78 | 41 | 71 | 41 | 0.54 |
| rX | ng/ml | 1.0E-9 | 1.0E-9 | 8.4E-2 | 6.4E-2 | 4.4E-1 | 3.7E-1 | 1.0E-9 | 1.0E-9 | 3.7E0 | 2.3E0 | 78 | 41 | 71 | 41 | 0.46 |
| lK | pg/ml | 7.5E1 | 7.1E1 | 1.6E2 | 1.6E2 | 1.9E2 | 2.0E2 | 1.0E-9 | 1.0E-9 | 7.4E2 | 7.9E2 | 81 | 44 | 74 | 44 | 0.46 |
| lL | pg/ml | 1.7E3 | 1.4E3 | 2.7E3 | 2.1E3 | 3.0E3 | 1.8E3 | 7.5E1 | 8.9E1 | 1.9E4 | 7.7E3 | 81 | 45 | 74 | 45 | 0.44 |
| lM | pg/ml | 1.1E3 | 1.3E3 | 2.2E3 | 5.9E3 | 3.0E3 | 1.1E4 | 1.3E2 | 2.6E2 | 1.6E4 | 5.1E4 | 81 | 45 | 74 | 45 | 0.58 |
| lN | pg/ml | 1.0E-9 | 1.0E-9 | 6.9E0 | 2.3E0 | 2.2E1 | 3.9E0 | 1.0E-9 | 1.0E-9 | 1.5E2 | 1.3E1 | 81 | 45 | 74 | 45 | 0.46 |
| lO | pg/ml | 1.0E-9 | 1.0E-9 | 5.0E-1 | 3.4E0 | 4.5E0 | 2.1E1 | 1.0E-9 | 1.0E-9 | 4.0E1 | 1.4E2 | 81 | 44 | 74 | 44 | 0.52 |
| zA | ng/ml | 1.9E7 | 2.0E7 | 1.9E7 | 1.9E7 | 6.6E6 | 5.9E6 | 6.7E6 | 5.9E6 | 3.4E7 | 2.8E7 | 50 | 24 | 49 | 24 | 0.49 |
| rW | ng/ml | 1.7E-2 | 2.2E-2 | 2.7E-2 | 3.5E-2 | 3.2E-2 | 4.4E-2 | 1.0E-9 | 1.0E-9 | 1.7E-1 | 1.9E-1 | 54 | 23 | 54 | 23 | 0.55 |
| rV | ng/ml | 1.0E-9 | 1.0E-9 | 1.2E-2 | 2.0E-2 | 4.0E-2 | 5.7E-2 | 1.0E-9 | 1.0E-9 | 2.2E-1 | 2.4E-1 | 54 | 23 | 54 | 23 | 0.52 |
| rU | ng/ml | 1.1E-1 | 7.6E-2 | 1.8E-1 | 1.9E-1 | 2.7E-1 | 3.9E-1 | 1.0E-9 | 1.0E-9 | 1.4E0 | 1.9E0 | 54 | 23 | 54 | 23 | 0.51 |
| rT | ng/ml | 6.5E0 | 5.6E0 | 6.8E0 | 7.4E0 | 4.2E0 | 5.3E0 | 7.3E-1 | 1.0E0 | 2.1E1 | 2.0E1 | 54 | 23 | 54 | 23 | 0.51 |
| rS | ng/ml | 3.5E0 | 5.8E0 | 5.8E0 | 1.3E1 | 6.6E0 | 1.8E1 | 7.6E-1 | 1.0E0 | 3.8E1 | 7.0E1 | 54 | 23 | 54 | 23 | 0.61 |
| sC | pg/mL | 5.8E3 | 8.3E3 | 9.5E3 | 1.7E4 | 8.6E3 | 2.0E4 | 1.7E3 | 2.2E3 | 4.4E4 | 8.0E4 | 54 | 24 | 53 | 24 | 0.61 |
| yL | pg/ml | 3.2E1 | 2.7E1 | 3.9E1 | 8.4E1 | 2.8E1 | 2.8E2 | 5.6E0 | 1.2E1 | 1.8E2 | 1.4E3 | 52 | 24 | 51 | 24 | 0.34 |
| rP | ng/ml | 9.5E1 | 8.7E1 | 1.6E2 | 2.2E2 | 2.2E2 | 2.3E2 | 1.0E-9 | 1.3E0 | 1.2E3 | 7.4E2 | 54 | 23 | 54 | 23 | 0.56 |
| rQ | ng/ml | 1.0E-9 | 1.0E-9 | 3.6E0 | 7.7E-2 | 1.6E1 | 3.7E-1 | 1.0E-9 | 1.0E-9 | 8.9E1 | 1.8E0 | 54 | 23 | 54 | 23 | 0.47 |
| rO | ng/ml | 2.5E-2 | 3.5E-2 | 4.8E-2 | 5.4E-2 | 8.5E-2 | 7.2E-2 | 1.0E-9 | 1.0E-9 | 4.4E-1 | 3.3E-1 | 54 | 23 | 54 | 23 | 0.57 |
| rR | ng/ml | 3.9E0 | 3.9E0 | 2.3E1 | 1.1E1 | 6.8E1 | 2.1E1 | 1.0E-9 | 1.0E-9 | 4.5E2 | 9.5E1 | 54 | 23 | 54 | 23 | 0.49 |
| rN | ng/ml | 6.6E-1 | 6.8E-1 | 7.4E-1 | 1.1E0 | 4.4E-1 | 1.0E0 | 5.1E-2 | 2.4E-1 | 2.1E0 | 4.4E0 | 54 | 23 | 54 | 23 | 0.57 |
| qO | pg/ml | 9.8E3 | 1.1E4 | 1.3E4 | 2.0E4 | 9.6E3 | 1.7E4 | 2.2E3 | 1.9E3 | 4.6E4 | 6.4E4 | 55 | 24 | 54 | 24 | 0.60 |
| qP | pg/ml | 3.6E2 | 3.6E2 | 4.4E2 | 6.2E2 | 3.0E2 | 6.0E2 | 1.0E-9 | 1.2E2 | 1.5E3 | 2.5E3 | 55 | 24 | 54 | 24 | 0.55 |
| qQ | pg/ml | 1.5E1 | 6.3E0 | 1.7E1 | 9.9E0 | 3.8E1 | 1.2E1 | 1.0E-9 | 1.0E-9 | 2.8E2 | 4.3E1 | 55 | 24 | 54 | 24 | 0.44 |
| nW | pg/ml | 1.1E5 | 1.2E5 | 1.1E5 | 1.2E5 | 2.4E4 | 3.1E4 | 5.8E4 | 6.7E4 | 1.8E5 | 2.1E5 | 105 | 49 | 97 | 49 | 0.52 |
| nY | pg/ml | 1.9E3 | 2.0E3 | 2.2E3 | 2.6E3 | 1.4E3 | 1.7E3 | 6.5E2 | 5.7E2 | 9.9E3 | 1.0E4 | 105 | 49 | 97 | 49 | 0.55 |
| oO | pg/ml | 7.5E4 | 9.8E4 | 1.0E5 | 1.3E5 | 1.1E5 | 9.1E4 | 1.5E4 | 3.3E3 | 6.2E5 | 3.4E5 | 51 | 30 | 49 | 30 | 0.59 |
| oP | pg/ml | 1.1E5 | 1.4E5 | 1.3E5 | 1.7E5 | 7.7E4 | 1.1E5 | 2.4E4 | 2.4E4 | 3.6E5 | 4.2E5 | 51 | 30 | 49 | 30 | 0.60 |
| oQ | pg/ml | 2.5E3 | 3.1E3 | 2.9E3 | 4.3E3 | 1.7E3 | 3.4E3 | 9.3E2 | 9.1E2 | 1.0E4 | 1.7E4 | 51 | 30 | 49 | 30 | 0.63 |
| oE | pg/ml | 1.8E2 | 2.3E2 | 4.0E2 | 4.5E2 | 6.0E2 | 5.1E2 | 1.0E-9 | 1.0E-9 | 4.7E3 | 2.0E3 | 105 | 49 | 97 | 49 | 0.54 |
| oF | pg/ml | 7.4E3 | 8.2E3 | 1.7E4 | 2.3E4 | 3.0E4 | 3.0E4 | 6.4E1 | 1.8E2 | 1.7E5 | 1.4E5 | 105 | 49 | 97 | 49 | 0.59 |
| oH | pg/ml | 4.4E1 | 4.5E1 | 9.5E1 | 7.2E1 | 1.5E2 | 7.3E1 | 4.2E0 | 4.4E0 | 8.6E2 | 2.8E2 | 105 | 49 | 97 | 49 | 0.49 |
| oK | pg/ml | 6.4E2 | 1.0E3 | 2.0E3 | 1.6E3 | 3.1E3 | 1.6E3 | 5.2E1 | 1.9E2 | 1.8E4 | 7.3E3 | 105 | 49 | 97 | 49 | 0.57 |
| oN | pg/ml | 4.9E2 | 5.6E2 | 7.8E2 | 7.2E2 | 1.8E3 | 6.5E2 | 1.5E2 | 1.6E2 | 1.8E4 | 4.6E3 | 105 | 49 | 97 | 49 | 0.59 |

Figure 4 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| oW | pg/ml | 2.1E2 | 2.2E2 | 4.8E2 | 3.3E2 | 1.1E3 | 2.4E2 | 7.7E1 | 9.0E1 | 6.0E3 | 8.5E2 | 27 | 13 | 26 | 13 | 0.54 |
| oT | pg/ml | 3.5E2 | 2.8E2 | 3.6E2 | 3.2E2 | 1.8E2 | 1.8E2 | 9.9E1 | 1.1E2 | 7.8E2 | 7.9E2 | 27 | 13 | 26 | 13 | 0.41 |
| oV | pg/ml | 1.4E2 | 9.8E1 | 2.1E2 | 4.4E2 | 2.3E2 | 8.3E2 | 1.0E-9 | 1.1E1 | 9.9E2 | 2.4E3 | 27 | 13 | 26 | 13 | 0.48 |
| oD | pg/ml | 1.7E4 | 1.4E4 | 1.9E4 | 1.4E4 | 8.2E3 | 5.7E3 | 9.3E3 | 6.6E3 | 4.6E4 | 2.5E4 | 27 | 13 | 26 | 13 | 0.30 |
| uL | ng/ml | 3.6E1 | 3.3E1 | 4.4E1 | 5.3E1 | 3.0E1 | 7.1E1 | 1.0E-9 | 1.1E1 | 1.6E2 | 3.7E2 | 52 | 24 | 51 | 24 | 0.49 |
| uO | ng/ml | 3.0E-1 | 4.2E-1 | 7.8E-1 | 7.7E-1 | 1.4E0 | 1.1E0 | 1.0E-9 | 1.0E-9 | 9.3E0 | 5.0E0 | 52 | 24 | 51 | 24 | 0.53 |
| uM | ng/ml | 6.4E-1 | 7.5E-1 | 1.1E0 | 7.9E-1 | 2.2E0 | 5.6E-1 | 1.0E-9 | 1.0E-9 | 1.3E1 | 2.5E0 | 52 | 24 | 51 | 24 | 0.52 |
| uI | ng/ml | 7.7E-2 | 8.9E-2 | 1.4E-1 | 1.1E-1 | 1.9E-1 | 8.3E-2 | 1.6E-2 | 1.5E-2 | 1.1E0 | 3.8E-1 | 52 | 24 | 51 | 24 | 0.48 |
| uN | ng/ml | 1.5E1 | 1.3E1 | 1.7E1 | 1.6E1 | 6.7E0 | 8.3E0 | 7.7E0 | 6.4E0 | 4.1E1 | 4.1E1 | 52 | 24 | 51 | 24 | 0.43 |
| uG | ng/ml | 2.1E1 | 1.9E1 | 2.5E1 | 2.7E1 | 1.4E1 | 2.7E1 | 7.6E0 | 6.7E0 | 6.9E1 | 1.3E2 | 52 | 24 | 51 | 24 | 0.44 |
| uR | ng/ml | 2.3E0 | 2.6E0 | 3.9E0 | 3.3E0 | 8.6E0 | 3.0E0 | 9.9E-1 | 7.3E-1 | 6.4E1 | 1.4E1 | 54 | 24 | 53 | 24 | 0.51 |
| uP | ng/ml | 2.2E0 | 2.4E0 | 2.5E0 | 2.9E0 | 1.3E0 | 1.3E0 | 1.1E0 | 1.3E0 | 9.1E0 | 6.1E0 | 54 | 24 | 53 | 24 | 0.63 |
| uV | ng/ml | 2.3E-4 | 1.2E-3 | 1.6E-2 | 1.1E-2 | 4.0E-2 | 1.7E-2 | 1.0E-9 | 1.0E-9 | 2.0E-1 | 6.1E-2 | 54 | 24 | 53 | 24 | 0.51 |
| uT | ng/ml | 5.8E1 | 6.8E1 | 8.3E1 | 9.6E1 | 9.2E1 | 8.8E1 | 1.2E1 | 1.3E1 | 5.8E2 | 4.1E2 | 54 | 24 | 53 | 24 | 0.58 |
| uU | ng/ml | 1.7E0 | 1.4E0 | 2.0E0 | 2.6E0 | 1.2E0 | 3.9E0 | 5.2E-1 | 5.9E-1 | 5.6E0 | 2.0E1 | 54 | 24 | 53 | 24 | 0.44 |
| uW | ng/ml | 7.2E0 | 7.1E0 | 7.6E0 | 8.5E0 | 2.9E0 | 3.4E0 | 4.0E0 | 4.4E0 | 2.2E1 | 1.9E1 | 52 | 24 | 51 | 24 | 0.56 |
| vB | ng/ml | 2.6E0 | 3.3E0 | 2.7E0 | 3.2E0 | 1.2E0 | 1.5E0 | 6.9E-1 | 1.2E0 | 5.6E0 | 7.7E0 | 52 | 24 | 51 | 24 | 0.60 |
| vC | ng/ml | 1.0E-9 | 1.0E-9 | 3.0E-3 | 1.0E-9 | 2.0E-2 | 0.0E0 | 1.0E-9 | 1.0E-9 | 1.4E-1 | 1.0E-9 | 52 | 24 | 51 | 24 | 0.48 |
| uY | ng/ml | 7.4E-1 | 8.3E-1 | 1.2E0 | 1.2E0 | 1.1E0 | 1.1E0 | 8.7E-2 | 1.9E-1 | 4.9E0 | 4.4E0 | 52 | 24 | 51 | 24 | 0.52 |
| uZ | ng/ml | 5.8E-1 | 4.0E-1 | 8.2E-1 | 7.3E-1 | 1.1E0 | 1.0E0 | 4.7E-2 | 1.2E-1 | 7.2E0 | 4.9E0 | 52 | 24 | 51 | 24 | 0.39 |
| uX | ng/ml | 1.1E1 | 1.2E1 | 1.3E1 | 1.9E1 | 7.2E0 | 1.9E1 | 4.0E0 | 5.1E0 | 3.3E1 | 7.8E1 | 52 | 24 | 51 | 24 | 0.57 |
| vA | ng/ml | 7.4E-2 | 7.0E-2 | 8.6E-2 | 1.0E-1 | 5.8E-2 | 9.3E-2 | 2.4E-2 | 2.6E-2 | 3.0E-1 | 4.2E-1 | 52 | 24 | 51 | 24 | 0.51 |
| vH | ng/ml | 1.2E-1 | 1.1E-1 | 1.6E-1 | 2.1E-1 | 1.4E-1 | 3.7E-1 | 1.5E-2 | 1.4E-2 | 8.0E-1 | 1.9E0 | 54 | 24 | 53 | 24 | 0.48 |
| vI | ng/ml | 1.4E0 | 2.3E0 | 1.7E0 | 2.5E0 | 1.1E0 | 2.4E0 | 6.2E-3 | 6.3E-3 | 4.5E0 | 1.0E1 | 54 | 24 | 53 | 24 | 0.59 |
| vP | ng/ml | 4.3E2 | 5.1E2 | 5.1E2 | 6.3E2 | 3.9E2 | 4.9E2 | 7.0E1 | 1.3E2 | 2.0E3 | 2.2E3 | 54 | 24 | 53 | 24 | 0.58 |
| vT | ng/ml | 7.7E1 | 9.2E1 | 1.1E2 | 1.0E2 | 1.2E2 | 5.9E1 | 3.7E1 | 4.5E1 | 6.9E2 | 3.3E2 | 54 | 24 | 53 | 24 | 0.55 |
| vU | ng/ml | 1.0E-9 | 1.0E-9 | 2.3E1 | 2.5E1 | 3.5E1 | 3.6E1 | 1.0E-9 | 1.0E-9 | 1.3E2 | 1.4E2 | 54 | 24 | 53 | 24 | 0.52 |
| vQ | ng/ml | 3.5E2 | 3.4E2 | 3.6E2 | 3.8E2 | 1.5E2 | 1.4E2 | 6.7E1 | 1.9E2 | 8.1E2 | 6.5E2 | 54 | 24 | 53 | 24 | 0.53 |
| vO | ng/ml | 1.7E3 | 1.8E3 | 1.8E3 | 1.9E3 | 4.5E2 | 4.3E2 | 1.0E3 | 1.1E3 | 3.0E3 | 2.7E3 | 54 | 24 | 53 | 24 | 0.57 |
| vS | ng/ml | 1.3E3 | 1.4E3 | 1.3E3 | 1.3E3 | 3.6E2 | 5.0E2 | 1.0E-9 | 1.0E-9 | 1.8E3 | 1.9E3 | 54 | 24 | 53 | 24 | 0.58 |
| vV | ng/ml | 9.7E2 | 1.2E3 | 1.4E3 | 1.7E3 | 1.6E3 | 1.9E3 | 1.1E2 | 2.2E2 | 1.1E4 | 9.0E3 | 54 | 24 | 53 | 24 | 0.55 |
| vW | ng/ml | 1.4E2 | 1.9E2 | 1.8E2 | 2.2E2 | 1.4E2 | 1.7E2 | 4.3E1 | 6.0E1 | 6.7E2 | 7.7E2 | 54 | 24 | 53 | 24 | 0.61 |
| pF | pg/ml | 5.1E-1 | 6.1E-1 | 6.9E-1 | 9.4E-1 | 9.9E-1 | 9.0E-1 | 1.0E-9 | 1.0E-9 | 9.4E0 | 4.4E0 | 105 | 49 | 97 | 49 | 0.59 |
| pH | ng/ml | 8.9E0 | 8.9E0 | 9.4E0 | 1.3E1 | 4.5E0 | 1.1E1 | 3.4E0 | 3.0E0 | 1.8E1 | 4.7E1 | 27 | 13 | 26 | 13 | 0.58 |
| pI | ng/ml | 7.0E1 | 6.7E1 | 7.0E1 | 7.1E1 | 3.2E1 | 4.3E1 | 2.6E1 | 2.7E1 | 1.5E2 | 2.0E2 | 27 | 13 | 26 | 13 | 0.46 |
| pK | ng/ml | 4.6E-1 | 4.0E-1 | 5.2E-1 | 4.5E-1 | 2.9E-1 | 2.2E-1 | 2.3E-1 | 1.7E-1 | 1.6E0 | 8.6E-1 | 27 | 13 | 26 | 13 | 0.45 |

Figure 4 Continued

Analyte panel data:

Unconstrained panels with 3 analytes, where 1.0E-10 >= 'model p-value' > 0. Contains 911 panels of 37,563,518 total panels evaluated. :
aC{Aw(AD aE aF aG aH al AJ aK AL aM AN AO AP aQ AR AS aU aV aW AX aY aZ BA BB BC bE bF BG bH bI bJ bL bM BN BO bP bQ
bR bS bU bV bW bX bZ cA cB cC cD cE cF cG CH cI cJ cK cL cM cN CO CP CQ cR CS CT CU CV CW CX cY cZ dA DB DC DD DE dF
DG dH DI dJ DK DL dM dN Fr) Ad(aD aH AJ aL aM aN Ao AR aW aX aZ BA Bb BC bE bF bM BN BO bQ bU bW cA cB cE cF cG Ch cK
cL cN Cp cS CT CW cZ Db De dF DI dJ dN) Bb(aJ aL aM aN AR aW aX BA bC bE bF bM Bn Bo bQ bU bW cB cE cF cG Ch cK cN CP CT
CW cZ De dF Dg Di DI dN) Cw(aH aL aN Ao Ap aR aS aW aX BA bC bE bF BN BO bU bW cB cF Ch cN Cp CT cW cZ De Dg Di dJ DI dN)
cB(aJ aN Ao AP aR aW aX BA BC bF Bn Bo bQ bW cA cF cG Ch cN Cp cS cT cW cZ De Dg Di DI dN) De(aL aN Ap aR aW aX BA bC bE
bF Bo bU bW cF Ch cN Cp cT Cu cW cZ Dg Di DI dN fR) Ba(aL aN Ap aR aW BC bE Bn Bo bU cF Ch cN Cp cT cW cZ Dg Di DI dN fR)
Ch(aJ aN Ap aR aW bA BC Bn bU cF cN Cp cT Cu Dg DI dN fR) Ap(aL aN aR aW bA bE Bn Bo cF cN Cp CT cW cZ Di dN) Cp(aN aR aW
bA BC Bo bU cF cN cT cZ Dg Di DI dN) fR(aD aW bA bC bF Bg bO cA cD cE Co CT cZ DI) Bo(aN aW bA BC Bn cF CT Dg DI dN) aW(Ao
Bc Bn cF Ct Cu Dc Dg DI) cT(Ao Ar Bc Bn Dg Di Dk DI) Dg(aL aN bA Bn cF Di) DI(aN bA bC cF Di dN) Ao(aN bC cF cN dN) Di(aN Bc bU
dN) cF(Hc Bn Ct) Ex(Dk Ef) On(It JI) dN(Bn Ct) ArbC CuaN} Ok{Nd(aA Et Fp Fr Hq Hr Hu Hv Hw Hx Ih Ii Ij Ik Il Im In Io Ip Iq Ir Is It Iu Iv
Jg Jh Ji Jj Jk Jl Jm Jn Jo Jp Jq Jr Js Jt Lh Li Lj Lu Lv Lx Ly Lz Ma Mb Mc Md Me Mf Mg Mh Mi Mj Mk Ml Mm Mn Mp Mq Mr Ms Mt
Mu Mv Mw Mx My Mz Na Nb Nc Ne Nf Ng Nh Ni Nj Nk Nl Nm Nn No Nq Nr Ns Nt Nu Nv Nw Nx Ny Oe Of Og Oh Oi Om On Oy Oz Pa Pb
Pc Pd Pe Pf Pg Po Pz Qa Qb Qc Qd Qe) Nc(aA Et Fp Hr Hx Ii Ij Il Im In It Iu Iv Jj Lw Mb Mc Mh Mj Mk Ms Mw My Nb Nf Ng Nh Ni Nj Nq
Ns Nx Of Og Oi Om Oy Pe Pg Po Qb) Ii(aA Et Fp Ij Ik Il Im In Is It Iv Ji Jj Lv Lw Lx Mb Mc Mm Mt My Ne Nf Ng Nh Nj Nk Nl Nr Nw Nx Of
Og Om On Oz Pa) Nl(aA Et Hr Ij Il Im In It Iu Iv Jj Lw Mb Mc Mj Mk Mn Ms Mw My Nf Ng Nh Ni Nm Nq Of Og Om Pe Po Qb) Ij(Et Fp Hr
Iv Jj Lx Mb Mt My Mz Ne Nf Nh Nj Nk Nr Nx On) Il(aA Et Fp Iv Jj Lx Mb Mc My Ne Nh Nj Nk Of Og Om) Nj(aA Hr In It Iv Jj My Nf Ng Ni
Nm Of Og Om) My(aA Et Fp Hr In Iv Jj Lx Mt Ne Nx Og) Iv(Hr In It Jj Mj Ms Ng Of Og Om Po) Jj(Et Fp Hr Hx Mb Ne Nk Nx) Hr(aA Fp Ne
Ng Nk Of) Of(Et In Nx On) Fp(In It) Mb(Ng Og) Nk(In Ni) EtNg ItOm} Et{Nd(aA Fp Fr Hr Hu Hw Ih Ii Ij Ik Il Im In It Iu Iv Ji Jj Jl Jn Jo Jq Jr
Jt Lh Lj Lu Lw Lx Ly Lz Ma Mc Me Mf Mg Mh Mk Mm Mn Mr Ms Mt Mu Mv Mw Mx My Mz Na Nc Nf Ng Nh Ni Nk Nl Nm Nn No Nq Nr
Ns Nu Nw Of Og Oh Oi Om On Oy Oz Pa Pc Pd Pe Pf Pg Pz Qa Qb) Nl(aA Ii Ij Il Jj Ng Of Og Qb) Nc(Ii Il Jj Ms Ng Ni Og Qb) Jj(Fp Iv Mb
Nj) Ii(Fp Iv Nj) FpIj NjaA} Nd{On(aA Ii Jj Mu Mv Mw My Ng Of Og Oy) Mm(aA Jj Mz Og Pa) aA(Fr Ji Nw Pa) JjJt} aN{bU(Aw bF)}

Unconstrained panels with 3 analytes, where 1.0E-9 >= 'model p-value' > 1.0E-10. Contains 3,060 panels of 37,563,518 total panels evaluated. :
Ok{Hr(Et Fr Hq Hu Hv Hw Hx Ih Ii Ik Il Im In Io Ip Iq Ir Is It Iu Jg Jh Ji Jk Jl Jm Jn Jo Jp Jq Jr Js Jt Lh Li Lj Lu Lv Lw Lx Ly Lz Ma Mb Mc
Md Me Mf Mg Mh Mi Mj Mk Ml Mm Mn Mp Mq Mr Ms Mt Mu Mv Mw Mx Mz Na Nb Nf Nh Ni Nm Nn No Nq Nr Ns Nt Nu Nv Nw Nx Ny
Oe Og Oh Oi Om On Oy Oz Pa Pb Pc Pd Pe Pf Pg Po Pz Qa Qb Qc Qd Qe) Jj(aA Fr Hq Hu Hv Hw Ih Ik Im In Io Ip Iq Ir Is It Iu Jg Jh Ji Jk Jl
Jm Jn Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx Mz
Na Nb Nf Ng Nh Ni Nm Nn No Nq Nr Ns Nt Nu Nv Ny Oe Of Og Oh Oi Om On Oy Oz Pa Pb Pc Pd Pe Pf Pg Po Pz Qa Qb Qc Qd Qe)
Nj(aR Et Fp Fr Hu Hw Hx Ih Ik Im Io Ip Iq Ir Is Iu Jn Jo Jr Js Lh Li Lj Lu Lv Lw Lx Ly Lz Ma Mb Mc Md Me Mf Mg Mh Mi Mj Mk Ml Mm
Mn Mp Mq Mr Ms Mt Mu Mv Mw Mx Mz Na Nb Ne Nh Nk Nl Nn No Nq Nr Ns Nt Nu Nv Nw Nx Ny Oe Oh Oi On Oy Oz Pa Pb Pc Pd Pe Pf
Pg Po Pz Qa Qb Qc Qe) Iv(aA Et Fp Fr Hw Hx Ih Ik Im Io Ip Iq Ir Is Iu Jn Jo Js Lh Lu Lv Lw Lx Ly Lz Ma Mb Mc Md Me Mf Mg Mh Mi Mk
Ml Mm Mn Mp Mq Mr Mt Mu Mv Mw Mx Mz Na Nb Ne Nf Nh Ni Nk Nm Nn No Nq Nr Ns Nt Nu Nv Nw Nx Ny Oe Oh Oi On Oy Oz Pa Pb
Pc Pd Pe Pf Pg Pz Qa Qb Qc Qe) Ij(aA Fr Hw Hx Ih Ik Il Im In Io Ip Iq Ir Is It Iu Jg Ji Jr Li Lj Lu Lv Lw Ly Lz Ma Mc Md Me Mf Mg Mh Mi
Mj Mk Ml Mm Mn Mp Mq Mr Ms Mu Mv Mw Mx Na Nb Ng Ni Nm Nn No Nq Ns Nt Nu Nv Nw Ny Oe Of Og Oh Oi Om Oy Oz Pa Pb Pc Pd
Pe Pf Pg Po Pz Qa Qb Qd Qe) Nk(Fp Fr Hq Hu Hv Hw Hx Ih Ik Io Ip Iq Ir Is Jh Ji Jk Jl Jm Jn Jo Jq Jr Js Lh Li Lj Lu Lv Lx Ly Lz Ma Md Me
Mf Mg Mh Mi Ml Mm Mp Mq Mr Mt Mu Mv Mx Mz Na Nb Nc Ne Nk Nn No Nr Ns Nt Nu Nv Nw Nx Ny Oe Oh Oi On Oy Oz Pa Pb Pc Pd
Pf Pg Pz Qa Qc Qd Qe) Il(Fr Hw Hx Ih Ik Im In Io Ip Iq Ir Is It Iu Ji Jo Jr Lj Lu Lv Lw Ly Lz Ma Md Me Mf Mg Mh Mi Mj Mk Ml Mm Mn Mp
Mq Mr Ms Mt Mu Mv Mw Mx Mz Na Nb Nf Ng Ni Nm Nn No Nq Nr Ns Nt Nu Nv Nw Nx Ny Oe Oh Oi On Oy Oz Pa Pb Pc Pd Pe Pf Pg Po
Pz Qa Qb Qe) My(Fr Hw Hx Ih Ik Im Io Iq Ir Is It Iu Ji Jo Jr Lj Lu Lv Lw Ly Lz Ma Mb Mc Md Me Mf Mg Mh Mi Mj Mk Ml Mm Mn Mp Mq
Mr Ms Mu Mv Mw Mx Mz Na Nb Nf Ng Nh Ni Nk Nm Nn No Nq Nr Ns Nt Nu Nv Nw Ny Oe Of Oh Oi Om On Oy Oz Pa Pb Pc Pd Pe Pf Pg
Po Qb) Ii(Fr Hu Hv Hw Hx Ih Io Ip Iq Ir Iu Jg Jh Jk Jl Jm Jn Jo Jp Jq Jr Js Jt Lh Li Lj Lu Ly Lz Ma Md Me Mf Mg Mh Mi Mj Mk Ml Mn Mp
Mq Mr Ms Mu Mv Mw Mx Mz Na Nb Ni Nm Nn No Nq Ns Nt Nu Nv Ny Oe Oh Oi Oy Pb Pc Pd Pe Pf Pg Po Pz Qa Qb Qc Qd Qe) Nc(Fr Hq
Hu Hv Hw Ih Ik Io Ip Ir Is Jg Jh Ji Jk Jl Jm Jn Jo Jp Jq Jr Js Jt Lh Li Lj Lu Lv Lx Lz Ma Md Me Mf Mg Mh Mi Ml Mm Mn Mp Mq Mr Mt
Mu Mv Mx Mz Na Ne Nk Nm Nn No Nr Nt Nu Nv Nw Ny Oe Oh On Oz Pa Pb Pc Pd Pf Pz Qa Qc Qd Qe) Mb(aA Et Fp Fr Hw Hx Ih Ik Im In
Ir It Iu Jo Lu Lv Lw Lx Ly Ma Mc Md Me Mf Mg Mh Mi Mj Mk Ml Mm Mn Mp Mr Ms Mt Mu Mv Mw Mx Mz Na Nb Ne Nf Nh Ni Nk Nm
No Nq Nr Ns Nt Nv Nw Nx Ny Oe Of Oh Oi Om On Oy Oz Pa Pb Pc Pd Pe Pf Pg Po Qb) Og(aA Et Fp Hw Hx Ih Ik Im In Io Ip Iq Ir Is It Iu Lu
Lv Lw Lx Ly Ma Mc Md Mf Mg Mh Mi Mj Mk Ml Mm Mn Mp Ms Mt Mu Mv Mw Mx Nb Ne Nf Ng Nh Ni Nk Nm Nq Nr Ns Nx Ny Oe Of
Oh Om On Oy Oz Pa Pb Pc Pe Pf Pg Po Qb Qc) Of(aA Fp Fr Hw Hx Ih Ik Im Ir Is It Iu Ji Lu Lv Lw Lx Ly Ma Mc Md Mf Mh Mi Mj Mk Ml
Mm Mn Mp Ms Mt Mu Mv Mw Mz Nb Ne Nf Ng Nh Ni Nk Nm Nn Nq Nr Ns Nt Nv Nw Ny Oe Oh Om Oy Oz Pa Pb Pc Pd Pe Pf Pg Po Qb)
In(aA Et Hw Hx Ik Im Io Is It Iu Jq Lu Lv Lw Lx Ly Ma Mc Mf Mg Mh Mi Mj Mk Ml Mm Mn Mp Mr Ms Mt Mu Mv Mw Mx Mz Na Nb Ne
Nf Ng Nh Ni Nm No Nq Nr Ns Nw Nx Oh Oi Om On Oy Oz Pa Pc Pd Pe Pf Pg Po Pz) Om(aA Et Fp Fr Ik Im Io Ip Iq Ir Is Iu Lu Lv Lw Lx Ma
Mc Mf Mg Mh Mj Mk Mm Mn Ms Mt Mw Mz Nb Ne Nf Ng Nh Ni Nk No Nq Nr Ns Nw Nx Oh On Oy Oz Pa Pb Pc Pd Pe Pg Po) Ng(aA Fp Fr
Hw Hx Ik Im It Iu Jg Ji Lu Lv Lw Lx Ly Ma Mc Mh Mi Mj Mk Ml Mm Mn Ms Mt Mw Nb Ne Nf Nh Ni Nk Nq Nr Nx Oh On Oy Oz Pa Pc Pe
Pg Po Qb) It(aA Et Hw Hx Ik Im Is Iu Lu Lv Lw Lx Ly Ma Mc Mg Mh Mi Mj Mk Mm Mn Ms Mt Mu Mv Mw Nb Ne Nf Nh Ni Nk Nm Nq Nr
Ns Nx Oh On Oy Oz Pa Pe Po) Ne(aA Et Fp Hw Hx Im Iu Jo Lv Lw Ma Mc Mg Mh Mj Mk Ml Mm Mn Ms Mv Mw Nb Nf Nh Ni Nk Nm Nq
Nr Ns Nx Oh Oi Oy Oz Pa Pd Pe Pg Po Qb) Et(aA Fp Hw Hx Im Io Iu Jl Jo Lh Lw Ma Mc Mg Mj Mk Mm Ms Mu Mv Mw Nb Nf Ni Nk Nm
Nq Nx Oi Oy Oz Pe Pg Po Pz Qb Qc Qe) Nk(aA Fp Hw Hx Im Iu Lv Lw Ma Mc Mg Mh Mj Mk Mm Ms Mw Nb Nf Nm Nq Nr Ns Nx Oi Oy
Oz Pa Pe Pg Po Qb) Fp(aA Hw Hx Im Iu Lw Ma Mc Mg Mh Mj Mk Mm Ms Mw Nb Nf Nm Nq Nr Nx Oi Oy Oz Pe Pg Po Qb) Ms(aA Hx Ik Ir
Is Iu Ji Lv Lw Lx Ma Mc Mj Mm Mn Mt Nf Nh Ni Nr Nw Nx On Oz Pa Pe Po) Nf(aA Hx Ik Im Iu Lv Lw Lx Ma Mc Mg Mj Mk Mm Mt Mw
Mz Nb Nh Ni Nm Nq Nx Oz Pa Pe) aA(Hw Hx Ir Iu Lu Lv Lz Mi Mj Mk Mw Nb Nh Ni Nq Ns Nx Oy Oz Pe Po Qb) Po(Fr Hw Hx Ji Jr Lj Lv
Lw Lx Mc Mt Nr Nw Nx Oz Pa Pz Qb) Nx(Iu Lw Mc Mg Mj Mk Mw Nb Nm Nq Oy Pe Pz Qb) Hx(Im Jo Lw Lx Mc Mj Mk Mm Mn Nr Pa Pe)
Lw(Iu Lv Mc Mj Mw Ni Nq Oz Pe) Mj(Lv Lx Mc Mx Nh Nr Oz Pa) Mw(Iu Lv Lx Mc On Pc) Oz(Iu Mk Nb Nr Pa Pe) Pe(Lv Nh Pa Pf) Iu(Ik
Im Mm) Nq(Lv Pc) Mc(Mk Oy) Pg(Nw Pa) LvMk LxQb} aC{Ap(AD aE aF aG aH aI AJ aK Al aM An AO aP aQ Ar AS aU aV AX aY aZ BB

Figure 4 Continued

BC bF BG bH bI bJ bL bM bN bO bP bQ bR bS bU bV bW bX bZ cA cC cD cE cG cH cI cJ cK cL cM CO cP CQ cR CS CU CV CX cY dA DB DC DD dE dF DG dH dI dJ DK DL dM FR) Cp(aD aE AF aG aH aI AJ aK AL aM An AO aP aQ Ar AS aU aV AX aY aZ bB bE bF BG bH bI bJ bL bM BN bO bP bQ bR bS bV bW bX bZ cA cC cD cE cG cH cI cJ cK cL cM CO cP CQ cR CS Ct CU CV cW CX cY dA DB DC DD dE dF dG dH dI dJ DK dL dM FR) Ba(aD aE AF aG aH aI AJ aK Al aM An AO aP aQ Ar AS aU aV AX aY aZ bA bB bF BG bH bI bJ bL bM bN bO bP bQ bR bS bV bW bX bZ cA cC cD cE cG cH cI cJ cK cL cM CO cP CQ cR CS Ct CU CV CX cY dA DB DC DD dE dF dG dH dI dJ DK dL dM Fr) De(aD aE AF aG aH aI AJ aK Al aM An AO aP aQ Ar AS aU aV Ax aY aZ bB Bc BG bH bI bJ bL bM BN bO bP bQ bR bS bV bX bZ cA cC cD cE cG cH cI cJ cK cL cM CO cP CQ cR CS Ct cU CV CX cY dA DB DC DD dE dF dG dH dI dJ DK dL dM Fr) Cw(aD aE AF aG aI AJ aK Al aM An aO aP aQ Ar As aU aV Ax aY aZ bB Bc BG bH bI bJ bL bM bP bQ bR bS bV bX bZ cA cC cD cE cG cH cI cJ cK cL cM CO cP CQ cR CS CU CV CX cY dA DB DC DD dE dF dG dH dI dJ DK dL dM FR) Ch(aF aK aL aM An Ao aP Ar AS aU aV Ax aY aZ bB Bc BG bH bI bJ bL bN bO bP bR bS bV bX bZ cA cC cD cH cI cJ cL cM CO CQ cR CS CU CV CX cY dA DB DC DD dE dG dH dI dJ DK dL dM Ex FR) cB(AA aD aE aF aG aH aI aK AL aM An aO aQ Ar aS aU aV Ax aY aZ bB bE BG bH bI bJ bL bM bN bO bP bR bS bU bV bX bZ cC cD cE cH cI cJ cK cL cM CO cP cQ cR Ct CU CV cX cY dA dB DC DD dE dF dG dH dI dJ DK dL dM FR) fR(Ad aF aG Aj aL aM aN AO aP aQ AS aU Aw AX aY aZ bB Bc bE bH bJ bL bM BN Bo bP bQ bR bS bW bX cF cG cI cJ cK cL cM cN cO CQ CS CU Cv cW cX DB Dc Dd dE dF Dg DI dJ Dk dL dM dN Fr) Ad(aE AF aG aI aK Al An aO aP aQ AS aU aV Ax aY bB BG bH bI bJ bL bP bR bS bV bX bZ cC cD cH cI cJ cM CO cP CQ cR Cs CU CV CX cY dA dB DC DD dE DG dH DK DL dM Fr) Ch(aF aK aL aM An Ao aP Ar AS aV AX aY aZ bB bE bF Bg bM bN Bo bQ bR bS bV bW bX cA cC cD cE cG cI cJ cK cL Co cP Cq cR CS Ct Cv cW Cx cZ Dc Dd dF dG dH DI dJ Dk dM Fr) Dg(Af aH AJ An Ao AR aX aZ BC bE bF Bg bN bO bQ bR bU cA cD cE cG cK cN Co cP Ct cW cZ Db Dc dJ DI dN Fr) Di(aJ aM Ao AR aW aX bA bC bE bF Bg bM BN Bo bW cF cG cN Co Ct Cu Cv cW cZ Dc dF Dk Fr) DI(aJ aL Ao aP AR aX Bc bE bF Bg Bn bQ bU bV bW cA cE cG cL cN Co cS Ct cW cZ dF dJ Fr) Bn(Af aJ aN Ao AR aX bA BC bE bF Bg bQ bU bW cG cN Co Ct Cu Dc dF Fr) Bo(aJ Ao AR aX bE bF Bg bU bW cA cG cN Co cS Cu Cv cW cZ Dc dF Dk Fr) cF(aJ aN AR bA bB bC bF Bg bQ bW cA cE cG cN Co cT Cu Dc dF Dk dN Fr) cT(Af Aj Al An As aW Ax Bg Co Cq Cs Ct Cu Cv Cx Db Dc Dd dN Fr) Ao(aJ AR aX bA Bc bE bF bQ bU bV bW cA cG Ct Cu cW cZ dF) aW(aN AR bA bC bF Bg bR bU bW cG Co Cv Dk dN Fr) Ct(aN AR BC bE bF bU cG cN cW dF Ex) Bc(aN AR bA bC bE bF bU cN cW dN) dN(AR bF Bg bR bU Co Cu Dc Dk) aN(Ar bF Bg bU Cu Dc Dk) Co(aR bA bC bU bW cN) Cu(aL aR bC bF cN cZ) On(aR Hx Iu Na Qb) bF(aR bR bU cN Dc) Bg(aR bA bC cN) Ar(bA bU cN) Dc(bA bC cN) Dk(bA bC) EtaR FrbC} Et{Nl(Fp Hr Hw Hx Im In Io It Iu Iv Jo Lw Mb Mc Mg Mj Mk Mm Mn Ms Mu Mv Mw My Nh Ni Nm Nq Ns Oi Om Oy Pa Pe Pg Pz Qc) Nc(aA Fp Hr Hw Hx Ij Im In Io It Iu Iv Jo Lw Mb Mc Mj Mk Mm Mu Mv Mw My Nh Nm Nq Ns Of Oi Om Oy Pa Pe Pg Pz Qc) Nd(Hq Hv Hx Io Ip Iq Ir Is Jg Jh Jk Jm Jp Js Li Lv Mb Md Mi Mj Ml Mp Mq Nb Ne Nj Nt Nv Nx Ny Oe Pb Po Qc Qd Qe) Jj(Hx Ii Ij Ik Il Im It Jr Lj Lv Lw Lx Ly Ms Mt Mu Mw My Ne Nh Ni Nk Nq Nr Nx Of Og Oh Om Oy Oz Pa Qa Qb) Ii(aA Ik Im Is Ji Jq Jr Lj Lw Lx Mb Mr Mt Ne Nk Nr Nx On Oz Pa Pe Po Qa Qe) Ms(aA Fp Iv Ji Lw Mb Ne Ng Ni Nj Nk Nx Of Pa) Mb(aA Ij Il Lw My Ng Nq Of Og Oy Pz) Nj(Ij Il In Ng Ni Nm Of Og Pz Qb) Iv(aA Ij Il In Ng Of Og Om Pz Qb) aA(Fp Hx Il My Ne Nx Og Oy Qb) Il(Fp Jr Lj Lz Ne Nk Of) Fp(My Ng Of Og Qb) Ne(Ij Ng Of Og Qb) Nk(Ni Og Qb) Of(Ni Nx Og) LxMy IjJi ImOg} Nd{Mm(Fr Ij Il Im In Iv Ji Jq Jt Lw Lx Mc Mn Mr Na Nc Ng No Nr Nw Of Om On Oz Pd Pe) aA(Is Iv Jg Jj Jp Jq Jt Lh Li Lw Lx Mn Mt Mz Nc No Nr Nv Nx Of Og Om Pc Po Qe) On(aN Ij Il In Iu Iv Jr Lw Mg Mk Ms Mz Nc Nm Nq Oi Om Oz Pa) Jj(Fr Is Ji Lh Li Lx Mn Mt Nr Nv Nw Po Qa Qe) Ji(Ij Im Lx Mn Og Pa) Lw(Fr Lx Nw) NwOg} aN{cB(AW BA Bb bC bF Cp cT) Aw(bM cF cK cT DI) On(Jl Nj Tj) bU(Ba Bb Cp) cF(bF Cp) DIcT} On{Jj(Iv Ms Nj NI) Ii(Iv Nj NI) TjJd JlaR} aW{cB(aR Aw bF) AwbU} Tj{Jd(Ir Pa)} RifNrN

Unconstrained panels with 3 analytes, where 1.0E-8 >= 'model p-value' > 1.0E-9. Contains 7,527 panels of 37,563,518 total panels evaluated. : Ok{Pz(aA Fp Fr Hq Hu Hv Hw Hx Ih Ik Im Io Ip Iq Ir Is It Iu Jg Jh Ji Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Ne Nf Ng Nh Ni Nk Nm Nn No Nq Nr Ns Nt Nv Nw Ny Oe Of Og Oh Oi Om On Oy Oz Pa Pb Pc Pd Pe Pf Pg Qa Qb Qc Qd Qe) Hw(Fr Hq Hu Hv Hx Ih Ik Im Io Ip Iq Ir Is Iu Jg Jh Ji Jk Jl Jm Jn Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx Mz Na Nb Nf Nh Ni Nm Nn No Nq Nr Ns Nt Nu Nv Nw Nx Ny Oe Oh Oi Om On Oy Oz Pa Pb Pc Pd Pe Pf Pg Qa Qb Qc Qd Qe) Qb(Fr Hq Hu Hv Hx Ih Ik Im In Io Ip Iq Ir Is It Iu Jg Jh Ji Jk Jl Jm Jn Jo Jp Jq Jr Js Jt Lh Li Lj Lu Lv Lw Ly Lz Ma Mc Md Me Mf Mg Mh Mi Mj Mk Ml Mm Mn Mp Mq Mr Ms Mt Mu Mv Mw Mx Mz Na Nb Nf Nh Ni Nm Nn No Nq Nr Ns Nt Nu Nv Nw Ny Oe Oh Oi Om On Oy Oz Pa Pb Pc Pd Pe Pf Pg Qa Qc Qd Qe) Lx(aA Et Fp Fr Hq Hu Hv Ih Ik Im Io Ip Iq Ir Is Iu Jh Ji Jk Jl Jn Jo Jr Js Jt Lh Li Lu Lv Lw Ly Lz Ma Mc Md Me Mf Mg Mh Mi Mk Ml Mm Mn Mp Mq Mr Mt Mu Mv Mx Mz Na Nb Ne Nh Ni Nk Nm Nn No Nq Nr Ns Nt Nu Nv Nw Nx Ny Oe Oh Oi On Oy Oz Pa Pb Pc Pd Pe Pf Pg Qa Qc Qd Qe) Mm(aA Fr Hu Ih Ik Im Io Ip Iq Ir Is Ji Jk Jl Jn Jo Jr Js Jt Lh Li Lj Lu Lv Lw Ly Lz Ma Mc Md Me Mf Mg Mh Mi Mj Mk Ml Mn Mp Mq Mr Mt Mu Mv Mw Mx Mz Na Nb Nh Ni Nm Nn No Nq Nr Ns Nt Nu Nv Nw Nx Ny Oe Oh Oi On Oy Oz Pa Pb Pc Pd Pe Pf Pg Po Qa Qc Qd Qe) Nm(aA Fr Hx Ih Ik Im Io Ip Iq Ir Is Iu Jg Ji Jo Jr Js Li Lj Lu Lv Lw Ly Lz Ma Mc Md Me Mf Mg Mh Mi Mj Mk Ml Mn Mp Mq Mr Ms Mt Mu Mv Mw Mx Mz Na Nb Ng Nh Ni Nn No Nq Nr Ns Nt Nu Nv Nw Ny Oe Oh Oi Om On Oy Oz Pa Pb Pc Pd Pe Pf Pg Po Qa Qc Qd Qe) Mg(aA Fr Hx Ih Ik Im Io Ip Iq Ir Is Iu Jg Ji Jo Jr Js Li Lj Lu Lv Lw Ly Lz Ma Mc Md Me Mf Mh Mi Mj Mk Ml Mn Mp Mq Mr Ms Mt Mu Mv Mw Mx Mz Na Nb Ng Nh Ni Nn No Nq Nr Ns Nt Nu Nv Nw Ny Oe Of Oh Oi On Oy Oz Pa Pb Pc Pd Pe Pf Pg Po Qa Qc Qd Qe) Mt(aA Et Fp Hu Hx Ih Ik Im Io Ip Iq Ir Is Iu Jk Jl Jn Jo Jr Js Lh Li Lu Lv Lw Ly Lz Ma Mc Md Me Mf Mh Mi Mj Mk Ml Mn Mp Mq Mr Mu Mv Mw Mx Mz Na Nb Ne Nh Ni Nk Nn No Nq Nr Ns Nt Nv Nw Nx Ny Oe Oh Oi On Oy Oz Pa Pb Pc Pd Pe Pf Pg Qa Qc Qe) Nb(Fr Hu Hx Ih Ik Im Io Ip Iq Ir Is Iu Jg Ji Jl Jn Jo Jq Jr Lh Li Lj Lu Lv Lw Ly Lz Ma Mc Md Me Mf Mh Mi Mj Mk Ml Mn Mp Mq Mr Ms Mu Mv Mw Mx Mz Na Nh Ni Nn No Nq Nr Ns Nt Nu Nv Nw Ny Oe Oh Oi On Oy Pa Pb Pc Pd Pe Pf Pg Po Qa Qc Qd Qe) Lv(Et Fp Fr Hq Hu Hv Hx Ih Ik Im Io Ip Iq Ir Is Iu Jh Ji Jk Jl Jn Jo Jr Js Lh Li Lj Lu Ly Lz Ma Mc Md Me Mf Mh Mi Ml Mn Mp Mq Mr Mu Mv Mx Mz Na Nh Ni Nn No Nr Ns Nt Nu Nv Nx Ny Oe Oh Oi On Oy Oz Pa Pb Pc Pd Pf Pg Qa Qc Qd Qe) Mj(Fr Hq Hu Hv Ih Ik Im Io Ip Iq Ir Is Iu Jg Jh Ji Jk Jl Jm Jn Jo Jp Jq Jr Js Jt Lh Li Lj Lu Ly Lz Ma Md Me Mf Mh Mi Mk Ml Mn Mp Mq Mr Mu Mv Mw Mx Mz Na Ni Nn No Nq Ns Nt Nu Nv Nw Ny Oe Oh Oi On Oy Pb Pc Pd Pe Pf Pg Po Qa Qc Qd Qe) Lw(aA Fr Hq Hu Hv Ih Ik Im Io Ip Iq Ir Is Jg Jh Ji Jk Jl Jm Jn Jo Jp Jq Jr Js Jt Lh Li Lj Lu Ly Lz Ma Md Me Mf Mh Mi Mk Ml Mn Mp Mq Mr Mu Mv Mx Mz Na Nh Nn No Nr Ns Nt Nu Nv Nw Ny Oe Oh Oi On Oy Pa Pb Pc Pd Pf Pg Qa Qc Qd Qe) Hx(Fr Hq Hu Hv Ih Ik Io Ip Iq Ir Is Iu Jg Jh Ji Jk Jl Jm Jn Jp Jq Jr Js Jt Lh Li Lj Lu Ly Lz Ma Md Me Mf Mh Mi Ml Mp Mq Mr Mu Mv Mw Mx Mz Na Nh Ni Nn No Nq Ns Nt Nu Nv Nw Nx Ny Oe Oh Oi Om On Oy Oz Pb Pc Pd Pf Pg Qa Qc Qd Qe) Po(Hq Hu Hv Ih Ik Im Io Ip Iq Ir Is Iu Jg Jh Jk Jl Jm Jn Jo Jq Jr Js Jt Lh Li Lj Lu Ly Lz Ma Md Me Mf Mh Mi Mk Ml Mn Mp Mq Mr Mu Mv Mw Mx Mz Na Nf Nh Ni Nn No Nq Ns Nt Nu Nv Ny Oe Oh Oi On Oy Pb Pc Pd Pe Pf Pg Qa Qc Qd Qe) Mc(aA Fr Hq Hu Hv Ih Ik Im Io Ip Iq Ir Is Iu Jh Ji Jk Jn Jo Jq Jr Js Lh Li Lj Lu Ly Lz Ma Md Me Mf Mh Mi Ml Mn Mp Mq Mr Mu Mv Mx Mz Na Nh Ni Nn No Nq Nr Ns Nt Nu Nv Nw Ny Oe Oh Oi On Oz Pa Pb Pc Pd Pe Pf Pg Qa Qc Qd Qe) Mk(Fr Hu Ih Ik Im Io Ip Iq Ir Is Iu Jg Ji Jl Jn Jo Jq Jr Js Lh Li Lj Lu Ly Lz Ma Md Me Mf Mh Mi Ml Mn Mp Mq Mr Ms

Ns Nt Nu Nv Nw Nx Ny Oe Oh Om On Pa Pb Pc Pd Pe Pf Pg Po Qa Qc Qd Qe) Mk(Fr Hr Hu Hv Hx Ih Ij Ik Il Im In Is It Jg Jk Jl Jn Jp Jq Jt Lh Li Lu Lv Lx Ly Lz Ma Me Mf Mg Mj Ml Mn Mp Mq Mr Mt Mx My Mz Na Nb Ni No Nq Nr Ns Nt Nu Nw Nx Ny Oe Oh Om On Oy Pa Pc Pd Pe Pf Pg Po Pz Qa Qb Qc Qd Qe) Hx(Fr Hq Hr Hu Hv Ih Ik Im Ip Iq Is It Jg Jh Jk Jl Jm Jn Jp Jq Js Jt Lh Li Lu Lv Ly Lz Ma Md Me Mf Mg Mi Mj Ml Mn Mp Mq Mt Mx Mz Na Nb Nn No Nr Ns Nt Nu Nv Nw Nx Ny Oe Oh Om On Pb Pc Pd Pe Pf Pg Po Qa Qb Qc Qd Qe) In(Fr Hq Hr Hu Hv Ih Ik Im Ip Iq Ir Is It Jg Jh Jk Jl Jm Jn Jp Js Jt Lh Li Lu Lv Lx Ly Lz Ma Md Me Mf Mg Mi Mj Ml Mn Mp Mq Mr Mt Mx Mz Na Nb Nn No Nr Ns Nt Nu Nv Nw Ny Oe Oh On Pb Pc Pd Pe Pf Pg Pi Po Qa Qc Qd Qe) Nx(Fr Hq Hr Hu Hv Ih Ik Im It Jg Jh Jk Jl Jm Jn Jp Jq Js Jt Lh Li Lu Lv Lx Ly Lz Ma Md Me Mf Mg Mi Mj Ml Mn Mp Mq Mr Mt Mx Mz Na Nb No Nr Ns Nt Nu Nv Nw Ny Oe Oh Om On Pa Pb Pc Pd Pe Pf Pg Po Qa Qc Qd Qe) Om(Fr Hq Hr Hu Hv Ih Ik Im Ip Iq Ir Jg Jh Jk Jl Jm Jn Jp Jq Js Jt Lh Li Lu Lv Ly Lz Ma Md Me Mf Mg Mi Mj Ml Mn Mp Mq Mr Mt Mx Mz Na Nb Nn No Nr Ns Nt Nu Nv Nw Ny Oe Oh On Pb Pc Pd Pe Pf Pg Po Qa Qc Qd Qe) Pa(Fr Hq Hr Hu Hv Ih Ik Im Ip Iq Is It Jg Jh Jk Jl Jm Jn Jp Jq Js Jt Lh Li Lu Lv Lx Ly Lz Ma Md Me Mf Mg Mi Mj Ml Mn Mp Mq Mr Mt Mx Mz Na Nb Nn No Nr Ns Nt Nu Nv Nw Ny Oe Oh On Pb Pc Pd Pf Po Qa Qc Qd Qe) Ni(Fr Hq Hu Hv Ih Ik Ip Iq Ir Is Jg Jh Jk Jl Jm Jn Jp Jq Js Jt Lh Li Lu Lv Ly Lz Ma Md Me Mf Mg Mi Mj Ml Mn Mp Mq Mr Mt Mx Mz Na Nb Nn No Nr Ns Nt Nu Nv Nw Ny Oe Oh On Pb Pc Pd Pe Pf Pg Po Qa Qc Qd Qe) Lx(Fp Fr Hq Hr Hu Hv iA Ih Ik Im It Jg Jh Jk Jl Jm Jn Jp Jq Js Jt Lh Li Lu Ly Ma Md Me Mf Mg Mi Mj Ml Mn Mp Mq Mr Mt Mx Mz Na Nb Nk Nn No Nr Ns Nt Nu Nv Nw Ny Oe Oh Pb Pc Pd Pe Pg Po Qa Qc Qd Qe) Nk(Fr Hq Hu Hv Ih Ik Ip Iq Ir Is Jg Jh Jk Jl Jm Jn Jp Jq Js Jt Lh Li Lu Lv Ly Lz Ma Md Me Mf Mg Mi Ml Mn Mp Mq Mr Mt Mx Mz Na Nb Nn No Ns Nt Nu Nv Nw Ny Oe Oh On Pb Pc Pd Pf Pg Po Qa Qd Qe) Pz(Fr Hq Hr Hu Hv Ih Ik Ip Iq Ir Jg Jh Jk Jl Jm Jn Jp Jq Js Jt Lh Li Lu Lv Ly Lz Ma Md Me Mf Mg Mi Mj Ml Mn Mp Mq Mr Mx Mz Na Nb Nn No Ns Nu Nv Nw Ny Oe Oh On Pb Pc Pd Pe Pf Pg Po Qc Qd Qe) Im(Hq Hr Hu Hv iA Ih Ik Is It Jh Jk Jl Jm Jn Jp Jq Jt Lh Li Lu Lv Ly Lz Ma Me Mf Mg Mj Ml Mn Mp Mq Mr Mt Mx Mz Na Nb Nn No Nr Ns Nt Nu Nw Ny Oe Oh Om On Pb Pc Pd Pe Pf Pg Po Qa Qc Qd Qe) Nq(Hq Hr Hu Hv iA Ih Ik Ip Iq Ir Is It Jk Jl Jm Jn Jp Js Jt Lh Li Ly Lz Ma Md Me Mf Mg Mi Mj Ml Mn Mp Mq Mr Mx Na Nb Nn No Nr Ns Nt Nu Nv Ny Oe Oh Oy Pb Pd Pe Pf Pg Po Qa Qc Qd Qe) Oy(Fr Hq Hr Hu Hv Ih Ik Ip Iq Ir Is It Jk Jl Jm Jn Jp Js Jt Lh Li Ly Lz Ma Md Me Mf Mg Mi Mj Mn Mp Mq Mr Mx Mz Na Nb Nn No Ns Nt Nu Nv Nw Ny Oe Oh Pb Pd Pe Pf Pg Po Qa Qc Qd Qe) Qb(Fr Hq Hr Hu Hv Ih Ik Ip Iq Ir Jg Jh Jk Jl Jm Jn Jp Js Jt Lh Li Lu Ly Lz Ma Md Me Mf Mi Mj Ml Mn Mp Mq Mr Na Nb Nn No Ns Nt Nu Nv Nw Ny Oe Oh On Pb Pc Pd Pe Pf Pg Po Qc Qd) Lv(Fp Hq Hr Hu Ih Ik Is It Jh Jk Jl Jn Jp Jq Js Jt Lh Li Lu Ly Ma Mf Mg Mi Mj Ml Mn Mp Mq Mr Mt Mx Mz Na Nb Nn No Nr Ns Nt Ny Oe Oh On Pb Pc Pd Pe Pf Pg Po Qa Qc Qd Qe) Hr(Hu Hv Ih Ij Ik Is It Jk Jl Jn Jp Jq Jt Lh Li Lu Ly Ma Me Mf Mg Mj Ml Mn Mp Mq Mr Mt Mx My Mz Na Nn No Nr Ns Nt Nu Nw Ny Oe Oh On Pc Pd Pe Pf Pg Po Qa Qc Qd Qe) Jq(aA Hq Hu Ik Ir Jh Jk Jl Jn Jp Js Jt Lh Lu Ly Ma Md Mf Mg Mi Mj Ml Mn Mp Mr Mt Mx Mz Nb No Nr Ns Nt Nu Nv Ny Oe Oh Pb Pc Pd Pe Pg Po Qa Qc Qd Qe) Fp(Fr Hq Hu Hv Ih Ik Ip Iq Ir Is Jg Jh Jm Jp Js Li Lu Ly Lz Md Me Mf Mi Ml Mn Mq Mr Mt Mx Mz Na Nb Nn No Nr Nt Nu Nv Nw Ny Oe Oh On Pb Pc Pf Qa Qd) Ne(Fr Hq Hu Hv Ih Ik Ip Iq Ir Is Jg Jh Jm Jn Jp Js Jt Li Ly Lz Ma Md Me Mf Mi Ml Mq Mr Mt Mx Nb Nn Nr Nt Nu Nv Nw Ny Oe Oh On Pb Pc Pf Po Qa Qd Qe) Mg(Hu Hv Ih Ij Ik Is It Jk Jl Jt Lh Li Lu Ly Ma Me Mf Mj Ml Mn Mp Mq Mr Mt Mx My Mz Na Ng Nn No Nr Ns Nt Oe Oh On Pc Pd Pe Pg Po Qa Qc Qd Qe) Mz(aA Hq Hu Ik It Jk Jl Jn Jp Js Jt Lh Lu Ly Ma Md Mf Mi Mj Ml Mn Mp Mr Mt Mx Nb Nn Nr Ns Nt Nv Ny Oe Oh Pb Pc Pd Pe Pg Po Qa Qc Qd Qe) Pe(Hu Hv Ik Is It Jk Jl Lh Li Lu Ly Ma Me Mf Mi Mj Ml Mn Mp Mq Mr Mt Mx Na Nb Nn No Nr Ns Nt Oe Oh Pb Pc Pf Pg Po Qa Qc Qd Qe) Ij(Fr Hq Hu Ip Iq Ir Jg Jh Jk Jl Jm Jn Jp Js Lu Ly Lz Ma Md Mf Mi Mj Mn Mp Nb Nn Ns Nu Nv Ny Oe Pb Pc Pd Pf Pg Qc Qd) Ml(Hq Hu Ik It Jk Jl Jn Jt Lh Lu Ly Ma Mf Mj Mn Mp Mr Mt Mx Nn Np Mr Mt Mx Nb No Nr Ns Nt Ny Oe Oh Pb Pc Pd Pg Po Qc Qd Qe) iA(aF aP BA bL Bo bS bU cC cE cM cN cQ cT Cw dD gL hB hG Hq Hu iH Iq Jg Jh Jj Mq Mr Na No Nv Oh oK On Pb Pc Qv) Nr(Hq Hu Ik It Iv Jk Jl Jm Jn Jp Jt Lh Lu Ly Ma Mf Mj Mp Mr Mt Mx Na Nn Ns Nu Ny Oe Pb Pc Pd Pg Po Qc Qd Qe) My(Hq Hu Hv Ih Ip Iq Ir It Jk Jl Jm Jn Jp Js Lh Lz Ma Md Me Mi Mj Mp Mq Nb Nn Nu Nv Ny Oe Pb Pd Pf Pg Qc Qd) Lu(Hq Hu Ik Is It Jk Jl Lh Ly Ma Mf Mj Mn Mp Mr Mt Mx Na Nb Nn No Ns Nt Oe Oh Pb Pc Pd Pg Po Qa Qc Qd Qe) Ns(Hu Ik Is It Jk Jl Lh Li Ly Ma Mf Mj Mn Mp Mr Mt Mx Na Ng No Nt Nu Oh On Pc Pd Pg Qa Qc Qd Qe) Iv(Fr Hv Ih Ik Iq Ir Is Jg Jh Js Li Lz Md Me Mx Nb No Nv Nw Ny Oh On Pb Pf Qa) Ng(Hq Hu Hv Ip Iq Ir Is It Jk Jm Jn Jp Js Lh Lz Ma Md Mi Mj Nb Nn Nu Nv Nw Ny Oe Pb Pd Pf Po) Mt(Hq Hu Ik It Jk Jl Jn Jp Jt Lh Ly Ma Mf Mj Mp Mr Mx Na Nn Ny Oe Pc Pd Pg Po Qc Qd Qe) It(Hu Hv Ik Ir Is Jn Jt Lh Ly Ma Me Mf Mp Mq Mr Mx Na Nn No Nt Nu Pg Qa Qc Qd Qe) Mf(aA Hu Ik Jk Jl Lh Ly Ma Mj Mp Mr Mx Na Nn No Nt Nu Oe Pc Pd Pg Qa Qc Qd Qe) Qc(Hu Is Jk Jl Jn Lh Li Ly Ma Mn Mp Mr Mx Na Nn No Nt Oe Oh Pc Pd Pg Qa Qe) aA(Fr Hq Hv Ik Ip Iq Ir Is Jg Jh Jn Js Jt Li Md Mn Mq Mr No Nv Nw On Pb Pf) Mp(Hu Ik Is Jl Lh Ly Ma Mn Mr Mx Na Nt Nw Oh On Pc Pg Po Qa Qd Qe) Il(Fr Hq Hu Ip Iq Ir Jh Jk Jm Jp Js Md Mi Mn Nv Ny Oe Pb Pg) Ly(Hu Jk Jl Lh Mj Mr Mx Na Nn No Nt Oe Pc Pd Pg Qa Qd Qe) Mx(Hu Jk Jk Jl Lh Ma Mj Nn Oe Pc Pd Pg Po Qd Qe) Qa(Hu Jk Jl Jp Jt Lh Ma Mj Nn Oe Pd Pg Po Qe) Lh(Ik Li Mn Mr Na No Nt Nw Oh On Pc Qd Qe) Pg(Ik Is Jl Mr Na No Nt Nw On Pc Pf Qd Qe) Mr(Hq Hu Jk Mi Mj Nb Ny Pb Po Qe) Nj(aN aW bA bR bU cT Di Ip Iq Ir) Ik(Hu Jk Lz Ma Na Nn No Oe Pd) Nd(aN aR aW bA bR cD cT Di) Qe(Is Jk Jl Mj Na No Nt Oe) iH(bU cM Di Jj oK qT qU tF) Jk(Is Jl Na No Nt On Pc) Of(Ip Iq Ir Jm Lz Md) Pc(Hu Ma Na Nn Oe Pd) Po(Jl Mj No Nw On) Di(aR gP qY tV) Mj(Is Na No Nt) Og(Ip Iq Ir Nn) oK(Cw Hf Jj Na) Tj(Fa Jd On) Qd(Lz Na No) aR(bR cT On) Mb(Iq Ir) NoMa Mslr NbJl HfqU JnJs KsqQ RirN OnaN UvtF tTzH tVqW} aC{On(AD aE aF aG aH al AJ Al aM An AO AP aQ Ar AS aU aV Aw Ax aY aZ BA bB Bc bE bF BG bH bI bJ bL bM BN BO bP bQ bS bV bW bX bZ cC cE cG CH cI cJ cK cL cM cN CO CP CQ cR CS cT cU cV cW CX cY dA dB DC dD De dF Dg dH dI dK DL dM dN Fp FR Fw Hu Hv Hw Ih Ik Im In Ji Jm Jn Jo Jp Jq Jr Jt Li Lu Lv Lx Ly Lz Ma Mc Md Me Mf Mg Mh Mi Mj Ml Mm Mn Mp Mq Mr Ms Mt Mu Mw Mx Mz Nb Nc Ne Ng Nh Nk Nl Nm Nn No Nq Nt Nu Nw Nx Ny Oe Og Oh Oi Ok Oy Oz Pb Pc Pd Pe Pf Pg Pz Qa Qc Qd Qe) Ok(Ad aE aF aG aH al aK AO Ar aS aV AW aX aY aZ BA Bb bC bE Bg bH bJ bL BN BO bQ bR bU bV cA cB cC cD cF CH cJ cK cN cO Cp cQ CT Cw DB dC DE dG Di dJ Dk dL dN Fp FR Hu Ii Ij Il Im In Io Ip Iq Ir Is It Iu Iv Jg Jh Jj Jj Jt Lw Lx Ly Lz Ma Mb Mc Mg Mi Mj Mk Mm Mn Mr Ms Mt Mu Mw My Mz Na Nc Ne Nf Nh Ni Nk Nl Nm Nn Nr Ns Nw Nx Ny Oh Oi Om Oy Pa Pb Pc Pd Pe Pg zH Tj) Bb(Aa cF Fp gL GP Hu Ih Ii Ij Ik Il Im In Ip Iq Ir Iu Iv Jg Jh Ji Jj Jp Jt Lh Li Lu Lv Lx Ly Lz Ma Mb Md Me Mf Mg Mh Mi Mj Mk Ml Mn Mp Mq Mr Ms Mt Mu Mw Mx My Mz Na Nb Nc Ne Nf Ng Nh Ni Nk Nl Nm Nn No Nq Nr Ns Nt Nu Nv Nw Nx Ny Og Oh Oi Om Oy Oz Pa Pb Pc Pd Pe Pf Pg Po Tj) Of(Ad Af aK aL Ao Ap Ar AW aX BA BC bE Bg bN bQ bR bU bV bW cB cF Ch cK Cp cR cZ Db De Dg Di dJ Dl dN FR Hr Hu Hx Il Io Ip Iq Ir Iv Jk Jl Jp Jq Jt Lh Li Mb Mc Mg Mk Mr Mt Mu Mv Mw My Mz Na Nd Ne Nf Nh Ni Nj Nk Nl Nm No Ns Nx Ny Oe Om Pd Po Qa Qb Qd Qe) dF(aD aE AF aG aH al AJ aK AL aM aO aP aQ AS aU aV AX aY aZ bA bB bC bE bG bH bI bJ bL bM bN bO bP bQ bS bV bW bX bZ cA cC cD cE cH cI cJ cK cL cM cN cO cP CQ cR CS cT cU cV cW CX cY cZ dA dB dC dD dE dG dH dI dJ dK dL dM Em} cG(aD aE AF aG aH al AJ aK Al aM aO aP aQ AS aU aV AX aY aZ bA bB bC bG bH bI bJ bL bM bN bO bP bQ bS bV bW bX bZ cA cC cD cE cH cI cJ cK cL cM cO cP CQ cR CS cT cU cV CX cY cZ dA DB dC DD dE dG dH dI dJ dK dL dM) bC(aD aE aF aG aH al aJ aK aL aM aO aP aQ aS aU aV aX aY aZ bA bE bG bH bI bJ bL bM bN bO bP bQ bS bV bW bX bZ cA cC cD cE cH cI cJ cK cL cM cO cP cQ cR cS cU cV cW cX cY cZ dA dB dC dD dE dG dH dI dJ dK dL dM Ex Jg Jh Mv Nw Om) aR(aA aD aE AF aG aH al Aj aK AL aM An aO aP aQ AS aU aV aX aY aZ bB bE bH bM bN bO bP bQ bV bW bX bZ cA cC cD cI cK cL cP Cq cR CS CV CX cY cZ DB DD dG dH dI dJ dL dM

Nv Nw Ny Oe Oh Oi On Pb Pc Pd Pf Pg Qa Qc Qe) Lh(Fr Ih Io Ip Iq Ir Is Jo Lu Ly Lz Ma Md Me Mf Mg Mh Mi Ml Mp Mq Mr Mu Mv Mx Mz Na Nm Nn No Nq Ns Nt Nu Nv Nw Ny Oe Oh Oi Oy Pb Pc Pd Pf Pg Qa Qc) Nu(Fr Ih Io Ip Iq Ir Is Ji Jo Jr Lj Lu Lz Md Me Mf Mi Ml Mn Mp Mq Mr Mt Mu Mv Mx Mz Na Nn No Nt Nv Nw Ny Oe Oh On Pb Pc Pd Pf Pz Qa Qc Qe) Qa(Fr Ih Ik Io Ip Iq Ir Is Ji Lu Ly Lz Ma Md Me Mf Mh Mi Ml Mn Mp Mq Mr Mu Mv Mx Mz Na Nn No Ns Nt Nv Nw Ny Oe Oh Oi On Pb Pc Pd Pf Pg) Lj(Fr Ik Io Ip Iq Ir Is Ji Jr Lu Lx Ly Lz Md Me Mf Mi Ml Mn Mp Mq Mr Mt Mu Mv Mx Mz Na Nn No Nt Nv Nw Ny Oe On Pb Pc Pd Pf) Qe(Fr Ih Io Ip Iq Ir Lu Ly Lz Md Me Mf Mi Ml Mp Mq Mr Mu Mv Mx Mz Na Nn No Nt Nv Nw Ny Oe Oh Oi On Pb Pc Pd Pf Pg) Jr(Fr Ih Ik Io Ip Iq Ir Is Ji Lu Ly Lz Md Me Mf Mi Mn Mp Mq Mr Mu Mx Mz Na Nn No Nt Nv Nw Ny Oe On Pb Pc Pd Pf) Qc(Fr Ih Im Io Ip Iq Ir Is Ly Lz Md Me Mi Ml Mp Mq Mr Mu Mv Mx Mz Na Nn No Nt Nv Nw Ny Oe Oh Pb Pc Pf Pg) aN(aH aR AW bR bU cA cB cD cF cK cN cW cZ Di Fw Ii Io Is It Lw Ly Ma Mb Mc Mv Ne Nf Nl Nr Of Oh Om On) Ji(Fr Ih Ik Ip Iq Ir Is Lu Ly Lz Me Mf Mn Mp Mq Mr Mt Mx Mz Na Nh Nn No Nr Nt Nv Nw Oe Oh On Pb Pc Pf) Lz(Fr Ih Io Ip Iq Ir Is Jo Md Me Mf Mi Mp Mq Mr Mu Mx Mz Na Nn No Nt Nv Nw Oe Oh On Pb Pc Pd Pf) Ip(Fr Ih Io Iq Ly Md Me Mf Mi Mp Mq Mr Mu Mv Mx Mz Na Nn No Nt Nv Nw Ny Oe Oh On Pb Pc Pd Pf) Nt(Fr Ih Iq Ir Is Jo Md Me Mi Mp Mq Mr Mu Mx Mz Na Nn No Nv Nw Oe On Pb Pc Pf) Mq(Fr Ih Io Iq Ir Is Jo Md Me Mf Mp Mr Mx Mz Na Nn No Nv Nw Oe On Pb Pc Pf) Nn(Fr Ih Iq Ir Is Jo Md Me Mi Mp Mr Mx Mz Na No Nv Nw Ny Oe Pb Pd Pf) Me(Fr Ih Iq Ir Is Jo Md Mf Mp Mr Mx Mz Na No Nv Nw Oe On Pb Pc Pf) Na(Fr Ih Io Iq Is Jo Md Mp Mr Mx Mz No Nv Nw Oe On Pb Pf) Nd(aG aH aL aW bA bC bR bU cA cB cF Ch cK cN cT Di gP) aR(aW bR bU cB cD cF cK cW Di Lw Ma Mv Nf Of Oh Om On) Pf(Fr Ih Iq Ir Is Mp Mr Mx Mz No Nv Nw On Pb) Mr(Fr Ih Iq Is Jo Mp Mx Mz No Nv Nw Pb) Ih(Fr Io Iq Mp Mx Mz No Nv Nw On Pb) Tj(aH bQ bR cB cF Fa It On Pa) Fr(Is Mt Mx Mz No Nw Oe On Pc) Mx(Io Iq Is Mz No Nw On) No(Is Jo Mz Nw On) iA(cA eD Nf Oh On) Mz(Is Mp Nw On) gP(Bo cF Di Nf) Iq(Jo Mp Nw) Jd(Ib Og) Jo(Mp Nv) Nw(Is On) eD(iH Rb) CwoK DiaH MdPb iHqU yHzH} On{Tj(AD aE AF aG aI aJ aK AL aM An Ao AP aQ Ar AS aU aV AW AX aY aZ BA BB BC bE bF BG bH bI bJ bL bM BN BO bP bS bU bV bW bX bZ cA cC cD cE cF cG CH cI cJ cK cL cM cN CO CP CQ cR CS CT CU CV CW CX cY cZ dA DB DC DD DE dF Dg dH DI dJ DK DL dM dN Dp Ef Ex Ez Fa Fb Fn Fp Fr Fw Gl GP Gz Ha Hc Hq Hr Hu Hv Hw Hx iA Ib Ic Id Ih Ii Ij Ik Il Im In Iq Ir Is Iv Iz Je Jf Jg Jh Ji Jj Jk Jm Jn Jo Jp Jq Jr Js Jt Kc Kd Kf Ki Kk Kn Ko Kp Kr Ks Kx Ky Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Ne Nf Nh Ni Nj Nk Nl Nm Nn No Nq Nr Ns Nt Nu Nv Nw Nx Ny Oe Of Og Oh Oi Om Or Oy Oz Pb Pc Pd Pe Pf Pg Ph Pi Pj Pk Po Pz Qa Qb Qc Qe Ql Qm Qu Qv Rb Rf Rg Rh St Tn To Tr Tt Tv Ua Ub Uc Ug Uk Ul Um Uo Ur Us Ut Uu Uv Vo) aN(AD aE AF aG aH aI AJ aK AL aM An AO AP aQ Ar AS aU aV AW AX aY aZ BA BB BC bE bF BG bH bI bJ bL bM BN BO bP bQ bS bV bW bX bZ cA cC cE cG CH cI cJ cK cL cM cN cO cP CQ cR cS CT cU cV cW cX cY cZ dA DB dC dD dF dG dH dI dJ dK dL dM dN Ij Il In Io Iu Iv Lw Mk Ms Mv Ng Ni Nm Nq Og) Nd(AD aE AF aG aH aI AJ aK aL aM AO aP aQ Ar AS aU aV aX aY aZ BA BB Bc bE bF BG bH bI bJ bL bM bN BO bP bQ bS bU bV bW bX bZ cA cC cE cG CH cI cJ cK cL cM cN cO cP CQ cR cS Ct CU CV CW cX cY cZ dA DB dC DD De dF dG dH dI dJ dK dL dM dN Qc Qd Qe) Jj(aA bR cB cK gP Hu Hw lH Ii Ij Ik Il Im In Ip Iq Ir Is It Iu Ji Jk Jm Jo Jp Jq Jr Jt Li Lj Lv Lw Lx Ly Mc Me Mf Mg Mh Mk Ml Mm Mn Mp Mq Mr Mt Mv Mx Na Nb Nf Ng Nh Ni Nk Nm Nn Nr Ns Nt Nu Ny Of Og Oh oK Om oN Oy Oz Pa Pb Pc Pe Pg Po Qa Qb Qe) Ii(aA aH aR aW bR cB cK Fp Hu Hx Ik Io Ip Is It Jd Jq Jr Jt Lj Lv Lx Mh Ml Mm Mu Mx Ng Nh Ni Nk Nm Nq Ns Nw Nx Of Og Om Oy Oz Pa Po) Jd(Aj Bg Cu Di Fn Fw Hq Hr Hu Hx iA Ib Ic Ij Il Io Ir Iu Jk Kk Lh My Nt Nv Of Og Om Po Qb Ql Qu Qw Qz Tr Ub Uc Uv Vo Vp) aR(aW Bb bR bU cB cD cK cT dE Di Fw Hq Hw iA Ic Il Io Is It Iu Jg Jh Ji Jk Jo Lh Mb My Na Nf Nn Nr Oh Om Pg Po Qb Uv) JI(Af aG aH Aj An aO Ap aQ Ar aS aX bA bC Bn bO bU bV cA cB cD cN CO cQ cS cT dD DE Di Fw Qv Uv Vo) iA(Af aK BB Bo bS cC cD cE cF cK cV Cw gP Hf Hq Ic iH Il Io Ip Iq Iu Jg Jp My Mz Nf Of Oh oK Pe Rb Uv) Mw(Fp Hr Hw Hx Ik Il It Iu Jg Jh Ji Lv Lw Lx Mm Ms My Ne Nh Ni Nk Nw Nx Of Og Om Oz Pc) Nl(aA Ij In Io Iu Iv Lw Mb Mk Mv Ng Nh Ni Nm Nq Og Om Qb) Ms(aA Hx Is It Iu Ji Lw Mb My Nc Ne Ng Ni Om Qb) It(Aj bR bU cB cK Di Fw Mu Mv My Oy Qv Rh Vo) Of(Hx Il Lw Mu My Nc Ne Ni Nq Og Oy Qb) Mb(aA Il Lw Mm Mu Mv Nc Ng Nq Og) My(cA cB Hx Lw Mu Nc Ne Og Oy Qb) Iv(Il Mk Mu Mv Nc Ng Ni Nq Og Om) bR(aW dE Hr Hx Il Iu Jg Po Qc) Oy(aA Hx Jg Ne Nx Oz Qb) Nc(Il Mu Mv Ng Ni Og) cK(Hr Hx Il Iu Na Qb) Mu(Ne Pc Qb) Hr(aO aW cB) Aj(Hx Jg) Il(Ar Ne) In(Id Tv) Hf(oK qU) Io(Di Og) Qb(cB Mv) iH(Bb qU) FiKk FwNa NqqC NiNk HxcB IubU PjhO} Nd{Fr(Fp Hq Hr Hu Hv Hw Hx Ih Ii Ij Ik Il Im In Io Ip Iq Ir Is It Iu Jg Jh Jk Jl Jn Jo Jp Jr Js Lh Li Lj Lu Lv Ly Lz Ma Mb Mc Md Mf Mg Mh Mi Mj Mk Ml Mp Mq Mr Ms Mt Mu Mv Mw Mx My Na Nb Ne Nf Nh Ni Nj Nk Nl Nn Nq Nr Ns Nt Nu Nv Nx Ny Oh Oi Om Oz Pb Pc Pd Pe Pf Pg Po Qa Qd Qe) Lx(Fp Hq Hr Hu Hv Hw Hx Ih Ii Ij Ik Im Ip Iq Is It Iu Jg Jh Jk Jm Jn Jo Jp Jr Js Li Lj Lu Lv Ly Lz Ma Mb Mc Md Mf Mg Mi Mj Mk Ml Mp Mq Ms Mt Mu Mv Mw Mx My Na Nb Nc Nf Ng Nh Ni Nj Nk Nl Nn Nq Nr Ns Nt Nu Nv Nx Ny Oe Of Oh Oi Om Oy Pb Pc Pd Pf Po Pz Qa Qb Qc Qd Qe) Nw(aN aR bA bR bU cB cD cT Fp Hq Hr Hu Hv Hw Hx Ih Io Ip Iq Ir Is It Jg Jh Jk Jl Jm Jn Jo Jp Jq Jr Js Lh Li Lj Lu Lv Ly Lz Ma Mb Mc Md Mf Mg Mh Mi Mj Mk Ml Mp Mq Mt Mu Mv Mw Mx Nb Ne Nh Ni Nj Nn Nq Ns Nt Nu Nv Nx Ny Oe Oh Oi Om Oz Pb Pc Pd Pf Po Pz Qa Qb Qd Qe) Jt(aR Di Hr Hu Ii Ij Ik Il Im In Ir Is Iu Iv Jg Jo Jp Jq Li Lj Lw Mc Me Mg Mp Ms Mt Mz Nc Nf Nh Nk Nl Nm Nn No Nr Nv Of Oh Oi Om Oz Pc Pe Pf Po Qa Qe) Jg(aG aH Aj aL Ar aS aW aY bA bC bM bN bQ bV cB cD cF cH cK cM cN cQ cT cW cZ Di Il Im Iv Jq Lj Lw Mn Mv Mw Mz No Nq Og Pa) No(Ij Il Im In Is It Iv Jl Jp Jq Lh Li Mc Mg Mp Mr Mt Mz Na Nc Nf Nl Nm Nn Nr Nv Nx Of Og Om Oz Pc Pd Pe Po Qa Qe) Jj(Fp Ih Ii Ij Il Ip Iq Jh Jo Jr Js Lv Ma Me Mr Mu Mv Mw Mx Na Nc Ng Nk Nl Nq Nt Ny Oe Om Oz Pd Pe Pf Qb Qc) Lw(aR cT Ih In Is Iv Jl Jq Lh Lj Ma Mc Mp Mr Mt Mu Mv Mx Nc Nl Nn Nr Nx Of Oh Om Oz Pe Pf Po Qa Qd Qe) Mn(Ih Im In Is Iv Jl Jp Jq Lh Li Me Mp Mt Mv Mx Na Nc Ne Nl Nm Nr Nv Nx Of Om Oz Pc Pd Pe Pf Po Qa Qe) Pa(Im Is Iv Jl Jp Jq Lh Li Me Mp Mr Mt Na Nc Nm Nn Nr Nv Of Og Oh Om Pd Pe Po Qa) Ji(aR Hq Hv Io Ir Jh Jk Jm Jn Jq Js Lh Lu Lv Mb Mg Mi Mj Mq Mx Nb Ne Nj Nx Ny Oe) Mz(Ij Im Is It Iv Jp Li Me Ml Mp Mt Nc Nf Nm Nn Nr Nv Og Oz Po Qa Qe) Jp(aN aR Il Im Is Iv Jq Lh Lj Me Mr Ng Nm Nr Og Oz Pe Po) Og(Iv Jl Jq Li Mp Mr Mt Nm Nn Nr Nx Of Om Pd Pe Po Qe) Nv(Ii Im In Iv Me Mr Ms Na Nc Nf Ng Nm Of Oz Pe) Lh(Hx Ii Il Im In It Iv Li Me Mt Nc Nf Ng) Jq(Im In It Iv Li Mt Nr Oz Po Qa Qe) Nm(aN aR Im Iv Li Mp Mt Nc Oz Qa) Mm(aN aR aW bA cT Di Hx Jk Qc) Im(Iv Me Mp Mr Mt Oz Pd Pe) aN(Bb Is Jh Mv Of Om Pd) Mp(Iv Mr Nc Oz Pe) In(Is Iv Li Po Qa) Mr(Iv Me Mt Nr) Qa(Iu Me Nh Qb) aR(Bb Jh Mv Of) Mt(Iv Oz Pe) Bb(bA cN) aA(Ij Ik) AdAj Dils Poll MePe MyOm} aN{Aw(aD aE AF aG aH aI AJ aK AL aM An AO AP aQ Ar AS aU aV AX aY aZ bA bB Bc bE BG bH bI bJ bL bN BO bP bQ bS bV bW bX bZ cA cC cD cE cH cI cJ cL cM CO CP CQ cR CS Ct CU CV CW CX cY cZ dA DB DC DD DE dF dG dH DI dJ DK dL dM dN Fp Fr Io Is Mm) cB(AA aD aE AF aG aH aI aK aL aM aO aP aQ Ar aS aV Ax aY aZ Bc bE BG bH bI bJ bL bM bN bO bP bR bS bV bX bZ cC cD cH cI cJ cM CO cP cR CS Ct CU CV Cw cX cY cZ dA dB DC dE dF dG dH dI dJ DK dL dM eO Fr Is Jg Nj Nw) bF(aE AF aH aJ aK aM AO Ap aQ AR As aU aV aY BA bB Bc BG bL bN Bo bP bQ bW bX bZ cA cC cD cG Ch cI cM cN CO CQ cT CU Cv CW Dc DD DE Dg dH Di dJ Dk dN eO Fr) eO(aD aE aI Aj aK aL As aW aX bA bB bC bE Bg bH bN bQ

Figure 4 Continued bU bV bX bZ cA cD cE cF cG CH cI cK cL cN cO cQ cY cZ DB dC Dd dE dF Dg DI dJ dK dN Dw Em Eo Ew FP) Cp(Ad aK Ap aQ aR aU aV Ax BA Bb BC bJ bM BN Bo bP bQ bR bW cE cG Ch cI cJ cN CQ Ct cW dD DE Dg Di dJ dN) Bb(Ad aK aQ AR aU aV Ax BA bB bC Bo bQ bR bW cE cG Ch cJ cL cP cQ Cs Ct cW dD De dF Dg Di Dl dN Is) bU(Af Ap AR bA BC Bg bQ bW cA cE cF cK cN Co Ct Cu Dc dF Dk dN Eo Fr It Jd Jg Jh Ji Nj Nw) cF(aI aJ Ao AR aU bA bB BC Bg bQ bR bW cA cE cG cK cN Co cQ Ct Cu Dc dD dF Di Dk dN Fr) Nj(aR Ba cN cT Fr Hu Is Jg Jh Ji Jj Jp Lw Lx Mm Mt Mu Mv Mw Nf Ni Nm Nr Ny Of Om Pa Pd) Is(aR Ba Bo bR Ch cK cQ cT dD It Iu Jg Jh Jj Mc Mv Na Nf Ni Nk Nw Of Og Qb) cT(Ao Ar aW Ax Ba BC Bg bM Co Cu Cv Cw Dc Dc Di Dk Em Fr Jg) Bn(Ad Ap aR aW Ba bC bM Bo bQ bR cG cK Co Cw Dg Di Dl) Dl(AR BA bC bR cG Ch cK cN cW Dc dF Eo fR) aW(Ao Ap Ba hC Bo bR cG cK Co Cu Cw De Di fR Jg) Ad(Aj BA bC bM Bo bR cG Ch cK cN cW De Di) Jg(Aj aR bR cK Di Jj Lw Ly Mc Ni Nx Of) cK(Ap Ba bC Bo cG Ch Cw De Dg Di Nw) Ch(BA bC bM bR cG cN Dc Dg) Ba(bC bM Bo bR cN Di) Eo(aE aO Ar bW Dk eM) Of(Bo It Ji Jj Lw Nw) bC(Ar Bo bR De fR) Di(bM bR Dg Io) Nf(Cw Ny Om Pd) Bo(Ct De Dg) bM(De Dw Ew) bR(cG De Dg) dW(aE bB dK) AfEm MvNw IcJd} cB{aW(aA aD aE aF aG aH aI aK aL aM An AO Ap aQ Ar aS aU aV aX aY aZ bB Bc bE BG bH bI bJ bL bM bN BO bP bR bS bV bX bZ cA cC cD cE cH cI cJ cL cM cN cO cP cQ cR cS Ct CU CV CW cX cY cZ dA dB DC dE dF DG dH dI dJ DK DL dM Em eO EW FR) bF(AD aF aG aJ aK aM aO aP aQ aU aV Aw aX aY Ba Bb bC bM bN bO bQ bR bU bW bZ cA cD cF cI cM cN cO Cp cQ cT cU cW cX dA dD DE dJ Dl dM dN) aR(aA Ad aJ aK aP aQ aS aU aV aX Ba BB bH bJ BO bQ bU bV bW cA cE cF cG Ch cK cL cN cQ cW dD dF DI Dl dN Jg Jh Nj) Aw(Ad aG aH aJ aK An aP Ar aS aV Ba Bb BC bJ bM Bn bO bQ bU cA cF cG Ch cM cN CQ Cv cW dD De DI Dl) cT(Af AJ Al An Ao Ap As Ax Ba BC Bg bM cA cF cK cN Co Cq Cs Ct Cu Cv Cw Cx Db Dc Dd Dg Dk Em FR) bA(aH An Ao Ap aQ Ar BC bM Bo bQ bU cA cE cF Ch cK cN Cp cR Cv Dc dD Dg Di Dk Dl dN Em eO Fr) Bn(Ad aJ An AP Bb bC Bo bQ cF cG Ch cK cN Cp dD Di Dl dN Tj) De(Ad aH aJ Ba Bb bC bU cF cK cN Di Ex Tj) cK(Ad aJ aP Ba Bb bC bQ cG cN Cp Di dN) Bb(cN Di dR eF Ex Fw gL gP gW Nj) cN(Ad Ba Cp dD EW Ex) bP(DW EO EW) Ad(aH Aj Ba Di Tj) Ba(bC cF Cp Di) dM(EO EW) Cp(eF gP Tj) Nj(Jg Ni Nw) Bo(dW eO) bQ(bC cF) dJ(dW eO) AoEx} aW{eO(aD Af aG aH aI AJ aK aM aO AP AR aS aU aV AX aY aZ bA BB Bc bE bF BG bH bJ bL bM bN BO bP bQ bR bS bU bV bW bX bZ cC cE cF cG cH cI cL cN Co cP cQ Cs CT cU Cv cW CX cY cZ dA DB dD dF DG dH Di dJ dK dL dM dN dW dX EM Eo eP EW FP FR Gd gV) bU(An Ao Ap AR BA Bn Bo cF cG cK Cp cT Cw Dg Di Dl dN Dw Eo EW Jd Jg) Ad(aH Aj AR aV Aw BA bC bF bM Bn Bo bR cG Ch cN Cp De Di dJ) cF(Ao Ap AR BA bC Bo bQ bR cG Ch cK cT Cw dD De Dg Di Dl dN) Bn(Ap aR Aw Ba Bb bF bM Bo bR Ch cK cT Dg Dl Em fR) cK(Ap aR Ba BC bF Bo cG Ch Cp De Dg Di Dl dN) Aw(aH aK aQ aV Bb bC bF bR Ch cT Dg dJ Dl) bM(Bb bF Ch Cp De DW Eo EW fR) bF(aH aR Bb bC cO Cp dJ Dl fR) cT(Bb Bo Ch Cp Dc Dg Dl Em fR) Nj(Bb Jg Mm Mv Nm Nw Om) Bo(Dl DW Eo EW) bR(cG Cp Dw EW Jg) Cp(aR aV dJ Dl) fR(bC Ch De Dl) dW(aD bB eP) Em(Af De) Ew(bH dX) aR(Bb Jg) eP(eW Ko) ChEx DwbB EfgV EoaD} Jd{Tj(Ad Ar Ax Bn Cp Cq Cs Cu Cw Dc De Di Hq Hw Hx Ib Ic Id Ii Ij Im Io Ip Iq It Iu Iv Jh Ji Jn Jq Jr Jt Kd Ke Kf Kj Kn Ko Kp Kq Kr Kx Lh Li Lw Mc Mj Ml Mm Mq Mt Mu Mv Mz Na Nb Nk Nm Nr Nv Nw Nx Ny Oa Og Oh Om Oy Pb Pd Pf Pg Ph Pi Pj Pk Po Qa Qe Qv Qx Qz St Tv Ub Ur Ut) Di(Aj AR Bg bU Fn Fw gP Hu iA Ib Ic Io Ip Iq Ir Is It Iu Iv Kk Lh Mc Mm My Ns Of Og Om Pj Qu Qw Qz Rh Tt Vo) Og(Fn Fy Hu Ib Ic Id Io Ip Iq Ir Is It Iu Iv Ji Jq Kk Lh Lw Mc Mm Mv Na Nk Oh Om Pa Pd Qz St Ub Uf Uk Un) Qz(De Hu Ib Ic Id It Iu Mv Om Pa Qv To Ub Uf Ut Uv Vo) Om(Ic Id Io Ip Iq Ir Is It Iu Iv Oh St Tt) bU(aR cC dB Fw Ic iH Iu Na Uv) Ib(Hu Ic Id Ki Mv Oh) Ic(aR cF cN Hu Ub) Id(In It Iv) Cw(iA oK) Mv(My Qu) Hu(Qu Tt) In(Kq Mr) Ip(jD lL) Kz(eD lL) AjTt FaFw HpoK TrIt HfqU QvPj JrJs LhOh} Ji{Ms(Fp Fr Ii Ij In Io Is It Iu Lw Lx Mc Mm Mt Nc Ne Ni Nj Nl Nm Nr Nx Of Og Oz Pa Qa Qb Qe) Jj(aA Fp Hx Ij Ik Il Im Is It Jt Lj Lx Mb Mm Mt Nc Ni Nj Nk Nr Nx Oz Pa Po Qa Qe) Iv(aA Hx Ij Il In It Mb Mm Mu Mv Mw My Nc Nf Nj Nl Nm Nq Og Om Oy Oz Po Qb) Nl(aA Ii Ij Il In It Lx Mm Mn Mu Mw My Nh Ni Nq Og Oy Qb) Ii(Fp Fr Im Jt Lx Mm Mt Nc Ne Nj Nr Nx Oz Pa Po Qa Qe) Nc(aA Ij Il In It Mb Mm Ni Og Qb) aA(Hx Ij Il Mb My Ne Nj Og Oy) Lx(Ij Il My Qb) aR(bU Mv Nj Of) Ij(Fp Mt Ne) Nj(In Og) MbMm MwJg NeIl NiNk ImOg} Jj{Iv(Fp Im Is Jg Jl Jo Jq Lh Li Lv Lw Mg Mn Mz Ne Nk Nm Nn No Nt Nv Of Oh Oz Pa Po Qa Qe) Nl(Fp Fr Im Is Jg Jq Lh Li Lw Lx Mg Mn Mt Nm No Nr Nv Nw Of Oh Pa Po Qa Qe) Nj(aA Ad aR bU cT Im Is Jg Jt Li Lx Mn Mt Nr Nv Nw Nx Pa Po Qa Qe) Nx(aA Fp Fr It Jg Jt Li Lj Lw Lx Mm Mt Ne Nk Nt Pa Po Qa Qd Qe) Nc(Fr Is Jg Jt Li Lx Mm Mt Nv Nw Po) Mm(Ik Lv Mb Ne Nr) Jt(aR iA Mb Nc) Jg(aR iA) CwoK LxIk OfaR} aR{Jg(aH Ar Aw bA bC BN bQ cF cK cN cQ cT cW Is Jh Lw Lx Ly Ma Mb Mc Mr Mt Mv My Na Nb Nf Ng Ni Nl Nw Nx Of Om Pa Pb) Nj(bA bU cT Di Fr Is Jp Jt Lw Lx Mm Mr Mt Mu Nb Nf Ni Nm Nr Ny Of Om Pa Pd) Aw(bF bM Bn cF cK cT Dl) Di(bU gP Io Is Jh Jt Of) Bn(bF Bo cF Ch cT) bF(bR bU cF cK) Cp(eF gL gP) Of(Bo Hr Ic) cT(Ad Bo cF) BbgP CwoK MvIc JhbU JtbR} Bb{tV(Bg gW Hu Ic Iz Jk Ky Kz Mz qW rC Ua) Nj(bA bR bU bV cN cQ cT dN gP Ni) jY(Hf hP qA qC qD qO qP qQ rS rW) lL(qI qO qP qQ rO rW sC uL) Hf(eD jV qU qW qX qY rC) eD(Ic Kz Na Nq Pa qO) gP(Aw Bo bU cF Cp Di) Mz(fN hO qC tT) iH(bU cF cM Mm) Nq(qC qD tS) bF(Bn bU cK) cT(bU cF cK) Ic(qC tN) Ri(rW tS) eF(Aw Cp) tT(Oi Pj) DifP NajD QvuU cKcN} Ad{cT(aH bF bM Bn Bo bU cK cN Ct gP) Aj(bF Bn bU cF cK fP gW Nj) cF(bA bF Bn cK cN gP iH) Di(Bn eF fP gL iA iH) Na(eD hA jM lK lL qU) Bo(dR eF fP gL gW) Hf(qT qW qY) bF(aH Bn cK) iH(qT qU qW) Qw(qQ tV) ExqA bAcK} Pj{Qv(hO Hu tV uP uT uU vO vS wE yL zH zI tM) iH(eD qT qV qW qX qY rA rB rC) hO(Ic jD lL Mq Nq Oi tF) Ic(hV qB qC qD tM) jD(cC qB qC qD qH) qD(jY lL Nq) Di(qY tT) Ri(rN yL) tV(Hu qW) CwoK TjFa IlsJ HfqU tTqW qCjY} bB{eO(aD aJ aK aM aP aQ As aY aZ bA bL Bo bP cE cI cM cN cP cQ cW dA Dc dE dG dH dJ dL dM Ew gV) Ew(aF aO bM bP bW) Eo(aD aJ bP dM) bM(Dw dX eP eW) bP(DW eW) aD(DW) BodW JgiA aFeW cFiH} Nj{Nw(aA aH bA bC bR bU cA cF cK cQ cT dE dN Ii) Ni(aA Ar bA bF bU cF cN cT Di Mm) Jg(aH Aj bA bU cF cQ cT dN) Mm(aA Ar cT Di Iv Og Pa) aA(Fr Iv Lx Nx Pa) Di(Ar Is)} cF{cT(An Ap Ar Bc Bo Ch Cp De Dg Di Dl Fr) Aw(bF Bn bU cK cN Dl gP) Cp(cK dR eF gL gP) bF(bR bU cK cN) gP(Ao Ba Cw Di) iH(bU cA cM dD) Bn(Ba Bo cK) CwoH DecK bMdW} Mm{Nl(aA Fp Il In Iv Lv Lw Mb Nh Ni Og Pa) Iv(aA In Lw Mb Ms Nc Ni Og Om) Mb(aA Jq Lw Mz Na Nc Og) Nc(Fp Lv Nx) Di(tO tT) CwoK NiNk} Bo{Dw(bM bP cN dM FR) cN(dW EO EW) Cp(dR eF gL gP) cT(Bn bU cK Dl) Ew(Co dM) dW(bP dM) eO(dB fP) DlgP} Cw{oK(Di Ib Ic Il In Io Ir It Iu Ko Kq Lx Mc Mz Nw Pi Rh Uv Vo) Nf(iA iP oF) eD(bQ iA) JgiA KodX} Aw{cK(bA BC bF bM Bn bU cG cN cT Dl dN) bU(bA bF bJ cN) cT(aH bM cN Dl) Vq(hO vB) bF(aH bM) dBeO} Jg{iA(bU cA Di Ez iH Lw Lx Na No Nw Pa Pc) bR(Aj cN Is Ly Mc) Aj(aH bU) Tj(Fa Pa) DiaH MwOm OyaA bUiH} bM{dW(bQ bV bX cA cD dE dI dJ Em) Dw(cU cY dE dK) dE(EO eW) bX(eO eW) BnbF EobJ bNeW cTfR} Nw{Nl(aA Ii Il Lw Ms Ni) Nc(Ii Il Ms Ni) Iv(Ii Il Ms Om) iH(qU uZ zH) NeIl QteP KzrX} bF{Bn(aF aH bC bR bU cK cO cT Dl fR) bU(aH cK cN De) fR(aO cT) DlaH} Mz{qC(cV gW Ic jD jY lL Qw) zH(gW iH oN pF yH) IphL iHvS qDlL} Vt{zH(gW jY oF) Ri(rW yK) qU(rP rT) tL(jY Qv) DiwH NutS QwtV iAyK jYqQ} cT{bU(Ar Bn Ch Cp De Di Dl) cK(Bn Cp De Dl) Bn(Ch Dl) ChcN} aO{dF(DW EO EW) dG(DW) EwcG} nN{mY(eD jE jT jY qY) nO(jT jY qT) jFqY} Nl{aA(Iv Ni Nx) Fr(Il Lw) LwIv LxIl ItJt} rS{jY(sF sH sI sJ) Nh(sF sH sI) MksF} iH{qU(Jt Nm) AaqW KczH VqsC bUcA bZlM} Ri{Tr(rN rU rW) rN(Ap Tt) fNtV} Fb{Kk(Rx Vh We) BnUw LhVh} Kq{Hf(gP qY rX tF) UsrX} Vq{Qv(sC uG uN vP) tFuM} aM{cV(Dw EO) EobJ cAeO} Tj{Fa(Io It Jt Kf)} Qt{eP(Kc Kp Kz) KcdX} Ap{rN(iA jY) DifP} Nx{aA(Iv Ms Nc)} dB{eO(cW dE dG)} Di{Is(bR Om)} Ip{IcjD tVlN} Jt{NcIt KkdX} Pc{sI(rX rY)} aK{bP(dW Eo)} cM{DuIh bAbR} fP{HrsH bQcO} qC{NqUn LhjY} BgDrgW DkJktV TiNyqY ExhOqQ TtUvtF IlKssJ JpKddX KfiArN KodKcP bCbWfR

Figure 4 Continued

Unconstrained panels with 2 analytes, where 1.0E-8 >= 'model p-value' > 0. Contains 185 panels of 199,257 total panels evaluated. : Ok(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe) aC(Ad Ao Ap Ar AW Ba Bb Bc bF Bg Bn Bo cB cF Ch cN Co Cp Ct Cu Cw Dc De Dg Di Dk Dl dN FR On) Et(aA Fp Hx Ii Ij Il Iv Jj Lw Mb Ms My Nc Nd Ne Ng Ni Nj Nk Nl Nq Of Og Om Oy Pz Qb) Nd(aA Ji Mm Nw On) aNcB Unconstrained panels with 2 analytes, where 1.0E-7 >= 'model p-value' > 1.0E-8. Contains 146 panels of 199,257 total panels evaluated. : Et(aC Fr Hq Hr Hu Hv Hw Ih Ik Im In Io Ip Iq Is It Iu Jg Jh Ji Jk Jl Jm Jn Jo Jp Jq Jr Js Jt Lh Li Lj Lu Lv Lx Ly Lz Ma Mc Md Me Mf Mg Mh Mi Mj Mk Ml Mm Mn Mp Mq Mr Mt Mu Mv Mw Mx Mz Na Nb Nf Nh Nm Nn No Nr Ns Nt Nu Nv Nw Nx Ny Oe Oh Oi On Oz Pa Pb Pc Pd Pe Pf Pg Po Qa Qc Qd Qe) aC(Af AJ Al AN aR As Ax bA bB bC bQ bR bU bW cE cG Cq Cs cT Cv Cx Db Dd dF Jg Jh Of Ok) Nd(Fr Jt Lw Lx Mn No) aN(Aw Bb bF Cp Ok On) cB(aR AW bA bF) On(iA Jj Tj) Jd(Di Og) MsJi JgaR Unconstrained panels with 2 analytes, where 1.0E-6 >= 'model p-value' > 1.0E-7. Contains 270 panels of 199,257 total panels evaluated. : aC(AA aE aF aG aH al aK aL aM aO aP aQ aS aU aV aX aY aZ bE bH bM bN bO bP bS bV bX bZ cA cC cD cH cI cJ cK cL cM cP cQ cR cS cU cV cW cX cY cZ dB dD dG dH dI dJ dL dM Ef Ex Is Ji Jt Mg Mm Mv Nm Nw Om Pd) Jd(aN AR bU Et Fn Hu Ib Ic Id Io Ip It Iu Jj Kk Lw Mc Mm Mv Oh Ok Om On Pa Pj Qv Qw Qz St Ub Uf Uv Tj) Nd(Im Is Iv Jg Jj Jp Jq Lh Li Mp Mr Mt Mz Nc Nm Nn Nr Nv Og Om Pa Pe Po Qa Qe) aN(Ad aW Ba Bn Bo bU cF Ch cT De Dg Di Dl eO Is Jg Nj Nw Of) cB(Ad aJ aP Ba Bb bC Bn bQ cG cK cN Cp cT dD De Di dN On) On(aR bR cK Fw Ii Iv Mb Ms Mu Mw My Nc Nj Nl Of Oy) Ji(aA Ii Iv Jj Lx Mb My Nc Ne Nj Nl Og) aW(Ad Aw Bb bF Bn bU cF Ch cK Cp eO fR) Aw(aR bF bM bU cF cK cT) Mm(Fp Iv Jj Mb Nc Nj Nl) Nl(aA Fr Jj Lw Lx Nw) cT(Ad Bn Bo cF fR Nj) Et(aR iA iH Ir) Nj(aA AR Nw) Jg(Aj bR iA iH) Jj(Iv Lx Mt Nx) cF(Ad bF Bn iH) nN(jE jF jY qY) Ok(aR cK iA) Ad(Aj Bn) Nw(Iv Nc) bF(Bn bU) CpgP CwoK MzqC JhaR NxaA PjhO bUiH Unconstrained panels with 2 analytes, where 1.0E-5 >= 'model p-value' > 1.0E-6. Contains 948 panels of 199,257 total panels evaluated. : Jd(aC Ad Af Aj Al An Ao Ap As AW Ax BA Bb BC Bg Bn Bo bR cB cF Ch cM cN Co Cp Cq Cs CT Cu Cv Cw Cx Db Dc Dd De Dg Dk Dl dN Dp Ed Ez Fa Fb Fp Fr Fw Fy Gp Ha Hb Hc Hf Hq Hr Hv Hw Hx iA IH Ii Ij Ik Il Im In Iq Ir Is Iv Iz Je Jf Jg Jh Ji Jk Jl Jm Jn Jo Jp Jq Jr Js Jt Ju Jv Jy Kc Kd Ke Kf Kg Ki Kj Kl Kn Ko Kp Kq Kr Ks Kx Ky Kz Ld Lh Li Lj Lu Lv Lx Ly Lz Ma Mb Md Me Mf Mg Mh Mi Mj Mk Ml Mn Mp Mq Mr Ms Mt Mu Mw Mx My Mz Na Nb Nc Nd Ne Nf Ng Nh Ni Nj Nk Nl Nm Nn No Nq Nr Ns Nt Nu Nv Nw Nx Ny Oa Oe Of Oi Or Ou Ow Oy Oz Pb Pc Pd Pe Pf Pg Ph Pi Pk Po Pz Qa Qb Qc Qd Qe Qg Qh Ql Qm Qn Qt Qu Qx Qy Ra Rb Rc Rf Rg Rh Ri Rj Rm Sr Ss Tn To Tr Tt Tv Tz Ua Uc Ud Ue Ug Uh Uk Ul Um Un Uo Up Ur Us Ut Uu Vo Vp Vq Vt Wm) cB(AA aD aF aG aH aI aK aL aM An aQ Ar aS aU aV aX aY bB Bc bE bH bI bJ bM bN BO bR bS bU bV bW cA cD cE cF Ch cI cJ cL cM cO cP cQ cR cS CW cX cY dA Dc dE dF dG dH dI dJ DL dM Ef Ex fP Fr gW Is Jg Nj Nw Ok Tj) Ji(aN aR Di Fp Fr Hr Hw Hx Ij Ik Il Im In Io Ip Is It Iu Jg Jr Li Lj Lu Lv Lw Ly Mc Md Mh Mk Ml Mm Mn Mr Mt Mu Mv Mw Mx Nb Nf Ng Nh Ni Nk Nm Nn No Nq Nr Ns Nt Nw Nx Ny Of Oh Om On Oy Oz Pa Pb Pc Pg Po Pz Qa Qb Qc Qd Qe) On(aA aH Aj aQ Ar aS aW bA bC BO bU cA cD cE cH cN cT dE Di dJ Fn Fp gP Hf Hx Ic iH Il Io Lv Lw Mm Mv Ne Ng Ni Nk Nq Og Om Pj Qu Qv Qw Qz Ri Rm Tt Uc Ur Uv Vo Vp) Nd(Aa Ad aN cT Cw Di Fp Ih Ij In It Jh Jl Jn Js Lj Lv Ma Mc Me Mg Mi Mu Mv Mw Mx Na Nb Ne Nk Nl Nq Nt Nx Ny Of Oh Oz Pc Pd Pf Qd) aN(Ao Ap Ar BC Bg bQ bR cE cG cK cN Co Ct Cu Cw dD dF dN Et FR It Jh Jp Jt Lw Mg Mm Mt Mu Mv Nm Ny Om Pd) nN(eD hA hX iB iC jD jG jH jI jK jL jM jO jP jQ jR jT jU jV 1K IL 1M 1N 1O mE qT qU qV qW qX rA) aC(aD bG bI bJ bL cO dA dC dE dK Em Gp Hu Io It Jp Lh Lw Lx Mt Mu Mw My Ng Nh Nj Nr Nx Ny Tj) Nj(Ad AW BA Bb bC bF bQ bR bU bV cA cF Ch cN Cw De Di dN Fr Iv Jj Jt Lw Lx Mt) aW(Ap AR aV Ba bC bM Bo bR cG cT Cw De Dg Dl dN Et Ex Jg Ko Ok) Mm(aA Jq Jr Lv Lw Lx Ml Mt Mz Ne Nh Ni Nk Nw Nx Oz Pa tN tQ tT tX) Aw(Ad aH aK aQ Ar aV bA bC bJ Bn bR cG Ch cN dD Dl dN eF fP gP) Ok(aH Ar bA bR bU cD cF cN cW Di dR eF fP Fw gP iH oK zH Tj tF) Bb(bF Bn bU cF cK cN cT dR eD eZ fN gP gW hB hO iH qC qD rC) Nl(Im Iv Jg Jq Jt Lh Li Lv Mn Mp Mt Mz Ni Nm No Nv Nx Om Pa) Jg(aH Ar bA bU cF cK cN cQ cT Di dN eF gP Jj Mw My Ng Oy) bF(Ad aH aR bA bC bM bR cK cN cO Cp CT De Dl dN fR) Nw(aA aR cK Ii Il Jj Lv Lw Mb Ms My Ne Ni Nk Om) Bn(aR Ba bC Bo bU Ch cK Dg Di Dl dN fR Tt) Et(bA bR cK cT Di eF gP oK Qv tT tV wL zH) Jj(Fp Fr Ik Is Jt Li Nc Nr Nt Nv Po Qa Qe) Iv(aA Fr In Jq Jt Lw Lx Mt Nc Ne Nm Nx) cF(aR BA bQ cG cK cN Cp dD De Dl eD) Ad(aR bA Bo bU cK cN Di gP gW iA iH) Pj(jD qB qC qD Qv tO tT tX yH zH xA) Lx(Dw Eo Ew Lw Mb My Nc Ne Ni Qb) cT(An Ap Ar bU Ch Cp De Dg Di Dl) aR(Cp Ic Is Jt Lw Mv Nm Of Om) Di(bU cK Dl fP Io Is Tt) Nc(aA Fr Jt Lw Ni Nx) Cp(bU cK dR eF gL Tj) iH(eD Jt Kq qU rC rX) Cw(eD iA iZ oH tF) De(bU cK Tt) Tj(Fa Kf Kq) Mz(fN hL qD) Ic(cN jD qC) fR(bA bJ gW) Ib(Gn Zx) BabU NeaA IptT IsbR SjoD JtiA KqgP KytV VcOy bBeO fPrX Unconstrained panels with 2 analytes, where 1.0E-4 >= 'model p-value' > 1.0E-5. Contains 2,996 panels of 199,257 total panels evaluated. : On(AD aE AF aG aI aJ aK AL aM An AO AP aS aU aV Aw AX aY aZ Ba bE bF BG bH bI bJ bL bM BN bP bQ bS bV bW bX bZ cC cE cG Ch cI cJ cL cM CO CP CQ cR CS Ct CU CV CW CX cY cZ dA DB DC DD De dF DG dH dI DK DL dM dN Dp dR ED EF Ex Ez Fa Fb Fi fP Fr GL Gp Gz HA Hb Hc Hq Hr Hu Hv Hw Ib Id Ih Ij Ik Im In Ip Iq Ir Is It Iu Je Jf JG Jh Jk Jl JM Jn Jo Jp Jq Jr Js Jt Ju Jv JY Kc Kd Ki Kk Kn Ko Kp Ks Kx Ky Kz Ld Lh Li Lj Lu Lx Ly Lz Ma Mc Md Me Mf Mg Mh Mj Mk Ml Mn Mp Mq Mr Mt Mx Mz Na Nb Nf Nh Nm Nn No Nr Ns Nt Nu Nv Nw Nx Ny Oa Oe OH Oi oK Or Ou Ow Oz Pa Pb Pc Pd Pe Pf Pg Ph Pi Pk Po Pz Qa Qb QC QD Qe Qg Qh Ql Qm Qn qO Qt Qx Qy Ra Rb Rc Rf Rg Rh Rj Sr Ss St Tn To Tr tT Tv tX Tz Ua Ub Ud Ue Uf Ug Uh Uk Ul Um Un Uo Up Us Ut Uu Vt wL zH) Ok(AD aE AF aG aI AJ aK AL aM An aO AP aQ AS aU aV Aw AX aY aZ Ba BB BC bE bF BG bH bI bJ bL bM BN BO bP bQ bS bV bW bX bZ cA cC cE cG CH cI cJ cL cM CO CP CQ cR CS CT CU CV CW CX cY cZ dA DB DC DD DE dF DG dH dI dJ DK DL dM dN eC eD Fb gL gW hB hC hF hG Ic iJ iO iP iZ Ko kQ kR kS Kx nW nY oE oF oH oN oP Pj Pk qC Qv Qz Rh sC tN tQ TT tV tX uL uM uN Ur Uv uZ vB vH vl wL yH tL xA Wm) Nj(aD aE aF aG aH aI aJ aK aL aM An AO AP aQ aS aU aV AX aY aZ bB Bc bE BG bH bI bJ bL bM BN BO bP bS bW bX bZ cC cD cE cG cH cI cJ cK cL cM CO CP CQ cR CS Ct CU CV cW CX cY cZ dA dB DC dD dE dF DG dH dI dJ DK DL dM Ex Fp fR Im In Is Jg Jp Jq Lh Li Lj Lv Mn Mp Mr Mz Na Nc Nd Ni Nl Nm Nn No Nr Nt Nv Nx Of Og Om Oz Pa Pe Po Qa Qe) Jg(aA aD aE aF aG aI aJ aK aL aM aO aP aQ aS aU aV Aw aX aY aZ bB bE bF bG bH bI bJ bL bM BN bO bP bQ bS bV bW bX bZ cA cC cD cE cG cH cI cJ cK cL cO cP cQ cR cS cU cV cW cX cY cZ dA dB dC dD dE dF dG dH dI dJ dK dL dM DR eC Fi fP fR gL hB hC hF hG Ic iJ iO iP Iv iZ kQ kR kS Lw Lx Mm Ms Mu Mv Nc Ne Nq nW nY oE OF Og oH oK oN pF Pj Qz Tj tF) Jd(aA aD aE aF aG aH aI aJ aK aL aM aO aP aQ aS aU aV aX aY aZ bB bE bF bG bH bI bJ bL bM bN bO bP bQ bS bV bW bX bZ cA cC cD cE cG cH cI cJ cK cL cO cP cQ cR cS cU cV cW cX cY cZ dA dB dC dD dE dF dG dH dI dJ dK dL dM dR eC eD EF Ex Fi fN fP GL gP gW hB hF hG iP jD jM jY kQ kR IL Lt oE oF oH oK oN pF qC qU Uw Vc Vs Vu

Constrained panels with 3 analytes, where 1.0E-9 >= 'model p-value' > 1.0E-10. Contains 656 panels of 37,563,518 total panels evaluated. :
aC{Bn(Af aN Ao AR bA BC bE bF Bg bU bW cG cN Co Cp Ct Cu Dc dF Di Dl FR) cF(aJ aN AR bA bB bC bF Bg bQ bW cA cE cG cN Co cT Cu Dc dF Di Dk dN Fr) Di(Ao AR aW bA bC bE bF Bo Ch cN Co Ct Cu Cv cZ Dc dF FR) Ct(aN Ao AR BC bE bF bU cB cG Ch cN cW dF Dg Dl Ex) aW(aN AR bA bC bF Bg bR bU bW cG Co cT Cv Dk dN Fr) Dl(aJ aL Ao AR aX bE bF cA cE cN cS cW cZ dF dJ) Bo(Ao aR aX bE bU Ch cN Co Cu Cv cW cZ Dc dF) Bc(aN Ao AR bA bE bF bU cN cW dN) fR(Ad aN aO Aw aX aY Bb bE bX cW dL) Ch(Ar aX bE bW cG cS cZ Dc dF Fr) bF(aN aR bR bU cN Cp Cu Dc Dg dN) Ao(aJ aR aX bA bE bU bW cZ dF) Co(aR bA bC bU bW cB cN cT dN) Bg(aN aR bA bC cB cN cT dN) Dg(AR bC bE cN cW cZ dN) Cu(aL aN aR bC cB cN cZ) Dc(aN bA bC cB cN dN) Ar(aN bA bU cB cN) Dk(aN bA bC cB dN) On(aR Hx lu Na Qb) Fr(aN bC cB cT) dN(aR bR bU cT) Ap(Bb bC) Cp(aX bE) cB(aA Cv) EtaR aNbU} Et{Ok(Hr Hw Hx In It Iu Iv Jo Mb Mm Ms Mw Ne Nj Nk Nm Nq Og Om Oy Po Pz Qb) Ii(aA Is Ji Jq Jr Lj Lw Lx Mb Mr Mt Nc Nk Nr Nx On Pa Pe Po Qa) Ms(aA Fp Iv Ji Jj Lw Mb Ne Ng Ni Nj Nk Nl Nx Of Pa) Nc(aA Ij In Io It Iu Iv Mb My Nq Of Oy Pz) Nl(In Io It Iu Iv Jo Lw My Nh Ni Nm Oy Pz) Mb(aA Ij Il Lw My Ng Ng Of Og Oy Pz) Nj(Ij Il In Ng Ni Nm Of Og Pz Qb) Iv(aA Ij Il In Ng Of Og Om Pz Qb) Jj(Hx Lj My Ne Nk Nq Nr Nx Pa) Ne(aA Ij Il Ng Of Og Qb) Fp(Il My Ng Of Og Qb) aA(Hx My Nx Og Oy Qb) Il(Jr Lj Lz Nk Of) Nk(Ni Og Qb) Of(Ni Nx Og) LxMy IjJi} Ok{Po(aA Fp Hx Ii It Jj Lx Mb Ne Ng Nj Nk Of Og) Hx(aA Fp Hr In Iv Lx My Ng Nk Nl Of Og) Ne(In It Iu Mj Ng Of Og Om Pe Qb) Nk(Hw It Iu Mj Mk Nf Ng Og Om Qb) In(Jj Jq Mb Mz Ng Nx Og Om) It(aA Ij Mb Ms My Ng Of Og) Nf(aA Iv Mb Ng Of Og Om) Nx(Mg Ms Ng Nm Og Pz Qb) Mb(Hr Mm Of Pe) Mj(Lx Nr Og Oz) Iv(Hw Iu Pz Qb) aA(Mk Nq Om Pc) Nj(aR Iu Jo) Og(Hw Lv Lw) Pa(My Pe Pg) Nm(Jj Of) Mk(Mc Oz) Ms(Ji Lw) Ng(Jg Lv) Ii(Hr Qa) Qb(Fp Lx) NrJj MwOn NcHw NlJo IjJi IuOz NwPg} Nd{aA(Is Iv Jg Jj Jp Jq Jt Lh Li Lw Lx Mn Mt Mz Nc No Nr Nv Nx Of Og Om Pc Po Qe) On(aN Ij Il In Iu Iv Ji Lw Mg Mk Mm Ms Mz Nc Nm Nq Oi Om Oz Pa) Mm(Fr In Iv Ji Jq Jt Lw Lx Mn Mr Na Nc Ng No Nw Of Oz Pc) Jj(Fr Is Ji Lh Li Lx Mn Mt Nr Nv Nw Po Qa Qe) Ji(Im Lx Mn Og Pa) Lw(Fr Lx Nw) NwOg} aN{cB(AW BA Bb bC bF Cp cT) Aw(bM cF cK cT Dl) On(Jl Nj Tj) bU(Ba Bb Cp) cF(bF Cp) DlcT} On{Jj(Iv Ms Nj Nl) Ii(Iv Nj Nl) TjJd JlaR} aW{cB(aR Aw bF) AwbU} Tj{Jd(Ir Pa)} RifNrN Constrained panels with 3 analytes, where 1.0E-8 >= 'model p-value' > 1.0E-9. Contains 968 panels of 37,563,518 total panels evaluated. :
aC{On(Af aK aL aN aW aX Bb bR bU cA cB cD Cw cZ Db dE dJ Et Hr Ii Ij Il Jh Jj Lh Mv Nd Nf Nj Nr Ns Nv Of Om Tj) aR(aJ aN Ar bA bC bR bU cE cG cN cT cW Dc dF Dk Fr Is Jg Jh Ji Jt Mv Nw Of Ok Om) Of(aN Bb Bo cA cD cN Cw Et Is It Iu Jg Jh Ji Jj Lw Lx Mm Nw Ok) Et(aL aW aX Bb bR bU cA cB cT cZ Di dJ Hu Is Jh Mv Nd Nj) aN(aJ aX bA bB bC bE bQ bR bW cE cG cN cS cT dF dN Is Ok) bU(bA bC Bg cA cE cG cN cT Cu Dc dF Dk Fr Jh) Ar(aJ bE Bg bW cE cG Cu cW cZ Dc dF Dk) cN(aW bA bB bC bR cG cS cT Dk dN Fr) Bb(Ef Io Is It Lw Mc Mm Mv Nd Nj) bR(aJ bA bC bQ cE cG dF Is Jg) bE(Bg cG Co cT Cu Dc Dk Fr) cZ(Bc Bg Co Ct Dc Dk Fr Ok) Ex(Ad AW Ba cB Ch De) Ct(aJ bQ bW Cu dJ Fr) Mv(Is Ji Lw Nj Nw Ok) aL(Bc Bg cG Fr Jg Ok) cW(cG Co Cu Dk Fr Ok) aW(aJ bM bQ cS dF) Aa(Aw Bo dN fR) Dc(aX bW cG dF) Tj(Ad Cp Cw Dk) Co(aJ aX dF) bC(bB bF cT) Bc(cG cK) Bg(aJ bN) Cw(Io Nf) Di(Io Is) Dk(aJ cS) Nj(Nw Ok) Jh(cB Is) bA(bF Fr) bM(bF cT) CpFw EffR NdOk NfPd JgcB bWcT cAdN} Et{Ij(aA Is It Jq Jr Lj Lw Lx Mh Mt Mz Nh Ni Nk Nr Pa Pe Qa) Fp(Hr Hw Im In It Iu Lw Mj Mw Ni Nm Nq Oi Om Oy Pz) My(Io Iv Jg Lw Mc Mt Ne Ng Ni Nk Of Og Om On Pa Pz) Nq(aA Iv Jg Ji Jr Lw Lx Ni Nk Om On Pa Pc) Oy(Iv Jg Ji Mc Ne Ng Ni Nj Nk Of On Pa Pz) Pa(Hx Il Mu Mw Nj Of Og Pe Pg Qb) Iv(Io It Iu Jo Lw Mb Ni Nj Nm) Ne(In It Iu Lw Nh Ni Nm Pz) Ng(Hx Lw Ni Nk Nr Nx Og Qb) Lj(Hw Hx In Ni Nm Om Pz Qb) Nk(aA Hx In Io Iu Of Pz) Il(Is Ji Lx Mh Ml Oz Pe) Mw(aA Jg Ji Jr Om On) Qb(Is It Jr Lw Lx Qa) Om(aA Jr Lw Mv Ni) Ms(Jr Lx Mc Og) Mu(Ji Mc On Pc) In(Jq Jr Mb Nx) Pz(It Lw Ni Nx) aA(Mk Ni Of Pe) Nm(Ji Mb Nx) Nj(aR Iu Jo) Lw(Hx Og) Mk(Mc Oz) Mv(Ji On) It(Ii Jq) Iu(Mb Oz) iA(cA Di) MrHx NiOg JoNx OfOn} Nd{Jj(Im It Iv Jg Jk Jl Jm Jp Jq Lj Lw Mg Mp Mz Nm Nn No Nx Of Oh Pa Qd) Lx(Fr In Iv Jl Jq Jt Me Mh Mn Mr Mz Nc Nm No Nw Og Oz Pa Pe Pg) Fr(Iv Ji Jq Jt Me Mn Mz Nc Ng Nm No Nw Of Og Oy Pa) Nw(Ii Iv Jt Mn Ms Na Nc Ng Nm Of Oz Pa) On(aR aW bR cB cD cF dE Di Nb Pz Tj) Lw(Im Jp Li Mn Mz No Nv Og Pa) Jg(aN aR bR bU dN Mu My Ng Oy) Ji(Ii In It Iv Ms Nf No Oz) Og(Im Is Jt Lh Mn Nv Qa) Mn(Jt Mr Mz No Pa) aA(Im Mp Pe Qa Qd) Ok(aN aR cD cW) Mm(Iu Lh Lj) Jt(It Ng Pa) No(Me Pa) Mz(In Pa)} aN{cB(Ad aJ Ao aR aX Bn Bo bQ bU bW cA cE cF cG Ch cK cN De Dg Di Dl On) On(aR bR bU cD cK dE Hr Hx Ii Il It Iu Jj Mb Na Nf Nr Of Om Qb) bU(Ad Ao aW Bn Bo cG Ch cT Cw De Dg Di Dl Is) Aw(Ad aR aW Ba Bb bC bF Bn bR cG Ch cN Dg) cF(Ad Ap aW Ba Bb Bn Bo Ch cT Cw De Dg Dl) bF(Ad aW Bb bC bM Bn bR cK Cp Ct Dl) cT(Ad Ap Bb Bn Bo Ch Cp Dg) Bb(aW bM Bn cK cN Nj) aW(Ad Ch Cp Dg Dl) Dl(Bo Cp Di) Nj(Nw Ok) Is(Di Om) BnCh CpcK TjOk} On{Tj(aH Aj aO aR bQ bR cB dG Hf It Jl My Ng Pa Qw Qz) Jj(aR Fp Hx iA Io Mb Mu Mw My Nc Ne Nq Nx) Nj(aA aR aW bR cB dE Mu Mw My Of Oy) Ii(Ji Lw Mb Ms Mw My Nc Ne) Nl(Il Ms Mu Mw My Of Oy) Iv(Ms Mw My Of Oy) Mb(Mw My Of Oy) Jl(aW bR cK Jd) iA(cA Hr Na) Ms(Io Of) Mw(Nc Qb) aR(Hr Hx) NcOy InPi ItJd QbbR} cB{aW(Ad aJ aP BA Bb bC Bn bQ bU bW cF cG Ch cK Cp cT De Di dN Ex) cT(Ad AR Aw Bb Bn Bo Ch Cp De Di Dl) aR(Aw bA bC bF Bn Cp De) bA(Ad Aw Bb bF Bn De) bF(aH Bn cK) AwcK BaBn bQcO} Jj{Iv(Fr Ji Jt Lx Mm Mt Nc Nj Nl Nr Nw Nx) Nl(Ji Jt Mm Nx) Mm(Fp Nj) Nc(Ji Nx) FrNj NrNx MsJi} aW{cF(Ad Aw Bb bF Bn Cp) bU(Ad Bb bF Ch De) Aw(aR bM cK) Ad(cK cT) BbcK NjOk bFbR} Ok{Nj(aH bR cW) Tj(aR Jd) Nm(Ji Ms) Jo(Lv Nx) NnPc LxPz MjLj MwJg bMgV} aR{Nj(Bb Jg Jh Mv Nw) Jg(Aj bR bU Di) AwbU} Bb{tV(Hc jY lL Nq Oi Qw) UbvB iHrC} Jd{Tj(Fa Ha Is Lx Mr Pe) IbTt InPi} Ad{cT(Aj cF) gP(Bo Di) hL(Ex Gz) HfqU} Pj{Qv(yH tL) hO(Bo jY) HuwD iHqU} Ji{Ms(aA Iv) Ii(aA Iv)} cF{Bn(bF cT) AwcT CwoK} Kq{lcgP HfqU} AwbUcT CwNfoK TiRcjY ThNyqY LuRitX MmNcNi MnPhdX MyOmaA NjJgbR TtqWvS Constrained panels with 3 analytes, where 1.0E-7 >= 'model p-value' > 1.0E-8. Contains 3,191 panels of 37,563,518 total panels evaluated. : aC{Mv(Ad aL aN Ap Ar aW aX BC bE bR bU cA cB cD cF cN Cw Di dJ Dl dN It Jg Jp Jt Lx Mg Mm Mt Na Nd Ni Nm Nx Of Pa Pd) Is(Ao Ar AW Ba Bg Bo bU cB cF Ch Cw De Dk dN Hu Il Iu Jg Jj Lw Mg Mm Mu Mw My Na Nd Nf Ni Nj Nk Nw Og Ok Om Pd Qb) Om(Ad Af aL aN Ap aW aX bC bR bU cA cB cD cN Cw Di dJ dN Et Il In Jg Lw Mc Mm Na Nd Nf Nj Nr Nw Of) Of(Ad aL Ao Ap Ar aW aX BC bR bU cB cF Di dJ dN fR Hr Il Jp Mc Mt Na Nd Ni Nj Nm Oe Pd) Nw(Ad aN AW Ba Bg bR bU cA cB cD cF Ch Ct Cw cZ De Di Hu Jg Jh Mg Na Nd Nm Oy) Jh(Ad aN aW aX Bb bC bR cN Cw Di dN Il Jg Ji Jp Lw Mc Mm Mt Na Nd Nj Nq Ok) Jg(Aj aN Ar aW aX bU cF Cw cZ Di dN Jj Lw Lx Mc Na Nd Ni Nj Nx Pd) Ok(AW bE bR bU cA cB cD cF Ch cN Cw Di Jj Lw Na Nf zH Tj) Ex(Af Aj Al BC bE Bg Bn bo bQ cA cD cN cT Dc Dd Dl) aR(aG bB bE bQ bW cA cS Ef Jp Lh Lw Mg Mm Mw Nj Nm Pd) Et(aH aN Ar Aw BA cD Ch Cw Il Iu Lh Mc Na Qb) bR(aP aX bE bW cA cL cS cT dG dH Eo Ji Jt Pd) Jt(aN AW Bb cB Di It Iu Jj Na Nd) bU(aJ aX bE bH bQ bW cS dB dJ Eo Ji) Ad(Il In Jj Lw Mc Na Nf Nj Og Pd) Ef(Aj Ao aW Ba Bo cB cF De Di Gd) Mm(aN Ar AW cA Cw De Di Nd Nj) bB(aJ aL aX bE bN bW cS cW cZ eO) Io(Ar Aw Ba Bo Ch Cp De Dk fR) Cw(In Jj Lw Mc Mu Nd Nj Nn) Pd(aN Aw Bb cB fR Nd Nj Nr) Ji(aN Aw cB Ch dN Hu Na) bQ(Aa bC bE bM bW cK cO) Bb(Jp Lx Mt Na Nl Tj) Eo(aD bM bW cS Cx dK) Mg(aN cN Di fR Iu Jj) Cp(Gp Hv It Jj Na) Lw(Ap Aw Ch Hu Nj) Dr(Ao Ba Bg Co) Tj(Aw cB De Dl) Nm(AW Di Nj) Aa(Ao aW Fr) Nj(Lx Mw Ni) cA(aN bM cS) cK(aP aX bA) fR(Jn Nc Og) Di(Ip It) dF(aL bC) eO(aW dB) AwIt DeNf FwOn MzzH HucB IcJd JpdX bAbE bZcG cEcT} aN{eO(aD aE aI Aj aK aL As aW aX bA bB bC bE bF Bg bH bN bQ bU bV bX bZ cA cB cD cE cF cG CH cI cK cL cN cO cQ cY cZ DB dC Dd dE dF Dg Dl dJ dK dN Dw Em Eo Ew FP) Nj(aR Ba bU cB cN cT Et Fr Hu Is Jg Jh Ji Jj Jp

Figure 4 Continued

Lw Lx Mm Mt Mu Mv Mw Nf Ni Nm Nr Ny Of Om Pa Pd) Is(aR Aw Ba Bb Bo bR cB Ch cK cQ cT It Iu Jg Jh Jj Mc Mv Na Nd Nf Ni Nk Nw Of Og Ok Qb) bU(Ap AR bA BC Bg bQ bW cA cE cF cK cN Co Ct Cu dF dN Eo Fr It Jd Jg Jh Ji Nw Ok) cF(Ao AR bA bB BC Bg bQ bR bW cA cE cG cK cN Co Ct Cu Dc dD dF Di Dk Fr Ok) Ok(aR Aw bR cB cG cK cN cW Di Fw Ii It Jg Ly Ma Mv Nf Nr Of Om) Bn(Ad Ap aR aW Ba bC bM Bo bQ bR cG cK Co Cp Cw Dg Di Dl) Dl(AR BA Bb bC bR cG Ch cK cN cW De dF Eo fR) aW(Ao Ap Ba bC Bo bR cG cK Co cT Cu Cw De Di fR Jg) Ad(Aj BA bC bM Bo bR cG Ch cK cN cW De Di) Bb(aR Ba bC Bo bQ bR cG Ch Cp De dF Di Nd On) Jg(Aj aR bR cB cK cT Di Jj Lw Ly Mc Ni Nx Of) Ch(BA bC bF bM Bo bR cG cK cN Cp De Dg) Nd(Et Jh Jp Mm Mv Nm Nw Of Om Pd) cK(Ap Ba bC Bo cG Cw De Dg Di Nw) Cp(aR Ba bC bM Bo bR cG cN Dg) bF(aF aO aR Ba cC cN Cw De Dg) cB(Ap Ar Bc Co Ct Cu Cw Dc Nw) On(Af Aj Fw iA Lh My Nv Pc) bC(Ar Ba Bo bR cT De fR) Di(Ba bM bR cT Dg Io) Eo(aE aO Ar bW Dk eM) Of(Bo It Ji Jj Lw Nw) bM(Ba cT De Dw Ew) Bo(Ba Ct De Dg) Nf(Cw Ny Om Pd) bR(Ba cG De Dg) cT(Ao Ar De) dW(aE bB dK) Aw(Io Mm) BacN MvNw IcJd} Nd{No(Im Is It Iv Jg Jl Jp Jq Jt Lh Li Mc Mp Mr Mt Mz Na Nc Nl Nm Nn Nv Of Og Om Oz Pd Pe Po Qa Qe) Jj(Fp Ih Ii Iq Jh Jo Jr Js Lv Ma Me Mr Mu Mv Mw Mx Nc Ng Nl Nq Nt Ny Oe Om Oz Pd Pe Pf Qb Qc) Lw(aR cT Is Iv Jg Jl Jq Jt Lh Lj Mp Mr Mt Mx Nc Nl Nn Nr Of Oh Oz Pe Pf Po Qa Qd Qe) Mn(Im In Is Iv Jg Jl Jp Jq Lh Li Mp Mt Mx Na Nc Nl Nm Nr Nv Of Om Oz Pd Pe Po Qa Qe) Pa(Im Is Iv Jg Jl Jp Jq Lh Li Me Mp Mr Mt Na Nc Nm Nn Nr Nv Of Og Oh Om Pd Pe Po Qa) Mz(Im Is It Iv Jg Jp Jt Li Me Ml Mp Mt Nc Nf Nm Nn Nr Nv Og Oz Po Qa Qe) Og(Iv Jg Jl Jp Jq Li Mp Mr Mt Nm Nn Nr Nx Of Om Pd Pe Po Qe) Jg(aH Aj Ar aW bA cB cF cN cT Di Im Iv Jq Lj Mv Mw Nq) Jp(aR Im Is Iv Jq Jt Lh Lj Me Mr Ng Nm Nr Oz Pe Po) Im(Fr Iv Jq Jt Lh Me Mp Mr Mt Nm Oz Pd Pe) Nv(Ii In Iv Me Mr Ms Na Nc Ng Nm Of Oz Pe) Lh(Hx Ii In It Iv Li Me Mt Nc Nf Ng) Ok(aH aL aW bR bU cB cF Ch cN Di gP) Jq(In It Iv Li Mt Nr Oz Po Qa Qe) Jt(aR Di Ii In Iu Iv Me Mt Nc Of) Fr(Is It Iu Lj Mr Na Oz Pe Qa) aR(Bb Et Jh Ji Mm Mv Nm Nw Of) Nm(Iv Li Mp Mt Nc Oz Qa) Et(aW bA bR cD cT Di) Nw(bA bR bU cB cD cT) Lx(Hx Iu Ml Ny Pb) Mp(Iv Mr Nc Oz Pe) In(Is Iv Li Po Qa) Mm(aW bA cT Di) Mr(Iv Me Mt Nr) Qa(Iu Me Nh Qb) Bb(bA cN On) Mt(Iv Oz Pe) AdAj ChOn DiIs MePe MyOm} On{Ii(aH aR aW bR cB cK Fp Hu Hx Ik Io Is It Jd Jj Jq Jr Jt Lj Lv Lx Mh Ml Mm Mu Mx Ng Nh Ni Nk Nm Nq Ns Nw Nx Of Og Om Oy Oz Pa Po) Jd(Aj Bg Cu Di Fn Fw Hq Hr Hu Hx iA Ib Ic Ij Il Iu Jk Kk Lh My Nt Nv Of Og Om Qb Ql Qu Qw Qz Tr Ub Uc Uv Vo) aR(aW Bb bR bU cB cD cK cT dE Di Fw Hq Ic Il It Iu Jg Mb My Na Nf Nn Nr Oh Ok Om Po Qb Uv) Mw(Hx Ik Il It Iu Jg Ji Lv Lw Lx Mm Ms My Ne Nh Ni Nx Of Og Om Oz Pc) iA(Af Bb Bo bS cD cE cK Cw Et gP Hf Ic iH Iq Jg My Nf Of Oh Rb Uv Tj) Nj(aH Aj cA cH Di Ij Il In Io Iu Iv Lw Mk Ms Mv Ng Ni Nm Nq Og) Jj(bR cB cK gP Ik It Lj Lv Lw Mv Ni Nk Nr Of Og oK Om Oy Oz) Nl(Ij In Io Iu Iv Lw Mb Mk Mv Ng Nh Ni Nm Nq Og Om Qb) It(Aj bR bU cB cK Di Fw Mu Mv My Oy Qv Rh Vo) Ms(Hx Iu Ji Lw Mb My Nc Ne Ng Ni Om Qb) Of(Hx Il Lw Mu My Nc Ne Ni Nq Og Oy Qb) Tj(bU Fn gP Ib Ic Kx Ql Qv Rg Uv Vo) Jl(aH Aj bA bU cB cN cQ Di Qv Uv Vo) Mb(aA Il Lw Mm Mu Mv Nc Ng Nq Og) My(aA cB Hx Lw Mu Nc Ne Og Oy Qb) Iv(Il Mk Mu Mv Nc Ng Ni Nq Og Om) bR(aW dE Hr Hx Il Iu Jg) Nc(Il Mu Mv Ng Ni Og) Oy(Hx Jg Ne Nx Oz Qb) cK(Hr Hx Il Iu Na Qb) Mu(Ne Pc Qb) Hr(aO aW cB) Aj(Hx Jg) Il(Ar Ne) In(Id Tv) Hf(oK qU) Io(Di Og) Qh(cB Mv) iH(Bb qU) FiKk FwNa NqqC NiNk HxcB IubU PjhO} aW{eO(aD Af aG aH aI AJ aK aM aO AP AR aS aU aV AX aY aZ bA BB Bc bE bF BG bH bJ bL bN bO bP bQ bR bS bU bV bW bX bZ cB cC cE cF cG cH cI cL cN Co cP cQ Cs CT cU Cv cW CX cY cZ dA DB dD dF DG dH Di dJ dK dL dM dN dW dX EM Eo eP EW FP FR Gd gV) bU(An Ao Ap AR BA Bn Bo cF cG cK Cp cT Cw Dg Di Dl dN Dw Eo EW Jd Jg) cF(Ao Ap AR BA bC Bo bQ bR cG Ch cK cT Cw dD De Dg Di Dl dN) Ad(aH Aj aR aV Aw BA bC bF bM Bn Bo bR cG Ch cN Di dJ) cK(Ap aR Ba BC bF Bn Bo cG Ch Cp De Dg Di Dl dN) cB(An Ao Ap Ar Bc Bo Cv Cw Dc Dg Dl EW FR) Aw(aH aK aQ aV Bb bC bF Bn bR Ch cT Dg dJ Dl) Bn(Ap aR Ba Bb bF bM Bo bR Ch cT Dg Dl fR) bF(aH aR Bb bC bM cO Cp dJ Dl fR) Nj(Bb Et Jg Mm Mv Nm Nw Om) cT(Bb Bo Ch Cp De Dg Dl fR) Cp(aR aV bM bR dJ Dl) bR(cG Dw EW Jg) fR(bC bM Ch De Dl) aR(Bb Jg Ok) bM(Bb Ch De) dW(aD bB eP) Ew(bH dX) cP(cW Ko) BoDl DwbB EfgV EoaD} Jd{Tj(Ad Ar Ax Bn Cp Cq Cs Cu Cw Dc De Di Et Hw Hx Ib Ic Id Ii Ij Im It Jh Ji Jq Jr Jt Kd Ke Kf Kj Kn Ko Kp Kq Kr Kx Lh Li Lw Mc Mj Ml Mm Mq Mt Mu Mv Mz Na Nm Nr Nv Nw Nx Ny Oa Og Oh Om Pb Pd Pf Ph Pi Pj Pk Po Qa Qe Qv Qx Qz St Tv Ub Ur Ut) Di(aR Bg bU Fw gP Hu iA Ib Ic Kk Mc My Ns Og Om Qu Qw Qz Vo) Qz(De Hu Ib Ic Id Mv Og Om Pa Qv Ub Uf) Ic(aR bU cF cN Hu Ib Og Om Ub) bU(aR cC dB Fw iH Iu Na Uv) Ib(Hu Id Kj Mv Og Oh Ok) Id(In It Iv Og Om) Tt(Aj Hu Om) Og(Kk Lw Ub) Cw(iA oK) Mv(My Qu) In(Kq Mr) Ip(jD IL) Kz(eD IL) Oh(Lh Om) FaFw HpoK HuQu TrIt HfqU StOm QvPj JrJs} cB{aR(aA Ad aJ aP Ba Bb Bo bQ cA cG Ch cK cN cW Di Dl dN Jg Jh Nj Ok) Bn(Ad aJ An aP Aw Bb bC Bo bQ cF Ch cK cN Cp Di Dl Tj) De(Ad aH aJ Aw Ba Bb bC bF bU cF cK cN Di Ex Tj) cK(Ad aJ aP BA bb bC bQ cG cN Cp cT Di dN) bF(Ad Aw Ba Bb bC bU bZ cF cN cO Cp cT Dl) bA(Ar Bo bQ cA cF Ch cN Cp Di Dl eO) Aw(aH aJ Ba bC bM bO bU cF cN Dl) cN(Ad Ba Bb Cp cT dD EW Ex) bP(DW EO EW) cT(aJ bC bM cA cF fR) Ad(aH Aj Ba Di Tj) Nj(Bb Jg Ni Nw Ok) Ba(bC cF Cp Di) dM(EO EW) Bb(Di Ex Fw) Bo(dW eO) Tj(Cp Ok) bQ(bC cF) dJ(dW eO) AoEx} Jj{Iv(Fp Im Is Jg Jl Jq Lh Li Lv Lw Mg Mn Ne Nm Nn No Nt Nv Of Oh Oz Pa Po Qa Qe) Nl(Fp Fr Im Is Jg Jq Lh Li Lw Lx Mg Mn Mt Nm No Nr Nv Nw Of Oh Pa Po Qa Qe) Nj(aA Ad aR bU cT Im Is Jg Ji Jt Li Lx Mn Mt Nr Nv Nw Nx Pa Po Qa Qe) Nx(aA Fp Fr It Jg Ji Jt Li Lj Lw Lx Mm Mt Ne Nk Nt Pa Po Qa Qd Qe) Ji(Fp Hx Lj Lx Mb Mm Mt Ne Nk Nr Oz Pa Qa) Nc(Fr Is Jg Jt Li Lx Mm Mt Nv Nw Po) Mm(Ik Lv Mb Ne Nr) Jt(aR iA Mb Ne) Et(iA iH oK) Jg(aR iA) CwoK LxIk OfaR} Ji{Iv(aA Hx Ij Il In It Mb Mm Mu Mv Mw My Nc Nf Nj Nl Nm Nq Og Om Oy Oz Qb) Ii(Fp Fr Im Jt Lx Mm Ms Mt Nc Ne Nj Nl Nr Nx Oz Pa Po Qa Qe) Ms(Fr Lx Mc Mm Mt Nc Ne Ni Nj Nl Nm Nx Of Og Oz Pa) Nl(aA Ij Il In It Lx Mm Mn My Nh Ni Og Qb) Nc(aA Ij Il In It Mb Mm Ni Og Qb) aA(Hx Ij Mb My Ne Nj Og Oy) Lx(Ij Il My Qb) aR(bU Mv Nj Of) Ij(Fp Mt Ne) Nj(In Og) EtIt MbMm MwJg NeIl NiNk ImOg} aR{Nj(bA bU cT Di Fr Is Jp Jt Lw Lx Mm Mr Mt Mu Nb Nf Ni Nm Nr Ny Of Om Pa Pd) Ok(bR bU cD cF cK cW Di Jh Lw Ma Mv Nf Of Oh Om) Jg(Ar bA Bn cK cQ cT Lw Ly Mc Of Om Pa) Di(bU Et gP Io Is Jh Jt Of) Aw(bF bM Bn cF cK cT Dl) Bn(bF Bo cF Ch cT) bF(bR bU cF cK) cT(Ad Bo cF Et) Of(Bo Hr Ic) bR(Et Jt) gP(Bb Cp) CwoK MvIc JhbU} Et{iA(BA Bo bS bU cC cE cM cQ cT Cw dD gL hB hG Hu iH Im Iq Jg Jh Mq Mu Mv Mw Na No Nv oK Pc Qv) iH(bU cM Di Mv oK qT qU tF) Nj(bA bR bU cT Di) Di(gP qY tV) Mr(Mk Nb Po) Mz(In It Nf) Jr(Js Mu Nf) Lj(Io It Iu) oK(Cw Hf Na) Pe(Mk Po) Pg(Lx Nw) TjFa NnPc NqIo MmNx HvIt InPi HfqU JnJs KsqQ RirN UvtF tTzH tVqW} Bb{tV(Bg gW Hu Ic Iz Jk Ky Kz Mz qW rC Ua) Nj(bA bR bU bV cN cQ cT dN Ni) Hf(eD jV jY qU qX qY rC) eD(Ic Kz Na Nq Pa qO) gP(Aw Bo bU cF Cp Di) iH(bU cF cM Mm) lL(rO rW sC uL) Mz(fN qC tT) bF(Bn bU cK) cT(bU cF cK) Nq(qC tS) Ri(rW tS) tT(Oi Pj) jY(rS rW) DifP NajD IctN QvuU cKcN} Ad{cT(aH bF bM Bn Bo bU cK cN Ct gP) Aj(bF Bn bU cF cK fP gW Nj) cF(bA bF Bn cK cN gP iH) Na(eD hA jM lK lL qU) Di(Bn fP iA iH) bF(aH Bn cK) iH(qT qU qW) Hf(qW qY) Qw(qQ tV) BogW ExqA bAcK} bB{eO(aD aJ aK aM aP aQ As aY aZ bA bL Bo bP cE cI cM cN cP cQ cW dA Dc dE dG dH dJ dL dM Ew gV) Ew(aF aO bM bP bW) Eo(aD aJ bP dM) Dw(aD bM bP) dW(aD Bo) eW(aF bM) JgiA cFiH} Mm{Nl(aA Fp Il In Iv Lv Lw Mb Nh Ni Og Pa) Iv(aA In Lw Mb Ms Nc Ni Nj Og Om) Mb(aA Jq Lw Mz Na Nc Og) Nj(aA Ar cT Di Ni Og Pa) Nc(Fp Lv Nx) Di(tO tT) CwoK NiNk} Pj{hO(Ic jD IL Mq Nq Oi Qv tF) Qv(Hu tV uT vS yL zI) qD(Ic jD jY IL Nq) Ic(qB qC tM) iH(eD qW rC) jD(cC qB qC) Di(qY tT) Ri(rN yL) tV(Hu qW) CwoK TjFa IlsJ HfqU tTqW qCjY} cF{cT(Ap Ar Bo Ch Cp De Dg Dl) Aw(bF Bn bU cK cN Dl) gP(Ao Ba Cw Di Ok) Nj(Jg Ni Nw Ok) bF(bR bU cK cN) iH(bU cA cM dD) Bn(Ba Bo cK) cK(Cp Dc) CwoH TjOk bMdW} Jg{iA(bU cA Cw Di Ez iH Lw Lx Na No Nw Pa Pc) Nj(aH Aj bA bU cQ cT dN) bR(Aj cN Is Ly Mc) Aj(aH bU) Tj(Fa Pa) DiaH MwOm OyaA bUiH} Nw{Nj(aA bA bR bU cT Ii) Nl(aA Ii Il Lw Ms Ni) Nc(Ii Il Ms Ni) Iv(Ii Il Ms Om) iH(qU uZ zH) CwoK NeIl QteP KzrX} bM{dW(bQ bV bX cA cD dE dI dJ Em) Dw(Bo cU cY dE

Figure 4 Continued dK) Aw(bF cK cT) dE(EO eW) bX(eO eW) BnbF EobJ bNeW cTfR} cT{bU(Ar Bn Bo Ch Cp De Di Dl) cK(Aw Bn Bo Cp De Dl) Bn(bF Bo
Ch Dl) Aw(aH cN Dl) BoDl ChcN NiNj} Ok{Tj(aH bQ bR Fa It Pa) iA(cA eD Nf Oh) Di(aH gP Nj) Nj(aL Ar) eD(iH Rb) gP(Bo Nf) CwoK
iHqU yHzH} Cw{oK(Di Ib Ic Il In Io Iu Ko Kq Lx Mc Mz Rh Uv Vo) Nf(iA iP) eD(bQ iA) KodX} Aw{cK(bA BC bF Bn bU cG cN Dl dN)
bU(bA bF bJ cN) Vq(hO vB) aHbF dBeO} Bo{cN(DW EO EW) Dw(bP dM FR) Ew(Co dM) dW(bP dM) cO(dB fP) DlgP} Mz{qC(cV gW Ic jD jY lL Qw) zH(gW iH oN pF yH) IphL iHvS qDlL} bF{Bn(aF aH bC bR bU cK cO Dl) bU(aH cK cN De) DlaH NiNj aOfR} Nj{Ni(aA Ar bA bU cN Di) aA(Fr Iv Lx Nx Pa) Di(Ar Is)} Vt{zH(gW jY oF) Ri(rW yK) qU(rP rT) tL(jY Qv) DiwH NutS QwtV iAyK} Nl{aA(Iv Ni Nx) Fr(Il Lw) LwIv LxIl ItJt} iH{qU(Jt Nm) AaqW KczH VqsC bUcA bZlM} Ri{Tr(rN rU rW) rN(Ap Tt) fNtV} Fb{Kk(Rx Vh We) BnUw LhVh} Vq{Qv(sC uG uN vP) tFuM} aM{cV(Dw EO) EobJ cAeO} Tj{Fa(Io It Jt Kf)} Qt{eP(Kc Kp Kz) KcdX} Kq{Hf(gP rX tF) UsrX} nN{mY(jE qY) nOqT jFqY} rS{Nh(sF sH sI) MksF} Nx{aA(Iv Ms Nc)} aO{dG(DW) EwcG} dB{eO(cW dE dG)} rN{Ap(iA jY) KfiA} Di{Is(bR Om)} Ip{IcjD tVlN} Jt{NcIt KkdX} Pc{sI(rX rY)} aK{bP(dW Eo)} eM{DuIb bAbR} fP{HrsH bQcO} qC{NqUn LhjY} DkJktV ExhOqQ TtUvtF IlKssJ JpKddX KodKeP bCbWfR

Constrained panels with 3 analytes, where 1.0E-6 >= 'model p-value' > 1.0E-7. Contains 9,177 panels of 37,563,518 total panels evaluated. : aN{Of(AR BA Bb bC bF bQ bR bU bV cA cB cD cF cK cN cT Cw Di Et Ex Hr Ic Jd Jh Jp Lx Mb Mc Mm Mt Mu Na Ni Nl Nm Nx Ny Oe Om Pd Tj) Nj(Ad Ao Ap Ar Aw bA BC bF Bg Bn Bo bQ bR bV cA cD cF Ch Cp Cw De Dg Di Dk Dl It Jt Lh Mc Mg Mn Mr My Mz Nk Nv Nx Oy) Mv(Ad aR aW Bb bC bR bU cA cB cD cF cK cN Di Dl Et Ic It Jd Jg Ji Jj Jt Lw Ly Mc Mm Mt Ne Nh Nl Nm Nx Ny Pa Pd) Di(Ao Ap AR aU aV BC Bo cG Ch cN Co Ct Cw De Et fP Ip It Jd Jh Ji Jp Jt Lw Mg Mm Mt Nd Nm Nw Om Pd) bR(aJ Ao Ap aR bA Bo bQ bW cE cK cL cN Co CT Cu Cw dF dN Et fR It Jd Jh Ji Jt Mm Nw Pd Qa) cK(Ao Ar bA Bc Bg bQ bW cE cN Co CT Cu Dc dD dF Dk dN Et Fr Jh Ji Lw Mm Mu Nm Ny Om Pd) Et(aR AW BA bC bU cB cD cQ cT De Hu Jh Jj Lw Mb Mc Mt Mu Nf Nl Nw Ny Om Pa Pc) Nm(aC AR AW BA bF Bo bQ bU bV cB cN cT It Jh Mc Mt Mu Nf Nl Nw Ny Om) Nd(Ad Ba bU cB cD Ch cT Cw Hu Io It Ji Jt Lw Lx Mg Mt Mu Mw My Nv Nx Ny Pa) Om(Ad aR aW Bb bC bU bV cB cD cT Il Io It Jd Jg Ji Mc Mm Mt Ne Nl Nr Nw Pa) Ch(Ap aQ AR aV bJ bQ bW cE Ct Cu Cw dE dF dN fR Io It Ji Lw Mm Nw) Jh(aR aW bA bC cB cQ cT Il It Jg Ji Lw Mc Mm Mt Ne Nf Nl Nq Nw Nx Pa) De(Ap aQ aR aV BA cG cN dE Dg dN Ic Io It Jd Ji Lw Mm Nf Nw Pa) aW(AR aU aV bA Bc Bg bM bQ bW cE Ct Dc dD dF Dk dN Ex Fr Ko Mm) It(aC Aw Ba Bb cB Cp cT Jg Jj Jt Lw Mg Mm Mt Mu Nf Nw Ny Pd) Jd(aR Bb bC cB cF Fw Hu Ib Kk Mr Og Ok On Pa Qz Uf Ut Uv Tj) aC(Aa Ef Hu Im Ip Jp Lh Lw Lx Mt Mu Mw My Ng Nr Nx Ny Oy) Ba(aV cG dE Dg fR Io Ji Jj Jt Lw Mc Mm Mt Nw Pa Pd) Bo(aK Ap aQ aR aU aV bA Bc bM cG cN Cu Cw dE dN Io) bU(aJ bB bH fP Hu iH Jj Jp Jt Li Mm Mt Mu Nl Ny Pd) Bb(fP gP Ic Io Jj Lw Mc Mm Mt Mx Ne Nf Nl Nw Pa) cB(Ef Ex fP fR Hu Ji Jp Jt Lw Mm Mt Mu Ny Pd Tj) Cw(aR bC bM cG cN Ct dE In Io Ly Nw oK tF) Ji(aR Aw bA bC cF cQ cT Hu Jj Mc Mt Mu Nf) Mm(AR bA Cp cT Hu Mb Mc Mu Nl Ny Pd) Ct(Ap Ar bC bM Bn bQ cG cN dF fR Nw) cT(aR bW cG cN dN Jt Lw Mg Mt Nw Pd) fR(aD aU bJ bM Bn bO bW cJ dB gW) Ic(Hu Jg Kq Mu Ny Ok On Uf Ut) aR(Ap bC Dg Jp Jt Lw Mg Nw Pd) Aw(Jj Jt Lw Mc Nf Nw Pa Pd) Co(bA bC bM bW cG cN dX eO) Cp(fP Fw Hv Io Jj Mc Nf Tj) Jg(bA cF cQ Na Ng Nw Pa Tj) Ao(bA bC bM Bn cG cN Io) Dg(Aj Ar bA bC bM cG cN) Ad(Jj Lw Mc Na Nf Pa) Jt(bA Jj Mc Mt Nf Tj) Ap(bA bC bM cG cN) Ar(cG eO Io Is Lw) Bn(bA cJ Cu dN Io) Pd(bA bV Mt Nr Oh) Dl(aV bQ cE dN) Tj(Ir Is Kf Lh) Mg(cN Jj Nw Ny) On(Hf Pj Qw Uv) bC(bB bQ cG dD) bM(Bg cG Cu dD) Lw(Hu Mt Nf) Nw(Bg cD Hu) Mt(cF Jj) Is(Al Hu) Ok(Jj Lh) cN(Cu dD) EodK NfPe TrsJ QvPj NycD} aC{Nj(Ao Ap Ar AW BA BC Bg Bo bQ bR bU cA cB cD cF Ch cN Cp cT De Dg Di Dk Dl dN Fr Hu Im Ip It Ji Jj Jp Jt Lh Mc Mg Mn Mr Mt Mu My Mz Nf Ng Nk Nr Nv Nx Ny Oy Pa) Lw(Ao Ar aW aX Ba bC Bg Bo bQ bR bU cA cB cD cF cN Cp CT Dc De Dg Di Dk Dl Fr Im Io It Jp Lh Mc Mg Mm Mt Mu Mw My Na Nd Nf Ng Nh Nl Nm Nr Nx Ny Oy) Nm(Ao Ar aX BA bC Bg Bo bQ bR bU bV cA cB cD cF Ch cN Cp cT Db De dJ Dk dN Fr Hu Jj Jp Lh Lx Mc Mt Mu Mw Na Nd Ne Nf Nh Nl Ny Pd) Mg(Ar aW aX bA bC bE Bo bR bU bV cA cB cD cF cT De dJ Dk dN Hu Il Ji Jp Lx Mc Mm Mt Mu Mw Na Nd Nf Ni Ny) Mm(Ao aX BA Bc Bg Bo bR bU cB cF Ch cN Cp CT cZ Db Dk dN Hu It Ji Mc Mu Mw Ni Ny Oy Pd Zq) Jt(Ao Ar aX BA bC Bg Bo bU cF Ch cN cT cZ Db De dN fR Hu Hx Il Lx Mc Mt Mu Nf Ni Nw Qb Tj) Lx(Ao Ap aR aX Ba BC Bg bR bU cA cB cD cF Ch Ct De Dg Di Dl Hu Io Jp Mh Mt My Nd Ng) Mw(Ap Ar aW aX BC bR bU cA cB cD cF cN Dg Di dJ Dl dN Io It Ji Jp Mc Mt Na Nd Nf Nx) Mu(Ao Ap AR aW BC Bo bR bU cA cB cD cF Ch Dg Di Dl Dr Gc Io It Ji Jp Mc Mt Nd) Pd(Ap aW aX Ba bC bU cA cD cF cN Cp cZ De Dg Di dN Hu Io Ji Jj Jp Mh Mk Mt Na Nn Oh) Mt(AR aW Ba bC Bo bR bU cA cB cD cF Ch cN cT De Di Hu It Ji Jj My Na Ny) Jp(aL Ar AW Ba bC Bg bR bU cB cF Ch Cp cT Dc Di dN Hu Mc My Nd Nx Ny Oy) Tj(Ap AR Ba Bc Bn bU cN Co Ct Cu Dc Dg Ef Et Ex Fr Ir Is Jd Kf Lh Of) aR(Aa Hu Im It Jd Jj Mc Mr My Mz Nf Ng Nr Nt Nv Nx Ny Oy Pa Po Qa Qd) Hu(Ad Ap Ar BC bR bU cF cN Dc Dg Di Dl dN Ic Io It Lh Nd Oh) Ji(aL Ao Ar aW Ba bC Bg cF cN Cp CT cZ De Di Mc My Nd Nf Oy) Jj(Ao Ap Ar Aw Ba Bc Bg bU cB Ch Ct Cu Dc De Dg Di Dk Dl It Lh) Ny(Ap Ar aX bC Bg Bo bU cA cB cD Ch cN Di Dl In Io Na Nd Nf) Lh(aL Ao Ar aW bC bR bU cB Ch cN Dc Di dN It Na Nd Nf Oy) Ef(Ap Ar aX bA BC cA cD Ch cN cT Dg dN eP Uw Vb) cB(eO Im Io It Jd Mc Mn Mr My Mz Nv Nx Oy Po Qa) It(Ao Ar aW Bg Bo bR bU Ch cN cT dN Fr My) Jd(aL Bb bU De Di Dk Ip Mv Of Og On Pj Uw) Dr(Bb Ch CT De Gp Jg Jh Jk Mv Of) Io(Ao Ap Bc Bg Bn Co Db Dl dN Fr) Mc(Ao Ap Aw Ba Ch Cp De Di) Ic(Bb De Dk Jh Kq Mv Of On) Aa(bA bC bM bR bU cR dF) My(Ar cA cN Di Dl dN Nd) Na(Aw Ba Dc De Dl Nx) Cp(Hq Hw Hx Ir Nf) Ch(Mr Nd Nl Qa) Di(Nf Ns Nx Oy) Je(Gh Hp Zq Yc) Pj(Bb Mv Of On) gC(Ao Ba cG cT) Bo(Mr Nx Oy) Ex(cK Jh Mv) Nf(Ar Aw Pe) De(Il Pa) Po(bR bU) Mr(Ap Nr) Ib(Gn Zq) Nw(dX eP) Ok(eP Fw) fR(gP gW) zH(Bc Qv) ArPa BbKf NdNx QabR JrJs KoaW OnUv VcOy aIcZ aVdJ bEdD} Jd{Ib(AR bR bU cB Ch Cw De Et Fn Fw Hq Hx Im It Jh Jp Jt Kf Kj Kk Kn Ko Kx Ky Lw Na Nk Nr Om Pa Pj Pk St Ub Uf Uk) Hu(Aj Ar Bg bU cB De Fw Hc Hq Id Jh Jj Kk Kx Lw Mc Mv My Nk Nq Oh Ok Om Pa Pd Pj Pk Qv Qw St Ua Ub Uf Uv Vo) Fw(AR Bn cB cF De Et Id Kf Ki Kk Kn Ko Kp Kx Lw Mc Mm Mv Og Oh Ok Pa Pd Pj Pk Qa Qv Qz St Tt Ub) Uv(aR Bn bR cB cF cT Cw De Et iA Ic Ji Kf Kj Kk Kn Ko Lw Mm Mv Mz Na Oh Ok Pa Pd Pj Pk Tt Uf tF) bU(aF aG Aj aL Ar Bb bH bR cB Dc Fn gP Hf iA Jj Kc Ki Ks Og Om On Pa Pb Qv Qw Qz Tr Tt Ub Vo Tj) It(Ad Bn Cp Cu Cw Dc Im Ir Ji Jq Jr Jt Kd Ke Kf Kn Kp Kq Ks Lh Lw Na Ok Pd Pe Pi Pk Qa Vo) iA(Aw Ba Dc Et Fa Hf Ic Ip Iq Ir Jg Jh Jt Kc Kf Kq Lx Mq Mr Mv No Nv Ok Om Ub Uf) Qw(Ar De Et Id Im Jh Ji Kf Kn Ko Kx Lw Mm Mv Na Nr Oh Ok Om Tt Ub Uf Tj) Ic(Ar aW bR cB cT Dc dN eD gP Id iH jD jG jM Lw Mc Mv Pj Pk qC Qv Vq) Om(AR Bn cB De Et In Kp Lw Mc Mm Mv My Mz Ok Pa Pj Pk Qa Qu Ub Uf) Tt(Ar Bn cF De Ez Jj Ks Lh Lw My Nd Ng Of Og Pj Qu Qz Tr Ub Vo Tj) aR(Bb bR cB cF cT De Ju lL Mr Mv Nf Of Og Ok On Pa Pj Ub Tj) Kk(Ar Fi Id Jj Kp Lw Mc Mv Ok Pk Qv Rx Ub Uf Vc We Tl Tj) Iv(Ad Cu Cw Dc Ij Jr Kd Kn Kp Kq Mr Na Pb Pi Pk Tv) Vo(Cw De Et Id Ji Jp Jt Kf Ko Mm Mv Ok Pj St Uf Tj) nI(Dr Gc Gn Ps Rt Uw Ux Uy Va Vb Vj Vw Wd Wc Wh Tl) Tj(aW bA bR cB cF cT dN Em Ex Ki Uc Uf Un Vs) De(Aj Bg cB Il Mc My Nf Nq Of Og Qu Qv Ub) Ok(Aj Bg Fn Ks Lh My Nt Of Qu Qz Rh Tr Ub) Mc(bR cB Hf Id Ki Lw Mv Pa Pj Pk Qv Ub) Mv(Aj Bg iH Jk Ng Nq Of Pj Qv Ua Ub) Tr(Di Et Id Ko Kp Lw Mz Oh Pj St Uf) On(aL aW bR cB cF Cq dG Hf Iz Ks Rm) Di(aH aX bR cB cM eD gW jM jY) Et(Aj iH Ks Lh Ng Of Qu Qv Rh) Id(Fn Hv Hw jY Nf Nr Qu Ub Vp) Qz(Ar bR cF Ko Lw Lx Mm Nx Pj) Cw(eD In jY lL oF oN qQ qU) Pj(hO iH Jj Ks Og qC Rh Ub) Pk(Fn In Jj Nf Nr Og Uf Ur) Ut(bR Hx Mt Mw My Nb Nv) iH(Bb cF cM eD Kq lL qU) Ar(Hq Il My Qu Rh Ub) In(Cq Jr Mz Na Pb Tv) bR(aW Bb cN Mr Og Rh) Fn(Bn Fa Kx Lw Na) Mm(Ki Ks Oh Qv Ub) Hf(eD jY lL Me oK) Ip(eD hA jO jY lN) Qu(Aw Ch

Figure 4 Continued

Im Jh Uf) Jj(cB Ki Kj Oh Pa) kP(Ry Si Uw Yg Yi) Mr(Hx Mj Mt Vp) Uf(Ki Pi Rh Ub) cB(cM Ny Og Ub) oK(Fi Yi Tm Tl) Aj(Ch Kf Kj) Lh(Jp Kp Mz) Vp(Kq Pi Tv) Pa(eD Pg qU) aW(cF Io Ko) zH(Kz oF Um) IL(fN Iu qC) Aw(Bg My) Bb(cM gP) Du(gC nJ) Nr(Pd Pe) Lw(Jl Ki) Nf(Na Pd) Hv(Jr Pi) Jh(My Nq) Qv(Oh Uk) Og(bC cF) Vj(mH mY) Pf(Mh Pe) oN(Ps Tl) BnUw DbeD EdFa PoLx UbcF HxJt IrgW lujD ZwmH JiJl JnJr KqgP KsOh RyoH RhUr VcVq aLdD} On{My(aH AW bA bC bR bU cD cF Ch cK cT dE Di Fb Fw Ic Ik Il Io Iu Jg Ji Lv Lx Mf Mm Mv Ng Nh Ni Nm Nw Nx Om Oz Ri Tt Uv Vo) Fw(aH Aj bR bU bV cA cB cF cG cK Di dJ Fb Hf Hr iA Ic Ko Kp Kx Nj Ok Om Pb Pj Pk Qv Qw Qz Us Uv) Hx(aA aH aO aW bA bU bZ cO cQ cT Di Hf Ic Ji Lw Mu Mv Nc Ne Ng Ni Nl Nm Og Qw Qz Uv Vo) aW(aH bU cB cD cF cK dE Di Hq Il Io It Iu Jg Jj Lh Mb Mc Na Nf Nr Nv Of Om Po Qb Uv) Mb(aH Aj bC bR bU cB cF cK cO dE Di Ij Iu Iv Ji Mk Na Ni Nj Nm Ns Om Oz Pz Qb) Mv(Hr Ii Ik Il Io Iu Jg Ji Lv Lw Lx Mm Ms Mt Ne Ng Nh Ni Nk Nw Nx Of Og Om Oz) Ic(bR cH cN cQ Di Fn Hf Hr Il It Iu jG Jj Jl Nt Of Pg Pk Qb qC Qv Qz Uv Vo) Jl(aH cA cB De Di Fp iH Io Ji Lj Lx Lz Mh Ms Mu Ng Nh Ni Nk Nw Oz Pj Po) Di(aH bR cK gP Hq iA Ii Iu Jj Mc Na Nn Nr Ns Nv Of Po Qw Qz Tt) Mu(Hr Hw Io Iu Jg Ji Lv Lw Lx Mm Ms Ng Nh Ni Nk Nw Nx Og Om Oz) iH(aJ bU cF cO dE dG eD Hr Io It Iu Jl Nf Nn Of Oh oK Qb qT Tj) cB(aH cA cD cK dE Ij Iu Lh Mc Mk Mp Na Nf Nn Nr Of Oh Om Pa) bR(Af aH Bb cA cD cK dJ Is Lh Mc Na Nl Nn Nr Of Oh Om Uv) Oy(Fp Hr Ik Io Ji Lv Lw Lx Mi Mm Mt Ng Nh Ni Nk Nw Om) cK(Af Aj Bb cA cD dE dJ Hq Lh Lw Mk Ni Nr Nv Of Om Po) dE(aH cA cD Hr Ii Jj Mp Na Nl Nn Nr Oh Om Pc Po Uv) Qb(Aj aQ bA bU Fp Iv Ji Nc Ne Ng Nj Pj Qv Qw Qz) It(aH aQ bA cT eD hA Hf Ji Kk Nc Nl oK Qz Rm) Jj(aH aO aQ bA bU cO cQ cS cT eD Fb hA jG Pk) Hr(aH Aj bU Dp Fb Fn Hf Ib Qu Qw Qz Uv Vo) Nc(Ij In Io Iu Jk Lv Lw Mk Mm Nq Ns Om) Ng(Fp Ik Ji Lv Lw Mm Ne Nh Ni Nq Og Om) Of(aH Fb Ik Ji Lv Mm Nh Ns Nx Om Oz Qw) Na(aH aQ bU cF eD gP jG jM oH oK Pj) Iv(aA Ij In Io Iu Jk Lw Ne Nm Oz Pz) iA(eD gW Kc Kf Ko Kp Pj Ql Qv Rh Us) Ii(Ad bC bO bU cD cO cT Nr Pj Qa) Og(Fp Ji Lw Mm Ms Ne Ni Nk Nq Om) aR(Af Aj Bg Fn Ha Ju Pj Qv Qw Vo) Nq(aA Io Jg Ji Lx Mm Ne qD) Nr(aH Aj Ar bA cF cT Cw Pk) Hf(eD gP jM Me oH rB rX uZ) Om(aA bA cT Io Lw Ne Ni Nj) aH(Af bA cD cT Iu Jg Uv) Ms(Lv Mc Ml Nm Nx Oz) Ne(Ij Iu Lw Mk Nh Ni) Nj(gP Ji Jk Mm Pa Pz) eD(Bb cA Jk Li Nt Rb) Aj(Ad Fb Io Iu Tt) qC(jY lL Mz Qw Rb) Po(Ar bA bU cT) Io(Ar Cq Lw Qw) Qz(Fb Iu Ri Vo) Jl(Fb oK Qu Qw) zH(gW Hu tT yH) Cw(Hw In oK) Ni(Ij Lw Mm) Nl(Jk Mm Pz) Lh(bA bU cT) gP(Bb cF Nd) Tj(Lt oN) Fi(cG Nw) Nu(lK rB) Nf(bA cT) Ij(Fp Ji) In(Kq Pk) Oi(rB tT) Pj(Nt Qv) bQ(bZ cO) ArHq BbjY CuFb DboK DugC ExVq NmJi NncD HwId IbTt IpwL IuaQ RbjM QwvB QlqQ NvcT UvbU cAhA} Nj{Jj(Ar aW BA Bb bC bR cB cF Ch cM Cp cQ Cw De Di Dl dN Fp Ih It Jk Jl Jm Jo Jp Jq Jr Js Lh Lj Lv Lw Mg Mp Mq Mr Mu Mv Mz Na Nc Ni Nm Nn No Nt Of Oh Om Pd Qd) cB(Ad Ar aW bA bC bQ bV cA cD cN cT De Et Fr Hu Io Is Jh Ji Jp Jq Jt Lw Lx Mc Mm Mn Mr Mt Mu Mv Mw Mz Nf Nm Nv Ny Of Om Pa Pd) aR(Ad Ao Ap Ar AW Ba BC bF Bg Bn Bo bQ bR bV cA cD cF Ch cN Cp Ct Cw Dc De Dk Dl Hu Lh Mc Me Mg Mn Mw Mz Nt Nv Nx Oy) Ar(Ad aW BA Bb bC bR bU cD Ch cN cT Cw De Dl Et Il Io Is It Jg Jh Ji Jp Jq Jt Lw Mc Mn Mt Mv Mz Nf Nm Nw Om Pa Pd) Di(Ad Ap Ba Bb Bc bU cN Cv Cw Dc De Dl dN Fr Hu Io Jg Jh Ji Jp Jt Lw Lx Mc Mn Mt Mv Mz Nb Nm Ns Nw Om Oy Pa Pd Qe) bR(Ad aW bA bF bQ cA cN cT Fr Hu Is Jh Ji Jp Jt Lh Li Lw Lx Mc Mm Mn Mr Mt Mu Mv Ni Nm Ny Of Om Pd Qa) cT(Ad bC bU cA cF cN dN Fr Hu Io Is Jh Ji Jp Jt Lw Lx Mc Mn Mt Mu Mz Nf Nk Nm Of Om Pa Pd) bA(Ad bC bU cA cF Fr Hu Io Is Jh Ji Jt Lw Lx Mc Me Mg Mm Mn Mt Mv Mz Nf Nk Nm Of Pa Pd) Mm(Aw Ba Bb Bn bQ cA cF cQ Cw De dN Fp Fr In Iu Ji Jq Jr Lw Lx Mb Mr Mz Na Nw Oz) aW(Ad bU cF dN Fr Is Jh Ji Jp Jt Lw Lx Mn Mt Mu Mw Mz Nb Nf Ni Nr Ny Of Pd) bU(bF bQ bV cA cN De dN Hu Is Jh Ji Jp Jt Lw Lx Mn Mt Mu Mv Ny Om Pa Pd) Ni(Ad Ap Aw Ba Bo Ch cK Cw De Dg Dk Dl Fr Iv Ji Li Lx Mn Mp No Nw) cF(Ad bQ cA cN Fr Is Jh Ji Lw Lx Mc Mn Mt Mu Mv Mw Nm Ny Of Om Pd) cN(Ad Hu Jh Jt Lw Mg Mn Mt Mv Nf Nk Nm Ny Of Om Pa Pd) Nw(Ba Ch De Il In Iu Iv Lw Ms My Na Nm Og Om Oy Pa) Fr(Ii Il In Iu Iv Ji Jq Lw My Ng Nq Og Om Oy Pa) Lw(aA Ad Aw Ba Bb bF bQ cA Ch De Iv Ji Lx) aA(Il Jg Jt Li Mn Mt Mz Na Of Og Po) Ad(Il In Mc Mv Na Ng Of Og Om Pa) Lx(Bb Il In Iv Ji Jq Jt Ms Og Qb) dN(cA Hu Io Ji Mn Mv Mz Nf Of Pa) Bb(De Mc Mn Mt Mv Om Pa Pd) cA(Mt Mu Mv Nm Ny Of Om Pd) Ji(Ch cQ Im It My Nm Pa) De(Il Mc Mt Nf Pa) bC(Hu Jh Mv Ny Of) In(Cw Iv Jt Mz) Et(aH Ba cQ) Nm(bF bQ bV) Jg(My Ng Oy) Of(bF cD fR) Cw(Mc Nf) Iv(Mn Og) Jt(Ii It) cQ(Is Jh) BaPd FwOk NycD bQcO} Nd{Om(aR aW bC bU cB cD cF cN cT Di Hx Im In Is It Iv Jl Lj Md Me Ml Mp Mt Mv Mw Nc Nf Nl Nn Nr Ny Oy Oz Pb Qd Qe) Of(aW bA bC bF cB cD cF cN Ih In Iv Jg Jl Jq Lj Me Mp Na Nc Nf Nl Nm Nn Nr Oy Oz Pf Qd Qe) Nm(Ar aW BA bC bF bQ bV cB cF cN cT Di dN In Is Jl Jq Lj Mr Nl Nn Nr Pe Po Qd Qe) Og(Fp Ih Ip It Jh Jk Js Lj Lv Me Mg Mu Mv Mw Mx Nb Nc Nl Nt Ny Oe Oh Oz Pc Pf Qb Qd) Me(aR bA cT Is Iv Jl Jq Li Mp Mt Mu Mx Na Nb Nc Nl Nn Nr Nt Nx Oz Pd Po Qd Qe) Nc(Im Is Iv Jg Jl Jq Li Lj Lv Mg Mr Mt Na Ni Nn Nr Nx Oz Pd Pc Po Qd Qe) Bb(aW bC bF bR bU bV bW cB cD cF cK cQ cT Di dN gP Is Lw Mm Pd tN tS) Lw(Ad Ao Ar AW BA bF Bo bQ bR bU bV cA cB cF Ch cK cN De Di) Oz(Is It Iv Jg Li Lj Mg Mv Na Nl Nn Nr Nx Oh Pa Pd Po Qa Qd Qe) Jl(Im In Iv Jp Jq Li Lj Mg Mp Mt Mz Na Nn Nr Oh Pd Po Qd Qe) Is(aR bA bR bU cB Ch cT Im Iu Iv Jg Jq Lh Mp Mr Mt Na Pe) Di(Ad AR Cv Cw Dc De Io It Jh Ji Jp Mt Mv Ns Nw Pd) Mm(Ar Aw Ba Bg Bn bQ bR bV cA cB cD cF Ch Cw De dN) Ji(Ao Ar BA bC bF Bg bR bU cB cD cF Ch cN cT De) Mr(Hx In Jg Jq Li Lj Ml Nl Nn Nx Oh Po Qa Qd Qe) Jp(Ar aW bA bR bU cB cD cF Ch cT De Li Mt Na Qa) Pd(aR bA bR bU cB cF cN cT In Iv Lj Mp Nn Nr Qd) Jh(aW bA bC bR bU cB cD cF cK cN cQ cT dN My) Pe(In Iv Jg Jq Li Lj Mk Nn Nr Nx Po Qa Qd Qe) Na(Iv Jg Mg Mp Mt Nl Nn Nr Nx Oh Po Qd Qe) Jt(Ar aW bA bC bF bR bU cB cD cF cN cT dN) aR(Ad bA bF Bg cD cT Cw Jj Lh Mg Mu Nx Ny) Et(Aj Ar Ba bC Bg bU cB cF Ch cN Cw De) Jg(De In Iu Li Mp Ms Mt Nr Po Qa Qe) Lj(Im In Jq Lh Mg Mn Mp Mu Mz Pa) Mv(aW bC bU cB cD cF cN dN) In(Ih Mt Nn Nr Nx Qd Qe) Mp(Jq Mt Ng Nl Nr Qe) Im(Li Nf Nn Nr Pf Qe) Iv(Li Nn Nr Po Qa Qe) Nw(aW bC cF Ch cK Cw) cD(bA cB cT Mu Mw Ny) Ad(Ar aW bA cT Jj) Ng(Li Mt Qa Qd) Io(Ar bA cT De) Jj(bU cB cT Pz) Jq(Lh Nf Nv Oh) Mg(bA cN cT) Qa(Il It Lh) Qe(Iu Mt Pa) Ny(bC bU cB) Ok(Ar Bg Tj) Nn(Mx Nl) cB(Hu Mu) PoNf TrsJ QdPa PjhO} Bb{jY(cW Id Kf Ki Kn Lw Lx Mm Mq Mw Mx Mz Na Nc Ne Nk Nl Of Oh Pa Pb Pk Po pS Uf uL uX vS wD yD yH xA Wm) tV(dR eC Ef fP Fw fY iH It jD Kk Mk Mv Na Ni Nt Nu Oy Pa Pc Pj qC Ql Qn qO QU Qv Ri Um Uu) gP(Ad An aV Ba bB bF Bn cD cN cT Cw De Dk Dl Et fR Ic Im Kf Kq Mc Ok Uf) iH(Ad aR Ba cK cQ dB dD Di eD Et Io Jg Jt Ko Kq Lx Mc Nf No Nw Pe qU vB) rC(Aj aL bH cD cW dB Di Ic Ks lL Mm Na oE Of Oi qY rW tR tS tT yH) aR(bF Bn bU cF cK cN cT gW hB Ic Is Kf Lw Mc Nb Of qO Qv Uv) aW(aK aU aV bA bC Bo bR bX cG Ch cN CP dD De Di dJ dN Ko) cB(aH aJ aK An aP Ar Ba bC bQ bU cF cG CP cQ dD dN Tj) eD(CW Fn fY Id Kf Kn Ky Mm Oh Oi Pb Pc Pk qP rW) tS(Bg fP Fw Hu Ic jV lL Mm Mv Mz Na NW Oi Pj rB) cK(Aw bA bC Bn bQ bU cF cG Cp De dF Di dN Lw Ni) tN(Bg fP Hu jV Mm Mv Mz Na Nq Nu Oi Pj rB Ri) Ic(cM cN cQ jD jR jV qI sM tR vB vS yH zG) zH(aX fP gW hB lL Mz oE oF qO rW tT yH) Mm(hA hO iA jD qB qI qY tO tR tT tX) lL(Hf Na qD uN vP vS vV wL yD yH) vB(fP Hf Ik Jv Kp Mz Na Nw Qw Ue) cF(bA bF Bn bU cN dD De gW hB) cN(Aw bE bF bJ Bn bR bU cT) fP(uM uO uT uU vH vO wQ xA) Pj(hO jD qY tO tR tX yH) Nq(jD jH lK tR tT tX) Na(hB jR jT jV oK qX) cT(bF bM Bn Ch cP De) Oi(jD rO rW tR tX) Hf(jD jT lK oK) bU(bA Bn De Di) tT(iO jV NW) tR(Bg Mz Nb rB) qO(aQ aV hV jR) Ri(rO rU vP) bF(aH bM bR) gW(Ad bM Bo) iA(Et Kf Ok) jV(Kz Ly tO) Cw(oK tF) Di(Bn hB) Nu(jH lK) Mz(qD tO) rB(tX wD) jD(Ip Of) uL(Qw Ua) vS(jF Ub) AwbM TjFa EtoK NtjH KzqY UvtF cMhB cVqC qIoE oFuU} Jj{Jg(aH aW bR bU cB cK Fp Hx iH Io Is It Ji Jq Jr Jt Lj Lv Lw Lx Mb Mm Ms Mt Mu Mw My Ne Ng Nk Nq Nr Oy Oz Pa Po Qa Qe) Nc(aA Fp Ik Im It Jl Jm Jo Jp Jq Lh Lj Lv Lw Mg Mn Mp Mr Mz Ni Nm Nn No Nr Nt Of Oh Om Pa Qa Qd Qe) Mm(Fr Hx Is It Jq Jr Jt Li Lj Lw Lx Ml Mr Mt Mz Nh Ni Nk Nt Nu Nv Nw Of Oh Oz Pa Po Qa Qe) Jt(Fp Fr Hx iH Ii Ik In Ir Is It Li Lv Lx Mj Mt Nh Nk Nr Nt Nv Nw Oh oK Pa Po Qa Qe tF) Mt(aR Fp Ik Is It Jq Li Lj Lv Lw Lx Mb Ms My Ne Nk Nm Nr Nt Nw Pa Po Qa Qe) Nr(Fp Fr Hx Ik Is It Jq Li Lv Lw Lx Ly Mb

Figure 4 Continued

KonU OmeM} Ip{lN(vH wD yJ) jD(cA hL) QctT RiwH tSqC} Jp{eP(Kc Ld) qQ(Rf tF) lnPi OrdX UpvS eDiA} gP{Bo(Ba Bc De Dk) Cp(cG
Dl) lz(Uy Vj)} Ri{fN(rU rW uG vS vW wD) LutN} bM{dW(aS bC dM) Mn(dX gV) DwbJ OfgV} mH{nA(Fd Op Rx Rz Yl Zw) XaRh}
Zq{Kn(kP mY nT) Hb(lY mS) bWlY} bB{eO(Aa Cv dB) AfeP JhiA RxnC} Ex{hO(Ef Kl Uc) AsyD kRsC} Nm{qC(jD jY IL) VusJ qDIL}
Uf{Nq(tN tO tT) bZtT iAsC} eD{CpUs TiqV RbOm JhQw KfiA} Fb{Uw(Af CX De)} In{Pi(Ko Qa) FpJq MyOm} Iz{Uy(eC hC kK) MaoD}
Qv{AavT BcuN LuvS WeoN} Mv{YfmZ TliJ RynH} Zw{Jn(mP mU) AonU} Xa{Rh(mE oH oK)} Kf{NoiA IlsJ UpsI} Oi{EmbR SfeM
kGIK} O uZ vS wH wL tL) Lx(Hx ll Jq Lv Ms Nh Om Oz) Mt(bA cT Jq Lj Lv Mb Ms My) bR(bC bQ cG cT Jh Ji Pd Qa) Ch(bA bF cG Dl Dr Ex Ji) Fb(Dr Ko Uw Vc Vh We Yg) Fr(Hx Jq Lv Mb Ms My Nk) Lh(qC tN tT tV tX wL xA) qY(Wc Wh Yl Zq Zx Tl Xa) cT(bC bM dN Is Jh Ji) cD(aF Bc cV Id jl Mz) Bo(bA bC bF Dl gW) Ip(tN tV tX wB wL) Kq(gW hA In uZ tF) qT(Va Vc Vh Vz Yd) Ba(bF bM Dl gP) Ji(Aw bA cQ qC) Ko(eP Fw Hf Qz) Fi(Ib Jk Tn) Mb(Jq Nv Qa) Mz(jM jY rW) Is(bA dD Og) Ri(rN rW tS) Un(jY qC qD) Bc(bF jY) Dl(bA bC) Po(Il Og) Ni(Li Nk) Ib(Lt Vb) In(Jq Pi) Qa(Og Qb) Qz(Jp Om) Uf(oH oK) Va(jH jI) bM(dD dW) fP(bB wL) gC(cG Du) gW(Dk Ex) AfeP AnbF AprN DrGp FwKf GnnI MvQw MyOm IdrX TrsJ HfqU JhhA WcqV WeKk QvvS TloD UwjF VhVq aMeW bZlM dBeO dDdN nNnT wDtL

Constrained panels with 2 analytes, where 1.0E-3 >= 'model p-value' > 1.0E-4. Contains 3,047 panels of 199,257 total panels evaluated. : aR(aA al aJ aK An Ap aQ Ar aU aV bA bB Bg bJ bM bQ bR cE cG cN Ct Cu Cw cY DD dF DG Dk dN cD Ef Fb fP Fr gW hB hR Ib Id jD jU Kc Ke Kl Kn Kp Kx lL IM Ly Mq Mr My Ne Nh Nr Oy Ph Pk qC qO Qv qX rC rW sO Ss Tn tO tR tS tX Ue Uf Un Ut Uu Uv Vs We Tj) Ic(Ad aP Aw Ba Bb bC bF Bn bR Ch Cp Cw cX Ex Fa Fb Fn gL gP hG Ib iH Im Io Is Je jG Ji Jj Jp Jq jR Jt Ke Kf Ko Kx Lh Li lN Lw Lx Mc Mm Mn Mq Mt Mu Mz Na No Nr Nw Oh oK Pd Ph Pj Qa Qe Qh Qv Qz rB Rc sM St Tn tS Tz Un Ur Ut vS zH) Cw(aH aK Ar aV Ba Bb bC bJ bM Bo bR cG Ch cN cP Di Fb gW hL hO hR Hw Id In Io jD Jj jY Lw Ly Mb Mc Mm Mt Mv Nc NF Nl Nn Nw Oh Pa Pj qC qD Qv Qw Qz rC rN rU rW tN tO tR tS tT tV tX Uf Ur Uv wG wL xA Tj) Jj(aA Ar Aw BA Bb Bn bR bU Ch cK cT Dc De Dg Dl eD Ef Id lH Ip Ir Jh Jk Jr Js Ke Kg Kj Kl Kn Ko Kp Kq Kx Ly Mb Mf Mp Mq Mr Mu Mv Mx Mz Ni Nk No Nu Ny Of Om Oz Pd Pe Ph Pj Pk Pz Qb Qc Tn Un) Uf(aC Ad Ar aW bA Bn bR bU cB cF cN cT De eD Fb hO Hu Id Im Io Is It Jg Ji jO Jp Jq Jt jY Kf Ko lL Lw Mc Mn Mt Mv Oh Pj Pk qC Qm qQ Qv Qw Qz rB rN TN tT tV Ur Vo wL yL zH tM xA Tj) iH(aI Ao aQ aV Bc Bn bW cB cD Ch cK cQ Dc De Dg dJ Dk Dl Fa Fr hB hR Hu iC Io Ir Is jD jL Jp Kf Lh lL lM Lw Lx Mg mH Mn Mr Mu Mw My Mz Nf Nv Nx Ny Of Pd Tt tV Un vS wL zH tF) bR(aA aJ Ar BA Bb bM Bo bU bW cE Ch cK cL. Cu dD dF DG Dl dN Ef Ex fP hB Hu Ib Io It Jp Jq Lh Li Lw Lx Mm Mt Mu Mv Nd Ne Nh Nl Nm Nv Ny Of Om Pj Po Qd Qe Tn Un Ut We) Pj(Ad Aw Ba bC bF Bo bQ bU cB cD cF Ch cQ dD De dN Fa Fb Fr Fw hG Ib Id Im Is Je Jh Ji Jp Ke Kf Ko Kq Kx Lw Mc Me Mn Mq Mt Og Oh Om Pd Pk Qz Ri Tn Ug Ur Uv Tj tF) bU(aJ Ao Ap aQ aS aU aV bB BC Bg bH bW cA cE cK Ct Cu dD dF DG Dk Fr hB Hu Id Io lt Je Jp Jq Jt Kc Lw Lx Mt Mu Mv Nh Nl Nm Nx Ny Of Om Pd Tn Un Ut Vh Tj) cN(al aK An Ao Ap aQ Ar aU aV bA bB BC bE bJ bM Bo bQ cG cM Co Ct Cu cY Dc Dg dN Ef Ex Fb Ib Is Je Jt Ke Kf Kj Kq Lw Mg Mt Mu Mv Nl Nt Nx Ny Om Pd Qw sO Ut) zH(Ad Ap Aw cI Cp Cu Dc Dg Dk Dl Fr Hf Im Ip Is It Jg Jh Jl Jt Ke Kf Kq Ky Kz Lw Lx Mq Ms Mv Mx Na Ni Nk Nv oE Oh Om Pd Pz Qe qO Qv Ri tN tT tV tX Um Un wD) eD(aK aN Ap Ar AW aZ Bo cA Cp cS cW Db Dk dN Et fP Fr gW Hb Hf hG jD Jg Jh Ji Jp Jt Ke Kf Kp Kq Ky Kz Lh lM Lx Mv Na Of oK Om Pa Po Qm Qw Qz Un Ut Vt) cF(Ax Co Dc Ex fN hR hX jD Jh Jp Jt Kf Kq lL lM Lw Lx Mg Mm Mu Mv Ne Nh Nl Nm Nt Nx Ny Of Om Pd qC qD qX qY rN rS rW TN tO tR tT tV Un Vh We wL Tj) Ar(aK aQ aU aV BA Bb bM Bo cG Ct Cu cY Dg dN Ef Fb Hq Id fl Jh Jp Kc Ke Kp Kq lL Mg Mh Mn Mv Nc Ne Nw Nx Oh Om Pa Pk Qv Qz Ss Tn Tr Un Tj) Nm(aA Aw Ba Bb bC bF Bo bQ bV Cp dD De Fi fP Fr hO iA lk Is Jp Li Lj Lv Mb Mt Mx Nh Nk No Nr Nt Nv Oz Pa Po Qa qD Qe Qv rN sJ tO tS xA Tj) cK(aA al aJ An Ao aP Ax bB Bg bM bW cE Co Ct Dc dD dG Dk Ef Ex Fr Hu Io It Jp Jq Lh Lx Mc Mg Mm Mn Mr Mv Mw Mz Nd Nh Ni Nl Nr Nt Nv Nx Oh Pa) cB(Dr hB Im Io It jD Je Jp Jq Kc Ke Kq Li lM Lx Mc Mg Mm Mn Mr Mw Mz Nc Ne Nh Nl Nn Nv Nx Oh Qa qX rN rW rX Tn tS TT tX Un Ut We tF) Bb(aJ aU Ax Ba bB bC bE bJ Bo bQ cE Ch cY dF dG Dl Dr Kx Lw Mb Mc Mm Mt Mv Nc Ne Nk Nl Om Pd Pk Qv qY Qz rN rW sC tO uM vB wL yH yL xA) Tj(aN Ax Bn cT Di Dl Du Fr Ha lb Id lm Ir lt Je Jh Jp Kn Kp Kx Li Lw Mq Mr Mt Mu Mv Nx Ny Oh Om Pf Ph Pk Po Qa Qe Ry Tv Un Vh We Xa) Jt(Aj aQ Aw Ba bC bF Bn Bo bQ cQ dD De Fi Fn Fp Fr Fw hO Hx Il Im In Li Lv Lw Ms Nh Ni Nk Nr Pa Po Qv Qw Qz rN tN tT tV tX Ug Ur Uv wL) Kf(Aj Di Fb gW hA Hu It Iu jM jY Lw Mc Mv Nn Og oH oK qC qQ qU Qv Qw Qz rB rN rO rR rU rX sJ tO tR tS tT tV tX Ug Ur Uv uZ vB wG wL xA) Id(aC Ad aN aW Ba Ch cT De Di Fb Fn Fr hA hR Hu In Io It jD Jg Jp jY lN Mc Mm Mn Mt Mv Nf Nr Og Oh Ok qC qU Qv Qw Qz Rc Tn Ur vS) Is(Aj Al An aQ aS Aw Ba bF Bn Bo Ch cQ De eP Fr Fw iA Il In Jg Jq Lh Lv Mb Ms Nc Nf Nh Ni No Nr Nt Nx oK Om Oz Pa Qg Qv Qw Qz Ur) Kq(aC Aj aW cA cW Di Fn Fw Hu Io jD jM jY Lh lL Mc Mm Mv Nf Og Om qC qO qY Qz rB rC rW rX sC tO tR tS tT tV tX Ur vB wG wL tM xA) Ke(aC aN aW Di Fb Fn Fw hA hL Hu Io It jY Mc Mv Nf Nr Og oK qC qD qO qQ Qv Qw Qz rX tN tO tR tS tT tV tX Uv uZ vB vH wG wL xA) Jg(Fb Fp gC Ib Io Jq Kx Lj Lt Lv Mb Mz Nh Ni Nk No Nx Oz Pa Pk Po Qa qC Qv Qw rN Rz tN tT tV tX Ur Uu Uw Ux Vb Vo Vw wL Yg) Ch(AJ aK An aQ aS aU aV Ax Ba bC bE bJ bM Bo bQ bW cE Cs Cu Cx cY Dc dD dF Dg dN fP Fr gW hB Io It Jq Mm Mt Nl Nw) Jp(aA aW bA Bn cT Di Fp hR Ib Jq Kx Lj Lv Lw Mb Ms Ne Nh Ni Nr Nt Og oK Pk qC qD qQ Qv Qw rB tN tT tV tX Uv vI Vo wL) bA(An Ao Ap Ba bC bM dD Dg Di Dk dN Dr Fb Hu Io It Ko Lw Lx Ly Mc Mg Mm Mu Mv My Mz Ne Nf Nh Nl Nt Nx Ny Of Om Pd) Di(aK aQ bJ cP dD dN Dp Ef Ex hR jD Je jY Kc Kn Kp Kx Lx Mc Mg Mn Mv Mz nF Om Pa Qa Qv Qw qY Qz rC Ss Tn Un) Lw(Ap aW Ba Bo bQ bV cA Cp dD Dg Dl Fb fP Ik Im Jl Jq Jr Ko Lh Lj Mn Mr Mx Mz Ni Nk Nn No Oz Pa Qd Tn tL) Vh(aC aW Bn bW Cs Dp Fi Gn Hb Hp Hr Hu Im Io iZ Je Jk Jr Kk Li Lj Lp Mb Mh Mu Ny Oi oK Pi Pk qY Rh Ut Vb) Mv(bC bF Bn bV cD cT Dl dN Dr Fb Fr gC iA Kc Ko Kp Kx Lt nF nK nN Om Pk Qu Qv Qz St TT tV Un Ur Vc) Lh(aA Fp hL Hx Ii Il Im Lj Lv Mb Ms Mw My Ne Nf Nh Nk Nr Nx Og oH oK Oy Pa qD qQ rN tO tR tS vB tL) Ba(aH Aj aK aQ aU aV Ax bC bJ Bo cG cP Cs Ct dF Dg dN Dr gC gW Io It Ji lX Mc Mm Mt nF Nl Nw Pd) Ad(Dr Ex Fi Fn hA Ib In Ji Ks lK Pk QU Qw qY Qz rB rC rN rW tO tR tS tT tV tX Ug Uv Vq xA) De(An Ex Fb Fi Fn iA Il It Kp lX Mb Mc Mm Mn Mt Mz Nc NF Nl Nw Nx Pa Pb Pd Pk Qv Qw Tn Ur) On(Dr Fc Fd hL hR hX Lt nF nK qY rB rN rW sC tN tO tQ tR tS tV Uw VB Vc vH Vq Vw Yg tL xA) cT(cG dD Dr Ef Ex Fb Io It Kc Ko Lx Ly Mc Mg Mu Mz Nc Ne Nf Nh Nl Nt Nx Ny Of Om Pd Qa Qz Un) Bo(aK An aQ As aU aV Ax Bc bJ bM cG cP Ct Cu Cx cY Dc dE dF Dg dN Ef Ex Io Mm Mt Nd Nl Nw) Dl(aA aJ aK An aQ aS aU aV bM bQ cE cG cP cY dD dF dN Ex Fi fP gW Hu Jh Mt Nd Nl Om qC Qv) Mb(Bn Cp Im Jl Li Lj Mg Mn Mp Mr Mu Mz Na Ne Nh Nn No Nr Nt Of Oh Om Oz Pa Pd Pe Po Qd Qe) bC(An Ao aQ aS aV Ax bB bJ bM bQ cG Cs Ct Cu dD Dg dN Ex fP Jh Ji Mt Nl Ny Of Om Pd Tt) Aw(Dr Ex hA iA Io It jM jV lK lL Mc Mn Mt My Nl Nw Pa Pd qO qU Qw Qz rB rC rN rW Ur) Cp(Fn Gp Hq Hr Hv Hw Hx Io Ir It jY lL Mc Mm Mt My Na Nf Nl Pa qC Qv Qw Qz rB Ur) Ji(aQ bF dD dN eP Fb gC hL hR hV jD Je qD Qv Qw Qz TN tT tV tX Ur Uv vI wL xA) Lv(Fp Im Jq Li Lj Mg Mn Mp Mx Mz Nh Nk Nn No Nr Nt Nv Og Oz Pa Po Qa Qd Qe tV) wL(Bc Fr gW Kc Ky Lx Mz Nv Of Oh Om Pa Pd Po Qa Ri sC sO tN Tr tT tV tX Vq wD) Dr(Af Aj aN Ao aU aW bF Bg cG Co Ct cY Gn Hr Io Jd Jk Mg Mu Nq Of Oi Rc Ss) Nt(aW cD Fp Fr gC Im In Jq Li Lj Mn Mt Mz Ne Nh Nk Nr Og Oz Pa Po Qa Qe) Tn(Aj aW Bn eM eP gC Hu iA Ib It Mc Mm Nr Og Oh Qu Qw Qz Rh Ur Uv Vc Vq) Ne(Aa bF Fp Im Lj Mg Mp Mr Mz Ni Nn Nr Of Og Om Oz Pd Pe Po Qa Qd Qe) Un(aC aN aW Fn Hu iA Io jM lN Og qU Qv Qz rB rX Ug uN Ur Uv uZ vS tL) tV(Aa bZ gW Hq Ih Kc Kz Ma Ms Mz Nw Of Om Pa Pd Pz Qv Qw Ri Tr TT) Ex(bF Bn bQ Ct dD Et Hf hO Je Jh Kc Kx Nd Nl Nn Nx Oh OK Qv Ss) Fr(Fp gW iA Jr Lj Mu Mw Ng Nh Ni Nq Og Om Oy Oz Pk Qw Qz sC tT xA) We(aW bW cU Dd eC Fd Fi Fn Gp Hr Im Io iZ Je Lj Oi Pk Rh Ss Vb Vq) Mm(An Bn bQ Fb hL hO iA Ib Ko Kx qC qD Qw Qz sJ sM Ur Uv yH) Nd(Ao Ap aW Ax Bc Bg Bn cA cG Co Ct Cu Cv Dc DD dF Dg Dk) Jq(Fp Ik Im It Li Lj Mn Ms Nf Nh Nk No Nr Og Oz Pa Po Qa Qe) Om(aA bF bV cD Fb Fp iA Lj Mw Nh Nv Nx qC Qv Qw tT tX Ur Vc) Fi(Ef Fb Fw Im Kj Ko Li Mu Mx Nv Ny Of Ph Qh Ss Tt Ut Xa) Nw(Bn Fb hA hV hX jM jY Pk qY qZ rB rU tN tQ tT tX vI tF) Ap(gP gW hO iA jD jY lL Pk qC qO qP qU rB rC rS tT tX) Hu(Fb Kc Ko Kp Kx Lt nF nK nN Pk Qm Qu Qv Qw Qz Tt Vt) Ok(eO Fn hA hL hO hR hX jG jY

Figure 4 Continued

Ks qD qQ qY rB Tr Vq yK) aW(Ef Fb Io Je Lx Mg Mu Mw Mz Nx Ny Of Pd Qa Ut Wd Wh) cG(uH aK An aQ aV bM bZ cO Ct cU dD Dg dN
IX nO nT tF) Nh(bF Eo Fp Im Li Lj Mn Mz No Nr Nv Oz Pa Pe Po Qe) Jd(jU kO nC nF nH nJ nL nT qI qQ qY rB tR tS vS Yi) iA(bB Fa hB Im
Ko IM Lx Mq Mu Mw Nv Ny Pd Tt Ut Vs) tT(Bc cI Dg Kg Lx Ma Ms Mz Nv Nx Of Pd qC sF sO vI) fP(Aa aC aD aI Bg Bn cD cM cO dD rC
rN uM uZ xA) Et(hA hR hV jG jM jP jY Ks qY rB sJ Tr Vq Tk) Qv(aN Fb Im Io It Ko Mg Mn Mt Oh Qm Ue uN uZ) Vt(hO jY qQ rO rV sJ sM
sO Tt uN wF yK yL xA) dN(aK aL An aQ aU aV bB bE bJ bM Ct NI rC rX) qC(Bc Cu gW Hb Ii Ip jD Kg KI Kp Oh Pd Qz Tz) Fp(fR In Mg
Mn Mp Mt Nf Ni No Nv Og Oz Pa) aC(Fb Hp Ib Je Ry Tt Ut Vi Wd Yg Yk Ye Xa) jD(Bc cA cV Fa Hb Je Qm Rc Tz Vq vS Ye) rN(Dg eC Fw
Hf jY Kg Kj KI rC Tt uU wG) Ur(Dc Fb Im It Ko Li Mt Oh Pd Pk Qa) aN(Fb Ib Je Kc KI Kp Kx IM Qz Tt Vs) bF(Ef Io IX Mt Mu NI Nx Ny Of
oN Pd) Mz(aA hR hV hX In Nr rB rC sO vI) Wh(eC eM hC Io iZ jH Lj My oK Vc) Nv(Hx Ii II Ms My Nj Nk Og Oy Oz) Bn(eP Gn Io It Mc Mt
Nf NI Qe) Ef(Aj gV Lt Ux Vb Vc Vw Zw Zx) Tt(bW cA hB Ih iP qQ tS uX Vb) Jh(aQ bV cQ Fb My Nj nK Qw Qz) Li(II In Ms Nf Nk Nx Og
Qw Qz) Of(bQ bV cA cD dD fR Lj tN tX) aA(Hx Ik Im Lj Mx Ni Nk Pa Pc) gW(An Ao Bc Ct Cu Dg Fa sO Ye) Po(In Ms Nf Ni Nx Oy Oz Qb)
Tr(qQ rW sM tS vS wG yL tL) Qa(Hx Il In It Iu Ms Ni Oz) Jk(Fc Fd Ho Lt Ps Rx Uw Yf) Ko(Fn gC Mc Na Og Pk Qw rX) Vq(hO Hp jY qU
uM yL Zq tL) tX(Ao cI Fw Kg Pd qU qW Ri) sO(aK aX Ip qO rY sC uM vB) Dg(Aj aK An aV bJ bM cP) Fb(Aj Mc Og Pd Pk Qz Ry) Nr(In Ni
No Og Oz Pa Qw) Mt(cD Ni Oz Pa Qw Qz Uv) Xa(bW Kk oH oK Rh Ss tF) Nx(Im In Lj Mn Nf Pe Qz) iC(mT mU mZ nA nI nK nR) Bc(hA IL
IN qD rC tS) Nj(JI Jr Mu Mx Pd Qd) Ip(hL qD sM vI yH zI) Zq(bW jH jO IM IY oK) Qe(II In Ms Ni Og Qb) Ky(rX sC uP uX wH xA) Ri(rU tN
uN vS wH xA) dF(An aQ aV bM dD gC) fR(Cs Io Iv Nc NI Ub) Fa(Ed Fn Fw jM rB) Gn(Ny Pi Pk Rj Vu) Lx(hO hR Qz rB wG) Wd(eM gP hC
Kk Lj) Ut(gP Lt oH Qz Rx) bQ(aQ bM cO Io NI) rC(aF cW Hf hG oE) IM(cA cV hR hV jI) Mn(nA nF nK Pk) Je(It jU Lt Oh) hB(dD Io rX Tl)
rZ(nD nJ nM nU) vS(jL IL IN Tk) An(aU aV bM) Ik(No Og Pa) Kk(Rt Rx Vi) Ny(cA cD Fd) bV(Mg Pd rX) eO(aD cW dJ) jI(hR IL nK)
qY(Uw Wf Ti) oD(Gh Ry Si) uZ(Kc Mq oE) Ao(eP gC) Ib(Qz Yg) Io(Kx Pk) Ss(Hp Lt) Qw(Im uX) Tl(gL Oi) Lj(Mg Ni) Tk(Pa Pf) Og(Jl Qd)
bM(Bg Ct) cD(Mu NI) cV(hR rX) nA(hV jQ) rB(Hf Kz) wD(rY wF) DkjM DwaM EoaD HmF InnK HbIL IzgC YiOi WfqT QzOh KcvB KgtS
RybW LtOy PddD aFrX gLIX wGqZ wFtL Unconstrained panels with 3 analytes, where 0.0E0 >= 'AUC p-value' > 0. Contains 50,000 panels of 37,563,518 total panels evaluated. :
oD{Ry(AA aC AD aE AF aG aH aI aJ aK AL aM AN AO AP aQ aR AS aV AW AX aY aZ BA BB Bc bE bF BG bH bI bJ bL BN BO bP bQ
bR bU bV bW bZ cA cB cC cE cF cG CH cI cJ cK cL cM CO CP CQ cR cS CT CU CV CW CX cZ dA DB DC DD De dF DG dH DI dJ dK DI
dM dN Dp DR Du eC Ed eF EM EQ Et Ex Ez fA FB Fc Fd Fi Fn fP FR Fw Fy Gb GC GL Gn GP GZ HB HC HF hG HI Ho Hp Hq Hr Hv Hw
Hx iA Ic Id iH Ii IJ Ik II Im In IO IP Iq Ir Is It Iu Iv iZ jB Jd Jf Jg Jh Ji Jj JI Jm Jn Jo Jp Jq Jr Js Jt Ju Jv Kc Kd KE KF KG KI Kj KK Kl KN KO
KP KQ KR KS Kx Ky Kz Ld Lh Li Lj Ll Lt Lu Lv LW LX Ly Lz Ma Mc Md ME MF Mg MH MI Mj Mk MI Mm Mn MP Mq Mr mS MT mU
MW Mx MY MZ NA NB NC ND Ne NF Ng NH NI NJ NK NL NM NN NO NR Ns NT NU Nv nW Nx NY Oa OE OF Og OH Oi OK Om oN
oO OP oQ Or oT Ou oV OW Oy Oz Pa Pb Pc Pd PF Pg PH pl Pj pK Po Ps Pz Qa Qb Qc Qd Qe Qg Qh QI Qm Qn Qt Qu Qv Qw Qx Ra Rb Rc
Rf Rg Rh Ri Rj Rm Rt Ru Rv Rx Rz Sf Sh Sr Ss St Tn To Tr Tv Tz Ub Uc Ud Uc Uf Ug Uh Uk UI Um Un Up Ur Us Uu Uv Uw Ux Uy Uz Va
Vb Vc Vh Vj Vo Vp Vq Vs Vu Vv Vw Vz Wb Wc We Wf Wg Yd Yg Yh Yi Yj Yk YI Zq Zw Ye Tm Tl Xa Wm Tj Ti Th tF Yf) Uy(Aa aC Ad
aE AF aG al AJ AL aN aO Ap aQ AR AS aU aV AW aX aY aZ BB Bc bE bF BG bH bI bJ bM BN BO bP bQ bR bS bU bV bW bX cB cC cD
cE cG CH cI cJ cK cL cN CO CP cQ cR CS CT CU cV CW Cx cY cZ dA dB DC DD DE dF Dg dH DI dJ DK DL dM dN DR DU Ed Ef EM
EQ Et Ez FA FB Fc Fd Fi Fn FP Fr Fw Fy GC Gd GL Gn gP GZ HB HC HF HI Hp Hq Hu Hv Hw Hx iA Ib Id IH Ii Ij Ik II Im In IO IP Iq Is It
Iu Iv Jd Je Jf Jg Jh Ji Jj Jk JI Jm Jo Jp Jq Jr Js Jt Jv Jy Kd KE KF KG KI Kj Kk Kl KO KP KQ KR KS Ky Kz Lh Li Lj Lp Lt Lu Lv LW LX Ly
Lz Ma Mb Mc Md mE MF Mg MH MI Mj MI MM Mn Mp Mq Mr MS MU Mv MW Mx MY mZ NA nB NC ND Ne NF Ng NH NI NJ NK nL
NM NN NO Nq NR Ns Nt NU Nv NW Nx NY Oa Oe OF Og OH Oi Ok Om oN oO Op oQ Or oT Ou oV OW Oy Oz Pa Pb Pd Pe PF Pg pH Pl
Pj PK Po Ps Pz Qa Qb Qc Qd Qe Qg Qh Qm Qt Qu Qv Qw Qx Qy Qz Ra Rb Rc Rf Rg Ri Rj Rm Rt Ru Rv Rx Rz Sh Si Sr Ss St Tn To Tr Tt Tv
Tz Ub Uc Ud Ue Ug Uh UI Um Un Uo Up Us Ut Uu Uv Uw Ux Uz Vb Vc Vh Vi Vj Vo Vp Vq Vs Vt Vu Vv Vw Vz Wb Wc We Wf Wg Wh
Yg Yi Yk Zq Zw Zx Ye Tm Xa Th tF Yf) Fi(aC AD aE Af aG al AJ aK AL aM An AO AP aQ AR aS aU aV AW Ax aZ BA BB BC bF Bg bH
bI bJ bL bM BN BO bP bQ bR bS bV bW bX bZ cA cB cC cE cG CH cI cK cL cM Co CP CQ cR CS CT CU CV Cw cX cY dA DB DC Dd dE
dF DG dH DK DL dM dN Dp DR Du eC Ed eF eM EQ Et Ez FB Fc Fd FP Fr Fy GC Gd Gh GL Gn GP GZ Ha HB HF HI Hp Hq Hr Hu Hv Hw
Hx iA Ib Ic Id Ih Ii Ij Il Im In IO IP Iq Ir Is It Iu Iv Iz Jd Je Jf Jg Jh Ji Jk JI Jn Jo Jp Jq Jr Js Jt Ju Jv Jy Kc Kd kE KF KG KI Kj KK Kl kN KO KQ
KR Ks Kx Ky Lh Li Lj Lp Lt Lv LW Lx LY Lz Ma Mc Md Me Mf Mg Mh MI Mj Mk MI MM Mn MP Mr Ms MT Mu Mv Mw Mx MY mZ
NA Nb NC ND Ne NF Ng Nh nl NJ NK NL nM NN NO Nq NR Ns nT NU Nv Nw NY OE OF Og OH Oi OK Om ON oO OP Or oT Ou oV
OW Oy Oz Pb Pd Pe PF Pg Ph PI Pj PK Ps Pz Qb Qd Qe Qg Qm Qt Qu Qv Qw Qx Qy Qz Ra Rb Rc Rg Rh Ri Rj Rt Ru Rv Rz Sf Sh Si Sr Ss St
Tn Tr Tz Ua Ub Uc Ud Uf Ug Uk UI Um Un Uo Up Us Ut Uu Uv Uw Ux Uz Va Vb Vc Vh Vi Vj Vo Vp Vt Vu Vw Vz Wb Wc We Wf Wg Wh
Yg Yi Yk YI Zw Ye Tm Xa Wm Tj Ti Th tF) Gh(aC AD aE aF AJ aK aL aM AN Ao AP aQ AR AS aU aV AW AX aY aZ bA bB BC bE bG bI
bL bM Bn BO bP bQ bR bS bU bV bW bX cA cB cD cE cF cG cI cJ cK cL cN cO Cp cQ cR cS CT Cu Cv CW CX cY cZ DB DC DD DE DG
Di dJ Dk DL dN Dp DR Du eC Ed eF eQ Ex Ez fA fB Fc Fn fP FR Fw Gb Gc Gd gL Gn gP Gz HB HC HF HI Hr Hv Hw Hx iA Ic IH Ii Ij Ik II
In IO IP Ir Is It Iu Iv Iz Jd Je Jf Jg Jh Jj Jn Jo Jq Jr Js Jt Ju Jv Jy Kc Kd kE KF KG Kj kK KI kN KO KP KR Ky Kz Lp Lt Lu LW LX LY Lz Ma
Mb Mc Md ME MF Mg MH MI Mj Mk MI mM MP Mq Mr mS mT Mu Mv MW Mx MY MZ Na nB Nc ND Ne NF Ng Nh NI Nj NK NL NM
Nn NO Nq Nr Ns NT Nu Nx nY Oa OE OF OH Oi OK oN oO oP oQ oT oV OW Oy Oz Pa Pc Pd PF Pg PH PI Pj Pk Po Ps Pz Qa Qc Qd Qg QM
QI Qn Qt Qu Qv Qw Qx Qy Qz Ra Rb Rf Rg Rh Ri Rj Rm Ru Rv Rx Sf Sh Si Sj Sr Ss St Tn Tt Tv Tz Ub Uc Ud Ue Ug Uh Uk Um Un Uo Up
Ur Us Ut Uu Uv Ux Uz Va Vb Vc Vh Vi Vj Vo Vp Vt Vu Vw Vz Wb Wc Wd We Wf Wg Wh Yd Yg Yh Yi Yj Yk YI Zw Zx Ye Tm Xa
Wm Tj Ti Th tF Yf) Tm(AA aC aD aE AF aG al aK AL aM AN AO aQ AR AS AW AX Ba Bb bC bE bF BG bI bJ bM BN bO bS bV bW cA cB
cC cE cF cH cL CO CP Cq cR CS Ct CU cW CX cZ DC DD DE dF dJ dK DL dN Dp dR eC EF eM EQ Et Ez FA FB Fc Fd Fn FR Fw Fy Gb
gC Gd gL gP gZ hB Hc Hf Hp Hq Hr Hv Hw Hx Ib Ih IJ II Im Io Iq Ir Is Iu Iv IZ jB Jd Jg Jh JI Jm Jo Jr Js Jt Jv Jy kC Ke kF KG Ki Kj Kk KN
KQ KR Ks Ky Ld Lh Lj Lp Lu Lv LX IY Ma MF Mg Mh Mk MI mM Mn MP Mq Mr mT MY MZ NA NB Nc ND Ne Nh nl nJ nK NL Nm NN
NO Nr Nt nU Nv nW Oa Oe Of Oh OK Om ON oO oQ Or oT Ou oV OW Oy Oz Pa Pc Pd Pf pH pl Pj pK Po Pz Qa Qb Qd Qe Qg Qm Qt Qw
Qz Rc Rf Rj Rm Rt Rv Rx Rz Sh St Tn To Tv Ua Ub Ue Uf Ug Uh UI Um Un Uo Up Ur Us Uu Uv Uw Va Vh Vi Vj Vq Vs Vu Vz Wb Wd We
Wf Wh Yd Yg Yk YI Tl Wm tF) Yd(aC Ad aE AF al aJ aK AL aM Ao aP Ar aS aV aW AX aY aZ Ba Bb BC hE bG bI bJ bL bM bN bO bP bQ
bR bS bU bV bW bX cA cC cE cG cH cl cL cN Co CP Cq cR Cs cU CV Cw cX dA DB Dd DE dH Di dJ dM dN dR dU eF eM Eq Et Fa fB Fc
Fd FP GC Gd GL GZ Ha hB Hc hG HI Ho Hp Hq Hu Hv Hw Hx iA Ib Ic IJ II Im IO Ip Iq Ir Is Iu Iz Jd Jf Jg Jh Ji Jl Jm Jn Jo Jq Jt Ju kC kE kF
Kg KI Kj KK KN Ko Kp KQ Kr kS Kx Kz Ld Lh Lu Lv lW Lx IY Ma ME Mf Mg MH MM Mn MP Mq Mr MS mT MU Mv Mw MZ Na NB
nC ND Ne nH NI nJ NL Nm Nn No Nq Nr NU Nv NY OE OF Og Oh Om On oO oQ oT Ou oV Ow Pa Pb Pc Pd Pe PF Ph pl pK Po Pz Qh Qm

Figure 4 Continued

Figure 4 Continued tF Yf) Yi(aA aC Af aH aM aN Ao aU aV aW bA bC bE Bg bH bJ bL Bn bU bZ cB cD cE cF cM cN Co CQ cR CT cV CX cZ dA Db dC dD De dF dH Di dJ Dp dU Ex Ez Fa fR Fw Gd gL hB Hf Hu iA Ib Id Im iO IZ jB Je Jk Jl Jm Jn Jo Jy kG KO kR Ks Ld Lh Ma Mb mE mF Ml MP MT Mu Mw mZ nA Nb nC nD Nh nl nK Nl Nu Oa Oe OF oK oO oP oQ oV Oy Oz Pe PH Pi Qa Qd Qe Ql Qn Qu Qv Qy Qz Rf Rh Rm Rv Rx Sf Sr St Uc Uk Un Uo Up Ur Va Vh Vs Wc Wd Wf Zx Tj Th tF) Sf(aC aG aK aL aM An AO aV aW aY bB BC bE bJ BN bP bU bW bX cH cI cK cL cM cN cR Cs Ct cW cY dA DD Di dK eF eM fA Fc fP Fw Gd gP gZ hC Hq Hu Hv Hw Hx iJ Il Je Jf Jh Jk kC Ke KG Kj Kk kN kQ kR kS Lh Lt Lv Lx lY mH Mj Ml MM Mn Ms MT Mu NA Nb nC Ne nl nl nK NN Nq Nr Nt NU Nw Ny Oe Of Oh Om On Or Ow Oy Pa Pd pK Po Qg Qn Qz Ri Sh Ss St To Tr Ub Uh Uk Ul Uo Up Ur Ut Vh Tj tF) Wd(Af aJ Al AP Ar aW Bb BC bE BG bJ bN bU bW cB Ch cI cL cM CO Cp cU dB dD Fb fP Fr Fy Gb Gl Gp Ib iJ Ik Ip Is jB Jg Ji Jk Jl Jp kC Ke kF kG Ki Kk kN Kq KS Lh Lj lW lY Ma MM Mn Mr Ms nA Nb nC nD nH nI nJ NL Nn No Nq nR nU Nw Ny Oh OK Om oN Op Ou Ow Oz Pb Pc Pe PF pI pK Po Qd Qg Qv Qz Rc Rf Rh Rz To Tr Tz Ub Uf Uh Ul Uo Ut Vi Vj Vt Vw Yh Xa Tj Ti) Op(aC aD all aK aL aM aN Ao aU aW aZ Ba Bb bE Bg bJ bU bX cB cG cL cM CQ cR Ct cW cY dA dD De dJ dN eM Ez fA Fw Gd gL gP Ha Hc Hq Hu Ib Ij Jm kC kG KN KO kR Ky Lh lY Ma Mb mH Ml mM Mp MS mT Mu Mv Mw mZ nA nC ND Ne Nh nI NK Nl Nm No Nt Nu nW Oe OF Og On oO oP oQ oT Ou oW Oy Pd Ph Pz Qd Ql Qm Rh Rm Rx St Uc Ug Uk Un Uo Up Ur Uu Va Vh Tj Th tF) Vi(AA aC aD aH aK aL aM An aW aZ bA bC bE bJ bL bM Bn bO bU cB cD cE cL cM cP cR cU cW cY dD dJ Ed Ez fA Fb fP Gb gP Gz Hb hC hG Hq Ib Im Jd Je Jh Jk Jl Jn Jp kG Ki Kk kN kQ kR Ld Lh Lv lW lY Ma Mb Mh Ml Mm Mn Ms Mu Mw Mz nA Nb nC nD NH nI nJ nK nL NN No Nq Nt nU Nv Ny Oa Oe Oh Om oQ OW Oy Pb Pc Pe Pi pK Ps Qu Qy Qz St To Tr Ua Ul Uo Up Ur Us Ut Wb tF) Gb(aC aD aM aN Ao aS aU aZ bB bC bE BG bJ bM bO bW bX cB cE cL cM cN cP Cq cV cY dA DD Dk Dl dR dU eM fB fR Gd gL Gz hB Hc Hq Hu Ib Ih Ij Im Iu Je Jk Jt Ju kC Ki KN Kp kR kS Lu Lv lW lX lY mH mM Mn Mp Ms mT Mu Mv Mw MZ Nb NC Ne Nh nI Nm Nu Nv nW Ny Oa Of oO oP oV Oy Pi Pz Qd Qg Qh Qm Qy Qz Rm Rv Sr St Tt Uc Un Up Va Vh Vu Vw Wf Zx Tj Th tF) We(aC aD Af aM AN Ao aV aW bC bE bJ BN bU bW cB cD cE Ch cL cM CO cR Ct cU cW cY dB dD De dJ Ez fP Gd gP Gz hB Hf Hu Id jB Je Jh Jk kF kG Kk kN kR kS Ky Lv lY Ma Mb Ml mM Mn Ms mT Mu Mv Mw My MZ nA Nb nC nD Ne Nh nI nJ nK NL Nm Nn Nq nU Nv Ny Of Oh oK Om ON oT oV Ow Oz pF Qu Qv Qy Qz Rh Rx St To Tz Ua Uo Up tF) Va(AD Af aI aN Ap aV Bb bJ bN bU bW cD Ch cL cM cN Co cR Ct dA dB dD Dg Et Ez Fb fP Fy gC Gd Gl HB hC Hu Ii jB Jg Jh Jp kC Kf Kg Kk Kl kN kQ kR Lh Li lY Ma Ml MM Mn Ms mT Mz nA nD NH nI nJ nK NL Nm Nn nR nU Nw Ny Oh Om On Ou Ow Pg pK Qe Qu Qv Qz Rf Rt Sr St To Tr Ua Uf Uh Um Uo Up Ur Ut Uu Ux Vo Tj Ti) Wf(Af aJ aK AP bB BC Bg bJ bN bO bW cB Ch cK cL cM cN Co cS cU dB Dc Dg eF Ez Fb Fr Gl gP Hb Hf Id Ii iJ Je Jg Jh Ji Jp kC Ke Kk kQ KR Lh Li Lt Lv lY Mb mE Mh Mj MM Ms Mu MZ nA Nb nD NH nI nK Nn nR NU Ny Oh oK Om Ou Ow Pb Pe pI Qh Qu Qv Qy Rh To Tr Ue Uf Ul Uo Up Ut Ux tF) Fc(aC aD aK aL AN aQ aU aV aW bE bJ bM bO cB cE cJ cL cM cN Cq cR Ct cU cW cY dA dD dN dR dU Ez fA fB gL gP Gz hB hC Hq Ib Ih iZ Jd Je Jk Jn kG kN kR Ky Kz lY Mh Ml mM Mq Mu Mv Mw mY MZ nA Nb nC nD Ne Nh Nl NJ NK nL Nq NU nY Oe oQ oV Ow pK Qh Qu Qy Rh To Uc Uo Up Wb tF) Ps(aC aD aL aM aS aU bC bE bG bI bJ bM bN bO bR cB cE cL cM cN Ct cU cW cY cZ dA DD dR Ez fB Gd gP HB Hq Ib Ih Im IZ Jc Jk Jl Jn kC kN kQ kR kS Lh Lv lW lY Mh MM Mw mZ nA Nb nC nD Nh nI nK nL Nq Nt Nv nW Ny Oe On oO oQ oV Oy Qd Qh Ql Qm Qz Tr Un Uo Up Vu Yk tF) Vh(Aa aD Af aI aM AN BB bC bE bN bU bW cB cL cM cN Co Cq Ct cU cW dD Et Ez Fb fP gC gP Hb hC Hq Hv jB Je Jg Jh Ji Jp Jv Kf Kk Kl kQ KR Ky Lh Ma Ml Mn Ms Mu Mz nA Nb nC Nh nI nJ nK Nl Nm Nn Nu Nw Ny Oh Om Ou Ow Oy Pb Pc pK Qu Qz Rf Rh Rt To Uh Uk Um Uo Up Uv Vo Ti) Gn(aK aN Ao aV aW bC bE bJ bN bU bW cB cE cJ cL cM cN cR Ct cU cW dA dD Ez Gd Gl gP hB hC Hq Hu Hv jB Jh Jm Jn kC kG Ki KN kQ kR Lh Lv lY Ma Ml mM Mn mP Ms mT Mu Mw Mz nA Nb nC nD NH nI nJ nK NL Nn Nt NU Ny Oe Of Oh oK Om ON Ow pK Qz Uk Uo Up Ut Ti tF) Vw(Aa aC aK Ao aV aW Bb bC bE bJ bN bU bW cB cE cL cM cR Ct cW dA dD Ez Fb Gd HB Hq Hu Iz jB Je Jk Jn Jp kC kG Kk kN kO kR kS Lh lW lY Ma Ml MM mT Mu MZ nA nC nD nI nJ nK Nl No Nt Nu Nv NW Ny Oh Ok Om On Ou oV Ow Oy Qu Qz Rf St Tr Ua Uf Uo Up Zx Tj tF) Zx(Aa aI aJ aK An Bc bE bJ bN bW cL cM cN cO Ct CU dB dJ Dk Ez FB Fr gC Hb Hr Hv Ib Id Ii Io Jh Ji Jo Jq kC Kf kN Ko Kp KQ kR Li Lj lY Mg Mj Ml mM Mn Ms Mz nA Nh nI Nm Nn NR Nu Nw Ny Oi Om Ou Ow pI Pj pK Qg Qu Rc Sr St To Uo Up Ur Ux Vj Vt Tj tF) Wb(Aa aK aV Bb bC bJ bM Bn bU bW cB cL cM cR dA DD Ez Fb fP Fw Gd Gl gP Gz HB hC Hq Ib Id Jd Jh Jp kG Kl Kk KN kQ Lh Li lY Ma Ml MM Mn Ms Mu MZ nA nC nD Nh nI nJ nK Nl Nn No nU NW Ny Oh Om oO Ow Pb Pc Pe Qu Qz Rh St To Tr Uo Up Ut) Sh(aD Af aK Ao aV bC bE bJ bN bU bW cB cL cM cN Co cR Ct cW dA DD Ez fP Gd Gl gP Ha hB hC Hq Id jB Jh Ju Jv kG Kk kN kR Lh Lv lY Ma MM Mn Ms Mu Mv Mw Mz nA Nb nC Nh nI nJ nK NL Nn nR nU Ny Oh Om Ow Oy Ph Qt Qu Rh St To Tr Tz Uo Up Uv Xa Ti) Zq(aC aD Af aN Ao Ap bA Bb bC bE bJ Bn bW cB cD cN Cq cR cT cV dJ Ez fR Gd GL gP HB Hf Hu Ib Ii Im Iz kC Kg Kl kQ kR Ld lY Ma Mb Ml MM Mu Mv Mw mZ Nb nD NH nI nJ Nl No Nq Nu nW oO oQ Oy Qe Qh Qu Qv Qy Qz Rh St Tr Tt Uk Uo Up Ux Tj Th tF) Vj(aC aD aL An aU aW bC bE bJ bU cB cE cL cM cN CQ Ct cU cW cY cZ dA dD Ez fA fP Gd gP Gz hB Hq Hu Ib Jk Jn kC kG Kk kR Lh lY Ma MH Ml Mm mP mT Mu Mv Mw Mz nA Nb nC nD Nh nI nJ nK Nl No Nu Oa oO oP pK Qh Qz Rf Rm To Tr Tt Ua Un Uo Up Ur Tj tF) Ux(aC aL aM aN aV aW Bb bE bJ bN bU bW cB cE cL cM cN Ct CW DD dR dU eM Ez fA Gd gP Gz Hq Hu Ib kG Ki KO kQ kR Lh lY Ma Ml MM Mp Mu Mv Mw MZ nC nD NH nI nJ nK NL Nm No Nq Nu Nv nW Of oO oP oQ Oy Qd Tr Tt Uc Ue Uo Up Ut Th tF) Lt(aC aK aL aM AN aQ aR aV aZ bE bJ bU bW cB cD cE cJ cL cM cN cR Ct cW dA dD dN dR dU Ez fA Gd Gz hB Hq Hu Ih Iz jB Je Jn Ju kC kG KN kO kR lW lY Ml mM Mu mY MZ nA Nb nC nD Ne Nh nI nJ NK Nt NU Oe pK Qh Qy Rh Uc Ue Uo Up Ut tF) Ho(aD aJ An Bb bE bJ bN bU bW Ch cL cM cN Ct cW dD dJ dK Ez fB fP Gd Gl Gp hC Hq Id Jh Ji Jp Jq kC kG Kk KN Lh Lv lY Ma mH Ml MM Mn mP Ms Mv Mw Mz nA Nb nC Nh nI nJ nK Nn Nq nU Oe Of Oh Om On Ow pF pI pK Qz Rh To Tr Up Ur Tj) Rt(AD Af aK aN aV aZ bE bJ bN bU bW cB cD Ch cM cN Co cR Ct cU cW dA De Ez fP Fw Gd Gl HB hC Hq Ii Iz Jh Ji Kg Ki kN kQ Lh lY MM Mn mT Mz nA NH nI nJ nK NL Nm nR NU Ny Oh oK On Pg pK Qu Qv Qz Rh Tr Tt Ua Uc Uo Ti) Lp(aC aD aK aM aV aW aX bC bE bI bJ bN bP bW bX cB cE cG cI cM cN cP cR Ct cU cW dA dR Ez fB Gd gP Gz hB Hc Id kG Ki kN kO kR lY Ml mM mS MZ nA Nb nC Nd Ne Nh nI nK Nl nU nW nY Oe Og On oO oV Oy Qh Qu Rh Rj To Ua Ug Yk Th) Du(Aa aC aI aM aZ bC bE bJ bN bW cB cL cM cN DD dJ Ez fP Fw gC Gd Gl gP Gz hB hC Hq Hu jB Jh Ji Jn kC KG Kk kN kQ kR Lh lY Ma mH Ml MM Mn Ms Mz Nh nI nJ nK nL Nn NU Oh Ok Om Ow Oy pK Qg Qz Tr Ua Uo Up Ut Tj) Fd(aK aM An aV Bb bC bJ bU bW cL cM cN Ct cU Et Ez Gd Gl gP Hq jB Jh Jv Kk kN KQ kR Kz Lh lY Ma MM Mn Mq Ms Mu Mw mZ nA Nb nC NH nI nJ nK Nn Nq NU Nw Ny Oe Oh Om Ow Qu Qv Qz Rf St To Tr Uk Uo Up Ut Tj Ti) Yk(aD AF aI aK Al aV aW bA bE bJ BN bU bW cD cM cN Co cR CT cW dA Db De dJ Fw gL gP Hb hC Hf Hu Id kN kQ Lh lY Mb mH Ml MZ nC Nh nI nJ nK Nl Nt Nu Nv On Oy Pa Pc pK Qu Qv Qz Rf Rh St Uk Up Ur Ut Tj Ti Th) Rx(aL An Ao aV Bb bJ bN bW cB cL cM Ct cU cY dA dD Ez Gd Gl gP Gz Hq Hw Hx Ii Jh kC kG Kk KQ kR kS Lh Ma mH Mm Mn Ms MZ nA Nb nC NH nI nJ nL Nn Nq NU Ny Oe Oh Om Ow Pb Pc pK Qz Rf Rh To Tr Uh Uo Up Ut) Th(Af aJ Ax Bb bC bE bJ bN bW cN Co Cs cU eC fB fP Fy gC Gl hC Hf Ic Jh Ji Jj Jq Ke Kg Kl kS Ky Lh Lu Ma mH Ml Mn Ms MZ Nb Ne NH nI NJ NL Nn nR nU Ny Oh Om Ou Ow Pg pI Qg Qh Rf Rh To Uc Uh Uk Uv Tj) Rv(aC Af An aO bE bJ bM BN bU cJ cL cM cN Co Cq cU cW dD dK Ez fP Fw Gl gP hC Hq Ip Jh Jq kF Kg Ki Kk kN kQ kR lY Ma MM Mu nA nC nD NH nI nJ NL Nn nU Nw nY Om oN Ow pK Qg Qt Qu Qz Tr Ub Uk Uo Ur Ut) Rz(aK aV Bb bC bE bJ bN bS bU bW cB cE cL cM cN Ct dD dU Ez fP Gd gP Hq Hu Ib Id Ih Ip Iq jB Jh Jm Kk kR Lh Ma Mb Ml MM Mn mT Mu Mv Mw Mz nC Nh nI nJ nK nL Nn Nq nU Nv nW Oe Om oT

Figure 4 Continued

Oy Qu Tr Tt Uo Up Tj tF) Wc(Af aK aM An bE bJ bN bW cB cL cM cU cW dA dD Ez fA fP Gd gP jB Jh Jq kC kG Kk kN kO KQ kR Ky Lh
lY Ma Ml MZ nA Nb nH nI nK nL Nn NU NW Ny Oe Of Oh Om Ow pl Qh Qz Uc Uo Up Ut Vo) Xa(aD aI aM Ba bC bE bJ bS cB cL cM cU
dD Dp Ez Gd gP Hc Hq Hu Il Iq Iu Jh Jk Ki KN kQ kS Ld Ma mM Mu Mv Mw My MZ NA nI nJ nK nL Nq Nt Nu oK Oy Pi Qg Qy Qz Rh St
Uk Uo Up Ut Vq Tj) Yf(aH aK aV aW bE bJ bM bO bU bW cB cE cL cM cN cR Ct cW Ez Gd gP Ha hB Hq Hu Ip iZ jB kN kR kS lY Ml mM
mP Mu Mw nA nC nD Nh nI nK Nl nW oK oO Pa Qz Rh Uo Up Ur Ut Ti) Yh(aD aF aI aK aM Ao bA bC Bn bQ cB cN cX Dp Ez Gd gP hC
Hq Hu Jn Ki KN kR Lh lY mH MZ nA Nh nI nJ Nu Pi Qu Qz Rf Rh Sr Ua Uk Up Ut Tj) Gd(Ad Ao bB Bg cG Ch Cq Dg Dl Et Ex Gl Gz hB Hr
Jg Jt Kr Ly Ng Nq Nt Oe Of Pi Qg Qh Ra Rg Ru Ss St Ub Ug Ur Uz Vc Vp Wg Yj Ye) Ye(aK aV bE bJ bU bW cB cL cM cN Ct Ez gP Hq Hu
jB KN kR lY mM MZ nA Nb nC Nh nI nK Nq NU Oc Qz Rh Uk Uo Up Ut Tj) Wg(aK bC bE bJ bU bW cB cL cM cN Ct Ez Hq Hu jB KN kR
lY Ml mM MZ nA Nb nC Nh nI nK Nq NU Rh Uk Uo Up Ut Tj) Ru(aK bC bE bJ bU bW cB cL cM cN Ct Ez Hq Hu jB KN kR lY Ml mM MZ
nA Nb nC Nh nI nK Nq NU Rh Uk Uo Up Ut Tj) Vc(aK bC bE bJ bU bW cB cL cM cN Ct Ez Hq Hu jB KN kR lY Ml mM MZ nA Nb nC Nh
nI nK Nq NU Rh Uk Uo Up Ut Tj) Uz(aK bC bE bJ bU bW cB cL cM cN Ct Ez Hq Hu jB KN kR lY Ml mM MZ nA Nb nC Nh nI nK Nq NU
Rh Uk Uo Up Ut Tj) mT(Ed Ef Fa Fb Fw Fy Gl Ib Jv Ke Kf Kl Kn Ko Kq Kr Ks Ky Ou Ow Ph Pj Qh Rc Rf Sr St To Uc Uh Uk Uv Vo Tj)
Yj(aD aK aV bQ cB cN cX dA gP Hb Hf Hq Kg kN Lh Lu lY Mb Nb nC Nh nI Nl Nu Qh Qu Qv Rf Uo Vq Tj) Ut(An Cs Cu Dc li In Js Ky Ma
Mf Mw Mz Nh Pb Pg Qa Qh Rf Rm Tr Uk Ur Uv Tj) Ld(Ar Ax bP cM Cs cU Fa Fp Hu Jl Lj nl nY Pe Qe Rf St To) Iz(Al Bb Bc cM Dg Ez Jt
Kl Lv nH Ou Pf Qe St Uc) Tj(bC bJ bU cD cM dR It Kc Kk kR Md Ms To) Ti(bE Kn kR Ml mZ Ne nI Qg Uk Ur) cM(Ex Ko Kz Nd Pj Ua Uk
Um Vq) bU(Fw Fy Kn Mb Nd Rg Uk) Lv(Fw Hb Hc Uk Vq Vu) Kk(Cs nC NH nJ Ur) Rf(cR Hq kR Nu Oy Tt) Qh(dR Qz Ua Vs Vv) Ko(Aa dB
Ma nH Uu) Vq(aM bJ cU nI Qe) Tt(nR Om Uh Uv) Uk(bX dR Ns To) Nu(cX Ex Up) Ky(bX Di Ns) cR(Oa Ou To) Ur(dR Nx) gL(St To) AaGl
AlUa CsFa FbfR UbbJ TrbX JukR QncU} nN{jT(Aa AD aF aG aH Aj aK Al aM aP aQ aS aU aV AX aY bB bC bE bF Bg bH bl bJ bL bM bP
bQ bU bV bX bZ cA cB cC cE cI cJ cK cO CP cQ CS cT Cu cV Cw cX Db DC Dd dF Dg dI dJ Dk dL dM dN dR eC fP gP gW hC hF Hq Hr
Hu Hv Hw Hx iA 1H Ii Ij Il In iP Iq Ir Is It Iu Iv jE jF Jg Jh Ji Jj Jk Jl Jm Jn Jo Jp JQ Jr Js Jt jY kQ kR Li Lj Lu Mg ml Mk mM Mq mS Mt MW
Mx MY Na Nc Nd Ne Nf Ng Nh Nl NJ Nk NM Nn nO NR Ns nT nU nW Nx NY oE OF Oi Om oN Oz Pa Pc Pd Pe Pg Pz Qa Qb Qc Qd Qe qY
Uc Ug Uh Uk Ul Um Up Ur Vv tF) jF(Af aI aN aW bA bF cE cG Cq cR cT cV cZ dJ dK dM dN eD eF Fp FrhG Hr Hu Hw Hx iB lh li iJ Ik Im
In lo Ip Ir Is It Iu Iv iZ jE JG Jh Ji Jj Jk jL Jm Jn Jp Jq Js jU jY kC kF kG kI kK kN kO kP kR kS Lh Li lM IN Lu Lw LY Lz Mb Mc Md ME MF
Mg Mh MI Mj Mk MI MM Mn Mp Mq Mr Ms MT Mu Mv Mw Mx MY Mz NA NB Nc Nd Ne NF Ng Nh nI NJ NK NL NM Nn nO Nq NR Ns
Nt nU Nv Nw Nx Ny OE Of Og OH Oi OK Om oO oP Pa Pb Pc Pe Pf Pg Pz Qa Qc Qd qT qU qV qW qX qY qZ rA Tz tF) IN(aD AF aG AJ aK
Al aM An AO AP aQ Ar aS aU aV AW AX BA Bb BC bF bl bJ bM Bn BO bP bR bS bU bX cA cB cC cE cG Ch cl cJ cK cL cN cO CP cQ cS
CT cU cV cW Cx cY dB dC Dd De dF DG dl DK DL dM dR eD gL gP gW hB hC hF hG Hr Hw Hx iH Ii iP Is iZ jE Jj jL Jm Jn JQ jU jY kC
kF kK kN kP kQ kR kS mF Mg Mk mM mW MY Na Nd Ne nF Ni nJ Nl nO nT nW nY oH Oi oK Om oN pF Qc qT qV qW qX qZ rA Tz Ua
Ud Ue Ug Uk Ul Um Uo Ur Ut Uu Vt Vv Wm tF) qY(aA aD Af aG aH aJ aK aM An AO AP aU aV AX aY Ba bB BC bE bH bl bJ Bn BO bP
bQ bR bS bU bV bX cB cE cG cJ cK cL CO CP CQ CS cT cU Cv CW CX dB Dc De Dg dI dK dL dM dN eC fP gL gP gW hB hF Hu hV hW
iA iC iH iJ iP Is iZ jE Jg jH jI Jj jL Jm Jn jP JQ jR jV jY kE kG kI kK kO kP kQ kR kS IK IX mH ml mM mP mS mT mW mY Na Nd Ni NJ nL
nO nT nW nY oE Og oN oP pF Qc qW qZ rB Ud Uh Uk Ul Um Un Us Uu Vo Vv tF) jH(aD Af aG aJ aK aM AN AO AP Ar aU Aw aY BA
bB bC bE bF pB cE cG cl cJ cK cN CO cP cQ cR cS cT cU cW cY dB dC dD De Dg dK dL dM dN dR eC Et fP Fr gL gP gW hB hF hG Hq Hr
Hu Hv Hw Hx iH li iJ iP Is iZ jE Jg Jh Ji Jj Jk Jl Jm Jn Jo Jp Jq Jr Js Jt jY kR kS Lh Li Lj Lx ml Mk Mq Mt Mu MY Na Nb ND Ni nJ nK nM
Nn NO Nq nW nY oE OH Oi Om Oz Pc pF Po Qa Qb Qc Qd Qe Uh Uc Uh Um Uo Us Vv tF) jQ(aH aJ aK aM aN aQ aS aV Aw aY bA
bC bE bF bH bl bJ bO bP bQ bR bU bV bX cA cB cC cE cG cJ cK cO Cp CQ Cs cU cV cW CX De dG dI dK dL dM dN eD fP gP gW hB hF
hW HX iH li iJ Is jD jE jG Jj jK jL jM Jn jO jP jU jY kC kG kI kK kO kP kQ kS IM lY mE mF Mg ml mM MT mW mY nA nC nF nI nJ nL nM
nO nR nT nU nW nY oE oH oN pF qT qW qX qZ rA rX rY Ud Ue Uh Uk Ul Um Un Vo Vv tF) jE(aA aJ aL aN Ar aV Ba Bg bJ Bo bV cP cR
cT dA dB dF dG Di dJ dN eD Fp hA hR hV hW HX iB iC iH Ii Ik Is jD jG jl jK jL jM Jn jO jP Jq jR jU jY jY kC kE kF kG kI kK kN kO kP IK
IL IM lO lW lX lY mE mF Mg mH ml mM mP mS MT mU mW mY mZ nA nB ND nF nl NJ nK nL nM nO NR nT nU nW Oe oH Oi
oK oO oP qT qL qV qW qX qZ rA rB rC rX rY rZ Vt tF) qV(aD Af aG aJ aK Al aN AP aQ aU aV Aw AX aY BA BC bE bl bJ Bn bO bP hQ
bR bU bV bX cC cE cG Ch cJ cK cL CO CP cQ CS cT cU Cv cW cX cY Dc Dd dG dl dJ dK dL dM dN eC eD fP gL gP hB hF Hx iH li iO iP
Is iZ Jj Jn Jq jR jY kK kQ kR kS IM mH ml mM mW MY Na nD nl nJ nM nO nR nT nU nW nY oE Oi oN pF qT qZ Ud Ue Ug Ul Um Vo Vv)
jl(aD aG aJ aK aM AP aS aU Ax aY aZ BA BB bC bE bF bl bJ bP bQ bR bU bV cA cB cE cG CH cl cK cL CO cP cQ cS cT cU cV cW cX cY
dB Dc Dd Dg dl dK dL dM dN eD fP gL gP gW hB hF iH li iJ iP Is iZ jG Jj jL jM Jn jY kG kO kQ kR kS IM ml mM mS mT mW mY Na Nd
Ni nJ nM nO nT nU nW nY oE oF oH oN pF qT qX qZ Ud Uh Um Us Uv Vo Vv tF) lM(aD aF aG aJ aK aM aN Ao AP aQ aS aU aV Aw AX
aY BA bB bC bE bF bJ bM bO bP bR bU bV cA cG Ch cJ cK CO CP CQ CS cT cU cV cW cX cY dC dG dl dJ DK DL dM dN dR eC eD fP
gL gP gW hB hF hV hW HX iH iJ Is iZ jL Jn jR jY kK kQ kS IX Mg MM mS mT mW mY nJ nO nT nY oE oH oN oP pF qX Ud Uk Us Uv tF)
jY(aA aI aJ aL aN aO Ap Ar aV BA Bg bJ bV bZ Co cP cR cW dA Dc dG Di eD hR Hu hV Hw HX iB iC iH iO Is jD jG jK jL jM Jn jO jP
Jq jR jU jV kC kE kF kG kI kK kN kO kP Lj IK lL lO lW lX lY Me mF Mg ml mM mS mT mU mW mY mZ nA nB ND nF nl NJ nK nL nM
nO NR nT nU nW Oi oO oP qT qU qW qX qZ rA rB rZ Vt) lO(aF aG AJ aK aM aN AO Ar aS aU aW Ax aY aZ bA bB bC bF BG bl bJ bL bM
bN Bo bP bQ bS bU bX bZ cA cB cC cD cE cI cN CP CQ Cs Ct CU cV cW CX cZ Db DC Dd De dF DG dH dl dK dM dN dR fP gL gP hB hG
iA iH iJ iP Is iZ Jj Jn kQ kR mY nO nW nY oE oK oN Tz Ua Ub Ug Uh Ul Um Un Ut Uv Wm tF) jU(aD aE aG aH aJ aK aM AN aP aQ aU aV
Ax Ba bB bC bE bH bl bJ bM Bn bP bQ bR bU bV bX cE cG CH cJ cK cL cN CO Cp cQ CS cT cU Cv Cw CX dA dB DC Dd De dG dH dl dJ
DL dM dN eC fP gP gW hF iH li iJ iP Is kR kS mS mY Na nJ nM nO nT nU nY oE oH oN pF qZ Ua Ud Ue Ug Uh Ul Um Us Vv tF) hA(aD Af
aG aJ aK aM AN Ao AP aQ aU aV Ax aY BA bC bE bl Bn BO bP bR bU bV cB cE cG cJ cK cL CO cP CQ cT CV cW cX cY dC dD De dG
dK DL dM dN dR eC fP gL gP gW hB hF Hu iH li iJ iO iP Is iZ Jg Jh Jj Jn Jq kS Mk mY Na Nd nO nW Nx nY oE oH Oi pF Tz Ua Ub Uc Ud
Ue Uo Up tF) iB(aD aF aG aJ aK aM An AO aP aS aU aV AX aY bA BC bE bF bH bl bJ bM bO bP bR bU bV bX cA cB cE Ch cJ cK cL cN
cO CP CQ cS cT cV cW dB dC De dG dl dK DL dM dR eC fP gL gP hB hF Hu iH iJ iP Is iZ Jj Jn Jq kQ ml mY Na Nd nO nW nY oE Oi qZ Tz
Ua Ud Ul Um Uu Vo Vt Vv tF) jO(aD aF aH Al aM aN Ao AP aQ Ar aS aU aV AX aY BA bB bE bF bH bl bJ bM bO bP bQ bR bU bV bX cA cB
cC cE cG cJ cK CO cP cQ cR CS cT cU Cv Cw CX cY De dI dK dL dN eC fP gL gP gW hF hG li iJ iP Is iZ Jj kQ kS mY nO nW nY oE oH
oN pF Ua Ud Ug Uh Ul Um Ur Uv Vo Vv tF) jR(aJ aM Ao aP aU aV Aw Ax aY bC bE bF bM Bn bO bQ bR bU bV bX cA cB cF cJ cK cL
CO Cp cQ cU cV cW CX DC De dG Dl dK dL dN eC eD fP gW hF Hx iH li Is jG jL Jn kE kN kP kQ kS lY ml mM MT mW mY nA nl nO nT
nU oE oK oN pF qT qX qZ rA Ue Ug Uh Ul Um Un Ur Vo Vv Wm tF) jV(aG aH aJ aK aM AO aU bA bB BC bl bJ Bn bP bQ bR bU bX bZ cB
cE cI cK CP CQ CS cU CW CX Db dC Dd De dG Di dJ dK dM dN dR fP gL gP gW hB hF iA iH li iJ iP Is iZ Jj Jn Jq kS mW mY Nd nO nW
nY oE oH Oi oN pF Ud Ue Ug Uh Ul Um Uu tF) eD(al Al aR aW aY bC bQ cF eM cS cW dE hC hG Hu hV Hw Hx iH iJ Il In Ip Ir Is Iu Jg Jh

Figure 4 Continued kI kK kN kO kP lW lX lY mE mF mH ml mM mP mS mT mU mW mY mZ nA nB nC nD nF nH nI nJ nK nL nM nO nR nT nU) jU(kC kE kF
kG kI kK kN kO kP lW lX lY mE mF mH ml mM mP mS mT mU mW mY mZ nA nB nC nD nF nH nI nJ nK nL nM nO nR nT nU) jV(kC kE
kF kG kI kK kN kO kP lW lX lY mE mF mH ml mM mP mS mT mU mW mY mZ nA nB nC nD nF nH nI nJ nK nL nM nO nR nT nU) IL(kC
kE kF kG kI kK kN kO kP lW lX lY mE mF mH ml mM mP mS mT mU mW mY mZ nA nB nC nD nF nH nI nJ nK nL nM nO nR nT nU)
lM(kC kE kF kG kI kK kN kO kP lW lX lY mE mF mH ml mM mP mS mT mU mW mY mZ nA nB nC nD nF nH nI nJ nK nL nM nO nR nT
nU) iB(kC kE kF kG kI kK kN kO kP lW lX lY mE mF mH ml mM mP mS mT mU mW mY mZ nA nB nC nD nF nH nI nJ nK nL nM nO nR
nU) jD(kC kE kF kG kI kK kN kO kP lW lX lY mE mF mH ml mM mP mS mT mU mY mZ nA nB nC nD nF nH nI nJ nK nL nM nO nR nT
nU) jT(kC kE kF kG kI kK kN kO kP lW lX lY mE mF mH ml mM mP mS mT mU mY mZ nA nB nC nD nF nH nI nJ nK nL nM nO nR nT
nU) jY(kC kE kF kG kI kK kN kO kP lW lX lY mE mF mH ml mM mP mS mT mU mY mZ nA nB nC nD nF nH nI nJ nK nL nM nO nR nT
nU) lN(kC kE kF kG kI kK kN kO kP lW lX lY mE mF mH ml mM mP mS mT mU mW mZ nA nB nC nD nF nH nI nJ nK nL nM nO nR nT
nU) lO(kC kE kF kG kI kK kN kO kP lW lX lY mE mF mH ml mM mP mS mT mU mY mZ nA nB nC nD nF nH nI nJ nK nL nM nO nR nT
nU) hA(kC kE kF kG kI kK kN kO kP lW lX lY mE mF mH ml mM mP mT mU mW mY mZ nB nC nD nF nH nI nJ nK nL nM nO nR nT nU)
iC(kC kE kF kG kI kK kN kO kP lW lX lY mE mF mH ml mM mP mT mU mW mY mZ nB nC nD nF nH nI nJ nK nL nM nO nR nT) Et(qQ
sK uG ul uL uM uO uW uX uY uZ vA vB vC vS vV wG zH) Nw(rX sJ uG ul uL uM uN uO uW uX uY uZ vA vB vC vS zH) zH(Bc Gz lp Jd Ji
Kc Mm Mz Nq Ok Um Un Vt) eP(cT De Di Ex Iz Jh Jp Kf KI Kq Lh On) Mz(qC rR rU rV tV uZ vB vI vS) dX(aH Jh Jp Jt Ko Kq Ns On)
Bb(rC tN tV uM uX vB) sJ(Ap Jg Mm Nm rS Tr) Ex(uL uN uZ zG) Mm(uZ vA vB wG) rS(sF sH sI) Gn(nf We) Gp(Yg Yi) Nm(qQ vB) Iz(Uy
Vb) Ok(rX uZ) AazG DugC TjWe XaRh} Eo{Lx(Aa aC AD aE AF aH al aJ aK AL aM AN Ao AP aQ aR AS aU AW aX aZ Ba bC bF bG bI bJ
bL bM Bn Bo bP bQ bR bS bU bW bX bZ cA cC cD cE cF cG CH cJ cK cL cN CO Cp Cq CS Ct CU Cv Cw CX cY cZ dA DB Dc Dd DE dF
dG dH DI DK DL dN DW dX Ef EM eP Et EW Ex Fp Fr Fw Gd GI gV Hr Hw Hx Ih lj Ik II Im In Io Ip Iq It Iu Jh Ji Jk JI Jn Jo Jq Js Jt Lh Li Lj
Lw Lz Ma Mc Md Me Mf Mg Mh Mi Mk Ml Mm Mn Mq Mr Ms Mt Mu Mw Mx My Mz Na Nb Nc Ne Nf Ng Nh Ni Nk NI Nm No Nr Ns Nt
Nu Nv Nw Nx Og Oh Om On Oy Oz Pa Pb Pc Pe Pg Po Pz Qb Qc Qd) aN(aC AD aE AF aG aI AJ AL aM An Ao Ap aS aU AW aX aZ Bb BC
bF Bg bI bL bM Bn Bo bP bQ bR bW bX bZ cA cC cD cG CH cJ cL cM cN CO Cp CQ cR cS CU Cv Cw CX cZ dA DB DC dD DE dF Dg DI
dJ dK DL dM dN DW dX Ef Em eP Et Ew Ex fP FR Fw Hq Hw Hx Ij Ik Im In Io Ip Iq Ir Is It Iu Iv Jh JI Jn Jr Js Lh Lu Lw Ly Lz Ma Mb Mc
Md Me Mf Mi Mj Mk MI Mm Mn Mp Mq Mt Mu Mv Mw Mx My Mz Na Nc Nd Ne Nh Ni Nj Nk NI Nm Nn No Nq Nr Ns Nt Nu Nx Ny Oe
Og Oh Om Oy Pa Pb Pd Pf Pg Pz Qa Qb) aC(Ad aE AF aG aH aI Aj aK aL aM An AO AP AR AS aU aV AW aX aY aZ BA bB BC bE bF BG
bH bI bL BN BO bP bS bV bZ cA cB cC cD cE cF cG CH cI cK cL cM cN CO CP CQ cR Cs cT CU cV cW cX cY cZ dA dB Dc De dE dF DG
dH DI dJ Dk DL dM dN DW dX Ef EM eP Et EW Fp Fr Gd gV Hq Hw Hx Ih Ii II Im Io Is It Jh Ji Jk Jn Jo Jp Jq Jt Lu Ma Mh Mn Ms Mt Mv
Mw Mz Nm Nv Nw Ny Oe Pe Pf Po Qb Qd) aW(Aa aE aF aI AJ aM AP aQ aR aV aX aZ bA bB bC bE Bg bH bI bJ bO bP bR bS bX cA cB cC
cD cE cJ cK cM cN CO CP Cq Ct Cu cW cZ DG DK DL dM Ef cM eP Et Ex fR gV Hr Hw Ih Ii In Io Iq Ir Is Iu Jg Jh Jj Jk Jm Jn Jp Jq Jr Js Lu
Lw Lz Mb Mc Md Mi Mk Mm Mr Ms Mt Mu Mv Mw Mz Na Nb Nd Ne Nh Ni Nj Nk Nn No Nq Ns Nt Nv Oe Og Oh Oi Om Oy Pc Pd Pe Pg
Po Qb Qe) bM(Aa Af aK An aV Aw aY aZ bA bB bC bF bN BO bP bQ bS cA cB cD cN cP cQ cT cV cW cY dA dB Dc De dI dJ dK dW Ef Et
EW fP fR Hu Hv Hw Ii Ij Ik Im Io Ip Is Iv Jk Jr Lj Lu Lv Lw Ly Me MI Mn Mp My Nh Ni Nk Nn No Ns Nu Nv Nw Nx Of Oh Ok
On Pd Pf Pg Qa Qb Qc Qe) Nh(aD aE AF aG al aL AR As aV bB bI Bn Bo bQ bR bU bZ cB cC cF cG CH cL cO CP cR cS dA dB dE dH DI
Dk dM Em fR gV Hq Hu Hv IIw Hx Ih II Im Io It Jh Ji Jl Jn Js Lh Lj Lw Ly Ma Mf Mh MI Mn Mp Mr Mw My Mz Nc Ne Nk NI Nv Ny Of Pa
Pe Pg Po Qc) Ok(aD Af aG Ao As Ax bL Bn Bo bP cB cC cD cN cP Cs Cx dB dD Di dM dN Fp fR GI gV Hr Hu Ih II It Jj Jl Jm Jo Jt Lj Ma Mj
Ml Mn Mq Mr Mw Mx My No Nr Nv Ny Oz Pg Po Qb Qd) bB(aP Aw aZ Bo cl cN cP Ef Fp Hq Hv Hx Im Iq Ir Is It Iu Iv Jl Jn Jp Jq Jr Li Lu
Ma Mb Mg Mh Mp Mt Mu Nc Nd Ne Nj Nk NI Nn Nr Nu Ny Of Og Oy Oz Pa Pb Pc Qc) bP(bE Bo Cw cY Et Hq Hr Hx Im Io Iq Ir Jg Jh Ji Jn
Jq Lj Lw Me Mf Mg Mj Mm Mn Mq Mr Mt Mx Mz Na Ne Nj Nk Nm Nn Nr Nx Oh Om Oz Pa Pb Pc Pd Pe Pf Pg Po Qb) Nu(aD Aj aP aR aS
Ax aY bA bI bL Bo bR cK Cq cT cW dM dN eM eP Ex In Ir Iu Jj Jn Jp Lj Lv Ly Me MI Mn Nb Nc Ne Nf Ni Nl Nw Oh Oz Pc Po) Nw(Aa Af
aG aL aM Ax bA Bn bR cB cC cD cF cL cN Cs cW dD dM dN Dw fP Hq Hu Hv Hx Ik II Im It JI Li Mj Mp Mq Mr Mx Nr Ny Pa Pc Qb Qd) Bo(Af
aM aX Bn bR bW Ch Co Cp CX dB Dd Dc DK DI Ef fP FR Hu II Im It Jl Jn Jq Lj Mq Mr Nr Nv Ny Pa Pc Po Pz Qd) cB(aJ aM Aw aY cH cN
cW dJ dM Ef fR Hv Hx II Jj JI Jo Jp Jq Jr Mb Mn Mr Nc Ne Nl No Nx Oy Pa Pb Pc Pd Pf Pz Qa Qb Qd) Mn(aD Af aJ Ar Aw aY aZ bG Bn Cs
cW Cx dB Fp Iv JI Jq Li Lj Mr Mt NI No Nt On Oy Pe Pf Pz Qa) bR(aP dB dG Hq Hx Im Iv Ji Jj Jp Lh Mt Nj Nm Nn Nr Nt Nv Om On Pa Pc
Pf Po Qa Qd Qe) Jn(aJ aM bA hJ cT cW dL dM dW Et Ex fR Fw GI gV Hv Ji Jj Ly Mt NJ NI No Nt) Et(Af aJ Bn cN Cx fR Hu II It JI Jo
Mq Mw My Nd Nr Nv Oz Pa Pf Po) Jj(Ad aM cC Co Cp Cq cX Dk DI Hq Hw Im Ip Jq Nn Nr Nv Oi Om On) Ne(aD aM bW cC Ch cS Cx dB
De DK DI Hw Is Jh Jq Ny On Po) Hv(Ap Bg Cu cW dB Dg DI Is Ji Jq Lh Mt Nm Nn Oh On Pg Pz) aM(Af An Aw cY De Ef eW fR Jg Jh Ji Mt
Nd NI Ns Pa Pf) Pa(aQ aR aS aV aY bJ cV dW Ef fP GI Hr Lj Mr Nd) aD(bQ Cu Ex Fw GI Iv Jq Js Lh Mt Nd On Pe Pf Pz) fR(Ih Ii Is Jh Ji Jq
Mf Mg Mz Nj Nm Om Oy Pd) Nl(bU bW Ch Co Cp Cx dB Hw Is Jq Nk Nv Po) Ly(Af Ih Jq Mt Mw Nr Nv Ny Pe Pg Qb) Il(Ad Ap Ch Co Cv
DI Iv Jl Jp Oh On) al(Ih Jh Jl Jo Mh Mp Mw Nv Pe Po Qd) cC(aY cW Jp Lh Nd Nx Oz Pb Pc Pf Pz) Ji(Aa Cs dB dM Hu Mp Nd Oz Po) Ef(AJ
bJ Io Mm Mp My Ng) Mt(bO cH cI dM Hx Iu Jo Mh) Lj(Is Lw Mp On Pg Pz Qd) dB(cP Hx JI Mz No Nx Qa) On(Cs cW Fp GI Jr Nd) Is(aR Cs
dM Nc Nj) Jl(bF Di Jp Lh Oh) Pe(aS cT gV Hw Lw) Cx(Jp Mb Nc Nj) Lv(Af Bn Cp Dc) Qd(aS Ax Cs cW) Jq(Aj bA dM Nd) Po(bJ cV eW)
Mh(Ex Fw GI) Ny(bA cW In) Nj(cR cX) Qb(aS cV) Jp(Bn It) aV(cN dM) cW(bU Im) dG(aO Dk) DIOg ExMy GlPg NrMz NtbW MacG MbdK
NcNk JoLh NvaS PfcP aKdM} jD{Wh(aA Et Fr hA Hq Hr Hu Hv Hw Hx iB iC Ih Ii Ij Ik Il Im In Io Ip Iq Ir Is It Iu Iv jE jF JG jH JI Jj JK JL
JM Jn Jo JP jQ JR Js JT jU jV jY Lh Li Lj IK !L IM IN IO Lu Lv Lw Lx Ly Lz Ma Mb Mc Md Me Mf Mg Mh Mi Mj Mk Ml Mm Mn Mp Mq
Mr Ms Mt Mu Mv Mw Mx My Mz Na Nb Nc Nd Ne Nf Ng Nh Ni Nj Nk NI Nm Nn No Nq Nr Ns Nt Nu Nv Nw Nx Ny Oe Of Og Oh Oi Ok
Om On Oy Oz Pa Pb Pc Pd Pe Pf Pg Po Pz Qb Qc Qd Qe Tz Ua Ub Uc Ud Ue Wc Wd We Wf Wg Wm) Zq(Et Fr hA Hq Hr Hu Hv Hw Hx
iB iC Ih Ij Ik Il Im In Io Ip Iq Ir Is It Iu Iv jE jF JG JH JI Jj JK JL JM Jn JO JP Jq JR Js JT jU jV jY Lh Li Lj IK IL IM IN IO Lu Lv Lw Lx Ly Lz
Ma Mb Mc Md Mf Mg Mh Mi Mj Mk Mm Mn Mp Mq Mr Ms Mt Mu Mv Mw Mx My Mz Na Nb Nc Nd Ne Nf Ng Ni Nj Nk NI Nm Nn No Nq
Nr Ns Nt Nv Nw Nx Ny Oe Of Og Oh Oi Ok Om On Oy Oz Pa Pb Pc Pd Pe Pf Pg Po Vz Wb Yd Yl Zw Zx Ye Tm Tl Xa) Ye(hA Hu Hx iC Ij Ik
Il In Io Iq Ir Is Iu Iv jF JG Ji Jj jK JL Jm Jn JO jP jQ jR jY Lh Li IN IO Lu Lv Lw Lx Ly Lz Ma Mc Md Me Mf Mg Mi Mj Mk MI Mm Mp Mq
Ms Mt Mu Mw Mx My Mz Na Nb Nc Nd Ne Ng Nh Ni Nj Nk Nl Nn No Nq Nr Ns Nt Nu Nv Nw Ny Oe Of Og Oh Oi Ok Oy Pa Pd Po Wb Yl
Zw Zx Tm Tl) Pj(Db eZ hL hO pY qB qC qD qG qH ql qO qZ rN rQ rR rS rT rV rW sC sK sM tN tO tQ rT tU tV tX uG ul uL uM uN uO uP
uR uU uW uX uZ vA vB vC vH vI vO vQ vS vT vU vV vW wC wD wG wP wQ yH yJ yK yL zA zG zH zI yE tL xA) kC(aC aE Af aH aI aJ aK
aN AO aQ aR As aV aX hI bL hO bP bR bS cA cB cD cF Ch cJ cK cM Co CP cS cU CX cY cZ dA Dc Dd dE dG Di dK DI dR cE eF hB hC hF
hG iP kR nY oE oF oH oN Ut) ml(Ad aF Aj An Ao aQ Ar AS aV aW AX aZ Ba bC bF Bg bJ bL bN bW cF cJ Co Cp cS Ct CW Cx dB Dc De
dF DG eC hB hG iJ iZ kQ nW oF pF Ub Ue) Gd(Ad Al aO Bb bE bG bM bN bS bU cA cD cJ CP Cx cY dA Dc DE dI dJ Fy Ir Iu Iz jF Jg jM Jn

Figure 4 Continued jR Jv Kc Ki Ks lN Mb Mf Mk Mr Mu Qc Rc Ss Uk) Zx(Hv Hx iC Ih Ii Ik In Io Iq Ir jF jK jL JM Jn Jp JQ JR jT jU jY Lj lO Mh Mk Mp Mr Mt Mu Mv Mz Nc Nd Nh Nj Nk Nl No Oi Oz Pd Pg Yd) Zw(Ih Ij Ik Im Ip Iq Is Iu Jg Jj JL Jn Jp JQ jR jU lK lM lO Mf Mh Mk Mn Mr Mu Mv Mw Nc Nd Ne Nh Nj Nl Nn Nq Nr Nu Oh Oi Pd Yd Tl) Wb(aA Hq Hr Hu iC Ih Ii Ik In Io Iq Ir jF Jg Jn Jp JQ jR jT lO Mf Mg Mh Mk Mp Mr Mu Mv Nc Nd Ni Nj Nk Nl Of Oh Oi Oz Pd Pf Pg Xa) Tl(aA Et Hu Ih Ii Jg Jk JL Jp JQ jR Jt jU lK lO Mb Me Mh Mk Ml Mp Ms Mu Mv Nc Nd Nh Ni Nj Nl Nv Nw Oi Om On Oy Pa Pd Yd) Wf(aA iC Ih Ik In Iq jF Ji Jk Jl jM Jn Jp JQ jR lK lN lO Ma Mh Mk Ml Mp Mr Ms Mt Mv Nc Nd Ni Nj Nl Nw Pa Qc Tz) Uy(aA hA iB iC jG jH jL jO jP jQ jR jT jU jV jY lK lL lM lN lO Uf Ug Uh Uk Um Us Uu Uv Uw Vb Vc Vj Vo Vq Vs Ti Th) Yd(aA Ih Ik Ip Iq Iu Jg Ji Jk Jl Jn Jp JQ jR lK lO Me Mf Mh Mk Ml Mn Mp Mu Nc Nd Ni Nj Nl Nn Oh Oi Om Pd) Uw(aA hA iB iC jE jG jL jM jO jQ jT jU jY lL lM lN Uf Ug Uh Ul Un Uo Up Ur Uu Ux Uz Va Vb Vc Vh Vp Vs Ti Th) Vc(hA iB jF jL jM jP jQ jR jT jU jV lK lL Uf Ug Uh Uk Un Uo Up Ur Ut Uu Ux Vb Vi Vq Vs Vw Th) Wc(Ih Ii Ik In Ip Iq jF jK JQ Mh Mk Mp Mr Mt Mu Mv Nd Nh Ni Nj Nk Nl Pd Po Qc Tz Ub) Tm(aA iC Ih Ii Ik In Iq jF Jg jL Jp Jq jR Mh Mk Mp Mr Mt Mu Mv Nc Ni Nj Nl Nr Oi Om) Yl(iC Ih In Iq Ir jF Jg Ji jK Jp JQ jR lO Me Mk Mp Mr Mt Mu Mv Nc Ni Nj Nk Nl Oi) cW(kE kF kI kK kO lW lX mF mH mM mP mS mT mY nA nC nD nF nH nI nJ nK nL nR nT nU) Wd(aA iC Ih In Io Iq Jg jL jM Jp JQ jR jY Mh Mk Mp Mv Nc Ni Nl Nq On Pd Tz) We(Ih Ij Iq Ji jM Jp Jq lM Mf Mk Mp Mr Mt Mu Mv Nc Nd Nj Nl Nr Nu Pd Po Pz Tz) bH(kI kK kN lY mE mF mH mM mP mS mT mU mW mY nA nB nC nD nF nK nL nO nR nT nU) Wg(aA Ih Ii In Iq Jg Ji Jp JQ jR lO Mh Mk Mu Nc Nl Nx Oi Om Pd Pg Qc Tz) Xa(aA Hv Ih Ik Ir Is jE jF jK JL Jp JQ Jr Js Mk Mu Nd Ni Nk Nl Nq Oi) nL(aK Ba bB bC bL Bn Bo bW CH Cq cR cY DB dF Di dR gL hG kS Tz Ue Vu) Vz(aA iC Ih Iq Jg jL JQ jR lO Mf Mh Mk Mu Nc Nd Ni Nj Nl Nn Nr Nu Oi) nC(aP aW aY aZ Bc bF bL bP bQ bW cC cN cP dB dE dF dG hB hG nW Tz) bL(kF kI kN kO kP lW lX mE mF mP mS nA nF nH nJ nK nT nU) Tz(fR kF kG kK kN kO lW lX lY mY nF nI nO nR nT nU) Va(aA iC jH jI jL jQ jR jT lM lO Ug Uk Ur Ut Vh) Vu(kE kI kK kO lX mH mM mY nF nI nO nU) lX(Co Db dM eF gL hG iP iZ nY oH oN) kF(aZ Bo cM cT Di gW iJ Uh Us Uu Vt) Vb(jM jQ jR lM lN lO Ug Uk Um Vq) Bo(kG kK kN kP lW mF mS mY nB) Vi(iC jQ jR lN Ug Uh Uk Un Vs) Ux(jQ lM lN Ug Uk Un Vt Th) Vj(aA iC jQ lM lO Ug Uk Vs) fR(Aw Bc Di dR Jg lK Ms Qg) Vh(jE jG jM jR Ul Ur Vs) Vw(jL jM jR lM lN Ug Vs) nI(Ba Ch hB hC hG iZ nW) Di(kG kN kP lW mF mY) zH(Bb Ic It Mz Nw Vt) Db(kP mF mS nF nO) Bb(tV uL uM vS) Ip(hL Ic qC tV) Vt(tV zA tL xA) Vo(lW lY mM nT) Co(lY mY nO) Ex(Ad hO Jg) Um(kK kN Uz) Vq(qU wL yL) kP(aQ dR tF) vS(Et Ic Lh) Gz(Ad hO) Uz(jR lN) dB(mW nH) nT(Ba gL) mF(aQ Ue) mS(Ch cT) kE(dG nW) kK(Uv tF) pF(nA nH) MzqC IttV UnnO aNmM cImW nKhG} gW{ Ye(Ad aE aH aI Aj aM AP aQ AR AS aV Ax bA Bb bE BG bJ bL bO bP bS bX cA cB cE cG cN Co cQ cS CT cW Cx cZ DC dD De dF dG DI DL dM dN Ed eF Et Fc Fr Fy Gb Gd gL hF Hp Hq Hu Hx Ih Ik Im In IO iP It Iu Iv Iz Je Jg Jl Jn Js Jt Jv Jy Ke Kg Kk Kn kR kS Kx Ky Kz Lh Li Lj Lw Lx Ma Me Mg Mj Mm Mp Mq Mr Mu Mv Mw Mx My Nb Nd Ni Nn Nr Nt Nu Nv Nw Nx Ny Oa Oe OH Ok Or Ou Ow pF Pj Ql Qn Rx Sh Si Yd Zx Tm) kF(aC aD aE aJ aN aP aS aV aZ bE BG bL bR bV bZ cC cF cG cH cI cK cL cN cO Cq cR cS cT Cu cV cW dB DC Dd dE dF dG dH DI dK dL dM eF Fr gL hA hB hG iA iB iO iZ jE jF jG jH jK jL jM jO jP jR jT jU jV jY kG kI kK kO kP kS lL lM lX lY mE mH mI mM nA nB nC nH nJ nL nO nR nT nU oF oN qT qV qX rA tF) Gb(aC Ad aH aJ aL Ao aP aU BA Bc bJ bZ cE CH cL Ct dB Dc dH dJ Et Fd Fr gL Ha Hb Hc Hf Hp Il Im It IZ Je Jf Jh Jl Jr Ju Kl Kr Li Lj Lu Lv Lw Lx Me Mh Mr Mt Mu Mv My Na Nc Nr Nt Nu nY Oa OE Oi Or Oz Pe PF Pg Rx Rz Sf Sh Zq Zw Tl) lX(aJ Al AR aZ Ba Bc bF bG Bo bQ bU cA cE cG Ch cK cL cN cS Ct cW DB dF dH Di dM gL hB hG iB iP jF jI jO kC kN kP lO mE mH mI mM oK oN pF qT qX) kP(aD Af aK aP aQ aV aW aX bB bE bG bH bI bM Bo cB Ch cI cK cM cO cQ Cs Cv dB dH Di dR iC iJ iZ jE jG jO jR kC kS nD nF nH nK nU oE qT qU qV qX) cW(kC kE kG kI kK kO Lp lW mE mF mI mM mP mS mT mZ nC nF nH nI nK nL nM nO Sf Sh Yd Xa) nC(aW aZ bL bW cB cC cD cF cY dA dB dG dL dN gL hG iC iZ jQ jR mS nB nD nH nK nW oK) Tl(aJ Ba Bb Co Cs Dl Ez Ha Hc Hx Ih Ik iP iZ Jh Kl Kp Ky Lp Mh Mt Mw Ng Nn No Qm) Iz(Em Fc Fi Hl Ho Hp Lp Lt Op Rx Ry Rz Sf Sh Si Sj Vz Wb Yd Yl Zq Zw Zx Tm Xa) kC(aH aL aM bE bW cH cI Cu cX cY cZ dC dE Di dL eD gP hG iJ jM jV lM mS oH pF) Zq(aA Ad bZ Cp cQ dB dH gL Hb Hc Hu iZ Jg Jt Kc Kl Kz Nf Ng oK On Oy Pb tF) bH(kE kI kK kN kO lW lY mE mF mI mM mP mY mZ nB nD nF nJ nL nM nO nR nT nU) nL(aL aW aZ Bo bW cF cI Cu dB dG dL gL hG iJ iZ jF jR mS oF qT) On(Fc Fi Hl Ho Hp Lt Rx Ry Rz Sf Sh Si Vz Wb Yd zH Zx Tm Xa) Bg(Dr Fi Gc Gn Ho Hp Lp Lt mS Op Rx Sf Si Sj Vz Wb Yl Zx) Kl(Fc Ho Lp Lt Rx Ry Rz Sf Sh Si Sj Vz Wb Yd Yl Zw Zx Tm) Jg(Fc Fd Fi Ho Lp Lt Op Rx Sf Sh Si Sj Vz Yd Yl Zx Tm) Bo(kG kK lW lY mE mF mH mI mM mY nF nI nJ nO nT nU) Di(kE kN kO lW lY mE mH mM mS nF nJ nM nO nR nT nU) Hp(Ad Aj Co Dl Hc Hf Ib Ik iZ Jd Jt Kf Mg No Po Qm) Rz(Ad Aj Ba Co Dk Dl Hc Hu iZ Jh Jt Kj Lv Ng Oy Pb) zH(Bb Et Ii Jp Kf Kg Kq Mz Nm Nw Ok Pa Pj Ri Um Vt) Oy(Fc Fd Hl Ho Lp Rx Ry Sf Sh Si Sj Vz Yd Zw Xa) dL(kG kN lW lY mE mF mH mI mS mU mY nH nI nJ nU) Si(aA Aj cF dB Dl gL iZ Jr Jt Ke Kf nY Pb) mS(aF AO Ba bF Db gL hC jI kG lM lN) Ho(cR cX dE Dl gL Hc iZ Jt Kf Oz Pc) Sj(Ba Co Ct Dl Hu Ib Je Ke Mz Ng Qm) Tm(Ba Co Ct Dk Dl Hu Jp Jt Ng No Po) Rx(Aj Ba Dl Je Jr Jt Kc Kf Ng Nv Qm) oK(kI kN lW mF mH mM mU mY nA nH nU) Fd(Ad Aj Ba Ch Dl Hf Ik Kf Mg Qm) Sh(Aj Ct Hc Hu Ii iZ Jr Jt Ke Ng) Zx(dE Dl Hu iZ Jd Jr Jt Ng Pa Pf) Xa(Ad cB cF Dg Dl Hc Mg Mt Ng Qm) Ry(Bc Ct Dg Hc Hu Ib Ik Kf Kj Ng) kK(aM bW cI cS dB jR lN nF pF tF) Pj(hO tQ tT tV uU wD wJ yL tL) Em(aJ Hc Jd Ke Kf Kj Qt Rc) Fi(Aj Co Dk Ke Kf Ng Nv Qm) Sf(Bc gL Hc Hu iZ Jr Jt Pb) Zw(Aj cF dE Hc Kf Lv Pa Qm) Lp(Aj Hf Jr Jt Kf Kj Mg Nf) Yl(Aj Ba Co Dk Dl Ik Jr Kf) cI(mP mT mU mY nA nH nI nK) cS(kN mF mI mM mW mY mZ nI) jR(mH mI mM mY nA nI nK nR) iZ(Gd mE nF nT nU Op Yd) kN(bW cZ dC gP iJ kS lN) Hl(Ad Aj dE Ik Jt Kj) Vz(Ad Ba Co Dk Im Jt) Fc(Aj Dl Kf Kj Kp) Yd(aA gL Jd Jr Kf) bW(lW mF mH mI nA) Gd(Jd Je nY Tn) Wb(Jt Ke Ng Pb) Lt(Jr Jt Ke Ng) Vq(uM wL yL tL) aJ(dX eM eP mE) dG(nB nH nJ nT) qT(fR nH nJ nU) Bb(tV wH yH) Db(kE mY nR) Gc(Ad Dl Ef) aZ(kI mI mT) mF(bC dN lN) mM(aM aQ iJ) nF(aW Ch hC) sJ(rS rT Tr) Et(vS tL) Mz(qC tV) dB(nO nR) mY(cB lN) nD(bL mI) sF(rS rT) sH(rS rT) jF(nI nK) AdOp ConU ExhO aDlY aNfR aPnT bMeM gLnB nAiJ nHnJ hGkI} kC{jM(aC Ad aE aF aH aI aJ aK AN aO AP AR AS aU aV aW aX aZ bA BB Bc bE bF bH bI bJ BN BO bQ bR bS bU bV bX bZ cA cB cC cD cE cF cG cH cJ cK cL cM cN Co CP CQ cR cT CU cV cW CX cY dA Dc DD dE dF dG dH DI dK DI dM dN eC eF fP gL hB hF hG iA iJ iO iP iZ kQ kR kS nW nY oH oK oN Vu) jE(aC Ad AF aG aI aK aN AO AP aQ Ar AS aU aV aW AX aZ bA BB BC bH bI bL Bn bO bQ bR bS bU bZ cA cB cD cE cG CH cK cM cN cO CP CQ cR Cs cT CU CV CW CX cZ dA Db DC DD DE dF DG dH dI dJ DK DL dM dN dR eF gL hB hC hF iA iZ kR kS Nr nW nY oE oF Ue Uh Ut Vu) jY(Aa aC Ad aE AF aG aI AO aP aR AS aV AW aX aZ bA BB Bc bE bF bH bI bL bO bQ bR bS bV bX bZ cA cB cD cE cF cG cH cK cL cN cO cP CQ cR Cs cT Cu cV cX cZ Db DC DD dE dF dH dI dJ DK dL dN dR eC fP gL gP hF hG iA iJ iP iZ kQ kR kS Nr nW oE oF oN pF Vu) iC(Aa aC aF aG aH aJ Al aM aO aP aR aS aU aV AW aX aY BA bC bE bF BG bH bI bN bP bQ bR bS bU bW cA cE cG cJ cK cL cM cP CQ cR cS cT cU Cx cY dA dC DD dH dI dK dL dM dN eC fP gL gP hC hF hG iA iO iZ kQ kR kS nW oE oH oK oN pF Uc Us tF) jF(Ad aE Af aG aI Aj aK AL aN aO aQ AR AS aV Aw Ax aY bA BB BC bF Bg bH bI bJ bL Bn bO bR bV bW cB cD cE cF CH cK cM cN cO CP Cq cR Cs CT Cv CW cY cZ dA dB Dc dD DE dH dJ dK Dl dM dR eC gL hC hG iO iP kQ kS nW nY oE oF) qU(Aa aE AF aI aK AO aP aQ Ar aV aW bA Bb bC bE bF bG bH bL bN bQ bR bU bV bW bX bZ cB cD cH cL cO Cq cR Cs cT Cu cX dA DC Dd dE dJ Dk DL dN dR eC eF hG iO iZ kR nW oE oF oH oN pF tF) lK(aE Aj aO As Aw aY Ba Bb Bc Bg bH bS bW bZ cA cC cD cF CH cI cJ Co Cp Cq Ct Cu CW DB dC dD De Dg Dl dJ Dl dR gP hC iA iJ iO kR oF oK pF tF) qT(Aa Ad Af Al Ao aP Ar aW Ba bE BG bH bJ bL bM Bo cB cF cH cI cJ cT Cu cW cX cZ Db DC Dd dE Dk dN eC iA iJ iZ kS oF oH oK) qV(aC Ad aH aI aJ aN aO aR aW aY bA bE BG bH Bn bP bW cB cF cH cJ Cp Cq CT Cu Cv cZ Dc dD

Figure 4 Continued oP pI) nI(Dr Du Eq Fc Fd Fi Gb Gc Gh Ho Hp Lp Lt Op Ps Ru Rv Rx Sf Sh Si Ux Uz Vc Vh Vi Vj Vw Yf) mZ(Du Eq Fc Fd Fi Gb Gc Gh Ho
Hp Lt Op Ps Rt Ru Rv Rx Rz Sf Sh Sj Uz Vc Vh Vi Vj Yf) Hp(dU jB kE kG kK kN kP lW lY mE mH mM mP mS mT mU nB nD nF nH nK
nM nO nR nT) Tl(dR eC fB gL hB hF hG iA iJ iO iP iZ kQ kR kS nW nY oE oH oK oN) Si(fA jB kG kK kN kP lY mE ml mM mP mS mT nH
nO) Vb(jB kE kG kK kN lW lY mH mM mP mS nO) Uy(dU kK kN lW lY mF mH mP mS mT nO) lW(Du Eq Fi Gc Gh Lt Rv Vj Yf) Tm(eQ
fA gZ oV oW pI pK) Du(kK nH nR nU pH pI) mH(Gb Ps Rt Sf Va Yf) Gc(kK nR oO pI pK) Yi(dU eQ fA gZ oT) Yg(dU fB gZ) Rt(lY mS mY)
fA(Gh Sf We) Yj(oK pH) Sh(kS nU) Sj(lY nR) Wh(pH pI) Ps(mS nO) GheQ SfmS WfeC RznU RukS YlpI UxmM VhnR VjlY fRjO nKjE} iC{dB(kE kG kK kN kO kP lW mE mF mI mP mS mT mU mW mY mZ nA nB nF nI nK nM nR nT nU) iJ(kE kG kK kN kO kP mE mH mM mP mS mT mW mZ nA nH nI nR nT nU) aZ(kG kK kO kP lW lY mT mU mY mZ nD nF nM nO nR nT nU) cC(kE kI kK kN kP mE mH mI mM mS nA nF nH nI nR nU) Db(kG kI kK kN lY mH mS nF nI nR nT) dC(kG kN lY mE mM mP mW mY nI nK nR) dR(kE kN kP lW mF mM mY nA nI nU) nU(Ar Bc bF bL bN cJ dE Vu) mH(aK aQ aU aW Bc bJ cY Ue) kP(aK aN aQ aU Ch Ub tF) nO(Bc bF bL dE Us Vu) nT(Bc bI Ch dE gL oK) mT(bI bL cX dA Mh nW) nI(aW bF cH Dc hC Us) fR(fP hB iA oH tF) mM(Bc bF bN cI Us) nH(aE aN bL cI dE) Wf(Mf Mk Oe Tz) aW(kI mF mI nK) mW(bN cI cS kS) kE(Bc bN cJ Us) Ch(kG kO nB) Wh(Im Jn jO) Ky(sF sH sI) Ug(Va Vb Vh) mS(hC nY Vo) mY(cT cV hG) nA(aE bF hG) kK(Us Uv tF) lM(Wd We Zw) Mk(Wd We) Tz(Wc Wg) Ye(Ji Lv) Va(aA jI) Vs(Vb Vj) aQ(kI lW) lY(Ub Vo) mI(aE Aj) nK(cI Na) kO(Bc dE) AdGz TinY GdSs HxZx IpsF WcPc WnzG UmkN VhjG VwjO bXkI dKkG} Wh{jT(aA Fr hA Hv Hx Ii Ik Io Iq Jj jK Jl jM JO jV Lh Li lL lM lN Lu Lx Ma Mg Mj Mk Mq Ms Mu Mx Nl Nm Nq Nr Nx Oe Of Oh Oi Oy Pd Pe Pf Pg Qd Ub Ue Wf) jL(aA Et Hx iB Ik Im Is Iv Ji jQ Js Lj Ly Ma Mk Mm Mu Mv My Nd Ni Nj Nm Of Og Ok Pb Pg Pz Qa Tz We Wm) jO(hA iB Ik Ji Lh Ly Mf Mk Ml Mp Ne Nl Og Oy Pa Pb Qa Qb Tz Wm) lM(Hv Ii Ik Iq Iv Jg Jr Lu Ly Mk Mv My Ne Ng Nl Ny Qa Qb Tz) hA(Hx Ik Io Iv jG Jh Lu Mh Mk Mm My Nf Nk Nl Nq Oe Po Tz) qX(Ip Is It Js Mf Nf Nk Pc qV Ua) mZ(aL bB Em Gp hC Hr Qv Um Wd) Tz(jE jI jM jP jV lN lO) eM(Aa hC Ib Ko Ks Oi) mF(bB cU Hr mH Qv Yj) rA(Hx Ip Iq Jo Mf Wf) qW(Hx Ip It Mf Mz Nk) jQ(Ik In Mk Pd Wc Wm) jY(Hx Iv Lu Mk Nc Ne) Gp(hC lY nD nI oO) Mk(jK lL lO) bW(dU eC hC) qV(Hx Mf Nj) Iz(eC gP) Uy(jB kO) bB(lW mY) mH(eQ nA) qU(Hx Ik) lL(Nk Qd) ThnI NjiB YekO KogP OgjU cXeC lYnA mShC} Gz{hO(Ap Aw Bg Ch Cp Ct Cu Cw Dk Dl Ef Et Fr Hb Hc hG Ii Iz Je Jg Jh Jt Kl Li Mg Mw Ng Of Ok On Oy Rb Ss Tn Tr Tt Tz Ua Uc Uf) Ad(eD eT eZ fN hA hP hR iB jE jK jL jM jO jQ jU jV jY lL lM lN pY qB qC qD qW qX rP rR rW rX tT uM uV uZ vB wP wQ yH xA) Bc(hA jO rN rX rY sC sM sO tN tQ uN vB vP wB wC wD wF wG wH wK wL wP wQ yD yL zH) Tt(qG qH qI qZ rN rO rP rR rV tQ tS uG uI uL vH vQ vS vU vW wC wH wK yH zG) On(hL sC tO tR tS tT tV tX uL uM uO uZ vB vH vP vV xA) Jg(eD hA hL jY lL qI rX tV uM uZ xA) Tr(qI tU uI uL uN uO vB wD) tV(Aw cI Dg Dk Dl Jt Mm sC) xA(Dl eF Ez gL iJ kQ Lh To) Jp(gV tS vP vV yD zG zI) To(uI uZ vW wC zA) hL(Cu Cw Dl Jh) yH(Et Kq qW zH) eD(Cp hG Jh) gV(Mn Ok Pa) tQ(Dk Dl Ng) sC(Hb rN sO) Et(uL vB) Tn(qI rV) Ss(uM zI) Lh(vV yD) rN(Vs wH) AwqX CpuM CwuZ DltT JhhA QvuN cIyD sOnY} jQ{kP(aD Af aJ aK aN aP aQ aY aZ bG bM bO bS bU bW bZ cA Ch cK cZ dA dB Dc dG dI dK dM dR hG iJ iO iP iZ kQ nW nY oE oK tF) kN(aC Af aW bC bG bW cI Cp Cx cZ dA dB dC gL gP hG kS oK pF Um Us Ut Vo) Db(kE kG kI lW lY mE mF mI mM mS nM nO nT nU) nH(aJ aN aW aZ bZ cH cI dB dM iZ oK) gL(lW mE mF mM mP mT nD nF nR nT) mH(Af aW aZ bN bW cB cK Dc De) cI(mI mP mT mU mZ nA nD nK) fR(Ad aO cM Dl eD hB Ms oF) dB(kI mF mI mM nA nK nR) iZ(kG kO mS nD nF nO nU) oK(lW lY mF mM mU nA nU) dM(kG kO nO nT nU) mF(aC aZ cZ dA oH) kK(cZ iJ Um Uv tF) Va(aA jI Uw Vs) Vu(kO nO nT nU) aJ(kO nO nT nU) aW(kI mI mW nR) lW(bE cB oH Uv) Ik(Yl Zx Tl) aZ(kI mI mT) mS(hG oH Vo) nY(mW nD nF) Zx(Hx Mk) Wf(Et Qb) Vs(Vc Vw) mU(aC dA) nA(bG bW) zH(Mz Wn) kI(cB cZ) ConU MhYd IunK ZwlM WcaA WeJr UsnI UwjL VhjG aNmP bLnO cSmW mMiJ mYoN} Uy{dU(An Ao Ba bB Bg bI bW cH cI cM Co Cq cU Cv Cw dB De fA Fy gZ Hc Hq Hu Hv Ib Ij Il Ip Iq Is Je Ko Ky Li Ma Mw My Na Ng Nl Nn Nq Nx Oh Ok Om On Ow Pe Ph Qm Qu Rv Rx Rz Sh St Tn Tv Ua Ue Uf Up Uu Ux Va Vs Wd We Yg Yi) Iz(dR eC eF gP hC hG iJ iP jB kQ lY mE mF mM nA nK nT nW nY oE oH oK oN tF) jB(An Ao Ba cG cH Cq Cv De Fy Hq Il Kl Ky Li Mv Nq Nv On Qz Rz Ss Up) Cq(eQ gZ lW lY mP mU mZ nB nD nI oO oQ) Uf(fA gZ lW mZ oO oV oW pH pI pK qX) Nq(fA gZ mP oO oP oQ oW pI pK) Ao(eQ fA lW mP mU oQ pH) cG(eQ fA gZ mF mZ nI oV) eM(Ef Ib Ng Om Vs) mP(cH It Rz Vw) eQ(Gh Mn Ph) lW(Co Jn Rz) nI(Gp Mw Om) pH(bB Jn Ko) Li(gZ oW) Ug(jI lM) Ut(jG jO) Vs(jY qW) aZ(fB mU) mZ(Om Tn) hB(lY mH) EfiJ FyoO ItoQ KooV UnhA VajI VwlM PhfA bBpK} jE{nK(Hq Hu Hw Ik Im In Io Ip Iq Ir Is Iu Jg Jj Jn Li Lu Lx Me Mj Mn Mp Mt Mu Mw Mx Mz Na Nd Ne Nf Nh Ni Nj Nk Nl Nr Nt Nv Nw Nx Ny Oe Oh Oi On Oy Oz Pa Pb Pc pF Pg Po Qb) nH(aO aQ aU aV bB bC bF bP bS bW cA cE cG cH cJ cL cR cY dB dC dR kS nY pF) hG(kG kI kK kN kP lW lY mE mH mI mM mP mT mU mY nI nO nR nT nU) bL(kE kG kI lW lY mE mF mI mP mS nA nB nM nO nR nT nU) mI(aW aZ bW cF cJ cS Ct dC iZ Ub) mM(cJ DB iJ kS Ur Us Vp tF) kP(aQ aV Ba cT DB dR Uv tF) nR(aQ cB Ch cT dB dE Uv) kK(DB Um Us Uv Vu tF) Tz(Wc Wd We Wg) Vu(kG kO mY nO) Ch(kO mY nF) Ik(Wc Yd Ye) Va(jI Uw Vs) mE(cS Us Uv) nI(Nj Nk Pg) Db(mS mY) Wd(Mk Wm) Ye(Ji Nd) Vo(lY nT) bF(mF mS) fR(Bc Ri) mW(aW nY) kN(aZ Um) UbkG IiWc WntM UxlM cGnT dBkO dEmZ nDnY} Tl{Mv(dU eC eF eQ gL gP hB hC hF hG iJ iP iZ jB kR mE nW nY oE oF oK oT oW pF pK tF) eQ(Aa Ax bB cR Cs cV Dd Gh Jn Jp Ko Li Lj mH mY Nq Qh Uf Um Ur Th) hB(cU dH Io kK KO kP lY mE mS mY nB nK nO nT oQ Pi) mF(aD bB Cw gL Ib Ih Iq jB Om Rz Tn Uf) Ko(dU gZ iP iZ jB oT oV oW pH pK tF) Ik(hA jI jK jM jO jP jT jV lM lN) Li(dU gZ iP jB oK oV pH pI tF) Mw(dU iJ kK mE nI nR oW) nA(aD aH bB cE Ih Jl mH) cR(fA gZ lW mM mP mU) Nq(mE oP oV pH pI) Oi(eM oH qV qW qX) bB(dU gZ iZ mE pH) hC(Bn De Ef Iz Qy) Aa(fA gZ oP oT) eC(aA cX De Iz) qW(Hx Mf Nj Nk) Ii(hA jO lM) dU(bW cX Up) qX(Nd Nj Pc) oW(Hr Nk Oz) Cq(mP mZ) Mf(qV rA) Mg(hA lM) Ih(oH oK) Jg(hA lL) Lj(gL pH) Nv(jO lM) jB(Rh Up) NoiJ MkjU NjqV HroT IbcM JhlL JnmE OaoV UfpK UtoK} jY{Nw(pS rU sC sF sI tN tQ tV uG uM uP vA vH vS vT wE yD zH zI yE tM tL) bL(kE kG kI kN kO lW lY mE mF mI mS mT mU mZ nB nF nK nM nO nR nU) Vu(kI kP lW lY mE mF mI mS mY nB nI nM nO nU) Wf(aA Ii Im Jh Ji Mh Mu Nn Nv Om Po Tz) Et(qC qQ rN rO sC tV vH vS wK) mI(aW aZ bW cF cJ cS dC hG) rN(Ad Ap Dg Dl Jt Kf Ri sI) Bc(Gd Hf Ic rW zA zH tL) Wd(Ih Mk Nl Nv Ny Po Qa) Ok(sH sI sK vB vH zH tL) Ji(sC tV vH vS Ye tL) Gd(Iz Je Jg Ss Vs) aA(Ux Va Vc Vj Wc) Db(kK kP mM mS) qC(Dl Lh Mz Un) Ke(vH zH tL) Vs(Va Vb Vc) mS(bF Ch hG) mW(aW aZ dB) nH(bF bS cA) jI(Va Vc Yd) kP(aV cM dR) Po(Wb Ti) Mz(rW tV) Nc(Wc Yl) Jg(fR Ye) Ut(Uz Vj) Vh(jG Vw) Vo(nT Uw) mY(Ch hG) sI(Il jL) kK(Um tF) TiqI MmuG IiWg ImWc LhxA WnvS UntL UgUx UmI VwlM mMkS} lM{Ux(aA iB jG jI jL jT lO Ul Un Up Ut Uv Uw Uz Vp Ti) mS(Ap aQ Ax bA bF bL BN Co Db dC dE dI kR Wm) Zw(aA Hq Hu Ik Jg Ji Jp Mn Nd Ng Nm Nv Nw On) Vw(hA jL jV Uf Ug Uh Um Uw Vj Vo) Wf(aA Iq Jg Jl Jo Mh Mk Tz Wm) Gd(Ad Ba Bg cM Cw dA Iz Tn) Wd(aA Ik Im Jg Mu Nl Pg) aZ(kN mE mF mI mY mZ nB) Db(kE kG kP mI mM nU) Ye(Ii Jg Ji Lh Mt Pd) Va(aA jI jL Ug Uw Vs) Wc(Ii Ji Of Om Uc) We(aA Ik Nv Pd Tz) dB(kE lY mI mW nK) fR(cM Kn Ms Nn Sr) mY(Co cT hG kS tF) kI(aK aQ aV cY dR) Vz(Ii Lh Pd Pg) Wg(Ii Ji Mk Pd) Yl(Ik Jg Mg Nv) Wb(Ii Mg Po) aW(mF mI nH) kS(nO nT nU) Yd(Jg Pd) Um(kK kN) Vi(Uh Vs) nK(Iu Lu) kP(aK dR) TiqQ TznU IkZx JgTm WnwH UnVj UgVb VcaA VunO aQlW bSkE tFkK mWnW} sF{Hf(eD Ky Nf rO rP rU rW rX rY rZ sC sK tN tO tT tV uG uI uL uN uO uP uX uY vC vH vI vU vV vW wE wG wL wQ yD yJ zH zI xA) Tr(Aj aN aX Ch cX Ef fP Ib Ik Iv Iz Jk Jp Lx Mk Ng Nq oF Og Oi Oy Qu Qw rB Us Uu) Ky(hX jG qC rT rX tN tS tT tV uY vB vC vH wC wD wG tM xA) Ib(Ad Ap aR Dg Ip Jg Jv Kl Ma Qt rT Tt Vv) tT(Hx jU Kf Ma Mw Mz Nr Or Oz Pc) tV(Et Hu Hw Hx Jg Jh Jk Jn Kz Nm) fP(Aa Hq Hr jM Nf Or rW wL) Hr(Ap cR Iq Pi Tt vB) tQ(Ap Mm Na Nw Ok Ou) Tt(Jj Ng oF pF) rT(Ic Jv Ra Us)

Figure 4 Continued

Figure 4 Continued kN mM nI) Vs(Uw Ux Vb Vi) bL(nH nO nT nU) Ji(Vz Wd Wg) We(Nl Nq) Wf(Ik Jq) Ug(Vc Vj) Uv(kK Vj) Vu(nO nU) dI(nD nU) mS(Ar Ch)
nI(As cH) nK(Ij Iu) kS(nO nT) WmWd TiKx GdIz MkWg HvVz HxYe YdOi VolY aKkP bXkE dBnH} qV{Wc(Hq Ih Ij Ik Ip Iu Ji Jj Jm Jo Jp
Js Jt Lj Lu Ma Mf Mk Mn Mr Nc Nj Nk Nm No Nt Nu Nw Ny Oe Og Oi Oz Pc Pe Qa Qb Qc Qd rA Ua Ub) hG(kE kK kN lW mH mM mY nD
nF nR) Wf(Mt Mu Oe Qa qX Tz) Yl(Hx Jg Mf Ni Oi Tm) Mp(Wb Yd Ye Tm) Hx(Wd We Wg Zx) qX(Ux Vj Zx Tm) Ti(eD fY pY) Tz(fR Wd
We) bL(nD nO nU) Mm(tQ tT) Ye(Lv Me) dB(mS nT) kP(aQ dR) EmbR MfWd NanK UbnI lmTm UoVa UmkK UgUx UvlW VunT VolY
aNmP aWmW bFkI fRkS tFmM} mZ{Cq(Em Gd Hp Sf Sh Si Uw Ux Vb Yd Yg Yj Ye) oH(Fd Hp Lp Ry Sh Uw Wd We Yh Yi Yj Ye) Rv(aD
bA bF dB Ha Ml mY Pk Ud Ut Tj) aL(Fi Gh Hp Rx Rz Yg Yi Yk Yl Yf) Tn(Gd Ps Si Uw Ux Wd Yg Yi) Vb(Ao Jp Ke Mw Om On) bB(Em Ho
Rx Vi Wd Yg) Du(aD bF cT Ml) Em(Bn dD Ld mH) Qv(Rz We Yg Yi) nT(Op Rz Sf Ye) bL(jL qU rA) Gd(aH Jg) Mw(Hp Yf) Hr(Yi Yk)
Wd(Iz Vs) Op(Gp Ou) Vi(cU Li) dB(Ry Yg) ChYh FiMv NcZx HqVj YkKj JpUw RzUm OkVw hGjU} Si{Jp(eQ gZ jB kI mF nH oT oV oW
pH pI) Tn(eQ hC mE nH oH oK oN oT pF) Jg(gP iA kE kI mF nH oH oK oT) On(eC gZ jB mF nK oH oK oN oV) Uf(eQ gZ jB nH oT oV oW
pH pI) Ko(eQ gZ jB mF oV oW pH) Li(eQ gZ oT oW pH pI) Ok(eQ gZ jB mF oT pI) Ij(eQ nK oT oV pI) oK(Ad Ef Ke Kf Vh) Nq(oP oW pH
pI) Ut(jB kP lY mY) Ad(fP hC oH) Ef(aC oH) Jn(mE pI) mF(Fb Ke) CqmP GpnI MneQ HqjB KfoH OpoW} qX{Wf(Ik Iu Jg Jk Jn Jr Mg Mk
Nc Nj No Nq Nr Nu Oz Pb Qc Qd Qe qU Ue Wd We) Oz(Vz Wb Wc Wd We Wg Yd Yl Ye Tm) Em(Af Bn cB Ch cQ cV Cx De) Wd(Hu Ip Js
Ma Mw Ni Nk Nr) Pc(Vz Wb Yd Yl Zx Ye Tm) kP(aK Ar aV cY dR tF) Mf(Vz Wb Yd Ye Tm) We(Ly Nf Pa Ue) Wc(Ip Nk Pa) Tm(Jg Nu Pa)
hG(kI lW mF) Ye(It Nc) Uv(kK lW) Vu(kO nO) Vs(fR Vw) bL(mW nT) oK(mI mM) ChnF TnfR UmkN UhVc UuVw aNmP bFmS} jL{bL(kE
kG kK kO mE mM mP mU mW nB nH nO nT nU) hG(kE kI kK kN kP lW lY mE mF mH mI mY) dG(kG kN kP lW mH mP mU nD nI nR nU)
mI(bC bW cB cF kS Uv) kP(aK aQ bB bF dR hB) mM(aD dB hB Um Vu) Gd(Bc cP Iz) Wb(aA Jg Pd) Wc(Ik Jg Wm) Vu(kE kG nO) bW(kK
kN mF) cS(lW mE mU) mS(Al Ba bF) Mk(Wd We) Tz(Wd Wf) Zx(Hx Mu) Va(Ur Vs) hB(kG nU) sI(uN vS) MeYe MhWf JgYl WgJq UmkN
UvlY VcaA VhjG aJkG dBmW tFkK nRnW} qU{bL(kG kN mE mH mP mS mT mU nF nI nK) tV(Cw Et Ip It Kf Ky Mm Mz Pb Uf) mI(AW
bG bW cJ cS hG Ue) Vu(kK kO mH mM mY nT nU) Et(Hf tN tR tS tT tX) Mm(tN tR tS tT tX) Kf(rN tO tR tS tX) kK(cJ Co Um Uv tF)
Cw(qC qD rN tN) fR(Co Im Mz Tz) kP(aK aQ aV dR) kG(Tz Ur Vp) Mf(Wd We) Mk(Wc We) Hf(Ad On) mF(aK dR) mW(aW dB) tT(Ip Nw)
AprN AsnO ChmY TiqC LvYe MuWf YlPc OkfN UmkN UvlW VaVs bFmS bUmT} sI{Ky(eT hX jK sC tN tO tR tS tT tV tX uG uP uX vP wC
wE wG yL xA) Ib(Ad Ap Dg Ez Ip Jg Kl Nm rX rY Tr Tt) Tr(cP fP Hu Ic Ng oF Or Oy Up Uu) Tt(Ct Hr Hw Jj Ng oF) Pc(Ad tO wB wG wL)
tQ(Ke Mm Nw Ok Ou) tV(Et Hw Hx Ip Nm) rT(aU fY qO Um Us) Hr(fP Iq Kg) Il(Et Ks Vv) Bn(qC yH) Mm(Fw Qg) Or(fP tT) Uf(cT rW)
Uh(qC uN) vB(Na Um) AafP FbrW NmwL QaVu JgUs KptF OuuZ UnuN PixA pYvS} hA{Ii(Gd Wb Wd Wf Wg Yl Ye Tm) aA(Va Vc Vj Vz
We Yd Yl Ye) Gd(aP Bg Cw dA dD Iz) Ye(Iq Ir Ji Nb Nv Pg) Vs(Ux Uz Va Vh Vj Vw) Jg(Vz Wb Wc Yd Yl) We(Mk Nc Nx Pg Tz) kK(dB iJ
pF Um tF) mI(aW bW dB hG) mS(bF Cw hC Vo) Ik(Vz Yl Zx) nH(aE dB iJ) kP(aK aQ tF) Et(tV vS) Mk(Wd Zx) Wf(Iq Of) bL(nO nT) fR(bC
Jh) lW(hG Uv) mW(cI cS) mY(Al hG) TiqQ HwWg YlPg UmkN UftV UgUx UsnI UtVj UwVa VhjG VunU VolY mMiJ} eQ{Gh(Cq Cx Hq
Hu Ib Mn Nc nT On Ph Qz Rt Tt Up Ut) Th(bF cT Hu Lu Lv lY mH Nx Tn To Tm) Mn(Sj Uw Vb We Yd Yi Tm) Tm(bB Dd Ko Li Mv Nq)
bA(Dr Fd Hp Vj Wb Yh) Ko(Gd Tr Uw Vb Yd) On(Ez Ub Uv Vo) mH(Gc Sj Yj Ye) Ao(Gd Ub Vb) Cq(Gd Qv Uk) Tj(aL Kx Mk) Tt(Ub Uv
Vo) cG(Gd Kr Qv) Mv(Ry Yj) Vh(aD oK) DeEm FiPh GcoH NqLt NtdB TocR YhcT YjQz WenW RyaD NxUr UmcM UfUw} nI{Gp(Du Eq
Fd Gb Gc Gd Gh Ho Hp Lp Lt Op Ps Rt Rv Ry Sf Sh Uw Ux Vb Vh Vi Vj Wb Wc Wd We Wf Yd Yg Yh Yi Yj Yk Yl Ye Ti Th Yf) lL(cI Ul
Um Up Us Uu Vv) Th(aE bF bP Co Sf) Em(Af bB Bn De) Ko(Gc Rt Vb Yf) Du(cD cG Ml) Mw(Dr Vi Yf) jP(hG Um Vu) oV(Gh Vj Ye) Aa(Gh
Va) Wd(Iz Om) AoVb GcMv MnRt InrX ltrB YdUf KkVj RvOi UpjU UslO VibB bLjM hGjV rAnY} jG{Vh(iB jK jM jO jU jV lO Uh Uk Ul
Uo Up Uw Uz Va Vc Vi Vo Vp Vw Ti Th) fR(Ad Af cA Ch cM Cw Jg Kl) nU(Ar Ba bL Ch Co kS) Tz(Wc Wd We Wg) Ik(Wd Wg Yl Zx)
Va(aA Ut Uu Vs) bL(kO nH nO nT) Vu(kG kO nO) Vs(Ux Vi Vw) mI(aW dC hG) Gd(Iz Ss) Mk(Wc Wd) Nc(Wd Ye) Wf(Mg Nn) Uv(lW lY)
cB(kK mM) ThVi HwWg IctV IvYe UmkN UwiB VpkG aNmU aQkP bFmS cImW dBkK nTkS mThG} Nq{pI(Du Eq Fc Fd Gb Hp Lp Lt Ps
Rv Ry Rz Sj Uw Ux Vj Vw Vz Wd Wf Yd Yg Yk Ye Tm Ti) oP(Gb Hp Lt Ry Yg Yi Tm) Uf(tN tO tS tT tX wQ) Ry(oO oQ oT oW pH) fB(Gb
Rv Vb Wc Wf) Lt(mH nU oQ pH) Uw(gZ mT oV oW) nU(Du Gh Rv) qC(Ad On Un) pH(Hp Vb Yi) Ap(rN tX) Mm(tN tX) Vj(oT oW) qD(On
Un) GhmH YegP KetS RvlW OkvB UxgZ kGrY} lL{dB(kG kK kO kP mI mT mW nD nH nK nR nU) Ad(Na qC qD qG qO qQ rN vS) Jg(Vz
Wc Yd Yl Zx Ye Tm) kP(aK aQ aW bS De dR) vS(Cw Et Mz Nw Tr) Mk(Wc Wd We Zx) Ip(sC tT tV yL) Ye(Im Js Me Nn) Ti(rB Rc) Et(rV
yL) Mz(qC qD) Tz(kG nB) Ik(Vz Wc) Nw(sC uN) Va(aA Vs) Vu(kO mI) mW(cB dC) kK(Um Uv) WmWd GdIz NcVz TtrN IunK WgOm
WfaA VbVs VolY aWnR lWhG} jO{Wb(Iq Jg Jh Mp Nn Of) fR(Cv Iq Kx Mu Oi Ss) Ii(Wc We Yd Ye Tm) Vw(lO Uf Ug Um Uw) Ye(aA Jg
Lh Mh) Va(aA Ut Uw Vs) aQ(kI kP lW mH) bL(kO nH nT nU) Gd(cP Iz Mu) Tz(Wd We Wf) dB(mI mW nH) dR(kP mF mH) hG(mI mU nR)
Zx(Hx Pd) We(aA Mk) Ug(Ux Vh) bW(kN mI) lY(Uv Vo) MuWc HwWg IkVz UmkN UtVj UwVi VcaA UxVs VunU aWmW nOkS mUiJ
mYnY} Yj{Qz(gZ hG iO jB kE kG kI kN kO kP lY mE mH mI mS mY nO nT oH oK oN oQ pH pI) mF(bF cL Cq De Hq Ib Iq) Iz(eC eF gP hC
hG oK) pI(Af Bn Cx De Ho Mv) oK(Ch Ef Iq Jk Uc) Mu(kP mH mM oQ) Mv(gZ oT oV oW) pH(aJ kQ Up) Ef(dR gP) cL(nT oP) mP(bW Ut)
BnmY ChgP CqnU DeoT HqmI IsmH PhfA cEmM cXoV} jP{hG(kG kI kK kN kP lW mF mM mT mU mY nR) mM(bM bW cI cS cZ dL tF)
Wf(aA Hw Ii Ji Mk Tz) Wc(aA Ii Ik Ji Tz) Uv(kK lW lY mE nR) Wg(Hw Ji Mk Tz) Vs(Ux Va Vb Vw) kP(aK aQ bF dR) Wd(Mk Tz Wm)
Vu(kO nF nO) bL(kK mY nT) nR(bF oK tF) Ji(Ye Tm) Yl(Ik Jg) bW(mI mT) kK(pF Um) CtmI TzWe YeLh VaaA bFkI dBnH} kG{rY(Et Fr Ii
Ij In Ip Iq Is Iu Iv Jg Jh Ji Jj Jl Jo Jq Lh Li Lv Lx Me Mg Mh Ml Mm Mq Ms Mt Mu Mx Na Nf Nh Nj Nm Nn Nu Nv Nw Nx Ny Of Og Oi Ok
Oy Pc Pg) rZ(Ip Ir Nc Nk Nl) Iu(rB rC rX) Du(aD Ml) Ii(rB rX) jV(Ar bS) AoVb MjhX TzeD ShhC VujK tFiB} nK{rZ(Ij In Iu Iv Jk Jl Jr Js Jt
My Mz Nn Pg Qb Qc Qd Qe) Iu(eD hR hV hW hX jM jV lO rB rX rY) Ih(hR hV hW hX rB rC rX) rY(Hw Ii Ij Iv Qb Qd Qe) It(hR hW hX rC
rX) hV(Hx In Iq Iv Qd) hX(Na Nr Nx) Cq(Yd Yg) In(hR hW) rC(Hx Ii) DuaD NajV bLjM cIjK} eD{Gd(aD aS bA cQ dA Fr Iz Je) fR(Ad aV Id
Jp Nn Qv) mS(aF An AO Co Vo) Ti(Pa Pb qO Rc Ut) Uv(kE kK kN lW lY) kP(aK aQ dR tF) Ue(kE lW lY) bL(nO nT nU) hG(lW mF mY)
Rb(Ok Un) aN(mP nH) aW(kO mI) dL(nO nT) AdHf ChmY TtrN JjkK OgmU OkiA UmkN VunO VolY aVnR cSmW dGnT} Mz{Fw(eT fN
fY hL hP pY qA qC qD rN tN tR tS tT tV) tV(Cw dR Ed Ic iZ Ql Qw St Tt Uf Um Vp) uZ(Cw fP hG KQ kS Kz oE oF pF) qC(cV Cw Ed Ic Ip
Ql Qw Qz Vp) vS(Cw Kz Qv Tt) Tr(wL yL tL) Cw(hO vB) Uf(hO tT) qD(Ic Qw) IphL KzvB} Et{tT(aJ BG bZ cF cL dA dG Fw Hu iA Il iP Jn
jV Nu nW Oi qC Qd) tV(bZ cG dG Fw Hu iA Jn Ky Nu Ql Qw) yL(eT jV Qv Qw Ua Ub) iA(rN rW tR tS tX) nW(tO tR tS tX) Qv(uZ vH tL)
Fw(tX wK) Oi(hO tQ) UbvS KsqQ OghO bZtR dGtX tFxA rNuU} jU{Va(aA Ur Uw Vp Vs) bL(kO mW nD nH nU) Mk(Wd We Wf Wg)
Tz(Wc We Wf Wg) Gd(Bc Ow Ss) Nk(Vz We Yl) Ik(Vz Wc Wf) Uv(kK kN Vh) Vu(kO nO nU) Vs(Ux Vb Vi) mI(aW bW hG) mW(aP aW
dB) Ch(kO nO) Um(kK kN) hG(mU mY) kP(aQ dR) ThVw MhWf NcYl NeVz HwWe UgUx bFmS tFkK} jV{Va(aA Un Ur Uw Vp Vs)
Vu(kO mI nO nT nU) mS(bF Ch nY Vo) Kz(rX rY rZ) Uv(kK kN lW) nT(bL gL Vo) mW(aD aW cI) nH(bL cX cZ) Gd(Iz Ss) Nc(Vz Yl)
Nk(We Yl) Ky(tV tX) Vs(Ux Vi) kP(aQ dR) TirB MkWe MuWf TzWg TtrN TryL JgfR QvuN VolY aNmP aWmI tFkK hGkI} Iz{Vb(dR gL gP
hC iO iZ kR kS mF nY oH oK oV pI tF) hC(Em Eq Fi Gc Ps Ru Ry Vh Vj Wd Yh) eC(Em Eq Gc Lt Ry Rz Ux Vj) Wd(gP kN lY mH mM nR)
oH(Hp Ry Uw Yg) gP(Em Gc Vj) oK(Hp Yh) GdjK YgmF UvnT cUoV} jM{bL(kK lW mE mF mH mI mS nF nH nR) mI(aW bW cS hG Ue

Figure 4 Continued

Vo) Tz(Wd We Wf Wg) Vu(kO mY nO nU) Vs(Va Vc Vi Vw) Wc(Hw Jk Ua) mS(bF Co dE) kK(Um Uv tF) We(Ji Mf) kP(aQ dR) AdHf GdSs
MkWg HxZx UmkN UvnR VonT mWnW} iB{nO(bF hB kS pF Tz Vu) Va(aA Ur Uw Vs) nT(bF bL gL Vu) mW(aW cF cJ dB) kP(aK aQ dR)
Mk(Wf Wg) Ik(Wc Yd) Vz(Jh Nc) Ji(Ye Tm) Vs(Ux Vw) dB(kK mS) iJ(mH mM) ChmS GdSs TzWf IvYe WbJh UmkN UvIW aNmP dRnF
mYhG} pI{Gh(Bn Cx Ko Me Na nU Uf) De(Du Fi Gd Rv Sf Ye) Ko(Gd Sf Uw Yd Tm) Bn(Du Rv Wb Yh) Cq(Gd Sf Yd) Du(Af Cx Mv) Gc(bW Hv Um) Th(lY mH) Fi(cG Uf) Mv(Ry Tm) Um(cM cU) Ur(cM Nx) AfYh HoHr TtUv UfUw} jK{Vs(Uw Ux Va Vb Vi Vj) Mk(Wc Wd We Wf Wg) Vu(mI nO nT nU) Ye(Iv Ji Lh) Gd(Je Ss) Tz(Wc Wg) Um(kK kN) Va(aA Uw) bL(nO nU) cI(mI mW) dB(mM mW) mS(bF Co) kP(aQ dR) WmWf HxZx JgTm WejT UtVj VolY mYhG} Mm{tT(Al bZ cF cI Fw iA Ip Mv Nu oE Of Pi qD rU tL tF) tX(Fw iA iZ Ky Nu nW) Kz(wG wH wL wQ) tQ(Lv wG tF) tV(bZ Jn Ky) oE(tO uZ tL) AltO QvwL RzmF PitS cFtR tFwQ rNuU} jT{Wf(aA Ii Ik Mh Mk Tz) Mk(Wc Wd We Wg) Va(aA Uu Uw Vs) bL(nO nT nU) hG(kI lW mU) Tz(Wc Wg) We(aA Hw) Jq(Wc Zx) Vc(Uw Vs) mW(aW dB) iJ(kK mI) GdSs MhWd IkWg UmkN UnVj UvkK VunU aQkP bFmS nDnY} fR{aC(aW Ba bC bF Bn bO bX cD cE cG Ch Co CT cZ) rZ(aF aN aR Bc bF BN cC CH CV CX dB) rY(bO cB CV dK) rX(Aj aN) AdrC cIrB} Fi{bB(kO lW mE mF nH nU oT) hC(Ad Co Jt Kf On Tn Uu) Jt(eC gP iZ nW oK) nU(Fy Ko Tn Uf) Ph(fA kK pH) eC(On We) mP(Ij Mw) FylY TnmF UpjB UtkP cGnR cMoV} Qv{We(eC hC iA iP kQ nW nY oK oN) Aa(sC tV uN vA vS vT vW zA) vS(Ap Lu Tt) Nm(uU uZ) Tr(tV tL) Ip(uN tL) mF(Rz Yi) BcuN LutV TtwG YgoN NwuZ VhoK} rA{Wf(Ik Iq Mh Mp Oi) Uv(kK kN lW mH) Vu(nF nO nU) bL(kO mW nT) mI(bW dB oK) Mf(Vz We) mW(aW iZ) kI(dB hG) kP(aK dR) AdHf TiqD MuVz NcYd HxZx IqWc WeOg bFmS} Cq{Yd(fB gZ mP mT mW nD nH oV oW pH) Yg(lY mP mT mU mW nH) Gd(mU mW nR) Uw(lY mP nD) Gh(fA fB) Yh(mF mP) Sf(lY mY) YiIY VzpH RtnD VbmP} lO{nH(aE aN dB iA iJ) Ik(Wc Yd Ye) Vo(kN lY mS) mW(aW cI cS) Tz(We Wg) Ye(Ji Nd) tF(kK kP) mS(bF hC) WmWd GdJe NfVz HxZx UvlW UwVa VbVs VunO bLnT mYhG} Vh{oK(Aa cF cN Hu Ib Je Jk kS Mh Mu Mv Nd Ni Qw Rh Ub) Mv(eC gP oN) Fb(Kk Lh) Ib(gP oN) TjhC MwoN JegP KnjB aAcC aDoW cUnY} Vb{Ao(kN kP lW lY mH mS mT mY nO nR nT oP oT oW) gL(Ad Dc Jg Jp Jt Kf Ko Tr) Ko(jB oV) BaoH EfaC QzoW UfgZ UtmY} mF{Du(aD Hq Hu Ib Mu Mv) mH(Eq Rz Yg Yi Yk) Yh(Bn Ch Ef Vs) Rz(Kn lY Rh) Lu(Yg Yi) bB(Rx Wd) lY(Sh Yg) GcaD IbRy KnOp UfUw VicU} tV{Qw(Ad Bc Dk Ip Jg Jt Kj Kq Tr) Ky(Bc IP Lu Uf wH xA tF) Aa(Ic QI) Ib(Tr Tt) Ip(bZ qC) Jk(Ad Dk) Uf(bZ iA) HuTr IcqC} Uw{Uf(gZ jB oT oV oW pH) Ko(gL jB oT oV pH) Jp(gL iZ mE mT) Fb(Af Bn Cx) Jg(gL iZ) oK(Ef Gp) MvmT LigL cGnT} Gc{Hv(gZ jB lW mP oT oV oW pH) Mv(eC iZ lW nU) bW(lW oQ oW) mH(fA gZ Qw) oH(jB oT) TjnU MlIY aDgZ} Nw{uZ(Af Gp Ic Kj kQ Kz) Ic(tS tX vS tL) tF(tO tR tS tT) Fw(tS tT tX) Kz(rX vB vS) Af(tS uN) CwvB} Ut{mY(Du Eq Rt Rv Sf Vj Wd Yd Yg) Yd(mE nU oV oW) kP(Du Rt Rv) Gh(fA lW) oV(cU Sh) EqmH YelW RylY} Ip{qC(Ic tN tQ tR tS tT tX) tT(Fw On Qc qD vI) Ic(tN tO tS) Ky(tN wH) wL(Iq On) wDtL kPrZ} lY{Th(Aa bE cL iP Kk Lp Ml) Ml(Du Lp Yg Yi) Yi(gL Gp Rh) Hp(gL It) EfWd YfMw EmbB LvQy YggL} Ad{Us(hR hV hW rX vS) Qw(qC qQ vB yL) Na(rX vB vH) Hf(rN xA) qQ(Ti Th) NtrN IcqC aCaW} Gp{Yg(eC hC iZ mH mS oK) Yi(iZ mH mS oK oO) oO(Sh Wd Yk) mH(Fd Vw) WdoK RznD VimT} We{gP(Dd Jn Jt Mn No Tj Th) Tj(eC hB hC nW oE) Fb(Kk Lh) Hr(eC nW) Il(eC hC) RhjB} Ti{bI(eT pY qC qD) eZ(Il Jf Ns Rc) qC(cJ qQ Rc) cF(pY qG) IdqB RcfY PaqD eTqQ pYqZ} oV{cM(Nb Nt Um Ur Tj) Ko(Gd To Tm) Nx(Hr Ur Tj) cU(Ua Vi) AnYh BaEq TjIt MvYk} Du{Ml(gZ mH nH nR oW) aD(kE kO mP mW nH) Mu(kP mY) Mv(nU pH) MwnR IbkI} Ok{vB(iA Ic Ky Nt Qw Rb) uL(Hf Ky Rb) uZ(fP iA Ic) NutT IcwH HfrX tFvH} Gh{oW(An Hq Hr Qz Up) fB(bW nT oH Rj) fA(aP Mv Mx) aPjB bIoT} rN{uU(Ap cF fP Hf Jg Kf On) iA(Ap Dg Kf Uf) Nu(Ap Dg Kf)} Tt{Hu(tR tS tX uX vS yE) vS(Bc Ms rB Vs) UvoW tFqA qQoF} jB{Mv(Ry Yg Yi Tm) Eq(Ba Qz) MlRv WdRh KoUx RyaD LpnD NxUr UmcM} Th{Mv(kN kP lW) Ny(fN fY) nB(Ef Mu) QmqC VsnR PaqD gZmH} Uf{bZ(tO tR tT tX) iA(sC tT yL) AanT GdgZ LvmS YdfA} Yi{Hr(mI nH nU) Mv(oW pH) FboK RhmH UmpH aDoO nRnW} On{Ql(qQ uZ vB tM) Hf(rX uZ vB) vB(Jk Qw) HpoK} gP{Wd(Aa Dd De Ko) Jg(Yl Ye) Jt(Hp Ye) GbJe QzVj} Ib{Tr(sM uX tL) Wd(lW mT nO) Ry(hC oE oH)} Rz{bW(kO lW mP) Rh(lW oQ) TjnU EqmS KnnT cUhC} bB{Em(kP mH) Vi(kP lW) TjnF WdlW WfiZ YeoH RxoP} Ko{Yd(oO oQ oW) dB(fA oT) YfnW EmiZ GdoW} Yh{Ch(eC fP) oK(Jg Jk) BnmY TnnU QzoW} Um{cM(fA fB gZ oT oW pH) YgpH} rZ{My(kP mU mW) Hx(mE nH) kP(Hr Og)} vS{Cw(fN pY Us) UbJg JpUp KfhL LhQl} Eq{Ba(fB kI kO mU) NgmS OyhC} Hp{gL(Dk Mv) oK(Jk Nv) JehB JgiZ} Tr{tS(Hu Ic) yL(Ky Ub) QuwG VstL} Ry{Jk(oE oH) EfhC MvkO QzoH dBmT} Nx{Ur(fA fB gZ oT oW pH)} Hr{nU(Op Rv Yg Yk) VimT} Kq{Na(rX uL vB) Hf(uL vH)} tT{qC(Ap Cu Dg) Fw(Cu Nm)} rY{mE(In It) nH(Hx Og) PekP} De{Wf(eC hC) YfeC EmnR} Jg{Gd(iZ tF) JeVw QwuM} Kk{Fb(Rt Rx Yl) UxnT} bW{Op(lW mP) WbmP UxhC} Aw{aC(bC Dl) tSnW} Cw{vB(Hu Kc) GdoW} Hq{YekO JunT UkgZ} Ic{AawG UnqC qQoF} Qw{Bc(wL tL) JtwL} fA{FdPh MwYe SfQg} mS{Lv(Ef Qy) hVqZ} Ao{UgoW VanT} Em{BnkK cGnR} Fw{KetS KftM} Je{TmhB LtcB} Kn{OpnD VjpH} Uv{Oy(nT nU)} fP{AauZ bZwL} TjcIpH FyNauL NuUnqC IjSfmH HfLhxA YgaDoO ShRhhC QzVjoH JpoEuZ KcKzvB KywHoF RxgZkQ VicUml

Unconstrained panels with 2 analytes, where 1.0E-8 >= 'AUC p-value' > 0. Contains 451 panels of 199,257 total panels evaluated. : Ok(aC aN aR eO Et Fp Hr Hw Hx Ii Ij Ik In Io It Iv Jj Jo Jr Lv Mb Mc Mj Mp Ms Mv Mw My Nb Nc Nd Ne Nf Ng Nh Ni Nj Nk Nl Nm Nq Nr Nx Of Og Oh Oi Om Oz Pa Pz tQ uL uZ vB zH) aC(Ad Af Aj Al An Ao Ap AR AW BA BB BC bF Bg Bn Bo bR bU cB cE cF cG Ch cN Co Cp CT Cu Cv Cw Cx Db Dc De dF Dg Di Dk Dl dN EO Et Ex FR Is On) Et(aA Fp hO Hw Hx iA iH Ii Ij Il In Io Iv Jj Jr Lv Lx Mb Mh Ml Mr Ms Nc Nd Ne Ni Nj Nk Nl Nr Og oK Om Oz Pa Pc Pz qC tQ tR tT tV tX wL zH) nN(eD gW hA hR hV hW hX iB iC jD jE jF jG jH jI jK jL jM jO jP jQ jR jT jU jV jY lK lL lM lN lO qT qU qV qW qX qY qZ rA rB rC rX rY rZ) oD(Dr Eq Fd Fi Gb Gc Gh Gn Hl Ho Hp Lt Op Rv Ry Sf Sh Si Uw Uy Va Vb Vi Vz Wf Wh Yd Yg Yi Yk Yl Zw Zx Tm Tl Yf) Pj(hO jD qB qC qD qI rW tN tO tQ tR tS tT tU tV tX uV wB wC wD wE wF wH wJ wK wL wP wQ yD yH yL zH tM tL xA) jD(Gd Uw Uy Uz Vb Vc Vj Vw Vz Wb Wd We Wf Wg Wh Yl Zq Zw Ye Tm Tl) qY(Uw Uz Vb Vh Vi Wc We Wf Wg Yl Zq Zw Zx Xa) Bb(eZ fN hO jY qC qD rC tN tR tS tV tX zH) Zq(jH jL jO jP jQ jR jT lM lY) eO(aN aW bB bM Bo cB dB Lx Mn) qT(Wb Wc Wf Yd Zw Zx Tm Tl Xa) Nd(aA Ji Jp Lx Mm Nv Nw On) Eo(aN aW bM Bo Lx Mn Nh) Wh(hA jF jH jL jO jT jY) Ew(aW bB Bo Lx Mn) gW(fR Gb kF kP Ye) zH(Jp Lh Mz On Vt) Dw(aW bM Bo Lx) Mm(tN tQ tT tX) Jd(Di nF Og Ub) Vh(jG oK qW qX) eW(aW bM Lx Mn) Ip(tT tV wB) We(eM jH nW) Xa(jO jP lL) On(aN iA Nj) Vc(jI qW qX) sJ(rS Tr Vt) Ad(iH qC) Mz(qC qD) Tn(dX cP) aW(cB cF) dW(bM Lx) eD(Cw iH) BcjY DugC FbgV GnnI NjNw JgiA WcqW WfqX YelK KoeP KqgP KytV RznJ UwjO VajI VtuZ VquM VwlM aRcB Unconstrained panels with 2 analytes, where 1.0E-7 >= 'AUC p-value' > 1.0E-8. Contains 398 panels of 199,257 total panels evaluated. : Et(bR eZ Fr Hr Hu Hv Ih Ik Im Iq Is It Iu Jg Jh Ji Jl Jm Jn Jo Jp Jq Js Jt Lh Li Lj Lu Lw Ly Lz Mc Md Me Mf Mk Mm Mn Mp Mq Mt Mu Mv Mw Mx My Mz Na Nb Ng Nh Nm Nn No Nq Nt Nu Nv Nw Nx Ny Oe Of Oh On Oy Pb Pf Po Qa Qb Qc QD Qe qI tN tO tS) Ok(aA aH bR Eo Fr gP Hu iA IH Il Im Ip Iq Ir Is Iu Jh Ji Jk Jl Jn Jp Js Jt Lh Lj Lu Lw Lx Ly Lz Md Mf Mg Mh Mi Mk Ml Mn Mq Mr Mt Mu Mx Mz Na Nn No Nt Nu Nv Nw Ny Oe oK On Oy Pb Pc Pd Pe Pf Pg Po Qa Qb Qc Qd Qe uG uM uN vH vI wL) aC(aG aJ aM aN aO aP As aV AX aY bE bM bN bQ bV bW bZ cA cD cL Cq cR CS cW dB Dd dG dH dJ Dw Ef Ew Jg Ji Jp Jt Nw Of Pd) Pj(eT eZ fN fY hL iH pY qA qZ rC rR rT uM uP uR uT uU vP vQ vS vT vU vV vW wG yJ yK zG zI yE) oD(Du Fc Ps Rt Ru Rx Rz Uz Vc Vh Vj Wb Wd Wg Zq Ye Tj) Nd(Fr Is Jg Jj Jt Lh Li Mn Mp Mt

Figure 4 Continued

No Nr Pa Po Qa Qe) zH(Bc It Ji Kz Mm Ms Nh Nm Of Oh Pd Po Qa Un) Jd(aN aR bU cB cF iH Ki On Pa Qw Qz Vc Tj) On(aH aR aW iI1 Ii Iv jG Nl tT Uv Tj) aN(Ad AW Bn bU cB cF Cp Dg dW Jg) Bb(aW eD hL jY IK pY qA qB tO tT) Nw(Dw Eo Fp Iv Nc Nl qC wL) cB(Ad Aw bA bF cN cT Di) iH(Aa bU cF Jg Nm rC) Mm(tV wD wL wP) Mz(fN hL hO jY) Vt(sM TV tL xA) fP(rX sJ uM wL) Ad(aW iA jM) Cw(oK qU vB) Nj(aA Fr Lx) Bo(dW eW) Dw(Jj Mn) Ex(hO xA) Ip(tQ tX) Iv(In Ji) Jg(Aj aR) We(eC gP) Tl(gL hB) Vq(wL tL) aW(Cp dW) HldU TtvS TneM IseP ZqmH QvuN LhxA OpnJ UnqC PeeO aMeW bFfR nNmE sHrS

Unconstrained panels with 2 analytes, where 1.0E-6 >= 'AUC p-value' > 1.0E-7. Contains 694 panels of 199,257 total panels evaluated. : Et(aN aR aW bA cQ Di eC eF eT fN gP hF hG hL hP Hq Ip Ir Jd Jk kR Ma Mg Mi Mj Nf Ns oH Oi oN Pd Pe pF Pg pY qA qB qG qH qO qQ Qv qY rN rO rP rR rS rU rV rW sJ tU Ug uM Uv vB vH vI wB wC wD wE wF wG wH wJ wK wP wQ yD yH zA tL xA Tj tF) aC(AA aD aE aF aH aI aK aL aQ aS aU aZ bG bH bI bJ bL bO bP bS bX cC cH cI cJ cK cM cO cP cQ cU cV cX cY cZ dA dC dD dE dI dK dL dM Dr Em Gc Gp Io Jd Jh Lh Mg Mt Mv Om Zq Xa) Ok(aG aO aW bZ cB cE cK cO cQ cS cU Di dK eF eP fP hO Hq Hv Jg Jm Jq Li Ma Me Mm Ns sC tN tO tT tX uI uO uW uX uY vA vC vP vW wG tL) Jd(Aj aW bR Fi Ic Ik In Io Iq It Jj Jk Jp Js jY Ky lL Lv Ma Mc Mk Mz Nc Ng Oh Or Pb Pj Ql Qm Qv Rh Ri To Tt Ua Um Ur Uv Uw zH) zH(Cw fP Fr Hf Hr Hw Hx Ii Ip Ir Is Jh Jl Jn Jo Jq Jr Js Kc Ky Lw Lx Mq Mr Mx Na Nv Nw Pa Ri Um) Pj(eD hA hP hR hV hW hX jO jY qG qH qO qU qY rN rO rP rQ rS rU rV rX sC sM uL uZ vB vO zA) Nw(aR Hx Ik Il Ip Is Lv Mb Mh Ml Mn Ms Mu Mv Mw My Ne Nk Nm Nq Nr Nx Om On Pa Pd tL) On(aO bR cA cK eD Fp gP Hf Hw Hx Ib Ic Jj Mb Nc Ne Of oK Om qC Qv Qz sC tO vH Vo) Ad(Aw Bn Bo cF cN cT Di eD fP gP gW hL In jD Jj lL Nj pY qD qO rN) Nd(Di Fp Iv Jq Lj Ma Me Mr Mu Mv Mz Nm Nn Nt Og Oh Om Pd Pe Qd) cB(aQ aU aV Bb bC Bn bQ bU cF cG cK cM Cp cQ cY dD Dw Ex Jg) Nj(aR Bb Di Is Jg Ji Jp Jt Li Mn Mp Mt No Nr Nv Nx Pa Qa) Vt(qC qD rP rU rV tN tR tS vS wC wF wG wH wL yK yL) aN(Ba Bb bC bF bR Ch Dc Di dX Ew fR Is Ji Mt Of Pd) Bb(bU eT fY hP hR hV iH iZ jD lL qI qO qP qQ) aW(Aw bM bR bU Dg Di Dl dX Em eP Ex fR Jg Ko) Nl(aA Fr Jg Jj Jt Li Lx Mm Mn No Nx) oD(Kk Lp Ut Ux Vw Wc We Xa Ti Th) Mz(eD eT eZ fY hP jD pY qT tV) Ji(aR Dw Ew Fp Mb Ms Oz Qa qC) Di(eD Ic iH Io Is It Mt Pd) Mm(tO tR tS tU wB wF wG wQ) Zq(iZ jF jM lK lL oK qT qV) Jg(aH bR bU cQ eF Fi Jj tV) cF(Aw BA bF Cp cT eD rC) Ip(qC sO tN tR tS wD wL) Iv(Fr Il Jj Jp Lx Mn Og) iH(Jt Kq qU rX rY Wc) Cp(aH aR Bo bU cK) Tr(sF sH sM tV yL) Jj(Ik Lx Mt Nr Nx) Xa(eC hA jL lM qV) Lh(tN tT tV wD wL) Tk(sC tS vP vS zG) qT(Uy Vj Wh Yl Ye) Fb(Dr Em Vc Vh) Kf(rN sJ uZ wL) Kq(cF iA oK oN) Uf(tN tO tV xA) jD(Ux Vi Yd Zx) qY(Uy Vw Vz Wd) Aw(bM bU Dl) Bc(eD lL lN) Nc(Fr Lx Nx) Wh(lK lL lM) Vh(jY rA Vq) aR(Is Jh Jt) jI(nJ nK nU) rZ(fP fR kP) Tj(Pa Tn) Nm(tT tV) Ic(qC tV) Tt(Aj rN) Qv(uZ vS) Jp(uZ wL) lM(Wd Zw) AphO CwlL DugL DwbB EfVb EoNu EwbM GnmE MnNh IsbR IzgC WfhC JtqC TmqW KkdX RxnJ RitS WnsC UnjY VcjH VqyL cWeO dRfR fPrY nNmH mTiC nAhV sFrS Unconstrained panels with 2 analytes, where 1.0E-5 >= 'AUC p-value' > 1.0E-6. Contains 1,885 panels of 199,257 total panels evaluated. : Jd(AF aG aH aM Ar aX Bb bC BN Bo bZ cM cN cT cV Cw CX cZ DB De Dk dN eC eD eF Ez Fb Fn Fp Fr Fy GL Gp Ha Hf Hq Hr Hv Hx iA Ib Id Ii Il Im Ip Ir Is Iv Je JG Jh Ji Jl jM Jn Jr Jt Ju Jv Jy Kc Kf Kj Kn Kp Ks Kx Ld Li Lj lN Lt Lw Lx Lz Md Me Mf Mh Mi Mj Ml Mm Mn Mp Mq Mr Ms Mt Mu Mv Mw Mx My Nb nC Nd Ne Nf Nk Nl No Nq Nr Ns NT Nu Nv Nw Nx Ny Oa Oe Of Oi Ok Ou Oy Oz Pc Pd Pe PF Pg Pi Po Pz Qa qC Qd Qe Qg Qh qI Qn Qt Qu Qx Qy Rc Rf Rg Ru Rz Ss St Tn Tv Tz Uc Ud Uf Ug Uk Ul Un Up Ut Ux Vh Vo Vq Vw Ye Tl Wm Yf) On(Ad aF aG aM aS aY bC bJ bO bU bZ cB cC cI cN cP cQ cS cV cZ dA Di dJ dK dM dR eF Fi Fn fP Fw gL hA HC hF hL hO Hr Hu hX Il IO Ip Iq Is It Iu Ji Jk jM Jr Kc Kk Kp kQ kR kS Kx Ky Lj lL Lv Lx Mc Mh Mk Ml Mr Ms Mv Mw Mx My Ng Nh Ni NK Nq Nu Nx nY oE oF Og oH oN Oy Oz Pa pF Qa Qb qI qO qP Qu qX qY qZ Rb Rf Rg Rh rW TN To tQ Tr tS TV tX Ua Ug Us vB wL yD zA xA) Nw(aA aN bR cB cK eD eO eW Fr hO Hq Hr Hu Hv Hw iA IH Ii Ij Im In Io Iq Ir It Iu Jg Jh Ji Jj Jk Jl Jm Jn Jo Jp Jq Jr Js Jt Lh Li Lj Lu Lw Lx Ly Lz Ma Mc Md Me Mf Mg Mi Mj Mk Mm Mp Mq Mr Mt Mx Mz Na Nb Nf Ng Nh Ni Nn No Ns Nt Nu Nv Ny Oe Of Og Oh Oi Oy Oz Pb Pc Pe Pf Pg Po Qa Qb Qc QD Qe qY rU tO tS tT tV tX uN vI) Ok(AD aI aK aL aM aP aQ Ar aS aU aV aY aZ bA bB bE bH bI bJ bM bN BO bP bQ bU cA cC cF cH cI cJ cM cN cP cR cT cV cW cX cY cZ dA dB dC dD dE dF dG dH dI dJ dL dM dR dW eD EW Fb Fw gL gW Hf hL Ic nW oF oH oN pS qC qI qO qP qQ Rb sK tR tS tV uP uU uV Vo vQ vS vV wB wC wD wE wF wJ wP wQ yD yH yK zA xA Tj tF) Et(aH aQ Ba bQ bU bV cA cC cK cN Cp cS cT dD dR eD Fb Fn fP Fw fY gL gW hB hC Hf hR hV Ic iJ iO iP iZ Kp kQ kS Kx nW nY oE oF Ou Pk pS qP Qz Rc Rh Ri Rm rQ rT sC sM sO Tn Tt Tv Tz Ub Uc Uh uI uL uN uO uP UR Us uT uU uV uW uX uY uZ vC VO vP vQ vS vT vU vV vW yK yL zG zI tM Tk Wm) cB(aA aD aE aF aG aH aI aJ aK aL aM AP aS aX aY aZ Ba bB Bc bE BG bH bI bJ bL bM bN BO bP bR bS bV bW bX cA cC cD cE cH cI cJ cL cO cP cR cS cU cV cW cX dA dB Dc DE dF Dg dH dI dJ Dk Dl dM dN dW Ef EW fP FR gW Is Nj rC We Tj) Ji(aA bR bU Di eP Fr gC gP Hw Hx Ii Ij Ik Il In Io Ip Ir Is It Iu Jg Jj Jp Jr Js Li Lu Lv Lx Mc Mg Mi Mn Mq Mt Mu Mx My Nc Ne Nf Nh Ni Nk Nl Nm Nn Nq Nr Nt Nx Oe Of Og Oh Om Pa Pc Qc Qe Tt tV uM vC vI) Ad(Aj aR bA bC bF bJ bM bU cE cG cK Cp De dF dR eF eT eZ fN fY gL hA hB hG hO hP Ii iJ Il iO iP iZ jG jO jU jV jY kQ lK Nd nW nY Of oH oK Om pF qA qB qI qP qQ qU qY rC rW tV xA Tj tF) Bb(aR bA bC bM Bo cE cF cK cN cT dD dN fP gL gW hA hB hC hG hX iB iC iO jE jF jG jH jK jL jM jO jP jQ jR jT jU kQ lM lO nW oK qG qH qX qY qZ rN rW uM vB yD yH xA tF) Cp(aG Al aM Ap Ar aU aV Ax aY bA bC bE bF bJ bM bO bQ bR bW bZ cC cE cG Ch cM cN cO Cq cR Cs CT cW dA dC dE Dg dH Dl DK Dl dM dN dR eD eF gL gP gW iH In) Jg(aD aG aQ Ar aY bA bC bM BN bV cA cH cI cK cM cN cP cT cW dE Di dJ dN dR Ex Fp gL gP hB hC hF iJ iO iP Iv iZ kQ kR kS Lx Nc Ne Ng nW nY oE oF oH oK oN Qz tF) zH(Cu Dl Hq Ic iH Ij Im In Iu Iv Jt Kf Li Lj Lv Lz Ma Md Mf Mi Mj Ml Mu Mv Mw Nc Ne Nf Ni Nk Nl No Nq Nr Ny Om Pb Pe Pf Pg Pz Qb Qd Qe tT Vq Tk) aC(dW eM eW Gd Gl Gn Hp Hu Im It Iv Jj Li Lx Mm Mp Mu Mw Na Nc Ne Ng Nh Nj Nl Nm Nq Nr Nv Nx Ny Oy Po Qa Qd Qe Vh We Wh Ye Tj) aN(Ap aU aV bA Bc Bg Bo bQ cE cG cN CT Cu Cw cY dF Dl dN Dw Ef eP eW Ex Io It Jh Jp Jt Mg Mn Mv Mx Mz Nf Nj Nx Om Oy Pa) Nd(Aa aR Ih Il Im In Io Ip It Jh Jk Jl Jm Jr Js Lv Lw Md Mg Mi Mq Mw Mx Na Nb Nc Nf Nh Nk Nl Nq Nx Ny Of Oz Pf Qb Qc) cF(aM An aR aU aV bB BC bE Bg bM Bn bQ bU cE cG cK cL cN cS Cu Cw cY dB dD De Dg Di Dk Dl dN fP Fr gW Nj tS Tt) Di(aV Aw bF bU cK Dg Dl dN Dp dR Fb fP gP gW hB hF iA Ik iO Ir Iv Jn Kq Ky Nh Nl oH oK Qa Qe rC Tt tF) Nj(bA cT eO Ex Fp Im Ip Iv Jh Jj Jl Jq Lh Lj Ma Mm Mr Mu Mv Mz Nb Ni Nn Nt Oh Om Pd Pf Po Qd Qe) Nl(Dw Eo Fp Il Im In Is Iv Jp Lv Ma Mg Mp Mt Mu Ne Ni Nk Nm Nn Nr Nt Nv Oh Pa Po Qa Qd Qe) Jp(aR bR Dw eD Fp Hx iA iH Il jG Kx Lv Lx Mb Nc Nx Of Om Pd Pk qQ Qz tS uN uY vH vI tL) Vt(hO jY qB qI rO rR rS rT rW sO tO tQ tT tU tX uU vH vT vW wB wD wE wJ wK wQ zA tM) aW(An Ap Ar aV BA bF Bg Bn cG Ch cK CT Cu Cw cY De dN eM fP Jt Kc Kq Vh) iH(Ap aR bB cM Cw dB dD Dg Io Jh Ko Lh lL mH Mm No nT Om qW qX rA rZ tV vB vS) Cw(fP hA iA iZ jM jV jY lK oH oN pF pS qD qQ qW qY rB rC rX uM vH xA) Lx(gV Hr Hw Hx Il Jr Jt Lv Mb Me My Mz Ne Nh Nq Nx Og Oz Pc Pd Qa) nN(cM kC kF kI kK lX lY mI mS mU mW mY nD nF nI nJ nK nM nO nT nU) Mm(Fp hL hO Mb Nc Ne qC qI rU sC sJ wC wE wH wJ wK yD yH tM xA) Kq(dR Fn hA Hf hG Ic In Io iP It jM oF oH uZ vB wL tM xA Tj tF) Pj(gP jQ jR lL pS qP qQ Qv rB sK sO uG uI uN uW uX uY vC vH vI) fP(Aa bB bR bU dD pS rC sF sH sI sM uI uZ vO vS wC wE wF wQ) Lh(Iv oK qC qD tO tQ tS tX uM vB vC vH vP wF wG wK yD tL) Fb(Fi Gc Lt Rt Rx Ry Sj Uw Ux Wc We Yd Yg Yl Zw Zx Tl) Mz(iC jF jL jM jP lL lO qA qB qZ rN rR rS rU rV rW tL) aR(Aw bF Bn bU Ic Io Je Ko lL Mt Mv Nb Nm Of Om qO tT) jI(kE kG kI kO lY mI mS mT mW mY nC nD nH nL nM nT) Kf(eD iA oK rP rW rX tO tS tT wG wK tM xA Tj) Aw(aK aV bF bJ BO cK cN Dg eD gW)

Figure 4 Continued

Vh(bW dR Gn hC Hp iZ Je Mh oH oN Rh) iC(kG kK kP lY mS mU mZ nA nI nK nR) Nc(Jj Jt Li Mn Mt Ni Nv Pa Qa) Nx(Fp Il In Iv Mn Nh nK Og Qe) Uf(hO iA jY tS tT wL yL tM tF) tV(Jo Jt Kc Ma Pz Qv Ri Tt Tk) Ne(Eo Fr Jj Jt Li Mn No Pa) Un(eD hL jM qD rX uN uZ tL) Vq(jD jY qU sC Tn vB yK zG) bU(BA bF Bo cG cT De Is) Ip(hL tO wG wH wJ yH zI) Tr(qI rW sI uM vS wL) Jt(iA Jj oK qD Qv wL) Ri(Mn rN rW tX uN xA) bM(bF Bn De dX eP gV) Bc(hA jD jM jV qC) Fr(Hx Jj Mb My Nk) Tt(Ar Bn Fi Ib Jj) dX(Kc Ko Kp Kx Mn) gC(cG Gh Ko Nt Op) oD(Gd Ld Qh Uk Yj) Ic(cN eD hR qD) Iv(aA Is Li Pa) bR(bF cG cN Jh) dW(Jn Mn Pa Pe) fR(bA bE bJ rY) Ap(rN sH tT) Bn(bF Dg dN) Fi(Jk Li Tn) Gn(Ib mZ nA) Zq(bW mS oH) Qa(Mb Ms Qb) We(hC iZ oE) Xa(jY nW oH) lX(De gL gW) qC(Hb Nm Ti) uZ(hB Kc Ke) Ar(Is Mn) Ch(Dr Jj) Dl(bF Bo) Dw(dB Pe) Ef(Vw Zw) Ex(oK Tn) Nh(eO Pa) Ib(Ry Uy) In(Om Pd) Je(jV Oh) Wd(eM nJ) Wh(eM nJ) Jk(Uw Vb) Tl(iO jB) Tk(wL yL) iA(Ke Ko) CuxA EoPz TiqY EmSs EwPe GbgL GzTn NtaA LvIs MbNv HqnK HxOh IdjY HfqU KceP KpsJ RzoH QmeD VbOy aYeO bEdN cGnT nAjQ sIrS wDtL

Unconstrained panels with 2 analytes, where 1.0E-4 >= 'AUC p-value' > 1.0E-5. Contains 4,975 panels of 199,257 total panels evaluated. : On(aA aD aE Af aI AJ aK aL An Ao AP aQ Ar As aU aV Aw AX aZ BA BB Bc bE bF BG bH bI bL bM BN Bo bP bQ bS bV bW bX cD cE cF cG CH cJ cL cM CO Cp cR Cs CT CU CW CX cY DB DC DD DE dF DG dH dI Dk DL dN Dp eC Ef eT Ex EZ Fa Fb fN Fr FY Gl Gp gW Ha HB hG Hq hR Hv Id Ih IJ Ik Im In iP Ir IZ Je Jf Jg Jh Jl Jm Jn JO Jp Jq Js Jt Ju Jv JY Ke Kf Kg Ki Kn Ko Kq Kr Ks Kz Lh Li lK Lt Lu Lw Ly Lz Ma Md Me Mf Mg Mi Mj Mm Mn Mp Mq Mt Mu Mz Na Nb NF Nm Nn No Nr Ns Nt Nv nW Ny Oa Oe Oh Oi Ou Ow Pb Pc Pd Pe Pf Pg Ph Pj Pk Po pY Pz Qc QD Qe QG qH Ql Qm Qn qQ QT qU QW Qx Qy RA Rc Ri Rj Rm rN rS Sr Ss St tR Tt Tz Ub Uc Ud Ue Uf Uh Ul UM UN UO Up Ur Ut Uu Uw uZ Vb VC vI VP Vt vV Vw wC WF wG wH wK wQ Yi tM tL Wm Th tF) Jp(aA aG aH Ar aW bA bU cB cF cJ cK cT Di Dp eC eF Eo Ex Fa Fb Fn fP Fr Gz hA hB HF hG Hq HR Hu Hv Hw Ib Ic Ih Ii IJ Ik Im In lO lP Iq Is Iu iZ Je Jf Jg Jj Jk Jl JM Jn jP Jr Js Jt Kd Kf Ki Kk Kn Kp Kq kR kS Ky Kz Lh Li Lj Lu Lw Ly Lz Ma Mc Me Mf Mg Mh Mi Mj Mk Ml Mn Mq Mr Ms Mt Mu Mv Mw Mx My Mz Na Nb Ne Nf Ng Nh Ni Nk Nm Nn No Nq Nr Nt Nu Nv nW Ny Oe oF Og OH Oi oK oN Or Ou Oy Oz Pa Pb Pc Pe PF Pg Ph Pi Pj Po Pz Qa Qb QC qD Qc Qm qO qP qU Qv Qw qX qY qZ rB Rc Rf Rg Rh Ri Rj Rm rW sC sK sO Ss tN tO tR TT tU tV tX Tz Ua Ub Ue uI UL uM uP uR uU Uv vB vC Vo vP vS vT vV wD wF wG yD yH yK zG xA Tj tF) Ad(AA aD AF aH aI aJ aK AL aM An AO AP aQ Ar AS aU aV AX aY aZ Ba BB Bc bE BG bH bI bL bN bO bP bQ bR bS bV bW bX bZ cA cC cD CH cI cJ cL cM CO cP CQ cR CS Ct CU CV CW CX cY cZ dA DB DC DD dE DG dH dI dJ DK DL dM dN eC Et Ex Fi Fp Fr Fw hC HF HR hV Hw hX iB IC Ih Ij Im Io Is Iu Jd jE jF Jg jH JI jK jL Jo jP jQ jR jT Kc Kp kR kS Kx lM lN lO Lu Lv Lw Lx Ly Lz Ma Mb Mc Mi Mn Mp Mq Mr Ms Mt Mv Mw Mx My Mz Na Nb Nc Ne Nf Ng Nh Ni Nk Nl Nn No Nr Nw Nx oE oF Og Oh oN Oy Pa Pb Pc Pd Pe Pj qG qH qT Qv qW QZ rB tO tR tS TT Ur Uv Vo wL zH) Jd(aA aD aE aI aJ aK AL An AO AP aQ AS aU aV Aw Ax aY BA bB Bc bE bF BG bH bI bL bM bO bP bQ bS bV bX cA cC cD cE cG CH cL CO CP CQ cR CS Ct CU Cv cW cY DC DD dF DG dH dI dJ dK DL Dp Ed Ef Em eQ Ex Fa fB Fc Fd Fw gP Gz hA HB HC hF hG hO hR Hu Hw Ih Ij iO Iu IZ Jf Jm Jo Jq Kd Ke Kg KK Kl KO KQ Kr kS Kz Lp lX Ly Mb mF Mg mM mS Na NH Ni NJ nL Nm Nn nR nU nW oK Om oN Ow Pk Qb Qc qQ qU Ra Rb Rj Rm Rx Ry Sf Sr Tr tV Ue Uh Uo Us Uu Uy Uz Vi Vj Vp Vs Vt Vu Vv Vz Wb Wc Wd We Wf Wg Wh Yd Yi Zw Zx Tm Xa Ti Th tF) Et(aD aE aF aG aI AJ aK AL aM An aO aP Ar aS aU aV Aw AX aY aZ BB BC bE bF BG bH bI bJ bM BN BO bP bS bW bX cB cD cE cF cG CH cI cJ cL cM CO cP cR Ct cU cV CW CX cY cZ dA dB DC DE dF dG dH dI dJ DK dL dM dN Dp Ed Ef Ex Fa Fy Gl Gp HA Hb hX Ib Id Iz jD JE JF jG jH jL jM jO jP jQ jR Ju Jv JY Kc Kd Ke Kf Kj Kk Kl Kn Kq Kr Ks Ky Kz Ld lK lL Oa Or Ow Ph Pi Pj Qg Qh Ql Qm Qn Qt qU QW QX Qy qZ Ra RB rC Rf Rg Rj sH sK Sr Ss St To Tr Ua Ud Ue Uf uG Uk Ul Um Un Uo Up Ut Uu vA Vp Vq Vt Vv yJ yE) Jg(aA aE AF aI aJ aK AL aM An AO AP AS aU aV Aw AX aZ Ba BB Bc bE bF BG bH bI bJ bL BO bP bQ bS bW bX bZ cC cD cE cF cG Ch cJ cL CO Cp Cq cR CS Ct CU CV Cw CX cY cZ dA DB DC DD De dF DG dH dI DK DL dM Dr eC Fn fP fR Hf hG Hw Ib Ic Il In Io Ip Is Iu Jf Jq Jr Kn Kp Kx Lh Li Lj Lt Lv Mb Mc Mh Ml Mn Mr Ms Mt My Nh Ni NK Nq Nr Nx Of Og Oh Om Or Oz Pa pF Pj Pk Po Qa qC Qe qI Qu Qv qY Rx Rz tS tT tX Tz Ub uM Un Uu Ux Vb Vo Vw Yd zH Tl Tj) Ok(aE AF AJ Al An Ao Ap As Aw AX Ba Bh BC bF BG bL Bn bS bV bW bX cD cG Ch cL Co Cp Cq Cs Ct Cu Cv Cw Cx Db Dc Dd De Dg Dk Dl dN Dw dX eC Ef eT Ex FN fY Gl Gp gV HB hC hF hG hR hX iJ iO iP iZ Jf jG Kc Kd Kf Ki Kj Kk Kn Kp KQ KR KS Kx Ky Kz nY oE Or Ou pF Ph Pi Pk qB qD qG QH Qt Qv Qz Rc Rg Rh Ri Rj Rm rN rR rS rU rV rW sJ sM sO To Tr Tt tU Tv Tz Ua Ub Uc Ud Ug Ul Un Uo Up UR Us uT Uv vO vT vU wH wK yJ yL zG zI yE tM Wm) Di(aH aK An Ap aQ AR aU aY BA Bb bC bE bJ bM Bn Bo bR Ch cM cN Co cP cQ cT cY Dc De eC EF Ex Fn Fp Fr Fw GL hC Hf hG Hq Hu Hx Ih iJ Il IP Iq Iu iZ Je Jf Jh Jj jL JM Jt jY Kf Ko KP kQ kR kS Kx Li Lj lL Lv Lx Ly Mb Mc Mg Mm Mn Mp Mr Ms Mx My Mz Na Nb Nc Ne NF NI Nk Nm Nn No Nq Nr NT Nu NW Nx nY oE OF Oh Oi Om oN Ow Oy Pa Pb Pc Pe PF Pj Po Pz Qd Qw qY Qz Rh Ri Ss Tn tO Tr tS tT tV Un Uv zH Tj) Kq(aC Af aH AJ aK aL aM aN aO AR aU Bb BG Bo bZ cA cB cC Ch CQ Ct Cu cV CW Db dG DK dL Dp eC eD Fb fP Fw gL Gp gW hB hC hF hO Hr Hx Ii IJ Ik Il iO Ip Ir Is Iu iZ Jj Jl jY Ki Kn Kp kQ KR kS Kx lL Lv Mc Mf Mi Mj Mn Mp Mt Mv Mw My Mz Na Nb Nc Ng Nk Nn Nq Nr Nt Nv NW NY oE Of Oh Oi Om Oy Oz Pa pF Pg Pj Pk Po qC qI Ql qO qQ Qw qY Qz Rh tR tS tV uM uN Uo vH wG yK zH) aN(aA aD aE AF aG Aj aK Al aM aO aP aQ AR As aX aY bB bE bH bI bJ bL bM bO bS bV bW bZ cA cD cJ cK cL cM CO CQ cU cV cW CX cZ dA DB Dc DD dG dH dI Dk dM EM fP Fr Hq Hu Ic IH Ik Il Im Iq Ir Iu Iv Jl Jm Jn Jo Jq Kf Ko Lh Li Lu Lw Lx Ly Mb Mc Mh Mm Mq Mr Ms Mu Mw My Na Nc Nd Ne Ng Nh Nl Nm Nn No Nr Nt Nu Nv Ny Oe Oh Oi Pc Pf Po Pz Qa rC Vh) Bb(aD aH aI aJ aK aL aM aP aQ aS aU aV Aw aY bB bE bF bJ BN bO bP bQ bR bV bW bX cG cJ cM cO CP cQ cY DE dF DG dH dK DL dM dR eC eF gP hF hW iA Ic iJ iP Is It jI Kc kR kS lN Mt Nb Nc Nd Ne Nh Nk Nl nY oE oF oH oN pF qT qU QV qW Qz rA rO rP rQ rR rS rT rU rV sM Tt uL Uv uX uY vP vS wB wD wL yJ yL zG zI) Tt(aC aR aW BC bH Bo bU bW cA cN Cs Cv Cw Cx Dc De dK dN Dr Fa Fb Fc Fn Fw Gc Gh gL hB Hf hG Hp Id IH Il Im Is It Kc Ke Kk Kn Ko Kp Ks Kx Ky Li Lj Lw Lx Mm Mt Mz Nd Ng No Nr Nw oD Of Oh oK Or Ou Pd Pf Pj QA Qe Qh qQ Qv qY Qz Ri rP Rx Ry Sr St tS tX Uf UG Un Ur Uv VB Vo Vt Vz Wb wL Yl Zq Zx Ye Xa Tj tF) Ji(Ar AW BA cB cF Ch cK cM Cp cQ CT dD De Dl eM fP hL hO hP Hq HR Hu Hv iA IH Im Iq Jh Jl Jm Jn Jo Jq Jt Lh Lj Lw Ly Lz Ma Md Me Mf Mh Mj Mk Ml Mm Mp Mr Mv Mw Mz Na Nb Ng No Ns Nu Nv Ny Oy Pb Pd Pe Pf Pg Po Pz Qb QD qI qY sC sO TN tO tR tS tT tX uG uI uN uY uZ vB wD wF wG wK wL wP tL xA Tj) Cp(aD aE AF aI AJ aK aL An AO aP aQ AS aX aZ Ba bB Bc BG bH bI bL BN bP bS bV bX cA cD cH cI cJ cL Co cP cQ cS CU CV Cw CX cY cZ DB Dc DD De dF dG dJ dL Ef Ex FP Fr Fw Gl Gn Io Is Mn Mt Mx My Mz Nd Nf Nj Nw Om Qa qC Qd Qe zH Tk Tj) fP(aC aD aI aK Ap aQ AR aU aV Aw aY BC BN cD cE Ch cM cO CU cW cY Dc Dg Dl dN eD Fr iH Lh Mz Nw rB rS sC sK sO tO tS tT tU tV uG uL uN uO uP uR uT uU uV uW uX uY vA vB vC VH vI vP vQ vT vU vV vW wB wD We wG wH wJ wK wP yD yH yJ yK zG zI yE tM tL xA) iH(aI aK aL aQ aS aU aV Aw BA BC bF bP bR bW cB cE cG cK cO cQ cT cU cX cY DE dJ Dl dN Fr hR iC iJ iO Is jD jL jM jU jV Ke Kf kG kI Kl kP lK lM LX Mg mM Mn Mv Mw Mz nI nJ nO nR Nt Of oH oK Pd pS qT qV qY sC sO Uf uI uL uM uN uO uX uZ Vh vW Xa tF) cF(AA aD aE AF aH aI AJ aK aL AO AP aQ Ar AS AX aY bG bH bI bJ bN Bo bP bR bW bX cA cC Ch cI cJ cM CO cP CQ cR Cs cU cV CX Dc dE dF dG dI dK dL dR EF gL hB hX Is Kc Kf lL Mn Mt Mz Nh Nw Nx qC TN tV tX Un Vh tF) Nj(Aa Ap Ar aW Ba bB BC bF BN bQ bR bU bV cG cN Co Cw Dc De dF Dg Dk Dl dN fR Hq Hv Ih Ik Il In Iq Ir It Jk Jn Jr Lv Lw Ly Lz Mb Mc Md Mf Mg Mi Mj Ml Mq Mw Mx Nc Nd Ne Nf Ng Nh Nk Nl Nm Nq Ns Nu Ny

Figure 4 Continued

Oe Of Og Oi Oz Pb Pc Pe Pg Pz Qb Qc zH) aC(dX eP Fp Fw Gb gC Hq Ic Ih Ii Ij Ik Il Ip Iq Ir Iu Je Jk Jl Jm Jn Jo Jq Jr Kf Ko Lj Lv Ly Lz
Ma Mb Mc Mf Mh Mk Mn Mq Mr Ms Mx My Mz Nb Nd Nf Ni Nk Nn No Ns Nt Oe Oh Oi Oz Pa Pb Pc Pe Pf Pg Pj Pz Qc Rx Rz Un Wd)
Cw(bU cB dR eC eF gL gP hB hC hF hG hL hO hR hV hX iC iJ iO iP jD jG jI jO jR jU kQ kR kS IN lO nC Nd nT nW nY oE oF qC qI qO qT
qV qX qZ rA rN rS rU rW rZ sK sM tS tT tV uG uL u0 uZ vA vI vS vV wL wQ yH Tj tF) aR(aW Ba bR cT De Dg eD Ef Fb Hq Hr Hu Il Im It
Iv jD Jj JL Jn JQ Jr jU Kc Kf Lh Li Lj lM Lw Lx Ly Mg Mm Mn Mr Mx My Mz Nf Ng Nh Ni Nl Nr Nt Nv Nx Ny Oh Oy Pa Pd Pe Pj Po qC qP
Qv rC rW sC sO tO Un We Xa) zH(Al Ap Aw Ax Ba Cq Ct Cv Db Dc Dg Dk Fp gW Hu Hv Ih Ik Iq Jj Jk Jm Kd Ke Kn Ko Kp Kr Ly Mb Mc
Me Mg Mh Mk Mt My Nb Nd Ng Nn Ns Nt Nu Nx Oe Og Oi Or Ou Oy Oz Pc Pi Pk Qv Qw Qx Rh Rj Sr tN Uf Up Ut Vp wD yH) Lh(bR eD
Fp hL hR Hw iA Il In Io Is jG Jj Lv Lx Mb Mc Mn Mt Mx Nc Ne Nh Nl Nu Og Oh oN Pd pS Qa qY rN sC sK sM sO tR tU uG uI uL uN uO uP
uV uW uX uY uZ vA vI vO vQ vT vV wB wC wE wH wJ wP wQ yH yK zA Tj) Lx(aA Ch Fp Fr Hu Ii Ij Ik In Iq Ir Is It Iu Jh Jk Jm Jq Js Li Lu
Lw Lz Mc Md Mf Mg Mi Mj Mk Ml Mm Mn Mq Mr Ms Mt Mw Mx Nb Nf Ng Ni Nk Nm Nn Nr Ns Nt Nu Nv Ny Oe Of Oi Pa Pf Pg Po Pz Qb
Qc Qd Qe Tn) Nw(aG aH aW bU bZ cA Ch cO cQ cU De eF eP Ew eZ Fb fN gP gW hA hL hR Ic jM jY Kx oK Pk Pz qB qH qI qO qP qQ qX
rO rS rV rW sC sJ TN tQ tR uI uL uM uO uP uY uZ vA vB vC vH vP vV wD wG wP yH xA tF) Mm(Fb Fr Ik Iv Jj Li Lv Ml Mt Nh Ni Nk Nr
Nx Oz Pa Po Qa qD Qe qH Qv rN rO rQ rR rS rV rW sH sM sO Tn uG uL uM uO uP uR uT uU uW uX uZ vA vB vC vI vO vQ vS vT vU vV
vW yJ yK yL zA zG zl tL) Fb(Aj Ar aW bQ cG cN cT Eq Ex Fd Fw Gb Gd Gh Hl Ho Hp Io Jj Kf Ki Kn Ko Lp Mc Mz Pj Ps Qv Qz Ru Rv Rz
Sf Sh Si Uf Uy Uz Va Vb Vi Vj Vw Vz Wb Wd Wf Wg Wh Yh Yi Zq Ye Tm Xa Tj Ti Th) Is(aE aH An aQ aS aU aV aW bA bE bL bN Bo Ch
cK cM cQ cS cT cU cY dD dE dK Dl dX Fp Fr Hw Hx Ic Il Iq Jj Jt Li Mb Ml Ms Mt Nc Ne Nh NK Nt Nv Nx Og Oz Qb Qv tV Ur Tj) Nl(Ar cB
Ih Ii Ij Ik Ip It Jh Jk Jl Jm Jo Jq Jr Lj Lu Lw Ly Mb Mc Md Me Mf Mj Ml Mq Mr Ms Mv Mw Mx My Mz Na Nb Nf Nh Nq Ns Nu Ny Oc Of
Og Oi Om Oz Pb Pc Pd Pe Pf Qb) Jt(bA Bo bR cB cK cN cQ cT dD dR eD eF Fi fN Fp gL gP gW hB hF hG hL hO hP hR Iv iZ jD kQ kR Li
Mb Ml Nh Nk nW Nx pY Qa qH qI qQ TN tT tX Ug Uv wD wG xA Tj Th) aW(AA AF aI Aj aK aL aM AO aP aQ aU bB BC bJ Bo bQ bX cD
cE cI cJ cL cM cN Co cP cQ Cv cW CX dA DC dD dF dH Dk Ef Fr Kf Mt Nx Pj Tn Uf Un We Xa) Oh(eO Fw Hr Hv Ib Ic Il In Iv Jf Jh Jv Lv
Lw Mc Me Mk Ml Mq Mw Mx Mz Nc Ne Nh Nu Nx Of Og Om Pd Pe Pf qC Qw Rh Ri Rm Tn Ua Uf Ur Ut Uv Vv wL Wm Tj) eB(Aa Af Aj
Al An AO Ar As Ax bZ Ch Co Cq Ct Cu Cv Cx cZ Db dC Dd dG dK dL dR eD eF Em Eo Fw GL GP Je Jh Jj Kf Mt Nh Om Qa Tn tT Vh Wh)
Mn(Ba bR eP Fi Fp gV In Ir It Je Jj Jr Kc Kx Ky Lv Mc Me Ml Mq Mr Mx nK Nr Ns Of Og Om Oz Pd Pe Pf Pi Po Qw Qy Rf Rg Rh Um Uo Ut
Vc Vp Wm Th) Mz(Ar bA Fp hA hV hX iB Il In Ir Iv jG jh jl Jj Jk jO jQ jR jU jY Kc IK IM IN Lv Mx Nc Nf Nh Nu Nx Pd pF Po rA rC rO rP
rQ rT sO uZ wG tF) Nd(bF De Ex Hq Hr Hu Hv Hw Hx Ii Ij Ik Iq Ir Iu Jn Jo Lu Ly Lz Mb Mc Mf Mh Mj Mk Ml Ms My Ne Ng Ni Ns Nu oD
Oe Oi Oy Pb Pc Pg Pz Vh) Tn(Ar bR bU dK Fn Fw gC Hf Hx iA Ib Ic Io Iu Ko Lw Mc My Nf Nr oK Om Oy Pd Pj Qb Qm Qu Qz Rh Ua Ub Uf
Un Uo Ur Uv Uy Vc Vp) Aw(aH An Ap aQ Ar aS aU aY bA bB BC bE BN bR cE cG Ch cM cO cP CQ cT cY dD DE dJ dN dR eF eO Fr gL
gP qO rB) Iv(Fp Hr Ip Ir It Jh Jq Jr Lj Lv Lz Ma Mf Mg Mp Mt Mu Nc Ne Nf Nh Ni Nm Nn No Nr Ns Nt Nv Of Om Oz Pd Pf Po Qa Qd Qe)
Kf(bR cN eF eP Fw gP gW hA jM IL oH oN qI qO qQ qU qY rC rO rQ rR rU rV sC tN tR tV tX uW vB vH wC wD wF wJ wQ zA tL) Vt(eD
hL hP jD pS pY qA qH qP qQ qZ rN rQ rX sC sK uL uM uN uP uR uT uV vB vI vO vP vQ vU vV wP yD yH yJ zG zl yE) Li(aA bR Fp Fr Hx
In Jj Jq Lv Mb Mr Mt My Nf Nh Ni Nk Nm Nq Nr Nt Nu Nx Og Oz Pa Qa Qb Qd Qe Qw Qz tV Vc Tj) Mt(aG aH Aj An Ar bR bU De Eo Fp
Fr Ic Il In Jr Lj Lv Mb Ms Ne Nh Nx Oz Pj Po Qa Qd Qe Qg QI Qv Qw Tj) Pj(cN gL gW hG iB iC jE jF jG jH jI jK jL jM jP jT jU jV lK IM IN
lO oK qT qW qX rA rY rZ sJ uO vA) Qa(bR Fi Fp Fr Hr Hw Hx Il In It Jj Jq Lv Ly Mg Ml My Ne Nf Nh Nk Nm Nt Nu Nv Nx Og Om Pe Tj)
jI(Bc eB Ic jY kC kF kK kN kP lW IX mE mF mH mM mP mU mZ nA nB nF nI nO nR o0 oP oQ Wc We Zq) tV(Aa Ap Bc Dg Dl Ed Fw Hf
Hq Ih Im Io It Iq Kj Kl Kz lK Lu Lv Ms Na Nu Nv Of Om Qw rW wL) Nh(aA cT Fp Fr Il Im In Jj Jq Lv Ma Mp Na Nb Nm Nn No Nr Nt Nv
Of Om Oz Pd Po Qd Qe) Ic(aP Ar BA cQ cT dD De dN Fr gL hW jD jG Jj jM jV Ld IL Qv rC Un Ur Uv wG xA) bU(An Ap Ar aU BC Bg bH
bM Bn bQ cN Cu dB dD dF Dg Dl dN Fr Jh Jj nN nT Un Vh) Nc(aA Ar Fp Il Im Jl Jr Lj Lv Ma Mb Mp Mr Mu Nb Nk Nm Nn No Nr Nt Pd Po
Qd Qe) Bc(cK gW hO hR iB iC jE jG jH jK jL jO jP jQ jR jT jU lK IM lO qD qU rC rW) Vh(Ch EF Fp gC gL gP Ib Im Io jF Jk Jn IN Mu nJ Nk
NY Oi Pk Ps Ut Vb) Un(bR cT De hA hP iA Io jD jG jH jO IL pY qB qU qY Rc rS uM uV vS wL yK) Vq(hO jO qB qX qY rB rN rO rU rX
sO tO tS tX uL uZ vI vT Zq yE tM xA) iC(eD jD kC kE kl kN kO lX mE ml mM mP mW mY nB nC nJ nL nM nO nT Wh) Nc(aA Fp Il Im Jq
Lj Lv Ma Mg Mp Mu Nm Nn Nr Nt Nv Nx Om Po Qd Qe) Kc(eD cF gP hA jY oK oN qC qD qQ rX sJ tO tR tS vB vH wG wL xA Tj) Uf(bR
eD jD jO oK Oy Pa qC Qv qY rX tQ tR tX uM uZ vB Vo vS wH wQ) nN(aA bF kE kG kN kO kP lW mF mM mP mT mZ nA nB nC nH nL nR
oP oQ) Tr(qO qQ rN rP rR tO tS tU uN uZ vB vQ vU wG wJ wQ yH zA tL xA) Nx(aA bR cK Fr Lj Mr Ms Nf Ng Nk No Nr Nt Nv Oz Pa Pc Pd
Po Qd) Ar(bA cT eD gW Io Jh Kc Kn Kp IL Lw Mh Nm Ow Pb Pd Qz Ss Ut) fR(aK aQ aS aU aV bM Bn bQ bW cE cG Ch cT cY dB GP jQ
rX) Ap(bA Bn cK cT eD iA qI qO qP rS rX sC sJ tQ tX uM uZ xA) Fr(aA Fi Hw Ik Jr Lv Ly Ml Ms Mw Nf Nt Og Om Pa Po Qz Tj) We(aO aX
aY bG bR cP Dc Dd Gn Gp Io kR oH oK oN Pk Rc Vb) Ko(aG aH bH bR cH cN cQ cT eM Ex Fi Fw gP Il oK Qv Qz Tj) Fp(Hw Jh Jj Lv Ma
Mg Nf Nm Nn Nt Nv Of Om Oz Pd Qd Qe) Xa(bW gP gW iA iJ iP iZ jR jV kQ kS nA oE Oy pF Rh Ss) oD(cM cX Ed Iz Kr Ky Nf Nt Nu Oa
Or Rf To Up Vp Yh Wm) Ip(hO hV Jj pS qD sM tU uP wE wF wK wP wQ yD zA yE) Ut(Fc Fi Gc Hp Lt Rt Ru Rv Rx Uw Vb Vc Vi Vw Wh
Tj) bF(aH An aY bC bE cC cK cN cO dD dE Dg dN EM IX) Ef(Bo cN Dr Fi Gc Hp Lp Lt Si Uw Va Vc Yg Zx Tm) cT(aK aU aV bC bM Bo
bR Ch cK cN Cu dD Dg Dl Kc) eD(aF cS cV Db Dk Hb Hf hG Id jD Ky Kz Po Qw vS) Qv(De Io It Kj Mg Pd sC o0 uU uV vA vB yJ zA) Jj(lt
Jk Lj Lv Mb Mg Nm Nt Nv Of Oi Po Qe) Dl(aS bA bC Bn bR dD De gW jY qC tS xA) Dg(aS aV bA bJ Bo cK cN dD De gW tT) Po(Hw Il In
Lv Nf Ni Nt Nu Og Oz zA) bR(bM Bn bQ De dF dN Ex Kc Om Qd Qe) Lv(aA Nn No Nr Nt Nu Nv Om Oz Pa) Ri(pS rU sC sM uZ vS wD wH
wL tM) qX(Hf Uy Uz Vb Vi Vj Vw Wd Wg Wh) qT(lX Pa Uw Ux Uz Vb Vi Vw Wd Wg) Bn(aK aU aV bJ Bo cN cP cY IX) Zq(eC gL gW hA
lb nI nJ nT Rh) De(aH aU aV Bo dN Il Qz Tj) Nv(Hx Lj Ml Mx My NK tT) Om(Hr Hw Il My Og Oz tT Uv) bA(bM Ch Cu Dr dX Em Io It)
eP(bB Hb Hc Kk Kp Kx Ou Ss) Ba(aH bM cK Ct gP nT tF) Eo(aP bB dB No Nt Pa Pf) Fi(Cu Dk Iz Oi Oy Qh Ss) Nr(Hw Il In ml nK Oz Tj)
Ib(Gc Vb Vj Zw Zx Tm Tl) Jh(Lt Rx Uy Vc Vi Vj Vw) Ex(cA Ch gW Je Ss uZ) Nt(eM In Nk Oz Pa Qe) Iz(Lt nT Uw Vb Vc Zx) Kc(aS cK rX
uN vB wL) Ky(sC sJ uP uX zA xA) dN(aQ aV bJ cK dD rC) sO(aX Hf Na sC uM vP) Cu(aV cK qC wQ Tj) Nm(hO Oz qD tN tS) Wh(eC hC Io
jP mF) Tl(hC nY Oi Qy tF) Rv(gC gL mZ nJ Oi) bM(bQ cE Ch Ct dD) tX(Ao Fw Lu nW Pd) rC(cS Hf hG Kz rN) rX(aF cV dB hB Hf) Bo(aU
aV cY gW) Gn(lW IX nJ Pi) Mb(AA eO Qe) Kg(rN rS tS tT) Tk(bG fN hG vV) nI(jF jQ oV Th) nK(hV Lu Mv Nq) wL(gW tT wD Wn) jD(Je
Pi Qm vS) qY(Wb Yd Ye Tm) Hl(gL mT mZ) Rc(Dr Hp Ti) Kz(uZ vB xA) Pf(DW gV) aM(DW eO) bQ(IX mW nF) cG(cK eO nO) nJ(Du Fd
Ry) qC(li Kl Tz) jH(mM Vj Wf) vS(ld IN Qw) Dk(Fc Lt) Tj(Kn Pe) Em(dB gW) Nu(Ma Oz) Nk(Qd Qe) Hx(aA zA) To(dU jB) Il(Ir Pa) Hb(qD
vB) It(Qg Ur) Kx(gV Io) Op(iZ mZ) Ou(dX gV) Uw(jG jM) Uy(dU Oy) Vw(jO jY) Pd(Hw tT) bB(dX eW) gL(Vc Tm) IX(cX oN) sF(Hf Hr)
jF(kG Vi) pK(Du Gc) BgDr ChnF FwtS GheQ GzhO MatT MquZ MspS NahV TzqU Inlr YgeM JelL SsLt WdhC QwuX KlrN PsOy UhsJ UvkF
PazA PeeW cKdF dJeO gCiJ gWnL nRIK wDuU jQkN

Figure 4 Continued

Unconstrained panels with 2 analytes, where 1.0E-3 >= 'AUC p-value' > 1.0E-4. Contains 11,942 panels of 199,257 total panels evaluated. :
Tt(aA aD aE AF aG al aJ aK AL aM AN AO AP aQ As aU Aw AX aY aZ BA bB bE bF BG bI bJ bL bM bN bO bP bQ bR bS bV bX cB cC cD
cE cG CH cI cJ cK cL cM CO CP CQ cR cS CT CU cV cW cX cY cZ dA DB dC DD dE dF DG dH dI dJ Dk DL dM Dp Du eC ED EF EM Eq
Ex Ez Fd FP Fr Fy Gb gC GI Gn GP gW Gz Ha Hb HC HL Ho Hq Hr Hu Hv Hw Hx iA Ic Ii IJ Ik In Io IP Iq Ir Iu Iv IZ Je Jf Jg Jh Jk Jl Jm Jn Jo
Jq Jr Js Jt Ju Jv Jy Kd Kf Kg Ki Kj Kl KQ Kr Kz Ld Lh Lp Lt Lu Lv Ly Lz Ma Mb Mc Md Me Mf Mg Mh Mi Mj Mk Ml Mn Mp Mq Mr Ms
Mu Mv Mw Mx My Na Nb Nc Ne Nf Nh Ni Nj Nk Nl Nm Nn Nq Ns Nt Nu Nv Nx Ny Oa OE Og oH Oi Om oN Op Ow Oy Oz Pa Pb Pc Pe pF
Pg Ph Pi Pk Po Ps Pz QB QC Qd Qg qI Ql Qm Qn qO Qt Qu Qw Qx Qy qZ Ra Rb Rc Rf Rg Rh Rj Rm rO rR rS rU RV rW Rz sC Sf Sh Si SJ
sM Ss TN To TR tT Tv Tz Ua Ub Uc Ud Ue Uh Uk UL Um Uo UP Us Ut Uu Uw uX Vc Vh Vi Vj Vp vQ Vs Vu Vv Vw wC wD We wG Wh
wK wP Yd yH yL zA zH Zw yE Tm TL Wm Ti) Tn(aC AD AF aH aI AJ aK AL aM AN AO AP aQ aR As aV Ax aY Ba Bb BC bE BG bH bI
bJ bL BN BO bP bQ bW bX cA cD cE cG CH cJ cL cM cN CO CP CQ cR CS Ct CU CV CW CX cY cZ dA Db DC Dd DE dF DG dI dJ Dk
DL dM dN Dp DR ED EF Em eQ Ez Fa Fb FP FR Gd GL GP Ha HB HC hF Hp Hq Hr Hu Hv Hw Id IH Ii IJ Ik Il Im In iO Ip Iq Ir Is It Iv IZ Je
Jf Jg Jh Jj Jk Jl JM Jn Jo Jp Jq Jr Js Ju Jv Jy Kc Kd Ke Kf Kg Ki Kk Kl Kn Kp KQ kR KS Kx Kz Lh Li Lj IL Lt Lu Lv Ly Lz Ma Mb Md Me
Mf Mg Mh Mi Mj Mk Ml Mn Mp Mq Mr Ms Mt Mu Mv Mw Mx Mz Na Nb NC Nd Ne Ng Nh Ni Nj Nk Nl Nm Nn No Nq nR Ns Nt Nu Nv
nW Nx NY Oa oD OE OF Og oH Oi Ok oN Or Ou Ow Oz Pa Pb Pc Pe Pf Pg Pk Po Ps Pz Qa Qc Qd Qe Qg Qh Ql Qn Qt Qv Qw Qx Qy Ra Rb
Rc Rf Rg Ri Rj Rm Sr Ss St To Tr TV Tz Uc Ud Ue Ug Uh Uk Ul Um Up Us Ut Uu Uw Vb Vh Vi Vo VS Vt Vv Vw Wd We Wf Wh Yd Ye
Tm Tl Wm tF) Kq(aA AD aE aF aG aI Al An Ao AP aQ aS aV Aw AX aY aZ BA bB BC bE bH bI bJ bL bM BN bO bP bQ bR bS bU bV bW
bX cD cE cG cH cI cJ cK cL cM cN CO CP cR CS cT cU Cv CX cY cZ dA dB DC DD DE dF Dg dH dI dJ DI dM dX Ed Ef eP eT Ex Ez Fa Fi
Fp Fr Fy gC GI gV Gz Ha Hb Hc hL Hq Hu Hv Hw Ib Id Ih Im Iq Iv Iz jD Je Jf JG Jh Ji Jk Jm Jn Jo Jq Jr Js Jt Ju Jv Jy Kc Kd Ke Kf Kg Kj Kk
Kl Ko Ks Ky Kz Ld Lh Li Lj 1K Lu Lw Lx Ly Lz Ma Mb Md Me Mg Mh Mk Ml Mm Mq Mr Ms Mu Mx Nd Ne Nf Nh Ni Nj Nl Nm No Ns Nu
Nx Oa Oe Og Or Ou Ow Pb Pc Pd Pe Pf Ph Pi pS pY Pz Qa QB Qc QD Qe QG QH Qm Qn qP Qt QU Qv qW Qy qZ Ra RC Rf Rg Ri Rj Rm rN
rW rX sC sM sO Sr Ss St tN TO tQ Tr tT Tv tX Tz Ua Ub Uc Ud Ue Uf UG Uh uI Uk UL Um Un uO Up Ur Us Ut UU UV uW uX uY vA vC
vI Vo VP vS Vt vU vV wH wJ wK wQ yD yH yL zI yE tL Wm Th) Jp(AD aE AF aJ aK AL aM An AO AP aQ AS aU aV Aw AX aY aZ Ba BB bE
BG bH bI bJ bL BN BO bP bQ bS bW bX bZ cA cC cD cE cG CH cI cL cM cN CO CP CQ cR CS Ct CU CV CW CX cY cZ dA DB DC DD
DE DG dH dI dJ DK DL dM dR dW dX Ed Ef eO eT Ez Fi fN fR Fw FY GL GP gW Ha Hb HC hL hP hV hW hX iB iC Id Ir It Iz jD jE jF JH jl
jK jL JO JQ jR jT JU JV JY Kc Ke Kg Kj Kl Ko kQ Kr Ks Ld IK IL IN IO Md Mm Mp nK Ns nY Oa oE Ow pS pY qA Qd QG QH qI Ql Qn
QT Qu qV qW Qx Qy RA Rb rC rN rO rP rQ rR rS rU rV rX rY rZ sJ sM Sr St To tQ Tr Tv Uc Ud Uf UG Uh Uk Um Un UO Up Ur Us UT Uu
uV uW uX vA vO Vp VQ Vs Vt VU Vv vW wB wC wE wH wJ wK wP wQ yJ yL zA zI yE tM Tk Wm) Di(AA aD aE AF aG al AJ AL aM AO
aP AS AX aZ bB Bc BG bH bI bL bN bO bP bQ bS bV bW bX bZ cA cC cD cE cG cH cI cJ cL cO Cq cR CS Ct CU CV CW CX cZ dA DB dC
DD dE dF dG dH dI dJ DK dL dM Ed Ez Fa fR Fy Gp HA Hb Hc HR HV HW IB iC Id Ii Ij Im In Iz jD jE jG Jk Jl JO Jq JR Js jT JU JV Jy Kc
Kd Ke KG Ki Kj Kk Kl Kn Kr Ks Kz Ld Lh IK IM IN IO Lu Lw IX Lz Ma Md ME Mf MH Ml Mj Mk Ml mM mP Mq MU Mv Mw mY nC nD
Ng nH nN nO Ns Nv Ny Oa Oe Og oO Or Ou Oz Pg Ph Pi Pk Qb QC Qg Qh Ql Qm Qn Qt QU QV qW QX Qy RA Rb Rc Rf Rg Rj Rm rW rX
sC St tN To tR Tv Tz Ua Ub Uc Ud Ue Uf Ug Uh Uk Ul Um Uo Up Ur Us Ut Uu uZ vB Vo Vp Vt Vv wG wH yH xA Tk Wm) Nw(aD aE AF
aI AJ aK AL aM An AO AP aQ Ar AS aU aV Aw AX aY aZ BA BB BC bE BG bH bI bJ bL bM BN BO bP bS bV bW bX cC cE cG cH cI cJ
cL cM cN Co cP Cq cR CS CT Cu CV CW CX cY cZ dA DB DC Dd De dF DG dH dI dJ DK DL dM dN Co cP Cq cR CS CT Cu CV CW CX cY cZ dA DB DC DD dE dF DG dH dI dJ DK DL dM dN dR dW dX eC Ed Ef eT Fa Fn Fw fY
gL gV hB HC HF hG hP hV hX Ib iC iJ iO iP iZ jD Je JF jG jH jO jQ jR Kf Kg Ki Kj Kk Kl Kn Ko kp kR kS Ky Kz IK IL nK nW nY oE oF
oH oN Or Ou pF Pi Pj pS pY qA qG Qh Ql qT QU Qv Qw QZ rB RC Rf Rg Rh Ri Rj Rm rN rP rQ rR rT rX sK sM sO Ss Tr tU Tz Uf uG Un
Uo UR uU UV uW uX Vh VO vQ vS vT vU vW wB wC wE wF wH wJ wK wQ yD yJ yK yL zA zG zl Zq yE tM Wm Tj) iH(aA aC aD aE aF
aG aH aJ aM An AO aP aW aX aY aZ bE BG bH bI bJ bL bM BN BO bQ bS bV bX bZ cA cC cD CH cI cJ cL cN Co cP cR cS Ct CV cW cZ
dA DC dF dG dH dI DK dL dM dR eC EF Fb Fw Fy GL gP gW hA HB hC hF hG Hu hV hX iA iB Ic Id Ii Ij Im iP Ir It IZ JE jF jG jH Jj jK jO
jP jQ jR jT jY kC kE kF Kg Ki kK kN kO Kp kQ kR kS Ky Li IN IO LW IY Mc mE mF ml mP Mq Mr mS MT MU mW Mx MY mZ nA nB
NC nD Ne NF Ng NH Nj nK nL nM NN Nq Nr nU Nv nW Nx NY oE oF Oh oN Oy Oz pF Ph Pi Po Qa Qh Qt Qu Qv rB Rc rN rS rU rW sK
sM Ss tN tO Tr tS tT tU tX Ue uG Un uR UU uV uW uY vA vC vH vI vP Vq vT vV wB wD wG wH wL wP wQ yD yH yJ zG zI tM TL) Is(aD
AF aG aI AJ aK AL aM AO AP As Aw AX aY aZ Ba bB bC bF BG bH bI bJ bM Bn bO bP bQ bS bU bV bW bX bZ cA cC cD cE cG cH cI cJ cL
cN CO cP Cq cR Cs Ct Cu CV CW CX cZ dA DB DC Dd De dF DG dH dI dJ Dk dL dM dN Ed eF Fb fP fR Fw GI GP Hb Hq Hr Hu Hv iA Ih
Ii Ij Ik In Io Ip Ir It Iu jD Je JF Jh Jk Jl Jm Jn Jo Jq Jr Js Ke Kf Kk Ko Kp Kx Ky Lj Lu Lw Ly Lz Ma Mc Md Me Mf Mg Mh Mi Mj Mk Mm Mn
Mq Mr Mv Mw Mx My Mz Na Nb Nf Ng Ni Nm Nn No Nq Nr Ns Nu Ny Oe Of OH Oi oK Om Oy Pa Pb Pc Pd Pe Pf Pg Pi Pj Pk Po Pz Qa QC
QD Qe Qg Qm qQ Qw Qz Rc Rg Rm sO Ss To Tr Tv Tz Ub Ud Ue Uf Ug Uh Uk Ul Um Un Uo Us Ut Uv Vb Vo Vp wG wL tL xA Th) Fb(aC
Ad AF aI aM aN AO aQ AS aU aV AX aZ BA BB BC bF bH bJ bL BN BO bP bR bS bU bV bX bZ cA cB cC cD cE cF Ch cJ cK cL cM Cp
CQ Cs Ct CV Cw CX cY cZ dC dD De dF DG dH dJ DK DL dM dN Dp Du dX Ed eP Ez Fc Fn fR Fy Gn Gp Gz Hf Hq Hu Ib Ic Id Ij Ik Il Im
Ip It Je Jf Jg Jh Ji Jn Jr Jt Ju Jy Kc Kd Ke Kg Kj Kk Kp Kr Ks Kx Ky Kz Ld Lh Li IL Lu Lv Lw Lx Lz Ma Me Mf Mh Mi Mk Ml Mn Mr Ms
Mu Mv Mw Mx My Na Nb Nc Nd Ne Nf Ng Nh Ni Nj Nk Nl Nm Nn No Nr Ns Nu Nx Of Og Oh Oi Om Op Oz Pa Pb Pd Pe Pf Pg Pi Pk Qg Ql
Qm Qn Qu Qw Qy Rb Rc Rg Rh Ri Rj To Tr TV Tz Ua Ub Uc Ue Ug uM Un Uo Up Ur Us Ut Uv uZ Vo Yj Yk zH xA Tk Wm Yf) Ko(AD aE
AF aI aJ aK aL aM aO aP aQ Ar AS aU aV AX aY aZ BA BB BC bE BG bI bJ bL bM BN bO bP bP bQ bS bU bV bW bX bZ cA cB cC cD cE cF
cG Ch cI cJ cK cL cM cO cP Cq cR CS CU CV CW CX cY cZ dA DB DC DD DE dF dG dI dJ dK dL dM dN dR eD EF Em Et Fn Fp FR gL
Gp gV Gz Hc HF hG Hp Hr Ic IJ Im In IO iP It Iu Iv iZ Jg Ji jY Kc Kk Kl Kn Kp Kr KS Kx Ky Lt Lw Lx Mc Me Mf Mh Mi Mk Mm Mn Ms
Mt Mv Mw My Mz Na Nb Nd Ne Nf Ng Nl Nn Nq Nr NT Nv nW Nx Ny oD Oe OF Og OH Ok oN Or oV Ow Oy Pa Pb Pc Pd pF Pi Pj Pk Qa
qO Qw Rh Ri Rm rX To Tr tS Tv Tz Ub Un Ur Uv Uw uZ Vc Vi Vo Wd We Wh Ye XA tF) Ji(aD aE AF aG aH aI AJ AL aM An AO AP aQ
AS aU aV Ax aY aZ Bb BC BG bH bI bJ bL bM BN BO bP bS bV bW bX bZ cA cB cC cD cE cG cH cI cJ cL cN CO cP Cq cR CS CU CV CW CX
cZ dA Db DC Dd dE dF DG dH dI dJ DK dL dM dN dR dX eD EF EO eT eW eZ fN fR Fw fY gL hA hF hG hV To Ib Ic iJ iZ jD Je Jf jG Jk jM jO
jY Kk kR kS IK nK oE oF oH Oi oK oN pF Pk pS pY qA qB qH Ql qQ QU Qv Qw qX Qz Rc Rf Rh Ri Rj rN rO rP rQ rR rT rU rV rW sJ sK
sM Ss To tQ tU Tv Tz Ub Ud Ue Uf Uk UL Un UO uP uR Us UT uU Uv uW uX vA vH vO VP vQ vS vT vU vV wB wC wE wH wJ wQ yD
yH yJ yK yL zA zG zI tM Wm) Bb(aE AF aG Aj Al An AO Ap Ar As AX aZ Ba Bc BG bH bI bL bS bZ cA cC cD CH cI cL Co Cq cR CS Ct
CU CV CW CX cZ dA DB DC dI dJ Dk Ef Ex Fa Fn Fp FR Fw GI Hf Ih Ij Ik Il Im Io Iv Je Jf Jj Jr Jt Ju Ke Kf Ki Kl Kn Kp Ks Kx Ky Lj Lu Lv
Lw Lx Ly Lz Ma Mb Me Mj Ml Mm Mn Mp Mq Mr Ms Mu Mv Mw Mx My Mz Na Nf Ng Ni Nn No Nq Nr Ns Nt Nu Nv Nx Oe Og Oh Oi
Om Or Ou Ow Oy Pa Pb Pc Pd Pe Pf Pj Pk pS Qa Qe Qh Qm Qt Qw rB Rc Rg Rh rX sC sK sO Ss St tQ tU Tz Ub Uf UG uI Uk UN UO uP
UR UT uU uV uW uZ vA vC vH vI VO vQ vT vU vV vW wC wE wF wG wH wJ wK wP wQ yK zA yE tM tL Tj) Jg(Dp ED Ef Em eP EZ Fa

St Uc) tX(eC iZ Ki Ma Mg Ms Pc Pi qU wL) Eo(aD aJ aM bP cC cW dG Nn Pe) Ti(eZ hR hV hW hX qD qV qX rB) Nq(Eq fB hV hX nA nF rN Vz Ye) Hp(Kj Mu Pz Qc Qg Qh Ua Us Uu) In(Cq Id Ik Jq Jr Kn Ma Nn Qm) Rz(bW hC iZ lY mF mZ nA oK Rh) Ux(jG Jn jO lM lN oH Pk qX qY) Vj(eF gP Kj Kk nW Qh qY Rh tF) nN(cU Hq Hr Hu Iu Mk Mv oN oO) jQ(kC kK mE mF mI mP mU nR nU) lL(Id Kn Ph qH Qm Qt rN sC Zw) Nk(Ik Jl Mb Mp Mr Mu Ni Nn) Lj(Jl Jq Jr Mb Nf Ni Nn Of) Uw(eC gP iZ jL lM oK qX Ua) Pe(gV Hr Hw Il Ir Nf Og Oz) eO(aD An bP cC cP cQ dG Pz) nT(bB cE dG hB nW Ph Sf Ub) rS(eC Fw Kj Mg Of uM uN zG) Wd(eC gP Io jF Kk nW oK) Qm(eM hA jG jM jV nF qD) Tk(Ir qI qO qP vB yK xA) Vc(Hc Jn Ow Qh qT qV qY) aV(Aa An As aY bC Ct Cx) gW(Ct Dr Ho kC mU pS Ry) hV(Hv kF kG lY mU nR Qw) jR(kC mF mI mU nA Wc Yl) Id(hA hR qD qY uN uZ) Jq(Ik Mb Nf Og Oz Uv) dB(dW EW gV Lw Ly) lX(Ao cM Db hB nY qX) sJ(aP Il jL Ou Uu yD) rN(eC Fw Kj uU wG yD) Gc(dR hC iZ Ua tF) Ma(Il Ly Mr Mx tN) Hl(iZ jB nU pH Vu) Hr(Dr dU mI sH sI) Ir(Iu Lw Og oK Tj) Jl(Hx Mb Ml Og wL) Jn(eW gV nF Vb Wf) Ps(Kj Of Rh Ua Wf) Ow(Ax dX gV Jr nL) Va(iB jL jM lN qX) eM(bB cE Hc Vi Vv) jF(kF mZ nA nR Vw) uZ(aP bX Fa Ms oE) An(aU bC Ct Mx) Gb(dR iZ Mh oK) Nn(Mb Ml Og Oz) Nb(kP mE nA oV) Qz(jD Kl qD qQ) Qy(Lt Rt Rv Rx) Ki(jD qX uX xA) aA(Hw Ik Ly Pc) aF(dW eW vB wL) cM(hB kP oV pF) wG(hB Kn Pi qZ) Aa(aQ cY Qw) Dr(cY Gp Uu) Dw(bP cC cW) Tj(Fa Oa St) Em(bB Hc mH) Gh(fA fB pI) Uc(Vb wL yL) Hq(jB Mr nA) Ii(hL pY qD) Yi(iZ lY mS) Jr(Il Og Oz) Ye(Dd hC oH) Kx(eQ pK Pz) Rg(kF kG mT) Op(mE mF nA) Ou(Io sH sI) Vw(bW jG oH) cV(hR rY xA) dW(hB cW Pz) yD(sF sH sI) qX(Vz Wc Tm) qU(cS Fn St) pS(cI tO tQ) rZ(cS kG nR) lM(bZ wH tM) vB(aO Gl Qw) Db(jU mH) Du(Mu oH) Ew(aM bP) Th(lW oP) Lu(nF tN) Mb(Eq Ry) Mh(Rt Rv) Mv(gZ tF) Ua(Rx Zx) Hc(gV Wf) Yg(eC iZ) Sh(hC nW) Kl(Aj uM) Uv(kG mT) Vb(Kj Of) Vi(bW jO) Pc(sI wB) Pi(qD xA) cK(bC cE) eW(aY cW) wL(Mp qO) jB(cX Uy) qZ(Ms mZ) qT(kF Vz) lK(kF kK) sC(cI Gz) CvjD CxcY FajM MlNy MxOz NdbV UbnU IkOg IohG WfrA QwqD QuRx TmhB KnxA RybW WndR UmeQ UgdU VsmF aIdX bBiA bHnD bXqQ nRrB mHmU mMhX sHoE qHuM jLoQ

Constrained panels with 3 analytes, where 1.0E-10 >= 'AUC p-value' > 0. Contains 40,402 panels of 37,563,518 total panels evaluated. : oD{Ut(Al aM An Bb cM Co Cq Cs CU Dc Dk Dp eC eQ Ez fP Fw Fy Ha Hf Hu Hv Hw Ib Ih Ii Ij In Is Jj Jk Jl Jm Jn Jp Jr Js Ju Kf Kl kR Ky Lh Li Lj Ma Mf Mj Mm mU Mw Mz Ne NH nI nJ Nm nR Nu Nv Ny Om Ou Pb Pc Pe Pg Pi Po Qa Qe Qh Rf Rh Rm Sf Sr St To Tr Ub Uh Uk Ur Uv Ux Vb Vo Vp Tj) Iz(Aa Al Ap Ba Bb Bc Bg bO Co Cq CU DG Dk eQ Ez Fb fP Fr gC Ib Ij Jg Jk Jp Jt Kf Kl KR Lh Lj Lv Mj Mm NH nI nJ Nm Nu Oh Ok Ou Ow Pb Pe Pf Qe Qh Rf Sr St To Tr Uc Uf Uk Uu Vb Vo Vw Yg Yi Zq Zw) Ry(aA aC aD aK aN aV bE bJ BO cB cE cQ cR cW cZ dA dI dJ Dr Fb Fd fR gL hB Hf hG Hp Hq Im iZ Jd Jl kN Ld Lv mE mT Mw Nb nC nD Nl No Nt Nu Nv Oa Oe oO oQ Or Qb Qd Ql Rm Uk Un Ur Vu Vz Tj) Th(Af aJ Al Ax Bb bJ cN Co eC Fb fP Fy Gb gC Gp Hf Ic Jh Ji Jj Kk Kl Ks Lh Li Lj Lu Ma Mn Ms Mz NH nJ nL Nn nR nU Ny Oh Om Op Ou Ow Pe Pg pI Rf Si To Uc Uh Uv Uw Vb Yd Yg Yi) Ld(Al An aO Ar Ax bO bP bX bZ cI cL cM Cs cU dM eQ Fa fB Fp Hp Hu Ib Id Jl kR Ky Li Lj Lv Lx Ma Ms Mw Nh nI Nu NY Oa Og Or Pb Pe Po Ps Qa Qe Rf Rh Sr St To Tz Uk Vi Vt Tm Tj) Tj(Ao aR bC bI bJ bU bZ cD cM cR cU Cv CX dR Du Ed Gb Gh Ho Hp iJ iO Kc Kk Kq kR Md Mk Mq Ms mT nI Ns nU Nv Nx Op Ql Rb Rz Si Uw Va Vb Vj Vw Wd Yd Yg Yi Yj Zq Zw Zx) Si(Ad Aj Ao Ax bP bU cM cU CW dA Dd Dg dU Fb Fy Gh hB Ij In Jd Jm Jn Jp Jt Kx Ky Mg mM Ms Nb No Nq Nr Nu On Pd Pz Qd Qy Qz Rz Tt Us Uu Va Vq Vw Wh Yk tF) Tm(aC aK aL aN aQ bE bJ bM bN bO cB cE cZ dD dJ eQ Fd hB Hf Hp Hq Hv Ib Ih Im Jd Jl Kg Lv mF Ml nD Ne Nl Nv Oa oQ Qd Qz Rx Uv Vi Vu Vz Wd Yd tF) Tl(aC aF aI aK AN aQ aV bC bE Bn cD cN cR cS cY dA dJ Hf Hw iH Il Je Jy kN kR lX Ml mS Mu Mv Mw Mz nB Ng Nl nN No Nu Qd Qz Ub Uk Un Up Us) Zw(aI aM An Ao Bg Dd De Ef Fa Gh gL Hc Ho Ih Iq Jk Jm kN Ky mP NA Nq Nr Nu Nv Oa Oe Of Oy Ph Pi Qy Qz Rh Rm Ua Ue Uk Us Va Wd Yd Yl) Uy(Aj aN Ap aZ Bg bJ bN bU cG cR cU dA Dd De dH Di DU hB HC Ih kO Ky Mg mM Mp nA Ng Nu Nv oQ Oy pH Pz Qz Rv To Uc Ue Us Vz Wf Wh) Gh(aJ aP Bc bW cB cI dB Ex Ez fB fP fR Gd gP iA Ii Jf Jh Jq kR Ma mP Mz Nh Nn Nu Oa Oh Ok Ow pI Qg Qn Rh Tz Uh Uk Up Vb Yg Yi) mT(Fb Fy Gb Gd Gl Ib Ju Jv Ke Kf Kl Kn Ko Kq Kr Ks Ky Nd Op Ou Ow Qh Rc Rf Rt Sr St To Tz Ua Ub Uc Uf Uh Uk Uv Vj Vo Yg Yi) Hp(aA aH aV cR dA Dr fR Gz HB Ib iZ Jd Jk kC kQ Kz Mq Ms Mu Mw Nb nD Nf No Nq Nt Nu Oa Oe On oO oQ Ps Qu Ua Uk Uo Vz) Uw(aD aG aH Bg bL cE cQ cR cW dA Dd Ef fR hB Hc Ib Jd Je Jk Jn Ms Mu Mv Mw Nb nD Nl No Nq Oe oO Oy Ql Ue Uf Uk Un Uo) Zx(aI Fb Fr Gb gC Hb Ii Jh Ji Jq Kf Ko Kq Lj Mn Ms Mz Nm Nn Nr Nu Nw Oi Om Ou Ow pI Pj Qu Rc Sr To Ux Vt Yd Yg Yi) Gd(Ad aH Ao Ap aZ Ba bB Bg cG Ch De Dg Dl Et Gc Gl Io Ir Jg Jp Jt Kr Mp mS ND Ng Oe Of Og On Pz Ss St Ug Wc) Wh(Al AP aW Ch cL Co Ct cW Db Di Eq Fi Fr Gb gP Hb Ik KG Kq Lv Ml Mz nD nK Ok pK Qg Qt Qu Rh Tz Ur Vq Xa) Yd(aL Ao aV aW aZ bG bW cP Di dN eM Gz kC Ki Ko kQ Kz mH Mq Nb Ne Nm Nu Oc Of On Pd pK Qz Tt Uc Up Ur Uu tF) Ps(aC bE bM bN bO dA Dr hB Ib Ih Im Je Jk Jl kN Lv lY Mh Mw Nb nD Nq Nv Oe oO oQ oV Qd Ql Qm Un Uo Vu Vz) Kk(aM Bb bW cM Cs cU gC Hf Hr Js Lh Lj Mm Mn Mv MZ nC NH nI nJ nR Nu Om Pe Qg Qh Rf Ub Uk Uo Ur) Yg(aN aV bH cB cD cE cQ cR dA De dF dU gL hB Hu Ib Jm Mb mE Mu Mw Mz Nb nD Nu Oa Oe oO oQ Rm Uo Wd) Tt(Aa Bb Cq eQ Fy Gb Js Kf Ks Li Ma Mn Mz nJ Nm nR Ny Om Pb Pg Qh Rf Rt To Tr Uc Uh Ux Vb) Yi(aN aV bH cE cR dA De dF dU gL hB Ib Id Jk Ma mE Mw Nb nD Nu Oa Oe oO oQ Qz Rh Rm Uk Uo) Eq(Aj aM bA cE Cq cU Cv Cw DG Dp Gc Ho Ic Jn kN MS Mz nA Nd Ng Nq Qz St Wc Wf Yl) Ko(Aa Af Bb Bc cM cU Dg Dk Ez gC Jg Jp Kf Kl Lv Ma NH nJ Nm nR Op Sr St Uf Uh Uu Vo) Hl(An cE Cq Cw dA dR fA hB Hc Jm Jt Ki lW Mz nD On oW Oy Qu Qz Rv Rx St Ua Uu Va) Rf(bJ bR cB cR cU cW DR Fa Fd fR hB Hq kR Lv Lx Nb nI Nt Nu Nv Oy Tn Ua Uk tF) Fi(aI aM An bJ bN cM cU Dd Dp Jn Ju Jv kN Ky lY mM mP nA nU oK oN Qz Sf Yl Ti) Sj(aF bC bL bV cL cN cT Cx Gb Ip Je kE Lv lY Mh Mv Nc Nt Oe On Qh Ql Rh Vu) Uk(bI bR bU bX cM Cs CX dR Ed Hq kR Lv mF Ms nH Ns Op Qn To Vb Vv Zq) Qz(Gb Hv In Jj Jm Jn Js Mf Mj Mz Ne Nh Pg Qh Rm Rt Ub Va Vb Vp We Yh) Vi(aA aC aD aK bE bM cB cD cY Dr Gz Ib Jd Je Jk Jl Mb Mu Mw Nb Nv Up) Wd(Al Ar Bb Ch Co Fy Gp Ib Ik Ip Jp Kq Ma Nw Om Pe Rh Rz Tz Uf Vb) Gb(Ao bJ cV dA DD hB Iu kC kN Kp Ms Mz Nb Nm Nu Of oO Sr Vw) Ua(Al Co Dc Jk Js Lv Ma Mz Nu Oa Ou Pb Pe Pg Po Qe Qh Rt To Vw) Vb(aN Bg De dU Ef gL Ha Jd Jm kC Ma Nb No Nt Oa Oe On oQ Rm Uc) Dr(cP Dk Hb Ib Im Ke Ki KQ Kz lW Mq Nf Ny Qe Qh Qu Up Vt) Op(aK aN Ao cR dA Ha KN Ms nC nD Nt Nu Oe Of On oO Oy Uc) Yl(aP aW cB Ct cW dD Ez fA Fw kG kR Ml Nh nK pI pK Qg Tz) Nu(cM cX Du Hr Ky Mk Qh Qn Tn To Ub Up Ux Vj Vw Zq Wm) Lv(Ed Ef Hb Hc Ib Jd Qh Qm Qv Qy Sh St Um Ur Vq Vu Wf) Lp(bI bP bX dR Gc Hc mS Nd Nl nY Oe Og On oO Oy Rh Ug) To(aG cR Cv CX dU Fa gL hB iZ Mq Nv Oy Rx Vq tF) Vz(cP Ez fA Fc Fw gP Hb jB Kq kR Pc pK Qg Tz Up) Wf(aJ Ap bN Co Dg Id Ii mM nH nR pI Rh Ux) Qh(bI dR Fa Hq Jk Mq Ns Nv Oy Tn Vs Vv Zq) cM(Di Ex Iv Nd Nf Nj Nr Ns Nt Nv Oi Pa Vq) We(aC aN aV cE Co cY hB Id Mz On Rh Rx) Va(Ad Ap Ch cN Co Dg Fy Ii Kf Kg Ma Uf) Sf(aW bW Ct cW Fw gZ Kg kR mH Ml nK) Zq(aN cR dU gL hB iA kC Nb Nq oQ Rh) dR(Gz Hf Hr Kr Nd Ou Tr Ub Ur Vo Vp) Fa(cR Cs Lj Nh nI Ny Pb Pe Po Qe) Yh(aI Ba Dp Hq Ki nA Ph Pi Rh Up) Yk(bW Ct cW Fw mH Mz nK pK Rh Ur) Rx(Hx mH Mz nC nH nJ nL Pb Pc Tr) Vh(Aa aI cN Cq Ji nC nJ Rt Uv Ti) Sh(aV Co cR Ha kN Nb Oy Rh Uv) Gc(cN gC Hv nC Ok Pj pK Ug) cR(Ha Oa Om St Tn Ur Vt Vw) fR(Fb Fw Ib Jf Ow St Ub Uh) Ho(Ch mH Nh pI pK Rh Tz) Wb(Gz Hb Kl Nl Uo Up) Kr(An Ao aZ bX Cv iJ Oy) Ky(aD bX Di gL Ns Oy Vq) Rt(Co De Ji Nm On Pg Rh) Ux(aV dU Mp Nl Nq Uc Ue) Vj(cQ dA hB kC Nb No tF) nI(Kc Kn Nf Ql Qn Rh Ub) Fc(aC aN bJ hC Ni Nj) Vw(aK aV dA hB kC On) bU(Ez Fw Nd Nj Oi Um) Yj(cB Hf Hq Jm Tv) Wc(bN nH nL pI Vo) Rz(aK aV Dd dU Oc) Vq(aM cU Ni oW Qe) Oy(Dp Ju Ou Ug Ur) bX(Ez Kf Kl Tr Ug) Ti(Kn kR Ml Qg) Xa(aI mM nA Rh) Kc(cX hB Hr Qg) bJ(Qn Qx St Ub) gL(Ib Ou St Tr) An(Fd Lt Ub) Ed(cW NH) Rv(Af Co nC) Aa(Gl Qm) Du(mH pK) Gp(Hr Qg) Ns(Ez Tr) Mz(Qn Vs) Qe(Ue Un) Nv(Oa St) cU(Qn Um)

Figure 4 Continued

Figure 4 Continued mS qW) Gz(qI rV uL wC) Ij(Fp Lx Nr sH) Qv(uN uU wG wH) aA(Hx My Om Oy) rB(bR DB wD) qW(sC vP vV Wc) jO(aR Hf rV sC) Fw(sH
sM wK) Wh(jL IM nJ) Pa(Hx Og Tj) gC(Gh Rv Yl) IL(aR rV sC) rO(Ip vP vV) uL(Db Hf Na) Ew(Ax Cs) My(Lx Mt) Hu(rT uR) Il(Mh ql)
Wf(jQ jU) Ye(gW IK) Ri(jT vU) Om(Fp Jr) aQ(vP vV) wQ(aL fP) sK(bV jI) jP(cC Rh) TjJd GbgW NujH IcjG IhsH IphL WdnJ JupK KsrC KysC OghR VtzA aFrU aPuX aRrW cLwK dXiZ ePhC fNrA iPqO wDwF wGoE kFrZ} Bb{jY(Ad Ba BC bH bW cA cM CW Di eD Fa Fn Fr Hf hG Ic Id iH Ik Jd Jh Ji Jj Jp JU JV Kf Ki Kn Kx lM Lw Lx Mm Mq Mw Mx Mz Na Nc Ne Nk Nl Of Oh On Pa Pb Pk Po pS Qa Ql Qm qY rC Rh rS rW sI tN tS tV tX Ub Uf uL uM Un Uo Ur uX vB Vq vS wD yD yH xA Wm) tV(aF aK aS Bg bH bQ bZ cK Co dR eC Ef fP Fw fY gW Hc Hu Ic iH Ip It Iz jD Jk Kk Ky Kz lL Mk Mv Mz Na Ni Nq Nt Nu Oi Oy Pa Pc Pj qC Ql Qn qO QU Qv QW rC Ri rU sH tO Ua Ub UM Uu vP Vs vV xA Tk) tT(aR aX BG bS cI cK dA eC eD Fb fP Fw Hf hL Hu In iO Ip Jp jU jV Kd Kf Kk Ky Ld Lh lL Mm Mn Ms Mz Na Nd Nh Nm Nq NW Nx Oi On Pa Pj qC Qn rB rC Ri rU Ua Ub Uf uU Vt yH) vB(Bg fP fY Gl gW hB Hf Hu Ic iH Ik Im It Ji Jj Jk Jp JU JV Kc Ke Kf Kp Kq Ky Kz Lh Lw Lx Mm Mz Na Nh Nl Nw oE oF Oi Ok On Pa Pj qO Qv QW Qz rC Ri Ua Ub Ue Ur) tX(aR aX BG bQ cF cK dJ eC Fp Fw Hf Hq Hu IO Ip It iZ jV Kd Ki Kk Ky lL Lu Mm Mv Mz Na Nb Nq Nt Nu NW Oi Pi Pj qI Qn qU Qw rB rC Ri rO Ua Um uU uV yH) tN(aF aX Bg cB cF cK eC fP Fw gW Hc Hq Hu Ic Ip Ir It Iv jF Jk Jp jT jV lL Mm Mv Mz Na Nd Nq Nu Nw oF Oi Pj Qw rB Ri rU rW sC Ua Ub Um Vt yH xA) tS(aF aR aX Bg cF cK dJ fP Fw Hq Hu Ic Ip It Jp jT jU jV lL Mm Mv Mz Na Nd Nm Nq Nu NW Oi Pj Qn Qw rB rC Ri rO rW sC Ua Um Vt Vu yH xA) aC(Ad aJ aM aN Ap aR AW BA bC bE bF Bn Bo bU cB cF Ch cN Cp cT CW De dF Dg Di Dl dN Ef fR Io Is Mc Mt Na Of On Pd Tj) eD(Ad aZ Bo cC CW Db Di Fn fY gW Hf hG Ic Id iH JD Kf Kn Ky Kz Mm Na Nq Oh Oi oK On Pa Pb Pc Pk Po qO qP Qv rW sC vP vV) uM(Fb fN FP hB Hf Hu Ic iH iO jD jF Ji Jk JU jV Kp Kq Ky Ml Mm Mw Na Ne Nl oE oF Pa Pc Pj Qw qZ rB Ua Ub Uf Ur Tj tF) rC(Aj aL Bg bH cD cW dB Di Hf Ib Ic iH jV Ks Kz lK lL Lw Lx Ma Mm Na Nt oE Of Oi Pa Qu qY Ri rW tO tQ tR uL wD wK yH yJ) tO(aR Bg cF cI cK fP Hu IO It Ji Jp jT jU jV Kf Kp Ky Lh Lx Mm Mv Mz Na Nd Nh Nq Nw oF Oi On Pj rB Ri Ua Um yH) tR(aR aX Bg cF cK fP Hu Ic IO Ip It Jp jV lL Mm Mz Nb Nd Nq NW Oi Pj qI rB Rh Ri rO rW sC Ua Um Vt yH) yH(Bg fN fY Hf Hu Ic iH Ik It Jk jV Ki Kk Kz lL Ms Mu Mz Na Nq Nw Oi Pj Ql Qv Qw Qz Ri Sr Ua Ub Vs tF) lL(aR Fn Hf Ik Il Ip Jd Kf Kx Kz Mm Mw Mz Na qD rO rW sC uL uN vP vS vV wL yD) rW(aR eZ Fw Hf iH iO jV Kk Mz Na Ne Nh Nk Nl Oe Oi qI Qn Ri Ub Tj tF) vP(hB Hf hV iO Jp jU jV Ky Mz Na Nh Ni Nw oE oF Ok Pa qW rB Ri Ub Vs) qI(aI Bo dD Hu Ib Ic iH iO Mm Na oE oF qC Ql Qu Qv Rf Ue Uf tF) uU(aP bV cT fP hB hW iH jE jL Jp lM oE oF Qv qX rN Ue Ur Vt) vV(hB Hf hV iO Jp jU jV Na Nw oF Ok On Pa qC Qv Ri Ub Ur Vs) qY(Fn Hf Ic Jg Kf Kp Kz Lh Mm Mz Nk Oi Pa Pj Ql Ri rS Vq) qO(aQ aR aV bR cM cW hV iO Jj jQ jR oE oF Pc qP Ri uL tF) yD(Bg fY iH Ik It Jp Kz Mk Ni Nq NW Oi Qv Qw Ub) vS(Fn Ic jD jE jF Jp jV Qv Qw Rg Ri Ua Ub Ue Ur Us) uX(gW Hf Ic iH Ik Ki Kz Mk Mu Nt Oi Qw Ua Ub Us) wL(jE jV Kf Ky Lw Nq Nw oE oH On qX Tr Tk) jD(Hf Ic Il Ip Kf lK Mm Mz Na Nq Of Oi vH) yL(cC iO JU JV Nq Oi Rf Ri Ub Vt Tk) qQ(aP cE fP iH jK Jp oF Ql Qv Qz Ue Uf) uZ(fP jE Ji Ke Lw Lx Mm Mz Nw oE On wD) qC(cL cV Hu Ip Mz Nq On Pa Qz Un Wm) xA(dR Ex fP Hf Jp Mm Mw Nh Ni Pa Pj) jV(Db gW Hf Ic iH Kf Kn Kz Ly Mz Na) wD(Hu iA Kd Ky Ns Nt Oi rB tF) lK(Fn gW Hf kK Kz Mw Nq Nu Pa) tQ(eC Lx Mz Na oF Pa Pc Ue) Ri(qH rO rU sC uL uY wH) rS(eC gW iO kR Ms Pa tF) rN(eC jF Nq Nt Nu qU tF) oF(sC uR uT vH vO wQ yJ) fP(sJ uO uT vH vO wQ) iH(bU cM Kq Mm Nf qU) uL(fY iC Na Qw Ua Ub) hO(dN Ex Lx Mm Pj) qX(Hf Na Nu Of Vq) vH(jK lM Mw oE Qv) Nq(jH qZ wB wK) aW(aN bU cB cK) jR(fY Ic Na Oi) Ub(sC vI zA) Hf(jT qU rX) cW(hA jG jM) fN(Jd Mz Wm) qD(Mz Qz Ua) jE(rV wH tL) jU(aR Kz Nu) oK(Ex Na Tl) Th(eZ nI) Nt(jH uG) Lw(wH tL) Mm(hA qB) Ic(sM zG) Zq(lY mH) Qu(rT uY) Ky(sJ wH) Oi(rO rU) Uw(gL iZ) Vs(yE tM) aV(fY qP) cM(hB jG) eO(Nd Ok) gP(Kq Lt) gW(hV Ye) tF(Uv yJ) nJ(Fi Rv) lM(vO tM) sC(hV Ue) DwNw EobP TjrU FnqU GhpI NujH NajT HuzI IznT QvuN TliZ KpsJ OniA VqhA aNbU aQfY aRcB ePhB qWuY jLkF} nJ{Du(aD An Ao As Aw BA bF Bg Bn bQ bZ cE cG Ch cL Co Cp Cq cT Cu Cx De dF Di dL dM eM Fy gL Gp Hc Hq Hr Ib Is Iz Je Jg Jh Jk Jl Jq Ke Ko lY Ma Mh Mk Ml Ms Mv Mw Mx My Na Nc Nd Ng nI Ns nT Nv Nx Ny Of Oi Om On Op Ou Oy Pd Ph Pi PK Pz Qn Qy Qz Rc Rx Ry Tn Tt Ua Uf Uu Vi Vs Vv Wd We Wh Yg Tl Tj) Op(aA Af An aP As Aw Ax Bn bQ bS cH cN cR Cs CX dC dH Di dM dU Fa Fb Fi Fp fR gL Gn HB Hc Hf Hl Hr Hu Hv Ib Ih Im It iZ jB Je Jh Jk Jl Jn Jr Kk Kp Li Lj lY Mb mF Mr mS Mu Mv Mw Mx My nA nI No Nq Nv Ny Oa Oy Pa Pe Qn Qt Qv Qw Qy Qz Rh Rj Rv Si Tn Ua Ul Um Ut Vp Vq Wd Wf Xa Tj tF) Rv(aD An Aw BA bF Bg Bn bQ cE cG cL Co Cp cT dB dF dH Dk dM Ef Fb GL Gn Gp Hc Hq Hr Hu Ib Ij Is It Iz Jd Je Jg Jh Jk Jq Mh Mk Ml Ms Mu MY Mz Nc Ng Nv Of Oi Om On Oy Pd Ph Pk Qt Qy Qz Rc Rj Rx Ss Tt Ua Uc Ud Ue Uf Ut Vi Vs Vv Wd Wh Yg Zq) Rx(aD Af aH aL An As Aw Ax BA bB Bn bO bQ bV cG cH Co Cw Cx dC dD De Di Fb Fi fP Fr gL Gn HB Hc Hl Hr Hu Hx Ib In Jp Jr Ki Kp Kx Li Lx lY mH mS Mu Mx My Nq Nv Oi Oy Pd Ph Qv Rb Rc Rj Rz Uf Ul Ut Vq Wd Wh Zw Tm Tl Xa Tj) Hl(aH Ao Bg Bn Ch Co Cu Cv De Dg Dk Ef Fd Fy Hq Hw Ih Iq Is Iz Jg Jk Jl Jm Jo Jq Js Ke Kf Kl Ko Kq Kx Mp Mw Ng Nm Nt Nv NW Oa Of Oh Om On Ou Ow Oy Ph Pz Qz Rm Rt Rz Tn Tt Tv Ua Uc Uf Ut Uu Ux Vh Vq Vs Yi) Fi(Ad Aj Ao Ba Bg cG Ch Co Cu Cv Cw Dg Dk Dl Ef Fd Fy Ij Iq Is Iz Jg Ji Jp Jq Jt Kf Kl Ko Kq Ks Li Mn Mw Ng No Nv Nx Ok Om On Ou Ph Qz Rt Rz Tv Ua Uf Ut Vs Zq) Gn(Ao Bg Co Dk Ef Fd Fy Ha Hc Hw Ij It Jg Ji Jj Jk Jm Jo Jq Js Jt Kf Kj Ko Kq Mn Ng nI Nv Nw Nx Oe Of On Ou Oy Pz Qb Qz Rj Rm Rt Tn Tt Tv Ua Uc Uu Vh Vs Wd) Rz(aD aH An As aW Ax bA bQ cL cR cW Db dH Di Eq Fp Gp Hb Hf Hr Ii kG Lj lY Mb mS Mx Nf Nq Pa Qm Qv Rg Rj Si Um Uy Vq Yh Zw Tj) Wh(aH An Ax aY aZ bB bL cE cR Cw dU Gp Hr Id Ji Jn Kx Lj lY Mk mS Mx Nf Nk Nq nW Og oO Qv Rg Rh Rj St Tr Um Th) Xa(aH An Ao aW Bg cE cG cL cR cW dU fA hB Hr Jd Kl Ko Mk mS nW Qz Rc St Tr Tt Uc Uo Uu Vh Vs Vv Wf Tj) Zq(aD aH aL aQ Aw Ba Bg cL cT Db dC dH Di Hb Hu Ib Jl lY mH mS Mu Mv Mx My Nc Nx Of Rj Ua Wd Yg Tj) Wd(aH aI aM An Ax aY aZ bB cE cR Cw Gp iJ Ji Lj lY Mk Mp mS Mx Nk nW Og oO Qv Rg Rh Rj Tr) Yg(aD aH An Ax aY aZ bB cH cR Cw dH Gp Hr iA Lj lY Mk mS Mx Nk nW Og Qv Rh Rj Yh Ye Tj) Zw(Ao Ch Co Dk Ef Fy gL Ib Is Iz Jg Jq Kf Kl Ko Kq Mu Mw Nv Om On Ph Qy Qz Tn Tv Vs Yi) Ux(aA aD aL As bA bQ cT dC dH Di Hr Ky Mb Mk Nf nT Um Ut Vq Tj) Si(Ao Ba Co Ef Fy Ij Iq Is Jg Ji Jn Ko Kq Ng Ok On Ph Tn) jH(AR Ba bR cW Dd dE hB Hq Ik Is kS Me Nj Oe Oi pF) Gc(aD As bA bQ dC dM Hq Hu Ib Jk Jl Mb Mu Mx Vi Tj) Tl(An bS cH cR dC dH hB Ih Je Li Nk Nq Oa Qt Qw tF) Yh(Ao Bg Ch Co Cq Ef Hc Ib Iz Nv Om Qz Tn Vs) Rt(An bQ dU Fb Gp hB Hr Hw Je mS Qv Um Vq Tj) Yi(aH An Gp Hr Hw In Lu lY mS Qv Rj Yj Tj) Jd(cM cU Ib Lt nF pH Ps Rg St Ub Uv Vj Vo) We(aH An cR dU hB Hr mS Qv Rh Rj Um Vs Tj) Fd(Aa aD An Cw Hr In Kp mS Qv Rc Rj Tj) Ho(Ao Bg De Hr Jq Kf Ko Nv On Qz Tt Ua) Vi(aH An aY aZ cE cR Cw iJ mT Og Rj Uc) Vh(aD aE An bU dC Hb Hr Rj Ul Vq Tj) Vw(aD aH bA bQ cE Hr nT Qv Rh Rj Tj) qT(aK Di dR gW Ih Jj Nv On Pa) Yk(An bQ cR dH hB Mk Rh Rj) jE(bF Bo bS Di oK Ub Us Uv) Wb(As bA bQ cL cT dF Tt) Wf(cJ dB lY Mk Mw Ng Rj) Ye(Iz Jl Jq Nv Om Qz Vs) Yj(cL Cq Mu Nv Qz Vs) Ry(aZ cE cR hB Og Th) Vj(An Cv Mk Rh Rj Tv) dU(Fc Kk Lt Tn Tv Uy) gW(dG dL kF nH nL) Eq(Ba Jg Rh Tj) Lt(Fb Hr Kl Nq) Uw(Iz Mk Rh Rj) aN(eD jQ jR lM) jF(bZ cZ iA Uo) qY(bF bS cA Uv) Em(Aw Bn Cw) Gh(gC Nq oW) Sh(Mk Mx Rj) Sj(cR hB Ih) Lp(bQ Ko lY) Yl(gC Rc Tr) Va(As Nq Um) nN(hX jT rZ) jQ(aJ dG dM) lK(Ba cG dG) Gb(bQ dF) Iz(Uv Vo) Sf(Ij Ko) Wc(Ao dC) Tm(An cH) dE(iC jI) jR(eF iA) jY(hG nW) BojV ChiC CqVo FcHr TteQ SsUy KppH UvjD VurA aKqX bHqV bLjT cWlL kPrZ} Pj{xA(Af AW aX Bc Bo bV cI Cu cV Cw dA Di fP Fr Hf hG hO Hu hW Ic Ip jD Jh Ji Jp Ju Jy KQ Ky Kz Lh lL Lv Ma Mw Mx Mz Nh Ni Nq oF Ok On Ou Pa Pd Pi Ql Qn Rh Ri rT rW tQ tT tV tX uL Un Ur Vq Vt yH tL tF) hO(Af Ap Ar Ba bG Bo Ch Cw Db Ex Fa Fw gW iA Ic Il Ip JD jE JF Jj Jm jO jY Kq Ks Kz lL Lx Mc Mq Mw Mz Na Nd Nq Oe oF Oi On Ph qC Qn Qv Qw rN tO tV tX Uf uM Ur VS wD yH Tk tF) jD(aR aZ Bc bS cA cC cE cI Db Di eD hA Hf iA Ic iH Il Ip Iu Jd Jj jO jR jY Ks Kx Kz Me Mn Mz Na Nn Nq Nt Oc Of Oh Oi Oz Pz

Figure 4 Continued

Figure 4 Continued dC gP iJ kS oH pF Um Vo) fR(aW cM Dp Fp gP iJ Ik Je jG Ms nW oF) mS(Cv dA eF fP hB hC hG oF oH oK oN Vo) nK(cI Hv Ij In Iq Iu Iv Jr
Js Mq Mx) Zw(Fr hA Hx Iv Lh Mt Nx Vz YI) Wc(Fr Is JI Mw Nv Oy Qa Ua Wf) YI(Fr Ih It Lh Mk Mw Oi Pe) mF(aN aW cI dA DB gP hG)
Gd(cX Fy Nc Ni Pc Tz) Vz(aA Hu Ih Ii It Nv) Wb(Hu Ik Jg jU Pd) nN(aU eD jL oK Wm) kK(iJ oK pF Us tF) nR(aN bI dA iJ) IW(bL dB gP tF)
mM(aM iJ oH pF) nA(bG bI hG kR) iZ(kO IX nO nU) As(kG mE ml) Zx(Hx It Pd) Vw(jG jO Vs) nT(aJ dM iA) nF(hC nW oH) We(Jr Mk)
cI(mE ml) IY(bH Vo) mT(aZ iJ) mW(cS oK) AaiH AphO ImYe QbWf UsnI UwjL aLmI aNmP dBnO dMnD nUhB IXoN mUpF mYoH}
eQ{Gh(Ao aQ Ba bF Bg cG Ch cK Cq Cx Di Dp Fc Hc Hq Hu Ib Jk kP Ks Lt Lv IY Mb Me mH Mn Mu Mx My Na Nc Ng Ns nT Nv Of Oi oK
Ph Pi Pk Qn Qz Rj Rt Tn Tt Ua Up Ut Uy Vp Wd We) Th(BA bF Bg bQ cG Ch cT eM Hc Hu Ib Lu Lv IY Ma Mb Me mH Mu My Na Ns Nv
Nx oH Pk Qn Tn To Ua Ut Tm) Mn(Aa cQ cR Fa Kk Ld Qn Rt Si Ub Uw Uy Vb We Yd Yg Yi Tm) Tm(aD aH bB bL bQ cG Dd Ij Ko Li Mb
Mv Nq oH Qu Yi) bA(Dr Fd Ub Vh Vi Vj Wb Yh Yj Zw Ti Yf) Tt(dB Gd Kf Kn Nm Pz Ub Uv Vo Ye) Um(Af Ao Bg Bn CX Nx Of oK Qw)
Qv(Ao Bg cG Cq De Hc Iz Of Uf) Uk(Ao cG Co Cq cT Cx Uf Ut) mH(Em Gc Ko Sj Ub Yi Yj Ye) cG(Gd Kr Ld Rb Ux Uy Yh) Ao(Gd Ub Uc
Uy Vb Vo) Lv(Hc Iz Tn Ua Uf Ur) Mv(Ed Hc Kc Kz Ry Vh) Cq(Gd Ld Rt Uv Vo) aZ(Ib Ld Qm Ua Ut) Dc(Em Pk Ud Vo) Tj(aL dK Kx Mk)
Ub(dF Om Rv Vs) Uy(Hc Om Ph Tn) Gc(bQ Mb oH) Ld(aS bB Ik) cR(Tn To Ut) nW(We Yg Yk) Ez(Ba Tn) Nt(dB Zw) Ua(Lp Wd) Jn(Fc Vh)
Nx(Gp Uv) cT(Ur Yh) ApJg FiPh NqLt HoQg TrKo IhZw HcPa IzdB KxaW OfUg OmVo VhoK} Ip{tT(aD Al aQ aR bX bZ cC cF cI cU cZ dB
Di dJ Fw Hf Hu iA Ih Iq iZ Jg Ki Ky Kz Lh Mk Mv Na Nu nW Of Qc qD Qg qW rB sO vI wK wL tL) tN(Aj cB cC cF Di Hf hO Ic Iv Ki Ky
Mk Mv Na Nu Of Oz Qc qW rB sO Ua Us vI) tX(aR cC cF Di Fw hL iA Iq Jg Ki Ky Mk Mv Na Nu nW Of Qc qW rB yH) wL(aF cC Hf iB iH
Iq Jg Ji Jp Kz Lh lL Mk Of Oh Um wD zI) hL(aQ AR cM cV cW dD Di dN Ic Jp Ke Kq Lh oF qW sM) wG(aR bJ Id iH Ij Jl Ke Kf Kq Lx oE
Po Qv sO tQ) qC(Bc cB cL cV Di Ic Jp Jt lL Oh qI tS Un wD yD) tS(aF cC cF Di Kc Ke Ky Mv Of Qc qW rB vI) lL(Di rN rO rQ sC sO wH yD
yL yE) tR(aR cF Di Ky Mv Of Qc rB) wB(cF Mk Na Nq Nu Qc wQ tL) wD(iA Ky lN rB rX wF tL tF) Qv(uN uW uZ vH tL) hO(Bc Jf Jt Lx Uf)
wQ(fP Fr iH Il Qw) wH(Di hW iB Ky oF) lN(rQ vH yJ xA Ti) Wn(tQ uM vP wC) sM(Ic Ky Tr) qT(Zw Zx Ye) xA(fP Hf Lh) Di(eD rC) Na(sO
yH) wF(iB Lh) qX(Wc Wd) qW(yH yL) kF(jL rZ) DupK IcqD QwtQ KzuZ VusH iCsF kPrZ rNuU} lL{Ye(Hu Hv Im In Js lO Lx Me Mj Mp
Mq Mv Mw Mx My Nb Nl Nn Nq Nr Oh Pd Po) sC(Ao Ap Ba Bc Cp Dg Di Dl Ed Fb Jg Ji Jt Ke Kl Kq Nm No Nx Om Tr Uf) kF(Aj aN aX aZ
bI bS bV bZ cH cI CU Dg dH iO) vS(Aw cF Dk Jg Ji Jt Ke Kf Ko Lh Nm Tr Tt Uf wL) Bc(aR cA Hf Kz Na qC qD qP rC rW uN uV wL)
Nm(hO iH qC qD rN rV tS tT uL vB wL yL) qC(Ic Jt Ke Kg Kq Lh Oh Tt Tz Un) rN(Ap Jt Kg Kj Kl Nq Qm Ss Tr Tt) Jg(aR Hf rV uN uP vA
wL Yd) nI(bH cI Ug Ul Um Us Uu Vv) qD(Ji Jt Ke Kq Lh Oh Tt Un) uN(Cp Di Ji Kc Ke Kq Un) Uf(hO qB qQ wL yL tM) kP(aW bF bS cA Db
De) Ke(qG uM uZ vB wL) lX(fP hB hG kQ oN) Tr(qZ rW wL yL) Wd(Il Mf Mp Oi) dB(kG kK kO mT) mW(cB cJ dC nW) Di(Io rW yH)
Na(Cp Kq nN) bH(lY nN nU) nK(aZ bW Hx) wL(fP Ji Kq) rB(Aw Kz Ti) Tz(kG nB) Ib(sF sH) Lh(Yd xA) Va(lN Us) cW(kG kO) gL(nD nF)
nA(dR hG) kC(As iJ) AaiH ApqP ArNu AwaR BokE CprW TiRc NnfR MkZx TtuG IkVz HfsF JiuZ WfaA QwuX JtxA KqaL VolY aWnR
bFmY nNhG} oK{Vh(AA aD aV Bo cB cF cN Cs Fw Hb Hc Hq Hr Hu Ib Ih iZ Je Jk Jl Kc Ki kS Li Lj Lu Mb Mh Mu Mv Mw Mx My Nd Nq
Nv Qt Qv Qw Qy Rh Rt Si Ss Ua Vb Wd Yj Zw) Yj(cA Ch Ef Ib Iq Is Iz Jg Jk Kf Mb Mu Nv Om Oy Pd Qy Qz Rz Uc Ux Yg) Tm(Ax Co Ef Ih
Ij Ir Jg Jp Ke Li Mb No Nv Oa Tn Ut) Hp(Ba Dk Ef Fb Iz Jg Jk Jp Ke Mu Nv Tn) Yg(Ef Fb Gp In Jg Ke Nv Qv Ss Yh) Vb(Ba Cu Ef Jk Ke Kf
Ko Oy Tn Uc) Si(Ef Ij Jg Jp Jt Kc Kf Ko Tn) Zw(Ef Iz Jg Jk Ke Kf Tn Uc) Uw(Ef Fb Gp Hr Jg Jk Ke Nq) Fi(Co Ij Jg Jt Kf Ko Tn) Yh(Ch Ef Iz
Jg Jk Nv Tn) Yi(Bg Ef Fb Gp Jg Ke) kC(jI jM jT qT qW rA) Du(Jk Kc Mb pK Rc) Wd(bB cB Fb Gp Ko) We(cB Fb Gp Qv) Kf(dX Hf Ho Jj)
Ut(Ru Rv Sh Vj) Ye(Ij Ko Nq) Vj(Iz Mb Qz) lX(hA lO qX) mI(qT qX rA) Fb(Ry Wf) Gb(aW Nq) Hf(Ko Kq) eD(mW nD) nN(jP qW) mM(jE
qX) iC(nO nT) DiIs EmKc GpYk NmiH MbSh NaKq UcUy TrRy TnRt WfhC KoVa RvcF UmfB aHdX nRjP mUqW} eW{Lx(AF Aj aM aQ
aV bL BN Bo bW cA cB cV CX cY dA De dK gV Hu Ik Is Iv Jm Jr Lv Ly Mg Mp Ns Nv Of Pd) aF(aI aM aY bA bF bM bP bQ bR bZ cE cG
cW dF dG dH dM dN fP fR Hx Jn Mn Mp Nx Oy Pf Qd) aM(aX aY bA bC bP bQ bR bV cN cT dI dJ dM eM Gd Jk Lv Mb Mr Nd Ni Ny Oc
Oz Pb Po) bM(AO aX aY bA bC bQ bR bW bZ Dd dE dI Em Gd Io Jg Jk Jt Lv Nx) Mn(aG cN cW Fp Fr gV Hu Li Mq Nx Qb Qe) aY(Ch Co
Cx Dk Ef Hx Is Jh Jn Ma My Qd) Jn(Ao Gd Jk Mb Ml Mu Ng Oe) Qb(bA cH eM Mb Nd Nj Oz) Nx(Ax cN Cs dB Hv Jr Lj) aO(dN Iv Jr Nj Nr
Po) bW(dF dG Nn Pe Pf Qe) aW(bH Co cR dC Iq) Nu(aS Nc Nf Pa) Pe(Gd Jk Ly Qa) cW(bR cN cP Fp) Ch(Aj Nd Oe) Co(cP Iu Nd) Mb(Hv
Hx Po) Jj(Cu Dk Mh) aI(cH cN dM) bP(aK cY Mu) cB(aG Fp Jo) Cv(Pb Pc) Ml(Ms Qd) Mr(aD Nj) Ji(Cs cV) bR(dN Oh) AoJq CxNl DkcP
PoPb FpbC NoMu LyMt NbIs NdJm QecH JlaG JpcV LjbO bBcN} Tt{vS(aD Aj Ap Ar Bc bW bZ cD cH cR cW dC Di dJ dK Dp eD Hu Ib Ic
Id Ji Jk Jm Jp Kc Kq Ky Lh Lu Ma Mf Ms Na oF Pa qA Qv qW rB rN sM tR Uf Un Vs wG wL Wn Wm Tj tF) rN(Ap aX bW cD cM cW eC eD
Fr iO jO jV Li Nt Nu Oi Pa sM Uf uX vQ Wn tF) qW(sC sM tN tS tT tX uG uI uL uV uX uY vA vP wP yH zI) Gz(hO qI tQ tS uL uM vH vU
wC wH yH zG) Di(eD rW sC sM tU uG uP uX yH zA) Hu(tN tR tS tX uX wP yH zI yE) Ib(qQ sC sK uG uX wG wK) Un(hL qC qD qZ rR rV
wH) Uv(cF fA iP oW pK tF) wG(Aj Lx OF Qv Wm) qQ(Aj Jj Jp oF pF Uf) Fi(hC Kk Li Mb Qh) qZ(Il Ji Lw Lx Uf) uG(bI Fw Ic Na Qv) Kk(Rv
Rx Wb Yl) Vs(uP wK tM tL) eM(Ao De Rc Wd) rP(cD eD sM Uf) Vb(gL Jc tF) qA(eD Nf tF) Bc(qC qD) Lx(hO wH) Hr(sF sI) Wb(gP oH)
Ye(eC oH) Wn(wC wL) tS(cR jV) jB(Om Si) oV(cU Jj) uX(Ql Qw) CtsI DufP LwhO MfwK NauL HpgL SfmY QvvQ RhwL OgsF UfsH cItX
tFqO tTjV} nA{Si(Ba bB cE Fb Ij It Jg Ji Jp Ke Ko Li Nq Oi Op Rc Rz Tn) Yj(bF bQ bS cA cE cG cL Cx De Hq Iq Jl Kx lY Mu Qv Vs)
Rz(aW Gd Gl Hv Ii Kn lY nI Nq Oh Qv Rh Um Ur Uw Zw Tj) Op(Fi Gd Gl Ii Kg Kn Lh Ma nI Nn Oh Ou Rh Uw Yd Tj) Fi(aH aL bB cG Fb It
Jg Li Mw Nx Qz Tn Uf) Zw(aH bB cE cG Ch Ib Iq Iz Jl Mu Uf) Du(aD bF bM cE Hq Ib Jl mII Mu pK) Yh(bF Bn cE cG Ch Cq Ef Iz Qv)
Yg(aH cE hB Ib Kg Kj lY Qv) Yi(aH bQ cE Fb Hr Hw Lu Qv) Hp(aH cE Hr Ib Jl Qv) Lp(Hr Hv lY Nq oH Qv) Rv(bF bM cE Ib oP Tj) mH(Em
Ux Vc Vj We Tm) Uw(cE Fb Jp Qv Uf) hG(jT jU jV lO rA) Gh(Hq lY Nq Qv) Sh(aH Lu lY Nq) Ye(Hq nI oH Qv) dR(jE jM lM lN) iC(aE iJ jL
mT) Gd(Cq Jg Ko) Ry(aD Fb Hv) Vb(cE Iz Rc) bW(hA jL jO) hV(It Me qT) pF(jU qW rA) Gc(aD bQ) Yd(Cq Uf) Uy(cG Uf) Vi(bB nI) bH(jK
qV) BaEq FnLd NrhX HonI HqaW YkbQ WdhB WeQv JlTm RxbB UmUx VcIY VhaD aJjL aZjK cWqT dIjI} mZ{Rz(aL bA dB Em Gd Gp
Hv Lj Mn Nf nT Pe Pf Qv Ub Um Uw Uy Vb) Rv(aD bA bF bQ cG dB Gp Hq Kk Ml mY Ph Pk Ud Ut Vi) Em(Af aL bF Bn Ch CQ dD De Ed
Iz Ld mH Qn) Tn(eM Eq Gh Gd Hp Si Uw Ux Uy Wd Yg Yh Yi Yf) oH(Gh Hp Lp Ry Sh Uw Uy Vh Vi We Yh Yi Yj Ye) aL(Fi Gh Hp Lp Rx
Ry Vh We Yg Yi Yj Yk Ye) Du(aA aD bA bF bQ cT Hq Ib Jq mH Qn Ut) Gd(aH Ba Bg Ch Cq Fb Jg Ke Ko Op Uf) Vb(Ao Cq Iz Jp Ke Mw
Om) Th(bF bQ cG Gp Qn Uf) Qv(Ry We Yg Yh Yi Yk) Rx(aA bB Bn Cx dD mH) Op(bA dB Gp Lh Oh Ou) Cq(Hp Uy Yd Yi Ye) Jp(Hp Lt Si
Uw Vw) Vi(bB cQ cU Gp Li) Mb(Gb Gc Hp Vj) Mw(Fi Hp Uw Yf) Yk(bB Gp Hr Kj) Wd(bB Iz Om Vs) Ye(Ib Mv Om Vs) Ry(bW cQ dB
Um) Uy(cG Ch Om Uf) Me(eD hX jG) Yi(Gp Hr Lu) We(aD bB Hr) Uw(Ke Om Uf) Ib(Hp Zx) Yg(bB Ke) Vj(bQ Hq) ChYh YfPh FiMv GcbQ
GpSh NcZx WbbA SiJi SfnT RtUm OgrC VhaD aQjO aZlM bLrA dEjE iCpF} iC{kC(Aa aO AW Bg bH bU cE Cq dC Dd dH iA Ii Jj kR Pe Pz
Uc) nK(aW bH cI Hx Ii Ij Iq Iu jE Jj Na Nm nR) kG(aN Ar bL Ch cW Db Dl dK Na pF qT) lX(aK aL aN aS Cv cX cY dI fP iZ oE) mH(Aj aK
aQ aU aV aW bJ cY Jj Ue) mT(bL bW cX dI kK kP Mh nI nR nW) nI(aW cH Cu Dc hC iJ Jj jL Us) kK(Db Jj jL Nm pF Us Uv tF) nH(aE aN
bZ cH dE iJ Me) kI(aQ aU aW bX cC cH Jj) kN(Cp dC dR Uc Um Ut Vo) kP(aU bJ Ch cT cU Ub tF) nT(bI Ch dE iZ kS oN) mM(aE bN cI dR
iJ Us) mW(bH cI cS hC kS nY) mE(aE Aj aW dC iJ) mY(bH bI cT cV dC) jO(Uw Vi Vw Vz Zw) lM(fR Wd We Wf Zw) Ti(Mk Nc Nh nY)
mI(aE Aj cH Ct) iH(Aa eD rX vS) kE(aW Bc hC iJ) Wf(Mf Mk Oe) dE(kO nO nU) mF(Aj aW dR) mS(hC nY Vo) sF(Hr Ib Ic) jL(mP mU nN)

Figure 4 Continued

Ch(kO nB) Hx(Zx Ye) Ug(Vb Vh) Va(aA Vi) nO(aM bL) nU(Ar Co) IW(aQ Di) IY(Ub Vo) BnsI DbkF LvYe MkWe

DknW KgqD KiKI OmuU} Mb{Ry(dR kK IW oP) fA(Sf Si We Tm) Uw(lW mT oP) kS(Ru Sh Vj) Du(pF pH) gZ(Yg Yi) SffB RzmM}
Fi{Fw(Iq Qh Qt Tn) bB(kC kO nH) Tn(Dd Kk) Oi(Rj Vh) mP(Ij Mw) FyIX MxSs ImcB WehB QzoE PhfA} Ky{sC(aR Ba cT iO wD) vS(fN Jc
To wL) wH(dH oF wD) Fw(tX uX) LutX MvlX QwuX bXxA hGuU} Ef{Vb(Af Bn cF CX Dd Dc dR) Lv(kK lX mS nF) Vw(Dd Dc Kk)
Uw(cB cX) EqmS} bQ{kK(Du Fd Hp Lp Ps Rz Vw Yh Yk Ye) Yk(mW nH oT) nF(bU Db) YhkF KzwB cOml} tX{Fw(Ao Kc Lu Nu) Lu(Ao
cF Qw) nW(Aw Dk Kg) Nu(Ao Pd) DgiA aRzG cFuN} Eq{Ba(kC kG kl kO mU) mS(Ng Om Rz) nO(Ib Om) CqnB TnnH IzoT RzoO}
Gh{fB(bB bL Db Jr Mx Rj) fA(aJ aP Ib Mx Oi) oT(bI cH) hBoO} Wd{Ib(lW mS nO oO) bB(lW mY pF) oO(hB Mv) HulW IzmM cMiO dBmT} oE{Ry(Ch Ib Iz Jk) Ao(tO vH) DlGd TjWe LuwG HbtL luwL QzVc KgvH} vS{Kz(Ez Id Kc Qm Wm) Id(Ki wG) AaFn DcUs LuVs TnKi HfqD cFwL} Yh{Bn(kC lW mY) Ao(lW mU) Iz(eF iA) CqmP QzmY OmmW PhgZ cXlW} nW{tS(Aw Cp Dk Kg) We(Hr Hx Tj) Vj(Ch cQ) tR(Aw Dk) YgVp} vB{Qw(Aw Cp Dk Kg Om) Cp(Jk Na) Hf(Lv Uc) DkJk NaKg KcKz} Hq{nO(cG dD Du Gc) bU(nF nH) DukP YekO UkgZ UvmT cRlX} cU{kF(Em Rg Us Uv Vo) Vh(hB iP) WehB RzkG UmpH VimI} Cq{nD(Rt Vh Yf) nH(Uv Vo) oO(Uw Yg) GdmU YdfB VzpH} Si{Tn(iA kI mT nH oT pF) AolX JnnN OpnD PhfA} Vb{Bn(Rc Ss) Je(hB Ss) AfJk AomS DcbH HrIb TnRh IzmY} Aa{Hu(sO uP wB yH) xA(Kz Na) RvlW QluN QmnD} aR{cB(Aw bA bF Bn cT) sO(aK qO qP) cltR} Kk{Rx(Iz Jk Ss Ua) Yl(Rc Ua) UbpH JeRt} Tj{CvoT HpLi WehB KxfB PaxA bBnF clpH} Rv{mY(It Mh Mu) mU(dB Qg) DdoP UbpH} fA{Sf(Ju Oi Qg) Fd(Mw Ph) HoPh YdOi} tS{cF(Dg Dl Kg qD) Cu(Fw Nu) NuKg} Mv{mT(Uv Uw) DupH MknF YgmS RgkG} Na{Dl(tN tQ) wG(Kg Pi) CpvH FyuL} bB{Rx(nH oP) Vi(kP lW) YeoP VjlW} bU{Rg(kF kG kK) nF(Fn Vs) WeoO} hV{qZ(lX mS) kF(Ii Oy) kP(Mn nN)} Ib{Yg(Mn No) DukI YekO RyLj} Hf{Dl(wL xA) uM(Ba Dg) FrxA} Yi{MlmS RhkK UmpH aDoO cQkQ} Je{cB(Lt Vc Wf) hB(Fc Vc)} iO{cM(Gb Rz Vj) cQ(Em Ho)} Cu{Nu(tN tO tR) HuwL} Gc{Hv(lW mP) UmmU aDkN} Iz{lX(Ez iA) LpiP UvkO} We{Rh(kC Oi) HpcB hBoO} Qw{uX(Fw Lu) MxxA IduN} mT{HrVi ToSf ItUw RydB} Em{kK(Af Bn) OibR} Yk{HrnI cTmU hBoO} Kc{Kz(uN wL) PdwL} Um{KxfB LpnO clpH} Vj{MkmP KnpH dBmU} mS{LvQy MwUw IsYg} kF{OgrC UscM VobI} Dg{tN(cF Ki)} Du{MhmY aPoQ} Fw{IiqA ImrW} Hp{MukC SsaS} Qz{qQ(Aw oF)} Ye{MwnN bLfB} Rz{Rh(oQ oT)} Vh{HrmP PikS} aD{YgoO RykN} gZ{RxkQ UkbI} lW{BnDr JnLt} lX{AoGd UwaH} nF{LuMn LvQy} NrInml NuaLfB MlRgkG MxKzxA ToShhB ImRmsC HbVwmY ItbZzA SsOitM KgcFtR KirWuX KnOpnD UgOymW Constrained panels with 3 analytes, where 6.4E-10 >= 'AUC p-value' > 1.0E-10. Contains 9,598 panels of 37,563,518 total panels evaluated. : zH{Na(Ax Cp Cw Dc Hx Ii In Jo Ke Kf Kg Kn Ko Kp Kq Lw Ml Mm Ms Or Pa Pe Po rN sI Ut) Hf(Ba bV cD Cp Cv cW Dg jD jL Ke Lx Lz Mw Mx Pf Po Qa rB tV wD tM) Ri(Cv fY It Jh Jp jQ jR Kp Kq Ky Kz Nm On qP Qv tO Uf) Um(aC cV Db jL Kc Kz Lh Mt Pa Qt qX sM tO Uf Un wD wL) Cw(aR cI cN dK dM Hu jD Ji jL oE rB Rh tO tS tM) Jd(aF cU cV jQ Kc Ki qA qP Qu rA rN tN tV vP vS) Bc(Ap aV bV jV Kf lK Mu oF qX rO tN tR uU) tM(Fr Jh Ky Lx Mq Ms Mv Mz Oh Om Qe) rW(Ad Cp Dk Ic Jp Kc Ke Ks Ne Nj Vq) On(aU Bg fY Ic jG Pg Ql Qu qX Up) gW(Aa bE cl Fy Ib oE rN Up Uv Vs) xA(Ad Fr Ke Kn Kq Ms Nh Om Pi Po) It(aC aP bS Fr Hq Nk qX rA rB) Kz(Ap aX bC bV Cv jU Lh qO rZ) Di(aC aX dR hB jQ Kc Ky qX) Qw(jL Lh Lw Mm tN tV Uf Tk) Of(Hu Mv Nm Ns rN rS Vs wD) Un(Ih Ns Oi Pc sC vV wG yH) Ad(jD jQ lL Pc rB tO tR) Lh(cI dK Nt oN qP rB rN) Tk(cB Ez fP Lx My Uh vV) qX(cF Kf Ky Nh Nm Nq Vq) Mm(Db dM Mv Ni rN sM) Jp(aC aK aR Ih jQ tX) Ke(fY qP sC tN wJ wK) Kq(aL cY tR vP wG wJ) Nm(aK cI hG oE wG) Ic(Ba dM jL Ns sC) Ky(aR cI Mq Ns yH) tX(Ap Mz Oh Om Pz) jD(Is Jt Qa Qu Rh) qO(Ap cF Cp Ji Om) oF(Ap Hb jR Lu Nu) Qv(jV Ok Ug vS) aK(Ji Kp Lw Mq) sC(cI Kf lL Pz) rN(cF Kc Kg Nj) pF(Kg Ki Nq Ug) Dl(qP tS wK) Mz(Jg Mu tL) Nk(Jl Jt Nh) aC(Fa Ny Om) fP(bZ wE wQ) tO(Dk Kf Nv) Cu(tN wG) Db(dM oE) Lw(Ms qU) Hu(Jg Jt) Im(Nq Qc) Jk(Dk Jh) Vq(Rh yH) Pa(Is Oh) Pc(Fr hG) aF(Ip Ns) tT(Fb Ug) tR(Om Pd) iH(cI sI) AfNw AjJo BbUb PotN MljV MqMs IkPz JguP JibE QzyH QutV KfaX VsrB OywD PitS} Et{iH(aO aR Ba Bb bM Ch cT hA Hu Iu Jh jM jO jY Mc Pi qD) iA(Aw Bb cE cT hB Iq Kr Mq Mu Mw No Ql Qt Ub Ug) vH(aP bA Bb fP Fr hW Iu jI Kz Lv Ok qC Qw vI) qQ(cB cC Cw fP hB Mn Nu Pb qW Rh Ri rN Us) Ok(Hw Il In Jo Mm Ms Mw My Ne Nm Nq Og) rX(Af cA cQ Db hG Ic Id oE oF Ua Ub Ue) Fp(Hr Hw Il Im In Mw Nq Og Oy Pz Qb) aC(aN Bb cB cD Ch Cw Hu Iu Mc Om wQ) hA(Af aL aZ cE cI Db Ks Ky Rc Rh tX) tL(Bc cT fP Ic Iz Lw Qw Rh tS yH) Pa(Il Mu Mw My Nq Of Oy Qb xA) eD(aR cA cB gW Ks Kz Ql Qv Us) oK(bU cA cC cM Fw Hu Il Ks Pc) Ij(aA Jr Mh Mt Nh Ni Nk Qa) jD(aZ cA cC Hf Ic Ql rN Up) Ne(In It Iu Nh Oy Pz Qb) Nj(aH aN bA bU cQ cT Di) xA(cB Ef lN qC rY Vt yH) Og(aA hV My Ni Of qY) sJ(dB Fy Hc kS Oy Pk) qD(aF Bc jO jV Na Qw) qU(aQ Bo cC Fn gL Kz) jM(Bc cW Ks Kz Uh tF) jP(cA Db Ly rN sC wK) Nd(aW Ba bR cD Ch) Qb(aA Jr Lx Qa qI) Nx(aA Ng Nm Of Pz) aR(bR cT Di jU uM) tX(Co lL Up vI yH) jO(Bc Db Ic rN uP) jY(aQ cA cC Hf Rb) uZ(aK dM Ic Ql Ub) Eo(Iv Jr Nc Pg) Nq(aA Io Jj Lx) Ii(Is It Mr Pe) Il(Jr Lx Of Oz) Qw(qC tN tO wL) Tk(cC Ic jQ yH) rB(Ic Kz Ql Us) qY(aV Bc bZ Qu) jR(qO Vz Wd Yl) vS(Bg Bo Db Ki) Di(Mb rC tF) Tj(Fa Ha Qv) Nk(Io Iu Of) Um(tR tV wL) hO(Lw Mh Us) yH(Iu Ki Na) rO(jF uM Vt) rN(cB iP Na) vB(Dp Ua Uo) Mv(tR tS) My(Io Jj) Ng(Hx Nr) Iv(Jo Lw) Jr(In Mw) aA(Mk Of) cC(rY tF) dG(qC wK) nJ(Fi Rv) tO(Kz Ua) tN(Ez Gp) qO(aQ uL) vI(Hu Jk) AjrV AlwK BbuM BotM NtuG McMs NiOm HlnU IuOz JdVo TliP KstF RheT VqzI aWbR bGyL cMiO wDrY} Jd{Tj(Ad aR aW Bn bU cB cF Cp Cs Cu Id Is Ji Ke Kj Kx Li Lt Nr Oa Pf Pj Po Qe Qv Qx Qz St Tv Ut) On(aR bR bU Cu Di Fi Hr Hu Ij It Jk jM Nt Nv Of Om Vo Vw) jY(cW Db iH Ir Ki Kq Ky Kz lL Pj Qa Rh rN tV Un Wm) bU(aC aF Bb bR cB Hf iA Ib Pa Pb Qv Qw Tr Tt Uv) Ub(aR aW bR cF dX Hu Mc Mm mP Mv nT Ok Pj Qw) iH(Ba Bb cF Fw Ic jD Jg jM Ko Kq No Ok Ql Uf) lL(aL aN bS iA Il jG Jj Ns Pa Pj Ql sC uN vS) Fi(aR bA Bn cB Jk Mx Of Pb Tt Uo Ut) iA(cB De Hf Jp Jt Lh Pa Tt Uf Wh Ye) aR(bR cB De Ic jD jU Nf Of Og Uw) Vc(cS Kz Lh Nf Og Ss Ut Yg) cF(aN cD fN Fw jV Og qI Qz) eQ(aN Bc cK Hu Kf Nm nW oK) qC(aG Bc cL jV Qz Rg Rh Un) qU(cB fN jI Na rN rS rW tS) Vq(fN hL Hp tO Wc Yl Zq) Ic(aN aW jV qQ Qz tS) Ib(Mv nT Ry Zw Zx) Uv(cB Kn Mz Oh Pa) Oy(lX nC nJ nL nT) eD(cB Jp Ky Na Us) jM(Cw Jp Jt Mz Un) Hq(lX nC nJ nL) Nw(Dr Hp Ry Yk) bR(aN aW cN Di) gP(Kq nC nJ nL) hA(Jp Lx Pa Pd) jD(aZ Bc Db jG) uZ(Kz Lh tX wD) vS(aF cV Lh Pa) Nq(jH jI tT) Nu(jV rN tS) Tt(My Qu Qz) Qw(Oh tS uM) Uw(Cx De Oh) Vb(Bn cT Kj) bW(Ru We Yj) tV(bZ Hu Ua) qQ(Aw cW Kz) Mf(kO nT) Mz(fN In) Hf(uM xA) Ir(oN qW) Yi(Af Bn) Qe(lY oD) Qz(Pa Qv) Ki(bC qX) Ky(nC sJ) Rz(De Kk) Vh(Lh nA) aW(Ko nH) nF(Kr Mm) nL(bZ Cu) jG(cB dC) jV(Jj tT) uU(cV hG) AjCh CwoN DiNs FceM FdUt GdoO MalX HutX HxnT IdoV InPi JkVw JrJs XaRh LpVt LtUs TkvV OitO VonU PhoD dUoQ qWsC} On{iH(Bb bZ cO dB hA jG Jl lL Nf Nm Nv Of oH oK Om Pj tF) qC(aL cA cE Fw Hf iP jQ jV Mk Mv Nv qP Qu Qz Ua tM) Nj(aA Aj cH Ij Il Mk Mw My Ng Og Om Oy Pa) aN(aR bU cD cK Ii Il Iu Jl Na Nf Of Pc Uv) iA(Af Bo cE cK Kc Pj qP Rb Rh rN rS sC tO) Jj(aR gP hA hL Hx Iv jG Mb nF Nl sC vH) aR(bR Fw gP It jG My Om Po qO Uv) Tj(Fn Ib Kx Nd Qz Rg Uv Vo) tO(Hf Ki Mk nW Pi qW wL tF) Qw(eD hL hO pY tS wL yL) Oi(eD Fi hA qD qP qX vH) aC(Cw Db Dr Fi Jh Mv Ns) aI(bR Hr Ii Il My Nr Uv) jG(cA hA Ii Ij lL Ly Og) uZ(aK Bo bV bX Ch Kp Mq) Mk(eD hL Iv nF Nl) Hr(aO aW nF nK oV) tF(eP rW tT Uv Zw) rB(qO sC tR uM vV) qD(aL dF dG Mn Mu) rN(Fw Hf Js lL Nt) vB(Bo Di Il Kp Ua) Nu(jT lK sC tV) Na(eD oH tQ yH) Nd(bR cB gP Nb) Ii(It Ji Mb Ne) Kk(Fd Lt Vc Vw) Ql(tS tV wH wL) Of(Iv Mb Nl Ok) fP(Du wL zI Zw) nK(Iu Iv jY Ma) hO(aL Jk jQ Vq) oK(Af Db Iu Jl) vH(Bb Cw Qv xA) Fi(Fb Mx nU) Fw(DW tR) Nt(jM jT tX) My(cK Lx Nl) Pj(hL qY rX) cA(cK eD lL) gP(Ic Wd Wh) tT(Hf Nm Ns) tS(Hu Ky Up) vS(Us Vs Vt) Db(jM qU) Eo(Mg Nn) Yl(jQ lK) Nw(Dr Wb) Uv(aW dG) aK(wL tL) eC(Vw Tm) eD(Kz Li) eM(Gn Yj) eQ(Gd Kl) tX(Ki Lu) wH(fN Vt) wF(gW Mm) lL(uN wL) AfxA BbvP FbVb ExhA NqIv MaqO MwNl InnF HfjO VzjR ShgC ZxjF QbbR QuwG KysC RitN WnuM UpjM VqzI PctV PftL aWnL hLqU iPrC jYrS} Ok{iA(Bo Fw gP

Figure 4 Continued

Kj Kk Ny Yg) Zw(Hq Nv Om Qz Wh) Rz(gP Ma Uk Uy) aH(Si Uw Wd Wh) Iz(Rv Yg Yj) Hq(Rv Yh) Hr(Yj Ye) In(Nb Nr) Sh(hC nW) Wh(Oa Yh) Vi(cU Du) hB(Tm Xa) ChYj LuYg NeIN NjjE IshV ItIK QyRv YeOf OmVb UrUx iCjF kPrZ} Nm{tO(aR aS cC Fw iA Ki Nt) tT(bZ cF Qd uV vl) tS(aF An bZ Ki qV) Qw(qD tN wL yL) tN(cC iA qV) rN(Nq Nt qU) Dw(Gl Hv) eD(Db Rb) tX(cF iZ) qC(Oi tF) qW(vV wL) vB(Na Wn) BouZ GleW aSwG dBrX nRIK nKrZ jDvS oFuT} jH{mY(bO cZ gP Nt Nu) nL(cD dL hB iA Nj) Wb(Fr Oz Pa) mS(aF dR nY) nC(hB iA Nj) Nq(kG Tm) Vz(jF Ne) aR(lX tX) tF(kG mM) nR(iJ oF) nU(hB kS) AatS TiKx NuJi LvZx MpYd NhnK HxYe InkC IsnH UmVh UwVo UxjF aMnO bQkE dDlX hBkO} fP{wL(cI Kc nW qW rB rN wQ) uZ(bQ Im Mf Mw Mx Om) rX(Lw Ml Mq Ny Pb) Du(gL Hu Iz Ut) bZ(rN sM vB) xA(dJ Jn Pd) oE(uM uT uV) Xa(Iz Ss) vS(jO lK) AarN GbgL YjOy QzVj JpYe KywH bQuX mEjE sFjU qWuM} We{eC(Af iZ Kp Mh Qz Si Ul) iZ(cI Hp Ql Vp) jI(Hq Ms Ne Pf) Gp(aO oO tF) jT(Mf Om Pg) Tj(cB Dd) Mh(jE lO) Oh(jO jU) Oi(bW qV) gP(Il Ki) MfiC NblM NlqV HraO IkjG RcVb JecB JpjL KjmS KphC RhkN UlnW bRcL} qU{tS(Dg Kj Mr Uc) Ji(qD rN vI) mI(cI dR kS) nC(Aa hC iO) nL(bG cY pF) tX(Dl Nh Pc) Ex(hL yL) Zx(Nj Oi) Wc(Ni Nk) tT(It Kg) iJ(kK mE) DltR TiPc FnvS NcYl TvwG IstN QtrS JqTm JsXa KlrN bBkP cDkK cJmM dEkF} Vh{iZ(aV cC Gp Mb Nq Oi Wh Tj) Kk(gL Hp Je Nq) oN(bQ bS Hb Wh) Um(jU lM qV) Vb(Ib Je Mh) oH(bU Jl Oi) Hr(Jk nU) cU(Hp Mu) hC(Pi Wd) TjPs FpcF MvnR JecB JunT RhPk aEkI bUmY bWiP cXeC fRkQ} Ex{hL(Aj Bg bL Kg Lu Ms Nh qX Uu Vv) uZ(cH cV pF Pz qH) Tj(cB Ko Ld Pi) xA(cS Lu Qh yJ) hO(Fp Ly) qB(Lu rU) vH(Cp Ph) ArwL EwMh QetN SlqQ aYeD bLwH cUnT tQjV zIkS pSsC oNvP} nC{cH(hA lN Yi) eD(aJ cF cR) qT(Aa cL iO) lM(bB iA oF) Cq(Uv Vo) aL(hA lO) jT(cF oN) kS(jI rA) DuHq IzVo YgbB ZqnD WhKo RznH UvUt aQjO aUjP aVqY aYjV bMjU bZlN cBjG cLjD cOjF dFjL hAoF iOjE} gP{Gb(Ch Jk Mu Nq Oy) Vj(cX De Jh Li Ss) fR(Bn Gl Ko Ua Ut) Zq(Bn cX Oy) Yj(Oy Uc) Wd(Io Kk) Ps(cX Dd) Uw(bW cX) AfEq AwDl CpaR YfKo NoYg NqXa ShUt SsLt hAlX lWqW mMjF mSjI} nL{eD(Aa aJ bZ cZ Uc) jV(bN cD cI iJ) jK(bG cZ eF) Cq(Uv Vo) Zw(Ch Om) Rv(cD Rc) aQ(jO qY) bF(qV qY) hA(bG kR) jI(dE kS) lM(bB eF) AoGd BnDu LvVs MvaH HqbU WhLj UvUt cDlK iPqT lNoF} jF{Wd(iC jK lO Mp) bZ(kN kO nT nU) mE(aP bR cI Iu) kG(aL bC bE) kN(bU dG dL) Zq(Lu Nl) Zx(Jp Nk) Vw(jL lK) mH(bB bV) kI(bQ cE) NmH MkYl WgjK JlkF cSlW dCmM tHY mShC nBkS} aR{cB(aA Ba bQ cG cK cN Cp cW) Nj(Jj Jp Mt Nf Pa) tT(Dg Dk Fw Ms) Tj(Ko Xa) Ji(hL tR) Ky(sM tM) Of(Hr Jj) cI(tO tX) sO(sC vH) ArIo AwqO TiiB JpqQ aMdW bFbU jDvS} bW{Oi(Uz Vi Wg Xa) mP(Du Ry Sh Vw) Kx(Ps Vi Wb) mU(Du Rz Xa) Hp(cG Vs) Yj(Mt Nq) gL(Gb Xa) hC(Gc Ye) DunN YgeC YdhB WbOf PslW RziZ RyoO bFfR nOiB nRjP lXqW mMlK jIkE} Wn{wL(cC cZ dE Hq Ms oE Om qC Qh Ub Ue vH wH) tS(Jr Mg Nu Oi) vP(Is It qP) wH(Qw Uh) AaqC LurX HquL IqzG IsvV ItzI IvvB KgwD PhrS aHrV bGwF uMuN} Vb{Ef(aS bA bR cT nH Uo) gL(Hq Li My Nq Pi Xa) Ib(Dd Gp Oi Rc) tF(Ba cG Mb) oH(Cu Ss Uc) Je(Rc Uu) Jk(Bn De) lM(Uw Ux) AoiZ BakG ZqmS KooE UuPk PhnT} eM{Tn(Ba dL Gp Jm Jp Kn Mu Ou Yi) Wd(Aa aD cE Gc lX oH) Yg(An Dr hB Ik) Wh(cG cS Du hB) Ib(Du Kx Tv) Xa(Ba Mb) AweO CqLp ThVs FyVi KkOf PfgV} lY{Th(bU Cx Hq Ye) Wh(Mk Up Wd) Ye(Dd Oi Yg) jI(cH hX jL) lN(cI Mt Nl) Ef(Hp Uw) Yi(In Kg) Kk(Op Vj) Uy(bS Ih) TiiP EmhB GhfA GcIt YgPa XaKi OilK gLjL mTiC} uZ{Ji(aO cV dN Kk Mq oF Ql) Kc(aP cV cW dN jE Lx) It(hB kQ Kz Mq) oE(Ao Bo Ms qW) oF(Aa Dg Ky) Fa(Kz Na) Jp(Lz Qu) AaMs LxHb QzjE KyaP KzwD} rB{tX(Ao Cp Fw It Jo Jp Mg Pc) Aw(Dp tN tR uM) tS(It Ji Jo Jr) Cp(tT uM Us) Jp(iA qQ) Kz(jV uL) tT(Ms Pa) BosC DktO TiKs NmK InmE ltnH} rN{Nu(Ba eC Kj Nh Pi Uc) Fw(Dg Im Kg Kj) eC(Aa Kg Kj uU) rC(cF Nj Pz) uU(cV OF) Kg(sH vB) jD(Gz Nq) wG(It Nj) DgdG KjOi KliA KxsH PatF} Ky{sC(eD hG oF qW wB wL) wH(Jp Mr oE) xA(jD Ni Pd) Fw(sM uP) lX(gL Hu) jB(pK Tj) wD(jV tF) wG(hG Jp) CvdX OynT aEtS bQnF dDpK tNjV jEvS oHuP} dU{Nx(Ed Kr To Tz Um Uv) Yi(cX Kk Nj Nl Om) Yk(Kk Kn Ma Ow) Pe(Ef Rg Tv) Tn(Ch Ma) CuUt FyKr LvUg MvVo MxcM NlYg UadG UbcU JfbM UmbO} nT{Iz(Na Om Ub Uw Yg Yi) Ko(bH cM Db Ti) cG(Aa jP Ry Uy) De(Sf Sh Uv) bB(qY Yd) iB(dR iO) AoKs GcGd HpgL HqUg SfKk ZqOw RznW dFlK} jE{cB(kI kK mE mI) mM(aE bF dC oE) mE(dC dF jI) mI(Aa bC dL) nR(bB cF) lX(bZ dF) kC(Lx Oe) kP(cJ cM) nY(kK nF) NrkG WbOz KivS cTmS nKjI} dX{Mn(bA bR cH dD Pb Qu) kQ(Jl Jq Mt Ng Om) Kx(aE Ao dM Mt) Ji(Aa bV cI) Uv(Cv Nv) FycN GdQy LxNj MeQt MpoF UbJr JjKs KceF} lK{kK(aL Ij Og Qc) dC(kN lW mY) mM(aD bG cJ) dF(kO nO) fR(Ct Pi) nU(cG hB) mS(cE oF) nF(eF nY) MnWh MsWd ZwOi YlNx cDkN eClW nOiA mYnY} Uy{mP(Co cR Ef Fr Fy Jn Li Ut) lW(Dd Fy Tn) Li(mM nN) Va(jT jU) ChhC DufB NqnN ItnB YkjB YjpH WboQ ZqmH JnmU VcjT VsiJ jGjO} oH{Du(gL Je Mb Oi Qy Ut) Yc(Cu Gc Jp Ko Nr) Wd(cG Jy Lv) Ry(Ba Nv Tn) Tm(bB Tn) Rz(kG Mx) AjSi BaGd GcmU HocQ WbVs ShUt} Dw{Aj(Jj Nc Pa Pf) Nl(Dd Is Me Pd) Jp(Cs Ma Mr Qb) Fw(Nn Oi) Qa(Bo Ef) Oh(Ct Ma) Pa(Fp Mh) AwPe CsMp GdMt GlPz NqNe IlPf} eD{Gd(As dG Ii Ir Mw Oh Pe) Na(Aw Dl Ko) Rb(Pd Po Vs) Qw(Mv Mw Oh) cF(jD vS) AwqO PoiA TiIr LykF aJnO aQkK cXnF dGkO} eQ{Cq(Kk Ou Ub) Kx(bA bQ pK) Gh(Yg Yk) Mn(Iz Uk) Ub(Cv Qz) Ld(Ao Mv) Qn(aZ Um) Vs(Lv Th) BnKk DeUk DpcT GcbA GzdB TnnW IzaZ KoNx} hC{Sh(cU Qy Qz Rc Ua Ut Tj) Wf(Cx Kc Mn Nl Qy Zq) Ua(Gh Wh) Wd(oN Ss) cU(Uw Vw) ChRy UcSi ZqkG WhVv QzTm mIjD mSiB} lN{kC(Ij Il In Mx Og) mS(aQ cI dI nY) mY(bA dI pF) kK(cM Iv My) oQ(Jl Qc) vS(aF cF) LumW MenK MhkF HrlW aQmM aUmH} qW{Ye(Io Mr Ng Nh) sC(Aa Kp Pc) Vz(Iu qX) fR(dR Rh) yH(Kz Tv) kS(kN kP) vS(Id Vs) DgtT DlvB NhrW QwuX UrVi PctX aMmM} nK{rZ(Ii Iq Mj Mq nD Ng Om) In(hA Nx qV) iC(jI Pd qY) hX(jI Jm) NqSi MeqT MshV Mult IjjV NxjP PdhA PeqV} Na{Aa(sK uP yH) Dk(tQ vB vH) rX(Dl Kd Kr) Aw(jV vB) Cu(vH xA) Pd(tX wL) DltT FavB FrxA FyvH UcuL PitS sIwG} Ut{nF(cU Ii Ne Nh) Sf(kC mE mI) oN(Ru Vj Xa) oV(Ii Rg Ub) Yj(lW mH) DunO EqmE UboW KkRu RtkK UvkO aZpK} eC{Bn(Du Vi Wf Wh) Qz(Eq Gb Ps Yl) Yg(Yh Yj) Ye(Ko No) BaOp BgVc ChDr EfTm MeWh IoWd ZqOy JkRy PscX nFiC} gL{Uw(aI Co Gb No Sr Tn) Hp(Ko Li Nq Ps Sr) Ry(Jp Li mY) Vc(Du No Nq) Kk(Rv Vj) DkYi DubR RcIX} Zq{iZ(cY Kn Nf Uw) Hq(kF kK) mH(cL Kk) mY(cN Um) kG(aL cX) BnlX HvnH IbNv RhPk OgqX PbkF bQoN mSkQ} tX{Fw(cF cI Dg Ii Kg oE xA) Ao(bQ cF Nt nW xA) jV(Kz Nj) CpnW DgcF NqKg KcuN KivS cBiZ} Xa{fA(Af Kn mH) Ss(Kk Rh) Uw(mS oO) rA(Nk Tm) AonR BgoN TonD KnoO RhbR OiqV UlmS cCkG cGnO cTlW} gV{Nj(Fr Ny Oy) Ef(cI cN) Kz(Dk Fr) Pb(Jn Nu) AwdR NrbR LxPc MnNc IbdM IiKl HcIr QucI JpJr OibM} lM{Yl(Hq Hu iC Ir) Wd(Js Ml Oh) Hu(Wb Wh) Wf(Ih Nn) Ux(Um Uo) mY(dI nY) MlWg IkfR JsYe bPlX} Yj{pH(cW dB Id Lv Og) cX(mP mU nN) FdmP MvmI IbmW TvnU YinN WhtF KjiP QnpI NxpK bBmE} lW{Vi(Bn Cx Th) Dr(aL bB) Mw(Ry Ye) DudL ThHc NqRy MkWh ImZw WcKo JjrY OgqY aQjV bLrA cBjL} Qw{vB(Jp Mw Uc) Aw(qQ vI) Dl(qC tN) Mx(wF wL) rX(Id Om) CpvS DcqQ DkyL IuqD LitL PdwL} nU{Hr(Fd Ho Wd) jI(aQ dE mE) Uv(Hq Mu) AoHo TjOp FdTn NrIn TzZw UbQy YgYe WdcR iCjL} lX{As(Ba Cp De) Iz(Cu In Lv) qT(jI Mr Oy) bF(dR rA) DeoN LvHc MvKc aJjP cJqY dGjD} Ti{qY(aQ iP Ms Pf Pi Qc) iO(eZ qC) qQ(oF Tv) NuqV LyhX JelO aGqZ dRqC iAiC} Ji{Nu(qD tR tT vC) tS(Af cF iA) Ms(aA Iv) AfxA TjPa NqqD MdvI RfqC hLvS jDtL} cB{cK(Aw bA bF cN cT) bA(Aw cF cN) bF(aH cT) cN(Bn cT) CpTj HpUu TzLt mYqY} tF{tT(Cu Dg Kg) rA(kI kN) xA(Jp Pa) BaHp EmRc GdbB MnUw MxWd KcqQ KgrS PcwD jIkG} mH{Aa(Wf Wh) Hp(bB Ko) Hr(Fd Vw) rY(Jj Nh) DlGd DuGp EmhB ThoF GhfA KoPs aKjI bLrA} jO{fR(aU bC bH bM Ii Pd) Yl(jK Ni Nj) Zx(Me Nj) MhmT HqWc VzOh VwjV dRkN} eO{An(bA bN dW) Aw(aD cW dW) aD(dK Em) dJ(Ao aY) AfcG DkbL EfJk bQbS cEcQ} mI{rA(aM bC dL) jM(bJ dL) rZ(Js kP) NrIw HrYg InjL ZwOm JjiB cFjP cHqV eFiC} Gp{Dr(Ch De) Vi(iZ nO) nF(Je Lv) sH(rW tS) DukN IbLt WheF RzoO cMpK tTsF} nR{jL(cN cQ hB iC) jP(aJ aV bS cA) cG(Hp Rv) AoGd NqYg YiUv RznW} mE{rY(Iq Li Nt Qb) Yg(Bg nW) Op(Rh Si) bU(bF bQ) GcMu NrIn TmcH KoUw} pK{Kx(aE cI Cv cX Rf) Gc(aY Fp) aL(Dr Iz) CvVp DgGd TnRf RccM} Jp{qQ(bX cI Jj Kp Lz Um) AavS FwtS QuuN KzrX OfwL iAqC} Oi{Wf(iC jK) BnUw DgtN DltS TjEm YdjT SsrW WgqV KlwK YljK OmtT} Ib{sF(Ch Ju Po Qu) Uw(Ko Mn) DdZx EqmS MvmT HrVc iOsH} fA{Gh(cG Cx Mp Pk) Mv(nH Zw Tm) aD(Kx Wf) ZwaA VibB} nF{Ba(As bU) De(bU

Figure 4 Continued

Figure 4 Continued qC sJ yH) Uf(hO iA jY tT wL yL tM) Un(eD jM qD rX uN uZ tL) fP(Aa bB bR dD rC uZ) iC(mU mZ nA nI nK nR) Bn(bF bM Dg dN Tt)
Fb(Fi Ry Uw We Yg) Fr(Hx Jj Mb My Nk) Jt(iA Jj qD Qv wL) Ri(rN rW tX uN xA) Vq(jD jY qU Tn yK) gC(cG Gh Ko Nt Op) Fi(Jk Li Tn Tt)
Iv(aA Is Li Pa) Vt(hO jY rO sO) Pj(gP jR IL Qv) bR(bF cG cN Jh) qC(Bc Hb Nm Ti) Ap(rN sH tT) Ar(Is Mn Tt) Gn(Ib mZ nA) Mz(jM rW tL)
Ic(cN eD qD) Tr(rW vS wL) Ip(hL yH zI) Zq(bW mS oH) Qa(Mb Ms Qb) uZ(hB Kc Ke) Bc(hA jD) Ch(Dr Jj) De(bM IX) DI(bF Bo) Ef(Vw
Zw) Tt(Ib Jj) Je(jV Oh) Wd(eM nJ) Wh(eM nJ) Tk(wL yL) bE(dN fR) nN(cM nT) iA(Ke Ko) oH(Rz Xa) oD(Ld Uk) CuxA EoPz TiqY ExoK NtaA LvIs MbNv NhPa HqnK IdjY InOm HfqU WeiZ JkUw QmeD aYeO bFbM bJfR cGnT gLlX nAjQ wDtL

Constrained panels with 2 analytes, where 1.0E-4 >= 'AUC p-value' > 1.0E-5. Contains 1,678 panels of 199,257 total panels evaluated. : Di(aK An Ap aQ AR aU BA Bb bC bJ bM Bn Bo bR Ch cN cP cT De Ef Ex Je Jh Jj Jp Jt jY Kf Ko Kp Kx lL Lx Mc Mg Mm Mn Mz nF Nm Nw Nx Om Pa Pj Qw qY Qz Ss Tn tO Tr tS tT tV Un zH Tj) aR(aN aW Ba bR cT De Dg eD Ef Fb fP jD Jj Jq jU Kc Kf Kq Lh lM Lw Lx Ly Mg Mm Mr My Mz Nf Nh Nl Nr Nt Nv Nx Ny Oy Pa Pd Pj qC qP Qv rC rW sC sO tO Tt Un We Xa) Jp(aA Ar aW bA bU cB cF cK cT hA hR Ib Ic Ik Im Jj Jr Lj Lw Mr Ms Ne Nh Ni Nk Nm No Nr Nt Og oK Oz Pa Pj qC qD Qv Qw qY rB tN tT tV tX Uv Vo Tj) aN(aQ Ar bB bM bW cK Co Dc dD Dk fP Fr Hu Ic Im Jn Jq Kf Ko Kq Lh Li Lw Lx Ly Mc Mm Mq Mr Mu Mw My Nc Nd Ne Ng Nh Nl Nm Nr Nt Nv Ny Po Qa) Jg(aA cF De Dr Ib Ic Io Is Jq Kx Lj Lt Lv Mb Ms My Nh Ni NK Nq Nx Of Og Oz Pa Pj Pk Po Qa qC Qu Qv qY Rz tT tX Uu Ux Vb Vo Vw zH Tj) cF(aA aI aJ Ao Ap aQ Ar aS Ax Bo Ch Co cQ Dc dF dG Ef Et hB hX Is Ji Kc Kf lL Mn Mt Mz Nh Nw Nx On qC TN tV tX Un Vh tF) Tt(aC bC bU bW cA cN Cx De hB Id IH Im Ko Lw Lx Mm Mt No oD Ok On Pj qQ qY Qz St tS tX Uf uG Ur Uv Vb Vt Tj) iH(aI aQ aV Aw Ba Bc bW cB cK cQ De dJ Dl Fr hR iC Is jD Ji jL Ke Kf Kl lM Lx Mg Mn Mv Mw Mz Nt Of Pd Uf tF) Ad(aH Ar aV Ba bQ bR Ch dN Ex Fi Ic Ji Jo Lw Mb Mc My Ng Nl Og Pd Pj Qv Qz rB tO tR tS tT Ur Uv Vo wL zH) Nj(Ap Ar aW Ba BC bF Bn bQ bR bU bV cN Co Cp Cw Dc De Dg Dk Dl dN fR In Jr Lv Lw Mx Nc Nm Of Og Oz Pe) Bb(aJ aK aU aV bB bE bF bJ Bn bQ bR cG cP cY De dF dG Dl gP Ic It Mt Nc Nd Ne Nk Nl Qv Qz Uv wL yL) aW(aK Ao aQ aU BC Bo bQ bX cE cN Co Cv Dc dD dF Dk Ef Fb Fr Is Ji Kf Mt Nw Nx Pj Tn Uf Un We Xa) Kq(aC Aj Ar cA cB Cq cW eD Fw gW Jj jY lL Mc Mt Mv Mw Nb Ny Om Pj qC qO Qw qY Qz tR tS tV wG zH) Jt(bA Bo bR cB cK cN cQ cT dD eD Fi Fp hO hR Iv jD Li Mb Mt Nh Nk Nx tN tT tX Ug Uv wG xA Tj) On(aA Aj bA cD cT dE Fb hR Ij jY Ks Lt Lw Mm Mu nF Ns Pj qD Qw Ri Rm rN tR Uw Vb Vc Vw Yi tL) Ji(Ar Aw BA cB Ch cK cQ cT dD De hL hR iA Lj Lw Mm Mv Mw Oy qD qY TN tT tX wL xA Tj) bU(An Ap Ar aU BC Bg bH Bn bQ cN Cu Cw dD dF Dg Dl dN Fr Jh Jj Mt nN nT Nw Tn Un Vh) Is(An aQ aS bA Bo Ch cK cQ cT dD Fr Ic Il Jj Lh Mb Ms Nc Ne Nh Nt Nx Og Oz Qv Ur Tj) Nh(aA cB cT Fp Fr Im Jj Jq Lh Li Lv Mm Mp Mz Nm No Nr Nt Nv Om Oz Pd Po Qd Qe) Ar(Aw bA cB cT eD Et Fb gW Ic Io Jh Kc Kp lL Lw Mh Mt Nc Nl Nm Pd Qz Ss Tn) Kf(aC cN eP Fb Fw gW hA jM lL oH qO qQ qU qY rC rO rR rU tN tR tV tX vB tL) Lv(aA Fp Fr Iv Jj Lh Li Mm Mn Mt Mz Nc Ne Nn No Nr Nt Nv Oz Pa Po Qa tV) bR(Aw bM Bn bQ cT De dF Dl dN Ex Lh Li Mn Mt Nx Om Qa Qd Qe Tn Uf Un We) eD(aF Ap cB cS cV Db Dk fP Hb Hf hG iC Id jD jI Ke Ky Kz Lh Po Qw Uf Vt) Ic(aC aP BA cQ cT dD De dN Fr gL jD jG jI Jj Mt Nw Oh Qv Tn Un Ur) Ne(aA Fp Im Iv Jq Lh Lj Mg Mp Mt Nm Nn Nr Nt Nv Nx Om Po Qa Qd Qe) Jj(cB Fb Fp Ip It Jk Lh Li Lj Mb Mg Mm Mn Mz Nm Nt Nv Of Po Qa Qe) Cw(cB hL hO hR jD jO nC Nd nT qC rN rU rW tS tT tV wL Tj tF) Et(Aj Aw bC Bn cB De Ex hA Id jG jM jP jY Ks Qw rB Tr Vq) Ke(hA jY oK qC qD qQ rX sJ tO tR tS vB vH wG wL zH xA Tj) Nx(aA cK Fr Li Lj Mm Ms Mt Mz Nf Nk No Nr Nt Oz Pa Po Qa) tV(Aa Bc Dl Fw Hf Hq Ih Jd Kj Kz lK Ms Na Nu Of Om Qw wL) Tn(cB gC iA Ib Lw Mc Mm Nr Oh Pj Qu Qz Rh Uf Ur Uv Vc) Ap(bA Bn cK cT iA qO qP rS sC sJ tQ tX uM uZ zH xA) Cp(aK aQ Ba Bn dD Dc Fw Io Mt My Nd Nf qC zH Tk Tj) Mz(aC bA fP hV hX In Iv Kc Mx Nc Nf Nl Pd rC sO wG) Lh(Fp hL hR iA Il In jG Mb Mn Nc Nl Og qY rN tR Tj) Ok(Aj cD Ex Fn hR hX jG Ks qD Qv Qz Rh sJ Tr Ur Uv) Mm(Fb Ik Iv Li Lx Ml Mt Ni Nk Nr Oz Pa qD Qv sM) cT(Aw bC bM Bo Ch cK cN dD Dg Dl Fb fR Kc Ko Un) Nt(aC Fp Fr In Iv Li Nc Nk oD Oz Pa Po Qa Qc) Mn(Ba Fp Je Jr Kx Mr Mx nK Og Om Oz Pd Pe Qw) Jd(eQ Fw Hu Kk kO nH nJ nL Om Pk qQ qU We Yi) Nw(Ch De Fb hA hR jM jY Kx Pk sJ tN tQ uP tF) zH(Aw Ba Dc Dg Dk gW Ko Kp Qv Qw tN Uf wD yH) Tj(Cu De Fb Fr Kn Ko Li Mt Nr Oh Pe Qa Ut) Nc(aA Fp Im Iv Mb Mp Mr Nm No Nr Po Qd Qe) aC(fP Je Jq Ko Lw Mc Mr My Nd Pa Pj Un Wd) cB(An Ao Ch Ct Cu Je Jh Mt Nl Om Qa tT Wh) Dl(aS bA bC Bn dD Dc fP gW jY qC tS xA) Fi(Cu Dk Ef Fr Iz Ko Oi Oy Qa Qh Ss Ut) Vh(gC Im Io jF Jk Mu nJ Ny Oi Pk Ut Vb) fR(aQ aS aU bM Bn bW cE cG Ch dB gP jQ) Dg(aS aV bA bJ Bo cK cN dD De gW tT) Mt(De Eo Fp Iv Lj Mb Ms Oz Pj Qv Qw) Li(aA In Jq Mb Nf Ni Nk Nm Og Qw Qz) fP(aD aI BC Bn cD Ch cM cO Dc xA) Aw(aH aQ bA bC Bn cG Ch eO qO rB) Fb(Aj bQ cN Io Ko Mc Pj Qv Qz Uf) Nm(Fp hO Iv Lx Oz Qa qD tN tS) Qv(Dc Io It Kj Ko Mg Pd sC Uf) Om(Fp Fr Iv My Nl Og Oz tT Uv) Un(iA Io jD qU qY Rc vS wL yK) bF(aH An bC cK cN cO dN lX Nd) Oh(eO Ib qC Qw Uf Ur Uv wL) oD(cM cX Iz Nd Nf Nu Rf To) Bo(aU aV Bn cY De Ef gW) Po(Il In Iv Nf Ni Og Oz) Lx(aA Ch Jq Lw Ms Ni Qb) bM(BA bQ cE Ch Ct dD) cK(Ba Bc cG Cu dF dN Kc) rC(Bc cS dN Hf hG Kz rN) jD(iC Je Pi Qm Uf vS Vt) rX(aF cV dB hB Kc Vq Vt) Ex(Ch gW Je Nd Ss uZ) Fr(aA Jr Ms Mw Og Qz) Nl(Jq Lw Mr Of Og Pe) Qa(Hx Il In It Jq Og) Lt(Dk Ef Iz Jk Ss Ut) Nv(Fp Hx My NK tT) wL(gW Kc Ri tT wD Wn) sO(aX Hf Na sC uM vP) De(aU dN Il Nd Qz) We(Dd Gp Io Pk Vb) Xa(bW gW nA Rh Ss) Ky(sC uP uX zA xA) Rv(gC gL mZ nJ Oi) Uf(jO oK qC qY Vo) Vq(hO jO qB Zq xA) lX(Bn bQ cX oN qT) nI(jF jQ oV Zq Th) Bc(gW hR qD rW) Ef(cN Vc Yg Zx) Tr(qQ tS wG tL) Iv(Jq Ni No Oz) Wh(eC hC Io mF) bA(Ch Dr Io It) dN(aQ aV bJ dD) nK(hV Mv Nq Nr) tX(Ao Fw Lu Pd) qC(Cu Ii Kl Tz) Ba(aH Ct gP) Fp(Mg Nf Oz) Hb(eP qD vB) Ip(hV qD sM) Iz(nT Uw Vc) Kg(rN tS tT) Ko(cN Fw Qz) Kz(uZ vB xA) Ri(rU vS wH) Pj(cN hG oK) nJ(Du Ry Zq) Bn(aV cN) Dr(Bg Rc) Eo(aP No) Nr(In Oz) Mb(aA Qe) Ib(Vb Zx) Rx(Jk Ut) Op(iZ mZ) Tk(bG hG) Uw(jG jM) Vt(qQ uN) cG(eO nO) dU(To Uy) tT(Ma Pd) jF(kG Vi) jH(mM Vj) vS(Id lN) pK(Du Gc) ChnF CuaV DwaM EmdB GnPi MquZ NahV NdJn NkQd HlmZ HpRc TzqU HxaA HfsF IoKx ItUr YgeM ZqRh JelL SseP WdhC QwuX TmgL TlOi KcvB KlrN UhsJ UvkF PfgV dJeO gCiJ gWnL nRlK jIjY jQkN Constrained panels with 2 analytes, where 1.0E-3 >= 'AUC p-value' > 1.0E-4. Contains 2,881 panels of 199,257 total panels evaluated. : aR(AA aI aK An Ap Ar aU aV bA bB bC Bg bM Bo bQ cE cG Ch cJ cK cN Co Ct Cu Cw cY dD dF Dk Dl dN Fr gW hB hR Ib Id Ke Kl Kp Kx Mc Mq Mu Mw Ne Pk qH qX rN rS rX Ry sJ Ss Tn tR tS tV tX Ue Uf uM Ut Uu Uv Vs Wh Yg yH Yk zG tM Tj) Jj(aA aN Ap Ar Aw BA Bb bR cF cK Cp cT De Dg Dl eD Ef hR IH Im Ir Iz jD Jh jI Jl Jm Jo Jq Jr Js jU Kc Kf Kg Kj Kl Kn Ly Mp Mr Mu Mv Mx Nk Nn No Nu Ny Oh Om Oz Pa Pd Pj Pz Qd Qm Ss Tn) Ic(Aw bC bF Bn bQ bR bU bV Cp Cw cX Ex Fa Fb Fn gP hG Hu Id iH Im Io Je Jh Ji jR Jt Ke Kf Ko Kx Lh Li lN Lx Mm Mn Mv Mz No Nr oK Om Pd Pj Pk Qa Qe Qh Qz Rc sM St tS Tz Uf Ut vS) bR(aA aI aJ aK An Ap Ar aU aV BA bB BC Bg Bo bU bW cE cL Co Cu Cw dD DG Ef FR hB Hu Im It Kx Lx Mm Mx Mz Nb Nc Ne Nh Nl Nm Nr Nt Oy Pa Pd Pe Pj Po Qh Qv Ss Ut Wh) Qv(aN Ap Ar Aw Ba Bn bU Ch Cp Cw Dg Di Dl Dp eD Ef Ex Fr Hu iA Ib Id Im Iz Jh Ji Kf Kg Kl Kq Li Lx Mn Mv Nm Nr Nw Oh Om Pa Qa Qc Qm Rc Ss St Tz Ue Un Uu yH) iH(Ao Bg Bn cD Ch Ct Cv Dc Dk Ef Fy hB Hu hV hX Id Im Ir It Je Kg Kp Ky Li Lw Mr Mt Mu My Nf Nj Nv Nx Ny Oh Po Qa Qh Qt Rc rS rW Ss Tn Tr tS tX Ue Un Uu wL) cB(Dr Fb Hp hR Hu Io It jD Jq jY Kc Li Lx Mm Mn Mu Mv Mw Mz Nc Nd Ne Ni Nm Nn Nv Nx Ny Oh Pj qC Qw qX Rt rW rX tN tO tS Tt tV tX Tz Un Ut vS Wd Yg zH Xa) Ba(Aj aK aQ Ar aV Ax bA Bb bF bJ Ch cP Cs De Dg Dl dN Dr eD Fi fP fR gW iA Io Is It Jp Jt Kc lL Lt LX Mt Mz nC Nd nF Nw Om Pj Qa Qe Qz sC Un Vc Tj) Dl(aK An aQ Ar aU aV bM bQ cE cG Ch cK cN cP cY dF dN eD Ex Fb Fi fR Il It Jh jM Kp Kx Mt Nc Nd Nl Om qD Qz rC rN tN tO tR tT tX uM vB wL Tj) cN(aK An Ao

Figure 4 Continued

Ap aQ aU aV bB bC bE Bg bJ bM Ch cK cM Co Ct Cu Cw cY dD De dN Ex Ib Is Je Ji Jp Kj Kq Ly Mg Mt Nd Nm Nt Nx Of Qw Qz rC sO zH)
Fb(aC aF aN Ax bA Bb bF Bn Bo bV cA cF Cw Dc Hu Ib Id Im Is It Jg Jh Ji Jt Ke Kx Ky IL Lw Lx Mv No Og Om Pd Pk Qm Qw uM Un Ur
uZ xA Tk) bU(aA aJ Ao aQ aS aV bB bW cA cE Ch cK Ct dG Dk Ef Ex hB hG Io It Je Jq Jt Kc Ke Ky Li IX mE Mn Mz Nb Nd Nh NI Nx Ny
oD Om Pa Pj Ut Tj) cF(Ct Ex hR iC jD Jh Jt jY Lh Li lM IN Lx Mg Nc Nd Ne Nl Nm Nt Om Ow Pa Pd Pj Qa qD qX qY rN rX tO TR tT Uf Uu
We wL zH Zq Tj) Pa(An Ar Aw Bb cK Cp De eD FP gV Ik Is Jh jI JI Jq Jr Jt Lh Mn Mt Mx Mz Nk Nm Nr Nv Om Qd rS sO tT tV Ur wL tL xA
Tk) aW(aJ bW dJ Dr eD Id Im It Je Ke Kj KI Kp Lh Li Lx Mm Mn Mz Nb Nh Nm Nr Nt Nv Om Pd Qa Qd Qe Qz rX Ss Tz Ut Vi Wd Wh Zq) Aw(Ex fR hA iA Io Is It jM Jt jV jY lK lL Mm Mn Mt My Nd Nj nN Nw Pd Pj qC qU Qw rC rN rS rW tS tT Un Uv vB xA Tj) Ar(aK aV Bb bC bF bM Bo cE Ch cK Cw cY Dc dF Dg Il It jD Jt jY Ke Kf Ko Mg Mm Mv Nd Ne Nw Nx Om Pj qU Tr Uf Tj) Qz(bA Bn Cp cT Dc dD Dk eD Is jD Je Ji Jt Ke Kf Kl Mm Mn Mt Mz Nr Nv Nw Oh Om Pj Qa qC qD qQ Ss Tz Uf Un Ut) Qw(Ad bA Bb Cp Cw dD De Fr hV Im Is It Jg Jh Ji Jt Kf Ko Lh Lx Mm Mz No Nr Nx Om Pd Qa qC qD rX Tn Tt Uf Un) Ch(An aV Bb bF bJ Bn Bo cE cG Cs Cu De dF Dg dN eD gW It Jp Kc Kx Li Lt lX Mn Mt Nj Nl nT Nx Pe Pj Qa Qe) eD(aK aN Bo cA cW dN Ex Fa Fn Fr Gl gW hV Jg Ji Jq Kg Kn Ko Kp lM Lx Nv oK Pk qO sC Tn Tt Tv Tz Ut Vq) Dg(aH Aj aK An aQ aU bC bE bM bQ cG cP Cw cY dN Ex iA Kx Nd Nl Pk qC rN sC tN tO tS tX uZ wL xA Tj) De(aK An aQ aV bA bC bE bF bJ cK cT dE Ex fP fR iA Io Is It Jt Mb Mn Mz nF Nl Nx Pb Pd Pj Tn Uf) Tj(aN Bb Co cT Fa Hb Ir It Je Kc Kp Lx Mn Mz No Nw Nx Oa Om Oy Pf Po Qc St Tz Uf Un Vh We Zq Xa) Fr(aU aV bJ Bn cK Fp gW hX iA Id Jq Jt Lt Lw Mu Mv Ng Ni Nm Nq Oz Pj Pk sC tT tV tX Ur Vc xA tF) bA(Aa aK An aU aV bC bF Bn Bo cK dD Dk dN eO Jh Kc Ko Ly Mg Mt Nd Nf Nh Nl Nm Nw Nx Pd Pj Un) Mn(An Bn cK Hx Ib Id Ik Ip Jl Jq Lj Lw Mb Mz nA nF Ni Nk Nm No Nt Nu Pj Pk Uf Un Ur Uv Wh) Om(Bb cK Fi Hx Is Jr Lj Lx Mb Md Mx Mz Nc Nf nK nN Nq Nr Nv Nx qC Qd Qe tN tR tX Ur Vc wG) Bo(aK aQ BC bF bJ cG cP Ct Cu dE dN Ex It Jp kC Mg Mt Mv Nc Nd Nj Nl Nm Nw Of Pj sC) Cw(aK aV Bb bF bJ bM cK Di dN gW In Io kC lX Mm Mt Nc NF Nl Nw Pj tN tO tR tX Uf wG) Jt(aA Aj aQ bC bF bQ Fn hV Ii Il In It Je jM jY Kc Lv Ni Nr Og Po qY rN sO Uf Ur Vo tL) Cp(Gp Hr Hv Hw Hx iA Ir It jY Kc Kp lL Lw lX Mb Mc Mm Na Nl Nm Nr qO rC Ur Uv vB xA) Mz(cA cK cT hR Ik Je Jg Jr Kp Kx Mb Mm Ne Nk Nm Nr Nt Oz Pe Qe qU rB sC tT tX vI yK) Is(Aj Al bF Bn Fw iA In Je Jf Jq Lw Nf Ni Nm No Nr oK Pj Pk qC qD Qg Rm Uf wL tL xA) Lh(cK eO Fn Fw hA Hx Ii jD jM jY Kq Lj Lw Ms Mw My Nb Nf Ni Nk Nm Nr Nx oH qQ Rc) Un(aN dD Fn Fw Hu It Kx lN Lx Mv Nr Og Oh Pk qQ rB rC rW sJ Ur Uv vB wG wH yL xA) cT(An bF Bn cG dN Ef Ex Io It Jh lX Ly Mt Nc Nd Ne Nf Nl Nw Nx Pd Pj Qa Uv Zq) tT(Ao Bc cI Cu Dk Fw Hf Ii Im Ke Kq Lu Lx Mg Ms Ng Of Po pS qW sF sH sO tV vI) Uf(Ad aN Di hA hL hR Hu Im Io Jg Ji Jp Jq lL Lw Mc Mt Mv oH Qm qQ rB sJ Ur) qC(Ao Ap Dc Di Gl hR It jD jL Kf Kp lL Pd Pi Po Qa Qc Qe Qm sC Tr Tt tV Uh) Fi(Dc Fw Gb Hc Ib Jn Jp Ke Kf Kl Kq Nq Nv Ok Ph Ps Qu Uc Vh We Zq Xa) Nm(fP Jl Jr Lj Lv Mb Mt Ni Nk Nr Nt Nv Nx Po Qd Qe rN sJ tO tX wL xA) Mm(aA Bb hR Hx iA jF Jr Ko Kq Kx Lj Mr Ms No Nt Og Pe Pk qZ Uv Zq Tk) sO(aF aK aU Bc bW cD cI gW It jY Ms Mx Nu qO rX rY tV vB vV wG wL yD) Di(cG dD fR hR Id jD Kc Ke Kn lM Lw Mv Ns rW rX sC tR uZ vB yH xA) Jg(gV hR Id jD Lw Mu Mv Mw nA No Oy rN tN Ur Uw Vc Vq wL Yg Yi xA) Og(Fp Ik Ir Jl Jq Jr Kf Ko Kq Lv Nc Nh Nn Nr Nt Nv Pj Qd Qe Tn Tz) dN(Aa aK aL An aU bB bC bM cG Ct eO hR Io Ji Kc Nd Nx rX Tn uZ zH) tX(Ad Hb Hf Im Jd jH Ke Kg Ki Kq Ma Mg Ms Na Nu Pc Pi qU qW wL zH) rC(aF aK aM Ap bW cV cW Fa hB Jd Je jI Ke Kg Kn Kq oE Ri sC Vt wD) jY(Ap Gl Hf Ji Jp Kf Ki Kn Ko Ok Pk Qm Rc rN rS sC tV Tz Ut uX Wd) Pd(Bb dD fP hV Je Jr Ne Nf Nk Nn Oz qD tR tV Ur Uv wG wL yK xA) Pj(aN bC bV cQ dD Fa Im Ke Kf Ko Kx Mq Mv Oh Ok Pk Ug Uv Tk tF) lL(Ap Dk fP Hb Hf Id Ke Kg Kn Kp Kz Na Ph Qm Qt Rc rN sC Tn Tz) Cu(aK aQ aU bC bM cY dD gP hL hO jM oK qD qU rX tO tS uZ wL) Jq(cP Fp Ik In Jp Lj Lv Mb Mt Nc Nf nK Nr Nt Nx Oz Po Qe Uv) Nv(aA Ii Il In Lw Ms nA NF Ni nN oD Of Oy Oz sC tO tS wL) bM(aA aK An aQ aS aU aV bB BC Bg bP cG Co cY dF Dk Ef) gC(aI aM dF dG Et Hc Kq nI Nj Nx Oi oO Rz Tr Tt Ux Tl Th) tV(aF aK aU bZ cI gW Ke Kg Kp Mv QU rS sC tO vI zH tL) Ex(bC bF Bn bQ cG cJ dD Hf hL Kc Kx Nl Nn Nx Oh Wm tF) Ap(aS aV bE bJ dD gP gW hA jD jM Kx Nd Pk rO tN wL) Dk(aS aU aV bE bJ cJ cY dD fP gW Io jM Kx Nd Nl xA) Po(aA cQ Eo iA jD lK Lw Mb Ms Oy Qb qD wF wG wL xA) Ko(Fn Hf Lw Mc Mv Na nT oD Pk qO rX tS Ur uZ Vc xA) Bn(An aQ bC cG dF Gn Jp Mb Mt nF Nl nT Nw Tn Vh) Qa(cQ dD Fw iA Iu Lw Ni oH oK Oz qD Qg Rm Ur wL) Je(aN cQ Io It Ji jM jU Li Lt My No Nr Qm qY We) Kq(eP Hu Iv jD Jy Nf rW rX sC tN tO Tr Ur Uv Vp) Dr(Ad cG Co cY Gp Hr Iz Jd Jk Oi On Ss Tn Uu) Mb(Bb Jl Lj Ne Nh Nk Nn No Nr Nt Nx Oh Qd Vh) Id(aC hA hR In Jp Oh Ok qD qY rX Tn uN uZ zH) fP(Ao Bg Ct hR iA Lw Mg Mr nN OH qQ qU rN) tS(aF Ao Bc cH Dc Hb Jd Kc Ki Kj Kn Pi Qm qU) Ke(aN Fw hL Io It Nf qO qU qY tN uM Uv Tk) dD(aK aQ aU aV bC cK Ct Ef It Jp Nh Nl Nx) jD(Hb Hf Ip Jd Jh Jl Jp Kf Ki Na Tz Xa) rX(Ad aZ BB BC bW cW Hb hG Ki Ky wD) Qe(aN cQ Il In Lv Lw Ms Ni No Oz Qb wL) fR(bB bC cK Io jO jR lK Nc Nl Of Ub Uv) nK(Hu jF Jh Ji jQ jR Mt Mu Mw No Ny Oi) Bb(Ax Fn Io Jr Kx Lw Mc Mv Pk sC Ur) Na(hR jI jT Nj sC sM uX vI vW wB yH) Im(iA Iv Lv Nx sC tN vB wG wL yH xA) Hf(hR jU jV lM nT rN rW uX vS yH xA) Rc(Du Em Rt Rv Ry Uz Vc Vi Wg Tl tF) Xa(fA Gn Io kG Mh nJ Oi oK Vh Vq tF) Kp(aC Fw iA Io Mt No Oh oK qQ uZ vB) zH(aF cI cS cV dM hB Kg oE qO sC wK) Ad(Fn Gn Ib Ks Pk Qu tN Ug uZ Vq) An(aU aV bC cG Ct dF eO It Jp Lx) Bc(aK aU aV bF bJ tO uU uZ wL xA) We(bW cU Fn Hr Lj Mh Oi Rh Ss Vq) Kc(aC Hu iA Ib Kn Kx Mv qQ sJ tN) Vh(Cs Dp Hb Hr Hu Jr Kk Li Lj Pi) aN(Aa aI Ao Ib Kl Qd Ss Tt Uh Zq) rN(Dc eC Fw Kj Nq Nu Ss uU wG yD) Lw(Fp Iv Li Nc Ne Nh Nr Nt Nx) Mt(aA bC cK Kx My Ni Nt Ur Uv) lX(Ao cG cM Db dF Ef hB Iz qX) hV(Ji Jp kF mU nJ nR Nu Nw Oi) Nh(bF cQ Jr Lj Mr Ni Pe rW) Tt(eM Hu iA iP Mv qZ tR uX) Tn(Aj eQ Hu It jM oD vS tF) Yg(aC eC Ib lZ nJ On Ss) Kf(Aj Mc Nn rB Ur Uv Vo vS) Kg(jM tO tR Ur uZ vB wG xA) nA(Hq jF jR Nq Nx Oi On Op) wL(aF Jl Ky Kz Mp Nx qO Uc) Ef(Aj aS bJ Eo gV Ux Yi) Ne(Aa bF Mr Ni Of Oz Pe) Nk(Jl Lv Mp Mr Mu Ni Nn) Jd(fN gW jU qY tR vS xA) Jp(aQ bQ cQ hL hX sJ Tk) Rz(bW iZ mF mZ oK Rh Vq) Nw(Fn hX qZ rB Ur vT Zq) cK(bC Bg bQ cE Co Jh Oh) eO(aD bQ cP cQ dF dG Pf) nN(cU Hq Hr Hu Iu Mv Nr) nT(dF gL hB Ky nW Sf Ub) Tk(Hb Ir Pf qI qO xA) On(Ed Eo eQ Fd rB Vq) Vc(Bg bQ Hc Oi Oy qT) Vi(aC bW eM gL jO nJ) aV(bC bQ cG Ct dF It) nF(Bg Co Lu Nq Nr Ut) iZ(Gc Hl Uw Wh Yi Tl) jI(hR Hv hX iC Ms Nu) wG(hB Kn Lx Pi qZ wD) jQ(kK mF mI mP mU nR) Dc(Nd qD qQ tR xA) Fp(aA In Mp Ni No) Lv(Lj Mp Mx Nx Qd) Nc(bF Mg Of Oz Pe) Ji(aQ bC hA sJ Uv) Wd(eC gP Io Kk oK) Li(iA Il Lt Ms Ur) aC(gL Ib Qy Ry Yk) eP(gW hC Kl St Uc) jM(Fa Hb Ok Ut Vt) rS(eC Fw Mg Of uM) vS(cE jL Ki Kz Qt) Gn(Pk Rj Rt Vu) Nr(aA Ni No Nt) Hp(Pz Ss Ua Uu) Tl(iP mE Mh qY) Lj(Jh Ni Nt Of) Nx(cQ dU Ni Pe) Vj(gL Kk nW Rh) Oz(Jr Mx Nn Qd) jH(lY mU mZ nR) wD(rY sJ tO wF) qU(cS Fn Ut Vt) lM(bZ Tz Ux tM) oH(Du Ux Vw Ye) oK(Gb Ir Uw Wh) oD(dC Hr Mq Ns) uZ(aP bX Fa oE) Co(aS bJ Nd) Eo(aD cW Nn) Gc(hC Ua tF) Lx(hO Qm tL) Hl(nJ nU Vu) Tr(qY qZ Uv) Ik(aA In No) Hb(qY uX Zq) Io(hG Ou Ut) Yi(lY mS nJ) Kx(eQ It pK) Lt(Bg Oy Qy) Oi(Em hX yH) Pe(gV Il Nf) aF(dW eW vB) bF(Ct Ly Nl) cG(aH aK tF) dF(aH aK aU) mH(Db Em mU) tN(Ma Nu Ri) qD(Ii Pi Qm) jF(kF mZ nR) jR(mI mU Yl) Aj(Kl Ss) Th(lW oP) Nt(bV cQ) Mh(Rt Wh) Ms(Qd qZ) Nj(Ao cA) Tz(rB Ur) In(Cq Ut) Sh(hC nW) Jh(cQ iA) Jk(Fd Yf) Ye(Dd hC) Ki(qX uX) Ps(Rh Vq) Ky(Oy wH) Kz(jV yH) Rv(Qy Ss) Rg(kF kG) Oh(Jr tL) Ok(hA qY) Pc(aA wB) bW(Ry Vw) cM(hB oV) eW(aY cW) gW(Ct pS) mF(Op Vs) qW(sC yD) qH(Ri uM) xA(Kn Pi) BgbJ DbjU TiqV GlvB NboV NdbV NlbC UaZx UbnU UcyL HxJl HcgV IpvI YjgL VzqT ZqPk QddW WfOy TmhB KluM UgdU UwgP UyjB UxnJ VtrB bBiA cIsC cVhR kGrZ kKlK

Figure 4 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.0E1 | 6.0E1 | 8.1E1 | 7.4E1 | 5.8E1 | 5.5E1 | 1.0E0 | 7.0E0 | 4.8E2 | 2.4E2 | 1595 | 22 | 266 | 22 | 0.46 |
| Ad | ug/mL | 3.8E-2 | 4.6E-2 | 9.4E-2 | 6.7E-2 | 4.1E-1 | 5.7E-2 | 2.7E-4 | 2.6E-3 | 8.5E0 | 1.9E-1 | 447 | 21 | 170 | 21 | 0.54 |
| Af | ng/mL | 1.2E0 | 1.2E0 | 1.8E1 | 1.7E1 | 6.7E1 | 5.1E1 | 1.7E-3 | 1.7E-3 | 5.3E2 | 2.4E2 | 447 | 21 | 170 | 21 | 0.54 |
| Aj | ug/mL | 1.4E0 | 7.6E-1 | 2.6E0 | 2.5E0 | 2.4E0 | 2.7E0 | 1.5E-3 | 1.1E-2 | 6.1E0 | 5.8E0 | 447 | 21 | 170 | 21 | 0.46 |
| Al | mg/mL | 8.7E-5 | 8.7E-5 | 2.5E-4 | 2.9E-4 | 4.1E-4 | 3.8E-4 | 2.3E-6 | 6.6E-6 | 1.9E-3 | 1.4E-3 | 447 | 21 | 170 | 21 | 0.54 |
| An | U/mL | 4.8E1 | 8.4E1 | 1.8E2 | 4.3E2 | 5.5E2 | 9.5E2 | 9.8E-4 | 1.4E1 | 7.8E3 | 4.0E3 | 447 | 21 | 170 | 21 | 0.64 |
| Ao | pg/mL | 9.2E1 | 1.3E2 | 5.1E2 | 5.6E2 | 3.5E3 | 1.2E3 | 1.5E0 | 4.1E0 | 3.9E4 | 4.5E3 | 447 | 21 | 170 | 21 | 0.61 |
| Ap | ng/mL | 3.3E1 | 4.5E1 | 4.7E1 | 6.1E1 | 5.0E1 | 6.8E1 | 8.4E-5 | 2.7E0 | 3.3E2 | 2.4E2 | 447 | 21 | 170 | 21 | 0.54 |
| Ar | ng/mL | 9.5E-1 | 1.7E0 | 1.2E1 | 7.0E0 | 1.9E2 | 1.3E1 | 3.4E-3 | 4.1E-2 | 4.1E3 | 5.1E1 | 447 | 21 | 170 | 21 | 0.62 |
| As | ng/mL | 8.7E-3 | 1.3E-2 | 1.6E-2 | 1.6E-2 | 6.1E-2 | 1.5E-2 | 1.7E-3 | 1.7E-3 | 1.2E0 | 7.0E-2 | 447 | 21 | 170 | 21 | 0.61 |
| Aw | pg/mL | 1.6E1 | 2.1E1 | 1.6E1 | 2.1E1 | 6.4E0 | 6.1E0 | 2.9E-2 | 1.1E1 | 5.1E1 | 3.2E1 | 447 | 21 | 170 | 21 | 0.74 |
| Ax | ng/mL | 2.1E0 | 1.7E0 | 1.6E1 | 9.0E0 | 6.3E1 | 1.3E1 | 1.2E-2 | 4.1E-2 | 7.7E2 | 5.2E1 | 447 | 21 | 170 | 21 | 0.50 |
| Ba | ng/mL | 6.1E1 | 9.4E1 | 4.1E2 | 2.1E3 | 1.1E3 | 3.9E3 | 3.7E-1 | 1.1E0 | 8.1E3 | 1.5E4 | 447 | 21 | 170 | 21 | 0.58 |
| Bb | ng/mL | 3.4E0 | 6.4E0 | 6.8E0 | 9.7E0 | 1.4E1 | 1.0E1 | 4.1E-3 | 4.1E-3 | 2.5E2 | 3.2E1 | 447 | 21 | 170 | 21 | 0.61 |
| Bc | ng/mL | 3.8E1 | 8.6E1 | 1.1E2 | 1.8E2 | 2.0E2 | 2.9E2 | 1.1E-1 | 2.9E-1 | 1.2E3 | 1.2E3 | 447 | 21 | 170 | 21 | 0.62 |
| Bg | ng/mL | 7.7E-2 | 4.1E-1 | 5.4E0 | 1.0E1 | 3.0E1 | 3.3E1 | 5.3E-4 | 5.3E-4 | 4.4E2 | 1.5E2 | 447 | 21 | 170 | 21 | 0.64 |
| Bn | ng/mL | 5.6E-2 | 7.5E-1 | 1.3E0 | 1.9E0 | 3.3E0 | 2.5E0 | 5.6E-2 | 5.6E-2 | 5.8E1 | 8.6E0 | 447 | 21 | 170 | 21 | 0.58 |
| Bo | ng/mL | 1.2E1 | 1.5E1 | 1.4E1 | 1.9E1 | 1.9E1 | 1.7E1 | 1.6E-2 | 1.6E-2 | 2.8E2 | 5.5E1 | 447 | 21 | 170 | 21 | 0.58 |
| Ch | uIU/mL | 9.7E-1 | 1.6E0 | 1.7E1 | 1.5E1 | 1.0E2 | 2.9E1 | 3.4E-3 | 1.5E-1 | 1.8E3 | 1.2E2 | 447 | 21 | 170 | 21 | 0.59 |
| Co | pg/mL | 3.8E1 | 6.7E1 | 1.8E2 | 2.3E2 | 9.6E2 | 4.5E2 | 1.5E-1 | 7.3E0 | 1.7E4 | 2.1E3 | 447 | 21 | 170 | 21 | 0.64 |
| Cp | ng/mL | 2.1E1 | 5.0E1 | 3.0E1 | 4.7E1 | 6.7E1 | 2.7E1 | 6.0E-1 | 4.7E0 | 1.3E3 | 9.6E1 | 447 | 21 | 170 | 21 | 0.75 |
| Cq | ng/mL | 2.8E-2 | 3.4E-2 | 2.5E-1 | 1.1E-1 | 2.5E0 | 2.4E-1 | 8.0E-4 | 8.0E-4 | 4.9E1 | 1.1E0 | 447 | 21 | 170 | 21 | 0.56 |
| Cs | ng/mL | 5.9E1 | 1.0E2 | 3.2E2 | 2.5E2 | 1.2E3 | 3.8E2 | 2.7E-2 | 8.9E-1 | 1.8E4 | 1.6E3 | 447 | 21 | 170 | 21 | 0.54 |
| Ct | ng/mL | 6.1E-1 | 3.8E-1 | 3.2E1 | 5.9E1 | 9.9E1 | 1.3E2 | 1.1E-4 | 3.8E-2 | 6.2E2 | 4.4E2 | 447 | 21 | 170 | 21 | 0.53 |
| Cu | ng/mL | 2.4E-1 | 4.8E-1 | 5.5E-1 | 7.0E-1 | 3.2E0 | 6.9E-1 | 9.6E-3 | 2.7E-2 | 6.6E1 | 2.4E0 | 447 | 21 | 170 | 21 | 0.65 |
| Cv | ng/mL | 5.8E0 | 2.4E0 | 2.8E1 | 3.6E1 | 6.9E1 | 1.0E2 | 1.4E-4 | 1.6E-1 | 5.3E2 | 4.7E2 | 447 | 21 | 170 | 21 | 0.45 |
| Cw | mIU/mL | 3.0E-2 | 4.6E-2 | 5.4E-2 | 5.2E-2 | 3.2E-1 | 3.5E-2 | 1.5E-4 | 5.5E-3 | 6.8E0 | 1.2E-1 | 447 | 21 | 170 | 21 | 0.61 |
| Cx | ng/mL | 4.6E-1 | 3.8E-1 | 6.0E1 | 9.0E1 | 1.1E2 | 1.4E2 | 9.3E-5 | 9.3E-5 | 3.9E2 | 3.9E2 | 447 | 21 | 170 | 21 | 0.48 |
| Db | ug/mL | 7.6E0 | 8.0E0 | 9.6E0 | 9.1E0 | 1.1E1 | 6.3E0 | 4.5E-1 | 1.2E0 | 1.4E2 | 2.9E1 | 447 | 21 | 170 | 21 | 0.53 |
| Dc | nmol/L | 1.9E-2 | 2.5E-2 | 8.6E-2 | 2.3E-1 | 6.7E-1 | 5.7E-1 | 5.2E-6 | 3.6E-4 | 1.4E1 | 2.2E0 | 447 | 21 | 170 | 21 | 0.54 |
| Dd | ug/mL | 7.8E-2 | 9.8E-2 | 1.9E-1 | 1.9E-1 | 3.1E-1 | 2.5E-1 | 1.9E-4 | 1.6E-4 | 3.6E0 | 7.9E-1 | 447 | 21 | 170 | 21 | 0.49 |
| De | ng/mL | 3.4E-3 | 1.7E-1 | 7.6E-2 | 1.6E-1 | 1.5E-1 | 2.4E-1 | 3.4E-3 | 3.4E-3 | 9.2E-1 | 1.1E0 | 447 | 21 | 170 | 21 | 0.65 |
| Dg | ng/mL | 3.4E1 | 3.8E1 | 4.6E1 | 4.2E1 | 4.1E1 | 3.5E1 | 1.0E-1 | 7.8E-1 | 1.9E2 | 1.2E2 | 447 | 21 | 170 | 21 | 0.49 |
| Di | pg/mL | 1.9E0 | 3.7E0 | 2.2E0 | 3.5E0 | 2.1E0 | 2.0E0 | 1.8E-1 | 1.8E-1 | 1.3E1 | 9.3E0 | 447 | 21 | 170 | 21 | 0.70 |
| Dk | uIU/mL | 1.6E-2 | 3.6E-2 | 8.7E-2 | 8.0E-2 | 5.1E-1 | 1.5E-1 | 1.1E-4 | 1.1E-4 | 8.9E0 | 6.3E-1 | 447 | 21 | 170 | 21 | 0.57 |
| Dl | ng/mL | 2.4E2 | 2.2E2 | 3.2E2 | 3.1E2 | 2.9E2 | 2.7E2 | 2.5E0 | 4.7E0 | 1.6E3 | 8.6E2 | 447 | 21 | 170 | 21 | 0.50 |
| Dp | ng/ml | 2.5E0 | 1.8E0 | 6.4E0 | 4.3E0 | 1.5E1 | 6.8E0 | 3.7E-3 | 7.7E-2 | 2.0E2 | 2.6E1 | 160 | 19 | 160 | 19 | 0.41 |
| Dr | pg/ml | 2.9E1 | 1.3E1 | 1.2E2 | 1.7E1 | 8.3E2 | 1.6E1 | 7.5E-1 | 7.5E-1 | 1.0E4 | 3.9E1 | 158 | 8 | 91 | 8 | 0.32 |
| Ef | ng/ml | 1.3E-1 | 2.6E-1 | 8.6E-1 | 2.2E0 | 1.9E0 | 3.2E0 | 5.7E-4 | 5.7E-3 | 1.0E1 | 9.9E0 | 325 | 19 | 167 | 19 | 0.59 |
| Wm | % | 7.2E-1 | 7.0E-1 | 3.2E1 | 3.8E1 | 1.8E2 | 1.3E2 | 5.4E-2 | 8.5E-2 | 2.4E3 | 6.1E2 | 353 | 25 | 182 | 25 | 0.53 |
| Ed | pg/ml | 5.2E-1 | 5.1E0 | 5.9E1 | 3.2E1 | 4.5E2 | 4.4E1 | 5.2E-1 | 5.2E-1 | 7.3E3 | 1.3E2 | 262 | 19 | 159 | 19 | 0.55 |
| Tj | pg/mL | 3.7E-1 | 3.7E-1 | 5.6E1 | 5.5E0 | 3.0E2 | 1.1E1 | 3.6E-1 | 3.7E-1 | 3.5E3 | 4.3E1 | 323 | 19 | 169 | 19 | 0.45 |
| Po | pg/ml | 5.4E-1 | 4.4E0 | 8.9E0 | 1.7E1 | 2.6E1 | 4.1E1 | 8.0E-3 | 2.6E-2 | 2.7E2 | 2.2E2 | 755 | 37 | 295 | 37 | 0.61 |
| Em | ng/ml | 2.9E-3 | 1.3E-2 | 7.8E-2 | 2.4E-2 | 1.9E-1 | 2.9E-2 | 1.9E-16 | 2.9E-3 | 1.9E0 | 9.1E-2 | 204 | 9 | 91 | 9 | 0.50 |
| Et | ng/ml | 1.4E3 | 2.0E3 | 1.7E3 | 2.2E3 | 1.2E3 | 1.4E3 | 7.5E1 | 7.9E1 | 5.0E3 | 5.0E3 | 754 | 37 | 295 | 37 | 0.60 |
| Fa | ng/ml | 4.0E1 | 5.9E1 | 1.3E2 | 1.9E2 | 5.6E2 | 4.8E2 | 3.4E-2 | 4.5E0 | 8.0E3 | 2.1E3 | 261 | 19 | 158 | 19 | 0.58 |
| Ez | ng/ml | 3.8E0 | 5.4E0 | 1.5E1 | 2.7E1 | 3.2E1 | 5.0E1 | 1.3E-2 | 1.3E-2 | 3.0E2 | 2.0E2 | 262 | 19 | 160 | 19 | 0.57 |
| Fb | ng/ml | 2.5E1 | 3.3E1 | 2.2E1 | 2.8E1 | 1.1E1 | 1.3E1 | 5.9E-1 | 8.9E-1 | 5.7E1 | 4.3E1 | 262 | 19 | 158 | 19 | 0.65 |
| Ex | ng/ml | 7.8E-2 | 1.6E-1 | 2.2E-1 | 5.5E-1 | 6.9E-1 | 1.0E0 | 3.5E-5 | 1.7E-4 | 8.9E0 | 4.1E0 | 245 | 16 | 117 | 16 | 0.67 |
| Fn | ng/ml | 2.1E-1 | 1.6E0 | 5.9E0 | 3.0E0 | 2.7E1 | 4.9E0 | 1.1E-14 | 2.1E-1 | 4.2E2 | 2.1E1 | 262 | 19 | 160 | 19 | 0.53 |
| Fp | ng/ml | 1.3E1 | 2.3E1 | 2.5E1 | 3.3E1 | 2.8E1 | 3.4E1 | 6.0E-3 | 4.3E-1 | 1.4E2 | 1.3E2 | 787 | 37 | 296 | 37 | 0.56 |
| Fr | ng/ml | 3.5E4 | 1.1E5 | 1.1E5 | 2.7E5 | 1.7E5 | 3.0E5 | 1.9E2 | 1.3E3 | 9.0E5 | 8.4E5 | 890 | 39 | 300 | 39 | 0.64 |
| Fw | pg/ml | 1.1E0 | 1.1E1 | 6.2E1 | 1.9E1 | 4.8E2 | 2.1E1 | 1.1E-14 | 1.7E-14 | 6.9E3 | 7.1E1 | 325 | 20 | 168 | 20 | 0.62 |
| Fy | ng/ml | 3.8E1 | 3.3E1 | 6.0E1 | 4.8E1 | 7.3E1 | 4.3E1 | 1.2E-1 | 1.2E-1 | 6.5E2 | 1.3E2 | 260 | 17 | 159 | 17 | 0.48 |

Figure 5

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Gc | ng/ml | 1.1E2 | 5.8E1 | 1.7E2 | 1.2E2 | 1.8E2 | 1.6E2 | 6.4E0 | 2.3E1 | 1.2E3 | 5.1E2 | 169 | 8 | 94 | 8 | 0.37 |
| Gd | ng/ml | 3.1E1 | 2.9E1 | 3.3E1 | 2.8E1 | 1.7E1 | 2.0E1 | 5.0E0 | 3.0E0 | 8.1E1 | 5.6E1 | 189 | 9 | 83 | 9 | 0.42 |
| Gn | U/ml | 2.8E-1 | 1.6E-1 | 2.1E0 | 3.6E-1 | 9.6E0 | 4.3E-1 | 1.3E-3 | 1.2E-2 | 1.1E2 | 1.0E0 | 152 | 8 | 89 | 8 | 0.41 |
| Gl | pg/ml | 7.1E3 | 1.3E4 | 1.1E4 | 1.5E4 | 9.1E3 | 1.1E4 | 9.1E1 | 5.3E2 | 3.4E4 | 3.2E4 | 316 | 20 | 166 | 20 | 0.62 |
| Gp | U/ml | 1.5E0 | 8.0E-1 | 4.1E0 | 2.3E0 | 7.0E0 | 3.0E0 | 1.3E-3 | 1.5E-2 | 6.7E1 | 9.2E0 | 327 | 19 | 168 | 19 | 0.41 |
| Gz | ug/ml | 1.4E0 | 1.6E0 | 8.9E0 | 5.0E0 | 3.7E1 | 5.4E0 | 2.9E-16 | 4.2E-2 | 4.8E2 | 1.3E1 | 181 | 16 | 106 | 16 | 0.45 |
| Ha | ng/ml | 2.3E0 | 3.2E0 | 9.5E0 | 1.2E1 | 2.1E1 | 2.5E1 | 6.4E-3 | 1.7E-2 | 1.3E2 | 1.1E2 | 260 | 19 | 159 | 19 | 0.57 |
| Nm | pg/ml | 1.5E4 | 1.4E4 | 3.4E4 | 3.2E4 | 8.7E4 | 4.2E4 | 1.0E-9 | 1.0E-9 | 1.6E6 | 1.5E5 | 758 | 37 | 297 | 37 | 0.50 |
| Nn | pg/ml | 1.5E2 | 7.3E2 | 1.7E3 | 8.4E3 | 7.6E3 | 2.3E4 | 1.0E-9 | 1.0E-9 | 1.0E5 | 1.1E5 | 758 | 37 | 297 | 37 | 0.68 |
| No | pg/ml | 1.5E1 | 1.9E1 | 3.9E1 | 8.6E1 | 1.2E2 | 1.8E2 | 1.0E-9 | 1.0E-9 | 2.5E3 | 7.7E2 | 758 | 37 | 297 | 37 | 0.57 |
| Nq | pg/ml | 1.7E0 | 6.3E0 | 1.7E1 | 4.2E1 | 6.8E1 | 7.6E1 | 1.0E-9 | 1.0E-9 | 1.2E3 | 3.0E2 | 758 | 37 | 297 | 37 | 0.62 |
| Nr | pg/ml | 9.7E-1 | 2.8E0 | 3.1E1 | 4.7E1 | 1.9E2 | 2.2E2 | 1.0E-9 | 1.0E-9 | 4.1E3 | 1.4E3 | 758 | 37 | 297 | 37 | 0.57 |
| Ns | pg/ml | 1.0E-9 | 1.0E-9 | 7.1E0 | 1.9E0 | 3.5E1 | 8.8E0 | 1.0E-9 | 1.0E-9 | 6.8E2 | 5.1E1 | 758 | 37 | 297 | 37 | 0.49 |
| Nt | pg/ml | 1.0E2 | 1.3E2 | 1.3E2 | 1.9E2 | 1.1E2 | 2.1E2 | 1.0E-9 | 1.4E1 | 1.7E3 | 1.2E3 | 758 | 37 | 297 | 37 | 0.59 |
| Nu | pg/ml | 2.0E1 | 3.8E1 | 5.3E1 | 9.5E1 | 8.9E1 | 1.3E2 | 1.0E-9 | 1.0E-9 | 8.9E2 | 6.3E2 | 758 | 37 | 297 | 37 | 0.61 |
| Lu | pg/ml | 1.0E4 | 1.0E4 | 1.8E4 | 1.0E4 | 6.5E4 | 1.2E4 | 3.5E2 | 1.3E3 | 1.3E6 | 7.5E4 | 761 | 37 | 297 | 37 | 0.42 |
| Lv | pg/ml | 1.0E-9 | 7.5E0 | 1.1E1 | 2.9E1 | 2.1E1 | 4.0E1 | 1.0E-9 | 1.0E-9 | 2.4E2 | 1.6E2 | 761 | 37 | 297 | 37 | 0.63 |
| Lw | pg/ml | 1.0E-9 | 1.0E-9 | 4.3E-1 | 2.4E0 | 4.1E0 | 9.1E0 | 1.0E-9 | 1.0E-9 | 8.0E1 | 4.7E1 | 761 | 37 | 297 | 37 | 0.53 |
| Lx | pg/ml | 1.0E-9 | 1.3E2 | 1.8E2 | 3.8E2 | 9.3E2 | 6.8E2 | 1.0E-9 | 1.0E-9 | 2.2E4 | 2.8E3 | 761 | 37 | 297 | 37 | 0.68 |
| Ly | pg/ml | 1.0E-9 | 1.0E-9 | 1.0E1 | 1.2E1 | 2.0E1 | 2.0E1 | 1.0E-9 | 1.0E-9 | 1.2E2 | 7.2E1 | 761 | 37 | 297 | 37 | 0.53 |
| Lz | pg/ml | 1.0E-9 | 1.0E-9 | 4.0E0 | 4.3E0 | 3.2E1 | 1.5E1 | 1.0E-9 | 1.0E-9 | 6.0E2 | 6.2E1 | 761 | 37 | 297 | 37 | 0.53 |
| Ma | pg/ml | 2.9E2 | 4.6E2 | 1.3E3 | 2.7E3 | 3.6E3 | 6.2E3 | 1.0E-9 | 1.0E-9 | 6.5E4 | 3.6E4 | 761 | 37 | 297 | 37 | 0.55 |
| Mb | pg/ml | 2.5E1 | 3.4E1 | 3.1E1 | 3.7E1 | 1.5E1 | 2.1E1 | 4.1E0 | 1.3E1 | 2.1E2 | 1.1E2 | 761 | 37 | 297 | 37 | 0.57 |
| Mc | pg/ml | 1.0E-9 | 1.0E-9 | 4.3E-2 | 3.8E-2 | 6.1E-1 | 2.3E-1 | 1.0E-9 | 1.0E-9 | 1.3E1 | 1.4E0 | 761 | 37 | 297 | 37 | 0.51 |
| Md | pg/ml | 1.0E-9 | 1.0E-9 | 4.5E-1 | 2.6E-1 | 3.9E0 | 1.1E0 | 1.0E-9 | 1.0E-9 | 6.8E1 | 5.9E0 | 761 | 37 | 297 | 37 | 0.52 |
| Me | pg/ml | 3.3E1 | 2.7E1 | 3.2E1 | 3.0E1 | 2.0E1 | 3.0E1 | 1.0E-9 | 2.4E-1 | 3.2E2 | 1.8E2 | 761 | 37 | 297 | 37 | 0.40 |
| Mf | pg/ml | 1.0E-9 | 1.0E-9 | 5.0E-1 | 4.1E-1 | 2.8E0 | 1.4E0 | 1.0E-9 | 1.0E-9 | 5.6E1 | 6.9E0 | 761 | 37 | 297 | 37 | 0.51 |
| Mg | pg/ml | 1.6E0 | 8.7E-1 | 7.0E0 | 1.1E1 | 1.2E1 | 2.6E1 | 1.0E-9 | 1.0E-9 | 9.2E1 | 1.5E2 | 761 | 37 | 297 | 37 | 0.49 |
| Mh | pg/ml | 1.0E-9 | 1.0E-9 | 1.5E0 | 1.3E0 | 1.0E1 | 3.9E0 | 1.0E-9 | 1.0E-9 | 1.6E2 | 1.8E1 | 761 | 37 | 297 | 37 | 0.55 |
| Mi | pg/ml | 1.0E-9 | 1.0E-9 | 9.4E-1 | 5.9E0 | 1.3E1 | 2.0E1 | 1.0E-9 | 1.0E-9 | 3.2E2 | 1.1E2 | 761 | 37 | 297 | 37 | 0.56 |
| Mj | pg/ml | 1.0E-9 | 1.0E-9 | 4.7E0 | 1.3E1 | 2.7E1 | 3.8E1 | 1.0E-9 | 1.0E-9 | 4.6E2 | 2.1E2 | 761 | 37 | 297 | 37 | 0.56 |
| Mk | pg/ml | 2.8E-1 | 4.3E0 | 1.4E1 | 2.3E1 | 9.2E1 | 8.3E1 | 1.0E-9 | 1.0E-9 | 1.7E3 | 5.0E2 | 761 | 37 | 297 | 37 | 0.57 |
| Ml | pg/ml | 1.0E-9 | 1.0E-9 | 6.0E0 | 2.6E0 | 8.1E1 | 8.2E0 | 1.0E-9 | 1.0E-9 | 2.1E3 | 4.3E1 | 761 | 37 | 297 | 37 | 0.50 |
| Mm | pg/ml | 6.1E2 | 8.4E2 | 1.1E3 | 1.4E3 | 1.4E3 | 1.7E3 | 1.0E-9 | 1.0E-9 | 1.2E4 | 6.5E3 | 761 | 37 | 297 | 37 | 0.54 |
| Mn | pg/ml | 5.4E0 | 7.2E0 | 1.0E1 | 1.0E1 | 2.0E1 | 1.1E1 | 1.0E-9 | 1.0E-9 | 3.5E2 | 5.1E1 | 761 | 37 | 297 | 37 | 0.55 |
| Mp | pg/ml | 1.0E-9 | 9.4E0 | 1.0E1 | 2.4E1 | 3.6E1 | 5.0E1 | 1.0E-9 | 1.0E-9 | 6.3E2 | 2.7E2 | 760 | 37 | 297 | 37 | 0.64 |
| Mq | pg/ml | 1.0E-9 | 1.0E-9 | 2.8E0 | 6.2E0 | 1.6E1 | 1.8E1 | 1.0E-9 | 1.0E-9 | 2.1E2 | 8.6E1 | 760 | 37 | 297 | 37 | 0.55 |
| Mr | pg/ml | 1.0E-9 | 1.0E-9 | 3.2E1 | 1.2E2 | 1.8E2 | 5.6E2 | 1.0E-9 | 1.0E-9 | 2.2E3 | 3.4E3 | 760 | 37 | 297 | 37 | 0.58 |
| Ms | pg/ml | 4.1E2 | 4.3E2 | 5.6E2 | 5.5E2 | 6.6E2 | 5.1E2 | 1.0E-9 | 1.0E-9 | 5.9E3 | 2.0E3 | 760 | 37 | 297 | 37 | 0.52 |
| Mt | pg/ml | 2.4E-1 | 1.9E0 | 7.3E0 | 9.8E1 | 4.5E1 | 5.3E2 | 1.0E-9 | 1.0E-9 | 8.7E2 | 3.2E3 | 760 | 37 | 297 | 37 | 0.63 |
| Mu | pg/ml | 1.0E-9 | 1.0E-9 | 9.0E-1 | 4.2E0 | 7.0E0 | 1.0E1 | 1.0E-9 | 1.0E-9 | 9.9E1 | 4.8E1 | 760 | 37 | 297 | 37 | 0.66 |
| Mv | pg/ml | 1.0E-9 | 1.0E-9 | 5.8E1 | 2.0E2 | 3.1E2 | 4.7E2 | 1.0E-9 | 1.0E-9 | 4.5E3 | 2.5E3 | 760 | 37 | 297 | 37 | 0.62 |
| Mw | pg/ml | 3.8E1 | 7.5E1 | 4.0E2 | 7.2E2 | 2.8E3 | 1.5E3 | 1.0E-9 | 1.0E-9 | 6.2E4 | 5.9E3 | 760 | 37 | 297 | 37 | 0.60 |
| Mx | pg/ml | 1.0E-9 | 1.0E-9 | 2.2E-1 | 7.8E-1 | 9.1E-1 | 3.2E0 | 1.0E-9 | 1.0E-9 | 9.6E0 | 2.0E1 | 760 | 37 | 297 | 37 | 0.58 |
| My | pg/ml | 1.0E-9 | 1.8E1 | 3.9E2 | 3.3E2 | 2.7E3 | 8.4E2 | 1.0E-9 | 1.0E-9 | 3.9E4 | 4.6E3 | 760 | 37 | 297 | 37 | 0.60 |
| Mz | pg/ml | 1.1E1 | 2.6E1 | 2.6E1 | 9.5E1 | 7.9E1 | 3.2E2 | 1.0E-9 | 1.0E-9 | 1.3E3 | 1.9E3 | 760 | 37 | 297 | 37 | 0.66 |
| Na | pg/ml | 1.0E-9 | 1.0E-9 | 7.4E-1 | 7.8E-1 | 3.2E0 | 2.9E0 | 1.0E-9 | 1.0E-9 | 4.2E1 | 1.6E1 | 760 | 37 | 297 | 37 | 0.50 |
| Nb | pg/ml | 1.9E0 | 3.2E0 | 4.0E0 | 9.8E0 | 1.3E1 | 3.4E1 | 1.0E-9 | 1.0E-9 | 2.3E2 | 2.1E2 | 760 | 37 | 297 | 37 | 0.62 |
| Nc | pg/ml | 3.4E2 | 1.5E2 | 5.8E2 | 3.5E2 | 7.5E2 | 4.0E2 | 1.0E-9 | 1.0E-9 | 9.2E3 | 1.3E3 | 760 | 37 | 297 | 37 | 0.42 |
| Nd | pg/ml | 2.9E1 | 1.6E1 | 3.0E1 | 2.1E1 | 9.0E1 | 2.1E1 | 1.0E-9 | 1.0E-9 | 2.1E3 | 9.4E1 | 760 | 37 | 297 | 37 | 0.43 |
| Ne | pg/ml | 4.5E2 | 3.2E2 | 5.9E2 | 4.0E2 | 5.9E2 | 3.8E2 | 1.0E-9 | 1.0E-9 | 7.0E3 | 1.8E3 | 760 | 37 | 297 | 37 | 0.40 |
| Nf | pg/ml | 1.0E-9 | 1.0E-9 | 2.9E0 | 4.2E0 | 1.1E1 | 1.8E1 | 1.0E-9 | 1.0E-9 | 1.6E2 | 1.1E2 | 760 | 37 | 297 | 37 | 0.47 |
| Ng | pg/ml | 1.9E1 | 3.2E0 | 1.1E2 | 1.0E2 | 2.2E2 | 2.2E2 | 1.0E-9 | 1.0E-9 | 1.6E3 | 1.2E3 | 760 | 37 | 297 | 37 | 0.44 |
| Nh | pg/ml | 6.9E1 | 5.2E1 | 9.2E1 | 6.3E1 | 8.3E1 | 6.5E1 | 1.0E-9 | 1.0E-9 | 5.6E2 | 3.5E2 | 760 | 37 | 297 | 37 | 0.39 |
| Ni | pg/ml | 1.0E-9 | 3.9E1 | 7.2E1 | 1.2E2 | 1.2E2 | 1.5E2 | 1.0E-9 | 1.0E-9 | 1.1E3 | 4.8E2 | 760 | 37 | 297 | 37 | 0.57 |
| Nj | pg/ml | 7.3E0 | 4.9E0 | 1.1E1 | 8.0E0 | 1.2E1 | 6.9E0 | 1.0E-9 | 1.0E-9 | 8.3E1 | 2.2E1 | 760 | 37 | 297 | 37 | 0.46 |
| Nk | pg/ml | 1.8E1 | 1.6E1 | 3.4E1 | 2.6E1 | 4.0E1 | 2.8E1 | 1.0E-9 | 1.0E-9 | 2.0E2 | 1.1E2 | 760 | 37 | 297 | 37 | 0.47 |

Figure 5 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nl | pg/ml | 4.6E1 | 3.2E1 | 6.2E1 | 3.9E1 | 7.0E1 | 3.5E1 | 1.0E-9 | 1.0E-9 | 1.1E3 | 1.3E2 | 760 | 37 | 297 | 37 | 0.40 |
| Tz | pg/ml | 4.6E3 | 8.9E3 | 1.3E4 | 1.4E4 | 6.3E4 | 1.8E4 | 1.0E-9 | 9.8E1 | 1.0E6 | 6.7E4 | 264 | 19 | 159 | 19 | 0.61 |
| Ua | pg/ml | 3.7E3 | 6.3E3 | 2.0E4 | 3.0E4 | 1.3E5 | 4.3E4 | 1.0E-9 | 2.7E2 | 2.1E6 | 1.3E5 | 264 | 19 | 159 | 19 | 0.60 |
| Ub | pg/ml | 5.7E2 | 2.7E2 | 8.7E2 | 5.0E2 | 1.1E3 | 5.1E2 | 1.0E-9 | 3.4E1 | 9.8E3 | 1.7E3 | 264 | 19 | 159 | 19 | 0.38 |
| Ue | pg/ml | 3.1E1 | 1.6E1 | 4.0E1 | 2.9E1 | 4.0E1 | 2.8E1 | 9.8E-2 | 6.7E0 | 4.4E2 | 1.1E2 | 264 | 19 | 159 | 19 | 0.35 |
| Uc | pg/ml | 9.2E2 | 1.0E3 | 2.0E3 | 1.2E3 | 4.4E3 | 1.2E3 | 1.0E-9 | 1.5E1 | 5.7E4 | 5.4E3 | 264 | 19 | 159 | 19 | 0.47 |
| Ud | pg/ml | 1.0E-9 | 1.0E-9 | 1.8E0 | 1.0E-9 | 2.4E1 | 0.0E0 | 1.0E-9 | 1.0E-9 | 3.9E2 | 1.0E-9 | 264 | 19 | 159 | 19 | 0.49 |
| Hq | pg/ml | 1.0E0 | 2.5E0 | 1.2E2 | 1.6E1 | 1.8E3 | 4.7E1 | 1.0E-9 | 1.0E-9 | 3.4E4 | 2.3E2 | 756 | 37 | 296 | 37 | 0.66 |
| Hr | pg/ml | 1.1E2 | 1.0E2 | 8.0E2 | 4.5E2 | 1.7E3 | 8.4E2 | 1.0E-9 | 1.0E-9 | 1.7E4 | 3.8E3 | 756 | 37 | 296 | 37 | 0.48 |
| Hu | pg/ml | 5.1E0 | 1.3E1 | 2.6E3 | 1.5E3 | 2.6E4 | 3.2E3 | 1.0E-9 | 1.0E-9 | 6.3E5 | 1.1E4 | 756 | 37 | 296 | 37 | 0.55 |
| Hv | pg/ml | 1.3E0 | 2.3E0 | 4.2E0 | 4.4E0 | 3.4E1 | 7.1E0 | 1.0E-9 | 1.0E-9 | 8.9E2 | 3.3E1 | 756 | 37 | 296 | 37 | 0.64 |
| Hw | pg/ml | 6.6E0 | 4.5E0 | 3.1E1 | 2.3E1 | 3.5E2 | 8.2E1 | 1.0E-9 | 1.0E-9 | 9.4E3 | 5.0E2 | 756 | 37 | 296 | 37 | 0.43 |
| Hx | pg/ml | 8.3E0 | 1.5E1 | 4.0E1 | 6.6E1 | 3.5E2 | 2.1E2 | 1.0E-9 | 1.0E-9 | 9.3E3 | 1.3E3 | 756 | 37 | 296 | 37 | 0.60 |
| Ib | ng/ml | 4.9E-2 | 1.4E-2 | 1.2E0 | 3.0E0 | 5.3E0 | 8.5E0 | 1.0E-9 | 1.0E-9 | 5.6E1 | 3.6E1 | 259 | 19 | 159 | 19 | 0.42 |
| Ic | U/ml | 2.2E2 | 2.2E2 | 1.1E3 | 2.0E2 | 7.3E3 | 1.1E2 | 1.5E0 | 2.1E1 | 9.3E4 | 3.9E2 | 259 | 19 | 159 | 19 | 0.49 |
| Id | U/ml | 6.8E-1 | 8.9E-1 | 3.0E0 | 2.1E0 | 2.7E1 | 2.5E0 | 1.0E-9 | 2.7E-1 | 4.3E2 | 9.4E0 | 259 | 19 | 159 | 19 | 0.58 |
| Tt | pg/ml | 1.6E2 | 1.8E2 | 1.7E2 | 1.8E2 | 5.4E1 | 5.1E1 | 4.3E1 | 1.0E2 | 4.4E2 | 2.8E2 | 246 | 17 | 153 | 17 | 0.54 |
| To | pg/ml | 1.6E0 | 1.8E0 | 1.9E0 | 1.9E0 | 2.3E0 | 1.8E0 | 1.0E-9 | 1.0E-9 | 2.3E1 | 6.0E0 | 254 | 19 | 156 | 19 | 0.52 |
| Tr | pg/ml | 3.3E0 | 3.9E0 | 6.6E0 | 5.5E0 | 2.1E1 | 4.2E0 | 1.0E-9 | 1.0E-9 | 3.1E2 | 1.4E1 | 251 | 19 | 155 | 19 | 0.57 |
| Tn | pg/ml | 2.8E1 | 7.2E1 | 8.2E1 | 1.5E2 | 2.5E2 | 2.5E2 | 2.4E0 | 6.6E0 | 2.3E3 | 1.1E3 | 254 | 19 | 156 | 19 | 0.65 |
| Tv | ng/ml | 1.2E1 | 1.2E1 | 5.2E1 | 1.5E1 | 4.5E2 | 1.9E1 | 1.0E-9 | 1.0E-9 | 7.1E3 | 6.5E1 | 254 | 19 | 156 | 19 | 0.44 |
| Ih | ng/ml | 6.8E1 | 8.9E1 | 2.4E2 | 3.1E2 | 4.3E2 | 5.3E2 | 1.0E-9 | 1.0E-9 | 3.6E3 | 2.8E3 | 760 | 37 | 296 | 37 | 0.58 |
| Ii | ng/ml | 9.1E1 | 7.2E1 | 2.4E2 | 3.2E2 | 6.3E2 | 7.8E2 | 1.0E-9 | 4.6E0 | 8.4E3 | 4.5E3 | 760 | 37 | 296 | 37 | 0.51 |
| Ij | ng/ml | 7.6E1 | 8.6E1 | 2.0E2 | 1.3E2 | 1.1E3 | 1.4E2 | 1.0E-9 | 9.4E0 | 2.4E4 | 6.8E2 | 750 | 37 | 294 | 37 | 0.54 |
| Ik | ng/ml | 1.1E1 | 7.3E1 | 9.1E2 | 2.4E2 | 8.9E3 | 4.1E2 | 5.9E-1 | 2.4E0 | 1.2E5 | 1.5E3 | 755 | 37 | 294 | 37 | 0.59 |
| Il | ng/ml | 3.2E2 | 2.3E2 | 1.3E3 | 1.0E3 | 2.8E3 | 2.8E3 | 1.0E-9 | 1.0E-9 | 1.3E4 | 1.2E4 | 744 | 35 | 295 | 35 | 0.44 |
| Im | ng/ml | 2.1E2 | 2.5E2 | 3.7E2 | 6.9E2 | 5.3E2 | 1.2E3 | 1.3E1 | 3.4E1 | 5.8E3 | 6.0E3 | 754 | 37 | 295 | 37 | 0.57 |
| In | ng/ml | 3.6E0 | 1.5E0 | 3.0E1 | 7.3E0 | 2.3E2 | 1.3E1 | 1.0E-9 | 1.0E-9 | 4.5E3 | 5.7E1 | 760 | 37 | 296 | 37 | 0.38 |
| Hb | ng/ml | 2.6E1 | 2.6E1 | 3.7E1 | 3.6E1 | 3.5E1 | 3.2E1 | 6.2E-1 | 4.8E-1 | 2.1E2 | 1.2E2 | 264 | 19 | 159 | 19 | 0.50 |
| Hc | pg/ml | 6.3E2 | 8.9E2 | 3.4E3 | 3.8E3 | 1.3E4 | 6.1E3 | 1.0E-9 | 2.2E2 | 1.0E5 | 2.2E4 | 264 | 19 | 159 | 19 | 0.60 |
| Hf | ng/ml | 1.5E2 | 1.1E2 | 3.5E2 | 2.3E2 | 4.9E2 | 4.0E2 | 1.0E-9 | 1.0E-9 | 2.5E3 | 1.8E3 | 264 | 19 | 159 | 19 | 0.45 |
| Io | ng/ml | 8.2E3 | 5.7E3 | 2.6E4 | 1.2E4 | 1.6E5 | 1.2E4 | 1.0E-9 | 2.4E2 | 4.0E6 | 4.3E4 | 752 | 37 | 296 | 37 | 0.46 |
| Ip | ng/ml | 8.8E0 | 3.0E1 | 1.9E1 | 3.4E1 | 2.4E1 | 4.7E1 | 1.0E-9 | 2.1E-1 | 2.6E2 | 2.4E2 | 752 | 37 | 296 | 37 | 0.62 |
| Iq | ug/ml | 9.6E-2 | 1.1E-1 | 1.9E1 | 6.8E0 | 5.0E2 | 3.6E1 | 1.0E-9 | 1.0E-9 | 1.4E4 | 2.2E2 | 752 | 37 | 296 | 37 | 0.50 |
| Ir | ug/ml | 3.4E-1 | 6.8E-1 | 3.7E0 | 7.9E0 | 2.7E1 | 2.8E1 | 1.0E-9 | 1.0E-9 | 5.1E2 | 1.3E2 | 751 | 37 | 296 | 37 | 0.61 |
| Is | ng/ml | 1.4E0 | 7.9E0 | 6.2E0 | 1.8E1 | 2.4E1 | 4.4E1 | 1.0E-9 | 1.4E-1 | 5.5E2 | 2.6E2 | 752 | 37 | 296 | 37 | 0.72 |
| It | ng/ml | 2.0E0 | 2.3E0 | 2.4E1 | 1.2E1 | 1.4E2 | 3.5E1 | 1.0E-9 | 1.0E-9 | 2.8E3 | 2.1E2 | 752 | 37 | 296 | 37 | 0.55 |
| Iu | ng/ml | 2.2E2 | 2.8E2 | 1.5E3 | 1.3E3 | 4.3E3 | 4.3E3 | 1.0E-9 | 1.0E-9 | 2.9E4 | 2.4E4 | 752 | 37 | 296 | 37 | 0.48 |
| Iv | ng/ml | 1.2E1 | 2.4E1 | 6.5E1 | 1.7E2 | 6.0E2 | 6.3E2 | 1.0E-9 | 1.0E-9 | 1.6E4 | 3.8E3 | 751 | 37 | 296 | 37 | 0.64 |
| Iz | ng/ml | 1.4E2 | 2.6E2 | 6.3E2 | 6.0E2 | 3.9E3 | 6.5E2 | 9.2E-1 | 4.1E0 | 6.2E4 | 2.1E3 | 264 | 19 | 159 | 19 | 0.60 |
| Rc | pg/ml | 6.1E3 | 5.5E3 | 7.3E3 | 9.0E3 | 5.5E3 | 9.5E3 | 1.9E2 | 5.5E2 | 3.0E4 | 3.9E4 | 261 | 19 | 159 | 19 | 0.51 |
| Rb | pg/ml | 8.6E-1 | 4.7E-1 | 2.8E0 | 1.3E0 | 5.5E0 | 2.0E0 | 1.0E-9 | 1.0E-9 | 5.6E1 | 7.8E0 | 261 | 19 | 159 | 19 | 0.46 |
| Pz | ng/ml | 4.4E3 | 3.3E3 | 8.3E3 | 7.0E3 | 4.0E4 | 1.1E4 | 1.3E1 | 6.3E1 | 1.0E6 | 7.0E4 | 753 | 37 | 295 | 37 | 0.50 |
| Qa | ng/ml | 3.4E3 | 8.3E3 | 6.3E3 | 1.1E4 | 1.1E4 | 9.2E3 | 1.2E1 | 4.3E2 | 2.2E5 | 3.2E4 | 753 | 37 | 295 | 37 | 0.65 |
| Qb | ng/ml | 8.7E1 | 2.1E2 | 2.1E2 | 2.5E2 | 5.0E2 | 2.1E2 | 7.9E-1 | 1.3E1 | 8.3E3 | 6.5E2 | 753 | 37 | 295 | 37 | 0.64 |
| Qc | ng/ml | 2.1E2 | 4.4E2 | 4.4E2 | 5.5E2 | 7.6E2 | 5.7E2 | 1.0E-9 | 5.8E0 | 1.1E4 | 2.8E3 | 753 | 37 | 295 | 37 | 0.60 |
| Qd | ng/ml | 8.9E3 | 1.4E4 | 1.9E4 | 4.9E4 | 7.8E4 | 6.5E4 | 1.5E2 | 1.2E3 | 2.0E6 | 2.3E5 | 753 | 37 | 295 | 37 | 0.64 |
| Qe | ng/ml | 9.1E2 | 1.7E3 | 1.8E3 | 2.8E3 | 4.0E3 | 3.7E3 | 1.0E-9 | 8.7E1 | 9.7E4 | 1.8E4 | 753 | 37 | 295 | 37 | 0.60 |
| Jd | ng/ml | 9.0E-1 | 4.6E0 | 6.6E0 | 4.8E0 | 4.3E1 | 4.7E0 | 1.0E-9 | 1.0E-9 | 6.5E2 | 1.8E1 | 262 | 19 | 160 | 19 | 0.69 |
| Je | ng/ml | 1.0E-9 | 1.0E-9 | 2.1E0 | 1.7E0 | 7.8E0 | 2.5E0 | 1.0E-9 | 1.0E-9 | 8.8E1 | 8.2E0 | 262 | 19 | 160 | 19 | 0.53 |
| Jf | ng/ml | 1.0E-9 | 1.0E-9 | 1.0E0 | 8.4E-1 | 2.2E0 | 1.4E0 | 1.0E-9 | 1.0E-9 | 1.2E1 | 4.1E0 | 262 | 19 | 160 | 19 | 0.52 |
| Jg | ng/ml | 5.0E2 | 8.9E2 | 7.7E2 | 1.3E3 | 9.2E2 | 1.6E3 | 1.0E-9 | 2.0E1 | 1.0E4 | 7.1E3 | 756 | 37 | 296 | 37 | 0.59 |
| Jh | ng/ml | 2.8E0 | 5.9E0 | 2.4E1 | 5.4E1 | 1.1E2 | 9.8E1 | 1.0E-9 | 1.0E-9 | 1.6E3 | 4.7E2 | 756 | 37 | 296 | 37 | 0.65 |
| Ji | ng/ml | 5.2E1 | 1.1E2 | 7.7E1 | 1.7E2 | 8.9E1 | 1.6E2 | 1.0E-9 | 8.5E0 | 1.3E3 | 6.7E2 | 756 | 37 | 296 | 37 | 0.71 |
| Sr | pg/mL | 3.9E2 | 5.7E2 | 9.8E2 | 1.3E3 | 1.8E3 | 1.7E3 | 1.0E-9 | 1.0E-9 | 2.1E4 | 5.4E3 | 259 | 19 | 159 | 19 | 0.56 |
| Ss | pg/mL | 9.4E4 | 2.0E5 | 1.5E5 | 1.2E5 | 1.9E5 | 9.0E4 | 2.7E3 | 7.1E3 | 1.8E6 | 2.4E5 | 259 | 19 | 159 | 19 | 0.49 |
| St | pg/mL | 2.6E7 | 5.3E7 | 4.8E7 | 2.3E8 | 6.1E7 | 4.5E8 | 1.0E-9 | 9.9E5 | 5.4E8 | 1.7E9 | 257 | 19 | 157 | 19 | 0.59 |

Figure 5 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ra | pg/ml | 1.0E-9 | 1.0E-9 | 8.4E-1 | 6.7E-1 | 4.1E0 | 1.1E0 | 1.0E-9 | 1.0E-9 | 6.4E1 | 3.4E0 | 261 | 19 | 159 | 19 | 0.55 |
| Qz | pg/ml | 1.0E1 | 9.8E0 | 6.0E1 | 4.8E1 | 9.9E1 | 7.0E1 | 1.0E-9 | 1.0E-9 | 7.1E2 | 2.6E2 | 261 | 19 | 159 | 19 | 0.47 |
| Qy | pg/ml | 4.4E-1 | 1.2E0 | 9.8E0 | 4.5E1 | 5.8E1 | 1.7E2 | 1.0E-9 | 1.0E-9 | 6.5E2 | 7.3E2 | 261 | 19 | 159 | 19 | 0.66 |
| Qx | pg/ml | 1.0E-9 | 1.0E-9 | 6.6E0 | 2.4E0 | 5.1E1 | 5.4E0 | 1.0E-9 | 1.0E-9 | 5.8E2 | 2.1E1 | 261 | 19 | 159 | 19 | 0.54 |
| Qw | pg/ml | 1.0E-9 | 1.0E-9 | 1.9E0 | 3.6E0 | 9.3E0 | 1.2E1 | 1.0E-9 | 1.0E-9 | 1.2E2 | 5.1E1 | 261 | 19 | 159 | 19 | 0.41 |
| Qv | pg/ml | 2.3E4 | 1.5E4 | 3.6E4 | 2.0E4 | 7.8E4 | 2.1E4 | 6.0E1 | 1.0E-9 | 9.4E5 | 9.1E4 | 261 | 19 | 159 | 19 | 0.38 |
| Qu | pg/ml | 7.8E0 | 2.0E1 | 8.6E1 | 1.1E2 | 1.8E2 | 1.9E2 | 1.0E-9 | 1.0E-9 | 9.8E2 | 7.3E2 | 261 | 19 | 159 | 19 | 0.53 |
| Qt | pg/ml | 1.0E1 | 1.5E1 | 5.0E1 | 4.8E1 | 1.3E2 | 8.7E1 | 1.0E-9 | 1.0E-9 | 1.0E3 | 3.3E2 | 261 | 19 | 159 | 19 | 0.53 |
| Qh | ng/ml | 1.6E1 | 2.7E1 | 3.8E1 | 5.3E1 | 6.6E1 | 7.8E1 | 1.0E-9 | 2.5E0 | 6.4E2 | 3.3E2 | 261 | 19 | 159 | 19 | 0.59 |
| Qg | ng/ml | 7.8E0 | 6.6E0 | 1.6E1 | 1.5E1 | 2.6E1 | 2.1E1 | 5.1E-2 | 1.4E0 | 2.2E2 | 7.5E1 | 261 | 19 | 159 | 19 | 0.48 |
| Jj | ng/ml | 6.3E2 | 1.9E2 | 1.8E3 | 3.5E2 | 1.3E4 | 3.4E2 | 1.5E0 | 2.5E1 | 3.4E5 | 1.5E3 | 756 | 37 | 296 | 37 | 0.27 |
| Jk | ng/ml | 3.0E0 | 4.1E0 | 1.9E1 | 3.5E1 | 4.1E1 | 6.3E1 | 1.0E-9 | 4.3E-2 | 2.8E2 | 2.4E2 | 756 | 37 | 296 | 37 | 0.57 |
| Jl | ng/ml | 3.8E-1 | 1.1E0 | 1.8E0 | 2.7E2 | 4.6E0 | 1.6E3 | 7.6E-4 | 5.4E-3 | 4.0E1 | 9.9E3 | 756 | 37 | 296 | 37 | 0.62 |
| Jm | ng/ml | 1.6E1 | 2.3E1 | 5.9E1 | 3.5E1 | 1.4E2 | 3.9E1 | 1.0E-9 | 2.3E-1 | 2.1E3 | 1.5E2 | 756 | 37 | 296 | 37 | 0.52 |
| Jn | pg/ml | 4.0E-1 | 9.0E-1 | 3.2E0 | 2.1E1 | 3.2E1 | 1.2E2 | 1.0E-9 | 1.0E-9 | 6.2E2 | 7.3E2 | 755 | 37 | 296 | 37 | 0.59 |
| Jo | pg/ml | 3.6E3 | 3.4E3 | 5.0E3 | 5.3E3 | 5.3E3 | 6.4E3 | 2.0E1 | 2.7E2 | 1.0E5 | 3.6E4 | 756 | 37 | 296 | 37 | 0.49 |
| Jp | pg/ml | 6.9E4 | 9.4E4 | 7.2E4 | 9.4E4 | 3.8E4 | 4.8E4 | 5.8E2 | 4.6E3 | 3.8E5 | 2.1E5 | 756 | 37 | 296 | 37 | 0.67 |
| Jq | pg/ml | 9.4E1 | 1.7E2 | 1.6E2 | 3.5E2 | 3.5E2 | 6.5E2 | 1.0E0 | 7.4E0 | 8.7E3 | 3.3E3 | 756 | 37 | 296 | 37 | 0.64 |
| Jr | pg/ml | 5.2E0 | 7.0E0 | 4.0E1 | 2.2E2 | 4.4E2 | 1.2E3 | 1.0E-9 | 1.0E-9 | 1.1E4 | 7.4E3 | 756 | 37 | 296 | 37 | 0.57 |
| Js | pg/ml | 1.3E1 | 1.6E1 | 5.5E1 | 1.0E2 | 4.0E2 | 4.7E2 | 1.0E-9 | 2.2E0 | 1.0E4 | 2.9E3 | 756 | 37 | 296 | 37 | 0.60 |
| Jt | pg/ml | 2.7E3 | 3.1E3 | 3.3E3 | 4.0E3 | 2.8E3 | 4.5E3 | 2.2E1 | 1.9E2 | 5.2E4 | 2.5E4 | 756 | 37 | 296 | 37 | 0.53 |
| Ju | mIU/ml | 9.1E0 | 6.4E0 | 2.0E1 | 1.1E1 | 3.1E1 | 1.4E1 | 4.8E-2 | 3.9E-1 | 2.3E2 | 6.2E1 | 262 | 19 | 160 | 19 | 0.44 |
| Jv | mIU/ml | 1.3E1 | 1.5E1 | 3.3E1 | 3.1E1 | 5.7E1 | 4.4E1 | 1.0E-2 | 2.4E-2 | 4.4E2 | 1.4E2 | 262 | 19 | 160 | 19 | 0.50 |
| Jy | ng/ml | 1.6E-3 | 1.4E-3 | 2.3E-3 | 4.5E-3 | 4.2E-3 | 9.1E-3 | 1.0E-9 | 4.5E-4 | 5.2E-2 | 4.1E-2 | 262 | 19 | 160 | 19 | 0.55 |
| Kc | pg/ml | 2.6E1 | 5.7E1 | 4.5E1 | 9.4E1 | 4.8E1 | 8.3E1 | 1.0E-9 | 1.1E1 | 2.7E2 | 3.2E2 | 264 | 19 | 159 | 19 | 0.72 |
| Kd | pg/ml | 1.0E-9 | 1.0E-9 | 3.3E2 | 7.1E2 | 2.4E3 | 1.4E3 | 1.0E-9 | 1.0E-9 | 3.8E4 | 5.2E3 | 264 | 19 | 159 | 19 | 0.63 |
| Ke | pg/ml | 1.3E4 | 1.9E4 | 1.6E4 | 2.4E4 | 2.2E4 | 2.5E4 | 3.4E2 | 6.7E2 | 3.2E5 | 1.1E5 | 264 | 19 | 159 | 19 | 0.62 |
| Kf | pg/mL | 7.4E0 | 9.6E0 | 7.8E0 | 9.2E0 | 7.4E0 | 7.5E0 | 1.0E-9 | 1.0E-9 | 7.8E1 | 2.2E1 | 264 | 19 | 159 | 19 | 0.57 |
| Kg | pg/mL | 1.2E3 | 1.5E3 | 2.0E3 | 3.7E3 | 2.9E3 | 8.4E3 | 7.7E1 | 1.7E2 | 2.7E4 | 3.6E4 | 264 | 19 | 159 | 19 | 0.49 |
| Ki | pg/ml | 5.9E1 | 6.1E1 | 6.8E1 | 7.4E1 | 5.2E1 | 4.5E1 | 1.0E-9 | 6.0E0 | 3.8E2 | 2.1E2 | 263 | 19 | 159 | 19 | 0.56 |
| Kj | pg/ml | 9.8E2 | 9.3E2 | 1.7E3 | 1.6E3 | 1.9E3 | 1.9E3 | 3.0E1 | 1.5E2 | 1.5E4 | 7.7E3 | 264 | 19 | 159 | 19 | 0.48 |
| Kk | pg/ml | 6.8E0 | 1.1E1 | 1.2E1 | 2.0E1 | 1.6E1 | 1.9E1 | 1.0E-9 | 1.0E-9 | 1.6E2 | 5.8E1 | 264 | 19 | 159 | 19 | 0.64 |
| Kl | pg/ml | 2.1E4 | 3.0E4 | 2.8E4 | 2.9E4 | 2.6E4 | 2.3E4 | 2.3E2 | 2.4E2 | 1.6E5 | 6.8E4 | 264 | 19 | 159 | 19 | 0.52 |
| Kn | pg/ml | 3.0E1 | 3.0E1 | 8.1E1 | 1.1E2 | 3.1E2 | 1.8E2 | 1.0E-9 | 1.0E-9 | 4.9E3 | 6.3E2 | 264 | 19 | 159 | 19 | 0.54 |
| Ko | pg/ml | 4.1E2 | 5.0E2 | 5.2E2 | 5.2E2 | 5.2E2 | 3.7E2 | 1.0E-9 | 1.0E-9 | 4.1E3 | 1.2E3 | 264 | 19 | 159 | 19 | 0.53 |
| Kp | pg/ml | 3.4E2 | 3.7E2 | 4.1E2 | 4.8E2 | 8.4E2 | 3.1E2 | 1.0E-9 | 1.0E-9 | 1.3E4 | 1.1E3 | 264 | 19 | 159 | 19 | 0.61 |
| Kq | pg/ml | 3.2E2 | 5.2E2 | 1.1E3 | 1.5E3 | 9.9E3 | 2.8E3 | 5.1E0 | 1.6E0 | 1.6E5 | 1.2E4 | 257 | 19 | 154 | 19 | 0.67 |
| Kr | pg/ml | 5.6E-1 | 2.9E-1 | 4.0E0 | 1.7E0 | 2.6E1 | 2.6E0 | 1.0E-9 | 1.0E-9 | 4.2E2 | 8.2E0 | 257 | 19 | 154 | 19 | 0.49 |
| Ks | pg/ml | 1.4E4 | 7.4E3 | 2.0E4 | 1.3E4 | 1.9E4 | 1.3E4 | 2.2E2 | 5.1E1 | 1.1E5 | 5.0E4 | 257 | 19 | 154 | 19 | 0.38 |
| Kx | ng/ml | 1.0E-9 | 4.6E-3 | 6.9E-3 | 1.0E-2 | 1.4E-2 | 1.8E-2 | 1.0E-9 | 1.0E-9 | 1.0E-1 | 7.9E-2 | 263 | 19 | 159 | 19 | 0.60 |
| Ky | ng/ml | 9.8E-2 | 2.1E-1 | 3.8E-1 | 6.4E-1 | 8.4E-1 | 1.1E0 | 1.0E-9 | 1.0E-9 | 6.4E0 | 4.4E0 | 263 | 19 | 159 | 19 | 0.62 |
| Kz | ng/ml | 1.0E-9 | 1.0E-9 | 3.7E-3 | 3.0E-3 | 5.8E-3 | 6.5E-3 | 1.0E-9 | 1.0E-9 | 3.6E-2 | 2.5E-2 | 263 | 19 | 159 | 19 | 0.45 |
| Ld | pg/ml | 1.0E-9 | 7.5E-1 | 3.7E0 | 4.2E0 | 9.2E0 | 7.6E0 | 1.0E-9 | 1.0E-9 | 8.4E1 | 2.9E1 | 264 | 18 | 158 | 18 | 0.59 |
| Lh | pg/ml | 1.3E4 | 2.6E4 | 2.1E4 | 4.2E4 | 3.3E4 | 6.9E4 | 1.0E-9 | 1.0E-9 | 4.8E5 | 4.1E5 | 756 | 37 | 297 | 37 | 0.64 |
| Li | pg/ml | 3.2E3 | 1.1E4 | 1.7E4 | 4.4E4 | 6.6E4 | 9.0E4 | 1.0E-9 | 1.3E1 | 1.3E6 | 4.1E5 | 756 | 37 | 297 | 37 | 0.61 |
| Lj | pg/ml | 2.9E3 | 4.3E3 | 2.4E4 | 3.0E4 | 6.8E4 | 6.9E4 | 1.0E-9 | 4.5E1 | 5.2E5 | 3.9E5 | 756 | 37 | 297 | 37 | 0.53 |
| Rm | ng/ml | 1.9E1 | 4.0E1 | 5.2E1 | 5.5E1 | 8.4E1 | 4.8E1 | 2.2E-1 | 1.9E0 | 6.5E2 | 1.6E2 | 256 | 19 | 158 | 19 | 0.61 |
| Rh | ng/ml | 1.3E2 | 9.2E1 | 4.0E2 | 1.7E2 | 1.4E3 | 1.4E2 | 4.7E0 | 7.6E0 | 1.7E4 | 4.0E2 | 256 | 19 | 158 | 19 | 0.44 |
| Ri | ng/ml | 1.0E-9 | 1.0E-9 | 4.4E0 | 3.8E0 | 1.6E1 | 1.1E1 | 1.0E-9 | 1.0E-9 | 2.2E2 | 4.5E1 | 257 | 19 | 159 | 19 | 0.44 |
| Rg | ng/ml | 1.0E-9 | 1.0E-9 | 5.0E-2 | 5.4E-3 | 3.0E-1 | 1.1E-2 | 1.0E-9 | 1.0E-9 | 3.0E0 | 3.7E-2 | 256 | 19 | 158 | 19 | 0.60 |
| Rj | ng/ml | 1.0E-9 | 1.0E-9 | 2.4E0 | 3.7E-1 | 1.8E1 | 8.6E-1 | 1.0E-9 | 1.0E-9 | 2.7E2 | 3.2E0 | 257 | 19 | 159 | 19 | 0.45 |
| Rf | ng/ml | 4.1E-1 | 3.7E-1 | 1.0E0 | 2.0E0 | 1.8E0 | 3.7E0 | 7.8E-3 | 1.8E-2 | 1.5E1 | 1.4E1 | 256 | 19 | 158 | 19 | 0.53 |
| Ql | pg/ml | 4.5E0 | 5.5E0 | 1.3E1 | 1.3E1 | 2.4E1 | 1.7E1 | 1.0E-9 | 1.0E-9 | 1.8E2 | 5.6E1 | 262 | 19 | 160 | 19 | 0.55 |
| Qm | pg/ml | 4.1E0 | 1.8E1 | 2.2E1 | 2.3E1 | 4.0E1 | 2.6E1 | 1.0E-9 | 1.0E-9 | 3.6E2 | 8.5E1 | 262 | 19 | 160 | 19 | 0.54 |
| Qn | pg/ml | 6.1E-1 | 6.0E-1 | 7.4E0 | 1.6E1 | 2.4E1 | 4.5E1 | 1.0E-9 | 1.0E-9 | 2.4E2 | 2.0E2 | 262 | 19 | 160 | 19 | 0.49 |
| Nv | pg/ml | 3.8E3 | 9.4E3 | 1.0E4 | 2.0E4 | 4.5E4 | 2.9E4 | 1.0E-9 | 1.9E1 | 1.1E6 | 1.1E5 | 762 | 37 | 297 | 37 | 0.66 |
| Nw | pg/ml | 8.8E3 | 1.8E4 | 1.3E4 | 3.2E4 | 1.7E4 | 4.8E4 | 8.6E1 | 1.9E2 | 2.1E5 | 2.2E5 | 762 | 37 | 297 | 37 | 0.70 |

Figure 5 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nx | pg/ml | 2.2E2 | 2.4E2 | 4.1E2 | 5.9E2 | 6.6E2 | 6.4E2 | 1.0E-9 | 1.0E-9 | 7.4E3 | 2.3E3 | 762 | 37 | 297 | 37 | 0.61 |
| Ny | pg/ml | 6.0E0 | 1.0E1 | 6.1E1 | 7.5E1 | 9.2E2 | 1.5E2 | 1.0E-9 | 1.0E-9 | 2.5E4 | 6.1E2 | 762 | 37 | 297 | 37 | 0.57 |
| Oa | pg/ml | 1.8E2 | 2.9E2 | 4.4E2 | 5.8E2 | 7.4E2 | 6.8E2 | 1.0E-9 | 1.0E-9 | 4.8E3 | 2.0E3 | 262 | 19 | 160 | 19 | 0.58 |
| Tk | ng/ml | 1.4E2 | 9.5E1 | 3.2E2 | 3.2E2 | 5.5E2 | 5.2E2 | 3.0E0 | 1.9E1 | 4.2E3 | 1.4E3 | 93 | 7 | 66 | 7 | 0.44 |
| Oe | pg/ml | 4.2E1 | 9.4E0 | 2.7E2 | 2.1E2 | 7.9E2 | 3.3E2 | 1.0E-9 | 1.0E-9 | 1.9E4 | 1.3E3 | 755 | 37 | 296 | 37 | 0.47 |
| Of | pg/ml | 1.6E2 | 9.7E1 | 5.3E3 | 3.6E3 | 2.9E4 | 9.7E3 | 1.0E-9 | 1.0E-9 | 6.2E5 | 4.7E4 | 761 | 37 | 297 | 37 | 0.46 |
| Og | pg/ml | 7.9E-2 | 6.4E-2 | 4.6E-1 | 1.2E-1 | 1.5E0 | 1.5E-1 | 1.0E-9 | 1.0E-9 | 2.0E1 | 5.0E-1 | 761 | 37 | 297 | 37 | 0.44 |
| Oh | pg/ml | 2.5E0 | 5.7E0 | 2.0E1 | 4.3E1 | 1.5E2 | 1.9E2 | 1.0E-9 | 1.0E-9 | 3.5E3 | 1.1E3 | 761 | 37 | 297 | 37 | 0.69 |
| Oi | pg/ml | 2.4E0 | 5.0E0 | 5.9E0 | 8.9E0 | 9.6E0 | 1.0E1 | 1.0E-9 | 1.0E-9 | 8.6E1 | 3.6E1 | 761 | 37 | 297 | 37 | 0.57 |
| Ok | pg/ml | 3.9E2 | 6.4E2 | 5.3E2 | 9.6E2 | 5.7E2 | 1.1E3 | 1.3E1 | 1.5E1 | 7.8E3 | 4.7E3 | 761 | 37 | 297 | 37 | 0.64 |
| Om | pg/ml | 3.8E2 | 9.9E2 | 8.2E2 | 1.7E3 | 2.6E3 | 1.9E3 | 1.0E-9 | 1.0E-9 | 5.1E4 | 6.9E3 | 761 | 37 | 297 | 37 | 0.69 |
| On | pg/ml | 1.8E2 | 3.1E2 | 2.8E2 | 7.1E2 | 4.2E2 | 1.4E3 | 1.0E-9 | 7.6E0 | 4.5E3 | 8.5E3 | 761 | 37 | 297 | 37 | 0.64 |
| Or | pg/ml | 1.4E1 | 1.5E1 | 3.5E1 | 4.7E1 | 6.7E1 | 7.6E1 | 1.0E-9 | 1.0E-9 | 5.1E2 | 2.9E2 | 265 | 19 | 159 | 19 | 0.53 |
| Ow | pg/ml | 3.3E1 | 5.6E1 | 1.5E2 | 1.9E2 | 5.7E2 | 3.6E2 | 1.0E-9 | 1.0E-9 | 8.1E3 | 1.5E3 | 265 | 19 | 159 | 19 | 0.53 |
| Ou | pg/ml | 5.1E2 | 6.4E2 | 9.5E2 | 1.8E3 | 1.5E3 | 2.3E3 | 1.0E-9 | 1.0E-9 | 9.8E3 | 9.3E3 | 265 | 19 | 159 | 19 | 0.58 |
| Ul | ng/ml | 1.0E-9 | 1.0E-9 | 1.8E0 | 9.7E-1 | 8.3E0 | 2.5E0 | 1.0E-9 | 1.0E-9 | 1.0E2 | 9.6E0 | 270 | 19 | 163 | 19 | 0.52 |
| Uo | ng/ml | 1.0E-9 | 1.0E-9 | 9.7E-2 | 6.0E-2 | 2.2E-1 | 1.8E-1 | 1.0E-9 | 1.0E-9 | 1.5E0 | 6.5E-1 | 270 | 19 | 163 | 19 | 0.41 |
| Uk | ng/ml | 1.0E-9 | 1.0E-9 | 8.5E-3 | 6.6E-4 | 2.7E-2 | 2.4E-3 | 1.0E-9 | 1.0E-9 | 3.2E-1 | 1.1E-2 | 270 | 19 | 163 | 19 | 0.34 |
| Um | ng/ml | 1.0E-9 | 1.0E-9 | 4.2E-1 | 2.8E-1 | 9.1E-1 | 6.9E-1 | 1.0E-9 | 1.0E-9 | 6.8E0 | 2.6E0 | 270 | 19 | 163 | 19 | 0.42 |
| Uf | ng/ml | 6.5E-2 | 1.6E-1 | 1.8E-1 | 5.5E-1 | 6.4E-1 | 1.2E0 | 1.3E-3 | 1.0E-3 | 8.6E0 | 5.1E0 | 270 | 19 | 163 | 19 | 0.63 |
| Uh | ng/ml | 2.1E0 | 2.8E0 | 3.4E0 | 3.5E0 | 3.7E0 | 3.8E0 | 1.3E-2 | 4.7E-2 | 2.1E1 | 1.5E1 | 270 | 19 | 163 | 19 | 0.52 |
| Un | ng/ml | 1.9E0 | 2.6E0 | 2.2E0 | 3.3E0 | 1.9E0 | 2.2E0 | 1.3E-1 | 3.4E-1 | 2.5E1 | 8.0E0 | 270 | 19 | 163 | 19 | 0.66 |
| Ug | ng/ml | 1.5E1 | 9.2E0 | 2.9E1 | 1.2E1 | 3.2E1 | 1.1E1 | 6.9E-1 | 8.8E-1 | 2.1E2 | 4.0E1 | 270 | 19 | 163 | 19 | 0.31 |
| Ur | ng/ml | 1.5E-1 | 7.8E-2 | 8.9E-1 | 2.3E-1 | 5.8E0 | 5.2E-1 | 1.0E-9 | 1.0E-9 | 9.3E1 | 2.3E0 | 269 | 19 | 162 | 19 | 0.40 |
| Up | ng/ml | 1.0E-9 | 1.0E-9 | 1.4E-2 | 3.9E-3 | 1.5E-1 | 9.6E-3 | 1.0E-9 | 1.0E-9 | 2.4E0 | 4.1E-2 | 269 | 19 | 162 | 19 | 0.53 |
| Us | ng/ml | 2.9E-3 | 2.8E-4 | 2.6E-2 | 5.0E-3 | 1.1E-1 | 7.4E-3 | 1.0E-9 | 1.0E-9 | 1.7E0 | 2.0E-2 | 269 | 19 | 162 | 19 | 0.41 |
| Uv | ng/ml | 3.1E-3 | 3.9E-3 | 1.4E-2 | 5.7E-3 | 4.7E-2 | 6.1E-3 | 1.0E-9 | 1.0E-9 | 4.3E-1 | 1.9E-2 | 269 | 19 | 162 | 19 | 0.51 |
| Ut | ng/ml | 6.6E-1 | 1.9E0 | 2.9E0 | 5.0E0 | 9.6E0 | 7.5E0 | 1.0E-9 | 1.0E-9 | 7.8E1 | 3.0E1 | 269 | 19 | 162 | 19 | 0.67 |
| Uu | ng/ml | 7.1E0 | 8.2E0 | 7.9E0 | 8.3E0 | 5.6E0 | 5.8E0 | 5.5E-1 | 1.0E0 | 4.0E1 | 2.3E1 | 269 | 19 | 162 | 19 | 0.53 |
| Vp | ng/ml | 1.0E-9 | 1.0E-9 | 5.6E-1 | 7.9E-2 | 4.6E0 | 2.1E-1 | 1.0E-9 | 1.0E-9 | 5.0E1 | 8.4E-1 | 270 | 19 | 163 | 19 | 0.54 |
| Vt | ng/ml | 6.8E0 | 6.1E0 | 9.9E0 | 1.3E1 | 1.3E1 | 1.8E1 | 4.3E-1 | 5.6E-1 | 1.6E2 | 7.6E1 | 270 | 19 | 163 | 19 | 0.51 |
| Vu | ng/ml | 1.0E-9 | 1.0E0 | 2.1E0 | 2.9E0 | 5.4E0 | 4.1E0 | 1.0E-9 | 1.0E-9 | 5.1E1 | 1.3E1 | 264 | 18 | 162 | 18 | 0.60 |
| Vq | ng/ml | 2.7E2 | 1.3E2 | 4.3E3 | 6.7E2 | 4.8E4 | 1.3E3 | 2.0E-1 | 1.8E1 | 6.8E5 | 4.5E3 | 201 | 12 | 131 | 12 | 0.49 |
| Vo | ng/ml | 2.6E1 | 2.5E1 | 2.5E1 | 2.3E1 | 4.7E0 | 6.8E0 | 6.7E0 | 4.7E0 | 3.5E1 | 3.4E1 | 270 | 19 | 163 | 19 | 0.45 |
| Vs | ng/ml | 1.0E-9 | 3.3E0 | 8.3E0 | 8.2E0 | 3.7E1 | 1.1E1 | 1.0E-9 | 1.0E-9 | 4.5E2 | 3.7E1 | 260 | 18 | 159 | 18 | 0.60 |
| Vv | ng/ml | 2.9E0 | 3.0E0 | 5.8E0 | 7.4E0 | 9.7E0 | 9.4E0 | 1.0E-9 | 1.0E-9 | 8.4E1 | 3.5E1 | 268 | 19 | 162 | 19 | 0.55 |
| Oy | pg/ml | 4.9E-1 | 7.1E-1 | 5.9E0 | 4.9E0 | 3.1E1 | 1.2E1 | 1.0E-9 | 1.0E-9 | 4.0E2 | 5.3E1 | 760 | 37 | 296 | 37 | 0.58 |
| Oz | pg/ml | 1.4E-3 | 2.4E-1 | 3.2E-1 | 1.1E0 | 1.4E0 | 4.6E0 | 1.0E-9 | 1.0E-9 | 2.9E1 | 2.8E1 | 760 | 37 | 296 | 37 | 0.64 |
| Pa | pg/ml | 3.8E-1 | 5.1E-1 | 1.7E0 | 7.6E0 | 6.5E0 | 3.7E1 | 1.0E-9 | 1.0E-9 | 1.0E2 | 2.3E2 | 760 | 37 | 296 | 37 | 0.58 |
| Pb | pg/ml | 1.0E-9 | 5.6E-2 | 9.0E-1 | 1.8E-1 | 1.8E1 | 3.4E-1 | 1.0E-9 | 1.0E-9 | 4.9E2 | 1.9E0 | 760 | 37 | 296 | 37 | 0.58 |
| Pc | pg/ml | 4.2E-2 | 3.8E-1 | 3.6E-1 | 1.6E0 | 9.3E-1 | 6.1E0 | 1.0E-9 | 1.0E-9 | 1.6E1 | 3.8E1 | 760 | 37 | 296 | 37 | 0.63 |
| Pd | pg/ml | 1.9E0 | 2.3E0 | 5.4E0 | 6.6E0 | 3.2E1 | 1.1E1 | 1.0E-9 | 1.0E-9 | 8.4E2 | 5.5E1 | 760 | 37 | 296 | 37 | 0.57 |
| Pe | pg/ml | 2.1E1 | 3.8E1 | 1.2E2 | 5.5E2 | 4.8E2 | 2.5E3 | 1.0E-9 | 1.0E-9 | 6.7E3 | 1.5E4 | 760 | 37 | 296 | 37 | 0.57 |
| Pf | pg/ml | 1.6E0 | 6.2E0 | 1.2E1 | 2.3E1 | 6.3E1 | 7.3E1 | 1.0E-9 | 1.0E-9 | 1.5E3 | 4.3E2 | 760 | 37 | 296 | 37 | 0.60 |
| Pg | pg/ml | 3.3E0 | 8.8E0 | 4.8E1 | 7.5E1 | 3.7E2 | 2.3E2 | 1.0E-9 | 1.0E-9 | 7.7E3 | 1.2E3 | 760 | 37 | 296 | 37 | 0.63 |
| Ph | ng/ml | 1.8E-1 | 2.8E-1 | 3.5E-1 | 5.7E-1 | 5.7E-1 | 7.2E-1 | 1.0E-9 | 1.0E-9 | 5.4E0 | 2.8E0 | 265 | 19 | 159 | 19 | 0.57 |
| Pi | ng/ml | 2.0E-1 | 2.4E-1 | 5.8E-1 | 3.3E-1 | 5.0E0 | 3.2E-1 | 1.0E-9 | 1.0E-9 | 8.2E1 | 1.2E0 | 265 | 19 | 159 | 19 | 0.54 |
| Pj | ng/mL | 5.7E0 | 4.8E0 | 6.4E0 | 8.7E0 | 4.5E0 | 1.2E1 | 3.8E-2 | 4.0E-1 | 3.1E1 | 5.5E1 | 265 | 19 | 159 | 19 | 0.47 |
| Pk | ng/ml | 8.8E-3 | 1.3E-2 | 1.8E-2 | 2.1E-2 | 9.4E-2 | 2.6E-2 | 1.0E-9 | 1.0E-9 | 1.5E0 | 1.1E-1 | 265 | 19 | 159 | 19 | 0.59 |
| aA | mg/dL | 8.0E-1 | 1.1E0 | 9.0E-1 | 1.5E0 | 4.3E-1 | 1.0E0 | 2.0E-1 | 5.0E-1 | 4.1E0 | 4.7E0 | 2356 | 52 | 452 | 52 | 0.74 |
| aC | mg/ml | 2.9E0 | 2.4E0 | 3.2E0 | 2.7E0 | 1.4E0 | 2.7E0 | 7.7E-1 | 9.7E-1 | 8.9E0 | 5.6E0 | 466 | 21 | 180 | 21 | 0.40 |
| aD | ug/mL | 3.2E0 | 3.2E0 | 4.5E0 | 5.5E0 | 4.0E0 | 5.6E0 | 4.3E-1 | 1.1E0 | 3.5E1 | 2.1E1 | 466 | 21 | 180 | 21 | 0.49 |
| aE | mg/mL | 5.6E-1 | 5.8E-1 | 5.7E-1 | 6.0E-1 | 1.5E-1 | 1.8E-1 | 1.8E-1 | 3.4E-1 | 1.1E0 | 1.0E0 | 466 | 21 | 180 | 21 | 0.55 |
| aF | ng/mL | 2.2E0 | 1.7E0 | 3.8E0 | 4.8E0 | 5.4E0 | 6.8E0 | 4.3E-1 | 4.3E-3 | 5.0E1 | 2.4E1 | 466 | 21 | 180 | 21 | 0.44 |
| aG | mg/mL | 1.3E-1 | 1.4E-1 | 1.5E-1 | 1.8E-1 | 8.7E-2 | 1.2E-1 | 1.7E-2 | 5.0E-2 | 5.4E-1 | 5.2E-1 | 466 | 21 | 180 | 21 | 0.53 |
| aH | ug/mL | 7.5E1 | 7.5E1 | 8.0E1 | 9.4E1 | 4.3E1 | 5.1E1 | 4.6E0 | 2.6E1 | 2.9E2 | 2.0E2 | 466 | 21 | 180 | 21 | 0.56 |
| aI | ug/mL | 1.9E2 | 1.9E2 | 1.9E2 | 1.8E2 | 6.0E1 | 5.7E1 | 2.8E1 | 8.0E1 | 3.7E2 | 2.5E2 | 466 | 21 | 180 | 21 | 0.49 |

Figure 5 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aJ | ug/mL | 2.4E0 | 4.2E0 | 3.0E0 | 5.8E0 | 2.0E0 | 5.0E0 | 7.3E-1 | 1.5E0 | 1.7E1 | 2.3E1 | 466 | 21 | 180 | 21 | 0.72 |
| aK | ng/mL | 1.5E0 | 1.6E0 | 2.4E0 | 2.5E0 | 2.6E0 | 2.5E0 | 2.9E-4 | 1.3E-1 | 1.8E1 | 1.0E1 | 466 | 21 | 180 | 21 | 0.52 |
| aL | mg/mL | 8.0E-1 | 8.3E-1 | 8.1E-1 | 8.4E-1 | 2.7E-1 | 2.0E-1 | 1.9E-1 | 4.4E-1 | 1.7E0 | 1.2E0 | 466 | 21 | 180 | 21 | 0.54 |
| aM | U/mL | 2.2E1 | 2.3E1 | 5.1E1 | 3.0E1 | 1.1E2 | 2.6E1 | 4.2E-2 | 4.2E-2 | 1.6E3 | 8.3E1 | 466 | 21 | 180 | 21 | 0.48 |
| aN | U/mL | 1.3E1 | 2.3E1 | 2.0E1 | 2.8E1 | 2.6E1 | 2.8E1 | 2.5E-3 | 2.8E0 | 3.3E2 | 1.1E2 | 466 | 21 | 180 | 21 | 0.63 |
| aO | pg/mL | 2.6E1 | 7.2E1 | 2.8E2 | 6.0E2 | 7.5E2 | 1.1E3 | 6.0E-2 | 6.0E-2 | 6.6E3 | 3.9E3 | 466 | 21 | 180 | 21 | 0.58 |
| aP | ng/mL | 1.6E0 | 2.4E0 | 2.0E0 | 3.9E0 | 1.8E0 | 5.7E0 | 4.5E-1 | 1.1E0 | 2.8E1 | 2.8E1 | 466 | 21 | 180 | 21 | 0.70 |
| aQ | ng/mL | 2.9E-1 | 4.5E-1 | 4.4E-1 | 3.9E-1 | 4.6E-1 | 2.7E-1 | 2.0E-4 | 5.2E-2 | 4.0E0 | 1.1E0 | 466 | 21 | 180 | 21 | 0.52 |
| aR | ng/mL | 1.8E0 | 2.0E0 | 2.8E0 | 3.2E0 | 3.3E0 | 3.3E0 | 1.8E-1 | 3.6E-1 | 3.4E1 | 1.5E1 | 466 | 21 | 180 | 21 | 0.54 |
| aS | ng/mL | 2.6E-1 | 3.8E-1 | 6.4E-1 | 7.6E-1 | 1.8E0 | 1.4E0 | 4.2E-3 | 2.8E-2 | 3.3E1 | 6.6E0 | 466 | 21 | 180 | 21 | 0.55 |
| aU | pg/mL | 7.5E1 | 8.4E1 | 1.3E2 | 1.0E2 | 1.5E2 | 7.7E1 | 7.4E-2 | 7.4E-2 | 1.3E3 | 2.4E2 | 466 | 21 | 180 | 21 | 0.50 |
| aV | ng/mL | 6.1E-1 | 5.3E-1 | 1.1E0 | 8.6E-1 | 2.0E0 | 7.7E-1 | 7.6E-4 | 1.0E-1 | 3.3E1 | 3.1E0 | 466 | 21 | 180 | 21 | 0.50 |
| aW | pg/mL | 1.8E1 | 2.4E1 | 1.9E1 | 3.9E1 | 1.9E1 | 9.0E1 | 7.2E-2 | 7.2E-2 | 2.4E2 | 4.3E2 | 466 | 21 | 180 | 21 | 0.57 |
| aX | ng/mL | 9.8E0 | 1.3E1 | 1.5E1 | 3.5E1 | 1.9E1 | 5.4E1 | 3.0E-1 | 2.1E0 | 2.2E2 | 2.1E2 | 466 | 21 | 180 | 21 | 0.59 |
| aY | pg/mL | 6.0E1 | 4.8E1 | 7.7E1 | 7.7E1 | 8.6E1 | 5.8E1 | 4.1E-1 | 1.2E1 | 1.2E3 | 2.1E2 | 466 | 21 | 180 | 21 | 0.52 |
| aZ | pg/mL | 2.3E2 | 3.0E2 | 4.9E2 | 3.9E2 | 9.2E2 | 4.0E2 | 1.7E0 | 2.4E1 | 1.2E4 | 1.8E3 | 466 | 21 | 180 | 21 | 0.54 |
| bA | ng/mL | 8.4E0 | 3.2E1 | 3.5E1 | 1.7E2 | 1.0E2 | 3.6E2 | 3.0E-2 | 3.0E-2 | 9.4E2 | 1.5E3 | 466 | 21 | 180 | 21 | 0.68 |
| bB | ng/mL | 3.0E2 | 3.2E2 | 3.1E2 | 3.6E2 | 1.6E2 | 2.2E2 | 2.1E0 | 6.6E1 | 8.2E2 | 7.8E2 | 466 | 21 | 180 | 21 | 0.55 |
| bC | ng/mL | 3.5E2 | 7.0E2 | 6.2E2 | 1.0E3 | 8.2E2 | 1.1E3 | 2.7E1 | 1.3E2 | 4.7E3 | 4.0E3 | 466 | 21 | 180 | 21 | 0.59 |
| bE | mg/mL | 5.6E0 | 5.5E0 | 5.8E0 | 6.7E0 | 2.1E0 | 2.7E0 | 9.8E-1 | 3.1E0 | 1.3E1 | 1.3E1 | 466 | 21 | 180 | 21 | 0.56 |
| bF | pg/mL | 2.1E1 | 2.1E1 | 1.6E2 | 2.2E2 | 9.3E2 | 4.8E2 | 5.0E-2 | 8.1E0 | 1.1E4 | 1.9E3 | 466 | 21 | 180 | 21 | 0.55 |
| bG | ng/mL | 1.6E0 | 2.4E0 | 2.7E0 | 3.6E0 | 3.2E0 | 5.6E0 | 2.2E-2 | 1.9E-1 | 2.3E1 | 2.6E1 | 466 | 21 | 180 | 21 | 0.55 |
| bH | pg/mL | 5.7E-1 | 5.7E-1 | 5.0E0 | 4.8E0 | 1.5E1 | 5.3E0 | 5.7E-1 | 5.7E-1 | 2.8E2 | 1.7E1 | 466 | 21 | 180 | 21 | 0.56 |
| bI | ng/mL | 4.0E-3 | 4.0E-3 | 6.5E-2 | 7.2E-2 | 1.6E-1 | 1.4E-1 | 4.0E-3 | 4.0E-3 | 1.3E0 | 5.4E-1 | 466 | 21 | 180 | 21 | 0.52 |
| bJ | mg/mL | 2.4E0 | 2.3E0 | 2.7E0 | 3.0E0 | 2.1E0 | 2.2E0 | 2.5E-4 | 2.5E-4 | 1.3E1 | 8.9E0 | 466 | 21 | 180 | 21 | 0.53 |
| bL | pg/mL | 3.7E0 | 5.6E0 | 8.4E0 | 8.8E0 | 1.1E1 | 8.6E0 | 4.6E-2 | 4.6E-2 | 8.0E1 | 3.0E1 | 466 | 21 | 180 | 21 | 0.56 |
| bM | mg/mL | 1.8E0 | 2.3E0 | 2.1E0 | 2.2E0 | 1.4E0 | 1.1E0 | 9.2E-3 | 5.1E-1 | 8.8E0 | 4.7E0 | 466 | 21 | 180 | 21 | 0.55 |
| bN | ng/mL | 4.6E1 | 2.6E1 | 1.3E2 | 9.8E1 | 2.8E2 | 1.5E2 | 1.4E-1 | 2.2E0 | 1.9E3 | 5.6E2 | 466 | 21 | 180 | 21 | 0.44 |
| bO | ng/mL | 4.0E-2 | 4.0E-2 | 1.1E1 | 1.1E1 | 2.5E1 | 2.7E1 | 4.0E-2 | 4.0E-2 | 2.0E2 | 1.2E2 | 466 | 21 | 180 | 21 | 0.47 |
| bP | mg/mL | 5.4E-1 | 8.6E-1 | 7.7E-1 | 1.0E0 | 6.9E-1 | 7.6E-1 | 4.9E-2 | 1.4E-1 | 4.8E0 | 2.7E0 | 466 | 21 | 180 | 21 | 0.62 |
| bQ | pg/mL | 1.6E1 | 1.8E1 | 6.2E1 | 4.7E1 | 6.3E2 | 5.8E1 | 1.5E-1 | 1.5E-1 | 1.3E4 | 1.9E2 | 466 | 21 | 180 | 21 | 0.56 |
| bR | ng/mL | 1.2E-2 | 1.2E-2 | 1.3E-1 | 1.1E-1 | 4.5E-1 | 1.7E-1 | 1.2E-2 | 1.2E-2 | 8.7E0 | 4.8E-1 | 466 | 21 | 180 | 21 | 0.47 |
| bS | pg/mL | 9.4E-1 | 9.4E-1 | 7.1E0 | 7.3E0 | 2.8E1 | 1.6E1 | 9.4E-1 | 9.4E-1 | 3.9E2 | 6.7E1 | 466 | 21 | 180 | 21 | 0.52 |
| bU | ng/mL | 1.2E-1 | 1.3E-2 | 2.0E-1 | 1.4E-1 | 3.7E-1 | 2.0E-1 | 1.3E-2 | 1.3E-2 | 6.6E0 | 6.2E-1 | 466 | 21 | 180 | 21 | 0.42 |
| bV | pg/mL | 4.6E2 | 6.3E2 | 5.5E2 | 7.6E2 | 5.8E2 | 4.3E2 | 1.5E2 | 3.0E2 | 1.2E4 | 1.9E3 | 466 | 21 | 180 | 21 | 0.68 |
| bW | pg/mL | 3.4E2 | 4.2E2 | 6.4E2 | 9.1E2 | 1.7E3 | 1.2E3 | 8.4E1 | 1.1E2 | 2.5E4 | 3.9E3 | 466 | 21 | 180 | 21 | 0.59 |
| bX | ng/mL | 6.9E-4 | 2.5E-5 | 2.7E-3 | 2.3E-3 | 3.4E-3 | 2.8E-3 | 2.5E-5 | 2.5E-5 | 2.0E-2 | 8.5E-3 | 466 | 21 | 180 | 21 | 0.48 |
| bZ | pg/mL | 2.3E2 | 3.9E2 | 8.5E2 | 1.1E3 | 4.0E3 | 1.7E3 | 1.5E-1 | 1.2E2 | 5.8E4 | 7.4E3 | 466 | 21 | 180 | 21 | 0.65 |
| cA | pg/mL | 6.0E-1 | 6.0E-1 | 2.8E0 | 2.1E0 | 1.8E1 | 4.9E0 | 6.0E-1 | 6.0E-1 | 3.7E2 | 2.2E1 | 466 | 21 | 180 | 21 | 0.48 |
| cB | ng/mL | 5.7E-2 | 5.1E-2 | 9.0E-2 | 6.7E-2 | 1.0E-1 | 6.2E-2 | 1.7E-3 | 1.7E-3 | 5.7E-1 | 2.1E-1 | 466 | 21 | 180 | 21 | 0.46 |
| cC | pg/mL | 4.6E1 | 3.8E1 | 4.8E1 | 4.2E1 | 4.0E1 | 2.7E1 | 1.0E0 | 1.0E0 | 4.5E2 | 9.4E1 | 466 | 21 | 180 | 21 | 0.46 |
| cD | pg/mL | 5.6E0 | 4.9E0 | 1.3E1 | 2.5E1 | 4.9E1 | 5.4E1 | 3.3E-1 | 3.3E-1 | 7.2E2 | 2.2E2 | 466 | 21 | 180 | 21 | 0.47 |
| cE | pg/mL | 3.7E1 | 4.7E1 | 1.7E2 | 2.0E2 | 4.8E2 | 3.6E2 | 1.2E-1 | 1.7E0 | 3.8E3 | 1.4E3 | 466 | 21 | 180 | 21 | 0.54 |
| cF | pg/mL | 1.3E1 | 5.3E-1 | 2.0E1 | 1.1E1 | 3.0E1 | 1.9E1 | 5.3E-1 | 5.3E-1 | 2.7E2 | 6.8E1 | 466 | 21 | 180 | 21 | 0.39 |
| cG | pg/mL | 4.5E1 | 5.7E1 | 1.1E2 | 1.3E2 | 5.1E2 | 1.5E2 | 6.4E0 | 1.8E1 | 1.0E4 | 4.9E2 | 466 | 21 | 180 | 21 | 0.57 |
| cH | uIU/mL | 2.8E0 | 3.7E0 | 5.8E0 | 1.1E1 | 1.1E1 | 2.6E1 | 8.6E-3 | 5.8E-1 | 1.6E2 | 1.2E2 | 466 | 21 | 180 | 21 | 0.56 |
| cI | ng/mL | 5.5E0 | 1.2E1 | 1.1E1 | 2.1E1 | 1.5E1 | 2.8E1 | 1.0E-3 | 2.3E-1 | 1.2E2 | 1.2E2 | 466 | 21 | 180 | 21 | 0.60 |
| cJ | ug/mL | 5.6E1 | 7.0E1 | 1.1E2 | 1.2E2 | 1.4E2 | 1.1E2 | 4.0E0 | 5.6E0 | 9.6E2 | 3.4E2 | 466 | 21 | 180 | 21 | 0.56 |
| cK | ng/mL | 3.8E-3 | 3.8E-3 | 5.1E-2 | 2.9E-2 | 1.8E-1 | 7.4E-2 | 3.8E-3 | 3.8E-3 | 1.7E0 | 3.4E-1 | 466 | 21 | 180 | 21 | 0.53 |
| cL | pg/mL | 2.0E2 | 2.3E2 | 3.7E2 | 4.4E2 | 1.3E3 | 5.1E2 | 1.6E1 | 7.5E1 | 2.4E4 | 2.0E3 | 466 | 21 | 180 | 21 | 0.58 |
| cM | pg/mL | 2.6E2 | 3.0E2 | 2.9E2 | 2.9E2 | 2.0E2 | 1.5E2 | 8.7E0 | 1.2E2 | 1.6E3 | 7.2E2 | 466 | 21 | 180 | 21 | 0.51 |
| cN | pg/mL | 1.2E2 | 1.4E2 | 1.3E2 | 1.6E2 | 6.5E1 | 5.4E1 | 3.8E1 | 8.6E1 | 1.1E3 | 2.8E2 | 466 | 21 | 180 | 21 | 0.69 |
| cO | pg/mL | 2.3E2 | 2.4E2 | 3.2E2 | 3.0E2 | 9.0E2 | 2.9E2 | 5.4E1 | 9.2E1 | 1.9E4 | 1.5E3 | 466 | 21 | 180 | 21 | 0.51 |
| cP | ng/mL | 2.5E3 | 2.9E3 | 2.6E3 | 3.0E3 | 9.1E2 | 1.3E3 | 6.2E2 | 1.4E3 | 5.7E3 | 5.6E3 | 466 | 21 | 180 | 21 | 0.58 |
| cQ | ng/mL | 5.3E-2 | 4.5E-2 | 1.5E-1 | 1.0E-1 | 3.0E-1 | 2.0E-1 | 2.0E-3 | 2.0E-3 | 2.2E0 | 9.3E-1 | 466 | 21 | 180 | 21 | 0.47 |
| cR | ng/mL | 3.0E2 | 3.4E2 | 5.2E2 | 4.7E2 | 8.2E2 | 4.0E2 | 2.0E1 | 4.9E1 | 8.9E3 | 1.5E3 | 466 | 21 | 180 | 21 | 0.53 |
| cS | ng/mL | 2.5E2 | 4.3E2 | 4.0E2 | 8.4E2 | 4.0E2 | 1.5E3 | 4.1E1 | 6.6E1 | 2.7E3 | 7.1E3 | 466 | 21 | 180 | 21 | 0.65 |

Figure 5 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cT | ng/mL | 3.3E1 | 6.5E1 | 8.4E1 | 2.7E2 | 1.9E2 | 4.3E2 | 3.7E0 | 4.4E0 | 2.1E3 | 1.5E3 | 466 | 21 | 180 | 21 | 0.61 |
| cU | ng/mL | 5.3E1 | 7.5E1 | 7.6E1 | 9.2E1 | 1.0E2 | 7.7E1 | 5.4E0 | 1.7E1 | 1.6E3 | 3.5E2 | 466 | 21 | 180 | 21 | 0.61 |
| cV | ng/mL | 1.8E-1 | 1.5E-1 | 4.0E-1 | 1.9E-1 | 2.2E0 | 1.2E-1 | 2.5E-2 | 3.4E-2 | 4.7E1 | 4.9E-1 | 466 | 21 | 180 | 21 | 0.44 |
| cW | mIU/mL | 5.3E-2 | 4.9E-2 | 1.5E-1 | 7.8E-2 | 7.0E-1 | 6.5E-2 | 3.7E-4 | 6.4E-3 | 9.7E0 | 2.9E-1 | 466 | 21 | 180 | 21 | 0.53 |
| cX | ng/mL | 1.1E-1 | 6.4E-2 | 1.2E0 | 4.0E-1 | 3.8E0 | 8.1E-1 | 2.3E-4 | 2.3E-4 | 2.8E1 | 3.0E0 | 466 | 21 | 180 | 21 | 0.43 |
| cY | ng/mL | 8.6E0 | 6.8E0 | 1.3E1 | 1.1E1 | 1.3E1 | 1.0E1 | 1.5E-1 | 6.0E-1 | 8.3E1 | 3.9E1 | 466 | 21 | 180 | 21 | 0.46 |
| cZ | ug/mL | 1.5E1 | 1.6E1 | 1.6E1 | 1.8E1 | 7.4E0 | 8.0E0 | 2.3E0 | 7.5E0 | 5.7E1 | 4.0E1 | 466 | 21 | 180 | 21 | 0.59 |
| dA | pg/mL | 3.2E2 | 3.9E2 | 3.7E2 | 4.2E2 | 3.1E2 | 1.9E2 | 9.0E1 | 1.7E2 | 5.8E3 | 8.7E2 | 466 | 21 | 180 | 21 | 0.61 |
| dB | ug/mL | 1.7E1 | 1.9E1 | 1.8E1 | 2.0E1 | 1.6E1 | 8.7E0 | 9.4E-1 | 2.4E0 | 2.5E2 | 3.7E1 | 466 | 21 | 180 | 21 | 0.63 |
| dC | nmol/L | 3.5E1 | 3.1E1 | 3.8E1 | 4.0E1 | 1.8E1 | 2.2E1 | 7.6E0 | 1.5E1 | 1.4E2 | 9.1E1 | 466 | 21 | 180 | 21 | 0.46 |
| dD | ug/mL | 3.6E1 | 3.4E1 | 3.7E1 | 3.5E1 | 1.1E1 | 9.6E0 | 1.3E1 | 2.3E1 | 7.6E1 | 6.2E1 | 466 | 21 | 180 | 21 | 0.44 |
| dE | ng/mL | 4.8E-1 | 4.8E-1 | 6.1E-1 | 6.6E-1 | 7.0E-1 | 7.5E-1 | 8.4E-3 | 8.4E-3 | 7.2E0 | 2.4E0 | 466 | 21 | 180 | 21 | 0.50 |
| dF | ng/mL | 2.3E2 | 2.5E2 | 2.8E2 | 3.4E2 | 1.9E2 | 2.3E2 | 5.6E1 | 1.0E2 | 1.3E3 | 8.3E2 | 466 | 21 | 180 | 21 | 0.57 |
| dG | ng/mL | 1.1E1 | 1.5E1 | 1.5E1 | 1.9E1 | 1.4E1 | 1.3E1 | 2.2E0 | 6.8E0 | 1.8E2 | 6.5E1 | 466 | 21 | 180 | 21 | 0.64 |
| dH | pg/mL | 7.5E0 | 8.9E0 | 1.3E1 | 1.5E1 | 3.9E1 | 1.7E1 | 4.0E-2 | 8.3E-1 | 6.7E2 | 7.6E1 | 466 | 21 | 180 | 21 | 0.58 |
| dI | pg/mL | 4.6E-1 | 4.6E-1 | 2.3E0 | 2.5E0 | 1.6E1 | 4.4E0 | 4.6E-1 | 4.6E-1 | 3.3E2 | 1.9E1 | 466 | 21 | 180 | 21 | 0.55 |
| dJ | ng/mL | 1.9E0 | 1.9E0 | 2.2E0 | 2.4E0 | 1.1E0 | 1.6E0 | 3.2E-2 | 5.6E-1 | 6.9E0 | 5.7E0 | 466 | 21 | 180 | 21 | 0.51 |
| dK | uIU/mL | 1.9E0 | 1.6E0 | 3.1E0 | 2.3E0 | 6.5E0 | 2.6E0 | 2.8E-4 | 1.4E-2 | 7.9E1 | 1.2E1 | 466 | 21 | 180 | 21 | 0.47 |
| dL | ng/mL | 8.8E2 | 1.2E3 | 1.0E3 | 1.2E3 | 5.9E2 | 4.1E2 | 2.6E2 | 5.9E2 | 4.8E3 | 2.3E3 | 466 | 21 | 180 | 21 | 0.64 |
| dM | pg/mL | 9.5E2 | 1.3E3 | 1.2E3 | 2.0E3 | 1.4E3 | 1.9E3 | 3.4E2 | 5.2E2 | 1.6E4 | 8.8E3 | 466 | 21 | 180 | 21 | 0.66 |
| dN | ug/mL | 9.4E1 | 1.2E2 | 1.0E2 | 1.3E2 | 4.1E1 | 4.2E1 | 1.6E1 | 6.6E1 | 3.3E2 | 1.9E2 | 466 | 21 | 180 | 21 | 0.67 |
| dR | pg/ml | 1.6E3 | 1.2E3 | 2.4E3 | 1.8E3 | 2.4E3 | 1.8E3 | 1.4E2 | 1.3E2 | 1.5E4 | 7.3E3 | 312 | 19 | 171 | 19 | 0.45 |
| dU | pg/ml | 1.1E4 | 8.5E3 | 1.6E4 | 1.2E4 | 1.5E4 | 1.2E4 | 6.9E2 | 1.7E3 | 8.1E4 | 3.5E4 | 47 | 7 | 44 | 7 | 0.40 |
| dX | ng/ml | 5.2E-2 | 1.0E-1 | 1.5E-1 | 9.4E-2 | 2.5E-1 | 8.7E-2 | 2.6E-3 | 2.6E-3 | 1.5E0 | 2.3E-1 | 140 | 8 | 46 | 8 | 0.48 |
| eF | ng/ml | 4.1E0 | 5.4E0 | 5.0E0 | 6.8E0 | 4.2E0 | 5.9E0 | 1.2E0 | 2.1E0 | 4.6E1 | 2.9E1 | 324 | 19 | 172 | 19 | 0.64 |
| eC | pg/ml | 3.0E2 | 2.5E2 | 3.8E2 | 3.3E2 | 2.9E2 | 1.8E2 | 9.9E0 | 1.1E2 | 2.0E3 | 7.1E2 | 246 | 16 | 160 | 16 | 0.45 |
| eD | pg/ml | 2.1E2 | 1.7E2 | 5.0E2 | 2.7E2 | 1.1E3 | 3.7E2 | 5.2E-1 | 5.1E1 | 8.3E3 | 1.5E3 | 196 | 14 | 131 | 14 | 0.40 |
| eM | ng/ml | 3.4E0 | 3.9E0 | 4.7E0 | 1.0E1 | 4.7E0 | 1.4E1 | 6.9E-1 | 3.3E-1 | 2.7E1 | 3.9E1 | 176 | 12 | 70 | 12 | 0.56 |
| eP | ng/ml | 3.7E-3 | 4.8E-1 | 6.4E-1 | 3.5E0 | 1.5E0 | 7.8E0 | 3.7E-3 | 3.7E-3 | 1.2E1 | 2.2E1 | 140 | 8 | 46 | 8 | 0.64 |
| eQ | pg/ml | 1.0E0 | 1.0E0 | 7.8E1 | 3.9E1 | 2.5E2 | 8.3E1 | 1.0E0 | 1.0E0 | 1.6E3 | 2.2E2 | 47 | 7 | 44 | 7 | 0.49 |
| fA | ng/ml | 1.5E2 | 3.6E2 | 4.0E2 | 5.7E2 | 4.5E2 | 4.9E2 | 2.6E1 | 7.6E1 | 1.5E3 | 1.3E3 | 47 | 7 | 45 | 7 | 0.65 |
| fB | ng/ml | 6.1E2 | 5.1E2 | 6.9E2 | 6.4E2 | 2.9E2 | 3.6E2 | 1.6E2 | 3.5E2 | 1.3E3 | 1.4E3 | 48 | 7 | 46 | 7 | 0.40 |
| fP | ng/ml | 2.6E2 | 3.1E2 | 2.9E2 | 2.9E2 | 1.7E2 | 1.9E2 | 8.4E0 | 1.8E0 | 1.0E3 | 6.9E2 | 298 | 18 | 163 | 18 | 0.52 |
| fR | ng/ml | 1.3E5 | 1.9E5 | 1.8E5 | 3.1E5 | 1.5E5 | 2.5E5 | 2.9E4 | 1.9E2 | 8.3E5 | 8.7E5 | 320 | 15 | 97 | 15 | 0.66 |
| gC | ng/ml | 2.3E2 | 2.6E2 | 2.6E2 | 2.8E2 | 1.3E2 | 1.6E2 | 8.3E1 | 9.7E1 | 1.1E3 | 5.9E2 | 135 | 10 | 79 | 10 | 0.51 |
| gL | pg/ml | 6.4E4 | 6.6E4 | 7.0E4 | 9.2E4 | 2.9E4 | 5.3E4 | 1.4E4 | 2.7E4 | 2.0E5 | 2.2E5 | 312 | 19 | 171 | 19 | 0.60 |
| gP | U/ml | 2.7E2 | 3.0E2 | 2.7E2 | 3.2E2 | 9.4E1 | 2.1E2 | 1.2E1 | 6.5E1 | 8.0E2 | 1.1E3 | 320 | 19 | 172 | 19 | 0.57 |
| gW | ng/ml | 6.1E2 | 6.6E2 | 1.3E3 | 1.1E3 | 1.7E3 | 1.2E3 | 3.1E-1 | 7.4E1 | 9.5E3 | 3.8E3 | 273 | 12 | 163 | 12 | 0.53 |
| gV | ng/ml | 2.0E1 | 2.5E1 | 2.1E1 | 2.5E1 | 7.4E0 | 6.6E0 | 2.9E-3 | 1.6E1 | 4.0E1 | 3.4E1 | 110 | 7 | 25 | 7 | 0.65 |
| tF | pg/mL | 1.5E3 | 2.0E3 | 1.2E4 | 1.2E4 | 3.8E4 | 2.2E4 | 1.2E1 | 1.8E1 | 3.2E5 | 7.6E4 | 246 | 16 | 160 | 16 | 0.55 |
| gZ | ug/ml | 8.0E-1 | 6.0E0 | 6.1E1 | 4.4E1 | 1.3E2 | 8.8E1 | 8.7E-2 | 4.6E-1 | 4.1E2 | 2.4E2 | 47 | 7 | 44 | 7 | 0.66 |
| hA | ng/ml | 2.1E0 | 2.4E0 | 9.9E0 | 4.5E0 | 3.7E1 | 5.6E0 | 1.7E-2 | 2.0E-1 | 3.5E2 | 2.0E1 | 197 | 14 | 131 | 14 | 0.54 |
| nM | pg/ml | 1.0E-9 | 1.0E-9 | 7.7E1 | 1.0E-9 | 8.9E2 | 0.0E0 | 1.0E-9 | 1.0E-9 | 1.0E4 | 1.0E-9 | 133 | 17 | 101 | 17 | 0.49 |
| nN | pg/ml | 1.2E3 | 2.4E3 | 4.2E3 | 6.1E3 | 2.3E4 | 1.1E4 | 1.1E2 | 2.3E2 | 2.7E5 | 4.4E4 | 133 | 17 | 101 | 17 | 0.66 |
| nO | pg/ml | 2.6E1 | 4.4E1 | 4.5E1 | 7.0E1 | 5.3E1 | 7.9E1 | 3.5E0 | 8.9E0 | 3.1E2 | 3.4E2 | 133 | 17 | 101 | 17 | 0.63 |
| nR | pg/ml | 1.5E1 | 1.9E1 | 3.2E1 | 1.3E2 | 4.5E1 | 2.6E2 | 1.0E-9 | 1.8E0 | 2.6E2 | 1.1E3 | 133 | 17 | 101 | 17 | 0.62 |
| nT | pg/ml | 8.0E1 | 7.2E1 | 2.0E2 | 4.7E2 | 7.9E2 | 1.3E3 | 1.0E-9 | 1.0E-9 | 6.6E3 | 5.5E3 | 133 | 17 | 101 | 17 | 0.57 |
| nU | pg/ml | 2.9E1 | 1.2E2 | 2.5E2 | 7.6E2 | 1.4E3 | 2.6E3 | 1.0E-9 | 1.0E-9 | 1.3E4 | 1.1E4 | 133 | 17 | 101 | 17 | 0.68 |
| IW | pg/ml | 1.0E-9 | 1.0E-9 | 1.4E1 | 1.2E1 | 4.9E1 | 2.6E1 | 1.0E-9 | 1.0E-9 | 3.9E2 | 9.7E1 | 133 | 17 | 101 | 17 | 0.51 |
| IX | pg/ml | 9.5E2 | 1.1E3 | 1.0E3 | 9.8E2 | 5.8E2 | 3.8E2 | 1.2E2 | 4.3E2 | 2.6E3 | 1.6E3 | 133 | 17 | 101 | 17 | 0.50 |
| IY | pg/ml | 1.9E1 | 2.3E1 | 2.2E1 | 2.7E1 | 1.9E1 | 3.6E1 | 1.0E-9 | 1.0E-9 | 1.4E2 | 1.5E2 | 133 | 17 | 101 | 17 | 0.49 |
| mE | pg/ml | 1.0E-9 | 1.0E-9 | 2.9E0 | 3.7E0 | 8.5E0 | 1.0E1 | 1.0E-9 | 1.0E-9 | 5.8E1 | 4.2E1 | 133 | 17 | 101 | 17 | 0.51 |
| mF | pg/ml | 1.0E-9 | 1.0E-9 | 2.4E0 | 1.6E1 | 9.4E0 | 5.9E1 | 1.0E-9 | 1.0E-9 | 1.1E2 | 2.5E2 | 133 | 17 | 101 | 17 | 0.52 |
| mH | pg/ml | 3.6E0 | 2.3E0 | 5.3E0 | 5.0E0 | 6.6E0 | 7.5E0 | 2.3E-1 | 5.4E-1 | 5.3E1 | 3.2E1 | 133 | 17 | 101 | 17 | 0.43 |
| ml | pg/ml | 1.0E-9 | 3.7E0 | 1.5E1 | 2.5E1 | 3.1E1 | 5.4E1 | 1.0E-9 | 1.0E-9 | 1.8E2 | 2.1E2 | 133 | 17 | 101 | 17 | 0.56 |
| mM | pg/ml | 2.2E1 | 2.7E1 | 6.9E1 | 5.6E1 | 1.3E2 | 8.0E1 | 1.0E-9 | 1.0E-9 | 9.8E2 | 3.3E2 | 133 | 17 | 101 | 17 | 0.54 |
| mP | pg/ml | 1.4E1 | 1.5E1 | 1.8E1 | 2.6E1 | 2.2E1 | 3.8E1 | 1.0E-9 | 1.0E-9 | 1.9E2 | 1.7E2 | 132 | 17 | 100 | 17 | 0.60 |

Figure 5 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| mS | pg/ml | 1.6E3 | 1.9E3 | 1.8E3 | 2.1E3 | 1.6E3 | 1.3E3 | 1.0E-9 | 6.4E2 | 1.3E4 | 4.7E3 | 133 | 17 | 101 | 17 | 0.56 |
| mT | pg/ml | 5.4E1 | 7.4E1 | 1.3E2 | 1.3E2 | 2.2E2 | 2.3E2 | 9.7E0 | 2.0E1 | 1.4E3 | 1.0E3 | 132 | 17 | 100 | 17 | 0.55 |
| mU | pg/ml | 2.2E0 | 2.9E0 | 4.0E0 | 3.8E0 | 8.3E0 | 3.7E0 | 1.0E-9 | 1.0E-9 | 6.8E1 | 1.6E1 | 132 | 17 | 100 | 17 | 0.59 |
| mW | pg/ml | 2.3E3 | 2.7E3 | 2.7E3 | 3.4E3 | 2.1E3 | 2.6E3 | 1.0E-9 | 2.0E2 | 1.8E4 | 1.1E4 | 132 | 17 | 100 | 17 | 0.60 |
| mY | pg/ml | 5.5E2 | 5.1E2 | 8.5E2 | 1.5E3 | 1.3E3 | 3.4E3 | 1.0E-9 | 6.1E1 | 1.1E4 | 1.4E4 | 133 | 17 | 101 | 17 | 0.47 |
| mZ | pg/ml | 1.7E2 | 5.5E2 | 2.9E2 | 6.3E2 | 3.0E2 | 6.1E2 | 1.0E-9 | 8.4E1 | 1.5E3 | 2.6E3 | 132 | 17 | 100 | 17 | 0.72 |
| nA | pg/ml | 1.6E0 | 3.4E0 | 1.0E1 | 1.2E1 | 4.3E1 | 1.8E1 | 1.0E-9 | 1.0E-9 | 4.4E2 | 5.5E1 | 132 | 17 | 100 | 17 | 0.64 |
| nB | pg/ml | 3.1E2 | 2.9E2 | 3.2E2 | 3.2E2 | 1.7E2 | 1.4E2 | 3.0E1 | 1.6E2 | 9.1E2 | 6.4E2 | 133 | 17 | 101 | 17 | 0.52 |
| nC | pg/ml | 1.0E-9 | 1.0E-9 | 2.5E4 | 4.3E4 | 1.5E5 | 1.7E5 | 1.0E-9 | 1.0E-9 | 1.5E6 | 6.8E5 | 133 | 17 | 101 | 17 | 0.55 |
| nD | pg/ml | 7.9E0 | 1.0E1 | 3.6E1 | 2.3E1 | 2.0E2 | 3.4E1 | 1.0E-9 | 1.0E-9 | 1.7E3 | 1.3E2 | 132 | 17 | 100 | 17 | 0.60 |
| nF | pg/ml | 1.0E-9 | 1.0E-9 | 4.5E0 | 5.6E0 | 2.5E1 | 1.3E1 | 1.0E-9 | 1.0E-9 | 2.4E2 | 3.8E1 | 133 | 17 | 101 | 17 | 0.53 |
| nH | pg/ml | 1.0E0 | 3.8E-1 | 2.2E2 | 6.2E2 | 1.3E3 | 2.4E3 | 1.0E-9 | 1.0E-9 | 1.0E4 | 1.0E4 | 132 | 17 | 100 | 17 | 0.54 |
| nI | pg/ml | 3.0E1 | 5.0E1 | 1.5E2 | 1.5E2 | 8.3E2 | 2.7E2 | 1.0E-9 | 1.0E-9 | 9.2E3 | 9.1E2 | 133 | 17 | 101 | 17 | 0.56 |
| nJ | pg/ml | 5.9E-2 | 6.1E-1 | 4.1E1 | 3.6E0 | 4.5E2 | 7.3E0 | 1.0E-9 | 1.0E-9 | 5.2E3 | 2.7E1 | 133 | 17 | 101 | 17 | 0.61 |
| nK | pg/ml | 1.0E-9 | 1.0E-9 | 5.6E1 | 1.4E2 | 3.4E2 | 4.8E2 | 1.0E-9 | 1.0E-9 | 3.2E3 | 2.0E3 | 132 | 17 | 100 | 17 | 0.51 |
| nL | pg/ml | 1.0E-9 | 1.0E-9 | 5.9E2 | 8.6E2 | 4.1E3 | 3.1E3 | 1.0E-9 | 1.0E-9 | 4.5E4 | 1.3E4 | 133 | 17 | 101 | 17 | 0.55 |
| hR | pg/ml | 2.6E4 | 2.4E4 | 2.7E4 | 2.3E4 | 1.1E4 | 5.9E3 | 1.0E-9 | 1.3E4 | 5.8E4 | 3.2E4 | 187 | 13 | 127 | 13 | 0.37 |
| hV | pg/ml | 4.4E2 | 3.3E2 | 4.6E2 | 5.4E2 | 2.4E2 | 6.3E2 | 1.0E-9 | 1.5E2 | 1.5E3 | 2.5E3 | 187 | 13 | 127 | 13 | 0.42 |
| hW | pg/ml | 1.6E3 | 2.0E3 | 2.1E3 | 3.0E3 | 3.0E3 | 3.1E3 | 1.0E-9 | 7.9E2 | 4.0E4 | 1.0E4 | 187 | 13 | 127 | 13 | 0.56 |
| hX | pg/ml | 9.0E2 | 9.9E2 | 1.0E3 | 1.1E3 | 7.3E2 | 6.7E2 | 2.5E0 | 5.2E2 | 8.6E3 | 2.6E3 | 187 | 13 | 127 | 13 | 0.51 |
| iA | pg/ml | 1.5E2 | 1.7E2 | 3.0E2 | 4.1E2 | 6.1E2 | 9.0E2 | 8.2E0 | 1.7E1 | 7.1E3 | 3.8E3 | 246 | 16 | 160 | 16 | 0.52 |
| iB | ng/ml | 4.8E0 | 6.7E0 | 6.1E0 | 1.0E1 | 5.0E0 | 9.3E0 | 3.3E-2 | 1.1E0 | 2.6E1 | 3.8E1 | 197 | 14 | 131 | 14 | 0.66 |
| iC | U/ml | 2.3E-1 | 5.6E-1 | 1.1E0 | 1.2E0 | 4.8E0 | 2.7E0 | 1.0E-9 | 5.5E-2 | 5.5E1 | 1.0E1 | 197 | 14 | 131 | 14 | 0.63 |
| iH | ng/ml | 1.6E5 | 1.6E5 | 1.6E5 | 1.6E5 | 4.8E4 | 5.0E4 | 2.9E3 | 8.1E4 | 2.7E5 | 2.5E5 | 246 | 16 | 160 | 16 | 0.54 |
| iJ | ng/ml | 4.9E4 | 5.0E4 | 5.2E4 | 6.4E4 | 2.6E4 | 5.5E4 | 1.8E3 | 1.2E4 | 2.5E5 | 2.5E5 | 246 | 16 | 160 | 16 | 0.55 |
| hB | ng/ml | 4.5E-1 | 5.6E-1 | 5.6E-1 | 7.1E-1 | 4.5E-1 | 7.0E-1 | 1.0E-9 | 1.2E-1 | 3.2E0 | 3.0E0 | 246 | 16 | 160 | 16 | 0.55 |
| hC | pg/ml | 3.8E3 | 1.0E4 | 6.8E3 | 1.0E4 | 8.7E3 | 1.2E4 | 1.0E-9 | 4.5E1 | 5.7E4 | 5.0E4 | 246 | 16 | 160 | 16 | 0.58 |
| hF | ng/ml | 1.0E-9 | 1.0E-9 | 2.0E1 | 1.0E-9 | 2.6E2 | 0.0E0 | 1.0E-9 | 1.0E-9 | 4.0E3 | 1.0E-9 | 246 | 16 | 160 | 16 | 0.49 |
| hG | pg/ml | 6.8E3 | 6.9E3 | 7.2E3 | 9.0E3 | 3.0E3 | 4.6E3 | 2.8E1 | 3.9E3 | 2.0E4 | 1.8E4 | 246 | 16 | 160 | 16 | 0.59 |
| iO | ng/ml | 3.7E5 | 3.7E5 | 3.9E5 | 3.9E5 | 1.8E5 | 1.7E5 | 1.1E4 | 1.0E5 | 1.1E6 | 6.6E5 | 246 | 16 | 160 | 16 | 0.52 |
| iP | ng/ml | 4.8E4 | 6.6E4 | 5.6E4 | 7.6E4 | 5.6E4 | 1.0E5 | 1.0E-9 | 1.1E4 | 5.7E5 | 4.4E5 | 246 | 16 | 160 | 16 | 0.56 |
| iZ | pg/ml | 1.6E3 | 2.1E3 | 1.8E3 | 2.3E3 | 7.4E2 | 1.3E3 | 4.7E2 | 8.4E2 | 5.1E3 | 5.7E3 | 247 | 16 | 160 | 16 | 0.63 |
| jB | ng/ml | 2.4E5 | 3.4E5 | 2.6E5 | 3.0E5 | 1.2E5 | 9.2E4 | 5.7E4 | 1.3E5 | 6.2E5 | 3.9E5 | 47 | 7 | 44 | 7 | 0.64 |
| rC | pg/ml | 1.7E3 | 1.2E3 | 2.1E3 | 2.5E3 | 1.8E3 | 2.9E3 | 1.0E-9 | 3.1E2 | 1.5E4 | 1.1E4 | 187 | 13 | 127 | 13 | 0.51 |
| rB | pg/ml | 2.6E1 | 5.8E1 | 4.6E1 | 7.5E1 | 8.9E1 | 7.3E1 | 1.0E-9 | 1.0E-9 | 9.5E2 | 2.8E2 | 187 | 13 | 127 | 13 | 0.70 |
| jD | ng/ml | 3.2E1 | 3.0E1 | 4.9E1 | 6.3E1 | 6.3E1 | 1.3E2 | 1.0E-9 | 1.0E-9 | 5.1E2 | 5.1E2 | 196 | 14 | 131 | 14 | 0.47 |
| jE | ng/ml | 1.0E-9 | 1.0E-9 | 6.9E0 | 1.0E1 | 1.6E1 | 1.7E1 | 1.0E-9 | 1.0E-9 | 1.2E2 | 5.1E1 | 196 | 14 | 131 | 14 | 0.57 |
| jF | ng/ml | 3.9E1 | 2.6E1 | 5.2E1 | 5.5E1 | 5.8E1 | 6.6E1 | 1.0E-9 | 1.0E-9 | 3.5E2 | 1.9E2 | 196 | 14 | 131 | 14 | 0.49 |
| jG | ng/ml | 4.2E3 | 6.0E3 | 4.3E3 | 6.1E3 | 1.9E3 | 2.0E3 | 6.0E2 | 2.6E3 | 9.6E3 | 1.1E4 | 197 | 14 | 131 | 14 | 0.75 |
| jH | ng/ml | 7.4E1 | 9.5E1 | 8.4E1 | 1.1E2 | 5.1E1 | 5.1E1 | 1.3E1 | 5.0E1 | 4.3E2 | 2.2E2 | 197 | 14 | 131 | 14 | 0.67 |
| jI | ng/ml | 6.8E1 | 9.2E1 | 7.6E1 | 1.1E2 | 4.1E1 | 6.0E1 | 1.9E1 | 3.1E1 | 4.4E2 | 2.3E2 | 197 | 14 | 131 | 14 | 0.72 |
| rA | pg/ml | 2.6E1 | 2.5E1 | 3.1E1 | 3.1E1 | 2.4E1 | 2.5E1 | 1.0E-9 | 6.9E0 | 2.0E2 | 9.6E1 | 197 | 14 | 131 | 14 | 0.48 |
| qZ | pg/ml | 4.4E1 | 5.9E-3 | 5.4E2 | 2.9E1 | 2.1E3 | 6.6E1 | 1.0E-9 | 6.5E-4 | 1.0E4 | 2.2E2 | 152 | 11 | 115 | 11 | 0.29 |
| qY | pg/ml | 2.6E1 | 1.8E1 | 5.0E1 | 5.8E1 | 6.4E1 | 7.7E1 | 8.7E-1 | 6.9E0 | 5.3E2 | 2.8E2 | 197 | 14 | 131 | 14 | 0.52 |
| qX | pg/ml | 6.0E1 | 8.6E1 | 6.7E1 | 8.6E1 | 4.7E1 | 4.8E1 | 1.0E-9 | 1.7E1 | 2.5E2 | 1.6E2 | 197 | 14 | 131 | 14 | 0.62 |
| qW | pg/ml | 8.8E0 | 7.1E0 | 1.3E1 | 1.2E1 | 1.5E1 | 1.3E1 | 1.0E-9 | 1.0E-9 | 1.2E2 | 3.9E1 | 197 | 14 | 131 | 14 | 0.46 |
| qV | pg/ml | 2.2E3 | 2.4E3 | 2.8E3 | 3.3E3 | 2.1E3 | 2.9E3 | 1.7E2 | 1.0E2 | 9.6E3 | 1.1E4 | 197 | 14 | 131 | 14 | 0.53 |
| qU | pg/ml | 6.4E1 | 4.4E1 | 1.8E2 | 8.6E2 | 2.8E2 | 1.2E2 | 1.0E-9 | 7.1E0 | 2.1E3 | 4.5E2 | 197 | 14 | 131 | 14 | 0.41 |
| qT | pg/ml | 4.1E1 | 6.2E1 | 7.6E1 | 7.5E1 | 1.1E2 | 7.3E1 | 1.0E-9 | 2.2E1 | 9.0E2 | 3.1E2 | 197 | 14 | 131 | 14 | 0.56 |
| jK | ng/ml | 1.6E3 | 1.7E3 | 1.7E3 | 1.7E3 | 6.6E2 | 6.0E2 | 2.8E2 | 8.0E2 | 4.3E3 | 2.6E3 | 197 | 14 | 131 | 14 | 0.52 |
| jL | ng/ml | 2.0E2 | 2.8E2 | 3.0E2 | 2.9E2 | 3.0E2 | 1.8E2 | 3.5E1 | 3.7E1 | 2.1E3 | 7.1E2 | 197 | 14 | 131 | 14 | 0.57 |
| jM | ng/ml | 7.0E4 | 8.6E4 | 7.5E4 | 8.7E4 | 3.9E4 | 4.3E4 | 3.9E2 | 5.7E3 | 1.9E5 | 1.5E5 | 197 | 14 | 131 | 14 | 0.60 |
| jO | pg/ml | 2.1E5 | 2.7E5 | 2.6E5 | 2.9E5 | 1.5E5 | 1.2E5 | 5.2E4 | 1.3E5 | 1.1E6 | 4.9E5 | 197 | 14 | 131 | 14 | 0.61 |
| jP | pg/ml | 2.3E5 | 2.7E5 | 2.7E5 | 2.9E5 | 1.9E5 | 1.5E5 | 3.6E4 | 7.4E4 | 1.9E6 | 5.6E5 | 197 | 14 | 131 | 14 | 0.56 |
| jQ | pg/ml | 2.5E3 | 4.5E3 | 3.5E3 | 8.7E3 | 3.3E3 | 1.4E4 | 1.0E-9 | 5.1E2 | 1.8E4 | 5.6E4 | 197 | 14 | 131 | 14 | 0.65 |
| jR | pg/ml | 5.9E3 | 1.0E4 | 1.1E4 | 2.4E4 | 1.3E4 | 4.6E4 | 1.0E-9 | 3.0E1 | 9.0E4 | 1.8E5 | 197 | 14 | 131 | 14 | 0.62 |
| jT | pg/ml | 1.7E5 | 1.8E5 | 1.7E5 | 2.1E5 | 6.2E4 | 1.0E5 | 6.8E4 | 9.9E4 | 3.9E5 | 4.7E5 | 197 | 14 | 131 | 14 | 0.59 |

Figure 5 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jU | mIU/ml | 4.3E0 | 3.7E0 | 1.0E1 | 5.1E0 | 1.7E1 | 5.1E0 | 4.2E-2 | 1.1E-1 | 1.1E2 | 1.6E1 | 197 | 14 | 131 | 14 | 0.43 |
| jV | mIU/ml | 1.3E0 | 2.1E0 | 3.3E0 | 4.9E0 | 5.7E0 | 9.1E0 | 1.7E-3 | 2.2E-3 | 3.3E1 | 3.5E1 | 197 | 14 | 131 | 14 | 0.56 |
| jY | ng/ml | 7.3E-4 | 2.1E-3 | 6.3E-3 | 4.6E-3 | 2.8E-2 | 5.9E-3 | 1.0E-9 | 1.0E-9 | 3.0E-1 | 2.0E-2 | 197 | 14 | 131 | 14 | 0.57 |
| kC | pg/ml | 9.7E1 | 1.4E2 | 1.9E2 | 3.1E2 | 4.3E2 | 4.1E2 | 2.1E1 | 3.7E1 | 3.5E3 | 1.5E3 | 133 | 17 | 101 | 17 | 0.62 |
| kE | pg/ml | 1.3E5 | 1.2E5 | 1.3E5 | 1.3E5 | 4.0E4 | 3.8E4 | 1.2E4 | 5.1E4 | 2.3E5 | 1.9E5 | 133 | 17 | 101 | 17 | 0.49 |
| kF | pg/mL | 6.1E1 | 6.9E1 | 6.9E1 | 7.8E1 | 4.9E1 | 2.7E1 | 2.6E1 | 5.3E1 | 5.1E2 | 1.3E2 | 133 | 17 | 101 | 17 | 0.64 |
| kG | pg/mL | 9.1E3 | 1.1E4 | 1.2E4 | 2.1E4 | 1.3E4 | 3.6E4 | 7.5E2 | 4.4E3 | 1.2E5 | 1.6E5 | 133 | 17 | 101 | 17 | 0.60 |
| kI | pg/ml | 1.9E2 | 2.3E2 | 2.2E2 | 2.5E2 | 1.4E2 | 1.4E2 | 4.4E1 | 7.6E1 | 8.7E2 | 6.7E2 | 133 | 17 | 101 | 17 | 0.58 |
| kK | pg/ml | 1.0E2 | 1.5E2 | 1.5E2 | 4.0E2 | 1.6E2 | 5.4E2 | 6.4E0 | 3.4E1 | 1.2E3 | 1.9E3 | 133 | 17 | 101 | 17 | 0.63 |
| kN | pg/ml | 9.9E2 | 1.1E3 | 1.5E3 | 4.9E3 | 2.2E3 | 1.3E4 | 7.6E1 | 7.3E1 | 1.7E4 | 5.5E4 | 133 | 17 | 101 | 17 | 0.53 |
| kO | pg/ml | 7.1E3 | 7.2E3 | 9.6E3 | 2.0E4 | 1.7E4 | 5.0E4 | 3.4E3 | 3.7E3 | 1.5E5 | 2.1E5 | 133 | 17 | 101 | 17 | 0.53 |
| kP | pg/ml | 5.8E3 | 4.4E3 | 7.2E3 | 6.5E3 | 6.2E3 | 5.1E3 | 8.6E2 | 1.3E3 | 4.8E4 | 2.0E4 | 133 | 17 | 101 | 17 | 0.44 |
| kQ | pg/ml | 4.1E3 | 4.7E3 | 5.2E3 | 5.2E3 | 3.8E3 | 2.5E3 | 5.6E2 | 2.1E3 | 2.5E4 | 1.1E4 | 246 | 16 | 160 | 16 | 0.55 |
| kR | pg/ml | 2.1E1 | 2.0E1 | 3.0E1 | 3.2E1 | 6.8E1 | 2.7E1 | 1.0E-9 | 8.3E0 | 1.0E3 | 9.5E1 | 246 | 16 | 160 | 16 | 0.52 |
| kS | pg/ml | 7.8E2 | 9.3E2 | 9.2E2 | 1.0E3 | 6.5E2 | 5.6E2 | 7.9E1 | 3.4E2 | 4.8E3 | 2.3E3 | 246 | 16 | 160 | 16 | 0.58 |
| rZ | ng/ml | 1.0E-9 | 5.1E-3 | 5.8E-3 | 3.2E-2 | 1.5E-2 | 8.5E-2 | 1.0E-9 | 1.0E-9 | 1.1E-1 | 2.9E-1 | 187 | 11 | 127 | 11 | 0.62 |
| rY | ng/ml | 6.1E-2 | 5.3E-2 | 1.4E-1 | 1.3E0 | 5.3E-1 | 4.1E0 | 1.0E-9 | 1.0E-9 | 6.3E0 | 1.4E1 | 187 | 11 | 127 | 11 | 0.41 |
| rX | ng/ml | 1.0E-9 | 1.0E-9 | 4.0E-2 | 2.1E-1 | 2.9E-1 | 7.1E-1 | 1.0E-9 | 1.0E-9 | 3.7E0 | 2.3E0 | 187 | 11 | 127 | 11 | 0.45 |
| lK | pg/ml | 7.9E1 | 1.1E2 | 1.7E2 | 1.8E2 | 3.1E2 | 2.3E2 | 1.0E-9 | 1.0E-9 | 3.3E3 | 7.9E2 | 196 | 14 | 131 | 14 | 0.49 |
| lL | pg/ml | 1.5E3 | 3.9E3 | 2.1E3 | 3.5E3 | 2.3E3 | 2.0E3 | 1.5E1 | 2.9E2 | 1.9E4 | 7.3E3 | 197 | 14 | 131 | 14 | 0.73 |
| lM | pg/ml | 1.1E3 | 1.6E3 | 3.6E3 | 8.6E3 | 7.0E3 | 1.6E4 | 1.3E2 | 4.1E2 | 4.4E4 | 5.1E4 | 197 | 14 | 131 | 14 | 0.56 |
| lN | pg/ml | 1.0E-9 | 1.0E-9 | 4.3E0 | 2.4E0 | 1.5E1 | 4.2E0 | 1.0E-9 | 1.0E-9 | 1.5E2 | 1.2E1 | 197 | 14 | 131 | 14 | 0.49 |
| lO | pg/ml | 1.0E-9 | 1.0E-9 | 1.8E0 | 8.2E0 | 1.4E1 | 2.3E1 | 1.0E-9 | 1.0E-9 | 1.4E2 | 8.1E1 | 196 | 14 | 131 | 14 | 0.56 |
| nW | pg/ml | 1.1E5 | 1.1E5 | 1.1E5 | 1.2E5 | 2.6E4 | 3.4E4 | 3.6E4 | 8.1E4 | 2.0E5 | 2.1E5 | 246 | 16 | 160 | 16 | 0.51 |
| nY | pg/ml | 2.0E3 | 2.6E3 | 2.3E3 | 3.4E3 | 1.3E3 | 2.7E3 | 5.1E2 | 5.7E2 | 9.9E3 | 1.0E4 | 246 | 16 | 160 | 16 | 0.61 |
| oO | pg/ml | 8.7E4 | 7.3E4 | 1.2E5 | 1.2E5 | 9.5E4 | 9.5E4 | 3.3E3 | 3.1E4 | 6.2E5 | 3.4E5 | 123 | 16 | 96 | 16 | 0.47 |
| oP | pg/ml | 1.2E5 | 1.5E5 | 1.4E5 | 2.1E5 | 8.2E4 | 1.3E5 | 2.4E4 | 4.3E4 | 4.5E5 | 4.6E5 | 123 | 16 | 96 | 16 | 0.64 |
| oQ | pg/ml | 2.9E3 | 3.6E3 | 3.8E3 | 4.6E3 | 3.0E3 | 3.8E3 | 7.7E2 | 1.4E3 | 2.0E4 | 1.7E4 | 123 | 16 | 96 | 16 | 0.57 |
| oE | pg/ml | 1.3E2 | 2.6E2 | 3.9E2 | 5.1E2 | 5.8E2 | 5.9E2 | 1.0E-9 | 1.0E-9 | 4.7E3 | 1.9E3 | 246 | 16 | 160 | 16 | 0.56 |
| oF | pg/ml | 8.0E3 | 1.1E4 | 2.1E4 | 3.4E4 | 3.3E4 | 6.1E4 | 6.4E1 | 1.8E2 | 1.7E5 | 2.5E5 | 246 | 16 | 160 | 16 | 0.55 |
| oH | pg/ml | 4.0E1 | 6.3E1 | 9.3E1 | 9.5E1 | 1.5E2 | 8.5E1 | 4.3E-1 | 1.1E1 | 9.9E2 | 3.1E2 | 246 | 16 | 160 | 16 | 0.61 |
| oK | pg/ml | 8.5E2 | 1.3E3 | 2.0E3 | 2.1E3 | 3.0E3 | 2.5E3 | 5.2E1 | 2.1E2 | 2.5E4 | 8.8E3 | 246 | 16 | 160 | 16 | 0.57 |
| oN | pg/ml | 5.1E2 | 5.5E2 | 7.6E2 | 6.3E2 | 1.4E3 | 2.9E2 | 1.1E2 | 1.6E2 | 1.8E4 | 1.2E3 | 246 | 16 | 160 | 16 | 0.55 |
| oW | pg/ml | 2.1E2 | 2.7E2 | 4.4E2 | 1.4E3 | 9.2E2 | 2.8E3 | 2.9E1 | 1.8E2 | 6.0E3 | 7.6E3 | 47 | 7 | 44 | 7 | 0.64 |
| oT | pg/ml | 3.5E2 | 2.8E2 | 3.6E2 | 3.0E2 | 1.9E2 | 1.6E2 | 9.9E1 | 1.1E2 | 7.9E2 | 5.3E2 | 47 | 7 | 44 | 7 | 0.41 |
| oV | pg/ml | 1.2E2 | 9.8E1 | 2.3E2 | 4.5E2 | 3.6E2 | 8.6E2 | 1.0E-9 | 1.0E-9 | 2.2E3 | 2.4E3 | 47 | 7 | 44 | 7 | 0.47 |
| oD | pg/ml | 1.6E4 | 1.7E4 | 1.8E4 | 2.0E4 | 7.7E3 | 9.1E3 | 6.6E3 | 8.7E3 | 4.6E4 | 3.2E4 | 47 | 7 | 44 | 7 | 0.55 |
| pF | pg/ml | 5.1E-1 | 8.3E-1 | 1.1E0 | 8.4E-1 | 5.6E0 | 5.9E-1 | 1.0E-9 | 1.4E-1 | 8.7E1 | 2.5E0 | 246 | 16 | 160 | 16 | 0.60 |
| pH | ng/ml | 8.9E0 | 8.7E0 | 1.1E1 | 1.0E1 | 9.1E0 | 7.1E0 | 1.2E0 | 3.0E0 | 4.7E1 | 2.3E1 | 47 | 7 | 44 | 7 | 0.49 |
| pI | ng/ml | 7.0E1 | 4.9E1 | 7.5E1 | 6.0E1 | 4.0E1 | 2.3E1 | 2.3E1 | 3.5E1 | 2.0E2 | 9.9E1 | 47 | 7 | 44 | 7 | 0.41 |
| pK | ng/ml | 4.8E-1 | 3.3E-1 | 5.3E-1 | 3.8E-1 | 2.9E-1 | 2.0E-1 | 1.6E-1 | 1.7E-1 | 1.6E0 | 7.7E-1 | 47 | 7 | 44 | 7 | 0.32 |

Analyte panel data:

Unconstrained panels with 3 analytes, where 1.0E-10 >= 'model p-value' > 0. Contains 159 panels of 14,487,373 total panels evaluated. :
Jj{Is(aA Et Fp Fr Hq Hr Hu Hv Hw Hx Ih Ii Ij Ik Il Im In Io Ip Iq Ir It Iu Iv Jg Jh Ji Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Mu(aA Fr Im Ip Ji Jm Jq Lv Nu Oh Oy Oz Pc Qa Qb Qc Qd) Ji(aA Fr Mn Nm Ny Oy Oz) aA(Lv Mg Oz Pc Qd) Qd(Ik Il Im) FrOz} aA{Ji(In Nm Oz) OzPc} Uc{Qd(Ba Cp cT)}

Unconstrained panels with 3 analytes, where 1.0E-9 >= 'model p-value' > 1.0E-10. Contains 346 panels of 14,487,373 total panels evaluated. :
Jj{Mu(Et Fp Hq Hr Hu Hv Hw Hx Ih Ii Ij Ik In Io Iq Ir It Iu Iv Jg Jh Jk Jl Jn Jo Jp Jr Js Jt Lh Li Lj Lu Lw Lx Ly Lz Ma Mb Mc Md Me Mf Mg Mh Mi Mj Mk Ml Mm Mn Mp Mq Mr Ms Mt Mv Mw Mx My Mz Na Nb Nc Nd Ne Nf Ng Nh Ni Nj Nk Nl Nm Nn Nq Nr Ns Nt Nv Nw Nx Ny Oe Of Og Oi Ok Om On Pa Pb Pd Pe Pf Pg Po Pz Qe) Ji(Et Hq Hv Hw Ij Ik Im In Io Ip Iq Iv Jh Jk Jl Jm Jn Jt Lh Lu Lv Lx Ly Mb Md Mg Ml Mm Mr Mt Mv My Nc Nd Ne Nh Ni Nk Nl Nn Ns Nt Nu Nw Oh Oi Om On Pa Pb Pc Pe Po Pz Qa Qb Qc Qd) Fr(aA Ij Ik Im In Io Ip Ir Iv Jh Jm Jq Lv Ly Mb Mn Mx Nc Nd Ne Nh Ni Nj Nl Nn Ns Nt Nu Nv Nw Nx Ny Oh Oi Om Oy Pb Pc Qa Qb Qc Qd) aA(Hq Ij Ik Im Ip Iv Jg Jh Jk Jm Jq Lw Lx Mb Mv Mz Nd Nh Nj Nl Nn Nt Nu Nv Nw Nx Oh Oi Ok Om On Oy Pa Pb Po Qb Qc) Qd(Ilw Io Ip Jk Jq Lv Mn Nm Nn Nw Ny Oh Oi Om Oy Oz Pb Pc Pz) Oz(Ip Jk Jl Jq Lv Nn Nv Nw Oh Qa Qb) Oy(Ip Jl Jq Lv Nv Nw Oh Qa Qb) Lv(Ip Nn Nv Nw Oh Qa Qb) Ip(Jk Nn Nu Oh Qa) Nw(Ij Md Ml) Nv(Mn Ny) QaPc} aA{Ji(Hr Hw Ih Ii Ij Jm Jo Jt Lh Mm Mn Ny Om Pc) Oz(In Is Jg Jq Lv Lx Mu Mz Nn

Figure 5 Continued

Nw Pe) Nw(Ij In Lh Md Ny Pg) In(Is Lv Mu Qd) MuOy} Qd{Uc(Aw bA Bg Ef Hc Mu Mv) BafP} Is{Jm(Fr Mu Oz) MuIn} MuOzfR HuPfmP VocLgC

Unconstrained panels with 3 analytes, where 1.0E-8 >= 'model p-value' > 1.0E-9. Contains 1,299 panels of 14,487,373 total panels evaluated. : Jj{Qd(cH cV Et FP Hq Hr Hu Hv Hx Ih Ii Ij In Iq Ir It Iu Iv Jg Jh Jl Jm Jn Jo Jp Jr Js Jt Lh Li Lj Lu Lw Lx Ly Lz Ma Mb Mc Md Me Mf Mg Mh Mi Mj Mk Ml Mm Mp Mq Mr Ms Mt Mv Mw Mx My Mz Na Nb Nc Nd Ne Nf Ng Nh Ni Nj Nk Nl No Nq Nr Ns Nt Nu Nv Nx Oe Of Og Ok On Pa Pd Pe Pf Pg Po Qa Qb Qc Qe Wm) Fr(Et Fp Hq Hr Hu Hv Hw Hx Ih Ii Il Iq It Iu Jg Jk Jl Jn Jo Jp Jr Js Jt Lh Li Lj Lu Lw Lx Lz Ma Mc Md Me Mf Mg Mh Ml Mj Mk Ml Mm Mp Mq Mr Ms Mt Mv Mw My Mz Na Nb Nf Ng Nk Nm No Nq Nr Oe Of Og Ok On Pa Pd Pe Pf Pg Po Pz Qe) aA(Et Fp Hr Hu Hv Hw Hx Ih Ii Il In Io Iq Ir It Iu Jl Jn Jo Jp Jr Js Jt Lh Li Lj Lu Ly Lz Ma Mc Md Me Mf Mh Mi Mj Mk Ml Mm Mn Mp Mq Mr Ms Mt Mw Mx My Na Nb Nc Ne Nf Ng Ni Nk Nm No Nq Nr Ns Ny Oe Of Og Pd Pe Pf Pg Pz Qa Qe) Qa(Hq Hr Hv Hw Ih Ij Ik Im In Io Iq It Iv Jg Jh Jk Jl Jm Jq Jt Lh Lj Lu Lx Ly Ma Mb Md Mg Mi Ml Mm Mr Mt Mv Mx My Mz Na Nc Nd Ne Nh Ni Nj Nl Nm Nn Nq Ns Nt Nu Nv Nw Nx Ny Og Oh Oi Ok Om On Pa Pb Pe Po Pz Qc) Nv(Et Hq Hr Hw Ij Ik Im In Io Ip Iq Ir Iv Jh Ji Jk Jl Jm Jp Jq Jt Lh Lu Lx Ly Ma Mb Md Mg Mi Ml Mm Mr Mt Mv Mx My Mz Nc Nd Ne Ng Nh Ni Nj Nk Nl Nm Nn Ns Nt Nu Nw Nx Of Og Oh Oi Om On Pa Pb Pc Pe Po Pz Qb Qc) Ip(Hq Hv Ij Ik Il Im In Io Ir Iv Jg Jh Jl Jm Jq Js Lh Lu Lx Mb Mg Mi Mj Mn Mp Mq Mr Mt Mv Mx My Mz Nc Ne Nh Nj Nk Nl Nq Nt Nw Nx Oi Ok On Pa Pb Pc Pe Po Qb Qc Qe) Ji(Fp Hr Hu Hx Ih Ii Il Ir It Iu Jg Jo Jp Jq Jr Js Li Lj Lw Lz Ma Mc Me Mf Mh Mj Mk Mp Mq Ms Mw Mx Mz Na Nb Nf Ng Nj No Nq Nr Nx Oe Of Og Ok Pd Pf Pg Qe) Lv(Hq Hv Ih Ij Ik Im In Io Ir Iv Jg Jh Jk Jl Jm Jp Jq Js Li Lx Mg Mi Ml Mp Mt Mv Mx My Mz Nc Nd Ne Nh Nk Nl Nq Nr Nt Nu Nx Oi Ok On Pa Pb Pc Po Qc Qe) Jq(Hq Hw Ij Ik Im In Io Ir Iv Jg Jh Jk Jl Jm Lu Lx Mb Md Mg Mi Ml Mn Mr Mv Mx My Nc Ne Nh Nk Nl Nn Nt Nu Nw Ny Oh Oi Om On Pa Pb Pc Po Qb Qc Qe) Nw(Hx Ik Im In Io Ir Iv Jh Jk Jl Jm Lh Lx Mg Mh Mi Mm Mn Mv My Nc Nd Ne Nh Nj Nl Nm Nn Nt Nu Nx Ny Of Oh Oi Om Pb Pc Pg Po Pz Qb Qc Qe) Oh(Hq Ik Im In Io Ir Iv Jg Jh Jk Jl Jm Lh Lx Mb Mg Mi Mn Mv Mx Nc Ne Nh Ni Nl Nn Nt Nu Nx Oi Ok Om On Pb Pc Po Qb Qc) Oy(Ik Im Ir Iv Jg Jh Jk Jm Js Lh Lx Mg Mi Mp Mq Mt Mv Mx Mz Nc Ne Nh Nj Nl Nn Nt Nu Nx Oi Ok On Pc Po Qc Qe) Qb(Hw Ih Ij Ik Im In Io Iq Iv Jg Jh Jk Jl Lh Lx Mb Mg Mj Mn Mt Mv Nd Ni Nl Nn Nt Nu Nx Ny Oi Om On Pb Pc) Jl(Hq Hw Ij Ik Im In Io Iv Jg Jh Jk Jm Lx Mb Mg Mn Mv Nd Ni Nl Nn Nu Nx Ny Oi Om On Pb Pc Qc) Oz(Im Ir Iv Jg Jh Jm Js Lh Lx Mg Mi Mp Mt Mv Mx Mz Nt Nu Nx Oi Ok On Pc Po Qc Qe) Nn(Ik Im Ir Iv Jh Jk Jm Lx Mx Nl Nt Nu Nx Ok Po Qc Qe) Jk(Im Io Iv Lx Mn Nl Nu Nx Oi Om Pc Qc) Lx(Ik Im Iv Jh Mn Nl Oi On Pc) On(Im Io Iv Mn Nl Oi Pc) Nu(Jg Jm Mv) Iv(Jg Jh Pc) Oi(Im Po Qc) Pc(Im Po) Mull MvMy NlJg InLh} aA{Oz(Et Fp Fr Hq Hr Hu Hv Hw Hx Ih Ii Ij Ik Il Im Io Ip Iq Ir It Iu Iv Jh Jk Jl Jm Jn Jo Jp Jr Js Jt Lh Li Lj Lu Lw Ly Lz Ma Mb Mc Md Me Mf Mg Mh Mi Mj Mk Ml Mm Mn Mp Mq Mr Ms Mt Mv Mw Mx My Na Nb Nc Nd Ne Nf Ng Nh Ni Nj Nk Nl Nm No Nq Nr Ns Nt Nu Nv Nx Ny Oe Of Og Oh Oi Ok Om On Oy Pa Pb Pd Pf Pg Po Pz Qa Qb Qc Qd Qe) Ji(Et Fp Fr Hq Hu Hv Hx Ik Il Im Io Ip Iq Ir Is It Iu Iv Jg Jh Jk Jl Jn Jp Jq Jr Js Li Lj Lu Lv Lw Lx Ly Lz Ma Mb Mc Md Me Mf Mg Mh Mi Mj Mk Ml Mp Mq Mr Ms Mt Mu Mv Mw Mx My Mz Na Nb Nc Nd Ne Nf Ng Nh Ni Nj Nk Nl Nn No Nq Nr Ns Nt Nu Nv Nw Nx Oe Of Og Oh Oi Ok On Oy Pa Pb Pd Pe Pf Pg Po Pz Qa Qb Qc Qd Qe) Nw(Hr Hw Ih Ii Io Is Jm Jt Lv Mb Ml Mm Mn Mu Mw My Nb Nd Nf Nm Ns Of Og Om Pb Pc Pe Po Pz) In(Fr Im Jg Jq Lh Lw Lx Mg Mz Nn Nt Nu Nv Nx Ok Om Pc Po Qa) Pc(Fr Hr Hw Ip Is Jq Lv Lw Lx Mb Mu Nd Ns Og Om Pe Qd) Is(Hr Hw Ih Ij Il Iu Jm Lv Mb Ny Og Om) Lv(Hr Hv Hw Ij Jo Md Ml Mu Nn Pb) Mu(Hr Hw Mb My Og Om) Qd(Hr Hw Jm Jt Om Uc) Hr(Jq Lw Nn Ok) LwMb MzJs JqOm PePg aNcV jGjQ} Is{In(Fr Hw Il Io Iq Iv Ji Jl Jm Jq Jt Lh Lv Mi Mm Mn Mz Ni Nl Nm Nt Nu Nw Ny Og Ok Om On Oz Pb Pc Pz) Jm(Hw Ij Il Io Ip Iq Ji Jt Lv Mm Mn Nm Nn Nw Nv Ny Og Om Oy Pc Pz) Og(Fr Mn Mu Nn Oz) Il(Fr Oz) NmJi IjNw} Qd{Uc(aF aO aX bC bG bH bM bN bR bX cF cL cN Co cP Ct Di fP Fr Hv fb Il Jg Jh Jk Kc Ms My Nb Ng Ou Tv Uu) fP(aX bM Dl gL Hr Hw Ii Il In Jo Kr Mv Nm Qw Rb Tv Ug Us Tj) Hw(aG Ih bN bX cH cP cT) TjcT} Mu{fR(Mb Uc Ue Ug) Dr(Hb Om) Gn(Hb Om) In(Ji Nw) CpUc EmQv} Ji{Nm(Fr In Oz) Mmln} AwaJdG CpaGdX aCaXgV Unconstrained panels with 3 analytes, where 1.0E-7 >= 'model p-value' > 1.0E-8. Contains 4,079 panels of 14,487,373 total panels evaluated. : Jj{On(Et Fp Hq Hr Hu Hv Hw Hx Ih Ii Ij Ik Il In Iq Ir It Iu Jg Jh Jk Jl Jm Jn Jo Jp Jr Js Jt Lh Li Lj Lu Lw Ly Lz Ma Mb Mc Md Me Mf Mg Mh Mi Mj Mk Ml Mm Mp Mq Mr Ms Mt Mv Mw Mx My Mz Na Nb Nc Nd Ne Nf Ng Nh Ni Nj Nk Nm Nn No Nq Nr Ns Nt Nu Nw Nx Ny Oe Of Og Ok Om Pa Pb Pd Pe Pf Pg Po Pz Qc Qe) Lx(Et Fp Hq Hr Hu Hv Hw Hx Ih Ii Ij In Io Iq Ir It Iu Jg Jm Jn Jo Jp Jr Js Jt Lh Li Lj Lu Lw Ly Lz Ma Mb Mc Md Me Mf Mg Mh Mi Mj Mk Ml Mm Mp Mq Mr Ms Mt Mv Mw Mx My Mz Na Nb Nc Nd Ne Nf Ng Nh Ni Nj Nk Nm No Nq Nr Ns Nt Nu Nx Ny Oe Of Og Ok Om Pa Pb Pd Pe Pf Pg Po Pz Qc Qe) Jk(Et Fp Hq Hr Hu Hv Hw Hx Ih Ii Ij Ik Il In Iq Ir It Iu Jg Jh Jm Jn Jo Jp Jr Js Jt Lh Li Lj Lu Lw Ly Lz Ma Mb Mc Md Me Mf Mg Mh Mi Mj Mk Ml Mm Mp Mq Mr Ms Mt Mv Mw My Mz Na Nb Nc Nd Ne Nf Ng Nh Ni Nj Nk Nm No Nq Nr Ns Nt Ny Oe Of Og Ok Om Pa Pb Pd Pe Pf Pg Po Pz Qe) Po(Hq Hr Hv Hw Ih Ii Ij Ik Il Im In Io Iq Ir Iv Jg Jh Jl Jm Jn Jo Jp Jr Js Lh Lj Lu Lw Ly Lz Ma Mb Md Mg Mh Mi Mj Ml Mn Mp Mq Mr Mt Mv Mx My Mz Na Nb Nc Nd Ne Nf Nh Ni Nj Nk Nl Nq Nr Ns Nt Nu Nx Ny Og Ok Om Pa Pb Pd Pe Pf Pg Qb Qc Qe) Jl(Et Fp Hr Hu Hv Hx Ih Ii Il Iq Ir It Iu Jn Jo Jp Jr Js Jt Lh Li Lj Lu Lw Ly Lz Ma Mc Md Me Mf Mh Mi Mj Mk Ml Mm Mp Mq Mr Ms Mt Mw Mx My Mz Na Nb Nc Ne Nf Ng Nh Nj Nk Nm No Nq Nr Ns Nt Oe Of Og Ok Pa Pd Pe Pf Pg Pz Qe) Nn(Et Fp Hq Hr Hu Hv Hw Ih Ii Ij Il In Io Iq It Jg Jn Jo Jp Jr Js Jt Lh Li Lj Lu Lw Ly Lz Ma Mb Mc Md Me Mg Mh Mi Mj Mk Ml Mn Mp Mq Mr Mt Mv Mw My Mz Nb Nc Nd Ne Nf Nh Ni Nj Nk No Nq Oi Om Pa Pb Pc Pd Pe Pg) Qb(Et Fp Hq Hr Hu Hv Hx Ii Il Ir It Iu Jm Jn Jo Jp Js Jt Li Lj Lu Lw Ly Lz Ma Mc Md Me Mf Mh Mj Mk Ml Mm Mp Mq Mr Ms Mw Mx My Mz Na Nb Nc Ne Nf Ng Nh Nj Nk Nm No Nq Nr Ns Oe Of Og Ok Pa Pd Pe Pf Pg Pz Qa Qc Qe) Oy(Et Fp Hq Hr Hu Hv Hw Hx Ih Ii Ij Il In Io Iq It Iu Jn Jo Jp Jr Jt Li Lj Lu Lw Ly Lz Ma Mb Mc Md Me Mf Mh Mj Mk Ml Mm Mn Mr Ms Mw My Na Nb Nd Nf Ng Ni Nk Nm No Nq Nr Ns Ny Oe Of Og Om Oz Pa Pb Pd Pe Pf Pg Pz) Jg(Fp Hq Hv Hw Ih Ij Ik Im In Io Ir Jh Jm Jn Jp Jr Js Lh Li Lu Ly Lz Ma Mb Md Me Mg Mi Mj Ml Mn Mp Mq Mr Mt Mv Mx My Mz Nc Nd Ne Ng Nh Ni Nj Nk Nr Ns Nt Nv Nw Nx Ny Of Og Oi Ok Om Pa Pb Pc Pd Pe Pg Qc Qe) Oh(Et Fp Hr Hu Hv Hw Hx Ih Ii Ij Il Iq It Iu Jn Jo Jp Jr Js Jt Li Lj Lu Lw Ly Lz Ma Mc Md Me Mf Mh Mj Mk Ml Mm Mp Mq Mr Ms Mt Mw My Mz Na Nb Nd Nf Ng Nj Nk Nm No Nq Nr Ns Ny Oe Of Og Pa Pd Pe Pf Pg Pz Qe) Iv(Et Fp Hq Hv Ih Ii Ij Ik Im In Io Ir Jm Jn Jo Jp Js Lh Li Lu Lw Ly Ma Mb Mg Mi Mj Ml Mn Mp Mq Mr Mt Mv Mx My Mz Nb Nc Nd Ne Nh Ni Nj Nk Nl Nq Nr Ns Nt Nu Nx Og Oi Ok Pa Pb Pd Pe Pg Qc Qe) Jq(Et Fp Hr Hu Hv Hx Ih Ii Il Iq It Iu Jn Jo Jp Jr Js Jt Lh Li Lj Lw Ly Lz Ma Mc Me Mf Mh Mj Mk Mm Mp Mq Ms Mt Mw Mz Na Nb Nd Nf Ng Ni Nj Nm No Nq Nr Ns Nx Oe Of Og Ok Pd Pe Pf Pg Pz) Nw(Et Fp Hq Hr Hu Hv Hw Ih Ii Il Iq It Iu Jn Jo Jp Jr Js Jt Li Lj Lu Lw Ly Lz Ma Mb Mc Me Mf Mj Mk Mp Mq Mr Ms Mt Mv Mw Mx Mz Na Nb Nf Ng Ni Nk No Nq Nr Ns Oe Og Ok Pa Pd Pe Pf) Lv(Et Fp Hr Hu Hv Hx Ii Il Iq It Iu Jn Jo Jr Jt Lh Lj Lu Lw Ly Lz Ma Mb Mc Md Me Mf Mh Mj Mk Mm Mn Mq Mr Ms Mw Na Nb Nf Ng Ni Nj Nm No Ns Ny Oe Of Og Om Pd Pe Pf Pg Pz) Mv(Hq Hv Hw Ih Ii Ij Ik Im In Io Ir Jh Jm Jp Js Lh Lu Lw Ly Mb Md Mg Mi Mj Ml Mn Mp Mq Mr Mt Mx Mz Nc Nd Ne Nh Ni Nj Nk Nl Ns Nt Nx Oi Ok Om Pa Pb Pc Pd Pe Pg Qc Qe) Jh(Fp Hq Hv Ih Ii Ik Im Io Ir Jm Jo Jp Js Lh Li Ly Mb Mg Mi Mj Mn Mp Mq Mr Mt Mx My Mz Nc Nd Ne Nh Ni Nj Nk Nl Nq Nr Nt Nu Nx Oi Ok Om Pa Pb Pc Pd Pe Pg Qc Qe) Ip(Et Fp Hr Hu Hw Hx Ih Ii Iq It Iu Jn Jo Jp Jr Jt Li Lj Lw Ly Lz Ma Mc Md Me Mf Mh Mk Ml Mm Ms Mw Na Nb Nd Nf Ng Ni Nm No Nr Ns Ny Oe Of Og Om Pd Pf Pg Pz) Jm(Hq Hv Hw Ij Ik Il

Figure 5 Continued

Im In Io Ir Jn Jp Js Lh Lu Ly Ma Mb Mg Mi Mj Mn Mp Mq Mr Mt Mx My Mz Nc Nd Ne Nh Ni Nj Nk Nl Nq Nt Nx Og Oi Ok Om Pa Pb Pc Pe Pg Qc Qe) Im(Hq Ii Ik In Io Ir Jo Jp Js Lh Li Lw Ly Mb Mg Mi Mj Mn Mp Mq Mr Mt Mx My Mz Nc Nd Ne Nh Ni Nj Nl Nr Nt Nu Nx Ok Pa Pb Pd Pe Pg Qc Qe) Oz(Et Fp Hq Hv Ih Ii Ij Ik Il In Io It Jn Jo Jp Jr Jt Li Lu Lw Ly Ma Mb Mj Mm Mq Mr Mw My Nb Nc Nd Ne Nh Ni Nj Nk Nl Nq Nr Om Pa Pe Pg) Qc(Hq Hv Hw Ij Ik Il In Io Ir Lh Lu Ly Mb Mg Mi Mj Mn Mp Mq Mr Mt Mx My Mz Nc Nd Ne Nh Ni Nj Nk Nl Nq Nt Nu Nx Ok Om Pa Pb Pc Pe Qe) Nu(Hq Hv Ih Ii Ik In Io Ir Jp Js Lh Li Ma Mb Mg Mi Mj Mp Mq Mr Mt Mx My Mz Nc Nd Ne Nh Nk Nl Nq Nr Nt Nx Oi Ok Pa Pb Pc Pg Qe) Nx(Hq Hv Ih Ik Il In Io Ir Jp Js Lh Li Lu Mg Mi Mj Mn Mp Mq Mr Mt Mx My Mz Nc Ne Nh Ni Nk Nl Nq Nr Nt Oi Ok Pa Pb Pc Pe Qe) Nv(Fp Hu Hv Hx Ih Ii Il It Iu Jn Jo Jr Js Li Lj Lw Lz Mc Me Mf Mh Mj Mk Mp Mq Ms Mw Na Nb Nf No Nq Nr Oe Ok Pd Pf Pg Qe) Oi(Hq Hv Ih Ii Ik In Ir Jo Jp Js Lh Li Mg Mi Mj Mp Mq Mr Mt Mx My Mz Nc Ne Nh Ni Nj Nl Nq Nr Nt Og Ok Pa Pb Pc Pe Pg Qe) Nt(Hq Hv Ih Ij Ik In Io Ir Jp Js Lh Mb Mg Mi Mj Mn Mp Mq Mt Mx My Mz Nc Nd Ne Nh Ni Nj Nk Nl Ns Ok Pa Pb Pc Pg Qc) Qa(Et Fp Hu Hx Ii Il Ir Iu Jn Jo Jp Jr Js Li Lw Lz Mc Me Mf Mh Mj Mk Mr Ms Mw Nb Nf Ng Nk No Nr Oe Of Pd Pf Pg Qe) Qd(Ad aG aH aM aO aX Ba bB bG bM bN bR bX cC cE cF cG cJ cP Cs cW cZ dF DG dH dJ dK dL Qw Tv Uc Ug Uh Us) Qe(Hq Hw Ij Ik In Io Ir Lh Ly Mb Mg Mi Mn Mp Mt Mx My Mz Nc Nd Ne Nh Ni Nj Nl Nq Ny Ok Om Pa Pb Pc) Nl(Hq Ih Ii Ik Ir Jo Jp Js Lh Li Mg Mi Mj Mp Mq Mr Mt Mx My Mz Nd Ni Nq Ok Pa Pb Pc Pe Pg) Pc(Hq Ih Ii Ik Ir Jp Js Lh Li Mg Mi Mj Mp Mq Mr Mt Mx My Mz Nc Ne Nh Ni Nr Ok Pa Pb) Ok(Hr Hv Hw Ij Ik In Io Ir Mb Md Mg Mi Ml Mn Mp Mx Na Nc Ne Nh Nm Pa Pb) Ik(Hq Hv In Ir Jp Js Lh Li Mg Mi Mj Mp Mt Mx My Mz Nc Nd Nq Pa Pe) Mi(Ih Ir Jp Mb Mg Ml Mp Mq Mt Mz Nc Nd Ne Nh Nj Pa Pb) Ir(Hq In Io Lh Mg Mn Mp Mq Mt Mx My Mz Nc Nq Pa Pb) Lh(Hr Ij Mb Md Mg Ml Mp Mt Mz Nc Nd Ne Nh Nj Pb) Mp(Mb Mg Mn Mt Mx Nc Nd Ne Nh Ni Nj Pb) Mg(Js Mt Mx Mz Nc Ne Nh Pa) Nc(Mr My Mz Ni) Wm(Fr Is Mu) Pb(Js Mx Mz) MxHq PePg} aA{Mu(Et Fp Fr Hq Hu Hv Hx Ih Ii Ij Ik Il Im Io Ip Iq Ir Is It Iu Iv Jg Jh Jk Jl Jm Jn Jo Jp Jq Js Jt Lh Li Lj Lu Lw Lx Ly Lz Ma Mc Md Me Mf Mg Mh Mi Mj Mk Ml Mm Mn Mp Mq Mr Ms Mt Mv Mw Mx Mz Na Nb Nc Nd Ne Nf Ng Nh Ni Nj Nk Nl Nm Nn No Nq Nr Ns Nt Nu Nv Nx Ny Oe Of Oh Oi Ok On Pa Pb Pd Pe Pf Pg Po Pz Qa Qc Qd Uc) Lv(Et Fp Fr Hq Hu Hv Hx Ih Ii Ik Il Im Io Ip Iq Ir It Iu Iv Jg Jh Jk Jl Jm Jn Jp Jq Jr Js Jt Lh Li Lj Lu Lv Lx Ly Lz Ma Mb Mc Me Mf Mg Mh Mi Mj Mk Mm Mn Mp Mq Mr Ms Mt Mv Mw Mx My Mz Na Nb Nc Nd Ne Nf Ng Nh Ni Nj Nk Nl Nm No Nq Nr Ns Nt Nu Nv Nx Ny Oe Of Og Oh Oi Ok Om On Oy Pa Pd Pe Pf Pg Po Pz Qa Qb Qc Qd Qe) Is(Et Fp Fr Hq Hu Hv Hx Ii Ik Im Io Ip Iq Ir It Iv Jg Jh Jk Jl Jn Jo Jp Jq Jr Js Jt Lh Li Lj Lu Lw Lx Ly Lz Ma Mc Md Me Mf Mg Mh Mi Mj Mk Ml Mm Mn Mp Mq Mr Ms Mt Mv Mw Mx My Mz Na Nb Nc Nd Ne Nf Ng Nh Ni Nj Nk Nl Nm Nn No Nq Nr Ns Nt Nu Nv Nx Oe Of Oh Oi Ok On Oy Pa Pb Pd Pe Pf Pg Po Pz Qa Qb Qc Qd Qe) Pc(Et Fp Hq Hu Hv Hx Ih Ii Ij Ik Il Im Io Iq Ir It Iu Iv Jg Jh Jk Jl Jm Jn Jo Jp Jr Js Jt Lh Li Lj Lu Ly Lz Ma Mc Md Me Mf Mg Mh Mi Mj Mk Ml Mm Mn Mp Mq Mr Ms Mt Mv Mw Mx My Mz Na Nb Nc Ne Nf Ng Nh Ni Nj Nk Nl Nm Nn No Nq Nr Nt Nu Nv Nx Ny Oe Of Oh Oi Ok On Oy Pa Pb Pd Pf Pg Po Pz Qa Qb Qc Qe) Nw(Et Fp Fr Hq Hu Hv Hx Ik Il Im Ip Iq Ir It Iu Iv Jg Jh Jk Jl Jn Jo Jp Jq Jr Js Li Lj Lu Lw Lx Ly Lz Ma Mc Me Mf Mg Mh Mi Mj Mk Mp Mq Mr Ms Mt Mv Mx Mz Na Nc Ne Ng Nh Ni Nj Nk Nl Nn No Nq Nr Nt Nu Nv Nx Oe Oh Oi Ok On Oy Pa Pd Pf Qa Qb Qc Qd Qe) Qd(fP Fr Hq Hu Hv Hx Ih Ii Ij Ik Il Im Io Ip Iq Ir It Iu Jg Jh Jk Jl Jo Jq Js Lh Lj Lw Lx Lz Ma Mb Mc Md Mg Mi Mk Ml Mm Mn Mr Mv Mw Mz Na Nd Ne Nf Ng Nh Ni Nj Nl Nm Nn No Nr Ns Nu Nx Ny Oe Of Og Oi Oy Pb Pd Pe Pf Pg Po Pz Qa Qb Qe Tj) In(Et Fp Hq Hr Hv Hw Hx Ii Ij Ik Io Ip Ir Iv Jh Jk Jl Jo Jp Jr Js Jt Li Ly Ma Mb Mh Mi Mj Mn Mp Mq Mr Mt Mv Mw Mx Nb Nc Nd Ne Nh Ni Nj Nl Nq Nr Ns Ny Og Oh Oi On Oy Pa Pb Pd Pe Pg Qb Qc Qe) Fr(Hq Hr Hw Ii Ij Il Im Io Ip Iq Iu Jm Jo Jq Lh Lw Lx Mb Mg Mi Mn Mr Mw Mz Nd Nf Ng Ni Nj Nl Nm Nn Nr Ns Nu Nx Ny Of Og Om Oy Pb Pe Pg Po) Nn(Hw Ii Ij Il Ip Iq Iu Jm Jq Lw Lx Mb Md Mk Mn Mq My Mz Nd Ne Nf Ng Nh Ni Nj Nl Ns Nu Nx Ny Of Og Ok Om Oy Pb Pe) Lx(Hr Hw Ih Ii Ij Io Ip Iq Iu Jg Jm Jq Jt Lh Lw Mb Mg Mm Mn Mw Nd Ng Ni Nj Nm Nr Ns Nx Ny Of Og Om Pb Pe Pz) Hr(Fp Hq Hw Ik Im Ip Jg Jh Jk Li Mb Mg Mq Mv Mz Nd Ni Nj Nl Ns Nu Nv Nx Oi Om On Oy Pa Pb Po Qc) Jq(Hv Hw Ii Ij Io Ip Iq Ir It Jg Jm Jo Js Jt Lh Mb Md Mg Ml Mn Nd Nf Nj Nl Nm Ns Ny Of Og Pb) Mb(Hw Ij Im Ip Jg Jh Jp Lz Mc Mg Ml Mv Mz Nd Ng Ns Nu Nv Nx Og Ok Om Pb Pe Qc) Jg(Hw Ii Ij Il Ip Jm Jt Lw Md Mg Mn My Nd Ng Nj Ns Ny Of Og Om Oy Pb) Lw(Hv Hw Ij Ip Ir It Jo Jt Md Ml Na Nd Nf Nj Nm Nx Og Om Pb Pd) Hw(Hq Im Ip Jh Mg Mq Mv Mz Nd Nj Nu Nv Nx Oi Ok On Pb Po Qc) Nd(Hq Ij Im Ip Jh Mg Mp Mv Mz Nq Nv Nx Og Oy Pa Pb Po) cV(aC An AW aX BA cF cH cI cN cT Di dN) Ok(Hv Ij Ir Jo Jt Md Ml Nf Nm Pb) Om(Ij Ip Jh Mg Mz Nv Nx Pb Po Qc) jG(cD jO jR jT jV lL lM mZ nR nU) Nx(Ij Il Jm Ng Ny Og Pb) Pb(Ij Ip Mz Nj Og Pe) Mg(Ij Iu Jm Ng Og) Ip(Ij Jm Nj Og) Mv(My Og Oy) Nv(Jm Lh Ny) Pe(Oy Pa Pd) Mz(Nf Nj) PoJm NiIj OgOi aCbE aJdG aNcZ} Qd{Uc(aC AD aE Af aG aH aI AJ aK AL aM AN Ao AP aQ AR AS aU aV aW Ax aY aZ BB Bc bE bF bI bJ bL Bn BO bP bQ bS bU bV bW bZ cA cB cC cD cE cG CH cI cJ cK cM cO CQ cR CS CU CV CW CX cY cZ dA DB DC DD DE dF DG dH dI dJ DK DL dM dN Dp Ed Et Ez Fa Fb Fn Fp Fw Gl Gp Ha Hb Hf Hq Hr Hu Hw Hx Ic Id Ih Ii Ij Ik Im In Io Ip Iq Ir Is It Iu Iv Iz Jd Je Jf Ji Jl Jm Jn Jo Jp Jq Jr Js Jt Ju Jv Jy Kd Ke Kf Kg Ki Kj Kk Kl Kn Ko Kp Kq Kr Ks Kx Ky Kz Ld Lh Li Lj Lu Lv Lw Lx Ly Lz Ma Mb Mc Md Me Mf Mg Mh Mi Mj Mk Ml Mm Mn Mp Mq Mr Mt Mw Mx Mz Na Nc Nd Ne Nf Nh Ni Nj Nk Nl Nm Nn No Nq Nr Ns Nt Nu Nv Nw Nx Ny Oa Oe Of Og Oh Oi Ok Om On Or Ow Oy Oz Pa Pb Pc Pd Pe Pf Pg Ph Pi Pj Pk Po Pz Qa Qb Qc Qe Qg Qh Ql Qm Qn Qt Qu Qv Qw Qx Qy Qz Ra Rb Rc Rf Rg Rh Ri Rj Rm Sr Ss St Tn To Tr Tt Tz Ua Ub Ud Ue Uf Ug Uh Uk Ul Um Un Uo Up Ur Us Ut Uv Vo Vp Vt Vv Wm Tj) fP(aC AD aE AF aG aH aI AJ aK aL aM aN AO aP aQ AR AS aU aV AW Ax aY aZ bA BB bC bE bF BG bH bI bJ bL BN bO bP bQ bR bS bU bV bW bX bZ cA cB cC cD cE cF cG CH cI cJ cK cL cM cN cO CP CQ cR CS cT CU CV CW CX cY cZ dA DB DC DD dE dF DG dH DI dJ DK dL dM dN eC Ed Ef Et Fa Fn Fp Fr Fw Gp Ha Hc Hf hG Hq Hu Hv Hx iA Ic Id IH Ij Ik Im Iq Ir Is It Iu Iv Iz Jf Jg Jh Ji Jk Jl Jm Jn Jp Jq Jr Js Jt Ju Jv Kc Kd Ke Kf Ki Kj Kk Kl Kn Ko Kp KQ Ks Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mu Mw Mx My Mz Na Nb Nc Nd Ne Nf Ng Nh Ni Nj Nk Nl Nn No Nq Nr Ns Nt Nv Nw Nx Ny Oa Oe Of Og Oh Oi Ok Om On Or Oy Oz Pa Pb Pc Pd Pe PF Pg Ph Pi Po Pz Qa Qb Qc Qe Qg Ql Qm Qn Qv Qx Qy Qz Ra Rc Rg Rh Rj Rm Sr Ss Tn Tr Tt Tz Ua Ub Ud Ue Uf Uh Uk Ul Um Un Uo Up Ur Uu Uv Vo Vp Vt Vv Wm) Hw(aC aD aE aF aH aI aJ aK aL aM aN aO aP aQ aR aS aU aV AW aX aY aZ BA bB BC bE bF BG bH bI bJ bL bM BO bP bQ bR bS bU bV bW bZ cA cB cC cD cE cF cG cI cJ cK cL cM cN CO Cp cQ cR cS cU cV cW cX cY cZ dA dB dC dD dE dF DG dH DI dJ DK DL dM dN Ex Hc Ks Pk Qw Ra Tv Ug Vo) Tj(bA bN cP Dg Il Iu Qw Ug) In(Ik Il Im Is Ji Mu Nw Wm) Il(Fr iA Is It Oz) Pz(Fr Is Ji Mu) Ji(Jt Mm Nm) Mu(Jm Ng) Ir(Dg Ug) Uk(Ef Ld) EdUg IsJm UscT} Is{Jm(Et Fp Hq Hr Hu Hv Hx Ih Ii Ik Im Ir It Iu Iv Jg Jh Jk Jl Jn Jo Jp Jq Jr Js Lh Li Lj Lu Lw Lx Ly Lz Ma Mb Mc Md Me Mf Mg Mh Mi Mj Mk Ml Mp Mq Mr Ms Mt Mv Mw Mx My Mz Na Nb Nc Nd Ne Nf Ng Nh Ni Nj Nk Nl No Nq Nr Ns Nt Nu Nv Nx Oe Of Oh Oi Ok On Pa Pb Pd Pe Pf Pg Po Qa Qb Qc Qe) In(Et Fp Hq Hr Hu Hv Hx Ih Ii Ij Ik Im Ip Ir It Iu Jg Jh Jk Jn Jo Jp Jr Js Li Lj Lu Lw Lx Ly Lz Ma Mb Mc Md Me Mf Mg Mh Mj Mk Ml Mp Mq Mr Ms Mt Mv Mw Mx My Na Nb Nc Nd Ne Nf Ng Nh Nj Nk Nn No Nq Nr Ns Nv Nx Oe Of Oh Oi Oy Pa Pd Pe Pf Pg Po Qa Qb Qc Qe) Og(Hw Ih Ii Ij Il Im Io Ip Iq It Iu Jg Jh Ji Jl Jn Jt Lh Lu Lv Mb Mm Mv Nd Ng Ni Nm Nw Ny Oi Om On Oy Pb Pc Pz) Il(Hw Io Iq Iu Ji Jl Jt Lv Mm Mn Mu Ng Nm Nn Nw Ny Om On Pa Pb Pc Pz) Oz(Fr Hr Hw Ii Ij It Iu Ji Jt Lv Mn Mu Ng Ni Nm Nw Pc Pz) Mu(Hr Hw Ii Ij Jo Jt Mg Mn My Ng Nm Ny Om Oy Pz Uc) Fr(Hr Hw Ii Ij Iq Jt Mg Mn Ng Nm Ny Of Om Oy Pz) Hw(Ij Io Iu Ji Lv Mn Ni Nm Nw Pz) Lv(Ij Io Jo Jt Mn Ng Nm Pz) Ji(Ii Ij Jt Lh Mm Mn Ny Pz) Nw(Jt Md Mn My Nm Ny Pb Pz) Ni(Ij It) PzPc} Ji{Nm(Hr Hw Ij Il Io Ip Iv Jh Jl Jm Lh Lu Lv Lx Mb Md Ml Mm Mn Mu Mv Ni Nn Nw Nx Ny Og Oh Om Oy Pb Pc Qa) In(Et Fr Hw Ij Io Ip Iv Jl Jt Lh Lv Mi Mn Mv Ng

Figure 5 Continued

Ni Nn Nt Nw Ny Og Om Oy Oz Pc Pz Qa) Mu(Ij Jm Jo Jt Lh Mg Mm Mn Ng Ny Og Om Pz) Oz(Ij Il Jm Jo Jt Lh Mm Mn Ng Og Pb Pz) Fr(Jg Jm Jt Lh Mm Mn Ng Ny Og Pz) Mm(Hw Il Jm Mn Og Om Pc) Mn(Ng Og) MdNw} Mu{Uc(bA bF cT Hq It Jg Kc Lh Mj Pg St Tn Uk Un Tj) fR(Hr In Jo Jt Nf Nm Om Pb Pd Ur) Pg(aC aG aH aN bN cH dJ fP Qw) Gn(aG Cw Dg Et Kf Kl) Nw(Ij Md My Og Pb) Dr(Aa aG Cw Et) Gc(bR Cw Et Om) In(Iv Jq Lv Qa) Em(aG Iz Om) aH(eM gC) DkUk TjfP} Nw{Md(Fr Hr Hw In Jh Jt Lj Lv Mn Mv Ni Nm Nn Ny Oz Pc Pz) In(Fr Im Iv Lv Mi Mn Mv Nt Nu Oz Pc Qa) Ij(Lv Oz) MiPg MvMy OzPb} aJ{dG(aX Ba cH cL cN Cp Di dN)} Mv{eM(Oz Pb) UefR} CpaGeP DrMyHb EfJtmH NcnUjH luqZjQ

Figure 5 Continued

Ma Mb Mc Md Me Mf Mh Mk Ml Mm Mn Mq Mr Ms Mw Na Nb Nf Ng Ni Nj Nk Nm No Nr Ns Ny Oe Of Og Om Pb Pd Pf Pg Pz) Ir(Et Fp Hr Hu Hv Hw Hx Ih Ij Il Iq It Iu Jn Jo Jr Jt Lj Lu Lw Ly Lz Ma Mb Mc Md Me Mf Mh Mj Mk Ml Mm Mr Ms Mw Na Nb Nd Nf Ng Ni Nj Nk Nm No Nr Ns Ny Oe Of Og Om Pd Pe Pf Pg Pz) Pc(Et Fp Hr Hu Hv Hw Hx Ij Il In Io Iq It Iu Jn Jo Jr Jt Lj Lu Lw Ly Lz Ma Mb Mc Md Me Mf Mh Mk Ml Mm Mn Ms Mw Na Nb Nd Nf Ng Nj Nk Nm No Nq Ns Ny Oe Of Og Om Pd Pe Pf Pg Pz) Nl(Et Fp Hr Hu Hv Hw Hx Ij Il In Io Iq It Iu Jn Jr Jt Lj Lu Lw Ly Lz Ma Mb Mc Md Me Mf Mh Mk Ml Mm Mn Ms Mw Na Nb Nf Ng Nj Nk Nm No Nr Ns Ny Oe Of Og Om Pd Pf Pz) Ok(Et Fp Hq Hu Hx Ih Il Iq It Iu Jn Jo Jr Jt Lj Lu Lw Ly Lz Ma Mc Me Mf Mh Mj Mk Mm Mq Mr Ms Mw My Nb Nd Nf Ng Ni Nj Nk No Nq Nr Ns Ny Oe Of Og Om Pd Pe Pf Pg Pz) Pa(Et Fp Hq Hr Hu Hv Hw Ih Ij In Io It Jn Jo Jr Jt Lu Lw Ly Lz Ma Mb Md Me Mf Mh Mj Mk Ml Mm Mn Mq Mr Mw My Nb Nd Ng Ni Nj Nk No Nq Nr Ns Og Om Pb Pd Pe Pf Pg) Mj(Et Fp Hq Hr Hu Hv Hw Ih Ij Il In Io Jn Jo Jr Jt Lj Lu Lw Ly Lz Ma Mb Md Me Mh Ml Mm Mn Mq Mr Mw My Na Nb Nd Ng Ni Nj Nk Nq Nr Ns Og Om Pb Pd Pe Pg Qe) Nu(Et Fp Hr Hu Hw Hx Ij Il Iq It Iu Jn Jo Jr Jt Lj Lu Lw Ly Lz Mc Md Me Mf Mh Mk Ml Mm Mn Ms Mw Na Nb Nf Ng Ni Nj Nm No Ns Ny Oe Of Og Om Pd Pe Pf Pz) Qe(Et Fp Hr Hu Hv Hx Ih Il Iq It Iu Jn Jo Jr Jt Lj Lu Lw Lz Ma Mc Md Me Mf Mh Mk Ml Mm Ms Mw Na Nb Nf Ng Nk Nm No Nq Ns Ny Oe Of Og Om Pf Pz) Pb(Et Fp Hq Hr Hv Hx Ih Ij Il In Io It Jn Jo Jr Jt Lu Lw Ly Lz Ma Mb Mc Md Me Mf Mh Mk Ml Mm Mn Ms Mw Na Nb Nd Nf Ng Nk Nm No Nr Ns Oe Of Og Pd Pe Pf Pg Pz) Oi(Et Fp Hr Hu Hw Hx Ij Il Io Iq It Iu Jn Jr Jt Lj Lu Lw Ly Lz Ma Mb Mc Md Me Mf Mh Mk Ml Mm Mn Ms Mw Na Nb Nd Nf Ng Nk Nm No Ns Ny Oe Of Om Pd Pf Pz) Nt(Et Fp Hr Hu Hw Hx Il Iq It Iu Jn Jo Jr Jt Lj Lu Lw Ly Lz Ma Mc Md Me Mf Mh Mk Ml Mm Mr Ms Mw Na Nb Nf Ng Nm No Nq Nr Ny Oe Of Og Om Pd Pe Pf Pz) Nx(Et Fp Hr Hu Hw Hx Ij Iq It Iu Jn Jo Jr Jt Lj Lw Ly Lz Ma Mb Mc Md Me Mf Mh Mk Ml Mm Ms Mw Na Nb Nd Nf Ng Nj Nm No Ns Ny Oe Of Og Om Pd Pf Pg Pz) Im(Et Fp Hr Hu Hv Hw Hx Ih Ij Il Iq It Iu Jn Jr Jt Lj Lu Lz Ma Mc Md Me Mf Mh Mk Ml Mm Ms Mw Na Nb Nf Ng Nk Nm No Nq Ns Ny Oe Of Og Om Pf Pz) Pb(Et Fp Hq Hr Hv Hx Ih Ij Il In Io It Jn Jo Jr Jt Lu Lw Ly Lz Ma Mb Mh Mk Mm Mn Mq Mr Mw My Nb Nd Ni Nj Nk No Nq Nr Ns Og Om Oz Pd Pe Pg) Qc(Et Fp Hr Hu Hx Ih Iq It Iu Jn Jo Jr Jt Lj Lw Lz Ma Mc Md Me Mf Mh Mk Ml Mm Ms Mw Na Nb Nf Ng Nm No Nr Ns Ny Oe Of Og Pd Pf Pg Pz) Jh(Et Hr Hu Hw Hx Ij Il In Iq It Iu Jn Jr Jt Lj Lu Lw Lz Ma Mc Md Me Mf Mh Mk Ml Mm Ms Mw Na Nb Nf Ng Nm No Ns Ny Oe Of Og Pf Pz) Jm(Et Fp Hr Hu Hx Ih Iq It Iu Jo Jr Jt Lj Lw Lz Mc Md Me Mf Mh Mk Ml Mm Ms Mw Na Nb Nf Ng Nm No Nr Ns Ny Oe Of Pd Pf Pz) Mv(Et Fp Hr Hu Hx Il Iq It Iu Jn Jo Jr Jt Lj Lz Ma Mc Me Mf Mh Mk Mm Ms Mw Na Nb Nf Ng Nm No Nq Ny Oe Of Og Pf Pz) Mr(Et Fp Hq Hr Hv Hw Ih Ij In Io Jn Jo Jr Jt Lu Lw Ly Ma Mb Ml Mm Mn Mq Mw My Nb Nd Ni Nj Nk Nq Nr Ns Om Pd Pe Pg) Hq(Et Fp Hr Hv Hw Ih Ij Il In Io Jn Jo Jr Jt Lu Lw Ly Ma Mb Mn Mq Mw My Nb Nd Ni Nj Nk Nq Nr Om Pd Pe Pg) My(Et Fp Hv Hw Ih Ij In Io Jn Jo Jr Lu Lw Ly Lz Ma Mb Mn Mq Nb Nd Ni Nj Nk Nq Nr Ns Og Om Pd Pe Pg) Iv(Hr Hu Hw Hx Il Iq It Iu Jr Jt Lj Lz Mc Md Me Mf Mh Mk Mm Ms Mw Na Nf Ng Nm No Ny Oe Of Om Pf Pz) Oz(Hr Hu Hw Hx Iq Iu Lj Lz Mc Md Me Mf Mh Mk Ml Mn Ms Na Nf Ng Nm No Ns Ny Oe Of Og Pd Pf Pz) Mq(Et Fp Hv Hw Ih Ij In Io Jn Jo Jr Lu Lw Ly Lz Ma Mb Mn Nd Ni Nj Nk Nq Nr Ns Om Pd Pe Pg) Jg(Et Hr Hu Hx Il Iq It Iu Jo Jt Lj Lw Mc Mf Mh Mk Mm Ms Mw Na Nb Nf Nm No Nq Oe Pf Pz) Nr(Et Fp Hv Hw Ih Ij In Io Jn Jo Lu Lw Ly Ma Mb Mn Nb Nd Ni Nj Nk Nq Ns Om Pd Pe Pg) Nq(Et Fp Hv Ih Ij In Io Jn Jo Jr Lw Ly Ma Mb Md Ml Mn Mw Nd Ni Nj Nk Pd Pe Pg) Pg(Et Fp Hv Hw Ih Ij In Io Jn Jo Jr Lu Lw Ly Ma Mb Mn Nb Nd Ni Nj Nk Ns Om) Pe(Et Fp Hr Hv Hw Ih Ij In Io Jo Lu Lw Ly Ma Mb Ml Mn Nd Ni Nj Nk Pd) Po(Et Fp Hu Hx It Iu Jt Mc Me Mf Mk Mm Ms Mw Ng Nm No Oe Of Pf Pz) Nj(Et Fp Hv Ih Ij In Io Jn Jo Jr Jt Lu Lw Ly Ma Mw Nb Nd Ni Pd) Ih(Et Fp Hv In Io Jn Jo Lu Lw Ly Ma Mb Mn Nb Nd Ni Nk Om Pd) Jo(Fp Hv Hw Ij In Io Lu Ly Mb Ml Mn Nd Ni Nk Om Pd) Et(Fp Hv In Io Lu Ly Mb Mn Nd Ni Nk Om Pd) Nn(Hx Iu Mf Mm Ms Na Ng Nm Ny Oe Of Pf Pz) Mb(Hv Jn Jt Lv Ma Mc Nb Nd Ni Om Pd) jG(Fr Is Jl Jq Nk Nv Nw Om On) Fp(In Io Lw Mn Ni Pd) Wm(Ji Nd Nw Oy) Mu(aG cH Em fR) Ni(Hv Ma Nk Pd) In(Jt Nb Om Pd) Ml(Hx Jt Om) Is(cH cV Us) Ly(Ma Nk) Hv(Lw Pd) Ij(Jt Om) Lxl1 MdOm NbNd NkPd HwJt StaX] Is[Il(Et Fp Hq Hr Hu Hv Hx Ih Ii Ij Ik Im Ip Ir It Iv Jg Jh Jk Jn Jo Jp Jq Jr Js Lh Li Lj Lu Lw Lx Ly Lz Ma Mb Mc Md Me Mf Mg Mh Mi Mj Mk Ml Mp Mq Mr Ms Mt Mv Mw Mx My Mz Na Nb Nc Nd Ne Nf Nh Ni Nj Nk Nl No Nq Nr Ns Nt Nu Nv Nx Oe Of Oh Oi Ok Oy Pd Pe Pf Pg Po Qa Qb Qc Qe) Hw(Et Hq Hr Hu Hv Ih Ii Ik Im Ip Iq It Iv Jg Jh Jk Jl Jn Jo Jp Jq Js Jt Lh Li Lj Lu Lw Lx Ma Mb Md Mf Mg Mh Mi Ml Mm Mp Mq Mr Ms Mt Mv Mw Mx My Mz Na Nb Nc Nd Ne Nf Ng Nh Nj Nk Nl Nn Ns Nt Nu Nv Ny Oe Of Oh Oi Ok Om On Oy Pa Pb Pc Pe Pf Qb Qc Qd) Oz(Et Fp Hq Hu Hv Ih Ik Im Io Ip Iq Ir Iv Jg Jh Jk Jl Jn Jo Jp Jq Js Lh Li Lj Lu Lw Lx Lz Ma Mb Md Mf Mg Mh Mi Mj Ml Mm Mp Mr Ms Mt Mv Mw Mx My Mz Na Nc Nd Nf Nj Nl Nn Nq Nr Ns Nt Nu Nx Ny Oe Of Oh Oi Ok Om On Oy Pb Pd Pe Pf Po Qb Qd Qe) Og(Et Fp Hq Hr Hu Hv Hx Ik Ir Iv Jk Jo Jp Jq Jr Js Li Lj Lw Lx Ly Lz Ma Mc Md Me Mf Mg Mh Mi Mj Mk Ml Mp Mq Mr Ms Mt Mw Mx My Mz Na Nb Nc Ne Nf Nh Nj Nk Nl No Nq Nr Ns Nt Nu Nv Nx Oe Of Oh Ok Pa Pd Pe Pf Pg Po Qa Qb Qc Qd Qe) Mn(Et Hr Ih Ii Ij Ik Im Io Ip Iq It Iu Iv Jg Jh Jl Jn Jo Jp Jq Jt Lh Lu Lw Lx Ma Mb Mg Mh Mi Ml Mm Mp Mt Mv Mz Nd Nf Ng Ni Nm Nn Ns Nu Nv Ny Oe Of Oh Oi Ok Om On Oy Pa Pb Pc Pz Qb Qd) Pz(Et Hr Ih Ii Ij Ik Io Ip Iq It Iu Iv Jg Jh Jl Jn Jo Jp Jq Jt Lu Lx Mb Mh Mi Ml Mt Mv Mz Nc Nd Ne Nf Ng Nh Ni Nj Nl Nm Nn Ns Nt Nu Nv Ny Oe Oh Ok Om On Oy Pa Pb Qb) Fr(Et Hq Hu Ih Ik Im Io Ip It Iu Ji Jk Jl Jn Jo Jp Lh Lj Lv Lx Ma Mb Md Mh Mk Ml Mm Ms Mu Mw My Nc Nd Ne Nf Ni Nj Nl Nr Ns Nw Nx Oe Oi Pb Pc Pd Pe Pf Pg Po Qb) Lv(Hr Hv Ih Ii Ik Im Ip Iq Ir It Iu Jh Ji Jk Jl Jn Jp Js Lh Lu Mb Md Mg Mh Ml Mm Mt Mu Na Nd Ni Nn Ns Nw Nx Ny Oe Of Om Oy Pb Pc Pd Pe Qa Qb) Ij(Hr Ih Ii Io Ip Iq It Iu Jg Jh Jl Jn Jo Jp Jq Jt Lh Lu Lx Mb Mg Mh Mi Ml Mm Mt Mv Mz Ng Nh Ni Nn Ny Of Ok On Pb Pc Qd) Mu(Cq Hu Ih Ik Im Io Ip Iq It Iu Ji Jk Jl Jn Lh Mb Md Mh Ml Mm Ms Mw Na Nd Nf Ni Ns Nw Nx Oe Of Oi Pb Pc Pe Po) Nw(Hr Hx Ih Ii Io Ip Iq It Iu Ji Jn Jo Lh Lx Mb Mg Mh Ml Mm Ms Mw Nd Nf Ng Ni Ns Nx Oe Of Om Oy Pc Pg Po) Io(Hr Ih Ii Ik Ip Iq It Iu Jh Ji Jl Jn Jo Jp Jt Lh Lx Mb Mg Mi Mm Ng Ni Nm Nn Ns Ny Of Om Pc Qd) Nm(Hr Ih Ip Iq It Iu Jh Jp Jq Lx Mb Mi Mv Mz Nd Ng Ni Nn Ns Ny Oe Oh Ok Om Pb Pc Qb Qd) Ji(Et Hr Hv Ih Ik Im Ip Iq It Iu Jg Jn Jo Lu Mb Md Mg Ml Ms Ng Ni Ns Nx Oe Of Om Pb Pc) Ng(Hr Ih Ip Iq It Iu Jg Jh Jl Jn Lu Lx Mb Mv Nd Ni Nl Nn Ny Ok Om On Oy Pb Pc Qd) Ny(Hr Ih Ii Ip Iq It Iu Jh Jo Jp Jq Lx Mb Mg Mi Mv Ni Nn Nv Ok Om On Pc Qd) Pc(Hr Ih Ii Ik Iq It Iu Jn Jo Lh Mb Mg Mm My Ni Ns Oe Of Om Oy) Iq(Hr Ih Ii It Iu Jh Jl Jn Jo Jp Lh Mg Mi Mm Ni Nn Of Om) Ni(Hr Hv Ih Ii Iu Jo Lh Mb Md Mg Ml Mm Nn Of Om Pb) It(Hr Ii Ip Iu Jn Jo Jq Lh Mb Mg Mm Of Om) Ih(Hr Iu Jo Lh Mb Mg Mm Mt Of Om Qd) Hr(Ip Iu Jl Jn Mm Nn Ok Om On) Us(BA bP bV cT fP gW Jm Nb) Nn(Ii My Ns Om Oy) Mb(Ik Iu Jo Mg) Om(Ii Iu Jh Jn) fP(Jm Tv Ug) Mg(Ip Jh) Qd(Ik Im) Wmln Lxli MiHq MvUc IuJl JnJs JoOk PePg] Qd[Tj(aC AD aE aF aG aH aI aJ aK aL aM aN aO aP aQ aR aS aU aV AW aX aY aZ Ba bB BC bE bF BG bH bl bJ bL bM bO bP bQ bR bS bU bV bW bX bZ cA cB cC cD cE cF cG cH cl cJ cK cL cM cN cO cQ cR cS cU cV cW cX cY cZ dA dB dC dD dE dF dG dH DI dJ DK DL dM dN Et Ex Fw Hc Hv Hw iA Ih Ik In Iq Jl Jm Jo Jt Kc Kf Kl Kr Ks Lh Lu Lv Lw Ly Mi Mm Mn Ms Mu Mv Nb Nc Nd Ng Ni Nm Nw Oe Og Om Oz Pa Pb Pz Ra Rg Rh Ss Tr Tv Ub Uc Uh Uk Us Vo) Hw(Ad Af Aj Al An Ao Ap Ar As Ax Bb Bn Ch Cq Cs Ct Cu Cv Cw Cx Db Dc Dd De Dp dR Ed EF Ez Fa Fb Fn Fr Fw Fy GL GP gW Gz Ha Hb Hf iA Ib Ic Id Ik Il iO Iz Jd Je Jf Ji Ju Jv Jy Kc Kd Ke Kf Kg Ki Kj Kk Kl Kn Ko Kp Kq Kr Kx Ky Kz Ld Mu Oa oF Or Ou Ow Ph Pi Pj Qg Qh Ql Qm Qn Qt Qu Qv Qx Qy Qz Rb Rc Rf Rg Rh Ri Rj Rm Sr Ss St Tn To Tr Tt Tz Ua Ub Ud Ue Uf Uh Uk Ul Um Un Uo Up Ur Us Ut Uu Uv Vp Vt Vv Wm) fP(Al An Ap Bc Bo Co Ct De Dp dR eF Ex Ez Fb Gl gP HB hC hF Ib iJ IO IP iZ Jd Je Jy Kg kR kS Kx Nu nW nY oE oF oH oK oN Ou Ow Pj Pk Qh Qt Qu Rf Ri St To Ut Vs Vu tF) Il(Aw aX bN bR bS cF cH Cq cT cZ Di dR eC Ed eF Fn Fw gL GP Gz hB hC hF Hv iH iJ iO iP iZ Jg Ji Jm kQ kR kS Lv Mu Nn NW nY oE oF Og oH oK oN Pb Pc pF Pz tF) Ir(aC aF aG aN aO Aw aX aZ BA BG bM bN bR bV bX cC cF cH cJ cN CP cS cT cV dA dB dG Di dJ Dl Kf Kl Ks Qw Tv Uk Us Vo) Fw(aG

Figure 5 Continued

BA bM bN bX cC cH cJ cP cT Dg Di hB Hv iA iJ In iO Iu Jm Jt Kf Kl kQ Ks Lh Mm Mn Nm nW Om Pb Qw Tv Ug Uk Us Vo tF) In(aC aG
Aw Ba Bg bN Bo bR cF cH cN CP cT cV Dg Di Ed Fn Fr Hc Ib Iv Jl Jq Kr Lh Lv Mi Nn Nq Nt On Pc Pk Pz Uh Us) Uc(dR eC eF Ex Fy gL gP
gW Gz hB hC hF hG iA iH iJ iO iP iZ kQ kR kS nW nY oE oF oH oK oN pF Vs Vu tF) Hr(aC aG aH aN Aw aX BA bG bM bN Bo bR bX cF
cH cJ cN CP cT cV dA Dg Di dJ Qw) Hv(aC aG aN bA bM bN cJ cP cT Dg Di Ks Qw Tv Ug Vo Wm) Ii(aC aF aG aN aO bA bG bM bN bR cF
cH cN cP cT cV Ex) Fn(aG bM bN bX cC cJ cT Dg Iu Kf Ks Qw Tv Ug Us) Ed(bN cC Dg Iu Jo Jt Kl Ks Nm Qw Tv Uk Us Vo) Fr(Ik Im Jm Jt
Lh Mm Mn Ng Nm Ny Og Om Oz Wm) Ji(Ij Ik Im Io Jm Jo Lh Mn Ng Ny Og Om Oz) iA(aF aO BG bM Cs dJ Ks Lh Mf Nc Nd Ug) It(aC aG
bN cP cT Dg Di Ik Im Ks Ug Wm) Iu(aX bN cH cV cZ Di Qy Tv Ug Ur Us) Mu(Cq Ik Jt Mg Mn Nm Ny Of Og Om) Dg(dR eC eF gL gP Iq kQ
oF pF) Nw(Ij Jt Md Mm Nm Og Oz Pz) Pz(Jg Lv Nn Oz Pc) Ug(gP hB iO oF oN) Us(BA Bg bV gW) Tv(cT gW Gz Mv) Jm(Ba cH cP Pc)
Ks(gL gW Gz oF) Iq(cT Di Qv) Cs(iJ iO) Jt(eM gL) Og(Nn Pc) cT(Ur Vs) AwCq ExUk GzJo LvNg IkOz QegP OmeM PbfR bMkR dGhG}
Ji{Mm(Et Fp Hq Hr Hu Hv Hx Ih Ii Ij Ik Im Io Ip Iq Ir It Iu Iv Jg Jh Jk Jl Jn Jo Jp Jq Jr Js Jt Lh Li Lj Lu Lv Lw Lx Ly Lz Ma Mb Mc Md Me
Mf Mg Mh Mi Mj Mk Ml Mp Mq Mr Ms Mt Mv Mw Mx My Mz Na Nb Nc Nd Ne Nf Ng Nh Ni Nj Nk Nl Nn No Nq Nr Ns Nt Nu Nv Nw Nx
Ny Oe Of Oh Oi Ok On Oy Pa Pb Pd Pe Pf Pg Po Pz Qa Qb Qc Qe) In(Fp Hq Hr Hu Hv Hx Ih Ii Ik Il Im Iq Ir It Iu Jg Jh Jk Jm Jn Jo Jp Jq Jr Js
Li Lj Lu Lw Lx Ly Lz Ma Mb Mc Md Me Mf Mg Mh Mj Mk Ml Mp Mq Mr Ms Mt Mw Mx My Mz Na Nb Nc Nd Ne Nf Nh Nj Nk Nl No Nq
Nr Ns Nu Nv Nx Oe Of Oh Oi Ok On Pa Pb Pd Pe Pf Pg Po Qb Qc Qe) Nm(Et Fp Hq Hu Hv Hx Ih Ii Ik Im Iq Ir It Iu Jg Jk Jn Jo Jp Jq Jr Js Jt Li
Lj Lw Ly Lz Ma Mc Me Mf Mg Mh Mi Mj Mk Mp Mq Mr Ms Mt Mw Mx My Mz Na Nb Nc Nd Ne Nf Ng Nh Nj Nk Nl No Nq Nr Ns Nt Nu
Nv Oe Of Oi Ok On Pa Pd Pe Pf Pg Po Pz Qb Qc Qe) Oz(Et Fp Fr Hq Hr Hv Hw Ii Ik Im Io Ip Iq It Iu Iv Jg Jh Jl Jn Jp Lu Lv Lx Mb Md Me Mf
Mg Mh Mi Ml Ms Mt Mu Mv My Mz Na Nd Ni Nn Nr Ns Nw Nx Ny Oe Of Oh Oi Ok Om On Oy Pa Pc Pd Pe Pf Qa Qb) Mn(Et Hr Hv Hw Ii
Ij Ik Il Im Io Ip Iq It Iu Iv Jh Jl Jm Jn Jo Jp Jt Lh Lu Lv Lx Mb Md Mg Mi Ml Ms Mt Mv My Nd Nf Ni Nn Nq Ns Nw Nx Ny Of Oh Om On Oy
Pa Pb Pc Pe Pz Qa) Lh(Hr Hw Ii Ij Il Io Ip Iq Iv Jh Jl Jm Jn Jo Jt Lu Lv Lx Mb Mi Mv Ng Ni Nn Nv Nw Nx Ny Og Oh Om Oy Pb Pc Pz Qa)
Fr(Et Hq Hr Hw Ii Ij Il Io Ip Iq Iu Jn Jo Lv Mb Md Mg Ml Mw My Nd Ni Ns Nx Oe Of Ok Om Oy Pb Pc Pe Po) Mu(Et Hr Hv Hw Ii Ik Il Io Ip
Iq It Iu Jg Jl Jn Lv Mb Md Ml Ms Mw My Na Ni Ns Nx Oe Of Oy Pb Pc Pe Uc) Og(Et Hv Hw Ij Io Ip Iv Jg Jh Jk Jl Jm Jn Jo Jt Lu Lv Ml Mv
Ng Ni Nn Nw Ny Oi Om On Oy Pb Pc Pz) Pz(Hr Hw Ij Il Io Ip Iv Jh Jl Jm Jo Jp Lu Lv Lx Mb Mi Mv My Ni Nn Nw Ny Oh Om Oy Pb Pc Qa)
Jt(Hw Ij Il Ip Iv Jh Jl Jm Jp Lu Lv Lx Mi Mv My Ni Nn Nw Ny Ok Om On Oy Pb Pc Qa) Ij(Hw Io Ip Iv Jh Jl Jm Lu Lv Lx Mb Mv Ni Nn Nw
Om Oy Pb Pc Qa) Ny(Hr Hw Io Ip Iv Jh Jl Jm Jo Lu Lv Lx Mv Ng Nn Nw Om Pc Qa) Jm(Hw Io Ip Iv Jk Jl Lu Lv Mv Ng Nn Nw Om Oy Pc
Qa) Ng(Hw Il Ip Jh Jl Lu Lv Mv Ni Nn Om Oy Pc) Om(Hr Il Io Ip Jh Jo Lu Lv Mv Ni Nw Pc) Lv(Hv Hw Il Io Jo Md Ml Nx Pb Pc) Jo(Io Ip Jl
Lu Mv Ni Oy Pc) Nw(Hw Ml My Nx Of Pb) Ni(Hv Hw Md Ml Pb) Il(Et Io Jl Nn Pc) Hw(Io Jl Lu) NrJl MbMl MiHq MvMy JnJs PbPc PePg
aJdG} Mu{Pg(aD aE aF al aJ aK aL aM aO aP aQ aR aS aU aV aW aX aY aZ bA bB bC bE bF bG bH bI bJ bL bM bO bP bQ bR bS bU bV
bW bX bZ cA cB cC cD cE cF cG cI cJ cK cL cM cN cO cP cQ cR cS cT cU cV cW cX cY cZ dA dB dC dD dE dF DG dH dI dK dL dM dN
Ex Gd Gz Kc Kf Kl mZ Nw Qv Rg Ss St Ue Ug Uk Us Vo) fR(aH aM Et Fn Fy Hv Hw Id Ii Ij Ir It Jh Jn Jq Jr Js Kf Kj Kn Kp Kq Kr Kz Lh Lw
Md Me Mg Ml Mm Mq Mt Na Nc Nd Ne Ng Nk Nl Nw Ny Pa Pc Pi Pk Qa Rb Rj Sr Tv Ud Up Us Uv Vp Vt Vu Vv Tj) Gd(Aa Ad As bl bN
CQ Cu cV Cw dC dG dH DL Dr Em Gn Hr Hu Hv Hw Ii Ij In Ir It Iv Jl Jn Jo Jr Js Jt Kz Lw Md Me Mq Mr Mt Nb Nf Nm Nn No Nr Om Oz Pb
Pd Pe Uc Vu Vv Tj) Uc(Ad aJ aP Aw Ba BG bV cN Co Cq Cw Dc dN Dr Ef Fb Fr Gc Gn Hc Hx Il Ip Iz Jh Jp Jt Kd Ke Kf Kp Lj Lx Md Ms
Mv Nb Nq Nw Of Oi Ok On Oy Pb Pf Qa Rb Rm Ua Uf Uu Vp) Hw(aC aE aG aH aJ aK aL aN aP aU bA bB bF bG bI bN bP bV cC cD cE cH
cJ cN CO CP cT cV cX cY cZ dA dB dJ dK Dr Em Ex fP Gc Gn In Lv Nw Og St) Dr(aC Af Al Ap Bo bR bW cF cV dC Dg dH Ez Ib Ii Ik Im Iz
Jh Jt Ju Jv Kf Kl Kq Ks Lh Lu Mm Ng Nm Nq Of Pb Pj Qa Ss Tr Tv Vo) Em(Aa aC Ap aS bA cT DC Dg dH Gc Hb Hv Hx Ib Ik Jo Kd Kf Kl
Ks Lh Lj Lx Mj Mz Ng Nk Nm Nw Ny Or Oz Pb Qm Ss St Ug Ul Vo) Gn(Aa Af Al Ao Ap dC dH Ez Ib Ic Ii Ik Im Iz Jd Jg Jk Jl Jt Jv Ke Kq Ks
Lh Lu Mm Ng Nm Ny Of Pb Pj Qa Qm Ss Tr Uf Uh Vo) Og(Fr Hr Im In Ip Iv Jg Jh Jl Jm Jq Lv Lw Lx Mb Mg Mi Mn Mt Mz Nc Nd Ng Ni Nj
Nl Nn Oh Oi Ok Om On Oy Oz Pa Pb Pc Qa Qb) Gc(Aa BA bN Bo cF CT dA Dd dH dI Gz Hb Hq Ik Ir Kf Kq Lh Lx My Nm Of Pb) In(Fr Hx
Im Ip Jl Lh Lx Mb Mi Mr Mz Ng Nl Nt Nu Oh Ok On Oz Pa Pc Pe Qb) Nw(Hr Jm Jt Lh Lv Mg Ml Mm Mn Mw Ng Nm Ny Of Om Oy Oz Po
Pz) Oy(aC aG aH aK aN bB bG bI bN cH cJ cP cV dJ fP Fr On Oz) Tj(aG bA cH dJ Dk Il Pb Qt St Tr Ue) Ng(Fr Ip Jh Jq Lv Lx Mb Oh Ok Oz)
Il(Ao bF Co Dk Je Lv Qy Rb Uk) Jm(Fr Ip Lv Lx Oz Qa Qb) Uk(fP Jd Je Mw My Nq) eM(aC aG Jt Om Oz Pb) Lv(Hr Mg Mn Of Oz) Hq(cH
cV dJ fP) bF(Mb Nf Oz Ug) Fr(Mg My Of) fP(bV Co Rb) gC(aC Jk Om) Dk(Nd Us) Iu(kK mZ) CocH CqPb MmcN MyOn HrOk JeUs}
Nw{In(Et Fp Hq Hr Hu Hv Hw Hx Ih Ii Ij Ik Il Io Ip Iq Ir It Iu Jg Jh Jk Jl Jm Jn Jo Jp Jq Jr Js Jt Lh Li Lj Lu Lw Lx Ly Lz Ma Mb Mc Me Mf
Mg Mh Mj Mk Ml Mm Mp Mq Mr Ms Mt Mw Mx My Mz Na Nb Nc Nd Ne Nf Ng Nh Ni Nj Nk Nl Nm Nn No Nq Nr Ns Nv Nx Ny Oe Of Og
Oh Oi Ok Om On Oy Pa Pb Pd Pe Pf Pg Po Pz Qb Qc Qe) Md(Et Fp Hq Hu Hv Hx Ih Ii Ij Ik Il Im Io Ip Iq Ir It Iu Iv Jg Jk Jl Jm Jn Jo Jp Jq Jr Js
Lh Li Lu Lw Lx Ly Lz Ma Mb Mc Me Mf Mg Mh Mi Mj Mk Ml Mm Mp Mq Mr Ms Mt Mw Mx My Mz Na Nb Nc Nd Ne Nf Ng Nh Nj Nk Nl
No Nq Nr Ns Nt Nu Nv Nx Oe Of Og Oh Oi Ok Om On Oy Pa Pb Pd Pe Pf Pg Po Qa Qb Qc Qe Wm) Ij(Fr Hq Hr Hv Hw Im Io Ip Ir Iv Jg Jh Jl
Jm Jq Js Jt Lh Lj Lx Mb Mg Mi Mm Mn Mv My Nc Nd Ne Nf Ni Nl Nm Nn Nu Ny Og Oh Om Oy Pb Pc Pg Pz Qa Qb) Pb(Fr Hw Il Im Io Ip Iv
Jh Jl Js Jt Lh Lv Mi Ml Mm Mn Mv Ni Nm Nn Nu Ny Og Om Oy Pc Pz) Oz(Fr Hr Il Im Jh Lh Lv Ml Mm Mn My Nm Ny Of Og Pc Pg Po Pz)
Lv(Hr Il Io Jm Lh Ml Mm Mn My Nm Ny Of Og Pg Po Pz) Fr(Lh Mm Mn My Ng Nm Ny Of Og Oy Pg Po Pz) Og(Ip Jh Lh Ml Mm Mv My
Nm Nn Ny Oi Pc) Mm(Hw Ip Jh Jm Lh Mn Ny Oy Pc) My(Jg Jh Lj Ml Mn Ni Nn Nq Pc) Ml(Hr Jm Mb Mi Mn Ns Oy) Mn(Hw Jm Lh Mn Pz)
Mv(fR Jd Uc) Jl(Nb Pg Po) Ny(Lh Mn Ni) PoPe GdUa MnPz JnJs} aJ{dG(aC aD aE aF aG aH al aM AN AO aP aQ AR AS aU aV aW Ax aY
aZ bA BB BC bE bF BG bH bI bJ bM bN bO bP bQ bR bS bU bV bW bX bZ cA cB cC cD cE cF cG Ch cI cJ cK CO cP cQ cR cS CT CU cV
CW CX cY cZ DC dD DE dF dH dI dJ dK dL dM Ef Fr Kc Mv) Aw(Ad aG cH cV Dg) cV(BA cT Di) Cp(Ad cH Dg) BaDg} Fr{Lv(Hr Hw Ij Il
In Jm Mg Mn Ng Of Og Om Oy Oz Pz) Ng(Im Ip Iv Jh Jq Mb Mn Nd Nh Ni Nl Og Oz Pc) Jq(Hw Ij In Jm Md Mn Nm Ny Og Om Oz) Og(Ip
Mb Mn Nd Nl Nn Oi Oz Pc) In(Im Iv Mx Nl Nu Oz Qa) Jm(Ip Nl Oz Qa Qb) fP(Kc Rb) WmOf MnOz} Mv{Gc(Ad aG Ap Cw Dg Et Lu Om
Ue) St(fP Jd Om Tv Uc) Dr(Ap Cw Lu Om) Gn(Ap Cw Lu Om) Uc(EM Gd) fR(Mx Oz Pb) Pg(kK nU) aH(eM gC) nA(IL Nq) GddH NjmZ
UcUn OzgC} mZ{IL(hW jG jH kG kK lM nA nJ nR qT rB rZ) jG(jH jI) NjHq UafP IiJk} Cp{dX(aH bN bO cD cP Em) Uc(fP Kc Un) cP(aH
bN bO) eM(Aa aH) UsfP} My{Dr(aH AI cV Et Fy Kl Lh Om Tr Ub) Gc(Al Hb) GnHb nlIL} In{Qa(Iv Jq Lh Lv Mi Ni Nt Ok Om Om) Jq(Lh Lv
Nt)} cT{gV(aC aD aF dC) Em(aG bN) aF(dX eP) aH(eM gC) TjKc bNeP} Nc{nU(eD jD jI jT IK IL lM qT qU) nAlM nKIL} Ba{Dg(cN fR)
aC(bE cZ) cV(cN fR) GccF cLgC} bA{cV(Aw Di EM eP) gV(aC aG) TjKc} Ef{Jt(mF mM) Uk(fP St) AdGc DcmI DgmH} eM{Tn(Af Dg Jo
Kl) AaQy AwaH MwPb} gC{cL(Ct Oz Pb) bC(Cv Ug) AfTn} Ua{Pb(ml oQ) fP(kC nH) CqkC} qZ{jQ(jl lL Pd Pe) rZlL} St{aX(Dg fP Il Mf)}
jG{jl(jQ jR lM) nRjH} Aw{AdfR bOeP} Nn{Og(Lv Oz)} Oy{kC(Pe Ug)} fP{TnUs KcbV} ExJoUf GdHuIi

Unconstrained panels with 2 analytes, where 1.0E-8 >= 'model p-value' > 0. Contains 19 panels of 108,068 total panels evaluated. : Jj(aA Fr Ip Is
Ji Jl Jq Lv Mu Nv Nw Oh Qa Qb Qd) aA(Fr Ji Nw Oz)

Figure 5 Continued

Unconstrained panels with 2 analytes, where 1.0E-7 >= 'model p-value' > 1.0E-8. Contains 52 panels of 108,068 total panels evaluated. : Jj(Ik Im Ir Iv Jg Jh Jk Jm Lh Lx Mi Mp Mv Nl Nn Nt Nu Nx Oi Ok On Oy Oz Po Qc Qe) aA(cV Hr Hw In Ip Is JG Jq Lv Lw Lx Mb Mu Nd Nn Nx Pb Pc Qd) Is(In Jm Og) Qd(fP Uc) NmJi Unconstrained panels with 2 analytes, where 1.0E-6 >= 'model p-value' > 1.0E-7. Contains 175 panels of 108,068 total panels evaluated. : aA(aH aL cZ Et Fp Hq Hu Hv Hx Ih Ii Ij Ik Il Im Io Iq Ir It Iu Iv Jh Jk Jl Jm Jn Jo Jp Jr Js Jt Lh Li Lj Lu Ly Lz Ma Mc Md Me Mf Mg Mh Mi Mj Mk Ml Mm Mn Mp Mq Mr Ms Mt Mv Mw Mx My Mz Na Nb Nc Ne Nf Ng Nh Ni Nj Nk Nl Nm No Nq Nr Ns Nt Nu Nv Ny Oe Of Og Oh Oi Ok Om On Oy Pa Pd Pe Pf Pg Po Pz Qa Qb Qc Qe) Jj(Et Fp Hq Hv Ih Ii Ij Jo Jp Js Li Lw Ly Ma Mb Mg Mj Mq Mr Mt Mx My Mz Nb Nc Nd Ne Nh Ni Nj Nk Nq Nr Pa Pb Pc Pd Pe Pg) Is(Fr Hw Ij Il Io Iq Ji Jt Lv Mn Mu Ng Nm Nw Ny Oz Pz) Ji(Fr Ij In Jt Lh Mm Mn Mu Og Oz Pz) Nw(Ij In Md Pb) TjQd MuOg aJdG mZlL Unconstrained panels with 2 analytes, where 1.0E-5 >= 'model p-value' > 1.0E-6. Contains 280 panels of 108,068 total panels evaluated. : aA(aC aF aG aI aJ aK aM AN Ar aV AW aX aY aZ BA bB bC bE bH bJ bL bN bP bQ bR bU bV bZ cB cD cF cH cI cJ cM cN CO Cp cQ cS cT cU cW CX dB dC dF dG dH Di dJ dL dN jQ Kc IL qU) Is(Hr Ih Ii Ik Im Ip It Iu Iv Jg Jh Jk Jl Jn Jo Jp Jq Lh Lu Lw Lx Mb Md Mg Mh Mi Ml Mm Ms Mt Mv Mz Nc Nd Ne Nf Ni Nl Nn Ns Nu Oe Of Oh Oi Ok Om On Oy Pa Pb Pc Pe Qb Qd Us) Ji(Et Hr Hv Hw Ii Ik Il Io Ip Iq Iu Iv Jg Jh Jl Jm Jn Jo Lu Lv Lx Mb Md Mg Mi Ml Ms Mt Mv Ng Ni Nl Nn Ns Nw Nx Ny Of Om On Oy Pb Pc Pe Qd) Jj(Hr Hu Hw Hx Il In Io Iq It Iu jG Jn Jr Jt Lj Lu Lz Mc Md Me Mf Mh Mk Ml Mm Mn Ms Mw Na Nf Ng Nm No Ns Ny Oe Of Og Om Pf Pz) Fr(Hr Hw In Ip Jm Jq Lv Mb Mg Mn Mu Nd Ng Ni Nl Nw Of Og Om Oy Oz Pc Qd) Mu(Dr Em fR Gc Gd Gn Hw In Jm Lv Ng Nw Oz Qd Uc Tj) Qd(eC Ed Fn Fw gL iA Il In kQ Lv oF Pz Us) Nw(Lh Lv Ml Mm Mn My Nm Of Og Oz Pg Pz) aJ(Aw Ba cH cV) Cp(dX cP) BafR EmcT InQa StaX jGjl kKJL Unconstrained panels with 2 analytes, where 1.0E-4 >= 'model p-value' > 1.0E-5. Contains 711 panels of 108,068 total panels evaluated. : aA(AD aE Af Aj Al AO AP aQ aR AS aU Ax Bb Bc bF BG bl bM Bn BO bS bW bX cA cC cE cG Ch cK cL cP Cq cR Cs Ct Cu Cv Cw cY dA Db Dc DD DE Dg dl DK Dl dM eD Ef fP fR gW hA iB iC jD jE jF jH jI jK jL jM jO jP jR jT jU jV jY Ks IM IN IO qT qV qW qX qY qZ rA Rb rY St Ug Uk Us Wm) Fr(Et Fp Hq Hu Hv Hx Ih Ii Ij Ik Il Im Io Iq Ir It Iu Iv Jg Jh Jl Jn Jo Jp Jr Js Jt Lh Li Lj Lu Lw Lx Ly Lz Ma Mc Md Me Mf Mh Mi Mj Mk Ml Mm Mp Mq Mr Ms Mt Mv Mw Mx My Mz Na Nb Nc Ne Nf Nh Nj Nk Nm Nn No Nq Nr Ns Nt Nu Nv Nx Ny Oe Oh Oi Ok On Pa Pb Pd Pe Pf Pg Po Pz Qa Qb Qc Qe Wm) Mu(aJ bF bV Cq Dk eM Et FP gC Hq Hr Hu Hv Ii Ij Ik Il Im Io Ip Iq Ir It Iv Je Jh Jl Jn Jo Jp Jq Jt Kc Lh Li Lj Lu Lw Lx Lz Ma Mb Md Mg Mh Mi Mm Mn Mp Mr Ms Mt Mx My Mz Na Nc Nd Ne Nf Nh Ni Nj Nl Nm Nn Ns Nt Nu Nv Nx Ny Oe Of Oh Ok Om On Oy Pa Pb Pc Pe Pz Qa Qb Qc Qe St Ug Uk) Qd(aX Ba bS Cq cT Dg Di dR eF eM Fa GP gW Gz hB hC hF hG Hw iH iJ Ik Im IO IP iZ Jg Jh Jl Jm Jq Jt kR KS Lh Mm Mn Ng Ni Nm Nn NW NY oE Og oH oK Om ON Oz Pc pF Qm Qw Tv Ug Uk Ur Vs tF) Nw(aX cZ Et fP Hq Hr Hv Hw Hx Ii Il Im Io Ip Iq Iu Iv Jh Jl Jm Jn Jo Jp Jq Jt Lu Lx Mb Mg Mh Mi Mp Ms Mv Mw Nc Nd Ne Nf Ng Nh Ni Nj Nl Nn Ns Nu Ny Oe Oh Ok Om On Oy Pc Pe Po Qa Qb Us Wm Tj) Ji(Fp Hq Hu Hx Ih Im Ir It Jk Jp Jq Jr Js Li Lj Lw Ly Lz Ma Mc Me Mf Mj Mk Mp Mq Mr Mw Mx My Mz Na Nb Nc Nd Ne Nf Nh Nj Nk No Nq Nr Nt Nu Nv Oe Oh Oi Ok Pa Pd Pf Pg Po Qa Qb Qc Qe Ug) Is(Et Fp Hq Hu Hv Hx Ir Jr Js Ks Li Lj Ly Lz Ma Mc Me Mf Mj Mk Mp Mq Mr Mw Mx My Na Nb Nh Nj Nk No Nq Nr Nt Nv Nx Pd Pf Pg Po Qa Qc Qe Ug Uk) aJ(aC aF aG aH aM AN As aW aX bA bB bN bU cF cI cJ cN Co CP cT cZ De Dg dH Di dK dL Ef jQ jT Kc) Lv(Hw Il Im In Io Ip Iv Jg Jh Jl Jp Jq Lx Mp Mt Mv Mz Ng Nn Nv Og Oh On Oz Pc Qa) St(Aw Ba cN cT cZ Di fP Fw Il Iq Jj Jm Ju Kc Ks Ms Mv Pb Tv Ug Uk Us) Kc(aG aX bA bN bV cH cP cT Di fP Jj Nd Ug Uk) Ba(aC aN aP Aw cN cV cZ Di Dr Em Gc Gd) IL(kG kN IW mW nA nI nJ nN nO nR oP oQ) Aw(Ad aP aX bA dX eP fP Jj) In(Jl Jq Lh Lx Nv Ok On) cT(Dr dX eM eP Gn gV) Cp(Ad aX Jj Jo Uc) Mv(Dr fR Gc Gd mZ) Ua(Gd kC ml mZ nH) bA(cV Di Em eP gV) jG(jQ lM Lw mZ nR) Og(Jq Nn Nv On) Oz(Jq Lx Nn On) jQ(aP iZ Jj qZ) Jj(qZ Wm) Un(Ug Us) mZ(Hq oP) DrMy EfUk GdHu TneM QaJm UmoO aPjT Unconstrained panels with 2 analytes, where 1.0E-3 >= 'model p-value' > 1.0E-4. Contains 2,297 panels of 108,068 total panels evaluated. : St(aC AD aE AF aG aH aI AJ aK AL aM AN AO AP aQ AR AS aU aV aW Ax aY aZ bA BB BC bE bF BG bH bl bJ bL bM BN BO bP bQ bR bS bU bV bW bX bZ cA cB cC cD cE cF cG CH cI cJ cK cL cM CO CP CQ cR CS Ct CU CV CW CX cY dA DB DC DD DE dF DG dH dI dJ DK DL dM dN Dp Ed Ef Et Ex Ez Fa Fb Fn Fp Fr GL Gp gW Gz Ha Hb Hc Hf Hq Hr Hu Hv Hw Hx Ib Ic Id Ih Ii Ij Ik Im In Io Ip Ir Is It Iu Iv Iz Jd Je Jf Jg Jh Ji Jk Jl Jn Jo Jp Jq Jr Js Jt Jv Jy Kd Ke Kf Kg Ki Kj Kk Kl Kn Ko Kp Kr Kx Ky Ld Lh Li Lj Lu Lv Lw Lx Ly Lz Ma Mb Mc Md Me Mf Mg Mh Mi Mj Mk Ml Mm Mn Mp Mq Mr Mt Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Oz Pa Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss Tn To Tr Tt Tz Ua Ub Uc Ud Ue Uf Uh Ul Um Un Uo Up Ur Ut Uu Uv Vo Vp Vt Vv Wm Tj) Qd(aC AD aE aF aG aH aI AJ aK aL aM AN aO aP aQ AR aS aU aV AW Ax aY aZ bA bB BC bE bF BG bH bl bJ bL bM bN BO bP bQ bR bU bV bW bX bZ cA cB cC cD cE cF cG dH dI dJ dK DL dM dN Ef Em Et Fb Fp Fy Hc Hq Hr Hu Hv Hx Ih Ii Ij Iq Ir It Iu Iv jG Jk Jn Jo Jp Jr Js Ju Kc Kf Kl Kr Kz Li Lj Lu Lv Lx Ly Lz Ma Mb Mc Md Me Mf Mg Mh Mi Mj Mk Ml Mp Mq Mr Ms Mt Mv Mw Mx My Mz Na Nb Nc Nd Ne Nf Nh Nj Nk Nl No Nq Nr Ns Nt Nu Nv Nx Oe Of Oh Oi Ok Ow Oy Pa Pb Pd Pe Pf Pg Po Qa Qb Qc Qe Ql Qv Ra Rb Rg Rh Rj Tr Ub Uc Uo Vo Wm) Kc(aC AD aE aF aH aI aJ aK aL aM aN aP aQ aR aS aU aV AW aY aZ bA bB bC bE bF BG bH bl bJ bL bM bN bO bP bQ bR bS bU bW bX bZ cA cB cC cD cE cF cG cI cJ cK cL cM cN cO Cp cQ cR cS cU cV cW cX cY cZ dA dB dC dD dE dF DG dH dI dJ dK DL dM dN Et Et Fb Fr Fw gL Hc Hr Hv Hw Ic Ik Il Im In Is It Iv Ji Jo Ju Jy Kd Kf Kl Ks Ld Lh Lu Lv Lw Lx Mi Mm Mn Mr Ms Mv My Mz Nb Ng Nh Ni Nj Nm Nw nY Of Og oO Ou Ow Pb Pf Qv Rh Tn Tr Tv Ua Ub Uc Un Ur Us Vo Tj) Ba(AD aE aF aG aH aI Aj aK aL aM An AO Ap aQ AR AS aU aV aW AX aY aZ bA BB BC bE bF BG bH bI bJ bL bM BN BO bP bQ bR bS bU bV bW bX bZ cA cB cC cD cE cF cG CH cI cJ cK cL cM CO CP CQ cR cS CT CU Cv cW CX cY dA dB DC DD DE dF DG dH dI dJ DK DL dM dN eM Fr Fw gC gL Gn Is Jj Mu Uc Ug Uk) Nw(aC aE aF aG aH aJ aK aL aM aN aP aW aY aZ bA bB bC bE bF bG bH bl bJ bM bN bO bP bR bU bV bX cC cD cE cF cH cI cL cN cP Cq cS cT cU cV cW cX dA dB dG dH Di dJ DK dN Fp fR Hu Ih Ik Ir It JG Jk Jr Js Ks Li Lj Lw Ly Lz Ma Mc Me Mf Mj Mk Mq Mr Mt Mx Mz Na Nb Nk No Nq Nr Nt Nv Ns Oi Pa Pd Pf Qc Qe Qx Tr Tv Ug Ur Vp) aA(Dp dR Ed eF Ex Ez Fb Fn Fw GL gP Gz Ha Hb Hc Hf hR hV hW hX Ic Id Jd Je Jf Ju Jv Jy Kd Ke Kf Kg Ki Kj KK Kl Kn Ko Kp Kq Kr Kx Ky Kz Ld IK mZ nR nY Or Ou Ow Ph Pi Pj Pk Qg Qh Qn Qu Qv Qw Qx Qy Qz Ra rB RC Rf Rg Rh Rj rX rZ Sr Ss Tn To Tr Tv Tz Ua Ub Uc Ud Ue Uf Uh Ul Um Un Uo Up Ur Uu Uv Vo Vp Vt Vv Tj) aJ(AD aE Af aI Aj aK AL AO AP aQ AR aS aU aV Ax aY aZ Bb BC bE bF BG bH bl bJ bL bM Bn BO bP bQ bR bS bV bW bX bZ cA cB cC cD cE cG Ch cK cL cM cO CQ cR CS Ct CU Cv CW CX cY dA DB DC DD dE dF dI dJ Dk Dl dM dN eP Ex FR Fw Gl gW hA Is jG Jj jM jR Lv Mv Ow Oz Pb Ug) Mu(aC aD aE aG aH Aj aK aL aM AN AO aP aU Aw aX aY aZ bA BB bG bl bL bN bP bQ bR bU cC cD cE cF cG cH cJ cN CO CP cT cV cW cX cZ dA dB Dg Di dJ dK dM dN Ex Fw Hx Ih Iu Jd JG Jk Jr Js kK Ks Ly Mc Me Mf Mj Mk Ml mM mP Mq Mv Mw mZ Nb Nk No Nq Nr Oi Pd Pf Pg Po Qv Qw Qx Rb Tv Ue Ur Us Ut Vp Wm) Lv(aX Di Et FP Hq Hr Hu Hv Hx Ih Ii Ij Ik Iq Ir It Iu Jk Jm Jn Jo Jr Js Jt Lh Li Lj Lu Lw Ly Lz Ma Mb Mc Md Me Mf Mg Mh Mi Mj Mk Ml Mm Mn Mq Mr Ms Mw Mx My Na Nb Nc Nd Ne Nf Nh Ni Nj Nk Nl Nm No Nq Nr Ns Nt Nu Nx Ny Oe Of Oi Ok Om Oy Pa Pb Pd Pe Pf Pg Po Pz Qb Qc Qe Ug Uk) Aw(aC aE Af aG aH Aj aL aM AN Ao As Ax aZ bB BC bE bG bH bN Bo bP bV bZ cF CH cJ cN Co CP Cq cS CT cV Cw CX cZ dB Dd Dc Dg Dl dJ Dk DL dM dN Dr EM FR gC Gd gL Hr Il In Is Jo kC Ng Of Uc Ug Uk Us) Jj(aP aX bA Bg bV bZ CH cN Co CT Cu cV cZ De Di dN Ef Ex Ez Fb fP gL gW hA Hc hR Iz jD jM jR jT Jy Kd Ld IL Qh qU Qv qX Rf Rm Tn Tz Ua Ub Uf Ug Uk Un) Ua(Dr eM Gc Gn kE kF kG kI kK kN kO kP IW IX IY mE mF mH mM mP mS mT mU mW mY nA nB nC nD nF nI nJ nK nL nM nN nO nR nT nU oO oQ Ug Uk) Jq(Hr Hw Ij Il Im Io Ip Iq Iv JG Jh Jl Jm Jo Jp Lu Lx Mb Md Mi Mn Mt Mv Mx Nc Ne Ng Nh Ni Nl Nm Nn Nt Nu Ny Oh Ok Om On Oy Pc Qa Ug) On(Hr Hw Ii Ij Il Im Io Ip Iv jG Jh Jm Jp Jt Lx Mb Mi Mm Mn Mv Mw Mx My Nb Nc Nd Ne Ng Nh Ni Nl Nm Ns Oe Of Oh Om Oy Pb Pc Pz Qa Ug) Ug(aP aX bA bV Cp cT cZ Di Ef Ez Fb fP Fr Hc Im Ip It Iv Jh Kd Kq Lw Lx Mg Mi Ms Mv Nb Nd Ni Nn Oi oO Oy Pb Pf Pj Qa Rm Tn Uf) Cp(aC aG aH Aj aN aP Ax bA bP bV cH cN Cq cS cT cV cZ dB Dg Di Dl eM fP gL Hr Hw Il In Jt Ks Lh Mn Ng Of Uk Us Tj) Lx(Di fP Hr Hw Im Io Ip Iv JG Jh Jl Jm Jp Ks Lu Mb Mi Mm Mn Mt Mv Mz Ng Nh Ni Nl Nm Nn Og Oh Ok Om Pa Pc Pe Pz) Is(Aa aC Ad aG Aj aN aP aX bN bP bV cH cP Cq cV dB Dd Dg Di fP Fy gW jG Kf Kl Qw Rb Tr Tv Ub Uc Ur Vo Wm Tj) IL(jG jQ kC kE kF kI kO kP IX IY mE mF mH ml mM mP mS mT mU mY nB nC nD nF nH nK nL nM nT nU oO qZ rY) bA(aM AN aP aW AX bE bP cF cH cN cZ De dM dN Dr dX cM FR Fw Gc Gd Rb Tv Uc Uk Us Uv Tj) jG(aP Fr hA iB iC iZ JH Ji jO Jp jR jT kK IO Mf Ml Mp Nd Nj Nk No Nv Om oP Pe qZ rX rY rZ) Mv(Ao bV Co EM fP gC Gn In Ip Jd Jl jT kC kK mM mP My nA Ng nI Og Ok Oz Uc Ue Uk) Nv(Hr Hw Il Io Ip Jh Jl Jm Jt Lh Mb Mg Mi Mm Mn Ng Ni Nm Nn Ny Of Om Oz Pc Pz) Ok(Hr Hv Hw Ij Il Im Ip Iv Jh Jo Jp Mb Md Mi Ml Mn Ng Nm Nn Og Oh Oz Pb Pc Qa) aP(aC aF aG aH aM AN aW aX bB cF cH cI cT cV cZ De dG Di Ef hA jM jR Oz Pb) In(Im Ip Ir Iv Jg Jh Jp Mi Mx Mz Nl Nn Nt Oh Oy Oz Pc Po Qb Qe rY rZ Un) Qa(Hr Hw Ij Il Io Ip Iq Jh Jl Mb Mi Mn Mt Ng Ni Nn Ny Og Om Oz Pc Pz Us) aX(aC AN cl De Di Dr fP fR Gd Im Iv Ji Kd Kk Nb Oz Pb Qv Uk) mZ(hR hW Ib Jk kK kN IO Ma mF Nc Nd Ng Nj Nn nR Pb qZ rX rY rZ) Nn(Il Im Ip Iv Jh Jl Jp kK Mb Mi Mx Ne Nh Ni Nl Ns Oh Oy) Oz(fR fl Im Ip Iv Jg Jh Jl Jp Lh Mi Mp Mt Mx Ng Nl Og Oh Pc) Di(AN cN cS cT fP FR gL Im Iv Ji kC Nb Pb Uk) Jl(Hr Hw Il Ip Iv Jh Jm Jp Mb Mn Ng Ni Og Oh Pc) Mi(Dr gC Hq Ip Iv Jg Jh Jp Mb Nl Og Oh Pc Uk) cT(An cN De dN FR Fw GC Gd Rb Uk Us Tj) jQ(aO dN dR gL gP hG hV jH jI Mf Nj Nk nY Pe) Un(Ad Hr Hw Il Jo Ks Nm Rb Rj Tv Uc Uk Uv) Fr(Dg Dr Em fP fR Gd Ks Rb Uc Uk Us) Ji(Aa Dg fP Ks qZ Rb Uc Uk Us Wm) Ip(Il Iv Jg Jh Jp Mt Og Oh Pc) Uk(cN Ex Im It Ld Nb Nd Pb Tn) nR(hW jH jI kC Nm Pb rX rY rZ) qZ(hA hV iB iC jI jO jR jT IO) Ef(Dr Gd kC kl IW mI mM mY) Jh(Iv Mt Mx Ng Nl Og Oh Pc) fR(aF aG aH aW cH cV Pb Uf) jT(bE cF dM gL gP hG iZ Nk) Jp(Io Mb Mn Ni Og Pc Wm) Us(bV Dc Ke Kq Lh Nb Tn) Dr(bC Co cS Ct Ez Hu) Tn(fP Il Ks Tv Uc) Og(Iv Jg Oh Pc Qb) kK(Hq jH jI IO Pb) My(Gc Gd Gn Jg) eM(aH Nu Pb pK) jM(gP iZ nW nY) Ng(Jg mM mP) Pc(Iv Mx Oh) Pe(kC rY rZ) bV(cV fP Pb) jR(iZ jI Nk) oP(qU rY rZ) Ex(cN gW) Kq(Cq Hw) cS(cN eP) fP(Kd Uf) gC(cL Ez) LwRb NarZ NenU HqmP HcoO ItKs QbJm aCbE bMkC dMgV mIpK nAIO iZjD Constrained panels with 3 analytes, where 1.0E-10 >= 'model p-value' > 0. Contains 50 panels of 14,487,373 total panels evaluated. : Jj{Mu(aA Im Ip Is Ji Jq Lv Nu Oh Oy Oz Pc Qa Qb Qc Qd) Is(aA Fr Hw Ih In Io Iq Lv Mn Ny Om Oy Oz Pc) Ji(aA Fr Mn Nm Ny Oy Oz) aA(Lv Mg Oz Pc Qd) FrOz} aA{Ji(In Nm Oz) OzPc} Uc{Qd(Ba Cp cT)}

Constrained panels with 3 analytes, where 1.0E-9 >= 'model p-value' > 1.0E-10. Contains 145 panels of 14,487,373 total panels evaluated. : Jj{aA(Fr Ip Jg Jk Jq Lx Mb Nd Nj Nn Nt Nu Nv Nw Nx Oi Oy Pb Po Qc) Fr(Ip Iv Jq Lv Mn Nd Nl Nu Oh Oi Oy Pc Qa Qb Qd) Qd(Io Ip Jk Lv Mn Nn Ny Oi Oy Oz Pc Pz) Oz(Ip Jk Jl Jq Lv Nn Nv Nw Oh Qa Qb) Lv(Ip Ji Nn Nv Nw Oh Oy Qa Qb) Ji(In Io Ip Jk Mm Nn Om Pc) Oy(Ip Jl Jq Nv Nw Oh Qa Qb) Ip(Jk Nn Nu Oh Qa) Nw(Ij Md Ml) Nv(Mn Ny) Mulv QaPc} aA{Ji(Hr Hw Ih Ii Ij Jm Jo Jt Lh Mm Mn Ny Om Pc) Oz(In Is Jg Jq Lv Lx Mu Mz Nn Nw Pe) Nw(Ij In Lh Md Ny Pg) In(Is Lv Mu Qd) MuOy} Qd{Uc(Aw bA Bg Ef Hc Mu Mv) BafP} Is{Jm(Fr Mu Oz) MuIn} HuPfmP VocLgC Constrained panels with 3 analytes, where 1.0E-8 >= 'model p-value' > 1.0E-9. Contains 488 panels of 14,487,373 total panels evaluated. : Jj{Nw(Ik Im In Io Ip Iv Jh Jk Jm Jq Lx Mm Mn Mv My Nc Nl Nm Nn Nu Nx Ny Oh Oi Om Pb Pc Pg Qa Qb) Oy(Im Ir Iv Jg Jh Jk Jm Lh Lx Mi Mp Mv Mx Mz Nc Ne Nh Nl Nm Nt Nu Nx Oi Ok On Pc Po Qc Qe) Nn(Ik Im Ir Iv Jh Jk Jl Jm Jq Lx Mx Nl Nt Nu Nv Nx Oh Ok Po Qa Qb Qc Qe) Jq(Im Ip Iv Jg Jh Jk Jl Lv Lx Mn Mv Nc Nl Nu Oh Oi Om Pb Pc Qa Qb) Oh(Ik Im Iv Jg Jh Jk Jl Lx Mg Mn Mv Ni Nl Nt Nu Oi On Pc Po Qb) Lv(Im Iv Jg Jh Jk Jl Jm Lx Mg Mp Mt Mv Nl Nu Nx Oi On Pc Qe) Ip(Im Iv Jg Jh Jl Lx Mi Mv Nc Nl Nt Nv Oi On Pc Po Qb) Jk(Im Io Iv Lx Mn Nl Nu Nx Om Pc Qa Qb Qc) Qb(In Io Jg Jh Mg Mn Ni Nu Oi On Pc) Lx(Iv Jh Jl Mn Nl Oi On Pc) On(Im Io Iv Mn Nl Oi Pc) Jl(Io Iv Mb Mn Oi Pc) Nv(Io Lh Mm Nm Om Pc) Qa(Io Mn Ny Oi) Nu(Jg Jm Mv) Iv(Jg Jh Pc) Qd(cH cV fP) Oi(Im Pu Qc) Pc(Im Po) MvMy NlJg InLh} aA{Nw(Hr Hw Is Jm Jt Lv Ml Mm Mn My Nb Nd Nf Nm Og Om Pb Pc Po Pz) In(Fr Im Jg Jq Lh Lw Lx Mg Mz Nn Nt Nu Nv Nx Ok Om Pc Po Qa) Pc(Fr Hr Hw Ip Is Jq Lv Lw Lx Mb Mu Nd Ns Om Pe Qd) Is(Hr Hw Ih Ij Il Iu Jm Lv Mb Ny Og Om) Lv(Hr Hv Hw Ij Jo Md Ml Mu Nn Pb) Hr(Jq Lw Mu Nn Ok Oz Qd) Ji(Ir Iu Mb Md Nf Pb) Mu(Hw Mb My Og Om) Qd(Hw Jm Jt Om Oz) FrOz LwMb MzJs JqOm PePg aNcV jGjQ} Is{In(Fr Hw Io Iq Iv Ji Jl Jm Jq Jt Lh Lv Mi Mm Mn Mz Ni Nl Nm Nt Nu Nw Ny Og Ok Om On Oz Pb Pc Pz) Jm(Hw Io Ip Iq Ji Jt Lv Mm Mn Nm Nn Nw Ny Og Om Oy Pc Pz) Og(Fr Mn Mu Nn Oz) Il(Fr Oz) NmJi IjNw} Qd{Uc(bC bM bN cN Co Ct Di fP Fr Hv Ib Il Jg Jh Jk Kc Ms My Nb Ng Ou Tv Uu) fP(aX bM Dl gL Hr Hw Ii Il In Jo Kr Mv Nm Qw Rb Tv Ug Us Tj) Hw(aG bN bX cH cP cT) TjcT} Mu{Dr(Hb Om) Gn(Hb Om) In(Ji Nw) fR(Mb Ug) CpUc EmQv} Ji{Nm(Fr In Oz) MmIn} AwaJdG CpaGdX aCaXgV Constrained panels with 3 analytes, where 1.0E-7 >= 'model p-value' > 1.0E-8. Contains 871 panels of 14,487,373 total panels evaluated. : Jj{Pc(Hq Ih Ii Ik Ir Jg Jh Jm Jp Js Lh Li Mg Mi Mj Mp Mq Mr Mt Mv Mx Mz Nc Ne Nh Ni Nl Nn Nr Nt Nu Nx Oi Ok Qc Qe) Nl(Im Ir Iv Jh Jm Lh Mg Mi Mp Mt Mv My Mz Ni Nt Nu Nx Oi Ok Oz Po Qc Qe) Jh(Ik Im Ir Jk Jm Lh Mi Mx Nc Ne Nh Nt Nu Nx Oi Ok On Pa Pb Po Qc Qe) Oi(Hq Ir Iv Jm Js Lh Mg Mi Mp Mr Mv Mx Mz Nc Nt Nu Nx Ok Pa Qe) Nc(Im Jg Jm Lh Mg Mi Mp Mr Mv My Mz Ni Nn Nx Ok On Oz Qc) Im(Ik Io Ir Iv Jg Mi Mn Mp Mt Mv Nt Nu Nx Ok Pa Pb Qc) Nn(Lh Mi Mn Mp Mq Mr Mv My Mz Ne Nh Ni Ns On Pb) Nu(Hq Ir Iv Lx Mg Mi Mp Mt Mz Nx On Po Qc Qe) Ik(Jp Js Lh Mi Mp Mt Mx My Mz Nd Oz Pa Qc) Nx(Hq Ir Iv Jg Jm Lh Mg Mi Mv Mx Nt On Qc) Mg(Ir Iv Js Mp Mx Mz Ne Nh Pa Qc Qe) Qd(aG aH Ba bN DG Qw Tv Ug Uh Us) Mv(Ij Ir Iv Jm Md Nt Pa Pb Qc Qe) Oz(Et Ih Ii Jp Li Mj Mr My Nh Nq) Qc(Io Iv Jg Lh Mi Mn Mx Nt On) Jm(In Iv Jk Lh Mi Mt Ni Nt On) Ok(Hr Ij In Io Ml Mn Pb) Mi(Ir Iv Jg Ne Nh Nj) Jk(Ir Mx Mz Nt Po Qe) Mp(Ne Nh Nj Nt Pb) Jg(Io Ir Mx Ne) Lh(Iv Mb Nd Nh) On(Ir Mb Nd Om) Nt(In Iv Nd) Pb(Ir Js Mz) Qe(Io Mn) Polv PePg} aA{Hr(Fr Ip Jg Lx Mb Mg Mq Mv Nd Ni Nj Nu Nx Om Oy Pb Po) In(Ip Jk Mb Mq Mv Mx Nh Ni Nj Nl Nq Oi On Oy Pb Qb Qc) Nn(Hw Ii Il Ip Jm Jq Mb Nd Nf

Figure 5 Continued

Nj Ns Og Om Oy Qd) Lw(Hv Hw Ij Ir It Jo Jt Md Ml Na Nf Nm Pb) Om(Fr Ij Ip Jg Jh Lx Mg Mz Nv Nx Pb Po Qc) cV(An AW aX BA cF cH cI cN cT Di dN) Hw(Fr Ip Jg Jq Lx Mg Mz Nu Nv Nx Ok Qc) Qd(fP Ih Il Io Iu Lh Lv Mu Nm Ny Pz Tj) Jq(Fr Ij Ip Jo Mb Md Mn Nf Ny Og Pb) Ok(Hv Ij Ir Jo Jt Mb Md Ml Nf Nm Pb) Jg(Ij Il Ip Jm Mb Nd Ng Ns Og Oy) Fr(Il Ip Jm Mb Mn Nd Ns) Mu(Il Is Jm Nd Ng Ns Uc) Mg(Iu Jm Nd Ng Og Pc) Is(Io Iq It Jt Mn Nd) Lx(Jm Mb Mn Nd Ny) jG(jO jR mZ nR nU) Mv(My Og Oy) Jm(Ip Nv Po) Pe(Oy Pa Pd) Lv(Il It) Mz(Nf Pc) Nv(Lh Ny) Og(Nx Oi) MpNd NiIj HxNw IlPc aCbE aJdG aNcZ} Is{Il(Hw Io Iq Iu Ji Jl Jt Lv Mm Mn Mu Ng Nm Nn Nw Ny Og Om On Pa Pb Pc Pz Qd) Og(Hw Ih Io Ip Iq It Iu Ji Jn Jt Lv Ni Nm Nw Ny Oi Om Pc Pz) Oz(Fr Hr Hw Ii Ij It Iu Ji Jt Lv Mn Mu Ng Ni Nm Nw Pc Pz) Mu(Hr Hw Ii Ij Jo Jt Mg Mn My Ng Nm Ny Om Oy Pz Uc) Fr(Hr Hw Ii Ij Iq Jt Mg Mn Ng Nm Ny Of Om Oy Pz) Lv(Hw Ij Io Jo Jt Mn Ng Nm Pz) Ji(Hw Ii Ij Jt Lh Mm Mn Ny Pz) Nw(Hw Jt Md Mn My Nm Ny Pb Pz) Hw(Io Iu Mn Ni Nm Pz) Ni(Ij It) In(Ng Nn) Pz(Pc Qd) Jm(It Pb)} Ji{In(Et Fr Hw Ij Io Ip Iv Jl Jt Lh Lv Mi Mn Mv Ni Nt Nw Ny Og Om Oz Pc Pz Qa Qd) Mu(Ij Jm Jo Jt Lh Mg Mm Mn Ng Nm Ny Og Om Pz) Nm(Hw Ij Ip Jh Jm Lv Mn Og Oy Pc Qd) Oz(Ij Jm Jo Jt Lh Mm Mn Ng Og Pb Pz) Fr(Jg Jm Jt Lh Mm Mn Ng Ny Og Pz) Mm(Hw Jm Mn Og Om Pc Qd) Mn(Ng Og) Qd(Jt Pz) MdNw} Qd{fP(Ad aO cT Dd Fw Hc Ih Iq Iu Jm Js Jt Ju Ks Mf Mm Nf Og Oz Pd Qe Uk Ur) Hw(Aw Ba Bg Bo Cp Dg Di Hc Ks Pk Qw Ra Tv Ug Vo) Tj(bA bN cP Dg Il Iu Qw Ug) Mu(In Jm Ng Pz) Il(Fr iA It Oz) Uc(Iu Ks Tn) Ir(Dg Ug) EdUg FrPz InNw UscT} Mu{Uc(bA bF cT Hq It Jg Kc Lh Mj Pg St Tn Uk Un Tj) Pg(aC aG aH aN bN cH dJ fP Qw) Nw(Ij Md My Og Pb) Gn(aG Dg Kf Kl) In(Iv Jq Lv Qa) Em(aG Iz Om) Gc(bR Om) aH(eM gC) DkUk DraG TjfP} Nw{Md(Fr In Lj Lv Mn Mv Ni Nm Nn Ny Oz Pc Pz) In(Fr Im Iv Lv Mi Mn Mv Nt Nu Oz Pc Qa) Ij(Lv Oz) MiPg MvMy OzPb} aJ{dG(aX Ba cH cL cN Cp Di dN)} CpaGeP DrMyHb EfJtmH NcnUjH IuqZjQ OmcLgC UmbHoO

Constrained panels with 3 analytes, where 1.0E-6 >= 'model p-value' > 1.0E-7. Contains 1,815 panels of 14,487,373 total panels evaluated. :
Mu{Gd(Ad As bI bN CQ Cu cV Cw dC dG dH DL Dr Em Gn Hr Hu Hv Hw Ii Ij In Ir It Iv Jl Jn Jo Jr Js Jt Kz Lw Md Mc Mq Mr Mt Nb Nf Nm Nn No Nr Om Oz Pb Pd Pe Pg Uc Tj) Uc(Ad aJ aP Aw Ba BG bV cN Co Cq Cw Dc dN Ef Fb Fr Hc Hx Il Ip Iz Jh Ji Jp Jt Kd Ke Kf Kp Lj Lx Md Ms Mv Nb Nq Nw Of Oi Ok On Oy Pb Pf Qa Rb Rm Ua Uf Uu Vp) Dr(aC Af Al Ap Bo bR bW cF cV dC Dg dH Ez Hw Ib Ii Ik Im Iz Jh Jt Ju Jv Kf Kl Kq Ks Lh Lu Mm Ng Nm Nq Of Pb Pj Qa Ss Tr Tv Vo) Em(Aa aC Ap aS bA cT DC Dg dH Hb Hv Hw Hx Ib Ik Jj Jo Kd Kf Kl Ks Lh Lj Lx Mj Mz Ng Nk Nw Ny Or Pb Qm Ss St Ug Ul Vo) Gn(Af Al Ao Ap dC dH Ez Hw Ib Ic Ii Ik Im Iz Jd Jg Jk Jl Jt Jv Ke Kq Ks Lh Lu Mm Ng Nm Ny Of Pb Pj Qa Qm Ss Tr Uf Uh Vo). In(Fr Hw Hx Im Ip Jl Lh Lx Mb Mi Mr Mz Ng Nl Nt Nu Og Oh Ok On Oz Pa Pc Pe Qb) Gc(BA bN Bo cF CT dA Dd dH dI Gz Hb Hq Hw Ik Lh Lx My Of Pb) Nw(Hr Hw Jm Jt Lh Lv Mg Ml Mm Mn Mw Ng Nm Ny Of Om Oy Oz Pg Po Pz) Og(Fr Hw Ip Jh Jl Jq Lv Mb Mn Ng Nn On Oz Pc Qd) Is(Cq Io Iq It Iu Jk Lh Lv Mb Mm Ni Oe Of Pc) Ji(Hr Hv Hw Ii Il Jg Md Ml My Nx Of Oy Oz Pb) Pg(Dg Kc Kf Kl mZ Qv Rg Ss St Ue Ug Uk Us Vo) Oy(aC aG aH bB bN cH cJ cV dJ fP Fr On Oz) Tj(aA aG bA cH dJ Dk lJ Pb Qt St Uc) Qd(Cq Hw Ik Il Jt Mg Mn Nm Ny Of Om) Ng(Fr Ip Jh Jq Lv Lx Mb Oh Ok Oz) Hw(aG bF cH cJ Co Cp fP Lv St) Il(Ao bF Co Dk Je Lv Qy Rb Uk) Jm(Fr Ip Lv Lx Oz Qa Qb) Uk(fP Jd Je Mw My Nq) Lv(Hr Mg Mn Of Oz) fP(aA bV Co Hq Rb) bF(Mb Nf Oz Ug) Fr(Mg My Of) Hq(cH cV dJ) Dk(Nd Us) Iu(kK mZ) Jj(aG cH) CocH CqPb MmcN MyOn NdfR HrOk JeUs OmgC aAaG} Is{Pc(Fr Hr Hw Ii Ij Io Iq It Iu Ji Jo Jt Lv Mb Mg Mn My Ng Ni Nm Ns Nw Ny Of Om Oy) Ni(Fr Hr Hv Ii Il Iu Ji Jo Jt Mb Md Mg Ml Mm Mn Ng Nm Nn Nw Ny Of Om Pb Pz) Ih(Hr Hw Ij Iu Ji Jo Jt Lh Lv Mb Mg Mm Mn Mt Ng Nm Nw Ny Of Om Oz Pz Qd) Nw(Hr Ii Io Iq It Iu Jn Lh Lv Mh Ml Mm Mw Ng Nx Of Om Oy Pg Po) It(Hw Io Iq Iu Ji Jq Jt Lh Lv Mb Mg Mm Mn Ng Nm Ny Om Pz) Hr(Io Ip Iq Iu Ji Jl Jn Lv Mm Mn Nm Ny Ok Om On Pz) Ij(Io Ip Iq Iu Jq Lx Mb Mm Mn Mv Nm Nn Ok Om On Pb Pz) Ji(Et Hv Io Iq Iu Jn Jo Mb Md Mg Ml Ng Nx Of Om Pb) Fr(Io Iu Jk Jn Jo Lh Lv Mb Mm My Nd Ns Oe Pb) Ny(Hw Io Ip Iu Jh Jp Lv Lx Ng Nn Nv Oz Pz Qd) Iq(Io Jt Lh Lv Mg Mm Mn Ng Nm Nn Om Oz Pz) Jt(Et Hw Ip Jh Jl Jp Jq Lx Nn Ok On Qd) Us(aA BA bP bV cT fP Jj Jm Nb) Nm(Io Ip Iu Jh Jp Lx Mb Mn Qd) Nn(Ii Mn My Ng Ns Om Oy Oz Pz) Lv(Ii Iu Lh Mg Mm Of Om Qb) Ng(Hw Io Ip Jg Jh Mb Mn Mv) Pz(Ip Jh Jp Lx Mb Mn) Mg(Il Ip Jh Mb Oz) Io(Iu Jp Mn Om Oz) Iu(Jl Mb Mn Om) Hw(Ip Jl Mm) Jj(cH cV jG) Jo(Mb Ok Oz) fP(Jm Tv Ug) Lx(Ii Mn) Mv(Il Uc) Jh(Mn Om) MbIk MiHq IlLh JnJs PePg} Qd{In(aC aG Aw Ba Bg bN Bo cH CP cT cV Dg Di Ed Fn Fr Fw Hc Ib Iv Jl Jq Lh Lv Mi Nn Nq Nt On Pc Pz Tj) Fw(aA aG BA bN cC cT Dg Di Hv Il Iu Jm Jt Kf Kl Ks Lh Mm Mn Nm Om Pb Qw Tv Ug Uk Us Vo) Tj(aG Ba Bg Di Hv Ik Kc Kf Kl Ks Lh Mm Mn Mv Nb Nc Nm Om Pb Ra Rg Rh Tv Ue Uk Us Vo) Il(Aw aX bN bS cF cH Cq cT Di Ed Fn Gp Gz Hv Hw Jg Jm Lv Nn Nw Og Pb Pc Pz) Ir(aG BA Bg bM bN cC CP cT Di Kf Kl Ks Qw Tv Uk Us Vo) Fn(aA aG bM bN bX cC cJ cT Dg Iu Kf Ks Qw Tv Ug Us) Ed(bN cC Dg Iu Jo Jt Kl Ks Nm Qw Tv Uk Us Vo) Fr(Hw Jm Jt Lh Mm Mn Ng Nm Ny Og Om Oz) Hr(aG Aw Ba bN Bo cH CP cT Dg Di Qw) iA(aF aO BG bM dJ Jj Ks Mf Nc Nd Ug) Hv(aG bN cP cT Dg Di Ks Qw Tv Ug Vo) Iu(aX bN cH cV cZ Di Qy Tv Ug Ur Us) Ji(Hw Ij Io Jm Jo Lh Mn Ng Ny Om) It(aC aG bN cP cT Dg Di Ks Ug) Nw(Ij Jt Mm Nm Og Oz Pz) Pz(Jg Lv Nn Oz Pc) Jj(Fy Kf Ko Kr Ks) Us(aA BA Bg bV) cT(Ii Iq Tv Ur Vs) Jm(Ba cH cP Pc) Gz(Jo Ks Tv) Hw(Kf Kl Rh) Ii(bN bR cP) Iq(Dg Di Qv) Cq(aA Aw) Og(Nn Pc) eM(Jt Om) DgeC LvNg MvTv UgoF dGhG} Ji{Lv(Hv Hw Ij Io Jm Jo Jt Lh Md Ml Mm Mn Ng Nx Ny Og Om Oz Pb Pc Pz) Fr(Et Hr Hw Ii Ij Il Io Iq Jo Mb Md Mg Ml My Nx Of Om Oy Oz Pb) Og(Hv Hw Ij Io Ip Jt Lh Lu Ml Mv Nn Nw Ny Oi Om Oy Pc Pz) Oz(Et Hr Hv Hw Ii It Lu Md Mg Ml Na Nn Nw Ny Om Pc Pd Pe) Mn(Hw Ij Io Jh Jm Jo Jt Lh Ml Nw Ny Om Oy Pb Pc Pz) Jm(Io Ip Jk Lh Lu Mv Nn Nw Ny Om Oy Pc Pz Qa) Jt(Ip Jh Jl Lh Lx Mm Mv Nw Ny Oy Pc Qa) Ij(Io Ip Jh Lu Mm Mv Ni Nw Oy Pb Pc) Pz(Hw Ip Jh Lu Mv Nw Ny Om Oy Pc Qa) Jo(Io Ip Jl Lu Mv Ni Ny Om Oy Pc) Ng(Ip Jh Jl Lu Mv Ny Om Oy Pc) Lh(Io Ip Jh Jl Lu Nw Ny Oh Pc) Nw(Hw Ml My Nx Ny Of Om Pb) In(Hv Hx Jk Md Ml Nu Pe) Ni(Hv Hw Md Ml Om Pb) Ny(Ip Jh Lu Mm Mv) Om(Io Jh Lu Mv Pc) Hw(Io Jl Lu) Mm(Ip Nx) Il(Jl Nn) NrJl MbMl MiHq MvMy JnJs PbPc PePg aJdG} Nw{Lv(Hr Il Io Jm Lh Ml Mm Mn My Nm Ny Of Og Oz Pb Pg Po Pz) Oz(Fr Hr Im Jh Lh Ml Mm Mn My Nm Ny Of Og Pc Pg Po Pz) Fr(Ij Lh Mm Mn My Ng Nm Ny Of Og Oy Pb Pg Po Pz) Og(In Ip Jh Lh Ml Mm Mv My Nm Nn Ny Oi Pb Pc) Pb(Io Jl Js Ml Mn Mv Ni Nm Nn Ny Oy Pc Pz) Ij(Im Ip Iv Jh Mi Mm Mn Mv Nm Nn Pc Qa) My(In Jg Jh Lj Ml Mn Ni Nn Nq Pc) Nm(Hw Ip Jh Lh Mn Ny Oy Pc) Ml(Hr Jm Mb Mi Mn Ns Oy) Mm(Hw Jm Lh Mn Pz) Jl(Nb Pg Po) Ny(Lh Mn Ni) Mv(Jd Uc) PoPe GdUa MdIo MnPz JjjG JnJs} aA{aN(aF aH aL aM Ba bB bE cF cH cQ dG dL) Kc(aG cH cV DG fP Mm Ow Tr Tj) Ba(aC aG aL aZ bA cH DG Di) Aw(Ad aG aH aL cH Cx DG) Ok(Ii It Iv Na Nr Pd) cQ(aG aH aX cF cH cZ) dG(aX cN Cp cX Di dN) jG(cT Jj kG kK Mc Mf) Ni(Hv Hw Md Ml Pb) aL(aC aF cX jT qW) cZ(aC aF cX Di jT) IL(jQ jR kG kK mZ) Cp(Ad Ax Cq cV) Il(Ip Mg Mv Qc) Om(Hv Hw Md Ml) On(Ii Ny Of Og) Di(aG aH Cx) cT(jM jQ jT) De(cV Cx) Mv(fP Jm) Nv(Mn Ng) aX(aC fP) bE(aG jT) cH(aF cX) jQ(cU qZ) ArcV PoNy NrJl MlMz MtNf JnJs aHcX aSjT bIqW nUjL} Jj{Pb(Hx Ih Jp Li Mr My Nc Ne Nh Om) Mz(Hq In Js Mb Ml Ne Nh Nj Pa) jG(Fr Jl Jp Jq Mp Nk Nv Om On) Nj(Mr Mt My Ni Nq Pa) Ml(Hx Jo Jt Om) Mn(Et Ii Jp Li) Mt(Mq Nc Ne Nh) Mb(Mr My Pe) Hq(Nc Ne Nh) Ij(Jo Jt Om) In(Jt Nq Om) My(Nd Ne) Ni(Jp Nk) NqNd MdOm MqPa MrNk NcIi IoJp StaX PdPe} Fr{Lv(Hr Hw Ij Il In Jm Mg Mn Ng Of Og Om Oy Oz Pz) Ng(Ip Iv Jh Jq Mb Mn Nd Nh Ni Nl Og Oz Pc) Jq(Hw Ij In Jm Md Mn Nm Ny Og Om Oz) Og(Ip Mb Mn Nd Nl Nn Oi Oz Pc) In(Im Iv Mx Nl Nu Oz Qa) Jm(Ip Nl Oz Qa Qb) fP(Kc Rb) MnOz aJdG} aJ{dG(An As bC bU bV bZ cF De Ef Kc Mv) Aw(Ad aG cH cV Dg) cV(BA cT Di) Cp(Ad cH Dg) BaDg} Mv{Gc(Ad aG Ap Cw Dg Et) St(fP Jd Om Tv Uc) Ap(Dr Gn) Pg(kK nU) nA(lL Nq) GddH NjmZ UcUn aHgC} In{Qa(Iv Jq Lh Lv Mi Ni Nt Ok Om On) Jq(Lh Lv Nt)} My{Dr(aH Al cV Et Fy Kl Lh Om Tr Ub) AlGc nIlL} mZ{lL(hW jH nA

Figure 5 Continued nR rB rZ) jG(jH jI) NjHq UafP IiJk} Ba{Dg(cN fR) aC(bE cZ) cV(cN fR) GccF cLgC} fP{Cp(Uc Us) Ua(kC nH) EfUk TnUs StaX KcbV} bA{cV(Aw Di Em eP) gV(aC aG) TjKc} Ef{Jt(mF mM) AdGc DcmI DgmH StUk} cT{Em(aG bN) gV(aC aF) TjKc bNeP} Nc{nU(jT lK qU) nAlM nKlL} gC{cL(Ct Oz Pb) AfTn UgbC} qZ{jQ(jI lL Pd Pe) rZlL} jG{jI(jQ jR lM) nRjH} Ua{Pb(mI oQ) CqkC} St{aX(Dg Il Mf)} Cp{Uc(Kc Un)} Nn{Og(Lv Oz)} Oy{kC(Pe Ug)} AaQyeM AdAwfR GdHuIi Constrained panels with 3 analytes, where 1.0E-5 >= 'model p-value' > 1.0E-6. Contains 4,450 panels of 14,487,373 total panels evaluated. : Mu{Gd(aG aH aM Ax aY Ba bB Bc Bg Bn bW cC cH cJ Cp cW dB Dc Dd eF Fa Fn fR Fw Fy Gc Ha Id Il Jh Jk Jq Jy Kd Ke Kf Kn Ko Kp Kq Kr Lj Lx Mb Mi Ml Mw Na Ni Nk Nw Ny Pi Pk Po Pz Qa Qg Qn Qv Qx Ra Rb Rc Rj Sr St Tr Tv Ua Ud Ul Un Up Ur Us Ut Uv Vp Vs Vt) Cq(aA aC aG Ao Aw bF bG bN bV cN Co Cp Dc Dg Di dJ Dk fP Hq Hr Hx Il It Iu Iv Jc Jj Kc Kd Mb Mj Mm Mw My Nb Nc Nd Nu Nw Oz Pa Qt Qv Qw Qy Rb St Ub Ue Ug Uk Un) bF(Ad aG aH aM Ba bN cH cV dJ Dk fP Hr Ii In Ir Iu Jj Jl Jo Js Kc Kj Ks Lh Md Mm Mt Mw Nd Nm Nw Om Ow Pb Pc Pd Qv Qw Rb Rj St Ue Uk Ur Us Uv Vp) Dk(aA aY Ba bQ bR bS bU bZ cA cF cG cK cL CO cP DG dH dI fP Hq Hw Jj Jy Kc Mb Md Mk Mm Mp Mt Nb Nw Of Oz Pb Pd Pf Qv Qw Rg St Tr Uv) Tj(aC Ao bB bV cJ cT Dg Hr Hw Ik Is It Iu Iz Je Jh Jj Kc Kf Lz Md Mj Mm Mn Mw My Nc Nw Om Oz Pa Qv Qw Qy Ra Rb Rg Ub Ug Uh Uk Us Vo) Uc(Ap Ar Bc Ch Cu De Di Ex fP Hv Ib Id Im Iv Jd Je Jj Jl Kq Li Lw Mt Mx My Mz Nd Nv Ou Oz Pa Pe Ph Qe Qh Qv Qx Rc Tt Vv) fP(aJ aX Dr Em Gc gL Gn hG Hr Il In Is Iu Jj Kc Kd Lx Mk Nf Of Oz Pb Qv Qw St Ue Ug Us Vp) Hw(Aw Dc Fr Hc Im Ip Je Jh Jl Jq Kc Kd Lx Mi Ng Oh Ok Oz Pk Qa Qv Qw Rb Rm Tn Ue Uk Un) Of(aC aG aN Aw Ba bG bN Cp Di Em Hc Ip Jh Jl Jq Kc Lx Mi Oh Ok On Qv Qw St Ug) Gn(aC aH Bo bR cF cV Dl eF Fb Fy Jh Jj Jp Ju Kp Li Mn Ow Pz Qd Qe Qu Tv Uo) Il(aG bA Bb bG Bo bV cN Fr In Ip Jd Jl Kc Nw On Qt Qw Qx St Ue Ug Ut Vp) aA(Ad aH aM cH cJ cV Cx DG dJ Fw Kc Ks Ow Qv Qw Rb St Ug Uk Us Vp) Jq(Hr Ij Ip Jm Jo Jt Lh Mb Md Mg Mn My Nm Ny Om Oy Oz Ph Pc Pz) Em(aH bE bN bW Et Ex Hq Ii Jm Jt Jy Lu Mm Ph Pj Qg Qu Tr Uc) Mw(aY bQ bR bS bU bZ cA cF cG cL cO cP dG dH dI gC St Tr Us) Uk(bV cH cJ cN cV dJ Kc Md Mt Nb Nv Ny Pb Po St Us Vp) Lx(Hr Ij Jt Lh Mb Mg Mn My Ni Nm Ny Oe Om Oy Oz Pz) Nf(aG bN bQ bR bU bV bZ cF cG cH cL cO cP dG dH dI) Co(aG aH aK aM bN cJ cV dG dJ In Md Mt Ur Us Vp) Hr(bA bV Fr Ip Jl Mb Mi Mn Ng Ni On Oz Pe Qa Qd) Qd(Dr Ij Io It Jo Lh Lv Mm My Oy Oz Pc Ur Us) Jj(aH aX bN bV cJ cV cZ Je jG Kc Qx St Ue Vp) Jm(Im Ir Iv Jh Jl Mb Mi Ng Nv Oh On Pc Qc Qe) Rb(bA bQ bU bV bZ cG cO cP cT dH Md Nq Pg) Gc(Af aG aY bW bX eM Ib Lu Qn Tr Tv Vv) My(dG Jl Mv Mx Nv Ok Oz Pc Qw Tr Us Uv) Je(aY bQ bU cG cO dG dH dI Md Mt Pd Qw) St(Ex Fw Iq Iu Ks Md Mt Po Tv Ug Us Vp) Fr(Ij Ip Mb Mn Nd Ns Ny Oe Om Oz Pz) Mg(Ip Iv Jh Jl Mb Mi Oh Ok Oz Pc Qa) Hq(aG aH aM bN cJ dG Mi Ur Us Vp) Jl(Ip Iu Jo Mb Mn mP Ng Nr Om Oy) Ok(Ij Jo Jt Mb Mn Nm Om Oy Pb Pz) Dr(Ao cN cT Ic Ke Li Qm Uf Uo) gC(Af bB cL Cx Ij Im Nu Ny Pa) Ip(Jo Mb Mi Mn Nm Om Oz Pz) mZ(mM mP Mt Nc Nj Oy Pd Po) Oz(aJ bV Ik Im Mi Mt Pc) Pg(iA iJ kK Ks Pe Qt Ur) Ng(Im Iv Jg Nv Qa Qc) Kc(aG bV cH cJ Dg Ug) Vp(bA Dg Md Mm Ue Us) Oy(Jh Mv Nn Nv Pc Qa) eM(iJ kC mF mH mI nH) Mn(Jh Mi Mz Oh Qa) In(Ir Jn Mx Nv Qe) Iu(cG cO kC nI nT) Nw(Ii Io Mh Ns Nx) Om(Jh Lv Mi Oh Qa) bV(Jo Mm Nd Po Us) Uc(bA bN cT cV) Is(aG Ks Ug Us) Ao(dG Mt Us) Mb(Ik Mi Pc) Mm(aJ aP bG) Lv(Ij Jo) Qa(Ij Pz) Ug(It Nq) Pc(Mi Ns) aJ(DG) mP(Pe Pf) kK(mM Po) CpJo ExQv MdQt MzPb NdcN JiPd JnJs LhOh UnUs UvbA} Qd{Gz(aA Ba bM bN bX cC cN Di Dl Et Fw Ha Ih Iu Js Jt Kf Kn Kr Lh Mf Mn Mr My Nf Nh Nm Ny Oi Om Oz Pd Po Qm Qv Tr Ue Ug Uk Ur Us Vo Vt) Di(aA aG aH aX bN cH Cq cV cZ Dg Ed Fn Gp Hq Hx Jl Jm Jo Jt Kf Kz Lh Ly Mm Mn Nd Ng Om Ow Oz Pb Po Qw Tv Ug Uk Ur Us Vs) Jm(Aw bN cV Ed Fn Hc Hw Io Ip Jg Jh Jk Jq Jt Kc Kz Lv Lx Mm Mn Mv Ng Nm Nn Nw Og On Oz Pz Qw Rg Rj St Tv Ug Uk Ur Us) Tv(aA Aw BA Bg Cp Cq Ex Fa Gp Hc Hr Ib Il Iq Is It Kc Lh Lx Mj Ms Nb Nc Nw Pb Qv Qw Rg St Tn Ug Uk Un Ur) Gp(aA aG Ba bN cH cJ cP Dg Dl Et Ik Iq Iu Jl Jo Jt Kf Kl Ks Lh Mm Mn Ng Nm Om Qw Ra Ue Ug Uh Uk Us Vo) In(Hx iA Io Ip Jg Jh Jk Jt Lx Mm Mn Mr Mt Mv Mz Nb Nc Ne Ng Nh Ni Nl Nm Nu oF Og Ok Om Oz Pa Pe) Us(Aw cN CP Fr Hc Hr Hv Il Iq Is It Ji Kc Kz Lh Lv Ms Mv Nb Nc Nd Nw Oi Pb St Tn Ug Uk Un Ur) Cq(aC BA Bg bN cN CP cT Dg Hc Is Iu Iv Kc Ks Lv Ly Mm Mn Mv Nb Nc Om Oz Pb Qw Rg Ug Uk) Ed(aA Ad aG Aj aX Ba bX cT Dl Et Fw Fy Ik Jl Kf Kr Lh Mm Mn Ng Om Rh Tr Ub Ue) Ur(aA Aw BA Bg bN Dg Fn Hc Ib Il Iq Ks Mm Ms Mv Nb Nc Pb Qw Ra Rh Uh Uk) Fn(Ba Dl Et Fw Fy Ih Ik Jl Jo Jt Kl Kr Lh Mm Mn Ng Nm Om Uk Vo) Ba(aC aG Dg Em Hq Hv Hx Il Iq It Iu Jt Kl Ks oF Qm Uk Vs) Hw(Io Ip Jh Jl Jq Jt Lv Mn Ng Ni Nm Nn Nw Og On Oz Pc Pz) Il(Bg Co Ef Fa Hc Ip Kc Kg Mv Nm Nx On Pa Qm Qw Rj Uk) Og(Io Ip Jg Jh Jl Jq Jt Lv Mn Mv Ng Nm Ny Oi On Oz Pz) eM(aH bN Dg Dl fP Kf Kl Lh Mm Nm Ny Oz Qa Qc Qe Uh Vo) Iq(aG bA Bg bN cH cP Fr Kc Ks Nw Pc Qw St Ug Uk Vo) Hr(Fr Fy Hc Ji Kf Kl Ks Nn Nw On Ra Rh Ug Uk Vo) It(Aw Cp Fy Hc Ji Kf Kl Kr Lv Qw Rh Ub Uh Uk Vo) Jt(bN Cp Ip Jg Jh Jl Jq Lv Lx Mv Nn Ok On Oz Pc) Ng(Ip Jg Jh Jl Mn Mv Ni Nn Nw Ok On Oy Oz Pc) cT(Ax Em Fy Ha Hq Hx Jo Ks Oz Po Rb Rj Ug Uk) Pc(Fr Io Lh Lv Mm Mn Ni Nm Ns Nw Ny Om Oz) Hx(aC aG bA bN cH cP Dg Ks Qv Qw Ug Uk) Ks(aA aG bM bN bS bX cH cV Fa Iu Mv) Oz(aX bS Jh Jq Lv Mn Mt Ni Nm Nn On) Uk(Fa Hq Hv iA Iu Kc Mv Pb Qm Qw) Lv(Io Jo Lh Mm Mn Nm Nn Ny Om) Pz(Ip Jh Jp Jq Lx Mv Nv Ok On) Iu(iA Kc Kf Kr Qw Rb Rj Vo) Fr(Ij Io Jo Mb Mg Nd Of) Hv(Aw Fy Kf Kl Kr Ra Rh) Nw(Io Lh Ml Mn Ny Om Po) aA(cH Cu cV DG Ha Vs) Nm(Ip Jg Jh Jq Nn On) Ug(cZ Fa Hq Kc Pb Qm) oF(aF aO bG Jj Mv Um) Dg(Aw aX bN Kc Mv) Fw(Fy Ra Rh Ub Ue) Ji(Et Ii Jn Of Qa) bA(Ax Em Ha Po Vs) Mn(Jh Jq Nn On) Hq(bG bN cP Qw) Ir(Fy Kr Rg Ue) Mv(Em Ue Vs) aC(aX bE cZ) bS(Jo Mm Pb) jG(Jj Nk Pe) Ny(Jq Nn) Vs(Bg Cp) cN(iA Jl) oN(aO Mc) AwJo TjFy EmLu FaQw IoJh JnJs JuiJ KccH LipF UmiA PbcZ PePg} aA{jG(aL aS bE bV Fr Hr Hv Hw Hx Ij In Ir Is Iv Jn Jo Jp Jr Js Md Me Mi Mj Ml Mr Mt Mx Mz Na Nb Nf Nk Nm Nr Nw oP Pb Pd Pe Pf Qa qZ) Kc(aH Ba bN bX Cx dF dH Di Fw Hr Hw Il Im Jj Kf Kl Ks Lh Ms Mv Nd Om Rb Ss Tv Uc Ug Uk Us) fP(Aw Ba Bg bU bZ cF cH Co Cp Di Ef Fr In Is Ji Jj Ma Nw Qv Rb St Tn Ug Us Vv Tj) Mv(Ad aG aH aL Ao bN cH Co cV DG dJ Jd Ks Rb St Uc Ue Ug Uk Us Tj) jT(aC aD aK aM aN aX bA bG bJ bQ bV cG cI cQ cW dF eC hC kR lL oE Wm) Cp(aG aH aL aM As cH cQ Cs Cu CW Cx cZ Dg Hr Hw Ii In Jo Uc Us) jQ(aD aM aS bA bJ bQ bV cG cH cI cQ dF dR hB hC hV kQ Mc oE Pe) Di(aL aN cQ Ii Il In Ir Jj Lh Mb Nf Nr Ow Oz Pb Rb Us) Pb(aG aH aL aM bN cH Cq cV cW cZ dG St Ug Tj) Us(Ba Bg Dc Ji Kq Lh Mz Nd Nw Qa St Tn Un) aG(Ao aX Ch Co De Ef Is Jj Mb Mg Nw Oz) St(Fw Ii Il Jj Ju Ks Lh Om Rb Tj) cV(Ef Im Is Iv Ji Jj Nb Nw Oz Pd) Aw(Af aM aN Ax aY cQ cW cZ Ii) Cx(aL aN Bn cH cZ dG Ef Jj Oz) Is(cH DG Ks Rb Uc Ug Tj) De(Ad Af aH aM Ax cW dG) qW(aK aQ aS bE cM cT dF) An(aH aL Ax cH cZ dG) Co(Ad aH Ax DG Ks) Tj(Lh Li Mj Nw Oz Tn) jM(aS bP bQ bU gP iZ) Rb(Ba Hc Ji Lw Nd) hA(aL bE cI cT dN) Dg(Ao Ap Bg Ch) Ks(Ba Im It Tn) Nw(aX bN cH dG) aH(Ao Ef Jj Oz) lO(kK mZ nA qZ) aX(aN bV dH) cH(cF Jj Oz) cX(aN Ar cF) dG(Ao Jj Mp) jL(kK mZ nR) jV(bA cG jU) Ax(Ar cT) Dc(Ad Cq) Ef(Aj Uk) Tn(Ii Uc) dL(aJ bP) qZ(hV jR) qU(rY rZ) rX(rY rZ) AfUf HwKq ImUg aCbJ aLqV bAjE bZdF} Is{Us(aJ aP Aw aX Bg bN cN Cp Di Ef Fr Hc Ib Il In Ju Kc Kq Ks Lh Mm Mn Ms Mv My Nd Ni Nw Oi Pb Rh Tn Tr Tv Ub Ug Uk Un) Jj(Aa Ad aG aH AX Ba bN cZ Dd DG Di fP hA Kc Kf Ko Ks qZ Tr Tv Uc Ug Uk Vo Vp) Ug(aG aX bN cT cV dH Di Il In Jm Kc Kf Kl Ks Lh Mm Mn Nb Ni Om Pb Tr Tv Tj) Ks(aG aX Ba bN bP bX cH cV Di fP In Jm Kc Kf Mv Nd St Uc Uk) fP(aX Di gL Ii Il In Jo Jt Ju Kc Og Qv Rb Rm Ub Uk Tj) Jm(Aa aG Ax Ba bN cH cV Dg Di jG Rb St Tr Tv Uc Uk) Jo(aG Aw aX bA bN cH Cp cT Di Ip Jl Nn) Di(Dg Il In Jt Kf Mn Tv Uc Uk) Uc(Aw BA Cp cT Fr Kc Nb) Il(aG Aw aX bN cH dB Dg Kc) Tv(BA cT Kc Mv Nb Ub) Lh(Ip Jh Lx Nn Nv Oh Uk) Aa(bN Hw Ih In Iq Ni) Of(Jg Jh Jn Mv Nn On) In(aG Dg Ju Tr Ub) Nn(Mg Ms Oe Pb) Mm(Ip Jh Jp Mb) Jq(Hv Md Ml Pb) Oy(Jg Mv On Pe) jG(Iu Mf Nk Pz) Dg(aJ aX Kc) My(Jg Mv On) Ii(aG bN Mb) Pe(Nr Pa Pd) Ml(Mb Ok) Nd(Ik Mi) Js(Jr Mt) Kc(aG Kf) Uk(Mn Pb) WmjT

Figure 5 Continued

TjbA GdUa NrJl MgMv Ihlp IuJn OeOn OkPb aCaX aJdG} Fr{Jq(Hr Hv Ii Il Io Ip Iq Jo Jt Lh Mb Mg Ml Mm My Nd Of Oy Pb Pc Pz) In(Hx Ip Jl Lh Mb Mn Mz Nc Nd Ne Nh Ni Nj Nt Oh Ok Pc Qb) Ip(Hr Hw Il Io Mb Mg Mn Nd Nl Nm Nw Ny Of Om Oy Oz Pz) Nw(Hr Hw Ii Il Io Jm Jt Lv Lx Mg Mh Ml Mw Nd Om Pc) Pz(Iv Lx Mx Nc Nd Ne Nh Nj Nl Oh Oz Pc Qa Qb) Mn(Hr Il Iv Jh Jm Kc Lx Mb Nl Of Oh Oy Qa) Ni(Hr Hw Ij Mg Nc Nj Nk Nl Of Om Oz Pb Pc) fP(aX gL Hr It Jj Kd St Tv Uc Ug Uk Us Tj) Jm(Im Ir Iv Mb Mx Nc Nd Ne Nh Nu Oh Pc) Mg(Il Iv Jh Mb Nd Ne Nh Nl Oz Pc) Hr(Iv Jl Nd Nl Nu Ok Om Oz Pc) Qa(Hw Ij Il Iq Jt Lh Nm Ny Om) Iv(Io Nm Ns Ny Of Og Oy Pc) Il(Jl Mb Nl Og Om Oz Qb) Nm(Lx Nd Nh Nj Nl Oh) Of(Mb Nd Nl Oh Oz Pc) Oy(Mb Nd Nl Nn Oz Pc) Kc(aG Dg Kf Kl Uc) Mx(Hw Ij Io Ny) Oh(Lh Mm Ny Om) Ns(Nn Nu Pc) My(Mv Nn Pc) Jl(Hw Ii Nr) Ok(Ij Jo Jt) Em(Ba cT) Mz(Ij Pb) Ny(Ir Qb) jG(jQ jT) DrcT LvIo MbOz MiHq NlHw UcUn HvJi JnJs PePg bAcV} Nw{Pc(Il Im Jh Jm Jt Lh Lv Mm Mn Mw Ng Ns Ny Of Oy Pg Pz) Mv(bF Co Dk fP Gd Je Jm Jt Mw Ng Of Oy Pg Po Pz) Jm(Im Io Ip Iv Lx Mi Mn Nn Oh Oy Oz Qa Qb) Of(Ip Iv Jg Jh Jk Lx Mg Mi Ni Nn Ok On Oy) Og(Im Io Iv Jg Jl Lu Mn Nu Oh Oy Pg Pz Qa) aX(aC bN Dg fP Jj Jl Lh Nd Pb Rb Us Tj) Hw(Im Io Ip Jh Jl Lv Lx Mi Ml Pz Qa) Jt(Ip Iv Jh Jl Lv Mi Ok Oy Oz Qa) Lh(Io Ip Jh Jl Mi Mn Oh Pg Po Pz) Tj(bA cT Cv Dg fP Pb Rb Uh) Pg(Im Jh Ji Mn Nt On Pa Pe) Po(Im Lx Mi Nt Ok On Pa) Ng(Ip Jh Jl Lv Mn Oy Oz) Io(Hr Ip Jh Jl Mi Mn Oz) Pz(Ip Iv Jh Ny Om Oy Qa) Uc(Aw Ba Cp cT Ef Hc) Mi(Hq Lx Mh Mn Ny) Mw(Jg Jh Mh Nf Nn) Jl(Hr Hx Il Mr Nr) cZ(Dg Jj Pb Rb Ug) fP(gL Kc Rb Us) Nn(Ns Oy Oz) Mm(Ip My Ny) Il(Im Ip Qa) Ji(Hr Ii Lv) Jj(cH cV qZ) jG(Nk Pe Pf) Ml(Ip Ni) Mn(Jh Lx) My(Dr Nm) Oz(Mh Pe) DgcN EtfR NsNy LvNx HrOk RbcT JhOm KccH aJdG} Mv{Gc(Aa aC Al Ao BO cF cN cP cV dH fP Gd Hv Hw Ib Ii Jd Jh Jj Jm Ju Jv Ki Lh Mg My Ng Nr Oy Pb Qh Qu Rh Tr Tv Ub) St(Ad Ao aX bF Co cZ Dg Fw Fy Hq Hr Hw Il Iq Je Jh Jj Jo Ju Ks My Of On Po Ue Ug Uh Uk Us Tj) Gd(aG Ao Ap cJ dB Ij Im Jd Lj Mj Oa Pb Vp) mZ(Ii Jj Jo kC Mf Mk mM Nd Nq Oy Pe Pg Po) fP(aJ bV Co gL In Jd Jj Kc Oy Ue Ug) kK(Hq Hr Ii Jo Mk mM Nj Of Oy Po) Ji(Hr Ii Jg Md Mg Ml Of Oy Pb) nA(Jh Jo Mf Oy Pe Pf Pg Po) Jj(Co Jd jG jQ Qt Uc Ue) Dr(Bo cN Co dH Ij Pk) Em(Ap bA Hv Mj Nm Ny) Kc(aG bP Co Dg Uc Ug) Lv(In My Ng Og Oz) Ue(Lw Of Pj Uk Un) Jd(kC mF ml Uk) gC(Af Ij Ny Om) In(Jq Lh Qa) Oy(mF nI nR) kC(Pc Pf Pg) Uc(Dc Qa) Il(Ao fR) Jo(Ex Un) mP(Mf Nj) AanK DgaJ PomF MknI JqOg UnUs VqbI qZjQ} In{Jq(Hw Hx Im Ip Iv Jg Jh Jk Jl Lx Mi Mn Mx Nb Ne Nh Nl Nn Nq Nu Nv Og Oh Ok Om On Oy Oz Pa Pc Pe Qb) Qa(Hw Hx Io Ip Jg Jh Jk Jl Jm Lx Mn Mq Mr Mt Mz Nb Nn Nq Nu Nv Ny Og Oy Oz Pa Pc Pe Pz) Lv(Hx Im Ip Iv Jg Jh Jl Jn Jr Lh Lx Mi Mt Mx Mz Nn Nt Nv Oh Ok On Oy Oz Pa Pc Pe Qb) Lh(Im Ip Iv Lx Mi Mz Nh Ni Nl Nn Nu Nv Oh Oz Pc Qb) On(Im Ip Iv Lx My Nl Nu Og Oh Oy Oz Qb) Nv(Iv Jl Mi Mn Mz Ng Nm Og Oz) Nn(Ip Iv Lx Nt Og Ok Oz) Lx(Iv Jl Nt Oz Pc) Qb(Iv Mi Nt Ok Oz) Ok(Im Mi Oz Pc) Jl(Im Ip Oz) fP(Aw Cp Tn) Gd(Hu Ua) Qc(rY rZ) jG(Lw rZ) jQ(Im qZ) NtMz HxJj OhOz} Kc{cT(aG cV Dg fP Hr Hw Il Jj Jo Kl Ks Lh Mm Ow Rb St Tr Tv Uc Ug Uk Us) fP(aO Aw aX Ba Bg Cp Di Ef gL hG Im Jj Kd Nd Nq St Tn Ua Ug Tj) Ug(Aw Ba bN bX cH Cp cZ Di Fb Hc Im Lw Ms My Nb Nd St Ua) Dg(aJ aO aX Ba bN bV bZ Di dN Ji Lx Nd St Uf) Jj(aG aH Ba bN bV cH cV cZ Ms Nd St Ua) bV(Il Lh Mm Ow Sr Tr Us Tj) Ba(aG cH cJ cV Kl Uc) Nd(aG bN Il Tv Uk Us) Il(aO bA bN Im St) St(bX cH Ju Ms) Ow(aJ aP bG Di) Uc(bA Nb Ua) aG(Bg Di) bA(Tv Us) DdoO EfUk EtJi GdUa LwcH aPdG} St{Jj(aH Aw Ba cH cV cZ Di Ef fP Fw Hc Hv It Ju Mi Ms My Nd Oy Pb) aX(aC Bg Di Fw Hb Hc Ju Kf Kl Ks Lh Mm Om Pb Tr Ug Uk Us Vo Tj) Il(Aw cN cT cZ Di Ef Im Kg Mg Mi Nn Pb) Us(Aw Ba bV cN Cp cT Di Ef Hc Nb Nd) Uk(Aw Ba cT Di Ju Mi Ms Pb) Ug(Aw cT cZ Ef Hc Ms Pb) fP(Aw Ba bV Di Ef gL Nq) Ks(cN Co cT Ef Hc Ms) cT(Fw Ii Ju Uc Tj) Aw(Ad Kf Tv Uc) Ms(Jm Lh Om) Pb(cZ Ju Tj) Uc(Ba Cp) AdEf ApDg DiJu TjbA GdUa IbTv TngC} Ua{Gd(aX bA Bb bC bN bU cN Cs cT dC Ex Hv Ib Im Jn Ky Lj Lx Ly Lz Me Mi Mj Mp My Ng Nx Oa Oi Om Pb Pk Qh Qv Tn Uf Vp Vu) kC(aC Dg Jk Jp Jt Kf Kl Lh Nm Om Oz Pb Qe Ss Tr Vo) mZ(Cq Jk Jp Kl Lh Ma Mf Mm Ni Oh Om Pb Qh Tr Vo) oQ(aP Cq Hx Il Jn Ju mI Oz Qh Ue Uv) oO(Hx mI Qh Ue Uv Vo) Mf(mH mI mM) fP(Ex Jj kF) Cq(kF nN) Qe(kF nT) Vo(mS mW) Pb(mP nA) mI(aC Oz) AdmS DdnT DrbR ExKs JjgW aHeM} Lv{Oz(Il Im Ip Jh Jl Jp Jq Lx Mt Mz Nd Ng Nn Nv Og Oh On Pc Qa) Nn(Hr Hw Il Ip Jh Jl Jm Lx My Ng Ns Oy) Og(Ip Jg Jh Jq Lx Mt Nv Oh Oi On Pc) Lx(Io Jl Jm Mn Mt Ng Nm Pc Pz) Il(Io Ip Jh Jl Jq Mt Oh On Pc) Ng(Ip Jg Jh Jp Nv Oh On Qa) Io(Ip Jh Jp Oh Qa) Ji(Hr Ii Na Of) Mt(Ip Jh Jl) Nv(Jm Lh Mn) Hr(Ok On) Jh(Mn Oh) MzPb HwJq QaJm JnJs JoOk LhOh OfOn PePg aJdG} Ji{Oy(Hr Ii Md Mg Nn Nx Of On Pb Pc Pe) Ip(Et Hr Hv Hw Io It Md Mg Ml Pb) Md(Hw Io Jh Jq Mb Og Om Pc) Jl(Hr Ii Io Ir Iu Mr Ni Pe) Pc(Hr Hv Hw It Ml My Ns) Nn(Hr Ii Ms My Ns Nx) Ml(Hw Io Jm Jt Om) Hv(Hw Io Jm Om) Jh(Et Jg Mg Of) Il(Jk On Pa) Pb(Hw Io Om) Mt(Js Nf) Ni(Hr It) Rb(cT fP) Jj(jG qZ) Nx(Lu On) Pc(Pa Pd) CpUc EfUk NtqZ MbIk MiNd HrIo JrJs OfOn} jG{Jj(Et Ii Ip jI Jk Jm Jn jO jQ jT Lh lM Lw Lx Mg Mj Ms Mw MZ Nd Nn No nR Ny Oh Po Qc) mZ(hA hW iC jD Jh jO kK lM lO Lu mF Mq nB nR nU oP oQ qT rZ) Lw(lM Mf Ml Na Nk Pd Pe Pf qZ) Om(Iu Jo Mf Pe Pf) jQ(aJ jH lL lM qZ) On(Nk Pe Pf Pz) No(Nk Nr Pf) nR(jl lL Mq) kK(jH jI mW) rZ(Nq qZ) lL(kG lM) MfMz NkJp aJjT jHlM jIrY} aJ{cV(aG aM AN As aW aX bV cF cH cI Cp De) cH(aG aM An As Ba cF cT De Di dL Ef) Cp(aG aH Ax bN Cq cW cZ DL Uc) dG(Hc Jj jQ Kg Mi Pb Tn Uf Ug) aC(Aw aX Ba bE cZ Di dL jT) Dg(Ap Bb Bg Co Di Ef) jQ(bM cU dR hA jM lK) Aw(aH bN cJ cW fP) aG(aM Ba Di dL Ef) Di(aH bN) aM(aH aN) BacW aNdL jMjT} Cp{Uc(aG aP aX BA bP bV cT Dc Im It Jj Kd Kg Kq Ks Lh Mn Nb Nd Ng Ni Nn Om Qa Rh Tn Tr Ug Uk) Ad(AN aP aX BA cT Dc Di dN fP Jj) fP(aX gL Ii Jo Oy Rb Tv Ue Ug Uk Tj) Jj(aH cH cV cZ) Dg(aP aX Hr) Jo(aX Pb) Us(Lh Ug) aC(aX bE) bA(Cq cV)} Dr{My(aC Ad Af aG Bb bN Bo bX cF Cv Cw dA dB dC Dg dH Ez Fb fP Hq Hv Hw Ib Jg Jm Jp Kf Kk Ko Kp Kq Lu Ma Mi Mm Nk Nn Pb Pi Pk Pz Rc Rg Rh Uh Ul Vo) cT(aG aH aU aX bC bW cF cN cS cV De) Ba(aG bC cN) Ef(Ad aH) Hu(Ng Ny) AwOm DebA MiNy} lL{kG(jH kK mM nA Nc nI rB rX rY rZ) nA(iC jH lK lM lO mH Nc nR) nK(My Nl Nq Pe Pf) nR(hW jH nJ rB) kK(jH lK mW rB) rZ(lW lY mH mI) Nc(kC nI nL) Lw(Mf qZ) Jj(jQ mZ) lW(mF rB) MqnI NdjT NlnU JhmZ qZjR kNlK} gC{cL(Af Ao AW bA cS Cv Dg Dl Et Ex Ez Gc Hq Hv Jr Jt Jv Kf Kl Kn Ng Nk Nl Nm Nx Ny Ph Qn Ra Rc Ss Ul Uo Ut) Tn(CX Ij Kn No Nr Pb) bC(Ba Ct Cx) aH(Ez Mi)} fP{aX(Aw Di Hc Jj Kd Ke Qv Tn Ug) gL(Aw Di Jj Kd Lx Qv Tn Ug Uk) bV(Aw Hc Kd Ug Us Tj) Ef(mM mY Oy Ug) Tn(Jj Tv Uk Tj) Aw(Jj kC Oy) Ke(Rb Us) Kq(Hw Ug) TjbZ IzkC} bA{gV(aD aF aO bL bM bP bU bW bZ dB dE) cV(aP bV cF cN De dN fR) Tj(Jj Kd Li Lw Mj Nn) Em(aG cA cK Co De dH) Us(Kd Qa Un) eP(cA cK dH) AdAw LwRb TvKd aCbE} Ba{Em(aC aG bN cH cV dB DC) cN(aC aG aN bI cE cH dG) cV(aP aX bV dN Jj) fR(Ad aG aH Ax Dl) Uc(Jj Qa Un) Ad(Aw Dc) aC(aL aX) DgaP FyIm aNcZ} Ef{Uk(bP dJ It Kl Lw My Nd Ng Un) Kl(kC kI lW mF mI) mI(Al Dg Mm Nm) Ad(mF mH mM) kI(Jt Qe Vo) Dc(kC lW) Pb(mF mM) AabN BbmH DgmM NmmF UcUn JjaH VolW} cT{Em(aF Co cX DC De) fR(aH Ax cV dF) Gn(aG cF cN) Uc(Kd Qa Un) Us(Kd Qa Un) eP(aG cH cV) gV(bM bU cD) Gc(Co Qy) AdAw TjJj GdbN LwRb TvQa ImUg UkcV} qZ{jQ(hA iB Ih Il Io Ir It Jh Jj jR Lj lO Ml Na Nk Nq Oh Pf Pg qW) hV(Iu jl Pe) jR(Iu jI Pe) MsJj rZlO} Og{Nn(Ip Iv Jh Jl Jq Lx Nv Ok On Qa) Jq(Ip Jg Jh On Oz Pc) On(Ip Jh Mb Oi Oz) Nv(Lh Mn Oz Pc) JgOz} Hq{mZ(Hr Ii Jj Jl Jm mM Nc Nm Pe Pf Po) mP(Nj Pe Pf Um) kC(bI Dc Pe Tj) Tj(kN nH) HrkK PemM} Pb{kC(bI bM bN bR bX Cv eC Pe Ug) Pe(kF mZ nR) Gd(Hu Im) Pf(mZ nR) CvkF NcmZ aHeM} Jj{Aw(aH cH cV) gW(Kd Rf Tz) hA(nR Om) jQ(Nj Nk) ExcZ NgmM JkmZ UnUs aCaX bVcV} Oz{Nn(Il Im Jh Jq Lx Ok Oy) On(Il Of Oy) Ng(Jg Nv) QaJm JqPc} Nc{nA(hA jK jO lO) jI(nI nK nT) lN(kK mF nR) jH(nI nT) JkmZ} Aw{Ad(aN aP Dc) aC(aX bE cZ) Uc(Qa Un) CqkC DgaP aHfR} Un{Us(aX bV Di Nb Nd Ug) Uc(Di Ib Nb)} eM{Mw(Aa aH Kl Uc Vo) CoGc MmUf QwaH aCbE} Hu{Gd(aX dH Ij) mP(Iq Mf) mZ(Lx Vs) GccF} kC{Oy(bM Cv Pf Ur) nR(Ir Nm) NnIu} My{Gc(cF Rh) Gn(Ub Uh) GdQv} Pc{Nq(rY rZ) Lx(rY rZ) OymZ} Ng{mZ(Ii Nj) MnNv mMkK} aC{bE(aP aX cP) DcaX} jQ{iZ(bM lK) aPcU lKnY} Nn{HrOk IukK QaJm} Uc{Kq(Hw Ud Vv)} Qa{Jm(Ip Pc)} Ug{AjoQ IzoO} Vv{bX(mU nH)} bC{CvGc nOpK} mZ{NjJk jLoQ} DdcLoO EmMiNy NqPfrZ LwRbhG LxMnJq NknTjI

Figure 5 Continued

Constrained panels with 2 analytes, where 1.0E-8 >= 'model p-value' > 0. Contains 19 panels of 108,068 total panels evaluated. : Jj(aA Fr Ip Is Ji Jl Jq Lv Mu Nv Nw Oh Qa Qb Qd) aA(Fr Ji Nw Oz)

Constrained panels with 2 analytes, where 1.0E-7 >= 'model p-value' > 1.0E-8. Contains 52 panels of 108,068 total panels evaluated. : Jj(Ik Im Ir Iv Jg Jh Jk Jm Lh Lx Mi Mp Mv Nl Nn Nt Nu Nx Oi Ok On Oy Oz Po Qc Qe) aA(cV Hr Hw In Ip Is JG Jq Lv Lw Lx Mb Mu Nd Nn Nx Pb Pc Qd) Is(In Jm Og) Qd(fP Uc) NmJi Constrained panels with 2 analytes, where 1.0E-6 >= 'model p-value' > 1.0E-7. Contains 65 panels of 108,068 total panels evaluated. : Jj(Hq Ih Ii Jp Js Li Mg Mj Mq Mr Mt Mx My Mz Nc Ne Nh Nj Nq Nr Pa Pb Pc Pe Pg) Is(Fr Hw Ij Il Io Iq Ji Jt Lv Mn Mu Ng Nm Nw Ny Oz Pz) Ji(Fr Ij In Jt Lh Mm Mn Mu Og Oz Pz) Nw(Ij In Md Pb) aA(aH aL cZ Il) TjQd MuOg aJdG mZIL Constrained panels with 2 analytes, where 1.0E-5 >= 'model p-value' > 1.0E-6. Contains 113 panels of 108,068 total panels evaluated. : Fr(Hr Hw In Ip Jm Jq Lv Mb Mg Mn Mu Nd Ng Ni Nl Nw Of Og Om Oy Oz Pc Qd) Ji(Hv Hw Ii Io Jm Jo Lu Lv Md Ml Ng Nw Ny Om Pb Pc) Mu(Dr Em Gc Gd Gn Hw In Jm Lv Ng Nw Oz Qd Uc Tj) aA(aF aM aN Aw Ba cH Cp cQ Cx dG Di jQ Kc IL qU) Is(Hr Ih Ii It Iu Jo Mb Mg Mm Ni Om Pc Us) Nw(Lh Lv Ml Mm Mn My Nm Of Og Oz Pg Pz) Qd(Ed Fn Fw iA Il In Lv Pz Us) aJ(Aw Ba cH cV) jG(jI Jj) EmcT InQa StaX kKIL Constrained panels with 2 analytes, where 1.0E-4 >= 'model p-value' > 1.0E-5. Contains 246 panels of 108,068 total panels evaluated. : Qd(aX Ba bS Cq cT Dg Di eM Fa Gp Gz Hw Io Ip Jh Jm Jq Jt Ks Mm Mn Ng Ni Nm Nn Nw Ny Og Om On Oz Pc Qm Qw Tv Ug Uk Ur) Mu(aJ bF bV Cq Dk fP gC Hr Il Ip Je Jl Jq Kc Lx Mb Mg Mi Mn Of Om Pc St Ug Uk) St(aA Aw Ba cN cT cZ Di fP Fw Il Iq Jj Jm Ju Kc Ks Ms Mv Pb Tv Ug Uk Us) Nw(aX cZ fP Hr Hw Il Im Io Ip Iv Jh Jm Jt Lx Mi Mw Ng Nl Ny Oh Pc Us Tj) Lv(Il Im In Io Ip Jh Jl Jp Jq Lx Mt Mv Ng Nn Nv Og Oh On Oz Pc Qa) aJ(aG aH aM An cF cI Cp cZ De Di dL Ef jQ jT) Kc(aG aX bN bV cH cP cT Di fP Jj Nd Ug Uk) Ba(aC aN aP Aw cN cV cZ Di Dr Em) aA(Ef fP jR Ks qZ Rb rY Ug Uk Us) In(Jl Jq Lh Lx Nv Ok On) Aw(Ad aP aX bA fP Jj) Cp(Ad aX Jj Jo Uc) mZ(Hq jG Mv oP Ua) jQ(aP iZ jG Jj qZ) Og(Jq Nn Nv On) Oz(Jq Lx Nn On) IL(kG nA nR oQ) Gd(Hu Mv Ua) Is(Ks Ug Uk) bA(cV Di Em) cT(Dr eP Gn) jG(lM Lw nR) Fr(Il Iv) Ua(kC mI) Un(Ug Us) DrMy EfUk GcMv QaJm JiUg JjqZ UmoO aPjT Constrained panels with 2 analytes, where 1.0E-3 >= 'model p-value' > 1.0E-4. Contains 806 panels of 108,068 total panels evaluated. : Ug(aJ aP Aw aX BA bV Cp cT cZ Di Ef Ez Fb fP Fr Hc Im Ip It Iv Jh Jq Kd Kq Lv Lw Lx Mg Mi Ms Mv Nb Nd Ni Nn Nw Oi On oO Oy Pb Pf Pj Qa Rm Tn Ua Uf) jG(aJ aP Fr iB iC Is iZ JH Ji jO Jp Jq kK IL IO Lx Mf Ml Mp Mu Nd Nj Nk No Nv Nw Om On oP Pe Qd qZ) Jj(aJ aP aX BA bV bZ CH cN Co CT cV cZ Di Ef Ez Fb fP gL Hc jR jT Kd IL Rm Tn Ua Un) Is(Aa Ad aG AJ Aw aX Ba bN cH Cq Dd Dg Di fP Fy Kc Kf Kl Qw Rb Tr Tv Ub Uc Ur Vo Tj) On(Hr Hw Il Im Ip Iv Jh Jm Jq Jt Lx Mb Mm Mn My Nd Ng Ni Nl Nm Ns Of Oh Oy Pb Pc Pz Qa) Cp(aH aN aP BA Cq cS cT cZ Dg Di fP gL Hr Hw Il In Jt Ks Lh Mn Ng Of Uk Us Tj) Mv(aJ Ao bV Co fP In Ip Jd Jl Jq jT KC kK mM mP My nA Ng nl Og Ok Oz Uc Ue Uk) Nn(Il Im In Ip Iv Jh Jl Jp Jq kK Lx Mb Mi Mx mZ Ne Nh Ni Nl Ns Nv Oh Ok Oy Qa) Jq(Hr Hw Ii Ij Ip Iv Jg Jh Jl Jm Jp Lu Lx Mb Md Mi Mn Ne Ng Nl Nm Om Pc Qa) Kc(Ba Dg Fr gL Hw Il Im Kf Ks Lv Lw Mm Mn Ms Nb Nw nY oO Ow Qd Qv Tr Tv Tj) Nv(Hr Hw Il Io Ip Jh Jl Jm Jt Lh Mb Mg Mi Mm Mn Ng Ni Nm Ny Of Om Oz Pc Pz) Oz(aJ aP aX fR Im In Ip Iv Jg Jh Jl Jp Lh Mi Mp Mt Mx Mz Oh Ok Pc Qa Qb) Di(AN aP aX cN cS cT fP FR gL Im Iv Ji kC Lv Lx Mu Nb Nw Pb Uk) Mu(aG aX cN Co Ex Jd kK Ks mM mP mZ Qv Qw Qx Rb Tv Ue Ur Us Ut Vp) Ok(Hr Hw Ij Il Im Ip Iv Jh Jo Jp Lx Mb Mi Mn Ng Nm Og Oh Pb Pc Qa) In(Aw Im Ip Ir Iv Jg Jh Jp Mi Mx Mz Nl Nt Oh Oy Pc Po Qb Qe Un) Uk(Aw aX BA cN cT Ex Fr Im It Ji Lv Mi Nb Nd Pb Tn Ua Un) Qa(Hr Hw Il Io Ip Iq Jh Jl Mb Mi Mn Ng Ni Og Pc Pz Us) aP(aC aG aH aM AN cF cH cI cT cV dG Ef hA jM jR Pb) aX(aC AN cI De Dr fP fR Im Iv Ji Kd Kk Lv Nb Pb Qv) Jl(Hr Hw Il Ip Iv Jh Jm Jp Lx Mb Mn Ng Ni Og Oh Pc) jQ(aO dN dR gL gP hG hV jH jI IL Mf Nj Nk nY Pe) Aw(aN cT Dr Gd gL Hr Il Jo kC Ng Of Qd Uc Us) Lx(fP Hw Ip Jh Jm Ks Mb Mi Mn Mt Ng Ni Og Pc) bA(aN aW cF cH cN cZ De Dr Rb Tv Uc Us Uv Tj) mZ(aA fb Jk kK IO Ma mF Nc Nd Ng Nj nR Pb qZ) Mi(Dr gC Hq Ip Iv Jg Jh Jp Mb Nl Og Oh Pc) Qd(aC cH cN cP DI Em Fy Kl Kr Kz Rj Tr Vo) Un(Ad Hr Hw Il Jo Ks Nm Rb Rj Tv Uc Uv) Nw(bN cH Cq Dk Ks Qx Tr Tv Ur Vp) Us(bV cT Dc Fr Ji Ke Kq Lh Nb Tn) nR(aA hw jH jI kC Nm Pb rX rY rZ) Ip(Il Iv Jg Jh Jp Mt Og Oh Pc) Dr(bC Co cS Ct Ef Ez Fr Hu) Jh(Iv Mt Mx Ng Nl Og Oh Pc) jT(bE cF dM gL gP hG iZ Nk) Fr(cT Dg Em fP Ks Rb Uc) Ji(Aa Dg fP Ks qZ Rb Uc) aA(eF Hc kK Ow Qv rZ Tj) aJ(eP hA jM jR Lv Ow Pb) Jp(Io Mb Mn Ni Og Pc) cT(aN cN De dN Rb Tj) fR(aF aG aH aW cH cV) qZ(hV iB jt jR IL IO) Tn(fP Il Ks Tv Uc) Og(Iv Jg Oh Pc Qb) kK(Hq jH jI IO Pb) St(gL Hc Nd Tj) fP(bV Kd Lv Uf) jM(gP iZ nW nY) Ba(An gL Uc) Ef(Gd mI mM) Ng(Jg mM mP) Pc(Iv Mx Oh) Pe(kC rY rZ) eM(aH Nu pK) jR(iZ jI Nk) oP(qU rY rZ) Ua(oO oQ) Kq(Cq Hw) bV(cV Pb) cN(cS Ex) EzgC LwRb MyJg NaiZ NenU HqmP HcoO ItKs QbJm aCbE bMkC mIpK nAlO Unconstrained panels with 3 analytes, where 1.0E-10 >= 'AUC p-value' > 0. Contains 7,255 panels of 14,487,373 total panels evaluated. : IL[mZ(aA eD Et Fp Fr hA Hq HR Hu HV HW HX iB iC Ih Ii Ij Ik Il Im In Io Ip Iq Ir Is It Iu Iv jD jE jF JG JH JI Jj JK JL JM Jn JO JP JQ JR Js JT jU jV jY kC kE kF kG kI kK kN kO kP Lh Li IK IM IN IO Lu Lv LW LX LY Lz Ma Mb Mc Md ME MF Mg MH MI Mj Mk Ml MM MP Mq Mr MS mT MU Mv MW Mx MY Mz NA NB NC ND Ne NF Ng NH Ni NJ NK NL NM NN NO Nq nR Ns NT NU Nv Nw Ny Oe Of Og Oh Ok Om On oO oP oQ Oy Oz Pa Pb Pc Pd Pe Pf Pg Po Pz Qa Qb Qc Qd Qe qT qU qV qW qX qY qZ rA rB rC rX rY rZ) nK(aA Fr Hq Hr Hu Hv HW Hx Ii Ij Ik Im In Io Ip Iq Ir Is It Iu Jg JH JI Jj Jk Jl Jn Jo Jq Jr kG Lj Lv Lw Lx Ly Lz Ma Mb Mc Md Me Mf Mg Mh Mi Mj Mk Ml Mm Mn Mp Mq Ms Mt Mu Mv Mw My Mz Na Nb Nc Nd Ne Nf Ng Nh Ni Nj Nk Nl Nm Nn No Nq Nr Ns Nv Nw Nx Ny Of Oz Pb Pc Pd Pe Pf Pg Pz Qb Qc Qd rB rZ) nI(aA eD Et Fp Fr Hq Hu Hv HW HX iB iC Il Im Io Ip Iq Ir Is Iu jD Jg JH JI Jj Jk Jm JO Jp Jq jR Jt kG Lj IK Lu IW Lx Ma Md ME Mf MH ml Ml Mp Mq MW Mx My NA nB Nc Nd Ne nF Ng Nh Ni NJ Nk Nl No Nq Ns Nv Nx Ny Of Og Oh Om On oQ Oy Oz Pa Pc Pd Pf Po Qc Qd qY qZ rB rC rZ) kG(aA hA HR HV hW HX iB iC Ir Is It Iu jD jE jF jG jH jI Jj jP jQ jR jT jU jY kC kF kI kK kN kO IK IM IN IO IW IX LY mE mF mH ml Mk mM MP mS mT MW MY NA nB NC Nd Ne nF nH NJ NL nN nO nR Nu Og oO oP oQ Oz Pc Pd Pz qT qU qW qX qY qZ rB rC rX rY rZ) oQ(aA eD hA hR hv hW hX iB iC jD jE jF jG jH jI jK jL jM jO jP jQ jR jT jU jV jY kC kF kI kK kN kO kP lK IM IN IO IW IX mE mF mH ml mM mP mS mT mU mW mY nA nD nF nJ nL nM nN nO nR nT nU oO qT qU qV qW qX qY qZ rA rB rC rX rY rZ) nA(aA Fr hA hV hW HX iC Ih jD jE jF jG jH jI Jj jM jQ jR jU kP IK IM IO IW IX Ma Md mE Mf mH ml Mp Mq mS Mv mW My Na nB Nc Ne Ng Nk NL nN nO Nq nR Om qU qW qX qY qZ rA rB rC rZ) aA(jG jQ jR kC kE kF kI kK kN kO kP IW IX IY mE mF mH ml mM mP mS mT mU mW mY nB nC nD nF nH nJ nL nM nN nO nR nT nU oO oP qU rY rZ) jH(kC kE kF kI kK kN kO kP IW IX IY mE mF mH ml mM mP mS mT mU mW mY nB nC nD nF nH nJ nL nM nN nO nR nT nU oO oP) Nc(kC kE kF kI kK kN kO kP IW IX IY mE mF mH ml mM mP mS mT mU mW mY nB nC nD nF nH nJ nL nM nN nO nR nT nU) NI(kC kE kF kI kK kN kO kP IW IX IY mE mF mH ml mM mP mS mT mU mW mY nB nC nD nF nH nJ nL nM nN nO nR nT nU) jI(kC kE kF kI kK kN kO kP IW IX IY mE mF

Cv Cx Dc Dd dG eC Ha hB oF oK oN Or Pe Rb Tv Ug Uk Um Ur Vp Tj) Hq(Aa aH Ax Bc bl bM Cq Cv Cx Dc dG cM Fn hB Je Kz oF oK oN
Or Pe Pf Rb Ug Uk Um Ur Vp Vu Tj) Aw(Af Cq Cx Dg Dk fP Jt Nm Om) Pe(iB jF JK jM lO Ng Nn Nq) Cx(Ba bR Hc Hv Um) Mu(Aa eM fP)
Jk(Aa Cq Pf) bX(Kc Vv) cL(Cv gC) IO(Pd Pf) CoJt NqSr NejG IzfP PzUg UmbH} gC{cL(aH Dl Et Ez Fy Hb Hf Hv Hw iA Ib Jd Jo Jt Jv Kf Kl
Kn kO Ks lY ml Ml Mt mY nC Ng nH nL Nm nO nT Nu Ny Om Oz Pb Ph Pj Qm Qn Ra Rc Sr Ss Ue Uf Uh Ul Um Uo Ut Uu Wm) Tn(Af aH
bP CX Dg Dl Et Hf Ij Im Io Jg Jt Ke Kf Kl Kn My Ng Nm No Nr Ny Ok Om Oz Pb Pj Qm St Uh Ut Uu Vo Wm) Mu(aC aH bB bP cD fP Hx
Im Jk Jt Kl Nu Ny Oz Pb Qm Rc Sr St Ue) bC(Ba Cv Fy Ir Jn Jt Kf Kl Mk Nl Nu Om Oz Pb Qm Ra Ub Ug Vo Tj) Mv(aC aH bB fP Jk Jt Nu Ny
Oz Pb Qm Sr St Ue) aH(Aw Ba bQ Cp cT Ez Hc Iz Kq Mi Mw Ou) Iz(Af Al Ba Jk Jn Jt Kl Nm Rc Vo) Hc(Af Al Cx Kl) Uf(Jo Jt Pb) bW(nC
nH Oz) My(Kc Oa) AfAw AlHq GzKc NqPb MaOz HfVv QdOm bMml bPmP} eM{Tn(Aa Af aH Ap Bb Bc cJ Cu Cw Dg Dl Et Ez fP Fy hB
iH Io Jg Jo Jp Jt Ke Kf Kl Kn Ko KQ kS nJ Nm Nw Ny Ok Om Oz Pb Pj Qa Qe Rc Sr Ss Tr Uf Uh Un Vo) Mu(aC aG aH bB iA iJ mH ml mM
mS mZ nD nH Oz Pb Qm Ue) Aa(Aw Cp Hu Jd Kq Mv Mw On Vs) aH(Aw Cp Fr Hc Iz Mv Mw pK Qw) Mv(aC iA Oz Pb Ue) Qd(Jt Kf Om
Oz Uh) pK(aS cL cZ mP) Mw(fP Pb Sr) Cp(cV Dg) HqnD IsPb OibN cLoQ} jG{mZ(Fp Fr Hq Hu Hv hW hX iC Im Iu jD Jg JH jI jO kK Lu Lx
Me mF Mh Mq Mu Mw Na Nk Nq nT nU Nv Om On oP oQ Pc Qa Qc Qd qT rB rZ) jI(jQ jR jT kG kK IM lW nO nR nU) jT(aJ aP iZ Jp Nv Om
On) Is(Iu Jm Mf Nk Pz) kK(Fr Iu Mq Mu Nq) Nq(nl rY rZ) Mf(Jq Nw Om) Iu(kF Om On) nR(jH Mq rB) In(rY rZ) dN(jQ nY) nU(Ne Nl) NoNr
MkOm MqkN NkOn HumP aliZ} Cp{eP(aC AD Af aG aH al aN Ap As AW aX bA bB Bg bN bO bU bX cD cE cF cl cK cN Co cP cQ Cs cU
Cw dC dD Dg Di DL dN dR eF Em fR Fw GL gP) dX(aC aD Af aG aH aN Ap As aW bA bN bO cE cN cP dC Dg Dl dN Em) fP(Ad Rb Us)
Uc(gW Qd) Pb(mM mP) KjgW} Mu{fR(aC Af aG aH Aj Ap cE Dg Dl In Iz Jo Jt Kl Ks Ly Ng Nk Nm Om Oz Pb Qm Qv Qz Ss Uc Ue Ug Uu
Vo) Em(aC aG aH Ap bN cJ dC Dg Iz Jy Kd Mh Ng Qm Qv Ue Ug) mZ(fP Iu Mt Pd Pg Po) Aa(kK nA nD nl nK) mP(Jl Pe Qe) oQ(Ug Um)
PejT} Mv{Pe(kE mE mF ml mP mW mZ nA nD nF nH nT nU oP) Ue(Em fR kE kN kP lW mF ml nB nD nH nl nT) Aa(fR kK kO nA nC nD
nH nK nL) Pf(ml nD nH nT nU) Em(aC aG aH bN) Jd(mZ nK oQ) fR(fP Oz Pb) nA(Dd jL Pg) Co(ml nT) Nm(mP nR) oQ(Kz Um) UcQd
OumP UvnT PdnD jVkK} gV{bA(aC aD aF aG aH al aJ aL aN aO aS aU aX bF bJ bL bM bN bO bP bQ bU bX cA cC cD cE cF cG cl cK cN
cO cP cV cW cX dB dC dE dF dH dl dM dX) cT(aC aD aF aG aH bN bP bU cD cl cN cP) dM(aC aD aG bN cV dR) aC(aX gL)} Hq(Tj(kN lW
mE mF mH ml mM mZ nA nD nH oQ) mP(Aa aY Dd Iq Nj Pe Pf Um Vt) mZ(bP Dc Ii Jm Nj Pe Pf) Pe(ml nD nF nH oQ) Pf(nA nD nF nH)
Um(kN mH mM) Aa(kK nA) Ur(mF oQ) blmH} Pb{kF(aC aZ Bc bG bl bN Bo bR Cv Dc Dd fP hB kQ oK oN Pe Tr Ub Ug Uk Um Uv Tj)
ml(Ba bQ Di Tn Uu Vv) mP(Hc Ib Pi Tn Us Vu) bQ(lW mM) mZ(bN Ib) nA(Ba bH) MwfR HcmM UmmU} nU{Nl(eD hA iB iC jD jE jH jI jK
jL jT jV lM IN qT qV qY) Ne(hA jD jH jL jT jV qV) Nk(jH jK jV) Nj(jD IM) Hu(Pe Pf)} jT{aJ(aC aD bE bM cl cQ hA jM) iZ(aD aG aM bE
bM cQ jM) Pe(Fr Is Jp Nv Om) aP(aC bE jM) jM(dG dM) Wmls aDjl bEcF} Em{Tn(Et Hw Jt Ks Om Uh) On(Aa Hb Hw Jt Ok Om) Fr(Dg Hb
Hw Om) Hu(Jo Ng Ug) My(Qv Ug) bN(Ba cT) AwaG MwUl HbLh} Is{Wm(qT qU qV qX qY rA) In(Nm Nu Om rX rY) Jm(fP Hw Om Pz)
Og(Hw Iq Ny Om) gW(Tv Us) lIPz RbfP} dX{Aw(aC aG aH bA bN bO cD cE cP Cs) cT(aF bM bN bU cD dB) bA(aF cC cV De) aC(aX bE)
aG(Cu Fr)} mP{Hu(Aa fP Io Jl Jt Lh Li Ma Mf Mm Nm Om Pe Pf) Hc(Dg fP Jt) DgIz IbbM UmaY VvbX nHpK} eP{Aw(aC aG aH bA bN bO
cD cP Cs) bA(aF cC De) cT(aF bN De) aC(aX bE) FraG} jM{aJ(cP jQ jR nW) aP(bU cD cL jQ) iZ(bU cP dN) jQ(dR nY) bUjl dNgP jHoK}
Hc{ml(Ad Al Cv fP hB oF) fP(kF kG mM mT) AlmZ} bX{Vv(lY mF ml mU nA nC nH nJ nL) ml(Di Tn)} gW{Ex(aJ cN Hw Jo Kg Ks Nd)
Qd(Tt Tv) QxiZ} jQ{jH(aF aM aO bF dN dR) dR(dN lK) aJlK aPhB} Iz{fP(kF kK oP oQ) oQ(Jp Lh Um) DgkF} fR{Tn(Aa Jo Kl Om) AaOn
AwDg EtFr MyUg} bH{Um(kN kO lW lY mT mW) LdlW} nA{lO(Ne Nk Nl Pf) Aa(Hu Ng) NelM} pK{nO(aK bC cL) dK(bP oF) bCcl cLkO}
mZ{jL(Im Mq) NkqT HuVs IiJk JhiC} kK{jV(Fr Ng Nl Nn) IN(Na Nl)} In{Qc(rX rY rZ) rZ(Pe qU)} cT{aH(oV oW) QdSs dFoW} oQ{Ug(Aj
Oy) DdcL NfQy} Nq{Pd(rY rZ) PfrZ} nT{Nk(jH jl) Hubl} hA{aJdN aPcD} nR{NujH NljV} AaHunD FrRbfP lbUrml IjOmPc KrTkOh
PemFlM bRcLjB bVdUiH Unconstrained panels with 3 analytes, where 1.0E-9 >= 'AUC p-value' > 1.0E-10. Contains 4,393 panels of 14,487,373 total panels evaluated. :
Jj{Qb(aA Et Fp Fr Hq Hr Hu Hv Hw Hx Ih Ii Im In Ir It Iu Iv Jg Jh Jk Jl Jm Jn Jo Jp Jr Js Jt Lh Li Lj Lu Lw Lx Lz Ma Mc Md Me Mf Mg Mh
Mi Mj Mk Ml Mm Mn Mp Mq Mr Ms Mt Mv Mw Mx My Mz Na Nb Nc Ne Nf Ng Nh Nj Nk Nl Nm No Nq Nr Ns Nt Nv Nw Ny Oe Of Og Oi
Ok On Pa Pb Pd Pe Pf Pg Pz Qa Qc Qd Qe qZ) Oh(Et Fp Fr Hq Hr Hu Hv Hw Hx Ih Ii Ij In Ir It Iu Jg Jl Jm Jn Jo Jp Jr Js Jt Lh Li Lj Lu Lw Lx
Lz Ma Mb Mc Md Me Mf Mg Mh Mi Mj Mk Ml Mm Mn Mp Ms Mt Mv Mw Mx My Mz Na Nb Nc Nd Ne Nf Ng Nh Nj Nk Nl Nm Nn No Nq
Ns Nt Nw Nx Ny Oe Of Og Oi Om On Pa Pb Pd Pe Pf Pg Po Pz Qc Qe) Qd(Et Fp Fr Hq Hr Hu Hv Hw Hx Ih Ij Ik Im In Iq Ir It Iu Iv Jg Jh Jl Jm
Jn Jo Jp Js Jt Lh Lj Lu Lw Lx Ly Lz Ma Mb Md Mf Mg Mh Mi Ml Mm Mn Mp Mt Mv Mw Mx My Mz Na Nc Nd Ng Nh Ni Nj Nk Nl Nm Nn
No Nq Nr Ns Nt Nu Nv Nw Nx Ny Of Og Oi Ok On Pa Pb Pc Pd Pe Pf Pg Po Qa Qc qZ) Nv(Et Fp Hq Hr Hu Hv Hw Hx Ih Ii Im In Ip Iq Ir It Iu
Iv Jg Jh Jk Jm Jo Jp Jq Js Li Lj Lu Lw Lx Ly Lz Ma Mc Md Me Mf Mg Mh Mi Mj Mk Ml Mq Mr Ms Mt Mv Mw Mx My Mz Na Nb Nc Ne Ng
Nh Nj Nk Nl Nn No Nq Ns Nt Nw Nx Oe Of Og Oi Ok On Pa Pd Pe Pf Pg Po Qa Qc) Mu(Et gW Hq Hr Hu Hv Hw Hx Ih Ii Il In Io Iq Ir It Jg Jh
Jk Jl Jm Jn Jo Jp Jr Jt Lh Lu Lw Lx Lz Ma Mb Mc Md Me Mf Mg Mh Mj Mk Ml Mm Mn Mp Mq Ms Mw Mx My Mz Na Nb Ne Nf Ng Ni Nk
Nm Nn No Nr Ns Nw Ny Og Ok Om On Pb Pd Pf Pg Po Pz Qc Qe) Ip(Et Fp Fr Hq Hr Hv Ih Ii Ij Il Im Iq Ir Jg Jh Jm Jo Jp Jr Js Jt Lh Li Lu Lw
Lx Ly Ma Mb Md Mg Mi Mj Ml Mm Mp Mq Mr Mv Mx My Mz Nc Nd Ne Nh Ni Nj Nk Nl Nm Nn Nq Ns Nt Nw Nx Ny Og Oi Ok Om On
Pa Pb Pc Pg Po Pz Qa Qc Qe) Oy(Et Fp Fr Hq Hr Hv Hx Ih Ii Ij In Io Ir Jg Jk Jl Jm Jo Jp Jr Jt Lh Li Lu Lw Ly Lz Ma Mb Mc Md Mf Mg Mh
Mi Mj Ml Mm Mn Mp Mq Mr Mt Mv Mw Mx My Nd Ne Ni Nj Nk Nn Nq Ns Ny Of Og Oi On Oz Pb Pc Pg Po Qe) Qa(aA Fp Fr Hq Hr Hw
Hx Ih Ij Ik Im In Ir Iu Iv Jg Jh Jk Jm Jn Jo Jt Lh Lj Lu Lx Ly Lz Ma Mb Mg Mh Mi Ml Mn Mp Mr Mv Mw Mx My Mz Na Nc Nd Ng Nj Nl Nm
Nn No Nq Ns Nt Nw Ny Og Oi Ok On Pa Pb Pe Pf Pg Qc) aA(cV Et Hq Hr Hv Hw Hx Ih Ii Ij In Io Iq Ir Iv Jh Jl Jo Jp Jr Js Lh Li Lj Lw Ly Lz Mb
Mc Mf Mh Mi Mj Ml Mq Mr Mt Mw Mx My Nc Nd Ne Nf Ng Nh Ni Nk Nl Nq Ns Nw Og Ok Om On Pa Pe Pg Po Qc Qe qU) Jq(Fp Fr Hq Hr
Hv Hw Ij Im Io Iq Ir Jg Jh Jm Jp Js Li Lu Lx Ly Mb Md Mg Mh Mi Mm Mq Mr Mt Mv Mx My Nc Nd Ne Nh Nj Nk Nm Nn Nq Nt Nw Nx
Ny Oi Ok Om On Pa Pd Pg Po Qc Qe) Nu(Et Hq Hr Hv Ih Ii Ik Im Io Ir Jh Jk Jl Jo Jp Lh Li Lv Lx Ma Mb Mg Mi Mm Mq Mr Mv Mw Mx My
Mz Nc Nd Ne Ng Nh Ni Nl Nn Nq Ns Nt Nx Of Oi Oz Pa Pc Pd Pg Po Qc Qe) Oz(Et gW Ih Ik Ir Jk Jm Jp Js Lh Li Lv Ma Mg Mi Mp Mx My
Mz Nc Nh Nl Nq Nt Nw Nx Oi On Pg Po Qc Qe) Iv(Fr Hq Ik Im Io Jg Jh Jk Jm Js Lh Lv Lx Mq Mv Mz Nh Ni Nl Nn Nt Nw Nx Oi Ok On Pc
Qc) Ok(Ij Ik Im Iq Jh Js Lx Ly Ma Mb Mx Na Nc Nd Nh Nl Nn Nq Nx Oi) Pc(Et Ik Im Ir Jg Jh Jk Jl Jm Jp Js Lx Mg Mv Mz Nn Nw On Qc Qe)
jG(Io Jn Jo jR Js kG Ml Nd Ng No Nq nU Nx Of Qe) Ik(Fr Ir Jg Jh Jm Jp Js Lx Mp Nd Nw On Pa Qc) gW(Al Bc Ch cN Ef It Iz Jl Jy Kd Mj Qx)
Fr(Ij Io Lv Ly Nc Nd Nh Nj Nl Nx Pa) Jk(Ir Jh Js Lv Lx Mz Nl Nt Nw Nx Qc) IL(Is jT Lw lY mS nC nD nH nL) Lv(Hv Ir Jh Js Lx Mr Oi Qc)
Ji(In It Li Me Mg Mt Oe Of) Nx(Il Im Jh Lx Mi Mv Mx Nn) Io(Jg Jp Lx Nw On Qc Qe) Jh(Lx Nc Ne Nh Nl Pb) Ni(Jm Js Lx Qc) Om(hA Ij In
Nw) qZ(hV Jm jR Og) Mv(jQ mZ Nl) Ua(fR mZ oQ) Im(Jm Ly Nl) Is(hA jD qU) Cp(aH cV) Jg(Nd Pb) Nw(Mm Nm) oO(bH Um) AwaH BacV
DrHq GnHu MqNh NkjQ kKlO} IL{nI(Hr hV Ih Ii Ik It Iv jE jF Ji Jl Jn jQ Jr Js jU jY kF kK kN kP Lh lM lO Lv Lw lX Lz Mc mF Mg Mi Mj
Mk Mm mP Mr Ms MT mY Mz Nb nC nD nL NN NR Nu Nw Oe oO oP Pb Pg Pz Qb Qc qT qU) mW(eD hX iB iC jD jF jM jP jQ jT jV jY kC

Ma Mf Mm) Em(Ap dC Hv) Jd(mF mH ml) Pf(mF mS mW) Pg(mF nD nU) nT(bI cE Qx) Dd(ml nU) aG(fR Kc) kK(jL Nm) AanI ComH
UemE aFoQ aHfR fPmM nAjY} jG{mZ(hA hV Hx Ip Is Jk jP jQ kN kO IM mT mU Mx nA nB nF Ng nJ NI nR Of Oz Qe qV rC rY) jI(jE jO
kF mE mH ml mT nA nB nI nN rY) Om(Hr Hw Jg jQ jR kK Of Og) Nk(Jp Lw Lx nU Nw rZ) kK(hX Lx mW Ng NI) Lw(IM NI On) jT(Fr gL
Jq) Mf(Ji On) Na(rY rZ) Is(NI Og) nR(hX mW) NoPf NqnK HwOn InrX IukG PzNw cFdN jQIM} gC{bC(Ao Bo Cp Ct Cx DI Gc Hf Io It Je
Mx Ng Nm Qc Qn Us Vt) cL(Af Hc Ic Ij Im Ju Kc Kd Ke Kq Nd NI No nU Or Qu Rb Ug) Tn(aO cJ dB Fy Ks Mt UI) Pb(bW Jh Mi Mw Qy)
bP(Ez Hc kG Kq Mi) Iz(Dg fP Om Qm) Af(bW Kq Vv) Hc(Bn Io Jt) Dg(Aw Cp) Ez(bB fP) Io(Vs Vv) Jt(Ba Nt) Oz(Mi Qd) CoGc MuaO QeOu
VoVv VsaH bBiH} Is{Jm(Io Iq Ji Jt Lh Lv Mm Mn Ng Ni Nm Ny Og Oz Pc) Og(Ih Ij Io Jt Lh Mm Mn Ng Ni Nm Nu Oz Pz) In(Io Iq Mm Mn
Mr Ni Ny Oz rZ) II(Hw Io Iq Jt Ng Nm Om Oz) Pz(Hr Hw Ji Lv Mu Ni Oz rB) Pe(jH rY rZ) Hw(Io Ny) fR(Et Om) gW(Ks Uk) DiKf WmqW
NmNi UgfP PfjT} Mu{Gn(Cq cV dA Dc Fb Ih Kg Kx Lh Mw No Ok Oz Pa Tt Ug Vs) Gc(bG bM cB dL Jc Mf Nx QI Uh Wm) fR(cJ Et fP Ii
Mh NI Pj Qn) Em(Aj bA cP dH Jo) eM(Aa fP IW mP nA) Pe(ml mZ nF oQ) mP(bM Ih Im Mf) fP(ml mM oQ) mZ(mM Nm) CpUc MmJi MzIj NfaC jVkK} Pb{kF(Aa bH bW bX Cq Cx hG kS oF Or Pf Qx Qz Rb Uh Up Ut) eM(aH bN Cp Jd Jk mF Nu Qy) mI(Bg Hc Qu Rc Ub Tj) mZ(Ba bH Pe Pf Qu) mP(Ba Co Dc Uu) Qu(lW mE mM) fR(Fr Hu Jk) Em(Hv Mw) GcNq IbkG TnnA UroP UumF VumE VvnJ bQmH} Hq{Tj(Gc kF lX mS mW nF nJ nK nN nT) Pe(kE kF kN kO mF mM mU nA nJ nT) mZ(Cv Jl Lx Mf mM Nm Ok Po Rb) Pf(kO mI mU nU) mP(Al Hw Pd Uo) Um(kO nF nJ) Aa(nD nF) Gc(cS Vv) EmQd GncF JofR UroP bInH eMmI} Cp{eP(aE aP aS Ax aZ Bb BC bE bG bI bM bP bV bZ cB Ch cT cZ De dG dM eM Fr) dX(Ad aX cD cI cK dR gL) Dg(aJ eF Ni) fP(Jo mP Uc) Ad(aN gW) AaEm JteM OmfR aJdG} bA{gV(aE aK aM aR aV aW aY bB bC bH bI bR bS bV bZ cB cJ cL cQ cS cU cZ dA dD dN dR) eP(aX bN bU cS) Em(bN Co De) Gc(Mi Nn Qy) cSdX eMpK} jT{aJ(aN bG cD cF cW dK) iZ(aC aN bG bU cI dC) bE(dM fP hG jH) aP(aL hB) jI(aG cZ) OnPe cFjM cIdM dChG} Hu{mP(Dg Jg jL Lj mM Mn Mt Or Pd Pz Tr) Gn(Aa Ii Jo Kn Lu) Gc(Jo Ug) Pe(nD nM) mZ(Lx mM) EmcP} eM{Tn(Bo bX Ks Li Ng nY Uu) pK(bC bJ bW cV mF) Aa(Om Po Uf) Mw(Kl Oz) gV(aJ dM) DgQd FrOz NunJ} jM{iZ(aI bE bN cA cD cR cX jQ jR nW oK tF) aP(cE hA hB) gP(bU lM nW) aJ(bU oK)} Em{Fr(aC aG bN Et Ul) Tn(Aa fP Hb Kf) On(bN Dg Ks Uh) Mw(Ap Hw) BaaG HvcF HbNw UtbN} Gn{Om(Co Hc Jk On) Hb(Aw Cu Iz) Aa(Cu Vv) Tn(Et Jt) Ul(Mw Ut) WmcF FrKf LuOu KnUt} cT{dX(aJ As Aw cI cQ) Gc(cF Im Li Nn) Dg(fR Kc) Qd(Uc Vo) eP(Aw Fr) gV(cF gP)} fR{Tn(Dg Et Jt Kf Ks Nm) Aw(Jo Ng Om) Ba(aC Dg) Om(Fr Nw) EtUf HvOz} jQ{jH(aI bE bM bZ dD dH fP) lK(aP cD cI nY) Nl(nU Nw) InhV cUlM} pK{bC(aW mI nC nH nL) mP(aW nC nL) cL(nF nH) mI(cV oE) bBcS dKfP} Gc{Co(bR cG Di Pa Rg) Fr(Cv Om) Hc(Jt Om) UbbC UfcF bRcS} mZ{Ib(aY Lh mI Nd Sr Ug Ur) Ng(Jl Ok) Hc(fP Jp) NjqT} nU{Nl(jF jO jR jY lK qX) Nk(hA jD jL) NejP NjjV} Aw{eP(aE Ar As cE) Dg(aJ aP) dX(As dC)} Hc{fP(lX mF mU) mI(mM Rb) AdnT UcmP UgoQ} Vv{bX(kF kN kO lW nD nN oP) UbmI} Iz{oQ(bI Tr Ug Ur) DgkG KlkF fPmU} Ba{As(dX eP) UcQd KcaG aCbE aFdX} aP{bI(qU qX rA) hA(bQ dN) hBjR} rZ{Pf(In Jh Na) NqPe NaPd InJm} gV{dM(cD cF cO dH) aCbE} Qd{Hw(bX gW) DiKf SsaO} Kc{Dg(bZ Fr) IlbN bFoQ} nA{NkjK NllM PelO PfrA} Um{bH(kI nI nL)} cL{oV(aG hC) nFpH} dX{AocP AsFr aGbZ} jV{kK(Jk Ne Nq)} kF{IbfP IujL OyPe} Ng{NmmP PcmI} In{HvOm JmrY} jH{NlnI PznR} AsFreP BoDimI ChUgkI CoJtmP ExKjgW GzTnKs MmJiOz NemFlN UrOyoQ aHbQoV

Unconstrained panels with 3 analytes, where 1.0E-8 >= 'AUC p-value' > 1.0E-9. Contains 7,753 panels of 14,487,373 total panels evaluated. : Jj{Fr(Et Fp gW Hq Hr Hu Hv Hw Hx Ih Ii Il Im In Iq Ir It Iu Jg Jh Jl Jm Jn Jo Jp Jr Js Jt Lh Li Lj Lu Lw Lx Lz Ma Mb Mc Md Me Mf Mg Mh Mi Mj Mk Ml Mm Mn Mp Mq Mr Ms Mt Mu Mv Mw Mx My Mz Na Nb Ne Nf Ng Ni Nk Nm Nn No Nq Nr Ns Nt Nv Nw Ny Oe Of Og Oi Ok Om On Pb Pd Pe Pf Pg Po Pz Qc Qe qZ) Nx(Et Fp Hq Hr Hu Hv Hw Hx Ih Ii Ij Ik In Io Iq Ir It Jg Jl Jm Jn Jo Jp Jr Js Jt Lh Li Lu Lv Lw Ly Lz Ma Mb Mc Md Me Mf Mg Mh Mj Mk Ml Mn Mp Mq Mr Ms Mt My Mz Na Nb Nc Nd Ne Nf Ng Nh Ni Nj Nk Nl No Nq Nr Ns Nt Nw Ny Of Og Oi On Pa Pb Pc Pd Pe Pf Pg Po Pz Qc Qe) Ik(Et Fp Hq Hr Hu Hv Hx Ih Ii Ij Im In Io Iq It Iu Jk Jl Jn Jo Jr Jt Lh Lj Lv Lw Ly Lz Ma Mb Mc Md Me Mf Mg Mh Mi Mj Ml Mm Mq Mr Ms Mt Mv Mw Mx My Mz Na Nb Nc Ne Nf Ng Nh Ni Nj Nk Nl Nm Nn No Nq Nr Ns Nt Ny Oe Of Og Oi Om Pb Pd Pe Pf Pg Po Pz Qe qZ) Lx(gW Hq Hr Hu Hv Hw Hx Ih Ii Ij Im In Iq Ir It Jg Jl Jm Jo Jp Js Lh Li Lj Lu Lw Ly Lz Ma Mb Md Mf Mg Mi Mj Mk Ml Mm Mn Mp Mq Mr Mt Mv Mw Mx My Mz Na Nb Nc Nd Ne Ng Nh Nj Nk Nl Nm Nn No Nq Nr Ns Nt Nw Ny Og Oi Om On Pb Pd Pg Pz Qc Qe) Iv(Et Fp Hr Hu Hv Hw Hx Ih Ii Ij Il In Iq Ir It Iu jG Jl Jn Jo Jp Jr Jt Li Lj Lu Lw Ly Lz Ma Mb Mc Md Me Mf Mg Mh Mi Mj Mk Ml Mm Mn Mp Mr Ms Mt Mw Mx My Na Nb Nc Nd Ne Nf Ng Nj Nk Nm No Nq Nr Ns Ny Oe Of Og Pa Pb Pd Pe Pf Pg Po Pz Qe) Ok(Fp Hq Hr Hu Hv Hw Hx Ih Ii Il In Io Ir It Iu Jg Jk Jm Jo Jp Jr Jt Li Lj Lv Lz Mc Md Me Mf Mg Mj Mk Ml Mm Mp Mr Ms Mv Mw My Mz Ne Nf Ng Ni Nj Nk Nm No Nr Ns Nt Nw Oe Of Og Om Pa Pb Pd Pf Pg Po Qc Qc) Oz(Fp Hq Hr Hu Hv Ii Ij Il In Io Iq It Iu jG Jn Jo Jr Jt Lj Lu Lw Ly Lz Mb Mc Md Me Mf Mh Mj Mk Ml Mm Mn Mq Mr Ms Mt Mw Na Nb Nd Ne Nf Ng Ni Nj Nk Nm No Nr Ns Ny Oe Of Og Om Pb Pc Pd Pe Pf Pz qZ) Nw(Et Hq Hr Hv Hw Hx Ih Ij Im In Iq Ir Jg Jh Jm Jo Jp Js Jt Lh Lj Lu Lv Ly Mb Md Mg Mh Mi Ml Mn Mq Mr Mv Mx Mz Nc Nd Ne Nf Nh Ni Nj Nk Nl Nn Nq Nt Ny Oi On Pa Pb Pd Pe Pg Po Pz Qc Qe) Nh(Fp Hq Hr Hv Ih Ij Im Io Ir Jg Jm Jo Jp Js Jt Lh Lv Ly Ma Mb Mc Md Mg Mi Mj Ml Mm Mp Mr Mv Mx My Mz Na Nc Nd Ne Ng Ni Nn Nq Ns Nt Ny Og Oi Om On Pa Pb Pc Pd Pg Po Qa Qc Qe) Lv(Et Fp gW Hq Hr Hw Ih Ii Ij Im In Io Jg Jl Jm Jo Jp Jr Lh Li Lu Lz Mg Mi Ml Mp Mq Mt Mv Mx My Mz Na Nc Nd Ne Ng Ni Nj Nk Nl Nn Nq Nr Ns Nt On Pa Pb Pc Pd Pg Po Pz Qe) Jh(Et Fp Hq Hv Hw Ih Ij Im Io Ir JG Jl Jm Jo Jp Js Lh Lu Ly Lz Ma Mb Mg Mj Ml Mn Mp Mq Mr Mv Mx My Mz Nd Ni Nj Nk Nn Nq Nr Ns Nt Og Oi Om On Pa Pd Pg Po Qc Qe) Js(Hq Hr Hv Hw Ih Ij Im Io Ir Jg Jm Jp Lh Lj Lu Ly Lz Ma Mb Mg Mh Mi Ml Mn Mp Mq Mr Mv Mx My Nc Nd Ne Nj Nl Nm Nn Nq Ns Nt Ny Og Oi Om On Pa Pb Pg Qa Qc Qe) Jg(Hq Hr Hv Hw Ih Ij Im Iq Ir jG Jm Jo Jp Lu Lw Ly Mb Me Mg Mj Ml Mp Mq Mr Mv Mx My Mz Na Nc Ne Ni Nj Nk Nl Nn Ns Nt Ny Oi Om On Pa Pd Pg Po Qc Qe) Nu(Ba Fp Hu Hw Hx Ij Il In Iq It Iu Jn Jr Jt Lj Lu Lw Ly Lz Mc Md Me Mf Mh Mj Mk Ml Mn Ms Mt Na Nb Nf Nj Nk Nm No Nr Ny Oe Og Om Pb Pe Pf Pz) Jm(aA gW Hq Hv Hw Ij Io Iq Ir Jk Jp Lh Lu Ly Ma Mb Mg Mi Mn Mp Mq Mr Mv Mx My Mz Nc Nd Ne Ng Nj Nl Nn Nq Ns Nt Ny Og Oi Om On Pa Pb Po Qc Qe) Ir(Hq Hr Hv Ih Ij Im Io Iq Jo Jp Lh Ly Ma Mg Mi Mj Ml Mp Mq Mr Mv Mx My Mz Nc Ne Ni Nj Nl Nn Nq Ns Nt Ny Oi On Pa Pb Pd Pg Po Qc Qe) Jq(Et Hu Hx Ih Ii Il In It Iu Jl Jn Jo Jr Jt Lh Lj Lw Lz Ma Mc Me Mf Mj Mk Ml Mp Ms Mw Mz Na Nb Nf Ng No Nr Ns Oe Of Og Pe Pf Pz) Qc(Hq Hv Hw Ij Il Im Iq Jo Jp Lh Lu Ly Ma Mb Mg Mi Mn Mp Mq Mr Mv Mx My Mz Nc Nd Ne Nj Nl Nn Nq Nt Ny Oi Om On Pa Pb Pd Pz Qc) Im(Et Hq Hr Hv Ih Ij Io Iq Jk Jo Jp Jt Lh Lw Mg Ml Mp Mr Ms Mu Mx Mz Nc Nd Ne Nf Ni Nj Nk Nn Ns Nt Og Oi On Pa Pd Pg Qe) jG(hV Hx iB iC Ij Il Iu jD jH jK jU kE kF lL lO Lz Ma Mb Mf Mh MM mP Mq Mr Ms Mt MW My Nj Nm Ns Nt Oe Oi rX rY) Nl(Et Hq Hv Ih Ij Io Jl Jo Jp Lh Ly Ma Mg Mi Ml Mm Mp Mq Mr Mx My Mz Nd Ni Nn Nq Ns Nt Oi Om On Pa Pb Pc Pg Po Qe) Oi(Et Hq Hv Ih Io Jk Jl Jp Ma Mg Mp Mq Mr Mv My Mz Nc Ne Ni Nj Nk Nn Nq Nt Og Om On Pa Pb Pc Pd Pg Po Qe qZ) Qa(Et gW Hu Hv Ii Il It Jl Jp Jr Li Lw Mc Md Me Mf Mj Mk Mm Mq Ms Mt Nb Ne Nf Nk Nr Oe Of Pd Pg Po Qe qZ) On(Hr Hv Ii Ij Jt Ly Mb Md Mg Mh Ml Mm Mn Mr Mv Mx Mz Nb Nc Nd Ne Ni Nj Nn Nr Ns Nt Ny Om Pa Pb Qe) Ip(Hu Hw Hx In It Iu Jl Jn Lj Lz Mc Me Mf Mh Mk Mn Ms Mt Mw Na Nb Nf Ng No Oc Of Pd Pe Pf qZ) gW(aJ aK aP Aw Bg Di Ez Fb gL Ha Hf Ib Jk Kc Ko Kq Mr Nb Oa Pe Qe Qh Qw Qz Rf Rm St Tr Uf) Pc(Hq Ih Ii Ij Jo Jt Lh Li Lw Ly Ma Mi Mm Mp Mq Mr Mt Mx My Ne Ng Ni Nk Nq Nr Nt Om Po) aA(Fp Hu Il It Iu Jn Jt lL Lu Md Me Mk Mm Mn Mp Ms Na Nb Nm No Nr Ny Oe Of Pd Pf Pz qZ) Ne(Hq Io Jp Lh Ly Ma Mg Mp Mq Mr Mv Mx My Mz Nd

Figure 5 Continued

My Qd) oW(eM kO nC nH nL) Cx(Ba cT Iz Ld) Mi(bL Nu Sr) Kq(Om Qe Sr) Af(Cp Qd) Ba(Io Kl) Ez(Nu Og) Iz(Ib Kf) Kc(aW bN) Vv(aW Kf) bW(kO nL) AwDl DgHc NmUf MwSr HqJt QubP} qZ{hV(Fr Ii Ij Im Ip Iq Jm jO Jq Jr lO Lx Ly Lz Me Mk Mr Mt Nb Nf Ni Nj Nx Ny Og Qd} jT(Fr In It Jh jl JQ Lu Lv Ms Mu Mv Mz Ng Nl Nn Nv Ny Om On Oy Pa) jR(Iq Ir jO Jq Lu Ml Mv Mw My Ne Ng Nl Nn Nv Nx Of On Pa Pd) Ji(hR HW jl jM jO jP Js lM lO Mq Nm On Pf) Nw(Et Hv Il lu jF Jl Jt jV IN Md Ni On Pz) jQ(eD iB jD jF jK jP jU jY 1K IN qV) mZ(hW hX jl jP kO IK mF mW nT rA) Lw(In jl jK jO jV) rZ(ln jU Na) Mj(Hw Pe) ll(Jp Lv) MyLh lojP hArX nlkP nJoP} Cp{eP(aF al aK AL AO aQ aU aV aY Ba bF bJ bL Bn Bo bQ bW cA cC cG cJ cL cM cO Cq cR cS Ct Cu CV cW Cx cY DB Dd dF dH dl DK) dX(aE aJ bB bM bU cA cF Co cQ CS cU cV Cw Dl dL dM eF gP) fP(aP Cq eM Hr li Jm kN Ks Og Ug Uk Tj) Dg(aN aP bA dL dN dR fR gL) Ad(aC aG aH bB) eM(aC Af aG Oz) Aa(bN cV dC) aH(Il Uc Us) gW(Hw Of Uk) mM(cV Jt Nm) Qd(Kf Om) NbOm UccN JtmP UsbB mloF} Hq{mZ(bH Cw Dd Hr Ib Ir Jo Li Lj Mm nA Nd oF Oh Qa Qe Qw Qx Vu) Tj(kE kG kl kK kP lY mP mT mU mY nB nl nM nO nR nU) Pf(kE kF kN mE mF mH mM mW nl nJ nT oQ) Pe(kK mE mH mW nB nC nl nL nU oP) mP(bM bR Dc lr lu Mf Nd Po Tn) Um(kE kG nD nM nO nT nU oQ) Em(bA cN Fr Hv Jo) ml(bl oF Qx Rb Vu) mM(bH Dd Kx) Aa(mU nK) Gn(cN My) Nm(kK nR) Vu(kN nH) Pd(nD rZ) CtTk MufR QekK UgoQ aHeM blkN bRnD} Mv{Gn(aD DC fP Iz Jo Ju Jv Ko Mg Ng Nm Of Pf Qh Tt Uh Uu) Ue(aZ cV kK kO lY mP mT mW mY mZ nA nC nL nM nO nR) mP(Co Dd Io Iq Nj nU Ow Pd Pf Pg Um) Em(cE cJ In Jo Mg Nm Oz Qm) mZ(li Jo Mf mM Ok Oz Pc Pg) Pe(kF mH mM mU nB nJ) Pf(kE kP mH nF nM) ml(aC Kz oF) nA(Pd Qe qU) kK(Jp Li nT) Uc(Fr Un) Qd(aG bN) Jd(lW nT) fR(Ks Vo) nU(Io Iu) mM(Co Or) oQ(aO bI) DdmH MmJi OyOz PdrZ bBeM fPnH} Mu{Gn(Aj aN Bg cD cF cJ cM Hf Id Ji Jq Jy Ly My Ni Pc Qb Qe) fR(Aa bB Co Kc Lv Mb Mm Mx Nd Ne Nu Of Pa Uh Ur) Em(Aa Dl Hv Mg Nk Nm Oz Qu Ss) Ji(Hw In Jm Jt Ng Nm Pz) mP(Aa fP Ii Nm Pd Pf Pg) mZ(Aa bI Bo Dc Nj Pf Rb) Pe(mU nI nT nU) fP(kF nA nH Rb) Cq(kP nD nO) Il(aC bN cH) eM(Dg mW nK) Aa(kI mU) Uc(It Ke) Pf(jT nT) Pg(aC nU) AlmI NmnR NljQ JtkK} Gn{My(Af Ao Bc bR cA cN GP Ha Hw Ij Ik Iz Je Jf Me Mg Ny Ow Ph Qh Qz Rg Ri St To Uv Vp) Lu(Aw Co Mi Mw Nq Ow Qy) Hw(Fr Hc Tn Ut) Tn(Cw Kf Ks) Jt(Hu Ut Vv) Ul(Fr Im Jk) Hb(Mi Ou) Kf(Hc Ut) On(Ke Uh) cF(Ba Hv) AaOu CtOm DlMw WmUb MmQy UtcN bRcS} jT{aJ(aG aL aY bA bC bJ bU bW cB cE cG cL cN cT cX dC dL iA jD kQ lN oE) iZ(aO cA cF cX dH dK hA jD) jI(aM bE bG cF dC) Pf(Fr Nv Om) aP(bG cI cW) bE(dG dH lN) jM(bP iP nY) WmNw JgPe bAcT bJhG cQjH dRjQ} eM{Tn(Ao Cq cX Hb Im Ir Jv kR Ma No Nv On Qn) aH(Ba bQ cG cT eF Jk My Oy pI Qt Qy Vs) Qd(Aa fP Kl Kq Nm Sr) fP(Aw eQ oV oW) Mw(Jt Ss Vo) pK(aR oH oW) Fr(Aa eP) AfAw NunU MmUf KqUh LiOz aCaX cPgV} mZ{Ib(bP Cq eC fP Ii Jl Jp Ju Kc Kl Kn Mj Mn Nj Nm Tr Tv) Ng(Ii jQ MM Nm) Hc(Ad Cv Dc Ii Jt) qU(hV oQ rZ) Jh(jQ jR) Jk(Jl Jm) Um(aY bH) Pc(jH qT) jL(oQ Qd) BamI DgIz NkqW NljH UbbH HuPe VvbX} jM{iZ(aK aO bB bM bO bV dI gP gW iB jE jI jL jU kR oF) aP(bC cG cI cT dG dI jR jU) jI(bN bO cF cP kR) aJ(aI bO cD dN) jH(aK cU gW) jQ(aQ bA nW) gP(oF oK) NlnU bCdL bObP cDjL iBnY} Em{Fr(Ad bA dC fP gP Ii Kf Kl Pj Ss Vo) Tn(Fy Ke Kl Mm Nm Ok Pj Ul) Hv(BA cT Di Hc Hu) bA(cF cO cV Rh) On(Ke Kf Pj) Aw(cP dC) Mw(dH Ik) My(bN Jy) Hu(cN Ny) HwJk HcbN} Ji{Mm(Fr Hr Hw Il In Io Ip Iq Iv Jm Jo Jp Jt Lu Mb Mr Mx Ni Ny Og Pc Pz) Nm(Fr Ip Ni Oz Pc) In(Hx Iv Mi Nq) Pz(Oz Pc Qa) Oz(Il Ng) FrJt} jQ{lK(aV bA bO cF dD dH dN fP gL iZ nW pF) jH(aD aG aS bJ cA cI cT dE eC hG oK) aJ(bM cU) cI(dN dR) hV(qU rB) NenU lmIn OmPe aOcU aPbQ bAcT bMiZ} mP{Hu(Cs Fp Hw Hx Ii Ik Ip Iq Jp mW Nf nU Of Ok On Pc Pg Qa Qe Vq) aY(Ih Tr Ub Ug Uk Vt) Hc(Jp Kl) pK(dK kO) MmNg IzJp UmOy} bA{gV(aQ aZ bE bG cH cM cR cT cY dJ dK dL fR gL) dX(As bC bM bN cF cI dB) eP(Ao aW bC bM cF cO dB) UcQd aCfR} Hc{fP(kI kP mH mS nJ nN nT) mI(bX Jt Qe Uc Ug) oQ(Cv Cx Ii Je Rb) mF(Al oF Qe Rb) Jt(kF kG lX) Al(nF nT) DgkF JpmH UgfR} Aw{eP(Af aN bV bZ cH cK cU DC Fr) dX(aE Af aJ Ar bL bM) fR(aC aG cJ Dl fP Nm) Qd(Kf Uc) fP(kF nH) aCbE aJdG} nU{Ne(eD iC jE jR jU lK lM qT qW qX qY) Nl(jP jU lO qU qW rA) NjjK HuPg PfjH} Om{Ij(Hv Me Mm Nm Nn Oh) fR(Ba Ez Jk Lh On) In(Nu Pc) Nw(bU Mm) Pe(jH rZ) MdPc PfrZ} Um{bH(kF mE mM mY nB nD nH nK nN nO oQ) aY(lW mI mM mU) kF(mM Uh) OymI bMmU} Kc{Dg(aO bN bV cS Fb) Il(aF aO cF cN) aG(cT Di Nd) DiKf LubN UkcT VtoP} Pe{Hu(mF mH mT mW nF nT) Ng(nD nT) Nw(rB rY) QcrZ mFlN nArA kKlO} cT{dX(cD Ch cS cV De dN) gV(aH aJ bO dM) fR(aC aH cV) bMeP} Qd{Ba(aG Fy Ss) Uc(bX Ib) Il(bN cF) TjbX TvfP SrcN KfOu KsgW} In{rZ(Ih Nq Qb) rY(Nq Qb qU) Nw(Jt Nu) gW(Bc Kd) qUrX} Iz{fP(kI kN mI nH) Dg(mI mT nN) oQ(Kl Nj Nm) NmlW} cL{jB(aW cM nC nH) oV(aW cJ kO) pK(aW cI mI) cJeQ} fR{Tn(Fy Jg Ok Uh) Uf(Cw Jo Nm Pj) AaKq AsdX DgEz} kK{Nk(jK jV lN) jK(Nj Nl) jV(Jg Nf) AaNg VvbX PflO} Ug{Vv(mF mU nJ) oQ(Kg Ng Tn) Oy(lW mI) CtmI} eP{Cu(aG bN) bC(aJ gP) AocP AsaX BabN aCgL aFbV} cD{jL(bJ bL dH eC jD jH kR lN)} gW{Ex(dM Il Mg Tv Tj) FrUc HwQa KsUn} gV{dM(bB bC bL bM dG) cP(dB dR) aGaX} aH{bF(oV pK) bQ(pH pI) dX(Bg Fr) cEoT} aP{dF(qT qU qX) bI(qT qW) hA(hB jE)} Nw{Wm(jH qV qY) Jt(Md Ml) NmOh} jV{nR(Fr Hv Mq Mx Nk) NknA} pK{bC(iA kO lY) bBdK bMmI nOoW} Nl{mF(lM lN) jH(kG nK) kIlM} Vv{bX(kI mM nB nT) DcnJ} Co{Dg(aJ mH mM) JtkN} Ib{nT(bI Ur) bMnN fPkG} dX{AocN AsaX BabN aFbV} rZ{rX(Pd Pf) NqPg NtQc} Fr{Uc(bC fP) TjfP} Oy{mI(Cv Tj) UrmF} bH{DimI ExnJ UolY} lW{Dd(Kg Ma) FyUt} Aa{NgnD HunK} Nq{PfrY nIjP} Oz{kF(Cv hB)} cQ{iZqU qVoF} dN{hA(dM iZ)} mF{NelM NklN} mM{ChTr FyUt} BaaCcN RbOnfP QwbMnN PdnAlO Unconstrained panels with 3 analytes, where 1.0E-7 >= 'AUC p-value' > 1.0E-8. Contains 14,116 panels of 14,487,373 total panels evaluated. : Jj{Mv(aG aH aK Ao aU bA cN Co cT Di dJ Em Et Fp fR gW Hq Hr Hu Hv Hw Hx Ii Im In Iq It Iu jD Jk Jl Jn Jo JR Jt Kc kK Li Lj Lw Ly Lz Ma Mb Mc Md Me Mf Mg Mh Mi Mj Mk Ml MM Mn MP Mq Ms Mt Mw Mx My Na Nb Nf Ng Nm Nn No Nq Nr Ns Ny Oe Of Og Om Pd Pe Pf Po Pz Qe Qt qU Qw qZ Uk Wm) Po(Et Fp gW Hq Hr Hu Hv Hw Hx Ih Ii Ij Il Im In Iq It Iu Jl Jn Jo Jp Jr Js Jt Lh Li Lj Lu Lw Lx Ly Lz Ma Mb Mc Md Me Mf Mg Mh Mi Mj Mk Ml Mm Mn Mp Mq Mr Ms Mt Mw Mx My Na Nb Nc Ne Nf Ng Nj Nk Nm Nn No Nq Nr Ns Ny Oe Of Og Om On Pa Pb Pd Pe Pf Pg Pz Qc Qe qZ) Jk(cH cZ Et Fp Fr hA Hq Hr Hu Hv Hx Ii Ij In Iq It Iu jD Jg Jn Jo Jp jQ Jr JT Kc Lh Li Lj Lu Lw Ly Lz Ma Mb Mc Md Me Mf Mg Mh Mi Mj Mk Ml Mm Mn Mq Mr Ms Mt Mw My Na Nb Nc Ne Nf Ng Nh Nj Nk Nm Nn No Nq Nr Ns Ny Oe Of Og On Pa Pd Pe Pf Pg Pz qU qZ) Jl(Et Fp Hq Hr Hu Hv Hx Ih Ii Ij Im Iq Ir It Iu Jg Jm Jn Jo Jp Jr Js Jt Lh Li Lj Lu Lw Ly Lz Ma Mc Md Me Mf Mg Mh Mi Mj Mk Ml Mm Mn Mp Mq Mr Ms Mt Mw Mx My Mz Na Nb Nc Ne Nf Ng Nh Nj Nk Nm No Nq Nr Ns Nt Nw Ny Oc Of Og Ok On Pa Pd Pf Pg Pz Qc Qe) Pg(Et Fp Hq Hr Hu Hv Hw Hx Ih Ii Ij Il In Iq It Iu jG Jm Jn Jo Jp Jr Jt Lh Li Lj Lu Lw Lz Ma Mb Mc Md Me Mf Mg Mh Mi Mj Mk Ml Mm Mn Mp Ms Mt Mw My Mz Na Nb Nc Nd Nf Ng Nj Nk Nm Nn No Nq Nr Ns Ny Oe Of Og Om On Pa Pb Pc Pd Pe Pf Pz Qc Qe) Ih(Et Fp Hr Hu Hv Hw Hx Ii Ij In Io Iq jG Jm Jn Jo Jp Jt Lh Li Lj Lu Lw Ly Lz Ma Mb Mc Md Me Mf Mg Mi Mj Mk Ml Mm Mn Mp Mq Mr Ms Mt Mx My Mz Na Nb Nc Nd Ne Ng Nj Nk Nm Nn No Nq Nr Ns Nt Ny Oe Of Og Om On Pa Pb Pd Pe Pz Qc Qe qZ) Mp(Et Fp Hq Hr Hu Hv Hw Hx Ii Ij In Iq It Iu Jn Jo Jp Jr Jt Lh Li Lj Lu Lw Ly Lz Ma Mc Md Me Mf Mg Mh Mi Mj Mk Ml Mm Mn Mq Ms Mt Mw My Mz Na Nb Nc Nd Nf Ng Nk Nm No Nq Nr Ns Nw Ny Oe Of Og Om On Pa Pb Pd Pe Pf Pz Qe) Hq(Em Et Fp Hr Hu Hv Hx Ii Ij Il In Io Iq Iu jG Jn Jo Jr Jt Li Lj Lu Lw Lz Ma Mb Mc Md Me Mf Mh Mi Mj Mk Ml MM Mn Ms Mt Mw My Na Nb Nd Nf Ng Ni Nj Nk Nm Nn No Nq Nr Ns Ny Oe Of Og Om On Pa Pb Pd Pe Pf Pz Qe) Lh(Et Fp gW Hr Hu Hv Hw Hx Ii Ij In Iq It Iu Jg Jn Jo Jp Jr Jt Li Lj Lu Lw Lz Mb Mc Md Me Mf Mh Mi Mj Mk Ml Mm Mn Ms Mt Mw Mx My Na Nb Nc Nd Nf Ng Nj Nk Nm No Nq Nr Ns Ny Oe Of Og Oi Ok Om On Pb Pd Pe Pf Pz Qe) Mq(Et Hr Hu Hv Hw Hx Ii Ij Il Im In Io Iq It Iu Jn Jo Jr Jt Li Lj Lu Lw Ly Lz Ma Mb Mc Me Mf Mg Mh Mi Mj Mk Ml Mm Mn Mr Ms Mt Mw Mx My Mz Na Nb Nf Ng Ni Nk Nm Nn No Nq Nr Ns Oe Of Og Ok On Pb Pd Pf Pz Qe) Nc(Et Fp Hr Hu Hv Hw Hx Ii Ij In Io Iq It Iu

Figure 5 Continued

Jr Js lM lO Lw Lz Md Mf Mg Mh Mp Mr Mu Mx mZ Nd Nh Ni Nj Nr Ny Og Oh Oy Oz Pc Pg Po Qc Qd Qe) Nw(eD hA Hq Hu hW iB iC Ir jE Jg Jh JK jL Jm Jo Jp Jr Js Lh Lu Lz Mg Mh Ml Mm Mt Ng No Nv Ny Pd Pg Qc Qd qU) hV(Fp Hq Hr Hu Hw Hx iC Ik Iv Jg Jl Jp Jt lM Lu Ma Mc Mg Mi Mm Mn Mp Mq Nd Nm Ns Nt Nu Oe Oi Ok Pz qT) jT(hA Hq Ih Il Im Ir Jg Jm Jo Jp Jr lM Lz Md Mf Mh Ml Mx Nd Nh Ni Nj Nx Oh Oz Pc Qc Qd Qe) Il(jE jF jH jK lM lN lO Ni Oz Qd qV rZ) mZ(iB jD jE jF jQ kP lX mE oQ qW rB) jQ(hR jE jL jV qX qY rB rC) rZ(eD iC jF jK jL lM lO Nq) Lw(jD jL jP lM lN) Qd(Hw Im Pa) Lh(Hr Mt Pa) jO(Io rX rY) Mj(Hr Ml) In(Jn Jr) Qa(Hw Ij) nR(mF nI) qX(iB jI) MhMs IoeD nNkK nOoP nIlO rYlM} Cp{Ad(aD aE aJ aK aL aP aY aZ bG bN bO bP bQ bS bU cE cG cH cJ cK cM cN cO cP cQ Ct cV cX cY dA dC dD Dg dJ dL dN eF gP It Lh Nh Of Qd Tr Tj) dX(aF aI Al Ar aS Aw Ax Bb bE Bg bI bJ bL bV bX bZ CT Cv CX cZ DD dG fR Fw Gl) fP(Af aJ BN bU bV cF cN cS dB Dg dN fR Kc kI mF mI mM nA Nm Of Oy Ss Ue Uv) Dg(aQ aU aV Aw aX aY aZ bC bV cG cL cP cT cX dD dG gP gW Kc mM Mn Mu Nh) Uc(aJ aX bB Lh Mv Ni Nn Qy Rh Tr Uk) eP(Aj aM An Ar bH bR bS cX dA dE dJ) Om(aG aR bA cV dN Em Nd Nw) mM(Al Bb Cq Jp Ju mI Tr) Aa(aG bO cA cK fR Hw) Mm(aC aG aH bB cX dN) cV(aJ Il Ks Of Uk Us) aH(Hr Oy Tr Uk Tj) eM(BB Dl Gc Uh) aG(Ii Kc Us Tj) Tr(mH Uk Us) aC(aJ Ii Us) bB(aJ aN Oy) Il(bN cZ) mP(Al Li) EmHv KlbV KsgW LhmH aNcN} Hq{mP(aC aM Ax bA bH bP cH cJ Cq Cs Cv Dg Dl Fw Hr Ii Il Jl Jm Ju Kd Kf Kr Kx Li mZ Nm Og Oh Or Ou Ow Oz Pa pF Pg Qa Qe Qg Qh Rm Sr Ug Uh Uk Up Vo Vq Vs Vu) mZ(Al Ao bI Bo Dp Fp Hb Ih In Iq Jg Jp Js Jt kI kK Lh mF Mg mI Mt Ne Ng Nh Nl No Nr Ny oP oQ Oz Pa Pd Pg Ub Ug Uk Um Vt) Pf(kG kK kP lW lX mS mT nB nC nK nL nM rZ) Pe(kG kI kP lW lX lY mS mT nK nM nN) mM(aF aO bI bQ Cq Hc kK Qx Uo Vu) Gc(Al aX bC bP Co Di Fr gL Qy) Um(lY mF mI mT mW nH nN nR) Aa(eM kF kO nH nI nJ) Cq(kN mE mF nD nH oQ) Em(bV Mu Mw My On) Gn(bP Jm Mu Tj) Qx(kN mH nH oQ) eM(Jo mH Nd Nu) kK(Dc Iq Jt Mm) Ug(kI mF mU) Dc(kF lY) Dd(kG mI) Tj(kO oP) Nj(nA nF) Tv(oQ Tk) Vu(mH nD) bM(kI mU) nH(oF Rb) kN(Bo Je) CvmI MuaC HvfR IjOm InIv OamF UomH VpoQ PdnF bHnA} Mu{Gn(aV aW Ax bB Bo Em FR gP Gz Il Ip Iq Ki Mh Mm Mp Nv Og Qh Qt Rb Rh St Tr Tz Ur Wm) fR(aJ bN cP dC Fy Io Jg Jv Kf Kz Nj Nq Pd Qu Rf Vq Vv) Pe(kI kP lW mE mF mH mM mW nA nB nC nD nH nJ nL nM) Em(Af aS Co Hw Ib Ii Ik Kl Ks Lx Ly Ml Mm Qg Ur) Uc(aP Aw bA bV De Hc Jh Kc Lx Ms Nb Pf) mZ(Ad Dg Dk Jl Jt Li Mf Mm mP Ok Oz Tj) eM(cV Ib kI Kl kN mE Mm mY nB oF) fP(kG kK kN lX mE mF nI nU oP Tj) aC(Bc Co Dk Hw Oy Pd Rb Tj) mP(Il Iq Ma Mm nA Nj Om Ug) Il(aG aH aO bA bG cF) Oh(Hw Ij In Iq Jk Ng) Cq(kI lY nM nT) Nf(aG aH bN Gz) Nw(Gc Ng Nm Pz) Pg(aG mF nA nD) Aa(bN nF nL) Tj(aG aH bB) Oz(cN Ng Og) mI(hB oF Pf) Mz(Ng Of) Hw(cH Ex) kK(Jl Nm) DcmE DkNb GcRc NuIn MfnU MrOf HvUk IunI RbaH PzQd JtnR JuoQ KcaG PfnF bInT} Mv{mZ(bP Co Dd Il Jg Jm Jp Jt kK Lh Ma mF Mg mI Mk nA nT Ny oQ Pd Pj Po Qe Uh) Ue(aG aI aL bB bJ cB cN cO cQ cY cZ dH dJ Ip Lw mH mM mS nF nN nU oP oQ) Gn(aI aN cF cM dN Fn Fy Jt Kg Kl Ni Ok Pc Pz Ra Tv Uc Vs Vt) fR(aC Aj Dg iA Ib Jo Kf Kl Ly Mx Qm Uc Ug) mP(cE Il Lh Lz Nn Nw Of Oz Pc Qe) Pf(kO lY mM nA nB nC nJ nL rZ) kK(Jk Jo Mm Nv Ok Pe Pz Qe) Dd(kF lW mM nH nL nT) Pe(jT mS nC nL nR oQ) eM(aG Dg fP Jo nH Vq) nA(Hw Iu Jl Jo Nj Uc) Il(aG aN dN nU Qw) Kc(cJ Dg fP nR Uc) Pd(mH mS mY nT nU) Pg(kI mE mH nJ oQ) Gc(bJ Mk Qz Rj) Aa(bN mU nJ) Tj(mH mI nT) Uc(cN Dc kN) nU(Mf mH Of) mF(bM Jl Vs) Dg(aJ aP) Em(Mm Ng) Jd(mS nD) Nw(aH Nm) mI(Bo Ju) mM(Cq Uo) oP(Im Qe) oQ(aP Ur) ConD ExJo MjTv NbUk HwaG IbQd UmnT UvkN OzcN cEmH} jM{iZ(aD aE aF aL aM aP aQ aS aW aX aZ bC bH bL bP bZ cB cC cE cG cI cK cL cT cU cZ dE dK dL dM eC hA hF hG iA iJ jD jF jK jO jP jY kS lM lN oE oH pF) aP(aD aK aZ bA bH bL bO bP bQ bV bZ cA cO cP dE dF dL fP gP gW iB iC jE jF jH jI jL lN tF) jI(aJ aK bC bQ bV cA cB cD cL cR cV cX cY dI dK dL dN gP gW iA nW oH pF) aJ(aD aK bB bC bN bV cA cB cF cG cL cX cZ dG dI hA iB jF kR) gP(aI aO bB bO cF dL hG iB jH jL jT kR) jQ(aV bC bO dD dN fP gL) bP(bU cI dN nW oK) jT(bZ fP gL iH) nY(dL dN hG jL) jH(cF nW) bAcT bOdM iPoK} Gc{Co(aC aM aO Aw bG Bn cB cJ cL De dF Em fP FR Fw Gn Hc Lu Oe Of Oz) My(aF aJ As bM bP bU cH cN cU cW Cx Di dK Gl Ip Ly Mh) cF(Ao Aw aX bA Bb cG De Ez Jh Mg Po Qy Tn Vv Tj) Hu(Aa aV bR dJ Ib In Jv Ly Ni Qy Ur) Aw(Ad aV bC bN cV dR Hw) Ct(bC cS Hv Hw Nn Om Qy) Ba(aU aX bJ bW cO Mp) Hc(Aa bN Ii Nn Rh Uf) bC(bA cN Di Dk Ib) cT(Aa aF bJ De Nq) cS(bU Di dR Tj) Fr(dA Di dR) Iz(Hb Hw Vo) Vv(Jt Nm Om) bA(De Li Mp) cG(bN cV Tj) Lu(Hv Nq) cN(De Uf) AlLx DiHv TjOn EzIb FbHb MmQy HwTn JkOm} Gn{My(aC aN aO Ar Bb bO bX cJ cV Dd Dl Fb fP Hv Ih Jg Jp Kc Kz Ma Mf Ml Ng Ni Ok Or Pc Ql Qw Qx Qy Ra Rb Rm Ud Uk Ur Ut) Lu(bU cF cS Ez Fr Hv Im Li Mp Nn Qd Uf Wm) Fr(aG Cv Dl Et Kl Nm Pj Vo) Hb(aX Ba Hc Hv On Qy Tn Vv) Ib(aW Hu Hv Jm Jv Ni) Aw(Ad aH cP Cw Hw) Lx(Aa Al Et Jm Pj) Mw(fP Ic Kf Qm Qu) Hc(Ad Al Hv Ii Nm) Ut(bN Ik Nm Ny Pj) cN(Ba cS Ct Hu Kg) Tn(Ke Nm Uh Ul) Om(Ez Im Jh Vv) Hu(Jv Ug Vo) Hw(Co Ct Iz) Vv(bN Kf Nm) bN(cS cT) CoJt CvcS DiHv NiNk QyUl KsOn aJcF} jT{aJ(aF aK aM aO aP aQ aR aV aX bI bL bZ cA cH cM cO cV cZ dG dH dI dN eD hB hC hG jF jK jL jP jQ jU jY oH oK oN pF tF) iZ(aF aL aQ aR aW aX bJ bW bZ cB cD cE cJ cP cT cW cZ dG dI dL dN eC eD fP hC hF hG iA jF jL jU jY kQ lN lO oF oK tF) aP(aD aN aQ aS aX bJ bQ cD cT cV cZ hA hC) dM(aC aM bG bJ bM cD cF dK lN oE) bE(aO bO bZ cI iB jD) Pe(iB Jh Jk Nw) jI(aC aN bU dH) Wm(Jh Lx Mz) Nk(Jp Na nU) cI(hG iB jL) aO(aX jQ) NaNj JpPf aCgL cDjL dHhA} Kc{Il(aC aG aN aZ bA bF bG bI bL bM bO bU bV bX bZ cA cJ cP cS cT cV cX dK dN) Dg(aF aP Aw BA bQ bX cF cN Co dF Di dM dN Hc Lx Mt My Nd Pf) Ug(aG aL bN bP bV bX cF cJ cN cT cV Ib Nb Nd) aG(aO Aw Bg bV Fr Hc Ib Lu Mf Nq Uk Tj) cT(Ic Jo Kl Mm Ow Tv Uc Tj) bN(Aa Di Ld Nd Ub Uk Tj) Uk(cJ cV Di Ld Nd) Di(cJ cV Ow) Uc(bA Fr Ib) Lu(aL cJ) bV(Ow Uh) lW(aO eM) oQ(Hc Ng) DdkF TjbA NbcJ InJn bXoP} Qd{bN(aF aO BA cT Dd Di Hw Iv Mf Nb Nf Nw Ok Oz Uc) Kf(Ba bM bV Ch cN Cw Hc My Nb Ok Qw Tj) Uc(aF aO Bg bM cN dN Hc Nb) Il(aC aF aO bR bX cT Ou) cN(aC bX dG Oz Ug Tj) cT(aC Fy Hw Pz Tt Tv) eM(Af aH Dl Fy Uf) Ss(aF bA Hc Ou) Ba(aC fP Vo) Ug(aH cF cJ) gW(cP dN Us) Di(Om Vo) Tv(bA Ex) Oz(aC bX) AwOm EmaS HwaC SrhG VobA bRbX nRjV nUjL nIqU} Em{Fr(Af Ap aS Bb cN cT cV Cw Dl dR Hv Ic Jt Lu) Hv(aS Aw Bg bV Ct Jk Lu Mw My Oi On Oy Vs) Tn(Af Ao Cw gP Ib Jg Jo Lh Ny Rc) On(aG Ao Ii Lh Mm Nm Of Ul Un Vo) bA(aF aU Aw aX bC bJ cS dB Di Hu) Mw(aS Dg Dl Ic Jy Om Pa Qv Ri) bN(aJ Aw Ct Hu Oi) Aw(Aa aH eP) My(aG aH Qm) Lx(Jm Mm) Hu(Ii Ly) BaaC PoJm HwIm HbJp UfPj} Nw{Nm(FR Hr Ij Im In Io Ip Ir Jh Jm Jq Lh Lj Lv Md Mh Mi Mm Mq Ni Nn Nu Ny Oy Pc Pe Qa) In(Hw Io Iv Mb Mm Nd Ng Ni Om Pz) Mm(Hw Io Jm Jt Lh Ni Pz) Jt(Fr Ij Ni Nn Ny Oh) Om(bH cF Jh Mh Ml) Hw(bH cZ Jh Mh) Pz(Md Ml Nu Qa) Oh(Ih Iq Lh Ni) Tj(aH cN Kf) Pe(hW jH rZ) Ni(Ij Iv) Kf(dB Di) WmNb NnOz IhIv HbbH IoLh SrcN JnJs PfrZ} mP{Hu(Ad Af aG Bc Cq dG Dl eD Et hB Ir It Iv Jo Jr Js jY Kl kN Ko lW Lz Mg Mk mT mU mZ Nd Nj Og Oh Ow Oz Pa Qb qU Um Vo Vt) aY(Ib Nd Nj Nx Ow Oz Qw Rb Uo Uv Vo Vq) Ib(mZ Nm Om Pc Um Vo) Hc(Af Al Bc Nm Or Tr) Ng(Jt Li Ma mM Pz) pK(aZ bP iA mI) Iz(fP Jt Kl) Tn(bX Ks) AwfP BaPc DdOy DgJg cLjB cTdU} mZ{Ib(Al Bb bH bI cV cZ Gp Jm Jt Kf Ma Mm mW nH Ni Ny Oh Om Qb Rh Um Uv Tj) Ng(Jg Jm Lh Nj oQ Pe Pf qX) Jk(Dc mM Nj Nm Pc Pe Pf Qh) qU(hR hW hX mF oP rC rX rY) Nl(qT qV qW qY) Hc(Hb Lh lW Rb) Iz(fP Hb Kl Tr) Nk(jH jQ jV) Hu(Nj Pf Rb) Im(Lj lN Nj) Qw(aY Nd) Pe(jH Oy) nH(hW rZ) AwDg CoUh FrmM MwPg UbVv PfjH eMpK} jQ{jH(aH aQ bC bL bO bR bU bW bX cC cD cE cF cK cL cQ cR cW dB dF dK eF gW iA kQ kR kS nW oE oF oN pF Wm tF) lK(aI aM bC bE bJ bR bU cS dE dG eF hC iJ iP oE oK tF) dR(cD cY dA dD eD oE) dN(bC cD cU jR) lM(bQ cD cI cT) hV(qV qW qX) aO(bQ cI) NoNl NqnI NknU InhR OkOm aPcU} Aw{eP(aJ An aW bB Bc bL bM cI cN cV dB dI eM) Dg(AN bA Cu dL dN eM kF Ni On Un) dX(aW bB bU cI cK cN dB Dc) aC(aJ aL aN aP BA cP) aN(Ad Aj bB bN cN cV) fR(Af aH bB cE cV Cw) fP(aP kK kN mI nA) Cq(mF mM nA nH) eM(aG bB cV Oz) aJ(aH cV) mI(Bo Dd) NgIv IlbN KfUn} eM{aH(bA dR Ez Im Jd kI Mi Mq Nq oT Qu Ut Vu) Tn(aI aO Cx Dc Ij Nk nU Qm Ug Vt) Aa(Ez Ij Jh Jk Ut) Mw(Dg Qm Uc Uh Uu) fP(Fr Jd Ut Vs) pK(aF bP cM cW) dU(cS kG oW) Hc(Dg Kl) Vs(mM nD) Vv(nJ nU) Oz(Nq Qy) aC(Ba bE) aJ(dX eP) AxnA TjnD NuMb IzbB JkVo KeUh

Figure 5 Continued

PjkG bAcV cLoV} Hc{fP(kE kK kN kO lW lY mE mW mY nD nF nI nM nO nR nU) mI(Ax Bc Dd Dg Ii Nk nW Or Ub Um) mF(Ad bX Cv Dc Jp Kl Nd oQ) lW(Ad Cv Jt Kl Ug) mM(Ad bH cV Jt Tr) Al(nI nJ nM nN) Kl(kF kG mH) Dc(lY nU) oQ(Uf Um) CqkI DgkG NmfR UckF QenN JtnR KmT} jL{cD(aJ aK aM aP aS aW bE bF bG bN bS bX cC cF cI cR cT cW dN fP hA hG iA iB iO jI oK tF) Mq(nO nR nU) Nq(nA nI) Nl(kF mU) dNhA nUjI nJoQ} Om{Ij(Hw Hx Il In Iv Lx Mc Md Mf Mk Ml Mq Mx Mz No Ny Oy Pa Pe Pf) In(Jn Oh Oz rX rY rZ) Pe(hA jD jR) jV(kK Mf nR) fR(cT Uf) MfhA NyPc PfjH} Fr{Uc(bB Ch cV Kg Ms Nb Ou) Il(aH cV fP Ng Ou Ss) Dg(bA dR eF pF) fP(Di Ex Ug Us) oQ(Hb Pe Tr Um) dX(aC Ap cT) Oz(fR Ng) WmIk JkOh aCeP} bA{dX(Ao aU aX bG bJ bP bU cA Ch CO Di) eP(As aU bJ bP cA cI cK Di) cN(aC cI cV) dG(gV oW) DiaN aCbE aHoV aPgV cVfR} Iz{Dg(kN lW lX mU nA nH nL nR oQ) oQ(Ao Hb Mn Nd Qx) Jp(kF kK mU oP) fP(kG lW mF mM) Nm(kF mI) HbmI JtkF KlnR} aP{bQ(iB jD jH jI jR) cG(qT qU qX qY rA) hA(aL bE bU dB) dF(qW qY rA) qU(cE cL cQ) Ba(aC Dg) qX(cQ dG) DgcT bIqY dMgV} cL{jB(cJ cO dB hF iA kO lY nF nL nU) Dd(mF mM mW nC nT oP) oV(bL iJ nC nH nL tF) pK(nC nL) DgOn cJdU} Pe{Ng(mF mH mM nF nH oP oQ) Hu(kE kP mI mM mS nB nH) rZ(Lx Nn Qa) kF(jF lO) JkmI KsgW nUjH mUlM kKlN} gV{dM(bU bV cI cP cU dA dC dE dK dL) cP(bQ bV bZ cF cU) cT(bJ cE cQ dB) aG(bV gL) aDbV bOdR} kK{Nl(iC jH jP lM lO) jV(Hx Iu Jp Nj Qc) lN(Iu Nf Nj Pa Pf) Ng(JP Jt Nm) CoJt NmNq NnMm NkjE} gW{Ex(aK Bc cP Di Hr Iu Ki Ue Uk Uv) Ks(Iv Jl Lx On) Un(Il Uk Us) AsaJ BcUg LvIl QxcN KdUk} nU{Ne(iB jF jI jK jO jY lN lO qU rA) Pd(jH jV lM) Nj(iB jH) Nk(jP lN) Pf(jV lM) jD(Mh Nq) VvbX} Vv{bX(kE kG lX mE mH mS mT mW nK nM nO oQ) nJ(bH Dd Gz Uv Vo) Ug(lW mI oQ)} fR{Ba(aG cV Vo) Tn(Af fP Vo) cT(Af aG Dl) Mw(Jo Ug) On(Et Jt) EzNm NtJo HvOi LiOz UfcJ aCcV} jH{Nl(kN lY mE nA nJ nR nT) bE(bO cR jR oK) dN(aK jR lN) jR(cQ fP) NmnR NcnI NknO} aJ{cP(As Ba cT dR) aC(Ba bE cF) Dg(Ch Di) cF(cH dG) AsdX DidG aLlM bMjR bUjF cDhA} In{Jn(hR hX rB rC) Nn(Oz rY) Qa(Io Oz) Nv(Nu Ny) LwhR HvIv IhrY ImjR IprZ JmrX} aH{bF(eQ oT oW pI) bQ(dU jB oT pK) dX(cG Cu Di) pK(cG dK) BacN} Aa{nK(Jg Jk My Ng) mU(mH Nb Ng) Jk(nC nL) nA(Jg My) TjbZ NgnH} kF{Um(Dd oF Oz) DgTn EdoQ NubX IbJt QwfP OrOz UomM UgOy VtbH PflO} nA{Nl(jK jO jP) Ne(lN rA) qU(Nk Nq) JkbM UmaY PdrA} pK{fA(nC nH nL) cV(dK nO) mI(bO nK) aKbB bCnF dKhB} Ch{lW(Kf Kl Ug Vo) Kf(kI mM) oQ(Ug Um) KlmY} Ng{mM(Ad Dc Nm) DiIv NmnR JhOh UkoQ VomH PfnT} bH{Uo(kN kO mT nC) lY(Ic Ub Tj) GpmM UmmU} dX{As(cG cS gL) cT(cC cU Di) DecP aXcI bNbV} eP{bZ(aG cN Di) bC(dB Dk) cT(cI Co) AscG BaaF} Nq{nI(hA iB iC jY qU) rZ(Hw Na qU)} nR{jV(Fp Mw Ne Nj Qc) Nl(jD lN) MqjP} Tn{Ex(Ks nJ) DcmT KfUk UgaL UsfP bXlW} Pf{Hu(kP nT) Jp(rY rZ) NnrZ mFlN kOlO} Co{Dg(kE lW mS) Tr(mH mM) JtkE} Oy{Tj(mF nH) Ug(kI mF) oQ(Gp Um)} mI{Ba(Dg Ub) Ct(Um Tj) DiaY UfVq} Nb{Uc(De Ez Im) Uk(Mi Mp)} Di{Kf(St Un) BokG ItTk} Ex{cZ(Lh Mm) CxcN UgbP} Nl{mU(jK lM) mFqU qYkG} iZ{aLlM bIqU bUhA cDjD} oQ{Ug(bF Jg) BaUk UmaY} Ib{TjnT UrmF bMkG} Nv{Ny(Hr Lv Og)} Ba{VokN aCdN} Fy{UtlX cFlW} Nn{Il(Nx Oz)} Hu{TjmH PgnO} Jh{IqOh PdrX} bI{hGqX qVoF} bM{cS(jB oV)} lM{NemE aLgP} DgMbOn WmLxqY UmaYnT PdkOlO aCbEcT bBbFoV nJqUoP

Unconstrained panels with 2 analytes, where 1.0E-8 >= 'AUC p-value' > 0. Contains 47 panels of 108,068 total panels evaluated. : Jj(aA Fr Ik Ip Is Iv Ji Jq Lx Mu Nu Nv Nx Oh Ok Oy Oz Qa Qb Qd) lL(kG mW mZ nA nI nN oO oQ) Gc(Ef Mu Mv My) aA(jG Ji Oz qU) Gd(Hu Ua) mZ(jG qZ) CpeP DrMy UaoQ IsOg UmoO bAgV qZjQ Unconstrained panels with 2 analytes, where 1.0E-7 >= 'AUC p-value' > 1.0E-8. Contains 60 panels of 108,068 total panels evaluated. : Jj(Hq Ih Im Ir JG Jh Jk Jl Jm Jp Js Lh Lv Mp Mq Mr Mv Mx Mz Nc Ne Nh Nl Nn Nq Nt Nw Oi On Pa Pg Po Qc Qe) lL(aA kK kO lW mE mH nB nO) Is(Hw Il In Jm Om Pz) aA(aH cV Cx Fr Lv qZ) GcUa GdMu MmJi IjOm jGjI Unconstrained panels with 2 analytes, where 1.0E-6 >= 'AUC p-value' > 1.0E-7. Contains 132 panels of 108,068 total panels evaluated. : Jj(Et Fp Hr Hu Hv Ii Ij In Io Iu Jo Jr Jt Li Lj Lu Ly Ma Mb Mg Mh Mi Mj Mk Mm Ms Mt Mw My Nb Nd Ng Ni Nj Nk Nm No Nr Ns Of Om Pb Pc Pd Pe Pz) lL(kC kE kF kN kP lX lY mF mI mM mP mS mT mY nC nD nF nH nJ nK nL nM nR nT oP) Is(aA Hr Ih Ij Io Iq Jn Jo Jt Lh Mm Mn Ng Ni Nm Ny Of Oz Pc) aA(aC aG aN cF cH cX Hw In Mb Nu Nw Pc qV) Ji(Hw Jm Jt Ni Nm Oz Pz) Cp(Ad Dg dX) Nw(Jt Nm qZ) Aw(eP Gd) Dr(bC cS) Mv(Gd mP) iZ(jM jT) CoGc UamZ HumP KcoO OmjG aJjT aPjM cWkC Unconstrained panels with 2 analytes, where 1.0E-5 >= 'AUC p-value' > 1.0E-6. Contains 361 panels of 108,068 total panels evaluated. : Is(Et FP Fr Hq Hu Hv Hx Ii Ik Im Ip Ir It Iu Iv JG Jh Ji Jk Jl Jp Jq Jr Js Li Lj Lu Lv Lw Lx Ly Lz Ma Mb Mc Md Mf Mg Mh Mi Mj Mk Ml Mp Mq Mr Ms Mt Mu Mv Mw Mx My Mz Na Nb Nc Nd Ne Nf Nh Nj Nk Nl Nn No Nq Nr Ns Nt Nu Nv Nw Nx Oe Oh Oi Ok On Oy Pa Pb Pd Pe Pf Pg Po Qa Qb Qc Qd Qe) aA(aF aI aL aM aO aR aS Aw aX aZ bB bC bG bH bN bO bP bQ bR bU cB cE cI cJ cN Cp cQ cS cT cZ dB dC dF DG dH Di dN gW Hq Hr Iq Iv Jg Jh Jk Jm Jp JQ Kc Lh Li lO Lw Lx Ma Mc Mh Mm Mu Mv Mw Mz Ng Ni Nm Nn Nr Nt Nx Of Og Oh Ok Om Oy Pb Pe qT qW qX rA) Ji(Fr Hr Ih Ii Ij Il Im In Io Ip Iq Iu Iv jG Jh Jn Jo Jp Lh Lu Lv Lx Mb Mg Mi Mn Mr Ms Mu Mv Mx Na Ng Nj Nl Ns Nu Nx Ny Of Og Oh Om Oy Pc) Jj(Aw Cp gW Hw Hx Il Iq It Jn Kc Lw Lz Mc Md Me Mf Ml Mn Na Nf Ny Oe Og Pf qZ Wm) Nw(Hr Hv Hw In Io Iq Iv Jm Lh Mh Mm Ng Ni Nu Ny Oh Om Oz Pc Pz) Cp(Aa aC aG aH aN bB fP Mm Om Uc Uk Us) Kc(aG bN cJ cN Nd Ug Uk) Aw(aC aG aN Dg dX Ng) Mu(Hv Ij mP Ng Of Oz) Oh(Il In Iq Jh Pc) jG(dN Jp lM Lw On) qZ(hV Il jI jR lL) kC(Cx Pe Ua Ug Um) Fr(Gd Ng Oz Uc) Nb(Di Uf Uk Tj) aJ(aC cH Di jM) lL(kI Lw mU nU) Hq(Dr Gd mZ) oO(Hc Rg Ug) Mv(mZ nU) In(Iv Om) Oz(Lx Nn) jM(bP gP) jT(aP bE) EmbA GdTn GnMy NgJh HunU IlOm QdbN NvNy cDjL dMgV Unconstrained panels with 2 analytes, where 1.0E-4 >= 'AUC p-value' > 1.0E-5. Contains 896 panels of 108,068 total panels evaluated. : aA(AD aE Af AJ aK An AP aQ As aU aV aW Ax aY BA bE bF bI bJ bL bM bS bV bW bX bZ cA cC cD cG Ch cK cL cM cO cP Cq cR Cs Ct CU CW cY dA Db dD DE dI dJ dK DL dM eD eP Et FP fR hR Hu Hv Hx iB iC Ih Ii Ij Ik Il Im Io Ip Ir It Iu jD jE jF jH jK JL jM Jn JO jP JR Js JT jU jV jY Kf Lj lK lM lN Lu Ly Lz Md Me Mf Mg Mi Mj Mk Ml Mn Mp Mq Mr Ms Mt Mx My mZ Na Nb Nc Nd Ne Nf Nh Nj Nk Nl No Nq Ns Nv Ny Oe Oi On Pa Pd Pf Pg Po Pz Qa Qb Qc Qd Qe qY rB rC rZ Sr) Cp(aD Af aI AJ aK AL Ao AP aR AS aW Ax aY aZ bA Bb BC bF Bg bJ bN BO bP bQ bR bU bW cB cE cG CH cI cN CO cP Cq cR Cs Ct CU CV CW CX cY cZ dA DC DD Di dJ DK DL dN Ex Gd gP gW Ij Ik Il Io Ir It Jg Jk Jm Js Kf Kl Ks Lh Ma Mc Mh Mn Ms My Nb Ng Ni Nr Nu Oe Of Og Pb Pz Tr Ug Tj) Ji(Et Fp Hq Hu Hv Hx Ik Ir It Jg Jk Jl Jq Jr Js Ks Li Lj Lw Ly Lz Ma Mc Md Me Mf Mh Mj Mk Ml Mp Mq Mt Mw My Mz Nb Nc Nd Ne Nf Nh Nk Nn No Nq Nr Nt Nv Nw Oe Oi Ok On Pa Pb Pd Pe Pf Pg Po Qa Qb Qc Qd Qe qZ Ug) Nw(bN cN Di Et Fp Hu Hx Ih Ii Ij Ik Il Iu JG Jh Jk Jl Jn Jo Jp Jr Js Lj Lu Lv Lw Lx Ly Lz Ma Mb Mc Md Me Mf Mg Mi Mj Mk Ml Mn Mq Mr Ms Mt Mu Mx Mz Na Nh Nk Nn No Nr Ns Nv Nx Oe Og On Pd Pe Pf) Aw(Ad aE Af aH AJ aL An AP aZ bB bG bN Bo bP cE cH cJ cN cP Cq Ct cV cX De Di dJ Dl dN Dr Ex fP fR Gc Il kC Kf Nb Om Uk) Nb(Ad Al Ao Ap Ax BA BC bO bU cN Co Cq Cs cT Cu Cw Dc Dk Hc Kc Kd Ou Qy Rb To Uc Ud Ug Ur Us Vp Vt Wm) Oh(Hr Hw Ij It Iu Iv Jl Jm Jn Jp Lh Li Lj Lv Lw Lx Mc Mf Mi Mj Ml Mm Mq Mu Mx Mz Ni Nn No Nq Nu Ok On Oz Pe) Kc(aC aD aF aJ aK aL aN aO aP bA bG bO bP bV bX cC cF cH cI cP cS cT cV cX dC Dg Di dK dN Il Iu Kf Tv) Mu(aC aN Dr fR Gn Hu Hw Ib In Io Jk Ly Mg Mr Mw MZ Nd Ni Nu Og Pc Pz Uc Uk) Jj(aP Ba bV Ch cT cZ Di Ef hA Hc hR jD jH jM jQ jT Ld lL qU Rm Tn Ua Vv) aJ(aH aM aN Ax bB bC bR bU cF cI cN cT cV dE Dg dN eP jF) jG(Fr iC jH jO

Figure 5 Continued

JQ kK IL Lx Nk No nR Nv oP oQ Qd qZ rZ) Lx(Hq Hw Ij In Iv Lj Lv Me Ng Ni Nm Nn Nu Of Pc Ug) Is(Aa aG bN Dg Di Gd Kf Ks Me qZ Tv
Ug Uk Us Vo) Jp(Hr Hw Iq Iv Jh Jm Mm Nd Ng Ni Nm Nu Om Oz) aP(aC aH cF cT Di hA Pb qT qU qV qW qX rA Ug) kC(aD Ax aY Ba Bg
bJ bM Ct Cv kS nW Or Ou Qw) Fr(Em fP Gc Hw Ij Io Jk Nd NI Nu Ny Pc Pz) Nv(Hr Hw In Iq Jh Jm Jt Lv Ng Ni Nm Nu Og) Qd(aC bX cN Di
Kf Pz qZ Ss Tv Ug Vo) Om(Hq Hv Hx Iu Mc Md Nm nU Ny Oz Pf) Oz(cN In Jh Jq Lv Mi Mv Ok On Qa) Di(AN bA cN Dr Gc Iv Pb Uk)
mZ(hR Hu Ib jI Nc Ng Nj Pb) qZ(hA iC jO jP jT Lh Ms Qc) Dr(cG Ct Ef Hu Mv Ou Ua) Hq(fR II In kK mP Nn Nq) Qa(Hw In Iq Jm Og Pz)
Jh(Hw In Iv Jq Nh Ug) Gd(Bg De Ef Hc My) bA(cF cN dL dX eP) IL(jH jQ rX rY rZ) Nn(In Lv Mz Pc) Mv(Ib Ng Of Ue) Ug(It Oy Pb Un)
cN(Ba cT Ex Pb) jT(dG dM gL hG) oO(Dd eM Ua Uo) Gc(bC cG cS) Lv(Hv Jq Mz) Lh(In Pc Tv) Ok(Hw Ng Pz) aC(Ba bE fR) jH(bE dN oK)
jM(dL nW nY) Dg(Cu Kq) Ef(dJ mM) Em(Hv Mw) Tn(gC Kf) Uk(Qy Ut) bV(dX eP) fR(aH Pb) jQ(dN hV) ExgW GncS UanT liOn IIIv QbJm
PdrZ cLjB mlpK iZqU Unconstrained panels with 2 analytes, where 1.0E-3 >= 'AUC p-value' > 1.0E-4. Contains 2,867 panels of 108,068 total panels evaluated. :
Cp(aE aF aM An aO aQ Ar aU aV aW aX Ba bE bG bH bI bL bM Bn bS bV bX bZ cA cC cD cF cJ cK cL cM cQ cS cT DB DE dF dG dH dI
dM DR EF EM Et Fp FR Fw Fy Gc GL Gp Gz Hb Hf Hq Hr Hv Hw Hx iA Ib Ih Ii Im In Ip Iq Is Iu Iv Iz Jd Je Jh Ji JI Jn Jo Jp Jq Jr Jt Ju Kc Kd
Ki Kk Ko Kr Li Lj Lv Lw Lx Ly Lz Mb Md Me Mf Mg Mi Mj Mk MI mM Mp Mq Mr Mt Mu Mv Mw Mx Mz Na Nc Nd Ne Nf Nh Nj Nk NI
Nm Nn No Nq Ns Nt Nv Nw Nx Ny Oh Oi Ok On oO Ou Oy Oz Pa Pc Pd Pe PF Pg Ph Po Qa Qb Qc Qd Qe Qm Qt Qu Qv Qw Rb Rc Rh Rj Ss
Tv Uo Up Ur Uu Uv Vo Vp Vs Vv) Kc(Ad aE aH aI aM An Ao Ap aQ aR AS aU aV aW aX aY aZ Ba bB BC bE bF Bg bH bI bJ bL bM Bo
bQ bR bS bU bW bZ cA cB cD cE cG Ch cK cL cM CO cQ cR Cs Ct cU cW cY cZ dA dB DD DE dF dG dH dI dJ DL dM Ef Et Ex Fb Fn fP
Fr gC gP Hb Hc Hq Hr Hu Hv Hw Hx Ib Ic Ik Im Iq Is It Iv Jd Je Jh Jk JI Jm Jn Ju kC Kd Kj KI Ko Kr Ks Ld Lu Lw Lx Lz Mc Md Mf Mg Mj
Mm Mn Mq Mr Ms Mu Mv My Mz Nc Nf Nh Nj Nk Nm Nw nY Of Og Oi Om Ou Ow Pb Pf Pg Qd Qn Qw Qx Ra Rb Rg Rh Rj Sr Ss Tn To Tr
Ua Ub Uc Ud Ue Uh UI Um Uo Ur Us Uv Vo Tj) Nb(aC aD AF aG aI aJ aL aM AN aO aP aQ AR AS aU aW aX aY Bb bF BG bI bJ bL bM
BN Bo bQ bR bS bV bW bZ cA cB cD cE cF cG CH cK cL cM cO cP cQ cS Ct cU CV cW CX cY cZ dA DB dC DD DE dF DG dH dI dK dL dM
dN Dp Dr Ed Ef Ez Fa Fb Fn Fy GI Gp gW Ha Hb Hf Ic Id In Iz Jd Je Jf Jp Ju Jv Jy Ke Kg Ki Kk Kn Ko Kp Kq Kr Ks Ky Ld Lx Nn Nw Oa Oh
Ow Pi Pk Qg Qh QI Qm Qn Qt Qu Qv Qw Qx Qz Ra Rc Rf Rg Rh Ri Rj Rm Sr Ss St Tn Tr Tv Tz Ua Ub Ue Uh UI Un Uo Up Ut Uu Uv Vo
Vu) Aw(Aa aD aF aI aK AI aM AO aQ AR AS aU aV aW AX aY BA Bb BC bE bF Bg bH bI bJ bL bM Bn bO bQ bR bS bU bV bW bX bZ cA
cB cC cD cF cG Ch cI cK cL cM CO cQ cR CS cT CU Cv CW Cx cY cZ dA DB DC DD dE dF dG dH dI DK dL dM EM Fp Fr Fw Gn Hr Hv
Hw Ib Ik In Ip Iq Is It Iv Jh Ji Jm Jo Jt KI Ks Lv Lx Ly Lz Ma Mb Mc Mg Mh mI Mm Mn Mr Ms Mx MZ Nd Ni NI Nu Nw Oe Of Og oO Oz Pa
Pb Pc Pz Qd Qw Ss Tv Uc Ug Us Vo Tj) Jj(aC aE aH aI aJ aK aL aM aN As aX aY bA bB BC bE BG bJ bN bP bW bZ cF cH cI cN Co cP cR cS
Ct CU cV Cw CX dA De dJ dK dL dM dN eD Ex Ez Fb Fn Ha hV hW hX IB IC Id Iz Jd jE jF jI jK jL jO jP jR JU jV jY Kd Kc Kg Kj Kk Kq
Kr Kx Ky IK IM IN IO mZ Oa oH Ou Ph Qh QI Qm Qn qT Qu qV QW qX QY Qz RA RB rC Rg Rh Ri Rj rZ Sr St Tz Ub Uc Ue Uf Ug Uk Un
Uo Us Ut Vo Vu Tj) Di(aC aG aH AI Ar As aY Ba Bc bG BN Bo bP bV bZ cH cJ Co cP cT Cu cV CX cZ dA dB Dc De dG dL dM dN dX eF
Em Ex Fb fP FR Gd gL Gn Hc Hw Ib II In Ip Ir It Jh Ji JI kC Kd Kf Kk Kq Lu Lv Lx Ly Lz Mb Mc mI Mj Mn Mr Ms Mt Mu Mx Nd Ne Ng Ni
Nu Oa Om On oO Ow Oy Oz Pa Pe Pf Pg Po Qa Qb Qe Qw Rg Rm St Tn Uf Ug Un Us Tj) Lx(Ax bN cN Cq Cs Dg Dr FP Gc Gd Hr Hu Hv Hx
Ih Ii II Io Ip Iq Ir It Iu Jh JI Jm Jo Jp Jq Js Ks Lh Li Lu Lw Ly Lz Mb Mc Md Mf Mg Mh Mi Mj Mk MI Mm Mn Mp Mq Mr Ms Mt Mu Mv Mw
Mx My Mz Na Nc Nd Ne Nf Nh NI Nq Nr Ns Nv Nx Ny Oe Og On Oy Pa Pb Pd Pf Pg Pz Qa Qb Qc Qd qZ Tv Uc Uk Us Wm) aJ(AD aF aG aI
aK aL aO aQ aR AS aU aV aW aX aY aZ BA Bc bE bF bG bH bI bJ bL bM bN BO bP bQ bS bV bW bX bZ cA cB cC cD cE cG Ch cJ cK cL
cP cR CS cU cW CX cZ dA dB dD De dF dG dH dI dK DL Ex fP fR gW Is jE Ji jQ Mv Ow Oz Pb qT qU qX Ug) Jp(Fr Hq Hu Hv Hx Ih Ii Ij Ik
II Im In Io Ip It Iu Jk JI Jn Jo Jq Jr Js Jt Kf Lh Li Lj Lv Lw Ly Lz Ma Mb Mc Md Mf Mg Mi MI Mm Mp Mq Mr Ms Mt Mu Mw Mx Mz Na Nc Ne
Nf Nh Nj Nk NI Nn No Nq Nr Ns Nt Nv Nx Oe Of Og Oi Ok On Oy Pb Pc Pe Pf Pg Pz Qa Qb qZ Wm) Is(aC Ad aE aH AL aM aN aP aW Ax
aY aZ bA bB bC bH bL bM bP bR bS bU bV bX cC cE cF cH cI cJ cL cN cP Cq cR cS cT CV cW CX cZ dA dB DC DD dG dH DK DI dN Fy
gW Hb iA Ib jH jT Ju KI IL mZ qX Rb Rg Rh Sr Ss Tr Ub Uc Uh Up Wm Tj) Mu(aD aG aH aP As bB bN cC cG cH cJ cN cP cV dC dE dF DG
Dk DL dN Em li II Ip Iq Iu Iv jG Jq Js Jt Jy Kf Ks Lv Lw Lz Mb Mc Mh Mm Mn Mp Mx My Nc Ne Nf Nh Nk NI Nm Nn Ns nU Nv Nx Ny Oe
Ok Oy Pa Pf Qa Qb Qd Qv Qw Ra Uc Ug Vo Wm) Fr(aC aH aN bB cN cV Dg Dr Hb Hf Hr Hv Ib Ii II In Ip Iq Iv Jg Jh Jm Jq Jt Kf KI Ks Lv
Ma Mb Me Mg Mm Mn Mr mZ Nc Ne Nf Nh Ni Nm Nw Nx Oe Og Oh Om Pa Pc Pf Ph Qb Qd Qt Qv Qw Rh Sr Ss Tv Ue Ug Uk Ur Us Vo
Wm) Oh(Fp Hq Hu Hv Hx Ih Ii Ik Im Io Ip Ir jG Jk Jo Jq Jr Js Jt Lu Ly Lz Ma Mb Md Me Mg Mh Mk Mn Mp Mr Ms Mt Mv Mw My Na Nd
Ne Nf Ng Nh Nm Nr Ns Nt Nv Nx Ny Oe Of Og Oi Oy Pa Pb Pd Pf Pg Pz Qa Qb Qc Qd Uk) Nv(Et Fp Hq Hu Hv Ih Ii Ij Ik II Io Ip It Iu Iv Jk Jo
Jq Lh Li Lw Ly Mb Mc Md Mg Mh Mi Mm Mn Mp Mr Mt Mx My Mz Na Nc Nd Ne Nf Nh Nj Nk NI Nn Nr Ns Nt Oe Of Ok Om On Oy Oz
Pb Pc Pg Pz Qa Qb Qd) mZ(Ef Hc HV hW hX iB Im JH Jk jL Jm jQ kC Kf kI kK kN kO Lj Lu MF ml MM Mq Mw MY nA Nd Ne Nh NI Nm
nN nO nR Om oO oP oQ Oy Oz Pc Pe Pf Pz Qd qT qV Qw qX rB rC rX rY rZ) Ug(aA aL Ba BC bE bJ bN bP bV cF Ch cN Co cS De dN Fb
Hc Hq Ib Im Ip Iv Jq Jr Kd Kg Kx Ld Lh Lv Ms Mt Mv My Mz Nd Ni Nq Oi Ok On Ou Oz Pa Pd Pf Pg Po Qa Qw Rm Tn Tz Ua Uf Vv)
Nw(aC aG aH aN aO bB bH bP bR bU cF Cv cZ dB Dg dN Hq Ib Im Ip Ir It Jq Kf Kr Li IL Mp Mv My Nc Nd Ne Nf Nj NI Nt Of Oi Ok Ou Oy
Pa Pb Pg Po Qa Qb Qc Qe Tr Tv Uk Us Vo Wm) cN(aC aH aM AN aP aX bC bN bP bV bZ cH cI Co cS Cu cV cX De dK dN Ef Ez Fn fR Gz
Hc II Im Iv Ji jM jT Kd Kk Ld Lv Mb Mv Mx Ni Nt Oi Ph Qx Rb St Tn Uc Ue Uf Uk Us Tj) kC(Aa aE AI aU aX Bc bE bG bH bI bS bU bX cF
cK cL cP Cq Cs cV cX cZ Db DC De dJ eC Ed Ef HB Hc Hq Ib iO Ju Ko kQ Mv Nc Nj nR Pd Pf pK Qv Rb Rf Uf Uk Uo Ur Us Tj) aA(AI Ao
Ar Bb Bc Bg Bn Bo Co Cv Dc Dd Dk dR dX Ex Fn Fw GL gP Gz hA Hb Hf hW hX Je jI Jv Kd KI Ks nO nR Ow pF Ph Qv Rb Rh rX rY Ss Tn
Tr Ub Ue Uk Us Uu Vo Tj) aP(aF aG aM aN As aU BA bB bC bN bQ bS bU bV cH cI cJ cK cV cW cX cZ dE DG dH dN Ex fP gW Hw II jF
jG Ji jQ jU jV Kf KI Mv Ng Om Ow Oz qY Sr Ss Uk Us Vo Tj) Jh(Hq Hr Hv Hx Ih Ii Ij II Ip Iq Ir Iu jG Ks Lh Lv Lz Mc Mg Mh Mp Mw Mx
Mz Nc Nd Ne NI Nm Nu Nx Of Og Ok On Pb Pc Pg Po Pz Qa Qb Qc Qd Qe Qw Rg Ue Uk Us) Qd(aG aH aN bB Bo bR bV cF cH cJ cP dC Dd
Dg dN fP gW Hw Ib In Io Iq Iu Iv Jm Jq Jt Kr Ks Lv Mm Ng Nm Ny Of Og Om Ou Oz Ph Qw Ra Ub Uc Ue Uk Us) jG(aI eD Et hA hW iB Iu
JL jP jR Js JT jU jY kG IO Mf MI Mp mW Mz nB Nd Nj NI nN Nq nW Ny Og oK Po qT qV qX rB rX rY) Mv(aD aG aH aI Aj aK aN aU aV
bN cP dA dC dJ dL dN Ex Gn Hv Hw In Io Ip Iv Jq Lv Mz nD nI nO nT Og Pc Qv Qw Uc Uk Un) Oz(bA bV Et fR Hq Hv Hx Ih II Im Ip Ir Iv
Jg Jk JI Js Lh Li Ma Mp Mq Mr Mt Mx My Mz Nh Nq Nt Nu Nx Pe Pg Po Qb Qc Qe) Lv(aC Et Hq II Ip Ir Iu Iv Js Lh Li Lu Mg Mp Mr Mx My
Nc Ne Ng Nh NI Nu Of Og Ok On Oy Pb Pc Pg Qa Qb) On(Dg Em Gd Hr Hv Hw Ij In Io Iq Iu Iv Jm Jt Kf Ks Mm Nd Ne Ng Nh Ni Nu Ny Og
Pc Pe Uk Us Wm) Nn(Hv Hw Hx Ij II Iu Iv JI Jn Jr Lh Lw Ly Lz Mc Mf Mh Mi Mp Mq Mr Mx Ns Nu Nx Ok Oy Pa Uk) In(Hv Hx JI Jq Js IL
Mi Mq Mt My Mz Nq Nt Nu Nx Ok Oy Pb Pc Pg Qb Qn qZ rX rY rZ Ut) Uk(bN Co Ef Ex Fb Hq Ip It Jd Ji JI Kq Ld Lh Mp Mt Nq Nx oO
Oy Pb Pf Pg Rm Tn Un) Qa(Hr Ij Io It Iu Iv Jq Jt Mb Mm Mn Nd Ne Ng Nh Ni NI Nm Nu Ny Of Ok Om Oy Pb qZ) oO(Aj An aW Ba Ch De
Ed Fb Fn Id Iz Ju Ke Kk Or Ph Qv Rf Tn Ur Uv Vo Vs Vu) Hq(Bc EM Gc Hr Hv Hw Ij Iv JI Kd Lw mM Mr Mx Mz nA nI nT nU Of Pc Vq)

Figure 5 Continued

Om(bV Cu hA Hr Hu Hw Io It Iv Jl Jr jV Lz Mf Mh Ml Na Ng Ns Nx Of Ok Pz) Jq(Hr Hw Il Ip Iq Iv Mb Mn Mr Mx My Nc Ne Nh Ni Nl Nu Ny Og Ok Oy Pb) bA(Aa aC aN AS bU cI cQ cV De dN Dr fR Gc Gd Gn gW Il Iv Nu Pb Tj) bV(aC aH aN bU cl dN Dr Ex fR gV Il Iv Ji jT Kd Kl Mb Ni Ow Pb Us Vo) qZ(eD hR Hv hW iB jK jM jU jV IM IO Mj Nc Ni nN nU Qb Qe) jT(aO aX bZ cF cl dH dN fP iH jl IL Na Nd Nj Nk nY oK Pe) Dr(aX Ba Bb bQ bZ cL Co cT cY De Ez Fw Gl Hc Hv Tn Ut) Lh(Hr Hv Hw Il Ip Iu Iv Jt Mz Ni Nm Nu Og Pe Pz Ur Us) IL(iB iC Jl jR jU IK IM Mf Nk No Og qU qW qY rB) Iv(cT Hv Hw Ip Jl Mp Mx My Mz Ng Ni Nq Ok Pb Pc) fR(Af aG aN Ap Ba bB cF cJ cT cV dB De Dg Dl eP) Ji(Aa cZ Dd Dg Hb Kf Qw Tr Tv Uc Ue Uh Us Wm) Mz(Jl Js Mc Mi Mk Mp Mq Mx Nm Nq Nu Ok Pc) dN(Ba cT De hA iB jl jK jL jM jY Mb Mx Pb) Tn(Ex fP Gz Il Kl Ks Ng Ra Ss Tv Uc Us) Ok(Hr Io Ip Iq Jm Jt Mb Nd Ni Nu Og Pc) Pc(Hv Ip Jl Ma Mi Mp Mq Mt Nx Pe Pg) jH(aK aL aQ cR cU gW jQ kK Nk nR nU) jQ(aF aO cl dR gL iZ Nj Nk Nl nY) Ba(aG aH aN cV dL dX Gc Ib Nu) Hc(Aa Gc lW mF ml mM mP nT oQ) Ks(Co Ef Ex Fb It Kq Ld Ua Un) bZ(aH aN bB cl Gc Gd Il Nu Pb) jM(aK bO bU cF cR dM iP oF oK) iZ(hA iB jD jE jF jL jU qT) jl(aL bU iB kK nH Nk nU qU) Ex(aF bN bP cL cZ Il Jo) Gd(Co Fb Im Iz Mw Uf Vu) Hw(Ir Jl Kq Mp Mt Pg Qb) Pb(bN bP De eM gC Kd mP) cT(aC aN cF dL dX gV Nu) kF(Aa cF Dd hB Nc Pe Um) Ef(Aa aG aH Ib mH nT) Ng(Cu Et mM mP nT Nx) Qb(Iq Mb Mi Mx Ni Og) Gc(cL Ct De Ez Hu) Ua(Aj fP mF ml Uc) Il(Co Kq Nx Pg Un) Kk(bN bX cF Nd Ou) pK(aF bP dK eM mP) Nq(Hv kK nF rZ) Kf(Cu Kq Uf Un) cl(bC cL iB jL) gC(bC cS ml mP) Gn(bC Hv Qy) Nm(Ip Jl nR) Hu(Em nA nD) Kq(Ij Nd Uc) Og(Ip Jl Po) dM(aC aH aN) Aa(bN mU) Dg(Fb Jg) Nu(aO eM) Un(Mm Nd) cS(dX eP) gV(aX cP) hG(qV qX) qU(oP oQ) jL(bJ oQ) ArOu BgnU CoJo EtMb NarZ NcNi NkjR HvJl IbmP TvPf JgJt QunT KdgW NyPg OibN UmmI UfPa VvnJ PemU aHeM cLoV dHhA qVoF

Constrained panels with 3 analytes, where 1.0E-10 >= 'AUC p-value' > 0. Contains 2,191 panels of 14,487,373 total panels evaluated. :
Mu{Gd(aH aM bB bI cH cJ CQ Cu cV cW dB dC dH Dl Dr Fn Gc Gn Hr Hu Hv Hw Id Ii Ij Il In Ir It Iv Jh Jn Jo Jr Js Jy Kq Kr Kz Lj Lw Lx Md Me Mq Nf Nk Nm Nn No Nr Nw Om Oz Pd Pg Pi Pk Qg Qv Ra Rb Rc Rj St Tv Uc Ud Up Ur Us Uv Vp) Gn(aC Af aG aH Al Ao Ap dC Dg dH Dl eF Ez fP Fy Hb Hw Ib Ic Ii Ik Im Iz Jd Jg Jh Jj Jk Jl Jt Ju Jv Ke Kf Kl Kq Ks Li Lu Ng Nm Ny Of Om Pb Pj Pz Qa Qd Qm Qu Ss Tv Uf Uh Uo Vo) Dr(aC Af aG Al Ao Ap cF cN cV dC Dg dH Ez fP Hb Hw Ib Ic Ii Ik Im Iz Jh Jt Ju Jv Ke Kf Kl Kq Ks Lh Li Lu Mm Ng Nm Of Om Pb Pj Qa Qd Qm Ss Tv Uf Uo Vo) Gc(Af aG aY BA bN Bo bR bW bX cF CT dA Dd dH dI eM fP Gz Hb Hq Hw Ib Ik Lh Lu Lx My Of Om Pb Qn Tr Tv Vv) Jj(aA aH Em Ip Is Iv jG Ji Jq Lv Nu Oh Oy Oz Pc Qa Qb Qd) Em(aC aG aH Ap bN dC Dg Iz Jy Kd Ng Qm Qv Ue Ug) mZ(fP Iu jG Mt Pd Pg Po) eM(aH iJ kC mH mI nH) gC(aH bB bP Im Nu Ny) oO(fP Ug Um Vo) mP(Jl Pe Qe) Ug(fR oQ) UmoQ PejT fPkC jGkK} Ua{Gd(aG bA Bb bC bN cH Cs cT dC eM Ex Hv Ib Im In Is Iz Jn Kc Ky Ld Lj Lx Ly Lz Mc Mi Mj Mp My Ng Nw Nx Oa Oi Om Pb Ph Pk Qh Qv St Tn Uf Vp Vu) mZ(aC Al Bb Cq Dc Dg fP Ii Jk Jl Jm Jp Jt Ju Kf Kl Kn Kq Lh Li Ma mI Mm Mn Ni Nm Oh Om oO oQ Oz Pb Qe Qh Rf Rh Rm Sr Ss Tr Ue Vo) kC(aC Ad Al Ax bM Cq Cs Dc Dg Dk Dl eM fP Fr Ih Ir Jk Jl Jp Jt Kf Kl Li Nm Ny Om oQ Oz Pb Qa Qb Qe Sr Vo) oQ(aF aP Cq cX Dc Dd Hx Il Im Jn Jo Ju Kc Kz mI nH Om Oz Pa Pb Qh Ue Um Uv Vo) oO(Dd Fw Hx Im Jo Ju Kc Kf mI Ny Om Pb Qh Rg Ue Ug Um Uv Vo) nT(aC bM Dd Li Qe Qh Rm Uc Ue Uv) mI(aC bM Dc Jk Oz Pb Qe Ue) kF(Cq Dg fP Kl Qe) mS(Ad Dg Dl Vo) bM(mF nA nH) Jj(fP gW) Pb(mP nA) nN(Cq Jk) nH(fP oF) CwGn DdmH DrKf NygC aHeM} Jj{jG(aA Et Fr Ii Ip Is Jl Jk Jl Jm jO Jp JQ jT kK Lh lM Lw Lx Mg Mj Mp Mv MZ Nk Nn nR Nv Nw Ny Oh Om On Po Qc Qd) Oy(aA Im Ip Is Iv Jh Ji Jq Lv Lx Mz Nc Nh Nl Nt Nu Nv Nw Nx Oh Ok Qa Qb Qc Qd) aA(Fr Ip Is Jg Ji Jk Jq Lv Lx Mg Nj Nn Nt Nu Nv Nx Oi Oz Pb Pc Qd) Oz(Fr Im Ip Is Iv Jg Jh Ji Jl Jq Lx Mv Nn Nv Oh Ok Qa Qb Qd) Ji(Fr Io Ip Jk Lv Mm Mn Nm Nn Ny Om Pc qZ) Is(Fr Hw Ih In Io Iq Lv Mn Ny Om Pc qZ) Oh(Ik Im Ip Iv Jh Jk Jq Lv Ni Nu Pc Qb) qZ(Il Jp jQ jT Lh Lx Mj Ms Nw Om Qc) Nu(Fr Ip Iv Jg Jm Jq Mp Nw On Qb) Jq(Ip Iv Jk Lv Nl Pb Pc Qa Qb) Nv(Io Lh Lv Mm Mn Nm Ny Om Pc) Qb(Io Ip Lv Ni Nn Pc) Qd(Io Ip Jk Lv Pz) lL(kK mZ nR nU) Ip(Iv Jk Lv) Qa(Io Lv Pc) Pc(Fr Ok) GcMv TzgW HqmZ hAnR} lL{nA(hV iC jD jH jI kG lK lM lO lX Ma mH Mq Mv My mZ Na Nc Ne Ng Nk Nl nR Om) nI(Fr Is Jh kG lK Lx Ma Mq Mv Mw Mx My Na Nc Ne nF Ng Nk Nl Nq Nx Of Om Pf) mZ(aA Fp Fr Hu hW Im Is JH Lx Mq Mx My Na nR Pe Pf rB rZ) kG(aA Is Iu jG jH kK Ly mM My Na Nc Nj Nl Pd rB rX rY rZ) nK(Fr Hx Is Iu Jr Lx Ly Mf My Nc Ne Nk Nl Nq Pe Pf) nJ(Fr hV Is Iu jD Lx Mf My Na Nd Nj Nk oP oQ) kK(aA hW HX jH lK Mf Mq mW Nl Nq rB) nU(Na Ne Ni Nj Nk Nl Pd) lW(iC kF mF nN oQ rB rZ) qZ(hV Ji jQ jR Lw rZ) mH(mF oP oQ rC rZ) nR(jH Mq Nu rB) nT(Fr Ne Nk Om) rZ(lY mE mI nN) jG(Lw mW oQ) kF(Iq Ir Iu) Na(kO rY) Nc(kC nL) aA(jQ jR) nN(jQ mP) lK(kN oP) oQ(jL qU) LwMf MqnO NekO HumP PfkC} Mv{Gc(Aa aC Ad aG Al Ao Ap BO bU cF cJ cN cP cV Cw dC Dg dH Et fP Gd Hv Hw Ib Ii Iv Jd Jh Jm Ju Jv Ki Lh Mg My Ng Nr Nv Oy Pb Qh Qn Rh Tr Tv Vv) Gd(aC aG aH cJ dB Ex gP Im Kr Lj Mj Mm Mx Nw Oa Oi Oz Pb Pk Qb Qv St Vp Vu) kC(aC Ad bM Co Cq Dc Dd Dg eM fP Jd oF oN Or Pd Pe Pf Uc Ue Ug Um Vo) Dr(aC aH Ap cN dC dH Hv Ij Pb) nA(Aa Dd jL Pc Pg) gC(aH bB Nu Ny) Pe(mF mP mZ) Gn(Ap Dg) Nm(mP nR) mI(Co Ue) qZ(hV jQ) oO(Kc Ug) AanK EmaC UcQd OumP UmoQ aAaH jVkK}
oO{Ug(Aj Ao aP Ba bC bH bQ Ch cL Hc Hq Iz Jh Kc KF Kg Ms My Ng Nq Nr Ns Nx Oy Pb Qy Rg Tn Vv) Kc(aF Ba bM bQ bX Dd Lu mU mZ Nd Nj Oy Pb Tj) Hc(Ad bH bI bP Cq fP Ii Je mZ Ur Vo) Dd(Aj aP cF cL Fb kF Mt Nq Nr Um) bH(Hq Hr Ic Mx Oy Pb Pk Qv Um Uo) Vo(Aj Ba Bg cL dF Fb Iz Ng Uu) Um(aO aP aY bM bX cL Mk Pb) Iz(fP Jp Jt Kf Ks Om Tr) Rg(cL Hr lX) Ur(Oi Oy Vs) Ba(mI mZ) Cp(fP mZ) Ks(Jh Nr) Oy(Jd Tj) Pb(aP dJ) aW(fA oW) FwcL JuJv OmUf VvbX PhaP aHeM} Dr{My(aC Ad Af aG aH Al Bb bN Bo bR bX cF cN cS CV Cw dA dB dC Dg dH Et Ez Fb fP Fy Hb Hq Hv Hw Ib Iv Jg Jm Jp Kf Kk Kl Ko Kp Kq Lh Lu Ma Mi Mm Mp Nk Nn Nw Om Pb Pi Pk Pz Rc Rg Rh Tr Ub Uh Ul Vo) Hu(bC cN Gd Ib Ju Jv Ng Ny Vo) Om(Aw Cp Ez Is On Tn Ut Vv) Hq(aX bR cS Jm Ju Tj) Ef(Ad Af aG aH cN) cS(bN bR cF dR gC) Hv(cF eM Hc Pb) Hb(Cu Kq On Tn) cN(Ba Kg Kj Ut) Vv(bN Kf Vo) aG(Aw Co Ou) LuOu KfOn} aA{jG(aL aS bE bV cI cT jO jQ jR kG kK Mc Mf Ml Mx mZ Nk nR nU Nw oP Pf qZ) jT(aC aD aK aL aM aN aS aX bA bE bG bJ bQ cG cI cT cW cZ dF hB hC oE Wm) qW(aC aK aL aQ aS aU aV bE bI bJ cI cM cT cW cY dF oH) Ji(Hw In Jm Jo Jt Lh Mm Nm Ny Om Oz Pc) jM(aS bP bQ bU cT gP iZ) qZ(hV jO jQ jR) hA(aL cT dN) jL(mZ nR nU) jV(bA cG dF) Oz(Nn Pc) qU(gP nY) DgKc NuIn aCbE aLqV cFcV cUjQ mZhR} kC{Oy(Ad Al Bc bH bI bM bX Cv Cx Dc Dd eC oK oN Pe Rb Tv Ug Uk Um Ur Tj) Hq(bI bM Cq Cv Cx Dc eM Je oF oK oN Or Pe Pf Rb Ug Uk Um Ur Vp Tj) Pb(Bc Bg bH bI bM bN bQ bR bX cD Cv Cx eC Ef Kc oK Pe Uf Ug Um) Aw(Af Cq Cx Dg Dk fP Jt Nm Om) Ef(Cx Dc Kl Kr Qe Sr Uc) Pe(iB jF Jk lO Ng Nn Nq) Cx(bR Hc Hv Um) Nc(hA jK) Jk(Cq Pf) bX(Kc Vv) cL(Cv gC) lO(Pd Pf) CoJt NqSr IzfP PzUg} Ef{mI(aH Al Ax bB Bc Cs Cw Dc Dd Dg Fa Jg Kl MM Nm Oz Pb Qe Qm Sr Uc Ug Uh Un Vt) mF(Ad Al fP Jt Kl Kr MM Nm Pb Qe St Uc Uh Un) mM(Ad Al Cq Cu Dg Dl fP Jp Jt Li Pb Qe Ue Vo) lW(Dc Fw Kl Pb Ss Uc Vo) Gc(Ad aH Ba cF cN cT) mH(Ad Ap Bb Dg Jo Jt) kI(Cq Jt Ny Qe) Gd(bA bN) Qe(kN nA) Uk(dJ fP) nT(Mm Nm) mY(Cq fP) BbnK PbmP} gC{cI{Dl Et Ez Gc Gd Hv iA Jt Jv Kf Kl Kn kO lY ml mY nC Ng nH nL Nm nO nT Ny Om Oz Pb Ph Qn Ra Rc Ss Ul Uo Ut) bC(Ba Ir Jn Jt Kf Kl Mk Nl Nu Om Oz Pb Ra Ub Ug Vo Tj) Tn(Af bP CX Ij Kn No Nr Pb St Uu) aH(Ez Kq Mi Mw) bW(nC nH Oz) My(Kc Oa) Uf(Jo Jt) CxHc GzKc HfVv QdOm bMml bPmP} qZ{jQ(hA Ih Il In Io Ir It Iu jG Jh jI Lj lO Ml Mw Na Nh Nk Nl Nq Oh Pd Pe Pf Pg) hV(In Io It Iu Jl Lj Mf Ms Mw Nk Nq Pd Pe Pf) jR(Ih In Io It Iu Jl Lj Ms Nw Om Pf) Is(Hw Io Iu Jl My) jG(Ji Lw Mg Nw rZ) jT(Io Iu Lj Pe) Nw(Hr jD My) mZ(lM lO nR) Ji(Ij Nt) nI(iC nN) LweD} jG{mZ(Fr Hu hW iC Im Iu jD JH jI jO kK Lu Lx mF Mq Mw Na nU Om On oP oQ Pc Qd qT rZ) jT(aJ aP iZ Jp Nv Om On) Is(Iu Jm Mf Nk Pz) jI(jQ jR kK lM nR) Nq(kK nI rY rZ) Iu(kF kK Om On) Mf(Jq Nw Om) Mq(kK kN nR) dN(jQ nY) nR(jH rB) FrkK NoNr MkOm NenU NkOn HumP InrZ aIiZ} Gd{Hu(aG aX bA

Figure 5 Continued bC bP bU cA cN cT dB dH Fb Ii Ij Il Im In Jm Jo Kc Ly Mi Mp No Nw Oa Pb Qv Rb Rh St Vu) Tn(cW Ii Tj) Im(Aw Ba cT) My(Qv St) AwaH
BaQd FrHc MweM IbVu HbOn IsJm QybA} Nc{jH(kF kK kN mZ nB nI nJ nK nR nT nU) IM(kl mF mM mP nA nl) hA(mF ml nA nl nK)
jI(mM nl nK nT) nU(jT IK qU) nA(jK jO IO) jY(nC nH nL) IN(kK mF nR) mZ(qT qW) IXjQ nBqT jVkK} Gc{My(AI aU aV Bo cA cF cK cV
dR Ez Kg Li Mi Mp Nn No Nr Qy Rh Uf) Ba(cF Co cS De Li Nn Qy) Co(bA cN CT eM) Hu(aX bC cF Mi) Mi(Hq Ng) Qy(cT Of) VucF}
Pb{kF(Bc bl bN Bo bR Cv Dd fP oK Pe Ub Ug Uk Um Uv Tj) ml(Ba bQ Di Tn Uu Vv) mP(Cp Hc Ib Pi Tn) mM(bQ Cp Hc) mZ(bN Ib) nA(Ba
bH) UmmU bQlW} Hq{mP(aY Dd Iq Nj Pe Pf Um Vt) mZ(bP Dc Ii Jm Nj Pe Pf) Tj(kN mF mM nH) UmmM UrmF PfnA blmH} gV{bA(aC
aD aF aG aO bL bM bP bU dB dE) cT(aC aF bM bP bU cD) aC(aX gL)} Is{Jm(fP Hw Om Pz) Og(Hw Iq Ny Om) In(Nm Nu Om) Wm(jT qY)
Gn(Aa Hb) IIPz RbfP PejT} eM{Qd(Jt Kf Om Oz Uh) pK(aH aS cL cZ mP) Aa(Kq Mw Vs) aH(Iz Mw Qw) MwfP cLoQ} jM{aJ(cP jQ jR jT
nW) aP(bU cD cL jQ jT) jT(dG dM iZ) jQ(dR nY) bUjI dNgP jHoK} Gn{Hb(Cp Fb Fr Kq Lh Lx Nw) My(Ub Uh Ul) Cp(Aa Om) AwaG LxUh
OmUt} Em{On(Aa Hb Hw Jt Ok Om) Tn(Et Ks Uh) bN(Ba cT) AwaG MwUl HbLh} Hc{mI(Ad Al Cv fP hB oF) fP(kF mM mP) mP(Dg Jt) AlmZ} mP{Hu(fP Lh Mf Nm Pe Pf) IbbM UmaY nHpK} jT{Pe(Fr Jp Nv Om) aC(aJ aP) aDjI aJbM bEcF} bX{Vv(mI mU nC nH nJ nL) mI(Di Tn)} nU{Ne(jL jV) Nk(jH jK) Nl(jL jV) NjjD} kK{jV(Fr Ng Nl Nn) lN(Na Nl) IzfP} pK{nO(aK bC cL) dK(bP oF) bCcI cLkO} Cp{fP(Ad Rb Us) aG(dX eP) UcQd} mZ{jL(Im Mq) NkqT HuVs IiJk JhiC} jQ{dR(dN jH lK) aJlK aPhB bFjH} oQ{Iz(Lh Um) Ug(Aj Oy) DdcL NfQy} nA{lO(Ne Nk Nl Pf) NclM} rZ{In(Pe Qc qU) Nq(Pd Pf)} cT{aH(oV oW) bNeP dFoW} Dg{AwfR IzkF} Nk{nT(jH jI)} aC{eP(aX bE)} fP{FrRb IzkF} hA{aJdN aPcD} nR{NujH NljV} rY{NqPd InQc} IbUrmI IjOmPc UmbHlW PemFlM bVdUiH Constrained panels with 3 analytes, where 1.0E-9 >= 'AUC p-value' > 1.0E-10. Contains 1,059 panels of 14,487,373 total panels evaluated. : Jj{Oz(Et Ih Ik Ir Jk Jm Jp Js Lh Li Lv Mg Mi Mp Mx My Mz Nc Nh Nl Nq Nt Nu Nw Nx Oi On Po Qc Qe) Pc(Ik Im Ip Ir Iv Jg Jh Jk Jl Jm Jp Js Lx Mg Mv Mz Nn Nu Nw On Oy Qc Qd Qe) Nu(Hq Im Ir Jh Jk Lv Lx Mg Mi Mv Mz Nl Nn Nx Oi Po Qc Qe) Iv(Fr Im Jg Jh Jk Jm Lh Lv Lx Mv Nl Nn Nt Nw Nx Oi On Qc) Ip(Fr Im Jg Jh Lx Mi Mv Nc Nl Nn Nt Nv Nw Oi On Po Qa) Oy(Fr Ir Jg Jk Jl Jm Lh Mi Mp Mv Mx Ne Nn Oi On Po Qe) Oh(Fr Jg Jl Lx Mg Mn Mv Nl Nn Nt Nw Oi On Po) Jh(Ik Jk Jq Lv Lx Nc Ne Nh Nl Nx Ok Pb Qb) Jk(Ir Lv Lx Mz Nl Nt Nw Nx Qa Qb Qc) Jq(Fr Im Jg Lx Mn Mv Nc Nn Nw Oi Om) Qb(Fr In Jg Mg Mn Nw Oi On) Ik(Jp Js Mp Nd Nw Pa Qc) aA(cV Mb Nd Nw Po Qc qU) Io(Jg Jp Nw On Qc Qe) Qa(Fr Mn Nn Nw Ny Oi) Qd(Fr Mn Nn Ny Oi qZ) Ok(Ij Im Nc Nl Nn Oi) Nx(Im Mi Mv Mx Nn) gW(Ch Ef Iz Jy Kd) Lv(Fr Lx Oi Qc) Om(hA Ij In Nw) jG(Jn Nd No nU) Mv(jQ mZ Nl) qZ(hV jR Og) lL(Is jT Lw) Cp(aH cV) Fr(Nd Nl) Nw(Mm Nm) AwaH BacV DrHq NnNv MuQc NiJm NkjQ NlIm UamZ InJi IshA kKlO} oO{Kc(aA aP bA Bg Hc Hr kC kF nB Nk Pk Uv) Ug(Aw bF bM Co hG Ib Jg Ji Mx mZ Ok Uo) Iz(Ad Bb bI Cq Dg Kl Nm Ur) Hc(mI Mj oF Om On Uk Tj) Rg(aK aQ aU aV bR Fb mZ) Dd(aJ cE Kf Mu Mv Tn) aP(Nf Om Vo Tj) bH(Aw eM Mu Pf) Ua(Il Jk kC) Aj(Om Pb) Nm(Fb Uf) Mu(Cq Ur) Mv(Ue Vo) Oy(bI Qx) CxaA DcPb NfQy NgUk HqbI TnbX eMiH} aA{jG(bJ In Ir Is Jp Md Mi Na Pb Pd Pe) Ji(Hr Ih Ii Ij Iu Mn Nf) Oz(Hr In Is Lv Pe) Mv(Dg fP Oy Ss) Is(Hw In Om) Nw(Jt Lh Nm) aN(aH cV Cx) jL(kK nJ oP) jT(cQ lL Pe) Aw(aH Dg) Cp(Dg fP) Kc(aG bN) cV(cH cI) qW(gP kQ) jQ(hV mZ) lO(bQ qZ) NtIn PerY aCaL bAjE cEjV nHrZ} kC{Hq(AD Bo cP Dk eC nW Pd Qx) Mv(Al bI bR Cv Cx Jy Sr) Kc(Ba Bg Ct Nk Ua) Dc(Ba Hc Jk Ng) Um(Bg eC Lj Qw) fP(Bg Cp Hc Nq) Ng(Ad Pf Ug) Ba(Cq Vo) Cx(Bn Nx) Ef(Oz St) Mu(Dk Pe) Ua(bO Ma) cL(Dd Nk) AwJp CoDg CvHc NmnR NljK TnbX JuOy LhbH NxUg OrbM PbPf} Dr{Hu(Hv Lu Ly Ni Nm Pb) bC(cS Di Hq Hv Nb Ub) Tn(Af aG Hw Kf Ks) On(Af aG Hw Ks Rc) cS(bA bU cV Di Tj) Hv(Ba CT Kg) Om(Cu Jg Kq Vu) Ou(bR cF Hb Ml) Mv(Ao Dg Mm) Ez(aG cN) Lu(Aw De) Ua(Kl Vo) Hb(Is Ji) Ut(bN Pb) BoMu CtVo HqaW aGcG} Is{Jm(Io Iq Ji Jt Lv Mm Mn Nm Ny Og Oz Pc qZ) Og(Ih Io jG Jt Mn Ni Nm Oz Pz) Il(Hw Io Iq Jt Ng Nm Om Oz) In(Io Iq Mm Mn Ni Ny Oz) Pz(Hr Hw Ji Lv Mu Ni Oz) Pe(jH rY rZ) Hw(Io Ny) DiKf NmNi NljG JkqZ UgfP PfjT} Gd{Mu(Ad aG As Ba Bn bW cC dG dL Em Jk Jq Mi Mr Na Nb Ni Pb Ua Ul Vs) Tn(Ba Bg bP Ij No Pz Rh Uv) Aw(aG bI bN dB Vu) Mv(bI dC Nk) Ua(bU cN Iv) Hu(Ao Kr Lu) Im(bA Ct Hc) My(Mb Uf) DecT DiVu EfaH FrRg HqgP HcUf} mZ{Hq(Cv Jl Lx Mf mM Nc Nm Ok Po Rb) Mv(Jl Li Mm Nc Nj Nm Pf) Ib(aY Lh mI Nd Ug Ur) jG(hA lM My nB Ng nR) Pb(Ba bH Pe Pf) Mu(mM Nm Pe) Ng(Jl Ok) Ua(Mf nH) Hu(Lx mM) Hc(fP Jp) NjqT qZoP} qZ{Ji(Et Ii Il In Jt Mm My Nx Pe) jR(hA Il Jh jQ Na Nk Nq Pe) hV(hA Hv Ih Il Nw Om) jT(Mg Na Nk Pd Pf) Nw(Nt Pf Po) MsjV MyJp NkjE HwLh IlqU InQa nNlW nIoP qWjQ} jG{Nk(Jp Lw Lx nU Nw rZ) Om(Hr Hw jQ kK Of Og) kK(hX mW Ng Nl) Lw(lM Nl On) jT(Fr gL Jq) Mf(Ji On) Na(rY rZ) nR(hX mW) lM(jQ lL) NoPf NqnK HwOn IukG PzNw jIrY} Ef{mI(bM Dl Il Jo Ny Ok Qa Ss) mM(Bb Il Jo Kf Mf Om Pj) Gc(aX bA bU cS Ct) lW(aH Dd Ue Uf) mF(Cq Ez Oz Sr) nT(Mp Un) AabN JonO UhmH PbkI} Em{On(bN Dg Ks Uh) Mu(bA dH Jo) Mw(Ap Hw Pb) Hv(cF Mv Pb) Tn(Aa fP Hb) Fr(aG Ul) bA(Co De) AaCp ApMv BaaG MbMy HqQd HbNw UtbN} gC{bC(Ao Ct Cx Dl Io Nm Qc Us) bP(Ez Hc kG Kq Mi Mv Ua) Af(bW cL Kq) Mi(Oz Pb) bB(Ez iH) cL(Nl nU) MuaO QdOz PbbW} mP{Hq(Al Nc Pd Uo) Mu(bM Ih Mf) Hu(jL mM Pd) Pb(Ba Co Uu) pK(aW nC nL) Mv(Mf Mm) CoJt CpfP NmNg UcHc} Ua{oQ(Jv Mf NA nB Nf Nm Qv Ug) nT(iA Ih Iu Vt) mW(Dc Nm Vo) mI(Nm Sr) DckF GnaG aCnH} lL{nJ(Hx lW Nq) Lx(nT nU) Mf(Ji nU) nI(hV nD) kK(Iu Mm) LwOg MhkF HqkG NwhA nMnK nNjR nRhW mMiC} Mv{Uc(aJ aP Nb) Jd(mF mH mI) Dd(mI nU) Pg(mF nU) kK(jL Nm) GcUb KcaG PenI PfmF fPmM} pK{bC(aW eM mI nC nH nL) eM(bJ bW cV mF) mI(cV oE) bBcS cLnH dKfP} Pb{mI(Bg Hc Qu Ub Tj) kF(bH bX Pf) TnnA UumF aHeM} Gn{Mu(cV Fb Lh) Aa(Cu Vv) Hb(Aw Cu) WmcF LuOu OmOn} jM{iZ(cA jQ jR nW) aP(cE hB) gP(lM nW) cFjT} Dg{Kc(bZ cT Fr) Aw(aJ aP) BafR CpaJ QdeM} Gc{Nn(bA cT) CoDi QybA LicT UfcF bRcS} Pe{Hq(mF mM nA) NqrZ OnjT OykF nAlO} jQ{lK(aP cD nY) NlNw InhV cUlM} jT{aJ(cD cF) bE(fP hG) aCiZ aPhB} rZ{Na(Nc Pd Pf) In(Jm Pf) JhPf} Cp{Uc(fP Mu) AdaN JofP aJdG} Qd{Uc(Ba cT) DiKf HwbX VocT} jV{kK(Jk Mu Ne Nq) NjnU} oQ{Iz(bI Ug Ur) HcUg KcbF} eM{Aa(Po Uf) NunJ MwKl} gV{bA(hZ dR) cFcT} mI{Hc(mM Rb) BoDi} nA{NkjK NlIM PfrA} kF{IbfP IujL IzKl} Ba{KcaG aCbE} Mm{Ji(Mu Oz)} cL{oV(aG hC)} ChUgkI MuMzIj NcnBqW NemFlN HqbInH IlKcbN InJmrY PznRjH aPhBjR Constrained panels with 3 analytes, where 1.0E-8 >= 'AUC p-value' > 1.0E-9. Contains 1,727 panels of 14,487,373 total panels evaluated. : Jj{Nn(Ik Im Ir Jh Jl Jm Lh Lv Lx Mn Mp Mr Mx Mz Nc Ne Nh Ni Nl Nt Nw On Pb Qc Qe qZ) Oi(Fr Hq Im Ir Jh Jl Jm Js Lx Mg Mp Mr Mv Mz Nc Nl Nt Nw Nx On Pa Pc Po Qc Qe) Pc(Hq Ih Ii Lh Li Lv Mi Mp Mq Mr Mt Mx Ne Nh Ni Nl Nr Nt Nx Oz Po) Nl(Ir Jg Jm Lh Lv Lx Mg Mi Mp My Mz Ni Nt Nw Nx On Po Qc Qe) Nw(Ij Im In Jh Jm Lv Lx Md Ml Mn Mv Nc Nx Ny Pb Pg) Nc(Hq Im Jg Jm Mg Mr Mv My Mz Ni Nx On Pb Qc) Im(Ik Io Ir Jg Jh Jk Lv Mp Mu Nt On Pa Qc) Mg(Ir Iv Js Lv Mx Mz Ne Nh Nx Pa Qc Qe) On(Ir Jh Jm Lv Lx Mb Mn Nd Nx Om Qc) Mv(Ij Ir Jm jT Lv Nt Pa Pb Qc Ue) Jh(Ir Jm Lh Mx Nt Pa Po Qc Qe) Nx(Hq Ir Jg Jm Lh Lv Nt Qc) Pb(Ir Jp Js Mz Ne Nh Ok Om) Jk(Io Jm Mx mZ Om Po Qe) Jl(Io Ip Iv Jq Lv Lx Mb) Mi(Ik Ir Iv Jm Nh Qc) Mp(Lv Ne Nh Nj Nt qZ) Mz(Hq Ik Ne Nh Nj) Qc(Jg Lh Mn Mx Nt) Mt(Ik Lv Nu Oz) Nk(jT lL Mr Ni) Jg(Ir Lv Mx Ne) Ok(Hr In Io Ml) gW(Ez Qz Rf Tr) Nt(In Jm Nd) Mu(aG bN cV) My(Ik Ne Nj) Hq(mP Ne Nh) Is(aH fP Kf) Lh(Ik Jm Nh) Om(lL Md Ml) Oz(Ii Mj Mr) qZ(Ip lO Mk) Aw(Bo cV) Cp(Ad fP) Mn(Fr Lx) Jp(hA Ni) jG(Ms Mw) BaNu EfmM PoIv LvJm MqPa MxIk NfjT QdqU KccT mZlO jQlL} Is{Pz(Fr Ih Ij Iq It Jh Jp jQ Lx Mb Mn Nn Nw Ny Pc Qd qZ) Hw(Ih In jG Ji Jt Lv Mm Mn Ng Ni Nm Nw Oz Pc) Jt(aA bN Et Fr Ji Lv Lx Mu Ni Nw Ok Oz) Og(aA Il In It Ji Jn Lv Mu Nn Oi Pc) Il(Lh Mg Mm Mn Ni Ny Pb Pc qZ) Iq(aA Hr Ij jG Lh Mm Mn Nm Oz) Jm(aA Fr In Ip Mu Nn Nw Oy Pb) Ng(Fr Ih Jh Mn Mu Mv Ni Oz) Ny(aA Fr Hr Ji Lv Mu Ni Nv) Om(bN Hr

Figure 5 Continued

Ih Ij Io Jh Lv Ni) Nm(Hr Ij Iu Ji Lv Mn Nw) In(Jq Mz Nl Nn Nt Pb Pc) fP(Di Rm Tv Uk Us Tj) Ni(Ij Mm Of Oz) aA(Hr Ih Lv Pc) Gd(Pb Ub Tj) bN(Aa Dg Jo) jG(jT Ml Nj) qZ(Ir Js) IL(Mf nO) DgKc MmJi MuUc NbTv Hrlo PfrZ} kC{Hq(Al Ao Bb bF bH bR bX fP Ha Hc Jd Jy Kc Tv Ut) Oy(cP Cq cW Dg fP Hb Kc Kf Kr Pf Sr Tr Ua Ub Uc) Mv(aD bO bX eC Je Kr oK Rb Tr Uk Tj) Aw(Bb bX cV Dc Dd eC Kf Kl Nv Ny) Ef(Af Ax Bc bM Cq Cs Dl Kf Ny Vo) Ua(Dd eC Fw Kn Lh Mm mZ Nu Tr) Um(Ax aY Ba bR bX Ct nI Or Pz) bM(Cv Jk Mp nl Nn Nu Ub) Ba(bA bR Cv eC mZ Ug) Cx(aY bF De Di Mu Ub) Bg(Cq Cv eC Kl) Ct(Cq Cv eC Or) Iz(Dg Jt Kl Or) Pe(Jh Mg mZ nR) Cp(Ad Dg mM) Hc(Al Ax eC) bX(Di Nu Qd) Mu(bl Pf) Ub(cL Pb) Vo(Ng Pz) Oz(De Kg) fP(Co My) nR(Jt Qe) AxbR BoDi CvNx DcTn EdMi NdKc NejK JkeC OrbH UgaY PfiB bCpK} aA{jG(Fr Hr Hv Hw Hx Ij Jn Jr Js Me Mj Mt Mz Nf Nm Nr oK Qa) Kc(dG fP Il Kf Kl Ks Mm Om Ow Ug Tj) Om(Fr Ij In Jq Mu Nn Nw Pc) cV(AW Ba cN Cp cT Di dN) Hw(Fr Jq Mu Mz Nn Nw Pc) Oz(Fr Jg Jq Lx Mu Mz Nw) oO(aW Dd Ph Rg Ug Uo) Lv(Hr Ij In Jo Pc) Mv(aG Il In Kl Uc) aH(Cp cQ cX Di Pb) Ji(Ir Mb Md Pb) qU(Nd nU rY rZ) Cx(cH dG Di) In(Mu Nn Nx) Pf(jT rY rZ) aC(aX Ba cZ) qZ(Mj Mz Pe) Aw(aG fP) Nw(Hr Ny) aN(cF cX) cI(hA jQ) jT(dL kQ) lL(Mf Nd) lO(hB nA) AdCp MbPc RbfP PbbN PerZ aKlK cFcX cTjQ cZqW dFjL nHrY} oO{Ug(Bg bR Cp cS dF Di Ez Kc Kj Nj Oi On Pk Pz Un Vu) Dd(Bg Co cS De dF dG Hq Lx Oi On Pf) Hc(Dp Fw Hr lW mP Of Pg Rb Tv) Rg(bV dR kF Mu Nj Nt Qu Uf Uo) Ua(bP Iq Mf Nf Nm Oz Ph Wm) bH(Aj Ba Di Gp Mv Nk No Oi) Mv(bM Cq fP Ju Kz Ur) Ur(Ba Bg Ib Ng Of) Vo(cE eF kF Nq Uf) Pb(bI bN cL Ph Uf) Oi(bI bM Dc Uo) Om(Bg Cp Fb Qu) Fw(aP Fb kF) mZ(Aw Id Vu) Cq(Aw Cp) Nr(bX Iz) Hq(Bo Qx) Kc(cL Qv) Uo(dE Oy) Ph(cL kF) aP(aW Kz) ChKf EdkF FbfP MubM TnKs IzJo QzOy aJaW mIpK} Dr{Hv(Bo bR Di Hq Of Oy Ri Ua Vs Tj) bC(Aw bA Ct Ef Ib Pb Ua Tj) cS(aV Aw Ba cN CT Ef Pb) Tn(aH dC Et fP Ib Uh) Hu(aG bR Ke Kf Rh) cN(Bb cT Hq Na Uf) Fr(aG cF cV Ul) On(Ib Jv Uh Vo) Co(Af Dg Kf) Ez(Hb Lu Pb) Hq(Hc Mi Ri) aG(bQ Ct Om) Lu(Kg Mi) Mu(bR Nq) aX(aC Ef) cF(cT gL) AfAw BoMv DiaM LxcV HbNw aHcG} jG{Om(Jm Jo Li mP Nd Nk Pd Pe Pf Po Pz) On(Hr Jg jQ jR Nj Og Pe Pf Pz) Fr(Iu jQ Li Lw Mf mP Pz) Nk(Jl Jq No Nv Qd) Iu(Ji Jq Lw No Nv Nw) Lx(jT Mf Pz rY rZ) Nw(jT Lz Nd Pe Pf) dN(bC bO gP jT nW) Mf(Jp Lw Mz Nv) jQ(aO aP Jp) Lw(Jp Nj) nR(hW lL) qZ(hV jR) jT(dG lM) MqnN NekO NlkG InJn aPcD mWjO jHkK} Gd{Mu(aY Bc Bg bN Cp eF fR Fw Jl Jt Kd Kp Mb Pe Tj) Tn(aH aX bU cA Jk Nr Pg) Im(Bg Di Hq My Ng Pz Ri) Aw(cA cJ cV dC gP Qd) My(dB Ez Nw Pb Ub) Hc(bN bU Li Vu) Ef(bH Qv St) Mv(Ap Co Qn) Ua(aX Di Hb) Jk(Ib Uf Vu) bA(Nn Uf Vu) Cp(Em Tj) Hu(Ad Ub) BagP FbHb IbUf cSgC} mZ{Hq(bH Dd Hr Ir Jo Li Lj Mm nA Nd oF Oh Qa Qe) Ib(bP Cq fP Ii Jp Ju Kc Mj Mn Nj Tr Tv) Mu(bI Bo Dc Nj Pf Rb) Mv(Ii Jo Mf mM Oz Pg) Ng(Ii jQ MM Nm) Ua(aY bP oF) Jk(Jl Jm Nc) Pb(aY bP Qw) Hc(Ii Jt) Jh(jQ jR) jL(oQ Qd) BamI UbbH HuPe UmaY PcqT} Ef{mI(Ap Ez fP Ii Jq Kr Ph Pj) mM(bH cV Kc Ko Ny Ok Uo) kI(aH Al Ax bB Ed Kl Uc) Oz(lW nC nH nJ nL) mF(Mz Nj oN Ss Vo) lW(Cw Kc Kf Uu) Gc(bC cP) Kc(aG Uk) aH(nT Uk) mH(Jg Ok) DgaJ NmnA} gC{bC(Aw Ha Kc mI Nk Or Ul Ur) Mu(Cq Cx Ij Iq Mw) Tn(aW Dc Dd Ir Kx) oW(eM kO nC nH nL) Qd(Af aH Pb) Kq(Om Qe Sr) Cx(Iz Mv) Ez(Nu Pb) Mi(Nu Sr) Kc(aW bN) bW(kO nL) MvIj QubP VvaW cLnF} Pb{mI(Aw aY bF Cp Cv Gp Pi Ug) nA(aY Bg bQ Pi Qu Vu) mP(Aw aY dJ Ub) mU(bR Pe Ug Uk) mF(bF bQ Us) kI(bH bM Ug) Hc(lW oQ) mM(bF Tn) kF(bP Vt) GcHu GnMw UmlW} Mv{mP(Dd Iq Nj Ow Pd Pf Pg Um) nA(Pd Qe qU Ue) mI(aC Kz oF) Gc(Cx Qu) Uc(Fr Un) qZ(jR jT) kK(Jp Li) EmNm GnUh UecV IunU QdaG JdlW OyOz PdrZ PemM PfnF fPnH nJlL} Mu{Ji(Hw In Jm Jt Ng Nm Pz) Em(Aa Hv Nk Qu Ss) mP(Ii Nm Pd Pf) Gn(cF Qe) Uc(It Ke) Pg(aC nU) fP(kF Rb) fR(Mb Nd) AlmI NmnR NljQ JtkK PenI PfjT} qZ{Nw(Il Iu Jl lL Md Ni Pz) Ji(Hw Mq Nm Pf) jR(jO Ml Nl Pd) In(jT Lw rZ) hV(lO Ni Qd) Mj(Hw Pe) jT(Jh Pa) rZ(jU Na) MyLh lIJp nIkP nJoP iBjQ} Cp{fP(aP Cq Hr Ii Jm Ks Og Ug Uk Tj) Dg(aN aP bA fR gL) aH(fl Uc Us) mM(cV Jt Nm) AabN NbOm UccN JtmP UkgW UsbB mIoF} eM{aH(cG eF Hq Jk Oy Qt Qy) Qd(fP Kl Kq Nm Sr) Mw(Jt Ss Vo) pK(aR oH oW) fP(oV oW) AaFr NunU MmUf KqUh cPgV} Em{Hv(BA cT Di Hc Hq Hu Ua) Hq(bA cN Fr Jo) Tn(Kl Mm Pj) On(Ke Kf Pj) bA(cV Fr Rh) FrfP MwdH} Gc{Co(Af bC Bo bV cF cS) Ba(bC Fr Mi) Hu(Ju Kc Rh) Hc(Li Mi Qy) Ct(cF Li) CvbC TjOu MydJ KgcN LiOf VvdR} lL{nJ(iB Iq mE nR) Pd(kO mW) nT(Jq My) nU(Nh Pf) jQ(jH lX) jT(Nd Nw) rZ(Na oP) FpnO FrkK LwNk IhmF nMnI mWjL rYoP} Ua{oQ(aO Bb Iu nD Ni Rg St) nT(Al Hx Im Tv Un) mI(aY Om Tr) Ex(fP Ks) nH(Dc Fr) DgKc GnHb} Ji{Mm(Fr Hw In Ip Jm Jt Ny Og Pc) Nm(Fr Ip Oz Pc) In(Hx Iv Mi) Pz(Oz Pc Qa) FrJt NgOz} Hq{mP(bR Dc Ir Mf Nd Po) mM(bH Dd Kx Pf) Nm(kK nR) oQ(Ug Um) PdrZ PfnI bIkN mIoF} Gn{Lu(Aw Mi Mw Ow) Ut(cN Hw Jt Kf) Hb(Mi Ou) On(Ke Uh) WmUb FrUl TnKf bRcS} Hc{mI(bX Jt Qe Uc Ug) mF(oF Qe Rb) mP(Jp Kl) kF(Dg Jt) AlnT CxoQ} jM{aP(bC dI jR) jT(bP iP nY) cD(aJ jL) gP(oF oK) aQjQ bObP cFjI iBnY} jQ{jH(aS cA cT) aJ(bM cU) iZ(bM lK) ImIn OmPe aOcU bAcT cIdR gLlK} Kc{Dg(aO bN bV Fb) aG(cT Di Nd) DiKf LubN IlaO UkcT} jT{Pf(Fr Nv Om) jI(aM bE cF) iZ(cA cF) WmNw bAcT bJhG} pK{bC(iA kO lY) cL(aW cI mI) dK(bB mP) bMmI nOoW mPkO} Qd{Ba(aG Fy Ss) Uc(Aw bA Ib) Il(bN cF) AwKf TvfP} rZ{In(Ih Nq Qb) Qc(Nt Pe) Om(Pe Pf) rX(Pd Pf) NqPg} Um{aY(lW mI mU) Oy(mI mP) UhkF bHmM bMmU} Ug{Oy(lW mI) oQ(Ng Tn) CtmI VvmF aYmP} kK{Nk(jK lN) jV(Jg Nf) lO(Pe Pf) NjjK} Aw{fR(aG cJ Dl) aCbE aJdG fPkF} mF{lN(Nk Nl Pe) lM(Ne Nl) UrOy} In{Nu(Nw Om) rY(Nq Qb) OmPc} fP{Fr(Uc Tj) Iz(kI kN) RbOn} Nw{Wm(jH qV qY) PerY} mP{aY(Ub Uk) MmNg HuIq} Om{Ij(Nn Oh) MdPc} eP{aCgL aJbC aWbA} fR{cT(aH cV) AsdX} hA{dN(dM iZ) aPhB} lW{Dd(Kg Ma) NmIz} mI{Oy(Cv Tj) DibH} Co{Dg(aJ mM)} Nj{IzoQ nUjK} Pf{NqrY nUjH} cL{oV(aW kO)} cQ{iZqU qVoF} nA{PdlO PerA} BaaCcN CvOzkF FyUtmM MqnRjV Constrained panels with 3 analytes, where 1.0E-7 >= 'AUC p-value' > 1.0E-8. Contains 2,619 panels of 14,487,373 total panels evaluated. : Is{Oz(Fr Hr Ih Ii Ij Io It Iu Ji Jo Lv Mg Mn Mu Nm Nn Ny Pc) Io(aA Fr Ij Iq It jG Ji Jp Lv Mn Mu Ng Nm Nw Ny Pc) In(Fr Iv jG Ji Jl Jt Lh Lv Mi Mu Ng Nw Ok On Pz) Ih(Hr Ij Jo Jt Lh Mb Mg Mm Mn Mt Nm Nw Ny Of) Iq(Aa Fr It Ji Jt Lv Mg Mu Ng Nn Nw Om Pc qZ) Ij(aA Fr Jq Lv Lx Mb Mm Mn Mu Mv Nn Nw Pc) Il(fP Fr Iu Ji Jl Lv Mu Mv Nn Nw On Pa Qd) Nm(bN Fr Ip It Jh Jp Lx Mb Mu Pc Qd) Ni(Hr Ii It Iu Ji Jo Md Mg Mn Nw Pc) Om(Di Fr It Iu Ji Mu Nn Nw Pc Ug Uk) fP(aA Aw bR Hr Ii Jo Ju Kr Mf Og Qv) Dg(aA aP Aw bP bV Di Jj Jm Nb Pb) Lv(Hr Ii Jo Lh Mg Mm Mn Ng Of Pc) Ny(Ip It Jh Jp Lx Ng Nn Nw Pc Qd) Ji(Ii Jn Jo Lh Mg Mn Ng Of Pc) Jt(Ip It Jh Jp Jq Nn On Pc Qd) Hw(cH Fr Ip It Iu Jl Mu) Jj(Aa aG cH cV Di jT Vo) jG(jH jI jQ Lw Nd Pe Pf) Ng(It Jg Mb Nn Nw Pc) Gd(Ba bN cF Di Hb) Mm(Hr Jp Mb mZ Nw) Mu(aA Jk Mg Of Tv) Hr(Jn Mn Pc qZ) Kf(Kc Ks Qd Ug) Og(Fr Ip Iu Nw) aG(Jm Kc Pb Ug) bN(Fy Ii Ks Vo) jT(lL Nj Nk qZ) Jn(Iu Js Of) Aa(eM Tv) Ks(bX cH) Lh(Jh Nw) aA(Iu qZ) FrJk MbIk MvUc NkIL IpPz ItJm OfPc UgcV UsbV PaqZ PfrY aHeM} aA{In(Fr Im Jk Jq Lw Lx Mb Mq Mz Nh Nj Nq Nv Nw Oi Oy Pb Pc Qa) Om(Aw bN Cp Cx Di Hr Jg Jh Lx Md Mz Nv Nx) Kc(aH bX cV dH Hw Jj Lh Nd Ss Tr Tv Uc) Lv(Hv Hw Il It Md Ml Mu Nn Nw Pb) jG(cH cR It Iv Jo Jq Mr Nb nW Ny) Hr(Fr Mu Mv Nn Nu Nx Oy Pb Pc) jQ(aS bQ cG cH cZ hB Nj Nk Nl) Cx(Aw Bn Cp Dc Il Jj kC Tj) Pb(aG cV Di Jq Ug Uk Tj) Pc(Fr Jq Lw Mg Mu Nw Pe) aN(aF Aw bB cH cZ dG Di) Mu(Jm Mb Nd Ng Og) Hw(Jg Lx Mg Nv Nx) Nw(Ij Jm Mm Pz qZ) dG(aJ Aw cN Cp cX) jT(bV kR Nd Nj Nk) Og(Jq Nn Nx qZ) cV(An Ar aX bA) qU(Ij Md Nr Oz) Dg(Ap Co Ji) Mv(bN Ks My) aG(Ba Cp Di) aH(De Ef Jj) cH(aF cF cX) qZ(Ji Ms Pf) Af(Aw De) Fr(Jm Mb) Nn(Jq Mb) Tn(Kl Ss) cI(jD jU) jO(dF mM) jR(aS Nk) rX(nH rZ) lO(cD mZ) oO(Fw Vo) DifP QdOz JqNy aCbJ bAqW bEhA bVjV hBlM} Jj{Mv(aG aH Ao cN Co dJ Em Im jD jR Kc kK Md mM mP My Nn Qe Qt Qw qZ Uk) Aw(aG bN cH Dg fP Ng Nu Oz Pb) Jk(cH cZ hA jD jQ jT Mn Nn qZ) Mt(Im Jm Mq Nc Ne Nh Nj Nl) Pb(Cp Di Ih Im Li Mp Mr My) jQ(Fr hV Mf Nc Nd Nf Nj Om) Ba(aG aH cH cN Di Iv Kc) Mi(Im Jg Jh Nc Ne Nj Oi) lL(Fr Ip jR Mf Nd Nj Nw) Cp(Aa aG bN DG Ij) Mn(Et Im Jl Jp Ok Qe) Kc(aG bN bV cH cV Nd) Mu(cH cJ mP mZ Tj) Lh(In Mb Nc Nd Oi) jD(Fr Jp Nv Om

Figure 5 Continued

Figure 5 Continued

Mp)} Di{Kf(St Un) BokG aYmI} Tj{Oy(mF nH) AabZ CtmI} Nn{II(Nx Oz) rZ(Pe Pf)} Tn{KfUk UgaL UsfP} Nv{Ny(Hr Lv Og)} Pf{Jp(rY rZ) mFlN} cT{DgaP aCbE aGfR} gV{cP(cF cU) bOdR} nR{jV(Ne Nj) NIIN} mM{CoTr GpbH HuPc} nA{NIjK JkbM Um

Jt) Ua(Dg Kl Ss) It(Tr Ug Uk) Jk(kK mP nA) Jm(lL rY rZ) fP(Bg Ct Fr) jD(Jh Ms Nw) Ef(aL cN) Nq(rY rZ) Mn(Ii Li) Hq(kK nA) Ij(Jo Jt)
In(Hx Jt) Iz(Dg oO) Ji(hA Uh) Oy(Ug Uk) Oz(aP cT) aM(Nt Nu) nU(jK jL) jR(Fr Nf) CxEx TjbA NnMi NolL NbUc HumZ KdcT KfUn OicN
aCbE gWhG nAlO jGrZ} oO{Dd(Ao aQ Aw bC cQ Ct Cw Di dL dN eF Fr Jg Jk Kg Kn Ma Mg mP Mq Ng Ni Nx oP oQ Pg Pz Qd Uf Uu)
Vo(aK Ao Ap Aw bQ cF Co De Di Hq Jd Jh Jp Kf Lx Mt Nr On oP Qu Tn) Fw(aQ Aw bF Bg bQ bV cF Iz Ke My Tn Uu Vs) Hq(Ao Bb Dc Dk
Jd Je Qz Rb Uk Vs) Aj(Ad Cq Dg Jp Jt Nm Ph Qv Ur) Iz(Ao Ko Mk My Nj Of Oy Qx Tj) bX(Aw Di Hr Kk Kn Mz No Nu Qu) Ug(bA Jk kG
Mz Ni Ou Qd) bM(De Iv Li Oy Qd Rg Vs) Qv(bl bP Mx Nj Nx Uo) Ph(Aw bF Cx dF Fb Mv) bH(Ch Fb Mz Nt Qu Vv) Cq(Co De dF Tn Vs)
Ed(bP cG cQ kP Uf) Nr(Bb Dg fP Ko Pj) Om(Ao cL Co dF Vs) Nm(Ap Cu Cw Qu) Ju(bF Jh Mx Uu) Kf(Cw Ke Uf Uu) Uo(cQ Mv My Ub)
Uk(Ba bF Kg Tn) bl(Ao Fr Of Uf) bP(Gp Jh Mv Oy) Dg(Ap Ke Uf) Tv(Aw Ba Ng) Rg(cK dJ Qd) Oi(Fn Us Vp) Vs(Hu mP Tj) aP(cl Fn Hr)
bQ(Dp Nj Tj) eM(dB iZ ml) Bg(Kl Qx) Co(fP Jo) Dc(bF Jg) My(Qx Ur) Nd(Kk mZ) Tn(In Ur) ApDl BocL CxMx DeNf PoHc NqfP MqbR
MvbB UaPf TrJh JebF JpKe aWkF clmZ nOpK nFoW} jG{Ji(Hr Hv Hw In Ir jH Jo Lu Mi Ml Nf Nj Nm Nr Og Pb Pc Pz) Fr(Hw Il In Io Lj lL
Lz Mh Mk mT nA Nj nO nU Og Pf) Nk(iC Il JH Jl jO jR mF nA Nd Oh Qc) jT(al bF cF dF Jh Mf Na Nd Nj No nY Qd) Nv(In Mc mP Nd nl Nj
nK Nl Og Pz) lM(iC Il jO kK Ml Nd Nj Nl oQ qZ) Lx(In Io Jm jQ Mc Ml Nd Nj Nl) Nw(Io JH Jm Jp lL Lu Na Pb) Om(lL Mc nA nl nK Qd qZ
rY rZ) jH(hA Jp jR lL Mp nW oK On) Lw(Hr Hv In Ir Mv Pb Pe) nU(Hr Mh Nh Nj Nq Pf Pg) rZ(Hq hV jO kG Ly Nd Nu) jQ(aJ dD gL iC lL
Og) No(Lz Nj Nl Oh Pa) Jp(Jm Li Nl Pz Qd) Jq(Jh Lu Nd Nj Og) On(In Jo lL Mc mP) qZ(iC jl lL Ms Mz) kK(hW Jg Mv oQ Pf) Ne(kG mF nA
nK) al(aJ aS bE nY) Mf(Jh Mp Qd) jl(Nd Nj Nl) rY(kG Pe Pf) nW(aJ bE nY) oP(hX lW mH) oQ(hW jL qT) Ng(mP nA) Iu(Et Mp) Qc(nl nK)
Qd(Nd Nl) bO(bB cl) jR(aJ nY) kF(Ir Pd) oK(nY tF) NqmP MhnB MlJr Mqnl InQa dNiZ lWrB nAlO qTkG} Kc{cT(bN cJ Et Hw Kd Kf Ks Lh
Nd Nm Of Qd Sr Ss Tr Us Vo) Dg(aJ aX Bg gL It Iv Iz Jd Mr Mw Nb Nq On Ou Pg Tn) Ug(cH Di Fb fP gC Hc Im It Iv Lw Mn Ms Mv My Oy
Qd) bV(bN Et fP Kf Kl Ks Lh Mm Nm Sr Tr Tv Uk Us Tj) Il(Aw Co Di Ef Fr Lx My Nb Nd Pf Pg Qd) aG(aJ aP bA Im Ju Jy Lw My Nb Nw
Qd Ua) Di(Bo bX cH Et fP Nd Ng Tr Tv Uc) bN(aJ Aw Ba cD Fr Hw Lw Nw Uc Us) Kf(Aw bA Fb Fr Mv Nb Nd Qd Tn) Uk(Aw bA cH It Ms
Nb Pb Qd) fP(aO Aw Ba Fr gL Lx Nb Nq) gC(Af aH bP eM Hc Id Om Ul) Tj(aP bP cP Ex Ha Nd) bA(Hw Jo Kl Mm Tr Us) cJ(Aw Ba Iv Ju Kd
Lx) Mv(aH lW mM Tv Ue) Mm(aO aP cH Ex) Kl(aJ aO Bg Fb) bX(aJ Lw Nw Qd) Nd(nY Tv Us) Uc(Aw Hc Nb) Ow(aJ aP bG) cH(Ks Lu Tv)
Ba(cV Gc) Ib(Gc Ur) Hc(Gd mM) Uh(aO eM) bM(kl mF) dG(aJ aP) oQ(bQ My) DdlW ExMn HbeM JoaO} Ji{Om(Aw Hv Io Jh Jo Lu Lv Ml
Mn Mv Ng Nw Pb Pc Pz Qd) Lv(Hr Hw Ii In Jo Jt Lh Mn Ny Of Og Oz Pc Pz) Fr(Dg Et Hr Ij Il Io Iq Jo Mb Mg Mn Nx Og) Ny(Ip Jh Jm Jo Jt
Lh Lu Mn Mv Ng Nw Og Qd) Oy(Hr Ii Jm Jo Jt Mg Mn Ng Of Og Pe Ug) Oz(Hv Ii It Jo Lu Md Mn Nn Nw Pc Pd) Mv(Ii Ij In Jg Jo Mg Of Og
Uc Uc) Hw(Hv Jl Md Ml Mn Ni Nw Pb Qd) In(Et Io Ip Jk Mn Nt Og Pz) Ip(Et Ij Io Jo Lh Ng Og) Pc(Hv Ij Jo Md Ml Mn Og) Dg(aJ aP Aw Hc
Nb Qd) Ni(Hv It Jl Md Ml Pb) Lh(Aa Io Jh Jt Mn Nw) Et(aJ aP Aw Di Tv) Ug(Hc Kf Ks Pb Uh) qZ(Im Iu Na Nr Pd) Mn(Io Jo Ng Og) Qd(Jm
Jt Kf Ng) Jh(Ij Mg Ng Of) Lu(Ij Jo Nx) Jm(Jk Nn Nw) Uk(Ef Pb Uh) Aa(eM Iq) Aw(Kf Ng) Di(Kf Uh) Ml(Jt Mb) Il(bN Jk) Io(Hr Jo) Og(Nn
Oi) Us(Mm Nb) IbTv IjPb PzNw JlJt JnJs UheM PdPe} Nw{Oz(Fr Hr Ij In Jh Jm Jt Lh Mh Mm Ng Nm Og Pc Pe Pz) Pz(Fr Hw Iv Jh Lh Lv Mv
Ny Og Om Oy Pb Pc Qd) Jt(bN Ip Iv Jh Jl Lv Lx Mi Mv Ok Oy Qa Qd) Mm(cN Fr Ij Ip lL Lv Mn Ny Og Pc) Om(Aw aX bN cN cZ Fr Lx Oh)
Nm(Hw Mn My Og Pb Qd qZ) Ng(Fr Jh Mv Ni Nn Oh Oy) In(Im Lv Mi Mn Nt Pc Qa) Jm(Io Iv Lv Mv Oh Oy Qb) Hw(cH Io Ml Ni Oh Pc)
Lh(Fr Jh Lv Ny Og Pc) Aw(aG aH Dg Gd Kf) lL(Iu jQ jR Lw Ok) Gd(Ef Iz Jk Oy) Ij(Fr Iv Jh Nn) Io(Hr Jh Md Og) bN(cN Di Ii Pb) qZ(Mq Ms
Nd Ok) Tj(aG fP Nb) Ni(Md Ml Nc) Og(Iv Jh Oy) Di(aH Pb) Mv(aG Uc) Nj(jQ jT) Hr(Iv Oh) Sr(aX bV) Ny(Fr Md) Pe(jD Pd) cN(Cv dG)
EfmF EtfR MbPc MhOh NdUs RbfP KfaX UkPb PfjT aCbE} Gd{Jk(Aw cS Di Ef Hb Hc Kr Ld Li Lx My Oa Pb Qd Rh Tj) Hc(aX bl bP cS dB
Ez Ii Lj Mi Nn Ow Pc Rh St) Vu(As Ct Fb Jm Kq Lx Nv Nx Ny Oy Uf) De(aH Ba bC Bg bN Ct Di gL Jn Pb) Tn(aW bC cJ cV Et Im Mp Nn Qy
Uf) Ef(Ch cN Lj Nu Oa Pb Qb Qh) Lx(Ba Ct cV Im Oy Qy Rg Uf) Fb(bN dC dH Im Om Pi Ri) Aw(Ad Ba bC cS Lj St) Bg(aG aH cA dB Fr
Qd) Pz(As Li Mw Oa Po Vp) Uf(cF Di gP Im Pb) bN(Co cT Iz Jg On) Ba(bM dB Li) Tj(Hq Lh Mw) Qd(eM Iz Pb) On(Qy Uh Uv) My(dI Li)
Hq(Mi Ms) Ib(bZ Me) Qv(Ct Iz) Ut(Gn Hr) CoSt DiPo DkEz FrcV MgbA MvUh MwVv NcQy UacF lmRc HbLi OugP PbPc aFcT} Mv{Ue(aJ
bA bN fP In It Ni Of Pj Qw Tv Uk) Uc(dL Il Ip It iZ Kd Ke kF Kq Mj Pg Tn) Il(aJ aP bN cN cV Kk nA nT qZ St Un) mZ(aC Hq Ij kI Lx Nd Nq
Of Oy Tr) nA(bM fP Ii Jt Mf Mk Oy Po Qa) ml(aY bB bl bM cE Pd Pg Um) aC(aJ bE cN Hw mM mP Qd) fP(aJ aP Ex hG Kd Qd) kK(jD Jl Jt
oQ Pf Pg) Qw(aJ cN It Of Ug) Em(Aa bA cP Mj) Ng(Iv Jh Lx Oh) Oz(aP bA In Og) Hw(aP cN dJ) Qd(cN Kf Tv) mM(bH bM Um) mP(iA Jl Jt)
Ex(Mn Of) Nb(Ao Fy) Ij(Mz Om) It(Ib Ks) Pg(kO nT) aG(aP Kk) nl(Mk Nc) CqKd DgkF MmnR NidJ NjnT HcoQ QemF KlaJ OmgC UgcV
OyPc PdrY aHaP bBnH blmH nCoF} Qd{Di(aG Em Il Kl Ks Mn Ng Oz Pb Qw Ss Tv Uc Ug Uk) eM(bN Cx Et iH Io Jp Ke Kn Ko Ny Pj Qa Ss
Un Vo) Kf(Fr Hw Ir It Jh Jp Ms Nd Pb Tn) Uc(bC Co Ct Ef Hv My Ng Ou Tv) cN(Ba bN Jl Kr Mm Om Ow Qw Ss) Pz(Fr In Jg Lv Nn Ok Oz
Pc) Aw(aC aG bN Dg Il Ng Ss) Ug(fP Hc Ms oF Oy Oz Pb) cT(aG aH fP Kl Ks Om Us) aG(Bg Hc Hw Mf Tj) Em(bA cF dH Lu) Tv(Ba Nc Pb
Uk) bN(Ir Iu Uk Tj) qZ(Iu Ms My Pe) Il(cH Co Hc) fP(aO Hc Tj) Ba(aH Kl) Dg(Lx Ok) aC(In Mf) mZ(Lj Nj) jQ(Nk Nl) BoHw FnbX FybA
GnHb MmcF NbQw NdUk JtgC PejT nljY} mZ{Hq(Ad aY Cq Dg iZ Ju nF Ni Nk nR Uh) Hc(bH Dg Kl ml Mm Mn Nd Nm Sr Tr Um) Nj(mF
mP mU Mx Oi Pb Pz Qw) Jk(bP Lh Li Lj Mm Pb Pg) Oz(Hu Im Ma mP Nc Nd Nn) Nm(Hu Jg Jh My Nq oP) Ng(Jt MF Mg Pc Qe) Ib(Mi Of Or
Pg Rb Ub) Aw(Dd fP Jp Ma ml) Mm(Hu Iz Jh Nn oP) Nc(kl Lu mF mU Mx) jV(Im Nl Om Pc Pd) Qw(bl Um Ur Tj) Im(iC Pc Pe) Pb(kK nR
Pd) Mw(mM Rb) Jh(jL Lh) Oy(Pf Rb) nH(Bg qT) BabP Ctml NnIu NqSr MxjL NiUb Hukl HvLj HbaY JloP LhbH VvkS PclN mUrC nCqT
hRkK hVjQ rZrX} ml{Hc(cP Cq Dc dG Di Dl Fa Fp Hb Jp Ju Kl Nd Nh Nm Om On oQ Sr Un) Ef(bH Et Hw Jm Jp Ke Kf Ko Mf Mp Mz nK
Nv Qc Tr Uk Um) Di(Af Ba bM Ct Dd Nm Oy Oz) aY(Aw Cv Hq Ju My Nd Pz Ug) Ng(Al bM Bo Cv Dd) Ua(Ic Mf Nd Oy Um) Tn(Qe Ub Ug
Tj) Um(Bg Nd Pz Tj) Aw(Al Dg Nm) Ba(Cv Dc Lv) gC(bO cZ oW) Ch(bX Ub) Ct(Dd Pb) Hq(oK Ug) Ib(bM Tj) Oy(Dd Ub) pK(aR eM) AjUg
BgDg NmQu NqSr NtbX MyfP TrIz VvkS cLoV} Aw{Dg(Ap bP bV bZ cN cS cT Fr gL Ip It Lx mP Mt nA) Ng(aP bP cH Cq Hr Il It Jh Of Pb
Uk) fP(aJ bl bP Ex Fr In mF Og Ug Uk Us) aG(aJ aP Ba cN Il In Oy) aP(aH aN cJ cV dG Om) Il(aH cV It Iv Kf) aC(Ad aX cJ cZ Oy) aN(BA
cT cZ) Nb(Cq Om Uc) Uk(It Kf Nd) nA(Dd Jt Nm) Ad(An fR) Gc(Bo cA) Om(Jh Nd) Pb(mM Of) aJ(cH cJ) mP(Dd Nm) CqkN FrUc NuIn
JpkF UgbP cHcN cLgC} Hq{Em(aG aJ As aX bP cT Di Ex Im In Lh Lx Mi Mj Nb Ng Ny) mP(aN cE Hu iA Ih In Jo Jt kK Lj Lx Mm Ne Nf Nh
Nl Ub) mM(aY cL Dp Iq kF Nc Nj Pd pF Ug Vt) Gn(Aa Al Ed Rh Ub Vo) nA(Dd Hr Jl Pd Qe Ur) kK(Hr Ir Jl Nc Nj Ok) Gc(Li Mp Nn Uf)
mF(Ha Jl Tv Vp) kF(Cv Dd Jl Li) kN(Ao Dk oK oN) oQ(bH bl Hc) AonH DplY ExJo NmoP HrnF IqnU UmmU PdrY aHfR} gC{bC(Af Ch Ez
Hw Jm Kg Mp nO Ou Tn Ua Uf) bP(Kg mT Mw nN Nq oW Qt Ug Vv) Nu(aX cS Fr Iz Mw Nq Ou) Ez(cV Cx No Om Oz Vo) bB(Kq Mi mP
nN oV oW) cL(aN Ao Ba Ct Jr mE) Tn(Fa Ju Mr Tz) Kq(Im Jt Ny Qm) bW(cN mY nO Ug) Mi(Ax Cx Oa) Mp(aH Oz Pb) Qy(Il Pa) Oz(Li Nn)
aF(mP pK) aW(Oa oW) cS(aH Gc) AfUt FaMy NtNy MmUf KgOg VvcX bSmP iAoW} Di{Nb(Cq Fy Hr Hw Il In Nd Of Uc Uk Us Tj) fP(aJ
aP bZ Ex fR gL Iv Lx) Kf(Fr Ip Ir It Iv On Tn) Pb(aJ aP cN Iv mP nA Ug) Gc(aM Ba cG Ct Dc) Uk(bV Ip It Oy Tn) Ug(aP bP Ip It Oy) aJ(aC
aH cH cV Ow) Bo(Mb mP nT) aP(aH DG) Ba(aC aN) Em(cP Fr) Iv(Il In) bA(cN cV) DgfR FbKl FrUc NiNk ItKs StUs KkcJ OwcN aCbE aNcT
bHmM} Ef{Uk(aP bP cJ cN cZ dA Il Ip It Kl Ks mF Nd oH Ss Un) mF(Bc Cs Cx Kq Ks Mf Mp Om Qc Qm Tr Ug) lW(Al Cv Ii Ir Ok oN Qm
Rc Vt) kl(Af Ez Jk Jp Kf Sr Ss Un) fP(aP bV Ex Il In Ug) mM(Ik Ju Lh Ni Nu) aH(aJ aP cN Il) Jo(dJ Ex mY) mH(Et Kr oN) Em(bA Hv) Uc(aP
cN) AaMr AffR CsnA DgaP GcbW KkaG KlaJ LinO UgaL} Fr{fP(bU bV cF Dg dK Hr It Iv Kd Ky Oy Tv Uk) Oz(Hr Il In Jm Jq Mb Ni Og Pz)

Figure 5 Continued

Dg(aJ Ba cN cT Iv Pb Qw St) Uc(bN Hc Hv Jh Ke Nd Oy Pb) Ng(Iv Jh Lv Mb Mn Nd Nl) Gc(bC cV De) Il(aG bN Uk) jQ(IL Nj Nk) In(Nt Nu) Jt(fR kK) Kl(bV eM) IL(jR jT) AaEm IqOh IvJm QemF JqNy UgaH} Gn{Ut(Aa Af Ke Ks Lu Ng Pb Uh Wm) Ou(aG Bo cF cN Cw Mm Pj) Mw(aG Al dH Et Hb Om) On(Cw Kl Mm Pj Ul Vo) Lu(Jh Kq Mq Mt) Tn(aG Ao Jg Kl) cT(bM cF cN Rh) Ct(Aa aG Hb) Hu(aG Ni Rh) Ib(aX bC cS) Mi(cN My) Ub(Hv Ow) Im(Kf Kn) Hb(Jl Jp) Vv(Hv Uh) bA(cF cV) AabC CwLx WmPb NicF KjcN VpbN} Em{Hv(aG bG cS dR Ib Iz Jg Jm Lh Lx Mm Nb Ny Of Po Pz Qw Tn) bA(aG bP bU dC dR Im Mw My Nn Nq Pi Qy Ua) On(Af cF cN dH Et Fy Jm Jo Kl Lu Pb) Mw(aC aG cT fP Lu) My(Aa aC Mj Nk) Hu(Aa cT Ni) Ut(Ik Ng Qv) De(cP cT) Tn(aG Al) PoLu UaKd JmRm LhaG LiPb} mP{Ng(Dd Dg Jl Jp Mf Mg oQ Pe Tr Vo) Hu(aY Dd iA Ij Ju Nh No Pb Po Vs) Hc(aY Cq Dd Dl hB oF Ok oQ Sr) Ib(bX cE Lh Mn Pg Wm) Pb(Bg bP Cu Cv Nc Pk) Tn(Dd Dg Nm Om Tr) pK(aN bS cM cR nO) aY(Lh Mx Ua) Nm(Nq Om) CoTr FyUt MfJh IzUm QhJk OyPe} In{Om(Hx Il Iv Jr Md Mi Mr Mx Mz Pa Pe Qa) Oh(Iv Jh Mq Ni Nn Nu Oy Oz Pc) Nu(Jp Jq Lh Nq Ok On Qa) Iv(Hx Jl Lh Nn Oy Oz Pc) rZ(Lx Nn Nv Pd rX) Qa(Jq Ni Nt Pz) Nv(Nl Nm) Oz(Jq Ok) jQ(lL Nj) rY(Ip Lx) LwlL NiLh UafP JnOu PbcN} kF{Oy(Al Cv Dd Dg fP hB Pf Uc Un) Hc(Al Bc Jp oF oQ) Um(Bo fP Jp kS oQ) Oz(bI Cx Pe Ug Tj) Nq(fP Kl Sr Uh) Dd(cF cV Or) Ib(bM Dg Qe) Jk(Cq fP Jl) Tn(Dc Ok) Qw(Qe Ug) Pd(lO Pb) fP(My Qy) BgKl ChJp CoDg CsUb CvEd FyUt NmnR UaQa UnbR UgoQ PemM} Pb{nA(bG bR De Ke Pk Ub Uu) lW(Cu Cv Gp Ju Kg Pk) kI(aD bX cL Pi Pk) Ug(aJ Fb It Un) mM(cG Co Ib Ke) aP(bN dG Tj) mF(aY bM eC) Gc(Im Li) Pe(kK nU) fR(aG cV) nT(Ph Pk) kG(Bo Rb) LwlL NbUk QgmU UvkK PfnR aCbE bFoQ bNcN tFkO} jT{jI(aL aX bA bJ cT oE Wm) Om(lL Mf Nj Nk Nt Wm) cF(cI dH gL hG jH) Na(Jq lL Nd Pe) Nk(Jq Nd Nq) Pe(Jq Lx Ng) aC(aO dG nY) lL(Lw Mf No) Wm(Jp On) bE(gP lM) dM(bC nY) qZ(iB lO) jM(cN hG) MlNc OnPf iZlM} Gc{Hu(Ba bU cT Ez Li Mp) Uf(BA Ib Lx Vv Tj) Co(aG aV dB Dg) Ct(aV De dR Tj) Qy(aS Iz Lx Ou) cF(bW Gl Kg Li) Ba(bM bU Ez) Mp(cT Hc Of) De(bV cA) Nn(Of Vv) Mwld UabU HcKg IrOn VvaV aEcS} Nb{Uc(aX Co Hc Jl Ke Kg Kq Lh Mi Nn Pf Qa Tn Uk) Uk(Ez Il It Lw Ms Nc Nd Nn Us Tj) Tj(Lx Mp Ne) Nc(Cq Ug Us) Mj(Tv Us) Im(Fy Ur) bN(bV cN) BaOf EzIl HwKg TvLh ItUg StJm KdUs cHcN} eM{aH(aJ aX bH bZ Co De Ib Jh Kq Mb Nt Om Ou oW Pz Rh Uf) Aa(Ke Li Tr) Nu(bN Mk Om) Mw(bB Pj Rc) Mm(Co Li) Rc(Dk Jk) bH(nI Ul) iH(aR pK) GlUa MknD QyfP JkKl JtKe UfUh OznU mHpK iOoV} jQ{Nk(hV jH Mf Na Nd Nq Og Om) Om(Mf Nj Nl Nt Pf Pz) lL(hV jI Mf Nl No) lM(dR hV Nj Nl) jM(bP gP iH) Mf(Nc Nl) Nj(Jh No) aO(cT lK) dR(iZ nY) jH(gL hV) PzJp aFlK aJhA bEdD cDjL dNnY} Hc{oQ(bH bI cL cO eC Mi nN) mF(bH Cq Jl Nm Qb Uc) Dg(aJ aP bV Kq mM) mM(Kl Nm Uo Vo) Ug(aL bP It) lW(Ii Ju Vo) kI(Dc Jp Kl) nT(hB Ii) AdlX AlmU} qZ{Il(Md Mj Ms Nd Pd Pf) hV(hW iB Md qU) Mj(Ik Nr Pa) Hw(Hv Mp Qc) Qa(Hr Ir Na) eD(Iu Ml Nk) Lh(Jl Nr) nN(jY nO) rZ(iB Pe) MljF MsNi MyQc LiPf hAnI nUlW nAlO} pK{cV(aW cI iA kO nC nH nL) aF(aO bF bQ cT) cL(hC iA lY mY) dK(aR bO jB oE) bC(bB mY nU) bP(bR bS cS) aW(fA oW) cG(bB nF) aCcS aRkE aUnO fAkO} Jh{Hw(Ir Iv Jp Jq Lh Lv Lx Mz Nh Nu Oh Pc Pe Qa Qb) Ng(Iv Lx Nv Oz) Oh(Jm Nm Og Oz) Ug(It Nd Oy) NmLx NnOz IjOm NvNy} jH{dN(aL aQ bA bE cQ cT hA jM) oK(aK aL aM aQ kQ) Nk(jR Mf nI) aL(aI lM nW) nR(Nt Pe Pf) jR(cF lL) NenT JlnU PemY bEiB bPjM nAlO} Ua{fP(Aj aP hG Kd Rb Tv Ug Uk) Uc(aJ aP bP cN dN) oQ(bP bS De Qt Wm) nT(Ax Cs Lv) fR(aG Et) ExJo IrmS VtnN aYnA bXnH} Nv{Ny(Hw Ip Jm Jq Mb Mi Mm Ng Ni Nm Pc Pz) Nm(Jm Lv Ni Og Oh) Ng(Jm Mn Ni Og Oz) Lv(Jm Og Pz) Og(Io Oz) MmJm} Dg{aJ(Ap Bg cT Cu De On) Ba(cN Ke Un) Co(aP fR mF) On(aX cZ) cN(bA Cu) fR(Ch De) ApFb BgaP MsKq TnUn IpbV IzkI KemF} Ug{Oy(bP It Ms Mz nA Nd Uk) aP(bN dG dH) aY(lW mF mU) mF(bM Kg) BgfP ExcZ LxcV NcNi NdIt TnlW TvLh OmUn cLoQ} nA{Ng(Ad jL Pe Qe qU) jL(Lx Om Qc) Iz(Jt Nm) Jk(Jl Nc) Pe(iB lM) Pf(iB lM) qU(Na Qc) NejK NljV UoaY} Ba{aP(aG cV dG fP Kl Ss) cV(aJ aN cN Kd Uk) cN(aN aZ cH) aC(aL cZ) fR(aH Dl) KfUn aJdG} lL{Lw(Hv Hw Ir Jo Js Mi Na Nj) jR(jI lM Mf Nk) No(Mf Nk) NqrZ LxPf MfOm HumM PznR rYrX} Tn{Ks(aL bP cH cZ fP Kf Us) Kl(aP bV Fb Uk) bX(mU nH nL) fP(Tv Uk Tj) IlKf OmmU} Oz{Nn(Iv Jl Jq Lv Lx Mx Mz Oh Ok) Jm(Lx Qa Qb) Mi(Lx Oh) On(Hr Ii) IjOm JqOg KglW} mM{Ng(Io Pf Pz Um Uo Vo) Co(Jp Jt Kf Nm Pj) Nm(Ch Ke On) Hu(kK Nc) IzUm JubQ} aJ{dG(bU cH cL cN dN) cV(aM cF cH cT) aC(aL aX cZ) IlKg aGcH aHcT cKeP hAjR} rZ{Pf(Ip Lh lM Lx Qc) Nq(Hr Jl Mn Nt) Na(Nk Nl Pe qU) Pe(Ip qW rX) NtqU} fR{aC(aF aH aM AX bE cJ Co cZ dL) aH(dR Hv) CtNg EzfP aScV bBcT} Om{Ij(Ir Jl Mi Mt Og) Pf(hA jD jR) MdHw MfjD NkhA OgjR PerY jUjV} jM{bP(aI bA bC lM tF) nW(aP dM iB nY) nY(jR oK) bCdN cDcN cFiZ} Ex{Mm(aX bP bW cL) cN(aZ bH bN bP) Uk(bP cL cZ) TrcZ fPgL} fP{Rb(Jp Kq Lx) Bg(Og Us) Tv(Lh Uf) ChmY TjaP ImhG JpUs KdbV} jL{cD(aL iZ lM nW nY) nU(Lx Nj No Nq) dN(bC cL) lWoQ} bA{Aa(bN Iv) cF(aN cN) cT(hA jR) cV(eP oV) aHoW bWgV cHcN} kK{Nq(Jt lN Mm) Nm(Jg Jk) lN(Mm Ne) NubX NhjV IzKl OyPe} oQ{Um(cL cS kG My Ou) Bg(Qx Ur) Iz(Ch Oy) HuVs} Oh{Il(Iv Nn Pc) Lv(Jm Og) Hw(Iv Nn) IiOn IuJl} oV{cV(cE cS cT kR) cL(aN cF dC) aHcY bFbP} mF{bM(cS Ma Uf) CoJt TrIz IuqU QeKe PdlN} rY{Nq(Hw Nt qU) Pe(Jp Nn Qc) Pf(lM Nn)} Jm{Qa(Hw Lv Pz) Qb(Hw Lv Ni) StcN} mU{Nj(aY bM jK) jV(Nl Pd) CvbM UmcV} bN{Aa(Jg Lx Ok Pk) NcNi IlbZ} cT{AaIv aHaP cIlM cLjB cNcV dUiH} nR{jV(Iu Mg Pd) Nm(Jk Nq)} nU{jD(Mf Pd Pf) NhjV PdlO} Pz{Ok(Ip Qa) DdnH NuJp} aP{cD(jU lO) aCbE jRlK} cN{IlKg OgOi dNhA dRgV} kI{Ch(Kl Nm Vo) NmIz} Ks{On(cH Kf) NdIt} dN{hA(dH gP jI)} lW{CoVo IzKl JuaY} nK{Pe(iB Oy) PfiB} iZ{bMjR bQlM qUkQ} Nu{NgJp bXnL} Ne{nTjE iCkO} Il{NnIv NxPc} Jq{LvOg QaNy} aC{bE(bV dM)} cL{jB(hC kR)} gL{QxgW cHeP} lM{NlmE aLjI} oW{aWhB bBbF} AsCudX DdcFkG MsqYjV NdLdUk NkJpjR TvImLh IiIvOn IpJtOk OrbHlY aHfAmH bLgPgV bMcSdU cIhGjU Constrained panels with 2 analytes, where 1.0E-8 >= 'AUC p-value' > 0. Contains 40 panels of 108,068 total panels evaluated. : Jj(aA Fr Ik Ip Is Iv Ji Jq Lx Mu Nu Nv Nx Oh Ok Oy Oz Qa Qb Qd) aA(jG Ji Oz qU) lL(kG mZ nA oQ) Gc(Ef Mu Mv) Gd(Hu Ua) mZ(jG qZ) DrMy UaoQ IsOg UmoO qZjQ Constrained panels with 2 analytes, where 1.0E-7 >= 'AUC p-value' > 1.0E-8. Contains 53 panels of 108,068 total panels evaluated. : Jj(Hq Ih Im Ir JG Jh Jk Jl Jm Jp Js Lh Lv Mp Mq Mr Mv Mx Mz Nc Ne Nh Nl Nn Nq Nt Nw Oi On Pa Pg Po Qc Qe) aA(aH cV Cx Fr lL Lv qZ) Is(Hw Il In Jm Om Pz) GdMu MmJi IjOm jGjl kKlL Constrained panels with 2 analytes, where 1.0E-6 >= 'AUC p-value' > 1.0E-7. Contains 61 panels of 108,068 total panels evaluated. : Is(aA Hr Ih Ij Io Iq Jo Jt Mm Mn Ng Ni Nm Ny Oz Pc) Jj(Ii Li Mg Mi Mj Mt My Nj Nr Pb Pc Pe) aA(aN cH Hw In Mb Nw Pc) Ji(Hw Jm Jt Nm Oz Pz) Nw(Jt Nm qZ) Cp(Ad Dg) Dr(bC cS) Gd(Aw Mv) mP(Hu Mv) iZ(jM jT) CoGc UamZ KcoO OmjG aJjT aPjM nRlL Constrained panels with 2 analytes, where 1.0E-5 >= 'AUC p-value' > 1.0E-6. Contains 132 panels of 108,068 total panels evaluated. : aA(aF aL aM Aw Cp cQ cZ dG Di Hr Jg JQ Kc Lw Lx Mu Nn Nx Pb) Ji(Fr Ii Ij In Io Is jG Jo Lh Lu Lv Mn Mu Ng Ny Og Om Pc) Nw(Hr Hw In Io Is Iv Jm Lh Mm Ng Ny Oh Oz Pc Pz) Is(fP Fr Ii It Iu jG Lv Mb Mg Mu) Cp(Aa aH aN fP Jj Om Uc Uk Us) Kc(aG bN Jj Nd Ug Uk) qZ(hV Il jI Jj jR lL) jG(dN Jp lM Lw On) Mu(mP Ng Of Oz) Oh(Il In Jh Pc) Aw(aN Jj Ng) Fr(Ng Oz Uc) Nb(Di Uk Tj) aJ(cH Di jM) kC(Pe Ua Um) oO(Hc Rg Ug) Hq(Dr mZ) In(Iv Om) Oz(Lx Nn) jM(bP gP) jT(aP bE) EmbA GdTn LwlL MvmZ NgJh NvNy cDjL Constrained panels with 2 analytes, where 1.0E-4 >= 'AUC p-value' > 1.0E-5. Contains 306 panels of 108,068 total panels evaluated. : Cp(aJ aP bA Cq cZ Di Gd Ij Il Jm Kf Kl Ks Lh Mn Ng Of Pb Tr Ug Tj) jG(Fr iC jH jO JQ kK lL Lx Nk No nR Nv Nw oP oQ Qd qZ) Jj(aP Ba bV Ch cT

Figure 5 Continued cZ Di Ef Hc jQ jT IL Rm Tn Ua) Is(Aa aG bN Dg Di Gd Kf Ks qZ Tv Ug Uk Us Vo) Nw(bN Di Ij Il Jh Ji Lv Lx Md Mi Ml Mn Mu Og) Oh(Hw Iv Jl Jm Jp Lh Lv Mi Mz Ni Nn Ok On Oz) Nv(Hr Hw In Jh Jm Jt Lv Ng Ni Nm Og) Oz(cN In Jh Jp Jq Lv Mi Mv Ok On Qa) Aw(Ad aJ aP Dr fP Il kC Kf Om Uk) Di(AN aP bA cN Iv Kc Pb Qd Uk) Mu(Dr Gn Hw In Mg mZ Og Pc Uc Uk) Ug(aP It Jh Ji Lx Nb Oy Pb Qd Un) Kc(bV cH cP cT Dg Il Kf Nb Tv) aA(Ba fP Il Ip jR mZ Nd Qd rZ) Lx(Hw In Lv Ng Ni Nn Pc) cN(BA cT Ex Nb Pb Qd) mZ(Hu Ib jI Nc Ng Nj Pb) Fr(Em fP Hw Nd Nl Pc) Qa(Hw In Iq Jm Og Pz) Jh(Hw In Iv Jp Jq Nh) Ji(Hv Ks Md Ml Pb qZ) aJ(aH aM cF cI cV eP) aP(aC aH cF cT hA Pb) Dr(cG Ct Ef Hu Ou) Qd(aC Pz qZ Tv Vo) kC(aY Ba Bg bM Ct) Gd(Bg De Ef Hc) Nb(Rb Uc Ur Us) Jp(Iv Ng Ni Nu) Nn(In Lv Pc) Lh(In Pc Tv) aC(Ba bE fR) jM(dL nW nY) jQ(dN hV lL) jT(dM gL hG) oO(eM Ua Uo) Dg(Cu Kq) Ef(dJ mM) Em(Hv Mw) Mv(Ng Uc) Hq(kK mP) Ok(Hw Ng) jH(bE oK) LvJq MdOm MsqZ TnKf IlIv QbJm PdrZ aHfR bAcF cLjB mIpK

Constrained panels with 2 analytes, where 1.0E-3 >= 'AUC p-value' > 1.0E-4. Contains 852 panels of 108,068 total panels evaluated. : Ug(aA aJ Aw Ba bE bV cN Co De Di Fb Fr Hc Im Ip Iv Jq Kd Lv Ms Mu Mv My Mz Nd Ni Oi On Pd Pf Po Qa Rm Tn Tz Ua Uf) Di(Ba cP cT Fb fP FR Gd gL Hc Il In Ip It Jh Ji kC Kd Lv Lx Mb ml Mu Nd Ni Ow Oz Pf Qw St Un Us) Cp(aX Ba cS cT Dr Em fR Fy gL Hr Hw Ii Im In Iq Jo Jt Mb mM Nd Nm oO Oz Qv Qw Rb Tv Ur Uv Vo Vs) Fr(aN cV Dg Dr Hr Il In Ip Iv Jm Jq Kc Kf Kl Ks Lv Mb Mg Mn Ni Nw Og Om Qd Qv Qw Tv Uk Ur Us) Qd(Aw cH cP Dg fP Hw In Io Jh Jm Jq Jt Kc Kr Ks Lv Mm Mu mZ Ng Nm Ny Og Om Oz Qw Uc Uk Us) Aw(aX BA cT Hr Hw Ik In Is Jm Jo Ks Mb ml Mn mZ Nw Of oO Pb Qw Ss Tv Uc Us Vo Tj) Oz(aJ aP bA bV Et fR Im Ip Ir Iv Jg Jl Lh Li Mp Mr Mt Mx My MZ Nt Nv Pe Po Qb Qe) Uk(aA aP bV cN Co Ef Ex Fb Ip It Jh Ji Kq Lx Mp Mv Nn Nq Nw On Oy Pb Pf Pg Tn Un) cN(aM AN aX bV cI cS De Ef Hc Il Im Iv Jj Kd Kk Lx Mb Mu Mv Ni St Us Tj) In(Hx Jl Jp Jq Js Mi Mq Mt Mv My Mz Nb Nq Nt Nu Nx Ok On Oy Pb Pc Pg Qb) Jh(Il Ip jG Ks Lh Lv Lx Mx Mz Nc Ne Nl Nu Og Ok On Pc Qa Qb Qw Ue Us) Kc(aX Ba fP gC Hw Im Is kC Ks Lw Mm Mn Ms Mu Mv Nw nY Ow Tr Tj) Dr(aX BA Bb bQ bV cL Co cT cY De Ez Fw Gl Hv Lx Nb Tn Ut) On(Dg Em Gd Hr Hw Iv Jm Jt Kf Ks Lv Lx Mm Nd Ng Ni Og Pc Us) Mv(aG aJ aP dJ Hw Ip Iv Jq kC Lv Mz nI Og Oh Pc Qv Qw Uc) Jp(Il Im Io Ip Jl Jq Kf Lv Mb Mi Mn Mx Nl Nn Og Ok Pc qZ) jG(aI aP iB kG lO Mf Ml Mp Mu mW Nd Nj Nl nN Nq nW Og oK) Lx(Dg fP Ip Jl Jm Jq Ks Mb Mi Mn Mt Mu Og Tv Uc Us) Il(aP bA bV bZ Co Ex Jq Kq Lh Lv Mu Nn Nv Nx Tn Un) Is(Ad aJ cH Cq Dd Fy jT Ju Kl lL Rb Tr Ub Uc Up Tj) Jj(aJ aX bA bZ cH Co Ct cV Ez Fb jR Kd mZ rZ St Un) aP(aG aM aN Ba cH cI cV dG fP Ji jQ Nb Ow Us Tj) Nw(cZ Dg Im Ip Kf lL My Nl Of Pb Pg Tr Tv Us) mZ(Hc Jk kK Lj MF Mw Nd Ne nR oP Pc Pe Qw) Ji(Aa aJ bV cZ Dg Kf lL Qw Tr Tv Uc Ue Us) Ks(aA Co Ef Ex Fb It Kq Ld Mu Nb Tn Ua Un) Nv(Io Ip Lh Mb Mg Mi Mm Mn Nn Of Om Pc Pz) Iv(bV Ip Jl Jq Lh Mp Mz Ng Ni Nn Ok Pc) kC(aX bH cF dC De Hc Hq Nc Nj nR Pf pK) Mu(aG Dk Em Ip Jq Lv Mb Mn Qv Qw Ue) aJ(aG Ba cZ De dG dL fP jQ Nb Ow Pb) Nn(Hw Jl Mi Mr Mx Ns Nu Ok Oy) Nb(aX bV cH cZ Fy Qv Qw Tv Uo) Ng(Cu Et Lv mM mP Nx Oh Qa Tn) Jq(Hr Hw Ip Mb Mn Ne Nl Og Qa) Pc(Ip Jl Lv Mi Mp Mt Mz Ok Pe) jQ(aO dR gL iZ jH Nj Nk Nl nY) jT(cF dN iH Na Nd Nj Nk nY Pe) Og(Ip Jl Lh Lv Oh Ok Po Qb) Gd(Co Fb Im Iz Mw Uf Vu) Mb(bV dN Et Oh Ok Qa Qb) Tn(fP Kl oO Ss Tv Uc Us) aA(nR Ow Qv Rb rY Us Tj) lL(iB jI jR lM Mf Nk No) Hw(Jl Kq Lh Mp Mt Qb) Qa(Hr Io Lv Mn Ni Ok) aN(BA bV bZ cT dM) oO(Aj aW Ba De Iz Ke) Ex(bN bP cL cZ Jo) Pb(bA bV dN Kd mP) jH(aK gW kK Nk nR) qZ(iB lO Mj Ni nN) pK(aF bP dK eM mP) Ua(Aj fP mI Uc) Hc(mI mM mP oQ) Ip(Lh Lv Oh Ok) Kf(Cu Kq Uf Un) dN(cT De hA jM) fR(aG bB cV eP) Ni(bV Nc Qb) Hq(Em mM nA) Hr(Lh Ok Om) Oh(Im Mn Mt) bA(cV De Tj) gC(cS mI mP) jI(aL kK nH) jM(bO cF oK) kF(Dd Nc Pe) Dg(Fb Jg) Kq(Ij Uc) Lh(Ur Us) Om(hA Ml) Un(Mm Nd) aH(bZ eM) bV(Kd Us) cI(iB jL) qU(oP oQ) rZ(Na Nq) AaEf BacV CoJo CtGc NmnR NueM MpMz NkjR IbmP TvPf aCdM dHhA qVoF jLoQ

Figure 5 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.2E1 | 7.6E1 | 7.3E1 | 8.2E1 | 5.0E1 | 5.6E1 | 2.0E0 | 2.0E0 | 2.9E2 | 2.6E2 | 936 | 64 | 159 | 64 | 0.54 |
| Ad | ug/mL | 2.4E-2 | 7.3E-2 | 5.2E-2 | 2.7E-1 | 7.0E-2 | 1.2E0 | 6.8E-4 | 4.3E-3 | 3.7E-1 | 8.5E0 | 218 | 51 | 87 | 51 | 0.71 |
| Af | ng/mL | 8.9E-1 | 1.2E0 | 1.6E1 | 1.5E1 | 7.0E1 | 4.4E1 | 1.7E-3 | 1.7E-3 | 5.3E2 | 2.6E2 | 218 | 51 | 87 | 51 | 0.58 |
| Aj | ug/mL | 1.4E0 | 2.6E0 | 2.6E0 | 2.9E0 | 2.4E0 | 2.5E0 | 1.5E-3 | 2.1E-3 | 6.1E0 | 6.1E0 | 218 | 51 | 87 | 51 | 0.51 |
| Al | mg/mL | 8.8E-5 | 7.2E-5 | 2.5E-4 | 2.4E-4 | 4.2E-4 | 3.9E-4 | 2.5E-6 | 1.3E-5 | 1.9E-3 | 1.7E-3 | 218 | 51 | 87 | 51 | 0.52 |
| An | U/mL | 4.1E1 | 6.0E1 | 1.8E2 | 2.9E2 | 5.5E2 | 1.1E3 | 9.8E-4 | 9.0E-1 | 5.5E3 | 7.8E3 | 218 | 51 | 87 | 51 | 0.57 |
| Ao | pg/mL | 8.1E1 | 1.0E2 | 2.3E2 | 9.2E2 | 1.1E3 | 5.4E3 | 2.8E0 | 5.4E0 | 1.6E4 | 3.8E4 | 218 | 51 | 87 | 51 | 0.58 |
| Ap | ng/mL | 2.6E1 | 4.3E1 | 3.6E1 | 5.9E1 | 3.2E1 | 5.6E1 | 9.9E-1 | 3.2E0 | 1.7E2 | 2.9E2 | 218 | 51 | 87 | 51 | 0.66 |
| Ar | ng/mL | 6.3E-1 | 1.3E0 | 2.3E0 | 4.8E0 | 4.7E0 | 1.1E1 | 3.4E-3 | 9.5E-2 | 4.3E1 | 5.4E1 | 218 | 51 | 87 | 51 | 0.61 |
| As | ng/mL | 8.6E-3 | 1.1E-2 | 1.3E-2 | 3.6E-2 | 1.7E-2 | 1.7E-1 | 1.7E-3 | 1.7E-3 | 1.1E-1 | 1.2E0 | 218 | 51 | 87 | 51 | 0.54 |
| Aw | pg/mL | 1.5E1 | 1.8E1 | 1.6E1 | 2.0E1 | 4.9E0 | 7.7E0 | 5.0E0 | 1.1E1 | 3.2E1 | 5.1E1 | 218 | 51 | 87 | 51 | 0.67 |
| Ax | ng/mL | 2.2E0 | 4.1E0 | 9.2E0 | 3.4E1 | 1.9E1 | 1.2E2 | 1.9E-2 | 4.2E-2 | 1.5E2 | 7.7E2 | 218 | 51 | 87 | 51 | 0.55 |
| Ba | ng/mL | 4.2E1 | 1.8E2 | 3.5E2 | 6.8E2 | 9.5E2 | 1.4E3 | 3.7E-1 | 2.4E0 | 8.1E3 | 8.1E3 | 218 | 51 | 87 | 51 | 0.67 |
| Bb | ng/mL | 2.3E0 | 4.7E0 | 4.8E0 | 8.1E0 | 8.2E0 | 1.1E1 | 4.1E-3 | 3.8E-1 | 6.6E1 | 6.4E1 | 218 | 51 | 87 | 51 | 0.66 |
| Bc | ng/mL | 3.2E1 | 4.4E1 | 9.6E1 | 1.5E2 | 1.8E2 | 2.6E2 | 1.1E-1 | 2.4E0 | 1.0E3 | 1.0E3 | 218 | 51 | 87 | 51 | 0.58 |
| Bg | ng/mL | 7.1E-2 | 2.9E-1 | 3.4E0 | 1.3E1 | 2.1E1 | 5.8E1 | 5.3E-4 | 5.3E-4 | 2.5E2 | 4.0E2 | 218 | 51 | 87 | 51 | 0.65 |
| Bn | ng/mL | 5.6E-2 | 5.6E-2 | 8.6E-1 | 2.7E0 | 1.6E0 | 8.3E0 | 5.6E-2 | 5.6E-2 | 9.7E0 | 5.8E1 | 218 | 51 | 87 | 51 | 0.56 |
| Bo | ng/mL | 1.1E1 | 1.9E1 | 1.2E1 | 2.4E1 | 8.8E0 | 3.8E1 | 1.6E-2 | 1.6E-2 | 4.4E1 | 2.8E2 | 218 | 51 | 87 | 51 | 0.64 |
| Ch | uIU/mL | 1.1E0 | 1.4E0 | 7.6E0 | 5.7E1 | 2.3E1 | 1.9E2 | 3.4E-3 | 3.9E-2 | 2.1E2 | 1.2E3 | 218 | 51 | 87 | 51 | 0.60 |
| Co | pg/mL | 3.0E1 | 5.3E1 | 8.0E1 | 1.8E2 | 2.0E2 | 6.2E2 | 3.9E0 | 1.5E-1 | 1.9E3 | 4.4E3 | 218 | 51 | 87 | 51 | 0.64 |
| Cp | ng/mL | 2.0E1 | 2.5E1 | 2.4E1 | 6.3E1 | 2.5E1 | 1.8E2 | 6.0E-1 | 6.0E-1 | 2.9E2 | 1.3E3 | 218 | 51 | 87 | 51 | 0.66 |
| Cq | ng/mL | 2.4E-2 | 4.2E-2 | 1.7E-1 | 1.0E0 | 1.2E0 | 6.9E0 | 8.0E-4 | 8.0E-4 | 1.7E1 | 4.9E1 | 218 | 51 | 87 | 51 | 0.59 |
| Cs | ng/mL | 6.0E1 | 1.2E2 | 2.4E2 | 6.0E2 | 4.4E2 | 1.7E3 | 3.9E-1 | 2.2E0 | 2.9E3 | 1.1E4 | 218 | 51 | 87 | 51 | 0.57 |
| Ct | ng/mL | 1.2E0 | 8.5E-1 | 3.1E1 | 6.9E1 | 9.4E1 | 1.5E2 | 6.2E-3 | 1.1E-4 | 6.2E2 | 6.2E2 | 218 | 51 | 87 | 51 | 0.50 |
| Cu | ng/mL | 2.1E-1 | 3.6E-1 | 4.2E-1 | 1.8E0 | 8.2E-1 | 9.2E0 | 9.6E-3 | 1.5E-2 | 9.2E0 | 6.6E1 | 218 | 51 | 87 | 51 | 0.67 |
| Cv | ng/mL | 3.9E0 | 8.0E0 | 1.6E1 | 4.4E1 | 5.3E1 | 1.1E2 | 5.6E-3 | 2.4E-2 | 5.3E2 | 5.2E2 | 218 | 51 | 87 | 51 | 0.55 |
| Cw | mIU/mL | 2.7E-2 | 4.4E-2 | 3.4E-2 | 1.8E-1 | 2.4E-2 | 9.4E-1 | 2.3E-3 | 4.7E-3 | 1.4E-1 | 6.8E0 | 218 | 51 | 87 | 51 | 0.67 |
| Cx | ng/mL | 1.7E-1 | 2.0E0 | 5.1E1 | 6.7E1 | 1.0E2 | 1.1E2 | 9.3E-5 | 9.3E-5 | 3.9E2 | 3.9E2 | 218 | 51 | 87 | 51 | 0.53 |
| Db | ug/mL | 7.3E0 | 8.4E0 | 8.3E0 | 1.1E1 | 5.7E0 | 8.3E0 | 5.0E-1 | 8.7E-1 | 3.9E1 | 4.1E1 | 218 | 51 | 87 | 51 | 0.58 |
| Dc | nmol/L | 1.8E-2 | 2.8E-2 | 5.7E-2 | 3.6E-1 | 1.4E-1 | 2.0E0 | 5.2E-6 | 1.3E-3 | 1.2E0 | 1.4E1 | 218 | 51 | 87 | 51 | 0.59 |
| Dd | ug/mL | 6.8E-2 | 1.1E-1 | 1.7E-1 | 2.5E-1 | 2.6E-1 | 5.4E-1 | 1.9E-4 | 3.2E-3 | 1.6E0 | 3.6E0 | 218 | 51 | 87 | 51 | 0.53 |
| De | ng/mL | 3.4E-3 | 3.4E-3 | 6.0E-2 | 1.3E-1 | 1.1E-1 | 2.1E-1 | 3.4E-3 | 3.4E-3 | 5.9E-1 | 9.0E-1 | 218 | 51 | 87 | 51 | 0.59 |
| Dg | ng/mL | 2.5E1 | 5.4E1 | 3.7E1 | 6.1E1 | 3.4E1 | 4.1E1 | 2.4E-1 | 2.3E0 | 1.9E2 | 1.9E2 | 218 | 51 | 87 | 51 | 0.70 |
| Di | pg/mL | 1.7E0 | 2.7E0 | 2.0E0 | 3.1E0 | 1.8E0 | 2.4E0 | 1.8E-1 | 1.8E-1 | 1.3E1 | 1.1E1 | 218 | 51 | 87 | 51 | 0.65 |
| Dk | uIU/mL | 1.5E-2 | 2.3E-2 | 1.0E-1 | 1.2E-1 | 6.8E-1 | 3.4E-1 | 1.1E-4 | 1.1E-4 | 8.9E0 | 2.3E0 | 218 | 51 | 87 | 51 | 0.66 |
| Dl | ng/mL | 2.1E2 | 3.9E2 | 2.7E2 | 4.6E2 | 2.4E2 | 3.7E2 | 1.7E0 | 1.0E1 | 1.4E3 | 1.6E3 | 218 | 51 | 87 | 51 | 0.66 |
| Dp | ng/ml | 2.4E0 | 2.6E0 | 4.5E0 | 9.5E0 | 6.6E0 | 3.0E1 | 3.7E-3 | 3.7E-3 | 4.3E1 | 2.0E2 | 111 | 47 | 86 | 47 | 0.49 |
| Dr | pg/ml | 2.2E1 | 3.2E1 | 4.6E1 | 5.9E2 | 6.4E1 | 2.2E3 | 7.5E-1 | 3.5E0 | 2.9E2 | 1.0E4 | 78 | 22 | 39 | 22 | 0.66 |
| Du | ng/ml | 2.7E1 | 6.3E2 | 5.5E2 | 1.9E3 | 1.3E3 | 5.3E3 | 1.2E0 | 1.2E0 | 7.0E3 | 2.4E4 | 45 | 19 | 35 | 19 | 0.65 |
| Dw | ng/ml | 2.6E-2 | 2.0E-2 | 8.9E-2 | 4.3E-2 | 1.5E-1 | 6.1E-2 | 9.2E-3 | 9.2E-3 | 6.7E-1 | 1.9E-1 | 29 | 8 | 6 | 8 | 0.39 |
| Ef | ng/ml | 9.5E-2 | 2.6E-1 | 5.6E-1 | 1.4E0 | 1.3E0 | 2.5E0 | 5.7E-4 | 1.1E-2 | 9.4E0 | 9.5E0 | 143 | 49 | 86 | 49 | 0.65 |
| Wm | % | 7.0E-1 | 1.1E0 | 3.4E1 | 4.8E1 | 2.1E2 | 1.9E2 | 8.5E-2 | 8.5E-2 | 2.4E3 | 1.0E3 | 173 | 51 | 101 | 51 | 0.54 |
| Ed | pg/ml | 7.1E0 | 4.4E1 | 1.0E2 | 3.6E2 | 6.9E2 | 5.0E1 | 5.2E-1 | 5.2E-1 | 7.3E3 | 1.9E2 | 111 | 47 | 85 | 47 | 0.51 |
| Eo | ng/ml | 2.3E0 | 1.8E0 | 4.1E0 | 2.8E0 | 4.6E0 | 2.6E0 | 1.3E-1 | 3.6E-1 | 1.6E1 | 6.9E0 | 29 | 8 | 6 | 8 | 0.47 |
| Yf | ng/mL | 1.7E1 | 1.4E1 | 1.6E2 | 7.3E1 | 9.1E2 | 1.5E2 | 2.9E-1 | 2.9E-1 | 6.6E3 | 5.9E2 | 52 | 19 | 41 | 19 | 0.43 |
| Tj | pg/mL | 3.7E-1 | 3.7E-1 | 8.9E1 | 1.4E1 | 4.0E2 | 3.8E1 | 3.6E-1 | 3.7E-1 | 3.5E3 | 2.1E2 | 141 | 49 | 86 | 49 | 0.45 |
| Po | pg/ml | 2.6E-1 | 5.2E0 | 7.7E0 | 1.5E1 | 2.5E1 | 3.3E1 | 8.0E-3 | 2.6E-2 | 2.7E2 | 2.2E2 | 316 | 77 | 135 | 77 | 0.64 |
| Ti | ug/mL | 2.5E0 | 4.9E0 | 3.7E0 | 5.8E0 | 3.4E0 | 4.2E0 | 1.2E-1 | 9.7E-1 | 1.5E1 | 1.8E1 | 77 | 24 | 61 | 24 | 0.69 |
| Em | ng/ml | 2.9E-3 | 8.2E-3 | 6.8E-2 | 1.1E-1 | 1.2E-1 | 3.7E-1 | 2.8E-16 | 2.8E-16 | 5.4E-1 | 1.9E0 | 93 | 28 | 40 | 28 | 0.47 |
| Et | ng/ml | 1.1E3 | 2.3E3 | 1.4E3 | 2.3E3 | 1.0E3 | 1.3E3 | 7.7E1 | 1.3E2 | 4.2E3 | 5.0E3 | 316 | 77 | 135 | 77 | 0.70 |
| Eq | pg/ml | 1.3E2 | 3.2E2 | 3.0E2 | 3.9E2 | 3.9E2 | 4.0E2 | 1.0E0 | 1.0E0 | 1.8E3 | 1.3E3 | 45 | 19 | 35 | 19 | 0.54 |
| Ew | U/ml | 2.0E0 | 1.9E0 | 2.2E0 | 2.1E0 | 1.5E0 | 8.8E-1 | 6.5E-1 | 1.3E0 | 8.8E0 | 3.5E0 | 29 | 8 | 6 | 8 | 0.54 |
| Th | ug/mL | 1.1E0 | 1.6E0 | 1.6E0 | 2.1E0 | 1.7E0 | 1.8E0 | 2.6E-3 | 3.7E-1 | 1.2E1 | 7.5E0 | 77 | 24 | 61 | 24 | 0.59 |
| Fa | ng/ml | 4.0E1 | 5.3E1 | 1.4E2 | 1.3E2 | 7.9E2 | 2.1E2 | 3.4E-2 | 6.0E-1 | 8.0E3 | 1.0E3 | 109 | 45 | 86 | 45 | 0.62 |

Figure 6

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ez | ng/ml | 5.0E0 | 5.0E0 | 2.4E1 | 2.4E1 | 7.6E1 | 6.7E1 | 1.3E-2 | 1.3E-2 | 7.1E2 | 4.5E2 | 111 | 47 | 86 | 47 | 0.55 |
| Fb | ng/ml | 2.3E1 | 2.7E1 | 2.2E1 | 2.7E1 | 1.2E1 | 6.9E0 | 1.0E0 | 6.6E-1 | 5.7E1 | 4.3E1 | 109 | 46 | 86 | 46 | 0.64 |
| Ex | ng/ml | 6.2E-2 | 1.2E-1 | 2.6E-1 | 2.3E-1 | 9.1E-1 | 3.0E-1 | 3.5E-5 | 1.7E-4 | 8.9E0 | 1.2E0 | 102 | 42 | 53 | 42 | 0.62 |
| Fc | pg/ml | 2.2E-1 | 2.2E-1 | 3.3E2 | 3.8E1 | 2.2E3 | 1.1E2 | 2.2E-1 | 2.2E-1 | 1.5E4 | 3.9E2 | 45 | 20 | 35 | 20 | 0.52 |
| Fd | pg/ml | 9.8E-1 | 1.2E2 | 1.0E3 | 1.6E3 | 4.9E3 | 5.6E3 | 4.5E-1 | 9.8E-1 | 3.3E4 | 2.5E4 | 45 | 20 | 35 | 20 | 0.55 |
| Fi | pg/ml | 2.5E-1 | 2.5E-1 | 3.5E2 | 1.1E2 | 2.1E3 | 4.1E2 | 2.5E-1 | 2.5E-1 | 1.4E4 | 1.8E3 | 45 | 20 | 35 | 20 | 0.51 |
| Fn | ng/ml | 2.1E-1 | 2.1E-1 | 9.2E0 | 2.6E0 | 4.0E1 | 5.1E0 | 1.1E-14 | 1.1E-14 | 4.2E2 | 2.7E1 | 111 | 47 | 86 | 47 | 0.44 |
| Fp | ng/ml | 1.0E1 | 2.3E1 | 2.1E1 | 3.4E1 | 2.7E1 | 3.4E1 | 6.0E-3 | 5.8E-2 | 1.4E2 | 1.3E2 | 333 | 77 | 136 | 77 | 0.62 |
| Fr | ng/ml | 2.5E4 | 6.2E4 | 9.7E4 | 2.1E5 | 1.7E5 | 2.6E5 | 6.4E2 | 1.8E3 | 8.4E5 | 8.4E5 | 398 | 81 | 137 | 81 | 0.67 |
| Fw | pg/ml | 8.5E-1 | 2.7E0 | 1.1E2 | 2.4E1 | 7.2E2 | 6.1E1 | 1.1E-14 | 1.2E-1 | 6.9E3 | 3.3E2 | 144 | 50 | 87 | 50 | 0.55 |
| Fy | ng/ml | 3.1E1 | 4.4E1 | 4.9E1 | 8.6E1 | 5.5E1 | 1.3E2 | 1.8E-1 | 1.2E-1 | 3.3E2 | 6.5E2 | 110 | 46 | 85 | 46 | 0.61 |
| Gh | pg/ml | 2.3E0 | 2.0E0 | 6.2E1 | 8.5E1 | 2.7E2 | 3.4E2 | 2.9E-2 | 2.9E-2 | 1.8E3 | 1.5E3 | 45 | 19 | 35 | 19 | 0.43 |
| Gb | % | 3.3E1 | 4.5E1 | 4.1E1 | 5.9E1 | 3.6E1 | 6.3E1 | 3.1E0 | 1.4E1 | 1.9E2 | 3.0E2 | 45 | 20 | 34 | 20 | 0.62 |
| Gc | ng/ml | 8.4E1 | 1.4E2 | 1.1E2 | 2.0E2 | 1.1E2 | 1.7E2 | 6.4E0 | 3.8E1 | 7.3E2 | 6.3E2 | 82 | 22 | 40 | 22 | 0.71 |
| Gd | ng/ml | 3.1E1 | 3.8E1 | 3.1E1 | 3.9E1 | 1.5E1 | 2.3E1 | 5.4E0 | 7.6E0 | 6.9E1 | 8.0E1 | 95 | 24 | 40 | 24 | 0.59 |
| Gn | U/ml | 5.1E-1 | 2.0E-1 | 1.8E0 | 5.6E0 | 4.1E0 | 2.4E1 | 1.3E-3 | 5.6E-3 | 3.0E1 | 1.1E2 | 74 | 22 | 39 | 22 | 0.41 |
| Gl | pg/ml | 6.0E3 | 1.1E4 | 9.8E3 | 1.3E4 | 9.0E3 | 9.3E3 | 2.3E2 | 6.7E2 | 3.2E4 | 3.1E4 | 140 | 50 | 87 | 50 | 0.63 |
| Gp | U/ml | 1.8E0 | 1.1E0 | 4.4E0 | 2.5E0 | 8.0E0 | 4.1E0 | 1.3E-3 | 1.5E-2 | 6.7E1 | 2.0E1 | 144 | 49 | 87 | 49 | 0.40 |
| Gz | ug/ml | 1.2E0 | 1.6E0 | 1.2E1 | 8.5E0 | 5.8E1 | 2.3E1 | 2.9E-16 | 8.0E-2 | 4.8E2 | 1.5E2 | 69 | 40 | 52 | 40 | 0.54 |
| Ha | ng/ml | 2.7E0 | 3.4E0 | 9.0E0 | 8.7E0 | 2.0E1 | 1.6E1 | 1.7E-2 | 1.4E-3 | 1.0E2 | 1.0E2 | 109 | 47 | 85 | 47 | 0.53 |
| Nm | pg/ml | 1.4E4 | 2.2E4 | 2.6E4 | 5.8E4 | 5.1E4 | 1.4E5 | 1.0E-9 | 1.0E-9 | 7.8E5 | 9.6E5 | 315 | 79 | 136 | 79 | 0.58 |
| Nn | pg/ml | 1.2E2 | 1.9E2 | 2.7E3 | 4.7E3 | 1.1E4 | 1.9E4 | 1.0E-9 | 1.0E-9 | 1.0E5 | 1.1E5 | 315 | 79 | 136 | 79 | 0.60 |
| No | pg/ml | 1.4E1 | 2.1E1 | 2.7E1 | 6.3E1 | 5.7E1 | 1.4E2 | 1.0E-9 | 3.2E-1 | 5.9E2 | 7.7E2 | 315 | 79 | 136 | 79 | 0.59 |
| Nq | pg/ml | 2.8E0 | 4.6E0 | 2.2E1 | 3.3E1 | 8.9E1 | 9.2E1 | 1.0E-9 | 1.0E-9 | 1.2E3 | 6.7E2 | 315 | 79 | 136 | 79 | 0.53 |
| Nr | pg/ml | 6.0E-1 | 3.2E0 | 1.4E1 | 4.5E1 | 6.9E1 | 1.7E2 | 1.0E-9 | 1.0E-9 | 9.8E2 | 1.4E3 | 315 | 79 | 136 | 79 | 0.63 |
| Ns | pg/ml | 1.0E-9 | 1.0E-9 | 1.3E1 | 7.5E0 | 7.8E1 | 3.6E1 | 1.0E-9 | 1.0E-9 | 1.1E3 | 2.4E2 | 315 | 79 | 136 | 79 | 0.49 |
| Nt | pg/ml | 9.9E1 | 1.3E2 | 1.4E2 | 1.8E2 | 1.3E2 | 1.7E2 | 1.5E1 | 1.2E1 | 1.5E3 | 1.2E3 | 315 | 79 | 136 | 79 | 0.61 |
| Nu | pg/ml | 2.0E1 | 4.3E1 | 5.2E1 | 6.5E1 | 8.8E1 | 7.9E1 | 1.0E-9 | 1.0E-9 | 8.9E2 | 3.7E2 | 315 | 79 | 136 | 79 | 0.58 |
| Lu | pg/ml | 1.0E4 | 1.0E4 | 1.6E4 | 1.1E4 | 4.2E4 | 1.1E4 | 6.7E2 | 1.1E3 | 5.6E5 | 5.9E4 | 317 | 79 | 136 | 79 | 0.46 |
| Lv | pg/ml | 1.0E-9 | 9.9E0 | 1.1E1 | 2.7E1 | 2.2E1 | 4.0E1 | 1.0E-9 | 1.0E-9 | 2.4E2 | 1.9E2 | 317 | 79 | 136 | 79 | 0.63 |
| Lw | pg/ml | 1.0E-9 | 1.0E-9 | 1.3E-1 | 2.2E0 | 1.8E0 | 1.0E1 | 1.0E-9 | 1.0E-9 | 3.2E1 | 8.0E1 | 317 | 79 | 136 | 79 | 0.53 |
| Lx | pg/ml | 1.0E-9 | 6.3E1 | 1.2E2 | 3.2E2 | 4.3E2 | 5.9E2 | 1.0E-9 | 1.0E-9 | 6.2E3 | 2.8E3 | 317 | 79 | 136 | 79 | 0.65 |
| Ly | pg/ml | 1.0E-9 | 1.0E-9 | 9.2E0 | 1.1E1 | 1.8E1 | 2.1E1 | 1.0E-9 | 1.0E-9 | 1.2E2 | 9.6E1 | 317 | 79 | 136 | 79 | 0.51 |
| Lz | pg/ml | 1.0E-9 | 1.0E-9 | 2.5E0 | 7.0E0 | 2.5E1 | 3.2E1 | 1.0E-9 | 1.0E-9 | 4.3E2 | 2.6E2 | 317 | 79 | 136 | 79 | 0.53 |
| Ma | pg/ml | 2.7E2 | 7.3E2 | 1.4E3 | 3.0E3 | 4.6E3 | 7.3E3 | 1.0E-9 | 1.0E-9 | 6.5E4 | 5.2E4 | 317 | 79 | 136 | 79 | 0.63 |
| Mb | pg/ml | 2.5E1 | 3.7E1 | 3.0E1 | 3.9E1 | 1.3E1 | 2.5E1 | 5.4E0 | 4.1E0 | 6.9E1 | 2.1E2 | 317 | 79 | 136 | 79 | 0.60 |
| Mc | pg/ml | 1.0E-9 | 1.0E-9 | 2.0E-2 | 1.8E-1 | 2.5E-1 | 1.5E0 | 1.0E-9 | 1.0E-9 | 4.0E0 | 1.3E1 | 317 | 79 | 136 | 79 | 0.51 |
| Md | pg/ml | 1.0E-9 | 1.0E-9 | 5.0E-1 | 9.6E-1 | 4.0E0 | 4.2E0 | 1.0E-9 | 1.0E-9 | 6.5E1 | 2.9E1 | 317 | 79 | 136 | 79 | 0.53 |
| Me | pg/ml | 3.2E1 | 2.7E1 | 2.9E1 | 3.2E1 | 1.6E1 | 4.3E1 | 1.0E-9 | 1.0E-9 | 1.2E2 | 3.2E2 | 317 | 79 | 136 | 79 | 0.42 |
| Mf | pg/ml | 1.0E-9 | 1.0E-9 | 3.8E-1 | 1.9E0 | 1.7E0 | 7.6E0 | 1.0E-9 | 1.0E-9 | 2.0E1 | 5.6E1 | 317 | 79 | 136 | 79 | 0.59 |
| Mg | pg/ml | 2.2E0 | 4.6E0 | 7.3E0 | 1.1E1 | 1.2E1 | 1.6E1 | 1.0E-9 | 1.0E-9 | 8.8E1 | 9.2E1 | 317 | 79 | 136 | 79 | 0.57 |
| Mh | pg/ml | 1.0E-9 | 1.0E-9 | 9.0E-1 | 1.2E0 | 8.0E0 | 3.6E0 | 1.0E-9 | 1.0E-9 | 1.1E2 | 1.8E1 | 317 | 79 | 136 | 79 | 0.57 |
| Mi | pg/ml | 1.0E-9 | 1.0E-9 | 7.8E-1 | 2.1E0 | 7.5E0 | 1.3E1 | 1.0E-9 | 1.0E-9 | 1.2E2 | 1.1E2 | 317 | 79 | 136 | 79 | 0.51 |
| Mj | pg/ml | 1.0E-9 | 1.0E-9 | 4.6E0 | 9.7E0 | 2.8E1 | 3.2E1 | 1.0E-9 | 1.0E-9 | 4.6E2 | 2.1E2 | 317 | 79 | 136 | 79 | 0.53 |
| Mk | pg/ml | 1.0E-9 | 3.7E0 | 1.7E1 | 1.8E1 | 1.1E2 | 6.4E1 | 1.0E-9 | 1.0E-9 | 1.7E3 | 5.0E2 | 317 | 79 | 136 | 79 | 0.54 |
| Ml | pg/ml | 1.0E-9 | 1.0E-9 | 9.5E0 | 1.6E1 | 1.2E2 | 7.1E1 | 1.0E-9 | 1.0E-9 | 2.1E3 | 5.1E2 | 317 | 79 | 136 | 79 | 0.57 |
| Mm | pg/ml | 4.6E2 | 9.4E2 | 8.4E2 | 1.6E3 | 9.7E2 | 2.0E3 | 1.0E-9 | 1.0E-9 | 6.0E3 | 1.2E4 | 317 | 79 | 136 | 79 | 0.61 |
| Mn | pg/ml | 4.9E0 | 9.7E0 | 1.0E1 | 1.2E1 | 2.6E1 | 1.3E1 | 1.0E-9 | 1.0E-9 | 3.5E2 | 7.8E1 | 317 | 79 | 136 | 79 | 0.64 |
| Mp | pg/ml | 1.0E-9 | 2.3E0 | 1.0E1 | 1.4E1 | 2.3E1 | 2.5E1 | 1.0E-9 | 1.0E-9 | 1.8E2 | 1.3E2 | 317 | 79 | 136 | 79 | 0.57 |
| Mq | pg/ml | 1.0E-9 | 1.0E-9 | 2.9E0 | 6.3E0 | 1.8E1 | 2.0E1 | 1.0E-9 | 1.0E-9 | 2.1E2 | 1.0E2 | 317 | 79 | 136 | 79 | 0.54 |
| Mr | pg/ml | 1.0E-9 | 1.0E-9 | 1.6E1 | 7.8E1 | 9.3E1 | 4.1E2 | 1.0E-9 | 1.0E-9 | 1.4E3 | 3.4E3 | 317 | 79 | 136 | 79 | 0.56 |
| Ms | pg/ml | 4.0E2 | 3.7E2 | 5.5E2 | 4.3E2 | 7.0E2 | 3.7E2 | 1.0E-9 | 1.0E-9 | 5.6E3 | 1.5E3 | 317 | 79 | 136 | 79 | 0.48 |
| Mt | pg/ml | 1.0E-9 | 1.2E0 | 1.1E1 | 4.9E1 | 6.7E1 | 3.6E2 | 1.0E-9 | 1.0E-9 | 8.7E2 | 3.2E3 | 317 | 79 | 136 | 79 | 0.63 |
| Mu | pg/ml | 1.0E-9 | 1.0E-9 | 1.7E0 | 4.3E0 | 1.1E1 | 2.7E1 | 1.0E-9 | 1.0E-9 | 9.9E1 | 2.3E2 | 317 | 79 | 136 | 79 | 0.56 |
| Mv | pg/ml | 1.0E-9 | 1.0E-9 | 9.5E1 | 9.7E1 | 4.5E2 | 2.1E2 | 1.0E-9 | 1.0E-9 | 4.5E3 | 9.2E2 | 317 | 79 | 136 | 79 | 0.58 |
| Mw | pg/ml | 2.3E1 | 4.6E1 | 6.3E2 | 4.9E2 | 4.1E3 | 1.3E3 | 1.0E-9 | 1.0E-9 | 6.2E4 | 7.9E3 | 317 | 79 | 136 | 79 | 0.59 |
| Mx | pg/ml | 1.0E-9 | 1.0E-9 | 2.1E-1 | 9.8E-1 | 8.3E-1 | 4.2E0 | 1.0E-9 | 1.0E-9 | 7.4E0 | 3.2E1 | 317 | 79 | 136 | 79 | 0.56 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| My | pg/ml | 1.0E-9 | 1.0E-9 | 6.1E2 | 3.8E2 | 3.7E3 | 1.5E3 | 1.0E-9 | 1.0E-9 | 3.9E4 | 1.1E4 | 317 | 79 | 136 | 79 | 0.50 |
| Mz | pg/ml | 9.2E0 | 1.2E1 | 2.3E1 | 6.9E1 | 6.3E1 | 2.6E2 | 1.0E-9 | 1.0E-9 | 8.4E2 | 1.9E3 | 317 | 79 | 136 | 79 | 0.60 |
| Na | pg/ml | 1.0E-9 | 1.0E-9 | 5.3E-1 | 1.3E0 | 1.7E0 | 5.1E0 | 1.0E-9 | 1.0E-9 | 9.6E0 | 4.2E1 | 317 | 79 | 136 | 79 | 0.52 |
| Nb | pg/ml | 1.9E0 | 2.4E0 | 4.9E0 | 7.9E0 | 1.7E1 | 2.6E1 | 1.0E-9 | 1.0E-9 | 2.3E2 | 2.1E2 | 317 | 79 | 136 | 79 | 0.57 |
| Nc | pg/ml | 4.8E2 | 1.9E2 | 7.1E2 | 3.3E2 | 8.7E2 | 4.3E2 | 1.0E-9 | 1.0E-9 | 9.2E3 | 1.8E3 | 317 | 79 | 136 | 79 | 0.34 |
| Nd | pg/ml | 3.0E1 | 5.8E0 | 2.6E1 | 1.6E1 | 2.0E1 | 1.7E1 | 1.0E-9 | 1.0E-9 | 8.4E1 | 5.8E1 | 317 | 79 | 136 | 79 | 0.34 |
| Ne | pg/ml | 5.2E2 | 2.9E2 | 6.7E2 | 3.8E2 | 6.7E2 | 3.9E2 | 1.0E-9 | 1.0E-9 | 7.0E3 | 1.7E3 | 317 | 79 | 136 | 79 | 0.35 |
| Nf | pg/ml | 1.0E-9 | 1.0E-9 | 2.8E0 | 3.8E0 | 8.7E0 | 1.9E1 | 1.0E-9 | 1.0E-9 | 8.2E1 | 1.3E2 | 317 | 79 | 136 | 79 | 0.46 |
| Ng | pg/ml | 3.8E1 | 4.9E1 | 1.5E2 | 1.4E2 | 2.9E2 | 2.4E2 | 1.0E-9 | 1.0E-9 | 2.3E3 | 1.2E3 | 317 | 79 | 136 | 79 | 0.52 |
| Nh | pg/ml | 7.7E1 | 4.2E1 | 1.0E2 | 6.5E1 | 9.1E1 | 6.9E1 | 1.0E-9 | 3.1E0 | 5.6E2 | 3.1E2 | 317 | 79 | 136 | 79 | 0.35 |
| Ni | pg/ml | 4.5E0 | 1.4E1 | 8.0E1 | 1.1E2 | 1.3E2 | 1.8E2 | 1.0E-9 | 1.0E-9 | 7.1E2 | 1.1E3 | 317 | 79 | 136 | 79 | 0.54 |
| Nj | pg/ml | 8.9E0 | 3.5E0 | 1.2E1 | 7.4E0 | 1.2E1 | 1.0E1 | 1.0E-9 | 1.0E-9 | 8.3E1 | 5.8E1 | 317 | 79 | 136 | 79 | 0.35 |
| Nk | pg/ml | 2.4E1 | 1.4E1 | 3.7E1 | 2.4E1 | 4.1E1 | 3.1E1 | 1.0E-9 | 1.0E-9 | 2.0E2 | 1.5E2 | 317 | 79 | 136 | 79 | 0.42 |
| Nl | pg/ml | 5.6E1 | 2.5E1 | 7.3E1 | 3.8E1 | 8.5E1 | 4.1E1 | 1.0E-9 | 1.0E-9 | 1.1E3 | 1.6E2 | 317 | 79 | 136 | 79 | 0.34 |
| Hl | pg/ml | 1.2E1 | 1.7E1 | 5.0E1 | 2.0E2 | 8.5E1 | 8.0E2 | 1.0E-9 | 1.0E-9 | 3.5E2 | 3.6E3 | 45 | 20 | 35 | 20 | 0.48 |
| Ho | pg/ml | 1.5E1 | 1.9E1 | 3.4E1 | 4.0E1 | 1.0E2 | 8.4E1 | 1.0E-9 | 6.7E0 | 7.0E2 | 3.9E2 | 45 | 20 | 35 | 20 | 0.63 |
| Hp | ng/ml | 1.7E0 | 1.6E0 | 6.4E1 | 1.8E2 | 2.2E2 | 3.6E2 | 1.0E-9 | 3.5E-1 | 8.9E2 | 8.9E2 | 45 | 20 | 35 | 20 | 0.53 |
| Tz | pg/ml | 4.8E3 | 7.5E3 | 8.4E3 | 1.7E4 | 1.2E4 | 5.4E4 | 7.4E1 | 3.3E2 | 8.8E4 | 3.7E5 | 113 | 46 | 84 | 46 | 0.60 |
| Ua | pg/ml | 3.8E3 | 5.6E3 | 1.3E4 | 1.4E4 | 2.5E4 | 1.7E4 | 3.5E2 | 5.3E2 | 1.4E5 | 6.6E4 | 113 | 46 | 84 | 46 | 0.61 |
| Ub | pg/ml | 5.3E2 | 4.4E2 | 7.9E2 | 7.0E2 | 1.2E3 | 8.1E2 | 1.0E-9 | 1.2E1 | 9.8E3 | 4.4E3 | 113 | 46 | 84 | 46 | 0.50 |
| Ue | pg/ml | 3.0E1 | 2.9E1 | 3.2E1 | 4.7E1 | 1.9E1 | 4.8E1 | 4.2E0 | 5.2E0 | 9.5E1 | 2.7E2 | 113 | 46 | 84 | 46 | 0.55 |
| Uc | pg/ml | 8.9E2 | 1.2E3 | 1.8E3 | 3.2E3 | 3.4E3 | 8.5E3 | 6.1E-1 | 5.5E1 | 2.9E4 | 5.7E4 | 113 | 46 | 84 | 46 | 0.59 |
| Ud | pg/ml | 1.0E-9 | 1.0E-9 | 3.7E0 | 1.2E0 | 3.7E1 | 7.9E0 | 1.0E-9 | 1.0E-9 | 3.9E2 | 5.3E1 | 113 | 46 | 84 | 46 | 0.50 |
| Hq | pg/ml | 1.1E0 | 1.9E0 | 1.2E1 | 1.5E1 | 6.3E1 | 4.7E1 | 1.0E-9 | 1.0E-9 | 9.5E2 | 3.4E2 | 317 | 77 | 136 | 77 | 0.58 |
| Hr | pg/ml | 1.3E2 | 9.0E1 | 8.2E2 | 7.9E2 | 1.5E3 | 2.1E3 | 1.0E-9 | 1.0E-9 | 9.7E3 | 1.4E4 | 317 | 77 | 136 | 77 | 0.47 |
| Hu | pg/ml | 1.4E1 | 4.0E1 | 3.5E3 | 4.8E3 | 3.7E4 | 3.0E4 | 1.0E-9 | 1.0E-9 | 6.3E5 | 2.6E5 | 317 | 77 | 136 | 77 | 0.57 |
| Hv | pg/ml | 1.3E0 | 1.8E0 | 3.6E0 | 1.5E1 | 1.5E1 | 1.0E2 | 1.0E-9 | 1.0E-9 | 2.5E2 | 8.9E2 | 317 | 77 | 136 | 77 | 0.54 |
| Hw | pg/ml | 6.8E0 | 7.3E0 | 2.7E1 | 1.4E2 | 1.1E2 | 1.1E3 | 1.0E-9 | 1.0E-9 | 1.7E3 | 9.4E3 | 317 | 77 | 136 | 77 | 0.49 |
| Hx | pg/ml | 8.3E0 | 1.4E1 | 6.7E1 | 5.5E1 | 5.3E2 | 1.8E2 | 1.0E-9 | 1.0E-9 | 9.3E3 | 1.3E3 | 317 | 77 | 136 | 77 | 0.55 |
| Ib | ng/ml | 6.6E-2 | 7.0E-2 | 7.9E-1 | 3.5E0 | 3.4E0 | 1.2E1 | 1.0E-9 | 1.0E-9 | 3.0E1 | 5.6E1 | 109 | 46 | 85 | 46 | 0.53 |
| Ic | U/ml | 2.2E2 | 2.2E2 | 3.3E2 | 2.3E3 | 1.5E3 | 1.0E4 | 2.9E0 | 6.6E0 | 1.5E4 | 6.5E4 | 109 | 46 | 85 | 46 | 0.66 |
| Id | U/ml | 6.2E-1 | 7.6E-1 | 1.1E0 | 1.1E1 | 1.3E0 | 6.4E1 | 1.0E-9 | 1.5E-1 | 7.2E0 | 4.3E2 | 109 | 46 | 85 | 46 | 0.57 |
| Tt | pg/ml | 1.6E2 | 2.0E2 | 1.7E2 | 2.0E2 | 4.3E1 | 6.4E1 | 8.0E1 | 7.6E1 | 3.0E2 | 4.4E2 | 101 | 40 | 78 | 40 | 0.69 |
| To | pg/ml | 1.6E0 | 1.8E0 | 1.7E0 | 2.3E0 | 1.8E0 | 2.7E0 | 1.0E-9 | 1.0E-9 | 7.1E0 | 1.2E1 | 108 | 43 | 81 | 43 | 0.55 |
| Tr | pg/ml | 2.8E0 | 5.1E0 | 4.0E0 | 8.6E0 | 4.2E0 | 1.4E1 | 3.5E-2 | 9.5E-2 | 2.4E1 | 7.6E1 | 106 | 41 | 80 | 41 | 0.63 |
| Tn | pg/ml | 2.5E1 | 4.6E1 | 4.8E1 | 1.8E2 | 7.0E1 | 4.6E2 | 2.6E0 | 1.1E1 | 3.7E2 | 2.3E3 | 108 | 43 | 81 | 43 | 0.71 |
| Tv | ng/ml | 1.1E1 | 1.5E1 | 2.0E1 | 1.8E2 | 5.0E1 | 1.1E3 | 1.0E-9 | 1.0E-9 | 4.9E2 | 7.1E3 | 108 | 43 | 81 | 43 | 0.57 |
| Ih | ng/ml | 6.8E1 | 7.7E1 | 1.9E2 | 3.2E2 | 3.2E2 | 5.3E2 | 1.0E-9 | 1.0E-9 | 2.5E3 | 2.8E3 | 317 | 79 | 136 | 79 | 0.55 |
| Ii | ng/ml | 8.1E1 | 1.1E2 | 2.9E2 | 2.8E2 | 8.2E2 | 6.5E2 | 7.5E-1 | 1.3E0 | 8.4E3 | 4.5E3 | 317 | 79 | 136 | 79 | 0.53 |
| Ij | ng/ml | 7.2E1 | 8.2E1 | 2.1E2 | 4.7E2 | 7.5E2 | 2.8E3 | 2.1E0 | 9.3E0 | 6.4E3 | 2.4E4 | 317 | 76 | 136 | 76 | 0.56 |
| Ik | ng/ml | 1.1E1 | 6.8E1 | 1.0E3 | 2.0E3 | 9.8E3 | 1.4E4 | 5.9E-1 | 1.7E0 | 1.2E5 | 1.2E5 | 316 | 78 | 136 | 78 | 0.61 |
| Il | ng/ml | 3.8E2 | 4.1E2 | 1.5E3 | 1.6E3 | 3.1E3 | 3.2E3 | 1.0E-9 | 1.0E-9 | 1.2E4 | 1.3E4 | 314 | 76 | 136 | 76 | 0.50 |
| Im | ng/ml | 1.9E2 | 2.7E2 | 3.1E2 | 5.2E2 | 3.5E2 | 8.2E2 | 1.3E1 | 2.0E1 | 3.1E3 | 6.2E3 | 316 | 77 | 136 | 77 | 0.61 |
| In | ng/ml | 4.2E0 | 3.3E0 | 3.5E2 | 6.4E1 | 2.4E2 | 5.0E2 | 1.0E-9 | 1.0E-9 | 3.9E3 | 4.5E3 | 317 | 79 | 136 | 79 | 0.44 |
| Hb | ng/ml | 2.0E1 | 3.0E1 | 2.6E1 | 4.0E1 | 2.4E1 | 4.0E1 | 1.1E0 | 6.2E-1 | 1.3E2 | 2.0E2 | 110 | 48 | 86 | 48 | 0.65 |
| Hc | ng/ml | 6.9E2 | 6.0E2 | 2.0E3 | 5.2E3 | 4.7E3 | 1.6E4 | 1.0E-9 | 1.0E-9 | 3.6E4 | 1.0E5 | 110 | 48 | 86 | 48 | 0.53 |
| Hf | ng/ml | 1.4E2 | 1.2E2 | 4.0E2 | 2.3E2 | 5.5E2 | 2.6E2 | 1.0E-9 | 1.0E-9 | 2.5E3 | 1.0E3 | 110 | 48 | 86 | 48 | 0.47 |
| Io | ng/ml | 8.4E3 | 1.1E4 | 1.8E4 | 1.9E4 | 5.5E4 | 2.6E4 | 6.6E1 | 6.6E1 | 8.8E5 | 1.1E5 | 315 | 77 | 135 | 77 | 0.54 |
| Ip | ng/ml | 9.7E0 | 2.0E1 | 1.9E1 | 2.7E1 | 2.6E1 | 3.1E1 | 1.0E-9 | 4.9E-3 | 2.6E2 | 1.6E2 | 315 | 77 | 135 | 77 | 0.54 |
| Iq | ug/ml | 1.1E-1 | 1.5E-1 | 4.4E1 | 4.3E0 | 7.7E2 | 2.5E1 | 1.0E-9 | 1.0E-9 | 1.4E4 | 2.2E2 | 315 | 77 | 135 | 77 | 0.56 |
| Ir | ug/ml | 3.2E-1 | 6.5E-1 | 3.2E0 | 9.4E0 | 2.1E1 | 4.6E1 | 1.0E-9 | 1.0E-9 | 2.4E2 | 3.7E2 | 314 | 77 | 135 | 77 | 0.62 |
| Is | ng/ml | 1.4E0 | 3.8E0 | 5.6E0 | 1.4E1 | 1.2E1 | 3.5E1 | 1.0E-9 | 2.2E-3 | 8.8E1 | 2.6E2 | 315 | 77 | 135 | 77 | 0.61 |
| It | ng/ml | 2.0E0 | 2.5E0 | 2.2E1 | 1.6E1 | 1.1E2 | 7.8E1 | 1.0E-9 | 1.0E-9 | 1.2E3 | 6.8E2 | 315 | 77 | 135 | 77 | 0.56 |
| Iu | ng/ml | 2.1E2 | 2.7E2 | 1.5E3 | 1.7E3 | 4.8E3 | 4.1E3 | 1.0E-9 | 1.0E-9 | 2.9E4 | 2.4E4 | 315 | 77 | 135 | 77 | 0.55 |
| Iv | ng/ml | 1.3E1 | 2.3E1 | 4.7E1 | 1.4E2 | 1.3E2 | 5.9E2 | 1.0E-9 | 1.0E-9 | 1.6E3 | 3.8E3 | 315 | 77 | 135 | 77 | 0.61 |
| Iz | ng/ml | 1.3E2 | 1.9E2 | 4.0E2 | 1.6E3 | 9.6E2 | 8.9E3 | 1.5E0 | 4.9E0 | 8.4E3 | 6.2E4 | 110 | 48 | 86 | 48 | 0.58 |
| Yg | pg/ml | 2.5E2 | 3.2E2 | 1.6E3 | 8.1E3 | 7.4E3 | 1.2E3 | 1.0E-9 | 1.0E-9 | 5.0E4 | 5.0E3 | 45 | 19 | 35 | 19 | 0.57 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yh | pg/ml | 2.1E2 | 3.0E2 | 5.1E2 | 5.0E2 | 1.2E3 | 6.1E2 | 1.0E-9 | 1.0E-9 | 7.8E3 | 2.3E3 | 45 | 19 | 35 | 19 | 0.56 |
| Yi | pg/ml | 2.2E2 | 4.3E2 | 5.6E2 | 2.1E3 | 1.2E3 | 5.9E3 | 1.0E-9 | 1.0E-9 | 7.6E3 | 2.6E4 | 45 | 19 | 35 | 19 | 0.64 |
| Yk | U/ml | 1.0E-9 | 1.0E-9 | 1.8E-1 | 3.4E-1 | 5.3E-1 | 1.3E0 | 1.0E-9 | 1.0E-9 | 3.0E0 | 5.6E0 | 45 | 19 | 35 | 19 | 0.48 |
| Yj | pg/ml | 1.7E2 | 1.6E2 | 3.9E2 | 6.3E2 | 5.6E2 | 1.6E3 | 1.0E-9 | 3.9E1 | 3.2E3 | 7.0E3 | 45 | 19 | 35 | 19 | 0.49 |
| Yd | ng/ml | 2.0E-1 | 2.8E-1 | 3.1E-1 | 4.4E-1 | 4.0E-1 | 5.7E-1 | 6.6E-3 | 1.7E-2 | 1.8E0 | 2.3E0 | 47 | 20 | 37 | 20 | 0.59 |
| Wb | | 3.0E4 | 3.3E4 | 3.4E4 | 4.2E4 | 1.8E4 | 3.0E4 | 2.2E3 | 1.0E4 | 8.5E4 | 1.5E5 | 47 | 20 | 37 | 20 | 0.58 |
| Vz | pg/ml | 3.2E0 | 2.8E0 | 4.9E0 | 4.5E0 | 5.8E0 | 4.6E0 | 1.0E-9 | 8.3E-1 | 2.9E1 | 2.2E1 | 47 | 20 | 37 | 20 | 0.52 |
| Si | ng/ml | 8.0E-1 | 1.1E0 | 1.5E0 | 2.2E0 | 2.2E0 | 2.4E0 | 1.9E-2 | 3.6E-1 | 1.0E1 | 1.0E1 | 45 | 20 | 35 | 20 | 0.65 |
| Sf | mIU/mL | 1.2E1 | 2.0E1 | 5.4E1 | 3.4E1 | 1.2E2 | 4.2E1 | 8.1E-2 | 2.5E0 | 7.2E2 | 1.7E2 | 45 | 20 | 35 | 20 | 0.56 |
| Sh | mIU/mL | 1.3E1 | 1.4E1 | 5.2E1 | 5.4E1 | 1.2E2 | 1.0E2 | 2.9E-2 | 7.8E-2 | 5.9E2 | 3.7E2 | 45 | 20 | 35 | 20 | 0.55 |
| Sj | ng/ml | 4.4E-1 | 4.1E-1 | 4.2E-1 | 4.3E-1 | 8.5E-2 | 1.0E-1 | 2.5E-1 | 2.5E-1 | 6.1E-1 | 7.0E-1 | 45 | 20 | 35 | 20 | 0.53 |
| Rc | pg/ml | 5.2E3 | 7.6E3 | 6.3E3 | 8.1E3 | 4.4E3 | 5.6E3 | 1.9E2 | 2.4E2 | 2.2E4 | 2.7E4 | 111 | 46 | 84 | 46 | 0.60 |
| Rb | pg/ml | 7.6E-1 | 6.3E-1 | 2.5E0 | 3.3E0 | 3.6E0 | 8.8E0 | 1.0E-9 | 1.0E-9 | 1.6E1 | 5.6E1 | 111 | 46 | 84 | 46 | 0.48 |
| Zq | 2.6ng/ml | 1.5E2 | 4.4E2 | 2.0E2 | 4.8E2 | 1.5E2 | 3.0E2 | 8.3E0 | 4.8E1 | 5.2E2 | 9.7E2 | 44 | 20 | 34 | 20 | 0.79 |
| Zw | 2.5ng/ml | 3.6E0 | 1.0E1 | 1.0E1 | 1.7E1 | 1.5E1 | 2.0E1 | 6.3E-2 | 2.4E-1 | 5.9E1 | 6.3E1 | 47 | 20 | 37 | 20 | 0.60 |
| Zx | 2.3mU/ml | 1.0E-1 | 1.3E-1 | 3.0E-1 | 2.4E-1 | 5.9E-1 | 4.1E-1 | 4.1E-2 | 3.2E-2 | 3.0E0 | 1.9E0 | 47 | 20 | 37 | 20 | 0.53 |
| Pz | ng/ml | 3.3E3 | 5.9E3 | 7.5E3 | 6.4E3 | 1.9E4 | 5.7E3 | 1.3E1 | 4.7E1 | 2.8E5 | 3.9E4 | 314 | 76 | 134 | 76 | 0.56 |
| Qa | ng/ml | 2.8E3 | 6.3E3 | 6.2E3 | 1.1E4 | 8.3E3 | 2.6E4 | 1.5E2 | 2.3E2 | 5.2E4 | 2.2E5 | 314 | 76 | 134 | 76 | 0.65 |
| Qb | ng/ml | 1.0E2 | 1.2E2 | 2.6E2 | 2.5E2 | 6.8E2 | 4.9E2 | 7.9E-1 | 4.4E0 | 8.3E3 | 4.1E3 | 314 | 76 | 134 | 76 | 0.55 |
| Qc | ng/ml | 2.5E2 | 2.8E2 | 5.2E2 | 4.8E2 | 1.0E3 | 5.4E2 | 8.1E-1 | 3.0E0 | 1.1E4 | 2.8E3 | 314 | 76 | 134 | 76 | 0.53 |
| Qd | ng/ml | 9.5E3 | 1.2E4 | 2.8E4 | 2.8E4 | 1.3E5 | 4.3E4 | 2.4E2 | 6.9E2 | 2.0E6 | 2.3E5 | 314 | 76 | 134 | 76 | 0.58 |
| Qe | ng/ml | 7.8E2 | 1.7E3 | 2.0E3 | 2.4E3 | 5.9E3 | 2.8E3 | 7.6E0 | 4.7E1 | 9.7E4 | 1.8E4 | 314 | 76 | 134 | 76 | 0.63 |
| Jd | ng/ml | 3.6E-1 | 1.8E0 | 7.1E0 | 5.9E0 | 6.2E1 | 1.4E1 | 1.0E-9 | 1.0E-9 | 6.5E2 | 9.1E1 | 111 | 47 | 86 | 47 | 0.74 |
| Je | ng/ml | 1.0E-9 | 8.0E-1 | 1.4E0 | 3.3E0 | 5.6E0 | 6.9E0 | 1.0E-9 | 1.0E-9 | 5.6E1 | 4.5E1 | 111 | 47 | 86 | 47 | 0.64 |
| Jf | ng/ml | 1.0E-9 | 1.0E-9 | 8.1E-1 | 1.4E0 | 2.1E0 | 2.6E0 | 1.0E-9 | 1.0E-9 | 1.2E1 | 1.0E1 | 111 | 47 | 86 | 47 | 0.54 |
| Jg | ng/ml | 3.7E2 | 9.7E2 | 7.2E2 | 1.2E3 | 1.1E3 | 1.2E3 | 5.8E0 | 1.3E1 | 1.0E4 | 7.1E3 | 317 | 77 | 136 | 77 | 0.67 |
| Jh | ng/ml | 2.3E0 | 5.7E0 | 2.5E1 | 5.1E1 | 1.0E2 | 1.5E2 | 1.0E-9 | 1.0E-9 | 1.2E3 | 1.1E3 | 317 | 77 | 136 | 77 | 0.61 |
| Ji | ng/ml | 4.6E1 | 7.1E1 | 6.7E1 | 1.3E2 | 6.9E1 | 1.9E2 | 1.1E0 | 5.2E0 | 5.3E2 | 1.3E3 | 317 | 77 | 136 | 77 | 0.64 |
| Sr | pg/mL | 3.0E2 | 6.1E2 | 7.6E2 | 1.5E3 | 1.3E3 | 3.2E3 | 1.0E-9 | 1.0E-9 | 9.8E3 | 2.1E4 | 106 | 46 | 82 | 46 | 0.63 |
| Ss | pg/mL | 7.6E4 | 1.9E5 | 1.3E5 | 1.9E5 | 1.3E5 | 1.7E5 | 9.5E3 | 1.1E4 | 6.7E5 | 8.5E5 | 106 | 46 | 82 | 46 | 0.61 |
| St | pg/mL | 2.2E7 | 5.4E7 | 4.7E7 | 1.0E8 | 6.0E7 | 2.5E8 | 7.8E5 | 1.0E-9 | 4.1E8 | 1.7E9 | 108 | 45 | 82 | 45 | 0.62 |
| Wc | ng/ml | 1.0E-9 | 1.0E-9 | 5.2E-2 | 1.0E-1 | 1.5E-1 | 4.0E-1 | 1.0E-9 | 1.0E-9 | 9.8E-1 | 1.8E0 | 47 | 20 | 36 | 20 | 0.53 |
| Wd | ng/ml | 8.9E0 | 1.2E1 | 1.8E1 | 9.0E1 | 4.3E1 | 2.7E2 | 1.0E-9 | 1.5E0 | 2.9E2 | 1.2E3 | 47 | 20 | 36 | 20 | 0.61 |
| We | ng/ml | 3.5E-1 | 7.1E-1 | 6.9E-1 | 4.1E0 | 9.7E-1 | 7.9E0 | 1.0E-9 | 6.6E-2 | 3.9E0 | 2.3E1 | 47 | 20 | 36 | 20 | 0.65 |
| Wg | ng/ml | 1.0E-9 | 1.0E-9 | 1.0E-9 | 2.7E-2 | 0.0E0 | 1.2E-1 | 1.0E-9 | 1.0E-9 | 1.0E-9 | 5.3E-1 | 47 | 20 | 36 | 20 | 0.53 |
| Wh | ng/ml | 8.7E-3 | 1.8E-2 | 1.9E-2 | 2.9E-1 | 5.1E-2 | 1.0E0 | 1.0E-9 | 1.0E-9 | 3.5E-1 | 4.5E0 | 47 | 20 | 36 | 20 | 0.70 |
| Wf | ng/ml | 1.0E-9 | 1.0E-9 | 1.4E-1 | 2.1E-1 | 2.6E-1 | 5.2E-1 | 1.0E-9 | 1.0E-9 | 1.1E0 | 2.3E0 | 47 | 20 | 36 | 20 | 0.50 |
| Ra | pg/ml | 1.0E-9 | 1.0E-9 | 7.5E-1 | 1.8E0 | 1.4E0 | 9.5E0 | 1.0E-9 | 1.0E-9 | 7.3E0 | 6.4E1 | 111 | 46 | 84 | 46 | 0.45 |
| Qz | pg/ml | 1.1E1 | 1.1E1 | 6.9E1 | 3.1E1 | 1.1E2 | 4.9E1 | 1.0E-9 | 1.0E-9 | 7.1E2 | 2.2E2 | 111 | 46 | 84 | 46 | 0.45 |
| Qy | pg/ml | 4.1E-1 | 5.4E-1 | 2.9E0 | 2.5E1 | 1.5E1 | 8.5E1 | 1.0E-9 | 1.0E-9 | 1.6E2 | 4.3E2 | 111 | 46 | 84 | 46 | 0.57 |
| Qx | pg/ml | 1.0E-9 | 1.0E-9 | 6.4E0 | 4.5E0 | 5.1E1 | 1.7E1 | 1.0E-9 | 1.0E-9 | 5.4E2 | 1.1E2 | 111 | 46 | 84 | 46 | 0.51 |
| Qw | pg/ml | 1.8E-1 | 1.0E-9 | 1.4E0 | 2.3E0 | 3.7E0 | 8.7E0 | 1.0E-9 | 1.0E-9 | 3.0E1 | 5.6E1 | 111 | 46 | 84 | 46 | 0.45 |
| Qv | pg/ml | 2.3E4 | 1.0E4 | 3.7E4 | 2.2E4 | 7.7E4 | 2.4E4 | 1.2E3 | 4.0E2 | 7.4E5 | 1.2E5 | 111 | 46 | 84 | 46 | 0.37 |
| Qu | pg/ml | 5.1E0 | 2.8E1 | 7.9E1 | 9.3E1 | 1.7E2 | 1.6E2 | 1.0E-9 | 1.0E-9 | 8.0E2 | 7.0E2 | 111 | 46 | 84 | 46 | 0.58 |
| Qt | pg/ml | 1.2E1 | 1.9E1 | 3.0E1 | 7.1E1 | 5.9E1 | 1.6E2 | 1.0E-9 | 1.0E-9 | 3.8E2 | 1.0E3 | 111 | 46 | 84 | 46 | 0.59 |
| Qh | ng/ml | 1.5E1 | 2.3E1 | 3.7E1 | 4.2E1 | 7.2E1 | 5.7E1 | 1.2E-1 | 7.8E-1 | 6.4E2 | 3.4E2 | 111 | 46 | 84 | 46 | 0.59 |
| Qg | ng/ml | 8.9E0 | 7.1E0 | 2.6E1 | 1.5E1 | 1.0E2 | 3.2E1 | 1.5E-1 | 3.3E-1 | 1.0E3 | 2.0E2 | 111 | 46 | 84 | 46 | 0.42 |
| Jj | ng/ml | 8.4E2 | 6.0E2 | 2.9E3 | 1.2E3 | 2.0E4 | 2.0E3 | 2.0E1 | 1.2E1 | 3.4E5 | 1.2E4 | 317 | 77 | 136 | 77 | 0.41 |
| Jk | ng/ml | 3.3E0 | 4.7E0 | 2.4E1 | 3.1E1 | 5.0E1 | 6.1E1 | 1.0E-9 | 1.1E-1 | 2.8E2 | 3.9E2 | 317 | 77 | 136 | 77 | 0.55 |
| Jl | ng/ml | 3.7E-1 | 8.5E-1 | 1.9E0 | 1.3E2 | 4.7E0 | 1.1E3 | 7.6E-4 | 1.9E-3 | 3.2E1 | 9.9E3 | 317 | 77 | 136 | 77 | 0.61 |
| Jm | ng/ml | 1.9E1 | 2.7E1 | 5.1E1 | 6.6E1 | 9.4E1 | 1.1E2 | 1.0E-9 | 3.0E-1 | 1.0E3 | 6.1E2 | 317 | 77 | 136 | 77 | 0.53 |
| Jn | pg/ml | 3.8E-1 | 4.6E-1 | 1.9E0 | 1.9E1 | 7.0E0 | 1.1E2 | 1.0E-9 | 1.0E-9 | 6.2E1 | 7.3E2 | 317 | 77 | 136 | 77 | 0.56 |
| Jo | pg/ml | 4.0E3 | 4.3E3 | 5.0E3 | 7.0E3 | 3.7E3 | 1.2E4 | 4.2E1 | 2.3E2 | 2.0E4 | 1.0E5 | 317 | 77 | 136 | 77 | 0.53 |
| Jp | pg/ml | 6.6E4 | 8.2E4 | 7.0E4 | 8.3E4 | 3.4E4 | 3.4E4 | 2.1E3 | 3.1E3 | 2.1E5 | 2.1E5 | 317 | 77 | 136 | 77 | 0.63 |
| Jq | pg/ml | 9.2E1 | 1.2E2 | 1.4E2 | 3.5E2 | 1.6E2 | 1.1E3 | 2.6E0 | 1.1E1 | 1.1E3 | 8.7E3 | 317 | 77 | 136 | 77 | 0.58 |
| Jr | pg/ml | 3.8E0 | 8.3E0 | 1.8E1 | 1.8E2 | 6.6E1 | 1.0E3 | 1.0E-9 | 1.0E-9 | 7.9E2 | 7.4E3 | 317 | 77 | 136 | 77 | 0.59 |
| Js | pg/ml | 1.3E1 | 1.4E1 | 4.5E1 | 1.1E2 | 1.5E2 | 4.8E2 | 1.0E-9 | 4.5E-1 | 1.6E3 | 3.0E3 | 317 | 77 | 136 | 77 | 0.53 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jt | pg/ml | 2.4E3 | 3.1E3 | 3.0E3 | 4.5E3 | 2.1E3 | 6.4E3 | 1.5E2 | 2.3E2 | 1.2E4 | 5.2E4 | 317 | 77 | 136 | 77 | 0.59 |
| Xa | pg/ml | 1.0E-9 | 8.7E0 | 9.8E0 | 7.7E1 | 2.1E1 | 2.7E2 | 1.0E-9 | 1.0E-9 | 9.6E1 | 1.2E3 | 47 | 20 | 37 | 20 | 0.65 |
| Ye | pg/ml | 1.0E-9 | 1.0E-9 | 3.0E0 | 4.8E0 | 1.0E1 | 9.1E0 | 1.0E-9 | 1.0E-9 | 6.9E1 | 2.7E1 | 47 | 20 | 37 | 20 | 0.53 |
| Tm | pg/ml | 1.0E-9 | 1.0E-9 | 3.2E0 | 2.9E0 | 5.4E0 | 6.1E0 | 1.0E-9 | 1.0E-9 | 1.8E1 | 2.5E1 | 47 | 20 | 37 | 20 | 0.48 |
| Tl | pg/ml | 1.1E-1 | 1.3E-1 | 2.7E-1 | 1.5E0 | 3.8E-1 | 5.5E0 | 1.0E-9 | 1.0E-9 | 1.8E0 | 2.5E1 | 47 | 20 | 37 | 20 | 0.53 |
| Ju | mIU/ml | 7.2E0 | 1.1E1 | 2.2E1 | 1.7E1 | 3.6E1 | 1.9E1 | 6.5E-2 | 1.9E-1 | 2.3E2 | 9.3E1 | 111 | 47 | 86 | 47 | 0.56 |
| Jv | mIU/ml | 1.1E1 | 1.5E1 | 3.9E1 | 3.2E1 | 7.4E1 | 4.6E1 | 1.0E-2 | 5.0E-2 | 4.4E2 | 2.2E2 | 111 | 47 | 86 | 47 | 0.53 |
| Jy | ng/ml | 1.5E-3 | 1.8E-3 | 2.3E-3 | 3.5E-3 | 4.9E-3 | 6.5E-3 | 1.7E-4 | 4.5E-4 | 5.2E-2 | 4.1E-2 | 111 | 47 | 86 | 47 | 0.57 |
| Kc | pg/ml | 2.1E1 | 3.4E1 | 3.5E1 | 5.0E1 | 4.0E1 | 4.5E1 | 1.0E-9 | 1.0E-9 | 1.7E2 | 1.6E2 | 111 | 48 | 86 | 48 | 0.64 |
| Kd | pg/ml | 1.0E-9 | 1.0E-9 | 2.4E2 | 9.6E2 | 7.3E2 | 5.6E3 | 1.0E-9 | 1.0E-9 | 4.8E3 | 3.8E4 | 111 | 48 | 86 | 48 | 0.49 |
| Ke | pg/ml | 9.6E3 | 1.4E4 | 1.3E4 | 2.6E4 | 9.5E3 | 4.8E4 | 3.4E2 | 2.0E3 | 5.9E4 | 3.2E5 | 111 | 48 | 86 | 48 | 0.62 |
| Kf | pg/mL | 5.9E0 | 8.6E0 | 6.5E0 | 1.1E1 | 5.7E0 | 1.1E1 | 1.0E-9 | 1.0E-9 | 2.6E1 | 7.8E1 | 111 | 48 | 86 | 48 | 0.65 |
| Kg | pg/mL | 9.9E2 | 1.3E3 | 1.5E3 | 2.7E3 | 1.5E3 | 4.5E3 | 7.3E1 | 1.3E2 | 8.4E3 | 2.7E4 | 111 | 48 | 86 | 48 | 0.58 |
| Ki | pg/ml | 6.4E1 | 4.7E1 | 7.2E1 | 5.7E1 | 5.2E1 | 4.1E1 | 1.0E-9 | 1.0E-9 | 2.9E2 | 2.0E2 | 111 | 48 | 86 | 48 | 0.39 |
| Kj | pg/ml | 9.3E2 | 1.3E3 | 1.5E3 | 2.1E3 | 1.7E3 | 2.6E3 | 1.4E1 | 3.3E1 | 1.0E4 | 1.5E4 | 111 | 48 | 86 | 48 | 0.57 |
| Kk | pg/ml | 6.9E0 | 6.8E0 | 1.1E1 | 1.3E1 | 1.8E1 | 1.5E1 | 1.0E-9 | 1.0E-9 | 1.6E2 | 6.1E1 | 111 | 48 | 86 | 48 | 0.51 |
| Kl | pg/ml | 1.8E4 | 2.9E4 | 2.5E4 | 3.4E4 | 2.2E4 | 2.7E4 | 1.6E2 | 1.6E3 | 1.1E5 | 1.3E5 | 111 | 48 | 86 | 48 | 0.61 |
| Kn | pg/ml | 1.5E1 | 3.0E1 | 5.8E1 | 1.7E2 | 1.1E2 | 7.0E2 | 1.0E-9 | 1.0E-9 | 7.3E2 | 4.9E3 | 111 | 48 | 86 | 48 | 0.60 |
| Ko | pg/ml | 3.0E2 | 5.3E2 | 3.9E2 | 7.6E2 | 4.0E2 | 8.5E2 | 1.0E-9 | 1.0E-9 | 1.8E3 | 4.1E3 | 111 | 48 | 86 | 48 | 0.66 |
| Kp | pg/ml | 3.2E2 | 3.4E2 | 3.4E2 | 6.5E2 | 3.0E2 | 1.9E3 | 1.0E-9 | 3.6E0 | 1.7E3 | 1.3E4 | 111 | 48 | 86 | 48 | 0.57 |
| Kq | pg/ml | 2.8E2 | 4.7E2 | 4.2E2 | 4.2E3 | 9.7E2 | 2.3E4 | 5.1E0 | 8.8E1 | 9.8E3 | 1.6E5 | 106 | 48 | 82 | 48 | 0.69 |
| Kr | pg/ml | 5.0E-1 | 2.9E-1 | 2.5E0 | 1.1E1 | 4.9E0 | 6.0E1 | 1.0E-9 | 1.0E-9 | 3.5E1 | 4.2E2 | 106 | 48 | 82 | 48 | 0.49 |
| Ks | pg/ml | 1.5E4 | 1.7E4 | 2.1E4 | 2.1E4 | 2.0E4 | 1.8E4 | 3.8E2 | 6.8E2 | 1.1E5 | 6.3E4 | 106 | 48 | 82 | 48 | 0.51 |
| Ps | ng/ml | 1.4E2 | 2.9E2 | 4.3E2 | 6.1E2 | 1.2E3 | 8.6E2 | 6.9E0 | 6.6E1 | 8.3E3 | 3.8E3 | 45 | 20 | 34 | 20 | 0.69 |
| Kx | ng/ml | 1.0E-9 | 3.4E-3 | 4.6E-3 | 1.2E-2 | 8.6E-3 | 2.0E-2 | 1.0E-9 | 1.0E-9 | 5.1E-2 | 9.5E-2 | 110 | 48 | 86 | 48 | 0.62 |
| Ky | ng/ml | 1.0E-1 | 2.0E-1 | 3.5E-1 | 5.3E-1 | 7.1E-1 | 7.7E-1 | 1.0E-9 | 1.0E-9 | 5.1E0 | 3.7E0 | 110 | 48 | 86 | 48 | 0.62 |
| Kz | ng/ml | 1.0E-9 | 1.7E-3 | 3.7E-3 | 5.1E-3 | 6.3E-3 | 6.1E-3 | 1.0E-9 | 1.0E-9 | 3.6E-2 | 1.8E-2 | 110 | 48 | 86 | 48 | 0.58 |
| Rz | ng/ml | 1.4E-1 | 3.9E-1 | 6.0E-1 | 1.3E0 | 1.0E0 | 2.0E0 | 3.6E-3 | 1.7E-2 | 4.4E0 | 6.5E0 | 45 | 20 | 35 | 20 | 0.66 |
| Ry | ng/ml | 1.6E-2 | 2.0E-2 | 1.8E-2 | 3.8E-2 | 2.0E-2 | 7.6E-2 | 1.0E-9 | 1.0E-9 | 1.0E-1 | 3.5E-1 | 45 | 20 | 35 | 20 | 0.58 |
| Rx | ng/ml | 1.0E-9 | 1.8E-5 | 2.6E-3 | 1.2E-3 | 4.4E-3 | 1.9E-3 | 1.0E-9 | 1.0E-9 | 2.0E-2 | 6.1E-3 | 45 | 20 | 35 | 20 | 0.47 |
| Ld | pg/ml | 1.0E-9 | 1.0E-9 | 4.0E0 | 3.7E0 | 9.9E0 | 5.9E0 | 1.0E-9 | 1.0E-9 | 6.9E1 | 2.3E1 | 108 | 49 | 85 | 49 | 0.54 |
| Lh | pg/ml | 1.1E4 | 2.2E4 | 2.0E4 | 3.7E4 | 2.9E4 | 6.4E4 | 1.0E-9 | 1.1E2 | 2.6E5 | 4.1E5 | 315 | 77 | 136 | 77 | 0.65 |
| Li | pg/ml | 2.6E3 | 5.7E3 | 8.5E3 | 2.6E4 | 2.3E4 | 5.3E4 | 1.0E-9 | 3.7E1 | 2.9E5 | 3.1E5 | 315 | 77 | 136 | 77 | 0.65 |
| Lj | pg/ml | 1.8E3 | 4.8E3 | 1.1E4 | 2.7E4 | 4.2E4 | 6.7E4 | 1.4E1 | 3.4E1 | 4.4E5 | 3.9E5 | 315 | 77 | 136 | 77 | 0.62 |
| Lp | pg/ml | 9.4E0 | 1.4E1 | 3.1E1 | 1.3E2 | 5.7E1 | 2.6E2 | 1.0E-9 | 1.0E-9 | 2.4E2 | 1.0E3 | 45 | 20 | 35 | 20 | 0.54 |
| Lt | pg/ml | 1.0E-9 | 1.0E-9 | 2.6E0 | 1.0E-9 | 1.0E1 | 0.0E0 | 1.0E-9 | 1.0E-9 | 6.0E1 | 1.0E-9 | 45 | 20 | 35 | 20 | 0.46 |
| Rv | ng/ml | 5.0E-4 | 8.4E-4 | 8.5E-4 | 2.8E-3 | 1.1E-3 | 4.6E-3 | 1.0E-9 | 1.0E-9 | 5.9E-3 | 1.6E-2 | 45 | 20 | 34 | 20 | 0.60 |
| Ru | ng/ml | 1.0E-9 | 1.0E-9 | 9.6E-3 | 3.9E-2 | 4.9E-2 | 1.1E-1 | 1.0E-9 | 1.0E-9 | 3.1E-1 | 3.6E-1 | 45 | 20 | 34 | 20 | 0.55 |
| Rt | ng/ml | 6.8E-2 | 1.0E-1 | 9.0E-2 | 5.1E-1 | 1.1E-1 | 1.6E0 | 1.6E-3 | 1.3E-3 | 4.5E-1 | 7.4E0 | 45 | 20 | 34 | 20 | 0.62 |
| Yl | pg/ml | 1.1E1 | 1.2E1 | 1.8E1 | 3.1E1 | 1.9E1 | 4.8E1 | 1.0E-9 | 1.0E-9 | 1.1E2 | 2.2E2 | 47 | 20 | 37 | 20 | 0.58 |
| Rm | ng/ml | 1.7E1 | 2.1E1 | 5.8E1 | 5.6E1 | 8.8E1 | 6.8E1 | 2.2E-1 | 3.9E-1 | 4.0E2 | 3.2E2 | 110 | 45 | 83 | 45 | 0.55 |
| Rh | ng/ml | 1.4E2 | 1.7E2 | 2.9E2 | 6.7E2 | 5.7E2 | 2.6E3 | 4.7E0 | 7.6E0 | 3.8E3 | 1.7E4 | 110 | 45 | 83 | 45 | 0.55 |
| Ri | ng/ml | 1.0E-9 | 1.0E-9 | 3.9E0 | 1.7E0 | 9.2E0 | 4.4E0 | 1.0E-9 | 1.0E-9 | 7.4E1 | 2.5E1 | 111 | 45 | 84 | 45 | 0.42 |
| Rg | ng/ml | 1.0E-9 | 1.0E-9 | 2.7E-2 | 1.1E-1 | 2.6E-1 | 4.6E-1 | 1.0E-9 | 1.0E-9 | 2.7E0 | 3.0E0 | 110 | 45 | 83 | 45 | 0.54 |
| Rj | ng/ml | 1.0E-9 | 1.0E-9 | 1.7E0 | 6.7E0 | 7.9E0 | 4.0E1 | 1.0E-9 | 1.0E-9 | 8.0E1 | 2.7E2 | 111 | 45 | 84 | 45 | 0.50 |
| Rf | ng/ml | 3.6E-1 | 5.0E-1 | 8.3E-1 | 1.3E0 | 1.6E0 | 3.1E0 | 7.8E-3 | 3.6E-2 | 1.4E1 | 1.7E1 | 110 | 45 | 83 | 45 | 0.56 |
| Ql | pg/ml | 7.3E0 | 7.3E0 | 1.4E1 | 1.8E1 | 3.1E1 | 3.4E1 | 1.0E-9 | 1.0E-9 | 2.9E2 | 1.8E2 | 111 | 47 | 86 | 47 | 0.48 |
| Qm | pg/ml | 1.7E0 | 1.7E1 | 1.9E1 | 2.8E1 | 4.4E1 | 3.3E1 | 1.0E-9 | 1.0E-9 | 3.6E2 | 1.3E2 | 111 | 47 | 86 | 47 | 0.63 |
| Qn | pg/ml | 6.1E-1 | 1.0E0 | 7.5E0 | 5.6E0 | 2.6E1 | 1.1E1 | 1.0E-9 | 1.0E-9 | 2.2E2 | 6.0E1 | 111 | 47 | 86 | 47 | 0.54 |
| Nv | pg/ml | 3.5E3 | 5.2E3 | 1.3E4 | 1.5E4 | 6.3E4 | 2.5E4 | 1.0E-9 | 3.4E1 | 1.1E6 | 1.6E5 | 318 | 79 | 136 | 79 | 0.61 |
| Nw | pg/ml | 7.4E3 | 1.3E4 | 1.2E4 | 2.0E4 | 2.2E4 | 3.4E4 | 8.6E1 | 5.7E2 | 2.1E5 | 2.2E5 | 318 | 79 | 136 | 79 | 0.65 |
| Nx | pg/ml | 1.7E2 | 2.6E2 | 3.9E2 | 5.5E2 | 7.1E2 | 7.7E2 | 1.0E-9 | 1.0E-9 | 7.4E3 | 4.1E3 | 318 | 79 | 136 | 79 | 0.60 |
| Ny | pg/ml | 4.7E0 | 1.2E1 | 1.1E2 | 8.8E1 | 1.4E3 | 3.5E2 | 1.0E-9 | 1.0E-9 | 2.5E4 | 2.8E3 | 318 | 79 | 136 | 79 | 0.62 |
| Oa | pg/ml | 1.6E2 | 2.5E2 | 4.4E2 | 5.1E2 | 8.0E2 | 6.1E2 | 1.0E-9 | 1.0E-9 | 4.8E3 | 2.4E3 | 111 | 47 | 86 | 47 | 0.58 |
| Op | pg/ml | 3.3E5 | 4.9E5 | 3.7E5 | 4.8E5 | 1.6E5 | 1.5E5 | 3.3E4 | 9.4E4 | 7.3E5 | 7.5E5 | 45 | 20 | 35 | 20 | 0.71 |
| Wn | ng/ml | 1.2E1 | 1.4E1 | 9.7E1 | 2.7E1 | 3.1E2 | 2.9E1 | 2.5E0 | 2.7E0 | 1.8E3 | 1.0E2 | 33 | 11 | 27 | 11 | 0.52 |
| Tk | ng/ml | 2.0E2 | 1.0E2 | 4.3E2 | 3.1E2 | 7.4E2 | 5.1E2 | 2.4E1 | 1.0E1 | 4.2E3 | 1.4E3 | 36 | 13 | 29 | 13 | 0.41 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oe | pg/ml | 9.7E1 | 6.6E1 | 2.7E2 | 3.2E2 | 4.2E2 | 5.5E2 | 1.0E-9 | 1.0E-9 | 2.7E3 | 2.3E3 | 314 | 79 | 136 | 79 | 0.50 |
| Of | pg/ml | 2.1E2 | 4.8E2 | 5.6E3 | 1.2E4 | 1.8E4 | 3.0E4 | 1.0E-9 | 1.0E-9 | 1.8E5 | 1.7E5 | 317 | 79 | 136 | 79 | 0.53 |
| Og | pg/ml | 9.4E-2 | 8.3E-2 | 7.2E-1 | 1.3E0 | 2.2E0 | 8.1E0 | 1.0E-9 | 1.0E-9 | 2.0E1 | 7.2E1 | 317 | 79 | 136 | 79 | 0.43 |
| Oh | pg/ml | 2.0E0 | 4.2E0 | 2.5E1 | 3.0E1 | 1.2E2 | 1.3E2 | 1.0E-9 | 1.0E-9 | 1.4E3 | 1.1E3 | 317 | 79 | 136 | 79 | 0.63 |
| Oi | pg/ml | 2.9E0 | 2.6E0 | 7.2E0 | 6.7E0 | 1.1E1 | 8.6E0 | 1.0E-9 | 1.0E-9 | 8.6E1 | 4.8E1 | 317 | 79 | 136 | 79 | 0.51 |
| Ok | pg/ml | 3.2E2 | 6.0E2 | 4.3E2 | 9.2E2 | 3.9E2 | 1.2E3 | 1.3E1 | 2.9E1 | 3.1E3 | 7.8E3 | 317 | 79 | 136 | 79 | 0.68 |
| Om | pg/ml | 3.6E2 | 5.5E2 | 7.6E2 | 2.0E3 | 2.1E3 | 6.2E3 | 1.0E-9 | 1.0E-9 | 3.0E4 | 5.1E4 | 317 | 79 | 136 | 79 | 0.63 |
| On | pg/ml | 1.4E2 | 2.7E2 | 2.8E2 | 5.7E2 | 4.8E2 | 1.1E3 | 8.4E-1 | 1.7E1 | 4.5E3 | 8.5E3 | 317 | 79 | 136 | 79 | 0.66 |
| Or | pg/ml | 1.0E1 | 2.2E1 | 3.1E1 | 5.7E1 | 6.4E1 | 1.1E2 | 1.0E-9 | 1.0E-9 | 5.0E2 | 5.1E2 | 110 | 49 | 86 | 49 | 0.55 |
| Ow | pg/ml | 2.8E1 | 5.5E1 | 1.0E2 | 2.8E2 | 3.0E2 | 7.9E2 | 1.0E-9 | 1.3E0 | 2.3E3 | 4.7E3 | 110 | 49 | 86 | 49 | 0.67 |
| Ou | pg/ml | 4.4E2 | 7.4E2 | 8.4E2 | 1.7E3 | 1.2E3 | 2.5E3 | 1.0E-9 | 5.4E1 | 9.4E3 | 1.1E4 | 110 | 49 | 86 | 49 | 0.63 |
| Ul | ng/ml | 1.0E-9 | 1.0E-9 | 1.1E0 | 3.3E0 | 3.7E0 | 1.2E1 | 1.0E-9 | 1.0E-9 | 2.2E1 | 5.6E1 | 119 | 46 | 88 | 46 | 0.50 |
| Uo | ng/ml | 1.0E-9 | 1.0E-9 | 1.1E-1 | 7.7E-2 | 2.4E-1 | 1.8E-1 | 1.0E-9 | 1.0E-9 | 1.3E0 | 6.8E-1 | 119 | 46 | 88 | 46 | 0.49 |
| Uk | ng/ml | 1.0E-9 | 1.0E-9 | 4.8E-3 | 8.9E-3 | 1.2E-2 | 2.4E-2 | 1.0E-9 | 1.0E-9 | 9.9E-2 | 1.4E-1 | 119 | 46 | 88 | 46 | 0.49 |
| Um | ng/ml | 1.0E-9 | 1.0E-9 | 3.8E-1 | 4.1E-1 | 9.8E-1 | 7.8E-1 | 1.0E-9 | 1.0E-9 | 6.8E0 | 2.7E0 | 119 | 46 | 88 | 46 | 0.51 |
| Uf | ng/ml | 4.5E-2 | 9.8E-2 | 9.4E-2 | 3.2E-1 | 1.2E-1 | 8.5E-1 | 2.8E-3 | 6.6E-3 | 6.6E-1 | 5.6E0 | 119 | 46 | 88 | 46 | 0.68 |
| Uh | ng/ml | 1.8E0 | 3.2E0 | 2.5E0 | 4.7E0 | 2.3E0 | 4.5E0 | 3.2E-2 | 1.3E-1 | 1.1E1 | 1.8E1 | 119 | 46 | 88 | 46 | 0.67 |
| Un | ng/ml | 1.6E0 | 2.5E0 | 1.9E0 | 3.1E0 | 1.2E0 | 3.6E0 | 2.0E-1 | 3.4E-1 | 7.0E0 | 2.5E1 | 119 | 46 | 88 | 46 | 0.68 |
| Ug | ng/ml | 1.4E1 | 1.3E1 | 2.7E1 | 3.2E1 | 2.7E1 | 3.9E1 | 6.9E-1 | 1.2E0 | 1.3E2 | 1.6E2 | 119 | 46 | 88 | 46 | 0.49 |
| Ur | ng/ml | 1.6E-1 | 7.6E-2 | 1.2E0 | 7.0E-1 | 8.6E0 | 1.6E0 | 1.0E-9 | 1.0E-9 | 9.3E1 | 7.3E0 | 119 | 46 | 88 | 46 | 0.45 |
| Up | ng/ml | 1.0E-9 | 1.0E-9 | 7.5E-3 | 5.3E-2 | 3.4E-2 | 3.5E-1 | 1.0E-9 | 1.0E-9 | 3.3E-1 | 2.4E0 | 119 | 46 | 88 | 46 | 0.49 |
| Us | ng/ml | 4.4E-3 | 1.7E-3 | 2.1E-2 | 5.0E-2 | 5.6E-2 | 2.4E-1 | 1.0E-9 | 1.0E-9 | 4.0E-1 | 1.7E0 | 119 | 46 | 88 | 46 | 0.46 |
| Uv | ng/ml | 3.2E-3 | 2.9E-3 | 1.2E-2 | 1.7E-2 | 3.1E-2 | 6.0E-2 | 1.0E-9 | 1.0E-9 | 2.3E-1 | 4.1E-1 | 119 | 46 | 88 | 46 | 0.50 |
| Ut | ng/ml | 5.3E-1 | 1.3E0 | 2.3E0 | 5.8E0 | 8.9E0 | 1.3E1 | 1.0E-9 | 1.0E-9 | 7.2E1 | 6.5E1 | 119 | 46 | 88 | 46 | 0.65 |
| Uu | ng/ml | 6.9E0 | 8.0E0 | 7.8E0 | 9.1E0 | 5.1E0 | 6.7E0 | 8.1E-1 | 1.2E0 | 2.6E1 | 4.0E1 | 119 | 46 | 88 | 46 | 0.56 |
| Uw | ng/ml | 1.8E0 | 2.4E0 | 2.9E0 | 5.0E0 | 5.2E0 | 8.4E0 | 1.0E-9 | 3.7E-1 | 3.7E1 | 3.9E1 | 53 | 20 | 42 | 20 | 0.63 |
| Vb | ng/ml | 1.0E0 | 1.1E0 | 1.0E0 | 1.3E0 | 4.2E-1 | 1.3E0 | 2.1E-1 | 2.6E-1 | 2.5E0 | 6.4E0 | 53 | 20 | 42 | 20 | 0.50 |
| Vc | ng/ml | 1.0E-9 | 1.0E-9 | 2.3E-3 | 1.0E-9 | 1.5E-2 | 0.0E0 | 1.0E-9 | 1.0E-9 | 1.1E-1 | 1.0E-9 | 53 | 20 | 42 | 20 | 0.47 |
| Uy | ng/ml | 1.0E0 | 9.0E-1 | 2.9E0 | 5.2E0 | 6.6E0 | 1.3E1 | 5.3E-2 | 2.0E-2 | 3.5E1 | 4.6E1 | 53 | 20 | 42 | 20 | 0.50 |
| Uz | ng/ml | 1.0E-9 | 1.0E-9 | 8.3E-3 | 1.7E0 | 6.0E-2 | 7.4E0 | 1.0E-9 | 1.0E-9 | 4.4E-1 | 3.3E1 | 53 | 20 | 42 | 20 | 0.51 |
| Ux | ng/ml | 1.2E2 | 2.0E2 | 1.6E2 | 2.1E2 | 1.3E2 | 1.2E2 | 5.8E0 | 3.2E1 | 4.6E2 | 4.7E2 | 53 | 20 | 42 | 20 | 0.64 |
| Va | ng/ml | 1.6E1 | 2.9E1 | 2.3E1 | 2.9E1 | 2.5E1 | 2.5E1 | 3.1E-1 | 1.2E0 | 1.2E2 | 7.8E1 | 53 | 20 | 42 | 20 | 0.58 |
| Vh | ng/ml | 4.4E-3 | 2.0E-2 | 1.1E-2 | 6.9E-2 | 1.9E-2 | 1.9E-1 | 1.0E-9 | 2.2E-3 | 1.2E-1 | 8.6E-1 | 53 | 20 | 42 | 20 | 0.81 |
| Vi | ng/ml | 2.4E-3 | 6.3E-3 | 2.6E-1 | 1.1E-1 | 1.9E0 | 4.0E-1 | 1.0E-9 | 2.8E-4 | 1.4E1 | 1.8E0 | 53 | 20 | 42 | 20 | 0.67 |
| Vj | ng/ml | 2.2E1 | 5.7E1 | 1.8E2 | 1.1E2 | 7.4E2 | 1.5E2 | 3.2E0 | 8.0E0 | 5.2E3 | 6.5E2 | 53 | 19 | 42 | 19 | 0.68 |
| Vp | ng/ml | 1.0E-9 | 1.0E-9 | 7.4E-1 | 1.1E0 | 5.2E0 | 7.2E0 | 1.0E-9 | 1.0E-9 | 5.0E1 | 4.9E1 | 119 | 46 | 88 | 46 | 0.51 |
| Vt | ng/ml | 6.1E0 | 8.0E0 | 7.6E0 | 1.3E1 | 6.1E0 | 2.3E1 | 6.0E-1 | 4.3E-1 | 3.2E1 | 1.6E2 | 119 | 46 | 88 | 46 | 0.59 |
| Vu | ng/ml | 1.0E-9 | 6.1E-1 | 2.3E0 | 4.5E0 | 6.0E0 | 1.1E1 | 1.0E-9 | 1.0E-9 | 5.1E1 | 7.1E1 | 118 | 44 | 88 | 44 | 0.57 |
| Vq | ng/ml | 1.2E2 | 3.1E2 | 5.5E2 | 4.6E2 | 1.2E3 | 4.5E2 | 2.0E-1 | 3.6E0 | 1.0E4 | 1.4E3 | 94 | 35 | 72 | 35 | 0.59 |
| Vo | ng/ml | 2.6E1 | 2.6E1 | 2.5E1 | 2.5E1 | 4.9E0 | 5.0E0 | 2.5E0 | 1.1E1 | 3.5E1 | 3.5E1 | 119 | 46 | 88 | 46 | 0.49 |
| Vs | ng/ml | 1.0E-9 | 2.7E-1 | 6.5E0 | 1.6E1 | 2.7E1 | 7.1E1 | 1.0E-9 | 1.0E-9 | 2.3E2 | 4.5E2 | 116 | 41 | 86 | 41 | 0.54 |
| Vv | ng/ml | 2.7E0 | 4.6E0 | 6.0E0 | 7.2E0 | 1.0E1 | 7.9E0 | 1.0E-9 | 1.0E-9 | 8.1E1 | 3.2E1 | 118 | 45 | 88 | 45 | 0.59 |
| Vw | ng/ml | 3.3E1 | 4.0E1 | 3.1E1 | 4.0E1 | 1.7E1 | 1.5E1 | 2.5E0 | 1.1E1 | 6.7E1 | 6.6E1 | 53 | 20 | 42 | 20 | 0.64 |
| Oy | pg/ml | 5.5E-1 | 9.2E-1 | 8.7E0 | 5.1E0 | 4.2E1 | 1.1E1 | 1.0E-9 | 1.0E-9 | 4.0E2 | 6.5E1 | 317 | 79 | 136 | 79 | 0.55 |
| Oz | pg/ml | 4.5E-3 | 1.1E-1 | 2.2E-1 | 6.4E-1 | 3.7E-1 | 3.1E0 | 1.0E-9 | 1.0E-9 | 2.6E0 | 2.8E1 | 317 | 79 | 136 | 79 | 0.55 |
| Pa | pg/ml | 3.4E-1 | 4.5E-1 | 1.3E0 | 4.1E0 | 5.8E0 | 2.5E1 | 1.0E-9 | 1.0E-9 | 8.6E1 | 2.3E2 | 317 | 79 | 136 | 79 | 0.58 |
| Pb | pg/ml | 1.0E-9 | 1.0E-9 | 1.8E0 | 8.5E-1 | 2.7E1 | 4.7E0 | 1.0E-9 | 1.0E-9 | 4.9E2 | 3.2E1 | 317 | 79 | 136 | 79 | 0.50 |
| Pc | pg/ml | 4.4E-2 | 2.1E-1 | 4.3E-1 | 9.0E-1 | 1.3E0 | 4.2E0 | 1.0E-9 | 1.0E-9 | 1.6E1 | 3.8E1 | 317 | 79 | 136 | 79 | 0.54 |
| Pd | pg/ml | 1.8E0 | 3.0E0 | 3.8E0 | 8.0E0 | 8.2E0 | 1.6E1 | 1.0E-9 | 1.0E-9 | 9.4E1 | 1.2E2 | 317 | 79 | 136 | 79 | 0.61 |
| Pe | pg/ml | 1.8E1 | 3.9E1 | 8.9E1 | 4.0E2 | 3.5E2 | 1.8E3 | 1.0E-9 | 1.0E-9 | 4.7E3 | 1.5E4 | 317 | 79 | 136 | 79 | 0.64 |
| Pf | pg/ml | 1.2E0 | 3.0E0 | 6.2E0 | 2.1E1 | 2.6E1 | 5.8E1 | 1.0E-9 | 1.0E-9 | 3.3E2 | 4.3E2 | 317 | 79 | 136 | 79 | 0.64 |
| Pg | pg/ml | 3.2E0 | 4.9E0 | 4.0E1 | 5.3E1 | 2.1E2 | 1.7E2 | 1.0E-9 | 1.0E-9 | 3.2E3 | 1.2E3 | 317 | 79 | 136 | 79 | 0.59 |
| Ph | ng/ml | 1.4E-1 | 2.5E-1 | 2.7E-1 | 4.5E-1 | 3.5E-1 | 8.3E-1 | 1.0E-9 | 1.0E-9 | 2.2E0 | 5.4E0 | 110 | 49 | 86 | 49 | 0.58 |
| Pi | ng/ml | 1.9E-1 | 2.4E-1 | 2.8E-1 | 2.0E0 | 4.4E-1 | 1.2E1 | 1.0E-9 | 1.0E-9 | 3.2E0 | 8.2E1 | 110 | 49 | 86 | 49 | 0.57 |
| Pj | ng/mL | 4.4E0 | 7.6E0 | 5.1E0 | 7.9E0 | 3.3E0 | 5.4E0 | 3.8E-2 | 5.0E-1 | 1.6E1 | 3.1E1 | 110 | 49 | 86 | 49 | 0.68 |
| Pk | ng/ml | 8.1E-3 | 1.2E-2 | 1.2E-2 | 4.9E-2 | 1.2E-2 | 2.2E-1 | 1.0E-9 | 1.0E-9 | 5.9E-2 | 1.5E0 | 110 | 49 | 86 | 49 | 0.58 |
| aA | mg/dL | 8.0E-1 | 9.2E-1 | 9.2E-1 | 1.2E0 | 4.3E-1 | 8.3E-1 | 3.0E-1 | 3.0E-1 | 4.2E0 | 4.7E0 | 1242 | 101 | 226 | 101 | 0.56 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aC | mg/mL | 3.1E0 | 2.2E0 | 3.3E0 | 2.5E0 | 1.4E0 | 9.8E-1 | 1.1E0 | 8.5E-1 | 8.2E0 | 5.6E0 | 221 | 52 | 91 | 52 | 0.32 |
| aD | ug/mL | 2.9E0 | 4.0E0 | 4.1E0 | 5.3E0 | 3.2E0 | 3.8E0 | 8.5E-1 | 7.7E-1 | 2.8E1 | 1.9E1 | 221 | 52 | 91 | 52 | 0.60 |
| aE | mg/mL | 5.8E-1 | 5.5E-1 | 5.8E-1 | 5.8E-1 | 1.5E-1 | 1.5E-1 | 2.1E-1 | 3.7E-1 | 1.1E0 | 1.2E0 | 221 | 52 | 91 | 52 | 0.49 |
| aF | ng/mL | 2.1E0 | 2.3E0 | 4.4E0 | 3.9E0 | 7.0E0 | 3.9E0 | 4.3E-3 | 5.2E-1 | 5.0E1 | 1.9E1 | 221 | 52 | 91 | 52 | 0.53 |
| aG | mg/mL | 1.3E-1 | 1.3E-1 | 1.5E-1 | 1.5E-1 | 7.8E-2 | 8.6E-2 | 5.0E-2 | 4.3E-2 | 5.0E-1 | 4.2E-1 | 221 | 52 | 91 | 52 | 0.46 |
| aH | ug/mL | 6.8E1 | 7.3E1 | 7.8E1 | 7.9E1 | 3.5E1 | 4.9E1 | 1.5E1 | 1.1E1 | 2.7E2 | 2.9E2 | 221 | 52 | 91 | 52 | 0.48 |
| aI | ug/mL | 1.8E2 | 1.7E2 | 1.9E2 | 1.7E2 | 6.0E1 | 5.6E1 | 5.8E1 | 4.7E1 | 3.7E2 | 3.0E2 | 221 | 52 | 91 | 52 | 0.43 |
| aJ | ug/mL | 2.5E0 | 2.5E0 | 3.0E0 | 3.8E0 | 1.9E0 | 3.2E0 | 9.0E-1 | 1.1E0 | 1.2E1 | 1.7E1 | 221 | 52 | 91 | 52 | 0.55 |
| aK | ng/mL | 1.8E0 | 1.2E0 | 2.7E0 | 2.4E0 | 2.7E0 | 3.2E0 | 8.4E-2 | 2.9E-4 | 1.8E1 | 1.8E1 | 221 | 52 | 91 | 52 | 0.41 |
| aL | mg/mL | 8.1E-1 | 7.7E-1 | 8.3E-1 | 7.7E-1 | 2.4E-1 | 2.2E-1 | 2.2E-1 | 2.7E-1 | 1.6E0 | 1.6E0 | 221 | 52 | 91 | 52 | 0.43 |
| aM | U/mL | 1.9E1 | 3.7E1 | 3.7E1 | 6.7E1 | 1.1E2 | 1.2E2 | 4.2E-2 | 4.2E-2 | 1.6E3 | 8.2E2 | 221 | 52 | 91 | 52 | 0.65 |
| aN | U/mL | 1.0E1 | 1.5E1 | 1.8E1 | 2.5E1 | 2.1E1 | 2.7E1 | 2.5E-3 | 2.5E-3 | 1.3E2 | 1.1E2 | 221 | 52 | 91 | 52 | 0.60 |
| aO | pg/mL | 3.9E1 | 5.8E1 | 3.7E2 | 3.2E2 | 9.9E2 | 6.0E2 | 6.0E-2 | 6.0E-2 | 6.6E3 | 2.4E3 | 221 | 52 | 91 | 52 | 0.55 |
| aP | ng/mL | 1.7E0 | 1.7E0 | 1.9E0 | 2.3E0 | 1.1E0 | 1.5E0 | 5.4E-1 | 8.0E-1 | 6.6E0 | 6.6E0 | 221 | 52 | 91 | 52 | 0.55 |
| aQ | ng/mL | 3.2E-1 | 2.5E-1 | 5.0E-1 | 3.8E-1 | 5.2E-1 | 4.0E-1 | 1.9E-2 | 2.0E-4 | 4.0E0 | 2.5E0 | 221 | 52 | 91 | 52 | 0.42 |
| aR | ng/mL | 1.6E0 | 2.4E0 | 2.4E0 | 3.9E0 | 2.5E0 | 5.3E0 | 1.8E-1 | 5.6E-1 | 2.1E1 | 3.4E1 | 221 | 52 | 91 | 52 | 0.64 |
| aS | ng/mL | 2.4E-1 | 3.0E-1 | 7.8E-1 | 6.6E-1 | 2.5E0 | 7.5E-1 | 4.2E-3 | 6.0E-2 | 3.3E1 | 3.1E0 | 221 | 52 | 91 | 52 | 0.58 |
| aU | pg/mL | 8.8E1 | 6.4E1 | 1.4E2 | 1.1E2 | 1.6E2 | 1.4E2 | 7.4E0 | 7.4E-2 | 1.3E3 | 8.5E2 | 221 | 52 | 91 | 52 | 0.40 |
| aV | ng/mL | 7.3E-1 | 4.9E-1 | 1.1E0 | 9.4E-1 | 1.1E0 | 1.8E0 | 3.1E-2 | 7.6E-4 | 8.7E0 | 1.3E1 | 221 | 52 | 91 | 52 | 0.38 |
| aW | pg/mL | 1.7E1 | 2.2E1 | 2.0E1 | 3.0E1 | 2.6E1 | 5.5E1 | 7.2E-2 | 7.2E-2 | 2.4E2 | 4.2E2 | 221 | 52 | 91 | 52 | 0.63 |
| aX | ng/mL | 1.0E1 | 8.2E0 | 1.3E1 | 1.5E1 | 1.2E1 | 2.0E1 | 3.0E-1 | 6.2E-1 | 6.7E1 | 1.3E2 | 221 | 52 | 91 | 52 | 0.48 |
| aY | pg/mL | 5.0E1 | 6.6E1 | 7.2E1 | 8.2E1 | 7.1E1 | 6.0E1 | 4.1E-1 | 4.1E-1 | 4.4E2 | 3.4E2 | 221 | 52 | 91 | 52 | 0.59 |
| aZ | pg/mL | 2.2E2 | 2.4E2 | 4.8E2 | 6.0E2 | 7.2E2 | 1.3E3 | 1.7E0 | 1.7E0 | 5.4E3 | 8.3E3 | 221 | 52 | 91 | 52 | 0.51 |
| bA | ng/mL | 8.0E0 | 1.3E1 | 2.6E1 | 6.1E1 | 6.2E1 | 1.4E2 | 3.0E-2 | 3.0E-2 | 7.1E2 | 9.4E2 | 221 | 52 | 91 | 52 | 0.64 |
| bB | ng/mL | 3.1E2 | 2.6E2 | 3.4E2 | 2.6E2 | 1.6E2 | 1.4E2 | 1.6E1 | 1.2E1 | 1.0E3 | 5.7E2 | 221 | 52 | 91 | 52 | 0.36 |
| bC | ng/mL | 3.5E2 | 3.6E2 | 5.1E2 | 7.9E2 | 5.3E2 | 1.1E3 | 2.7E1 | 3.5E1 | 4.0E3 | 4.7E3 | 221 | 52 | 91 | 52 | 0.54 |
| bE | mg/mL | 5.6E0 | 5.6E0 | 5.9E0 | 5.5E0 | 1.7E0 | 2.1E0 | 1.9E0 | 1.3E0 | 1.3E1 | 1.1E1 | 221 | 52 | 91 | 52 | 0.43 |
| bF | pg/mL | 2.0E1 | 3.0E1 | 8.6E1 | 3.5E2 | 4.4E2 | 1.1E3 | 5.0E-2 | 6.1E0 | 5.0E3 | 6.3E3 | 221 | 52 | 91 | 52 | 0.63 |
| bG | ng/mL | 1.8E0 | 1.7E0 | 3.0E0 | 3.2E0 | 3.7E0 | 4.7E0 | 2.2E-2 | 1.1E-1 | 2.6E1 | 3.0E1 | 221 | 52 | 91 | 52 | 0.49 |
| bH | pg/mL | 5.7E-1 | 5.7E-1 | 5.4E0 | 4.7E0 | 2.0E1 | 6.3E0 | 5.7E-1 | 5.7E-1 | 2.8E2 | 2.7E1 | 221 | 52 | 91 | 52 | 0.53 |
| bI | ng/mL | 4.0E-3 | 4.0E-3 | 6.8E-2 | 8.5E-2 | 1.7E-1 | 1.9E-1 | 4.0E-3 | 4.0E-3 | 1.3E0 | 8.8E-1 | 221 | 52 | 91 | 52 | 0.51 |
| bJ | mg/mL | 2.2E0 | 2.2E0 | 2.5E0 | 2.5E0 | 1.9E0 | 1.9E0 | 2.5E-4 | 2.5E-4 | 1.3E1 | 8.5E0 | 221 | 52 | 91 | 52 | 0.49 |
| bL | pg/mL | 4.1E0 | 3.1E0 | 7.8E0 | 8.1E0 | 9.3E0 | 8.8E0 | 4.6E-2 | 4.6E-2 | 4.9E1 | 3.2E1 | 221 | 52 | 91 | 52 | 0.50 |
| bM | mg/mL | 1.5E0 | 2.2E0 | 1.8E0 | 2.6E0 | 1.2E0 | 1.6E0 | 9.2E-3 | 1.8E-2 | 7.1E0 | 8.4E0 | 221 | 52 | 91 | 52 | 0.66 |
| bN | ng/mL | 3.2E1 | 5.8E1 | 1.1E2 | 9.5E1 | 2.6E2 | 1.4E2 | 9.7E-1 | 5.9E-1 | 1.9E3 | 7.5E2 | 221 | 52 | 91 | 52 | 0.55 |
| bO | ng/mL | 4.0E-2 | 4.0E-2 | 1.1E1 | 1.0E1 | 2.4E1 | 2.0E1 | 4.0E-2 | 4.0E-2 | 1.9E2 | 7.1E1 | 221 | 52 | 91 | 52 | 0.46 |
| bP | mg/mL | 5.6E-1 | 4.6E-1 | 7.9E-1 | 7.5E-1 | 6.6E-1 | 7.7E-1 | 8.2E-2 | 9.7E-2 | 3.8E0 | 3.5E0 | 221 | 52 | 91 | 52 | 0.46 |
| bQ | pg/mL | 1.4E1 | 2.3E1 | 2.4E1 | 9.4E1 | 3.5E1 | 3.4E2 | 1.5E-1 | 1.5E-1 | 3.2E2 | 2.4E3 | 221 | 52 | 91 | 52 | 0.63 |
| bR | ng/mL | 1.2E-2 | 1.2E-2 | 1.4E-1 | 5.9E-2 | 2.8E-1 | 1.0E-1 | 1.2E-2 | 1.2E-2 | 3.4E0 | 4.8E-1 | 221 | 52 | 91 | 52 | 0.39 |
| bS | pg/mL | 9.4E-1 | 9.4E-1 | 8.1E0 | 5.9E0 | 2.9E1 | 1.3E1 | 9.4E-1 | 9.4E-1 | 3.4E2 | 6.1E1 | 221 | 52 | 91 | 52 | 0.50 |
| bU | ng/mL | 1.6E-1 | 6.1E-2 | 2.1E-1 | 1.1E-1 | 2.6E-1 | 1.3E-1 | 1.3E-2 | 1.3E-2 | 1.8E0 | 4.7E-1 | 221 | 52 | 91 | 52 | 0.38 |
| bV | pg/mL | 4.7E2 | 5.2E2 | 5.3E2 | 6.1E2 | 2.5E2 | 3.7E2 | 1.7E2 | 2.2E2 | 1.6E3 | 2.0E3 | 221 | 52 | 91 | 52 | 0.54 |
| bW | pg/mL | 3.5E2 | 3.4E2 | 4.7E2 | 9.7E2 | 4.2E2 | 3.4E3 | 1.1E2 | 1.2E2 | 3.4E3 | 2.5E4 | 221 | 52 | 91 | 52 | 0.52 |
| bX | ng/mL | 3.1E-3 | 2.5E-5 | 3.2E-3 | 2.3E-3 | 3.8E-3 | 2.8E-3 | 2.5E-5 | 2.5E-5 | 2.0E-2 | 8.5E-3 | 221 | 52 | 91 | 52 | 0.44 |
| bZ | pg/mL | 2.5E2 | 2.7E2 | 7.5E2 | 1.9E3 | 3.2E3 | 7.2E3 | 1.5E-1 | 3.5E1 | 4.4E4 | 4.3E4 | 221 | 52 | 91 | 52 | 0.53 |
| cA | pg/mL | 6.0E-1 | 6.0E-1 | 1.9E0 | 2.4E0 | 3.4E0 | 4.6E0 | 6.0E-1 | 6.0E-1 | 1.4E1 | 1.8E1 | 221 | 52 | 91 | 52 | 0.51 |
| cB | ng/mL | 6.0E-2 | 2.7E-2 | 9.0E-2 | 4.0E-2 | 1.0E-1 | 4.3E-2 | 1.7E-3 | 1.7E-3 | 5.4E-1 | 2.1E-1 | 221 | 52 | 91 | 52 | 0.33 |
| cC | pg/mL | 4.6E1 | 4.9E1 | 4.9E1 | 4.2E1 | 3.9E1 | 2.9E1 | 1.0E0 | 1.0E0 | 3.7E2 | 1.1E2 | 221 | 52 | 91 | 52 | 0.46 |
| cD | pg/mL | 6.1E0 | 4.5E0 | 1.3E1 | 1.5E1 | 4.0E1 | 4.3E1 | 3.3E-1 | 3.3E-1 | 4.8E2 | 2.9E2 | 221 | 52 | 91 | 52 | 0.44 |
| cE | pg/mL | 3.1E1 | 7.3E1 | 9.3E1 | 2.5E2 | 2.7E2 | 5.5E2 | 1.5E0 | 1.2E1 | 3.1E3 | 3.1E3 | 221 | 52 | 91 | 52 | 0.64 |
| cF | pg/mL | 1.3E1 | 5.3E-1 | 2.4E1 | 9.1E0 | 3.6E1 | 2.0E1 | 5.3E-1 | 5.3E-1 | 2.2E2 | 1.3E2 | 221 | 52 | 91 | 52 | 0.34 |
| cG | pg/mL | 4.2E1 | 5.8E1 | 6.4E1 | 1.2E2 | 8.8E1 | 1.9E2 | 1.1E1 | 1.8E1 | 1.1E3 | 1.2E3 | 221 | 52 | 91 | 52 | 0.63 |
| cH | uIU/mL | 2.9E0 | 2.2E0 | 6.0E0 | 5.7E0 | 8.9E0 | 9.7E0 | 8.6E-3 | 8.6E-3 | 8.7E1 | 5.3E1 | 221 | 52 | 91 | 52 | 0.44 |
| cI | ng/mL | 6.0E0 | 3.8E0 | 1.1E1 | 1.0E1 | 1.3E1 | 1.9E1 | 1.0E-3 | 1.0E-3 | 9.4E1 | 1.2E2 | 221 | 52 | 91 | 52 | 0.41 |
| cJ | ug/mL | 7.2E1 | 5.1E1 | 1.2E2 | 8.4E1 | 1.5E2 | 1.1E2 | 4.0E0 | 8.4E0 | 9.6E2 | 6.3E2 | 221 | 52 | 91 | 52 | 0.42 |
| cK | ng/mL | 3.8E-3 | 3.8E-3 | 7.5E-2 | 2.0E-2 | 2.2E-1 | 5.4E-2 | 3.8E-3 | 3.8E-3 | 1.7E0 | 3.1E-1 | 221 | 52 | 91 | 52 | 0.46 |
| cL | pg/mL | 1.9E2 | 2.4E2 | 2.7E2 | 3.6E2 | 5.1E2 | 8.0E2 | 2.5E1 | 3.7E1 | 7.1E3 | 5.9E3 | 221 | 52 | 91 | 52 | 0.56 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cM | pg/mL | 2.9E2 | 2.6E2 | 3.2E2 | 2.9E2 | 1.8E2 | 2.1E2 | 3.7E1 | 4.7E1 | 1.2E3 | 1.4E3 | 221 | 52 | 91 | 52 | 0.43 |
| cN | pg/mL | 1.2E2 | 1.2E2 | 1.2E2 | 1.4E2 | 4.4E1 | 5.7E1 | 3.8E1 | 6.5E1 | 2.7E2 | 3.2E2 | 221 | 52 | 91 | 52 | 0.59 |
| cO | pg/mL | 2.3E2 | 2.4E2 | 2.8E2 | 3.0E2 | 2.0E2 | 3.2E2 | 5.4E1 | 9.9E1 | 1.7E3 | 2.4E3 | 221 | 52 | 91 | 52 | 0.50 |
| cP | ng/mL | 2.4E3 | 2.8E3 | 2.5E3 | 2.8E3 | 8.9E2 | 9.3E2 | 6.2E2 | 1.3E3 | 5.7E3 | 5.3E3 | 221 | 52 | 91 | 52 | 0.59 |
| cQ | ng/mL | 4.0E-2 | 5.5E-2 | 1.1E-1 | 1.5E-1 | 1.8E-1 | 3.2E-1 | 2.0E-3 | 2.0E-3 | 1.2E0 | 2.1E0 | 221 | 52 | 91 | 52 | 0.56 |
| cR | ng/mL | 2.8E2 | 3.7E2 | 4.3E2 | 6.5E2 | 4.6E2 | 1.2E3 | 2.3E1 | 2.0E1 | 3.8E3 | 7.7E3 | 221 | 52 | 91 | 52 | 0.55 |
| cS | ng/mL | 2.4E2 | 3.1E2 | 3.9E2 | 4.3E2 | 4.2E2 | 3.2E2 | 5.3E1 | 4.8E1 | 2.7E3 | 1.3E3 | 221 | 52 | 91 | 52 | 0.58 |
| cT | ng/mL | 2.8E1 | 4.0E1 | 7.4E1 | 1.4E2 | 1.5E2 | 2.6E2 | 4.6E0 | 8.8E0 | 1.7E3 | 1.4E3 | 221 | 52 | 91 | 52 | 0.63 |
| cU | ng/mL | 5.5E1 | 5.5E1 | 7.4E1 | 7.8E1 | 7.2E1 | 6.7E1 | 1.0E1 | 1.4E1 | 7.7E2 | 3.4E2 | 221 | 52 | 91 | 52 | 0.51 |
| cV | ng/mL | 1.7E-1 | 2.2E-1 | 4.9E-1 | 6.0E-1 | 3.2E0 | 1.3E0 | 3.4E-4 | 3.6E-2 | 4.7E1 | 8.7E0 | 221 | 52 | 91 | 52 | 0.58 |
| cW | mIU/mL | 4.6E-2 | 6.5E-2 | 2.2E-1 | 8.7E-2 | 1.0E0 | 7.5E-2 | 3.7E-4 | 1.9E-2 | 9.7E0 | 3.9E-1 | 221 | 52 | 91 | 52 | 0.63 |
| cX | ng/mL | 1.1E-1 | 2.2E-1 | 1.8E0 | 1.5E0 | 5.4E0 | 4.5E0 | 2.3E-4 | 2.3E-4 | 2.8E1 | 2.8E1 | 221 | 52 | 91 | 52 | 0.53 |
| cY | ng/mL | 1.0E1 | 7.3E0 | 1.4E1 | 1.1E1 | 1.4E1 | 1.2E1 | 4.4E-1 | 1.7E-1 | 8.3E1 | 7.5E1 | 221 | 52 | 91 | 52 | 0.40 |
| cZ | ug/mL | 1.4E1 | 1.4E1 | 1.5E1 | 1.5E1 | 5.8E0 | 7.1E0 | 5.3E0 | 2.8E0 | 3.9E1 | 3.4E1 | 221 | 52 | 91 | 52 | 0.49 |
| dA | pg/mL | 3.3E2 | 3.1E2 | 3.6E2 | 3.6E2 | 1.6E2 | 1.9E2 | 9.0E1 | 1.4E2 | 1.3E3 | 1.1E3 | 221 | 52 | 91 | 52 | 0.47 |
| dB | ug/mL | 1.7E1 | 2.1E1 | 1.9E1 | 1.9E1 | 2.1E1 | 8.7E0 | 1.9E0 | 2.2E0 | 2.5E2 | 4.0E1 | 221 | 52 | 91 | 52 | 0.60 |
| dC | nmol/L | 3.4E1 | 3.8E1 | 4.1E1 | 4.0E1 | 2.0E1 | 1.5E1 | 9.1E0 | 1.9E1 | 1.4E2 | 9.2E1 | 221 | 52 | 91 | 52 | 0.53 |
| dD | ug/ml | 3.7E1 | 3.3E1 | 3.8E1 | 3.4E1 | 1.0E1 | 1.0E1 | 1.3E1 | 1.4E1 | 7.6E1 | 5.6E1 | 221 | 52 | 91 | 52 | 0.40 |
| dE | ng/mL | 4.8E-1 | 4.5E-1 | 6.7E-1 | 5.7E-1 | 8.3E-1 | 6.0E-1 | 8.4E-3 | 8.4E-3 | 7.2E0 | 2.8E0 | 221 | 52 | 91 | 52 | 0.47 |
| dF | ng/mL | 2.1E2 | 2.5E2 | 2.6E2 | 3.7E2 | 1.8E2 | 2.7E2 | 7.5E1 | 9.7E1 | 1.2E3 | 1.2E3 | 221 | 52 | 91 | 52 | 0.63 |
| dG | ng/mL | 1.1E1 | 1.3E1 | 1.3E1 | 1.8E1 | 8.4E0 | 1.5E1 | 3.1E0 | 5.5E0 | 6.4E1 | 8.7E1 | 221 | 52 | 91 | 52 | 0.59 |
| dH | pg/mL | 7.5E0 | 9.2E0 | 1.2E1 | 1.4E1 | 2.4E1 | 2.8E1 | 4.0E-2 | 4.0E-2 | 3.1E2 | 2.0E2 | 221 | 52 | 91 | 52 | 0.56 |
| dI | pg/mL | 4.6E-1 | 4.6E-1 | 1.9E0 | 2.1E0 | 4.4E0 | 4.0E0 | 4.6E-1 | 4.6E-1 | 3.4E1 | 2.3E1 | 221 | 52 | 91 | 52 | 0.53 |
| dJ | ng/mL | 1.9E0 | 2.0E0 | 2.1E0 | 2.2E0 | 1.1E0 | 1.6E0 | 3.2E-2 | 3.2E-2 | 5.9E0 | 6.9E0 | 221 | 52 | 91 | 52 | 0.50 |
| dK | uIU/mL | 2.0E0 | 1.5E0 | 2.7E0 | 2.6E0 | 2.9E0 | 3.4E0 | 2.8E-4 | 2.9E-2 | 1.6E1 | 2.2E1 | 221 | 52 | 91 | 52 | 0.47 |
| dL | ng/mL | 8.8E2 | 9.1E2 | 1.0E3 | 1.2E3 | 4.8E2 | 8.2E2 | 3.4E2 | 4.5E2 | 3.4E3 | 4.8E3 | 221 | 52 | 91 | 52 | 0.53 |
| dM | pg/mL | 9.7E2 | 9.2E2 | 1.2E3 | 1.5E3 | 1.1E3 | 1.7E3 | 4.4E2 | 4.1E2 | 1.2E4 | 9.6E3 | 221 | 52 | 91 | 52 | 0.49 |
| dN | ug/mL | 9.0E1 | 1.1E2 | 9.7E1 | 1.2E2 | 3.4E1 | 4.9E1 | 2.5E1 | 4.1E1 | 2.4E2 | 3.3E2 | 221 | 52 | 91 | 52 | 0.64 |
| dR | pg/ml | 1.6E3 | 1.2E3 | 2.5E3 | 2.2E3 | 2.6E3 | 2.6E3 | 1.9E2 | 1.4E2 | 1.5E4 | 9.4E3 | 131 | 45 | 88 | 45 | 0.41 |
| dU | pg/ml | 8.8E3 | 2.0E4 | 1.3E4 | 1.9E4 | 1.2E4 | 1.4E4 | 2.5E3 | 6.9E2 | 5.3E4 | 4.6E4 | 28 | 10 | 26 | 10 | 0.64 |
| dX | ng/ml | 3.4E-2 | 6.7E-2 | 9.5E-2 | 1.8E-1 | 1.5E-1 | 2.6E-1 | 2.6E-3 | 2.6E-3 | 7.4E-1 | 8.1E-1 | 65 | 14 | 21 | 14 | 0.56 |
| dW | ng/ml | 1.9E-1 | 2.0E-1 | 2.3E-1 | 3.0E-1 | 1.6E-1 | 2.6E-1 | 5.0E-2 | 6.8E-2 | 5.8E-1 | 8.0E-1 | 29 | 8 | 6 | 8 | 0.55 |
| eF | ng/ml | 4.0E0 | 4.3E0 | 4.6E0 | 5.1E0 | 2.6E0 | 2.5E0 | 1.5E0 | 2.0E0 | 1.8E1 | 1.5E1 | 138 | 45 | 88 | 45 | 0.58 |
| eC | pg/ml | 3.1E2 | 2.6E2 | 3.8E2 | 3.7E2 | 2.5E2 | 3.7E2 | 4.5E1 | 7.1E1 | 1.4E3 | 2.0E3 | 100 | 44 | 86 | 44 | 0.41 |
| eD | pg/ml | 2.3E2 | 1.9E2 | 7.7E2 | 4.3E2 | 1.4E3 | 1.1E3 | 5.2E-1 | 5.2E-1 | 6.8E3 | 7.0E3 | 77 | 41 | 64 | 41 | 0.43 |
| eO | ng/ml | 5.7E1 | 8.0E1 | 3.5E2 | 1.2E2 | 4.1E2 | 9.6E1 | 2.0E1 | 4.3E1 | 1.2E3 | 3.3E2 | 29 | 8 | 6 | 8 | 0.54 |
| eM | ng/ml | 3.6E0 | 2.5E0 | 4.4E0 | 5.0E0 | 3.5E0 | 6.2E0 | 8.1E-1 | 7.2E-1 | 2.2E1 | 2.6E1 | 87 | 19 | 34 | 19 | 0.44 |
| eP | ng/ml | 3.7E-3 | 3.7E-3 | 1.0E0 | 2.3E0 | 2.1E0 | 7.3E0 | 3.7E-3 | 3.7E-3 | 1.2E1 | 2.8E1 | 65 | 14 | 21 | 14 | 0.47 |
| eT | ng/ml | 2.7E2 | 2.5E2 | 5.6E2 | 7.0E2 | 6.1E2 | 8.6E2 | 1.0E2 | 7.1E1 | 2.5E3 | 2.9E3 | 51 | 23 | 49 | 23 | 0.53 |
| eQ | pg/ml | 1.0E0 | 1.0E0 | 1.1E2 | 3.9E1 | 3.2E2 | 6.0E1 | 1.0E0 | 1.0E0 | 1.6E3 | 1.5E2 | 28 | 10 | 26 | 10 | 0.52 |
| eW | U/ml | 6.7E-3 | 3.9E-2 | 5.5E-2 | 2.5E-1 | 9.2E-2 | 5.3E-1 | 6.7E-3 | 6.7E-3 | 3.1E-1 | 1.6E0 | 29 | 8 | 6 | 8 | 0.59 |
| fA | ng/ml | 2.2E2 | 1.2E2 | 4.0E2 | 3.1E2 | 4.6E2 | 4.4E2 | 2.6E1 | 4.0E1 | 1.5E3 | 1.4E3 | 28 | 10 | 26 | 10 | 0.43 |
| eZ | ng/ml | 6.1E1 | 5.4E1 | 6.4E1 | 5.7E1 | 2.6E1 | 2.4E1 | 2.3E1 | 1.8E1 | 1.2E2 | 1.2E2 | 51 | 23 | 49 | 23 | 0.43 |
| fB | ng/ml | 6.1E2 | 6.6E2 | 6.8E2 | 6.7E2 | 2.8E2 | 2.4E2 | 1.6E2 | 2.6E2 | 1.3E3 | 1.0E3 | 28 | 12 | 26 | 12 | 0.52 |
| fN | ng/ml | 2.1E-1 | 2.1E-1 | 2.7E0 | 1.8E0 | 5.8E0 | 6.5E0 | 2.1E-1 | 2.1E-1 | 3.2E1 | 3.2E2 | 51 | 23 | 49 | 23 | 0.58 |
| fP | ng/ml | 2.3E2 | 3.6E2 | 2.7E2 | 3.5E2 | 1.7E2 | 1.6E2 | 8.4E0 | 3.7E1 | 1.0E3 | 8.2E2 | 127 | 45 | 88 | 45 | 0.67 |
| fR | ng/ml | 1.3E5 | 1.7E5 | 1.6E5 | 2.7E5 | 1.1E5 | 2.1E5 | 3.1E4 | 1.9E2 | 6.1E5 | 6.8E5 | 162 | 31 | 44 | 31 | 0.65 |
| fY | ng/ml | 2.5E2 | 2.6E2 | 2.4E2 | 2.6E2 | 8.9E1 | 1.0E2 | 6.5E1 | 3.6E1 | 4.2E2 | 4.7E2 | 51 | 23 | 49 | 23 | 0.56 |
| gC | ng/ml | 2.3E2 | 2.4E2 | 2.5E2 | 2.5E2 | 9.4E1 | 1.0E2 | 1.2E2 | 8.3E1 | 6.4E2 | 4.0E2 | 71 | 12 | 39 | 12 | 0.54 |
| gL | pg/ml | 6.1E4 | 6.9E4 | 6.8E4 | 7.4E4 | 2.9E4 | 3.1E4 | 2.2E4 | 3.4E4 | 1.8E5 | 1.7E5 | 88 | 45 | 88 | 45 | 0.57 |
| gP | U/ml | 2.5E2 | 3.0E2 | 2.6E2 | 2.8E2 | 7.9E1 | 1.1E2 | 8.5E1 | 1.2E1 | 5.3E2 | 6.5E2 | 137 | 45 | 88 | 45 | 0.59 |
| gW | ng/ml | 7.0E2 | 5.1E2 | 1.5E3 | 1.1E3 | 1.9E3 | 1.6E3 | 3.7E1 | 3.1E-1 | 9.5E3 | 5.8E3 | 109 | 36 | 79 | 36 | 0.42 |
| gV | ng/ml | 2.0E1 | 1.6E1 | 2.1E1 | 1.7E1 | 6.7E0 | 8.7E0 | 1.0E1 | 8.1E-2 | 3.9E1 | 3.0E1 | 59 | 9 | 15 | 9 | 0.37 |
| tF | pg/mL | 2.6E3 | 1.2E3 | 2.2E4 | 1.1E4 | 5.6E4 | 4.2E4 | 1.2E1 | 1.8E1 | 3.2E5 | 2.5E5 | 100 | 44 | 86 | 44 | 0.39 |
| gZ | ug/ml | 8.9E-1 | 6.1E-1 | 4.5E1 | 4.1E1 | 1.1E2 | 1.3E2 | 8.7E-2 | 1.1E-1 | 4.1E2 | 4.0E2 | 28 | 10 | 26 | 10 | 0.45 |
| hA | ng/ml | 2.3E0 | 2.6E0 | 7.4E0 | 6.8E0 | 2.4E1 | 1.1E1 | 1.7E-2 | 1.7E-2 | 1.6E2 | 6.1E1 | 77 | 43 | 64 | 43 | 0.53 |
| nM | pg/ml | 1.0E-9 | 1.0E-9 | 1.9E2 | 1.0E-9 | 1.4E3 | 0.0E0 | 1.0E-9 | 1.0E-9 | 1.0E4 | 1.0E-9 | 54 | 30 | 47 | 30 | 0.48 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nN | pg/ml | 1.1E3 | 3.2E3 | 2.1E3 | 1.6E4 | 2.7E3 | 5.1E4 | 1.1E2 | 6.8E2 | 1.7E4 | 2.7E5 | 54 | 30 | 47 | 30 | 0.72 |
| nO | pg/ml | 3.1E1 | 3.6E1 | 4.5E1 | 5.2E1 | 4.7E1 | 6.5E1 | 5.5E0 | 4.0E0 | 2.4E2 | 3.1E2 | 54 | 30 | 47 | 30 | 0.50 |
| nR | pg/ml | 1.6E1 | 3.0E1 | 4.5E1 | 9.3E1 | 7.3E1 | 1.9E2 | 1.0E-9 | 1.0E0 | 3.6E2 | 8.2E2 | 54 | 30 | 47 | 30 | 0.61 |
| nT | pg/ml | 8.5E1 | 8.6E1 | 3.5E2 | 1.1E2 | 1.2E3 | 1.2E2 | 1.0E-9 | 1.0E-9 | 6.6E3 | 6.4E2 | 54 | 30 | 47 | 30 | 0.53 |
| nU | pg/ml | 2.9E1 | 6.0E1 | 5.1E2 | 1.3E2 | 2.2E3 | 2.8E2 | 1.0E-9 | 1.0E-9 | 1.3E4 | 1.5E3 | 54 | 30 | 47 | 30 | 0.60 |
| lW | pg/ml | 1.0E-9 | 1.0E-9 | 1.6E1 | 1.9E1 | 5.5E1 | 5.9E1 | 1.0E-9 | 1.0E-9 | 3.9E2 | 2.9E2 | 54 | 30 | 47 | 30 | 0.47 |
| lX | pg/ml | 9.5E2 | 8.2E2 | 9.2E2 | 9.2E2 | 4.4E2 | 6.3E2 | 2.3E2 | 1.3E2 | 1.9E3 | 2.5E3 | 54 | 30 | 47 | 30 | 0.45 |
| lY | pg/ml | 1.7E1 | 1.9E1 | 2.2E1 | 2.1E1 | 2.5E1 | 1.4E1 | 1.0E-9 | 1.0E-9 | 1.4E2 | 5.5E1 | 54 | 30 | 47 | 30 | 0.55 |
| mE | pg/ml | 1.0E-9 | 1.0E-9 | 3.3E0 | 1.7E0 | 1.0E1 | 3.3E0 | 1.0E-9 | 1.0E-9 | 5.8E1 | 1.6E1 | 54 | 30 | 47 | 30 | 0.57 |
| mF | pg/ml | 1.0E-9 | 3.6E-1 | 1.4E0 | 2.1E0 | 3.0E0 | 3.7E0 | 1.0E-9 | 1.0E-9 | 1.5E1 | 1.3E1 | 54 | 30 | 47 | 30 | 0.60 |
| mH | pg/ml | 3.6E0 | 2.9E0 | 4.9E0 | 3.9E0 | 5.0E0 | 3.8E0 | 2.3E-1 | 4.0E-1 | 3.2E1 | 1.9E1 | 54 | 30 | 47 | 30 | 0.44 |
| mI | pg/ml | 1.0E-9 | 4.9E0 | 1.2E1 | 1.4E1 | 3.1E1 | 1.9E1 | 1.0E-9 | 1.0E-9 | 1.6E2 | 6.7E1 | 54 | 30 | 47 | 30 | 0.61 |
| mM | pg/ml | 3.0E1 | 5.2E1 | 5.2E1 | 1.6E2 | 5.9E1 | 2.7E2 | 1.0E-9 | 1.0E-9 | 2.3E2 | 1.1E3 | 54 | 30 | 47 | 30 | 0.60 |
| mP | pg/ml | 1.5E1 | 1.5E1 | 2.0E1 | 2.4E1 | 2.2E1 | 3.7E1 | 1.0E-9 | 1.6E0 | 1.5E2 | 1.9E2 | 53 | 30 | 46 | 30 | 0.50 |
| mS | pg/ml | 1.8E3 | 1.8E3 | 2.2E3 | 1.8E3 | 2.2E3 | 8.9E2 | 1.0E-9 | 1.0E-9 | 1.3E4 | 3.5E3 | 54 | 30 | 47 | 30 | 0.47 |
| mT | pg/ml | 5.0E1 | 7.6E1 | 1.2E2 | 1.4E2 | 2.2E2 | 2.0E2 | 1.0E1 | 1.2E1 | 1.4E3 | 9.7E2 | 53 | 30 | 46 | 30 | 0.56 |
| mU | pg/ml | 2.5E0 | 2.2E0 | 4.2E0 | 1.2E1 | 8.5E0 | 4.2E1 | 1.0E-9 | 5.5E-1 | 5.8E1 | 2.2E2 | 53 | 30 | 46 | 30 | 0.52 |
| mW | pg/ml | 2.5E3 | 2.1E3 | 2.7E3 | 2.5E3 | 1.7E3 | 1.6E3 | 4.3E2 | 1.0E-9 | 1.0E4 | 6.2E3 | 53 | 30 | 46 | 30 | 0.45 |
| mY | pg/ml | 4.7E2 | 7.9E2 | 1.0E3 | 9.5E2 | 1.8E3 | 1.0E3 | 1.0E-9 | 1.0E-9 | 1.1E4 | 5.6E3 | 54 | 30 | 47 | 30 | 0.61 |
| mZ | pg/ml | 2.6E2 | 2.4E2 | 5.0E2 | 3.8E2 | 6.0E2 | 3.8E2 | 2.1E1 | 3.9E1 | 3.1E3 | 1.5E3 | 53 | 30 | 46 | 30 | 0.45 |
| nA | pg/ml | 1.3E0 | 2.1E0 | 1.6E1 | 7.0E0 | 6.6E1 | 1.3E1 | 1.0E-9 | 1.0E-9 | 4.4E2 | 5.1E1 | 53 | 30 | 46 | 30 | 0.52 |
| nB | pg/ml | 2.6E2 | 3.2E2 | 3.1E2 | 3.2E2 | 1.6E2 | 1.6E2 | 3.0E1 | 3.7E1 | 7.2E2 | 8.2E2 | 54 | 30 | 47 | 30 | 0.55 |
| nC | pg/ml | 1.0E-9 | 7.9E1 | 8.7E3 | 1.4E4 | 5.0E4 | 7.0E4 | 1.0E-9 | 1.0E-9 | 3.7E5 | 3.8E5 | 54 | 30 | 47 | 30 | 0.58 |
| nD | pg/ml | 7.2E0 | 7.6E0 | 7.0E1 | 1.0E1 | 3.1E2 | 9.6E0 | 1.0E-9 | 1.0E-9 | 1.7E3 | 3.0E1 | 53 | 30 | 46 | 30 | 0.52 |
| nF | pg/ml | 1.0E-9 | 1.0E-9 | 9.5E0 | 1.9E0 | 4.0E1 | 6.9E0 | 1.0E-9 | 1.0E-9 | 2.4E2 | 3.5E1 | 54 | 30 | 47 | 30 | 0.51 |
| nH | pg/ml | 3.0E-2 | 3.9E0 | 2.1E2 | 1.0E2 | 1.4E3 | 4.8E2 | 1.0E-9 | 1.0E-9 | 1.0E4 | 2.6E3 | 53 | 30 | 46 | 30 | 0.60 |
| nI | pg/ml | 4.6E1 | 1.6E1 | 2.9E2 | 5.6E1 | 1.3E3 | 1.0E2 | 1.0E-9 | 1.0E-9 | 9.2E3 | 5.2E2 | 54 | 30 | 47 | 30 | 0.41 |
| nJ | pg/ml | 1.7E-1 | 5.1E-1 | 9.9E1 | 1.4E0 | 7.0E2 | 3.1E0 | 1.0E-9 | 1.0E-9 | 5.2E3 | 1.7E1 | 54 | 30 | 47 | 30 | 0.52 |
| nK | pg/ml | 1.0E-9 | 5.4E0 | 1.2E2 | 1.7E1 | 5.4E2 | 2.6E1 | 1.0E-9 | 1.0E-9 | 3.2E3 | 1.2E2 | 53 | 30 | 46 | 30 | 0.61 |
| nL | pg/ml | 1.0E-9 | 4.3E0 | 9.3E2 | 2.0E2 | 6.1E3 | 7.9E2 | 1.0E-9 | 1.0E-9 | 4.5E4 | 4.3E3 | 54 | 30 | 47 | 30 | 0.58 |
| hL | pg/ml | 1.7E4 | 1.8E4 | 2.3E4 | 2.1E4 | 2.2E4 | 1.3E4 | 2.6E3 | 2.6E3 | 1.4E5 | 6.0E4 | 51 | 23 | 49 | 23 | 0.51 |
| hO | pg/ml | 1.6E4 | 1.6E4 | 1.7E4 | 1.6E4 | 3.2E3 | 3.1E3 | 1.1E4 | 1.1E4 | 2.8E4 | 2.3E4 | 51 | 23 | 49 | 23 | 0.44 |
| hP | ng/ml | 4.4E5 | 4.4E5 | 3.7E5 | 4.8E5 | 1.7E5 | 5.4E5 | 2.8E4 | 3.4E4 | 9.0E5 | 2.8E6 | 51 | 23 | 49 | 23 | 0.51 |
| wJ | pg/ml | 1.5E5 | 1.0E5 | 1.6E5 | 1.7E5 | 8.7E4 | 1.3E5 | 2.8E4 | 3.6E4 | 4.0E5 | 5.8E5 | 48 | 25 | 44 | 25 | 0.44 |
| wK | pg/ml | 3.4E4 | 4.2E4 | 4.3E4 | 5.0E4 | 2.7E4 | 4.2E4 | 5.2E3 | 8.1E3 | 1.2E5 | 2.0E5 | 48 | 25 | 44 | 25 | 0.51 |
| wL | pg/ml | 6.5E0 | 1.9E0 | 7.0E1 | 2.0E1 | 1.5E2 | 6.4E1 | 1.0E-9 | 1.0E-9 | 8.4E2 | 3.2E2 | 48 | 25 | 44 | 25 | 0.37 |
| wP | pg/ml | 2.8E4 | 2.8E4 | 4.3E4 | 6.5E4 | 4.3E4 | 8.2E4 | 2.8E3 | 4.5E3 | 1.6E5 | 3.0E5 | 48 | 25 | 44 | 25 | 0.55 |
| wQ | pg/ml | 3.4E1 | 4.1E1 | 6.0E1 | 5.4E1 | 7.7E1 | 6.1E1 | 1.0E-9 | 1.0E-9 | 3.7E2 | 2.4E2 | 48 | 25 | 44 | 25 | 0.50 |
| hR | pg/ml | 2.7E4 | 2.5E4 | 3.0E4 | 2.5E4 | 1.1E4 | 1.0E4 | 1.8E3 | 1.0E-9 | 5.8E4 | 4.5E4 | 75 | 39 | 62 | 39 | 0.40 |
| hV | pg/ml | 4.4E2 | 3.9E2 | 4.7E2 | 4.4E2 | 2.4E2 | 2.6E2 | 1.3E2 | 1.0E-9 | 1.5E3 | 1.3E3 | 75 | 39 | 62 | 39 | 0.46 |
| hW | pg/ml | 1.6E3 | 1.9E3 | 2.1E3 | 3.1E3 | 1.6E3 | 6.2E3 | 5.7E2 | 1.0E-9 | 1.0E4 | 4.0E4 | 75 | 39 | 62 | 39 | 0.56 |
| hX | pg/ml | 9.6E2 | 8.4E2 | 1.2E3 | 9.8E2 | 1.1E3 | 5.2E2 | 4.8E2 | 2.5E0 | 8.6E3 | 2.9E3 | 75 | 39 | 62 | 39 | 0.43 |
| iA | pg/ml | 1.7E2 | 1.9E2 | 4.2E2 | 2.7E2 | 9.2E2 | 2.1E2 | 1.8E1 | 1.1E1 | 7.1E3 | 7.8E2 | 100 | 43 | 86 | 43 | 0.55 |
| iB | ng/ml | 5.4E0 | 6.5E0 | 6.7E0 | 7.9E0 | 4.7E0 | 6.1E0 | 2.5E-1 | 8.8E-2 | 2.0E1 | 2.4E1 | 77 | 43 | 64 | 43 | 0.54 |
| iC | U/ml | 2.4E-1 | 4.6E-1 | 5.0E-1 | 1.6E0 | 8.7E-1 | 5.1E0 | 1.0E-9 | 1.0E-9 | 6.4E0 | 3.2E1 | 77 | 43 | 64 | 43 | 0.65 |
| tQ | pg/ml | 1.1E3 | 1.4E3 | 1.2E3 | 1.4E3 | 5.5E2 | 6.8E2 | 2.8E2 | 5.3E2 | 2.5E3 | 3.3E3 | 46 | 24 | 43 | 24 | 0.58 |
| tT | pg/ml | 1.5E1 | 2.1E1 | 1.7E1 | 3.2E1 | 7.4E0 | 2.7E1 | 7.4E0 | 6.7E0 | 3.9E1 | 1.2E2 | 46 | 24 | 43 | 24 | 0.70 |
| tS | pg/ml | 1.0E0 | 1.2E0 | 1.1E0 | 2.3E0 | 8.6E-1 | 2.9E0 | 1.0E-9 | 1.0E-9 | 4.0E0 | 1.0E1 | 46 | 24 | 43 | 24 | 0.59 |
| tX | pg/ml | 8.1E-1 | 1.3E0 | 9.5E-1 | 2.4E0 | 7.0E-1 | 2.6E0 | 2.5E-2 | 3.7E-1 | 3.3E0 | 1.0E1 | 46 | 24 | 43 | 24 | 0.68 |
| tO | pg/ml | 4.0E0 | 4.7E0 | 4.4E0 | 6.3E0 | 2.5E0 | 4.9E0 | 1.0E-9 | 1.6E0 | 1.1E1 | 1.9E1 | 46 | 24 | 43 | 24 | 0.57 |
| tR | pg/ml | 2.1E-1 | 2.4E-1 | 2.5E-1 | 5.0E-1 | 2.1E-1 | 6.7E-1 | 1.0E-9 | 1.0E-9 | 9.1E-1 | 2.5E0 | 46 | 24 | 43 | 24 | 0.58 |
| tU | pg/ml | 9.0E0 | 1.1E1 | 1.1E1 | 1.5E1 | 6.9E0 | 1.6E1 | 1.6E0 | 1.5E0 | 3.1E1 | 8.0E1 | 46 | 25 | 43 | 25 | 0.58 |
| tN | pg/ml | 1.7E1 | 1.9E1 | 1.9E1 | 3.9E1 | 1.0E1 | 3.9E1 | 1.0E-9 | 9.4E0 | 5.4E1 | 1.6E2 | 46 | 23 | 43 | 23 | 0.64 |
| tV | ng/ml | 3.7E2 | 9.5E2 | 4.8E2 | 9.4E2 | 4.0E2 | 6.4E2 | 6.6E1 | 2.2E2 | 2.6E3 | 3.1E3 | 48 | 25 | 44 | 25 | 0.74 |
| iH | ng/ml | 1.5E5 | 1.8E5 | 1.5E5 | 1.8E5 | 4.3E4 | 4.3E4 | 7.1E4 | 6.7E4 | 2.4E5 | 2.4E5 | 100 | 43 | 86 | 43 | 0.69 |
| iJ | ng/ml | 5.1E4 | 4.3E4 | 5.3E4 | 5.1E4 | 2.0E4 | 3.8E4 | 8.7E3 | 7.7E3 | 1.2E5 | 2.5E5 | 100 | 43 | 86 | 43 | 0.42 |
| hB | ng/ml | 4.3E-1 | 6.2E-1 | 5.2E-1 | 7.5E-1 | 3.5E-1 | 5.7E-1 | 1.2E-1 | 1.4E-1 | 1.9E0 | 2.4E0 | 100 | 43 | 86 | 43 | 0.64 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| hC | pg/ml | 3.6E3 | 5.7E3 | 5.9E3 | 9.5E3 | 7.5E3 | 1.2E4 | 1.0E-9 | 2.3E2 | 5.5E4 | 5.7E4 | 100 | 43 | 86 | 43 | 0.61 |
| hF | ng/ml | 1.0E-9 | 1.0E-9 | 4.9E1 | 1.0E-9 | 4.1E2 | 0.0E0 | 1.0E-9 | 1.0E-9 | 4.0E3 | 1.0E-9 | 100 | 43 | 86 | 43 | 0.49 |
| hG | pg/ml | 7.4E3 | 7.6E3 | 7.8E3 | 8.5E3 | 2.9E3 | 3.8E3 | 1.7E3 | 3.3E3 | 1.8E4 | 2.0E4 | 100 | 43 | 86 | 43 | 0.54 |
| iO | ng/ml | 4.1E5 | 3.7E5 | 4.2E5 | 4.0E5 | 2.0E5 | 1.9E5 | 1.1E5 | 8.3E4 | 1.1E6 | 9.2E5 | 100 | 43 | 86 | 43 | 0.47 |
| iP | ng/ml | 6.1E4 | 4.1E4 | 5.5E4 | 7.0E4 | 3.1E4 | 1.1E5 | 5.8E3 | 3.8E3 | 2.5E5 | 5.7E5 | 100 | 43 | 86 | 43 | 0.44 |
| iZ | ng/ml | 1.7E3 | 1.7E3 | 1.8E3 | 2.0E3 | 6.8E2 | 9.3E2 | 4.7E2 | 7.5E2 | 3.5E3 | 4.6E3 | 100 | 43 | 86 | 43 | 0.55 |
| yH | pg/ml | 1.2E3 | 1.4E3 | 2.0E3 | 3.9E3 | 3.0E3 | 6.5E3 | 1.0E-9 | 2.4E2 | 1.5E4 | 2.5E4 | 48 | 25 | 44 | 25 | 0.61 |
| yK | U/ml | 1.8E1 | 2.8E1 | 4.9E1 | 5.1E1 | 8.5E1 | 6.3E1 | 1.0E-9 | 1.0E-9 | 3.8E2 | 3.0E2 | 48 | 25 | 44 | 25 | 0.62 |
| yJ | pg/ml | 3.6E4 | 3.6E4 | 4.7E4 | 4.4E4 | 3.5E4 | 3.4E4 | 1.7E3 | 2.7E3 | 1.6E5 | 1.3E5 | 48 | 25 | 44 | 25 | 0.47 |
| yD | ng/ml | 1.5E-2 | 1.8E-2 | 1.5E-2 | 1.7E-2 | 5.8E-3 | 7.9E-3 | 1.0E-9 | 1.0E-9 | 2.9E-2 | 3.0E-2 | 48 | 25 | 44 | 25 | 0.59 |
| jB | ng/ml | 2.6E5 | 1.8E5 | 2.7E5 | 1.8E5 | 8.8E4 | 4.6E4 | 5.7E4 | 9.9E4 | 4.1E5 | 2.3E5 | 28 | 10 | 26 | 10 | 0.18 |
| wB | ng/ml | 8.8E3 | 1.1E4 | 9.8E3 | 1.3E4 | 7.3E3 | 1.0E4 | 1.7E3 | 3.1E3 | 4.1E4 | 4.2E4 | 48 | 25 | 44 | 25 | 0.59 |
| pY | pg/ml | 6.0E0 | 6.6E0 | 1.1E1 | 7.7E0 | 2.7E1 | 3.7E0 | 2.1E0 | 3.5E0 | 2.0E2 | 1.8E1 | 51 | 23 | 49 | 23 | 0.57 |
| sI | ng/ml | 5.4E-2 | 5.6E-2 | 6.4E-2 | 6.5E-2 | 4.6E-2 | 3.4E-2 | 1.6E-2 | 2.5E-2 | 2.5E-1 | 1.5E-1 | 25 | 14 | 25 | 14 | 0.54 |
| sF | mIU/mL | 4.8E0 | 7.1E0 | 1.2E1 | 1.2E1 | 1.9E1 | 1.4E1 | 1.4E-1 | 9.3E-2 | 7.5E1 | 4.5E1 | 25 | 14 | 25 | 14 | 0.56 |
| sH | mIU/mL | 2.3E0 | 3.8E0 | 4.7E0 | 4.1E0 | 7.2E0 | 4.4E0 | 7.9E-2 | 1.0E-9 | 3.2E1 | 1.7E1 | 25 | 14 | 25 | 14 | 0.54 |
| sJ | ng/ml | 1.5E-1 | 1.5E-1 | 8.5E-1 | 1.7E-1 | 1.8E0 | 1.6E-1 | 1.0E-9 | 1.0E-9 | 6.4E0 | 6.1E-1 | 25 | 14 | 25 | 14 | 0.45 |
| rC | pg/ml | 1.9E3 | 1.2E3 | 2.6E3 | 1.6E3 | 2.8E3 | 1.5E3 | 1.0E2 | 1.9E2 | 1.5E4 | 7.3E3 | 72 | 39 | 59 | 39 | 0.38 |
| rB | pg/ml | 2.2E1 | 2.6E1 | 5.5E1 | 4.5E1 | 1.4E2 | 5.1E1 | 1.0E-9 | 1.0E-9 | 9.5E2 | 2.1E2 | 72 | 39 | 59 | 39 | 0.56 |
| zG | 2.5ng/ml | 2.0E-1 | 2.2E-1 | 4.5E-1 | 4.7E-1 | 7.8E-1 | 7.5E-1 | 1.0E-9 | 1.0E-9 | 4.4E0 | 2.7E0 | 48 | 25 | 44 | 25 | 0.49 |
| zH | 2.3mU/ml | 1.1E-1 | 8.8E-2 | 1.2E-1 | 9.1E-2 | 6.9E-2 | 3.5E-2 | 1.0E-2 | 1.9E-2 | 4.4E-1 | 1.7E-1 | 48 | 25 | 44 | 25 | 0.37 |
| zI | 2.6ng/ml | 1.8E0 | 2.5E0 | 3.2E0 | 5.6E0 | 3.3E0 | 7.2E0 | 6.1E-1 | 4.3E-1 | 1.5E1 | 2.7E1 | 48 | 25 | 44 | 25 | 0.60 |
| qA | ng/ml | 1.0E7 | 9.4E6 | 1.1E7 | 1.4E7 | 7.3E6 | 1.0E7 | 3.7E6 | 3.4E6 | 3.7E7 | 4.6E7 | 51 | 23 | 49 | 23 | 0.57 |
| qB | ng/ml | 6.3E5 | 5.4E5 | 8.3E5 | 8.9E5 | 5.8E5 | 8.2E5 | 2.1E5 | 1.9E5 | 2.9E6 | 3.8E6 | 51 | 23 | 49 | 23 | 0.48 |
| qC | ng/ml | 4.8E5 | 3.4E5 | 8.2E5 | 5.8E5 | 1.2E6 | 9.5E5 | 2.0E4 | 2.1E4 | 7.1E6 | 4.7E6 | 51 | 23 | 49 | 23 | 0.42 |
| qD | ng/ml | 1.6E7 | 1.5E7 | 1.9E7 | 1.7E7 | 9.4E6 | 6.9E6 | 4.9E6 | 4.9E6 | 5.2E7 | 3.4E7 | 51 | 23 | 49 | 23 | 0.44 |
| jD | ng/ml | 2.2E1 | 3.2E1 | 4.4E1 | 5.7E1 | 7.2E1 | 5.0E1 | 1.0E-9 | 1.0E-9 | 5.1E2 | 1.8E2 | 77 | 43 | 64 | 43 | 0.64 |
| jE | ng/ml | 1.0E-9 | 1.0E-9 | 8.0E0 | 6.5E0 | 2.1E1 | 1.2E1 | 1.0E-9 | 1.0E-9 | 1.2E2 | 3.9E1 | 77 | 43 | 64 | 43 | 0.52 |
| jF | ng/ml | 3.5E1 | 2.8E1 | 5.0E1 | 5.0E1 | 5.8E1 | 6.7E1 | 1.0E-9 | 1.0E-9 | 2.5E2 | 3.5E2 | 77 | 43 | 64 | 43 | 0.48 |
| jG | ng/ml | 4.5E3 | 4.2E3 | 4.6E3 | 4.5E3 | 1.9E3 | 1.9E3 | 7.6E2 | 6.7E2 | 9.5E3 | 8.7E3 | 77 | 43 | 64 | 43 | 0.48 |
| jH | ng/ml | 7.9E1 | 7.9E1 | 8.6E1 | 9.6E1 | 4.5E1 | 6.8E1 | 1.9E1 | 1.5E1 | 2.3E2 | 4.3E2 | 77 | 43 | 64 | 43 | 0.53 |
| jI | ng/ml | 6.9E1 | 8.2E1 | 7.4E1 | 9.2E1 | 3.4E1 | 6.5E1 | 2.8E1 | 3.6E1 | 2.5E2 | 4.4E2 | 77 | 43 | 64 | 43 | 0.60 |
| sK | pg/mL | 4.2E3 | 3.4E3 | 4.3E3 | 4.5E3 | 1.6E3 | 4.3E3 | 1.7E3 | 2.1E3 | 9.2E3 | 2.3E4 | 49 | 24 | 45 | 24 | 0.41 |
| sM | pg/mL | 8.0E4 | 8.4E4 | 7.9E4 | 9.1E4 | 2.4E4 | 4.1E4 | 3.3E4 | 4.5E4 | 1.5E5 | 2.0E5 | 49 | 24 | 45 | 24 | 0.57 |
| sO | pg/mL | 2.8E8 | 2.4E8 | 2.9E8 | 2.3E8 | 9.9E7 | 8.9E7 | 7.9E7 | 6.6E7 | 4.9E8 | 4.4E8 | 49 | 24 | 45 | 24 | 0.35 |
| wC | ng/ml | 1.6E0 | 1.4E0 | 2.1E0 | 1.7E0 | 2.2E0 | 1.1E0 | 2.5E-1 | 6.1E-2 | 1.5E1 | 4.8E0 | 48 | 25 | 44 | 25 | 0.46 |
| wD | ng/ml | 2.0E1 | 2.3E1 | 8.1E1 | 5.1E1 | 3.1E2 | 6.5E1 | 2.8E0 | 5.0E0 | 2.1E3 | 2.9E2 | 48 | 25 | 44 | 25 | 0.65 |
| wE | ng/ml | 5.0E1 | 5.0E1 | 5.4E1 | 4.7E1 | 2.4E1 | 1.8E1 | 7.0E0 | 3.2E0 | 1.4E2 | 8.4E1 | 48 | 25 | 44 | 25 | 0.42 |
| wG | ng/ml | 9.6E-2 | 3.8E-2 | 1.3E-1 | 7.6E-2 | 1.3E-1 | 1.4E-1 | 1.0E-9 | 1.0E-9 | 4.8E-1 | 6.8E-1 | 48 | 25 | 44 | 25 | 0.37 |
| wH | ng/ml | 2.3E-2 | 2.6E-2 | 2.1E-1 | 2.1E-1 | 5.5E-1 | 4.4E-1 | 1.0E-9 | 1.0E-9 | 2.9E0 | 1.9E0 | 48 | 25 | 44 | 25 | 0.50 |
| wF | ng/ml | 2.1E-1 | 1.3E-1 | 2.9E0 | 1.2E0 | 1.0E1 | 2.3E0 | 1.0E-9 | 1.0E-9 | 5.7E1 | 9.6E0 | 48 | 25 | 44 | 25 | 0.49 |
| rA | pg/ml | 2.4E1 | 2.6E1 | 2.7E1 | 3.1E1 | 2.2E1 | 2.1E1 | 1.0E-9 | 1.0E-9 | 1.2E2 | 9.3E1 | 74 | 43 | 61 | 43 | 0.56 |
| qZ | pg/ml | 4.3E1 | 5.3E1 | 2.1E2 | 1.1E3 | 1.3E3 | 2.9E3 | 2.8E-4 | 3.2E-2 | 1.0E4 | 1.0E4 | 63 | 33 | 54 | 33 | 0.55 |
| qY | pg/ml | 2.1E1 | 2.6E1 | 4.6E1 | 4.3E1 | 7.5E1 | 4.3E1 | 8.7E-1 | 2.1E0 | 5.3E2 | 1.6E2 | 74 | 43 | 61 | 43 | 0.56 |
| qX | pg/ml | 5.1E1 | 6.8E1 | 5.9E1 | 7.7E1 | 3.9E1 | 5.6E1 | 1.0E-9 | 1.0E-9 | 1.8E2 | 2.1E2 | 74 | 43 | 61 | 43 | 0.56 |
| qW | pg/ml | 9.4E0 | 7.6E0 | 1.2E1 | 9.8E0 | 1.3E1 | 9.4E0 | 1.0E-9 | 1.0E-9 | 7.1E1 | 3.6E1 | 74 | 43 | 61 | 43 | 0.44 |
| qV | pg/ml | 2.1E3 | 2.1E3 | 2.7E3 | 2.7E3 | 1.9E3 | 1.8E3 | 2.3E2 | 4.3E2 | 8.5E3 | 6.9E3 | 74 | 43 | 61 | 43 | 0.49 |
| qU | pg/ml | 4.5E1 | 8.3E1 | 1.3E2 | 1.6E2 | 2.2E2 | 2.3E2 | 1.0E-9 | 1.0E-9 | 1.4E3 | 1.1E3 | 74 | 43 | 61 | 43 | 0.58 |
| qT | pg/ml | 3.8E1 | 4.1E1 | 6.4E1 | 6.7E1 | 1.2E2 | 6.4E1 | 1.0E-9 | 1.0E-9 | 9.0E2 | 3.0E2 | 74 | 43 | 61 | 43 | 0.57 |
| qI | ng/ml | 5.8E4 | 6.4E4 | 6.4E4 | 6.5E4 | 3.2E4 | 2.9E4 | 5.4E2 | 2.5E4 | 1.6E5 | 1.6E5 | 48 | 23 | 46 | 23 | 0.53 |
| qH | ng/ml | 6.5E4 | 5.5E4 | 7.3E4 | 5.9E4 | 3.9E4 | 3.2E4 | 1.0E4 | 1.1E4 | 1.8E5 | 1.6E5 | 48 | 23 | 46 | 23 | 0.40 |
| qG | ng/ml | 1.8E5 | 1.9E5 | 1.9E5 | 2.0E5 | 6.2E4 | 5.9E4 | 3.1E4 | 1.0E5 | 3.3E5 | 3.2E5 | 48 | 23 | 46 | 23 | 0.51 |
| jK | ng/ml | 1.6E3 | 1.4E3 | 1.7E3 | 1.6E3 | 5.7E2 | 5.7E2 | 5.5E2 | 7.5E2 | 4.1E3 | 3.1E3 | 77 | 43 | 64 | 43 | 0.44 |
| jL | ng/ml | 1.8E2 | 2.1E2 | 2.6E2 | 3.4E2 | 1.9E2 | 3.3E2 | 3.6E1 | 6.4E1 | 7.9E2 | 1.7E3 | 77 | 43 | 64 | 43 | 0.57 |
| jM | ng/ml | 7.1E4 | 7.5E4 | 7.0E4 | 7.7E4 | 3.4E4 | 3.8E4 | 3.9E2 | 1.1E4 | 1.5E5 | 1.7E5 | 77 | 43 | 64 | 43 | 0.55 |
| jO | pg/ml | 2.2E5 | 2.5E5 | 2.8E5 | 2.6E5 | 1.5E5 | 1.3E5 | 5.2E4 | 9.6E4 | 7.7E5 | 5.9E5 | 77 | 43 | 64 | 43 | 0.49 |
| jP | pg/ml | 2.3E5 | 3.1E5 | 2.6E5 | 3.0E5 | 1.5E5 | 1.6E5 | 7.0E4 | 5.8E4 | 9.1E5 | 7.0E5 | 77 | 43 | 64 | 43 | 0.58 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jQ | pg/ml | 2.5E3 | 2.4E3 | 3.0E3 | 3.6E3 | 2.3E3 | 4.4E3 | 4.2E1 | 1.0E-9 | 1.2E4 | 1.8E4 | 77 | 43 | 64 | 43 | 0.48 |
| jR | pg/ml | 6.5E3 | 4.7E3 | 9.5E3 | 1.1E4 | 9.9E3 | 1.6E4 | 1.0E-9 | 1.0E-9 | 5.5E4 | 9.0E4 | 77 | 43 | 64 | 43 | 0.46 |
| jT | pg/ml | 1.6E5 | 1.8E5 | 1.7E5 | 1.8E5 | 6.9E4 | 5.9E4 | 6.8E4 | 8.8E4 | 4.5E5 | 3.5E5 | 77 | 43 | 64 | 43 | 0.53 |
| xA | pg/ml | 3.9E0 | 5.7E0 | 1.7E1 | 1.2E1 | 5.7E1 | 2.3E1 | 1.0E-9 | 1.0E-9 | 3.9E2 | 1.2E2 | 48 | 25 | 44 | 25 | 0.54 |
| yE | pg/ml | 7.8E1 | 7.9E1 | 8.2E1 | 8.9E1 | 4.9E1 | 4.6E1 | 6.4E0 | 1.4E1 | 3.0E2 | 2.5E2 | 48 | 25 | 44 | 25 | 0.55 |
| tM | pg/ml | 4.3E1 | 3.9E1 | 4.3E1 | 3.9E1 | 2.0E1 | 2.3E1 | 1.0E-9 | 1.0E-9 | 1.0E2 | 1.1E2 | 48 | 25 | 44 | 25 | 0.44 |
| tL | pg/ml | 1.0E-9 | 1.0E-9 | 7.8E0 | 1.5E-1 | 3.8E1 | 3.9E-1 | 1.0E-9 | 1.0E-9 | 2.6E2 | 1.8E0 | 48 | 25 | 44 | 25 | 0.46 |
| jU | mIU/ml | 3.8E0 | 5.1E0 | 1.0E1 | 8.0E0 | 1.7E1 | 9.1E0 | 8.9E-2 | 4.2E-2 | 8.1E1 | 5.3E1 | 77 | 43 | 64 | 43 | 0.56 |
| jV | mIU/ml | 1.6E0 | 1.3E0 | 3.5E0 | 2.7E0 | 5.4E0 | 3.1E0 | 2.1E-2 | 1.7E-3 | 3.1E1 | 1.4E1 | 77 | 43 | 64 | 43 | 0.47 |
| jY | ng/ml | 9.7E-4 | 7.4E-4 | 1.1E-2 | 3.7E-3 | 4.2E-2 | 6.4E-3 | 1.0E-9 | 1.0E-9 | 3.0E-1 | 2.6E-2 | 77 | 43 | 64 | 43 | 0.46 |
| kC | pg/ml | 9.7E1 | 1.1E2 | 2.4E2 | 1.4E2 | 5.6E2 | 1.1E2 | 2.1E1 | 2.1E1 | 3.5E3 | 5.9E2 | 54 | 30 | 47 | 30 | 0.53 |
| kE | pg/ml | 1.3E5 | 1.4E5 | 1.3E5 | 1.5E5 | 3.3E4 | 4.9E4 | 4.1E4 | 1.2E4 | 2.0E5 | 2.7E5 | 54 | 30 | 47 | 30 | 0.60 |
| kF | pg/mL | 6.6E1 | 6.6E1 | 8.0E1 | 6.8E1 | 7.0E1 | 2.0E1 | 3.2E1 | 2.6E1 | 5.1E2 | 1.2E2 | 54 | 30 | 47 | 30 | 0.48 |
| kG | pg/mL | 9.1E3 | 9.2E3 | 1.2E4 | 1.2E4 | 1.4E4 | 1.1E4 | 7.5E2 | 1.1E3 | 9.1E4 | 5.8E4 | 54 | 30 | 47 | 30 | 0.52 |
| kI | pg/ml | 2.2E2 | 1.8E2 | 2.4E2 | 2.1E2 | 1.4E2 | 1.2E2 | 5.4E1 | 1.0E-9 | 8.7E2 | 6.2E2 | 54 | 30 | 47 | 30 | 0.40 |
| kK | pg/ml | 1.2E2 | 1.4E2 | 1.7E2 | 1.7E2 | 1.8E2 | 1.7E2 | 2.2E1 | 2.1E1 | 1.2E3 | 9.1E2 | 54 | 30 | 47 | 30 | 0.51 |
| kN | pg/ml | 1.0E3 | 9.4E2 | 1.5E3 | 2.2E3 | 1.9E3 | 3.5E3 | 2.1E2 | 3.0E2 | 1.3E4 | 1.7E4 | 54 | 30 | 47 | 30 | 0.55 |
| kO | pg/ml | 7.7E3 | 7.7E3 | 1.1E4 | 8.3E3 | 1.8E4 | 3.7E3 | 4.0E3 | 4.2E3 | 1.3E5 | 2.5E4 | 54 | 30 | 47 | 30 | 0.49 |
| kP | pg/ml | 5.4E3 | 6.6E3 | 6.7E3 | 7.1E3 | 5.5E3 | 4.4E3 | 8.6E2 | 9.6E2 | 3.3E4 | 1.7E4 | 54 | 30 | 47 | 30 | 0.56 |
| kQ | pg/ml | 4.3E3 | 5.0E3 | 4.9E3 | 6.3E3 | 2.3E3 | 4.9E3 | 5.6E2 | 2.0E3 | 1.2E4 | 2.5E4 | 100 | 43 | 86 | 43 | 0.57 |
| kR | pg/ml | 2.4E1 | 2.1E1 | 4.0E1 | 2.8E1 | 1.0E2 | 2.4E1 | 1.0E-9 | 4.8E0 | 1.0E3 | 1.1E2 | 100 | 43 | 86 | 43 | 0.46 |
| kS | pg/ml | 7.7E2 | 9.3E2 | 9.9E2 | 9.9E2 | 1.4E3 | 5.5E2 | 8.2E1 | 2.6E2 | 1.4E4 | 2.5E3 | 100 | 43 | 86 | 43 | 0.57 |
| pS | ng/ml | 2.0E5 | 1.3E5 | 2.2E5 | 1.9E5 | 9.5E4 | 1.6E5 | 7.5E4 | 6.0E4 | 5.0E5 | 8.3E5 | 49 | 24 | 45 | 24 | 0.31 |
| rZ | ng/ml | 1.2E-3 | 2.0E-3 | 7.9E-3 | 1.0E-2 | 2.1E-2 | 2.1E-2 | 1.0E-9 | 1.0E-9 | 1.1E-1 | 1.1E-1 | 73 | 40 | 58 | 40 | 0.58 |
| rY | ng/ml | 5.4E-2 | 6.5E-2 | 2.5E-1 | 5.7E-1 | 8.3E-1 | 3.2E0 | 1.0E-9 | 1.0E-9 | 6.3E0 | 2.0E1 | 73 | 40 | 58 | 40 | 0.53 |
| rX | ng/ml | 1.0E-9 | 1.0E-9 | 9.2E-2 | 8.5E-2 | 4.5E-1 | 4.9E-1 | 1.0E-9 | 1.0E-9 | 3.7E0 | 3.1E0 | 73 | 40 | 58 | 40 | 0.46 |
| lK | pg/ml | 7.1E1 | 7.1E1 | 1.4E2 | 1.5E2 | 1.8E2 | 1.9E2 | 1.0E-9 | 1.0E-9 | 7.0E2 | 7.2E2 | 77 | 42 | 64 | 42 | 0.49 |
| lL | pg/ml | 1.8E3 | 1.4E3 | 3.4E3 | 2.1E3 | 5.5E3 | 2.0E3 | 7.5E1 | 8.9E1 | 4.2E4 | 7.7E3 | 77 | 43 | 64 | 43 | 0.40 |
| lM | pg/ml | 1.0E3 | 1.3E3 | 3.3E3 | 5.1E3 | 7.5E3 | 9.1E3 | 3.9E1 | 9.5E0 | 5.1E4 | 4.0E4 | 77 | 43 | 64 | 43 | 0.54 |
| lN | pg/ml | 1.0E-9 | 1.0E-9 | 7.3E0 | 3.2E0 | 2.2E1 | 6.3E0 | 1.0E-9 | 1.0E-9 | 1.5E2 | 2.9E1 | 77 | 43 | 64 | 43 | 0.46 |
| lO | pg/ml | 1.0E-9 | 1.0E-9 | 5.2E-1 | 3.5E0 | 4.6E0 | 2.1E1 | 1.0E-9 | 1.0E-9 | 4.0E1 | 1.4E2 | 77 | 42 | 64 | 42 | 0.52 |
| zA | ng/ml | 1.9E7 | 2.1E7 | 2.0E7 | 1.9E7 | 6.8E6 | 6.0E6 | 6.7E6 | 5.9E6 | 3.6E7 | 2.8E7 | 44 | 25 | 40 | 25 | 0.51 |
| rW | ng/ml | 1.3E-2 | 2.2E-2 | 2.4E-2 | 4.2E-2 | 3.1E-2 | 5.4E-2 | 1.0E-9 | 1.0E-9 | 1.7E-1 | 1.9E-1 | 49 | 23 | 46 | 23 | 0.61 |
| rV | ng/ml | 1.0E-9 | 1.0E-9 | 9.2E-3 | 2.0E-2 | 3.7E-2 | 5.7E-2 | 1.0E-9 | 1.0E-9 | 2.2E-1 | 2.4E-1 | 49 | 23 | 46 | 23 | 0.55 |
| rU | ng/ml | 9.5E-2 | 8.1E-2 | 1.4E-1 | 1.9E-1 | 2.3E-1 | 3.9E-1 | 1.0E-9 | 1.0E-9 | 1.4E0 | 1.9E0 | 49 | 23 | 46 | 23 | 0.57 |
| rT | ng/ml | 6.7E0 | 5.3E0 | 6.8E0 | 6.8E0 | 4.1E0 | 5.0E0 | 7.5E-1 | 1.0E0 | 2.1E1 | 2.0E1 | 49 | 23 | 46 | 23 | 0.47 |
| rS | ng/ml | 3.4E0 | 5.8E0 | 5.6E0 | 1.2E1 | 6.8E0 | 1.8E1 | 1.0E0 | 1.0E0 | 3.8E1 | 7.0E1 | 49 | 23 | 46 | 23 | 0.61 |
| sC | pg/mL | 5.6E3 | 8.3E3 | 8.5E3 | 2.0E4 | 7.1E3 | 2.3E4 | 1.7E3 | 2.2E3 | 3.2E4 | 8.0E4 | 49 | 24 | 45 | 24 | 0.66 |
| yL | pg/ml | 3.4E1 | 2.7E1 | 4.2E1 | 8.3E1 | 2.8E1 | 2.8E2 | 5.6E0 | 1.2E1 | 1.8E2 | 1.4E3 | 47 | 25 | 43 | 25 | 0.32 |
| rP | ng/ml | 7.7E1 | 8.7E1 | 1.7E2 | 2.4E2 | 2.3E2 | 2.6E2 | 1.0E-9 | 1.3E0 | 1.2E3 | 8.0E2 | 49 | 23 | 46 | 23 | 0.55 |
| rQ | ng/ml | 1.0E-9 | 1.0E-9 | 3.4E0 | 5.4E0 | 1.5E1 | 2.6E1 | 1.0E-9 | 1.0E-9 | 8.9E1 | 1.2E2 | 49 | 23 | 46 | 23 | 0.50 |
| rO | ng/ml | 2.5E-2 | 3.5E-2 | 3.9E-2 | 5.6E-2 | 7.1E-2 | 7.1E-2 | 1.0E-9 | 1.0E-9 | 4.4E-1 | 3.3E-1 | 49 | 23 | 46 | 23 | 0.61 |
| rR | ng/ml | 3.9E0 | 3.9E0 | 2.2E1 | 1.4E1 | 6.6E1 | 2.5E1 | 1.0E-9 | 1.0E-9 | 4.5E2 | 9.5E1 | 49 | 23 | 46 | 23 | 0.50 |
| rN | ng/ml | 6.4E-1 | 6.8E-1 | 7.0E-1 | 1.1E0 | 3.8E-1 | 1.0E0 | 5.1E-2 | 2.4E-1 | 2.1E0 | 4.4E0 | 49 | 23 | 46 | 23 | 0.47 |
| qO | pg/ml | 9.7E3 | 1.2E4 | 1.2E4 | 1.8E4 | 8.2E3 | 1.5E4 | 2.2E3 | 1.9E3 | 3.9E4 | 6.4E4 | 50 | 23 | 47 | 23 | 0.62 |
| qP | pg/ml | 3.6E2 | 3.6E2 | 3.9E2 | 5.6E2 | 2.5E2 | 4.6E2 | 1.0E-9 | 1.2E2 | 1.1E3 | 2.2E3 | 50 | 23 | 47 | 23 | 0.59 |
| qQ | pg/ml | 3.1E0 | 6.3E0 | 1.5E1 | 1.0E1 | 4.0E1 | 1.2E1 | 1.0E-9 | 1.0E-9 | 2.8E2 | 4.3E1 | 50 | 23 | 47 | 23 | 0.51 |
| nW | pg/ml | 1.1E5 | 1.2E5 | 1.1E5 | 1.2E5 | 2.5E4 | 2.9E4 | 5.8E4 | 6.7E4 | 1.8E5 | 1.7E5 | 100 | 43 | 86 | 43 | 0.56 |
| nY | pg/ml | 1.9E3 | 2.2E3 | 2.3E3 | 2.5E3 | 1.4E3 | 1.3E3 | 6.5E2 | 5.7E2 | 9.9E3 | 5.5E3 | 100 | 43 | 86 | 43 | 0.57 |
| oO | pg/ml | 8.2E4 | 1.0E5 | 1.2E5 | 1.2E5 | 1.1E5 | 8.0E4 | 4.0E4 | 3.3E3 | 6.2E5 | 3.0E5 | 52 | 26 | 45 | 26 | 0.57 |
| oP | pg/ml | 1.3E5 | 1.6E5 | 1.4E5 | 1.7E5 | 8.4E4 | 1.1E5 | 4.8E4 | 2.4E4 | 3.5E5 | 4.2E5 | 52 | 26 | 45 | 26 | 0.58 |
| oQ | pg/ml | 3.0E3 | 3.5E3 | 3.2E3 | 4.9E3 | 1.6E3 | 4.2E3 | 1.1E3 | 9.1E2 | 1.0E4 | 2.1E4 | 52 | 26 | 45 | 26 | 0.61 |
| oE | pg/ml | 2.1E2 | 2.7E2 | 4.6E2 | 5.7E2 | 6.4E2 | 7.0E2 | 1.0E-9 | 1.0E-9 | 4.7E3 | 3.4E3 | 100 | 43 | 86 | 43 | 0.55 |
| oF | pg/ml | 8.6E3 | 1.5E4 | 2.0E4 | 2.9E4 | 3.3E4 | 3.5E4 | 6.4E1 | 1.0E3 | 2.3E5 | 1.4E5 | 100 | 43 | 86 | 43 | 0.61 |
| oH | pg/ml | 4.2E1 | 4.1E1 | 9.3E1 | 7.3E1 | 1.5E2 | 8.3E1 | 4.2E0 | 4.4E0 | 8.6E2 | 3.2E2 | 100 | 43 | 86 | 43 | 0.48 |
| oK | pg/ml | 6.2E2 | 1.2E3 | 1.9E3 | 1.7E3 | 3.2E3 | 1.6E3 | 5.2E1 | 1.9E2 | 1.8E4 | 6.8E3 | 100 | 43 | 86 | 43 | 0.59 |
| oN | pg/ml | 4.7E2 | 6.3E2 | 8.0E2 | 7.8E2 | 1.9E3 | 7.1E2 | 1.5E2 | 2.5E2 | 1.8E4 | 4.6E3 | 100 | 43 | 86 | 43 | 0.64 |

Figure 6 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| oW | pg/ml | 2.0E2 | 3.6E2 | 4.7E2 | 4.7E2 | 1.1E3 | 5.1E2 | 7.7E1 | 9.0E1 | 6.0E3 | 1.8E3 | 28 | 10 | 26 | 10 | 0.60 |
| oT | pg/ml | 3.1E2 | 2.7E2 | 3.5E2 | 3.4E2 | 1.8E2 | 1.9E2 | 9.9E1 | 1.3E2 | 7.8E2 | 7.9E2 | 28 | 10 | 26 | 10 | 0.47 |
| oV | pg/ml | 1.4E2 | 1.1E2 | 2.4E2 | 3.1E2 | 3.2E2 | 6.8E2 | 1.0E-9 | 1.1E1 | 1.4E3 | 2.2E3 | 28 | 10 | 26 | 10 | 0.50 |
| oD | pg/ml | 1.6E4 | 1.3E4 | 1.8E4 | 1.4E4 | 8.1E3 | 5.3E3 | 8.7E3 | 6.6E3 | 4.6E4 | 2.5E4 | 28 | 10 | 26 | 10 | 0.30 |
| uL | ng/ml | 3.8E1 | 3.3E1 | 4.1E1 | 5.3E1 | 2.4E1 | 7.1E1 | 1.0E-9 | 1.1E1 | 1.6E2 | 3.7E2 | 48 | 24 | 44 | 24 | 0.47 |
| uO | ng/ml | 3.5E-1 | 4.2E-1 | 8.5E-1 | 7.6E-1 | 1.5E0 | 1.1E0 | 1.0E-9 | 1.0E-9 | 9.3E0 | 5.0E0 | 48 | 24 | 44 | 24 | 0.50 |
| uM | ng/ml | 6.3E-1 | 6.6E-1 | 1.2E0 | 7.6E-1 | 2.3E0 | 5.5E-1 | 1.0E-9 | 1.0E-9 | 1.3E1 | 2.5E0 | 48 | 24 | 44 | 24 | 0.50 |
| uI | ng/ml | 6.5E-2 | 8.9E-2 | 1.3E-1 | 1.1E-1 | 1.9E-1 | 8.3E-2 | 1.6E-2 | 1.5E-2 | 1.1E0 | 3.8E-1 | 48 | 24 | 44 | 24 | 0.53 |
| uN | ng/ml | 1.5E1 | 1.5E1 | 1.6E1 | 1.7E1 | 6.5E0 | 8.5E0 | 7.8E0 | 6.4E0 | 4.1E1 | 4.1E1 | 48 | 24 | 44 | 24 | 0.46 |
| uG | ng/ml | 2.2E1 | 1.9E1 | 2.5E1 | 2.6E1 | 1.3E1 | 2.7E1 | 9.8E0 | 6.7E0 | 6.9E1 | 1.3E2 | 48 | 24 | 44 | 24 | 0.42 |
| uR | ng/ml | 2.3E0 | 2.7E0 | 4.2E0 | 3.3E0 | 9.1E0 | 3.0E0 | 9.9E-1 | 7.3E-1 | 6.4E1 | 1.4E1 | 48 | 25 | 44 | 25 | 0.51 |
| uP | ng/ml | 1.8E0 | 2.4E0 | 2.2E0 | 2.9E0 | 1.3E0 | 1.3E0 | 1.1E0 | 1.3E0 | 9.1E0 | 6.1E0 | 48 | 25 | 44 | 25 | 0.72 |
| uV | ng/ml | 1.0E-9 | 1.1E-3 | 1.1E-2 | 1.1E-2 | 3.3E-2 | 1.6E-2 | 1.0E-9 | 1.0E-9 | 2.0E-1 | 6.1E-2 | 48 | 25 | 44 | 25 | 0.55 |
| uT | ng/ml | 6.2E1 | 6.4E1 | 8.8E1 | 9.5E1 | 9.6E1 | 8.7E1 | 1.2E1 | 1.3E1 | 5.8E2 | 4.1E2 | 48 | 25 | 44 | 25 | 0.56 |
| uU | ng/ml | 1.6E0 | 1.4E0 | 2.0E0 | 2.5E0 | 1.1E0 | 3.8E0 | 6.0E-1 | 5.9E-1 | 5.4E0 | 2.0E1 | 48 | 25 | 44 | 25 | 0.45 |
| uW | ng/ml | 7.5E0 | 7.1E0 | 7.9E0 | 8.1E0 | 2.8E0 | 2.7E0 | 4.0E0 | 4.4E0 | 2.2E1 | 1.4E1 | 48 | 24 | 44 | 24 | 0.50 |
| vB | ng/ml | 2.7E0 | 3.3E0 | 2.7E0 | 3.2E0 | 1.3E0 | 1.5E0 | 5.9E-1 | 1.2E0 | 5.6E0 | 7.7E0 | 48 | 24 | 44 | 24 | 0.60 |
| vC | ng/ml | 1.0E-9 | 1.0E-9 | 7.5E-3 | 1.0E-9 | 3.5E-2 | 0.0E0 | 1.0E-9 | 1.0E-9 | 2.0E-1 | 1.0E-9 | 48 | 24 | 44 | 24 | 0.47 |
| uY | ng/ml | 8.3E-1 | 7.7E-1 | 1.3E0 | 1.1E0 | 1.2E0 | 1.1E0 | 8.7E-2 | 1.9E-1 | 4.9E0 | 4.4E0 | 48 | 24 | 44 | 24 | 0.45 |
| uZ | ng/ml | 5.9E-1 | 4.2E-1 | 8.8E-1 | 7.5E-1 | 1.1E0 | 1.0E0 | 1.4E-1 | 1.2E-1 | 7.2E0 | 4.9E0 | 48 | 24 | 44 | 24 | 0.39 |
| uX | ng/ml | 1.1E1 | 1.2E1 | 1.2E1 | 1.8E1 | 6.7E0 | 1.8E1 | 3.6E0 | 5.1E0 | 3.3E1 | 7.8E1 | 48 | 24 | 44 | 24 | 0.57 |
| vA | ng/ml | 6.8E-2 | 7.0E-2 | 8.5E-2 | 9.9E-2 | 5.8E-2 | 9.2E-2 | 2.5E-2 | 2.6E-2 | 3.0E-1 | 4.2E-1 | 48 | 24 | 44 | 24 | 0.49 |
| vH | ng/ml | 1.2E-1 | 1.2E-1 | 1.7E-1 | 2.2E-1 | 1.6E-1 | 3.7E-1 | 1.5E-2 | 1.4E-2 | 8.0E-1 | 1.9E0 | 49 | 24 | 45 | 24 | 0.48 |
| vI | ng/ml | 1.8E0 | 2.3E0 | 1.9E0 | 2.6E0 | 1.2E0 | 2.4E0 | 6.2E-3 | 6.3E-3 | 5.1E0 | 1.0E1 | 49 | 24 | 45 | 24 | 0.56 |
| vP | ng/ml | 3.8E2 | 5.6E2 | 4.4E2 | 6.4E2 | 3.2E2 | 4.8E2 | 7.0E1 | 1.3E2 | 1.5E3 | 2.2E3 | 48 | 25 | 44 | 25 | 0.62 |
| vT | ng/ml | 7.7E1 | 9.2E1 | 1.2E2 | 1.0E2 | 1.2E2 | 5.8E1 | 4.1E1 | 4.5E1 | 6.9E2 | 3.3E2 | 48 | 25 | 44 | 25 | 0.54 |
| vU | ng/ml | 1.0E-9 | 1.0E-9 | 2.3E1 | 2.6E1 | 3.2E1 | 3.5E1 | 1.0E-9 | 1.0E-9 | 1.0E2 | 1.4E2 | 48 | 25 | 44 | 25 | 0.52 |
| vQ | ng/ml | 3.4E2 | 3.4E2 | 3.4E2 | 3.8E2 | 1.3E2 | 1.4E2 | 6.7E1 | 1.9E2 | 7.0E2 | 6.5E2 | 48 | 25 | 44 | 25 | 0.58 |
| vO | ng/ml | 1.7E3 | 1.8E3 | 1.8E3 | 1.9E3 | 4.6E2 | 4.3E2 | 1.0E3 | 1.1E3 | 3.0E3 | 2.7E3 | 48 | 25 | 44 | 25 | 0.58 |
| vS | ng/ml | 1.3E3 | 1.4E3 | 1.3E3 | 1.3E3 | 3.5E2 | 5.0E2 | 1.0E-9 | 1.0E-9 | 1.8E3 | 1.9E3 | 48 | 25 | 44 | 25 | 0.59 |
| vV | ng/ml | 8.4E2 | 1.2E3 | 1.1E3 | 1.7E3 | 9.9E2 | 1.9E3 | 1.1E2 | 2.2E2 | 5.0E3 | 9.0E3 | 48 | 25 | 44 | 25 | 0.61 |
| vW | ng/ml | 1.5E2 | 1.7E2 | 1.7E2 | 2.2E2 | 1.3E2 | 1.6E2 | 4.3E1 | 6.0E1 | 6.7E2 | 7.7E2 | 48 | 25 | 44 | 25 | 0.62 |
| pF | pg/ml | 5.0E-1 | 7.1E-1 | 6.8E-1 | 9.9E-1 | 1.0E0 | 9.4E-1 | 1.0E-9 | 1.0E-9 | 9.4E0 | 4.4E0 | 100 | 43 | 86 | 43 | 0.61 |
| pH | ng/ml | 7.3E0 | 1.2E1 | 8.6E0 | 1.4E1 | 4.0E0 | 1.2E1 | 3.4E0 | 5.9E0 | 1.8E1 | 4.7E1 | 28 | 10 | 26 | 10 | 0.74 |
| pI | ng/ml | 7.1E1 | 6.8E1 | 7.0E1 | 7.6E1 | 3.2E1 | 4.6E1 | 2.6E1 | 2.7E1 | 1.5E2 | 2.0E2 | 28 | 10 | 26 | 10 | 0.48 |
| pK | ng/ml | 4.5E-1 | 5.5E-1 | 5.0E-1 | 5.5E-1 | 2.9E-1 | 1.9E-1 | 2.0E-1 | 2.7E-1 | 1.6E0 | 8.6E-1 | 28 | 10 | 26 | 10 | 0.63 |

Analyte panel data:

Unconstrained panels with 3 analytes, where 1.0E-10 >= 'model p-value' > 0. Contains 815 panels of 38,530,102 total panels evaluated. :
Et{Nd(aA aO aW Bo Cw Db Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nc(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Mb(aA Fp Fr Hq Hr Hu Hv Hw Hx Ih Ii Ij Ik Il Im In Io Ip Iq Is It Iu Iv Jg Jh Ji Jj Jk Jl Jm Jn Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nl(aA Fp Fr Hq Hr Hu Hv Hw Hx Ih Ii Ij Ik Il Im In Io Iq It Iu Iv Jg Jh Ji Jj Jk Jl Jm Jn Jo Jp Jq Jr Js Jt Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Ne Nf Ng Nh Ni Nj Nk Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ne(Hx Ii Ij Il In Jj Jo Lu Lv Lw Mf Mh Ml Ms My Nb Ng Nh Of Oi Oy Pd Pz Qb Qc) Ms(Fp Hx Ik Ji Jr Li Lv Lx Mf Mh Ml Mt My Nb Nh Nj Nk) Ii(Fp Hx Ik Jr Lh Li Lj Lv Mf Mh Ml Mt Nj Nk On Po Qa) Hx(aA Jj Jr Lj Mh Nj Nk Of Ok) Nj(Db In Jj Mh Oi) My(Mt Mv) MfJo NiNk] Ok{Nd(aA Fp Fr Hv Hx Ih Ii Ij Ik Il Im In Io Ip Iq Ir Is It Iu Iv Jg Jj Jj Jn Jo Jp Jq Jr Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Ne Nf Ng Nh Ni Nj Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qe) Nc(Fp Fr Hr Hv Hx Ii Ij Il Im In Iq Ir It Iu Iv Jj Lu Lv Lw Lx Ly Lz Ma Mb Mc Me Mf Mh Mi Mj Mk Ml Mm Mn Mr Ms Mt Mu Mv Mw Mx My Na Nb Ne Nf Ng Nh Ni Nj Nk Nm No Nr Ns Nt Nu Nv Nx Ny Oe Of Og Oh Oi Om On Oy Oz Pb Pc Pd Pe Pf Pg Qc) Nl(Ii Ij Il In It Lv Mb Mf Mn Ms My Nb Nh) Mb(Fr In Mm Ne Nk) Ii(Ne Nk On) Nelt NjIn} Nd{On(aA Ii In Iu Jj Lw Mm Ms Mw My Nc Of Og Oi Oy Pf) Mm(aA Cw Fr Im Is Ji Li Lv Mr Mz Nc

Figure 6 Continued

No Pe Pf) Fr(Jj Nc)} aC{Ad(Aj aM aW Bo cF cN cZ Di fR) fR(BC Ch Co Cv Db Dg Dl) Bo(Dg Dl) CwcZ DgaW DrEf} li{On(Mb Nc Ne Nj Nl)} Ad{Aj(aW Bo) BoaM} MbMmNc

Unconstrained panels with 3 analytes, where 1.0E-9 >= 'model p-value' > 1.0E-10. Contains 1,524 panels of 38,530,102 total panels evaluated. : Et{Ms(aA Fr Hq Hr Hu Hv Hw Ih Ii Ij Il Im In Io Ip Iq Ir Is It Iu Iv Jg Jh Jj Jk Jl Jm Jn Jo Jp Jq Js Jt Lh Lj Lu Lw Ly Lz Ma Mc Md Me Mg Mi Mj Mk Mm Mn Mp Mq Mr Mu Mv Mw Mx Mz Na Nf Ng Ni Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Hx(Fp Fr Hq Hr Hu Hv Hw Ih Ij Ik Il Im In Jg Jh Ji Jl Jm Jn Jo Jq Js Jt Lh Li Lu Lv Lw Lx Ly Lz Ma Mc Md Me Mf Mg Mi Mk Ml Mm Mn Mp Mq Mr Mt Mu Mv Mw Mx My Mz Na Nb Nf Ng Nh Ni Nm Nn No Nq Nr Ns Nt Nu Nv Nw Nx Ny Oe Og Oh Oi Om On Oy Oz Pa Pb Pc Pd Pe Pf Pg Po Pz Qa Qc Qe) Ne(aA Fp Fr Hq Hr Hu Hv Hw Ih Ik Im Io Ip Iq Is It Iu Iv Jg Jh Ji Jk Jl Jm Jn Jp Jq Jr Js Jt Lh Li Lj Lx Ly Lz Ma Mc Md Me Mg Mi Mj Mk Mm Mn Mp Mq Mr Mt Mu Mv Mw Mx Mz Na Nf Ni Nj Nk Nm Nn No Nq Nr Ns Nt Nu Nv Nw Nx Ny Oe Og Oh Ok Om On Oz Pa Pb Pc Pe Pf Pg Po Qa Qd Qe) Nj(aA aO aR aW Bo cR Cw Fp Fr Hr Hv Hw Ih Ij Ik Il Im Io It Iu Iv Ji Jl Jn Jo Jq Jr Js Jt Li Lj Lu Lv Lx Ly Lz Ma Mc Me Mf Mk Ml Mm Mn Mp Mq Mr Mt Mu Mv Mw Mx My Mz Na Nb Nf Ng Nh Ni Nk Nm No Nr Ns Nt Nu Nv Nx Oe Of Og Ok Oy Oz Pa Pb Pd Pe Pf Pg Pz Qa Qb Qc Qd Qe) Mh(aA Fp Hq Hr Hv Ij Ik Il Im In It Jg Ji Jj Jn Jo Jq Jr Li Lj Lu Lv Lw Lx Mf Mi Mj Mk Ml Mn Mt Mv Mw Mx My Na Nb Nf Ng Nh Ni Nk Nm Nv Nx Ny Oe Of Og Oi Ok Oy Oz Pb Pd Pg Po Pz Qb Qc Qd) Nd(aC aE AF aG aH al Aj aK aL aM aQ aR aV aX aY aZ bA bB bC BG bH bM bN bQ bR bU bW cA cB cC cF cG Ch cK cM cN cQ cR cT cW cY cZ dB dC dE DI dJ Dk dM dN) Ii(aA Fr Hu Ih Im Is Iv Jg Ji Jj Jl Jn Jq Jt Lu Lw Lx Me Mn Mq Mr Mu Mv Mx My Mz Na Nb Nh Nm Nn No Nr Nx Of Og Oh Ok Om Oy Oz Pa Pd Pe Pf Pz Qc Qd Qe) Mf(Fp Hr Ij Il Im In It Iu Iv Jj Jr Li Lj Lu Lv Lw Ml Mt Mv Mw My Nb Nf Ng Nh Nk Nm No Of Og Oi Ok Oy Pd Pz Qb Qc Qd) My(aA Fp Ir Ik Im In Jg Ji Jj Jo Jr Li Lj Lu Lv Lw Lx Ml Mu Mx Nb Nh Nk No Nr Of Oi Ok Om On Oy Pf Po Qa Qc) Lv(aA Ij Il Im In It Jj Jo Jr Li Lj Ml Mt Mv Mw Nb Ng Nh Nk Nx Of Oi Oh Oy Pg Pz Qb Qc) Nk(Fp Hr Il In Jj Jo Jr Li Lj Lu Lw Ml Mt Mv Mw Nb Ng Of Oi Ok Oy Pz Qb Qc Qd) Ml(aA Hr Ij Il Im In Jj Jo Jr Lj Lw Mt Mv Mw Nf Ng Of Oi Ok Oy Qc) Oy(Fp Ik Jg Jj Jr Li Lu Mt Nb Nh Of On) Jj(Fp Ik Iv Jr Li Lj Mt Nb Nh Nr) Of(Fp Ik Jg Jr Lj Mt Nb Ng Nh Ok) Oi(Fp Ik Jd Jr Li Lj Mt Nb Nh) Jd(Fn It Iu Na Nt Nu Tj) Lj(Il In Jo Lu Qb Qc Qd) Fp(Ij Il In Jo Qb Qc) Li(Ik Il Im Qc Qd) Ng(Ik Jr Mt Mv) Nl(Ip Ir Is Lh) Il(Jr Lz Pf) aR(aC aW Mb) Ik(In Jo) Ok(Hr Jo) LxPg MbIr NaKx InJr QaQb} Ok{Mb(aA Fp Hr Hx Ih Ii Ij Ik Il Im Iq Ir It Iu Iv Jg Jj Jo Li Lj Lu Lv Lw Lx Ly Lz Ma Mc Md Me Mf Mg Mh Mi Mj Mk Ml Mn Mp Mq Mr Ms Mt Mu Mv Mw Mx My Mz Na Nb Nf Ng Nh Ni Nj Nm Nn No Nq Nr Ns Nt Nu Nv Nw Nx Ny Oe Of Og Oh Oi Om On Oy Oz Pa Pb Pc Pd Pe Pf Pg Pz Qc) Nl(aA Fp Fr Hr Hv Hx Ih Ik Im Io Iq Ir Iu Iv Jg Jj Jn Jo Li Lj Lu Lw Lx Ly Lz Ma Mc Md Me Mg Mh Mi Mj Mk Ml Mm Mp Mq Mr Mt Mu Mv Mw Mx Mz Na Nc Ne Nf Ng Ni Nj Nk Nm Nn No Nq Nr Ns Nt Nu Nv Nw Nx Ny Oe Of Og Oh Oi Om On Oy Oz Pa Pb Pc Pd Pe Pf Pg Pz Qb Qc Qd) Nc(aA Hq Hu Hw Ih Ik Io Ip Is Jg Jh Ji Jk Jl Jm Jn Jo Jp Jq Jr Js Jt Lh Li Lj Md Mg Mp Mq Mz Nn Nq Nw Pa Po Pz Qa Qb Qd Qe) Nj(aR Bo cW Db Fr Hr Hx Ii Ij Im Iq Ir It Iu Lv Lx Mf Mh Mm Mn Ms Mt Mx My Nb Ne No Nt Of Og Oi) Ne(Fr Hr Hx Ij Il In Iq Ir Iu Jj Lv Lw Mf Mh Mm Mn Ms My Nb Nf Nh Nk No Nt Of Og Oi Pd) Nd(Bo CW Hq Hu Hw Jh Jk Jl Jm Js Jt Qb Qc Qd) Ii(Fp Fr Ik Jg Lh Lv Lx Mf Mh Ml Mt Nb Nr Po) Nk(Hr Hx In It Lv Mf Ms My Nb) My(Fr Lv Lx Mf Mt Mv On) Ms(Hx It Lv Mf Ml Mt) Hx(Fr Jj Li Lx Mt) FpIt IkIn} Nd{On(Bo Cw Fr Hr Hv Hx Ih Ij Ik Il Im Io Ip Iq Is It Iv Ji Jk Jl Jn Jo Jq Jr Js Li Lj Lv Lx Ly Lz Ma Mb Mc Me Mf Mg Mh Mj Mk Ml Mn Mr Mt Mv Mx Mz Na Nb Ne Nf Ng Nh Nk Nl Nm No Nr Ns Nt Nu Nv Nx Oe Om Oz Pa Pb Pc Pd Pe Pg Po Pz Qc) Mm(aW Bo Db Fp Ih Ij Il In Iq Iu Iv Jg Jj Jl Jn Jp Jq Jr Jt Lh Lj Lu Lw Lx Ly Lz Ma Mb Mc Mh Mi Mj Ml Mn Ms Mt Mv Mw Mx Na Nb Ne Nh Nk Nl Nm No Nr Nw Of Og Oi Om Oz Pa Pd Po Qa Qe) Fr(aA Ih li Im In Is Iu Iv Ji Jl Jn Jq Jr Jt Li Lj Lv Lw Lx Me Mf Mn Mr Ms Mx Mz Na Nk Nl Nm No Of Og Oi Oz Pd Pe Pf) Ji(aA Cw Ij Im In Iq It Jj Li Lx Mn Ms Mt Nc No Og Qa) Jj(Jg Jt Lh Li Lx Mt Qa) Lx(aA Hx Li Pg) Im(Li No Pf) Cw(Jp Lw) aA(Lh Li) AdBo NoNc JgOy} aC{Ad(aF al aJ aL aO AR Aw aX aZ Bb bC bE bJ bM Bn bQ bU cB cE cG Ch cR CT CW Db De dF dI dJ dN) fR(aM Ao Ap Ar aW Ax Ba BB Bg bH Bn Bo bQ cE Cs Cu Cw Dc De Di Dk Fr) Cw(aF aM aO aR AW aX bC bE Bo bU cF cN cW Dg Di dN) Dg(Aj aM aR Aw bC bU cB cF Ch cN cW cZ Db Di) Bb(aM aR AW bC bM Bo bU cF cN Di dN) Ap(aM aR AW Bo cF cZ Di) Aw(aR bM bU cZ Db Dl) Bo(BC bU cZ Dc) DkDr EfGc} Ad{Bo(aF aH aK aO aQ aR aU aV aW bC bM bU cB cF cK cN Co cW cY cZ Db dR eF gL gP) Aj(aK aM aR aU bC bM bU cB cF cG cK cN cR cT cW cY cZ Db dF Dg Di dN) aW(bM cF)} On{Ii(Fp Hx Ik It Iv Lv Mf Mh Ml Ms My Nk) Mb(Jj Mm Ms My Nc Ng Nl Of Oi Oy) Ms(Hx Nc Nl) Jj(Hx Nc Nl) Nj(Bo Db) NcOy IiJd} Mm{Mb(aA Fr Na Nl) Lv(Nc Nl) DbNj MlNc JntV} Fr{Mb(Nc Nl) LvNc NlJj} aM{IcJd bBfR} CwNiNj GpeMhB NmNttV NcJgJj ZqhGiZ aObFfR aWbBeP Unconstrained panels with 3 analytes, where 1.0E-8 >= 'model p-value' > 1.0E-9. Contains 5,377 panels of 38,530,102 total panels evaluated. : Et{Nj(aC AD aE AF aG aH aI AJ aK AL aM AN aP aQ Ar aS aU aV Aw AX aY aZ bA BB BC bE bF BG bH bI bJ bL bM BN bO bP bQ bR bS bU bV bW bX bZ cA cB cC cD cE cF cG CH cI cJ cK cL cM cN cO cP CQ CS cT cU cV cW cX cY cZ dA dB DC dD DE dF DG dH DI dJ DK dL dM dN Hq Hu Ip Iq Ir Is Jg Jh Jk Jm Jp Lh Md Mg Mi Mj Nn Nq Nw Ny Oh Om On Pc Po) Jd(Bg Db Dp Ed Ez Ha Hf Hq Hr Hu Hv Hx Ic Ih Ii Ij In Io Ip Iq Ir Is Iv Jg Jh Jj Jl Js Jt Ju Jv Ki Kk Kp Kr Kx Lv Lw Ly Mb Mc Mh Mj Ml Mp Ms Mu Mv Mx My Nc Nd Ne Nf Ng Nh Nk Nl Nq Ns Nv Nw Oa Of Og Oh Ok Om Oz Pc Pd Pe Pg Pz Qb Qh Ql Qn Qu Qv Qw Qy Qz Rb Rf Rg Rh Ri Rm Tn To Tv Ua Ub Uc Ue Uk Ul Um Uo Ur Us Uu Uv Vo) Ok(aA Fp Fr Hq Hu Hv Hw Ih Ij Ik Il Im In Io Ip Iq Ir It Iu Iv Jg Jh Ji Jj Jk Jl Jm Jn Jp Jq Jr Js Jt Lh Li Lj Lu Lw Lx Ly Lz Ma Mc Md Me Mg Mi Mj Mk Mm Mn Mp Mq Mr Mt Mu Mv Mw Mx Mz Na Nb Nf Ng Nh Ni Nm Nn No Nq Nr Ns Nt Nu Nv Nw Nx Ny Oe Og Oh Oi Om On Oy Oz Pa Pb Pc Pd Pe Pf Pg Po Pz Qa Qb Qc Qd Qe) Nh(aA Fp Fr Hq Hr Hu Hv Hw Ih Ij Ik Il Im In Io Iq It Iu Iv Jg Jh Ji Jk Jl Jm Jn Jo Jp Jq Jr Js Jt Li Lj Lu Lw Lx Ly Lz Ma Mc Md Me Mg Mi Mj Mk Ml Mm Mn Mp Mq Mr Mt Mu Mv Mw Mx Mz Na Nb Nf Ng Ni Nk Nm Nn No Nq Nr Ns Nt Nu Nv Nw Nx Ny Oe Og Oh Om On Oz Pa Pb Pc Pd Pe Pf Pg Po Pz Qa Qb Qc Qd Qe) Oi(aA aC Fr Hq Hr Hu Hv Hw Ih Ii Ij Il Im In Io Iq Is It Iv Jg Jh Ji Jj Jk Jl Jm Jn Jo Jp Jq Js Jt Kx Lh Lu Lw Lx Ly Lz Ma Mc Md Me Mg Mi Mj Mk Mm Mn Mp Mq Mr Mu Mv Mw Mx Mz Na Nf Ng Ni Nm Nn No Nq Nr Ns Nt Nu Nv Nw Nx Ny Oe Of Og Oh Om On Oy Oz Pa Pb Pc Pd Pe Pf Pg Po Pz Qa Qb Qc Qd Qe) Jr(aA Fp Fr Hq Hr Hu Hv Hw Ih Ij Ik Im Io Ip Iq It Iu Iv Jg Jh Ji Jk Jl Jm Jn Jo Jp Jq Js Jt Lh Li Lj Lu Lw Lx Ly Lz Ma Mc Md Me Mg Mi Mj Mk Mm Mn Mp Mq Mr Mt Mu Mv Mw Mx Mz Na Nb Nf Ni Nm Nn No Nq Nr Ns Nt Nu Nv Nw Nx Ny Oe Og Oh Om On Oz Pa Pb Pc Pd Pe Pf Pg Po Pz Qa Qb Qc Qd Qe) Jj(aA Fr Hq Hr Hu Hv Hw Ih Ij Il Im In Io Ip Iq Ir Is It Iu Jg Jh Ji Jk Jl Jm Jn Jo Jp Jq Js Jt Lh Lu Lw Lx Ly Lz Ma Mc Md Me Mg Mi Mj Mk Mm Mn Mp Mq Mr Mu Mv Mw Mx Mz Na Nf Ng Ni Nm Nn No Nq Ns Nt Nu Nv Nw Nx Ny Oe Of Og Oh Om On Oz Pa Pb Pc Pd Pe Pf Pg Po Pz Qa Qb Qc Qd Qe) Of(aA Fr Hq Hr Hu Hv Hw Ih Ij Il Im In Io Ip Iq Is It Iu Iv Jh Ji Jk Jl Jm Jn Jo Jp Jq Js Jt Lh Li Lu Lw Lx Ly Lz Ma Mc Md Me Mg Mi Mj Mk Mm Mn Mp Mq Mr Mu Mv Mw Mx Mz Na Nf Ni Nm Nn No Nq Nr Ns Nt Nu Nv Nw Nx Ny Oe Og Oh Om On Oz Pa Pb Pc Pd Pe Pf Pg Po Pz Qa Qb Qc Qd Qe) Fp(aA Fr Hq Hr Hu Hv Hw Ih Ik Im Io It Iu Iv Jg Jh Ji Jk Jl Jm Jn Jp Jq Js Jt Lh Li Lj Lu Lv Lw Lx Ly Lz Ma Mc Md Me Mg Mi Mj Mk Ml Mm Mn Mp Mq Mr Mt Mu Mv Mw Mx Mz Na Nb Nf Ng Ni Nm Nn No Nq Nr Ns Nt Nu Nv Nw Nx Ny Oe Og Oh Om On Oz Pa Pb Pc Pd Pe Pf Pg Po Pz Qa Qd Qe) Oy(aA Fr Hq Hr Hu Hv Hw Ih Ij Il Im In Io Ip Iq Is It Iu Iv Jh Ji Jk Jl Jm Jn Jo Jp Jq Js Jt Lh Lj Lw Lx Ly Lz Ma Mc Md Me Mg Mi Mj Mk Mm Mn Mp Mq Mr Mu Mv

Figure 6 Continued

Figure 6 Continued

Me Mf Mg Mk Mp Mq Mu My Nf Ng Ni Nj Nq Ns Nt Nu Nv Nx Ny Oe Oh Oy Pb Pc Pg Pz Qb Qc Qd) Cw(Ad Aj An Bb Bg Bo Ch cR Cv Dc Di Dk Hu Hv Hw Hx Im In Io Is It Jg Jh Jj Jl Jn Jo Jq Lh Li Lx Me Ml Mn Mt Mu Mv Na Nf No Nw Om Oy Oz Pd Po Pz Qa Qb Qc Qd Qe) Lx(Hq Hv Im In Iq Is Jg Jl Jn Jp Jq Jr Jt Lh Lv Lw Me Mf Mh Ml Mn Mr Ms Mt Mv Mx Mz Na Nc Nl Nm No Nr Nw Ny Of Og Oi Om Oz Pa Pb Pd Pe Pf Qa) No(aA In Is It Jg Jj Jl Jp Jq Jr Jt Lh Li Lv Lw Ma Me Mf Mn Mr Mt Mv Mw Mx Mz Na Nc Nl Nm Nw Of Og Om Oz Pd Pe Pf Po Qa) On(Af Aj aO aR aW Bb cB cR Db Di Fp Hq Hu Hw Ir Jg Jh Jm Jp Jt Lh Lu Md Mi Mp Mq Mu Ni Nj Nn Nq Nw Ny Oh Qa Qb Qd Qe) Jg(aA Aj aR Bo bR bU cB Db Im In Is Jl Jq Li Lv Lw Mh Ms Mt Mx My Mz Na Nc Ng Nr Of Og Oi Pd Pe Pf) Li(Ik Il In Is Jl Jp Jq Jt Lh Lv Lw Mf Mn Ms Mt Mw Mx Mz Na Nc Nm Nw Of Og Oi Pd Qa) Im(aA Is Jj Jl Jp Jt Lh Lv Lw Mf Mj Mn Mr Mt Mx Mz Nc Nm Nw Og Pd Pe) Mn(aA Is Jj Jl Jp Jt Lh Lw Mt Mv Mx Mz Nc Nl Nw Pd Pe Pf Po Qa) Nw(aA In Jj Lv Lw Mf Ms Mt Mv Mx Na Nc Nl Nm Og Pd Pf) Mt(aA In Is Jl Jp Jq Jr Jt Lh Lv Lw Nc Pd Pf Po) aA(Ip Iq Jp Jt Lv Nc Nn Nr Nv Of Og Po Qa Qe) Jj(Iq Is Jk Jl Jp Mv Nr Nv Po Qe) Lh(Bo Ii In Lw Ms Nc Og Pf) Bo(Dc Dk Jp Nm Of) Lw(Is Jp Pf Qa) Nc(Jp Jt Lv Pf) Ad(Aj Na) In(Jt Qa) Jp(aR Lv) ItJt QaQb} aC{Dg(AD aE AF aG aH al aJ aK AL AN AO AP aQ Ar AS aU aV AX aY aZ BA BB Bc bE bF BG bH bl bJ bL bM BN bO bP bQ bR bS bV bW bX bZ cA cC cD cE cG cH cI cJ cK cL cM CO CP CQ cR CS CT CU CV CX cY dA dB DC DD DE dF dG dH dI dJ DK DL dM dN Dr Fr) Cw(aD aH al AJ aK AL AN Ao Ap aQ Ar AS aU aV Ax aY aZ BA BB Bc bF BG bl bJ bL bM BN bO bQ bR bV bW bX cA cB cC cD cE cG Ch cI cJ cK cL Co CP CQ cR CS CT Cu CV cX cY dA Db DC DD DE dF dG dH dl dJ DK Dl dM Dr Fr) Ad(aD aE Af aG aH aK Al AN Ao AP aQ AS aU aV Ax aY BA bB Bc bF BG bH bI bL bN bO bP bR bS bV bW bX bZ cA cC cD cH cI cJ cK cL cM CO CP CQ CS CU CV CX cY dA dB DC DD dE dG dH DK DL dM Fr) Ap(aD aF aH Aj aL aO AX aZ bA BB bC bE bM Bn bQ bR bU cB cG Ch cJ cN CP CQ cR Cs cT Cu cW Db Dc De dF dJ Dk dM dN Fr) Bb(aD aJ ArAS AX aY bA bB bE bF bJ Bn bQ bR bV bW cB cE cG Ch cK CP cR cS cT Cu cW cZ Db Dc De dF dG Dk Dl dM Fr) fR(Aa Af Aj Al An aO As Aw aX bA bF bO bR bU bW bX cB cF cG cI cJ cK cL cM CP Cq cR CT cW Cx cZ Dd dF dN Ef Ji) Bo(aF aK aM AO aR aU AW AX BA bE bM Bn cB cF cG Ch cN CP cR CT Cu Cv cW Db Dd De dF Di Dk dN Fr) Aw(aF aL aM An aO Ar aW AX Ba BC bE bJ bQ bR bW cB cF cG Ch cK cN cR Cu cW Dc dF Dl dJ Dk dN Fr) Di(aF aM aR aX BC bE bM bU cB cF Cu cZ Db Dc Dk Dl dN) Dl(aR aW bC bE bU cB cF Ch cN Cp cW cZ dF dN Dr) Dk(aR aW bC bM bU cB cF cZ Db dN Ex) cF(Ao Ba Bc Ch Cp Cu Db Dc De Fr) Ch(aR aW bC bU cN cZ) Dr(Ao Bg dF Fr On) Fr(aR aW cB cZ) Cu(aW bC cZ) Ef(Em Gn) cB(aR Bc) cZ(Cp Dc) DebU NaOn} Ad{Aj(aD aE AF aG aH al aJ AL AN AO AP aQ Ar AS aV Aw AX aY aZ BA BB Bc bE bF BG bH bl bJ bL BN bO bP bQ bR bS bV bW bX bZ cA cC cD cE CH cl cJ cL cM CO CP CQ CS Ct CU CV Cw CX dA dB DC DD DE dG dH dI dJ DK DL dM FR Hx Mb Na Nj) Bo(aD aE Af aG al aJ AL AN Ao AP Ar AS Aw AX aY aZ BA BB Bc bE bF BG bH bl bJ bL BN bO bP bQ bR bS bV bW bX bZ cA cC cD cE cG CH cl cJ cL cM cO CP CQ cR CS CT CU CV Cw CX dA dB DC DD DE dF DG dH Dl dJ DK DL dM dN fP Fr Nj) aW(aK aM aR aU aV Aw bC bU bX cB cJ cK cN Ct cY Di) cF(aM aR aU Aw bM cK cN Ct Db dl) aM(Aw cB cK cT Di) Ct(bA bM cB cT) Nj(Db Na Ni) bM(Aw cN Di) aR(Aw cB) ExqA cBcN}
On{li(Hv Ih Io Ip Iq Ir Is Iu Ji Jj Jo Jq Jr Lh Li Lj Lw Lx Me Mm Mt Mv Mw Na Nb Ng Nh Nm Nq Nr Ns Nx Of Oy Oz Pd Po Qa) Mb(Hx Ij Il In It Iu Ji Jo Jq Jr Lj Lv Lw Mf Mv Mw Mx Na Ne Nf Nj Nk Ns Og Oz Pb Pd Pg Pz Qb Qc) Nc(Hx In It Iu Lv Lw Mf Mh Ml Mm Mv Mw My Ng Nh Ni Nk Of Og Oi Qb) Nl(Hx Il In It Iu Lv Lw Mf Mh Mw My Nb Ng Nh Ni Nk Of Og Oi Oy) Ms(Io It Iu Iv Ji Jj Mf Ml My Ne Nj Of) Nj(Af Aj aM aO aR aW Bb cR Cw dE Jj) Jd(Iu My Na Nt Nu Tj) Ne(Jj My Of Oy) Jj(Lv Mf) NacK HxOf Ttlt} Mm{Mb(Fp Hv Hw Ih Ij Il Im In Is Iv Jg Ji Jj Jl Jn Jp Jq Jr Jt Lh Li Lj Lu Lv Lw Lx Lz Ml Mn Mr Ms Mt Mv Mx My Mz Nb Ne Nh Ni Nj Nk Nm No Nr Nw Of Og Om Oy Oz Pa Pb Pd Pe Pf Qa) Nc(Fp Fr Hx In Iv Jg Ji Jj Jq Li Lx Me Mf Mh Mn Ms Na Nb Nh Ni Nk No Of Og Pe Pf) tV(Di Ij Il Jr Lv Mn Mp Mt Nq Nt Oh Qb Qc Qd wQ) Nl(Fr In Ji Jj Ml Mn Nb Nh Ni No) Jd(Db Fn Iq It Iu Na Qv Qz) Di(tO tT wJ) Lv(Jj Ne tQ) Nj(aW Bo Cw) tX(Nq Qd)} Nc{Fr(Hv Hx Ii In Ji Jj Jq Lw Mf Mh Ml Ms My Nb Ng Nh Ni Nk Nm Oi Oy) Lv(aA Im In Jj Ji Jj Li Lw Lx Ma Mf Mn Mt Nb Ni Nk Nm No Nw Pf) Ji(Hx Ii In It Jj Lx Mb Mn Ms Ni Nk Qb) Jg(Ii In Mb Mh Ms Ni Of Oi Oy) Mb(Jt Li Lx Mt Na No Nw) Jj(Jt Lh Li Lx Mt Po) Ms(Lh Nw) Li(In Ni) LxPg liLh} Nl{Fr(Hv Hx Ii Il In Iu Ji Lv Lw Mf Mh Ml Mn Ms My Na Nb Ng Nh Ni Nk Nm Of Og Oi Oy) Lv(aA Im Jg Ji Jj Li Lx Mn Nb No) Ji(Hx Ii Ij In It Jj Mb Mn Ms) Jj(Jg Lh Li Lx Mn Mt) In(Jg Li Nb) Jg(Ms Oy) LxPg MnNb liLh} Bo{Dl(aK aM aQ aR aU aV AW bC bM bU cB cF Ch cK cT cW cY) Dg(Aj aK aM aR aU aW Bn cF) Nj(Cw Ni Of) BbaM} Jd{Tj(Cw Ip Iq Ir Lh Lx Po Qa Ut) It(Cw Ji Lh Lw Qa Tn) Iv(Cw Kq Lw Om Tv) Ic(Cw Iq)} Dg{Aj(aK aM aR AW Bn cF cK cY) aW(aD aM aR aU bM bU cF cK)} Nj{Cw(Aj Ch Db Fr In Jj Lx Nf Nk) Db(Ch Fr Jg Ji Jp Lx Nw) AjJg} Pj{Qv(tV uT vH vS yH tL) Di(tO tT) Ic(qB qD) CwoK HutV} Mb{Fr(Ji Jj Lw Na Ne) Ji(Im Ms Mt) Jj(Jg Mt)} fR{bB(aN bA bC Db Dl) DIcE aMbF bCbW} tV{Bb(Nq Qw) Vt(Jl Qw) Illp KyfN} Ne{Jj(Fr Jg Li) MsJi IiLh} Ic{Kq(aM jD jM) CwoK} Jg{Aj(aR Db Hx) LvJj} Vq{Jp(vP vV) SsyL iHsC} hB{oD(bH cX mM mZ)} Bb{aMcK aWbM bBcF} Ms{Ji(Fr Lx Mt)} Zq{Hx(aM Or) OrbW} aW{ApcF AwbM} fN{JpvS RirN} CwcFoK DitSuU NqJtrN LvMtJj TtqWvS aNbBdX sFrSqP Unconstrained panels with 3 analytes, where 1.0E-7 >= 'model p-value' > 1.0E-8. Contains 17,343 panels of 38,530,102 total panels evaluated. : Et{aR(AD aE AF aG aH al AJ aK AL aM AN AP aQ Ar aS aU aV Aw Ax aY aZ bA BB BC bE bF BG bH bl bJ bL bM BN bO bP bQ bS bV bW bX bZ cA cC cD cE cF cG CH cl cJ cL cM cN cO CP Cq cR CS Ct cU cV Cw cX cY cZ dA DB DC DD DE dF DG dH dI dJ DK DL dM dN eF Fb Fp Fr Fw Gl gP Hf Hq Hr Hu Hv Hw iA Ic IH Ii Ij Ik Il Im In Io Iq Is It Iu Iv Jd Jg Jh Ji Jj Jk Jl Jm Jn Jo Jp Jq Jr Js Jt Kr Kx Lh Li Lj Lu Lw Lx Ly Lz Ma Mc Md Me Mf Mg Mh Mi Mj Mk Ml Mm Mn Mp Mq Mr Ms Mu Mv Mw Mx My Mz Nb Nc Ne Nf Ng Nh Ni Nk Nl Nm Nn No Nq Nr Ns Nt Nu Nv Nw Nx Ny Oe Of Og Oi Ok Om On Oy Oz Pa Pb Pc Pd Pe Pf Pg Po Pz Qa Qb Qc Qd Qe) aW(AD aE AF aG aH al AJ aK aL aM aN aP aQ Ar aS aU aV Aw AX aY aZ bA bB bC bE bF BG bH bl bJ bL bM bN BO bP bQ bS bV bW bX bZ cA cB cC cD cE cF cG CH cI cJ cL cM cN cO cP CQ cS cT cU cV cW cX cY cZ dA DB dC DD dE dF dG dH DI dJ dK dL dM dN Ef Fb Fp Fr Fw Gl Hf Hq Hr Hu Hv Hw Hx Ic Ih Ii Ij Ik Il Im In Io Iq Is It Iu Jd Jg Jh Ji Jj Jk Jl Jm Jn Jo Jp Jq Jr Js Jt Kx Lh Li Lj Lu Lw Lx Ly Lz Ma Mc Md Me Mf Mg Mh Mi Mj Mk Ml Mm Mn Mp Mq Mr Ms Mu Mv Mw Mx My Mz Nb Nc Ne Nf Ng Nh Ni Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Qv Ri) aC(aD aE AF aG aH AJ aK aM AN aP aQ Ar aS aU aV Aw Ax aY aZ bA BB BC bE bF BG bH bl bJ bL bM bN bO bP bQ bR bS bU bV bW bX bZ cA cB cC cD cE cF cG CH cI cJ cK cL cM cN cO cP CQ cS cT cU cV cW cX cY cZ dA dB DC DD DE dF DG dH DI dJ dK dL dM dN Dr Fp FR Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mc Md Me Mf Mg Mh Mi Mj Mk Ml Mm Mn Mp Mq Mr Ms Mt Mu Mv Mw Mx My Mz Nb Nc Ne Nf Ng Nh Ni Nk Nl Nm Nn No Nq Nr Ns Nt Nv Nw Nx Ny Oe Of Og Oh Ok Om On Oy Oz Pa Pb Pc Pd Pe Pf Pg Po Pz Qa Qb Qc Qd Qe) Na(aA aK aN aO aQ aU bA Bn Bo bR bU cQ cR cT cY De Di Dp Ed Ef Ez Fa Fb Fn Fr Fw Gl Gp Ha Hf Hq Hr Hu Hv Hw iA Ic IH Ij Il Im Io Ip Iq Ir Is Iu Iv Je Jf Jg Jh Ji Jk Jl Jm Jn Jp Jq Js Jt Ju Jv Jy Kd Ke Ki Kk Kn Ko Kp Kq Kr Ky Kz Ld Lh Lu Lw Lx Ly Lz Ma Mc Md Me Mg Mi Mj Mk Mm Mn Mp Mq Mr Mu Mv Mx Mz Nb Nf Ni Nm Nn No Nq Nr Ns Nt Nu Nv Nw Nx Ny Oa Oe Og Oh oK Om On Or Ou Oz Pa Pb Pc Pd Pe Pf Pg Ph Pi Pj Pk Po Qa Qb Qd Qe Qg Qh Ql Qm Qn Qr Qu Qw Qx Ra Rb Rc Rf Rg Rh Rj Rm Sr Ss Tn To Tt Tv Tz Ua Ub Uc Ud Uf Ug Uh Uk Ul Um Un Uo Up Ur Us Ut Uu Uv Vo Vp Vt Wm Tj tF) Jd(aA Ad Af Aj AL aM An AO Ap Ar As Aw Ax Ba Bb Bc Bn Bo bU cB Ch Co Cp Cq cR Cs Ct Cu Cv Cw Cx cZ Dc Dd De Dg Di Dk Dl Ef Fa Fb Fp Fr Fw Fy Gl Gp Hb Hc Hw Ib Id

Mi Mk Mm Mn Mp Mq Mr Mv Mw Mx Mz Nb Nf Ni Nm No Nq Nr Nv Nw Nx Oe Og Om Oz Pa Pb Pd Pe Pf Pg Po Pz Qa Qb Qc Qd Qe)
Nw(aA Fr Hr Hv Hw Ih Ij Ik Il Im In Io It Iv Jg Jh Ji Jk Jl Jn Jo Jp Jq Js Jt Lu Lw Lx Lz Mc Me Mg Mi Mk Mm Mn Mp Mq Mr Mv Mx Mz Nb Nf Ng Ni Nm No Nq Nr Nv Nx Oe Og Om Oz Pa Pb Pd Pe Pf Pg Po Pz Qa Qb Qc Qd Qe) Pa(aA Fr Hr Hv Hw Ih Ij Ik Il Im In Io It Iv Jg Jh Ji Jk Jl Jn Jp Jq Js Jt Li Lu Lw Lx Lz Mc Me Mg Mi Mk Mm Mn Mp Mq Mr Mt Mv Mw Mx Mz Nb Nf Ni Nm No Nq Nr Nv Nx Oe Og Om Oz Pb Pd Pf Pg Po Pz Qa Qb Qc Qd Qe) Mg(aA Fr Hr Hv Hw Ih Ij Il Im In Io It Iv Jg Jh Ji Jk Jl Jn Jp Jq Js Jt Li Lu Lx Lz Mc Me Mi Mk Mm Mn Mp Mq Mr Mv Mw Mx Mz Nb Nf Ng Ni Nm No Nq Nr Nv Nx Oe Og Om Oz Pb Pd Pe Pf Pg Po Pz Qa Qb Qc Qd Qe) Mq(aA Fr Hr Hv Hw Ih Ij Ik Il Im Io It Iv Jg Jh Ji Jk Jl Jn Jp Jq Js Jt Li Lu Lw Lx Lz Mc Me Mi Mk Mm Mn Mp Mr Mv Mw Mx Mz Nb Nf Ni Nm No Nq Nr Nv Nx Oe Og Om Oz Pb Pd Pe Pf Pg Po Pz Qa Qb Qc Qd Qe) Jk(aA Fr Hr Hv Hw Ih Ij Il Im In Io It Iv Jg Jh Ji Jl Jn Jo Jp Jq Js Jt Lu Lw Lx Lz Mc Me Mi Mk Mm Mn Mp Mr Mv Mw Mx Mz Nf Ni Nm No Nq Nr Nv Nx Oe Og Om Oz Pb Pd Pe Pf Pg Po Pz Qa Qb Qc Qd Qe Qy) Fr(aA Fn Hf Hr Hv Hw Ih Ij Ik Im In Io It Iv Jg Jh Ji Jl Jn Jp Jq Js Jt Li Lu Lw Lx Lz Mc Me Mi Mk Mm Mn Mp Mr Mt Mx Mz Nb Nf Ni Nm No Nq Nr Nv Nx Oe Og Om Oz Pb Pd Pe Pf Pg Po Qa Qb Qd Qe) Mi(Hr Hv Hw Ih Ij Ik Il Im In Io It Iv Jg Jh Ji Jl Jn Jo Jp Jq Js Jt Lu Lw Lx Lz Mc Me Mk Mm Mn Mp Mr Mv Mw Mx Mz Nb Nf Ni Nm No Nq Nr Nv Nx Oe Og Om Oz Pb Pd Pe Pg Po Pz Qa Qb Qc Qd Qe) Hw(aA Hr Hv Ih Ij Ik Il Im In Io Iv Jg Jh Ji Jl Jn Jp Jq Js Jt Lu Lw Lx Lz Mc Me Mk Mm Mn Mp Mr Mv Mx Mz Nb Nf Ni Nm No Nq Nr Nv Nx Oe Og Om Oz Pb Pd Pe Pf Pg Po Pz Qa Qb Qc Qd Qe) Jh(aA Hr Hv Ih Ij Ik Il Im In Io It Iv Jg Ji Jl Jn Jp Jq Js Jt Lu Lw Lx Lz Mc Me Mk Mm Mn Mp Mr Mv Mx Mz Nb Nf Ni Nm No Nq Nr Nv Nx Oe Og Om Oz Pb Pd Pe Pf Pg Po Pz Qa Qb Qc Qd Qe) Js(aA Fn Hr Hv Ih Ij Il Im In Io It Iv Jg Ji Jl Jp Jq Jt Lu Lw Lx Lz Mc Me Mk Mm Mn Mp Mr Mv Mw Mx Mz Nb Nf Ni Nm No Nq Nr Nv Nx Oe Og Om Oz Pb Pd Pe Pf Pg Po Pz Qa Qb Qc Qd Qe) Pb(aA Hr Hv Ih Ij Il Im In Io It Iv Jg Ji Jl Jn Jp Jq Jt Lu Lw Lx Lz Mc Me Mk Mm Mn Mp Mr Mv Mw Mx Mz Nb Nf Ng Ni Nm No Nq Nr Nv Nx Oe Og Om Oz Pd Pe Pf Pg Po Qa Qb Qc Qd Qe) Mk(Hr Hv Ih Ij Il Im In Io It Iv Jg Ji Jl Jn Jp Jq Jt Lw Lx Lz Mc Me Mm Mn Mp Mr Mv Mw Mx Mz Nf Ni Nm No Nq Nr Nv Nx Oe Og Om Oz Pd Pe Pf Pg Po Qa Qb Qc Qd Qe Qz Rm Tj) Jp(Hr Hv Ih Ij Ik Il Im Io It Iv Jg Ji Jl Jn Jq Jt Lu Lw Lz Mc Me Mm Mn Mp Mr Mv Mw Mx Mz Nf Ng Ni Nm No Nq Nr Nv Nx Oe Og Om Oz Pd Pe Pf Pg Po Qa Qb Qc Qd Qe Rm) Om(aA Hr Hv Ih Ij Ik Il Im In Io It Iv Jg Ji Jl Jn Jq Jt Lu Lw Lx Lz Mc Me Mm Mn Mp Mr Mx Mz Nb Nf Ni Nm No Nq Nr Nv Nx Oe Og Oz Pd Pe Pf Pg Po Pz Qa Qb Qc Qd Qe) Mm(aA Hr Hv Ih Ij Il Im Io It Iv Jg Ji Jl Jn Jq Jt Lu Lw Lx Lz Mc Me Mn Mp Mr Mv Mw Mx Mz Nf Ni Nm No Nq Nr Nv Nx Oe Og Oz Pd Pe Pf Pg Po Qa Qb Qc Qd Qe tV) Mr(aA Hr Hv Ih Ij Ik Im Io It Iv Jg Ji Jl Jn Jq Jt Li Lu Lw Lx Lz Mc Me Mn Mp Mv Mx Mz Nf Ni Nm No Nq Nr Nv Nx Oe Og Oz Pd Pe Pf Pg Po Pz Qa Qb Qc Qd Qe) Jl(aA Hr Hv Ih Ij Ik Im Io It Iv Jg Ji Jn Jq Jt Lu Lw Lx Lz Mc Me Mn Mp Mv Mw Mx Mz Nb Nf Ni Nm No Nq Nr Nv Nx Oe Og Oz Pd Pe Pf Pg Po Qa Qb Qc Qd Qe) Nv(aA Hr Hv Ih Ij Il Im In Io It Iv Je Jg Jn Jq Jt Lw Lz Mc Me Mn Mp Mv Mw Mx Mz Nf Ng Ni Nm Nq Nr Nx Oe Og Oz Pd Pe Pf Pg Po Pz Qa Qb Qc Qd Qe Ut) Mz(aA Hr Hv Ih Ij Il Im Io It Iv Jg Ji Jn Jq Jt Li Lu Lw Lx Lz Mc Me Mn Mp Mv Mx Nb Nf Ni Nm No Nq Nr Nx Oe Og Oz Pd Pe Pf Pg Po Qa Qb Qd Qe) Jt(aA Hr Hv Ih Ij Il Im In Io It Iv Jg Ji Jn Jq Lu Lx Lz Mc Me Mn Mp Mv Mw Mx Nf Ni Nm No Nq Nr Nx Oe Og Oz Pd Pe Pf Pg Po Pz Qb Qc Qd Qe) Og(Di Fn Hf Hr Hv Ih Ij Io It Iv Jg Jn Jq Kr Lu Lx Lz Mc Me Mn Mp Mv Mx Nf Ni Nm No Nq Nr Nx Oe Oz Pd Pe Pf Pg Po Qa Qb Qd Qe Qz Rm Tj) Pd(aA Fn Hr Hv Ih Ij Il Im Io It Iv Jg Ji Jn Jq Lz Mc Me Mn Mp Mv Mw Mx Nf Ni Nm No Nq Nr Nx Oe Oz Pe Pg Po Pz Qa Qb Qc Qd Qe Rm Tj) Mn(aA Hr Hv Ih Ij Il Im Io It Iv Jg Ji Jn Jq Lu Lw Lx Lz Mc Me Mp Mv Mw Mx Nf Ni Nm No Nq Nr Nx Oe Oz Pe Pf Pg Po Qa Qb Qc Qd Qe Rm Tj) Ih(aA Hr Hv Ij Ik Im Io It Iv Jg Ji Jn Jq Lu Lw Lx Lz Mc Me Mp Mv Mw Mx Nb Nf Ni Nm No Nq Nr Nx Oe Oz Pe Pf Pg Po Qa Qd Qe) Ij(aA Hr Hv Il Im In Io It Iv Jg Jn Jo Lu Lz Mc Me Mp Mv Mw Mx Nf Ni Nm Nq Nr Nx Oe Oz Pe Pf Pg Po Pz Qb Qc Qd Qe sF tV) Db(Aj Bn Di Ef Fb Fw Gp Hf iA Ic Je Jf Kd Kg Kk Ko Kp Kr Ky Kz Ld Lv Nc Ne Nl oK Or Ou Ph Pi Pj Pk Ql Qy Ue Ur Tj) Po(aA Hr Hv Ik Im Io It Iv Jg Ji Jn Jq Lu Lw Lx Lz Mc Me Mp Mx Nb Nf Ni Nm No Nq Nr Nx Oe Oz Pe Pf Pg Qa Qd Qe Tj) Hf(Aj aM An Ax cQ cR Di Dk Fa Fh Fw Gl iA Ic In Je Ji Jj Kk Kp Lv Me Ms Nd Nf No Oi Ou Ow Oz Pk Qy Ue Uo Tj tF) Qe(aA Hr Hv Ik Im Io It Iv Jg Ji Jn Jq Lu Lw Lz Mc Me Mp Mv Mx Nf Ni Nm No Nq Nr Nx Oe Oz Pe Pf Pg Qa Qd Rm Tj) Pe(aA Hr Hv Im Io It Iv Jg Ji Jn Jq Li Lu Lw Lx Lz Mc Me Mp Mv Mx Nf Ni Nm No Nq Nr Nx Oe Oz Pf Pg Qa Qb Qd) Jg(aA Aj Hr Hv Ik Im It Iv Ji Jn Jq Lu Lw Lx Lz Mc Me Mp Mx Nb Nf Ni No Nq Nr Nx Oe Oz Pf Pg Qa Qb Qd) Qz(Fb Fn Ha Ic In Je Ji Ju Jv Jy Lu Lx Ml Ms Mv My Nd Oi Ow Oy Ql Qn Qy Rf Rg Rh Rm Tn Ue Ur Us Ut Tj) Mc(aA Fb Hr Hv Im Io It Iv Ji Jn Jq Lx Lz Me Mp Mv Mx Nf Ni Nm No Nq Nr Nx Oe Oz Pf Pg Qa Qd) Ni(aA Hr Hv Im Io It Iv Ji Jn Jq Lx Lz Me Mp Mv Mx Nf Nm No Nq Nr Nx Oe Oz Pf Pg Qa Qb Qd) Fn(Hx Ic In Je Jj Lv Ms Mv Nd Nh No Oi Ow Pz Ql Qw Qy Rf Rg Rj Rm Ue Un Uo Ur Us Vo Tj) Lz(aA Hr Hv Io It Iv Ji Jn Jq Lu Lx Me Mp Mv Mw Mx Nf Nm No Nq Nr Nx Oe Oz Pf Pg Qa) Mp(bM Hr Hv Il Im Io It Iv Jn Jq Me Mv Mw Mx Nf Nm No Nq Nr Nx Oe Oz Pg Qa Qb Qd) Mx(aA Hr Hv Im Io It Iv Ji Jn Jq Lu Lx Me Nf Nm No Nq Nr Nx Oe Oz Pf Pg Qa Qd) Nx(dU Hr Hv Il Im Io It Iv Jn Me Mv Mw Nf Nm No Nq Nr Oe Oz Pf Pg Qa Qb Qd) Nq(Hr Hv Io It Iv Jn Jq Me Mv Mw Nf Nm Nr Oe Oz Pf Pg Pz Qa Qb Qc Qd) aA(Hr Ik Im In Io Iv Ji Jn Jo Jq Li Lw Lx Nf Nm No Nr Oe Oz Pf Pg Qa) Tj(Cw Fa Fb Hx Im Je Li Lx Mh Ml Nd No Oi Ok Oy Pf Qa Qy Rg Us Ut) It(Hr Il In Io Lx Mv Mw Nf Nm Nr Oe Ow Oz Pf Pg Pk Qb Qd Un Ut) Jn(Hr Hv Im Io Iv Ji Jq Lu Lw Lx Me Nm No Nr Oe Oz Pf Pg Qa Qd) Kr(An Cw Fb Gl iA Ic In Kk Kp Oi Ou Ow Qw Qy Rf Rm Ue Um Vo) Qd(Hr Hv Il Im Io Jq Me Mv Nf Nm Nr Oe Oz Pg Pz Qb Qc tV) Cw(Aj EF Fw Gl Hx iA Ic In Lv My Nf Nl oK Ou Ow Up) Di(aF aH aX bR cQ cR eF Fb Hx iA iH Lv My Ne Nl Ow qY) Qa(Hv iA Ik Im Iv Ji Jq Lu Lx Me Nf No Nr Oz Pf Pg Rm) Oe(Hr Hv Io Iv Ji Jq Me Mv Mw Nf Nm No Nr Oz Pf Pg Qb) Lv(aE Aj aN aQ aX bC bR bU cB cQ cR cS cT cZ dE) Qy(Ic In Jj My Nd Ng Oi Ql Qu Qw Rg Rm Ur Us Uv) Oz(Hr Hv iH Im Io Jq Lx Me Mv Nf Nm No Nr Pf Pg) Nj(Ao Ap As Ba Co Cp Ct Cu Cv Cx Dd Dl fR Wm) Rm(Ic Im Je Ji Li Lx Mv Nl Ou Ow Oy Ue Un Us) Pg(Hr Hv Il Im Io Iv Me Mv Mw Nf Nm Nr Qb Qc) No(Hv Im Io Iv Ji Jq Lu Lx Me Nf Nm Nr Pf) iA(bU cA cF Ic iH Im iZ Jj Me Mh oK Pz tF) iH(aF bP cF cM cQ dB dE Jj Mh Nd oK tF) Hv(Hr Im Io Jq Me Mv Mw Nf Nm Nr Qb) Ow(Af Aj Fb Fw Hx In Jj Ms Oi Pk Pz) Ic(aM aX bC cN cQ cR cZ Ms Ql Ur) Jq(Im Io Iv Ji Lw Lx Me Nm Nr Pf) Nf(Hr Il Io Iv Mv Mw Nm Nr Qb) cR(aQ aU bR cY Fb Hx Nl oD Oi) Me(Ik Im Io Iv Ji Lu Nm Nr) Wm(Ii In My Nc Nd Ng Oi) Lx(bR Im Io Iv Ji Nr Pf) Hr(Il Mv Mw Nm Nr Qb) Oi(cQ Fw Je Ou Pk Uk) bR(dl Gl Ml Ne Nl Qb) Fb(Aj Ax cC Jj Ky) Hx(Aj bA cQ cT Ut) In(Kq Pk Tv Vp Vu) Nr(Im Iv Ji Pf) Io(Nm Pf Qb Qc) Im(Iv Ji Lu) Us(Je Mv Ue) Aj(Ad Ef) Nm(Il Lu) Nd(fR Gp) Nl(bU dE) Iv(Ik Pk) Ji(Lw Pf) tV(fN Qw) AnPk EqmE ExcQ FpfR FwaM MwIl UeUr QbQc JeQl JjeF KdKq UpVu aHbB bUcC dUhC} Ok{Lj(aA Fp Fr Hq Hu Hv Hw Ih Ij Ik Il Im Io Ip Iq Ir Iu Iv Jg Jh Ji Jk Jl Jm Jn Jo Jp Jq Jr Js Jt Lh Li Lu Lw Lx Ly Lz Ma Mc Md Me Mg Mh Mi Mj Mk Ml Mm Mn Mp Mq Mr Mu Mv Mw Mx Mz Na Nb Nf Ng Nh Ni Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qd Qe) Fr(Fp Hq Hv Hw Ih Ij Ik Il Im In Io Ip Iq Ir Is Iu Iv Jg Jh Ji Jj Jk Jl Jm Jn Jp Jq Jr Js Jt Lh Li Lu Lw Lx Ly Lz Ma Mc Md Me Mg Mh Mi Mj Mk Ml Mm Mn Mp Mq Mr Mt Mu Mv Mw Mx Mz Na Nb Nf Nh Ni Nm Nn No Nq Nr Ns Nt Nu Nv Nw Nx Ny Oe Og Oh Oi Om On Oy Oz Pa Pb Pc Pd Pe Pf Pg Po Pz Qb Qc Qd) Li(aA Fp Hq Hu Hv Hw Ih Ij Ik Il Im Io Ip Iq Ir Iu Iv Jg Jh Ji Jk Jl Jm Jn Jp Jq Jr Js Jt Lh Lu Lw Lx Ly Lz Ma Mc Md Me Mg Mh Mi Mj Mk Ml Mm Mn Mp Mq Mr Mt Mu Mv Mw Mx Mz Na Nb Nf Ng Nh Ni Nm No Nq Nr Ns Nt Nu Nv Nw Nx Ny Oe Og Oh Oi Om On Oy Oz Pa Pb Pc Pd Pe Pf Pg Po Pz Qa Qb Qd Qe) Jj(Hq Hr Hu Hv Hw Ih Ii Ij Il Im In Io Ip Iq Ir Is It Iu Iv Jh Ji Jk Jl Jm Jn Jo Jp Jq Jr Js Jt Lh Lu Lw Ly Lz Ma Mc Md Me Mg Mi Mj Mk Ml Mm Mn Mp Mq Mr Mu Mv Mw Mx My Mz Na Nb Nf Ng Ni Nm Nn No Nq Nt Nv Nw Nx Ny Oe Of Og Oh Oi Om On Oy Oz Pa Pb Pc Pd Pe Pf Pg Po Pz Qa Qb Qc Qd Qe)

Figure 6 Continued

Figure 6 Continued aV bA bC bM bR bU cB Ch cN CP CQ CT Cu Cw Db Dc De Di Dk Ef Fr) cF(aD aM aR aU Bn cK cN) aM(cJ cK cT) CosF aRcB} Bb{bM(aK aM aU bA bQ cF cK cN cT cY dF Di) aM(aK aU aV bF bU cB cF cJ cT cY) cF(aU bA cK cN) cK(dF dN) fN(tT yH) bUcN} Ef{Dr(Af al Aj aM aU aV aY bE Bn bR cB cF Ct cY dD) Gc(Af Aj aM aR aU aY Bn bR cF Ct cY dD) AjEm GnaM} Lv{Jj(Fr Im Lh Li Lx Nr Po Qa) Li(aA Ii Im In Mf Ms Mt) Fr(Hx Ii My Nk) Mt(Lj Ms My) Lx(Hx Pg) NhaA liLh QaQb} Cw{cF(cK cN dR eF gL gP oH) oK(aR bW Ct Dr Ir Iv Oz) AjtF DraM TjLx NooD UcQv Inls dBiH gCnW} Ms{Mt(Jj Jq Jt Lh Li Mf Ml Po) Fr(Hx Iv Mf Ml) Lh(aA Ii Jj Lx) LxHx} aH{nA(Fi Gn Rz Sh Ye) Rz(mF nL) lX(Du Gn) MqoD Nvpl OmdU cFpH} Jj{Fr(Hx Ik Mf My Nk) Hx(Lh Li Lx Mt) Mt(Li Mf) IkLi} Vq{To(sC ul uM vP yH zG) Tt(sC sK) QvsC dRyL} mE{Du(aJ Ao bN cR Ij Jn Mn Nq Nw) GcJl} No{oD(Bn bX cX iJ) eQ(cX nI) jB(Mk Oz) aLoT} eP{Hb(aM cG Jl Po) Ko(Lx Qx Ur) FrKc QxNw} fN{Jp(rX yL tL) Di((tS tT) Mz(Il Vp) KevH NwvS} Lh{li(lm Li Lw Lx Mt Po) aDgV} aM{Eo(An cV cY) Ap(cF cK) AfGc cVeO} aO{dF(DW EO EW) FrbF} Tt{qW(sC ul yH) rN(jV Ri) TjFa} bM{bX(dW eO eW) AabQ DwdK aSdW} cR{Sj(mP mU nN) NioD YemU RzmW} Di{wH(Ky Vt) qO(uV wL) FyqY} Nq{rN(Ap Kf Kj) GnnN UftT} Dr{Dk(aU Em Hr) XamS} Fr{My(Hx Lw Mf) NkHx} Kq{Hf(jY oK tF) PafB} Lx{dX(Hb Ko) QaQb} cF{Ap(Bn cK) OzjB} iH{NwvS bUtF bZrC} rS{sF(jF Pc) Mwsl} Ko{EqkG gCnW} aD{EodE bAdX} cB{DlaR bZeO} AanWpl DdExYe ThaGoO MtllLi NkNvoD HqWhUt TrRirW QvVtuZ KfiArN KpsJkS OzmTjB Unconstrained panels with 2 analytes, where 1.0E-8 >= 'model p-value' > 0. Contains 118 panels of 200,591 total panels evaluated. : Et(aA aR Fp Fr Hr Hv Hx Ii Ik Il Im In Io It Iv Jd Ji Jj Jn Jo Jq Jr Li Lj Lu Lv Lx Lz Mb Mc Me Mf Mh Mi Mm Mn Mp Ms Mt Mv Mw Mx My Na Nb Nc Nd Ne Nf Ng Nh Ni Nj Nk Nl Nm No Nq Nr Oe Of Og Oi Ok Oy Oz Pd Pf Pg Pz Qa Qb Qc Qd Qe) Ok(Fp Hx Ii Ik In It Lv Mb Mf Ms Mt My Nb Nc Nd Ne Nh Nj Nk Nl) aC(Ad Ap Aw Bb Bo Cw Dg fR) Nd(Cw Fr Ji Lx Mm On) Ad(Aj Bo) Fr(Nc Nl) Mb(Mm On) MmNc liOn Unconstrained panels with 2 analytes, where 1.0E-7 >= 'model p-value' > 1.0E-8. Contains 209 panels of 200,591 total panels evaluated. : Ok(aA Fr Hr Hv Ih Ij Il Im Io Ip Iq Ir Is Iu Iv Jg Ji Jj Jn Jo Jr Li Lj Lu Lw Lx Ly Lz Ma Mc Md Me Mg Mh Mi Mj Mk Ml Mm Mn Mp Mq Mr Mu Mv Mw Mx Mz Na Nf Ng Ni Nm Nn No Nq Nr Ns Nt Nu Nv Nw Nx Ny Oc Of Og Oh Oi Om On Oy Oz Pa Pb Pc Pd Pe Pf Pg Po Pz Qa Qc Qd Qe) Et(aC aO aW Bo cK Fn Hf Hq Hu Hw Ih Ij Ip Iq Ir Is Iu Jg Jh Jk Jl Jm Jp Js Jt Kx Lh Ly Ma Md Mg Mi Mj Mk Mq Mr Mu Mz Nn Ns Nt Nu Nv Nw Nx Ny Oh Om On Ow Pa Pb Pc Pe Po Qv Qy Qz Ri Rm Tj) Nd(aA Im Is Jg Jp Jt Lh Li Mn Mt No Nw Po Qa) Nl(Jg Ji Li Lv Lx Mm No On) aC(cB Ch Cu De Di Dk Dl Fr) Nc(Jg Ji Li Lv Lx Nw On) Ad(aM aW bM cB cF cN) Jd(Cw Ic Ip Iq Mm On) Mm(Lv tV tX) Bo(Dg Dl) Mb(Fr Ji) Ne(Ji On) AjJg CwNj MsOn bBfR Unconstrained panels with 2 analytes, where 1.0E-6 >= 'model p-value' > 1.0E-7. Contains 510 panels of 200,591 total panels evaluated. : Et(AD aE AF aG aH al Aj aK aL aM aN aQ Ar aS aU aV Aw AX aY aZ bA bB bC bE bG bJ bL bM BN bO bQ bR bU bV bX bZ cA cB cC cE cF cG Ch cJ cM cN cO cQ cR CS cT cU cV CW cY cZ DB dC dD DE DG Dl dJ Dk dL dM Dp EF Fa Fb Fw Gl Gp Ha iA Ic iH Je Jf Ju Jv Jy Kd Ki Kk Kp Kr Ks Ky Kz Ou Pj Pk Qg Qh Ql Qn Qt Qu Qw Qx Ra Rb Rc Rf Rg Rh Rj Sr Tn To Tt Tv Tz Ua Ub Uc Ud Ue Uf Ug Uh Uk Ul Um Un Uo Up Ur Us Ut Uu Uv Vo Vp Vt Wm) Jd(Ad aM Bo bU Db De Di Ed Fn Fr Hf Hq Hu Hv Im In Io Ir Is It Iu Iv Jg Jh Ji Jj Jp Jq Ju Jv Ki Kk Kn Kp Kq Kx Ky Lh Li Lu Lv Lw Lx Ma Mc Mg Mn Ms Mt Mu Mv Mw Na Nc Ne Nk Nl Nm No Ns Nt Nu Of Og Oh Oi Ok Om Ou Ow Oz Pd Pf Pj Po Pz Qa Qe Qm Qv Qw Qy Qz Sr St Tn To Tt Tv Uc Uf Uh Uk Ul Un Ur Vt Tj) Ad(aK aR aU aV Aw bA bB bC bF Bn bQ bU cE cG Ch cK cR CT CW cY Db dF Di dN iH Mb Na Nd Nj) Nc(aA Im In Iv Jj Jq Jt Lh Lw Ma Mb Mf Ml Mn Mt Mv Nb Nd Ni Nk Nm No Nx Om Pd Pf Po Qa Qe) Nl(aA Im In Jj Jp Jq Jt Lh Lw Ma Mb Mf Mn Mt Mv Na Nb Nd Nk Nm Nn Nw Of Om Pd Pf Po Qa Qe) Nd(Bo Ih Jj Jl Jq Lv Lw Ma Mp Mr Mv Mw Mx Mz Nm Nn Nr Nv Om Pd Pe Pf Qe) Ok(aC aR aW Bo cK cQ cW Hq Hu Hw Jh Jk Jl Jm Jp Jq Js Jt Lh Qb) aC(Ao Ar Ax Ba Bc Bg Bn cF Co Cp Db Dc dN Dr Gc On Zq) Bo(aK aM Ap aU Aw Bb bM bU cF Cw cY Ef Fr Jg Nj On) On(aR cK Hf Hx Jj Lv Mf My Ng Nj Oy Tj) Ji(aR FR Hx Ii Lv Lx Mm Ms Mt Nj) Ne(Fr Jg Li Lv Lx Mm Mn No Nw) Mm(Fp Ml Nj Ow tN tQ tT) Dg(Aj aM AW cF Di) Lv(aA Fr Jg Li Lx Mt) Nj(aR Bn cR Db Dk Fr) Mb(Jg Li Lx Mt Nw) Jj(Fr Jg Lh Li Mt) fR(bF bQ cE Dl) tV(Ic Ky Pj Qw) Aw(aR bM Dl) Bb(aM bM cF) Zq(aM bW Or) Cw(cF oK) Ef(Dr Gc) Fr(Hx My) Ms(Jg Lh) aR(cB Jg) IcKq liLh aWcB bUiH hBoD Unconstrained panels with 2 analytes, where 1.0E-5 >= 'model p-value' > 1.0E-6. Contains 1,465 panels of 200,591 total panels evaluated. : Jd(Af Aj Al An Ao Ap AR As Aw Ax Ba BB BC Bg bM Bn bR bX cB cF Ch Co Cp Cq cR Cs Ct Cu Cv Cx Dc Dd Dg Dk Dl dN Dp Ef Ez Fa Fb fN Fp Fw Fy Gl Gp Ha Hb Hc Hr Hw Hx Ib Id Ih Ii Ij Ik Il Iz Je Jf Jk Jl Jm Jn Jo Jr Js Jt Jy Kc Kd Ke Kf Kg Kj Kl Ko Kr Ks Kz Ld Lj Ly Lz Mb Md Me Mf Mh Mi Mj Mk Ml Mp Mq Mr Mx My Mz Nb Nd Nf Ng Nh Ni Nj Nn Nq Nr Nv Nw Nx Ny Oa Oe Or Oy Pa Pb Pc Pe Pg Ph Pi Pk Qb Qc Qd Qg Qh Ql Qn Qt Qu Qx Ra Rb Rc Rf Rg Rh Ri Rj Rm Ss Tr Tz Ua Ub Uc Ud Ug Um Uo Up Us Ut Uu Uv Vh Vo Vp Vu Vv Zq Wm) Ok(AD aE aF aG aH al AJ aK aL aM AN aO aP aQ Ar aS aU aV Aw aX aY aZ bA BB bC bE bF bG bH bl bJ bL bM bN bO bP bQ bR bS bU bV bW bX bZ cA cB cC cD cE cF cG cH cI cJ cL cM cN cO cP cR cS CT cU cV Cw cX cY cZ dA DB dC dD dE dF dG dH Dl dJ DK dL dM dN EF Fb fR Fw gP Hf Ic iH Kx Ky Ow Pj Tj) Ad(aD aE AF aG aH al aJ AL AN AO AP aQ Ar AS AX aY aZ Ba Bb Bc bE BG bH bl bJ bL bN bO bP bR bS bV bW bX bZ cA cC cD cH cI cJ cL cM CO CP CQ CS CU CV CX cZ dA dB DC DD DE DG dH dl dJ DK DL dM dR eF FR gL gP Ji Jj Lv My On Ow Tj) Et(aJ Al An Ao AP As Ba Bb Bc bF Bg bH bl bP bS bW cD cH cl cL Co CP Cq Ct Cu Cv CX dA Dc Dd dF dH dK Dl dN DR Ed Ex Ez fR Fy gL gP HB HC hF hG Ib Id iJ iO iP IZ Kc Ke Kf Kg Kj Kl Kn Ko KQ kR kS Ld nW nY Oa oE oF oH oK oN Or pF Ph Pi Qm Ss St Tr tT tV Vs Vu Vv tF) Cw(aK aR aU AW bM Bn bU cB Ch cK cN cY Dg Di Dl dR EF FR Fw gL gP hB hC hF hG iA Ic iH iJ In iO iP Is iZ Jg Ji Jj kQ kR kS Ky Lv Lw Mb Mm Ne Nf Nl Nn nW nY oE oF oH ON Ou Ow pF Pj Qv Qz Tn Tt tV Ue Uh Up Ur Tj tF) On(aD aF Aj aN aO aQ aU aW aX BB bO bR bU cB cF cJ cN cQ cR cY Db dE Di Dr Ex Fn Fp Fw Ha Hv Ic iH In Io It Iu Iv Ji Jk Jr Kx Ky Li Lj Lw Lx Mh Ml Mm Mt Mv Mw Nh Nk Of Og Oi Ow Pf Pj Pz Ql Qv Qw Qz Ri Rm Tn To Tt Uh Us) Mm(aA aC AW Bo Fr Hf Hx Ic iH Ik Is Iv Jg Jj Jn Jq Jr Kq Kx Ky Lh Li Lj Lx Mf Mh Ms Mt Nb Nh Nk No Nr Nw Ou Pf Pk Po Qa Qv Qz Ri sC Tn tO tR tS Tt tU wB wC wD wE wF wG wH wJ wK wL wP wQ yD yH zA) Ji(aA aC aW Bo bR bU bX cB cK cQ Db Dr eM Fp Hv Ij Ik Il Im In It Iu Iv Jg Jj Jr Lh Li Lj Ma Mc Mf Mh Ml Mn Mv Mw Mx My Nb Nf Nh Nk Nn No Nr Nx Ny Og Oi Oy Oz Pb Pf Pg Po Pz Qa Qb Qc Qd Qe Tt) Nl(Fp Ih Ij Ik Il Iq Is Iv Jh Jl Jn Jo Jr Lj Lu Ly Lz Mc Md Me Mg Mh Mi Mj Mk Ml Mp Mq Mr Ms Mu Mw Mx Mz Nc Ne Nf Nh Ni Nj Nq Nr Ns Nt Nu Nv Nx Ny Oe Og Oh Oi Oy Oz Pa Pb Pc Pe Qd) Jg(aA aC aD aE aM aO aQ Ar aU aW bA bB bM bR bU bX cB cF cJ cK cQ cR cT Db Di dN Dr Fp Hx Ic iH Il In Io Iv Jq Kx Li Lj Lw Lx Mf Mh Ml Mt Mw Mx My Ng Nh Nj Nk Of Og Oi Ow Oy Pf tV) Nc(Fp Hx Ih Ij Ik Ip Iq Is Jh Jl Jn Jo Jp Jr Lj Lu Lz Mc Md Me Mg Mh Mi Mj Mp Mq Mr Ms Mu Mw Mx Mz Na Ne Nh Nj Nn Nq Nr Ns Nt Nu Nv Ny Of Og Oh Oi Oy Oz Pa Pc Pe Qd) Bo(aQ aR As aV aW Ax BA bB BC Bg Bn bR cB cG Ch cK CP Cs CT Cu Db Dc De dF Di Dk dN DW EO EW fP fR Is Lh Lv Mg Nm Of Ow Pd Pj) Nd(Aa Ap Bb Ch Dg Dk Ij In Iq Iv Jh Jk Jn Jr Lj Lz Me Mf Mg Mi Mj Ml Mq Mu Na Nb Ne Nh Nk Nq Nx Ny Of Og Oh Oz Pa Pc Qd) Ne(aA Ij Im In Iv Jj Jp Jq Jt Lh Lj Lw Ma Mb Mf Mt Mv Mx Mz Na Nb Nm Nn Nr Nx Ny Of Om Pd Pf Po Qa Qe) Nj(aA aM Ap Ar AW BA bB bF bQ bR bU cB cG Ch cN cT Cu Dc De dF Dg Di dN Im Lh Li Lv Lx Mt No Nw) aC(Aa Af Aj Al aM An aR As aW bB bC bF bM bQ bR bU cE

Figure 6 Continued cG cN Cq cR Cs CT Cv Cx Dd dF Em Ex Gd Jp Lh) Fr(aA aU AW bM cB cF Dg Dr fR Hv Ic Ii Iv Jq Jr Li Lj Lw Mf Mh Ml Ms Ng Nh Nk Oy Tj) Aw(aK aM Ap aQ aU aV aW BB bC bF bQ bU cB cF cG Ch cK cN cR cY Db dN) fR(aK aM aN aU aW bA bC Bn bR bW cB cG Ch cJ Co cT Cv cY Db Ef Gp gW Zq) Lv(lm lv Jj Jp Jt Lh Lj Lw Mb Mf Mn Mx Nh Nk No Nr Nw Pd Pf Po Qa) Dg(aD aK aQ aR aU aV bA bB bM Bn bU cB Ch cK cN Cp Cs cT cY De) Mt(Hv Hx In Iv Jl Jn Jq Jr Jt Lh Li Lj Lw Mf Ml Ms My Po Vh) Zq(aO Ap aU bR cB cR dH dM Dr Fb Hx iP Lj Lt lY mM mS Pk Rg) Lx(DW Eo Ew Hv Hx Jj Jq Jr Li Lw Mf Ms My Nh Pg Tj) Mb(AA Im Is Jl Jp Jq Jt Lh Lw Na No Nv Pd Po Qa Qe) cB(aD aJ aM BB bF bM Bn bQ cF cG cN cR Di Dk Dl) Pj(aM cN iH Kq Ow qB Qv rN rW sC Tn tT tX yH xA) tV(Bb Hf ll Ip Jo Kc Lh Ms Nm Nt Of Qc Qv Uf Vt) lc(aM aR cN fN gW hP jD jl qC qD rN rW tS Uh) Bb(aK aR aU aW bB bU cG cK cN cY dF Di dN) Kq(aR aW cR Db Fn Hf iH It Na Nt Ow Tj) Li(aA Hx Ik Im In Jq Lw Mf Ms Nh Ni Nk) Vh(bU Ex Fb gW Hr Im Je Jr Lj Pk Rg) Dr(bB Bg cG Ch Co Dk Fb Ko) cF(Ap aW bB bF bQ Dk Dl iH) Ap(Aj aM aW Bn cK Di) Dl(aU aW bF Ch dF Di) Jj(Ik Nr Po Qa Qe) Lh(aR cK tS tT Tj) bM(Aa aW bF bQ Dk) Nw(aR Mf Ms Nk) Nh(aA Mn No) aR(Is Jh Jp) aW(bF bU eP) Di(bU tS) Tn(Sr Uh) EfGn EmKo NmiH NaOw TtUh IptT QaQb bBeO bQbR Unconstrained panels with 2 analytes, where 1.0E-4 >= 'model p-value' > 1.0E-5. Contains 4,906 panels of 200,591 total panels evaluated. :
Zq(AD aE AF aG aH aI AJ aK AL AN Ao aP aQ AR AS aV AW AX aY aZ BA BB BC bE bF BG bH bl bJ bL bM BN BO bP bQ bS bU bV bX bZ cA cC cD cE cF cG CH cl cJ cK cL cM cN CO CP CQ CS CT CU CV CW CX cY cZ dA dB DC DD De dF DG dH dI dJ DK DL dM dN Dp dR Ed Ef Et Ex Ez Fa Fc Fd Fi Fn Fr Fw Fy Gb Gc Gd Gl Gp Gz Ha Hb Hc Hf Hl Ho Hp Hq Hr Hu Hv Hw Ib Ic Id Ih Ii Ij Ik Il Im In Io Ip Iq Ir Is It Iu Iv IZ Je Jf Jg Jh Ji Jj Jk Jl Jm Jn Jo Jp Jq Jr Js Jt Ju Jv Jy KC Kd Ke KF Kg Ki Kj KK Kl Kn Ko KP Kq Kr Ks Kx Ky Kz Ld Lh Li Lp Lu Lv Lw LX Ly Lz Ma Mb Mc Md ME MF Mg MH Mi Mj Mk Ml Mm Mn Mp Mq Mr Ms Mt Mu Mv MW Mx My Mz Na Nb NC Nd Ne Nf Ng Nh Nl Nj Nk Nl Nm Nn No Nq Nr Ns Nt Nu Nv Nw Nx Ny Oa Oe Of Og Oh Oi Ok Om On Op Ou Ow Oy Oz Pa Pb Pc Pd Pe Pf Pg Ph Pi Pj Po Ps Pz Qa Qb Qc Qh Ql Qm Qn Qv Qw Qx Qz Rf Rh Ri Rj Rm Ru Rv Rx Ry Rz Sf Sh Si Sj Sr Ss Tn Ue Uf Ug Ul Uo Up Us Ut Uy Vc Vh Vi Vp Vw Vz Wb Yd Yg Yk Yl Zw Zx Ye Tm Tl Xa Wm Tj) On(aA aE Af aG aH aI aJ aK AL aM An Ao AP Ar AS aV Aw Ax aY aZ BA BC bE bF BG bH bl bJ bL bM BN bP bQ bS bV bW bX bZ cA cC cD cE cG CH cl cL cM CO CP Cq CS CT CU CV cW CX cZ dA dB DC DD De dF DG dH dI dJ DK DL dM dN Dp dR Ed EF Ez Fb Fc Fd Fi fN FR Gc Gl GP Hb Hl Ho Hq Hr Hu Hw iA Ib Id Ih Ij Ik Il Im Ip Iq Ir Is Iz Je Jf Jg Jh Jl Jm Jn Jo Jp Jq Js Jt Ju Jv Jy Kd Ki Kk Ko Kp Kq Kr Ks Kz Ld Lh Lp Lt Lu Ly Lz Ma Mc Md Me Mg Mi Mj Mk Mn Mp Mq Mr Mu Mx Mz Na Nb Nf Ni Nm Nn No No Nq Nr Ns Nt Nu Nv Nw Nx Ny Oa Oe Oh Om Op Ou Oz Pa Pb Pc Pd Pe Pg Pk Po Ps Qa Qb Qc Qd Qe Qg Qh Qm Qn Qt Qu Qx Qy qZ Ra Rb Rc Rf Rg Rh Rj Rv rW Rx sC Sf Sr Ss St Tr tT TV Tz Ua Ub Uc Ud Ue Uf Ug Uk Ul Um Un Uo Up Ur Ut Uu Uv Ux Va Vb Vc Vh Vo Vp Vt Vw Vz Wd We Wh Yg Yl Zw Zx Wm Th Yf) Cw(aD Af aH Aj aI aM AN AO Ap aQ Ar aV Ax BA BB bC bF Bg bQ bR bW bX cE cG cJ CP Cq cR Cs CT Cu Cv Cx Db Dc Dd De dF dJ Dk dN Dp Dr dU eC ED Fb Fn fP Gl Gp Ha Hb Hc Hf hL Hq Hr Hu Hv Hw Hx Id Ih Ii Ij Ik Il Im Io Iq Ir It Iu Iv Je Jf Jh Jk Jl Jm Jn Jo Jp Jq Jr Js Jt Ju Jv jY Kc Kd Ke Kf Ki Kk Ko Kp Kq Kx Kz Ld Lh Li IL Lu Lx Ly Lz Ma Mc Md Me Mf Mg Mh Mi Mj Mk Ml Mn Mp Mq Mr Ms Mt Mu Mv Mw Mx My Mz Na Nb Nc Ng Nh Ni Nk Nm No Nq Nr Ns Nu Nv Nw Nx Ny Oe Of Og Oh Oi Om Or Oy Oz Pa Pb Pc Pd Pe Pf Pg Ph Pi Pk Po Pz Qa Qb Qc Qd Qe Qg Qh Qi Qu Qw Qx Qy Ra Rb Rc Rf Rg Rh Ri Rj Rm rN sK Sr Ss St tN To Tr tS Tv Tz Ua Ub Uc Ud Uf Ug Uk Ul Um Un Uo Us Ut Uu Uv vB Vh Vo Vp Vs Vt Wm) Vh(AA aC aD aE Af aG aH aI aM AR aU aW aY aZ bB bH bJ bL bM Bn bP bQ bR bW cB cD cF cG Ch cM Co cR Cs Cu cV cX cY Db dC DD Dc dF Dk Dp Dr Ef Et Fp Fr Gn Hq Hx Ih Ii Ij Ik Il In Io Ip Iq Ir Is It Iu Iv jD Jg Jh Ji Jj Jk Jl Jm Jn Jp Jq Js Kk Kn Ko Kp Kx Ld Lh Li Lt Lu Lv Lx Ly Lz Ma Mb Md Me Mf Mg Mh Mj Mk Ml Mm Mn Mp Mq Mr Ms Mu Mv Mw Mx My Mz Na Nb Nc Nd Ne Ng Nh Ni Nj Nk Nl Nm Nn No Nq Nr Ns Nv Nw Nx Ny Oe Of Og Oh Oi Ok Om Op Or Ow Oy Oz Pa Pb Pc Pd Pe Pf Pg Pi Po Ps Pz Qa Qb Qc Qd Qe Qg Qh Qm Qt Qu Qv Qw QX Qy Qz Ra Rb Rc Rh Ri Rj Rm Rt Ru Rv Sr Ss St Tn To Tz Ua Ub Uc Ud Ue Uh Uk Ul Um Uo Ur Ut Uu Uv Uw Vb Vc Vi Vp Vq Vu Wb Wc Wd We Wf Wh Wm Tj Th) Ji(aD aE AF aG aH aI AJ aK AL aM AN AO AP aQ Ar AS aU aV Aw AX aY aZ BA BB BC bE bF BG bH bl bJ bL bM BN bO bP bQ bS bV bW bZ cA cC cD cE cF cG CH cl cJ cL cM cN CO CP Cq cR CS CT CU CV cW CX cY cZ dA dB DC DD DE dF DG dH Dl dJ DK DL dM dN dR dU EF Em eP Ex Fn fP Fw gC gP Hf Hq Hr Hu Hw iA lc lH Io Ip Iq Ir Is jD Jh Jk Jl Jm Jn Jo Jp Jq Js Jt Kp Ky Lu Lw Ly Lz Md Me Mg Mi Mj Mk Mp Mq Mr Mu Mz Na Ng Ni Nm Nq Ns Nt Nu Nv Nw Oe Of Oh Om Ow Pa Pc Pd Pe Pj Ps Qv Qy Qz Ri Rm Ru Tn tV Ue Uf Uh Wd We Wh Wm Tj Ti Th) Jg(Ad AF aG aH aI aJ aK AL AN Ao AP AS aV AW AX aY aZ Ba Bb BC bE bF BG bH bl bJ bL BN bO bP bQ bS bV bW bZ cA cC cD cE cG CH cl cL cM cN CO CP Cq CS Ct CU CV cW CX cY cZ dA dB DC DD DE dF DG dH dI dJ DK DL dM dR EF Fn FR Fw Gc gL gP Hf Hq Hr Hu Hw iA Ih Ij Ik Il Im Ip Iq Ir Is It Iu Je Jh Jk Jl Jm Jn Jo Jp Jr Js Jt Jv Kp Ky Kz Lh Lu Ly Lz Ma Mc Md Me Mg Mi Mj Mk Mn Mp Mq Mr Mu Mv Mz Na Nb Nf Ni Nm Nn No Nq Nr Ns Nt Nu Nv Nw Nx Ny Oe Oh Om Or Ou Oz Pa Pb Pc Pd Pe Pg Pj Pk Po Pz Qa Qc Qe Qv Qz Tn Tt Uh Ur Uu Tj) Mm(Ad aN AR bA Bb cK cR cT Db De Di Dk Ef Fa Fb FN Fw Fy Gl Gp Hb Hq Hr Hu Hv Hw iA Ib Ih Ii Ij Il Im In Io Iq Ir It Iu Iv Jd Jf Jh Jj Jk Jl Jm Jn Jp Jq Jr Js Jt Jv Kc Kf Kg Kj Kl Kn Kp kQ Kr Kz Ld Lu Lw Ly Lz Ma Mc Md Me Mg Mi Mj Mk Mn Mp Mq Mr Mu Mv Mw Mx My Mz Na Nf Ng Ni Nm Nn Nq Ns Nt Nu Nv Nw Nx Ny Oe Of Og Oh Oi Om Or Oy Oz Pa Pb Pc Pd Pe Ph Pi Pj Pz Qb Qc Qd Qe Qt Qu Qw Qy Rb Rc Rg Rh Rj Rm rN rW sM sO Sr Ss To Tr Ue Uf Uh Ul Un uP UR Us UT uU UV vB vl vO vP vQ vS VT vU vV vW yJ yK yL zG zH zl yE tM tL xA Tk Tj) tV(Ad Ao Ap aU Aw Bc bG Bo bZ cF Dc Dd Dg Di Dk Dl Ed Fr Fw Gp gW Hb Hc Hq Hr Hu Hv Hw Hx Ih Ii Ij Im In Io Iq Ir Is It Iu Iv Jd Jf Jh Jj Jk Jl Jm Jn Jp Jq Jr Js Jt Jv Ke Kf Kg Kj Kl Kn Kp Kq Kx Kz Li Lj IK Lv Lz Ma Mc Mf Mg Mh Mj Ml Mp Mq Mr Mu Mv Mw Mx Mz Na Nd Ne Ng Nk Nn Nq Ns Nu Nv Nw Nx Oh Oi Ok Om Oy Oz Pa Pb Pc Pd Pe Pf Pg Po Pz Qa Qb Qd Qe Qg Ql qO qP Qu Rb Rh Ri Rm rW sC Sr Ss St tO Tr TT Tz Ua Ub Ug Uk Um Un UR Ut Uv Vo VP xA Wm) Pj(Ad aR AW AX bA bB bC bQ bU cB Ch cQ cR cT cV Db De dF Di Dk dN dR EF eT eZ Fb fN Fr fY gL gP gW hB hC Hf hG hL hO hP iA Ic iJ Im iP Iq Is iZ jD Jh Jp Kp kQ kS Ks Ky Lh Lw Lx Mt Mv Na No nW Of oH oK Om Ou Pd pF Pk pS pY QA qC qD qG qH ql qO qP qZ rO rP rQ rR rS rT rU rV sM sO Ss tN tO tQ tR tS Tt tU uL uM Un uP uR uT uU uV uZ vB vH vO vP vQ vS vT vU vV vW wB wC wD wE wF wG wH wJ wK wL wP wQ yD yJ yK yL zG zH zl yE tM tL tF) Kq(aE AF aH al Aj aK aL aM AN aO Ar aS aV aX aY aZ bA bC BG bH bM bN Bo bQ bR bU bX cA cB cD cF cG cl cK cN cQ cS cT Cu cV cW cZ dB dC dE dF Dl dJ Dk dN Dp DR eF Ex Fa Fb Fw gP Ha Hq Hv Hx iA In Io Ip Iq Ir Is Iu Iv Jj Jl Jp Js Kc Kd Ki Kk Ko Kp Kr Ks Kx Ky Ld Lu Mb Mj Mn Mr Ms Mt Mw My Mz Nb Nd Ne Nf Nj Nk Nl Nn Nq Nu Nv Ns Ny Of Og Oi Ok Ou Oz Pa Pd Pe Pg Pk Qv Qz Ri Rm Tt Ue Uh Ur tF) Bo(Aa aD aE AF aG aH aI AJ AL AN AO aP aR aS aX aY aZ bE bF bG bH bl bJ bL bN bO bP bQ bS bV bW bX bZ cA cC cD cE cH cl cJ cL cM cN CO CQ cR cS cU CV cW CX cZ dA dB dC DD dE dG dH dl dJ dK dL dM dR eF eM Fp GL gP gW hB Ic Ii IJ Im Io Jh Jo Jp Jq Jt Kf Ko kQ Kx Li Lw Lx Ma Mb Ml Mn Mt Mv Nc Ne Nh Nl No Nw Nx Oe Og Oh Om Ou Oy Pb Pe Qa Qe Tn Tt Ue Un tF) Ad(aA Dr Ef Ex FN FP Fw Gl Gp gW hB hC Hf Hq Hr Hu Hv Hx iA Ic Ih It Ij Ik Il Im In Io Is It Iu iZ Jh Jk Jo Jp Jq Js Jt Kp kQ Kx Ky Lh Li Lu Lw Lx Ly Lz Ma Mc Md Me Mf Mg Mh Mi Mj Mk Ml Mn Mp Mq Mr Ms Mt Mu Mv Mw Mz Nb Nc Ne Nf Ng Nh Ni Nk Nl Nm Nn Nq Ns Nt Nu Nv Nx Ny Oe Of Og Oh Oi Om Ou Oy Oz Pa Pc Pd Pe PF Pg Po Pz Qa Qe qO Qv Qz rN rW tS Tt Uh Ur Us) Nj(Aa aC aD aE AF aG aH aI aJ aK aL aN aO aP aQ AS aU aV AX aY

Figure 6 Continued aZ BC bE BG bH bI bJ bL bM BN bO bP bS bV bW bX bZ cA cC cD cE cF cH cI cJ cK cL cM CO CP CQ CS Ct cU CV cW cX cY cZ dA dB dC DD dE dG dH dI dJ dK DL dM Ex fR In Is Iv Jj JI Jp Jq Jt Lj Lw Ma Mb Mf Mn Mp Mv Mx Mz Na Nb Nd Ne Nh Nm Nn Nr Nv Nx Om Ow Pd Pf Po Qa Qe) Fr(aD aK aO Ap aQ aR aV bA BB bC bF Bn bQ bR bU cE cG Ch cJ cK cN Cp cT cY De Di DI dN Dp Ex Fn Fp Gc Hf Hq Hr Hu Hw Ih Ik Il Im In Io Ip Iq Ir Is It Iu Je Jh Jk Jl Jm Jn Jo Jp Js Jt Lh Lu Lx Ly Lz Ma Mc Md Me Mk Mn Mp Mq Mr Mt Mv Mw Mx Mz Na Nb Nf Ni Nm No Nq Nr Ns Nt Nv Nw Nx Ny Oe Of Og Oi Om Ow Oz Pa Pb Pc Pd Pe Pf Pg Po Pz Qa Qb Qc Qd Qe Qz sC TT Uh) Ic(aC aN aP Ar aU AW aY bA bB bC bQ bU cG cQ cR cV cW Dc dD De dF Dk dN eD eT eZ fY gL gP hA hB hL hO hR hV hW hX iB iC iH Im Iq iZ jE jF jG JH jK jL jM jO JP jQ jR jT jU jY Kc Ko Kp kQ Kx Ky Lh IK IL IM IN lO Lx Ma Mv No oF Oh oK Om Ou Ow Pd pI pF Pk pY QA qB Qe Qt Qv rB rO rP rQ rR rS rT rU rV sM Sr TN TT tX Uf Un Ut vS tF) Aw(aD aE AF aG aH aI aJ AL AN AO aP Ar AS AX aY aZ BA Bc bE BG bH bI bJ bL BN bO bP bR bS bV bW bX bZ cA cC cD cE cH cI cJ cL cM CO CP CQ CS CT CU CV cW CX cZ dA dB DC DD DE dF dG dH DI dJ DK dL dM fR Is Lw Mb Nd Ow Qe Uh) Li(Fp Hq Hr Hu Hv Hw Ih Ii Ij Il Io Ip Ir Is It Iu Iv Jh Jk Jl Jm Jn Jo Jp Jr Js Jt Lh Lj Lu Ly Lz Ma Mc Md Me Mg Mh Mi Mj Mk Ml Mn Mp Mq Mr Mu Mv Mw Mx My Mz Na Nb Nf Ng Nm Nn No Nq Nr Ns Nt Nu Nv Nw Nx Ny Oe Of Og Oh Oi Om Oy Oz Pa Pb Pc Pd Pe Pf Pg Po Pz Qa Qb Qc Qd Qe Tt Uh) Mt(aA aC aE aR cR Dr Fp Hq Hr Hu Hw Ih Ii Ij Ik Il Im Io Ip Iq Ir Is It Iu Jh Jk Jm Jo Jp Js Lu Lx Ly Lz Ma Mc Md Me Mg Mh Mk Mn Mq Mr Mu Mv Mw Mx Mz Na Nb Nf Ng Nh Ni Nk Nm Nn No Nq Nr Ns Nt Nv Nw Nx Ny Oe Of Og Oi Om Oy Oz Pa Pb Pc Pd Pe Pf Pg Pr Qa Qb Qc Qd Qe Tt Uh) Dg(aE AF aG aH aJ Al AN AO AP Ar AS AX aY aZ Ba Bb BC bE bF BG bI bL bN bO bQ bR bV bW bX bZ cE cG cH cI cJ cL cM CO cP CQ cR cS Ct Cu CV cW cX Db DC DD dE dF dG dI dJ Dk DL dM dN DR Ef fR gP iH Kx Lv Lw Mb Ok Ow Pd Qv) Jd(aA aC aD aE aF aG aH aI aJ aK aL aN aO aP aQ aS aU aV aW aX aY aZ bA bE bF bG bH bI bJ bL bN bO bP bQ bS bV bW bZ cA cC cD cE cG cH cI cJ cK cL cM cN cO cP cQ cS cT cU cV cW cX cY cZ dA dB dC dD dE dF dG dH dI dJ dK dL dM Dr Ex iH jD II. Lp Vq Vs We Ye Ti Th) aC(aA aD aE aF aG aH aI aJ aK aL aN aO aP aQ aS aU aV aX aY aZ bA bE bG bH bI bJ bL bN bO bP bS bV bW bX bZ cA cC cD cH cI cJ cK cL cM cO cP cQ cS cU cV cW cX cY cZ dA dB dC dD dE dG dH dI dJ dK dL dM dX Ef eW gV Im Io Is Jh Jt Lx Mg Mw Nm Nw Of Om Pd We) cB(aA aF aG aH aK aL aN aO AP aQ Ar aS aU aV AX aY BA BC bE Bg bH bN bR bS bU bV bW bZ cA cE CH cI cJ cK cL cM CP cQ CS cT Cu CV cW cX cY dA DC dD DE dF dG dH dI dJ dL dM dN Dr Ef Ex fP Gc Is Jh Jp Lh Nd Nw Om rW Un) Lx(aA aR eO eW Fp Hq Hr Hu Hw Ih Ii Ik Il Im In Ip Is It Iu Iv Jh Jk Jl Jm Jn Jo Jp Js Jt Lh Lj Lu Lz Ma Mc Me Mh Ml Mn Mq Mr Mv Mw Mx Mz Na Nb Nf Ng Ni Nk Nm Nn No Nq Nr Nt Nw Nx Ny Oe Of Og Oi Om Ow Oy Oz Pd Pe Pf Po Pz Qa Qb Qc Qd Qe Tn Tt) Lh(aA aD aN aQ aU aW bB bR bU cQ cT Di Fn Fp Fw Ha Hf Hx iA iH Im In Iu Iv jD Jo Jq Jr Kx Ky Lj Lw Mf Mh Ml Mx Ng Nh Nk Of Ow Oy Pd Pf Po Qa Ql Qv Qy Qz Ri Rm sC TN tO tR Tt tX Ue Uh uP Ur vB vP vV wC wF wG wL wP yD zH xA tF) Ok(Aa Af Al Ao Ap As Ax Ba Bc Bg Bn Ch Co Cp Cq Cs Cu Cv Cx Dc Dd De Dl DR dX Ex Fn fP GL Gp Hb iA Kd Kf Ki Kk Kn Ko Kp Kr Ks Kz Ld oK Or Ou Ph Pi Pk Qv Qy Qz Ri Rm sC Sr TN tO tS TT tX Ue Uf Uh Ur vB vH vV yH Wm tF) Lv(Ap aR Bb Fp Hu Hv Hx Ih Ii Ij Ik Il In Ip Iq Ir Is It Jh Jk Jl Jm Jn Jo Jq Jr Js Lu Lz Ma Mc Md Me Mg Mh Mi Mj Mk Ml Mp Mq Mr Ms Mu Mv Mw My Mz Na Nb Nf Ni Nm Nn Nt Nu Nv Nx Ny Of Og Oh Oi Om Ow Oy Oz Pa Pc Pe Qd Qe) Ne(Aa Fp Hq Hu Hv Hw Hx Ih Ii Ik Il Ip Iq Is It Iu Jh Jk Jl Jm Jn Jo Jr Js Lu Ly Lz Mc Md Me Mg Mh Mi Mj Mk Ml Mp Mq Mr Ms Mu Mw My Nf Ng Nh Ni Nk Nq Ns Nt Nu Nv Oe Og Oh Oi Oy Oz Pa Pb Pc Pe Pg Qd) Ow(Ap AR Bb Ch cR Db Dc Dd De Di Dk Dr Fb Fn fR Hb Hf Hq Im In Io Iq Jh Jj Jp Jq Js Jt Kc Kf Kg Ko Kp Kx Ky Lw Ma Mg Mv Nk Nm Nu Of Oi Om Oz Pd Pk Pz Qa Qe Qv Qz Tn Tr Tt Ue Uf Uh Un Ur Tj Ti) Nd(AR BA bB bC bF bQ bU cG cN Cp cR cT Cu Dc Dd De dF Di Dl dN Fp Hq Hr Hu Hv Hw Hx Ii Ik Il Io Ip Ir It Iu Jm Jo Js Lu Ly Mb Mc Md Mh Mk Ms My Nf Ng Ni Ns Nt Nu Oe Oi Oy Pb Pg Pz Qb Qc) Tt(Aj aM Ap Ar Bb bU cF Db Dc De Di Dk Fn Hb Hu Id Im In Ip Iq Is It Iu Je Jh Jj Jp Ke Ko Kp Kx Ky Lw Mu Mv Na Nk No Nu Nw Oh Om Or Ou Qa Qe Qv Qw Qy Qz Ra Rg rN Sr St Tn Uf Un Ur vS Vt Tj) fR(aD Af aH aI Aj aL An aO AP aQ Ar aS aV Ax aY Ba Bb Bc bE Bg bH bJ bM bN bO bU bX cF cI cK cM CP cR Cs Cu cV dB Dc DD De dF Di Dk dN dR Ex Fb Fw Gc Gl Hb Is Ko Mn Nw) cF(aD aJ aK aM Ao aQ AR aU aV Ax BA BC bE Bg bM Bn bR bU cE cG Ch cI cK cM cN Co Cp cR cT Cu cY Db Dc dD De dF dG Di dN dR EF Gc gL gP hB rW tS tT) aR(Ap aW bB bF Bg bM Bn bQ bR bU cE cG Ch Cp Cu Di Dk Dl Ef iH Io Ij Jq Jt Kf Ko Lw Mg Ml Mw Mz Nm Nq Of Om Pd Qa Qe rW tT tX Uh Un) Bb(aD aJ aQ aV Ax aY BA bC bF Bn bQ bR bV bX cE Ch cJ CP Cs cT De dG DL dR eF fN gL gP Kx Lw Mb Nl rC tS) Jp(aQ Ar aU aW bB bF bU cJ cK cR cT FN Fp Hf iH jD Kp Kx Ky Mf Pk Qv Qy QZ Rg Rh Ri Rm Tn Ue Uf Uh vS zH Tj) Nw(aA aW bB bR bU cK Fp Hx iH li Ik Il Im In Iv Jj Lj Lw Mh Ml Mn Mw Mx My Na Nb Nf Nh Nm Nr Oy Oz Pd Pf Po Qa rW) Ko(aW cR Db Fb Fd Fn Gb Gd Hf iH Kp Kx Ky Lp Lt Na pH Ps Qz Ru Rv Sf Uh Ux Vb Vc Vi Vj Vw Wd We Wf Wh Ye Ti Th) Ap(aD aK aQ As aU aV Ax bA bB bF bM bQ bR bU cG Ch cJ cN Cp Cs cT Cu cY Dc De dF Dl dN DR gP iH Lw rN) Mb(Dk Ih Ij In Iv Jj Jn Jo Jr Lj Ma Mf Mg Mn Mp Mr Mu Mv Mw Mx Mz Nh Nk Nm Nn Nr Nx Ny Of Om Oz Pe Pf) Tn(Db Di Dr Ex Fn Hf Im In Iq It Iu Jj Kp Lw My Na Nk Nu Oh Qa Qu Qw Qy Qz Ra Ri Rm Ue Uf Un Ur Vp Tj) Di(aK aM aU aW Ba bC bM bR cG cK cT Cu cY Db Dc dF Dk eD Ef fP gW hR hX iH Is jY Qe qY tN tO tT) Dl(Aj aK aM aQ Ar aV BA bB bC bM Bn bQ bR bU cE cG cJ cK cN CP cT cV cY Db De Dk dN Dr) Dr(aM Ao aU Ba bQ cE cY dF Gp Hc Ij Iz Kf Ma Mg Mn Mv Nn Nq Nx Oh Om Pd Pf Rc Rz Sr Ss Ut) Uh(aM bU Db De Hq Im Iq Is Je Jh Kp Kx Mv Nm Of Oh Om Oy Pd Pk Qa Qv Qy Qz Ri Tr Ue Uf Un) Dk(aK aQ aU aV aW bC bF bR bU cG Ch cJ cK cT cY dF dN Fx Gc Gn Is Kx Lt Qz Ye Tj) Nc(Aa Hq Hr Hu Hv Hw Ii Il Io Ir It Iu Jk Jm Js Ly Mk My Nf Ng Oe Pb Pg Pz Qb Qc) bB(aM aW bA bF bM bQ bU cN cT dN DW dX Ef EM Eo eP EW Gc iH Is Jh Nm) Gc(Af aM aU aW Bn bQ cG Ch cN cY dD dF dR cF Et Fb Im Mv Om Pf Pk Ut tF) Nh(Im In Iv Jj Jq Jt Lj Lw Ma Mf Ml Mx Na Nb Nm Nn Nr Nx Pd Pf Po Qa Qe) Nl(Aa Hq Hr Hu Hv Hw Hx Ii Io Ip Ir It Iu Jk Jm Js My Ng Pg Pz Qb Qc) iH(Aa cM dB eD Jt Kf lL Mw No Oz qT qU qV qW qX qY rA rC rY Ue tF) Po(aA Hx Ii Il Im In Iv jD Jq Lj Lw Mf Mn Ms Nf Nm No Og Oy Tj) Et(Aa eC fN fP Gz jD rN rW sC tN tO tQ tR tS tX uP Vq yH) Ch(aK aM aU aW Ax BA bM Bn bU cG cK cN Cs cT Cu dF) aW(aU aV Ba bQ bR cE cG Cp Cu Dc dF dN Ef Ex Is Nrn) Mf(aA Fp Im Is Iv Jj Jl Jq Jt Lj No Nr Nx Qa Qe) Qa(aA bR Hx In Jq Lw Mh Ml Ms Nx Pf Qc Rm Tj) Uf(Fn Im In Iq Qv Qy Qz Ri tN tS tT Ue Un Ur) bM(Ar BA Bg Bn cE cG Cp cT Cu dD De dF Jh) Jj(Fp Im Is Iv Jl Jt Lj Mv Nv No Nt Nv Nx) Ef(aJ aM cN cR Em Eq Lp Lt Ru Rv Vb Zx) cK(Ba Bc Cp Cu De Is Jh Lw Mw Nm Om Pd) Un(bR Fn Hf Mv Na Nu Qv Qy Qz Ur Tj) bF(aD aF aM aO bC Bn bR bU cI cN dN) Ut(Fc Fi Lt Ps Ru Rv Rx We Wh Tj) bU(Ar Bn bQ cG cN Cp De dN Is Jh) Ba(aD Aj aK aM aU Bn Ct) No(eQ Hx Ik Iv jB oD oT) Lj(aA Lw Mv Of Om We Wh) bR(cE cG cN dF dN Is We) nN(eD kC kI mE nI nT qU) tS(Ip Ke Kf Kg Nm Ri Vt) Im(Fn Iv Ml Pf Rm Tj) aA(Fp Hx Iv Ml Nx Qe) aU(Ar Ax Cp Cu De Is) Lw(Ar cR Fp Ik Iv) Vt(sO tX uZ vS tL) Cp(aK aM cG Db) Cu(aK bC cN cY) Fb(Ax Em Mc We) Nm(cR tN tT tX) Mz(fN jD qC rW) Ip(tN tR tX wB) aD(bQ cE cG gV) hB(lX nC nH nL) rN(Kf Kg Kj Ri) Is(aQ cR cY) Op(Or Pk Ru) Tk(qO qP yL) Pf(Ik Nx Ti) aH(jB pH pl) aM(Eo eW We) De(aK cY) Tr(Db Sr) Jq(Fp Iv) Ky(sC uP) cR(Om Pd) wL(sC tT) AjKl AraK BncG ThMn ExYe UeQv HxJl HbeP JefN WeRg KfiA KxeM RirW OftT VajI VqtL OzjB jDqZ Unconstrained panels with 2 analytes, where 1.0E-3 >= 'model p-value' > 1.0E-4. Contains 10,885 panels of 200,591 total panels evaluated. :
Lh(aE aF aG aH al AJ aK aL aM AO AP aV aS aV Aw AX aY aZ BA Bb bC bE bF bG bH bI bJ bL bM BN bO bP bQ bS bV bW bX bZ cA cC cD cE cF cG CH cI cL cM cN cO CP cR CS Ct cU CV cW cX cY cZ dA DB DC dD DE dF DG dH dI dJ DK DL dM dN Dp DR Ed EF Ez

Md Me Mg Mh Mj Mk Ml Mq Mr Ms Mu Mw Ni Nk Nq Nt Ny Of Og Oh Oz Pa Pc Pe Qd rN rW) Jh(aD aE aF aK aM aN aO aQ Ar aU aV Ax aY bA bC bQ bR bW bX cE cG cJ cN cQ cR cT cV cW cY Db dD dE dF dN FN Fp Iv jD Jj Kp Kx Mf Op Ou Qv Qz rW Sr tX Tj) Mn(aA Ar DW dX EM EO EW Fp Gn Ik Iv Jj Jq Kp Kx Lp Lt Lw mE Mf Mh mI Ml mM Mx mZ nA nC NK nL No Nr Nx oQ Pf Qv Qz Rt Rv Sr Uw Vi We Wh Ti) cG(AF aH aK aM AN AO aQ Ar aS aU aV Ax BA BC bE Bg bQ bX cI cK cN Co cP CQ cR Cs CT CU Cv cW cY Db Dc dD De dJ dN Ex gC Io jB Nl) bM(Af aI aK aL aM AN Ao aQ AS aU aV Ax aY BC bE bP bR bU bZ cI cJ cK cN Co cP CQ cR Cs Ct CV cY Db Dc dG dN DW dX EO eP EW gV) Lx(Aa aN aQ aU bR bU Ch cJ cK cR cY dE Fn Ij Io Iq Ir jD Kp Ly Md Mg Mi Mj Mk Mp Mu Ns Nu Nv Oh Pa Pb Pc Qy Qz rW sC Sr tN tO tS tX Ue wG Wm Ti tF) No(aA cK dU Fn Fp gZ Hf In Ip Je Jl Jn Jo Jq Jr Kp Kx Lt Lw Mh Ml Ms Mv Mx Nb Ni Nk Nn Nr Nx Of oV oW Oz Pf pH pI pK Qy Qz Ri Sr Ue We Tj Ti Th) tX(Ao bG bZ cI dI fP Hf Hq Ii Il Jo jV Kc Ke Kg Li lK Lv Ma Mf Mg Mh Mq Ms Mu Mv Mw My Mz Na Ne Ng Nl Nx Of Oh Oi Pc Pf qP qW rB Ri sC wG wL tL) Jj(aA Ba bU cK Dc dW EO Ew Ih Ij Ip Iq Ir It jD Jk Jm Jo Jq Jr Kg Kl Kp Kx Lw Ma Mg Mh Ml Mq Mu Mw Mx Mz Nb Nk Ny Of Oh Ou Pc Pf Pz Qd Sr) bQ(aF aJ aK aM aN aO aQ Ar aU aV aY BA BC bE Bg Bn bW bX cC cE Ch cI cJ cK cM cN cO CP cT Cu Cv cY Dc dD De dF dH dJ dN Ex Io Lw Nl) bU(aD Af aJ aK aM aN Ao aQ aU aV Ax aY BA BC Bg bH cE cK Co cP cR Cs cT Cu CV cY Db Dc dD dF dG fP hB Io Jq Li Lv Lw Ml Nl Sr Tr) Ch(Aa aD aF aJ aN aO aQ Ar As aV aY BC Bg bR bV bW bX cE cH cJ CP Cq cR Ct Cv cY Db Dc De dG dJ dL dN Jq Kx Li Lv Lw Ne Nl) Mf(Aa Ih Ij Ik In Ip Jn Jr Lw Lz Ma Md Mg Mh Ml Mp Mq Mr Ms Mu Mv Mw Mx Mz Na Nb Nf Ni Nk Nn Nt Nv Ny Of Og Oh Oz Pa Pe Pf Qd) Op(aM As Ax Bn Cs Dc De eM Ex Hc Id Ij Je Jn Jr Kx Li Ml Mq Mr Mw Mx Mz Na Nr Ny Pe Ph Pi Qx Ra Rb Rj Rt Sr Tr Ue Uo Us Vi We) tS(Ao Bc bR bX cH cI Cp cS Cu cV cZ Dc Dd dI dJ Fa fP Gl Hf Ii jK Jo Kc Kj Kn Kp Li Lv Mu Mv Mw Of Pi Qw qZ rC rS sC Tr Ue Tk) De(aD aM aQ Ar aV Ax BA bC bR bX cE cJ cN CP cT Cu Db dF dN Em Fn Io jB Kp Lv Lw Ma Na Nl Ou Qv Qz Sr Tr Ur Tj) Kp(aM Ar cN cR Db Dc fN Hb Hc Hf Id Iq Ke Kx Kz Li Lv Lw Ma Mg Mv Mw Na Of Ou Qv Qy Qz rW sC Sr tN tO Tr Ue Ur) Lv(Aa aN Ar aU Ba bC Bn bR cK cN Cp cR cT Db Dc Dd Ex Hq Hr Hw Io Iu Ly Ng Nq Ns Oe Pb Pg Pz Qb Qc Sr tN) Lw(aA aU Ax Ba bR Co cT Db Dc Ex Fn fP Hb Jl Jq Jr Kx Ma Mh Ml Mv Mx Nb Nk Nn Nr Nt Nv Nx Ou Oz Pf Qy Sr) Oh(cK cR Dp Fn Fy Ib Id Je Jy Lp Lt Qm Qt Qv Qy Qz Rc Ri Rv rW Rx Sr Ss Tr Ue Ur Vc Vi We Wh Wm Tj Ti Th) sC(cE cS cV eD fN fP Hf jY Kc Ke lL lM Ma Ms Mu Mv Mw Na Of pS Qv qW rC Ri rN rS sO tN Tr Vq zH tL Tk Wn) jD(cA eD Hq hR Hu Hv Hw HX iC Iq Jk Jl Jm Jn Jo Jq Jr jY Li lL lN Mu Mv Mw mY Na Ny Uw Vi Vq vS Wm) Ar(aD aM aQ aV BA bC Bg bR cE cJ cK cN Cp cT Cu cY dF dN Fn Io Jq Mg Nc Ne Nl Ou Sr Ss Tr Ue Tj) Ke(An cR Db FN Hf hL iA Iq It Iv Ki Kx Ma Na Nu Qv Qz rN rW Sr tN tO tR Ue uZ vB vH vV wJ Tj tF) Cp(aD aN aQ aV Ax aY BA bC Bn bR bX cE cJ cN cP cR Cs cT Cu cY dF dG dJ dN FN It Na rW Tj) Iv(Fp Ik In Jl Jn Jr Ma Mh Ml Mq Mr Ms Mu Mv Mw Mx Mz Na Nb Nk Nn Nr Nv Nx Ny Of Oz Pe Pf) Ba(aO aQ As aV Ax bA bC Bg bR bX cJ cN cP Cq cR Cs cT Cu Cv cY Db Dc dF dN Kx Na Nl) Ip(aA eZ fN hL hO qA qC qD rW tO tQ tU uP Ur wD wF wG wH wJ wK wL wP wQ yD yH zI yE) Sr(Em Hf Hu Id In Kx Li Lp Lt Ma Mv Nk Nu Qv Qy Qz Rv To Tv Ue Ur Vi We Wh Ye Ti) cK(Ao Ax Bg Bn cE Co Cs Cv Db Dc dF dN Io Jq Ma Mg Ml Mu My Mz Nl Nq Nv Nx Ny Of) Fp(Ik In Jl Jn Jr Ma Mg Ms Mv Mx Mz Na Nb Nf Nk Nn Nr Nt Nv Nx Ny Of Og Oz Pf) Kx(Db dU dX eQ Ex Fn gV Hb Io jB Je Kl Ma Mv Na oD Ou Qv Ss Tr Ue Ur Tj Ti Th) Nr(aA Hx Ik In Jl Jn Jq Jr Mh Ml Ms Mv Mx Mz Na Nb Ni NK Nx Oz Pe Pf We) Bn(aK aM aQ aU aV Ax bA bC Bg bR cE cJ cN cP cT Cu cY Db dF dN EM jB) Dc(aK aQ aU aV bA bC cE cJ cN cT cY dF dN fP Lt Na Qz Rv rW Ur Vi We) Jq(aA Hx Ik In It Jl Jr Ma Mh Ml Ms Mv Mx Nb Nf Nk Nn Nt Nx Ny Oz Pf) Hf(eD Ex jR jY Li lL Ou qU qW qX rB rC rN rW rX rY rZ tN Tr Ue yH) Nx(Ih In Jl Jn Jr Mh Ml Ms Mv Mx Mz Na Nb Nk Og Oz Pe Ru Rv Vi We) aU(Af Ao bA Bc Bg bR cN Co Cq cR Cs CT Cv Db Dd dF dN Ex Io Nl) Cu(aD Aj aM aN aQ aV bA bR bW cE cJ cP cR cT Db dE dF dN Lt Tj) fP(aD aO bR cW rN rW rY sM uM uV uZ vS vV wE wL wQ yH zH tL xA) Ik(aA In Jl Jn Jr Lz Ma Mh Mj Ml Mr Ms Mx Mz Na Nk Nn Og Pe) rW(aD Bc bX cW jY Kg Kj Ms Mv Mw Na Nc Nl Of qW rC Tr Vq Tk) Qv(Hb Io Iq Kg Kj Kl Li Ma Mg Mv Ou Qm Qy Ss Uc uN vS yH) aA(Hv Ir It Jl Jo Jr Lu Ma Mh Ms Nb Nk Nn Nt Nv Of Pf Pz) bR(aJ aK aM aN Ax bA bC Bg bZ cT dG eW hB Li Nl Qd Vi Wh) dF(aD aF aK aO aQ aV Ax Bc bE cM Cv cY Db Em jB Nl Ue Vc) dN(aD aK aL aQ aV bA bE Bg cE cI cM cN cR cT cY dD jB Ue) Ex(aM cN cY Du Fc hL Lp Lt Nc oK Ru Rx Rz Si We Wh Yd) We(cD cR Cs Dd Je Jr Kn Li Nn Or Pe Pf Pk Qb Qm Rv) cT(aD aK aM Ao Ax aY BC Bg cN Co Cv Db Io Mg Nl) Tr(cR Fn Iq Iu Li Na Ou Qy Qz sM St Ur vS wJ yH) Pf(gV Il Jl lL Lp Ml Nb NK Nt Nv Va Vc Tj Th) hB(eM eP eQ jB kC kF kO mS nI nJ nO nT nU oV pK) Mz(eT eZ fY hL hO hP jY lL pY qA qB qD rN rP) Ou(cR Db Fn Io Iq Li Ma Mg Na Pk Qz Rh Ue Ur) Vq(cV hO jY qI qU qX qY rN uM vP vV yK yL xA) aM(Ao Bg cE Co DW eO Ew Gl Gn gV Kl rC Rz) tN(Jo Kc Kg Li Ma Ms Mu Mv Na Of Pc Qw Ri wL) Ml(Aa cR Jl Ma Mu Mv Mw Mx Nb Nk Nn Nv Ny) Ue(Ax cN cV Db Fa Fn Iq Li Na Qz Ur Vi) Bg(aD Aj aK aV Ax bA bC cN Cs cY Db) Or(Lp Lt Ru Rx Rz Si Uw Ux Vw Wh Ye) Ur(eM Gd Iq Kg Kj Kl Li Mg Mv Of Uc) Rv(Dd Iz Mg Nn Oi Pi Pk Qy Ss Wm) aK(Ao Ax Bc cE cN Co Cs Cv Db rC) cR(Io Mg Mu Mw My Nc Nl Nq Ny Of) jB(Af Ax cX Ij mE Mk Nn nW Ny oN) rN(bX eC Kl Mg Na Nq Of rC Ss vV) Th(eQ Ir kI mE Ny oD oO oP Wm) Mv(FN Hx lL Nk Qw Qz tO tR) Li(Fn Iq Je Qw Qy Qz Ri Wm Tj) aH(dU eQ fB gZ oD oT oV oW pK) cY(Ao Ax Bc cN Co Cs Cv Db) Dd(Ps Uw Ux Vi Vj Wd Wh) aD(bA DW EO EW) dX(aN bA dD Hb Kc Kk Qx) qU(kO mW mY nD nH nJ nL) Ti(Ir Ma Ny Pk St Wm) Ne(Hr Io Ir Pz Qb Qc) Nk(Jl Ma Nb Ni Nn Nv) Qz(Id Je Kl Ma Mu Of) cN(aV Bc cE Co Gl Mg) Ax(aQ aV bC cE pH) Wh(Jr jT Pe Qm Rg) Tk(jQ vP vV wH wL) eM(Af Hb Kk Qx Yi) rS(Of sF sH sI sJ) oD(Fa Ld Mq nW oQ) Ms(Jl Nv qZ zH) Mw(fN iA lL qZ) Na(Hb Kl lL yH) Ir(Lt nA nK Tj) Pk(Gn Uw Ux Vi) cW(eD eO hR rC) eP(aN bA Kc Kk) sO(qO qP vP vV) qX(Si Uw Vb Vc) Bc(aQ aV fN) Cs(aV bC Ye) Fn(Fy Id Ma) Je(Iq Ma Tj) Jl(In Mh Nb) Kz(dU rX rY) Ri(rC rU tO) Rg(Rt Vi Vw) Of(qZ tO tR) bX(qO qP rU) cV(eD hR hX) nW(Du eQ gC) Co(bC Gn) Db(eD Kl) Em(Af Kc) Nq(nK pH) Mu(lL Tj) Io(bA kQ) Iz(Lt Zx) Qy(Iq Ma) Kg(tO tR) Kn(Lt Ru) Nv(Hx Mh) Vc(gL jT) Va(jK Pe) gV(cP Qx) vS(fN lK) DumE GnPi MgbA MquZ HlVu HcYe QwuX KczH WnpF UxPe VilM aNcE gWmS wDtL qTkO

Constrained panels with 3 analytes, where 1.0E-10 >= 'model p-value' > 0. Contains 258 panels of 38,530,102 total panels evaluated. : Et{Ms(Fp Hx Ik Ji Jr Li Lv Lx Mb Mf Mh Ml Mt My Nb Nc Nd Nc Nh Nj Nk Nl) Ii(Fp Hx Ik Jr Lh Li Lj Lv Mb Mf Mh Ml Mt Nc Nd Ne Nj Nk Nl On Po Qa) Nc(Hx In Io It Jj Lv Mb Mf Mh Ml My Nb Nd Nh Ni Of Oi Oy Qb) Nd(aA aO aW Bo Cw Db In Jj Jo Li Lj Lw Mh No Of Oi Ok Pf) Nl(aA Hx In Io It Iu Jj Jo Lv Mb Mh My Nb Nh Of Oi Oy) Ne(Hx In Jj Jo Lv Mb Mf Mh My Nb Nh Of Oi Oy) Mb(aA Hx Jj Jo Lj My Na Nk Of Oi Ok) Hx(aA Jj Jr Lj Mh Nj Nk Of Ok) Nj(Db In Jj Mh Oi) My(Mt Mv) MfJo NiNk} Ok{Nd(Fr Hr In Iq It Jj Jo Li Lw Lx Me Mf Mm Mn Nc Nk No Og) Nc(Hr Hx Ii In Iq Ir It Iu Jj Lv Mb Ms My Nb Oi) Nl(Ii In It Lv Mb Mf Mn Ms My Nb Nh) Mb(Fr In Mm Ne Nk) Ii(Ne Nk On) NeIt NjIn} Nd{On(aA Ii In Iu Jj Lw Mm Ms Mw My Nc Of Og Oi Oy Pf) Mm(aA Cw Fr Im Is Ji Li Lv Mr Mz Nc No Pe Pf) Fr(Jj Nc)} aC{Ad(Aj aM aW Bo cF cN cZ Di fR) fR(BC Ch Co Cv Db Dg Dl) Bo(Dg Dl) CwcZ DgaW DrEf} Ii{On(Mb Nc Ne Nj Nl)} Ad{Aj(aW Bo) BoaM} MbMmNc Constrained panels with 3 analytes, where 1.0E-9 >= 'model p-value' > 1.0E-10. Contains 569 panels of 38,530,102 total panels evaluated. : Et{My(aA Fp Fr Hx Jj Jr Li Lj Lv Lw Lx Mf Mh Ml Nb Nh Nk Ok Om) Ii(Fr Ih Iv Jg Ji Jq Lw Lx Mr Mv Nb Nh No Nr Nx Of Ok Pe) Oy(Fp Hx Ik Jg Jr Li Lu Lv Mf Mh Ml Mt Nb Nh Nj Nk Of On) Of(Fp Ik Jg Jr Lj Lv Mf Ml Mt Nb Ng Nh Nj Nk Ok) Oi(Fp Hx Ik Jd Jr Li Lj Lv Mf Ml Mt Nb Nh Nk) Lv(aA Hx Jj Jo Lj Mf Mh Ml Mw Ng Nk) Nj(aA aO aR aW Bo cR Cw Jo Li Mf Ok) Jj(Fp Ik Jr Lj Mf Mh Ml Mt Nh Nk)

Figure 6 Continued

Ml(aA Hx In Jo Mf Mw Ng Nk) Jd(Fn It Iu Na Nt Nu Tj) Fp(Hx Ij In Jo Qb Qc) Nd(aR bC bU Ch cR Di) Nk(In Jo Mf Mh Nb Ok) Hx(Jo Li Lx Mf Mt) Lj(In Mf Ms Qb Qc) Ng(Ik Jr Mt Mv) Mh(aA In Mf) Ne(aA It Iu) aR(aC aW Mb) Ik(In Jo) Li(Qc Qd) Ok(Hr Jo) LxPg NaKx InJr QaQb} Nd{Mm(aW Bo Db Ih In Iq Iv Jg Jj Jl Jn Jp Jq Jr Jt Lh Lj Lw Lx Lz Mb Ml Mn Mt Mv Mx Na Nr Nw Of Og Oz Pd Po Qa) Fr(aA Ii Im Is Ji Jl Jq Jr Li Lj Lv Lw Mf Mn Mr Ms Mx Mz Na Nk Nl Nm No Of Og Oi Pd Pe Pf) Ji(aA Cw Im In Iq It Jj Li Lx Mn Ms Mt Nc No Og) On(Bo Cw Jo Li Mf Mh Mv Ng) Jj(Jg Jt Lh Li Lx Mt Qa) Lx(aA Hx Li Pg) Cw(Jp Lw Ok) Im(Li No Pf) Bo(Ad Ok) aA(Lh Li) NoNc JgOy OkcW} aC{Cw(Ad aF aM aO aR AW aX bC bE Bo bU cF cN cW Dg Di dN fR) Ad(aL aR Aw aX aZ bC bE bM bU cB cR cW Db dF dJ dN) fR(aM Ao Ap aW Ba BB bH Bo cE Cu Dc De Di Dk) Dg(Aj aM aR Aw bC bU cB cF Ch cN cW cZ Db Di) Bb(aM aR AW bC bM Bo bU cF cN Di dN) Ap(aM aR AW Bo cF cZ Di) Aw(aR bM bU cZ Db Dl) Bo(BC bU cZ Dc) DkDr} Ok{Ii(Fp Fr Ik Jg Lh Lv Lx Mb Mf Mh Ml Mt Nb Nj Nr Po) Ne(Hr Hx In Iq Ir Iu Jj Lv Mf Mn Ms My Nb Nh Of) Nj(aR Bo cW Db Hr Hx It Iu Mf Ms Nb) Nk(Hr Hx In It Lv Mf Ms My Nb) My(Fr Lv Lx Mf Mt Mv On) Hx(Fr Jj Li Lx Ms Mt Nl) Mb(Hr It Jj Li Mt Nm) Ms(It Lv Mf Ml Mt) Nl(Hr Ir Iu Jj) FpIt IkIn} Ad{Aj(aK aM aR aU bC bM bU cB cF cK cN cR cT cW cY cZ Db dF Dg Di dN) Bo(aF aH aK aO aQ aR aU aV aW bC bM bU cB cF cK cN Co cW cY cZ Db) aW(bM cF)} On{Ii(Fp Hx Ik It Iv Lv Mf Mh Ml Ms My Nk) Mb(Jj Mm Ms My Nc Ng Nl Of Oi Oy) Ms(Hx Nc Nl) Jj(Hx Nc Nl) Nj(Bo Db) NcOy ItJd} Mm{Mb(aA Fr Na Nl) Lv(Nc Nl) DbNj MlNc JntV} Fr{Mb(Nc Nl) LvNc NlJj} aM{IcJd bBfR} CwNiNj GpeMhB NmNttV NcJgJj ZqhGiZ aObFfR aWbBeP

Constrained panels with 3 analytes, where 1.0E-8 >= 'model p-value' > 1.0E-9. Contains 1,428 panels of 38,530,102 total panels evaluated. : Nd{Lx(Cw Hq Im In Iq Is Jg Jl Jn Jp Jq Jr Jt Lh Lv Lw Me Mf Mh Ml Mn Mr Ms Mt Mx Mz Na Nc Nl Nm No Nw Ny Og Oz Pb Pd Pe Pf) No(aA In Is It Jg Jj Jl Jp Jq Jt Lh Li Lv Lw Ma Me Mf Mn Mr Mt Mv Mw Mx Mz Ne Nl Nm Nw Of Oz Pd Pe Pf Po Qa) Jg(aA Aj aR Bo bR bU cB Cw Db Im In Is Ji Jl Jq Li Lv Lw Mh Ms Mt Mx My Mz Na Nc Ng Nr Of Og Oi Pd Pe Pf) Li(In Is Jl Jp Jq Jt Lh Lv Lw Mf Mn Ms Mt Mw Mx Mz Na Nc Nm Nw Of Og Oi Pd Qa) Im(aA Is Jj Jl Jp Jt Lh Lv Lw Mf Mj Mn Mr Mt Mx Mz Nc Nm Nw Og Pd Pe) Mn(aA Is Jj Jl Jp Jt Lh Lw Mt Mv Mx Mz Nc Nl Nw Pd Pe Pf Po Qa) Cw(Ad Aj An Bo Ch cR Dk Fr In Is Jj Lh Me Mu Na Nf Nw Pd) Nw(aA In Jj Lv Lw Mf Ms Mt Mv Mx Na Nc Nl Nm Og Pd Pf) Mt(aA In Is Jl Jp Jq Jr Jt Lh Lv Lw Nc Pd Pf Po) aA(Ip Iq Jp Jt Lv Nc Nn Nr Nv Of Og Po Qa Qe) Mm(Ad aM Aw bA Bb Ch cR cT De Di Dk) Jj(Iq Is Jk Jl Jp Mv Nr Nv Po Qe) On(Af Aj aO aR aW Bb cB cR Db Di) Lh(Bo Ii In Lw Ms Nc Og Pf) Bo(Dc Dk Ji Jp Nm Of) Ok(aR aW cF Ch Db Di) Ji(bU Ch Db Mv Pf) Lw(Is Jp Pf Qa) Nc(Jp Jt Lv Pf) Ad(Aj Na) In(Jt Qa) Jp(aR Lv) ItJt QaQb} Ok{Ms(Fp Fr Hr Ii Ik Iq Ir Iv Jg Ji Jj Jo Lh Li Lj Lx Mh Mm Nb Nh Nm Nr Nx Of On Po) It(Et Fr Hx Ik Im Iq Iv Jd Jg Li Lj Lv Lx Mf Mh Mt My Nb Nh Nr Qa) Ii(Hx Im Iq Iv Ji Jq Jr Li Lj Lw Mm Mv Mx Nh Nn Nw Nx Of Pd Qa) Of(Fr Hx Ik In Iq Ir Jg Li Lv Lx Mm Mt My Nb Nh Nk Nr On) Hr(Fp Hx Ik Iq Li Lj Lv Lx Mf Mh Ml Mm Mt My Nb Nh Po) In(Et Fp Hx Iq Iv Li Lj Lv Mf Mh Ml Mt My Nb Nh Nr) Jj(Fp Ik Jg Li Lj Lv Lx Mf Mh Mt Nh Nj Nk Nr) My(Ik Iq Jg Li Lj Mm Mx Nb Nh Nm Nr Po Qa) Hx(aA Fp Iq Jg Jo Lj Lv Mf Mm Mn Nm Nr On) Ng(Et Fr Ik Jg Lx Mm Mt Mv On) Lv(Jo Li Lj Mf Mm Nh Nm) Nj(aL aW cQ cR Cw Di Jo) Mf(Jo Li Lj Mh Nh Nm) Lx(Hv Nx Pg Qc) Mt(Hv Jn Nx Pz) Nk(Iq Ir Iu Nm) Ik(Iu Jo Og Oi) Mm(Fp Mh Ml) Nf(Fp Ml Pf) Jo(Fr Jg Li) Qc(Li Lj) Pf(Pd Pg) EtOi NmNe MhIr MwJg QaQb aCeP aRcW} aC{Bo(aF aM aR AW aX Ba bE bM Bn cB cF cN cR Ct Cu cW Db De dF Di Dk dN Et Fr) Di(aF aM aR Aw aX BC bE bM bU cB cF Cu cZ Db Dc Dk Dl dN) fR(Aa aO bA bF bO bR bW cG cI cK cM cP cR cT cW cZ dN Ef) Ap(Aj aO aX bC Bn bU cB Ch cN Cp cR CW Db De dN) Aw(aF aM aW aX BC bE cB cF Ch cN cR Cu Dc dN Fr) Dl(aR aW bC bE bU cB cF Ch cN Cp CW cZ dF dN Dr) Bb(aX bB bE bQ cB cG Ch cP CW cZ Db De dF Fr) Et(aI aL aO aW aX cR Cw cZ Db Mb Na Nu Oi) Dk(aR aW bC bM bU cB cF Cw cZ Db dN) cF(Ao Ba Bc Ch Cp Cu Db Dc De Fr) Cw(aH An aS bM cB Ch Dr Fr) Ch(aR aW bC bU cN cZ) Dg(aF aO aX Cp De Dr) Dr(Ao Bg dF Fr On) Fr(aR aW cB cZ) Cu(aW bC cZ) cB(aR Bc) cZ(Cp Dc) DebU NaOn} Et{Jd(Bg Db Hf Ic Jv Ki Kk Kp Kr Kx My Ql Qv Qz Ri Rm) aO(aR aW bA Bo cK cR cT Di gL iH Kx Lv Mb Mt Ne Nl) Mw(Ik Jg Ji Jr Li Lu Lx Mt Nb Om On) It(Fp Hv Iv Ji Jn Jq Kx Lj Me No) Mb(aW bC Bn bR bU cK cQ Cw Di) aA(Fp Mf Nb Ng Nh Nk Nq Oi Oy) Qv(Ic Na Nu Qy Qz Ri Ue Tj) aR(Bo bR bU cK Di Lv Na) Mv(Ji Li Lu Lx Of Om) Ng(Fr Jg Li Lx Nb Nh) In(Iv Jq Mt Nb Nh Pi) aW(bR bU cK Lv Mt Na) Na(cK Ow Qy Ue) Ji(Ij Nx Oy Pg) Jo(Jr Li Mt Nh) Kx(Db Nt Nu Oi) Pf(Pd Pg Qc Qd) Lx(Oi Qb Qc) Io(Li Lj Mt) Ow(Db Js Nu) tV(Di Il Nt) Qa(Qc Qd) Jn(Js Nf) BoLv DiNj NoPg LzQd MrNb MtPz IkOg HfoK IvOi QbQe QzRi LiOf PaPe bUiH} Nc{Mm(Fp Fr Hx In Iv Jg Ji Jj Jq Li Mf Mh Mn Ms Na Nb Ni Nk Of On Pf) Lv(aA Im In Jg Ji Jj Li Lw Lx Ma Mf Mn Mt Nb Ni Nk No Nw On Pf) Fr(Hv Hx Ii In Ji Jj Lw Mf Mh Ml Ms My Ng Ni Nk Oi Oy) On(Hx In It Iu Mf Mh Ml Mv Mw My Ng Ni Nk Of Oi Qb) Ji(Hx Ii In It Jj Lx Mb Mn Ms Ni Nk) Jg(Ii In Mb Mh Ms Ni Of Oi Oy) Mb(Jt Li Lx Mt Na No Nw) Jj(Jt Lh Li Lx Mt Po) Ms(Lh Nw) Li(In Ni) LxPg IiLh} On{Ii(Hv Ji Jq Lh Li Lj Lw Lx Me Mm Mt Ng Nh Nm Nq Nx Of Oy Oz Pd Po Qa) Nl(Hx Il In It Iu Lv Lw Mf Mh Mw My Nb Ng Nh Ni Nk Of Og Oi Oy) Mb(Hx Ij In Iu Jo Lw Mv Mw Na Nc Nk Og Pz) Nj(Af Aj aM aO aR aW Bb cR Cw dE Jj Ms) Ms(Io It Iu Ji Jj Mf Ml My Ne Of) Jd(Iu My Na Nt Nu Tj) Ne(Jj My Of Oy) Jj(Lv Mf) NacK HxOf} Mm{Mb(Hv Hw In Is Iv Jg Ji Jj Jl Jn Jq Jr Jt Lh Li Lj Lv Lw Mr Mt Mz Ne Nk No Nr Of Og Om Pd Pe Qa) tV(Di Il Jr Lv Mn Mp Mt Nq Nt Oh Qb Qc Qd wQ) Nl(Fr In Ji Jj Ml Mn Nb Nh Ni No) Jd(Db Fn Iu Na Qv Qz) Di(tO tT wJ) Lv(Jj Ne tQ) Nj(aW Bo Cw) tX(Nq Qd)} Ad{aW(aK aM aR aU aV Aw bC bU bX cB cJ cK cN Ct cY Di) cF(aM aR aU Aw bM cK cN Ct Db dI) Aj(Aw Ch Cw fR Hx Mb Na Nj) aM(Aw cB cK cT Di) Ct(bA bM cB cT) Nj(Bo Db Na Ni) bM(Aw cN Di) aR(Aw cB) ExqA cBcN} Nl{Fr(Hv Hx Ii In Iu Ji Lv Lw Mf Ms My Nb Nh Oi Oy) Lv(aA Im Jg Ji Jj Li Lx Mn Nb No) Ji(Hx Ii In It Jj Mb Mn Ms) Jj(Jg Lh Li Lx Mn Mt) In(Jg Li Nb) Jg(Ms Oy) LxPg MnNb IiLh} Bo{Dl(aK aM aQ aR aU aV AW bC bM bU cB cF Ch cK cT cW cY) Dg(Aj aK aM aR aU aW Bn cF) Nj(Cw Ni Of) BbaM} Jd{Tj(Cw Ip Iq Ir Lh Lx Po Qa Ut) It(Cw Ji Lh Lw Qa Tn) Iv(Cw Kq Lw Om Tv) Ic(Cw Iq)} Dg{Aj(aK aM aR AW Bn cF cK cY) aW(aD aM aR aU bM bU cF cK)} Nj{Cw(Aj Ch Db Fr In Jj Lx Nf Nk) Db(Dk Fr Jg Ji Jp Lx Nw) AjJg} Pj{Qv(tV uT vH vS yH tL) Di(tO tT) CwoK HutV IcqB} Mb{Fr(Ji Jj Lw Na Ne) Ji(Im Ms Mt) Jj(Jg Mt)} bB{fR(aN bC Db Dl) BbcF aNdX} tV{Bb(Nq Qw) Vt(Jl Qw) Illp KyfN} Ne{Jj(Fr Jg Li) MsJi IiLh} Ic{Kq(aM jD jM) CwoK} Jg{Aj(aR Db Hx) LvJj} Vq{Jp(vP vV) SsyL iHsC} hB{oD(bH cX mM mZ)} Ms{Ji(Fr Lx Mt)} Zq{Hx(aM Or) OrbW} aW{bM(Aw Bb) ApcF} fN{JpvS RirN} fR{DlcE bCbW} BbaMcK CwcFoK DitSuU NqJtrN LvMtJj TtqWvS sFrSqP Constrained panels with 3 analytes, where 1.0E-7 >= 'model p-value' > 1.0E-8. Contains 4,368 panels of 38,530,102 total panels evaluated. : Nd{Lw(aA Ad Ap aR Bb Bo Ch cR Dg Dk Ih In Iq Jj Jl Jt Lj Lv Lz Ma Mp Mr Mv Mw Mx Mz Nc Ne Nl Nn Nr Nv Ny Of Og Oz Pa Pd Pe Po Qe) Lh(Ad Ap aR bR bU cB Ch cQ Db De Di Dk Hx Is It Iu Jg Jl Jo Jp Jr Lv Ma Me Mf Mv Mw Mx Mz Na Nl Nw Ny Of Oi Pd Pe Qa Qe) Jp(Ad aO Ap bR bU cB Ch cR Db De Di Dk Iq Is Jl Jq Jt Lj Lz Me Mf Mh Mr Ms Mv Mx Mz Na Nl Nm Nr Og Pd Pe Pf Po Qa) Nc(In Iq Is Jj Jl Jq Jr Ma Me Mf Mg Mp Mr Mu Mv Mw Mx Mz Na Nb Nk Nm Nn Nr Nv Ny Of Og Om Oz Pd Pe Po Qa Qe) Lv(Ih Iq Is Jj Jl Jq Jt Lj Ma Me Mf Mn Mp Mr Mv Mw Mx Mz Na Ne Nm Nn Nr Nv Ny Of Og Pd Pe Pf Po Qa Qe) Mv(Bo Ih Im In Iq Is Jg Jl Jq Jr Jt Lj Me Mf Mr Mt Mx Mz Na Nl Nm Nn Nr Og Oz Pa Pd Pe Pf Qa Qe) Pf(aA Ih In Is Jj Jl Jq Jt Ma Me Mf Mg Mp Mw Mz Na Nb Ne Nl Nm Nn Nr Nv Ny Of Om Pd Po Qa Qe) Mn(Ih In Iq Iv Jg Jn Jq Jr Lj Lz Ma Mf Mp Mr Mw Na Nb Ne Nh Nm Nr Nv Of Og Om Oz Pa Qe) Qa(Bo Im Is It Iu Jg Jl Jq Jt Me Mf Mr Mt Mx Mz Na Nh Nm Nw Of Og Oi Oz Pd Pe) Qe(Im In Is Jl Jq Jr Jt Li Me Mf Mr Mt Mx Mz Na Nl Nm No Of Og Pd Pe) Po(Im In Iq Is

Figure 6 Continued

Jg Jl Jq Jr Jt Li Me Mf Mr Mx Mz Na Nm Nw Og Pd Pe) Jj(Ad Ih Ij Jm Jo Jq Lj Ma Mf Mg Mp Mw Mx Mz Nl Nm Nn Ny Of Pd Pe) Jg(aM aW bB bM cF Ch cR De Di dN Iu Jn Jr Lj Lz Mf Mr Mw Nl Oz) Jl(aA In Iq Jq Lj Ma Me Mf Ms Mw Mx Mz Na Nm Nn Nr Nw Ny Og Pd) Mt(Iv Jn Lj Ma Me Mf Mr Ms Mx Mz Na Nm Nr Of Og Oz Pe) Im(In Iv Jn Jq Jr Lj Lz Ma Me Mp Na Nl Nn Nr Om Oz Pa) Is(aA Bo In Iq It Ma Me Mf Mp Mw Nm Nn Nw Ny Of Og Pd) Pd(aA Ad Bo Dg In Jt Ma Mp Mw Nl Nn Nr Nv Og) Mz(aA In Ma Me Mf Mp Mw Nl Nm Nn Nr Nv Oz) Bo(Ap Bb Ct Dg Dl Fr Jh Jt Mg Nx Om Oy) Cw(aM aR aW aX bU bW cF cN cQ cW Jd Nm) Ji(Ad Ap aR Bb Bg bR cB De Dg Di Dk fR) aA(Jq Lj Ma Ml Mw Mx Na Nl Nx Ny Om Pc) Jt(Iq Jo Mf Ms Mw Mx Nl Nw Og Oi) Li(Ih Iq Ma Mg Nl Nn Nr Nv Ny Qd) Pe(In Ma Me Mf Mp Mw Nn Nr Nv) Ad(aM aW Ch cN cR Db Di Lx) Mx(Ma Mp Mw Nm Nn Nr Nv Of) Mm(aR Ax Bn bQ cB Dc Dd) Mr(Ma Me Mf Mp Mw Nn Nr) Nm(aR cR Dk Nl Nv Og) Nn(In Jq Na Nl No) Nv(li In Ms Og Oi) Jh(aR bM bU cB) Jq(In Mw Nr Og) No(Mg Mp oD) Lx(Bb Ch Iv) Nw(Iq Me Nk) Lj(Of Om) Og(Mw Of) AjDg BbaM DkNa TjEt MaNl MyfR IhIn JdKp OndE} Et{aO(Aj aQ Ar Aw bB bF bQ bR bU bV cB cQ Cw cY Db dI Fb fP hC Hf iA Ic Iu iZ Jd Jj Kp Kr Ky Lu Lx Ml Na Nc On Qv Ri Ur Tj) Tj(Cw Db Fn Hf Hq Im Iq Je Kx Li Lx Mb Mk Ml Nu Oh On Oy Pf Po Qy Qz Rg Us Ut) Kx(aM aR aW Bo bR cR Fn Hf iA Ic Ih Iu Kd Kp Kr Mj Nn Qv Qz Rf Ri Rm Us) Di(aC aF aH aW aX bR cK cQ cR Db Hx iA iH Is My Na Ne Nl Ns Og qY) Kr(An aR Fb iA Ic In Iu Kk Kp Na Nu Og Oh Oi Ou Ow Qv Qw Ri Ue) Bo(aF aH aW bR cK cQ cZ Hx iA Is Kk Ne Nl Og oK Ow Ri Ue) Db(Aj aR Bn cK iA Ic Je Kp Lv Nc Ne Nl Oh oK Qv Ue) Hf(aM aR aW cQ cR Fb iA Ic Iu Je Ou Ow Qv Qy Ue tF) Cw(Aj cK Hx iA Ic In My Nf Nl oK Ow Qv Ri Up) cR(aQ aU bR cK cY Fb Hx Jd Lv Na Nl Ns oD Oi) Nt(Fb Ic Je Kp Kq Ou Ow Pk Qv Qy Tn Tt Un) Ic(aM aR aW Fn iA Iq Iu Ly Na Nu Qz Ri) Qy(Fn Iu My Ng Ns Nu Oi Qw Qz Ri Us) iA(aR bU cA Hq iH Im Iq iZ Jj Mh Na) Fb(Aj aR aW Ax cC Jj Mb Mc Nu Qz) Qv(aL An aW cZ Fn It Iu Kk Ow Uk) Rm(Hq Im Iq Is Oh On Ou Ow Oy Qa) iH(aR cF cM cQ dB dE Jj oK Oz tF) Ri(Aj aW Fn Iq Iu Kk Kp Ow Oz) Na(Bn bR bU cQ cT Je oK tF) Fn(Iu Nu Oi Ow Ql Qz Ue) Hx(aC Aj bA cK cQ cT Ut) Jd(aL aM aR aW bU cB cZ) In(Kq Ow Pk Tv Vp Vu) Je(Ly Nv Oi Ql Qz Us) bR(dI Is Lv Ml Ne Nl) cK(Aj Iu Jj Lv Nk Oi) Nu(Kk Kp Ou Qz Tt) Ow(It Iu Ms Oi Qz) Aj(Ad aR Jg Lv) aW(aQ Ml Nl Oi) tV(fN Ij Qd Qw) It(Pk Un Ut) aC(bU Dr Iu) bM(Mp Nn Oh) Lv(bC cQ) Mb(Ad bA) Nl(bU dE) Ue(Ur Us) Nv(Lh Ut) Pk(An Iv) dU(hC Nx) EqmE MvUs IjsF IqUr IuQz KdKq QlOh OicQ OndE UpVu aHbB bUcC} Jd{It(Ad Bn Cp Cu Dc Hv Hw Id Ii Ij Im Ir Is Jh Jn Jo Jq Jr Jt Ke Kf Kq Kx Lx Mi Na Nm Om Pb Pd Pe Pk Qe Tr Tt Tv Uc Ul Un Up Us Ut Vt) Tj(Db Fn Fr Hf Hq Im Jh Ji Jp Kf Kp Kq Kx Ky Li Lw Ml Mm Mr Mt Mu No Of Oh Ok Om Ow Oy Pd Pe Pf Pj Qe Qv Qz St Tn Tt Tv Uh Un Ur) Fn(aM bU Cw Ic Id Im Ji Jp Jq Kp Kq Kx Ky Lh Lv Lw Na Nm Nu Oh Ok Om On Ow Pd Pj Qa Qe Qz Tn Tt Ue Uh Ul Un) Ic(aR bC Bo bU cB cF cN dN fN Fr Hf Im jG Kn Kp Kq Kx Ky Mm Nu Ok On Pj Pk Qa Qv Qz Uh) Cw(aM An Bg bU Ha Hu Hv Hw Hx Ib In Jn Ju Jv Kp Ky Mm My Na Nf Nt Nu Qw Qz Up Vp) On(Bg Db Ez Ha Hf Hr Hu Hx Jl Js Jv Kd Ki Kk Kp Kr Kx Ky Nv Oi Qw Qz Ri Rm) Qz(Ip Ji Jp Kp Lh Lw Lx Mu Of Og Oh Ok Pj Qa Qe Qv Tt Ue Uh Ul Ut) Nu(Fr Im Ji Jp Kp Lh Lw Mm Oh Ok Ow Pd Qa Qe Qv Tn Tt Uh Ul Un) Na(Ad bU Im Iv Ji Jp Kp Kq Kx Lh Oh Ok Ow Pj Qa St Tn Tt Ue Un) Mm(aM Bo Di Hf Ki Kp Kr Kx Ky Nt Oi Ow Ri Tt) Iv(Ad Cu Dc Id Ij Ji Jq Jr Pb Pd Pi Pk Un) Kp(aM Db Hf Ki Kk Kx Ky Of Ow Pj Ue Uh Ul) In(Ip Iq Kq Lh Lw Ok Pi Qa Tv) Oi(Im Ip Lh Oh Qa Qe St Uk) Pj(aM Db fN Hf Jv Kr Kx Qv) Nt(Im Kq Lh Oh Ok St Tt) Ue(Bo Db Hf Ky Og Qv Uh) Iq(Jv Kk Nk Og Qw Ur) bU(aM aR Db Hf iH Iu) Hu(Fr St Tn Tt) Kq(Kd Nb Nv Vp) aM(Ip Ky Of Qw) Iu(Im Qa Qe) Lh(Hx Js Ms) Ut(Hx Nb Nv) fN(lL Nq tV) Db(Ky Nj) Hf(Ok Ow) Ip(Pz Ur) St(Jv Nk) Qv(Uh Uk) Rm(Im Qa) MhPf MvUa TtOg JsOh OfaR} aC{Dr(Ad Af aJ AP Ba bB Bc bE bH Bn bQ cE cF cG Ch cL cN Co Cu cX De Gc Jg Ji Ng Nq Zq) Bc(aM AR aW aX bE bF bM bQ bR bU cE cG Ch cN Cp Cu cW cZ De dF Dk dN Fr) De(aF aM aR aW aX bC bM cB cG Ch cN cR Cu cZ Db dF Di Dk Dl dN Fr Gc) Ch(aF aM aO Ar AX bE bM Bn cB cG cR Cu Db Dc dF Di Dk dN Fr) cB(aJ aM Ao Ar aW aX Ba bF Bn bQ cF cN Cp cR Cu Cv Db Dc dN) aR(Ao aW Ba Bg Bn bU cF Co Cp Ct Cu Db Dc Jg Jp Lh Ok On) Ba(aF aM aO aW aX bC bE bM bU cN cR cW cZ Db Di dN) Db(Ao aW bC Bg Bn bU cG cN Cp Cu Dc dF Dl dN Fr) Cp(aM aW aX bC bE bM bU cG cN cR dF Di dN) Fr(aF aO aX bC bM bR bU cG cN cR Di Dl dN) aW(Ao Ar Bg bM bU cF Co Dc Di dN Mm Ok) Dl(Aj aM Ar aX bF bQ cE cG cR Dk) cF(aM bB Bg bQ cG cN Co cR dN Gc) Ao(aM aX bC bM bU cN cZ dF dN) Dc(aX bC bE bM bU cG cN dF dN) Zq(Ap Cq cW Fb Hx Je Mm Or Ye) Cu(aF aM aX bE bU cN cW dN) Dk(aM aX bE cG cJ cN cR dF) Ok(aL Bo cW dX Io It Na Oi) Co(aM bC bU cN cZ dN) Di(aO cG cN cR Cv dF) Bg(aM bC bM bU cZ) Gc(Af bE Bn cN dF) Ar(bC bU cZ) Bn(bU cZ dN) Bo(Aa Of On) Cw(Iv Mm Nj) Eo(bM bR) Na(Ad Jg) Nj(fR Mm) On(It Iu) AabM AxbC DwcP ExfR bQbR} Bo{Nj(aM Ap aR Bb Bn Ch cR Ct Db Dc De Dg Dk Dl Fr Im Is Jg Ji Jp Lh Lv Lw Lx Ma Mg Mn Mt Mv Nk Nm Nw Om Oy Pd) Dg(aD aF aH aO aQ As aV Aw bA bC bM bR bU cB cK CP cQ cT Cu Cw cY Dc) aU(aM Ap aR AW Ax bA Bb Bc bM Bn bU cF cR cT Cu Cw cZ Dc Dk dN FR) Ew(aG aL aW Ax aZ Ba bI bO bV cH cI cM Co cR Cs cV dM dN eP) aM(aK Ap aQ aR aV AW Ba bM bU cF cK cT cY Ef Eo Ok) aK(Ap aR AW bA Bb Bc bM Bn cF cT Cw Dc Dk Fr) Eo(aR Ba bM bR bZ cB cO cT cV cW dB dF dN fP) aR(aQ Aw Bb Bn bU cB cY Ef Jg Nm Of Ok On) cF(Ap AW Bb Bc Bn cK cT Cw Dc Dk Fr) bM(Aa AW Bb Bn cT Cw cY Dk Dw) eO(aW bR bV bZ cB cV dB dN fP) Ok(aH aO aW bR cK cQ cW Lv) dW(aW bP bR cB cV dN fP) eW(aW bV cK cN cT cV dN) Dw(aW bV cK cN CV) Ad(Lv Mb My Og Tj) Dl(bR cP dF dN fR) On(aO Mb My Na Nv) Bb(aV bU cK cY) bU(AW Bn) Ef(aO Dr) cK(Bc Of) ApBn CvfR CwoK DccY MmTk aOdF} Nl{Jj(Ik Im Iq Iv Jl Jp Jq Jt Lw Ma Mb Mf Mg Mv Nb Nm Nn No Nr Nv Nw Nx Ny Of Pd Po Qa Qe) Jg(aA Hx Ii Io Iu Li Lw Lx Mb Mf Mh Mm Mn Mw My Na Nb Ng Nh Ni Nk Of Og Oi Pf) Li(aA Hx Ii Im Ji Lh Lw Lx Mb Mf Mm Mn Ms Mt Nb Nh Ni Nk Oi Qd) Lv(In Iv Jp Jt Lh Lj Lw Ma Mf Mt Mv Mx Na Nh Nm Nw Og Pf) Mn(Im In Jq Lw Lx Mb Mf Mh Ms Mt Mv Na Ni Nk Nm No Nw Pf) In(Im Iv Jt Lh Lw Lx Ma Mt Nm No Nw Of Pd Po Qa Qe) Mb(aA Im Jp Jq Jt Lh Lw Lx Mt Na Nm No Nw Om Pd) Nb(aA Im Ji Lh Lw Lx Ma Mf Mt Nh Nk Nm No Nw Pf) Mm(aA Fp Hx Iu Iv Jq Jr Lj Mf Mh Ms Na Of Pf) No(Hx Lw Mf Mt Nh Ni Nk Nm Of) Lx(Hv Hx Ji Lw Mf Ms Nh Nk Ny) Lw(Im Lh Ma Mt Nw Of Pf) Mt(Jq Mf Ms Nh Nk) Nw(Ii Mf Ms Na Nh) On(Hv Jk Mv Qb) Ji(aA Nh Og) Im(Mf Pf) It(Is Jt) Lh(aA Ms) NkaA QaQb OkcW} Nc{Mb(aA Im In Is Jj Jl Jp Jq Lh Lw Ma Mn Mp Mr Mu Mv Mw Mx Mz Nb Ni Nk Nm Nn Nv Nx Ny Of Om Pd Pe Pf Po Qa Qe) Jj(Fp Ik Im Iq Is Iv Jl Jo Jq Lj Lw Ma Mf Mg Mn Mv Nb Nk Nm Nn No Nr Nv Nw Nx Ny Of Pd Qa Qe) Nk(aA Im Iv Jg Jt Lh Li Lx Mf Mn Mt Mv Nb No Nw Po Qa) In(Iv Jt Lh Lx Ma Mf Mn Mt Nb Nm No Nw Nx Po Qa Qe) Li(aA Hx Ii Im Jg Ji Lh Lw Lx Mf Mn Ms Mt Nb Oi Qd) Nb(aA Ji Lh Lw Lx Ma Mf Mn Mt Nm No Nw Pf) Jg(aA Hx Io Iu Ji Lx Mf Mw My Na Ng Og Pf) Mt(Hx Ji Jq Lw Mf Ml Mn Ms Ni Nm No) Lx(Hv Hx Lw Mf Mn Ms Ni Ny Qb) Lh(aA Hx Lv Lw Mf Mh Ni Oi Pf) No(Hx Lw Mf Ml Ni Nm Nx Of) Lv(Iv Jt Lj Mx Na) Mf(Im Ma Mn Nw Of) Ni(aA Im Mn Nw Po) aA(Ji Ml Mm Nx) Mn(Lw Mh Pf) Nw(Hx Ii Lw) Im(Ml Pf) Jt(Ii It) On(Hv Il) MmJr ZqbW QaQb} Nj{Mm(aA Ad aM AR Aw bA Bb bQ cB Ch cR cT De Di Dk Fr In Li Lv Ml On) Db(Aw Bb Bn Ch De Dg Di Jh Jj Lh Lv Lw Mn Mt Ni Nk Nm No Om Pd Pf) Fr(aA aM aR aW cR Di Hx Ii In Ji Jj Lv Lw Mb Mf Ms My Na Oi Oy) Cw(aM aR aW aX bU cQ cR Dk Hv Hw It Iu Jg Ji Lw Na Nw Oi) cR(Ad Dk Jg Ji Jp Lw Lx Mt Mw Ni Nk Nm Nw Of Om Pd) On(Di Hx In Iu Lv Mf Mh Mw My Ng Ni Of Og Oi Oy) aR(Ad Dk Is Jg Jh Ji Jp Lh Lw Lx Ni Nk Nm Nw Om) Nk(Ad aM bA bB bF bQ cG Ch cN cT dF Dk dN) Ad(aM Ar aW Ch Di In Jj Lx Mb Oi Pf) Ni(aM Ap Bb bU cB cF Ch dF Dg Di Dk) Lh(aM bR bU Ch cQ Di Ii Jj) Jg(aM aW bR bU cB Di Jj) Dg(Aj aM Jj Lx Na Oi) Ji(bU cB Ch fR In Ms) Bb(aM bB Lx Pf) Nw(aM bU cB Ch) Dk(Iu Na Oi) Lx(cB Ch Pg) Li(Im In Jj) LvaA MtJj JpbU hBoD} Ad{aM(aK aQ AR aU aV bA BB bF bM Bn bQ bU cE cG cJ cN cR Ct cW cY dF dI) Ct(aK aR aU Aw aZ bC bQ bU cE cG Ch cK cN cR Cw cY Db dF Di dN) aR(aK aU bC bF bM Bn bQ bU cE cJ cK cN cT cW cY dF Di dN) Di(aF aK aO aU bC bR bU cB cF cK cN cY Db dN iH) bM(aU bA bF Bn bQ cB cE cG cK cR cT cY

Figure 6 Continued dF dI) cN(aF aK aU aV Aw bE bR bU Ch cJ cK cT cY Db) cK(Aw bC bQ bU cB cG Db dF dI dN Na) Aw(aK aU bC bU cB cR cY Db dN)
Aj(iH It Jg Lv My Og Ok Pd) cB(aJ aU bA Bn cF cR cW dI) aU(bA cR cT Db dN fR) Na(eD jR IL Ow) aO(bF bQ dF dN) aW(bR cG dN fR)
cF(bA Bn cT iH) Hf(eD rB rN) cY(cR dJ dN) tV(Ky Nt Qw) Bn(Db dN) aF(bF dF) aK(dJ fR) iH(bU Oz) NqrN MbMm} On{Ne(Hv Hx Il In It Iu Jk Lv Lw Mf Mh Mm Mv Mw Ng Nh Og Oi Qb) My(Cw Hf Hx In Jj Li Lv Lw Lx Mf Mh Ml Mm Mt Nh Of Oy Pf) Jj(aO aR Fp Hv Ik Iv Lj Mh Ml Mt Mv Mw Ng Nh Nk Oy) Hx(Aj Dr In Ji Lj Lv Lx Mh Mm Mw Ng Nk Og Oi Oy) Na(Aj aN aO aQ aR aU aW cQ dE Kx Ow Pj Tj) Ms(Fp Ik Lv Lw Mh Mt Ng Nh Nk Oz) Oy(Ik It Jg Li Lv Mf Ml Mt Nh Of) It(aO Ic Kx Ow Qv Qz Tv) Mb(aA Aj aR cQ Cw) Cw(Ii In Tj) Nt(Ow Pj Tt) Hf(Ic Ow Tj) Jg(Aj aR Mw) Dr(cB Vp) Lv(Ng Of) Mf(Mw Of) Iq(Ha Tj) Zq(mM mS) Js(aR Ow) Ok(Jo Nx) ExvV NgIk NiNk UeQv IcaM QaQb JkaO NvcR} bB{eO(Aa aD aE aH Aj aL aM aN Ao aP aQ aW Ax aY bA Bb Bc bL bP bV cE cH cI cM cN Co cP Cs cW cX cZ DC dG dI dJ DL dM dN eM eP Gd gV) Eo(aD aE aH Aj aN aP aW Ax bA bL bV cI cM cN cP Cs dG dK dM dN eM eP gV) fR(aK aO aU aW Bb Bc bH bM Bn bQ bR bW cE Ch cP cT Cv cY dN DR Ef Ji) Dw(aD aG aH Aj aW bM cH dM) Zq(kC lY mE mF mH mM mS nC) dW(aD aN aW Ax cI dM eP) eW(aF Aj aW bM cN dM eP) Ew(aF aW bM dM eP) dU(Ny Oz Pb) Bb(aM bM) Dg(Aj cF) aR(cB Jg) pH(Nb Nu) AapI DrEf KoeP} Mm{tV(aU bF bZ cG cM dF fN Gp iO Ky Mv Na Of qV QW rW sC St tT yH zA tL) Ne(Fp Fr Hx In Iv Jg Ji Jj Jq Li Lj Mf Mh Ml Mn Ms Na Nb Nh No Pf) Lv(aA Fp Hx Iv Li Lj Mh Ml Ms Mt My Nb Nh Nk Oy Pf tT) tQ(Di fN Mn Nq Pc sC wG yH) tT(fN Mn Mp Nq Nu Pc Qd yH) tX(Di fN Hx Mn Mp Nu Pc yH) Mb(AW Bn Cw Dc) Ml(aA In Ms Mt) Hx(Fr Ji Li Lx) Jj(Fp Ik Mt) Cw(Fw oK) Di(tS wP) Mn(tN tU) Na(Kx Ow) Ic(hP qB) Ii(Ji Lh) DbOw FrMy NqtN MsJi NiNk UeQv InPi ZqmS JoOk} Zq{mS(aF aH Ap aS Bb Bc Bn bP bQ bW bX cF Cq cV De Di dL Fc Fy Hb Hq Hv Id Ij Ir Is Jp Jr Ky Lx mE MF Mn Mv mW Nr nT Qn Yi) aH(kE kF kG kK kN kO kP lW lX lY mE mF mH mI mM mY nB nC nI nJ nL nO nR nT) Or(aO bR dM kP Lt mY Nw) lY(Ap cR Hq Ky Mn Mv) mM(aA bQ cR Hq Kq Ky) aM(bW kP Lt Ng) mH(Ax Bb Cs Mx) Rg(bR Hx Pk) cR(kP lX mY) kF(bQ Jr Nr) Bb(kC kK) Nq(kP mW) AxmE FbbW LukP IvkC KnlW LjmW OamY bLkK cZnC} Jg{aR(aW bM bR bU cB cJ cQ Di Ji Jj Lv Lw Mb Ml Na Oi Ok) Aj(bM bR bU Ch cQ cR Cw cZ Kx Lv Mb Mg Na Nm Ok Pd) Ne(Ii In Lv Mb Mh Ms Mw My Ng Nh Of Og Oi Oy) Mb(aA Ji Jq Lx Ms My Na Ng Of Oi Oy) Jj(Fp Hx Iv Lj Lx Mf Mh Ms Mt Nk) Ms(Ji Lv Lx Mf Mh Ml Mt Of) Ok(Ij Iu Mh Nm Oi Oy Pz) Lv(Ii Mw My Ng Of Oy) Lx(Hx Ii My Ng Oy) Ii(Ji Lh Po) Na(cQ Kx) aW(bM bU) DrcF NttV MtOy MwOm IcaM OibM bUiH} Ok{Jo(Fp Iq Ir Iv Lh Lx Mh Ml Nr Nx Po) aR(AW bR cK Di Lv Mb Na Nf) Ji(Ij In Mw Nb Nf Nx Pg) cW(bR cK It Mb My Na Nf) Fr(Hv Jj Mw Nx Oy) Of(Lu Mw Ng Nx Oy) aW(bR cK eP Mb Na) Po(Jj Lx Nf Ng) Nm(Hv In Mh Ml) Li(Hv Nf Ng Oi) aA(Hv Ir Ml Nq) Qc(Nr Qa Qe) Qd(Lz Qa tV) Jj(Iq Iv Nb) Jr(It Js Nf) Mu(Mw Oy) Na(cK cQ) Kx(dX eP) GzuL NrNg NttV LxNy MbcQ MxNf HvLj IcaM InJq QbQe NwPg aDgV sJrW} Ji{Ms(aA Hx Ik Im It Iv Jj Lh Li Lv Mf Ml Mn Nh Nr Nx Oz Po Qa) Ne(Fr Hx Ii In It Jj Li Lv Lx Mb Mn My Nh Og Oy) Mb(aA Ii In It Jj Li Lj Lx Mn My Na Og) Ii(Fr Im Lh Li Lx Mt Oz Po Qa) Hx(aA FR Im Li Lx Mt) Mt(In Jj My Oy) Fr(Mw My Oy) fR(aW Fp gP) aR(bR bU) mE(Du Si) hB(gZ oV) LxMy QaQb aDgV aHdU fNtV} tV{Ic(Bb bQ Di fN iO jF jG Jn lK Pe Pj rA RB rW) Ky(aZ bQ Di iP Lv Pj wG wH zG tF) Vt(Di fN Ih jY Nq Qb Qd Ql Rm) fN(Bb Hf It Jp Lh Qv Qw Ri) Pj(Jk Nq Qb Qc Qd Ql Qw) Ip(Di Nt Qc Qw rW) Bb(Gp jF Qv sC) Nm(Il Qc Qd Qv) Cw(bQ Lv) Di(It Uf) Mz(Il St) Jt(Nt Qd) Kc(Jl Qb) HuTt ItSt JkOf} aW{Dg(aK aQ aV Aw Bn bR bX cB cJ cT Cw cY Di dJ fR) bM(Aa Ap bF bQ cB Cw Dk DW EO eP) fR(aK aM aU bF cE Ch cJ Cv cY Db Dl Ef) Ap(aD aK aM aR aU bU cK) bU(aR Aw Bb bF Cw Dl) cF(Aw Bb Cw Dl Fr) Dl(aU Aw cB) eP(bR Fr Nw) Cw(aK aU) BbaM DwbR aRcB cPcO} Mb{Mt(aA Im In Is Jl Jn Jq Jr Jt Li Lj Lv Lw Ms Na Ne Nm No Pd) Fr(aA Hx Ii Jn Jq Jr Jt Ms My Ng Nk Nm Oy) Li(aA Im In Jj Jq Lv Lw Na Ne) Lx(Jj Jq Jt Lw Na Ne Pg) Jj(Jl Jt Lh Qa) Ne(Mn No Nw) Lh(aA Ii Ms) Nw(Ms Na) QaQb} Ne{Fr(Hv Hx Ii Iu Iv Lv Lw Mf Mn Ms My Nb Ng Nh Oi Oy) Lv(aA Im Jj Li Lw Lx Mf Mn Mt Nb Nm No Nw Pf) Jj(Jt Lh Lx Mn Mt No Po Qc) Li(In Lw Mn Ms Nh) Lx(Hx Ms Pg) Mn(In Lw Nb) No(Mf Nb) Ms(Lh Nw) ItJt} Aw{bM(Aa aK aM Ap aQ aR aU bA Bb bQ bU cB cF Ch cK cN cR cT cY Db Dg Dk Dl Fr) Dg(aD aK aM aR cF cK Ct) Dl(aM aR bU cB cF cK Db) Ap(aM aR cF cK) aR(bU cB cK) aM(Bb cK) cFcK dBeO} Ic{Kq(aR cN cZ eD Fn gP iC jG jQ jR tF) Di(eD hR jD tN tS) Pj(jQ Qv tM xA) Cw(aM oH tF) jG(Fr Mu Mw) Bb(rW tN) Bc(fN hP) Qh(jM jR) rN(jF Ss) RirW OfaM VtqD PfjD} Dg{Aj(aD aO aQ As aU aV bA bC bM bR bU cB Ch CP CQ cT Cu Cw Dc De Di Ef Fr) cF(aD aM aR aU Bn cK cN) aM(cJ cK cT) CosF aRcB} fR{Dl(Aj aK aU bA bC bF bQ bR cY) cE(aD aK aM aN aO bM bR cM Cs) aM(aK aU bW cJ cT cY) bQ(aD aK aO bR cO) bF(aN bR) AjEf ChaO DbbA aDgW aUbW bCbE} Bb{bM(aK aM aU bA bQ cF cK cN cT cY dF Di) aM(aK aU aV bF bU cB cF cJ cT cY) cF(aU bA cK cN) cK(dF dN) fN(tT yH) bUcN} Lv{Jj(Fr Im Lh Li Lx Nr Po Qa) Li(aA Ii Im In Mf Ms Mt) Fr(Hx Ii My Nk) Mt(Lj Ms My) Lx(Hx Pg) NhaA IiLh QaQb} Ef{Dr(Af aI Aj aU aV aY bE Bn cB cF Ct cY dD) Gc(Aj aM aR aU aY Bn cF cY dD) AjEm} Pj{Qv(Ow qB Ss tQ Ue vB vO) Di(qY tS vP vV yH tM) rN(Nq Ri sC yH) Cw(oH tF) IlsH qBjD qWsC} hB{oD(bU iJ Jl kS Mk Mz nC Nk pI Qc Qe) Th(kC kE kO) gC(Qn Qz Ut) eM(Gc Ur)} Cw{oK(aR bW Ct Dr Ir Iv Oz) cF(cK cN oH) AjtF DraM TjLx NooD UeQv InIs dBiH gCnW} Ms{Mt(Jj Jq Jt Lh Li Mf Ml Po) Fr(Hx Iv Mf Ml) Lh(aA Ii Jj Lx) LxHx} aH{nA(Fi Gn Rz Sh Ye) Rz(mF nL) lX(Du Gn) MqoD NvpI OmdU cFpH} Jj{Fr(Hx Ik Mf My Nk) Hx(Lh Li Lx Mt) Mt(Li Mf) IkLi} Vq{To(sC uI uM vP yH zG) Tt(sC sK) QvsC dRyL} mE{Du(aJ Ao bN cR Ij Jn Mn Nq Nw) GcJl} No{oD(Bn bX cX iJ) eQ(cX nI) jB(Mk Oz) aLoT} cP{Hb(aM cG Jl Po) Ko(Lx Qx Ur) FrKc QxNw} fN{Jp(rX yL tL) Di(tS tT) Mz(Il Vp) KevH NwvS} Lh{Ii(Im Li Lw Lx Mt Po) aDgV} aM{Eo(An cV cY) Ap(cF cK) AfGc cVeO} Tt{qW(sC uI yH) rN(jV Ri) TjFa} bM{bX(dW cO eW) AabQ DwdK aSdW} cR{Sj(mP mU nN) NioD YemU RzmW} Di{wH(Ky Vt) qO(uV wL) FyqY} Fr{My(Hx Lw Mf) NkHx aObF} Nq{rN(Ap Kf Kj) GnnN UftT} Dr{Dk(aU Em Hr) XamS} Kq{Hf(jY oK tF) PafB} Lx{dX(Hb Ko) QaQb} cF{Ap(Bn cK) OzjB} iH{NwvS bUtF bZrC} rS{sF(jF Pc) MwsI} Ko{EqkG gCnW} aD{EodE bAdX} cB{DlaR bZeO} AanWpl DdExYe ThaGoO NkNvoD HqWhUt TrRirW QvVtuZ KfiArN KpsJkS OzmTjB

Constrained panels with 3 analytes, where 1.0E-6 >= 'model p-value' > 1.0E-7. Contains 12,541 panels of 38,530,102 total panels evaluated. : On{My(aC Ad Af Aj aR AW Bb bR cB Ch cK cQ cR Db Di Fb Fn Fp Fr Ic iH It Jg Ji Lj Mv Mx Ng Ni Nk Og Oi Ow Pj Ql Qv Qy Qz Ri Tt Ue Tj) Cw(aC Aj aR cK Cu Fw Ha Hq Hr Hv Hw Hx iA Ic It Iu Iv Jk Jl Jn Jo Js Mj Mp Mu Nf Ng Nl Nn Nv Oh Ow Pa Pj Qz Rm Tv Ue Up Vp) Hf(aF Aj aM An aO aR aW cQ cR Fb Gl Ha Hq Hr Hu Hx Ii In It Iu Jj Jl Ko Kx Mc Mm Ms Nd Nj Nn Nt Nv oH oK Pg Pj Qv Qz Ue uZ) It(aF aQ aR aU bA Bn Bo bR bU cB cK Cp cQ Cu cY Dc Dp Fb Fn Id Ji Kk Kp Kq Mh Mv Mw Ou Pi Pj Pk tV Ue Tj) Tj(An aO aR Bo Db Fb Fn Hx Ic Jg Kd Kp Kx Lh Lx Ly Mb Mh Ml Nd Nt Nu Nv Oh Oi Ow Po Ql Qv Qz Rg Us) Ic(aN aR cN Db dE Fn hP Iq jG Jl jM Kd Kp Kr Kx Ky Ly Na Nd Nt Nu Nv Ow Pg Pk qC qD Qv Qz Ri) iH(aF aJ aO aR bU bZ cF cQ dB dE iA Io Jj Mh Mj Mm Mu Nh Nm Nn Oh oK Oz Pe Pg Pj tF) aC(aF aL aO aW aX Bb cB cR cZ Db dJ Hx Ij Jg Jj Jk Jl Jp Js Mb Nk Nt Nu Nv Oi Ye) cK(aF Aj aO aR aW Bb Bo cB cR Db dE Hx Ii Iu Jg Jj Jk Jl Js Mb Ml Nk Nt Nu Nv Oi) Hx(aA aF aO aW bB Bo bR cB cQ dE Fp Iu Jo Li Lw Mf Ml Mt Mv Nh Ow Pf) aR(aF Aj aO aW Bb bR cJ dE Di Hq Hr Ii Jd Ji Jk Jl Lv Ml Mu Nn Nv) Oi(aN aO aW Fn Fp Ik Iv Ji Kx Li Lj Lv Mf Mh Ml Nh Nk Of rW Tt) Mw(Fp Fr Ik In Io Iv Ji Li Lv Lw Lx Mh Ml Mm Mt Nh Nk Of Om) aO(aN cB cR Ex Hr Ii Il Iu Jd Jg Jl Js Mb Nv Ok Qv Rm Zq) Bo(aF aH aN aQ aU aW cQ dE Fw Hv Jg Jl Js Lv Nm Ow Pj) Mh(Ij Il In Lv Lw Mf Mm Mv Nf Ng Nh Nk Of Oy Pg Qh Qc) Na(Ad cY Fb Ha Hb iA Kd IL Nj oH oK Pk Ql Qv Qz Ri Ue) Tt(Aj Db Fn Hr Hu Iu Nh Nk Of Pz Qw Qz Rb Ri Rm Uc Vp) Fn(Ha Hr In Js Kx Mm Ms Nh Nt Nu Ow Ql Qv Qz Ue) Ml(aW Il In Jo Lv Lw

Figure 6 Continued

Figure 6 Continued sF(Mu Up) iAsC} eP{Hb(bZ cP dF) Tn(cQ Jp) KkcY} Mz{uZ(aP dN) OmjD VpqC yHzH} nN{qU(kO mW nL) HxeD mYjD} No{MfNh
YebW cUeQ iJoT} aM{DwcV EoaV aAdW aDgV} cR{Sj(fB oP) GppK RzmU} Tj{Fb(Ir Ml Po)} Ri{Tr(rR rU) QvuZ} Ut{DdRv WeVp PapK} eM{GnQm VbgL UyiA} Aa{IqpI qWsC} Fa{AfpI cGeQ} Ha{Hr(oT oW)} Mn{YkmE OrgV} My{Om(aA Mf)} Na{ImKo yHzH} Jp{UpvS yHzH} Oi{NmtT KfrB} Un{FnNu HfjY} aD{bQ(Eo gV)} dX{BcRg TnHb} qZ{nTmP mWjD} rW{MrsJ bZfP} ChaOdF DumEnW EmMeOr ThWboQ FiPhoP GpKetS GzcIyD MsNxaA HIKoVu IbVvsF TvImIn QdJttX WnPaIK UhcXeQ

Constrained panels with 2 analytes, where 1.0E-8 >= 'model p-value' > 0. Contains 72 panels of 200,591 total panels evaluated. : Et(aA aR Fp Hx Ii Jd Jj Jo Jr Li Lj Lv Mb Mf Mh Ml Ms Mt My Nc Nd Ne Ng Nh Nj Nk Nl Of Oi Ok Oy) Ok(Hx Ii Ik In It Lv Mb Mf Ms Mt My Nb Nc Nd Ne Nh Nj Nk Nl) aC(Ad Ap Aw Bb Bo Cw Dg fR) Nd(Cw Fr Ji Lx Mm On) Ad(Aj Bo) Fr(Nc Nl) Mb(Mm On) MmNc IiOn Constrained panels with 2 analytes, where 1.0E-7 >= 'model p-value' > 1.0E-8. Contains 83 panels of 200,591 total panels evaluated. : Et(aC aO aW Bo cK Fn Hf Kx Ow Qv Qy Qz Ri Tj) Nd(aA Im Is Jg Jp Jt Lh Li Mn Mt No Nw Po Qa) Ok(Hr Iq Jj Li Lj Mh Ml Nm Of) Nl(Jg Ji Li Lv Lx Mm No On) aC(cB Ch Cu De Di Dk Dl Fr) Nc(Jg Ji Li Lv Lx Nw On) Ad(aM aW bM cB cF cN) Mm(Jd Lv tV tX) Jd(Cw Ic On) Bo(Dg Dl) Mb(Fr Ji) Ne(Ji On) AjJg CwNj MsOn bBfR Constrained panels with 2 analytes, where 1.0E-6 >= 'model p-value' > 1.0E-7. Contains 293 panels of 200,591 total panels evaluated. : Jd(aM Bo bU Db Di Fn Hf Im In Ji Jp Ki Kk Kp Kq Kx Ky Lh Lw Na Nu Og Oh Ok Ow Pj Qa Qe Qv Qz Tt Ue Uh Tj) Nc(aA Im In Iv Jj Jq Jt Lh Lw Ma Mb Mf Ml Mn Mt Mv Nb Nd Ni Nk Nm No Nx Om Pd Pf Po Qa Qe) Nl(aA Im In Jj Jp Jq Jt Lh Lw Ma Mb Mf Mn Mt Mv Na Nb Nd Nk Nm Nn Nw Of Om Pd Pf Po Qa Qe) Ad(aK aR aU aV Aw bA bC bF bQ bU cE cG cK CT cY Db dF Di dN iH Mb Na Nd Nj) Nd(Bo Ih Jj Jl Jq Lv Lw Ma Mp Mr Mv Mw Mx Mz Nm Nn Nr Nv Om Pd Pe Pf Qe) Bo(aK aM Ap aU Aw Bb bM bU cF Cw cY Ef Fr Jg Nj Ok On) aC(Ao Ar Ba Bc Bg Bn cF Co Cp Db Dc dN Dr Gc Ok On Zq) Et(Aj bR cR cT Cw Db Di iA Ic iH Kk Kp Kr Ql Tt) On(aR cK Hf Hx Jj Lv Mf My Ng Nj Oy Tj) Ji(aR FR Hx Ii Lv Lx Mm Ms Mt Nj) Ne(Fr Jg Li Lv Lx Mm Mn No Nw) Mm(Fp Ml Nj Ow tN tQ tT) Dg(Aj aM AW cF Di) Lv(aA Fr Jg Li Lx Mt) Nj(aR Bb cR Db Dk Fr) Mb(Jg Li Lx Mt Nw) Jj(Fr Jg Lh Li Mt) Ok(aR aW cK cQ cW) fR(bF bQ cE Dl) tV(Ic Ky Pj Qw) Aw(aR bM Dl) Bb(aM bM cF) Zq(aM bW Or) Cw(cF oK) Ef(Dr Gc) Fr(Hx My) Ms(Jg Lh) aR(cB Jg) IcKq IiLh aWcB bUiH hBoD Constrained panels with 2 analytes, where 1.0E-5 >= 'model p-value' > 1.0E-6. Contains 784 panels of 200,591 total panels evaluated. : Jg(aA aC aD Ar aW bB bM bR bU cB cK cQ cR Cw Db Di Dr Fp Hx Ic iH Ii In Io Iv Ji Jq Kx Li Lj Lw Lx Mf Mh Ml Mm Mt Mw Mx My Ng Nh Nj Nk Of Og Oi Ow Oy Pf tV) On(Ad Aj aN aO aW Bb bR cB cR Cw Db dE Dr Ex Fn Fp Fw Ha Ic iH In Iv Ji Kx Ky Li Lj Lw Mh Ml Mm Mt Mv Mw Nh Nk Of Og Oi Ow Pf Pj Ql Qv Qw Qz Ri Rm Tt Uh Us) Mm(aA aC AW Bo Cw Fr Hf Hx Ic iH Ik Is Iv Jj Jn Jq Jr Kq Kx Ky Lh Li Lj Lx Mf Mh Ms Mt Nb Nh Nk No Nr Nw Ou Pf Pk Po Qa Qv Qz Ri sC Tn Tt yH) Cw(aK aR aU AW bM Bn bU cB Ch cK cN cY Dg Di Dl FR Ic In Is Ji Jj Ky Lv Lw Mb Ne Nf Nl Nn oH Ok Ow Pj Qv Qz Tn tV Ue Uh Up Ur Tj tF) Bo(aQ aR As aV aW Ax BA bB BC Bg Bn bR cB cG Ch cK CP Cs CT Cu Db Dc De dF Di Dk dN fR Is Ji Lh Lv Mg Nm Of Ow Pd Pj) Ne(aA Im In Iv Jj Jp Jq Jt Lh Lj Lw Ma Mb Mf Mt Mv Mx Mz Na Nb Nd Nm Nn Nr Nx Ny Of Om Pd Pf Po Qa Qe) Nj(aA aM Ap Ar AW BA bB bF bQ bR bU cB cG Ch cN cT Cu Dc De dF Dg Di dN Im Lh Li Lv Lx Mt No Nw) Ji(aA aC Ad aW bR bU bX cB cK cQ Db Dr Ik Im In It Iv Jj Li Lj Mf Mh Mw My Nf Nh Nk Nr Oy Pg Tt) Nd(Ap Bb Ch Dg Dk In Iq Iv Jh Jk Jn Jr Lj Lz Me Mf Mg Mu Na Nb Nq Nx Ny Of Og Oz Pa Qd) Fr(aA aU AW bM cB cF Dg Dr fR Ic Ii Iv Jq Jr Li Lj Lw Mf Mh Ml Ms Ng Nh Nk Oy Tj) Aw(aK aM Ap aQ aU aV aW BB bC bF bQ bU cB cF cG Ch cK cN cR cY Db dN) fR(Ad aK aM aN aU aW bA bC Bn bR bW cB cG Ch cJ Co cT Cv cY Db Ef Gp gW) Lv(Ad Im Iv Jj Jp Jt Lh Lj Lw Mb Mf Mn Mx Nh Nk No Nr Nw Pd Pf Po Qa) Dg(aD aK aQ aR aU aV bA bB bM Bn bU cB Ch cK cN Cp Cs cT cY De) aC(Aa aM aR aW bB bC bF bM bQ bR bU cE cG cN cR cT dF Ex Jp Lh) Nc(Fp Is Jl Jn Jp Jr Lj Mg Mh Mr Mx Mz Na Nn Nv Ny Of Pe) Mb(AA Im Is Jl Jp Jq Jt Lh Lw Na No Nv Pd Po Qa Qe) cB(aD aJ aM BB bF bM Bn bQ cF cG cN cR Di Dk Dl Jd) Lx(DW Eo Ew Hv Hx Jj Jq Li Lw Mf Ms My Nh Pg Tj) Pj(aM cN iH Kq Ok Ow qB Qv rN rW sC Tn tT tX yH xA) Zq(Ap bR dM Dr Fb Hx iP Jd Lj Lt lY mM mS Pk Rg) Bb(aK aR aU aW bB bU cG cK cN cY dF Di dN tV) Nl(Is Iv Jl Jr Lj Mx Mz Nh Ni Nv Nx Ny Pe) Li(aA Hx Ik Im In Jq Lw Mf Ms Mt Nh Ni Nk) Vh(bU Ex Fb gW Hr Im Jd Je Jr Lj Mt Pk Rg) tV(Et Hf Il Ip Kc Lh Ms Nm Nt Of Qv Uf Vt) Kq(aR aW cR Db Fn Hf iH It Na Nt Ow Tj) Ok(Aj bR cF Di Fb Hf Ic iH Kx Ky Ow Tj) Mt(Hx In Iv Jq Lj Lw Mf Ml Ms My) Dr(bB Bg cG Ch Co Dk Et Fb Ko) Ic(aM aR cN jD jl rN rW tS Uh) cF(Ap aW bB bF bQ Dk Dl iH Jd) Ap(Aj aM aW Bn cK Di) Dl(aU aW bF Ch dF Di) Jj(Ad Ik Nr Po Qa Qe) aR(Is Jd Jh Jp Lh Nw) bM(Aa aW bF bQ Dk) Jd(bR cR dN fN) Lh(cK tS tT Tj) Ad(My Ow Tj) Nh(aA Mn No) Nw(Mf Ms Nk) aW(bF bU eP) Di(bU tS) Et(tT tF) Tn(Sr Uh) NmiH NaOw TtUh IptT QaQb bBeO bQbR Constrained panels with 2 analytes, where 1.0E-4 >= 'model p-value' > 1.0E-5. Contains 1,723 panels of 200,591 total panels evaluated. : Lh(aA aD aN aQ aU aW bB bR bU cB cQ cT Di Fn Fp Fw Hf Hx iA Ic iH Im In Iv jD Jo Jq Kx Ky Li Lj Lw Mf Mh Ml Nh Nk Of Ow Pf Pj Ql Qv Qy Qz Ri Rm sC TN tO tR Tt tX Ue Uh uP Ur vB vP vV zH xA tF) Tt(Ad aM Ap Ar Bo bU cF De Di Dk Fn Fr Hb Ic Id Im In Iq Is Je Jh Jj Jp Ke Ko Kp Kq Kx Li Lw Lx Mt Mu Mv Na Nk No Nu Oh Ok Om Ow Pj Qa Qe Qv Qy Qz Ra rN Sr St Tn tV Uf Un Ur vS Vt Tj) Ic(Ad aP Ar Aw bC Bo bQ bU cG Dc dD De dF Dk dN eD iH Im Iq jG Jh Ji Jp jR Ke Ko Kp kQ Kx Ky Lx Ma Mv No oF Oh Om Ou Ow Pd Pj Pk Qa Qe Qt Qv rB sM Sr TN tT tX Uf Un Ut vS tF) aR(Ap aW bB bF Bg bM Bn bQ bR bU cE cF cG Ch Cp Cu Di Dk Dl Ef Fr iH Io Jj Jq Jt Kf Ko Lv Lw Lx Mg Ml Mm Mt Mw Mz Nd Nm Nq Of Om Ow Pd Pj Qa Qe rW tT tX Uh Un) Pj(Ad AW Ax bU cB Ch cQ cR cT Db De dF Di Dk Fb Fr Hf Im Iq Is jD Jg Jh Ji Jp Kp kQ Kx Ky Lw Lx Mt Mv Na No Of Om Ou Pd Pk Qa rR Ss tO uL Un vB wD tF) Mm(Ad aN Ar bA Bb cK cR cT Db Dc Di Dk Fb FN iA Ib Im In Ki Kp kQ Kr Me Mx Mz Ni Nx Oz Pd Pe Qe Qy rN rW Sr Tr Ue Uh Un Ur vB Tk Tj) Ow(Ap Bb Ch cR Db Dc De Dg Di Dk Dr Fb Fn FR Hb Hf In Io Jh Ji Jj Jp Ke Kf Ko Kp Ky Lw Mv Nm Nu Om Pd Qv Qz Tn Tr Ue Uf Uh Un Ur Tj) cF(aD aK aM Ao Ar aU Ax BA Bc bE Bg bM Bn bR bU cE cG Ch cI cK cM cN Co Cp cR cT Cu Db Dc dD De dF dG Di dN Ef Gc hB rW tS tT tV Vh) Nj(Ax Bc Bg Bn Co Cp Cs Dl Ex fR In Is Iv Jj Jl Jp Jq Jt Kq Lj Lw Ma Mb Mf Mn Mp Mv Mx Mz Na Nb Nh Nm Nn Nr Nv Nx Om Pd Pf Po Qa Qe) Bo(Aa aD cI cJ cN gW Ii Ij Im Io Jh Jo Jp Jq Jt Kf Ko Kq Kx Li Lw Ma Mn Mt Mv Nc Ne Nh Nl Nw Nx Og Oh Om Ou Oy Qa Qe Tn Ue Un) Dr(Ad aM Ao Ap aU Ba bQ cB cE Cw cY dF Dg Dl Gp Hc Ij Iz Jd Kf Kq Ma Mg Mn Mt Mv Nn Nq Nx Oh Ok Om Pd Pf Rc Rz Sr Ss Tn Ut Vh) Fr(aD aK aO Ap aQ aV bA BB bC bF Bn bQ bR bU cE cG Ch cJ cK cN cT cY De Di Dl dN Dp Fn Fp Gc Hf Ik Mt Nm Qz sC tT tV Uh) Cw(aD Aj aM Ap aQ aV BB bC bF bQ bR bX cG cP cT Dk dN eD Fb Fn fP Hb hL Hw Je jY Ko Kq lL Oh Qw rN sK tN tS Un vB Vs) tV(Ad Ao Ap aU bG bZ Dd Dg Di gW Ke Kf Kg Kj Kp Kz lK Lv Ma Mv Na Nc Ok qO qP Qu Rh rW sC St tO Tr tT Ua Um uR vP xA) Uh(Ad aM Aw bU Db De Hq Im Iq Je Jg Jh Ji Jp Ko Kp Kq Kx Li Mv Nm Of Oh Ok Om Oy Pd Pk Qa Qv Qy Qz Ri Tr Ue Uf Un) Bb(aD aQ aV Ax aY BA bC bF Bn bQ bR bV bX cE Ch cJ CP Cs cT De dG DL fN fR Kx Lv Lw Mb Nl rC tS Zq) Di(aK aM aU aW Ba bC bM bR cG cK cT Cu cY Db Dc dF Dk eD Ef fP gW hR hX iH Is Ji jY Nd Qe qY TN tO tT) Mb(Aw Dg Dk Ih In Iv Jj Jn Jo Jr Lj Ma Mf Mg Mn Mp Mr Mu Mv Mw Mx Mz Nh Nk Nm Nn Nr Nx Ny Of Om Oz Pe Pf) Ap(aD aK aQ As aU aV Ax bA bB bF bM bQ bR bU cB cG Ch cJ cN Cp Cs cT Cu cY Dc De

Figure 6 Continued dF Dl dN iH Lv Lw rN) Jp(aQ Ar aU aW bB bR bU cB cJ cK cR cT FN Fp Hf iH jD Kp Kx Ky Mf Pk Qv Qy Qz Tn Ue Uf vS zH Tj) Dl(Aj aK
aM aQ Ar aV BA bB bC bM Bn bQ bR bU cE cG cJ cK cN CP cT cV cY Db De Dk dN Nd) fR(aH aO aQ Ar aV Aw Ax Ba Bc bE bH bM cl
cM cP Cs Cu dD De dF Dg Dk dR Fb Gc Hb Is Jg Mn Nw) Nw(aA aC aW bB bR bU cB cK Fp Hx iH li Ik In Iv Jj Lj Lw Mh Ml Mt Mw My
Nh Oy Po Qa rW) Vh(aG aM bB bR cR Cs Dd Dk Dp Gn jD Ji Jn Kp Li Om On Or Pf Pi qX Qy Ut Vp Vq Wb Zq) cB(Ar aU aX BA Bc Bg Ch
CP Cs cT Cu Cv Dc De dN Ef Ex Gc Is Jh Kq Nd Om rW Un) Kq(Aj aL aM aX cW Dp Ex Ha Hx In Iv Jj Kp Kx Ms Mt Nb Nd Nu Nv Qv Qz
Ue Ur tF) Dk(aK aQ aU aV aW bC bF bR bU cG Ch cJ cK cT cY dF dN Ex Is Kx Lt Qz Ye Tj) Nh(Im In Iv Jj Jq Jt Lj Lw Ma Mf Ml Mt Mx Na
Nb Nm Nn Nr Nx Pd Pf Po Qa Qe) Gc(Af aM aU aW bB Bn bQ cG Ch cN cY dD dF dR eF Fb Im Mv Om Pf Pk Ut tF) Nd(Ar Aw BA bB bC
bF bQ bU cG cN Cp cR cT Cu Dc Dd De dF dN Fp Jo) Ji(aU Ch Dg dU eP Ex Fn Hf iA iH jD Kp Kx Ky Qv Qy Qz Ri Tn Ue Uf Tj) Ad(FN fP
Hf iA Kp Kx Ky Lw Ne Nl Oi Ou qO Qv Qz rN rW tS Ur Us) Jg(Fn Hf iA Je Jr Jv Kp Ky Na Ni No Ou Oz Pk Pz Qa Qv Qz Ur Uu Tj) Ok(Fn
iA Kp Kr Qv Qy Qz sC Sr tN tO tS tT tX Ue Ur vB vH vV yH tF) aW(aU aV Ba bB bQ bR cE cG Ch Cp Cu De dF dN Ef Ex Is Ko Nm) Po(aA
Hx Ii In Iv jD Jq Lj Lw Mf Mn Ms Nf Nm No Og Oy Tj) aC(aJ aX bA Ef Im Io Is Jh Jt Lx Mg Mt Mw Nm Of Om Pd We) iH(Aa bB cM dB Dg
eD Jd Jt Kf Ko IL Mw No Oz rC Ue tF) Ch(aK aM aU Ax BA bM Bn bU cG cK cN Cs cT Cu dF) Lv(Dg Fp Ih Ik Jl Jq Ma Ml Mv Mz Nb Nm
Nn Nx Oz Qe) Tn(Db Fn Hf Im It Kp Na Nk Nu Oh Qz Ri Ue Uf Ur Tj) On(aA Fb fN iA Ik Kd Ki Kp Kr Lt Pk rW sC tT Ue Yg) Mf(aA Fp Im
Is Iv Jj Jl Jq Jt Lj No Nr Nx Qa Qe) bM(Ar BA bB Bg Bn cE cG Cp cT Cu dD De dF Jh) Dg(aN Ax bC bF bQ bR cG cJ cP dN Kx Lw Pd Qv)
Qa(aA bR Hx In Jq Lw Mh Ml Ms Nx Pf Qc Rm Tj) Ko(cR Db Fb Fn Hf Kp Kx Ky Lt Na pH Qz Sf Ye) Jj(Fp Im Is Iv Jl Jt Lj Mv Nn No Nt Nv
Nx) bB(aM bA bF bQ bU cN cT dN Ef Eo Is Jh Nm) Zq(Ef Gl iZ Kj kK kP mH mW Ns Up Ut Yk) cK(Ba Bc Cp Cu De Is Jh Lw Mw Nm Om
Pd) Uf(Fn Im In Iq Qv Qy Qz tN tS tT Ue) Un(bR Fn Hf Mv Na Nu Qv Qy Qz Ur Tj) bF(aD aF aM aO bC Bn bR bU cl cN dN) Et(fN jD rN rW
sC tN tS tX uP yH) bU(Ar Bn bQ cG cN Cp De dN Is Jh) Aw(Ax BA bR cT cT dF Is Lw Qe) Mt(aA cR Fp Lx Mh Nk Nm No Pf) Ne(Aa Fp Is Jl
Jn Jr Ml Nv Pe) aA(Fp Hx Iv Lj Lx Ml Nx Qe) Ba(aD Aj aK aM aU Bn Ct) No(eQ Hx Ik Iv jB oD oT) bR(cE cG cN dF dN Is We) tS(Ip Ke Kf
Kg Nm Ri Vt) Ef(Aj aM cN cR Rv Zx) Lw(Ar cR Fp Ik Iv Lj) Lx(Ik In Iv Ml Nk Ny) Im(Fn Iv Ml Pf Rm Tj) aU(Ar Ax Cp Cu De Is) nN(eD kl
mE nl nT qU) Nm(cR Li tN cT tX) Jd(jD IL Lp We Ye) Lj(Mv Of Om We Wh) Vt(sO tX uZ vS tL) Cp(aK aM cG Db) Cu(aK bC cN cY) Mz(fN
jD qC rW) Ip(tN tR tX wB) Ut(Lt Rv Rx Tj) aD(bQ cE cG gV) hB(lX nC nH nL) rN(Kf Kg Kj Ri) Fb(Ax Mc We) Is(aQ cR cY) Li(Iv Mh Nx)
Op(Or Pk Ru) Tk(qO qP yL) aH(jB pH pl) aM(Eo eW Ww) Aa(Nc Nl) De(aK cY) Tr(Db Sr) Jq(Fp Iv) Ky(sC uP) Pf(Ik Nx) cR(Om Pd) wL(sC
tT) AjKl AraK BncG ExYe UeQv HxJl HbeP JefN WeRg KfiA RirW OftT VajI VqtL OzjB jDqZ Constrained panels with 2 analytes, where 1.0E-3 >= 'model p-value' > 1.0E-4. Contains 3,527 panels of 200,591 total panels evaluated. : Dr(aA
Af aH al Aj aK aN aQ aV AW aY bA Bb bF bM Bn Bo bR cF cN Cu dD De Di Ez fR Gc Gl Gn hC Hr Ib Ii Im Io Is jB Jh Jk Jn Jp Jq Jt Kl Kn
Kp Kx Lh Li Lv Ly Lz Ml Mm Mw My Nc Ng Nj Nm No oD Of Oi Op Or Ou Oy Pi Pj Pk Qa Qb Qc Qh Qm Qt Qu qX Qy Qz Rg Rv St Tr Tt
Tz Ua Uc Ue Uh Un Us Uu Uw Ux Vi Vj We Wh) Di(Aa aD aN aQ Ar aV Ax bA bB Bc bF Bg Bn bQ bX cE Ch cl cJ cM cN CP Cv De dN Fb
fN Gc Gl hB Ic Im Io Jh Jp Jt Kf Ko Kp Kx Li IL Lv Lw Mb Mg Mn Mt Nl Nm No Ns Nw Nx Om Ou Pd Qa Qd rC rU rW sC tR tX Uf Un uZ
vP vV yH Tj tF) aR(aK aQ Ar aU aV Ax BA bC cl cJ cK cN Co Cs cT cY Dc De dF dG dN Fb fP Fy Im Je Jl Kc Ke Kl Kp Kx Ky Li Ma Mb
Mf Mq Mu Mv My Ne Nh Nl No Nv Nx Ny Ou Po Qd qP Qv sC sO Sr TN tO tR tS Tt tV Uc Ue Uf Ut Vt vV) Kp(aM Ap Ar Aw Bb Bo cN
cR Db Dc De Dg Dk Dl Fb fN Fr Hb Hc Hf Id iH Im Iq Is Jh Jj Ke Kf Kx Ky Kz Lh Li Lv Lw Lx Ma Mg Mn Mt Mv Mw Na Nj Nm No Nw Of
Om Ou Pd Qa Qe Qv Qy Qz rW sC Sr tN tO Tr tS tT Ue Uf Un Ur) iH(Ao Aw Ba Bb Bc bW cB cH cK Cp cQ Cu Dc dD De dJ Dk Dl Fr hB hR
hX iC Ii iJ Im Io Iq Ir Is Jh Jj Ke Kl Ky Li Lw Lx Ma Mg mM Mt Mz Nj nN Nv Nx Ny Of Oh Om Ow Pd Qa Qe rW sC Tt tV Uc Uf Un Ut)
tS(Ao Ap Aw bB Bc bR bX cB cH cl Cp cS Cu cZ Dc Dd Dg dl dJ Dk Dl Fa fP Fr Gl Hf li Jd Jg Ji jK Jo Jp Jt Kc Kj Kn Ko Kq Ky Li Lv Lx
Mu Mv Mw Nw Of Om On Ow Pd Po Qw rC rS sC Tr Tt Ue Tk) Im(aA cB cK Fb Fc Fp fR Hf Hx iA Ik In Je Jl Jn Jp Jq Jr Jt Ko Kx Ky Lj Lt
Lw Lz Mh Mj Mn Ms Mx Mz Nb Nk Nm nN No Nr Nt Nx Op Oz Pd Pe Ps Qe Qv Qw Qy Qz Ri Rv Rx sC Sr Tr Ue Un Ur We) Jj(Ap Ba BB
bU cB cK Dc Dg Dk Dl Ef cO Fb Ic Ih Ij Ip Iq Ir It Jh Jk Jm Jo Jp Jq Jr Kf Kg Kl Ko Kx Lw Ma Mg Mh Ml Mn Mq Mu Mw Mx Mz Nb Nk Nm
Ny Of On Om Ou Pd Pe Pf Pj Pz Qd Sr) Op(aC Ad aM As Ax Bn Cs Cw Dc De eM Et Hc Id Ij Is Jd Je Jh Jn Jr Kq Kx Li Lj Mb Ml Mq Mr Mt
Mw Mx Mz Na Nm Nr Ny Ok Om Pd Pe Ph Pi Po Qa Qx Ra Rb Rj Rt Tn Tr Ue Un Uo Us Vi We) Gc(aK Ao Aw aY Bg bR cE cL cP Cu De eC
eM gL gW HC Ib Ij Is IZ Jh Jk Kx Ly Ma mE Mt My Ni Nn Nq nW Nx Ny Of Oh Or Oy Pd Pj Qh Qu Qy Qz Sr Ss Si Tn Tt Us Vi We Ye Wm)
bB(AA aH aJ aK aN Ar aU Ax Ba BC Bn bR cG Ch CP Cu cY Db De dF dG Dk Ex fP Io Jt Lv Lw Lx Mb Mg Ml Mm Mt Mw Mz Nc Ne Nh
Nl nN Nx Of Om Oy Pd pH sC Ue Vt We Ye tF) sC(Ad Ap Bb bF Bo cB cE cS cV Dg eD fN fP Hf Ic Jd Jg Ji Jp jY Kc Ke Kf Kq IL IM Lx Ma
Ms Mu Mv Mw Na Nm Nw Of Om pS Qv qW rC Ri rN rS sO tN Tr TT tX Uf Vq zH tL Tk) Qe(aC Ap aQ Ar aU aW BA Bb Bn bR bU cB Ch
cK Cp cT De Dk Fn Fp fR Hx Ik In Iv Je Jq Jr Kx Lj Lw Mh Ml Ms Mv Mx Nk Nm No Nx Pd Pf Qb Qc Qv Qy Qz Rm Sr Tr Ue Ur Tj) tT(Ad
Ao Ap Bb Bc bX cB cH cl Cw Dg Dk Dl Hf li Jd Jg Ji Jo Jp Jt Kc Ke Kf Kg Kq Li Lv Lx Ma Mg Ms Mt Mu Mv Mw Na Ng Nk Nw Oh Om Pd
Pf Po pS rC Ri rU sO uP zH tL) tX(aC Ad Ao Ap Bb bG bZ cB cF cl Cw Dg dl Fr Hf li Jd Jg Ji Jo Jp Jt jY Kc Ke Kf Kg Ky Li IK Lx Ma Mg
Mq Ms Mu Mv Mw Na Ng Nw Of Oh Om On Pd Po qW rB Ri Tt tV tL) De(aD aM aQ Ar aV Ax BA bC bF bQ bR bX cE cG Ch cJ cN cP cT
Cu Db dF Dk dN Fb Fn Io jB Jp Ky Lh Lv Lw Ma Mb Mt Na Nl Nm Nw Ou Qa Qv Qz Sr Tr Uf Un Ur Tj) rW(aD Ap Aw Bb Bc bX Cp CW
Dc Dk fP Fr Hf Ip Jd Jg Jh Ji Jp Jt jY Ke Kf Kg Kj Ko Kq Lh Lx Ms Mt Mv Mw Na Ne Nh Nj Nl Nm Of Oh Ok Om qW rC Tr Uf Un Vq Tk)
Ic(Ap Ba Bb Bn Ch Dg Ef Ex Fa Fb Fn Fy Hc Hf Hq Ib Id Ij Is Jq Jt Jy Kf Kl Kn Li Lv Lw Mg Mn Mt Mu Mw Nv Nw Ny Of Oz Pf Po Qd Qh
Qy Qz Ss St Tr Ue Ur yH) Ar(aD aM aQ aV aW bA bC bF Bg bQ bR cE cG Ch cJ cK cN cT cY dF dN Ef Fb Fn Io Is Jh Jq Jt Kf Lv Mb Mg Mn
Mt Nc Ne Nl Nm Om Ou Pd Qa Sr Ss Tn Tr Ue Tj) Lw(aA aC aL aW Ba bQ bR bU cB Ch cT Db Dc Dk Dl Ef Ex Fb Fn fP fR Hb Is Jl Jp Jr Kx
Ky Ma Mf Mh Ml Mn Mv Mx Nb Nk Nn No Nr Nt Nv Nx Ou Oz Pf Qy Sr) bU(aD aJ aM aN Ao aU Ax aY BA Bc Bg bH bM cE Co cR Cs cT
Cu cV cY Dc dF dG fP hB Io Jq Jt Li Lv Lx Ml Mt Nh Nl Om Ow Pd Qa Sr Tn Tr Un Ut Vt) (R(Aa Dp Fp Fy Hq Ij Io Iq Iv Jh Jn Jq Jt Kx Lh Lj
Lv Lx Mg Mi Mj Ml Mq Mr Mw My Nc Nd Ne Nh Nl Nm Nn No Nq Ny Om Ou Pd Pc Pj Qc Qx Sr Uh Uk Ur) aW(aD aJ aK aM Ao aQ Ax bA
BC Bg Bn bX cl cJ cK cM cN Co cP Cs cT Cv cW cY Dc dD dG dL eO fP Io Jt Kf Lv Lx Mg Ml Mm Mt Om Ow Pd Qa Uf Un) Nm(Ap Aw
Ax BA Bb bF bQ cB Ch cN cQ cT Db Dg Dk FN FP hB fk Iv Jl Jp Kx Ky Lj Mf Ml Mx Nk No Nr Nx Ou Pf Qa Qv rN tO tR uP vB yH) Kf(aM
Bb cN cR Db eD Fb Fn Fw Hf In It lu jM jY Kx Ky Lt Ma Mb Na Nd Nk No Nu Oi oK Ou Qv Qz rB Rm tN tO tR Uh Ur uZ vB vS wF tL xA
Tj) Ap(bC bE cP cR fN fP Hf hO Id Jh Jq Ke kQ Kx Ky Li Lx Mb Md Ml Mt Na Nc Ne Nl Om Ou Pd Pe Pf Pk Qa qO qP Qv Qz rS tN Tr Ue
Ur Tj) Jt(aJ aQ aU bR cB cK cR cT FN Fp Hx iA li Ik In It Iv jD Jr Kx Ky Lj Mh Ml Mn Ms Mx Nb Nk No Nr Nx Pf Qv qZ rN Rv tN Ur Tj)
Kx(Ba Ch Db Dl dU Ef eQ Ex Fb Fn Fr Hb Io Je Jh Ke Kl Ky Ma Mn Mt Mv Na Nb Nw oD Om Ou Qa Qv Sr Ss Tn Tr Ue Uf Un Ur Tj Ti)
Bb(eD Ef Fb Fn fP hB hC Hf Is Jh Ky Li Lx Lz Mg Mt Na Nc Ne Nk nW Om Ou Pd Pf Pk Qa qO Qv Qz rN rU tN tO tR Ur yH Tj) aC(Hp Ip Iq
Jq Li Lp Lv Ma Mb Ml Mu Mv My Mz Na Nc Ne Nh Nk Nl Nq Nv Nx Ny Oh Oy Po Qa Qd Rz Uw Ux Vi Vw Wb Wh Yi Ye) bR(aJ aK aM aN
aU Ax BA bC Bg bM Bn bZ Ch Cp cT Cu dG eW fP hB Jh Li Lv Lx Mm Mt Nd Nl Om Ow Pd Qd Uf Ut Vi Vt Wh) Is(aK aN cF Ch cQ cT Db

Figure 6 Continued

Dg Fp Hx Ik In It Iv Je Ky Lj Ma Mn Ms Nb Nh NK No Nr Nx Qg Qv Qy Qz Rm Sr Tr Ue Ur Tj) Dk(aD aM Ax bA Bn bQ bX cE cN cP Db dG dL Fn fP Hf Jh Ky Kz Lv Mt Na Nc Ne Nh Nl Ou Pd Pk Qa Qv Qw Sr Ue Ur Tk) Fb(aM Aw Bo bQ cN cR Cs Db Hf Id Iq Jh Ji Ke Ky Li Lx Ma Mb Mv Na Nj No Nw Om Pd Qa qC Qv Qz Ru Ue Ur Ti Th) cB(Ao eD fN hB Io Jq kQ Li Lv Lx Mb Mg Ml Mm Mt Mw Nl No Nq Ny Ow Pd Qa qO qP rC rN rU TN Tt Ue Ut Vt tF) cK(Ao Ax bF Bg Bn bQ cE cG Co Cs Cv Db Dc dF dN Io Jq Lv Lx Ma Mg Ml Mt Mu My Mz Nl No Nq Nv Nx Ny Of Oh Qa) Jp(Aw cQ Db hP HX iA Ik Iv jO Jq jY Lj IL Mh Ml Ms Nh Nk nN No Nr Nx Pd Pf qQ qY rB rN tN tR We wG tF) Un(Aw cF cQ cR cT Db fN fP Hu iA In Iq It Iv jD jY Ki Ky Lt Ma Ms Oh Pd qC qD Ri Tr Ue uN uZ vS We tL tF) Ch(aD aJ aN aQ aV bC bQ bV bX cE cJ CP cR Cv cY Dc dG dL dN Jq Lh Li Lv Lx Mb Mt Ne Nl Nw Om Qa) Qv(Aw Dl Ef Fr Hb Io Iq Jh Ke Kg Kj Kl Ko Li Ma Mg Mn Mv Oh Om Ou Pd Qa Qm Qy Sr Ss Uc uN vS yH) tN(Ad cF Fr Hf Jd Jg Ji Jo Kc Ke Kg Ky Li Lv Lx Ma Ms Mu Mv Na Nw Of Om On Pc Pd Po Qw Ri tV wL) No(aA Aw Fn Fp Hf Je Jq Jr Lj Lt Mh Ml Mn Ms Mx Nb Nk Nn Nr Nx Pd Pf Qy Qz Ri Sr Ue We Tj) Ke(An Bo cR Db Dg FN Hf hL iA Iq It Iv Ki Ky Ma Na Nu Qz Sr tO tR Ue uZ vB vH vV Tj tF) jD(cA eD Fr hR Hv Iq Jg Jh Lx Mm Mu Mv Mw mY Na nN Nw Ny Ok On Pd Qa Uf Uh Ut Uw Vi Vq vS) We(cD cR Cs Dc Dd Ex Fr Je Jr Kn Lh Li Mn Mt Nn Nr Nx Oh Or Ow Pe Pf Pk Qb Qm Rv Sr Uh) Dg(Fn Hf iA Id Jh Jq kQ Kr Ky Li Lx Lz Ml Na Ne Nl Oi Om Ou Pf Pk Qa Qz rN Ue Ur Tj) dN(aD aK aL aQ aU aV BA bE Bg bM Bn bQ cE cl cM Cp cT Cu cY Dc dD Ef jB Ow Tt Ue) Mn(Aw dX Fp Ik Iv Jq Ky Lj Lp mE Mf Mh Ml Mx mZ nA NK nN Nx Pd Pf Pj Qz Sr Wh) cN(aK aU aV Ba Bc Bg bM Bn bQ cE cG Co Cp cT cY Dc Ex Gl Ko Lh Lv Mg Mm Ow Ue Uf) Nr(aA Fp Hx Ik In Iv Jl Jn Jq Jr Lj Mh Ml Ms Mx Mz Na Nb NK nN Nx Oz Pd Pf) Sr(Aw Bo Fr Hf Hu Id In Jh Ji Ko Ky Li Lv Lx Ma Mv Nk Nu Om Pd Qy Qz Uc Uh Ur) cR(aU bM Io Jh Lv Lx Mg Ml Mu Mw My Ne Nh Nl Nq Nw Ny Of Oh Ou Tn Tr Tt Uf Uh) Mf(Ih In Jn Jr Ma Ml Mr Mu Mv Mx Mz Na Nb Nk Nn Nv Ny Of Og Om Oz Pd Pe Pf) Nx(Fp Ih In Iv Jl Jn Jq Jr Lj Mh Ml Ms Mv Mx Mz Na Nb Nk Og Om Oz Pd Pe Ru) Bn(aK aM aQ aU aV Ax bA bC Bg bQ cE cJ cP cT Cu cY Db dF jB Mb Mm Nd Uh) Dc(aK aQ aU aV bA bC bF bM bQ cE cG cJ cT cY dF fP Ky Lt Lv Mb Na Qz Ur) Ue(Ax cV Db dF Fa Fn Fr Hf Iq Jg Ky Li Lx Mt Na Oh Ou Pd Pj Qa Qz Ur Vi) Tr(Bo Fn Fr Hf Iq Iu Ji Ko Ky Li Mt Na Oh Ou Pj Qa Qy Qz sM St Ur vS yH) Ik(aA In Jl Jn Jq Jr Lj Lz Ma Mh Mj Ml Mr Ms Mx Mz Na Nk Nn Og Om Pd Pe) Aw(Aa eD Ex FN Io kQ Ky Lh Lv Mt My Na Nl Nw Pd Qa qO Qw Qz Ur Tj) On(eQ hA hX jB jE jM jY IL mZ nK nN qO qP qY rB rN tO tR vB vH vP yH) Bo(Ex Hb Id Jr Kg Kj Kl Ky IL IO mE Or pH Pk Pz Ss Uc Uf Ug Vt Tj) Ou(Db Fn Hf Io Iq Jh Ko Ky Li Ma Mg Na Om Pd Pk Qa Qz Tn Uf Uh Ur) Iv(Fp In Jl Jn Jr Lj Ma Ml Ms Mv Mx Mz Nk Nn Ny Om Oz Pd Pe Pf) bQ(aF aK aM aO aQ aU aV Ba BC Bg cl cO Cp Cu Cv cY Io Mm Nl) fN(Bc cF Cp Fr Jg Jh Ji Ko Kq Lh Mv Mw Nw Ok Om tV Uf Ut vS Vt) Cw(gW hO jM IX mS nC nF nT pS qU rB rC tO tR uZ vH vI yH Ye) Nj(Ef FP hB Ih Iq Jn Jr Mg Ml Mq Mr Mu Mw Ni Ny Of Pe rN) Lj(Hx In Jh Jl Jq Lp Mg Mu Mx Na Nb Ni Nk Pd Rt Rz Ux Vi Vw) bM(Af aK aL Ao aQ aS aU Ax Bc bP Co Cs Ct cV cY Dw Ef Nd Om) cT(aD aK aM aU aY BC cG Cp Cu Db Io Jh Lv Mg Mt Nl Nw Qa) Fr(aN Ba gW hX Ki Ko Ky Kz Lp Lt nN Pk Rx tO tR vP vV xA) Ur(Ef Gd Ip Iq Kg Kj Kl Ko Li Mg Mv Of Oh Om Pd Pj Qa Uc) Tj(Cp Cu Dl Ef Ir Je Jh Ko Li Mt Mu Nw Oh Om Pd Pf Uf) Qz(Id Je Jh Kl Li Lx Ma Mt Mu Mv Of Oh Om Pd Pj Qa Ut) aM(Ao Bg cE Co Cu Ex Gl gV Kl Ko Ky Nd Ow rC Rz Tn Uf) cF(Aa Cs eD fP Mt Nd Ow qO qP rC rN rS rU Tn tO tR tF) Db(aK aU Ba Bg Cu cY eD Ef Jh Kl Ky Nd Nw Om Pd Uf) Lh(dE hA hL jY Kr IL Lt oH oK qC qD qY qZ rN yK tL) Uh(Ax cQ Fn Fy Hf Ib Id jB Kg kQ Lp pH Pj Ss Wh tF) tV(aK cl cS cY fP hA jF jQ jR IM rS uP Vq vV tL Tk) Cp(aD aQ aV Ax bA bC bF cE cJ cY dF Fn It Mb Na) Ml(Aa Jl Jq Ma Mu Mv Mw Mx Nb Nk Nn Nv Ny Pd Pf) jB(Af Ax cG cX dF Et Ij Ji Ko mE Mk Nn nW Ny oN) rN(bX eC fP Hf Jd Jg Kl Mg Na Nq Of rC Ss Vq vV) Fp(In Jl Ma Mb Mg Mv Mx Nb Nh Nk Of Oz Pd Pf) Jq(aA Hx In Jl Ma Mh Ms Mv Nb Nf Nk Nn Oz Pf) Uf(cQ Hf Jg jY Kr Na oH oK Pd Pj Pk tO xA tF) Ut(eD Fn HX jY Mt Mw My Nb Nd Nv Ny Qx Vi) aU(bA Bc Bg cG Cs dF Ex Io Jh Lv Lx Mm Mt Nl) Qa(Fi Fn Fw Ha Hf Je Ky Lt Qg Qw Qy Rc Rx) Kq(gW hA hX jM jY Lt qO uZ vB Vp yH Ye Tk) nN(cJ Et hB Ir Jg Ji Jn Mt mW Nq oH Pf Po) Ad(Gn jM Jv jY Kr Lp Lt qP rB tO tR Ye) Cu(aD aN aQ aV bA bF cG cJ cP dF Lt Mb) Dl(Ef Ex fP Jh Ky Lv Lx Mb Mt Na Nl Om) Rv(Dd Iz Jg Mg Nn Oi Pi Pk Qy Ss Tt Wm) Ax(aK aQ aV bC bF Bg cE cY Mm Nd pH) Fn(Fy Id Jh Li Lx Ma Mv Oh Om Pd Pj) Nk(aA Jl Ma Mv Nb Ni Nn Nv Om Pd Pf) Vq(cV hO jY qX qY uM vP vV yK yL xA) Mb(Ba Cv Dd gV Hv Hw Jk Ko Nb Qd) Ky(Ef Iq Jh Ma Mg Mv Of Om Pd Ss) Nw(aN cJ cQ Eo Hf iA qZ uP tL tF) aK(Ao Bc bF Bg cE cG Co Cs dF rC) Ex(cG cY hL Lt Lv Nc Nd oK Pj) Lx(Aa aN aQ cJ cY Qy tO wG tF) Nh(Jl Jn Jr Mv Mz Ny Of Om Pe) Ji(Je Ki Lt Sf tO tR uP yH tF) Vh(eC gL hC iZ jG jY qT qY rA) aA(Ip It Ma Mh Ms Nb Nn Nt Nv) Ba(aQ aV bC cJ cY Lv Na Nl) Bg(aD Aj aV bA bC Cs cY Nd) Jg(Eq fP Kr Qw Qy qZ Ri uP) Vt(cQ cV Ma Mv Oh qD uM wF) Pf(gV Jl IL Lp Nb nK Nt Nv) Pj(Hc Ib Je jY Qt Qy Ri sH) dF(aD aO aQ aV bE cY Nl Vc) qU(Hf Jd kO mW nD nH nI nL) Bt(dU Eo jY qZ rB vB Tk) Mm(aQ cQ cY hO qB qZ tF) Tt(bC bW hB hR tR uX yH) Ko(In Iq It Kr Nu Tn tF) Or(Lp Rz Si Ux Vw Wh Ye) Nd(Ao Bc cE Co Cs Cv) Je(Iq Li Ma Oh Ok Pd) Qy(Iq Li Ma Mt Oh Ow) Lt(Ir Iz Kn Mt Oh Om) IL(Hf Mu Mv Mw Mz Na) oD(Fa Ld Mq nW oQ Th) Ef(aD cG Ct Na Yg) Jd(gW oO tR vS zH) Wh(Jr jT Mt Qm Rg) Tk(jQ vP vV wH wL) Ok(hX qZ uP vP yK) Pk(Gn Uw Ux Vi Ti) cW(eD eO fP hR rC) Bc(aQ aV bF cY) Cs(aV bC cY Ye) Ms(Jl Nv qZ zH) Mv(Hx Qw tO tR) Tn(bL eM eP Ye) Hf(eD jY Li yH) Ip(uP yH zI yE) Ri(Li rC rU tO) Of(qZ rS tO tR) bX(Jh qO qP rU) cG(aQ Io Mt Nl) fP(aD aO Pd xA) hB(eP kO nI nT) sO(qO qP vP vV) Th(eQ kI mE) Lv(Aa aN bC) Na(Hb Kl yH) Qw(Li Pd uX) Jl(In Mh Nb) Rg(Rt Vi Vw) Om(Cq My Vp) Vc(gL jT qX) bA(aD Io Mg) cV(eD hR hX) dX(dD Kk Qx) eM(Kk Qx Yi) nW(Du eQ gC) Co(bC cY) Nq(nK pH) Mw(iA qZ) Ir(nA nK) Jh(aD aQ) Ye(Hc Ow) Kg(tO tR) Nv(Hx Mh) Vi(Dd IM) jY(Mz Po) DumE GnPi MquZ MtLp HlVu IdOh InPd IokQ IzZx SiqX ZqfB KczH KnRu KzdU OwnT VajK aNcE gWmS wDtL qTkO lKvS

Unconstrained panels with 3 analytes, where 0.0E0 >= 'AUC p-value' > 0. Contains 50,000 panels of 38,530,102 total panels evaluated. :
Zq{IY(aA aC AD aE AF aG al AJ aK AL aM AN AO aP aQ AR AS aU aV AW AX aY aZ BA Bb BC bE bF BG bH bI bJ bL bM BN BO bP bQ bR bS bU bV bW bX bZ cA cB cC cD cE cF cG CH cI cJ cK cL cM cN CO CP CQ CS CT CU CV CW CX cY cZ dA DB DC DD DE dF DG dH DI dJ DK DL dM dN Dp DR Du eC Ed EF EM Eq Et Ex Ez Fa FB Fc Fd Fi Fn FP FR Fw Fy Gb Gc Gd Gh Gl Gn gP Gz Ha HB HC HF HI Ho Hp Hq Hr Hu Hv Hw Hx iA Ib Ic Id IH Ii IJ Ik Il Im In Io IP Iq Ir Is It Iu Iv IZ jB Jd Je Jf Jg Jh Ji Jj Jk Jl Jm Jn Jo Jp Jq Jr Js Jt Ju Jv Jy KC Kd KE KF KG KI Kj KK Kl KN KO KP Kq KR KS Kx Kz Ld Lh Li Lj Lp Lt Lu Lv LW LX Ly Lz Ma Mb Mc Md ME MF Mg MH MI Mj Mk Ml MM MP Mq Mr MS MT MU MW Mx MY MZ NA NB NC ND Ne NF Ng NH NI NJ NK NL NM NN NO Nq NR Ns NT NU Nv NW Nx Ny Oa OE OF Og OH Oi Ok Om ON oO OP oQ Or Ou OW Oy Oz Pa Pb Pc Pd Pe PF Pg Ph PI Pj PK Po Ps Pz Qb Qc Qd Qe Qg Qh Ql Qm Qn Qt Qu Qv Qw Qx Qy Ra Rb Rc Rf Rg Rh Ri Rj Rm Rt Ru Rv Rx Ry Rz Sf Sh Si Sj Sr Ss St Tn To Tr Tt Tv Tz Ua Ub Uc Ud Ue Uf Ug Uh Uk Ul Um Un Uo Up Ur Us Ut Uu Uv Uw Ux Uy Uz Va Vb Vc Vh Vi Vj Vo Vp Vq Vs Vt Vu Vv Vw Vz Wb Wc Wd We Wf Wg Wh Yd Yg Yh Yi Yj Yk Yl Zw Zx Ye Tm Tl Xa Wm Tj Ti Th tF Yf) mM(aC AD aE AF aG aH al AJ aK AL aM AN AO AP aQ AR AS aU aV AW AX aY aZ BA Bb BC bE bF BG bH bI bJ bL bM BN BO bP bR bS bU bV bW bX bZ cA cB cC cD cE cF cG CH cI cJ cK cL cM cN CO CP CQ CS CT CU CV CW CX cY cZ dA DB DC DD DE dF DG dH DI dJ DK DL dM dN Dp DR Du eC Ed EF Em Eq Et Ex Ez FA Fb Fc Fd Fi Fn FP FR Fw Fy Gb Gc Gd Gh Gl Gn Gp Gz Ha Hb HC HF hG HI Ho Hp Hq Hr Hu Hv Hw Hx iA Ib Ic Id Ih Ii IJ Ik Il Im In IO IP Iq Ir Is It Iu Iv Iz Jd Je Jf Jg Jh Ji Jj Jk Jl Jm Jn Jo Jp Jq Jr Js Jt Ju Jv Jy KC Kd KE KF KG KI Kj KK Kl KN KO KP kQ KR KS Kx Kz Ld Lh Li Lj Lp Lt Lu Lv LW LX Ly Lz Ma Mb Mc Md ME MF Mg MH MI Mj Mk Ml Mm Mn Mp Mq Mr MS Mt Mu Mv Mw Mx MY Mz Na NB NC Nd Ne

Figure 6 Continued dU(aH aN Ax Bb bL bW cK cR Cs dC Eq Fc Fp hC Hf Kc Ky Lt Mx Nd Nx Pa Tv Uw Uy Vo Yh) aD(gW hA iB iC jE jF jG jH jI jM jP jQ jR jU jV jY lK lL lM lN pH qT qV qX rA) Fb(Ap bW Cq Dr eC fP Gl gP hG iH iJ jL jQ jU kS lM nW nY oF oK oN qW qX tF) qX(aO aQ aV cE Cq dH dM Fa Hp jQ Kx Ky Mf Nc Oa Qy Rg Rh Ri Rm Ss Vb Ti) rA(Ax bA bL bR bW cJ cY dH Hp It Jo Ky Qy Rg Rh Ri Rm Ss Uf Vb Zx Tm) oD(aH Ax bL Cs dA Eq Gd hB Hf iH Kc Kn Kx Mx Nu nW Oa Pe Qv Si Yd Yh) gC(aH Ax bB bL Cs dC Eq Ez gP hB Lj Mx nW Of Rg Rj Rv Ur Vb Vo Yh) lM(aI Aj bJ cD Co Ct dD Fw Ic Il Io Jf Me Mg Mz Qz Ri Rm Vq Zw) Rg(aJ bH bL bR bS bW cI dM dR eM fR gP hC Hx kQ oP oQ pH Pk) eM(An Bb Bg bL bW Ch Eq Fp hB hC Ih Ik Lj oH Rv Sh Xa) pH(aH aW Ax bL bQ Db Eq Fn Fp Ii Jd Mx Oz Pa Si To Um) Vq(bR hA iC jH jL jM jO jP jQ jR jV jY lK lL lN qY) oP(aH Ax BB bQ cR Cs Fp hB Jl Kn Mx Nq Qv Rv Si) Ri(jG jH jI jL jM jO jP jQ jR jU jV lK lL qT qV) qY(bR cF cP Cu cW Dc Fw Im Ji Lv On Ou Pg Po Qe) jK(aH Bc bI cJ Cq Fd It Je Nr Oa Rf Rh Rm Ss Tm) oQ(aH Bb Bc bW cJ cR Cs Fp hB Kn Ky Mx Nq Rv Si) bR(Ex jL qT qV Qz Rh Rj Ss To Ut Vh Vu) jO(Dc dD Eq Fi Fw Lu Nv On Ou Pg Qz Vs) bW(aR Bb Dc Fa fR Kx Lu Nc Ns Rj Vh) pK(aH Aj Ax bB cR Cs hB Mx Nq Pa Vo) oW(Ax bB cR Cs Eq hB Hl Kn Mx Yh) eQ(aH Ax bB bL Cs Hf Kn Mx nW) gZ(aH Ax bB Cs dC hB Kn Mx Yh) oT(aH Ax bB Cs gP Kn Mx Si Yh) cR(fA hB hC hG nW oE oK pF) pI(aH Eq hB Lj Rv Si Yh) Rj(dR eC hC kQ kS tF) fA(aH Ez Hf Mx Pa Yh) jR(Db Ef Iq Kj Ry Th) jU(Ad dD dH Fw Ss Th) lL(cJ cP cW jI Rf Rh) oK(bO Fa fR Io nW Yk) oV(Ax Cs hB Mx Qv Yh) hC(aZ cM Rh To Ue) hG(cM cQ Fa Gd Mm) qT(cN cT Ky Lv Tm) jY(Dc Ji Ky Po Rf) cW(jF jG jI jM) dM(Ex Jd jE lN) eC(bF cM dB Jf) jQ(Io Mg Zw Th) kQ(Bb Cs Fa nW) Ss(lK qV qW) fR(aH Nk Op) hA(dD Fa Qz) nY(aZ Ue Yk) Dc(jH lO) iC(Qm Qy) jV(dD Ef) BbtF DrcB MniO IcjI ImjL HcbF JujP KyqW RhqV RfqU NxgW VslK cMkS} Tk{qP(AA aC Ad aE AF aG aH aI AJ aK AL aM aN AO AP AR AS aU AX aY aZ BA BB BC bE bF Bg bH bI bJ bL bM Bn BO bP bQ bR bS bU bV bW bX bZ cA cB cC cD cE cF cG CH cI cJ cK cL cN CO CP CQ cR CS cT CU CV CW CX cZ dA Db Dc dD DE dF DG dH dI dJ DK DL dM dN Dp dR eC Ed EF ET eZ Fa Fb FN FP Fr Fw FY GL GP gW HA hB HC HF hG hL hO Hq HR Hu HV Hw Hx iA IB iC Id IH Ii IJ Ik Im IO IP Iq Is Iu Iv IZ jD JE JF Jg jH JI Jj JK JL JM Jn JO JP JQ jR Js JT JU JV Kc Kf Kg Ki Kj Kk Kl Kn Ko Kp Kq KR KS Kx Kz Ld Li Lj lK lL lM lO Lu Lv Lw Ly Lz Ma Mb Mc Md Me Mf Mg Mh Mi Mj Mk Ml Mm Mn Mq Mr Ms Mt Mv Mw Mx Mz Na Nb Nd Ne Nf Ng Nh Ni Nj Nl Nm No Nq Nr Ns Nt Nu Nv Nw Nx NY Oa OE Of Og OH Oi OK Om ON Or Oy Oz Pa Pb Pc Pd Pf Pg Ph Pi Pj pS pY Pz QA QB QC QD Qe QG QH qI Ql Qm Qn qO qQ QT qU QV QW QX Qy Qz RA Rb RC Rf Rg Rh Ri Rj Rm rO rP rQ rR rS rT rU rV rW rX rY rZ sK sM sO Sr Ss St TN TO tQ TR tT tU tX Tz Ua Ub Ud Ue Uf Uh uI Uk UL uM UN Uo uP UR Us UT uV uW uX uY uZ vB vC vH vI vO VP vQ Vs VT VU VV vW wB wD wE wF wG wH wJ wK wL wP wQ yD yH yJ yK yL zG zH zI yE tM tL xA Wn Wm Tj) yL(AA AD aE AF aG aH aI AL aM AN AO AP AR AS AW AX aY aZ bA bB BC bE bF BG bH bI bJ bL bM BN BO bQ bR bS bU bV bW bX bZ cA cB cC cD cE cF cG CH cI cJ cK cL cM cN CO cP Cq cR CS CT CV CW CX cY cZ dA DB Dc DD DE dF dG dH DI dJ DK DL dM dR eC ED EF Et EZ Fa FN Fr Fw Fy GL gP gW HA Hb HC HF hG hL hO hP Hq HR Hu Hv HW HX iA IB Id iH Ii IJ Ik Il Im In IO IP Iq Ir Is It Iu Iv IZ JD JE JF Jg Jh Ji Jj JK JL JM Jn jO Jp JQ JR Js Jt Ju jV JY Kc Kd Ke Kf Kg Ki Kn Ko Kp KQ KR kS Kx Ky Kz Ld Lh Li lM lO Lu Lw Lx Ly Lz Mb Mc Md Me Mf Mh Mi Mj Mk Mn Mp Mq Mr Ms Mt Mu Mv Mw Mx My Mz Na Nb Nc Nd Ne Nf Nh Nk Nl Nm Nn No Nq Ns Nt Nv nW Nx NY Oa OE OF Og OH Oi oK Om ON Or Ou Ow Oy Oz Pa Pb Pc Pd PF Pg Ph Pi Po pS pY Pz QA QB QC QD Qe QG QH qI Ql Qm Qn QT QU Qv QW QX QY QZ Ra rB RC Rf Rg Rh Ri Rj Rm rN rQ rR rS rT rV rX rY rZ sC sK sM sO Sr Ss St Tn tO tQ Tr tS TT tU Tv tX Tz Ua Ub Uc Ud Ue Uf UG Uh uI Uk UL UM UN UO UP UR Us UT UU UV uW uX uY uZ vA vB vC vH vI VO VP vQ VS vT vU Vv vW wF wG wH wJ wK wL yD yH yJ yK zA zG zH zI yE tM tL xA Wn Wm Tj tF) wL(aA aC aF aH aI aJ aK aL aM AN AO Ap Ar AS aU aV aW AX aY BA BB Bc bE bF BG bH bI bL Bo bP bQ bR bV bX bZ cC cE cF cH cI cJ cL cN Cp cR cS Ct CU Cv cW Cx cY dA DB dC DD DG DI dL Dp dR Ed EF Et EZ Fa Fb FP Fw FY Gp gW HA Hb Hc Hf hO HR HV hW HX Ic Ii Ij Ik Io IP Iq Ir Is It Iu Iv IZ JD Je JF Jg jH JI Jj Jk JM Jn JO Jp Jq JR JT jU Jv jY Kc Ke Kf Kg Ki Kj Kp KQ KS Kx Ky Ld lK lL lN lO Lu Lv Lx Ly Lz Md Mf Mg Mk Mr Ms Mu Mw Mx Mz Na Nb Nc Ne Nh Ni Nj Nk Nm Nn No Nq Nr Ns Nt NW Nx NY Oa OE OF OH Oi Ok Om ON Or Oy Oz Pa Pb Pc Pd Pg Ph Pi Pj Pk Po Pz QA qB qC Qe QG QH qI Qm qO qT QU QV qW QX Qy Qz RB Rc Rf Rh Ri rP rS rU rV rW rZ sC sM Sr tO tQ tS tV tX Tz Ub Uc Ue Uf Ug Uh uI Uk uM UN uO UP UR Us UT uU Uv uX uZ vA vB vH vO VP vQ vS Vt vU Vv wB wC wD wE wF wG wJ wK wP wQ yD yJ zG zI yE tM tL xA Wm Tj tF) qO(aA AD aE Af aG aH aI AJ aL aM AN Ao AP aQ AR aS aV AW Ax aZ bA Bb bC bE BG bI bL bM bN Bo bP bQ bS bV bX bZ cE cF cG cI cJ cL cN Cp cQ Cs CT CU CW cX cY dA Db DC dF DG dH Di dJ DK DI Dp dR eC ED Et EZ Fa Fb FN Fp Fw Fy GI GP gW HA Hb hC Hf hG hL Hq Hr Hu HV HX iA IB iH Ii Ij Ik Im In Io IP Iq Is Iu Iv iZ JD Jf JG Ji Jj jK JL Jm Jn Jo JP Jq JR Js JT JU JV jY Kd Kf Kg Ki Kk Kp KQ KR KS Kx Ky Kz Lh Li Lj lK lL lM lN lO Lu Lv Lx Ly Ma Mb Mf Mg Mk Ml Mn Mp Ms Mt Mu Mv Mw Mx My Mz Na Nb Nc Nd Ng Ni Nj Nm No Nq Nr Ns Nt Nv nW Nx Ny Oa OE Og OH Oi Ok Om On Ou Ow Oy Oz Pa Pc Pd Pe pF Pg Ph Pi Pj Pk Po pY Qa Qc QD QH Qm Qn qQ Qt QU QY QZ rA RB rC Rf Ri rP rR rV rX rY sC sM sO Sr Ss tQ Tr tU tV Tz Ua Ub Ue Uh Ul Um Un UP Us Ut Uu uV uX uY vB vH vI Vo vQ vS VT Vu vV wF wG yH yK zH zI tM tL Wn Tj tF) rW(aA AD Af AJ aK Al aM aN Ap aQ aR aS aV AW aX aZ BA BC bE BG bI bL bN BO bQ bR bS bV bX bZ cD cE cF cG cI cJ cL cM cN cQ cS CT Cu Cv CW cX cY dA Db DC DD DG dH Di dK dM Dp dR eD EF EZ Fa FN FP Fw FY Gl Gp HA HB hC Hf hG hL hO hP Hq Hr Hu Hw HX iA IB Ic Id IH Ii iJ Ik Il Im In IO IP Iq Is IZ JD Jf Jg Ji Jj JL Jm Jn Jo Jp Jq Jr Js Jt JU Jv JY Kd Ke Kf Kg Ki Kj Kk Kn Kp Kq Ks Kx Ky Kz Ld Lh Li lN Lu Lv Lx Ly Ma Mb Mf Mg Mh Mj Mk Ml Mn Mp Ms Mx My Na Nc Ng Nh Ni Nj Nk Nm Nn No Ns Nt Nu Nv Ny Of Og Oh Oi Om ON Oy Oz Pa Pd Pe pF Pg Ph Pi Pk Po pS Qa QB qC Qe QH qI Ql Qm Qn QU qV Qw Qx Qy Qz rA RB RC Rf Ri Rm rN rP rR rU rV rX rY rZ sC sK sM sO Sr Ss tQ Tr tS tU tV Ua Ub Ue UG Uh uI UL Um Un Uo Uu uV uW uX vH vI Vo vT vW wE wF wJ wP wQ yD zG zH zI tL Wn Tj tF) vP(AA Ad aE Af aH aI aJ aL AN Ap AR aU aV Aw Ax bA Bb Bc bE Bg bI bL bM bN Bo bP bQ bS bV bX bZ cF cJ cN cQ cT cX cY dA DC Dd dF DG dH Di Dk dM Dp dR eC Et eZ Fa Fn Fp Fr Fw Fy Gl Gp Ha Hf hO Hq hV Hx iA Ii Io IP Iq Ir Is It Iv iZ JG Jh Ji Jj jK jL Jm Jn Jp Jq JR Js Jt JU Jv jY Kd Ke Kf Kg Kk Kp Ks Kz Li Lj lL lN lO Ma Mg Mk Ml Mm Mn Mp Mt Mu Mw Mz Nb Nh Nj Nm No Nr Ns Nt Nu Nv nW Ny Oa Oe Of Og OH Oi Ok Om On Oy Pa Pc Pd Pe PF Pg Ph Pi Pj Qa QC Qd QH Qm Qt QU Qv Qw Qy RB rC Rf Ri rT rV rX rZ sC Sr tQ Tr tS Tz Ub Uc Ue Uf uG Uh uM Un uO Up Us Ut Uu uV uY uZ vI vQ vS vT vV yJ yK tM tL xA Tj tF) sC(aE aG aH AJ Al aM An Ao AR aS aZ Bb bC bE bG bI bL bO bX bZ cC cD cF cG Ch Co cQ cR Cs Ct cU cX cZ dB dE dF dG Di dM Dp eD Ef ET eZ Fb fN Fw Fy gL HA Hb hC hO Hr Hw IJ Il In Io IP Ir Is IZ Jd Jc JF JM Jn jO jP jQ Jr JY Kd Kl Kp kQ Kr lK lL lN Lv Lx Ma Md Me Mf Mk Ml Mp Ms My Mz Na Nb Nc Nd Nf Ng Ni No Nq Nr Ns Nt Nw Ny Of oK oN Pa Pe pF Ph Pi Pj pS Qc qD qI Ql Qm Qn qT Qu Qw Qx Qy Ra rB RC Rf Rh Ri rN rR rS rT rV rX rY Ss tN tQ tS tV Ub Uf uI Uk UL Ur Uu uV uY uZ vB vI Vp vS VT Vu Vv wH zG zH xA Wm Tj tF) qU(aC aG Aj aK aL aM AN Ap aR As aU AX bE BG bH bM Bn bP cB cH cO CP cR cS cU CX cY DB dC dD dE dI dN dR eC Ef Ex Fb fP fY gW Gz HB Hc Hf hG iH iO Iz jQ Kf Kg Ki Kj Kk Ko kR kS Kz Ld oK Pa pF Ph Pi Pj Pk Qx rO rU tR tS tV tX uL uN Up uV vS Vt wH yH xA Wm) wH(aF aH aK aL aN Ap aQ aR aY bE Bg bL bM bQ bX Cq dD Di ET FN fP Hc hP hV Hx Ib iH Ik Il It jD Je jM jU JY Ke Kk Kz Lv Lx Mk My Mz Nc Nk Nq Nr Nw Of Oi Pa Pc Pj qA Qe QH Ql Qu Qw QX Qy rA rN rO rP rS rU Ss Tn To tR tT tV Ua Uh uP Us Uu Vv yD yK zG xA) Mm(Aa AJ aL aM aP aU aV AW aX bE bF bG Bo bU bV cC cG cK Ct Cv cY dA Db DC DI Dk dM dN eD fY gL Hc Hf hG hO iH iZ Kd Ke Kg Kq Kr kS Ky nY PF qB qI qV qZ Rb rN rQ rS rV sK sO tN tV Ub Ug uN uP Us uU vA vB vC vS vT wB wE wF wJ wK wP yJ yE tM tL Wn) tS(Al An aW

Yg Yi Yj Yk Zw Zx Ye Tm Ti) iB(Fc Fd Fi Gb Gh Op Rz Sh Sj Vz Yg Yh Yi Yj Zx Ye Tm Tl) jI(Dr Du Fc Fd Fi Gb Gn Op Rz Sf Sh Si Sj Va Zx Ye Tm Xa) uM(Aw Bc Cw dR fP gW Je Js kR Kz Ms Mt Nj Nk Nl pF Qv Qw) lN(Eq Fd Gc Gn Hl Ho Lp Op Rz Si Wb Yg Yh Yi Yj Zw Tm) Aw(hL hO rU sK tQ tR uI uR uZ vB vO vT wC yH zG zI) jK(Dr Du Fc Fd Fi Gn Op Rz Sh Sj Va Yg Zx Ye Tm) Qw(tN tO tU tX uL uX vA vW wB wL zG zH zI xA) Qv(sM uG uI uN uR uZ vI wH wJ yH yK zG zI) lO(Dr Eq Fd Gb Gc Gh Gn Op Rz Yd Yg Ye Tm) Mz(fN rR rV uL uO uV uZ vS zG zH xA) Tt(hL hO qG qI rN sK uI vH wC wK tM) Kz(pS uL uX uY uZ vB wH wL zH xA Wn) jG(Dr Du Fc Fd Gh Rz Zx Ye Tm Ti Yf) jV(Fd Gb Gc Gn Hl Rz Yg Yi Yj Zx Tm) Ad(fY hL hO qG qO rN rR sK uI zG) lt(sK uL uZ vH wC yH yK xA) vB(fP Jn Ke Lu Mm Ms Mt Nw) hL(Cw Ex hC Jd Nn On rN) zG(Bc Di Je rN tQ wD wH) jE(Dr Fd Op Rz Yj Ye Tm) rW(iA Je Na Nl qU wL tF) uL(Cw Ky Lv Mm Mt Na Pj) aH(gC oD oT oV pI pK) fP(uI uY wP wQ zI xA) Mm(tU wK wP wQ xA) Uf(sK tN tO tX wP) bX(sK uZ yK xA Wn) qU(fN fY Sh tO tX) rN(cB Cw kR uG Vs) pF(tQ tS tX zH) Mt(tQ wP xA) Tr(rR vS yH) Jd(fN sM tR) Je(fN qO qP) Kf(sK vH wK) dU(Et Im Ir) hO(Cu Cw eF) rA(Fc Fi Si) qX(Hp Zx Tm) pS(aK aU gW) Di(uU yK) Lv(tQ wH) Jg(qI rR) Og(tN tX) On(tR tX) cB(rU uI) dR(uI wL) fY(sO zH) gC(nW oO) qO(eD tF) oD(cR nN) BcsO CwsK NaxA TnwC YipH SfqW SjqT JieP PshV KyuP NwvS OwtS UswH eFvT rBuN} aH{pH(Af aG aJ aM aQ aR Ax BA bB bC bG bH bL bM Bn BO bP bU bV bX cF cL cO Cp CQ cR Cs cT Cu Cv Cw CX cZ dC De dF Dg dH Di dK dN Dp dR DU Ed Ef Em Et Ez Fd Fi Fn FP FR Fw Fy GL Gn GP Ha Hb HC Hf Ho Hp Hq Hr Ib Ic Id Ih Ii iJ In Ip Iq Ir Is It IZ Jf Jh Ji Jn Jp Jq Ju Jv Jy Kd KE Kf Kg Ki Kj Kl Ko KP KQ Kr KS Kx Ky Kz Ld Li Lj LW LX Ly Md Mc MF mI Mk MM Mn Mq Ms MT mW MY NB Nc Nd NJ Nm NN No Nr Ns Nu Nv Nx NY Oa oF Oh Oi Ok Om ON oQ Or Ou oV Ow Oy Pd Pe pF Ph Pl Pj Pk Qa Qc Qg Qh Ql Qm Qn Qt Qu Qv Qw Qx Qy Ra Rb Rf Rg Ri Rj Rt Ru Sf Si Sr Ss Tn To Tr Tt Tz Ub Uc Ud Ug Uh Uk Ul Um Un Us Uu Uv Uy Va Vj Vt Vz Wc We Yd Yi Yj Yk Yl Zx Ye Tl Xa Wm Th tF) jB(Aa aE Af aM Ao aR Ax bF Bn bO bZ cF cR Cs cT Cw CX Dc De dF dH Du Ef Et Ex Fa Fp fR Fw Fy GL Ha Hc Hq Hw Ih Ii Ij In Iq Ir Is It Jh Ji Jm Jn Jq Jy Ke Kj Kl Kn Ko kR kS Kx Kz Ld Li Lj Lx Ma mE Mq Mr mT Na Nb Nj Nm Nn No Nq Nr Nv Nx NY Oa Oh Om ON Oz Pd Pe PF Ph Pj Po Qa Qc Qe Qn Qy Rz Sh Sr Tn Tt Uc Uh Um Un Up Us Ut Uu Vh Vv Vw Ti) dU(Af Ao Ax bF Bn Cq Cs Cw cX De Dg dK Et Ex Fp fR gP Hc Hq Hu Ih Ii Ij Il Im Iq Ir Is It Jd Je Jg Jh Ji Jn Jo Jq Jt Jy Ke Kf Kn Ko KQ kS Kx Ky Kz Ld Li Lj Lx Ma Mf Mg Mm Mn Mq Mr Mw My Na Nm No Nq Nr Nv Nx NY Oa Oh Ok ON Oy Oz Pb Pd Pe Pf Ph Pj Pk Po Qa Qc Qe Qn Qt Qu Qy Rz Sr Tt Tv Uc Ue Uf Ur Ut Vh Vs Wd We Yk Zx Ti) pI(Aa Ad Af Ao Ap Ar Aw Ax Ba bF Bn bS bZ Co Cp Cw cX De Dg dK Dl Du Ef Et Fa Fp fR Fy gP Hq Hu Ih Ij Ik Il Im Iq Is It Je Jg Jh Ji Jn Jy Ke Kn Ko Kx Ld Li Lj Lx Ma Mg Mh Mq Mr Mw My Na No Nq Nr Nx Ny Oa Ok Om ON Ow Oy Oz Pd Pe PF Ph Po Qu Qy Qz Ue Uf Uu Vs Wd Wh Yi Th tF) nA(Dr Du Eq Fc Fd Gb Gc Gh Hl Ho Hp Lp Lt Op Ps Rt Ru Rv Rx Ry Sf Si Sj Uw Ux Uy Uz Va Vb Vc Vh Vi Vj Vw Vz Wb Wc Wc Wg Wh Yd Yg Yh Yi Yj Yk Yl Zw Zx Tm Tl Xa Th Yf) Th(eQ fA fB gC gZ kC kE kF kG kI kK kN kO kP lW lX lY mE mF mH mI mM mP mS mT mU mW mY mZ nB nC nD nF nH nI nJ nK nL nM nN nO nR nT nU oD oO oP oQ oT oV oW) nD(Dr Du Fc Fd Fi Gb Gc Gn Hl Ho Hp Lp Lt Op Rt Rv Rx Ry Rz Sf Sh Si Sj Ux Va Vb Vh Vw Vz Wb Wc Wd We Wf Wh Yd Yg Yh Yi Yj Yk Yl Zw Zx Ye Tm Tl Xa) oV(Af Ax Bn Cu Cw cX De dK Du Fa fR Hq Ih Ii Im Ip Is Jd Je Ji Jm Jn Kn Ko Kq Ld Li Lj Lx Mq No Nv Oa On Pe Qa Qe Qz Rz Ue Wd Wh Yi) Dr(jD kC kE kF kG kI kK kN kO kP lW lX lY mE mF mH mI mM mP mS mT mU mY mZ nB nC nF nH nI nJ nK nL nM nN nO nR nT nU oD) eQ(Af Ax Bn Cw cX De Ex Fp fR Ip Jd Je Ji Kn Ko Kq kS Kx Li Lj Lx Mq Mt No Oa On Pe Qz Rz Tn Tt Ue Ut Vb Wd We Wh Ti) gZ(Af Ax Bn bO Cw cX Du Ex Fa fR Fy gP Jd Je Kn Ko Kx Ld Li Lj Lp Lx Mq No Nv Oa On Pe Qa Qz Rz Ue Ut Wd Wh Yi Xa) nK(Du Fc Fi Gb Gc Gd Gn Hl Hp Lt Op Rv Rx Ry Rz Sf Sh Si Sj Vb Vw Vz Wb We Wf Yd Yh Yi Yk Yl Zw Zx Ye Tl Xa) oW(Af Ax Bn Cw cX De Du Fa fR Ih Is Jd Je Ji Kn Ko Kx Ld Li Lj Lx Mq No Nv Oa On Pe Qz Rz Tt Ue Ut Wd Yi) Vw(gC kE kF kG kI kK kN kO kP lW lX mE mF mH mM mP mS mT mY mZ nB nC nF nH nI nJ nL nM nN nO nR nT nU) oT(Af Ax Bn Cw cX Du Fa Fp fR Jd Je Ji Ko Kx Ld Li Lj Lx Mq Na No Oa On Pe Qz Rz Ue Ut Vb Wd Wh Yi) mP(Fc Fi Gc Gn Lp Lt Op Rv Rx Rz Sf Sh Si Va Vj Wb Wd We Wh Yg Yh Yi Yj Yk Yl Zx Ye Tm Tl Xa Ti) lX(Eq Fi Gb Gc Gh Hl Ps Rt Ru Rv Uw Ux Uy Uz Va Vb Vc Vh Vi Vj Wc Wd We Wf Wg Wh Zx Ye Ti Yf) oD(Af Ax Bn Cw cX dK Du Ex Fp fR Jd Je Kn Ko Kx Ld Li Lj Lx Mt No Nv Pe Qz Rz Ue Ut Vb Wd Wh) pK(Af Ax Bn Cw cX Du Fa fR Jd Je Kn Ko Kq Kx Ld Li Lj Mq No Nv Oa Om On Pe Qz Ue Ut Wd Wh Yi) mZ(Du Fi Gb Gc Gd Gn Hl Ho Lt Rv Rx Rz Sh Si Vb Vh Vz Wd We Wf Wh Yi Yk Zx Ye Tm Tl Xa Ti) gC(Du Fa Jd Je Ji Kn Ko Kq Ld Mq Oa Ok Qz Rz Tn Tt Ue Ut Uw Vb Vh Vv Wd We Wf Wh Yi Ti) nL(Du Fd Fi Gb Gc Gn Hl Ho Op Rv Rx Rz Sh Uw Vb Vh Wd We Wf Wh Yi Yk Yl Zx Ye Tl Xa) dX(hC hF hG iH iO iP Kc Kk Kp kR kS Kx nW nY oE oF oH oK oN pF Qx tF) mF(Du Fi Gb Gc Gn Op Rv Sh Uw Ux Vb Vh Vj Wd We Wf Wh Yi Yk Ye Xa Ti) mE(Du Fi Gb Gc Gn Hl hX Op Rx Rz Uw Ux Vb Vj Wb Yi Yj Ye Tl Xa Ti) kE(Du Gb Gc Gn Lp Rz Sh Vb Wd We Wf Wh Yh Yi Zx Ye Tl Xa Ti) Gc(kC kF kG kI kN kP lW mH mY nC nH nI nO nT nU qX) Gn(kC kF kG kI kP mH mI mT mW mY nB nC nH nJ nR nU) Wh(kC kF kG kI kN kO kP lY mH mI mW mY nC nH nI nJ) eP(eC Hb hC hG iA iJ Kc Ko kQ kR nW nY oF pF tF) Wd(kC kF kG kI kN kO kP mH mI mW mY nC nH nJ) Rz(kF kG kI kK mI mW mY nB nC nH nI nJ nR nT) Vb(kC kG kI kN kO lW mI mT nB nC nH nR nT qX) fA(Af Bn cX Fa Gb gP Jd Je Ko Kx Ld Qz Xa) fB(Cw Ex Fa Fp Fy Jd Je Ji Ld Pd Ue Ut) We(kC kG kI kN kP mH mI mY nC nH nJ) Yi(kF kI mW mY nB nC nH nI nR) Du(kI kP mT mY nC nH nJ) Bo(DW EO EW) Ye(jM kI mI mW nC nJ) eM(Ko kQ Lp Op oQ Si) Ti(kG kO lY mT nI) jD(Em Gb Op Si Yg) Lx(EO EW) Wf(kG kI nC nH) Tl(kK mW nB nT) Va(kF lW mY) bB(dW EW) Gb(mI nC) Rv(nC nH) Vh(jY qX) Vi(mT qY) Pj(rN tT) lW(Fc Op) HlmI JidW TmqY LtmY WnVt VjqX aWeO nRhW} bB{pH(aM aW bM cF CW dN Dp Dr Ed Ef Em Eq Et Ex Ez Fa Fb Fi Fp Fw Gd Ha Hb Hc Hf Hp Hq Hr Hu Hv Hw Hx Ib Ih Ii Ij Ik Il Im In Io Iq Ir Is It Iu Iv IZ Je Jf Jg Jh Ji Jj Jk Jl Jm Jn Jo Jp Jq Jr Js Jt Jv Jy Ke KG Ki Kj Kk Kp KQ Kr Ks Kx Ky Kz Ld Lh Li Lj Lu Lv Lw Lx Ly Lz Ma Mb Mc Md Me Mf Mg Mh Mi Mj Mk Ml Mm Mn Mp Mq Mr Ms MT Mu Mv Mw Mx MY Mz Na Nc Nd Ne Nf Ng Nh Ni Nj Nk Nl Nm Nn No Nq Nr Ns Nt Nv NW Nx NY Oa Oe Of Og Oh Oi Ok Om On oO Or Ou Oy Oz Pa Pb Pc Pd Pe Pf Pg Pi Pj PK Po Qa Qb Qc Qd Qe Qg Qh Ql Qm Qn Qt Qu Qv Qy Rc Rm Rv Sr To Tt Ub Uk Um Un Uo Ur Ut Uv Uy Vi Vt Vu Vz Yh Tj Th) eO(AA aC Ad aE AF aG aI AJ aK Al An aO Ap AR AS aU aV AW aX aZ Ba bC bE bF BG bH bI bJ bM BN BO bP bQ bR bS bU bW bX bZ cA cB cC cD cF cG Ch cI cJ cK cL cO Cp CQ cR cS CT CU CV Cw Cx cY dA DB DD DE dF Dg dH Di dJ DK dM DW dX EM Eo eP Et EW FP FR gV Hq Hr Hv Hw Ih Ii Ij Ik Il Im Io Iq Ir Is It Iu Iv Jg Jh Ji Jj Jk Jl Jm Jn Jo Jp Jr Lu Lx Ly Lz Ma Mb Mc Md Me Mf Mg Mh Mi Mj Mk Mm Mn Mp Mq Mr Mt Mu Mv Mx My Mz Na Nb Nd Ne Nf Ng Nh Ni Nk Nl Nm Nn Nq Ns Nt Nu Nv Ny Of Oh Oi Ok Om On Oy Oz Pa Pb Pc Pd Pe Pg Pz Qa Qb Qc) Eo(aA aC aD aF aG aJ aK Al aM aN AO Ar AS Aw aY Bc bE bG bI bM bN BO bP bR bS bX bZ cA cB cH cP cR cS CT Cv cW CX cZ dA DC Dd dE dF dH Dl dJ Dk DL dM Dw dX Ef eM Et Ew FP FR Gd Hq Hu Hw Ih Ii In Iq Ir It Iu Jg Jh Ji Jj Jk Jl Jm Jo Jp Jq Jr Js Lv Lw Lx Ly Lz Mb Mc Md Mh Mi Mj Mk Ml Mm Mp Mq Mr Mt Mu Mx My Mz Na Nb Nd Ne Nh Ni Nj Nl Nn No Nq Nr Nt Nx Oe Of Og Oh Ok Oy Oz Pa Pb Pc Pe Pf Pz Qa Qb Qe) dU(Aa aX Cw dN Et Fp fR Gh Hb Hf Hv Hw Hx Ih Ij Im Ir Jh Ji Jj Jl Jn Jq Jt Jy Ke Ko Kq Kx Ky Kz Ld Li Lj Lv Lx Ma Mb mE Mf Mk Ml Mn Mq Mr Mt Mu Mv Mw mY Mz Na Nc Ne Nf Ni Nl Nm Nn No Nq Nr Nt Nu Nv NW NY Oa Of Om ON Oy Oz Pa Pc Pd Pf Pg Qc Qn Sr St Uh Ur Ut Tl) Ew(aA aC aD aF aG Aj Al aN AO AX Bc BG bI bO bP bR bS bW bX cF cH cI cK cN cP cQ Cs Ct Cw cY Dc dF dJ dK Dl EM Fp gV Hv Ii Im It Jj Jk Jo Jq Jt Lj Lx Ly Mc Mp Mw Mz Nc Nd Nl No Nq Ny Oe Of Pc Pg) Dw(aC aF aJ Al aN AO As Ax BG bI bO bR bW cI cN cP cR Cs DC dJ dK eM eP Fp Gl gV Hv Ii Il Im Ip Iq Iu Jj Jk Jo Jt Lj Lv Ly Ma Mg Mp Mw Nc Nd Ng Ni Nl Nm Nq Nu Nv Ny Oe Of Og Oi Om Pg) eW(aA aC aD aG aN Ao Ax aY bA bI BO bR bS cH cI

No Nq Nw Oa Oz Qv Tn) Op(aC Ax cR Cs Fa Hl Hr Jk Jn Ky Li Lj Mx Nd No Oa Oz Pb Qn Ye) Ax(Dr Fi Gb Hp Lp Ps Rx Rz Sh Si Uw Vh Vz Wb We Yd Yg Zx) Rv(Ao bN cR Fy Ij Jg Jn Jp No Ok On Tn Ut Th) Ye(Ao cR Cw It Jl Lj Nw Ok On oO Tn Un Yi) Fi(Ao Cw Hb Ij Jp Li Lj No Nr Ok Sr Tn) cR(Eq Fd Hp Ry Rz Sf Ux Vh Wb Yi Xa) Ao(Eq Gd Hl Ho Lp Rt Va Yh Yj) No(Gh Lp pK Rz Sf Ux Wb Yk Xa) hX(aX bN bV bW bZ cB cS cX dN) Rz(Cs Jd Jn Lj Mx oO Or Rg) Eq(Ap Cw Dg Jg Ok On Ut) Th(aM kI oO Or Rg Uh Vt) Hl(Cw Ih Ir Kx Nw On Un) Ux(Cs Jn Kj Ky Li Lj Mx) Gb(Fa Jl Lj Mx Oa) Yi(Hr Kg Kj mS oO) Lj(Vb Vh Vw Tl) Dr(cG Cw Nq) Jn(Lp Vh Yd) Kx(fA oV oW) Vj(cP Mx Rj) Nq(Gh Vh) Yj(Iq oO) bQ(Yg Yk) rX(dC Nk) AsjR CtjE NjgW UeeD TnYh YdUt LiVh LtNw RtOn VojG aWlK aYhV bHhW} Wn{Vt(aD aE aG aI aJ aK aL aM aN aO aP aQ aS aU aW aX bF bH bI bJ bL bN bP bQ bR bS bU bV bX bZ cA cC cD cE cG cJ cK cL cO cR cS cT cU cV cW cX cY dA dB dD dE dF dG dH dI dJ dK dM dN eC eD eF Ex fP fY gW hA hC hF hG hL hO hP iA iO iP jE jF kQ kR kS nW nY oE oF oH oK pF pS pY qA qC qD qG qH qI qO qP qQ qV qW qZ rN rO rQ rR rS rT rU rV rW rY sO tN tO tQ tR tT tU tX uG uI uL uM uN uO uP uR uT uU uW uX uY uZ vA vC vH vI vO vP vS vT vU vV vW wB wC wD wE wF wH wJ wK wL wP wQ yD yH yJ yL zH zI yE tM tL xA tF) sC(Aj aS Bb Bg bQ bS bX cC cF Ch dB dK Fn Hv Hx Ic Ip Is It Iv Iz jF Jr JY Ky Lj lL Mr Mz Na Ng Ni No nY Oa Og Oi oK Pc qC Ql qP QU Qv qW rN rW rX Up Us uV vB vQ vS vT wL zH tL Wm Tj) Pa(eD eT fN fY hA hO hP hV jG jL jM pY qB qC qH qI qO qP rW rX tN tO tQ tR tS tU uV vP wB wD wF wG wH wJ wK wL wQ yD zA zI xA) qP(Ad Ap aR Bb Cw cY Dc Dd Dg Dk Et Fa Hb Hq Ic Ip Iv Jd Jp jY Kg Kz Lh lL My Na Ok On Pc Pg Qc qD Qw Ri rX Uo Us uV wL xA) wL(aC aR Bc bG fN Hq hW Ip Is Iu Jd Jh Jo jR Kg lK Mg Oy qG Qh qO qT tS Ub vH Vv wH) tS(Al aN Hb Jd jY Ky Lu Mu Na Nu Pc St Um Up uU wH) wH(bX cS Di In Ip Is It oE Pc Qv Qw tX Us vS xA) uV(bX Ez fP Hx Ic jF Mz Pc qO Qu Qx rW Uk vP yL) rW(AD bX Dc Dd Et Jd Kp qC qW Tr Uf) yL(Dg Dk Et fN Hq Ip Kj Ng Of Tr Tt Uf) qO(Ad Aw Bb Di Et Hb jY Pc Qc Qw Us) Ip(fY hC hO Jp Nj qI tQ wC wP) xA(cR Iq Is It lK lO Pi Qy Tt) Us(Et eZ fN hW jV lK qC rX) Pc(eZ fN hL qC qI rX zH) Et(Kr rU tT vP vV zG) Ic(aM aV eZ Is qI yD) Jd(fN fY tO tR tX vP) qC(aU fY gW jQ jR vP) vS(hA jY Mk Mu Tt) zH(aN vP vV) jF(Dp uR vI) Na(jV wJ) Tt(Ha rP) Qc(fY vP) Li(aN bG) pF(bG fN) NthX MuuU HqpY HbtO HfqU aRzG jEtM} Va{jI(aD aI An aS aU bH bO cF cQ dK Dl dN Dp Fn Gd hA Hb Hq hR Hu HW hX Ib IC Ik Im In Iq Is jH Jj JK Jo JP Ju Jv jY Ki Kj Kk Kx Lh lN Lw Ly Ma Mc Mf Mg Mi Mj Ms Mu Mv Na Nl Nq Ns Nw Of Og Oi Ok On Op Or Ou Pg Qa Qc Qd Qh Ql Qm Qn Qt QW Qz RA Rg Ri Rm Ru Sf St Tn To Tz Ua Ub Uc Ud Uf Ug Uh Uk Ul Um Un Uo Ur Uu Uw Uy Uz Vb Vj Vu Vv Wd We Wf Yh Yi Yj Yl Zw Zx Wm Tj Th Yf) hV(Ez Fr Hu Io lq Iv Jg Jh Jk jR Mg Mh Ml Mt Nb Nc Nl Ns Of Oy Pa Pd Qh Ql Qt Qu Tn Tv Tz Ua Us Vs Wd We Wf Wh) jK(aA AD aM Bg Ch dD Dk Ef Ex Ib Iq Iz Jd Kc Mg Mw Nb Nc Nq Qh qT qV Qz Rm Tz Uw Vi Vu Yh Yi) Qh(eD hA hR hW hX iB jF jG jH jL jM jP jU jV jY lK lL lN lO) Or(hA iB iC jE jF jG jH jL jM jO jP jR jU jV jY lK lL lN lO) aD(hA iB iC jE jF jH jL jM jO jP jQ jR jU jV jY lK lL lN lO) jR(aI cI Cu dD Et Im Kc Mj Mw Pd Qa Ql Rm Tz Vu Zw Zx) rB(Fn Jd Je Jg Mt Oy Pc Pd Pz qT Qu Qy rC Ua Vs Wf) jQ(aE Al bS Cu Dc Et Ex Gz Im Ki Mw Mz Uw Yh Yi Zw) eD(Fr Hq Il Jd Jg Jk Mu Nn Om On Pf Tr Ua) hX(Fr Hu Ib Jd Jk Mb Mu Mv Nq Oy Qw Ut) jU(cZ Dk Ib Jq Kc Mj Mv Ql Ua Un Uw Vu) jY(aI cW Dc Dk Fr Im Iz Nq Om On Ou Vs) hR(Fr Ib Jd Jg Jk Mz Qw Ua Vs Wd Wh) lK(cW dD Dk Fr Fw Gl Ib Iz Uw Vs) jO(aI dD dF Ib Jd Mv Om Ou Tz) jP(aI Ib Jk Mj Mv Om Ou Pf Rm) lN(cW dD Fw Jd Mv Om Qv) hA(dD Fr Fw Hq Jd Uw) jH(Fr In Mv Nq Ou Zx) jV(Dk Ib Jq Mv Ua Uw) hW(Fr Ib Jd Jk Ua) iC(Ib Im Jq Mv Mw) gW(bO Ex Ii Ut) jF(cP dD Jq Qe) Tz(jE jG lL) Uw(iB jE lO) aM(qT qV) iB(Dc Rg) rC(Jk Vs) rA(Nc Qy) jM(Ou Zx) lL(dD Jd) EtmT NoeQ InlO RmqW OnjL VhjG cRmU eMgL} gW{mS(aA aC Af aG aI Aj aL aN aQ aW bC bF BG bJ bP bW bZ cB cD cF cG cH cI cK cM cS Ct cW Cx cY cZ dA dB Dd dE dN gP Hc hG iJ jK jM jP Kd Kf kG Ki KN kO kP Kq kS Kz lK lX lY Mg mH Mk Ml Mt Mx My Na nC Ng Nk NL Nm nR Nt nY oK pF Pi qT qW tF) Ye(aD Co Cu Dk Ic Ii Ij Im Jd Jl Jp Js Ke Kr Ld Lh Lj Mj Ml Mp Mq Mv Mx No Nq Nw Oa Oh Or Ou Ow Pf Pg Qa Qc Qd Si Vh) Mg(Fc Fd Fi Gb Gc Hl Ho Hp Op Ry Rz Sf Si Sj Uw Ux Vh Vi Vw Vz Wb Wc Wf Yd Yl Zx Tm Xa) Gc(Ch Ef Hc Hu Iq Jk Jn Kg Lj Mh Ms Mx Nf Nk Nu On Oy Oz Pa Pb Pf Qu Rb Ss Ua Uf) Ic(Fc Fd Gb Hl Ho Hp Jd Lp rN Rt Sf Sh Si Sj tS uV Ux Wb We wG zH Zw Zx Tm Tl) Vh(bJ bO cM Cq cR cY Db dG eC Fn Hr Hw iJ Iz Jj Jk Nx nY Oh Qy Qz Sj Ua Wc) Si(bM bO bZ cD cF Ho Ii Iz Kg Kp Kz Mk Nf Oz Pg Qc Ss Wh Tm) Ii(Fd Gb Gn Hl Lt Op Ps Rv Rz Ux Wb Yd Yj Zx) Yd(Bg cW Ef Ex Hf lZ Kp Nx Ou Ow Ss) Hc(Gh nC nH nK Sf Sj Ux Vb Vw Wb Zx) Sf(cW Ex hC Hf lZ Jh pF) Jk(Fc Hp Op Rz Uy Yl Zx) Dc(Ps Uw Uy Yg Yi Yl) Iz(Eq Op Ps Wb Zx Tl) Vz(Im Ko Om On Po Qa) Sj(Ef Fr Ke Qc Un Vi) Qa(Du Lp Rx Uy Tm) Op(Ad aV cQ Jt Ko) mZ(bH bW Db Hf Kz) Co(Gb Wh Yk Yl) Cu(Fd Fi Hp Yl) Di(nC nH wH zH) Nj(kO mF mI nO) Zw(eC Ex Ow Wh) Rz(hC Kf Ng Sr) Rv(Kj Nx Pa Qu) bP(dX eM nC nH) nD(Bn Cx dK Nt) rS(sF sH sI sJ) Gb(bO cD Ko) Gd(aD cW jR) Ho(bO Ih Oh) Wd(Mh Or Po) Wf(hC Sr Tz) Tl(Jr Ke Lh) Ps(Ef Jy Qu) Nx(Lp Ru Sh) Ut(Fd Rt Vw) Pf(nC nJ nL) fR(aD bH jR) nN(Ct Ik mI) mP(Af Mh Nt) Em(hC Ko) Me(nC nH) Hp(Im Qz) Yh(Fn Jn) Yk(bQ eC) Wb(Ke Kj) Wh(bN Im) Yl(cQ Jr) On(Dr Gn) Uw(aO eC) pS(sF sI) AnYg AsmT BanK CqVi DemW DuKg EfVb PoFc NfYi HuUy ZxKj QyRt XaKe KinH KpRy aMmY bHlY dGnJ nRnF} rS{sF(Ad Af Aj An Ao Ap Ar As aU Ba Bb Bc bG cD Cs Ct CU Cv Cw Cx cY Db De Dg Dl eC Ef Et Fb Fr Fw fY Gl gP HC Hf Hv Hx Ih Ii Ij Ik Il In Ir Is It Iz JF Jg Jh Jm Jn Jo jQ Js Jt Kc Ke Kj Kk Kl Kp Kr Lh Lj Lv Lw Ly Lz Ma Mb Md Me Mf Mg Mh Mj Mk Mn Mr Ms Mt Mv Mw Mx My Mz Na Nb Nc Ne Nf Ng Ni Nj Nk Nl Nq Nr Ns Nu Ny Oc Of Og Oi Ok Om oN Ou Oy Oz Pa Pb Pd Pe Ph Pi Pk Po qO Qt QU Qx Rg rU Ss Uf Uk Un Us Vo tF) sJ(Ad aF aL An aQ aR aU bG cD CU Cw cY Db dR Ef Fa Fb Fn Fw fY GL Gp hC Hv iA iB Ii Ik Il iO Is It Iv jF Jn Jo Jp jQ Jt Ke Kn Kp KR kS Lh Mb Md Me Mg Mh Mk Mr Ms Mt Mw Na Nb Nc Ne Nk Nl Nm Ns Nv Nw Ok ON Ou Ow Oy Oz Pa Pb Pc Pd PF Pg Pi qG qO qP Qt qU rA Rj rU rW Us Ut yD tF) sI(Ad aF aK aL An aU bG bO cB cD Cu Cw cY Db dR Fa Fb Fn Fw fY GL Gp hC iA Ih Ii iO Is It jF Jn jQ JR Ke Kn Kp KR Ks Ky Lh Li Lv Ly Md Mg Mh Mk Mn Ms Mt Na Nb Nc Ne Ng Nj Nk Nl Nm No Ns Oi Ok Om ON Ou Oy Oz Pa Pb Pc Pd PF Pg Pi qO qP Qt qU rC Rj rU Us) sH(aL An aR aU bG cD CU Cw cY Db dR Fa Fb Fr Fw fY Gp Hc Ii Ik Im Io Iq Is It Iv jF Jn Jo Jp jQ JR Ju Kf Kg Kn Kp Kr Ld Lh Ly Mb Md Me Mg Mh Mk Mn Ms Mt Mv Mw Na Nc Ne Nf Ni Nk Nl Nm No Nr Nv Nw Oi ON Ou Oy Oz Pa Pb Pc Pd Pe Pg Pi Pk qO qP qU rU Uh Us vP) Ic(Bb tS) Ri(fN Tr) ExsC VtiA} dX{iJ(aD Ao cC Dp Et Hb Hc Hf Hq Hx Id In Ip Jf Jh Jj Jo Jp Jt Ke Kf Kq Kx Ky Lz Ma Ml Mn Ms Mv Mx Mz Nc Nf Nw Ny On Ow Oz Pe Ph Pz Qa Qc Qd Ql Qm Qn Qu Qx Qy Ss Tz Ua Ue Uh Um Uv Vs Vt Vv tF) Kk(aG aM Ao aQ Ba bO bW cP Cq Cw dD dF eC Ef Et Fr Gp Hb Hw Il Im It Jl Jp Kd Kq Ky Ma Mn Mv Ng Nq Nw Oe Of Ok On Ow Po Ql Qm St Ul Vu) Hb(Aa aC aM AR Ax aY bA Bb bM bQ bV bZ cP Cs dD dL dN Ex Fa Fr gL hC Hx lO Jj Jl Jn Jp Kx Ld Mk Ml nW Po Qv Qx Tr Ur) Ok(aC aD Aj aN aW bE cP dD Dl Ez Fa GL gP Gz Ii iP Iz Kc Kg Ki Kj Kl Kn Kp Ks Ld Nd Nj nW Or Ph Qv Ss Vo Vt Vv) Kx(aG aI aL aM aN bR cM cN dD Et Fp Gd Ik Jl Jp Kc Ko Kp Ld Li Lv Me Mh Mn Nd Nw Oe On Pe Pz Qw Ur Vs) Ko(aC aM Ax bA Bb bQ bX cP Cs dD dN Fa Hf Ir Iv Jn Jp Kj Ld Lv Mk Ml Mn Mr oE Qv Qx Tn Ur Wm) Jp(aC eC Fn Fy hG iO iP lZ Ju Jv Kc Kg Ki Kj KQ Kr Ky Ld nW Or pF Ph Pi Pk Ql Qn) Kc(aM Ax bO cP Cs Et Fy Im Ir It Jl Lj Ml Mq On Ow Pf Po Qa Qb Qe Qt St Wm) Nw(aC dR eF Kn kQ Nd nW pF Ph Qx Rg Tn) Tn(bF bR Hq Iq Jl Qn St Uh Un) eC(Ik Jd Jy Kp Ql Qw Rb Ri Uf) Tv(dD Jl Ld Ow Po Qx St) aM(Dw eO Kp Ld Ou Ql) nW(Cv Et Id Jg Kn Pz) Fr(Ju Jv Qu Qw tF) On(Fa iP Kn Rg Vo) Uh(bA bV cN iO Qx) Mn(kQ Nd Ph Ql) Qx(aC Cw dD) Ld(Et St Wm) tF(cP hC iO) Po(Kp Ur) To(Ir St) Jl(Qw Ut) Rg(Bc Lh) CvKy DwbM EmKp FbdD GceF GndR MbgV JnaN QlaI NxeO VscP OziO} eO{aW(aD aM aP aS Aw bI bL bN bO bR bU bZ cF cG cT Cu Cv cW CX dB dE dF dG Di dJ dL dN eW Hx Ij Ir Is Jn Jp Jr Js Lh Lv Nb Ni Nu Nw Ny Of Og Ok On Pa Pe Po Qd Qe) Mn(aC aD aI aJ An Ar Aw aY bM bP bR bW Cs Cu cV cW dB dJ Et Fr Ip Iv Jp Jr Li Lj Lv Ly Mt Mw Nc Nd Ne Ni Nl Nt Nu Nw Oh Ok On Oy Pa Pe Pf Pz) Ok(aC aD aE

Mm Ms Mt Mw My Nb Nc Nd Ne Ng Nh Ni Nj Nk Nl Nr Of Og OK Oy Oz Pa Pf Po Pz Qa Qb Qd Qe Qv Qw Qy Qz Rf Ri Rm Tn TT tV tX
Us Tj) Zq(aC aM aO bC bR bS bW cB cF cM Dc dM eC eM FB fR hC hG iP iZ jT kC kE kF kG kI kK kN kO kP lW lX lY mE mF mH ml mM
mP mS mT mW mY mZ nA nB nC nD nF nH nl nJ nK nL nM nN nO nR nT nU oH oK oO Or Pk Rg Ss) Vh(aI aM aY bR bU cM Dd Dp Dr eD
Ef Ex gL Gn hC Hr Im Jd Je jF jG Ji jY lN Mn Mt Mw Nl Nn Om Or Pi Pk Qh qT qX rA Rg Sr Ut) Pj(hL iH Jd qB rN rQ rR rT rU rW sC sH tN
tO tQ tR tS tT tU tV tX uL vB vS vV wB wD wE wF wH wJ wK wL wQ yH tM tL xA) tV(Ad Bb Cw Di Ed Ic Ip Jg Jo Jt Kc Ky Kz Lh lK Ma
Mm Nm Ok Pz Qv Qw St Tr Tt Uf Um Vq Vt Tk) Mm(Jd Nd Nl sC tN tO tQ tR tS tT tU tX wB wC wD wE wF wG wH wJ wK wL wP wQ yD
yH zA Tk) qX(Dr Du Em Eq Fc Fi Gn Hl Ps Rt Ru Rv Si Uw Ux Uz Vb Vc Vj Vw Wd We Wg Zx) Ok(aC aO aR aW cK eO eP Fp Hx li ln Lv
Mb Ml Nc Nd Ne Nh Nj Nk Nl Oz vB) aC(Ad Ap Aw Bb Bc Bo cB Cu Cw Dg Di Dk Dl Dr DW Eo EW FR Gc) Jd(Cw Di FN Hu Ic Io Ip Iq It
Ki Lh Na Og Oi On Qv Ri Ub Um Tj) Nd(aA Cw Fr Jg Ji Jl Jp Lh Li Lx Ma Mn Mt No Nv Nw On Qa Qe) Tk(qO qP rW sC tS vP vV wH wL
yL) Dr(Ef jB Jg jM jP jT oD On Ut) Ji(aR dU DW eM Eo eP Ew fR) Ad(Aj aM aW bM Bo cF cN iH) Mn(DW EO EW Ne Nl) Nc(Fr Jg Lh Li
Lv Ma Nw On) bB(DW dX EO EW pH) Nl(Fr Im Jg Lh Li Ma On) jB(aH aX Cw Hb Mk No Oz) Bo(DW EO EW) Nj(Cw Fr Ma Nw On Qa)
No(dU eQ oD oT pK) Lx(Dw EO EW) On(Hf iH Ii Mb Ne) jD(Ic Ry Uw Vi Yi) jT(Gb Gh Hp Vc Wh) Jg(Aj aR iH Ne) Jj(dW EO Ew) Kx(dU
dX gV oD) tS(Bb Di Ic Vt) Gc(Ef jQ jR) Va(hV jI jK) tT(Bb Kf Lh) qY(Ps Vi Zx) oD(hB Ld Ut) pH(aH Cw Ko) Aw(bM Dl) Eo(Nw Oh)
Th(eQ oO) Lv(dW eW) sC(Vq Wn) rN(Ic Tt) CwoK DumE DwbM NmiH HbeP HfKq YijQ SirA ZxqT QaQb KodU LhvV NwdW UftO UwjO
VtuZ aHpl aMeW aWeO gWmS nNqU lXhB

Unconstrained panels with 2 analytes, where 1.0E-7 >= 'AUC p-value' > 1.0E-8. Contains 809 panels of 200,591 total panels evaluated. : Et(aA
aD aE aF aG aI aJ aK aL aM aN aP Ar aS aU aV aX aY aZ bA bB bC bF bG bH bI bJ bM bN bO bP bQ bS bU bV bW bX bZ cA cB cC cD cE
cF cG cH cI cL cM cN cO cP cR cT cU cV CW cX cY dA dB dC dE dF dH Di dJ dK dL dM dN DR EF Fa fR Fw GL GP hC Hq Hu Hv Hw Ib
Ih Ij Il Im lo Ip Iq Ir Is Iu iZ jB Je Jf Jh Ji Jk Jl Jm Jn Jp Jq Js Jt Ju Jv Kd Kk Kp kS Ky Ld Lh Lj Lw Ly Lz Ma Mc Md Mg Mi Mj Mk Mn Mp
Mq Mr Mu Mv Mx Mz Na Nf Nm Nn No Nq Ns Nt Nu Nv Nw Nx Ny Oe Oh Oi Om On Ou Ow Pb Pc Pd Pe Pg pI Pk Qc Qg Qh Ql Qn Qt Qx
Ra Rb Rc Rg Rh Rj rW Sr Ss tN To tS Tv Tz Ua Ub Uc Ud Ue Ug Uh Uk Um Un Uo Up Ur Ut Uu Uv Vh Vo Vt Wm tF) Vh(Aa aC aG aH aJ
aK aN AR aS aX bB bC bJ bL bM bN bO bW cD cF cI cP cQ cR cX cY dD dG dH Dk dM dN eF Fb Fp Fr gP Hp Hq hR Ij Il Iv iZ Jj jM Jn Js
jT jU Kp Li Lj lM Lx Lz Mb Ml Mm Mp Mq Mr Mv Mx Mz Nb Nc Ne Nf Ng Nh Ni Nk Ns nW Nx Ny OH Ok On Oy Oz Pb Pc Pe Pf Qa Qb
Qg Qm Qv Qy Rb Rf Rh Ri Rj Rm Rv St Tn To Ud Vb Vp Vq Wc We Zq) Jd(aM An aR bM Bo bU cF Db Dr Ez Hv Ik Im Ir Is Iv Jp Js Jv Ky
Ly Ml Mn Ms Mt Mw Nb Nc Nd Ne Ng Nh Ni Nk Nl Nq Ns Nt Nu Nv Nx Ny Of Oh Ok Oz Po Qa Qe Qm Qu Qw Qz Ra Rf Rg Ss Tt TV Uh
Uk Un Uo Uv Zq) Ok(aF aN bG bM BO bR bU bZ cB cJ cN cO cQ cW dE dG dI Eo Fr Hf Hr iH Ik Io It Iv Jj Jo Jr Li Lu Lx Lz Mf Mh Ms Mt
Mw My Na Nb Nf Ng Ni Nm Nq Nr Nx Of Og Oh Oi Pa Pd Pf Pg Pz Qa sC tS tX) Zq(aD aG aK aN aR aS aU aW aY aZ BB bL bM bO bV bX
cA cD cI cQ cR cW cY dD dH Dk Dr dU Fa Hc Hx iO jB jD jK Kj Lt Mt mU nW rY pF pI Ri Ut) Pj(Cw eZ fN fY hO jB pS qC qD qG qH qI
qO qZ rO rP rS rV sM uM uP uR uT uU uV vH vl vO vP vQ vT vU vW wC wG wP yD yK yL zG zH zI yE) aC(Ao AR Ba Bg cF Ch Co Cp Db
Dc De dN Em eO Ex Gd gV Jg On) Nc(Im Ji Jp Lx Mb Mm Mn Mt Nb Nd Nk No Nv Nx Pd Pf Po Qa Qe) Jg(aW Bo bR bU cB Db Fp Jj Lv
Mb Mh Ml Ms Ng Nh Nj Nk) Ad(aR Aw bA bU cB cK CT Db dF Di Mb Nd Nj rN rW) Nl(Ji Jp Lv Lx Mf Mt Mv Nb Nk Nn No Nv Nw Pd Qa
Qe) Cw(dU eQ fB IL oD oH oV pI qU vB vI Tj) Nd(Im Is Jt Mp Mv Mw Nn Nr Ny Pd Pf Po) tV(Ao Ap Hf II Ji Kf Kj Kl Li Lv Ms Ri) Mm(iH
Ne rW uP vQ vS zH zI tM tL xA) On(aO aR cK jB Lt Nh Qz rW tT We Tj) jB(cX Ex Hc Ji Ni Or Oy Qe Uh Th) Nj(aR Im Jl Jp Lh Li Lx Mt
Qe) Dr(Dk Fb Fr Ji Ko Mt Tn) Ne(Fr Ji Lh Li Lv Ma Nw) Ic(jl jV qC tN tX wG xA) Lh(Ms tN tO tS vP wG) Dg(AW Bo cF Di) jD(Gc nN Yg
Zw Xa) Fr(Hx Mb Nk Tj) Ut(Ps Ru Rv We) fR(cE dR Gp gW) Bb(aM fN tN) Ef(Bo Lt Rv) Ip(tS tT tX) Ji(bU gC We) Vt(tX vS xA) Vq(vP vV
tL) bB(dU eP gZ) Di(tO tT) Mb(Li Nw) Tn(eP Tj) Jp(aR fN) Kg(rN tS) Ko(EM) Kq(Fn Na) Uf(tN tS) Vi(jF jO) BoDl GcjU NmtT NqpH LvLi
MnNh MzfN YilM ZwjQ XajT KfrN KkdX NvoD WnwL aNeO aWeP bMdW eMhB Unconstrained panels with 2 analytes, where 1.0E-6 >= 'AUC p-value' > 1.0E-7. Contains 1,621 panels of 200,591 total panels evaluated. :
Vh(AD aE AF Aj aL An aO AP aQ As aU aV AW Ax aZ BA Bb bE bF bG bH bI Bn Bo bP bQ bS bV bX bZ cA cB cC cE cG CH cJ cK cl. cN
CO Cp Cq CS CT cU CV CW cZ dA DB DC DE dF DI dJ DK DL dR Ed Em Eq Fc Fd Fn Fy Gp Gz hA Ho Hu Hv Hw Hx Ic lh li iJ lk In lo lp
Iq Ir Is It Iu Jg Jh Jk Jl Jm JO Jp Jq Jr Jt Ju Kc Kk Kn Ko Kq Kz Ld Lh IK IL IO Lt Lu Lv Lw Ly Ma Mc Md Me Mf Mg Mh Mi Mj Mk Ms Mu
My Na Nd Nj Nm No Nq Nr Nt Nu Nv Nw nY Oe Of Og Oi oK Op Ow Pa Pd Pg Ph Pj Po Ps Pz Qc Qd Qe Ql Qn Qt Qu QW Qx Qz Ra Rc Rt
Ru Rx Ss Tv Tz Ua Ub Uc Ue Ug Uh Um Un Up Ur Us Ut Uu Va Vc Vo Vp Wm Ti) Zq(aD aE aF aH aI aJ aL An AP aQ As aV aX bA bE bF bH bI
bJ bN bP bQ bU bZ cC cE cG CH cJ cK cL cO cP Cq cS cU cV cX cZ dA DB dC dE dF dG dI dJ dK dN dR Ed EF Fd Fn fP Fr Gl gP Hq Hr iA
iJ Im lu lv lz JR Kd Ko kQ kS Ky Kz Lj Lu Lv Ly Mm Mn Mz Nb Ne Ni Nk Nl Ns Oh Om On OP oQ Ou oW pH Pi Qh Qm Qn qY Qz rA Rf
Rh Rj Rm Rz Uf Up Yk Tm Tl Tj tF) Et(Ad Af Aj Al An Ao As Aw Ax Ba Bb Bc bE Bg bL Bn Ch cJ Cp Cq Cs Ct Cu Cv Cx Dc DD De DG
Dk Dl Dp eC Ed Ez fB fP Fy Ha HB Hc hF hG Id iJ iO iP Jy Kc Ke Kf Kg Ki Kj Kl Kn Ko KQ kR Ks Kz nW nY Oa oE oF oH oN On Or pF Ph Pi
Pj Qm Qu rN sC St tO tQ TR tU Uf Ul uP vB Vp Vs Vu Vv yH zH) Ad(AF aG aH aJ aK Al AN AO aP aQ Ar aS aU aV AX aY aZ BB bC bE
bF bG bL Bn bP bQ bR bV bW bX cC cE cG cI cJ cL CP cQ cR Cs CV CW cY cZ Dd DE DG dH dI Dk DL dM dN DR eF fN Fr gL gP Hf Ji Jj
My Na qC qO tS) On(aF aH aN aW Bo bR bU cA cB cQ cR Db dG dJ dU Ex Fi Fn Fp Fw Gc gP Ho Hx iA Ic Iv Jj Lv Lx Mh Ml Ms My Nk
oD Of Op Ow Pk Ps Ql Qv Ra Rb Ri Rm Rv Rx Tn To TV tX Up Us Uv Vc Yl) Jg(aD aE aM aO aQ Ar Aw bB bM bX cF cJ cK cQ cR cT Cw
cZ Di eF fN FR Hf Hx Ic li In Ip Iu Iv jB Ji Lh Li Lj Lu Lx Me Mf Mq Mt My Na Nb Nw Nx Of Oi Oz Pd Pf Pj Po Pz Qa Qe) Cw(bM cF DR
eD eF Fw gL gP hB hC hF hG hL hO iA Ic iH iJ iO iP ls iZ jM jY Ko Kq kR Mm Nf Nl nT nW nY oE oN Ou OW pF pK qS sK Tn tS TT Un
Ur yH tF) tV(Aw Bo Dc Dd Dg Dk Fw Fy Hq Hu Hx iH ti Io It Jn Jp Jr Ke Kg Kp Mf Mg Ml Mp Mz Na Ne Nq Nt Nw Nx Of Om Pc Pd Qc Qd
Ql Qu Rh rW Uk Up Uv Vo VP) Nl(aA Fp Ik In Iq Is Iv Jj Jl Jt Lj Mb Mg Mh Ml Mp Mq Mu Mw Nd Ne Nh Ni Nm Nq Nr Nx Ny Oh Om Pa
Pf Po Qd) Pj(aW cN Db cT Fb gP hP jD kQ nW oK pF pY qA qP Qv sK sO uG uI uN uO uW uX uY uZ vC yJ zA tF) Mm(Kx Mb Nh Nj Ow
Qv rN rQ sM sO Tn uL uR uT uU vB vH vl vO vP vT vU vV vW yK yL zG yE) Nj(aA Ar Bb Bo Db Dg Di Dk Fp Is Mn Mp Mu Mv Mw Nb
Nn No Nr Nv Nx Pd Pf Po) Dg(aD Aj aK aM aN aR aU aV bA bB bM Bn bR bU cB cK cN cQ cT cY Db iH) Nc(Fp Ik In Jj Jt Mf Mg Mh Ml

Figure 6 Continued

Mp Mq Mr Mu Mv Mw Mz Ni Nm Nn Nr Ny Om) Nd(Aa Dk Fp Ih In Jj Jq Lj Lv Lw Me Mf Mr Mu Mx Mz Nm Og Oh Om Pe Qd) jB(bB cG cO Dc Dl dN Hu Hx Io It Jt Ko Kx Kz mE Nk nN Ny Qc Qm) aC(Af Al aW bC bF bM Bn bQ bR bU cE cG CT Cv Dd dF Ji Lh) Ic(aM aR cN eD fN Fr hR iC jG jL jM jR Kq qB rW vS tF) Lh(aR FN jD Mb Nk tQ tR tX uP vB wF wL yD zH xA Tj) Ne(Im Jj Jp Lx Mf Mt Mv Nb Nn No Nv Ny Pd Po Qa Qe) Dr(bB Bg cB cG Ch hC iB Iz Kq Mn Oh Om Ow qT Qu) Fr(Aw Bo cF fR Ik Iv Ji Jj Lv Ml Ms My Nh sC vP) Ef(Di Eq Fc Fi fR Gn Lp Op Ps Ru Vb Vc Zw Zx) Gc(bQ cE dD Dk eC eF fR hC iZ mE qX Ut tF) Ji(cK dX Em eW fB Mb Ml Ms Nh oV Oz pl Qa) Ut(Fc Lt Rt Vi Vz Wc Wd Wf Wg Wh) cF(aM Ap AW BB bF Bo Dl iH) Di(Ap cB eD hX Is IL qY tN uZ) Kq(aR aW Db iH In Io It Nt Nu) qX(Fd Gb Gh Uy Va Vi Wc Wf Wh) Bo(Ap Aw Ba Bb Ct cY Of pH) Jp(Lv Mb uP uZ vS vV zH tL) Tk(qH ql rU tX uM vS zG xA) bM(Aa aW Bb Bn cB Cp De Eo) iH(Aa Ap aR bU eD Jt qW rC) Vt(rP rV sC tN tR tT tL) qU(kO mW mY nD nJ nL oO) Nw(cO Fp Ik Lv Ml Nk) cB(aD aR aW bQ eO rW) pH(Du Nu Uh Um Uy Vj) Th(Ir kl oD oP oQ) Mt(Eo Jj Lj Lv Ms) Nh(Li Lv Lx Ma Pf) Qa(Mb Ms Nk Rx We) eP(hB hC Kc Ko nW) fR(aU bB bF cY hB) Bb(bA bB tO tX) Tn(dX It My Qz) Kf(rW tO tS tM) Op(eM mE Pk Ru) iT(Ap Kg Uf Vq) Aw(aM Ap aR) Lx(Hx Li Lv) Tt(tS Uh vS) Wh(jD IK rA) Ow(dX Na nT) Pf(Dw gV Nf) tX(Ao Ms Pd) rW(Mz Ri Tr) oD(Cu Mq oQ) Cp(aM Dl) Ex(Dk hL) Gb(jU IM) Nm(tN tS) Ma(Fp Lv) Hb(dX eM) Yi(jR oO) Jj(Dw Ik) Ko(Lt Vw) Ky(sC uP) Li(Hx Nk) Wn(qO qP) Oh(eO Lt) Un(fN tL) Uw(jF qY) Vq(yK yL) aR(Io Is) aW(Cu Dl) bB(eM pK) dU(aH Mv) eD(Fi nN) hB(nC nH) jT(Va We) rS(sH sJ) nW(Du gC) EoaM NooW HojR InPd IptN YglM SiqT SfqW ZxrA WcrB KetS KjrN KpdX PsjD KxoV UfxA aDgV

Unconstrained panels with 2 analytes, where 1.0E-5 >= 'AUC p-value' > 1.0E-6. Contains 3,192 panels of 200,591 total panels evaluated. : On(AD aE Af aG aI AJ aK AL aM An aP aQ Ar AS aU aV Aw aX aY aZ BA BB BC bE bF BG bH bI bJ bL bM BN bO bP bQ bS bV bW bX bZ cC cD cE cF cG CH cI cJ cL cM cN CO cP cS CT CU cV CW cX cY cZ dA dB dC DD DE dF dH DI DK dL dM dN Dp dR Ed EF Em Eq Fc Fd fN fR Gb GL Gp gZ HA Hb Hc HL hO Hp Hq Hr Hv Hw Ib Id Ik In Ip Iq Is It Iu jD Je Jg Ji Jk jM Jo Jr Js Ju Jv Jy Ki Kk Kn Kp Kr Ks Kx Ky Kz Ld Lh Li Lj lL Lp Lu Me Mf Mp Mt Mv Na Nb Nf Ng nK Nq Nr Nw Oa Og Oi oK Om Oz Pf Pg pH Pj Po Pz Qa Qc Qd Qe QG Qh Qm Qn qO Qt Qu Qw Qx Qy qZ Rc Rf Rg Rh Rj Rt Ru Ry Rz sC Sf Sh Si Sr Ss St tO Tr tS Tt Tz Ua Ub Uc Ud Ue Uf Uh Um Un Uo Ur Ut Uw Ux Uy Uz Va Vb vH Vi Vo VP Vt Vw Vz Wb Wc Wd Wf Wg Wh Yd Yg Zw Zx Ye Tm Xa Wm Ti Th) Zq(Af Aj Al Ar Aw Ax Ba Bc BG Bn cN Co Cp Cs CT Cu Cv Cw Cx Dd De Dg Di DL Dp Du Em Ex Ez fA Fc Fi Fw Gb GC Gd Gh gL Gp Gz Ha HB HF Hl Ho Hp Hu Hv Hw Ib Ic Id IH Ii Ij Ik Il In Io Ip Iq Ir Is It Je Jf Jg Ji Jj Jk Jl Jm Jn Jo Jp Jq Jt Ju Jv Jy Ke Kf Kg Ki Kk Kl Kn Kp Kq KR Ks Kx Ld Lh Li lM Lp Lw Lx Lz Ma Mb Mc Md Me Mg Mh Mi Mj Mk Ml Mp Mq Mr Ms Mu Mv Mw Mx My Na Nc Nd Nf Ng Nj Nn No Nq Nr Nu Nw Nx Ny Oa OE OF Og Oi Ok oN oT Ow Oy Oz Pa Pb Pc Pe Pf Pg Ph Pj pK Po Ps Pz Qa Qb Qc Qe Ql Qt Qw Rc Rt Ru Rv Rx Ry Sf Sh Sj Sr To Tt Ua Ue Uh Ul Um Uo Us Uy Vb Vc Vi Vp Vq Vs Vu Wb Wf Yd Yg Yh Yl Zx Ye Xa Wm) Jg(aA Ad AF aG aH aJ aK AL AN AP aS aU aV AX aY BA BC bE Bg bH bJ bL BN bO bP bQ bS bV bW bZ cA cC cD cE cG CH cI cL cM cN cO cP Cq CS Ct cU CV cW CX cY dA dB DC dD DE dF DG dH dI dJ DK dL dM dN dR Eq Fn Gc gL gP Hq Hr Hu Hv Hw iA Ih Ij Ik Il Im Io Iq Ir Is It Jh Jk Jl Jm Jn Jo Jp Jq Jr Js Jt Jv Kx Ky Kz Lw Ly Lz Ma Mc Md Mg Mi Mj Mk Mm Mn Mp Mr Mu Mv Mx Mz Nf Ni Nm Nn No Nq Nr Ns Nt Nu Nv Ny Oe Og Oh Om Or Ou Ow Pa Pb Pc Pe Pg Pk Qb Qc Qd Qv Qz tS tT tX Uu Tj) Cw(aD aK aM aR aU aV aW Bo cK Dg Di Dk Dl Dp eC Ed Ef Fb Fn fP FR Gl Gp gZ HA Hb Id In Iu Je Jf jG Ji Jj JO Jp jR JV Kc Ke Kf Kp kQ kS Kx Ky Ld lK lO Lv lX Mb Mt My NC Ne Nh Nn nO Nw oF Oh Or oT Pi Pk pS Qa qC Qe Qu Qv QW Qx Qz Ra Rg Ri rN rX tN Tr Tv tX Ud Ue Uf Uh UM uO Up Uv uZ Vo Vp VS wQ zG zH tL xA Wm) Jd(aE Af aG aJ aK AL aQ As aV AW AX Ba BB Bc bG BN bO bP bV cD CH cJ cL cM Co Cp cQ CS CT CV CX cY dB DC Dd Dg dJ Dk dN Ef Fy Gl Hb Hc Hr Ib Id Iz jG jV Jy Kd Kl Ko Ks Ld Lp Lt Mv nF Nj Nm Nn No Or Ph Qb Rb Rh Rj Rm Rt Ru sC To Tz Uc Ul Ux Uz Vi Vs Vt Vu Vv Wc Wd We Wf Wh Ye Th) Ad(aD aE aI aL Ap As Ba Bc Bg bH bI bJ bN bO bS bZ cA cD CH cM CO Cq cS CU CX dA dB DC dD dJ dK eT Ex eZ Fn fP fR Fw fY Gp gW hB hL hO hP iA Ic Ii In Is It Iu iZ Jk Jo kQ Kx Ky Lv Lx Lz Ml Mm Mt Mu Nc Ne Ng Nl Nt Nu NW Of Oi Ow pF Pj pY qA qB qD qP Qv Qz tO tT Uh Ur Tj) Vh(aA Al Ao Bc Bg Cu Cx Dg Du Ez Fa Fi fP fR Fw Gb Gc Gd Gh Gl Ha HB Hc HF Hl iA IB Id iH iP Iz jE Jf jL jQ jR JV Jy Kd Ke Kf Kg Ki Kj Kl kQ KR KS Kx Ky Lp Oa oE oF oN Ou qY Ry Rz Sf Sh Si Sj Tr Tt Uf Uk Ul Uo Ux Uy Uz Va Vs Vv Vw Yd Yg Yl Zw Zx Ye Tm Tl Xa Tj Yf) tV(Af aU Bc bG bZ cF cI cS Cu Dl Ez Fb fP Fr gW Hb Hc Hr Hv Hw Ib Ih Im Iq Ir Is Iu Iv Je Jf Jh Jj Jk Jl Jm Jq Js Jv Jy Kd Ki Kn Kq Lj Ly Me Mr Mu Mv Ng Nk Nn Nu Oh Oy Pb Pi Pk Po Qa Qb Qe Qg Qm qO qP Qx Rb Rg Rm sC sJ Ss Tv Tz Ua Ub Ue Ug Uh Ul Un Uo uP Ur Ut Vu vV wL tL Wm) Ji(aN aQ Ar aU aV AW bA bB bC bJ bM bN Bo bR bX cB cF Ch cJ cM cP cQ cR CT cW cY cZ Db dE Di Dk Ef eO eQ fA fN Fp Gc gV gZ Hf iH Ik In Ip It Iu Iv Jp Lh Li Lt Lu Lv Lx Mt Nb Nf Nj Nk oT pH pK Po Ps Qc Ri Rt Ru sC Sf Tn tS TT tX Ux Va Vi Vw Wd Wf Wh Zx Th) Ok(aA Af Al An Ao Ap As Aw Ax Ba Bb Bc Bg Bn bV Ch Co Cp Cq Cs Ct Cu Cv Cx Dc Dd Dg Di Dl dN dR dU Dw eM Fb Fn fP gC GL Gp Hb iP Kd Kf Kq Kr Ks Ky Kz Ld Mm oK Or Ou Ow Pj Pk Qv Qz Ra Rb Rg Rm sK tN tO tR uN uP uY vC vI vP vQ wC wF wG wJ wQ yD yH yK tL Wm tF) Fr(aK aO aQ aR aU aV aW bM bR bU cB cK cT cY Dg Di Dp Fi Fn Fp Gc Hf Hq Hr Hu Hv iH Ii In Ip Iq Is It Iu Jh Jk Jl Jm Jn Jo Jp Jq Jr Jt Lh Li Lj Lp Lt Lx Me Mf Mh Mm Mt Mv Mw Nb Nf Ng Nm nN Nq Nr Nt Nw Nx Of Og Oi Om Oy Oz Pd Pf Pj Po Qa Qe Qz tS tT) Dg(aE AF aG aH Al An aO aQ Ar AS AX Bb Bc bE bF bG bI bL bN bO bQ bX cA cD cE cG Ch cI cJ cL cM CP Cq cR CS Ct Cu CV cW Cx cZ dB Dc DD De dF dG dI Dk Dl dM dN dR EF Ex fR gP Hf jB Kx Mb Nd Or Qv) Pj(aM aN aR bA bB bC Bo bQ cM cP cQ cR cT cV Di Dk dN dR EF gL hB hC HF hG hR hV hX iA iJ iO iP Iq iZ Jp jQ jR jY Kq Kr kS Kx Lh Mt Na nY oE oF oH oN Ou Ow qQ Qt qY rB rC sF Tn Un vA) Tn(Bg Ex Fn Fp Gc Ha Hf Hq Hr Hv Hx Ic Im Io Iq Ir Iu Iv Ju Jv Lh Lw Lx Mi Mj Ms Na Nb Nc Ng Nk Nt Nu Nv Pd Pz Qg Qh Ql Qu Qw Qx Ra Rf Rg Ri Rm Ss Ua Ue Uf Uh Un Us Uv Vp Vt Wm) jB(Aa Af aG aI bI bU cF Cs Dd dF dM Fa Gh hB hC Hw lJ Ik Im In Ij Jn Jo Jq Jy kE Mm Mq Mr Ms Na Nb Nc Ne Nf Nl Nm Nn Nr Nt Nv nW Nx oD Ow Pa Pb Pc PH Qa Qd Qg Qn Sr) Lh(aW bU cK Fp Hf hL Hv Hx Ic iH Ii In Iv Jj Kx Ky Lj Lv Lx Mh Ml Mt Nb Nh Po pS Qa Ql Qv Qz Ri sC Ss Tt tU Uc uL uM Ur uZ vC vH vQ wB wC wD wE wH wJ wK wP wQ yK zA tL) Nj(Aa aM Ap aW Ba bB bM bQ bU cB cF cG cN cR cT Cu Dc Dl dN Dr Ex Ih In Ip Iq Iv Jq Jt Kq Lj Lv Lz Md Mf Mh Ml Mq Mx Mz Nc Nd Ne Nh Ni Nk Nl Nm Nt Ny Oh Om Pa Pc Qd) Nl(Aa Hq Hu Hv Hx Ih Ii Ij Il Ip It Jh Jk Jm Jn Jo Jq Jr Lu Lw Ly Lz Mc Md Me Mi Mj Mk Mr Ms Mx My Mz Na Nc Nf Ng Ns Nt Nu Oe Of Og Oi Oy Oz Pb Pc Pe Pg Pz Qb rW) Et(Ap Co EM eO eP eQ Ex fN GC Gz hL hO hP Iz jD oD oV pH qB qD qG qI qO rQ rU vH vP Vq vV wB wC wD wE wF wG wH wJ wK wL wP wQ yD zI tL xA Tk Ti Th) Nd(Ap aR Bb Bo Di Ii Ij Il Io Ip Iq Ir It Iv Jh Jk Jm Jn Jo Jr Js Kq Ly Lz Mb Md Mg Mh Mi Mj Mk Ml Mq Ms Na Nb Nc Ng Nh Nk Nq Ns Nt Nx Of Oz Pa Pc Pz Qb) aC(Aa aD aF AJ aM An aP As aV AX aY aZ bA bB bE bH bV bZ cA cI cJ cL cN cP Cq cR CS cU cV cW Cx cZ dB dC dJ dX Ef Gn Hp Im Is Jp Jt Mm Nw Pd Wc) Mm(aR aW Db Fb fN Fp Hb Hf hO Ic Ik Ki Kq Li Lv Ml Or Ou pS Qa qI qO Ri rO rP rR rS rU rV sH sJ sK Tt uG Uh uM UN uO uV uX uY uZ vA vC yJ Wn) Nc(aA Hq Hu Hx Ih Il Ip Iq Is It Iv Jh Jk Jl Jo Jq Lj Lu Lw Lz Me Mj Mk Ms Mx Na Ne Ng Nh Nq Ns Nt Nu Of Og Oh Oi Oz Pa Pb Pc Pe Pg Pz Qb Qd) Ef(Aj aM cN Du Em Fd Gb Gh Hl Ho Hp Rt Ry Rz Sf Sh Si Sj Uw Ux Uy Uz Va Vi Vj Vw Vz Wb Wc Wd We Wf Wg Wh Yd Yg Yk Yl Ye Tm Tl Xa Yf) Ne(aA Fp Ih Ik Il In Ip Iq Is It Iv Jh Jk Jl Jq Jt Lj Lw Mb Mg Mh Ml Mp Mq Mu Mw Mx Mz Na Nh Nk Nm Nq Nr Nt Nx Og Oh Om Pa Pf Qd) Kq(aE Aj aK aL aM An aO bG Bo cB cQ cW Di dJ dR eF Ex Fa gP Iq Ir Iu Iv Kd Ki Kr Kx Lt Ly Mb Ms My Nb Nk Nv Pg Ql Qz Rm uZ Tj Th) Jp(Ar

Figure 6 Continued bR cJ cT Eo Fn Fp Ic iH Ik jD Kx Ky Lx Mt Nh Nk Ow Pk Po qQ QZ rB Rm rW sK Ss tS Tt uM uN uY vB vH vP wG yH zG) Gc(aM aU aW
bB Bg cB cF Ch cN cY dF dR eM Fb iJ Im jF jT 1M Mg Mt Mv mY nW oH Om Pi Pk Qh Qy Qz rA Ss St Wm) Nw(aR cB Dw eP EW fN Hx
iH Im In Ip Iv Li Lj Lx Me Mf Mg Mh Ms Mt Nb Nh Nm Nr Pd Pf Po Qa Qe rW tX uP tL) Lx(Hr Hv Ik Il In Iq Iv Jh Jj Jt Ma Mb Ml Mn Ms
Mt My Nb Nk Nr Nx Of Og Om Oz Pc Pd Qa Qb Qc Qe Tt) Tt(Aj Ar Bo cF Di Dr Hb Im Iq Is Je Jj Kx Kz Na Oh Op Or Ou Ow QA Qe Qv Ra
sC Sr tX Un Ur) Ut(DU Fd Fi Gb Gh Gn Hl Ho Hp Lp Op Ri Rx Ry Rz Sf Sh Si Ux Uy Uz Vc Wb Yl Zx Tm Tl Xa Ti) Ic(Di fY gW hL iB Iq iZ
jH jP jT jU jY kS Ky IL IN Mw oF Qa qD sC Uh Un uP uV wF wJ yD zA) Dr(Ba Co dF eC fB Ij Kf Kl Kx lK Ma mT Mv Nn nW Nx Or Qc Qh
Qz rA Rc Rz Ss Uc Uh Ux We) Vt(qH ql rN rQ rR rS rT rW sK sM sO tO tQ tU uM uW vH vV wC wD wF wG yH zA zI Tk Wn) Nh(Eo Fp Ih
Im In Jj Jl Lj Mb Mf Ml Mt Mu Mx Na Nb Nm Nn No Nv Nx Om Pd Po Qa Qe) cB(aK aM Ap Ar aU aV Aw bA BB bF Bo cF cI cK cM cN Cp
cT cY Dc dD Dk Dl fR Is) Di(aM aR aU aV Aw Ba cF cY Db Dl gW hR hW iH Io jR jY Ky lK Ow sC vP yH) Qa(Fi Fp Hr Hx In It Li Lt Lv
Mf Ml Mt My Nb Nf Nt Nx Of Op Oy Pd Rm Tj) Ko(aM aR aW Db dX Fd fR Gb Gd iH Lp Na oT Ps Ru Rv Sf Vi Vj We Wf Wh Ye) cF(aD
aR BA Bc Bg bM Bn bQ cE cG Ch cI Cp Cq cT Cu cW Dk dN tN tS) Bo(aK aM aQ aR aU aV aW Bg bU Db Dk dR fP fR gV Is Mg Nm nN Ou
Ow) iH(bB cM cQ dB dD Dl iJ jV Kf lL lX qT qU qV qX qY rA rX rY Ue tF) bM(Af BA Bc bF Bg bQ bR cE Ch Co Ct Cu Cv Dc Dk eO EW
gV) Bb(aR AW Ba bR bU cK cN cT dF dN eZ qA qD qO rC rW tR yH) aR(Ap bB bF bU Im Jh Jt Mt Ou qO qP rW sC tO tR tT tX Un) Li(Fp
Hv Im In Iv Jj Lw Mh Ml Ms Mt My Nf Nm Pd Qc Qe) Lv(aA Fp Jr Lj Mn Mz Nk Nn Nr Nu Nv Ny Oh Pa Pf Po) Mb(AA Ap Dk eW gV Jj Jl
Ma Mn Mt No Nv Op Po Qe) nN(cJ jO kC kF kl lM mE mP mS Mt mZ nl oH ql qV qY rA) Uf(Fn Na Qv Qz sC tQ tR tX vB vS wH wJ wP wQ
tM) Dk(aV AW bU cJ Dl Gn Is Lp Lt Na tT Zx Ye) Kf(aM iA Na oK ql sC tN tR uZ wF wK wQ zA xA) qU(kC kF kG mE mF mZ nB nH nM
nR oP oQ Vq Tk) pH(Ax Eq Ex Gh Kg Kx Lj Qm Qu To Ub Yj Th) Fp(Jh Jt Mn Mt Nf Nm Nn Nt Nv Of Om Pd) We(aM bR Dc Im Lj Mt nW
Oh Om Ow Qm Uh) Vq(jD jY ql qY rN rW sO tX uM uZ vT zG) fR(aK aN aV aW bA bE bQ cG cJ Dl Is Ow) Ap(aD Aj aM aW bA bB Bn cT
hO rN sC) Aw(aK aU aV aW Ba bB bU cK cN cY Db) Mn(Iv Lp Me Mf Ml Mt Pd Pf Po Ri Th) Ow(Db Dd Em eP gV Hf Lt Nu Ye Th) aM(Ba
Bg Cu Dl DW cO Fb Op Uh) Om(Lt Ml Ru Rv tT Uy Vb Vc Wf) Un(bR cV Fn Iv jY Nu Qz uN uZ) hB(aW dN Em eQ gC oD oV oW pl) Mt(li
In Ma Ml My Pf Po Qe) tS(Ao Dd Dl Kj Ky Ri Tr Wn) oD(aH dF Fa Gh Oz Qe Vz Zx) Kx(eQ fA gZ mF oT oW Ti) Tk(jQ rN tN tR ul vB vI)
tT(li Jo Jt Ma Ms uP wL) Ip(hL tQ tR uP wB yH) Op(jH nJ Pi qX qY Us) fP(sC uM vS wE wF wL) nK(Ir Nr Nv Ny Oh qZ) jD(Hp Iq Mz Si Vz
Zx) Cu(aF aU aV cJ cK) Ex(aW hO uZ Ye xA) Ma(Iv Mf Nb Nk tX) In(Ik Ir Iv Nr Po) Wh(bR eD Jn Qm qY) Qv(sC Ue uN uZ vS) eM(Qm Si
Yd Yi Xa) qX(Lp Sf Sj Yd Yf) Dl(bR bU cE cJ) Mz(hL hP qC qD) Oh(Fc SF Yl Zx) Pe(DW eO Ew) aH(fB gZ oV pK) aW(Ba bU Cp cW)
tX(Kg Ky Na Nm) hB(nB nL nT pK) No(gZ oV pl) Ml(Nv Ny Qc) Tr(vS wJ yH) Si(gW jT lM) Va(iB jQ jR) Pf(dW Hr My) dU(Kz Qn Uh)
dX(aN bA Ou) eO(aD cW dB) eP(iJ Kk Ou) Ba(Ar Ct) Po(Il Og) Ti(Ir rW) Th(gZ kC) Ms(uP zH) Nk(Jl Qe) Hf(gV sH) Is(aN bR) Jj(eW Nr)
Xa(lK mY) Ry(jQ lM) Ri(rN sC) Vc(gL jP) fN(Je Jt) gW(Ho nD) rS(Mg sI) pK(bQ Nq) DumF EoaD Tjlr FiqY FnUh GhfA NmrN HxJl IzZx
YimE SfnW QxgV KgtR PsOy RvjT RuNx OgPd UwrA VjiJ bRcE cJoQ wLsC qZkN Unconstrained panels with 2 analytes, where 1.0E-4 >= 'AUC p-value' > 1.0E-5. Contains 6,708 panels of 200,591 total panels evaluated. :
Kq(aC aD AF aG aH al aJ AI aN Ao AP aQ Ar AS aU aV Aw AX aY aZ BA BB BC bE bF Bg bH bI bJ bL bM BN bO bP bQ bR bS bU bV
bW bX bZ cA cC cD cE cF cG CH cI cJ cK cL cM cN CO CP Cq cR CS CT CU CV CX cY cZ dA dB DC DD DE dF DG dH dI DK DL dM dN
Dp Ed Ef Em Fb Fc Fd Fi FP FR Fw gC Gd Gl Gp Gz Ha Hb HC hF Ho Hq Hr Hu Hv Hw Hx iA Ih Ii Ij Ik Il Im IP Is Iz jB Je Jg Jh Jj Jk Jl JM
Jn Jp Jq Jr Js Jt Ju Jv Kc Kf Kg Kj Kk Kl Kn Ko Kp Ks Ky Kz Ld Lh Li Lj Lp Lu Lv Lw Ma Mc Md ME Mf Mg Mh Mi Mj Mk Ml Mn Mp Mq
Mr Mt Mu Mv Mw Mx Mz Nc Ne Ng Nh Ni Nl Nm Nn No Nq Nr Ns Nw Nx Ny Oa oD Oe OF Og OH Oi oK Om ON Op Or Ou Ow Oy Oz Pa
Pb Pc Pd Pe pF PH Pi Pk Qd Qm Qn Qt Qv Qw Ra Rb Rf Ri Rx sC Sf Ss tS Tt Ue Uh Un Uo Ur Us vB Vp Yl Zx Ye Tk Ti tF) Cw(AJ AN Ap
aQ Ar Aw BA Bb bF Bg Bn bU cB Ch cJ cM cN CP CT Cu Cv cY Dc dI dJ dN Em cT Ex EZ Fa fN FY GC Gn gW Hc Hf hP Hq HR Hu HV
Hw HX IB iC Ii Ij Ik Il Im Io Ip Iq Ir It Iv Iz jD jE jF JH jl JK JL Jm Jn jP JQ Jr Js JT JU Jy Kd Kg Ki Kj Kk Kl Kn Kr Ks Kz Lh Li Lj lM IN Lu
Lw Lx Lz Ma Mc Md Me Mf Mg Mh Mi Mj Mk Ml Mn Mp Mq Mr MS Mu Mv MW Mx Mz Na Nb nF Ng Ni Nk Nm No Nr Ns Nu Nv Nx Ny
Oa Oe Of Og Oi Om Op Oy Oz Pa Pb Pc Pd Pe Pf Pg Ph Po pY Pz qA Qb Qc Qd Qg Qh ql Ql Qm Qn qO qQ QT qV qX QY qZ rA RB RC Rf
Rh Rj Rm rP rR rS rU rW sC sM sO Sr Ss St TO tQ tR Tz Ua Ub Uc UG ul Uk UL uN Uo uP uR Us UT UU uV uW UX uY vA Vb vC vH Vi
vO vP VQ VT VU VV Vw wC We wF wH wJ wK wL wP yD yJ yK yL zl yE tM Ti Th) Lh(aA AD aF aN aO aQ Ar Aw bA bB bM Bn Bo bR
bS bX cB cE cF cG cJ cN cQ cS cT DE Di Dk Dp Dr Ed eF EO Fw HA hO hP Hq Hr Hu Hw iA Ib Ih Ik Il Im Io Ip Iq Ir Is It Iu Je Jf jG Jh JK Jl
jM JO Jp Jr Js Jt Ju JV JY Kd Kk Ko Kp Kr Kz Ld Li lL Lu Lw Ly Lz Ma Mc Md Me Mf Mg Mi Mj Mk Mm Mn Mp Mq Mr Mu Mv Mw Mx
My Mz Na Nf Ng nK Nm Nn No Nq Nr Ns Nt Nu Nv Nw Nx Ny Oe Ot Og OH Oi oK Om Ou Ow Oy Oz Pa Pb Pc Pd Pe Pf Pg Pk Pz Qb QC
QD Qe Qg Qh qO Qt Qu Qw Qx QY qZ Ra Rb Rc Rf Rg Rh Rj Rm rN rW sK sM sO Sr St To Tr Tv Tz Ua Ub Uc Ud Uf UG Uh ul Uk UN UO
Up uR Us UT UU UV uW uX uY vA vl Vo Vp vS vT vU vW We yH yJ yL zG zl yE tM Wm Th tF) Ji(aA aD aE AF aG aH aI AJ aK AL aM
An AO AP AS AX aY aZ Ba Bb Bc bE bF BG bH bI bL Bn bO bP bQ bS bV bW bZ cA cC cD cE cG cH cI cL cN CO Cp Cq CS CU CV CX
dA dB DC DD De dF DG dH dI dJ dK DL dM dN dR eF Ex Fc Fd Fi Fn fP Fw Gb Gd GL Gn gP Hr Hu Hx iA Ic Ih Ii Ij Il Im Io Ir Is Je Jh Jj Jl
Jm Jq Jr Js Jt Kd Kk Kp Kx Ky Ld Lj Lp Ly Lz Ma Mc Me Mf Mg Mh Mi Mn Mq Mu Mw Mx My Na nK Nm Nn No Nq Nr Nt Nu Nw Nx oD
Oe Og Oh Op OW Pa Pc Pd Pc Pf Pg Pj Qb Qc Qd Qu Qv Qy Qz Rg Rm Rv rW Rx Rz Ss tN TO tR Uf Un uP Uw Uy Uz Vb Vc Vj Wb Wc Wg
Ye Tm TL Wm Tj Ti Yf) Tn(Ad AF Aj AL aM An aO Ap AR AS aW Aw Bb BC bG bL Bn Bo bR bU cB cF cI cN Co Cq Cs Ct Cu Cv cW Cx
Db Dc DE Dg Di Dk Dp Ed eM Ez Fa Fb FR Fw Gp Gz Hb Hu Hw Ib Id Ih Ii Ij Ik Il In Ip Is Je Jf Jg Jh Jj Jk Jl Jm Jn Jo Jp Jq Jr Js Jt Jy Kd Kf
Ki Kk Kn Ko Kp Kx Ky Kz Li Lj Lu Lv Ly Lz Ma Mb Mc Md Me Mf Mg Mh Mk Ml Mn Mp Mq Mr Mt Mu Mv Mw Mx Mz Nd Ne Nf Nh Ni
Nj Nl Nm Nn No Nq Nr Ns Nw Nx Ny Oa Oe Of Og Oh Oi Om Op Or Ou Ow Oy Oz Pa Pb Pc Pe Pf Pg Pk Po Qa Qb Qc Qd Qe Qm Qn Qt Qv
Qy Rb Rc Rh Rj Sr St To Tr Tt Tv Tz Ub Uc Ud Ug Uk Ul Um Uo Up Ur Ut Uu Uy Vc Vo Vq Vs Vv Zq Ti) Pj(aC aD aE aF aG aH al aJ aK aL
aO AP aQ Ar aS aU aV Aw aX aY aZ Ba Bb Bc bE bF bG bH bI bJ bL bM Bn bO bP bR bS bU bV bW bX bZ cA cB cC cD cE cF cG CH cI cJ
cK cL cO Cp cS Ct cU Cv cW cX cY cZ dA dB DC dD DE dF DG dH dI dJ dK DL dM eC eD Fa Fn FP Gl gV gW hA hW iB IC Ih Im In Is Iu
jE jF jG jH jI Jj jL jM jO jP jT jU jV Kc Kf Kk Kl Kn Kp kR Ks Ky Kz IL IM IN IO Lv Lw Ly Ma Mb Md Mg Mk Mm Mn Mq Ms Mu Mv Mw
Nn No Nr Nt Nu Nw Of Og Oh Oi Om Or Oy Pd Pf Pk Po Qa Qe qT QU qX Qy Qz rA Rg Ri rX rY rZ sI sJ Sr Ss To Tt Uh Tk Th) Jp(AD aF
aN aO aQ aS AW bA bB bG bM Bn Bo bU cB cF cK cN cQ cR Ct Db dD DE Di Dk Dl Dp Dr ED EF Ex Ez Fa Fb fR Fw Gc Gp hA Hc Hf hP
HX Ib Id Im Is Iv Je jM jO Jr Ju Jv JY Kd Kf Ki Kk Kp Kr Kz Ld Li Lj lL Ma Me Mf Mg Mh Ml Ms Mv Mx Nb Nm Nr Nw Nx Of Om On Or
Ou Pd Pf Ph Pi pS Qa qD Qe qG ql Ql Qm Qn qO qP QT Qv qW qX QY Ra Rc Rf Rg Rh Ri Rj sC sJ sO Sr tN tO TR tT tU tX Ua Ub Ue Uf Uh
ul uL Un UO UR UT uU UV vC vl vO vQ vT vU vW wB wF wL yD yJ yK yL zA zl yE tM xA Wm Tj tF) On(Ao Ap Ax Cp Cq Cs Cv Cx
Dc Dg Dl Du eD Eo eP eQ eT EZ Fa Fb fP Fr FY gC Gh Gn Gz hB hC hF hG hP Hu hX Ih IJ Il Im IO iP Ir IZ Jf jG Jh jK Jl Jm Jn jO Jq Jt jV
jY Kc Kd Ke Kf Kg Kj Kl Ko kQ kR kS lK IM Lw lX Ly Lz Ma Mc Md mE Mg Ml Mj Mk Mm Mn Mq Mr Mu Mw Mx Mz nA nC Ni Nm NN

Figure 6 Continued

Figure 6 Continued cP cQ Cs Cu cW cY Db dD dG Dk DL dR eD EF eT Fb fY gL gP hB hL hO hP hR Is iZ jV jY Mb Mt Ne Nl nW pY qB qC Qv rN rU sC uL vP)
cF(Aa aE Af Aj aK aL AN Ao aQ Ar aS aU aV Ax aY bC bE bH bO bP bR bU bX cJ cK cL cM cN Co cP cQ cR CS CV cX cY DB DC dD DE
dF dG dl dK dL eD Ef fP hB Is Mt Mz rW tX tF) Aw(aD AF aH aJ aN aO aQ Ar AX aY bA BC bE bF Bg bO bP bQ bR bV bX cE cG Ch cI cJ
cM Co cP cQ CS cT Cu cV cW Dc dD dF dG dH dI dJ dL dM dN Ef eO fN fP Io Is Mb Na Nd Qe tS) Ap(aK aN aQ Ar aU aV bE bF bM bQ bR
bU bX cE cG cJ cK cN CP CQ cR Cs Cs Cu Cv cY Db Dc dD De dF Dg Dk Dl dN dR EF fP fR gL gP Is iZ Jj Kx Lv Or Pk qO qP Qv rS tN tS
tX) Po(Fp Hr Hx Ii Ij Ik Im Iv Jh Jj Jk Jm Jr Jt jY Lj Lx Ma Me Mf Mg Ml Mr Ms My Mz Nb Nf Ng Ni NK Nm NN No Nr Nt Nx Ny Of Oh Oi
Om Op Ow Oy Oz Pd Pf Qb Qc Qe tS tT Tj) Dg(aI aJ aL Ao aP aY aZ Ba bC Bg bH bJ bP bS bV bW bZ cC cH CO cU cX dA dC dE dH dJ dK
dL Fn Fw gC GL Gp iA Is Jj Kr Ky Lv Na Nc Ne NI Oi Ou Pk Qz rN sC tS tT Tj) Dk(aK aM aQ aU BA bB bC bF bR cE cG Ch Cp cT Cu cY
Db dF Ef Em Fc Fd Fi Fw Gl Gp Hl Ho Hp Io Jj Kx Ky My Nc Ne Nl Op Ow Qe Qv Qz Rx Ry Rz Sf Sh Si Vz We Wh Yl Xa Tj) Mt(aD aM aU
aW bB Bo bR bU cR dC Hu Hv Hx Ik Il Im Ip It Iv Jh Jk Jl Jq Jt Lp Mf Mg Mh Mv Nb Ng Ni NK No Nq Nr Nt Nx Ny Oe Of Og Oi Om Oz Pd
Pe Pz Qb Ql Qv Va Wh Tj) Lx(Fp gV Hq Hu Ii Ij Im Ir It Jk Jl Jm Jo Jq Jr Js Lj Lu Lw Lz Mc Md Me Mf Mg Mh Mi Mk Mq Mr Mu Mv Mx
Mz Nf Ng Ni Nm Nn Nq Ns Nt Oe Oi Pa Pe Pf Pz sC tX wF zH Tj) Bo(Aa bA BC bM Bn bR bX cE cG cJ cK Co CP cT Cu Dc De dF dJ dN dU
eF Fb gL gW hB iJ Ik Jt Kg Ko kP Lv mE mF Mv Nc Ne NI oE oF oH oK Om Oy Pd Qe sC Ue tF) Kf(Db eD eZ fN gP gW Hf hL hO hR Im jM
jY kR Kx Ly Nu oH Ow pF qG qO qP Qv rB rP rQ rR rS rU sK tQ tX Ur uT vB vH vI vP vS vV wC wD wE wG wH wJ wP yD tL) Ko(bH bN
bR bU cQ cR cZ Du Ex FB Fc Fi Fn Gh Gn Hf Hl Ho Hp Iq Kx Ky Mb My oD Op Ou Qv Rt Rx Sh tS Uw Ux Uy Uz Va Vb Vc Vz Wc Wd Wg
Yk Yl Ti Th Yf) Cu(aK aN aO aQ bA bB bE bF bJ bO bQ bR bU bW cA cC cE CH cI cL cM cN cO Cp cS cT cU Cv cW cX cY dD dE dH dJ
Dl dM dN gP Lt Nd oK Rx tS tT wQ Tj) Vt(fN hL hP pS qB qD qG qO qP qQ rO rU qG uI uL uN uO uP uR uT uU uV uX uY vB vC vI vO vP
vQ vT vU vW wB wE wH wJ wK wL wP wQ yD yK yL zG zH yE tM) Ne(Aa Hq Hr Hu Hv Hw Hx Ii Ij Io Ir Jm Jn Jo Jr Js Lu Ly Lz Mc Md
Me Mi Mj Mk Mr Ms My Nf Ng Ni Ns Nu Oe Of Oi Oy Oz Pb Pc Pe Pg Pz Qb Qc rW) Ow(aM Ar Dc De Fc Fn Gd Gn Hb Hp Hq Hv In Iq Jh
Jj Js Jt Kg Ky Lp IX mW Pd Pk Ps Pz Qv Qw Qz Ri Rt Ru Sf Sh Sj Tr Ue Ut Va Vc Vz Wh Yg Yl Ti) nN(bB hA hB iB iC Ir jE jH jL jM jP jQ
jV jY kK kO IL IN iY mF mH ml mM mW mY nA nB nD nF nH nJ nM nO Nr nT nU Nv qT qW qX qZ) Oh(Fd Fi Fn Gd Hl Ho Hp Hx Jh Lp
Mf Ml Op Ps Rt Ru Rx Ry Rz Sh Si Sj tX uP Ux Uy Uz Vc Vi Vz Wc Wd Wg Wh Zw Ye Tm Tl Tj Th) fP(aD aF aN aO Ar aW bB bU cW dD
pS rW rX rY sM uP uR uT uV uW uZ vI vO vP vT vV wB wC wD wH wP wQ yD yH yJ zG zH tM tL xA) Dl(aD Aj aK aN aQ Ar aS aU aV
BA bB bF bG bM Bn bQ bX cG Ch cK cN cP cR cT CV cY Db Dc dD De dF dN eF gP Is Nd Op) Lv(Dw Eo Ew gV Hr Ii Ik Il Im In Ir Iv Jh Jj
Jl Jn Jq Jt Mb Ml Mr Mu Mv Mw Mx Na Nb Ni No Nt Nx Og Om Oz Pe Qe tS tT) Op(Af aH Bn Cs Dc Dd Fy Hc Ib Ij Im Iz jD Je Jk Jn Kj Lj
lY Mx mZ NA Nm Or Oy Pd Ph Qz Ra Rb Rj Tr Ue We Wh Xa) Ma(Hx Ik In Ip Ir Is Iu Jj Lj Lu Me Ml Mq Mx My Nf Ng Ni No Nq Ns Nt Nu
Nx Oi Om Oy Pd Pe Pf sC tS uP) Nd(aM Ao Ar Ba bB cG Ch Co cR cS Dc dN fR Hq Hr Hu Hv Hw Hx Ik Iu Lu Mc My Nf Ni Nu Oe Oi Oy
Pb Pg Qc) Qe(aW bR Cp De dU Fp fR gC Ik Im In Iv Jj Kx Lj Mf Mh Ms Mv Na Nb Nf Nt Nx Of Om Pd Pf Qb Qc Ss Tj Th) bM(aN Ao Ar AS
aU aV Ax aY aZ bB bU cG cK cL Cq cR cT cV Cx cY Db dD dF dN dX Ef fR Is Mg Of Pd uZ) Fp(Hu Hv Ik In Iv Jk Jl Jm Jo Jq Lu Lw Mb Mf
Mg Ms Mz Nb Ni Nk Nr Nx Ny oD Oz Pa Pf Qb Qd) Cp(Af aH aN Ar aV Ax aY bA bB bF bQ bR bU bZ cE Ch cK cN Co Cs cY Db Dc dF dH
dN fN Na) Jt(bA bB bR cT eF gP hP iA In iZ jD kQ Mb Nk nW qC qD qI qO Qv qZ rN Rv rW tS tX wG) Om(Du Em Gn Hr Hw Ir Mb Mf Nr
Pe Pf Ps Rt Sf tX Uw Ux Uz Va Vi Vj Vw Wc Wd Wg Wh Th) Vq(fN hL hO jO pS qO qP qV qX rS rU sM tO uI uL uP uY vB vI wC wL zH zl
tM xA) Is(aQ Ar aS aU aV aW BA bB bU bX cJ cK cM cQ cT cY Db dN Iv jD Mb nK) qU(Hf kE kI kK kN kP IW IX lY mH ml mM mP mS
mT mU nA nF nI nK nO nT nU) Pf(Ik Il In Ir Iv Je Lw Lz Md Mf Mi Mj MI nK Nm Ns Nu Nx Ny Of Pd) Nc(Aa Hr Hv Hw Ii Ij Io Ir Jm Jn
Jr Js Ly Mc Md Mi My Nf Oe Oy Qc) fR(aH aM aQ Ba bH Bn bR Ch cM Co cP cT Cv Db dD dF Ex Gl Hb Jq oD) pH(al bP bQ bU cO Cs Dp
Fb Gp iJ Io Ir Jn Kp mY Nn Qn Sr Yh Yk Xa) Ut(Eq Fn Iq Iv oV Sj Uw Va Vb Vj Vw Yd Yg Yh Yj Zw Ye Tj Th Yf) Ip(eZ fN hO qA qB qC
qD tO tU wD wF wG wH wJ wK wL zl yE Wn) Im(aW Je Kc Mb ml Ml NK pK Qv Qw Rt sC Ss Tr Ux Wh Tj) Hf(eD jY IL pS qW qX rN rW
rX sC sF sO tT tX vY uZ yH zH) Vh(eC cM hG hX iC iO jD jH jl jK jP mE pF Yh Yi Yj Yk tF) bB(aH BA bR bU Ef Ex fB Gd gV Hx Io mE
Nl Nm oT Pd tF) Tk(bG bX fN fY hO jR rX sK tO tQ tT uP uV vQ yD zH tL) Ef(aN Ar aW cG Ct dL dN Ex Jj Na Qv Rx Ur Yh Yi Yj) Tr(Db
eZ Iq qG qI rN sC sF sH sl sJ sM tO uZ vB yL) tT(Ao Ex fN Kc Kj Mf Mg Na Ng Nx Of Pc Pd uV wG zH) hB(dM dU eQ fB gC gZ kF kG kO
mE mM mS nO nU oV oW) Dc(bA cT Gb Ky Lt Mb Ps Rv Sf tS Uy Vi Vj Wh Ye) Nr(Hr Hx Jm Jr Lw Mb mE Mf ml MI Nu Nx Og Pd Wh)
aW(aM Ar aV bA bF Bg bR bX cE cG Co cT dF dN dX) sC(AI eD Ex jY Ke IL Mp Ms Mw Mz Na QW rC zH) oD(Ax dN Du iJ Ir mT Ng Nn
nW Ny Pb Pe Qn Vi Vw) Qv(Db Fb Io Iq Kj Kl Mg Nm Pd Ss uG uO yH tF) Lj(Ew Ik In Iv Mb Mf Mu Mv Ni Nv Nx Of Pd Ux) dU(Gp Ij Ir Jq
Ky Mz Nv Nx Ny Oz Sr St Tv Us) Wh(Ax bL gW hC Ir jO No Nq Nx Pz Qc Qd Up) Ke(fN Na qG rW tN tO tR tX uZ vB vH wG wJ) aM(Af
bF Bn bQ bR cE Ch cT Hb Kl Ky Kz Sr) Ba(Aj aK aQ aU aV Bn bU Cs cY Db Mb Na) Th(fB kE Kx IW mE mU mY nA Ny Ou oV Wm)
Mz(eT eZ fY hO IL Mb pY qA qB rV tX zH) We(Cs Dd Ex hC Ir Jr Jr No Or Pe Pk Wm) Ar(aK aV bU cE cT cY dF Fb Io Sr Ss) Ti(Fb Iq mE
No Ny Pk rU rZ St Wm) Nm(In Mb Ps qO tO tR uP vB wB wD) Iz(Du Eq Fc Lt Rv Rx Sj Vb Vj Yl) Pe(eW gV Hr Hw Lw Mf Mi Ml NfTj)
dN(aQ aV bE bF Bg Bn bR bU cK dD) tS(Bc cH Ex Gl Kc Kn Kp Kz Qw Ue) Na(Hb jD IL Mb tN tU vW yH zH) Rv(gL Jk kG mE Pi Pk qY
Rc Ss) Fb(cR Db Eq Jj Oz Rx Si Ue) Nl(Db Hr Hw Io Ir Iu Js Qc) Nx(In Jj Ml Ms NK Og Pd) Vi(Dd hA jL jM jY IL Pk rA) bR(bF bQ cG cN
cW dF dG Jh) tX(Jo Mg Mq Ny Pc Qw Ri yL) vS(cS cV fN Id IK qA Qw Ri) Ex(bQ Du Lt oK Si tO tU) Kx(Ch eM cP Hb mE pI pK) nK(Hq Ik
Iq Jm Mv Mw Nn) tN(Jo Kg Ki Pc Qw uP wL) jD(Gb mS Sf Sh Vc Yd YI) No(Eo gC Ik Iv Lp Ml) Mb(eO Ew Nk Nn Nt Pd) Mf(Ir Iv Me Nk
Nv Ny) Kz(pS uZ vB yH zH xA) eM(Du Kc Kk Lp Sr Ur) sO(cS qO qP uP vP vV) nW(Gb Sh Si Va Vj Yi) Ml(Jh Jl Mw Nn Nt) Ps(jF jT Qz Ss
Ue) Ky(vW wG wL zH xA) Nv(Hx Ik mZ Nk pK) bA(aV bF bU cI eP) dX(cG dD dF iJ Kc) uP(cS Kp IK pS rS) Bg(Aj bU Em Gn) Du(gL nJ
Qy tF) Gb(gW jK jO jR) Iv(Mu Mv Og Pd) Jn(dW eO Uw Wf) Ou(Je sH sJ Ur) Va(hA hW jP rB) aH(eQ fA oT oW) fN(Bc Jh Qh yL) jT(Ry
Wd Yi YI) rN(eC KI Nq Ss) Nk(Ik Nt Qd) Sf(gW jU qT) Kg(tO Ur wG) Vj(mE Qh Wm) Pd(aN Ii yK) cG(eO gZ nT) qY(Fc Yd Yj) qX(Gd Lt
Ry) rW(Bc sJ Wn) Ik(aA Og) Hb(gV Ss) Je(Iq Ir) Wd(gW Qm) Qw(Qt uX) KI(Aj Jj) Yl(jM Rc) Ri(rC rU) Vc(hC jI) aY(eO eW) bU(bF cT)
dF(cY Em) IX(gL pF) tO(Ao pS) wD(vP tL) qT(kO nL) oO(Fy qZ) BcjY DbeD DwdB EwaD FnQm GheQ GdUr GnmE GpRt MspS HpQc
YiiZ SiQz ZwlK WfhC YegW RzOr OiyH UwjM UxPk OzpK aNeP aPuZ iCkF sFrS Constrained panels with 3 analytes, where 4.8E-12 >= 'AUC p-value' > 0. Contains 50,000 panels of 38,530,102 total panels evaluated. :
Zq{mM(aF aH aN AO Ap aQ aS Bb Bc bF BG Bn bS bW bZ cE Ch cJ cK cL Cp cR cV dE Dk eF Em fA Fc Fp Hc Hf Hq Id Ij Il In Iq Is Jd Jh
Jl Jn Jp Jr Jy kl kP Kx Lh Lt Lx Ma mE MF mH Mn Mt Mu Mv Mw Mx My Mz Nb Ng Nj Nn Nq Nr nT nU Nv Nx Om oO Or Ou Pf Pg Qa Qd
Qn Qv Rg Rv Rx Ry Tn Ua Uy Vi Wc Zx Tl Th) lY(aA aF AO aS Bb Bc Bn bQ bW bZ cJ cK Cq cR cV dB dE Dk eF Em Fp Hq Id IJ Il In Is Jd
Jf Jl Jp Jr Jy kP kS Lh Lt Lv lW Lx Ma mE MF mH Mj Mt Mu MW My Mz NC Ng Nn Nq Nr nU Nv Oi On Or Ou Pf Pg Qd Qh Qn Ry Tn Tt
Up Ut Uy Vi Wc Tl) kF(aH al AS aX BB bQ bV bW bZ Cu cV dC dE dF Dl Ed Ex Fa Fc Fi Fp fR Fy Gb Gd gL Gp hB hC Id Ih Is Jd Jl Jn kN
Ky Lj Lu Lx Ma Mn Mt Mv mW Mz Nb nl Nn No Nq Nt Nu Nv nW Oa oE oF On Pe Pf Po Qa Si Tn Tr Um Ur Ut Uy Vi Yi Xa Wm Th) jD(al

Figure 6 Continued

AL Ao bB bF Bg bH bI cB cD Ch cQ cV Cx cZ dC DD Fw Gn Hc Hu Il Im In Ir Jf jH JK Jp Jq jT jU lK lM Lv Mf Mj Mn Ms My Mz Nb Ne Nq Ns Nw Of Og Ok On Oz Pb Pc Pf Po Qc Qe Qh Qt Qw Rt Rx Ry Tn Tr Ua Uc Up Us Vc Wd Yl Zx) lM(aI Aj aL aP aZ bB bG bJ bN bV cD Ch Ct cU cX dD dM Dr Fb Fn Fr Fw Hc Hl Ic Ik Il Io Ir Is It Iv Jf jK Jm jO Jq Kg Kj Lv Me Mg Ms Mu Mz Nc Nd Ne Ni Nl Nm Ns Nv Of Oh On Ou Po Qz Rm Si Ub Ug Va Vc Vh Wd Wf Yi Yj Yk Yl Zw) kC(aQ Ar Ax bQ bZ Cs dC dD dE Du Ed Fa fB Fp Gd hC Id Ih Ij Im It Jh Jn Jr Js Kc Kx Ld Li Lj Lx Lz Ma Mh Ml Mq Mx Na nK Nn No Nr Oa oF Oh Ow Pe Po Qa Qt Qx Ra Rf Rh Ru Tn Uu Uy Yi Th Yf) kP(aD aG aH An Ax aY bQ bZ cN Cs Dl dU Eq Fa fB Fn Gd Gh Gl GP Hf iA Ii In Io iP Jd Jl Jn Jr Ju Jv Ki KK Kn Lj Lx MF Mv Nq Nu nW Oa Of Oz pF Qn Rg Sf Sh Si Uk Um Uv Yh Yk Yl Tj) mH(Ar bQ bZ dC dE eC Ed eM Eq Fa fB Gd Gl gP hB hC Hf Im It Iv Jl Jn Kx Ld Li Lj Lx Lz Ma Mf Mh Ml Mx No Nr nW Oa oE OF oO Pe Pf Qa Qx Ra Rf Rh Rj Ru Rv Si Us Uy Vo Yd Yh Yi Wm Yf) fB(aA Ap Bc bJ bM bW cK dB Dr Fp Gd HC Hl Hv Ic Id iH Ii Jl Kl Kn Kr Ky Lt Mb Mk mS mT Mu Mv mW Ng nI nT Nv Nx Ny oH pH Qv Qy Qz Si Tv Ut Uw Uy Vb Vi Vz Wb Wc Yh Zw Tl) iP(aN aZ BB bJ cA Ch Cu cX Dd dI Fb Ha Ih Io Ir Iu Jm Ju kQ Kx Ld mE mU mW mZ NC Ne Ng nI nJ Nk NL nN Ns oK On Pk Qa Qz Sf To Ub Ue Us Ut Vc Yi Yj Yk) mW(aH Aj Ar bB bL Bo bQ Cs Du Eq Ez Fa Fn Gl Hf Hl iZ Jd Jl Jr Kg Kj Ld Li Lx Mh Ml Mv Mx nB nI No Oa oD Of oH Or Pa Qv Rg Rj Rv Ur Uu Vo Yh Yl Ye Xa) iZ(aA aJ aN aO aP aS aX aZ bB bF bI bJ bO bR cD cR dA Dc dG dM Dr eC Eq Ez Fb Gc Gh iJ Ir Iu Jf Jm kK Ko kQ lX Mn Nc Ne Nl Ns oD To Ue Vc Vh Yi Yj) jR(aE Al bA bJ bS bX cD cM Cu cX Db dM Fc Fi Fw Gd Gn Hc Ho Hx Ic Ik Jf jT Kj Kn Me Mz Nc Ne Ni Nl Ns Nv Ou Pd qW Rm Ry To Va Vz Yh Yi Yl Zw Tj Th) jB(AD Aj aW Bc bL bQ bW Ch cQ Ct cW Db dE Di Ed eM Ex Ez Fd Gh Hc Hf Ii Ik Jd KG Kn mT Mv nD Ng nI Nt Nu nW Ok Oz Si To Uh Um Uw Uy Zw Tl) lX(Ao Bb bL bZ Dl Ed eQ Gb Gp hB iH In Is Jd Jl Jn Jq Jr kS Lh Lx MF Mj Mn mT Mv Nn Nq Nr Nu Nv nW oF Oi On Op Ou Pe Pf Qa Qn Qz Rm Up Ut) kK(aA aN aQ Ar Bc bW cJ cK cX dE Ed Fa Fp Gd Ha hB Hl Id iH Im Kc Kl Kx Ky Ld Lt Mn Mv Ng nI No Nx oK oO Pa Pe Ry Ss Ur Ut Uy Vb Vo Wc Yl Xa) jO(aY cB cF cI Co Ct dD Eq Fi Fw Gl Gn Ik Iv jI Jq jT Ju Ky Lu Lx Ly Mt Nb Nc Nv Of Og On Op Or Ou Pf Pg Qe Qz rA Ri Rx Rz Sf Vh Vs) bW(aC aM aU Bb bR cM Cq Cu Dc dM Dr dU eC Fb Fr Fw hC Hx Jd Kj Kx Lj Lu mP Nc Ne Nk Nl Ns nU On Or Qa rA Rg Ss To Ug Vh Yk Yl Ye) jT(aA aJ aK aO aP aQ aS aY bI bJ Bn Bo cD cG cM cU dE dG Dk Em Fb Fn Gd Hv Ic Iu jF jG lK lL Me Mg Nq Nu Op Rz Ue Va Vc Vj Wc Th) mE(aC aH aI aM bE Cs cZ dB Du Eq Fa Fi Fn Gd Hl Hr Jd Jn Kg Kj Kn Ky Li Lj Mh Ml Mn Mt Mx No Nq Oa Of oO Rg Rj Uk Ur Vo Yh Ye) Or(aC Af aO aP aQ bR bS Cq cU dM Dr Fb Fd Fn Gp Ho Hq Hr Hx Jm Kk kQ Lt Mj mS mY nC nH Nw Pk Ri Ru Tt Ue Uo Vp Yg Yk Tj) nI(aC aL aY bB bC bE bZ cJ cR dD Em Gd GP iH Ii In Jr Lu mF Mn Mz Ni Nr Oe Of Og oH Rb Rg Rv Ry Tn Ur Ut Vo Vp Ye Th) qX(AO aP aX bV cD cE cG cN Cq cU cV dF dG dH dM Du Fd Ha Hp iB Ip jM Jo Kk Ks Kx Ky lK Me Mf Mw Nf Nk Nu Oa Og Rv Ss) rA(Al AX bA bL Bo bR cB cJ cY dA dH Ef Hp It Jo Ki Ky Nf Nk Nq Nu Oe Og Qm qY Rh Ss Ua Uf Vb Vz Yd Zx Tm Ti) aM(aC Af aN AP Bb Bc bR Cq cX dG Dr hG Hx iA Jd kQ Lt mF Mj Mm NC Ng nJ nT oK Op qT Ri Ru To Ut Vh Ye) jQ(aE aR aS bJ bS bV cD cM Cu Db Fb Gn Hx Io Iu Iv Ki Kj Mf Mg Mz Nc Ne Ni Nl Ns qW To Uv Yh Yi Yl Zw Th) oO(aG aI aL Ap bB Bn bU bZ Cq cV dC dD Di Gp Hb hC Hl Hr Ii In Jd Jr Lx Ma mF Mn nC Nr oD oH Qh Rx Wc Xa) oD(Ar aV Ch dA eM Fa Gd iH Jh Kc Ld mT nC Nd Nl nN NU nW Oa Pe Qh Qv Ry Si Uo Ur Uu Uv Uw Vz Yd Th) dU(aN aQ Bb Bg cJ cK Db dC Fc Fp hC Hl Hx Kc Kr Ky Lt Mg Mw Nd Ng Nx oH Pa Tv Ut Uw Uy Wc Wf Th) mS(Af AL As cH cJ cR dB dE Dl Gb Iq Jf Ji Jj Ks Lt Lu mT Mv Mw Mz Nc Nn Nv Op Qa Qe Qz Tr Uf) qT(aH aJ Al Ap aV Ba bR bV cL cN cT Cv cY dA dM Du Hp iB Jf Kj Kl Kx Ky lK Lv Mf Mh Mw Nf Yd Tm) jL(aE aR aS bR cD Fb Gd Gn Im Ir Is Jf jK Kg Mg Mz Nc Ne Ni Ns On Ou Qe Rx Ry Un Vc Vh Yd Zw Th) mT(Aj Ax dK Eq Ez Fn Gd Gn Gz Hf Hl Kf Kg Kj Nd Oa oH Qy Rj Uh Um Ur Uu Va Vb Vo Vq Vw) dM(Ap Bb cF cW eD Ef Ex Fb Fp HC Hx Jd jE jI Lj lN Lt Lu Mm Ou Qv Rg Ru Rv Ut Vh) mF(aH aI Ax Bb bL Bo Cs Dc Du Eq Ez Fa Fp Gl Kj Kn Kx Li Lj Mh Ml Mx Of Rj Vo Yh) aC(Ap Bb bE bH cJ Cq cW Dr Ef Fb Hx Jd Je Kj Mm mZ nC Ok Qm To Ue Yk Ye Tl Tj) jK(aG aH aO Bc bI cJ Cq Cs Ct Eq Fd Ik Io It Je Jh Nd Nk Nr Oa Oz Pa Ss Ua Tm) Rg(bL bR cI Dd Dr Fb Hx Lt mZ nC Ne nJ Nk nL Ns Pi Pk Qc Qw Ri Uo Up Us Vh) nU(Aj Ax bQ Db Dc Du Eq Ez Hl Hr Hv Kg Kj Kn Kr Mg nT Of Pa Qv Rj To Uy Yh) Dc(Ap Bb bS cF Ed Fa Fd Ha Ho Hq Hr Hx Jm Lt nR Ri Uf Ur Ut Vq Yk Tj) oK(bO cD cR Cs Cu Dr Ex Io Jd Kp Kx Lj Mh Nk nW Oa Qa Qm Qv Us Ut Yk) qY(bR cF Cu cW dF Ed Fw Il Iu jP Mb Mh Nb Nl Nq Nr Nx Oi Po Qu Yd) jU(Ad bA cD cL cO dD dH Fb Fw Ic It jP jV Kg Ky Pa Ss To Ua Th) pH(AD Ap aW Ch Ct cW Db Dl eM Eq Fn Fp Hr Ii Jd Ng Nu Pa Si) bR(Ap Bb cW dK Ef gW Hx Jd lK Lt Mm qV Qz Rv Ut Vq Vu Yc Tl) kQ(Cs Cu Dd Du Fa Fp hC Hv Iv Jd Jl Mf Mx nB No nW Oa Pi Pk) nC(aI Ax bE Db Du Eq Fa Fp iH Ji Kn Lj Mn Mx Pa Qv Rj Yl) hG(aA bJ cQ dI Fa fR Gd Ik Jd Jn Ld Mm Mt No nW Pk Qv Tm) lL(cB cJ cP cW Dd Eq Fr Gz Hc jI Mm Nj Nk Ps Rf Rh Ss Tm) nT(aH An Ax aY dH hC Jh Jv Kn Kx mP Nu nW Pe Qn Sf Yk) Fb(aN aO Ap Bb Dr Fi Gl Hx iH Lj Lt Pk qW Uo Up Yg) hC(aO aP cU eM fA Fi It kG mZ Rj To Ue Uo Wf Tm Tj) jP(As bN Cu Dl Fw Hc Ju Jv Lh On Ou Pg Qh Sj) mZ(aI aL aY bE cV cZ dD Dl Ic Id iH Mz oH Rv) Ss(bB bL Cs dH Dr Lj lK Lt Pk qV qW Up Ut) eC(Ap Bb bZ cK dB Jd Jf Lt To Up Ut Tm Tl) mP(Aj Ap Bc Db Hc Ii Ky Mg Pa Qv Us Uw Zw) Hx(aI bB cR Dk Jd Ko Lj lK Mn On Ow Qh) kI(aD Bb dC Eq Fp Jh Of Si Tv Uy Vo Th) nH(aH aI Db Eq Fa Fn Fp gP Lj Mx Rv) nW(aP cU dA dG eQ gC Kp lW nR Qv Ut) aO(bZ Ch Fr Hc Jd Lu Ma On Op Ut) iO(Ap Bb Bc cW Jd Mn No Qm Ur Uy) lK(Bg Ct Du Fr Fw Ik Ky Oz Po Vs) Kj(Ap Bb cR Gl Hr Jd Lj nR Qv) bB(Cq jY kG Mm nL nO pF pK Ye) Ri(bL cR Cs cW Ez Rv Up Us) nR(Eq Gl Hl Kn Mn Of Vo Yh) mY(aH Cs Fn Gd Gl hB Kn Yl) Ap(Ad aU cM dD Iz Jd Vh) Cq(aN bL cR Dk Hc Lv Ut) hA(Ct Cu dD Fa Fr Ou Qz) jI(aP bV Fn Ic Ub Ug Uv) Dr(bO cB cF Hr Mt Qv) Pk(Lt On Ps Vh Ye Tj) aH(kE lW nB nD nJ nL) cR(hB iA oN pF Vh Yc) iC(cL dD Kn Qm Sr Vi) jF(Gd Jf Mz Ut Vc Ti) jY(It Iz Ji Ky Po Rf) jG(cP Dd dI Nu Rf) pK(Aj Kf Pa Um Vo) Ch(bF bL Ne Ns) Cs(bV hB iA pF) Qz(bL dH gW oH) Ut(dH Hq nB Vp) cF(Nc Ne Ns To) nJ(aI As cZ Qn) jV(dD Fn Ju Sf) nY(aZ cU Ue Yk) oP(bQ hB iA Nq) oW(hB Hl Kx Pa) Lu(bV dG dH) Mm(bL bM cD) Qv(nA nK oV) Kn(kN lW oT) Rh(kN nD qV) On(bV Gl Vp) Vh(bL Gl Yk) eM(Bg hB oH) eQ(Hf Mn Th) gW(bO Nx Ye) nB(Tt Up Th) nL(aI Mn Nq) qW(bI Kx Ky) Bb(cB Ko) Ef(bF Hq) Mx(iA pF) Hc(bF Hq) aN(An Yk) cJ(Lt oQ) cW(cM dD) gC(Vb Vo) gP(lW oT) nA(aI Dl) nD(Nk Wc) jE(cP dH) qV(bI Oa) BcoQ TjFa EzkN YhpI QapF JdUf JlIW YebC RxfA LjaP RfqU PanK aLkG aXiB cUoN dCgZ kOoH} tV{Vt(Af aJ Al aM aR Ax Bo bQ cF Cq Cw dA dE dG Di Ex fN HA Hf hP Hu Hx iA Ic Ih Ij Il In It Iu jG Jk Jl Js jY Kd Ky Lv Mk Mn Mu Na Nd Nf Nh Nn Nq Ns Nt Nu Nx Oe Og Oh Oi Pc Pe Pj Po Qb Qc QD Qg Qh Ql qT QU Qv QW Ri Rm Sr St Tt uU uX uZ Vp VQ vS Vu wG tL Tk) Di(Ad aK Al Ao Ap aQ aU aV bH cA cR cS cU Cw cY Dc Dg dR Et fN fP FY gW Hc Hf Hu Ic iH Io Ip It iZ jF Jk Jo jQ jR Jt jY Kc Kf Kg Kj Kl Kp Ky Kz Lu Mm Mu Mz Na Nm Nq Ns qO qP Qu Qw qX rA Rh rU rW sC tO Tr TT Ua Uf Ug Um uU uV vP vV yH tM) Bb(aU Ba Bo cS cU Cw dR Ex fN fP fY Gp gW Hf Hu Ic iH Il Ip Iz jF Jk jQ jR Js JV jY Kc Kd Ky lK Lv Mm Na Nq Nt Nv Oi Or qA Qb Qc Qd QG ql Ql qO qP Qv Qw rA RC Rm rW sC sF sJ St Tz Ua Um uU Uv vB vP vS Vu vV wQ yH) Ad(aK aU BA Bg Bo cM cU Cw Ef Gp gW Hc Hf Hu Ib iH Ij Il It Iz Jk Jn jQ Js Ju Jv Kp Ky Kz lK Lv Mn Mu Na Nn Nq Nt Nv Oe Of Oi Pc Qb Qd QG Qh Ql qO qP Qu Qv QW rA Rh Rm rN rW sC St Tz Ua Us uZ VP Vq vS vV wG) Et(Aj Ba Bg Bo bQ cG cL Co Ef fN Gp gW hA Hf Hu iA Ib IH Ij Il In Ip Is It Iz jF Jk Jn Js JV jY Ky lK Mv Na Nq Nt Nv Of Oh Qc Qd qG Ql Qv QW Rm rN rW sC sF sH sJ St Tz Ua Um uP vI Vp Vq Vu yH Tk) Tk(Af Ao aP Ar bQ cF cL cN cQ dD dF eZ Fn fY hA Hb iA IC iO It iZ jF Jn JY Kx Ky Kz Lu Mp Mu Mx Mz Na Nc Nh Nk Nl Nw Og Oi Pa Pc qU QV Rf tU Ua Uc uM uO uP uX uY vB vT vV wH wL zI yE tM tL Tj) Pj(aK aU Bo cA cM cY fN Fw Gp gW Hf Hu Ib Ic iH Il Iz jD jF Jk Jn Js JV jY Kc Ky lK Lv Ma Mn Nl Nq Nt Nv Oe Of Ph Qb Qc Qd Ql qP Qv QW rA Rh Rm rN rW sC St tO tT Tz vB vH vP vS vV wQ yH zI xA Wn) Vq(Ao Ap aU Aw bX cB cH cI dE dR fP gW Hb hL Ic iH It iZ Jd

Figure 6 Continued

Jg Ji Jp Jt Ju Jv jY Kc Ke Ky Kz lL Lv Mk Mm Mu Mx Mz Na Nn Nu Nw Og Oi Oz pF qU QV Qw rU To Tr Tt Ul uM Up vB vP wH wL yK zG tL xA) Ip(bH Bo bX Cw Dd Ed fN Fr Gp Hq iA IH Il Im In It JD jF Jg JV Kc Ky Kz Lh lK lN Mr Ms Mv Na Nm Nt Nv Of Oh Qb Qc Qd Qg Ql Qv QW rA rB Rm rS rW St Tr Tt Tz Uf uP vI Vp Vu yH tL tF) Qw(Aa Ao aZ Bc bQ bZ cI Cw dE Dk Dl EZ fN Fy Ic Id Ii Io It Jg Ji Jt jV Kc Kf Kg Kj Ko Kq Ky lK Mf Ml Mm Ms Mx Mz Nm Ns Ok oN Pz qW rB rN rT Tr Tt Uc Uf Ug Uk Um Un Ur Vo wF wQ zH Wn) Qv(Aa aJ Ao Ap Bc bH bO bQ Cw dA dE Dg Dk Dl Ed Ez fN Fy Hb hP iZ Jd Jg Jo Jt jV Kg Kj Kl Kp Kq Lv Mg Mm Nm Ns Ok qT rB rS rW sC Tr Tt Uf Ug Uk Um uN Ur uU uV uZ Vo vS wB wF wG zI Wn) Kc(aK aU Bo Cw dR Ed fN Fw Gp gW iH Il Im JF Jl jQ Js JV jY Kz lK Lv Ly Lz Ml Mn Na Nm Nq Ns Pc Qb Qc Qe Ql qO qP qX Ri Rm rU rV rW sC St Tr Tt Tz uN uZ vB VP vS wB tL Tj) Mm(Af aU bF Bo bZ cG cM Co dF fN Fw Gp gW hA Hf hP Ic Il iO iP jG jM Jn Jr Jv Ky lK Lv Mn Mp Mt Mv Na Nq Nt Of Oh Qb Qc Qd Ql qV qW Ri Rm rW sC St TT Tz vB vI Vu wQ yH zA tL) Ql(Aa Ao Ap Aw bH bX cI Cp Cu Cw Dc dE Dg Dk Dl Ez Fy Hb Ic Ii Im Is It Jd Ji Jo Jt Ke Kf Kg Kj Kn Kq Lh Lu Lv Mz Ne Nm Ns Nw Ok On Pd Pk Tr Tt Uc Uf Uk Um Un Vv zG tM) St(Ao Ap Bc bX cI cS Cu Cw dA Dc dE Dg Dk Dl Ex Fy Hb Ic Im Is It Jd Jg Ji Jo Jt jY Ke Kf Kg Kj Kp Kq Ky Lh Lv Ma Mz Nm Ns Nw Ok On Pz Qa Qe qU Uf Ug Uk Um Ur zG tM) Cw(aJ bH bQ cH cI dE fN Ha Hu lC iZ jF jG Jk jM jY Kn lK Lv Ly Me Ml Mu Mz Nf Nq Ns nY Of pY qU qV qW rB Rh rN rP rW sC sK Tr Um uU uZ VS wG zG tL tF) Tr(BA bF Bg bQ cG cL dD dE Ef Gp Hf Hu Ib lC Iz jF JV Ky Kz Ma Mf Mh Mu Mz Ng Nq Nt Oi Pc qA qW Qy Rh Ri rW Ua Um vS wB wG) Nm(aK aU Bo fN Fw Gp gW hA Hf iH Il In Is It jD Jn Js JV jY lK Na Nt Nv Of Oh Qc Qd Qg qP qW Rm rN rW sC uP vB vQ yH yK tL tF) Kf(Af aK Bo bQ Cs dE dG dR gW Ha Hu iA Ij Il jG Jk Jl jM Js Lv Mk Mu Na Nn Nq Ns Nt Oe Oi Qb Qd qG qU qW rN Sr uZ vS vV tL xA) Hf(Ao Bc bP bX cH cI dE Dg Dk Dl fN iC iZ Jd jF Jg Ji Ke Kg Kj Kl Kq Kr Lu Lv Ly Me Ml Mz Ns Nw qU qV qW rW sC Um vS zG tL) Uf(bQ bZ cG Co fN Gp gW hA Hu iA iO jF jM Jn Js JV Ky lK Mp Mu Mz Nq Nt Oi Pe Qb Qc Qd qG qT qW rB rN rW Tz wQ zI tL xA) Kj(Aj Bo Ct Fw gW Hc Hu iH Il Iz Jk Js Jv Mu Na Nq Nt Oe Of Oi Pc Qb Qc Qd Qe Qg Qu qV qW rB Rm rN rS Ua vH wG tL) Mz(aK aU bA Bo cA cU dR Ed fN fP Fw Gp gW iH Il Im JF jQ JV Kz lK Qg qO qP rA Rm rW sJ Tt Tz Um Uv Vp) Lv(aF Ao Ap Aw Bo cS cV cX Dd Dg fP Fw Hc iH Il It Jp jV Kd Ke Kg Kp Ky Ma Ms Na Nt Of Qc qW rA rB rS rW) Na(Aa Ao Aw Bc cI Dc Dk Dl Ii Jg Ji Jo Jp Jt Ke Kp Kq Lh Ml Nw nY Ok Om Pd Pi Pz qU Rh sC sJ Um yH Wn) Nq(aK Ao Ap Aw Bc bH cI CU Dc Dd dE Dg Dl Ez fP iH Jd Ke Kg Kl Kq Kz lK Ok qO qP rN rW Um Un) It(Bc cI Cu Ed fN Fw Gp Il jD Jg Ji Jo Jt jU JV Kd Lh lK Ma Ok On Qg qW Rm rW sH sJ Tz Vp Wn) Ky(aZ Bc bQ cI dE Dk Ed fN hA hP iC iP JD jF jV jY lK Ly Ml Ns qD rB sC Um uZ wG wH zG tF) Ic(Bc bQ Ed fN Gp hP iC JD jF jG Jn Jr jU jV lK Pe Qb Qc qG qU rA RB Ri rN rW vS wG) Ao(aK aU Bo cU dR Gp gW Hu iH Jn jQ Kp lK Mu Oi qO qP Qu qW Qy Rh sC vP vS vV zI xA) Tt(Bc bF bL bQ bU Ch cI dD dE Hu Ib Iz jD Jk jV Ng Ns Of qA qW Rh rN rP Um VS wG) sJ(Aj Ha Hq Hw Hx Ir Jh Jn Jq Jr Js Kl Lj Mb Md Pd Qa Qb Qu Qz rW Ss Tz Ug Uk Ur Vu) Jg(Ba Bo bQ Gp Hc Hu Il In Jk JV Nk Nt Nu Nv Oi Pc Qc Qd qG Qu qW rA rN Ua) Jo(Bo bQ Hx IH Il In Is Jk Jn Js Mk Ne Nt Qb Qc Qd qU qW rB rN Up wG yK tL) Um(bP bX cV dE Dk Ed gW iH Mu Ne Nn Nt Nu Oh Oi Pe Qb Qc Qe qV qW uV vB wF tL) Ji(Af aU Bo fN Gp gW Il jQ jV jY Kk Kz Nt Pc Qc Qd qG qT qW rA Rm rW Tz wP) Ke(Af aU dR fN Gp gW Hu Jn Js Mn Mu Nt Nv Qb Qd qG qO qP vH vP vS vV zI xA) Kg(aU Bo Fw gW Hc Hu iH Jk Js Mu Nt Oe Of Qb Qc Qd qU qW rN vB Vp vS tL xA) Nw(Af aK aU Bo cU dR fN fY Gp gW iH Il Jn jV jY lK Nt Qc qG qO qP Ri rW) Kp(Aw Dd Ed fN gW iH jY lK Qb Qc qP qW rZ sC uZ vB vS vV zI tL xA tF) Wn(aM dE hA Hb iB Jd Jn jY Kz Ml Nt qP qU qV qW rZ uM Up wF wL yE xA) Hu(Ap Aw Bc cF Cu Dg Dk Dl Hb Jd Kl Kq Ma Of Ok Pz Ri rS Ur vI Vo) Lh(aU Bo bQ fN gW Il In Is Jk Jn Js jY Mt Nt Oi Qa Qb Qc Qd qT tL) Kz(Bc bQ cI dE Ed fN hP jM jV Pe qT qV qW rB rN rS uV vS wF wG) Ok(Hx iH Ij Il Im In Is Jk Jn Js jY Nt Nu Nv Qa Qb Qc Qd Rm Vp) Dg(aU Ba Gp Hc Il jG Mn Mu Oe Oi qP rN sC sF vS wQ zI xA) Ap(Gp gW Jv Oe Oi qP QU qW rN sC sF Uv vQ vS vV wQ) Qb(Aw Bc bH bX cH cI Cu Dc Dd dE Dk Dl Ex Hb Kq qV) fN(Aw Bo Dd Gz Io Jd Jp Ms Nj Ns Qu Rh Ri Ua Ut) Mu(Aw cI Cp cS Dd Dk Dl Ed fP Kn Kq rW Uv) Jd(Gp Hc Jf Jk JV Nt Oi qG Qu Rh Ua vS) Jt(Ih Il In Is Jn Js Nt Oh Oi Qc Qd qW Rm) Jk(Aw Bc Cp Cu Dk Fr Ma Mg Ng Of On Oy) Dd(aK aU bQ dR Ed gW vS wG zI tL xA) Ms(hP Il iZ jG Jn jY Qc Qg qU qV tL) Dc(Il Jl Pc Qd rW Up uU uZ zI tL) Ex(As Dl Ed Lx Mw Qe uZ vH zI xA) Nt(Dk Ii Is Kq Li Ma Om On Pz Uk) Qc(Fy Hb Ii Im Li Ma Om On Pz qV) iH(bZ Fy Ks Ly Mf Ml Ue Ug Ur Uv) Ns(cM Ed Fw gW lK qO qV qW tF) Qd(Cu Dk Ii Im Li Ma Om On Pz) Qg(bQ bX cI dE Dk iC iZ jD zG) Gz(aD Bc cI Dk Hb jD On qH) Kq(Bo Hc Jn Js Us uU uZ yK) lK(Aa Bc bZ cI cK Qu Rh tL) rW(cF dI Hb Io qW Ri Uk tL) Ml(bH cI Cs jV qW rB rS) sF(Cs jD Jh Ju Kl Mt Pc) Bo(bH cI Dl Kl Kr qU) Il(Ii Im Jp On Pd Pz) Qu(Bc jD jV Ss wF wG) Jn(Aa fP Jp Nn sC Tv) Jv(Bc bX dE Dk iZ zG) Rm(bX cI Cu dE Dk tM) Aw(bQ Mv rB Ua uZ) Lu(cF cH cI qV qW) Js(Cu Ma Om On Tv) Rh(Ed jV sC uV wF) Pc(Ma qU qV qW rS) Mf(bH fP qU rB) Ur(Oi qW sH wF) Vp(bX cI Cu dE) Dk(Hc Ua Vu) Nu(fP qP Uv) Jp(bQ qT wG) Kn(dE uU vS) Uk(qW wF wH) qU(Cu Fb Hx) Bc(jY uU) Dl(jY xA) Fw(jG qV) Ly(cV rS) Ua(rZ wF) Hq(wF wG) Kl(Ba Hc) Of(Fy Oe) Oi(Ug Un) Uv(zG tL) bZ(cS fP) vS(cF cS) AafP CuSr EdbX MbcI TzHb HrsI TvwG IojD JhsH RigW RgqW NvOn UniZ UgzG PdyK} Tk{wL(aA aC aH aL aM aN aX aY bA Bc bG bH Bo bQ bX bZ cC cH cJ cL cR dB dG Dp Et eZ Fb Fp FY Ha Hb Hf hO hV Hx Ii Io Ip Iq Is It Iu Iv Jd jF Ji Jm Jo Jp jR Jt Jv Kg Ki Kp lK Lu Mx Nb Nm Nn Nw Oe oH Oy Pd Ph Pi Pj qG Qh qI Qm qO qP qT qU qV qW Qx Qy Ri rW rZ sC sM tO tS Ub Ue Uh uM Un uO uR UT vH vP vS Vv wE wP wQ yD yL zG yE tM) rW(AD Af aM bC bE BG bQ bV bX bZ cF cG cI cL cQ cW dC Dd dG Dp eF eZ Fn hA Hb hL hO Hq iA Ic Ii Io Iq iZ Jd Jf Jg Ji Jp Jq Jr Jt Ju jY Ke Kg Kp Kq Ky Kz Lh Li lN Lu Mb Mf My Na Nm Nn No Og Oh Oi Oz Pa Pe pF pS Qa qB qC qI Qm QU Qw Qz Rb Rf rP rZ Ss tQ Tr tU Ua Ub Um uP Uu uV vI vT vW wE wP wQ yD zH zI tL Tj tF) yL(Aa Ad Ap Aw bG bU bX cB cF cM Ct Cw cY dH Di Dk dL dR Ef Et fN Fy gW hA hG hO Hq iB iJ Ip Iv jD jE JF Jk jQ JR Jt jV jY Kn Kp kS Kz Lu Mk Mr Mu Nm Oe OF Pa Pc Ph Pi pS Qb qH qP qT QU Qw Ri rS rX rZ sC sK tO tQ Tr tS Tt Tv tX uG Uk uN Up UV vA vI vO vP Vs Vv wF wH yD yJ yK zG xA) Mm(Aa AJ aK aM aP aU aV AW aX bE bF Bo bU bV cC cK cY dA Dc Di Dk dM dN eD fY gL Hc Hf hG Hw In Ir iZ Je jM jQ jR Kd Ke Kg Kq Kr KS Ky Lx Mg Mh Mr Mt Mx Nm Nn No Nt Nw Oi PF qB Qc qI qP Qv Qx QZ Rb Rg rN rS sK sO Ub Ug Up Us vA vP VT wB wK) vP(aA Ad aL aN aR aV bM bN cQ cY dA Dc dH Dp Et Fy Gp Ha Hf iA Ii Io Is iZ Jj jL Jm Jp JR Js jU jY Kd Ke Kg lL lN Ma Mz Nb Ns Nt Nv Ny Oh On Pa Pc Pd Pe Pg Pi QC QH rB Rf Ri rV rX Sr Tr Ub Uf uG uM Us uV vI vV yJ tF) wH(aF aH aK aL aN Ap aQ Bg bL bM bQ bX Cq dD ET FN fP hV Hx Ib iH Ik It jM JY Kz Lv Lx Mk Mz Nc Nk Nq Nr Oi Pa Pc Pi Pj Ql qP QU Qw QX rA rN rP sC Ss Tn tR TT Ua Uh uM uP Us Ut Uu Vv yD zG xA) jQ(Ad Ao Bb bF cK Dc dI Dk eD Et Fr Hb Hf Hq Id iH In Ir Is Je Jp Jq Jy Kd Ke Kq Ky Lw Lx Mt Mu Mz No Nu Nw Ny oE Oi Pa Pf Pg Pj pS qI qY QZ Rf rP rR St tQ tU uG Uo uR Us Ut uU uV vI vQ VT wP zI yE tM tL) fY(Ao Aw Bb bF cK Dc dI Dk Et fN Fr Hb Hv Id In Ip Ir Is Jd Jh Jj Jp Jr Jy Ke Kq Ky lM Lw Lx Ma Mt Mu Mw Mz No Nq Ny oE Pa Pf Pg Pj Qd qU Qv Rf rP rR rX St tQ Uh Ut uU uV vB vI vQ vS VT zH yE tM tL xA tF) qP(aA Aj aN bJ bU cC dA dJ eC Ed Fw Gl Gp Ha hC iH Ik Iv jD Je Jj jK Jp Kf Kk Kz lL Lu Mk Ms Mt Mw Mz Na Nd Nj Nl Nr Ns Nu Og Oi On Or Pa Pc Pg Ph Qc Qv Qw Rb Ri rR rV rX tN Uk uN Uo Ur Us Vt wG yH xA) qO(aD Af Aj aN Ao Ar Aw bG bN bS bX dA dC Et Gl HA Hb iA iH Iv iZ Jd Jj jL Jp Jr jY Kd Kp kQ Ky Kz lL lN Lu Lx Mu My Mz Na Oa Oi On Ow Pa Pc Pe Pg QU QZ Rb rP rR sO Ul Up Us Uu uV Vt tL tF) vV(Ad aN aQ aR bG bN cQ cY dA Dc Dp Et Fb Fw Fy Gp Hb Io Is Jj Jm Jp Kd Ke Kg Kk Ky Lh lN Lu Lx Ma Ms Nb Ns Nw Oe Oh Pa Pc Pd Pe Pg Pi qC qD Qh Qy Rf rR rV rY Sr Tr Ub Uf uN Uo Us uU uV vB vI Vt yH) vS(aG Ap bG bL bX cB cL cS Cw Dg dH dN Dp fP Hb Hf Hq Hw iH Io jF Jo Jp Jt jY Kf Kg Ki Kj Kk Kz Lu Mb Na Nj Oi Ok Pa Ph Pj Pk qB qT QU Qv Rb Rf rX rZ sC tR Tt tU Tv uG Up uV vQ wF yK) xA(Aa aC aL BG bQ bX cD cR cT Dp eD eZ Fb fP Fy gP Hb Io Is Jm jR jY kR lK lL Mz

Figure 6 Continued mE mY Mz Ni Nm nN Nw NY Oa ON Rg Sr St Tv Ur Us Tl) Tv(Aa Af Ar aX Bg bZ cA Dp Ed Gp hC Iz Jj Jk Kd Lv Mz Nd Ni No Ny oF oH
Ou Oy Pb Qm Rt Sr St Ul Ur Zx Tl) Cw(AJ An cV hC Kl Kr Mg Mk mP Mv Mw Ni Nr nT nY oH Pb Pg Ss Uc Ux Uy) cX(Ha Ih Ir Jg Jt Mz
Nm Nr Nw Ny Ok Qa Qb Qe Rf Rm Sr St Un Vu Yi) Pb(An aQ cF Cp Cq Ef Fc Hl Jq mE Mv Ng Nr Nx On Ss Tt Us Uy Xa) Mv(aC aL AX bE
Jj Jq Lj mE Mz Nm nN Nr Ny Ok Pk Zx) On(aD al aL bE cB cJ cS cZ dA dD HC IX mE Mx oD Qy) St(Af aL Ax Bn Cx De Id Li Lv Mk Mn
Nd Nx Qy Ub Th) Ul(Ax Cs Fp Ir Li Lj Mb Mn Na Nd Nk No nY oP Zx Th) oH(Dr Fd Fy Gc Ha Jt Kq Ks oN Pd Vh Yj Zx Ti Yf) Nr(Aa aJ aX
cS Hf Hr mE Mk mY Nj Pc Pg Qy) Us(aN aR hC Hx It Nd Ng nW oE Ub Uy Wc) cR(Du Gp Hr Jf Lp Ly Nq Rv Sf Sh Yk) We(bC eM hC Li Lj
Mb Mn Ny Zx Th) Qy(Ao Fy Ij Im Ks Li Lu No Ok Ph) hB(Ax cO Cs Dr Em Gh Gp Lj Ow Pj) Af(Fa Ha Ke Mz Oa Rf Sr Uy Xa) Nj(bR Hr Im
Ir Ni No Ny Ps Vi) Fa(Bn Cx Lv Ma mE Mk Og Oi) Nd(Gp Iq Ke Kn Op Yd Yi Xa) Uy(aX cJ Iq Mb mY Ni Ok Tl) aL(Dr Ha Ir Jg Jt Nv Um
Ur) No(aK cS Hf Ic Id Jf oD) Gp(Ha Mz Nm Nx Oa Sr) Hf(Fy Ij Li Mm Ok Sr) Io(Ar bZ Fp Ma Mz nW) Ir(aD Hl Kd Mk Nq Vq) Ny(Cx dC
dD Jf Kd oD) aX(Fc Li Lj Na Nq Um) Aa(dD Hx Iq nW Qb) Th(Kd Oe Of Rz Sj) Ni(Ha Jq mY Nx Pd) Zx(Cq Mw Ng nW Nx) Jg(Fp hC Mz
Oy Ss) Vq(Fy Il Im Vw Yi) Mk(Lx Ng Rf Tn) Rz(eM Mb Mn Ss) Lj(Fd mE mU Ng) cV(Ha Kq Nm Sr) Ma(aJ Ez Ss) Mz(Ng Nx oD) Tn(Ed Lv
mE) Ij(Ic Ju Vb) Oa(Bn De Mj) Dr(aC dD) Fp(oD Sj) Mb(Yh Yi) Qe(Mj oD) Sr(Bn Cx) Xa(eM Vh) Li(Pd Ye) Nv(Je Jk) Nx(mY Tl) Ok(mP
Nq) Ur(al Oe) cS(Ow Yi) mE(Kq Tr) ArJq BoOf CqOu DuHx YfMx FdMe FyIc GhNk NgJj TznW TthC IlQv ImdD SjeM KrPj YIoF UpeC
bQcO} oD{hB(Ax bB bH Bo bP bR bU bX cH Cq cR Cv dA dE Di DK dR Em Fw Gn Hr Hx iJ In Io It Iu Ji Jq Kn Ko kQ kS Kx Kz Lj Lu lW
lX Md mI Mk Mq Mt NC Nd Nc Nf Nh Nj Nl No Nr Ns nY On Ou oV pI Pj Pz Qc Qe Qy Rb Rc Ss Tn Tt Uc Ut Uu Vt Wm tF) Kx(aC aD Af
aM aQ bC Bn bQ bU bX cE cT Cu cX dF dG dM dN DR EF Fa Fb Fi fR iJ IZ Jk Jl Jq kQ Ld Lv mE mF Mk Mq Ms Ns NW Ny Oa Oe Om On
oO Ql Qn Qz Rx Si To Tt Ua Ue Un Uo Vu Vv Vz) Vz(Ao Ar Ax bW bZ cR Cw cZ dK dN eM Et Ex Fa Fp Fy gL Ih Ij Il Im Ir Jn Js kF Ky Ld
Li Lx Lz Ma Mh mI Mt Mx Na Nn Nr Nt nW oE oF Oh oK ON oQ OW Pe Pf Po Qa Rf Rh Tn Tt Vh Yi Ti Th) Ld(Aa Af aH aI Ao aX aZ Bg
cG Cw Cx dL dN eM Et Fw Gc hG Hu iJ Je Jf Ji Jk Jt Ko Kr kS mE mI Mk Mn mS Mu Nc Nd Nm nN No nW Oe Og oO Oz Pc Ps Pz Qn Qw
Rh Ri St Ua Uc Ug Uo Vh Vi Zx) Nv(aH aI Ar Ax Bg dN Dp Du eM Et Gc Hq Hv Je Jk Kz Li Lj Ly mI My Nc Nd Ne Nh Ni Nl nN No nW oO
Ou oW Oy Oz Pb pK Qh Qn Qw Sh Uv Vs Wd Yg Zx Ye) Ut(aM Ba BG Bo cD cE Ct dN Dp Ed eM Hq Ib iJ Jj Kg Lh mT Mu Mv MY Nd Ne
Ng Nh nN No nW Og oO Ou Oz Pb Pg Pz Qn Qw Ry Sh Ua Uo Uv Vs Yd Xa) No(Af aG aI aL As hC bF bN bU cQ cR Cv Cx dF dG dR Fa iJ
In iO Kc Kk Kn kQ kS Md Mk Mq Ms mT Ng Ns Nt nU Nx oQ oT pI Qh Qn Rf Ri Ry tF) Th(aA aH aS aX bF BG cE cX Ed eQ fR hC Ik iZ Jk
kI kQ Lv mE Mk MY Nd Ne nI Nl nW oQ Ou Oz Pa Pb Pg Pz Qh Qw Uo Wc Wf Yg Zx Tl) mT(Cw dF dN Dr Ed Et Fa Fp Iz Ji Jk Jv Kq Kz Lj
Ma Mk Mz Nc Nd Ni Nk nW Oa oF On Ou Oz Pa Pb Pk Qe Qh Qn Qw Ua Un Zx Tl) cR(Dr Fw Gp Hl Hr Hv Ik Jg Ji Jk Kn Ko Ky Lp Ly Ma
Mv Mz Nc Nd Nl Nq Ny Oe Of On Oz Pa Pb Pd Qc Qe Si Ua Uf Wb We Yj) Dr(Af aZ bB bP Cx Dd Dg dH dL Du eM Et Fw Ji Kr mH Ml mS
Nd nH nI nW Og Oz Pb Qu Rc St Tt Uc Ug Uo Vh Vq Tm) Zx(Ao aV bJ Ef Fb Fc Gc Gh Ih Il It Iz Mt Mv Ng Nn Nt Oe Oh Om On oO Op oQ
Ph Qn Qz Rm Rx Tt Ua Uo Yi) nW(Af aG Bn Bo bP cJ Cs CX dC De Di dK Du Ex Fp Gb Kn Ko Li Lj lW Mq Mt Nk Nm Ny On Qe Rh Sr Tl
Xa) Fa(Af aX Bn cI dL dN eM Et Gc Is Jr ml Mk mS My Nc Nd Ne Nh nN Og oO oW Oz Pb Qh Qn Qw Rh St Uo) oQ(aE Af aH Ax bB cO Cs
CX De eF eM Et Hu Je Ji Jk Ko kS mI Mk Mn Nc nN oF On pK Uh) Qn(Ar aS Ax bG bI bR bX cD Cs Cu dN eM Ex Fp fR gL Jn Lj Nk Nl Oa
oF Pe Qa Ry Sr) Oa(Af aI aM Gc Hv Jr Mf Mj Nc Nd Ne Ng NH Nl Qg Qh Ub Uw Vh Vi Vp Tm) On(Af aG Bo dR Hq iJ In kQ Lu Mk Mq Ms
Nc Nd Ns oO Pa Pz Qw Uw Va Wb Yg) oO(Ax Bo dK Du Et Ex Fp Jy Kn Li Lj Lp Lx Mq Mt Na Po Qe Rh Sr Yi Tl) fR(aH Gc Hr Je Ko Mz
Nc Ne Qe Qh Qw Ri St Ua Uh Uo Up Vh) Nd(Ar Fb Gh Im Iz Nr Nw Ny Rh Ru Rx Tt Uy Vi Vj Vv Yi) Fp(Af aI aM Cw dG Gc Hr iJ Ko Ng
Op Rx Rz Ux Vh Wc) Yg(Gh Ij Li Nn Nt Oe Oh Ow Qa Qz Rm Tn Ur Vi Yi) Mq(dN Et Jk mE mI mY Nc Nk nN oF oW Oz Pb Uo) Gh(BG cD
cE Jk nA Nc Nf Ou Oz Pb Qw Vs) Gc(Bg bZ dN Hf Ih Kg Kz mE Nc Ni Ou Oz Pz) Tt(Ba BG Ez Hq Jk mY Nc Ng Ou Pz Qw) Vh(aA dI Lj mE
nB nC nH nL Tr Ur Wb Yd) Ha(aG aH Cw Dp Du Fi Hr Nh Nl Si Yh) Qe(Af aG Bn bU bX cX dF gL iZ kQ Mk) Qz(Dp Eq Jj Jk Nc Ne Nk Nl
Qh Sh) Ax(Af aG cX dF dN Fd Hp Mk Wb) Cw(Ad Ap Ed Gd kQ Nc Ry Sh Yd) Du(aV dN kR mE Ny Pi Qd Qh Uo) Et(Gd iZ kQ Lu Ms Ns
Pe pI Yd) Oz(Ho Md Mt Ns Nx Rh Rz Sf Vw) nN(Mt Rt Rx Sh Va Wd We Wh Yk) cX(bI Li Lj Nn Ny Qa Sr Un) Ko(gL Jy nC nH nL Ry Tr)
Nc(dF Ny Om Rx Uy Yi) Nk(Af Bn bZ dF Fd Mt) Qh(gL Hx kR Mt Vw Yj) aH(dK Hl Jd Kn Pe Vb) dN(aL bB kQ Nx Rh Xa) Ed(Rv Rz Vb
Vw Wh) Mk(Ar Li Lx Po Tn) Yi(Jk Ng Rh Ua Uo) Ry(Ih Lj Nm Ny Un) Pb(Md Mt Ns Nx Uy) gL(Qw Ua Uh Uw Wd) Af(Im Nn Rf Un)
Rx(Cs Jk Ou Pe) Ny(bO bX fP iJ) Vw(Ez Ng Ou Uw) kQ(Ar Lj Nn Nt) Eq(Ao Dl Ph) Nl(Bn Tv We) Yk(Uh Up Ur) Yd(Ji Nm Vv) Wb(dK eM
mI) dF(Bo Cs Lj) Bg(Uy Vi) Mt(aX Ng) Qa(bX Fi) Wd(Jk Nq) Kq(cW Kg) Ps(eM Im) Un(nC nH) Ph(Si Uy) iZ(dK Uh) ArJq CsaG CtRz YfPe
NnbX IhUw YjUr SjbZ WhkR JkVi XaeM TlUo LjaM RtUp QlVs} qY{Yd(aC An Ax aY bA bG bI bJ Bn bQ bV cE cG CP Cq cT Cu Cv dJ Dl
dN Dr Em Et Ex Fa Fp Fr Fw Gc Gl Gn Gp hA Hl Hp Hq Hr Hx Ic Ii Ij In Iq Ir Is It Je Jo Jr jY Kd Kg Kj Kk Kn Ko Kq Kr Kx Ld Li lO Lu Lw
Mc Mg Mj Ml Mp Mq Mr Mu Mv Mx My Mz Na Nb Nf Ni Nn Nq Nr Nt Nx Ny Oh Ok Ow Pa Pf Pi Po Qg Ql qT Qv Qx RA Rj Ru Ry Sr Tn
To Uc Uf Ug Ul Un Up Ur Us Uv Uy Uz Vp Vt Vu Wd We Wg Yl Tl Xa Ti) Op(aI aL aM AS Ax bA Bc bI bJ Bn Bo cQ Cs Ct Cu CW cZ Dc
Dd De Di Dk dL dM Du Ef Em Ex Fa Fc Fd Fr Fw Fy Gc Gn Ha Hf Hl Ho Hp Hv Hx Ii Ij In Is It Iz Jd Jh Jn Jo Jt Ke Kf Kk Ko Kp Li Mb Md
Me Mj Ml Mp Mq Mu Mw Mx My Mz Nf Ni Nm Nn No Nr Nt Nv Nw Ny Oa Of Ok Ow Oy Pa Pd Pe Pi Pk Qh qX Ra Rb Rm Rt Ru Rv Ry Sr
Tn To Uc Ud Ul Un Uo Ur Ut Uv Uw Uz Vb Vh Vp Vt Wd We Wf Wg Yl Tl Xa) Uw(aW bM bN cH Dc dE Ez Fn Gb Gc Gh Hr Iq Jg jR Js Ki
lK Mh Ms Mt Mv Mx Nk No Oi Oz Pa Qn Qw Qy rA Ri Rj To Uh Uk Uu Uv Vu Vz Wh Wm Tj) Wh(aI Aj aX bH Dg Fw In Iv Jj Jo jU Lh Li
Lj Lv Ly Lz Mb Me Mh Mj Ml Mp Mq Mx Ng Nl Nq Oh Oi Ow Pa Pb Pc Pf Qh Qv Ry Sf Ux) Fi(aF Ao aR bS bW cG cL Cu dC Et Gc Hb Ic
In Jf Jy Kr Ms Mv Nb Nq Nw Ny Oi Ps Qa Qc Qd Qh Qm Qw St Uh Zx Th) Wc(aC aI Bg Ch Co cT Cx dD Jh Jl jP Jy Kk Kr Lv Mj Mk Mm
Mn Mz Nn Nq Ok Om Pb Pc Qc Qd Ql Qm rB Rg St Vh Vq) Ho(aC aM aZ bH Cx Dl Ed Gd Hb Jy Kr Ld Lp Lz Ml Mn Mv Nb Nq Ny Oh Ow
Oz Ph Qb Qg Qh Qx Tv Uh Ur Ut Zx Ti) Vi(Af aJ aK AW Ax bL Bn bV Cq De Dg dH Ez Gb Jh Kx Nc Nf Nq Pb Pc Qu Qw rB Rj Rx Uh Ux
Vv Tm Th) Yj(Ad Al aM bU Cq cT Cu cX Dd Fy Ib Io Iq Is Kc Kn Mf Mg Ni Nk Nv Qc qX rA Rt Ry Up Vu Yh Yi Zw) Zx(aY bC cH cP cQ
dJ Fc Fw Gp Hx Ii Ir Iv jE jH Kg Kj Kn Md Nc Nl Qc qX Rc Sj Ug Wm Tj Yf) Di(Ad Dp Et Fn Fy Gd Hf Hq Ic iH Io Iq Jd Jg lL Lp lW mH
Mm mZ nC nK Pj Tt Vb Vq) Gh(aA Bc Bn Co Dc De Dk Et Gz Hf Ib Jg Ko Kq Nc No Nv Ny Oa Om Qc Ua Uc Vs We) Sf(Dk Et Gc Ib Ii Iz Jg
Ju Kf Kp Mg Mn Nd Ok Pd Pe Pj Ps Qa Qd Qm qT Up Tl Ti) Rt(Aj bH bO bR bX CT dC Dd Fr Hl Kj Kr Nb Oa Oh Pf Ps Qd Qm Rv Rx Uh
Vo Ti) Fc(aM aZ Bg Ch Cx In Is Jy Ki Kr Mm Nq Nw Ny Oz Qa Qc Qd Qm Qw Rm St) Vz(aA aI bR cZ dD De Hf Il Jd Jy Kk Nb Nl Ny Om
Pe Po Qy Up Vs) We(AN Ba bR cD cH Cx Ex Gb Ke Ki Nl Pj Qv Qw Rg Rj Uh Ut Th) Wd(AN Ba Bb cT Cu Ez Ir Ki Ld Nl Oh Pe Pj Qy Rg
Rj Vb) Rx(aM bJ Cp Dk Dr Gc Hc Iq Jl Jq Jy Nb Nx Of Pi To Tl Wm) Yk(aR Bn cB De DK Gz Hf Ib Iz Jh Kq Mt Nv Ny Pe Po) Yf(aI bH Cx
cZ Ed iB Jd jK Kk Kr Mw Pf Rm St Vh Ti) Gc(bU cF Eq Hu Iz Jk Ly Mg Qt Qz rA Sj Ua Ut Uv Yi) Sj(aM bB bR Fr Ic Jf Mk Pj Ps Qa Qd Ql
Qy St) Rz(aM aY Bg bQ cE dF Gl Mg Ng Nv Of Ou Qz Uf) Gb(Bc Cw Et Hf Ir Jt Kk Mv Nv Ny Ok Om Vs) Gn(Ao bH cT Hu In Mn Nq Nw
Oz Pf Qd Qm St) Xa(bH bM Cx Fn In Jd Jf Kp Kz Oi Om Qc Uh) Yg(Bb Dk Ed Gd Iz Jl Mh Mz Ok Qa Qv Vu) Yi(bN bR cP cW Ed Fw Lh Nl
Nx Ow Qc Qv) Si(Bg bN Fw Gl Lu Nd Nw Qa Qu Qz rA Ua) Ps(cF cW DD Hc Ih Ju Nc Qa qT qX Up) Tl(bH bR Fa Gd jP Ju Mb Qc Qv Ua
Uh) Vc(bQ cE cG cS Gl hA jT Nn Qv Uf Vq) Vj(bU Dd Ed jG jT Lu Mg Nd Ng Ni Qv) Du(aM Ao bH cT In Iq Lh Po Sr) Lp(Fr In Iz Kj Kp Nv

Figure 6 Continued

Figure 6 Continued

Om On Qv Rz Tn Um Us Yi) rA(aJ Ao AP AW bB Bc Co dB dD dJ Ef Et Ex Fc Gc Gn Hc Hu Jp Jv Kf Kx Ld Mg Mm Mp Nj Nk Om Ow Pd
Pf Qa qT Sr Ub Uc Un Uu Vh Wb) jF(aH Aw bB bH cB cG dD dE dF Ex hA Hb Im Jl Jp Js Jv Ke Mm Mn Nn Nv Nw Ok Op Pe Qa Qh Rm St
Tn Uh Vj Zx) Cw(aM bW Ed Ha Hl Hr Hx Ii Iu iZ Jd kC kl Lt mE Mn mY Nd nT oK Or oW Pk Ps Rg Rx Sf Uf Ur Vw Yf) On(aM aY bB bR
cB cF eC eM Ex fB Fw Gp Ha Hr Hx Jd Lt lY Nd Nj Nv Nw Pg Ps Qm Rg Rv Ur Vp Zw) Jg(Af aM aY bB bR bW cB cF cX FB Ha hC Hr Hx
In Kp Lt Lz mH Ml Nx Or Qv Rg Rv Vp Tj) Fb(aH bB Bn cl dD dF eM Et Gp Jd Ji Ko Kq Mn Mv Nc Nd Nl Nq Ow Oz Rc Rx Up Vh Yf)
qT(aY bQ cZ Em Gc Jv Kf Ko Ni Nk Nn Pj Qu Rt Sf Sh Si Uf Un Up Va Vt Vz Wd Yd Ti) Ef(Af al aU aV aW aY bB bE Bn Bo cB cF cG Ct
cY dD Gn Gp Hr Ji Ml Mn Or qX Rv) jP(aD aY cJ cO cP Cq Ct Db dE dH Hr Ik Iz jH jU jV Kf Kl Kp Kz Oz Pk Ry To Vz) iB(aJ An aP bP cH
Du Fi Ho Ic Il jE jH Lx Md Nk Nx Qc Qw Ss Ua Uh Wc Wm Yf) IK(bH dD Du Et Fp Gc In Is jl Jv Lx Mh Mt Nj Nq Or Oz Qe Rg Vb Vt)
qX(aJ aY bU Co cP dD dE Dk Ez Fr Fw Ii Ip Iz Lp Ni Rf Uc Un Vh) jl(Ap cQ Dl Ez Fr Gb Gc Jt Kf Kg Kl Ko Ms Nm Oi Pd Qu Ry Uu) oO(aL
bQ bU cV dD gC Gn Gp Hl Hr Mv Mw Nq oH Qv Sj Um Yj Xa) Vh(aM bB bU cF Ch cX dF Dk Fr Gn Hr Jd Lv Mt Nx oK Om) Et(aM aR aY
bR cB cF Ch Dk fB jH jR lY mH nl Pk Ss) Mn(aN cB eC eQ iJ IZ jH nB nl Nj Nx Ss Vp Ye tF) Ji(aY cF Ch dF eQ fB Hr Hx iZ Lt mH nl Nw
Ru Ss Tt) jK(Ba bC Bg bY cA Jt Kf Kg Nm Of Ry Uc Uu Ux Wh Yg) Ko(eM fB Fd Gb iZ jU kl IL Lt mH Rg Rj Sf Vp Ti) bB(Ch eM fR gZ IZ
Jd jH lY mP mT mY mZ Ss tF) jQ(Aj aK Ap Db Dg Gl Jt Kf Mw Pd Qu Uc Ux Vv Vw) Nq(cB eM fA Iz Jd kl mH mM mP mT mU nN Pk Ss)
Ut(Ad aM Dd eM Gp Hr Jd Ps Ru Rv Ss Vp) fB(Ao Ba cE Cq Dd Dg Du Fy Gc Jt Rc Rz) jH(aD aZ dD dE Fw Hq Ik Jq Js Mt Qe Tn) Dk(aR cF
Ch Dc dD Em Hr Mt Nj Rj Vp) eM(Du Fr Hb Io Jn Jq Kq Om Op Ow Tn) jL(aP Aw Ex Hu Ik Kx Pd Pf Pg Uo) Mt(Af Bn cB De Lt Ps Qz Rc
Ye) Ss(aH dF Jr Li Lj Or Rg Rv Uh) lY(Ao Bn bQ dF gC Gn Gp Jq oV) jR(aK Ap Gc Gl Jt Kf Ua Ux Vw) Jd(Af Bn cB cF De dF Of Yf) Qv(fA
kG kI mH mP mT mU nR) IL(aA Gb Ic Jt Kf Pk Ub Yg) Rv(Ad Dd dF Dg Iz Kl Tt) hA(bH Du Ic Ik Je Oi Va) qU(dD Jh Nc Nj Nk Qh Wb)
jU(Ap Db dD Fw Pd Tt Uu) Hr(Ad kE kG nC nR Tn) mH(Aa bQ Gn Gp nK Oz) mT(aL dB Du Fi kC mE) hC(De Fi Gc Rj Sh tF) Or(Ad Ch Dg
Kl Tt) fA(Af aL Ax Bn cJ) kl(cR iJ Pa Rj Th) oW(aU cG cY nU oH) Gn(kP nl nR Rt) Iz(aY cF Rg Uh) aM(Ng Ok Rz Uh) bQ(kC mF nl nO)
dF(jO kF Rg Rj) nT(aY cG Gc hB) jV(dD Jv Kf Tt) Fr(Gp Lt Rx) Hl(kE nR pK) Tn(Hq Qm Vp) cR(mU nB nC) mY(aG Aw Bn) hB(IX nO nU)
oH(kE nC nN) Ch(Qb Uh) Du(gL mE) Tj(nC nK) Fi(nR pK) Rg(Dg Kl) aP(jO qW) cB(aY lm) cF(Ok Ow) eC(Bn Nc) nB(Cq Th) iC(bR Sr)
nW(Ng nR) oK(Cu Kf) oV(aU cY) AakC AdUh AolX AxkG EzqV NotF MvnO lbqW YjlO KejY LtOh RjpK aHkO aLlW bHjE cJoQ cXnA
eQnU} Pj{xA(Af aP aW aX Bc bQ bV cV Cw Db dH Di Ex Fb fP Fr Gp Hf hG Hr Hu hW Ic Ip Jp JU Jy kQ Ky Kz Lh Lv Ma Mn Ms Mw Mz
Ne Ni Nq Oc Oi Ok Ou Pa Pd Pz Qn Ri rR rS rW sC tN tQ tT tX Un Ur Us Vt tL) sH(aN Ax Bg Bo Ch Co Ct Dc Ef Hb Hq Hr hW Ib Ij In Ir It
Iu Iz Jk Js Kd Kk Kp Kr Ld Mg Mj Mv Nd Ng Nj Nq Oe Of Og Oi Ou Oy Pc pF Pz Qb Ql Qy Rm rZ Vu Vv) rN(Af aU aW cB cF cL Cw Db fN
Gp gW Hf Hr iA iH jF Js Ju JV jY Kd Kf Kk IK Ma Mn Na Nq Nt Qd Qn Rf Rh Ri rR rW sC sF St tO tT vB VP vS vV yH tL) wD(aU bP fN
Fw Hf Hu iA jF Js Jt JV jY Kd IK Ma Mn Ms Mz Na Nq Nt Pz Qd Ql qP Qw Rf Rm rW sC sF St tO Us uZ vB vH Vp vS Vt vV tL Wn)
qB(Af aP Bc BO cB cH CW Db Di Fa fN gW Hf hG Hr Ic iH Ip iZ jE jV jY kQ Kr Ks IL Ma Mq Mw Na Oe Oi On Qn Qv QW Un vS yH)
yH(Af Aj Bb Bo cV Cw dH Di Fb fN gW Hf Hu iH jF Jv jY Ky Kz IL Lv Mn Mz Oe Qv QW Ri sl tO tT tX Ur Us zH tL Wn) uL(Af aW aX
Bo Cw Db dH Fb fN fY gW Hf Ic iH jF jQ Kr Ky Kz IK Lv Na Ok Pc qO qP QW rW sC tO TT Us Wn) vS(aA Aj aP bA Bo bQ bV cC cV Db
iH Jd Jj Jm Jp Ks Kz Lw Ma Mn Mz Ou Qv qW Ri St To Tt tX Ub Ug Ur Us tM Wn) vH(Aw bA Bc Cp Cu CW Di Fa hC hG hW jE jl Kp KQ
Lh Lv Lw Md Ml Mq Mw Ny oF Ok Om Pb Qv qZ Un) tO(Aj Bo cH Cw cZ Di Fa Gp Hv hW Iu Jm Ks Kz Lv Mn Nd Nq Oe Og Oi Ph Pz Qd
Ql QW Ri St Us) vB(Af Bc bQ bV Cu cV Cw Db dH Di Hr Jp Jv Kp Kq Ky Kz Lh Lv Mn Mz Ok On Qv QW Wn) tT(Aj bP cH cl Di fN Gp Hu
iC Ip Iv jV Ks Lv Mn Nl Nq Oi Ph QD QW Ri sC St) sC(Af Aj Al aX bA Bc Bo bQ cV dH Di fN hV iH Jj jO jY Ky IL Nq Ph qW Ur zH)
sF(aN Co Hq Ij Il In Ir Iv Jm Js Kr Ks Lz Mg Mj Nd Nq Ns Of Ou pF Qb Us) rW(aD aG aR Bc bZ cE cF cL Di Hf iA iH Iv jY Mn Mz Nq Oe
Oi Qv qW Ri) gV(aD Ax bl cK Cs dM eP Gl Ir Iu Jj Kk Kn Lx Mz Ny Og Ug Ut) tX(Af Gp Hf Hu jV Ks IK Mn Nl Nq Ph Qd Ql QW Ri St)
tM(Bo bP cH Di Fa Gp Ic Ip Kf Ma Mw Mz Nq Oi Ph Pz Vt) vV(bA Bc bQ cW Di Fr hC hV hW Jp kQ Oe oF Ok qW Ri sM) hO(Bo Cw Db Di
Ex Fa Fb gW Hf iH Kr Ks Na Oi Qv) tN(Af bP Di iC Iv Ks IK Lv Mn Nl Nq Qd QW Ri) rR(Bc Di Fw iA Kr Ma Mz Nq Oi Qb Qv qW tS tL
Wn) eP(aG bB Bc Ch dF Ef hB Iq Ko Ld Mp Ok Ou) tS(Af bP cH Cw Di Jp Lh Lv Nd Nl Oe Oi Ri) tL(bA bC bV Fa Fb hC hW jE jF Jj Md Qv
Un) fN(Bb Jd Je Jj Jp Mz Oe Qh qW Ri tF) qD(Cw Db Hf iH Kr Mn Na Nt Rf Us wJ) tQ(Di iC jF jV IK Na Pc Qv Qw rV) uZ(aA aP cW Di dN
Fa Kq Lw Mq Mw) wK(bP jY Kp Nq Oe Oi qW uW Wn) iH(Ad cQ hL Jg jY Nn oK rB tF) wH(Fw Hu Nl Nq Ph Qc Qd sK) jR(Db fY Gn Hl
Ho Ic Ry Ye) Qv(bC hL Jd qQ uT vO tF) Wn(pF qP rS rT rU uI wL) uW(Bc eF hC hG iZ kQ oF) gW(Ho Vz Wd Wf Ye Tm) rA(Gc Hp Uw Uy
Yj Ye) jQ(Eq Hl Ic Ux Zw Ye) vP(Di hC hV hW Oe qW) hL(Cw Db Di hC Lh) sM(aK Ic Ip Ql Qw) yL(Ju JV Qw Ri) Fi(mE mF nU oO)
dX(eC iJ iO Kk) oK(Cw Db Hf Na) Di(hR hX jY) Ic(eD iC uR) Xa(eM gZ oO) eQ(Gh nW oO) jI(Em Rv Va) qX(Fd Rv Si) qT(Du Vz Yl)
jO(Gc Rz Wh) Cw(oH sK) Gn(mE nI) Hf(jY qU) Qd(qZ wF) Qw(uV uX) Uw(jF jL) fA(hB Wb) iA(rS vW) iC(Wh Ye) tR(bP Pd) lO(Eq Na)
DbeD EfYg FbqC NquR MnwF HpjL SfjU JsqZ OefY UsuV VcgL PhtU aPuX tFrQ gZiJ hWsK hBoT yJqV zHrZ kRrS} Et{Eo(AD Aj aP aW
aY bA Bb bI bM bP bR bV bZ cH cO cW dB Dc dD dG dJ dK Dl dN Ef eP Ex Gd Gl Gp Hv Ii In Jj Jk Jm Jq Jr Jt Lj Lv Ly Mb Mk Nc Nd Ne
Nl Nm Ny Og Pa Pb Pc Pf) tT(Al aR BG bZ cF Di fN Gp hA Hr iA lC Il In Ip It Iu jV Kd lK Na Nk Nq Nu Oi Qc QD qU QW rB Ri St vI yH
zH Wn) eO(aG AO aR aY bR cR dJ Dw Hu Ih Io Jk Jo Jr Js Jt Ly Mb Mt Mu Mv Mw My Nb Nh Nl Nv Ny Oe Pa Qa) rN(aR aU bZ cB cE cL
Cw Db dG Gp Hf iA Ic Ih Js Kk kR Na Nq Nt Qb Rf Ri rW sC vB vH vP vS vV tL) Nd(aA aO aR aW bC Bo bU Ch cR Cw Db Di Ii In Jj Jo Li
Lj Lw Mh Ms Nc No Of Oi Ok Pf) Qv(aF aO Fn iA Ic Jd Kk Kr Na nL Nt Qy Ri sC tS Ue Uk uZ vB vH vS vV yH yL tL Tj tF) Mb(aA aC aO
aR aW Bn bR cQ Fb Hx Ii Jj Jo Lj Ms My Na Nc Ne Nk Nl Of Oi Ok) tX(aR BG cF dG fN Gp iA Il In It jV lK Na Nt Oi Qd qG Ql qU qW Ri
St yH) aO(aC aR aW Bo cK cQ Di Fb fP gL hC Hf iA iH iZ Jd Kr Kx Mt Na Ne Nj Nl) Di(aR iA iH jM Nj rO rU rW tN tO tR tS uZ vB vH vP
vV wP yH tM xA) tS(Af Al Bg bZ cF fN Gp iA Ic Ky lK Oi QW rB Ri rW St yH Wn) Na(aC aR aW cK iA Jd Je Kr Kx oK Ow Qy rW sC tQ
Ue uL yH tF) Nc(Hx Ii In Io It Jj Lv Mf Mh Ml Ms My Nb Nh Ni Of Oi Oy Qb) Nl(aA Hx Ii In Io It Iu Jj Jo Lv Mh Ms My Nb Nh Of Oi Oy)
Jd(aM Db Fn Hf Ic It Iu Jv Kr My Nt Nu Oi Ql Qz Ri Rm Tj) yH(Af Bo gW Gz Hf Hu iH In Iu jY Ky Mh Mn Oi qW Ri rX zH) sC(Al eD fN
gW iA lH Il jP jY Ky lL qW Ri rW sJ wL zH) Ne(Hx Ii In It Iu Jj Jo Lv Mf Mh Ms My Nb Nh Of Oi Oy) Nj(aA aR aW Bo cR Cw Db Hx In Li
Mf Mh Ms Of Ok Oy) iA(aR Bo bU Cw Db Hf iH Kr Kx Mh rW tR vP vV wK) eP(aC aW bB eC Fb hB iP Ju Kk Ko Ld Ou Ow Qn) Ii(eW Fr
Hx Ik Jg Lh Lx Ml Mt Nh Nr On Po) Wn(fY pF qG qO qP rU tR vH vP vV wC wQ yL) aR(aC aW Bo bR bU cK iH Kr Lv oK rW sH xA)
rW(aG Gp Ic iH Iu jY Oi qW Ri sJ uP zH) vB(Af Cw Db Fr Hf Ic Il Kp Ky Lx QW) Th(eQ kC kI lW lY mP mU nB nI nN oO) Rv(kK lY mE
mM mU mZ nB nI nJ qT rA) tO(Aj Ba Bg cF Gp Il Oi Qd Ql qW Ri) vS(Aj aP fN gW Ic iH qW Ri Ub Ur Us) Eq(jK jO lK lL mH mP nD nI nJ
oQ) Ms(Hx Ik Lv Lx Mf Mh Ml Mt Nh Nk) Hf(FB Kx oK pI qU rB uL xA tF) eQ(Ax Cs Fp Gh Ha nW Oa Pe Qn) jR(Em Gn Ho Lp Rt Ry Va
Vc Yl) Fi(mE mF mP nA nJ nK nL nU) Nk(Hx In Lv Mf Ml Ni Ok Oy) Si(kE kF mP nA nD nK nL nR) jQ(Em Gn Lp Ry Va Vc Yd Yl) Ic(Fn
jG jM rB wJ xA tF) mE(Du Gd Hl pI Sf Yh Ye) iH(bU cM oK qT Ue vV tF) Ri(Kr tN tR vH vP vV) gV(aD bM Kk Qx Rg Vo) mP(Hl Vb Wc
Yh Zw Ye) yL(fN jF jU JV Qw) oO(gC Gn Hl Vh Wc Xa) pI(aA aH hC lX Mv Pa) Fb(Aj aW cR Kr Nt) Hx(aA Jj Jo Li Lx) Va(hR hV jK jL
mT) dX(bA iJ iO Kx nW) tN(cF Oi Pc qU Qw) Du(nC nJ qX rA) Gh(lY mM mS nN) Gp(tR wC wD wF) Yh(mF nA nJ nN) Xa(eM kF mW nL)

Figure 6 Continued

Figure 6 Continued

Jr Ki Kj Nh Pk) Af(kO lY mS mY nD nF nJ nL) Fc(cM dl Fn lk Ki Pd Qm Uc) Ux(aD aX bC bR dH dK Hb Yd) mW(Aj Bb Bc Bg cX cY Ef Iz) Gh(lc Ii Ik Kg Ko Nm Un) mS(Bc Cv cY Gl iA Kk Kp) nL(Cv gL hB Kf Kp oH Ow) Gd(cX Iv Je Nc Ni Nl) Yj(Jr Pd qW Qy Sr Un) Xa(Aj Hc Ib Mz Ri Wm) Vh(aU bE Cx hV jR Ki) nJ(Cv eF hB iA Kp oH) Di(Ic Ip lY mH wH) Du(cM dH Ql Qy Rm) Fi(cM Cu dl Ik Qy) Ye(Ex Fp ll Qa Ql) Lp(aD DK Ik Pd) Vw(aD bR Jq Ki Ns) nH(gL hB oH Ow Tv) Cx(kO mP mZ nK) Yd(Ex Je Kn qW) Tl(eD Im Is Iz) Wn(It Nt uM uV) Vc(Ap Cu Gl Ql) mH(Bo Dc Kd Pi) iJ(mM mY nD nU) Hl(Id Qm Qy) Ic(Ad Bb Kq) Wb(Ik Qm Sr) Op(Jd Pk Ug) cY(mY nD nF) mF(cD Dc Ez) kO(iA Kp oH) Dl(Vb Zx) Fd(Ik Pd) Fn(Rx Vj) Gn(Qa Uc) Yk(Ib Pd) Tm(Iz Kg) Lh(Sj vB) Rt(bJ Ql) aR(uO tL) fR(cM kQ) gL(kC mZ) mE(Cp Ct) mM(aM pF) nK(bL Cv) sl(pS rT) AdOi AnnD BbqO Eqls MgSh HxZx WcUt KftL RgkI OukP VunA aYoP cWmZ cXmU dBnO dJnN nUpF mYoH iZkC sFrS} eP{Hb(aC aG aH Ao AR Ba BB Bc bM bQ bZ cP cT Cu Cw dD dF dG dL Ef fP Fr Fy Hc Hw Ih Ij Il Im Iq Ir It Iv Ji Jn Jr Ju Jv Kx Ld Lh Li Lj Lz Ma Mg Mh Mk Ml Mn Mq Mr Mt Mv Ng Nn No Nq Nr Oa Oh Ok On Ow Pa Pc Pf Po Qa Qb Ql Qt Qu Ra Rf Rh Rm St Ut Vu Vv) hB(Ad aK Ap aU Bc Bg bM BO cC cF Ch cI cM cP cQ CW cY Dd Di dR eF eM Ex Fp Fr Ic iJ Ik Im In Io Iq Ir Iu Iz Jg Jh Jp Jt Kf Kp Kq Ks Kx Lu Lw Mf Mn Mp My Nd Ng Nj Nm Nn Nw Nx Oe Om On Ou Pz Qv Ub Ur) aW(aC Ad aG aH aI aL aM Ao AP Ar Ax aY BA bB Bc bF bI bM Bo bQ bR bU bV bZ cE cG cI Co cP Cs cT Cu Cw Db dD dF DG Dk dL Ef Ew Ex fP FR Fw Gc Ir Ji Jn Jp Lh Lx Mt Nw Oh Ok On Ou Ow Qa Qe Sr) Kc(aH aP AR Ax bA bM bO bQ bV bX bZ cG cP Cs Db dD dF dG dL dN dR eC Ex Fa Fy HC iA iJ Jp Kq Kx Ky Lh Lx Mg Mp Mr Mv Nn No Nq nW oE oF Ou Ow pF Qa Qb Qe Qv Qx Rf Tn Uf Un Ur) Ko(aH aM Ao bL cG cK Co cR Cu hC Ih Ij Im Ir Is Iv Ji Jl Js Kk Ld Lh Li Lj Lz Mg Mh Mj Mq Mr Mt Mx Nq nW oF Oh Ok On Or Ow Pe Pf Po Pz Qa Qb Ql Qm Qt Qy St Tv Vu) Tn(aK aX Bb bC bM bO bP bV cK cM cP cS Db dI Em Ex Fr Ha Im In Io Iq Ir Jn Kn Kp Kx Ld Lh Mb Mf Mp Na Nf Ni Nj Nk Ny Oa Ok On Ou Ow Oz Pz Qm Qx Rb Ri Sr Tv Un) nW(Ad aF aG aH aI AN aO Bc Bg cE cF cG Cw cX dC dF Dg Dk Em Gz hC Hx iJ Jq Kf Kk Kp Ky Ld Lh Mm Mn Nc Ne Nh Nv Ou Oz Pi Qn Qt Sr Um Uo) Ji(Aa aC Af aK aM aU BB bM Bn cK Co dB Dc dD Dk Ef Ez Fn Fr gV Gz It Iv Jr Ju Kl Lu Mw My Mz Nd Nj Ny Qn Qt Qu Ri Uc Ue Un Vt Vv tF) Ok(aC aK aM aU aV BB Bc bE bP cK dM eC eO Ez Fr IH Ip Iv Jr Ki Kk Ld Mq My Nd Nj Oa Of Or Ou Ow Pa Pb Qb Qt Rh Ri Uh Un Vt Tj) hC(aD aI aK Ar aV bH bM Bo bR bS bU bX cI cM cQ Db De Dl dL dX Ex fR Hu Ic Id In Iq Iz Kk Kp kQ Kx Ld Mu oK Ou Pd Pi Qm Ub) Kk(aK aM aQ Ar aU bW bZ cG Cw cY Db dD dF Di Ex Fr Gl iA Ik Jp Kq Kx Lh Ma Mg Ng No Nw Oh oN Ou Ow Ql Qm Sr Uk Un Ut) bB(Af Bn Ef eO gL Is Iv Iz Jq Kf Mf Mt Ou Qd Qm Qn Rf St Tz Ua Uh Un Vs tF) Nw(aC aU bA dM dW Ex Fn Gp Ib Ih Ir Kl Kn Qt Rg St Uc Ut Vu Vv tF) iJ(Aj aQ aV cF Ct dL Dp gP iH Jj oF Og Ou Ow Ri Ur Vs) On(aC bR gP iH Ju Jv Kg Kp Ks Ld Or Pk Qt Uh Um Uv) Ow(aE Af aG Bc Bn cM Cv Cx dH dI Kf Vs) kQ(aH aI aM aQ bR cG cM dD dL iA Lh) oF(bC Bo cM cQ Cw Fr Id Kp Me Qm Qn) Ld(iA Ib iO kR oN Pz St Uc Vu) aH(eC hG Kp kR Kz nY Ou tF) Ef(aC aM dD Ke Mn Ng Uh) Tv(Ar bV dD dF Lh Un) Kp(Ar Fr gL iA Kx Qx) Ou(aE cK dI gL Qn Qt) tF(aI Ao aV Fr Iq Nq) Uh(aX Bc Iu Qt Vv) iH(dF dG Lh Ql) oK(aG bA Fa Fr) oN(aG cM Fr Qn) Ar(iO Qx Ur) Ex(iZ Kn Kz) Qm(Dc eM pF) Eo(Ly Mt) Gc(aL dD) Id(dR eF) eO(cB Ly) iZ(bR Fr) oE(Ao cM) oH(dF Mt) BcOr BnSt FyIn GzgL MbdW MnUc TofP JnQn KqeC LhUt QlaI UnUr aMiP aVkS cPpF dXiO} Eo{Jp(aD aI Aj AR Ax bA BB bE bQ cB cC cE cG Cs cT cW dB dD dF fP Hr Ij Is It Iv Jj Jn Jr Li Lj Lv Lz Mh Mj Ml Mn Mq Mr Mt Mu Mx Nd Nf Nh Ni Nn Nu Ok Pe Pf Po) bB(aC aD aG aJ aN Ar As Aw aY bI bN bZ cB cP cR cT cX dA DC dF Dl DL dM Ef eM Ew Fp Hu Ii In Iu Jg Jk Jq Jr Js Mb Mk Ml No Nr Og Oh Oz Pa Pb Pc) Mt(aC aD aI Aj aL aN aR Ax aY bA bI Bo bR cB cH cI cK cR Cs cT dC dM Gd Hv Hw Hx Ih In Iq Ir Iu Jj Jk Jn Lj Lv Me Mk Ml Mv Mw Mz Nd Ng Oe Oh Ok) Oh(aD aI Aj aM An aP bF bN Bo bW cB cC cF cG cM cO cP dA dL eW fR Fw Gd Gl Hv Ik Il Ip Js Lv Ly Mg Mj Mm Mn Mp Ne Nf Nl No Nu Of Ok Pf Qd) Jj(AD Ap Bc bM cG cI Ct CW dB dF Dg Di Dk Dl Ex Hv Hw Ih Im Io Ir Is Iu Jg Jh Jn Js Jt Ma Mm Ng Nh Nr Nv Ny Of Om On Oy Pg Pz) Ok(aE aI Ar Aw Ax Ba Bb bM Bo bP cD Ch cL Ct cY dC dD dX eM Ex fP gV Jg Jr Jt Lv Mb Ml Mq Mx Nc Ne Nh Nl Nm Nn No Oi Pf Po Qb) Jn(aD aJ aM aN aS bA bF bJ bM bP cE cT cV cW cZ dA dH dL dM dW Ex fP gV Iv Lh Ly Mz Nh Nl Nn No Nu Nw Pb Pg Pz Qa Qb Qe) bM(Aw bA bJ Bn bO cQ dX Fw Hv Hw Im In Ir Iv Ji Jo Js Lh Li Lj Lx Mr Nh Nt Nw Ny Oi On Oy Oz Pb Pc Pf Po Qb) Is(aC aD aI Aj aN AR Bo cR Cs Ct cV cW dB dL dW fP Gl Hr Hv Iu Lv Ly Mg Nc Nd Ne Nh Nl Og Pg) Nw(aD aR aS aX bA bQ bX cB cF cJ cM cR cT cZ dB dC dD dF dJ fP Hx Mk Mp Ms Mw Pa Pc Pf Qe) On(aD aI Aj aN Bc Bo bR cD cP Cs Ct cW dL Ex FP Gd Gp Hr Hv Im Jk Jr Lv Ly Mg Ne Nh Of) aM(aC Af aK aN aU aV Aw bF bJ Bn cB Cp Cu De Di dW dX eW fR Ir Jh Lh Nc Ne Nh Ni Ns Pa Pz) Nh(aH aQ As Bo bR bU cC CP cQ Ct Di Ex Hr Hx Ji Me Mm Mn Mz No Of Og Pa) Lh(Aj aS bA bP bR cT Di eW Gl gV Hv Hx Ik Ip Jl Lw Ly Mm Mn My Mz Ng Of Pa) bR(aJ aP Aw aY bA bL Bo cG cW dF dG dL Iv Ne Nn Nv Om Pg Po Pz Qa Qe) Bo(Ad cG Ct Cu Dg Dl dN eW It Jl Js Mg Mz Nm Nr Of Om Pf Po) aI(cP Hx Ir Lj Lv Lz Me Mh Mk Ml Na No Nr Of Pa Pc Pe Po) bP(Hw Ih Ir Js Mg Mh Mj Mk Ml Mq Mr Mx Nk Nn Nr Oz Pb Pe) aD(bA bQ bZ Cu cW dF Ir Js Lv Mr Mz Ne No Nr Nu Pc Pf) Lv(Ao bF Bn Cs cV dB Di dW dX eW Hu Ly Mh Ni Nu) Mz(aC AR aY cR dC FP Fr Li Ml No Nr Pf) Po(Aj cQ cV Ex fR Ip Nd Ne Ni Nl Nu) No(aN cB cE cW Cx dB Hw Ly Mp Pf) Mn(aJ An aP Ar Cu dL Fp Li Nn Pf) Ji(aR aS bA bQ cR dB dC dN It Ni) Ly(Cu Ex Ir Js Nn Ny Pe Pf Qa) Mm(Ar aW Cs Jk Li Lj Ne Pe Pf) Ex(Hw Jq Lj Nk Nm Nu Oz) aC(bL bU CP cQ Ew Im) cB(aY bA bZ cW Jl Jo Qa) Pf(cC dA gV Hv Jl Lw) Aj(Cu Dg Ef Js Om) cC(aY cW dF Ne Pz) Cs(Im Pg Pz Qb) Cu(Hv Ip Jo Ng) Nn(cR Gl Hv In) Hx(aU bL Nc Nl) cW(Ct Hv Mp Qd) Ne(aH bU Ew) Jr(aO cR Nu) Pe(bA gV Lw) Ar(Lw Mp) Ax(Mp Qd) Nc(aR bW) Ir(bA dL) Li(dA Pa) Ny(cV fP) dB(Qa Qb) dF(Hq Ma) NuIn LxaV MbcR IjdL IvaO QdaR JqfP PgcP} jR{Yi(aA aL Ap aQ bP cO cP Cq CW Db Dd Dg Ez Fc Fn Gb Gl Ho Hu Ii Ik Ii Ir Iv Jd Je Jg jH Ji jM Jr Jt JU jV Kl Ko Kp Nl Nm No Nr Nv Nx On Op Or Ow Pb Pd Pf Qa Qm qT Sf Sj St Tz Uh Uo Us Ux Vw Wc Yj Ti) Va(aD aE aI AJ AI aP aY BG cI cM cS CU Cw DD dF Fi Gl Hc hV Hx iB Iv Jl Jt Kc Kf Kg Kk Ko Kr Mj Mm Mn Nc Ne Nl Ns Nu Nv Pd Ps Qd Ql qW Rm Rv Sr St Tn Tz Uc Vu We Wh Tl) Ho(aD aF Ao bB bS bX Cu CX Db dK Fn Gb Gc Hb Is Iv Je Jq Jv Ke Ki Kx Lh lN Lv Mm Mt Mw Mz Nc Ne Ni Nl Ns Nu Nw Ph Ps Qb Qe Ql Qm Rf Ry St Tz Ut We Yl) Yl(aD Aj Ap aQ cI Db Fi Gb Gl Id Ik Im jE jM Jt Ke Kg Ko Lh Md Mg Ng Nl Nm No Nx On Qc Qe Qm Qu Qy Rt Si Sr St Ua Uh Uu Vi Wd Wm) Vz(Aj Ap Cw Db Dg Fd Gb Gd Gl Hf Ii Ik Il Ir Is jH Jt Ke Kf Kg Kj Kl Kp Lh Mg Mz Nf Nm No Nx On Ow Qe Ql Qm Si Sr St Uh Uu Ux) Zw(aO Bc bM bN bS cI Co CP dE DK Ez Fn Fp Fr Gb Hx Ic Iv Jg Jp Jt Ke Kf Kl Lh lK Lv Mt Nd Nx Oa Op Pd Pk Qm Wc) Gb(Al bS cH cT Cv Db dK Fb Fc Fi Fn Gn Gz Hc Hw Ik Is Kx Lh Mf Mw Nc Ne Ng Ni Nl Ns Pd Po Ry Sr Ug Up Tj) Si(aD aE bS cI Cv cX Db dK Fb Fn Fr Fw Hc Ik Io Kg Ki Mw Nc Ne Ng Nh Ni Nl Ns Pa Pd Qt Ry Ua Wd We) Ps(Bc cP cQ Db Dg Dl Eq Fr Fw Id jF Jg jH Md Mg Mt Oi Oy Oz Pd Pk Po Qu Qw Ry We Tj) Ux(aD aF aK aO aR aX bC bH bJ bR bS cM DK Ex Hf Hp Im Ke Ki Ld Mt Ph Ry Rz Yh Ti) Gc(aD Aj Ax Bg bR dH Ez Fn Gl Hl Ik It Iv Kg Ki Kj Ky Lj Mk Nr Qh Qn Ss Uh Yh) Ry(cO Gl Hu Ic Ik Is Je Jg Ke Kl Nw Op Pz Qc Ql Qm Sr St Ua Uc Uh Uu) Wd(aK aO aS aV bO bR Dl Hp Ih Il Im Jc Op Qa Qb Ql Rm St Ti) Yh(Ap cP Gl Hx Ic Ik Ji Jn Qa Qb Qe Qm St Wf Wm Ti) We(Ax bR cY Gd Gl Ir Jr Kf Mt Ny Op Qb Qe Qt Uh Un) Wh(bJ cF Dp Hp Ih Ik Il Ir Is Ks Qb Qc rA Rb St) Yg(Al aS Cu Db Ik Iv Jq Jr Mt Ph Rc Ug Uv) Ic(Ad aR Bb Dc Di Hf hG iH Qh qO qP Tr) Hp(cI Fa Hc Jt Kg Mf Mg Mz Ng Po Qm) Lp(Ap dK Fr Ik Iz Jg Mg Mt Pd Sr Uc) mS(Af bF Cv Cx dR Hc iA Kf Kn nY) hG(kC kF kN kO lY nC nH nJ nK nL) Fc(cM Db Ex Ik Je Mm Qm Qy Uc) Vi(aD Db dK Dl Kg Ki Kj Nh Pd) Vh(aE aU Cx cY Db Fn hV Ki) Du(cM Db dH Is Ql Qy Rm) Op(cM Jd Kg Mt Pk Ql Ug) mW(As aZ Bc Bg Ct Cv Iz) oH(kC kG kO nC nH nJ nL) Fi(Ik Je Kn Mh Mm Pd) Is(Em Rx Yd Yc Tl) Yj(Iq Jr qW Qy Un) Wb(Co Ik Jd Mg Sr) Wn(Pa qP uV wL zH) Vc(Ap Gl Mt Mw Ql) Vw(aD aM bS Jq Ki) nC(gL hB Hf Ow Tv) nH(gL hB Kz Ow Tv) Db(kG mF nL Uw) Di(Ip mH Na wH) Gd(cX Im Ki Qt) Yd(Ex Jd Kn qW) fR(bH Fp gP oF) nA(St Tv Ur Vu)

Figure 6 Continued tF) Ex(hL hO tU) Sf(qT qV qW) hR(Jg Tr Wh) tO(aR Jy Rb) Bc(rP tL) Eq(iB lO) Tt(uG yE) Sh(qT qW) aC(rS rT) gV(bM Mn) zH(kR oE)
jY(Qh Zx) vB(Lh Nw) AauR AdqG AphO ChiC ThoV GpzA WfiB UfhL VijF VjqT cNuN dXoE eMhB wKsH iAuX hGuV jEuZ} rA{Wh(aF
Aj An aS aX aZ bA bH bL bS bW cL Cv dG Dk dN Hf Hl In Is Jf Jq Jr Ke Ki Ko Ld Lx Nc Nk No Nw Of Pe Po Qa Qc Qe Ql Qx Rg Rt Si Tv
Un Ur Vc Vt Vv Yd Zx Ti) Zx(aE Al aN aS aZ BC bE bH cA Ch cM cO CV cX cZ dE Dk Ed Em Fc Hp Ii Io Ir It Iz Jg Jp Kc Kk Kx Ld Mf Mk
Mp Mu Nd Nl Qm qT Ub Uk Ux Uy Vu Yj Yk Yf) Vc(aK aP aZ bB Bc bH bP bX cE cG Co cP Ct Cw dD dF Ef Fr Gl hA Hc Hq Ii Iz jI jP Kx
Ld Lh Mm Mp Nn Nv Ny On Ou Ow Pf Pg Po Qa Qh Rm Sr Un Ut Vi Vt Vu) Fc(Bc cP cQ Dd Ef Fd Gn Ho Hp Hv Hw Ib Ii Im Iq Ir Is It Jh Jk
Jq Jr Lp Lv Me Mt Mu Ne Nl No Nx Pa Pg Po Qe Qh Ql Ue Ug Un Us Uy Vt Wc Wm) Si(Al An aQ aU aZ bC bH bS cA Ct Ii Ik Io Iq Iv Iz Jv
Kc Mg Mp Mu Nd Og Ri Sh Uk Vz Ye) Uw(aG aX Ba bR cT Em Hq iC Ip Jk Jn Kx Ky Mj Mx Of Oz Qz Ru Tv Ug Uk Uy Vz Ye) Yd(aK aU
Ch cP Ct Ib Iq Iz Kx Ld Mg Mp Mu Nj Nn Nx Oh Om Ow Pb Qg Qh Ry) Vb(Bn CT De Hp Hr Hu Jk Jq Kc Ny Om On Pd Po Qy Uc We Yj
Yk) Ye(aD bR Dk Ke Ko Ny Or Ps Qa Ql Qx Rm Tz Vj Vt Ti) Hp(aR aV cT dG Ef Im Jr Ko Nf Nw Pi Qm Un Yj Ti) Eq(aV bP Ch Co dD Ef
Jd Ji Mg Qh Qt Vs Wm) We(aD Ba bB dC Hb Hl Ir Ke Lp rB Rg Vt) Du(cT Jq Ke Ld Lh On Po Qa Sr Un Vt) Yj(aD Bc bR Ib Iz Jr Kx Mu Qm
Ug Un) Sj(aV aZ cP Fr Jg Ut Vi Vs Wm) Uy(bW Dk Hf Jr Ko Lx Nw Qm Uh) Vz(aA aQ Jh Jp Nj Nl Un Yl) cT(Gn Rt Ru Uz Wc Wd Wg Yk)
Fi(cP Hc Ii Jh Lh Nx On) Rv(Ch Dk Iv Ke Qa Tz Vj) Em(Kn Nw Nx Oz Ps Ti) Vj(Bc Dp Hr Nx Ql Ur) Gb(An bH Jf Nl Un) Zw(aQ IK Qg Rh
Tz) Ps(aV cY Hr Jh Nk) Rz(aZ bH bP bR Iq) Sf(cO Kc Ko Ti) Tl(Jv Mp Nj Qg) Lp(cM Qm Rg Ri) Rt(Dc Iq Iz Vs) Nw(fR tO tS tX) aQ(Op Yi
Yl Yf) Bo(mM nA nK) Fd(Jk Ko Nc) Hl(Ef Iz Kc) Yg(An aO Jf) Sh(aD bR cO) Wf(aZ bH Ld) Ry(Ii Jf Nc) Vi(aO cM Ma) Dc(Wd Yi) Ex(hL
xA) Yk(aD bR) Xa(cM Jf) Tm(Ir Kq) aW(mW nN) aZ(mW nB) nA(Fn Kz) GnNc HanC MzuZ HobR YhNx WbRi RbmF JkVw JqYl RubH
OpPi VarB VtfN aYoO mSpF sJrS} lK{Ye(Aj Ao aY bB Bc Bg bP bR Cs DD dF Fa Fi Fw Gl Hc Ho Ih Ij Il Im Iq Is Jg Jp Jt Kf Kl Ms Mu Mz
Ng Nn No Nr Nv Nw Nx Ny Oh Ok On Ou Ow Pe Po Qa Ql Ry Sr Ua Uc Uf Ut Uu Yg) Wh(bA bB Bc bL bP cA Ch Cp Cq Ct Hc Hx Jh jM Ju
Kc Kl Lh Mg Oe Oh Oi Om Ow Po Qn Qw Qz Ub Ug Wf) Ry(aA aD Af aY Bn cO cX Fr Hu Jg Jp Jq Kl Lh Nc Nl Nx On Pd Pf Pg Qm Qv Ss)
Va(AJ aP Ba bQ cI cW dD dF Dk Fr Fw Gl Jg Kl Kr Mj Oy Pd qT) Zw(Bc bN bP bR Du Iu Jh Jp Nc Nk Oe Po qT Rh Ss Uc Yh Yi) nC(Af As
Cv Dd Ed Fn Ha Hf hG Jd Kf Kp oF Ou Ow Pi Qm) Du(Aj Ap Ba Bc Cw Dd Ez Jh Jt Kg Mw Qu Sr Ss Ua Uw) kO(Dd Fn hB hG Jd Je Kf Ou
Ow Qm Qy Rf Rm Sr Tz) Vz(cW Gl Hu Ii Ik Jg Jt Ng On Pd qT Ss Tt Ut) Xa(bP cW Il Im Jt Kf Ng Oi On Ou Pa Po Ql Qu) Yh(Ap Bc bR cP
Gl Hx Ii Jd Mw Nc Po Qu Ss) Sf(Aj aY Ez Hu Ii Ik Jd Jg Jk Jt Pd Sr Ux) mS(Al bS Ch Cw Dd De hG Kn Kp oF Oh pF) Fc(Bc Ch Ct dE Ez Jg
Jh Oy Qz Rc Ut) Ho(bH bI cA Cp dE Hx Je Jf Kl Qz Ss) Eq(Cu Id Is Jg Kf Lh Mw Ql Ua Ug) Fi(bH cA Ch dE Ez Jg Jh Oy Qz Ub) We(Bg bQ
Cw Fr Hc Kl Kx On Po Qw) mY(Af An As Bo Cv Cx Db Ou Pk Rb) nH(Af Ct Cv Dd Fn hG Kf Kp oF Ow) nL(Fn hG Jd Kf Kp Ou Ow Qm Rf
Sr) nK(Ch Db Fn Ha Kf Ou Ow Pi Qm) nD(Af An As Ax Ba Cs Cx Fa) vS(aR cB iH Jp Lh Mz Nw wL) Yi(Ap cW Dg Gl Mw Oi Ss) Cw(pS sK
tN tX uL Uy) Gh(Aj Hc Mg Qu Qz Wd) Rv(aD Dk Lx Nw Qa Qe) Yl(aA cW Em On Po Ri) fR(Ba bN Ch Ct Id Kl) mW(Af Ax Cp Cs Kx Ou)
Yg(cW Hw Jd Po qT) Sh(bR cP Ex Oi Tz) Ba(Em Wc Yd Yf) Bb(tN tR tS tX) Bg(Fd Vw Wc Wf) Ib(kF mM Op Sj) Jg(Em Sj Yj Yk) Wd(Ad
Bc Oi On) Rt(eD Kl Pk Ut) Ux(cW dD Iz Po) Fd(Gl Lh Qz) Yd(Bc Oi Pk) Rx(cW Fr Ou) Uf(tR tT tX) Uw(Dl qW Uv) Vi(cQ jF Oi) nN(Kn Um
Vs) Ef(Gd Sj) Em(bB Tr) Fn(kC kG) Gb(cI Po) Zx(Hx Oi) Jh(Gd Lp) Wf(Ad Jd) Tm(Hc Mw) Ps(Nu Vs) Ou(nJ nT) Vw(dD Iz) aW(mF nR)
AsmT CtnR ExvH lqWb SiSs SrUy KfyL KynA LhxA LpcW RirN OpbI aRtL aZmU cDmF tFmZ} lL{Uw(aC aK aQ aU aY Ba bB Bg cP cQ
dC Du Fw Hc Ik Je Jh jM Ky Mk Ng Nh Oy Pd Po Qw Qz Ss) Sf(aJ aP aY Ba Bg cO cP Cw dD Dk Ez Gl Ik Iz Jd Jg Kf Mt Ou Oy Pd Pg Sr Vu
Wh) Eq(aJ bB Dk Id Im Is Jd Ji jP Js Kx Mp Mv On Or Ow Pe Qa Qb St) Yh(aP Bg cP dF Dg dK Ez Gl Jd Ke Kl Kn Mg Nc Nv Ou Ow Pg Vi
Vu) Wh(aZ bN bX Db Du Ed Fr Fw Ik Il jI JU Lh Nk Og Qh Rf Rh Vp) sC(Ap Bb Bo Cw Fb Hf Ip Jg Ji Ke Ky Mm Na Nw Ok Qv Ri Tr Uf Vt)
Du(Al Bg bH Ch Il Iz Jh Jq Mh Mu Mv Of Pg Po Qh Qz Ss We) Yi(aO bP CW dF Dg dK Ez Gl Is Jd Je Jl Kn Mg Nv Pg Sr) Jd(Cw fN Gb Gd
Gh Gn Hf Ip Na Ps Rv Sj Vj Wf Yg Tm) Ye(aY bB Co Cs Cu Fw Il jI jP Kr Lx Or Ou Ow Tz) Cw(fN hL Mz Nf Of Oh qD qU rN rW vB Vj vS
wJ) Fi(bH dD eD Fa Gh Jh Jq Ld Mv Nj Oh Ow) Xa(Ex Fr Ii Ik Lh Md Nc Nj Nk On Ou Oz) Rz(aD Ed Ef Fr Fw Jh Jq Lh Lv Or Qx Rh) Fw(Gh
Hp Op Ry Sh Ux Uy Vi We Yk) Vz(Ba Bg bP Ez Fa Nx Ow Sr Ss Tt) Rt(aY bX dE Dk Ex Ik Oh Ow Pf Uo) nN(Ba Cp Ct dI Dp Iz Kl St Tr Ua)
Tz(Fd mS nT nU Rv Uy Vj Yg Zw) Sh(aJ aY cP Ex Fa Fr Lh Or Ou) Sj(Ap cW Ez Ib Ik Iq Jq Mg Rm) Va(aA aY dD hA Hq jP Kr Mj Nn)
Wf(Cu dF Hc Nv On Pg Po Tn) Vi(bN cP hR Ik jF Oi Rh Ss) Gh(aY Dk Fr Hc Jg Qz Wd) Lh(Em Fd Gn Hp Ry Uy Yk) Op(Bg cP dA Hc jH Oy
Qz) mW(aY aZ Bg Cu Ef Fb Jf) Zx(Ba Bc bP Hx Iz Ss) Vw(cP dD Gl Jh jU Rh) nA(Af Cv Cx Fn hG Kz) nL(As Kl Kp Pg Ss Uu) Fd(Dk Jt On
Po Ua) Fr(Em Hp Rx Vj Tl) Rb(mF mI mM mY nO) Ho(dD Iu Oe Qh) Hp(cW Hc Or Ou) Tr(nI nJ Vb yH) Yj(aD Dd Uy Vs) Wd(Il Nc Nk Nl)
Ry(Nc Ow Qy Vc) Vj(Gl Iz Jp Ou) Ef(kI lX Vc) Em(bB Ex Jp) Gn(Mg On Sr) Hl(Bg Dk Ow) Si(cP Ji Lu) Zw(bN Ib Mg) Wc(Nn Oh Qy)
We(bP Nc Nk) Tm(bB dD jP) Uy(On Pg Sr) Ux(Jg jI Nn) aZ(kE kI mF) cW(kO nK Vb) Db(mY mZ) Gd(Ba Ow) Na(Ad Kq) Tt(rN Tl) Yg(Ib
Iz) Rv(Jp Po) Um(mT nR) Vo(lY nT) bH(lY mZ) BbyH FaRx EzmF FcJq MzfN HfOw YkaD WbOr JeVc SrlW SsnI QyYl PsPg VumY aWnR
aYoP kIkS} jU{Sf(aD Ap Ar aY Co Cs Cu cW Cx DK Ed Ez Fa Fp Fr Fw Hb Hf Id Ii Ij Im Iq Is Iu Jd Je Jg Jh Jq Js Ke Kn Kr Kx Ld Lh lN Lv
Lz Mj Ml Mp Mq Mt Mw Mx Mz Nq Nv Nw Oa On Ou Ow Pd Pe Pf Ph Po Qa Qb Qc Qh Qw Rf Rm Ry Sr St Tn Ut Vt Vu Yi Zx) Gb(aE Af
An aR cI cT DI Fc Fi Fn Gz Hf Hx Ii Iq jE jF jM Kc Ke Kf Kx Lv Md Ml Oz Pa Pd Po Qw Va Wc We Tj) Wh(bV cG cL cU dF dG Fn Hv Jf Ki
Qy Ri Rm Rz Si Uf Ug Uv Va Vc) Vc(Aj Ba Bc Dg Ez Ii Ik Iz Jg jH Jt Kf Kl Oi Oy Pd Sr Uc Vw) Si(Ad Aj Bc cI Ct DK Fn Ib Jd Mg Oy Oz Pa
Pd Qu Ux) We(aE aY bJ cO Db Dl Ex Gl Hp Ir Je Kf Qm Qy Rm St Uv) mW(aC aM As Ba bC bL bM Cp cW De dG Ju Ki Ri Tr Uk Ur)
mZ(As bI bM Ch Co Fn gP Hf hG Kf Ki Kn Kx St Tv Vs Vu) Vz(Co dD Ex Fa Hc Jd Kn Nk Or Ow Qh Qm Sr Tt Un Ut) Va(aE Bc cO cP cZ
Dk Gz iB Kc Kg Pd Ql Ua Uc Vu Wf) mS(aC aJ aM Ar bF bI Cq gP iO Kz oH Or Pi Vu Wm) mY(bL cW gP Hf hG Ki Ky pF Pk Rb Um Us
Wm) Yi(bN CO Fn Hl Jd Ju Nj Nk Qh Qm) Rt(Db Hb Im Jd Lx Mq Ow Ph Qa Qb Ur) Ux(aF aR bF bR cE cS cU dH qW Ti) Ry(Bc cO Ju Lh
Nn Ow Qm Ua Yh) Vw(bR cM cO Gl hA Ql qW Ye Ti) nH(bL hG Kf oE Ow Rm Tv Ur Vu) Db(Ru Uw Uz Vi Wc Wd Wg Xa) Zw(CO Gh Je
Qh Tz Vs Ti) Rv(bB Fn Fw Im Ju Lh Ou Po) Yl(Jd Jv Nk Nn Ow Oz Qz Un) nC(bL dB Ed hG kS Rm Tv Vu) Wd(aE Ow Qm Qy Un Uv Ti)
Vj(Ba Ct Kq Nn Oh Ow Qm) nK(Hf Jv Ke Rg Rm Ur Vu) Yd(Ex Ik Jd Jg Mg Pd) Sh(dD Lh Lv Qb Vs) Jd(fN Gd Lp Op Yj) Bo(kC kF kG nB)
Em(bB Kr Lh Om) Eq(Mg Mw Qb Vs) Yg(aD aO Gz Vs) Ju(nN Uw Vi Zx) Bb(tO tS tT) Bc(Yh Yj Yk) Tr(kN nF vS) Ye(Ex Rm Un) Lh(Fd Hp
Uy) Co(Fd Yh) Dl(Fc Uw) Du(Ii Ql) Fn(mF nF) Gh(cM Kg) Yk(cP Tz) Jt(Fi Vb) Xa(Ex Ua) Tm(aH bB) Tl(dD Ut) Ps(Im Oz) Lp(dD Fw)
Op(Ct Qh) Ow(Gd Gn) Uv(Uw Vi) Uy(Jr Ko) bL(nD nF) cO(Ho Rx) mP(Jv Qu) nA(bM Ez) AdfY HpVs TtrN IlZx YhQm YjcP WcqV RhVi
OrkO UmmT bHlY cJoP cWkG cXnD dBkI dJlX mUpF} hA{Uw(aD bG cA Ch Dl Du Fn Fr Fw Jh Kg Kl Mg Mw Ng Of Oi Ou Oz Pa Po Qn
Qu Qw Qz Sr Ss Ub Wd) Wh(aD Ar bX Cs cW Ex Fr Hb Hf Il Ju Kx Ld Lh Lx Mj Nq Oa On Ou Pf Qg Qx Sf Sr Uh Vj) Ry(Af aY Ba bG bL
bP Cu Cw Dk Fw Hu In Jg Jq Kr Lx Mw Nc Nq Op Or Ow Pg Zx) Sf(cW dD Ex Ez Fr Hu Ii Ik Iz Ju Kf Mg Oy Pf Sr Tt Uc Ux Vu) Vz(aY Ba
bP bQ CO dD Ex Ez Gl Oh Ow Sr Ss Ut Uu) Va(bG cL dD dH dI eD Fr Fw Gz Hq Kr lN Mj Nn qU Vc) Sh(aD dD Ex Fa Fr Jd Lh On Or Ou Pd
Po Sr Ut Vu) Ye(aI bB cW dF Dk Fw Im Jd Kr Nv Ou Pg Po Tn) Rz(aD Cu Fa Fr Fw Im Jq Mv On Or Ou Ut) Hp(Co dD Dk Fr Fw Hc Lh Mf
Mw Ou Qz) Rv(Co cW Fr Lh Mw Of Oy Pf Sr Ss) Vi(Ch cI cJ cP Fw Hc Ii jF Oi Rf) Du(cC dH Hq Iz Mg Mu Mv Qh Qt) Yi(Ba bP Cu CW dB
Oh Ow Sr) We(aD Ar cI Co Cs cW Ke Oh Sr) mW(Aa Ba Bc Ct Cu De Iz Kl Tr) Em(Aw Co Fa Fr Jd Kr Lh Nv) Hq(Fc Fi nN Op Rt Ux Vw

Figure 6 Continued

Figure 6 Continued bL(mM mY mZ) lX(Ap Kp Kz) mW(aY Dg Fb) nH(dR Jd Rf) Em(Nw Oz) Gn(Hb Rm) Sh(Fb Qm) Wd(aO Nl) We(cT Qa) Ry(aO dG) Rt(bV cT) On(Fi tT) Uh(sF sH) Uw(aF Kp) aZ(nB oO) fR(iC Jp) nO(Ap As) mY(Ow Vu) DlkE ThNy FcIi FnYh GdKo HlJk TvnD JiXa RxbR RuNx YlUn NwsF OunT UydG VtsO mMpF iJkN} dW{Lv(AA Ad Al AO BC Bg bM bO bS bV bW Ch cI Co Cq Cv Cx Dc dI Dk Dl Ef Fw Gp Hx Ih Ik Iq Ir Is Iu Jg Ji Jm Jo Jp Jq Jt Lu Me Mf Mh Mn Ms My Nf Ng Nj Nm Nx Oy Pd Pe Pz) Jj(AD Af Al An Ao aU bM bP cI Co Dc Dl eM Im Ir It Iu Ji Jn Jp Jq Lh Ma My Mz Nc Ng Nm Nq Nw Nx Oe Oh Oi Om On Oy Pa Pf Pz Qb) Nw(aF aG Aj aM An Ao Ap aS bA Bg bI bO bS cI cP Cq cW Dl dM Gd Ii Iq Iu Jg Jo Mb Mp Mz Ng Nj Nm Nu Ny Of Og Om) Pe(aA An aO aX bP bS bW cF cK cQ Fw Gd Ik Jo Jp Me Nc Nd Nf Ny Oz Pa Pb Pc Pz) Mb(Aa An aO Bo bS bW cS dI Dk Hx Ik Ir Is Ji Jo Jq Lu Ms Mz Of Oz) Gp(Aj Bb Hv Hx Ih Ii Iu Jg Jp Lj Me Mh Mw Nb Ni Nu Oe Of Og) Jn(aF aO bP bS bW cP Cq Ex Fr Fw Gl Hw Jo Js Mu Nv Of Oz Pb) Ji(aF aH Al Ao bI bM bP bS Cs Dc dM dN eM Gd Gl Jh Og Oz) bM(aM bN bX cD Cx Dd dE dI Dl Gd Jm Jq Jt Ms Mu Qd) Pz(Aj aM bS bW cC Gl Jo Lj Ml Of Oi) Pf(aO bF bS bZ cG cL cU dH Fw Hq Ma) Mf(aF aO bP bW cL Hq Jo Jp Of Og) Ms(Aj aS cP Cs cW Fp Fw Jk Nl) aM(aX bP cQ cV cZ Nd Pb Po Qd) Is(Fw Gd Gl Ii Jk Nd Nv Oe) aC(aF aR bF bG cG dH Hq Lu) Fw(Ij Im Lh Nq On Qb) aO(aP cG Iv Jr Lh Mt) Mn(bH cB dI Pb Qd) Jo(Co Dg Ef Mt On) Aj(bC Co Iu On) Ly(aF aY Iv Mv) Ok(bS Ct Gd Oi) aA(Bo Li Lj Mh) bB(aF Ii Im Jm) Lx(cH Cs Jm) Nd(Ir Mv Ny) bW(dG Lh Nh) cB(dB dJ Pc) Aa(Lj Mk) Gd(Ih On) Mt(bS Oe) Jp(Mu Oe) Of(aI Lh) aF(bP cG) bR(aN Bo) AxQd CoOg GlOn HqcG HxcY IrPb QbPa PgbS aDdC aWcP} tS{Lh(Al aR bQ dA dE fN Hu iA Il In Ip It Jn Js Kd Ky Na Nt Nu Oi Qc Qd Ql qU Qv Qw rB Ri Rm vV zH tL) Kf(Af cF dG Fp iA Ih Il jG Jl jV Ky Lv Na Nf Nq Nu Oe Oi Pi Qd Ql qU Qw rB Ri rN rO uZ vS tL) Ri(aR Bb cH Gl Ip Ji Kc Ke Kg Kp Ky Lv Md Mf Mz Nm Nw Oi Ok Qv Qw rN rW Tt Uf Um UV Vt) Vt(Al Bo bZ cF dA Ez fN Gp hP Jl jV Ki Lv Mn Na Nq Nu Ph Pi Qd Qv QW rB Uf Us uZ) Ip(Ad Al aR cZ dJ Hq Hu Il Iq Jg Ji Jp Kc Ke Ky Mv My On qW rB rO rS rW vI yH) Cw(aO bP bQ dJ eD fN hL Hu Jd jM jV Me Mz Nq NW qU rB sK Um uU uY uZ) Qw(Ad cH Id Jd Ji Jt Kg Ko Li Mz Nm Ok On Pd Po rN Tr Tt Uc Uf) Ke(Af bZ cF fN Gp jV Kd Lv Mn Na Nq Oi rB Rm rW uU uZ vS zI) Bb(aR cF cH fN Gp Hf jV Kc Ky Md Nd Nq rC rW rX rY sC yH) Ad(Gp Hf Il JV Kd Kp Ky Mn Na Nq Oi Pc Qd rW uZ vS) Uf(Al Bg bZ cF dJ Gp iP Lv Mp Nq Pi Qv rB Um) fN(Aw Cp Jd Jg Ji Jj Jp Kn Kp Ky Tn To Tt) Kg(Aj cF Jk Nq nW Oe Of qU rB rW tL) On(Gz Hf Il Jk Kd Ky Ql rB rW St) Ex(Af As Aw bP Cq Dl qU sC yH) Nw(Af bP Gp Hf Il JV Ky rW) Nm(cF cZ jV Nt qU qW rN rW) Lv(Ao aX Hf Kc Ky qU qW rB) Tt(cI dJ Hu iC jV Qv qW) Ji(Af Al aR Hf Il jV rW) Ok(cF iA Il Kd Na Nt Qd) Jd(Hf JV Nq Oi Qv) Ky(aR bP Cu iP Jp jV) rB(Aw Cu Jo Jp Pd) qU(Cu Fa Kp Md) Bc(Hf Na Nq) Tr(Gp jV Nq) Jp(dE qQ) Kp(bP qW) Kq(jV Na) Oi(Dd Dg) rW(aR Ki) FauU GzaD NqKo MzSt QdJt QvVo KndJ bZfP cFuZ} Ex{xA(Ao As Bb Bc Bg bH bX cH CQ cS Cw Dg Dk Dl eF Ez fN iH iP Iz jE Jg Jh Jo Jt Kk Kl Kn Ko Kq kS Lv Ly Lz Mk Ms Mz Ng Nj Nm Nn Ns Nt Oh oK qH Qt Qu rZ sC Ss tN TO tR tU tX Uc Un Uu Vt vW wE yH) hL(aD Aj Ap aQ As Aw Ba Bb Bc Bg bL bP cA cI Cp Cq Ct Cv Dd Dg Dl eC eF Hc Id Ii Ip Jh Jo Kg Kj Kl kS Lv Md Nm Ns Nv Or Oy Po pY Qw qZ Rb rR rU rV rW rX rZ sC Ss tT tU Tv Uc Ug Uu Vo vS yH) hO(Aj aQ Bb Bc bP Ch cI Ct Dk Ed Fb fN Gl Hc Ib iJ Ik Ip Iz Jh jV Kg Kj Lv Mf Mg Ne Ng Nm Ns Of oK Oy qO rW Ss Ub Ue Uu uZ Vo vS zG) sC(aA cQ dR Ez Ha jK oN Pk rS tN tO tR tT Tv tX vB wL wP zH) uZ(bH bX cK dB fY jE jH Kn kS Mk Mu qO qW Rg tO wD wK wQ) oK(Ad Cw Dg fN fY jV qH qI rU rV uP vP wP) tQ(Ap As Cp Cw Dk Dl fN Jg jV Ng rT Ua) Yc(bR cR Dd jH jK jV Ko Mn Nk qV Up) vH(Cw fN jE jH Lv tN TT tU wF) On(aM aW fY qO qP rU sK vP yK) Bc(qB rW tR vP vV wP zA zG) tO(As Aw Bb bP bZ cS Dk Dl) tT(As Aw bP bZ cS Dk Kf) bZ(fN fY qD qO tU) wK(Ao Ed Kf Tr Tt) tR(As Aw bP Dl yH) oN(fN qO qP rW tX) Vt(tU uL vB wP) As(tN tX vP) Lv(uI uL zH) Lh(vP vV wE) eW(aM aW Mu) qU(fN Sf Sh) Th(eQ nI) Tt(sK uL) Tr(sM uV) St(qQ wQ) bP(tN tX) fY(cU zH) tU(cG Jd) qW(Sf zG) AwtX CwwP DcLt DdWe DukI TzyH JguM XakE KquL KrgV RzmS VajK aCfR aHeQ bCuY cMoV gCoO jEtL wHvV}
jL{Wh(aR aS cQ dH dK Hb Ih Im In Iz Js Ki Kx Ld Lh Lx Lz Mf Mh Mk Ml Mt Nw Ny Oa On Op Ou Pb Pc Pe Po Qd Ql Qu Qx Rm Rz Tv Tz Uh Un Ur Uv Vc Yl Zw Th) Uw(aE aF Al aR aW bJ cH Cv dK Hx Im Io Iq Iv Jj Ki Ks Kx Mw Nc Nh Nk Nl Ns Qa Qe Ry Ub Un Uv Vc Yl Wm) nN(Aa aD An Ar aZ Ba bL bM bN cD cM cQ Ed Hc Hf Ju Mt Nc Nl Ou Qt qU Us Ut) nR(aD bL bM cO cW dC Ed Fw Fy hG Jf Jy Ks Ql Sr Ul Um Us Ut Vo Vt) Hp(cO Im Is Lv Mf Mt Nf Oa On Op Ou Po Qe Un) Vc(aA aJ aP cG cI De dF Jg Kx Nv Pd Tz Uf Vu) Yi(aE An Bn cO Dk Gh Ii Jh Ld Mr Ni Nl Qy) Ye(aD aH Hf Ir Is Kk Ld Lv Nw Or) Yj(aD aR dK Hf Jp Jr Or Qe Tz) We(Ar aS aX bB Co Ir Oa Po Uv) As(kE kF kG mM mP mU nC nH) Yl(aA Af An cO cX Gh Jp Ug) Op(Hr Iq Je lO Pa Pd Pk Ry) Kx(Gb Ho mF mS Ps Si Yd) Gh(Dc Dd Hf Im Un Yh) Yk(aD Jr Lv Or Qe Un) Qy(Du Fi Gn nC nH Ry) mS(Al Cw Dc Ou Pi Pk) nA(bL Cv Db Kn Kp Ky) hG(kC kN kO nC nH nL) Ug(Ps Rv Vb Vi Zx) mP(Ct Ez Rb Um Us) mU(Ct Ez Rb Um Us) Ky(nC nH nK sI) Uy(Im Mt Qe Ql) mM(aD bL Jv Um) Ho(eD Hr Th) Iq(Du Gd Wb) Lp(Ke On Un) Vi(Kr Uv Vv) nC(aZ hB Hf) nH(aZ hB Ki) nK(bL Db Pk) Ad(Yg Zw) An(nD nF) Gb(cW Jq) Mg(Rz Si) Mv(Fd Fi) Tz(Hl Rx) Yd(Mp Pd) Ps(Af cR) aE(Sf Xa) cO(Ry Yh) mW(Aj Tr) oP(cJ cQ) CtnD DkRv TiNu GnQm LvYg IiZx ZwJp WcqV LdRt OwnJ OunF UmmT PkmY}
eW{Lv(Ad Aj Al aM aW Bb BC Bg bO bU cF Ch Co Cv cW Cx DK Dl Ef Hr Ii In Iq Is Iu Jh Jm Jo Jq Jt Lu Lx Mf Mg Mn Mp Ms Mu Ng Nj Nm Oi Om Oy Pa Pd Pf) aM(aC aF aW aX bA bC bM bQ bR bV cN cT cZ Db dI dJ dM Dw eM Jk Lx Mb Mn Mr Mu Nd Ni Ny Oe Ok Oz Pb Po) Lx(AF aQ bJ bX cA De Gl Is Jj Jm Ly Mg Mp Mw Ns Nx Of Pd Pg) Mn(aN Ao aP Ar As Bb Cs cW dG Fp Fr Hq Hu Hv Jp Li Mb Mk Ml Nj) Aj(Ad aK BC Bg bM cB Ch Co cW Jm Me Mf Mg Ms My Nx) Ok(Ad Af aW Bb Bn Ct cV cX Gd Ip Jg Ly Mk Ng Ns Oi Om) Mb(aH aI bB cS dA dK Fr Hw Hx Is Jn Ml Mu Mz Nt Po) Nx(aC aI Cs Gl Hr Jk Jn Jr Lj Mk Ml Mu Oe Og) aY(Aa aF aO bS bW Hx Ir Is Jn Jp Jq Ms Mt Mz) Ly(Cu Ih Is It Jl Mv Nn No Nr Po Pz Qa) Ml(As bC bO cM Co cW Jn Li Me Mp Qc Qd) aF(aC aD aI bM bP bZ cG dF Mp Nw Pf Qd) cB(aL aO aW bR bW cI cN Dl Gd Jt Of) aC(aL aO As bN bO cH cK Dw Me) bM(bN bW Cx Dd Dl Dw Gd Ni Ns) aW(aI Aw bH bR bS Jr Pa Qb) bB(aA Ao bI bS Cs dM eM Im) bW(cG cW dF dG Nj Pe Qe) Gd(Iv Jm Jn Mg On Pe) Co(Bb Ef Iu Jo Of) Nu(aD bP In Nc) Oe(Bo cW Is Mz) aO(Bo cG Iv Jr) bR(bX cG Dk In) Nj(Ew Jo Mr) Qb(aG cW Nd) Ji(Ad Ao Jg) Mu(Hx Qa) Jk(Ms Pe) Jo(cW cY) Nw(cC Mp) AlJj AoIs BbGp BoIi PoPb FpbC MtMw NdaH NgJn NibP InIv PzcC aGaI} On{eQ(aC aH aI Ar Ax bB bE cG cR Cs cZ Ez Fp Hc kE kF Ko Kx Lj Mx Nd No nW Oy Ua Vo Wd) Nd(aA aO aR aW Bo Cw Db Ii In Iu Jj Jo Li Lw Mf Mh Ms My Nc Ng Of Og Oi Pf) Hf(aO eD hL hO It oH oK qC qD rB rW tN tO tR tT tX uZ vB vP vS vV zG tL) Ql(eZ fN qO qP qQ qZ rW sC tN tO tR tT tX uN uZ vP vS vV yH tM) tT(dE fN Il It Jk Na Nk Nn Nt Nv Oi Qd Qw rB Rm rW) Eq(gZ mF mT mY nC nD nH nK nL nN nU oV) Jd(aO Hr Hu It Jl My Na Nt Nu Nv Oi Tj) rW(Fp iA It Js Mn Oi Ri uZ wF zH) Gn(eC mF mT nJ nU Pi Pk qW Ue) Nj(aM aO aR aW Bo Cw Db Ii Of) Qw(hL tN tO vB vH vS wQ zH tL) Il(sC tN tO tQ tR tX vH yD) Jk(aO sC tN tO tX vB vC vP) rN(dG Js Kd Nn Nq Qb Ri Tt) Fi(aR Fb mF nA nJ nK tF) Rv(iB jM mF nD nJ Nw Pk) Gl(Dw Ew Lp Lt We Ye) Na(aC cK oK sC tN vP) tX(Gz Nt Qc Qd Rm St) It(Qv sC vC vH zH) We(aM bR Hr Hx Vp) Ye(aC aO bW eD nN) Lt(aM aO bU Kk Pk) fN(aO sC vH vS yL) iH(aO My Nm uZ vB) qW(Ru Sf Sh vP vV) oV(aH aI aL hB iP) Ew(aN Cs Jj Mn) Gz(sK tN uL vU) Hl(eM nJ nN nU) Ii(Mb Nc Ne Nl) Nt(sC tO vP) Lp(aC bW iP) eD(Gd Si Va) gC(aC aM nW) gV(aD Qx Vo) zH(qP sC yH) qZ(kN mM nK) lN(Fd Gh Sf) Ms(Nc Nl) Ij(sF sH) Wc(eM qV) Xa(aO eM) Oi(qO tO) Vp(Hp Yl) gZ(aI iP) vB(Cw Ky) NqqD MbNc MusJ NlOf WbfB SioH SfjP QcsC StvS QvuZ PsPk RxbU RtmT VcjH UyjV VajI aHpI aQqO tOrB} fN{tT(Ad Ao Ap Aw Ba Bb Bc Bo cB Ch Co Cp Cw Dg Dk Fa Fr Fw Gl Hb Hc Hf Ip Iz Jd Je Jg Jj Jp Ke Kf Kg Kp Kq Ky Lh Lx Ma Ms Mu Mv Mw My Mz Nh Nm Nv Nw Ny Of Ok Om Ow Pd Pf Pg Rc Ri Sr Tr Tt Uf) vS(Ad Ar Aw Bb Bc Cw Hf iH Jd Je Jg Ji Jp Kc Ke Kf Kn Ko Kp Ky Kz Lh Ms Mz Nh Nj Nw Ok Qv Sr Tn To Tr Tt Tv Ur Vt) Jd(Aj Bc bZ cF cL cV Cw eD Hf Ip jV Kp Ky lN Ma Mz Nq Ns Oe Oi Pf QU Qw rN tX uG uL uP vT yH yL tL) tX(Ao Aw Bo Cp Cw Jg Ji Jp Ke Ky Lh Mz

Figure 6 Continued

Figure 6 Continued nR Sf Vz) nN(aY cG cU Cx) nC(aZ Ed Oa Pi) Yh(Jh Qm Vu) Ye(bH Uh Un) Rf(nL Vi Zw) Yf(dL Rm) Yd(lk Jd) We(bH Po) Rh(Ps Zw) mY(Id Ow) kO(hG Oa) AamW DdYg DuQy WmSf GlVj NuVi HoaO IIVc VzJh RbnA WcQh WdbH WhaX KnnH RtRm OunT dBlY mMpF} Ji{Si(kE kF mF mI mP mZ nA nC nD nJ nK nL nU) Yk(lW mH mP mU nJ nN tF) Eq(mH mP mT mU nN nU) fR(Fp gP Hx Nd Nj oV) pl(li Mj mZ Nh Pa) Gh(mU mZ nC nN) Hl(mP nJ nN nU) Hf(uZ vV zG xA) oV(iZ Ld nl oQ) Wb(fB nA nD) Sf(mT nJ qV) Qw(tN tO vB) Rv(mT nI oQ) nC(Lp Rz Wh) Ef(Yg Zx) It(vC zG) Wc(mT mZ) fB(Qg Vz) gC(aM Yd) mP(Uy Zw) tX(Ip Ql) oT(nH nL) FrNd HxWe SsLt XamW YecR RtmH RmuP VcgL PctN gZoQ yHzH} qV{Wc(aD bR Ju Jv Kr Lv Mp Nc Nl Nn Ow Qc Rg Ut Zx) Bo(kl lW mF mH ml mZ) Db(mP mW nA nF nJ) Rm(Uw Uy We Ye Xa) bR(Rz Sh Si Vw) Ef(Fd Ho Rv) Mt(Sf Yh Yi) Tz(mY nF Rv) Or(mW Ry Ye) Uw(bL cX Fn) nC(cW Ou Um) Im(Sf Tm) Iz(Ps Vb) Yi(Jn Pk) Yj(Hw Ug) Qy(Wh Yl) Xa(cM jE) bH(kC nL) bL(kO nT) mW(Af Cx) iJ(mP nN) jG(Uy Uz) DdRt Eqlb FcdC FnkP HuSf IsnK YhJn ZwQa JdnF TmOw KfmS KnnD YljE UxaM aZmF cEnR} fA{Gh(aJ aW bB bC bW cJ cR CX Dd eF Ez Fp HC Hl Kl Kx Kz lW mF Mj mM mZ nA nC Nd nH nL Oh oP Pa Qg Ur Wc Zw Zx Xa) Wb(Af Ax bB Bn cG cJ cX De Hu Mn mT Ur) Kx(aD bU cG dC Eq Fc nJ) cJ(Eq Fc Mk Rt Rv Zw) No(bU Sf Yk Xa) Ph(Eq Uy Yj Zw) cR(Lp Si Yj Ye) Dd(Fd Gb) Jn(Rv Wc) Ko(cM Fp) Ks(Zw Ye) Ur(Ho Lp) AxFd TjmF HlQa YlcG UnPa} hX{dF(kl kN kP mF nA nF nl nL nN nO nT oP) bF(kl kO mM mT nC nO oP oQ) aY(mM nA nC nH nK nL oQ) bQ(kP mF nl nL nN oP) Rt(Jp Jr Ml Qg Rc) cU(kG IX mM mS mW) cX(kG kN mF mZ nl) oP(bH bL cJ cS cV) cB(kl kN mF mH) nK(bL Hq Is Nr) cS(lW nC nO) mF(bV bW cV) kN(bN bV bW) bG(nC nN) nR(bH cl) ml(Hq Nr) Emlk MemU liWc HfKq IskE aKnD aMmS aXnC aZmT bLnU cEnH cVnN cWnO} jG{Vc(Ez Iz Mg Qt Qy Qz Ut Uu) Ye(bB Co Cu cZ dD Kr Rm) Yi(bl cB Ct Ib Rc Vs) Mg(Gh Hl Si Ux Vb) Tz(Eq Fd Ps Vj Wf) Ut(Gh Rv Uy Wh Yj) nR(cW Jf Ug Ul Vv) mW(Aa Af aM Bg Cp) Mz(Em Rz Sh Uw) Yl(Bc Ct Rc) Uw(aU Ub Uv) nN(Dl Jf Ul) Bo(mY nH) Wm(Vz Zx) Ti(rZ Sh) Yd(Ct Ib) Si(cP Qz) Zw(bH dE) Nx(Vj Wd) mM(dC Fb) DcYg EmNw ImVj LzYj YhRc WeUr XaRi KfmS Kysl RycO OunT VbOy} hV{We(Fn Im Ny Ps Qm St Uh Uv) Vw(Fn Iq Jj Nc Ne Nl Ns Pa) Ps(Oi Oz Pc Qu Ug Vs Wd) mH(aX bC bN bW cB cl dN) nR(aM aO bA bB bZ cX) Ux(Iq Jk Jq Pa Ti) cY(mS nD nl nK nL) Wd(Dp Fn Ih Ug) aU(kE kl mY nT) kP(aV aX bL cX) Wh(Ir Ur Uv) aK(mP mS mY) Fn(Uw Vj) aZ{kN nF) cX(kG mU) BbvV EmKn MlRt IdVc IqUy WcQm WfUn JtVj UgVi aVnB aYmW bNmF cMfR cUnK} Rz{mF(aM Ax Bo Cs Ct Fa fB Lj Mx No Nw Oa Uh Ur) nL(Ax bB Cs Lj Mn Mx Nq) mZ(Ct Mn Mz oH Uh Ye) nJ(aM iP Lj Mx Or Rg) lO(Bg cW Gl Jd Om Tz) Eq(mS mT mY nR nU) cR(fB kN IX mU nC) mW(Ax Cs Jd Lj Nq) fB(Aa Mb Pa Vz) Fp(kE mS mT) nA(Fa Nq Or) Lj(nC nH) Ur(gC nU) Oz(kF oT) bW(kO nU) nK(Cs Nq) kQ(No Or) AxnT FwoH GplY MxnC IrmS} Du{mT(aJ Ih Im It Jl Mb Mw mY Ni Nv Ny Pb Pi Sr Wb) nJ(aG Ao bZ dF iA Nv oF Op Us Ut Tj) mF(aS bl bS Hp Ld Mb mH Sr Tj) nU(aD cR Hr Mb Nq oH Pa) cR(lW mM mU nN) gC(dN Hx Oz) oT(Mb No Oz) Bn(nL pl) Nq(mU oP) Ko(kQ oV) Ld(hG mW) cM(gL iO) nR(Aa bJ) ml(Jd Mw) lO(cN dH) Afpl EdgZ JlnL UtmY VcgL PhnT cDtF dFnK nNoH} tX{Uf(Al bZ dG Gp iA Mn Mp Mu Nq Qd St uR) Ip(aR Hu Il Iq Jg Jp Ky Na Nw Qc Qd) Nq(Ao Ap Bb Bc Jd Kg Tr) uZ(aR cF Kc Ky Ri) Gp(Ao Ap Jg Tr) Tt(cl Hu It sK) Jd(Hf Oi Qw uV) Bb(Hf Kd yH) Nm(Nt Oe Oi) Tr(Bg Ky Ri) Ao(bZ yH) Jg(Mh Oi) Jp(aR Jn) Jt(lt Qd) Kf(Fp iA) Ky(aR Kg) ApBg BcGz LyHf IINw OiOm bGcl bZfP} Op{nJ(Af As Ax cX Fp Hf Jk Kx Nd Nk Oa Oz Pa Pb Zx) lO(aO Ch cJ cN Cq dE Ik Je Lj Mk Oi Vs Ye) Mb(nD nH nK nL Ru) Pa(ml nD nK nN nU) Aa(fB iP mM nU) nN(bW Hl Nq oH) lY(Af Jk Nd Zx) mZ(Jk Kz Nd Zx) Pk(Rg Rj Ru) mF(Ar Fa Ij) Oz(nD nL) tF(Dd No) mY(cX Fp) jE(cJ Ye) NdmS NimT KoiZ QnnL UrnU aAmW} tN{Uf(Af Al Bg bZ Gp iA iP Jv Lv Mp Mu Nq Oi Pi Qd Qv Qw Ri xA) Ip(Il Jg Jp Ky Na Nm Qc Qg Qw Ri) Kf(Fp iA Na Nu Oi Ql Qw Ri) Bb(Hu Na Nq Oi qA Qw yH) Nm(ln Na Nt Nu Oi Qv Qw) Na(cl Dc Jt Ke) Ri(Kc Nu Nw uV) Nq(Jd Ke Kg) Qw(Ko Mz Vo) Nw(Af Il) GpKe LvKy Hrsl HuTt JgPc KgOf cFuZ} bB{gZ(bZ cG Me mY Nb NN Nt Nu Qg Qy Qz Rc Rg Rt Rv Uo Ur Ut Uv Vz Wb Yd Yl Tj) Rx(ml mW nC nD nJ nL nN nU) Vz(kE nA nD nK nL) Hp(kE nA nD nK) Wb(mP nA nD nK) Zx(kE mZ nA nJ) Gb(mF nC nL) fR(gP Hx oW) dN(oV oW) tF(Gh Yf) FcoQ FpfB HlnU WfiZ QznF RvmT QnoV VbnC VinA OzpI bPoW dGgC} cR{We(fB kE kl lW mM mP mU nB nJ nN) Ye(hC Jp Ko IX nC nH No pF Uh) Fd(kl lW mM mP mU nN) Xa(gZ kl lW ml mM mN nN) Yh(kI mM mP mU nN) Sj(kl lW mM nN nU) Lp(gZ nC nH oW) IX(Hp Ow Oz Yj) nR(Gh rX rZ) lW(Rv Si Uy) Yj(nC nH) Wf(kE nH) nN(Em oH) mU(Ed Tm) oW(Uk Wb) oT(Nr Qn) YfkE HpnC VcgL VwfB} rZ{Ti(aZ bH cC cP cQ Hf Nh Nu Qg Ri) bL(kO nB nC nD nH nL nO nT) nR(aD aF aG bF bH bO dD dE) nN(bF bZ cE cH cV Hx) mF(aF aO aW bQ cF cG) aM(kF mU nB nC nT) dC(mM mS mY nl) aY(mM mS mW) aZ(kN nF nl) Aa(mW mY) bF(mM mS) bG(kF nC) bH(mM oP) cW(kP mZ) MenK IjmW aKnD cGkP cJnF dBnO} jE{bL(mM mS mY mZ nD nl nJ nK nR) Yl(bH Ch Gh Je Jh Rc) nR(Ct cW Ed Jy Us Uv) Wh(Nj Og Rh Vp) Ed(mU nD nN) Gb(Ju Qh Sf) Tv(mS nA nD) Yi(aZ cC dE) Ow(mF mH mY) Ct(mP nU) Fn(Sf Zx) Gh(Iz Ua) Tz(mS Rt) bH(Ry Ye) nN(Ar dE) mF(dB Nk) AnmW BcFc HamS TmU IkYd SicP StnK KyyL RhVw OunL aZlY cWkG lXiA hGkO} Eq{mY(Ao Dg Fy Jg Jo Qz Uc Ut) Ko(gL mT nD nH nN nU oW) Jg(kG mT nC nD nH nL) mS(Ao Fy Ph Pi Tn Ut) Qz(eC hC mF nD nK) Ao(kl lX nB nN) Ef(bR Dd hC Zx) Ij(mH mP mU oP) nO(Jd Nv Tn Ut) cG(gC mF nJ) mT(Fy Ih Kq) Nv(nA nK) Ut(kG mP) lO(Qm Si) CutF NgnY TnnN IzhC KxgZ PhkI} uZ{Mz(aP bM Bo bV bX cU cW dN fP Gp Hf iH Kz Qv Ri) Qv(Aa Ap Jt Kf Nm Nw Qc Ri Uf) aP(lt Kc Ky Mu Nq Nu Nw Oi) Hf(Fr Ke Kq Lw Lx Mq) Jp(aR bQ Gp Ky qO) Un(bX Nq Qw Tt) Gz(Kz To wD) Ke(Bo Fb iH) Nw(Gp iH Kz) sl(Il pF) AaiH FbKy NaKq KfqO} No{oT(Af al aU aV bE Bn bU cB cO cU cV Cx cY dA dD dJ Hl Hr Hx iJ In Mj Nh nR nU Pa Qv Vu) Ye(aM aO bR bW eC hG iP kQ) Yk(gZ mP mU nN oQ) Lp(iP mF mW nA) Ef(Ps Yg) Yl(mU nN) iJ(Ru Vj) FrNd GhmF HlnU WefB VcgL UymP UxmT bUoW} Hl{nU(Ao Ax Ih Ij Iq lr Js Ko Mp Nm Nr Oa Ow Qe) Qe(lW mM mP mU nN oW) lr(mH mP mS mU nN) Qa(lW mM mP mU nN) Vu(Dc Dd Jt Ko Mn) Ij(fB gC mP oW) nN(Ao Iq Jm) lO(cM Mz Qm) ml(Ao Kq) oW(Ko Li) NqoP IhmW IqmZ KxmF UhmT} Rv{Ef(Af Bn bR cF cX Dd Pk Ur Vp Zx) nJ(cG Ko oF Qz Uc Us Ut Vv) Aa(fB kE kN mF mT) Ut(Dd kP mY oV Qd) gL(Dd kE Ko mY) nN(Ao Ij Jn Nq) mT(aA Mb mY) Nq(nU oP) Jl(mF nA) mY(lt Tt) mZ(Pi Us) ChgP HrnU IjmP JdmI JgnC KonD NvnA} yH{zH(Bb Bc Gz Hf Im Ip Jp Kc Mz Na Nq Ns Nw Of Oi) sl(Bn Co De Ha Hf Ib Kn Pc Ql Qw) Tr(Hf Hu iH Ky Qv Ri wG tL) Bb(fP Qv Qw tR) Tt(Gz Hu Ri Vs) Aa(fP Na Qv) Hf(Jg Lv Mz) Na(Kq Nw) Qv(Ap Lu) GzMk NmiH} Ti{rU(aL aR bL cB cF Co dD dE Ha Hq iA Ih Ij Il In It Iu Jj Kd Ks Ld Mk Ml Ms Nf Nq Ns Nu Oa Oi Qb Ql Vp) rO(aR cB cF dD Ih Il Iu Ms Nu Oi) rQ(bl qC) oH(nN oW) NulO XamS cFrR gLlY} fB{Aa(iJ Ny Rt Tn Uc Uw Ux Vi) Wb(Ao Fy Ij Jg Ko Nm Up) Vz(Ao Cq Dg Fy Ij Jo Ko) Vw(Mb Mg Mk Oz Pa Qv Uo) Ij(Ju Sf Yj) Qg(Ih It Nv) Ko(Pb Yd Yl) Hr(Im Ks) Ux(Mb Pa) BaOz FyYd MkYi NcUt ltUr IzZx JdNy KqbW KsaG} rX{aY(kl mF nK nN nO nT oP) kP(aM aS bL cZ dA dC dH) aD(mT nC nK nL nN nR) mF(bV cF cJ Nc Nk Nl) cW(kG kO lY nO) dC(IX mU nD oP) dH(mP nH nN) cJ(nN nT) nO(cH dB) mU(aM bR) NknK aGnU aXnC bLnL cEnR cMnN cYlX dElY} tO{Uf(Aj Al Bg bZ cF Gp iP Ky Mn Mp Mu Nq Oi Pi Qd Qw Ri St Ua Um) Kf(aR cF Fp iA Ih Nf Ql Ri) Ke(Gp Hf Mn Nq Oi Qd Ql) Nm(Nt Oi Qw) Tr(Bg Hu Ky) Nw(Gp Il Ri) aR(cl Ky) BcHf KcRi KgOf} lO{mW(Af Aj Bb Bc Bg Cp Ct Cv Cx Dc Dg Ef Fb Fw Iz Kl) Yj(aE Fn Io Iq) Mz(Wc Yh Yi) Si(Hc Lu Ua) Ye(bH Cx Uh) iJ(mM mY nU) Fn(Sf Zx) aD(Ps Vw) DgVj EfHp EzmF Fdli GbUp HobW TzYk IkYd WfcM OwnT UxdG cWmZ dRmS} Ut{Ye(lW lY mM mP mU nN) oV(aM Kx Nc Nk Yg) Dc(Fd Ho Lt Ps) Ru(aO ol I oK Or) lY(Yd Yg Zx Tl) mY(Sh Yd Yg Zx) We(bR Lj Vp) oW(Kx Nc Nk) bR(Gh Lp) DdRx HpVp HqWh PsLj KznF LtaO VcgL VjiJ aMgC} Jd{Tj(Fn Im Iq Ir Kq Li Ml Oy Pe Qa Qe Tt) Tt(Hu It Nu uP) We(aM bR cD Nk) bU(aR iH Ki Na) Oh(Js Na Oi) Nq(qC tR) Iq(Nk Og) oW(Af aL) GpzA HuWh IvKq WdnJ YebM KyuP LpbR RivV OitR fPzH} Nq{Un(hP qC qD uN zH tL) Yj(mW nA nK nL oP) Uf(tR wK wP wQ tM) Gh(mF mW oP) gZ(Kx Lp Wh) tR(Bb Ke Kg) pl(aX Yg Zx) Kq(oV vB) bR(Wh Ye) wK(Ke Tr) oP(Vz Yi) BbqA KxoT LpnA

Figure 6 Continued

LtnN} Gz{Bc(hP rV sO uN wD wF wH yL) Tr(hL qI rR tR uI wB wC yL) Tt(qI rU uI vH vP wC wD) cl(hL sO wH zl) Jp(yD zG zI) hL(aD Fa Jh) MtxA TouY TnqI aDtR} mT{Uh(Ho Rt Wb Yk Tl Xa) Vi(Li Lj Nd Oz Pb) Yf(It Kq Lj Mx) Ux(Aj Li Lj Ur) Uw(Nd Oy Pa) Gp(Wb Zx) It(Rt Vw) Sr(Ho Tl) Pb(Gh Wh) AxWe ToVz IhRt StYe KqgC LjVw} Nd{Fr(aA Ii Jj Li Nc Nk Nl Of Og Pd Pf) Jg(aA Aj aR Bo bU Db Jj Nc Of) Li(aA Im Lx Mt) Yi(mS oQ) Jp(aA aR) BoOf LxaA NcNw QaQb XamY} Ef{Yg(bR Cs Ko Li Lj Mn Nn Ow Ur) Zx(aM bR Cs Lj Mn Or Rg) Cs(Fc Fd Ho Lt Ps) Lj(Lt Ps Tm) Aj(Em fR) Lt(aM Or) Vb(Af Dd) NkZw LpRj} Aa{Qv(uI uX vA vT vV vW) Yi(hG iP kF mM mW) Vi(lY mM nB nI nJ) Yf(kI mF mH nU) Gh(hG kE kN) Na(uL vU xA) hG(Gb Yk) NroT ZwmW cPpI} Kx{oW(aG bU cE gL mF Mk Nv) gZ(aD aG bU cG Mx Rx) oT(aG bR bU cE Jp Nr) oV(aG bU cE mF Nv) gC(aM nD oQ) mF(nT Rx) WebR} Un{tL(aR Hf Ih Na Oi Ql Qw Rm Tt) Ql(uG uN uU uW tM) Na(qD uL vB wH) Qw(qD vB zH) Tt(hL qD) mS(Wc Xa) NuqD KywH RmyK OihP iArS} Ye{mF(Ax Jl Nj Nv) Dd(Fp Lj Qb) bR(Fp Qa Qc) Ao(lX nN) Jq(mZ nJ) Nv(nA nJ) hC(Ur Vj) AxmW FdnN FrbW HqmI JlnA OfnU UhaM UpiZ UsmZ} sI{rS(bG dM Fn Jn kR Ne Nl pF) Ky(eT vP vV tM) rT(aU fY qO) Tt(Aj Je) Il(Nw zH) HrIq HuTr KeuN KptQ RhyL UsaF pSqO} Qv{Nm(oV uT uU vB vH) Tt(qQ uG uY wG yD) Tr(vH wJ tL) Bb(uU vV) Ri(uN uW) Uf(uT vH) vB(Ap Nw) BcuU IqnL KywH UguN} Hf{Kq(hL oK qB sK uL vB vH zG xA) xA(Jg Nw Tr) Lv(vI yE) zG(Bc Jp) zH(hC oE) AphO FrvP NmhL TrvI NwvV VjnR} Yi{Rh(kG kN mF nD) Pa(nK nL nU oW) mW(bQ Kg mY Tj) mS(Gp mY Pz) nN(Hr oH) TjmF GpnU YklY OznK aJiZ} Xa{gZ(cG Hu Kr Mn Mx) mY(mW Og Qe Qz St) mS(Ir Qb Qe Uh) Pb(oP oW) nR(Uo Ur) mI(Kq Ky) UpnU} Jg{Aj(aR Db Hx Mb Na) aR(bR bU cJ cQ) iH(bU Nm Oi Oz) Qw(uM vB) Jj(Nc Nl) DbNj IptR aMgC} Kf{tM(Ax iA It Ky Nf Ql Rm) Ql(qO qQ wQ) iA(tR vP vV) Fp(tR wK) QwvB RmrP OiwK xAvH tLqO} Ko{oW(aL Gd Iu nT oH Yh) oV(Ax Fp Ou Rx Yd) gL(Vb Vc Yk) oT(Qn Yk) GbiZ WcnU LtVu ViVp} Ri{Tr(rR rU tR vP vV yL tM xA) Nw(tR vP vV xA) Tt(tR wD) Ip(rS wH) BbvV WeLj KctR} pI{Gh(Ax Lj Zx) Oz(bU cM Ng) Af(Ld Oa) Bn(Fa Oa) aX(Li Mv) CxFa FyKg TthC KqPa UmcM UhmZ} We{aM(bR Dd Nk Uh) bR(Fp Om Or) Ax(mH nJ) Dd(Lj Rg) Pk(Or Rg) hC(mS Tj) FpmH UhnD} Ao{Vb(kP mY nJ oQ) Ho(mI mW nJ) Uy(kI nB nN) nN(Yh Yj) mS(Wf Zx) ShgC WhnB} Ip{Jp(hL tR uY wG zI) tR(aR Il Iq Ky) fP(wQ xA) iH(vU yE) QghO KywH UfwP} Tt{Hu(tR uX zI yE) hC(oV oW) qQ(Aj Oi) GpzA MzuP NfqA QwuX aIgC cHyL} Nw{vB(cL iH Jv Kk) vV(Af aV iH) Il(uP xA) tR(aR Gp) AfxA LtmF iHvP} gZ{Hr(Jm Ks Oa) cG(bU hC Wb) Ha(Ur Yj) Oz(Fa Nv) AxFd DpKs UhbU UriJ} Ky{wH(dH Lv oF Uf uP) Jp(zG xA) yL(Tr Uf) uP(oH oK) LvwL OwnC} Vw{mH(Ax Cs Fp Gp Kj Lj Oy) mS(bQ cV Mb) RjkI gClY kEoH} gL{Vc(Dd hC Jn Mx Or Sr Up) Wd(kC kF lY nI) YkUh} oV{Fa(aI aX) Gh(nA tF) Mx(Qn Yf) iJ(Ld Nt) AxQn CuYh HrJm KnlY} Na{Kq(uL vB vH vP vV zG xA) Nm(hO uL) Jt(hO uL)} aR{qO(Bb sO uO zG tL) zG(iH Jp qP) GhgC cItR tLqP} oT{Oz(Lp Nx Sf Wb) Qg(Ax Fa) Qn(Lj Oa) GhbI HaHr LiaI} iH{Nm(hL Nn Oh oK vB) cG(nO nT) BnlX MzvB bUnH} aM{gC(dF Kq oF Uh) Bo(Bb Dg) AwDg GpfR LtUh} mZ{Cq(Vz Yg) Us(Wf Yh) Vb(Om Tn) YfMx WdNv UhVi} nN{Jn(Uy Yl) oH(cJ Sj) FpGh HrIr IjYk IqYj} hC{Wh(mS Rj) Wf(bW Nj) ChVj QzVc RxkQ UybW} Fb{bW(Lp Wh) AphO BbqC GdUr RuaG VckS} Tr{Ma(qO qP) DbuL LxwG QwvB JvyL aNwJ} Jp{zH(Il Jn qO qP vV) NkvB qQvV} fR{Gp(dR gP) FpJq QelW RgmI UhgP aNcE} Mz{fP(zH xA) qC(Qw Vp) IlhP KzvB} Ij{Sf(lW mH mP) Yk(mH mP) LpmS} Vj{Qz(oH oN) iJ(Or To) AfmF TvnU} nK{Pa(Ho Wb) CqVz IvNy YgbQ YlcG} Fd{mH(Ax Gp) nJ(mS Nk) HrnU} Gh{Fp(lW mU) FamF JfoQ JnoP} Yj{Iq(eF mF mY nU) GplY} Ke{iA(vP vV) GptR tFvV hPvH} gC{Kq(aY dL) FamS WboF LdiJ} Ap{Oi(qO qP) GptQ aQqO} Cu{wQ(It Ql) ZxoK StyL} Fr{Nl(Ii Ms) MbNc LpbW} Yk{Uh(kG mP) MwmI SrtF} Uf{bZ(qO rU tR) cVxA} oW{GboH HaHr NncX KkbW} Wb{MnoQ PanD dFoP} Vz{Cq(nA nD) TonR} Lp{FamF UrnR UpnB} mS{Ir(Wc Yf) WcNy} nJ{oF(Rx Yl) AxYf} Bb{KpvB aQqO} Bc{Qw(zH tL)} Nm{NttR IntQ} Ue{MtLt HoiZ} Ih{WdkC UykE} Zx{IzLj OwoK} Wh{bR(Cs Up)} cF{DgaW KgtR} nT{CoMy OwcG} mY{FciJ WdNv} AxRxnU GbKqnA YgbQkF KcKzvB UrUxkN VbkEoH VpParS

Constrained panels with 2 analytes, where 1.0E-8 >= 'AUC p-value' > 0. Contains 363 panels of 200,591 total panels evaluated. : Et(aC aO aR aW Bo bR cK Db dU Eo Fn Fp Hf Hx iA Ic iH Ii Jd Jj Jo Jr Kr Kx Li Lv Mb Mf Mh Ml Ms Mt My Nc Nd Ne Ng Nh Nj Nk Nl Of Ok Oy Qv Qy Qz Ri TT tV tX Tj) Vh(aM bR bU Dd Dp Dr Ex gL Gn hC Hr Im Jd Je jG Ji jY Mt Om Or Pi Pk qT qX rA Rg Ut) tV(Ad Bb Cw Di Ic Ip Jg Kc Ky Kz Lh lK Ma Mm Nm Ok Pj Qv Qw St Tr Tt Uf Um Vq Vt Tk) Nd(aA Cw Fr Jg Ji Jl Jp Lh Li Lx Ma Mm Mn Mt No Nv Nw Ok On Qa Qe) Zq(aC aM bR bW dM FB iP iZ jT kK kP lY mH mM mS mW Or Pk Rg) aC(Ad Ap Aw Bb Bc Bo cB Cu Cw Dg Di Dk Dl Dr FR Gc Ok) Ok(aR aW cK Hx Ii In Lv Mb Ml Nc Ne Nh Nj Nk Nl vB) Pj(iH Jd qB rN rR rW sC sH tO tT tX uL vB wD yH xA) Jd(Cw Di FN Ic Ki Lh Mm Na Og On Qv Tj) Tk(Mm qO qP rW sC tS vP vV wH wL yL) Dr(Ef jB Jg jM jP jT oD On qX Ut) Nl(Fr Im Jg Lh Li Ma Mm Mn On) Ad(Aj aM aW bM Bo cF cN iH) Nc(Fr Jg Lh Li Lv Ma Nw On) Mm(sC tN tQ tT tX yH) Nj(Cw Fr Ma Nw On Qa) On(Hf iH Ii Mb Ne) jD(Ic Ry Uw Vi Yi) qX(Fc Hl Si Vc Zx) oD(hB Kx Ld No Ut) Eo(bB Lx Nw Oh) Jg(Aj aR iH Ne) Ji(aR dU eP fR) tS(Bb Di Ic Vt) jB(aH Mk No Oz) jT(Gh Hp Vc Wh) Gc(Ef jQ jR) Va(hV jI jK) eO(aW bB Jj) tT(Bb Kf Lh) qY(Ps Vi Zx) pH(aH bB Ko) Aw(bM Dl) Dw(bM Lx) No(eQ oT) eW(aM Lv) rN(Ic Tt) CwoK DumE EwLx TheQ NmiH MnNe HbeP HfKq YijQ SirA ZxqT QaQb KxdU LhvV UftO UwjO VtuZ VqsC aHpI gWmS nNqU lXhB Constrained panels with 2 analytes, where 1.0E-7 >= 'AUC p-value' > 1.0E-8. Contains 305 panels of 200,591 total panels evaluated. : Ok(Bo bR cQ cW Hf Hr iH Ik It Jd Jj Li Mf Mh Ms Mt My Nb Nm Of sC tS tX) Nc(Im Ji Jp Lx Mb Mm Mn Mt Nb Nd Nk No Nv Nx Pd Pf Po Qa Qe) Jd(aM aR Bo bU cF Db Dr Im Jp Ky Nu Oh Qa Qe Qz Tt Uh Zq) Jg(aC aW Bo bR bU cB Db Fp Jj Lv Mb Mh Ml Ms Ng Nh Nj Nk) Et(aA cR cT Cw Di Dr jB Kk Kp Lj Oi Ow Ql rW tN tS tF) Vh(aG bB cF cR Dk Fb iZ Jn Kp Li Lj On Pf Qy Vp Vq Zq) Ad(aR Aw bA bU cB cK CT Db dF Di Mb Nd Nj rN rW) Nl(Ji Jp Lv Lx Mf Mt Mv Nb Nk Nn No Nv Nw Pd Qa Qe) aC(Ao AR Ba Bg cF Ch Co Cp Db Dc De dN Ex On) Nd(Im Is Jt Mp Mv Mw Nn Nr Ny Pd Pf Po) On(aO aR cK jB Lt Nh Qz rW tT Tj) Nj(aR Im Jl Jp Lh Li Lx Mt Qe) Dr(Dk Fb Fr Ji Ko Mt Tn Zq) Ne(Fr Ji Lh Li Lv Ma Mm Nw) tV(Ao Ap Hf Il Kf Kj Lv Ms) Cw(lL oH Pj qU vB vI Tj) Zq(Bb Hx jD jK Kj Lt Ut) Dg(AW Bo cF Di) Lh(Ms tN tO tS vP) jB(cX Ex Ji Qe Uh) Fr(Hx Mb Nk Tj) fR(cE dR Gp gW) jD(nN Yg Zw Xa) Bb(aM fN tN) Ic(jI tN tX) Ip(tS tT tX) Vq(vP vV tL) Bo(Dl Ef) Di(tO tT) Mb(Li Nw) Mm(iH rW) Tn(eP Tj) Jp(aR fN) Kg(rN tS) Kq(Fn Na) Rv(Ef Ut) Uf(tN tS) Vt(tX vS) NmtT NqpH LvLi MnNh MzfN YilM ZwjQ JibU XajT KfrN KkdX NvoD WnwL VijO aNeO aWeP Constrained panels with 2 analytes, where 1.0E-6 >= 'AUC p-value' > 1.0E-7. Contains 596 panels of 200,591 total panels evaluated. : On(aN aW Bo bR cB cR Db dU Ex Fn Fp Fw Hx iA Ic Iv Jj Lv Mh Ml Ms My Nk oD Of Ow Pk Ql Qv Ri Rm tX Us) Jg(aD Ar bB bM cK cQ cR Cw Di fN fR Hf Hx Ic Ii In Iv Ji Li Lj Lx Mf Mt My Na Of Oi Oz Pf Pj Pz Qa) Cw(bM cF Dr eD hL hO Ic Is jM jY Ko Kq Mm Nf Nl nT Ok Ow sK Tn tS tT Un Ur yH tF) Nj(aA Ar Bb Bo Db Dg Di Dk Fp Is Mm Mn Mp Mu Mv Mw Nb Nn No Nr Nv Nx Pd Pf Po) Dg(aD Aj aK aM aN aR aU aV bA bB bM Bn bR bU cB cK cN cT cY iH tV) Nd(Dk Fp Ih In Jj Jq Lj Lv Lw Me Mf Mr Mu Mx Mz Nl Nm Og Om Pe Qd) Ad(aK aU aV bC bF bQ cE cG cY dN Dr fN Hf Ji Jj My Na qO tS) Ne(Im Jj Jp Lx Mf Mt Mv Nb Nn No Nv Ny Pd Po Qa Qe tV) Nl(aA In Is Iv Jj Jl Jt Lj Mb Nh Ni Nm Nx Ny Om Pf Po) Fr(Aw Bo cF fR Ic Ik Iv Ji Jj Lv Ml Ms My Nh sC vP) Nc(Fp In Jj Jt Mf Mg Mh Ml Mr Mv Mz Ni Nm Nn Ny Om) Dr(bB Bg cB cG Ch hC Iz Kq Mn Oh Ok Om Ow qT Qu) Jd(bR cB Hf iH In Ji Kk Kp Kq Kx Lw Op Ow pH Ue) Lh(aC aR FN jD Mb Nk

Figure 6 Continued tR tX uP vB zH xA Tj) aC(aW bC bF bM Bn bQ bR bU cE cG cT dF Ji) jB(cG De Dl dN Hx It Jt Ko mE nN Ny Qc Qm) Ok(Aj cF iA Ic Iq Kx Lj rW tT vH vV Tj) tV(Dd iH Ke Kg Kp Na Nt Of Qu Rh rW vP) Gc(bQ cE dD eC eF fR hC iZ mE Ut tF) Di(Ap cB eD Ef hX Is IL qY tN uZ) Ic(aM aR cN eD jG jR Kq rW vS tF) cF(aM Ap AW BB bF Bo Dl iH) Zq(Ap Ef Gl Lj Ns qY rA Up Yk) Bo(Ap Aw Ba Bb Ct cY Of pH) Mm(Kx Mb Nh Ow Qv rN Tn vB) Kq(aR aW Db iH In It Nt Nu) Pj(aW cN Db Fb jD kQ Qv tF) bM(Aa aW Bb Bn cB Cp De) iH(Aa Ap aR bU eD Jt rC) Et(Aj rN sC uP vB yH) Lv(Jp Lx Ma Mt Nh Nw) Nh(Ji Li Lx Ma Pf) cB(aD aR aW bQ rW) fR(aU bB bF cY Ef) tX(Ao Bb Ms Pd Tk) qU(kO mW nD nJ nL) pH(Du Uh Um Uy Vj) Mt(Eo Jj Lj Ms) Nw(Fp Ik Ml Nk) Op(eM mE Pk Ru) Vh(Cs Jr qW Wb) tT(Ap Kg Uf Vq) tS(Ke Kf Nm Tt) rW(Kf Mz Ri Tr) oD(Cu Mq oQ Th) Aw(aM Ap aR) Bb(bA bB tO) Mb(Ji Jp Qa) Tn(dX It Qz) Wh(jD IK rA) Li

Lv Mf Mh Ms Mv Nx Pd Pf Qb Qc Tj) Pj(Aw bU cB Ch De dF Fn Im Is Jj Kp Ky Lw Mv No Of Om Pd Pk Qa Qy Qz Ri Ss Tk) Cw(Aj aQ Aw bF Bn bU cB Ch cN cP cT cY dN gW Hw Lw mS nF rB rC rW tO tR vH) Nj(Aw Ax bA Bc bF Bg Bn bR Ch Cp Dc dF fP fR Jj Jn Jr Lw Mb Mg Mr Na nK Of) Nw(aN aW bR bU cJ cK Db Fb Hf Ii Jj Lw Mw My Oy sC sJ tR tS tT vB yH zH) bB(aH BA bM bR bU Cp Cu Ef Ex fP Io Is Jt mE Mt Nd Nl Nm nN Pd tF) cB(aJ Ba Bc Bg Bn cG cP cR Cu Cv De dN Ef Ex Je Mt Qa rU TN tS tT) fR(aH aM aQ Ba bH bM Bn bR Ch cM Co cP cT Cv Db dD dF Hb Jq Nd Nh oD) Aw(aQ Ax bA bC bF bQ bR cG Ch cT dF dN eO fN Io Is Mb Na Nd Qa tS) Qv(Db Ef Fb Im Io Iq Jt Kf Kj Kl Ko Kq Mg Mt Nm Ow Pd Qa Ss yH tF) aW(aM Ar aV bA bF Bg bR bX cE cG Co cT dF dN Ef fP Im Is Mt Qa Uf) Dg(bC Fn iA Is Jj Kr Ky Lv Na Ne Nl Oi Ou Pk Qz rN sC tS tT Tj) Jg(fP jD Je Kp Kr Mw Oy Qw Qy Ri rN Rv rW sC tN tR Ue Uf uP Ur) Kq(aX cR Dp Ha Hx Jj jM Kp mE Mt Ow sC tS Ue Ur vB Vp Ye Tk tF) On(Eo eQ Fb hX jY Kd Lw mE Mw nN Oy qP qY rN tN tR vB vV zH tL) Cu(aK aN aQ bA bF bQ bR bU Ch cN cT cY dN Lt Nd Rx tS tT Tj) aC(Io Iq Jh Lp Mg Mt Na Nm Of Om Po Qa Rz Uw Ux Vw Wh Yi Ye) jB(Ax Bn bW bZ cE cW Fd Gp Ir Lj Mv oF oN Qb Um Ut Uy Vh) Ar(aK aV bM bU cE cT cY dF Ef Fb fP Io Is Nd Sr Ss Tn) Cp(aV Ax bA bF bQ bR bU cE Ch cK cN cY Db dF dN fN Na) Po(Hx Ii Iv Jj jY Lj Mf Ms Nf nK Nm nN No Oy tS tT Tj) Lv(Ik Im Iv Jj Jl Jq Jt Mb Ml Mv Mx Nb No Nx Oz tS tT) sC(eD Hf Im jY Ke Li IL Lx Ma Ms Mw Na QW rC Tr zH) Mb(Ba Dc Fp Im Is Jt Ko Lj Mz Na Nk Nm Nn Nr Om Pd) Pf(Fp Ik Iv Je Lw Ma Mf Ml nK Nm Nr Nx Of Om Pd Qa) aM(bF Bn bQ bR cE Ch cT Hb Kl Ky Nd Ow Rz Sr Tn Uf) bM(Ao aS aU Ax bU cG cR cT cV cY dD dF dN Ef Of uZ) Mt(aU bR bU cR Hx Iv Jq Lp Mf Mh NK No Wh Tj) Nh(aA Is Iv Jn Jq Jr Jt Lw Mv Mz Nr Ny Of Pe rW) Kf(Db eD Hf jM jY Kx Nu Ow qO rB tX Ur vB vS tL) tS(Bc cH Dc Ex Gl Jd Jt Kc Kn Ko Kp Li Ma Qw Ue) Ad(jM Jv jY Kp Kr Lp Lw Ou rB tN tR tX Us vB) Qa(bR Fn Ha Je Jj Jq Kx Lw Mh Nm Qc Qg Qz Tr) Fp(In Iv Jl Jq Lw Mf Mg Nb Nk Nr Nx oD Oz) Ma(Hx Ik In Is Jj Ml Mx No Nt Om Pd Pe uP) Jt(bA bR cT iA In jD Nk qZ rN Rv rW tX wG) Li(aA Ik Jq Mf Ni Nx Qw Qz Ri tX Ue We Tj) Ow(Dc De Fn Hb In Jh Jj Ky Pd Qz Tn Tr Ue) Uf(Db fN Hf hL hO Im In Iq Kr Kx Ue Tj tF) dN(aQ aV bE bF Bg Bn bR bU cK dD Ef Nd oD) tT(Ao Ex fN Hf Jd Kc Mg Na Ng Of Pd tV zH) pH(aI bP bU Cs Dp Fb Gp iJ Io Jn Qn Sr Xa) Ba(Aj aK aQ aU aV Bn bU cY Db Na Nd) Tn(bL bU Db eM Ko Kp Kx Oh Ou Sr Ur) Lj(Ik In Iv Mf Mu Mv Ni Nx Of Pd Ux) dU(Ij Ir Jq Ky Mz Nx Oz Sr St Tv Us) fN(Bc Jh Ke Ok Qh tV Vq vS Vt yL Tk) tX(Hf Jd Jo Ke Lx Mg Mq Oh Om Qw Ri) Na(Ef Hb jD Ke lL tN tU vW yH zH) Is(aQ aU bU cK cQ cT cY Db Iv nK) We(Cs Dd Ex Ir Jn Jr No Or Pe Pk) Nr(Hx Jr Lw Mf Ml nN Nx Pd Wh) Jd(cR gW kO lL nC oO uP vS yH) Ml(Im Jh Jl Mw Nn No Nt Nx) Hf(eD jY Ko lL qU rN rW yH) Rv(gL Iz Jk mE Pi Pk Rc Ss) tV(aK cY hA jF jQ rS tO uR) oD(Du iJ mT Ng Nn nW Pe Qn) Fb(cR Db Jj Ko Oz Ue Ti) Mf(Iv Lx Nk Nv Ny Om Pe) Ke(rW tN tO tR uZ vB vH) bR(bF bQ cG cN dF dG Jh) fP(aD aF aO bU cW rW xA) uP(Kp lK Nm pS rS sO tN) Nd(Ao cG Ch Co cR Dc) Ne(Aa Jn Jr Of Pe rW) Nk(Ik Im Nt Nv Nx Qd) Ko(cR Fn Iq Kx Ky Ou) Ok(hX Je Kp Qy Sr Ur) jD(mS Sf Sh Vc Vh Yl) Tj(Im Lx Oh Pe Ut) Ti(Iq mE Pk rU rZ) Qw(Im Qt tN uX vS) Nx(In Jj Ms Og Pd) Vq(hL hO qX tO xA) nN(hB Ir mW nT Nv) nK(Et Hq Im Iq Mv) nW(Gb Sh Si Vj Yi) Dc(bA cT Ky Lt) Ef(cG Ct Jj Ur) Ex(Lt oK tO tU) Nm(In tO tR vB) No(Eo Ik Iv Lp) Lx(gV Jq Lw zH) Tr(Db Im Iq sM) Wh(hC Qc Qd Up) Tk(bG bX fY jR) bU(bA bF Bg cT) mE(Gn Kx Vh Th) tN(Jo Kg Pc wL) sO(qO qP vP vV) rN(eC Kl Nq Ss) Du(eM nJ Qy) Fn(Oh Qm Ut) Nc(Aa Jn Jr) Sf(gW jU qT) Je(Im Iq Ou) Ri(rC rU vS) Ur(Gd Kg Ou) Aj(Bg Kl) Bc(jY rW) Db(eD Nl) Et(jY rB) Mz(lL zH) Ik(aA Og) Hb(Kx Ss) Ip(zI yE) Iv(Mv Pd) Ps(Ss Ue) Kz(uZ yH) Nv(Hx mZ) Va(hW rB) Vi(Dd Pk) Pe(gV Lw) aY(eO eW) bA(aV cI) cG(eO nT) eM(Kk Lp) lX(gL pF) tO(Ao Kg) wD(vP tL) qY(Fc Yd) qT(kO nL) lK(vS Zw) oO(Fy qZ) ChKx ThmU GpRt IdvS IzLt YiiZ SiQz WdQm JjKl YegW RzOr YljM OiyH Vcjl UxPk VheC VtqD PdyK aPuZ cYdF dDdX hBkO sJrW Constrained panels with 2 analytes, where 1.0E-3 >= 'AUC p-value' > 1.0E-4. Contains 3,198 panels of 200,591 total panels evaluated. : Op(aC AR As Ax aY bA bB bQ cF cG Cp CQ Cu De dF dN Du Fp fR hC Hv Hw iB Id Ii In Ir Is Iv Jh Jo Jq Jr Js Jt Kd Kc Kn Kp Kr Kx Lh lO Lp Lt Lv Lw Lx Md Mi Ml Mq Mr Mt Mu Mv Mw Mz Nb Nf Nq Nr Nv Ny Of Ok Om Oz Pa Pb Pe Pf Qb Qc Qh Qu Qx Rt Rv Ry Ss St Tv Uc Ug Ul Uo Up Uw Uz Vi Vp Vs Vt Wc Wg Yl Ye Tl Wm) Qv(Aa aM Ao Aw Ba Bc cB cG Ch Dc De Dl Dp eD Ex Fn Hb iH Ii Is It Iu Iz Je Jh Jk Jm Jo Kg Kk Kp Ky Li Lx Ma mE Mn Mv Mw Nv Nw Oe Of Oh Om Ou Oy Po Pz Qd Qe Qm Qt Qu Rc Sr St tS Tz Ua Uc Ug Uk Uu Vq) aR(AA aI aK Ao aQ Ar aU aV bA BC Bn cG Ch cI cK cN Co cT cY dD Dc eD Fn Fy Gl HB hR Ke Kl Kp kQ Kx Ky lL Ml Mq Mu Ne Ny Qd rC rN sJ Sr tN Tr Uc Uf uM Ur Ut uZ Vt We yH zG tM Xa Ti) Ar(aM aQ aU bA bB bC bF Bg bQ bR cG Ch cJ cK cP Di dN Dp Fn fR Gl Hf iH Je Jh Jq Jt Kf Kl Kp Ky Lv Lw Mb Mg Mn Mt Mv Na Nc Ne Nh Nl Nm oD Om Ou Pd Qa Qe Qz Tr Ue We Ye Tj) Im(aN Bo bR bU bX cB cF cK cN cR Di Fn Fp fR Hx iA Ik In Iv jD Jj Jl Jt Ki Kl Ko Kx Ky Lj lL Lt Mf Mm Mn Ms Nb Nm nN Nr Nt Nx oD Ou Oz Pd Pf Ps Ri Rm Rv rW Sr tS uP yH) bR(aJ aK aN aU aV aY BA Bc Bg cL Co cR cT Cw cY Dc dH Dr Du eW Ex fP hB Jj Jl Ky Li Mm Mn Mz Nd Nh Nl Nx Oh Om Ow Pd pH Po Pz Qd Qm rW Rz tS Uf Uw Vi Vt Ti tF) Jt(aD Aj aQ aU aW bQ bU cB cJ cK cN cQ cR cY Db dU Fn fR Gp Ic Ik Iv Jj Kx Ky Lj Lt Mf Ml Mn Nb Nr Nx Ou Pf pH Qz Ri sC sJ tN tR uP Ur vB yK zH Tj tF) Dr(aA Af aH aI Aj aK aL aM aN Ao Ap aV aW aY Bb bM Bn Bo cF cN De Di dR Ez fR Gc Hr Ii Io Is Jh kI Kn Kp Lv Ly Lz Ml My Nm No Pd Pj Qb Qm Qy Rg Wh) Di(Aa aD aN bA BC Bn bQ bX Ch cI cM Cv De Ex Gc Hb Hf Je Jh Kl Ko Kp Kx Li Lv Ma Mn Na Nc Nm No Nw Nx Om Pf Po Qd qO Qy Qz rU Sr Ue Un Tj) bU(aD aM aN Ao aU aY Bc bH Bn bQ cE cG Ch cN Co cY Dc De dF hB hC Ic Je Jh Jj Kc Ky Li Mb Mf Mz Nd Nh Nl Nx oD Om Ou Ow Po Qa Qe Qm Tr Vt) bB(Aa aK aM aN aU BC bF Bo bQ Ch cN cP cT Cw cY Db Fb Fn Je Jh Jj Ky Lp Lv Mb Mg Mm Mz Nc Ne Nh nL Nw Nx Of Oy sC Ss Ue vS Vt We Yc) Ur(aM Ap Aw Ba Bb Cu Dc Dg Dk Dl dX Fb fR Ii Ip Iq Is Jk Jm Kj Kl Ko Li Ma Mg Mn Oh Om Ow Oy Pd Pj Po Qa Qe Sr Ss Tr Ua Uc Ue tF) cB(Ao Ax Ch Cs eD hR jD Jh Jj Kc Kx Li Lv Lx Mm Mn Mz Nc Nd Ne Nh Nl Nm Om Ow Qe qO qP rC rN rS sC tO Tr Tt tX Vq Vt yH Yi Ti tF) Bo(aD As Ax Ch cI cN Cs eD Ex Gd Hb Ii Ij Io Jh Jo jR Kf Kj Kl Kp Kx Ky Li lL lO Lw Ma Mn Nw Nx Og Oh Pk Pz Ss Tr Uc Ug Wm) Fb(Aj aW bQ cG cT cV De Dl Fn fR Hb Hf Ic Iq Ji Kf Ki Kx Ky Li Lx Lz Ma Mb Na Nj Ow Pd Qa qC Qz Ru sC uP uZ Vt We Tk Tj Th) Bb(Bn bQ bV Ch Cp De Fn fP fR hC Hf jD Jj Kf Kx Ky Li Lv Lx Lz Mm Na Nc Nk Om Ou Ow Pd Pf Pk Qa Qe Qz Sr uP vB vV zI Tj) Jj(Ba Cu Dl fN Fp Ic iH Ip It Iv Iz Jk Jl Jo Jp Kf Kg Ky Lj Mf Mg Mh Mn Mv Mw Nk Nm Nn No Nt Nv Ny Of Ou Pd Sr Ss tF) Ap(As Ax bC Ch FN Hf Jh Ke kQ Ky Md Ml My Na Nc Ne Nl Ou Ow Qa Qe Qz rW tO tQ Tr uP uZ vB vP vQ Vt vV yH Tj) Nm(AW bQ cK cQ cR Db Dk dU fN fP fR hB Ik Is Iv Jl Jr Lj Lv Ma Mf Ml Mn Mt Nk Nr Nv Nx Ow pH Qe rW sC yH zH) Db(aU aV bA Bg cT Cu cY Ef Fa Hb Io Je jR Kc Ke Kl Kn Kp Kx Ky Li lL mH Mn Mt Nc Nd Ne Nh Ou Qa rB Uh Ti) Qe(aN aQ BA Bn Ch cK cN cQ cT cY Fn Hf Hx iA Je Jq Jr Ky Lw Mx nN No oK Qz Ri Rm Rx Sr Tr Ue We Wh tF) Om(bM cK cR Dg FN fR Hb Hx Ic Ik In Iv Jr Lj Mh Mx My Nb Nx Ny Ow Oz Pb Qz rW sC tN tO tS Tt Vp zH Tj) Mm(aA aQ aU Ax bA bQ cQ cR cT cY Dc Hx Ib In Iv jD Ji Jr Me Mh Ms Mz Ni No Oz Pd Pe Pf qZ Sr Tr Ue Tj) Is(aK Ch cR FN Fp Gp Hf iH Ik In It Je Kp Kx Ky Lj lL Ml Nb Nk nN Nr Nx Pf Qg Qw Qz Rm Sr Tr Ue Tj) Qa(aA aN bA cF Ch cK cQ cT dD DE Dg Eo fP Fw Gp Hf iA jD jY Kp Ky nI nN oK Ou Qw Qy rB Rc Ue zH tF) aM(Aa Ao aV bA Bc cJ cK Co CV Dc De Ex Fy Gl gV Je Kc Ke Kp Ou pH Qw rC Si Ss Tr Ux Vj Vw Wh Yi Xa) Mb(aC Bc Bn Cp Cu Cv Dd De Dl dX Ih In Iv Jk Jq Kf Lw Mg Mp Mr Mu Mv Mw Mx Nb Nx Ny Of Oz Pe Pf Qd) Nk(AA aC aN cN Ef In Ip Iv Kf Lj Mg Mu Mv Mw Nb Ni Nn No Nr Ny oD Pd Pf pH Rz Sr St tT zH Ti) Ou(cF cR Dl dN Fn fR Fy Hb Hf Io Iq jY Kf Kn Ky Kz Li Lx Ma Mg Mn Na Nj Nu Nw Pd Pk Qz Tr Uf Uh) iH(Ao Bc Bn Cu Dc Fy hV hX Ip Iu Je Kg Kx Ky Lw Lx Ma Mt Nx Ny Oh Qt rN Ss Tn Tr tS tX Ut Uu Tk) Ex(aN aU Aw bA cF cG Ch cJ cN cT cV cY dD Dl dN Gp gW Hb Ic Kc Kx Lv Nc

Figure 6 Continued

Nd Nl Nx Pj Ss tR tF) aW(Aa aD aK Ao aQ aU Bc Bn bQ Ch cl cJ cK cM cP Cv cY Dc dD De Gl Hb Kf Nh Nv Nx Ow Po Pz rC) fP(Aa BC Bn
Ch cM Cp Dc De Dk Dl eD hR hX Io Iq Lw Mg My Mz Nd Oz Pd rB rN rS tS Vt Tk tF) fR(Aa aO Aw BC bW cl Cs Cu De Dk Fp Fy iJ Io Jh
Jn Kx Lh Lj Mg Mv Nc Nl Nw Pd Pj Qc Qd Sr) Na(cT Cu Dc De Dl Fa Fy hB Ik Jh jR Kl kQ Kx Ky Lj Nr Nt Ny Pf pS rN rW sO Uc Ut uX
wB) Nw(aA Aw Ch cQ cR cT De Fn gV iA Ic jD Je Ki Kp Kx Ky IL pH Pk QZ Ri tN tO tQ Tj tF) tS(cI Cp cS cZ dI dJ Dk Fa Hf Ii jK Jo Lx
Mg Ms Mv Mw Nv Of Ow Pd pS Um uP Uv Vo Vq yL) Mn(aN Aw cF Ch dU Hb Jl Jn Jp Ki Kn Lj mE Mr Ms Mu Mv Mx MZ nN No Nt Oz
Pk Vt) aC(Ip Jq Li Lv Lw Lx Ma Mv Mw My Mz Nc Ne Nh Nl Nq Nv Nx Ny Oh Oy Pz Qd Vi Wb Xa) Ic(Bn Ch Fa Fy Hc Ib Id Ij Jq Jy Ke Ko
Kp Li Lv Lw Lx Mg Mu Nv Pk Qy Sr St Ue) nN(bF bQ bS Co cR De Et Hq Il Jg Ji Jn Jp kQ Lh Nc Ng Nq nW oD Ok oN Pb PF) Dk(aD Ax Bn
bQ bX cK cN cP De dG dN Fn Hf Jh Kp Kz Lv Mt Pd Pk Qw Sr Ue Us) Mz(aN bA bM bQ cK cR dN Ik In Jr jY Ma Mf Mv mZ Nf Nr oD Pf
qZ uP Wh yH tF) We(cD cR Cu Fp Hf Ih Jp Jq Js Kn Kx Lx Nn Nr Nx Ny Pj Qb Qc Qh Rg Sr Tz Vu) Uh(Ax Bn cR De dX eP Fy Ib Id Ji Ko Lp mT Qy Rt Rv sC Sr tT tX Uz vS Xa tF) Dc(aK aU aV bF cE cN cY dF dN fN hB Hf Ne Nl qO Qz rN rW tN tO tR tT Th) Dg(gW Id Jh Jq Ke Kp kQ Lw Lx Lz Ml Ow Pd Pf Rv tN tO tR tX Ue uP Vo Vt) sC(Ad Ba Bc bS cI cS dD fN hC Id Kc Kp Kz Mu Mv Of pS rN rS sJ sO uP zI) No(Aw Ef Fc Fn Fp Hx Je Jp Jr Kf Lj Lt Mf Nb Nr Nx Pd Qz Ri Tr Yg Tj) Kx(Ba Dl Ef Fn Io Iq Je Kc Kg Kl Ky Li Ma MW Of Qt Rc Si Ss Tr Tj) zH(Bc Cu Fr gW Iq Jd Ji Kc Lw Md Mq Mw Of Oh Pa Pd qO qP Qw tX uP yH) rW(aD Aw Ii Ip Jd Je jY Kg Ki Kj Ko Kq Ms Mt Nj qW rC sO Uf Un uP wL) Lx(AA Ch Ef Hb Je Kg Ki Pg Pj Qm Qx Qy Ri Ss tO Tr tT vP wG yH) oD(Af aG Bn cX dG dK gL kQ Lj Mr Mt Nd Nt Oa oF oN pH Ql Rh Sr Yi) Ma(bM Fn Hb Ih Je Jl Jn Jq Jr Kf Kp Ky Lw Mh Oz Qw Sr tN tO Tj) Kf(cN cR Fn Fw Ha Hx In It Iu Kp Ky Nd Oi qU Qz rC Rm yH Tj) Pd(Aw cK dU Hb Ik Jr Lv Mf Ml Nb Nn Nt pH rS Rv tN tR Uf Un) aU(aJ Ax bA Bc Bg Bn Ch Cp Cs cT De dF dN gV It Jp Lh Nc Nl) Dl(bC Ef FN Jq Ky Lv Mt Nc Ne Nh Nl Pf pH Pk rN tO Tj) Mv(Fp Hb In Jl Kc lL Nb Nt Nx Ow pH Qm Qw tO TT tX Ti) Tr(Fn Fr Hb Hf Iu Ji Ko Kr Li Mt Mw Oh Pj Po qY Ra Sr St) Ye(Ad Ax Co cR Cu Cw Dd dF hC Ke mE nU Pj St Tn Tt Un Vj) dN(Af aK aL BA Bc bQ cE Ch cI cM Co cT cY Hb Nx Ow uZ) cF(Gl hR hX Mg Nc Nh Nl Ow pH qO rC rN tO tR tT Yi Ti) dF(aD aK aO aQ aV Bn Ch cK Cu eO Gb Io Nd Si Vc Vt Ti) tX(Bc bG dI eC fN Ii jV Kc Kp Kq lK Mu Mw Ng Of Po tV) uP(Aa aX cV eC fN gW Jh Li Mw On Pc qO qP qY rU tO tL) Tj(Aw Ba Co Cp Ef Fa Hq Iq Je Ko Nx Ow Oy Pf Qd Qm) Rz(bW Cs Hf jO Jr Lj mF Ml mS Mx Ni Pe Pk Rj Ue Up) tN(Ao Aw cS Cu Dd fN Fr Ii Kc Ky Li Lv Ms qW Ri tV) Bc(aK aQ aV bF cE cK cT cY hB Nd qO tO tT yH tL) Bg(aK aQ aV Ax bA bC Bn bQ bX cJ cK cN cR Cs cY) Ch(aQ aV BA bQ cE cG Cs cT cY Kc Lh Li Ow pH) Mt(aA Aw cK cT De Fn Ky Lt Lw mE Qy Qz tT Ue Ti) Jh(aD bM cK Fn jD Lj Mh Nb Pe Pf Pj pS Qm Qw Tt) Ko(cN fN Fr In It Kp Kr Nu oO Ow qO Qz Ra tO tF) rN(bX Ii Ip Jp lK Ng Nj Ok Qm rC Uf UG uU yD) Co(aK aN aQ aV Ax bA cK cN Cv cY Lp lX nF Nj) Cu(aD bC Bn cG cP De Fi Fw Gp hL Io tO uZ xA) Nr(dU Ik Iv Jl Jn Jq Lj Lt Mh MS Mx Nb Oz) Hb(Ax cN FN Hf Id Iq Je Kn Kp Ky Lw Sr Wh) Ke(Fn hL iA Iq Lt Nu Ow qO tT vP vS vV xA Tk) Rv(bQ Dd eC Ii Jm Mg nJ Oi Qc Qy Tt Tz Ua Wm) Ny(bM Hx In Iv Je Jl Jn Jr lL Lw Mh Mx nA Wh) Pf(Fn Gc Jl Jn Jr mI Mx Nb Nn Nt Nv Pe Ss tT) eD(Aw cV cW Fn jD Kg Ky Kz qO qP Rt Tn Tt Un) yH(Ad Jg Ji Kc Kq Li Lv Ms Nl On Pc QW Ri) Ba(aD bC bQ cJ cK cN De Fn Hf Ky Lv Nc Nl) Po(aA aN jD Je Jq lL Lw mE rB Ss wF wG tF) Uf(cN cQ cR De jD jY Kp oH oK Ow Pj Pk Qy) Cp(aD aK aQ bC cG cJ cT Gp Hr Io My Nd) Mf(aA aN In Jl Jq Jr Lv Nb Nn Nx Og Oz) Iq(dU fN hB Jy Ky lL Qg Qw Qy Sr Ss Ue) Qz(Ef Ii Jl Kl Nv Oh Qd Rc Ss Uc Ut Wm) Li(Ef FN Hf iA Je Ky Lp Qy Sr tR tT) Lj(aA Hx Jl Jq Lw mE Mg Mx Nb Rt Vw Wh) Lt(Ad Gc Ii Ir Jk Jn Jp Lh Qd Qm Tz Un) bM(aA aK aL aQ bP cN Cs Jn Jq Lv Nd sO) cE(aD aK Ax Bn cK cM cN cP Cs cY Nd vS) uZ(Ad bW bX cH cS cU cW Fa hB hC Kc Mq) Aw(Aa cR lL My Nl qO Qw rU tO tT Ue) In(Jl Jr Kl lL Mg Nn Nt Nv Oh Qd Ut) bQ(aD aV cK Cw cY eO Io Nd Nx Vc Vt) tF(cG Fa Fr hB hC Ji Ky Kz oF oN Un) jD(hR Ip Jd Ji Ki mW Ok Un vS Vt yL) Mw(dU Kc lL Qw Rc Ri tT vP vV wG) Je(Fy Hq jV Ky Mg My Oh Pj Qm St) Wh(cR Cs Fp Hf Jr Js Mx Pj Qb Ti) Kq(hA jY nF qO qP tO tT vP vV xA) bF(aD aK aO bC Bn cI cK cN eO Nd) cT(aD aK aV Bn De Io Nd Nh Nl Vt) rS(eC Fr Ip kR Ms Ng Of On Pa vV) Gc(Ao Dc Ij Kn My Nq Oh Oy Sr) Ik(Jl Jq Lw Mh Ml Ms Mx Nn Pe) Iv(Jl Jq Ml Ms Mx Nn Nx Oz Pe) bA(aD aK Ao bC Bn cK Io Nl Pz) cG(aD aK Bn cK Cw Mg Nc Nl Vc) cY(aJ Ax aY Bn cN Cs De gV It) qO(aD aQ aV bX Ii Kg Kj Kp wL) pH(Aa bW cA cI Hr Lw Mk nW oN) Fr(De hX Ki Kp Pk Sr tR xA) Ss(Aj Eq Hf Ky Si St Tz Ut) nK(iC kI mM Mp nI Nq Oy rY) sO(aX cU fY gW lK Ms qG tT) pS(gW Of Pc qW rU tR tT tL) Kc(Ef Kz Mg Of Pk vB tL) Nx(aA cK Mh Mx Nb Oz Pe) Ow(cR Io Kp Lw Qy tO tT) Vi(Af Jn Kj Oy Pi Pj Ue) aV(Ao Ax aY Bn Cs Cv De) dU(aX Ha Io Ng Oa Pb Ul) fN(Fa Id Ii Jq Kl Sr Ut) hB(Ao cM Hf iA Io NJ) jY(cW Id Or Pa Ut uX Vt) Ti(Hq Ly Qh Qt Rc Ug) Ml(AA Jq Jr Mu Nb) Jp(iA Jl Jn Jq Lw mE) Ps(Af Ir lM Rg Ug Up) Kz(jV lL mS mW nF rC) Lh(hR hX Jq rB Rx sJ) Lp(cR Cs Ij Nq Qc St) Nv(cK Ii Mh Ms Mx Oz) Tk(Ad aX hG kR kS Pa) wL(cU gW jQ lK qP wD) tR(Ao Ii Jd Kj Lv Vq) nW(eQ lX nC nH nL nT) vV(Ad cV hC qW Ri wD) Du(eC gW mT Mu nU) Nn(Mh Ms Nb oV oW) Ue(Fa Ji Oh Ok Pj) Tt(hR Kp qY uX Yl) Hf(hR hX Kl Qd rU) Ky(Dd De Ef Io Kl) Qm(eP Hu Oy Qy Ri) Un(hX jM Oh qC yL) aA(Fp Hx Mh Nt On) cJ(aN mE mM nF oP) lL(Hq Jg Of Ok Tn) lM(Ho tV vS Zw tM) Gn(Ad mT Pi Pk) Si(aH Or Qy Up) Ji(Ki Oy sJ Sr) Xa(mE mW oO Ug) Ut(Io jM My nF) aD(Ef hR Mg rC) aK(Ao Bn De rC) cV(hR vP Vq Vt) tT(cI qW Ri rU) tO(Dd Ii Kp Ri) rB(Kj On Or Pa) qZ(Et Jg nT Ok) qY(Ho Jg Ok Rt) oN(kN lX mS oO) Aa(cP Lv Nh) Fn(Kl Qd qU) Ms(Jl Nt tL) Nd(cN Dd De) Tn(cR iA jM) Ir(iJ nA oQ) Jd(nH nL qU) Jr(Nf Of Oh) Uw(bW eC Pk) Ux(Cs oH Or) Pj(Ax Hc Ib) eW(aF aI Aj) Bn(aQ cP) Cw(bC bX) Gb(gL hC) Lv(Ih Lw) Mg(aN cN) Mx(Fp Nt) Nb(Jl Jq) Hl(Pe Vu) Yi(mS mY) Wn(uV wH) Oh(cK Qy) On(jE mZ) Vj(cM Dp) Vt(cQ Th) cW(hR rC) cM(Gh Qx) eP(Jq St) gW(mZ uV) mE(Mp Oa) mF(bS jF) nJ(qT Vh) tV(jR xA) jQ(Ho Yl) lK(Ry yL) vB(Kg Kp) vW(It Qw) CsNj EfcR EoPg EtnA FycN NqjB NuSr MhJl TzoO Hvjl IbRu IdOf IoQt YjjT YdqT RcRt ZwjR QdRi OrVw VcjH UyeC VqwH PcwB aPvS bXqP cSrC dGgC dJeO mIrX hCwG qWvP

Figure 6 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ad | ug/mL | 3.9E-2 | 6.7E-2 | 7.4E-2 | 8.5E-1 | 8.9E-2 | 2.5E0 | 2.7E-4 | 4.3E-3 | 5.4E-1 | 8.5E0 | 534 | 11 | 204 | 11 | 0.60 |
| Af | ng/mL | 1.2E0 | 7.5E-1 | 1.6E1 | 2.8E1 | 6.0E1 | 7.7E1 | 1.7E-3 | 1.7E-3 | 5.3E2 | 2.6E2 | 534 | 11 | 204 | 11 | 0.51 |
| Aj | ug/mL | 1.5E0 | 2.0E-1 | 2.6E0 | 1.8E0 | 2.4E0 | 2.6E0 | 1.5E-3 | 2.1E-3 | 6.1E0 | 5.8E0 | 534 | 11 | 204 | 11 | 0.40 |
| Al | mg/mL | 8.8E-5 | 9.3E-5 | 2.5E-4 | 2.7E-4 | 4.1E-4 | 3.5E-4 | 2.3E-6 | 3.9E-5 | 2.2E-3 | 1.1E-3 | 534 | 11 | 204 | 11 | 0.59 |
| An | U/mL | 5.0E1 | 9.5E1 | 1.7E2 | 9.3E2 | 4.4E2 | 2.3E3 | 9.8E-4 | 4.3E1 | 5.5E3 | 7.8E3 | 534 | 11 | 204 | 11 | 0.73 |
| Ao | pg/mL | 8.8E1 | 1.3E2 | 4.6E2 | 5.8E2 | 3.2E3 | 1.3E3 | 1.5E0 | 5.4E0 | 3.9E4 | 4.5E3 | 534 | 11 | 204 | 11 | 0.54 |
| Ap | ng/mL | 3.3E1 | 2.7E1 | 4.8E1 | 6.0E1 | 5.1E1 | 7.5E1 | 8.4E-5 | 8.4E0 | 3.3E2 | 2.4E2 | 534 | 11 | 204 | 11 | 0.51 |
| Ar | ng/mL | 9.7E-1 | 4.0E0 | 1.1E1 | 4.3E0 | 1.8E2 | 4.0E0 | 3.4E-3 | 2.2E-1 | 4.1E3 | 1.4E1 | 534 | 11 | 204 | 11 | 0.71 |
| As | ng/mL | 8.7E-3 | 1.0E-1 | 1.3E-2 | 1.2E-1 | 1.8E-2 | 3.7E-1 | 1.7E-3 | 1.7E-3 | 1.3E-1 | 1.2E0 | 534 | 11 | 204 | 11 | 0.49 |
| Aw | pg/mL | 1.6E1 | 2.1E1 | 1.7E1 | 2.3E1 | 6.2E0 | 1.1E1 | 2.9E-2 | 1.3E1 | 4.8E1 | 5.1E1 | 534 | 11 | 204 | 11 | 0.71 |
| Ax | ng/mL | 2.1E0 | 7.2E0 | 1.6E1 | 7.0E1 | 6.0E1 | 1.2E2 | 1.2E-2 | 6.1E-1 | 7.7E2 | 3.7E2 | 534 | 11 | 204 | 11 | 0.69 |
| Ba | ng/mL | 6.5E1 | 5.8E2 | 4.5E2 | 3.1E3 | 1.1E3 | 4.6E3 | 2.7E-1 | 1.6E1 | 8.1E3 | 1.5E4 | 534 | 11 | 204 | 11 | 0.77 |
| Bb | ng/mL | 3.1E0 | 2.8E0 | 6.6E0 | 7.1E0 | 1.4E1 | 8.2E0 | 4.1E-3 | 6.8E-1 | 2.5E2 | 2.5E1 | 534 | 11 | 204 | 11 | 0.55 |
| Bc | ng/mL | 3.9E1 | 8.9E1 | 1.1E2 | 2.2E2 | 2.0E2 | 3.0E2 | 1.1E-1 | 9.6E0 | 1.2E3 | 1.0E3 | 534 | 11 | 204 | 11 | 0.66 |
| Bg | ng/mL | 8.5E-2 | 7.3E-1 | 5.4E0 | 3.7E1 | 2.9E1 | 1.2E2 | 5.3E-4 | 1.0E-2 | 4.4E2 | 4.0E2 | 534 | 11 | 204 | 11 | 0.66 |
| Bn | ng/mL | 5.6E-2 | 1.4E-1 | 1.2E0 | 6.3E0 | 2.0E0 | 1.7E1 | 5.6E-2 | 5.6E-2 | 9.7E0 | 5.8E1 | 534 | 11 | 204 | 11 | 0.55 |
| Bo | ng/mL | 1.2E1 | 2.2E1 | 1.4E1 | 2.4E1 | 1.8E1 | 1.7E1 | 1.6E-2 | 1.6E-2 | 2.8E2 | 5.3E1 | 534 | 11 | 204 | 11 | 0.68 |
| Ch | uIU/mL | 1.0E0 | 9.5E-1 | 1.6E1 | 1.1E2 | 9.4E1 | 3.6E2 | 3.4E-3 | 1.8E-1 | 1.8E3 | 1.2E3 | 534 | 11 | 204 | 11 | 0.49 |
| Co | pg/mL | 3.8E1 | 6.6E1 | 1.7E2 | 1.5E2 | 8.9E2 | 2.0E2 | 1.5E-1 | 1.5E-1 | 1.7E4 | 5.6E2 | 534 | 11 | 204 | 11 | 0.59 |
| Cp | ng/mL | 2.2E1 | 5.6E1 | 2.9E1 | 1.5E2 | 3.1E1 | 3.7E2 | 6.0E-1 | 1.4E1 | 3.7E2 | 1.3E3 | 534 | 11 | 204 | 11 | 0.69 |
| Cq | ng/mL | 3.0E-2 | 3.9E-2 | 1.4E-1 | 4.6E0 | 8.1E-1 | 1.5E1 | 8.0E-4 | 8.0E-4 | 1.7E1 | 4.9E1 | 534 | 11 | 204 | 11 | 0.57 |
| Cs | ng/mL | 6.1E1 | 2.2E2 | 3.1E2 | 1.1E3 | 1.1E3 | 1.8E3 | 2.7E-2 | 2.9E1 | 1.8E4 | 5.1E3 | 534 | 11 | 204 | 11 | 0.71 |
| Ct | ng/mL | 5.9E-1 | 1.3E-1 | 3.8E1 | 8.9E1 | 1.1E2 | 1.8E2 | 1.1E-4 | 5.7E-2 | 6.2E2 | 4.7E2 | 534 | 11 | 204 | 11 | 0.53 |
| Cu | ng/mL | 2.5E-1 | 6.4E-1 | 5.1E-1 | 6.9E0 | 1.4E0 | 2.0E1 | 9.0E-5 | 4.6E-2 | 2.1E1 | 6.6E1 | 534 | 11 | 204 | 11 | 0.71 |
| Cv | ng/mL | 5.5E0 | 8.5E0 | 2.5E1 | 1.2E2 | 6.3E1 | 2.0E2 | 1.4E-4 | 1.9E-1 | 5.3E2 | 5.2E2 | 534 | 11 | 204 | 11 | 0.54 |
| Cw | mIU/mL | 3.0E-2 | 5.1E-2 | 3.9E-2 | 6.6E-1 | 3.3E-2 | 2.0E0 | 1.5E-4 | 1.4E-2 | 2.4E-1 | 6.8E0 | 534 | 11 | 204 | 11 | 0.66 |
| Cx | ng/mL | 3.2E-1 | 1.6E-2 | 6.1E1 | 7.6E1 | 1.1E2 | 1.4E2 | 9.3E-5 | 9.3E-5 | 3.9E2 | 3.9E2 | 534 | 11 | 204 | 11 | 0.44 |
| Db | ug/mL | 7.4E0 | 1.3E1 | 9.1E0 | 1.1E1 | 1.0E1 | 5.7E0 | 4.5E-1 | 1.4E0 | 1.4E2 | 1.9E1 | 534 | 11 | 204 | 11 | 0.66 |
| Dc | nmol/L | 1.9E-2 | 2.0E-2 | 6.0E-2 | 1.5E0 | 1.4E-1 | 4.2E0 | 5.2E-6 | 1.3E-3 | 1.6E0 | 1.4E1 | 534 | 11 | 204 | 11 | 0.61 |
| Dd | ug/mL | 7.0E-2 | 8.2E-2 | 1.7E-1 | 4.7E-1 | 2.6E-1 | 1.1E0 | 8.3E-5 | 6.2E-3 | 1.9E0 | 3.6E0 | 534 | 11 | 204 | 11 | 0.53 |
| De | ng/mL | 3.4E-3 | 3.4E-3 | 8.1E-2 | 1.6E-1 | 1.5E-1 | 2.4E-1 | 3.4E-3 | 3.4E-3 | 1.2E0 | 7.9E-1 | 534 | 11 | 204 | 11 | 0.59 |
| Dg | ng/mL | 3.3E1 | 4.4E1 | 4.5E1 | 5.7E1 | 4.0E1 | 5.4E1 | 1.0E-1 | 4.7E0 | 1.9E2 | 1.9E2 | 534 | 11 | 204 | 11 | 0.56 |
| Di | pg/mL | 1.9E0 | 4.2E0 | 2.2E0 | 3.7E0 | 2.0E0 | 2.3E0 | 1.8E-1 | 1.8E-1 | 1.3E1 | 9.0E0 | 534 | 11 | 204 | 11 | 0.72 |
| Dk | uIU/mL | 1.7E-2 | 4.6E-2 | 7.9E-2 | 1.8E-1 | 4.7E-1 | 2.4E-1 | 1.1E-4 | 5.8E-3 | 8.9E0 | 6.3E-1 | 534 | 11 | 204 | 11 | 0.66 |
| Dl | ng/mL | 2.3E2 | 2.3E2 | 3.1E2 | 3.8E2 | 2.9E2 | 4.5E2 | 1.7E0 | 1.8E1 | 1.5E3 | 1.6E3 | 534 | 11 | 204 | 11 | 0.52 |
| Dp | ng/ml | 2.4E0 | 1.0E0 | 5.4E0 | 2.5E0 | 8.0E0 | 6.3E1 | 3.7E-3 | 3.7E-3 | 5.6E1 | 2.0E2 | 332 | 10 | 193 | 10 | 0.40 |
| Dr | pg/ml | 2.5E1 | 2.8E2 | 5.0E1 | 1.5E3 | 7.0E1 | 3.6E3 | 7.5E-1 | 4.6E0 | 5.2E2 | 1.0E4 | 185 | 8 | 107 | 8 | 0.78 |
| Du | pg/ml | 5.2E1 | 1.2E0 | 7.3E2 | 4.8E3 | 2.7E3 | 8.8E3 | 1.2E0 | 1.2E0 | 2.6E4 | 2.4E4 | 111 | 7 | 87 | 7 | 0.54 |
| Ef | ng/ml | 1.3E-1 | 1.3E0 | 8.8E-1 | 3.2E0 | 1.9E0 | 3.6E0 | 5.7E-4 | 1.1E-2 | 1.0E1 | 9.4E0 | 398 | 10 | 200 | 10 | 0.68 |
| Wm | % | 4.9E-1 | 5.6E0 | 3.3E1 | 9.8E1 | 1.8E2 | 2.8E2 | 5.4E-2 | 8.5E-2 | 2.4E3 | 1.0E3 | 432 | 14 | 217 | 14 | 0.66 |
| Ed | pg/ml | 5.2E-1 | 6.8E1 | 5.5E1 | 7.3E1 | 4.0E2 | 4.7E1 | 5.2E-1 | 4.4E0 | 7.3E3 | 1.5E2 | 332 | 10 | 192 | 10 | 0.80 |
| Tj | pg/mL | 3.7E-1 | 3.7E-1 | 4.9E1 | 3.0E1 | 2.7E2 | 5.0E1 | 3.6E-1 | 3.7E-1 | 3.5E3 | 1.4E2 | 396 | 10 | 203 | 10 | 0.54 |
| Po | pg/ml | 6.9E-1 | 2.8E1 | 8.0E0 | 4.6E1 | 2.2E1 | 6.3E1 | 8.0E-3 | 5.3E-1 | 2.7E2 | 2.2E2 | 932 | 16 | 343 | 16 | 0.83 |
| Ti | ug/mL | 3.4E0 | 5.5E0 | 4.8E0 | 7.1E0 | 4.6E0 | 6.2E0 | 8.7E-3 | 8.7E-3 | 3.7E1 | 1.8E1 | 185 | 8 | 137 | 8 | 0.60 |
| Em | ng/ml | 2.9E-3 | 6.0E-2 | 6.7E-2 | 2.6E-1 | 1.4E-1 | 6.3E-1 | 1.9E-16 | 8.4E-4 | 7.6E-1 | 1.9E0 | 236 | 9 | 107 | 9 | 0.62 |
| Et | ng/ml | 1.4E3 | 3.3E3 | 1.7E3 | 2.4E3 | 1.2E3 | 1.4E3 | 7.5E1 | 7.9E2 | 5.0E3 | 5.0E3 | 931 | 16 | 343 | 16 | 0.81 |
| Eq | pg/ml | 1.4E2 | 3.1E1 | 3.1E2 | 2.0E2 | 3.9E2 | 3.6E2 | 1.0E0 | 1.0E0 | 1.8E3 | 1.0E3 | 111 | 7 | 87 | 7 | 0.38 |
| Th | ug/mL | 1.1E0 | 2.2E0 | 1.6E0 | 2.3E0 | 1.5E0 | 1.1E0 | 2.6E-3 | 4.8E-1 | 1.2E1 | 4.2E0 | 185 | 8 | 137 | 8 | 0.72 |
| Fa | ng/ml | 4.4E1 | 2.2E2 | 1.2E2 | 2.4E2 | 5.1E2 | 2.1E2 | 3.4E-2 | 7.5E0 | 8.0E3 | 7.3E2 | 327 | 10 | 190 | 10 | 0.80 |
| Ez | ng/ml | 3.8E0 | 2.2E1 | 1.7E1 | 3.1E1 | 5.0E1 | 3.2E1 | 1.3E-2 | 1.1E-1 | 7.1E2 | 8.8E1 | 332 | 10 | 193 | 10 | 0.71 |
| Fb | ng/ml | 2.5E1 | 2.7E1 | 2.3E1 | 2.9E1 | 1.2E1 | 5.5E0 | 5.9E-1 | 2.4E1 | 5.7E1 | 4.1E1 | 328 | 10 | 190 | 10 | 0.64 |
| Ex | ng/ml | 7.6E-2 | 2.4E-1 | 2.2E-1 | 8.3E-1 | 6.5E-1 | 1.3E0 | 3.5E-5 | 4.2E-2 | 8.9E0 | 4.1E0 | 293 | 9 | 138 | 9 | 0.78 |
| Fc | pg/ml | 2.2E-1 | 6.3E0 | 1.4E2 | 5.2E1 | 1.4E3 | 1.1E2 | 2.2E-1 | 2.2E-1 | 1.5E4 | 3.1E2 | 113 | 7 | 87 | 7 | 0.69 |
| Fd | pg/ml | 1.4E1 | 2.8E2 | 1.0E3 | 4.1E3 | 3.9E3 | 9.3E3 | 4.5E-1 | 9.8E-1 | 3.3E4 | 2.5E4 | 113 | 7 | 87 | 7 | 0.71 |

Figure 7

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fi | pg/ml | 2.5E-1 | 2.5E-1 | 1.8E2 | 3.7E1 | 1.3E3 | 9.5E1 | 2.5E-1 | 2.5E-1 | 1.4E4 | 2.5E2 | 113 | 7 | 87 | 7 | 0.54 |
| Fn | ng/ml | 2.1E-1 | 2.1E-1 | 5.5E0 | 2.9E0 | 2.4E1 | 8.3E0 | 1.1E-14 | 2.1E-1 | 4.2E2 | 2.7E1 | 332 | 10 | 193 | 10 | 0.38 |
| Fp | ng/ml | 1.3E1 | 6.2E1 | 2.5E1 | 6.0E1 | 2.8E1 | 3.8E1 | 6.0E-3 | 6.8E0 | 1.4E2 | 1.3E2 | 965 | 15 | 344 | 15 | 0.79 |
| Fr | ng/ml | 3.9E4 | 5.5E5 | 1.1E5 | 4.5E5 | 1.7E5 | 3.1E5 | 1.9E2 | 1.0E4 | 9.0E5 | 8.4E5 | 1079 | 17 | 348 | 17 | 0.80 |
| Fw | pg/ml | 1.1E0 | 9.4E0 | 5.6E0 | 4.0E1 | 4.4E2 | 9.6E1 | 1.1E-14 | 1.2E-1 | 6.9E3 | 3.3E2 | 398 | 11 | 201 | 11 | 0.65 |
| Fy | ng/ml | 3.3E1 | 1.1E2 | 5.6E1 | 2.1E2 | 6.6E1 | 2.3E2 | 1.2E-1 | 1.2E1 | 5.3E2 | 6.5E2 | 328 | 9 | 192 | 9 | 0.75 |
| Gh | pg/ml | 3.9E0 | 2.3E0 | 6.6E1 | 1.3E1 | 2.5E2 | 3.0E1 | 2.9E-2 | 2.9E-2 | 1.8E3 | 8.0E1 | 111 | 7 | 87 | 7 | 0.41 |
| Gb | % | 3.9E1 | 3.7E1 | 4.6E1 | 8.0E1 | 3.9E1 | 1.0E2 | 2.2E0 | 2.8E1 | 2.3E2 | 3.0E2 | 113 | 7 | 86 | 7 | 0.62 |
| Gc | ng/ml | 1.0E2 | 1.2E2 | 1.5E2 | 1.5E2 | 1.7E2 | 1.4E2 | 6.4E0 | 3.1E1 | 1.2E3 | 4.7E2 | 198 | 8 | 111 | 8 | 0.53 |
| Gd | ng/ml | 3.0E1 | 1.2E1 | 3.1E1 | 2.9E1 | 1.7E1 | 2.7E1 | 3.0E0 | 7.6E0 | 8.1E1 | 8.0E1 | 221 | 9 | 98 | 9 | 0.40 |
| Gn | U/ml | 2.8E-1 | 1.3E-1 | 1.2E0 | 1.5E1 | 2.9E0 | 4.0E1 | 1.3E-3 | 5.6E-3 | 3.0E1 | 1.1E2 | 179 | 8 | 105 | 8 | 0.48 |
| Gl | pg/ml | 7.2E3 | 2.3E4 | 1.1E4 | 2.1E4 | 9.3E3 | 9.9E3 | 9.1E1 | 1.3E3 | 3.4E4 | 3.2E4 | 388 | 11 | 199 | 11 | 0.77 |
| Gp | U/ml | 1.5E0 | 6.1E-1 | 3.9E0 | 1.6E0 | 6.6E0 | 2.4E0 | 1.3E-3 | 1.5E-2 | 6.7E1 | 7.3E0 | 400 | 10 | 201 | 10 | 0.36 |
| Gz | ug/ml | 1.2E0 | 1.4E0 | 7.8E0 | 3.5E0 | 3.4E1 | 4.5E0 | 2.9E-16 | 1.0E-1 | 4.8E2 | 1.1E1 | 224 | 9 | 126 | 9 | 0.46 |
| Ha | ng/ml | 2.7E0 | 5.6E0 | 9.4E0 | 1.8E1 | 2.0E1 | 3.2E1 | 6.4E-3 | 6.4E-1 | 1.3E2 | 1.0E2 | 330 | 10 | 192 | 10 | 0.61 |
| Nm | pg/ml | 1.4E4 | 3.3E4 | 3.3E4 | 9.0E4 | 7.8E4 | 2.0E5 | 1.0E-9 | 1.0E-9 | 1.6E6 | 8.2E5 | 935 | 16 | 345 | 16 | 0.63 |
| Nn | pg/ml | 1.6E2 | 2.1E3 | 1.7E3 | 1.5E4 | 7.6E3 | 3.2E4 | 1.0E-9 | 1.1E2 | 1.0E5 | 1.1E5 | 935 | 16 | 345 | 16 | 0.81 |
| No | pg/ml | 1.6E1 | 8.2E1 | 3.6E1 | 2.0E2 | 1.1E2 | 2.5E2 | 1.0E-9 | 9.0E0 | 2.5E3 | 7.7E2 | 935 | 16 | 345 | 16 | 0.83 |
| Nq | pg/ml | 2.0E0 | 2.4E1 | 1.8E1 | 5.9E1 | 7.2E1 | 7.7E1 | 1.0E-9 | 1.0E-9 | 1.2E3 | 2.4E2 | 935 | 16 | 345 | 16 | 0.71 |
| Nr | pg/ml | 9.9E-1 | 7.4E0 | 2.8E1 | 1.6E2 | 1.7E2 | 3.7E2 | 1.0E-9 | 1.0E-9 | 4.1E3 | 1.4E3 | 935 | 16 | 345 | 16 | 0.67 |
| Ns | pg/ml | 1.0E-9 | 1.0E-9 | 9.0E0 | 1.0E-9 | 5.1E1 | 0.0E0 | 1.0E-9 | 1.0E-9 | 1.1E3 | 1.0E-9 | 935 | 16 | 345 | 16 | 0.45 |
| Nt | pg/ml | 1.0E2 | 2.2E2 | 1.3E2 | 3.0E2 | 1.1E2 | 3.0E2 | 1.0E-9 | 4.4E1 | 1.5E3 | 1.2E3 | 935 | 16 | 345 | 16 | 0.74 |
| Nu | pg/ml | 2.0E1 | 7.4E1 | 5.4E1 | 1.2E2 | 8.9E1 | 1.1E2 | 1.0E-9 | 1.0E-9 | 8.9E2 | 3.7E2 | 935 | 16 | 345 | 16 | 0.71 |
| Lu | pg/ml | 1.0E4 | 5.5E3 | 1.8E4 | 7.0E3 | 6.1E4 | 5.8E3 | 3.5E2 | 1.3E3 | 1.3E6 | 2.2E4 | 938 | 16 | 345 | 16 | 0.31 |
| Lv | pg/ml | 1.0E-9 | 4.2E1 | 1.1E1 | 6.2E1 | 2.2E1 | 6.3E1 | 1.0E-9 | 1.0E-9 | 2.6E2 | 1.8E2 | 938 | 16 | 345 | 16 | 0.76 |
| Lw | pg/ml | 1.0E-9 | 1.0E-9 | 3.9E-1 | 5.7E0 | 4.0E0 | 1.2E1 | 1.0E-9 | 1.0E-9 | 8.0E1 | 4.0E1 | 938 | 16 | 345 | 16 | 0.62 |
| Lx | pg/ml | 1.0E-9 | 6.3E2 | 1.4E2 | 9.7E2 | 4.1E2 | 9.2E2 | 1.0E-9 | 1.0E-9 | 6.2E3 | 2.8E3 | 938 | 16 | 345 | 16 | 0.82 |
| Ly | pg/ml | 1.0E-9 | 1.0E-9 | 1.0E1 | 3.4E0 | 2.0E1 | 7.4E0 | 1.0E-9 | 1.0E-9 | 1.6E2 | 2.6E1 | 938 | 16 | 345 | 16 | 0.43 |
| Lz | pg/ml | 1.0E-9 | 1.0E-9 | 3.8E0 | 9.2E0 | 3.0E1 | 2.0E1 | 1.0E-9 | 1.0E-9 | 6.0E2 | 6.2E1 | 938 | 16 | 345 | 16 | 0.56 |
| Ma | pg/ml | 2.8E2 | 2.7E3 | 1.3E3 | 7.4E3 | 3.5E3 | 1.4E4 | 1.0E-9 | 8.7E1 | 6.5E4 | 5.2E4 | 938 | 16 | 345 | 16 | 0.74 |
| Mb | pg/ml | 2.5E1 | 3.7E1 | 3.1E1 | 3.7E1 | 1.5E1 | 2.0E1 | 5.4E0 | 4.1E0 | 2.1E2 | 7.1E1 | 938 | 16 | 345 | 16 | 0.56 |
| Mc | pg/ml | 1.0E-9 | 1.0E-9 | 4.1E-2 | 1.0E-9 | 5.6E-1 | 0.0E0 | 1.0E-9 | 1.0E-9 | 1.3E1 | 1.0E-9 | 938 | 16 | 345 | 16 | 0.49 |
| Md | pg/ml | 1.0E-9 | 1.0E-9 | 3.9E-1 | 2.2E0 | 3.4E0 | 7.4E0 | 1.0E-9 | 1.0E-9 | 6.8E1 | 2.9E1 | 938 | 16 | 345 | 16 | 0.56 |
| Me | pg/ml | 3.3E1 | 8.7E0 | 3.2E1 | 2.5E1 | 2.0E1 | 4.5E1 | 1.0E-9 | 1.0E-9 | 3.2E2 | 1.8E2 | 938 | 16 | 345 | 16 | 0.27 |
| Mf | pg/ml | 1.0E-9 | 1.0E-9 | 5.2E-1 | 1.0E0 | 2.9E0 | 2.0E0 | 1.0E-9 | 1.0E-9 | 5.6E1 | 5.5E0 | 938 | 16 | 345 | 16 | 0.59 |
| Mg | pg/ml | 1.6E0 | 2.0E0 | 7.4E0 | 7.8E0 | 1.3E1 | 9.9E0 | 1.0E-9 | 1.0E-9 | 9.4E1 | 2.7E1 | 938 | 16 | 345 | 16 | 0.53 |
| Mh | pg/ml | 1.0E-9 | 2.9E-2 | 1.3E0 | 3.4E0 | 9.4E0 | 6.1E0 | 1.0E-9 | 1.0E-9 | 1.6E2 | 1.8E1 | 938 | 16 | 345 | 16 | 0.65 |
| Mi | pg/ml | 1.0E-9 | 1.0E-9 | 4.8E-1 | 1.0E1 | 5.2E0 | 2.8E1 | 1.0E-9 | 1.0E-9 | 1.2E2 | 1.1E2 | 938 | 16 | 345 | 16 | 0.61 |
| Mj | pg/ml | 1.0E-9 | 1.2E0 | 4.3E0 | 3.5E1 | 2.4E1 | 6.6E1 | 1.0E-9 | 1.0E-9 | 4.6E2 | 2.1E2 | 938 | 16 | 345 | 16 | 0.67 |
| Mk | pg/ml | 9.1E-1 | 5.7E0 | 1.4E1 | 4.0E1 | 8.4E1 | 1.2E2 | 1.0E-9 | 1.0E-9 | 1.7E3 | 5.0E2 | 938 | 16 | 345 | 16 | 0.62 |
| Ml | pg/ml | 1.0E-9 | 1.0E-9 | 4.9E0 | 4.3E1 | 7.2E1 | 1.3E2 | 1.0E-9 | 1.0E-9 | 2.1E3 | 5.1E2 | 938 | 16 | 345 | 16 | 0.62 |
| Mm | pg/ml | 5.9E2 | 1.7E3 | 1.0E3 | 2.5E3 | 1.2E3 | 3.1E3 | 1.0E-9 | 6.2E1 | 1.1E4 | 1.2E4 | 938 | 16 | 345 | 16 | 0.68 |
| Mn | pg/ml | 5.5E0 | 1.1E1 | 1.0E1 | 1.8E1 | 2.2E1 | 1.4E1 | 1.0E-9 | 2.8E0 | 3.5E2 | 5.1E1 | 938 | 16 | 345 | 16 | 0.73 |
| Mp | pg/ml | 1.0E-9 | 2.3E1 | 8.9E0 | 3.7E1 | 2.9E1 | 4.2E1 | 1.0E-9 | 1.0E-9 | 6.3E2 | 1.3E2 | 937 | 16 | 345 | 16 | 0.75 |
| Mq | pg/ml | 1.0E-9 | 3.5E0 | 2.7E0 | 2.2E1 | 1.6E1 | 3.5E1 | 1.0E-9 | 1.0E-9 | 2.4E2 | 1.0E2 | 937 | 16 | 345 | 16 | 0.72 |
| Mr | pg/ml | 1.0E-9 | 1.2E1 | 2.5E1 | 3.4E2 | 1.4E2 | 8.8E2 | 1.0E-9 | 1.0E-9 | 2.2E3 | 3.4E3 | 937 | 16 | 345 | 16 | 0.75 |
| Ms | pg/ml | 4.1E2 | 2.2E2 | 5.6E2 | 3.1E2 | 6.6E2 | 3.0E2 | 1.0E-9 | 1.0E-9 | 5.9E3 | 9.8E2 | 937 | 16 | 345 | 16 | 0.39 |
| Mt | pg/ml | 2.5E-1 | 9.7E0 | 6.8E0 | 2.3E2 | 4.1E1 | 8.0E2 | 1.0E-9 | 1.0E-9 | 8.7E2 | 3.2E3 | 937 | 16 | 345 | 16 | 0.79 |
| Mu | pg/ml | 1.0E-9 | 3.3E0 | 1.2E0 | 5.9E0 | 1.0E1 | 9.4E0 | 1.0E-9 | 1.0E-9 | 2.3E2 | 3.5E1 | 937 | 16 | 345 | 16 | 0.82 |
| Mv | pg/ml | 1.0E-9 | 1.6E1 | 6.8E1 | 1.9E2 | 3.1E2 | 3.0E2 | 1.0E-9 | 1.0E-9 | 4.5E3 | 9.2E2 | 937 | 16 | 345 | 16 | 0.71 |
| Mw | pg/ml | 3.8E1 | 4.2E2 | 5.0E2 | 1.2E3 | 3.2E3 | 1.8E3 | 1.0E-9 | 1.0E-9 | 6.2E4 | 5.3E3 | 937 | 16 | 345 | 16 | 0.80 |
| Mx | pg/ml | 1.0E-9 | 1.0E-9 | 2.4E-1 | 2.1E0 | 1.3E0 | 5.0E0 | 1.0E-9 | 1.0E-9 | 3.2E1 | 2.0E1 | 937 | 16 | 345 | 16 | 0.66 |
| My | pg/ml | 1.0E-9 | 3.7E1 | 4.5E2 | 2.7E2 | 2.9E3 | 5.3E2 | 1.0E-9 | 1.0E-9 | 3.9E4 | 1.9E3 | 937 | 16 | 345 | 16 | 0.60 |
| Mz | pg/ml | 1.1E1 | 2.9E1 | 2.7E1 | 2.5E2 | 6.3E1 | 5.5E2 | 1.0E-9 | 1.0E-9 | 1.2E3 | 1.9E3 | 937 | 16 | 345 | 16 | 0.71 |
| Na | pg/ml | 1.0E-9 | 1.0E-9 | 6.6E-1 | 4.9E0 | 2.6E0 | 1.1E1 | 1.0E-9 | 1.0E-9 | 3.6E1 | 4.2E1 | 937 | 16 | 345 | 16 | 0.61 |
| Nb | pg/ml | 2.1E0 | 5.4E0 | 3.8E0 | 2.5E1 | 1.1E1 | 5.5E1 | 1.0E-9 | 1.0E-9 | 2.3E2 | 2.1E2 | 937 | 16 | 345 | 16 | 0.69 |
| Nc | pg/ml | 3.4E2 | 2.7E2 | 5.6E2 | 3.7E2 | 7.2E2 | 3.7E2 | 1.0E-9 | 1.0E-9 | 9.2E3 | 1.1E3 | 937 | 16 | 345 | 16 | 0.47 |

Figure 7 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nd | pg/ml | 2.9E1 | 1.1E1 | 2.7E1 | 2.2E1 | 4.4E1 | 2.6E1 | 1.0E-9 | 1.0E-9 | 1.2E3 | 9.4E1 | 937 | 16 | 345 | 16 | 0.43 |
| Ne | pg/ml | 4.4E2 | 2.9E2 | 5.7E2 | 2.7E2 | 5.7E2 | 1.8E2 | 1.0E-9 | 1.0E-9 | 7.0E3 | 5.8E2 | 937 | 16 | 345 | 16 | 0.34 |
| Nf | pg/ml | 1.0E-9 | 8.7E-1 | 2.6E0 | 1.6E1 | 9.4E0 | 4.1E1 | 1.0E-9 | 1.0E-9 | 1.6E2 | 1.3E2 | 937 | 16 | 345 | 16 | 0.63 |
| Ng | pg/ml | 1.9E1 | 7.6E0 | 1.3E2 | 3.9E1 | 2.5E2 | 5.8E1 | 1.0E-9 | 1.0E-9 | 2.3E3 | 1.7E2 | 937 | 16 | 345 | 16 | 0.42 |
| Nh | pg/ml | 6.9E1 | 3.7E1 | 9.0E1 | 4.0E1 | 8.2E1 | 2.3E1 | 1.0E-9 | 4.1E0 | 5.6E2 | 7.5E1 | 937 | 16 | 345 | 16 | 0.30 |
| Ni | pg/ml | 1.0E-9 | 2.2E2 | 7.2E1 | 2.5E2 | 1.2E2 | 2.9E2 | 1.0E-9 | 1.0E-9 | 7.1E2 | 1.1E3 | 937 | 16 | 345 | 16 | 0.69 |
| Nj | pg/ml | 7.5E0 | 4.9E0 | 1.1E1 | 7.2E0 | 1.2E1 | 6.5E0 | 1.0E-9 | 1.0E-9 | 1.1E2 | 2.0E1 | 937 | 16 | 345 | 16 | 0.43 |
| Nk | pg/ml | 1.7E1 | 2.8E1 | 3.3E1 | 2.7E1 | 3.9E1 | 2.2E1 | 1.0E-9 | 1.0E-9 | 2.0E2 | 6.6E1 | 937 | 16 | 345 | 16 | 0.52 |
| Nl | pg/ml | 4.5E1 | 3.0E1 | 6.1E1 | 3.3E1 | 6.8E1 | 2.5E1 | 1.0E-9 | 1.0E-9 | 1.1E3 | 8.2E1 | 937 | 16 | 345 | 16 | 0.38 |
| Hl | pg/ml | 1.4E1 | 2.4E1 | 3.6E1 | 5.6E2 | 6.2E1 | 1.3E3 | 1.0E-9 | 1.0E-9 | 3.5E2 | 3.6E3 | 113 | 7 | 87 | 7 | 0.56 |
| Ho | pg/ml | 1.7E1 | 2.2E1 | 2.8E1 | 7.1E1 | 6.7E1 | 1.4E2 | 1.0E-9 | 2.0E0 | 7.0E2 | 3.9E2 | 113 | 7 | 87 | 7 | 0.58 |
| Hp | ng/ml | 1.6E0 | 7.7E0 | 1.2E2 | 3.8E2 | 3.0E2 | 4.7E2 | 1.0E-9 | 1.4E0 | 8.9E2 | 8.9E2 | 113 | 7 | 87 | 7 | 0.76 |
| Tz | pg/ml | 5.1E3 | 1.0E4 | 2.0E4 | 1.1E4 | 1.3E5 | 7.9E3 | 1.0E-9 | 8.1E2 | 2.1E6 | 2.5E4 | 334 | 10 | 191 | 10 | 0.64 |
| Ua | pg/ml | 3.8E3 | 9.5E3 | 2.0E4 | 1.7E4 | 1.2E5 | 1.9E4 | 1.0E-9 | 1.1E3 | 2.1E6 | 5.8E4 | 334 | 10 | 191 | 10 | 0.66 |
| Ub | pg/ml | 5.6E2 | 3.5E2 | 8.3E2 | 6.1E2 | 1.0E3 | 8.3E2 | 1.0E-9 | 1.2E1 | 9.8E3 | 2.8E3 | 334 | 10 | 191 | 10 | 0.39 |
| Ue | pg/ml | 2.7E1 | 2.0E1 | 3.8E1 | 3.5E1 | 4.1E1 | 4.0E1 | 9.8E-2 | 5.9E0 | 4.4E2 | 1.4E2 | 334 | 10 | 191 | 10 | 0.41 |
| Uc | pg/ml | 8.9E2 | 1.6E3 | 1.7E3 | 7.4E3 | 2.6E3 | 1.8E4 | 1.0E-9 | 5.5E1 | 2.9E4 | 5.7E4 | 334 | 10 | 191 | 10 | 0.57 |
| Ud | pg/ml | 1.0E-9 | 1.0E-9 | 1.3E0 | 5.8E0 | 2.1E1 | 1.7E1 | 1.0E-9 | 1.0E-9 | 3.9E2 | 5.3E1 | 334 | 10 | 191 | 10 | 0.60 |
| Hq | pg/ml | 1.1E0 | 2.2E0 | 9.6E1 | 1.9E1 | 1.6E3 | 4.6E1 | 1.0E-9 | 1.0E-9 | 3.4E4 | 1.8E2 | 933 | 16 | 344 | 16 | 0.59 |
| Hr | pg/ml | 1.1E2 | 1.2E2 | 7.5E2 | 1.3E3 | 1.6E3 | 2.5E3 | 1.0E-9 | 1.0E-9 | 1.7E4 | 8.9E3 | 933 | 16 | 344 | 16 | 0.55 |
| Hu | pg/ml | 5.3E0 | 1.8E2 | 3.0E3 | 4.8E2 | 2.6E4 | 6.6E2 | 1.0E-9 | 1.0E-9 | 6.3E5 | 2.4E3 | 933 | 16 | 344 | 16 | 0.69 |
| Hv | pg/ml | 1.4E0 | 1.7E0 | 3.3E0 | 6.1E1 | 1.2E1 | 2.2E2 | 1.0E-9 | 1.0E-9 | 2.5E2 | 8.9E2 | 933 | 16 | 344 | 16 | 0.58 |
| Hw | pg/ml | 6.4E0 | 8.8E0 | 1.8E1 | 6.2E2 | 6.9E1 | 2.3E3 | 1.0E-9 | 5.1E-1 | 1.7E3 | 9.4E3 | 933 | 16 | 344 | 16 | 0.54 |
| Hx | pg/ml | 8.8E0 | 1.7E1 | 3.7E1 | 1.6E2 | 3.1E2 | 3.6E2 | 1.0E-9 | 1.0E-9 | 9.3E3 | 1.3E3 | 933 | 16 | 344 | 16 | 0.70 |
| Ib | ng/ml | 4.9E-2 | 1.2E-1 | 1.7E0 | 5.8E0 | 6.5E0 | 1.8E1 | 1.0E-9 | 1.0E-9 | 5.3E1 | 5.6E1 | 324 | 10 | 190 | 10 | 0.58 |
| Ic | U/ml | 2.2E2 | 2.2E2 | 1.0E3 | 2.1E2 | 6.6E3 | 1.5E2 | 1.5E0 | 4.2E1 | 9.3E4 | 4.2E2 | 324 | 10 | 190 | 10 | 0.52 |
| Id | U/ml | 6.9E-1 | 1.0E0 | 1.4E0 | 4.5E1 | 2.4E0 | 1.4E2 | 1.0E-9 | 3.0E-1 | 2.3E1 | 4.3E2 | 324 | 10 | 190 | 10 | 0.67 |
| Tt | pg/ml | 1.6E2 | 1.7E2 | 1.7E2 | 2.1E2 | 5.1E1 | 1.0E2 | 4.3E1 | 1.1E2 | 3.6E2 | 4.4E2 | 308 | 8 | 184 | 8 | 0.59 |
| To | pg/ml | 1.6E0 | 1.8E0 | 1.9E0 | 2.7E0 | 2.3E0 | 3.6E0 | 1.0E-9 | 1.0E-9 | 2.3E1 | 1.2E1 | 321 | 9 | 188 | 9 | 0.56 |
| Tr | pg/ml | 3.0E0 | 5.6E0 | 5.9E0 | 1.9E1 | 1.8E1 | 2.9E1 | 1.0E-9 | 7.6E-1 | 3.1E2 | 7.6E1 | 317 | 8 | 187 | 8 | 0.62 |
| Tn | pg/ml | 2.8E1 | 1.6E2 | 7.4E1 | 5.7E2 | 1.9E2 | 9.0E2 | 1.0E-9 | 2.1E1 | 1.8E3 | 2.3E3 | 321 | 9 | 188 | 9 | 0.77 |
| Tv | ng/ml | 1.2E1 | 1.5E1 | 2.3E1 | 8.0E2 | 6.2E1 | 2.4E3 | 1.0E-9 | 1.0E-9 | 7.9E2 | 7.1E3 | 321 | 9 | 188 | 9 | 0.54 |
| Ih | ng/ml | 7.2E1 | 3.5E2 | 2.4E2 | 6.3E2 | 4.8E2 | 7.3E2 | 1.0E-9 | 1.0E-9 | 7.4E3 | 2.8E3 | 937 | 16 | 344 | 16 | 0.70 |
| Ii | ng/ml | 9.5E1 | 1.8E2 | 2.4E2 | 6.8E2 | 6.6E2 | 1.3E3 | 1.0E-9 | 2.3E0 | 1.0E4 | 4.5E3 | 937 | 16 | 344 | 16 | 0.59 |
| Ij | ng/ml | 7.6E1 | 1.4E2 | 1.7E2 | 1.7E3 | 5.7E2 | 6.0E3 | 1.6E-1 | 2.5E1 | 6.4E3 | 2.4E4 | 924 | 16 | 342 | 16 | 0.71 |
| Ik | ng/ml | 1.3E1 | 6.0E1 | 7.9E2 | 4.1E2 | 8.0E3 | 7.0E2 | 5.9E-1 | 5.5E0 | 1.2E5 | 2.5E3 | 932 | 16 | 342 | 16 | 0.67 |
| Il | ng/ml | 3.3E2 | 5.4E2 | 1.3E3 | 2.3E3 | 2.8E3 | 3.9E3 | 1.0E-9 | 1.0E-9 | 1.3E4 | 1.2E4 | 916 | 16 | 342 | 16 | 0.56 |
| Im | ng/ml | 2.1E2 | 7.0E2 | 4.0E2 | 1.2E3 | 7.6E2 | 1.5E3 | 1.3E1 | 4.7E1 | 1.5E4 | 6.2E3 | 931 | 16 | 343 | 16 | 0.80 |
| In | ng/ml | 3.3E0 | 4.1E0 | 2.1E2 | 3.0E2 | 1.5E2 | 1.1E3 | 1.0E-9 | 1.0E-9 | 3.9E3 | 4.5E3 | 937 | 16 | 344 | 16 | 0.50 |
| Hb | ng/ml | 2.5E1 | 2.3E1 | 3.6E1 | 3.3E1 | 3.5E1 | 2.4E1 | 4.8E-1 | 6.2E-1 | 2.1E2 | 8.0E1 | 333 | 10 | 191 | 10 | 0.52 |
| Hc | pg/ml | 6.6E2 | 5.7E2 | 3.4E3 | 7.0E3 | 1.2E4 | 1.6E4 | 1.0E-9 | 1.0E-9 | 1.0E5 | 5.0E4 | 333 | 10 | 191 | 10 | 0.47 |
| Hf | ng/ml | 1.6E2 | 9.7E1 | 3.7E2 | 2.1E2 | 5.1E2 | 2.5E2 | 1.0E-9 | 1.0E-9 | 3.2E3 | 6.7E2 | 333 | 10 | 191 | 10 | 0.41 |
| Io | ng/ml | 8.3E3 | 6.1E3 | 2.5E4 | 1.1E4 | 1.4E5 | 1.1E4 | 1.0E-9 | 1.3E3 | 4.0E6 | 3.3E4 | 928 | 16 | 344 | 16 | 0.47 |
| Ip | ng/ml | 1.0E1 | 3.0E1 | 2.0E1 | 2.9E1 | 2.4E1 | 2.2E1 | 1.0E-9 | 3.7E-2 | 2.6E2 | 5.7E1 | 928 | 16 | 344 | 16 | 0.61 |
| Iq | ug/ml | 1.0E-1 | 3.9E-1 | 3.0E1 | 1.6E1 | 6.3E2 | 5.5E1 | 1.0E-9 | 1.0E-9 | 1.4E4 | 2.2E2 | 928 | 16 | 344 | 16 | 0.63 |
| Ir | ug/ml | 3.5E-1 | 1.3E0 | 3.4E0 | 4.0E1 | 2.4E1 | 9.7E1 | 1.0E-9 | 1.0E-9 | 5.1E2 | 3.7E2 | 927 | 16 | 344 | 16 | 0.74 |
| Is | ng/ml | 1.6E0 | 1.3E1 | 6.4E0 | 4.4E1 | 2.2E1 | 6.9E1 | 1.0E-9 | 4.9E-1 | 5.5E2 | 2.6E2 | 928 | 16 | 344 | 16 | 0.81 |
| It | ng/ml | 2.0E0 | 3.9E0 | 2.3E1 | 5.9E1 | 1.4E2 | 1.7E2 | 1.0E-9 | 1.0E-9 | 2.8E3 | 6.8E2 | 928 | 16 | 344 | 16 | 0.60 |
| Iu | ng/ml | 2.2E2 | 4.8E2 | 1.3E3 | 2.3E3 | 4.0E3 | 6.0E3 | 1.0E-9 | 1.0E-9 | 2.9E4 | 2.4E4 | 928 | 16 | 344 | 16 | 0.56 |
| Iv | ng/ml | 1.3E1 | 7.8E1 | 6.0E1 | 5.5E2 | 5.4E2 | 1.2E3 | 1.0E-9 | 1.0E-9 | 1.6E4 | 3.8E3 | 927 | 16 | 344 | 16 | 0.73 |
| Iz | ng/ml | 1.4E2 | 2.0E2 | 5.9E2 | 4.8E2 | 3.5E3 | 5.6E2 | 9.2E-1 | 4.9E0 | 6.2E4 | 1.7E3 | 333 | 10 | 191 | 10 | 0.57 |
| Yd | ng/ml | 2.0E-1 | 1.9E-1 | 3.4E-1 | 4.6E-1 | 3.9E-1 | 8.3E-1 | 6.6E-3 | 1.7E-2 | 1.9E0 | 2.3E0 | 116 | 7 | 90 | 7 | 0.46 |
| Wb | pg/ml | 3.1E4 | 4.6E4 | 4.1E4 | 6.3E4 | 6.1E4 | 4.0E4 | 2.2E3 | 3.3E4 | 6.4E5 | 1.5E5 | 115 | 7 | 90 | 7 | 0.77 |
| Vz | pg/ml | 3.0E0 | 6.3E0 | 4.4E0 | 7.9E0 | 5.7E0 | 6.8E0 | 1.0E-9 | 1.9E0 | 4.0E1 | 2.2E1 | 115 | 7 | 90 | 7 | 0.73 |
| Si | ng/ml | 1.0E0 | 7.9E-1 | 1.9E0 | 1.7E0 | 2.6E0 | 2.0E0 | 8.6E-3 | 2.4E-1 | 1.3E1 | 5.6E0 | 113 | 7 | 87 | 7 | 0.50 |
| Sf | mIU/mL | 1.3E1 | 8.1E0 | 3.8E1 | 1.3E1 | 8.1E1 | 1.1E1 | 8.1E-2 | 9.4E-1 | 7.2E2 | 3.3E1 | 113 | 7 | 87 | 7 | 0.40 |
| Sh | mIU/mL | 1.2E1 | 4.2E0 | 4.6E1 | 1.2E1 | 1.0E2 | 2.1E1 | 2.9E-2 | 3.4E-1 | 5.9E2 | 5.8E1 | 113 | 7 | 87 | 7 | 0.33 |

Figure 7 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Sj | ng/ml | 4.0E-1 | 4.3E-1 | 4.1E-1 | 4.4E-1 | 1.0E-1 | 5.1E-2 | 1.1E-1 | 4.0E-1 | 7.2E-1 | 5.1E-1 | 113 | 7 | 87 | 7 | 0.61 |
| Rc | | 5.6E3 | 7.1E3 | 7.1E3 | 8.2E3 | 5.7E3 | 5.4E3 | 1.9E2 | 2.1E3 | 3.9E4 | 1.7E4 | 331 | 10 | 191 | 10 | 0.57 |
| Rb | pg/ml | 8.2E-1 | 7.2E-1 | 2.6E0 | 8.3E0 | 4.2E0 | 1.7E1 | 1.0E-9 | 1.0E-9 | 4.3E1 | 5.6E1 | 331 | 10 | 191 | 10 | 0.55 |
| Zq | 2.6ng/ml | 2.4E2 | 3.9E2 | 3.1E2 | 5.0E2 | 2.7E2 | 2.4E2 | 8.3E0 | 3.0E2 | 9.7E2 | 9.7E2 | 113 | 7 | 87 | 7 | 0.75 |
| Zw | 2.5ng/ml | 4.4E0 | 1.3E1 | 1.0E1 | 2.6E1 | 1.3E1 | 2.6E1 | 6.3E-2 | 7.7E-1 | 5.9E1 | 6.3E1 | 116 | 7 | 90 | 7 | 0.70 |
| Zx | 2.3mU/ml | 1.1E-1 | 1.3E-1 | 3.4E-1 | 4.1E-1 | 1.1E0 | 6.5E-1 | 3.2E-2 | 7.0E-2 | 1.2E1 | 1.9E0 | 116 | 7 | 90 | 7 | 0.61 |
| Pz | ng/ml | 3.8E3 | 1.0E4 | 8.1E3 | 7.0E3 | 3.7E3 | 4.1E3 | 1.3E1 | 6.5E2 | 1.0E6 | 1.3E4 | 929 | 16 | 342 | 16 | 0.62 |
| Qa | ng/ml | 3.5E3 | 1.5E4 | 6.3E3 | 2.9E4 | 7.4E3 | 5.3E4 | 1.2E1 | 1.5E3 | 5.2E4 | 2.2E5 | 929 | 16 | 342 | 16 | 0.83 |
| Qb | ng/ml | 9.7E1 | 2.8E2 | 2.1E2 | 3.5E2 | 4.8E2 | 2.4E2 | 7.9E-1 | 5.1E1 | 8.3E3 | 8.8E2 | 929 | 16 | 342 | 16 | 0.76 |
| Qc | ng/ml | 2.3E2 | 5.4E2 | 6.3E2 | 6.5E2 | 5.5E3 | 7.2E2 | 1.0E-9 | 1.3E1 | 1.7E5 | 2.8E3 | 929 | 16 | 342 | 16 | 0.61 |
| Qd | ng/ml | 9.2E3 | 3.5E4 | 2.1E4 | 6.3E4 | 7.7E4 | 7.0E4 | 1.5E2 | 4.6E3 | 2.0E6 | 2.3E5 | 929 | 16 | 342 | 16 | 0.77 |
| Qe | ng/ml | 9.2E2 | 3.6E3 | 1.8E3 | 5.3E3 | 3.8E3 | 4.9E3 | 1.0E-9 | 4.1E2 | 9.7E4 | 1.8E4 | 929 | 16 | 342 | 16 | 0.82 |
| Jd | ng/ml | 9.4E-1 | 4.7E0 | 5.8E0 | 7.3E0 | 3.8E1 | 6.1E0 | 1.0E-9 | 1.4E0 | 6.5E2 | 2.1E1 | 332 | 10 | 193 | 10 | 0.84 |
| Je | ng/ml | 1.0E-9 | 4.3E0 | 2.0E0 | 4.4E0 | 7.0E0 | 4.3E0 | 1.0E-9 | 1.0E-9 | 8.8E1 | 1.1E1 | 332 | 10 | 193 | 10 | 0.70 |
| Jf | ng/ml | 1.0E-9 | 8.4E-1 | 1.1E0 | 1.5E0 | 2.2E0 | 1.7E0 | 1.0E-9 | 1.0E-9 | 1.2E1 | 3.7E0 | 332 | 10 | 193 | 10 | 0.59 |
| Jg | ng/ml | 4.9E2 | 1.8E3 | 8.2E2 | 2.0E3 | 1.0E3 | 1.8E3 | 1.0E-9 | 8.7E1 | 1.0E4 | 7.1E3 | 933 | 16 | 344 | 16 | 0.74 |
| Jh | ng/ml | 3.0E0 | 5.2E1 | 2.7E1 | 8.5E1 | 1.1E2 | 1.2E2 | 1.0E-9 | 1.0E-9 | 1.6E3 | 4.9E2 | 933 | 16 | 344 | 16 | 0.76 |
| Ji | ng/ml | 5.3E1 | 2.3E2 | 7.7E1 | 3.3E2 | 8.0E1 | 3.2E2 | 1.0E-9 | 2.0E1 | 6.9E2 | 1.3E3 | 933 | 16 | 344 | 16 | 0.86 |
| Sr | pg/mL | 3.8E2 | 3.1E3 | 8.5E2 | 4.4E3 | 1.3E3 | 6.1E3 | 1.0E-9 | 2.3E2 | 9.8E3 | 2.1E4 | 322 | 10 | 188 | 10 | 0.82 |
| Ss | pg/ml | 9.5E4 | 1.7E5 | 1.5E5 | 1.4E5 | 1.8E5 | 1.1E5 | 2.7E3 | 1.4E4 | 1.8E6 | 3.6E5 | 322 | 10 | 188 | 10 | 0.54 |
| St | pg/mL | 2.6E7 | 1.0E8 | 5.6E7 | 2.3E8 | 9.4E7 | 5.0E8 | 1.0E-9 | 2.3E6 | 1.2E9 | 1.7E9 | 326 | 10 | 189 | 10 | 0.75 |
| Wc | ng/ml | 1.0E-9 | 1.0E-9 | 5.8E-2 | 2.6E-1 | 1.3E-1 | 6.7E-1 | 1.0E-9 | 1.0E-9 | 9.8E-1 | 1.8E0 | 116 | 7 | 90 | 7 | 0.44 |
| Wd | ng/ml | 9.4E0 | 1.8E1 | 4.3E1 | 1.1E2 | 1.4E2 | 1.6E2 | 1.0E-9 | 4.3E0 | 1.2E3 | 3.8E2 | 116 | 7 | 90 | 7 | 0.73 |
| We | ng/ml | 3.8E-1 | 4.7E-1 | 1.2E0 | 4.1E0 | 3.0E0 | 8.4E0 | 1.0E-9 | 2.0E-3 | 2.3E1 | 2.3E1 | 116 | 7 | 90 | 7 | 0.58 |
| Wg | ng/ml | 1.0E-9 | 1.0E-9 | 1.4E-4 | 7.6E-2 | 1.5E-3 | 2.0E-1 | 1.0E-9 | 1.0E-9 | 1.6E-2 | 5.3E-1 | 116 | 7 | 90 | 7 | 0.57 |
| Wh | ng/ml | 9.8E-3 | 4.5E-2 | 1.1E-1 | 9.1E-2 | 4.9E-1 | 1.2E-1 | 1.0E-9 | 3.7E-3 | 4.5E0 | 3.4E-1 | 116 | 7 | 90 | 7 | 0.70 |
| Wf | ng/ml | 1.0E-9 | 1.0E-9 | 1.7E-1 | 4.7E-1 | 5.2E-1 | 8.4E-1 | 1.0E-9 | 1.0E-9 | 4.6E0 | 2.3E0 | 116 | 7 | 90 | 7 | 0.58 |
| Ra | pg/ml | 1.0E-9 | 1.0E-9 | 6.1E-1 | 7.0E0 | 1.2E0 | 2.0E1 | 1.0E-9 | 1.0E-9 | 7.3E0 | 6.4E1 | 331 | 10 | 191 | 10 | 0.48 |
| Qz | pg/ml | 1.0E1 | 1.4E1 | 6.3E1 | 3.9E1 | 1.0E2 | 4.8E1 | 1.0E-9 | 1.0E-9 | 7.1E2 | 1.4E2 | 331 | 10 | 191 | 10 | 0.58 |
| Qy | pg/ml | 4.4E-1 | 3.1E0 | 1.6E1 | 8.4E0 | 7.6E1 | 1.6E1 | 1.0E-9 | 1.1E-1 | 6.5E2 | 5.4E1 | 331 | 10 | 191 | 10 | 0.75 |
| Qx | pg/ml | 1.0E-9 | 1.0E-9 | 5.4E0 | 1.4E1 | 4.5E1 | 3.4E1 | 1.0E-9 | 1.0E-9 | 5.8E2 | 1.1E2 | 331 | 10 | 191 | 10 | 0.59 |
| Qw | pg/ml | 1.0E-9 | 1.0E0 | 2.9E0 | 3.6E0 | 1.4E1 | 6.9E0 | 1.0E-9 | 1.0E-9 | 1.3E2 | 2.3E1 | 331 | 10 | 191 | 10 | 0.66 |
| Qv | pg/ml | 2.3E4 | 7.9E3 | 3.5E4 | 1.1E4 | 5.5E4 | 1.2E4 | 1.0E-9 | 4.0E2 | 7.4E5 | 3.3E4 | 331 | 10 | 191 | 10 | 0.24 |
| Qu | pg/ml | 7.8E0 | 5.8E0 | 8.2E1 | 1.1E2 | 1.7E2 | 2.1E2 | 1.0E-9 | 1.0E-9 | 9.8E2 | 6.7E2 | 331 | 10 | 191 | 10 | 0.51 |
| Qt | pg/ml | 1.0E1 | 5.4E1 | 4.9E1 | 9.2E1 | 1.2E2 | 1.1E2 | 1.0E-9 | 1.0E-9 | 1.0E3 | 3.1E2 | 331 | 10 | 191 | 10 | 0.68 |
| Qh | ng/ml | 1.7E1 | 5.3E1 | 4.0E1 | 6.4E1 | 7.7E1 | 5.5E1 | 1.0E-9 | 5.1E0 | 8.0E2 | 1.6E2 | 331 | 10 | 191 | 10 | 0.70 |
| Qg | ng/ml | 8.3E0 | 4.1E0 | 2.0E1 | 2.1E1 | 6.3E1 | 4.3E1 | 5.1E-2 | 1.5E0 | 1.0E3 | 1.4E2 | 331 | 10 | 191 | 10 | 0.40 |
| Jj | ng/ml | 6.0E2 | 1.1E2 | 1.7E3 | 4.2E2 | 1.2E4 | 8.0E2 | 2.3E0 | 1.2E1 | 3.4E5 | 3.3E3 | 933 | 16 | 344 | 16 | 0.23 |
| Jk | ng/ml | 3.1E0 | 1.6E1 | 2.1E1 | 4.8E1 | 4.7E1 | 6.5E1 | 1.0E-9 | 2.4E-1 | 3.9E2 | 2.4E2 | 933 | 16 | 344 | 16 | 0.69 |
| Jl | ng/ml | 4.4E-1 | 1.5E1 | 1.9E0 | 6.3E2 | 5.6E0 | 2.5E3 | 7.6E-4 | 1.4E-1 | 1.1E2 | 9.9E3 | 933 | 16 | 344 | 16 | 0.82 |
| Jm | ng/ml | 1.8E1 | 4.7E1 | 5.8E1 | 5.6E1 | 1.3E2 | 5.3E1 | 1.0E-9 | 4.7E-1 | 2.1E3 | 1.5E2 | 933 | 16 | 344 | 16 | 0.58 |
| Jn | pg/ml | 4.0E-1 | 1.4E0 | 2.5E0 | 8.7E1 | 2.2E1 | 2.3E2 | 1.0E-9 | 1.6E-1 | 6.2E2 | 7.3E2 | 932 | 16 | 344 | 16 | 0.76 |
| Jo | pg/ml | 3.6E3 | 3.7E3 | 4.7E3 | 1.2E4 | 3.8E3 | 2.5E4 | 2.0E1 | 2.3E2 | 2.4E4 | 1.0E5 | 933 | 16 | 344 | 16 | 0.50 |
| Jp | pg/ml | 7.0E4 | 9.8E4 | 7.4E4 | 1.1E5 | 3.8E4 | 4.7E4 | 5.8E2 | 4.5E4 | 3.8E5 | 2.1E5 | 933 | 16 | 344 | 16 | 0.75 |
| Jq | pg/ml | 9.4E1 | 3.1E2 | 1.5E2 | 1.1E3 | 2.1E2 | 2.2E3 | 1.0E0 | 1.1E1 | 4.0E3 | 8.7E3 | 933 | 16 | 344 | 16 | 0.76 |
| Jr | pg/ml | 5.2E0 | 2.3E1 | 3.3E1 | 8.2E2 | 3.6E2 | 2.2E3 | 1.0E-9 | 2.6E0 | 1.1E4 | 7.4E3 | 933 | 16 | 344 | 16 | 0.81 |
| Js | pg/ml | 1.3E1 | 2.0E1 | 4.9E1 | 4.0E2 | 3.6E2 | 1.0E3 | 1.0E-9 | 3.0E0 | 1.0E4 | 3.0E3 | 933 | 16 | 344 | 16 | 0.65 |
| Jt | pg/ml | 2.6E3 | 4.4E3 | 3.2E3 | 8.0E3 | 2.4E3 | 1.3E4 | 2.2E1 | 4.1E2 | 2.2E4 | 5.2E4 | 933 | 16 | 344 | 16 | 0.60 |
| Xa | pg/ml | 1.0E-9 | 1.7E1 | 1.5E1 | 2.0E2 | 5.5E1 | 4.5E2 | 1.0E-9 | 4.9E0 | 5.6E2 | 1.2E3 | 115 | 7 | 90 | 7 | 0.81 |
| Ye | pg/ml | 1.0E-9 | 1.0E-9 | 7.7E0 | 1.0E-9 | 3.5E1 | 0.0E0 | 1.0E-9 | 1.0E-9 | 3.5E2 | 1.0E-9 | 115 | 7 | 90 | 7 | 0.35 |
| Tm | pg/ml | 1.0E-9 | 1.0E-9 | 3.8E0 | 1.0E-9 | 8.8E0 | 0.0E0 | 1.0E-9 | 1.0E-9 | 6.8E1 | 1.0E-9 | 115 | 7 | 90 | 7 | 0.35 |
| Tl | pg/ml | 1.3E-1 | 1.0E-9 | 2.9E-1 | 3.7E0 | 3.6E-1 | 9.3E0 | 1.0E-9 | 1.0E-9 | 1.8E0 | 2.5E1 | 115 | 7 | 90 | 7 | 0.45 |
| Ju | mIU/ml | 8.7E0 | 8.2E0 | 1.9E1 | 1.0E1 | 2.9E1 | 8.4E0 | 4.8E-2 | 1.9E-1 | 2.3E2 | 2.6E1 | 332 | 10 | 193 | 10 | 0.47 |
| Jv | mIU/ml | 1.2E1 | 4.6E0 | 3.3E1 | 9.1E0 | 5.7E1 | 1.2E1 | 9.4E-3 | 2.1E-1 | 4.4E2 | 3.7E1 | 332 | 10 | 193 | 10 | 0.36 |
| Jy | ng/ml | 1.6E-3 | 4.0E-3 | 2.1E-3 | 9.3E-3 | 3.8E-3 | 1.3E-2 | 1.0E-9 | 8.6E-4 | 5.2E-2 | 4.1E-2 | 332 | 10 | 193 | 10 | 0.79 |
| Kc | pg/ml | 2.6E1 | 2.6E1 | 4.6E1 | 5.3E1 | 4.9E1 | 5.7E1 | 1.0E-9 | 6.9E0 | 2.7E2 | 1.6E2 | 333 | 10 | 191 | 10 | 0.49 |
| Kd | pg/ml | 1.0E-9 | 1.0E-9 | 2.1E2 | 4.4E3 | 6.4E2 | 1.2E4 | 1.0E-9 | 1.0E-9 | 5.0E3 | 3.8E4 | 333 | 10 | 191 | 10 | 0.52 |

Figure 7 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ke | pg/ml | 1.3E4 | 1.4E4 | 1.5E4 | 5.8E4 | 1.1E4 | 9.9E4 | 3.4E2 | 4.2E3 | 7.0E4 | 3.2E5 | 333 | 10 | 191 | 10 | 0.60 |
| Kf | pg/mL | 7.2E0 | 6.7E0 | 7.4E0 | 1.5E1 | 6.0E0 | 2.3E1 | 1.0E-9 | 1.7E0 | 4.4E1 | 7.8E1 | 333 | 10 | 191 | 10 | 0.55 |
| Kg | pg/mL | 1.1E3 | 6.9E2 | 1.9E3 | 3.5E3 | 2.4E3 | 8.3E3 | 7.3E1 | 1.3E2 | 2.2E4 | 2.7E4 | 333 | 10 | 191 | 10 | 0.37 |
| Ki | pg/ml | 5.9E1 | 9.5E1 | 7.0E1 | 1.0E2 | 5.3E1 | 4.2E1 | 1.0E-9 | 5.9E1 | 3.8E2 | 2.0E2 | 332 | 10 | 191 | 10 | 0.74 |
| Kj | pg/ml | 1.0E3 | 4.0E2 | 1.6E3 | 2.0E3 | 1.6E3 | 4.5E3 | 1.4E1 | 1.2E2 | 1.0E4 | 1.5E4 | 333 | 10 | 191 | 10 | 0.31 |
| Kk | pg/ml | 6.9E0 | 1.2E1 | 1.2E1 | 2.3E1 | 1.5E1 | 2.1E1 | 1.0E-9 | 5.0E0 | 1.6E2 | 5.9E1 | 333 | 10 | 191 | 10 | 0.72 |
| Kl | pg/ml | 2.0E4 | 2.7E4 | 2.8E4 | 3.0E4 | 2.5E4 | 2.6E4 | 1.6E2 | 1.6E3 | 1.6E5 | 7.8E4 | 333 | 10 | 191 | 10 | 0.52 |
| Kn | pg/ml | 3.0E1 | 6.7E1 | 6.3E1 | 5.7E2 | 1.0E2 | 1.5E3 | 1.0E-9 | 1.0E-9 | 7.3E2 | 4.9E3 | 333 | 10 | 191 | 10 | 0.65 |
| Ko | pg/ml | 3.5E2 | 2.9E2 | 5.0E2 | 7.7E2 | 5.1E2 | 1.2E3 | 1.0E-9 | 6.5E1 | 3.8E3 | 4.1E3 | 333 | 10 | 191 | 10 | 0.55 |
| Kp | pg/ml | 3.4E2 | 3.8E2 | 3.6E2 | 1.6E3 | 2.6E2 | 4.1E3 | 1.0E-9 | 3.7E1 | 1.7E3 | 1.3E4 | 333 | 10 | 191 | 10 | 0.53 |
| Kq | pg/ml | 3.3E2 | 1.3E3 | 4.7E2 | 1.8E4 | 7.6E2 | 5.0E4 | 1.6E0 | 1.7E2 | 9.8E3 | 1.6E5 | 325 | 10 | 185 | 10 | 0.81 |
| Kr | pg/ml | 4.5E-1 | 1.0E-9 | 2.4E0 | 4.2E1 | 4.6E0 | 1.3E2 | 1.0E-9 | 1.0E-9 | 3.9E1 | 4.2E2 | 325 | 10 | 185 | 10 | 0.39 |
| Ks | pg/ml | 1.4E4 | 1.7E4 | 2.0E4 | 1.9E4 | 1.8E4 | 1.7E4 | 5.1E1 | 1.3E3 | 1.1E5 | 5.0E4 | 325 | 10 | 185 | 10 | 0.49 |
| Ps | ng/ml | 1.6E2 | 9.4E2 | 6.2E2 | 1.3E3 | 1.8E3 | 1.1E3 | 4.1E-1 | 4.5E2 | 1.2E4 | 3.8E3 | 113 | 7 | 87 | 7 | 0.88 |
| Kx | ng/ml | 1.1E-4 | 1.2E-2 | 6.7E-3 | 1.8E-2 | 1.3E-2 | 2.3E-2 | 1.0E-9 | 1.0E-9 | 1.0E-1 | 6.4E-2 | 330 | 10 | 190 | 10 | 0.72 |
| Ky | ng/ml | 9.8E-2 | 7.4E-1 | 3.9E-1 | 8.4E-1 | 8.5E-1 | 8.1E-1 | 1.0E-9 | 3.0E-2 | 6.3E0 | 2.7E0 | 330 | 10 | 190 | 10 | 0.76 |
| Kz | ng/ml | 1.0E-9 | 1.4E-2 | 3.4E-3 | 8.9E-3 | 5.6E-3 | 7.8E-3 | 1.0E-9 | 1.0E-9 | 3.6E-2 | 1.8E-2 | 330 | 10 | 190 | 10 | 0.68 |
| Rz | ng/ml | 3.1E-1 | 3.3E-1 | 1.0E0 | 1.1E0 | 1.5E0 | 1.5E0 | 3.6E-3 | 1.0E-1 | 6.7E0 | 4.2E0 | 113 | 7 | 87 | 7 | 0.59 |
| Ry | ng/ml | 1.6E-2 | 1.6E-2 | 2.2E-2 | 6.7E-2 | 2.2E-2 | 1.3E-1 | 1.0E-9 | 1.6E-2 | 1.2E-1 | 3.5E-1 | 113 | 7 | 87 | 7 | 0.59 |
| Rx | ng/ml | 1.0E-9 | 3.5E-5 | 1.8E-3 | 1.7E-3 | 3.2E-3 | 3.2E-3 | 1.0E-9 | 1.0E-9 | 2.0E-2 | 8.4E-3 | 113 | 7 | 87 | 7 | 0.51 |
| Ld | pg/ml | 1.0E-9 | 7.5E-1 | 3.6E0 | 5.5E0 | 8.6E0 | 8.5E0 | 1.0E-9 | 1.0E-9 | 8.4E1 | 2.3E1 | 331 | 10 | 190 | 10 | 0.58 |
| Lh | pg/ml | 1.3E4 | 4.0E4 | 2.1E4 | 8.5E4 | 2.6E4 | 1.2E5 | 1.0E-9 | 1.8E3 | 2.6E5 | 4.1E5 | 932 | 16 | 345 | 16 | 0.75 |
| Li | pg/ml | 3.5E3 | 1.7E4 | 1.7E4 | 6.1E4 | 6.2E4 | 8.6E4 | 1.0E-9 | 3.7E1 | 1.3E6 | 3.1E5 | 932 | 16 | 345 | 16 | 0.71 |
| Lj | pg/ml | 2.8E3 | 1.3E4 | 2.3E4 | 4.8E4 | 6.4E4 | 9.7E4 | 1.0E-9 | 2.4E2 | 5.2E5 | 3.9E5 | 932 | 16 | 345 | 16 | 0.69 |
| Lp | pg/ml | 9.5E0 | 1.8E1 | 8.2E1 | 2.0E2 | 2.1E2 | 3.8E2 | 1.0E-9 | 1.0E-9 | 1.4E3 | 1.0E3 | 113 | 7 | 87 | 7 | 0.53 |
| Lt | pg/ml | 1.0E-9 | 1.0E-9 | 2.4E0 | 1.0E-9 | 8.8E0 | 0.0E0 | 1.0E-9 | 1.0E-9 | 6.0E1 | 1.0E-9 | 113 | 7 | 87 | 7 | 0.45 |
| Rv | ng/ml | 5.0E-4 | 1.0E-9 | 1.3E-3 | 2.1E-3 | 2.2E-3 | 4.6E-3 | 1.0E-9 | 1.0E-9 | 1.6E-2 | 1.2E-2 | 113 | 7 | 87 | 7 | 0.41 |
| Ru | ng/ml | 1.0E-9 | 1.0E-9 | 1.7E-2 | 5.8E-2 | 7.0E-2 | 1.3E-1 | 1.0E-9 | 1.0E-9 | 3.8E-1 | 3.4E-1 | 113 | 7 | 87 | 7 | 0.60 |
| Rt | ng/ml | 6.2E-2 | 3.6E-2 | 1.1E-1 | 1.2E0 | 1.4E-1 | 2.8E0 | 1.0E-3 | 8.6E-3 | 6.3E-1 | 7.4E0 | 113 | 7 | 87 | 7 | 0.53 |
| Yl | pg/ml | 1.1E1 | 4.0E1 | 1.7E1 | 5.8E1 | 1.8E1 | 7.3E1 | 1.0E-9 | 1.0E-9 | 1.1E2 | 2.2E2 | 116 | 7 | 90 | 7 | 0.76 |
| Rm | ng/ml | 1.9E1 | 8.6E1 | 5.2E1 | 8.9E1 | 8.1E1 | 8.1E1 | 2.2E-1 | 3.9E-1 | 6.5E2 | 2.5E2 | 326 | 10 | 190 | 10 | 0.70 |
| Rh | ng/ml | 1.3E2 | 1.5E2 | 3.5E2 | 1.9E3 | 1.2E3 | 5.3E3 | 3.6E0 | 2.8E1 | 1.7E4 | 1.7E4 | 326 | 10 | 190 | 10 | 0.56 |
| Ri | ng/ml | 1.0E-9 | 1.0E-9 | 4.3E0 | 4.1E-2 | 1.5E1 | 1.3E-1 | 1.0E-9 | 1.0E-9 | 2.2E2 | 4.1E-1 | 327 | 10 | 191 | 10 | 0.30 |
| Rg | ng/ml | 1.0E-9 | 1.0E-9 | 6.7E-2 | 6.4E-2 | 4.1E-1 | 1.9E-1 | 1.0E-9 | 1.0E-9 | 4.6E0 | 5.9E-1 | 326 | 10 | 190 | 10 | 0.50 |
| Rj | ng/ml | 1.0E-9 | 1.0E-9 | 1.3E0 | 2.7E1 | 5.2E0 | 8.5E1 | 1.0E-9 | 1.0E-9 | 8.0E1 | 2.7E2 | 327 | 10 | 191 | 10 | 0.47 |
| Rf | ng/ml | 3.9E-1 | 1.5E0 | 9.7E-1 | 4.1E0 | 1.7E0 | 6.0E0 | 7.8E-3 | 1.8E-1 | 1.5E1 | 1.7E1 | 326 | 10 | 190 | 10 | 0.76 |
| Ql | pg/ml | 4.5E0 | 1.4E1 | 1.4E1 | 3.0E1 | 2.9E1 | 3.1E1 | 1.0E-9 | 4.3E-1 | 2.9E2 | 9.3E1 | 332 | 10 | 193 | 10 | 0.73 |
| Qm | pg/ml | 3.2E0 | 2.0E1 | 2.0E1 | 2.7E1 | 3.7E1 | 2.3E1 | 1.0E-9 | 1.0E-9 | 3.6E2 | 6.9E1 | 332 | 10 | 193 | 10 | 0.67 |
| Qn | pg/ml | 6.1E-1 | 8.6E-1 | 8.0E0 | 3.6E0 | 2.6E1 | 4.7E0 | 1.0E-9 | 1.0E-9 | 2.4E2 | 1.2E1 | 332 | 10 | 193 | 10 | 0.59 |
| Nv | pg/ml | 4.0E3 | 1.3E4 | 1.1E4 | 2.7E4 | 4.2E4 | 3.0E4 | 1.0E-9 | 1.3E3 | 1.1E6 | 9.4E4 | 939 | 16 | 345 | 16 | 0.72 |
| Nw | pg/ml | 8.9E3 | 2.4E4 | 1.3E4 | 5.2E4 | 1.6E4 | 6.7E4 | 8.6E1 | 6.2E3 | 2.1E5 | 2.2E5 | 939 | 16 | 345 | 16 | 0.81 |
| Nx | pg/ml | 2.2E2 | 7.5E2 | 4.1E2 | 9.4E2 | 6.4E2 | 1.1E3 | 1.0E-9 | 1.0E-9 | 7.4E3 | 4.1E3 | 939 | 16 | 345 | 16 | 0.68 |
| Ny | pg/ml | 6.2E0 | 2.9E1 | 5.2E1 | 2.8E2 | 8.3E2 | 6.9E2 | 1.0E-9 | 1.0E-9 | 2.5E4 | 2.8E3 | 939 | 16 | 345 | 16 | 0.80 |
| Oa | pg/ml | 1.8E2 | 4.8E2 | 4.6E2 | 9.3E2 | 7.3E2 | 9.0E2 | 1.0E-9 | 6.5E1 | 4.8E3 | 2.4E3 | 332 | 10 | 193 | 10 | 0.71 |
| Op | pg/ml | 4.1E5 | 4.9E5 | 4.1E5 | 4.5E5 | 1.6E5 | 2.0E5 | 3.3E4 | 9.4E4 | 7.3E5 | 7.5E5 | 113 | 7 | 87 | 7 | 0.58 |
| Oe | pg/ml | 7.1E1 | 4.7E0 | 2.9E2 | 1.7E2 | 7.4E2 | 3.3E2 | 1.0E-9 | 1.0E-9 | 1.9E4 | 1.1E3 | 930 | 16 | 344 | 16 | 0.42 |
| Of | pg/ml | 1.8E2 | 6.4E1 | 5.9E3 | 6.6E3 | 2.8E4 | 1.7E4 | 1.0E-9 | 3.5E0 | 6.2E5 | 6.6E4 | 938 | 16 | 345 | 16 | 0.45 |
| Og | pg/ml | 8.2E-2 | 2.6E-2 | 7.1E-1 | 6.2E-1 | 4.7E0 | 8.7E-2 | 1.0E-9 | 1.0E-9 | 8.3E1 | 3.2E-1 | 938 | 16 | 345 | 16 | 0.35 |
| Oh | pg/ml | 2.6E0 | 1.5E1 | 1.8E1 | 1.1E2 | 1.4E2 | 2.8E2 | 1.0E-9 | 1.1E0 | 3.5E3 | 1.1E3 | 938 | 16 | 345 | 16 | 0.77 |
| Oi | pg/ml | 2.6E0 | 1.0E-9 | 6.3E0 | 4.2E0 | 9.8E0 | 8.1E0 | 1.0E-9 | 1.0E-9 | 8.6E1 | 3.1E1 | 938 | 16 | 345 | 16 | 0.38 |
| Ok | pg/ml | 3.9E2 | 1.1E3 | 5.4E2 | 1.9E3 | 5.7E2 | 2.0E3 | 1.3E1 | 1.8E2 | 7.0E3 | 7.8E3 | 938 | 16 | 345 | 16 | 0.79 |
| Om | pg/ml | 3.9E2 | 1.6E3 | 8.2E2 | 5.3E3 | 2.1E3 | 1.2E4 | 1.0E-9 | 2.5E2 | 3.6E4 | 5.1E4 | 938 | 16 | 345 | 16 | 0.79 |
| On | pg/ml | 1.8E2 | 9.3E2 | 2.8E2 | 1.5E3 | 3.9E2 | 2.1E3 | 1.0E-9 | 2.6E1 | 4.5E3 | 8.5E3 | 938 | 16 | 345 | 16 | 0.80 |
| Or | pg/ml | 1.4E1 | 1.1E2 | 3.5E1 | 1.5E2 | 6.6E1 | 1.6E2 | 1.0E-9 | 1.0E-9 | 5.0E2 | 5.1E2 | 334 | 10 | 191 | 10 | 0.77 |
| Ow | pg/ml | 3.3E1 | 1.1E2 | 1.2E2 | 4.9E2 | 3.3E2 | 9.3E2 | 1.0E-9 | 1.8E1 | 3.2E3 | 3.0E3 | 334 | 10 | 191 | 10 | 0.72 |
| Ou | pg/ml | 4.8E2 | 8.3E2 | 9.8E2 | 3.7E3 | 1.6E3 | 4.2E3 | 1.0E-9 | 3.4E2 | 9.8E3 | 1.1E4 | 334 | 10 | 191 | 10 | 0.71 |
| Ul | ng/ml | 1.0E-9 | 1.0E-9 | 1.6E0 | 8.9E0 | 7.5E0 | 1.9E1 | 1.0E-9 | 1.0E2 | 5.6E1 | | 340 | 10 | 195 | 10 | 0.56 |

Figure 7 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Uo | ng/ml | 1.0E-9 | 1.0E-9 | 9.9E-2 | 1.0E-1 | 2.6E-1 | 2.0E-1 | 1.0E-9 | 1.0E-9 | 2.6E0 | 6.3E-1 | 340 | 10 | 195 | 10 | 0.55 |
| Uk | ng/ml | 1.0E-9 | 1.0E-9 | 7.2E-3 | 1.4E-3 | 2.4E-2 | 3.4E-3 | 1.0E-9 | 1.0E-9 | 3.2E-1 | 1.1E-2 | 340 | 10 | 195 | 10 | 0.39 |
| Um | ng/ml | 1.0E-9 | 1.0E-9 | 4.0E-1 | 3.0E-1 | 9.5E-1 | 7.1E-1 | 1.0E-9 | 1.0E-9 | 7.2E0 | 2.3E0 | 340 | 10 | 195 | 10 | 0.47 |
| Uf | ng/ml | 6.0E-2 | 2.1E-1 | 1.4E-1 | 7.2E-1 | 2.7E-1 | 1.7E0 | 1.0E-3 | 3.6E-2 | 2.5E0 | 5.6E0 | 340 | 10 | 195 | 10 | 0.72 |
| Uh | ng/ml | 2.0E0 | 3.6E0 | 3.2E0 | 5.7E0 | 3.4E0 | 5.8E0 | 1.3E-2 | 7.1E-1 | 1.8E1 | 1.7E1 | 340 | 10 | 195 | 10 | 0.65 |
| Un | ng/ml | 1.9E0 | 3.6E0 | 2.2E0 | 5.7E0 | 1.3E0 | 7.1E0 | 1.3E-1 | 1.8E0 | 8.0E0 | 2.5E1 | 340 | 10 | 195 | 10 | 0.78 |
| Ug | ng/ml | 1.5E1 | 9.6E0 | 2.8E1 | 1.8E1 | 3.0E1 | 2.5E1 | 6.9E-1 | 1.7E0 | 2.1E2 | 8.5E1 | 340 | 10 | 195 | 10 | 0.39 |
| Ur | ng/ml | 1.6E-1 | 1.0E-9 | 7.6E-1 | 7.8E-1 | 5.2E0 | 2.3E0 | 1.0E-9 | 1.0E-9 | 9.3E1 | 7.3E0 | 339 | 10 | 194 | 10 | 0.31 |
| Up | ng/ml | 1.0E-9 | 1.0E-9 | 5.0E-3 | 2.4E-1 | 2.2E-2 | 7.5E-1 | 1.0E-9 | 1.0E-9 | 3.3E-1 | 2.4E0 | 339 | 10 | 194 | 10 | 0.55 |
| Us | ng/ml | 3.5E-3 | 1.0E-9 | 1.9E-2 | 1.7E-1 | 4.4E-2 | 5.2E-1 | 1.0E-9 | 1.0E-9 | 4.0E-1 | 1.7E0 | 339 | 10 | 194 | 10 | 0.39 |
| Uv | ng/ml | 2.7E-3 | 4.2E-3 | 1.1E-2 | 6.9E-2 | 3.8E-2 | 1.4E-1 | 1.0E-9 | 1.0E-9 | 4.3E-1 | 4.1E-1 | 339 | 10 | 194 | 10 | 0.58 |
| Ut | ng/ml | 6.3E-1 | 2.8E0 | 2.6E0 | 1.3E1 | 8.0E0 | 2.1E1 | 1.0E-9 | 1.0E-9 | 7.8E1 | 6.5E1 | 339 | 10 | 194 | 10 | 0.75 |
| Uu | ng/ml | 7.1E0 | 5.6E0 | 8.1E0 | 5.9E0 | 5.8E0 | 3.8E0 | 4.5E-1 | 1.2E0 | 4.0E1 | 1.2E1 | 339 | 10 | 194 | 10 | 0.40 |
| Uw | ng/ml | 2.3E0 | 5.8E0 | 3.0E0 | 9.0E0 | 3.8E0 | 1.4E1 | 1.0E-9 | 1.1E0 | 3.7E1 | 3.9E1 | 122 | 7 | 96 | 7 | 0.70 |
| Vb | ng/ml | 1.0E0 | 1.3E0 | 1.0E0 | 1.8E0 | 4.4E-1 | 2.1E0 | 8.5E-2 | 3.5E-1 | 2.5E0 | 6.4E0 | 122 | 7 | 96 | 7 | 0.60 |
| Vc | ng/ml | 1.0E-9 | 1.0E-9 | 7.1E-3 | 1.0E-9 | 6.0E-2 | 0.0E0 | 1.0E-9 | 1.0E-9 | 6.5E-1 | 1.0E-9 | 122 | 7 | 96 | 7 | 0.48 |
| Uy | ng/ml | 1.3E0 | 7.0E-1 | 4.9E0 | 1.3E1 | 1.3E1 | 2.1E1 | 3.1E-2 | 2.0E-2 | 9.9E1 | 4.6E1 | 122 | 7 | 96 | 7 | 0.44 |
| Uz | ng/ml | 1.0E-9 | 1.0E-9 | 6.2E-3 | 4.7E0 | 4.8E-2 | 1.2E1 | 1.0E-9 | 1.0E-9 | 4.4E-1 | 3.3E1 | 122 | 7 | 96 | 7 | 0.56 |
| Ux | ng/ml | 1.7E2 | 1.9E2 | 1.9E2 | 2.2E2 | 1.4E2 | 1.1E2 | 4.5E0 | 1.0E2 | 5.3E2 | 3.9E2 | 122 | 7 | 96 | 7 | 0.59 |
| Va | ng/ml | 1.7E1 | 3.1E0 | 2.6E1 | 1.4E1 | 2.7E1 | 2.8E1 | 1.2E-1 | 1.2E0 | 1.2E2 | 7.8E1 | 122 | 7 | 96 | 7 | 0.30 |
| Vh | ng/ml | 1.0E-2 | 1.8E-2 | 1.6E-2 | 1.3E-1 | 2.0E-2 | 3.2E-1 | 1.0E-9 | 2.2E-3 | 1.2E-1 | 8.6E-1 | 122 | 7 | 96 | 7 | 0.61 |
| Vi | ng/ml | 3.1E-3 | 4.3E-2 | 1.2E-1 | 2.9E-1 | 1.2E0 | 6.8E-1 | 1.0E-9 | 2.0E-4 | 1.4E1 | 1.8E0 | 122 | 7 | 96 | 7 | 0.75 |
| Vj | ng/ml | 2.5E1 | 8.6E1 | 1.9E2 | 8.4E1 | 9.0E2 | 5.4E1 | 1.4E0 | 1.3E1 | 8.4E3 | 1.7E2 | 120 | 7 | 94 | 7 | 0.70 |
| Vp | ng/ml | 1.0E-9 | 3.6E-2 | 3.5E-1 | 5.0E0 | 3.1E0 | 1.6E1 | 1.0E-9 | 1.0E-9 | 5.0E1 | 4.9E1 | 340 | 10 | 195 | 10 | 0.67 |
| Vt | ng/ml | 6.7E0 | 9.5E0 | 9.4E0 | 2.9E1 | 9.8E0 | 4.7E1 | 4.3E-1 | 1.8E0 | 8.6E1 | 1.6E2 | 340 | 10 | 195 | 10 | 0.63 |
| Vu | ng/ml | 1.0E-9 | 3.1E0 | 2.3E0 | 4.8E0 | 6.4E0 | 5.1E0 | 1.0E-9 | 1.0E-9 | 7.1E1 | 1.4E1 | 334 | 8 | 195 | 8 | 0.72 |
| Vq | ng/ml | 2.0E2 | 1.0E3 | 3.4E3 | 2.0E3 | 4.2E4 | 2.6E3 | 2.0E-1 | 1.0E1 | 6.8E5 | 7.1E3 | 255 | 8 | 158 | 8 | 0.71 |
| Vo | ng/ml | 2.5E1 | 2.6E1 | 2.4E1 | 2.4E1 | 5.2E0 | 6.0E0 | 2.4E0 | 1.1E1 | 4.8E1 | 3.1E1 | 340 | 10 | 195 | 10 | 0.50 |
| Vs | ng/ml | 1.0E-9 | 1.4E0 | 6.1E0 | 5.9E1 | 2.2E1 | 1.6E2 | 1.0E-9 | 1.0E-9 | 2.3E2 | 4.5E2 | 325 | 8 | 190 | 8 | 0.60 |
| Vv | ng/ml | 3.0E0 | 2.6E0 | 5.9E0 | 6.7E0 | 9.5E0 | 8.0E0 | 1.0E-9 | 1.0E-9 | 8.4E1 | 2.1E1 | 339 | 9 | 195 | 9 | 0.53 |
| Vw | ng/ml | 3.6E1 | 4.6E1 | 3.5E1 | 4.8E1 | 1.7E1 | 1.3E1 | 2.5E0 | 3.0E1 | 7.0E1 | 6.6E1 | 122 | 7 | 96 | 7 | 0.73 |
| Oy | pg/ml | 4.9E-1 | 3.7E-1 | 5.7E0 | 3.5E0 | 2.8E1 | 8.6E0 | 1.0E-9 | 1.0E-9 | 4.0E2 | 3.3E1 | 937 | 16 | 344 | 16 | 0.45 |
| Oz | pg/ml | 1.2E-2 | 1.0E-9 | 3.2E-1 | 1.8E0 | 1.3E0 | 7.0E0 | 1.0E-9 | 1.0E-9 | 2.9E1 | 2.8E1 | 937 | 16 | 344 | 16 | 0.40 |
| Pa | pg/ml | 3.9E-1 | 4.2E-1 | 1.4E0 | 1.6E1 | 4.9E0 | 5.6E1 | 1.0E-9 | 1.0E-9 | 8.6E1 | 2.3E2 | 937 | 16 | 344 | 16 | 0.55 |
| Pb | pg/ml | 1.0E-9 | 1.0E-9 | 7.4E-1 | 2.1E0 | 1.6E1 | 7.9E0 | 1.0E-9 | 1.0E-9 | 4.9E2 | 3.2E1 | 937 | 16 | 344 | 16 | 0.42 |
| Pc | pg/ml | 5.4E-2 | 1.0E-9 | 3.5E-1 | 2.9E0 | 8.4E-1 | 9.3E0 | 1.0E-9 | 1.0E-9 | 1.6E1 | 3.8E1 | 937 | 16 | 344 | 16 | 0.47 |
| Pd | pg/ml | 1.8E0 | 4.8E0 | 4.8E0 | 1.6E1 | 2.8E1 | 3.0E1 | 1.0E-9 | 7.3E-2 | 8.4E2 | 1.2E2 | 937 | 16 | 344 | 16 | 0.66 |
| Pe | pg/ml | 2.2E1 | 1.1E2 | 1.0E2 | 1.6E3 | 3.4E2 | 3.9E3 | 1.0E-9 | 2.0E1 | 4.7E3 | 1.5E4 | 937 | 16 | 344 | 16 | 0.78 |
| Pf | pg/ml | 1.6E0 | 1.6E1 | 1.0E1 | 5.8E1 | 5.7E1 | 1.1E2 | 1.0E-9 | 3.3E-1 | 1.5E3 | 4.3E2 | 937 | 16 | 344 | 16 | 0.79 |
| Pg | pg/ml | 3.5E0 | 1.6E1 | 4.1E1 | 1.7E2 | 3.3E2 | 3.5E2 | 1.0E-9 | 4.6E-1 | 7.7E3 | 1.2E3 | 937 | 16 | 344 | 16 | 0.71 |
| Ph | ng/ml | 1.8E-1 | 2.4E-1 | 3.5E-1 | 8.1E-1 | 5.5E-1 | 1.6E0 | 1.0E-9 | 3.5E-3 | 4.4E0 | 5.4E0 | 334 | 10 | 191 | 10 | 0.58 |
| Pi | ng/ml | 2.0E-1 | 4.3E-1 | 2.9E-1 | 8.5E-1 | 4.2E-1 | 2.6E1 | 1.0E-9 | 1.0E-9 | 4.8E0 | 8.2E1 | 334 | 10 | 191 | 10 | 0.72 |
| Pj | ng/mL | 5.4E0 | 7.1E0 | 6.2E0 | 6.9E0 | 5.2E0 | 4.6E0 | 3.8E-2 | 1.4E0 | 5.5E1 | 1.7E1 | 334 | 10 | 191 | 10 | 0.56 |
| Pk | ng/ml | 8.9E-3 | 2.2E-2 | 1.3E-2 | 1.7E-1 | 2.0E-2 | 4.8E-1 | 1.0E-9 | 1.1E-3 | 2.5E-1 | 1.5E0 | 334 | 10 | 191 | 10 | 0.68 |
| aA | mg/dL | 8.1E-1 | 1.6E0 | 9.5E-1 | 2.1E0 | 4.9E-1 | 1.3E0 | 2.0E-1 | 5.5E-1 | 4.2E0 | 4.7E0 | 2722 | 21 | 517 | 21 | 0.80 |
| aC | mg/mL | 2.8E0 | 2.0E0 | 3.1E0 | 2.6E0 | 1.4E0 | 1.5E0 | 7.7E-1 | 7.4E-1 | 8.9E0 | 5.5E0 | 551 | 11 | 213 | 11 | 0.38 |
| aD | ug/mL | 3.1E0 | 6.0E0 | 4.4E0 | 7.7E0 | 3.9E0 | 6.6E0 | 4.3E-1 | 1.1E0 | 3.5E1 | 2.1E1 | 551 | 11 | 213 | 11 | 0.62 |
| aE | mg/mL | 5.6E-1 | 5.8E-1 | 5.7E-1 | 6.3E-1 | 1.5E-1 | 2.5E-1 | 1.8E-1 | 3.9E-1 | 1.1E0 | 1.2E0 | 551 | 11 | 213 | 11 | 0.54 |
| aF | ng/mL | 2.2E0 | 1.6E0 | 4.0E0 | 5.0E0 | 5.7E0 | 5.0E0 | 4.3E-3 | 5.2E-1 | 5.0E1 | 1.3E1 | 551 | 11 | 213 | 11 | 0.52 |
| aG | mg/mL | 1.4E-1 | 9.4E-2 | 1.6E-1 | 1.5E-1 | 8.7E-2 | 1.1E-1 | 1.7E-2 | 7.0E-2 | 5.4E-1 | 4.2E-1 | 551 | 11 | 213 | 11 | 0.44 |
| aH | ug/mL | 7.5E1 | 6.3E1 | 8.2E1 | 7.0E1 | 4.4E1 | 4.3E1 | 4.6E0 | 1.1E1 | 2.9E2 | 1.5E2 | 551 | 11 | 213 | 11 | 0.42 |
| aI | ug/mL | 1.9E2 | 1.6E2 | 1.9E2 | 1.5E2 | 6.0E1 | 5.5E1 | 2.8E1 | 7.5E1 | 3.7E2 | 2.4E2 | 551 | 11 | 213 | 11 | 0.34 |
| aJ | ug/mL | 2.5E0 | 5.6E0 | 3.1E0 | 7.5E0 | 2.2E0 | 6.1E0 | 7.3E-1 | 1.5E0 | 1.7E1 | 2.3E1 | 551 | 11 | 213 | 11 | 0.78 |
| aK | ng/mL | 1.5E0 | 1.4E0 | 2.4E0 | 2.0E0 | 2.6E0 | 1.9E0 | 2.9E-4 | 1.3E-1 | 1.8E1 | 5.5E0 | 551 | 11 | 213 | 11 | 0.48 |
| aL | mg/mL | 8.0E-1 | 8.0E-1 | 8.1E-1 | 7.5E-1 | 2.6E-1 | 2.5E-1 | 1.9E-1 | 2.7E-1 | 1.7E0 | 1.0E0 | 551 | 11 | 213 | 11 | 0.46 |
| aM | U/mL | 2.2E1 | 5.3E1 | 4.6E1 | 1.2E2 | 9.3E1 | 2.3E2 | 4.2E-2 | 5.2E0 | 1.6E3 | 8.2E2 | 551 | 11 | 213 | 11 | 0.69 |
| aN | U/mL | 1.4E1 | 2.6E1 | 2.2E1 | 3.3E1 | 3.0E1 | 3.2E1 | 2.5E-3 | 1.9E0 | 3.8E2 | 1.1E2 | 551 | 11 | 213 | 11 | 0.62 |

Figure 7 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aO | pg/mL | 3.3E1 | 2.4E2 | 3.0E2 | 6.4E2 | 7.7E2 | 8.7E2 | 6.0E-2 | 2.1E0 | 6.6E3 | 2.4E3 | 551 | 11 | 213 | 11 | 0.69 |
| aP | ng/mL | 1.7E0 | 3.2E0 | 2.1E0 | 5.6E0 | 1.8E0 | 7.6E0 | 4.5E-1 | 1.4E0 | 2.8E1 | 2.8E1 | 551 | 11 | 213 | 11 | 0.78 |
| aQ | ng/mL | 3.0E-1 | 4.4E-1 | 4.5E-1 | 3.6E-1 | 4.5E-1 | 1.8E-1 | 2.0E-4 | 5.1E-2 | 4.0E0 | 6.2E-1 | 551 | 11 | 213 | 11 | 0.51 |
| aR | ng/mL | 1.8E0 | 3.1E0 | 2.8E0 | 3.0E0 | 3.3E0 | 1.9E0 | 1.8E-1 | 2.5E-1 | 3.4E1 | 5.9E0 | 551 | 11 | 213 | 11 | 0.59 |
| aS | ng/mL | 2.7E-1 | 4.0E-1 | 6.3E-1 | 9.6E-1 | 1.7E0 | 1.0E0 | 4.2E-3 | 8.5E-2 | 3.3E1 | 2.8E0 | 551 | 11 | 213 | 11 | 0.58 |
| aU | pg/mL | 7.5E1 | 6.8E1 | 1.2E2 | 8.8E1 | 1.5E2 | 7.8E1 | 7.4E-2 | 9.6E0 | 1.3E3 | 2.3E2 | 551 | 11 | 213 | 11 | 0.44 |
| aV | ng/mL | 6.2E-1 | 4.2E-1 | 1.0E0 | 1.1E0 | 1.8E0 | 1.5E0 | 7.6E-4 | 1.0E-1 | 3.3E1 | 5.4E0 | 551 | 11 | 213 | 11 | 0.49 |
| aW | pg/mL | 1.8E1 | 2.1E1 | 1.9E1 | 5.5E1 | 1.8E1 | 1.2E2 | 7.2E-2 | 7.7E0 | 2.4E2 | 4.2E2 | 551 | 11 | 213 | 11 | 0.57 |
| aX | ng/mL | 9.5E0 | 1.4E1 | 1.6E1 | 3.7E1 | 2.6E1 | 5.7E1 | 3.0E-1 | 2.6E0 | 3.1E2 | 1.7E2 | 551 | 11 | 213 | 11 | 0.59 |
| aY | pg/mL | 5.7E1 | 9.2E1 | 7.5E1 | 1.1E2 | 8.2E1 | 6.7E1 | 4.1E-1 | 1.2E1 | 1.2E3 | 2.0E2 | 551 | 11 | 213 | 11 | 0.70 |
| aZ | pg/mL | 2.2E2 | 4.2E2 | 5.4E2 | 4.5E2 | 1.1E3 | 3.0E2 | 1.7E0 | 8.2E1 | 1.2E4 | 1.3E3 | 551 | 11 | 213 | 11 | 0.64 |
| bA | ng/mL | 9.0E0 | 1.6E2 | 3.5E1 | 4.0E2 | 9.2E1 | 5.5E2 | 3.0E-2 | 2.0E0 | 9.7E2 | 1.5E3 | 551 | 11 | 213 | 11 | 0.84 |
| bB | ng/mL | 3.0E2 | 1.9E2 | 3.2E2 | 2.2E2 | 1.7E2 | 1.4E2 | 2.1E0 | 3.3E1 | 1.0E3 | 4.2E2 | 551 | 11 | 213 | 11 | 0.33 |
| bC | ng/mL | 3.4E2 | 4.3E2 | 6.0E2 | 1.2E3 | 7.9E2 | 1.4E3 | 9.8E0 | 1.4E2 | 4.7E3 | 4.7E3 | 551 | 11 | 213 | 11 | 0.65 |
| bE | mg/mL | 5.5E0 | 5.9E0 | 5.8E0 | 6.7E0 | 2.1E0 | 3.2E0 | 9.8E-1 | 1.3E0 | 1.3E1 | 1.2E1 | 551 | 11 | 213 | 11 | 0.58 |
| bF | pg/mL | 2.0E1 | 5.7E1 | 1.5E2 | 7.9E2 | 8.8E2 | 1.9E3 | 5.0E-2 | 1.5E1 | 1.1E4 | 6.3E3 | 551 | 11 | 213 | 11 | 0.74 |
| bG | ng/mL | 1.6E0 | 1.7E0 | 2.7E0 | 4.6E0 | 3.2E0 | 8.4E0 | 2.2E-2 | 5.8E-1 | 2.6E1 | 3.0E1 | 551 | 11 | 213 | 11 | 0.56 |
| bH | pg/mL | 5.7E-1 | 9.2E0 | 4.7E0 | 8.8E0 | 1.4E1 | 7.9E0 | 5.7E-1 | 5.7E-1 | 2.8E2 | 2.2E1 | 551 | 11 | 213 | 11 | 0.70 |
| bI | ng/mL | 4.0E-3 | 4.0E-3 | 6.0E-2 | 1.6E-1 | 1.5E-1 | 2.9E-1 | 4.0E-3 | 4.0E-3 | 1.3E0 | 8.8E-1 | 551 | 11 | 213 | 11 | 0.60 |
| bJ | mg/mL | 2.3E0 | 2.4E0 | 2.6E0 | 3.1E0 | 2.0E0 | 2.1E0 | 2.5E-4 | 2.5E-4 | 1.3E1 | 7.0E0 | 551 | 11 | 213 | 11 | 0.57 |
| bL | ng/mL | 3.8E0 | 3.2E0 | 8.5E0 | 9.0E0 | 1.1E1 | 1.0E1 | 4.6E-2 | 1.1E0 | 8.0E1 | 3.2E1 | 551 | 11 | 213 | 11 | 0.54 |
| bM | mg/mL | 1.7E0 | 2.3E0 | 2.1E0 | 3.3E0 | 1.4E0 | 2.3E0 | 9.2E-2 | 1.8E-2 | 8.9E0 | 8.4E0 | 551 | 11 | 213 | 11 | 0.68 |
| bN | ng/mL | 4.2E1 | 3.1E1 | 1.3E2 | 1.0E2 | 2.7E2 | 1.5E2 | 1.4E-1 | 1.4E0 | 1.9E3 | 4.8E2 | 551 | 11 | 213 | 11 | 0.45 |
| bO | ng/mL | 4.0E-2 | 4.0E-2 | 1.0E1 | 1.5E1 | 2.3E1 | 2.5E1 | 4.0E-2 | 4.0E-2 | 2.0E2 | 6.1E1 | 551 | 11 | 213 | 11 | 0.52 |
| bP | mg/mL | 5.3E-1 | 9.0E-1 | 7.6E-1 | 1.1E0 | 6.9E-1 | 9.0E-1 | 4.9E-2 | 2.9E-1 | 4.8E0 | 3.5E0 | 551 | 11 | 213 | 11 | 0.66 |
| bQ | pg/mL | 1.6E1 | 6.2E1 | 5.8E1 | 8.4E1 | 5.8E2 | 6.8E1 | 1.5E-1 | 1.2E1 | 1.3E4 | 2.2E2 | 551 | 11 | 213 | 11 | 0.84 |
| bR | ng/mL | 1.2E-2 | 1.2E-2 | 1.3E-1 | 4.5E-2 | 4.2E-1 | 8.2E-2 | 1.2E-2 | 1.2E-2 | 8.7E0 | 2.8E-1 | 551 | 11 | 213 | 11 | 0.38 |
| bS | pg/mL | 9.4E-1 | 9.4E-1 | 7.0E0 | 6.9E0 | 2.6E1 | 2.0E1 | 9.4E-1 | 9.4E-1 | 3.9E2 | 6.7E1 | 551 | 11 | 213 | 11 | 0.48 |
| bU | ng/mL | 1.2E-1 | 1.3E-2 | 1.9E-1 | 1.2E-1 | 3.5E-1 | 1.5E-1 | 1.3E-2 | 1.3E-2 | 6.6E0 | 4.1E-1 | 551 | 11 | 213 | 11 | 0.41 |
| bV | pg/mL | 4.7E2 | 1.1E3 | 5.9E2 | 1.0E3 | 8.9E2 | 4.7E2 | 1.5E2 | 3.6E2 | 1.7E4 | 2.0E3 | 551 | 11 | 213 | 11 | 0.82 |
| bW | pg/mL | 3.3E2 | 4.9E2 | 5.1E2 | 3.0E3 | 5.5E2 | 7.4E3 | 8.4E1 | 1.5E2 | 6.4E3 | 2.5E4 | 551 | 11 | 213 | 11 | 0.62 |
| bX | ng/mL | 2.5E-5 | 2.5E-5 | 2.7E-3 | 2.0E-3 | 3.4E-3 | 2.5E-3 | 2.5E-5 | 2.5E-5 | 2.0E-2 | 7.1E-3 | 551 | 11 | 213 | 11 | 0.45 |
| bZ | pg/mL | 2.5E2 | 8.9E2 | 8.5E2 | 5.2E3 | 3.7E3 | 1.2E4 | 1.5E-1 | 1.9E2 | 5.8E4 | 4.3E4 | 551 | 11 | 213 | 11 | 0.77 |
| cA | pg/mL | 6.0E-1 | 6.0E-1 | 2.7E0 | 6.0E-1 | 1.6E1 | 0.0E0 | 6.0E-1 | 6.0E-1 | 3.7E2 | 6.0E-1 | 551 | 11 | 213 | 11 | 0.43 |
| cB | ng/mL | 5.5E-2 | 6.4E-2 | 8.7E-2 | 6.6E-2 | 1.0E-1 | 6.7E-2 | 1.7E-3 | 1.7E-3 | 5.7E-1 | 2.1E-1 | 551 | 11 | 213 | 11 | 0.46 |
| cC | pg/mL | 4.6E1 | 5.4E1 | 4.7E1 | 4.6E1 | 3.9E1 | 2.5E1 | 1.0E0 | 1.0E0 | 4.5E2 | 7.3E1 | 551 | 11 | 213 | 11 | 0.54 |
| cD | pg/mL | 5.2E0 | 8.5E0 | 1.5E1 | 1.2E1 | 5.2E1 | 1.6E1 | 3.3E-1 | 3.3E-1 | 7.2E2 | 4.9E1 | 551 | 11 | 213 | 11 | 0.53 |
| cE | pg/mL | 3.9E1 | 2.4E2 | 1.5E2 | 3.8E2 | 4.3E2 | 4.6E2 | 1.2E-1 | 1.2E1 | 3.8E3 | 1.3E3 | 551 | 11 | 213 | 11 | 0.74 |
| cF | pg/mL | 1.3E1 | 5.3E-1 | 2.0E1 | 1.0E1 | 3.0E1 | 1.5E1 | 5.3E-1 | 5.3E-1 | 2.7E2 | 3.8E1 | 551 | 11 | 213 | 11 | 0.39 |
| cG | pg/mL | 4.6E1 | 1.2E2 | 1.1E2 | 1.9E2 | 4.7E2 | 1.7E2 | 6.4E0 | 3.5E1 | 1.0E4 | 4.9E2 | 551 | 11 | 213 | 11 | 0.74 |
| cH | uIU/mL | 2.8E0 | 1.4E0 | 6.0E0 | 1.1E1 | 1.1E1 | 1.8E1 | 8.6E-3 | 8.6E-3 | 1.6E2 | 5.3E1 | 551 | 11 | 213 | 11 | 0.45 |
| cI | ng/mL | 5.7E0 | 9.6E0 | 1.2E1 | 1.9E1 | 1.7E1 | 3.3E1 | 1.0E-3 | 1.2E0 | 1.2E2 | 1.2E2 | 551 | 11 | 213 | 11 | 0.56 |
| cJ | ug/mL | 6.2E1 | 5.0E1 | 1.1E2 | 6.5E1 | 1.4E2 | 5.9E1 | 4.0E0 | 5.6E0 | 9.6E2 | 1.9E2 | 551 | 11 | 213 | 11 | 0.41 |
| cK | ng/mL | 3.8E-3 | 3.8E-3 | 4.7E-2 | 2.5E-2 | 1.7E-1 | 3.1E-2 | 3.8E-3 | 3.8E-3 | 1.7E0 | 8.2E-2 | 551 | 11 | 213 | 11 | 0.59 |
| cL | pg/mL | 2.0E2 | 2.4E2 | 3.9E2 | 3.7E2 | 1.3E3 | 3.6E2 | 1.6E1 | 1.4E2 | 2.4E4 | 1.4E3 | 551 | 11 | 213 | 11 | 0.61 |
| cM | pg/mL | 2.7E2 | 2.3E2 | 2.9E2 | 2.4E2 | 1.9E2 | 1.3E2 | 8.7E0 | 5.7E1 | 1.6E3 | 4.7E2 | 551 | 11 | 213 | 11 | 0.42 |
| cN | pg/mL | 1.2E2 | 1.8E2 | 1.3E2 | 1.8E2 | 6.2E1 | 7.5E1 | 3.8E1 | 8.6E1 | 1.1E3 | 2.9E2 | 551 | 11 | 213 | 11 | 0.70 |
| cO | pg/mL | 2.2E2 | 3.1E2 | 3.0E2 | 3.1E2 | 8.3E2 | 9.0E1 | 5.4E1 | 1.6E2 | 1.9E4 | 4.4E2 | 551 | 11 | 213 | 11 | 0.70 |
| cP | pg/mL | 2.5E3 | 3.4E3 | 2.6E3 | 3.3E3 | 9.0E2 | 1.1E3 | 6.2E2 | 2.0E3 | 5.7E3 | 5.0E3 | 551 | 11 | 213 | 11 | 0.69 |
| cQ | ng/mL | 5.1E-2 | 6.7E-2 | 1.4E-1 | 2.0E-1 | 2.8E-1 | 3.0E-1 | 2.0E-3 | 2.0E-3 | 2.2E0 | 8.7E-1 | 551 | 11 | 213 | 11 | 0.58 |
| cR | ng/mL | 3.0E2 | 5.0E2 | 5.2E2 | 4.5E2 | 8.3E2 | 1.9E2 | 2.0E1 | 1.4E2 | 8.9E3 | 6.9E2 | 551 | 11 | 213 | 11 | 0.61 |
| cS | ng/mL | 2.6E2 | 7.2E2 | 4.4E2 | 1.3E3 | 1.0E3 | 2.0E3 | 4.1E1 | 1.6E2 | 2.2E4 | 7.1E3 | 551 | 11 | 213 | 11 | 0.77 |
| cT | ng/mL | 3.3E1 | 1.7E2 | 8.8E1 | 6.0E2 | 2.0E2 | 7.2E2 | 3.6E0 | 1.1E1 | 2.1E3 | 1.9E3 | 551 | 11 | 213 | 11 | 0.79 |
| cU | ng/mL | 5.4E1 | 8.8E1 | 7.7E1 | 1.1E2 | 9.6E1 | 6.7E1 | 5.4E0 | 4.0E1 | 1.6E3 | 2.3E2 | 551 | 11 | 213 | 11 | 0.71 |
| cV | ng/mL | 1.8E-1 | 2.8E-1 | 4.0E-1 | 5.3E-1 | 2.1E0 | 7.0E-1 | 3.4E-4 | 7.6E-2 | 4.7E1 | 2.5E0 | 551 | 11 | 213 | 11 | 0.67 |
| cW | mIU/mL | 5.2E-2 | 9.9E-2 | 1.3E-1 | 1.4E-1 | 6.5E-1 | 1.2E-1 | 3.7E-4 | 3.6E-2 | 9.7E0 | 3.9E-1 | 551 | 11 | 213 | 11 | 0.72 |
| cX | ng/mL | 1.1E-1 | 1.2E-1 | 1.3E0 | 4.2E-1 | 4.3E0 | 7.4E-1 | 2.3E-4 | 2.3E-4 | 2.8E1 | 2.5E0 | 551 | 11 | 213 | 11 | 0.47 |

Figure 7 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cY | ng/mL | 8.6E0 | 6.9E0 | 1.2E1 | 9.2E0 | 1.3E1 | 8.1E0 | 1.5E-1 | 9.3E-1 | 8.3E1 | 2.7E1 | 551 | 11 | 213 | 11 | 0.43 |
| cZ | ug/mL | 1.4E1 | 1.6E1 | 1.6E1 | 1.6E1 | 7.1E0 | 6.6E0 | 2.3E0 | 3.3E0 | 5.7E1 | 2.6E1 | 551 | 11 | 213 | 11 | 0.55 |
| dA | pg/mL | 3.3E2 | 5.4E2 | 3.7E2 | 5.5E2 | 2.8E2 | 2.6E2 | 9.0E1 | 1.7E2 | 5.8E3 | 1.1E3 | 551 | 11 | 213 | 11 | 0.73 |
| dB | ug/mL | 1.7E1 | 2.2E1 | 1.7E1 | 1.9E1 | 1.5E1 | 8.2E0 | 9.4E-1 | 3.7E0 | 2.5E2 | 2.7E1 | 551 | 11 | 213 | 11 | 0.64 |
| dC | nmol/L | 3.5E1 | 3.6E1 | 3.8E1 | 4.0E1 | 1.8E1 | 1.7E1 | 7.6E0 | 2.1E1 | 1.4E2 | 7.9E1 | 551 | 11 | 213 | 11 | 0.52 |
| dD | ug/mL | 3.6E1 | 3.0E1 | 3.7E1 | 3.6E1 | 1.1E1 | 1.5E1 | 1.3E1 | 2.1E1 | 7.6E1 | 6.4E1 | 551 | 11 | 213 | 11 | 0.43 |
| dE | ng/mL | 4.7E-1 | 7.0E-1 | 6.0E-1 | 8.9E-1 | 6.9E-1 | 8.6E-1 | 8.4E-3 | 8.4E-3 | 7.2E0 | 2.4E0 | 551 | 11 | 213 | 11 | 0.61 |
| dF | ng/mL | 2.3E2 | 6.7E2 | 2.8E2 | 5.7E2 | 1.9E2 | 3.3E2 | 5.6E1 | 2.0E2 | 1.3E3 | 1.2E3 | 551 | 11 | 213 | 11 | 0.79 |
| dG | ng/mL | 1.2E1 | 2.4E1 | 1.5E1 | 3.3E1 | 1.3E1 | 2.7E1 | 2.2E0 | 9.8E0 | 1.8E2 | 8.7E1 | 551 | 11 | 213 | 11 | 0.77 |
| dH | pg/mL | 7.9E0 | 1.4E1 | 1.3E1 | 1.8E1 | 3.6E1 | 2.1E1 | 4.0E-2 | 3.2E0 | 6.7E2 | 7.6E1 | 551 | 11 | 213 | 11 | 0.64 |
| dI | pg/mL | 4.6E-1 | 5.0E0 | 2.2E0 | 5.0E0 | 1.5E1 | 5.3E0 | 4.6E-1 | 4.6E-1 | 3.3E2 | 1.9E1 | 551 | 11 | 213 | 11 | 0.75 |
| dJ | ng/mL | 1.9E0 | 2.7E0 | 2.2E0 | 2.4E0 | 1.2E0 | 1.1E0 | 3.2E-2 | 4.9E-1 | 6.9E0 | 3.7E0 | 551 | 11 | 213 | 11 | 0.59 |
| dK | uIU/mL | 1.9E0 | 1.2E0 | 3.0E0 | 3.3E0 | 6.0E0 | 6.3E0 | 2.8E-4 | 1.4E-2 | 7.9E1 | 2.2E1 | 551 | 11 | 213 | 11 | 0.42 |
| dL | ng/mL | 8.8E2 | 1.3E3 | 1.0E3 | 1.7E3 | 5.2E2 | 1.3E3 | 2.6E2 | 5.3E2 | 3.8E3 | 4.8E3 | 551 | 11 | 213 | 11 | 0.62 |
| dM | pg/mL | 9.7E2 | 2.5E3 | 1.2E3 | 3.2E3 | 1.3E3 | 2.7E3 | 3.4E2 | 7.1E2 | 1.6E4 | 9.6E3 | 551 | 11 | 213 | 11 | 0.78 |
| dN | ug/mL | 9.3E1 | 1.7E2 | 9.9E1 | 1.7E2 | 3.7E1 | 7.0E1 | 1.6E1 | 9.4E1 | 2.8E2 | 3.3E2 | 551 | 11 | 213 | 11 | 0.86 |
| dR | pg/ml | 1.6E3 | 9.9E2 | 2.3E3 | 1.4E3 | 2.3E3 | 1.2E3 | 1.4E2 | 4.0E2 | 1.5E4 | 4.1E3 | 378 | 8 | 202 | 8 | 0.38 |
| eF | ng/ml | 4.1E0 | 8.9E0 | 5.0E0 | 1.1E1 | 4.3E0 | 8.2E0 | 1.2E0 | 3.4E0 | 4.6E1 | 2.9E1 | 393 | 8 | 203 | 8 | 0.83 |
| eC | pg/ml | 3.0E2 | 1.9E2 | 3.7E2 | 4.3E2 | 2.6E2 | 7.1E2 | 9.9E0 | 7.1E1 | 1.6E3 | 2.0E3 | 304 | 7 | 190 | 7 | 0.27 |
| fP | ng/ml | 2.6E2 | 4.0E2 | 2.9E2 | 3.2E2 | 1.9E2 | 1.4E2 | 1.8E0 | 9.5E1 | 1.6E3 | 4.4E2 | 358 | 8 | 193 | 8 | 0.58 |
| fR | ng/ml | 1.4E5 | 3.6E5 | 1.9E5 | 3.8E5 | 1.5E5 | 2.8E5 | 2.9E4 | 1.9E2 | 8.3E5 | 8.7E5 | 363 | 10 | 111 | 10 | 0.72 |
| gL | pg/ml | 6.4E4 | 1.0E5 | 7.1E4 | 1.2E5 | 3.2E4 | 6.1E4 | 1.1E4 | 4.5E4 | 3.2E5 | 2.2E5 | 378 | 8 | 202 | 8 | 0.77 |
| gP | U/ml | 2.7E2 | 2.7E2 | 2.8E2 | 3.0E2 | 1.1E2 | 8.8E1 | 1.2E1 | 1.9E2 | 1.1E3 | 4.4E2 | 389 | 8 | 203 | 8 | 0.57 |
| iF | pg/mL | 1.4E3 | 2.1E3 | 1.3E4 | 2.0E3 | 4.0E4 | 1.3E3 | 1.2E1 | 2.6E2 | 3.2E5 | 3.7E3 | 305 | 7 | 190 | 7 | 0.52 |

Analyte panel data:

Unconstrained panels with 3 analytes, where 1.0E-10 >= 'model p-value' > 0. Contains 5,249 panels of 11,919,473 total panels evaluated. :
aA{Lv(Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Po(Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Et(Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Fp(Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Fr(Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Ma(Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Mu(Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Mb Mc Md Me Mf Mg Mh Mi Mj Mk Ml Mm Mn Mp Mq Mr Ms Mt Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Ni(Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Mb Mc Md Me Mf Mg Mh Mi Mj Mk Ml Mm Mn Mp Mq Mr Ms Mt Mv Mw Mx My Mz Na Nb Nc Nd Ne Nf Ng Nh Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Ji(Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lw Lx Ly Lz Mb Mc Md Me Mf Mg Mh Mi Mj Mk Ml Mm Mn Mp Mq Mr Ms Mt Mv Mw Mx My Mz Na Nb Nc Nd Ne Nf Ng Nh Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Jl(Hq Hr Hu Hv Hw Hx Ih Ii Ij Ik Il Im In Io Ip Iq Ir Is It Iu Iv Jg Jh Jj Jk Jm Jn Jo Jp Jq Jr Js Jt Lh Li Lj Lu Lw Lx Ly Lz Mb Mc Md Me Mf Mg Mh Mi Mj Mk Ml Mm Mn Mp Mq Mr Ms Mt Mv Mw Mx My Mz Na Nb Nc Nd Ne Nf Ng Nh Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Pf(Hq Hr Hu Hv Hw Hx Ih Ii Ij Ik Il Im In Io Ip Iq Ir Is It Iu Iv Jg Jh Jj Jk Jm Jn Jo Jp Jq Jr Js Jt Lh Li Lj Lu Lw Lx Ly Lz Mb Mc Md Me Mf Mg Mh Mi Mj Mk Ml Mm Mn Mp Mq Mr Ms Mt Mv Mw Mx My Mz Na Nb Nc Nd Ne Nf Ng Nh Nj Nk Nl Nm Nn No Nq Nr Ns Nt Nu Nv Nw Nx Ny Oe Of Og Oh Oi Ok Om On Oy Oz Pa Pb Pc Pd Pe Pg Pz Qa Qb Qc Qd Qe) No(Hq Hr Hu Hv Hw Hx Ih Ii Ij Ik Il Im In Io Ip Iq Ir Is It Iu Jg Jh Jj Jk Jm Jn Jo Jp Jq Jr Js Jt Lh Li Lj Lu Lw Lx Ly Lz Mb Mc Md Me Mf Mg Mh Mi Mj Mk Ml Mm Mn Mp Mq Mr Ms Mt Mv Mw Mx My Mz Na Nb Nc Nd Ne Nf Ng Nh Nj Nk Nl Nm Nn Nq Nr Ns Nt Nu Nv Nw Nx Ny Oe Of Og Oh Oi Ok Om On Oy Oz Pa Pb Pc Pd Pe Pg Pz Qa Qb Qc Qd Qe) Qe(Hr Hu Hv Hw Hx Ih Ii Ij Ik Il Im In Io Iq Ir Is It Iu Jg Jh Jj Jm Jn Jo Jq Jr Jt Lh Lu Lw Lx Ly

Om Pd Pe Pf Pg Po Qa Qd Qe) Om(Fp Is Jk Jr Lh Lu Lv Lx Ma Mq Mr Mv Mw Ni Nn No Nt Og Pf Po Qa Qe) Nn(Et Is Lu Lv Me Mq Ni Ok) Ni(Is Jk No Nw Po Qa Qe) Mq(No Nw Ok) Lu(Et Ok) PoJj NoLv} Ni{Dr(aY Ba Bg bQ bZ cG Cu Dk Et Ez Fr Fy Gp Hu Im In Is Iz Jd Jg Jk Jn Jr Kq Lh Lv Ma Mg Mn Mt Mu Mv Mw My Nk Nn Nq On Op Ou Pg Po Qa Qe Qy Rz Tn Tv Ua Ut Yd Xa Th) Fr(Et Fp Hu Ih Im Is Jj Jn Jq Jr Lj Lv Me Mm Mq Ms Mu My Ne Nk Nl Nn No Nw Of Og Oh Oi Ok On Oy Pb Po Qa Qb Qe) On(Fp Hu Ii Im In Is Jh Jj Jn Jo Jr Lj Lv Ly Me Mg Ms Mu Mw My Nb Nn No Ns Nx Of Og Oh Oi Oy Pb Pf Po Qa Qe) Mu(Et Im Is Jj Jn Jq Jr Lj Lv Me Mm Mn Ms No Nw Og Oh Ok Pf Po Qa Qe) Nn(Et Im In Is Jj Jn Jq Jr Lv Me Mq Ms Ne No Nw Og Oi Ok Pb Qa Qe) No(Et Im In Is Jj Jq Jr Lv Me Mm Mq Ms Nw Og Oi Pb Pc Qa Qe) Is(Et In Jj Jr Lv Lx Mm Ms Nw Og Oi Pe Pf Po To Vz Wf) Qe(Du Et Jj Jq Jr Lv Lx Nw Og Oi Pc Rv Ux Yl Ti Th) Po(Et Im In Jj Jo Jq Jr Lv Ms Nw Og Oi Oy Pb Pc) Nw(Im Jj Jr Lv Ly Ma Ms My Og Oh Pb Pc Pf Qa) Qa(Et In Jj Jq Jr Lv Og Oi Pc Rv Yl) Yl(aC bN cP Jr Nr Oa Oh Pe Qb) Xa(Af cX Dp In Jm Qb Uu) Jj(Fp Jk Jn Jr Oh Pf) Rv(Et Jm Mw Nr Ny) Vz(Fy Jm Jr Rm) Im(Jr Lv Pf) Et(Jr Oh) Qb(Vi Wc) bN(Ps Zq) LvPf MmJr HlRi WfJm} On{Oy(Et Fp Fr Hq Hr Hu Hv Hw Hx Ih Ii Ij Ik Il Im In Io Ip Iq Ir Is It Iu Iv Jg Jh Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nj Nk Nl Nm Nn No Nq Nr Ns Nt Nu Nv Nw Nx Ny Oe Of Og Oh Oi Ok Om Oz Pa Pb Pc Pd Pe Pf Pg Po Pz Qa Qb Qc Qd Qe) My(Et Fp Fr Hu Im In Io Is Jg Jh Jj Jn Jq Jr Jt Lu Lv Ly Ma Mb Me Mf Mi Mq Mr Ms Mu Mv Mw Nc Nd Nf Nh Nk Nl Nn No Nq Ns Nw Oe Og Oi Om Oz Pa Pb Pc Pf Po Qa Qe) Ms(Et Fp Fr Hu Im In Is Jj Jn Jq Jr Lv Lw Ly Me Mq Mu Mw Nn No Nw Og Oh Oi Pb Pc Po Qa Qe) Og(Fp Hq Hu Im In Is Jn Jq Jr Lj Lv Lw Ly Ma Me Mq Mu Nf Nn No Nv Of Oh Pc Po Qa Qe) Jj(Fp Jr Lv Me Mq Mu Nf Po Qa Qe) Mu(Hu Jk Lv Mv Mw Oe Of Oi) Hu(Fp In Lv Ma Me Mq Oi) Of(Hw Jq Lv Me Qa) Oi(Fp Jr No Qa) In(Fp Me Qa) NoLv Meli QaOe} Mu{Dr(Af Aj aW bJ BN bU Cx cZ dA dE dN Fi Fn Hb Hu Ik Jd Kc Kg Ki Kj Ky Kz Lv Mr Mt Mw Mz Nc Nd Nf Nk Nu Nx Oe Of Og Oy Oz Pb Pg Qc Ri Sf To Ua Uk Uo Up Ur Us Uu We Yd Ye Tl) Lv(Et Fp Fr Hu Ih Im In Io Is Jj Jn Jo Jq Jr Lj Lu Lw Ly Me Mg Mm Mq Mr Ms Mt My Mz No Ns Nw Oe Of Og Oh Oi Ok Oy Oz Pa Pb Pe Pf Po Qa Qe) Jj(Et Fp Fr Hw Im Is Jm Jn Jo Jq Jr Jt Lh Lw Me Ma Me Mh Mi Ml Mq Mr Ms Mz Nf Nh Nn No Nt Nw Og Oh Oi Ok Om Pd Pe Pf Po Qa Qb Qd Qe) Og(Et Im Is Jn Jq Jr Jt Lh Lw Me Mq Mr Mz Nb No Nt Nw Ok Om Pa Pe Po Qa Qe) Me(Et Fr Hu Im In Is Jn Jq Jr Ma Mm Ms No Nw Oi Ok Pf) Oi(Et Fp Im Is Jn Jq Jr No Nw Oh Ok Pe Po Qa Qd Qe) Oy(Et Fr Jq Lh Mi Nb No Nw Ok Pe Pf Po Qa) Ms(Et Is Jn Jq Jr No Nw Ok Qa Qe) Et(Hu Jq Jr Mg My Oe Qa) Hu(Fr Nw Ok Om) In(Jn Jr Qa) Jq(Fp Mq) NoOe MyNw} Jj{Po(Et Fp Fr Hu Hv Hw Ik Im In Io Is Jk Jn Jo Jq Jr Jt Lh Lj Lu Lv Lw Lx Ly Ma Me Mn Mq Mr Ms Mv Mw Mz Nd Ne Nf Nh Nk Nn No Ns Nt Nw Oe Og Oh Oi Ok Om Oy Oz Pa Pb Pc Pe Qa Qe) Fr(Et Fp Hw Im Is Jn Jq Jr Lv Me Mq Mz Nf Nh No Ns Nt Oh Oi Oy Pe Qa Qe) Lv(Et Fp Im Is Jn Jr Mq Mw Nn No Nt Nw Oh Ok Om Pe Pf Qa Qe) Fp(Is Jk Jq Lh Mq Nn No Nt Nw Ok Om Qa Qe) Mq(Im Is Jn Jq Jr Nn No Nw Oh Pf Qa Qe) Nn(Jr Me Mr Oi Qa Qe) Nf(No Qa Qe) Ma(Qa Qe) Me(No Nw) QaOm QeJq} Fr{Me(Et Fp Hu Im Is Jn Jq Jr Lv Mm Mq Ms My No Ns Nw Og Oh Oi Oy Qa) Mq(Fp Hu In Jn Jq Jr Lv Mg Ms My Mz Ns Oe Of Og Oi Oy Pb Qa) Fp(Et Hu In Jq Jr Lv Lw Mm Ms My Og Oi Oy Oz Pb) Lv(Hu Im Jn Jq Jr Ms My Mz No Ns Og Oi Oy Qa) Oy(Is Jn Jq Jr Lh Nb No Pe Po Qa Qe) Oi(Is Jn Jq Jr No Oh Qa Qe) Jr(Hu Jq Ms My Ns Og) Og(Is Jq Qa Qe) Ms(Is Jq) HuJq} Lv{No(Fp Ii In Io Jr Lu Me Mm Mq Ms Mt Nf Nn Ns Og Oi Oy Oz Pa Pb Pc) Nn(Me Ms Og Oi Oy) Lu(Im Nw) BnDr} Mq{Og(Is Jq Nn No Nw) Nn(Ms Oi) No(In Oi) Nw(Ms My) InJr} Kq{Bb(Dp Fp Kj Kr Oy Us) Oy(aW Dp Kr Tv Us) KjPb} Oi{Nn(Et Fp Is No Qa) Fp(No Nw) NoPc} Og{Om(Hu Qa Qe) Dr(Jd Qy)} Dr{CxbA IbQy} Oy{NnNb NoeF} EtLuJr MwUugL Unconstrained panels with 3 analytes, where 1.0E-9 >= 'model p-value' > 1.0E-10. Contains 8,959 panels of 11,919,473 total panels evaluated. : aA{Is(Hq Hr Hu Hv Hw Hx Ih Ii Ij Ik Il Im Ip Iq Ir It Iu Iv Jg Jh Jj Jk Jm Jn Jo Jp Jq Js Jt Lh Li Lj Lu Lx Ly Lz Mb Mc Md Mf Mg Mh Mi Mj Mk Ml Mn Mp Mt Mv Mw Mx My Mz Na Nb Nc Nd Ne Nh Nj Nk Nl Nm Nq Nr Ns Nt Nu Nv Nx Ny Of Oh Ok Om On Oy Oz Pa Pb Pd Pe Pg Pz Qa Qb Qc Qd) Lh(Hq Hr Hu Hv Hw Hx Ih Ii Ij Ik Il In Ip Iq Ir It Iu Iv Jg Jh Jk Jm Jn Jo Jp Js Jt Li Lj Lu Lx Ly Lz Mb Mc Md Mf Mg Mh Mi Mj Mk Ml Mn Mp Mt Mv Mw Mx My Mz Na Nb Nd Ne Nf Nh Nj Nk Nl Nm Nq Nr Ns Nt Nu Nv Nx Ny Of On Oy Oz Pa Pb Pd Pe Pg Pz Qa Qb Qc Qd) Mr(Hq Hr Hu Hv Hw Hx Ih Ii Ij Ik Il In Ip Iq Ir It Iu Iv Jh Jj Jk Jm Jo Jp Js Jt Li Lj Lu Ly Lz Mb Mc Md Mg Mh Mi Mj Mk Ml Mp Mt Mv Mx My Mz Na Nb Nc Nd Ne Ng Nh Nj Nk Nl Nm Nq Nr Ns Nt Nu Nv Nx Ny Oe Of Oy Oz Pa Pb Pd Pe Pg Pz Qb Qc Qd) Jg(Hq Hr Hv Hw Hx Ih Ii Ij Ik Il Im In Ip Iq Ir It Iu Iv Jh Jj Jk Jm Jo Jp Js Jt Li Lj Lu Lx Ly Lz Mb Mc Md Mg Mi Mj Mk Ml Mn Mp Mt Mv Mw Mx Mz Na Nb Nc Nd Ne Nh Nj Nk Nl Nm Nq Nr Nt Nu Nv Nx Ny Of Om On Oz Pa Pb Pd Pe Pg Pz Qb Qc Qd) Me(Hq Hr Hu Hv Hw Hx Ih Ii Ij Ik Il Ip Iq Ir It Iu Iv Jh Jj Jk Jm Jo Jp Js Jt Li Lj Lu Ly Lz Mb Mc Md Mg Mh Mi Mj Mk Ml Mp Ms Mt Mv Mx My Mz Na Nb Nc Nd Ne Ng Nh Nj Nk Nl Nm Nq Nr Ns Nt Nu Nv Nx Ny Oe Of Oy Oz Pa Pb Pz Qb Qc Qd) Jn(Hq Hr Hu Hv Hw Hx Ih Ii Ij Ik Il Im Ip Iq Ir It Iu Iv Jh Jj Jk Jm Jo Jp Js Jt Li Lj Lu Ly Lz Mb Mc Md Mg Mh Mi Mj Mk Ml Mp Mt Mv Mw Mx My Mz Na Nb Nd Ne Nh Nj Nk Nl Nm Nq Nr Nt Nu Nv Nx Ny Of Oy Oz Pa Pb Pe Pg Pz Qa Qb Qc Qd) Jq(Hq Hr Hu Hv Hw Hx Ih Ii Ij Ik Il Ip Iq Ir It Iu Iv Jh Jj Jk Jm Jo Jp Js Jt Li Lj Lu Lx Ly Lz Mb Mc Md Mg Mi Mj Mk Ml Mp Mt Mx My Mz Na Nb Nc Nd Ne Nh Nj Nk Nl Nm Nq Nr Nt Nu Nv Nx Ny Oe Of Om Oy Oz Pa Pb Pd Pg Pz Qb Qc Qd) Nf(Hq Hr Hu Hv Hw Hx Ih Ii Ij Ik Il Io Ip Ir Iv Jh Jk Jm Jo Jp Js Jt Li Lj Lu Ly Lz Mb Mc Md Mf Mg Mh Mi Mj Mk Ml Mp Ms Mv Mw Mx My Mz Na Nb Nc Nd Ne Ng Nj Nk Nl Nm Nq Nr Ns Nu Nv Nx Ny Oe Of Oy Oz Pa Pb Pd Pg Pz Qb Qc Qd) Lx(Hq Hr Hu Hv Hw Hx Ih Ii Ij Ik Il Ip Iq Ir It Iu Iv Jh Jj Jk Jm Jo Jp Js Jt Li Lj Lu Ly Lz Mb Mc Md Mf Mh Mj Mk Ml Mp Mt Mv Mw Mx My Mz Na Nb Nc Ne Nh Nj Nk Nl Nm Nq Nr Nt Nu Nv Nx Ny Of On Pa Pd Pe Pg Pz Qb Qc Qd) Im(Hq Hr Hu Hv Hw Hx Ih Ii Ij Ik Il Ip Iq Ir It Iu Iv Jh Jj Jk Jm Jo Jp Js Jt Li Lj Ly Lz Mb Mc Md Mg Mi Mj Mk Mp Mt Mv Mw Mx My Mz Na Nb Nc Nd Ne Nh Nj Nk Nl Nm Nq Nr Ns Nt Nu Nv Nx Ny Of Oy Oz Pa Pb Pg Pz Qb Qc Qd) Mn(Hq Hr Hu Hv Hw Hx Ih Ii Ij Ik Il In Ip Iq Ir It Iu Iv Jh Jj Jk Jm Jo Jp Js Jt Li Lj Lu Ly Lz Mb Mc Md Mg Mi Mj Mk Ml Mp Mt Mv Mw Mx My Mz Na Nb Nk Nl Nm Nq Nr Nu Nv Nx Ny Of Oy Oz Pa Pb Pg Pz Qb Qc Qd Wm) Pd(Hr Hu Hv Hw Ih Ij Ik Il In Io Ip Jh Jm Jo Jp Js Jt Li Lj Lu Ly Lz Mb Mc Md Mf Mh Mj Mk Ml Mp Ms Mt Mv Mw Mx My Mz Na Nb Nc Nd Ne Nh Nj Nk Nl Nm Nq Nr Ns Nt Nu Nv Nx Ny Oe Of Oy Pa Pe Pg Pz Qb Qd) Mm(Hq Hr Hv Hw Hx Ih Ii Ik Il In Ip Iq Ir It Iu Iv Jh Jj Jk Jm Jo Jp Js Jt Li Lj Lu Ly Lz Mb Mc Md Mg Mi Mk Mp Ms Mt Mx My Mz Nb Ne Nh Nj Nk Nl Nm Nq Nr Ns Nu Nv Nx Ny Of Oy Oz Pa Pb Pz Qb Qc Qd) Pe(Hq Hr Hu Hv Hw Hx Ih Ii Ij Ik Il Ip Iq Ir It Iu Iv Jh Jk Jm Jo Jp Js Jt Li Lj Lu Ly Lz Mb Mc Md Mg Mh Mi Mj Mk Ml Mp Mt Mv Mx My Mz Na Nb Nd Ne Nh Nj Nm Nq Nr Nt Nu Nv Nx Ny Of Pg Pz Qb Qc Qd) Oh(Hq Hr Hu Hv Hw Hx Ih Ii Ij Ik Il Ip Iq Ir It Iu Iv Jh Jk Jm Jo Jp Js Jt Li Lj Ly Lz Mb Mc Md Mg Mh Mi Mj Mk Ml Mp Mt Mv Mw Mx My Mz Na Nb Ne Nk Nm Nq Nr Ns Nu Nv Nx Ny Of Oy Pa Pg Pz Qb Qc Qd) Jr(Hq Hr Hw Hx Ih Li Ij Ik Il Ip Iq Ir It Iu Iv Jh Jk Jm Jo Jp Js Jt Li Lj Lu Ly Lz Mb Mc Md Mg Mi Mj Mk Ml Mp Mt Mv Mx My Mz Na Nb Nd Ne Nm Nq Nr Nu Nv Nx Ny Of Oy Oz Pa Pg Pz Qb Qc Qd) Oi(Hq Hr Hv Hw Hx Ih Ii Il In Io Ip Ir It Iu Iv Jh Jj Jm Jo Jp Js Jt Lu Ly Lz Mb Mc Md Mg Mi Mk Mp Ms Mx My Mz Na Nb Nc Nd Ne Ng Nj Nk Nl Nm Nq Ns Nu Nx Oe Of Og Oy Oz Pa Pb Pz Qb Qc Wm) On(Hq Hr Hv Hw Hx Ih Ii Ij Ik Il Ip Iq Ir It Iu Iv Jh Jk Jm Jo Jp Js Jt Li Lu Ly Lz Mb Mc Md Mg Mi Mj Mk Ml Mp Mt Mv Mw Mx My Mz Na Nb Ne Nk Nl Nm Nq Nr Nt Nu Nv Nx Ny Om Pa Pg Pz Qb Qc Qd) Qa(Hq Hu Hw Hx Ii Ij Il Ip Iq Ir It Iu Iv Jh Jk Jm Jo Jp Js Jt Li Lj Lu Ly Lz Mc Md Mg Mi Mj Mk Ml Mp Mt Mv Mx My Mz Na Nb Nd Ne Nh Nj Nm Nq Nr Nt Nu Nv Nx Ny Of Pa Pg Pz Qb Qc Qd) Lw(Hq Hr Hv Hw Hx Ih Ii Ij Il Ip Iq Ir It Iu Iv Jh Jj Jk Jm Jo Jp Js Jt Li Lu Ly Lz Mc Md Mg Mi Mk Mp Mx My Mz Na Nb Ne Nj Nk Nl Nm Nq Nu Nv Nx Oe Of Oy Pa Pg Pz Qb Qc Qd)

Mr Mt Mv Mw Mx Na Nd Ne Nf Nh Nj Nk Nl Nm Nn No Nq Nt Nv Nw Nx Oh Ok On Oz Pa Pc Pe Pf Pg Po Pz Qb Qd Qe) Lv(Et Hq Hv Hw
Ih Ii Ij Il In Io Ip Iq Ir Is Iv Jh Jk Jm Jo Js Jt Lh Lj Lu Lw Lx Ly Lz Ma Mg Mh Mi Ml Mm Mr Mt Mv Mw Mx Na Nb Nd Ne Nf Nh Nj Nl Nn
Nq Nt Nu Nv Nw Ny Oe Of Oh Ok Om On Oz Pa Pb Pc Pe Pf Po Pz Qb Qd Qe) Jj(Hq Hu Hv Ih Ij Ik Il In Io Ir It Iv Jk Jm Jo Jp Js Jt Lh Lj Lu
Lw Lx Ly Ma Mb Mf Mg Mh Mi Mj Ml Mm Mn Mr Ms Mt Mv Mw Mx My Na Nb Nc Nd Ne Nj Nl Nm Nn Nr Nu Nw Nx Ny Oe Of Og Ok
Om On Oz Pa Pb Pc Pd Pf Pg Qb Qd Wm) Jr(Et Hq Hr Hv Hw Ii Il Im In Io Iq Is Jk Jm Jn Lj Lu Lw Ma Mb Mf Mg Mm Mr Mv Mw Mz Nc Nd
Ne Nh Nj Nk Nl No Nt Nv Nw Oe Of Oh Ok Oz Pa Pb Pc Pe Pz Qa Qe Wm) Me(Ih Ii In Iq Jh Jk Jo Lj Lw Lx Lz Ma Mb Mg Mn Mr Mt Mv
Mw Mx Mz Ne Nh Nl Nn Nq Nt Nu Oe Of Ok On Oz Pb Pc Pe Pf Po Qb Qd Qe Wm) Jq(Et Ii Im In Is Jh Jn Jo Lj Ma Mb Md Mg Mm Mr Mv
Mw Mx My Ne Nh No Ns Nv Nw Oe Of Oh Ok Om Oz Pa Pb Pc Pf Po Qa Qe) Oy(Et Hu Hv Hw Im Ir Jo Jt Lj Lw Lx Mr Ms Mx Mz Na Ne
Nh Ns Nt Nw Og Oh Oi Ok Om Pd Pf Qb Qd Wm) Oi(Et Hu Ih Im Ir Jt Lh Lj Lw Mr Ms Mt Mx My Mz Ne Nh Nn Ns Nt Nw Ok On Pe Po Qb
Qd) Og(Et Ij Im Jn Jt Lh Lw Mr Mz Ne Nf Nh No Nt Nw Oh Ok Om On Pe Po Wm) Qa(Et Hu Ii Il In Io Iq Jk Jm Lw Ma Mb Mg Ms My Ns
Nw Oe Of Pa Pb) Jn(Et Hu In Lw Mg Ms My Ns Oe Pa Wm) Is(Hu Ii Il In Jk Jm Mg My Ns Oe) Ms(Et Im No Nw Oh Ok Om Qe Wm) My(Im
Nb Nh No Nw Om Qe) Hu(Im Ne Nh Nw Om On Qe) Dr(bE Cv Cx dD) No(Io Oe Pa Wm) Oe(Im On Qe) Mg(Et Ok) WmLj MwOn QeJm}
On{Ms(Hq Hr Hv Hw Hx Ih Ii Ij Ik Il Io Ip Iq Ir It Iu Iv Jg Jh Jk Jm Jo Jp Js Jt Lh Li Lj Lu Lx Lz Ma Mb Mc Md Mf Mg Mh Mi Mj Mk Ml Mm
Mn Mp Mr Mt Mv Mx Mz Na Nb Nc Nd Ne Nf Nh Nj Nk Nl Nm Nq Nr Ns Nt Nu Nv Nx Ny Oe Of Ok Om Oz Pa Pd Pe Pf Pg Pz Qb Qc Qd)
My(Hq Hr Hv Hw Hx Ih Ii Ij Ik Il Ip Iq Ir It Iu Iv Jk Jm Jo Jp Js Lh Li Lj Lw Lx Lz Mc Md Mg Mh Mj Mk Ml Mm Mn Mp Mt Mx Mz Na Nb
Ne Nj Nm Nr Nt Nu Nv Nx Ny Of Oh Ok Pd Pe Pg Pz Qb Qc Qd) Og(Et Hr Hv Hw Ij Ik Io Iq Ir Iu Jg Jh Jj Jo Jp Jt Lh Lu Lx Mb Md Mf Mg
Mh Mj Mk Ml Mm Mn Mr Mt Mv Mw Mx Mz Na Nc Nd Ne Nh Nj Nl Ns Nt Nu Nw Nx Ny Oe Oi Ok Om Oz Pa Pb Pd Pe Pf Pg Qb Qd) Jj(Et
Hu Hv Hw Ik Im Io Is Jn Jq Lh Lj Lu Ly Ma Mh Mr Mw Mz Na Nd Ne Nf Ng Nh Nj Ns Nt Nw Og Ok Om Pd Pe Pf Qd) Qa(Et Hu Ik Im In
Io Jh Jk Jn Jo Jq Jr Lj Lu Lw Me Mg Mm Mq Mt Mv Mw Mz Nn Ns Nv Nw Oe Oh Oi Pb Pc Pf Po Qa) Hu(Et Ii Im Io Is Jn Jq Jr Lu Mc Mk Mr
Mv Nd Nf Nh Nn No Ns Nw Oe Om Pa Pb Pc Pf Po Qa Qe) Oi(Hq Im In Is Jn Jq Lj Lu Ly Me Mg Mh Mq Mr Mt Mw Mz Nf Nn Ns Of Oh Pb
Pc Pf Po Qd Qe) Me(Fp Im Jo Jr Ma Mg Mq Mv Mw No Ns Nw Oe Pb Pf) Oe(Fp Im Is Jn Jr Lj Ly Mq Nn No Of Oh Po Qe) Fp(Ii Jo Jq Lw Ly
Mg Mq Mv Mw Ns Of Pb) In(Is Jn Jq Jr Mq Mv Mw No Ns Of Po Qe) Ns(Hq Im Jr Ly Mq Nn No Of Qa) Mq(Ii Jq Jr Mw No Of Pb) Of(Hv Ij
Jo Jr Ma Om) Ii(Jq Jr No Po Qa) Qa(Jk Jq Ma Pb) Jq(Ma Md Pb) No(Io Pb) Mw(Jr Pc) WmOy PoPb NnMv} Jj{Po(Hq Hr Hx Ih Ii Ij Il Ip Iq Ir
It Iu Iv Jg Jh Jm Jp Js Li Lz Mb Mc Md Mf Mg Mh Mi Mj Mk Ml Mm Mp Mt Mx My Na Nb Nc Nj Nl Nm Nq Nr Nu Nv Nx Ny Of Pd Pf Pg
Pz Qb Qc Qd) Lv(Hu Ij Ik Io Jg Jk Jm Jp Jq Jt Lh Li Lj Lu Lw Lx Ma Me Mm Mn Mr Mt Mv Mx Mz Nb Nf Nh Nr Nu Nv Nx Ny Pa Pc Pd Pg
Qb Qd) No(Et Hu Hw Ij Ik Im Io Is Jg Jk Jn Jo Jq Jr Lh Lj Lu Lw Ma Mr Ms Mw Nc Nd Nh Nn Ns Nt Oh Oi Ok Om Oz Pa Pc Qa Qe Wm)
Nn(Et Hu Hv Hw Ik Im Ir Is Jn Jo Jq Jt Lh Lu Lx Ma Mh Ms Mz Na Nd Ne Nf Ng Nh Nj Ns Nt Nw Og Ok Om Pd Pe Pf Qd) Qa(Et Hu Ik Im In
Io Jg Jq Jr Lh Lu Lw Lx Me Mn Mr Mt Mv Mw Mz Nt Nw Og Oh Oi Ok Pb Pc Pd Pe Pf) Qe(Et Hu Ik Im Is Jg Jn Jo Jr Lh Lu Lw Lx Me Mr
Mv Mw Mz Nt Nw Og Oh Oi Ok Om Pc Pe Pf) Fp(Et Hx Ij Im Jg Jn Jo Jp Jr Jt Lw Lx Ma Me Mn Mr Mv Mw Mz Nv Ny Oh Pc Pe Pf Pg Qd)
Mq(Et Jg Jk Jp Lh Ma Me Mn Mt Mw Mz Nt Ok Om Pc Pe Pg Qd) Jr(Et Hu Ik Im Is Jg Jk Jq Lh Ma Me Nt Nw Ok Om Pf) Is(Et Hu Ik Lh Lu
Ma Me Mr Nf Nt Oi Om Pe Pf) Jq(Lu Ma Mr Mv Nt Oh Pe Pf) Me(Et Lh Ma Oh Ok Om Pf) Nf(Et Jn Nt Nw Ok) Lh(Im Jn Mr Oh Pf) Om(Mr
Ng Og Oh Pf) Et(Jn Lu Oh) Nt(Oh Pf) Ma(Jn Nw) Ng(Jg Jk) LuOk} Lv{No(Et Hq Hr Hu Hv Hw Hx Ih Ij Ik Il Im Ip Iq Ir Is It Iu Iv Jg Jh Jk Jm
Jn Jo Jp Jq Js Jt Lh Li Lj Lw Lx Ly Lz Ma Mb Mc Md Mf Mg Mh Mi Mj Mk Ml Mn Mp Mr Mv Mw Mx My Mz Na Nb Nc Nd Ne Nh Nj Nk
Nl Nm Nq Nr Nt Nu Nv Nw Nx Ny Oe Of Oh Ok Om Pd Pe Pf Pg Po Pz Qa Qb Qc Qd Qe Wm) Nw(Et Fp Hu Im Io Jn Jq Jr Lw Ly Ma Me
Mm Mq Ms Mw My Mz Ng Nn Ns Og Oh Oi Ok Oy Oz Pa Pb Pc Pe Pf Po Qa Qe) Nn(Et Fp Hu Ii Im In Io Is Jn Jo Jq Jr Lu Mm Mq Mr Mt My
Mz Ns Oe Ok Pb Pc Pe Pf Qa) Po(In Io Jo Jq Jr Lu Mm Ms Mt Mz Ng Og Oi Oy Pb) Jr(Et Im In Io Lu Mm Mq Mw Oi Ok Pc Pf) Dr(AF bH cV
CX Fn Mw Og Oz Pb) Mm(Fp Im Io Is Jn Jq Lu Me Mt Mz) Mq(Im Is Jq Mt Mz Oh Pf Qa) Lu(Et Is Jn Oh Ok Pf Qa) Io(Et Im Is Jn Qa Qe)
Oi(Is Oh Ok Pf Qa Qe) Pf(Im Jq Me Ng Oy) Im(Mt Mz Pe) Qa(In Mt Og) Lx(Ng Oy) Og(Is Om) FpJq NgOk} Kq{Bb(aE AF Aj aL Ar aW Ax
BA bH bJ BN BO bR bX cI Cq Cs CX cZ Db De dI dN Ed Ef Fb Fn Fw Hc Hf Hu Ii Im Ir Iu Iv Jd Je Jn Jv Kd Kf Kg Ki Kl Ko Kp Kx Kz Lj Ly
Md Me Ml Mq Mr Nc Nf Nl Nn No Nr Nv Nx Of Og Oi Ow Oz Pa Pb Pc Pg Pk Ql Qn Qy Qz Rf Ri Sr To Uc Un Up Ur Uu Uv Vo) Oy(Af Ao
Ba bJ bO bX cI Cx cZ dA Dc dN dR Ed eF Fn Fp gL gP Hc Hu Ii Io Jd Je Jt Jv Kd Kj Ko Lu Ly Md Mq My Nc Nf Nl Nn No Of Og Oi Oz Pg
Ql Qy Ri Tn To Up Uu Uv) Kj(Ao bJ bN Ch cl Cq Dk Dp gL Ib Jd Md Mr Ms Mw My Nb Nv Ny Pg Qx Ur Vp Tj) Uu(bH cZ Ef Pg) Oz(aW Dr
gP Tv) dN(Co Fn Kg Ly) Ed(Fw Pg Ur) Dp(Ao Kg) Dr(cZ dA) AjKr HccZ JvaE} Ng{Jg(Hr Hv Hw Hx Ih Ii Ik Il In Ir Iu Iv Jm Jo Jp Js Jt Lw
Mb Md Mf Mg Mh Mi Mj Mk Ml Mm Mn Mp Ms Mt Mx Na Nc Nd Ne Nj Nk Nl Nq Ns Nu Nv Nx Ny Of Og Oi Oy Oz Pa Pc Qb) Om(Et Hu
Ik Im In Jn Jp Ly Md Me Mh Mi Mj Ml Mm Mn Mp Ms Mt Mx Nb Ne Nf Nh Nq Ns Nw Oh Oi Ok Oz Pa Pb Pc Pd Pe Pg Qb Qd) Nn(Fp Im In
Jh Jn Jq Jr Jt Lh Lx Ma Mi Mr Mv Nb No Nt Nw Oi Pe Po Qa Qe) Nw(Et Jh Jk Jo Jr Lh Lu Ma Me Mv Po Qa Qe) Et(Is Jk Jr Lx Mq Mv Po Qa
Qe) Po(Is Jq Lh Lu Ma Mq Ok) Mq(Is Jq Ma Pf Qa) Ok(Jk Jr Mv Pc Qe) Mv(Is Lh Lx) No(Lu Pc) Ma(Lh Qa) LuIs TrQy} Nw{Og(Fp Hw Ij Im
Is Jo Jq Jr Lh Lu Ma Me Nf Nn Om Pc Pe Po Qa Qe) Me(Et Im In Jr Lu Ma Mm Mq Ms My Nn No Oh Oi Oy Pb Pc Pf) Mq(Im In Jn Jq Jr Lu
Ly Ma Ns Nv Oi Oy Pb Qa) Ms(Fp Is Jr Lu Mv Nn Oi Om Pc Po Qa Qe) Oi(Is Jr Lu Ma Nn No Oh Po Qa Qe) Ma(Jq Jr Qa) Nn(My Oy) Qa(In
Pb) LuMy MdJq NbOy} Mq{No(Ii Io Jn Jq Jr Lu Ma Me Ms Nk Nn Ns Oe Oy Pb Pc) Jq(Et Fp In Jr Ma Nn Ns Oh Ok Pc Pf Po Qa Qe) In(Is Jn
Mz Nn Oh Ok Po Qa Qe) Og(Im Jr Mz Oh Ok Om Po Qa Qe) Nn(Hu Jr Me Ns Ok Oy Pb) Oi(Is Oh Ok Po Qa) Jr(Et Ns Pc) Lu(Et Ok) MsIs}
Oi{No(Et Ik In Io Is Jg Jn Jq Jr Lh Lu Ma Me Ms Nf Nt Oh Ok Om Po Qa Qe Wm) Nn(Im Jn Jq Jr Lh Me Mr Ms Nh Nt Ok Pc Po Qd Qe) Et(Is
Jr Lu Oh Po Qa Qe) Is(Fp Lu Nt Pc Pf Po) Qa(Jg Jq Om Pc Po) Ok(Fp Lu Po) QeOm} Og{Nn(Et Fp Is Jq Jr Lh Me Nb No Ok Om Pe Po Qe)
Is(Et Jg Jq Lh Lu Mm Nf No Om Pc Po Wm) Om(Fp Im Jr Lu Ms My No Oh Pe Po) Po(Jq Lh Lw Nb Ok Pc) Dr(Fb Gp Mv Nq) Jq(Fp Pf Qa
Qe) WmNo LuOk ImLh} In{No(Is Jq Jr Me Ok Qa Qe Wm) Jr(Et Nn Ok Om Po Qa Wm) Ok(Fp Is Nn Po Qa Qe) Me(dN Is Nn Po) Qa(Et Jq
Om) Po(Is Jq) Nn(Fp Jn) EtIs QeJq} Dr{Mv(Bn Ib Oy Oz Vs) Jd(Ap Ii Nm Wh) bA(bF bU bZ) Lh(Ii Ke) bF(Ba cT) BgOy BnJy MtbH NjRi
OrbU} Et{Lu(Fp Im Is Jn Jq Me No Oh Pb Qa Qe) Ms(Is Jr Nn Oh) Io(Is Qa) NnMe} No{Me(Lu Ma Nn Pc) Ms(Nn Om) Pc(Jq Lu) eF(Hc Us)
IoIs} Ms{Nn(Is Jq Jr Me Ok) Om(Jr Oh Qa Qe)} dN{cT(Bg bO bR cA) Jy(Ed Hq Ly) bA(bR dH)} Oy{Po(Jq Nb) Om(Pf Tn) NnPe SreF JqPf}
eF{Sr(Aj Hc Uu) MwUu} Jq{Ma(Qa Qe) FpNn} Lu{Ok(Fp Jr)}

Unconstrained panels with 3 analytes, where 1.0E-8 >= 'model p-value' > 1.0E-9. Contains 20,461 panels of 11,919,473 total panels evaluated. :
Ji{Mz(Et Hq Hr Hu Hv Hw Hx Ih Ii Ij Ik Il Im Io Ip Iq Ir Is It Iu Iv Jg Jh Jk Jm Jn Jo Jp Jq Js Jt Lh Li Lj Lw Lx Ly Lz Mb Mc Md Me Mf Mg
Mh Mi Mj Mk Ml Mm Mn Mp Mt Mv Mw Mx My Na Nb Nc Nd Ne Nf Nh Nj Nk Nl Nm Nq Nr Ns Nt Nu Nv Nw Nx Ny Oe Of Oh Ok Om
On Oy Oz Pa Pb Pc Pd Pe Pg Pz Qa Qb Qc Qd) Pg(Et Hq Hr Hu Hv Hw Hx Ih Ii Ij Ik Il Im Io Ip Iq Ir Is It Iu Iv Jg Jh Jk Jm Jn Jo Jp Jq Js Jt Lh
Li Lj Lw Lx Ly Lz Mb Mc Md Me Mf Mg Mh Mi Mj Mk Ml Mm Mn Mp Mr Mt Mv Mw Mx My Na Nb Nc Nd Ne Nf Nh Nj Nk Nl Nm Nq Nr
Ns Nt Nu Nv Nw Nx Ny Oe Of Oh Ok Om On Oy Oz Pa Pc Pd Pe Pz Qa Qb Qc Qd) Lz(Et Hq Hr Hu Hv Hw Hx Ih Ii Ij Ik Im Io Ip Iq Ir Is It Iv

Lh Li Ly Mb Me Mf Mg Mr Mv Mw Na Nd Ne Nf Nh Nk Nm Ns Nt Nv Nw Oe Oh Ok Om Oz Pa Pc Pe Qa Qc) Jo(Hu Hx Ii Ij Il Im Io Is Jg Jh
Jm Jn Jq Js Jt Li Ly Mb Mf Mg Mk Mw My Na Nd Ne Nh Nk Nm Ns Nt Nv Nw Nx Oe Of Oh Ok Om Oy Oz Pa Pb Pc Qc) Lh(Et Hu Hx Ij Il
Im Is Iu Jg Jh Jm Jn Jq Js Jt Li Mb Mf Mg Mk Mr Mv Mw My Na Nd Ne Nf Nh Nk Nm Ns Nt Nv Nw Oe Oh Ok Om On Oz Pa Pe Qa Qc)
Ok(Et Hu Hx Ii Ij Il Im Is Iu Jg Jh Jm Jn Jq Js Li Mb Mf Mg Mk Mv Mw My Na Nd Ne Nf Nh Nk Ns Nt Nv Nw Oe Of Oh Om On Oy Oz Pa Pe
Qc) Jt(Hu Hx Ii Ij Il Im Io Iu Jg Jh Jm Jn Jq Js Li Ly Mb Me Mf Mg Mk Mw My Na Nd Ne Nf Nh Nk Nm Ns Nv Nw Nx Oe Of Om Oy Oz Pa
Pb Qc) Mf(Et Hu Ii Im Io Is Jg Jn Jq Ly Mb Me Mg Mr Mv Mw My Na Nd Ne Nf Nh Nm Ns Nt Nw Nx Oe Of Oh Om On Oy Oz Pa Pb Pc Pe
Qa Qc) Li(Et Hu Ii Im Io Is Jg Jn Jq Ly Mb Me Mg Mr Mv Mw My Na Nd Ne Nf Nh Nm Ns Nt Nw Nx Oe Of Oh Om On Oy Oz Pa Pb Pc Pe
Qa Qc) Nv(Et Hu Hx Ii Im Io Is Jg Jn Jq Ly Mb Me Mg Mr Mv Mw My Na Nd Ne Nf Nh Nm Ns Nt Nw Nx Oe Of Oh Om On Oy Oz Pa Pb Pc Pe
Qa Qc) Il(Et Hu Ii Im Io Is Jg Jn Jq Ly Mb Me Mg Mr Mv Mw My Na Nd Ne Nf Nh Nm Ns Nt Nw Nx Oe Of Oh Om On Oy Oz Pa Pb Pc Pe
Qa) Jm(Et Hu Ii Im Io Is Jg Jn Jq Js Ly Mb Me Mg Mv Mw My Na Nd Ne Nf Nh Nm Ns Nt Nw Nx Oe Of Oh Om On Oy Oz Pa Pb Pc Pe Qc)
Hx(Et Hu Ii Im Io Is Jg Jn Jq Ly Mb Me Mg Mw My Na Nd Ne Nf Nh Nm Ns Nt Nw Nx Oe Of Oh Om On Oy Oz Pa Pb Pc Pe Qa Qc) Jh(Et
Hu Ii Im Io Is Jg Jn Jq Ly Mb Me Mg Mr Mw My Na Nd Ne Nf Nh Nm Ns Nt Nw Nx Oe Of Oh Om On Oy Oz Pa Pb Pc Pe Qa) Mk(Et Hu Ii
Im Io Is Jg Jn Jq Ly Mb Me Mg Mr Mv Mw My Na Nd Ne Nf Nh Nm Ns Nt Nw Nx Oe Of Oh Om Oz Pa Pb Pc Pe Qa) Nk(Et Hu Ii Im Io Is Jg
Jn Jq Ly Mb Me Mg Mv Mw My Na Nd Ne Nf Nh Nm Ns Nt Nw Nx Oe Of Oh Om On Oy Oz Pa Pb Pc Pe) Iu(Et Hu Ii Im Io Is Jg Jn Jq Ly Mb
Me Mg Mv Mw My Na Nd Ne Nf Nh Nm Ns Nt Nw Nx Oe Of Oh Om On Oy Oz Pa Pb Pc Pe) Of(Ii Im Io Is Jg Jn Jq Ly Mb Me Mg Mw
My Na Nd Ne Nf Nh Nm Ns Nt Nw Nx Oe Of Oh Om On Oy Oz Pa Pb Pc Pe) Qc(Et Hu Ii Im Io Is Jg Jn Jq Ly Mb Me Mg Mw My Na Nd Ne
Nf Nh Nm Ns Nt Nw Nx Oe Of Om On Oy Oz Pa Pb Pc Pe) Js(Et Hu Ii Im Io Is Jg Jq Ly Mb Me Mg Mv Mw My Na Nd Ne Nf Nh Nm Ns Nt
Nw Nx Oe Of Om On Oy Oz Pa Pb Pc Pe) Jn(Hu Ii Im Is Jg Jq Mb Mg Mw My Na Nd Ne Nf Nh Nm Ns Nt Nw Nx Oe Of Oh Om Oy Oz Pa
Pe) Na(Et Hu Im Is Jg Jq Mb Mg Mw My Nd Ne Nf Nh Nm Ns Nt Nw Oe Of Oh Om Oy Oz Pa Pe) Nd(Et Hu Ii Io Jg Jq Mb Mc Mg My Ne Nf
Nh Nm Ns Nt Nw Nx Oe Of Om Oy Oz Pa Pe) Jg(Et Hu Ii Im Is Jq Ly Mb Mv Mw Ne Nf Nh Nm Nt Nw Oe Of Om On Oz Pa Pc Pe) Oe(Et Hu
Ii Im Is Jq Mb Me Mg Mw My Ne Nh Nm Ns Nw Nx Of Om Oy Oz Pb Pc) Om(Et Hu Ii Im Io Is Jq Mb Mw Ne Nf Nh Nm Ns Nt Nw Oh On
Oz Pa Pc Pe) Nm(Hu Ii Io Is Jq Mb Mg Mw My Ne Nf Nh Ns Nw Nx Of Oy Oz Pa Pe) My(Hu Ii Im Is Jq Ly Mb Mg Mw Ne Nh Ns Nt Nx Of
Oy Oz Pa Pb) Ne(Hu Ii Io Is Jq Mb Mg Mw Nh Ns Nt Nw Nx Of Oy Oz Pa Pe) Mg(Ii Im Is Jq Ly Mb Mw Nh Ns Nw Nx Of Oy Oz Pa Pb)
Nh(Hu Ii Io Is Jq Mb Ns Nt Nw Nx Of Oy Oz Pa Pe) Wm(Jj Jl Lu Ma Mu Mv Ng Ni Nn No Oi Oy Pf Qe) Jq(Et Hu Im Is Mb Mw Nf Nt Nw Of
Oz Pa Pe) Ni(aW Gn Kr Rv Tn To Tr Tv Ux Wf Yd Ti) Nw(Et Hu Ii Is Mb Mw Nf Nt Oh On Oz Pe) Of(Ii Im Io Is Ly Mb Ns Nx Oy Oz Pb)
Oz(Et Hu Ii Is Mw Nf Ns Nt Nx Pa) Nt(Et Hu Is Mw Ns On Pe) Mb(Hu Ii Io Nf Ns Nx Oy) Mw(Hu Im Is Nf Pa Pe) Nx(Ii Ly Ns Oy Pa Pb)
Oy(Ii Kq Ly Ns Pb) Is(Hu Im Pe Qa) Ii(Im Ns Pb) Pa(Hu Nf Ns) Dp(aA Lu) Pe(Hu On) BbKq JlUs) aA{Mx(Hq Hr Hu Hv Hw Hx Ih Ii Ij Ik Il
In Ip Iq Ir It Iu Iv Jh Jj Jk Jm Jo Jp Js Jt Li Lj Lu Ly Lz Mb Mc Md Mf Mg Mh Mi Mj Mk Ml Mp Ms Mt Mv My Mz Na Nb Nc Nd Ne Ng Nh
Nj Nk Nl Nm Nq Nr Ns Nt Nu Nv Nx Ny Oe Of Oy Oz Pa Pb Pg Pz Qb Qc Qd) Il(dN Hq Hr Hu Hv Hw Hx Ih Ii Ij Ik In Ip Iq Ir It Iu Iv Jh Jj Jk
Jm Jo Jp Js Jt Li Lj Lu Ly Lz Mb Mc Md Mg Mh Mi Mj Mk Ml Mp Ms Mt Mv My Mz Na Nb Nc Nd Ne Ng Nh Nj Nk Nl Nm Nq Nr Ns Nu Nv
Nx Ny Oe Of Oy Oz Pa Pb Pg Pz Qb Qc Qd) Jp(Hq Hr Hu Hv Hw Hx Ih Ii Ij Ik In Ip Iq Ir It Iu Iv Jh Jj Jk Jm Jo Js Jt Li Lj Lu Ly Lz Mb Mc Md
Mg Mh Mi Mj Mk Ml Mp Ms Mt Mv Mw My Mz Na Nb Nd Ne Ng Nh Nj Nk Nl Nm Nq Nr Ns Nu Nv Nx Ny Oe Of Og Oy Oz Pa Pb Pg Pz
Qb Qc Qd) Mb(Hq Hr Hu Hv Hw Hx Ih Ii Ij Ik In Ip Iq Ir It Iu Iv Jh Jj Jk Jm Jo Js Jt Li Lj Lu Ly Lz Mc Md Mf Mg Mh Mi Mj Mk Ml Mp Ms
Mt Mv My Mz Nb Nc Nd Ne Ng Nh Nj Nk Nl Nm Nq Nr Ns Nu Nv Nx Ny Oe Of Oy Oz Pa Pb Pg Pz Qb Qc Qd) Hw(Hq Hr Hu Hv Hx Ih Ii Ij
Ik In Io Ip Ir Iv Jh Jj Jk Jm Jo Js Jt Li Lj Lu Ly Lz Mc Md Mf Mg Mh Mi Mj Mk Ml Mp Ms Mt Mv My Mz Na Nb Nc Nd Ne Ng Nh Nj Nk Nl
Nm Nq Nr Ns Nt Nu Nv Nx Ny Oe Of Oy Oz Pa Pb Pg Pz Qb Qc Qd) Jk(Hq Hr Hu Hv Hx Ih Ii Ij Ik In Ip Iq Ir It Iu Iv Jh Jm Jo Js Jt Li Lj Lu
Ly Lz Mc Md Mg Mh Mi Mj Mk Ml Mp Ms Mt Mv Mw My Mz Na Nb Nc Nd Ne Nh Nj Nk Nl Nm Nq Nr Ns Nt Nu Nv Nx Ny Of Oy Oz Pa
Pb Pd Pg Pz Qb Qc Qd) Jt(Hq Hr Hu Hv Hx Ih Ii Ij Ik Ip Iq Ir It Iu Iv Jh Jj Jm Jo Js Li Lj Lu Ly Lz Mc Md Mg Mh Mi Mj Mk Ml Mp Ms Mt
Mv Mw My Mz Na Nb Nc Nd Ne Nh Nj Nk Nl Nm Nq Nr Ns Nt Nu Nv Nx Ny Oe Of Oy Oz Pa Pb Pg Pz Qb Qc Qd) Nd(Hq Hr Hu Hv Hx Ih
Ii Ij Ik In Ip Iq Ir It Iu Iv Jh Jj Jm Jo Js Li Lj Lu Ly Lz Mc Md Mf Mg Mh Mi Mj Mk Ml Ms Mt Mv My Mz Nb Nc Ne Ng Nh Nj Nk Nl Nm Nq
Nr Ns Nt Nu Nv Nx Oe Of Oy Oz Pa Pb Pg Pz Qb Qc Qd) Li(Hq Hr Hu Hv Hx Ih Ii Ij Ik Ip Iq Ir It Iu Iv Jh Jj Jm Jo Js Lj Lu Ly Lz Mc Md Mg
Mh Mi Mj Mk Ml Mp Ms Mt Mv Mw My Mz Na Nb Ne Nh Nj Nk Nl Nm Nq Nr Ns Nt Nu Nv Nv Ns Ny Oe Of Oy Oz Pa Pb Pg Pz Qb Qc Qd)
Jo(Hq Hr Hu Hv Hx Ih Ii Ij Ik Ip Iq Ir It Iu Iv Jh Jm Js Lj Lu Ly Lz Mc Md Mf Mg Mh Mi Mj Mk Ml Mp Ms Mt Mv My Mz Na Nb Nc Ne Nh
Nj Nk Nl Nm Nq Nr Ns Nt Nu Nv Nx Ny Oe Of Oy Oz Pa Pg Pz Qb Qc Qd) Ne(Hq Hr Hu Hv Hx Ih Ii Ij Ik In Ip Iq Ir It Iu Iv Jh Jj Jm Js Lj Lu
Ly Lz Mc Md Mg Mh Mi Mj Mk Ml Mp Ms Mt Mv My Mz Na Nb Ng Nj Nm Nq Nr Ns Nt Nu Nv Nx Ny Oe Of Oy Oz Pa Pb Pg Pz Qb Qc
Qd) Nu(Hq Hr Hu Hv Hx Ih Ii Ij Ik Ip Iq Ir It Iu Iv Jh Jm Js Lj Lu Ly Lz Mc Md Mg Mh Mi Mj Mk Ml Mp Mt Mv My Mz Na Nb Nc Ng Nh Nj
Nk Nl Nm Nq Nr Nt Nv Nx Oe Of Oy Oz Pa Pb Pg Pz Qb Qc Qd) Nb(Hq Hr Hu Hv Ih Ij Ik In Io Ip Ir Jh Jj Jm Js Lj Lu Ly Lz Mc Md Mh Mi
Mj Mk Ml Mp Ms Mt Mv Mw My Mz Na Nc Ng Nh Nj Nk Nl Nm Nq Nr Ns Nt Nv Nx Ny Oe Of Oy Oz Pa Pb Pg Pz Qb Qc Qd) Ni(Hq Hr Hu
Hv Hx Ih Ii Ij Ik Ip Iq Ir It Iu Iv Jh Jm Js Lj Lu Ly Lz Mc Md Mg Mi Mj Mk Ml Mp Ms Mt Mv My Mz Ng Nh Nk Nl Nm Nq Nr Ns Nt Nv Nx
Ny Oe Of Oy Oz Pa Pb Pg Pz Qb Qc Qd) Nk(Hq Hr Hu Hv Hx Ih Ii Ik In Io Ip Iq Ir It Iu Iv Jh Jj Jm Js Lu Ly Lz Mc Md Mg Mi Mj Mk Ml Mp
Ms Mt Mv My Mz Nc Ng Nl Nm Nq Nr Ns Nv Nx Ny Oe Of Og Oy Oz Pa Pb Pz Qb Qc Qd) Mz(Hq Hr Hu Hv Hx Ih Ii Ij Ik Ip Iq Ir It Iu Iv Jh
Jj Jm Js Lj Lu Ly Lz Mc Md Mg Mh Mi Mj Mk Ml Mp Ms Mt Mv My Mz Ng Nh Nl Nm Nq Nr Ns Nv Nx Ny Oe Of Oy Oz Pa Pg Pz Qb Qc Qd)
Ik(Hq Hr Hu Hv Hx Ih Ii Ij Ip Iq Ir It Iu Iv Jh Jm Js Lj Lu Ly Lz Mc Md Mg Mh Mi Mj Mk Ml Mp Ms Mt Mv My Nc Nh Nl Nm Nq Nr Nt Nv Nx
Ny Oe Of Oy Oz Pa Pb Pg Pz Qb Qc Qd) Jm(Hq Hr Hu Hv Hx Ih Ii Ij Ip Ir Iu Iv Jh Js Lj Lu Ly Lz Mc Md Mh Mi Mj Mk Ml Mp Ms Mt Mv
Mw My Na Nc Nh Nl Nm Nq Nr Ns Nt Nv Nx Ny Oe Oy Oz Pa Pb Pg Pz Qb Qc Qd) Lu(Hq Hr Hu Hv Ih Ii Ij In Io Ip Ir Iv Jh Jj Js Lj Ly Lz Md
Mh Mi Mj Mk Ml Mp Ms Mt Mv Na Nc Ng Nh Nl Nm Nq Nr Ns Nv Nx Ny Oe Og Oy Oz Pa Pb Pg Pz Qb Qc Qd) Nv(Hq Hr Hu Hv Hx Ih Ii Ij
Ip Iq Ir It Iu Iv Jh Js Lj Ly Lz Mc Md Mg Mi Mj Mk Ml Mp Ms Mt Mv Mw My Na Nh Nl Nm Nq Nr Nt Nx Ny Of Oy Oz Pa Pb Pg Pz Qb Qc Qd)
Nr(Hq Hr Hu Hv Hx Ih Ii Ij Ip Iq Ir It Iu Iv Jh Js Lj Ly Lz Mc Md Mg Mi Mj Mk Ml Mp Mt Mv My Na Nh Nl Nm Nq Nt Nx Ny Of Oy Pa Pb
Pg Pz Qb Qc Qd Wm) Ly(dN Hq Hr Hu Hv Ii Ij In Ip Ir Iv Jh Jj Js Lj Lz Md Mg Mh Mi Mj Mk Ml Mp Ms Mt Mv Na Nc Ng Nl Nm Nq Ns Nx
Ny Oe Og Oy Oz Pa Pb Pg Pz Qb Qc Qd) Mk(Hq Hr Hu Hv Ih Ii Ij In Ip Ir Jh Jj Js Lj Lz Mc Md Mf Mh Mi Mj Ml Mp Ms Mt Mv Mw Na Nc
Ng Nh Nl Nm Nq Ns Nx Ny Oe Oy Oz Pb Pg Pz Qb Qc Qd) Mv(Hq Hr Hv Hx Ih Ii Ij Ip Iq Ir It Iu Iv Jh Js Lj Lz Mc Md Mg Mi Mj Ml Mp Mt
Mw My Na Nc Nl Nm Nq Nx Ny Of Oy Oz Pa Pb Pg Pz Qb Qc Qd Wm) Nl(Hq Hr Hu Hv Hx Ih Ii In Io Ip Ir It Iv Jh Jj Js Lj Lz Mc Md Mg Mi
Mj Ml Mp Ms Mt My Ng Nm Nq Ns Nx Ny Oe Of Oy Oz Pa Pb Pz Qb Qc Wm) Hv(Hq Hr Hu Ih Ij In Io Ip Ir Jh Jj Js Lj Lz Mc Mf Mh Mi Mj
Ml Mp Ms Mt Na Nc Ng Nh Nm Nq Ns Nx Ny Oe Of Oy Oz Pa Pg Pz Qb Qc Qd) Nx(Hq Hr Hu Hx Ih Ii Ij Ip Iq Ir It Iu Iv Jh Js Lj Lz Mc
Md Mg Mi Mj Ml Mp Mt My Na Nc Nh Nm Nq Ny Oe Of Oy Oz Pa Pg Pz Qb Qc Qd) Nq(Hq Hr Hu Ii Ij In Io Ip Ir Jj Js Lj Lz Md Mf Mh Mi
Mj Ml Mp Ms Mt Mw My Na Nc Nh Nm Ns Nt Ny Oe Oy Oz Pb Pg Pz Qb Qc Qd) Mp(Hq Hr Hu Hx Ih Ii In Ip Iq Ir It Iu Iv Jh Jj Js Lj Lz Mc

Figure 7 Continued

Md Mg Mi Mj Ml Mt My Nc Nm Ny Oe Of Oy Pa Pb Pg Pz Qb Qc Qd) Hq(Hr Hu Ij In Io Ip Ir Jh Jj Js Lj Lz Md Mh Mi Mj Ml Ms Mt Mw Na Nc Ng Nh Nm Ns Ny Oe Oy Oz Pa Pb Pd Pg Pz Qb Qc Qd) Qb(Hr Hx Ih Ii Ij Ip Iq Ir It Iu Iv Jh Js Lj Lz Mc Md Mg Mi Mj Ml Ms Mt My Na Nh Nm Ny Of Oy Oz Pa Pb Pg Pz Qc Qd) Wm(Fp Fr Im In Is Jg Jj Jn Jq Jr Lh Lw Lx Me Mm Mq Ms Mw Na Ng Ni Nn Nw Oh Ok Om On Oz Pb Pc Pe Pf Po Qa Qd Qe) Hu(Hr Hx Ih Ii In Ip Iq Ir It Iu Iv Jh Js Lz Mc Md Mg Mi Mj Ml Mt My Na Nc Nh Nm Ny Oe Of Oy Oz Pa Pb Pz Qc Qd) Js(Hr Ih Ij Ip Ir Jh Jj Lj Lz Mc Md Mh Mi Mj Ml Ms Mt Mw Na Nc Ng Nh Nm Ns Nt Ny Oe Oy Oz Pa Pb Pg Pz Qc Qd) Lj(Hr Hx Ih Ii Ij Ip Iq Ir It Iu Iv Jh Lz Mc Md Mg Mh Mi Mj Ml Ms Mt My Na Nm Ny Of Oy Pa Pb Pg Pz Qc Qd) Jj(Dp Hr Hx Ih Ii In Ip Iq Ir It Iu Iv Jh Lz Mc Md Mg Mi Ms My Nc Ng Nm Ns Oe Of Og Oy Oz Pa Pb Pz Qc) Mj(Hr Hx Ih Ii Ij Ip Iq Ir It Iu Iv Jh Lz Mc Md Mg Mh Mi Ml Mt My Na Nh Nm Ny Of Oy Pa Pg Pz Qc Qd) Oe(Hr Hx Ih Ii In Ip Iq Ir It Iu Iv Jh Lz Mc Md Mg Mi Ml Ms My Nc Ng Nm Ns Of Og Oy Oz Pa Pb Pz Qc) Pb(Hr Hx Ih Ii In Ip Iq Ir It Iu Iv Jh Lz Mc Md Mg Mi Ms My Nc Ng Nm Ns Of Og Oy Oz Pa Pz Qc) Ms(dN Hr Hx Ih Ii In Ip Iq Ir It Iu Iv Jh Lz Mc Md Mg Mi My Ng Nm Ns Of Oy Oz Pa Pz Qc) Mt(Hr Hx Ih Ii Ij Ip Iq Ir It Iu Iv Jh Lz Mc Md Mg Mi My Nh Nm Ny Of Oy Pa Pg Pz Qc Qd) Nc(Hr Hx Ih Ii In Io Ip Iq Ir It Iu Iv Jh Lz Mc Md Mg Mi My Ng Nm Ns Of Oy Oz Pa Pz Qc) Ml(Hr Hx Ih Ii Ij Ip Iq Ir It Iu Iv Jh Lz Mc Md Mg Mh Mi My Na Nh Nm Of Oy Pa Pz Qc) Qd(Hr Hx Ih Ii Ij Ip Iq Ir It Iu Iv Jh Lz Mc Md Mg Mi My Nm Ny Of Oy Pa Pg Pz Qc) Oz(dN Hr Hx Ih Ii Ip Iq Ir It Iu Iv Jh Lz Mc Md Mg Mi My Ng Nm Ns Of Oy Pa Pz Qc) Pg(Hr Hx Ih Ii Ij Ip Iq Ir It Iu Iv Jh Kq Lz Mc Md Mg Mi My Nm Ny Of Pa Pz Qc) Ns(Hr Hx Ih Ii Ip Iq Ir It Iu Iv Jh Lz Mc Md Mg Mi My Ng Nm Of Oy Pa Pz Qc) Na(Hr Hx Ih Ii Ij Ip Iq Ir It Iu Iv Jh Lz Mc Md Mg Mi My Nm Of Oy Pa Pz Qc) In(Hr Hx Ih Ii Ip Iq Ir It Iu Iv Jh Lz Mc Md Mg Mi My Ng Nm Of Oy Pa Pz Qc) Mh(Hr Hx Ih Ii Ip Iq Ir It Iu Iv Jh Lz Mc Md Mg Mi My Nm Of Oy Pa Pz Qc) Nh(Hr Hx Ih Ii Ip Iq Ir It Iu Iv Jh Lz Mc Md Mg Mi My Nm Of Oy Pa Pz Qc) Ny(Hr Hx Ih Ii Ip Iq Ir It Iu Iv Jh Lz Mc Md Mg Mi My Nm Of Oy Pa Pz Qc) Mf(Hr Hx Ih Ii Ip Iq Ir It Iu Iv Jh Lz Mc Md Mg Mi My Nm Of Pa Pz Qc) Ng(Hr Hx Ih Ii Ip Iq Ir It Iu Iv Lz Mc Md Mg Mi My Nm Of Oy Pa Pz Qc) Ij(Hr Hx Ih Ii Ip Iq Ir It Iu Iv Jh Lz Mc Md Mg Mi My Nm Of Pa Pz Qc) Io(fP Hr Hx Ih Ii Ip Iq Ir It Iu Iv Jh Lz Mc Md Mg Mi My Of Oy Pa Qc) dN(Ap Bg bH bM bO bR bV cA cR cT Cx dH Dp Ed eF Fp gP Ma Me Nf Ni Oi) Mw(Hr Hx Ih Ii Ip Iq Ir It Iu Iv Jh Lz Mc Md Mg Mi Nm Of Pa Pz Qc) Nt(Hx Ih Ii Ip Iq Ir It Iu Iv Jh Mc Md Mg Mi My Nm Of Pa Pz Qc) Og(Ih Ip Iq It Iu Iv Ki Lz Mc Md Mg Mi My Nm Of Oy Pa Pz Qc) bM(bA bF Bg bO bZ cT Cx EF gP Ma) Dp(Bg Jy Kq Ma Ni No Oi Pf Qv Sr) Pd(Hx Ii Iq Ir It Iu Iv Mg Mi Qc) Lz(Hr Ip Ir Jh Md Nm Oy Pz) Kq(Ef Ii Kj Oi Oy Us Uu) Hr(Ip Ir Jh Oy Pz Qc) Jh(Ip Ir My Oy Pz) Oy(Ip Ir Md Nm) Nf(Iq It Iu) Ni(aW Dr Tn) Ma(Ki Ri) Ir(Ip Pz) Oi(fP Iq) DrEf FafP MdPz bRdI} Jl{Jn(Hq Hr Hu Hv Hw Hx Ih Ij Ik Il Im Ip Iq Ir Is It Iu Iv Jg Jh Jk Jm Jp Jr Jt Lh Li Lj Lu Lx Ly Lz Mb Mc Md Mf Mg Mh Mi Mj Mk Ml Mm Mn Mp Mr Mt Mv Mw Mx My Mz Na Nb Nd Ne Nf Nh Nj Nm Nn No Nq Nr Nt Nu Nv Nw Nx Ny Of Oh Ok Om On Oz Pa Pb Pc Pd Pe Pf Pg Po Pz Qa Qb Qc Qd Qe) Nw(Fr Hq Hr Hu Hv Hw Hx Ih Ij Ik Il Im Ip Iq Ir Is It Iu Iv Jg Jh Jk Jm Jo Jp Jr Js Jt Lh Li Lj Lu Lx Ly Lz Mb Mc Md Mf Mg Mh Mi Mj Mk Ml Mm Mn Mp Mr Mt Mv Mw Mx Mz Na Nb Nc Nd Ne Nf Nh Nj Nl Nm Nn No Nq Nr Nt Nu Nx Ny Of Oh Om On Pc Pd Pe Pf Pg Po Pz Qa Qb Qc Qd Qe) No(Et Hq Hr Hu Hv Hw Hx Ih Ij Ik Il Im Ip Iq Ir Is It Iu Iv Jg Jh Jk Jm Jo Jp Jr Js Jt Lh Li Lj Lx Ly Lz Mb Mc Md Mf Mg Mh Mi Mj Mk Ml Mm Mn Mp Mr Mt Mv Mw Mx My Mz Na Nb Nd Ne Nh Nj Nm Nn Nq Nr Nt Nu Nv Nx Ny Of Oh Ok Om On Pd Pe Pf Pg Po Pz Qa Qb Qc Qd Qe Wm) Fr(Hq Hr Hv Hw Hx Ih Ij Ik Il Im In Ip Iq Ir Is Iu Iv Jg Jh Jm Jo Jp Js Jt Lh Li Lj Lu Lx Ly Lz Ma Mb Mc Md Mf Mh Mi Mj Mk Ml Mm Mn Mp Mr Mt Mu Mv Mw Mx Mz Na Nb Nc Nd Ne Nf Nh Nj Nl Nm Nn Nq Nr Nt Nu Nx Ny Of Oh Om On Pa Pc Pd Pe Pf Pg Po Pz Qb Qc Qd Qe) Jr(Fp Hq Hr Hu Hv Hw Hx Ih Ij Ik Il Im Ip Iq Ir Is It Iu Iv Jg Jh Jk Jm Jo Jp Js Jt Lh Li Lj Lx Ly Lz Mb Mc Md Mf Mg Mh Mi Mj Mk Ml Mn Mp Mr Mt Mv Mw Mx My Mz Na Nb Nd Ne Nf Nh Nj Nm Nq Nr Nt Nu Nv Nx Ny Of Oh Om On Pa Pd Pe Pf Pg Po Pz Qa Qb Qc Qd Qe) Oz(Hq Hr Hu Hv Hw Hx Ih Ii Ij Il Im Ip Iq Ir Is Iu Jg Jk Jm Jo Jp Js Jt Lh Li Lj Lu Lx Ly Mb Mc Md Mf Mg Mh Mi Mj Mk Ml Mm Mn Mp Mr Mt Mv Mw Mx My Mz Na Nb Nc Nd Ne Nf Nh Nj Nl Nm Nn Nt Nu Nv Ny Of Om On Oy Pa Pb Pc Pd Pe Pg Pz Qa Qb Qd Qe Us Wm) Mq(Hq Hr Hu Hv Hw Hx Ih Ij Ik Il Im Ip Iq Ir Is It Iu Iv Jg Jh Jk Jm Jp Js Jt Lh Li Lj Lx Lz Mb Mc Md Mf Mg Mh Mi Mj Mk Ml Mm Mn Mp Mr Mv Mw Mx My Na Nb Nc Nd Ne Nf Nh Nj Nm Nq Nr Nt Nu Nv Nx Ny Of Oh Om On Pa Pd Pe Pf Pg Po Pz Qa Qb Qc Qd Qe) Nk(Dr Hq Hr Hu Hv Hw Hx Ih Ii Ij Ik Il Ip Iq Ir Is It Iu Iv Jg Jh Jk Jm Jo Jp Js Jt Lh Li Lj Lu Lx Ly Lz Mb Mc Md Mf Mg Mh Mi Mj Mk Ml Mm Mn Mp Mr Mt Mv Mw Mx My Nb Nc Nd Ne Nf Nj Nl Nm Nq Nr Nt Nu Nv Nx Ny Of Om On Pa Pd Pe Pg Pz Qb Qc Qd Qe) Io(Hq Hr Hu Hv Hw Hx Ih Ii Ij Ik Il In Ip Iq Ir It Iu Iv Jg Jh Jk Jm Jo Jp Js Jt Lh Li Lj Lu Lx Lz Mb Mc Md Mf Mg Mh Mi Mj Mk Ml Mm Mn Mp Mr Mt Mv Mw Mx My Mz Nb Nc Nd Ne Nf Nh Nj Nl Nm Nn Nq Nt Nv Nx Ny Of Om On Pa Pb Pc Pd Pe Pg Pz Qb Qd Qe) Ma(Hr Hv Hx Ih Ij Ik Ip Iq Ir Is It Iu Iv Jg Jh Jk Jm Jp Js Jt Lh Li Lj Lu Lx Ly Lz Mb Mc Md Mf Mg Mh Mi Mj Mk Ml Mm Mn Mp Mr Mt Mv Mw Mx My Na Nb Nc Nd Ne Nf Nh Nj Nl Nm Nn Nq Nr Nt Nu Nv Nx Ny Of Oh Om On Pa Pd Pe Pf Pg Po Pz Qb Qc Qd Qe) Ns(Hq Hr Hu Hv Hw Hx Ih Ii Ij Ik Il Ip Iq Ir Is It Iu Iv Jg Jh Jk Jm Jo Jp Js Jt Lh Li Lj Lx Ly Lz Mb Mc Md Mf Mg Mh Mi Mj Mk Ml Mm Mn Mp Mr Mt Mv Mw Mx My Mz Na Nb Nd Ne Nh Nj Nm Nq Nr Nt Nu Nv Nx Ny Of Pa Pb Pd Pe Pg Pz Qb Qc Qd Qe) Et(Hq Hr Hu Hv Hw Hx Ih Ij Ik Il Ip Iq Ir Is It Iu Iv Jg Jh Jk Jm Jp Js Lh Li Lj Lx Lz Mb Mc Md Mf Mh Mi Mj Mk Ml Mm Mn Mp Mr Mt Mv Mw Mx My Na Nb Nd Nc Nh Nj Nm Nq Nr Nt Nu Nv Nx Ny Of Oh Ok Om On Pd Pe Pf Pg Po Qa Qb Qc Qd Qe) Ok(Hq Hv Hw Hx Ih Ij Ik Il Im Ip Iq Ir Is It Iu Iv Jg Jh Jk Jm Jp Js Lh Li Lj Lx Lz Mc Md Mf Mg Mh Mi Mj Mk Ml Mm Mn Mp Mr Mt Mv Mw Mx My Mz Na Nb Nd Ne Nh Nj Nm Nq Nr Nt Nu Nv Nx Ny Oh Om On Pd Pe Pf Pg Po Pz Qa Qb Qc Qd Qe) Fp(Hq Hu Hv Hw Hx Ij Ik Il Im Ip Iq Ir Is It Iv Jg Jh Jk Jm Jp Js Jt Lh Li Lj Lx Lz Mb Mc Md Mf Mg Mh Mi Mj Mk Ml Mn Mp Mr Mt Mv Mw Mx My Na Nb Nd Ne Nf Nh Nj Nm Nq Nr Nt Nu Nv Nx Ny Of Oh Pa Pd Pe Pf Pg Po Qa Qb Qc Qd Qe) In(Hq Hr Hx Ih Ii Ij Ik Il Ip Iq Ir It Iu Iv Jg Jh Jk Jm Jo Jp Js Jt Lh Li Lj Lu Lx Ly Lz Mb Mc Md Mf Mg Mh Mi Mj Mk Ml Mm Mn Mp Mr Mt Mv Mw Mx Nb Nc Nd Ne Nh Nj Nl Nm Nq Nr Nt Nu Nv Nx Ny Of Oy Pa Pb Pd Pg Pz Qb Qc Qd Wm) Lw(Hq Hr Hv Hw Hx Ih Ij Ik Ip Iq Ir Is It Iu Iv Jg Jh Jk Jm Jp Js Jt Lh Li Lj Lx Lz Mc Md Mf Mg Mh Mi Mj Mk Ml Mm Mn Mp Mr Mv Mw Mx Na Nb Nc Nh Nj Nm Nn Nq Nr Nt Nu Nv Nx Ny Oh Om On Pc Pd Pe Pg Po Pz Qa Qb Qc Qd Qe) Nn(Hq Hr Hv Hw Hx Ih Ij Il Im Ip Iq Ir Is Iu Jh Jm Jo Jp Js Jt Lh Lj Lu Lx Ly Mb Mc Mf Mg Mh Mi Mk Ml Mm Mn Mr Mt Mu Mv Mw Mz Na Nc Nd Ne Nf Nh Nj Nl Nm Nq Nt Of Oh Om On Pa Pc Pe Pf Po Pz Qa Qb Qd Qe) Oy(Hq Hr Hu Hv Hx Ih Ii Ik Il Ip Iq Ir Is Iu Iv Jh Jk Jm Jo Jp Js Jt Kq Li Lj Ly Mb Mc Md Mf Mg Mh Mi Mj Mk Mm Mn Mp Mr Mv Mw Mx My Na Nd Ne Nh Nj Nl Nm Nq Nt Nu Nv Nx Ny Of Pa Pb Pd Pg Pz Qb Qd Qe Wm) Nc(Dr Hq Hr Hu Hv Hw Hx Ih Ii Ij Il Ip Ir Is Iu Jg Jk Jm Jo Jp Js Jt Lh Lj Lu Lx Ly Mb Mc Mf Mg Mh Mi Mk Ml Mm Mn Mr Mv Mw Mx My Na Nb Nd Ne Nf Nj Nl Nm Nt Nv Ny Of Oh Om On Pa Pc Pd Pe Po Pz Qd Qe) Mz(Hq Hr Hu Hv Hw Hx Ih Ii Il Ip Iq Is Iu Jg Jk Jm Jo Jp Js Jt Lj Lu Ly Lz Mb Mc Mf Mg Mh Mj Mk Mm Mn Mr Mv Mw My Na Nd Ne Nf Nh Nj Nl Nr Nv Of Oh Om On Pa Pc Pe Pf Po Pz Qa Qb Qc Qc) Im(Hq Hr Hu Hv Hw Hx Ih Ii Ij Il Ip Iq Ir Is Iu Jk Jm Jo Jp Jt Lh Lx Ly Mb Mc Mf Mg Mh Mi Mj Mk Ml Mm Mn Mr Mt Mx My Na Nd Ne Nf Nh Nl Nm Nv Of Oh Om On Pa Pb Pc Pe Pf Po Pz Qa Qb Qe) Ms(Hq Hv Hx Ih Ii Ik Il Ip Iq Ir It Iu Iv Jh Jk Jm Jo Jp Js Jt Lh Li Lj Lx Lz Mb Mc Md Mf Mg Mh Mi Mj Mk Mp Mx My Nd Ne Nh Nj Nm Nq Nr Nt Nu Nv Nx Ny Of Pa Pd Pe Pg Pz Qb Qc Qd Wm) Nl(Hq Hr Hu Hv Hw Ih Ii Ij Il Ir Is Iv Jm Jo Jp Js Jt Lh Lj Lu Lx Ly Mb Mf Mg Mh Mi Mk Ml Mm Mn Mr Mt Mw Mx My Na Nd Ne Nf Nj Nm Nt Nv Of Oh Om On Pa Pb Pc Pe Pf Po Pz Qa Qd Qe) Om(Hq Hr Hv Hw Hx Ih Il Ip Iq Ir Is Iu Jh Jk Jm Jp Jt Lj Lu Ly Mb Mc Md Mf Mh Mk Ml Mm Mr Mt Mu Mv Mw Mx Na Nb Nd Ne Nf Nh Nm Nq Nx Ny Oh On Pa Pc Pe Pf Pg Po Pz Qa Qd Qc) Lu(Hq Hr Hu Hv Hw Ii Ij Il Ir Is Jk Jm Jo Jp Jt Lh Lj Lx Ly Mb Mf Mg Mh Mi Mk Ml Mm Mn Mr Mt

Nl Nq Ns Nt Nu Nv Nx Ny Oe Of Oi Oy Oz Pb Pd Pg Pz Qb Qd Rv To Th) Pf(Aj Fp Hq Hr Hu Ih Il In Ip Ir Iv Jg Jk Jo Js Jt Lh Lj Lu Lx Ly Lz
Ma Mg Mi Mp Mr Ms Mt Mv Mw Mx My Mz Na Nb Nc Ne Nf Nh Nj Nk Nl Ns Nt Nv Nx Ny Oe Of Oh Om Oz Pa Pe Qb Qd Rv Yl) Qa(Aj
aW Fp Hq Hv Hw Hx Ih Ij Ik Il Ip Iq Iu Iv Jh Jk Jm Js Jt Li Lj Lz Mb Mc Md Mf Mg Mh Mj Mk Ml Mx My Nb Nc Nd Nh Nl Nm Nq Nr Nt Nu
Nv Nx Ny Of Pd Pg Qb Qc Qd Tn Tv Ux Ti Th) Im(Fp Hr Hu In Io Ir Jg Jk Js Jt Li Lj Lw Ly Lz Ma Me Mf Mh Mj Mk Ml Mp Ms Mv Mw Mx
Na Nb Nc Ne Nf Nh Nj Nk Nl Nr Ns Nt Nv Ny Oe Oi Oy Oz Pb Pd Pg Qb Qd Tn To Tv Ye) Yl(aS Ax bA bR Cx dE dN Dp Du Ed Et Fw Ha
Hw In Is Jd Jn Jp Js Kc Ld Lh Mj Mq Mt Mv Mw Mz Ne Nh Nk Nl Nu Nw Nx Ny Ok Ow Oz Pb Pg Ps Ql Ra Ri Rm Sr Wc Tm Xa Ti Th)
Po(Aj aW Hv Hw Hx Ij Ik Il Io Ip Iq Ir It Iv Jh Jk Jm Js Jt Li Lj Lz Mb Mc Md Mf Mh Mj Mk Ml Mv Na Nb Nd Nf Nm Nq Nr Nu Nx Ny Pd Pg
Pz Qc Rv To) Et(Fp Ih In Jg Jk Jo Jp Lh Li Lj Lw Lz Ma Me Mg Mh Mi Mj Ml Mn Mp Mr Ms Mv Mw Mx Mz Nc Ne Nf Nh Nj Nl Ns Nt Og
Oi Ok Om Oy Oz Pa Pb Qb Qd Ux Th) Nn(Aj aW Hq Hv Hw Hx Ij Ik Il Io Ip Iq It Iu Iv Jg Jh Jk Jm Js Li Lz Mc Md Mf Mj Mk Ml Mp Mv Mx
Nb Nd Nf Nm Nq Nr Nu Nv Nx Ny Pd Pg Pz Qc Th) Nw(Hv Hw Hx Ij Ik Il Io Ip Iq Ir It Iu Iv Jg Jk Jm Js Jt Lh Li Lx Lz Mb Mc Mf Mg Mj Mk
Ml Mt Mz Nb Nc Nd Nf Nh Nm Nq Nr Nu Oe Om Pd Qc Wf Xa) Xa(Aj Ap aZ Bb dC Dg dH dN Du Eq Ha Hc Hf Is Jt Ki Kl Lj Mb Mp Ng Nu
Og Or Ow Oy Oz Pc Pi Rc Ri Rm Rt Rv Ss Us Uy Vo Vt Wb Th) Is(Aj bV Hc Hq Hv Hw Hx Ik Iq Iv Jh Jk Js Mc Md Mf Mj Mk Ml Nb Nd Nm
Nq Nr Nu Nv Nx Qb Qc Qd Tn Tr Tt Tv Wb Ti Th) Oh(Fp Jk Jn Jo Jt Lh Lu Lw Ly Ma Me Mi Mr Mt Mv Mw Mz Nb Ne Nh Nj Nk Nl Ns Nt
Ny Oe Oy Oz Pa Pb Pe Qb Qd Rv) Ok(Fp In Jn Jo Jp Jq Lh Lj Lu Lw Lx Ly Ma Me Mg Mh Mi Mn Mp Mq Ms Mt Mv Mx Mz Ne Nk Og Oi
Oz Pa Pb Pe Qb Qd) Th(bH bW Cv dK dN Dp Ed Ez Jd Jk Kq Lh Lw Lx Mm Mp Mq Mt No Ny Or Ou Ow Qb Qh Rv Sh Sr Uf Uh Ul) Qb(Du
Fd Gn Hp In Jp Jq Lt Lv Lx Mm Mn Pc Ps Rt Rv Ry Sf Sj Uy Vb Vj Vz Wb We Wf Yd Tm Tl Ti) Lv(Fp Ih Jg Jq Jt Lh Li Lj Lw Ly Ma Mi Mp
Mq Mr Mv Mw Mx Ne Nt Ny Og Om Pa Pc Qd) Jn(In Jg Jp Jq Lh Lw Ly Ma Me Mi Mn Mp Mq Mr Ms Mv Mw Ng Og Oi Om Pa Pe) On(Hw
Hx Ij Ik Il Iq It Iu Iv Jg Jm Lh Mc Nd Nr Nt Nu Pd Qc Vz Wf Ti) Lx(Fp Hq In Jg Jp Jq Lj Ma Me Mm Mn Mq Ms Mw My Ne Ny Of Pc Pg Qd)
Pe(In Jg Jo Jp Jq Lw Ly Ma Mn Mq Ms Mt Mw Ng Og Oi Om Oy Oz Pa Qd) Jq(Fp Jg Jp Lh Li Lu Ly Ma Mh Mm Mn Mr Ms Mv Mw Og Pa
Qd) Jj(Dp Ij Jg Jm Jt Li Mm Mp Mr Mt Mv Mz Nv Ny Pc Pg) No(Aj Ao aW Bb Co dI dM dN Dp Hc Tn Tv Uu Wm) Rv(Cx Ez Fy Ih Jk Ks Mt
Ow Oz Pg Ps St Ua Ut) Fr(Aj Hx Ij Iq It Jg Jm Mk Nm Qc Wm) Ng(Jd Jp Kq Lh Ma Mn Mq Mv Nv Qd Tn) Lh(Lw Ly Mm Mn Ms Og Pb Pc
Vz Wf) Om(Fp Hu In Lj Ly Me My Of Pb Qd) Mq(Jp Ma Mi Mm Mn Mt Mz Pc Qd) Ti(Ed Jk Mt Ny Ow Oz Ri St) Tn(Ed Kg Lw Ly Pc Ri Sr
St) Jp(Fp Lw Me Mm Ne Nk Pc Wm) Aj(dN Fy Hu Jd Jk Kq) Pc(aW Fp Qd To Tr Tt) Mm(Fp Mt Mv Mz Qd) Mn(Fp Ne Nh Pa Qd) Wf(Jk Mt
Mw Or Ut) Kq(Ao Hc Kj Of Uu) Ps(Ap Cx Dp Oe Ri) Lw(Ed Fp To Tv) Jg(Ms My Og Qd) dN(Ed Ly Me Nk) Fd(bN dE Ri) Mt(Gn Ux Vz)
Mw(To Wb Wh) Oz(aW Wb Ye) Cx(Du Hp) Nk(aW dM) To(Qd Sr) Tr(Hc Or) Jm(Sj Tl) Ri(Du Uy) ApZq DpVi FpMa NrdM MsUn HpNx TtOr TvSt WbOw VzPg JdOy OpPa bRdI} Fr{Jn(Hq Hr Hv Hw Hx Ih Ii Ij Ik Il Im Io Ip Iq Ir Is It Iu Iv Jg Jh Jk Jm Jo Jp Js Jt Lh Li Lj Lu Lx Ly Lz Ma Mb Mc Md Mf Mh Mi Mj Mk Ml Mm Mn Mp Mr Mt Mv Mw Mx Mz Na Nb Nc Nd Ne Nf Nh Nj Nk Nl Nm Nn No Nq Nr Nt Nu Nv Nw Nx Ny Of Oh Ok Om On Oz Pb Pc Pd Pe Pf Pg Po Pz Qa Qb Qc Qd Qe) Qa(Hq Hr Hv Hw Hx Ih Ij Ik Im Ip Ir Is It Iu Iv Jg Jh Jo Jp Js Jt Lh Li Lj Lu Lx Ly Lz Mc Md Mf Mh Mi Mj Mk Ml Mm Mn Mp Mr Mt Mv Mw Mx Mz Na Nb Nc Nd Ne Nf Nh Nj Nk Nl Nm Nn No Nq Nr Nt Nu Nv Nx Ny Oh Ok Om On Oz Pc Pd Pe Pf Pg Po Pz Qb Qc Qd Qe Wm) Is(Et Hq Hr Hv Hw Ih Ij Im Io Ip Iq Ir Iu Jh Jo Jt Lh Lj Lu Lw Lx Ly Ma Mb Mc Mf Mh Mi Mk Ml Mm Mr Mt Mv Mw Mx Mz Na Nc Nd Ne Nf Nh Nj Nk Nl Nm No Nq Nt Nu Nv Nw Of Oh Ok Om On Oz Pa Pb Pc Pe Pf Po Pz Qe) Jq(Hq Hr Hv Hw Hx Ih Ij Ik Il Io Ip Iq Ir It Iu Iv Jg Jk Jm Jp Js Jt Lh Li Lu Lw Lx Ly Lz Mc Mf Mh Mi Mj Mk Ml Mn Mp Mt Mz Na Nb Nc Nd Nf Nj Nk Nl Nm Nn Nq Nr Nt Nu Nx Ny On Pd Pe Pg Pz Qb Qc Qd Wm) Oi(Hq Hr Hv Hw Ij Ik Il In Io Iq It Iv Jg Jh Jk Jo Jp Js Li Lu Lx Ly Lz Ma Mb Mc Md Mf Mg Mh Mi Mj Ml Mm Mn Mp Mv Mw Na Nb Nc Nd Nf Nj Nk Nl Nm Nq Nr Nu Nv Nx Ny Oe Of Og Om Oz Pa Pb Pc Pd Pf Pg Wm) No(Et Hq Hu Hv Hw Ii Ij Il Im In Iq Ir Jk Jm Jo Jt Lh Li Lj Lu Lw Ma Mb Mf Mg Mh Mm Mr Mt Mv Mw Mz Nc Nd Ne Nf Nh Nj Nk Nl Nn Nq Nr Ns Nt Nv Nw Of Oh Ok Om On Oz Pb Pc Pe Pz Qe) Me(dN Hq Hr Hv Hw Hx Ij Ik Il Io Ip Ir It Iu Iv Jg Jm Jp Js Jt Lh Li Lu Ly Mc Md Mf Mh Mi Mj Mk Ml Mp Na Nb Nc Nd Nf Nj Nk Nm Nr Nv Nx Ny Om Pa Pd Pg Pz Qc) Jr(Hx Ih Ij Ik Ip Ir It Iu Iv Jg Jh Jo Jp Js Jt Lh Li Lx Ly Lz Mc Md Mh Mi Mj Mk Ml Mn Mp Mt Mx Na Nb Nf Nm Nn Nq Nr Nu Nx Ny Om On Pd Pf Pg Po Qb Qc Qd) Og(Dr Hu Hv Hw Hx Ih Ii Ik In Io Ir Iv Jo Js Lj Lx Ma Md Mf Mg Mh Mi Ml Mm Ms Mt Mw Mx My Na Nb Nd Nj Nl Nn Ns Nu Ny Oz Pa Pb Pc Pf Qb Qd) Oy(dN Hx Ih Ij Ik In Io It Iv Jp Js Kq Lz Ma Mb Mf Mg Mh Mi Mj Mk Ml Mm Mn Mt Mv Mw My Nc Nd Nf Nj Nl Nn Nq Nu Nx Ny Oe Oz Pa Pc Pg Pk Un) Qe(Et Hv Hw Ii Ij Il Im In Io Iq Ir Jk Jo Jt Lw Ma Mb Mg Mm Mr Mt Mv Mw Mz Na Nd Ne Nh Nj Nl Ns Nw Of Ok Oz Pa Pb Pc Pe Pz Wm) Im(Et Hv Hw Io Ir Jo Jt Lh Lj Lu Lw Ma Mg Mh Ml Mr Mt Mv Mw Mx Mz Na Nd Ne Nh Ns Nt Nw Oh Ok On Oz Pa Pb Pe Pf Po Qd) Et(Hq Hu Hv Hw Ii In Io Ir Jo Lj Lu Lw Mh Mr Mt Mx My Mz Nd Ne Nf Nh Nl Ns Nw Oe Of Oh Ok Oz Pa Pb Pe Po Pz Qd) Ok(Hu Hw Ii In Io Jo Jt Lj Lu Lw Ly Ma Mb Mr Mx My Mz Nd Ne Nf Nh Nm Nn Ns Nw Oe Of Oh Oz Pa Pb Pc Pf Po Pz) Ms(Hu Hv Hw Ij In Ir Jo Jt Lh Lw Lx Ml Mm Mr Mw Mx Mz Na Nb Ne Nf Nh Nn Ns Nt Nu Oz Pb Pc Pe Po Qb Qd) Hu(Hv Hw Ij Ik Io Ir Jo Jt Lh Lw Lx Ma Mr Mt Mx Mz Na Nd Nf Nj Nl Nn Ns Nt Oh Oz Pe Pf Po Qb Wm) Nw(Hq Hv Hw Ii In Ir Jo Jt Lj Lw Ly Ma Mg Mr Mv Mw Na Nd Ne Nh Nq Ns Nv Oe Of Oh Oz Pa Pb) Dr(aD aL An aW BA Bc bH bJ bL Bn cM cT cX cZ Ef Ex Gc Ii Kc Kg Mw Nd Oz Pb To Us Vh) My(Hv Hw Hx Ij In Ir Jh Jt Lh Lw Lx Ml Mr Mt Mx Mz Na Ne Nf Nl Nn Nt Ny Oh Pe Po Qb Wm) Lv(Hr Hx Ik It Iu Jg Jp Li Mb Mc Md Mf Mj Mk Mn Mp Nc Nk Nm Nr Nx Pd Pg Qc Wm) Oe(Hv Hw Ih Ir Jt Lh Lw Mr Mx Mz Na Ne Nh Nn Nt Oh Om Pe Po Qb Qd Wm) Fp(It Jg Lx Lz Mb Mc Md Mj Mk Ml Mr Nb Nf Nj Ny Pd Pg Qb Qc Wm) Ns(Hv Hw Ir Jt Lw Mg Mr Mz Na Ne Nf Nh Nl Nn Nt Oh Om On Pe Po) Mq(Hx It Jg Jp Li Lz Mc Md Mj Mp Nb Nc Nr Nu Ny Om Pd Qc Wm) Jj(Hr Hx Ii Ip Iq Iu Jg Jh Li Lz Mc Md Mk Mp Nk Nq Nv Pz Qc) Pb(Hv Hw Ij Jo Jt Lh Lw Lx Mr Mx Mz Ne Nh Nt Oh On Pe Po Wm) Mg(Hv Hw Ir Jo Jt Lh Lw Lx Mz Nh Nt Oh Om On Pe Po) Nh(Hv Hw Ir Lj Lw Ly Mr Mz Nc Nf Of Oh Oz Pe Po) Mz(In Lw Ma Mm Mr Mv Mw Ne Of Oh Pa) Of(Hv Hw Ij In Jo Jt Lh Om On) Oh(Hv Hw Ii Nd Ne Oz Pa) Oz(Mr Ne Pe Po Wm) Lw(Mr Ne Pe Po) On(Ii Jk Mv Nv) Wm(Ly Na) Po(In Pa) Kq(Bb Uu) Om(Mv Mw) Pe(In Pa) dN(cT Ed) MbHw NcNe JkLh JoJt} Jj{Is(Hr Hv Hw Ih Ii Ij Il Im In Io Iq Ir It Jg Jh Jk Jn Jo Jp Jq Jt Li Lj Lw Lx Ly Mb Mc Md Mf Mg Mh Mi Mj Mk Ml Mm Mn Mp Ms Mt Mv Mw Mx Mz Na Nb Nc Nd Ne Ng Nh Nj Nk Nl Nm Nq Nr Ns Nu Nv Nw Nx Ny Oe Og Oh Ok Oy Oz Pa Pb Pc Pd Pg Qa Qb Qd Wm) Qe(Hq Hr Hv Hw Hx Ih Ii Ij Il In Io Ip Iq Ir It Iu Iv Jh Jk Jm Jp Js Jt Li Lj Ly Lz Mb Mc Md Mf Mg Mh Mi Mj Mk Ml Mm Mn Mp Ms Mt Mx My Na Nb Nc Nd Ne Ng Nh Nj Nk Nl Nm Nq Nr Ns Nu Nv Nx Ny Oe Of Oy Oz Pa Pb Pd Pg Pz Qa Qb Qc Qd Wm) Qa(Hq Hr Hv Hw Hx Ih Ii Ij Il Ip Iq Ir It Iu Iv Jh Jk Jm Jn Jo Jp Js Jt Li Lj Ly Lz Mb Mc Md Mf Mg Mh Mi Mj Mk Ml Mm Mp Ms Mx My Na Nb Nc Nd Ne Ng Nh Nj Nk Nl Nm Nq Nr Ns Nu Nv Nx Ny Oe Of Oy Oz Pa Pg Pz Qb Qc Qd Wm) No(Dp Hq Hr Hv Hx Ih Ii Il In Ip Iq Ir It Iu Iv Jh Jm Jp Js Jt Li Lx Ly Lz Mb Mc Md Mf Mg Mh Mi Mj Mk Ml Mm Mn Mp Mt Mv Mx My Mz Na Nb Ne Ng Nj Nk Nl Nm Nq Nr Nu Nv Nw Nx Ny Oe Of Og Oy Pb Pd Pe Pf Pg Pz Qb Qc Qd) Nn(Dp Hq Hr Hx Ih Ii Ij Il In Io Ip Iq It Iu Iv Jg Jh Jk Jm Jp Js Li Lj Lw Ly Lz Mb Mc Md Mf Mg Mi Mj Mk Ml Mm Mn Mp Mt Mv Mw Mx My Nb Nc Nk Nl Nm Nq Nr Nu Nv Nx Ny Oe Of Oh Oy Oz Pa Pb Pc Pg Pz Qb Qc Wm) On(Hq Hr Hx Ih Ii Ij Il Ip Iq Ir It Iu Iv Jg Jh Jk Jm Jo Jp Js Jt Li Lw Lx Lz Mb Mc Md Mf Mg Mi Mj Mk Ml Mm Mn Mp Mt Mv Mx Nb Nc Nk Nl Nm Nq Nr Nu Nv Nw Nx Ny Of Ok Om Pc Pd Pg Pz Qb Qc) Fp(Hq Hr Hu Hv Hw Ih Ii Ik Il In Ir Iu Iv Jh Jm Js Li Lu Ly Mc Md Mf Mg Mh Mi Mj Mk Mm Mp Ms Mt Mx My Na Nb Ne Nf Ng Nh Nl Nm Nq Nr Ns Nu Nx Oe Of Og Oi Oz Pa Pb Pd Pz Qb) Lv(Hq Hr Hv Hw Hx Ih Ii Il In Ip Iq Ir

Figure 7 Continued

It Iu Iv Jh Jo Js Ly Lz Mb Mc Md Mf Mg Mh Mi Mj Mk Ml Mp Ms My Na Nc Nd Ne Ng Nj Nk Nl Nm Nq Ns Oe Of Og Oi Oy Oz Pb Pz Qc Wm) Jr(Hv Hw Ij In Jm Jn Jo Jp Jt Lu Lw Lx Mf Mg Mi Mm Mn Mr Ms Mt Mv Mw Mz Nb Nc Nd Ne Nf Ng Nh Nj Nr Ns Nu Nv Nx Ny Of Oh Oi Oz Pa Pc Pd Pe Pg Qb Qd Wm) Om(Et Hu Hw Ih Ik Im In Jk Jm Jn Jq Lh Lj Lu Ly Ma Mg Mh Mj Ml Mn Ms Mt Mv Mw Mx My Mz Na Ne Nf Nh Nj Nl Nr Ns Nt Nw Oi Ok Oy Oz Pb Pc Pd Pe Pg Qb Qd) Mq(Hu Hv Hw Ih Ij In Ir Jm Jo Js Jt Li Lj Lu Lw Lx Ly Mi Mj Ml Mm Mp Mr Mv Mx Na Nb Ne Nf Ng Nh Nj Nm Nq Nr Ns Nu Nv Nx Ny Og Oi Oz Pa Pb Pd Pz Qb) Lh(Et Hu Ik Io Ir Jk Jq Lu Lw Lx Ly Ma Mh Mi Mm Mn Ms Mt Mv Mw Mz Na Ne Nf Ng Nh Ns Nt Nu Nw Ny Og Oi Ok Oy Oz Pb Pc Pd Pe Pg Qb Qd Wm) Pf(Et Hu Hv Hw Ij Ik Im In Ir Jg Jk Jn Jo Jt Lj Lu Lw Lx Ma Mn Mr Mt Mw Mz Na Nb Nf Ng Nh Ns Nv Nw Nx Ny Oh Oi Ok Oy Oz Pa Pb Pc Pe Qd) Nw(Et Hu Hv Hw Ij Ik Im Io Ir Jk Jn Jo Jq Jt Lu Ly Mh Mr Ms Mv Mw Mz Na Ne Ng Nh Ns Nt Og Oh Oi Ok Oz Pa Pb Pc Pd Pe) Oh(Hu Hv Hw Ij Ik Im In Jg Jk Jn Jo Jt Lu Lw Lx Ma Mn Mr Ms Mv Mw Mz Nb Nf Nh Nv Ny Oi Ok Oz Pc Pd Pe Pg Qd) Pe(Et Hu Ik Im Jg Jk Jn Lu Lw Ma Me Mm Mn Mr Ms Mt Mv Mw Mz Nf Nh Ns Nt Nx Ny Og Oi Ok Oy Oz Pa Pb Pc) Jq(Et Hu Ik Im Jg Jk Jm Jn Lx Me Mh Mj Mn Ms Mt Mw Ne Nf Nh Nr Ny Og Ok Pa Pc Pd Pg Qb Qd Wm) Nt(Et Ij Im Jk Jn Lu Lx Ly Ma Me Mn Mr Mt Mv Mw Mx Mz Ng Ny Og Oi Ok Pc Pg Qb Qd) Et(Hu Hw Ij Ik Im Jk Lx Ma Mh Mr Mt Mv Mw Mz Nb Ne Nh Nr Oi Pc Pd Pg Qb Qd) Jn(Hu Ij Ik Im Jg Jk Jo Lu Lw Lx Me Mm Mn Mr Mv Mw Nh Oi Ok Pc Pd Pg Wm) Ok(Hu Im Jk Lx Ma Mh Mr Ms Mt Mv Mw Mz Ng Nh Nr Og Oi Pc Pd Pg) Im(Hu Jk Jo Jt Lu Lx Ma Me Mj Mr Mv Mz Nb Nf Pd Pg) Me(Jg Jk Lx Mm Mn Mr Mt Mw Nv Pg Qd) Ma(Jk Jt Mr Mz Nh Qd) Mr(Jg Jk Mn Mw Pc) Nf(eF gL Jg Mt Qd) Dp(Jp Jy Kq Sr) Wm(Jp Po) Kq(Bb Oy) MnNh JkOi} Lv{Po(Et Fp Hq Hr Hu Hv Hw Ih Ii Ij Ik Il Im Ip Iq Ir Is It Iu Jg Jh Jm Jn Jp Js Jt Lh Lj Lw Lx Ly Lz Ma Mc Me Mg Mh Mi Mj Mk Ml Mn Mp Mq Mr Mv Mw Mx My Na Nb Nc Nd Ne Nf Nh Nj Nk Nl Nm Nn Nr Ns Nt Nu Nv Nx Ny Oe Of Oh Ok Om Oz Pa Pc Pd Pe Pf Pg Pz Qa Qb Qc Qd Qe) Nn(Hq Hr Hv Hw Hx Ih Ij Ik Il Ip Iq Ir It Iu Iv Jg Jh Jk Jm Jp Js Jt Lh Li Lj Lw Lx Ly Lz Ma Mb Mc Md Mf Mg Mh Mi Mj Mk Ml Mn Mp Mv Mw Mx Na Nb Nc Nd Ne Nf Nh Nj Nk Nl Nm Nq Nr Nt Nu Nv Nx Ny Of Oh Om Oz Pa Pd Pg Pz Qb Qc Qd Qe) Nw(Hq Hr Hv Hw Hx Ih Ii Ij Ik Il In Ip Iq Ir Is It Iu Iv Jg Jh Jk Jm Jo Jp Js Jt Lh Li Lj Lx Lz Mb Mc Md Mf Mg Mh Mi Mj Mk Ml Mn Mp Mr Mt Mv Mx Na Nb Nc Nd Ne Nf Nh Nj Nk Nl Nm Nq Nr Nt Nu Nv Nx Ny Oe Of Om Pd Pg Pz Qb Qc Qd) On(Et Hr Hv Hw Hx Ih Ij Ik Il Ip Iq Ir Is It Iu Iv Jg Jm Jp Js Jt Lh Li Lx Ly Lz Ma Mb Mc Md Mf Mh Mi Mj Mk Ml Mn Mp Mr Mx Na Nb Nc Nd Ne Nf Nh Nj Nk Nl Nm Nq Nr Nt Nu Nv Nx Ny Ok Om Oz Pa Pd Pe Pg Pz Qb Qc Qd Qe) Qa(Et Fp Hr Hu Hv Ih Ii Im Iq Is It Iu Jg Jm Jn Jo Jp Jq Jr Lh Lw Lx Ly Ma Me Mi Mm Mn Mr Ms Mv Mw Mx Mz Nb Nc Nf Ng Nh Nk Nl Ns Nt Oe Oh Ok Om Oy Oz Pa Pb Pc Pe Pf Pz Qb) Jr(Fp Hr Hu Hv Iq Is Jg Jn Jo Jp Jq Jt Lh Li Lw Lx Ly Ma Me Mi Mn Mp Mr Ms Mt Mv Mx Mz Na Nb Nc Ne Nf Ng Nh Nk Nl Ns Nt Nu Ny Oe Og Oh Om Oy Oz Pa Pb Pd Pe Qb Qd Qe) Im(Et Fp Hu Hw In Is Jg Jn Jp Jq Jt Lh Lw Lx Ly Ma Me Mh Mi Mj Ml Mn Mr Ms Mv Mw Mx Na Nb Ne Nf Ng Nh Ns Nt Nu Oe Og Oh Oi Ok Om Oy Oz Pa Pb Pc Pd Qb Qe) Pf(Et Fp Hq Hu Hw In Io Ir Is Jg Jn Jo Jp Jt Lh Lw Lx Ly Mg Mm Mn Mr Ms Mt Mw Mx Mz Na Nb Nd Nf Nh Nk Ns Nt Ny Of Og Oh Ok Om Oz Pa Pb Pc Pe Qd Qe) Et(Fp Hu In Is Jn Jo Jq Lh Lj Lw Lx Ly Me Mi Ml Mm Mq Mr Ms Mt Mv Mw Mx Mz Nb Ne Nf Ng Nh Ns Nt Og Oh Oi Ok Om Oy Oz Pa Pb Pc Pe Qe) Ok(Fp Hu Ii In Io Is Jn Jo Jp Jq Lj Lw Lx Ly Me Mg Mm Mq Mr Ms Mt Mw Mx Mz Nf Nh Ns Og Oh Oy Oz Pa Pb Pc Pe Qe) Mq(Fp In Io Jn Jp Lh Lj Lu Lw Lx Ly Ma Me Mi Mm Mn Mr Ms Mw Mx Ng Nh Ns Nt Og Oi Om Oz Pa Pb Pc Pe Qd Qe) Oh(Fp Hu In Io Is Jg Jn Jp Jq Lh Lw Lx Ly Me Mm Mr Ms Mt Mv Mw Mz Nf Ng Ns Nt Oe Om Oy Oz Pa Pb Pc Pe Qe) Is(Fp Ii In Jm Jn Jo Jp Jq Lh Lw Lx Ly Ma Me Mr Ms Mt Mw Mz Nf Ng Og Oi Om Oy Pa Pc Pe Qe) Mm(Hu In Jp Lh Lj Lx Ly Ml Mr Mv Mw Mx Na Nb Nf Ng Nh Ns Nt Og Oi Om Oy Pa Pc Qd Qe) Mz(Fp Hu In Io Jg Jp Lh Lu Lw Lx Ma Me Mr Mv Mw Nh Nt Og Oi Om Oy Pa Pb Pc Pe Qe) Pe(Fp In Io Jg Jo Jp Jq Lu Lw Ly Me Ms Mt Mw Ng Ns Og Oi Om Oy Oz Pa Pb Pc Qe) Mt(Fp In Io Jp Jq Lh Lu Lw Lx Ma Me Mr Mw Na Ng Nh Nt Og Oi Om Pa Pc Qe) Fp(In Io Jg Jp Lh Lu Lw Lx Ly Ma Mr Mv Mw Og Oi Om Pa Pc) Jq(Dr In Io Jg Jp Lh Lu Lx Ma Mr Mv Mw Nt Og Pa Pc Qe Wm) Qe(In Lh Lu Lw Lx Me Mr Ms Mw Nf Ng Og Om Oy Pc Qb) Om(Hu In Jo Lj Lu Ly Me Mg Ms My Ns Of Oi Oy Pb) Dr(Dc dE Hu In Jy Lu Mp Nk Nu Pa Pg Qn Qy) Lx(Hq Io Lu Ly Me Mw Ns Of Og Oi Pb Pc Pg) Lu(Jp Jt Lh Li Lj Lw Mn Mw Nt Pc Qd) Mw(Io Lw Me Mr Ms Ng Og Oi Pa) Lh(In Io Lo Lw Ng Og Oi Pb Pc) Mr(Io Lw Og Oi Pb Pc) Og(Jg Nb Nt Pa Pc) Ng(Jp Ma Mv Nt) Io(Jp Lw Pa Qd) Jp(Me Oi) Kq(Bb Oy) NtOi} Kq{Oy(aC AD aE aF aG aH aI aJ aK AL aM AN aO AP aQ AR AS aU aV aW aX aY aZ bA bB BC bE bF BG bH bI bL bM BN Bo bP bQ bR bS bU bV bW bZ cA cB cC cD cE cF cG CH cJ cK cL cM cN CO CP CQ cR CS CT CU CV CW cX cY DB dC DD DE dF DG dH DI dJ DK DL dM Dr Ef Et Ez Fa Fb Fw Gl Gp Ha Hb Hf Hq Hr Hv Hw Hx Ib Ic Id Ih Ij Ik Il Im In Ip Iq Ir Is It Iu Iv Iz Jf Jg Jh Jk Jm Jn Jo Jp Jq Jr Js Ju Jy Kc Ke Kf Kg Ki Kk Kl Kn Kp Ks Kx Ky Kz Ld Lh Li Lj Lw Lx Lz Ma Mb Mc Me Mf Mg Mh Mi Mj Mk Ml Mm Mn Mp Mr Ms Mt Mv Mw Mx Mz Na Nb Nd Ne Ng Nh Nj Nk Nm Nq Nr Ns Nt Nu Nv Nw Nx Ny Oa Oe Oh Ok Om On Or Ou Ow Pa Pb Pc Pd Pe Pf Ph Pi Pj Pk Po Pz Qa Qb Qc Qd Qe Qg Qh Qm Qn Qt Qu Qv Qw Qx Qz Ra Rb Rc Rf Rg Rh Rj Rm Sr Ss St Tr Tt Tz Ua Ub Uc Ud Ue Uf Ug Uh Uk Ul Um Un Uo Ur Ut Vo Vp Vt Wm Tj) Bb(aC AD aG aH aI aJ aK AI aM AN AO AP aQ aR AS aU aV Aw aX aY aZ bB BC bE bF BG bI bL bM bP bQ bS bU bV bW bZ cA cB cC cD cE cF cG CH cJ cK cL cM cN CO CP cQ cR cS CT CU CV CW cY dA dB DC DD dE dF DG dH Di dJ DK DL dM DR Et Ez Fa GI GP Ha Hb Hq Hr Hv Hw Hx Ib Ic Id Ih Ij Ik Il In Io Ip Iq Is It Iz Jf Jg Jh Jk Jm Jo Jp Jq Jr Js Jt Ju Jy Kc Ke Kk Kn Ks Ky Ld Lh Li Lu Lw Lx Lz Ma Mb Mc Mf Mg Mh Mi Mj Mk Mm Mn Mp Ms Mt Mv Mw Mx My Mz Na Nb Nd Ne Ng Nh Nj Nk Nm Nq Ns Nt Nu Nw Ny Oa Oe Oh Ok Om On Or Ou Pd Pe Pf Ph Pi Pj Po Pz Qa Qb Qc Qd Qe Qg Qh Qm Qt Qu Qv Qw Qx Ra Rb Rc Rg Rh Rj Rm Ss St Tn Tr Tv Tz Ua Ub Ud Ue Uf Ug Uh Uk Ul Um Uo Ut Vp Vt Wm Tj) Kj(aD aE aF aG aH aI aK aL aM aN aQ aR aS aU aV aW aX aY aZ bA bC bE bF bG bH bM bO bP bQ bR bS bU bV bW bX bZ cA cB cC cD cG cH cJ cK cM cN cO cQ cS CT cU cV cW cX cY cZ dA dB dC dD dE dF dH dI dJ dK dL dM dN DR EF fP gP Hb Hc Hx Ii In Jv Kd Kr Ly Mt Mv Nc Nx Of Og Oi Oz Pa Ri Th) Aj(Ao aW bJ bO Ch Cq cZ Dk dN Dp dR EF gL gP Hu Ib Il Jt Jv Kd Ke Ko Lu Ly Ma Md Ms My Nb Nf Nl Nv Nx Ny Of Oi Oz Pa Pb Pg Qy Ri Us) Uu(Ao aW Ba bO Co dI Dk Dp eF Fn Fw gP Hu Ib Ii Jo Jt Kd Kg Ki Ko Kr Lu Ly Md Ms My Ng Nv Nx Ny Of Oi Oz Pa Pb Qw Qy Us Tj) Kg(Ao aW bJ bN bO bR bX cI Cq cX cZ Dk gL Ib Kd Kr Md My Nv Of Og Oi Pb Pg Ur Us Vp) Ng(aW Ba bJ bO bX Cq cZ dA dN Dp Ii Jt Kd Ko Kr Ly Mj Mz Oi Oz Qy Tv Ur Us) Dr(bE Bn dD dI Dp Fi Hw Ii Je Jt Jv Kc Ke Ko Nc Nf Og Ok Pa Up Us Vh) dN(Ao bO Cp De Dk Ed Hq Ii Jo Jt Ko Kr Md My Nv Nx Of Om Oz Pg Us) Ao(aW Cx Ed Ef Fn Fp Hc Jt Jv Kr Ly Og Oi Oz Pa Qy Ur Us) Of(aW dA Dp Ed Hc Jt Jv Jy Ko Kr Ly Nf Nl Og Oi Oz Pa Us) Oz(bH Dk dM dR eF gL Ib Jg Jt Kr Md My Nv Og Ur Us) Jv(aW Cq Dk Ib Md My Nv Og Pb Pg Ur Us) Dp(Co Ib Ii Jo Jt Md My Nv Pg Ur Us) Ed(bH Cq Ii Jt Kr Nv Oi Tv Us Vp Tj) Co(aW bJ dA Jt Kd Kr Ly Og Us) Fn(aW cZ dA dI Pb Tv Ur) Hc(aW bH gL Md My Pg) Us(aW bH Md My Oi Pg) Ko(Cq Md Pg Ur) Tr(Ct Pb Pc) Kr(Ii Iz My) De(Pg Ur) CpbA No

Mx My Na Nc Nd Nj Nk Nl Nm Nq Nr Nv Nx Ny Oe Of Oy Oz Pb Pz Qb Qc Qd) Og(Hq Hr Hv Hx Ih Ii Il Ip Ir It Iu Jh Jk Jm Jn Jp Js Jt Jv Li Lj Ly Lz Mb Mc Md Mf Mh Mj Mk Ml Mn Mp Mx My Na Nc Nd Ne Ng Nj Nk Nl Nm Nq Nr Ns Nv Nx Ny Oe Of Oy Oz Pb Pg Qb Qc Qd) Mq(Hq Hr Hu Hv Hw Ih Ij Ik Il Ip Iq Ir It Iu Jg Jo Jt Lh Lj Lx Mb Mc Mf Mg Mh Ml Mn Mr Mv Mw Mx My Na Nb Nc Nd Ne Nf Nh Nj Nl Nm Nt Nv Of Om Oz Pa Pd Pe Pz Qb Qc Qd Qe) In(Hu Ik Il Im Ip Iq Ir Jg Jm Jp Li Lj Ly Md Mh Ml Mn Mp Mv Mw Nb Nc Ne Nh Nj Nk Nl Nm Ns Nu Ny Oe Oy Oz Pa Pb Pg) Ng(Fp Ij Im Io Jk Jo Jp Me Mi Mn Mr Ms Mt Mz Nb Nc Nl Nq Nv Oh Pd Pe Pg Qe) Po(Fp Hr Hu Il Iq Jo Jr Lw Ly Ma Mm My Nc Nk Nl Ns Ok Oz Pa Pc) Lu(Aj dN Dr Hu Il Io Jm Lx Ma Mr Mz Nn Ns Nt Oh Om Oy Pb Pc Pe) Ms(Fp It Jp Jq Jr Ma Me Mi Mn Mr Mt Mv Mw Mz Nb Nc Nf Nq Oh Pe) Pf(Fp Hu Ii Il Jm Jr Lw Ly Mm Nc Nk Nl Ns Oe Ok Oz Pa Pb Pc) Ok(Fp Ii Jq Jr Jt Ma Me Mm Mr Nf Ns Oe Oy Pa Pb Qe) Me(dN Io It Jm Jq Jr Lh Lw Lx Mt Oh Om) Nn(Il Io Jm Jr Lw Ma Mm Mr My Pb) Lh(Ii Io Jo Jr Lw Ma Mm Oe Oy Pb) Om(Fp Hu Ii Jr Mg Ns Oe Oy Pb) Pc(Fp Io Jq Jr Ma Mr Ns Oy Pe) Io(Jp Jq Lw Ma Mr Nt Pe) dN(bO Hc Ii Jo Jt Kg Kr) Mm(Ma Mr Mz Nf Oe Pe) Jr(Jq Lw Ma Nc Ns Oe) Dr(Jt Ke Nj Oz) Lx(Jq Ly Oe Pb) Oy(Jg Jq Nb Pe) Lw(Ma Mr Ns) Fp(Jp Ma) Jq(Mr Qe) Rv(Nj Nk) Oe(Nt Pe) WmJi MaMz MyJg JnJs PbPe} Mq{Jr(Hq Hu Hv Hw Hx Ih Ii Ij Ik Ip Iq Ir It Iu Iv Jh Jk Jm Jo Js Jt Li Lj Lz Mb Mc Md Mf Mg Mh Mj Ml Mp Mr Mx My Na Nb Nc Nd Ne Nf Nl Nm Nq Nu Nv Nx Ny Of Oz Pa Pd Pe Pg Pz Qb Qc Qd) Nn(Hx Ih Ij Ik Il Ip Iq It Iu Iv Jg Jh Jk Js Li Lj Lx Lz Mb Mc Md Mf Mh Mj Mk Ml Mn Mp Mv Mw Mx Nb Nc Nd Nf Nj Nl Nm Nq Nr Nu Nv Nx Ny Oh Om Pa Pd Pg Pz Qb Qc) Jq(Hq Hv Hw Hx Ii Ij Ik Il Ip Iq Ir It Iu Iv Jh Jk Jm Js Jt Lz Mc Mf Mg Mj Mk Mp My Na Nb Nc Nd Nf Nk Nl Nm Nq Nr Nu Nv Nx Oe Pd Pz Qc Wm) Po(Fp Hq Hu Hw Ii Io Jm Jo Jp Lh Ly Ma Mg Mi Mm Mn Mx My Nh Nk Oe Of Oh Om Oz Pa Pe Pf Qd Qe) Et(Fp Hu Io Ir Lh Lj Lw Lx Ml Mn Mr Mv Mw Mx My Nf Oe Ok Oy Oz Pb Pe Qd) Ok(Hr Ii Io Jp Jt Lw Lx Mh Mn Mr Mv Mx My Nf Nm Oe Of Pa Pe Pz Qd) Pf(Fp Hq Hr Hu Ir Jo Jp Lh Lw Mg Mi Mm Mn Ms Mt Mx Nk Oh Om Qd) Qe(Hr Ii Im Io Jm Jp Lh Lx Ly Me Mi Mn Mr Nk Oe Oh Om Oy Pb) Mz(Jn Jp Lu Lx Ly Me Mi Mn Ms Mw Ns Nt Om Oy Pe Qd) Oh(Fp Ii Im Jg Jp Jt Lh Lw Ly Mi Mt Oe Om Oy Oz Pc) Im(Io Jp Lh Lx Ma Me Mm Mn Mr Ms Mx Oe Om Pe) Jn(Jp Lw Lx Me Mi Mm Mn Mw Ns Nt Om Pb Pe Qd) In(Ir Jt Lh Lx Ma Me Mm Mr Mw Ns Nt Pc Qd) Fp(Lw Ma Mi Mn Mt Ng Ns Om Pc) Jp(Lu Lw Ma Me Mi Ms Ns Oi Pc) Mt(Lw Ma Me Ms My Ng Om Pc) Og(Jk Ma Mm Mn Mr Mw Nb Pa) Ns(Lw Lx Ma Mi Om Pe) Mc(Lx Ma Mm Mn Om Pc) Ng(Jh Jt Jy Mm Nv Pg) Lh(Oi Oy Pb Pc) Om(Ly My Of Qd) Pe(Ms Oi Pb Pc) Jg(Hu My Oi) Lu(Mn Qd) Ma(Lw Qd) Ms(Mn Pc) WmJi LxHq MiPb MrPc UtOy} Po{Og(Hq Ih Ii Ik Il Ip Iq It Iu Iv Jh Jk Jm Jp Js Li Ly Lz Mb Mc Md Mf Mg Mh Mj Mk Ml Mp Mv Mx My Na Nc Nd Ne Nj Nl Nm Nq Nr Nu Nv Ns Nx Ny Oe Of Pd Pf Pg Pz Qb Qc Wm) Jq(Hq Hu Hv Ih Il Io Iq It Iu Jg Jm Jn Jp Jt Lh Lw Lx Ly Mb Md Mf Mg Mi Mn Mr Mt Mv Mw My Nc Nd Ne Nh Nk Nl Nn Nt Nx Oe Of Oh Om Oz Pc Qd) Oi(Hq Hu Hv Hw Ih Ii Ij Il Io Iq Ir Iu Jm Jo Lj Lx Ly Lz Mb Mf Mi Ml Mn Mr Mv Mw Mx My Na Nb Nc Nd Ne Nf Nl Nm Nu Ny Of Oz Pa Pd Pf Pg Qb) Ng(Fp Hu Hv Hw Hx Ii Ij Ik Io Iq Ir Iu Jm Ly Lz Md Mg Mh Ml Mp Mr Ms Mx Na Nc Ne Nf Nl Nm Nq Ns Nv Nx Ny Oe Of Oh Pa Pf Pg Pz Qd) Et(Fp Hr Hu Hv Hw Im Io Jm Jn Jt Lw Ly Ma Mr Mt My Mz Ne Nh Nn Ns Of Oh Ok Oz Pa Pc Pe Qe) In(Hr Hu Ih Ij Il Io Jp Lx Ly Mi Mn Mw My Na Nb Ne Nf Nj Nk Nl Nm Nn Nu Oe Pa Pf Qd) Ok(Fp Hu Im Io Iq Jn Jt Lw Ly Mg Mm Mt My Mz Nh Nk Nm Nn Ns Oe Of Oh Oz Qe) Oy(Hr Hv Hw Im Jg Jn Jo Jp Jt Lx Me Mi Mm Mn Ms Mt Nh Nk Ns Nt Oh Pd Qe) Pb(Fp Hv Hw Ij Jo Jr Jt Lw Lx Ma Me Mm Mr Ms Mz Nn Nt Oe Om Pc Qe) Me(Hr Ii Im Jo Jp Jr Lu Lw Ma Ms Mt Mz Ns Oh Om Pc) Ms(Im Jg Jn Lh Lu Mm Mn Mz Nb Nk Oh Oz Pe Qe) Jr(Hr Im Lh Lu Lw Nc Nk Nn Ns Oe Om Pa Pc) Lw(Fp Im Jn Lu Ma Mz Pa) Oe(Im Lh Nn Nt Qe) Ns(Lu Nn Pc) Ma(Jn Mz Qe) Lu(Jn Mm) My(Jg Om) Jo(Jt Lh) AjeF WmJi NnIi MzIm QeJm OfOm} Dr{bA(Ad Af aK aL An AO Ap aR aV aW aX aY aZ Ba Bb Bc bE bH bL bM BN bO bP bQ bR bV bX cA cE cF cH cI cL cM cP CQ cS CU cZ dA Dc DD dF dH Dk dN fR Fw Gc Gn In Jy Mv) Ba(Af AJ An Ap aW aY Bb bE BG bH bJ Bn Bo bU bX cF cP cS Ct cU dA dD Dl dM dN Ef Ex fR Gc Gn In Jy Nm Oz Pb) Og(Ao aX aY bF bQ Co Hu Im In Je Jn Jr Jy Kn Lu Mg Mi Mj Mr My Nn Ow Pf Ps Pz Ql Qt Qw Ri Rm Ua Ut Ux Vp Vw Xa) Oz(aX bF Bg bZ CH Dk dM Ez Fb Gn Hc Je Jy Lh Mj Mt Mw Nq Or Rb Ua Ud Ut Zx) Mv(Af aX Cx cZ De Dp Fn Ii In Jt Kg Ki Ky Kz Lu Mr Mt Mw Nc Nu Or Ri Ye) Jy(aX cP cT dI dM dN Dp Gn Jd Jv Kc Lh Mi Mw Or Oy Pb Ql Rb Rf Us Ye Tl) In(aW cS cT Fn Gp Ik Im Je Ki Ky Lh Mz Nd Nn Nq Qy Uk Vw Ye Th) Ou(aW bJ cZ Fn Ib Ik Jd Kc Ki Kj Mr Mt Nc Nd Nk Nu To Uk Us Ye) bZ(aJ Ao bH Ef Fi Fn Ki Mt Mw Ng Nu Pb Qy Ri Rv) Lu(aV Bg bU Cx dA Dp Jd Ji Mr Mw Nq Or) Jd(Ib Ng Nj Om Or Pb Pc Qz Rb Vs) cT(aL aZ Bg bH bU Co cS dA dN fR) Bg(Ii Jt Ke Nf Nm Or Pa Us) Nq(Af Cx Ib Ju Kj Rv Vh) Mt(aX Nj Nm Or Ud Vt Wc) Mw(Bb bH Ez Ib Jt Ke Nj) Ef(cP Cs cU dF dG) Lh(dI Nc Nk Nm Ri) Pb(Ez Fb Iz Ma Qy) Tn(cZ Jt Nf Vh) Oy(bF Ch Hc My) cS(bF bH Co Cx) fR(CH cX dD) Im(aY Ii Jt) Jr(Ii Nc Nk) Or(bN Nk Ri) Co(dI Nm) Cx(bQ dF) Rb(Nj Wc) Je(bF Nd) ChaJ DkJt NmMa RiQl UsUt bFdM bHbX bQdD} Nn{Oi(Hq Hr Hx Ii Ij Ik Il Io Ip Iq It Iu Jh Jk Jm Li Ly Lz Mc Md Mf Mg Mj Mk Ml Mp Mv Mw Nc Nf Nk Nm Nq Nr Nv Nx Ny Oe Of Oh Oz Pd Pg Pz Wm) Me(Hr Ih Il Io Iq Ir Jg Jm Jp Lj Ly Mb Mc Mg Mh Mi Mj Mn Mt Mv Mw Mx Na Nb Nc Nk Nl Nu Of Oh Om Oz Pc Qd) Ng(Hq Hr Ih Il Ip Iq It Iu Jd Jm Js Jy Li Ly Lz Mb Mc Mf Mh Mj Mp Mx Nc Nf Nm Nr Nu Of Oh Pz Qb Qc Wm) Og(Hu Hx Ik Io Iv Jg Jo Jp Ma Md Mh Mj Ml Mm Mn Mt Mw Na Nd Ne Nf Nj Nl Ns Nu Nx Ny Oy Pc Qd Wm) Et(Hv Hw Ii Im Ir Jt Lh Lj Lx Ma Mg Mh Mi Mt Mv Mz Ne Nh Nm Nt Of Ok Oz Pa Pb Pe Pf Qd Qe) Fp(Hu Hw Ii Im Ir Jm Jn Jo Jp Jr Jt Lh Ly Ma Mi Mm Mn Mr My Mz Nh Nk Nt Om Oz Pc Pe) Ms(Hu Hv Hw Ij Io Ir Jg Jo Jp Lu Ma Mm Mn Mt Mw Mz Nc Nh Nk Ns Nt Nx Oz Pb Pc Pf Qd) Jq(Hu Ii Io Jn Jo Lh Lw Lx Mb Md Mg Mh Mm My Ne Nl Nt Oe Of Om Pa Pc Pe Qd Wm) Ok(Hr Im Io Iq Jn Jt Lw Lx Ly Mb Mh Mt Mz Nd Ne Nh Nk Nm Of Oz Pc Pe Pf Qd) Jr(Hu Hw Ii Im Io Iq Jm Lh Lx My Mz Nc Nd Nh Nk Nt Om Pa Pb Pc Pe Pf Qe) Im(Lh Lu Mr Mz Ns Oe Oy Pe) Jn(Ii Lu Ma Mr Ns Oe Oy) In(dN Hu Jt Mz Nh Ns) Mr(Hu Lw Mm My Oe) Oe(Lh Nt Pe Qc) Oy(Nh Om Qc) My(Nb Om) Lh(Hu Jo) Pe(Ns Pa) AjeF QeJm} Et{Jr(Fp Hq Hr Hu Hv Hw Hx Ih Ij Ik Il Ip Ir It Iu Iv Jg Jh Jk Jm Jp Js Li Lj Lz Mb Mc Md Mf Mg Mh Mj Mk Ml Mn Mp Mx My Na Nb Nd Ne Nj Nl Nm Nq Nr Nu Nv Nx Ny Of Pd Pg Pz Qb Qc Qd) Lu(Hr Hx Ii Ij Ik Il Ip Iq It Iu Iv Jg Jh Jk Jm Jp Js Li Lz Mb Mc Md Mf Mj Mk Ml Mm Mn Mp Mv Nb Nc Nd Nj Nk Nl Nm Nq Nr Nu Nv Nx Ny Pa Pd Pg Pz Qc) Qe(Fp Hr Hw Ii Im Jm Jn Jt Lh Lw Lx Ly Mg Mt Nf Ns Oh Ok Om Oz Pa Pb Pe Pf Pz) Jq(Im Jn Jt Lh Ly Mb Md Mg Mh Mi Mt Mv Mw Ne Nf Nh Ns Nt Ok Oy Pa Pb Pe Qb Qd) Me(Fp Io Lh Lw Mg Mh Mi Mn Ms Mv Mw Ne Nf Nh Ns Nt Ok Om Pa Pb Pe Qb Qd) Oi(Im Jk Ma Mh Mi Ms Mv Mw Nb Ne Nf Ng Nh Nt Ok Om Qb Qd) Fp(In Jn Lw Lx Ly Ma Ms Mt Mv Mz Ng Og Oh Ok Om Pc Pf) Pf(Im In Io Jn Jo Lw Ms Mz Nf Og Oz Pa Pb Pc) Oh(Im Io Jn Ma Mr Mz Ns Ok Oy Oz Pa Pc) Ms(Im Lh Mr Mv Mw Mz Nb Nf Pc Pe) Ng(Ij Io Mi Mz Nh Nq Nv Pg Qb Qd) Jn(Im Jo Jt Lx Mr Nf Oe Og Oy Pc) Og(Im Mr Mt Mv Mz Nb Nf Pc Pe) Im(Io Lh Lx Mr Mt Mz Pe) In(Lh Lx Nf Ok Om Pe) Pe(Jo Oy Pa Pb Pc) Lx(Hq Mg My Pb) Mz(Ma Mr Pc) Lh(Oy Pb) Om(Hu Mg) MrPc NbOy} Ok{Jr(Fp Hr Hu Hv Hw Ih Ii Im Iq It Jg Jn Jo Jp Js Jt Lh Lj Lw Lx Mg Mh Mi Mn Mp Mr Mt Mv Mw Mx My Mz Nc Nd Ne Nf Nh Nk Nl Nm Oe Oh Om Oz Pe Pz) Lu(Hq Hr Hv Hw Ii Io Ir Jp Lh Lj Lx Lz Ma Mf Mg Mh Mi Ml Mm Mn Mp Mt Mw Mx My Mz Na Nc Ne Nf Nh Nk Of Om Pa Pe Pz Qb Qd) Ng(Hw Hx Ii Ij Ik Io Jp Jt Lw Ly Mh Mi Mk Ml Mn Mp Ms Mx Mz Ne Nh Nr Ns Nv Ny Og Oz Pa Pb Pd Pg Qb Qd) Qe(Fp Hr Hu Ih Il Im Io Iq Jm Jt Lw Lx Ly Me Mg Mm Mr Mt My Mz Nc Nf Nk Nl Ns Oe Of Oh Oz Pa Pf) Oi(Hu Im Io Ig Lh Ly Ma Me Mh Ml Mv Mw Mx Ne Nf Nh Nt Og Om Pa Qd) Fp(Jn Jo Jp Lw Lx Ma Me Mm Mn Ms Mt Mv Mz Nm Ns Oh Oy Oz Pb Pf) Og(Im In Io Jg Jn Lw Ma Mh Mi Mr Ms Mt Mv Mz Nb Nt Pa) Jq(Im Io Jo Jt Lx Me Mh Nf Ns Oh Oy Pb Pe) In(Im Lh Lw Lx Mh Mr Ms Mt Mv Mz Om Qb) Ms(Jn Lx Me Mr Mv Mw Nb Nf Om Pf) Pc(Jn Ma Mz Ns Oh Pe Pf Qd) Me(Im Jo Lx Ma Mr Mt Oh) Lx(Ly Oy Pb) Ma(Jn Oh) Oy(Nb Pe) Pa(Pe Pf) MgOm JoLh OzPf} Jq{Qe(Hr Hu Ih Ik Il Im Ip Iq Ir It Iu Jg Jm Jn Jp Jt Lh Lw Ly Mb Md Mf Mh Mi Ml Mn Mp Mt

Figure 7 Continued

Mv Mw Mz Na Nb Nc Nd Ne Nf Nh Nk Nl Ns Nt Nu Oe Of Oh Om Oz Pe Qb Qc Wm) Pf(Hq Hr Hu Ih Ii Ik Il Io Ip Iq Jg Jm Jn Jo Jp Jt Lh Lj Lw Lx Ly Lz Mb Mc Mg Mi Mn Mt Mv Mw My Na Nb Nc Nd Ne Nf Nh Nk Nl Ny Oe Of Oh Om Pd Pe Qb Qd) Fp(Hx Im Jn Jo Jr Ly Md Mi Mp Mr Ms Mw Ng Nh Ns Nt Om Oy Oz Pb Qd) Og(Hu Ik In Jk Jn Mi Ms Mt Mw Ne Nh Nu Qb Qd) Ma(Im Jn Lh Lx Me Mr Nt Oh Pa Pc Pe Qd) In(Im Jn Lh Lu Lx Me Mm Mr Mv Nt Pc Wm) Ms(Im Jr Lh Lu Lx Mr Mv Mw Nb Pa Pe) Jr(Im Jg Lh Lu Lx Mr Oh Oi Pe) Pc(Im Lh Lx Mc Ng Nt Oh Oi Qd) Pe(Im Lu Mm Ng Oi Oy Pa Pb) Mr(Im Jg Lu Mn Oh Oi) Lx(Im Md Of Oy Pb) Mm(Im Lh Me Mv Oh) Lu(Ns Oh Oi Pb) Wm(Ji Jp Oi) Ng(Im Jk Nt) Lh(Im Pb) BaUu NtOi MeOh TnOz} Ji{Wm(Fp Hq Hv Il Im Jn Jo Jr Jt Lh Mb Me Mg Mn Mw My Na Nb Nc Ne Nf Nh Nm Nq Nr Ns Nx Oe Of Oh Oz Pa Pb Pc Pe Pz) Il(Hv Hw Hx Ih Ij Ip Iu Iv Jh Jm Js Li Lw Lz Mc Mf Mi Mk Mp Nb Nj Nk Nl Nq Nr Nv Qc) Jh(Hv Hx Ih Ij Ip Iu Iv Jm Js Li Lw Mc Mf Mi Mk Mp Nb Nj Nk Nq Nr Nu Nv Qc) Iu(Hv Hx Ih Ij Iv Jm Jo Js Li Lw Lz Mc Mf Mi Mk Mp Nb Nk Nq Nu Nv Qc) Mk(Hx Ih Ij Iv Jm Js Li Lw Mf Mi Nb Nk Nq Nr Nv Qc) Ij(Hx Ih Ip Jm Js Li Lw Mf Mi Nk Nv Qc) Js(Hr Hx Iq Li Mf Mp Nj Nk Nq Nv Qc) Mf(Hx Jh Jm Li Lw Mi Nj Nk Nv) Nk(Hx Iq Jm Li Mc Nq Nv Qc) Kr(Bg dR Ed eF gL Lu Ma Ri) Mi(Li Mp Nb Nq Nr Nv) Lw(Hx Mp Nq Nu Nv) Jm(Hx Li Nq Nv) Lu(aW bO dN) Li(Hx Nq Nv) Me(aW dN) Nv(Iv Nr) AfgL Hxlh TnOy} dN{bA(aD aE aF aG AJ aK aL aM An aO aP aR aS aU aV aZ bB BC bE bF bG bJ bL Bo bQ bW bX bZ cB cE cF cG CH cl cJ cK cL cN cO cP cS cU cX cY DB DC dD dE dl dJ Dk dL dM eF Jy Oy Oz Pb) cT(Ad Af Al Ao Ar As Aw Ax Ba Bb Bn Cp Cq Cs Ct Cu Cw Dd De Di Dl Dp Ef Fn Hc Jy Ly Ms Oy Oz Pb Pc) Me(aW Ax Ba bH bO bV Cv dl Dk Jn Jo Jp Jr Jy Ky Lu Oy Pc Ur) Jy(bO bQ bR cG Dp Fn Jo Kg Kz Nf Of Pc Uk Uu) Ly(Aj Bg In Kg Kk Ky Lu Lx Mr Or Ql Rf Ri) In(Fp Im Jn Jr Kz Mr Nf Nr Qe Qw Sr) Bg(aJ Ba dM Kg Kr Ms Nf Oy Rf) Ba(Aj bO bS Dc dH Ng Oy) Lu(bR Dp Fp Im Jr Rf) Jd(Kg Ms Oi Oy) Oy(Nq Nr Tn) aJ(bR cA dH) Ma(dH Oi) Sr(bO fP) Rf(fP Oz) cA(bV dA) eC(Dc Pk) EfKg TnOz ImOi KrOu] Jr{In(Hu Hw Ij Ik Jg Jk Jn Jo Jt Lu Mi Mn Mt Mv Mw Mz Nb Nf Nh Ns Nu Nx Ny Oi Pa Pd Pg) Om(Fp Im Jo Lw Ly Me Mg Mr My Oe Of Oh Pa Pb Pc Pf Qe) Mm(Fp Hu Hw Lx Ms Mv Mz Nc Nf Ng Ns Nt Pc Pe Pf Qe) Im(Io Lw Lx Me Mr Ms Mz Nc Ng Nk Ns Oe Pe Pf) Ma(Fp Io Jg Lx Mr Ms Mz Nh Ns Oe Oy Pe Pf) Oi(Fp Jp Lu Lw Lx Mr Mt Mv Mw Nh Pe Wm) Pc(Lh Lu Lx Me Mr Ms Ng Ns Pe Pf Qe) Lw(Fp Lh Me Mr Ms Ns Pe Pf Qe) Qe(Io Lh Lu Me Ms Nc Ng Nk) Pf(Lh Lj Lu Ng Ns Og Pa) Og(Mi Mr Mw Nt Oh) Lu(Me Mn Ns Oh) Lx(Me Ms Oy Pb) Ng(Jh Mw Nt) Jg(My Ns Oy) Lh(Me Oe Oy) Nc(Ne Nh) Oh(Mc Ms)} Om{Og(Hr Hv Hw Ih Ii Ij Ik Il Ip Iq Ir It Iu Iv Jg Jk Jm Jp Js Jt Li Lz Mb Mc Mf Mj Mk Mp Mv Nc Nd Nj Nk Nl Nm Nq Nr Nu Nv Nx Ny Oe Pd Pg Pz Qc) Ms(Hu In Lh Lw Lx Me Mg Mh Mi Mn Mw Mz Na Nb Ns Oi Oz Pa Pb Pe Qb Qd) Qe(Fp Il Jm Jo Lu Ly Ma Me Ns Oe Of Pa) Fp(Jo Lu Lw Mg Mm My Of Oh Pb) Oi(Hu Im Jn Lj Lu Mr Pe Qd) Oy(EF gL Jy Mk Pa Qd) Lu(Im Lj Mg Oh Pb) Mr(Hu In Ly Mg My) Pf(In Me Mg My Pb) Hu(Im Ma Me Oh) In(Lj My Pe) Lx(My Of) Me(Im Oh) WmNg MaMg LhOf PbPe] Ng{Qe(Hu Im In Jk Lw Mi Mm Mr Mt Mw Mz Nb Nf Nt Oi Pe) Lh(Fp In Jh Jn Jp Lu Lw Lx Mr Mt Nt Nv Oh Pb Qd) Pf(Im Jh Jk Jt Lu Lw Ma Me Mm Mn Mw Nb Nv) Lx(Fp Ij Jh Jk Jn Jp Jt Lu Ly Mw Nt Pc) Mv(Jk Jn Jt Ma Mi Mn Nb Nx Oh Pe) Jd(Ba Ed Hu Ly Ms Rh Ri Tn Tt) Ma(Fp Jh Jt Me Mr Qy) Jy(BA cT Sr Tn) Pe(Im Lu Mm Pc) Nt(Im Jp Mw) Tn(Ba Mw Oz) Sr(EF) Jk(Jh Mm) BaUu MeNv MwTt MzIm QycT} Oi{Oh(Im Jn Jp Jt Lx Ma Me Mr Ms Mt Mz Nb Nh Pc Pe Pf Qd) Fp(aJ Im Jn Lw Lx Mm Mn Mv Mz Pc Pe Pf Qd) Qe(Hu Im Jn Jp Lw Mi Mm Ms Mv Nb Nf Pe) Jn(Jg Lh Lu Lx Ma Mm Nt) Nt(Im Mt Mz Pc Pf) Pf(Jg Me Mz Pc) Ef(aJ bV Sr) Im(Lx Mr Pe) Lh(Ma Pc Qd) Ed(Ez Qy) Jg(Mr Pe) Ql(bV dM) DpaJ WmJp MsJd QdPc SreF bVfP} Og{Qe(Fp Hu Hv Hw Ij Im Jn Jo Jt Mi Mm Mn Mv Mw Nc Nt Oh Pa) Lh(In Lx Me Mr Mt Mv Mw Nf Nh Nt Pb Pe Qd Wm) Im(Lu Me Mr Mt Pa Pc Pf) Pe(Fp Jn Lu Lw Mm Oh) Jg(Jn Lx Mr Mz Oh) Fp(Lw Lx Nb Pc) Pf(Me Mz Nb Nt) Jn(Nb Pc Wm) Ed(Jd Lw) Me(Lx Oh) WmQd NtNf LuUn JdJv} Oy{Pf(Im Jg Jn Jt Lw Me Mz Nt Pc) Lx(Fp Im Jn Jt Lh Lu Mv) Tn(Jy Qe Ql Sr St Un Vq) Ut(Ba Dp Jd Jv Kr Ri Us) Nb(Im Ma Mv Oh Qe) Lh(Im Jg Mv Pc Qe) Jy(aW cT Sr Un) Un(bZ Ma Ms) Sr(dR gP) Pe(Im Pc) NrdM MwTv SteF} In{Qe(Fp Hv Hw Jo Jt Ma Mr Mt Na Nf Nt Oh Pc Pf) Jn(Fp Im Jg Lu Lw Lx Ma Nf Nt Oh Pe Pf Wm) Fp(Lw Mz Oh Pe) Lh(Lw Mm Oh Pf) Me(Im Lx Pe) Pe(Mm Pc) MzIm JtOh} Me{Pf(Jg Jn Jp Lh Lu Lw Mn Oh Oz Pb Qe) Oh(Im Jg Jp Lx Ma Mm Ms Pc) Im(Lh Lx Mm Mt Mz Pc) Qe(Lw Lx Ma Mm Pc) Mm(Jn Mr Pc) NrdM LxHq PcPe] Im{Lu(Jn Jt Lx Mn Mr Na Oe Oh Pc Qe) Lh(Io Jo Lw Ma Ms Pc Pf) Pe(Ms Oe Pb Pc) Mz(Ma Pc Pf) Sh(Bg Jy) MsNb} Jy{Ed(aW bR bS cA cT dM eF Tj) Co(cN cT dA) Hq(aW cT dA) Ly(aW dM) bA(Of Uu) EqEz PsUs OzeF PgcT} Qe{Lw(Fp Lu Ma Mr Ms Mz) Ms(Jg Lh Lx Pc) Ma(Jn Lh Pc) Lx(Ly Pb) Lh(Jo Pb) Pc(Mr Mz) TiNk ThNj} eF{Sr(Ch Jo Jv Kg Kl Kr Kx Ly Oz Ri Us) Aj(Fa Jh Mr Mw Un) Ch(Jh Mw) MwMy JhUu} Lu{Un(Aj Kj Oz Pb Uu) Fp(Lw Mm Oh) Jn(Lw Pc) Pe(Mm Pb) DpSr} Tn{Aj(Ba Dp Ef Ez Jd Nk Sr) Oz(Jv Rf Rv Us Vq)} Ms{Oh(Jg Lh Lw Nb) Lh(Jn Lw) AjJd UnOz} Fp{Lh(Lw Mm Pb) LwMa LxLy} Sr{Uu(Ba Bg) AjfP ChJv KjgL} Ps{Oz(Nk Qm Qn) NlOe NxUs} Wm{Ly(Lx Pe Pf) LwJp} Ch{Jh(gL gP) MwgL} bA{bR(bW dl) CxEm} Lx{NsMh LyNh} Ma{MmJn LhPb} Mw{My(dR gP)} Oz{FybH SfJd} cT{CxEm aDdl} DpNjXa EdFwUn EzMrRv LwLhPb JhUugL QyKcVi KjPkeC PaPcPe Unconstrained panels with 2 analytes, where 1.0E-7 >= 'model p-value' > 0. Contains 855 panels of 87,101 total panels evaluated. : aA(bM dN eF Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Jl(Et Fp Fr Hq Hr Hu Hv Hw Hx Ih Ii Ij Ik Il Im In Io Ip Iq Ir Is It Iu Iv Jg Jh Ji Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Us Wm) Ji(Et Fp Fr Hq Hr Hu Hv Hw Hx Ih Ii Ij Ik Il Im In Io Ip Iq Ir Is It Iu Iv Jg Jh Ji Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Mu(Dr Et Fp Fr Hu Hv Hw Ih Im In Is Jj Jn Jq Jr Jt Lh Lj Lv Lw Lx Ly Ma Me Mh Mi Mm Mn Mq Mr Ms Mt My Mz Ng Nh Ni No Ns Nt Nw Oe Og Oh Oi Ok Om On Oy Pb Pe Pf Po Qa Qd Qe) Fr(dN Dr Et Fp Hu Hv Hw Im Ir Is Jj Jn Jq Jr Jt Lh Lj Lv Lw Me Mg Mm Mq Mr Ms Mx My Mz Na Ne Ng Nh Ni No Ns Nt Nw Oe Og Oh Oi Ok On Oy Oz Pb Pe Pf Po Qa Qb Qd Qe Wm) On(Et Fp Hu Ii Im In Io Is Jj Jk Jn Jq Jr Lj Lu Lv Lw Ma Me Mg Mh Mk Mq Mr Ms Mv Mw My Mz Ng Nh Ni No Ns Nw Oe Of Og Oh Oi Ok Oy Pb Pe Pf Po Qa Qd Qe) No(dN Et Fp Im In Io Is Jj Jn Jq Jr Lh Lj Lu Lv Lw Ma Me Mm Mq Ms Mz Nc Nf Ng Nh Ni Nk Nl Nn Ns Nw Oe Og Oi Ok Om Oy Oz Pb Pc Pe Po Qa Qe Wm) Nw(Et Fp Hv Hw Ij Im In Ir Is Jj Jn Jo Jq Jr Jt Lh Lu Lv Lw Ly Ma Me Mq Mr Ms My Na Ng Ni Nn Ns Og Oi Ok Oy Pa Pb Pc Pe Pf Po Qa Qe) Lv(Et Fp Im Is Jj Jn Jp Jq Jr Lh Lu Lw Lx Mm Mq Mr Mt Mw Mz Ni Nn Nt Oh Ok Om Pe Pf Po Ps Qa Qd Qe Yl Xa Th) Is(Et Fp In Io Jj Jq Jr Lh Lu Lw Ma Me Mm Mq Mr Ms Ng Nn Og Oi Ok Om Pf Po) Qa(Et In Jj Jq Jr Lh Lu Lw Lx Ma Me Mq Ng Nn Og Oi Ok Om Pe Pf Po) Ji(Et Fp Im Jk Jn Jq Jr Lh Mq Nn Nt Oh Ok Om Pe Pf Pg Po Qe) Et(Fp Jn Jq Jr Lu Lx Me Mq Mr Mz Ng Nn Oh Oi Pf Po Qe) Ok(Fp In Jq Jr Lu Me Mq Ms Ng Nn Og Oh Oi Pc Pf Po Qe) Jr(Im In Jq Lh Lw Ma Mm Mq Nn Om Pc Pf Po Qe) Kq(Aj Ao Bb Dr Jt Kg Kj My Ng Of Oy Pg Us Uu) Po(In Jq Lw Me Mq Ms Ng Og Oi Oy Pb) Nn(Fp Jn Jq Me Mq Mr Ms Ng Og Oi) Dr(BA bZ cS cT Jy Mv Og Oz) Mq(Im Jn Jq Mz Oh Pf Qe) Om(Fp Ms Ng Og Qe) Jq(Fp Mr Pf Qe) dN(BA cT Me) Im(Lh Lu) Qe(Og Oi) MePf NgJg LhOg Unconstrained panels with 2 analytes, where 1.0E-6 >= 'model p-value' > 1.0E-7. Contains 1,100 panels of 87,101 total panels evaluated. :
Qa(Fp Hr Hu Hv Hw Ih Ii Ij Ik Il Im Io Ip Iq Ir Is It Iu Jg Jh Jm Jn Jo Jp Js Jt Li Lj Ly Lz Mb Mc Mf Mg Mh Mi Mj Ml Mm Mn Mp Mr Ms Mt Mv Mw Mx My Mz Na Nb Nc Nd Ne Nf Nh Nj Nk Nl Nm Nq Nr Ns Nt Nu Nv Nx Ny Oe Oh Oy Oz Pa Pb Pd Pe Pg Pz Qb Qc Qe) No(eF Hq Hr Hu Hv Hw Hx Ih Ii Ij Ik Il Ip Iq Ir It Iu Iv Jg Jh Jk Jm Jo Jp Js Jt Li Lx Ly Lz Mb Mc Md Mf Mg Mh Mi Mj Mk Ml Mn Mp Mr Mt Mv Mw Mx My Na Nb Nd Ne Nj Nm Nq Nr Nt Nu Nv Nx Ny Of Oh Pd Pf Pg Pz Qb Qc Qd Ri) Fr(bA cT dM Ed Hq Hr Hx Ih Ii Ij Ik Il In Io Ip Iq It Iu Iv Jg Jh Jk Jm Jo Jp Js Li Lu Lx Ly Lz Ma Mb Mc Md Mf Mh Mi Mj Mk Ml Mn Mp Mt Mv Mw Nb Nc Nd Nf Nj Nk Nl Nm Nn Nq Nr Nu Nv Nx Ny Of Om Pa Pc Pd Pg Pz Qc) Nw(Hq Hr Hu Hx Ih Ii Ik Il Io Ip Iq It Iu Iv Jg Jh Jk Jm Jp Js Li Lj Lx Lz Mb Mc Md Mf Mg Mh Mi Mj Mk Ml Mm Mn Mp Mt Mv Mw Mx Mz Nb Nc Nd Ne Nf Nh Nj Nk Nl Nm Nq Nr Nt Nu Nv Nx Ny Oe Of Om Oz Pd Pg Pz Qb Qc Qd) On(Dr Hq Hr Hv Hw Hx Ih Ij Ik Il Ip Iq Ir It Iu Iv Jg Jh Jm Jo Jp Js Jt Lh Li Lx Ly Lz Mb Mc Md Mf Mi Mj Ml Mm Mn Mp Mt Mx Na Nb Nc Nd Ne Nf Nj Nk Nl Nm Nn Nq Nr Nt Nu Nv Nx Ny Om Oz Pa Pc Pd Pg Pz Qb Qc) Mu(dN Hq Hr Hx Ii Ij Ik Il Io Ip Iq Ir It Iu Iv Jg Jh Jk Jm Jo Jp Js Li Lu Lz Mb Mc Md Mf Mg Mj Mk Ml Mp Mv Mw Mx Na Nb Nc Nd Ne Nf Nj Nk Nl Nm Nn Nq Nr Nu Nv Nx Ny Of Oz Pa Pc Pd Pg Pz Qb Qc) Po(Fp Hq Hr Hu Hv Hw Ii Ij Il Im Io Iq Ir Iu Jg Jm Jn Jo Jp Jt Lh Lj Lu Lx Ly Ma Mg Mi Mm Mn Mr Mt Mw Mx My Mz Na Nb Nc Nd Ne Nf Nh Nk Nl Nm Nn Ns Nt Oe Of Oh Om Oz Pa Pc Pe Pf Qd Qe) Is(dN Hr Hu Hv Hw Ih Ii Ij Il Im Ip Iq It Iu Jg Jm Jn Jo Jp Jt Lx Ly Mb Mf Mh Mi Ml Mn Mp Mt Mv Mw Mx Mz Na Nb Nc Nd Ne Nf Nh Nk Nl Ns Nt Nu Ny Oe Oh Oy Oz Pa Pb Pc Pd Pe Pg Qd Qe) Lv(dN Dr Hu Hv Hw Ih Ij In Io Ir Jg Jk Jo Js Jt Li Lj Ly Lz Ma Me Mh Mi Mj Ml Mn Mp Ms Mv Mx Na Nb Ne Nf Ng Nh Ns Nu Nv Ny Og Oi Oy Oz Pa Pb Pc Pd Pg Qb) aA(aC aM aW aZ BA bF Bg bH bP bR bS bW bZ cA Ch cN cP cR cT Dc dF dl Dk dM Dp dR Ed Ef fP gL gP Jy Ki Kq Ou Ow Pk Rf Ri Sr Tn Un) Ok(Et Hu Hw Im Io Jn Jo Jp Lh Lw Lx Ly Ma Mg Mh Mi Ml Mn Mp Mr Mt Mv Mw Mx Mz Na Ne Nf Nh Nm Ns Oe Om Oy Oz Pa Pb Pe Qb Qd) Ni(aJ aW bA bV cN dM Du Ed Fd Fp Hp Jg Jj Kq Li Lw Ma Mm Mt Mv Mw Mz Nv Ny Pa Pc Pg Qb Rv Sr Tn Vi Vz Wb Wf Zq Tm Ti) dN(aJ An aW bF Bg bH bN bR bW bZ cA Dc dF dI dM eC Im In Jd Jl Jn Jr Jy Kq Lu Ly Mq Mr Ms Nf Oe Og Oi Rf Sr tF) Jr(Fp Hu Io Jg Jp Jt Lu Lx Me Mi Mn Mr Ms Mt Mv Mw Mz Nb Nc Nf Ng Nh Nk Ns Nt Ny Og Oh Oi Pa Pe Qd Wm) Dr(aJ Ao bF Bg bQ Co Cx dF Ef fR Gp Im In Jd Je Jl Ky Lh Lu Ma Mr Mt Mw Nd Nn Nq Nu Or Ou Pb Qy Ri) Kq(aW bH Co Cq cZ De Dk Dp Ed Hc Ib Ii In Iz Jg Jo Jv Ki Kl Kr Ly Md Ms Nb Nv Nx Og Oi Oz Pa Pb Ur) Et(Hv Hw Im In Io Lh Lw Ma Mh Mi Ms Mt Mv Mw Mx Na Nb Ne Nf Nh Nt Og Om Pc Pe Qb Qd) Nn(Hu Hv Hw Im In Ir Jt Lh Lu Lw Lx Ma Mi Mz Na Ne Nh Ns Nt Oe Om Oy Pe Pf Qd Qe) Mq(Fp In Jg Jp Jt Lh Lu Lw Lx Ma Me Mi Mm Mn Mr Mt Mw Ng Ns Nt Og Oi Om Pc Pe Qd) Jq(Im In Jg Jn Jp Lh Lu Lx Ma Mm Ms Mt Mv Mw Nh Nt Og Oh Pa Pc Pe Qd Wm) Om(Hu Im In Jn Lj Lu Ma Me Mg Mr My Mz Ns Of Oh Oi Oy Pe Pf Qd) Qe(Fp Im In Jn Lh Lu Lw Lx Ma Me Mm Mr Ms Mt Mz Ng Pc Pe Pf) Jj(Ij Jg Jt Lx Ma Me Mr Mt Mv Mw Mz Nh Nv Ny Qb Qd) Pe(Fp Im In Lu Lw Ma Me Mm Og Oi Oy Pa Pb Pc) Jn(Im In Lh Lu Lw Lx Ma Me Mm Og Oi Pc Pf) bA(aD aJ aM aW bJ bM bP bR bW Ch Dc dM Jy) Lh(Fp In Lw Ma Mm Ng Oh Oi Oy Pb Pc Pf) Pf(Fp Im In Jt Lu Lw Mz Ng Og Oi Oy) Im(Lx Mc Mr Mt Mz Og) Ng(Jd Jk Lx Ma Mv) Fp(Jp Lw Ma Oi) Sr(eF gL Oi Ri) Oh(Lu Me Ms Oi) Lx(Me Og Oy) Ji(gL Kr Ri) Oy(Tn Ut) cT(aJ dM) WmJp NtOi LuUn MaMe Unconstrained panels with 2 analytes, where 1.0E-5 >= 'model p-value' > 1.0E-6. Contains 2,066 panels of 87,101 total panels evaluated. :
dN(aC AD aE AF aG aH aI Aj aK AL aM aN AO AP aQ AR AS aU aV Aw aX aY aZ BB BC bE bG bI bJ bL bM Bn BO bP bQ bS bU bV bX cB cC cD cE cF cG CH cI cJ cK cL cM cN CO CP CQ cR CS Ct CU CV CW CX cY cZ dA DB dC DD DE DG dH Di dJ DK DL Dp DR Ed EF Et Ez Fa Fb Fn FP Fy GL Hc Hf Hu Hv Ih Ij Il Io Iv Ji Jj Jk Jo Jp Jq Ke Kf Kg Ki Kk Kr Kx Ky Kz Lh Lw Lx Ma Mb Mi Mj Ml Mn Mt Mv Mw Na Nb Nc Nd Ng Nj Nk Nl Nn Nq Nr Nt Nv Nw Nx Ny Oa Oh Om On Or Ou Ow Oy Oz Pa Pb Pc Pe Pf Pg Pk Po Qa Qb Qd Qe Qh Ql Qn Qt Qv Qw Qy Qz Rh Ri St Tn Ud Uh Un Ur Us Vp) Kq(AD aE AF aG aJ aK AL aM Ap aQ aR As aU aV Aw aX aY aZ bA bC bE bF Bg bJ bL bM BN bO bP bQ bR bS bV bW bX bZ cA cB cD cG CH cI cJ cK cN Cp CS CT CU Cv CX cY dA DB DC DD dE Dg dH dI dJ Dl dM dR eC EF Fn Fp Fr Fw gL GP Ha Hb Hf Hq Hu Hv Hx Im Io Ip Iq Ir Is Iu Jd Je Jh Ji Jj Jk Jl Jn Jr Ju Kd Ke Kf Ko Ks Kx Ky Kz Lh Lj Lu Lv Lw Ma Me Mg Mj Mk Mq Mr Mt Mu Mw Na Nc Nd Nf Nj Nk Nl Nm Nn No Nq Nr Ns Ny Oa Oe Oh Ok Or Ou Ow Pc Pk Po Pz Qe Qh Ql Qu Qv Qx Qy Qz Ra Rf Rh Ri Rv Sh Sr Ss Tn To Tr Tt Tv Tz Uc Ud Ue Uf Ug Uk Um Ut Vo Vp Tj Ti Th) aA(AD aE AF aG aH aI aJ aK AL AN AO AP aQ AR AS aU aV Aw AX aY BB BC bE bG bI bJ bL BN BO bQ bU bV bX cB cC cD cE cF cG cH cI cJ cK cL cM CO Cp CQ CS Ct CU CV CW CX cY cZ dA DB dC DD DE DG dH Di dJ dK DL Dr Ex Ez Fa Fb fR Fw Fy Gl Hc Ic Id Iz Jd Jv Kd Ke Kf Kj Kk Kn Ko Kp Kr Kx Ky Kz Ld Oa Or Pi Pj Ql Qm Qt Qu Qv Qx Qy Qz Ra Rb Rh Rm St Uc Ud Uf Uh Ul Up Ur Us Ut Uu Uv Vp Vt tF) bA(aC Ad aE AF aG aH aI Aj aK AL AN AO AP aQ AR AS aU aV Aw AX aY aZ Ba BB BC bE bF BG bH bI bL BN BO bQ bS bU bV bX bZ cA cB cC cD cE cF cG cH cI cJ cK cL cM cN CO CP CQ cR CS CT CU CV CW CX cY cZ dA DB dC DD DE dF DG dH DI dJ DK DL Dp Ed Ef fR Gl Jd Ji Jl Jq Jr Jv Me Mu No Oi Oy Oz Qa Qe Ql Qv Rf Ri Sr Un Ur Us) Dr(An aO aP Aw aX aY bC bE bG bH bV bW bX cE cG Ch cO CP CU cV Cw dA dG dH DI Dk dM Dp Ed Et Ex Ez Fb Fn Fy Gl Gn Hc Hu Hw Ib Ih Ii Ij Ik Il Is Iz Ji Jj Jk Jn Jp Jr Jt Kc Kg Ki Kj Kk Lx Ly Lz Me Mh Mi Mj Mk Mn Mp Mq My Mz Nb Nc Nf Ng Nj Nk Nl Nm No Nr Nv Nw Ny Oe Oh Oi Ok Om Ow Oy Pa Pc Pe Pf Po Ps Pz Qa Qb Qe Ql Qm Qu Qv Qw Rb Rf Rm Si Tn To Ud Ug Uk Ur Us Ut Vi Ye Xa Th) Ni(aD Aj aM aP Ax aY Ba Bg bM Bo bQ bR bS bW bZ CS cT Cv dA Dc dF dG dI Dk Dp eF Em Eq Fa Fc Fi Fy Gb Gd Gh GL Gn Hc Hl Ho Ih Ij Jd Jk Js Jt Jy Kx Ky Kz Lj Lp Lt Ly Me Mi Mj Mp Mr Mx Ne Nh Nk Nl Nt Oa Og Op Or Ou Oz Pd Qh Ql Qv Qy Rf Ri Rt Ru Rx Ry Rz Sf Sh Si Sj St To Tr Tt Tv Uf Un Ur Uw Ux Uy Uz Va Vb Vc Vh Vj Vp Vw Wc Wd We Wg Wh Yd Zw Zx Ye Tl) Jr(dM Hq Hr Hv Hw Hx Ih Ii Ij Ik Il Ip Iq Ir It Iu Iv Jh Jk Jm Jn Jo Js Jy Li Lj Ly Lz Mb Mc Md Mf Mg Mh Mj Mk Ml Mp Mx My Na Nd Ne Nj Nl Nm Nq Nr Nu Nv Nx Oe Of Oy Oz Pb Pd Pg Pz Qb Qc Ri Ur Us) Et(Hq Hr Hu Hx Ih Ii Ij Ik Il Ip Iq Ir It Iu Iv Jg Jh Jk Jm Jo Jp Js Jt Li Lj Ly Lz Mb Mc Md Mf Mg Mj Mk Ml Mm Mn Mp My Nc Nd Nj Nk Nl Nm Nq Nr Ns Nu Nv Nx Ny Oe Of Oy Oz Pa Pb Pd Pg Pz Qc) Qe(Hr Hu Hv Hw Ih Ii Ij Il Io Iq Ir Jg Jm Jo Jp Js Jt Ly Mb Md Mf Mh Mi Mj Ml Mn Mp Mv Mw Mx Na Nb Nc Nd Ne Nf Nh Nj Nk Nl Nm Ns Nt Nu Nv Nx Ny Oe Oh Oy Oz Pa Pb Pd Pg Pz Qb Qc Qd) Nn(dM Hr Ih Ii Ij Il Io Iq Iv Jg Jk Jm Jo Jp Js Lj Ly Mb Mc Md Mf Mg Mh Mj Ml Mm Mn Mt Mv Mw Mx My Nb Nc Nd Nf Nj Nk Nl Nu Nx Ny Of Oh Oz Pa Pb Pc Pd Pg Qb Wm) Jq(cT Ed Hu Hw Ih Ij Ik Io Iv Jk Jo Jt Li Lj Lw Ly Lz Mb Md Me Mf Mh Mi Mj Mk Ml Mn Mp Mx Mz Na Nb Ne Nf Ng Nl Nq Nr Ns Nu Nv Nx Ny Oe Oi Om Oy Oz Pb Pd Pg Qb) No(aD Aj Ap aW Bb bH bO bR bS bV cN Co cP cT Cv cW dl dM Dp dR Ed Ef fP gL gP Hc Iz Ju Jv Jy Kg Ki Kj Kl Kr Ky Or Ou Ql Qv Qz Sr Tn To Ud Ur Us Uu Tj tF) Ok(Hq Hr Hv Hx Ih Ii Ij Ik Il Ip Iq Ir It Iu Iv Jg Jh Jk Jm Js Jt Li Lj Lz Mb Mc Md Mf Mj Mk Mm My Nb Nc Nd Nj Nk Nl Nq Nr Nt Nu Nv Nx Ny Of Pd Pg Pz Qc) Mq(eF gL Hr Hu Hv Hw Ih Ij Io Ir Iv Jh Jk Jo Js Li Lj Ly Lz Mf Mh Mj Ml Mp Ms Mv Mx Na Nb Ne Nf Nh Nj Nl Nm Nq Nr Nu Nv Nx Ny Oe Oy Oz Pa Pb Pd Pg Qb) Pf(Hu Hv Hw Ij Io Ir Iv Jg Jo Jp Js Lj Lx Ly Ma Mi Mm Mn Mr Ms Mt Mw Mx Na Nb Nc Nd Ne Nf Nh Nk Ns Nt Nv Nx Ny Oe Oh Oz Pa Pb Pc Pe Qb Qd) Om(Hq Hv Hw Ih Ii Io Ir Jh Jo Jp Jt Jh Lw Lx Ly Lz Mb Md Mf Mh Mi Mj Ml Mm Mn Mt Mv Mw Mx Na Ne Nf Nh Nl Nt Nu Ny Oe Oz Pa Pb Pc Qb) Im(Fp Hv Hw Ij In Io Ir Jg Jo Jp Jt Jy Lw Ma Mh Mi Mj Ml Mm Mn Ms Mv Mx Na Nb Ne Nf Ng Nh Ns Nt Oe Oh Oi Oz Pa Pc Pd Pg Qd) Pe(Hr Hv Hw Il Io Ir Jg Jn Jp Jt Lh Lx Ly Mi Mn Mr Ms Mt Mv Mw Mx Mz Na Nc Ne Nf Ng Nh Nk Nl Ns Nt Ny Oe Oh Oz Qd) Lv(dM Hq Hr Hx Ii Ik Il Ip Iq It Iu Iv Jh

Figure 7 Continued

Jm Mb Mc Md Mf Mg Mk My Nc Nd Nj Nk Nl Nm Nq Nr Nx Oe Of Pz Qc Sr Wm) Is(aW bV dM Hc Hq Hx Ik Ir Iv Jh Jk Js Kr Li Lj Lz Mc Md Mg Mj Mk My Nj Nm Nq Nr Nv Nx Of Pz Qb Qc Qv Us Wm) Lh(Hu Ii Io Jg Jo Jp Lj Lu Lx Ly Mb Me Mg Mi Mn Mr Ms Mt Mv Mw Mx My Mz Ne Nf Nh Nl Ns Nt Ny Oe Of Oz Qb Qd) Po(Hx Ih Ik Ip It Iv Jh Jk Js Li Lz Mb Mc Md Mf Mh Mj Mk Ml Mp Mv Nj Nq Nr Nu Nv Nx Ny Pd Pg Pz Qb Qc Wm) Fp(Hw Hx In Ir Jg Jn Jt Lu Lx Ly Me Mi Mm Mn Mr Mt Mv Mw Mx Mz Na Nb Nt Nv Ny Og Oh Pa Pc Qd) Sr(Aj Dp dR Ed Fr gP In Ji Jj Jl Jv Jy Kg Ki Kj Lu Ly Ms Mu Nc Ng Oe Og Oy Oz Qv Ug Ur Uu) Oh(Hv Hw Ij In Jg Jn Jo Jp Jt Lw Lx Ma Mi Mm Mn Mr Mt Mv Mz Nb Ng Nh Nt Og Pc Qd) Jj(Dp Ef Hu Hw Ii Ik Jm Jo Jp Js Jy Li Lw Mi Mj Mm Mn Mp Nb Nf Nr Nx Pd Wm) Jn(Hu Io Jg Jp Mi Mn Mr Ms Mt Mv Mw Mz Nb Nc Nf Ng Nh Ns Nt Oe Pa Pg Qd Wm) Fr(Ad AJ An As aW bM Cu Cw Dc dI Ef Hc Jv Ki Kz Pk Un Us Uu) Lx(Hq Hv Hw In Jp Jt Lw Ly Ma Mh Mm Mr Mz Nh Nt Of Oi Pb Pc Qd) cT(aD aM aP aW aY bM bP bW cS Cv Dc dG dI dL fR Ji Jl Jy Un) Jl(Aj aW bR Dp eF gL Hc Kj Kr Ky Qv Ri Tn To Tv Ur Uu) Jy(AJ aW bR bS bV dM Ed Ji Ly Ng Oy Oz Rf Sh Un Ur) Mz(In Jg Jp Lw Ma Me Mm Mr Mt Mv Nt Og Oi Pc Qd) Ji(aW dI dM Dp Ed eF Hc Jv Kg Qv Qy Rf Tn Ur Us) Me(Cv dM Jg Jp Lw Mm Mn Mr Mt Nt Nv Qd) Qa(eF Hq Hx Iv Jk Kr Md Mk Of Qd Us Wm) Un(eC Ed In Kg Ly Ma Ms Og Oi Oy Oz Us) Mr(aW dM Jg Jp Jt Lw Ma Mm Mn Pc Qd) dM(Ba Cp cS Dc dF dI Ed GI Nr Oi) Qd(Jg Lu Lw Ma Mm Ng Og Oi Pc) Nt(In Jp Lu Lw Mt Ng Og) Dc(aJ Ba bW bZ dI eC) Oi(aJ bV Jd Jg Ma Mt) Ed(eF Jd Lw Mu On) Og(Jg Jt Nb Nv Xa) Oz(Fy Ps Tn Vi Xa) Ba(AJ Ng Uu) Lw(Jp Ma Mt Mv) Mu(Ao Bb Co Wm) On(Bb Jv Sh Wm) Fy(bH Kg Lu) Rf(eF Lu Ou) Ma(Jt Nh) Ng(Nv Tn) AjTn WmNw LuKe MsJd MtSh NbOy NkPs TrPc SteF

Unconstrained panels with 2 analytes, where 1.0E-4 >= 'model p-value' > 1.0E-5. Contains 3,824 panels of 87,101 total panels evaluated. : Dr(aC AD aE AF aG aH aI Aj aK AL aM aN Ap aQ AR AS aU aV aW Ax aZ BB Bc bI bJ bL bM BN BO bP bR bS bU cA cB cC cD cF cH cI cJ cK cL cM cN CQ cR Cs Ct Cv cW cX cY cZ DB DC DD DE Dg dJ dK DL Du Em Eq Fa Fc Fd Fi Fw Gb Gc Gd Gh Gz Ha Hb Hf Hl Ho Hp Hq Hr Hv Hx Ic Id Io Ip Iq Ir It Iu Iv Jf Jg Jh Jm Jo Jq Js Ju Jv Kd Kc Kf Kl Kn Ko Kp Kr Ks Kx Kz Ld Li Lj Lp Lt Lw Mb Mc Md Mf Mg Ml Mm Ms Mx Na Ne Nh Ns Nt Nx Oa Of Op Pd Pg Ph Pi Pj Pk Qc Qd Qg Qh Qn Qt Qx Qz Ra Rc Rg Rh Rj Rt Ru Rv Rx Ry Rz Sf Sh Sj Sr Ss St Tv Tz Ua Ub Uc Ue Uf Uh Ul Um Un Uo Up Uu Uv Uw Ux Uy Uz Va Vb Vc Vh Vj Vo Vp Vq Vs Vt Vw Vz Wb Wc Wd We Wf Wg Wh Yd Yl Zq Zw Zx Tm Tl Wm Tj Ti) Ni(aC Ad aE AF aG aH aI aK AL AN AO Ap aQ AR AS aU aV Aw aX aZ BB BC bE bF bG bH bI bJ bL BN bO bP bU bX cA cB cC cD cE cF cG CH cI cJ cK cL cM CO CP CQ cR Ct CU cV CW CX cY cZ DB dC DD DE Dg dH Di dJ dK DL dR Ef Ex Ez Fb Fn Fw Gc GP Ha Hf Hq Hu Hv Hw Hx Id Ii Ik Il In Iq Ir Iu Iv Je Jf Jh Jm Jo Jv Kd Kc Kf Kg Ki Kj Kk Kn Ko Kr Lu Lz Mb Mf Mh Mk Ml Ms Na Nb Nc Nf Ng Nj Nm Nq Nr Ns Nu Nx Oi Ow Pb Ph Pi Pk Pz Qc Qm Qn Qt Qw Qz Ra Rc Rh Rm Ss Tz Ua Ud Ue Ug Uh Uk Um Us Ut Uu Uv Vo Vt Tj) No(aC Ad aE AF aG aH aI aJ aK AL aM AN AO aP aQ AR AS aU aV Aw AX aY aZ Ba bB BC bE bF BG bI bJ bL bM BN Bo bP bQ bU bW bX bZ cB cC cD cE cF cG CH cI cJ cK cL cM cO Cp CQ cR CS Ct CU cV Cw CX cY cZ dA DB DC DD DE dF DG dH Di dJ DK DL eC Ez Fa Fb Fn Fw Gl Gp Ha Hb Hf Ib Ic Id Jd Je Jf Kc Kd Ke Kf Kk Kn Ko Kp Ks Kx Kz Ld Oa Ow Ph Pi Pj Pk Qg Qh Qm Qn Qt Qu Qw Qx Qy Ra Rb Rc Rf Rg Rh Rj Rm Sh Ss St Tv Tz Ua Ub Uc Ue Uf Ug Uh Uk Ul Um Un Uo Up Ut Uv Vo Vp Vt) Jy(AD aE aF aM aN AO aP aU aV AX aY aZ Bb bC bE bF bH bJ bL bM bN bO bP bQ bU bW cA cC cE cF cG cH cI cK cL cN CO cP CS CU CV CW cX cZ dA dB DC dE dF dG dH dI dL Dp eF Eq Et Fa Fp Fr Fy Gd Hc Hq Hu Hv Hw Id Ij In Is Jd Jl Jn Jp Jq Jv Kd Ke Ki Kj Kn Kp Kq Kr Kx Ky Kz Lh Lj Lu Lv Lw Me Mk Mq Mr Ms Mu My Na Nc Nd Nf Nn Nr Nv Oa Of Og Oh Oi Ok Or Ou Ow Pc Pe Pf Pg Pi Pk Po Ps Qa Qd Qe Ql Qv Qz Ra Rh Ri Rj Rv Sf Tn To Tv Ud Uf Uk Up Us Uu Uv Vt Vz Wb Wf Yl Ye Xa Tj) Jl(aC AD aE Af aG aH aJ aK AI aM AN Ao AP Ar AS aU Aw aX aY aZ Ba BB bC bF BG bH bI bJ bM BN BO bP bQ bS bU bV bW bX bZ cA cC cE cF CH cI cK cL cM cN Co CP CQ cR CS Ct CU CV CW CX cZ dA DB DC DE dF Dg dH DI dJ dK DL dM dR Ed Ef Ex Fa fR Fw Gl GP Hf Id Iz Jd Jv Kd Ke Kg Ki Kk Kl Kn Kp Ks Kx Kz Or Ou Ow Pi Pk Ql Qn Qu Qy Qz Ra Rf Rh Rj Sh Ss St Tr Tt Tz Ud Uf Ug Uk Ul Un Uo Up Uv Vo Vp Vt Vz Yl Ye Xa Tj) Fr(aC aD aE AF aG aH aI aK AL aM aN AO AP aQ AR aS aU aV Aw AX aY aZ Ba BB BC bE bF BG bH bI bJ bL BN BO bP bQ bR bS bU bV bW bX bZ cA cB cC cD cE cF cG CH cI cJ cK cL cM cN CO CP CQ cR CS Ct cU CV cW CX cY cZ dA DB dC DD DE dF DG dH Di dJ DK DL Dp dR eF Fa Fw Fy GL Hf Id Iz Kd Ke Kf Kg Kj Kk Kl Kn Kp Kr Kx Ky Oa Or Ou Ow Pi Ql Qu Qv Qy Qz Ra Rf Rh Ri Rj Tn Tv Ua Ud Ul Up Ur Uv Vt) cT(aC Ad aE Af aG aI Aj aK AL AN AO Ap aQ Ar AS Aw AX aZ Ba BB BC bE bF Bg bH bI bJ bL Bn BO bQ bR bV bZ cA cE cF cG CH cK cN CO CP Cq cR Cs Ct CU CW CX dA DB dC Dd DE dF Dg dH Di dJ DK Dl Dp Ed EF Em Ex Fa Fb Fw Gd GL Gn gP Hu Is Jd Jj Jn Jr Jv Ki Lu Lv Lw Me Mq Mr Ms Mu Nn Nw Og Oi Oy Oz Pc Pe Pf Po Qa Qd Qe Ql Qv Qy Rf Ri Sr St Uf Ur Us Uu) bA(dR eF Em Et Ex Ez Fa Fb Fn FP Fw Fy Gd gL gP Ha Hc Hq Hu Hv Hw Ib Ic Id Ij Im In Io Is Iv Je Jf Jj Jn Ju Kc Ki Kj Kr Kx Ky Kz Lh Lu Lv Lw Lx Ly Ma Mg Ml Mm Mn Mq Mr Ms Mv Mw Mz Na Nb Nc Nd Nf Ng Nj Nk Nl Nn Nr Ns Nt Nw Ny Oa Oe Og Oh Om On Or Ou Ow Pa Pb Pc Pe Pf Pk Po Qd Qg Qh Qm Qn Qt Qu Qw Qx Qy Qz Ra Rb Rc Rh Rj Rm St Tn Tz Ua Ub Uc Ud Ue Uf Ug Uh Uk Ul Um Uo Up Ut Uu Uv Vo Vp Vt Wm) Ji(aE AJ An AP Ba Bb bE bF BG bH bJ bN BO bP bQ bR bV bZ cA cC Ch cI cN cP CS Cv Cx cZ dA DB dE dF dJ Dk Dl dR eC Ef Ez Fa Fb Fn fP Fw Fy Gl GP Ha Hb Hf Ib Ic Jd Je Jf Ju Kd Ke Kf Ki Kj Kk Ko Kx Ky Kz Oa Or Ou Ow Ph Pj Pk Qg Qh Ql Qm Qn Qt Qu Qw Qx Qz Ra Rb Rc Rg Rh Rj Rm Ss St To Tr Tt Tv Tz Ua Ub Uc Ud Ue Uf Ug Uh Uk Ul Um Un Uo Up Ut Uu Uv Vo Vp Vt Tj Ti tF) Kq(aC aH aI AN aO aP Ar aS Ax Ba bB Bc bG bI Bo bU cC cE cF cL cM cO cP cQ cR cV CW dF dG Di dK dL Eq Et Ex Ez Fa Fb Fi fP Gb Gl Hr Hw Ic Id Ih Ij Ik Il It Iv Jf Jm Jp Jq Js Kc Kk Kn Kp Ld Li Lx Lz Mb Mc Mf Mh Mi Ml Mm Mn Mp Mv Mx Mz Ne Nh Nt Nu Nw Om On Pd Pe Pf Ph Pi Pj Qa Qb Qc Qd Qg Qm Qn Qt Qw Rb Rc Rg Rj Rm Sf Si St Ua Ub Uh Ul Un Uo Up Uv Va Vs Vt Vz Wc Yd Ye Xa Wm) Sr(Af aJ aM Ao AP aW aY Ba Bb Bg bH BO bP bQ bR bV bW bZ Ch cN Co cS Cv Cx dA Db Dc dF Dg DI DI dM eC Ef Fa Fb FP Fy Gl Gp Hc Hf Hu Ih Ii Io Is Iu Jd Jn Jo Jp Jq Jr Jt Ju Kd Ke Kk Kl Kr Ks Kx Ky Kz Lw Lx Ma Me Mg Mi Ml Mn Mq Mr Mz Na Nb Nf Nj Nk Nl Nn Ns Nw Oh On Or Ou Ow Pa Pb Pc Pf Pk Po Qa Qd Qe Ql Qn Qu Qy Qz Ra Rf St Tn To Tv Ud Uf Uk Un Us Ut Uv Vo Vp Vt tF) dN(Ex fR Fw Gd GP Ha Hb Hq Hr Hw Hx Ib Ic Id Ii Ik Ip Iq Ir It Iu Iz Je Jf Jg Jh Jm Js Jt Ju Jv Kc Kd Kj Kl Kn Ko Kp Ks Ld Li Lj Lz Mc Md Mf Mg Mh Mk Mm Mp Mx My Mz Ne Nh Nm Ns Nu Of Ok Pd Ph Pi Pj Pz Qc Qg Qm Qu Qx Ra Rb Rc Rg Rj Rm Ss Tz Ua Ub Uc Ue Uf Ug Uk Ul Um Uo Up Ut Uu Uv Vo Vt Xa Wm Tj) Jq(AJ aP aW Ba Bb Bg bH bJ bM bN Bo bQ bR bV bW bZ cN cP CS Cx dA dF dI dM Dp eC EF Fa Fn gL Hc Hq Hr Hv Hx Ii Il Ip Iq Ir It Iu Jd Jh Jm Js Jv Kg Ki Kj Kr Kx Ky Kz Mc Mg My Nc Nd Nj Nk Nm Of Or Ou Ow Pz Qc Ql Qn Qv Qy Qz Rf Rh Ri Tn To Uf Ug Uk Un Ur Us Uu) dM(aC AD aI aJ aM An aO aP Ar As aU Aw Ax bF Bg bH bM Bn bQ bV bW bZ cA cE cG Ch Cq Cs Cu Cv CW Db dG Di Dk dL Ef Fy Hu Jd Jj Jn Ky Lh Lw Ly Ma Mn Mq Mu Nf Nw Og Om On Or Ou Ow Oz Pc Pe Pf Pk Po Qa Qd Qe Ql Qt Rf Ri Un) Jn(Cv dI Ed Hc Hq Hr Hv Hw Hx Ih Ii Ij Ik Il Ip Iq Ir It Iu Iv Jh Jk Jm Jo Js Jt Jv Kr Li Lj Ly Lz Mb Mc Md Mf Mg Mh Mj Mk Ml Mp Mx My Na Nd Ne Nj Nk Nl Nm Nq Nr Nu Nv Nx Ny Of Ou Oy Oz Pb Pd Pz Qb Qc Qv Rf Ri Ur Us) Un(AJ aW Ba Bg bH Bo bR bZ cN Cv dI Dl Dp eF Fn gL Hc Hu Ii Im Is Jd Jj Jo Jp Jr Jt Jv Ki Kj Kr Kx Ky Lv Lw Me Mq Mr Mu Nc Nf Ng Nl Nn Nr Oe Ou Ow Pa Pc Pf Qa Qe Ql Qv Qy Rf Ri Tn Ud Ug Ur Uu) aJ(aC AD aM An As AW Ax aY bB bC bF Bg bH bI BN bO bQ bR bS bU bV bW bZ cA cE cG CH cN CP Cq CS Cu Cv Cw dA Db Dd dF dI Dk dR EF GL gP Is Jr Lv Me Mq Mr Mu On Ou Ri Tn) Im(eF Hq Hr Hu Hx Ih Ii Ik Il Ip Iq It Iu Iv Jh Jk Jm Js Jv Ki Li Lj Ly Lz Mb Mc Md Mf Mg Mk Mp Mw My Nc Nd Nj Nk Nl Nm Nq Nr Nu Nv Nx Ny Of Ou Oy Pb Pz Qb Qc Qv Ri Sh Tn Tv Vz Yl) Mr(bR bV cN Cv Dc Ed eF

Figure 7 Continued gL Hu Hv Hw Ij In Ir Jk Jo Ky Li Lu Ly Mi Mp Ms Mt Mv Mw Mx Na Nb Ne Nf Ng Nh Nm Nt Nv Ny Og Oi Pa Pg Qb Qv Ri Ru Rv Sh Tn To Tv Ud Vi Vz Yl Xa) Pe(aW Co Cv eF gL Hq Hu Hx Ih Ii Ij Ik Ip Iq It Iu Iv Jh Jk Jm Jo Js Li Lj Lz Mb Mc Md Mf Mg Mh Mj Mk Ml Mp My Nb Nd Nj Nm Nq Nr Nu Nv Nx Of Pd Pg Pz Qb Qc Ri Wm) Qd(eF Hu Hv Hw Ij Ik Il In Io Ir Jh Jo Jp Jt Ly Md Mh Mi Ml Mn Mp Ms Mt Mv Mw Mx Na Nb Ne Nf Nh Nk Nl Ns Nt Nu Nv Nx Ny Oe Oy Oz Pa Pb Pd Pg Qb Qv Ri Tn Wm) Oh(Hr Hu Ih Ii Ik Io Ip Ir Iv Jh Jk Jm Js Li Lj Ly Mb Mc Md Mf Mh Mj Mk Ml Mp Mw Mx Na Nc Nd Ne Nf Nj Nk Nl Nm Nq Ns Nu Nv Nx Ny Oe Oy Oz Pa Pb Pd Pg Qb Wm) Lh(Hq Hr Hv Hw Hx Ih Ij Ik Il Ip Iq Ir It Iu Iv Jh Jk Jm Js Jt Kg Li Lz Mc Md Mf Mh Mj Mk Ml Mp Na Nb Nc Nd Nj Nk Nm Nq Nr Nu Nv Nx Pa Pd Pg Pz Qc Wm) Fp(Cv Hr Hu Hv Ih Ii Ij Ik Io Iv Jh Jk Jm Jo Js Li Mb Md Mh Mj Mk Ml Mp Ms My Nc Nd Ne Nf Ng Nh Nj Nk Nl Nm Nq Nr Ns Nu Nx Oe Oy Oz Pb Pd Pg Qb) Pf(bR Cv Dc Ed Hq Hr Hx Ih Ii Ik Il Ip Iq It Iu Jh Jk Jm Ky Li Lz Mb Mc Md Mf Mg Mh Mj Mk Ml Mp Mv My Nj Nl Nm Nq Nr Nu Of Pd Pg Pz Qc Qv Ri Wm) Jj(Dc Ed eF Ez Fa Fy gL Hv Ih Il In Ir Iv Jd Jh Kz Lj Lu Mf Mg Mh Mk Ml Mx Na Ne Ng Nj Nl Nm Nq Nu Oa Or Ou Oz Pa Pc Pz Qc Ql Qy Rf Ri Tn Ud) Lx(Hu Hx Ih Ij Ir Iv Jg Jk Jo Js Li Lj Lu Md Mf Mg Mi Mj Ml Mn Mp Ms Mt Mv Mw Mx My Na Nh Nd Ne Nf Nj Nk Nl Nm Ns Nv Nx Ny Oe Oz Pd Pg Qb) Jp(Dp Ed Hc Hv Hw Ij In Io Ir Jo Jt Jv Kr Kx Lu Ma Mf Mh Mi Ml Mm Ms Mt Mv Mw Mx Na Nb Ne Nf Ng Nh Ns Nu Ny Og Oi Pa Pc Pg Qb Rf Ud Us) Ma(Aj Dc Ed Hv Hw Ih Ij In Io Ir Jg Jo Ke Lj Lu Mh Mi Ml Mm Ms Mt Mv Mw Mx Na Nb Ne Nf Nl Ns Nt Nu Nv Ny Og Pa Pc Pg Qb Ri Wm) Me(aP aW Ax Ba bQ bV Nb Cs Dc dF dG Dk eF gL In Jd Jk Jt Ke Kk Li Lu Mi Mp Mv Mw Mx Nb Nh Ny Ou Pa Pc Pg Qb Ql Rf Tn Ur) Mq(Aj aW bV Cv Dc dI Dp dR Ed Fy gP Hq Hx Ii Ik Il Ip Iq It Iu Jm Jv Ky Mb Mc Md Mg Mk My Nc Nd Nk Of Ou Pz Qc Qv Rf Ri St Tn) Jr(Aj aW Ba bH bR bV bW bZ cN Cv dA Db dF dI Dp eC Ed eF Fb Hc Jd Jv Kg Ki Kj Kr Kx Ky Kz Or Ou Ow Ql Qt Qv Qy Rf Rh Tn Uf) Qa(Aj aW Ba bH Bo bR bV bW bZ Co Cv dI Dp eC Ed Fn gL gP Hc Jd Jv Kg Ki Kj Ky Ou Ql Qv Rf Ri Sf Sh Tn To Tv Ur Uu Vz Ye) Fy(Aj aW Bb bW Co Dp Ed Hc Ii In Jd Jo Kd Ki Kj Ly Mu Nc Nf Nj Nl Og Oi Or Ou Oy Pa Pc Ql Qv Qz Ri To Uf Ur Us Vz) aA(eC Fn Gp Gz Ha Hb Hf Ib Je Jf Ju Kc Kg Kl Ks Ph Qg Qh Qn Qw Rc Rg Rj Ss To Tr Tt Tv Tz Ua Ub Ue Ug Uk Um Uo Vo) Nn(Aj Dc Dp Ed eF Hc Hq Hx Ik Ip It Iu Iv Jg Jk Jm Js Li Mc Mk Mp Nb Nc Nd Nj Nk Nm Nq Nr Nv Nx Pd Pg Pz Qc Qv Rf Ri Sh Ur Us) Om(Aj Ed Hr Hx Ij Ik Il Ip Iq It Iu Iv Jg Jk Jm Js Li Mc Mk Mp Nb Nc Nd Nj Nk Nm Nq Nr Nv Nx Pd Pg Pz Qc Wm) Mz(Hu Ij Ik Jk Jt Li Lj Lu Ly Mh Mi Mj Mn Mp Ms Mw Mx Na Nb Ne Nf Ng Nh Nl Ns Nv Nx Ny Oz Pa Pb Pd Pg Qb) Qe(aW Cv eF Hq Hx Ik Ip It Iu Iv Jh Jk Kg Kj Kr Ky Li Lj Lz Mc Mg Mk My Nq Nr Of Ou Qv Rf Ri Tn Tv Us Wm) Oi(aP Ba Cs Dc dF dG Dk Ed EF Ez Fa Id Ij Jt Ke Ky Li Mv Mw Nv Ny Or Ou Ow Pg Qb Ql Qy Rf St Tn Uf Xa) Og(Ba bV Dc Dk Ed Ez Id Ij Jd Jk Jo Ke Ki Lw Mi Mm Mt Mv Mw Nh Ny Or Ou Pa Pc Pg Ps Qb Ql Rf Vi Zw Wm) Is(aD Aj Al aM bH bP bR bW cN Co Cv dA dI Dp Ed eF Jd Jv Kg Ki Kj Ky Ou Ql Ri Tn To Tv Tz Ud Ur Uu) Lw(Dp gL Hu In Jd Jg Jt Jv Li Lj Lu Mh Mi Mj Mn Ms Mw Mx Nb Ne Nh Nv Ny Pa Pg Qb Qv Qz Rf Ri Tn) Ed(Ba bQ bV bZ cN Cv dA Dc dI Df Et Ez gL Hu Ke Lu Lv Mv Nw Oe Ou Oz Po Ql Qy Rf Ri Tn Uf Ur) Lv(aD Aj aP aW Ax aZ bH bM bV bW Cs CV cX dI Dp Jd Kr Ky Ql Qn Qv Qy Rf Ri Tz Uf Ur Us) Mu(aD Aj aW aY bR bV Cs Cv Dc Dk Ki Kj Ky Or Ou Ps Qv Rf Rv Us Uu Vz Yl Zw Ye Tm Xa Th) On(Aj Ao Ap aW bV Co Cs eF Eq gL Hc Jd Kg Ki Kj Kr Oa Qy Rf Ri Rv Sf Tv Us Uu Vz Ti Th) Ba(AD aM An aP As aW Ax bM Bn bV bW bZ cN Cp Cq Cs Cu Cv Cw dF dG dI dL Kl Oy) Lu(Ad bV Cv Dc Dp Fa Id Jd Jg Jt Ky Mi Mm Mn Mt Mw Ny Or Ou Ow Qb Ql St Uf Vt) Jd(Aj Ao bV Co Cv dI Hc In Jv Kj Ky Ly Or Ou Oy Oz Pc Qv Rf Ri Ud Us Uu Wh) Ke(Aj aW bH bZ dI Dp eC eF Fn gL Hc In Jv Kg Kj Kr Ly Ms Nf Oy Oz Ri Ur Us) Nt(Hv Hw Ij Ir Jt Ly Mh Mi Mm Mn Mp Ms Mv Mw Mx Na Nf Ns Ny Oe Pc Pg Qb) Mt(eF Hv Hw In Jg Jo Jt Mi Mm Ms Mw Na Nb Nf Ng Pa Pc Rv Sf Si Vz Yl Tm) Tn(Co Cv Dp Hc Jv Kg Kj Kz Ly Mw Nc Nf Nk Nw Ny Pc Ql Rf Ri St Ur Us Uu) Dc(aP aW bF bH bM Bo bQ bV cS dF dG Dp eF GL Ou Oy Oz Ur) Jt(In Jg Mi Mm Mn Ms Mv Mw Ne Ng Nh Nv Ny Pc Pg Qb Vi) Vi(aX bN Cx cZ dA Dp Ez Kc Nc Nf Nk Oy Pa Pb Ql Ri) Mm(Hu Hv Hw Ij Ir Jo Mh Mi Mv Na Nb Nf Nh Pg Qb) Oz(bV Hl Hp Or Ou Rf Uw Vb Vw Wb Wd Wh Yl Zx Ye) Ou(aW Cv Jv Ki Kr Ly Nc Nw Oy Pc Qv Ur Th) dF(aD aW bH bM bV bW cA cP cS Cv dI Ef Oy) Mi(In Jg Mn Mv Mw Ng Nh Nv Ny Pc Qb Wm) eF(Fa Hc Kx Ky Kz Mw Nw Ny Oa Po Ql Ri) Xa(Af dA Nj Nk Nu Or Oy Ql Rb Ri Sh) Po(Aj aW Co Cv gL Kg Qv Ri Ur Us) Ly(Fa Ki Kk Ky Or Ql Rb Rf Uf Wm) Jg(Hw Mh Ms Mx My Na Nf Ns Qb) bV(cA Ef fP Io Iv Nc Nr Ql Rf) bZ(Ad As bM bW Cp Cq Cu Cv Cw) Ng(Dk Ef Ij Mw Nb Ny Pg Ut) Or(gL Ky Ms Rf Ri Tr Tt Vw) dI(Ad bR cA CP Cq Cu Cw) Mw(gL Ms Nh Tv Ye) Ri(Cv Fa Nr Ql Rf) eC(Id Kd Kn Pi Pk) Nh(Mn Mv Ny Pc) Qv(Dp Ql Rf Ud) Ut(Ao Bb My Of) aP(An aW bR Ef) fR(aW cP CX) gL(bW Kz Nw Ny) Dk(Ms Oy Uu) In(Nv Pg Qb) Ye(Je Ql Qy) Yl(bN Nj Ra) Pc(Mx Na Tt) Aj(Ef Hu) Cv(Nr Qn) Wm(Et Ok) Mn(Na Ne) Ms(Nb Nv) Ps(Nj Us) AdKj CsEf GlaW MyNb NfKy UdRf KgOk QlOe bMbQ

Unconstrained panels with 2 analytes, where 1.0E-3 >= 'model p-value' > 1.0E-4. Contains 9,665 panels of 87,101 total panels evaluated. : Fy(AD aE AF aJ aK Al aM AN Ao AP Ar As aU Aw AX aY aZ Ba BC bE bF BG bI bJ bM BN BO bP bQ bR bS bU bV bX bZ cA cD cE cF CH cI cK cN cO CP Cq CS CT Cu CV CW CX cZ dA DB DC DD DE dF DG dH DI dJ Dk DL Du Ef Et Ex Ez Fa Fb Fc Fd Fi Fn Fp fR Fw Gc Gd Gl Gp Gz Ha Hb Hf Hq Hr Hu Hv Hw Hx Ib Ic Id Ih Ij Ik Il Im Io Ip Iq Ir Is It Iu Iv Iz Je Jf Jg Jh Jk Jl Jm Jn Jp Jq Jr Js Jt Ju Jv Kc Ke Kf Kk Kl Kn Ko Kp Kq Kr Ks Kx Ky Kz Ld Lh Li Lj Lp Lv Lw Lx Lz Ma Mb Mc Md Me Mf Mg Mh Mi Mj Mk Ml Mm Mn Mp Mr Ms Mt Mv Mw Mx My Mz Na Nb Nd Ne Ng Nh Nk Nm Nn No Nq Nr Ns Nt Nu Nv Nw Nx Ny Oa Oe Of Oh Ok Om On Ow Pb Pd Pe Pf Pg Ph Pi Pj Pk Po Ps Pz Qa Qb Qc Qd Qe Qg Qh Qm Qn Qt Qu Qw Qx Qy Ra Rb Rc Rf Rg Rh Rj Rm Rv Sf Sh Si Ss St Tn Tv Tz Ua Ub Uc Ud Ue Ug Uh Uk Ul Um Un Uo Up Ut Uu Uv Va Vi Vo Vp Vq Vs Vt Wc Wh Yl Ye Tm Xa Wm Tj Ti Th) Un(aC AD aE AF aG aH al aK AL aM AN AO AP aQ AR AS aU aV Aw AX aY aZ BB BC bE bF BG bI bJ bL bM BN bO bP bQ bS bU bV bW bX cA cB cC cD cE cF cG CH cI cJ cK cL cM CO CP CQ cR CS Ct CU cV CW CX cY cZ dA DB DC DD DE dF DG dH Di dJ DK DL dR Ef Et Ez Fa Fb FP Fw Gl GP Ha Hb Hf Hq Hr Hv Hw Hx Ib Ic Id Ih Ij Ik Il Io Ip Iq Ir It Iu Iv Iz Je Jf Jg Jh Jk Jm Jn Js Ju Kc Kd Ke Kf Kk Kl Kn Ko Kp Ks Kz Ld Lh Li Lj Lx Lz Mb Mc Md Mf Mg Mh Mi Mj Mk Ml Mm Mn Mp Mt Mv Mw Mx My Mz Na Nb Nd Ne Nh Nj Nk Nm Nq Ns Nt Nu Nv Nw Nx Ny Oa Of Oh Ok Om On Or Pb Pd Pe Pg Ph Pi Pj Pk Po Pz Qb Qc Qd Qg Qh Qm Qn Qt Qu Qw Qx Qz Ra Rb Rc Rg Rh Rj Rm Ss St To Tr Tt Tv Tz Ua Ub Uc Ue Uf Uh Uk Ul Um Uo Up Ut Uv Va Vo Vp Vt Xa Wm Tj Ti Th tF) Qa(aC AD aE AF aG aH al aJ aK AL aM AN AO AP aQ AR AS aU aV Aw AX aY aZ BB BC bE bF BG bI bJ bL bM BN bO bP bQ bS bU bV bX cA cB cC cD cE cF cG CH cI cJ cK cL cM cN cO CP CQ cR CS Ct CU cV CW CX cY cZ dA DB DC DD DE dF DG dH Di dJ DK DL dR Du Ef Eq Ez Fa Fb Fc Fd Fi fR Fw Gb Gc Gh Gl Gn Gp Ha Hb Hf Hl Ho Hp Ib Ic Id Iz Je Jf Ju Kc Kd Ke Kf Kk Kl Kn Ko Kp Ks Kx Kz Ld Lp Lt Oa Op Or Ow Ph Pi Pj Pk Ps Qg Qh Qm Qn Qt Qu Qw Qx Qy Qz Ra Rb Rc Rg Rh Rj Rm Rt Ru Rv Rx Ry Rz Si Sj Ss St Tr Tt Tz Ua Ub Uc Ud Ue Uf Ug Uh Uk Ul Um Uo Up Ut Uv Uw Ux Uy Uz Va Vb Vc Vh Vi Vj Vo Vp Vs Vt Vw Wb Wc Wd We Wf Wg Wh Yd Yl Zq Zw Zx Tm Tl Wm Th) Jy(aC Af aG aH al aK AL An Ap aQ AR AS Aw Ba bB Bc BG bI Bn Bo bX bZ cB cD Ch cJ cM Cp CQ cR Ct Cx cY Db DD De Dg Di dJ DK Dl dR Du Ef Em Ex Ez Fb Fc Fd Fi Fn fR Fw Gb Gc Gh GL Gn GP Gz Ha Hb Hf Hl Ho Hp Hr Hx Ib Ic Ih Ii Ik Il Io Ip Iq Ir It Iu Iv Iz Je Jf Jg Jh Jk Jm Jo Js Jt Ju Kc Kf Kg Kk Kl Ko Ks Ld Li Lp Lt Lx Lz Ma Mb Mc Md Mf Mg Mh Mi Mj Ml Mm Mn Mp Mt Mv Mw Mx Mz Nb Ne Nh Nj Nk Nl Nm Nq Ns Nt Nu Nw Nx Ny Oe Om On Op Pa Pb Pd Ph Pj Pz Qb Qc Qg Qh Qm Qn Qt Qu Qw Qx Qy Rb Rc Rg Rm Rt Ru Rx Ry Rz Si Sj Ss St Tr Tt Tz Ua Ub Uc Ue Ug Uh Ul Um Uo Ut Uw Ux Uy Uz Va Vb Vc Vh Vi Vj Vo Vp Vw Wc Wd We Wg Wh Yd Zq Zw Zx Tm Tl Wm Th) Mr(aC AD aE Aj aM AN aO aP As Aw AX aY aZ Ba

Me Qa) NoLv MeIi QaOe} Ng{Jg(Et Fp Hu Ij Im Io Is Jh Jk Jn Jq Jr Lh Lu Lv Lx Ma Me Mq Mr Mv Mw Mz Nb Nf Nh Nn No Nr Nt Nw Oh Ok Om Pd Pe Pf Pg Po Qa Qd Qe) Om(Fp Is Jk Jr Lh Lu Lv Lx Ma Mq Mr Mv Mw Nn No Nt Og Pf Po Qa Qe) Nn(Et Is Lu Lv Me Mq Ok) Mq(No Nw Ok) Lu(Et Ok) PoJj NoLv} Jj{Lv(Et Fp Im Is Jn Jr Mq Mw Nn No Nt Nw Oh Ok Om Pe Pf Po Qa Qe) Po(Is Jq Jr Lu Ma Me Mq Nf Nn Ns Og Oi Oz Pb Qa Qe) Mq(Fp Im Is Jn Jq Jr Nn No Nw Oh Pf Qa Qe) Fp(Is Jk Jq Lh Nn No Nt Nw Ok Om Qe) Nn(Jr Me Mr Oi Qa Qe) Nf(No Qa Qe) Ma(Qa Qe) Me(No Nw) QaOm QeJq} Lv{No(Ii In Io Jr Lu Me Mm Mq Ms Mt Nf Nn Og Oi Oy Oz Pa Pc) Nn(Me Ms Og Oi Oy) Lu(Im Nw) BnDr} Mq{Og(Is Jq Nn No Nw) Nn(Ms Oi) No(In Oi) Nw(Ms My) InJr} Kq{Bb(Dp Fp Kj Kr Oy Us) Oy(aW Dp Kr Us) KjPb} Oi{Nn(Et Fp Is No Qa) Fp(No Nw) NoPc} Og{Om(Hu Qa Qe) Dr(Jd Qy)} Dr{CxbA IbQy} Oy{NnNb NoeF} EtLuJr MwUugL

Constrained panels with

Im Lw Mi Mn Mt Om Pe) Qe(Jn Lu Lw Ma Ms Mt Ns Pc) Im(Jn Lu Lw Mi Mt Ns Pc) Oh(Jl Lu Me Ms Ns Pb) Jn(Fp Lu Ma Ms Pc) Om(Hu Mg Ms Oy Pb) Lx(Ly Oy Pb) Pc(Mi Ns Qd) AjeF WmaA FpJp MsJg NbOy} Og{Qa(Et Hu In Io Is Jg Jr Lh Lu Lw Lx Ma Me Mi Mm Mn Mr Mt Mz Nb Nf Nn Ok Pa Pc Pe Pf Po Wm) Om(Dr Hq In Jh Jn Jq Lh Lj Lx Ly Ma Me Mg Mh Mi Mr Mt Mz Ne Nf Ns Of Oy Oz Pa Pb Pc Pf Qd) Is(Dr Fp Hu In Io Jr Lw Lx Ma Me Mi Mr Ms Mt Mv Mw Mz Nb Nt Oh Oi Ok Pa Pe Pf Qc) Po(Et Im In Jg Jn Jr Jt Lu Ma Me Mm Mr Mt Mz Ng Nh Nt Oh Oi Oy Oz Pa Pb Pe Qe) Qe(Dr Et In Io Jg Jr Lh Lu Lw Lx Ma Me Mr Mt Mz Nb Nf Oi Ok Pc Pe Pf Wm) Nn(Hv Hw Ii Ij Im In Ir Jn Jt Lu Lw Lx Mi Mr Ms Mz Ng Nh Nt Oi Pa Pf) Dr(BA Bg bZ cT Dk Ez Fy Iz Jl Lh Ma Mt Mw Or Ou Rb Rz Tn) Jq(Et Im Jg Jr Lh Lu Lx Ma Mm Mr Mv Nb Nt Oh Ok Pa Pc Pe Wm) Jr(Et Im Jg Lh Lw Lx Ma Mm Nb Ok Pc Pe Wm) Lh(Et Fp Jg Jn Lw Ma Mm Oh Ok Pc Pf) Ok(Fp Lx Me Nf Oh Pc Pe Pf) Et(Lu Lx Me Oh) Im(Lx Mz Nb Pe) Jg(Fp Pe) CxXa WmJp LxJn NbOh SrJv KiaA PcPe} Jl{My(Et Im Io Is Jr Lu Ml Mt Mv Mw Nb Nf Nl Oz Pc Po Qa) Hu(Et Im Io Is Jg Jr Lu Mv Mw Nf Nl Oy Oz Pf Po Qa Qe) Pb(Hv Hw Ij Im Io Is Jn Lh Lx Mm Mr Nl Oh Pc Pe) Nl(Im Is Mr Mz Na Ne Oh Oy Oz Pe Pf Po Qa) Jo(Hv Hw Ij Is Jt Lh Mr Na Nf Nm Nn Ns Pf) Dr(aW Cx Dc Ii Jt Ke Mj Nc Nk Pg Qd Vs) Ly(dN Iq Lx Mb Mm Mr Nd Nh Ns Om Pf) Pc(Hw Ii Im Io Jn Lu Mr Mz Nc Nf Qa) Oy(Hv In Is Jp Mm Mv Na Ny Oz Pd) Ii(Hv Hw Ij Im Lh Mz Na Pf Qe) Lu(Is Jn Mm Na Oh Pf Po Qa) Nc(Is Na Ne Nn Oh Om Oz Po) Mm(Hw In Io Mz Na Nf Ns) Us(dN Ji Oz Tn Tv Ul Un) Mb(Hv Hw Ij Na Om Qa) Io(In Jp Mz Nf Nn Qe) Of(Hw Ij Lh Lx Nn Qa) Oz(Im Is Jn Nn Om Qa) Pa(Nn Oh Om Pe Po Qe) Hq(Lx Mi Om Pf Po) In(Ij Jt Lh Mt) Po(Hr Il Jm) Ns(Is Qe) Mw(Jg Om) Im(Jn Mt) dN(bO Me) EtQa MlHx NeNh NfHr NkPe IlQe Irlu IsJm JkOm JrJs} Nn{Me(Fp Hu Ii Im Is Jn Jo Jq Jr Lu Lw Lx Ma Mm Mr My Nh Ns Oe Ok Oy Pa Pb Pe Pf Qa Qe) Ng(Hu Hv Hw Ii Ij Ik Ir Jk Jo Jp Lw Mn Ms Mt Mw Mz Nc Nh Nx Pf Qd) Oi(Hu In Ir Jp Jt Lu Lx Ma Mb Mh Mi Mt Mz Nd Ne Ns Om Oy Pa Pf) Ms(Fp Im In Jn Jt Lh Lw Lx Mi Mr Na Nb Om Oy Pa Pe Po Qa Qe) Ok(Fp Hu Ii Is Jo Jq Jr Lu Ma Mg Mr My Ns Oe Oy Pa Pb Qa Qe) Et(Fp Hu In Io Is Jn Jo Jq Jr Lu Mr My Ns Oe Oy Qa) Jq(Im In Is Jr Lu Ma Mr Nh Ns Oy Pb Pf Qa Qe) Oy(Fp Is Jr Lh Lx Mi Mr Pf Po Qa) Jr(Lu Lw Ma Mm Mr Ns Oe) Fp(Is Lu Lw Ns Oe Pb) In(Is Lh Mr Pe Qa Qe) Is(Hu Ii Ns Oe) Qa(Ii Ma Oe) Pb(Lh Mr Pe) NsMr HuOm IiLh} Po{Ng(Im In Jh Jk Jn Jp Jr Jt Lj Lw Lx Me Mi Mm Mn Mt Mv Mw Mz Nb Nk Nt Oi Oy Oz Pb Pc Pe Qa Qe) In(Et Hv Hw Ir Jn Jo Jt Lh Lu Lw Ma Mm Mr Ms Mt Mz Nh Ns Nt Oh Oi Om Oy Oz Pb Pc Pe Qa Qe) Oi(Hr Im Jg Jn Jp Jq Jr Lh Lu Lw Ma Mm Ms Mt Mz Nh Ns Nt Oh Om Oy Pb Pc Pe Qd Qe) Jq(Et Hr Ii Jo Jr Lu Ma Mm Ms Ns Ok Pa Pb Pc Qe) Oy(Et Is Jr Lh Lu Lw Ma Mz Ok Om Pc Pe Pf Qa) Ok(Hr Ii Jo Jr Lu Ma Me Ms Pa Pb Pc) Et(Ii Jo Jr Lu Me Mg Ms Oe Pb) Is(Ii Io Jm Lu Me Ms Oe Pb) Ms(Jr Lw Om Pc) Pb(Lh Lu Pe Qa) Mm(Jr Me) Om(Hu Mg) NsLw LuIm MaJr IiQa JnJs} Et{Me(Im In Is Jn Jo Jq Jr Lx Ma Mr Mt Mz Ng Oh Oi Pc Pf Qa Qe) Lu(Hu Lj Lw Ly Mg Mh Mr Ms My Mz Na Ns Ok Oy Pc Pe Pf Qd) Ng(Hu Im Jh Jn Jq Lh Ma Mr Mt Mw Nb Nf Nt Oh Ok Pc Pe Pf) Jq(Fp In Io Is Jo Jr Lx Ma Mr Ms Oh Oi Pc Pf Qa Qe) Qe(In Io Jo Jr Ma Mr Ms Mz Oe Oy Pc) Is(Fp Ii Jr Jt Ma Ns Oe Oy Pc Pf) Qa(Ii Jo Jr Jt Ma Ms Nf Oe Oy Pc) Oi(Fp Jn Lh Lx Mr Mt Mz Pc Pe Pf) Jr(Im Io Lx Ma Ns Oy Pc) Jn(In Io Ma Ms) Lx(Ly Ms Oy) In(Mz Oh) MsOm JoLh OeOh OyPf} In{Is(dN Fp Hv Hw Io Jn Jo Jq Jr Lh Lu Lw Lx Ma Mm Mr Ms Mt Mz Na Nf Ng Nt Oh Oi Om Pc Pd Pe Pf Qa Qe) Qa(Hu Io Jg Jn Lh Lw Lx Ma Me Mi Mm Mn Mr Mt Mz Nb Nf Ng Nt Oh Oi Pc Pe Pf) Jr(Fp Im Jq Lh Lw Lx Ma Me Mm Mr Nt Oh Pc Pe Pf Qe) Dr(Bg bU Cx Jd Mr Mt Mw Nu Oz Pb Ri) Ok(Jn Jq Lu Me Nf Ng Oh Oi Pc Pe Pf) Qe(Jn Lh Lw Lx Me Mz Oi Om Pe) Jn(Lh Me Mm Om Pc) Jq(Fp Oh Pe Pf) Om(Fp Hu Me Oh) Me(Oh Pf) Im(Lh Pe) WmaA FpLh} Oi{Is(Hu Io Jg Jr Lh Lw Lx Ma Mm Mr Ms Mt Mv Mz Nf Oh Ok Om Pd Pe Qa Qe) Qa(Fp Hu Jr Lh Lu Lw Lx Ma Mm Mn Mr Mt Mz Nf Nt Oh Ok Pa Pe Pf) Qe(Fp Jg Jq Jr Lh Lu Lx Ma Mr Mt Mz Nt Oh Ok Pc Pf) Ok(Jn Jq Jr Lx Mr Ms Mt Mz Ng Oh Pc Pe Pf) Jr(Im Jg Lh Ma Mm Nt Oh Om Pc Pf) Fp(bV Jg Jp Jq Lh Ma Nt Oh Om) Oh(Jg Jq Lh Lu Nt Om) Pf(Im Jn Jq Lh Om) Dp(aA bV Sr) Im(Lh Lu Mz) Jd(Ed Ng) Pc(Jn Pe) WmJi aAdN} Dr{Mv(Aj Bb dA dI Ed Hu Kc Kj Nf Ng Of Pb Uu) Oz(bA bH cT Gp Iz Jd Jr Lu Ma Mi Ou Qy Tn) Ou(Af BN Cx dA Mw Pb Ri Vh) Ef(aA aJ bA cS cT fR Gd) Jy(bE cZ dA Je Mt Ri) bA(BG bJ Ch Co cX) bZ(Ba cP cT Cx Je Oy) Nq(Bn Jt Jv Oy Sf) Lu(Mt Pb Rf Ri Rm) cT(bG bJ Ch CX) Ez(Ii Mr Nd Nm) Ba(CH Cx) Ii(Is Mt Mw) Jd(Bb Ke Oy) Je(Bg Ma Tn) Cx(fR Mi) Ke(Lx Mt) Or(Fn Nj) BgcS MwaY Nkls QyOy QwYc JrJt aJbF} Ng{Ok(Fp Hu Im Is Jh Jn Jq Lh Lx Ma Me Mr Mt Mw Nb Nf Nq Nt Oh Pe Pf Qa) Is(Hu Jh Jq Jr Lh Lw Lx Ma Mm Mw Nf Nt Pc Pf) Qa(Hu Jh Jq Lh Lu Lx Mi Mm Mn Mv Nb Nf Pc Pf) Ma(Jk Jn Jq Jr Lx Nb Nt Pe Qe) Lh(Im Jk Jq Jr Mm Mw Pc Pf Qe) Mv(Im Jq Jr Lw Mm Nt Nv Qe) Qe(Jh Jq Lu Lx Pc Pf) Lx(Im Jq Jr Me) Jd(dN Jy Tr) Wm(Ji Jp) Lu(Im Jq) Pf(Jq Nt) NbIm JydN} Jq{Fp(Is Jg Jp Lh Lu Lw Lx Ma Mm Mv Oh Ok Pa Pc Pe Qe) Pf(Im Is Jr Lu Ma Me Mm Ms Ns Ok Oz Pa Pb Pc Qa Qe) Qe(Ii Jo Jr Lu Lx Mm Mr Ms Ok Oy Pa Pc) Qa(Ii Io Lu Me Mm Ms Nc Ok Oy Pc) Ok(Jr Lu Ma Mr Ms Pc) Mm(Is Jr Lu Ma Mr) Pc(Jr Lu Mr Ms Pc) Wm(aA Ly) Lu(Im Is) Ma(Is Jr) Ms(Jg Oh)} dN{aA(Ap Bg bH bM bO bR bV cA cR cT Cx dH Dp Ed eF gP Il Ly Ma Me Ms Nf Oz) bA(Ap Bg bO bS bU bV cA fP Ly Me) Jy(Aj Co dH Kr Oy Oz Pg Us) Ly(Jd Ki Ou Qy Rb Ur) Me(Aj Bg cT dM Oz) Ba(Ap bR cA) cT(bJ dH fP) Ed(Gp Jd) bR(dI Ma) AjEf FyKg HceC bVfP cAdI} Ok{Lu(Hu Im Is Jn Lw Ly Me Mr Ms Ns Oh Oy Oz Pb Pc Pf Qa Qe) Jr(Io Ma Me Mm Ms Ns Oy Pa Pc Pf Qe) Pc(Fp Is Me Mr Ms Qa Qe) Qa(Ii Io Jt Ma Ms) Qe(Jo Ma Ms Oy Pb) Pf(Me Oy Pb) Ms(Is Oh) FpLy IoIs} Om{Qa(Hs Ii Jm Jo Jr Jt Lu Ma Me Mg My Ns Oe Of Oy Pb) Oy(Fp Jr Lh Lu Lx Mi Mr Ms Nb Oh Pc Qe) Ms(Fp Im Is Jn Lu Mr Pc Pf) Hu(Fp Jr Lu Pf Qe) Qe(Ii Mg My Pb) Jr(Lu Ma Mm Ns) Lu(My Of) FpLy} aA{Wm(Is Jg Jn Jr Lh Lw Me Mm Ms Mw Na Oz Pc Qa Qe) bM(bA bF Bg bO bZ cT Cx EF gP Ma) Dp(Bg Ji Jy Ma Pf Qv Sr) Ma(Ki Ri) FafP NbOy HuJh bRdI} Is{Lu(Fp Hc Im Jr Lw Me Mm Ms Oe Pf) Ms(Io Jg Lh Lw Lx Mm Pc Pf) Me(Ma Mm Pc Pf) Mm(Fp Io Jr) Io(Jr Pf) Oy(Lx Pf) FpLw} Jr{Ma(Im Lh Lu Lw Me Mm Pc Qa Qe) Mm(Im Io Lh Lu Me Mr Qa) Im(Lh Lu Pc) Ms(Jg Lh) Pf(Me Oy) WmLy LuLw QaPc LhPb} Oy{Lx(Jg Me Nb Qa Qe) Pf(Lh Nb Qa Qe) Wm(Ji Jp) Tn(Cv Mw) Jg(Nb Pe) Jy(bA Tv) LuUn} Lu{Im(Lh Lw Me Mm Mz Pe Pf) DpJi LwQa MeOh MmJn} Qa{Ma(Lw Me Pc) Ms(Jg Pc) Pb(Lh Lx) MePc} Jy{bA(Co Hq Oz Pg) Uu(Ba Sr) Oz(aW dM)} Aj{Tn(Mw Oz Qy) eF(Ny Pk) BgSr} Qe{ThNk MaMz NjYl UseF} Sr{Uu(Ef gL) HcgL KjeF} Pf{Me(Im Mm Pc) LhPb} Ji{Lx(Ml Ny) JgJt} Jp{Wm(Ly Ms) FpLw} Im{Lh(Oe Pb)} Oz{CxXa PsRi} CsEfGd Constrained panels with 3 analytes, where 1.0E-7 >= 'model p-value' > 1.0E-8. Contains 11,815 panels of 11,919,473 total panels evaluated. : Kq{Jt(aA aF aK aL aW Ax bH bJ bM BN bV bW bX Cq Cs Ct cZ De Dk Hc Ib Ii Im Iz Jd Jg Jj Jk Jn Jr Jv Kg Ki Lj Ly Md Mk Ms Mw My Ni Nr Nv Nx Oa Og Oh Oi Ow Pa Pb Pc Pg Qe Ql Rf Ri Sr Un Ur Us Ut Tj) dN(aA Ad AF Ap As aW bA bH bN bR cG Cq CT cZ Dg dH DL Dp Dr eC Hb Hc Hf Hu Ib In Jg Jh Jv Kd Ke Kf Ki Kl Kz Lu Me Ms Mw Nb Nf Ni Nl Nm Ny Oa Oe Og Oi Ok On Pa Pb Pc Qy Qz Ri Ur Ut Uu) Ed(aA Aj aW aY bJ bO cA cN Co Cu cZ dA dl Dk dM Dp eC Ha Hc Hx Ib In Iq Ir Iz Jg Jj Jo Jv Kd Kg Kj Kl Kn Ko Md Mj Mr Ms Mt Mw My Nb Nc Ni Nk Nx Ny Oe Og Oz Pa Pb Qh Ri Tz Uu) Dr(Af al Aj aL aV aW aX BA bL bO bP bU Cv Cx Dc Fn Gn Ib In Jg Jp Ju Jy Kd Kf Kg Ki Kz Lu Mw Nd Nj Nk Nm Nu Pb Pg Ql Ri Rt Rv Sf Sh Si To Tv Uc Ud Ur Vs Wc Yc Tl) Ng(aA Ao bH bN bR Cx Dc dI Dk Fn Hb Hc Hu Hx Ib In Iq Ir Jd Jv Jy Ke Kf Kg Kl Lu Ma Md Mq Mr Ms Mt Mu Mw My Nb Nc Nf Nj Nl Nv Nx Ny Og Ow Pa Pb Pg Qz Rh Ri Up Vp Tj) Ib(aA Ad Af Al Ao aW BA bH bJ cl cT Cx cZ dM Fn Fp Hc Hf Hu Ii Jd Je Jo Kd Kf Kl Ko Kp Kr Kz Lu Ly Mq Mu Nc Nf Ni Nl Nm Og Oi Pa Pb Ph Ql Qy Qz Ri Tr Ur Us Vo) Pg(Ad Af Ao aW Ax bA bH Bn bX cl cN cO Cs cT Cx cZ dA dl dM Fn Fp Hf Ii Jg Jo Kd Kf Ki Kl Kp Kr Kx Kz Lu Ly Me Ms Nf Ni No Oa Og Ow Oz Pa Pb Pc Ql Ri Sr Uc Ur Vo) Co(aA Af bA bH bQ bR bX bZ cl cN cO Cq cT CX cZ Db Dc dI Ef Hc Hx Jg Jv Jy Kl Ko Lu Ma Md Me Mj Ms Mv Mz Nc Nf Ni Nn Nx Oi Oz Pa Pb Pc Qy Ri Tv Up Ur Vp) Ur(aA Aj Ap Ar bH Bo Cp cZ Dk Fp

Figure 7 Continued

Hb Hc Hq Hu Ii Iz Jd Jg Jh Jl Jo Ki Kl Kr Kx Kz Lu Ly Md Ms My Nb Nf Nn No Nv Oa Of Ok Om Pa Pc Qw Qy Qz Ri Uc Ue Us Uu) aA(aE Af Aj Ao aW bH bM bO bX Cq Cu Cx dC Dk Dl Fw Hc Io Iz Jd Jg Jv Kd Ke Ki Kl Ko Kr Ly Ma Md Mr Ms Mw My Nb Ni Nl Nv Nx Ny Oe Of Og Oz Pb Qu Ri Vp) Md(Ad Af Al Ao aW bA bH cN Cp cT cZ dA De dl dM Fn Fp Ii Ir Iz Jf Jg Jo Kd Kf Kl Kp Kr Kx Lu Ly Mq Nf Ni Nm Og Oi Ow Pa Pb Ql Ri To Tv Uc Vo) My(Ad Af Ao aW Ba bJ Bn bO bR cl cP Cq cT Cx cZ De dM Fn Ii Jd Je Jo Kd Kf Kl Ko Kp Lu Ly Mq Nc Nf Ni Nl Nm Og Oi Pa Pb Ph Ql Qy Qz Ri Uc Vo) Us(Af bA bM bN bP bV bW cl cN Cq cS cZ dl Dk dM Fi Fn Fr Hb Hc Ii Iz Jd Jo Kd Ki Kl Ko Lu Ly Ms Mu Mw Nb Ni Nl Nv Ny Og Pa Pb Pc Ql Qz Ri Uf) Jv(aK bH bJ bN bO bX cH cl Ct dB DE Dp Fw Hc Ii In Jd Jg Jo Kd Kg Kl Ko Kr Ly Ma Mr Ms Mw Nb Nc Nx Ny Oi Oz Pa Pc Qx To Tv Uu Vp Tj) Oz(aE aY bA bO bV bX bZ cK cN Cq CT cZ DE dl Dp Hc Ii In Iz Jd Jo Kg Ki Kl Ko Ly Mk Ms Mw Nb Nc Ni Nx Ny Oi Pb Qz Ri Sh Vp Tj) Ao(aE Af BA bH bJ BN bR bZ cl Cq cT cX cZ De Dk Dl Ii In Jd Jy Kd Kf Kl Ko Ma Mu Nc Nf Nl Nv Ny Of Pb Ql Qz Ri Vo Vp) Ii(aW bA bH bJ bN bX cl cZ DE dl Dk Hc Hu Im Is Jl Jn Jr Ki Kl Kz Ly Me Ms Nc Nf Ni No Nx Of Og Oi Pa Pb Pc Ql Rf Ri) De(aE aL aW bA bH bJ bM bP bW cl cN Cq cZ dl Dk Dl dM Dp Fw Hc Kd Kl Kr Lu Mr Ms Nv Ny Og Oi Pa Pb To Tv Uu Vp) Ly(aE aL bH bM bO bW cl cN Cq Cu cZ dl Dk dM Dp Fw Iq Ir Iz Jg Jj Jo Kg Ki Kl Ni Nv Og Oi Pb Qu Qv Ri To Tv Vo) Kj(Ad Ba Bg Cw Dc Dd eC Ex Fn Fw Hf Hu Hv Hw Id Ir Iv Js Ki Kn Ma Me Mj Mz Nd Nl Nr Ph Pi Pk Rv To Tv Tz Um Uu) aW(Af aR Bn Cp Ct cZ Dk Dp Hb Hq Hu Iz Jg Jh Jk Jo Ki Kl Ko Kr Me Ms Nc Ni Nj Nl Nv Nx Oi Om Pa Pb Pc Ri Ut) Nv(Ad bA bH cN Cs cZ dl dM Fn Fp Hc Jl Jo Kd Ki Kl Ko Kr Kx Kz Lu Mq Nf Ni Nn No Og Oi Ow Pa Ql To Uc) Dp(aE bH bV Cq Ct cZ Dk In Iz Jd Jg Jk Ki Kl Kr Ks Lu Ms Mw Nb Ni Nx Ny Og Oi Pb Qv Si Ue Ug Yd Tj) Fn(aF bA bH bJ bP cl cN Cq cT Dk dM Hx Jd Jg Kd Kl Mj Mr Ms Mt Mw Mz Nc Nx Ny Of Og Pa Vp Tj) Hc(aL bA bO cl Cq Dk dM eC eF In Ir Iz Jg Jo Kd Kg Ki Kr Lu Ma Ms Nb Og Oi Pb Ql Qy Ri) Kl(aX aY BA bH bV bW Ct dl Dk dM Ha Jd Kd Kg Ki Kr Ma Ms Mw Nb Nc Ni Nx Ny Of Ri Tj) Kg(Cx Hx In Io Jd Jg Ki Ma Mj Mr Ms Mt Mw Mz Nb Nc Ni Nx Ny Ow Pa Pk Qx Rh Ri Tv) Kr(Af bH Bn cl Cq Cx Dk In Jd Jg Jj Jl Jo Ki Ms Nb Ni Og Oi Ou Pb Qe Qu Ri To) Of(Ad Af Al Ba Bg bH bJ bR cl cN Cx cZ dl Fw Jg Kd Kf Kp Lu Mq Pb Ql Qy Ri Vo) Oi(aF aJ bH bN bV Cq Ct cZ Dk dM Hq Iz Jd Jg Jo Ki Ms Mw Nb Nd Nx Oa Ri Ut) Uu(Aj bA bV cH Cq Ct dD eC gL Ha Hb Ma Mr Nb Nc Nl Og Ou Ow Pc Ql Ri Sr) Aj(Bg bH bN bR cl Cx Fr Hb Io Ki Me Mr Mu Mw Nc Nj Og Pc Qx Vp) Cq(bA bH Cp dA dl Fp Iz Jo Kd Kx Kz Nf Ok Om Qz Uc) Ni(cl Dk Iz Jg Jo Ko Ms Nb Nx Pc Rv Sh Ux Wf Yl) Hq(aV bA bH bX cl cN cZ dA dl Kd Og Pb Tv) Iz(bH cZ Ef Hu Ko Mu Nc Nl Nx Og Pa Pb Pc) Om(bA bH bJ cN cT cZ dl dM Kd Pb Tv) Dk(cZ Fp Jo Ko Mq Nf Og Pa Pb Vo) Hu(bA bJ cl cT cZ Og Pa Pb Tv) Jo(bZ Ki Ma Ms Mw Nb Ny Og Ri) bH(Af bR Cp Jg Ki Nx Pb Tt) Kc(Rv Sh Vz Wb Yd Zq) Ko(cl Jg Ki Ms Pb Vp) cZ(Cp Jg Jh Ms Oa Og) Nx(Jg Ki Ql To Tv) Pb(Cp dl Kd Kx Qz) Cp(bJ cN cT) Uc(Jl Ri Vp) Kd(Lj Oa Vp) Oy(Fc Fi Wh) Af(gL Sf) Fp(Nh Ny) Ms(Ad Vo) Tv(Lj Oa) Jg(Lu Pa) Qx(Tr Tt) Ki(Db dE) bL(gL To) bW(Ap Bn) CtMq MwPa NbbA NcdI NfNy HbOg ShbO JhbJ cNdH} Ni{Ed(aA aD aW BA bF bV bZ cN Cv dI dM Dp Fd Fn Fr Fw Gc Hu In Is Jd Ji Jj Jl Jp Jq Jy Ky Lv Ly Ma Mm Mn Ms Mu Nk Nn No Oe Og Oi On Op Oz Pc Pf Po Qa Qe Qv Qy Rf Ri Sr St Tr Uf Uh Un Ur Vi Wb Zq) dN(aW bA Bg bH bN BO bR bV cT dH dI dM Dp Fd fP Fr Hc Hu Im In Is Jd Ji Jl Jn Jo Jr Kr Kx Kz Lu Lv Ms Mu Na Nc Ne Nf Ng Nn Nr Oe Og Oi Or Ou Oy Oz Pc Pf Po Qa Qd Qe Ql Qw Ri Rv Tn To Tr) Rv(aC Ad Al bF bQ bZ CS dF Fd Fr Hu Il Im Iz Jd Jn Jp Js Lj Lx Ma Mj Mn Mq Mu Mv No Nq Nv Nw Nx Oa Of Ok Or Pb Pe Qc Qd Qh Ql Sr Tn Tv Tz Vi Zw) Mn(Aj bV dM Hc Ih In Jg Jk Jp Li Lj Lu Lw Ly Ma Me Mh Mi Mm Mp Mr Ms Mt Mv Mw Mx Mz Na Nc Nj Nk Nl Ns Nt Ny Og Oi Om Pb Pc Vz Wf Yl Th) Yl(Af aG An Bb bF bM bQ bV bZ cC cT Cu cV Ez Fn Fr Gd Gl Hr Ij Il Ks Kx Li Ma Mh Nt Og Or Pk Qc Qn Rf Rh Ru Sj Uh Ut Uv Va Vi Zw Ye) Pc(bA bV bW cN dM Du Fd Jd Jg Jt Li Lj Ma Me Mi Mj Mm Mr Mt Mv Mw Mx Mz Ne Ng Nk Ns Nt Nv Ny Og Om Pa Pg Ri Ru Sr Uf Vi Zw Th) Fd(aC Af aM aZ Bn bR cC cX Dp Du Ez In Jd Ji Jn Kc Lj Ml Mt Nj Nk Nn Nw Oa Og Oh Or Ow Oy Pb Pi Pk Qh Qn Sj Us Ye Tm Wm) Wf(Dp Et Fr Fy Hu Ih Im Jd Jn Jp Lv Lx Mj Mv Mz No Nq Nr Nx Ny Op Ou Ow Pe Pg Pi Qc Qd Qh Ql Qy St Tv Ua Uh Vi Th) Mm(Hu Ih In Jg Jk Js Li Lj Lu Ly Ma Me Mh Mi Mj Mr Ms Mw Na Nb Ne Ng Nh Nk Nl Nt Nv Ny Og Oi Om Pa Pg) Nk(aD aJ aM bA bR bV bW bZ cN dF dI Jg Jj Jn Jq Lh Lx Ma Mq Mw Ny Om Ps Qb Qd Tn To Un Vi Vz Wb Zq) Mt(Du Fp Jg Jp Jq Lh Lt Lw Lx Ly Ma Mr Ms Mv Mw Mz Ng Nt Ny Og Oi Om Pa Qb Qd Rz To Wb Wc) Tn(aJ aV bV bW cN Co Cv dA dI Dp Hf Jo Jv Kj Kz Me Ms My Nf Oa Pa Pb Ql Qu Qw Rf Uf Us Uu) Vz(aC bN Dp Et Ez Ih In Jn Js Ks Lj Lx Mj Mv Nn No Nx Oa Oh Ow Pe Pf Pi Po Ql Tz Ut Zw Th) Mq(aW Fp Ih In Jg Jk Lh Li Lj Lw Ly Mp Mr Ms Mv Mw Mx Ne Ns Nt Ny Og Oi Om Pa Pb Pg Qb) Jj(Hu Ih Ii Ik Il Jo Js Lj Lw Me Mh Mi Mj Mx Nb Nc Ne Nh Nj Nl Nm Nr Nx Oz Pa Pd Pz Qc) Ps(aD aE Af aZ Bb cC dE Dg Dl Du Hc Hf Ji Kc Kl Mb Me Nj Nx Og Ow Pa Pb Us Uu Uv Vo Th) No(aD aM Ap bO bR bV cN Cu Cx Dl fP Fw Hf Iz Jv Kd Kg Kj Kl Ko Kr Ou Qu Ra Ri Ug Us) aW(bA bV Fr Hu Im Jd Jk Jn Jy Lv Lw Lx Ly Ma Me Mu Mw Nw Ny On Oy Pe Pf Qd Ri Sr St) Fp(Gd Hx In Jg Jk Jn Jt Lh Ly Mi Mp Mr Mv Mw Mx Mz Ng Nt Ny Og Oi Pa Pb Pe Qb Qd) Ma(Aj Ih Jg Jp Lh Lj Lw Me Mi Mr Ms Mz Nc Ne Nh Nj Nl Nt Og Oi Om Pa Pb Qb Qd) Hc(aJ bA eF Fr Hu Jd Ji Jl Jp Jr Nn On Op Pf Po Qa Qd Qe Qy Rz Sr Tt Vi Zq Th) bV(Aj bR cA cN cR Dp fP Fr Hu Ji Jl Jr Ly Me Ms Mu Nn Nr Og Oi Oz Pf Po Qa Qe) Lh(Hp Ih In Jg Jo Jp Lj Me Mi Mv Mw Mz Ne Nh Ny Of Oi Oy Pa Qb Qd Ux Wb) Th(Bo cM cN Cx dI Dk dM Fr Gz Jp Kc Ki Nj Oa Oy Pf Qg Ql Qy Wb Zq Tm) Is(aD aK aM Ao BO bR bW cN Co dI dM Jv Kg Kj Kr Ri Us Uu Ux Yd) Qb(Jg Lu Lw Ly Me Mi Mr Ms Mv Mw Mz Ne Ng Nt Og Oi Om Oz Pa Pb Pe) Jd(aA Ao Bb Co Du Gn Kg Kj Lt Ly Me Ms Oi Oz Rz Sj Uu Ux Wc Wd Wh) Wb(bA bQ Dp Du Et Ez Fy In Jr Lj Mv Nn Nr Nw Oh On Pe Qh Rm Ut) Jp(Kr Lj Lu Mh Mi Mr Ms Mv Mw Mz Nh Nj Nl Nt Og Oi Om Pa Pb Qd) Aj(Ba cN Dk EF Im Jn Jr Mu Mw Nr On Qd Sr St Tr Ua Uf Un) Qe(aK Ap aV bA bH bO Co Cv dA dI Dl dM Fn Kg Kj Qv Ri Us Uu) Jl(aE aK bA BO bR cC Co Cx dE dI dM Dp Kg Kj Kr Qv Ri Uu) Jq(In Jk Lj Md Me Mi Mj Mp Ne Ng Nh Nt Ny Oz Pb Pg To Wm) aA(aD aM aV Bg bM bR bW Cx dC dI dJ Kx Ou Ow Pk Ri Sr Tr) Ly(bA bW cN Cv dM Jg Ne Nh Nl Nt Qd Ql Ri Sr St Uf Un) Jg(Hu Lj Lw Me Mh Mi Mr Mw Mz Ne Ns Of Oi Oy Pa Pb) Og(dM Hp Jk Jt Li Mi Mr Mv Mw Mz Nb Nt Nv Ny Pa Qd) Lx(Hu Hx Ih Lw Md Mg Mh Ml Mv Nh Nl Ns Oi Om To) Nn(aM bR cN Co dI dM Dp Eq Jv Kg Kj Kr Ra Sh) Qa(aV bA bO bR Co Cv dI dM Dp Kg Kj Kr Ri Us) Om(Ih Jo Lw Mg Mh Mi Mr Mz Ne Ns Oi Oy Oz Pa) Sr(Dp In Jv Ki Kj Lt Ms Ng Oi Oy Oz Ri Uu) Vi(Af bN Hf In Kc Kz Nf Nj Oy Pa Pb Us) Du(Af bO bQ cC Jk Mu Mw Nq Or Pb Rb) Lw(Jk Li Lj Mr Mv Mw Mz Nt Ny Pa Qd) Jr(bA bR cN dI dM Kg Kj Kr Sj Us Tm) Dp(aJ Fr Ji Ky Pf Po Rz Va Zq Tm) Qd(Mi Mr Ms Mv Mw Mz Ne Oi Pa Pb) Me(bA bW cN Cv dM eF gL Lv Zq) Ng(Ba Dk Jt Li Mi Mw Nt Ny Pg) Hp(aC Af bN Et Ez Nw Pg Qh Sj) Oz(bA cN dI dM Jn Lt Ri St Un) Ji(bR dM Hf Ri Rz Si Uw Wc) Pf(bR Co dM Jv Kg Kj Kr Ri) Po(aM bO Co dI dM Kg Kj) Lv(Jk Lu Lz Nb Nh Nv Pb) Mw(Ih Mr Ms Mz Ne Pa Sj) Lt(Ih Nw Or Pb Pi St Un) Oy(bA cN Dk Ri Rt Un Ut) Fr(Co dM Jv Kj Us Uu) Hu(aD cN Co dI dM Uu) Sj(Im Jn Mu Pi Ql Qy) Zq(Af Bb Kc Pb Uu Vo) Ux(Ez Ih Jk On Rm St) Pa(Mv Mz Ny Rt Zw Tm) Ms(bA Dk Mp Nv Ri) Sh(Ks Nx Ny On Ut) Jn(cN dI dM Lu Ye) Mu(Ao Bb bR Tm) To(Dc Fy Rf Un) Op(Af Hf Kz Nf) Zw(bN dE Ri) Wc(Ow Pi Un) Rt(Af Ih Pb) Uu(Ba Un Vw) Cx(Cv Em) Tr(cN dI) Im(bW Ri) Tm(bN In) Oi(aJ Nt) Pb(Nv Pg) bA(aD aM) AfEm BbNw CoPe TibH EqQh GdNr MvMz NeNy HlRm JkKj XabO RuOr VwbN bRcN} Dr{Og(aA An Ao Aw aX aY bC bF bG bH bQ bR cE Ch Co Cp cS Cu Cx dF dI Ed Gl Gn Hu Ih Ik Im In Je Jg Ji Jn Jr Jy Kl Kn Ky Lu Mg Mi Mj Mr My Nn Nr Nu Oh Ok On Ow Pf Ph Po Ps Pz Qa Ql Qm Qt Qu Qw Rf Ri Rm Sr St Ua Uc Ud Uf Ut Uw Ux Vp Vw Wd Zq Ye Xa Wm Th) Jl(Af aZ Ba Bb bE Bn bU bZ cF Cp Cq cR Cu Cv cZ dA Dd dI dN Dp Du Ez Fd Fi Fw Gn Ho Hv Hx In Ip Iq Ir Is It Iv Jd Je Jn Jq Jr Js Jy Kc Kd Ko Kr Lu Mr Mt Mv Mw Mx Na Nf Nh Nj Nl Nm Ny Oy Pa Pb Pi Qh Ql Rt Tv Tz Up Ur Vp) Jy(aA Af AJ An aX BA bC Bg bR cF cN cP cS cT Cx dD dI dM dN Dp Ez Fb Fn Gn Gp Im In Jd Ji Jn Ju Jv Kc Kj Kx Ky Kz Lh Mi Mj Mp Mr Mw Nd Nf Nn Nq Nu Of Or

Figure 7 Continued

Oy Oz Pb Qb Ql Qm Qy Rb Rf Rm Sf Sh To Ud Up Ur Us Ye Tl) Mv(aA Af aJ aV aW aX aY bA bU bZ cT cU Cx cZ De dM dN Dp Fn fR Gn
Gp Ii Ik Im In Jo Jt Jv Kf Kg Ki Kp Ky Kz Lu Lv Mr Mt Mw Mz Nc Nd Nk Nm Nu Oe Oi Om Or Pa Qz Rb Ri Sh To Uk Up Vh Wh Ye Tl)
In(Af An Ao aW aY BA bG BN bQ bX bZ Co cP Cq cS cT cZ dI dN Dp Ez Fb Fn Fr Fy Gn Gp Hu Ib Ik Im Is Je Ki Ky Lh Lu Ma Mj Mz Nd
Nk Nn Nq Nr Qw Qy Rm To Uk Vj Vw Zq Ye Th) Oz(aX aY Ba bF BG bQ bZ CH cS Cu Cx Dk dM Ez Fb Fy Gn Hc Hu Im Is Je Jn Ky Lh Mj
Mr Mt Mw Mz Nb Nn Nq On Or Pf Qa Qe Qg Ql Qu Qw Rb Ri Ua Ud Ut Vi Vq Vs Zx) Ou(aV aW bE bJ bU cZ dI dM Dp Fn Gn Ib Ii Ik Im Jd
Je Jq Kc Kg Ki Kj Ky Lu Lv Mr Mt Mz Nc Nd Nf Nj Nk Nn Nq Nu Oy Qw Qy Rv Si To Uk Up Ur Us Ye Tl) Lu(Af aV aW Bg bR bU Cx cZ
dA Dp Et Fn Gn Gp Ih Im Is Jd Je Ji Ki Ky Lh Mr Mw Mz Nd Nn Nq Nu Or Oy Qa Qe Ql Qy Rb To Uk Un Zq Ye Th) Bg(aJ bH cT Cv dI dM
Dp fR Ib Ii Im Jd Jt Jv Kc Ke Kg Kj Lv Mi Mr Mt Mw Nf Ng Nj Nm Nu Of Or Pa Pb Ql Ri Sh Ud Ur Us Uu Vs Tl) bZ(aJ An Ao bE bH cS dD
dM Dp Ef Eq Ex Fi Fn fR Im Jo Ki Ky Lv Mi Mr Mt Mw Mz Nd Ng Nm Nu Oi Or Pa Pb Pc Ql Qy Rb Ri Rv To Ud) Lv(aW aX aZ Ba bE bJ
bU cF cL cS cZ dA dI Fd Gn Im Is Jd Je Ki Mr Mt Nd Nj Nn Nq Oe Oi Oy Pc Ql Qw Rb Tz Us Wc Th) Mw(aX BA Bb bF bH bQ Cx dA Dd dI
Dp Ez Gn Ha Hx Ib Iq Je Jt Kd Ke Li Ma Nc Nj Nk Nm Oe Or Oy Pb Ql Qm Ud Vs) Fr(aV bO Dp Du Ed Fn Im Iu Kd Ki Mr Nm Nq Nu Oi Or
Oy Ps Qb Ql Qn Qw Qy Rb Ri Rm Rv Ye Th) Jd(Af aX aY cS Cx dI Ed Ib Jo Jt Kc Kg Ki Mg Ng Nj Oi Om Or Pb Pc Qz Rb Si Ud Uh Vh Vs
Wc) Mt(aX aY BA bF cH dI Ez Jt Kd Li Ma Nc Nj Nk Nl Nm Or Qg Qy Sh Ud Uh Uy Vt Wc Tj) Nq(Af bA Bb bU cT Cx dA Dd dI DI Gb Ib Ii
Ju Kj Nk Nm Om Pa Pb Ql Rv Up Us Uu Vh) Lh(Cx cZ dA dI Du Fn Gp Ib Je Jt Kc Kf Mr Nc Nj Nk Nm Oy Pb Qm Rb Ri Uh Vt) Or(aW Ba
bN bQ cS Cx cZ dA Ez fR Gn Hb Je Ke Nk Nn Nu Pb Qy Ri Vw Th) Cx(aA Af aJ Ao aX bC bH bQ cS dF Ef Ez Fb Gp Je Ma Mr Qy) Pb(aX
aY BA bF bH cT Ez Fb Gn Hc Iz Je Ma Ql Qy Tn Ud) bF(aA bE cS dA dI dM Ex fR Je Mi Mr Nf Nu Oy Ri) Tn(aX bA cZ dA Fi Ii Jt Kc Ke Nf
Oy Pa Up Vh) bH(aJ bA bX Co cP cS cT fR Ky Mr Mz Nu Ri Ye) Ef(aP aX bQ bV cP Cs cU dF dG dM dN Gc) Qy(Af aY bQ bU Ky Ma Nd
Nj Nu Ri Us Ye) fR(aW Ba bE bL CH cT Cv cX dD dI Du) Ii(Ba Dk Fy Im Ji Jr Mj Nn Qa Ql) Je(Af bG cS Jp Ky Mn Mz Nd Nn Qv) Nm(Ba
bQ Co Et Im Ma Nn On Ql) Nj(bA Is Ji Ky Rb Rm Xa Th) Jt(Ba Dk Im Is Jn Mj On Qa) Mr(aX Ch cS Fb Gn Hx Ud) On(dI Kj Nc Oy Pa Us
Vh) Co(aA aJ cS dA dI dM) Ez(bN Ed Kg Ki Ky Nu) Ma(aX bA Ki Oy Pc Ri) Ch(aJ cS Kj Nu Oy) Nk(Im Jr Mj Nn Qa) Ke(Is Jr Mj Qa) Ri(aX
cS Ql Ud) bQ(Cv cX dD Ki) cT(bE bU dN Pa) Nn(dA Dp Rb) Oy(Hc Iz My) Nu(aX cH) Nc(Is Jr) Rb(Si Wc) Us(Dk Ut) aJ(bG cH) bA(bE dD)
AncS BabX MibU NlJr UdKy ImaY YeQl UtcZ aAcX dDdF} dN{Jy(aA aF Ao As aW aX bA Bb bF BN bO bQ bR bS bV cA cE cG cL CT Db
De dL Dp Fn Gp Hc Hf Im In Jn Jo Jt Jv Kd Kg Ki Kj Ky Kz Md Me Mk Ms Na Nc Nd Nf Nl No Oa Of Og Oi Pa Pb Pc Ql Qz Rf Rh Ri Uk Uu
Tj) Ly(Aj Ba Bg bN bR bV cT dI Dk dM Dp Ed Fr Gp In Is Je Ji Jj Jn Jr Kg Kk Kx Ky Lu Lv Lx Mq Mr No Nw Oe Oi On Or Oy Ql Qv Rf Ri
Sr St Uf Ug Un Ut Vp) No(Aj Ap bA Bb bH bN bR cA cT Cx dH DL Dp Ed Gp Hc Hf Ii In Jo Jv Kd Ke Kg Ki Ko Kr Li Lu Lv Ms Nc Nf Ng
Nl Oe Og Oi Oz Pa Qz Ri Us) Me(aW Ba bH bO bV dI Ed Im Is Jd Ji Jj Jn Jo Jp Jr Kg Ki Ky Lu Lv Lx Mr Nn Nw Oe Og Oi On Ou Oy Pc Qa
Qe Ql Qy Rb Ri Ur) Mu(Ao Ap bA Bg bN bO bR cT dH Ed Hc Hq Hu Im In Jo Jt Kg Ki Kj Kr Kz Lj Lu Lv Ma Ms My Nc Nf Nv Oa Oe Og Oi
Oz Pc Uk Us) Jl(Aj Ap aW bA Bg bN bR cT dH DL Dp Hc Hf Ii In Jo Jt Kg Kr Lu Ma Ms Nc Nd Nf Ng Nl Oe Og Oi Oy Oz Ri) Bg(AJ Ba bR
cA Dc dI dM Dp Ed Hc Im In Jo Jr Kg Ki Kr Kx Kz Lu Mq Mr Ms Nf Ng Oe Og Oi Oy Rf Sr) Fr(Aj Ap aW bH bM bN bO bR cA Dg dH Dp
Fp Hc In Jo Jv Kg Ki Kr Kz Ms Nf Ng Oe Og Oi Oz Us Uu) Lu(bA bR cT dH Dp Ed Im In Is Ji Jn Jr Lv Mr Nf Nw Oi Oy Oz Pb Pc Po Qa Qd
Qe Ql Rf Un) In(bA bN cT Dp Ed Fp Im Jd Ji Jn Jr Kz Lh Mr Nf Nn Nr Ow Oz Pc Po Qa Qe Ql Qt Qw Sr) aA(Ba Bc bL bQ bS eC Io Kd Ki Kz
Lv Nr Oe Og Or Ou Ow Oy Pk Qe Ql Rf Rh Ri Tn Us) Oy(BA bF cT Ef Hu Is Jd Jr Lv Ma Mr Ms Nn Nq Nr Oe Ou Pf Sr Tn Ut) bA(Dp Ed eF
Fn Hc Is Jn Jq Jr Ki Kr Ma Mr Ms Nf Oi Oz Pb Pc Ql Rf) cT(Dp Ed Fn Hc Il Is Jn Jq Ki Kr Mr Ms Oe Og Oi Oz Pb Pc Ri) Oi(bN bV Dp Ed Im
Is Jd Jn Jr Lv Ma Mr Nf Nn Qa Ql Rf) eC(Ad Aj aV bM bO cK Cq cS Cu Cw Dc Dp Jq Kx Pk Ri Un) Ba(aC Aj aW bO bS Dc Dg dH Ed fP Jo
Kg Kl Ms Ng Uu) Is(Aj aW bO bR Hc Ii Jo Jt Kg Kr Ms Nc Oe Og Us) Kg(Ef Im Jd Jr Lh Ma Nf Nn Nr Ou Sr Tn) Ms(Ef Im Jd Ji Jn Jr Lv Nn
Ql Qy) Aj(Hu Jd Ma Mq Mr Nn Qt Tn) Kr(Im Jn Jr Lv Nn Ou Qa Qe) aJ(bN bO bR bS cA dH dL) Lv(bN Fn Hu Oe Oz Pc) Jd(bO Hc Jo Og Oz
Us) Rf(Dp Ed Nf Ou Oz Pc) Sr(bO Dp Jv Ki Oz) Jo(Ef Fy Mq Mr Nf) cA(bH bV bZ dA dM) Ma(bS dH Ql Ri) Ng(Ef Hu Nq Qy) bR(bH bZ dM
Mr) Ed(dL Ef Qy) Im(Ki Oe Ri) Jr(bN bO Ri) Dp(Jj Qv) Mr(aW Ri) Nf(Jj Ur) Ki(Db Og) Ql(Oe Og) Ou(Oz Pc) fP(Bo Mq) DcbH GpOr TrPc
TnOz HcQy KzeF bNtF dHdI} Jj{Ma(Dp Hu Hv Hw Ih Ij Ik In Ir Jg Jo Jp Li Lu Lv Mh Mn Mt Mv Mw Mx Na Nb Ne Nf Ng Nj Nl Nr Nu
Nv Nx Ny Oi Pa Pc Pd Pg Qb Wm) Mw(Hu Hv Hw Ij Ik Im Ir Jg Jk Jm Jo Jt Lu Lw Lx Mh Mi Mj Ml Ms Mt Mv Mz Na Nb Ne Nf Nh Nl Nr
Nu Nv Ny Pc Pd Pg Qb Qd Wm) Lx(Hq Hu Hv Hw Ij Ik Ir Jg Jk Jo Jp Jt Lw Ly Mm Mn Mr Mt Mv Mz Ne Nf Ng Nh Nr Nv Nx Ny Og Oy Pb
Pc Qb Qd) Mr(Hu Hv Hw Ii Ij Jm Jo Jp Jt Li Lu Lw Mm Mp Mt Mv Mz Nb Nf Nh Nj Nr Nv Nx Ny Pd Pg Pz Qb Qd) Im(Dp Hv Hw Ij Ik In Io
Ir Jg Lw Mh Mi Mk Ml Mn Mt Mx Na Ne Nh Nr Nu Nv Pa Pc Qd Wm) Qd(Dp Hu Hw Ij Jg Jk Jo Jt Lu Lw Mn Mt Mv Mz Na Nb Nh Nv Nx
Ny Oi Pc Pd Pg Wm) Dp(bA bZ cT Fr Is Jn Jq Jr Lu Lv Mq Mv Nf Nr Oa Pe Pf Po Qa Qe Tn Un) Nv(Hu Hv Hw Jo Jq Jt Lu Lw Mh Ms Mv Mz
Na Ne Nf Ng Nh Ns Og Oi Pc) Jk(Hw Jo Jt Lw Mh Ml Mm Mn Ms Mt Mz Nf Nh Nu Nx Ny Og Oy Oz Pg) Ny(Hu Hw Ij Ik Jo Jt Lu Lw Me
Mv Mz Na Ne Nf Nh Nr Pc Pd Pg) Ij(Jp Lu Lw Me Mm Mn Ms Mt Mv Mz Ng Nh Og Oi Pb Pc Qb) Me(gL Jm Jp Li Lw Mp Mv Mz Nh Nr Nx
Pc Pd Pz Qb) Mt(Hv Hw Jo Jt Lu Lw Mn Mv Mz Na Nb Oi Pc Pd Pg) Mn(Hu Hw Ik Jo Jt Lu Mv Mz Ne Nf Nr Pg Wm) Mv(Hw Jo Jt Lw Mm
Mz Ng Nh Nx Pg Qb Wm) Et(Hv Io Ir Jo Jt Mi Mj Na Ng Ok Wm) Mz(Hu Ik Jg Jm Lw Mm Nh Nr Pc Pg Qb) Qb(Hu Ik Jg Jo Jt Lu Lw Nf Pd)
Pg(Hu Hw Jt Lw Nf Ng Nh Oz Pb) Jg(Hw Jo Lu Mh Nh Oi) Jp(Ik Lh Nf Nh Nt) Jl(bO Kr Ri Us) Jt(Ik Lu Nh Pc) Ed(Ef Fr Jy) Mm(Jq Lu Nf)
Nx(Jq Lh Nf) Wm(Ly On) Jy(Fp Ly) Kr(Is Qa) Kz(eF gL) EfUu NoJv NtNa NfNh LhOf OzPd bVfP} Oy{Mu(aC Ad Ao As aW Ax bA Bn bR
bS Cp Cq cT Cu dA Dc Fa Hc Hl Id Ir Iz Kd Ke Ki Kn Kp Kr Kx Ky Kz Mj Ml Mp Nx Oe Ou Pi Ps Sr Wf Xa) Tn(aA aJ Ba bW Fr Id Im Is Ji Jl
Jq Jy Lw Mq Mt Nj Nk Nn No Nw Oz Qe Ql Rf Ri Sr St Uf Un Vq) Jy(aA aJ aW bV cN cT Cw dA dM Id Ij In Jd Ji Jq Mi Mq No Ny Om Pb Pi
Qa Qe Sr Un Uv) Pf(Hv Hw Ij Im In Ir Jg Jn Jo Jp Jt Lu Lw Me Mm Mn Mr Mw Mz Na Nt Nv Oh Oi Pc Pe Qd) Lx(Fp Hv Hw Ij Im Jn Jo Jq Jr
Jt Lh Lu Lw Ly Ma Mv Mw Nf Nl Nw Oi Ok Pc Pe Po) Om(Bg Ef Et Hu Im In Is Jd Jn Lj Ma Me Mh Mk Ne Nn Oi Ok Oz Pa Pc Qb Qd Qy)
Po(eF Hr Hw Im Jg Jn Jp Jt Me Mi Mk Mm Mn Ms Mt Nh Ns Nt Oz Pa Qe) No(aW dM Dp Hw Im Jn Jo Lj Lw Mm Ms Mz Nf Nh Nk Nl Ns
Ou Pd Pe Ri) Nn(dM Hw Im In Ir Jn Jt Lu Mk Mz Na Ne Nh Ns Nt Pa Qd Qe Un Ut) Nw(eF Hv Im Io Ir Jg Jk Jn Jt Lw Mi Mk Mr Mw Ne Nh
Nt Oh Pa Pd) Lh(Et Fp Im Is Jg Jn Jq Jr Lv Lw Ma Mq Mv Nb Oh Ok Pc Qa Qe) Pe(Et Im In Is Jq Jr Lu Ma Mm Mq Mv Nb Oh Ok Pc Qa Qe)
Ut(aA aW BA bH dA Dp Jd Jv Kr Mq Qy Ri Sr Us) Nb(Et Fp Im Is Jr Lv Ma Mv Oh Ok Pc Qa Qe) Qa(Hu Jg Ma Mi Mm Mr Mt Mz Nf Ok Pc
Qy) Fr(aW Cs Dc dM Ed Ke Ki Ql Sr Tv Vt) Lv(Jg Jp Li Ma Mi Mv Nt Pc Pd) Is(Jg Jq Lu Ma Mm Mr Mz Ok Pc Pd) Jq(bZ Et Im Lu Ma
Oh Ok Qy Wm) Mq(Et Jg Jn Jp Oh Pc Qd Qe) Et(Im Jn Mr Mv Mz Oh) Ok(Fp Mr Mv Oh Pc) On(Dp eF Jv Vz Wh) Ma(dM Jr Qe Un) Jd(bA
Ms Oi Sr) Qe(Jr Mz Pc) Un(bZ gL Ms) Vi(Ez Fb Ql) eF(Ji Ny St) Mw(Tr Tv) Ri(Jl Sr) BgaA NrdM MtVz MzIm TrJh JgJr JigL QybA}
Ng{Qe(Hu Hw Im In Is Jk Jn Jo Jp Jr Jt Jy Lw Me Mi Mm Mn Mr Mt Mw Mz Nb Nc Nf Nk Nq Nt Nv Nx Oh Oi Pc Qa) Jd(aA aW BA bR cT
Ed Fr Hu Jl Jv Ki Lu Ly Ma Me Mq Ms Mu Nc Nn No Nr Og On Oz Pf Qt Rh Ri Sr Tn) Lh(Fp Hu In Jh Jn Jp Lu Lw Lx Ly Me Mi Mn Mp Mr
Ms Mt Nb Nf Nh Nl Nt Nv Ny Og Oh Oi Pb Pe Qb Qd Wm) Lx(Fp Hu Hv Hw Ij Jh Jk Jn Jo Jp Jt Lu Lw Ly Mm Mn Mt Mw Nb Nf Nh Nt Nv
Ny Oh Oz Pb Pc Pf Qd) Pf(Ij Im Jh Jk Jn Jo Jp Jr Jt Lj Lu Lw Ma Me Mi Mm Mn Mt Mv Mw Mz Nb Nv Nx Pc Pe) Ma(Fp Ii Im Jh Jo Jt Lu Lw
Me Mi Mm Mr Mt Mv Mw Mz Nh Nv Oh Pc Qd Qy) Et(Fp Hw Ij Ik In Io Jt Mh Mi Mz Ne Nh Nq Nr Nv Oi Pa Pg Qb Qd) Mv(Fp Ii Jh Jk Jn Jp

Jr Lh Lu Lx Mi Mn Mr Mv Nc Nf Nk Nt Oh Pa Pb Pc Pe Pe Po) Nc(Is Jg Jn Jp Jr Lh Lw Lx Mm Mn Mr Mt Mz Ne Nh Nt Pa Pc Pe Pf Po) Nk(Fp Is Jg Jr Lh Lu Lx Me Mm Mn Mr Mt Mz Nn Pa Pc Pe Pf Po Rv) Me(It Jg Jm Jp Jr Lh Lu Lw Lx Mm Mn Mt Mz Oh Ok Pe Pf Po) Lu(Fp Im Jr Lh Lx Ma Mm Mn Mr Nn Ns Oh Pb Pc Pf Po) Pb(Jg Lw Ma Mi Mr Mz Nb Nf Nn No Ok Pa Pc Pe Pf) Lx(Hq Ii Jm Jr Lw Ly Ma Mh Nn Ns Of Pa Pc Qe) Lw(Fp Jr Lh Mr Mt Mz Nn No Ns Pe Pf Po) Mm(Hu Is Jn Lh Ma Mr Mt Mz Nf Pe Po) Pc(Jm Lh Mr Mt Mz Nf Ns Pe Pf Po Qe) Nn(Fp Hu Im Jm Jo Jr Mr Ns Pe Pf) Ii(Is Jg Lh Ma Mn Nf Oh Pe) Pf(Im Jr Lj Ns Ok Oz Pa) Po(Hr Jm Jo Jr Ma Ns) eF(Aj Hc Kg Kj Kr Us) Ma(Lh Mt Mz Pe Qe) Jg(Hu Jm Mr My Ns) Nf(Hr Jm Ns Ok) Pe(Jo Mt Nl Pa) No(Iq Ns Ok) Nj(Rv Vz Yl) Ly(Iq Om) Mn(Jm Mr) Im(Ih Mz) Jo(Lh Ok) Jr(Lh Ns) Kr(Ou Ri) Us(Jl Mu) Pa(Ok Om) MrNl MtQc IsJm JnJs bRdl] Po{Pb(Hv Hw Ij Im Io Jn Jo Jr Jt Lw Lx Ma Me Mm Mr Ms Mz Nk Nn No Nt Oe Om Pc Qe) Ma(Et Hv Hw Ii Im Is Jn Jo Jt Lh Lw Me Mg Mm Mq Ms Mz Ns Oe Oz Pc Pe Qe) Oe(Im Jg Jn Jp Jr Jt Lh Lu Lw Mm Mz Nk Nn No Nt Nw Oh Om Oz Pc Pe Qe) Ns(Et Im Is Jg Jn Jp Jr Lh Lu Me Mm Ms Mz Nn No Ok Om Pc Pe Qe) Ms(Im Jg Jn Jp Jt Lh Lu Me Mm Mn Mw Mz Nb Nk No Oh Oz Pe Qe) Lu(Hr Hu Jn Jr Jt Lw Me Mm My Mz Nh Nk Nw Oh Pc Qd Qe) Nk(Hr Hu Im Is Jn Jr Lh Lw Mz Ne Nh No Pc Pe Qe) Jn(Et Hr Ii Im Io Jm Jo Lw Mm Nc Nw Pa Pc Qe) Pc(Hw Im Is Jr Lh Me Mr My Mz Pe Qd Qe) Lw(Ii Im Is Jr Lh Me Mt Mz Nw Pa Qe) Im(Ii Io Jr Lh Me Mt Mz Nw Pe) Jo(Hv Hw Jt Lh Me Mq Nt Om Pe) My(Et Jg Lh Mt Nb Nn Om) Hu(Et Jg Lh Mq Nn Nw Ok) Ii(Jt Lh Mq Nn No Om Qe) Mz(Et Hr Mm Nc Pa Qe) Me(Hr Jp Jr Mt Oh) Oz(Et Mq No Ok Pe) Nc(Jr Ne Nh No) Qe(Hr Il Jm Pa) Lh(Hr Mg Mm Of) Ly(Fp Mq Nw) Io(Et Jp Ok) Is(Mm Ok Pa) No(Lj Pa) Jr(Hr Pa) eF(Aj Kj) EtNw NnOk MiHq MmHw OfOm} No{eF(Af Ao bL bO Co Cq De Dg dH fP Fw Gp Hf Hq Hu Ii Iu Jk Jo Jt Ju Kc Kd Ko Ly Nd Nf Nl Nv Oz Pa Pb Pz Qz Ri Rm Vo) Pb(Hv Hw Ij Jg Jo Lj Lw Lx Ma Mz Nf Nl Nw Pe Pf Qe) Ii(Dp Ef Ij Ir Jg Jo Jt Lh Nf Or Pe Qe Ud Un) Ns(Im Io Jg Jn Lh Lj Lw Ma Mm Nf Nw Qe) Mm(Fp Hw Jn Lh Ma Ms Mz Nc Nf Nk Pa) Im(Iq Jn Lh Lj Lw Mz Nc Nk Nn Oe Pe) Nc(fP Jn Jv Mt Mz Nl Nw Oz Qe) Nf(Io Iq Lj Lw Ma Ne Nh Nk Oc) Lh(Io Jo Jt Lw Ma Nk Nl Oc Pa) Qe(Iq Jm Lj Lw Nl Nn Om Pa) Oz(Jv Ma Oh Pe Pf Ri Tn Us) Lu(bO bR bS cA Hc Jv Uu) Oe(Jg Jn Nh Nt Nw Oh Pe) Pa(Jg Jn Lw Mz Oh Pe Pf) Aj(Dp Ef gP Me Ri Tn) Ms(Jn Lj Mn Mw Nk Pe) My(Jg Mt Mw Nb Nw) Nk(aW Fp Ne Nh Pe) Jv(CH Kr Ly Us) Nl(Mr Ne Nh Pe) Jt(Ad Jo Om Un) Lj(Io Mt Mz Pf) Us(bA Jl Lv Mu) Uu(Ba Jy Qy Ri) Bb(Jd Jy Ri) Dp(Kg Qv Ur) Jn(Io Lw Nw) fP(bV Mq Qv) Co(Ef Lv) Me(aW dM) Mh(Lx Oh) Hu(Jg Jh) Pe(Io Nr) gP(Kg Kj) BgSh EfIz FwbA NnLw MaMz MgJg MiHq MnNh MpNd JfgL KrOu bRdI} Mu{Pb(Hv Hw Ih Ij Jo Jp Lj Lu Ly Mh Mj Ml Mn Mt Na Nb Nf Nh Nn Ny Oe Om Pa Pd Qb Qd) My(bS Hw Hx Ij Jg Jh Jp Jt Ly Ml Mm Mn Mw Na Nf Nn Nx Ny Pa Pc Qb) Oz(Bb Ih Lx Mh Mi Mj Ml Mn Ne Nh Ns Nt Oe Oh Om Pa Qb Qd Rx Wf) Bb(Ax bA bR bS cA Cs cT Ed Et Fp Is Ji Jn Jr Me Mq Sr Un) Ns(Hv Hw Jp Jt Lj Ly Mh Mj Mt Nf Oe Pa Pd Qd) Mg(Hv Hw Ij Jo Jp Mn Nb Nf Nn Ny Oh Pa Pc Qb) Ly(Lj Ml Mm Mx Ne Nh Nu Oh Om Pa Qb Wm) Mm(Hv Ih Jt Lu Ml Mt Na Nf Nt Oh) Of(Hv Hw Ij Jo Mn Nb Nf Nn Nt Pa) Lx(Hv Hw Jk Jt Mh Mv Nh Oe Pg) Nh(Jp Mn Nc Nf Nk Nn Pa Pc) Oe(Ed Hw Jp Mn Na Nf Ny Qb) Hu(bR bS cA Mh Mw Pa Qb) Ne(Mn Nc Nf Nk Nn Pc) Oh(Hv Hw Jt Lu Nt Pc) Us(bA Ed Ji Jr Ps Sr) Om(Jh Jk Jo Mv Mw) Aj(Fy Is Me Sr) Mn(Hv Hw Ih Lj) Mt(Hv Hw Na Nt) Pc(Hw Mi Na Qd) Jk(Nn Nt Pa) Lj(Io Nk Nt) bN(Wf Yl Zq) Ao(bS Ed) Co(aW bS) Wm(Jq Ms) Mb(Jt Na) Sr(Kj Uu) MaNa MhNk MiQd MwNb IoJp QbJm KcVi UubA} Mq{Mt(Fp Jn Jp Jt Lh Lw Lx Ma Me Mi Mm Mn Mr Ms Mw My Na Ns Nt Oh Om Pc Pe Pf Qd) Jp(Im Io Jn Lu Lw Lx Ma Me Mi Mr Ms Mz Nh Ns Oh Ok Pb Pc Pe Pf Qd) Om(Fp Im Jn Jo Lj Lu Lw Ly Ma Me Mi My Mz Ns Of Oh Pc Qd Qe) Pc(Fp Ir Jt Lh Lu Lw Lx Ma Me Mn Mr Ms Mx Na Nh Nt Oh Pe) Mi(Fp Jg Jn Lu Lw Ly Ma Me Mm Mn Ms Mw Ns Oh Pb Qd Qe) Fp(Et Ik Jg Lh Lu Lw Lx Ly Ma Mm Mn Ms Mx Ns Pe) Jn(Jg Lh Lw Lx Me Mm Mn Mw Mz Ns Nt Oh Pb Pe Qd) Im(Io Lh Lx Ma Me Mm Mn Mr Ms Oe Oh Pe Qe) Lw(Et Lh Lu Ly Ma Me Ms Ns Oh Pe Pf Qd) Qd(Et Io Lu Lx Ma Me Mn Ms Mz Ns Ok) Ns(Jg Lu Lx Ma Mn Mp Mr Mz Pe) Ms(Lh Lx Ma Mn Mw Mz Nb Pe Pf) Me(Jg Lx Ma Mm Mn Mz Pe Qe) Ma(Jo Lh Lu Mg Pb Pe) Qe(Hr Io Jm Lx Oh Pb) Et(Io Lx Ok Oz Pb) Lh(Jo Ly Mm Oh Pb) Pe(Lu Ly Mm Oz Pb) Mn(Lu Mr Mz Ok) Oh(Ii Jg Ly Oz) Aj(gL Tn) Lu(Mm Mz) Jg(Hu My) Ok(Ii Of) ChgL NtLy LxHq MwMz} Lv{Io(Hu Ih Jg Jt Li Lj Ly Ma Me Mi Mn Mp Mv Mx Na Nb Nf Nh Nt Nv Ny Om Oz Pb Pc Qb) Me(Jg Jq Lh Li Lj Lu Lw Ma Mi Mn Mp Mr Mv Mx Nb Nh Nt Nv Ny Pa Pc Qd) Nh(Jg Jp Jq Lh Lu Lw Lx Ly Ma Mi Mn Mr Mv Mw Mx Nb Nf Ny Oz Pa Pc) Pc(Hu Jp Jt Li Lj Ma Mi Ms Mv Mw Mx Na Nb Ne Nf Ns Nt Ny Pa Qd) Pa(Hu Jg Jp Lu Lw Ly Ma Mr Ms Mv Mx Nf Ny Oe Oz Pb Qd) Mr(Jg Jo Jp Jt Lh Lu Ly Ma Mn Mv Nf Nt Om Oz Qd) Lw(Hu Jg Jp Li Lj Lx Ma Ms Mv Mx Nb Nf Nt Qd) Lu(Ih Jg Js Ma Mp Mv Na Nb Nf Ny Pd Qb) Ms(Jg Jp Jq Jt Lh Li Lx Mn Mp Mv Nb) Nt(Fp Jo Jp Ly Ma Mv Mw Mx Nf Pb) Hu(Aj Co Jg Lj Ly Mt Mv Mx Uu) Fp(Hx Jt Mi Mn Mx Nb Qe) Ma(Li Lj Mx Na Nb Ne Nf) Jg(Lj Mx My Ne Nf Ns Qd) Wm(Iq Jn Jr Ly Mt Nw) Nf(Jp Mn Mw Ne Qd) Lx(Jp Mx Oz Qd) Ly(Lh Mi Ne Nu) Nb(Lj My Of Pb) Mi(Jq Lj Pb) Mw(Lh Lj Mx) Jp(Lh Ml Mx) Li(Jq Pb) MnNe MvLj HcQy JlUs JoJt OzdM} Nw{Ly(Et Ik Io Jo Lh Lu Lw Mf Mr My Nd Ne Nh Nj Ns Nt Nu Oe Oh Pe Pf) Im(Hv Io Jn Jo Jt Lh Mm Mr Na Nn Ns Oe Ok Pa Pb Pc Pe Pf Qe) Pc(Et Hu Hv Hw Ir Jn Jo Jt Lh Lu Mr Na Ne Pa Pb Pe Tr) Ns(Et Hv Io Jn Jo Jt Lw Mr Mv Na Nf Oh Ok Pe Pf) Pa(Hv Hw Ir Is Jn Jo Jt Lh Lw Mr Na Ne Nn Oe Oh) Ii(Hv Hw Ij Ir Is Jo Jt Lh Mv Na Nf Nn Pe Qe) Et(Hv Hw Io Jn Mr Na Ne Nn Oe Oh Ok Pf) Io(Ir Jn Jt Lw Mi Mm My Nt Pb Pe) Lh(Hq Hu Lw Mg Mw Nv Oe Of Pg) Pb(Is Jn Mr Mv Na Nf Nt Oh Om) Pf(Hv Hw Is Jn Lj Lw My Ok Oz) Nn(Hv Hw Jn Mr Mv Mw Nv Of) Oe(Lu Mv Na Nt Oh Om Pe Qe) My(Jn Mn Mr Mt Nt Oh Oz) Of(Hv Jt Mv Nf Ok Om Pe) Hu(Ij Jo Mv Nf Nt Om) Lw(Mh Mr Mv Pe Qe) Mm(Ij Is Lu Mr Na) Jo(Jt Lu Nx Ny Oh) Oz(eF Ne Nh Oh Pe) Mw(Lu Mv Nb Om) Md(Hv Ij Om) Nf(Ne Nh Nt) Hq(Mi Pd Pe) Hw(Is Ny Qe) Me(aW gL) Mg(Mv Om) Kz(eF gL) Ok(Is Oh) WmMs MhPe NcNe HvQe NvOm} Jr{Lu(Fp Jg Jn Jp Jq Lh Lx Me Mn Mr Mw Nc Nh Nk Ns Nt Oh Pc Pe Pf Qd Qe) Lw(Fp Im Is Jg Jp Jq Lh Lx Me Mr Ms Mv Mw Ns Oh Om Pc Pe Pf Qe) Pc(Fp Is Lh Lx Me Mm Mr Ms Mz Nc Nh Nk Ns Nt Om Pe Pf Qd Qe) Jq(Fp Im Is Jg Jp Lh Lx Me Mr Ms Mv Mw Nh Nt Oh Pa Pe Wm) Ms(Im Is Lx Ma Mm Mn Mv Mw Nb Nq Nt Oh Pe Pf Qe Wm) Lx(Hq Im Is Ly Ma Me Mh Mm My Nh Nk Ns Pb Qe) Pf(Im Is Lh Lj Ma Mm Nc Nk Ns Om Oz Pa Pb Qe) Me(Im Is Jg Jp Lh Mn Mr Mw Oh Om Pa Pe Qe) Im(Ih Io Mr Mz Nc Nk Nn Ns Oe Om Pe) Qe(Io Lh Mm Mr Mz Nc Nk Ns Oe Om Pe) Ma(Fp Io Is Jg Mr Mz Nh Ns Nt Pe) Is(Js Lh Mr Nc Nk Nl Nn Ns Oe) Pe(Mm Nk Nl Nn Ns Oe Pa Pb) Nc(dI Mm Ne Nh Nl Nt Ri) Om(Fp Ly Mg My Oe Of Pb) Jg(Hu Io Mr My Ns Oe) Nn(Fp Ii Lh Nk Pb) Mm(Fp Mv Mz Nf Ns) Lh(Jo Ns Oe) Nh(Nk Nl) Jp(Fp Io) Us(Jl Jy) NqMy NtOe MnMr IiSr} Et{Ms(Fp Im Io Jg Jk Lh Lw Me Mi Mr Mt Mv Mw Mz Nb Nf Nh Ok Pa Pc Pe Pf Qb Qd) Fp(Hx Ik Im Io Jn Jo Lh Lw Lx Ly Ma Me Mi Mr Mt Mv Mz Oh Ok Om Pc Pe) Lx(Hq Hu Im Io Jn Jo Ma Mg Mh My Mz Nf Nh Ns Oe Of Oz Pb Pc Qe) Ma(Hw Im Jo Lh Lw Mg Mr Mt Mz Na Nf Nn Oh Ok Om Pc Pe Qb Qd) Im(Io Jn Jq Lh Lw Mh Mi Mr Mt Mz Nf Nn Oe Om Pc Pe Pf) Pe(Io Jo Jq Ly Me Nf Ns Oe Oz Pa Pb Pc) Pf(Io Jn Jo Lw Mz Nf Ns Oz Pa Pb Pc Qe) Mr(Io Jn Jo Lw Ly Mt Mz Oh Oz Pc) Lh(Io Jt Lw Ly Mg Oe Of Pb Pc) Nn(Ii Mg Mz Ne Nh Pa Pb Qe) Jo(Hw Jn Jt Mv Mz Nf Nt Om) Oh(Io Mz Ns Ok Oz Pa Pc) Qe(Ii Jn Jt Mt Nf Ns) Om(Hu Me Mg My Of Pb) Pc(Jn Mi Mz Ns Ok Qd) Mv(Hu Jq Mg Mz) Nf(Jn Mi Ne Qd) Io(Mi Mz Qd) Jn(Js Jt Oe) Mt(Lw My) LyNh MhJq MwMy JlUs} Is{Io(Fp Im Jp Jq Lh Lu Lw Lx Ma Me Mi Mr Mz Na Nn Ns Nt Oh Om Pb Pc Pe) Ms(Fp Jp Jq Ma Me Mi Mn Mr Mt Mv Mw Mz Nb Nc Nf Nq Oh Pe) Oe(Im Jg Jp Lh Lx Ma Mm Mr Mv Nf Nt Oh Ok Om Pa Pc Pe Pf) Pc(Fp Jm Jq Lh Lu Lx Ma Mr My Mz Nk Ns Nt Pe Pf) Pe(Ii Im Jm Lu Ma Mm Nc Nk Nl Ns Oz Pa Pb) Om(Fp Hu Ii Lu Ma Me Mg Mr My Ns Of Pb) Pf(Ii Jm Lw Mm Nc Nk Ns Ok Oz Pa Pb) Lx(Hq Ii Jq Ly Ma Me Mh My Ns Pb) Lh(Fp Ii Im Jo Lw Ma Me Mm Of Pb) Lu(Aj aW bR Mr Nn Ns Oh Pb Uu) Ma(Fp Lw Mm Mr Mz Nn Ok Qe) Me(It Jm Jq Lw Mt Oh Ok) Mr(Jq Lw Ly Mm Nl Nn Ns) Fp(Jm Jp Ly Nk Ok) Nn(Jm Lw Mm My Pb) Ns(Jg Lw Mm Oh) Mz(Im Lw Mm Nc) Ok(Ii Jq Jt Pb) Nt(Ii Nc) Hc(eF Tn) Jg(Hu My) Rv(Nj Nk) bV(Kr Us) WmJq LwMt LyIq MmNf NcNe QeJm JnJs} Jq{Ma(Im Io

Figure 7 Continued

Jg Jn Jo Jp Lh Li Lj Lu Lw Lx Me Mh Mn Mr Ms Mt Mv Mw Ne Nh Nt Oh Pa Pc Pe Qb Qd Wm) Lu(Jn Jp Lh Lj Lw Me Mh Mn Mr Ms Mw Ne Nh Ns Nt Oh Pb Pe Qd Wm) Mm(Im Jn Jp Lh Lx Me Mh Ms Mv Ne Nf Nh Nn Nt Oh Pa Pc Pe Qb Qd) Im(Fp Io Lh Lx Me Mh Mr Ms Mv Nh Nt Oh Pa Pc Pe Wm) Pc(Jn Jp Lh Lx Me Mi Mt Mx Ne Nh Ns Nt Oh Pa Qd) Ms(Fp Jp Lh Lx Mi Mr Mt Mv Mw Nb Nq Nt Pa Pe) Lx(Hq Ly Md Me My Nh Ny Of Oh Om Pb Pg) Oh(Jg Jp Lh Me Mr Nh Nt Ok Pb Pe) Mr(Jg Jp Lh Ly Mn Mv Mw Pe) Lh(Jo Lw Md Me Nh Of Pb) Nn(Hu Ii Jn Md Ne Pe) Jg(Hu Md My Ns Of Pe) Ok(Io Jo Jt Me Mh) Fp(Ly Md Mw Nt) Pe(Md Me Pa Pb) Wm(Jp Mv) BaUu EdFw NtLy MnNh TnOz liPf JlUs} Qe{Ma(Fp Hv Hw Im Io Jm Jn Jt Lh Lu Lw Lx Me Mi Mm Mr Ms Mt Na Nn Om Pc Pe Pf) Lx(Hq Il Im Jm Jn Lu Lw Ly Me Mh Ms My Mz Ns Oe Pa Pb Pc) Lw(Fp Im Io Jn Lh Lu Me Mr Ms Mt Mz Nn Ns Om Pf) Lu(Fp Im Jn Me Mm Mr Mz Nn Oh Om Pc Pf) Me(Im Lh Mm Mr Mt Mz Oh Ok Om Pc Pf) Mz(Im Mm Mr Ms Nc Nn Pb Pc Pf Qc) Om(Fp Il Jm Jo Ly Mr Ns Oe Of Pa) Ms(Jg Lh Mr Nb Oh Pc Pe Pf) Ok(Fp li Io Jt Ly Mr Oz Pa) Nn(Ii Jm Jn Mr Ns Oe Pb) Lh(Ii Io Jo Oe Pb Pc Pf) Pc(Fp Jn Mr Ns Pe Pf) Pf(Jm Nk Oz Pa Pb) Kr{eF Ji Ou Tn) Us(Jl Jy Tn) My(Jg Jl) MmMr NkWb TnKg JnJs JyUu KjeF PbPe} Om{Hu(Im Io Jn Lh Lx Ly Ma Me Mr Ms Mv Mw Ne Nh Ns Nt Oh Ok Pe Qb Qd) Mg(Fp Im Jn Lh Lu Lx Ma Me Mh Mr Ms Nn Ns Nt Oh Ok Pc Pe Pf Qd) Fp(Ik Im Jn Jo Jp Lu Lw Ma Me Mm My Nn Ns Of Oh Pb Pc Qd) Ms(Lh Lw Lx Me Mh Mi Mn Mw Na Nb Ns Ok Oz Pa Pb Pe Qb Qd) Mc(Im Jn Jo Lj Lu Ma Mm Mr My Of Oh Pb Pf Qd) Pf(Im Jo Lu Ly My Ns Of Oz Pa Pb) My(Lh Lx Mr Mt Nb Nn Oh Pe) Lu(Im Jn Lj Ns Oh Pb Qd) Mr(Im Ly Of Pb Pc) Of(Lh Lx Ok Pe) Oh(li Ns Oe Pb) Nn(Ns Oe) Ma(Jn Qd) Pb(Lh Pe) AjeF LxHq ImOe JlUs PaPe} Im{Lu(Fp Hu Hv Hw Io Ir Jn Jo Jp Jt Lx Ma Mi Mj Mn Mr Mt Na Nf Nn Ns Nt Oe Oh Pa Pc) Nn(Hu Hw Io Jn Lh Lw Lx Ma Mr My Mz Nh Ns Oe Pe Pf) Me(Jp Lh Lw Lx Ma Mm Mn Mr Mt Mz Oh Ok Pa Pc Pe) Mz(Fp Io Lh Lw Lx Ma Mm Mr Ms Ok Pa Pc Pe Pf) Lh(Fp li Io Jn Jo Lw Ma Mm Ms Mt Of Pc Pf) Pe(Io Jn Lw Ma Mm Ms Mt Oe Pb Pc Pf) Lx(Hq Jn Lw Mh Ms Ok Pb Pc) Ok(Io Ma Mr Ms Pc) Lw(Fp Mr Mt Pf) Jn(Ma Pc Pf) Ms(Nb Oh) Sh(Bg Jy) Pc(Mr Pf) eF(Aj Hc) AoJy PbPf} Ok{Ms(Fp Io Jn Lh Lw Lx Me Mi Mr Mt Mv Mw Mz Nb Nf Nq Oz Pa Pb Pe Pf Qb) Pc(Hu Io Jn Jp Lx Ma Mg Mz Nf Nh Ns Oh Pe Pf Qd) Ma(Fp Jn Lw Lx Me Mg Mr Mt Mz Oh Pe Qd) Fp(Jo Jp Lw Me Mm Mn Mv Oh Oz Pb) Lx(Hq Hu Jn Ly Me Mg Mh My Oz Pb) Oh(Io Me Mr Ns Oe Oz Pa Pb) Pf(Hu Io Jn Ly Nn Ns Oz Pa) Mr(Lw Ly Me Mn Oz Pb) Pe(Jo Ly Oz Pa Pb) Nn(Io Jn Nm Of) Ly(Io Nh Wm) Me(Jo Mm Mt) Mv(Hu Mg) Jn(Io Jt) Jo(Lh Nf) JlUs LhPb} Nn{Jn(Fp Hu li Io Js Lh Lu Lw Ma Mm Mr Ns Oe Pa Pe) Fp(Hu Ir Jm Jp Jt Lh Ly Ma Mm Nk Pc Pe) Ns(Jt Lh Lu Lw Lx Ms Mz Na Ne Nh Pe Pf) Ms(Hw Ij Ir Lu Mn Mt Mz Nh Nt Qd) Lh(Hu Jo Lw Ma Mg My Nh Oe Of) Pe(Hu li Jo Lu Ma Nh Oe Pa) Mr(Hu Lw Mm My Oe Oz) Oe(Jt Nh Nt Pa Qd) Lx(Hq Hu My Pb) Aj(eF Me Tn) Mz(Lw Ma Pb) Lu(Hu Lw) My(Jg Nb) Nc(Ne Nh) li(Jt Un) Oz(Rv Vz) MedM HceF JiKr JoJt} Jl{Us(AD aM As aW bA Bn bV Cp Cq cT Cu CW Dc Di dM Dp eF Hc Hu Hv Hw Id Ij Ir Iu Jd Jn Jo Jt Jv Jy Kd Ke Kn Kp Kr Lw Ly Mc Mr Na Nc Nf Nj Nl Nm Oe Ou Ow Pb Pi Pk Ql Qv Qz Ra Rb Ri Rj Sr Uc Ud Up Vp Tl Xa) Ur(Dp Ly Me Nf Oz Ri) aW(Mc Nc Nk Oe) Aj(Me Ri Tn) Ly(Dp Qv Ri) Uu(Ba Ef Jy) bR(dA dl) CxYl DpQv MlNy IiUn JiKr} Jy{Ed(aD aW bA bR bS bV cA cP cT dM eF Ri Ur Tj) bA(Aj Ao aW Kg Kj Ly Of Uk Us Uu Tj) Hq(aW bV cN cT dA dl dM) Co(aW cN cT dA dl Tn) Aj(Sr Tn Un Uv) cT(Oz Pg Uk Uu) Us(Ji Ps Un) bS(cN Lj Oa) Eq(Ez Ih) Ly(aW dM) Sh(Ih Jn) Uu(Nr Un) Pg(aW dA) bV(cA Oz) BbbR DpWc TnbL VzRf JiKr SrKj cNdH} Me{Oh(Fp Jg Jn Jp Lh Lw Lx Ma Mm Mn Mr Ms Pc Pe Pf) Mm(Fp Jn Jp Lh Lu Lx Ma Mr Mt Mz Pe) Pf(Jg Jn Jp Lh Lu Lw Mn Ns Oz Pb) Lx(Hq Jn Jp Ly Ma Of Pb Pc Pg) Ma(Fp Jn Lh Lw Pc Pe) eF(Aj Ji Sr Ur) Jn(Lh Lu Pc) Jp(Fp Lw Wm) Ji(aW gL) Lh(Lw Pb) Pc(Mr Pe) dM(Nr Oz)} Sr{eF(bO bX Ch Co Dg Jo Kg Kl Kr Kx Kz Ly Mg Ms Nc Nl Oz Pa Rb Rf Ue Ug Um Us) Aj(Dp Ef Jd Ma Qy Tn) Ri(Ed Jv Kg Kj Ko) Uu(Ba Bg eC Jd Qy) Dp(Lu Qv Ur) Tn(Jv Kg Oz) Ch(gL Jv) Ed(Fw gL) Kj(Ba Bg) QvJv} Lu{Un(Aj bO Dp Hc Ii Kj Ly Ms Oz Pb Pc Rf Ri Ur Us Uu) Ji(Af Aj aW bJ bN bO bR Cx Kr Rf Ri Us) Fp(Jp Lw Ma Mm Mn Oh Pf) Jn(Lw Ma Oh Pc Pf) Pe(Lw Mm Pb Pc) Dp(Fy Rf) Lw(Oh Pf) AjFy LhPb RfOu} Lh{Pb(Fp Jn Lw Ma Mm Mr Ms Nh Oh Pc Pe) Fp(Jo Jp Lw Ly Ma Mm Ms Oh Pc) Pf(Jo Lw Ms Oz Pa Pc) Jn(Lw Ma Mm Ms Pc) Lw(Jo Ma Ms) Oh(li Ms Oe) Ma(Jo Mm) Pc(Mr Ms) MmJo} Oz{Tn(Ji Jv Kj Lw Rf Ri Rv Sh St Un Us Uu Vq) Ps(bS cA Nj Nk Oe Qm Qn) Fy(aW bH dM) Un(bA gL Ms) Jd(Sf Sh) Rf(dM Ou) BaUu MtVz JvVi} Fp{Lw(Jn Lx Ly Ma Mr Mt Mv Mz Oh Pe Pf) Jp(Io Jn Ma Mm Oh Pc Pe) Ma(Jn Mm Mz Pc Pe) Mm(Jn Mz Pe) LxLy MsJg PcPe} Ji{Kr(Bg bZ Ed Jp Ma Nj Ou Qy Ri) gL(Af Ao Hc Nf) Ms(Ef Qy) Kg(Dp Tn) Ri(Ed Ly) eF(Aj Us) BaUu HcQy} Aj{Tn(Ba bJ Dp Ef Ez Jd Nj Nk Qt) eF(Fa Ij Jh Kx Mr Mw Pe Un Ut) MaUn MsJd TrPc} Jn{Pc(Lx Ma Mr Ms Pe Pf) Mm(Io Ma Mr Pf) Lw(Ma Ms Pf) Lx(Js Mh Ms) Pf(Lj Pa) WmLy MaPe MsJg} bA{bM(aW Bg bO bR bZ Ch Dc) aD(bE bF bJ bW bZ) bR(bW bZ dl) CxEm DcbJ HcQy aCbE aWbW} Pe{Pc(Ma Ms Nk Pa Pb) Pb(Ma Mm Pf) Ms(Jg Oh) MmPa MyJg KgeF} Un{eC(Ii Us Uu) Ba(Kj Uu) Ma(Jv Kg) EdFw MsKj TrPc} Ms{Oh(Jg Jt Lw Nb) EdJd MrJg NbPf} eF{Ny(Hc Jv Kj) MwIz HcSt JhUu} Lx{NsMh LyNh MaHq MyJg JtPb} Mw{gL(Ao Iz) CoTn MyeC} Ps{Nk(bN Oe) NlOe NxUs} Vi{Us(Dp Je Qy) QyKc} dl{EdJd TrPc PfbR aDcT} Mr{EzRv MmMz MyJg} Nj{DpXa FyVz YlOw} Kj{eC(Ad Id Pk)} Ba{BbDc OrUu} Ed{LwRi NkTn} bV{fP(Fa Ur)} cT{CxEm DcbJ} BbFyJd DpNbWc NsLwPf LyKkbW MaMmMz TrPccN JhUugL OrVwbN

Constrained panels with 2 analytes, where 1.0E-7 >= 'model p-value' > 0. Contains 613 panels of 87,101 total panels evaluated. : Mu(aA Dr Et Fp Fr Hu Hv Hw Ih Im In Is Ji Jj Jl Jn Jq Jr Jt Lh Lj Lv Lw Lx Ly Ma Me Mh Mi Mm Mn Mq Mr Ms Mt My Mz Ng Nh Ni No Ns Nt Nw Oe Og Oh Oi Ok Om On Oy Pb Pe Pf Po Qa Qd Qe) Fr(aA dN Dr Et Fp Hu Hv Hw Im Ir Is Ji Jj Jl Jn Jq Jr Jt Lh Lj Lv Lw Mc Mg Mm Mq Mr Ms Mx My Mz Na Ne Ng Nh Ni No Ns Nt Nw Oe Og Oh Oi Ok On Oy Oz Pb Pe Pf Po Qa Qb Qd Qc) aA(bM dN eF Et Fp Im Io Is Jg Ji Jl Jn Jq Jr Lh Lv Lw Lx Ma Me Mf Mh Mm Mn Mq Mr Mt Mw Na Nf Nh Ni Nn No Ns Nt Nw Ny Og Oh Oi Ok Om On Pc Pd Pe Pf Pg Po Qa Qd Qe Wm) On(Et Fp Hu Ii Im In Io Is Ji Jj Jk Jl Jn Jq Jr Lj Lu Lv Lw Ma Mc Mg Mh Mk Mq Mr Ms Mv Mw My Mz Ng Nh Ni No Ns Nw Oe Of Og Oh Oi Ok Oy Pb Pe Pf Po Qa Qd Qe) Jl(Et Fp Ii Im In Io Is Ji Jj Jn Jq Jr Lu Lv Lw Ma Me Mq Ms Mz Nc Nf Ng Ni Nk Nl Nn No Ns Nw Oe Og Oh Oi Ok Om Oy Oz Pb Pc Pf Po Qa Us) Nw(Et Fp Hv Hw Im In Ir Is Jj Jn Jo Jq Jr Jt Lh Lu Lv Lw Ly Ma Me Mq Mr Ms My Na Ng Ni Nn No Ns Og Oh Oi Ok Oy Pb Pc Pe Pf Po Qa Qc) No(dN Et Im In Io Is Ji Jj Jn Jq Jr Lh Lj Lu Lv Lw Ma Me Mm Mq Ms Nc Nf Ng Ni Nk Nn Ns Oe Og Oi Ok Om Oy Pc Po Qa Qc) Lv(Et Fp Im Is Ji Jj Jn Jp Jq Jr Lh Lu Lw Lx Mm Mq Mr Mt Mw Mz Ni Nn Nt Oh Ok Om Pe Pf Po Qa Qd Qe) Ni(dN Dr Et Im Is Ji Jn Jp Jq Jr Lh Lx Mn Mq Nn Oh Ok Om Pe Pf Po Ps Qa Qd Qe Yl Xa Th) Ji(Fp Im In Io Jj Jr Lu Ly Ma Me Mq Mr Ms Mv Ng Nn Og Oh Oi Pb Pc Pf Po Qa Qe) Is(Et Fp In Io Jj Jq Jr Lh Lu Lw Ma Mc Mm Mq Mr Ms Ng Nn Og Oi Ok Om Pf Po) Qa(Et In Jj Jq Jr Lh Lu Lw Lx Ma Me Mq Ng Nn Og Oi Ok Om Pc Pf Po) Jj(Et Fp Im Jk Jn Jq Jr Lh Mq Nn Nt Oh Ok Om Pe Pf Pg Po Qe) Et(Fp Jn Jq Jr Lu Lx Me Mq Mr Mz Ng Nn Oh Oi Pf Po Qe) Ok(Fp In Jq Jr Lu Me Mq Ms Ng Nn Og Oh Oi Pc Pf Po Qc) Jr(Im In Jq Lh Lw Ma Mm Mq Nn Om Pc Pf Po Qe) Kq(Aj Ao Bb Dr Jt Kg Kj My Ng Of Oy Pg Us Uu) Po(In Jq Lw Me Mq Ms Ng Og Oi Oy Pb) Nn(Fp Jn Jq Me Mq Mr Ms Ng Og Oi) Dr(BA bZ cS cT Jy Mv Og Oz) Mq(Im Jn Jq Mz Oh Pf Qe) Om(Fp Ms Ng Og Qe) Jq(Fp Mr Pf Qe) dN(BA cT Me) Im(Lh Lu) Qe(Og Oi) MePf NgJg LhOg Constrained panels with 2 analytes, where 1.0E-6 >= 'model p-value' > 1.0E-7. Contains 547 panels of 87,101 total panels evaluated. : Ni(aJ aW bA bV cN dM Du Ed Fd Fp Hp Jg Jj Kq Li Lw Ma Mm Mt Mv Mw Mz Nv Ny Pa Pc Pg Qb Rv Sr Tn Vi Vz Wb Wf Zq Tm) Dr(aJ Ao bF Bg bQ Co Cx dF Ef fR Gp Im In Jd Je Jl Ky Lh Lu Lv Ma Mr Mt Mw Nd Nn Nq Nu On Or Ou Pb Qy Ri) Kq(aA aW bH Co Cq cZ Dc Dk dN Dp Ed Hc Ib Ii In Iz Jg Jo Jv Ki Kl Kr Ly Md Ms Nb Nv Nx Og Oi Oz Pa Pb Ur) aA(aC aM aW BA bF Bg bH bR bW bZ cA Ch cT Dc dI Dk dM

Figure 7 Continued

Dp Ed Ef gP Jy Ki Ou Ow Pk Rf Ri Sr Tn Un) dN(aJ An Bg bH bR cA Dc dI dM eC Im In Is Jd Jl Jn Jr Jy Lu Lv Ly Mq Mr Ms Mu Nf Oe Og Oi Rf Sr) Nn(Hu Hv Hw Im In Ir Jt Lh Lu Lw Lx Ma Mi Mz Na Ne Nh Ns Nt Oe Om On Oy Pe Pf Po Qd Qe) Et(Hv Hw Im In Io Lh Lw Ma Mh Mi Ms Mt Mv Mw Na Nb Ne Nf Nh Nt Og Ok Om Pc Pe Qb Qd) Mq(Fp In Jg Jp Jt Lh Lu Lw Lx Ma Me Mi Mm Mn Mr Mt Mw Ng Ns Nt Og Oi Om Pc Pe Qd) Lv(Hu Io Jg Jt Li Lj Ma Me Mi Mn Mp Mv Mx Na Nb Ne Nf Nh Nv Ny Og Oi Pa Pc) Jq(Im In Jg Jn Jp Lh Lu Lx Ma Mm Ms Mt Mv Mw Nh Nt Og Oh Pa Pc Pe Qd Wm) Jr(Fp Jg Jp Lu Lx Me Mi Mn Mr Ms Mt Mv Mw Mz Nc Ng Nh Ns Nt Og Oh Oi Pe) Om(Hu Im In Jn Lj Lu Ma Me Mg Mr My Mz Ns Of Oh Oi Ok Oy Pe Pf Po Qd) Qe(Fp Im In Jn Lh Lu Lw Lx Ma Me Mm Mr Ms Mt Mz Ng Pc Pe Pf Po) Pe(Fp Im In Is Lu Lw Ma Me Mm Og Oi Ok Oy Pa Pb Pc Po Qa) Po(Hr Hw Im Jn Jt Lh Lu Ma Mm Mz Nh Nk Ns Oe Oz Pc) Jj(Ij Jg Jt Lx Ma Me Mr Mt Mv Mw Mz Nh Nv Ny Qb Qd) Ok(Im Io Jn Jp Lh Lx Ly Ma Mh Mn Mr Mt Mv Mz Nf Qd) bA(aD aJ aM aW bJ bM bP bR bW Ch Dc dM Fr Jy) Qa(Io Is Jg Mm Mn Mr Ms Mt Mz Nc Nf Nk Oe) Jn(Im In Lh Lu Lw Lx Ma Me Mm Og Oi Pc Pf) Lh(Fp In Lw Ma Mm Ng Oh Oi Oy Pb Pc Pf) Pf(Fp Im In Jt Lu Lw Mz Ng Og Oi Oy) Is(Jm Lx Mz Ns Nt Oe Oh Pc) Fr(cT dM Ed Jo Ma Nl) Im(Lx Me Mr Mt Mz Og) Ng(Jd Jk Lx Ma Mv) Fp(Jp Lw Ma Oi) Mu(Jp Mg Pa Qb) Sr(eF gL Oi Ri) Oh(Lu Me Ms Oi) Lx(Me Og Oy) Ji(gL Kr Ri) No(eF Ri) Oy(Tn Ut) cT(aJ dM) NtOi LuUn MaMe JhOn

Constrained panels with 2 analytes, where 1.0E-5 >= 'model p-value' > 1.0E-6. Contains 810 panels of 87,101 total panels evaluated. : Ni(aD Aj aM aP Ax Ba bM Bo bQ bR bW bZ CS cT Cv dA Dc dF dG dI Dk Dp eF Fa Fy GL Hc Ih Ij Jd Jk Js Jt Jy Kx Ky Kz Lj Ly Me Mi Mj Mp Mr Mx Ne Nh Nk Nl Nt Oa Og Or Ou Oz Pd Qh Ql Qv Qy Rf Ri St Tr Uf Un Ur Vp) Dr(aA An aP Aw aX bC bE bG bH bW cG cP dA dG dI dM dN Ed Ex Ez Fb Fn Gl Gn Is Ki Mi Mj Mz Nk Oy Pf Qa Ql Qw Rb Tn To Uk Ut Ye Xa Th) No(aD Aj Ap aW bA Bb bH bO bR bS bV cA cN Co cP cT Cv cW dI dM Dp Ed Hc Ju Jv Jy Kg Ki Kj Kl Kr Or Ou Qv To Ud Ur Us Uu Tj) dN(Dp Ed Ef Fy Gl Hc Hu Ji Jj Jq Kg Ki Kr Kx Ky Kz Ma Nc Nn Nr Nw Or Ou Oy Oz Pc Po Qa Qd Qe Ql Qt Qv Qw Qy Rh Ri Tn Un Ur) Im(Fp Hv Hw Ij In Io Ir Jg Jo Jp Jt Jy Lw Ma Mh Mi Mj Ml Mm Mn Ms Mv Mx Na Nb Ne Nf Ng Nh Nt Oe Oh Oi Pa Pc Pd Pg Qd) Kq(Ad aE Af Ap bA Bn bV cI Ct dI Dl dM eC Jd Jj Ko Lu Me Mg Mw Nc Ny Pc Qu Qv Ri Rv Sh Ug Vo Vp Tj) Fp(Hw Hx In Ir Jg Jn Jt Lu Lx Ly Me Mi Mm Mn Mr Mt Mv Mw Mx Mz Na Nb Nt Nv Ny Og Oh Pa Pc Qd) Sr(Aj bA Dp Ed Fr In Ji Jj Jl Jv Jy Kg Ki Kj Lu Lv Ly Ms Mu Nc Ng Oe Og Oy Oz Qv Ug Ur Uu) Oh(Hv Hw Ij In Jg Jn Jo Jp Jt Lw Lx Ma Mi Mm Mn Mr Mt Mv Mz Nb Ng Nh Nt Og Pc Pe Pf Qd Qe) bA(bF bZ Dk Dp Ed Jd Ji Jl Jq Jr Jv Me Mu Oi Oy Oz Qa Qe Ql Qv Rf Ri Un Ur Us) Jj(Dp Ef Hu Hw Ii Ik Jm Jo Jp Js Jy Li Lw Mi Mj Mm Mn Mp Nb Nf Nr Nx Pd Wm) Jq(cT Ed Li Lj Lw Me Mh Mi Mj Mn Mx Mz Nb Ne Ng Ns Ny Oi Om Oz Pg Qb) Pf(Hv Hw Ij Ir Jg Jo Jp Mm Mn Mr Mt Na Nb Nh Ns Nt Oz Pa Pb Pc Pe Qd) Lx(Hq Hv Hw In Jp Jt Lw Ly Ma Mh Mm Mr Mz Nh Nt Of Oi Om Pb Pc Qd) Lh(Jo Jp Lu Ly Me Mi Mn Mr Ms Mt Mv Mw Mz Ne Nh Oe Of Om Pe Qb Qd) Fr(Ad AJ An As aW bM Cu Cw Dc dI Hc Jv Ki Kz Pk Un Us Uu) Jy(AJ aW bR bS bV cT dM Ed Ji Jr Ly Ng Oy Oz Rf Sh Un Ur) Mz(In Jg Jn Jp Lw Ma Me Mm Mr Mt Mv Nt Og Oi Pc Pe Qd) Qe(Hv Hw Io Jg Jm Jo Jp Jt Mi Mn Mv Na Nf Nh Nt Oe Oy) cT(aD aM aP aW aY bM bP bW cS Cv Dc dG dI dL Ji Jl Un) dM(Ba Cp cS Dc dF dI Ed Gl Is Ji Jr Lv Me Mr Nn Nr Oi) Mq(eF gL Hw Ir Js Li Lj Ly Ms Mv Mx Na Nh Ny Pg Qb) Jn(Io Jg Jp Mi Mn Mr Ms Mv Mw Nc Nf Ng Nt Pa Pe Qd) Ji(aW dI Dp Ed eF Hc Jv Kg Qv Qy Rf Ur Us) Jl(Aj aW bR Dp gL Hc Kj Kr Ky Qv Ri Ur Uu) Om(Jp Lw Ly Mh Mi Mm Mt Mx Na Ne Nh Oe Pb) Qd(Jg Lu Lw Ma Mc Mm Mr Ng Og Oi Pc Pe) Un(eC Ed In Kg Ly Ma Ms Og Oi Oy Oz Us) Me(Cv Jg Jp Lw Mm Mn Mr Mt Nt Nv) Pe(Jg Jp Mn Ms Mt Ng Nk Ns Nt Oz) Mr(aW Jg Jp Jt Lw Ma Mm Mn Pc) aA(Fy Jd Kx Or Ql Qv Rh Uf Us) Nt(In Jp Lu Lw Mt Ng Og) Dc(aJ Ba bW bZ dI eC) Nn(Jo Jp Mh Mm My Pb) Is(aW bV Hc Kr Qv Us) Oi(aJ bV Jd Jg Ma Mt) Ed(eF Jd Lw Mu On) Og(Jg Jt Nb Nv Xa) Oz(Fy Ps Tn Vi Xa) Ba(AJ Ng Uu) Lw(Jp Ma Mt Mv) Fy(bH Kg Lu) Mu(Ao Bb Co) Qa(eF Kr Us) Jr(Ri Ur Us) Rf(eF Lu Ou) On(Bb Jv Sh) Ma(Jt Nh) Ng(Nv Tn) AjTn WmLv LuKe MsJd MtSh NbOy NkPs TrPc SteF Constrained panels with 2 analytes, where 1.0E-4 >= 'model p-value' > 1.0E-5. Contains 1,681 panels of 87,101 total panels evaluated. : Jy(aD aM Ao Ax Bb bF cA Co cP Cs Cv Dc Dp eF Eq Et Fa Fp Fy Gd Hc Id In Is Jd Jl Jn Jq Jv Ke Ki Kj Kr Kx Ky Kz Lj Lu Lv Lw Me Mk Mq Ms My Nc Nd Nf Nn Nr Oa Og Oh Oi Or Ou Ow Pc Pf Pi Pk Po Ps Qa Qd Qe Ql Qv Rh Ri Sf Ud Us Uu Uv Vt Ye Xa Tj) dM(aC Ad aJ An Ar Aw Ax bF Bg bQ bV bW bZ cE Ch Cq Cs Cu Cv Cw Db dG Di Dk Ef Fy Hu Jd Jj Jl Jn Jq Ky Lh Lw Ly Ma Mn Mq Mu Nf Nw Og Om On Or Ou Ow Oz Pc Pe Pf Pk Po Qa Qd Qe Ql Qt Rf Ri Sr Un) Un(AJ aW Ba Bg bH Bo bR bZ cN Cv dI Dp eF Fn gL Hc Ii Im Is Jd Jj Jl Jo Jp Jq Jr Jt Jv Kj Kr Kx Ky Lv Me Mq Mr Mu Nc Nf Ng Nn Nr Oe Ou Ow Pa Pc Pf Qe Ql Qv Qy Rf Ri Sr Ug Ur Uu) cT(An Bg bH bJ bQ bV bZ cN cW dA dF Dp Ed Hu Is Jd Jj Jn Jr Jv Ki Lu Lv Lw Me Mq Mr Ms Mu Nn Nw Og Oi Oy Oz Pc Pe Pf Po Qa Qd Qe Ql Qv Qy Rf Ri Sr St Uf Ur Us Uu) Mr(aJ bA bR bV cN Cv Dc Ed eF gL Hv Hw Ij In Ir Jk Jo Ky Li Lu Ly Mi Mp Ms Mt Mv Mw Mx Na Nb Ne Nf Ng Nh Nt Nv Ny Og Oi Pa Pg Qb Qv Ri Ru Tn Ud Vi Yl Xa) Jp(Dp Ed Hc Hv Hw Ij In Io Ir Jo Jt Jv Kr Kx Lu Ma Mf Mh Mi Ml Mm Ms Mt Mv Mw Mx Na Nb Ne Nf Ng Nh Ns Nu Ny Og Oi Pa Pc Pg Qb Qd Rf Sr Ud Us) Ed(Ba bQ bV bZ cN Cv dA Dc dI Ef Et Ez Fy gL Hu Is Jj Jl Jn Jr Ke Lu Lv Ma Mq Mv Nn Nw Oe Og Oi Om Ou Oz Pf Po Qa Ql Qy Rf Ri Tn Uf Ur) Jq(AJ aW Ba Bb Bg bH bJ Bo bV bW bZ cN Cx dI Dp eC eF Fa Fn Hc Jd Jv Kg Ki Kj Kr Ky Kz Ou Ow Ql Qn Qv Qy Qz Rf Rh Ri Sr Uf Ug Ur Us) Me(aJ aP aW Ax Ba bQ bV bW bZ cN Cs Dc dF dG Dk eF gL In Jd Jk Jt Ke Kk Li Lu Mi Mp Mv Mw Mx Nb Nh Ny Ou Pa Pc Pg Qb Ql Rf Sr Tn Ur) Jj(bA Dc eF Ez Fa Fy gL Hv Ih Il In Ir Iv Jd Jh Kz Lj Lu Mf Mh Ml Mx Na Ne Ng Nj Nl Nm Nu Oa Or Ou Oz Pa Pc Pz Qc Ql Qy Rf Ri Tn Ud) Fy(Aj aW Bb bW Co Dp Fr Hc Ii In Jd Ji Jo Kd Ki Kj Ly Mq Mu Nc Nf Nj Nl Og Oi Or Ou Oy Pa Pc Ql Qv Qz Ri Sr To Uf Ur Us Vz) Ma(Aj bA Dc Hv Hw Ih Ij In Io Ir Jg Jo Ke Lj Lu Mh Mi Mm Ms Mt Mv Mw Mx Na Nb Ne Nf Nl Ns Nt Nu Nv Ny Og Pa Pc Pg Qb Ri Sr) aJ(aC Ad An As AW bF Bg Bn bQ bR bS bZ cE Ch CP Cq Cu Cv Cw Dd dF dI Dk Ef Gl Is Ji Jr Lv Mq Mu On Ou Ri Sr Tn) Fr(aC Ba Bn bV bW Cp Cq CS Dp Id Iz Kd Ke Kg Kj Kn Kr Kx Ky Oa Or Ow Pi Ql Qv Qz Ra Rf Ri Rj Tv Ud Up Ur Uv Vt) bA(Hc Hu Io Is Jn Ki Kx Ky Kz Lu Lv Lw Lx Ly Ml Mq Ms Nc Nf Ng Nn Nr Nw Oe Og On Or Ou Pc Pf Pk Po Qy St Uf Uu) Jd(Aj Ao bV Co Cv dI Hc In Is Ji Jl Jr Jv Kj Ky Lu Lv Lw Ly Og On Or Ou Oy Oz Pc Qa Qv Rf Ri Sr Ud Us Uu Wh) Sr(aM aW Bg bH BO bR bV bZ cS Cv dI eC Gp Hc Is Jr Ju Kr Kx Ky Lw Na Nf Nl Nn Ou Pc Ql Rf Tn Ud Uk Us) Oi(aP Ba Cs Dc dF dG Dk EF Ez Fa Id Ij Jt Ke Ky Li Mv Mw Ni Nv Ny Or Ou Ow Pg Qb Ql Qy Rf St Tn Uf Xa) Qa(Aj aW Ba bH Bo bR bV bW bZ Co Cv dI Dp eC Fn gL Hc Jv Kg Ki Kj Ky Ou Ql Qv Rf Ri Sf Sh Ur Vz Ye) Lw(Dp gL Hu In Jg Jt Jv Li Lj Lu Mh Mi Mj Mn Ms Mw Mx Nb Ne Nh Nv Ny Og Pa Pg Qb Qv Qz Rf Ri Tn) Jr(Aj aW Ba bH bR bV bW bZ cN Cv dA dI Dp eC eF Hc Jv Kg Ki Kj Kr Kx Ky Kz Or Ou Ql Qv Qy Rf Uf) Og(Ba bV Dc Dk Ez Id Ij Jk Jo Ke Ki Mi Mm Mt Mv Mw Nh Ny Or Ou Pa Pc Pg Ps Qb Ql Rf Vi Zw Wm) Lu(Ad bV Cv Dc Dp Fa Id Jg Jt Ky Lx Mi Mm Mn Mt Mw Mz Ni Ny Or Ou Ow Qb Ql St Uf Vt) Lv(aD Aj aP aW aZ bH bM bV bW Cs CV cX dI Dp Kr Ky Ql Qn Qv Qy Rf Ri Tz Uf Ur Us) Ba(AD aM An aP As aW Ax bM Bn bV bW bZ cN Cp Cq Cs Cu Cv Cw dF dG dI dL Kl Oy) Ke(Aj aW bH bZ dI Dp eC Fn gL Hc In Jl Jv Kg Kj Kr Ly Ms Nf Ni Nn Oy Oz Ri Ur Us) Tn(Co Cv Dp Hc Im Jv Kg Kj Kz Ly Mq Nc Nf Nk Nw Pc Qd Qe Ql Rf Ri St Ur Us Uu) Dc(aP aW bF bH bM Bo bQ bV cS dF dG Dp eF GL Jl Mq Mu Nn Ou Oy Oz Pf Ur) Mt(eF Hv Hw In Jg Jo Jt Lx Mi Mm Ms Mw Na Nb Nf Ng Pa Pc Qd Rv Sf Si Vz Yl) Is(aD Aj Al bH bR bW Co Cv dA dI Dp eF Jv Kg Ki Kj Ky Ou Ql Ri Tz Ud Ur Uu) Mu(aD Aj aW aY bR bV Cs Cv Dk Ki Kj Ky Or Ou Qv Rf Rv Us Uu Ye Tm Xa Th) On(Aj Ao Ap aW bV Co Cs Eq Hc Kg Ki Kj Kr Oa Qy Rf Ri Rv Sf Us Uu Vz Th) Nt(Hv Hw Ir Jt Ly Mh Mi Mm Mn Mp Ms Mv Mw Mx Na Nf Ns Ny Oe Pc Qb Qd) Ni(Ez Hf Hu In Jv Kr Lz Mh Na Nb Nc Nj Nr Nx Ow Pk Qt Qw Qz Ua Uh Us) Jl(aD aE

Figure 7 Continued bO bV Cv cW Db dI Hf Jv Kg Kl Ks Kx Kz Ow Pk Ud Vz Yl Ye) Jt(In Jg Mi Mm Mn Ms Mv Mw Mz Nc Ng Nh Nv Ny Pc Pg Qb Qd Vi)
Ri(Cv el· Fa Im Jn Mq Nn Nr Or Pe Pf Po Qd Qe Ql Rf Vi Xa) Ou(aW Cv Im Jn Jv Ki Kr Ly Mq Nc Nw Oy Oz Pc Qe Qv Ur Th) Lx(Hu Ir Jg
Jo Mn Ms Mv Mw Mx My Na Ne Ns Ny Oz Pg Qb) Qd(eF Hv Hw Ij In Jo Mi Mn Ms Mv Mw Na Nb Nf Nh Qv) Nn(Aj Dp eF Hc Kg Ki Kj Kr
Ky Or Qv Rf Sh Ur Us) Mm(Hu Hv Hw Ij Ir Jo Mh Mi Mv Na Nb Nf Nh Pg Qb) Vi(aX bN Cx cZ dA Dp Ez Kc Nc Nf Nk Oy Pa Pb Ql) Oz(bV
Hl Hp Mz Or Rf Uw Vb Vw Wb Wd Wh Yl Zx Ye) Ji(Bb Bg bH Bo bV bZ cN Db eC Fn Hf Ki Ql Ti) Mi(In Jg Mn Mv Mw Mz Ng Nh Nv Ny
Pc Qb Wm) eF(Fa Hc Im Kx Ky Kz Nw Ny Oa Pe Po Qe Ql) Cv(bZ dF Fp Jn Mq Nr Pe Pf Po Qe Qn) Xa(Af dA dN Nj Nk Nu Or Oy Ql Rb Sh)
dI(Ad bR cA CP Cq Cu Cw dF Jn Mq) Ly(Fa Ki Kk Ky Or Ql Rb Rf Uf Wm) Mz(Mn Mp Mw Ne Nh Nv Ny Pa Pg Qb) Qv(Dp Im Jn Mq Pf Po
Qe Ql Rf Ud) bV(cA Ef fP Io Iv Mq Nc Nr Ql Rf) Jg(Hw Mh Ms Mx My Na Nf Ns Qb) Fp(Hv Ij Jk Jo Mp Nf Nh Pg) Ng(Dk Ef Ij Mw Nb Ny
Pg Ut) aW(aP dF fR Gl Mq Pe Po Qe) bZ(Ad As bM bW Cp Cq Cu Cw) Oh(Ir Mw Na Nc Ns Ny Oe) dF(aD bM bW cA cP cS Oy) gL(bW Kz
Nw Ny Or Pe Po) Mq(Aj Dp Jv Ky Rf St) Im(Jv Ki Sh Tv Vz Yl) Qe(Kg Kj Kr Ky Rf Us) Jn(Hc Jv Kr Rf Ur Us) Kq(Eq Ex Fi Sf Vs Wc) eC(Id
Kd Kn No Pi Pk) Po(Aj Co Kg Ur Us) Ms(Dk Mw Nb Nv Or) Nh(Mn Mv Mw Ny Pc) Ye(Je Mw Ql Qy) Ut(Ao Bb My Of) Aj(Ef Hu Om)
In(Nv Pg Qb) Ky(Nf Or Pf) Yl(bN Nj Ra) Pc(Mx Na Tt) aP(An bR Ef) fR(cP CX) Dk(Oy Uu) Mn(Na Ne) Kg(Lh Ok) Ps(Nj Us) Rf(Or Ud)
Pe(Co Qb) AdKj CsEf WmOk NoSh MyNb IrLh QlOe OrVw PfbR bMbQ Constrained panels with 2 analytes, where 1.0E-3 >= 'model p-value' > 1.0E-4. Contains 4,016 panels of 87,101 total panels evaluated. : Rf(AD
AJ aM aP As aW aY Ba bC Bg bH Bn bQ bR bW bZ cE cG cN Cp Cq cS Cu Cv CW dA Dc dF dG dI Dk dL Dp Ef Ex Fa GL Hu Hv Hw Id Ij
Im In Ir Is Jt Jv Kd Ke Ki Kj Kk Kn Kp Kr Kx Ky Kz Lh Ma Mi Ml Mr Ms Mv Mw Na Nc Nf Ng Nr Oe Ok Om Ow Oy Pb Pc Pe Pf Pi Pk Po
Qd Ql Qy Ra Rb Rj To Tv Uc Uf Ul Up Ur Us Ut Uu Vi Vp Vt Vz Yl Xa) Ri(Ad aM An aP As aW Ax Ba bQ bV bW bZ cN Cp Cq CS Cu Cw
dA Dc dF dG dI Dk dL Dp Du Et Fp GL Hl Hu Hv Hw Id Ij In Ir Jp Kd Ki Kk Kn Kp Kr Kx Ky Kz Lh Lu Lx Ly Me Mi Ml Mn Ms Mu Mv
Mw Mz Na Nb Nc Nf Nw Ny Oa Og Oh Oi Ok Om Ou Ow Oy Oz Pb Pc Pi Pk Ps Qb Qv Qy Ra Rj St Tv Uc Ud Uf Ul Up Ur Us Ut Uv Uw Vp
Vt Yl Zq Zw Ye Tm Th) Lu(aJ aM An aP Ar As Aw Ax Ba Bn bQ bR bW bZ cN Cp Cq CS Cu Cw Dd dF dG dI Dk dL dM Ef Ex Ez Fb Gl Hv
Hw Ij Ir Jo Js Kd Kf Ki Kk Kn Ko Kp Kr Kx Kz Li Lj Mj Mp Mv Mx Na Nb Nf Nh Nv Nx Oa Pa Pc Pd Pg Pi Pj Pk Ps Qh Qm Qy Ra Rb Rh Rj
Rm Tn Uc Ud Uh Up Ur Us Uv Vp Yl Zw Xa Wm) bV(Ad aM An As AW Ax bF Bg bH bM Bn bP bQ bR bW bZ cE cN CP Cq cR Cs Cu Cv
CW dI Dk Dp Et Fa Fp Fy GL Hu Ij Im In Jj Jn Jv Kd Kc Ki Kk Ko Kx Ky Lh Lw Lx Ly Ma Ml Mn Ms Mt Mv Nb Nf Nn Nq Nw Ny Oe Oh
Om Or Ou Ow Oy Pc Pe Pf Pk Po Qd Qe Qv Qy Qz Tn Ud Ur Us Ut Vp) Ed(AD aJ aM aP As AW aY Bc bF Bg bH bJ Bn bR bW cE Ch cK Cp
Cq cS Cu CW dF dG Di Dk Dp Ex Fa Fb Gl Hw Id Ij Im In Je Jv Kd Ki Kk Kn Kp Kr Kx Ky Lh Lx Ly Me Mm Mn Mw Na Nc Nf Nj Nk Nl Nr
Oh Ok Or Ow Pb Pc Pe Pi Pk Qe Qt Qv Ra Rb Rj St Tv Ud Up Us Ut Uv Vq Vt Xa) Og(Ad aJ An aP As Ax Bn bW bZ cN Cp Cq Cs Cu Cv Cw
dF dG Dp EF Ex Fa Fb Gl Hl Hp Hu Hv Hw Ii Ik In Ir Js Jv Kd Kf Kk Kn Kp Kr Kx Ky Kz Li Me Mj Mn Mp Mx Na Ne Nf Nu Nx Oa Ow Pd
Pi Pk Qh Qt Qv Qw Qy Ra Rb Rj Ry St Tn Tv Ua Uc Ud Uf Ul Up Us Ut Uv Uw Vp Vs Vt Vw Yl) gL(Ad An As Ax bM Bn Ch CP Cq CS Cu
Cv Cw Dd Dk dL dM Et Fa Fp Fw Ha Hv Hw Id Ij Im In Ir Is Iv Jd Jn Jr Jt Jv Kd Kf Kn Kp Kr Kx Ky Lh Lv Lx Ly Ml Mu Mx Mz Na Nb Nf
Nt Oa Oi Ok Om Ou Ow Oy Oz Pb Pf Pi Pk Qd Qe Ql Qt Ra Rb Rj St Tn Tv Uc Ud Uf Up Us Ut Uv Vp Vt) Ql(AD AJ aM aP aW aY bH bQ
bR bW bZ cN cS Cu Cv CW dA Dc dF dG dI Dp Fa Hc Hu Hw Id Ij Im In Jd Jn Jp Jv Kd Kc Ki Kn Kx Ky Kz Lh Lw Lx Ma Mq Mr Ms Mu Nc
Nf Ng Nn Nr Nw Om On Or Ou Ow Oy Oz Pc Pe Pf Pi Pk Po Qd Qe Ra Ru Sh Tv Ud Uf Up Ur Us Uy Va Vt Yl Xa) In(Ad aJ aP As Ba Bn bW cN Cp Cq Cs cT Cu Cv
Cw Dc dF dG Dk dM Dp eC Ex Fa Gl Hv Hw Id Ij Ir Jg Jk Jo Js Kd Kf Kn Kp Kr Kx Ky Kz Li Lj Mj Mm Mn Mv Mw Mx Na Nb Nf Nh Ny Oa
Or Ou Ow Pa Pc Pd Pi Pk Ra Rb Rj Uc Ud Uf Up Ur Us Ut Uv Vp Vt) Ur(Ad aJ As Bg Cp Cq Cu Cv Cw dA dF Dk dM Dp EF Fa Fp Hu Hv
Hw Id Ij Im Ir Iv Jp Jt Kd Kn Kp Kr Kz Lh Lw Lx Ly Ma Mj Ml Mq Mr Mu Mz Na Nf Nr Oa Oi Ok Om On Or Ow Oz Pb Pc Pe Pf Pi Pk Qd
Qe Ra Rb Rj Tv Uc Ud Up Us Ut Uv Vi Vp Vt) Ky(Ad aJ aP Ax Ba bQ cN Cp Cs cT Cu Cv Cw dA Dc dF dG Dp Ef Fa Fp Hu Hw Id Ij Im Jj
Jn Jp Jv Kd Ke Ki Kk Kn Kr Kz Lh Lw Lx Ma Me Mi Ms Mv Mw Na Nb Nc Nf Nw Oa Oh Om On Ou Ow Oy Oz Pc Pe Pf Pi Pk Po Qd Qv Qy
Ra Tn Ud Uf Ut Uv Vt) Cv(An aP AW bQ CP CS Cu Cw dA dG Dp EF Et Fa Gl Hc Hu Hw Ij Im Iv Jj Jp Jv Kd Ki Kn Kx Kz Lh Lx Ly Ma Mi
Mj Ml Ms Mt Mv Mw Nb Nf Nn Nt Nw Oe Oh Oi Om On Or Ow Oy Oz Pc Pi Pk Qd Qv Qy Qz Tv Ud Ut Uv Vp Vt) Qv(Ad aJ aM aP Ba bH
cN Cu dA Dc dF dG Dk dM EF Et Ez Fa Fp Gl Hu Id Ij Jp Kd Ke Ki Kn Kx Kz Lh Lx Ly Ma Me Mi Mn Mv Mw Nf Nr Nt Nw Ny Oa Oh Oi
Ok Om On Or Ow Oz Pc Pe Pi Pk Ps Qy Ra St Tn Uf Ul Uv Vt) Oi(Ad An Ar Aw Ax Bg bQ cE cN Cp cS Cu Cw dL Dp Ex Fb Gl Hu Jk Jo Js
Kd Kf Ki Kk Kn Ko Kp Kr Kx Kz Lj Lw Mi Mj Mm Mn Mp Mx Na Nb Nf Nh Oa Pa Pc Pd Pi Pk Ps Qh Qt Ra Rm Ua Uc Ud Ul Up Ut Uv Vp
Vt Wm) Me(Ad aM An aO As bF Bg bH Bn bR cE cG CP Cq cS Cu Cw dA dL Dp Ef Ex Ez Fa Fb Fy Gl Id Ih Ij Je Js Kd Ki Kn Kx Ld Lj Mj
Na Ne Nf Nq Nu Nx Oa Or Ow Oz Pd Pz Qy Ra Rb St Tr Tv Uf Ut Vp Vt Wm) Jj(Ad aJ aP As Aw Ax Ba Bg bH Bn bQ bR Ch cN Cp Cq CS
Cu Cw dA Dd dF dG Dk Ex Fb Gl Ha Hf Id Jv Kd Ke Kf Ki Kk Kn Ko Kp Kr Kx Ow Pi Pk Qh Qm Qt Qw Ra Rb Rj Rm St Ua Uc Uf Up Us Ut
Uv Vp Vt) eF(Ad An As Ax bL bM Bn bW Ch Cp Cq Cs Cw dL dM Fp Fw Gl Hf Hx Id Ij Ir Iv Jn Jv Kj Lh Li Lj Lv Lw Lx Ly Ma Mi Ml Ms
Mu Mv Mz Nb Nc Nf Ng Nk Nr Nt Oh Om Or Ow Oy Oz Pc Pf Pk Rg Rh Us Ut Uu Vt) Nr(AD AJ aM aP As aW bH bR bW cN Co Cp Cq cT
Cu CW dA Dc dF Dp Fi Gd Hc Id Jv Kd Ke Kg Ki Kj Kn Kp Kr Kx Kz Or Ow Pi Pk Qz Ra Rv Sf Sh Tn Ud Uf Up Us Uu Va Vt Vz Yl Ye)
Or(aJ aP aW Ba bJ bR bW cS cT Db Dc dF Dp Et Fa Gl Gp Hc Hu Im Jn Jp Jv Ki Kr Kx Kz Lw Ma Mq Mr Mw Nc Nf Ng Nj Nl Ns Nw Oe On
Oy Pc Pf Pk Po Qd Qe Qy Rh St Tn Uf Us Vi Wb Yl Th) aJ(Dp Hc Hu Hv Hw Id Ij Io Jn Jv Kd Ke Ki Kn Kp Kr Kx Lh Lw Lx Ly Ma Ml Ms
Mt Mz Na Nb Nc Nf Nn Nw Ny Oe Om Ow Oy Oz Pb Pc Pe Pf Pi Pk Po Qy Ra Rb Rj Ud Up Us Ut Uv Vp Vt) Ou(aD Aj aM An aP Ba bR CS
cT Dk Dp Ex Fa Fp Gl Hc Hp Hu Jp Kd Ke Kx Kz Lw Ma Mr Ms Mw Nf Ng Nj Nl Nn Oa Oe On Pe Pk Po Qd Qz Rh Rv Sf St Tn Ud Us Uu
Uv Vt Vz Xa) Im(AD Aj As aW bQ bW cN Cp Cq cT Cu Cw Dc dF dM Dp Hc Hl Id Ju Kd Ke Kj Kk Kn Kp Kr Kx Pi Pk Ra Rb Rj Rv Sf Ud
Uf Up Us Ut Uu Uv Uz Vi Vt Wg Ye Tm Xa) Nw(AD aM An Ao As aW aY Bb bH Bn bQ bR cN Cp Cq Cu CW dA Dc dF dG dL Dp Ef Hc Id
Jv Kd Ki Kn Kp Kr Kx Kz Ow Pi Pk Qw Qz Ra Rb Rj To Tv Ud Up Us Uu) Ly(aP Ax Ba bQ bW cN Cp Cs cT Dc dF dG Dk Dp Ex Ez Fb Id Je
Kd Kf Kn Ko Kp Kr Kx Ld Mt Mx Nh Oa Ow Pi Pk Qy Ra Rj St Tv Uc Ud Ul Up Us Ut Uv Vp Vs Vt) Xa(aA Aj aM Ap bA bN bQ bU Ch cP
CS cT CX Dp Fr Fy Je Jf Jv Kc Ki Kk Ld Lh Lv Mi Mz Nb Nc Nf Ng Nl Nn Pb Pc Qe Qx Ra Sf Sr Tn Ud Un Uu Vi Yl Ye) dM(Dp Et Ex Ez
Fa Fp Gp Hc Hw Id Ij Iv Kd Ke Ki Kk Kn Kx Kz Ml Mt Mv Mw Mz Nb Nc Nt Nv Ny Oa Oe Oh Ok Oy Pg Pi Qm Qn Qy Ra Rh St Ud Uf
Ut Uv Vp Vt) Ba(aC aY bH bP bQ cA cP cS dA Dg Dp Em Ex Fp fR Gn Hc Hw Id Jn Jv Kd Kg Ki Kj Kx Kz Lw Mg Mr Ms Nf Oa Oe Oz Pc

Em Ex Hl Hp Id Kk Kn Kp Pi Ra Rj Rv Sh Tv Ud Up Uv Vt Zw) Ba(Eq Fa Hl Hv Ij Io Iz Jo Kk Kn Kp Lx Ml Mz Na Om Pb Pi Rj Rt Sh Up Uv Uz Va Vo Vp Wg Yl Zw Tl) Lx(aD An As Bn bS bU cA cF CP Cq Cu dH dI Ef Gp Id Kd Kn Kp Pi Qn Ra Rj Sf Tv Up Vt Yl Th) Ud(Ax cE Cs cW dG Ex Ez Fp fR Id Ij Lh Me Mm Mt Nb Ny Ok Om Qh Qt Ry Ug Uh Uk Ut Vp Zq Zw Th) Ri(Ar Bn cU Em Ex Ez Fd fR Gn Hp Iv Jt Kf Md Mj Mp Nm Nq Nt Nv Pg Qt Rb Rt Ry Uz Vh Vs Wg Tl) An(Aw Ax aY bC bM cG cP Cq Cs cU CW dL Ef Et Ez Im Jp Lh Ly Mi Ml Mn Mw Ny Pg Qt Rf) Gp(Ad As Bn Cp Cq Cu Cw Hv Hw Id Ij Ir Kd Kn Kp Lh Mz Na Pb Pi Ra Rb Rj Tv Uc Up Vp Vt) Cs(AD As bC bM Bn cG cP Cq Cu Cw Db Di dL Et Hw Ij Jp Mw Nk Om Pi Qt Qz Ra Up Ut) Fp(Ad As Aw Bn bQ cE cF cG CP Cq Cu Cw dG DI Ef Gl Kp Pi Ra Rb Rj Uc Up Ut Uv) aX(aC bM Du Hl Id Kd Kn Kp Pi Ps Ra Rb Rj Rt Tv Uc Up Ut Uw Uz Vh Vp Vs Wg Yl Zw Tl) bZ(Du Eq Fa Hp Ir Js Jt Mj Mx Ok Qz Rb Rt Ry Sh Ut Uv Uw Uz Vb Vc Vh Vs Wc Wg Zw Tl) cE(AD As Ax Bn cA CP Cq Cv CW Dd dL Ef Hv Hw Ir Iv Jj Ly Ml Mz Na Tv Vt) dI(Em Ez Gn Hx Ib Ir Jo Jp Js Jt Kf Kk Lj Lw Mt Mw Mx Nt Nv Pb Pg Qb Qt Qz Tv Vs) Sh(Ad Ch Cu Cw dF fR Ij Ir Iz Jk Js Kn Nq Nt Nv Nx Om Ph Pi Qd Qm Uw Vw Zq Th) Ug(Ad As Cp Cq Cu Cw Hv Hw Id Ij Jo Jt Kd Kn Kp Na Nm Om Pb Pi Ra Rj Uc Up Vt) Ly(aC AD Ar As Aw aY bM Bn cP Cq CU Cw dL Ef Gl Ne Nl Nu Nx Pd Qx Tr) Kk(Ad As aY Cu Cv CW Ef Hv Hw Ir Mi Mw Na Ny Pi Ps Qt Qw Qz Ra Rj Up Uv) Th(BC bQ Cv Ez Hl Jj Lv Ml Nj Nl Rb Rt Tn Ul Uz Vb Vh Vq Vs Vt Wg Tl) Tv(aJ aP Bo bQ bV dM Fa Fn Jj Mm Mn Nd Nj Nk Nq Nr Nv Pb Pg Qm Qn Rm Vq) eC(Bn Cp dL Hx Jo Js Jt Kf Lh Mj Ml Mt Mz Nb Ni Ny Ok Om Pb Pe Ra Uc Uv) Et(Ad Ap As Cp Cq Cu Cw Id Kd Kn Kp Pi Qz Ra Rf Rj Rv Up Uv Va Vp Yl) Mw(aC Ad As Ax Bn bV CP Cq Cu Cw Id Kn Kp Pi Ra Rj Up Ut Uv Vp Vt) Uh(Ad As Bn Cq Cu Cw gL Hv Hw Id Ij Kd Kn Kp Me Mz Na Pb Pi Ra Rj Up) Nk(Ax bQ Fd gL Gn Hl Ho Ne Qh Rt Ru Tr Uw Uz Vh Vp Vw Wg Zq Zw Tl) Rv(Ad Cw dF dG Ez fR Ij Li Mj Ml Mq Nt Nv Nx Ok Om Qx Ut Uw Vh Yl) aD(aO cG Ef Ez Ij Iv Jp Mi Mn Mt Mx Nb Nq Nt Nv Ny Ok Om Pg Ps Qt) cP(Ad As Aw Ax bC bM Bn cG Cq cU Cw Dd Di Ef Fc Im Mn Mt Ny Uw) Fn(As Bn Cp Cq Cu Hl Hv Kp Na Om Pb Rj Rt Uc Uz Vu Wg Yl Tl) Qt(As Ax Bn Cq Cv Cw dL Hv Hw Id Kp Mi Na Pb Pi Ra Rb Rj Up) Uk(Ad Cp Cw dG Hv Hw Id Ij Ir Kn Om Pd Ra Rb Tr Uc Ul Up Ut) aP(Gn Hv Hw Id Ij Im Iv Kd Kn Mz Na Ny Om Pi Qz Ra Up Vp Vt) bQ(Hv Hw Id Ij Iv Kd Kn Kp Ml Mz Na Pi Qz Ra Rj Tr Up Uv Vp) Gl(Gn Hv Hw Id Ij Ir Kd Kn Kp Ml Na Om Pb Pi Ra Rj Up Vt) Yl(Af Ax bU cX Ed fR Jf Lv Mh Mj Mq Nq Qb Qm Qn Tn Ut Wm) Pa(Cu fR Gn Hl Ir Jk Jo Js Lj Mj Nx Pb Pd Uw Vs Vu Zw Tl) Cv(Ad As Ax bM cG Cq cU Cx Di dL Hv Id Mz Na Pb Ra Up) Mn(As Bn CW Hf Id Kd Kn Kp Pi Ra Rj Uc Up Uv Vp Vt) Nj(Gn Hl Ho Hp Kf Rt Ry Uw Uz Vb Vh Vp Vw Wg Zq Zw Tl) bN(Du Em Gn Hl Rt Ry Uz Vb Vh Vs Vw Wc Wd Wg Zq Zw Tl) Cx(Du Em Gn Hl Ps Rt Ry Uz Vb Vh Vs Wc We Wg Zq Tl) Ed(fR Hl Rt Tr Uw Uz Vb Vh Vw Wd Wg Wh Zq Zw Tl tF) Ax(Ad As Aw bC bM Bn cG Cq cW Di Om Qz Up Ut Wh) Fa(Ad aY Cu Cw Id Ij Kn Mi Na Pi Qz Ra Up Uv Vt) Gd(Ad As Aw Cp Cq Cu Cw Dc Em Pi Rb Sr Un Ut Vu) Tr(bS bU cA cF CO dH Hq Jj Lz Mk Nd Ns Rg Tj) gL(Aw Ez Hx It Jo Js Li Lj Mi Mj Nm Nr Qb Qh Rg) Ef(Ad aE As bC cG Cq cU CW Fw Iz Lj Uv Vp) Me(Kf Ko Kp Pi Qx Rj Uc Ul Up Uv Vs Vw Wh Zq) Mh(Em Gn Hl Hv Hw Ij Jk Jo Ne Nu Nx Pd Wg Tl) Pb(bJ Bo Em Ex Kn Nx Pd Ry Vs Vw Wc Wd Zq Zw) Nq(Ao dL Em Gn Hl Hp Ne Ps Sf Uz Wg Zw Wm) Va(Ad Bc Jk Kn Nt Nw Ok Om Qm Vw Wd Zq Zw) bM(aO As aZ Bn cG Dd Di Mz Na Nb Ny Ok Om) Mj(Hv Ij Ir Jk Jo Lz Mp Na Nb Ne Ns Nx) Rf(bB Em Hl Iv Jo Js Nb Rt Uw Uz Vs Wg) bU(Du Fd Mt Rt Uz Vb Vh Wd Wg Zq Zw Tl) Kc(Fd Hl Hp Rt Vb Vh Vw Wd Wg Zw Tl) bP(Ad Aw Cw Id Kd Kn Om Pi Ut Uv Vt) Jp(Ad As Bn Cp Cq Cu Cw Eq Sf Zw) Nx(Hv Hw Ij Ir Lj My Na Ne Ns Sf) Bo(Bn Hv Jt Kp Rj Uc Vp Vt Vu) Wm(Fd Hv Hw Ih Jo Mx Nm Qc Rt) Mm(Kd Kn Kp Pi Ra Rj Up Uv Vp) Qz(dG fR Lh Mi Pg Vs Vt Vu Wd) Jk(Eq Hv Ij Ir Lj Ml Mx Ne Ns) Pd(bS cA Hq Hv Hw Ir Nb Nd Ne) bV(dR Ez Id Kn Pi Ra Vs Vt Vu) Ex(Id Ij Lw Mz Na Ra Up Vt) Nl(Cu Kd Kf Mp Qh Vp Vs Vu) Vw(Af Ap Ld Lv Ml Qb To Uo) Qd(As cW Id Kd Pi Up Vt) Ut(Hq Jd Je Lj Mk Nv Tj) cG(Ad As Bn cA Cq Cu Cw) dG(Hq Im Iv Mk Ml Nd Ns) Af(Rt Uz Vh Vs Wg Zq) Ez(Du Em Fc Rj Uz Wg) Gn(aJ Ao Co cX Jf Qm) Mp(Hq Ir Lj Ml Nd Nu) Om(aE Ap Iz Si Ue Wc) bJ(Id Ij Kd Kn Pi Up) Ne(Ir Js Lj Mx Ns) To(Vq Vs Vu Zq Zw) Sf(Ij Ir Nt Po Qb) Jo(Ad Cw Kf Kn Uc) Ny(aY Kp Ra Rj Tj) cW(cU Iv Nb Nt Vp) dE(Id Ra Rb Vs Vt) Ap(Lh Ok Uw Wd) Db(Mx Nt Rb Vs) Em(aJ Ao cX Jf) Wc(Cu Kn Mz Un) Qm(Rt Uz Wg Tl) aY(Im Nb Rb Vp) fR(Mi Mk Pi Ps) Aw(aE cA dL) Co(Ij Nv Pg) Di(Iv Qb Uv) Du(bS cA Qn) Ns(Ii Na Nu) Nd(Hp Zq Zw) Ir(Lj Mx Nu) Jf(Hl Zw Tl) Vu(dM Ii Jj) dF(Id Io Kd) Bb(Ok Vs) Fi(Fc Po) Mt(bS cA) Nb(Hv Hw) Ij(Lj Na) Im(bC Bn) Jh(Lj My) Wg(Nw Vq) Wh(Js Wd) bE(aC dL) CuIo DdaO EqTn LvHp MzcU HlPf TlJj QbUw PsbC UvVp UzVq VscX

Unconstrained panels with 3 analytes, where 4.0E-15 >= 'AUC p-value' > 0. Contains 50,000 panels of 11,919,473 total panels evaluated. : Dr{Fr(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp Du Ed Ef Em Eq Et Ex Ez Fa Fb Fc Fd Fi Fn fR Fw Fy Gb Gc Gd Gh Gl Gn Gp Gz Ha Hb Hc Hf Hl Ho Hp Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Op Or Ou Ow Oy Oz Pa Pb Pc Pd Pe Pf Pg Ph Pi Pj Pk Po Ps Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tv Tz Ua Ub Uc Ud Ue Uf Ug Uh Uk Ul Um Un Uo Up Ur Us Ut Uu Uv Uw Ux Uy Uz Va Vb Vc Vh Vi Vj Vo Vp Vq Vs Vt Vw Vz Wb Wc Wd We Wf Wg Wh Yd Yl Zq Zw Zx Ye Tm Tl Xa Wm Tj Ti Th) bZ(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX cA cB cC cD cE cF cG CH cI cJ cK cL cM cN CO CP CQ cR CS CT CU CV CW CX cY cZ dA DB DC DD DE dF DG dH DI dJ DK DL dM dN Dp Du Ed Ef Em Eq Et Ex Ez Fa Fb Fc Fd Fi Fn fR Fw Fy Gb Gc Gd Gh Gl Gn Gp Gz Ha Hb Hc Hf Hl Ho Hp Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Nj Nk Nl Nm Nn No Nq Nr Ns Nt Nu Nv Nw Nx Ny Oa Oe Of Og Oh Oi Ok Om On Op Or Ou Ow Oy Oz Pa Pb Pc Pd Pe Pf Pg Ph Pi Pj Pk Po Ps Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tv Tz Ua Ub Uc Ud Ue Uf Ug Uh Uk Ul Um Un Uo Up Ur Us Ut Uu Uv Uw Ux Uy Uz Va Vb Vc Vh Vi Vj Vo Vp Vq Vs Vt Vw Vz Wb Wc Wd We Wf Wg Wh Yd Yl Zq Zw Zx Ye Tm Tl Xa Wm Tj Ti Th) Lu(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX cA cB cC cD cE cF cG CH cI cJ cK cL cM cN CO CP CQ cR CS CT CU CV CW CX cY cZ dA DB DC DD DE dF DG dH DI dJ DK DL dM dN Dp Du Ed Em Eq Et Ez Fa Fb Fc Fd Fi Fn fR Fw Fy Gb Gc Gd Gh Gl Gn Gp Gz Ha Hb Hc Hf Hl Ho Hp Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lp Lt Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Op Or Ou Ow Oy Oz Pa Pb Pc Pd Pe Pf Pg Ph Pi Pj Pk Po Ps Pz Qa Qb Qc Qd Qe Qg Qh Ql Qm Qn Qt Qu Qv Qw Qx Qy Qz Ra

Rz Si Tv Tz Ua Ud Uh Uw Ux Uy Uz Va Vp Vt Wb Wc Wd Wf Wh Xa Tj Ti) Mi(Ad aI Al aM AO Aw bB bF bG bN bU bX cE cG Ch Co cR cU cV CX De dF Di Dl Du Et Fy Gh Gn Hc Hq Hu Il Jk Jm Jp Ki Kk Ks Ky Li Lj Lx Mj Mm Mn Mz Nr Nv Nx Oe Oi Ok Om Op Pc Pf Qa Qe Qt Qu Qv Qw Rg Ri Rm St Ua Ug Uk Ut Uw Ux Vi Wc Wf Yd Zx Ye Wm Th) Fb(aI An AO aS aW bB bF bG bX cE Ch cO CU cV Cx dF Dl Du Ed Et Fn Fy Gl Gz Hc Hq Hu Ic Ii Il Ji Jk Ke Ki Kk Ky Li Mf Mj Mk Mn Mz Nd Nk Nl Nm Nr Nu Nv Oe Oi Om Op Pa Pc Pf Pg Pk Qa Qe Ql Qw Ri Rx To Ua Uk Ut Va Vi Vp Vt Wb Wf Yl Zx Ye Tm Th) Nm(AO Ap Aw cE cG Ch Co Cp Cu Cw dF Dg Di Et Fy Gl Gn Hu Ij Jg Jh Ji Jk Jn Jp Kf Kk Kl Kn Ko Ky Lx Mj Mn Mz No Nr Nt Nu Nv Nw Ny Oh Ok Om Op Ow Pf Pg Ps Pz Qa Qc Qd Qe Qh Ql Qm Qt Qu Qw Rc Rm Rz Sr St Ua Uc Uf Ut Uw Ux Vp Vw Wd Wh Xa Th) Pc(aA An aO AW bA bR bV bX cE cF cG Co CP cT Cu Db dF Di Fn Fy Gl Gn Hu Je Jg Ji Jp Ki Kk Kl Kp Ky Lx Mj Mz Nk Nr Nu Om Pe Pf Ps Qa Qe Ql Qm Qt Qu Qw Rc Rf Ri Rm Rz Si Ss St Ua Uc Ud Uf Uk Um Ut Uw Ux Va Vq Vs Vw Wd Wh Yc Xa Th) Ud(Ad aI Al AO bF bG bN bU cE Ch Co Cq cR CU cV Cx dF Di Em Et Fy Gn Hc Hq Hu Ij Il Jg Ji Jk Jm Jn Jp Ks Ky Mf Mj Mn Mz Nd Nk Nr Nv Nx Oe Ok Om Op Pf Ph Ps Qa Qc Qe Qh Qt Qu Qw Rg Ri Rm St Ua Uk Ut Ux Vi Vp Wc Yd Zx Ye Th) Co(aA AJ An As AW bA bC bE bV bX cE cO cP cT Cv Cx dA dD dG dI Dl dM Du Ed Gc Gd Gl Hf Ho Ib Ii Je Jf Jo Jt Ju Jv Kc Ke Kg Ki Kj Ko Ky Me Mg Nc Ng Nk Nu Oe Oi Oy Pa Pj Qg Ql Qw Qz Rv Sf Sh Si To Uh Us Uy Vh Vt Ye Ti) Ql(aI Al Ao aW bF bG cE Ch cR Cu cV Cx dF Di Dl Du Fi Fy Gn Hc Hu Ii Il Ji Jp Kc Ki Ky Li Mn Nc Ne Nk Nr Oe Oi Op Pf Pj Ps Qa Qe Qh Qt Qu Qv Qw Ri Rx Si Ua Uf Ug Ut Uw Ux Va Vi Vj Vp Vq Vt Wb Wc Wd Yl Zx Ye Xa Th) bA(aC Ad aI Al aM AO Aw bB bF bG bN bU bX cB cE cF Ch cU cV CX dF Di Dl Du Et Fy Gh Gn Hc Hq Hu Ii Il Jk Jm Jp Ki Ks Ky Li Lj Mj Mm Mn Mz Nr Nv Nx Oi Ok Op Pf Qa Qe Qu Qw Rg Ri Rm Ut Ux Vi Yd Zx Ye Th) Ky(aA AW cE cO cT Db dI DL Dp Du Fc Fi Fy Gc Hu Hv Hx Ii Je Jf Jt Kd Ke Ki Kk Mj Nc Nd Ne Nk Nl Oe Oi Om Oy Pa Pf Pj Pk Qe Qg Qt Qw Ri Rv Rx Rz Sf Ua Uh Ux Uy Vb Vq Vt Wc Wd Wf Wh Yl Zx Ye Ti Th) Qw(aA An Aw bC bV bX cE cF cG cP cT Dd dF dN Du Ed Et Fn Fy Gl Gn Gz Hu Je Jf Ji Jp Jt Kk Lx Mj Nd Nk Nu Nv Nw Oa Oe Oi Ok Om Pe Pf Qa Qc Qe Qg Qm Ri Rz Si Sr St Ua Uf Ug Uw Va Vp Vq Wc Wd Ye) Ut(aA AJ aW Bb bC bE Bn bV cN cP cQ cT cZ dA dD dI dM Du Fd Gn Ho Ii Je Jf Ji Jo Jt Ju Jv Ke Kg Ki Kj Kz Mq Nc Nf Nk Nl Nu Oi Oy Pa Pj Qg Rf Ri Rt Sf Sh Uh Up Ur Us Uy Vh Ye Tl Ti) Du(aA aO Aw cE cF Cp Cu dF Et Fa Fw Fy Gn Hu Ir Jg Ji Jn Jp Ki Kk Lx Mj Mx Mz Nd Nk No Nr Nu Nv Nw Oa Ok Om Pe Pf Po Ps Qa Qc Qd Qe Qh Qt Ri Rm Rz Sr St Ua Uf Uw Ux Vp Wd Xa Th) Pf(aA Af An As aW bE bV cN cP cT Cx cZ dA DD dI dM Dp Ed Fn Gn Hf Ii Je Jf Ji Jt Ju Jv Kc Ki Me Ng Nk Nu Oy Pa Pj Ps Qe Qg Rf Ri Rv Sf Sh To Uk Us Uy Vp Vq Vt Ye Tl Ti) Fy(aA Ap aW Bb bV bX cQ Cx Dc Dd Dl Dl Ed Fn Gc Gn Ho Hu Ii Je Jf Jo Jt Jv Ke Kg Ki Kk Nc Nd Nk Nl Nu Oe Oi Oy Pa Pj Pk Qg Ri Si To Ug Uh Uk Uy Va Vq Vt Wc Wf Ti Th) Qe(Ap Aw Bb cE cT Cx Dc Dd Dl DL Fd Fi Gb Gn Ha Ho Hu Hv Hx Ii Iq Ir Je Jt Ke Ki Me Mk Nc Nk Nl Nu Oe Oi Pa Pj Qg Ri Rx Si Uk Uy Vq Vt Wc Wd Wf Wh Zx Ye Ti Th) Mj(An Ao aW bO bP bU cT Cx dA Db dI DL Dp Fd Fi Fn Fw Gn Hf Ho Hu Hv Ii Ir Je Jt Kc Ke Kf Ki Mx Nc Nd Ne Nk Nl Nu Oe Oi Oy Pa Ri Rv Ry Si Uk Vh Vt Wc Yl Ye) Qa(Ap aW bO cT dA Dc dI DL Dp Fd Fn Fw Gn Ho Hx Ii Ir Je Jt Jv Kc Ke Kf Ki Me Mk Nc Ng Nh Nk Nl Oe Oi Oy Pa Pj Ri Rv Rx Sh Uh Uk Ur Vh Vt Yl Ye Ti) Vp(Ao aW bR cE Db dF dN Fd Fn Gl Gn Ho Hu Hv Hx Id Ii Je Ke Ki Nc Nd Ne Nh Nk Nl Oe Oi Op Pa Pk Ps Pz Qc Qm Qn Rj Rz Ug Ur Ux Vq Vt Wc Zx Yc Ti) Ki(AO Aw bV cE cG cL cO cT dF Dg Di Gl Gn Hu Jg Ji Jk Jp Kl Lx Mn Nd No Nr Nv Oh Ok Om Po Qc Qm Qt Ri Rz Sr Ua Uf Uw Ux Vq Wd Xa Th) Ps(bF Ch Dd dF Di Dl Fd Fi Fn Gb Gn Ha Hc Hu Hv Hx Ic Ii Ir It Jt Kd Ke Kk Lp Mx Nk Nl Oe Oi Pj Pk Ri Rx Si Tz Ug Va Vt Wc Wf Zx Ye) Ii(Aw cE Cp Cu dF Gl Hu Ij Jg Jh Ji Jk Jn Jp Kk No Nr Nt Nv Nw Ny Ok Om Pe Pg Qc Qd Qh Qt Rz St Tz Ua Uc Uf Uw Ux Vq Wd Wh Xa) Nk(aO bV cE cG Ch Cp Cu Cx dF Di Ed Gn Hu Jg Ji Jk Jp Mn Mz Nr Nu Nv Ny Pg Qc Qd Qh Ri Rm Rz St Tv Tz Ua Uc Wd Zx Xa Th) Jp(aA Aj aW bE cQ cT cZ dA dD dI dM Ed Fc Gn Hf Je Jt Jv Kc Ke Kg Kj Nc Nf Oy Pa Pj Qg Rf Ri Sf Sh Us Uy Vh Vt Tl Ti) Hu(An aW Bb bV cE cT Cx Ed Gn Ho Ib Ji Jt Ke Nc Nd Ng Nl Nu Oe Oi Oy Pa Qm Qz Ri Rx To Uk Ur Va Vt Wc Wh Ye Th) Je(Ad aS bF bG bU cF Ch cU cV Cx dF Et Hc Hq Il Ks Li Lx Mf Mn Mz Nd Nr Oi Ok Op Qc Qu Ri Rm Vi Wc Yd Zx Th) cT(Ad aI Al AO Aw bF bG bU bX cE cG Ch cU cV CX dF Em Et Gn Hc Hq Il Jk Li Lj Mn Op Qu Ri Rm Vi Yd Zx) Ri(aA AO bV dF dI Ed Gl Gn Jg Ji Kk Mz Nd Nl Nr Nu Nv Op Qc Qd Rx Rz St Ua Uc Ux Vt Wd Wf Zx Xa Th) bF(aA aJ aP bC bE cP dA dD dG dI dM Ed Ho Ip Jf Jo Ju Jv Kg Mq Nf Nu Oy Qg Rf Sf Sh Sr Vq Wd Xa Ti) Th(AW bR cE cY Fn Gn Gz Ji Kk Lx Nc Nd Nl Nv Nw Oi Om Op Po Rx Ua Uw Va Vq Wc Wd Wf Wh Zx) Ke(Aw Cp Cu dF Jg Ji Jk Kk Lx Mn Mz No Nr Nv Nw Ny Ok Om Pe Qd Qh Qt Rz St Ua Uf Uw Ux Wd Xa) Ch(aA aJ bE cP dA dG dI dM Ed Jf Jo Jv Kg Nc Nf Nu Oy Qg Rf Rx Rz Sf Sh Sr Uy Vq Wd Xa Ti) Jt(Ao cE cG Cp Cu dF Dg Et Ij Jg Ji Jk Jn Ko Mn Nr Ok Om Pz Qd Qh Qu St Ua Uc Uf Uw Ux) Vt(aI aO cE Cu dF Et Gl Jg Ji Mz Nr Nv Nw Ok Om Op Qc Qd Qt Rm Rz Ua Uc Uf Uw Ux Zx) dF(aA An aW bE Bn bP bX CX dA dD dI dM Ho Me Nc Nl Nu Oe Oy Pa Rv Sh Wc Ye Ti) Ao(aA aJ bE bV cP Cv Cx dD dM Ed Gc Jf Jo Jv Oy Qg Sh Si Va Wc Ti) Ua(aW cO Cx Ed Gn Ho Ib Ji Kf Nc Ng Nl Nu Oe Oy Pa Uk Ur Uy Wc Ye) Wd(Ap bU Dp Ed Fn Ib Li Nd Ng Nl Nu Oe Oy Pa Qz To Uk Vs Wh Ye) Kk(Cx Fd Fi Ho Kc Ly Nd Oe Op Rv Ry Sf Si Uy Vi Vw Wb Ye Tm Xa) Vi(aA aJ bE bV cN cP cZ dA dD dI dM Gn Jf Jv Nu Qg Rf Sh Ti) Il(aA bE bV cN cP cQ cZ dA dD dI Gn Jf Jv Qg Rf Sf Sh Ti) Hc(aA aJ bE bV cN cP cQ dA dD dI dM Ed Jf Kg Nu Oy Qg Ti) cE(An Cv Cx dI Ed Ex Gc Ho Ic Jo Jv Nd Nu Oe Oi Pa Uy Ye) Ux(Ap Cx Dl Ed Gc Ho Ic Ji Kc Nd Oe Pj Si Uk Uy Wc Ye) Cu(Cv Cx Fd Fi Ho Hv Hx Iq Ir Kd Nc Nl Oe Uy Wc) Ti(Ad bG Et Mm Mn Mz Nr Nv Nx Ok Op Qu Rm Yd Zx) aA(Ad bG bU cU CX Et Li Mn Mz Op Qu Rm Yd Zx) Nr(aW dI Fi Ho Nc Oi Oy Pa Pj Qg Sf Si Uy Vq) Ji(Ap aW Dl Ed Gc Me Nc Nl Pj Si Uh Va Wc Zx) Om(Af Ap Bb Cx Ed Ng Nu Oe Oy Rx Uy Vh Wc Ye) Nu(dL Oe Oi Op Qt Qu Rz Vq Wh Yd Zx Xa) dI(Aw bG bX Cp cV Lx Mz Nv Ok Qc Qu Zx) Ed(Aw Dg Gn Jg Op Qt Qu Rz Uw Wh Zx) Xa(bX cR Dl Gn Nl Oi Si Uk Va Zx Ye) Ye(Aw Gn Jk Kl Nv Qt Rz Vq Wh Zx) bG(aJ bE dM Mq Nf Oy Pa Qg Rf Sh) Yd(aJ bE cZ dA dD dM Jf Oy Qg) Qu(Aj cP dA Gn Ng Oy Pa Qg Sh) Oe(Aw Cp Jg Jk No Nv Qd Qt Wh) Uy(Jk Mz Nv Nx Ok Op Pg Uw Zx) Cx(aO Aw bC cG Cp Gl Qg Uw) Wc(Gl Jg Jn Nd Nw Pg Qc Rm) Ho(Cp Jk Nv Pg Qd Rm Uc) Aw(As cX Ex Gl Ng Uk) Mn(Gn Hf Jv Pj Qg Sh) Cp(Dl Nl Oi Si Vs) Nd(Hf Qg Qt Rz Tl) Jn(Nl Oi Rx Si Va) Rm(cQ Gn Nl Ur Va) Mz(Pa Qg Sh Us) Nc(Jk Pg Qh St) Op(bV dM Jv Pj) Uk(Qt Rx Rz Zx) Dl(Kl Qd Vw) Wh(Ib Jh Si) Jk(aW Gn Oy) Nv(aW Oy Pa) Bb(Jg Uw) Di(Oi Rx) Et(Pj Qg) Qt(Ib Pa) Rz(Ap Nl) ExcY FdQd FnRx GccG GnTm NoOi LxYl ToWf QgaO VaVw bEcV} Ni{Th(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp Du Ed Em Eq Et Ez Fa Fb Fc Fd Fi Fn Fp FR Fw Fy Gb Gc Gd Gh Gl Gn Gp Gz Ha Hb Hc Hf Hl Ho Hp Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Nj Nk Nl Nm Nn No Nq Nr Ns Nt Nu Nv Nw Nx Ny Oa Oe Of Og Oh Oi Ok Om On Op Or Ou Ow Oy Oz Pa Pb Pc Pd Pe Pf Pg Ph Pi Pj Pk Po Ps Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tv Tz Ua Ub Uc Ud Ue Uf Ug Uh Uk Ul Um Un Uo Up Ur Us Ut Uu Uv Uw Ux Uy Uz Va Vb Vc Vh Vi Vj Vo Vp Vq Vs Vt Vu Vv Vw Vz Wb Wc Wd We Wf Wg Wh Yd Yl Zq Zw Zx Yc Tm Tl Xa Wm Tj Ti) Du(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp Ed Em Eq Et Ez Fa Fb Fc Fd Fi Fn FR Fw Fy Gb

Figure 7 Continued cC Cs CX dE Dp Ed Et Ez Fn Gl Ha Hc Hf Hr Hu Hw Ib Ih Im In Is It Jd Ji Jk Jl Jm Jn Jp Jr Js Ki Kq Ks Kz Ld Lh Lj Mb Me Mj Mn Mp Mq Ms Mt Mu Mv Mw Mz Nf Ng Nj Nk Nn No Nr Nu Nw Nx Ny Oa Og Oh Ok On Or Ow Oy Pa Pb Pc Pe Pi Qa Qb Qd Qe Qh Ql Qm Qy Rf Ri Rm Sr Ss St To Tz Uh Un Us Ut Uv Vt) Gc(aD Af Aj Ap aZ Bb bN bR bU cA cC Cs cX dE Dp Ed Et Ez fR Fy Gd Gl Hc Hf Hr Hu Ih Im In Ir Is Jd Ji Jk Jl Jm Jn Jp Jr Js Kc Kq Ks Kz Lh Lj Ly Me Mj Mn Mp Mq Mt Mu Mw Mv Nf Nk Nn No Nq Nr Nu Nw Ny Oa Og Oh Ok On Or Ow Oy Oz Pa Pb Pc Pe Pi Qa Qb Qd Qe Qh Ql Qm Qy Ri Rm St To Tz Uh Un Us Uv) To(aA aD aM bQ bV cN Cv Dc dF dJ Ed Em Et Fy Gl Hc Hu Ih Im Ir Is Jd Ji Jk Jl Jn Jq Jr Jy Ki Kn Kq Lh Lw Lx Ly Ma Me Mn Mp Mq Mr Ms Mt Mu Mw Mz Nk Nn No Nr Nw Ny Oh Oi On Or Oy Oz Pb Pc Pe Pf Pg Po Qa Qb Qd Qe Qh Ql Qt Qy Rf Ri Rm Sr St Uh Un Ut Vq Vt Vu) aW(aD aJ aK aM Bo bS bU bV cN Cs cU dM Dp Ed Em Et Ex Fn Fp Gl Hc Hu Ih Im Is Jd Ji Jk Jl Jn Jq Jr Ki Kq Lh Lx Me Mp Mq Mr Ms Mt Mu Mw Ng Nk Nn No Nr Nw Nx Ny Oe Oh Or Ow Oy Oz Pa Pb Pc Pe Pg Po Qa Qb Qd Qe Ql Qt Qy Ri Sr St Uh Un Ut) Tn(Aj aM bH cN Co dJ Dp Ed Fp Gl Hc Hf Hu Ih Im Is Jd Ji Jk Jl Jn Jr Jv Ki Kj Kq Kx Kz Ly Me Mg Mq Mt Mu Mw Nf Ng Nn No Nw Ny Oa Or Ow Oy Oz Pa Pb Pc Pe Pf Pk Po Qa Qb Qd Qe Qh Ql Qt Qz Rf Rg Ri Rm Sr St Uh Un Us Ut Uu) dM(aC aD Aj aM Ap aZ bJ bN Bo bR bS cA cC cN Cs CX DB dC dE Dp eC Ed Em Fn Fp Hc Hf Hu Im Jd Jl Jm Jn Jr Kz Ly Mb Me Mj Mq Ms Mv Nf Ng Nk Nn No Nr Nx Ny Oa Og Or Oy Oz Pa Pb Pc Pe Pf Pk Po Qb Qe Ql Ri Sr Uv) eF(aA aD Aj aM Ch cN Cs Ed Fa Gl Ha Hc Hf Hx Ih Im In Is Iv Ji Jk Jl Jn Jr Kq Kx Kz Lj Ly Me Mq Mw Nf Nk Nn No Nw Ny Oa On Or Oy Oz Pc Pe Pf Pk Po Qa Qb Qd Qe Qh Ri Sr St Uh Un Uu Vt) Aj(Al aM bA bF Bo bQ bR bS bZ cA cS cU dR Em Ex Ez Fb fP Fy GL gP Hu Im Is Jd Jk Jl Jn Jr Lh Lv Ma Mn Ms Mu Nk Nn No Nr Oh Ow Pf Pg Po Pz Qa Qd Qe Ql Qy Ri Tr Tt Ua Un tF) Tv(Ed Em Et Fn fR Gd Gl Hc Ih Im Is Jd Ji Jk Jl Jn Jr Kq Lh Lw Lx Ly Me Mp Mq Mt Mu Mw Nk Nn No Nw Ny On Or Ow Oy Oz Pc Pe Po Qa Qb Qd Qe Qh Ql Ri Rm Sr St Uh Un Ut Vq) cN(aK Ap aU aZ bH bJ bN bR bS bX cA cC cH cI cL CX DB dC dE dH dI Dp dR Ed Ef Fn FP gL gP Hu Jd Jh Jn Jr Lv Ly Mb Me Mn Nk Nr Ns Oe Og Ri) gL(aA aD Cs Ed Fa Gl Ha Hc Hf In Is Ji Jk Jl Jr Kz Li Ly Me Mq Mw Nf Nk Nn No Nw Ny Oa Or Oy Oz Pc Pe Pf Po Qa Qb Qd Qe Qh Ri Sr St Un Uv Vt) dR(aA aD aP bV Ed Fa Gl Ha Hc Is Ji Jj Jk Jl Jn Jr Kq Kx Me Mq Mw Nk Nn No Nw Ny Oa On Or Oz Pc Pe Pf Po Qa Qb Qd Qe Qh Rf Ri Sr St Un) gP(aA aD aJ aP Ed Fa Gl Hc Is Ji Jl Jn Jr Kq Lx Ly Me Mq Mt Mw Nk Nn No Nw Ny Oa On Or Oz Pc Pe Pf Po Qa Qb Qd Qe Qh Ri Sr St Un Vt) Tt(Ed Gl Hc Im Is Jd Ji Jk Jl Jn Jr Kq Ly Me Mp Mq Mu Mw Ng Nn No Ny Or Oy Oz Pc Po Qa Qb Qd Qe Qh Ri Rm Sr St Un Ut) Tr(Ed Gl Hc Hf Im Is Ji Jk Jl Jn Jr Ly Me Mp Mq Mw Ng No Ny Or Oy Oz Pc Po Qa Qb Qd Qe Qh Ri Rm Sr St Un) Ed(aA aD aE bA bF bV bZ cI dI Hu In Jd Jp Jr Ki Mn Ms No Nr Oe Og Oi Qg Qv Qy Ri Sr Un Ur) cI(aM cW Em Et Gd Gl Hu Jd Ji Jl Jn Jr Kq Lh Me Mq Nk Nn No Nw Pe Po Qa Qd Qe Ri Sr Uh) No(aE aK Ap Bb bH bO bP Cx Dg dI Dl Jv Kc Kj Kl Ko Kr Qu Qz Ri Ss Us Uu Vo) Og(Ax bA bV bW Co Cs dJ Em Ex Gd Jd Ji Jl Ki Lx Mu Nw Om On Po Uf Un) Em(aE Af Ax bI bN bR bV cC Cs Cx Fp Ir Jd Nk Oh Qn Ri Uu Vo) dI(aD aE aM bA bR bV Cs cX dC Fa Hu Jd Lx Ms Nk Nr Oi Po) Nr(aE aK Ao bH bI bP bV Co Gd Iz Kg Ki Kj Uu Vo) Jd(aE Ao bP Gd Ii Iz Kg Kj Kl Ms Ng Oi Oy Ue Uu) bV(aE bR bX Cx dC Dp FP Ly Ng Oe Ri Us) Ji(aA Fp In Jj Jr Ly Ms Ng Nm Ns Oi Pb) Hu(aD aE Ao Ax bA bP Co Cs Kj Uu) aA(aD bA bR CX dC Dp fP Lv Ri) Nk(aE aK aN bA bl bP Cs Ki) Kj(Jr Kq Ma Mn Nn Pf Po Sr) Uu(Ba Dk Fr Jp Kq Mn Nn Pf) Ri(aE Ax bP Cs Ir Iu Ki) Fp(aD FR Gd Mn Nw) Ng(Fr Nn Nw Om On Po) Un(aE Ii In Ir Lu Ms) Jj(Dp Po Qa Qb Qe) Cs(bH Ms Na Oe) aE(bH bS Jn Mu) bA(aK Hc Ly Oy) Ex(Ap Gd Jt) Kq(Jt Kl Vo) aD(bH dJ Jn) Po(bH Pb) Ly(Ki Nw) Mn(Kr Us) BaKI DpQv FaFP FyKg NnIz MaVo IiSr JnbP JrNw} Kq{Uu(aA aC AD aE AF aI AJ aK AL aM An Ao Ap aQ Ar AS aU aV AW Ax aY aZ BA Bc bE bF Bg bH bJ Bn BO bP bR bS bV bW bX bZ cA cB cC cD cE CH cI cK cL cM cN CO Cp CQ cS CT CU Cv CW CX cY cZ dA DB Dc DD DE Dg DI dJ Dk DL dM dN Dp dR Du eC Ed EF Et Ex Ez Fa Fb Fc Fd Fi Fn FP Fr Fw GL GP Ha Hb Hc Hf Hp Hq Hr Hu Hv Hw Hx Ib Ic Id Ih Ii Ij Il Im In Io Ip Iq Ir Is It Iu Iv Iz Jd Jf Jg Jh Ji Jk Jl Jm Jn Jo Jp Jq Jr Jt Ju Jv Jy Kd Ke Kf Kg Ki Kj Kl Kn Ko Kr Kx Ky Kz Ld Li Lj Lt Lu Lv Ly Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Nj Nl Nm Nn No Nq Nr Ns Nt Nu Nv Nw Nx Oa Oe Of Og Oh Oi Ok Om On Op Or Ou Ow Oy Oz Pa Pc Pe Pf Pg Ph Pi Pj Pk Po Ps Qa Qb Qc Qd Qe Qg Qh Ql Qm Qn Qt Qu Qv Qw Qx Qy Qz Ra Rb Rc Rf Rg Rh Ri Ry Sf Sr Tn To Tr Tv Ub Uc Ud Ue Uf Uh Uk Ul Um Un Uo Up Ur Us Ut Uv Uw Uy Uz Vb Vh Vj Vo Vp Vt Vz Wh Yd Ye Tm Xa Wm Tj Ti Th tF) Kj(aC aD aE AF aH aI aj aK AL aM AN Ao Ap aQ AR AS aU aV AW AX aY aZ Bb Bc bF BG bH bJ bM BN BO bP bQ bR bS bU bV bX bZ cA cC CH CL cK cM CO Cp CQ cR CS CU CV cW CX cY cZ DB dC dD DE dF Dg dH DI dJ Dk DL dM dN Dp dR eC Ed EF Em Eq Et Ex Ez Fb Fc Fd Fi Fn FP Fr Fw Fy Gc Gh GL GP Hb Hc Hf Ho Hp Hq Hr Hu Hx Ib Ic Ih Ii Ik Il Im Io Ip Ir Is It Iu Iz Jd Jf Jg Jh Ji Jk Jl Jm Jn Jp Jq Jr Jt Ju Jv Jy Kc Kd Ke Kf Ki Kl Ko Kp Kr Ks Kx Ky Kz Ld Li Lj Lp Lv Lw Lx Ly Lz Ma Mb Mc Md Me Mf Mg Mh Mi Mm Mn Mp Mq Mr Ms Mt Mu Mv Mw Mx My Na Nb Nd Ne Nf Nh Nj Nl Nm Nn No Nt Ns Nu Nv Nw Ny Oa Oe Of Og Oh Oi Ok Om On Op Or Ou Ow Oy Oz Pa Pb Pc Pd Pe Pf Pg Ph Pj Pš Qa Qb Qc Qd Qe Qg Qh Ql Qm Qn Qt Qu Qv Qw Qx Qy Qz Ra Rb Rc Rf Rh Ri Rj Rm Rx Sh Sr Ss St Tn Tv Tz Ua Ub Uc Ud Uh Uk Ul Un Uo Up Ur Us Uv Va Vo Vp Vs Vt Vw Vz Wb Yl Zq Zw Xa Wm Tj Ti tF) Us(Ad aE Aj aK aL Ao aW bH bJ bO bP bV cI cK cN Co Cq Cu dJ dJ Dk dM dN Dp dR Du eC Ed eF Eq Fc Fd Fn Fp Gb Gc Gh gL Gn gP Hb Hc Hl Ho Hp Hu Ib Ih Ii Ir Iu Iz Jt Jv Kd Kg Ki Kl Ko Kr Lp Lt Lu Md Ms Mu Mw My Nb Ng Nm Nv Of Oi Op Oz Pb Pg Ps Ql Qu Qz Ri Rt Ru Rv Rx Ry Sf Sh Sj Tn To Tr Tt Tv Ur Uz Vb Vc Vh Vi Vj Vo Vs Vw Vz Wb Wd We Wf Wg Wh Yl Zw Zx Ye Tm Tl Xa Wm Ti Th) Sh(Af al Aj aK aL Ap aQ As aU aV aW Bb bE Bg bH bI bJ bL bN bO bQ bR bU bW bX bZ cC Ch cU CX cY cZ dA Db dD dG dI dJ Dk dL Dp Du Ed Em Eq Fi Fn Fw Hc Hp Ib Ih Ii Ij Im Je Jg Jh Jm Jn Ju Jv Kd Kf Kl Kr Ks Ld Lx Mt Mu Nf Nj Nk Nu Oe Og Om Oy Pa Pb Pi Pk Ql Qm Qt Qu Qy Qz Rb Rc Ri Rm Rv Ry Rz To Tv Uf Uk Vi Vo Vz Wd Wf Wh Ye Tm Xa Th) Rv(Af Aj aL Ap aV Ax Bb bJ BN bO bR bW bZ cA cO cR Cs cT CX dA Db dH dN Dp Ez Fa Fd Fi Fw Gh Hb Hc Ih Ii Im Io Ir It Je Jg Jh Jv Jy Kd Ke Kf Ki Kr Lj Lt Lz Ma Mh Mq Mr Mt Mw Nc Nf Nj Nk Nl Nn Nr Nu Nv Oe Oh Oi Ow Oy Oz Pa Pb Pf Pg Qd Qh Ql Qn Qu Qv Qx Qy Qz Rb Rc Rf Rh Ri Ru Sf Tz Uy Uz Wh Zw Xa Wm) gP(AF Aj aK AL aM Ao Ap Bb bF BG bJ bL bN bR bX Ch Co Cp Cs Cx DB dC De Dg dH Dk DI dN Ed Fn Fp Hc Hf Hq Hu lv Iz Jg Jt Jv Kc Kd Kf Kl Ko Kr Kz Lj Ly Md Me Ml Mq Mr My Nc Nf Ng Nk Nl Nm No Nu Nv Nx Oa Of Oi Ok Oy Pa Pb Pe Pk Qa Qv Qz Rb Rg Ri Rj Sr Ss Uc Ue Um Ut Uv Vo Vp) Oy(aE aW Bb bJ bP bX cI cN dI dM dN dR Du Ed eF Eq Fn Fp Gb Gc Gh gL Gn Hl Ho Hp Hu Ii Ir Jd Kx Lt Nr Og Op Ps Ql Ri Rt Ru Rx Ry Rz Sf Si Sj Tn To Tr Tt Tv Uw Ux Uy Va Vb Vc Vh Vi Vj Vo Vw Vz Wd We Wf Wg Wh Yd Yl Zq Zw Zx Ye Tm Tl Ti Th) dR(AF Aj aK AL aM aU bF bG bJ bL BN bX Ch Co Cq Cx DE Dg dN Ed Fn Fp Hc Hf Hu Iz Jg Jt Jv Kc Kf Kg Kl Ko Kr Kz Lj Ly Me Mq Mr My Nc Nf Ng Nl No Nv Nx Oa Of Oi Om Pa Pb Qz Rb Ri Sr Ue Uv Vo) Ed(Ad aE aF Aj aN aW bA Bb bH bJ bO bV bX cI cK cN Co Cq Cu cX dA dI dJ Dl dM dN eC EF Fi Fn Fw gL Ih Ii Ir Iu Iz Jg Jt Jv Kd Ki Kl Ko Kr Nv Oe Of Og Oi Pb Pg Qu Qy Ri Tn To Tr Tt Tv Ur Vo Vp) Dp(aA Ad Aj Ao aW cI Dl dN Eq Fc Fd Fi Gb Gc Gh Ho Ii Ir Iz Jj Jo Jt Kg Kl Lp Lt Lu Nm Oi Ps Qv Rt Ru Rx Ry Sf Si Sj Tn To Tr Tt Tv Uw Ux Uy Va Vc Vo Vz Wb Wc We Wf Wh Yd Zq Zw Ye Tm Tl Ti Th) Kl(aK Ax BA bE bH bJ bP bR bV bZ cT Cx cZ dA Dc dI dJ dM dN eC eF Ex Fn Fp Fw gL Gp Ha Hb Hu Hv Is Jn Jv Kd Ki Ko Kr Kx Kz Ly Nf Nn No Nr Nx Og Ow Pg Qw Qy Ri To Ur Wm Th) Aj(aW Bb bH bJ bO bR cI Cq Cx cZ Db dI dM dN eC EF Fd Fi Fn FP gL Hb Hc Hp Hu Ii Jt Kd Ke Ki Ko Kr Lu Ly Ms Mu Nb Nl Nr Og Ps Qz Ri Tn To Tv Ur Vj Vw Vz Yl Zq Xa Th tF) Kr(aK Ao aW bH bP cI Co Cq Cs Cu dJ dM dN EF Eq Fp gL Hp Ib Ii Ir Iu Iz Jg Jt Jv Kg Ki Lu Md Mw My Nb Ng No Nv Of Og Oi Pg Ps Qu Qy Ri Rz Tn To Tr Tt Ur Vh Vo Vs Th) Oz(aW cI dM dN Du Fc Fd Fi Gb Gc Gh Gn Hl Ho Hp Jt Lp Lt Op Ps Rt Ry Rz Sf Si Sj Tn To Tr Tt Tv Uw Uz Va Vc Vh Vi Vj Vw Wb Wd Wg Wh Yd Yl Zq Zw Zx Ye Tm Tl Xa Ti Th) dN(aK Ap

Figure 7 Continued aV Bb bH bO bX Co Cx De dH dI dL eC Ef Eq Ex Fn FP gL Hc Kd Ke Kf Kg Ko Kz Ly Mc Nf Ng Nx Of Og Om Pa Pc Pg Qw Qz Ri) eF(AF AI aM Ao Bb bL bN bX Ch Co Cx De Dg fP Hc Hf Hq Ic Jg Jt Jv Kf Ko Kz Ly Me Mq Nf Ng Nl No Nx Of Pa Pb Pc Rb Sr Uc Ue Vo) Eq(aF Ap Bb Bn bO cG Cp Cx cZ Dc DE dH Ez Fi Fn Id Ii Im Je Jq Jv Jy Kd Ke Nm Og Om Pb Pg Ql Qn Qy Qz Ri Sf Uc Up Zx Th) Fp(Ad Ao aW bA Bb Co Cq Dk Dl dM Gd Ih Ii Ir Iu Iz Jj Jo Jt Jv Kg Kn Lu Md My Nb Nm Nv Of Og Oi Pg Tn To Ur Vo Vp Vs Ti Th) Hc(aE aW Bb cI dM Fi gL Ih Ii In Ir Iu Iz Jt Lu Nm Oi Ps Ru Sf Tn To Tr Tt Tv Uy Vo Xa Ti Th) Kc(Du Gb Gc Gh Gn Ho Lt Op Ru Rx Rz Uw Ux Uy Uz Va Vb Vc Vh Wd We Wf Wg Wh Zq Zw Zx Ye Tm Xa) gL(AF Ao bL bN Ch Co De Dg fP Hf Jg Jt Jv Ko Kz Ly Me Mg Mq Nf Ng No Oa Of Pa Pc Sr Uc) Bb(aF aK bJ cI cX Db Ex Fi Fn Jd Kx Ly Nf No Nr Og Pa Pk Ps Rf Sf Un Vz Wb Yl Ti Th) Cx(aW dM Fi Gc Iz Jt Kg Of Sf Si Tn To Ur Ux Vc Vh Vj Vz Wb Wc Yd Yl Zx Ye Tl Xa) Jg(bH dI Fc Fi Fn Ho Hp Lt Nv Of Op Sf To Uy Vb Vc Vj Vz Wc Zq Ye Tm Xa Ti Th) De(aK aN aW bJ bO bP bX cI cK dI dM Fi Hp Vz Wb Yl Xa Th) Og(bJ Co dI dM Ef Fn Hb Hp Jv Ki Md Of Pg Ps Qz Yd Xa Wm) Fi(aV BN bO Fc Fn Im Iv Je Ki Mr Nf Pb Qz Ri Vo Vz) Ly(aW cI Cu dI dM Ii Ir Iz Jt Jv Ki Qu Tn To Tr Tt Vo) Nf(aW cI Ii Ir Iu Iz Tn To Tr Tv Ur Uw Vo Wb Ye Th) Pb(aW Gc Hp Ps Rx Sf To Tr Uw Vh Vz We Yd Yl Ye Xa) eC(aA Ao aW bP cI cN Co Cs dI Ii Jt Kg Ng Of Uc Vo) Ko(aW cI dM Hp Iz Ps To Tv Ur Vo Vz Wb Yl Zq Th) Ef(aA Ao aW bA Dl Jt Lu Oi Tn To Tt Vo Ti Th) dI(bR Cp Cs Dg Fn Jv Lj No Nv Of Oi Om Vo) Jt(aK aL bJ bX Ex Jn Jv No Ps Ql Rf Wm) Vz(BN Fn Fy Ih Im Jv Nu Ql Ri Up) Ps(Af Dc dH Fw Kf Kp Nc Nk Uc Up Vs) Th(Bn bO Hf Kf Nc Ng Nk Pa Ri Uc) Me(aW cI dM Iz Tn To Tr Tt Tv Vo) Sf(Ap aV bJ bN bO cX dH Ih Im Pc) Yl(Af BN Fn Nj Qn Ra Ri Up Vs) To(fP Hf Jv Kz Mr Ng Of Pa Ri) Hp(Af bL BN Jv Uc Up Ur) Tv(Ih Im Iv Kp Kz Mr Pa Qb) Tr(Hf Kz Mk Ng Or Pa Pc) Xa(Af BN dH Kf Kp Vs) bX(Co Fn Ii Kg Ng Of Ur) Jv(aK aW bH cI Rz Vo) Ri(Rz Uc Uw Vh We Yd) fP(Ao aW bA bV Tn Ur) Bn(Gh Rz Uw Vh Wb) Tt(bH Hf Or Pa Pc) Iz(Db Hf Pa Qy tF) bO(bA Gb Si Va Tl) Ap(Fd Vw Wc Zq) Fn(aF cI dM Ur) Af(Yd Zq Tl) Ng(aF bJ cT) Tn(Hf Kz Pa) Ii(Is Kz No) Wb(Nk Up Vs) Of(cI Hu Vo) Co(cI cK) Cp(bA dM) Kd(Uc Vo) Rz(cZ dA) Oi(aK aU) Ur(aK bJ) Ux(cZ Nk) aV(Si Va) bN(Ye Tl) tF(Ao Vo) DlbJ FcFw FyKg NoKf JeWc WeQy KidE PaaW} Oz{Ps(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp Du Ed Em Eq Et Ez Fa Fb Fc Fd Fi Fn FR Fw Fy Gb Gc Gd Gh Gl Gn Gp Gz Ha Hb Hc Hf Hl Ho Hp Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kr Ks Kx Ky Kz Ld Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Nj Nk Nl Nm Nn No Nq Nr Ns Nt Nu Nv Nw Nx Ny Oa Oe Of Og Oh Oi Ok Om On Op Or Ou Ow Oy Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tv Tz Ua Ub Uc Ud Ue Uf Ug Uh Uk Ul Um Un Uo Up Ur Us Ut Uu Uv Uw Ux Uy Uz Va Vb Vc Vh Vi Vj Vo Vp Vq Vs Vt Vw Vz Wb Wc Wd We Wf Wg Wh Yd Yl Zq Zw Zx Ye Tm Tl Xa Wm Tj Ti Th) Xa(Af Aj aM Ap aW BC bF Bg bH bJ BN bO bQ bS bU bZ cA cC cE cF cH cJ cL cP cR cS CX cZ dA Db dD De Dg dH dI dL dN Dp Du Ez Fi Fn Fr Fy Gd Hc Ih Im Io Is Iz Jd Je Jf Ji Jl Jr Ju Jv Jy Kc Kd Ki Kl Ks Kz Lh Li Lu Lv Mj Mq Mr Mt Mu Mv Mw My Nb Nc Nj Nk Nl Nu Nw Nx Oe Og Oi On Op Or Ou Oy Pi Qa Qe Ql Qm Qn Qw Qy Rb Ri Rm Rv Sf Sh Tn Ua Un Us Ut Uu Uv Vi Vp Vq Vz Wb We Zx Ye) Wb(aA aJ aP aS Ax BA bC bQ bV bZ cF Co cP CS CT Cu cW dF dG Dk dM dN Ez FR Fy Hc Hu Ih Ij Im Ir Is Iz Jd Je Ji Jk Jl Jn Jp Jr Js Jv Jy Kk Kn Kx Ky Ld Lh Lu Lv Lx Mi Mj Mk Mn Mq Mr Mt Mu Mv Mw Mz Nb Nd Nj Nk Nn No Nr Nt Nu Nv Nw Ny Oh Ok Om On Or Ou Ow Pe Pf Pg Pi Po Qa Qb Qd Qe Qt Qv Qw Qx Qy Ra Rb Rf Ri Rm Ru Sr Tn Ua Ud Ut Uv Va Vi Vq Wd Zw) Vi(Af aW aX bA BC bH bL Bn bU cN cP cS cT Cx cZ De dM dN Ez Fb Fr Fy Hu Ih Ik Im Is Iu Iz Jd Je Jf Ji Jk Jl Jr Ju Jv Kc Ki Lh Lv Mi Mj Mp Mq Mr Mt Mu Mw Nj Nk Nn Nu Nw Or Ou Ow Oy Pi Qa Qb Qe Ql Qn Qy Rf Ri Rm Rv Sf Sh Sr Tn Tz Ua Ud Un Us Vq Vz) Hp(aX BA bC bF Bg bR bU bZ cF cS Cx Ez Fr Fy Hc Im Ir Is Iz Jd Jk Jl Jp Jr Jv Ki Kk Lh Lu Lv Lx Ma Mj Mr Mt Mu Mv Mw My Mz Nd Nj Nk Nl Nn Nr Nw Oe Og Oi Ok On Or Ou Pe Pf Pg Qa Qd Qe Qh Qn Qy Rb Ri Tn Ua Uv Va Vq Ye) Sh(Ba Bg bQ bZ Co cS Cu Dk Ez Fb FR Fy Hc Hu Ih Ij Im Is Iz Jd Jk Jl Jn Jp Jr Jy Lh Lv Mn Mr Mt Mu Mv Mw My Mz Nb Nd Nj Nn No Nq Nr Nt Nu Nv Nx Ny Ok Om On Or Ou Pf Ph Pi Qa Qd Qe Ql Qy Rb St Tn Ua Ut Uw Vw Wd Zx) Vz(Ba bQ bZ cF Co cS Cu Ez Fb FR Fw Fy Hc Hu Ih Im Is Iz Jd Jk Jl Jn Jp Jr Jy Lh Lv Ma Mj Mr Mt Mu Mv Mw Mz Nb Nd Nj Nn No Nq Nr Nu Oh Ok On Ow Pe Pf Pi Qa Qe Ql Qt Qy Rf Ri Rm Tn Ua Ut Vq Vw) Sf(Ba bQ cS Cu Dk Ez Fr Fy Hc Hu Ih Ij Im Is Iz Jd Ji Jk Jl Jn Jp Jr Jy Kk Lh Lv Mr Mt Mu Mv Mw Mz Nb Nd Nj Nn No Nq Nr Nt Nu Nv Nw Ny Ok On Or Pf Pg Pi Qa Qd Qe Ql Qy Rb Rm St Tn Ua Un Ut Vq) Rv(aM Ba bQ cS Ct Cu dF Dk Ez Fr Fy Ih Im Is Iv Iz Jd Jk Jl Jn Jp Jr Jy Kk Lh Lv Mj Mr Mt Mu Mv Mw Mz Nb Nj Nn No Nr Nv Nw Ny Oh Ok On Or Ou Ow Pf Pi Qa Qd Qe Qy Rm Tn Ut Uw Vq) Wd(AF aW bJ BN bO bR bS bU cA CX Dp Ed Ez Fb Fy Ih Im Is Jd Jl Jn Jr Jv Kc Mr Mt Nj Nr Nu Ow Pd Pi Pk Qa Qb Qe Ql Qm Qn Qy Rf Ri Rm St Tz Us Ut Uu Vq Wf Ye Th) Jl(aW dN dR Du eF Eq Fc Fd Fi Gb Gc Gh gL gP Hl Ho Lp Lt Op Rt Ru Rx Ry Rz Si Sj Tn To Tv Uw Ux Uy Uz Va Vb Vc Vh Vj Vw Wc We Wf Wg Wh Yd Yl Zq Zw Zx Ye Tm Tl Ti Th) Jd(dM dN Du Eq Fc Fd Fi Gb Gc Gh gL Gn Hl Ho In Lp Lt Ms Og Oi Op Rt Ru Rx Ry Rz Si Sj Uw Ux Uy Uz Va Vb Vc Vh Vj Vw Wc We Wf Wg Wh Yd Yl Zq Zw Zx Ye Tm Tl Th) Mr(dN Du Eq Fc Fd Fi Gb Gh gL Hl Ho Lp Lt Op Rt Ru Rx Ry Rz Si Sj Tn Uw Ux Uy Uz Va Vb Vc Vh Vj Vw Wc We Wf Wg Wh Yd Yl Zq Zw Zx Ye Tm Tl Ti Th) Qa(Du Eq Fc Fd Fi Gb Gc Gh gL Gn Hl Ho Lp Lt Op Rt Ru Rx Ry Rz Si Sj Uw Ux Uy Uz Va Vb Vc Vh Vj Vw Wc We Wf Wg Wh Yd Yl Zq Zw Zx Ye Tm Tl Ti Th) Ez(Du Eq Fc Fd Fi Gb Gc Gh Gn Hl Ho Lp Lt Op Rt Ru Rx Ry Rz Si Sj Uw Ux Uy Uz Va Vb Vc Vh Vj Vw Wc We Wf Wg Wh Yd Yl Zq Zw Zx Ye Tm Tl) Mt(Du Eq Fc Fd Fi Gb Gh Hl Ho Lp Lt Op Rt Ru Rx Ry Rz Si Sj Uw Ux Uy Uz Va Vb Vc Vh Vj Vw Wc We Wf Wg Wh Yd Yl Zq Zw Zx Ye Tm Ti Th) Vw(Af Ap bC bQ cS Cx Dg Dp Ed Hu Ih Im Is Jk Jr Jv Ki Kl Lh Mj Mu Mw Mz Nb Nd Nj Nk Nl Nu Nw Og On Or Qb Qe Ql Qn Qy Ri Uv Vq Yl) Is(dN Du Eq Fc Fd Fi Gb Gc Gh Gn Hl Ho Lt Op Rt Ru Rx Si Sj Tv Uw Uy Uz Va Vc Vh Vj Wc We Wg Wh Yd Yl Zq Zw Zx Ye Tm Ti Th) Jr(dN Du Eq Fc Fd Fi Gb Gc Gh Gn Hl Ho Lp Lt Op Rt Ru Rx Ry Rz Si Sj Ur Uw Ux Uy Uz Va Vb Vc Vh Vj Wf Wh Yl Zx Ye Tm Ti Th) Im(dN Du Eq Fc Fd Fi Gb Gc Gh Gn Hl Ho Lp Lt Op Rt Ru Rx Ry Si Sj Uw Uy Uz Va Vb Vc Vh Vj Wc Wf Wg Yd Yl Zw Zx Ye Tm Tl) Qy(Du Fc Fi Gb Gc Gh Gn Hl Lp Lt Op Rt Ru Rx Ry Rz Uw Ux Uy Uz Va Vb Vc Vh Wc We Wf Wg Wh Yd Yl Zq Zw Ye Tm Tl) Nj(Du Eq Fc Fd Fi Gb Gh Hl Ho Lp Lt Op Rt Ru Rx Ry Rz Si Sj Uw Ux Uy Uz Va Vb Vh Yl Zq Zw Zx Ye Tm Tl Ti Th) dN(bF bQ bR bZ Db dI Ed Fy gL Gp Hf Hu In Jn Jy Lu Lv Ly Ma Me Mu Nq Nr Og Ql Qm Ri Tn Uk Us Vp Zx Th) Yl(bN bQ bZ cS Cu Cx Fb Fr Fy Iz Jk Jn Lh Ma Mw Nb Nn No Nr Nt Nu Nw On Ow Pe Pf Pi Qe Ql Tn Ut Vq) Tn(aA Aj Cv dI Em Eq Fc Fi Gl Ji Jq Jv Jy Kg Kj Lw Mu Ng No Nw Qd Rf Ri Sr St Un Us Vh Vq We) Vq(aW dM Fc Fi Gc Gh Gn Lp Lt Ru Rx Ry To Tv Uw Uy Uz Va Vb Vj We Wg Wh Zq Zx Ye Th) Ye(Ba bC Ct Fy Hu Iz Jh Jk Jy Lh Mu Mv Mw Nb Nk On Or Pi Qe Ql Rf Rm St Ua) gL(aA Ed Fa Jy Ke Me Mq Mw No Nw Ny Pe Po Qd Qe Sr St Un Vt) Th(Fr Ji Lh Lx Mq Mu Mw Nk Nn Nw Ny On Ou Ow Qd Qe Un) Fc(bZ cS Fr Fy Jk Ma Mu Mv Mw Mz Nb Nn Nw Pf Qe Ri) Fi(Dk Fy Jk Lh Mu Mw Mz Nb Nn Nr Nw On Or Pi Qe Ut) Cx(Gb Gn Hl Lp Rt Ry Uw Uz Vb Vh Wf Wg Wh Zq Tl) Mu(Du Hl Ru Rx Ry Si Sj Uw Va Vh Wf Zw Tm) Un(aW dR eF Gn In Lu Ms Og Si Tr Tt Tv Va) Qe(Du Gc Gn Hl Lt Si Uy Va Vb Vh Wh Ti) Pi(Fd Gc Gn Ho Op Rt Rx Si Uy Va We Zx) eF(aA Aj Jy Mw No Nw Ny Pe Qd Sr St) Fy(Aj bH dM Du Gn Hl Qv Rt Vh Yd) Zx(BC Ih Iv Je Jv Nu Ow Rf Ri) Or(Gh Gn Ho Lt Op Ru Vj Zq Zw Tm) Eq(bQ Fr Iz Jk Jp Jy Nn On Ua) Ri(Fd Ho No Ry Uw Vb Wh Zq Zw) Du(Bc Ih Jn Nk On Ow Pe) Mw(Lt Op Rx Si Zq Zw Tm) Wh(Af cX Dp Ih Jn Ql Qn)

Nf Pa Qn Sf Sh Up Uu Uv Vo Vz) Jt(Ad As bQ Cu Dc Fy Ij Kn Lh Mt Mz Om On Pi Ra Rb Tn Up Uz Vi Vp Wg) Lv(Af Aj Bb bN Hc Hf Kr
Nc Nf Up Uu Vo) Oi(bN Cx dE dH dI Dp Fn Hf Jd Je Nc Qn) Mu(Af Aj Bg bN Cx De Ed Kj Kr Nf Uu) Ye(aE bN bR bS cA cX Fi Qm Qn Rb
Vz) Uu(Bg bQ Fr Jd Lh Lu Mv Nq Ou Rb) Ed(cX Dl Fa Fw Hu Il Qn Qy Tz) Vi(Aj De Fn Kf Ki Kj Kr Qn Sh) bN(aR cX Mi Mr Ng Rb Tz Ud)
Nc(bR Fy Jr Mw Mz On Pi) Tn(Aj De Eq Kj Kr Pa Up) bQ(Af Aj Dp Hc Kr Pa Sh) Cx(bA Je Lu Mi Mr Ud) Rb(Af Aj Kf Ko Va Wc) Dp(lu Jl
Lu Nb Va) Ez(Hc Kl Ng Nu Pc) Fr(Af Dg Hc Nf Pa) Mr(Af Bb bS cX Qn) Mt(Hc Kf Ko Pa Yl) Ii(Hl In Ji Mz Uv) Bb(bR Fy Uv) Bg(Eq Nf Sh)
Dg(bZ Ma Pf) Mz(Kf Ko Qn) Kr(Nx On Ou) Pc(Cs Ld Nn) Aj(Nx Ut) Dl(Nr Ra) Eq(bZ Ma) Lu(Hc Kl) Nf(bF Ou) Lh(Af Fi) On(Pa Up) ChSh
DeUt NubU MaVz TzKi IoaA RaYl JldA KjNx} Sr{gL(aA Ad AF aH Aj Al aM Ao Ap Ar As aW aZ Bb BC bE Bg bH bJ bL bM BN BO bR bS bV bX cA cF Ch cM cN Co CQ Ct cW CX Db dD De Dg dI dK Dl Ed Fa Fb fP Gp Hc Hf Hq Hu Hx Ic Ii Ik Il Iq Iu Iv Iz Jd Jf Jh Jj Jk Jl Jo Jr Js Jt Ju Jv Jy Kc Kd Kg Ki Kj Kl Ko Kr Kx Ky Kz Lu Ly Md Me Mg Mq Mr Ms Mt Mu Mv Mw My Na Nb Nc Nd Nf Ng Nh Nj Nk Nl Nn Ns Nv Nx Ny Oc Of Oi Ow Pa Pb Pc Pk Po Pz Qa Qc Qd Qe Qh Ql Qn Qt Qu Qv Qy Qz Rb Rg Ri Rj Rm Ss Tz Ue Ug Uh Uk Um Un Uo Ur Us Uu Uv Vo Vt) dR(aA Ad Af aH aI Aj Al aM Ao aZ BA Bb bE bH bJ bL BN BO bR bU bV bW bX Ch cI cM cN Co CQ cR CT cW Cx cZ dA Db Dd DE dF dI dJ dK Ed Ez Fa Fb fP Gp Hc Hf Hq Ic Ii Ik Iq Iu Iv Jd Jf Jh Ji Jj Jk Jl Jm Jo Jr Jt Ju Jv Jy Kd Kg Ki Kj Ko Kr Kx Ky Kz Lu Lw Ly Ma Me Mg Mq Mr Ms Mt Mu Mw My Nb Nc Nd Nf Ng Nh Nj Nk Nl Nn Ns Nt Nx Ny Oe Oi Pa Pb Pc Pk Po Pz Qa Qc Qe Qh Ql Qn Qt Qu Qv Qw Qy Qz Rb Rc Rf Rg Ri Rj Rm St Tz Uc Ue Ug Uk Um Uo Ur Us Uu Vo) eF(aA Ad AF aH Aj aK Al aM Ao Ap As aU aZ Bb Bc bG bJ bL bM BN BO bR bV bX cC Ch cI cJ cM Co CQ Cs Ct cW CX DB dC DE Dg dH dI Dl Ed Fa Fn fP Fw Gp Hc Hf Hq Hu Ic Ii Ik Iq Iu Iv Iz Jf Jg Jh Jj Jk Jl Jo Jr Jt Ju Jv Jy Kd Kf Kg Ki Kj Kl Ko Kr Kx Ky Kz Lu Ly Me Mg Mk Mq Mr Ms Mv Mw My Nc Nd Ne Nf Ng Nh Nj Nk Nl Ns Nx Ny Oa Oe Of Oi Pa Pb Pc Pk Po Pz Qa Qe Qg Qh Ql Qn Qt Qu Qv Qz Rb Rg Ri Rj Rm Ss St Tz Ue Ug Uk Um Uo Up Ur Us Uu Uv Vo Vt) gP(aA Af Aj Al aM aP aZ BA Bb bE bH bJ bL bM BN BO bQ bR bV bX bZ Ch cI cN Co CQ cR cT Cx cZ dA dB dE Dl Ed Ez Fa Fb Gp Hc Hf Hx Ic Ii Ik Iq Iu Iv Jd Jh Jj Jl Jm Jo Jr Jt Ju Jv Jy Kd Kg Ki Kj Ko Kr Kx Ky Kz Lu Ly Me Mg Mq Mr Ms Mu Mv Mw Nb Nc Nd Nf Ng Nj Nk Nl Nn Ns Nx Ny Oe Oi Pa Pb Pc Pk Po Pz Qa Qc Qe Qh Ql Qn Qt Qv Qw Qy Rb Rf Rg Rh Ri Rj Rm St To Tz Ue Ug Uk Um Uo Ur Us Uu Vo) fP(aA Aj aW bV dM Iu Jj Jv Kj Lu Oi Qv To Ug Ur Uu) Kj(Bg bZ Ch eC Ef Jy Lv Ma Tn tF) tF(aA Aj aW Iu Jj Kg Ue Uu Vo) Ef(Aj Lu Oi Qv Ue Ug Uu) Dp(In Lu Oi Qv Va Vi) eC(aK bO cI dI Ii Uu) Ed(Fw In Jd Ki Ri) Uu(Bg Hu Jd Jy) Fp(In Lu Oi) Sh(bF Jy Vi) bO(In Lu Oi) Cx(Fi Yl) Nj(Wb Yl) Ii(Is Jr) Rb(Sf Ye) dI(bR Ma) EqJy LyKi MuOi TrPc TnHc} Sh{Jy(aC Ad aE AF aG Aj Ar Ax aZ BC bJ bL BN bR bU bX cN Cs Cx dB Dc DE dF dG Dp Du Ed Eq Et Ez Fa Fd Fn Fw Fy Gb Gl Ha Hb Hc Hp Hw Ib Ih Ii Ij Ik In Ir Is It Iu Iz Jd Jf Ji Jk Jl Jm Jn Jp Jr Js Ju Kc Ke Kf Kn Ko Ks Kx Kz Ld Lh Li Lj Mb Mc Mq Mr Ms Mt Mv Mw Nf Ng Nm Nn Nr Nt Nu Nv Nw Nx Ny Oa Oh Ok Om On Ow Pa Pb Pc Pe Ph Pi Pj Pk Po Qa Qb Qc Qd Qe Qh Ql Qm Qy Rf Ri Rm Sf St To Uf Uh Un Us Ut Uu Uv Vi Vw Vz Wb Wf Yl Zq Zw Ye Tm Xa Tj Th) Mt(aA Af AJ AP aU Bb bF BG bH bJ bL bM bN bO bR bU bW bZ cC CH Cx DD dE Dg dH dL Du Ed Ez Fi Fn Fr Gc Gz Hc Ic Ii Il In Jd Jl Jn Jp Jt Ju Kc Kd Ke Kl Ks Li Lt Lu Ma Mr Mu Mw Mz Nc Nd Ne Nf Nj Nk Nl Nn Nq Nu Nx Ny Oe On Or Pa Pb Pc Pi Pk Ql Qm Qv Qy Rb Rg Ri Si St Tn To Uf Uh Uo Us Ut Vh Vi Vs Vz Wb Wc Yd Yl Ye Tm Xa) On(Af aK Ap aU aV Bg bH bJ bM BN bO bR cC Ch CX dA dD De dH dI dL Dp Du Fn Hc Ii Je Kc Ki Ko Lx Mr Mu Mw Nc Nf Ng Nj Nk Nu Oe Pa Pb Pc Ql Qy Rb Ri To Up Us Uu Vs Vz Yd Yl Zq Ye Tm Xa) Vi(aX Bc bH bL Bn bZ cZ De dM Dp Ed Ez Fb Fi Fn Hb Ih Is Jd Jn Kc Kx Ky Kz Lj Mi Mr Mu Mw Nf Nk Nn Nr Nu Ny Ow Pa Pb Qa Qb Qe Ql Qm Qy Ri St To Uh Up Us Zq Xa Th) Ql(bF Bg bQ bZ Ch Il Jd Jp Ma Mr Mu Mw Mz Nn Nq Pf Rb Ri Tn Xa) Nn(aV bO dA dH Dp Jd Je Mr Mw Nj Or Pc Pi Qy Ri Wb) Mu(Ar bN Cs Cx De Fy It Kc Ld Mw Nf Pb Pf Ri Us Xa) Bg(Ih Jd Jn Mr Mw Nr Nu Ny Pe Qa St Un Xa) Nj(Is Jd Ji Jn Mw Ny Ow Qa Qe Rm St Ut Xa) bQ(dH Ih Jd Jn Mw Nr Qe Qm Qy St Wb Xa) Mw(aC bF bN Ch Cx Kc Ks Qz Ri Ye) Mr(bF Ch Cx Ez Il Nx Qy Ri Xa) Qa(bO Ch dL Du Nk Pb Pc Rb Ri) Jd(Ap bW dH Ed Kc Qv Qz Wh Ye) Ut(Af bN bO Cx Kc Nk Pb Ri Us) Xa(bF bZ Ch Jl Ma Mv Or Rb) Nq(Ed Eq In Kz Nf Pi Pk) Nu(bF Ch Ez Is Mv Nx Tn) Pb(Cu Dk Jn Mz Ny Om Tn) Nk(Is Jl Ny Pi Qe St) Ri(Jn Nr Ny Qe Rm St) Tn(Je Nf Qy Us Wb) bZ(Jn Ny Pi Qy Un) Ch(Ih Jn Nr Ny) Jl(bO dH Dp Kc) Jp(bO dA Kc Nf) Mv(Dp Kc Pk) Nl(Is Jn Qe) Qy(bB dF fR) Or(Cx Ra Th) Pf(Je Pa Pc) Ma(Je Ny) FybH NrbO IqIs RbSt dHfR} Jl{Dp(Aj aW Du Eq Fc Fd Fi Gb Gc Gh Gn Hl Ho Hp Jj Lp Lt Op Qv Rt Ru Rx Ry Rz Sf Si Sj Tn To Tr Ur Uw Ux Uy Uz Va Vb Vc Vh Vi Vj Vw Vz Wb Wc We Wf Wg Wh Yd Yl Zq Zw Zx Ye Tm Tl Xa) Us(aW bA bI dM dR Du Ed eF Em Fc Gb Gc Gh gL Gn gP Hl Hp Ih Iu Jd Jn Ki Oi Qz Ri Rt Ru Rx Ry Rz Tn To Tt Tv Uw Uy Uz Vb Vh Vi Vw Vz Wb Wc We Wf Wg Yl Zq Zw Ye Tm Tl Xa Ti) Kc(Du Eq Fc Fd Fi Gb Gc Gh Gn Hl Ho Hp Lp Lt Op Rt Ru Rx Ry Rz Sf Si Sj Uw Ux Uy Uz Va Vb Vc Vh Vi Vj Vw Vz Wb Wc Wd We Wf Wg Wh Yd Yl Zq Zw Zx Ye Tm Tl Xa) Vz(Aj aV aW Ax bJ bN bR bU Cs Cx cZ dA DE dH Ed Fn Fy Hv Jn Jr Jv Jy Kr Ld Mh Mr Mt Nc Nj Nk Nn Nr Nu Oh Ow Pb Pf Qe Ql Qn Ra Rf Ri Uu Ye Xa Wm) Nk(dR Du eF Eq Fc Fi Gh gL gP Hp Lt Rx Ry Rz Sf Si Sj To Tv Ux Vc Vj Wb Wf Yd Yl Zx Ye Tm Tl Xa Ti Th) dR(aA Aj Al Ch Co Db Ed Hf Jj Kj Kr Kx Kz Lu Ly Me Mq Nc Ng Nj Nl Oe Oi Qv Rg Ri Uu) gP(aA Aj bR Ch Db Hf Jj Jv Jy Kr Kx Kz Ly Me Mq Mr Nc Nf Nj Nl Oe Oi Qv Rg Ri Ur Uu) gL(aA Af Aj Al Ao Ch Ed Hc Kl Kr Kx Kz Ly Me Mg Mq Nc Nf Ng Nl Oi Pa Rg Ri Uu) eF(aA Af Aj bN Ch Ed Hc Jj Kj Kl Kr Kz Ly Me Mg Mq Nc Nf Nl Oi Pa Rb Ri Uu) Yl(Af Aj aW BN bR bX CX dA dE dH Fn Nc Nj Pb Ql Qn Ri Uu Vp) Ye(aI aV bO Cx cZ dA dH dI Hp Je Nf Ql Qy Rb Ri Xa) Uu(Ba bH bO dI dM Ef Hu Jd Jy Ly Mu Ri Tn To Vb Xa) Cx(Du Eq Gn Hl Rt Rx Sf Uz Vh Vi Wg Zq Tl Xa) Fp(aA Aj aW Gd In Jj Ng Oi Qv To) Me(aW cI dM Tn To Tr Tt Tv) dA(Fi Lp Si Sj Va Wb Wc Tm) Ly(aW cI Tn To Tv Wm) Hc(aW Tn To Tr Tt Tv) bO(bA Gh Va Tm Tl Xa) Ng(Hu Nf Nn Po Wm) Kr(Jd Ow Tn To Tv) Pb(Hl Uz Vb Wg Xa) dH(Fc Sf Yd Zq Xa) Ri(aW To Tm Th) Ex(aW Tn Tv) Zq(Af bN Qn) dI(bR cA Ed) Aj(Ef Tn) Nc(Ti Th) Nf(aW To) Yd(Ql Rb) Sf(aV Rb) Je(Rz Wf) Jj(Ef fP) Xa(Af Qn) Pc(Tr Tt) ApVw BaKl EdOe EqJy FcFi NjWb JdKj VaaV bVfP} eF{Hc(aA AJ aP Ax Ba Bc bV Cs Cu Ed Et Fa Fr Fw GL Id Ir Is Iv Jd Jh Ji Jj Jn Jr Jy Ke Kx Ky Ld Lh Lj Lw Lx Ma Mq Mr Mt Mw Mz Nb Nn Nr Nt Nv Nw Ny Oa Oh Ok On Ow Pe Pf Pk Po Qa Qd Qe Ql Qy Rf Ri Rm St Tn Uh Un Ur Ut) Aj(Bc Cw Ed Fa Fp Ha Hf Hu Hw Ih Ij In Ir Is Iv Jd Jh Ji Jk Jn Kx Kz Ld Li Lj Ly Me Ml Mq Mr Mv Mw Nc Nf Nk Nn Nr Nt Ny Oa On Pc Pe Pi Pk Po Qa Qb Qd Qe Ql Qm Qt Ri St Ua Un Ut Uv Vt) Mq(aA aP bV cF Ch Co Cv Dc Fr gL Ik Is Ji Jj Jo Jq Jr Jv Jy Kd Ke Kg Kj Kr Kx Ky Lw Ly Mg Mr Ms Mu Mw My Mz Ng Nt Nw Ny Oe Oi Pc Pk Qa Qd Qe Qu Qv Rf Rg Ri St Un Ur Us Vt) aA(aC aM Bc bL bM cP cS cW Dp Ed Et Fa Fp Gl Io Ji Jv Kx Kz Lj Ly Me Mr Nf Nw Oa Oi Ow Pe Po Qa Qe Us Uu Uv Vt) Me(Ch Cs Cv Ed Fa Ji Jj Jy Ke Kg Lw Lx Mr Mw Nw Ny Oa On Qa Qd Qe Un Ur) Uu(Ba Dk Fa Hu Jd Jg Jh Jk Jy Mr Mw Nv Nw Ny On Qa Qd Ql St Ua Un Ut) Kj(Cs Cw Fa Ha Ij In Jh Mr Mw Nf Ny Oa On Pe Pi Pk Po Qa Qe Ql Un) Ed(Fa Jh Jy Ke Kr Kx Ly Mr Mu Mw Nk Nw Ny Oi Pc Rf Ri Un Us Vt) Kz(Cv Fr Ji Jj Jy Ke Lw Lx Mw Nw Ny On Qa Qd Qe St Un Ut) Ny(Af Bb bL bN Ch Co Iz Jv Kl Kr Ly Nf Ng Pa Ri Us) Nf(Ji Jj Jo Jy Ke Kg Lw Mw Nw On Qd St Un Ur) Us(Fa Ji Mr Mw Nw On Po Qa Qd Qe Ql St Un) Ly(Fa Jf Ji Ki Mr Mw Nw On Ql St Un) Qa(Ch Cq Jj Jo Kg Kr Nc Nk Oi Ri Ur) Ch(Jd Jh Mr Mv Mw Po Qy St) Mw(Co Hu Iz Jv My Nc Rg) Mr(Kr Kx Mg Qe Rg Ri) Kg(Fa Ha Oa Pe Po Qe) St(Nc Nj Nl Oi Pa) Kr(Ji Qd Qe Un) Fa(Co Pc Rg) Af(Ji On) Mg(Nn Ql) Oa(Jj Jo) Pe(Co Pa) InUr QebM} Vz{Mt(Ad Af aH Aj Ao Ap aW aX BA Bb bC bH bI bL BN bR bU cC cF Co cP cS cT CX dA dD DE Dg dI Dl Dp Ed Eq Ez Fi Fn Fy Gb Hb Hc Hu Ii In Jd Je Jf Jg Jh Jo Jt Ju Jv Jy Kc Kd Ke Kg Ki Kj Kl Ko Kr Ld Lj Lt Lu Me Mf Mg Mi Mr Mu My Nc Nd Ne Nf Ng Nh Nj Nk Nl Nn Nr Nu Oe Oh Oi Om Or Pa Pb Pc Pj Ql Qm Qn Qu Qz Ra Rc Ri Sf Si Sj To Ud Uh Up Us Uu Va Vc Vh Vq Vt Wb Wc Wf Wh Yd Zq Zx Ye Tm Xa Wm Th) Fy(aA Af Aj Ap bA Bb bH bR Cx dD Du Ed Fb Fn Fr In Je Jf Jn Jy Kd Kg Ki

Figure 7 Continued

Yd Ye Tm Ti) To(Hc Kg Kj Kr Me Nc Ng Nj Nk Pc Us) Ed(aW Cq dI Fi Ii In Kj Lu Oi Qv) Nk(Sf Si Va Wc Yd Ye Ti Th) Nc(aW Eq Hl Hp Sf
Ye Tm) Kg(aW bR Ly Tn Tv Uv) Kj(bV Ly Ms Nr Tn tF) Nj(Eq Sf Yd Ye Tm) Hc(Gc Jj Lu Tv Uy) Je(Si Sj Va Wc Ye) Uu(Ba bV Hu Lu)
dI(bR Oi Qv Ye) Af(Sf Vj Ye) Me(aW dM Tv) Ii(bR Kr Un) Jj(Dp Fp Kr) Va(bO dA Dp) Pc(Sf Tr Tt) PoNg FpOi NuSf LubR MraW YdQl
YebH} Mt{Kc(Du Eq Fc Fd Fi Gh Ho Hp Lp Lt Rx Ry Rz Sf Si Uw Ux Uy Va Vb Vc Vh Vj Vw Wc Wd We Wf Wh Yd Zx Ye Tm) Sf(Af Ap bN bO Hc Hf Nf Pa Pb Pc Us) Tm(Af Ap Bb Dg Kj Nl Pa Pb Us) Fi(Af Dg Ed Nf Pb Pc Us) Si(aV bO Dp Hc Nf Pa Pc) Eq(Ap bZ Dg Fn Nj Pb) Ye(Nf Pa Pb Qy Us) Ap(Fd Ho Lt Wc) Hl(Ii Jt Kf Nm) Hc(Ho Va Wc Wh) We(Pa Pb Pc Qy) Af(Ho Lt Tl) Us(Gh Lt Ry) Pa(Hp Rx Wh) Dg(Fd Lt) Dp(Va Wc) Nf(Du Vh) Wg(Jt Kf) Uz(Jt Kf) bO(Va Wc) YdPb WhQy LdVh} Qe{Nk(Du Eq Fc Fd Fi Gb Gc Gh Gn Hl Ho Hp Lp Lt Op Rt Ru Rx Ry Rz Sf Si Sj Tn To Tv Uw Ux Uy Uz Va Vb Vc Vh Vj Vw Wc Wd We Wf Wg Wh Yd Zq Zw Zx Ye Tm Tl Ti Th) Nj(Du Eq Fi Hl Hp Lt Rz Sf Sj Ux Yd Ye Tm Ti Th) Jj(dR Ef Fp gP Io Jr Lv Nf Ng) Tn(Aj Hc Kg Kj Kr Us) Me(Aj aW dM Tv) Th(bO Nc Nl) Mr(aW Du Ti) Kr(dR gP Iu) Aj(Ef Lv) Nl(Hp Ti) In(Kz Nf) Ye(bO Jc) Va(bO Dp) Pc(Tr Tt) NnNg LvKj WdKc bRdI} Mw{Kc(Fc Fi Gb Gc Gh Hp Lp Lt Op Ru Rx Ry Rz Sf Si Sj Uw Ux Uz Vc Vj Vw Wg Wh Yd Zq Zw Zx Ye Tm Tl) dR(Aj Ch Ed Iz Jj Jv Kj Kz Ly Ms My Nc Oi Ua Us Uu) gP(Aj Ch Ed Hu Iz Jv Kj Ly Mq My Oi Us Uu) Ye(bN bU Cx Dp Ju Jv Mr Nc Nk Nl Ql Sf) Tn(Aj Ed Hc Iz Jv Kj Us Uu) Nk(Lt Sj Ti Th) Dp(Sf Va Wc) Ng(Lv Tr Tt) Tr(Hc Pc) Va(aV bO) CxWd DuNj EdTv FpJj TtPc RxPb} Qy{Ye(Ap cP Cs cT Ed Jv Kc Ld Lu Me Mq Nf Nk Nn Oa Oh Pc Qv Qx Ra Rf Va Zw) Ed(bA cT dM Fi Ms Oe Oi Qv Rx Zw Tm Ti) Ld(Du Fd Fi Ho Lt Rz Vh Wh Tm) Kc(Hl Rt Uw Uz Vh Wc Wg Tl) Va(aV bO Dp Hc Mr Rb Tm) Qv(Eq Hc Ly Nf Tm) Pb(Gn Hl Rt Uz Wg) Ng(bA cT Tr Tt) Eq(bQ bZ Ma) Tn(Aj Hc Iz) Wh(bQ Cs Ra) bA(Ct Hc Ib) Ap(Zw Tm) Tr(Hc Pc) Jr(Kg Kj) DuNj FiNr LydM MsUn MzWe UuUw} Dp{Va(Ba bQ Cu Dk Ez fR Ih Ij Iz Jh Jn Jp Lh Mr Mv Mz Nb Nj Nn Nq Nr Nt Nu Nv Nw Ny Oa Om Pe Ql Qm Rm St Ut Vw Wd Wh) Jj(Bg bZ Il Jp Lu Lv Ma Mv Nn Nr Pf Tn) Nb(Fd Fi Gb Lp Si Uy Wc Wh Ye Tm) Lu(Fa Jn Jr Nw Pe Po Rf Un) Mr(Fi Lp Si Uy Wc) Nn(Aj Gd Oi Ye) Mv(Sf Wc Ye Tm) Tn(Aj Kg) Si(Ij Nt) Oi(bV fR) YefR} Cx{Mr(Du Eq Fc Fd Fi Gb Gc Gh Gn Hl Ho Hp Lp Lt Op Rt Ru Rx Ry Rz Sf Si Sj Uw Ux Uy Uz Va Vb Vc Vh Vj Vw Wc Wd We Wf Wg Wh Yd Zq Zw Zx Ye Tm Tl) bA(Em Fc Gc Gh Gn Vc Ye Tm) Je(Uw Va Vh Wc Zw) Jr(Kg Si Wc Wh) Mi(Wc Zq) Sf(Kk Ny) Ql(Uy Va) EdWh EmcT FiNy GnfR LuUn JqUr UwPb} Ed{Oi(Ba Dk Et Fb Hu Jn Jr Nn Nr Om Ql Rf Un) Un(bZ Fn Fw In Lu Lv Ms Oc Tn Ur) Lv(bJ cN dI dM Ki Mq Ur) Nk(Tn Zq Zw Ti Th) Hu(bA Lx Ms Oe Rf) dI(Et Jp Ma Pf Tn) Ez(Eq Fc Fi Lt) Oe(Dk Jr Ql) Ti(bH Nj) Lx(dR Nc) Tn(Nc Vq) Jh(dR gP) Uu(Ba Dk) tF(aP Fa) AdFi EfJj FnJq FwUw LuRf MrdM NjZq JpJv KjLh} Fp{Jj(Bg bZ Ch Et Jk Jm Jp Jq Jr Lv Ma Mn Mv Nn Nv Nw Ny Ok Om Pg Po Qd) Oi(Ba bV cE dI Dk Et Jg Jp Ky Lx Nn Nw Oh Ok Om Po Uf Un) Nw(In Io Lu Lv Ly Ma Ms Ng Ns) Gd(Bg bQ Ef Lv Mv Nn Ou Ut) Ng(Jg Lx Nn Om) Lv(Co Lx Mm) Lu(Cv Un) AjTn PoIn} Jr{Kj(Dk Ef Fb Hu Lv Ly Ma Mv Nc Nl Nr Oi Qz Ut) Lu(Aj bJ dI Hc Hf Kr Kz Us Uu) Af(Fi Rz Uz Vb We Wh Tm) Nc(Kg Tn To Tv) Hu(Aj Kg Uu) Ur(Hc Ly Pc) Ba(Kl Uu) Ng(Nn Om) In(Hc Kz) Jj(Lv Po) Pc(Tr Tt) dI(bR cA) DubN FnYd MedM MrHp NkTo SibO SfPb JeWc JfTm UsbH} Tn{Aj(Ba bJ Ef Et Ex Ez Gl Hc Hp Hu Jk Kz Mr Nc Nj Nk Nn Ny Pa Pc Qt Un) Hc(Ba bW Co Cv Ju Jv Kg Lw Mm Uf Ur Vq) Eq(Bn Ez Pb Up) Kc(Fc Hp Vw Zq) Us(Fi Hp Mr Zq) Nw(Kz Ly Nf) Me(Co Lw) Kj(Gl Un) BaUu FiPb NgbJ} Ng{Nn(Hu Ik Jn Lh Lu Lv Me Mq Mr Mv Ne Nf Nh Oi Om Pd Po Wm) Hu(cT Jg Lx Om Ow Rh Tr) Po(Et In Lv Ma Mv Om) Et(Lu Lv Mq Mv) Lv(Lx Nw Oh) Tr(Ez Jk Pc) Om(Mq Mv Nf) Ba(Kl Uu) Lx(Jm Me) FatF MaMq MpMv NfJg} Un{Lu(Aj bN bR bX Hc Jv Kj Kr Kz Ly Nc Nf Oi Us Uu) Kj(Bg bZ Ef Lv Ly Ma Ms tF) Uu(Ba bZ Ef In Lv Ou tF) Ma(Aj Ii Jo Jt Kg) bZ(Aj Jv Ko Us) In(Kz Nf) Pc(Tr Tt) cT(gP Ms) AjLv BaKl NnIi LyUr} Rb{bN(Sf Uw Uz Va Vb Vh Vw Wc Wd Wg Wh Zq Zw Ye Tm Tl) Sf(Cs Ld Nn Nu Oa Pe St) Wc(Ih Ld Pe Pi Pk) Si(Cs Jn Ld Pe) Fi(Ld Oa Pe) Ye(Ld Oa Pe) Va(Ih Ql St) Uu(Vw Wd) CsWh DuNj FaLy HoLd YdNw} dI{Nr(aM bR bS bU cA cF cW Ml Nc Nl Oi Uv) bR(bA cS dF Lh Lx Mq Mr Nn Pe Pf Po) bZ(aM Me Uv Vt) Fa(dR Ly tF) Lv(aM Cs Mq) Ma(Ml Uv Vt) Jn(aD Lu Oi) Pf(cA Ml Uv) Nn(cA Me) TrPc JpKz} Me{dM(bZ CS Et Jn Mn Nn Nr Nw Oh Pb Pf Qd) Lx(Ha Jq Js Mn Na Nc Ns Nx Of Pb Qz Tj) Jj(dR Ef gP tF) Nw(aW dR gP To) Nn(Aj Ye) NsMp QvtF JncN UrgP bHbZ} tF{Fa(Aj Ao Bg Ch Co Hc Hu Ik Iq Iu Iz Jj Jo Jv Kj Lu Ly My Oi Tz) Jj(Cs Ha In Kz Mq Nf Oa Pk) Kj(Ad Cw Ij Ok Om Pk) Aj(Nn Po) BaUu QvVt} Lv{Mq(Aj aK bH Co dA dM Jq Kj Mp Nw Oh Uu) Nf(Co Jj Lx Mm Nw Oh) Hp(bN Kc Us) Af(Vw Zq) Ba(Kl Uu) Lx(Nd Pa) Jj(Po Qb) Kj(Jn Ql) AjEz ExbN IoNw ZqKc VoVw} Nj{Qb(Du Gh Hp Lt Rx Ry Sf Sj Yc) Rm(Eq Lt Sf Ye) Fd(Kc Kz Nf) Du(Pb Pc) Eq(Ez St) Ih(Lt Sf) Zq(Ap Kc) Zw(Hf Pc) Kz(Op Rt) Ow(Sf Th) Uw(Hc Kc) NfRt HlPb HpNw TmPi} Ef{Gd(Ar Cs cT Fa Ld Lj Oa Pe Qx Ra) Aj(bM cW Fa Mq Nn Pf Po) Fa(Co Jo Kg Kj Oi Ue) Uu(Ba fR Jj Nw Uf) Kj(Cs Pe Po) Mq(Oi Qv) JjOa} Je{Ye(bN Mz Nr Pf Rm) Hl(bZ Ma Nn Pf) Zw(Bg bZ Ma Pb) Nr(Fi Si Wh) Wc(Mz Pi Rm) bN(Sj Uw Yd) Sf(Nn Pf) Ld(Op Yd) Rm(Si Va) EqMa SjPf} dR{Mq(aJ bV Jj Ky Nw Po Qd Rf) Jj(Ha Kz Mr Nf Po) Aj(Jh Ny Ut) Kz(Ke Lw Nw) Nf(Lw Nw) Jh(Ch Uu) CoPc FaRg LyNw JvNy} Ly{Ki(aP bA bQ bV dM Fa Ky Lx Nn Oh Pe Ql Qv) Nw(gP To Tv Wm) Kj(Lh Om) dM(Mr Ql) ExLu} Ye{Ez(Ap Hp Mr Nu Pc) Ql(bN Kc Mr Pc Pi) Hu(Kc Ld) Qw(bN Ld) NnJv NrHp NkRm NlJn LhbN RfPc UsUt} Uu{Ba(Bg In Jq Nr Oi Ou Pc) Mv(Gb Hp Ux Vw Zq) Hu(bV dF fR Ma) Dk(bH Th) EtLu JhgP OuVw} gP{Mq(Jj Jq Ky Nw Oi Qd Rf) Jj(Kz Nf Po) Aj(Jh Ut) Kz(Ke Nw) BoMl ChJh FaRg NfNw JvNy} Nk{Th(Lx Nw Ny Ou Ow St Tm) Rm(Hl Lt Sf Si Va Wc Tm) TiSt IhVa YdLh SfPi} Pc{Tt(cN Mr Nw Qd) Tr(Aj Gl Mr Qd) Nn(Fc Fi Sf) BaKl FiNr GnLd LuRf LxHp SfPf} Jn{Lu(Hc Ki Kr) Kj(Hu Ma Oi) Nc(Va Wc) Nl(Si Tm) Oi(Kg Ki) BaKl FiVq InHc VabO} Kc{Nb(Op Ux Vw Zq) Jp(Fc Hp Wd Wf) Mv(Eq Hp Zq) Ou(Hp Vw Zq) FcMz LuZq} Us{Ut(Eq Fi Hp Lt Ry Sf Tm Tl) Mz(Fc Hp) Ou(Rf Th) EmMv EtLu HpJp JkTm} Mr{Ez(Eq Fi Rz Ux) Ap(Vw Zq) Bb(Op Zq) AfVw FdPb FicX NnSf HpOe QlVa} Ma{Kj(Cw Hw Ij Jq Kr Pi Pk Up) Eq(Fb Hu Jk) Hc(bA dM)} Fi{Nr(dA Fc Hf Pa) Lh(bN bO Pb) Pb(Ny Ut) NfJp} Hc{Lu(Et Mn Nn Oh Rf) Nn(bA dM In) JpbA} Sf{Nn(aV bO) Nu(Ks Nx) Ny(Oe Pb) NrbO NlRm UtbN} Ez{Eq(bF Bg bZ Ch) Ap(Vw Zq Tm) VabO} Th{Ny(Ki Oe) NcNw NfOu QlVq} Hp{Pb(Jp Mz) AfbQ AjUt JvPf} bO{Lh(Si Va Wc) Va(Nr Nw)} Nf{Jp(Kj Rt) DuMz InNw} bN{Em(bA cT) ExbA ZqOu} Ba{Kl(Et Ki) ApZq} Lx{MbNa MqNd bHbR} Kj{Vw(Mz Nx) NrOu} Rf{Eq(Bg bZ) KrOu} Oi{NnMq NrKi ToNy} Pb{PoJj GnPi YdLh} Et{Lu(Aj Kl)} Si{dA(Mz Nw)} Ql{KiLt UybQ} AfZqbQ FddHfR MqInQb NlTmRm

Unconstrained panels with 2 analytes, where 1.0E-7 >= 'AUC p-value' > 0. Contains 1,651 panels of 87,101 total panels evaluated. : Ni(aD aE aG AJ aK aM aN aP aW Ax bA bH bI Bo bP bR bV bZ cI cN Cs cT cW dC dI dM dN DR Du Ed eF Em Eq Et Fa Fc Fd Fi Fp Fr Gb Gc Gd Gh gL Gn gP Hl Ho Hp Is Jd Ji Jl Jp Jr Ki Kj Kx Lp Lt Lx Mn Mp Mu Nn No Nw Oh Ok Om On Op Pf Po Ps Qa Qb Qe Qv Ri Rt Ru Rv Rx Ry Rz Sf Sh Si Sj Sr Tn To Tt Tv Ue Ug Un Uw Ux Uy Uz Va Vb Vc Vh Vi Vj Vw Vz Wb Wc Wd We Wf Wg Wh Yd Yl Zq Zw Zx Ye Tm Tl Xa Ti Th) Ji(aA Dr Ed Et Fp Fr Hq Hr Hu Hv Hw Hx Ih Ii Ij Ik Il Im In Io Ip Iq Ir Is It Iu Iv Jg Jh Jj Jl Jm Jn Jo Jp Jq Jr Js Jt Lh Li Lj Lu Lv Lw Lx Ly Lz Ma Mb Mc Md Me Mf Mg Mi Mj Mk Ml Mm Mn Mp Mq Mr Ms Mt Mu Mv Mw Mx My Mz Na Nb Nc Nd Ne Nf Ng Nh Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Us Wm) No(aA Ap Bb Bg bH bO bR cH Cx Db dI Dl dN Dp dR eC Ed EF Et FP Fr gL gP Hc Hf Hu Ih Ii Ik Im In Io Is Iu Jj Jl Jp Jr Jv Jy Kd Ki Kj Kl Kr Kz Lh Lj Lu Lv Lx Ly Ma Mb Me Mf Ml Mn Mp Mq Mr Ms Mu Mv Mw Nc Nd Ne Nf Ng Nh Nj Nl Nn Ns Nw Nx Oe Og Oh Oi Ok Om On Or Ou Oy Oz Pa Pb Pd Pf Pg Pj Po Qa Qb Qd Qe Qy Qz Ri Tn To Us Uu Yl Wm tF) Dr(aA AO Aw aX BA Bg bH bQ bZ cE cG Co Cp cS cT Cu dF dI Du Ef Ez Fb FR Fy Gl Gp Hu Im In Is Iz Jd Je Jk Jl Jp Jr Jy Ki Kk Kq Ky Lh Lu Lv Ma Mi Mj Mr Mt Mu Mv Mw My Nb Nj Nn Nq Nr Nu Nv Og Om

Figure 7 Continued

On Or Ou Oz Pb Pc Pf Ps Qa Qd Qe Ql Qt Qu Qw Qy Rb Rz St Tn Ua Ud Uf Ut Uw Ux Vp Vq Wd Wh Zx Xa Th) dN(aA An aO aZ BA bB bF BG bH bN BO bQ bR bU bV bZ cA cC cE CH cO cS cT Cu Cx dA DB dE dF DI dJ Dk dR eC Ed EF FP FR GL Gp Hu Im Is Jd Jl Jn Jr Jy Kq Kz Lu Lv Ly Ma Me Mr Mu Mv Nc Nf Nn Nq Nr Og Or Ou Oy Oz Pc Ps Qa Qe Ql Qw Qy Ri Wb tF) Mu(aA bA cT Du Ed Et Fa Fp Fr Hv Hw Hx Ih Ij Im Io Ir Is It Iv Jj Jk Jl Jn Jp Jq Jr Js Lh Li Lj Lu Lv Lx Lz Mb Me Mh Mj Ml Mn Mp Mq Mr Ms Mt Mw My Mz Na Nd Ne Nf Ng Nh Nj Nn Nq Nr Ns Nw Nx Ny Oe Of Og Oh Oi Ok Om On Oy Oz Pb Pd Pe Pf Pg Po Ps Qa Qb Qe Qv Wm) Qa(aA dl Du eF Et Fi Fp Fr Hu Ih li Il Im In Io Ip Iq Ir Is It Iu Jg Jj Jm Jo Jp Jq Jr Lu Lv Lw Lx Ly Ma Mb Me Mm Mn Mp,Mq Mr Ms Mw Nc Nd Ne Nf Ng Nh Nj Nk Nl Nn Ns Nw Ny Oe Og Oh Oi Ok Om On Oy Oz Pb Pf Po Pz Qb Qc Rv Sf Sh Vz Yl Ye) Im(aA dM Du Et Fc Fd Fi Fr Gc Gh Gn Hl Ho Hp Is Jj Jl Jq Jr Lp Lt Lu Lv Lw Lx Mm Mq Ne Ng Nh Nn Nw Og Oi Ok Om On Op Pf Po Qd Qe Rt Ru Rx Ry Rz Sf Sh Si Sj Uw Ux Uz Va Vc Vh Vi Vj Vz Wb Wc Wf Wg Yd Yl Zq Zx Ye Tm Tl Xa) Po(aA dl Ed Et Fp Fr Hu Ih li In Io Iq Is Iu Jg Jj Jl Jm Jo Jp Jq Jr Lj Lu Lv Lx Ly Ma Mb Me Mg Mm Mn Mq Mr Ms Mv Mw My Na Nc Ne Ng Nh Nk Nl Nn Ns Nw Ny Oe Of Og Oh Oi Ok Om On Oy Oz Pa Pb Pf Qd Qe Wb) Jl(aA Aj aW dl dM dR Ed eF Et l-p gL gP Ih li In Io Is Jj Jo Jr Kj Kr Lu Lv Ly Mb Me Mq Mr Ms Mw Nc Nd Nf Ng Nh Nk Nl Nn Ns Nw Og Oh Oi Oy Oz Pa Pb Pf Qe Ri Rv Sf Sh To Us Uu Vz Yl Ye Tm Xa Wm) Qe(aA Aj aW dl Et Fp Fr gL Ih li In Io Is Jj Jm Jr Kr Lu Lv Lx Ly Ma Mq Mr Ms Mw Nf Ng Nh Nn Ns Nw Og Oh Oi Om On Oy Oz Pb Pf Ri Vz Ti Th) Ed(aA aP BA bF bQ bV bZ Dk dM eF Et Fa Fr Fy gL Hu Is Jd Jn Jp Jq Jr Jy Kq Ky Lh Lv Lx Ma Nn Nw Oi Om On Pf Ps Qy Ri Sr Uf Un Vi Xa) Ps(Ap aR Bb bN bR bS cX dE Dl Fi Fy Je Kc Ki Ld Lv Mr Ms Nc Ng Nj Nk Nl Oe Og Oi Or Oy Oz Pb Qn Qy Qz Rb Ri Rv Tz Vq Vz Yl Ye Th) aA(aC aM bF bM bN bR bU cU CX Dp dR EF Et Ex FP Fr GL Is Jn Jr Lh Lv Ma Me Mm Mn Mv Nn Nw Og Oh Ok Om On Pf Pg Qb Ri tF) Lx(Ap bO FP Hc Hw Ih Ij Ik Ir It Iu Iv Jq Jr Js Lv Mb Me Mq Mr Mw My Na Nd Nf Ng Ns Nu Ny Oe Og Oi Or Oy Oz Pa Pd Qb Wb) Kq(Ad Aj aW Bb cl dM Dp dR EF Eq Fp gP Hc Ii Iz Jg Jt Jv Kg Kj Kl Kr Ly Ng Of Og Oi Oy Rv Sf Sh To Ur Us Uu Vo Vz We Th) Jr(Aj dI Et Fp Fr In Is Jj Kg Kj Lv Ma Mq Ms Mt Mv Mw Nc Ng Nh Nn Ns Nw Og Oh Oi Ok Om On Pb Pf Ri Rv To Ur Us Vz Wb Wm) Is(Aj aW bV dl dM Fp Ih In Iq Jj Kg Kj Kr Lu Lv Mc Mq Ms Nf Ng Nn Ns Nw Oe Og Oi Oy Pb Rv Sf To Ur Us Vz Wb Ye) Jd(Aj bA bP bV cT dI Jv Ki Kj Ly Mc Mr Ms Nc Ng Og Oi Oy Oz Ri Sh Uu Wh Ye Tm) Lv(Et Fp Fr Jj Jn Jq Li Mm Mn Mp Mt Mw Mx Nn Nw Ny Oh Ok Om On Pe Pf Qb Qd) Nw(Fp In Io Jj Lu Ly Ma Me Mq Mr Ms Mv Nf Ng Nh Nn Ns Og Oi Oz Pa Pb Pf) Fr(bO dI Fp Hc Jn Kj Kr Kz Mb Me Mq Mr Nd Nf Ng Og Oy Pa Pe Qb Us Uu) Nn(dI Fp Jj Ki Kj Kr Lu Me Mq Mr Ms Ng Nh Ns Og Oi Oy Pc Rv Sh Vz) On(dI Eq Fp Jj Kj Me Mq Mr Nf Ng Og Oi Oy Pa Pb Rv Sh Us Vz Wb Yl) Et(Fp Hu In Jj Lu Mb Me Mq Mr Ms Mv Mw Nf Ng Nh Og Oi Oy) Mr(bA bV dI dM eF Fi Hp Jj Lt Mn Mw Ok Rv Sh Yl Ye Xa) Fp(Jg Jj Jp Jq Jy Lw Ma Mm Mn Oh Oi Ok Om Pf Qd) Mq(eF gL Jp Jq Ma Mm Mn Mp Mt Mw Og Oh Ok Om Pf) Me(bA bV bZ dM eF gL Mn Mt Mw Oh Om Ur) Ng(Ba bQ Jg Ma Mv Mw Oh Ok Om Pe Pf Tn) Xa(Af Jy Kc Nj Nk Nl Og Oi Or Oy Oz Ql) Wb(bA cT Ez Ir Ld Mt Oh Ow Oz Pf Ql) Sr(dI dR eF gL gP In Ki Lu Ly Og Oi) Jj(Ij Jm Jn Lh Mv Ok Pe Pf Pg Qb Qd) Og(Hp Nt Oh Ok Om Pe Pf Qd Un Vi) dI(aM bQ CS dF Fy Jn Nr Pe Pf) Un(bZ eC gL In Lu Ly Ms Oi) Sh(Jy Mt Mw Nq Ny Ut Vi) Yl(Jn Ma Mt Nj Pe Pf Ql) Or(Kj Ru Tr Tt Vi Zw Tl) Oz(Hp Tn Uw Vi Vw Wd Wh) Oy(eF Ok Pf Tn Ut Vi) bV(Dp fP Hc Qy Ri tF) Aj(bQ EF Jy Tn) Fy(bH Kg Kj Rv Vz) Mw(dR eF gL Sf Ye) Pf(Hc Oi Pa Rv Vz) Mt(Eq Rv Sf Vz) Qy(bA cT Va Ye) Jy(aE Kx Rv Uu) bQ(bA cA cN Ki) Fa(Ef Ly tF) Nf(Ok Om Qv) Jn(Kj Oi Vz) Lh(Kj Rv Yd) Ba(Kl Uu) Lu(Ok Rf) Hc(cF Tn) Oi(Oh Pe) Om(Ms Pb) Vi(Jv Kc) bA(Hu Ri) CxfR DkUu ExKi NrVz LyQl InPe KjUt RmVa NyeF OuUs

Unconstrained panels with 2 analytes, where 1.0E-6 >= 'AUC p-value' > 1.0E-7. Contains 1,593 panels of 87,101 total panels evaluated. : No(aD aE Af Aj aW aY bA bJ bN bP bQ bS bV bZ cA Ch cI cN cX dA dB Dg dM Dr Ex Fw Gp Hb Hq Hr Hv Hw Hx Ij Il Ip Iq Ir It Iv Jd Jg Jh Jk Jm Jn Jo Jq Js Ju Kk Ko Kx Ky Li Lw Lz Mc Md Mg Mh Mi Mj Mk Mm Mt Mx My Mz Na Nb Nk Nm Nq Nr Nt Nu Nv Ny Of Ow Pc Pe Pk Pz Qc Ql Qn Qu Qv Ss Ug Uk Ut Vo Vp Vz Tj) Jl(bO bR dA Dp Du Eq Fi Fr Gh Hc Hq Hr Hu Hv Hw Hx Ij Ik Il Ip Iq Ir It Iu Iv Jd Jg Jh Jk Jm Jn Jp Jq Js Jv Kl Kx Lh Li Lj Lt Lw Lx Lz Ma Mc Md Mf Mg Mi Mj Mk Ml Mm Mn Mp Mt Mv Mx My Mz Na Nb Nc Nj Nm Nq Nr Nt Nu Nv Nx Ny Oe Of Ok Om On Pc Pd Pe Pg Pz Qa Qb Qc Qd Qv Rx Rz Tn Tv Vb Wh Yd Zq Th) dN(aC AD aF aG aH aI AJ aK AL aM aN Ao AP aQ AR aS aU aV Aw AX aY Bb BC bE bJ bL bS bW cD cF cG cI cJ cK cL cM cN Cp Cq Cs cU cV CW cX cY cZ DC DD dG dH Dl dM Fy gP Hf Ij Il In Kr Ky Lh Mb Mq Ms Mt Mw Nb Ny Oe On Ow Pb Pe Po Qm Qn Qt Qz Uk Us Vi Xa) Ps(Af Aj AX bA bC Bg cA cC Ch cO Cs Cx dB De dH Dp Em Ez Fn Fw Gc Gd Gz Hf Hr Hu Ii Ik Il Im In Iu Jt Jy Kk Kq Ks Ky Lt Lu Me Mi Mv Nf Nq Nu Nw Nx Pc Pf Pi Pj Qd Ql Ra Rc Si Sj Tn Ud Ug Uk Un Us Ut Uu Uv Va Vi Vo Vs Wb Zw Tm Xa) Is(bR Eq Et Fr Gc Hr Hu Ii Il Io Ip Ir It Iu Jg Jm Jp Jq Lh Li Lj Lw Lx Ly Ma Mb Mc Mg Mi Ml Mn Mp Mr Mv Mw My Na Nc Nd Ne Nh Nj Nk Nl Nt Nu Nv Nx Ny Oh Ok Om On Oz Pc Pd Pe Pf Pz Qc Qd Qv Ri Sh Tv Uu Wc Yd Yl Tm Xa Wm Ti) Qe(bA dM dR Ed eF Hq Hr Hu Ij Ik Il Ip Iq It Iu Iv Jd Jg Jn Jp Jq Js Jy Kj Lw Mb Mc Me Mf Mg Mi Ml Mm Mn Mp Mt Mv Mx My Mz Na Nc Nd Ne Nj Nk Nl Nq Nt Nu Ny Of Ok Pc Pe Pz Qa Qb Qc Qv Rv Sf Sh Tn To Ur Us Vi Yl Ye Wm) Ni(aA aC aF Ao aQ Ar aS aU aY aZ Bb bF bJ bL bM bO bQ bS cA cH cK cM CO cP cS cU cV cX dB dE dG dH dJ Dl Ex Fn Hc Im Jf Jj Jn Jq Jv Kg Kk Kr Lj Mt Mw Ny Oa Ow Pe Pk Ql Qz Ra Rf St Tr Uh Ur Us Uu Vo) Qa(aW dM Eq Fn gL Hq Hr Hv Hw Hx Ij Ik Iv Jh Jk Jn Js Jt Kr Lh Li Lj Lz Mc Md Mf Mg Mh Mi Mj Mk Ml Mt Mv Mx My Mz Na Nb Nm Nq Nr Nt Nu Nv Nx Of Pa Pc Pd Pe Pg Qd Ri Ur Us Wb Tm Xa Wm) Po(Aj Dr eF gL gP Hq Hr Hv Hw Hx Ij Ik Il Ip Ir It Iv Jh Jk Jn Js Jt Lh Li Lw Lz Mc Md Mf Mh Mi Mj Mk Ml Mp Mt Mx Mz Nb Nd Nf Nj Nm Nq Nr Nt Nu Nv Nx Pc Pd Pe Pg Pz Qb Qc Ri Wm) Nw(Dr Et Fr Hu Hv Hw Ii Ij Ik Ip Iq Jm Jn Jp Jq Lh Lj Lx Mb Mf Mh Mi Mk Ml Mn Mp Mt Mw My Mz Na Nc Nd Ne Nj Nk Nl Nt Nu Ny Oe Oh Ok Om On Oy Pd Pe Qb Qd) Im(aW bV cN eF Eq Fp Gb Hu Il In Io Jg Jp Ki Lh Me Mf Mi Mn Mp Mr Ms Mt Mw Mx Mz Nj Nl Ns Nt Nu Nv Nx Ny Oh Pd Pg Qv Ri Rv Uy Wd Wc Wh Zw) Jd(aA Ao aW Bb bJ bQ bS bX cA cK cN Cs cW Du Fa Fi Gh Hc Hu Iz Jr Kr Kx Lu Lx Ml Mq Nf Nj Oe Qv Qy Ru Rv Rz Sf Sj Sr Tn Tr Uk Ur Us Va Vc) Jr(aW bA bH bV cN dM Hc Hp Hr Hu Jf Jg Jp Jq Ki Kr Lu Lw Ly Me Mm Mn Mp Mr Na Ne Nf Nj Nk Nt Nu Ny Oy Pc Qb Qd Ql Qy Qz Ug Uu Yl) aA(aD aN aY BG bH bJ bQ bZ cA Ch cS cW DB dC dF Fy gP Jg Jm Jp Ki Lw Lx Mf Mh Mp Mq Nh Oi On Ow Oz Pb Pc Pe Qd Un Wm) Et(Dr Fr Ii Ik Io Ip Iq Jn Jo Lj Lw Lx Ly Ma Mg Mi Ml My Nd Ne Nj Nl Nm Nn Nq Ns Nt Ny Oe Oh Om On Oz Pb Pe Pf Qb Qd) Nn(Aj dM Fr Hc Hu In Io Jn Jq Jv Lh Lx Mb Mg Mt My Na Nc Nd Ne Nk Ny Oe Ok Om On Oz Pb Qb Qd Ri Sf Us Uu Yl Wm) Kq(aE aK bH bP bX Cx Dg dI Dl eC Fi gL Hf Hp Jo Ki Ko Kx Kz Lu Me Ms Nf Nv Oz Pa Qz Ri Ss Tn Tr Tt Vh Yd Yl Tl) Lx(aZ bR bX cI Cx Dr Hq Ii Jn Ki Kz Ly Lz Mc Mi Mk Ml Mp Mt Mv Mz Nb Nx Pb Pe Pk Qd Ri Vz Yl) Mr(bH bQ bR cN Du Gh gL Jp Lv Mp Ny Oh Om Op Pe Pf Ri Sf Si Sj Tn To Va Vi Vz Wc Tm Th) Mu(aF bJ bX Cs Hq Iu Kx Lw Ly Ma Mc Mf Mg Mi Mx Nc Nk Nl Nm Nt Nu Pc Qc Qd Rf Rh Sh Uu) Ed(cN Cv dF dI Dr Ex Ez Gl Jj Jk Ki Kk Lu Lw Mn Og Oh Pc Pc Qd Ql Qv Rf Uh Ur Ut Zq) Dr(aJ aY bV dG Di Ex Jg Mn Nk Oh Oi Ok Op Pe Qc Qg Qh Ri Rm Rx Sr Va Wc Wf) bA(aM bF Bg bH bJ bZ cA Ch cS CX Db dI Fr Hc Jn Ly Og Oy Oz Pc Ql Qm Un) bQ(aC aF aG aJ bM bP bR bV cI Cs cT cX dA dC dM Jv Me Mq Rv Sh Vz) Fr(Aj Eq Hf Ih Ik Jj Lj Ms Na Ne Nh Nj Ns Oi Oz Pb Pc Pd Vz Wm) dI(aC AD bV cU cW dD Ir Ji Lh Lv Mj Ml Mq Mz Ok Pi Tn Ut Uv) Jj(Dp Ef Ik Jk Jp Ma Me Mj Mn Mq Mt Mw Nh Nt Nv Nx Ny Oh Om) On(Io Jn Jt Lj Lu Ly Mb Mg Ms My Nc Nd Nh Ns Oz Pc Pe Qb Sf) bV(bJ bN cA Cx Db Ef gP Hf Jn Ki Kz Ly Nc Og Oi Or Oy Ql) Mw(Fp gP Hu Jq Mb Mg Mt My Ns Ny Of Og Pf Ri Tn To) Jn(Aj cN In Kg Ki Mq Ms Og Om Pf Ri Rv Sh Ur Us Va) Oz(Fc Fd Lv Ok Om Qv Sf Sh Sr Un Va Vz Yl Zq Zw Zx) Fp(dF Hx In Jk Lh Lu Mq Nh Nt

Figure 7 Continued

Nv Ny Og Pg Sr) Jy(Ax cI Cs dM Eq Jv Me Og Ri To Us Vz Zw) Sr(bH bO eC Ef fP Mb Ms Oe Qv Tn Uu tF) Xa(Aj bN Cx Jv Ki Ng Nu Pb Pc Ri Rv Sh) Og(Ba dM Fa Jg Nu Nv Ny Ow Qb QI Vw Zw) Ok(In Jo Jt Kj Ly Me Ms Nh Oi Pb Qb) Om(Hu Io Kj Lu Ly Mb Ns Oi Oy Pe Qb) Ny(eC Ma Me Mq Ng Ns Of Ri To Th) Lv(Jp Lj Mq Mz Ng Nh Nu Un Ur) Or(bJ bP bZ dA dM Ur Vj Zq Wm) eF(Ch Cs Fa Gl Kz Nf Oa St Un) Pf(Me Ms Nh Ns Pb Qb Us Uu) Fa(dR fP gL gP Oi Qy Ri) Ql(Lu Oi Ri Sh Va Vz Ye) Pe(bH Ki Mm Ms Pb Vz Wm) Me(aP Ax bF cN Mm Tn) Mq(bF bZ Ki Mz Nq Qb) Mt(Ik Nd Nf Ns Oi Oy) Ji(Cx Jk Kj Kr Mh To) Yl(bZ cT Ez Lh Nr Oh) Nr(Ki Rv Sh Wb) Ly(Ex Ki Kk Qy) Ng(Fy Jk Jp Nt) Tn(Kj Qy Ri Rv) Vi(Ki Qb Qy Rf) Lh(Kg Vz Wb) Oh(Ms Nf Vz) eC(Dc Pk Vt) Ex(Lu Oi) In(Ow Qb) Qd(gL Wm) Qv(Pc Qy) Kj(Ou Un) Rv(Cu Ut) Oy(Dk Uw) aJ(bN bR) AjBa EfGd FyUr LuQb MaUu MnNh MpNd NfJp IrPb ZwJe YeRm KiKy KrOu KxOi UnUs bOdF bZdM cXfR

Uncon

Oy Pb) Uw(Af Ap Bb bN bO Hf Kc Kq) bZ(Co Jv Me Nj Nk Oy Qu Qz) Bo(aM aY Jv Me Ne Nk Tv) Fa(bH bO Cx Fn fP Na Qz) Lu(aM bJ
Ow Pk Ql Rf Vt) Mu(Jp Lj Lx Oh Ok Pe Pf) Rz(Af Ap Bb bN bO Me Mt) Fy(bH Co Ii Iz Jo Kg) Qv(Hf Is Jv Nf Pc Ql) Kq(aK Ii Iz Jt Kl Oy)
Bb(Gb Ry Si Vh Wd) Fr(Lj Mg My Ne Nh) Lx(Hq Lj Oy Pb Qz) Kg(Ex Is Jp Lh Pf) Ug(Nk Oz Pk Qz Tt) bH(aM bM Oa Vt Ti) Jv(bF bQ Jp
Ky) Ur(Cx Me Nk Qz) bN(Ex Ry Vh Wd) bO(aP Jl Pf Vh) Yd(Is Nx Oy) Ru(Or Pa Pc) aK(Jl Jp Oa) aM(cT Nk Oe) Ao(Is Lh) Ap(Ex Uf) Ba(Kl
Ss) Bn(Uz Wg) Eq(Jp Qh) Mw(Jq Wh) Tv(Fn Vq) Ir(Ry St) Qy(Ue Vb) Jo(Ex Ok) Tl(Jm Nx) Kc(Vh Wd) Om(Lj Of) Pb(Jl Ok) aP(fP Qz) bM(cC dE) CoPf CvCx GnMt GlIi NsMp MgTt MmPe MqOh NkRy UaIz IbVj QubQ KlUf OaOe UyVt} Og{Hp(aM AS Ax BA Bc bQ bR bU bV bZ CP Cq CS CT Cu Cw dF dN Et Ez Fb Fr Fy Hv Hw Id Ij In Jd Ji Jp Jq Jy Kd Ke Kk Kn Kq Kr Kx Ky Ld Lh Lv Lw Lx Ma Mh Mi Mj Mk Ml Mq Mt Mv Mz Na Nb Nf Nj Nk Nn No Nq Nr Nt Nu Nw Oa Oh Ok Om On Ow Oz Pa Pb Pd Pf Pk Po Qb Qv Qx Qy Ra Rf Rh Ri Ru Sr St Tn Tv Uf Up Ut Uw Uz Vp Vq Vw Wh Zw Tl) Mu(aA aD AJ aM bA Bb bR bV cN Cs cT dM dN Ed Et Fp Fr Fy Hu Hv Hw Ij Im In Is Jd Ji Jj Jl Jn Jo Jq Jr Jt Jv Ki Kj Kx Ky Lh Lv Lw Lx Ma Me Mh Mi Ml Mm Mn Mq Mr Ms Mt Mz Nb Nf Ng Nh Nn No Ns Nt Nw Oa Oh Oi Ok Om On Oz Pa Pc Pe Pf Pk Po Ps Qa Qd Qe Ql Qv Qz Ra Rf Rh Ri Sr Un Us Uu Zw Xa Wm) Jd(aA Aj Ao Ap Ax bA Bb bM bV bW cN Co Cs cT Cv dI dM dN Ed Em Gn Hb Hc Hl Hq Hu Is Iz Ji Jj Jn Jr Jv Jy Ki Kj Kx Ky Kz Lu Lw Ly Me Ml Mq Mr Ms My Nc Nf Ng Nn Nr Oa Or Ou Oy Oz Pk Po Ps Qa Qe Ql Qv Qw Qy Qz Ra Rf Ri Ru Rv Rz Sh Sj Sr Uf Ul Un Uu Uz Vi Vz Wg Wh Yl Zw Wm) No(aA aD aW bA Bg bO bR bS bV bW cA Co cT Cv dM dN Dp Ed Et Ez Fp Fr Fw Hc Ik Im Io Is Jg Ji Jn Jo Jq Jr Jt Ju Jv Jy Ki Kq Kr Lh Lj Lu Lv Lw Ma Me Mf Mi Mm Mq Mr Ms Mt Mz Nb Nf Nh Nn Ns Nt Nw Oh Ok Om On Or Ou Pc Pe Qa Qe Ql Qw Qy Qz Ri Sf Sh Sr Ud Ul Vz Yl Wm) Nn(aA bV cN Co dA dI dM dN Dp Ed Eq Et Fc Fp Fr Hc Hw Hx Ii Ij Im Ir Is Ji Jj Jl Jn Jo Jq Jr Jt Jv Jy Ki Kj Kr Lh Lu Lv Lw Lx Me Mi Mq Mr Ms Mt Na Nb Ne Nf Ng Nh Ns Nt Nw Oi Ok Om On Pa Pe Pf Po Ps Qa Qd Qe Ql Qz Ri Rv Sf Sh Sr Uf Ul Vz Yd Yl Tm Xa Wm) Ki(aA aP Ax BA Bc bQ bV Cs cT Cw dA dF dG Di Dk Dl dM dN Ed Et Ex Ez Fa Fr Fy Hu Ij Im Is Ji Jl Jn Jq Jr Jy Ke Kq Kx Ky Lh Lu Lw Ml Mq Mw Mx Nf Nr Nt Nv Ny Oa Oh Ok Om On Or Ou Ow Oz Pd Pe Pf Pk Po Qa Qd Qe Ql Ra Ri Sr St Tn Tt Uf Un Ut Vi Vw Wm) Mq(aA Ad bA Bg bR bV cT Cu Cv Cw Dc dM dN Dp Ed Et Fb Fp Fr Fy Hu Hx Ih Ij Im Is Jg Ji Jk Jl Jn Jp Jq Jr Jv Jy Kd Ky Lh Lv Lw Lx Ma Me Mm Mn Mr Mt Mw Mz Ne Nh Nv Nw Ny Oh Ok Om On Or Ou Pe Pf Pg Po Ps Qa Qb Qd Qe Ql Qy Rf Ri Sr Tn Uf Wb Wm Th) Is(aA Al Ao aW bJ bO bV bW Co dM dN Ed Et Fp Fr Hb Hc Hu In Io Jg Ji Jj Jl Jq Jr Ju Jv Jy Kg Kr Lh Lu Lv Lw Lx Ma Mc Mi Mm Mr Ms Mt Mv Mw Mz Nb Nf Nt Nw Oh Oi Ok Om On Pa Pc Pe Pf Po Qa Qe Ql Qv Qy Qz Ri Sf Sh Sr Tz Uf Ul Us Vw Vz Yd Yl Wm) Ps(aA Af Ap BA bC bJ bO bQ bS bU cR CT CX dA dH dI Dp Ed Em Ez Hb Hl Hu Io Jy Kq Kr Kx Lh Lu Me Mi Mr Mt Mv Mw Nb Nf Nj Nk Nr Nt Nu Oe Of On Or Oy Oz Pd Pf Pi Pk Ql Qn Qv Qw Qx Qy Ra Rb Rg Ri Sr Tn To Tz Uh Us Uv Va Vb Vi Vz Yl Zw) Qe(aA aW bA bO bV Co dA dI dM dN Ed eF Et Fp Fr Hu Hw Im In Io Jg Ji Jj Jn Jo Jq Jr Jt Jv Jy Kg Kr Lh Lu Lv Lw Lx Ma Me Mi Mm Mr Mt Mv Mw Mz Nb Nc Nf Nt Nw Oh Oi Ok Om On Pa Pc Pe Pf Po Qa Ql Qv Qy Qz Ri Tn Us Vi Vz Yl Zw Wm) Kq(aA Ad aF Aj aL Ao aW Bb bH bJ bO bV Co cZ De Dk dM dN Dp Ed Fn Hb Hc Hq Hu Ib Ii Iz Jg Jh Jl Jo Jt Jv Kg Kj Kl Ko Kr Lj Lu Ly Md Ms Mw My Nb Ng Nv Oa Of Oy Oz Pa Pg Ql Qu Qz Ri Rv Sf Sh Sr Tt Us Ut Uu Vp Vs Vz Yd Yl Zw Wm) Ed(aA aJ aP BA Bc bQ bV cN Cv dF Dk dM dN Et Ex Ez Fa Fb FR Fy Hu Ji Jl Jn Jp Jq Jr Jy Ke Kk Lh Lv Lw Ma Mm Mn Mr Mw Nr Nv Nw Oh Ok Om On Pe Pf Po Qa Qd Ql Qy Rf Ri Sr Tn Uf Un Ut Vb Vi Vq Vs Vw Wh Zq Zw Xa) Jl(aA Aj aW bA bO bR bS bV cA Co Cv dM dN Dp Et Fp Fr Hc Hu Im Io Jg Ji Jj Jn Jq Jr Jv Kr Ky Lv Lw Ma Me Mf Ml Mz Nc Nd Nf Ng Nk Nl Ns Nw Oi Ok Om On Oz Pc Pk Po Ql Qv Qz Ra Rf Ri Sr Ul Un Ur Us Uu Vz Yl Zw Tj) Lx(aA bR bS cA Et Fc Fp Fr Hq Hu Hv Hw Ii Ij Im In Ir Jg Ji Jk Jn Jo Jp Jr Jt Lh Lu Lv Lw Ly Ma Me Mf Mm Mn Mr Mt Mv Mw Mz Na Nb Nd Nf Ng Nh Ns Nt Nv Ny Oh Ok Om Oy Oz Pb Pc Pd Pf Pg Qa Qb Qd Qz Vz Wb Yl Wm) Fr(aA bO dN Dp Et FP Hc Hu Hw Ij Im In Ir Ji Jn Jo Jq Jr Jv Kj Kx Kz Lh Lv Lw Me Ml Mr Mt My Na Nb Ne Nf Nh Nl Ns Nt Nu Nw Oh Om On Oy Oz Pa Pe Pf Pk Po Qa Qb Qd Ql Qz Ri Sr Un Uu Wm) On(aA Bb Co dI dM Et Fb Fp Hq Hu Im In Io Jh Ji Jj Jn Jq Jr Jv Kx Lj Lv Lw Ly Ma Me Ms Mw My Nd Nf Ng Nh Nv Nw Oa Of Oh Om Ow Oy Oz Pb Pc Pf Pg Po Qa Qd Ql Qz Rv Sf Sh Vz Yl Zw Wm Th) Jr(aA BA bH bJ bV cN dI Dk dM dN eC Et Fb Fc Fi Fp Hu Im Jg Ji Jv Jy Kg Kx Lv Lw Ma Mm Mn Mv Mw Nh Nt Nu Nw Oh Ok Om Pf Po Qa Qd Ql Qv Qy Ri Sf Sr Uf Ul Ur Us Vw Vz Wh Wm) Vw(aA aM An Ap Ax bL bQ bU cT dA Dg Dp Hl In Iv Je Jv Jy Kc Kd Kk Kl Kn Kr Kx Kz Ld Me Ml Mr Mw Nb Nf Nk Nr Nu Nw Or Ow Oz Pi Pk Qb Ql Qx Rf Sh To Uu Vz Yl Zw Tm) Po(aA bO bV Co dM dN Dp Et Im In Jg Ji Jj Jn Jq Jt Jv Jy Lh Lu Lv Lw Ma Me Mm Mr Mt Mz Nb Ng Nh Nt Nw Oh Oi Ok Om Oy Oz Pa Pb Pc Pe Qa Ql Qv Qy Ri Uf Ul Wb Wm) Un(aA Aj bA Bb bH bV bW Co cT Cv dM dN eC Ez Fn Hb Hu Ii In Jj Jt Jv Jy Kd Kg Kj Lu Lw Ly Ma Ms Nc Nf Nj Nl Oi Ow Oy Oz Ql Qw Qy Qz Rf Ri Sr Uf Us Uu Uy Zw Wm) Qa(aA bA bJ Co dI dM eC eF Et Fn Fp Hu In Io Jg Ji Jq Jv Kg Lh Lu Lv Lw Ma Me Mi Mm Mn Mr Mt Mw Mz Nb Nf Nt Nw Oh Ok Om Pa Pc Pe Pf Ql Qz Ri Rv Sf Ur Vz Wm) Yl(Ax Ba bJ bN bQ bZ Cs cT Cu Cx Ez fR Fy Ih Ij Im Ir Jn Jy Kx Ld Ma Mh Mr Mt Mw Nb Nj Nq Nr Nt Nu Ny Oa Oh Ow Pe Pf Ql Qy Rf Rh Ri Rm Sr St Vi Zw Xa Wm) Om(aA Bb dI eC Fp Hq Hu Im In Jh Ji Jj Jn Jq Jv Kj Lh Lj Lu Lv Ly Ma Me Mg Mh Mi Mr Ms Mt My Mz Ne Nf Ng Ns Nw Of Oh Oy Oz Pa Pb Pc Pe Pf Qd Qz Uu Wm) Vi(Af aV aX BA bJ BN cT Cx cZ dA Dc dI Dp Ez Fi Fn Ih Im Je Jv Kc Kr Mi Mr Mw Nc Nf Nj Nk Nu Ow Oy Qb Ql Qn Qy Rb Rf Rg Ri Sf Sh St Up Us Vz) dN(aA BA Bg bJ bN bR bV cT Dk Dp eF Ez Fb Fy Gp Hu Im Ji Jn Jv Jy Ky Kz Lu Lv Ly Ma Me Mr Nc Nf Nr Or Ou Ow Oy Oz Ql Qt Qw Qy Qz Rh Ri Sr Wb) Ji(aA aW Bb bJ bV dI Dp Et Fb Fn Fp Hu Ik In Io Jg Jk Jv Jy Kr Lh Lu Lv Ma Mr Ms Mv Mw Nb Nf Nt Nw Oh Pa Pc Pd Pe Pf Ql Qy Rf Ri Us Wm Th) Sr(aA aW bA Bb Bg bH bJ bO bV Cx dI dM Dp eC eF Ez fP Hu In Jv Jy Kd Kj Ko Lu Lv Lw Ma Ms Nc Nf Nj Nl Ou Ow Oz Pk Ql Qw Qy Qz Ri Uf Vz Wm) Im(aA bV bW cN Cv dM eF Et Gn Hl Hu Lh Lu Lv Lw Mm Mn Mr Nb Ne Nh Nt Nv Nw Oh Ok Pe Pf Qd Rt Rv Ry Sf Sh Uf Uw Uz Vb Vh Vz Wg Zw Tl Wm) Xa(aA Af aV bA bC bJ bN bO bQ bS bU cA cT CX dA dH dI Dp Ez Fy Jv Mt Mw Nj Nk Nu Or Oz Pk Ql Qn Qw Qy Ra Rb Rf Rg Ri Ru Sh Vz Zw) Vz(Ax BA bQ Cs CT Cu Fy Ih Ij Ir Jn Js Kx Ld Lh Mr Mt Mz Nq Nr Nt Nu Ny Oh Ok Ow Pd Pe Pf Pi Ql Ra Rf Rm Ru St Tn Ut Zw) aA(aM bM Dp Et Ez Fp Ik Jg Jk Jn Jq Jv Jy Lh Lv Lw Ma Mf Mm Mn Mv Nh Nw Oh Ok Ou Ow Pc Pd Pe Pf Pg Qd Ql Qy Ri Uf Zw Wm) Zw(Ba bH bM bO bQ cE dA Dk Ez Fb Fc fR Hu Ih Je Jn Jy Mr Mw Nb Nj Nk Nq Nu Nv Nw Ny Or Oz Qb Ql Qy Ri Rm St Wb) Ql(aJ aP Ax BA bV cN Cv cW dI dM eF Fa Hu Jj Jn Jv Jy Kx Lu Lw Ly Ms Nr Ow Pf Qv Ri Ru Uf Ul Uw Uy We) Qy(Ax bA bV Cs Cv dM Em Fa Fc Gn Hl Jn Kx Lp Lw Oa Ow Pe Pf Qv Rt Ru Ry Uz Vh Wc Wg Ye Tm Tl Wm) Jv(Ba bQ bV dF Dk Et Ez Fa fR Hu Jn Jp Jy Lh Ma Mn Mr Mw Nr Nv Oh Ok Ou Ow Pe Pf Qd St Uf) Fp(Ba bV bW Cv Dk Em Et Hx Jg Jk Jp Jq Jy Lh Lv Lw Ma Mm Mn Mw Nt Nv Nw Oh Ok Pf Pg Qd) Wm(cN Dk Et Fd Jg Jj Jk Jn Jp Jq Jy Lh Mi Mp Mv Mw Nb Nt Nv Nw Ny Oh Ok Pe Pg Qb Qd) dM(Ez Hu Ij Jn Jy Ma Me Mr Mv Mw Nc Nf Nk Nr Nt Ny Oa Or Ow Oz Pe Pf Pk Qt Qw Ri St) Ri(aJ aP Ax BA bV cN eF Ez Fa Hu Jn Jy Kx Lw Mn Mr Mw Nr Oz Pe Pf Qd Zq) Nw(Et Ij Io Jg Lh Lu Lv Ma Me Mi Mr Mv Mw Nb Nf Nt Oh Ok Oz Pe Pf Qw Qz Th) Et(bV Hu Io Jn Lh Lu Lv Lw Me Mi Mr Mv Mw Nc Nf Nh Nt Nu Oh Pe Pf Qb) Wb(bA bQ Cs cT dA dF Ez Jy Kx Ld Li Ml Nb Nu Oh Ow Pd Pf Qx Ra Rf Ru) Jy(aJ Ao Ax bV Cs Hu Jn Kx Lj Nr Oa Oh Ow Oz Qz Sf Sh Uu Wf) Ez(Aj bV cN Eq Fc Fd Gn Hl Lp Lu Lw Qv Rt Ry Uz Vb Wg Tl) Jn(bV bW cN dI Jg Kg Kr Kx Lv Oh Ou Pf Sf Sh Uf Ul Wh) Ow(bV cN Fc Hl Hu Lu Lw Rt Rv Ry Uw Uz Vb Wd Wg Tl) Pf(bO Dp Fc Fd Jq Lh Lv Me Mw Nf Ng Nh Nt Oh Ok Oy) Oh(dI Fc Hu Ik Lh Lu Lv Me Mv Ne Nh Nt Ok Qd) Ba(cN Dp Eq Fc Hc Io Kl Me Ng Oa Qu Sh Uu) Ok(dI Hu Io Lu Lv Me Mr Ms Mv Mw Nf Nh Nt) bV(bJ Dk Dp fP Hu Me Mr Nc Nf Nr Oz Rf St) Lv(Jg Li Mm Mn Mw Nu Nv Ny Pe Qb Qd) Sh(Cu Ij Mt Mw Nr Nt Nv Ny St Ut) Pe(bJ In Jg Jj Lw Mm Mn Mw Oi Uf) Sf(Ij Js Mt Nr Nt Nu Ny Rm Ut) cF(Aj Cs Hc Iv Kx Nf Ny Oa Pk) Fc(Ax

Figure 7 Continued bQ Cs Fy Js Mw Ra Rf) Fd(Ax Mh Nj Nq Qx Ra Rf) Nu(Hl Mm Mw Ny Uw Wh Zq) Lw(eC Fy Kz Mv Oa Qz Rf) Mr(aJ aW cN Jg Kx Mn Ru)
Nf(Cv Dk Ex Jg Ou Uf Zq) Ih(Gn Hl Uw Uz Vb Wg Tl) Oz(bA Fa Fb Kk Kx Tn Uf) dI(aM Cs Fa Lh Ml Nr Nt) St(Hl Ru Ry Vb Vh Tl) Rv(bQ
Ij Mt Nt Ny Ra) bJ(bA Hl Or Ou Ry Uw) eC(Cu Id Jq Kd Pi Pk) Me(Ax Cv Jg Mm Mn) Hu(bA cN Cs Cv Uf) Cx(Em Ry Uw Vb) Fy(Co Du Kg
Uf) Zq(Ax Iv Ld Nj) Jj(Dp Ef Ij Jm) Lh(Kg Kj Mm Yd) Ex(Ly Qw Qz) Hl(bQ dA Nq) Qb(Jg Lu Nt) Ry(bQ dA Nq) Rf(Cv Lu Ou) Uf(Ly Ml
Nr) Uw(bN bO dA) Pc(bA Tr Tt) Dk(Oy Uu) Fa(Dp Qw) Fi(Ir It) Nh(Jg Mn) Tm(Jk Ut) bN(Vb Tl) CoNr CvOa DuIr GbbQ GdV

Qm) Ye(bH Ez Lu Nu Qy Rb) On(Bn dD Jg Jt Kj Qz) Mt(dI Jt Kf Kj Qu) Eq(bZ Ez Ma Tn) Nu(bU Dp Ju Lv) Nf(Bg CH cS) Qu(bQ bZ Jl Lu) Vi(Jt Ju Kf Kj) Tn(Bn De Kj) Rb(cJ Ld Mq) Jl(aW Qn Vs) Pi(Fd Kj Qn) dI(Fy Is Qe) Dg(bZ Pf) Dp(Lu Va) Mz(dA Kf) Iq(Is Rm) Je(bU dC) Ld(bH Du) Ut(Bn De) dD(bU Fy) EzVo LudC LvPa MwHu NbOe Q

Qv Si Ug Ur Va Wc) Tn(Aj Gl Hc Jv Kg Kz Me Mq Nc Nf Nj Pa Pc Ql Rf St Ur Us) Th(aP cS dG Ez Fa Fr Ji Lh Lx Mq Nj Nk Nv Nw On Ou Vq) Lu(Et Ex Fp Ji Jn Kx Mr Nr Pe Pk Po Qb Ql Rf Sr Zq) Ql(bP cN dM Hl Jj Me Mr Ms Nc Oe Or Po Qv Sr Wb) Pc(aJ aP Ax bA bZ dM Fa gL Jj Pf Po Qv Tr Tt Zw) Jn(Aj aW bP cN dM In Jo Kg Kr Me Ms Nc Ur Wc) gL(Fa Iv Ji Jj Me Mq Mr Nf Nw Ny Oa Pe Po Qd) Nr(Aj cN dM Fi Jj Me Ms Sf Si Ur Va Yd) Mr(AJ aW bA bH cN dM Fi Jj Ky Qv Ur) Sf(Ih Mt Nn Nu Nv Ny On Ow Qb Rm St) Nj(bA Du Fd Gc Hl Hp Ry Uy Zq Zw) Fp(dF Fr Jj Jp Ky Lw On Qv Ur) bA(bO eC Fn Hc Me Nc Nf Nl Pk) Aj(Ef Fy Jp Lh Ma Nn Pf Po) Sr(bH bO Cx Ii In Ms Nc Qv) Du(bQ bZ Mw Nk Nq Oa Qy) Nn(bO dM Fd Hc Jv Kr Nc) Me(bZ dM Ji Kk Nw Oh Ur) Fa(bO dA Dp Ms Qy Wb) On(Eq Kr Us Vh Wc Yd) Va(Ih Qb Qm Qy Rm St) Nc(dM Ji Lx Or Po) Hl(bQ bZ Nk Nq Nu) Zw(bH Je Nl Pb Qy) Fi(Ir Lh Pe Pi) Hp(bZ cS Ky Nk) Wb(cS Ez Ld Rf) Wc(Lh Mt Qb Rm) Kr(Fr Ji Mn Qd) Eq(Ez Jp St) Mw(aW cI Wh) Or(Ax dM Ur) bZ(Kx Mq Nf) Em(cT Nl) Fd(Nk Pi) Fy(Co Kg) Lv(Mq Ur) Mt(Si Yd) In(Iv Ow) Hc(Fr Pf) Jj(Dp Ef) Lh(Kg Yd) dM(Pk Qd) BaKl CxZq FccS LweC LxNl MacN NfQv IiPe JiaW WdKc JpKx UzPi PfbO} Fp{Oi(aJ aO aP BA bF Bg bH bQ bV bZ cE cG cN cS Cu Cv dF dG Di Dk dM Et Ez Fb Fr Gl Hx Id Is Jg Ji Jj Jk Jl Jn Jp Jq Jt Ke Ky Lh Lv Lw Lx Ma Mm Mn Mq Mv Mw Mz Nh Nn Nt Nv Nw Ny Oh Ok Om On Or Ou Pc Pf Pg Qa Qd Qe Ql Qt Qv Qy Rc St Uf Ur) Jj(Bg bQ bZ Ch cS dF Dk Ef Et Ez Fr GL Hu Hw Hx Ii Ij Ir Is Jg Ji Jk Jl Jm Jn Jo Jp Jq Jt Ky Lh Lu Lv Lw Lx Ma Me Mi Mm Mn Mq Mr Mt Mv Mw Mx Mz Na Nb Nf Nh Nn Nt Nv Nw Nx Ny Oh Ok Om On Ou Pa Pc Pd Pe Pf Pg Qd Qe Ql Qt Qy Ua) Fr(aD Aj aM Ao Bb bO bR bW Co dM Et Gd Hu In Ir Is Iz Ji Jl Jn Jq Jv Kg Kr Lv Lw Ly Me Mg Mm Mq Ms Mw My Nh Ns Oe Ok Pb Qa Qv Tz Ur Us) Lw(Bg bZ Et Hx In Is Jg Jl Jp Jq Lh Lu Lv Lx Ly Ma Me Mi Mn Mq Mr Mt Mv Mw Mx Mz Nb Nn Ns Nt Nw Oh Ok Om On Pa Pe Pf Qa Qd Qe tF) Lu(aD aM Ba bR bS bV cS Cv cW Dc dF Dk Et Is Ji Jl Jp Jq Ke Ki Lv Lx Mm Mn Nn Nw Ok Om On Pj Qa Ql Qy Rf St Uf Uh Ur Vq Ti) On(Aj bH Co Dc Et Gd Ha Hq Hu Ii In Jh Jk Jl Jo Jq Jt Kg Lv Ly Ma Mg Mk Mm Mq Ms Mv Mw My Nn Ns Nv Oe Of Ok Pb Ur Us Tj) Lv(bV bW Co Cv Et Gd Hx Is Jg Ji Jn Jp Jq Lx Ly Ma Mm Mn Mq Mt Mw Mx Mz Nn Nw Oh Ok Om Qc) Lx(Et Hq Hv Hw In Ir Jn Jp Jq Jt Ly Me Mh Mm Mn Mq Ms Mv My Mz Na Nk Ns Oh Pb Pc Qd) In(bV Cv cW Et Hx Is Jg Ji Jl Jp Jq Mm Mn Mq Mw Nn Nv Nw Ny Oh Ok Om Ow Pf Qd Qe) Om(Et Hu Ik Is Jn Jo Jp Ly Ma Me Mg Mm Mq Ms My Nn Ns Of Oh Pb Pc Qd Qe) Nn(Et Gd Hu Is Ji Jl Jp Jq Ly Me Mm Ms Nk Ns Nw Oe Ok Pb Pc Qa) Nw(bH bV Et Is Jn Jq Jt Ly Ma Mm Ms My Ns Ok Pb Pc) Jl(Gd Ii Io Iu Jo Ly Ma Nc Nk Nl Oe Pb Pc Pz) Jq(bH Et Is Jg Jp Ma Md Mm Mn Mq Mv Mw Ok Pc) Ms(bV dF Dk Et Is Jg Ji Jp Mn Ok Qe Qy) Gd(bF Bg Ef Fy Mv Nx Ou Pf Rb Ut) Jp(Io Is Kr Mm Mq Oh Pf Ur Us) fR(bN bR bS CX Dl Mv) Mn(Me Mq Mr Nh Ok Qd) Et(Hx Io Jo Ly Mq) Ly(Cv Ji Mm Ok) Ma(cN Ji Mq) dF(Aj Jo Kg) Cv(bZ Me) Ji(Pb Pc) Ok(Jo Pb) aD(Ba cE) bV(bF fP) DkOe EmbZ FyIi NsMp MmQd IsJm QyQv KiKy KrOu LjPf} Is{Kg(AD aM An As aW bA bH bR bV Cp Cq cT Cu CW Dc dM Hl Hu Hv Hw Id Ij Ir Ji Jn Jo Jp Jq Jv Kd Kn Kp Kr Lh Lu Lv Ly Me Ms Na Nc Nf Nl Nr Oe Oi Ok Om On Pb Pe Pi Pk Po Qa Ql Qv Qy Ra Rj Sr Tn Tt Tv Tz Uc Ud Un Up Us Ut Uv Vt) Aj(aW BA bC bH bJ bQ bR bV bW bZ cN cS cT Cv cW dA dF Dp Ef Ez Hb Hu Ju Jv Kr Lu Lv Ly Ma Me Mr Ms Nc Nl Nr On Pf Po Qt Qy Tn Tz Wd Wh) Ii(An bA bR bV Cp cT Cu Dc Fa Fy Gl Hc Id Ji Jv Kd Ke Kr Kx Ky Kz Mq Nw Pk Po Ql Qm Qv Qy Rf Sr Ud Un Uv Uz Vt Vu Wg Th) Jj(Bb bH bO bR Dp Et Hc Hu Ik Io Jv Kr Lh Lu Lv Me Mq Mr Ms Mv Nf Oi Pd Pe Po Qe Us Wm) aW(bR Hc Jl Ju Jv Kr Lu Ly Me Mq Mr Ms Nc Nf Nj Nk Nl Oe Oi Pa Pc Ur Us) bV(bH bN bO bR Dp fP Hc Jo Jt Jv Kl Kr Lu Ly Me Ms Nc Nf Nl Oe Pa Pc Us) Oi(bH dM Hc Hu Ji Ki Kr Lv Mq Mv Nf Nn Nw Oh Pc Pd Po Qa Ql Ur Us) Lu(aD bR Co Ct Dp Eq Hc Jv Ki Kr Kx Lv Nw Po Rf Sf Ur Us Ye) Sf(Af bH bO bQ bR Cx Mr Mw Nu Or Pa Pb Pc Ql Qv Qy Uo Us) Ye(Bb bH bO CX dA Je Jv Nc Nf Nj Nl Nu Ql Qn Qy Tz Uo) Jo(bA Cq cT Cu Dc Jv Pi Pk Rj Sr Tn Tv Uc Un Up Vt) Us(bA bH bI cN dM Fr Hu In Ir Jp Ki Ms On Ql Qv Tn) Ur(Ao bH Dp Hc Ir Jv Ki Kr Kz Ly Me Ms Nc Nf Pc) Qv(bH bO dM Hc Jv Ki Kr Ly Me Nc Nf Nl Pa Pc) dM(bR Hc Kr Ly Me Mq Mr Ms Nc Nf Nl Pa Pc) Kr(bH Ih In Ir Iu Jl Ki Ky On Ou Tn) Pb(Gn Hl Mq Nw Po Rt Uw Uz Vb Wg Tl) Hc(gL Ih In Ir Iu Tn Uy Wc Wd Wh) Wb(Nc Nj Nk Nl Pg Qd Qh Ql Qm Tz) Po(In Io Me Mq Ms Ns Oe Pa) In(Ji Jv Kz Mq Qa Wm) Va(aV bO Cx dA Dp Ql) Ly(cN Iq Jf Jv Ki) Ms(bH bR Lv Mq Nw) Wc(dA Jv Nb Pi Rb) Fi(bN Fc Pc Pi) Me(bI cN Co gL) Si(bO Cx dA Nk) Jt(bA Un Uz Wg) bR(bH cN Co Ir) Af(Uw Wh Zq) Eq(Bg bZ Ma) Mq(Io Lv Nn) Nj(To Tm Tl) Ho(Ny Pi Ra) Kz(gL Ir Iu) Fn(Nc Nl) Nm(Uz Wg) Tn(Cq Pa) Io(Ji Lv) Yd(Nk Ql) Kf(Uz Wg) cN(dH Nc) BaKl DuNu TiaM NlTm ToNw JfLt WdKc JvbH RuPa VbbN} Me{dM(Ax BA bF Bg bQ bR bV bZ CS cT Cv Dk eC Et Ez Fa Fb Fr gL Hu In Ji Jj Jl Jn Jp Jq Ki Ky Lh Lv Lw Lx Ma Mn Mq Mr Nc Nn Nr Nw Oa Oe Oh Oi Ok Om On Or Ou Ow Pc Pe Pf Pk Po Qa Qd Qe Ql Qv Qy Rf Sr St) gL(AJ Ba bV bW Ch cN Co Cv Dk dL Dp Fa Fr Jh Ji Jj Ke Ki Li Lu Lw Lx Mq Mr Mw Nc Nj Nk Nn Nw Ny Ou Qa Qd Qe Ql Qt Qv St Uf Un Ur) Lx(aW bR bS bV cA dH Ha Hq Hx In Jn Jq Lv Lw Ly Mn Mq Mw My Nn Ns Ny Of Oi Om Pb Pc Pg Qa Qe Qz Ur Us Tj) Nn(Aj aW bH cN Co Fr Ha Hu In Ji Jj Jn Jv Kg Ki Lu Lv Mq Ms Ns Nw Oi On Qe Uk Ur Ye) Ur(Bg bZ Ch Ef Fr Hu In Ji Jl Jn Ki Lu Lv Ma Mr Nr Oh On Ou Qe Ql Qy Rb Tn Ut Uv) Aj(Ad BA bV bZ dF Dk Ef Et Ez Fr Jl Jn Jp Lh Ma Mn Nr Oh Ok Om Pf Qe Tn) On(aW Ax bA Bb bP bV cI cN Co Cs cZ De Hu Ji Jn Ki Mk My Nb Of Pb Po Ql Us) Jj(Dp Ef Et Fr Ji Jl Jm Jn Ki Lh Lv Mn Nw Ok Om Po Pz Qa Qb Qe Ql Qy Rb) aW(aP Ba bQ dF Et Ex Fr Ji Jl Jn Lh Mr Mt Mw Nw Oh Ok Pf Qa Qd Qe St) Fr(Ax bH bO Cs Hu Ji Jn Kg Lj Lv Ms My Ne Nh Ns Of Oh Pb Us) bZ(bS bW cA Co Eq Hp Je Ji Jv Kg Ki Kx Lu Lw Mq Nc Nw Qy) In(aP Ax BA bV Cs dG Et Ji Jl Nw Ow Po Qa Qe Ql Un) Ki(Ax bA bQ bV Cs cT Fa Jn Ky Nr Oh Pe Ql Qv Sr Tn) cN(Ax bR bS bV cA cL Cs Jn Lu Ma Mn Nr Oh Oi Qe Qv) bV(Ax bH bR cA Cs Ef fP Jn Mn Nr Oi Qe Ql) Lu(Ax bA Cs Et Ex Ji Nw Ql Rf Un) Lv(Et Ji Jq Mm Mn Nw Oh Om Po Qa) Tn(bW Co Cv Lw Mm Nk Nw St Uf) bH(aP Ax Cs Ji Nw Pe Qv Rf) Qv(Ef Jl Qe Ql Qy Un) Jn(aJ aP bP Cv Kg Uk) bA(aM bO Oi Pc Qe Qy) Ji(cI Ma Oh Pc Ql) Ye(Mv Nq Ql Qy) Nw(Ma Ms Pb Qa) Po(Jo Ms Pb) Mn(Jv Kg Mq) Mp(Hq Nd Ns) Mt(Ho Mw Uy) Wb(Ez Nj Ql) Jl(aE bO Us) Ax(Oi Qy) Co(bQ Nr) Cs(Oi Qy) Jq(Lw Mw) Kg(bQ Ma) Om(Ms Pb) Pc(Ok Tr) bI(Qd Qe) CvNr EtJo GnQa MqOh NjHp IiUn JeeC JpJv aJgP} Us{Jl(AD aM As aW bA Bn bV Cp Cq cT Cu CW Dc Di dM Dp Du Em Et Fr Gh Gn Hc Hl Hu Hv Hw Id Ij Ir Iu Ji Jj Jn Jo Jq Jt Jv Kd Ke Kn Kp Kr Lv Lw Ly Mr Na Nc Nf Nj Nl Nm Oe Oi Ok Om On Ou Ow Pb Pi Pk Qa Qe Ql Qv Qz Ra Rb Rj Rt Rx Ry Sr Tn Tv Uc Ud Ul Un Up Uw Uz Vb Vh Vp Vs Wc We Wf Wg Zw Tl) Fr(Ad aM As Ax bA bV cN Cp Cq Cs cT Cu Cw dA Dc Dd dM Dp Fa fP Fy Hc Hp Hv Hw Id Ij In Ir It Iv Ji Jn Jq Js Jv Kd Ke Ki Kk Kn Kr Kz Lh Lj Lw Ly Ml Mq Mr Mz Na Nf Nr Oa Oi Om On Or Ow Pb Pc Pe Pi Pk Po Qa Qd Qe Ql Qz Rb Rf Rj Rm Rx Sr Tn Tv Un Up Uv Vp Vt Wb) On(Aj Ao Ap aW aY bA Bb bH bV Co Dk dM Ez Fi fP Fy Hp Hu In Jh Jn Jp Jv Ki Lj Lu Lv Ly Mk Mr My Nn Nr Nv Oa Of Or Ou Pa Pb Pc Pf Pg Po Qa Qd Qe Qh Ql Qw Qx Qz Rf Sf Sr Tv Uk Un Wb Wm Th) Tn(Aj Ba bW Co Cv Ez Fi Hp Ji Ki Lw Mm Mq Mr Mt Mw Nw Ny Qa Qd Qe Ql Qy Sr St Uf Un Ut Vc Vq Wb) Ji(Bg bH bZ Ch eC Ef gL Hu Jp Ki Lu Lv Ly Ma Nc Nn Nr Ql Qy Th) Qe(aW bH bV dM gL Hu In Iu Lu Lv Ms Nc Oi Ql Qv Sf Tv Vb Wf) Qa(aW bH dM Du eC Fw gL Hu Ih In Ir Iu Ki Lu Oi Ou Sf) Ou(Ax bV Cs dA dM Fa Jn Lx Nn Nr Pe Po Ql Rf Un) Un(Bg bZ Ch eC In Jp Lu Lv Ly Ma Ms Nn Oi Pf) eC(Ad Aj bA Cu Dc Id Ir Jn Ke Pk Sr Up) Lv(bW Cv Ex Hp Lw Mm Mq Sr Uf Wb Zq) Jp(dA Eq Hp Jv Mq Mr Nf Ql Sf Sr) Mr(aW bV dM Fi Hu Lu Ru Tv) Jn(bH In Ki Lu Ms Oi Pf Tm) Dk(bV Jv Ki Oi Wb Zw Ye) Mv(Em Ex Fd Hp Lp Wg) Lh(Fi Ki Lu Ms Wb Ye) Ut(bH Gd Hp Ki Sf Wb) Nn(dM Ki Ql Qz Sf) Sr(bH bZ Ef Ki Ma) Tm(Jk Mt Nb Nv Ny) Pc(bV Lx Pf Tr Tt) Hp(Mt Mz Nx Rb) Fy(bH Fi Kg) Nq(Du Em Rt) Lu(Et Qd Ql) Wb(Mt Mz Nx) Qy(bA Ye Tl) Or(Ki Pf Vw) bZ(Em Lw Mx) Ef(Fa Jj) Ql(bV Pf) gL(Ke Qd) ChdM CxUw DuRb FiNr LwMa MtSf MwTv RmVa bVfP} Ly{Ki(aJ aP Ar Ax BA bQ bV bZ cN CS cT Cv dF dG Di Dk dM Et Ex Fa Fb Fr Fy gL Hu Je Ji Jj Jl Jn Jp Kk Kx Ky Ld Lh Lu Lv Lw Lx Mn Mq Mw Nn Nr Nt Nv Nw Oa Oh Oi Ok Om On Or Ou Ow Pe Pf Po Qa Qd Qe Ql Qv Qx Qy Rb Rf Sr St Tn Uf Un Ur Ut Vp) Ql(aJ aP bA bQ bV cN Cv cW dM Ex Fa Fb Fr Ji Jj Jl Kk Lu Lw Lx Mm Mq Mr Nn Nr Nw Oe Oh Oi On

Figure 7 Continued

Or Pf Qe Qv Qy Sr Uf Un) Un(Aj BA bH bV bZ cN cT dM eC Fn Fr gL Ih Ii In Ir Jj Jo Jt Jv Kg Kk Ky Lu Lx Ms Nn Oe Oi Ou Pf Qv Qy Rb Ug Ur) dM(aC eC Et Ez Fa Fb Fr Ji Jl Jn Mq Mr Nn Nr Nw Oa On Or Ou Ow Pe Pf Pk Qa Qd Qe Qv Qy Sr St Uf Ur Ut) Qy(aJ aP Ax bA bV bW cN Cs Cv dG dL Fa Ji Jj Jn Kk Kx Ky Lu Lw Lx Mq Nr Nw Oi Qv Sr) Ur(Ef Ex Fr Jl Jn Jq Lh Lx Mr Nn Nr Oh Ok On Or Ou Ow Pf Po Qa Qe Rb Sr Tn Ut) Ji(aW Bb Fb Fn gL Hu Io Lu Lx Mq Mr Nd Nh On Pe Qv Rb Wm) Jl(aE Aj aW bA bO bR cl Dp Io Jv Kr Kx Ow Qu Qv Rb Rf Uf) Nw(Fb gL Ik Io Jv Lu Lv Mq Mr Ms Nd Nh Nu Po Qv Tn To) Fa(bH bO Dp Fb gL Je Jv Lu Lw Mm Mr Oe Oi Ou Rb tF) Jv(Dk Et Fr Jn Jp Nn Nr On Qa Qd Qe Sr Uf) Ex(cN In Iq Jf Jj Kr Lu Oi Qv Tn Uo) Rb(aP bV cN Cs Jj Lx Mq Ow Pf Po Sr) Sr(bH bO Dp Ih In Ir Lu Oe Oi Qv) On(Aj aW Dp Hc Jf Kg Kr Lv Nh Vo) Qe(Aj aW cN gL Kg Ky Lx Qv Tn) Mq(Et gL Kk Lv Ok Om Po Tn) Mr(aW bA bV cN Kk Lv Qv Tn) Wm(Et Jj Jn Jp Jq Qd) Kk(bC bW Cv Lw Mm Uf) Aj(Fr Om Ou Tn Uf) Lx(Fb Nd Nh Qa To) Jj(Dp Ef Ez gL Or) Jn(cN Fb Kg Qv Uf) Kg(Lh Nn Ok Qa) Fr(bO Kx Pk) Lu(Et Pj Rf) Tn(bW Co Uf) Qv(cN Lh Nn) gL(bC Qd Uf) Fb(bA Oi) Mm(Lv Or) Ow(cN In) Pc(Tr Tt) bV(Dp fP) BaKl CsOu PoNh FybH NuJq ToVq JePf KycN OrUf} Wb{Ez(Aj aM Ap Ar As bA bC bL cP Cq Cs cT Cw cX dA dC dM Du Eq Fc Fy Gn Hl Id Ih Ij In Ir Ji Jn Kc Kk Kl Kn Kp Kr Ld Lh Lv Lw Lx Md Mi Ml Mq Mt Mw Mz Nb Nd Nf Nj Nk Nn Nr Nu Nw Oa Oh Oi Om On Or Ow Pb Pe Pf Pi Pk Po Qa Qb Qe Ql Qm Qv Qx Ra Rb Rf Rj Rm Ru Sr Tn To Un Up Uv Uz Vh Vt Wg Ye Tl Th) Nj(Ax bA cP Cs cT Du Et Fy Ih Ij In Ir Ji Jn Js Kx Ld Lh Lj Lx Mj Ml Mq Mt Mv Mw Mz Nf Nn Nr Nu Nw Oa Oh On Or Ow Pc Pe Pi Po Qa Qb Qe Ra Rf Rm Sr Ut Uv Zw Th) Nk(aJ aP bA bQ bV cP CS cT dF Fy Ih Ij Ir Ji Jn Js Ld Lh Lx Mj Mq Mt Mv Mw Mz Nn Nr Nu Nw Oa Oh On Ow Pe Pf Pi Po Qa Qb Qe Qh Ql Ra Rf Rm Sr St Tn Ut Th) Ql(aD aM aS Ax bQ cP Cs cT cW Cx Fy Ji Jv Kc Ld Lh Lj Lv Lx Mj Ml Mq Mt Mz Nb Nr Oe Oh Oi On Or Ow Pe Pf Qm Qn Qv Qx Ra Rb Rf Ru Sr Uv Va Vq) Qa(Cx Fd Fi Ho Hx Ii Ir Iv Js Jt Kd Nc Nl Pg Qd Qh Qm Uz) Or(bJ bN bQ bZ Cs Cx cZ dA Kc Ld Mh Nn Oh Pf Rf Rh Zw Wm) Nl(bA cT Fy Ir Ji Jn Lh Mt Mz Nr Oh On Ow Pf Pi Rm) Ld(aX Ba Bg bH bQ bR bZ Du Fr Lu Lv Ma Mv Nq Ou Rb) Kc(bQ Dk Fr Kk Lh Lv Mv Nb Nn Om On Ou Pf Tn Ut) Nc(bA bQ Fy Ji Lh Mt Mz Nr Oh On Ow Pf Pi) Lh(Bb bN Fi Fw Nf Pg Qd Qh Qn Ra Up) Pf(Ap bL bS cA Dp Jf Jv Nf Qm Sf) Fi(bA Fy Mt Nr On Pe Po Sr Tn) Mt(Bb bL Jt Ko Pg Qd Up) Nf(bQ bZ cS Lv Mv Nd Tn) Cx(bA Kk Mi Mw Sr Ud) On(Bb bL cZ Kr Pg Up) Lv(bN Mq Ra Rf Zw) Fy(Pg Qh Qm Tz) Ra(aX Jf Jt) Rf(bF Nx Ou) Qm(Lx Ow Po) bA(Kd Mx Tz) Fb(Ji Ml) Nn(dA Pa) Mz(Kr Up) Oh(aZ Tz) Uv(bZ Uy) Pb(Ml Qx) bL(bQ Fr) bN(Kk Ou) FaRb FdSr NrQh HlbZ TnUp InOw KdPe} Ye{Qy(AD Af aM Ap As bA Bb bN bQ bU cA Cq CS cT Cw CX dA Dc dH Dp Ez Fr Fy Gn Hc Hl Hp Id Ih In Jl Jn Jq Js Jv Kc Kk Kn Kr Kz Ld Lh Lu Lv Lw Mb Md Mi Mj Ml Mr Mt Mz Na Nf Nk Nn Nr Nu Nx Ny Oa Oh On Or Ow Pb Pc Pe Pi Pk Qa Qb Qe Ql Qv Qw Qx Ra Rb Rf Rj Rm Rt Rz Sr Tn To Tv Ud Uh Un Uo Up Uv Uz Va Vp Vt Wg Zw Wm) Ql(Ap bH bN bR Cx Dp Ez fR Fy Jl Jn Kc Lu Mr Mv Mw Nb Nj Nk Nn Nr Nu Ny On Pb Pc Pi Qa Qe Qv Qw Rb Rf) Mw(Af Ap Bb bN bO bU Cx dA Dp Ez Je Jl Ju Jv Kc Mr Nc Nf Nj Nk Nl Nu Oh Ow Ra Rb Sf To) Ez(Af Ap bL bO cX Hp Ih Je Jl Jn Kl Ld Nf Nj Nu Ny Or Pc Pi Qa Qb Qe Rm St To) Qa(aV bH bO bR Cx cZ dA dD dH Fn Je Ju Jv Ke Nc Nf Nj Nl Pa Qw Rb Sf Uh Up) Rb(bN Cx Hp Ih Jl Ld Mq Mr Nf Nn Nu Ny Oa On Pe Qb Qe Rf Rm Sr St) Je(bN cS Cx Ih Jl Jm Jp Ks Lh Mj Mr Mt Mz Nn Nr On Qe Rm St Zw) Jl(aV bH bN bO bR Cx cZ dA dH Kr Nc Nf Nj Nk Nl Pa Qd) Qe(Ap bH bN bO Cx cZ dA Ju Jv Lu Nc Nf Nj Nl Sf Uh) Rm(bH Cx fR Iq Jf Lu Mi Nj Nk Nl Qn Ud Va) Nn(aV bO Dp Hp Ju Jv Kc Nk Or Pa Pc Sf) Nf(Fr Iz Jk Mv Nj On Qw St Tn Ua Ut) Cx(bA cT Jn Mi Ny On Pi Qw Sr Ud) Nj(Fd Ih Jn Kz Ny Ow Qb Sr St) On(aF aV Bn bO cX cZ dA Or Up) Nk(Ih Jk Jn Mv Ny Pi Ua Ut) Qw(bN Ih Kc Ld Mq Nw Qb Rf) bH(aM Fy Ih Ld Mr Qb Zw) Hp(cS Fr Jp Mj Oh Tn) Kc(Dk Hu Iz Mv Ut Wd) Or(bJ Fn Ih Jm St Zw) Ny(Bb cZ Jv Ki Nc) bN(Dk dM Jn Lh Ou) bO(Fr Fy Lh Mt Nr) Mv(dA Dp Ih) Jm(bA Mi Ud) Jn(Fb Nc Nl) Ut(Bn Nl) Pc(Ba Rf) dA(Mj Mz) DpJh NuLh LuIh MtcZ HuLd KsbA aFbQ dHfR} Aj{Tn(aM Ba bC bJ bL Dk Dp Ef Et Ez Fa Fb Fr Gl Hc Hp Hu Jg Ji Jk Jl Jn Jv Kf Ki Kz Lh Lw Ma Mn Mq Mr Mt Mw Nc Nf Nj Nk Nl Nn Nr Nw Ny On Ow Pa Pb Pc Pf Po Pz Qa Qd Qe Ql Qm Qn Qt Qw Qy Rf Rg Sr St Ua Uf Uh Un Ut Vq Vw Zq) Ef(aD aJ aM bA bC bM bV CS cW dG Fa Fr Fy Gl Gn Ji Jl Jp Ki Ky Lx Mq Mr Ms Nc Nn Nr Oa Oh Oi On Pe Pf Po Qa Qd Qe Qv Sr Ut) eC(Ad As Cp Cq Cu Cw Dc Hv Hw Hx Ib Id Ij In Ir Iv Jn Jq Js Kd Kn Kp Kr Mz Na Nb Nf Pb Pe Pi Pk Qa Rj Sr Uc Un Up Uv Vp Vt) Lv(Ba bJ bV cN Dk Et Ez Hu Iv Jl Jn Kx Mq Nf Nn Nr On Ow Pe Po Qa Qd Qe Ql Qt Qy Sr Un) Fy(bH bW Cv Ez Fb Fr Hu Ji Jl Ki Lu Lw Mm Nn On Ou Ow Qe Ql Qt Qw Qy Uf) Jl(aW bH bO bR dA Dp gL Hc Hu Lu Mr Ms Nc Nf Nl Nr Oe Qe Qy Tv Wh) Hu(aM bV cT dF Et Ez Fr Ji Jn Ma Ml Mr Nn On Or Ou Qa Qe Sr) Fr(Dp Hp Hw Iv Jn Kx Kz Mr Nf Nr Pi Pk Qe Ql Qz Un) gL(Fa Iv Ji Ke Lh Mq Mr Ny Pe Po Qa Qd Qe Un Uv Vt) bZ(Id In Ji Jq Lh Ml Or Pi Pk Qa Sr Un Uv Vt) Nn(Dp Ez Ki Lu Mr Ms Or Ou Qv Qz Sf Un tF) Qy(bA cT dF Hl Jn Ma Rt Uw Uz Vh Wg Zw Tl) Ez(Jn Nr On Ou Pk Rt Uw Wd We Wg Tl) Lu(Et Ji Jn Lh Nr Po Qa Qe Ql Un Zq) Ma(Dp Jn Mq Mr Or Qe Ql Sr Tv Un) Qe(BA bQ Mr Ms Nc Nf Nl Wh) Ou(Jn Nf Nr Pk Rf Un Zq Th) Dp(Ba Cu dF Jp On Pf Sr) Jn(Bg Ch cS Mr Nc Pf) Jp(Hp Kx Kz Ql Sr Un) Un(bF Bg Ch Ms Oi) Rb(Uw Wd Wh Zq) Pf(bR Mr Nc Nf) Ba(aM Mr Pc) Nr(Mr Nc Nk) Lh(bJ Ms Nc) On(Bb Sf Ux) tF(Bc cW Mq) Bg(Sr Zw) Qa(Ms Wh) Tm(Jk Mt) Pc(Tr Tt) bQ(Hl Zw) AoUt ChSr CxUw DkTh MwTv WdRm OrVw bVfP} Oi{Nn(bJ bO Dp Et Hc Hu Ir Ji Jj Jl Jn Jp Ki Kr Kz Lh Lu Lv Lx Mb Mi Mq Mr Ms Mt Nd Ne Nh Ns Nt Nw Om On Pa Pe Pf Po Qa Qd Qe Ql Qz Rf Un) Qa(aW bH bO dM Dp Et Fr Hc Hu In Jg Ji Jj Jq Kg Ki Kr Lu Lv Lw Lx Ma Mm Mn Mq Mr Mt Nf Nt Nw Oh Om On Pc Pf Po Ql Qy Ur) Po(bO Dp Et gL Hr In Ji Jj Jl Jn Jp Jq Ki Lu Lv Lw Ma Mm Mq Ms Nh Ns Nt Nw Oh Ok Om Pb Pc Qd Qe Ql Qy) Un(BA bH bN bO bV bZ cT dM eC Fn gL Hu Ii In Jn Kg Ki Kr Kx Lu Ma Mq Ms Nc Nf Nr Ql Qv Qw Qy Rf Ur) Jn(aW bH bZ cN dA dM Dp Fb Fr Hc Jg Jj Jv Kg Ki Kr Kx Lv Lx Mq Nw Oh Om Or Pc Pf Ql Qy Rf Ur Wm) Ql(aP aW bA bH bV cN Cs dM Fa Fb gL Hu Jj Jl Ki Kx Lu Mr Ms Nr Qe Qv Qy Rf Tn Ur) Qc(aW bH bO dA dM gL Ji Jj Kg Ki Kr Lv Lx Mv Nf Oh Pc Qv Qy Ur) Ji(In Io Jj Lu Lv Ma Mq Mr Ms Mv Nf Nt Oh On Pc Pe Pf Wm) Qy(Ax bV cN Cs dM Fa Hp Ih Kx Lj Nf Nr Oa Pk Qv Rf Tm Th) Dp(aP Ba bQ bV Fa FR Jj Jl Jp Ky Lu Nr Nt Pf Sr Uf) Mr(aP aW bA bR bV bZ cN dM Et gL Kx Mn Nw Om) Jl(aW bO dM Hc Jj Kr Kx Mq Nf Ns Oh To) Sr(bH bO Cx Ef Hu In Ki Ky Lu Ms) Nr(aJ bV cN dM Fb Hc Jv Ki Ur) Mq(Ef Et Fr gL Mm Nw Oh Om Pf) Hu(bV Cs Et Fa Ki Kx Oa Rf) Ef(bV Cs Fa Jj Kx Oa Ur) gL(Fa Hc Kz Nf Ny Oa Qd) Ki(Ba bQ Ex Nq Pe Rf) Nw(Lv Ma Ms Mv Nt Pf) Et(Jj Lu Lv Mv Nf) Fr(bO Hc Kx Kz Nf) Oh(Ik Lv Mv Nt) Ba(Hc Kl Ss) Ex(bN bV Mv) Lx(Ih Lv Qb) St(aW dM To) Kx(bZ Ma Mw) Pe(Jj Lv Om) bH(Fy Ih Rf) Ez(dM Hp) Nf(Fb Tn) Hc(Mn Tn) Qd(dA Kr) Kg(Fy Lh) fP(aP bV) NqJv LuRf MvJj MwaW SfNy ZqbN ZwJe OrbJ PkeC} Hc{Fr(aF aO aU aW Ax bA bO bV cN Cs cT Cu Cw Dc dM Fy gL Hv Hw Id Ij In Jj Jn Jv Kd Ki Kp Kx Ky Lj Lv Lw Mn Mq Ms Na Nn Nr Oa Oe Oh Ow Pi Pk Ql Qv Qy Qz Ra Rf Rh Rj Sr Tn Tv Ud Up Ur Zq Th) gL(aJ BA Bc cT Cv cW dG Dk dL dM Et Ez Fa Id Iv Jh Ji Jj Jl Jn Jq Ke Lh Li Lw Lx Mq Mr Mt Mx Nd Nn Nw Ny Ok Om On Or Ou Ow Pe Pf Po Qa Qd Qc Ql Rb Sr Ul Un Ut) Tn(aJ BA bE bH bV bW Co cS Cv dM Fb Id Ji Jj Jl Jn Jq Ju Jv Ke Kg Ki Ky Lh Lu Lw Mq Mr Mt Mw Nc Nj Nk Nn Nw Ny Oh Ou Ow Qa Qd Qe Ql Qy Sr Uf Un Ur) Lu(Ax BA Dk Et Fy Ji Jl Jn Jp Jq Js Lh Lv Lw Ma Mn Nn Nr Nw Oh Ok Om Ow Pe Pf Pj Po Qa Qe Ql Qy Rf Sr Tr Un) Lv(aJ aP Ax bA bV bW cN dG dM Ex Fa Jj Lw Mn Mq Nn Oh Pf Qv Sr Uf Ur) bA(bF Bg bZ Ch Dk Hu In Jp Ma Mn Nj Nn Nr Or Ou Pf Qy Sr) Nn(aW bV cN cT dM In Jj Jv Ki Ky Ms Oe Qv Sf Tv Ur) In(dF Ji Jl Jn Lh Lx Oh Ow Pe Pf Po Qa Qe Sr Un) bV(Jn Lx Mn Nq Nr On Or Ou Pf Qy Ut) dM(bZ Fy Jl Jp Ma Mr Nj Nr On Pf Qa) Qy(cT Fa Pf Qv Ru Tr Uw Va) Jl(aE aW Ii Ms Oe Qv Ru Ur) Ou(Ax Fa Qv Rf Ur Th) bZ(cT Id Ji Lw Sr Un) eC(Ad Id Mw Ny Om Pk) On(aW Sf Ur Ti Th) Ba(Jp Qv Tv) Lx(bR cA Ma) Qa(aW Ur Wh) Lh(Ms Qv Uy) Uw(Ez Nj Ql) cT(Bg Jp Ma) Fy(bH cN) Jj(Jn Nr) Pf(Kk Ql) FatF EzFc MrUx NbOp NjZq QeWh JpJv OrVw} eC{Pk(aD aE aJ aP aW bA bI bP bV Ch cI cK cN Co Ct Dc dG dJ dM Id Jj Jo Ju Jv Kg Ki Kk Kr Kx Lu Mg Ms Na Of Qg Qu Qv Un Ur Vo) Un(aD Ao aW bH bI bO bP bX Ch cI Co dM Ih Ii Ir Iu Iz Jg

Figure 7 Continued

Figure 7 Continued

Rg) Po(bL Co Nc) Nw(Pa Qz Rg) Iv(cN Jf) Kg(Uv Vt) On(Af Kl) Ur(In Uv) CoOa LwHf NybL} Jl{Kr(aW bA bH dM Et Id In Jj Jn Jv Kx Lu Lw Ms Nn Oe Ow Qv Sr Tn Tv Un Tm) bO(aD aE aW bA bR bV dM Gh Ii Io Iu Jv Kx Lu Ms Oe Qv Ru Sr Va) Cx(aW dM Du Eq Gn Hl Rt Ru Uw Uz Vb Vh We Wg Zq Tl) Nf(aE aW bV dM Et Ii In Io Jj Jo Kx Ms Ns Pb Qv Ur) Pb(Gn Hl Io Jj Po Rt Tv Uw Uz Vb Vh Wg Tl) aW(bR Db dH Hf Jv Kz Mr Nc Nk Nl Oe Pc Pk) dM(bR Db dH Hf Kl Kz Nc Oe Pa Pk) Po(Ii In Io Jj Ms Nc Nl Pa) bR(aV bH cC dA Ii Lu Ms Nc) bN(Uz Vb Vh Wg Zq Tl) Eq(Bg bZ Ez Ma Vp) Ii(Kx Kz Pk Rf Un) Jj(Hu Io Nc Nd Ns) Fc(dH Fi Fw Kc) Nk(Sj Ux Wf Yd) To(Hv Jv Pk Rf) dA(bS cA Gd Nd) Af(Ru Vb Zq) Fi(Iv Pi Rb) Ms(Io Nn Un) Nc(aE Ne Nh) Pa(Ru Tn Tm) Ba(Kl Ss) Db(Iz Ki) Nl(Kx Ne) In(Kz Pk) Io(Jn Ns) Qv(Jv Kx) Kc(Vb Vw) CqJn ExGd FdPi FnTv MaKl HuIz IrKz QyTm JvbH VaaV bVfP} Lu{Et(Ap bO bR Co dA Dg Hu Jj Jn Jv Ki Kl Kr Kx Kz Lj Lw Mg Mq Ms My Nn Ns Nw Pb Pc Pe Pk Po Ql Qz Rf tF) Un(Af aW bA bH bN bO bR bX Cx Fn Ii Iz Jo Jt Jv Kg Kl Kr Ma Mr Ms Nc Oe Ow Pa Pb Pc Qu Rf Rh Ur) Nw(Hu Jj Jn Kz Lw Mq Ms My Na Ns Oe Oh Ok Pb Pc Po) Rf(aM bO Jn Jv Ki Mr Nf Nr Oe Or Ow Pc Pk Ql Vt) Po(bO bR fP Hu In Jj Mq Ms Ns Oe Pb) Ki(Ex Jn Kx Kz Nf Nn Nr Pe Pk Ql Sr) Mr(aW bA bR bV dM Kx Pk Ql) Jn(bO bR Eq Jv Kr Kx Kz Ur) Sr(bO bR Cx fP Jv Oe Ql) Kz(Cv Lw Lx Mn Nr Ql Qy) Nf(bQ Cv Fb Pj Ql Qy) Nn(bO bR fP Jv Mq) Zq(Af bN Cx Kc Kl) Mq(bR Mm Oh Om) Ql(Kx Nc Pk) bO(Lh Nr Zw) Cx(Cv Em) Eq(Rm St) Ex(bN Pb) Qb(Jj Lx) Qy(Pk Tm) Pc(bJ bR) CsEf GbKc NrJv MyOn IhTm JjJm OkPb OwPc bVfP} On{Eq(aV Bb bH Bn bO bZ Cx cZ dD dE Ez Fd Fi Fn Ii Je Jf Jt Kd Ke Ko Kr Nc Nf Nj Nk Nu Ok Pa Pb Pg Ql Qn Qy Uh Up Wc) Kr(Ao aW Bb bH bV Co Cs dM Hu Jn Jp Ki Kk Lj Mn My Nn Nr Nv Oa Of Or Ow Pb Pf Qd Ql Tv Wh Th) Fi(Af Ap Bn cX De Fc Ki Kz Mr Or Pc Qz Rb) Nf(aW bV dM Ii In Jj Kg Ki My Ns Of We) Pb(Hl Jj Jn Mb Mq Mr Nd Ns Pe Po) Po(Ii Jj Jo Ms My Ns Pa Pc) Th(Af bO Cx De Je Nk Up) Kz(aW cN dM In Jo Kg Ki) Pa(aW Ax Cs My Pf We) Tm(Ap Jv Nc Nk Nl) Ki(aZ Db dE Kx Lt) Hp(Jt Kc Nk Nl) Yd(dH Nk Ql Rb) bO(Si Va Wc Tl) Nd(Hu My Of) Je(Wd Wf Wh) Kf(Hl Uz Wg) Ap(dM Uf) Fc(Fw Kc) Mq(Et Ms) Hf(Rt We) Wc(dA De) Wh(Qy Up) Tl(Af Cx) Va(aV Kc) BaKl GddA MbNa MraW NcUx HlIi InQb SiaV WfUp JvbH bVfP} Qy{Kc(Fc Fd Gb Gn Hl Rt Ru Ry Uw Uz Va Vb Vh Wc Wg Zq Zw Tm Tl) Tm(Ap bQ Cs cT Jv Nf Nu Ny Or Pc Qv Ra Rc Ru Va) Ms(bA bV Cs dM Fa Jn Kz Nf Nr Pk Ql Qv Sr Un) Wh(bQ cT Lx Ml Mq Mt Nr Pf Po Qx Ra Sr Tn) Pb(Gn Hl Rt Ry Uw Uz Vb Vh Wc Wg Tl) bA(aW Ct Hu Ib Ma Mr Oa Of Pc Rf) bN(Em Gn Hl Rt Ry Uw Uz Vb Wg Tl) Va(bO bU Ih Jn Mr Ql Qz Rb Rm) Eq(bQ bZ Fr Ma Mt Nr Pf Tn) Tn(Co Hu Iz Kx My Nf Of) Qz(Hl Rt Ru Uz Wg Zw Tl) Qv(Ki Kx Kz Lt Nf Pc Th) bV(cA fP Ki Kz Nc Nf Oe) Du(bS cA Cx Nj Nk) Fi(Ld Lh Nr Pe Pi) Ld(Fc Fd Ho Lt) Mr(aW Ru Sj) Ux(bQ bZ dF) Ap(Uf Zw) Em(Af cT) Fa(Lt tF) Ex(Gd Ki) Ib(Uz Wg) Tr(Mk Pc) Ii(Pe Sr) Sj(Nk Nu) We(Mt Mz) Rz(bQ cT) Oe(Cs Mq) GdbQ WcPi RaVb RuPc RfaW} Fr{Kr(Ad Cq Cs Cu Cw Ij Iv Jn Js Jv Ki Kn Lh Lj Ml Mq Nf Nn Nr Om Or Ow Pe Pi Pk Ql Qz Rj Sr Un) Nf(aW bO bR bV cN Co Cs dM Hu In Iz Jj Jk Jv Ki Mg Ms Mv My Ne Nh Nj Nl Nt Of Qu Qv Ur) Kz(Ao aW bH bO Co Cs De dM Ii In Jj Jv Kg Ki Kl Qv Ur) bO(aM bA Cs cT Eq Mq Nr Po Qv Qz Sr Va Zw) Kc(Eq Fc Fd Gb Gc Hp Uw Vw Zq) Eq(bN Cx Ez Ih Jm Nk St) Ms(Jn Mq Nw Po Un Wm) Nd(Hu Jn Mp Na Nw Qb) Pk(Bb De dM Jv Kg Ki) My(Jn Lj Mq Mr Na) Kl(Ba Et Jn Ma Rf) Pa(Cs Kx Pe Po) Af(Hp Vw Zq) Jj(Mq Po Qb) fP(bV Fa Qv) Nc(Ne Nh) Hp(Pb Qz) Kx(Jv Ki) Un(bX Ko) CxGn PoPb ThNk MbNa MqdM MraW HuIz UxaV} Kc{Zq(bQ Dk Iz Jk Jp Kk Mr Mv Mw Nb Nj Nn Nu Or Ou Rb Tn Ut Vp) Uw(bH bO Cx Jp Ki Mr Mv Nb Nj Nu Or Ou Pb Pc Ql Rb St Tn) Hp(bZ Co cS Dk Ez Jp Kk Mv Mz Nn Nq Ou Rb Tn) Vw(Dk Kk Lh Mr Mv Mz Nb Nx Or Ou Pc Rb Tn Ut) Wd(aM cX Et Jn Jp Mz Nw Or Ql Rm St) Mv(Du Eq Gb Gc Hl Ho Uz Vh Wg Tl) Jp(Fc Hl Rt Uz Vb Vh Wf Wg Wh Tl) Ux(Dk Mr Mz Nb Ny Or) Fc(Ez Mz Nn Ql Ut) bZ(Hl Rt Uz Wg Tl) Tn(Eq Fi fR Vq) Tm(Iz Jk Nv Ut) Ql(Ru Uy Va Tl) Or(Rz Vb Wh Zw) Op(Kk Nb Nu) Dk(Ru Va) Fd(Nj Pf) Gb(Nn Ou) Hl(bQ Nq) Wh(Mz Rm) CuFi DuPe EqIz GcMw NnVc StWf RxNy RmVa} Pb{Po(Et In Io Jj Jq Lw Lx Mq Ms Nk Nw Ok Om Pe) Hl(bQ bZ Cx Ez Fb Gn Mr Mw Nj Nk Nn Nq Ql) Mq(Et Jq Lx Mt Nn Nw Oh Ok Om Pf Tn) Ez(Gn Hp Rt Ry Uz Vb Vh Wc Wg Tl) Cx(Gn Rt Ry Uw Uz Vb Vh Wg Tl) Fi(Cu Lh Mz Nb Nr Ny Ok Pi Tn) Lx(Hw Ij Ir Jn Jq Na Nf) Nj(Du Fd Rt Ry Uw Vb Tl) Fb(Gn Rt Uz Vb Wg Tl) Uw(Af bJ bN Ih Je Ql) Mt(Eq Uz We Wg Tl) Lh(Fc Fd Ho Jj Lt) Vb(Af bN Nw Ql St) Tl(Ih Mr Mw Nw) Or(Hp Vw Zq Zw) Fd(Mz Pf Pi) Mr(Ru Tn) Wh(Jn Pi) Ki(bA Ex) Un(Ms Va) Vw(Ap Uv) BaKl FcPf MwTm NbOp NfNw TnVq ZwJe WeOm JjPe PkdM} Ki{Sr(aZ bH bO bR bZ cC Cx DB dJ Fn In Kr Ky Ms Nf Oe Qv Tn) Ex(bA bR bS bV cT Ip Jj Ky Nl Nt Pc Pi Ql Qv Ra Ur) Nn(bO bR Db Hf Jv Kr Kz Ms Nc Nf Oe Pc Tm) Jn(bV bZ DB Hf In Kg Kr Ky Ms Oe Qv Ur) bQ(bR Eq Fc Fi Jv Kx Ky Lt Nf Pk Th) bV(aZ bR Db dE Pc Pk Ql) Qv(Db Kz Nf Nr Pc Ql) Ky(Db Kz Mq Nf Nr Or) bA(cC Db Fn Pc Ql) In(Kz Mq Ow Pk) bZ(Kz Or Pk Un) Mt(Fi Lt To) Ql(Lt Ms Ru) Pc(cT Tr Tt) Db(Fa Pe) Po(bH bO) Nr(Oe Or) Mq(Oe Tn) Jp(Kz Nf) BaKl DuLd ThNk LxbR MaKx HuKz TmNy PcbH} Un{Ms(BA bH cT Ef Fn Ii In Jo Jt Jv Kg Kr Ma Mq Mv Nc Nf Nj Nl Nn Or Ow Pa Pc Ql Qv Ur) Ii(BA bZ cT Gl Jn Ma Mr Mv Nf Nn Nr Pe Pf Po Rf Rh Sr Tn Th) In(bA Bb cT Jn Jv Kr Kz Ma Mq Nc Nf Nn Ow Qv Qz Rh) Ma(Ao bH dM Eq Jo Jt Jv Kg Kl Kr Ur Vo) bZ(Ao Bb Co Jt Jv Kl Ko Kr Nc Ph Qz) Nj(aW Lt Tn To Tl Th) Tn(Jv Ko Kz Nk Nl) Jt(cT Jn Nn Pf Rh) bA(bO Cx Fn Nc Nl) bH(bR cT Qv Rf Rh) Kr(Nn Ou Pf) Cx(aJ Ur) Va(Ke Rb) bV(fP Nc) BaKl BbbF DlcT ThNk FnNl NfQv TrPc KobQ} Mr{dM(Bg bR Db dE Hu Jn Kr Ma Ms Nc Nf Nn Nr Oe Pa Pc Pk) Fi(Af bQ bS CX Fc In Lh Nr Nx Pc Pi Rb) Af(Hl Rt Ru Uw Ux Uz Vw Wg Wh Zq Tl) Jj(bR Et Jm Jn Lh Mn Nw Nx Ok Qb) bV(aW bH bR cA fP Ms Nc Oe) Tn(Co Jv Kg Kr Pc Rg Ur) Ru(bH Cx Or Pa Pc Rb) Va(aV Jn Nr Ql Qn St) aW(cS Jn Mw Nn Oe Pc) Ap(Rz Ux Vw Wh Zq) bH(aD bA bR Th) Du(Ih Ld Ow) Ms(bA cN Ql) In(Nw Ow Pk) Th(bW Nk) Mt(Si Wc) To(Jq Nw) Kr(Nn Ou) Pi(Fd Wc) aJ(bR gP) cN(bR Oe) BaKl EqEz MnMq MvWf TrPc IuSr QvKx LtbC OrUy} Mq{In(dM Et Ex Ih Jn Jq Js Kz Mm Mn Nn Nw Oh Ok Om Ow Pd Pk Po Qb) Et(Io Jj Jo Lw Lx Mg Ms Ns Nw Pc Po) Ms(Ef Mn Mp Nn Nw Oh Ok Om Po) Jj(Jn Jp Ma Mn Nn Nw Ok Po) Lx(Ir Jn Jq Nd Ns Of) Pc(bA Jq Nn Qv Tn Tr) Po(Ii Jo Ma Ok) Th(Cx Nc Nk Nl) Nn(Hu Ii Mg Ns) Mn(Jq Ne Nh Ns) Om(Hu Mg Ns Of) dM(Bg Ch Ma Nr) fP(aJ aP bA bV) Ap(bF Ex Vw) Ef(aE Ik Qv) Tn(Kr Of Rf) Nw(Ii Ma Ns) bR(bQ bZ Hu) Jv(bF bZ) FiRb MpNd IiVu IoJp QubZ JnaW KrOu OfOk aJgP} Or{Zq(Af bN cT CX dE dH Fn Hb Jv Mh Nj Oh Ow Qn Rh Wm) bJ(aE aW bA bV Gc Hl Ms Rt Si Tv Uz Vh Wg) Vw(Af bN Cx dE dH Fn Jt Kl Nf Pa Up Vo) bN(Du Gn Hl Uw Ux Uz Vb Vj Wg Wh Tm) Zw(bO cZ dE Fn Je Nc Nk Qn) Fi(Ax In Ld Lx Nr Pe) Nc(bV dM Jn Ru Ur) Hp(Cx Fn Mh Nj Rh) Fd(In Ld Pe Pi) Eq(bQ Ma Nn) Fn(bA cT Ru) Ld(Fc Ho Lt) dM(bR Db Nl) Th(Nk Ow) Nr(Co Kg) Lx(bR Nd) Ru(fR Nk) bZ(Jv Kx) BaKl DuIh WmLt ExKr NnTm NfQv NjTl TrUk TnOf JnaW RhVj} Nj{Du(bO Cx dA Et fR Hf Ih Je Kz Mt Mw Nf Nq Pa Pc Ql Rb St Th) Zq(Ap Bb bN Dg Kl Kz Ld Nf Oa Pc Pi To) Tm(Fd Ih Jn Mt Nn Ny Oa Ow Pi Rm St Th) Fd(bN Cs Ez Ld Lj Nf Ra Tl Th) Hp(Et Ez Ld Lh Lj Mt Nw Pc Th) Eq(Ez Jp Nn St Ut) Nf(Hl Op Rt Uw) To(Nw Qd St Vq) Kz(Hl Op Rt Uw) Pc(Hl Ru Vw Zw) Th(Mw Nw Ry) Hf(Rt Uw Zw) Sj(Et Mw Ql) Lt(Et Ih Ir) Rm(Si Va Wc) St(aW Tv) Tl(Pi Ut) Pa(Hl Zw) FnbA SraW QlUy PkdM} Nf{Qv(bH bZ Dk Ef Hu In Jn Jp Jq Lx Mm Mn Nn Ou Pc Qd Ql Tn) Jj(Et Jn Jp Lh Ma Mm Mn Nn Nw Ok Om Pf Pg Po Qb Qd) Lx(bR bS cA Fn Hq Hx In Jp My Ny Of Tj) In(Et Ex Nw Ok Om Ou Ow Sr Uf) Tn(bW Co Cv Jv Lw Nw Qd St) Jp(Du Jv Kg Qu Ur) Nw(Ii Ms Nc Nh Ns) Et(Jo Ms Ne Nh) dM(Bg bZ Ch Ou) Du(Mt Nr) Op(Nb Nu) Ok(Jo Ms) bV(bF fP) CxUw FiLh GdNr LwbZ MnNh MzWc QdaW NxUy OuUr} Pc{Tr(bH Bo bV cN Db dM Gl Jj Jv Kg Kx Mp Na Nk Nw Po Qd Rf Sr St Uh Ur) Tt(bH cN Db Jj Na Nw Uh Ur) Qv(bV dM Hu Jn Jv Kx Nn Po) Fi(Cu Jn Mt Nn Nr Pe Tn) Ow(dM In Wd Wh Th) Ur(Jn Pf Po Tn) Zw(bZ Je Nq) Wd(Oh Rf Wm) Ql(bV Ru Va) Vw(Ld Nk Pf) bA(bJ Hu Pk) dM(Ma Nn Rh) Po(In Ms) Eq(bZ Ez) Tn(Jv Kg) bV(bJ Rf) BaKl BcUy EzRu GnLd NnJv LxbR MtSi} fP{bV(aD aJ aP Ax Ba bB bE Bo bR cA cE Ch cN Cs cT Cv cW Dc dF Dk dM Et Fa Hx In Jh Jj Jn Jq Jv Ke Kg Kr Ks Kx Ky Kz Lw Lx Mi Ml Ms Mv Mw Nb Nc Nk Nn Nw Ny Oc Oh Om Ou Ow Pe Pf Po Qd Qv Rf Rh Rj Sr St Ud Uh Ur Ut) Fa(aJ aP aX bA cS cT Jj Ky Rf Ur tF) Sr(Bo Qv Ur) ExbA UraP}

Figure 7 Continued

Cx{Ql(Du Gn Hl Lw Rt Ru Uw Uy Uz Va Vb Vh Wg Tl) Je(Du Hl Rt Ru Sj Va Wc Zw) fR(aW bl bR cT Gn Hl Uz Wg) Sr(bH dJ dM Fi Nc Uk Ur) Em(bA cT Ud Ur) Mw(Si Wd Wf Wh) Wc(Jn Mi Nb Pi) Jq(bH cN dM Ur) Cv(bA cT Th) Eq(bQ Tn Ut) Si(Jn Mt Ny) Zq(bA Nu Ud) Va(Jn Rb Rm) Th(Uw Vs) Fi(Lh Ny) Nb(Tm Tl) cT(Uz Wg) BaGn LwUr MiTm HlbH HpUd JncN NwbA UwPa} Nk{Th(bC bH bW cN Cv Du Et Ez Fd Gz Hl Hp Jk Lh Lw Lx Mm Mp Mw Mx Nv Nw Ou Po Qd Ql Sr Uf Ul Vq Vs Tm) Hp(Jp Lh Mj Mt Mv Nr Nw Qb Qh) Va(Ih Jm Jn Ql Rm St) Du(bQ Mw Oa Ql St) Mt(Si Sj Ux Wc Yd) Tm(Nn Nw Ny Rm) Mw(Ru Sj Wh) St(Tn To Tv) Si(Jn Rm) Wc(Jn Ow) EqJp FdPf NrdM HlRm ToVq TnJv IhLt SjQl QbVw} Eq{Ez(Ap bF BG bN bO bQ bZ Ch Il Jp Ma Mt Mw Nb Nq Nu Ny Ou Pi Qv Rb St Tn Ut) bZ(Ba bQ Fb fR Ih Jk Jn Mt Mw Nn Nu Ny Ow Pi Ql Rf St Ut) Ma(Fb Fd Hu Je Jk Mt Mw Ny Qb Qd Ql St Ua Ut) bQ(Af bN Jn Mw Ql) Bg(Mt Ow Rf) Ut(BN De) Nq(Ow Pi) Mt(bF bH) Tn(Fi Up) MvOw NcJp RfbF} Rb{bN(Du Em Hl Ru Uw Uz Va Vb Vh Vw Wd Wg Wh Zq Tm Tl) Wc(aM Cs Ih Jn Mz Nw Ny Ow Pe Pi Pk Qb Rm Sr St) Fi(Cs Fa Ih Iv Ld Nn Nu Nw Ny Oa Pe Pi Sr) Va(Bc bJ Ih Jn Ql Rm St) Si(Ih Jn Ow St) Wh(Cs Nu Oa Pe) Ld(Hp Uw Ux Vw) Af(Uw Vw Zq) Pe(Fd Lp Uz) ExGd HoIh ZwJf QlUy} Ef{Gd(aD aM Ax bA Bc bV Cs cT cU Ex Fa Kx Ld Lj Nr Oa Oh Ow Pe Pk Ql Qx Ra Sr) Jj(aD Cs Ha Jn Ky Lj Oa Oh Ql Uv Vt) Fa(Co Hu Ii Jo Jv Kg Ms) Sr(Ao Ik Iz Jo Kg Ms Ue) Kg(aD Cs Pe Po) Pe(Co Ii Jo) Cs(cN Ur) Qv(Kx Oa) bV(cA Nc) AfGn PoJo LxKr OaUr} Mt{Tm(Af Ap Bb bH bO Dg dH Nc Nl Oe) Si(Af aV bO bR bU dA Ql) Hl(Ii Jt Ke Kf Nm) Wc(bO dA Hf Je Jv) Wg(Jt Kf Ko Kp) Uz(Jt Kf Ko Kp) Af(Lt We Tl) Wh(Fn Je Pa) Fd(Ii Kf) Fi(bN Kz) Hp(Jt Nl) Tn(Jv Pa) Sj(dD Je) We(Fn Pa) Va(aV bO) Vw(Ap Dg) DuLd NcUx ToJv ZqJt JfLt TlbO KfRt} Po{In(bO Et Hw Ir Jn Jq Lw Ma Ms Nh Nn Ns Nt Nw Oe Oh Ok) Ms(Et Jg Jn Jp Lh Ma Mn Mw Nn Ns Nw Oh Ok Om) Ii(Jp Mn Nh Nn Nt Nw Om) Pa(Nw Ok Om Pf Qv Tn) Jj(Jq Ma Nn Ns) Et(Io Jo Oe) Ns(Jp Nw) Nh(Nc Nl) Qv(bH bO) IoJp JoOk bAbO bHbR} Jn{Ms(cN Jv Nn Nw Om Ql Ur) Jj(Et Ik Ma Mv Ok Pf Wm) Nc(bV cN dM Kg Tm) In(Jv Kr Kz Nw Wm) Jt(Ba Dk Sr Uf) cN(bR Db Nl Oc) Ii(Gl Sr Vq) Kg(cS Hu Oe) Kr(Nn Ou Pf) Af(Uw Ux) Si(Mw Ql) Jv(bZ Tn) ApWh BaKl BbWd FiVq NlTm JfLt QvPa OebV VabO} Tn{Pa(Co Fi Jv Lw Mm Nw Sr St Uf Vq) Mw(Ch Co Hu Iz Jk Jv Kr Of) Kg(Et Ez Gl Lh Rm Sr) St(Hf Jv Kr Kz Nc) Kz(Co Cv Lw Nw) Fi(Af Fc Qb) Hp(Af Jv Qz) Hf(Lw Nw Sr) Jc(Wc Wf) Sr(bO Jv) Kr(Nw Qd) NcNw JvNy QlOe VabO} Va{bO(Et Ez Gl Jp Kn Lh Mw Mz Nn Nr Nw Ok Ql Rm St Ut) Rm(Af bH bN dA Ez Iq Je Nc Nl Qn) aV(Jp Lh Mw Mz Nn Nr Nw Ql Sr St) dA(Jm Ks Lh Mz Nr Nw Nx St) Ql(bN cX Jm) Je(cX Nr) MwcX} Nn{Jv(bH bQ bR Kr Ms Nc Nl Qv) Kr(dM Lw Nc Ou Qv Qz) Pa(dM Et Nw Qv) bO(bA Gh Qv Tm) Ap(fR Zq Tm) Ms(bJ Nw Ql) Nc(dM Ne Nh) Gd(dA Je) Kz(dM In) bR(cN dM) AfZq BaKl ChtF FcFi NhJj SjJe TmaV KgUv} Sr{bH(aM bN bR bZ Jv Kr Ma Ms Nc Nl Qv) Jv(bF Bg bO bZ CH In Ma Qv) bO(bA bZ cS In Ma Ms Oe Qv) In(aM bJ Kz Pk Ql Qz) Kr(bZ Jp Ou) Et(Ii Jt) Ms(Hu Ql) BaKl DubU NrIi PabZ} Kl{Ba(aD aM aY bP bZ Dc dF Et Ex Fb In Jp Jq Jv Kk Ky Lh Lw Lx Ma Ms Mw Nc Nr Nw Oe Oh Ou Pe Pf Pk Qd Ql Qv St Uf Vt) Ez(Fc Hp Vj Vw Zq)} bN{Ez(Uw Uz Vb Vh Wc Wg Tl) bH(Uw Uz Vb Vh Wc Wg Tl) Zq(bA cT dM Mi Ou Ud) Ex(Jj Kk Mi Ud Uo) Tm(dM Mw Nb) Vw(Mi Ou Ud) Em(cT Ud) Je(Sj Zw) Ql(Uw Vb) dA(Uw Wd) FiLh MiOp MwVb} Jj{Et(Hu Ik Io Ma Mv Pe Qb) Nw(Hu Ik Ma Ms Mv) Qb(Hu Ik Ma Mv) Lh(Io Ms Nh Wm) Jm(Hu Ik Nx) Mn(Ik Nh) Pe(Ma Pa) tF(cW Tj) WmQd NrKz HuOk} Fi{Nr(As bH Bn bO dA dD De Fc Fn Je Pa Ql) Pi(bZ Mw Nu Nw Pe Vq) Lh(Af bO Nu Yd) Fc(Mw Nw) Ny(Oe Qn) AfOk CuPa NqLd} Je{Zw(bF BG bZ cX Dl In Oe Qv Ug) Wc(Et Lh Lx Mz Nr Pf Pi) Pf(Rz Wd Wh) Op(Ld Qv) ThVq GdNr WhLh} Ql{Uy(Af bQ bZ Oe Qv) Ms(bV dM Oe Qv) In(aM Kz Ow) Yd(bZ Jp Lh) Af(Uw Vw) Oe(bV dM) ApVw FdPi GdaY NcbV ZxJv UwPa} Af{Ez(Gn Hl Rt Uz Wg Zq Tl) bQ(Fd Hl Hp Uw Vc Zq) Zq(Mv Ou) Rm(Uw Wd) Vw(Ou Ut) bZ(Uz Wg)} Ap{Zq(Ba bZ cP cT Ez Mj Mw Nu) Ez(Fc Hp Vw Tm) Ex(Ba Mv Uf) Vw(Mw Nw) fR(Nr Rf) KrUf} tF{Fa(Al Ao Bg bP Ch Co cW Hu Iz Kg Ks Mg My Qu Tz Ua) Cs(Cv Lw) Ur(cW Pk)} bH{bR(aJ aP bA Fa Lx Pe Pf) Tm(aM Cs Ld Pe) Th(aM Ow) Lx(bS cA) MsPe RfaM UrUv} Nw{Ms(Io Ma Mv Mw Oh Om Wm) Th(bO Nc Nl) Pa(Pf Tt) BgYd FdPi NlHp InKz SidA} Kr{Ou(Ax Cs Fa Lj Oh Pe Pk Qd Rf Th) Jp(dA Jv Lw) LwMa MzHp OfUt} Lh{Yd(Bg bR bS dH Fw) Ms(bO dA Jv Kg) Si(aV bO dA) DuLd FwHp LxOf WcbO} In{Kz(Ke Lx Mn Oh Ow Qd) Ow(aM Iv Nc Pk) Qb(Et Lx Ok) IvaM PebJ} Nr{Nc(bV cN dM) bO(bV Gd Si) Jv(Ms Qv) Pa(bV dM) dA(Gd Si) CobQ NlHp} Nl{Tm(Mw Ny Rm Ut) Th(Cv Ou) Ez(Em Hp) FnJq LxbR MzHp StbA} Nc{Th(Cv Dk Ou Vs) bA(Fn St) LxTo HpJp HubV TmNy} Jv{Mw(aW Tm Th) Hp(Mv Nq) Jp(Kx Kz) Tm(Ny Ut) ToNy} Mz{Si(aV bO dA) Fc(Fw Up) HoIh HpUp WcdA JtVw} bQ{Hl(Bn Kf Pa) bR(aJ bM dM) DuQn aCbE aJdH} Pi{Fd(bA cT Mi) Wc(dA Mi) EzYd ExGd FnLx} bA{bF(aM bJ) EtJt IiVu QdbO OfUt aCbJ} bZ{Dg(Vw Zq) Hl(bO Pa) Kz(dM Lw) DubO} Lx{FnPk NsMp MsQb NaNd HubR dHdM} dA{Si(Jp Mj Ok St) WcNx PfbR} Du{Ez(bO Cs Ld) OabU dHfR} Mw{BbGb MkTr TvUr TmJu} Kz{dM(Bg Ch Jp) MnJo} Ut{BnTm ExGd OfcT} Vu{Ur(Qz Vs) ThUf} Pa{Pf(aW dM Qv)} fR{EzRz HldH bRcX} Wm{Qd(Ms Oe)} Fd{Ii(Pe Ra)} Nu{EzUx ZqbU} Ma{HpbL KgVt} Nb{FnTm HoJm} Yd{IhOu RfNx} EtMsHu MiHoJm MpNdOk JfLtRm OcbJbV OuVoVw

Constrained panels with 2 analytes, where 1.0E-7 >= 'AUC p-value' > 0. Contains 1,074 panels of 87,101 total panels evaluated. : Ni(aD AJ aM aP aW Ax bA Bo bR bV bZ cN Cs cT dI dM dN Dr Du Ed eF Et Fa Fd Fp Fr gL Hp Is Jd Ji Jl Jp Jr Kx Lx Mn Mp Mu Nn No Nw Oh Ok Om On Pf Po Ps Qa Qb Qe Qv Ri Rv Sr Tn Un Vi Vz Wb Wf Yl Zq Tm Xa Th) Dr(aA Ao Aw aX BA Bg bH bQ bZ cG Co cS cT dF dI Ef Ez Fb FR Gl Gp Im In Is Jd Je Jl Jy Ki Kq Ky Lh Lu Lv Ma Mi Mj Mr Mt Mu Mv Mw Nn Nq Nu Og On Or Ou Oz Pb Pf Qa Ql Qw Qy Rb Tn Ut Xa Th) No(aA Ap Bb bH bO bR dI dN Dp eC Ed eF Et Fr Hc Im In Io Is Ji Jj Jl Jr Jv Jy Ki Kj Kl Kr Lh Lj Lu Lv Ma Me Mq Ms Mu Nc Nf Ng Nn Ns Nw Oe Og Oi Ok Om On Or Ou Oy Po Qa Qe Ri To Us Uu Yl) Mu(aA bA cT dN Ed Et Fa Fp Fr Hv Hw Ih Im Is Ji Jj Jl Jn Jp Jq Jr Lh Lj Lv Lx Me Mh Mn Mq Mr Ms Mt My Mz Ng Nh Ns Nw Oe Og Oh Oi Ok Om On Oy Pb Pe Pf Po Qa Qb Qe Qv) dN(aA An BA Bg bH bR cA cT dI eC Ed Ef Fr Gl Hu Im Is Jd Jl Jn Jr Jy Kq Kz Lu Lv Ly Ma Me Mr Nc Nf Nn Nr Og Or Ou Oy Oz Pc Ps Qa Qe Ql Qw Qy Ri Wb) Jl(aA Aj aW dI dM Ed Et Fp gL Ii Im In Io Is Ji Jj Jr Kj Kr Lu Lv Me Mq Ms Nc Nf Ng Nk Nl Nn Ns Nw Og Oh Oi Oy Oz Pb Pf Po Ri Us Uu Vz Yl Ye) Ed(aA aP BA bF bQ bV bZ Dk dM eF Et Fa Fr Fy gL Hu Is Jd Ji Jn Jp Jq Jr Jy Kq Ky Lh Lv Lx Ma Nn Nw Oi Om On Pf Po Qy Ri Sr Uf Un Xa) Qa(aA dI eF Et Fr In Io Is Jg Ji Jj Jq Jr Lu Lv Lw Lx Ma Me Mm Mn Mq Mr Ms Nc Nf Ng Nk Nn Nw Oe Og Oi Ok Om On Pf Po Rv Sf Sh Vz Ye) Jr(aA Aj dI Et Fp Fr Im In Is Ji Jj Kg Kj Lv Lx Ma Mq Ms Mt Mv Mw Nc Ng Nh Nn Ns Nw Og Oh Oi Ok Om On Pf Po Qe Ri Ur Us Vz) Im(aA dM Et Fr Hl Ji Jj Jq Lu Lv Lw Lx Mm Mq Ne Ng Nh Nn Nw Og Oi Ok Om On Pf Po Qd Qe Sf Sh Uz Vi Vz Wg Yl Ye Tm Xa) Qe(aA Aj aW dI Et Fp Fr gL In Io Ji Jj Jm Kr Lu Lv Lx Ma Mq Mr Ms Nf Ng Nh Nn Nw Og Oh Oi Om On Oy Pf Po Ri Vz) Po(aA dI Et Fr In Is Ji Jj Jq Lu Lv Ma Me Mm Mq Ms Ng Nh Nk Nn Ns Nw Oe Og Oi Ok Om On Oy Oz Pb) Kq(Ad Aj aW Bb cI dM Dp Eq Hc Ii Iz Jg Jt Jv Kg Kj Kl Kr Ly Ng Of Og Oi Oy Rv Sf Sh Ur Us Uu Vo) Is(aA Aj aW bV dI dM Fp In Jj Kg Kj Kr Lu Lv Me Mq Ms Ng Nn Ns Nw Oe Og Oi Sf Ur Us Vz Ye) aA(aC aM bF bM bR Dp EF Et Fp Fr Ji Jn Lh Lv Ma Me Mm Mn Nn Nw Og Oh Ok Om Pf Pg Ri) Lv(Et Fp Fr Ji Jj Jn Jq Li Lx Mm Mn Mp Mt Mw Mx Nn Nw Ny Oh Ok Om On Pe Pf Qd) Jd(Aj bA bP bV cT dI Jv Ki Kj Ly Me Mr Ms Nc Ng Og Oi Oy Oz Ri Sh Uu Wh Ye) Ji(Fp Fr In Io Jj Lu Ly Ma Me Mq Mr Ms Mv Ng Nn Og Oh Oi On Pb Pc Pf Us) Fp(Et Fr Jg Jj Jp Jq Jy Lw Lx Ma Mm Mn Nn Nw Oh Oi Ok Om On Pf Qd) Ps(Ap bR Je Kc Nc Nj Nk Nl Oe Og Oi Oy Oz Pb Qy Rb Ri Tz Vz Yl Ye) Nn(dI Jj Ki Kj Kr Lu Me Mq Mr Ms Ng Nh Ns Nw Og Oi Oy Rv Sh Vz) Mq(eF Et Fr gL Jp Jq Lx Ma Mm Mn Mt Mw Nw Og Oh Ok Om On Pf) Lx(Hc Hw Ir Jq Me Mr Mw My Na Ng Ns Ny Og Oi Oy Oz Qb) Me(bA bV bZ dM eF Et Fr gL Mn Mt Mw Nw Oh Om On Ur) Ng(Ba bQ Et Fr Jg Ma Mv Mw Nw Oh Ok Om On Pe Pf Tn) Og(Et Fr Hp Nt Nw Oh Ok Om On Pe Pf Qd Sr Un Vi Xa) Mr(bA bV dI dM eF Et Fr Jj Mn Mw Nw Ok On Yl Xa) Jj(Et Ij Jm Jn Lh Mv

Figure 7 Continued

Nw Ok On Pe Pf Pg Qb Qd) Fr(dI Hc Jn Kj Kr Kz Oy Pe Qb Us Uu) Xa(Af Jy Kc Nj Nk Nl Oi Or Oy Oz Ql) On(dI Eq Kj Oi Oy Pb Rv Sh Us
Vz Yl) Nw(In Lu Ly Ma Ms Ns Oi Pb Pf) dI(aM CS dF Fy Jn Nr Pe Sr) Et(In Lu Ms Mv Mw Nf Nh Oi) Un(bZ eC gL In Lu Ly Ms Oi) Oz(Hp
Tn Uw Vi Vw Wb Wd Wh) Pf(Hc Oi Oy Pa Rv Vz Wb Yl) Sh(Jy Mt Mw Nq Ny Ut Vi) Sr(eF gL In Ki Lu Ly Oi) Yl(Jn Ma Mt Nj Pe Ql)
Qy(bA bV cT Va Ye) Fy(bH Kg Kj Vz) Vi(Jv Kc Or Oy) Aj(Ef Jy Tn) Mt(Rv Sf Vz) Jn(Kj Oi Vz) Uu(Ba Dk Jy) Oy(eF Tn Ut) bV(Dp fP Ri)
Lu(Ok Rf) Ly(Fa Ql) Mw(Sf Ye) Nf(Ok Qv) Hc(eF Tn) Wb(Ez Ld) Ki(bQ Ex) Kj(Lh Ut) Oi(Oh Pe) Om(Ms Pb) bA(Hu Ri) BaKl CxfR NrVz
InPe JyKx LhRv RmVa NyeF OuUs bQcA

Constrained panels with 2 analytes, where 1.0E-6 >= 'AUC p-value' > 1.0E-7. Contains 732 panels of 87,101 total panels evaluated. : Qc(bA dM
Ed eF Jd Jg Jn Jp Jq Jy Kj Lw Me Mi Mm Mn Mt Mv Mz Na Nt Ok Pc Pe Qv Sf Sh Tn Ur Us Yl Ye) Ni(aA bM bQ cS dG Hc Im Jj Jn Jq Jv Kr
Lj Mt Mw Ny Oa Ow Pc Pk Ql Qz Rf St Tr Uh Ur Us) Im(aW bV cN eF Fp In Io Jg Jp Ki Lh Me Mi Mn Mr Ms Mt Mx Mz Nt Oh Pd Pg Qv Ri
Rv) Jd(aA Ao aW Bb cN Cs Hc Hu Iz Jl Jr Kr Kx Lu Mq Nf Oe Qv Ru Rv Rz Sr Tn Ur Us Va) Nn(Aj dM Et Hc Hu In Jn Jq Jv Lh Lx My Na
Ne Oe Ok Om On Pb Qd Ri Sf Us Uu Yl) Ed(cN Cv dF dI Dr Ex Ez Gl Jj Ki Kk Lu Lw Mn Og Oh Pc Pe Ql Qv Rf Ur Ut Zq) Is(bR Et Fr Io Jm
Jq Lh Lw Lx Ma Mr Nt Oh Ok Om On Pc Pe Pf Qv Ri Sh Uu) Jn(Aj bA bV cN Et In Jl Kg Ki Lx Mq Ms No Nw Og Om On Pf Po Ri Sh Ur Us)
Ps(Af aX bC Bg Cx Dp Ez Jy Kk Lu Mi Mv Nf Nq Nu Pc Pf Ra Tn Ud Us Uv Va) aA(Bg bH bZ cA Ch Fy gP Jg Ki Lw Lx Mf Mh Mq Nh Oi
On Ow Pc Pe Qd Un Wm) Jr(aW bA bH bV cN dM Hc Jg Jp Jq Ki Kr Lu Lw Me Mm Mn Mr Nt Pc Ql Qy) Jj(Dp Ef Fr Ik Jk Jp Ma Me Mj Mn
Mq Mt Mw Nh Nt Nv Nx Ny Oh Om) Jl(bO bR Dp Fr Hc Jq Jv Kl Kx Lw Ma Mz Oe Ok Om On Pc Qa Qv) No(aD Aj aW bA bS bV cA cN dM
Jq Ju Lw Mm Nk Pc Qv Vz Tj) Og(BA bV dM Fa Fp Jg Jy Mw Nu Nv Ny Ow Qb Ql Vw Zw) dI(AD bV cW Ir Ji Kq Lh Lv Mj Ml Mq Mz Ok
Pi Ut Uv) Et(Fr Io Lw Lx Ma Mi Ne Nt Nw Oh Om On Pe Pf Qb Qd) Kq(aE bH Dl eC Fi Jo Ki Ko Lu Me Ms Nv Oz Pa Ri) Fr(Aj bA Eq Lj Ms
Na Ne Nh Ns Nw Oi Oz Pb Vz) Lx(bR Hq Ki Kz Ly Mt Mv Mz Pb Pk Qd Ri Vz Yl) Mr(bH bR cN gL Jp Lv Mp Ny Oh Om Pf Ri Tn Vi) dN(aJ
Dc dM Fy In Kr Ky Mq Ms Oe Po Qt Vi Xa) Fp(dF Hx In Jk Lh Lu Mq Mw Nh Nt Nv Ny Pg) Qa(aW dM Fn gL Kr Lh Mt Mz Pc Pe Ri Ur Us)
Po(Aj eF gL Hr Hw Jt Lh Lw Mz Pc Pe Ri) Mu(Cs Kx Lw Ly Ma Mg Mi Nt Qd Rf Rh Uu) bA(aM bF bJ bZ Ch Hc Ly Oy Oz Pc Ql Un) bQ(aJ
bM bR bV Cs cT dM Jv Me Rv Sh Vz) Xa(Aj bN Cx Jv Ki Ng Nu Pb Pc Ri Sh) Nw(Hv Hw Jq Lh My Na Oh Ok On Oy Pe) Me(aP Ax bF cN
Jy Mm Ny Ok Pf Tn) On(Io Lj Lu Mg Ms My Nh Ns Pe Sf) bV(cA Ef Ki Kz Ly Nc Oi Or Oy Ql) Sr(bH bO eC Ms Oe Oz Qv Tn Uu) eF(Ch Cs
Fa Gl Kz Nf Oa St Un) Om(Hu Kj Lu Ly Ns Oi Oy Pe) Lv(Jp Lj Mq Mz Nh Un Ur) Jy(Ax Cs dM Eq Jv Ri Us) Ny(eC Ma Mq Mw Ng Ns Ri)
Yl(bZ cT Ez Nr Oh Oz) Ql(Lu Oi Ri Sh Va Ye) Pe(bH Ki Mm Ms Pb Vz) Dr(aJ dG Ex Nk Ri) Ly(Ex Ki Kk Ok Qy) Oi(Ex Fa Kx Mt Ok) Pf(Nh
Ns Pb Us Uu) Mq(bZ Ki Mz Qb) Mw(Jq Mt Ns Ri) Or(bJ bZ dM Ur) Fa(gL Qy Ri) Nr(Ki Rv Sh) Ng(Jk Jp Nt) Tn(Kj Ri Rv) In(Ok Ow Qb)
Qv(Oz Pc Qy) Un(Kj Oz Us) eC(Dc Pk Vt) Lu(Ex Qb) Ms(Oh Ok) Mt(Nf Ns) Vz(Lh Oh) Kr(Ji Ou) Vi(Qy Rf) Oy(Dk Uw) AjBa EfGd FyUr
MaUu MnNh MpNd NfJp ZwJe ZxOz QdgL YeRm KgLh KiKy KjOk RvUt aJbR bZdM cXfR Constrained panels with 2 analytes, where 1.0E-5 >= 'AUC p-value' > 1.0E-6. Contains 1,232 panels of 87,101 total panels evaluated. : Jd(Ap bH bM Co Cu dA dM Dp Ij In Is Ji Jj Jn Jy Ky Kz Lv Lw Ma Mg Mk My Nn Oa Oh Or Ow Pc Pe Pf Pi Pk Po Ps Qa Ql Qu Rf St Tv Ud Vi Yl) Ed(Ad aJ aM aY Bc bH bR cE cS cT CW dA Dc dG Fb Im In Je Jv Ke Kx Ly Mr Mw Nc Nj Nk Nl Nr Oe Ok Or Ou Ow Qa Qt St Tn Vq Vw Wd Wh) Nn(aW bA bH bR bV cN Co dA Dp eF Hv Hw Ir Jo Jp Kg Kz Lw Ma Mh Mi Mm Mz Nt Pe Pf Ps Ql Qv Sr Un Ur Ye Tm) dI(aA aJ aP Aw Ax Ba bB bU bZ cF cP cT Cu Cw Dc dG Et Fa Gl Ij Im Jp Kn Kx Ma Me Nb Ny Oa Oh Or Ow Pg Qd) Mr(aA aJ aP aW cS cT Fa Fp Jg Jn Jq Kr Kx Ky Lh Li Lw Ma Mm Mq Mt Nv Oi Or Pg Qb Qd Qv Qy Ru Ur Us) Sr(aA Aj aW bR bZ dJ dM dN Dp Hc Is Jj Jr Jv Jy Kj Kr Kx Ky Lv Ma Me Mu Nc Nf Ng Nl Oy Pc Ql Ri Ug) Jy(aJ Ao aW bA bV Dp Fa Hc Jn Jr Ki Kj Kr Kz Lj Ly Mq Nf Nr Oa Oi Ow Oy Oz Po Qa Ql Rf Sf Un Ye) Mw(aA aW Hv Hw Ih Ij Ir Jn Lh Lw Mh Mi Mj Ml Ms Mx Mz Na Nb Nf Nu Oh Oi Pa Pc Qb Qd Qv Rv Yl) Og(aP bQ cT dF dG Dk eF Ex Ez Ij Jk Jp Jq Ki Kx Lh Li Lv Mn Mt Mv Oa Ou Pg Qy Rf Zq Wm) Fr(Cs cT dM Dp Hu Jq Jv Ki Kx Lh Mg My Mz Nl Nt Oe Oh Ok On Pf Pk Ps Qd Rf Un Yl) Qd(Aj dN eF In Jn Jv Kj Kr Ma Mq Ms Nf Ng Nh Ni Oh Oi Ok Om On Pe Pf Ri Us Uu) dM(aA aC bF cS Db dF Dr Fy Gl Jn Kz Ly Mq Mu Mv Nf Nr Oy Oz Pc Pe Pk Ql Qy Ri) Fp(aP bF bQ bV bZ cE Cv Dk Ir Jt Ky Ly Me Mi Mp Mt Mv Mx Mz Na Nb Pa Pc Pe) bA(aA bM bP bR Dc Io Is Jl Ki Lu Lv Mq Ms Nc Nf Ng Nr Oe Oi On Or Pk Qa St) Lu(bQ bR Cs Dp Fa Fy Gl Jn Jp Kx Kz Lv Mn Oa Oh Ow Pe Pf Pk Ri Vt Xa) Jj(eF Hu Ii Il Jg Jq Js Kq Lj Lx Mh Mm Na Ne Ng Nr Pd Pz Qc Ql Ri Wm) Lh(Aj Et Jr Lv Mt Ng Ni Of Oh Oi Om Oy Pb Pf Qe Ri Sf Ur Us Uu Yc Xa) On(Aj Hc Hu Ii In Jq Ki Kz Lw Ma Mh Mk Mz Oe Of Oh Ok Pf Ri Uu Ye Th) Im(Hv Hw Ij Ir Jn Jo Jt Ma Mh Mj Ml Mv Na Nb Nf Oe Pa Pc Pe Tn Tv) bV(aM An bF bH bZ dR Gl Hu Ji Jl Lv Ms Mu Nf Nr Oe Oz Pc Qe Rf Us) Me(Ba CS Cv dF dG Dk Jg Jn Jp Ki Kk Lv Lw Ma Mp Na Pe Qb Un) Ni(bW Cv dA dF Dk Dp Ez Gl Jg Kq Ky Li Lv Mm Nv Or Qh Qt Qy Vp) bQ(aD aM aW Ax bW cP cS dH Dp Hu Nw Oi Oy Ps Qe Ri Uu Uv Wb Yl) Jp(dA Jn Jv Kr Kx Kz Lx Ms Nh Nt Oh Oi Pe Pf Qb Sh Us Uu) Xa(aM Ap bU cS cX Jf Lv Mu Nb Nc Nf Qe Rb Sf Un Uu Yl Ye) Ki(cT dN Fa Fy Hu Is Kx Kz Mu Or Pf Po Qa Qe Ql Ri Tn) Ny(aA gL Jq Lw Mi Mt Mv Mx Na Nu Oh Oi Qb Rv Sf Ye Tm) Un(Aj bH cT dN Fn Ii Jt Kr Ma Nc Oe Oy Qv Ri Ug Ur Uu) Lx(Hv Jo Lw Mn Ms Mx Ne Nh Nt Of Oh Ok Om Pg Pi Qy) Or(aA cT Fa Jn Jr Jv Kx Ly Ql Qv Rf Rh Ri Us Vw Wb) Pe(eF gL Jg Jq Jr Kj Lw Ma Mn Mq Ns Ok Oy Oz Pa Ri) Pf(Aj bR In Jq Kj Kr Kz Lw Mn Na Nt Oh Ok Om Oz Ri) Qe(bH bR cN dA Hv Hw Jo Jt Jv Kg Ky Oe Ql Uu Va) Kq(aA Af Ao Ap Bn Co Cq cZ De Nc Pb Pc Qu Qv Ug) Mu(aD Aj aM bR Fy Jt Kj Ky Mm Oa Pa Tn Ur Th) Yl(Ax Ba bN Cs Fy Mj Mz Nb Nk Nu Ow Pb Qy Wm) Oi(dN Ez Fb Ky Ma Nt Oa Qb Qt Qy Rf St Uf) Om(In Lj Ma Mg Mh My Na Ne Nh Oe Of Oh Ok) Mt(aA Et Hv Hw Jq Lw Mi Mn Ms Ng Oh Si) Tn(dN Eq Jv Kz Mq Nf Pa Pc Rf Sh Us Uu) Ri(aJ aP bZ cN eF Ji Kk Ly Rf St Ut Th) Dr(An aP bC bW cP dN Fn Mz Nd Uk Ye) Lv(Aj cN Cs Hu Kx Ma Ne Nf Nt Nv Wb) Et(Hv Hw Jq Mh Mz Na Nb Ok Pc Sh) Is(Al bH dA Hc Jv Ky Mm Mz Ql Va) Qa(Aj bH Bo bR eC Jv Kg Kj Qv Ug) Jn(bH Jg Jv Kr Mv Ng Nt Oh Ok Qy) Jr(bR bZ eC Jv Kx Ky Kz Mi Mz Qv) Ps(aD aM bZ cP cS Io Ma Pa Qx Sh) Oz(aJ Fa Fy gL Kk Ky Rf St Vb Ye) eF(Fw Kj Kx Ly Nw Pk Ql Rf Us Uu) No(Co cP cT cW Fy Kg Sh Ud Ur) Mq(Fy In Ir Jg Ky Nh Qv Vi Wb) Vz(cS Ma Mz Nb Nj Nu Ow Rm Ut) Ji(aW Bb bH bZ dN gL Qv Ur Th) aA(cT Dk Jq Nf Ns Nt Pd Pk Ql) Ly(aJ aP cN Fb Ky Qv Rf Ut) Qb(Jq Lw Ma Mn Ms Ng Nh Ye) Oh(In Mv Ne Nh Ns Nt Oe Ok) Po(bH bO Kj Ky Qv Ur Us) Fa(bH Dp In Ky Ms Oy Pc) Jl(aE Db Hf Ky Kz Pk Ur) Vi(cZ Je Nf Nu Pb Ql Rv) bZ(aJ An Cs cT Kx Kz Uv) eC(Cu Id Kd Ml Mz Nb Pi) Aj(Cu Ez Fy Hu Ma Ou) Nw(gL Ir Jo Jt Lw Pc) Oy(dF Jg Kk Ou Vp Wd) Ma(cN Mp Ne Nh Ok) Ur(dN Nr Ou Pi Vu) Ef(aJ cN Cs Qv) Mn(Kz Ms Ne Ng) Mv(Jq Ok Sh Ye) Hu(cT cW Qv Uu) Wb(cS Ml Ra Rf) dF(Hc Nf Rv Uu) dN(Dp Hc Kx Rf) gL(Hc Iv Kz Nf) Dk(Kj Kr Us) Ez(Rv Sh Ye) Fy(cN Ii Jo) Nr(cN Gd Sf) Ng(Ij Li Nv) Qy(Cs cW Tm) Ql(Ms Oe Qv) Ut(bH Of Us) Pc(Tt Vw Zw) cS(cN cT dA) Ba(Dg Ss) Th(Nk Vq) Gl(aW dA) Nu(Sf Zq) St(Sh Va) Kc(Uw Wd) Ky(Dp Nf) Ok(Io Rv) bF(aJ dA) bH(cT Rf) bR(aP dG) fR(aC bN) ApUf BgUu CuKj FdNj NsJh LwIr IhVa InIv SfRm JkYe UwPb aMcT Constrained panels with 2 analytes, where 1.0E-4 >= 'AUC p-value' > 1.0E-5. Contains 1,767 panels of 87,101 total panels evaluated. : bV(Ad As aW Ba Bg bM bP bR cE Cq cR Cs cT CW Dc dM Et Fa Fr Fy gL Io Iv Jq Jv Kk Kq Kx Ky Lh Lu Lx Ml Mn Mq Mt Mv Mw Nq Nw Ny Oa On Ow Pe Pf Pi Pk Po Qa Qd Qv Sr St Ut Vt Wb) Lu(aJ aM An aP Ar Ax bZ cN cS cT dF dI Dk dM Ef Ez Fb Jg Jj Jq Jy Ki Kk Ko Ky Lx Ma

Figure 7 Continued

Mm Mp Mq Mt Mw Na Ny Or Pj Qd Qm Qy Rm St Uf Uh Zq) bZ(Ad aM As Bn cA CP Cq Cu Cv Cw Dc dL Ex Fa Gl Hc Hu In Iv Jn Jv Ki Lh
Lw Ml Mu Ng Ny Oa Oi Ow Oz Pi Pk Qa Qe Ql Rf Uu Vt Vz Xa) Ri(Ax Ba CS dA dF dG dI Dk Et Ex Ez Fd Fp Fr GL Hp Ir Jp Kx Ky Me Mq
Mu Mz Nb Nr Nv Nw Oa Og Oh Oi Oz Qb Qv Qy Vi Yl Zq) dI(An bM bR cE Cp Cq Dk Ef Ez Fp fR Hu Hw Hx Iv Jq Js Ky Kz Lj Lx Ly Mt
Mu Mv Mw Nf Nt Nw Oi Om Ou Pk Qb Ql Qv Rf Uf Un Vi) Qv(aA Ba bH cN dA Dk dN Dp Et Ez Fa Fp Fr Fy Gl Jn Jy Ki Kx Ky Kz Lh Ma
Me Mv Nr Nw Ny Oa Oi Ou Pe Pf Ps Qb Qd Rf St) dM(An Ba Bg cE Ch Cs Cu Dk Ef Et Ez Fp Gp Hc Hu Ij Iv Ji Ki Lh Lv Ma Mw Nb Nc Ny
Oa Oi On Ow Pf Po Qd Qm Qt Rf St Un) Jj(bR Ex Ez Fy GL Hv Hw Ih In Ir Iv Jh Jo Jt Jy Kz Li Lw Mf Mi Ml Mp Mz Nb Nj Nl Nm Nu Oa Or
Pa Pc Qy Rf Un) Oi(aJ aP Ar Ax Ba cN CS cT dA dF dG Dk EF Fy gL Hp Ih Ij Iv Jg Ki Kk Kz Li Lj Mn Mv Nh Nv Ow Qh Tn Ur Vu) Me(aM
An aW bH bR bW cE cG cT Cu dA Dc Ed Fa Jq Kx Ky Lh Mv Mz Nq Nv Nx Ou Ow Pc Pz Qd Ql Qy St Uf Ut Vp) Ki(aP Ax aZ Ba Cw dA Db
dF Et fR Ji Jp Lh Lv Ma Ml Mv Mw Nf Nq Ny Oa Oh Ow Oz Pc Pk Qt Rf Ut Vp Vu Vw Zq) bQ(Ad An As Ba cO Cp Cq Cu Cv Cw Dc Eq Jn
Kx Kz Ly Ml Ms Nc Nf Oa Oe Oz Pc Qd Ql Qy Rf St Ur Us Vt Xa) Jd(AD aJ aM As aY bW Cv Cw Dc Fy gL Hv Hw Id Im Jq Kd Kg Kn Kp
Mi Mu Na Nr Ou Qd Ra Rj Un Up Vt) Og(aJ An Ax cN Cs Cv Fb Fd Fy Gl Hu Iv Jv Ke Kk Ky Lw Ma Mp Mx Nb Nh Ni Or Qh Qt St Tn Uf
Yl) Ur(aM bA Cu EF Ex Fp Fr Hu Im Jq Jy Lx Ly Mj Mw Mz Nf Ok Om On Ow Pe Pf Qd Ql Sr Tn Ut Uv) Qy(aD aJ aP aW Ax cN dF Gn Hl
Ji Kx Ky Ml Mq Ms Nf Ng Oz Pe Ql Rf Rt Tv Un Uw Uz Vh Wg Tl) Ed(aD AW Bg bJ Ch cK Cp Di Ef fR Id Kd Kn Mm Mq Mv Nf Oz Ra Rb
Tr Uv Uw Vt Yl Zw tF) Mr(aD aM Ba dF dG Dk Gl Id Ij In Jk Jv Ly Ms Mv Mz Na Ne Ng Nh Nt Ou Ow Pk Ql Rf Uf Un) cT(aD An aY Bg bJ
bP cN cW Dc dF Hc Is Ji Jl Jn Jr Ly Mq Mw Nn Oe On Pc Qd Qe St Vi Vz) Jn(aD aJ aP aW Ba cS eC Fp Hc Io Jq Kx Ky Kz Lh Lw Ma Mi
Mm Mn Nc Nf Pc Ql Tn Uu) Un(aJ Ba Bo bR Gp Im Is Jl Jo Jr Jv Kx Ky Mq Mu Nf Ng Nr Ou Pc Pf Qe Ql Rf Sr Va) Ni(Ba Dc eC Fy Hf Ih Jk
Js Jt Jy Ke Kz Ma Mh Mv Mz Na Ne Nh Nt Ou Pc Pg Ua Uf) Jp(Aj Eq Hc Io Jq Kj Lh Lw Ma Mi Ml Mv Mw Mx Ne Ns Nu Ny Ok Om Qd Rf
Sr Vz) Ql(aD aJ aP cN cS cW Fa Fr Hu Im In Ji Ky Lx Mu Mw Nc On Oz Pf Po Qa Tn Uy) Ly(Ba dF dG Dk Ez Je Ke Kn Kx Ld Mt Nh Nt Oa
Ou Ow Pi Rb St Tn Uf Vp Wm) aJ(aC An bA Bg bS cE Ch dF Fr Gl Hc Hu Is Jr Lv Mq Nc Nf Nr Oe Or Oy Pc) Jq(dN eC In Lh Lj Lw Ma Mh
Mi Mn Ms Nb Ne Ng Ns Nt Oh Ok Om Pc Qd Wm) Jy(aA aD aM Bb bR cP Et Gd Im In Is Ji Jl Ms Nc Ng Nn Pf Pk Uv Vt Th) Rf(Bg cN Hu In
Jr Jv Ma Mq Ms Mw Ng Nn Oe Ou Pc Pf Qd Qe Sr Vz Yl Ye) Jv(bA dF Dk Et Fa Fy Hu Im Ky Lh Lv Ma Mn Mu Mw Nr Ny Pe Pf Po) Or(aP
cF Et Fr Gp Hu Kr Ky Mq Ms Nc Ng Nn Nr Oy Pf Pk Po Qe Tn) Lh(Fi Hc In Jo Kr Lw Ma Mm Mn Mq Ms Ne Nh Oe Ok Pe Qb Qd Sh) Ny(Hv
Hw Ij In Ir Mh Mj Ml Mm Mn Ms Mz Nb Ne Nf Nh Nt Pa Pc) Mt(eC Hc Ij Ir Mh Mv Mx Mz Na Nb Ok Om Pa Pc Pe Pf Qb Qd) aP(An Bg cA
Dp Ef Hu Im Lv Mq Ms Nc Nf Nr Oc Oy Oz Pc Qz) Fr(aC An aW Hv Hw Ir Jo Jt Kg Lw Ma Mm Mx Oa Ow Qz Xa) bA(aD Dk Dp Ji Kq Kz
Lw Lx Ma Nw Ou Pf Po Sr Uu Vi Vz) eC(Ad Cp Cq Cw Hv Hw Hx Ij In Ir Iv Kn Om Pe Rj Up Vp) Mq(aD bR cS dF Js Kk Lj Lw Ms Mv Ng
Nt Ou Pg Pi Yl) Mu(aC Ax Bb cN dF Hu Kr Kz Ow Pi Pk Rv Tv Us Ye Tm) Tn(aA Dp Gl Kg Kr Nc Nj Nk Nn Nw Po Qd Qu St Vz Yl) Sh(Cu
Dk fR Fy Ih Ij Jr Mn Mz Nu Nv Ok Om Pi Qd Rm) Oh(Hc Hv Hw Ij Ir Jg Kz Lw Ma Mi Mn Mz Na Nb Pe Rv) Lv(bH bM Fa Hc Hp Io Jg Jt
Lw Mi Mv Na Nb Us Yl) Lx(bS cA Cu Cw Ef Jg Kr Kx Ma Mh Mm Pc Qz Us Th) Hu(bM bR cN Cs dA dF Kx Ky Kz Mm Mn Ng Ow Qb Ye)
Pf(Dp Hv Hw Ij Ir Jg Jo Jt Kx Ky Mm Mz Nb Pc Pe) eF(bL Fp Hf Hx Is Iv Ji Jr Lj Mv Nb Nc Nt Oz Pc) Ye(fR Hp Ih Nf Nq Nr Nu Oa Ow Qd
Sr St Ua Ut) Oy(Ba Cu Dc dG Dr Ex Fy Ky Nv Pg Vw Wh Yl Zq) Ma(Fa Hc Hp Je Kj Kx Li Lj Ms Mw Nl Nu Vo) Pe(Aj aW bR Kg Kr Ky Mz
Nk Nt Pc Qb Qz Us) Vz(Cu dF Ih Ij Ir Js Ok Pi Ra St Vi Th) Qd(aW bH bR dA Jg Lw Mm Mn Mv Na Nt Pc) Sr(aM bF Bg Bo cS Gp Jl Ju Ou
Uk Us Xa) Yl(cP cS Cx dN Ih Mh Nq Oa Pi Qm St Ut) On(Ap aW Bb bH bR cN De Jh Jk Kg Kr Mv) Fa(Bg bR dA Hc Mi Nc Ng Oe Ou Qz
Ud) Nr(Aj bH dA Fi Hc Kg Kj Kr Us Uu Va) Mw(Aj bR Jg Lj Mn Ne Nh Nt Pg Us Vi) Im(bR bW Cv dG Ke Kj Kk Kx Ky Ou Uf) In(aM Cs Ij
Kq Kz Li Nt Nv Pd Pg Pk) Qb(Jg Mi Mm Mv Mx Mz Na Nb Ns Nt Vw) aA(aW Ba bW Dc Io Kx Na Ou Ps Us Zw) Fp(Ba cG cN cS Hv Hw Ij
Jo Nf Ou) Nn(aD An bS Eq Jt Ky Pk Qz Tv Uk) Ms(Ba cS Ex Jg Ky Mp Mv Nt Nv Ow) Kq(Dk Ib Md Mg My Nb Nx Pg Vp Wc) Vi(bH bL Bn
Cx Ez Kj Nk Pa Sf Xa) Pc(cN Ex Kx Ky Ok Ow Tr Uf Wh Zq) dF(An aW bM cA cP Dp Kz Ng Oz Us) Nf(cN cS Ex Kk Mp Nt Ou Uf Wb)
Jr(Ba bW dA Dp Fd Fi Ou Uf Wh) Om(Aj Kr Lw Mi Mm Mx Mz Us Uu) Po(aW bR cA Dp Hc Kg Kr Uu) Mn(Hc Kr Mi Mv Ns Nt Nu Ok)
Ji(Bo Db Fn Hf Kg Sf Si Va) Xa(cP dA Dp Fy Je Kk Ld Mz) Kz(bF cN cS Dk Kk Ky Nw Ou) bH(aD Cs Dc Gl Kx Pi Pk Uv) Aj(cS Cw Et Jk
Ok Qt Ut) Mp(Ij Ir Mj Nb Nh Ns Nt) Wb(cP dG Kx Nj Nk Qx Zw) St(aW gL Nc Nk Oe Rv Sf) Oz(cN Ex Gl Hl Kx Ut Tl) fR(aW bR cP dA dC
Dp Ps) Ba(aC aD Hc Oe Qe Us) Cs(bF cE cS GL Ou) Qa(bJ Db Fw Gp Hc Ky) Kj(Ad Cw Ij Mj Pg Uc) Rv(Et Ij Kk Mj Nv Ow) Ez(Eq Fc Hl
Ng Va) Mv(Ex Lw Mm Ne Nh) Nj(Du Hp Ry Zq Zw) Is(aD Co gL Ju Tz) Qe(bS Hc Pk Qz Ud) Jg(Io Ne Nh Ns Uu) Uf(Hc Kr Ng Us Uu)
dA(cE Dr Ky Nw Ps) Et(Kr Us Uu Va) Fy(Bb Co Gd Jf) Nc(cN Ex Ky Ut) Jl(aD cW Kg Ow) Tm(Jk Nb Pi Ut) Pb(Ex Nb Nv Vb) Dr(bE Cx To)
Ef(Ax cW dG) Th(Dk Lw Ou) Nt(Mm Ns Oe) Sf(Ih No Ow) cN(Gl Ky Ow) cP(bF cE Ex) cS(An bR Hp) dN(Kg Nw Rh) gL(Oa Uv Vt) Nh(Mm
Nv) Hc(Tr Ut) Kr(Ps Ut) Ok(Mh Mz) Ou(Pk Uu) Uw(Af Cx) Va(Dp Rb) dG(Db Us) AxGl CuUu CvNo FdNk NgPg ToVq ZqKc WcPi QzNw
KyOa OwVp cWtF Constrained panels with 2 analytes, where 1.0E-3 >= 'AUC p-value' > 1.0E-4. Contains 2,736 panels of 87,101 total panels evaluated. : Og(aM
Aw bC bM bR bW bZ cE Cp cS Cu Cw dA Dc dI dL Ef Em Fc Gb Hl Id Ih Ii Ik Jh Js Jt Kd Kf Kn Kp Kz Lj Lu Me Mf Mi Mj Mm Mr Ne Nr
Nx Pd Pi Pk Qv Qw Ra Rb Rh Rm Ry Ua Uc Ud Ul Up Ur Ut Uv Uw Vb Vh Vp Vq Vs Vt Vu Vz Wb Wd Wh Tl) Ki(AD aJ aM An bR cE cG
cN Cp Cq CS Cu Cv cW Dc dE dG DI Dk Ef Fp GL Hf Hv Hw Id Ij Ir Iv Jj Jq Js Kd Kn Kr Lw Mi Mj Mn Ms Mt Mz Na Nb Nv Nw Oe Ok Om
Ou Oy Pb Pg Pi Qh Qy Ra Rj St Tt Uc Ud Uf Up Ur Uv Uw Vt Yl) bZ(aD Aj aW Ba bH bM bR bW cS Dd Dp Du Ef Em Hl Hp Hv Hw Id Ij Im
Ir Jj Jq Js Kd Ke Kn Kr Ky Ly Mj Ms Mx Mz Na Nb Nc Nf Nw Oe Ok Om Oy Pb Pc Qd Qv Qy Qz Ra Rb Rj Sh Tv Ud Up Us Ut Vp Wb Zw)
Ur(Ad aP aY bV Cp CS cT cU CW Dc dF Dk dM Et Ez Fa Gl Hw Ij In Ir It Iv Jk Jp Js Kk Kn Kx Ky Kz Lu Lw Ma Ml Mq Mv Nb Nv Ny Oa
Oh Oz Pc Pg Pk Qb Qh Qy Rf Ri Rm St Uc Ud Uf Up Vp) Oi(aM An aO Aw aY Bc bF bR bW cE cG cP CU CW Di Fw Gl Hu Id Ik Ir Je Jh Jk
Jq Js Kf Kn Ko Kp Lv Mh Mm Mp Mq Mz Nb Ne Nq Nu Or Ou Pd Pg Ph Qw Rh Rm Ua Uh Ut Uv Zq Wm) Lu(Ad As Aw Ba bW Cp Cq
Cu Cv Cw Dc Dd dG dL gL Hp Hu Id Ij Iv Jk Js Kd Ke Kn Lh Li Lj Lw Me Mr Mv Ne Nh Ni Nt Nv Nx Pd Pg Pi Qh Qt Ra Rh Rj Tn Ud Up Ut
Uv Vz Wb Yl Zw Wm) Ql(Aj aM aW Ax aY Ba bB bH bR Cs cT Cv dA dF dG Di Dk Et Ex Fp Fy GL Jp Jq Jv Kj Kk Kx Lh Lv Lw Ma Mq Nb
Ng Nr Nw Oh Ok Om Ou Ow Oy Pc Pe Qd Qt Rf Ru St Uf Us Ut Vq) bH(Ad aM An Aw Ax Ba bM cG CP cS CU CW Dk Du Et Hu Id Ij Im Ir
Jp Jq Js Kd Ke Kk Kn Ky Kz Lh Lw Lx Ma Ml Mu Mz Nb Nt Nw Ny Oa Oh Ok Om Pg Qb Qh Ri St Uf Vt) Ky(aD aJ aM aP Ax aY BA bQ bR
CS cW dM EF Ex Ez Fr Gl Hp Jj Jp Jy Kk Kx Lh Lv Lx Ma Ml Mv Mw Nj Nl Nr Nw Ny Oe Oh On Ow Pk Qd Qh Qt Rf Sh Uf Uv Vt Vz)
Rf(aA Ad Aj aM aP aW aY BA bC bR bW cE cG cS Cu Cv cW dA dF dG Ex Fa GL Is Ji Jn Jq Kj Kk Kx Kz Lh Lw Me Mv Nc Nf Om On Ow
Oy Po Qa To Uf Ut Uu Tm Xa) Qv(aJ aM aP aX bA Bc bQ CS cT dF dM eF Ex Fb gL Jk Jp Jv Kk Lv Mi Mn Mp Nc Nt Nv Oh Ok Om On Ow
Pg Pk Qh Qm Qt Qw Rm Tn Ud Uf Ut Uv Vp Vt Vu Vz Wb) Me(Ad aJ aO As Bg Bn CP Cq Cw dL Ex Ez Fb Fy Id Ih Ij Je Jk Jt Ke Kn Ko Ld
Li Lj Mi Mq Mr Mx Nh Nt Nu Oa Or Pa Pg Qx Rb Tr Tv Uh Vs Wm) Qy(Aj aM bR Cu Cw dA dG dI Em Fp Gl Id Ij Ir Jq Js Jv Kj Kk Kn Kz
Lj Lv Lw Ma Mz Na Nc Ny Oa Oe Oh Or Ow Pc Pi Pk Ra Rh St Uu Uv Vt) Oz(aD An Ar Ax Ba bF bR cE CS cT Cu cW dA dG DI Dk Ez Fb
Id Jj Jq Jv Ke Kn Oa Or Ou Ow Pg Pi Pk Qh Qm Rt Tv Uf Uz Vp Vq Vu Wg) Kx(AJ aM aP BA Bg bR cN cS dA dF dG Dk dM Et Ez GL Jj Jv

Figure 7 Continued

Kk Kz Lh Mn Mq Ms Mw Nb Nf Nj Nr Nw Oe Oh On Ou Ow Oy Qd Qt) Ma(aJ aP bV Co cT dA dG Eq Ex Hv Hw Ih Ij In Io Ir Jg Kg Kl Kz Lw Mh Mi Mt Mv Mx Mz Na Nb Nf Ns Nt Nv Or Pa Pg Qu Ri Us Wb) Kj(Aw Ba Cp Cq Dc Et Ex Ez Gl Hu Hw Id In Ir Jk Jq Jt Kf Kn Kr Mi Mn Mv Mw Mz Na Nf Nv Ny Oh Pi Pk Qh Rb Ua Ud Uf Up Uv Vp) Jj(aM BA bF Bg bQ bV Ch CS Cu dF Dk dN Fa Fb Ha Hf Jv Kf Mx Nf Ou Ow Pk Qh Qm Qt Qw Rm St Tn Ua Uf Ut Uv Vp Vu) Ri(aM An Ar cT CU fR Fy Hu Ij Iv Jq Kn Kz Lv Mn Mp Ms Mv Nc Nf Nq Nt Ok Om Ou Ow Oy Pc Pg Pi Qt Uf Uw Vp Zw Ye Tm) Oy(Ad Aw Ax aY bF cE cG cN Cp CS cT cW Di Em Fb Fd GL Jk Ke Kn Kp Mv Nb Pd Pi Qh Rt Ry St Tv Uf Vb Vh We Zw) dM(Ad aJ Ar Aw Ax bA Cp cT Cw Dc dG Dl Dp eF Ex Fa gL Lx Ml Mn Nt Nv Nw Oe Oh Ok Om Ou Pg Qn Rh Uf Ut Uv Vp Vu) Jv(Ad aJ aP Ar Ax Ba bF cE cN CS cT dA eF Ex Fp fR Gl Ij Kk Lx Ly Mt Nq Nv Nw Oh On Ow Pc Pg Qh St Uf Ut Zq) Vz(aP Ax Ba bR bU bV cP Cs Ed Fa Fw Il Jk Ld Lj Mn Mv Nd Nq Nt Nv Oa Ou Pg Po Qd Qm Qx Ru Sr Va Vw Zw Ye Wm) Ba(aJ aM aP aW bP cA cN cP Cs dF Dp Ex Fa FR Io Kk Kz Mg Nc Nf Or Pc Pk Qa Qd Qu Sh Tn Uv Vo Wb Ye) cS(aC aD aM aW Ax bF cA cE CP Cu Cw dF dG Dk Dp Ef Fb Fr GL Im Iv Kk Lv Ly Nc Oa Oe Or Pc Qt Ye) Ms(aJ aM Ar cE cN Cs cT Cw dA dF dG dI Dk eF Ez Fb Gl Ij Jk Kk Li Mm Nh Nu Oa Pg Pk St Tn Uf Uh Va) eF(Ad An As Ax bM bW Cp Cq Cv Cw Dc dL Id Ij Ir Jn Jy Lh Li Lx Mt Mz Ng Nk Nr Oh Ow Pf Rg Ut Vt) Nf(aD Aj An aY bB Bo cE cG Cs cT Cv dG Di Dk eC Fb Fy Jg Mn Mr Ne Or Qb St Tr Vp Vw Wd Zq Wm) dA(aO bB Bg bM cA Ch Cp Cs cT Di Dk Et Fb Jn Lh Lv Lx Mn Mv Mw Oa Oh Ok Qt St Uf Ut Va Vi Vp) Hu(aD aM An aW Ax Cv dG dL Hc Jg Kk Lj Lw Lx Mh Mp Mx Na Ni Nv Oa Ou Pk Ra St Uf Us Uv Tm) Ng(aP cT Cu dG Dk Ef Ex GL Ik Iv Mj Mm Mp Nh Nu Nx Ou Ow Pd Qh Qt St Tr Ua Ut Vu Wm) Us(Ad aJ aP bA cT Cu eC Ed Fa Fy Gl Jq Ke Lw Mn Mq Mt Mz Nv Nw Ny Oh Ok Pi Qh Uc Uw Vi) Mr(Ad As bW Cp Cu Cv Cw Dc Hv Hw Ir Jt Kd Kn Kp Kz Mi Mx Nb Ni Pa Pc Pi Qt Ud Up Vt) Jp(cN Cs Dp Fa Hv Hw Ij In Ir Kg Mf Mh Mm Mt Mz Na Nb Or Ow Pa Pc Pd Pg Pk Sf Un Yl) bV(Aw Ax Bn bW cN CP Cu Cv Dk Ez Id Ij In Kn Ko Lw Nb Oh Om Ou Qz Ra Tn Ud Vp Vu) Ow(AJ An aP bR Dk Fa GL Jn Kk Kr Lw Lx Mw Nc Nr Nw Ny Oc Qd Qe Sh St Un Ut) bQ(Ef Hp Hv Hw Id Ij Im In Iv Kd Kn Kp Kr Mz Na Nk Pi Pk Qz Rj Tv Ud Up Vp Th) Aj(Aw Bg Cp Fa Ij Im Iv Jq Kn Lx Mn Mq Mt Mv Nt Nv Ny Pg Qh Uc Uf Uv Vu Zq) Ly(An Ar Ax bM cE Cp Cs Cv Ef Fy GL Id Ko Lh Mq Ne Nu Pk Qx Tr Tv Vs Vt) Uu(cE Cp dG Ef Ez Fb fR Gl Im Jk Kf Mn Mw Nq Nv Nw Ok Pg Qh Qt St Ua Vw Wd) Pc(Ax bM Cs cW dF dG Ez Fy gL Jg Jy Kk Lh Lv Nh Nt Oa Oh Qb Qt Rh St Uw Wd) Kz(aD aJ Ax cE Cv dG Et Fb Jq Lh Lv Lw Mt Mw Nr Nv Om Or Pe St Uf Ut Vp) dI(As Bg Bn cA dL Ib Id In Jo Kk Mx Na Nv Oe Qt Ra St Tv Uc Ud Up Vp Vt) Nn(aC Ad aJ aM As bW Cp Cu Cv Cw Dc Gd Id Kd Ke Ou Pi Ra St Up Vt Xa) aW(aJ aP bA cE cG cT Cu dG Et Ex Ez Fa Lh Lx Mt Mu Nb Ny Or Pf Rm Un) Ed(As Bn bW Cq Cu Dp Hw Ij Kp Kr Na Pb Pi Pk Rj Rt Tv Ud Up Vb Vh) Mn(Hf Hv Hw Ih Ij In Ir Jg Lj Lw Mh Mj Ml Mx Mz Na Nb Nl Pa Pd Pg) Ye(Fb Fd Fr Ib Ij Iz Jm Js Kk Mj Mq Nv Oh Om Qw Rb Un Vq Wd Wh Zw) cN(Cs cW Dp Et Fa Hc Iv Ji Lh Ml Mw Nk Nt Oe Oh Ok Pk Qd Rh Un Ut) Tn(aJ aM aP Bb bL bW Co Et Ez Fi Ir Lw Oa Oe Pb Rm Uf Vq Tm Xa) Jg(Hv Hw Ij In Ir Jq Lj Lw Mh Mi Mj Mt Mx My Mz Na Nb Oe Pa Pg) gL(An Ch cP Dk Fp Fw Ha Id Im Jn Jr Li Lj Nt Or Pf Qb Qh Qt Ut) Fa(Ad aM aY bW Cu Cv Cw Dc Id Ij Jq Kn Kr Lw Na Pi Pk Up Uv) Mv(bM Cs Cv Em Hl Hp Ir Kk Lh Lj Mx Mz Na Ns Nt Pg Rv Wb Yl) Mw(aM Cs Id In Kk Kq Li Mm Nl Oa On Or Pd Pi St Ud Uf Up Vp) aJ(Ad Cp Cq cT Cu Cw Dc Dk Dp Lh Mu On Ou Pe Pf Pk Po Sr Ut) Fr(Ad As bM bW Cp Cq Cu Cw Dc Fy Iz Pi Sr Tv Ud Uv Vt Tm) Nc(Cs cT dF dG Dk Ez Gl Kk Ne Nh Ni Oa Qh Rm Uf Vi Vp Th) Jy(bF bS cA Co cT Dc Fy Lv Lw Mk My Nd Oh Or Pi Qd Rh Tj) In(aP cT Ex Gl Ih Jk Js Lj Lx Mt Mu Nh Nu Oa Or St Wb) bR(cG Fp Hp Ir Jn Lh Lv Mt Nb Nr Nw Ny Oh Or Ou Pi Yl) Qd(aM bS cP cW Dp Hc Hv Hw Ij Jo Jt Kg Mi Mz Nb Pk) Uf(aA bA Dp Fp Fy Jn Kl Lv Mg Nq Oe Or Pe Qa Vu Th) Lx(Ad aM An Cp Cq cT dH Dp Id Jt Kn Rj Tv Ud Vt) Sh(Ad dF Fb Iz Ji Jk Ko Nt Oh Pe Pf Ph Sr Vw Zq) Ou(aP cT Ex Fy Hc Hp Is Jn Nr Pe Po Qa Qe Rv Xa) Gl(aM An bP Cu Cv Cw dG Ef Fp Kg Oa Oe Oh Tv) Mu(An Ao bM bS cA Co Cw Dk Hc Id Kn Qz St Vt) Nh(Jk Jq Li Lj Mh Mi Mj Mz Na Ne Nq Ns Pd Pg) Ni(Ij Lz Mi Mj Mq Mx Nb Nl Nr Nx Pa Pd Qw Wm) Ud(bF Et Ex Is Jl Jn Mt Ny Pe Pf Po Sr St Wb) Kr(dG eC Ex Fy Id Ke Lv Lw Mz Nv Nw Oh Ok Vi) Pb(eC Fd Gb Hl Hp Ij Pg Ry Vh Vw Wd Wh Zq Zw) Kg(Ad Cw dF Et Ij Ok Om Pf Sr Un Ut Uv Vu) aM(An bF cE Cp Fb Fp Im Mq Nr Ny Po Vp Wb) cT(aP bM Cv dG Jq Lv Nw Pe Pf Pk Po Qa Sr) Bo(Ad Cp Cq Cu Dc Hv Hw Ij Jq Na Pk Vu) Fy(aY bW Hc Ji Jl Kd Ks Or Pa Qz Sr To) Mp(Hv Hw Lj Lw Mh Ml Mx Mz Na Ne Nu Qb) Qe(AD Cv Cw Dc dF Dp Id Kd Ke Ra Vt) St(Fp Hl Mi Ml Mq Nj Nl Or Qz Tv Uz Wg) Cs(An Aw cG Cp Dk Oe Om On Qt Rv Ut) Wb(Ar bC Hl Nd Nx Om Pk Ru Uv Wh Yl) Qb(Hv Hw Ij Ir Jt Li Mh Pa Sf Uw Yl) Nv(Lj Mh Mi Mm Mx My Na Ne Ns Oe Tm) aP(aC Ad bM Cp Cq Cu Cw Dc Dk Pk Vp) bF(aD An Ax Cp Cw Dr Iv Ml Oa Qa Uv) bW(bA dF Fp Is Jn Lv Nr Pe Po Qa Th) eC(As Bn Dd Ji Js Ke Kp Mj Na Ra Uv) fR(An Bg bI bO CH Ef Pi Qz Rv Yl) Dp(dG Dk Is Jn On Pe Qa Uw Vi Wd) Nt(Hv Ir Lw Mh Mi Mt Mx Mz Na Rv) Mq(Cu Cv Jt Kn Li Mi Mx Na Ns Pk) Im(aD aY bC dF Id Ju Or Rb Ut Vt) Jq(bA Cx Fn Li Mj Mx Mz Pa Pg Sr) Hc(Ax Cu Dk Et Ji Kk Om Pe Un) Oa(cE Di Dk Ef Et Lw Oc On Ut) Or(Db dF Nj Nl Ns Nw Oe On Th) Cv(Is Jl Jr Lv Pe Qa Sr Th) Cx(Hl Rt Uz Vh Vs Vw Wg Zq) Fn(Cu Ij Om Pi Pk Vi Vu Yl) Fp(aD Bg cF cW Dc dG Di Ut) Mm(Js Lj Mi Mj Ml Ne Oh Pg) Pf(An bS cA Co Pk Qz Sf Vt) Lw(Ij Li Lj Mh Mj Mz Sr) Nk(Hl Hp Ne Qh Rm Zq Tm) Rv(Dk dN Nx Om Sr Uw Vw) Oe(Ax aY dF dG Dk Ez Vu) Th(bC Ez Nj Ul Vs Wh) Ex(aD An dR Ef Mi Uv) Nq(Hp My Ne Zw Tm Wm) Qz(Et Kk Lh Nr Oh Pg) Nw(aY Ef Qw To Va Wg) cE(aD An Ax bM cA cW) Gd(Cu On Pi Un Vu) Ns(Ij Jk Li Nu Pg) Lv(aF bP Pa Pk Wm) Mz(bJ Jn Lh Mi Wc) Na(Ij Li Nb Pg Sr) Tm(Iz Kk Nj Ua Vq) Yl(aX Et Fb Rm Sr) Ut(Ao Bb bP Lj Uk) Va(Jm Lh Qm Vw Zq) bN(Uw Vb Vi Wd Zq) dG(An Bg cA cL Jn) Co(Nr Pe Po Qa) Ne(Ij Jk Li Lj) Oh(Jo Jt Kk Qt) Vp(cW Et Nj Pk) Vw(Af Ap Kc Ld) Pa(Jn Un Uw Zw) bM(Aw cG Cp Ef) dF(aD Jn Nr Pk) Bg(Hp Ji Un) Wm(Ih Mi Ok) Po(aD Dc Pk) Ez(Du Uz Wg) Mx(Ij Ir Jk) Sf(Ij Pe Sr) Jl(Dc Ke Ks) On(Ax Kl Pk) Vi(Af aX Jt) An(Ax cU) Dr(bG Gn) Ti(Et Ji) Mi(Ir Lh) Mt(bS cA) Zq(Af Ap) Xa(aA Ch) Kk(Qt Qw) Kq(Vs Tj) Lj(Jh Nx) Pe(Ha Jn) bP(Aw Cp) cG(cA cP) cW(Fb Nr) DkcP EfaD EqJk MlbA NjHl IiVu IrLh ZwJf JdKe JiSr WcUn WdbU WhKc RhaA NyPg

Constrained panels with 2 analytes, where 1.0E-2 >= 'AUC p-value' > 1.0E-3. Contains 3,205 panels of 87,101 total panels evaluated. : Us(An Aw Ax Bo cN Cp CS Cw Db Dc dI dL Ef Em Ez Id Ij Im Ir Iv Jj Jk Js Jt Kf Ki Kj Kn Ky Lu Me Mj Nb Nf Nt Oa Og Oi Oz Pc Pg Ph Pk Qb Qv Qy Rb Rf St Ua Ur Uv Vp Vs Vt Wb Wd Yl) cS(Ad As Aw Ba Bn bW Cq Cv Dc Dd Em Ez Gn Hv Hw Id Ij In Ir Js Kd Kn Kp Kr Lx Mj Ml Mn Mv Mx Mz Na Nb Nt Ny Ok Om Ou Ow Pb Pi Pk Qh Qz Ra Rb Rj St Tn Tv Uc Up Ut Uv Vp Vt Tm) dA(Ad aM An As aV AW Ax Ba Bn bR bU bW cF cK cP Cv Cw dL Ez Id Im Iv Jj Ke Kk Kz Ly Mj Ml Mt Nb Nc Nd Nf Ng Ns Nt Nv Ny Oe Ow Oy Pc Pk Qb Qn Qz Rb Uc Uk Ur Uw Wb Yl Ye) Ky(Ad As aW Bg Bn bW Cp Cq cT Cu Cv Cw Dc dF dG Dk gL Hl Hv Hw Id Ij In Ir Jq Kd Kn Kp Kr Lw Md Mi Mz Na Nb Nt Ok Om Ou Pb Pi Ra Rb Rj Tn Tv Uc Ud Ul Up Ut Vp Vq Zw Tm) cN(An Ax bM bR bU cA cP Cu Cw Dc Dk Hq Hv Hw Id Ij In Ir Jj Jq Js Jt Kd Kk Kn Kp Kr Mj Mk Mz Na Nb Nd Ng Ns Nw Ny Om Pb Pi Qz Ra Rb Rj St Uc Ud Uk Up Ur Uv Vp Vt Ye Th) Nf(aC Ad aM aW Ax bF BG bH bR bW Cp Cu Dc dL Em Gl Gp Hl Hu Id Ir Je Jk Jv Ke Kn Ko Kp Li Lj Lu Lw Me Mj Mm Mv Mx Nb Nh Nv Og Oi Ow Pa Pb Pg Pk Ql Ru Up Uw Vt) Rf(aD aJ An As bB Bn Cp Cq cT Cw Dc Dk dL Ef Em Et Hl Hv Hw Id Ij Im Ir Iv Js Kn Kp Kr Lv Mi Ml Na Nr Ok Pb Pe Pi Pk Ra Rb Rj Rt Tv Uc Ud Ul Up Uw Uz Vp Vs Vt Wg) Qv(Ad As aW Ax Bg Bn bW Cp Cq Cu Cv Cw Dc dG Fd fR Hp Hv Hw Id Ij Ir Iv Jq Jt Kd Ke Kf Kn Kp Kr Lw Lx Ml Mm Mz Na Nm Pb Pi Ra Rb Rj Uc Ul Up Uw Vq Vw Wd Zq Tm) Ud(AJ aM aP Ax Ba bH Cs cT cW dF dM Fp Fy GL Hu Im Jj Jp Jy Kk Kx Lh Ly Ma Me Mn Mq Mu Nr Nw Oi On Ow Oy Oz Pk Qd Ql Qy Ri Tn Uf Uh Ut Vz Zq Zw Xa Th) Jv(An aO Aw bB Bc bH cG Cu CW dG Dl Ef Ez Fb gL Gp Hp Id Iv Jg Ji Jk Jq Kn Ko Kz Lw Mq Mv Nb Nt Oa Ok Om Ou Pk Qb Qm Qt Qw Ri Tr Uh Ur

Ed(Hl Uz Wg Tl) Zw(bU Fb Fr Jp) Kq(Ct Ex Jd Ny) Ou(Jp Jy Mw Qd) Vu(Co Ni Ug Uk) aX(aC Fy Hp Zq) Ap(Et Lh Uw) Mn(Js Li Vp) Mx(Li Nh Pg) Mz(dM Nv Pg) Iv(cE dG Fi) Rb(Fp Gd Wh) Wd(Af Bb Lj) Jk(Lj Mj Na) bU(Fd Vh Zq) cA(aO cU cV) Ti(Ok Un) Em(Ez Pf) Fb(Hl Vp) Ex(Jy Na) Gp(Lh Ul) Mu(eF Or) Mw(aC Kp) My(Jh Nx) Qd(dF Or) Wh(Js Lj) Xa(bA Qx) Kk(dM Ny) Oh(Uk tF) bM(aO aZ) AfVb CoLh PoFi EqIz EzMg GdSr MkfR MpHq HpJf UcUg TrHf ImKp IodF UkdG VsbV aCbE cEdL cVcX

Figure 7 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ad | ug/mL | 4.1E-2 | 7.1E-2 | 7.5E-2 | 1.1E0 | 9.0E-2 | 3.0E0 | 2.7E-4 | 4.3E-3 | 5.4E-1 | 8.5E0 | 454 | 8 | 168 | 8 | 0.59 |
| Af | ng/mL | 1.1E0 | 4.4E-1 | 1.5E1 | 3.7E1 | 6.0E1 | 9.0E1 | 1.7E-3 | 1.7E-3 | 5.3E2 | 2.6E2 | 454 | 8 | 168 | 8 | 0.48 |
| Aj | ug/mL | 1.6E0 | 1.6E-1 | 2.6E0 | 1.0E0 | 2.4E0 | 2.0E0 | 1.5E-3 | 2.1E-3 | 6.1E0 | 5.8E0 | 454 | 8 | 168 | 8 | 0.29 |
| Al | mg/mL | 8.7E-5 | 8.4E-5 | 2.5E-4 | 1.3E-4 | 4.0E-4 | 1.3E-4 | 2.3E-6 | 3.9E-5 | 1.9E-3 | 4.4E-4 | 454 | 8 | 168 | 8 | 0.52 |
| An | U/mL | 5.1E1 | 8.1E1 | 1.8E2 | 1.2E3 | 4.4E2 | 2.7E3 | 9.8E-4 | 4.3E1 | 5.5E3 | 7.8E3 | 454 | 8 | 168 | 8 | 0.69 |
| Ao | pg/mL | 8.9E1 | 6.3E1 | 5.1E2 | 1.4E2 | 3.4E3 | 2.0E2 | 2.8E0 | 5.4E0 | 3.9E4 | 6.0E2 | 454 | 8 | 168 | 8 | 0.42 |
| Ap | ng/mL | 3.3E1 | 1.9E1 | 4.5E1 | 4.3E1 | 4.4E1 | 5.2E1 | 8.4E-5 | 8.4E0 | 2.9E2 | 1.6E2 | 454 | 8 | 168 | 8 | 0.43 |
| Ar | ng/mL | 9.7E-1 | 3.3E0 | 1.2E1 | 4.7E0 | 1.9E2 | 4.4E0 | 3.4E-3 | 5.0E-1 | 4.1E3 | 1.4E1 | 454 | 8 | 168 | 8 | 0.74 |
| As | ng/mL | 9.0E-3 | 1.1E-2 | 1.3E-2 | 1.6E-1 | 1.9E-2 | 4.3E-1 | 1.7E-3 | 1.7E-3 | 1.3E-1 | 1.2E0 | 454 | 8 | 168 | 8 | 0.54 |
| Aw | pg/mL | 1.6E1 | 1.8E1 | 1.6E1 | 2.2E1 | 6.1E0 | 1.3E1 | 2.9E-2 | 1.3E1 | 4.8E1 | 5.1E1 | 454 | 8 | 168 | 8 | 0.64 |
| Ax | ng/mL | 2.4E0 | 7.9E0 | 1.7E1 | 9.3E1 | 6.5E1 | 1.4E2 | 1.2E-2 | 1.7E0 | 7.7E2 | 3.7E2 | 454 | 8 | 168 | 8 | 0.73 |
| Ba | ng/mL | 7.0E1 | 3.8E2 | 4.4E2 | 1.3E3 | 1.2E3 | 1.8E3 | 3.7E-1 | 1.6E1 | 8.1E3 | 4.4E3 | 454 | 8 | 168 | 8 | 0.70 |
| Bb | ng/mL | 3.1E0 | 2.8E0 | 6.5E0 | 5.7E0 | 1.4E1 | 6.7E0 | 4.1E-3 | 6.8E-1 | 2.5E2 | 1.9E1 | 454 | 8 | 168 | 8 | 0.52 |
| Bc | ng/mL | 3.9E1 | 1.1E2 | 1.1E2 | 2.4E2 | 2.0E2 | 3.3E2 | 1.1E-1 | 9.6E0 | 1.2E3 | 1.0E3 | 454 | 8 | 168 | 8 | 0.68 |
| Bg | ng/mL | 9.1E-2 | 1.7E-1 | 5.9E0 | 7.0E-1 | 3.5E1 | 1.0E0 | 5.3E-4 | 1.0E-2 | 4.4E2 | 2.9E0 | 454 | 8 | 168 | 8 | 0.56 |
| Bn | ng/mL | 5.6E-2 | 9.7E-1 | 1.2E0 | 8.3E0 | 2.0E0 | 2.0E1 | 5.6E-2 | 5.6E-2 | 9.7E0 | 5.8E1 | 454 | 8 | 168 | 8 | 0.55 |
| Bo | ng/mL | 1.2E1 | 2.2E1 | 1.5E1 | 2.6E1 | 1.9E1 | 1.9E1 | 1.6E-2 | 1.6E-2 | 2.8E2 | 5.3E1 | 454 | 8 | 168 | 8 | 0.69 |
| Ch | uIU/mL | 1.2E0 | 8.4E-1 | 2.1E1 | 8.1E-1 | 1.1E2 | 3.8E-1 | 3.4E-3 | 1.8E-1 | 1.8E3 | 1.4E0 | 454 | 8 | 168 | 8 | 0.36 |
| Co | pg/mL | 4.0E1 | 4.2E1 | 1.7E2 | 6.4E1 | 9.5E2 | 7.4E1 | 1.5E-1 | 1.5E-1 | 1.7E4 | 2.2E2 | 454 | 8 | 168 | 8 | 0.47 |
| Cp | ng/mL | 2.2E1 | 2.1E1 | 2.9E1 | 1.9E2 | 3.2E1 | 4.4E2 | 6.0E-1 | 1.4E1 | 3.7E2 | 1.3E3 | 454 | 8 | 168 | 8 | 0.60 |
| Cq | ng/mL | 3.0E-2 | 3.5E-2 | 1.6E-1 | 6.1E0 | 8.8E-1 | 1.7E1 | 8.0E-4 | 8.0E-4 | 1.7E1 | 4.9E1 | 454 | 8 | 168 | 8 | 0.49 |
| Cs | ng/mL | 7.3E1 | 4.6E2 | 3.4E2 | 1.5E3 | 1.1E3 | 2.0E3 | 2.7E-2 | 3.0E1 | 1.8E4 | 5.1E3 | 454 | 8 | 168 | 8 | 0.78 |
| Ct | ng/mL | 6.0E-1 | 1.1E-1 | 4.0E1 | 6.9E1 | 1.1E2 | 1.6E2 | 1.1E-4 | 5.7E-2 | 6.2E2 | 4.7E2 | 454 | 8 | 168 | 8 | 0.47 |
| Cu | ng/mL | 2.5E-1 | 3.6E-1 | 5.0E-1 | 8.8E0 | 1.4E0 | 2.3E1 | 9.6E-3 | 4.6E-2 | 2.1E1 | 6.6E1 | 454 | 8 | 168 | 8 | 0.62 |
| Cv | ng/mL | 5.1E0 | 7.3E0 | 2.1E1 | 1.6E2 | 5.2E1 | 2.3E2 | 1.4E-4 | 1.9E-1 | 5.3E2 | 5.2E2 | 454 | 8 | 168 | 8 | 0.58 |
| Cw | mIU/mL | 3.0E-2 | 3.4E-2 | 3.8E-2 | 8.8E-1 | 3.1E-2 | 2.4E0 | 1.5E-4 | 1.4E-2 | 2.4E-1 | 6.8E0 | 454 | 8 | 168 | 8 | 0.61 |
| Cx | ng/mL | 2.2E-1 | 7.8E-3 | 5.6E1 | 1.0E2 | 1.0E2 | 1.6E2 | 9.3E-5 | 9.3E-5 | 3.9E2 | 3.9E2 | 454 | 8 | 168 | 8 | 0.45 |
| Db | ug/mL | 7.3E0 | 1.1E1 | 8.8E0 | 1.1E1 | 9.4E0 | 6.6E0 | 4.5E-1 | 1.4E0 | 1.4E2 | 1.9E1 | 454 | 8 | 168 | 8 | 0.62 |
| Dc | nmol/L | 1.9E-2 | 1.6E-2 | 6.2E-2 | 2.0E0 | 1.5E-1 | 4.9E0 | 5.2E-6 | 1.3E-3 | 1.6E0 | 1.4E1 | 454 | 8 | 168 | 8 | 0.56 |
| Dd | ug/mL | 6.9E-2 | 6.1E-2 | 1.7E-1 | 5.4E-1 | 2.6E-1 | 1.2E0 | 1.9E-4 | 6.2E-3 | 1.9E0 | 3.6E0 | 454 | 8 | 168 | 8 | 0.52 |
| De | ng/mL | 3.4E-3 | 3.4E-3 | 8.0E-2 | 1.5E-1 | 1.4E-1 | 2.7E-1 | 3.4E-3 | 3.4E-3 | 9.2E-1 | 7.9E-1 | 454 | 8 | 168 | 8 | 0.54 |
| Dg | ng/mL | 3.5E1 | 2.5E1 | 4.6E1 | 5.2E1 | 4.0E1 | 6.2E1 | 1.0E-1 | 4.7E0 | 1.9E2 | 1.9E2 | 454 | 8 | 168 | 8 | 0.48 |
| Di | pg/mL | 1.9E0 | 3.3E0 | 2.2E0 | 3.5E0 | 2.1E0 | 2.8E0 | 1.8E-1 | 1.8E-1 | 1.3E1 | 9.0E0 | 454 | 8 | 168 | 8 | 0.66 |
| Dk | uIU/mL | 1.7E-2 | 3.2E-2 | 8.5E-2 | 2.0E-1 | 5.1E-1 | 2.7E-1 | 1.1E-4 | 5.8E-3 | 8.9E0 | 6.3E-1 | 454 | 8 | 168 | 8 | 0.64 |
| Dl | ng/mL | 2.4E2 | 3.0E2 | 3.3E2 | 4.6E2 | 3.0E2 | 5.0E2 | 1.7E0 | 1.8E1 | 1.5E3 | 1.6E3 | 454 | 8 | 168 | 8 | 0.56 |
| Dp | ng/ml | 2.4E0 | 1.0E0 | 5.3E0 | 3.1E1 | 8.2E0 | 7.0E1 | 3.7E-3 | 3.7E-3 | 5.6E1 | 2.0E2 | 290 | 8 | 162 | 8 | 0.42 |
| Ef | ng/ml | 1.5E-1 | 2.4E-1 | 8.9E-1 | 1.4E0 | 1.8E0 | 2.5E0 | 5.7E-4 | 1.1E-2 | 1.0E1 | 7.0E0 | 344 | 7 | 165 | 7 | 0.54 |
| Wm | % | 4.7E-1 | 7.5E0 | 3.9E1 | 1.1E2 | 1.9E2 | 3.0E2 | 5.4E-2 | 8.5E-2 | 2.4E3 | 1.0E3 | 358 | 12 | 178 | 12 | 0.69 |
| Ed | pg/ml | 5.2E-1 | 6.8E1 | 6.1E1 | 7.1E1 | 4.3E2 | 4.7E1 | 5.2E-1 | 4.4E0 | 7.3E3 | 1.5E2 | 290 | 8 | 161 | 8 | 0.79 |
| Tj | pg/mL | 3.7E-1 | 3.0E0 | 5.6E1 | 3.8E1 | 2.9E2 | 5.4E1 | 3.6E-1 | 3.7E-1 | 3.5E3 | 1.4E2 | 339 | 8 | 167 | 8 | 0.59 |
| Po | pg/ml | 8.0E-1 | 2.9E1 | 8.3E0 | 5.0E1 | 2.2E1 | 6.6E1 | 8.0E-3 | 5.3E-1 | 2.7E2 | 2.2E2 | 799 | 14 | 262 | 14 | 0.82 |
| Et | ng/ml | 1.5E3 | 3.5E3 | 1.7E3 | 3.4E3 | 1.2E3 | 1.4E3 | 7.7E1 | 7.9E2 | 5.0E3 | 5.0E3 | 798 | 14 | 262 | 14 | 0.81 |
| Fa | ng/ml | 4.8E1 | 2.5E2 | 1.3E2 | 2.8E2 | 5.4E2 | 2.2E2 | 3.4E-2 | 7.5E0 | 8.0E3 | 7.3E2 | 286 | 8 | 160 | 8 | 0.83 |
| Ez | ng/ml | 4.5E0 | 1.4E1 | 1.8E1 | 2.4E1 | 5.3E1 | 2.9E1 | 1.3E-2 | 1.1E-1 | 7.1E2 | 8.8E1 | 290 | 8 | 162 | 8 | 0.65 |
| Fb | ng/ml | 2.6E1 | 2.6E1 | 2.4E1 | 2.9E1 | 1.1E1 | 5.8E0 | 5.9E-1 | 2.4E1 | 5.7E1 | 4.1E1 | 287 | 8 | 160 | 8 | 0.61 |
| Fn | ng/ml | 2.1E-1 | 2.1E-1 | 5.8E0 | 3.5E0 | 2.5E1 | 9.3E0 | 1.1E-14 | 2.1E-1 | 4.2E2 | 2.7E1 | 290 | 8 | 162 | 8 | 0.36 |
| Fp | ng/ml | 1.4E1 | 6.2E1 | 2.6E1 | 6.1E1 | 2.9E1 | 3.9E1 | 6.0E-3 | 6.8E0 | 1.4E2 | 1.3E2 | 828 | 13 | 264 | 13 | 0.78 |
| Fr | ng/ml | 4.1E4 | 4.2E5 | 1.2E5 | 4.0E5 | 1.8E5 | 3.2E5 | 1.9E2 | 1.0E4 | 9.0E5 | 8.4E5 | 916 | 14 | 265 | 14 | 0.76 |
| Fw | pg/ml | 1.1E0 | 8.2E0 | 6.3E1 | 4.8E1 | 4.7E2 | 1.1E2 | 1.1E-14 | 1.2E-1 | 6.9E3 | 3.3E2 | 342 | 8 | 166 | 8 | 0.61 |
| Fy | ng/ml | 3.5E1 | 7.3E1 | 5.8E1 | 2.2E2 | 6.9E1 | 2.6E2 | 1.2E-1 | 1.2E1 | 5.3E2 | 6.5E2 | 288 | 7 | 161 | 7 | 0.70 |
| Gl | pg/ml | 7.5E3 | 1.9E4 | 1.1E4 | 1.9E4 | 9.3E3 | 1.1E4 | 9.1E1 | 1.3E3 | 3.3E4 | 3.1E4 | 334 | 8 | 165 | 8 | 0.71 |
| Gp | U/ml | 1.4E0 | 1.2E0 | 3.9E0 | 2.1E0 | 6.8E0 | 2.5E0 | 1.3E-3 | 1.5E-2 | 6.7E1 | 7.3E0 | 344 | 8 | 166 | 8 | 0.44 |
| Gz | ug/ml | 1.2E0 | 2.2E0 | 8.2E0 | 4.2E0 | 3.6E1 | 5.0E0 | 2.9E-16 | 1.0E-1 | 4.8E2 | 1.1E1 | 196 | 7 | 104 | 7 | 0.47 |
| Ha | ng/ml | 2.6E0 | 5.8E0 | 9.4E0 | 2.2E1 | 2.0E1 | 3.5E1 | 6.4E-3 | 6.4E-1 | 1.3E2 | 1.0E2 | 288 | 8 | 161 | 8 | 0.62 |

Figure 8

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nm | pg/ml | 1.7E4 | 3.4E4 | 3.4E4 | 1.0E5 | 8.2E4 | 2.1E5 | 1.0E-9 | 1.0E-9 | 1.6E6 | 8.2E5 | 802 | 14 | 264 | 14 | 0.66 |
| Nn | pg/ml | 1.7E2 | 2.1E3 | 1.9E3 | 1.7E4 | 8.2E3 | 3.5E4 | 1.0E-9 | 1.1E2 | 1.0E5 | 1.1E5 | 802 | 14 | 264 | 14 | 0.79 |
| No | pg/ml | 1.7E1 | 1.0E2 | 3.7E1 | 2.2E2 | 1.1E2 | 2.6E2 | 1.0E-9 | 9.0E0 | 2.5E3 | 7.7E2 | 802 | 14 | 264 | 14 | 0.84 |
| Nq | pg/ml | 2.3E0 | 2.0E1 | 2.0E1 | 4.3E1 | 7.7E1 | 6.2E1 | 1.0E-9 | 1.0E-9 | 1.2E3 | 2.2E2 | 802 | 14 | 264 | 14 | 0.67 |
| Nr | pg/ml | 1.3E0 | 7.4E0 | 3.0E1 | 1.7E2 | 1.9E2 | 3.9E2 | 1.0E-9 | 1.0E-9 | 4.1E3 | 1.4E3 | 802 | 14 | 264 | 14 | 0.65 |
| Ns | pg/ml | 1.0E-9 | 1.0E-9 | 9.6E0 | 1.0E-9 | 5.5E1 | 0.0E0 | 1.0E-9 | 1.0E-9 | 1.1E3 | 1.0E-9 | 802 | 14 | 264 | 14 | 0.45 |
| Nt | pg/ml | 1.1E2 | 1.9E2 | 1.4E2 | 3.0E2 | 1.1E2 | 3.2E2 | 1.0E-9 | 4.4E1 | 1.5E3 | 1.2E3 | 802 | 14 | 264 | 14 | 0.70 |
| Nu | pg/ml | 2.4E1 | 7.4E1 | 5.6E1 | 1.2E2 | 8.9E1 | 1.2E2 | 1.0E-9 | 1.0E-9 | 8.9E2 | 3.7E2 | 802 | 14 | 264 | 14 | 0.69 |
| Lu | pg/ml | 1.0E4 | 5.6E3 | 1.8E4 | 7.8E3 | 6.5E4 | 5.7E3 | 3.5E2 | 2.6E3 | 1.3E6 | 2.2E4 | 805 | 14 | 264 | 14 | 0.36 |
| Lv | pg/ml | 1.0E-9 | 3.8E1 | 1.1E1 | 5.0E1 | 2.3E1 | 5.7E1 | 1.0E-9 | 1.0E-9 | 2.6E2 | 1.6E2 | 805 | 14 | 264 | 14 | 0.72 |
| Lw | pg/ml | 1.0E-9 | 1.0E-9 | 3.2E-1 | 6.6E0 | 3.7E0 | 1.2E1 | 1.0E-9 | 1.0E-9 | 8.0E1 | 4.0E1 | 805 | 14 | 264 | 14 | 0.64 |
| Lx | pg/ml | 1.0E-9 | 9.8E1 | 1.5E2 | 1.1E3 | 4.3E2 | 9.5E2 | 1.0E-9 | 1.0E-9 | 6.2E3 | 2.8E3 | 805 | 14 | 264 | 14 | 0.81 |
| Ly | pg/ml | 1.0E-9 | 1.0E-9 | 1.0E1 | 3.9E0 | 2.0E1 | 7.8E0 | 1.0E-9 | 1.0E-9 | 1.6E2 | 2.6E1 | 805 | 14 | 264 | 14 | 0.44 |
| Lz | pg/ml | 1.0E-9 | 1.0E-9 | 3.8E0 | 1.0E1 | 3.1E1 | 2.1E1 | 1.0E-9 | 1.0E-9 | 6.0E2 | 6.2E1 | 805 | 14 | 264 | 14 | 0.58 |
| Ma | pg/ml | 3.0E2 | 1.7E3 | 1.3E3 | 4.5E3 | 3.8E3 | 8.2E3 | 1.0E-9 | 8.7E1 | 6.5E4 | 3.1E4 | 805 | 14 | 264 | 14 | 0.70 |
| Mb | pg/ml | 2.5E1 | 3.0E1 | 3.1E1 | 3.4E1 | 1.5E1 | 2.0E1 | 5.4E0 | 4.1E0 | 2.1E2 | 7.1E1 | 805 | 14 | 264 | 14 | 0.51 |
| Mc | pg/ml | 1.0E-9 | 1.0E-9 | 4.3E-2 | 1.0E-9 | 6.0E-1 | 0.0E0 | 1.0E-9 | 1.0E-9 | 1.3E1 | 1.0E-9 | 805 | 14 | 264 | 14 | 0.49 |
| Md | pg/ml | 1.0E-9 | 1.0E-9 | 3.7E-1 | 2.5E0 | 2.8E0 | 7.9E0 | 1.0E-9 | 1.0E-9 | 6.5E1 | 2.9E1 | 805 | 14 | 264 | 14 | 0.57 |
| Me | pg/ml | 3.3E1 | 1.6E1 | 3.2E1 | 2.8E1 | 2.0E1 | 4.7E1 | 1.0E-9 | 1.0E-9 | 3.2E2 | 1.8E2 | 805 | 14 | 264 | 14 | 0.29 |
| Mf | pg/ml | 1.0E-9 | 1.0E-9 | 5.5E-1 | 8.1E-1 | 3.0E0 | 1.8E0 | 1.0E-9 | 1.0E-9 | 5.6E1 | 5.5E0 | 805 | 14 | 264 | 14 | 0.57 |
| Mg | pg/ml | 1.8E0 | 9.2E-1 | 7.6E0 | 7.6E0 | 1.2E1 | 1.0E1 | 1.0E-9 | 1.0E-9 | 9.2E1 | 2.7E1 | 805 | 14 | 264 | 14 | 0.50 |
| Mh | pg/ml | 1.0E-9 | 1.5E-2 | 1.3E0 | 3.9E0 | 9.8E0 | 6.4E0 | 1.0E-9 | 1.0E-9 | 1.6E2 | 1.8E1 | 805 | 14 | 264 | 14 | 0.64 |
| Mi | pg/ml | 1.0E-9 | 1.0E-9 | 4.8E-1 | 1.1E1 | 5.4E0 | 3.0E1 | 1.0E-9 | 1.0E-9 | 1.2E2 | 1.1E2 | 805 | 14 | 264 | 14 | 0.60 |
| Mj | pg/ml | 1.0E-9 | 1.0E-9 | 4.3E0 | 3.8E1 | 2.4E1 | 7.0E1 | 1.0E-9 | 1.0E-9 | 4.6E2 | 2.1E2 | 805 | 14 | 264 | 14 | 0.63 |
| Mk | pg/ml | 9.1E-1 | 5.7E0 | 1.5E1 | 4.4E1 | 9.1E1 | 1.3E2 | 1.0E-9 | 1.0E-9 | 1.7E3 | 5.0E2 | 805 | 14 | 264 | 14 | 0.60 |
| Ml | pg/ml | 1.0E-9 | 1.0E-9 | 5.2E0 | 4.9E1 | 7.7E1 | 1.4E2 | 1.0E-9 | 1.0E-9 | 2.1E3 | 5.1E2 | 805 | 14 | 264 | 14 | 0.65 |
| Mm | pg/ml | 6.4E2 | 1.8E3 | 1.1E3 | 2.7E3 | 1.3E3 | 3.2E3 | 1.0E-9 | 7.1E1 | 1.1E4 | 1.2E4 | 805 | 14 | 264 | 14 | 0.69 |
| Mn | pg/ml | 5.7E0 | 1.1E1 | 1.1E1 | 1.7E1 | 2.4E1 | 1.5E1 | 1.0E-9 | 2.8E0 | 3.5E2 | 5.1E1 | 805 | 14 | 264 | 14 | 0.73 |
| Mp | pg/ml | 1.0E-9 | 2.7E1 | 9.3E0 | 4.2E1 | 3.0E1 | 4.3E1 | 1.0E-9 | 1.0E-9 | 6.3E2 | 1.3E2 | 804 | 14 | 264 | 14 | 0.79 |
| Mq | pg/ml | 1.0E-9 | 3.5E0 | 2.7E0 | 2.5E1 | 1.7E1 | 3.7E1 | 1.0E-9 | 1.0E-9 | 2.4E2 | 1.0E2 | 804 | 14 | 264 | 14 | 0.72 |
| Mr | pg/ml | 1.0E-9 | 7.2E0 | 2.8E1 | 3.9E2 | 1.5E2 | 9.4E2 | 1.0E-9 | 1.0E-9 | 2.2E3 | 3.4E3 | 804 | 14 | 264 | 14 | 0.72 |
| Ms | pg/ml | 4.1E2 | 2.2E2 | 5.5E2 | 3.3E2 | 6.5E2 | 3.1E2 | 1.0E-9 | 1.0E-9 | 5.9E3 | 9.8E2 | 804 | 14 | 264 | 14 | 0.41 |
| Mt | pg/ml | 4.8E-1 | 9.7E0 | 7.2E2 | 2.6E2 | 4.4E1 | 8.6E2 | 1.0E-9 | 1.0E-9 | 8.7E2 | 3.2E3 | 804 | 14 | 264 | 14 | 0.78 |
| Mu | pg/ml | 1.0E-9 | 2.4E0 | 1.4E0 | 5.8E0 | 1.1E1 | 1.0E1 | 1.0E-9 | 1.0E-9 | 2.3E2 | 3.5E1 | 804 | 14 | 264 | 14 | 0.79 |
| Mv | pg/ml | 1.0E-9 | 5.9E1 | 7.6E0 | 1.4E2 | 3.3E2 | 2.8E2 | 1.0E-9 | 1.0E-9 | 4.5E3 | 9.2E2 | 804 | 14 | 264 | 14 | 0.67 |
| Mw | pg/ml | 4.0E1 | 2.8E2 | 5.5E2 | 1.2E3 | 3.5E3 | 1.9E3 | 1.0E-9 | 1.0E-9 | 6.2E4 | 5.3E3 | 804 | 14 | 264 | 14 | 0.78 |
| Mx | pg/ml | 1.0E-9 | 1.0E-9 | 2.6E-1 | 2.4E0 | 1.4E0 | 5.3E0 | 1.0E-9 | 1.0E-9 | 3.2E1 | 2.0E1 | 804 | 14 | 264 | 14 | 0.66 |
| My | pg/ml | 1.0E-9 | 1.0E-9 | 5.1E2 | 2.1E2 | 3.1E3 | 5.1E2 | 1.0E-9 | 1.0E-9 | 3.9E4 | 1.9E3 | 804 | 14 | 264 | 14 | 0.56 |
| Mz | pg/ml | 1.2E1 | 2.9E1 | 2.8E1 | 2.7E2 | 6.5E1 | 5.8E2 | 1.0E-9 | 1.0E-9 | 1.2E3 | 1.9E3 | 804 | 14 | 264 | 14 | 0.71 |
| Na | pg/ml | 1.0E-9 | 1.0E-9 | 6.3E-1 | 5.5E0 | 2.7E0 | 1.1E1 | 1.0E-9 | 1.0E-9 | 3.6E1 | 4.2E1 | 804 | 14 | 264 | 14 | 0.64 |
| Nb | pg/ml | 2.1E0 | 4.4E0 | 4.0E0 | 2.7E1 | 1.2E1 | 5.9E1 | 1.0E-9 | 1.0E-9 | 2.3E2 | 2.1E2 | 804 | 14 | 264 | 14 | 0.66 |
| Nc | pg/ml | 3.4E2 | 2.0E2 | 5.6E2 | 3.6E2 | 7.4E2 | 3.8E2 | 1.0E-9 | 1.0E-9 | 9.2E3 | 1.1E3 | 804 | 14 | 264 | 14 | 0.45 |
| Nd | pg/ml | 2.8E1 | 1.4E1 | 2.7E1 | 2.4E1 | 4.7E1 | 2.8E1 | 1.0E-9 | 1.0E-9 | 1.2E3 | 9.4E1 | 804 | 14 | 264 | 14 | 0.45 |
| Ne | pg/ml | 4.5E2 | 2.6E2 | 5.8E2 | 2.6E2 | 5.9E2 | 1.9E2 | 1.0E-9 | 1.0E-9 | 7.0E3 | 5.8E2 | 804 | 14 | 264 | 14 | 0.33 |
| Nf | pg/ml | 1.0E-9 | 8.7E-1 | 2.5E0 | 1.8E1 | 9.5E0 | 4.4E1 | 1.0E-9 | 1.0E-9 | 1.6E2 | 1.3E2 | 804 | 14 | 264 | 14 | 0.64 |
| Ng | pg/ml | 2.8E1 | 7.6E0 | 1.3E2 | 3.7E1 | 2.5E2 | 6.0E1 | 1.0E-9 | 1.0E-9 | 2.3E3 | 1.7E2 | 804 | 14 | 264 | 14 | 0.39 |
| Nh | pg/ml | 6.8E1 | 3.6E1 | 9.1E1 | 4.0E1 | 8.5E1 | 2.4E1 | 1.0E-9 | 4.1E0 | 5.6E2 | 7.5E1 | 804 | 14 | 264 | 14 | 0.30 |
| Ni | pg/ml | 1.0E-9 | 1.5E2 | 7.4E1 | 2.2E2 | 1.2E2 | 3.0E2 | 1.0E-9 | 1.0E-9 | 7.1E2 | 1.1E3 | 804 | 14 | 264 | 14 | 0.64 |
| Nj | pg/ml | 7.3E0 | 3.4E0 | 1.1E1 | 7.0E0 | 1.2E1 | 7.0E0 | 1.0E-9 | 1.0E-9 | 1.1E2 | 2.0E1 | 804 | 14 | 264 | 14 | 0.42 |
| Nk | pg/ml | 1.7E1 | 2.4E1 | 3.3E1 | 2.6E1 | 4.0E1 | 2.3E1 | 1.0E-9 | 1.0E-9 | 2.0E2 | 6.6E1 | 804 | 14 | 264 | 14 | 0.51 |
| Nl | pg/ml | 4.6E1 | 2.4E1 | 6.1E1 | 3.1E1 | 6.9E1 | 2.7E1 | 1.0E-9 | 1.0E-9 | 1.1E3 | 8.2E1 | 804 | 14 | 264 | 14 | 0.37 |
| Tz | pg/ml | 5.6E3 | 1.0E4 | 2.2E4 | 1.0E4 | 1.4E5 | 8.1E3 | 1.0E-9 | 8.1E2 | 2.1E6 | 2.5E4 | 292 | 8 | 160 | 8 | 0.59 |
| Ua | pg/ml | 3.9E3 | 6.5E3 | 1.4E4 | 8.4E3 | 2.7E4 | 6.3E3 | 1.0E-9 | 1.1E3 | 1.9E5 | 1.9E4 | 292 | 8 | 160 | 8 | 0.58 |
| Ub | pg/ml | 5.5E2 | 3.5E2 | 8.1E2 | 6.8E2 | 1.0E3 | 9.2E2 | 1.0E-9 | 1.2E1 | 9.8E3 | 2.8E3 | 292 | 8 | 160 | 8 | 0.42 |
| Ue | pg/ml | 2.7E1 | 1.6E1 | 3.8E1 | 3.7E1 | 4.2E1 | 4.6E1 | 9.8E-2 | 5.9E0 | 4.4E2 | 1.4E2 | 292 | 8 | 160 | 8 | 0.39 |
| Uc | pg/ml | 9.8E2 | 9.8E1 | 1.9E3 | 8.1E3 | 2.7E3 | 2.0E4 | 1.0E-9 | 5.5E1 | 2.9E4 | 5.7E4 | 292 | 8 | 160 | 8 | 0.48 |
| Ud | pg/ml | 1.0E-9 | 1.0E-9 | 1.4E0 | 6.7E0 | 2.3E1 | 1.9E1 | 1.0E-9 | 1.0E-9 | 3.9E2 | 5.3E1 | 292 | 8 | 160 | 8 | 0.56 |

Figure 8 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Hq | pg/ml | 1.1E0 | 2.2E0 | 1.1E2 | 1.8E1 | 1.7E3 | 4.8E1 | 1.0E-9 | 1.0E-9 | 3.4E4 | 1.8E2 | 800 | 14 | 263 | 14 | 0.59 |
| Hr | pg/ml | 1.1E2 | 1.4E2 | 7.4E2 | 1.5E3 | 1.6E3 | 2.6E3 | 1.0E-9 | 1.0E-9 | 1.7E4 | 8.9E3 | 800 | 14 | 263 | 14 | 0.59 |
| Hu | pg/ml | 7.3E0 | 1.3E2 | 3.1E3 | 3.3E2 | 2.7E4 | 4.3E2 | 1.0E-9 | 1.0E-9 | 6.3E5 | 1.3E3 | 800 | 14 | 263 | 14 | 0.66 |
| Hv | pg/ml | 1.5E0 | 2.5E0 | 3.3E0 | 7.0E1 | 1.2E1 | 2.4E2 | 1.0E-9 | 1.0E-9 | 2.5E2 | 8.9E2 | 800 | 14 | 263 | 14 | 0.60 |
| Hw | pg/ml | 6.3E0 | 1.2E1 | 1.9E1 | 7.1E2 | 7.4E1 | 2.5E3 | 1.0E-9 | 5.1E-1 | 1.7E3 | 9.4E3 | 800 | 14 | 263 | 14 | 0.58 |
| Hx | pg/ml | 9.2E0 | 2.1E1 | 4.0E1 | 1.8E2 | 3.4E2 | 3.8E2 | 1.0E-9 | 1.0E-9 | 9.3E3 | 1.3E3 | 800 | 14 | 263 | 14 | 0.71 |
| Ib | ng/ml | 4.9E-2 | 7.6E-2 | 1.9E0 | 7.2E0 | 7.0E0 | 2.0E1 | 1.0E-9 | 1.0E-9 | 5.3E1 | 5.6E1 | 283 | 8 | 159 | 8 | 0.55 |
| Ic | U/ml | 2.2E2 | 2.2E2 | 1.2E3 | 2.5E2 | 7.1E3 | 1.4E2 | 1.5E0 | 5.2E1 | 9.3E4 | 4.2E2 | 283 | 8 | 159 | 8 | 0.59 |
| Id | U/ml | 7.1E-1 | 1.2E0 | 1.4E0 | 5.7E1 | 2.5E0 | 1.5E2 | 1.0E-9 | 5.5E-1 | 2.3E1 | 4.3E2 | 283 | 8 | 159 | 8 | 0.73 |
| To | pg/ml | 1.6E0 | 1.8E0 | 1.9E0 | 3.0E0 | 2.0E0 | 4.1E0 | 1.0E-9 | 1.0E-9 | 1.0E1 | 1.2E1 | 280 | 7 | 157 | 7 | 0.56 |
| Tn | pg/ml | 3.1E1 | 5.2E1 | 7.9E1 | 4.2E2 | 2.1E2 | 8.4E2 | 2.4E0 | 2.1E1 | 2.0E3 | 2.3E3 | 280 | 7 | 157 | 7 | 0.69 |
| Tv | ng/ml | 1.2E1 | 1.0E1 | 2.5E1 | 1.0E3 | 6.5E1 | 2.7E3 | 1.0E-9 | 1.0E-9 | 7.9E2 | 7.1E3 | 280 | 7 | 157 | 7 | 0.47 |
| Ih | ng/ml | 7.7E1 | 4.9E2 | 2.4E2 | 7.0E2 | 4.9E2 | 7.6E2 | 1.0E-9 | 1.0E-9 | 7.4E3 | 2.8E3 | 804 | 14 | 263 | 14 | 0.71 |
| Ii | ng/ml | 9.8E1 | 2.1E2 | 2.5E2 | 7.7E2 | 6.8E2 | 1.4E3 | 1.0E-9 | 2.3E0 | 1.0E4 | 4.5E3 | 804 | 14 | 263 | 14 | 0.61 |
| Ij | ng/ml | 8.1E1 | 1.4E2 | 1.8E2 | 1.9E3 | 5.5E2 | 6.5E3 | 1.6E-1 | 2.5E1 | 6.4E3 | 2.4E4 | 794 | 14 | 261 | 14 | 0.68 |
| Ik | ng/ml | 1.3E1 | 4.2E1 | 9.0E2 | 3.6E2 | 8.7E3 | 6.9E2 | 5.9E-1 | 5.5E0 | 1.2E5 | 2.5E3 | 800 | 14 | 261 | 14 | 0.65 |
| Il | ng/ml | 3.7E2 | 5.4E2 | 1.3E3 | 1.7E3 | 2.8E3 | 3.2E3 | 1.0E-9 | 1.0E-9 | 1.3E4 | 1.2E4 | 787 | 14 | 261 | 14 | 0.53 |
| Im | ng/ml | 2.3E2 | 7.0E2 | 4.1E2 | 1.3E3 | 6.1E2 | 1.6E3 | 1.3E1 | 4.7E1 | 6.8E3 | 6.2E3 | 800 | 14 | 262 | 14 | 0.78 |
| In | ng/ml | 3.3E0 | 5.5E0 | 2.2E1 | 3.4E2 | 1.5E2 | 1.2E3 | 1.0E-9 | 1.0E-9 | 3.9E3 | 4.5E3 | 804 | 14 | 263 | 14 | 0.57 |
| Hb | ng/ml | 2.5E1 | 2.3E1 | 3.6E1 | 3.1E1 | 3.5E1 | 2.4E1 | 4.8E-1 | 6.2E-1 | 2.1E2 | 8.0E1 | 292 | 8 | 161 | 8 | 0.49 |
| Hc | pg/ml | 6.7E2 | 3.6E2 | 3.7E3 | 2.3E3 | 1.3E4 | 4.7E3 | 1.0E-9 | 1.0E-9 | 1.0E5 | 1.4E4 | 292 | 8 | 161 | 8 | 0.37 |
| Hf | ng/ml | 1.6E2 | 2.1E2 | 3.7E2 | 2.5E2 | 5.2E2 | 2.7E2 | 1.0E-9 | 1.0E-9 | 3.2E3 | 6.7E2 | 292 | 8 | 161 | 8 | 0.45 |
| Io | ng/ml | 9.2E3 | 6.1E3 | 2.7E4 | 1.1E4 | 1.6E5 | 1.1E4 | 1.0E-9 | 1.3E3 | 4.0E6 | 3.3E4 | 796 | 14 | 263 | 14 | 0.44 |
| Ip | ng/ml | 1.2E1 | 3.0E1 | 2.0E1 | 3.1E1 | 2.4E1 | 2.2E1 | 1.0E-9 | 3.7E-2 | 2.6E2 | 5.7E1 | 796 | 14 | 263 | 14 | 0.63 |
| Iq | ug/ml | 1.1E-1 | 3.9E-1 | 1.8E1 | 1.8E1 | 4.8E2 | 5.8E1 | 1.0E-9 | 1.0E-9 | 1.4E4 | 2.2E2 | 796 | 14 | 263 | 14 | 0.65 |
| Ir | ug/ml | 3.7E-1 | 2.2E0 | 2.6E0 | 4.6E1 | 1.5E1 | 1.0E2 | 1.0E-9 | 1.0E-9 | 2.4E2 | 3.7E2 | 795 | 14 | 263 | 14 | 0.73 |
| Is | ng/ml | 1.6E0 | 1.3E1 | 6.0E0 | 4.7E1 | 1.3E1 | 7.4E1 | 1.0E-9 | 4.9E-1 | 1.5E2 | 2.6E2 | 796 | 14 | 263 | 14 | 0.80 |
| It | ng/ml | 2.0E0 | 6.0E0 | 2.0E1 | 6.8E1 | 1.3E2 | 1.8E2 | 1.0E-9 | 1.0E-9 | 2.8E3 | 6.8E2 | 796 | 14 | 263 | 14 | 0.66 |
| Iu | ng/ml | 2.3E2 | 4.8E2 | 1.3E3 | 2.6E3 | 3.8E3 | 6.4E3 | 1.0E-9 | 1.0E-9 | 2.9E4 | 2.4E4 | 796 | 14 | 263 | 14 | 0.56 |
| Iv | ng/ml | 1.4E1 | 9.8E1 | 4.5E1 | 6.3E2 | 1.6E2 | 1.3E3 | 1.0E-9 | 1.0E-9 | 3.8E3 | 3.8E3 | 795 | 14 | 263 | 14 | 0.76 |
| Iz | ng/ml | 1.6E2 | 1.7E2 | 6.3E2 | 2.6E2 | 3.7E3 | 3.3E2 | 9.2E-1 | 4.9E0 | 6.2E4 | 1.0E3 | 292 | 8 | 161 | 8 | 0.47 |
| Rc | pg/ml | 6.0E3 | 4.5E3 | 7.1E3 | 7.0E3 | 5.2E3 | 5.5E3 | 1.9E2 | 2.1E3 | 2.7E4 | 1.7E4 | 289 | 8 | 160 | 8 | 0.48 |
| Rb | pg/ml | 9.7E-1 | 6.4E-1 | 2.7E0 | 9.1E0 | 4.4E0 | 2.0E1 | 1.0E-9 | 1.0E-9 | 4.3E1 | 5.6E1 | 289 | 8 | 160 | 8 | 0.50 |
| Pz | ng/ml | 4.7E3 | 1.0E4 | 8.8E3 | 6.8E3 | 4.0E4 | 4.3E3 | 1.3E1 | 6.5E2 | 1.0E6 | 1.3E4 | 796 | 14 | 261 | 14 | 0.59 |
| Qa | ng/ml | 3.6E3 | 1.5E4 | 6.5E3 | 3.0E4 | 7.6E3 | 5.6E4 | 1.2E1 | 1.5E3 | 5.2E4 | 2.2E5 | 796 | 14 | 261 | 14 | 0.82 |
| Qb | ng/ml | 1.0E2 | 3.0E2 | 2.2E2 | 3.8E2 | 4.8E2 | 2.5E2 | 7.9E-1 | 5.1E1 | 8.3E3 | 8.8E2 | 796 | 14 | 261 | 14 | 0.77 |
| Qc | ng/ml | 2.6E2 | 4.4E2 | 6.8E2 | 6.1E2 | 5.9E3 | 7.5E2 | 1.0E-9 | 1.3E1 | 1.7E5 | 2.8E3 | 796 | 14 | 261 | 14 | 0.56 |
| Qd | ng/ml | 1.0E4 | 3.2E4 | 2.2E4 | 6.5E4 | 8.3E4 | 7.5E4 | 2.4E2 | 4.6E3 | 2.0E6 | 2.3E5 | 796 | 14 | 261 | 14 | 0.73 |
| Qe | ng/ml | 1.1E3 | 3.6E3 | 1.9E3 | 5.5E3 | 4.1E3 | 5.2E3 | 7.6E0 | 4.1E2 | 9.7E4 | 1.8E4 | 796 | 14 | 261 | 14 | 0.80 |
| Jd | ng/ml | 1.0E0 | 4.1E0 | 6.1E0 | 6.2E0 | 4.0E1 | 6.2E0 | 1.0E-9 | 1.4E0 | 6.5E2 | 2.1E1 | 290 | 8 | 162 | 8 | 0.81 |
| Je | ng/ml | 1.0E-9 | 4.3E0 | 2.2E0 | 4.3E0 | 7.5E0 | 4.1E0 | 1.0E-9 | 1.0E-9 | 8.8E1 | 1.1E1 | 290 | 8 | 162 | 8 | 0.71 |
| Jf | ng/ml | 1.0E-9 | 8.4E-1 | 1.2E0 | 1.5E0 | 2.4E0 | 1.7E0 | 1.0E-9 | 1.0E-9 | 1.2E1 | 3.7E0 | 290 | 8 | 162 | 8 | 0.59 |
| Jg | ng/ml | 5.4E2 | 1.8E3 | 8.6E2 | 2.0E3 | 1.0E3 | 1.9E3 | 1.0E-9 | 8.7E1 | 1.0E4 | 7.1E3 | 800 | 14 | 263 | 14 | 0.70 |
| Jh | ng/ml | 3.3E0 | 3.2E1 | 2.9E1 | 8.7E1 | 1.2E2 | 1.3E2 | 1.0E-9 | 1.0E-9 | 1.6E3 | 4.9E2 | 800 | 14 | 263 | 14 | 0.73 |
| Ji | ng/ml | 5.4E1 | 2.8E2 | 7.6E1 | 3.5E2 | 7.6E1 | 3.3E2 | 1.0E-9 | 2.0E1 | 5.4E2 | 1.3E3 | 800 | 14 | 263 | 14 | 0.85 |
| Sr | pg/mL | 4.0E2 | 3.3E3 | 9.0E2 | 4.9E3 | 1.3E3 | 6.8E3 | 1.0E-9 | 2.3E2 | 9.8E3 | 2.1E4 | 280 | 8 | 157 | 8 | 0.81 |
| Ss | pg/mL | 1.1E5 | 1.1E5 | 1.6E5 | 1.3E5 | 1.9E5 | 1.2E5 | 2.7E3 | 1.4E4 | 1.8E6 | 3.6E5 | 280 | 8 | 157 | 8 | 0.46 |
| St | pg/mL | 3.3E7 | 1.0E8 | 6.3E7 | 2.7E8 | 1.0E8 | 5.6E8 | 1.0E8 | 2.3E6 | 1.2E9 | 1.7E9 | 284 | 8 | 158 | 8 | 0.72 |
| Ra | pg/ml | 1.0E-9 | 1.0E-9 | 6.1E-1 | 8.8E0 | 1.2E0 | 2.2E1 | 1.0E-9 | 1.0E-9 | 7.3E0 | 6.4E1 | 289 | 8 | 160 | 8 | 0.51 |
| Qz | pg/ml | 1.0E1 | 1.3E1 | 6.2E1 | 4.2E1 | 1.1E2 | 5.3E1 | 1.0E-9 | 1.0E-9 | 7.1E2 | 1.4E2 | 289 | 8 | 160 | 8 | 0.57 |
| Qy | pg/ml | 4.8E-1 | 1.8E0 | 1.7E1 | 2.7E0 | 8.1E1 | 3.1E0 | 1.0E-9 | 1.1E-1 | 6.5E2 | 9.7E0 | 289 | 8 | 160 | 8 | 0.70 |
| Qx | pg/ml | 1.0E-9 | 1.0E-9 | 5.9E0 | 1.8E1 | 4.8E1 | 3.7E1 | 1.0E-9 | 1.0E-9 | 5.8E2 | 1.1E2 | 289 | 8 | 160 | 8 | 0.63 |
| Qw | pg/ml | 1.0E-9 | 8.1E-1 | 2.9E0 | 1.2E0 | 1.4E1 | 1.9E0 | 1.0E-9 | 1.0E-9 | 1.3E2 | 5.6E0 | 289 | 8 | 160 | 8 | 0.59 |
| Qv | pg/ml | 2.1E4 | 4.2E3 | 3.3E4 | 9.8E3 | 5.7E4 | 1.2E4 | 1.0E-9 | 4.0E2 | 7.4E5 | 3.3E4 | 289 | 8 | 160 | 8 | 0.22 |
| Qu | pg/ml | 1.2E1 | 1.0E-9 | 8.7E1 | 3.2E1 | 1.7E2 | 5.8E1 | 1.0E-9 | 1.0E-9 | 9.8E2 | 1.5E2 | 289 | 8 | 160 | 8 | 0.39 |
| Qt | pg/ml | 1.2E1 | 1.5E1 | 5.1E1 | 5.6E1 | 1.2E2 | 7.6E1 | 1.0E-9 | 1.0E-9 | 1.0E3 | 2.2E2 | 289 | 8 | 160 | 8 | 0.60 |
| Qh | ng/ml | 1.7E1 | 4.3E1 | 4.3E1 | 5.4E1 | 8.1E1 | 5.2E1 | 1.0E-9 | 5.1E0 | 8.0E2 | 1.6E2 | 289 | 8 | 160 | 8 | 0.64 |

Figure 8 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Qg | ng/ml | 7.7E0 | 4.0E0 | 1.8E1 | 8.2E0 | 6.5E1 | 1.2E1 | 5.1E-2 | 1.5E0 | 1.0E3 | 3.7E1 | 289 | 8 | 160 | 8 | 0.35 |
| Jj | ng/ml | 6.6E2 | 1.1E2 | 1.8E3 | 4.0E2 | 1.3E4 | 8.4E2 | 4.8E0 | 1.2E1 | 3.4E5 | 3.3E3 | 800 | 14 | 263 | 14 | 0.20 |
| Jk | ng/ml | 3.4E0 | 1.4E1 | 2.3E1 | 4.7E1 | 4.9E1 | 6.9E1 | 1.0E-9 | 2.4E-1 | 3.9E2 | 2.4E2 | 800 | 14 | 263 | 14 | 0.66 |
| Jl | ng/ml | 4.7E-1 | 6.7E0 | 2.1E0 | 7.2E2 | 6.0E0 | 2.7E3 | 7.6E-4 | 1.4E-1 | 1.1E2 | 9.9E3 | 800 | 14 | 263 | 14 | 0.79 |
| Jm | ng/ml | 1.9E1 | 4.7E1 | 6.0E1 | 5.5E1 | 1.3E2 | 5.1E1 | 1.0E-9 | 4.7E-1 | 2.1E3 | 1.5E2 | 800 | 14 | 263 | 14 | 0.57 |
| Jn | pg/ml | 4.0E-1 | 2.3E0 | 2.0E0 | 9.9E1 | 1.0E1 | 2.5E2 | 1.0E-9 | 1.6E-1 | 2.4E2 | 7.3E2 | 799 | 14 | 263 | 14 | 0.75 |
| Jo | pg/ml | 3.8E3 | 3.7E3 | 4.9E3 | 1.3E4 | 3.8E3 | 2.7E4 | 4.2E1 | 2.3E2 | 2.4E4 | 1.0E5 | 800 | 14 | 263 | 14 | 0.49 |
| Jp | pg/ml | 7.3E4 | 9.8E4 | 7.6E4 | 1.1E5 | 3.7E4 | 4.4E4 | 2.1E3 | 4.5E4 | 3.8E5 | 2.1E5 | 800 | 14 | 263 | 14 | 0.74 |
| Jq | pg/ml | 9.3E1 | 3.4E2 | 1.5E2 | 1.2E3 | 2.1E2 | 2.4E3 | 1.4E0 | 1.1E1 | 4.0E3 | 8.7E3 | 800 | 14 | 263 | 14 | 0.76 |
| Jr | pg/ml | 5.4E0 | 2.3E1 | 2.4E1 | 9.3E2 | 1.3E2 | 2.3E3 | 1.0E-9 | 2.6E0 | 2.4E3 | 7.4E3 | 800 | 14 | 263 | 14 | 0.79 |
| Js | pg/ml | 1.3E1 | 2.9E1 | 4.2E1 | 4.5E2 | 1.7E2 | 1.1E3 | 1.0E-9 | 3.0E0 | 3.0E3 | 3.0E3 | 800 | 14 | 263 | 14 | 0.67 |
| Jt | pg/ml | 2.8E3 | 4.7E3 | 3.3E3 | 8.9E3 | 2.2E3 | 1.4E4 | 7.7E1 | 4.1E2 | 1.8E4 | 5.2E4 | 800 | 14 | 263 | 14 | 0.62 |
| Ju | mIU/ml | 1.0E1 | 8.2E0 | 2.0E1 | 9.6E0 | 3.0E1 | 6.4E0 | 4.8E-2 | 1.9E-1 | 2.3E2 | 1.8E1 | 290 | 8 | 162 | 8 | 0.46 |
| Jv | mIU/ml | 1.4E1 | 4.6E0 | 3.6E1 | 6.8E0 | 6.0E1 | 6.6E0 | 1.0E-2 | 5.5E-1 | 4.4E2 | 1.9E1 | 290 | 8 | 162 | 8 | 0.32 |
| Jy | ng/ml | 1.6E-3 | 3.6E-3 | 2.3E-3 | 8.2E-3 | 4.2E-3 | 1.4E-2 | 8.7E-5 | 8.6E-4 | 5.2E-2 | 4.1E-2 | 290 | 8 | 162 | 8 | 0.73 |
| Kc | pg/ml | 2.6E1 | 2.4E1 | 4.5E1 | 5.9E1 | 4.8E1 | 6.3E1 | 1.0E-9 | 6.9E0 | 2.7E2 | 1.6E2 | 292 | 8 | 161 | 8 | 0.51 |
| Kd | pg/ml | 1.0E-9 | 1.0E-9 | 2.4E2 | 5.4E3 | 6.7E2 | 1.3E4 | 1.0E-9 | 1.0E-9 | 5.0E3 | 3.8E4 | 292 | 8 | 161 | 8 | 0.55 |
| Ke | pg/ml | 1.3E4 | 1.7E4 | 1.5E4 | 7.0E4 | 1.1E4 | 1.1E5 | 3.4E2 | 4.2E3 | 7.0E4 | 3.2E5 | 292 | 8 | 161 | 8 | 0.64 |
| Kf | pg/mL | 7.7E0 | 5.4E0 | 7.7E0 | 1.7E1 | 6.0E0 | 2.6E1 | 1.0E-9 | 1.7E0 | 4.4E1 | 7.8E1 | 292 | 8 | 161 | 8 | 0.53 |
| Kg | pg/mL | 1.2E3 | 6.9E2 | 1.9E3 | 4.0E3 | 2.2E3 | 9.4E3 | 7.3E1 | 1.3E2 | 1.7E4 | 2.7E4 | 292 | 8 | 161 | 8 | 0.35 |
| Ki | pg/ml | 5.9E1 | 9.4E1 | 6.9E1 | 1.0E2 | 5.5E1 | 4.7E1 | 1.0E-9 | 5.9E1 | 3.8E2 | 2.0E2 | 291 | 8 | 161 | 8 | 0.74 |
| Kj | pg/ml | 1.1E3 | 3.7E2 | 1.6E3 | 2.1E3 | 1.7E3 | 5.1E3 | 1.4E1 | 1.2E2 | 1.0E4 | 1.5E4 | 292 | 8 | 161 | 8 | 0.24 |
| Kk | pg/ml | 6.9E0 | 9.8E0 | 1.2E1 | 2.5E1 | 1.6E1 | 2.4E1 | 1.0E-9 | 5.0E0 | 1.6E2 | 5.9E1 | 292 | 8 | 161 | 8 | 0.71 |
| Kl | pg/ml | 2.3E4 | 1.6E4 | 3.0E4 | 2.5E4 | 2.6E4 | 2.7E4 | 1.6E2 | 1.6E3 | 1.6E5 | 7.8E4 | 292 | 8 | 161 | 8 | 0.42 |
| Kn | pg/ml | 3.0E1 | 6.7E1 | 6.6E1 | 7.0E2 | 1.0E2 | 1.7E3 | 1.0E-9 | 1.0E-9 | 7.3E2 | 4.9E3 | 292 | 8 | 161 | 8 | 0.64 |
| Ko | pg/ml | 4.3E2 | 2.2E2 | 5.4E2 | 8.3E2 | 5.3E2 | 1.4E3 | 1.0E-9 | 6.5E1 | 3.8E3 | 4.1E3 | 292 | 8 | 161 | 8 | 0.51 |
| Kp | pg/ml | 3.4E2 | 3.5E2 | 3.7E2 | 2.0E3 | 2.6E2 | 4.6E3 | 1.0E-9 | 3.7E1 | 1.7E3 | 1.3E4 | 292 | 8 | 161 | 8 | 0.52 |
| Kq | pg/ml | 3.6E2 | 8.2E2 | 5.1E2 | 2.2E4 | 8.2E2 | 5.5E4 | 1.6E0 | 1.7E2 | 9.8E3 | 1.6E5 | 283 | 8 | 155 | 8 | 0.75 |
| Kr | pg/ml | 5.6E-1 | 1.0E-9 | 2.6E0 | 5.2E1 | 4.8E0 | 1.5E2 | 1.0E-9 | 1.0E-9 | 3.9E1 | 4.2E2 | 283 | 8 | 155 | 8 | 0.36 |
| Ks | pg/ml | 1.4E4 | 1.7E4 | 2.0E4 | 1.7E4 | 1.9E4 | 1.4E4 | 5.1E1 | 1.3E3 | 1.1E5 | 3.7E4 | 283 | 8 | 155 | 8 | 0.48 |
| Kx | ng/ml | 1.0E-9 | 1.3E-2 | 7.1E-3 | 2.1E-2 | 1.4E-2 | 2.4E-2 | 1.0E-9 | 1.3E-3 | 1.0E-1 | 6.4E-2 | 289 | 8 | 160 | 8 | 0.77 |
| Ky | ng/ml | 1.1E-1 | 5.6E-1 | 4.4E-1 | 7.9E-1 | 9.0E-1 | 9.0E-1 | 1.0E-9 | 3.0E-2 | 6.3E0 | 2.7E0 | 289 | 8 | 160 | 8 | 0.71 |
| Kz | ng/ml | 1.0E-9 | 1.4E-2 | 3.2E-3 | 9.4E-3 | 5.4E-3 | 7.9E-3 | 1.0E-9 | 1.0E-9 | 3.6E-2 | 1.8E-2 | 289 | 8 | 160 | 8 | 0.70 |
| Ld | pg/ml | 1.0E-9 | 1.7E0 | 3.7E0 | 6.8E0 | 8.9E0 | 9.0E0 | 1.0E-9 | 1.0E-9 | 8.4E1 | 2.3E1 | 291 | 8 | 160 | 8 | 0.66 |
| Lh | pg/ml | 1.4E4 | 3.4E4 | 2.2E4 | 8.6E4 | 2.7E4 | 1.3E5 | 1.0E-9 | 1.8E3 | 2.6E5 | 4.1E5 | 799 | 14 | 264 | 14 | 0.71 |
| Li | pg/ml | 3.6E3 | 3.1E4 | 1.6E4 | 6.8E4 | 4.8E4 | 9.0E4 | 1.0E-9 | 5.5E2 | 9.2E5 | 3.1E5 | 799 | 14 | 264 | 14 | 0.75 |
| Lj | pg/ml | 3.0E3 | 1.7E4 | 2.3E4 | 5.4E4 | 6.4E4 | 1.0E5 | 1.0E-9 | 1.5E3 | 5.2E5 | 3.9E5 | 799 | 14 | 264 | 14 | 0.73 |
| Rm | ng/ml | 1.9E1 | 8.6E1 | 5.5E1 | 9.5E1 | 8.5E1 | 8.8E1 | 2.2E-1 | 3.9E-1 | 6.5E2 | 2.5E2 | 284 | 8 | 159 | 8 | 0.68 |
| Rh | ng/ml | 1.3E2 | 1.5E2 | 3.0E2 | 2.3E3 | 8.1E2 | 6.0E3 | 4.7E0 | 5.4E1 | 1.2E4 | 1.7E4 | 284 | 8 | 159 | 8 | 0.57 |
| Ri | ng/ml | 1.0E-9 | 1.0E-9 | 3.9E0 | 5.1E-2 | 1.5E1 | 1.4E-1 | 1.0E-9 | 1.0E-9 | 2.2E2 | 4.1E-1 | 285 | 8 | 160 | 8 | 0.32 |
| Rg | ng/ml | 1.0E-9 | 1.0E-9 | 5.5E-2 | 7.4E-2 | 3.4E-1 | 2.1E-1 | 1.0E-9 | 1.0E-9 | 3.3E0 | 5.9E-1 | 284 | 8 | 159 | 8 | 0.46 |
| Rj | ng/ml | 1.0E-9 | 1.0E-9 | 1.3E0 | 3.4E1 | 5.5E0 | 9.5E1 | 1.0E-9 | 1.0E-9 | 8.0E1 | 2.7E2 | 285 | 8 | 160 | 8 | 0.50 |
| Rf | ng/ml | 3.9E-1 | 1.5E0 | 1.0E0 | 4.7E0 | 1.8E0 | 6.6E0 | 7.8E-3 | 5.0E-1 | 1.5E1 | 1.7E1 | 284 | 8 | 159 | 8 | 0.80 |
| Ql | pg/ml | 5.5E0 | 1.4E1 | 1.5E1 | 2.8E1 | 3.1E1 | 3.1E1 | 1.0E-9 | 4.3E-1 | 2.9E2 | 9.3E1 | 290 | 8 | 162 | 8 | 0.71 |
| Qm | pg/ml | 4.4E0 | 1.6E1 | 2.0E1 | 2.6E1 | 3.8E1 | 2.5E1 | 1.0E-9 | 1.0E-9 | 3.6E2 | 6.9E1 | 290 | 8 | 162 | 8 | 0.63 |
| Qn | pg/ml | 6.1E-1 | 8.6E-1 | 7.3E0 | 4.1E0 | 2.4E1 | 5.2E0 | 1.0E-9 | 1.0E-9 | 2.4E2 | 1.2E1 | 290 | 8 | 162 | 8 | 0.60 |
| Nv | pg/ml | 4.1E3 | 1.3E4 | 1.2E4 | 2.9E4 | 4.6E4 | 3.2E4 | 1.0E-9 | 1.3E3 | 1.1E6 | 9.4E4 | 805 | 14 | 264 | 14 | 0.69 |
| Nw | pg/ml | 9.4E3 | 2.7E4 | 1.3E4 | 5.7E4 | 1.6E4 | 7.0E4 | 8.6E1 | 6.2E3 | 2.1E5 | 2.2E5 | 805 | 14 | 264 | 14 | 0.81 |
| Nx | pg/ml | 2.2E2 | 7.5E2 | 4.2E2 | 9.7E2 | 6.6E2 | 1.1E3 | 1.0E-9 | 1.0E-9 | 7.4E3 | 4.1E3 | 805 | 14 | 264 | 14 | 0.68 |
| Ny | pg/ml | 7.1E0 | 3.5E1 | 5.9E1 | 3.2E2 | 8.9E2 | 7.3E2 | 1.0E-9 | 1.0E0 | 2.5E4 | 2.8E3 | 805 | 14 | 264 | 14 | 0.79 |
| Oa | pg/ml | 1.9E2 | 4.8E2 | 4.7E2 | 9.9E2 | 7.6E2 | 9.9E2 | 1.0E-9 | 6.5E1 | 4.8E3 | 2.4E3 | 290 | 8 | 162 | 8 | 0.70 |
| Oe | pg/ml | 8.8E1 | 4.7E0 | 3.0E2 | 1.9E2 | 7.9E2 | 3.5E2 | 1.0E-9 | 1.0E-9 | 1.9E4 | 1.1E3 | 797 | 14 | 263 | 14 | 0.42 |
| Of | pg/ml | 2.1E2 | 5.8E1 | 6.5E3 | 6.6E3 | 2.9E4 | 1.8E4 | 1.0E-9 | 3.5E0 | 6.2E5 | 6.6E4 | 805 | 14 | 264 | 14 | 0.40 |
| Og | pg/ml | 8.5E-2 | 4.5E-2 | 7.9E-1 | 7.0E-2 | 5.0E0 | 9.0E-2 | 1.0E-9 | 1.0E-9 | 8.3E1 | 3.2E-1 | 805 | 14 | 264 | 14 | 0.37 |
| Oh | pg/ml | 2.7E0 | 2.4E1 | 2.0E1 | 1.2E2 | 1.5E2 | 3.0E2 | 1.0E-9 | 1.1E0 | 3.5E3 | 1.1E3 | 805 | 14 | 264 | 14 | 0.78 |
| Oi | pg/ml | 2.9E0 | 1.0E-9 | 6.6E0 | 4.8E0 | 9.9E0 | 8.6E0 | 1.0E-9 | 1.0E-9 | 8.6E1 | 3.1E1 | 805 | 14 | 264 | 14 | 0.39 |
| Ok | pg/ml | 4.2E2 | 1.1E3 | 5.6E2 | 2.0E3 | 5.2E2 | 2.1E3 | 1.3E1 | 1.8E2 | 5.2E3 | 7.8E3 | 805 | 14 | 264 | 14 | 0.78 |

Figure 8 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Om | pg/ml | 3.9E2 | 1.6E3 | 8.5E2 | 5.8E3 | 2.2E3 | 1.3E4 | 1.0E-9 | 2.5E2 | 3.6E4 | 5.1E4 | 805 | 14 | 264 | 14 | 0.77 |
| On | pg/ml | 1.9E2 | 9.3E2 | 3.0E2 | 1.6E3 | 4.0E2 | 2.2E3 | 1.0E-9 | 2.6E1 | 4.5E3 | 8.5E3 | 805 | 14 | 264 | 14 | 0.78 |
| Or | pg/ml | 1.6E1 | 8.0E1 | 3.9E1 | 1.2E2 | 7.2E1 | 1.7E2 | 1.0E-9 | 1.0E-9 | 5.0E2 | 5.1E2 | 293 | 8 | 161 | 8 | 0.70 |
| Ow | pg/ml | 3.6E1 | 1.5E2 | 1.2E2 | 6.0E2 | 3.0E2 | 1.0E3 | 1.0E-9 | 1.8E1 | 2.7E3 | 3.0E3 | 293 | 8 | 161 | 8 | 0.72 |
| Ou | pg/ml | 5.4E2 | 6.0E2 | 1.1E3 | 2.3E3 | 1.8E3 | 3.2E3 | 1.0E-9 | 3.4E2 | 1.1E4 | 8.2E3 | 293 | 8 | 161 | 8 | 0.62 |
| Ul | ng/ml | 1.0E-9 | 1.0E-9 | 1.7E0 | 1.1E1 | 7.8E0 | 2.1E1 | 1.0E-9 | 1.0E-9 | 1.0E2 | 5.6E1 | 297 | 8 | 164 | 8 | 0.58 |
| Uo | ng/ml | 1.0E-9 | 1.0E-9 | 1.0E-1 | 1.2E-1 | 2.6E-1 | 2.2E-1 | 1.0E-9 | 1.0E-9 | 2.6E0 | 6.3E-1 | 297 | 8 | 164 | 8 | 0.54 |
| Uk | ng/ml | 1.0E-9 | 1.0E-9 | 8.0E-3 | 1.8E-3 | 2.6E-2 | 3.8E-3 | 1.0E-9 | 1.0E-9 | 3.2E-1 | 1.1E-2 | 297 | 8 | 164 | 8 | 0.41 |
| Um | ng/ml | 1.0E-9 | 1.0E-9 | 4.1E-1 | 3.8E-1 | 9.9E-1 | 7.8E-1 | 1.0E-9 | 1.0E-9 | 7.2E0 | 2.3E0 | 297 | 8 | 164 | 8 | 0.51 |
| Uf | ng/ml | 6.8E-2 | 1.2E-1 | 1.5E-1 | 8.3E-1 | 2.8E-1 | 1.9E0 | 1.0E-3 | 3.6E-2 | 2.5E0 | 5.6E0 | 297 | 8 | 164 | 8 | 0.67 |
| Uh | ng/ml | 2.2E0 | 4.1E0 | 3.3E0 | 6.4E0 | 3.4E0 | 6.3E0 | 1.3E-2 | 7.1E-1 | 1.8E1 | 1.7E1 | 297 | 8 | 164 | 8 | 0.65 |
| Un | ng/ml | 2.0E0 | 3.8E0 | 2.2E0 | 6.6E0 | 1.3E0 | 7.8E0 | 1.3E-1 | 1.8E0 | 8.0E0 | 2.5E1 | 297 | 8 | 164 | 8 | 0.81 |
| Ug | ng/ml | 1.5E1 | 1.1E1 | 2.9E1 | 2.0E1 | 3.2E1 | 2.8E1 | 6.9E-1 | 1.7E0 | 2.1E2 | 8.5E1 | 297 | 8 | 164 | 8 | 0.40 |
| Ur | ng/ml | 1.5E-1 | 1.0E-9 | 8.3E-1 | 9.4E-1 | 5.5E0 | 2.6E0 | 1.0E-9 | 1.0E-9 | 9.3E1 | 7.3E0 | 296 | 8 | 163 | 8 | 0.30 |
| Up | ng/ml | 1.0E-9 | 1.0E-9 | 5.2E-3 | 3.0E-1 | 2.3E-2 | 8.4E-1 | 1.0E-9 | 1.0E-9 | 3.3E-1 | 2.4E0 | 296 | 8 | 163 | 8 | 0.55 |
| Us | ng/ml | 4.3E-3 | 1.0E-9 | 2.0E-2 | 2.1E-1 | 4.6E-2 | 5.9E-1 | 1.0E-9 | 1.0E-9 | 4.0E-1 | 1.7E0 | 296 | 8 | 163 | 8 | 0.35 |
| Uv | ng/ml | 2.9E-3 | 2.3E-3 | 1.1E-2 | 8.0E-2 | 3.5E-2 | 1.5E-1 | 1.0E-9 | 1.0E-9 | 4.3E-1 | 4.1E-1 | 296 | 8 | 163 | 8 | 0.50 |
| Ut | ng/ml | 7.2E-1 | 2.3E0 | 2.9E0 | 1.4E1 | 8.6E0 | 2.3E1 | 1.0E-9 | 1.0E-9 | 7.8E1 | 6.5E1 | 296 | 8 | 163 | 8 | 0.70 |
| Uu | ng/ml | 7.5E0 | 3.4E0 | 8.4E0 | 4.7E0 | 5.7E0 | 3.1E0 | 5.5E-1 | 1.2E0 | 4.0E1 | 8.8E0 | 296 | 8 | 163 | 8 | 0.29 |
| Vp | ng/ml | 1.0E-9 | 1.0E-9 | 3.8E-1 | 6.2E0 | 3.4E0 | 1.7E1 | 1.0E-9 | 1.0E-9 | 5.0E1 | 4.9E1 | 297 | 8 | 164 | 8 | 0.61 |
| Vt | ng/ml | 6.8E0 | 1.2E1 | 9.3E0 | 3.5E1 | 9.4E0 | 5.1E1 | 4.3E-1 | 4.5E0 | 8.6E1 | 1.6E2 | 297 | 8 | 164 | 8 | 0.73 |
| Vo | ng/ml | 2.5E1 | 2.5E1 | 2.5E1 | 2.3E1 | 5.1E0 | 5.9E0 | 2.5E0 | 1.1E1 | 4.8E1 | 3.0E1 | 297 | 8 | 164 | 8 | 0.41 |
| Vv | ng/ml | 3.3E0 | 2.0E0 | 6.2E0 | 3.4E0 | 9.7E0 | 5.1E0 | 1.0E-9 | 1.0E-9 | 8.4E1 | 1.4E1 | 296 | 7 | 164 | 7 | 0.38 |
| Oy | pg/ml | 5.1E-1 | 3.7E0 | 6.0E0 | 3.8E0 | 3.0E1 | 9.1E0 | 1.0E-9 | 1.0E-9 | 4.0E2 | 3.3E1 | 804 | 14 | 263 | 14 | 0.45 |
| Oz | pg/ml | 1.2E-2 | 1.0E-9 | 3.2E-1 | 2.1E0 | 1.4E0 | 7.5E0 | 1.0E-9 | 1.0E-9 | 2.9E1 | 2.8E1 | 804 | 14 | 263 | 14 | 0.42 |
| Pa | pg/ml | 4.0E-1 | 5.8E-1 | 1.5E0 | 1.9E0 | 5.2E0 | 6.0E0 | 1.0E-9 | 1.0E-9 | 8.6E1 | 2.3E2 | 804 | 14 | 263 | 14 | 0.59 |
| Pb | pg/ml | 1.0E-9 | 1.0E-9 | 8.5E-1 | 2.4E0 | 1.7E1 | 8.4E0 | 1.0E-9 | 1.0E-9 | 4.9E2 | 3.2E1 | 804 | 14 | 263 | 14 | 0.44 |
| Pc | pg/ml | 6.4E-2 | 1.0E-9 | 3.6E-1 | 3.3E0 | 8.9E-1 | 9.9E0 | 1.0E-9 | 1.0E-9 | 1.6E1 | 3.8E1 | 804 | 14 | 263 | 14 | 0.50 |
| Pd | pg/ml | 2.0E0 | 5.3E0 | 5.0E0 | 1.8E1 | 3.0E1 | 3.2E1 | 1.0E-9 | 7.3E-2 | 8.4E2 | 1.2E2 | 804 | 14 | 263 | 14 | 0.72 |
| Pe | pg/ml | 2.3E1 | 1.3E2 | 1.1E2 | 1.8E3 | 3.6E2 | 4.2E3 | 1.0E-9 | 2.0E1 | 4.7E3 | 1.5E4 | 804 | 14 | 263 | 14 | 0.78 |
| Pf | pg/ml | 1.8E0 | 1.6E1 | 1.0E1 | 6.1E1 | 5.8E1 | 1.1E2 | 1.0E-9 | 3.3E-1 | 1.5E3 | 4.3E2 | 804 | 14 | 263 | 14 | 0.78 |
| Pg | pg/ml | 3.8E0 | 1.6E1 | 4.6E1 | 1.8E2 | 3.6E2 | 3.7E2 | 1.0E-9 | 4.6E-1 | 7.7E3 | 1.2E3 | 804 | 14 | 263 | 14 | 0.68 |
| Ph | ng/ml | 1.8E-1 | 2.4E-1 | 3.6E-1 | 9.1E-1 | 5.7E-1 | 1.8E0 | 1.0E-9 | 3.5E-3 | 4.4E0 | 5.4E0 | 293 | 8 | 161 | 8 | 0.57 |
| Pi | ng/ml | 2.0E-1 | 4.3E-1 | 3.0E-1 | 1.1E1 | 4.4E-1 | 2.9E1 | 1.0E-9 | 1.0E-9 | 4.8E0 | 8.2E1 | 293 | 8 | 161 | 8 | 0.71 |
| Pj | ng/mL | 5.7E0 | 7.3E0 | 6.3E0 | 7.9E0 | 4.6E0 | 4.6E0 | 3.8E-2 | 1.5E0 | 3.1E1 | 1.7E1 | 293 | 8 | 161 | 8 | 0.62 |
| Pk | ng/mL | 8.8E-3 | 2.7E-2 | 1.3E-2 | 2.1E-1 | 2.0E-2 | 5.3E-1 | 1.0E-9 | 5.4E-1 | 2.5E-1 | 1.5E0 | 293 | 8 | 161 | 8 | 0.79 |
| aA | mg/dL | 8.1E-1 | 1.6E0 | 9.4E-1 | 2.1E0 | 4.7E-1 | 1.3E0 | 2.0E-1 | 5.5E-1 | 4.2E0 | 4.7E0 | 2235 | 17 | 391 | 17 | 0.80 |
| aC | mg/mL | 2.7E0 | 2.0E0 | 3.0E0 | 2.4E0 | 1.3E0 | 1.4E0 | 7.7E-1 | 7.4E-1 | 8.2E0 | 5.5E0 | 465 | 9 | 174 | 9 | 0.37 |
| aD | ug/mL | 3.1E0 | 6.0E0 | 4.4E0 | 8.7E0 | 3.4E0 | 6.8E0 | 7.5E-1 | 2.1E0 | 3.1E1 | 2.1E1 | 465 | 9 | 174 | 9 | 0.71 |
| aE | mg/mL | 5.5E-1 | 5.0E-1 | 5.7E-1 | 6.3E-1 | 1.5E-1 | 2.8E-1 | 1.8E-1 | 3.9E-1 | 1.1E0 | 1.2E0 | 465 | 9 | 174 | 9 | 0.49 |
| aF | ng/mL | 2.3E0 | 1.4E0 | 4.1E0 | 4.7E0 | 5.8E0 | 5.6E0 | 4.3E-3 | 5.2E-1 | 5.0E1 | 1.5E1 | 465 | 9 | 174 | 9 | 0.45 |
| aG | mg/mL | 1.3E-1 | 1.3E-1 | 1.5E-1 | 1.7E-1 | 8.1E-2 | 1.2E-1 | 4.3E-2 | 7.3E-2 | 5.0E-1 | 4.2E-1 | 465 | 9 | 174 | 9 | 0.49 |
| aH | ug/mL | 7.5E1 | 6.8E1 | 8.0E1 | 7.7E1 | 4.2E1 | 4.7E1 | 9.6E0 | 1.1E1 | 2.9E2 | 1.5E2 | 465 | 9 | 174 | 9 | 0.48 |
| aI | ug/mL | 1.8E2 | 1.6E2 | 1.8E2 | 1.6E2 | 6.0E1 | 5.2E1 | 4.7E1 | 7.6E1 | 3.7E2 | 2.4E2 | 465 | 9 | 174 | 9 | 0.41 |
| aJ | ng/mL | 2.5E0 | 5.6E0 | 3.2E0 | 6.5E0 | 2.2E0 | 3.6E0 | 7.3E-1 | 1.5E0 | 1.7E1 | 1.2E1 | 465 | 9 | 174 | 9 | 0.79 |
| aK | ng/mL | 1.5E0 | 1.7E0 | 2.3E0 | 3.0E0 | 2.6E0 | 2.3E0 | 2.9E-4 | 1.3E-1 | 1.8E1 | 6.5E0 | 465 | 9 | 174 | 9 | 0.61 |
| aL | mg/mL | 7.9E-1 | 8.0E-1 | 8.0E-1 | 7.9E-1 | 2.5E-1 | 2.4E-1 | 2.2E-1 | 2.7E-1 | 1.7E0 | 1.0E0 | 465 | 9 | 174 | 9 | 0.52 |
| aM | U/mL | 2.2E1 | 6.3E1 | 4.5E1 | 1.8E2 | 9.2E1 | 2.6E2 | 4.2E-2 | 1.9E1 | 1.6E3 | 8.2E2 | 465 | 9 | 174 | 9 | 0.77 |
| aN | U/mL | 1.5E1 | 2.9E1 | 2.3E1 | 3.7E1 | 3.2E1 | 3.4E1 | 2.5E-3 | 1.9E0 | 3.8E2 | 1.1E2 | 465 | 9 | 174 | 9 | 0.65 |
| aO | pg/mL | 3.5E1 | 1.5E2 | 3.3E2 | 6.2E2 | 8.2E2 | 9.4E2 | 6.0E-1 | 2.1E0 | 6.6E3 | 2.4E3 | 465 | 9 | 174 | 9 | 0.63 |
| aP | ng/mL | 1.7E0 | 4.1E0 | 2.0E0 | 3.7E0 | 1.3E0 | 1.7E0 | 5.4E-1 | 1.4E0 | 1.1E1 | 5.8E0 | 465 | 9 | 174 | 9 | 0.80 |
| aQ | ng/mL | 2.9E-1 | 4.8E-1 | 4.4E-1 | 4.4E-1 | 4.6E-1 | 2.5E-1 | 2.0E-4 | 5.1E-2 | 4.0E0 | 9.0E-1 | 465 | 9 | 174 | 9 | 0.58 |
| aR | ng/mL | 1.8E0 | 3.1E0 | 2.8E0 | 3.4E0 | 3.4E0 | 1.7E0 | 1.8E-1 | 9.8E-1 | 3.4E1 | 5.9E0 | 465 | 9 | 174 | 9 | 0.69 |
| aS | ng/mL | 2.8E-1 | 4.0E-1 | 6.9E-1 | 9.0E-1 | 1.8E0 | 1.1E0 | 4.2E-3 | 8.5E-2 | 3.3E1 | 2.8E0 | 465 | 9 | 174 | 9 | 0.52 |
| aU | pg/mL | 7.4E1 | 9.3E1 | 1.2E2 | 1.5E2 | 1.5E2 | 1.6E2 | 7.4E-2 | 9.6E0 | 1.3E3 | 5.1E2 | 465 | 9 | 174 | 9 | 0.58 |
| aV | ng/mL | 6.0E-1 | 1.3E0 | 1.0E0 | 1.5E0 | 1.9E0 | 1.6E0 | 7.6E-4 | 1.0E-1 | 3.3E1 | 5.4E0 | 465 | 9 | 174 | 9 | 0.62 |
| aW | pg/mL | 1.9E1 | 2.6E1 | 2.0E1 | 6.8E1 | 1.9E1 | 1.3E2 | 7.2E-2 | 7.7E0 | 2.4E2 | 4.2E2 | 465 | 9 | 174 | 9 | 0.67 |

Figure 8 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aX | ng/mL | 9.6E0 | 1.2E1 | 1.4E1 | 1.0E1 | 1.5E1 | 8.0E0 | 3.0E-1 | 2.6E0 | 1.4E2 | 2.6E1 | 465 | 9 | 174 | 9 | 0.43 |
| aY | pg/mL | 6.0E1 | 6.6E1 | 7.7E1 | 9.7E1 | 8.4E1 | 6.6E1 | 4.1E-1 | 1.2E1 | 1.2E3 | 2.0E2 | 465 | 9 | 174 | 9 | 0.62 |
| aZ | pg/mL | 2.3E2 | 4.2E2 | 5.3E2 | 4.2E2 | 1.0E3 | 3.4E2 | 1.7E0 | 8.2E1 | 1.2E4 | 1.3E3 | 465 | 9 | 174 | 9 | 0.60 |
| bA | ng/mL | 9.5E0 | 1.2E2 | 3.4E1 | 2.0E2 | 8.4E1 | 2.9E2 | 3.0E-2 | 2.0E0 | 9.4E2 | 9.4E2 | 465 | 9 | 174 | 9 | 0.83 |
| bB | ng/mL | 2.9E2 | 2.9E2 | 3.1E2 | 2.3E2 | 1.7E2 | 1.4E2 | 8.6E0 | 3.3E1 | 1.0E3 | 4.2E2 | 465 | 9 | 174 | 9 | 0.38 |
| bC | ng/mL | 3.5E2 | 3.3E2 | 5.9E2 | 1.1E3 | 7.6E2 | 1.5E3 | 2.7E1 | 1.4E2 | 4.7E3 | 4.7E3 | 465 | 9 | 174 | 9 | 0.58 |
| bE | mg/mL | 5.4E0 | 5.7E0 | 5.7E0 | 5.9E0 | 2.0E0 | 2.7E0 | 1.4E0 | 1.3E0 | 1.3E1 | 1.1E1 | 465 | 9 | 174 | 9 | 0.54 |
| bF | pg/mL | 2.2E1 | 5.7E1 | 1.9E2 | 2.7E2 | 1.0E3 | 6.0E2 | 5.0E-2 | 1.5E1 | 1.1E4 | 1.9E3 | 465 | 9 | 174 | 9 | 0.72 |
| bG | ng/mL | 1.7E0 | 2.6E0 | 2.9E0 | 3.6E0 | 3.6E0 | 4.5E0 | 2.2E-2 | 5.8E-1 | 3.0E1 | 1.5E1 | 465 | 9 | 174 | 9 | 0.56 |
| bH | pg/mL | 5.7E-1 | 9.2E0 | 4.9E0 | 7.0E0 | 1.5E1 | 6.9E0 | 5.7E-1 | 5.7E-1 | 2.8E2 | 2.0E1 | 465 | 9 | 174 | 9 | 0.64 |
| bI | ng/mL | 4.0E-3 | 4.0E-3 | 6.5E-2 | 1.8E-1 | 1.6E-1 | 3.1E-1 | 4.0E-3 | 4.0E-3 | 1.3E0 | 8.8E-1 | 465 | 9 | 174 | 9 | 0.59 |
| bJ | mg/mL | 2.1E0 | 2.9E0 | 2.4E0 | 3.5E0 | 1.9E0 | 2.1E0 | 2.5E-4 | 2.5E-4 | 1.3E1 | 7.0E0 | 465 | 9 | 174 | 9 | 0.66 |
| bL | pg/mL | 3.8E0 | 3.2E0 | 8.4E0 | 8.6E0 | 1.0E1 | 1.0E1 | 4.6E-2 | 1.1E0 | 4.9E1 | 3.2E1 | 465 | 9 | 174 | 9 | 0.55 |
| bM | mg/mL | 1.8E0 | 2.3E0 | 2.1E0 | 3.3E0 | 1.4E0 | 2.7E0 | 9.2E-3 | 1.8E-2 | 8.9E0 | 8.4E0 | 465 | 9 | 174 | 9 | 0.63 |
| bN | ng/mL | 4.6E1 | 3.1E1 | 1.3E2 | 9.4E1 | 2.5E2 | 1.6E2 | 1.4E-1 | 1.4E0 | 1.9E3 | 4.8E2 | 465 | 9 | 174 | 9 | 0.41 |
| bO | ng/mL | 4.0E-2 | 4.0E-2 | 9.5E0 | 1.7E1 | 2.3E1 | 2.7E1 | 4.0E-2 | 4.0E-2 | 2.0E2 | 6.1E1 | 465 | 9 | 174 | 9 | 0.53 |
| bP | mg/mL | 5.2E-1 | 8.2E-1 | 7.3E-1 | 1.0E0 | 6.7E-1 | 9.9E-1 | 8.2E-2 | 2.9E-1 | 4.8E0 | 3.5E0 | 465 | 9 | 174 | 9 | 0.62 |
| bQ | pg/mL | 1.6E1 | 3.5E1 | 6.1E1 | 7.8E1 | 6.3E2 | 7.0E1 | 1.5E-1 | 1.2E1 | 1.3E4 | 2.2E2 | 465 | 9 | 174 | 9 | 0.81 |
| bR | ng/mL | 1.2E-2 | 1.2E-2 | 1.3E-1 | 2.2E-2 | 4.5E-1 | 3.0E-2 | 1.2E-2 | 1.2E-2 | 8.7E0 | 1.0E-1 | 465 | 9 | 174 | 9 | 0.34 |
| bS | pg/mL | 9.4E-1 | 9.4E-1 | 7.2E0 | 3.5E0 | 2.8E1 | 7.8E0 | 9.4E-1 | 9.4E-1 | 3.9E2 | 2.4E1 | 465 | 9 | 174 | 9 | 0.48 |
| bU | ng/mL | 1.1E-1 | 1.3E-2 | 1.9E-1 | 1.1E-1 | 3.7E-1 | 1.4E-1 | 1.3E-2 | 1.3E-2 | 6.6E0 | 4.1E-1 | 465 | 9 | 174 | 9 | 0.41 |
| bV | pg/mL | 4.6E2 | 1.0E3 | 5.7E2 | 9.5E2 | 8.0E2 | 5.1E2 | 1.5E2 | 3.6E2 | 1.7E4 | 2.0E3 | 465 | 9 | 174 | 9 | 0.78 |
| bW | pg/mL | 3.4E2 | 3.7E2 | 5.0E2 | 3.1E3 | 5.6E2 | 8.2E3 | 8.4E1 | 1.5E2 | 6.4E3 | 2.5E4 | 465 | 9 | 174 | 9 | 0.56 |
| bX | ng/mL | 2.5E-5 | 3.9E-3 | 2.7E-3 | 3.2E-3 | 3.4E-3 | 2.6E-3 | 2.5E-5 | 2.5E-5 | 2.0E-2 | 7.1E-3 | 465 | 9 | 174 | 9 | 0.56 |
| bZ | pg/mL | 2.4E2 | 5.1E2 | 9.4E2 | 1.3E3 | 4.3E3 | 1.7E3 | 1.5E-1 | 1.9E2 | 5.8E4 | 5.1E3 | 465 | 9 | 174 | 9 | 0.72 |
| cA | pg/mL | 6.0E-1 | 6.0E-1 | 2.8E0 | 6.0E-1 | 1.8E1 | 0.0E0 | 6.0E-1 | 6.0E-1 | 3.7E2 | 6.0E-1 | 465 | 9 | 174 | 9 | 0.44 |
| cB | ng/mL | 5.1E-2 | 4.7E-2 | 8.2E-2 | 5.5E-2 | 1.0E-1 | 5.0E-2 | 1.7E-3 | 1.7E-3 | 5.7E-1 | 1.6E-1 | 465 | 9 | 174 | 9 | 0.46 |
| cC | pg/mL | 4.6E1 | 5.4E1 | 4.8E1 | 4.1E1 | 4.0E1 | 3.1E1 | 1.0E0 | 1.0E0 | 4.5E2 | 7.3E1 | 465 | 9 | 174 | 9 | 0.49 |
| cD | pg/mL | 5.2E0 | 8.7E0 | 1.3E1 | 1.0E1 | 3.6E1 | 1.5E1 | 3.3E-1 | 3.3E-1 | 4.8E2 | 4.9E1 | 465 | 9 | 174 | 9 | 0.52 |
| cE | pg/mL | 3.9E1 | 1.6E2 | 1.5E2 | 2.9E2 | 4.5E2 | 4.0E2 | 1.2E-1 | 1.2E1 | 3.8E3 | 1.3E3 | 465 | 9 | 174 | 9 | 0.69 |
| cF | pg/mL | 1.2E1 | 5.3E-1 | 2.0E1 | 8.3E0 | 3.1E1 | 1.3E1 | 5.3E-1 | 5.3E-1 | 2.7E2 | 3.6E1 | 465 | 9 | 174 | 9 | 0.38 |
| cG | pg/mL | 4.7E1 | 8.4E1 | 1.1E2 | 1.5E2 | 5.1E2 | 1.5E2 | 6.4E0 | 3.5E1 | 1.0E4 | 4.1E2 | 465 | 9 | 174 | 9 | 0.67 |
| cH | uIU/mL | 2.8E0 | 1.4E0 | 6.2E0 | 6.0E0 | 1.2E1 | 1.3E1 | 8.6E-3 | 8.6E-3 | 1.6E2 | 3.9E1 | 465 | 9 | 174 | 9 | 0.37 |
| cI | ng/mL | 5.5E0 | 9.6E0 | 1.2E1 | 2.0E1 | 1.7E1 | 3.6E1 | 1.0E-3 | 1.1E0 | 1.2E2 | 1.2E2 | 465 | 9 | 174 | 9 | 0.54 |
| cJ | ug/mL | 5.6E1 | 7.6E1 | 1.1E2 | 8.9E1 | 1.4E2 | 6.7E1 | 4.0E0 | 8.4E0 | 9.6E2 | 1.9E2 | 465 | 9 | 174 | 9 | 0.52 |
| cK | ng/mL | 3.8E-3 | 3.8E-3 | 4.9E-2 | 4.7E-2 | 1.7E-1 | 6.8E-2 | 3.8E-3 | 3.8E-3 | 1.7E0 | 2.1E-1 | 465 | 9 | 174 | 9 | 0.63 |
| cL | pg/mL | 2.0E2 | 1.9E2 | 4.0E2 | 3.2E2 | 1.3E3 | 3.9E2 | 1.6E1 | 1.4E2 | 2.4E4 | 1.4E3 | 465 | 9 | 174 | 9 | 0.53 |
| cM | pg/mL | 2.7E2 | 2.3E2 | 3.0E2 | 2.5E2 | 1.9E2 | 1.4E2 | 8.7E1 | 5.7E1 | 1.6E3 | 4.7E2 | 465 | 9 | 174 | 9 | 0.43 |
| cN | pg/mL | 1.2E2 | 1.8E2 | 1.3E2 | 1.8E2 | 6.5E1 | 6.6E1 | 3.8E1 | 1.0E2 | 1.1E3 | 2.9E2 | 465 | 9 | 174 | 9 | 0.76 |
| cO | pg/mL | 2.2E2 | 3.0E2 | 3.1E2 | 3.2E2 | 9.1E2 | 1.1E2 | 5.4E1 | 1.6E2 | 1.9E4 | 5.0E2 | 465 | 9 | 174 | 9 | 0.69 |
| cP | ng/mL | 2.5E3 | 3.1E3 | 2.6E3 | 3.2E3 | 9.5E2 | 1.1E3 | 6.2E2 | 2.0E3 | 7.3E3 | 4.5E3 | 465 | 9 | 174 | 9 | 0.66 |
| cQ | ng/mL | 5.3E-2 | 6.7E-2 | 1.4E-1 | 1.9E-1 | 2.8E-1 | 2.8E-1 | 2.0E-3 | 2.0E-3 | 2.2E0 | 8.7E-1 | 465 | 9 | 174 | 9 | 0.60 |
| cR | ng/mL | 2.9E2 | 5.0E2 | 4.8E2 | 6.1E2 | 6.9E2 | 6.4E2 | 2.0E1 | 1.4E2 | 7.7E3 | 2.2E3 | 465 | 9 | 174 | 9 | 0.62 |
| cS | ng/mL | 2.6E2 | 6.0E2 | 4.3E2 | 5.3E2 | 1.1E3 | 3.3E2 | 4.7E1 | 1.4E2 | 2.2E4 | 9.9E2 | 465 | 9 | 174 | 9 | 0.65 |
| cT | ng/mL | 3.5E1 | 1.5E2 | 8.9E1 | 3.7E2 | 2.0E2 | 5.2E2 | 3.7E0 | 1.1E1 | 2.1E3 | 1.4E3 | 465 | 9 | 174 | 9 | 0.78 |
| cU | ng/mL | 5.4E1 | 8.8E1 | 7.7E1 | 1.1E2 | 1.0E2 | 6.1E1 | 5.4E0 | 4.0E1 | 1.6E3 | 2.3E2 | 465 | 9 | 174 | 9 | 0.73 |
| cV | ng/mL | 1.8E-1 | 2.8E-1 | 4.4E-1 | 3.4E-1 | 2.3E0 | 2.7E-1 | 3.4E-4 | 7.6E-2 | 4.7E1 | 9.3E-1 | 465 | 9 | 174 | 9 | 0.62 |
| cW | mIU/mL | 5.1E-2 | 9.4E-2 | 1.4E-1 | 1.5E-1 | 7.0E-1 | 1.2E-1 | 3.7E-4 | 3.6E-2 | 9.7E0 | 3.9E-1 | 465 | 9 | 174 | 9 | 0.74 |
| cX | ng/mL | 1.2E-1 | 6.9E-2 | 1.5E0 | 4.5E-1 | 4.6E0 | 8.2E-1 | 2.3E-4 | 2.3E-4 | 2.8E1 | 2.5E0 | 465 | 9 | 174 | 9 | 0.45 |
| cY | ng/mL | 8.5E0 | 1.2E1 | 1.2E1 | 1.5E1 | 1.3E1 | 1.1E1 | 1.5E-1 | 9.3E-1 | 8.3E1 | 3.6E1 | 465 | 9 | 174 | 9 | 0.60 |
| cZ | ug/mL | 1.4E1 | 1.5E1 | 1.5E1 | 1.5E1 | 6.4E1 | 5.8E0 | 2.7E0 | 3.3E0 | 3.9E1 | 2.3E1 | 465 | 9 | 174 | 9 | 0.55 |
| dA | pg/mL | 3.3E2 | 5.4E2 | 3.6E2 | 5.7E2 | 3.0E2 | 2.6E2 | 9.0E1 | 1.9E2 | 5.8E3 | 1.1E3 | 465 | 9 | 174 | 9 | 0.79 |
| dB | ug/mL | 1.7E1 | 2.4E1 | 1.8E1 | 1.9E1 | 1.6E1 | 9.2E0 | 9.4E-1 | 3.7E0 | 2.5E2 | 2.7E1 | 465 | 9 | 174 | 9 | 0.60 |
| dC | nmol/L | 3.5E1 | 3.6E1 | 3.9E1 | 4.1E1 | 1.8E1 | 1.8E1 | 7.6E0 | 2.1E1 | 1.4E2 | 7.9E1 | 465 | 9 | 174 | 9 | 0.54 |
| dD | ug/mL | 3.5E1 | 2.9E1 | 3.6E1 | 3.3E1 | 1.1E1 | 1.2E1 | 1.3E1 | 2.1E1 | 7.6E1 | 5.6E1 | 465 | 9 | 174 | 9 | 0.38 |
| dE | ng/mL | 4.6E-1 | 7.8E-1 | 5.8E-1 | 8.5E-1 | 6.9E-1 | 7.5E-1 | 8.4E-3 | 8.4E-3 | 7.2E0 | 2.4E0 | 465 | 9 | 174 | 9 | 0.64 |
| dF | ng/mL | 2.3E2 | 3.7E2 | 2.9E2 | 5.2E2 | 2.0E2 | 3.5E2 | 5.6E1 | 2.0E2 | 1.3E3 | 1.2E3 | 465 | 9 | 174 | 9 | 0.74 |

Figure 8 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| dG | ng/mL | 1.2E1 | 2.4E1 | 1.5E1 | 3.1E1 | 1.3E1 | 2.7E1 | 2.2E0 | 9.8E0 | 1.8E2 | 8.7E1 | 465 | 9 | 174 | 9 | 0.77 |
| dH | pg/mL | 7.5E0 | 1.4E1 | 1.3E1 | 1.3E1 | 3.7E1 | 8.7E0 | 4.0E-2 | 3.2E0 | 6.7E2 | 2.8E1 | 465 | 9 | 174 | 9 | 0.63 |
| dI | pg/mL | 4.6E-1 | 5.0E0 | 2.3E0 | 3.4E0 | 1.6E1 | 2.9E0 | 4.6E-1 | 4.6E-1 | 3.3E2 | 7.5E0 | 465 | 9 | 174 | 9 | 0.70 |
| dJ | ng/mL | 1.9E0 | 2.9E0 | 2.1E0 | 2.7E0 | 1.2E0 | 1.2E0 | 3.2E-2 | 4.9E-1 | 6.9E0 | 4.0E0 | 465 | 9 | 174 | 9 | 0.67 |
| dK | uIU/mL | 1.9E0 | 8.2E-1 | 3.1E0 | 3.6E0 | 6.4E0 | 7.0E0 | 2.8E-4 | 2.9E-2 | 7.9E1 | 2.2E1 | 465 | 9 | 174 | 9 | 0.41 |
| dL | ng/mL | 8.9E2 | 1.3E3 | 1.0E3 | 1.7E3 | 5.3E2 | 1.4E3 | 2.6E2 | 5.3E2 | 3.8E3 | 4.8E3 | 465 | 9 | 174 | 9 | 0.63 |
| dM | pg/mL | 9.7E2 | 2.5E3 | 1.3E3 | 3.6E3 | 1.4E3 | 3.0E3 | 3.4E2 | 8.3E2 | 1.6E4 | 9.6E3 | 465 | 9 | 174 | 9 | 0.81 |
| dN | ug/mL | 9.3E1 | 1.9E2 | 9.8E1 | 1.9E2 | 3.5E1 | 7.1E1 | 1.6E1 | 1.1E2 | 2.4E2 | 3.3E2 | 465 | 9 | 174 | 9 | 0.90 |
| eC | pg/ml | 3.0E2 | 1.9E2 | 3.7E2 | 4.3E2 | 2.6E2 | 7.1E2 | 1.9E1 | 7.1E1 | 1.6E3 | 2.0E3 | 268 | 7 | 162 | 7 | 0.28 |
| fP | ng/ml | 2.7E2 | 3.9E2 | 3.1E2 | 3.0E2 | 2.0E2 | 1.5E2 | 1.8E0 | 9.5E1 | 1.6E3 | 4.4E2 | 314 | 7 | 164 | 7 | 0.53 |
| fR | ng/ml | 1.4E5 | 2.7E5 | 1.8E5 | 3.1E5 | 1.4E5 | 2.3E5 | 2.9E4 | 1.9E2 | 8.3E5 | 6.8E5 | 302 | 8 | 87 | 8 | 0.67 |
| tF | pg/mL | 1.6E3 | 2.1E3 | 1.4E4 | 2.0E3 | 4.2E4 | 1.3E3 | 1.2E1 | 2.6E2 | 3.2E5 | 3.7E3 | 269 | 7 | 162 | 7 | 0.49 |

Analyte panel data:

Unconstrained panels with 3 analytes, where 1.0E-9 >= 'model p-value' > 0. Contains 6,892 panels of 7,079,861 total panels evaluated. :
Ji{Ms(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ng(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Jj(aA Et Fp Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Og(aA Et Fp Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe Wm) aA(Et Fp Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe Wm) Po(Et Fp Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) Fp(Et Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) No(Et Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) Mq(Et Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) Mu(Et Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mr Mt Mv Mw Mx My Mz Na Nb Nc Nd Ne Nf Nh Ni Nj Nk Nl Nm Nn Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) Ni(Et Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mr Mt Mu Mv Mw Mx My Mz Na Nb Nc Nd Ne Nf Nh Nj Nk Nl Nm Nn Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) Im(Et Fr Hq Hr Hu Hv Hw Hx Ih Ii Ij Ik Il In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mr Mt Mv Mw Mx My Mz Na Nb Nc Nd Ne Nf Nh Nj Nk Nl Nm Nn Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) Io(Et Fr Hq Hr Hu Hv Hw Hx Ih Ii Ij Ik Il In Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mr Mt Mv Mw Mx My Mz Na Nb Nc Nd Ne Nf Nh Nj Nk Nl Nm Nn Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) Jl(Et Fr Hq Hr Hu Hv Hw Hx Ih Ii Ij Ik Il In Ip Iq Ir Is It Iu Iv Jg Jh Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mr Mt Mv Mw Mx My Mz Na Nb Nc Nd Ne Nf Nh Nj Nk Nl Nm Nn Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) Jr(Et Fr Hq Hr Hu Hv Hw Hx Ih Ii Ij Ik Il In Ip Iq Ir Is It Iu Iv Jg Jh Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mr Mt Mv Mw Mx My Mz Na Nb Nc Nd Ne Nf Nh Nj Nk Nl Nm Nn Nq Nr Ns Nt Nu Nv Nw Nx Ny Oe Of Oh Oi Ok Om On Oy Oz Pa Pb Pc Pd Pe Pf Pg Pz Qa Qb Qc Qd Qe) Pc(Et Fr Hq Hr Hu Hv Hw Hx Ih Ii Ij Ik Il In Ip Iq Ir Is It Iu Iv Jg Jh Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mr Mt Mv Mw Mx My Mz Na Nb Nc Nd Ne Nf Nh Nj Nk Nl Nm Nn Nq Nr Ns Nt Nu Nv Nw Nx Ny Oe Of Oh Oi Ok Om On Oy Oz Pa Pb Pd Pe Pf Pg Pz Qa Qb Qc Qd Qe) Me(Et Fr Hq Hr Hu Hv Hw Hx Ih Ii Ij Il In Ip Iq Ir Is It Iu Iv Jg Jh Jk Jm Jn Jo Jp Jq Js Jt Lh Li Lj Lu Lv Lw Lx Ly Lz Ma Mb Mc Md Mf Mg Mh Mi Mj Mk Ml Mm Mn Mp Mr Mt Mv Mw Mx My Mz Na Nb Nc Nd Ne Nf Nh Nj Nk Nl Nm Nn Nq Nr Ns Nt Nu Nv Nw Nx Ny Oe Of Oh Oi Ok Om On Oy Oz Pa Pb Pd Pe Pf Pg Pz Qa Qb Qc Qd Qe) Pb(Et Fr Hq Hr Hu Hv Hw Hx Ih Ii Ij Ik In Iq Ir Is It Iu Iv Jg Jk Jm Jn Jo Jp Jq Js Jt Lh Li Lj Lu Lv Lw Lx Ly Lz Ma Mb Mc Md Mf Mg Mh Mi Mj Mk Ml Mm

Mc Md Me Mf Mg Mh Mi Mj Mk Ml Mn Mp Mr Ms Mt Mu Mv Mw Mx My Mz Na Nb Nc Nd Ne Nf Ng Nh Ni Nj Nk Nl Nm Nn Nq Nr Ns Nt Nu Nv Nx Ny Oe Of Og Om On Oy Oz Pa Pb Pd Pe Pf Pg Pz Qa Qb Qc Qd Qe) Jq(Fr Hq Hr Hu Hv Hw Hx Ih Ii Ij Ik Il Im In Io Iq Ir Is It Iu Jg Jh Jj Jk Jl Jm Jn Jo Jp Jr Js Jt Lh Li Lj Lu Lv Lx Ly Lz Ma Mb Mc Md Me Mf Mg Mh Mi Mj Mk Ml Mn Mp Mr Ms Mt Mu Mv Mw Mx My Mz Na Nb Nc Nd Ne Nf Ng Nh Ni Nj Nk Nl Nm Nn Nq Nr Ns Nt Nu Nx Ny Oe Of Og Om On Oy Oz Pa Pb Pd Pe Pf Pg Pz Qa Qb Qc Qd Qe) dN(aC aD aE aF aG aH aI aJ aK aL aM aN aO aP aQ aR aS aU aV aW aX aY aZ bA bB bC bE bF bG bH bI bJ bL bM bN bO bP bQ bR bS bU bV bW bX bZ cA cB cC cD cE cF cG cH cI cJ cK cL cM cN cO cP cQ cR cS cT cU cV cW cX cY cZ dA dB dC dD dE dF dG dH dI dJ dK dL dM Dp fP Nf) Lx(Fr Hq Hr Hu Hv Hw Hx Ih Ij Ik Il Im In Io Ir Is Jg Jh Jj Jk Jl Jn Jo Jr Jt Lh Li Lj Lu Ly Ma Mb Mc Md Me Mf Mh Mi Mk Ml Mn Mp Mr Ms Mt Mu Mv Mw My Na Nc Nd Ne Nf Ng Nh Ni Nj Nk Nl Nm Nn Nq Ns Nt Nx Ny Oe Of Og Om On Oy Oz Pa Pb Pd Pe Pf Pg Qa Qb Qc Qe) Om(Fr Hq Hr Hu Hv Hx Ih Ii Ij Ik Il Im In Io Is Iu Jg Jh Jj Jk Jl Jm Jn Jo Jr Jt Li Lj Ly Lz Ma Mb Mc Md Me Mf Mg Mh Mi Mk Ml Mn Mp Mr Ms Mu Mv Mw My Na Nb Nc Nd Ne Nf Ng Nh Ni Nj Nk Nl Nn Nq Ns Nu Nv Nx Oe Of Og On Oy Oz Pa Pb Pd Pe Pf Qa Qb Qc Qe) Mu(Hq Hr Hu Hv Hw Ih Ij Il Im In Io Ir Is Jg Jh Jj Jk Jl Jn Jr Js Jt Lh Li Lj Lu Ly Lz Ma Mb Me Mf Mg Mh Mj Ml Mn Mp Mr Ms Mt Mv My Mz Na Nc Nd Ne Nf Ng Nh Ni Nj Nk Nl Nm Nn Nq Ns Nt Nv Ny Oe Of Og On Oy Oz Pa Pb Pd Pe Pf Qa Qb Qc Qe) Jj(Fr Hr Hu Hv Hw Ii Ij Ik Im In Io Ir Is Jg Jk Jl Jm Jn Jo Jr Js Jt Lh Li Lj Ma Me Mf Mg Mh Mk Ml Mn Mp Mr Mt Mv Mw Mz Na Nc Ne Nf Ng Nh Ni Nj Nl Nm Nn Nr Ns Nt Nu Nv Nx Ny Oe Og On Oy Oz Pb Pd Pe Pf Pg Pz Qa Qb Qd Qe Wm) On(Hq Hr Hu Hv Ih Ii Il Im In Io Jh Jk Jl Jn Jr Li Lj Ly Ma Mb Md Me Mf Mh Mk Ml Mn Mr Ms Mv Mw My Na Nb Nc Nd Ne Nf Ng Nh Ni Nj Nk Nl Nn Nq Ns Nt Nv Nx Oe Of Og Oy Oz Pa Pb Pe Pf Qa Qb Qc Qe) Ng(Fr Hu Ij Ik Im Is Jg Jh Jk Jl Jn Jr Jt Lh Li Lj Ma Me Mf Mg Ml Mn Mp Mr Mt Mv Mw Na Nc Nf Nh Ni Nn Nt Nv Nx Ny Og Oz Pb Pd Pe Pf Pg Pz Qa Qb Qe) Nn(Hr Hu Ih Il Im Io Jh Jk Jl Jn Jr Li Lj Ma Me Mh Ml Mn Mr Ms Mv My Na Nc Ne Nf Nh Ni Nj Nk Nl Nq Ns Oe Of Og Oy Oz Pb Pe Pf Qa Qe) Ni(Fr Hu Im Io Is Jg Jl Jn Jr Lh Li Lj Ly Ma Me Mf Mh Ml Mn Mp Ms Mw Na Nc Nf Nh Nl Ns Nx Ny Oe Of Og Oy Oz Pb Pd Pe Pf Qa Qb Qe) Og(Fr Ij Ik Il Im Io Is Jg Jl Jn Jr Lh Li Lj Ma Me Mf Ml Mn Mp Mr Mt Mw Na Nc Ne Nf Nh Ns Nt Nu Nx Ny Oz Pd Pe Pf Qa Qb Qe Wm) Jr(Fr Hr Hu Hv Ih Il Im Io Is Jg Jl Jn Lh Li Ma Me Mf Ml Mn Mp Mr My Na Nc Nf Nk Nl Ns Nx Oe Oy Oz Pb Pd Pe Pf Qa Qe) Mn(Hu Il Im Io Jg Jl Jn Li Lj Ma Me Mf Mh Ml Mr Ms Na Nc Ne Nf Nh Nq Ns Nt Oe Oy Oz Pb Pe Pf Qa Qe) Nf(Fr Hu Im Io Is Jg Jl Jn Li Lj Ma Me Ml Mp Mr Mt Na Ne Nh Nl Ns Nt Oe Oy Pb Pd Pe Pf Qa Qb Qe) Me(Fr Hu Im Io Is Jg Jl Jn Lh Li Lj Ma Ml Mp Mr Nc Nk Nl Ns Nx Oe Of Pb Pe Pf Qa Qb Qe) Pf(Hq Hu Ih Il Im Io Jg Jl Jn Ml Ms My Na Nc Nk Nl Nq Ns Nx Oe Oy Oz Pa Pb Qa Qe) Li(Fr Hu Hv Il Im Io Jg Jl Jn Ma Ml Ms My Nc Nk Nl Nq Ns Oe Oy Oz Pb Qa Qe) Im(Fr Hu Ih Io Jg Jl Jn Lh Ma Mf Mh Ml Na Ns Oe Oy Oz Pb Pd Pe Qa Qe) Jg(Hu Io Jk Jl Jn Lj Ml Mr Ms Mv Mw My Na Ns Oe Of Oy Pb Pe Qa Qe) Oe(Fr Is Jl Jn Lh Lj Ma Mr Mw Na Ns Ny Oz Pb Pe Qa Qb Qe Wm) Qa(Hr Hu Hv Ih Il Io Ma Ml My Nc Nk Nl Nq Of Oy Pb Qc) Jl(Hr Hu Ih Il Io Jn Ma Ml My Nc Nk Nl Nq Ns Oy Oz Pb) Jn(Fr Hu Hv Ih Io Ma Mf Nc Nl Ns Oy Oz Pb Qe) Pe(Hu Il Io Ma My Nc Nk Nl Ns Oy Oz Pa Pb) Qe(Hr Hu Ih Il Io Ma Ml My Nc Oy Pb Qc) Io(Fr Is Lh Lj Ma Mp Na Qb) Oy(Fr Is Lh Ma Nx Pd) Fr(Hu Lj My) Pb(Ml Nx Pd) Hu(Lh Ma) aD(bJ dI) bM(bX dC) MwMy NcNe}
On{My(Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Ng(Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Oy(Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Nh Ni Nj Nk Nl Nm Nn No Nq Nr Ns Nt Nu Nv Nw Nx Ny Oe Of Og Oh Oi Ok Om Oz Pa Pb Pc Pd Pe Pf Pg Po Pz Qa Qb Qc Qd Qe Wm) Hu(Et Fp Fr Hq Hv Hw Ii Il Im In Io Ir Is Jj Jn Jo Jq Jr Lv Lw Lx Ly Ma Mc Me Mk Ml Mq Mr Ms Mu Mv Na Nc Nd Ne Nf Nh Ni Nk Nl Nn No Ns Nw Oe Og Oh Oi Ok Om Oz Pa Pb Pc Pe Pf Po Pz Qa Qc Qe) Jj(Et Fp Hq Im Is Jl Jn Jq Jr Lj Lv Lw Ly Me Mq Ms Mu Mv Mw Na Nf Nh Ni Nn No Nq Ns Of Og Oh Pb Po Qa Qe) Og(Fp Hq Im Is Jq Jr Lj Lw Ly Me Mq Mu No Nv Of Qa) Of(Fp Hv Hw Ij In Jn Jo Jq Jr Me Ni Oi Ok Qa) Ms(Fp Hq Im Lw Me Mq Mu Nn No Oh Pc) Mv(Hq Ly Me Mu Nn Pc) Mw(Me Pc) Hq(Ns Oi) NoOi MdJq} Jj{Po(Et Fp Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Pz Qa Qb Qc Qd Qe) No(Dp Et Fp Fr Hw Ij Ik Im Io Ir Is Iv Jg Jl Jn Jo Jq Jr Jt Lh Lj Lu Lv Lw Me Mq Mu Nf Ni Nn Ns Oh Oi Ok Om Pa Pc Qa Qe Wm) Fp(Et Fr Hx Ii Ir Is Iv Jg Jk Jl Jn Jq Jr Jt Lh Lv Lw Lx Mn Mq Mr Mu Mz Nf Nn Nt Nw Oh Ok Om Pc Pe Pg Qa Qe) Mq(Et Fr Im Ir Is Jk Jl Jn Jq Jr Js Jt Li Lw Lx Me Mn Mt Mu Mw Mx Mz Nn Nw Oh Ok Om Pc Pd Pe Pf Qa Qb Qe) Mu(Et Ir Is Iv Jl Jn Jq Jr Jt Lh Lv Lw Me Ml Mz Nf Ng Ni Nn Nt Nw Oh Ok Pd Pe Qa Qb Qe) Nn(Ir Is Iv Jl Jn Jq Jr Lh Lv Me Mr Nf Ng Nh Ni Oi Ok Pc Qa) Nf(Dp Et Fr Is Jl Jn Nt Nw Oh Ok Om Qa Qe) Jl(Et Jn Jq Jr Lv Lw Me Ni Oh Ok Om) Oh(Et Fr Jq Jt Lv Lw Me Ni Ok Om) Qa(Et Fr Jq Lw Me Nw Om) Jr(Et Fr Jq Lw Ok Om) Me(Et Fr Is Nw Om) Fr(Jn Jq Ng) Lw(Is Qe) NgOm QeJq NwOk} Ng{Fr(Et Fp Hv Hw Hx Ii Ij Ik Im In Ir Is Iv Jg Jh Jk Jl Jn Jo Jq Jr Jt Lh Lw Lx Md Me Ml Mm Mq Mr Mu Mw Mz Na Nb Ne Nf Nh Ni Nn No Nt Nw Oh Ok Om Oy Pc Pe Po Qa Qb Qe) Mu(Et li Im Ir Is Iv Jg Jh Jl Jn Jo Jq Jr Jt Lh Li Lv Lw Lx Ma Me Mi Mm Mn Mp Mq Mr Mt Mw Nb Nf Nn No Nt Nw Ny Oh Ok Om Pa Pc Pd Pe Pf Po Qa Qe) Jg(Et Fp Hu Hw Ii Ir Is Jk Jl Jn Jq Jr Jt Lh Li Lv Lw Lx Ma Me Mi Mm Mn Mp Mq Mr Mt Mw Nb Nf Ni Nn No Nt Nw Ny Oh Ok Om Pd Pe Pf Po Qa Qd Qe) Om(Fp Jk Jl Jr Lx Mq Nn No Nw Og Oh Ok Pc Pf Po Qa Qe) Nn(Et Jl Mq Ni Nw Ok) Ok(Mq No Nw Pc Po) No(Mq Pc) Jl(Jq Lw) Nw(Me Mq) PoNi} No{Mq(Jq Nn Og Oi Pc) dN(bO dH fP Oy) Mu(Me Oi Oy) Pc(Me Ni Oi) Nn(Ni Oi) EtIo} Nw{My(Jh Me Mq Mu Mw Nb Ni Ok) Og(Me Mq Mu) MdJq MeMu MqMs OfOk} Mu{Oy(Et Nb Pe) Jq(Mq Og) EtMe HuOk IsOg} Lw{Uu(Ba Cx Fp Jd) JlOg} Jq{Mq(Fr Nn Og Pc) JlOg} dN{Aj(Ly Me) SrbO bRdA} Nn{FpOi NbOy} Kj{Kq(bJ Dp)} NfJlOg SrUudI

Unconstrained panels with 3 analytes, where 1.0E-8 >= 'model p-value' > 1.0E-9. Contains 9,426 panels of 7,079,861 total panels evaluated. :
Ji{Wm(Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Oh Ok Om On Oz Pa Pb Pc Pd Pe Pf Pg Po Pz Qa Qb Qc Qd Qe) Nk(Et Fr Hq Hr Hu Hv Hw Hx Ih Ii Ij Ik Il In Ip Iq Ir Is It Iu Iv Jg Jh Jk Jm Jn Jo Jp Jq Js Jt Lh Li Lj Lu Lv Lw Lx Ly Lz Ma Mb Mc Md Mf Mg Mh Mi Mj Mk Ml Mm Mn Mp Mr Mt Mv Mw Mx My Mz Na Nb Nc Nd Ne Nf Nh Nj Nl Nm Nn Nq Nr Ns Nt Nu Nv Nw Nx Ny Oe Of Oh Ok Om On Oy Oz Pa Pb Pe Pf Pg Pz Qa Qb Qc Qd Qe) It(Et Fr Hq Hr Hu Hv Hw Hx Ih Ii Ij Ik Il In Ip Iq Ir Is Iu Iv Jg Jh Jk Jm Jn Jo Jp Jq Js Jt Lh Li Lj Lu Lv Lw Lx Ly Lz Ma Mb Mc Md Mf Mg Mh Mi Mj Mk Ml Mm Mn Mp Mr Mt Mv Mw Mx My Mz Na Nb Nc Nd Ne Nf Nh Nj Nl Nm Nn Nq Nr Ns Nt Nu Nv Nw Nx Ny Oe Of Oh Oi Ok Om On Oy Oz Pa Pd Pe Pf Pg Pz Qa Qb Qc Qd Qe) Ik(Et Fr Hq Hr Hu Hv Hw Hx Ih Ii Ij Il In Ip Iq Ir Is Iu Iv Jg Jh Jk Jm

Figure 8 Continued

Mj Ml Mm Mr Mv Mw My Ne Nf Nh Ns Nt Nw Ny Om On Oz Pa Pd Pe Pz Qa Qb Qe) Lh(Hq Hr Hu Hv Hx Ih Ii Ij In Is Iv Jg Jn Jo Jt Lj Lu Lv
Lw Lx Ly Ma Md Mg Mi Mj Ml Mm Mr Mv Mw Na Ne Nf Nh Ns Nt Nw Ny Om Oz Pd Pf Pz Qa Qb Qc Qe) Om(Et Hq Hr Hv Hx Ih Ii Ij In Is
Iv Jg Jn Jo Jt Lj Lu Lv Lw Lx Ma Md Mi Mj Ml Mm Mr Mw Na Ne Nf Nh Ns Nt Nw Ny Oh Oz Pa Pd Pe Pf Pz Qa Qb Qc Qe) Jg(Et Fr Hq Hr
Hv Hx Ih Ii Ij In Is Iv Jn Jo Jt Lj Lu Lv Lw Lx Ma Md Mi Mj Ml Mm Mr Na Ne Nf Nh Nt Nw Ny Ok On Oz Pa Pd Pe Pf Pz Qa Qb Qe) Mw(Hq
Hr Hv Hx Ih Ii Ij In Is Iv Jn Jo Jt Lj Lu Lv Lw Lx Ma Md Mg Mi Mj Ml Mm Mr Mv Na Ne Nf Nh Ns Nt Nw Ny Oz Pa Pd Pe Pf Pz Qa Qb Qe)
Pd(Et Fr Hq Hr Hv Hx Ih Ii Ij Is Iv Jn Jt Lj Lu Lv Lw Lx Ma Md Mi Mj Ml Mm Mr Mv Na Ne Nf Nh Ns Nt Nw Ny Ok On Oz Pe Pf Pz Qa Qb
Qe) Mi(Et Hr Hv Hx Ih Ii Ij In Is Iv Jn Jo Jt Lj Lu Lv Lw Lx Ma Md Mg Mj Mm Mr Mv Na Ne Nf Nh Ns Nt Nw Ny Oz Pa Pf Pz Qa Qb Qc Qe)
Mj(Hq Hr Hu Hv Hx Ih Ii Ij In Is Iv Jn Jo Jt Lj Lu Lv Lw Lx Ma Md Mg Ml Mm Mv Na Ne Nf Nh Ns Nt Nw Ny On Oz Pa Pe Pz Qb) Hx(Hq
Hr Hu Hv Ih Ii Ij In Is Iv Jn Jo Jt Lj Lu Lv Lw Md Mg Ml Mm Mv Na Ne Nf Nh Ns Nw Nx Ny Oy Oz Pf Pz Qa Qb Qc Qe) Ij(Hq Hr Hu Hv Ih
Ii In Is Iv Jn Jo Jt Lj Lu Lv Lw Lx Md Mg Ml Mm Mv My Na Ne Nh Ns Nw Nx Ny Of Oy Oz Pa Pe Pz Qb) Lx(Fr Hr Hv Ih Ii In Is Iv Jn Jo Jt
Lj Lu Lv Lw Ma Mm Mr Na Ne Nf Nh Ns Nt Nw Ok On Oz Pa Pe Pf Pz Qa Qb Qe) Hq(Hr Hu Hv Ih Ii In Is Iv Jn Jo Jt Lj Lu Lv Lw Ly Md Mg
Ml Mm Mv My Na Ne Nh Ns Nw Nx Ny Oy Pz Qa Qb Qe) Iv(Hr Hv Ih Ii Is Jn Jt Lj Lu Lv Md Mg Ml Mr Mv Na Ne Nf Nh Ns Nt Nw Ny Ok
On Oz Pa Pe Pf Pz Qa Qb Qe) Nw(Fr Hv Ih In Is Jn Jo Jt Lj Lu Lv Lw Ma Mg Mm Mr Na Ne Nf Nh Nn Nt Ok On Oz Pe Pf Pz Qa Qb Qe)
Md(Hr Hu Hv Ih Ii In Is Jn Jo Jt Lj Lv Lw Mg Ml Mm Mv Na Ne Nh Ns Nx Ny Of Oy Oz Pz Qa Qb Qe) Is(Hr Hv Jn Jo Jt Lj Lu Lv Ma Mg Ml
Mr Mv Na Ne Nf Nh Nt Ny Ok On Oz Pa Pe Pf Pz Qa Qb Qe) Jt(Hr Hu Hv Ih Ii In Jn Jj Lu Lv Lw Mg Ml Mr Mv Na Ne Nf Nh Ns Ny Oz Pa
Pe Pz Qa Qb Qe) Jn(Hr Hv Ii Jo Lj Lu Lv Ma Mg Ml Mr Mv Ne Nf Nh Nt Ny On Oz Pa Pe Pf Pz Qa Qb Qe) Hv(Hr Hu Ih Ii In Jo Lj Lv Lw Ma
Mg Ml Mm Mv Nf Nh Ns Ny Of Oz Pa Pe Pz Qb) Pz(Hr Ih Ii In Jo Lj Lu Lv Mg Ml Mv Ne Nf Nh Ns Nx Ny Oy Oz Pa Pe Qb) Lj(Hr Hu Ii
Jo Lv Mg Ml Mr Mv Na Ne Nh Ns Nt Ny Of Oz Pa Pe Pf Qa Qe) Ny(Hr Hu Ih Ii In Jo Lv Lw Mg Ml Mm Mv Na Ne Nh Ns Oy Oz Qa Qb Qe)
Mg(Hr Hu Ih Ii In Jo Lv Ml My Ne Nh Ns Nx Of Oy Qa Qb Qe) Ii(Hr Hu Ih In Jo Lu Lv Lw Ml Mv My Ne Nh Ns Nx Oy Qb) Hr(Hu Ih In Jo
Lv Lw Ma Ml Mm Mv Nh Ns Pa Qb) Oz(Lu Lv Ml Mr Mv Na Ne Nh Nt On Pe Qa Qb Qe) Jo(Hu Ih In Lu Lv Lw Ml Mv My Ne Nh Ns Oy)
Qb(Ih Lu Lw Ma Ml Mm Mv Nh Nt On Pe) Qe(Lu Lv Ml Mr Ne Nh Nt On Pe Pf Qa) Lv(Ih In Ma Ml Mr Mv Nh Pa Qa) Nt(Lu Mr Ne Nh Ok
On Pe Qa) Ml(Hu Lw Mm Mv Ne Nh Of) Lu(Ih Nf Nh On Pa Pe) Mv(Ih In Lw Ne Nh) Qa(Mr Ne Nh Pc Pf) Pe(Mr Na Ok On) Nf(Ih Mr Pa)
Kr(bO Jv Uu) Nh(Mr Pa) Ih(In Pa) On(Fr Ok) LwMm UsbJ} aA[Qb(Fr Hq Hr Hu Hv Hw Hx Ih Ii Ij Ik Il Im In Ip Iq Ir Is It Iu Iv Jg Jh Jk Jl Jm
Jn Jo Jp Jr Js Jt Lh Li Lj Lu Ly Lz Ma Mb Mc Md Mf Mg Mh Mi Mj Mk Ml Mn Mp Mr Ms Mt Mv Mw Mx My Mz Na Nb Nc Nd Ne Nh Nj
Nk Nl Nm Nn Nq Nr Ns Nt Nu Nv Nx Ny Of Oy Oz Pa Pb Pd Pe Pf Pg Pz Qa Qc Qd Qe) Is(Fr Hq Hr Hu Hv Hw Hx Ih Ii Ij Ik Il Im In Ip Iq Ir
It Iu Iv Jg Jh Jk Jl Jm Jn Jo Jp Js Jt Lh Li Lj Lu Ly Lz Ma Mb Mc Md Mf Mg Mh Mi Mj Mk Ml Mn Mp Mr Ms Mt Mv Mw Mx My Mz Na Nb
Nc Nd Ne Nh Nj Nk Nl Nm Nn Nq Nr Ns Nt Nu Nv Nx Ny Of On Oz Pa Pb Pd Pe Pf Pg Pz Qa Qc Qd Qe) Lh(Fr Hq Hr Hv Hw Hx Ih Ii Ij Ik Il
In Ip Iq Ir It Iu Iv Jg Jh Jk Jl Jm Jn Jo Jp Js Jt Li Lj Lu Ly Lz Ma Mb Mc Md Mf Mg Mh Mi Mj Mk Ml Mn Mp Mr Ms Mt Mv Mw Mx My Mz
Na Nb Nc Nd Ne Nf Nh Nj Nk Nl Nm Nn Nq Nr Ns Nt Nu Nv Nx Ny Of Om On Oz Pa Pb Pd Pe Pf Pg Pz Qa Qc Qd Qe) Mr(Fr Hq Hr Hu Hv
Hw Hx Ih Ii Ij Ik Il Im In Io Ip Iq Ir It Iu Iv Jh Jk Jl Jm Jn Jo Jp Js Jt Li Lj Lu Ly Lz Ma Mb Mc Md Mf Mg Mh Mi Mj Mk Ml Mp Ms Mt Mv
Mw Mx My Mz Na Nb Nc Nd Ne Nh Ni Nj Nk Nl Nm Nq Nr Ns Nt Nu Nv Nx Ny Of Oy Oz Pa Pb Pd Pe Pf Pg Pz Qa Qc Qd Qe) Na(Fr Hq Hr
Hu Hv Hw Hx Ih Ii Ij Ik Il In Ip Iq Ir It Iu Iv Jh Jk Jl Jm Jn Jo Jp Js Jt Li Lj Lu Ly Lz Ma Mb Mc Md Me Mf Mg Mh Mi Mj Mk Ml Mp Ms Mt
Mv Mw Mx My Mz Nb Nc Nd Ne Nh Nj Nk Nl Nm Nq Nr Ns Nt Nu Nv Nx Ny Of Oy Oz Pa Pb Pd Pe Pg Pz Qa Qc Qd Qe Wm) Lj(Hq Hr Hu
Hv Hw Hx Ih Ii Ij Ik Il Im In Ip Iq Ir It Iu Iv Jh Jk Jl Jm Jn Jo Jp Jr Js Jt Li Lu Ly Lz Ma Mb Mc Md Mf Mg Mh Mi Mj Mk Ml Mp Ms Mt Mv
Mw Mx My Mz Nb Nc Nd Ne Nh Nj Nk Nl Nm Nq Nr Ns Nt Nu Nv Nx Ny Of Oy Oz Pa Pb Pd Pe Pf Pg Pz Qa Qc Qd Qe) Fr(Hq Hr Hv Hw
Hx Ih Ii Ij Ik Il In Ip Iq Ir It Iu Iv Jg Jh Jk Jl Jm Jo Jp Js Jt Lu Ly Lz Ma Mb Mc Md Mf Mg Mh Mi Mj Mk Ml Mn Mp Ms Mt Mu Mv Mw Mx
Mz Nb Nc Nd Ne Nh Nj Nk Nl Nm Nn Nq Nr Ns Nt Nu Nv Nx Ny Of On Oz Pa Pb Pd Pe Pf Pg Pz Qa Qc Qd Qe Wm) Ml(Hq Hr Hu Hv Hw
Hx Ih Ii Ij Ik Il In Io Ip Iq Ir It Iu Iv Jh Jk Jm Jn Jo Jp Js Jt Lu Ly Lz Ma Mb Mc Md Mf Mg Mh Mi Mj Mk Mp Ms Mt Mv Mw Mx My Mz Nb
Nc Nd Ne Nh Nj Nk Nl Nm Nq Nr Ns Nt Nu Nv Nx Ny Oc Of Oy Oz Pa Pd Pe Pg Pz Qc Qd) Ma(Hq Hr Hv Hw Hx Ih Ii Ij Ik Il In Ip Iq Ir It Iu
Iv Jg Jh Jk Jm Jo Jp Js Jt Lu Ly Lz Mb Mc Md Mf Mg Mh Mi Mj Mk Mp Ms Mt Mv Mw Mx My Mz Nb Nc Nd Ne Nh Nj Nk Nl Nm Nq Nr Ns
Nt Nu Nv Nx Ny Of Oz Pa Pb Pd Pf Pg Pz Qc Qd) Io(dN Hq Hr Hu Hv Hw Ih Ii Ij Ik Il In Ip Ir It Iv Jh Jk Jm Jo Jp Js Jt Lu Ly Lz Mb Mc Md
Mf Mg Mh Mi Mj Mk Ms Mt Mv Mw Mx My Mz Nb Nc Nd Ne Ng Nh Nj Nk Nl Nm Nq Nr Ns Nt Nu Nv Nx Ny Oe Of Oy Oz Pa Pb Pd Pg Pz
Qd) Oe(Hq Hr Hu Hv Hw Hx Ih Ii Ij Ik Il In Ip Iq Ir It Iu Iv Jh Jk Jm Jo Jp Js Jt Lu Ly Lz Mb Mc Md Mf Mg Mh Mi Mj Mk Mp Ms Mt Mv Mx
My Mz Nb Nc Nd Ne Ng Nh Nj Nk Nl Nm Nq Nr Nt Nu Nv Nx Of Og Oy Pa Pd Pg Pz Qc Qd) Pe(Hq Hr Hv Hw Hx Ih Ii Ij Ik In Ip Iq Ir It Iu
Iv Jh Jk Jl Jm Jn Jo Jp Js Jt Li Lu Ly Lz Mb Mc Md Mf Mg Mh Mi Mj Mk Mp Ms Mt Mv Mw Mx Mz Nb Nd Ne Nh Nj Nm Nq Nr Nt Nu Nv
Nx Ny Of Pd Pf Pg Pz Qa Qc Qd Qe) Oy(dN Hr Hu Hv Hw Ih Ii Ij Ik Il In Ip Ir Iv Jh Jk Jm Jo Jp Js Jt Lu Ly Lz Mb Mc Md Me Mf Mg Mh Mi Mj
Mk Mp Ms Mt Mv Mw Mx My Mz Nb Nc Nd Ne Ng Nh Nj Nk Nl Nm Nq Nr Ns Nt Nu Nv Ny Og Oz Pa Pb Pg Pz Qd Wm) Qe(Hq Hv Hw Hx
Ii Ij Ik In Ip Iq Ir It Iu Iv Jh Jk Jl Jm Jo Jp Js Jt Lu Ly Lz Mb Mc Md Mf Mg Mh Mi Mj Mk Mp Ms Mt Mv Mw Mx Mz Nb Nd Ne Nh Nj Nk Nl
Nm Nq Nr Ns Nt Nu Nv Nx Ny Of Oz Pa Pd Pg Pz Qa Qd) Jg(Hq Hr Hv Hw Hx Ih Ii Ij Ik Il In Ip Iq Ir It Iu Iv Jh Jm Jo Jp Js Jt Lu Ly Lz Mb
Mc Md Mf Mg Mh Mi Mj Mk Mp Mt Mx Mz Nb Nc Nd Ne Nh Nj Nk Nl Nm Nn Nq Nr Nt Nu Nv Nx Ny On Oz Pa Pd Pg Pz Qc Qd Wm)
Me(dN Hq Hr Hv Hw Hx Ih Ii Ij Ik Il In Ip Iq Ir It Iu Iv Jh Jk Jm Jo Jp Js Jt Lu Ly Lz Mb Mc Md Mf Mg Mh Mi Mj Mk Ms Mt Mv Mw Mx My
Mz Nb Nd Ne Nh Nj Nm Nq Nr Nt Nu Nv Ny Oz Pa Pd Pg Pz Qc Qd Wm) Jn(Hq Hr Hw Hx Ii Ij Ik Il In Ip Iq Ir It Iu Iv Jh Jk Jm Jo Jp Js Jt Lu
Ly Lz Mb Mc Md Mg Mh Mi Mj Mk Mp Ms Mt Mv Mw Mx My Mz Nb Nd Ne Nh Nj Nk Nm Nq Nr Nt Nu Nv Nx Ny Of Pa Pd Pg Pz Qa Qc
Qd Wm) Im(Hq Hr Hv Hw Hx Ii Ij Ik Il In Ip Iq Ir It Iu Iv Jh Jk Jm Jo Jp Js Jt Lu Ly Lz Mb Mc Md Mg Mi Mj Mk Mp Ms Mt Mv Mw Mx My
Mz Nb Nc Nd Ne Nh Nj Nk Nl Nm Nq Nr Nt Nu Nv Nx Ny Of Pa Pg Pz Qc Qd) Nf(Hq Hr Hv Hw Hx Ih Ii Ij Ik Il In Ip Iq Ir It Iu Iv Jh Jk Jm Jo
Jp Js Jt Lu Ly Lz Mb Mc Md Mf Mg Mh Mi Mj Mk Ms Mv Mw Mx My Mz Nb Nc Nd Nj Nk Nm Nq Nr Nu Nv Nx Ny Of Oz Pa Pg Pz Qc Qd)
Jl(Hq Hv Hw Hx Ii Ij Ik In Ip Iq Ir It Iu Iv Jh Jk Jm Jo Jp Js Jt Lu Ly Lz Mb Mc Md Mf Mg Mh Mi Mj Mk Mp Ms Mt Mv Mw Mx Mz Nb Nd
Ne Nh Nj Nm Nr Nt Nu Nv Nx Ny Of Pa Pd Pg Pz Qa Qc Qd) Li(Hq Hr Hv Hw Hx Ih Ii Ij Ik In Ip Iq Ir It Iu Iv Jh Jk Jm Jo Jp Js Jt Lu Ly Lz Mb
Mc Md Mf Mg Mh Mi Mj Mk Mp Mt Mv Mw Mx Mz Nb Nd Ne Nh Nj Nm Nr Nt Nu Nv Nx Ny Of Pa Pd Pf Pg Pz Qc Qd) Mn(Hq Hr Hv Hw
Hx Ih Ii Ij Ik In Ip Iq Ir It Iu Iv Jh Jk Jm Jo Jp Js Jt Lu Ly Lz Mb Mc Md Mg Mi Mj Mk Mp Mt Mv Mw Mx My Mz Nb Nd Nj Nk Nl Nm Nr Nu
Nv Nx Ny Of Pa Pd Pg Pz Qc Qd Wm) Qa(Hq Hw Hx Ii Ij Ik In Ip Iq Ir It Iu Iv Jh Jk Jm Jo Jp Js Jt Lu Ly Lz Mb Mc Md Mf Mg Mh Mi Mj Mk
Mp Ms Mt Mv Mw Mx Mz Nb Nd Ne Nh Nj Nm Nr Ns Nt Nu Nv Nx Ny Oz Pa Pd Pg Pz Qd) Jr(Hq Hv Hx Ii Ij Ik In Ip Iq Ir It Iu Iv Jh Jk Jm
Jo Jp Js Jt Lu Ly Lz Mb Mc Md Mg Mh Mi Mj Mk Ms Mt Mv Mw Mx Mz Nb Nd Ne Nh Nj Nm Nq Nr Nt Nu Nv Ny Of Pa Pg Pz Qc Qd Wm)
Pd(Hq Hr Hu Hv Hw Ih Ii Ij Ik Il In Jh Jk Jm Jo Jp Js Jt Lu Ly Lz Mb Mc Mf Mg Mh Mj Mp Ms Mt Mv Mw My Mz Nc Nd Ne Nh Nj Nk Nl
Nm Nn Nq Ns Nt Nu Nx Ny Of On Oz Pa Pf Qc Qd) Pf(Hr Hv Hw Hx Ii Ij Ik In Ip Iq Ir It Iu Iv Jh Jk Jm Jo Jp Js Jt Lu Ly Lz Mb Mc Md Mf
Mg Mh Mi Mj Mk Mp Mt Mv Mw Mx Mz Nb Nd Ne Nh Nj Nm Nr Nt Nu Nv Ny Of Pg Pz Qc Qd) Ni(Hq Hr Hv Hw Hx Ih Ii Ij Ik Il In Ip Iq Ir

Nv Of Oh Oi Ok Oy Pb Pc Pe Pf Pg Qa) My(Et Fp Fr Hv Hw Ij Im In Ir Is Iv Jg Jl Jn Jo Jq Jr Jt Lh Lv Lw Ly Mt Mv Na Nf Nn No Oi Om Pc Pe Po Qa Qe) Og(Et Fp Fr Hv Hw Ij Im In Ir Is Iv Jl Jn Jo Jq Jr Jt Lh Lw Na Nb Nf Ni Nn No Oh Ok Om Pc Pe Po Qa Qe) Mq(Et Fp Hu Im Ir Jn Jq Jr Lw Ly Mg Mw Ni No Nq Ns Nv Nx Of Oh Oi Ok Oy Pb Pc Pz Qa) Ms(Fp Hv Hw Ij Ir Is Iv Jl Jn Jo Jq Jr Jt Lw Mu Na Nf Ni Nn No Oh Ok Pc Pe Po Qa) Ok(Fp Hu Ii Im Jo Jr Lw Ly Md Mg Mm Mu Mw Nv Nx Ny Oh Oi Oy Pa Pb Pc Pg) Oi(Fp Ir Is Jl Jn Jr Jt Mu Na Nn No Oh Pc Pe Qa) Ni(Et Im Is Jl Jr Ly Mm Nn No Oh Oy Pb Pc Qa) Oy(Iv Jo Jq Jt Mu Nb Nn Pe Qa) Qa(Et Md Mm Ny Of Pb) Jq(Fp Jl Jr Mm Mu Pc) Of(Hw Ij Jo Jt) Lw(Fp Is Jr) Jr(Et Mm) MdHw MuHu HqPe JnJs JoJt} No{Mq(Et Fp Fr Hr Hu Ii Il In Io Jn Jo Jr Lu Lv Lw Me Mg Mj Mm Ms Mt Mu My Mz Ni Nk Nr Ns Oe Ok Oy Pb Pz) Ni(Et Fr Im Io Is Jl Jq Jr Lv Lw Me Mm Ms Mu My Og Oh Oi Ok Oy Pb Qe Uu) Oi(Et Fp Fr Io Is Jg Jl Jn Jq Jr Lu Lv Lw Me Mm Mt Nf Oh Ok Om Qa Qe) Pc(Et Fp Io Jn Jq Jr Lu Lv Lw Ms Mu My Nc Nk Ns Og Ok Oy Qa Wm) Ok(Hu Ii Io Jo Jq Jr Jt Lv Lw Me Ms Mu My Nl Nn Og Oy) Lw(Fp Io Is Jl Jr Lv Lw Me Ms Mu Ns Og Oy Us Uu Wm) dN(aF Aj aO Ch Co Dg Dp Ef Hc Ii Jt Kg Kr Us Uu) Mu(Et Hu Io Jn Jq Jr Lv Mm Ms My Nk Ns Oe Og) Lv(Im Io Jn Jq Jr Lu Me Mm Mt Nf Nn Oy) Nn(Et Io Jq Lj Me Ms My Ns Og Oy) Jq(Et Fp Io Jl Md Me Mm Og Oy) Dp(Ao Ch Co Hq Qv) Et(Jr Lu Me Ms Nf) Io(Is Jl Jr Me Mm) Kj(Cw Id Kq Pi Pk) Om(Hu Ms My Og Oy) Wm(Ly Og Oy) Fr(Me My Oy) Ch(bO Nf) Mm(Jr Me) Jn(Js Lj) Og(Jl Nf) UsdM UubO} Mu{Et(Hu Ir Is Iv Jn Jo Jq Jr Lj Lw Mg Ms My Ni Ns Of Og Oi Qa) Jq(Fp Hu Is Jl Jr Lj Md Me Mm Ms Of Oi Ok Oy Pc Qa Qe) Og(Ir Iv Jl Jn Jr Jt Lh Lw Me Mq Mr Mz Ok Pe Po Qa Qe) Oy(dN Is Jl Jr Lx Mi Mq Ok Pf Po Qa) Me(Hu Jl Jn Jr Lj Lw Mm Oh Ok) Is(Hu Il Lw Mm Ms My Oe Oi) Ok(Jo Jr Lw Ly Mg Ms My Of) Jr(Lw Mm Mq Ms Ni Oi) Oi(Fp Jn Lj Oh Qa) Mq(Hu Jn) LwJn MyNb HuOm SrUu} Jq{Mq(Et Fp Is Jl Jn Jo Jr Li Lx Md Mm Ns Oh Ok Om Oy Pb Pf Po Qa Qe) Jl(Et Fp Hu Ii Io Jo Lw Md Me Mm Ms My Ni Ns Of Oh Oi Oy Pc) Og(Fp Fr Lx Nn Ok Pc Po Qa Qe Wm) Fr(Fp Hu Jr Me My Oy) Et(Jr Oh Pc Qa Qe) Fp(Mm Nn Ok Pc) Pc(Ok Qa Qe) Oy(Pf Po) BaUu NnOk LxHu MmJr} dN{Aj(Ba bJ bN bR cT Cw dA Ef Nf) Ch(Ba bJ bN Bo cT Ly Me Ni) Hc(eC Jd Je Jn Lw Rf Rh) Oy(Ba Kr Ms Nr Oe Qg) bO(bA Gp Jn Me Rf) bR(bA bX cT dI dM) Nf(Jo Kg Kr Ur) dH(bA bQ cT dA) Uu(Ba Jy Sr) Dp(Qv Rf) Kq(aF Kj) Kr(Jn Kx) dA(bU cA) fP(Qv Rf) JoKz} Lw{Uu(Ax bJ Cw Dp Ef Ez Hu Ij Im Is Jg Jn Kq Lh Ma Mq Nf Nr Ow Pk Qy Rf Sr Uf Un) Jl(Fp Jn Jr Me Ns Oy) Jr(Et Mq Ok Wm) Og(Is Po Qe) Us(bJ bN dA) Dp(Aj Ur) Fp(Fr Ok) Mq(Jn Ns) Kj(bJ Pk) Kr(Cs Ml) WmJn} Ok{Nn(Fp Hu Jo Jr Me Mq Ms My Of Og Oi) Pc(Fp Jo Jr Mg Mq My Of Og) Jo(Fp Fr Jl Mq Oh Po) Po(Hu Of Og Oy) Fr(Hu My Of Oy) Lx(Hu Oy) Jr(Mm Of) Oh(Ms Oi) FpLy MqOf JlOg} Og{Jl(Et Fp Io Jn Jr Me Mq Mz Ni Nn Oh Om Pc Po) Mq(Fr Is Jr Mz Nn Oh Pc Po) Is(Et Mm Nn Om Pc Po) Om(Hu Jr Oh Qa Qe) FpFr NnMe} Kq{Kj(aF aK aL aU aV Ba bN bO cI cZ dA Fn Hu Hw Pd Rf Ua) Uu(aF Ba bJ cZ Kr Qc Qg) Oy(aW Tn To Tv) Aj(bJ Dp Kr)} Mq{Fr(Hu Jn Jr Me Ms My Oy) Nn(Jr Ms Ns Oi Oy) Ns(Is Jr Oh Pc) Et(Jn Jr Mz) Pc(Jn Jr Mz) Oi(Is Oh) LxOy} Et{Me(Fr Jl Jr Lx Nn Oh Pc) Ms(Is Jr Nn Oh) Ni(Is Jr Oh) Io(Is Jr Qa) Oi(Is Nn Oh) JrPc} Fr{Me(Hu Jr Mm Oh) My(Is Jn Jr Nb) Oy(Fp Jr Nb Pe) Oi(Fp Jr) HuOm} Uu{Sr(Ba bJ Jd Qg) Un(Ba Cv Ni) CvJd} Jl{Oi(Fp Jn Nn Oh) MwMy NiOh OmOy} Oy{Nb(Lx Om Po) Pe(Jg Nn) LxOm} Nn{Oi(Is Jn Jr)} Mm{Ni(Is Jr) MeJr} bJ{Kj(Ad Id) AjSr} AjDpSr

Unconstrained panels with 3 analytes, where 1.0E-7 >= 'model p-value' > 1.0E-8. Contains 15,920 panels of 7,079,861 total panels evaluated. : aA{dN(Ad Al An Ap Ar As Aw Ax Ba Bb Bc Bn Bo Co Cp Cq Cs Ct Cu Cv Cw Db Dc Dd De Dg Di Dk Dl Ed Et Fn Fr Fw Gp Hb Hf Hq Hr Hu Hw Hx Ih Ii Ij Ik Il Im In Ip Iq Ir Is It Iu Iv Iz Jd Jg Jh Ji Jj Jk Jl Jm Jn Jo Jp Jq Jr Js Jt Jv Kd Ki Kj Kl Ko Kr Kx Lh Li Lj Lu Lv Lw Lx Lz Ma Mb Mc Md Mf Mg Mh Mi Mj Mk Ml Mm Mn Mp Mq Mr Ms Mt Mu Mv Mw Mx Mz Na Nb Nc Nd Ne Ng Nh Ni Nj Nk Nl Nm Nn No Nq Nr Ns Nt Nu Nv Nw Nx Ny Oe Of Og Oh Oi Ok Om On Ow Pa Pb Pc Pd Pe Pf Pg Ph Pk Po Pz Qa Qb Qc Qe Qg Ql Qu Qz Rf Ri Us Uu Wm Tj tF) Wm(Hq Hr Hv Hw Hx Ih Ii Ij Ik Il Im In Io Ip Iq Ir Is It Iu Iv Jh Jk Jl Jm Jo Jp Js Jt Lh Li Lj Lu Lx Lz Ma Mb Mc Md Mf Mg Mh Mi Mj Mk Ml Mp Mr Mt Mv Mw Mx My Mz Nb Nc Nd Ne Nf Nh Ni Nj Nk Nl Nm Nq Nr Ns Nt Nu Nv Nx Ny Of Oh Om Pa Pb Pd Pc Pf Pg Pz Qa Qb Qc Qd Qe) bW(aC aE aF aH aI aJ aK aL aM aN aO aP aQ aR aS aU aV aX aY aZ bA bB bC bE bF bG bH bI bJ bL bM bO bP bQ bS bU bV bX bZ cA cB cC cD cE cF cG cH cI cJ cK cL cM cN cO cP cQ cR cS cT cU cV cW cX cY cZ dA dB dD dE dF dG dH dI dJ dK dL dM Dp) dI(aC aE aF aG aH aI aJ aK aL aN aO aP aQ aR aS aU aV aW aX aY aZ bA bB bC bE bF bG bH bI bJ bL bN bO bP bQ bS bV bX bZ cA cB cC cD cE cF cG cH cI cJ cK cL cM cN cO cP cQ cR cS cT cU cV cW cX cY cZ dA dB dC dD dE dF dG dH dJ dK dL dM) aM(aC aD aE aF aG aH aI aJ aK aL aN aO aQ aR aS aU aV aX aY aZ bA bB bC bE bF bG bH bI bL bN bO bP bQ bR bS bU bV cA cC cD cE cF cH cI cJ cK cL cM cN cO cP cQ cR cS cT cU cV cW cX cY cZ dA dB dC dD dE dF dG dH dJ dK dL dM Dp) Hx(Hq Hr Hu Hv Hw Ih Ii Ij Ik Il In Io Ip Iq Ir It Iu Iv Jh Jk Jm Jo Jp Js Jt Lu Ly Lz Mb Mc Md Mf Mg Mh Mi Mj Mk Mp Ms Mt Mv Mw Mx My Mz Nb Nc Nd Ne Nh Nj Nk Nl Nm Nq Nr Ns Nt Nu Nv Nx Ny Of Oy Oz Pa Pb Pd Pg Pz Qc Qd) Iq(Hq Hr Hu Hv Hw Ih Ii Ij Ik Il In Io Ip Ir It Iu Iv Jh Jk Jm Jo Jp Js Jt Lu Ly Lz Mb Mc Md Mf Mg Mh Mi Mj Mk Mp Ms Mt Mv Mw Mx My Mz Nb Nc Nd Ne Nh Nj Nk Nl Nm Nq Nr Ns Nt Nu Nv Nx Ny Of Oy Oz Pa Pb Pd Pg Pz Qc Qd) bM(aC aE aF aG aH aI aJ aK aL aN aO aP aQ aR aS aU aV aX aY aZ bB bC bE bF bG bH bI bL bN bP bS bU bV cA cB cC cD cE cF cG cH cI cJ cK cM cN cO cP cQ cR cS cU cV Cx cY cZ dA dB dD dE dF dG dH dJ dK dL dM Dp Fp Oi Oy) Iu(Hq Hr Hu Hv Hw Ih Ii Ij Ik Il In Io Ip Ir It Iv Jh Jk Jm Jo Jp Js Jt Lu Ly Lz Mb Mc Md Mf Mg Mh Mi Mj Mk Mp Ms Mt Mv Mw Mx My Mz Nb Nc Nd Ne Nh Nj Nk Nl Nm Nq Nr Ns Nt Nu Nv Nx Ny Of Oy Oz Pa Pb Pd Pg Pz Qc Qd) It(Hq Hr Hu Hv Hw Ih Ii Ij Ik Il In Ip Ir Iv Jh Jk Jm Jo Jp Js Jt Lu Ly Lz Mb Mc Md Mf Mg Mh Mi Mj Mk Mp Ms Mt Mv Mw Mx My Mz Nb Nc Nd Ne Nh Nj Nk Nl Nm Nq Nr Ns Nt Nu Nv Nx Ny Of Oy Oz Pa Pb Pd Pg Pz Qc Qd) Mc(Hq Hr Hu Hv Hw Ih Ii Ij Ik Il In Ip Ir Iv Jh Jk Jm Jo Jp Js Lu Ly Lz Mb Md Mf Mg Mh Mi Mj Mk Mp Ms Mt Mv Mw Mx My Mz Nb Nc Nd Ne Nh Nj Nk Nl Nm Nq Nr Ns Nt Nu Nv Nx Ny Of Oy Oz Pa Pb Pg Pz Qc Qd) Qc(Hq Hr Hu Hv Hw Ih Ii Ij Ik Il In Io Ip Ir Iv Jh Jk Jm Jo Jp Js Jt Lu Ly Lz Mb Md Mf Mg Mh Mi Mj Mk Mp Ms Mt Mv Mw Mx My Mz Nb Nc Nd Ne Nh Nj Nk Nl Nm Nq Nr Ns Nt Nu Nv Ny Of Oy Oz Pa Pb Pg Pz Qd) Lu(Hq Hr Hu Hv Hw Ih Ii Ij Ik Il In Ip Ir Iv Jh Jk Jm Jo Jp Js Jt Ly Lz Mb Md Mf Mg Mh Mi Mj Mk Mp Ms Mt Mv Mw Mx My Mz Nb Nc Nd Ne Nh Nj Nk Nl Nm Nq Nr Ns Nt Nu Nv Nx Ny Of Oz Pa Pb Pg Pz Qd) Mi(Hq Hr Hu Hv Hw Ih Ii Ij Ik Il In Ip Ir Iv Jh Jk Jm Jo Jp Js Jt Ly Lz Mb Md Mf Mg Mh Mj Mk Mp Ms Mt Mv Mw Mx My Mz Nb Nc Nd Ne Nh Nj Nk Nl Nm Nq Nr Ns Nt Nu Nv Nx Ny Of Oz Pa Pd Pg Pz Qd) Ip(Hq Hr Hu Hv Hw Ih Ii Ij Ik Il In Ir Iv Jh Jk Jm Jo Jp Js Jt Ly Lz Mb Md Mf Mg Mh Mj Mk Mp Ms Mt Mv Mw Mx My Mz Nb Nc Nd Ne Nh Nj Nk Nl Nm Nq Nr Ns Nt Nu Nv Nx Ny Of Oz Pa Pd Pg Pz Qd) aD(aE aG aH aI aJ aK aL aN aO aP aQ aR aS aU aV aX aY aZ bB bE bF bG bI bL bP bS bV cA cB cC cD cE cF cG cH cI cK cL cM cP cQ cR cS cU cV cW cY dB dC dD dE dF dG dH dK dL Ef FP tF) Iv(Hq Hr Hu Hv Hw Ih Ii Ij Ik Il In Jh Jk Jm Jo Jp Js Jt Ly Lz Mb Md Mf Mg Mh Mj Mk Mp Ms Mt Mv Mw Mx My Mz Nb Nc Nd Ne Nh Nj Nk Nl Nm Nq Nr Ns Nt Nu Nv Nx Ny Of Oz Pa Pd Pg Pz Qd) Pz(Hq Hr Hu Hv Hw Ih Ii Ij Ik Il In Ir Jh Jk Jm Jo Jp Js Jt Ly Lz Mb Md Mf Mg Mh Mj Mk Mp Ms Mt Mv Mw Mx My Mz Nb Nc Nd Ne Nh Nj Nk Nl Nm Nq Nr Nt Nu Nv Nx Ny Of Oz Pa Pb Pd Pg Qd) Jm(Hq Hr Hu Hv Hw Ih Ii Ij Ik Il In Ir Jh Jk Jo Jp Js Jt Ly Lz Mb Md Mf Mg Mh Mj Mk Mp Ms Mt Mv Mw Mx My Mz Nb Nc Nd Ne Nh Nj Nk Nl Nm Nq Nr Nt Nu Nv Nx Ny Of Oz Pa Pb Pg Qd) Mg(Hq Hr Hv Hw Ih Ii Ij Ik Il In Ir Jh Jk Jo Jp Js Jt Ly Lz Mb Md Mf Mh Mj Mk Mp Ms Mt Mv Mw Mx My Mz Nb Nc Nd Ne Nh Nj Nk Nl Nm Nq Nr Ns Nt Nu Nv Nx Ny Of Oz Pa Pb Pg Qd) Mk(Hq Hr Hv Hw Ih Ii Ij Ik Il In Ir Jh Jk Jo Jp Js Jt Ly Lz Mb Md Mf Mh Mj Ms Mt Mv Mw Mx My Mz Nb Nc Nd Ne Nh Nj Nk Nl Nm Nq Nr Ns Nt Nu Nv Nx Ny Of Oz Pa Pb Pd Pg Qd) Mv(Hq Hr Hv Hw Ih Ii Ij Ik Il In Ir Jh Jk Jo Jp Js Jt Ly Lz Mb Md Mf Mh Mj Mp Ms Mt Mw Mx My Mz Nb Nc Nd Ne Nh Nj

Mg(Et Is Lv Mu Oh Ok Om Pf Po) Jo(Et Hw Ir Iv Jt Na Oh Ok Po) Kr(Ao Bg Co dN Iz My Ng) Ok(Jh Ly Mu Nb Nx Oh Pc) Et(Is Jh Mu Mz Oh) Ch(bJ Dp Nf Us) Mu(Jh Lv Nv Pc) Uu(Ly Pk Sr Un) Wm(Hu Ly Mk) Nb(Hv Hw In) Lv(Jh Oh) Jl(Mk Nv) Kj(Kq Pk) dN(Hc Ly) PoNv MmMz} dN{Aj(Ad aF aM An aQ As aV AW Ax aZ bA Bc bF BG bM Bn BO bS bU bV bX cA Ch cM Cp Cq Cs Ct Cu CV cW Cx cZ DB Dc Dd dH Dl DK dL dM Dp eC Fp Fr Gp Hc Hu Hv Ib Ij Im Is Jd Ji Jn Jq Jr Jy Kf Kq Kr Kx Kz Lw Mq Mr Ms Mu Ni Nn Nr Ny Oe Oi Pd Pk Qt Rf Rh Sr Un) bR(aC aD aF aG aJ aK aL aM AN aO aP aQ aR aU aV aW AX aZ bB bC bF bG bH bI bJ bM bN BO bQ bS bV bW bZ cA cB cC cD cE cF cG Ch cl cJ cK cL cM cN CO cQ cR CS cU Cv cW cY cZ dD dE dF dG dH dJ DK dL Hc Jn Kx Nf Ni Oy Oz) Hc(aQ aV aW Ax BA Bc bJ bN BO bX cK cT Cv Cx cY dA Db Dc dl dJ dM Dp Fb Fr Gp Hu Ic Id Im In Is Ji Jl Jq Jr Jv Jy Ke Kg Ki Kq Kr Kx Ld Lu Lx Ly Mq Mr Ms Mu Nf Ni Nn Nr Oe Oh Oi Ow Pk Qg Ql Qv Qy Ra Ri Sr St Uh Un Ur Us) Ch(aM aV AW Ax aZ bA bF BG bM bO bU bV bX cA Cs Cv Cw dA DB Dc dE dl D

Figure 8 Continued

Mv Oh Pc Pf Qa Qe) Qa(Jh Mi Mm Nb Nf Ni Pe) Qe(Jh Jt Mi Nb Ni) Oh(Jh Jt Nb Ni) Pc(Jn Jr Jt Pe) Im(Mi Nb Pe) Pf(Jt Nb Ni) Mm(Jr Pe) MweC} Fr{Me(Fp Ih Im Is Jn Lj Lv Lx Mg Ms Mt Mv My Mz Ne Nh Ni Ns Of Og Oi Oy Pb Pc Pe Pf Po Qa Qe) Jr(Fp Hu Hv Hw Il Im Io Ir Is Iv Jn Lv Mg Mm Ms Mv Ne Nh Ni Nj Ns Oe Og Oh Pa Pc Pe Qa) Fp(Hu Hw Ik Im Ir Is Iv Jn Jo Jt Lv Mg Mm Ms My Mz Ni Ns Oe Oh Pb Pc Pz Qa) Oy(Im Ir Is Iv Jn Lx Mz Ni Oh Pf Po Qa Qe) My(Ir Iv Js Jt Ni Oh Om Pe Po Qa) Og(Is Iv Jn Mz Oh Om Pe Po Qa Qe) Oi(Im Ir Is Jn Lj Mz Oh Po Qa Qe) Ni(Im Is Jn Lj Oh Po Qa Qe) Hu(Im Ir Is Jn Po Qa) Is(Il Mm Ms Oe) Jn(Im Lv Mm Ms) Qa(Il Of) WmLj MsOh ImIr} Og{Om(Fp Im Ir Iv Jh Jn Lh Lj Lx Ly Me Mg Mi Ml Mr Ms Mt My Mz Ne Nf Nn Of Oy Pa Pc Pe Po Qd) Po(Im Ir Iv Jg Jn Jr Jt Lh Lv Me Mm Mr Mt Mz Nb Nf Ni Nn Nt Oh Oy Pc Pe Qa Qe) Is(Fp Im Io Jg Jn Jr Jt Lh Lx Me Mr Mt Mz Nb Nf Ni Oh Oi Pe Pf Qa Qe Wm) Nn(Fp Ir Iv Jn Jr Jt Lh Lv Lx Mr Mz Nb Ni Oi Pe Qa Qe) Lx(Im Jn Jr Jt Me Ni Qa Qe) Jr(Jg Lh Mm Nb Pc Pe Wm) Oh(Iv Jt Lh Me Nb Ni Pe) Qc(Jg Mz Nf Ni Pc Pe) Qa(Jg Nb Nf Pc Pe) Im(Lh Nb Pe) Pc(Lh Pe) SrJv} Ni{Po(Hr Hu Im In Is Jn Jo Jr Lv Ly Me Mg Mm Mn Ms Mt My Ne Nn Ns Of Oh Oi Oy Pa Pb Pc Pe Qa Qe) Nn(Fp Hu Im Ir Is Iv Jn Jo Jr Lv Lx Me Mi Mm Mr Ms Ne Ns Oi Oy Pa Pb Pe Pf Qa Qe) Lx(Hq Hu Im Is Jr Ly Of Oh Oy Pb Pc Qa Qe) Is(Im Jr Li Ms Oh Oi Pc Pf Qa) Jr(Im Oh Om Pc Pe Pf Qa Qe) Oh(Im Me Mm Ms Oi Om Pc) Pc(Im Jn Pe Pf Qa Qe) Mm(Im Jn Pe Qa) Im(Mt Pe) Jd(Aj Ch) JiKr} Oi{Nn(Hu Im Ir Iv Jt Lh Lj Lv Lx Me Mr Ms Mz Ne Nh Ns Nt Pa Pc Po Qa Qd Qe) Oh(Fp Ir Is Jg Jn Jr Jt Lh Lv Me Mz Nb Nt Om Pc Pe Po Qa Qe) Is(Fp Jn Jr Lh Li Lx Mm Mt Mz Pc Pe Pf Po Qa) Po(Fp Ir Jn Jr Mt Mz Pc Qa Qe) Qa(Fp Jg Lx Mt Om Pc) Pc(Jn Jr Pe Qe) Om(Fp Jr Qe) ChJd MmJr MzQe} Mm{Jr(Fp Hw Im In Io Ir Is Iv Jn Jt Lh Lu Lv Lx Mf Mr Ms Mz Na Nb Nc Nf Nn Ns Nt Oh Om Pa Pc Pe Pf Po Qa Qe) Is(Fp Il Im In Io Ir Jn Lv Lx Me Mr Ms My Mz Nf Nn Ns Oe Oh Pb Pc Pf Po Qa) Me(Im Jn Lv Lx Mt Mz Nn Oh Pe Pf Po Qa) Jn(Fp Im Io Lv Po) LvMz NbOy UnUs} Kj{Ad(Ba dI Dp Hu Jd Po Qc Qy Rf Sr Ua Un) Id(Ba Dp cC Hu Jd Pd Qe Qy Rf Sr Uf Un) Sr(Cw Dp Ij Om Pi Pk Qg Ri Tv Up) Un(Cw Fn Ij Jv Kr Ms Pi Ra Up) Pi(Ba bJ Hu Jd Pd Rf Uf) Cw(bJ Hu Jd Qy Rf Ua) Pk(eC Hu Nn Po Qe Rf) Ij(bJ dI Dp Hu Pd) Up(Ba Jd Rf) bJ(Dc In) QaQc JiKr} Oy{Lx(Hw Ij Ir Is Iv Jg Jn Jo Jr Jt Li Lv Ly Me Nf Nn Pc Qa Qe) Po(Ir Is Jg Jn Jr Lv Mz Nn Om Pc Pe) Nb(Im Is Jg Jr Oh Pc Pf Qa Qe) Om(aW bJ Jr Mi Oh Pe Pf Qa Qe) Nn(Is Jr Me) Un(aW Ms) Pe(Oh Pc) JiKr} Ji{Kr(AF Aj Ao aW Ax bJ Bn bP Ch cl cN Cs Cx cZ De dI dM Dp Ed Hb Hc Ii Ir Iu Iv Kg Ki Kx Ld Lu Ms Nn Oh Ow Qg Ql Qy Rh Ri Us Vo Wm) Uu(Ba bJ dI Qg) Us(cZ Jv Qg) Dp(aW Kg) AjbJ HcaW} Nn{Me(Fp Hu Ii Im In Is Jn Jo Jr Lv Lx Mr Ms My Ns Pa Pe) Ms(Fp Is Iv Jn Jr Lh Nb Om Pe Po) Is(Fp Hu Ii Il Io Ir My Ns Oe) Jr(Ir Lv Ns Oe) Jo(Iv Jt) MyNb HuOm} Uu{Sr(Aj aK aV Bg BO Cv dA dJ Dk Dp eC Ez Hu Jv Jy Kx Nc Nl Qy Ri Uf Un) Un(bJ eC Hb Jy Kr Lu Ms Ow Qv Qy Rf Rh Us) Ba(Ke Vt) FnKe} Lx{Hu(Ir Is Jh Jn Jr Jt Me Om Qa) Hq(Ir Is Jn Jr Li Me Mi Qa) Me(Im Jr Of Oh Pc Pg) Qa(Il Of Pb) My(Jg Om) Jn(Js Of) WmLy NsMh IHs JrPc OfOm} Po{Is(Il In Io Jo Ms My Oe Pb Pc) Jn(Im Jo Js Lv Pc) My(Jg Nb Om) Jo(Ir Iv Jt) Pc(Jr Me Ms) Om(Hu Ms) MiHq ImJr PbPe} Om{Hu(Fp Is Jr Me Oh Pf Qa Qe) Ms(Fp Is Jr Oh Qa Qe) Qa(Jo Mg My Of) My(Jr Nb) AjDp ChbJ MeOh} Aj{Sr(Ef Fp Hu Jd Jv Kx Nf Qy tF) bJ(Ad Id Ke Un) Dp(Id Ke) NfUn QybA} Pc{Jr(Im Ir Is Me Ns Pe) Me(Is Oh Pf) Is(Fp Ms) NsQa} Un{Us(bW Ch Co cC Jv Oz Uf) DpKg EdFw JvKr} Ch{Jd(Ly Nf) Qy(bA cT) bJ(Mw Ny) FatF} My{Jg(Is Jr Nb) Mw(Is Nb) HuJh} Dp{Sr(Kg Qv Ur) KeKg} Qe{Qc(Jn Jr) IHs} Qa{Qg(Kr Us)} Oh{MsNb JoJt} Pk{dM(Hc Oz)} IoIsJr

Unconstrained panels with 3 analytes, where 3.2E-7 >= 'model p-value' > 1.0E-7. Contains 17,762 panels of 7,079,861 total panels evaluated. : dN{Hc(aC AD aE AF aH aI aJ aK AL aM AN AO AP AR AS aU Aw aZ BB bC bE bF BG bH bI bL bM Bn bP bQ bS bU bV bW bZ cA cB cC cD cE cF cH cI cL cM cN CO Cp CQ CS Ct CU cV cW cX cZ dB Dd DE dF DG dH Di DK DL Ed Et Ez Fa Fn Fw Fy Ha Hb Hf Hr Hv Hw Ib Ih Ii Ij Ik Il Io Iq Ir It Iu Iv Iz Jf Jg Jk Jo Jp Js Ju Kc Kd Kf Kj Kk Kn Ko Kp Ks Ky Kz Lh Li Lj Lv Lz Ma Mb Mc Md Me Mf Mh Ml Mm Mn Mp Mt Mw Mx My Mz Na Nb Nc Ne Ng Nh Nj Nk Nl Nm Nq Nt Nu Nv Nx Ny Oa Of Og Om Ou Oy Oz Pc Pd Pe Pf Pg Pi Po Qa Qb Qc Qd Qe Qm Qn Qt Qw Qx Qz Rb Rc Ss Tz Ua Uf Ug Uk Ul Um Uo Ut Uu Vp Vt Wm) No(aC aG aH aJ aL AN aP aQ aR aS Aw AX aY aZ BA bB BC bE bH bI bL Bn Bo bP bQ bU bV bW bZ cB cC cD cE cF cH cI cJ cK cL cM cN cO cP cQ cR CS CT cU Cv CW cX cY DB dC Dd dE Di dJ DK eC Et Fa Fn Gl Gp Ha Hb Hr Hw Hx Ij Ik Il Im In Ip Iq Is It Iu Iv Jd Jf Ji Jj Jl Jm Jn Jq Jr Js Kc Kn Ld Lj Lv Lw Lz Ma Mb Mc Md Mf Mh Mi Mk Mm Mn Mp Mq Mt Mu Mv Mw Na Nb Ne Nh Nn Nr Ns Nt Nu Nw Ny Oa Oh Om Ou Ow Pc Pd Pf Pg Pj Pz Qa Qb Qd Qe Qg Ql Qn Qv Qw Ra Rf Rg Rm Ss Ua Ur Ut Uv Vo Tj) bN(aC aD aE aG aH aI AL aN AO aP aQ AR AS Aw AX aY aZ Ba bB bC bE bF bG bH bI bL bM bP bQ bS bU bX bZ cB cC cD cE cF cG cH cI cJ cL cM cO cP CQ cR CS Ct CU cV cW CX cZ DB dC dD dE dF dG DI DK dL Ef Et Fr Hu Ih Im In Io Is It Iv Jd Je Jl Jy Kg Ki Kq Kr Kz Lu Lv Lx Mb Ml Mm Mq Mr Mu Mw My Nc Ng Ni Nl Nn Nr Oe Og Om On Ow Pc Pd Pe Pf Pk Po Qa Qc Qd Qe Qg Ql Rh Ri Uh Un Us Uu) Aj(aC aD aE Af aG aH aI aJ aK AL aN AO AP AR aS aU aX aY BB bC bE bH bI bL bP bQ bW bZ cB cC cD cE cF cG cH cI cJ cK cL cN CO cP cQ cR cS cU cX cY dC dD DE dF DG dJ DI Ez fP Hf Hq Hw Hx Id Ih Ii Il In Ir It Iv Jk Jl Jt Ke Ki Lh Lu Lx Ma Md Mg Ml Mt Mv Mw Mz Na Nb Nc Nj Nm Nq Nt Nw Og Om On Ow Oy Oz Pa Pb Pc Pe Pf Pg Pi Po Qa Qc Qd Qg Ql Qn Qy Ra Ua Ut Vt) Ch(aC AD aE AF aG aH aI aJ aK AL AN AO AP aQ AR AS aU aX aY BB BC bE bH bI bL Bn bP bQ bS bW bZ cB cC cD cE cF cG cH cI cJ cK cL cM cN CO CP CQ cR cS Ct CU cV cW CX cY cZ dC DD De dF DG dH Di dJ Dl Fn Fp Hv Ib Ij Im Iv Jh Ji Jl Jq Kf Ki Lu Lx Mv Nc Nq Nw Oe Og Oi Om On Ow Oy Oz Pd Pe Pk Po Ql Rh Uh Un) Me(AD AF aJ aK Al aM An aO Ap Ar As Aw Ba Bb Bc bH bI bJ bM Bn bP bR bS bV bW bX cA cC cD cF cK cN Cp Cq cS Cu Cw Cx cY Db Dc Dd DE Dg dH Di Dk Dl Dp fP Fr Gp Hr Ih Ii Ik Im Io Ir Is Iu Jd Je Jl Jp Jq Jr Jv Ki Kq Kr Ky Ld Lj Lu Lx Ly Lz Mg Mh Ml Mm Mq Mr Ms Mu Mv My Nc Ng Ni Nn Ny Oe Of Og Oh Oi On Pb Pc Pe Pk Qa Qc Qe Qg Ql Rf Rh Ri) Kr(Ad Af aJ Al An Ao Ap Ar As aV Aw aX bA Bb Bc BG bM Bn Bo bW bX cK cM cN Co Cp Cq Ct Cu Cw Cx Db Dc Dd DE Dg Dl Dl dM eC Et Ez Fa fP Fr Gl Id Ih It Iv Je Jp Jq Js Jv Ke Kg Kj Kk Ky Ld Lj Lu Ly Lz Ma Ml Mp Mw Nq Nr Nt Nv Nx Oa Oe Og Oi Om Pa Pc Pd Pf Pj Po Qb Qd Qn Qv Qw Qy Qz Rc Rg Ri Uf Ur Us tF) Nf(aF aJ aK Al aM An AO aU Aw Ax Ba BG bH bM bP bS bU bV bW bX cB cI cM cN Cq CS Ct cV cY cZ Dc De dH Di dJ dL eC Ed Fn Fr Fw Ha Hq Hu Ih Io Ir Is Iu Jd Je Jl Jr Ju Jy Ke Kq Kx Lu Lx Ly Mb Mh Mj Ml Mm Mq Mr Mt Mu My Nc Nd Ne Ng Nj Nm Nr Nt Oe Of Oz Pk Qc Qd Ql Sr St Ug Uk Um Us Uu Uv tF) eC(aD AF aK Al An Ao aQ Ar aU aV AW AX BA Bb BC Bg bJ Bn Bo bR bS bW bX cA cB cC cF cI cM cN CP Cs CT cU cV Cx cY Db Dd DE dH Di dJ DK DL Ed Gp Hf Hu Hv Hw Id In Jd Je Jn Jo Jq Jr Kd Kg Ki Kk Kn Kx Lw Ly Mg Mh Na Ng Nw Ny Og Oy Pc Pi Qd Qy Rf Ri Us Uu Vp) bO(AD Af aK AL aM An Ao aP Ar As aV AW aX aZ BB Bc bF Bg bJ bM Bn bQ bU bV bW bX cH cK cM cN Co Cp CQ cR cS Ct Cu CW Cx cY dB dD DE Dg dH DI dJ Dl Dp Ed Fn Gl Ij Jo Jq Jy Ke Ki Kz Lu Lw Lx Ma Ml Mn Nc Nv Ny Oe Og Oi On Ow Pc Pd Pe Pf Pk Po Qa Qb Qd St Ur Uu) cT(aC aE aG aH aI aL aN Ao aP aQ aR aX aY aZ bA bB bC bE bF bG bH bI bL bM Bo bP bQ bS bU bV bW cC cD cE cF cG cH cI cJ cL cM cN cO cP cQ cR Ct cU cW cX cZ dB DC dD dG dI dK dL Ef Fn Hv Jo Jv Kg Ki Kx Kz Ms My Ng Ni Oz Pb Pc Pk Rf Us Uu tF) Dp(aJ Ao AW Ax BA BG bJ bR bV bX cA cK cN Cs cW Cx Dc dE dH dI dK dM Fa Fn Fr Hv Id Ik In Iu Jd Je Jf Jl Jn Jr Jv Ke Ki Kj Ky Kz Mg Ml Mq Mr Mu Nc Ni Nj Nl Nn Nr Ny Oe Og Ow Oy Oz Pc Pk Pz Qd Ql Qn Rc Ri St Ug Uh Um Un Us Uu) Ly(AF Al An Ao Ap Ar aV AW Ax Ba Bb Bc Bg bJ Bn bR bS bV bW cA cN Cq Cs Ct Cu Cw Cx Dc Dd De Dg Di dJ Dk Ed Fa FP Gp In Is Jl Jq Jr Jv Ke Kk Kz Ld Lu Lz Ml Mm Ms Nd Ne Ng Ni Nt Oe Oi Ow Oz Pd Pe Qe Ql Qv Qy Rb Sr Uf Ug Un tF) bR(Ad aE Af aH aI Al Ao Ap Ar AS Aw aY Ba Bb Bc bE Bg bL Bn bP bU cH CP Cq Ct Cu cV Cw CX DB DC Dd De Dg Di Dl FP Fr Gp Im Is Jd Ji Jo Jq Jr Kg Ki Kj Kz Lu Lw Ma Mq Mr Ms Mu Nc

Figure 8 Continued

My) Kr(bW Uf} AjbJ DpUr MeOh QcJn PbPe} Kj{Ad(aK cZ dA eC Fb Fn Fy Jk Jn Kx Ma Nr Oh Ow Pd Pe Pf Pk Ql Ri Uf) Id(bA cZ dA dl Ez
Fa Fn Fy Jk Jn Kx Ma Nf Nr Oh Pe Ql Ua) Cw(Ba dA dl Dp Fn Jk Pd Qe Ql Uf) Ij(Ba Fn Jd Jk Mm Qe Qg Rf Uf) Pi(dl eC Fy Qe Qy Ua)
Pk(Ba bJ Jd Kx Nr Uf) Up(Hu Pd Qe Uf) Kr(Hu Ke Rf) Dc(Dp Qy) Nf(Kn Kp) bJ(Kd Kn) dl(In Ra) MwTv NaJd} Oh{Ni(Fp Ir Iv Jg Jn Jp Jt Lh
Li Lv Ly Mi Mn Mr Mt Mz Ne Pa Pb Pe Pf Qe) Me(Im In Jg Jn Jo Jp Lh Lu Lv Mi Mn Ms Mt Mz Nb Ng Pa Pe Pf) Oi(Hw Im Iv Jp Lu Mr Ms
Mt Ne Nh Qd) Ms(Ir Iv Jg Jt Lh Lv Pe) Mm(Fp Ir Iv Jn Lv) Ng(Iv Mi Nm Pe Qe) Og(Ir Jg Mr Mz) Lv(Ir Iv Jn) IrPc JnJs} Mm{Jn(Lh Lu Mr Nf
Ng Og Oi Pa Pc Pe Pf Qe) Pe(Fp Im Io Ir Lv Mz Og Oy Pa Pc) Fp(Ir Iv Lh Lv Mz Ni Oi) Mc(Lh Li Mr Pa Pc Qe) Lv(Im Ir Iv Js Mt) Ng(Iv Mv
Nb Pf Qe) Ni(Mt Mz Pf Qh Qe) Og(Iv Lh Mz Nb Qe) Mz(Im Qe) Imlv IrPf} Ng{Qe(Ir Jn Jo Ma Mt Mv Mz Nf Pc Pf) Pf(Im Ir Iv Jh Lv Me Nt
Pc) Lh(Jh Jk Jn Ma Mw Ni) Im(Jn Jt Mz Ni Pc) Pc(Nb Nt Nv Qd) Ni(Jk Li Pe) Ma(Jt Nb) BaUu MvNb JdRh JhPe QycT} Im{Ni(Jn Lh Li Mi
Mr Mz Pa Pf Qe) Pe(Io Jn Lv Mt Mz Oi Oy Pc) Mz(Io Lv Me Og Oi Pc) Jn(Lv Og Pa Pc) Me(Mt Pc Pf) Og(Iv Mr) LvMt LhOi} Qe{Og(Ir Iv Jn
Jt Lh Mi Mr Mt Nb Wm) Ni(Aj Jn Li Mt Mz Oi Pe Pf) Oi(Fp Jn Lh Mt Pe Pf) Pc(Ir Jn Me Ms Mz) Qc(Mt Mz) llPe} Ch{Jd(aW BA cT dl Ed Hu
Jv Kr Kx Ms Nc Us) Hu(aD cN Kx Ni) Mw(aW bX eC) bJ(Jh Ut)} Pc{Pe(Fp Il Ir Jn Lv Me Ms Nk Ns Pa) Jn(Fp Lh Lv Me Og) Og(Fp Iv Jt Nb)
Fp(Ir Oi)} Oy{Nb(Fp Li Mv Pe) Pf(Ir Lh Lv Ni) Ke(aW bJ cZ) dM(Nr Pk) HuJh NybJ} Uu{Ba(Cv Dc Jy Mg Ni Oi Pk) Jd(Kc Ni Pk) Ke(bJ Kr)
CvJn} Og{Jn(Jg Lh Nb Pe Wm) Fp(Lh Nb Pe) Pe(Jg Ni) HuJh lvPf} Ni{Aj(Hu Jk) Pf(Jn Me) TnHc PbPe PkdM bVfP} Oi{Fp(aJ Jg Lh Mz Pe)
bV(Dp fP) PkdM} Ke{Hc(aW eC Rh) Dp(Ao Ur) JvbX UsbJ} My{Mw(aW bJ eC Pa Pe) JgPe} bA{aM(bJ bO) HcRi aDbJ bRdA} Aj{bJ(Dc
Kn) AdDp BaVt} Cv{Nf(Jv Qn) DpQv KzQn} Co{Fy(Jd Nf) UsPe} Dp{Vt(Qv Ur)} Jo{Jt(Fp Pf)} WmLyPe FabVfP MlJvdl UfUsPi PkdMeC Unconstrained panels with 2 analytes, where 1.0E-7 >= 'model p-value' > 0. Contains 444 panels of 61,235 total panels evaluated. : aA(aC aD aG
aM aW bA bC bJ bM bP bR bW cN cT cW cX dA dC dl dM dN Et Fp Fr Hq Hr Hu Hv Hw Hx Ih Ii Ij Ik Il Im In Io Ip Iq Ir Is It Iu Iv Jg Jh Ji Jj
Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw
Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc
Pd Pe Pf Pg Po Pz Qa Qb Qc Qd Qe Wm) Ji(Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr
Js Jt Kr Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb
Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz
Qa Qb Qc Qd Qe Wm) Nw(Et Fp Hv Hw Im Ir Is Iv Jj Jl Jn Jo Jq Jr Jt Lv Lw Me Mq Ms Mv Ng Na Ng Ni No Og Oh Oi Ok Oy Pe Qa) Jj(Et
Fp Fr Im Is Jk Jl Jn Jq Jr Jt Lh Li Lx Mq Mu Nn No Nt Oh Ok Om On Pd Pe Pf Po Qa Qe) No(dN Et Io Is Jl Jn Jq Jr Lu Lv Lw Me Mm Mq Ms
Mu Ng Ni Nn Oi Ok Om On Pc Qa Wm) On(Fp Hu Jq Jr Lj Lw Me Ms Mv Mw My Ng Ni Nq Ns Of Og Oi Oy Qa) Ok(Fp Im Is Jl Jq Jr Lw Mu
Ng Nn Oh Pc Po Qa) dN(Aj aV bA bN bR cA Ch cT dA dM Hc) Jl(Et Jn Jq Jr Lw Me Ng Ni Og Oi) Jq(Et Fp Fr Mq Mu Pf Po Qa Qe) Mu(Et Is
Jn Jr Me Ng Og) Et(Is Jr Me Oh Qa) Ng(Fr Jg Nn Om Po) Mq(Fr Jn Jr Nn) Lw(Is Jr Uu) Jr(Fr Mm) Kq(Kj Uu) PoNi Unconstrained panels with 2 analytes, where 1.0E-6 >= 'model p-value' > 1.0E-7. Contains 722 panels of 61,235 total panels evaluated. : dN(aC
aD aE AF aG aH al aJ aK AL aM AN AO AP aQ AR AS aU AW AX aY aZ Ba bB BC bE bF BG bH bl bJ bL bM BO bP bQ bS bU bV bW bX
bZ cB cC cD cE cF cG cH cl cJ cK cL cM cN CO cP CQ cR CS Ct cU CV cW CX cY cZ DB DC dD dE dF DG dH Dl dJ DK dL Dp eC FP Fr
Gp Hv Im Is Jd Ji Jj Jn Jo Jq Jr Jy Kg Ki Kq Kr Kx Kz Lu Lw Ly Me Ml Mq Mr Ms Mu Nc Nf Ni Nr Nw Oe Og Oi Oy Oz Pk Qg Rf Rh Sr Un
Uu tF) No(bO Ch Co Dp Fp Fr Hc Hq Hr Hu Hv Hw Hx Ih Ii Ij Ik Il Im In Ip Iq Ir It Iu Iv Iz Jg Jh Jk Jm Jo Jp Js Jt Kl Kr Lh Li Lj Lx Ly Lz Ma
Mb Mc Md Mf Mg Mh Mi Mj Mk Ml Mn Mp Mr Mt Mv Mw Mx My Mz Na Nb Nc Nd Ne Nf Nh Nj Nk Nl Nm Nq Nr Ns Nt Nu Nv Nx Ny Oe
Of Og Oh Oy Oz Pa Pb Pd Pe Pf Pg Po Pz Qb Qc Qd Qe Us Uu) Nw(Fr Hq Hr Hu Hx Ih Ii Ij Ik Il In Io Jh Jk Jm Js Lh Li Lj Lu Lx Ly Lz Ma
Mb Mc Md Mf Mg Mh Mi Mj Ml Mm Mn Mp Mr Mt Mv Mw Mx Mz Nc Nd Ne Nf Nh Nj Nk Nl Nm Nn Nq Ns Nt Nu Nv Oe Of Om On Oz
Pa Pb Pc Pd Pf Pg Po Pz Qb Qc Qd Qe) aA(aE aF aH al aJ aK aL aN aO aP aQ aR aS aU aV aX aY aZ bB bE bF bG bH bl bL bN bO bQ bS bU
bV bX bZ cA cB cC cD cE cF cG cH cl cJ cK cL cM cO cP cQ cR cS cU cV cY cZ dB dD dE dF dG dH dJ dK dL Dp) Ok(Et Fr Hu In Io Jn
Jo Li Lj Lu Lv Lx Ly Me Mg Ml Mm Mn Mp Mq Mr Ms Mt Mw Mx My Mz Ne Nf Nh Ni Ns Of Og Oi Om On Oy Oz Pb Pe Pf Qb Qd Qe)
On(Et Hq Ii Il Im Ir Is Iv Jh Jk Jl Jn Jo Js Lv Mg Mk Mm Mq Mu Mz Na Ne Nh Nv Oe Oh Pb Pe Pf Po Qd Qe) Jl(Fp Hu Hv Hw Il Im Io Ir Is Js
Jt Lv Mm Mq Ms Mt Mu Mz Na Nf Nk Nn Ns Oe Oh Om Oy Pc Pf Po Qa) Et(Fp Fr Im Io Ir Iv Jn Js Lh Lu Lv Lw Lx Mq Mr Mt Mz Nf Ng Ni
Nn Oi Om Pc Pe Pf Po Qc) Jj(Dp Hw Ii Ij Ir Iv Jg Jm Jo Js Lv Lw Me Mn Mr Mt Mw Mz Nb Nf Nh Ni Nv Ny Pg Qb Qd) Is(Fp Fr Im Io Jn Jq
Jr Lx Me Mm Mq Ms Mz Ng Ni Nn Og Oh Oi Om Pc Pf Po Qa) Mu(Fp Hu Im Ir Iv Jt Lj Lv Lw Mm Mq Mz Ni Oh Oi Oy Pe Po Qa Qe) Po(Im
Ir Iv Jn Jr Jt Lv Lw Me Mm Mq Ms Mz Og Oi Oy Qa) Jq(Im Jn Jr Lh Li Lx Mm Mr Nn Og Oh Pa Pc Pe Qb Wm) Qa(Fr Jn Jr Lw Lx Mm Mq
Ng Ni Nn Og Oi Om Pc Pe) Mq(Im Js Lw Lx Mt Mz Ng Ns Oh Om Pc Pf Qe) Jr(Im Ir Lh Lv Lx Ni Nn Oh Om Pc Pe Pf Qe) Nn(Fp Ir Iv Jn Lv
Me Ms Ni Og Oi) Lw(Fp Fr Im Jn Lh Pe Qe) Fr(Fp Ir Jn Me Ni) Jn(Im Mm Pc Qe) Oh(Me Ni Oi Om) Lx(Hq Ng Oy) Om(Hu Ms Og) Aj(Kq Sr)
Ni(Pf Qe) Un(Us Uu) MePf MzIm JiUs SrUu KqOy PcPe Unconstrained panels with 2 analytes, where 1.0E-5 >= 'model p-value' > 1.0E-6. Contains 1,308 panels of 61,235 total panels evaluated. :
dN(Ad Bb Bn Cp Cu Cw Dd De Dl Ed Ef Et Ez Fa Fb Fn Fw Fy Gl Ha Hb Hf Hq Hr Hu Hw Hx Ib Ic Id Ih Ii Ij Ik Il In Io Ip Iq Ir It Iu Iv Iz Jc Jf
Jg Jh Jk Jl Jm Jp Js Jt Ju Jv Kc Kd Ke Kf Kj Kk Kl Kn Ko Kp Ks Ky Ld Lh Li Lj Lv Lx Lz Ma Mb Mc Md Mf Mg Mh Mi Mj Mk Mm Mn Mp
Mt Mv Mw Mx My Mz Na Nb Nd Ne Ng Nh Nj Nk Nl Nm Nn Nq Ns Nt Nu Nv Nx Ny Oa Of Oh Ok Om On Or Ou Ow Pa Pb Pc Pd Pe Pf Pg
Ph Pi Pj Po Pz Qa Qb Qc Qd Qe Qh Ql Qm Qn Qt Qu Qv Qw Qx Qy Qz Ra Rb Rc Rg Ri Rm St Tz Ua Ub Uc Ud Ue Uf Ug Uh Uk Ul Um Uo
Up Ur Us Ut Uv Vo Vp Vt Wm Tj) Po(Fp Fr Hq Hr Hu Hv Hw Ih Ii Ij Ik Il In Io Ip Iq Iu Jg Jm Jo Jp Js Lh Li Lj Lu Lx Ly Ma Mc Mf Mg Mh
Mi Mj Ml Mn Mp Mr Mt Mv Mw Mx My Na Nb Nc Nd Ne Nf Nh Nj Nk Nl Nm Nn Nq Nr Ns Nt Nu Ny Oe Of Oh Om Oz Pa Pb Pc Pd Pe Pf
Pz Qb Qc Qd Qe) Qa(Fp Hr Hu Hv Hw Ih Ii Ij Ik Il Im In Io Iq Ir It Iu Iv Jg Jm Jo Jp Js Jt Kj Lh Li Lj Lu Lv Ly Lz Ma Me Mg Mh Mi Mj Ml
Mn Mp Mr Ms Mt Mv Mw Mx My Mz Na Nb Nc Ne Nf Nh Nk Nl Nm Ns Nt Nx Ny Oe Oh Oy Oz Pa Pb Pd Pf Pz Qb Qc Qe) Is(Hr Hu Hv Hw
Ih Ii Ij Ik Il In Ip Iq Ir Iu Iv Jg Jm Jo Jp Js Jt Lh Li Lj Lu Lv Ly Lz Ma Mc Md Mg Mh Mi Mj Ml Mn Mp Mr Mt Mv Mw Mx My Na Nb Nc Ne
Nf Nh Nj Nk Nl Nm Ns Nt Nu Nv Ny Oe Of Oy Oz Pa Pb Pd Pe Pg Pz Qb Qc Qd Qe) JI(Fr Hq Hr Hx Ih Ii Ij Ik In Ip Iq It Iu Iv Jg Jh Jk Jm Jo
Jp Lh Li Lj Lu Lx Ly Lz Ma Mb Mc Md Mf Mg Mh Mi Mj Mk Ml Mn Mp Mr Mv Mw Mx My Nb Nc Nd Nc Nh Nj Nl Nm Nq Nr Nt Nu Nv
Nx Ny Of Oz Pa Pb Pd Pe Pg Pz Qb Qc Qd Qe Wm) Jr(Fp Hr Hu Hv Hw Ij Ik Il In Io Ip Iv Jg Jk Jn Jo Jp Jt Li Lj Lu Ly Ma Mc Me Mh Mi Mj
Ml Mn Mp Mr Ms Mt Mv Mw Mx My Mz Na Nb Nc Ne Nf Ng Nh Nj Nk Nl Nm Ns Nt Nu Nv Nx Ny Oe Og Oi Oy Oz Pa Pb Pd Pg Qb Qd
Wm) On(Bg Ch Co Fr Hr Hv Hw Hx Ih Ij Ik In Io Ip Iq It Iu Jg Jm Jp Jt Lh Li Lu Lx Ly Lz Ma Mb Mc Md Mf Mh Mi Mj Ml Mn Mp Mr Mt
Mx Nb Nc Nd Nf Nj Nk Nl Nm Nn Nr Nt Nu Nx Ny Om Oz Pa Pc Pd Pg Pz Qb Qc Uu Wm) Et(Hq Hr Hu Hv Hw Ih Ii Ij Il In It Jg Jk Jo Jt Li
Lj Ly Lz Ma Mb Mc Md Mg Mh Mi Mj Ml Mm Mn Mp Ms Mv Mw Mx My Na Nb Nc Ne Nh Nj Nl Nm Ns Nt Nu Ny Oe Of Og Oy Oz Pa Pb
Pd Pg Pz Qb Qd) Jq(Aj bJ Dp Hc Ih Ik Io Ir Iv Jg Jk Jp Jt Kj Lj Lu Lv Lw Lz Ma Md Me Mh Mi Mj Ml Mn Mp Ms Mt Mv Mw Mx Mz Na Nb

Dp(Ao Ch Co Hq Qv) Et(Jr Lu Me Ms Nf) Io(Is Jl Jr Me Mm) Kj(Cw Id Kq Pi Pk) Om(Hu Ms My Og Oy) Fr(Me My Oy) Og(Jl Nf Wm)
Ch(bO Nf) Mm(Jr Me) Jn(Js Lj) UsdM UubO} On{Jq(Fp Hq Ii Im Jh Jk Jo Jr Lj Me Mm Mq Ms Mu Mv Mw Nb Ns Nv Oh Om Pb Qa) Of(Et Il
Im Ir Jt Lv Lw Md Ml Mq Ms Mu Mv Mz Na Nf Ns Oe Om Pe Po) Me(Hq Ii Il Im Jh Jk Jo Lj Lw Mm Mu Nq Ns Oh Pb) Mw(Fp Hq Im Io Jo
Jr Lw Mq Mu Ni Nn Ns Oe Og Oi) Og(Jh Jl Jn Ms Mv Nf Ni Nn Nq Oh Pc Pg Po Qe) Fp(Hq Ii Ik Il Jk Jo Lw Mg Mv Nq Ns Oi Pb) Ni(Hq Im
Jh Jo Jr Lj Ms Mv Nb Oh Pb Qa) Lw(Il Im Jk Jn Jr Lj Mv Ns Oe Pb) Ms(Et Is Jn Jr Lj Ly Pb Po Qa) Mv(Im Io Jo Jr Lj Nv Oh Pb Qa) Oi(Im Is
Jn Jr Lj Nq Oh Qa) Ns(Im Jr Lj Ly Mg Mq Qa) Il(Hq Im Is Jr Lj Qa Qe) Oe(Hq Im Is Jr Lj Oh Qa) Jk(Im Mu Qa) Mq(Hq Mg) ChKr WmaA
NqPc} Ng{Jg(Hr Hv Hx Ij Im Io Iv Jh Jo Js Li Lv Lw Md Ml Mp Mt Mv Mx Mz Na Ne Nh Nr Nv Pa Pg Qb) Nn(Fp Im Ir Is Iv Jh Jn Jq Jr Jt Lh
Lu Lv Lw Lx Me Mi Mr Nb Oi Pe Po Qa Qe) Ok(Et Fp Im Is Jh Jk Jl Jq Jr Lw Lx Ma Mm Mp Mv Mw Nf Ni Oh Pf Qa Qb Qe) Om(Et Im Is Jn
Lh Li Lu Me Mi Mm Mr Mv Mw Nb Nf Ni Nt Pa Pe Qb) Jl(Et Jh Jn Jr Lx Me Mm Mq Mt Nf Ni Oh Pc Po) Mq(Et Is Jq Jr Lx Mz Oh Pc Pf Po
Qa) Et(Is Jk Jq Jr Lx Oh Pc Po Qa) Mu(Fp Ij Ly Ml Mv Mz Ni Qb) Lx(Is Jq Me Ni Pc Qa Qe) Po(Is Jq Lw Mm Nb Pc) Is(Lw Mm Pc) Qe(Jq
Pc) WmFr QaPc} Mu{Et(Hu Ir Is Iv Jn Jo Jq Jr Lj Lw Mg Ms My Ni Ns Of Og Oi Qa) Jq(Fp Hu Is Jl Jr Lj Md Me Mm Ms Of Oi Ok Oy Pc Qa
Qe) Og(Ir Iv Jl Jn Jr Jt Lh Lw Me Mq Mr Mz Ok Pe Po Qa Qe) Oy(dN Is Jl Jr Lx Mi Mq Ok Pf Po Qa) Me(Hu Jl Jn Jr Lj Lw Mm Oh Ok) Is(Hu
Il Lw Mm Ms My Oe Oi) Ok(Jo Jr Lw Ly Mg Ms My Of) Jr(Lw Mm Mq Ms Ni Oi) Oi(Fp Jn Lj Oh Qa) Mq(Hu Jn) LwJn MyNb HuOm SrUu}
aA{dN(Aj Ch Cx eC Hc Hv Io Kz Ly Me My Oy Oz Rh) Wm(Fr Jq Jr Ly Me Mm Mn Mq Na Oy Pc) aD(bM bO bW bX cT cZ Dp eC) bJ(aC
aM aW bA bM cT cW dC) Of(Hw Ij In Jo Lh Nx) bM(aW bO bR cT cX dl) Io(Mt Nt Nx Ny Pd) bW(aG aW bN bR dC) Oy(Mf Mp Na Nb)
My(Jh Mt Nv) Nl(Nc Nc Nh) dI(aM bR bU) Dp(Oi Qv) Hu(Jh Nx) Pb(Lh Mf) FrJk NsMp NcNh NeNk OzPd aMaW bRdA} dN{Aj(Ba bJ bN
bR cT Cw dA Ef Nf) Ch(Ba bJ bN Bo cT Ly Me Ni) Hc(eC Jd Je Jn Lw Rf Rh) Oy(Ba Kr Ms Nr Oe Qg) bO(bA Gp Jn Me Rf) bR(bA bX cT dI
dM) Nf(Jo Kg Kr Ur) dH(bA bQ cT dA) Uu(Ba Jy Sr) Dp(Qv Rf) Kq(aF Kj) Kr(Jn Kx) dA(bU cA) fP(Qv Rf) JoKz} Jq{Mq(Et Is Jl Jr Lx Md
Mm Ns Oh Ok Pf Po Qa Qe) Jl(Et Io Jo Mm Ms Ni Of Oi Oy Pc) Og(Fp Fr Lx Nn Ok Pc Po Qa Qe Wm) Fr(Fp Hu Jr Me My Oy) Et(Jr Oh Pc
Qa Qe) Fp(Mm Nn Ok Pc) Pc(Ok Qa Qe) Oy(Pf Po) BaUu NnOk LxHu MmJr} Lw{Uu(Ax bJ Cw Dp Ef Ez Hu Ij Im Is Jg Jn Kq Lh Ma Mq Nf
Nr Ow Pk Qy Rf Sr Uf Un) Jl(Fp Jn Jr Me Ns Oy) Mq(Jn Jr Ns) Og(Is Po Qe) Us(bJ bN dA) Dp(Aj Ur) Fp(Fr Ok) Jr(Et Ok) Kj(bJ Pk) Kr(Cs
Ml)} Ok{Nn(Fp Hu Jo Jr Me Mq Ms My Of Og Oi) Pc(Fp Jo Jr Mg Mq My Of Og) Jo(Fp Fr Jl Mq Oh Po) Po(Hu Of Og Oy) Fr(Hu My Of Oy)
Lx(Hu Oy) Jr(Mm Of) Oh(Ms Oi) FpLy MqOf JlOg} Og{Jl(Et Fp Io Jn Jr Me Mq Mz Ni Nn Oh Om Pc Po) Mq(Fr Is Jr Mz Nn Oh Pc Po) Is(Et
Mm Nn Om Pc Po) Om(Hu Jr Oh Qa Qe) FpFr NnMe} Kq{Kj(aF aK aL aU aV Ba bN bO cI cZ dA Fn Hu Hw Pd Rf Ua) Uu(aF Ba bJ cZ Kr
Qc Qg) Aj(bJ Dp Kr) OyaW} Mq{Fr(Hu Jn Jr Me Ms My Oy) Nn(Jr Ms Ns Oi Oy) Ns(Is Jr Oh Pc) Et(Jn Jr Mz) Pc(Jn Jr Mz) Oi(Is Oh) LxOy}
Et{Me(Fr Jl Jr Lx Nn Oh Pc) Ms(Is Jr Nn Oh) Ni(Is Jr Oh) Io(Is Jr Qa) Oi(Is Nn Oh) JrPc} Fr{Me(Hu Jr Mm Oh) My(Is Jn Jr Nb) Oy(Fp Jr Nb
Pe) Oi(Fp Jr) HuOm} Uu{Sr(Ba bJ Jd Qg) Un(Ba Cv Ni) CvJd JiKr} Jl{Oi(Fp Jn Nn Oh) MwMy NiOh OmOy} Oy{Nb(Lx Om Po) Pe(Jg Nn)
LxOm} Ji{Kr(bO Jv) WmHv UsbJ} Nn{Oi(Is Jn Jr)} Mm{Ni(Is Jr) MeJr} bJ{Kj(Ad Id) AjSr} AjDpSr

Constrained panels with 3 analytes, where 1.0E-7 >= 'model p-value' > 1.0E-8. Contains 5,698 panels of 7,079,861 total panels evaluated. :
dN{Kr(aA Aj Ax bJ bO Ch Cs cT Cv dA Dp Ed Gp Hc Im Is Jd Ji Jj Jl Jr Jy Ki Kq Kz Lw Lx Mm Mq Mr Ms Mu Mx Nc Ni Nn Nw Ny Oh On
Ow Oz Pe Pk Qa Qe Qg Ql Rf Rh Sr St Uh Un Uu) Oy(aM aV Aw Ax aZ bA bF bG bJ bN BO bR bV cA cT Cv Cw dA DB Dc dl dK dM Fr Gp
Hu Is Jd Jl Jn Jq Jr Jy Ke Kf Kq Lw Ly Ma Me Mq Mr Nf Ni Nw Ny Oi Om Pd Rf Sr Un) Aj(Ad Aw aZ bA bG Bn bO Cp Cq Ct Cu Cv Db Dc
Dd dK Dp Gp Hu Hv Ib Ij Im Is Jd Ji Jn Jq Jr Jy Kf Kq Kx Kz Mq Mr Ms Mu Ni Nn Nr Ny Oe Oi Pd Pk Qt Rf Rh Sr Un) Ly(bA bN bO Co cT
Cv dA dl dM Dp Hc Jd Je Ji Jj Jn Jo Jy Kg Ki Kj Kq Kx Ky Lw Lx Mq Mr Mu No Nw On Pk Qg Rf Rh Ri Ur Us Uu) Hc(aV Ax BA bJ bN bO
cT Cv dA dl dM Gp Is Ji Jq Jr Jv Jy Ke Kq Kx Lu Ms Mu Ni Nn Nw Oi Ow Qg Ql Qv Qy Ri Sr Uh Un Ur) Ch(bA bO bR Cv dA Db dl Dp eC
Ef Fr Gp Hu Is Jd Je Jn Jr Jy Kq Kx Kz Lw Ma Mq Mr Ms Mu Mw Nf Nn Nr Ny Qg Qt Qy Rf Sr) bO(aJ Ax Bo Cs cT Cv Dc eC Fr Im Is Jd Ji
Jj Jl Jr Kq Kx Mq Mr Ms Mu Mw Nf Ni Nn Nr Nw Oz Qe Qg Ql Qt Qv Rh Uh Un) No(Ad Al Ao Ap Bg bJ bN Cu De dF Ed Hq Iz Jo Ju Jv Kd
Ki Kj Kl Ko Kz Me Nd Nf Nv Nx Ok Oz Ph Qc Qh Qu Qz Rh) Nf(aV bA bJ bN Bo bR Co cT Cv dA dl dM Dp Gp Hv In Ji Jn Jq Jv Ki Kj Lw
Ms Ni Nw Og Oi Qg Qv Rf Rh Ri Un) bN(aJ aV aW Bg bJ bR cA cK Cv dA dH dJ dM Dp Gp Hv Ji Jj Jn Jo Jq Jr Kx Lw Me Ms Nw Oi Oz Rf
tF) Dp(bM Bo Co cT Cv eC Gp Ji Jo Jq Jy Kg Kq Kx Lu Lw Ms Nw Oi Qg Rh Sr Ur) Me(aW bA Bg Co dA dl dJ dM In Ji Jj Jn Jo Kg Kj Kx
Lw Nw Oz Ur Us Uu) dH(aJ aP aV Ax Ba bF bM Bo bX bZ cN cO Cs Cv dE dl dJ dM Lx Mq Mr) Co(Bo cT dA Db Im Is Jd Je Jn Kz Lx Mq
Mr Ni Pe Pf Rf) aA(Ed Fn Iz Jv Kd Ki Ko Kx Ms Oi Ow Pk Qu Rf Us Uu) dA(aY Bg bJ bQ bS bZ cF cG cL cO cU dB dl eC Nd Ni) Uu(aV bJ
Gp Hu Jd Jq Ke Kq Lw Mr Mu Ni Rf Un) eC(Ad As bM cK Cq Cu Cw Dc dl dM Kq Mu Pk Un) Ni(aF aV aW Bg bR dl fP Jo Kx My Nk Oz)
Rf(Ao aV bX Ed Ii Jo Kg Kx Kz Oz Pa Qg) bJ(bX Cv Dc Ed Jq Kx Ms Ng Oe Og Oz Pk) Kg(Cw Ef Fy Jd Kq Kz Pk Rh Sr Un) Kj(Ad Cw Ij Kf
Lw Nr Pi Pk Sr) Kz(Cv dl dM Jj Jv Ki Lw Nw Ur) Us(Jd Ji Kq Lw Mr Mu Oz Ql Un) fP(Bo bV cT Fa Gp Mq Ms Rh Sr) aF(BA Bo cT Dc Gp
Jy) bR(bM bQ dJ Jj Jn Kx Oz) Ko(Ji Jn Ke Kq Lw Un) Rh(bM Ki Lw Pc Qg Un) cT(aM aV Bg cK Cv cY) Kx(aK aV Gp Oi Qg) cA(aV bA bM
bX dJ) Bg(BA Bo Jy) Ed(Gp Jd Qg) Fn(Kq Lw Pk) Jn(Jv Ms Qc) Jo(Is Mq Mr) aJ(bM bX dL) Ba(Kl Ng) Cv(Cx Fp) Jv(Gp Sr) Ki(Db Pk)
bA(aM aV) MraW MsPk MwMy NcdI HqNy JiNx KqOf} Jj{Dp(aP Ax bA bV Cs cT Cu Cv Cw Dc Fa Fy Ha Hw Hx Ij Im Is It Iv Jd Ji Jl Jn Jq
Jr Jy Kd Ke Kq Kx Ly Ma Md Me Mq Mv Mz Nn Nr Nt Oa Oh Ow Pe Po Qa Qe Ql Ra Rf Rh Un Uv Vt) Lv(Hu Hw Ii Ij Ik Ir Iv Jg Jm Jo Js Lj
Ma Me Mi Ml Mm Mn Mp Mr Mv Mx Na Nb Ne Nh Ni Nr Nu Nv Nx Ny Pa Pc Pg Qb Qd) Lw(Hu Hw Ii Ij Ik Ir Jg Jm Jo Jp Js Jt Lj Ma Mh Mi
Ml Mn Mp Mt Mv Mw Mx Na Nb Ne Nh Ni Nr Nv Ny Pa Pd Pg Qd Wm) Me(Hu Hw Ii Ij Ir Jm Jo Jp Js Jt Lj Ma Mi Mp Mr Mt Mv Mw Mx
Mz Nb Ne Nf Nh Nl Nm Nr Nx Ny Oz Pa Pc Pg Pz Qd Wm) Mz(Hu Ii Ij Ik Iv Jg Jk Jm Jo Li Lx Ma Mm Mn Mp Mr Mt Mv Mw Ne Nf Nh Ni
Nv Nx Ny Ok Oz Pa Pc Pd Pf Pg Qb Qd) Iv(Hu Ij Ik Jg Jk Jm Jn Lh Li Lj Ma Mm Mn Mp Mr Mt Mw Nf Nh Ni Nt Nv Nx Ny Ok Pc Pd Pf Pg
Qb Qd Wm) Lx(Hu Hv Hw Ij Jk Jm Jo Js Lh Li Lj Ly Mh Mw My Na Ne Nh Nt Nx Ny Of Og Oy Pb Pc Pd Pf Qb Qd Wm) Im(Hu Hv Hw Ii Ij
In Io Jg Jk Js Li Lu Mi Ml Mm Mt Mv Mx Na Nb Ne Nh Nu Pa Pc Pf Pg Qd Wm) Ir(Ij Ik Jg Jk Jm Lh Li Lj Ma Mm Mn Mp Mr Mt Mw Nf Nh
Nt Nv Nx Ny Pc Pd Pf Pg Qb Qd Wm) Mr(Hw Ii Ij Jg Jk Jm Jo Jt Lh Li Mm Mn Mt Mw Nf Nh Ni Nv Ny Pc Pd Pf Pg Qb Qd) Nf(dl dM Hu
Hw Ii Ij Ik Jm Jo Jp Js Lj Ma Mm Mn Mp Ni Nl Nr Nu Nv Nx Pc Wm) Qb(Hu Hv Hw Ij Is Jg Jn Jo Js Lh Ma Mm Mt Mw Na Nb Nh Nt Nw Pc
Pd Pe Pg Wm) Ni(li Jg Jm Js Jt Lh Lj Mi Mm Mn Mp Mt Mw Nt Nv Ny Pa Pc Pd Pg Qd) Hw(Jg Jk Jm Li Ma Mm Mn Mt Mw Nh Nt Nv Ny Pc
Pf Pg Qd) Nt(Jk Js Lh Li Ly Mn Mt Mw Mx Na Ng Oi Pc Pd Pf) Et(Hv Io Jo Js Jt Li Lu Mh Ml Mv Mw Nb Nl Wm) Nh(Ii Ij Jg Jk Jo Jt Ma Mn
Mw Nb Ny Pc Pd Pf) Lh(Jk Jm Li Lj Mm Mw Na Ne Ng Ny Og Ok Pd Wm) Jk(Jn Jo Js Jt Li Ml Na Og Oy Pd Pf Wm) Jo(Jg Jm Li Lj Mn Mt
Mw Ny Pc Pf Qd) Pd(Jt Li Mw Na Ng Ny Oy Oz Pa Pb Pc) Wm(Is Jp Ly Mn Mu Na Nw On Qd Qe) Ij(Lj Mm Mn Mt Mw Ne Ng Pb Pc Pf)
Jt(Io Li Mn Mt Mw Ne Ny Pc Pf) Pc(Hu Js Li Ny Pf Qd) Mw(Jn Js Na Pf Pg) No(bO fP Jv Uu) Nb(Li My Oy Pf) Jn(Jm Li Nv Ny) Na(Jg Nv
Pg) Ny(Is Jq Ne) Qd(Jg Jq) Js(Jg Mm) Uu(Ef Sr) Pc(Li Pf) FpJv MnNe NgNv HvPf LjNw} Lw{Uu(aA Ad aF aK Ap Ar aW bA Bc BN bR bX
Cs CT cX cZ DB dE dl Dk eC Ed Et Fa Fb Fn Fr Fy Gl Hc Hw Ib Ih Ik It Iv Ji Jk Jl Jp Jr Kf Ko Kx Kz Li Lj Ly Me Mm Mu Mv Mw Ng Ni Nn
Nq Oa Oh On Oy Oz Pe Pf Po Pz Qa Qd Qe Ql Rc Rh St Uu Uh Us Vt Wm) Us(aA aF Aj aK aV aW Ax bA bO bX Ch Cs cT cX DE dl Dp eC

Jl Mr Ms Mz Ni Ns Og Oh Oi Pe Qa Qe) Jl(Ii Io Jo Mg Ms Mz Nf Ni Ns Oe Oh Oi Oy) Jq(Fp Fr Io Is Jo Md Me Mr Ne Og Oy Pf Wm) Oh(Io Ir Is Iv Lu Mz Ns Oe Og Oy Qa) Fr(Fp Hu Jr Mg Ms My Mz Ni Oi Oy) Me(Im Io Is Jo Lu Mt Mz Pf Qa Qe) Ni(Im Lj Mt Mz Pe Pf Qa Qb Qe) Jo(Ir Is Iv Jt Lh Mz Pe Qa Qe) Og(Jr Mt Mz Nf Om Pe Qa Qe) Oi(Fp Jr Mt Mz Pe Qa Qe) Oy(Is Jr Nb Pe Pf Qa Qe) Io(Im Iv Mz Pe Qe) Ms(Nf Om Qa Qe) Jr(Ir Lu Ns) Mt(My Qa) Mz(Im Qe) Is(Ns Oe) Om(Hu Mg) MwMy} Jq{Mm(Fr Im Io Is Iv Jn Lh Li Lj Lv Lx Me Mh Ml Mr Na Ne Nf Ng Nh Ni Nn Nt Og Oh Pa Pc Pe Pf Po Qa Qb Qe Wm) Pc(Fr Im Is Iv Jn Jr Lh Li Lj Lx Md Me Mr Ms Na Ne Ng Nh Ni Ns Nt Oh Pa Pe Pf Po Qd Wm) Nn(Hu Is Jo Jr Lv Md Me Mr Ms Ne Nh Ni Ns Of Oi Oy Pa Pe Pf Qa Wm) Og(Im Is Jg Jr Jt Lh Li Mi Mr Nb Nt Oh Om Pa Pe Pf Qb) Fr(Im Is Jn Lj Md Ms Ne Nh Ns Of Oh Oi Qa Qe Wm) Lx(Fp Hq Im Jr Md My Ny Of Oh Om Oy Pb Pg Qe) Ng(Fp Im Is Jk Jr Lh Li Mv Oh Pe Pf Qa Wm) Oh(Fp Is Jg Jr Lv Me Ms Ni Oi Oy Pe) Qe(Fp Io Jl Jr Md Ni Oi Oy Pf Wm) Po(Hu Jo Md Ms Ni Oi Pb) Fp(Is Jg Md Mr Oi Pa Pe) Jr(Im Is Ni Pa Pe Pf) Wm(Ly Md Na Oi Oy) Qa(Io Jl Md Ni Oi) Dp(Aj Kj Ur) Ni(Is Li Pf) Uu(bJ Jd Uf) Jg(Hu My) Pf(Md Me) bJ(Aj Kj) IoIs JiKr OyPe} Og{Om(Fp Fr Im Ir Iv Jh Jn Lh Lj Lx Ly Me Mg Mi Ml Mr Ms Mt My Mz Nf Nn Of Oy Pa Pc Pe Po) Po(Fr Im Ir Iv Jg Jn Jr Jt Lh Lv Me Mm Mr Mt Mz Nb Nf Ni Nn Nt Oh Oy Pc Pe Qa Qe) Is(Fp Fr Im Io Jg Jl Jn Jr Jt Lh Lx Me Mr Mt Mz Nb Nf Ni Oh Oi Pe Pf Qa Qe Wm) Nn(Fp Ir Iv Jn Jr Jt Lh Lv Lx Mr Mz Nb Ni Oi Pe Qa Qe) Jl(Hw In Ir Jt Md Ml Mm Mt Ng Qa) Fr(Iv Jn Jr Me Mz Oh Pe Qa Qe) Lx(Im Jn Jr Jt Me Ni Qa Qe) Jr(Jg Lh Mm Nb Pc Pe Wm) Oh(Iv Jt Lh Me Nb Ni Pe) Qe(Jg Mz Nf Ni Pc Pe) Qa(Jg Nb Nf Pc Pe) Im(Lh Nb Pe) Pc(Lh Pe) SrJv} Jl{Ni(Im Jn Jo Jr Li Ly Me Mm Ms Mt Nn Oi Oy Pb Pc Pf Po Qa) Jr(Il Im Io Jo Lv Me Mm Ms My Nk Nl Ns Oe Oi Oy Pc) Me(Fr Il Jo Mm Ms Mt Nl Nn Ns Oe Oh Oi Pc) Oi(Fr Im Is Li Mt Mz Nf Ns Om Pc Po Qa) Oy(Fr Jn Lx Mz Nb Nf Nn Oh Pf Po Qa) Ng(Hu Im Io Is Jt Mv Mw Mz Pf Qa) Oe(Fp Im Is Nf Nn Oh Om Po Qa) Fp(Fr Ik Mm Nk Nn Pc Pz) My(Fr Jg Jh Jn Mt Nn Om) Ms(Nf Nn Oh Om Pc Po) Jn(Im Io Jo Mm Ns Pc) Om(Hu Jo Mg Ns Of) Oh(Ii Il Io Ns) Po(Hu Il Jo) Nn(Hu Ii Ns) Mz(Mm Pc) FrHu NsPc LxHq NaIo IlQa} Kj{Kq(aA aW Ax bA Bb bX Cs Ct Cw Cx dI eC Ez Fa Fb Fp Fw Fy Hc Id Ij Is Iu Jd Jk Jn Jr Kd Kx Kz Li Lj Ma Mj Ms Mz Nf Nn Nr Oa Oh Ow Oy Pi Pk Po Qe Qg Ql Qy Rh Ri Sr Uf Un Up Us Uv Wm) Ad(Ba dI Dp Hu Jd Po Qe Qy Rf Sr Ua Un) Id(Ba Dp eC Hu Jd Pd Qe Qy Rf Sr Uf Un) Sr(Cw Dp Ij Om Pi Pk Qg Ri Tv Up) Un(Cw Fn Ij Jv Kr Ms Pi Ra Up) Pi(Ba bJ Hu Jd Pd Rf Uf) Cw(bJ Hu Jd Qy Rf Ua) Pk(eC Hu Nn Po Qe Rf) Ij(bJ dI Dp Hu Pd) Up(Ba Jd Rf) bJ(Dc In) QaQc JiKr} Ng{Lx(Fp Hv Hw Ij Im In Ir Iv Jh Jk Jn Jo Jp Jr Jt Lh Li Lj Lv Ly Mg Mm Mn Mv Mw Nb Nf Nt Ny Oh Po) Po(Im Ir Iv Jh Jk Jn Jp Jr Jt Lh Lu Lv Me Mi Mn Mt Mw Mz Nk Nt Oi Pe Qa Qe) Nn(Hv Hw Ii Ij Jo Md Mn Mt Mv Mw Mz Ne Nh Nt Pa) Is(Io Jh Jr Jt Lh Lu Mi Mv Nb Nf Ni Oh Pd Pe Pf) Lh(Im Jr Mm Mv Oh Pc Pf Qa Qe) Qa(Jh Mi Mm Nb Nf Ni Pe) Qe(Jh Jt Mi Nb Ni) Oh(Jh Jt Nb Ni) Pc(Jn Jr Jt Pe) Im(Mi Nb Pe) Pf(Jt Nb Ni) Mm(Jr Pe) WmOm MweC} Fr{Me(Fp Im Is Jn Lj Lv Lx Mg Ms Mt My Mz Ne Nh Ni Nn Ns Of Oi Oy Pe Pf Po Qa Qe) Fp(Hu Ik Ir Is Iv Jn Jr Jt Lv Mg Mm Ms My Mz Ni Ns Oh Pb Qa) Oy(Im Ir Is Iv Jn Lx Mz Ni Oh Pf Po Qa Qe) Jr(Hu Im Ir Jn Lv Mm Ms Mv Ni Ns Oe) My(Ir Iv Js Jt Ni Oh Om Pe Po Qa) Oi(Im Ir Is Jn Lj Mz Oh Po Qa Qe) Ni(Im Is Jn Lj Oh Qa Qe) Hu(Im Ir Is Jn Po Qa) Is(Il Mm Ms Oe) Jn(Im Lv Mm Ms) Qa(Il Of) MsOh ImIr} aA{Dp(aM Ao aW bM bP bW Ch cN Cv cW dC eC Fa Io Iz Ji Jv Kx Ml Ms Ni Nl Ow Oy Oz Qu Rf Rh Ri Sr Uf Ur Us Vt) cN(bN bR bS cA cL cT cX dH) dA(bQ bS bU cA cL cO dH) aC(aL aV cK cZ dC dM) cT(aG aL aM bP dC dI) bJ(aG bW Io Oe Oi) cW(bP cX dC dI tF) Uu(Ji Kq Sr Un) bR(aM aV aW bX) Ef(Fa Kq Sr) Jv(Rf Sr Un) bM(Cx Oi Oy) Ji(Kr Us) Qu(Ow Rh) Kx(Oi Oy) bB(aE aL) bU(aW bX) bW(aM cX) eC(In Me) CvCx FafP IoaF UnUs aObZ bAbO bPbX cXdI} Nn{Ni(Fp Hu Im Ir Is Iv Jn Jo Jr Lv Lx Me Mi Mm Mr Ms Ne Ns Oi Oy Pa Pb Pe Pf Po Qa Qe) Oi(Hu Im Ir Iv Jt Lh Lj Lv Lx Me Mr Ms Mz Ne Nh Ns Nt Pa Pe Po Qa Qd Qe) Me(Hu Ii Im In Is Jn Jo Jr Lv Lx Mm Mr Ms My Ns Oy Pa Pe) Is(Fp Hu Ii Il Io Jr Mm Ms My Ns Oe Oy) Ms(Fp Iv Jn Jr Lh Nb Om Pe Po) Jr(Ir Lv Mm Ns Oe Oy) Jo(Iv Jt) Oy(Lx Po) MyNb HuOm} Uu{Kq(aK aV aW bH bO bW cN Co Cv dA dI dJ Dp Ez Fn Fw Hb Hq Hu Ih Ii Jd Kd Kg Ko Ni Oi Ow Oy Oz Pg Pk Qy Sr Uf Ul Un Us) Sr(Aj aK aV Bg BO Cv dA dJ Dk Dp eC Ez Hu Jv Jy Kx Nc Nl Qy Ri Uf Un) Un(bJ eC Hb Jy Kr Lu Ms Ow Qv Qy Rf Rh Us) Ji(Ba bJ dI Qg) Ba(Ke Vt) FnKe} Po{Ni(Hr Hu Im Is Jn Jo Jr Mm Ms Mt Of Oh Oi Oy Pb Pc Qe) Is(Il In Io Jo Mm Ms My Oe Oi Oy Pb Pc) Oi(Ir Jn Jr Mt Mz Oh Pc Qa Qe) Oy(Ir Jg Jn Jr Lv Mz Om Pc Pe) Jn(Im Jo Js Lv Mm Pc) My(Jg Nb Om) Jo(Ir Iv Jt) Jr(Im Mm Pc) Me(Mm Pc) Ms(Om Pc) MiHq HuOm PbPe} Lx{Oy(Hw Ij Ir Is Iv Jg Jn Jo Jr Jt Li Lv Ly Me Nf Ni Pc Qa Qe) Ni(Hq Hu Im Is Jr Ly Of Oh Pb Pc Qa Qe) Me(Hq Hu Im Jr Mm Of Oh Pc Pg) Hu(Ir Is Jh Jn Jr Jt Om Qa) Hq(Ir Is Jn Jr Li Mi Qa) Qa(Il Of Oi Pb) My(Jg Om) Is(Il Oi) Jn(Js Of) Jr(Mm Pc) NsMh OfOm} Mm{Jr(Fp Im Io Ir Is Iv Jn Lh Lu Lv Mz Nf Ns Oi Om Pc Pe Qa) Is(Fp Io Ir Jn Lv Me Ms Mz Nf Oh Oi) Me(Im Jn Lv Mt Mz Oh Pe Pf Qa) Ni(Im Jn Oh Pe Qa) Jn(Fp Im Io Lv) LvMz NbOy UnUs} Oi{Oh(Fp Ir Is Jg Jn Jr Jt Lh Lv Me Mz Nb Ni Nt Om Pc Pe Qa Qe) Is(Fp Jn Jr Lh Li Mt Mz Ni Pc Pe Pf Qa) Pc(Jn Jr Pe Qa Qe) Om(Fp Jr Qa Qe) Qa(Jg Mt) ChJd MzQe} Ji{Kr(aF Aj aW Ax bJ bP Ch cI cN Cs Cx cZ De dI dM Dp Ed Ii Iv Kg Ki Kx Ms Ni Oh Ow Qg Ql Rh Ri Us Vo Wm) Us(cZ Jv Qg) Dp(aW Kg) AjbJ HcaW} Om{Oy(aW bJ Jr Mi Oh Pe Pf Qa Qe) Hu(Fp Is Jr Me Oh Pf Qa Qe) Ms(Fp Is Jr Oh Qa Qe) Qa(Jo Mg My Of) My(Jr Nb) Ni(Jr Oh) AjDp ChbJ MeOh} Kq{Dp(Ao Ch Co Iz Kg Of Oy Ur) Oy(bJ cI cZ Kr Us) Ch(bJ Kr Nf Us) Hc(aW cZ eC) bJ(aF Iz Of) Aj(Nf Us) Kr(Iz Of) CoUs EdFw JvaE KlcZ} Ni{Pc(Im Is Jn Jr Oh Pe Pf Qa Qe) Is(Im Jr Li Ms Oh Pf Qa) Jr(Im Oh Pe Pf Qa Qe) Im(Mt Oh Pe) Jd(Aj Ch) Oh(Me Ms)} Aj{Sr(Hu Jd Jv Kx Nf Qy) bJ(Ad Id Ke Un) Dp(Id Ke) NfUn QybA} Pc{Jr(Im Ir Is Me Ns Pe) Me(Is Oh Pf) Is(Fp Ms) Oy(Nb Pe) NsQa} Un{Us(bW Ch Co eC Jv Oz Uf) Oy(aW Ms) DpKg EdFw JvKr} Nb{Oy(Im Is Jg Jr Oh Pf Qa Qe) My(Jg Mw) MsOh} Ch{Jd(Ly Nf) Qy(bA cT) bJ(Mw Ny) FatF} Dp{Sr(Kg Qv Ur) KeKg} My{Is(Jg Mw) HuJh JgJr} Qe{Qc(Jn Jr) IlIs} Qa{Qg(Kr Us)} Oh{JoJt OyPe} Pk{dM(Hc Oz)} IoIsJr

Constrained panels with 3 analytes, where 1.0E-6 >= 'model p-value' > 1.0E-7. Contains 11,865 panels of 7,079,861 total panels evaluated. : dN{Kg(Aw Ax aZ BA bJ bN bR cT Db Dc dK Gp Hu Ib Ij Im In Is Ji Jl Jn Jq Jr Jy Kd Ke Kf Kn Kx Lh Lw Ma Ml Mq Mr Mu Ni Nn Nr Ny Oe Oi Ow Oz Pd Pe Pi Po Qa Qh Ql Qn Qt Ra Ri Uh Uv Vt) Kj(aV Aw Ax aZ BA bG bJ bR Cp Cq cT Cu Db Dc dK Gp Hf Hu Hw Ib Id In Is Jd Ji Jl Jn Jq Jr Jy Kd Ke Kn Kz Mq Mr Mu Na Ni Nn Oe Oi Om Ow Pd Pe Qa Qn Qt Ra Rf Un Up Vp) Us(Ax BA bJ bN bO bR bV cT Cv dA Dc dI dM eC Gp Hv Id Im Is Je Jl Jn Jq Jr Jy Ke Kf Ki Kx Kz Lx Ml Mq Ms Mx Nf Ni Nn Nr Nw Oi On Ow Pc Pd Pk Qa Qe Qg Qt Rf Sr Uf Uh) Uu(Aw bA Bc bM bN BO bR cT Cv Cw dA Db Dc dI eC Ef Ez Fr Hf Hv Id Ij Is Jg Ji Jl Jn Jr Kf Kz Ma Mq Ms Nr Nw Oe Oi Om On Ow Oz Pc Pd Pk Qg Ql Qn Qt Qy Rc Uf Uh) Fn(Ad As bA bO Ch Cq cT Cu Cw dA Dc Ed fP Hv Hw Id Ij In Is Ji Jn Jq Jr Jv Jy Kd Ke Kn Kx Kz Ml Na Nf Ni Om Ow Oy Oz Pb Pc Pi Qa Ra Rf Ri Sr Un Up Vp Vt) Jo(Ax Ba bJ bO bR cT Cw dA Db Dc Fy Gp Ij Im In Iv Jd Ji Jn Jq Jr Jy Ke Kf Kq Ma Ml Mu Nn Nr Oe Ow Pd Pe Pi Pk Po Qa Ql Qn Qt Rh Sr Uh Un) Co(Ax Cs dB Dc Fa Fp Fr Fy Gp Hu Ib Ij Iv Jl Jr Jy Ke Kf Kq Kx Ma Mh Ml Mt Mu Mv Mw Nn Nr Ny Og Om On Ow Pd Pk Po Qm Qt Sr Uh Un) Kq(aK AO aW Bb bF Bg bJ bN bR bX Cp De Dg dH Ed fP Hq Ii Iz Jt Jv Kd Kl Kp Kz Me My Nf Ng Nx Ok Ow Oz Pa Pk Qc Qz Uc Ur Ut) bJ(Ad Bn Bo Cq Cs Cu Cw Hw Id Ij In Is Ji Jj Jn Jr Jy Kd Ke Ki Kk Kz Lw Ml Mq Mr Mu Mz Na Nc Ni Nw Oi Pc Pi Qa Qv Sr Un Ur) Oz(aV aW bA Bo cA cT dA Db Dc dI dM Dp Gp Hf Hu In Jd Jq Jy Ke Ki Lw Lx Ly Mq Ms Mu Nr Nw Oe Oi Ow Pk Qg Qv Ri Sr St Un) Jd(aF Ao Ap Bg bN bR De dH Dp eC fP Hb Hu Hv Iz Jv Ki Ko Kz Me Ms Mv My Ng Ni Oe Of Oi Ok Pk Qu Rh) Ed(aV BA BO bR bX cK cT Cv dA dI dL Jn Jq Jy Ke Lw Mr Mu Ni Nw Oe Oi Qv Ri Sr Uh Un Ur tF) Pk(bA BO Ch cK cT Cv dI dM Gp Ji Jj Jy Lu Lw Me Mq Mr Ni Of Oi Oy Qg Ql Qt Qv Qw Qz Un Ur tF) Kz(aF aV bN bO bR bS dA dH Dp Fw Gp In Je Ji Jq Jy Ke Kx Ms Mu Ni Oi Oy Qg Ql Qv Rh Ri St Un) Ki(aV aZ bM bN BO bR cT dB dE Dp Gp Hf Im Jn Jr Kf Kx Me Nr Oe

Figure 8 Continued

Og Oi Ow Oy Qg Qv Ri Sr) Jv(Ax BA bM Bo bX cT Cv dI Im Is Jr Jy Ly Ma Me Ml Mq Mr Mu Ni Nr Oe Og Qg Qv Un Ur) eC(Hv Hw Id Ij In Ir Je Jn Jq Jr Kd Ke Kn Kp Kr Kx Na No Pb Pc Pi Qa Rf Ri Rj Up) Oy(Cp Fy Hf Hq Ij Jl Kn Kx Lx Nn On Pe Po Qa Qc Qn Qt Qv Qx Rh Tn Uf Uh Uo) dH(Gp Im Is Ji Jj Jl Jn Jr Jy Ke Kx Lu Lw Ma Mu Ni Nw Ny Pe Qg Sr Uh Un Ur) bO(Fa Fy Gl Id Jq Jy Ke Kf Lw Ma Ml Ny Og Oi Ow Pe Pf Po Qa Qd St Ur Ut) Aj(Ez Fy Hf Id In It Kd Ke Kn Md Ml Nb Om Ow Pi Qa Ql Qn Ra Uh Vt) Ch(Fa Fy Hv Ib Ij Im Jh Ji Jq Ke Kf Oi Om On Ow Ql Rh Ri Ua Uh Un) Ri(Ax bN Gp Hv Im Jn Jr Kr Kx Me Ml Mr Ms Nc Ni Pc Ql Qv Rf Sr) fP(Ax BA Cs dB Dc Fr Jy Ke Kf Lu Ma Mr Nn Nr Oe Qg Qt Uf Uh) Ng(Bo dA Gp Hu Is Jn Jy Lw Mq Mu Ni Nn Nr Ny Om On Ow Rh Sr) Un(aF Ao aW bN bX Ii Iz Jt Kl Lu Ly Ms Nm Oi Ok Ow Qg Qv) My(Ba Bo cT dA Fr Je Jh Jn Jy Lw Mq Mu Ny Om On Sr) bR(Gp Is Ji Jr Jy Lw Mq Mr Nc Ny Ow Ql Qv Ur tF) Bg(dI Fr Gp Je Lw Mq Mr Mu Mw Ny Om On Qt Sr) Kx(aQ aU bG Bo cA cY cZ Db Hf Ms Nf Oe Rh Sr) aF(Ax Db Fr Fy Is Jq Ke Ma Mq Mr Mu Nw Qv Sr) dA(Gp Hq Ky Mi Mk Nc Ns Of Pd Qg Qw Rf Uk Ur) Ql(aK aV bN Bo Hf Ly Me Ms Oe Og Oi Qg Qv) Ow(bN Cv Dp Ly Ms Nc Ni Nw Oe Og Oi Pc Qg) Ao(Bo Dc Im Is Je Jq Jy Ke Mu Nw Ny St) Ni(dM Dp Jr Ko Ly Ms Nd Nj Oe Pc Qg) Rh(Cv dI Gp Je Ji Jq Me Ms Mu Nw Sr) Qc(Im Is Jr Ny Qa Qb Qd Qe Rf Sr) Ur(aV aZ Hf In Kr Ms Nr Oi Pa Pc) bX(bU Ji Jl Jq Jr Ke Lw Mu Nw St) Jn(aV Hf Hv Ii Jt Oe Oi Ph Qu) Rf(bM dI Hb Kd Ko Lw Oe Oi Ok) Mq(aK aW cY Hv In Jq Pc Qu) Ji(aK aV aW bG Jt Ms Oi Ok) Jj(aV bG DB Hf Nr Oi Pa) Jy(aO bF bN cG Hq Iz Kl Nf) Kr(bA Id Jq Js Ke Qb Qd Uf) Lw(bM Hf Nd Pa Qg Qz Up) Im(aW bS cA dM Ii Oi Qv) Ko(cT Dc Is Jq Jr Qa Sr) Ny(aK aW Bb bG Hu Ii Of) Gp(aO aV Kl Pb Qu Wm) Pc(Bo cA cT dM Qg Qv) Me(Je Ky Ld Qg Ug) Mu(aK Hq Iz Kl Pa) Is(aW Ii Ir Jt Ok) Ba(aO Dg Jt Mg) Lx(bG Nd Nl Pf) Ly(Ld Qv Qy Sr) Hu(aD Bo Je Mw) Qz(aV Cv Jq Nw) Of(Cw Ij In Om) bA(Fw Hv Pb Qu) bN(Je Qg Sr Uh) cT(Hv Pb Qu Rg) Ml(Fw Mj Nc) Jr(aV Oi Qg) Kd(Dc Jq Nw) tF(aZ bG Nr) Dp(bV Ik) Nf(St Ug) Hc(Fy Tn) Qv(aV Hv) Kl(Sr Uh) Nw(Ok Pa) bM(aD Io) bZ(bQ Ma) AxRg DgUh FpIk MsQy NcaV HqPg IiJl QeaW NxOn PadM aKcM bVcS} Lw{Kr(Ad Aj aM bO Ch Cq cT Cu Cw Cx Dc dE Dp eC Fa Fp Hc Hu Hv Hw Id Ih Ij Im Iv Jd Jl Ju Jv Kc Ki Kj Kn Kq Kx Kz Lh Li Lj Lx Me Mj Mm Mr Mx Mz Na Nf Ni Nn Nr Nw Oa Og Ow Oy Oz Pe Pf Pi Po Qb Ql Qz Ra Rj Sr Uf Up Ur Uv Vt) Us(Bb Co Cx Db Fa Fn Fp Hc Hw Ih Im In Ir Is Iv Ji Jj Js Ju Ki Kj Kq Kx Lx Ly Me Ml Mm Mr Mu Mv Nc Ni Nl Nn Nr Ny Oa Og Oh Oi On Ow Oy Pc Pf Pi Po Qa Qb Ql Qu Qy Ra Rf Rh Sr Uf Ug Ur Ut Uv Wm) Hc(aA aF Aj aM Ax BA Bc bO bR Ch Cs cT Cx cZ DE Dp Ed Fa Fr Hu Im Is Iv Jd Jf Ji Jj Jl Jr Ju Ki Kj Kk Kp Kx Ld Lj Mq Mr Nf Ni Nn Nr Oa Og Oh Oi Pf Qa Qe Ql Qy Qz Rh Ri Sr Un Ur Wm) Kj(Ad Ax Ba Bn Ch Cq Cs Db Dc De Ed Fa Fp Hw Id Im Is Iv Jd Jq Jv Kn Kp Kx Kz Lj Ly Me Mq Na Nn Nr Oa Og Oi Om Ow Oy Pi Qa Qe Ql Qz Ra Rf Rh Sr Un Up) Dp(aF Ao Ax Bb bG Bo bX Cs cT Cx Ed Fa Hu Hx Ii Iz Jf Jn Jo Jr Ju Jv Kx Kz Ld Lj Lu Ly Me Mg Nf Ni No Oa Og Oi Ow Oy Oz Qu Qz Rh Sr Ug Vo) Jv(aA aE aF aK aW Ax bJ BN bX Cs Cx Db dE Ed Fa Fn Hf Im Jd Jn Ju Kx Kz Lj Ly Mb Me Mq No Nr Og Ow Oy Oz Pa Pk Ql Rf Rh Sr Ur) Fp(Hx Im In Ir Iv Jg Ju Kg Lh Lv Lx Ly Ma Me Mi Mr Mx Mz Nb Ng Ni Ns Nt Oh Oi Om Pa Pc Pe Pf Qe Qu Ue Ug Ur) Ed(AF Aj aK aW bN bR Ch Cq CX cZ Dc Fn Jd Ko Kx Nf Ni Nl Og Oi Ow Oy Oz Pa Pk Qg Qz Rh Ri Uc Ur tF) Me(aF Aj Ax bJ bN bO Ch cI Cs Cx dM Jn Jp Jq Lh Li Lv Lx Ma Mr Mt Mz Nt Og Om Pa Pc Pe Qb Qe Ur Wm) Oy(aW bA Ez Fa Fn Jd Ju Ki Kk Kp Kq Kx Lh Li Mi Nn Oa Oh Om Pf Pk Qe Ql Qy Qz Rf Rh Ri Sr Ur Wm) Jq(Im Ir Iv Jg Jn Jp Lh Li Lj Lu Lv Ma Md Mh Mi Ml Mr Ms Mt Nb Ne Ng Nh Ni Nt Pa Pe Qb) aA(aD aE Af aG Aj aW Bg Bn bR bX Ch cX Db dC De Fn Iz Ko Kx Kz Ow Pk Rf Rh Ri Up Ur) Og(bJ Et Fn Ir Jg Js Jt Ki Li Lv Lx Mi Mt Mv Mz Nf Nt Pa Pc Pf Qb Qd Qz Rf Rh) Pe(Et Fr Hq Il Io Ir Jn Jo Li Lv Ms Mt Mz Nh Ni Nn Oh Oi Om Pa Pb Pc Pf Qa Qc) Lv(Et Fr Im Ir Iv Js Lh Li Lj Lx Mq Mr Mz Nb Ng Nn Oh Om Pa Pf Po Qe) Rh(aE aF Aj aK aU aW bJ bN bO bX Ch cI cQ Cx dC DE Jn Nf Pk Qu Un) Et(Fr Im Ir Iv Jo Js Lh Mh Ml Mr Ms Ne Nf Ni Ns Nt Oi Pc Pf Qb) Mq(Aj Ch In Ir Iz Jp Kl Lh Li Lx Mr Ni Oi Om Pb Pc Pf Qu Ss Vo) Im(Ir Iv Js Li Lu Lx Mi Mr Ms Nb Nn Ns Nt Oh Oi Om Pa Pf Qe) Jn(In Kf Kl Ko Lh Lu Lx Mr Ms Nn Ns Nt Oh Oi Pa Pc Pf Qb Uc) Mt(Fr Iv Lh Li Mr My Ng Nh Ni Nn Nt Oh Oi Om Pa Pf Po Qb) Mz(Iv Lh Li Lx Mr Ng Nh Ni Nn Nt Oh Oi Om Pa Pc Pf Qa Qb) Fn(aE aF Aj aK aM aW bJ bN bO bX cC Ch cI cT cX dA Pk) Fr(Hu Js Lh Lj Mg Ml Mr Ms Ne Nh Ni Nt Oh Oi Qb Qe) Nf(Aj aW Ch Iz Jf Ju Kg Ki Qg Qn Qu Qv Qz Ri Ug Vo) Iv(Io Jo Jp Li Lx Ma Mr Ng Ni Nn Oh Om Pc Pf Qb Qe) bJ(Ch Iz Kg Kl Ko Kp Oa Qg Qv Rf Ug Ur Uv Vo Wm) Lh(Io Jo Lj Ms Nh Ni Nn Ns Of Oh Oi Pb Pf Qe) Aj(Ez Fa Fb Hu Ib No Oa Pk Ql Qy Rf Sr Un) Ng(eC Jk Jp Jt Li Ma Mr Nb Nt Nv Oh Qb Qd) Om(Ir Jo Lj Mg Mr Ms Ni Ns Of Oh Oi Pf Qe) bN(Hf Jd Qn Qx Qz Rf Ri Ss To Uc Up Ur Vo) Ch(eC Fa Hu Jd Kx Kz Ow Pk Ql Qy Rf Sr) Nn(Hu Io Ir Js Lx Mr Ms My Ne Nh Ns Nt) Lx(Hu Ir Ly Ni Ns Of Oh Pb Pg Qa Qe) Pk(Bg Kg Ki My Qg Ql Qz Rf Up Ur Vo) Pf(Io Ir Mr Nb Ni Ns Nt Oi Pb Qe) bX(Jd Ki Qg Rf Ri Uk Ul Un Up Ur) aF(Fa Jd Ko Ql Qz Rf Ri Uc Ur) Cx(Fa Ju Kg Ki Qu Qz Un Ur) De(Hf Jd Oa Ql Qx Rf Un Uv) Oh(Io Ir Jt Lu Mr Nb Nh Nt) No(aW Ef Iz Kf Kg Ko Vo) Ni(aW Jp Li Lj Mr Pa Qb) Qe(Io Ir Jm Mr Ms Ns Pc) Rf(aE aK aU aW bO Oi) eC(Bg Hf My Qg Ss Vo) Po(Io Ir Jo My Qa) Uc(bA bR cT dE Kq) Ur(aK dE In Kz Ly) Up(aW cT cX dA dE) bO(Fa Jd Oa Ql Sr) Li(Io Ir Ns Oi) Mr(aW Ns Pc) Kz(Ju Ki Ri) Un(Ii Jt Kl) Bg(Hu Jd) Fa(Ef fP) Ms(Nb Qa) Hf(aE aW) Iz(Hu Jd) Ko(bR Cs) dA(Nd Uk) BaKl NtMu LyKi MyNb TnUu QlaE} No{Aj(aA AD aM As aW bJ Bn bO Cp Cq Cu Cv CW dA Dc dM Hc Hq Hv Hw Ib Id Ij In Io Ir Jd Ji Jn Jo Jq Ju Kd Ke Kg Kn Kp Kq Kr Md Me Ml Mq Mz Na Nc Nj Nk Nl Nm Om On Pb Pi Pk Qa Qy Ra Rb Rj Sr To Tv Uc Ud Ul Um Un Up Us Uv Vp Vt) Us(AD aM Ao As aW bA bC bI bJ Bn bV bW cK cN Cp Cu Cv Cw Dc dI dL Et Hc Hv Hw Id Ij Iz Je Jj Jn Jq Jr Kd Ke Ki Kj Kl Kn Kq Kr Mm Mq Mu Na Nc Nf Ni Oi Om On Oz Pg Pi Pk Qa Ql Qu Ra Rb Ri Rj Sr Tv Ud Uf Ul Um Uo Up Tj) Kr(aA Ad Al Ao As aW bA bC bS bW cN Cu Cv Cw cX Dc dI dL Ef fP Hc Hv Hw Id Ij Iv Jj Jn Jq Jr Ju Kd Ke Ki Kl Kn Ko Kp Kq Me Mm Mq Na Nf Ng Ni Nq Oi Ow Oy Pi Pk Qa Qu Ra Rb Ri Rj Sr Tv Ua Ud Uf Ul Un Up Vo Vt) Dp(aE aM Bb Bg bO bX Cq Cv cW Dg dH dM Fw Ha Hc Hu Ik Ir Iu Jg Ji Jk Jm Jt Ju Jv Kg Kx Ld Li Lu Ly Me Mg Mh Ml Nc Ng Nj Nk Nv Oe Og Oz Pk Pz Qc Qu Rh Ri Tz Ua Ut Vo Tj) Co(Ad aM aW bJ bN bO bR Cs CW Cx dA Db Dc dI Hc Hq Ij In Io Iv Jd Je Jh Ji Jq Jv Kq Kx Kz Lv Ly Me Mq Nc Ne Nk Nl Ny Og Oi Om Ow Oy Pd Pe Qa Qx Qy Ra Rh Ss Un) Hc(aD aM Ao bA bH bI bX Ch cN cT Cv cW cZ dI Ii Io Ir Iu Je Ji Jj Jq Ju Kj Kl Kx Lu Ml Mz Nc Ng Nk On Ow Pg Pk Qc Qh Qu Qv Qy Rh Sr Ul Ut Vo Tj) bO(aC aJ Al Ao aP aW bA Bg bI bM bR bS bV bW cA cN cP dI dL Fw Hb Hq Hu Ii Ji Jr Ju Kj Ks Kx Lu Me Mq Nc Nf Nk Oe Oi Ow Pk Qz Ri Ss Ua Ur Vo Tj) Jv(aD aE aK aX Bb bJ Cv dH dI Ha Ii Iz Jk Kj Ks Kz Ld Lu Ly Me Ms Nc Nd Nf Ng Ni Nk Nl Nv Oe Oi Ow Oy Oz Pa Pk Pz Qh Qv Ri Sr To Ur Tj) Ef(Ad aM bS cA cP cT CW Dc Id Ji Jq Kd Ke Kn Kp Me Ml Mq Nc Nf Nk Nl Om Ow Pi Pk Qh Ra Rb Rh Ri Rj Rm Ud Ul Un Uo Up Ur Tj) Kj(aA aD bJ Bn Cp Cq Cu dA dM Hv Hw Ji Jn Jo Jq Jr Kd Ke Kn Kp Me Mq Na Nc Nf Ni Nj Nl Nm Pb Qa Rb Ri Rj Sr Tv Ud Ul Un Uv Vt) Iz(aA aD aM Bc bJ bN bX Cq dA Dc dI Ib Id In Jd Jh Ji Jq Kq Kx Kz Ly Me Mq Nc Nj Nk Nl Om Pk Ra Sr Un Ut) Oy(aD aM bI bV cN Cv CW dA dG dI dL Id Kq Kx Pk Qh Ql Qv Ra Ri Sr To Ul Un Up Tj) fP(aA aE Bb bI bV cS cW Fa Hb Io Ir Ju Ks Kx Mg Mq Mz Nc Ni Nm Oc Og Ri Tz Ur Ut) aW(aD aM bR bS cA Cv cW dH Hq Io Ji Jj Ju Me Mq Nc Nf Oe Oi Oz Pk Qu Ri Ua) Kl(bC bW Ch Cv cW cZ dA dI Hq Io Jj Ju Mm Nc Nj Nk Nl Ow Qc Qh Rh Uf) Ri(aA aD aF Al aM aN Bb Bg bX Hq Ir Jj Ki Kz Nc Ng Oi Pk Qh Qu To Ua) Pk(bJ Ch Cq Cu dM Fw Hq Ii Ir Jj Jk Jt Kg Ko Mj Oi Qc Qu Uc Ur) aD(aA Ad Al Ch Cq cZ Dc dI dM Io Ir Jj Jt Kg Ni Oe Oi Qc Ur Vo) Qu(aA Al aM Ao bJ bX cT cW dM Jj Kz Ly Me Mq Nc Nf Ni Nl) Hq(Ao Bb bH bJ bR Ch Cx dA dI dM Hf Kx Kz Pd Qn Qz Vo) Jt(Ad aM As Cw Dc Id Ii Kd Ke Kq Pi Ra Sr Un Up) Uu(aA bH bJ bS bW cN Ed Ez Hu Mq Oa Om Qv Rm Um) Ko(Ad Cw Dc Id Jq Kd Ke Kp Kq Na Pi Un Up Vv) Ch(bX cN dM Fw Kd Kx Kz Lu Ml Mu Oe Pg Um) Ni(aF aK aM aV Bb bJ Cq dI dM Kg Kx Ss Vo) Ao(Io Jd Ji Ju Jy Me Nc Nk Ns Oe Qy Un) Kg(Cw Id Jq Kq Nf Pi Ra Sr Un) Oe(aM bJ dM Im Jg Ki Lh Nt Qh) dI(aM bR cP dH Me Ml Nc Nf Qz) dM(aM dH Io Me Nc Nf Oi Pa) Ju(aE bJ bX Kx Nc Og Oi) Kq(Bb Bg Cu Of Ur) Cq(Ji Jq Me Un) My(Jh Lh Mz Po) Nc(Dg Mt Mz Nl) Ii(aM Jo

My(Jg Mt) Mz(Im Mm) Oe(Im Nt) EtMg MePf MiHq HwJo IiNw HcdM SrUu} Ng{Jr(Im Ir Iv Jh Jk Jo Jp Jt Li Lv Ma Mg Mi Mn Mp Mr Mv Mw Mz Nb Nf Ni Nm Nt Nv Ny Oh Pa Pd Pe Pf Qa Qe Wm) Qe(Hu Hw Ii Ir Is Iv Jk Jn Jo Li Lv Ma Me Mg Mm Mn Mp Mr Mt Mv Mw Mz Na Nf Nt Nx Oh Pd Pe Pf Qa) Pf(Hw Ii Ij Im Ir Iv Jh Jk Jn Jo Lj Lv Me Mi Mm Mn Mr Mt Mw Mz Nt Nv Nx Pc Pe Qa) Lh(Fp Jh Jk Jn Jp Li Lv Ma Me Mn Mp Mt Mw Nf Nh Ni Nt Nv Ny Pb Pd Pe Qb Qd) Oh(Hw Im Ir Iv Jk Jn Jo Lu Lv Me Mi Mm Mr Mv Mz Nm Nt Pc Pe Qa) Im(Ir Is Iv Jh Jk Jn Jt Lv Mm Mr Mt Mv Mz Ni Nt Pa Pc Pd) Pe(Fp Jh Jk Jn Jt Lu Lv Ma Mg Mn Mt Mv Mw Mz Nb Ni Nt Nv) Jt(Fp Jh Jk Jn Li Lv Ma Mm Mp Mt Mv Mw Ni Nv Qa Qb) Is(Fp Hu Jk Jn Li Me Mt Mw Mz Nt Oi Qa Wm) Mm(Iv Jk Jn Li Lv Me Mi Mv Mz Nb) Qa(Hu Iv Jn Ma Mn Mr Mt Mv Mz Pa) Pc(Fp Ij Iv Jh Jk Li Nb Nt Nv Qd) Nb(Jk Jn Li Ma Mp Mt Mv Mw) Mi(Fp Jh Jk Jn Li Mv Nv) Jn(Jh Jk Lv Ma Mv Ni) Et(Fp Hw Ij Js Pa) Li(Iv Jh Lv Me Ni) Nt(Ma Mv Nf) Ni(Jd Jk Nv) Sr(Dp eC Jv) Mv(Nv Nx) Jh(Jk Qd) Rh(Jd Un) eC(Ny Un) BaUu WmNw MaIv MeNv JibJ QycT} Un{Us(Aj Ao aW Ax bA bJ bM bO bX cN Cs cT Cv dA dI dM Dp Ed Fn Hb Hc Ih Ii Ir Iz Jl Kg Ki Kx Ly Ms Nf Nm Oi Ow Oy Qg Qy Rf Rh Wm) Uu(aV aW bF bO bR bW Co cT cZ dA dI Fn Hu Hv Ih Ii Io Ir Jd Jv Ly Ma Mj Nf Oi Oy Oz Pk Qg Ri Ss Uf Ul Ur) Aj(Ao aW Ba bR bX Dp eC Ed Hb Hu Io Jd Jv Jy Kd Kr Kx Lu Ly Ms Nc Ni Nl Nr Oi Ow Pk Qt Qy Ra Rh Ri Wm) Kr(aW Ax bW Ch Co Cs Cv Ed Ih Ii Ir Iu Iv Iz Kg Ki Kx Mm Ms Ni Oh Oi Ow Oy Oz Qg Rf Rh Ri Uf Vo) Jv(aE aK aW bJ bN Bo bX dI eC Fn Hc Ii Jo Kg Ko Kx Kz Ly Ms Nf Og Oi Ow Oy Qg Qv Rh Sr Ur) Oy(Ba bJ cI Cv cZ dI dM eC Fn Hb Ih Ii Io Ir Iu Kx Lu Ni Qg Qv Rf Rh Ri Ur) Ms(Ch Dp eC Hc Ii Ir Iz Jt Kg Kl Ni Oi Oz Qu Rh Ur Vo) Rh(Ao aW bO Ch Co Dp Hc Ii Ir Iz Jt Kg Kl Oi Qu Vo) eC(aW bO Ch cI Ed Hc Ii Jt Kg Kl Ly Ss Vo) Ii(bR Ed Fy Kx Ly Nf Ow Rf) Ch(bJ Hu Lu Ly Nf Og) Hc(aW Cv Ni Oi Ow Ri) Co(bR Ly Nf Og) aW(Nc Ni Oi Oz) Dp(Lu Qv Ur) Iz(bR Ly Nf) Kg(bJ Nf Ow) BaKl bRdI} Et{Ms(Fp Hw Im Io Ir Iv Jg Js Jt Lh Lu Lv Mi Ml Mp Mr Mt Mv Mw Na Nb Ne Nh Ni Nt Ok Pa Pe Pf Qb) Io(Fp Hw Ih Ir Js Jt Lh Li Lj Lv Ly Mh Mi Ml Mr Mt Na Ne Nf Nt Og Oi Ok Pa Pc Pf Qb Qd) Og(Fp Hv Hw Ij Im In Ir Iv Jg Jk Jt Lh Li Lu Mi Ml Mr Mv Na Nb Ne Nh Nt Pa Pf Qb Qd) Oi(Im Ir Iv Js Jt Lh Li Lj Lu Lv Mi Ml Mr Mx Nb Ne Nf Nh Nt Ok Pa Pf Qb Qd) Pc(Hv Hw Im Jo Js Jt Lh Lj Lu Lv Mg Ml Mt My Na Ne Nf Nh Nt Oy Pf Qd) Jo(Fp Hv Hw Ij In Js Li Lv Mi Mr Mv Na Nb Nf Nh Ni Nt Pa Pd Pf) Nf(Im Ir Iv Lj Lu Lv Ne Nh Nl Ns Nt Ok Pe Pf Qe) Lv(Im Ir Js Li Lj Lu Ml Mr Mt Mz Ne Oy Pf) Ni(Fp Ih Iv Li Ly Mh Mi Mr Nc Nk Pa Qd) Mt(Fp Hw Im Iv Na Ne Nt Ok Pe Qe) Lu(Fp Im Js Li Lj Na Ne Oy Qb) Mg(Jt Lh Mv Nb Nh Nt Ok Pe) Oy(Lh Mr Mv Ne Nh Nt Pd Qb) Fp(Hx Ik Ir Iv Ly Mz Pe) Im(Ir Iv Js Lh Ml Mr Pe) Ly(Mr Ne Nh Nt Wm) Nb(Lj My Of) Lh(Hu Of Pb) Oc(Mr Nt Pe) Ir(Pf Qe) Iv(Jt Pf) Uu(Pk Sr) Pe(Pa Pb) MiHq MxHu MyJg JtOk} Mm{Pe(Fp Il Im Io Ir Iv Jn Jo Js Lv Ly Ms Mt Mz Nf Ns Og Oh Oi Ok Oy Pa Pb Pc Po Qa Qe) Lv(Fp Im Io Ir Iv Jl Js Jt Lh Li Lj Ml Mr Mt Na Nb Nf Ni Oh Ok Pf Po Qa Qe) Me(Fp Ir Jg Jp Lh Li Lj Ma Mi Ml Mn Mr Na Nb Nh Ni Nt Nv Og Pa Pc Qb Qd Qe) Po(Hu Hv Hw Im Io Ir Iv Jo Js Jt Lh Mg Ms Mz Na Ns Oi Oy Pb Qa) Fp(Hx Ir Iv Jp Js Jt Lh Ly Mr Mt Mz Na Ni Og Oh Oi Pc Pf Qa Qe) Jn(In Ir Iv Lh Lu Mr Nb Nf Nt Og Oh Oi Pa Pc Pf Qa Qb Qc) Mz(Im Io Iv Lh Mr Na Ni Nt Og Oh Oi Ok Pa Pc Pf Qa Qe) Jl(Hv Hw Ij Im Io Ir Iv Js Mg Ms Mt Na Nf Ns Oy Qa) Qa(Io Ir Iv Kr Lh Mr Mt Na Nf Og Oh Oi Pf Us) Ni(Iv Js Lh Li Lj Mr Mt Pa Pc Pf Qb Qe) Iv(Im Io Is Mr Mt Nf Og Oh Pc Pf Qe) Ok(Io Lj Lu Mg Mr Ms Mt My Nf) Oh(Hv Hw Ir Jt Lh Ms Og Oi) Lh(Im Io Jo Og Oi Pb) Us(bA Dc Pi Pk Sr) Ir(Im Mr Pf Qe) Is(Jm Ml Na) Qe(Js Og Oi) Nb(My Og) Im(Io Js) Sr(Kr Uu) MiHq MrOg MtNa UuPk} Jl{Io(Fp Hu Im Ir Is Js Jt Lj Lv Ly Ms Mt My Mz Nf Ns Oe Oy Oz Pc Pe Pf Po Qa Qe) Oy(Hv Hw Ij Im In Ir Is Jg Jo Jt Lh Li Lv Md Ml Mt Na Ns Ny Pc Pd Pe) Pc(Hv Hw Im Ir Is Js Jt Lv Mr Mt My Na Nf Nk Oe Pe Po Qa) My(Ij Ir Js Jt Ml Mv Mz Na Nb Nf Ny Oh Pf Po Qa) Il(Fp Ij Im Ir Is Iv Js Jt Ml Na Nf Pe Pf Qe) Jo(Fp Hv Hw Ij Ir Iv Jt Lh Na Nf Nm Of Pe Qa) Nk(Im Js Li Lj Na Ne Nh Oh Pe Pf Po Qa) Nl(Fp Hu Is Iv Js Lj Na Ne Nh Pe Qa) Im(Hu Hw Ir Js Lv Mt Mz Na Nf Ns Po) Pb(Hv Hw Ij In Jt Lh Nf Pe Pf Po Qa) Ms(Ir Is Jg Ml Mt Mz Na Ns Qa) Hu(Ij Is Jg Jh Lh Mx Nf Pf) Qa(Jn Jr Mt Nf Ns Of Oh Oz) Ns(Ir Mt Mz Nf Pf Po) Of(Hv Hw Ij In Jt Md) Nc(Js Mt Mz Ne Nh) Oz(Is Oh Pe Pf Po) Lv(Mt Mz Nf Oh) Hq(Mi Pd Pe Po) Nf(Ch Hr Ii) Oe(Ir Mz Na) Us(Ji Pk Tv) Fp(In Ly) Mt(Hw Na) Ni(Aj Uu) Ii(Is Po) Oh(Hw Ir) Pa(Pe Pf) LyNh SrUu} Po{Oy(Cv dM Hw Im Iv Jt Lh Lj Mi Mk Mt Nh Nl Nt Oh Oi Oz Pd Pf Qa Qe) Pb(Hv Hw Ij Io Ir Iv Jn Jo Jr Jt Lh Lv Me Mr Ms Mz Nt Oe Oi Pc Qa) Pc(Hu Hv Hw Im Ir Iv Jm Js Jt Lh Lv Mg My Mz Nh Ns Oe Pe Qa Qe) Im(Hu Hw Ih Il Io Ir Is Iv Jt Lh Lv Me Ms Mt Mz Oe Oi Pe) Ms(Ir Iv Jg Jr Jt Lh Lv Me Mz Nb Oh Pe Qa Qe) Lv(Hu Io Ir Iv Jo Jr Me Mt Mz Ns Oi) Jt(Hr Hu Ii Il In Io Mg My Oe Of Oi) Pe(Hq Hr Hu Il In Io Jo My Ns Oe Oi) Lh(Hr Hu Ii Il Jo Mg My Oc Of Oi) Me(Hr In Is Jo Jr Mt Mz Oh) My(Ir Iv Jh Jn Mt Mw Mz) Hu(Hw Ir Is Jg Jh Mx Nk) In(Hw Ir Iv Jn Jr Mz Qa) Jo(Hv Hw Ij Jr Mz Nt Qa) Il(Iv Mr Nt Pa Qa Qe) Ns(Is Jr Mp Oh Qe) Qa(Ii Io Jm Oe) Qe(Hr Ii Jm Oe) Oi(Hr Iv Nh Nt) Ch(Jd Je Ni) Nk(Iv Ne Nh) Is(Ii Jm Nl) Ni(Aj Co) Ir(Hr Jr) Oe(Nt Oh) Og(Pa Wm) HwOf JnJr} Ji{Uu(aV aW bA bE bO CT cZ dA Db Dp Ez Fb Fn Hb Hc Hf Hu Hv Jd Jv Jy Kx Ly Ma Ms Nf Ni Nr Pd Pk Qc Qy Rf Rh Ri Sr Tz Us Wm) Us(aK aV aW bA bE bN bO bV cI cK cN Co cT dA dI dM Dp Ed Fn Hb Hc Hu Ki Ms Nf Ql Rf Rh Ri Tz Wm) Dp(aE Aj Ao Ch Cq Hc Jo Jv Lu Ly Mg Ms Ni Oi Qg Qv Rf Rh Ri Uc Ur) aW(Af Aj bJ bN Ch cZ Db eC Hv Jv Ly Me Mr Ms Nc Nf Ni Oy Rh Ri) Hc(bJ bO cI cZ dI dM Jd Je Ju Jv Ms Ni Ow Pk Qg Qy Rf Rh Ri) Jv(aE Aj aK aV bJ bN bX Db dI Ko Kx Kz Ly Nf Og Oy) bJ(aE Af Ao bN Ch dE dI Kg Lu Mg Ms Oe Og Oy) Aj(Ba cZ dA Hu Ms Nf Ni Qy Ri) cZ(aD bN Ch Ly Ms Nf Og Oy) Ri(bX Ko Kz Ly Nf Oy) Qg(bX Ko Nf Oy) dI(bR Ly Nf Oy) bO(Fn Me Rh) dM(Nf Oy Pk) Kr(bX dA) ChHu KgRh OybE cIeC} Oh{Ms(Fp Hw Ij Im Ir Is Iv Jg Jn Jo Jr Jt Lh Lv Me Mi Mn Mr Mz Na Oi Pa Pc Pe Qa Qe) Og(Fp Hv Hw Ii Ij Im In Ir Jg Jn Jo Jr Lv Md Mi Mr Mt Mz Nm Nt Pa Pc Qa Qe) Ni(Fp Hc Ir Iv Jg Jn Jp Jt Lh Li Lv Ly Mi Mn Mr Mt Ne Pa Pb Pe Pf Qa Qe) Lv(Fp Im Io Ir Is Iv Jn Jr Jt Lh Lu Me Mr Mt Mz Nb Oe Oy Pc Pe Qa) Oi(Hw Im Iv Jp Li Lu Mi Mn Mr Mt Ne Nh Nm Pa Pf Qd) Jr(Fp Im In Ir Is Iv Jn Jt Lh Lu Me Ns Pc Pe Qa) Pe(Fp Hq Il Im Jn Jo Me Ns Oe Pb Pc) Pc(Fp Ir Is Iv Jn Jt Lh Mz Qa) Me(Im In Is Jg Lh Mn Mt Pf) Ir(Fp Im In Is Jg Jo Oy) Jt(Ii Im In Io Oe Oy Pb) Jg(Fp Hu Jn My Ns Qa) Lh(Ii Im Jo Oe Oy Pb) Is(Il In Io Jm Oe) Iv(Il Im In Jo) Qa(Ih In Jo Oe) Jn(Fp Im In Js) FpJp MiHq MyNb MzIm HcdM} Jr{Og(Im Ir Iv Jn Jo Jt Li Lv Ma Me Mi Mn Mr Mt Mw Mz Nf Nh Ni Nm Nt Pa Pd Pf Qa Qe) Oi(Fp Im Ir Jg Jn Jt Lh Li Lv Ma Mi Mr Mt Mw Mz Ne Nh Ns Nt Pa Pd Pe Pf Qa Qe Wm) Im(Fp Ih Io Ir Is Iv Jg Jn Lh Lv Me Mr Mz Ns Oe Oz Pa Pe Pf Qe) Lv(Fp Io Ir Jn Mr Mt Mz Ni Pc Pe Pf Qa Qe) Jg(Fp Hu Ir Jn Me Ms Mv Mw Ni Ns Oe Oy) Pc(Fp Iv Jn Jt Lh Mr Ms Mz Pf Qa Qe) Me(In Is Lh Li Ma Mn Pa Pc Pf Qe) Pf(Ir Is Iv Jn Ns Oy Qa) Ni(Lh Li Mi Mn Mr Pa) Qe(Il Io Ir Jn Mz Ns) Pc(Fp Il Oy Pa Ph Qa) In(Ir Jt Lh Mr Wm) Lh(Jo Ms Oy Pb) Wm(Ly Ms Oe) Nh(Mn Nc Nl) Io(Jt Mr Qa) Jn(Js Ma Pa) Mi(Hq Oy) My(Mw Nb) Nl(Is Mr) Us(Co dM) ChJd FpPa NsMp MaIv MsNb NcNe HcdM QaQc JoJt} Ni{Im(Ir Iv Jg Jn Js Jt Lh Li Lv Me Mi Mj Mn Mp Mr Mz Ne Og Oi Oz Pa Pf Qe) Pf(Aj Hc Ir Iv Jn Lh Lv Me Mn Mt Ne Og Oy Pa Pb Pc Qa Qb Qe) Qe(Aj Ch Fp Is Jn Li Ly Mi Mn Ms Mt Mz Oi Pa Pb Pe) Jn(Aj aW Jg Lh Li Lv Mi Mn Mr Og Oi Ok Pa Pe Qa) Pe(Co Jo Li Lv Ly Mn Ms Mt Og Ok Oy Pb Qa Qb) Aj(Ba bV cN dA Fa Hu Is Jk Kx Qa Rf Sr Tn) Qa(aW Ch Mi Mn Mr Mt Og Oi Pa) Li(Lv Me Mi Mt Og Oi Ok Pa Pc) Hc(aJ Cv dM Is Sr Tn) Is(aW Ch Fp Mt Qb) Ok(Mg Mp My Pa Qb) Pc(Fp Lh Lj Qb Qd) Jd(Co Iz Uu) Sr(aW Jv Uu) Ch(Bo Hu) Jg(Lj My) Oy(cN Tn) aW(Nw Oz) BaUu CoRf CvCx FpJp MnNe LhOg PkdM bRdI bVfP} Is{Pc(Il Im Io Ir Jm Jn Lh Lv Mr My Mz Na Nh Ns Oe Oy Pe Pf Qa Qe) Io(Im Jn Jt Lh Li Lv Ma Ms Mz Na Ns Pe Pf Qa Qe) Il(Fp Im Iv Jg Lh Li Mi Mr Nt Pa Pe Pf Qa) Ms(Im Jg Lh Mt Mw Mz Nb Nf Pe Pf Qe) Oe(Im Jg Lh Nf Nt Pa Pe Qa Qe) Pe(In Jm Jo Lv Nl Ns Oy Pb) Pf(Hu Im Jm Jn Me Nl Oy Pb) In(Fp Ir Jn Jt Me Qa) Lv(Im Jn Li Mt Mz) Lh(Hu Ii Jo Oy Pb) Og(Ii Iv Mi Mw Pd) Oi(Im Ne Nf Nt Pd) Hc(aW Cv dM Qv) Fp(Ih Jm Nl) Mt(Im Me My) Jg(Hu Ns Oy) Mi(Hq Oy) Nh(Nf Nl) Im(Jn Mz) Uu(Cv Sr) ChbJ MeJm MyNb NeNl JnJs JoJt OyPd} Sr{Uu(Ap aW bA bE bF bH bP bQ bW cN Fb Fn Gp Ih Ir Jg Kc Ke Kf Ki Ko Kp Ma Mn Nb Og Oi Ow Pz Qe Qt Qv Rc Rf St Uh Uk Ur Us) Jv(aK aW BO bX Cv dI Dp Ed Gp Hc Kg Kr Kx Kz Ly Ms Nc Nf Nl Oe Oi Oy Oz Qg Qv Ri Ur Us

Figure 8 Continued

Figure 8 Continued aW bJ bN Ch cZ dI dM Dp Hc Jv Kg Kj Qg Rh Ri Uu) Pf(Hw Im Ir Iv Jn Jt Lh Lv Mm Mz Ng Og Oi Oy Pc Qa) Kq(aF Ao Bb Bg Ch Co eC Ef
Hc Iz Kg Kl Kr Of Us) Et(Hv Hw Jt Li Lj Ml Ms Na Ne Nh Nt Og Qb Qd) Jn(Fp Jg Jr Lh Li Lv Me Mr Ng Ni Og Oi Pa) Jr(Fp Iv Jg Jt Ma Me
Mr Mz Ng Ns Og Oi) Lh(Fp Im Is Lv Me Mm Ng Og Pb Pc Po Qa) Un(Aj eC Hc Ii Jv Kg Kj Kr Ms Oi Oy Rh) Lv(Fp Im Is Iv Jt Li Mm Mt Mz
Qa) Kj(Ad Cw Dc Id Ij Ke Kn Pi Qa Sr) On(Bg Ch Co Hv Hw Io Li Mr Uu) Fp(Ir Iv Jp Jt Mm Mz Pc) Im(Ir Iv Jt Me Mr Mt Ni) Mm(Ir Iv Js Me
Mz Ni) Qa(Io Ir Iv Me Mt Mz) Po(Hu Hw Ns Pb Pc) Ke(Aj Dp Hc Oy Uu) Is(Ir Jm Li Oe) Sr(Dp Jv Oi Ri) Jt(Ng Og Pc) Li(Ir Me Ni) bA(aD
aM dM) dN(Ql Qv Us) Nb(Og Oy) Pc(Iv Mz) BaUu ChJd DceC NiQb PkdM aMcT Constrained panels with 2 analytes, where 1.0E-4 >= 'model p-value' > 1.0E-5. Contains 948 panels of 61,235 total panels evaluated. : Kq(aE aK
aL aM aW bF bH bJ bM bO bP bW bX Cq cZ De dI dM Dp Ed Fn Hq Ii Jg Jj Jo Jt Jv Ki Kx Ly Mg Ms My Ng Nq Nx Og Oi Ow Oz Pk Qu Rf
Rh Sr Ua Uc Uf Ur Vo) Un(aD Ao aW bA bJ bO bW bX Ch Co Cv dI dM Dp Ed Fn Hb Ih Io Ir Iz Jj Jo Jt Kl Ko Kx Lu Lw Ly Mg Mq Nc Nf
Ng Ni Nm Oe Og Ow Oz Pk Qg Qu Qv Rf Ri Ur Vo) Lw(aW bA bJ Ch Cs cT dM Fa Fn Hf Jd Jg Jt Ju Kg Ki Kx Kz Lj Lu Ma Mh Mi Ml Mn
Mp Ms Mv Mw Mx Na Ne Nf Ng Nh Ns Nv Ny Oi Pa Pc Pk Qu Ri Sr Ug) Ni(aD AJ aP aW Ax bA bV bW Ch cN Cs Cv dA dI dM Dp Ed Fp
Hc Iv Jg Jp Jt Kx Lh Lj Lv Mi Mn Mp Mr Mt Mw Mz Nt Ny Pa Pc Pd Pk Qd Rf Ri Sr) Sr(aW BO Ch Co Cv dI dM eC Ed Hc Iz Jj Jq Ju Kg Ki
Kl Kr Kx Ly Ms Nc Ng Nl Oe Og Oy Oz Pk Qg Qu Qv Rf Ug Ur Us Vo) Jq(aE aF aM Ao aW bA Bb bM bN bW Ch Co Cs Cx dA dl dM eC Ed
Fn Iz Jv Kg Ki Kr Kx Kz Ow Pk Qg Qv Rf Rh Ri Uf Ur Us) Ke(Ao aW bJ bO bX Ch Co cZ dI dM eC Ed Fn Iz Jj Jv Kg Ko Kr Kx Lu Ly Mq
Ms Nf Oi Ow Oz Pk Rf Rh Ri Ur Us) Cv(aD Aj aM aW bA bV Ch Cs cT Cx dA Dc dM Dp Fp Hc Iv Jn Jr Jv Kz Me Mq Mr Nf Nr Oy Pe Pk Po
Qa Qn) Im(Fp Hv Hw Ij In Io Jo Js Li Lu Mi Mj Ml Mm Mn Mx Na Nb Ne Nf Ng Nh Nt Og Oi Pa Pc Pd Qd Qe) Jn(Ch Co dM Hc In Io Ir Iv Jp
Jt Jv Kr Kx Lj Ma Mp Mt Mw Mz Nf Nh Nt Nv Ny Pg Qb Qd Us Uu) Fp(Hv Hw Hx Ij Ik Jg Jo Js Ly Ma Me Mi Mn Mp Mr Mt Mv Mw Mx Na
Nb Nf Ng Nt Og Oi Pa Qd) Mz(Iv Jg Jp Jt Lh Li Lx Ma Me Mn Mp Mr Mt Mw Na Ne Ng Nh Nt Ny Og Oi Oz Pa Qb Qd) Lv(Ir Jg Jp Js Lj Me
Mi Mn Mp Mr Mw Mx Na Nb Ne Nf Nh Nt Ny Pa Pc Pd Qb Qd) Lx(Ch Co Hv Jo Jp Js Li Lj Mm Ms Mv Mx Na Ne Nh Ns Nt Ny Oi Pb Pf Pg
Qb Qd) Me(aJ dM Jd Jg Jp Kx Lj Ma Mi Mn Mp Mr Mt Nh Nt Nv Pa Pc Pd Qb Qd Rf Ur) Iv(aW bV Jg Jp Lh Li Lj Ma Mn Mp Mr Mt Mw Ne
Nf Ng Nh Nv Ny Og Pd Qb Qd) Pk(AJ aP aW bA bJ bW Ch cN Dp eC Ji Jj Jv Ki Kj Kx Mq Nw On Rf Uf Ur) dM(aC aD aM bQ bR bV cT Dc
dI Ed Is Jj Jr Kx Mq Mr Nf Nr Nw Oi Po Rf) Ch(bA Dc Dk Fa Fr Fy Hu Is Jh Jl Jr Jy Kx Mq Nn Ny Pe Po Qa Rf Ut) Li(Hv Hw Ij Jo Js Jt Lh
Mi Mm Mr Mt Nb Ng Nh Nt Og Oi Om Pc Pe Qe) bA(aJ aP aS aW bJ bM bR bW cK cN dA Dc Hc Jj Jv Kx Oy Ur Us Uu) Oh(Ij In Jg Jo Jp Js
Lu Mi Mn Mt Na Ne Nh Nm Ns Nt Oe Pf Qd) Aj(Ad Cp Cw Dc Fy Id Ij Jd Kd Kn Mq Nn Om On Qa Vt) Mm(Hv Hw Ij In Jo Jt Mi Ml Mr Mt
Na Nb Nf Nt Qb Qd) Dc(aW bJ bM bW Co dI Dp Hc Jj Kx Mq Oy Ur Us Uu) Ir(Jg Jp Lj Ma Mn Mp Mr Mt Nh Nt Nv Ny Pc Qb Qd) Lh(Hu Jo
Lj Mr Ms Mt Ne Nh Of Oi Om Oy Qb Qd) Fr(Ih Ij Jo Mg Ml Mt Mx Nf Nl Nn Oe Qd) Qe(Hv Hw Il Jo Js Mi Ml Ms Na Nf Nh Nt) Jt(Io Jo Jp
Lj Mr Mt Ne Nh Oi Qb Qd) Uu(Dk Fy Id Is Jd Jl Jr Jy Mq Om Rf) Pf(Hv Ij Jo Js Mr Mt Na Nb Nh Ns Nt) Ng(Jd Jk Ma Mi Mv Nb Nt Nv Pd
Qd) Ji(aE cl dA eC Ed Fn Ko Kx Rf) Qd(Jg Mr Na Nn Og Oi Pc Pe) Jj(dA Fy Jy Kx Kz Rf Uv Vt) Jr(aW eC Hc Jv Kr Kx Ur Us) Om(Bg Co Iz
Js Nh Pb Pc Qb) Is(aD aW Co Hc Jv Kr) Qa(aW Dp Hc Kr Ur Us) Kj(Fy Kd Kp Kr Na Up) On(Ao Hc Iz Jv Qu Us) Mr(aW Mn Og Pc Qb)
Kx(bV Jv Oi Qv Ri) aD(aJ aP cT Hu Jd) Wm(Jp Ly Mu Na) Fy(Ao bW Co Hc) Nn(Jo Lj Mi Pa) Nt(Mt Og Oi Pc) Mq(aW Dp Jv Rf) aJ(aM bR
cT Oi) Id(eC Hc Kr) Pe(Kr Lj Qb) Bg(Mu No) Co(Jd Po) Mt(My Na) Nb(Ms My) Qv(aA Dp) Js(Pa Pc) Nw(aM aW) Oi(aP Rf) Ur(In Vt) Ut(Iz
Oy) FaJv NoVv MiHq MnNh NaPc JgOg JlUs KdeC aPcT bRdA Constrained panels with 2 analytes, where 1.0E-3 >= 'model p-value' > 1.0E-4. Contains 2,440 panels of 61,235 total panels evaluated. : Rf(AD AJ aM Ao aP As aW bA Bc bM Bn bV bW cK cN Co Cp Cq cT Cu Cv CW dA Dc dG dI dL Dp Ed Fa Hc Hv Hw Id Ij In Io Ir Is Iv Jd Jn Jr Jt Jv Jy Kd Kj Kl Kn Kp Kr Kx Kz Lh Lu Ly Md Ml Ms Na Nf Ng Nn Oe Og Ok Om On Ow Oy Oz Pb Pe Pi Qa Qe Ql Qv Ra Rb Ri Rj Tn Tv Uc Ud Uf Ul Up Us Vp Vt) Kx(AD AJ aM aP As aW Ax bJ bW Co Cp Cq Cs cT Cu Cv Cw dA dG dI dL Dp Ed Et Fa Fr Fy Hc Hu Hv Hw Id Ij In Ir Is Iv Jd Jl Jy Kd Ki Kn Kp Kr Lu Ly Ml Mq Mr Ms Mu Mx Mz Na Nf Ng Nr Nw Ny Og Ok Om On Ow Oy Oz Pb Pc Pe Pi Po Qa Qe Ql Ra Rh Rj Tv Uf Up Ur Us Uu Uv Vp Vt Wm) dM(Ad An Ar As Ax Ba Bn Ch Cp Cq Cs Cu Cw Dk Dp Et Fa Fp Fr Fy Gl Hc Hu Hv Hw Id Ij Im In Iv Jd Jl Jy Kd Kn Ky Kz Lj Lx Ly Ma Ml Mn Mt Mu Na Nc Nn Ny Oe Og Oh Ok Om On Ow Oy Oz Pc Pd Pe Pf Pi Qa Qd Qe Ql Qt Qv Ra Rh Ri St Ur Us Uv Vt) Cv(aC Ad Af aJ aP As Ax bJ bQ cI Cp Cq Cu Cw dF dG dI dL Ed Fa Hu Hv Hw Id Ij Im Io Ir Is Jd Jj Jl Jy Kd Kn Kq Kr Ky Lv Lx Ly Ml Mu Na Nn Oe Og Oh Oi Om On Ow Oz Pb Pf Pi Qe Ql Qv Qx Qz Ra Rh Ri Tv Up Us Uu Uv Vt) Dp(AD aJ aM aP As aW Ax bA Bn bV bW cN Cp Cq Cs cT Cu Cw dG dL Ed Fa Fr Fy Hv Hw Id Ij Ir Is Iv Jl Jn Jr Jy Kd Kn Kp Kr Ky Me Ml Na Nf Nn Nw Oh Oi Ok Om On Pb Pe Pf Pi Po Qe Ra Rj Tv Uf Up Ur Uv Vp Vt) Vt(aD aE aJ aK aP aW bA bJ bP bW Ch cN Co Cs cT dA dI dJ eC Ed Fa Fr Hc Im Jd Jn Jr Jv Jy Kg Kj Kr Kz Lu Ly Me Mm Mq Mr Ms Mu Nc Nf Ni Nn Nw Og Oi On Ow Oy Oz Qe Qg Ql Qv Rh Ri Sr St Uf Us Uu) Me(aD aM aP aW Ax BA bJ bP bQ bV bW bZ Ch cN Cs cT dA Dc dF dG dI dL Ed Fa Fb Id Ih Ir Je Js Jv Jy Kk Kq Mj Ml Mv Mw Mx Na Nb Ne Nf Ni Ny Og Ow Oz Pg Ql Qv Qy Rh Ri Sr St Uf Uh Us Wm) Aj(As Aw BA Bn bV Cq cT Cu dG Dk Et Fa Fr Hu Hv Hw In Ir Is Iv Jl Jn Jo Jr Jt Jy Kf Kg Kp Kr Lh Lw Lx Md Ml Mu Mz Na Nf Nr Ok Ow Pb Pd Pe Pf Pi Po Qe Ra Rj Tn Tv Uc Up Us Ut Uv Vp) Nf(aD aJ aM aP aW Ax bA bV bW Ch cN Cs cT dA Dc dG dI dL Ed Fy Id Jd Jg Jp Jv Kd Kj Kq Li Lj Ma Mn Mp Mr Mt Mw Ne Nh Ni Ns Nt Nv Ny Og Ow Pc Pk Qb Qd Qg Ql Qv Ri Sr St Uf Ur Wm) Us(Ad aP As Bn Cp Cq Cs cT Cu Cw dG dL Fa Fy Hv Hw Id Ij Ir Is Iv Jd Jj Jt Jy Kd Kf Kj Kn Kp Kr Lh Lx Mq Mr Mu Na Ni Nn Nw Ok Om Pb Pe Pi Pk Po Qe Ql Ra Rb Uc Up Ur) Ch(Ad aJ aP Aw Ba Bo bQ bV cN Cp Cs cT Cw dA dF dG Ef Et Gl Id Ij Im In Iv Je Kd Kf Kn Kz Lh Ma Ml Mr Mt Mw Nb Nr Nt Nv Nw Oh Ok Ow Pd Pf Qd Qe Ql Qx Qy Ra Tn Uv) Hc(Ad aJ aP As Ax Cp Cs cT Cu Cw dG Et Fa Fr Hw Ij Iv Jd Jj Jl Jy Kd Kf Kk Kn Kp Lh Lx Ml Mq Na Nn Nr Nw Oh Ok Om Ow Pe Pf Pi Pk Po Qc Ql Qy Ra Tn Tv Up Ut) Jj(AD aJ aM aP As Ax bJ Bn bO bV cN Cp Cq Cs cT Cu Cw Dd dF dG dI Ed Ez Fa Fb Ha Id Jd Jv Kd Kf Kn Kp Kr Oa Ow Pi Ql Qy Ra Rh Ri Rj Rm Uc Ul Up Ut Vp) Pk(aM bP bV cK Co Cs cT dA dG dI Ed Et Fa Fr Hu Is Jd Jl Jn Jr Jy Kg Kk Kr Lu Lx Ly Mm Mr Ms Mu Nc Nn Nr Og Oi Ow Oy Oz Pe Pf Po Qe Ql Qv Rh Ri St Uh Uu) Ni(aM aV bJ bM bR cI Co cT Dc eC Fa Fy Id Ih Ij Ir Jd Jk Js Jv Kj Kr Ky Kz Lz Ma Mj Mv Mx Na Nb Ne Ng Nh Nk Nl Nv Oa Og Ow Oz Pg Ql Qv St Uf Uh Ur Uu) aW(Ad aJ aM aP As Bn bQ bW Cp Cq cT Cu Cw dA dF dG dL Et fR Fy Id Ij In Jd Jl Jn Jy Kd Kn Lx Ml Mt Mu Nn Ny Ok Om On Ow Pe Pf Po Qd Qe Ra) Uu(Ad aP Aw Ax Cp Cs cT Cu Cw dG Et Ez Fa Fr Hu Ij Iv Jg Jt Kd Kf Kn Kp Lh Ma Mu Nn Nr Nv Nw Ok Ow Pd Pe Pf Pi Po Qa Qd Qc Ra Tn Uf Ut) aD(Ax Ba Bc bQ bV bW cE cN Cs dA dF dG dI Ed Fa Fp FR Iv Jl Jn Jr Jy Kq Ky Lw Lx Ma Mq Mr Mu Nn Nr Nw Oh Om On Ow Pe Pf Po Qa Qe Sr) aM(aP Ax Ba bF bJ Bo bQ bR bV bW cE Cs cU dA Dc dF dG dI Fa Fy Hu Is Iv Jd Jn Jr Jy Ke Lw Lx Mq Mr Mu Nn Nr On Pe Po Qv Ri Sr St) Ed(Ad aP bA bJ bV cN cT Cw dA Dc dI Et Fr Fy Id Ij Is Jd Jn Jv Jy Kd Kn Mq Mr Mu Nw Oi Om On Pe Qa Qv Ra Rh Ri St Uf Up Ur) aJ(Ad An As Bn bQ bX Cp Cq Cs Cu Cw dA Dc dI Id Ij In Io Is Iv Jn Jr Jv Jy Kd Lw Ml Mq Mr Ny Oe Om On Oy Pe Qv Ra Ri Sr) Ur(Ad As Cp Cq cT Cu Cw dA Fy Hv Hw Id Ij Ir Is Iv Jl Jn Jt Jy Kd Kn Kp Kr Md Mq Na Om On Pb Pe Pi Po Ra Rj Up Uv Vp) dI(Ad As Bn bR Cp Cq Cs cT Cu Cw Et Hv Hw Id Ij In Ir Is Iv Jd Jn Jr Jv Kd Kn Ml Mq Na Ny Ok Om On Pi Qa Qe Ra Vp) Fy(aA aE Al Bb bH bM bO bX Hb Hq Ii Iz Jf Jo Jv Kg Ki Kl Kr Kz Lu Lw Mm Mq Nl Ow Oy Oz Pa Ql Qu Qv Qz Ri Uf Vo) Og(Cs Dc Hv Hw Id Ij Ir Jd Jk Jo Jp Js Kd Ke Kn Lj Lv Ma Mi Mm Mp Mt Mv Mw Na Nh Nv Ny Pa

Figure 8 Continued

Pc Pd Pg Qb Ra Uv Wm) bW(Ad An As Ax Bn bR Cp Cq Cs cT Cu Cw Fp Hw Ij Im In Is Iv Jn Jr Kd Kn Ml Mr Na Nr Ny Om Pc Pi Qa Ra Sr Tv) Mt(Hv Hw Ij Jg Jo Jp Js Lj Ma Mi Mj Ml Mn Mp Mr Ms Mv Mw Nb Ne Ng Nh Ns Nu Nv Ny Oi Pa Pc Pd Pg Qb Qd Wm) Nw(Ad Ao As bA Bb Bg bJ Bn bV cN Co Cp Cs cT Cu CW dA dL Id Jv Kd Kr Kz Ow Pi Qv Ra Rh Ri Rj Sr Tv Up) Mr(aP bV Cw Dc Hv Hw Ij Jg Jo Jp Js Jv Lj Ma Mi Ml Mp Mv Mw Mx Na Nb Ne Ng Nh Nt Nv Ny Oi Pa Pd Ri) Qv(aP dA Dc Fa Fp Id Im Is Iv Jd Jl Jn Jr Jy Kd Ke Kq Lx Mq Nn Nr Oh Ow Pe Po Qa Qd Qe Ql Ri Ul Uv) Oi(Ax bA bV Cs Dc dG dL Fa Id Ij Ir Jd Jg Jp Lj Lv Ma Mm Mp Na Nb Nh Nv Ny Ow Pc Pd Qb Ql St Uv) Pc(Hv Hw Ih Ij In Jo Jp Lj Ma Mi Mj Ml Mm Mn Mp Ms Mw Mx Nb Ne Ng Nh Ns Nv Ny Pa Pd Pg Qb) Sr(aE aK aN Ao aP bA bH bJ bV bX cK cT dA dJ Io Iu Jo Jr Ky Lu Lx Mg Mq Mu Ow Rh Uf Uk) Jv(aP Ax bV Cs cT Cw Dc Et Fr Id Im Iv Jd Jl Jy Kd Kn Kz Nn Nr Om Ow Pe Pf Po Qa Qe Tn) Kj(As Cp Cq Cu Fa Hv Hw Is Jd Jl Jn Jr Jt Kf Mq Nm Nn Nr Ok On Pb Pd Pe Po Qe Ra Tv) Cs(aP bJ bM bO bV cN Co cT Cw dA Hu Io Jd Jy Kq Kr Lu Ly Mu Nc Oe Om On Oy Ri Uf) Nh(Hv Hw Ij Jg Jo Jp Js Lj Ly Ma Mi Mj Mm Mp Mw Mx Na Nb Nt Nv Ny Pa Pd Qb Qd) Ri(aP Ax bA cT Dc dL Fa Id Is Iv Jl Jn Jr Kd Kq Kz Mq On Pe Po Qa Qe Ql Tv Uv) Co(Ax bA cT Cw Fa Fp Id Ij Iv Jh Jl Jr Jy Kd Mq Mu Nn Nr Ny Pd Pf Qa Qe Ut) Kr(Ax bA Dc dL eC Et Fa Iv Jl Kd Kn Lh Mq Nn Oh Ok Om On Ow Pi Po Qd Qe Ra) Lj(Hv Hw Ij In Jg Jh Jo Jp Js Jy Ma Mi Mm Mn Mp Mw Mx Na Nb Nt Nv Pa Pd) bJ(Ad As Cq cT Cu Cw Id Ij In Iv Jn Jr Kd Kn Ml Mz Pe Pi Qa Ra Up Uv Vp) Ng(BA Dk Id Ij Jh Jo Jp Jy Kc Lv Mm Mn Mp Mw Na Nx Ny Pa Pg Qb Ut) Oy(Ad aP Ax Ba Cp cT Cw dG Fa Id Jd Jy Kd Kf Kn Kp Mi Pd Pi Ra Tn Tv) eC(Ad As Cp Cq Cu Cw Hv Hw Ij In Ir Iv Jn Kn Kp Na Om Pi Qa Rj Up Vp) Nt(Hv Hw Ij Jg Jp Js Ly Ma Mi Ml Mn Mp Mv Mw Mx Na Ny Oe Pd Qb Qd) cT(bM bP bR bV cK cN cW dA dG dL Iv Jl Jy Ki Ml Oz Qa Qe Qu St Uf) Mm(Hu Io Jg Jp Kd Lu Ma Mh Mj Mn Mp Mv Mw Mx Ne Nv Ny Pa Pd Pg) Qb(Hv Hw Ij Jg Jo Jp Js Li Ma Mi Ml Mn Mp Ms Mx Na Nb Pa Pd) Id(aP Bo dA Fn Jd Jy Kg Ki Lu Ly Mq Ms Oe Of Ow Oz Qg Rh) Jn(aE aP bA bM bO bP bV cN dA Iz Jy Kg Ki Kl Ow Qu Rh Uf) Na(Jg Jp Li Ma Mi Ml Mn Mp Mw Mx Nb Ne Nv Ny Pa Pd Pg) On(aE Ap Ax Bb bF bV De Dk Jd Kg Ki Kl Kz Oa Qt Qy Rh) bA(Io Is Iv Jr Ju Jy Ki Kz Ly Ml Mq Oz Qa Qe Ql Qu Uf) Dc(aP Bo cN Fn Jd Kg Ki Lw Nc Of Ow Oz Qg Ql Rh Uf) Ne(Hv Hw Ir Jg Jo Jp Js Ma Mi Mn Mp Mw Nb Ny Pa Qd) Kq(cI Cp Dk Ib Jk Kz Md Mq Nb Nc Nv Pa Pb Pg Qg Ut) bV(aX bR cA fP Io Is Jr Jy Lw Ml Mq Mu Nc Nr Pe Ql) Kd(Bo Fa Fn Jd Kg Ki Ly Mq Nn Ow Oz Qg Ql Rh Uf) Hw(Jg Jp Lv Ma Mi Mn Mp Mw Nv Ny Pa Pd Pg Qd) Is(Al Ao aP bM bP bR cW dA Iz Ju Kg Qu Tz Ua) Js(Jg Jp Ma Mi Mn Mp Mw Nb Nv Ny Oz Pd Qd Wm) Pa(Hv Ij Ir Jg Jp Li Ma Mn Mp Mw Ny Pd Qd) Qa(BO Fn Fw Iz Kg Ki Qg Qu Rh St Uf) Mq(Cw dA Ki Kn Ky Pi Ql Qu Ra St Uv) Hv(Jg Jp Ma Mi Mn Mp Mw Nv Ny Pd Qd) Ly(Fa Jd Ki Kk Kn Ld Ow Ql Ra Uf) Ml(aP bM cN dA Jp Lv Mp Mw Nv Ny) Jo(Jg Jp Kn Ma Mn Mp Mw Nv Ny Qd) Jr(aE bM bO cN dA Kg Kz Ow Rh Uf) Mi(Ir Jg Jp Mn Mp Mw Ny Qd Wm) Kg(Ad Cw Ij Kf Kn Ok Om Pe Po) Pd(Ir Jg Jp Mn Nb Ns Ny Pb Qd) dA(bU cA cF fR Iv Ke Ky Qe) Lw(aE Ax Bg bN cI Ky Ow) bM(Ad As Cp Cq Cu Cw Iv) Ao(Jd Jy Mu Om Pe Ut) Wm(Iq Ir Lv Mn Mz Qd) Ms(Fa Jd Jg Mp Nv Ow) Tv(Im Jy Mw St Uf Uh) Ij(Jp Ma Mn Mp Ny Qd) aP(aC bR bX Fp Iv Qu) Bg(Jd Jy Mw Ny Ut) Nb(Jp Ma Mp Ny Qd) Pe(bO Iz Ki Qu Uf) Bo(Ad As Cw Ra) Lv(Ih Ma Mv Nv) Mx(Ir Jg Jp Mn) Jl(aE bO Kl Qu) Kn(Fn Qg Rh Uf) cW(Fp Iv Ql tF) Cw(Fn Lx Of) Ns(Jg Mp Nv) My(Jd Jg Ut) Ir(Mv Mw Pg) St(Kz Ow Ra) Jy(Ax bF Uv) bR(bQ cN dG) Mu(Ax bF) Iv(cN dG) Jd(Iz Qu) Jp(In Io) Ke(aK bP) BaKl PobO FafP FnPi LxKz MnQd HuJg IbOm TnOz RaUf OwUv bNfR dGdH Constrained panels with 2 analytes, where 1.0E-2 >= 'model p-value' > 1.0E-3. Contains 3,590 panels of 61,235 total panels evaluated. : Rh(AD AJ aM An aP As aW Bn bV bW Ch cN Cp Cq Cs Cu Cw dA Dd dF dG dl Dk dL Dp Et Fa Fb Fp Fr Gl Hc Hu Hv Hw Ij In Ir Is Iv Jd Je Jl Jo Jp Js Jt Jv Jy Kf Ki Kk Kp Kr Ky Kz Lh Lx Ly Md Mj Ml Mm Mp Mr Mu Mw Mz Na Nf Ng Nm Nn Nr Oa Oe Og Oi Ok Om Or Ou Oz Pb Pc Pd Pe Pi Po Qb Qd Qe Ql Qv Qy Ra Rb Ri Rj St Tn Tv Uc Uf Uh Ul Up Ur Us Ut Uv Vp) Jv(AD An Ar As aW Ba Bc bF bJ Bn bQ bW bZ cN Cp Cq Cu dA Dd dF dG Dk dL dM Dp Fp Gl Hc Hu Hv Hw Ij In Ir It Jh Jo Jp Js Jt Kf Kk Kr Kp Ky Lh Li Lj Lv Lx Ly Ma Md Ml Mm Mn Mp Ms Mt Mu Mv Mw Mz Na Nb Nm Nt Nv Ny Oa Og Oh Oi Ok Or Ou Oz Pb Pc Pd Pg Ph Pi Qb Qd Ql Qt Qv Ra Rb Ri Rj St Tv Uc Uf Uh Ul Up Ur Us Ut Uv Vp) Kr(Ad aE aJ aM An aP As aW bJ bM Bn Bo bP bW Ch cN Cp Cq cT Cu Cw dA Dd dG dl Dk Ed Fn Fr Hc Hv Hw Ij Im In Ir Jd Jo Jp Js Jt Jy Kf Kg Ki Kk Kp Ky Li Lj Lx Ly Md Mj Ml Mm Mn Mp Mr Ms Mu Mx Mz Na Nf Ng Nm Nr Nt Oa Og Oi Oy Oz Pb Pd Pf Qb Qg Ql Qv Rb Ri Rj St Tn Tv Uc Uf Uh Up Ut Uu Uv Vp) Ri(AD Aj An Ar As aW Bn bV bW Ch cN Cp Cq Cu Cw dA dF dG dl Dp Et Fp Fr Gl Hc Hu Hv Hw Ij Im In Ir Jd Jt Jy Kf Ki Kk Kn Kp Ky Lh Lj Lu Lx Ly Md Ml Mn Ms Mu Mw Mz Na Nc Ng Nm Nn Nr Ny Oa Og Oh Oi Ok Om Or Ow Oy Oz Pb Pc Pd Pf Qb Qd Ra Rb Rj St Tn Uc Uf Uh Ul Up Ur Us Ut Uu Uv Vp) Ki(AD aJ aM An aP As aW Ax Bn bQ bV cN Cp Cq Cs Cu CW dA Db Dd dF dl dL Dp Ed Et Fr Hc Hu Hv Hw Ij Im In Ir Iv Jd Jo Js Jt Jy Kf Kn Kp Ky Kz Lh Lu Md Mj Ml Ms Mu Mw Mx Na Nf Nm Nn Nr Nw Oe Og Oh Oi Ok Om Ow Oy Oz Pb Pe Pd Pf Pi Po Qe Ql Qv Ra Rb Rj St Tv Uc Up Ur Us Ut Vp) Uu(aJ aM An Ar As aW Bc Bg bJ Bn bQ bV bW cN Cq dA Dd dF dl DL Dp Ef Fb Fp Gl Hv Hw Im In Ir It Je Jk Jo Jp Js Kg Kk Ko Ky Li Lj Lv Lx Md Mj Ml Mm Mn Mp Mr Mv Mw Mz Na Nb Nf Nm Nq Nt Ny Oa Oh Or Ou Oz Pb Pc Pg Ph Pj Qb Ql Qv Rb Rj St Tv Ua Uc Uh Ul Up Us Uv Vp Wm) Ch(aC aM An Ar As aW Ax BC bF Bg bJ bM Bn bR bW bZ cE cG cP Cq cS Ct Cu Dd De DI dL Dp Ed Ez Fb Fp Hv Hw Hx Ib Ir Jk Jo Jp Js Jt Kg Kk Kp Ky Li Lu Lv Ly Md Mi Mj Mn Mp Mv Mx Mz Na Nm Oa Of Or Ou Pb Pg Ph Pi Qb Qt Qv Rb Rj St Tv Ua Uc Uf Uh Ul Up Ur Us Vp) dA(Ad Aj An aV Ax Ba bS bV bW cB cC cK CP Cu Cw dF dL Et Fa Fr Hc Hq Hu Hv Hw Ij Im In Ir Jd Jt Kd Kf Kk Kn Kp Kz Lh Lj Ly Md Mj Mk Mr Ms Mu Mx Mz Na Nb Nc Nd Ng Nn Nr Ns Ny Oa Og Oh Oi Ok Om On Ow Oy Oz Pi Qd Ql Qw Ra Rj St Ua Uf Uh Uk Up Us Ut Uv Vp) Uf(AD Aj aM An Ap As aW Ax BN bR Cp Cq Cu Cw Dd Fp Hc Hv Hw Id Ij Im In Ir Iv Jd Jo Js Jt Jy Kf Kg Kj Kk Kl Kp Ky Kz Ld Lh Lu Lv Md Mg Mj Ml Mr Ms Mz Na Ng Nm Nr Nw Oa Og Oh Oi Ok Om Or Ow Oy Oz Pb Pc Pi Qb Ql Qv Rj St Tn Uc Up Us Uv Vo Vp) Hc(aD aM An Ar aW Ba Bc bJ Bn bQ bV bW cN Cq Dd dF dl Dk dL Fb Hu Hv Im In Ir Je Jo Jp Js Jt Kg Ky Ld Li Lj Lu Lv Ma Md Mj Mm Mn Mr Mt Mu Mw Mx Mz Nb Nf Nm Nt Nv Ny Oa Oi Or Ou Pb Pd Pg Ph Qb Qd Qv Qx Rb Rj St Uc Uh Ul Ur Us Uv Vp Wm) Ql(AD AJ aM An aP As aW Ax Bn bW cN Cp Cq Cs cT Cu Dd dG dl dL Dp Ed Fa Fp Fr Hu Hv Hw Id Ij In Io Ir Iv Jd Js Jt Jy Kj Kn Kp Ky Kz Lu Lx Ml Mr Ms Mu Na Nc Ng Nm Nn Nw Oe Og Ok Om Ow Oy Oz Pb Pf Pi Qe Ra Rj St Tv Ul Up Ur Uv Vp) Qv(AD As aW Ax Bc bJ Bn bV bW cK cN Cp Cq Cs cT Cu Cw dG dl Dk dL Et Ez Fr Hu Hv Hw Ij Ir Jt Kf Kk Kn Kp Ky Kz Lh Ly Md Ml Mm Mp Mr Mu Mw Mz Na Nc Nm Nt Ny Oa Oi Ok Om On Oz Pb Pc Pd Pf Pi Pj Qb Qy Ra Rj St Tn Uc Ud Up Us Uv Vp) aW(aD An Aw Ax Ba Bc bM bR bV cE cG Cs cU cW Dd Dk Ed Fa Fp Fr Gl Hu Hv Hw Im Ir It Jo Js Jt Kf Ky Kz Lh Lv Ly Ma Md Mj Mm Mw Mx Mz Na Nb Nc Nk Nm Nr Nt Oe Oh Oi Or Oy Oz Pb Pc Pd Pg Pi Qb Qt Rb Rj St Uc Uh Up Us Ut Uv Vp) Oi(AD aM An Ar As Ba Bc bJ bM Bn bQ bW cN Cp Cq cS cT Cu CW Dd dF dl Dk Dl Ez Fb Gl Hu Ih Je Jk Jy Kd Kf Kk Kn Kp Ky Kz Ld Mi Ml Mn Mv Mw Mx Ne Nf Nl Nu Nx Oa Or Pa Pg Ph Pi Qy Ra Rb Rj Tn Uc Uh Ul Up Ur Us Vp Wm) cN(Ad Aj An As Ax Bn bV cA Cp Cq Cu CW Dd Et Fp Fr Hu Hv Hw Id Ij Im In Ir Js Jt Kd Kf Kn Kp Ky Kz Lh Ly Md Mj Mr Ms Mx Mz Na Nb Nc Ng Nn Nr Ny Oe Og Oh Ok Om Oy Oz Pi Qd Ra Rb Rj St Uc Uk Up Ur Us Ut Uv Vp) aD(Ad An Ar As Aw aZ bF bJ Bn bZ cG Cp Cq CU Cw dJ Dk dL Et Ez Fb Gl Hv Hw Id Ij Im In Ir Je Kk Kp Kz Ld Lh Li Lj Lv Ly Mm Mt Mw Mx Na Nb Nc Nv Ny Oa Ok Ou Pb Pd Pg Pi Qd Qt Qy Ra St Tn Uh Ur Us Ut Uv) Ow(Ad aJ aM An aP As Ax bJ Bn bV bW Co Cp Cq Cs Cu Cw dL Dp Ed Fa Fp Fr Hv Hw Ij Io Ir Iv Jd Jl Jt Jy Kf Kn Kp Kz Lh Lu Lx Ml Mr Mu Mx Mz Na Nc Ng Nr Oe Og Ok Om Oy Oz Pb Pc Pi Qd Qe Ra Rj Tv Ul Up Ur Vp) Us(aE aJ An Aw Ax Ba bJ bM Bn Bo bP bV bW Dd dF dl Dk Dp eC Ed Et Fr Hu Im In Jo Js Kg Kk Ky Lv Ly Md Mj Ml Mm Mp Ms Mw Mz Nf

Figure 8 Continued

Ng Nm Nr Nt Nv Oa Og Oh Oy Oz Pd Pf Pg Qb Qd Qg Rj St Tn Tv Uh Ul Ut Uv Vp) Kz(Ad AJ aM As Ax Bn bR bS bV bW cA Co Cq Cs cT dF dG dI dL Dp Et Fr Hu Id Io Iv Jd Je Jl Jn Ju Jy Kk Kp Lu Md Ml Mm Mn Mr Mu Mz Nf Nn Nr Oe Og Oh Ok Om Pb Pd Pe Pf Qe Qy Ra Rj Tn Tv Up Ur Uv) St(Ad Aj Al An As bJ bM Bn bV bW Co Cp Cq Cu CW dG dL Dp Et Fp Hv Hw Id Ij In Ir Iv Jd Jo Js Jt Kj Kn Kp Lh Lu Ly Md Ml Ms Mz Na Nc Ng Nl Nm Nn Nr Oc Og Ok Om Oy Oz Pb Pi Rb Rj Uc Up Uv Vp) Aj(aJ An aP Ax BC bM bQ bW Dd dF dI dL Dp Ef Ez Fb Fp Gl Ha Hx Ib Im It Jk Js Kj Kk Ky Li Lv Ma Mj Mn Mp Mr Mt Mv Mw Mx Nb Nm Nt Nv Nw Ny Oa Oh Or Ou Pg Ph Qb Qd Qt Qy Rb Ua Ud Ul Wm) Ed(aJ aM An As Ax Ba Bc Bn bO bQ bW cK Cp Cq Cu cW dF dG dL Fa Hu Hv Hw Iv Je Jl Jt Kk Kp Lx Md Ml Mm Na Nc Nk Nm Nn Nr Oe Og Ok Oz Pb Pd Pf Pi Po Qe Qy Rb Rj Tn Tv Uh Ul Ut Uv Vp tF) Ms(Ad aJ aM An aP As Aw Ba Bc bM Bn bV Cp Cq Cs cT Cu Cw Dd dF dG Dk dL Dp Fb Ij In Jy Kd Kf Kk Kn Kp Ky Mi Mn Mw Nf Nx Ny Oa Or Pa Pd Pg Pi Qx Qy Ra Rb Rj Uc Uh Ul Up Ur Ut Uv Vp Wm) dI(An Aw Ax bM cA cF cP cW Dd Dk dL Dp Fa Fp Fr Hu Hx Ib Im Jl Jo Js Jt Kf Kk Kp Ky Lh Lj Lv Ly Md Mj Mr Mu Mx Mz Nb Nc Nm Nn Nr Nt Oa Oh Oy Oz Pb Po Qd Rb Rj Tv Uc Ud Uh Up Ur Ut Uv) bV(Ad As Ax bJ bM Bn bQ bW Cp Cq cS Cu CW Dk Et Fa Fp Fr Hu Hv Hw Ij Im In Jd Jl Kd Kj Kk Ld Lu Lx Ly Mn Mt Mx Na Nb Nn Ny Og Oh Ok Om Oy Oz Pb Pc Pf Pi Po Qe Qu Ra Up Ur Ut Vp) Ur(aJ aM An Ax bJ Bn Cs Dd dF dG dL Et Fa Fp Fr Ha Hu Im It Jd Jo Js Kf Lh Lu Lv Lx Ly Mj Ml Mr Mu Mz Nm Nn Nr Nw Ny Oa Oh Ok Or Oy Oz Pc Pd Pf Qd Qe Rb Tn Tv Uc Ud Ul Ut Wm) Og(Ad aJ aM An aP As Ax Ba Bc bJ bM Bn bW Cp Cq Cu Cw Dd Dk Dp Ez Fa Fb Hu Ih Ii Ik In Jy Kf Kk Kp Lz Md Mj Ml Mn Mx Ne Nl Nu Nx Oa Or Oz Pi Qy Rb Rj Uc Ul Up Ut Vp) Co(Ad As Aw Ba bQ Cp Cq Cu dF dG Dk Et Fr Gl Hu Hv Hw Im In Ir Jo Js Jt Kf Kk Kn Kp Lh Li Lj Lv Ma Md Mj Ml Mr Mz Na Nb Nf Nv Oa Oh Ok Pb Pg Pi Qd Rj Tn Uc Uv Vp) Jd(Ad aJ Ap As Ax bM Bn bO bP bW Cq cT Cu Cw dL Dp Hv Hw Ij Ir Iv Kg Kl Kn Kp Ky Lj Lx Mg Mr Na Nc Nw Ny Oa Oe Oh Om Oz Pb Pc Pi Qe Qy Ra Rj Tv Ua Up Ut Uv) Kj(An Aw Ax Ba Bn Cs cT Dd dG Dk dL Et Fp Fr Gl Hu Im In Ir Iv Jk Jo Js Jy Kg Lh Li Lx Ma Md Mj Ml Mp Mu Mw Mx Mz Nv Oa Oh Pf Pg Ph Qd Rb Rj Tn Uc Ut Uv Vp) bM(An Aw Ax Ba Bn bQ Dd dF Dk Dp Fr Hu Hv Hw Ij Im In Ir Jo Js Jt Kd Kn Kp Lh Lv Ly Mj Mr Mt Mu Mx Mz Na Nb Ny Oe Ok Om Pb Pi Ra Rj Uc Up Ut Uv Vp Vt) bW(bQ Dd dF Fa Hu Hv Hx Ib Id Ir Jo Js Jt Jy Kf Kk Kp Ky Ld Lh Lj Lv Ly Md Mj Mt Mu Mz Nb Nn Oa Oh Ok Or Oy Pb Pd Po Qb Qd Qx Rj Tn Uc Up Ut Uv Vp) Ng(Ad aP Aw Ax Bn Bo bQ Cp Cq cT Cw Dd dF dG Ez Fa Gl Hu Hv Hw Ii In Kf Kn Kp Lj Md Mj Ml Mx Ne Nf Nh Nr Nu Oz Qy Ra Rb Tn Uc Ul Vp Wm) Dp(An Ar bB cW Dd dF Et Hx Im In Jo Jp Js Jt Kf Kk Ld Lh Li Lj Lu Lv Lx Ly Md Mj Mm Mr Mz Nm Nr Nt Oa Or Oz Qd Rb Tn Uc Uh Ut) bJ(An Ax Bn Cp dL Hv Hw Js Jt Jy Kk Kp Ky Lh Lj Lv Lx Md Mj Mt Mu Mx Na Nb Nf Nn Ny Oe Oh Ok Om Or Pb Qd Rb Rj Tn Tv Uc Ut) Ly(aJ aM aP Ar As Ax Bn bQ Cp cT dF dG Dk dL Fb Je Jy Kf Kp Ky Mi Ne Nu Oa Or Pi Qx Qy Rb Rj Tn Tv Uc Uh Ul Up Ut Uv Vp) Nf(aC Ad An As Bo bQ bR Cp Cq Cu Cw dF eC Fa Je Jy Kg Kk Kn Kp Ky Mi Mj Ml Mv Mx Nb Nl Pa Pd Pg Pi Ra Uh Up Uv) Oy(An Ar As Aw Bc Bn bQ bZ Cq Cu cW Dd dF Dk dL Ez Fb Gl Jg Kg Kk Ky Nv Oa Or Ou Pg Ph Qy Rb Rj Uc Ul Up Uv Vp) Kg(As Bn Cp Cq Cu Dd Et Hv Hw Ir Jo Jt Kp Lh Mz Na Nm Nn Nr Oh Pb Pd Pf Pi Qe Ra Rb Rj Uc Up Ut Uv Vp) Lx(Ad aJ An Ao As BG Bn bR bS cA Cp Cq cT Cu dH dL Id Kd Kn Kp Ky Pi Qz Ra Rg Rj Tv Up Uv Vp Tj) Ax(aC Ad aJ aP As bC Bn bO bR Cp Cq Cw dG dL Hu Hw Id Ij Io Ju Lu Na Nc Nw Oe Om Pi Qu Qz Ra Up) Jy(Ad aP As Cu Cw dL Et Fp Hv Hw Ij Im Iv Iz Kn Kp Ky My Na Nc Nq Nr Oa Oh Oz Pi Qe Qu Ra Rj Up) aE(Ad As Cp Cq Cu Cw Dk Hv Hw Id Ij In Jt Kd Kf Kn Kp Md Mt Nb Ny Ok Om Pb Pd Pi Ra Rj Up Ut Vp) Uh(Ad As Bn Cq Cu Cw dM Hv Hw Id Ij In Ir Jt Kd Kn Kp Lu Mz Na Nm Pb Pe Pi Ra Rj Tn Uc Up Uv) aJ(Dd Hu Hv Hw Ir Jt Kn Kp Ld Lv Mt Mu Mz Na Nb Nr Ok Oz Pb Pd Pi Po Rb Rj Tn Tv Up Ut Uv Vp) aM(An Aw Cp Et Fp Fr Gl Id Ij Im Jl Kd Kn Lh Li Lj Ma Mt Mx Ny Oc Oh Om Pd Pf Qd Qe Qg) aP(Ad An As Bn Cp Cq Cu Cw Hu Hv Hw Ij In Io Kd Kn Na Nc Nr Ny Oe Om Oz Pi Ra Tv Up Uv) Ky(Bn Cq dG Fp Hu In Io Ir Iv Kk Lu Md Mr Mu Mx Mz Nc Nn Nr Nt Oz Pb Pd Pf Ul Uv Vp) Fa(Ad Ao bO Cu Cw dL Id Ij Io Is Iv Iz Kl Kn Ml Na Nw Oe Oz Pc Pi Qu Ra Tv Up Uv) Nn(aC Ad An As Bn hO Cp Cq cT Cu Cw Id Iz Kl Kn Kp Pi Qu Qz Ra Rj Tv Up Uv) Mx(bR cW Hu Hv Hw Ij Jo Ma Mi Ml Mp Mt Mv Mw Nb Ne Nl Nu Nx Ny Pa Pg Wm) bP(Hv Hw Id Ij In Ir Jt Kd Kn Kp Md Mz Na Nb Ny Om Pi Ra Rj Up Ut Uv Vp) eC(An Bn dL Hx Is Jo Js Jt Kf Lh Md Mj Ml Mt Mz Nb Ny Ok Pb Pe Ra Uc Uv) Oz(An bQ cW dF dG Gl Hv Ij In Kf Kk Kn Kp Mt Ns Oa Or Pi Rj Tv Ut Uv) Pf(Ad An As Bn bO bR bS Cp Cq Cu Cw Iz Kp Pi Qu Qz Ra Rj Tv Up Vp) Mr(Ad An As Bn bR Cp Cq cT Cu dG dL Id Kd Kn Kp Pi Ra Rj Up Uv) Hu(aC Ad An As Bg Bn Cp Cq cT Cu Cw dL Iz Jh Mv Nv Pc Qu Ua) Oh(aC Ad An As Bn Cp Cq Cw Id Kd Kp Pi Qz Ra Rj Tv Up Uv Vp tF) Nr(Ad As Bn bO Cp Cq Cu CW dL Kd Kl Kn Kp Pi Ra Rj Up Uv) Qg(Ad As Bn Cp Cq Cu Cw Hv Hw Ij Ir Kp Na Pb Pi Ra Rj Tv Up) Mu(aC Ad Al An As Bb Bn cT Cu CW dL Iz Kp Oa Pi Tv) Mv(Hv Hw Ih Ij In Jg Jo Lj Mi Ml Mn Ne Nh Ns Pa Pc Wm) Qu(Ba Cw dF dG Et Fr Ij Im Jt Kf Ma Ok Om Pd Qe Tn Ut) Ao(Ba Cp Dk Et Fr Ij Im Jl Lh Ny Ok Pd Po Qd Qe) Bo(Bn Cq Cu Hv Hw Ij Jn Kn Kp Na Pb Pi Rj Tv Up) Cs(Ad As bC Bn bR Cp Cu dG dL Id Iv Ju Kd Ra Rf) Fr(aC As Bg bO bR Iz Kl Kp Oa Pi Rj Tv Ua Uv) Qe(Ad As Bn bO Cw Id Iz Kl Kn Pi Ra Rj Up Uv) Jg(Ih Ij Io Lz Ma Mg Mh Mj Ml Mp Mw Nl Ny Pc) Wm(Hv Hw Ih Ij Jo Lz Ma Mw Ni Nm Ny Oe Pc) Fn(Ad As Cp Hv Hw Ij Kp Na Om Pk Ra Tv Up) bR(bH bZ cU dF dJ dL fR Ir Jl Mi Mt Pd Qd) Im(An As Bn Cq CW Iz Ju Ra Rj Uv Vp) Po(Ad cT Cw Id Iz Kd Kn Pi Ra Up Tj) Mw(Ih Ij In Mh Mj Mn My Nb Nl Pd Ut) Tn(Bg bL cH Iz Jj My Nc Nk Pc Pj Rg) Jl(Ad As CW Id Iz Kn Pi Ra Rj Up) Jo(Ad Cw Id Ih Kd Kf Mi Pa Pg Pi Rf) dG(bN cA cL Hq Io Mk Nc Nd Ns Oc Uk) Ml(Hv Hw Ih Jk Ma Mj Mn Ne Pd Pg) Et(aC An Cq Dg Hb Iz Kl Tv Vp) Mm(Kn Kp Pi Ra Rj Tv Up Uv Vp) Fp(As Bn cM cT Cw dF dL Ul) Lu(Ar Kf Lj Mn Oa Pc Pj Uv) Me(Ad As Cp Cq Cu Cw Ld Tv) Mj(Lz Mn Mp Ne Nl Ns Nx Ny) Nc(bQ Kd Kf Kn Or Pi Uv Vp) Id(aK bO cK cT dE dJ On Ug) Qd(An bl Bn bO cW Iz Kl Tv) Oe(Ba cT dF Dk dL Oa Ul Uv) Of(Ad Cq Kn Pi Ra Up Ut Vp) Mp(Hq In Mh Nd Nl Nu Ny) Ij(Ih Iz Mi Ne Ns Nv Pg) Nw(An Cq kp No Tv Uv Vv) Ut(Bb bF Hq Je Lj Nq Oa) bQ(bF Bg bZ cA cO dH dL) cW(Kk Ld Lj Nb Nt Oa Vt) In(Ih Ma Mn Ne Nh Pa) Rf(An bC Dd Js Kf Or) Pd(Bg bS cA Hq Iz Ne) Pg(Hv Lj Ne Nh Ns Pa) fR(aC aV bO bX cP cX) Ba(aC Iz Mg Ss Vo) Mi(Ih Ma Nb Nl Nv) Kl(Cw Is Lh Ma Om) Bg(Aw Jh Mt Nb) Mn(Ih Mh Nb Nl) My(Jh Nv Nx Qx) Tv(Gl Jj Nk Qt) Io(cT dF dL Oa) Om(Oa Qy Ua Ue) On(Al fP Je Ua) Uv(aK cT dJ Ou) Vv(cT Jn Jr Kq) Pc(Kk Lz Nl Nu) dM(Oa Qn Up Vp) Cw(Iz Mg Vo) Hw(Ih Lz Nb) Lj(Ne Nx Ny) Vt(aV bX Qa) Dk(aC Iz) Ns(Ii Nu) Ma(Ih Nl) Lh(bO Iz) Nv(Ne Pa) Ny(Nl Tj) AwaC MgKf MzaK NbHv JhQy QzPc KnUg UlUk

Unconstrained panels with 3 analytes, where 4.1E-11 >= 'AUC p-value' > 0. Contains 50,000 panels of 7,079,861 total panels evaluated. :
dN{Ly(aA aC AD aE AF aG aH al AJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM Dp eC Ed Ef Et Ez Fa Fb Fn FP Fr Fw Fy Gl Gp Gz Ha Hb Hc Hf Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tv Tz Ua Ub Uc Ud Ue Uf Ug Uh Uk Ul Um Un Uo Up Ur Us Ut Uu Uv Vo Vp Vt Vv Wm Tj tF) Nf(aA aC AD aE AF aG aH aI aJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ

Mw My Nb Nd Nj Nk Nl Nn Nq Nr Ny Oa Oh Om Ow Pb Pc Pd Pe Qb Qc Qe Qg Qm Qn Qt Qw Qy Qz Rf Rg Rh Rm Tz Uh Uk Um Un Wm) Mq(Ad AF aI aL Ap aQ AS aU aX aZ BC bE Bg bH Bn bP bS bU bW cA cB cC cE cF cI cK cL Co cS cV Cx cZ dB dD De DG dH dJ dM Fn Hf Hq Hr Hu Hv Hx Ih Io Is Iz Je Jg Jh Jr Jv Jy Kg Ki Kl Ko Lh Lx Mb Mh Mk Mn Mv My Nd Ng Nh Nj Nk Nl Nr Nx Ny Oe Of Ok Pb Pc Qb Qc Qg Qu Qw Uk) dJ(aC aD aE aF aG aH aI aL aM AN aO AP aQ aR aS aU aW AX aY aZ BA bB bC bE bF BG bH bI bL bM bP bQ bS bU bV bW bZ cA cB cD cE cF cG cH cI cJ cK cL cM cN cO cP cR CS cT cU cV cW cX cZ dB dC dD dF dG dH dK dM Hf Is Jr Jv Jy Mu Mw Nd Nr Ny Pb Pc Qm Qw Rf Un) Jy(Ad AF aI AI aM aO Ap As aU Ax aZ Bb bF BG bH Bn Bo bS bW cA cB cC cE cG cI cL Co Cp Cs Ct Cx cZ dB De dH Fn Hf Hq Hu Hv Is Iz Jg Jh Jk Jr Jv Kd Kg Ki Kl Ko Lj Mb Md Mk Ml Mn Mv My Nd Ng Nh Nl Nq Ns Nv Nx Ny Oa Of Pb Pc Pg Qc Qg Qh Qu Qz Ss Ua Uk Un Up Vo Wm) Jr(Ad AF aI AI aO Ap aQ As aU aZ Bb bE BG bH bL bM Bn Bo bS cA cB cC cK Co Cp Cq cV Cx cZ dB dD De Dg dH Fn Hf Hq Hu Hv Ii Is Iz Jg Jo Jv Kd Kg Ki Kl Ko Lx Mb Ml Mn Ms Mu My Nd Ng Nh Nj Nk Nl Nr Nx Ny Oe Of Oi Ok Pb Pc Qc Qg Qw Qz Rf Uk Ur Uv) Hf(aF aH aO aU Ax Ba Bg bH Bo bQ bS bV cA cB cC cD cK cL Cs cT cZ dH Di Fn Fy Hq Hu Hv Ih Ij Iq Is Js Jv Ki Kk Ko Kq Lj Lu Lw Lx Lz Ma Ml Ms Mt Mu Mw Nb Nh Nj Nk Nl Nn Nq Nr Ny Oa Oe Of Oh Oi Ow Pb Pe Qg Qv Qw Qx Qy Qz Rf Rh Sr St Uk Ur Uv Wm) Is(Ad AF aI AI AO Ap As aU aZ bE Bg bH bM Bn Bo bS cA cB cC cG cL Co Cp Cq cS cV Cx cZ dB dD De dF DG dH Hq Ii Jg Jo Jt Jv Kg Ki Kl Ko Lh Lx Mb Mg Mj Mn Ms Mv My Nd Ng Nh Nj Nl Nr Nx Oe Of Oi Ok Pb Pc Qc Qg Qh Qw Qz Ug Uk Ur Uv) dH(aG aH aJ aM An aP aQ AR aU AX aZ Ba bB bC bF bG bH bL bM Bo bQ bU bZ cA cB cC cD cE cJ cK cO cR Cs CU dB dC dG Dk dM Fn fR Hu Hv Ij Js Jv Kg Kq Ky Lx Mb Mu Mw Nd Nn Nq Nr Ny Ow Pd Pe Qe Qg Qn Qw Qy Qz Rf Uk Un Ur) Mu(AF aI aO Ap As aU aZ BG Bn Bo bP bS bW cA cB cC cE cL Cp cT cV Cx cZ dB Fn Hu Hv Ih Io Iz Jg Jv Kd Kg Ko Ky Lz Ma Mb Ml Mp Ms My Nb Nd Ne Nj Nl Nx Ny Oe Oi Pb Pe Qc Qg Qz Rf Rh Ua Uk Ur Wm) aU(aC aE aF aG aH aI aL aM aO aQ aR aX aY aZ BA bB bC bF bG bH bL bM bQ bS bU bV cA cB cD cE cG cH cJ cK cO cR cT cU cV cX dB dC dF dG dK dM Gl Ij Jv Kq Mw Nd Nn Ny Ow Qg Qm Qn Qt Qw Qz Rf Ur) Qw(AF Ap As Ax aZ bE Bg bM Bn Bo bS cA cB cC cK Co cQ Cs cZ dB De Fn Fw Hu Hv Iz Jv Kg Ki Kl Ko Ky Mb Mn Ms Mv My Nd Ne Ng Nh Nl Nq Ny Oe Of Oi Pb Pc Pe Qc Qg Qn Qu Qz Rf Ua Uk Ur Uv) Jv(Ar As aX aZ Ba bH bM Bo bQ cC cK Cs Cw dB Fn Hu Hv Ib Ij It Js Ju Kf Kg Kq Ky Lj Mv Mw My Nb Nk Nl Nn Nq Nr Ny Oa Pb Pc Pe Qb Qe Qg Qm Qn Qt Qy Qz Rc Rf Sr Uh Uk Un Ur) aF(aM An Ar As AX aZ Ba bH bM Bo bQ cK cO cR Cs Cu Cw dB Dc Di Dk dM fR Fy Hu Hv Ij Jq Kq Lx Mw My Nb Nd Nq Nr Nw Ny Pd Pe Qg Qm Qn Qt Qz Rf St Uk Un Ur) cB(aG aQ aX aZ BA bC bF bI bM Bo bQ bU bZ cA cE cO cR cT cX cZ dB dK Fn Gz Hu Hv Ib Ih Ij Kd Kf Kq Mw Nd Nq Nr Ny Oe Ow Qe Qg Qm Qn Qt Qy Qz Sr Uh Uk Uo) aM(aG aH aO aQ aR aW aX aY aZ bB bC bE bF bG bH bI bL bM Bo bP bQ bS bU bV bW bZ cA cC cD cE cG cH cI cJ cK cO cP cR cS cT cU cV cX cZ dB dC dF dK dM Qg) Rf(Af aQ As aZ Bb Bg bH bM cC cD cK Co cS Cx cZ Fn Hb Hq Hu Ii Iz Je Jt Kd Kg Kl Ko Lw Lx Mk My Na Ng Nl Nx Oi Ok Pc Qc Qg Qy Qz Ra Uk Un Uv) bQ(aI aL aN aO aQ aS aX aY aZ bC bE bF Bg bH bI bL bM bP bS bU bZ cA cD cE cG cI cJ cK cL cO cR cS cU cV cX cZ dB dD dF dG dM My Nd Ng Pb) Kg(cK cT Cx Et Ez Fy Gl Hu Hv Ih Ij Iq Jm Js Ki Ks Lh Ma Ml Mw Ng Nn Nq Nr Ny Ow Pc Pd Pe Pj Qa Qb Qe Qm Qn Qt Qy Ra Rh Rm Tz Un Wm) bM(aI aN aX aZ bA bB bC bE bF Bg bH bI bL bP bU bV cA cD cH cJ cK cL cR cT cU cV cW cX cZ dB dD dM Fn Hu Hv Ml Nr Oe Ow Pd Rh Wm) bH(aH aI aO aQ aR aX aY aZ bA bB bC bE bF Bg bI bL bP bS bU bV cA cD cE cG cH cJ cK cL cR cT cU cV cX cZ dB dK dM Fy Nd Rh) Pb(aH Ax aZ Ba Bo Cs dB dM Gl Gz Hu Hv Kd Ki Kq Lu Lx Mb Ms Mw Nd Ng Nl Nq Nr Ny Oe Ow Pd Pe Qc Qg Qm Qn Qy Qz Uk Ur) Ng(Ar Ax Ba Cs Ct Ez Fn Fy Hv Ih Ij Js Kq Lj Lx Lz Ma Ml Mv Nn Nq Nr Nt Oh Ow Pd Pe Qa Qm Qt Qz Rh Sr Uk Un) Un(Ap Bb Bg cC Cp cT Cx cZ dB De Fn Hv Ii Iz Jg Kd Kf Kl Ko Ms My Nl Nx Oe Of Oi Ow Qc Qv Qz Rh Uc Up Ur) Pc(Ax Cs cT cZ Fn Fy Hu Hv Kd Ki Ko Ky Ld Lj Lz Mb Ml Ms Nd Nn Nr Oe Ow Pe Qg Qv Qx Qz Ra Rh Uk Ur Wm) Bg(aH An aZ Ba bF Bo bZ cA cC cE cO Cw cZ dB Gl Hu Hv Ij Je Kq Ma Mw Nr Ny Pd Pe Qm Qn Qt Qy Qz Uk) cK(aX aY aZ bC bF bI bL bU bV cA cD cE cG cJ cL cR cV cX cZ dB dC dK Fn Ld Nd Ow Qn Qz Rh Uk Ur) aZ(aQ AS aX bC bG bI bL bU cA cD cG cH cJ cL cR Cs cT cV cX dB Dc dM Hu Hv Ki Nd Uk Ur) Nd(Ba Bo cC cZ dB Hu Hv Ij Jl Lw Lx Mw My Nb Nj Nk Nl Nn Nq Nr Ny Of Pd Pe Qe Uk) Ko(Ax Ba Cw Dc Hu Ij Ji Jq Ke Kn Kq Lw Mw Nq Nr Ny Pd Pe Pi Qa Qc Qm Qn Qt Sr) aX(aI aL aO aQ aY bE bF bI Bo bU bV cA cD cE cL cO cR cT cU cV cX cZ dB dM fR) Uk(Af aO Ap bL cC Co Cx dB Hu Hv Ib Kl Mw My Nl Nq Nr Ny Qb Qm Qn Qy Qz Rg) Of(Ad Cq Cw Dc Hu Hw Id Ij In Kq Ml Nb Nq Ny Om Pi Qa Qm Qt Qy Qz Ra Up) Qc(Ax cC Cs Hu Ih Ij Jm Js Kq Ml Mw Nn Nq Nr Ny Pe Qa Qb Qe Qm Rm St) Hv(Al Ap Bb Bo cC Cs Hu Je Jo Ki Ky Ld Lj Mv Nr Ny Pi Qg Qy Qz Ur) Cx(bW Cv Dc Ji Jq Ke Ki Kq Lw Ms Nw Ny Oe Qg Qn Qt Sr St Um Ur) Qz(cZ Fn Hu Iz Kq Lw Mw My Nk Nl Nn Nq Nr Oa Pd Pe Qg Qn Qy St) Fn(Cq Cw Dc Hu Hw Id Ij In Kq Lw Ml Na Nq Pi Qa Ra Up Vp) Ny(aI Ap As Bb cG cZ dB Dg Hq Ii Kd Kl Mb My Nx Oe Ok Qg) Ba(Af aI Ap As bS cA cG Co cV De Dg Iz Jg Kl My Ss) Hu(Af Ap bS cA Co dB De Iz Je Ml My Nk Nx Oe Qy Rh) Kq(Ad Ap As Cp cZ De Hq Iz Kf Kl Kp My Nx Ok Uc) dB(aE aG aQ bF bG bL bU cA cD cE cH cR cX dM Ki) My(Ij Je Jl Mv Mw Nq Nr Pd Pe Qm Qn Qt Qy) cA(aG aQ bC bG Bo cC cD cE cO cR cX dM) Qg(Af Cs cT Ml Mw Nn Ow Qa Qb Rh Wm) Ki(Ax cC Cs Ky Nn Nq Nr Oi Qn Sr Ur) Kl(Et Ez Ij Ma Mw Nn Nq Nr Qt Sr) dM(aW aY bI bL bW cL cT cV cX) Co(Ij Je Nr Ow Pd Pe Qt Qy) cZ(An cO cR Cs Dk Mw Qb Qm) Ap(Bo bU Ij Mw Nn Ow Qt) Iz(Mw Nq Nr Qm Qt Qy) cR(aO bL bU cD cV cX) As(Ax Cs Ml Ow Qn) Lx(Ax Cs Ow Pe Po) Je(Ao Bb Hq Ow Rh) Nx(Ji Mw Pd Pe Qn) Nl(Ih Pi Rm St) cT(aS cS cX dD) cV(Ax Bo Cs Nr) It(Tn To Tv) Qy(Ms Rh Ua) Qt(De Ss Vo) bA(aS cS dD) cG(bF cE cO) Wm(cC Ur) Nr(Ms Oe) Mb(Nj Nk) Qu(Ow Rh) Qn(cC De) bW(aQ fR) cO(bU cL) BobS EtOk MjPi NaRh NjIh IiRm JoPd bFcE cXfR} No{Uu(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM Dp eC Ed Ef Et Ez Fa Fb Fn FP Fr Fw Fy Gl Gp Gz Ha Hb Hc Hf Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tv Tz Ua Ub Uc Ud Ue Uf Ug Uh Uk Ul Um Un Uo Up Ur Us Ut Uv Vo Vp Vt Vv Wm Tj tF) Kr(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM Dp Ed Ef Et Ez Fa Fb Fn FP Fr Fw Fy Gl Gp Ha Hb Hc Hf Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Ks Kx Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tv Tz Ua Ub Uc Ud Ue Uf Ug Uh Uk Ul Um Un Uo Up Ur Us Ut Uv Vo Vp Vt Vv Wm Tj tF) bO(aA aC AD aE AF aG aH aI AJ aK AL aM AN AO AP aQ AR AS aU aV AW AX aY aZ BA BB BC bE bF BG bH bI bJ bL bM BN Bo bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM Dp eC Ed Ef Et Ez Fa Fb Fn FP

Sr Ss St Tn To Tv Tz Ua Ub Uc Ue Ug Uh Um Un Uo Up Ur Ut Uv Vo Vp Vt Wm Tj tF) Kj(Ad AF al Aj aK aL aM AN aO Ap Ar As aU aV Ax aY aZ bA Bb BC Bg bH bJ Bn Bo bP bQ bR bS bU bX cA cI cK cN Cp Cq CT Cu Cw CX cZ dA Db DC Dd De DG dH dI dM Ed Et Ez Fb Fn Fp Fy Gl Hb Hf Hq Hr Hu Hv Hw Hx Ib Ic Id Ij Im In Io Ip Ir Is It Iv Jd Je Jg Jh Ji Jn Jo Jq Jr Js Jt Ju Jy Kc Kd Ke Kf Kg Ki Kn Kp Kq Kx Kz Lh Lv Lw Lx Ly Lz Md Me Mh Mi Mj Ml Mm Mn Mp Mq Mr Ms Mu Mw Mx Na Nb Nc Nd Ne Nf Ng Nh Ni Nj Nl Nm Nn Nq Nr Ns Nu Nv Nw Nx Ny Oe Of Og Oh Oi Ok Om On Or Ou Ow Oy Oz Pa Pb Pc Pd Pe Pg Ph Pi Pk Po Qa Qc Qe Qh Ql Qm Qn Qt Qw Qy Qz Ra Rb Rc Rf Ri Rj Sr Ss Tv Ua Ub Uc Ud Ue Ug Ul Um Un Up Uv Vp Vt Vv Wm tF) dI(AD aE AF aG aI AJ aK AL aM aN AO Ap Ar AS aU aV AX aY bA Bb bF BG bH bJ bM bN bP bQ bR bS bU bX bZ cA cC cD cE cF cG cK cL cN CO CP cR Cs CT CU Cw CX cY cZ DB DC dD DE dF DG dH Dl dM eC Ed Fp Fr Fw Fy Hf Hq Hr Hu Hv Hw Hx Id Ij Il Im In Io Is Iv Iz Jg Jh Ji Jk Jn Jp Jq Jr Js Jt Ju Kd Ki Kn Kx Ky Kz Lh Lv Lw Lx Ly Lz Mb Mc Me Mg Mi Mj Mk Ml Mn Mp Mq Mr Ms Mv My Na Nc Nd Ne Nf Ng Nh Ni Nl Nq Ns Nt Nu Nv Nx Ny Oe Og Oi Om On Ou Ow Oy Oz Pa Pb Pc Pd Pf Pg Pi Pk Qa Qe Qh Qw Qy Qz Rc Rf Ri Sr Ss Ua Uk Um Un Up Uv Vo Vp Vt Tj tF) Ss(Ad aF aI Aj aK AL aM AN aO Ap aQ Ar As aU aV Aw Ax aY BA Bb bC bE Bg bH bJ BN Bo bP bQ bR bS bU bV bW bX cA cB cK Co Cp Cs CT Cu CV CW CX cY cZ dA Db DC dD DE Dg Di dJ Dk dM eC Ez Fa Fb Fp Fw Gl Gp Hb Hf Hq Hu Hv Hw Id Ii Ij Io Is Iv Iz Jd Je Jg Jh Jn Jq Jr Jt Ju Jy Kc Kd Ke Kf Ki Kn Ko Kp Kq Kx Ky Kz Lj Lu Lv Lw Lx Ly Md Me Mh Mm Mq Ms Mu Nc Nf Ng Nh Ni Nj Nl Nq Ns Nt Nv Oe Og Om Or Ou Ow Oy Oz Pa Pb Pc Pd Pg Ph Pi Pj Pk Qc Qg Ql Qm Qn Qt Qw Qy Qz Ra Rh Ri Ua Ub Uf Ul Um Un Up tF) Fp(aA aC aD aE AF aG AJ aK AL aN AO AP Ar aS aV aW aY aZ bA Bb BG bH bI bJ bL bM bN bP bR bS bV bW bX cA cH cI cK cN Co cP CQ cR Cs CT Cu Cv cW cX cZ DB dC DD DE Dg dJ DK Dl dM Fr Fw Gl Hb Hr Hu Hx Ih Ik Il Im In Io Iq It Iu Iz Jf Jg Ji Jj Jk Jo Jp Jq Js Ju Kg Ki Ks Kx Lj Lv Lw Lx Ly Lz Ma Mc Mh Mj Ml Mm Mn Mp Ms Mt Mu Mv My Na Nd Nc Nf Ng Nh Nj Nl Nm Nq Nr Ns Nu Nv Nw Nx Oe Of Og Oh Oi On Oz Pb Pc Pf Po Pz Qb Qc Qg Qh Qv Ri Rm Tz Ua Ug Ur Ut Vo Wm Tj) tF(aA aC AD aE AF aG AJ aK AL aM aN AO AP Ar aS aU aW aZ bA Bb bF BG bH bl bJ bM bN bP bR bS bV bX bY bX cA cH cI cJ cK cN Co CP CQ cR CS Ct Cu cW CX dB DC DE Dg dJ DK Dl dM Ed Fa Gl Hb Hf Hu Ih Ii Ik In Io Ip Iq Ir It Iu Iz Jf Jg Jh Jj Jk Jo Js Jt Ju Kd Kg Ki Kn Ko Ks Kx Ky Kz Lu Ly Me Mg Ml Mq Ms Mt My Mz Na Nc Nf Ng Nh Nl Nm Nq Nt Nu Nv Oe Of Og Oi Ok On Oy Pa Pj Pk Pz Qc Qg Qn Qt Qv Qx Qy Qz Ri Rm Tz Ua Uc Ue Ug Uo Ur Ut Uv Vo Vt) Aj(AD Af Al aM An Ao Ap Ar As aV aW Bb bH bJ Bn bR Cp Cq Cu Cw dA Dc Dd Dg dM Ed Fa Fb Gp Hb Hf Hr Hu Hv Hw Hx Ib Ic Id Ih Ij In Io Ir Is Iu Iv Iz Jd Je Jg Ji Jn Jo Jq Jr Js Ju Jy Kc Kd Ke Kf Kg Ki Kk Kn Kp Kq Kx Ky Kz Ld Lh Lu Lv Lw Ly Md Me Mj Ml Mq Mr Mu Mz Na Nc Nd Nf Ni Nj Nl Nm Nx Ny Oe Ok Om Or Ou Ow Oy Oz Pa Pb Pc Pd Pe Pi Pj Pk Po Qa Ql Qm Qt Qx Qy Qz Ra Rb Rc Ri Rj Sr St Tn Tv Uc Ud Ue Ug Uh Ul Um Un Uo Up Ut Uv Vp Vt Vv) bJ(aA aC aD aE AF aG aJ Al aM aN AO AP aS aW aY aZ bA Bb Bg bH bI bN bP bR bS bV bX cA cC cI cN Co Cq Cs CT CW CX dA dB DC DE Dg dK DL dM Ed Fw Hb Hf Hq Hu Hv Hw Id Ih Ii Il In Io Ir Iz Jg Jh Jn Jo Jr Jt Ju Kd Kg Ki Kk Kn Kq Kx Ky Lu Lv Ly Me Mg Ml Ms My Na Nc Nd Nf Ng Nl Nm Nq Ns Nt Nu Nv Ny Oe Og Oi Oy Pa Pb Pi Pj Pk Pz Qm Qt Qv Qx Qy Qz Rc Ri Tn To Tv Ua Um Up Ut Uv Vo Vv) Ng(aF aN aV aW BA Bb bH bN bR bS bX cA cK cT CX cZ dA Db DE Dg dM eC Et Fr Fw Hb Hf Hu Hw Ih Ii Ij Ik Il Im In Io Is Iu Iv Jd Jg Jh Ji Jk Jo Jp Jq Jr Jt Ju Kd Ki Kx Kz Li Lj Lu Lv Lx Ly Lz Ma Mb Mc Me Mf Mg Mk Ml Mm Mn Mp Mq Mt Mu Mv Mw Na Nd Ne Nf Nh Ni Nj Nl Nn Nq Ns Nu Nw Nx Og Oh Oi Ok Om On Ow Oy Oz Pb Pc Pd Pe Pf Pk Po Qa Qb Qe Qg Qh Ql Qn Qx Qy Qz Rf Rh Ri To Ub Um Un Vo Wm) Ri(aD aE AF al aK AL aM aN Ao Ap aU aV aW Bb Bg bH bl bP bS bX cI cK cN Cp Cq Cu CX cY dA dC dD De Dg Dl dM Ed Hf Hu Ih Ii In Io Ir Iu Iz Jg Jh Jk Jo Jr Jt Ju Kd Kg Ki Ko Kx Ky Kz Ly Me Mg Ms My Mz Nc Nd Nf Nl Nm Nq Nv Oe Og Oi On Oy Oz Pa Pc Pg Pk Qc Ql Qt Qy Qz Rc Rf St Tn Tv Ua Uc Un Ur Ut Vo) Iz(Af aM aU aV bH bN bR bS bX cA cK Cq CX cZ dA Db Dc DE dH Et Ez Hf Hu Ib Id Im In Io Is Iv Jd Jh Ju Kc Ki Kq Kx Kz Lw Lx Ly Me Mk Mp Mr Mu Mw Nc Ne Nf Nh Ni Nj Nk Nl Ns Ny Oe Og Oi Om Oy Oz Pa Pc Pd Pk Ql Qm Qt Qy Qz Ra Rf Tv Um Un Ut Vp) Oy(aC aD aE aG aJ aK AL aN Ao AP aR aV aW aY bA Bb bH bI bM bP bR bS bV bX cA cH cI cK cN Co cT cW cZ dA dC Dg dJ dK dM Fa Hb Ic Jd Je Jf Jr Ju Ki Kk Ks Kx Ky Mu Qg Qh Ql Qm Qv Qx Qy Qz Rc Tn To Tv Tz Ua Ub Ul Um Uo Ur Ut Vo Vv Wm) Wm(aA Hq Hu Hx Ih Ii Ik Il In Io Iq Ir It Iu Jh Ji Jj Jn Jo Jr Js Jt Lv Lw Lx Ly Me Mg Mj Mk Ml Ms Mu Mw Mx My Mz Na Nc Ne Nf Nh Nl Nm Nn Nq Ns Nt Nu Nv Nx Ny Oc Of Og Oi Oz Pa Pb Pc Pf Pg Po Pz Qb) Jg(bR Cv Cx dA eC Ez Fa Fb Fn Fw Hb Hf Ib Ic Id Jd Je Ju Jy Kc Kd Ke Kf Ki Kk Kn Ko Kp Kq Kx Ky Kz Ld Oa Or Ou Ow Ph Pi Pj Pk Qg Qh Ql Qm Qn Qt Qw Qy Qz Ra Rb Rf Sr Ua Ub Uf Uk Ul Um Un Uv Vt) Kx(AF AL aM Ao Ap aW Bb Bg bH bP bS bX cK Co Cq Cu CX cZ dA De Dg dM eC Ed Hq Ii Io Ir Jf Jh Jt Ju Kg Ki Ly Ms Nc Nf Nl Nm Nv Oe Og Oi Oz Pa Pk Ql Qn Qy Qz Ua Ut Vo) Og(aF Bb Co Cx cZ dA Dg dM eC Ed Fw Hb Hf Hu Ik Io Is Jd Ji Jr Ju Kd Ki Kz Lv Lw Lx Me Mq Mu Nd Ne Nf Nh Nj Nq Ns Nw Oh Oi Om On Pd Pk Po Qa Qb Ql Qy Qz Rc Ua Ul Um Un Vo) Nf(aA aE Ao Ap aW bA Bb Bg bH bl bP cI cK cN Co Cq dA Dg dJ Dl dM Hb Ih In Io Ji Jj Jr Ju Ki Kn Ko Ks Lv Mp Mu Ne Nh Ns Oi Qh Qn Qt Tn To Tv Ua Ug Ur Ut Uv Vo Vv) Vo(aK aV bH bP bR bS bU bX cK Cx cZ dA Db dM eC Ez Hb Hf Hq Hv Io Ju Ki Kz Ly Me Mu Nc Ni Nj Nl Oe Oi Oz Pa Pc Pd Pg Pk Qc Qh Ql Qy Qz Rf Ua Um Un) Pk(Ad aK Al aN Ao aU aW Bb Bg bH bP bX cK Co Cq Cu cZ dA Dc Dg dM eC Ed Hq Ii Io Ir Jk Jt Ju Kd Kg Ki Ko Ms Na Nc Nt Nv Oe Oi Pa Qc Qg Qh Qz To Ua) eC(aA aE aF aN Ap aW bA bI bX cI cK cN Co Cq Cu cZ dA Dc Dg dM Ed Hu Hv Hw Id Ij In Io Jn Jr Kg Kq Ma Na Nd Nm Oe Oi Pi Pj Qh Qz Rj Un Up Vp) dA(aD aE AF aG AO Ap Bb Bg bN bQ bR bS bX cA cG Co Cu cX dB dC De Dg dH Dl Ed Gz Ii Io Jk Jt Ki Me Ms My Na Nc Nd Ns Nv Oe Oi Ua) Oe(AF al aK aL aN aO Ap aU aV aW Bb Bg bH bN bP bR bS bX cG Co Cu cX cY cZ dD De Dg dM Ed Hf Kd Kg Ki Kz Qh Ql Qz Ua Um) Ed(aF aV bH bS bX cI cK Co cZ dM Fa Fw Hq Ii Io Jd Je Jh Jt Ju Kd Lw Nc Ni Nl Nt Nv Oi Pa Pg Qc Qg Qh Ua Ub Um) Co(aM Ap aV bR bX Cx Db dE Hu Ib Io Is Iv Jd Je Ki Kz Ly Me Mr Nc Nd Ne Ni Nl Oi Pa Pd Ql Qx Qy Qz Um) Dg(aV Bb bH bP bR bW bX cK Cx cZ Db dM Hf Hv Io Is Jh Ju Ki Kz Me Mu Nc Ni Pa Pd Qc Qh Ql Qy Ua Uf Un) cK(bR bS Fn Fy Gz Hb Hf Id Ki Kk Ky Kz Me Nd Pa Pi Qg Qh Qn Qt Qw Qy Qz Rf Sr Ua Ub Uk Um Un Up Vt) Io(AF aK Ap aU aV aZ Bb Bg bH bN bR bX Cx De dH Hf Im Ji Jr Kg Kz Lv Mu Ns Oi Pb Qb Qt Qz Ua) Ko(Ad As Cp Cq Cu Cw Dc Hv Hw Id Ij Ji Jn Jq Jr Kd Ke Kn Kp Kq Lw Na Om Pi Qa Ra Rj Tv Un Up Vv) Oi(aF aV bR bX Cx dM Hf Im Jd Ji Jr Ju Kd Ki Kz Lv Mu Nh Nn Ns Pb Pc Pd Qb Qh Ql Qz Rf Ua Up) Ki(aK Ap aU aZ Bg bH bP bX cC Cx DB DE Gz Hf Hv Jh Kz Ly Ms My Na Nv Qz To Ua Um) dM(AF aO Bg bR bX Cx Db dE dH Hf Hq Jt Kz Ly Me Mk Mr My Nc Nd Ni Nl Oz Pa Pb Pc Ua) Jt(Ad aM bR Cq Cu Cw Dc Id Ji Kd Kn Kq Kz Ow Pi Qz Ra Rj Um Un Up Vp) bX(bP bR bS cA Fw Hb Jd Je Ju Ke Nd Ow Ql Qx Qy Qz Rc To Ua Um Un) Pa(aE Ao Ap aW bA bH bl bP cT Jr Qv Qx Tn To Tv Ua Um Ut) To(aF aO bN Cx Hq Im Iv Ly Me Nc Ni Nk Oz Pc Qb Rg) Me(Ao aV aW Bb Bg bH bl bP cI cZ De Jr Kg Ua) Ni(Ad aE aK Ao aU aW Bb bP cI Cu Dl Tn Tv) Cx(aA aW bH Cv Hq Ju Lu Ms Qc Qh Ua Vv) Ua(aK aV bH Db Hf Hu Jd Kz Ly Qy) Un(Ad aK Ao Bb Cu Ii Ke Kf Ms Nv) Qz(aF aK aL Bg bP cI cX Ms Nt) Jr(Ih Ii Il Ji Jj Ms Mu Nh Ns) Kz(Ao aW cI Cu Ii Ir Je Jh Nm) Ly(aW Je Ju Kg Qh Ql Ub Ut) aF(cA Fa Fn Fw Jd Mq Qm Tj) Bg(Hu Jd Je Mu Ql Qy Um) aV(aD Ao bR bS cA Gz Nd) Bb(Fw Fy Jd Jq Kq Um) Mu(Hu Ml Ms My Nq Ns) Ji(aA Ii Jh Ke My Qc) aK(Fw Hq Ju Mq Uv Vt) Ao(Db Hv Jd Nc Qy) aW(Ju Mr Nc Nk Oz) Ap(bW Gz Jd Uf) Fw(aU cI cX Nv) Ii(aM bR Hf Ql) Kf(Dc Jq Kq Lw) My(Jd Lv Po) Nc(aE bP cN) Nv(Jd Je Ql) bH(Af bR Nd) cI(Hq Ju Mq) Cu(Iv Ra) Tv(Hf Oz) Kq(Of Uc) aD(cZ Qc) DeUm NmHf NeNl HqbP TnOz JhbR KdaO} Kj{Kq(aA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH Dl dJ DK DL dM Dp eC Ed Ef Et Ez Fa Fb Fn FP Fr

Figure 8 Continued

Fw Fy Gl Gp Gz Ha Hb Hc Hf Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kk Kl Kn Ko Kp Kr Ks Kx Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tv Tz Ua Ub Uc Ud Ue Uf Ug Uh Uk Ul Um Un Uo Up Ur Us Ut Uu Uv Vo Vp Vt Vv Wm Tj tF) Un(aA aC AD aE AF aG aH al AJ aK AL aM AN AO AP aQ aR AS aU aV AW AX aY aZ BA BB BC bE bF BG bH bI bJ bL bM BN BO bP bQ bR bS bU bV bW bX bZ cA cB cC cD cE cG Ch cI cK cL cN CO CP CQ cR CS CT CU CV CW CX cY cZ dA DB DC DD DE dF DG dH DI dJ DK DL dM Dp eC Ed Ef Et Ez Fa Fb Fn FP Fr Fw Fy Gl Gp Gz Ha Hb Hc Hf Hq Hr Hu Hv Hw Hx Ib Ic Id Ih Ii Ij Ik Il Im In Io Ip Iq Ir Is It Iu Iv Iz Jd Jf Jg Jh Ji Jj Jk Jl Jm Jn Jo Jp Jq Jr Js Jt Ju Jv Jy Kc Kd Ke Kf Kg Ki Kk Kl Kn Ko Kp Kr Ks Kx Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oa Oe Of Og Oh Oi Ok Om On Or Ou Ow Oy Oz Pb Pc Pd Pe Pf Pg Ph Pi Pj Pk Po Pz Qa Qb Qc Qd Qe Qg Qh Ql Qm Qn Qt Qu Qv Qx Qy Qz Ra Rb Rc Rf Rh Ri Rj Rm Sr Ss St Tn To Tv Tz Ua Ub Uc Ud Ue Uf Ug Uh Uk Ul Um Uo Up Ur Us Ut Uu Uv Vo Vp Vt Vv Wm Tj tF) Sr(aA aC Ad AF aH al Aj aK AL aM AN AO Ap aQ AR AS aU aV AW AX aY aZ BA BB Bc bE bF BG bH bI bJ bL bM bN bO bP bQ bR bS bU bV bW bX bZ cA cB cC cD cF cH cI cK cL cM CO CP Cq cR Cs CT CU CV Cw CX cY cZ dA DB DC DD DE Dg dH DI dJ Dk Dl dM Dp eC Ed Ef Et Ez Fb Fn FP Fw Fy Gl Gp Ha Hb Hc Hf Hq Hr Hu Hv Hw Hx Ib Ic Id Ih Ii Ij Ik Il Im Io Ip Iq Is It Iv Iz Jd Je Jg Jh Ji Jk Jl Jm Jn Jo Jq Jr Js Jt Ju Jv Jy Kc Kd Kf Ki Kk Kl Kn Ko Kp Kr Ks Kx Ky Kz Lh Li Lj Lv Lw Lx Ly Ma Mb Mc Md Me Mf Mh Mi Mj Mk Ml Mm Mn Mp Mq Mr Ms Mt Mu Mv Mw Mx My Mz Na Nb Nc Ne Nf Ng Nh Ni Nj Nk Nl Nn Nq Nr Ns Nu Nw Nx Ny Oa Oe Of Og Oh On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qw Qx Qy Qz Ra Rf Rg Rh Ri Rj Rm Ss St Tv Tz Ua Ub Uf Uh Uk Ul Um Up Us Ut Uu Uv Vo Vp Vt Vv Wm Tj tF) Jr(aA Ad aF al Aj aK AL aM An Ao Ap aQ AR As aU aV aW Ax bA Bb bE BG bH bJ bL BN BO bQ bR bS bV bW bX cA cB cD Ch cI cK cN Co Cp Cq CT Cu CV Cw cX cY cZ dA dB Dc DD DE dH DI dJ Dk Dl dM Dp eC Ed Et Fa Fb Fn Fw Gp Ha Hb Hc Hf Hq Hr Hu Hw Hx Ib Ic Id Ih Ii Ij Ik Il In Iq Ir Is Iu Iv Iz Jd Jf Jg Jh Ji Jk Jn Jo Jp Jq Jt Jv Jy Kc Kd Kf Kg Ki Kk Kl Kn Ko Kr Ks Kx Ky Kz Ld Lh Li Lu Lv Lw Ly Lz Ma Mc Md Me Mf Mg Mh Mj Mk Ml Mn Mq Mr Ms Mt Mu Mv Mw Mx My Mz Na Nb Nc Nf Ng Nh Ni Nl Nm Nn Nq Nr Ns Nt Nu Nv Nx Ny Oa Oe Of Og Oi Ok Om On Or Ou Ow Oy Oz Pa Pb Pc Pd Pg Ph Pi Pk Pz Qa Qb Qc Qd Qe Qg Qh Ql Qt Qw Qx Qy Qz Ra Rb Rc Rf Rh Ri Rj Rm St Tn Tv Tz Ub Uc Ud Ue Uh Uk Ul Um Uo Up Ur Us Ut Uu Uv Vp Vt Vv Wm Tj tF) Cw(aA AD AF aH AJ aK AL aM AP aQ aR aU aV AW Ax aZ BA Bb BC bE bF bG bH bJ bM BO bP bR bS bU bV bW bX cA Ch cI cK cN CO Cp cQ CS CT cU Cv Cx cY cZ dA Ch cI cK cN CO Cp cQ CS CT cU Cv Cx cY cZ dA Db DG dI dJ Dk DL dM Dp eC Ed Et Ez Fa Fb Fn FP Fr Fw Fy Gl Ha Hc Hf Hr Hu Hw Ic Id Ih Ij Im In Ip Is It Iu Iv Jd Je Jf Jh Ji Jj Jk Jl Jm Jn Jp Jq Js Jt Ju Jv Jy Kc Ke Kf Ki Kk Kl Ko Kp Kr Ks Kx Ky Kz Lh Li Lj Lw Lx Ly Ma Me Mf Mh Mj Ml Mm Mn Mp Mq Mr Ms Mt Mu Mw Mx Na Nc Nf Ni Nk Nm Nn Nr Nt Nv Nw Nx Ny Oa Of Og Oh Oi Ok Om On Ou Ow Oy Oz Pb Pc Pd Pe Pf Pg Ph Pi Pj Pk Po Pz Qa Qb Qd Qe Qg Qh Ql Qm Qn Qt Qu Qy Rc Rf Ri Rm St Tn Tz Ua Uc Uf Uh Up Ut Vt Wm tF) Pk(aA AD Af aH aJ aK AL aM AP aQ AR As aU aV Aw AX aY aZ BA Bb BC bE bF bG bH bJ bL bM BO bP bQ bR bS bV bW bX bZ cA cG cI cK cM cN cO Cp cQ CS cT CU Cv cW cY cZ dA DB Dc dE dF DG dI dJ Dk DL dM Dp eC Ed Et Ez Fa Fb Fn FP Fr Fy Gl Gp Ha Hc Hu Hv Hw Ic Id Ih Ij Im Ip Is It Iu Iv Jd Je Jg Jh Ji Jk Jl Jn Jp Jq Js Jt Jy Ke Kf Ki Kk Kl Ko Kp Kx Ky Kz Lh Li Lj Lw Lx Ly Ma Mm Mn Mp Mq Mr Ms Mt Mu Mw Mx Na Nc Nf Ni Nk Nm Nn Nr Nt Nv Nw Nx Ny Oa Of Oh Oi Ok Om On Ou Ow Oz Pd Pe Pf Pg Ph Pi Pj Po Pz Qa Qb Qd Qe Qg Qh Ql Qm Qn Qt Qy Rc Rf Ri Rm St Tn Tz Ua Uc Uf Uh Up Ut Vt Wm tF) Id(Ad aF aK AL AP aQ Ar aU aV Ax aZ BA Bc bE bG bH bJ bM BN bO bP bQ bR bV bX bZ cI cK cO cQ CS CT CU Cx cY cZ dA Db Dc dE dI dJ Dk Dl Dp eC Ed Ef Ez Fa Fb Fn FP Fr Fy Gl Ha Hc Hf Hq Hr Hu Hv Hw Ib Ic Ih Ij Ik Im Is It Iu Iv Iz Jd Je Jg Ji Jk Jl Jm Jn Jp Js Jt Jv Ke Kf Kg Ki Kk Ko Kp Kr Ks Kx Ky Kz Ld Lh Li Lj Lx Ly Ma Me Mg Mj Ml Mm Mn Mp Mq Mr Mt Mu Mv Mw Nc Nf Ng Ni Nl Nm Nn Nq Nr Nt Nv Nw Ny Oa Of Og Oh Ok Om On Ou Ow Oy Oz Pa Pc Pd Pe Pf Pg Ph Pi Pj Po Pz Qa Qb Qd Qe Qg Qh Ql Qm Qt Qy Qz Ra Rf Rh Ri Rm St Tn Tz Ua Uf Uh Up Us Ut Vt Vv Wm tF) Ad(aA AF Aj aK aL aM AP aQ aR aU aV Ax aZ BA Bb Bc bE bG bH bJ bM BN BO bP bQ bR bV bX bZ cI cK cO cQ CS CT CU CX cY cZ dA DB dE dI dJ Dk Dl dM Dp eC Ed Ef Et Ez Fa Fb Fn FP Fr Fy Gl Gp Ha Hc Hf Hq Hu Hv Hw Ib Ic Ih Ij Im Is It Iu Iv Jd Je Jg Ji Jk Jl Jm Jn Jp Js Jt Jv Jy Kf Ki Kk Ko Kp Kr Ks Kx Ky Kz Ld Lh Li Lj Lx Ly Ma Mb Me Mg Mh Ml Mm Mn Mp Mq Mr Mu Mv Mw Nc Nf Ni Nm Nn Nr Nt Nv Nw Ny Oa Og Oh Oi Ok Om On Ou Ow Oy Oz Pd Pe Pf Pg Ph Pi Pj Po Pz Qa Qb Qd Qe Qg Ql Qm Qt Qy Qz Rc Rf Rh Ri Rm St Tn Tz Ua Uf Uh Up Us Ut Vt Vv Wm tF) Ij(aA aD Af aJ aK aL AP aQ Ar aU aV Aw Ax BA Bb BC bE bH bJ bM BO bP bQ bR bV bW cI cK cN CO Cp cQ CS Cv cY cZ dA Db dG dI dJ Dk Dl dM Dp eC Ed Et Ez Fa Fb Fn Fp Fr Fy Gl Ha Hc Hf Hu Hw Ib Im Ip Is It Iu Iv Jd Je Jg Ji Jk Jl Jm Jn Jp Jq Jt Jy Ke Kf Ki Kk Kl Ko Kp Kr Ks Kx Ky Kz Lh Li Lj Lw Lx Ly Ma Me Mm Mn Mp Mq Mr Mu Mw Na Nc Nf Ni Nm Nn Nr Nv Nw Nx Ny Oa Of Og Oh Ok Om On Ou Ow Oz Pc Pd Pe Pf Pg Ph Pi Pj Po Pz Qa Qb Qd Qe Qg Qh Ql Qm Qt Qy Rc Rf Rh Ri Rm St Tn Tz Ua Uf Uh Up Us Ut Vt Vv Wm tF) Ji(AF aI aK aL aM aQ Ar aU aV Ax aZ bE bG bH bJ BN BO bQ bR bX bZ cB cC cH cI cK cO Cq Cs Ct cV CX cY cZ dA DB Dc dD DE dI dJ Dk Dl dM Dp eC Ef Et Ez Fb Fn FP Fy Hc Hf Hq Hu Hw Ib Ih Il Im Is Iv Jd Jn Js Jv Jy Kd Kf Kn Ko Kr Ks Kx Ky Kz Ld Li Lj Lw Lx Ly Ma Mb Me Mn Mp Mq Mv Na Nc Nd Nf Nh Nl Nn Nr Nx Ny Oa Of Og Oh Om On Ow Oy Oz Pa Pb Pd Pe Ph Pi Pz Qc Qe Qg Qh Ql Qm Qn Qt Qw Qy Qz Rf Ri Rj Tv Ua Uf Um Up Us Uu Vt Vv Wm tF) Jn(aD aH Aj aK AL aM An Ao aP aQ Ar As AW bA Bc bJ Bn bO bP bV bX Ch cN Co Cp Cq CT Cu Cv Dc Dd dI Dk dM Dp eC Ed Fa Fb Fr Ha Hc Hf Hr Hu Hv Hw Ib In Ir Is Iu Iv Jd Jf Jh Jo Jp Jq Jt Jv Jy Kd Kf Kg Ki Kl Kn Kr Kx Ky Kz Lh Lw Lx Ly Ma Md Me Ml Mn Mp Mq Ms Mu Mv Mz Na Nc Nf Ng Ni Nl Nm Nn Nr Ns Nx Ny Oe Og Oi Ok Om On Or Ou Ow Oz Pa Pb Pc Pd Ph Pi Qa Qe Qg Ql Qu Qy Qz Ra Rb Rf Ri Rj Tv Tz Ub Uc Ud Uh Ul Up Ut Uu Uv Vp Vt Vv) Lw(aD AF aI aK aL aM aQ Ar aU aV Ax aZ bA Bc bE bG bH bJ BN bO bP bR bV bW bX bZ cC cI cJ cL cQ cS cT CX cY cZ dA DB dC DE dH dI dJ Dk Dp eC Ed Ef Et Ez Fb Fn FP Fy Gl Hc Hf Hq Hu Hw Ib Ih Ik Im Iv Jd Jm Jo Js Jv Kf Ko Kr Ks Kx Kz Lh Lj Lx Ly Ma Mb Mm Mn Mq Mt Mw Nc Nf Ng Nl Nm Nn Nr Nw Ny Of Og Oh Ok Ow Oy Oz Pd Pe Pf Ph Pi Pj Po Pz Qa Qb Qe Qg Ql Qm Qt Qy Rf Rh Ri St Tz Ua Uh Us Uu tF) Qa(aA Aj aK aL aQ As aU aV aW Ax bE bG bH bI bJ BO bP bR bS bX cB Ch cI cK Co Cp Cq Cu cY cZ dA Db Dc dI dJ Dk dM Dp eC Ed Ef Fb Fn FP Fw Gp Hc Hf Hu Hw Ib Ih Ii Ir Iu Jd Je Jq Jv Jy Kd Kf Kg Ki Kk Kn Kp Kx Kz Lj Ly Mh Mj Mn Mp Mu Mx My Na Nc Nf Nh Ni Nl Nr Nx Oa Oe Og Oi Om Ow Pa Pb Pc Pi Po Qc Qg Qh Ql Qm Qn Qu Qy Qz Ra Rf Ri Rj Rm Tn To Tv Ub Um Uo Up Ur Us Uu Vt Vv Wm tF) Pi(aA aJ aK aL AP aQ aR aV Aw Ax BA Bc bE bF bH bJ bM Bo bP bQ bV bZ cN Cp CS Cu Cv cY cZ dA dE DG dI dJ Dk Dl dM eC Ef Et Ez Fa Fb Fn Fp Fr Fy Gl Hu Im Is It Iv Jd Jg Jk Jl Jp Jq Jt Jy Ke Kf Ki Kl Ko Kx Kz Lh Li Lj Lx Ma Me Mm Mn Mp Mq Mr Mu Mw Nc Nf Ni Nl Nm Nn Nr Nv Nw Ny Oa Oh Ok Om On Ou Ow Pd Pe Pf Pg Pj Po Pz Qb Qd Qe Qg Ql Qt Qy Rf Ri Rm St Tn Ua Uf Uh Vt Wm tF) Om(AF aK aL aM aQ aU aV Ax Bc bG bJ BN bO bP bR bX bZ cI cJ cO Cs CX cY cZ dA DB DE dI Dp eC Ed Et Ez Fa Fb Fn Fp Fr Fy Gl Ha Hc Hf Hq Ic Ih Im Is It Iv Jm Jo Jp Ki Ko Ks Kx Kz Ld Lh Li Lj Lx Ly Ma Me Mh Ml Mn Mp Mq Mr Mu My Nc Nd Nf Ni Nl Nn Nr Nw Ny Oa Of Og Oh Ok On Ow Oy Oz Pa Pc Pd Pe Pf Pj Po Pz Qb Qd Qe Qg Ql Qm Ra Rf Rh Ri Rm Uf Uh Uu Uv Vt Wm tF) Jq(AF aK aL aQ ArAU aV Ax BA bG bJ BN BO bQ

Figure 8 Continued bR bX bZ cB cl cO Cs Ct CX cY cZ dA Db DE dI Dk Dp eC Ed Ef Et Fb Fn Fp Fy Hc Hf Hu Hw Ib Ic Im Is Iv Jd Je Jm Js Kf Kp Kr Ks Kx Kz Ld Lh Li Lj Lx Ly Ma Me Mg Mn Mq Mu Mv Nc Nf Ng Ni Nl Nn Nq Nr Oa Og Oh On Ow Oy Oz Pd Pe Pj Po Pz Qb Qe Qg Ql Qm Qn Qx Qy Qz Rf Rh Ri Rm Tv Uf Us Wm tF) Kn(aF aK aL aM aQ Ar Ax Ba bH bJ bO bP bV bX cO Cs Cx cZ dA dI Dk dM Dp eC Ed Et Ez Fa Fb Fn Fp Hc Hu Hw Im Is Iv Jd Jk Kf Ki Kr Kx Kz Lh Li Ly Ma Mn Mp Mq Mu Mw Nf Ni Nn Nr Nw Oa Ok On Ou Ow Oy Oz Pd Pe Pf Pj Po Pz Qd Qe Qg Ql Qt Qy Rf Ri Ua Uf Uh Wm) Up(Ax BA Bc bJ bV Cs cZ dA dI Dk eC Et Ez Fa Fb Fn Fp Fy Gl Hu Im Is It Iv Jd Jk Jl Jp Kf Kx Kz Lh Li Lj Lx Ma Mm Mn Mp Mq Mr Mu Mw Nf Nn Nr Nv Ny Oa Oh Ok On Ow Pd Pe Pf Pj Po Pz Qd Qe Qg Ql Qt Qy Rf St Ua Uf Uh Vt) Dc(aF aK Ar Ax Ba Bc bJ bV cO Cs cZ dA dI Dk eC Et Ez Fa Fb Fn Fp Fr Gl Hu Hw Im Is Iv Jd Jk Jl Kf Ki Kx Kz Lh Li Lj Lx Ma Mn Mq Mw Nf Ni Nn Nr Ny Oa Ok On Ow Oz Pd Pe Pf Pj Po Pz Qd Qe Qg Ql Qt Qy Rf Ua Uh Vt Wm) Jd(An As Ax bA Bg Bn bV Ch Cp Cq Cs cT Cu Cv Dd Ed Fy Hv Hw Ir Is It Iv Jo Js Jt Jv Kd Kf Kg Kp Kr Kx Kz Lh Md Me Mi Mj Ml Mq Ms Mx Mz Na Nf Ni Nm Oi Ok Pb Pd Pe Ra Rb Rj Tv Uc Ud Ul Us Uv Vp Vt Vv) Is(aA As aW Ax bJ Bn bV Cp Cq Cs Cu Dd eC Ed Fb Fp Hu Hv Hw In Ir Iu Jo Jt Kd Kf Kg Kr Kx Ly Md Me Mq Mz Na Nf Nm Nr Pb Pe Ql Ra Ri Rj Tn Tv Uc Us Uv Vp Vt Vv tF) Lh(As bJ Bn bO Cp Cq Cu cY cZ Dp eC Ed Fb Fn Fy Hv Hw In Ir Jo Js Jt Kr Kx Ly Me Mj Ml Mz Na Nf Ni Nm Nr Pb Pd Pj Qg Ql Ra Rf Tv Uc Ut Uv Vp Vt Vv tF) In(aJ aK aP aQ aU aV bA bE bF bH bJ bM bP bQ bV bZ cK cN cO cT cY cZ dA dE dF dG dI dJ dM eC Et Ez Kf Kx Ma Nn Nr Pd Pj Qe Ql Qy Rf Uh tF) Tv(Ba Bc bJ Dk Et Ez Gl Hu Im It Iv Jk Jl Jt Ma Mm Mr Mt Mw Ni Nm Nn Nr Ny Oh On Pd Pe Pf Pj Po Pz Qd Qe Ql Qt Qy Rf Rm St Ua Uf Uh Ut) Na(aQ Ax Ba bJ dI Dk eC Et Ez Fa Fb Fn Fy Gl Hu Im Jk Jl Kx Ma Mn Mp Nn Nr Nw Oh On Pd Pe Pf Pj Po Qd Qe Qg Ql Qt Qy Rf Ua Uf Uh Vt) On(aF bO bR bX Cq Cx Db dI Dp Ed Ef Et Ez FP Fy Hc Hf Hw Ib Kr Ks Kx Kz Ly Me Mp Nc Nd Nf Ni Nl Nr Pd Ql Qm Rf Ri Uu Uv Vv tF) Cp(aK aM aU bJ bN bX Cx cY cZ dA Dp eC Fn Hc Hu Ib Iv Js Kf Kx Kz Ly Ma Me Mq Nf Nl Nr Oz Pd Pz Qb Qe Ql Qy Qz Rf Ri tF) Nr(aA As bA Bn Cq Cu Cv dM Hv Hw Ir Iv Jo Js Jt Kd Ke Kf Kr Ml Mq Mz Nf Ni Nm Ok Pb Pd Pe Rj Uc Ul Us Ut Uv Vp Vt Vv) Rf(aA As bA Bn Cq Cu Dd dG dM Hv Hw Ir Jo Jt Kd Ke Kf Kp Kr Mq Mx Mz Nf Ni Nm Pb Pe Rb Rj Uc Ud Ul Us Ut Uv Vp Vt Vv) eC(aA As bA Bn Cq Cu Dd Hv Hw Hx Ir Iv Js Jt Kd Ke Kf Kp Kr Me Ml Mr Mt Mz Nb Nf Nm Ny Pb Pe Ra Rj Uc Us Ut Uv Vp Vt) Fy(aA As BA bH bJ bW Cv dA dI Dk dM Ed Et Fb Hu Iv Je Jy Ke Kf Ki Mh Mm Mp Mq Mu Nn Ou Ow Pd Qe Ql Qy Ri Uf Ul) Pd(aA aD As Ax bA Cq Cs Cu Hv Hw Ir Jo Js Jt Ke Kf Kr Kx Me Ml Mq Nf Ni Nm Oi Pb Pe Po Rj Ud Ul Us Uv Vp Vt Vv) Pe(As bA bH bO cK dA dI dM Dp Ef Et Fb Fp Hu Hw Iv Je Jv Kd Ke Ki Kr Kx Ma Mu Ni Nn Oh Qe Ql Ri Uh Vv tF) Kr(Ax Ba bJ dI Et Ez Fb Hu Im Jl Ke Kx Lx Ma Mn Mw Nf Nn Oa Oh Ok Ow Pf Pj Po Qd Qe Qy Ua Uf Uh Vt) Hw(Ax Bc bJ Dk Et Ez Fb Fn Gl Hu Kf Kx Lx Ma Mn Nn Oh Ok Pf Pg Pj Po Pz Qb Qd Qe Ql Qy Ua Uh tF) Vt(aV Ax Ba bJ cZ dA Ed Ef Et Ez Fp Iv Kf Kx Lx Ma Nf Ni Nn Oh Ow Pj Pz Qe Ql Qy Ri Vv Wm tF) bA(bJ dI Dp Ed Et Ez Fb Fn Hc Hu Jk Jv Ks Ma Nf Oy Oz Pa Pc Po Qd Qe Qg Ql Qm Qn Qt Qy Ri Uh) Me(Ap Ax Ba bF bQ bV bZ Cv dA dI dJ Dk dM Fr Jy Ko Kx Lx Ma Mm Mn Nn Oh Pz Qy Ri Uf Ur) Vv(Ax Ba bJ Dk Et Ez Fb Hu Im Jk Jl Kx Ma Mn Mu Nn Oh Pf Pj Po Pz Qd Qe Qg Qy Ua Uf Uh) Nf(aA As bV Cv dG Dk dM Et Ez Fr Jp Kd Ke Kf Kp Lx Ma Nn Oh Pj Po Pz Qe Qg Ql Ri Uh) Kf(aM bJ Cq Cu Dp Fp Hv Ir Jo Jt Ke Kz Mz Nm Ok Pb Ql Ri Rj Uc Ut Uv Vp) Nn(As Cq Cu dA Fp Hv Ir Jo Jt Kd Kp Mz Ni Pb Ra Rj Uc Ud Us Uv Vp) Ql(Cq cT Cu dM Hv Iv Jo Jt Kd Ke Ml Mz Ni Nm Ok Pb Uc Ul Uv Vp) bJ(As Cq Cu Ir Jt Kd Ke Kp Ml Mt Mz Nb Nm Ny Ok Pb Us Ut Uv Vp) Kx(aA As Cq Cu Hv Ir Iv Jt Kd Ml Mq Mz Ni Nm Ok Rj Uc Ul Ut) Qe(aA As Cq Cu Hv Ir Jo Jt Kd Ke Pb Ra Rj Tn Uc Vp) Ez(Cq cT Hv Ir Jt Kd Ml Mz Nm Pb Uc Us Ut Uv Vp) Ml(cY dI Dk Fb Hu Lx Mn Pj Qg Qy Ri Ua Uh tF) Ni(Ax bV cN dI dM Hu Mn Nj Nk Oh Pf Po Ri tF) Et(As Cu Hv Ir Jo Jt Ke Ly Pb Uc Ut Uv Vp) Mq(Cu dA Db Im Kd Kp Ly Ma Ph Qm Qy) Fp(aA Cv dF Fa Fr Jy Kd Ke Kp Ut) Pj(Cu Hv Ir Jo Mz Rj Uc Ut Uv Vp) Ma(Cq Cu Hv Ke Pb Rj Uc Uv Vp) tF(aA Cu Fa Iv Jt Nm Ok Ut) Po(As bO dA Ef Kd Ra Vp) Ke(bX Cx Fn Ks Ly Us Uu) Dp(aA Jj Jt Kp Ok Ut) Ri(dM It Iv Jt Ok Ut) Hu(As cT Kd Ra Us) Kz(bV Cv dM Kp Lx) Uv(Ba dA dI Lx Pz) Vp(bV cZ dA dI Uh) Cq(bV cZ dl Uh) Qy(cT Kd Mz Ok) aA(Hc Ow Oy Oz) dM(Im It Iv Mw) Cu(Fa Pb Uh) Ly(Mx Ok Rb) Fa(Ef fP) Tn(It Oz) Im(As Kp) Hc(Jt Kp) Iv(bV Fb) Rj(Oh Qg) Ok(aL cZ) Ut(aF cZ) CsMu FnJt LxJo MwMy MzOw QdcT RadI JsUh bVfP}

CU CV CW CX cY cZ dA DB DC DD DE dF DG dH DI dJ DK DL dM eC Ed Et Ez Fa Fb Fn Fp Fr Fw Fy Gl Gp Ha Hb Hc Hf Hq Hr Hu Hv Hw Hx Ib Ic Id Ih Ii Ij Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kk Kn Ko Kp Kq Kr Ks Kx Ky Kz Ld Lh Li Lj Lv Lw Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nl Nm Nn Nr Ns Nt Nu Nv Nw Nx Ny Oa Oe Of Og Oh Oi Ok Om On Or Ou Ow Oy Oz Pa Pb Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tv Tz Ua Ub Uc Ud Ue Uf Ug Uh Uk Ul Um Un Uo Up Ur Us Ut Uv Vo Vp Vt Wm Tj) eC(aC AD aE aF aG aH al AJ aK AL aM AN AO AP aQ AR AS aU aV AW AX aY aZ BA Bb BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY DB DC DD DE dF DG dH dI dJ DK dL dM Ed Et Ez Fb Fr Fw Gl Gp Ha Hb Hc Hf Hq Hr Hu Hv Hw Hx Ib Ic Id Ii Ij Il Im In Io Ip Iq Ir Is It Iu Iv Jd Jf Jg Jh Ji Jk Jl Jm Jn Jo Jp Jq Jr Js Jt Ju Jv Kc Kd Ke Kf Kg Ki Kk Kl Kn Kp Kq Kr Ks Kx Ky Kz Ld Lh Li Lj Lv Lw Ly Lz Ma Mb Mc Md Me Mg Mh Mi Mj Mk Ml Mp Mq Mr Ms Mt Mu Mv Mw Mx My Mz Na Nb Nc Ne Nf Ng Nh Ni Nj Nk Nl Nm Nn Nr Ns Nu Nv Nw Nx Ny Oa Oe Of Og Oh Oi Ok Om Or Ou Ow Oy Oz Pa Pb Pc Pe Pg Ph Pi Pj Pk Po Pz Qa Qb Qc Qd Qe Qg Qh Ql Qm Qn Qt Qu Qw Qx Qy Qz Ra Rb Rc Rf Rh Ri Rj Rm Sr Ss St Tz Ua Ub Uc Ud Ue Uk Ul Um Un Up Ur Us Ut Uv Vo Vp Vt Tj) Fp(aC AD aE AF aG aH al AJ aK AL aM AN AO AP aQ AR aS aU aV AW aX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB Dc DD DE dF dG dH DI dJ DK DL dM Ed Ef Et Fa Fn fP Fr Fw Gl Gp Hb Hc Hr Hu Ib Ik Iv Iz Jf Jg Ji Jj Jl Jq Jr Ju Jv Kd Kf Kg Ki Ko Kx Kz Li Lv Lw Lx Ma Me Mf Mm Mn Mp Mq Mu Mw Nf Ng Nl Nn Ns Nw Oe Og Oh Oi Ok Om On Ow Oz Pb Pc Pf Ph Pi Pk Po Qa Qb Qe Qg Qh Ql Qn Qu Qw Qy Qz Rc Ri Rj Rm Sr Tz Ua Ub Uf Ug Uh Ul Un Ur Uv Vt Wm Tj tF) Hc(aC Ad aF aH al AJ aK aL aM aP AR As aV aW AX aY aZ BA bF BG bI bJ bL bM bN Bo bP bQ bR bS bV bW bX bZ cA cB cF cG CH cI cL cO cP CQ CS cT CU cV CW CX cY cZ dA Dc dF DG dI dJ Dk DL dM Ed Et Fa Fb Fn fP Fr Gl Hf Hu Hv Hw Ic Ij Im In Io Iq Ir It Iv Iz Jd Jn Jp Jr Js Ju Jv Kc Kf Ki Ko Kp Kq Kr Kx Ky Kz Lh Li Lj Lu Lv Lw Lx Ly Lz Ma Me Mg Mj Mk Ml Mm Mn Ms Mw Mx My Na Nc Nf Ni Nj Nl Nm Nn Nr Ns Nt Nw Oa Oe Of Og Oh Oi On Ou Ow Oy Oz Pb Pd Pe Pf Pi Pk Po Pz Qa Qc Qe Qg Ql Qn Qt Qv Qx Qy Qz Ra Rf Rh Ri Sr Tn Ua Uf Uk Ul Up Ur Us Uv Vp Wm Tj) Jv(aC aD aE AF aG Aj aK aL aM aN aO Ar aU aV AX bA Bc bF BG bH bJ bM bN bO bP bQ bR bS bU bX bZ cA cC cI cK cO cQ CS cT cU CW CX cY cZ dA DB dC dE dH dI dJ dK dM Ed Ef Et Ez Fa Fn fP Fy Gl Gp Hf Hu Hv Hw Im Io Is It Iv Jd Ji Jn Jr Js Ju Kf Ki Kq Kr Kx Ky Kz Lh Lj Ly Ma Me Mm Mp Mq Mr Ms Mw Nc Nf Nl Nn Nr Ny Oa Oe Og Oh Oi Ow Oy Oz Pa Pb Pc Pd Pe Pj Pk Po Qa Qb Qe Qg Ql Qm Qt Qz Rf Ri Sr Uh Un Us Uv Vt Tj tF) Oy(aC aD aE aF aG aH AJ aK aL aM aN AO aP aQ AR aV aW AX aY bA bC bF Bg bH bI bJ bL bM bO bP bR bS bU bV bW bX bZ cA cB Ch cI cK cL cM cN CO cP CS cT cU Cv cW cX cY cZ dA dC dG dI dJ Dk dL dM Ed Ef Fa Fb Fn fP Fr Fy Gl Hb Ic Id Iz Jd Je Jf Jg Ji Kc Ke Kf Ki Kk Ko Kr Kx Lv Lw Mm Mn Mu Nn Nw Om On Ou Ow Pc Ph Pk Po Qg Ql Qu Qy Qz Rf Ri Sr Tn To Tv Ub Uf Uh Um Un Ur Us Uv Vt Wm tF) Ji(aF bJ bX Cx Ef Et fP Fr Fq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Ko Kr Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oz Pa Pb Pc Pd Pe Pf Pg Po Pz Qa Qb Qc Qd Qe Us Wm) Nf(aC aD aE aF aG aH al AJ aK AL aM aN AO aQ aU aV aW AX aY aZ bA Bb bC BG bH bI bJ bL bM BO bP bR bS bU bV bW bX cA cB Ch cI cK cL cN CO cP cS CT cU CV cW CX cY cZ dA dB Dd De dH dI dJ dL dM Ed Ef Et Fb Fn fP Fr Fw Hb Ic Iz Jd Je Jf Jg Jr Ju Kg Ki Kr Kx Lv Lw Mm Mn Mu Nn Nw Om Ow Pc Ph Pk Po Qg Qh Ql Qn Qu Qw Qy Qz Ri Tv Ua Ub Uf Uk Ur Us tF) bJ(aC aD aE aF aG aJ aM aN aO bA bC bE bM bN bP bR bS bU bV bX cA Ch cP CS cT cW cX cL dL dM Ed In Io Iv Jr Ki Kl Kx Kz Lj Ly Me Ml Mq Mr Ms Nc Ng Nr Nw Oe Og Oi Ow Oz Pe Pk Po Qe Qu Rf Ri Un Us Uv Vt) bM(aF al aK aL aM aO aP aU aV aX aZ bA bF bH BN bO bP bQ bR bS bU bX bZ cA cC Ch cI cK cL cO cQ cR cT CX cZ dA DB dC DE dH dI dJ dL dM Ef fP Hf Kr Kx Kz Ly Nc Oe Og Oz Pa Pk Ri Us tF) cX(aF al AJ aK aL aM aN aP aQ aU aV aY bA bC bE bF bG bH bL bO bP bQ bR bS bU bW bX cA Ch cK cO cR cT cU cW cY cZ dA dG dH dI dJ dL dM Ed Ef fP Io Is Jn Jr Kx Kz Mr Ni Oe Oz Pk Ql Ri tF) Ef(aC aD aE Aj aM Ar Ax BA Bc bN bR cP CS cT cW Et Ez Fa Fr Gl Io Is Jd Jl Jr Kq Kx Lh Li Lj Lx Ma Me Ml Mq Ni Nn Nr Oa Oh Oi Ow Pe Pf Pk Po Qa Qe Ql Rf Rh Ri Sr Uv Vt) Po(Aj bO Ch Et fP Hq Hr Hu Hx Il Io Jh Jj Jn Jr Kr Lv Ly Me Mm Mn Mp Mq Ms Mu My Na Ne Ng Nh Ni Nj Nl Nn Nq Ns Nu Nw Nx Oe Of Og Oh Oi Oz Pa Pb Pc Qb Qc Us Wm tF) Me(aF Aj aK aV aW Ax bA bE bO bP bR bX cB Ch cI cK cO cT Cx cY cZ dA dI dJ dM fP Fr Hr Jd Jg Jr Ki Kx Lv Lw Mm Mn Mp Mu Nn Oh Om Pc Pk Qg Ql Qu Qy Ri Ua Wm tF) Cx(AF aM aY bA bC Bg bP bU bW cA Ch cT Cv dl dM Ed Et fP Gl Io Is Iv Jq Jr Ju Ki Kx Kz Lw Mm Mp Mq Mr Nc Ni Nw Oe Ow Oz Pa Ql Qn Qu Ri Sr Ua Uf Un) fP(aC aD aE aM aX bA Bc bN bV cP CS cT cU cW Ed Fa Fr Gl Io Kx Kz Lh Li Lj Ly Ma Ml Mq Ml Mq Ms Og Oh Oi Pe Pf Pk Sr Uv Vt Tj) Kr(bP Ed Et Is Iv Jd Jn Jr Ki Kx Lh Lw Mm Mp Mq Mr Ni Nw Oh Ow Oz Pj Qd Qe Ql Rf Ri Sr Un) Og(Et Fr Ik Im Is Jg Jl Jr Ki Kx Li Lw Mm Mq Mu Nn Nw Oh Om On Ow Pc Pd Qa Qb Qe Ql Wm) Aj(bA bU Ed Et Gl Hu Is Iv Jd Jn Jr Kx Kz Ly Ni Nr Ow Pa Pd Pk Qe Ql Ri Sr Un) Ed(bR bX cK cZ dM Fw Io Ki Kx Nc Ni Nl Oe Oi Oz Pk Ql Qu Qy Rf Ri Un Uv) bA(aF aK aL aO aS aV bN bO bP bR bU bX cK cY cZ dA dI Ni Oz Pa Pk) Ng(Et Fr Fy Im Jr Lw Ma Mm Mu Nn Nw Oh Om On Pd Pf Qa Qb Qe Wm) bP(aC aO bN bR bU bX cT Io Is Iv Kx Kz Mr Ni Oe Oz Pk Ql Ri Un) bX(aC aF bR bU cA cS dM Et Io Is Iv Jd Jr Ki Mr Ow Qe Ri Un) Jr(aL Et Fr Hr Im Kz Lw Mm Mu Nn Nw Pb Pc Qa Qb Ri Wm) Kx(aD Io Iz Ki Ly Mr Nc Ni Oe Oi Oz Pa Ql Qu Ri Wm) Io(aF bN bO bR bU Db Et Fy Kz Ow Pk Ql Rf Ri Un) Wm(Et Im Jn Ly Mn Mp Mq Oe Oi Oz Pb Qa Qb Qe) aC(aK aL aU aV bE bO bR cK cY cZ dA dl dJ dM) Qu(cT Db Et Fy Im Kz Ly Ma Mq Nr Ow Rf Rh) aF(bR dM Fy Gl Is Jq Kq Lw Ly Ni Oe Ri Un) Ow(aE aL Bg bO bR cK dC Kl Ly Pa Ri Ss) Mq(bO cK dA dl Hr Lw Mm Mp Mu Nn Pc) Oz(aE cT dM Et Ki Mu Nw Pk Qb Ri Tn) Kz(aO dM Iz Jn Ki Lw Oe Pk Ql Ri) bR(aN aO bU cT cU dl dM Is Mr Ni) Oe(Et Im Nw Qa Qb Qe Ql Rf Un) bU(aE aO aW bN cC cK dl dM) Oi(Jd Nn Oh Ql Rf Ri Un) Ly(dM Ki Mu Ql Rf Ri) Qb(Il Lw Nl Ns Pc Qc) Qe(bO Hr Lw Nn Pc Qc) Nw(Hu Hx Jh Mu Pb Pc) aO(bQ bZ cT cU dM Is) Ki(Db Nr Pk Ql Ri) aL(cT cW Is Jn Ni) bN(bH bW cT dl dM) Un(Bb Ko Ms Ri) Pk(cK dM Qg Ri) Lw(Im Jn Qa) Mu(Hu Lj Ml) Iz(Fy Jd Rf) Kl(Et Ez Is) Uv(aV bO dA) dI(aD cT cW) Bg(Is Jd) Co(Fy Rf) Ni(dM To) Qa(Il Qc) dA(aD aG) DgEt EzSs FrMy SrbO RiRf OfOm PacT} Ji{Kr(AD aE AF aG aI AJ aK AL aM AN AO AP aQ aR AS aU aV AW Ax aY BA BB bE BG bH bI bJ bL BN BO bP bQ bR bS bV bX bZ cA cB cC cD cF CH cI cJ cK cL cM cN CO CP Cq Cs CT Cu Cw CX cY cZ dA dB DC dD DE DG dH dI dJ DK dM eC Ed Ef Et Ez Fa Fb Fn FP Fr Fw Gl Gp Ha Hc Hf Hq Hr Hu Hw Ib Ic Id Ih Ii Ij Ik Il Im In Ip Iq Ir Is Iu Iv Iz Jd Je Jf Jg Jh Jj Jk Jl Jm Jn Jo Jp Jq Jr Jt Jv Jy Kc Kd Ke Kf Kg Ki Kk Kl Kn Ko Kq Kx Ky Kz Ld Lh Li Lj Lu Lv Lw Lx Ly Ma Mb Md Me Mf Mg Mj Mk Ml Mn Mq Mr Ms Mt Mu Mv My Mz Nb Nc Nd Ne Nf Ng Nh Ni Nk Nl Nm Nn Nr Ns Nt Nu Nv Nw Nx Ny Oa Of Og Oh Oi Om Ou Ow Oy Oz Pa Pb Pc Pe Pf Ph Pi Pj Pk Po Pz Qa Qc Qd Qe Qg Qh Ql Qm Qn Qt Qu Qv Qw Qx Qy Qz Rb Rc Rf Rg Rh Ri Rj Sr Ss St Tn To Tv Ua Ub Uc Ud Ue Uf Ug Uh Uk

Ng Nr Ns Nu Ny Oe Og Oi Om Oy Pa Pb Pd Pf Pg Pi Pk Pz Qv Qw Qz Rh Rj Sr Ss Tn To Tv Ua Ub Ud Uk Ul Um Uo Up Ut Vp Vv Wm Tj)
bA(Ad aK aM aP AR aV aW Ax bE bH bJ bO bR bV bW Ch cN Cs Cu Cv cY cZ dA Dc dF dG Dk Ed Ez Fa Fb Fn Fr Fw Fy Ha Hu Ic Id Ij Iv
Jd Je Jl Jn Jo Jp Jq Jr Ju Jv Jy Kc Kd Ke Kf Ki Kk Kn Ko Kp Kq Kx Ky Ld Lh Li Lj Lu Lw Md Mg Mh Ml Mn Mq Mt Mu Mx Mz Na Nc Ng
Ni Nj Nn Nr Nt Nv Nw Ny Oa Og Oh Oi Ok Om On Or Ou Ow Oy Pc Pe Pf Pi Pk Po Qa Qc Qd Qe Qg Qh Ql Qu Qv Qy Rf Rh Ri Sr St Tn Tv
Ub Uc Uf Uh Uk Ul Uo Up Ur Ut Vp Vt Tj) bV(aC Ad aF aJ aO aP aQ AR As aU aV aW AX aY bB bF bG bJ Bn Bu bP bQ bS cA cD cJ CP
CQ cR cS cT Cu CV CW cX dA Dc dD dG Dp Fn fP Fr Gp Hf Hv Hw Ic Ih Ij Io Ip Iq Ir It Iu Iv Iz Jd Jh Jn Jp Jq Jr Jt Ju Jv Ki Kk Ko Ks Kx Ky
Lu Lw Me Ml Mn Mq Ms Mt Mu Mz Na Nc Ne Nh Ni Nn Nr Ns Nw Ny Oe Of Oh On Pa Pf Pi Pk Pz Qc Ql Qv Qy Rc Rf Rg Rh Ri Ss St Ub
Uc Ug Uk Ul Up Ur Ut Vp tF) Qv(Ad As Ax Bn bQ Cp Cq cT Cu Cv Cw Dc Fr Hv Hw Id Ih Ij In Ir Is Jd Jn Jq Jr Jt Jv Kn Ko Kp Kr Kx Lw
Md Ml Mn Mx Mz Na Nm Nn Nr Oh Pb Pi Po Ql Qy Rf Ri Rj Sr Uc Uf Ul Up Us Vp) Fa(Ad aJ aW bP Cp cT Cu Cv Cw dA Dc Dp Ef Fb fP
Hu Hv Hw Ic Ij In Io Ir Jd Jq Jt Ju Jv Ki Ko Kp Kq Kr Kx Lw Mh Ml Mn Mq Mz Na Nw Ny Oh Om Pb Pi Ql Qy Rf Rh Ri Sr Up Vp tF) aP(aD
aJ aI aN Ar aS aW AX Bg bI bP bR bS cA cL Cs cT Cw dA dH Ed Fb Hu Ic Ij Jd Jn Jv Ko Kq Kx Ky Lw Ml Mn Ms Mt Mz Na Ni Nl Nr Oi Pk
Ql Rf Rh Ri Sr Tv Ua Uo Up Wm tF) aJ(AR aS Ax bQ bR Cs cT Cu Cw dA Fy Hu Ic Ij Jd Jn Jp Jr Kq Kx Lu Lw Ly Ml Mn Mq Mt Na Nf Ni
Nr Ny On Ow Pi Pk Qa Ql Qx Qy Ra Rf Rh Ri Sr Tn Tv Uo Wm) Ax(Ba bW cE cN Cv Cx dF dG Dk Et Fb Fr Hu Jd Jl Jp Jq Jr Ju Jv Jy Ke Ki
Kq Kx Ky Lu Lw Mm Mu Ng Ni Nw Oi Om On Po Qy Ri Sr St Uf Uh Ur Ut Vt) Tn(Ba bW Ch Co Cv Et Fr Ib Id Is Jl Jq Jr Ju Jv Jy Ke Kq Lw
Mm Mt Mw Ni Nn Ny Oh Ok On Pf Qa Qe Qu Ri Sr Uf Uh Ur Ut) cT(cN Cv dA Dc dG Fb Fr Hu Id Jd Jc Jn Jp Jq Jr Jv Jy Ki Kk Kx Lw Mu
Nn Nw Oi Qd Qu Qy Rf Ri Sr St Tv Ur Vt) Lw(Ar bJ bM bN bP bZ cJ cP Cs dA dK eC Fp Kx Lj Mb Ml Nr Oh Pc Pf Qx Rf Rh Ur Wm) Kq(aE
aF Ao aW Bb bl bJ bM bP cl eC Ih Ii Ir Iu Iz Jv Kx Mz Ng Nm To Tv Ur Us Vo) Tv(Ba Et Fr Is It Jl Jn Jr Jy Mt Ni Nn Ny Oh On Pf Po Qa Sr
Uh) Sr(aW bP Cs dJ Ih In Iu Jo Jv Kg Kx Ms Og Oi Qg Qx To Ug Ur) Fr(aW bI bO bP Ch cK Co Cs dA Jv Kx Oi Pk Qx Ri To Ua Wm) Ur(dG
dL Fy Id It Iv Jd Jn Jq Jr Js Ml Mq Nf On Pe Pk Qa) Kx(Ba Cv cW dA dG dL Jd Jv Lu Mq Mx Ni Oh On Pf Uf) aW(dF Et Is Jl Jn Jr Jy Ni Nn
Oh On Pe Pf Po Qa Qe) Jn(bP cN Co Ih In Ir Iu Iz Jv Ks Lu Ms Ng Oi) Jr(bP cN Ih Ii In Ir Iu Iz Jv Kg Lu Ms Oi To) Oh(aD bI cN Iu Jd Je Jv Kk
Lu Ms Oi) Nn(Ch Co Iu Iz Jv Lu Ms Ng Oi To) Cs(Cv Jd Jq Jv Jy Ke Mu Nw On) dG(bR dK Jv Kr Ml Nr Oi Ri Us) On(aE bP cl Jo Kg To Vo
Wm) Fy(bH cN Co Iz Kg Lu Ng) Lu(Et Jd Pc Pf Po Rf) To(Is Jl Mt Ni Ny Qa) Cv(Ml Nr Qx Rh Wm) Jd(bP Ch Jv Ms Oi) eC(Id Mw Ny Om
Pk) Ml(Bo cN Kg Qg) Is(Ih Ir Iu Rm) Jv(bQ Jp Pf Po) Oi(Ba dA Nr Rf) Co(Nr Pe Po) cN(Ni Pk Rf) Wm(Dc Jq) dA(cW Mn) BaKl ChPf PoRi
QxKe KkOw] Ch{Jd(aC AD aE AF aG aH al aJ aK AL aM AN AO AP aQ AR AS aU aV AW AX aY aZ BA BB BC bE bF BG bH bI bJ bL
bM BN BO bP bQ bR bS bU bV bW bX bZ cA cB cC cD cE cF cG cH cI cJ cK cL cM cN CO CP CQ cR CS CT CU CV CW CX cY cZ dA DB
DC DD DE dF DG dH Di dJ DK DL Dp eC Ed Ef Et Ez Fa Fb Fn Fp Fr Fw Fy Gl Gp Gz Ha Hb Hf Hq Hr Hu Hv Hw Hx Ib Ic Id Ih Ii Ij Ik Il
Im In Io Ip Iq Ir Is It Iu Iv Iz Je Jf Jg Jh Jk Jl Jm Jn Jo Jp Jq Jr Js Jt Ju Jv Jy Kc Kd Ke Kf Kg Ki Kk Kl Kn Ko Kp Kq Kr Ks Kx Ky Kz Ld Lh Li
Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf
Ng Nh Ni Nj Nk Nl Nm Nn Nq Nr Ns Nt Nu Nv Nw Nx Ny Oa Oe Of Og Oh Oi Ok On Or Ou Ow Oy Oz Pa Pb Pc Pd Pe Pf Pg Ph Pi Pj Pk Po
Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tv Tz Ua Ub Uc Ud Ue Uf Ug
Uh Uk Ul Um Uo Up Ur Us Ut Uv Vo Vp Vt Wm Tj tF) Hu(aC aD aE aJ Al aM aN aP AR aV Ax aY aZ BA bB BC bF bH bJ bM bN bP bQ bR
bS bU bV bX bZ cA cG cN cO cP CS cT cU CW cZ dA Db dE dF dG dL eC Ed Et Ez Fa Fp Fr Fy Gl Ij Im Io Is It Iv Jl Jn Jp Jr Jv Ki Kq Kx Ky
Kz Lh Lj Lu Lw Lx Ly Lz Ma Me Ml Mn Mp Mq Mr Ms Mv Mw Nc Nf Ni Nj Nk Nl Nn Nq Nr Nt Oe Og Oh Oi On Ow Oy Oz Pa Pd Pe Pf Pk
Po Qa Qb Qe Ql Qt Qv Qy Rf Rh Ri Sr Tn Uf Ur Us Wm tF) bJ(Ad aP Aw bA bV cT Dc dF dG Fa Fr Fy Id Is Jh Jl Jn Jq Jr Kd Ke Kf Kn Kq
Kx Lv Lw Mt Mu Mw Mz Nn Nr Ny Ok Om On Pe Pf Pk Po Qa Sr Tn Ut Uv Vt) Kx(aP BA bV cT dA Ed Et Fa Fb Is Je Jl Jn Jr Jy Kq Ly Mc
Mq Mr Mu Nf Ni Nn Pe Pf Pk Po Qt Qy Rf Sr) Je(aP Ax BA bM bV CS cT cW eC Ed Fa Fr Fy Li Lx Ma Mq Nf Nn Nr Oh Ow Pe Pf Po Rf Sr
Tn) Qy(aP Ax bA bV Cs cT cW dK Fa Is Jn Jr Lx Ly Ma Ml Mq Nn Nr Pe Pf Pk Po Ql Rf Sr Tn Tv) Nf(aJ aP bA bV cN cT Fb Fr Is Jh Jl Jp Kc
Kk Kq Lw Lx Mu Nn Ny Om On Sr Tn) dA(aC aD Fa Fy Id Jl Kq Mq Nn Nr Nw Pe Pf Pk Po Qe Ql Rf Ri Sr Ua Uv) Nn(aW bH bO bR cl Dp
Ed Fp Jv Kr Kz Lu Ly Me Og Pa Pk Ql Ri tF) Kq(aF aK aU bO bX cl cK Cx Db eC Ed Fn Fp Kl Kr Ly Og To Us Vo) bV(bO Dp Ef fP Im Is Jn
Kr Kz Ly Mr Ni Oy Pk Ql Rf Ri Us tF) Sr(aK aU bH bO bX cK dJ Dp FP Jv Kr Ly Og Us tF) Me(aP Ax BA bF bZ cN Et Jn Lx Mn Oh Tn Ur)
Kr(dG Dk Et Fr Id Is Jn Jr Ke Mu Ok Om On Ut) Fp(aP Ba Cv Fa Fr Jh Jy Lw Lx Mu Nw Om On) Ni(aE aP aW Ax bA bP cl cN Ed Nr Po Rf
Tn) Us(Ba dG Dk Fr Jn Jr Jy Mq Mu On Ut) Tn(aV bO Ed Im Is Kz Mw Oy Oz Pa) Is(aW cN Ih Ir Iu Lu Og To Tv) bO(aP bA dF dG Fr Jr Pe
Pf Po) eC(Dc Kd Lw Mu Mw Ny Om Pk) Fa(Dp Ef fP Ly Ql Ri tF) Jn(aW cI cN Lu Ms Oi Ri) Kz(aP bA cN Fr Lx Mu) Ba(cI Ed Kl Og Ss)
Pk(aP bA bQ cN Ki) Mq(bA bE bF cK) Mw(bA cT To Tv) Ql(bA bQ Ly Ms) Cx(Lw Mu On) Ed(Jy Ma Rf) To(Mt Ny Ut) Ri(bA bQ Jr) Dp(aP
bQ) Po(aV tF) Lu(Et Rf) Mu(bN bX) Im(aW cN) On(bX cI) FybH LwbN LyUf MlQg TvIt QeaW JlOg JrUr RfcN aDbQ aPtF} Fp{Lw(AF al
aK AL aM aN Ao Ap aQ aS aU Ax aZ BB BG bH bI bJ BN BO bR bS bU bV bX bZ cA cC cH cI cL cN Co CQ cR Ct cW CX cY cZ DB dC
Dd DE Dg dH dJ dK Ed Fa Fn fP Fr Fw Gp Ha Hx Ib Ik Il Im Ir Is Iv Jd Je Jg Jp Jq Jr Ju Jv Jy Kd Kf Kg Ki Kl Ko Kr Kx Kz Ld Lx Ly Mi Mj
Mm Mn Mq Mr Mt Mu Mx Mz Na Nb Nf Ng Nj Nn Ns Nw Og Oh Oi Ok On Pa Pc Pe Pk Po Qb Qg Qh Ql Qn Qx Qy Qz Rb Rh Ri Rj Rm Ss
Tz Ua Uc Ue Ug Uo Up Ur Us Ut Vo Vp tF) Lx(Ar aU aW bF BG bQ bR bS bZ cA Co Ct cU De Dg Ed fP Hq Hr Hu Hv Hw Hx Ij Ik Il In Io Ip
Iq Ir Is It Iu Iv Jg Jk Jn Jp Jq Jr Js Lj Lv Ly Lz Mc Md Me Mf Mg Mh Mj Mk Ml Mm Mn Mp Mq Mu Mv Mw Mx My Mz Na Nc Nd Ng Nh Nl
Nm Nr Ns Nu Nv Nw Nx Ny Of Og Oi Ok Om On Oy Oz Pb Pc Pd Pg Pz Qa Qb Qc Qh Ri Ss Tz Ue Vo Wm) Nw(Al Ao aW bV cN cW Fa Fr
Hq Hr Hu Hv Hw Hx Ih Ii Ij Ik Il Im In Io Ip Iq Is It Iu Iv Jg Jh Jk Jm Jn Jp Jq Jr Js Li Lj Lu Lv Ly Lz Ma Mc Me Mf Mg Mh Mi Mj Mk Mn
Mp Mq Mr Ms Mt Mu Mx My Mz Na Nb Nc Nd Ne Nf Ng Nh Ni Nj Nk Nl Nm Nn Nr Ns Nt Nu Nv Ny Oe Og Oh Oi Ok Om On Oy Oz Pa Pb Pc
Pd Pe Pg Po Pz Qa Qb Qc) On(Ao aW cN Co Cq De Dg Hq Hu Hx Ih Ik Il Im In Ip Iq It Iu Iz Jh Jo Jp Jq Jr Kg Kr Li Lj Lu Lv Ly Lz Ma Mb
Mc Mf Mi Mk Mm Mn Mp Mq Mr Ms Mt Mu Mv Mx My Na Nb Nc Nd Ne Nf Ng Nh Ni Nj Nk Nl Nm Nn Ns Nt Nu Ny Of Og Oh Oi Om Oy
Oz Pa Pb Pc Pd Po Qb Tz Ur Us) Cv(Af Al aM aZ Bb bJ bN bO bR bV bX cJ Co Cq cW CX DB De Dg Fa Hx Ii Ik Iu Jg Jo Jv Kg Kr Lu Ly Mg
Mq Ms My Nc Ni Nj Nl Og Oi Oy Pz Qg Qn Ri Tz Ug Ur Us Vo) Fa(Ar aW Bb Bg bS bV Co Ed Fn Hq Hu Hx Ik Iq Iu Iv Jo Jv Jy Ki Kq Ly
Me Ms Mv My Ng Ns Oi Pi Qg Qt Qy Ri Tz Ue Ug Tj) Oi(aJ Ba bV cE cN Dk Et Fr Is Jd Jg Jl Jy Ke Kq Li Mm Mu Nn Oh Ok Om Po Qa Qv
Qy Ri Sr Ur) Sr(aW Co Cq Ih Ii Ik Ir Iu Iz Jo Jv Kg Kr Lu Ng Og Qg Qv Ri Tz Ue Ug Ur Vo) Kq(aF Al Ao aW Bb Bg Co Cq Dl Ii Iz Jg Jo Jt
Kg My Of Pg Ue Ur Vo) Fr(Co Hu Ik Io Jq Ly Mg Mq My Na Ng Nh Ni Nq Nr Ns Og Pb Po Wm) Jq(Al Ao Bb bJ Co Jg Kg Md Mm Mn Mp
Mq Mu Nn Ur) Mu(Al Ao Bg Co Hu Hx Mq Ng Ns Og Po) Ng(Ba Et Jg Jl Mm Nn Oh Ok Om Po) Og(Et Jg Jl Mm Nn Oh Ok Om Po) Ur(aD
aP cN Id Jl Me Ri Uv Vt) Co(Dc Jy Ke Nn Pe Rf St) Ik(bV Et Mm Nn Oh Po) Ke(Cq Jo Kg Ko Kr Us) Om(Hu Jo Mq Ms Ns Oy) Mq(aD bV
Oh Qv) Jy(Ao aW Jv) Ri(aP bV Qv) Vt(Kg Lu Qv) Po(In Jo) Mm(Hx Ly) Ni(bV cN) BaMg BgMw QaKg JlaW JoOk UtOy bRcN] Ng{Nn(bJ
bO dA Dp Et Fr Hq Hr Hu Hv Hw Hx Ih Ii Ij Ik Il Im In Io Ip Iq Ir Is It Iu Iv Jh Jk Jl Jn Jo Jp Jq Jr Js Jt Jv Kr Lh Li Lj Lu Lv Lw Lx Ly Lz Mb
Mc Md Me Mg Mh Mi Mj Mk Ml Mm Mn Mp Mq Mr Ms Mt Mu Mv Mw Mx My Mz Na Nb Nc Nd Ne Nf Nh Ni Nj Nk Nl Nm Nq Nr Ns Nt
Nu Nv Nw Nx Ny Of Og Oh Oi Ok Om On Oy Oz Pa Pb Pc Pd Pe Pf Pg Po Pz Qa Qb Qc Qd Qe Wm tF) On(bJ Et Hq Hu Hv Hw Hx Ih Ii Ij Ik

Figure 8 Continued

Im In Io Ip Iq Ir Is It Iu Iv Jk Jl Jm Jn Jp Jr Js Jt Kr Lh Li Lu Lv Lw Lx Ly Ma Mb Mc Md Me Mf Mg Mh Mi Mk Ml Mn Mp Mq Mr Ms Mt Mu Mv Mw Mx My Mz Na Nb Nc Nd Ne Nf Nh Ni Nj Nk Nl Nm Nq Nr Ns Nt Nu Nv Nw Nx Ny Of Og Oh Ok Om Oy Oz Pa Pb Pd Pe Pf Pg Po Qa Qb Qd Qe Us Wm) Po(bJ bO Et Fr Hr Hu Ih Ij Il Im Io Iq Is Iu Iv Jg Jh Jk Jl Jp Jq Jr Li Lj Lu Lv Lw Lx Ly Ma Mc Me Mg Ml Mm Mn Mp Mq Ms Mt Mu Mv Mw My Na Nc Nd Ne Nf Nh Ni Nk Nl Nq Ns Nt Nu Nw Ny Og Oh Oi Ok Om Oy Oz Pb Pc Pd Pf Qa Qb Qc Qe Wm) Lx(bO Db Ed Et Hu Ih Ik Im Is Iu Iv Jk Jm Jn Jo Jq Jr Jt Lh Lv Me Mg Mm Mn Mp Mu Mv Mw Na Nd Ne Nf Nh Ni Nl Nu Nv Nw Nx Ny Og Oh Ok Om Oy Oz Pd Pe Pf Pg Pz Qa Qb Qc Qd Qe Wm) Mq(aN aV BA bE bF bJ bP bQ cI cK cT dA Et Fr Fy Is Jd Jg Jr Kx Ma Mm Mn Mp Mu Nw Oh Om Pf Qa Qb Qy Rf) eC(Ad Cp Cu Cw Dc Dk Hu Hx Ib Id Ij Iv Jd Je Jq Jr Kd Kn Kq Lw Me Mt Mu Mw Nb Ny Om Pe Pi Pk Qa Sr Ut) Om(Et Hu Ik Im Io Is Jn Jr Li Lj Lu Lv Ly Mc Ml Mr Ms Mv Nf Nh Ni Nt Og Oh Oy Pf Qa Qb Qe) Mu(Et Fy Hu Im Jr Li Lj Ma Ml Mn Mp Nf Nh Nw Nx Og Oh Ok Ow Pf Qa Qb Qe Wm) Jd(Ax BA Cs cT Ed Fy Hu Jv Kr Kx Nc Ni Nr Oh Oi Ow Ql Rf Rh Ri Us) Nf(BA bV cT Et Fa Fr Jg Jl Nw Oh Ok Pf Qv Ur) Fr(Et Hu Ij Ik Im Jn Jr Ni Oy Qa Qb Qe Wm) Qa(bJ Et Hu Ih In Is Jh Jr Mm Mp Oh Wm) Jr(Et Im Is Li Mv Nw Oh Ok Pf Wm) bJ(bA bV cT Fa Fy Kq Pe Pf Pk Tn) Hu(cT Et Fy Jg Jl Kx Oh Ow Rh) Mv(Et Is Mm Mp Nw Oh Ok) Ni(Ax bV cN Cs Kx Nw Tn) Ba(Jv Kl Me Rf Ss) Im(Jg Lw Nw Ok Pf) Et(Lu Lv Nh Pc) Sr(bO Jv Kr Us) Fa(Dp fP tF) Oh(Ik Lv Me) Wm(Jl Qd) Fy(bH Qg) Qy(bA cT) Kq(Kr Us) LuRf LvOk JeOw JlOg PfbO bVfP} Kq{aF(Ad Af aK aL aU aW Ax aZ Bb Bg bH bJ bO bQ bX bZ cC cI cK cN cO Cp Cq Cs Cx cZ dA Db DE Dg Dl eC Ed Fa Fn Iz Jt Jv Kf Kg Kl Ko Kr Kx Kz Ly Mc Nf Nm Of Og Oi Oy Pk Qz Ri Ss To Uc Ue Ur Us Vo) eC(Ad aE aK aL aN Ao aW Ax Bb Bg bH bI bJ bO bP bX cH cI cN Co Cq Cs Cu Dc De Dg Dl Ed Fn Hu Ih Ii Ir Iu Iz Jf Jg Jo Jt Kf Kg Ki Kl Ko Kr Kx Lu Ma Mg Nm Of Og Pk Qg Qu Qz Ra Ss Uc Ur Us Vo) Of(aK Ax bA Bb bJ bN bP bR bX bZ cI cO cT CX cZ dA Db Ed Fn Fy Hu Jd Jg Jv Ko Kr Kx Kz Lx Ly Ma Mq Nf Nn Nr Og Oh Ow Oy Pk Ql Qx Qz Rf Rh Tn To Uc Us Vo Wm tF) Us(aK aL Ao aQ aW Bb Bg bH bJ bP bV bX cI cN Co Cu cY cZ dJ Ed Ef Fn Hq Ii Iz Jg Jv Kg Ki Kl Kx Lw My Oy Oz Ql Qu Qz Tn To Vo Wm) bJ(aC aD aE aG aM aN Ao Bb Bg bP bX Co Cp Cs dC De Dg Ed Ef Iz Jg Jo Jt Jv Kg Ki Kl Ko Kx Lj Me Ms Og Oi Oy Qg To Uc Ur Vo) Kl(aK aV BA Bb cT cZ dA De dJ Ed Ef Et Ez Fn Hb Hq Iz Jk Jv Kx Nf Nn Oh Ow Oy Oz Qc Ql Ri Ua Wm tF) Vo(aK aL aV Bg bO bX cK Cx cZ dA Dp Ed Ef Ez fP Hv Is Jv Kd Ko Kr Kx Kz Ly Me Nc Nf Ni Oz Ri Wm tF) Ed(aW bO bX cK Cu cZ Ef Fn Fw Hq Ii Iz Jg Jt Jv Ki Kr Kx Oe Oi Oy Qg Ri Tv Uc Ur tF) Kr(aK aL Ao Ax Bb Bg bP cI cN Co Cs Cu Ef Hq Ii Iz Jv Kg Ki Kx My Oy Qu Qz Ri Tn) Ef(Ao aW Bb Bg bN bX Cs cZ Fa Iz Jo Kg Kx Ld Lj Ly Mq Mv Nn Ql Qv Rh) Oy(aE aW bA bP cI Fn Hu Ih Ii Ir Iu Iz Jd Ki Kx Ql Ri Tn To Tv) Dp(Ad Ao aW Bb cI Ii Ir Iu Iz Jt Kg Nm Qv Tn To Ur) Nf(Ao Bb bP cI Co Ii Ir Iu Iz Jo Qg Tn To Tv Ur) Iz(aK bX Cx cZ fP Hf Hu Im Jd Kz Ly Me Pa tF) Ly(Bg bP cI Ii Ir Jt Jv Ki Qu Tn) Uc(Bb cZ Fn Jv Ki Mm Ow Ri Wm) fP(Ao aW bV Cs Fa Qv Uc Ur) Bg(bO bX cI Hu Jd Je) Jv(aK bX Kg Kx Og To) Oz(aW cI Tn To Tv) bO(aE bP Cp Fa Fn) Ki(bX De Kx Pk) Me(dA Tv Ur) Jg(bH Pg Qg) Kz(Tn To Tv) aK(Jt Mq Oi) bX(Co Ii Qu) cI(Fn Hq Mq) tF(Ao aW Fa) BbJd CoCx FyKg TvIv JtaV PaaW} Lw{Us(AF aK aL aM aP Ar aU aV Ax bA bJ bN bO bP bQ bV bX bZ cB cC cN cO Cs cT CX cZ dA Db dE eC Ed Et Ez Fa Fn fP Fy Hu Hw Ib Ih Im In Ir Is It Iv Jd Jl Jm Jn Jr Jv Ki Kr Ks Kx Kz Ld Li Lj Lv Lx Ly Me Ml Mq Mr Mt Mv Mw Nc Nf Ni Nl Nn Nq Nr Ny Oa Og Oh Ow Oy Oz Pc Pi Pk Po Qa Qb Qe Qg Ql Qm Qy Rf Rm Sr St Wm) Kr(AF aK aM Ar Ax aZ bJ bN bV bZ cO Cs CX cZ dA dE eC Ed Et Fa Fn Fy Hu Ih Im Is It Iv Jd Jn Jr Ki Kx Kz Ld Li Lj Ml Mq Mr Nf Nn Nr Oa Oh Ow Oy Oz Pe Pk Po Qa Qb Qd Qe Ql Qy Rf Sr St Uh Ur) Nf(aE aK aW bA Bg bP bV cI cN Cs cT Ed Fa Iz Jf Jv Kf Kg Ki Kk Kl Kx Lx Qg Qn Qv Qx Rg Ss Tn To Tv Uc Ue Ug Ur Uv Vo) bJ(aC aD aE aG Ao bN Cs Cx dC Ed Fn Iz Jv Kf Kl Ko Kx Lj Nd Oa Og Pk Qg Qz Rb Rf Ss To Tv Uc Ue Ug Ur Uv Vo) eC(aK Ap aU aW Bg bO bX cI cN Dg Ed Fn Jd Jf Kf Kg Ki Kl Ko Og Qg Qt Qu Qv Qz Ra Rb Ss Uc Uo Ur Vo Vp) Cx(bN bX cN dE Ed Fa Fn Jd Jv Kf Kg Ki Kl Ko Kx Ld Nd Oa Og Pk Qg Ql Qv Rf To Tv Uc Ur Vo) Oy(aE Ar aW Ax bA bV bZ cI cN Cs cT dC Ed Fa Jd Ki Kk Kx Pk Qg Qv Qx Tn To Tv Ue Ur Vo) bN(aK aN aU aW bO bP cK dA dJ Ed Ef Fn Jd Jv Kf Ko Kx Nd Og Qn Qz Ri Ss Tn To Tv Vo) Ed(aF aK aU bO bX cC cK cX cZ Db dE Fn Fw Jd Ko Kx Nl Og Pk Qg Ri Ur Vo tF) Kz(aK aW Ax bP bV Kg Kk Kl Kx Og Qg Qv Qx Tn To Tv Uc Ur Vo) Vo(bX Db dE Ez Im Jn Kx Ly Nr Ow Pk Ql Rf Rh) Rf(aF aK aU bO bX Dg Jg Jt Kf Kl Ko Og) Kx(Af aU bO Hf Jv Kf Ki Kl Ko Og Pa) Jd(aF Bb Bg bX Cp De Iz Jg Ko Ly) Me(aW Ax cI Cs Rh Tn To Tv Ur) Pk(aK bX cK Kf Ki Ko Ly Og Uc) bO(cW Fa Fy Lj Ml Nr Oa Sr) Cs(Dp Ef fP Hf Ko Pa tF) To(Db Ih Im It Iv Ni) Kl(Ba Im Jn Ma Nn Nr) Og(Is Lx Mq Mu On Po) Fa(aF bX Dp fP tF) Mq(aK dA Ef Mp) Im(aW Iz Tn Tv) Ly(Ld Ql Ur) Uc(Ih Jn Ow) Ko(Jn Nn Nr) bX(Jv Ki Oa) fP(bV Ml Qx) Ax(Hf Pa) Dp(Qv Ur) Kf(Jn Nr) EfMv FnaF FyKg MldD NiTv KidE} Og{Lx(bO Ed fP Hq Hr Hv Hw Hx Ih Ii Ij Ik Im In Ip Iq Ir It Iu Iv Jd Jk Jm Jn Jo Jq Jr Js Lh Li Lj Lv Lz Mc Md Me Mg Mi Mj Mk Mp Mq Mr Mt Mu Mv Mw Mx My Mz Na Nb Nc Nd Ne Nf Nh Ni Nj Nl Nm Nn Nq Nr Ns Nt Nu Nv Nx Ny Oe Om On Oy Oz Pa Pd Pe Pf Pg Po Pz Qa Qb Qc Qe Qy Wm) Mu(Et Fr Hr Hv Hw Hx Ih Ii Ij Ik Im In Io Ir Is Iv Jh Jk Jl Jn Jo Jp Jq Jr Jv Kx Lh Li Lj Lu Lv Lz Ma Mb Me Mf Mh Mi Mj Mk Ml Mn Mq Mr Mv My Mz Na Nb Nc Nd Ne Nf Nh Ni Nj Nl Nn Nq Ns Nt Nu Nw Nx Oh Oi Ok Om On Oy Oz Pc Pd Pe Pf Pg Po Qa Qb Qc Qe Wm) On(bJ Hq Hv Hw Hx Ih Ii Ij Ik Im In Io Iq Is It Iv Jh Jn Jr Js Kr Li Lj Lu Lv Ly Mb Mc Md Me Ml Mq Mr Mt My Na Nc Nd Ne Nf Nh Ni Nj Nl Nn Ns Nt Nu Nv Ny Of Oh Om Oy Oz Pa Pb Pc Pd Pe Pg Po Qa Qb Qc Qe Wm) Po(bJ bO dA Et Fr Hu Hx Im Io Iq Is Iu Iv Jg Jl Jq Jr Lu Lv Me Mm Mn Mq Mr Ms Mw My Na Nb Ne Nf Nh Ni Nl Nn Ns Nt Nw Oh Oi Ok Om Oy Pa Pe Qe Wm) Mq(bJ cK dA Et Fr Im Is Jd Je Jl Jq Jr Jv Ki Kx Lv Ma Mm Mn Mp Nn Nw Oh Ok Om Qa Qb) Om(eC Hu Im Io Is Iv Jr Lj Lu Lv Me Ml Ne Nf Nh Ni Ns Nt Nu Nw Pd Pe Qa Qb Qe Wm) Sr(aF aK aV bH bJ bO bX cK cZ dA dJ Dp eC Ed Ef fP Jv Ki Ko Nf Wm) Wm(Fr Is Iv Jl Jn Jq Jr Nn Nw Pe Qa Qd Qe) Nf(bW cN Cv Et Fr Is Jl Ki Nn Nw Ok Pf Uf) Ki(dA Jd Jn Kx Ml Ni Nn Ow Pe Pk Qa Ql) Jl(bJ bO Hu Ih Io Jv Kx Me My Nd Ne) Nw(dA Im Is Jr Lv Ni Nn Nt Nu Oh Qa) eC(bA Dc Hx Id Jq Jr Nb Ny Pi Pk Vt) bJ(bA bV Cv dL Id Jq Jr Ke Ok Pe) Jv(Ax Ba Is Jd Jn Kx Ni Nn Pk) Co(Fy Is Jd Jn Ni Pe) Nn(Jr Lv Me Ne Qe) Ok(Ik Lv Mb Me Ni) Fa(Dp Ef fP tF) Fr(Ik Me My Nd) Jd(Bg Ed Iz Kx) cN(dA Iv Jn Ni) bO(aJ aP Pf) bV(fP Ni Ql) Cv(Ed Kz) Is(Hu Jr) Pk(bW Uf) BaKl EtJr MeOh MpNd NiKx IhQa QybA aPfP} Sr{bO(aC aD aE aJ aK Al aM aN aP aW Ax aY bA Bb Bg bI bJ bM Bo bP bV bX bZ cI cK cN CO cS cT cU cW CX dA Dd De dG DL eC Ed Fa Ii In Io Ir Iu Iz Jg Jh Jn Jo Jr Jt Ju Jv Ki Kk Kx Ky Lu Lv Lx Ly Ms My Nc Ne Ni Nl Nm Ns Oe Oh Oi Oy Pf Pk Po Qc Qg Ql Qn Qu Qv Qx Rf Rh Ri Ss Tn To Tv Ua Ue Ug Uk Ur Vo) Jv(aK aU aV aW bH bJ bP bX cI cK dA dE dJ Dp eC Ed Ef fP Hf Hu Ir Jd Je Jo Kg Ki Kl Kr Kx Kz Ly Mb Nf Oy Pa Pk Qg Qv Ur Us Vo tF) bJ(aE aK aN aW Bg bP bV cI cK Co Cq dC De Dl Ed Ii Ir Iz Jg Jo Jt Kg Ki Kr Kx Mg Ms My Nm Oe Of Oi Qg Qu Ss To Tv Ug Ur Us Vo) Us(aK bH bW cN Co dA dJ eC Ed Kg Ki Kx Lx Mm Mq Mr Mu Nl Oi Oy Oz Qg Ql Qz Ri Uf Ur) eC(aK aU aW bH bI bX cI cK cN Co Cq Dg dJ Ed Ii Iu Jo Jt Kg Kl Kr Kx Nm Qu Ss Vo) Ef(aW Bo bV Fa Hu Ih Ir Iu Iz Kr Kx Ld Lu Ly Ms Ni Oi Qv Qx Ri Ug Ur Vo) Oy(aW bA bP cK cN dA dJ Ih Ir Iu Kg Ki Kr Kx Lu Qg Qv Tn To Tv) Dp(Ao aW Ih Ii Ir Iu Iz Jo Kg Lu Ms Qv Tn To Tv Ue Ug Ur Vo) Kr(bH Co dJ Kg Ki Lx Mm Mp Mu Nl Ow Qg Ri Uf) fP(aW bV Fa Ih Ir Iu Iz Lu Oi Qv Ue Ug Ur Vo) tF(Ao aW Ed Ih Ir Iu Iz Kg Ms Oi Qv Ue Ug Vo) aK(aQ Bb cX cY Ed Kf Ki Ko Kx Ni Qg Ql Ri) Ed(aU cK cZ dJ Fn Fw Jd Kx Qg Ri) Qg(aU aV Bb bX cK Cx dA Ko Nf) Ki(bX Cx dE dJ Kx Ly Pk Ri) dA(bX Co Cq Fw Kx Nl Oi Ri) Ni(aW cI Tn To Tv Vo) Ri(cK Kl Tn To Uc Vo) Ii(Cx Im Jn Jr Rf) Nf(Jo Kg Oi Tv) Iz(Hu Im Jd Je) Kx(aU aV Kg Vo) Kz(aW bP To) Cx(dJ Kg) cK(bX Qz) BaKl BgJd FyKg NcTo VoaV} Oy{Tn(aJ aP Ba bW Co Cv Cx dG Dk Et Fr Hw Id In Is Jd Jl Jq Jr Jv Jy Ke Ki Lx Mm Mp Mr Mt Mu Mw Ni Nv Nw Ny Om On Pd Po Qd Qe Qn Ri St Uf Uh Ut Vt) Tv(aP Cv dE Dk Et Fr Gl Hu Is Jd Jh Jk Jl Jq Jr Jy Ke Lx Mr Mt Mu Mw Ni Nn Nq Nv Nw Ny Om On Pa Pd Po Qd Qe Qy Ri St Ua Uh Ut) Jd(AD aJ Ao aP As aW Ax bA bP bV cN Co Cq cT Cw Dc Hw Id Ij In

Figure 8 Continued

Jv Kn Kx Me Mi Ml Ms Na Nf Ny Oi Om Pb Pd Pe Pi Pk Qv Vp) bA(bJ bO Cv dA Dc Dk Dp Fa Fb fP Hu Je Jn Jq Jy Ke Kg Kk Kx Mu Ni Nw
Ny On Pe Pk Qg Ql Qy Ri Uh Ut Vt tF) aW(dG Dk Et Is Iv Jl Jn Jq Jr Jy Ke Kn Lx Mr Mw Ni Nn Nv Ny Om On Pd Pe Pf Po Qa Qd Qe Ut)
bV(cA Cv Fb fP Hu Io Ip Is Iv Je Jn Jq Jr Jv Ki Kk Kx Lx Mu Nc Ni Nr Ql Qu Rf Ri tF) Kx(aJ aP cN Cv dG Fa Fr Hu Id Je Jq Jr Ke Ki Lu Lx
Mu Ni Ny Om On Pf Qv) To(Cv Dc Dk Fr Is Jl Jq Jr Ke Lx Mt Mw Ni Nw Ny Om On Pd Po Qd St Ut) Lx(bR Ih Ij Ik In Iv Jm Js Me Mq Mu
Na Nc Nf Pd Pe Qa Qb) On(aE Ax cl cN Ik Io Jr Kk Me Nc Nd Nf Pa Po) cN(Iv Jn Jq Jr Ke Ni Nr Pd Pk Rf) Hu(aD aJ aP Ax cT Cv dG dL Pk)
Mu(Ax Fa Jr Ml Oh Pc Pf Po) Ax(aJ Cv Jq Ke Nw Ri) Ny(bJ cl Ed Fn Ql Ri) Fa(Cv dA Pd Ri tF) Ke(aE bP cl cK Ir) Om(bJ cl Ed Jr Kr) aJ(bO
Jn Nr Pk Ri) aP(bO Je Nr Pk Ri) Wm(Fr Jp Po) Jq(cI Cs Ed) Jr(cI Et Ur) dG(bO Kr Us) Cv(Cs Kk) Fy(bH Co) EdPd PoEt FrbO LuRf MpIv
IdKr JlcI KkRi VtcT aDdA} eC{Pk(aE aJ aK aN aP aQ aW bA bI bP bV cI cK cN Co Cs Ct dA dJ Dl Ed Fa Fn Hu Ih Ii In Ir Iu Iz Jd Jo Jt Ju Jv Kc Kg Ki Kk Kr Kx Lu Mg Ms Nm Of Oi Qg Qu Qv Ra Ue Ug Ur Us Vo Vp) Dc(aK Ao aW bH bI bO bP cI cN Co Cq Cs Ed Ii Ir Iu Iz Jo Jt Kg Ki Kl Kr Kx Lu Mg Qg Qu Ur Us Vo) Kg(Ad Cq Cu Cw Hv Hw Id Ij In Ir Is Iv Jn Jq Jr Kd Kn Me Ml Mz Na Pi Qa Rj Up Uv Vp Vt) Jo(bA Cp Cu Hw Id In Ir Is Iv Jn Jq Jr Kd Kn Me Mz Nf Ny Om Pe Pi Qa Rj Up Vt) Ny(aK aL Ao aU aW Bb Bg bV cI cN Co Cs Dl Ii Iu Iz Kl Lu Nm Of Qu Vo) Id(aK aW cI cN Co Cs Ed Jt Kl Kr Kx Lu Mg Of Qg Qu Ur Us Vo Vp) aW(Cu Iv Jq Jr Kd Kn Me Mt Mz Nb Ni Om Or Pe Pi Qa Ut Vt) Mg(Cp Cu Cw Hx Ij Jn Jq Jr Kd Kn Mz Om Pi Qa Up Vp) Co(Jd Jh Jq Jr Kd Kn Mt Mu Mw Mz Om Pe Po Ut Vt) Vt(aK bH bO cI Cs Ed Kl Kr Kx Qg Ur Us Uv Vo) cN(Cu Hv Hw In Ir Iv Jn Jr Kd Me Ni Pi Up Vp) Kd(Ao bH bO cI Cs Ed Ii Iu Ki Kl Kx Vo) Jq(aK bH bO bX cI Ed Ii Kl Kr Us Vo) Pi(bP cI In Ki Lu Of Qg Qu Ur Vo Vp) Jr(bP cI Cs Ed Kr Qg Qu Ur Us Vo) bA(cT Hu Jd Kr Qu Qy Ra Ri Us) Me(bP bV cK dA Je Kc Ky) Ke(bX cI Ed Kl Kr Us Vo) Vo(Cu Is Kn Mz Qa Ut) Cs(Cu Mt Mz Ni Om) Ur(Cq Hw Ir Jn Up) Ed(Kk Kn Mt Ut) Ni(aE Ax bP cI) Qa(cI In Kr Us) Bg(Jh Mu Mw) Kl(Kn Om On) Cu(cI Us) Ml(Qg Ug) Ir(bV Qg) Jd(aD Ao) Kn(cI Ii) On(Ap Dg) MzUg HuaD HwOf QuOm JnUs} Fa{tF(aK AL aM Ao aQ Ar aU aV AW Bb bE bF BG bH bJ bO bQ bR bS bU bV bX bZ cA cB cL cN CO Cq CT cV Cw CX cY cZ dA dB dD Dg dH Di dJ Dl Ed Fn fP Gl Gp Ha Hf Hq Hu Hw Hx Ic Ih Ii Ik Il Ip Iq Ir Iu Iv Iz Jd Jf Jg Jh Jo Ju Jv Jy Kg Ki Kl Kr Ks Li Lu Ly Lz Mc Md Me Mg Mk Mp Ms Mu Mv Mw My Nb Nc Nd Ni Nj Nl Nq Ns Nv Nx Ny Oe Of Oi Om On Pi Pk Pz Qb Qc Qg Ql Qm Qn Qt Qu Qv Qw Qy Rh Ri Rm Tz Ua Ug Uk Ur Us Vo Tj) fP(aD aJ Al aP AR aW BA Bg bP bQ bR bV bW bZ cE cF cK cN Co cQ cS cU Cv cW Dc dF dG Dp Ed Fr Hq Hx Ih Ii Ik Io Iu Iz Jl Jm Jo Jp Jq Ju Jv Jy Kd Ke Kg Ki Kr Ks Ky Lj Lu Lx Ly Mg Mn Ms Mu My Ni Nj Nl Nn Ns Nw Oa Oe Oi On Qd Qg Ql Qv Qy Rf Ri St Tz Uh Ur Us Tj) Dp(Bb Bg bH bJ bO bS bV cA cN Co Ct dA Di Ed Fb Fn Fw Gp Hf Hx Ik Ip Iq Iu Jm Jv Ki Ks Ky Lj Lu Lx Ly Lz Me Mk Ms Mu Mv My Nc Ns Nx Oe Of Oi Qb Qc Qg Qh Qn Qt Qv Qy Ri Rm Tz Ub Ue Ug Uk Ur Vo Tj) Ef(Ar aW Bg bS bV Co Cv Hx Ik Iu Iz Jv Jy Lu Ly Me Mu My Ni Nj Ns Nt Oa Oi On Pc Pk Qd Ql Qn Qy Rg Ri Tz Vo Tj) bO(bA cT Io Jr Jv Ki Lx Ly Me Ni Nw Oe Ql Qy Ri) dA(Bg bS Co dH Hq Jv Ly Me Ri) Ly(bJ Je Jv Ki Ri) Jv(Kx Nf Pc Ri) Ed(cK Ri) Me(bJ Qg) Us(Mu On) MsbJ NfRi HqaV IzJd OzcK} bV{fP(aD aJ aM An aP aS aW bB Bc bF bG bJ bN Bo bQ bR bS bU bZ cA cF cH cS CU Cv cW Db Dc dE Dk Dp Ed Ef Et Ez Fb Fn Fr Fw Gl Gp Ha Hb Hf Hr Hu Hx Ib Ic Id Ii Ij Ik Im In Io Ip Iq Ir Is It Iu Iv Iz Jd Je Jf Jg Jh Jk Jl Jn Jo Jp Jq Jr Jt Ju Jv Jy Kc Kd Ke Kf Kg Ki Kk Kl Kn Ko Kp Kr Ks Kx Ky Kz Ld Lh Li Lj Lu Lv Lx Ly Ma Mc Md Me Mf Mg Mk Mm Mn Mp Mq Mr Ms Mt Mu Mw My Mz Na Nb Nc Nd Ne Nf Nh Ni Nj Nk Nl Nm Nn Nq Nr Ns Nt Nu Nv Nw Nx Ny Oa Oe Oh Oi Ok Om On Or Ou Ow Oz Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Ss St Tz Ua Ub Uc Ud Ue Uf Ug Uh Uk Ul Um Uo Up Ur Us Ut Uv Vo Vp Vt Wm Tj tF) Dp(Ar aX bJ BO cA Ed Iv Jy Kx Mq Nc Ni Oi Ql Qv Qy Ri Ur) Ri(bJ bN bO dA Ed Hf Iv Ki Kx Me Nc Nf Ni Pa Rf tF) bJ(Ed Iv Jv Kx Kz Ly Me Nf Ni Pc Pe Pk Rf Uv Vt) Me(aK aV bO cK cY dJ Ef Qc Qg Qy tF) Us(Is Iv Jd Jr Kx Mu Nc Ni On Oz Ql) Nf(cA Io Jv Ki Nw Qu Ur) Jv(Jd Kx Ly Pc Pk Rf) bO(Is Iv Kx Nw Po Rf) Ni(aK bX Ed Kx Ss) tF(bN Ed Iv Mq Nl) Ly(Ki Ql Qu) Kr(Is Iv Ql) Kz(cA Qu Qy) Ki(Kx Pk) Kl(Ba Et) Uv(aV dA) EdcK MqdA ImQu KxPc} Lx{Mc(aF aG aI aK AL aN aO Ap aQ Ar aU aW Bb bF Bg bH bI bJ BO bQ bR bS bX bZ cE cG cI cJ cL cN Co Cq Ct cV cX cY cZ dA dB dC De Dg dJ Ed Ef fP Fw Ha Hq Hu Hw Hx Ih Ij Ik Il Ir It Jq Js Kg Kl Kr Lj Lv Mc Md Mi Mj Mk Ml Mn Mv My Mz Na Nd Nf Nm Ns Nu Nx Ny Oe Of Pb Pd Pg Qb Qc Qg Qh Qw Qz Ss Ua Uk Ur Us Uv Vo Wm Tj) Nf(Bg bR bS cA Co Ct Hq Hr Hu Hv Hw Ij Il Iq Iv Je Jk Lj Lv Mb Mc Mk Mn Mu Mv My Na Nm Nx Oe Of Pb Pc Pg Qb Qh Qu Tv Ur Us Tj) fP(aF AL Ap Ar aZ Bb bR bX cI Co cX De Dg dJ Hu Jf Kl Mh Ml Pf Rm Ss Ue Vo) bO(aC aG AI aM aN Bg bR cA Co cW dC Dg Dp Ed Hq In Jv Kl Kx Lj Ml Nd Uv Vt) Ed(aK aU bJ bR cI cK Co dC Dp Hu Jd Ki Kl Kx Nc Nd Nl Qg Ri Vo tF) Mq(Hq Ih Io Jq Js Kr Lv Mp Mu Nd) Mu(Bg Hq My Na Nc Nq Ns Oi Pa) Kz(Ao aW bP cI cN Jo Kl Tv Vo) bR(bH bJ bN bX cC Hf Kl Pa) Ih(Im Mg My Na Nc Ns Qb) Jd(Bg bX Co Dg Kl Ly) Of(Hw Ij In Pi Pk Qa) Na(Ik Iv Mb Nd Pa) Co(Hu Je Pk Qy) Ly(Je Ki Vo Wm) Kl(Ba dA Jn Ri) Pa(bS Kx Mj) Bg(Hu Je) Im(aW Oi) Qb(Ii Il) Us(Ni Pc) bH(Af Dg) dA(bN Uv) CsbJ NsIk LvNd MbJq MwMy IbKr KiPk OrbX} Ni{cN(aF aI aK aL Ap aQ aU aV aW Bg bH bJ BN bO bP bR bS bX cA cC cI cL Co cQ CX cY cZ DB dC DE dH Dp Ed Ef Fn fP Hu Jh Jn Jr Jv Kl Kr Kx Kz Ly Mb Me My Nd Nf Nj Nk Nr Ns Oe Pa Pk Qg Rf Ri Ss To Tv Us tF) aW(aM bJ Dp Ed Hu Ih Is It Iv Jd Jk Jl Jn Jr Jv Ki Kx Me Mp Mq Mw Nj Nk Nn Nw Oz Pc Pk Po Qa Qb Qd Qe Ri) To(Ed Ih Is It Jl Jn Jr Kx Ly Me Mp Mt Mw Nw Ny Oz Pc Pe Pk Po Qa Qb Qd Qe Rf Ri Rm St Vt) Tn(Ed Hf Ih Is It Jl Jn Jr Kx Me Mp Mq Mw Nf Ny Oz Pa Pc Po Qa Qb Qe Qu Ri St) Kx(aK Ao aU cI Co Ed Hu Iz Jd Jf Jo Jv Kg Ki Ms Oi Qg Qu Ri Tv Ur Us Vo) Tv(Ed Ih Is It Jl Jn Jr Kz Mq Mw Ny Oz Pc Qa Qb Qe Ri St Uh) cI(Is Jl Jn Jr Mp Mq Mw Nk Nw Pe Po Qa Qe Ri) Jd(Ao Bg Co Iz Jv Kl Vo) Ed(aE bA cK In Qg Ri) Hu(aD Ao bP Co Cs Iz) aK(aD bA cW Jv Nk Po) Us(aJ Co Ki Po Uf) aD(bJ cZ dA dJ) Co(Fy Nr Rf) Cs(bJ Jv Qg) Kl(Ba Mn Nn) bO(aJ bA Po) Ax(Jv Ri) Dp(Qv Ur) Jr(Nw Vo) Ki(Kr Nk) Rf(Ao Iz) PoPb FyKg NnOi LyNw RihP aEbJ aPfP} Jd{Jv(aC aD aE aF aG aK aL aM aP aQ Ar aU aV aW Ax aZ bA Bg bH bJ bM bN bO bP bQ bR bS bX bZ cA cB cI cJ cK cN Co Cs cT cW cY cZ dA dB dC dE dJ dK Ed Iz Kr Kx Ky Lj Ly Ms My Nc Nr Oe Oi Pk Qv Rf Ri Ur Us) Iz(aP aW Ax bA Bg bP Co Cs cT Dc Ed Fy Hu Im Is Iv Jq Kx Kz Lu Ly Me Ml Mq Ms Nn Oi On Pe Pk Po Qa Rf Ri Tn Ut Vt) Co(Ax bA bR Cs cT Ed Fy Im Is Jn Jr Kx Kz Ly Ma Ml Mq Nf Nn Nr Oh Oi Ow Pe Pf Pk Po Rf Rh Us) Bg(bA bP Ed Hu Ih Io Jy Kr Kx Lu Ly Ms Mu Mw Oi Qe Qv Qx Ri Tn Ur Us) Ed(aD bA bJ bP cK In Io Jy Ki Kr Kx Ms My Oe Oi Qg Qu Rf Ri Us) Oi(aF aK aU aV Bb bJ bO cK cY dA Kx Kz Lj My Nf Pk Us) bA(bO Ct Dc Hu Mv My Of Uc Us) Of(Cw Ij In Ml Pi Pk Tv) Us(Ao Cv dL Ml Mq Ms Ul) bP(Hu Kz Ly Me Nf Pk Ri) Qu(Cs cT Ly Mq Nf) Ms(bJ Pk Ua) Qv(Dp fP Nf) Kg(Fy Mc Pk) Ki(Kx Ly Pk) Ao(Kx Rf) BaKl FyIi LycN MeUr UaKx KrdL aDbJ} Us{On(AF aK aM aU aW Ax Bg bH bO bX cI cK cN Co Cs dA Dg Dp Ed Ef fP Hf Iv Jg Jn Jr Jv Ki Kl Kx Kz Lj Ly Me Nc Nf Oa Oz Pk Ql Qz Rf Ss Vo Wm) Ki(bA cT Jn Jr Kc Ml Mq Mx Nn Ok Pe Pk Qa) Mu(aD Ax bA Bg Cs cT dG dL Id Mq Pf Po) Jn(bW cN Co Cv Jv Kx Mm Mq Oi Uf Ul) bA(bJ bW Jl Jv Mm Mq Mr Oz Ql Qy Uf) Jr(bH bW cN Co Jv Kx Mq Qg Uf Ur) Ke(bJ bX cK cZ dA Ed Fn Jv Oz Qz) Qa(bH bJ cN Co Mm Qc Qg Ql Uf) Jl(aW bH dA Kx Qz Tn To Tv) Ql(Cv cW dG dL Id Is Jq Ul) Mq(cK cT dA Lv Ly Qy Rf) Uf(Fy In Is Me Nf Pi Pk) dG(bO bR Ed Kx Nf Oz Pc) Co(Fy Ij Is Js Pe Po) Id(bJ Ed Jv Oz) Qe(aW Tn To Tv) Pk(aJ bW Cv Mm) dL(bJ Hu Qy) Cv(Ed Rf) Po(bO Oz) Fr(Me Nf) Mw(Tn Tv) Pi(bW Mm) aP(fP Oz) cN(Et Iv) BaKl BgDk EdOm FybW MrTv ToNy JqbJ JvPe RfUl} bJ{aD(bQ Cs Cv Dc Ed Hu Iv Jn Jq Jr Jy Kk Kx Ky Mr Mu Nc Nn Oh Pe Qa) Ed(aP Cv Dc Fr Fy Id Jq Kd Ke Kk Kn Mt Mu Mz Rf Vt) Jq(aE aF aG Ao Cs Cx dC Jv Kl Ko Kr Lj Ml To Vo) Qa(aW bP cN In Jo Kg Mg Ms Oi Qg Qu To Tv Ur) Vt(cT Jo Kg Kx Ms Qg Qv Tv Ug Uk Ur) Pe(Ao aW bP Co Ii Iz Jv Lu Ms Oe Oi) Pk(aJ bA cN Co Jv Ki Ms Nw Oi Qg Ur) Me(aJ Ax bP bZ cN Kc Kk Qv Ur) Cs(Cv Dc Jv Mu Nw Oe Oi) Ke(aE bX Iz Kl Ko Kr Ms) Fy(Ao Co Ii Iz Jo Kg) Jr(aW Kg Lu Mg Oi Vo) Jv(bA Dc Id Mz Nn) Oi(Jn Kx Nn

Figure 8 Continued

Qd) On(Ao dC Iz Vo) Ur(Id In Pi Uv) Tv(Nw Qe St) Iv(aE aW cN) Lj(Cv Mu Ny) bA(Mg Pc Qg) Ao(Dc Mz) Ml(Nw Qg) Mw(Bg My) Iz(Ny Ut) Qe(aW Iu) Uv(Kg Ms) DcaC MraW NfQv IdOf TnNw KrdL} Nf{Nw(aW bA bI bP cI cN Ih Ii In Iz Jr Lv Ms My Ns Tn To Tv) Ur(aD aJ cN cT Cv dA Is Je Jr Jv Ki Mp Mu Oh Oi Ri Wm) Qv(bP bW cK Cv Dp Io Jq Jv Ki Mm Qg Qu Qy Ri St) Tv(Is Jl Jn Jr Ke Mt Mw Ny On Qa Qd Qe) cN(bR bS cA cT Je Jn Jv Oe Oi Qy Rf Ri) Co(Fy Lv Mu Nr Pe Rf St Tn) Ke(aW bP cl Ii Iz Kg Tn To) On(aW bP cI Kg My Ns Tn) Mu(Bg Lj Lv Ml Ne Oi) bA(Je Jo Kg Qg Qy Ri) Cv(cI Cs Qn Ug Vo) Oi(dA Fb Je Ki Qy) aW(Is Jl Jy Qe Ri) Kg(Jn Jq Jr Vt) Lv(Mm Oh Ok) Iz(Fr Om Ut) Jo(Et Id Ok) Jv(aP bF Jp) Ri(aJ bP) JeaJ JlcI KiKx} Mq{dA(aD aE aW bA Bg bP bR bS cA Co CT dB Di In Io Jo Kg Kr Kx Lu Lv Ms Mu My Nd Ns Oe Oi Qu) Mu(aK Bg cI Hx Io Ip Jh Jk Lj Mg Ml Mn My Nd Nq Nu Of Oh Oi Po) Mp(Hv Hx Jn Lv Ml Ms My Nd Ns Of) Ef(Cv Dc Jq Ke Nw Rf St) Jv(cK Jn Kx Rf Tn) bO(aD aJ bA Jq Nw) Co(Fy Je Pd Rf) aW(Is Jn Jr tF) cK(Ed Oe Pk Ri) Wm(Jq Mz On) In(Jr Pd Qb) Io(Mm Nw Oh) Qv(Dp fP tF) Qu(bQ Jn Pk) Kr(bA Qy Rf) Bg(Je Lv) Nn(My Oi) Jq(aK cI) Kx(Ki Oi) Of(Mt Pi) bP(Oe Ri) PoJo LvOn LyJe IhNw JnKg aDtF} Kr{On(AF aK aN Ap aU Ax Bg bX cI cK Cs Cx Ed fP Iz Jv Ki Kx Lj Ly Nc Oa Ow Pk Qb Qg Ql Qz Rf Ri) Qa(bW Co Ih Ir Ki Mm Qc Qg Tv Uf) Jn(bW cN Co Cv dL Jv Ki Kx Uf) Qe(aW Ih Iu Qv Tn To Tv) Ki(bA Id Ke Nn Ok Pe Pk) Ed(Cv Et Fr Id Ke Om) Jr(cN Co Kg Kx Ri Ur) Cs(Cv Et Ke Mm Mu) Pk(aJ bW Cv Mm Uf) Is(Ao Iu Iz Uf) Iv(aJ cN dG Ur) Bg(Mu Mw Om) bA(Mu Nw Uh) Nn(Jv Mx) Id(Jv Oz) Uf(Pe Pi) bO(dG dL) AxMu CoPe CvNr FyKg MwMy TvUh QydL KeaF RfUl NwdA OfOm} bO{aJ(bR Cs Fy Iv Jn Jr Kx Kz Ly Me Nr Oa Oz Pc Pk Po Ql Rf Ri) Po(aD bA cN Co cW Ed Io Jv Ki Lu Ms Oi Qv Ug Ur) bA(aM Cs Ed Jl Jr Kx Me Pe Pk Qa Qd Qe Rf Vt) aP(bR Ed Fy Iv Jv Kx Me Nr Oi Pk Ql Uv) Oi(dG Jn Jr Kx Nn Nr Pe Pf Rf) Pe(bM Co cW Io Jv Ki Ms) Fy(bW Co Iz Kg Ki) Nw(Cs cW Kx Ml Nr) Fr(Ed Kx Me Pk) aD(Ba Jn Nn Pf) Nn(Jv Qu) Qa(Fn Tv) Qe(aW Qv) Jr(Ms Ur) Kx(cW On) dG(bR Pk) EdOn MePf MlQg IsQv IvcN JnJv RfcW VtcT} Me{Ur(aV bA bP cT Cv dA dJ Dp fP Hu Io Is Iu Iv Iz Je Jn Jr Jv Ki Kx Mr Mu Pk Qg Ql Qy Ri Um Wm tF) dA(Af bB bF Bo bW cN cW Di Kc Kg Ki Kx Ky Lu Mn Oi Qg Qv Uf Ug Ul) On(aW Hq Lv Mb My Na Of Pb Tn Wm) Mu(Lj Mn Mp Na Of Oi Qv) aW(Cv Et Is Jl Jy Nw Qe) Co(Ax bQ bZ Nr Rf) Kg(bQ Jn Jr Kx Rf) Mp(Hq Nd Ns) To(Cv Jl Jy) Qv(Dp fP tF) Tn(Jl Jy) Tv(Nw Qe) bH(bZ Rf) WmFr InOw QcbZ QgbA JncN KiKx aVcW} Pk{Ki(aJ aK aR Ax bA bL bP bQ bZ cK cN CO cT cW dA DB dJ Ed Fn Gp Gz Hu Jm Jr Jv Kg Kx Ky Lu Ly Ms Oe Oi Ow Qc Qg Qv Ri Ue Uk Ur) Jv(aJ aP bA bF bH Bo bQ cN dJ Kx Qg Ur) Co(bQ cK Fy Jn Jr Kx Nn Nr Rf) Kg(bA Et Is Jn Jr Kx Lh Ow Qe) cN(bR Dp Ef Oz Qg Ri) aJ(bX cK Cx Dp fP) Qg(aM aP Kx) Ii(Is Jr) BaKl CvCx DpQv EdUr LybW IsIz KxaK UfcK} Kx{Jv(aP bA Cs cT dA Ed Et Hu Id Is Jl Jn Jr Jy Ly Mr Nr Oi Oz Pc Qv Rf) Ki(bQ dA Ed Hu Im Iv Jn Jr Jy Kz Ly Ml Nr Oi Oz Pe Ql Qv Ri) Ed(dA Je Jn Jy Ke Nw Oi Ri Vt) Qv(Dp Oz Ql Qy Ri tF) Co(dA Im Jn Jr Pe) Kg(Fy Is Jn Jr) Oi(dA Jn Ql Ri) Bg(Mu Mw) Cv(Af Cx) Ii(Jn Jr) Jy(Ao Vo) Kl(Ba On) Ri(bA Oz) dA(Qg Vt) IvUr aMcK} Dp{Qv(aJ aM aP Ar Bc cN Cs Cv Ed Fr Hx Id Im Is Iv Jl Jn Jp Jq Jr Jv Ke Ki Ld Lj Ly Nn Nw Oa Oh Oi Pc Pe Pf Po Qa Qd Qe Ql Ri St Ur Vt) Ur(bA Cs Fy Id Is Iv Ke Pe Po Qa Vt) Kg(bA cT Fy Jr Ml Pe Qa) Cs(Cv Jy Lu Nw Oi) Jo(bA cT On Pe) Jy(Ao aW Tn) Pe(Co Ii Lu) bA(Bo Ue) BaKl CoNn LuRf} Mu{Oi(Cs Ed Im Jn Jr Li Lj Ml Nn Oh Pe Pf Po Qa Qb Qe Rf Rh) Ml(aO Bg Hq Jh Jk Jq Ly Mp Mv My Na Ns Nw Of Pb) Po(Hu Ii Io Jk Jr Ms My Ns Oe Of Pb) My(Hx Jr Li Lj Nd Oh Pe Qa Qe) Bg(bN Kz Ma Mv Nn Rh Tn) Of(Ij In Ir Na Pe Qa) Io(Lj Nw Oh Ok) Cs(Ef Oe) Fy(Co Iz) BaKl NqOh MbJq MsNw NaNd IhQa} Kl{Ba(aJ Ax Bg bP cN Co Cv dA Dc Dk Ed Et Fb Fr Hu Id Is Iv Iz Jl Jn Jq Jr Jv Jy Kd Ke Kf Ki Kk Kn Kp Ky Lh Ma Mm Mn Mp Mr Ms Nc Nn Nw Oe Oh Oi Ok On Pc Pd Pe Pj Qa Qd Qe Qg Ql Qn Qu Qy Rf Ri St Uh Vt Vv tF) dA(Et Fr Nn Nw) Jn(Cv On Uf) Rf(Cv Uf) EtLu NnJv IsUr} Ed{Rf(cN Co Cv Je Jv Ki Lu Nl Oe Oi Qg Qv Ri Ur) Jy(aD aE aW cI cN Jv Ki Ri To) Ri(aP bA cN Jq Nw Qv Tn) Oi(Fb Is Je Jn Ql Qy) Fy(bH Co Je Ki Qg) tF(aP Cv Qv Ur Vt) Fw(Dc Jq Kc Kn) Qg(bA Jn Jq Qa) Nw(bA dA Jv) Cv(bX Cx) Ke(bX Ko) Oe(Jl Ql) Vt(cT dJ) FnJq NnJv MsQy OncK aDdA} Co{Fy(aK bH bX Cx dA Db dE Hf Hu Kz Ly Oz Pa Pc Qy Ri Vo) Pe(dA Db Ef fP Je Ri tF) Rf(Hu Kz Ly Vt) Nn(Je Jv tF) Im(aW Tn Tv) Jn(bN Db Oi) Po(dA Je) Qy(bA cT) IsbR JrKz} Kg{Fy(aF bH Cw Hw Id Ij Is Jq Jr Ke Ki Kn Mp Ow Pi Ql Qy Ri) Jn(aD Jv Kz Oe Oi Ri Uv) Jr(bX Cx Jv Kz Qy Ri) Is(aW Tn Tv Uv Vt) Qa(Qg tF) Rf(Uv Vt) Pd(aD Uv)} Ly{Ki(aP Ax Cs Jn Ky Nn Oh On Pe Ri Ur) Wm(Et Fr Jl Jq Jr Nw On Qd) Nw(Jr Jv Tn To Tv) On(cI Mb Tn To Vo) Ld(bW Cv Mm Uf) Ri(aP Ql) IvcN QybA JrUr} Kz{cN(bR bS cA Fb Jn Jr Oi Ql Qy Ri) Nw(aW bI bP cI Ir Tn To Tv) aW(Jl Jr On Qd Qe Uh) Cv(cI Tn Vo) Tv(Jr Ke Ny) On(cI Vo) JeaJ QgbA JlcI JvUr KcKi} dA{Oi(Hf Ki Nw Oa Qy Rf Ri) aD(Bo fR Gz Ky Nc Ur) Ao(Et Nw Rf St) Qg(Ml Qa Uv) bR(aJ cN Nw) Gz(bN Ld) BoUv CsJv MwMy InUr QeaW NwbN} Jv{Jn(aE Ms Oi Ur) aW(Im Jr Mr Mw) Ny(Tn To Tv) Ur(Is Iv Jr) Qv(Im Rf) bX(Ke On) ArRi AxPc CsJy LuRf MwMy PcaK bAbM} fP{Qv(aP cS Jl Nn Oh Po Qe Vt) bA(Jo Jy Qg Qy St Ue Ur) Cs(Jy Ke Nw On) Po(Lu Ur) BoMl JlaW OiaP} Rf{Oz(aW cN Tn To Tv) Ao(Jy Qy Ri) Dg(bW Gz Uf) Ap(Gz Uf) Ri(cN Ki) LutF IiVt JeOi} aW{Im(bW Cv Iv Ki) Is(Nc Nk Oz Pa) Qe(Jy Mr Qc) Iv(Mw Ri) Oz(Jy Mr) GzIt JltF} Qy{bA(Bg Hu Ib Iz Mk Mv My Of Qg Qu) cT(Mg Qu) BgTn FyIz} Iz{Hu(aM bA cT Im On Qa) Im(Dc Jq Vt) Mw(Tn Tv)} Qg{Ml(aK aQ bE cY Fn) Qa(aU Fn Jt) HfbA} Jr{Ri(aK Jo Ur) Oi(Nn Po) Ur(Pa Pc) MsNw IhIm} Jn{Oi(aK Ki Nn Vo) cN(bN Nc Ri) AoJy} Mw{My(aF bA bP cI cT) Bg(Lv Mb)} On{Mb(Hq Na) My(Hu Nd) Im(Lv Oi) NaNd} tF{Nn(Ao Oi) Qv(Po Vt) CsOi LuVt UrcW} Ef{Cs(Jy Nw) BoMl QvVt UrPe} Ki{Ri(Ax Nr Pe) FnQa FybH} Cx{Cv(Cs Ql) JqUr OfOm} Mp{Mb(Hq Ns) Nd(Mj Na)} Tv{Oz(It Ny) QaPa QcQe} Nw{To(Im Oz) LvIo MlaK} aF{FybH JybA NyOf} bR{MrcN IiIs bXdG} Bg{Je(Pf Po)} Hu{Qu(cT Ow)} aV{UrUv aDfR} FyIiQl ToRiNy TnQcQe InOfbQ

Unconstrained panels with 2 analytes, where 1.0E-7 >= 'AUC p-value' > 0. Contains 715 panels of 61,235 total panels evaluated. : dN(aA aC Ad aE AF aG aH aI AJ aK AL aM AN aO AP aQ AR AS aU aV AW AX aY aZ BA BB BC bE bF BG bH bI bJ bL bM bN BO bP bQ bR bS bU bV bW bX bZ cA cB cC cD cE cF cG CH cI cJ cK cL cM cN cO CP CQ cR CS cT CU cV CW cX cY cZ dA DB dC DD DE dF DG dH DI dJ DK dL dM Dp eC Ed Ef Fn FP fR Gl Gp Hc Hf Hu Hv Ih Ij Im Is Iv Iz Jd Jn Jr Js Jv Jy Kd Kg Kj Ko Kq Kr Kx Ky Kz Lj Lx Ly Lz Ma Mb Me Ml Mq Mr Mu Mv Mw My Nb Nc Nd Nf Ng Ni Nj Nk Nl Nn No Nq Nr Ny Oa Oe Of Og Ok Ow Oy Oz Pa Pb Pc Pd Pe Pk Qb Qc Qe Qg Ql Qm Qn Qt Qw Qy Qz Rf Rh Ri Uk Un Ur Us Uu Wm tF) Ji(aA Fp Hq Hu Hw Hx Ih Ii Ij Ik Il Im In Io Ip Iq Ir Is It Iu Iv Jh Jj Jm Jn Jo Jp Jq Jr Js Kj Kr Lh Li Lj Lu Lv Lw Lx Ly Ma Mb Mc Md Me Mf Mg Mh Mi Mj Mk Mn Mp Mq Mr Ms Mt Mu Mv Mw My Mz Na Nb Nc Nd Ne Nf Ng Nh Ni Nj Nk Nl Nm Nn No Nq Ns Nt Nu Nv Nw Nx Ny Oe Of Og Oh Oi Om On Oy Oz Pa Pb Pc Pe Pg Po Pz Qa Qb Qc Qd Qe Us Uu Wm) No(Aj Ao aW Bb Bg bJ bO bX Ch Co Cx dA Dg dI dM Dp Ed Ef FP Hc Hu Ih Ii Il Im In Io Is Iu Iz Jj Jr Jv Ki Kj Kl Kr Kx Lv Mb Me Ml Mq Ms Mu My Ne Nf Ng Nh Ni Nj Nl Nq Ns Nw Og Oi Oy Oz Pa Pb Pk Po Qb Qu Qz Ri Ss To Ua Us Uu Vo Wm tF) aA(aC aF aM bA bJ bM bN bP bR bU bX cT CX dI dM Dp eC Ed Et Fp Hc Im Is Jr Jv Kx Kz Lv Lw Mm Mp Mu Nn Nw Oh Pc Po Qa Qb Qe Uu) Mu(Fp Hw Jj Jr Li Lj Lv Lx Me Ml Mq My Nd Nf Ng Nw Og Oh Oi Oy Pe Po Qa) Kj(Ad Cp Cw Id Ij Jn Jq Jr Kn Kq Lh Lw Me Ml Ok Om On Pe Pi Pk Qa Sr Un) Lx(bO Ed FP Hc Ih Im In Iv Kz Mb Me Mq Nf Ng Og Oy Qb Uu) Jj(Dp Et Fp Im Is Jm Jn Jr Mq Nf Nn Nw Nx Pd Pe Po Qa Qb Qe) Uu(Ba Cv Dk dM Et Fr Id Is Jd Jl Ke Kq Lw Nn Om On Sr Un) dI(aM Cs Fy In Ir Kx Me Ml Mq Ni Nr Pe Pf Po Qa Rf Sr) Po(Et Fp In Iu Jo Mq Ms Ng Ni Nw Og Oi Oy Pb) Ng(Et Is Jd Jl Nn Nw Oh Ok Om On Pf Qa Qe) Fp(Et Fa Fr Jl Jq Lw Mm Nn Nw Ok Om On) Og(Et Is Jl Mq Nn Nw Oh Ok Om On Qa Qe) dM(bN bR Im Iv Kz Me Mq Nf Ni Oy Pk Us) Aj(Is It Iv Jd Jn Jr Kq Ni Pe Sr Un) Un(bX Ch eC Ed Iz Ko Kr Ms Oy Us) Hc(aJ aP bA bV dG Fa Fr Qv) Nw(Im Io Jr Mq Ms Nf Ni) Fa(bO Ch Dp Ef fP tF) On(Im Lv Mb Oy Us) Ch(bQ Hu Jd Nn) Mq(dA Et Mp Oh)

Figure 8 Continued

Qa(Ih In Jr Oi) Sr(aK bJ bO Jv) Kq(aF Kl Kr Vo) bV(Dp fP Kz Me) Nf(cN Et Qv) Ni(aW cN Kx) Jd(Bg Ed Jv) Jr(Et Im Kg) Me(dA Ur) Ki(Kx Pk) BaKl DpQv EdRf

Dk Fr) Ow(aA Mz Pb) Pj(Hv Rj Us) dM(Im It Mr) Fn(Hv Uc) Nm(cZ tF) Mu(Ax Cs) Mw(Bg My) bV(Dp fP) Cv1b DbRb DkIr ImUl QgRj
JoNw JyaD aAbU cWtF] Uu{Ba(aA AD Aj aM An As AW Ax bA Bn bO bP bV Ch cN Cp Cq Cs Cu Cv Cw dA Dc Dd dl Dk dM dN Dp Ed
Fb Fr Hc Hu Hv Hw Id Ij In Io Ir Is Iv Jd Je Ji Jj Jl Jn Jo Jq Jr Jt Jy Kd Ke Kf Ki Kk Kl Kn Kp Kq Kr Kx Lw Md Me Mg Ml Mq Mu Mz Na Nf
Ng Ni Nm No Nr Nw Ny Oi Om On Or Oy Oz Pb Pc Pi Pk Qa Qd Qe Ql Qu Qy Ra Rb Rf Ri Rj Sr St Tn Tv Uc Ud Ul Un Up Us Ut Uv Vp Vt
tF) Jd(aA AD aJ As AW Ax bA bC Bg bM Bn bV bW Ch cN Co Cp Cq Cs cT Cu Cv Cw dA Dc dG dl Dk Dl dM dN Ed Ez Fa Fr Fy Hu Hv
Hw Id Ij Ir Is Iv Ji Jj Jl Jn Jq Jr Jt Jy Kd Ke Kf Ki Kn Kp Kq Kr Kx Lv Lw Lx Ly Ma Me Mi Mq Ms Mu My Na Nc Nf Ni Nm Nn No Nr Oi Ok
Om On Ow Oz Pb Pc Pd Pe Pf Pi Pk Po Qa Qe Ql Qt Qv Ra Rb Rf Rh Ri Rj Sr St Tn Uc Ud Uf Ul Un Up Us Uv Vt) Cv(aA Ad aM aP Ar Ax
bA Bc bJ bQ bV Cs CT Cu Cw Cx dA Dk Dl dM dN Dp Ed Ef Et Ez Fa Fb Fp Fr Fy Hu Hw Ib Id Ih Ij Im Is Iv Jk Jl Jn Jp Jr Js Jt Jy Kf Kk Ko
Kq Kx Ky Kz Lh Li Lj Ly Ma Me Ml Mn Mq Mr Mu Mv Mw Nf Ni Nn No Nq Nr Nv Nw Oa Oh Ok Om On Ou Ow Oz Pd Pe Pf Pi Pj Pk Po
Qa Qb Qd Qe Ql Qn Qt Qy Ra Rf Rh Ri Sr Tn Ua Uf Un Vt Wm) Lw(aA Ad aF aK Ap Ar aW Ax bA Bc bJ BN bR bX Cs CT Cw CX cZ DB
dE dl Dk dN Dp eC Ed

Ch Cp Cq cT Cu CW Dc dM Dp Ed Fa Hc Hv Hw Id Ij In Ir Is Iv Jd Ji Jn Jq Jr Ju Jv Kd Ke Kn Kp Kq Kr Kx Kz Lu Ly Me Ml Mq Ms Na Nb Nc Nf Ni Nm Ny Oe Og Oi Ok Om Oz Pb Pi Pk Qa Qv Rb Ri Rj Sr Tv Ud Ul Un Up Uv Vp Vt) bR(aA aJ aM aP Ax bA Bc bQ bV Cs cT cU cW dF dG dM Ed Et Fa Fp Fr Fy Hw Hx Ij Im In Ir Is It Iv Ji Jl Jn Jq Jr Js Kq Kx Kz Lh Lj Lv Lx Me Mj Ml Mq Mr Mt Mx Mz Na Nf Ni Nn Nr Nw Ny Oa Oh Oi Ok On Ow Pe Pf Pi Pk Po Qa Qb Qe Ql Sr Un) Jv(aA AD aM aP Ar Ax bA bV Cs cT Cw Ed Et Fa Fp Fy Hx Id Ij Im In Is It Iv Jd Ji Jl Jn Jp Jr Jt Ke Kq Kx Kz Ld Lh Li Lj Ly Me Ml Mq Mz Na Nb Nf Ni Nn Nr Nt Oa Ok Ow Pe Pf Pi Pk Po Qa Qb Qd Qe Ql Qx Ra Sr Un Uv Vt) aM(aA aD aJ aW Ax bA Bo bU bV cA cF Ch Cs cT dM Ed Fa Fp Fy Hu Ij In Is Iv Jd Jn Jr Ki Kn Kq Kr Kx Ky Kz Lh Lj Ly Me Mq Ms Na Nc Nd Nf Ni Nn Nr Ns Ny Oe Oh Oi Om On Oz Pe Pk Po Ql Ra Rh Ri St Uk Us Uv) Ch(aA aP Aw Ax BA Bc bQ bV cP Cs cT dF dG Et Fa Fp Fr Fy Hu Ij Im Is Iv Jd Ji Jl Jn Jr Js Kq Kx Kz Li Ma Me Ml Mq Nf Ni Nn Nr Nt Oa Oh Ok On Ow Pd Pe Pf Pk Po Qa Qb Qe Ql Qt Qx Ra Sr Tn Un) Oy(aA AD aJ aP Aw Ax bA Cq Cs cT Cu cW Dc dL dM Fa Fr Hw Ij In Ir Is It Iv Jd Ji Jn Jq Jr Kc Kf Kk Kn Kp Kq Kx Lh Ml Mz Nb Nf Ni Nm Nn Nr Ny Ok On Pe Pf Pi Pk Po Qa Sr Tv Un Up Vp Vt) Nf(aA aD aJ aP Ax bA bS bU cA cH cP Cs cT Cv Dk dL dM eC Fa Fr Id Is Iv Jd Ji Jj Jl Jn Jp Jq Jr Ke Ki Kk Kq Kx Ky Lw Ly Ml Mq Ms Ni Nr Nw Og Oi Ok On Oz Pe Pf Pk Po Qa Qv Ri Sr Un Ur Vt) eC(aA Ad An As bA Bn Cp Cq Cu Cw Dc Hv Hw Hx Id Ij In Ir Is It Iv Ji Jn Jq Jr Js Kd Kc Kn Kq Kr Lh Md Mj Ml Mr Mz Na Nb Ni Ny Ok Om Pb Pi Pk Po Qa Ra Rj Sr Uc Un Up Us Uv Vp Vt) Cs(AD As bJ bO bS bU cA CP Cq cT Cu Cw Dc dH dM Et Hc Hv Hw Ij In Io Ir Is Iv Jd Jq Jr Ju Ki Kx Kz Ly Me Mq Na Nb Nc Ni Nj Nk Nl Ny Oe Oi Om Oz Pc Pi Ql Qy Ri Uv) Mq(aD aJ Ax bA Bg bS bU cA cD cF cL Co cT Cu Cv Cw Dc dH Ed Hw Ij In Io Ir Is Iv Jn Jq Jr Kk Kn Kq Kr Kx Ky Ly Me Ml Mz Na Nc Ng Ni Ns Ny Om Oz Pk Qa Ql Qu Un Us Vt) Nr(Ad Ao As Bg bQ bS bU cA cF CO CP Cq Cu CW dH Dp Ed Hc Hq Hv Hw Ij In Ju Kz Me Mk Ml Mz Na Nb Nc Nd Ni Ns Nw Ny Oe Oi Oz Pb Pi Pk Qw Ra Ri Rj Ua Up Vp) Ly(aD aJ aP Ax bA bV cP cT cW dG dL dM Ed Fa Fr Id In Is Iv Jd Ji Jl Jn Jr Ke Kq Kx Li Lj Ml Mz Ni Nn Nw Oh Ok Pf Pi Pk Po Qa Qe Qv Ra Ri Sr Un Ut Uv Vt) Kx(AD Ax bA bS bU cA cF cL cT Cu Cw Dc dH Ed Hc Hv Hw Id Ij In Ir Is Iv Jn Jr Ju Kn Kz Mc Ml Mz Na Nb Nc Ni Ny Oi Ok Oz Pi Pk Qa Ql Ra Sr Uv Vt) Pe(aD Ao bF BG bJ bQ bS bU bZ cA cC cF cG cK cL CO cP cU dH Hq Ju Kl Kz Mk Mp Nc Nd Ng Ni Nl Ns Oz Pa Pd Pf Pg Qu Qw Qz Rh Ua Uk Tj) Ed(aD aJ aP bA Bc cP cT cW dM Et Fr Fy Ij Is Jd Ji Jn Jq Jr Ke Kq Me Ml Nc Ni Nn Nw Oe Oi Ok On Pk Qa Ql Qv Ra Rh Ri Sr Un Ut Uv Vt tF) Me(aA aJ aP aR Ax bA bS bU cA cF cP cT dM Fa Fr Is Iv Jd Jl Jn Ju Kq Ml Nc Ni Nn Oh On Ow Qa Qe Ql Qv Qx Ra Rh Ri Sr Uf Ur Us Wm) Qa(aW bG bJ bN BO bS bU cA cF Co Cq dM Dp Fn Hc Iz Jo Ju Ki Kr Mj My Nc Nd Ng Nw Oe Of Oi Oz Ph Qg Qu Rh Ri Ua Uk Us) Sr(aW bJ bN bO bS bU cA Cx dM Dp Hc Iz Ju Ki Kl Kr Ky Kz Nc Ni Nl Ns Oe Of Og Oi Pk Qg Qz Rh Ri Ug Uk Us Vo) Ni(aD aJ aP aW Ax bA bM bS cA cT dM Fa Fp Hc Hu Jd Ji Jn Lj Ms Nj Nk Nn Nw Oa Pf Pk Po Qb Qz Ri Vt) Kz(aD aJ aP Ax bA bM cA cP cT Dc dL dM Fr Io Jd Ji Jj Jn Jr Ki Nn Nw Oh Oi On Pf Po Ql Qv Ri Vt) Pk(aA aD aJ aP bA bW cA Co cT dM Fa Fn Jd Ji Jn Ju Kg Ki Ms Nc Of Oi Oz Qe Qg Qv Ri Uf Ur) Ml(aW bJ bS bU bW cA Dp Hc Hu Jd Jl Ju Ki Lw Nc Nw Qe Qg Ql Rh Ri Us) Lj(aD As Bn bU cP Cq cW dM Hw Io Jd Lw Na Nc Nm Ny Oe Oi Om Oz Pb Ri) Iv(aD aJ aP aW bA bS bV cA cP cT cW dM Fa Io Kr Oi Ri Ur Us) Oz(aA aD aJ aP Ax bA cP cT dM Fa Hw In Ir Jr Kk Lv Pf Po Qv) cA(bA Fa Fy In Ir Is It Ji Jl Jr Kq Lx Nn Ow Pf Pi Po Qe) Nc(aD aP Ax bA bV Fa Fp Fy In Jd Ji Jn Jr Oa Pf Pi Po) Us(bA cT dL Id Is Ji Jn Jq Jr Ke Kq Lw Mx Ok On Un Vt) Ri(Ax bA cT Fa Fy Hw In Ir It Jn Jr Kq Mz Ny Oa Pi) Po(bF Bg bJ bO bS bU cG cL Co dH Hq Hw Na Nd Ng) Hc(aJ aP Ax bA cT Fa Fr Fy Jn Jr Nn Oh On) Is(aD Al Ao aW bS bU bV Co Kl Ms Og Oi Qv) Oi(Fp Ih Im It Jd Jn Jr Js Nn Qb Qe Ql) aD(aA Ax Et Im Jd Jn Jr Mr Nn Oh Ow Qe) Kr(bA cT dL Id Ji Jn Jr Ke Kq Ok On) Fy(aF aO Co Hq Jo Ju Kg Ng Nl Qz) bS(In Ir It Jr Ld Lx Nn Pf Pi) Kq(aF Cp De Dg Fn Kl Uc Vo) bU(aA Ax Fa In Ir Ld Lx Pf) Jd(Ao Ax Bg bM Ms Ng Oa) Ji(bG bJ bN Ms Nd Rh Up) Uv(aA Ax bJ Ow Ql Rh Ur) Fp(cF Cv cW Ik Jq Ju) Jn(bM Dp Ki Kl Ms Oe) Dp(bA cT Fa Qv) Nn(Kl Ng Qu Qz) Lx(bF dH Hq Nd) In(bJ Fn Rh Ur) Pf(Bg cL dH Ng) aA(bM cT cW cX) Ao(Et Ij Im) Fa(bO dH Ql) Qe(cT Io Tv) Jr(bJ cP Nl) bA(Jl Ju Ql) Ax(Pc Ql) Im(cP dM) Rh(Un Vt) On(aF bN) bJ(Un Vt) BaKl BgJh CxJq NgOw TnbL IjOf IrcF ItOe RaKi PccT}

Nb Nh Ni Nw Ok Om Pc Pd Pe Pg Wm) Im(Et Hu Hv Hw Ij In Io Ir Is Iv Jn Jq Js Jv Lh Lu Lv Lw Lx Me Mi Mj Ml Mq Mt Mu Mx Mz Na Ne Nh Ni Nw Ok Pa Pc Pd Pe Wm) Qe(bO Et Hu Hw Ir Is Iv Jn Jo Jq Jt Kr Lh Lv Lw Lx Me Mq Mr Mt Mu Mz Na Ni Nn Nw Oh Ok Om On Pc Pd Pe Wm) Me(bJ dA dM Et Ii Is Ji Jm Jn Js Kx Lv Mm Mn Mp Mu Mw Nn Nw Nx Ny Oh Ok Om On Pd Pe Po Pz Qa Wm) Mq(Et Is Ji Jm Jn Jq Kx Lv Lw Lx Mn Mu Mw Ng Nn Nw Ny Oh Ok Om On Pd Pe Po Qa) Kz(aL bJ cK dA dM Fb Hu Io Is Jd Jc Jn Jv Ki Kx Lw Mu Nr Nw Pk Ql Qy Ri St) Mu(Et Ih Ji Jm Jn Lj Lv Ml Mr Ng Ni Nw Oh Pd Pe Po Qa Wm) Qa(bO Et Hu Jl Jq Kr Lh Lv Lw Lx Ni Nw Ok Om On Pc) Kx(bJ bO Ed Jd Jn Jv Ki Kr Ly Mr Ni Pk Ql Qy Ri) Lv(Hu Ik Is Jm Jn Mp Mw Nh Nw Ny Pd Pe Po) Is(bJ bO Et Hu Io Jv Kr Ni Pd Pe Wm) Jm(Hu Ir Jn Jq Ml Na Nc Nh Ni Og Ok) Ly(Ik Jd Ki Nh Ql Qy Rf Ri Wm) Pd(Et Jn Mr Mw Ng Ni Oz Pa Pb) fP(aP bV dF Fa Ma Nr On Pe Sr) Ed(bJ dA Ef Jd Ql Qy Rf Ri) Jv(Ef Jd Jn Nr Pk Ql Rf Sr) Po(bO Ji Jq Lw Ng Ni On) Et(Io Jn Mr Ne Nh Ni) Pk(bJ dM eC Ki Kr Ql) Mw(Jn Ml Ne Nh Nx) Ni(Ji Jn Mp Nw tF) Og(Jl Nn Om On Wm) Ng(Ij Mv Nn Om) Kr(Iv Jn Ql Sr) bJ(In Iv Ji Uv) Rf(bO Oz Pa) tF(bN cW Tj) Ef(aG Oi) Wm(Ji Jn) Nn(Ji Oi) Mp(Ik Mr) Pe(Oz Pa) bO(Nr Sr) dA(bR Nd) eC(In Pi) BgJd MlNy MnNh NaNw HuJn RiQl} Ng{Nn(bJ bO dA Dp Et Fp Fr Hv Hw Ii Ij Im Ir Is Iv Jd Jg Jh Ji Jl Jn Jo Jq Jr Jt Jv Kr Lh Lu Lv Lw Lx Md Me Mi Mn Mq Mr Mt Mu Mv Mw Mz Nb Ne Nh Ni Nt Nw Oi Ok Om On Pa Pe Pk Po Qa Qe Ql Ri tF) Lx(Et Fp Hv Hw Ij Im In Is Iv Jd Jg Jh Ji Jk Jl Jn Jo Jp Jq Jr Jt Kz Lh Lv Lw Ly Ma Me Mg Mm Mn Mq Mt Mu Mv Mw Nf Nh Ni Nt Ny Oh Ok Om Oz Pb Po Qa Qb Qe) Po(Ba bJ bO dA Et Fr Im Ir Is Iv Jd Jg Jh Ji Jk Jl Jn Jp Jq Jr Jt Lh Lu Lv Lw Me Mi Mm Mn Mq Mt Mu Mw Mz Nb Ni Nk Nt Nw Oi Ok Om Pc Pe Qa Qe) eC(Ad Cp Cq Cu Cw Dc Dd Dk Hv Hw Hx Ib Id Ij In Ir It Iv Jn Jq Jr Kd Ke Kn Kq Lw Mw Mz Nb Nf Ni Ny Om Pb Pe Ph Pi Pk Qa Sr Up Ut Vp Vt) Et(Fp Fr Hu Ij Im Io Ir Is Iv Jh Jl Jn Jr Li Lu Lv Lw Me Mi Mq Mr Mt Mu Mv Mw Nb Ne Nf Nh Ni Nt Nw Oh Om Pa Pc Pd Pe Pf Qa Qb Qe Wm) Mq(BA bJ bR cK cT dA dM Fr Fy Im Is Jd Jg Ji Jl Jp Jq Jr Kx Lw Ma Mm Mn Mp Mu Mv Mw Nw Ny Og Oh Ok Om On Pf Qa Qb Qe Qy Rf) Mu(Fp Fr Fy Ii Im Iv Ji Jl Jn Jq Jr Lh Li Lv Ma Me Ml Mn Mp Mv Mw Nf Nw Ny Oh Ok Om On Ow Pd Pe Pf Qa Qb Qe Rh Wm) Oh(Fp Fr Hu Ii Im Is Iv Jg Jh Jk Jl Jq Jr Kz Lh Li Lv Lw Me Mv Mw Na Nh Ni Nt Ny Ok Om Pd Pf Qa Qd Qe) Nf(aJ aP Ax BA bV cN cT Cv dM Fa Fr Is Jd Jg Ji Jl Nw Ok Om On Pf Qa Qe Qy Rf Sr Uf Ur) Jd(aW Ax BA bJ bM bR cT dA Ed Fy Hu Io Jv Kr Kx Ly Ms Nc Ni Nr Oi Ow Oz Pk Rf Rh Ri) Qa(bJ Fn Fr Hu Is Iv Jg Jh Jq Jr Lw Ma Mi Mm Mn Mt Mv Nb Ni Nw Ok Om Pa Pc Pe Pf Wm) Im(bV dM Fr Hu Is Jg Jk Jl Jr Jt Lh Li Lu Lw Mm Mn Nh Nw Ok Om On Pc Pd Pf) Om(Fp Fr Is Ji Jl Jn Jr Li Lu Me Mr Mv Mw Ni Nt Nw Og Ok Pc Pe Pf Qb Qe) Ni(aP Ar Ax bA bJ bV cN Cs Fr Jg Ji Jl Kx Li Nw On Pf Rf Sr Tn) Mv(Is Ji Jl Jn Jq Jr Ma Mm Mn Mp Mw Nw Ny Ok On Qe Wm) bJ(bA bV Cs cT Fa Fy Ji Jn Jr Kq Ml Nr On Pe Pf Pk Tn) Fr(Fp Hu Hw Ij Ik Is Ji Jn Jr Me Nh Nt Nw Qb Qe Wm) Is(aW bV Hu Jg Jl Jr Li Lw Mw Nt Oi Ok Pc Pf Wm) Ba(aD Cs Fp Jv Kl Me Nr Pk Ql Rf Ri Ss Vo) Fp(Cv Jg Jk Jp Jq Lw Ma Mm Mn Ok On) Qe(Jg Jr Lv Lw Ma Mg Mm Mp Pc Pf Wm) Hu(bA cT Jg Jl Kx Mm Ow Ql Rf Rh) Ji(Jg Jk Jl Jr Ma Nt Ok Pc Pf Wm) Jr(Jg Li Ma Mn Mw Nw Ok Pf Wm) Qy(Ax bA Cs cT Fy Kx Ow Rf) Wm(Jn Jp Lh Mw Nw On Qd) Sr(bO dA Jv Kx Rf Rh) Pc(bO Jg Lv Lw Mm Mn) Fa(bO dA Dp Ri tF) Kq(aF bX Jv Kr Rh) Rf(bV cN cW Lu Ri) On(Io Kr Me Pa Pc) Pf(bO Jl Lv Me Mw) Nw(Lu Me Mg Nt) bA(Fn Me Ql Ri) Lv(Li Mw Ny) Jl(Io Mw Og) Mp(Jn Mw) Mr(Jg Mn) Kx(dA Jn) Li(Jh Jq) Ri(Ax bV) Ok(Lw Qb) cT(Fb Ql) NtMm MlJg JeOw KzbV} Og{Mu(Et Fp Hu Hv Hw Ii Ij Im In Ir Is Iv Ji Jl Jn Jo Jq Jr Js Jt Jv Kx Lh Li Lj Lv Lw Lx Me Mi Mj Ml Mn Mq Mr Mt Mz Nb Nf Ni Nn Nt Nw Oh Ok Om On Ow Pa Pc Pd Pe Pf Po Qa Qb Qe Wm) Lx(Et Fp Hq Hv Hw Ii Ij Im In Ir Is Iv Jn Jo Jq Jr Js Lh Lv Lw Me Mm Mq Mw Mz Na Nb Nd Nf Nh Ni Nn Ns Nt Ny Oh Ok Om Oz Pb Pd Pf Pg Qa Qb Qd Qe Wm) Mq(Ax bJ dM Et Fp Fr Ih Im Is Jg Ji Jl Jq Jr Jv Ki Kx Lj Lv Lw Mm Mn Mp Mt Mw Nh Nn Nw Ny Oh Ok Om On Pd Pe Pf Pk Po Qa Qb Qe Ql Qu Rf Wm) Po(bJ bO Et Fr Im Ir Is Iv Jg Ji Jl Jn Jq Jr Jt Jv Ki Lh Lv Lw Me Mm Mr Mt Mz Nb Nf Ni Nn Nt Nw Oh Ok Om On Pa Pc Pe Qa Qe Wm) Om(Ed Et Fp Hu Im Ir Is Iv Jh Jl Jn Jq Jr Jv Lh Lj Lw Ly Me Mi Ml Mr Ms Mt My Nf Nn Nw Of Oh Ok Pa Pc Pe Qa Qe Wm) On(bJ Ed Fp Hq Hu Im Is Jh Ji Jl Jn Jq Jr Lj Lw Ly Me Ms Mv My Nf Ni Nn Nv Nw Of Oh Pc Pg Qa Qe Wm) Jv(Ar Ax Ba bV Cs Dk dM Fa Hu Id Is Iv Jd Ji Jl Jn Jr Kq Kx Ni Nn Nr Ow Pe Pf Pk Qd Qe Rf Sr) eC(bA Bn Cp Cq Cu Hv Hw Hx Id In Ir Is It Ji Jn Jq Jr Kd Lw Mz Pb Pi Pk Qa Rj Sr Up Vp Vt) Nn(Et Fp Fr Is Iv Ji Jl Jn Jq Jr Ki Lh Lv Lw Me Na Ne Nf Nh Ni Nt Nw Oi Ok Pe Qa Qe Wm) Jl(bJ bO dM Et Fp Hw In Io Ir Is Ji Jq Ki Kr Kx Lw Me Ml Mt Nf Ni Nw Oh Ok Pc Qa) bJ(aD bA bV Cs Cv Dc dG dL Id Iv Ji Jq Jr Kc Kq Lw Mx Ni Ok Pe Pk Qa Sr Ul Vt) Ki(Ax bV Cs dA Is Iv Jd Jn Jr Jy Kq Kx Lw Ml Nf Ni Ow Pd Pe Pk Qa Ql Ra Sr) Nw(Ed Et Fp Im Io Is Iv Jr Li Lv Lw Me Na Nf Ni Nt Nu Oh Ok Pc Pf Qa Qe Wm) Wm(Et Fr Ir Is Iv Ji Jk Jn Jp Jq Jr Lh Mp Nv Oh Ok Pe Qa Qb Qd Qe Sr) Is(Ao aW Co Ed Et Fp Io Iv Jq Jr Lw Me Nf Oh Oi Ok Pd Pe Qa Qe) Nf(aJ aP bA bW cN Cv dM Et Fr Jg Ji Oh Ok Pf Qa Qe Sr Uf) Qa(Et Fr Io Iv Jq Jr Lw Me Mi Mm Nb Ni Oh Ok Pa Pe) Ji(bN bO cZ Ed Fr Io Jg Jr Kx Ni Nt Pa Pc Pe Pk) dM(Ed Ez Im Iv Jd Kx Kz Me Mr Ni Oz Pk Ql Ri Sr) Qe(Et Fp Fr Io Jg Jq Jr Lv Lw Mm Ni Oh Ok Pc) Lw(bN Ed Et Fp Im Jr Kr Kx Kz Pk Qb Rf) Sr(aF bO Co cZ Dp Ed fP Kg Ko Kr Kx Pk) Jd(Ao Bg Co Ed Hu Iz Kx My Ni Qu) Oh(Et Fp Hu Jr Lv Me Nh Ni Nt Pd) Fr(Ed Fp Im Jr Me My Nh Ni Qb) Et(Fp Io Jr Lu Ne Nh Qb) Mm(Fp Im Jr Me Nt Pe Pk) Co(Fy Iv Jn Ni Pe Rf) bV(Dp fP Iv Ni Ql Ri) Cv(Cx Ed Fp Kz Pk) Jr(Im Li Nh Ok Pf) Kx(dA Ed Ni Pk Ri) bO(aJ aP bA dG Pf) Fp(Hx Jg Jq Ok) cN(Iv Jn Kz Rf) Ni(Ax bW Cs) Ba(Ed Kl) Mp(Nd Ns) Ok(Me Qb) Pk(bW Uf) CsQy EdJy NtJq NuLv KqaF RfUl aPfP} eC{Pk(aE aJ aM aP aW bA bE bH bI Bo bP bV cI cK cN Co Cv dM Ed Fn Hu Id In Jd Jo Jr Ju Jv Jy Kd Kg Ki Kk Kq Kr Kx Lu Lw Lx Mg Ms Na Of Qg Qu Qv Ra Ri Ug Ur Vo Vp) Kq(aD aE aF aL Ao aW Bb Bg bH bJ bO bP bX cI cN Co Cp Cq Cs Ct De dM Ed Fn Ii Iz Jf Jg Jo Jv Kf Kg Ki Kl Kr Kx Ma Mg Of Qg Qu Ra Uc Ur Vo) Ed(Ad bA Cq Cu Cv Cw Dc dM Hv Hw Id Ir Jd Ji Jn Jq Jr Kd Ke Kk Kn Kp Lw Mt Mu Ny Om Pi Sr Up Ut Vp Vt) dM(Ad aM Cq Cu Cw Dc Hv Hw Id Ij In Ir Iv Jn Jq Jr Kd Kn Kz Ly Na Nf Ni Ny Or Pi Qa Rj Sr Up Vp Vt) Mg(Ad Cp Cq Cu Cw Dc Hv Hw Hx Ib Id Ij In Ir Is Iv Ji Jn Jq Jr Kd Kn Na Nf Om Pi Qa Sr Up Vp Vt) cN(Ad Cu Cw Dc Hv Hw Hx Id Ij In Ir Is Iv Jn Jr Js Kd Kn Ml Mz Na Nb Ni Ny Pi Qa Rj Sr Up Vp Vt) Kg(Ad Cq Cu Cw Dc Hv Hw Id Ij In Ir Iv Jn Jq Jr Kd Kn Kr Lh Mz Na Pi Qa Rj Sr Up Uv Vp Vt) aW(An Cp Cu Dc Id Ir Iv Ji Jn Jq Jr Kd Ke Kn Md Mr Mt Mz Nb Ni Ny Om Pe Pi Qa Sr Vt) Qu(Ad bA Cp Cq Cu Cw Dc Hw Hx Id Ij Jn Jr Kd Kn Nb Ny Om Pi Qa Sr Up Ut Vp Vt) cI(Bn Cp Cu Dc Id Ir Iv Ji Jq Jr Kd Ke Kn Lw Mz Nb Ni Ny Om Pe Pi Qa Sr Vt) Jo(Cp Cq Cu Cw Hv Hw Id Ij In Ir Iv Jn Jr Kn Kr Na Om Pb Pi Sr Uc Up Vp) Co(Cp Dc Id Ij Jh Jq Jr Kd Ke Kn Mt Mu Mw Mz Nb Ny Om Pe Po Sr Ut Vt) Qg(Cu Cw Dc Hv Hw Hx Id In Ir Iv Jn Jr Kd Lw Ml Pi Qa Sr Up Vp Vt) Kx(bA Cu Dc Hv Hw Hx Id Ij In Ir Jn Jr Kd Ni Ny Pi Rj Sr Up Vt) Ur(Ad Cq Cu Cw Hv Hw Id Ir Iv Jn Jr Kd Na Pi Qa Rj Up Uv Vp) bP(Cu Dc Id Ij In Ir Iv Jn Jq Jr Kn Ni Pi Qa Sr Up Vp) Vo(Ad bA Dc Id Is Ji Jq Jr Ke Kf Kn Lw Ni Pi Qa Sr) Sr(aK aN aU bH bO bX cK dA dJ Jv Ki Kl Kr Lu) Pi(aE aJ cK Ct Jd Jv Ki Kk Kr Lu Ms Of Qv) Jr(aE bI cK Fn Hu Jd Ki Kr Lu Of Ra Ri) Ny(aL Ao Bb Bg bV cK Cs Hq Iz Ki Of Ra) Dc(Ao bH bI bJ Hu Jf Jv Ki Kr Lu Ra) Kd(Ao bH bO Cs Hu Jd Jf Ki Lu Ra) Kl(Id Ji Jn Jq Kc Kf Kn Lw Om) Kr(bA Cu Id Jn Jq Ke Lw Qa Vt) Vt(bH bO cK dA dJ Hu Ki Lu) bA(cT Hu Jy Ra Rf Ri St) Lu(Cu Id In Ir Ji Jn) Lw(Ap Bg Dg Hf Mf Ss) Jq(aF aK Ao bH Hu Ii) Cs(Ir Nb Ni Om Vp) Id(Dl Fn Jd Of Ug) cK(Ir Iv Ml Mz Qa) Bg(Jh Mu Mw Om) aD(Hu Jd Je Mu) Ke(bO bX Jt) bV(Ir Iv Nb) Ap(Jd On) Me(Je Kk) Ml(dA Hu) Mz(aK Hu) Ni(aE Vp) Ji(Ao Cq) Kn(bH Ii) Of(Hw Up) CuKi MwMy IvVp} bJ{Kq(aC aD aE aF Al aM aN Ao aW Ax bA Bb Bg bP bV bX cN Co Cp Cs De Dg Ed Ef Fn Fp Iz Jg Jo Jt Jv Kg Ki Kl Ko Kx Lj Ly Me Mq Ms My Nf Oa Oe Of Oi Pk Qg Uc Ue Ug Ur Ut Uv Vo) Ji(aD aE Af Ao Ap aW bA bN bP bV bX cC Co Cs dA dB dE Ed Ii Iu Iz Jo Jt Jv Kg Kk Kl Ko Kr Kx Lu Mg Ms Oe Oi Pk Qg Qv Ue Ug Ur Uv Vo) Lw(aC aD aE Ao aW Bg bN bV Cs dC Dp Ed Fn Fp Iz Jv Kg Kl Ko Kr Kx Ld Lj Mg Mq My Nd Nf Nr Oa Oi Pk Qg Qv Rf Uc Ug Ur Uv Vo) Jq(aC aD aE AF aM Ao aW Ax bA Bb Bg bN bP bV bX Cs Cx De Ed Fp Iz Jo Jv Kg Kl Ko Kr Kx Lj Me Mq Ms Oi Pk Qg Ug Vo) Sr(aE aN aW bP bV bX cK Co

Figure 8 Continued

Cx Ed In Iz Jo Jv Kg Ki Kk Kr Kx Ky Lu Ly Mg Ms Oe Oi Pk Qg Qu Qv Ri Ue Ug Ur Vo) bV(aM Ed fP Iv Jr Jv Ki Kl Kx Kz Lj Ly Me Ml Mq Mr Ms Nc Nf Ni Nw Oe Oi Pc Pe Pk Qb Ql Qu Rf Ri Uv Vt) aD(Ax bQ Cs Cv Dc Ed Hu Iv Jd Jn Jr Jy Ki Kk Kx Ky Lx Mq Mr Mu Mz Nc Nf Ni Nn Nw Oe Oh Pe Pk Qa) Ed(aP bA cN cT Cv Dc dM Fr Fy Id Jd Jr Jy Kd Ke Kk Kn Kx Lv Mt Mu Mz Nw Ny On Pe Rf Ut Vt) Pk(aJ aP bA cN Co cT Cv dG dL dM Iz Jo Jv Ke Kg Ki Kk Kx Lu Lx Ms Nw Oe Oi Qg Qv Ur) Oi(Ax Cs Dc Id Ih Iv Jn Jr Kn Kx Lj Ml Mz Nn Ny Or Pe Qa Qd Ut Uv) Me(aJ aP aW Ax bA bP bZ cN Cv dG Kk Ky Lu Lx Ms Qg Qv Ur) Vt(Ax Cs cT dA dM Jo Kg Kk Kx Ky Lu Ms Oe Qg Qv Ug Uk Ur) Qa(aW cN Co dM Ih Iu Jo Jv Kg Kr Kx Lu Ms Oe Qg Qu Ur) Pe(aE Ao aW Co dM Ih Ii Iu Iz Jo Jv Lu Mg Ms Oe Qu) bA(aM Cs Dc Iv Jv Kr Kx Mg Nf Ni Pc Qg Rf Ri St Vv) Cs(Cv Dc Jv Jy Ms Mu Mz Ni Nw Ny Oe On Ri Ut) Jr(aE aW cN Co Iu Iz Kg Kl Lu Mg Ms Oe Qv Ur) Ke(aE Ao bP bX Iz Jo Kl Ko Kr Kx Ly Mg Ms Vo) Ms(Dc Fa Iv Jd Jn Kn Kx Ni Or Po Uv) Ao(Dc Fy Jy Kd Mt Mz Ny On Rf Ut) Uv(aJ bP cN dM Jo Kg Lx Nw Qv Ur) Id(aE bP Jo Jv Mg Of Qg Ur Vo) Ni(aE aJ aW Ax cI cN Kx Tv) Dc(aC Iz Jv Ki Kx Mq Qg) In(Iv Jo Kg Nw Qg Ur) Iz(Fy Mz Ny Om On Ut) Iv(aE aW bP cN dM) Fy(cN Ii Jo Kg) Ml(cN Lx Nw Qg) Tv(Nw Qd Qe St) Kn(bP Jo Jv Kg) On(Ap Co Jg Kx) Pi(bP Jo Qg Ur) aW(Is Mr Qd Qe) Cv(aC Fp Lj) Oe(Fa Jl Po) Bg(Mw Om) Nn(Jv Kl) Nr(cN Co) Mz(aE Jv) Nf(Qg Qv) Iu(Is Qe) Jn(aE cN) Kx(aM Qv) Lj(Mu Ny) Of(Cw Om) BaKl BbNy MgcT MwMy TnSt QgaM KrdL RfVv} Kr{Lw(aF aM Ax bN bO bX cI Cs CX dA DE Ed Et Fa Fp Fy Hu Hw Id Ih Ij Im Is Iv Jd Jl Jn Jr Js Jv Ki Kk Kx Kz Ld Li Lj Lx Me Ml Mq Mr Nc Nf Ni Nl Nn Nr Nw Ny Oa Oh Ow Oz Pe Pk Po Qa Qb Qd Qe Ql Qy Rf Ri Sr Uf Uh Ur Wm) Kq(aF aL Ao aW Ax Bb bF Bg bP cI cN Co Cs De dM Dp Ed Ef Fn Hb Hq Ii Iu Iz Jg Jo Jv Kg Ki Kl Kx Lj Mq My Nq Of Oi Oz Pg Ql Qu Ri Ua Uf Ur Vo) dM(aM Cs Ed Et Ez Id Im Is It Iv Jd Ji Jl Jn Jr Ke Kz Me Mq Mr Mw Ni Nn Nr Nw Ny On Ow Oz Pe Pj Pk Po Qa Qd Qe Ql Rf Ri Sr St) On(aF aM Ax Bb Bg cI cN Co Cs dA Dp Ed FP Hq Iv Iz Jg Jn Jv Ki Kk Kx Ld Lj Ly Me My Nd Nn Oa Oh Ow Pk Ql Rf Ri Tv Wm) Ji(aF aW Ax bO bP bX cI cN Cs Cx cZ dA De Dp Ed Ii Iv Jq Jv Kg Ki Kx Ms Ni Oh Ow Qg Ql Rh Ri Vo Wm) Sr(bW cN Co Cs dJ Ed Iv Jd Jv Kg Ki Kx Lx Mm Mr Mu Ni Nn Oi Ow Oz Qe Qg Ql Ri Uf Ur) Jn(aJ bM bW cN Co Cv dG dL Jv Ki Kx Lx Mm Mq Oi Po Qg Ri Uf Ur) Ke(aF Ax bO bX Cs Cx cZ dA De Ed Fn Fp Jv Ki Kx Nn Ow Pk Ri Wm) Jd(Ao Ax bA Bg bV Co Cs Cv dL Ed Id Iv Jv Kx Ml Mq Mx Ul) Mq(aJ Ax bA cK dA Id Jr Ki Kk Kx Lx Nn Oh Qy Rf Vp) Qe(aW Ax bA bI cN Cs dL Ih Iu Jv Kx Qv Ri Tn Tv) Uf(Cs Fy In Ir Is Jr Ml Nf Ni Pe Pi Pk Qa Vt) Cv(Ax Cs Ed Fp Iv Lj Nn Nr Pe Pk Qa Ql Rf) Kx(aM bV dL Et Iv Jl Jr Ki Mx Ni Pk Qa Ri) Ed(aP dG Et Fr Id Jq Lx Nn Om Pf Po Vt) Is(Ao aW bV bW Co Ih Ii Ir Iu Iz Jv Vo) Cs(Et Jl Jv Jy Mm Mp Mu Ni Ow Qy Ri) Ki(bA Id Jq Jr Mx Ni Nn Ok Pe Pk Qa) Iv(aJ aP Ax bV cN dG dL Lx Mm Ur) Ni(Ax bV cN Fa Lx Mn Nn Oh Po) Qa(aW bW Co Ih Ir Iu Mm Qc Qg) dL(bO Hu Mr Mu Pk Ql Qy Rf Ri) Id(Jv Mn Mr Mu Ow Oz Ql Ri) Jv(Ax Fa Jr Nn Om Pe Pk) dG(bO Dp Nf Pc Ql Rf Ri) Pk(aJ bW cN Lx Mm Uh) Ax(Et Mr Mu Ow Ri) Nn(aM dA Mx Oi Ul) Jl(bA dA Ow Ri Tv) Jr(cN Co Qg Ri Ur) Fa(dA Dp Mu Ri) Mm(aM Ml Pi Vt) Rf(bV cN Mx Ul) bA(Mr Nw Ql Uh) Bg(Dk Mw Om) Lx(Me Pc Vv) bV(fP Nc Ql) Po(bO Oz) Et(Ao Lu) Mr(aW cN) Nw(cT dA) Uh(Pi Tv) CoPe FyKg GzIt MucT MwMy KkOw OfOm OzaP PibW} dM{Me(aD aM Ax bV bW Cs Cv Ed Et Fp Hu Jd Ji Jn Jq Jr Jv Jy Ki Kx Ky Ld Lj Lw Lx Ma Mn Mq Mr Nc Nf Ni Nn Nr Nw Ny Oh Oi Om On Ow Oz Pc Pe Pf Pj Pk Po Qe Ql Qy Rf Rh Ri Sr Ur Vt) Nf(aC aD Ax bV Co Cs Cv Dc Ed Et Is Iv Ji Jn Jq Jr Jv Jy Ke Ki Kq Kx Ky Lw Lx Ly Mn Mr Ni Nr Nw Oe Oi Oz Pf Pj Pk Po Qe Qg Ql Qu Qv Rf Rh Ri Sr St Uf Uh Ur Vt) Kz(aD aM bR bS bW cA Cs Cv Dc Dp Et Fr Hu Jd Ji Jn Jq Jr Jv Jy Ke Ki Kq Kx Lw Lx Mn Mr Mu Ni Nn Nr Nw Oe Oi On Oz Pe Ql Qu Qv Rf Rh Ri Sr St Uf Uh Ur Vt) Ly(Ar Cs Ed Et Ez Fa Hu Id Is Iv Jd Ji Jl Jn Jv Jy Ke Ki Kq Kx Ld Lx Mq Mr Ni Nn Nr Nw On Ow Oz Pe Pj Pk Po Qa Qe Ql Qy Rf Ri Sr St Uf Uh Ur Vt) Ni(aD aG Bo bV bX Cs Dp Ed Fn Fp Hf Hu Iv Jd Ji Jn Jr Jv Kx Li Lj Mq Nj Nk Nn Nr Nw Oa Oz Pa Pc Pe Pk Po Qe Ql Rf Ri Sr Vt tF) Pk(BO bR bW Cv Cx Dp Hv Jd Ji Jv Jy Kg Ki Kq Kx Lw Mq Mr Nc Nk Nw Oi Ow Oz Pa Pb Pc Qg Qv Rf Rh Ri Sr Uf Uh Ur) Oz(Db Ed Fa Fy Hu Im Is Jd Jn Jr Jv Jy Ke Kq Kx Mq Mr Nn Nr Nw Oi Pe Po Ql Qm Qt Rf Ri Sr St Uh Ur Vt) Ed(bR Db Jd Ji Jq Jy Kq Kx Mq Mr Mu Nc Nk Nw Oe Oi Pc Ql Rf Ri Sr Ur tF) Mq(aD Cv Dc Dp Hv Jn Jq Jr Jv Kl Kq Kx Lw Nr Nw Oe Oi Pc Ql Qu Rf Ri) Pa(Cs Fa Fy Is Jl Jn Jr Kq Lx Mr Nn Nr Oh Pe Pf Po Qa Rf Sr) Ri(aM bX Cs Db Im Iv Jn Jr Kx Ml Mr Nc Pe Ql Rf) bN(aM bQ bW Cv fR Ji Jq Jr Lw On Pe Po) Kx(aM bO Iv Jd Jn Jv Mr Oi Pb Pc Ql) bX(bR Is Iv Jd Ji Jy Kq Mr Qe Rf Sr) Im(aD Co Jv Ki Nc Oe Oi Qu) Jv(Iv Jn Jr Mr Nr Ql Rf) Nc(Is Iv Jn Pe Rf Sr) Kq(aF Bg Cp De Kl Uc) bR(aM bQ It Mr Pc Ql) Rf(Al aM Hf Oi Pc) bO(Fa Pe Po Qa Sr) Cx(Cv Jq Qn Sr) Oi(Fp Jn Mr Ql) Db(Iv Mr Sr) Dp(Fa Qv Sr) Jd(Bg Iz My) Kl(Ba Nn) Ql(Hf Oe) Pc(Ow Rh) FafP FpNw FyKg LxdH MlQg MrOe MwMy QcQe} bO{Sr(aC aD aE aJ Al aM aN Ao aP aW bA bI bM Bo bP bR bV bW cK cN Co cS cT cW dA dG dL Dp Ed Fr Io Iu Iz Ji Jq Jr Ju Jv Ki Kl Kq Kx Ky Lu Lw Lx Ly Me Ms Mu Nc Ni Nl Nn Nw Oe Oh Oi Ow Oz Pf Pk Po Qa Qg Qn Qu Qv Qx Rf Rh Ri Uf Ug Uk Ur Uv Vo Vt) Fa(aJ aP bA bV cT Cv cW Dc Ed Io Is Iv Jd Ji Jn Jq Jr Jv Jy Kq Kx Lw Ly Me Ms Ni Nw Oe Oi Pf Pk Qe Ql Rf Ri St) bA(aM bR Cs Ed Fn Fr Is Iv Jd Ji Jl Jn Jr Jv Ke Ki Kx Me Mq Nf Ni Nn Nw Pe Pk Po Qa Qe Ql Qv Qy Rf Ri Vt) aJ(Ar bR Cs Ed Fy Hu Is Iv Jd Ji Jn Jr Kx Ly Me Ml Mq Mr Ni Nr Ow Oz Pe Pf Pk Po Qa Qe Ql Rf Ri Uv Vt) aP(bR Cs Ed Fy Iv Ji Jn Jr Jv Ki Kx Ly Me Mq Mr Nf Ni Nr Oi Ow Pe Pk Po Qe Ql Rf Ri Uv Vt) Po(aD aM aW bR bV Co cT Ed Ii Io Iz Jn Jo Jr Jv Ki Kx Lu Ms Nc Ni Nw Oe Oi Qv Ri Ur) Ji(aK bP bV Cs cT Ed Fn Fy Jv Kg Kx Lu Mq Ms Nd Nf Oi Pk Qv Rf Rh Ug Ur) Lx(aM bR bS cA Co cP cW Ed Jr Kx Me Ml Nd Nf Nr Oa Pk Uv Vt) Kq(aE aF Bg bM bP Cs De Ed Fn Io Jt Jv Kx Mq Of Oi Vo) Kx(bV cS cW dG Fr Jl Jr Ke Nw Oi On Pf Qe Qv) Pe(aD bV bW Co cW Io Iz Jv Kg Ki Lu Ms Oi Ur) Fy(Ao bM bW cN Co cW dL Iz Kg Ki Lw Uf) Oi(dG Is Jd Jl Jn Jr Mq Nn Nr Pf Qa Rf) bV(Is Iv Jr Ki Me Mq Ni Nr Nw Qe Ql Rf) aD(Ba fR Jd Jl Jn Jr Mq Nn Oh Pf) Nw(Ax Cs cW Ed Ml Mq Nf Nr Pk) Nn(cN Io Jv Ki Ms Qu Qv Vt) Rf(Ao cN cW dG dL Ed Lu Lw) Jr(cN Lu Mq Ms Oe Ri Ur) Ed(Fr Jq Ke Lw On Pf) Qa(aW Bo Fn Jo Qg Qv) Me(dG Fr Pf Qv Ur) On(Bg Cs Iz Lj Ml) Jn(bM cN Jv Ms) Pf(bR Jv Ki Ni) cT(Jl Qd Qe Vt) Cs(Cv Ke Lw) Fr(Nf Pk Uv) Mq(Dc Jq Mu) Is(Iz Lu Qv) Nr(Co Cv) Ms(Jd Oh) Qe(aW Qv) Jl(aE Oe) Pk(dG Ki) bM(Dc Jd) cW(Ql St) EtQv LwOa bRdG} Ed{Ri(aJ aP Ax bA bV cK cN cT Cv dA Et Fa Fr Jd Je Ji Jl Jn Jq Jy Ke Ki Kk Kq Kx Lw Lx Nc Ni Nw Oi On Pe Po Ql Qv Rf Sr Tn Uh Ur Vt) Kq(aF aW Bb Bg bH bX cK Cq Cu cZ Fn Fw Hq Ii Ir Iz Jg Jt Jv Kd Ki Kx Mj My Nc Nv Oe Of Oi Pb Pg Qg Qu Rf Tv Uc Ur Ut Vp) Jd(aD aW bA Bg bR cK Co cT Cv dA Io Iz Jv Kx Lw Ms My Nc Ni Oe Oi Qc Qu Qv Rf Sr Tz Ua Ur Vt) Kx(Bc cK cN Cv dA Et Fr Hu Id Io Je Jq Jv Jy Ke Ki Lw Mr Mu Ni Nw Oe Oi On Qv Qy Sr Ur Vt) Jv(An Ax bF bQ Cv Dk Fy Hu Id Ji Jq Jy Kk Lw Lx Mu Ni Nn Nr Nw On Pk Ql Rf Sr Vt) tF(aJ Ax bA bV Cv cW Fa Fr Id Jq Jy Ke Lu Lw Lx Ni Nn Nw Po Qv Sr Uf Ur Vt) Oi(Ba dA Et Fb Fy Hu Is Je Jn Jr Jy Mu Ni Nn Nr Om Pd Ql Qy Rf Sr Vt) Lw(aF aK bN bR bX CX cZ De Fn Fw Ko Nf Ni Nl Oz Pk Qg Qz Ur) cK(aP bV cW Et Fa Fr Ji Jl Jq Ke Mq Ni Nn On Pe Pf Pk Qv Rf Sr) Ur(Cv dA Hu Id Is Iv Ji Jn Jq Kn Ml Ni Ny Pd Pk Ql Rf Sr Vt) Qg(bA Dc Id Ji Jn Jq Jr Kd Ke Kn Ml Ni Pe Po Qa Sr Vt) Rf(aW bV cN Co Cv cW Io Je Ju Lu Ni Oe Qu Qv Uf) Oe(Fy Hu Jl Jn Jr Jy Lx Mu Nn Nw Ql Qy Sr Vt) Ni(aD aJ aW bA bV cI cN Hu Nw Qv Sr Vt) Sr(bH Cq cZ dA dJ Dp Fw Io Nc Qc Qu) Ji(aK aV Cq cZ dA Fn Fw Nc Qc) Jq(aK bX Cx cZ Fn Fw Nc Nl) Fy(bH cN Co Fw Ii Qv Qz) Jy(aD aW bA bV Dp Ki Ql) dA(aD bA Cv Nw Qv Uh Vt) Nc(bV Je Lx Nw On Vt) Ke(aK bX cZ Fn Fw Ko) Qy(bA bV cT Ms Qv) bX(aP Cv Fr Mu Nw) Lx(bR Co Nl Pf) Ki(bV Cw Dc Mu) bA(bE Fw Nw St) Cv(Cx Nf Pk) Dp(aP bV Qv) cN(bR Jn Pk) Ba(Kl Qu) Fw(Dc Kn) Vt(cT dJ) PoJe FnKn MucT MwMy NkTn TvUh InIv IrIs OnaW aPfP} Nf{Ur(aD aJ aP Ax bA bP bV cK cN cT Cv dA Hu Id Io Is Iv Je Ji Jn Jq Jr Jv Ki Kq Kx Lw Lx Me Mu Nw Oi Pd Pk Po Qa Qe Qv Rf Ri Sr Ul Vt) Co(bA bQ Dc Fr Fy Hu Jd Ji Jn Jq Jr Kd Ke Kk Kq Kx Lv Lw Lx Mu Nn Nr Nw Om On Pe Rf Sr St Tn) Qv(aJ aL aW bP bV bW cK cN Cv dA Dc Dp Ji Jn Jq Jr Jv Ki Kx Lw Lx Mm Oi Ql Qu Qy Rf Ri St Uf) Jv(aJ aP Ar Ax bA bF bQ bV cN Cv dA Fa Fr Hu Id Jd Je Jn Jp Jq Kq Ky Lw Lx Nn Nw Rf Sr Tn) cN(bR bS bV cA cL cT Io Iv Jn Jq Jr Ki Kq Ky Nd Ni Nw Oe Oi On Pk Ql

Im Jk Jo Jq Lv Mg Ms Mv Ns Oe Of Pb) Bg(Ba bN Cx Fy Ij Kz Lj Lx Ma Ml Nr Rf Rh) Ms(Ji Jn Jr Lj Ml Nn Nw Oh Pe Qa Qb Qe Wm)
Of(Hw Ij In Ir Iv Ji Jn Lx Ok Pe Qa) Ns(Jr Li Lv Lx Ml Nw Oh Pe) Hu(Ji Jr Li Lx Nn Nw Oh Pe) Lv(Ih Jr Js Lj Nw Oh On) Ly(bA Ji Ml Nh
Nw Wm) Fy(Ao Co Ii Iz Kg) Lj(Io Jq Jv Nw On) Ml(Im Iz Mg Pb) Lx(Hq Hw Mv) Im(Ao Ji Nw) Jr(Et Jq Ok) Kz(bV cN Ki) Mv(Ji Nn) Iz(bA
Tn) Qa(Jk Jo) Jv(Qv Rf) Kl(cT Ow) CsOe MgOh MpNd HqPe JiPb bVfP} Me{Ur(aJ Ax bA bP bW cK cT Cv dA Hu Is Iv Je Ji Jn Jq Jr Jv Jy Lw Lx Mm Mq Mr Nr Nw Oh On Ow Pd Ql Qy Rf Rh Ri Sr Uf Ul Wm) Lx(aW bR Co cZ Ha Hq Hu Hx Jn Jq Jr Kg Lv Lw Ly Mq My Ns Ny Of Ok Om Pb Pc Pg Qh Rh Tj) aW(Cv Et Is Ji Jl Jn Jy Lw Mm Mr Mw Nn Nw Oh On Qa Qc) Co(Ax bQ bZ Cs dA Fy Jn Nn Nr Pe Rf Tn) Kg(Ax Is Jn Nn Nr Oh Pd Qy Rf) On(cI Hq In Jr My Nb Ns Of Pb) dA(Fa Ms Nn Nw Qg Qv Ri Uf Uk) cN(Ax bS cA cL Iv Jn Ri) Lw(aF Ax cI Cs Cx Rh) Ax(Cv Jy Ki Qu) Nn(Ji Jr Lv Oi) cK(Cs Fa Qv Uf) Cv(cI Cs Cx) Mp(Hq Nd Ns) Jq(Lv Pc Wm) Nw(Im Jr My) bV(fP Qy Ri) Ba(Kl Vo) Ji(cI Pc) Qv(aV Qy) Jy(bP cI) Ow(In Je) CsQu PoJo EtJr FaQg FrMy LuRf MqOh NaPc OfOk} Jv{Sr(aE aK aN aV aW bP bX cI cY dA dJ Hu Iu Kg Ki Kz Ly Ms Oe Oi Oz Pa Qg Qv Rf Ur Vo) Ly(aP Ar Ax bA bV cN Cs Et Fa Ji Jn Lx Nn Nr Nw) Ur(bA Fy Is Iv Ji Jn Jq Jr Kz Mq Nr Pe Qa Qb Rf) Rf(bV cN Co Cs Hu Lu Lw Mq Oi Qv Ri) bX(aP Cv Fa Fr Id Ji Ke Lw Nn On Pe) Jn(aE aW bA bP cN Mq Ms Oi Qv Ri) aW(Im Is It Jr Mr Mw Nn Qa) Pc(aP Ax bV Cs cT Fa Qv) Nn(bN Co dA Ms Ri tF) Cs(cK dA Hu Jy Ri) Fa(dA fP Im Ri tF) Lw(aF aK bN Cx Kz) Qv(Hu Im Kz Nr Ql) Jr(aE aK Kg Mq Ri) bA(Fn Qg Ql Ri) Mq(aE dA Ky) Im(cN Tn Tv) Kz(bV cN Nw) Pe(Co Kg Qg) Ar(Jy Ri) To(Mt Ny) Qa(Kg Qg) Ji(aK aU) dA(Nw Oi) BaKl FybH NrMs MrHu MwMy TnOz} Mq{dA(aD aE Bg bQ bR bS cA CO Cv Hq Io Ki Ky Mk My Nd Ns Nw Qu Ur) Jr(aW Co Cq Et In Kg Lv Lw Lx Mm Nn Oi Pb Vo) In(Ih Is Nn Oh Pd Po Qa Qb Qe) Lx(Hq Jn Jq Js Lv My Ns Of) Oi(Et Is Nn Nw Oh Om Po Qa) Ms(Je Ji Mp Nn Nw Oh Po) Ly(Je Ji Kk Nw Rb Ur) Rf(Ao cK Co Iz Oe Qu) Ef(Dc Fr Jq Kc Sr) Lv(Mm Mt Mx Mz Oh) Lw(aU cI Kl Ss Vo) Ji(aK aU Im Pb Pc) Jn(aE aW Co Kg Qu) Po(Hu Jo Mg Pb) Et(Io Jo Lu Ns) Mp(Mg Ml Nd Ns) Jq(aK cI Pc Wm) Nw(Hu Nv Of Pb) cK(bR Ky Qu Sr) Co(Fy Je Pd) My(Fr Je Nn) fP(aJ aP bV) Bg(Hu Je) Fy(Ii Iz) Qu(bV Qv) Ki(Oe Ri) Of(Pi Vp) bR(cI dJ) CvcI DcaK NnMv HuIz IsaW OmPb aEtF} Lw{Cx(Fa Fn Iz Kg Ki Kl Kz Ld Nd Oa Ql Qv Qz Sr Ss Ug Ur Vo) bN(aW Ax Bg cI Fn Hu Nr Qn Qx Qz Rf Ri Ss To Up Ur Vo tF) Rf(AF aK aU Bb bX Co De Dg Jg Jt Kg Kl Ko Ly Vo) Kz(aW Bg Co Cs Fn Iz Jg Kg Ki Lu Qn Uc Ug Ur Vo) Vo(cT Db Im Is Iv Jn Jr Ly Ma Nn Nr Ow Ql Rh) Kl(Ba dE Im Jn Ma Nn Nr Oh Ow) Ko(aF Cs Jn Lj Nn Nr Pe) Fa(aF De Ef fP Ly Pa) Cs(Db Hf Pa Qg tF) Ly(Ki Ld Ql Ri Ur) bX(Ki Nd Qg Ur) Kf(dE Jn Nn) Pa(Ax Qv Rh) aF(Fn Uc Ur) Fy(Kg Nm) Ki(Db dE) aK(Ri Ur) AfQl AxHf BaSs BgHu EfMv PoOi FnNl UcJn ImIz IvaW bVfP} Ly{Ki(aJ aP Ar Ax bA bQ bV cN Cs cT dA dG Fa Fr Id Je Ji Jl Jn Ky Lx Nn Nr Nw Oh On Ow Pe Ql Qv Rf Ri Sr Ur) Ri(aJ aP Ax bA bV cN Cs dG Fa Ji Kk Nw On Ql Sr) Sr(bH Co dJ Ir Iz Qg Qu Ur Vo) Wm(Et Ji Jn Jp Jq Jr Nx Qd) Ql(bV cN Cv Fa Ji Lx On Qv) Co(Fa Jn Ld Nr Pe Rf) Ur(Cv Iv Jn Jr Ow Vt) Fa(dA Je Qu Rb tF) Ji(aW cI Io Kg Mr) Nw(dA Io Ne Nh To) Qu(bV Cs Lx On) Ld(bW Cv Mm Uf) aW(Is Jl Mr On) Iz(Is Jl Nn) Uf(Cs Kl Vo) cN(Iv Jn Rf) Tn(On Uh) Kg(Is Lh) Vo(Ke On) BaKl LxNh QybA bVfP} fP{bV(aC aD aM aW bB bF Bo bR cA Cs cU Cv cW Dc dF Dk Et Fa Fr Hx Io Iv Ji Jl Jn Jq Jr Jy Ke Ks Ky Lu Lx Ma Mr Ms Nc Nk Nn Nw Ny Oe Oh Oi Om On Ow Pe Pf Po Qe Qg Qv Rh Ri Sr St Uh Ur Ut) Fa(aJ Al aP aW bA bW cS cT Cv cW Dc Fr Hb Hx Io Ji Jp Jq Jy Kd Ke Ky Ms Nn Nw Oe Oi Ow Qd Qg Qv Qy Rf Rh Ri Sr St Tz Uf Ur Vt tF) Qv(aP cS Fr Gl Jl Jp Nn Oh Po Sr) aP(Jy Ld Nc Oi Sr Ur) Sr(Bo Lu Ug Ur) Lu(Nn Po) On(Cs Ur) LxbR QybA} Kl{Ba(aD aJ aM aP Ax Bg bP bV cN Cs Cv dA Dc dG Et Fa Fb Fy Hu Id Is Iv Ji Jl Jn Jq Jr Jy Kd Ke Kf Ki Kk Kn Kp Ky Lh Lj Lx Ma Md Ml Mp Ms Mz Nn Nr Nw Oa Oe Oh Oi On Oz Pc Pd Pe Pf Po Qa Qd Qe Ql Qu Rf Ri Rj Sr St Ua Uf Up Uv Vt Vv tF) Jn(aP bV bW Cv Fr Lx On Pf Qg Uf) dA(Et Fr Nn Nw Sr Uf) Rf(bW Cv On Uf Ul) Et(bV Lu Lx Sr) Nn(Cv Jy Ki Ri) Lx(Ez Ow Ql) Sr(Ki Qg Ri) Fy(Co Uf) Nr(Cv Ji) bV(Ez Is) FatF JicZ JyUf OnOw UhbA} Co{Rf(aM bA bQ Cq Cw Hu Id In Iv Jn Jr Kz Mi Ml Nn Nr Ny Or Pb Pi Ri Sr Uv Vt) Fy(aM bH bQ bX Cx dA Hu Jn Kz Mv Na Ow Oz Pa Pc Qy Ri Vo) Kz(Dc Fr Jn Jr Lv Lx Nn Nr Nw Pe Tn) Pe(bR bX dA Db dE Hu Je Pa Qy Ri) Jn(aD Db dC Lx Nn Oe Oi Po) Je(bA Lx Nn Oh Pf Po Qa) dA(Fa Ji Nn Nr Pf Po Sr) Im(aW Hu Kk Tn Tv) Is(bR bV Hu Ur) Nn(Pd Ri tF) Nr(bQ Db Iv) Lx(Hu Ql Qy) Cx(Ji On) Qy(bA cT) Qg(Po Qa) Jr(Ri Ur) FatF JibQ SraK} Ji{dA(Af Ao aW Bg bN bR Cq dB De Nd Qg Up) bX(bP bV cZ Fn Hu Kg Lu Qg Qv Ri) Po(Hu Im Jo Ms Nx Of Oi Pb Qc) Of(Lx Nb Nn Nt On Pa Pe) My(Fr Jl Lx Mv Nn Ok) Kg(cZ Db Fy Nr Rf Ri) Ms(Io Jr Nn Oh Wm) Ii(Db Kz Nn Ql Rf) Pb(Io Jl Nn On Pe) aK(bN Qg Qv Ri Ur) cZ(aW bN Cx Qv Vo) Im(Io Iz Jl Pc) Qc(Cx Oh Ok Qa) Vo(aV Nr Rf) aW(bN Db Mr) Hu(Bg Iz) Io(Jl Na) Kz(Ir Ur) bN(bP dJ) AoaV CxQg WmOi LxHq NcNe JoOn JtRf KocI UraU} Kg{Fy(Ad As bH Cp Cq Cu Cw Dc Et Hq Hv Hw Id Ij Ir Jn Jo Jq Kd Ke Kn Kp Mm Na Om Pb Pi Qa Ql Ra Rb Ri Rj Sr Up Vp Vt) Jn(aD aE bM Ki Oc Oi Ri Sr Uv Vt) Jr(aM Hu Nc Nl Oz Qy Ri Uv) Qa(Et Fn Fw Qg Rf Ri) Is(Ao Sr Tv Uv Vt) Uv(dA Nr Pd Rf) Sr(aK Ql Ri) bA(Et Qc Ql) Cx(Jq Ke) Tn(It Qe) Rf(Lh Vt) tF(cW Fa) CwKi TvIt InUr PdaD} dA{Oi(Cs Hu Iv Ki Lj Nn Nr Nw Oa Qd Ql Qy Rf Ri) Fa(Bg bR bS cA dH Hq Mk Oz Qg Qu Ri) Sr(Ao Bg bR bS Jo Nc Nl Qg Qu Qz Vo) aD(bW cA fR Gp Iv Ky Nc Ri Uh Ur) bR(aJ aP bW cN dG Jl Nw Po) Qg(aM Cs Ml Qa Uv Vt) Ao(Et Is Nw Rf St) Ki(Kz Nr Ri) Nw(Al Cs Ms) Ur(In Pi Uv) Po(Bg bS) Vt(Bo Ri) bN(fR On) NnQu MgOw MsQl IvaE QeaW cAcN} Sr{Ki(aK aZ bX cC Cx Db dJ Fn Qg Ri Ur Vo) Qg(aK aV Bb bX cK Iz Jg Ko Kz Vo) Ef(bA Fa Jy Lx Nn Qx Rf) aK(bH bX Fw Jr Ju Oe Ur) Ii(Is Jn Jr Ql Rf) Vo(aV Gp Jr Nc Ri) bX(aJ bP dJ Ri) cK(Nc Nl Oz Qz) Iz(Hu Im Je) Kz(aW Jo Qu) Ur(aL Hf Pa) Cx(cN dJ) BaSs BgHu EtJt RibP bNdJ} Kz{cN(bR bS cA cL Io Jn Jr Nr Nw Oi Ql Rf Ri Uk) aW(Cv Fr Jl Jq Jr Jy Lx Nw On Qe Uh) Ki(aD bV Ky Nw Oi Qv Ri Ur) Lx(bS cA Je Lu Qu) Ur(Hu Jr Po Ri Vt) On(bP cI Jg Jo) bV(cA Qu Qy Ri) Cv(cI Cx Qn) Ir(Is Jr) Qu(Ba Nn) Ri(aJ bA) Uh(Tn Tv) IiJq IsIu JobA} Oi{Jr(Et Im Is Li Nn Nw Oh Pc Po Qa Ur Wm) Nn(Hu Im Jn Lv Ne Nh Ns Po Qa Qe) Jn(aW cN cZ Ki Pc Ri Ur Wm) Im(cN Ki Lu Lx Oh On Po) Po(Is Lv Nh Pb Qa) Ql(bV cN Cs Rf Ri) Rf(Ki Oz Ri) Lx(Qa Qb) CsQy NrKi IsaW IvcN} Ri{Jn(aW bP cN Iu Jo Ki Ms Nc Ur) bV(aX Iv Ki Mr Nc Pc Ql Rf) Jr(aW bP cN Jo Ms Nc Ur) Ki(Ax Cs Fa Nr Pe Rf) aW(Im Iv Mr Qe) bA(aK Fn Nl Pc) Rf(Ao cN Lu) Ql(bP cN Ms) Ur(It Iv) Pc(Ax Fa) bX(aP On) MrcN TnOz} Lx{Of(Hw Ij In Ir Iv Jn Jq Jr Js Lv Na Pi Qa) My(Ij In Iv Mw Qb) Pb(In Iv Jr Po Qa) Qb(Il Ms Ns Pg) Im(aW Io Iz) Bg(Hu Je) Iv(aW Hq) Pa(bV Tv) Pi(Mj Uc) AoJe NsMp LvNa bRbX} Im{Iz(Cv Dc Fr Hu Id Jq Kd Ke Vt) aW(bC bW Cv Ju Ki On Uf) Tv(bW Ki Uf) Jr(Ih Mm Ns) On(Io Lv Ns) Nw(Io My) cN(bS cA) CvVo IiVt QubV} tF{Fa(Al Ao Ar Bg bP Cv cW Hu Iz Ks Lu Mg Ms My Qu Qy Tz Ua) Nn(Ao Iz Lu Mg) Cs(Cv cW) NcbV QvaM UrcW} Rf{Ao(Hu Je Jn Jy Ql Qy) Ii(Is Iv Qa Vt) Oz(aW cN Lu Tv) Cv(Cx Vo) Dg(bW Uf) Iz(Hu Iv) ApUf BgMw NccN JgOn UlVo PabV} Jr{Ur(bX Ki Ms Nc Oz Pa Pc) Et(Io Lu Ms Nn Ns) Ms(Nn Nw Po Wm) Nw(Hu My Ns) PoNs FrMy QcQe QvPa OnPb bNcN} aW{Is(Al aM Mr Nc Nj Nk Oz Pa) Qe(Iv Jy Mr Qc) Oz(Jl Jy Mr) Iv(Mr Nw) Pa(On Pe) NcJn} bA{Qy(aL Bg De Hu Iz Mv My Of Qu) Fn(Ki Nc) Qg(Pb Ql) Jy(aF Bg) CvCx HuIz IsJo UrPa aMaV} Qa{Qg(aK Cq cZ Fn Iz Jt Ki Uc Vo) Fn(Ki Ur Vo) PoJo FrMy MiOf HuIz} Jn{cN(bR Db Nc Nl Oe) Ii(aD Fy Vt) Cv(Jt Vo) AoJy FrMy MsUr QcQe JoUv} Fy{bH(aF aM Bb Hq Ii Jo Ki Vo) Ii(Mw Qe Ql) ApUf IzQy} Po{Jo(Et Iv Lv Na Ok Pe) Nw(Ii Ms Pa) BgJe EtIo FrMy} Cx{Cv(cN Cs Fa Ql Qx Tn) Jq(cN Ur) Om(Bg Of)} On{bX(Iz Ki Nd) Lv(Of Pb) Hu(Bg Iz) AxPa MwMy HwOf} bR{cN(bQ Is Iv Mr) bX(aJ aP dG) dG(aK bN) cXfR} My{Fr(Mr Qb Qe) Mw(aF Ir Mt) WmNy LvNw} Hu{Iz(aM cT Is Ml) Qu(cT Ow) BgMw} Nw{Ms(Io Wm) To(It Oz) AxPa LvIo IjOf} aV{Fa(bS cA Hq) Ur(In Uv) aDfR} Mp{Nd(Ir Mj Na) NsLv} Iv{cN(Db Oe) InaM QgbV} Ki{Db(bV Cs) Fn(Ij Pe)} Ao{Jy(Et Nr) IsUr} Bg{NrMw TnQy JePf} Ml{Qg(aM bH cN)} Tv{MwIz QcQe StOz} Ql{CwOf IiIs OebP} Cs{CvHf QuQt} Wm{EtMg MsQd} Fa{EfIz OzcK} Nn{LvIo NcNe} Qc{Qe(Mt Mz)} Qy{cT(Mg Qu)} Of{InbQ OmbN} Ur{Uv(aK dJ)} bX{JlOe KcbP} EtIoLj IiIsVt QvOzcK JyaMcI bQcNdH

Figure 8 Continued

Constrained panels with 3 analytes, where 1.0E-8 >= 'AUC p-value' > 1.0E-9. Contains 13,604 panels of 7,079,861 total panels evaluated. :
Aj{Kx(aP As Aw bJ Bn Cq Ct Cu cW Dc Dk dL Ed Fb Fr Fy Hw Ib In Ir Jt Kd Ki Kn Kp Kr Kz Lu Md Mz Na Nb Nm Nt Ny Pb Pi Qt Ra Rb Rf Ul Up Uv Wm) Qe(Ad As BA bV Cp Cq Cu Cv Cw Dc Ez Hv Hw In Io Ir Jn Jq Jr Kd Kn Md Me Ml Mr Mu Mz Na Nf Oi Om Ow Pb Pi Ra Rf Rh Rj Up Ut Vp) Nr(aP As bA Bc bJ Cq Cv cW Dc dG dL Hv Hw In Ir Jn Jr Jt Kd Ki Kn Kz Lh Md Ml Ms Mz Na Nk Nm Ny Pb Pi Qy Ri Up Uv Vp) Fb(Ad As Cp Cq Cu Cw Dc Fy Hv Id In Ir Jn Jq Jr Js Jt Kn Kr Kz Lh Md Na Nm Om Pb Pi Rj Tn Uc Up Us Ut Vp) Is(aD aJ An aP bA bC cW dG Fa Ib Io Kd Kn Kp Lw Nm Nn Ok On Qv Qy Ra Rf Tz Uc Ud Ul Us Ut Uv Vt) dA(aD As Aw bU Cq Cw Dc Gl Hu Hv Hw Ib Ir Jo Jt Kd Kp Kr Mr Mz Na Nb Pb Qd Ql Ra Rj Uc Ul Us Vp) Mq(Ad aJ An aP Bn bR bV Cw Et Fa Im Io Iv Ji Jq Ke Kn Ma Mz Nb Nm Ns Oh Pf Pi Qa Tn Uc Ut Vt) Pe(Ad As aW bA bR Cp Cq Cu Cw Dc Et Hv Hw Ij In Ir Kn Kz Lj Lu Lw Ly Na Nl Om Pb Pi Ql Ul Up) Nf(An aW Bc bW Cq CS Et Fy Hv Hw In Jv Li Lu Mm Mt Mx Ne Nv Pb Pi Pk Qg Qy Up Us Uv Vp) Pf(aA Ad As Cp Cq Cu Cw Dc Hc Hv Hw Id Ij In Jq Kd Kn Kr Me Na Om Pb Pi Ra Ri Rj Up Vp Vt) Et(As bV Cp Cq Cu Cw Dc dI Fp Hw Ij In Ir Jn Jr Lu Ms Mu Pb Pi Ra Rj Uc Up Uv Vp) Qy(Ad An Cq Cs Cu Dc dL Hv Hw Ij Ir Jq Js Jt Kn Kr Lh Lw Md Na Pi Pk Rj Ud Up Vt) Iv(aD aJ bM Cp cS CW dF dG Di Dk Fr Ij Jl Jv Jy Lh Lu Lw Md Ml Nt On St Uf) Po(bR bV Co dI Ez Id Jv Ke Kf Kg Lh Lu Lw Ly Md Ok Om On Rb Ul Ut Uv Tj) Ni(Aw Cp Dk Fr Jm Ky Kz Mt Mv Nv Nw Ny Ok On Oz Pg Pi Qt Ua Uf Ul Uv Wm) Ez(bV Cp Cv Cw dM Fp Fy Hw Id Jq Jy Kd Kn Kr Md Nc Om Pi Qa Ri Up Vt) Ql(aM aP Cu dG dL Fa Fy Hu Id Ij Jq Ke Lh Lw Me Ms Nm Ok Ri Tn Ut Vt) Mr(As Ax Ba bR cN Cp Cu Dc Hw In Ir Jq Lh Lw Md Me Nn Ok Tv Ut) Pk(Ad aM AW Bc bE CS Ef Fn Fy Ij Jq Ma Oh Om Oz Us Ut) Ba(aD aM As Ed Ib Jt Jv Kd Kp Lw Mj Mz Nm Ny Om Pc Tn Ut) Nn(aD An bA bJ bV Dd It Jt Kf Ki Lh Lw Mj Ms Nm Ny Ok Ph) Lx(Ad Cq Cu Cw Dc Dp Hw Ib Id In Ir It Jd Jn Om Qa Up Vt) Mw(Ad As bA Cq Cu Cw Hv Ib Ir Kd Kn Kr Na Pb Uc Ud Us Vt) Fy(aA Ad bO Cq Cw Hb Id Jq Jv Ke Nc No Om Pi Qv Ri Up) Me(Ar bZ cN Cp Cw Dc Fa Fr Im Jt Kk Li Lv Ma Mn Mu Pd) Jn(Ad bC bM Bn dL Hv Ib Id Io Jy Kn Kp Mz Om Ra Up Vp) Rf(BC cN cT dG Hu Ib Jl Kd Md Nm Ny On Ow Ra Ud Ut) Hu(aP dF Fa Fp Hx Im Jv Kf Nt Ny Ph Rb Tn Ud Ut) Jr(aP bA Bc cT CW dG Hv Jy Ki Lw Pd Qt Qv Tz) Vt(aA bA bQ bZ cT cZ Dp Ed Fa Ma Oh Oz Pd Rh Ur) Qt(Cs Cu Cw Dc Id In Kn Lh Nm Ok Pi Tv Ut) Ri(Ad aP bV Cs cT dG It Ji Jl Kz Lh On Ow) Ef(As bM Cp Cq Cw Hw Ij In Jv Pb Uc Uv) Fa(cT Js Kg Md Mi Ml Mz Ny Rb Ul Uv) Qa(aW bA bV cN Cp Jv Ma Mj Nc Qc Ur) Om(Af Cs cZ Ed Fn Hc Kj Lj Oa Og Ow) Pd(bA bN bO Ch dM Gl Ml Nk Rh Tn Uv) Jl(bA bO Hw Ij Jd Jv Kz Ly Nc Tn) dI(Aw dL Fp Hx Id Jq Ke Kn Mz Nb) Mu(Ad Ax Ed Hw Id Ma Nt Oh Qv) Kz(aJ Dc Dk Je Jp Kf Kn Lh Tn) bV(aM bR Ed Ib In Js Ow Pc Uv) dM(aM It Js Mv On Ow Qd Qn St) bA(aM bR Ji Jy Kr Ly Nc Oz) Dp(Ad Cs Cw Dk Jt Ke Lh) Id(bX cZ Ed Hc Ly Rh Us) Im(dG Io Jq Ms Oe Oi Ul) Jd(bC bM cM Cv Jj Mk On) Fp(An Bc cW Gl Lu Rb) On(aW Ax bR bX Oz Tn) Ut(aF Ao Cs Lj Ow Oz) eC(Dd Jt Kc Mj Ph Ra) Cw(Je Kr Lu Ms Us) Ml(cN Gl Ki Qd St) Jq(Ax Cs Fn Ow Wm) Jy(aD aM Ax Cs Ed) Fr(Ed Hc Ij Pi) Ly(aP Ok Ow Uf) Kr(dG Ij Lh Nm) aA(Ji Nl Oh Wm) aM(bF bJ bQ cT) bR(Ad aP It Ok) cZ(Ad Cp Kn Ok) Fn(Ke Kn Pi) Tn(Mt Nj Pa) Tv(Gl Rm Uh) In(bE bZ Ur) Hc(Ad Ke Ok) cN(Ij Kq Ra) Dc(Ow Wm) Ed(Cv dG) No(bC Nk) Lw(Cs Nd) Ji(aW Lu) AxJv BoIj MpRa NddG KnUs KqPb UvbQ PibW bJcT} Kj{On(As Ax Bb bF Co Cp Cs Cu Dd dM Hq Hu Ir Js Jt Kf Ki Lj Mk My Mz Nm Nq Nv Pc Po Qa Qe Ra Rh Uc Ud Vp Wm) As(Ba bV Cs cZ dI Dk Ed Ez Fa Gl It Jk Jl Kz Mq Ny Oa Oh Om Ow Pj Qb Qd Qg Qt Ri Uf Uh Vt) Ni(aA bM Cv dA dG Dk Dp Et Gl Jl Jt Kr Ky Li Ly Ms Mu Nf Pb Pg Qb Qd Qy Ut Uv) Iv(aA aP Aw Bn bQ cN Cs cT dA Et Hv Ir Jo Kp Lh Me Nm Pb Pd Pf Qe Qy Rj Uc Uv) Mq(aA An bA Cq Cv Et Hv Jo Jt Kz Md Me Nm Ns Oh Pb Pc Po Qd Rj Tv Uc Vp) Cq(aJ aK bE bM cS cT Gl Im Jt Lw Mr Nw Oh Ow Pj Pk Qd Qg Uf Vt) Na(aA aJ aP Ar aV bE bP cN Cs Cv dE Dp Fr Je Jh Mm Nv St Ut) Nf(Ax Ba dI Fn Gl Hw Im Je Jl Mp Mr Mw Mx Mz Nm Pf Tv Ua Ul) Ri(An Aw Bn Cs cT Et Jd Kd Mj Mr Mx Nn Pb Ph Qe Ql Ra Tv Ud) Uf(bA Cp Cu Dc Hv Hw In Ir Jn Jo Jr Ke Lh Ml Mz Pb Pe Rj Vp) Uv(aA aV bQ bV Cp Cu dJ Hu Jt Kn Lw Mm Mr Mw Nw Ok Ow Wm) Pb(bA Dk Fb Fn Im Jt Ke Lw Mn Mr Mw Ok Pf Pj Qd Qg Qy) Pd(aW bR bS Cv dL Fp Is Jv Ki Kp Nc Oh Oz Qe Ql Rf Uu) Cp(Ax bR bS bV dI Hq Lw Mw Nw Oh Om Pf Qd Qg Us Vt) Cu(Ax cZ dI Dp Gl Hu Im It Mi Nc Nl Nw Qd Tz Vt) Nm(Dp Ed Fb Fn Gl Hu Im Lx Me Mr Mw Oh Om Qt Uh) Ok(aK aU bO bR cK cY Fy Hf Im Kz Lx Ma Nn Po Qe) Up(aJ bE bF cN Dc dE DG Dp Ef Je Lw Nt Rh Ut) Vp(aJ aK aL aV bE cN cS cT Fb Gl Im It Mr Nw Qd) Me(Ar Bc Hu Jl Ml Mu Mz Nv Pg Ql Tv Uc Ul tF) Kr(aA aV bE Bo Ef Fr It Jp Jt Jy Kf Nv Wm tF) Vt(aK bF bV Cs dJ dM Hu Lw Ly Mm Pf Ph Qg Tv) Pe(aA Ax Bn bW cT Cv Dd Im Ly Lz Nj Oi Rb Uc) Om(aW Dd Ib Iz Jd Ke Kp Ms Mv Ng Nq Qx Us) Ut(aM Ax Hq Hw Im Jv Kz Lj Ly Ma Oa Ow Oz) Ra(Dk dM Fn Gl Jk Ki Ma Mn Nw Pk Ql Ua) Jo(Ax Cv dI Dk Fn Mn Mr Mw Pf Qd Qg tF) Lh(An Ax dM Hc Jy Ms Ow Ph Rb Rh Rj Us) Po(aA Bn Dd dM Kg Ly Md Nr Ql Ud Ul) Et(Ax bV Ib Kz Md Mj Nr Ql Tn Ul Us) Uc(cZ Dk Dp Fb Im It Lx Mn Mw Oh Qd) Hv(Dk Fb Gl Im Lw Mr Mw Nw Ny Qd Qg) Tv(bV cZ dI Fn Fr Jm Mp Mu Qg Qn Tn) bA(aA dN Kz Lx Ly Mm Mp Mr Mw Rj Us) Dc(aA bC bW cN Jv Lw Nc Oh Pi Rh) Fy(bC bO bV Dp Hc Jn Jt Nc Oz Qz) Qe(An aW bV dK Jv Md Nr Oi Ql Ul) Kd(bM bV Cs dA dI Dp Fa Hc Ki Ow) Nn(aA An dM Kx Og Oi Pc Ql Rf) Ma(aM An Kg Md Mr Mx Rb Ud Ul) Tn(bJ Dp Gl Nr Ql Qt Rf Rm St) Js(bV Cv Dk dM Ez Mn Oh Qy Ul) Kf(cZ Dd Kg Ly Md Mr Oh Oy Oz) In(Ba Gl Hu Im Mr Nw Of Qd) Ir(Fn Gl Hu Im Mw Nw Qd Qg) Kx(Bc Dd Kg Mj Mu Nb Nr Qd) Rj(Dk Fb Fn Im Nw Ny Qd Ua) Hw(aJ aP cT dE Jy Ow St) Is(bI cT Hb Je Lu Nc Ph) Jn(Ax dA Io It Nw Qc Qd) Kz(Ax cT dG Kk Mn Nr Pf) Mz(Gl Lx Mr Mw Oh Uh) Ud(Ez Lx Nr Qy Uh tF) Jt(Gl Jk Jv Ly Mr Nw) Ke(Cs cZ dI Ph Sr Wm) Rf(Aw cT dL Ed Mu Nb) Lw(aW Ba Kp Li Qz) Jd(Ao bM dA Og Pf) Ql(An Cv dG dL Mx) Ul(Db Ez Fp Kn Qm) Nr(An dA dL Ow) Hu(Ax Cs Ed Kp) Im(Bn bV Mx Rb) Jr(dG Ez Mi Nw) Oh(Bn Dd Kg Md) bJ(Hx Mj Or Rb) Lx(Dd Ib Md) Ml(Cv cZ Jk) Ji(aA dK Ms) Us(dI Fb Qy) Pc(Ax bV Pf) dA(Oa Ow Qd) dG(bR Dp Fp) dM(Ph Qm Qt) Aw(Dp Fp) Ba(aD Qa) No(Nk Uo) Ly(dL Jl) Mu(Bg Fa) Sr(Ch dL) Kg(Dk eC) Kn(bG Rh) Kp(Ed Qt) Ny(bF bM) Pj(Hx Md) bV(Mr Oz) cT(aA Jl) AdaJ CsJy DbMx DdUh EzPh MjQy MtaM NbcZ IitF QabW JhPi JqaW} Uu{Cv(Aw bZ cN Cp Cq Dc dF dG Gl Ha Hv In Ir Jg Jo Ke Kr Lv Mm Mz Na Nb Nm Nt Ny Pb Pc Ph Qx Qz Rj St Uc Uh Up Ut Uv Vp) Et(aD Bc bO cI Cq Dd Dp Hv Hw Ib Ij In Ir Jg Jt Ma Md Me Ml Na Nb Ow Pb Pc Pd Qa Qe Qt Qy Rb Rj St Uc Up Us Vp tF) Nw(An Aw Bc dI Dp Ed Ez Fa Fp Fr Ib Id Kz Md Me Ms Oz Pf Po Qa Qt Qw Rf Tv Ud Uf Ul) Mu(Ad An Aw Cw dA Dc Dl Fa Fb Fp Gl Iv Jt Kd Ki Kz Lv Me Mr Nf Nm Oe Ou Qt St Ur) bV(Ad aX Bc Cp Fb Gl Im Jg Jk Ki Kk Ko Lh Ma Mn Mt Oz Po Qt St Ua Uh Ut Vt) Nn(AD As AW bJ Bn Cp dG Ez Kn Kp Kr Lu Md Oz Pi Qg Qv Rb St Ul Ut) dM(An cT Dc dF dI Fa Fr Fy Gl Js Jt Kd Li Lj Mm Nt Oa Oh Or Ow Pg Pi Uh) cN(Ax bA cT Ez Fy It Jg Js Kn Ly Ma Mw Nf Nv Oh Ow Pj Qd Qt Ri St Ut) Kx(Ad cT Cw dF dI Fa Fb Fy Iv Kd Mr Mx Nv Oz Pc Pf Po Ql Qt Qy Ut) aP(Ax bS Cp Ef Fb Ij Jt Kd Kf Ki Kn Me Mn Mt Nf Nk Ny Po St Ut Vt) Qd(aM Bc bJ bO dI Id Iv Je Kf Lu Ma Me Ml Nf Ok Oz Pk Ql Qt Qy) Rf(aM Aw Bn bQ Dc Di Dl Ez Fa Iv Kn Lh Nm Ny Pd Pk Ql Up Ut Vt) Uh(Hv In Jt Jy Kr Lh Md Mq Nb Nf Nm Ok Pd Ph Qa Ra Rj Ul Uv Vp) dA(Ax bA Fb Gl Iv Jj Jk Li Lx Ma Mn Mp Mr Mw Ou Ql Qy Ri St) Po(bA bR Co cT Dc Id Kd Lu Mq Ow Pk Qg Qv Ur Ut Vt Tj) Fr(Aw bA bC bG Bn dG It Jo Jv Md Mm Ra Uc Ul Us Ut Uv) aJ(Ad Ax bA Bc dI Ef Ez Id Im Lh Ly Mw Ow Oz Pd Qt Vt) Nr(BC bW Ez Iv Jv Kf Ki Ly Ms Nc Oi Ok Pk Qv Qy) Ni(aD aK Cp Cs cT dF Jj Ko Ky Li Mp Ow Qa Ql Qy Ri) Qe(Aw Di Ih Jg Kd Kf Kn Ly Ms Nc Oe Pd Pk Qg Ql Vt) Fb(bQ cT Dc Hu Jg Kd Kf Kn Me Mq Mx Ow Ul Ut Vt) Hu(An cT Cw dI Ed Ij Js Kd Kn Nm Oa Qv Ri Ut) Jy(bF bR bW Cw Dl Gl Iv Ma Me Mw Oa Qb Qy Tv) Ql(aD Ax cT cW Dc dF Di Fa Jj Jp Jr Kd Qv Ri) Pk(cK cT dF Dg Jn Jp Jq Jr Kf Mn Mq Pf Qg Qy) Id(aK Bo bP bW dJ Jp Jr Lh Ma Oh Qa Rh Ur) dI(aD Bc cH Cp dL In It Jp Kd Mx Mz Nb Uv) Is(AD aM bC Cw dL Hc Jg Ju Kd Nj Og) Vt(bF dF Ed Lu Ly Ow Oz Pf Qg Qt Qv Ri) Jn(aD aW BC cT Ez Hc Io Me Nc Ut) Pd(aW bA bW Co Ky Lh Oi Qv Qy Ri Uf) Qa(aW Bo cT eC Jj Jv Ki Kr Oi Ur) Jr(aW Bc bP Ez Jg Kr Nl Ow Oz Ul) Kf(bO Co Jv Kd Mm

Ky Lx Rf) Ms(dA Ji Jp Mq Nr Pc Po Ql) Jd(aD Ao aW cN Co Nn Og Po) eC(Cw Hw Ij In Jq Jr Kd Vt) Fa(aM cN Dd dL Et Mu Ra) Lw(bX Cx dE Fy Kk Mq Ra) bV(aM bR Et Hu Jo Mj Wm) Lu(dA Ma Pd Pj Pk Vt) Lx(Bn Dd Ly Ni Nm Uc) Tn(aM Bc Nj Nk Pj Rg) Ml(bW Jp Mn Mq Uf) aD(aA dF Jr Ni Ql) Id(bP bZ dA Rf) Ki(Jn Nr On Pe) Og(Jl Nn Po Un) aW(Iv Mr Pd Un) Co(bQ Qa Rf) Wm(Fy Kd Kk) Tv(Mw Nw St) Kq(cZ Fn Io) Ql(cN cW Po) On(Iu Lj Pk) aE(Ba Jl Jr) bM(bQ Jq Kk) Cv(Fp Nn) Fy(Il Uf) Nr(dL Mq) Iv(cN In) Ji(cK cZ) Rh(Jh Mu) Rf(bI cW) Un(Iu Ow) aA(Is Ke) NnaN MncW MqKy NiKk QacN JncI} Og{Jv(aP bA Et Ez Jy Lh Li Lw Lx Mn Mr Mw Nf Nt Nv Nw Oh On Oz Qa Ql Uf) Nn(bO Co dA dM Hv Hw Ii Ij Im Ir Jo Jt Mi Mr Ms Mt Nb Pa Qu) Mq(aJ bO bV Cv Dp Iv Jk Jn Jp Js Li Me Mr Mx Mz Ne Ns Pa Pc) Is(bO bV dM Fr Ii Jg Jn Jt Kx Lh Mi Mm Mr Mt Mz Nb Ni Pc Pf) Et(Fr Im Iv Jn Jq Lh Li Mi Ml Mr Mt Mv Nb Nt Pa Pc Pe Pf) Wm(Ih Im Jd Ki Kx Li Lj Ly Mr Mv Mw Mz Nt Ny Pd Pg) Qe(dM Hw Ir Iv Me Mi Mr Mt Na Nb Oi Pd Pe Pf Qa) Jd(Bb bV Cs Cv dA Iv Ly Ms Nq Ow Oz Pk Qy Ri Ua) Ki(aP Ba cT Cw Dl Fy Ji Kz Lx Mx Nr Oh On Pf Ri) Nw(Hv Hw Ii Ij In Jg Jn Jq Lh Mi Mr My Mz Nb Pc) Oh(Fr Ii Im Ir Iv Jq Lh Li Lw Mi Na Nb Ok Pe) Qa(Co Fn Jg Jn Jt Lh Mr Mt Mz Pc Pf Qg) Un(aW bO Ih Ir Ju Nl Nm Qg Sr Uf Vo) Fr(Iv Jn Lj Lv Lx Ne Nt Nu Om Pe) Jl(aW Dp Jn Jr Jt Md Mm Mz Pk Ri) Kx(aM bV Cv Iv Jn Jr Ly Oz Ql Qy) eC(Ad As Cw Dd Ij Js Kn Na Nf Uc) Lw(Cs Fn Jn Li Mv Nt Ok Pe Ql) Co(dN Ij Im Jr Kq Nr On Po) Fp(bW Jp Mn Mp Nt Nv Qd Uf) dM(Hu Jn Jy Nc Nr Ny Ow Qt) Mu(Bg bV cT Mm Oa Rf Rh) Nf(bV dG Ke Li Mm Qv Ur) Qb(Jg Li Lv Mm Nh Nt Pf) Lx(Jg Jj Jt Ly Ml Pc) Jr(Jg Lv Mn Mw Nt Sr) Ni(aA Jg Li Pf Uf) Im(cN Nh Ok Pd Pf) Iv(aW Cv Ql Ri Uf) Rf(Ao bV bW Cv Uf) Me(Ax Jg Mn Pf) Ji(bE Fn Kg Ri) Sr(aA Iz Oz Ql) Jq(aA Li Nu Pf) Pk(aJ cN Hu Ql) bV(bO Mr Nc Qy) Lv(Li Mm Pe) Nh(Li Mn Pf) Ri(Ax cN Po) Ok(Jn Lj Pe) On(aF Bb Mw) Nu(Mw Ny) Mm(Jn Mv) Om(Mg Mz) bO(Fa Kq) AxQl JgPe JjLh NxaA UfdA dFfP} Ni{Nw(aF bX Hu Im Is Jl Lj Lw Mm Mq Ms Nn Of Oh Oi On Pc Qa Qe) Po(cN Et Hu Im Is Jl Lw Mm Mq Ms Nn Of Oh Ok On Pc Qe) Jr(aK Fr Im Is Jg Jl Kg Li Mm Mn Mu Oh Ok Om On Qe) aA(aD aW cN cT Et Fr Jg Li Mm Nn Oh Om Pk Qa Qe Ri) Vo(Ax Cv Et Id Is Jq Ma Mp Pd Pe Qe Ql Rf Uh Vt) aW(aP bW Co Cv dA Et Hf Kz Mt Ny Oh On Pd Ql St) aK(aC Ax cT Fr Jd Lj Lx Nc Ne Nn Oa Pe Pf Vt) cI(aD aP bR bW Jd Jq Ms Mu Nf Nj Ow Pc Uh) Lx(aF bR Co dM Hq Kx Lj Lv Mn Of Pb Qa) Un(bA cN Co Cs Fn Qg Qv Ri Ug Ur) aD(Bo cN eC Jd Jn Kg Kx Mu Nk Nr) dM(Et Is Jq Lw Ne Oi Ow Pf St Uh) Fp(Et Jg Jp Jv Lw Mm Mp Oh Ug) Jj(Hf Js Kz Mn Nf Nn Nx Oh Pe) Ly(Ax bA Co Cs Fa Kx Ok Om) aE(aM bS bW dA Jd Jn Ql Qy) Mu(aF Li Mn Oh Pe Qa Qb) Iz(Im Is Jn Nr Pe Qe Tn) Jv(Ar Bo Fa Ky Lj Rf Ri) bV(cA cV eC Hu Mq Nk Ql) Nn(Ao cN Lv Mq Qe Qu) Kg(cN Dp Jn Lh Ri Sr) bA(aL aQ cN cY Me Pc) Ax(aM Dp Hu Me Nk) Co(Jn Oh Pe Pf Tn) Cs(aV bO Io Oi Pa) Qb(Et Fr Mm Mn Om) Ki(Bo cC Fn Nr Sr) Ri(Fa Ms Nr Ql Qu) aJ(bN bR Cx Hu Pk) My(Fr Jd On Tn) Kx(Dp Lw Sr Vt) Nf(Qv Ug Ur) Hu(aM bM Ur) Qa(Et Mn Oi) Ji(Ao Jl Pc) Jo(cN Dp Pk) Oh(Lv Mq Oi) On(Im Lj Ms) bP(bN Jn Nj) Tn(Bg Rg) Sr(Ir Jt) Qu(cN Mq) Kl(aP Pf) Kq(aF Of) Pk(eC Ur) AoNr BoTv CvCx FydN MmQe MnNe MseC NaPc NjQz NkQg UetF IuQl LiOi RhcN OfOk UvdJ} Jj{Me(aM Ax Cs Fr Ih Ij Ik Jd Jl Jp Jq Jt Li Lj Lx Ma Mq Mt Mv Nh Nv Pf Pg Pk Ql) Mq(aA Fr Ih Ir Iv Jg Jk Jl Js Jt Lh Li Lj Ma Mi Mr Mt Mx Mz Na Pc Pf Qd Wm) Jm(Hv Hw In Iv Jo Js Lh Lw Lx Mi Mm Mn Mr Mt Mw Mx Mz Nb Nu Pa Pc Wm) Nw(Hv Hw Ir Is Iv Jn Jo Jq Jt Lh Lj Lw My Oh Pc Pe) Et(Hw Iv Lh Lu Lv Ml Mv Mw Nb Nl Nn Oh On Pe Wm) Im(Fr Ii Jo Jt Li Mm Mr Mv Nb Nu Om On Pf Pg Qd) Nh(Hw Ii Ij Jq Lj Mp Mv Na Nn Nx Ny Oh On Pd) Jn(aA bO eC Is Jq Lh Lw Lx Mm Nn Ok Om On Pc) Kz(aV bA bO Cv cZ Jq Kk Kq Lx Oh Pd Rf Sr Vt) Mu(aA Is Iv Jl Jq Lh Li Lx Nn Ok Pf Qd) Nf(aW Hv Iu Kq Ml Mr Mx Mz Nm Nr Nu Uv) Kx(dA Hu Iv Jr Nj Nr Oi Rf Sr Uv) Pk(aK bO dA Hf Jd Ly Mr Nc Rf Ri) Mw(Hu Jv Lj Lx Mr Na Nl Ok Wm) Nn(aA Lv Mr Na Ne Ns Pd Qa) Jv(dA Jr Ly Mr Oz Pc Qe) Nx(aA Hw Lv Lx Mv Na Ne) Pd(aA Jq Li Na Ny Oh Ok) Wm(Iv Lh Mp Mv Ny Qd) Ik(Jq Lj Mm Mn Na Oz) Is(Jq Lw Lx Ok Om Pc) Pe(Jq Lw Mm Ok Om Pc) Lv(Hw Jq Lj Ne Oh) Ri(Mr Nr Qb Rf Un) Mp(Hu Ml Ne Nu) Ny(Hu Na Ne Nl) dN(bN bR Db dH) Fr(Qa Qb Qe) Ly(Lx Ok Ow) Mn(Hu Mr Ne) Lh(aA Na Pb) Ql(dA Hf Oi) Oh(aA Hu Oi) Un(Ms Nc Pa) Nt(Qb Qe) Mr(aW Na) Jd(Co Iz) Jl(Io Oz) Jr(eC Jg) On(My Pb) FyOz MvNe IdeC IjPb InUr KqaF OkaA} bO{Pf(aM aP Bg bS bV cA dM Io Iv Jn Jr Kq Lu Lx Ly Ms Mu Nw On Pk Ql Qu Qv Ri Un Vt) Fa(AD aM bM bW Cq Cu Cw dA dG Et Fr Id Ij In Jl Kn Ml Nn Oh Ow Pi Up Uv) aP(cA Et Fp Id Io Is Jd Jq Kq Lj Lx Ml Ms Nw Oa Oe Oz Qv Un) Po(aC Al Ao Bg Cs Jd Jm Kg Kq Lw Ly Me Ml Mq Pk Ql) aJ(aM Ax Et Jl Kq Lh Lx Nn Nt Nw Oi On Qv Un) Cs(aA dF Et Fr Gl Io Is Jd Jq Jv Jy Mu) Nn(aN Co dM Ju Kl Lu Lx Me Nw Oe Ri Un) Qv(Jd Jl Jn Jr Mp Mq Nf Nw Pe Ql Rf Vt) Ji(Ao aU cI dA Db Hu Io Jd Me Ql Ri) bV(Et Fy Io Jd Jn Lx Ml Nc Pk Qb Uv) Jr(aA aW bM cT cW dG dM Fr Io Nw) Kx(aD aM cT dL Id Jd Jy Mq Pe Qa) Un(aA aE Ao bM bX Io Mq Oh Rf Sr) bA(cA Dc Id Jy Kq Kz Ly Mu Oh Oi) Qa(cT eC Io Jv Mj Nw Oe Ur) Qe(cN dM Iu Jv Lu Ms Oi Sr) Nr(aA cN dG dM Io Ki On) Mq(Fr Fy Io Jn Ky Rf St) Kq(aD aM Ao cI Lj Ow Ur) Lx(aD bG Ij Ir Jd Pi) Sr(Cv Dc dF Fy Gp Jy) Nw(aM cT Kz Ow Pe Ra) Jn(aA Io Ki Lu Oe) Oh(aA cN cW Jd Vt) On(aM bM Nd Oa Pk) Pe(Ao Cv Jo Ri Uf) Is(Jv Ms Ur Vo) Jl(aW Io Iz Jv) Fr(aM Jv Oi) Et(aA Lu) Fy(bH Lu) Me(bZ dF) Jd(cW Io) Ql(aD Oi) Ur(Pk Uv) aM(cT fR) dG(Jv Ly) AxGl BaKl MsLh MtcW MwMy OwaD VtaA PkdL} Oi{Nn(Et Ih Ir Is Iv Jl Ki Kx Lj Lx Ml Mr Ms My Na Nt Nw Ok On Pa Pe Pf Qd) Nf(aA aJ aP Ax Ba bQ bW Cs Dk Fa Is Jv Ke Kf Kk Ky Pf Ql St Uf) Im(aW Fr Is Jd Jv Kx Li Lw Mm Mx Ne Nh Nw Ok Om Pc Pd Pf Qe) Jn(aA aM bP dA eC Fr Jd Li Lv Lw Lx Oh Om On Po Ql Rf) Fp(aM Dc Ir Iv Jk Ki Lh Mp Mv Mz Nh Ny Pd Pe Pk Uf) Mu(aM Ax bA bV dM Jq Jv Mi Mr Mt Mz Nt Oa Om Ow Pc) Kx(aJ aP BA bW Cs Is Jl Kq Lw Oh On Oz Qa Qv Wm) Jd(aM Ax bV cN dM Ih Iv Je Kg Mk Nr Oz Qt Qy) Po(Et Hr Ir Iv Jl Jq Mm Nt Nw Oh Ok Pc Qe) dA(aM Ar bR Fa Fb Ih Ky Kz Mr Qb Qe Uv) Jr(dM Jg Jv Lv Lx Mm Nh Om Pf Qe Ri) aA(bM Is Jg Jl Lj Ma Nw Ok Pf Qe Sr) Qa(Et Is Lw Mm Nw Oh Om On Pc Pf) Dp(aJ Ar Ax Kq Mq Oh Pe Sr Un) Ql(aW bA Fa Hu Ki Ms Pk Qv Ur) Rf(aM cN Co Iv Kz Lu Ow Pk) Oh(Is Ji Lv Me Ne Nh Nw Qe) Un(Ao bV Co Ir Mq Nm Ow Rh) Lx(Ih Kz Lj Lv Mq Nh) Pk(bV Hu Mq Mr Qg Ur) Is(Co Li Ne Pc Ur) Kz(Cv Hu Je Lw Ur) Mq(Fr Mm Pf Qb) Lj(Et Om On Qy) Ri(bV Cs Fa Nr) dM(bN Hf Iv Qm) Me(Ax cN Cs) Kq(cY Ef Vo) Pe(Ki Lw Pc) aW(Iv Mr Qe) CsHu EtLu NrJv MrOm MyOn IdeC IvUr JiPc KgdN} Jv{Pk(aW Ax cT dF Dk Et Fr Hu Id Is Ji Jl Jp Jr Ky Mm Mw Nc Ow Pe Qe Ql Ri Uf) Ur(aA Cs cT Cw Im It Kn Lh Lw Ly Nn Or Pd Pi Po Qe Ql Uv Vt) Ly(aJ cT dG Dk Id Jl Jr Kk Lw Oh Om On Qe Ql Rf Uf Vt) Nf(Cs cT dF dG Dk Ji Jl Jr Jy Ke Kx Mn On Pe Pf Vt) Jd(Ao Fp Id Im Lw Oa Oh Ow Pc Pe Po Qu Qy Rh Tn Tv) Qv(dN Et Fy Is Jr Mq Mr Mw Nn Ny Qb Qe Qy Vt) Kz(aP Ar Cs Cv Dk Je Jy Kk Kq Kx Lx Nn Un Vt) Jn(aD bV Co eC Fa In Ky Nc Oz Pa Pc Rf) Kx(Ad Ba Bc Cv Ma Mu Om Ow Qa Ut Vt) dM(Ar Db Mv Mw Nn Pc Pe Po Qe Qm Ri) Rf(Ax bQ dA Fa Me Nn Ow Oz Ql To) bV(aX Dp Hu Im Iv Mr Nc Oz Ql Ri) Cs(bF Dp Im Lw Me Ms Mu Ql St) dA(Ar Ld Lj Nr Oa Pc Po Vt) Jr(bA cN eC In Ms Nc Ql) Nr(bA bQ cN Co cT Lw) Kq(Ao cY Dc Jg Mg Oz) Un(aE Co cT Ky Nm Ow) Nn(aK aV Ki Nc Pc) Jy(aE Ax cI Lj To) bA(aK eC Hu Pc Qy) bX(Dk Jl Jq Om Qd) Ar(bQ Hu Me Pc) Iv(aW cN Fa In) Ri(aP Ax Pe Po) dN(Cv Fy Lu Oe) eC(Id Kd Qa Vt) Ji(dE Kg Mb) Oz(aP Hu Kk) aK(Id Ke On) Bo(Qa Sr) Cv(aA Cx) Fp(Jq Ke) Lu(Et Im) Mq(In Jq) Ms(Im Ql) Is(Jo Kg) Pa(Ax Pe) Pc(bQ Pf) BaaA CoFy CwKg LwJu LxbR HubQ IdbN QeaW JoPe QlcT} eC{cK(bA Cp Cu Cw Hv Hw Hx Id In Ji Jn Mr Nb Nf Om Up Vp) Ki(Cq Cw Hv Hw Id In Jn Jq Kn Ml Nb Om Rj Up Vp) Kx(aM Cq Cw Iv Jq Kn Ml Mz Na Nb Nf Om Pb Qa Vp) Pk(Ad As Cu Hv Hw Kp Mu Nw On Pi Qy Rj Sr Up) Hu(Cu Cw Hw Id In Is Kn Na Pi Rj Sr Up Vp) aW(Ad Cw Hv Hw Hx Ij In It Js Ml Nf Up Vp) Lu(Hv Hw Ij Is Jq Kn Lw Mz Na Om Qa Up) cI(An As Cw Hx Is Jn Js Kp Nf Rj Ut Vp) Jd(Cu Hv Hw In Jn Me Ml Up Vp Vt) cN(An As bA Cp Md Mr Nf Om Pb Uv) Qu(Hv In Iv Ke Mt Na Pb Pe Rj) Ms(Cu Cw Jn Jr Kd Kn Sr Vt) Kg(As Cp Js Ke Kp Nf Pb Pe) Pi(aD aP bH bI Co Fn Ra Ri) bP(Cq Cw Hv Hw Ji Kd Ke Rj) Mg(As Kp Nb Nm Ny Pb Rj) Qg(Cq Ij Jq Na Nf Pb Rj) Iv(aD aJ aP dA Ug Vo) Ny(dA Lj Mv My Nv Qt) dM(As Hx Ke Pe Ra Uv) Id(aD aE dA Ra Rf) In(Kk Of Qv Ug Ur) Qa(bH bI Co dJ Jc) Jq(Bb Cx dA Jf Ra) Ir(Kk Ri Ug Vp) aD(Dc Jr Jy Kd) Cs(Cw Lw Ut) Ly(bA

Figure 8 Continued

Sr Vt) Jn(aJ aN Kk) Ke(aK bH Ii) Of(Cw Om Vp) Ur(Ij Nf Pb) bV(aX cA Nc) Ao(Kn Mt) Co(Cu Pd) Lw(bA Me) Sr(aL Ug) Ra(Cu Vp) Jr(bH Jf) Kl(Cv Kp) Kq(aO Qt) Vt(bI Qv) BoUp CtVp DcaE MeMh QdbA JoJt KkKz KpVo UvdA} Nf{bV(bR Co cT Dp Fr Jn Jq Ju Jy Kk Kq Mn Nc On Pk Rf St Ug) aW(aJ Iv Jd Jn Jq Jr Mu Pf Qa Qy Sr St Uh Ur) Ki(aP Ax cT dA Dc Jd Jq Ms Mu Oe Oh On Pk) Ur(Co Cs Dp Fr Lu Nr Pe Qd Ql Tn Uf Uv) Qv(bE bH bM Co Is Kd Ke Me Nw Ul Vt) cN(Ax cO Cs Dc Kd Ke Ml Mr St Vt) Co(aJ Fa Is Jp Kn Pf Pk Ut Vt) Qu(aJ Ax bA Fa Kq Mn Pf Uf Un) Kg(dG Is Kd Kn Kp Nm Ok Om Rf) aA(Hu Im Lx Ma On Pe Rf Uh Vt) Sr(cK Ih Io Ir Iu Ms Of Vo) bA(bE Cv Dc Ji Jq Mg St Vt) Qg(Cs Dc dL Id Jr Kd Ke) Ri(aD Ax cT Kk Kx Po Ug) Un(Cq Fn Io Ko Oe Of) Cv(cT Cx dA Kx Pk) Fr(Ef Kl Nl Oe Ua) Lx(aD aJ Kx Mm Nl) Iz(aP Jn Jp Jr Pe) Ao(Jq Mu Rf St) Et(Im Lj Lu Pc) Lv(Jp Mn Ne Nh) Mm(Ne Nh Qa Qe) Ms(aP Jl Ql Qy) Jo(dG Jl Kn Om) Nw(Kx Mv Nv Of) aJ(Oe Qn Qw Ua) Lu(bP Rf Vt) Mu(aD aE Hu) Jd(Bg Oc Of) Jq(cI Cs Vo) Ji(cZ dA) Kq(Cu Ef) Ug(Ke Ul) BaKl BgOm CtcT FaOe FybH LwbN MnNe HubP IiJl JeKx JnKs OfUp OkPc aDdA aPbS bRdG bWdM} Jd{Iz(An As Aw Bn Cp Cq Cv cW dA Et Ib In Io Jn Js Jt Jy Kp Lh Mr Na Nm Oa Ok Oz Pb Pd Qd Rh Rj Ud Ul Vp) Bg(aM bS Co Cu Cv dA Dc dF dG Dp Fa Id Ij Jl Jn Ke Kl Kn Kz Mr Nb Nw Oz Pd Pe Qu Rh Uf Ul) Ms(aA aM Ao dA Dp Iv Jn Jr Ki Kx Mq Mr Qv Qy) Co(aM dA Ji Js Ld Lv Mr Nc Oa Oz Pd Ql Qu) Kx(Al aM Ap bS cA Cs Iv Ju Kg Me Mr Pk Qy) Ao(aA Et Fy Im Is Jn Jr Nc Ri Sr Un) My(aA aW Cs Lw Lx Mq Mw Nc Qv Sr) Kl(aA aJ bA bM bV dM Ji Ow Pf Sr) Of(Ad As Dc Hw Lw Na Qa Ra Vp) Iv(aE aW bP dM In Jo Kg Ri) Qu(Ax bA bP bX Nc Nn Pk Rf) Ly(aD aW bV Cv Fa Ql Ur) Ki(Ax Ky Kz Qv Ri Ua) Kg(aD bA cT Qa Vt) Ri(aW bV Cs dM Nc) bP(bS Oz Qy Sr Ua) Bb(Fy Jq Lx Un) Lw(Af Ap Bn Vo) Hu(aA bX cI dM) Me(aW cK dA) Pk(bM Jo Nc) bX(aD bV Cv) De(Cv Un) Ua(bV Sr) Ii(Jr Pe) Kq(Jg Uc) Kz(Io Ur) Oz(aW Qv) ApbM CsDp EfPe LxNd MvcT NcdM HqbA SrJt KeKo OeaA aPfP} Mq{Ly(cT dA Et Kx Ld Mm Mu Oh Ok Om On Qg Ql Ri Vo) Nn(Et Fp Hu Ii Im Jo Jq Lv Lx Me Mg Ns Pb Po) Qu(Ax cT Hu Im Je Ki Kx Lw Ms Qy Rh Ri Sr Un) Un(Bg Co dM Fn Ih Ir Iu Jo Nm Oe Of Ur) Et(Hu Jq Kl Lw Lx Ml Ms Nw Oh Pc Po) Is(Co Il Io Iz Jo Ms Nw Oh Pb Po Vo) Mu(Co Im Iz Js Me Mi Mz Pb Pc Qe) Im(Io Lw Lx Ns Nw Oh On Po) Jr(Fr Iz Jq Ns Ok On Pc Ur) Om(Hu In Jo Mg Ms My Ns Of) Pk(aW Io Kg Kx Ms Of Qg Ur) dA(bG cD cL cU Oz Qw Rf Vv) aW(Iv Ji Jy Me Mr Pc Qe) Lx(Ir Iv Kl Mt Pb Qa) Jq(aL Ns Nw Oh Po Vo) Dp(aP bA In Kg Kx) Lw(aL Iz Oh Po Uc) Mn(In Me Ms Ne Nh) Rf(Ii Kg Kl Lu Vo) Nw(Me Mg My Oh Pc) dM(Ky Rh St Ur Vt) aA(Hu Io Iz Ok) Fp(In Lv Mm) Jn(aD Cq Vo) Jo(dN Oh Pd) Of(Cw Id Ok) Pb(Oh Ok On) aL(bA Dc Kq) cK(bS Qv Vt) Cv(Cx Kl) Lv(Ir Js) Mp(Hq Nh) Ms(Qb tF) Io(Kx Qa) aK(Kd Ke) BaKl BgbQ DbKi DcUc FyUa MlMm MyOn IndN IzKq JyVo KgPd VtdJ PcbA aVbR} Kx{Ki(AD aM aP As Cp Cq Cw Fr Hv Hw Id In Is Ji Jl Jq Ke Kp Mz Na Nb Nm Ok Pb Rh Rj Up Ut Vp Vt Wm) Pk(aJ cK cN Cv dA Io Ji Jo Lu Mm Mr On Oz Qv Sr Uf) Ly(aP bA Jl Jn Lw Mm Mr Nw On Ql Qv Sr Ur) dA(Bg bR bU bW cA cF Io Ky Pc Ql Qw Uk Ur) Co(aA aM bQ Iv Jc Jy Lx Mr Nn Nr Qa Ri) Qv(Bc Iv Ji Jl Jn Jr Mw Nj Nl Po Qe Uv) Kq(Cq Cx Dg Ii Jo Jt Kg Oz Qu) Dp(aJ aP bA dM Jl Lu Sr Ur) Ri(Ax Iv Ji Kz Ms Pc Ql) Oz(bA Jr Lu Lw Ms Nw Sr) dM(Et Hu Jr Jy Nr Qt Sr) Un(bR Ju Nc Nj Qc Rf) bV(aM cA Iv Me Qu Qy) Lu(Jr Mr Ql Rf Vt) Jy(aD aM Bg Iz Me) Ur(In Kz Mu Pc Sr) Lw(aA Bg Kg Ss) Ms(aM Jr Mr) Io(Jr Mr Nr) Sr(Iu Iz Ko) Qy(bA Cs cT) Jn(bP Ju Oe) Kg(Lh Pe Uv) aA(dC Ow Ua) Ji(bN cZ) Jl(Ii Iz) Ke(bX Ko) Kz(Cv Nw) On(Cq Jg) Vt(aK aV) AoJe CxJq FrfP LxNl MwMy Irls QcQe JubA KlUf} Un{cT(Al aM cZ Ef Fn Hb Ki Mj Oz Pa Ph Qc Ua Ur) Kg(Ao aW Ax cW Dp Fn Jn Nc Nn Oz Uv Wm) Lu(Ef Jg Jt Of Ow Oz Pa Qu Ur Vo) Ly(aD bH bM Iq Jf Kl Ko Lw Ow Rh) Nc(bA bP dM Fn Ir Jt Nm Pk Ur Vo) bR(bP bX dA dJ dM Jt Of Qv Vo) aA(aE Ef Iz Jg Kl Ml Ow Rh) Jt(cW Et Fn Fy Kq Pk Sr) Ri(Co dM Kz Nm Oz Rf Rh) Qv(aM Ao cZ Io Me Nl) Qg(aM bP Fn Iz Kl Nm) Bb(cI Mu Nr Nw St) Rf(Al bX dM Kf Ph) Ow(aE dM Ih Mg Qu) Ur(aD aM bP Iv Pc) Ao(BA Fy Pk) Ax(Al Cq Fw Ph) Cs(Io Nl Ph Qc) Fn(dM Ii Kz Rh) Jg(Kq Ma Nn Sr) Ki(aK Bo DB) aW(dN Mr Nk Nl) Co(cO Kz Pc) Hb(dE Pk Vo) Io(Iz Jo Kz) Kf(Nn Nr Sr) Ko(cI Hu Kq) bA(Bg Mg Qc) bP(Bo Nl Pk) Ba(Bg Ef) Dp(Iz Ue) Nm(dN Nn) Me(Ih Vo) Ms(Cu Mg) Kl(dF Nr) bX(Mm Oz) AdFy EfMa MrIr IhPk IjOf JocZ JyVo RhbH PadM aXbV bNcN} Mu{Me(aF bA bV dM Ih Im Jn Jq Lv Lw Mt Mz On Pc Pe Pf Qe) My(bN Et Ih Im Ir Is Iv Jn Jq Js Lh Mh Mz Nn Ok) Lj(Et Fr Hw Im Ir Is Iv Jn Lh Lw Mz Nt Ok Om Pe) Hu(Bg Et Ih Im Lv Mn Ok On Pf Qa Qb Qe) Ns(Et Hw Im Mn Na Nn Pf Qb Qe) Ms(Et Is Li Lv Lx Mn Ok On Pf) Po(Ir Iv Jm Jn Lw Mm Mz Pe) Nw(Is Mv Nq Nv Oe Of Pb Qa) Lv(Li Lx Ml Mz Pe Qa Qe) Pb(In Lx Oh Ok Pe Qa Qe) Bg(bR Cs Kq Pe Ur) Lx(Hv Ir Jn Mh Oe) Ly(Cs dM Ne Ok Pe) Mg(cT Et Qe Wm) Jr(Is Lw Oe On) Of(Hv Is Jq Lh) aA(aF Jq Mn Ok) Fp(aM Jl Jt) Ml(aF Lw Mm) Iz(cT Kz Sr) Jk(Is Lh On) Jo(dN Et Fy) Kl(bA dN Rf) Oe(Oh Pe Qa) Vo(cT Rf Sr) bX(aD Fa Qv) Nn(Ne Nh) Mn(Ne Nh) Iv(aE aW) Jm(Qa Qb) Oh(Jq Mr) Oz(dM Pe) Pa(Ax Pe) CoRf DpbV EfSr HqdN ImIo JiNx KzUr} Kq{Uc(aL Ba bM Cs Fp Hq Jl Nr On Pf Po Rf Sr Ur) bX(aJ aL Ao bM bP cI De Jo Mv My Nq Ow) Jg(aL aW Bb bW cZ Nr Nx Ow Rf Uf Ur) Kl(aA Co Kg Lw Mm Ms Nq Pk Rf Sr Uf) Bb(cI Cs cZ Fn Jt Me Oz Qg Ur) Bg(bR cZ Kd Pa Qy Ri Ur) Vo(Hq Lw Ms Pg Qc Qe Sr) Fp(Fw Kn Mj Nb Nq Ut) Ly(aK aL Ao Cu Hq Tv) Ii(aL bN dN Is Pk Rf) Iz(aW cI Ko Nc Qy Rf) Ki(aK cZ Db dE Kz Ri) Ur(aL aU Cx Kz Oz Qz) Dp(aF Cq Jo Mg Of) Co(cO dE Kz Nr) De(aK aL bH cN) My(cI Cx dM Ko) Of(aA aW Nl Pa) dN(Jo Jt Ow Ut) Ao(aK cZ Im) Ss(cZ Qc Ri) Kg(Ow Pk Rf) aF(aV bA Lx) dM(bN Cx Fn) Cp(cI cZ) Cu(dA Jn) Ef(cI Ms) Tv(Im Pk) Iu(Kz Pa) Jt(Pk Ri) aK(Hq Io) CxaA FnNc LufP QzcK QvaL JoKz OzbP aMbH} Ly{Ki(aM Ba Cv dF Di Dk Et Jp Jr Jy Lh Li Lj Lu Oa Pf Po Qa Qe Qx Tn Ut Vt Wm) dM(aC bM Fp It Jr Ky Li Lj Nt Oh Pf Qd Qv) Ur(Is Kn Lh Lx Mr Or Pi Pk Po Qe Ql) Sr(aW cK cN dA Dp Fw Ih Kg Qc Ql) Je(aJ aP bM Cs dG Oh Pf Po) Lx(Co Jr Ne Pk Po Qa Qe) Nw(aW Iz Lv Ms Nj Ns Po) On(Dp Ef Iz Kl Nh Ns Pk) cN(Fp Is Mr Ow Qv Qy Wm) Ql(aJ aP bA Cs Mm Uf) Fa(bW Cv Mm Oe Uf) Ji(cZ dA Fn Ok Qg) Qu(aP Ax Jn Li Nn) Rf(bV bW Cv Lu Uf) Cs(Cv Ke Lw Qy) Et(Fp Ne Nh Vo) Ri(Cv Jl Jn Ke) Qy(aJ bV Qv) Kk(bW Mm Uf) Ok(Jr Nh Wm) aA(bW Uf Vt) Is(Co Iq) Qe(aW Iz) Uh(Qx Tv) bV(Pk Rb) DpaP WmMp PoNh FpJl LwJf QaQg QvVt cWtF} Kg{Is(AD bI bR bV Cq Cw Hu Hv Hw Id Ij Jn Jr Kn Lh Lw Ms Na Pb Pi Qa Ra Ri Rj Up Vp) Pk(aJ aM aP bV cN cS Ez Fr Iv Jl Lx Mm Mn Mp Mr Oh Pd Pf Qa Ql Qy Rf Ri Uf) Rf(Ad bA Cq cT Cw Hw Id In Jq Jr Ke Kn Ml Na Om Pb Pi Ul Up) Fy(bA Bn bW dA Ez Jt Lh Nc Nm Ok Pe Uc) dN(dK Jl Jq Jt Kd Kn Md Nb Po Up Uv Vp) Jr(aD Bc cT cW dA Oe Ow Rh Sr Tz Vt) Et(Fp Me Ml Sr Tv Uv Vt) Jn(aM cN cW Io Nc Nl) Me(Ba Lh Ma Ri Uf) Sr(Ki Nc Nr Qe Qg) Dp(Id Kn Lh Tn) Qa(cZ Ki Nr Ql) Ji(bN dA Qg Ql) Fp(Ok Ut) Qe(cT Tv) Kz(Om On) Uv(Ma Nn) Vt(Im Nr) MlQl RiPe OzbA} aA{Io(Ax Bg Cs Fp Fr Iz Jg Jl Jr Mm Mn Mp Nn Om Uv) Mm(bN Im Jn Lj Na Nw Oe Oh Pe) Ki(Ax bP Et Iz Ml Ms Oh Wm) Ri(aE bU Fy Ji Ms Sr Ua Wm) Oe(Jl Jn Lh Lj Ok On Oz Sr) Lw(Bn Ko Li Ml Oh Ok Pk) Hu(Fr Iz Li Lx Pf Qu) Pc(Ml Mr Nk Oh Ok Wm) Me(bW Cv Jl Ma Rh) dA(bS bU cA Pk Vt) Nn(Lj Mv My Ok) Nc(aD dM Jn Ql) Ua(Is Jr Qe Rf) Iz(Ez Nr Qc Qy) On(Ef Lj Ns Pb) aE(Et Iv Qe Ql) aM(bW Fn Ms Nl) Lx(aF aO Hq) Om(Ms My Pb) Vt(bP Cx Wm) Oz(aD cW Pd) aW(bR Mr Ow) Co(Is Pk) Fn(Qa Uv) Lv(aF Pf) Ji(bN Up) Sr(bX Qg) Qu(Ba Iv) Kc(bX Ko) aO(Ma Rf) cT(aG cN) AdEf AoEt CqIs CvcX DbbW WmNa FrLj FyHq NlbM HvbP QaQg QeKl QlcW NwaF OfOk} Ur{Dp(aD aM Cp cT Cu Dc dG Hx In Ir Jy Kn Mz Oa Ok On Pf Ut Uv) Pk(aJ aM bA bP cK cN Co Fn Hu Is Kz Ms Nr Ow Oz Pc Po Qe Rf) Me(aM aR aW bV Dc Fb Fr Id Ke Ms Nn Pe Qa Qv Vt) Kz(aD cN Cv dA Io Is Iv Je Jn Kk Lx Ql Rf Sr) Fp(aM cW dG Ik Ms Nw Pc Ul Ut) Iv(aW bP cK dM Io Ki Ms Pc Uv) Ri(aM Qa Qb Ql Sr) Vt(aK aV dA Hf Oz) dN(Dc Id Ms Pi Ra) Lw(Af aU Bn cZ) In(Bo dJ Fn Hu) Ji(Af aL cZ Hf) Jn(aD Ki Qu Uv) Qa(aL Ki Qg) Sr(aU dA Kl) Jr(aM Hb Uv) Oz(Lv Po Tn) Pc(dM Ow Po) Ml(Ny Qg) Is(Ms Ql) Qe(dA Kl) Uv(aU cY) Pe(fP Pa) Pi(Fn Ki) dM(Im Mr) HuaM HwdA KlPd} Co{Rf(Ad As Bc bR bV Cp cT Cu cW dA Dc Dd dM Hv Hw Ib Ij Ir Is Jo Js Kd Kn Kp Lh Lu Md Mr Mv Na Nb Om Ow Pe Po Qa Ql Qx Rj Tv Ud Up Ut Vp) Fp(aP bQ Dk Jr Lv Ma Pg Qd Ut) Jn(aE Ar bQ Hu Ld Lv Ri Sr Vt) Fy(Fb Je Jy Nn Nr Pe Ql) Pk(aJ dA Et Hu Im Mr Qb) Me(Ba Is Jr Ld Ma Oh) Ji(Ax bZ Db dE Kz) dN(dB Kf Ma On Uh) Is(aW bQ Cs Nr) Sr(bX Cx Db dE) Jr(Ar Hu Nr Qy) Kz(Jq Kk Oh St) Nn(bR Hu Mr) Lx(Iv

Figure 8 Continued

Ow Ri) Je(Ax Cs Fa) Im(bA bV) It(Tn Tv) Qa(Db Fn) Pe(Nc Oe) bQ(bR Qe) CxJq NrRi MlQg NwdA OnbX} Ri{Ki(aM aP Ar bA cT dM Fp Fy Im Jr Ky Lj Lx Ml Nn Po Qa Ql Qv) Cs(cK dA Dp Jy Lw Me Nc Pc) Fa(Bg Hu Iz Kz Me Ms Oz Ql) Qv(aM dA Me Mr Pc Qb Ql Rf) aW(Ih Is Ji Jl Pe Qa Rf Sr) dM(Fp Lj Nn Nr Oa Pc Qa) Oz(aJ bA bV cN Kk Rf) Ql(bA Iv Jr Pk Sr) Me(Ax bP Lw Lx) Nc(Ax bA cN Sr) Iz(Im Jn Nn Pe) Qa(aK Fn Jo Qg) Fp(Ik Lu Ms) Iv(aE bP cN) Qu(bA Jn Pe) Kz(aP Kk Nw) Rf(aM aP dA) bX(aJ Ke Lw) Mr(Ax bP) Sr(Jo Ko) Jn(bV Lu) dA(Ms Nw) PoPa NrcN Mwcl NjbA NlJr IiPe IuQe JiKo JlKl PcaP bVcA} Fp{Mm(Is Jl Lu Me Mi Mn Mr Mt Mz Nt Oh Ok Pa Pc Pe Qa Qe) Jq(aM bW cW Is Kd Mr Pa Pe) cN(bS cA cF Fr Ik Ms Nc Nk) Oh(In Jg Jp Lv Mi Ms Pc) Ok(Hu Ik Mg My Nn Pc) Om(Et Ir Is Jn Pc Pe) Fr(Al Ir Jt Lv Qa) Jy(Bg bV bW dM Tz) Nn(In Is Jl Oe) Lu(bV Mn Pj Uh) Ms(bV Dk Et Jg) On(Al Jk Nq Pz) Cv(aD Oz Qv) Ik(Ba Pf Qe) Jl(Oe Pc Rm) Jo(dF dG Jt) Ke(Fw Mj Tz) Nw(Bg bW Tz) Ao(Lx St) Et(Hx Pc) Lw(aG dM) Mp(Hq Nd) bV(aW Mg) AlSt MnNe MrdM HuJh IhIs IoJp QvaD} Dp{Qv(aW bC bM bW Cu Cx dG Fy Jt Kd Kk Kn Li Md Ml Mm Nm Ok Om On Ow Uf Ul) Fa(Ad As bW Cq Cu Dc Id Ij Jn Jr Ju Kn Kp Na Pk Rf Rh Rj Tv Uf Up Vt) Lu(Ar Ax Id Ji Jn Jr Lj Nn Nt Nw Oa Oh Pf Pk) bV(bA cR Ko Mg Mn Mt Nb Nw On Pe St Ut Vt) Cs(dM Ik Jq Ks Ky Ms) Bo(Ij Pk Qa Ra Tv) Sr(Ki Ks Oc Of Qg) cN(cT Ml Nn Ow) dM(Jy Nn Pe) Ao(On Rf) Ax(Jy Lw) Qa(Jo Ug) Ld(aJ aP) NnMs LwLj MgPf IuJl JqdN KiPk aPbX} Me{Lw(aM bN Im Jq Ld Ok On Ql Vo) On(Ax Bg Cs Im Jq Lj Ms Nn) Lx(cA Im Li Mm Nn Oh Qa) Jr(aW cN Fr Im Mm Oh Om) bV(AX Ki Nc Ql Qu Rf) In(Nn Ok Po Qa Qe Ql) dM(Fy Kk Qg Qu Ra Uf) Cs(cN dA Io Ki Mm) Et(cI Io Jo Nn Po) Oh(cN Ki Lv Nw Qg) Om(Lv Ms Of Pb) aW(Ba bQ Iv Mt) dA(aD aJ bR Uh) cN(Ml Nr Oz) Ba(Iz Jo) Wm(Jp Qd) Nn(Hu Ns) Qv(cZ Ql) Jl(aE cI) Jn(Iz Ki) Nw(Hu Ms) bP(Mr Qy) PoPb FrOf MmIm MpJq MwNa TnOz TvUh IrSr IsbI JeRh KibQ bWbZ} Po{Jo(dA Hv Hw Ij Ir Is Jl Jn Jq Jr Js Jt Lh Lw Mr Mz Nm Nt Om On Qe) Ms(Et Fr Im Is Jg Jl Lv Nn Oh Ok Om On Pb Pc Qe) Pb(Et Io Is Iv Jq Lw Nw Ok Om On Pe) Hu(Et Jh Lv Lx Nw Om On) Ii(Et Is Jl On Pk Qa Qe) My(Je Ji Jp Lw Nw) Im(Ih Il Io Nw Oe) Io(Jl Lv Na Qa) Et(Mg Ns Oe) Ns(Jl Nw) Ne(Nc Nl) Il(Is Qa) Jr(Lw Mm) Oz(aW Jl) Pa(Qv Tv) dA(cA Nd) LxMg HqOn InQc QgPk KzdM OfOk} Sr{aK(aZ Bo Cx Jo Ky Lx Ms Nn Ow Pk Qv Rf Rh Ug Vo) dA(Bo bQ cA Hq Iz Nd Ns Of Oz Pd Ua) bX(aP bE bV Jo Lu Lx Qu Qv Ug Uk) Kl(dJ Ez Gp Jy Lw Lx Nn Oh) Ef(cT Dc Jl Jp Lw On Ra) Qg(aM bP Cs dM Jr Oz) Vo(Ba dJ Ez Jy Nl) Ki(Bo bR dB Ky) Cx(bH cK Cv) Pk(bH dJ Iz) Bg(aV Je) Mr(Ir Iu) My(dN Hu) Ii(Iv Nc) Jo(aV Jr) Jt(Jn Jr) Oz(aW bP) cK(Bo Kz) NldM UaHu IzQy JucI JyaF bHbN} dM{bR(aC Ar bV Cs dA Jl Lj Nn Ny Oz Qa) bX(cA Et Jr Ke Nw On Qa Qd Qn Vt) Oz(Ar Et Gl Iv Ji Kd Kn Ky Qv) Mr(aD Jn Jr Nn Nr Ql Rf) Pa(Ar Ax cT Ji Nw Ow Qe) Db(Cs Ji Jl Ki Oa Pe) Nc(Jl Jr Nr Qa Ql) Kz(Ax Io Oh Ow Pf) Im(aM bW Io Uv) Iv(Io Oe Ql tF) Kl(Mw Ny On Rf) Pc(Cs dN Pe Ql) bN(Md Nn Ow) Qa(Fn Qg) AlIs AoRf BgMw MsQl HqNy JiKo JyUv aMbF bVfP} Pk{Qg(Cs Cv Fa Hu Is Iv Ji Jn Lu Nn On Ow) Ki(aD Bo Cv Hv Jq On Uh) cN(bA Bg Bo dH Ms Qv Rh) Lw(aW Bg cZ My Ql Rf) Oz(aJ aP aW bA Tn) Ms(dA Jn Mr Qy) Ir(Is Ji Mr Qe) aK(bA dG Fr Jl) aW(Is Jl On Uh) Et(Iz Jo Lu) Lx(Hq Nl Qz) Qe(Ih Iu Qc) bP(Mr Ql Uh) bV(cA Ql Qu) Ba(Qu Vo) Is(Jo Vo) Rf(Ao Lu) Nw(bX dA) On(bX Jg) CqJi IiJn IzQy QvaM JybA KeKo KlUf UhcK aJbN} Lx{My(Hx Im Ir Is Js Lv Mt Na Nd Ny Qa) Pb(Im Ir Is Ji Jn Lv Na Pe Qb Qe) Im(Ao Hq Hu Lv Ms Nh Of Qa) Kz(bR Hq Ki Pf Qh Ua Tj) Qa(Hq Il Jr Md Ms Ns) Qb(Hu Lw Mh Na Of) Lv(Jr Lj Ne Nh) Kl(Fb Hu Lh Nr) Hq(Jl Jr Pd) Il(Is Na Qe) Ms(Jn Jr) Of(Is Lh) aK(Uv Vt) bX(bS cA) AoJn EtJr FnPi MdJi MtNa MvIj NlSs UcHw KyfP PcbR cNdH} Kl{Ba(Ad As aW BC bM bW Cq Cu Cw dL Hv Hw Ij Im Ir Kz Mg Na Nm Or Pi Qv Ra) Et(aP Jy Lw Ms Nn On Qv) Jn(cN dG Ki Mm Nn Nw) Lw(Ax Cs Ez Pe Ql) Ji(Ax Fn Ma Nn Rf) Cv(Cx Im Ma Ow) On(dA My Nn Ql) Jy(Oh Ow Pf) Nn(Nw tF) Rf(bV Mm) Ow(Dk Nw) Uf(Jr Ma) dA(Fa Jl) FrtF FybW QcQe UhcT} dN{Jo(Ax Ba cT Jy Ma Ml Nn Ow Qa Qn Ra Rh) Ke(aF Bg dH Fn Nx Pa Qz) Fn(Ji Jq Om Tv Vt) cT(Bg Cv Ki Vv) Bo(Ao Hq My) Fy(dH Ko Nl) Rg(Ax Cs Nr) Fw(Ml Pi) Iz(On Ut) Qv(aF bR) Qu(Ba Qt) Kd(Dc Nw) Ow(Ms Vv) aW(Qn Qt) bM(aD Io) dH(cN Lu) AoJy BgFr DgUh LwQg MabZ MwHu MyOm InKo HfJe JiOk RhVv RfOe NybF PbbA} Kz{cN(Bg bU bV cT Je Ki Kn Ns Ny Oe Oh On Rh St) aW(aJ bV Dk Et Id Jn Oh Om) Iz(Dk Fr Jr Nw Om Rf) Lu(Ji Jn Jr Ki Rf) Ki(aJ Ax Fr Oh) aD(Cv dA Ql Qy) Qu(bQ Jp Pf) Ao(Fr On) Cs(Cv Nw) Lw(cZ Jf) Ms(Ql Qy) Ii(Is Jr) Kk(bW Uf) aJ(bS cA) bA(Je Jy) BgFr CqJi IuJl QvcK QgJq NwdA OfOm} Lw{Im(Ao Iv Jq Jr Lu Mi Ns Qe) bN(bV Cs Db Jn My Qg Uc) Fn(Af aK bX cX Ki Vo) Ql(aF aK Bn cI Ko) Rf(Ao Ii Pa Ss) Bn(Fa Ki Vo) Cx(Ju Ky Uk) Jr(Et Ko Nw) Rh(Af cI Hf) Fy(bX Vo) Uc(dE Qa) Qz(aF Cs) Lj(Hf Qg) Up(aK bX) DgNr NnSs NdaM IoNw KidB KodE VocZ PacT} dA{aD(Ar aW bR bU cF Cs Cv Hu Ki Li Mr Oa Ow Ql Rf) Nw(Bb Bg bS Iz Ml Nd Qz) bR(aC bA bV dL Ki Pf Qe) Fa(bQ cO Ms Nd Ns Pc) Ao(Gl Jl Nn Uh) Ji(bG Fn Ms My) Ki(bV cW Ky Ml) Qe(Ih Ms) Qv(Nc Ql) BoaM EtMg NnIz IvaW bUcN bVcA} Jr{Nw(Et Hw Ir Iv Jn Jq Mm Ok) Io(Im Jl Lv Mn Qa Qe) Ms(Jl Oh Om On Qy) Nc(aW cN Ne Qg) Im(Jq Oe On Pc) Nn(Hu Lv Ns) Qy(Ao Ii Iz) aW(Mr Nk Oz) Bg(Hu Mw) Et(Jq Pc) Ns(Mp On) Ok(Jo Of) BaVo WmOe LvOh HqOn HuOm IiQl QaQc QvOz bRcN} Ji{cZ(Af Ao cC Jo Lu Ms Ug) Nn(Hu Mv Ns Nx) aK(Lu Ms Rf Rh) bX(aP bE Qc Rf) Ko(Ax Hu Qg) Fr(Of Pb) Lu(aU aV) Ms(Cx Jl) Nc(aW cI) Ii(dE On) Nw(Md My) AfaW AoIm BaSs BbQg EtIo FnVo FyJo MvPc KidE OfOk bRdJ} Qa{Qg(aV aW bP bX Fw Jo Ko Mj Nc Of Qc Ql) Io(Et Lv Mn Na Ok On) Qc(aW Ih Jn Mt Mz) Of(Je Nb Nw On Pa) aW(Mr Nc Nk Oe) Et(Jo Ms) Pb(Nw On) BgHu FafP FnNc MyOm IhOh IlIs JoOk JyVo} On{Im(Hq Il Jo Mg Ms Oe Pb) Pb(Ne Nh Ns Pe Qe) Of(Hv Ij In Ml) Lv(Hq Ns Nv) Ms(Jn Nw Wm) My(Io Nc) Lj(Io Pa) bN(bP Jg) bR(bX cI) ApaF BgJe CsPa CxIz WmOe InQb IvaW QeJo QvfP} aW{Iv(aJ aM Nc Nk Oc Oz Pc) Is(bR Ju Ms Nl Oe Qc) Oz(Fy Gl Ke Nw Pe Qe) Mr(aM Et Jn Mw Nn) Nk(Jn Qe) Im(Oe Ul) Jy(aM Ow) CvCx NcQc JlPa JnNw} Rf{Ao(aM bQ Iv Mr Mw Uf) Lu(Pc Ql Qu) bV(Nc Oz Pc) Cv(Af Dg) Jo(bA Ul) Ke(Jt Ko) cN(bS Pc) DgMm MwMy HuQu IrIv IzJn QvOz VobW aPfP} Nw{Ms(Is Na Nn Oh Om Pe Qe) Io(Hu Is Iv Lj Na Qe) Im(Iz Lv Tv) Pa(cT Oh Pf) Wm(My Pz) To(Iv Mr) Pb(Is Pe) LufP HwOf TvbX} Ki{Fn(Cu Cw Dc Id Pi Ra) Qv(Db Im Jn Nr Ql) Db(Ax Fa Jn) Lu(Im Jn) Qg(bA Ml) AxHf CxJq NnQu NrOe MsJn IiPe IjOf QlbA} Im{Io(Et Fr Jl Ok Om) Iz(cN Cp Kn Md Mz) Ok(Jo Lv Of) Ao(Cv Jy) Qe(Ih Lv) FrMy QvQu OecN} Is{Jo(Cq Cu Dc Tv) bV(Dg Nc Pa Vo) Ao(Jy Nc) My(Fr Mw) AlcI WmMg FnNl NrVo IiaM IuQl IzbR QvPa} Jn{Ms(cN Ql Qy Wm) aD(cZ Qc Qg) Mp(Nd Of) Iz(Hu Nc) cN(Bg dH) CvCx EtIo MgQg QvPa JyVo} bA{Qg(aL aM cY Oz) aM(aK bE cY) Qy(Ef Pa) Jy(aL Vo) Ql(Ct Pa) FnNl NcSt QcQe aSbR bVfP} Et{Io(Li Lv Ne Nn Pe Qb Qe) Lu(Dg fP Lv) Ms(Qb Wm) Jo(Lv Pd) DgbV FrMy} Iv{cN(Bg bS cA dH Nc Nd) Mp(Nd Ns) bV(bR Qu) CvCx CwOf FrMy HuIz JocT} fP{Fa(dL Id Qz Ra) aP(Cs Mr Nl Nr) Qv(Nr Om Qy) bV(bM Ml) FrQx LdaJ} Hu{Iz(Fa Jl Ow Qe) Oz(aD aJ Qv) Nn(Lv Qu) CwOf MpNd MraD UaQe} My{Mw(Bg bM bR bX Cs Tn Ua) Fr(Ih Jq Na Nh) NnNa} Mp{Nd(Ij Jq Js Mr Ny) Ns(Ml Ny Pe) NbOf QvbX} bV{bR(aM bH Mr) Ql(Nc Oe) Of(In Pi) CvCx aMaX aVcA} Cs{Qg(aM Dc Jq) Qy(Ms Oe) MrOe QuJy JqPa KeKo} Nn{Lv(Nh Ns) Vv(aK aU) BgJe MsQe NaIo IzPc QubX} Fy{bH(AO Iz Jf Nc Nl Pa) IiOz} tF{Fa(AF) Lu(Lj Oa) AoFr MgcW NcQv IzPe} Bg{Je(aP Fa Fr) QycT JycN OmbN} Cv{Cx(cI cT Nr Qv) AfcT AxHf} Of{Ij(cN Fn) LvOk MwTv InbZ OwPi} bX{Ke(aK aM cZ) QeQv VtaJ bRfR} Jq{AxPa CxbH EfFa FnNl aFbQ} Jy{Ao(Ow Ql) NrVo MlaF QzaE} Tv{Oz(Pd Uh) ItQg JlPa} Io{Lv(Oh Qe) LjOk} bQ{aDbF bMbR cAcN} cT{Qy(Iz Mv) QuQl} Wm{FrMg QdOe} Ok{MsQb JoPd} aV{TjFa aJbR} cN{MrdH QlbR} MmPaPe TnQuOz Constrained panels with 3 analytes, where 2.5E-8 >= 'AUC p-value' > 1.0E-8. Contains 7,249 panels of 7,079,861 total panels evaluated. : Aj{Pe(Bn bV Cv cZ Ez Ib Kd Kp Md Ms Nj Oi Qt Ra Rb Rj Tv Uc Ur Us Ut Uv Vp Vt) Jl(Ad As Cp Cq Cu Cw Dc Hv Id In Jn Jq Kr Ml Mq Mu Na Om Pb Pi Qa Ra Up) Et(Ad Cs Cv Hv Hx Ib Id It Kn Kz Md Na Nr Ny Om Ql Us Ut Vt) Qe(Bn Dd Id Jo Jt Kp Lh Lu Lw Ly Nm Ny Ql Uc Us Uv Vt Wm) Ez(Ad An As Cq Cu Hv Ij Ir Jr Mr Ms Mz Na Nf Pb Rj Ut) Pf(dA Dd dM Hu Ib Ir Jn Jr Ke Kp Ml Mr Mz Qa Uc Us Uv)

Figure 8 Continued dA(aC bV cT Cu dF Hx Kf Kg Li Lj Md Nm Oh Rb Ri Ud) Fy(aM As Cp Dc Hv Hw Ij In Kn Kp Mm Na Pb Uc Vp) Lx(Cp Dd dM Hu Hv Jq Jr Kr Kx Ml Pc Rj Uv Vp) Qy(As Ax bV Fa Id In Jo Kd Ly Mz Ok Pb Uv Vp) Rf(aP Aw BA cW Ji Js Lu Ly Mz Nb Nc Tn Vt) Ql(aD Ax Cp Dc Ed Jt Kn Kz Ml Nf Ny Oi Om On) Mr(aD aM aP Bn Cq Cv dG Hv Jt Ms Na Ny Pb) bV(bO bU Ef Ij Jq Ml Ny Pi Qt Up Us Ut Vp) Mq(bA Cs Cv Dd dG Hw Lh Oi Ok Rh Up Vp) Iv(Ad Aw Hv Hw Ir Mw Na Nf Ok Ow Rh Wm) Pd(aD Ba Cp Cq Fa Hv Hw Ij In Ji Mu Pi) Kx(aD An Dd dF Dp Ef Hr Hv Hx Rj Vp) Ba(Bn Ch Hu Hx Jd Ke Kg Kq Ph Ul) Nr(aM Aw cN cT Di Ib Kp Qt Ra Rj) Om(Ax bN dM Fr Im Kr Ma Oh Us) Uf(Ad Cu Cw Hw Ij Ml Pi Up Uv) bA(Cp Cu Cw Dc Jq Ny Po Uc Up) Mu(Bc Dc dM Hv Jd Jq Pi Rh) Nf(Fp Ib Ko Kr Ml Na Ny St) Kz(Dl Nv Nw Ny Ok Pk Qd) On(aA Ap Dp Ki Lj Ml Ms Nn) Fr(Hv Id In Kr Pb Up Vp) Me(Fb Jp Mx Mz Nm Qd Ri) Ij(cZ Jr Ki Oh Qa Qg Us) Qt(Ax Hw Ir Kd Kp Ri Vp) Ow(Ad Kd Kn Lw Md Ms Vt) Ef(bC cN cS Jj Pi Up) Fp(aJ Hv Hw Na Ny Pb) Ni(Im Jg Jy Qv Rh Ut) Hu(aJ cM Cv Ma Ms Ul) Qa(Cw Dk Lw Md Ms Oi) dl(Kf Kg Mj Nm Nn Ut) Fa(bO Jv Ok Pc Tv) Fb(aM Bn Kd Kp Ok) Mw(Cp It Kp Md My) Tn(Ly Nl Qd Qn Uh) Oh(Dc Id Ml Pi Uv) Pk(Ax Bg Kf Uh Vt) dM(Dk Ha Lh Mt Oa) Cw(cN cZ Uu Wm) Dp(Bc Cp Kf Qd) Nn(aM Aw bR Lu) Im(cN Id Nc Rb) Jy(Jd Lj Oa Po) Fn(As Cp Dc) Ma(Hw Id Uv) Ml(aA Je Jk) Ji(Hv Jv Ms) Jr(Io Lh Nj) Kr(dL Jt Kn) Ri(aM Js Ny) Us(Jq Jt Nm) bJ(Dd Js Lv) Ax(Ut Uv) Bo(Na Ra) Ed(Bc Dc) Po(aM cT) Lw(Ar Mv) Ly(Kk Ou) Kq(Hq Vp) cC(Bn Jo) AdUu AwIs CvNo UaTv HcLh StcT QgVt JnKd JqaA KebO KiUt bNdG bRdF} Kj{Fy(Cp Cq cT Cu Dc dL Hv Hw Jr Kd Kn Kp Nf Nl Ra Uc Us) Ax(Cq Hv In Ir Jt Jy Kf Mq Mw Mz Ok Oz Pb Ql Rj Vp) Mq(bR cT In Ir Je Jk Js Mr Nf Nw Ok Ra St Us) Ni(As Aw Ba bW Fr Ha Hv Jk Mm Na Nw Pc Ua Wm) Jl(Hw Jn Jo Jr Jt Kz Og Pd Pe Ra Ri Uv Vt) As(aK Bo dM Ha Hc Jp Lj Lx Mn Mr Pg) Nf(cZ dL It Jk Ki Kk Mm Pb Rb Tn Uc) Ra(aA Bo cN Cp Ed Fa Jp Ke Mw Qb Uf) Ba(Cq Cu Ir Iv Jn Jo Jr Ke Lh Om) Ri(Cu dG Fa Hr Ib Kg Md Or Rb Rf) Nr(Aw Bc bV dG Dk Ez Jv Jy Nn) Iv(bJ Cv cW dG Fr Lv Md Mu Ul) Kr(aJ aP bM Cp dE Dp Nt Tn Ut) On(An Ao bJ Dk Md Mv Mw Oh Us) Pf(Cq Cu In Jn Jr Jt Mz Rj Uv) It(Cq Et Hv In Ir Mz Nm Pb) Kf(aK Fb Gl Hu Na Nl Qy Rb) Kx(An Aw Dk Fr Oh Po Us Vp) Ow(Aw bV Cu In Jt Ny Ok Rf) Mr(Ir Jd Ml Pd Rj Uc Ut) Mu(aD Ed Fp Kd Kz My Oa) Gl(Cp Dd Jo Ml Pb Uc) Na(bM bZ Db dG Jy Qm) Hu(Cq dL Hv Mx Uc Vp) Jt(aK dl Rj St Uf Vt) Pd(Hc Ly Ng Nw Pc Qv) bV(Bc Ez Ml Ny Pb Pe) dM(Ez Jo Mt Nb Pb Pj) Et(dI Kp Mi Oi Rj) Me(Cq Dl In Ou Wm) Mz(Bc Dp Hc Im Kz) Hw(aA bM cA Gp Tn) Tv(Bo Fa Ki Nk Om) Oh(dA Mj Ny Us Ut) Vt(aA bE bO cT Hc) Bn(Fb Lx Sr tF) Nm(Dk Qd Tn Ua) Nn(bR Je Jy Oz) Kz(Je Jp Rb Ul) Uf(Js Kp Uc Us) Uv(Ef Fr Nv Qd) dI(Ir Nb Ny Pb) Cs(Cv dA Ut) Fb(Kg Md Ud) Lx(An Jd Ul) Is(aP Oe Qc) Jo(aA bJ St) Jv(Cu Ke Ml) Ki(Cq Cu Jd) Us(Fn Mn Qg) bW(Js Mt Ny) cT(Ji Jy St) Ch(Ef Tn) Cp(Fw Ur) Dp(aP Ml) Ma(Ny Tn) In(Mm My) Io(Jr Qa) Qe(Ms Qc) Sr(Iu Qv) Kc(cI Oz) Lh(cK Oi) Rj(Bc Lw) Nw(Kg Pb) Ok(aQ dA) Om(Je Ul) Ut(Of Rh) Ph(bJ eC) ArCq CvQb PobR EzLv MdMn UdQg IbbJ ImdL JdPc LjPb RfdA VpdG} Uu{Rf(As Cq Cu Hw Ij In Jr Kd Kr Me Ml Na Nb Pb Pi Ra Rj Us Vp) Mu(Ao bJ dL Ij Jh Js Ko Ly Mw Mz Na Oz Rj Uc Ul Ut Uv) Nr(Ad aM Aw Bn Cp cT dL Fy Kn Mz Ny Qa St Ur) Kf(aJ Ax cN Dc Iv Jj Kr Nw Oi Ow Ul Ur Wm tF) Nn(aV bW Cq Cu Cw Jj Jt Ly Mz Qa Rj Uc Ur) Qd(Ad Ez Jh Jt Kp Ly Mr Nm Tn Tv Ul Vt) Uf(Aw bV Cq Cu Dd Et Kp Nf Nt Pi Uc Vp) Vt(cN Di Je Ma Mn Mq Nf Nv Oh Pk Qa) aP(Cu Hw In Ml Mz Nm Pf Pi Uc Uv Vp) Ni(Ar bJ bQ bW eC Ed Jg Jy Pd Pk) Ql(Ad Cw dI Iv Jg Ma Mq Nw Pk Ul) bV(Cu Ef Kn Me Mw Nf Ny Oh Ow Pf) Cv(As Dd Kd Kn Kp Mj Mx Or Us) Dc(bA cN cZ Ki Lh Ma Oh Qg Wm) Nv(Ad bJ Ch Dp Ez Me Qt Qv Ul) Mq(bF bZ cT Kk Nq Pe Qe Ut) Jy(Aw Dp Jj Jk Jt Kp Nm Uv) bJ(aJ Kp Lh Ny Ok Pd Pf Tn) dM(Bn In Ir Kp Nm Ou Rj Uc) Qa(bF cN Co Kx Nc Qv Qy) Jg(Jv Lu Ma Nw Pd Pk Tn) dI(Li Na Nf Nm Oh Ow Pi) Iv(dG Fa Je Ky Mn Uh) Qc(An bO Cp Kp Md Mz) Ri(Cs Jp Ma Oh Pk Tn) Nw(Ad Jt Ou Pc Qv Ra) Ut(aJ Ax dA Dg Ez Ur) Pe(Kd Kr Ly Mh Oz Qv) Pf(Ki Lj Ly Md Oz St) Po(Dp Ez Ly Oi Ul) Id(aW Ax Lu Qv Rc) Pk(bQ cE dA Ma St) bW(Cw Et Ij Kd Tn) Ki(Ax bQ Kn Oh) Kx(Bc Cs Lh Ly) Ny(aJ cN dG Oy) Ad(aW bE Qy) Aw(Fb Lx Uh) Cp(cN Qt Us) Et(Io Nf Nm) St(aM Dl Jr) Jj(Jl Mw Ow) Jn(bO cZ eC) Jp(Ed Mr Nf) Kk(Ez Ow Oz) Lh(Ch Kr Ly) dA(Bc Cs Nt) dG(Ax Ez Kd) An(eC Oh) Fy(bC Mh) Hu(Im Jt) Tn(Co Mr) Je(dF Gl) Qy(cN Lv) Jq(bM Rh) Ok(Lu Pc) Uh(Dl Js) bA(aM cZ) AxPc CwFb DpdF EdPd FrRb LxaW MeOh MlbE MnKd QvPj QgKn UrPi} Us{Jl(Ad As Bn bX Cq cT Cv Cw dL Hc Hv Hw In Ir Is Jn Jr Kn Kp Ml Mq Na Nf Om Ow Pi Po Ra Rf Rj Ud Up Vp Vt) Po(aM bV cN Cw dG Id Iv Jt Jy Kp Me Mr Na Nf Oi Ok Om Rj Up Vt) Fa(Ch Cv Cw Ed Hc Is Iv Jd Jq Kq Kx Me Rb Up) Sr(Ad bM Bn Cu Cw Id Ij Jy Kn Om Pi Ra Vt) Ki(aM An Ax Bn Dk Hv Ir Kp Kx Mr Nm Rj) Mq(aD Bn dL Ed Ke Nn Ok Qa Qd Ri Ut) On(aJ Hu In Js Kn Ms Mv Of Pg Qt) Uf(Cq Hv Ib Jq Kd Mz Om Or Ut Uv) Id(bV Co dA Dp Iv Jn Kx Nf Ni) Nn(bA bV cN Co dI Iv Jr Me) Qe(bS dG Ed Hu Kq Mu Rb Ri) Jd(As bP Cp Mi Mz Tn Tv Ud) dA(aA aD aP Cs Me Qa Qd Vt) dM(Ad Ax dL eC Fr In Nt Rb) Ni(Fr Jj Li Mp Ne Nk Vt) Iv(bW dL Hu Mu Nw Oh Pf) Ql(Ch Cp dF Et Fr Jv Kx) aM(aJ bA bW Fr Mm Om Qg) bV(cW Ez Hu Mx Qd Ul) Cs(aA dI Dk Fr Qy) Is(aJ eC Kg Ms Qv) Jv(Nr Ok Om Pf Ut) Kx(Bc Dk Fr Mu Ok) Vt(Ba Ed Oz Qg Ur) cN(Ly Mu Ow Rb Ul) dG(bN Hq Mk Oi Ow) Co(Ke Kn Ml Nr) Lx(Jq Ly Nl Qa) Jn(bJ Me Nl Pk) aP(Dp Ly Mx Ri) bA(aJ bE bO Rf) bW(Hx In Ml Tn) eC(Cp Hx Jt Ng) Ch(Ok Pk Qd) Ed(dl Nw Pd) Qz(Et Jq Pe) Ke(aV bP Ri) Oi(bJ Lw Qd) Oz(Jp Ok Pe) Mm(Ij Nf) Mr(aD Hu) Mu(Hw Ow) Tv(Et Oy) Qa(cK Iu) Jq(bM Fn) Jy(aD Ax) Uh(Kr Up) Pf(Me Ul) aJ(Or Pc) dI(Mz Pk) dL(Nr Oy) CvIm WmQd FybH LwQu MlQg NfNw KgOk UvaA} dI{Nf(aC bW Cp Cu Cw Dc Fy In Kn Mz Nb Ow Pi) Jv(cP Dc Dd Ib Jq Kk Kr Ky Mw Ny Qv Ud) aD(bR Ch dM Ez Ji Ky Me Ml Mw Oa Po Ri) Kz(As Is Kd Kk Ld Nb Ny Om Rb Ur Ut) Ed(Cp Cq Hv Jt Ju Kd Kr Md Pb Rj) Fa(Bg bZ Cw In Ju Ng Nl Pc Pi Uv) Ly(cN dF Ij Ky Ld Mj Mx Pe Rb Ul) Jn(aW bS Co dM Io Jd Ng Qv Ur) Ri(cP Cw Hx Is Na Ok On Qb Ra) Nn(Ao Bg bU Hw Ki Na Ns Uk) Qe(Ad As Co In Mq Ni Ny Ua) Ch(cW Ez In Jh Mr Mt Vt) Ml(aJ bA Co cT Kg Kr Mu) Kx(Et Kp Md Rb Uc Uk Wm) aM(Cv Fr Jl Ke Ng Qg Qz) Ax(bS cA Et Ju Kr Rg) Nc(cT Lh Li Qb Tn Un) Is(bO Dp Kg Ni Nw Oe) Ra(bJ Fn Jd Og Oz Qg) Oi(aA Ar bU Hu Ld Qd) Oy(Bn Id Kd Mj Pd Rj) bM(As Cp Cq Dc Ij Ny) cP(Cq Cu Cv Hu Po Qd) Mq(bZ cG cK Mp Pi) Jr(bO bU Co Oe Qv) Kq(Bb bF bS Io Rh) Oh(bU cA Ng Oz Qz) Nr(bJ bV cC Io) Me(Et Hu Id Jj) Ni(Jl Jq Qu Un) Iv(Dc Jq Oz Ql) Rh(Dc Ir Mz Oa) bR(Ad dL Tn Ut) bS(Lh Mj Mt Mz) cA(Bc bQ cT On) Bg(Mt Ny Ut) Co(Cs Pf Sr) Lx(bZ cG Pg) Ij(Fn Hc Ng) It(cW Hq Og) Qv(Im Pc Uv) Jl(cL Kl Nd) Oz(Id Jd Kn) Cs(Kp Ut) Et(aA Dg) Fp(Hw Ql) Hc(Jd Ji) Io(Pe Rf) Qb(Ms Oe) Qx(Ao Oa) Kg(Qa Sr) Kl(Fr On) Lj(Ib Lu) Ow(cL Hu) Ur(Fy Hw) Vt(bN Kr) Pf(bQ cG) Pi(bJ bU) aP(Ql Qz) BoIn CvPk DdRf DpcW PocF MraJ MzbU IdbJ JicZ JoeC KicT OaOg UnVo} bJ{bV(cW Fp Hv Hw Id Ij Jn Kd Kn Ky Md Mt Nn Om Po St) Nw(bA Cq Cw Hv Hw Id Ij Jn Jr Mq Nf Oi Pb Pe Vt) Vt(aE bO Jd Jn Ki Ly Ni Nr Ow Pk Rf Ri) aD(Ba Cq Cw In Li Ly Mt Mx Oa On Ow Uh) Ms(aM dG Kf Kk Kp Mz Ny Ok Om Up Ut) Pk(aW Id In Jr Kd Mg Mm Mq Oy Qa) Kn(aA aC cN Ki Mg Mq Ng Qg Ue) Oi(An bQ Cp dF In Lx Oh Qb Rj) Cs(aC cN cT dG Iv Ke Ki Uv) Ed(Ad CW In Is Ni Oh Pi) Id(aC bA Fn Jj Ly Oe Qu Ue) Kq(aO bN dL Dp Ib Ow Qu Uk) Kx(dL Iv Jn Lu Om Pe Ut Uv) Ch(aC Ax cN Ef Kr Pa Pb) Ml(Ki Mg Mu Og Po Ug Ur) Kc(Af Ap bN Jg Ki Nf Oe) Co(Jn Lv Mt Ny Ok Ut) Dc(bP cT dM Fn Lu Of) Me(aR Fr Mz Nn Og Un) Ng(Jl Mz Ok Rf Sr Ut) Qv(Fy In Is Mz Qb Qe) Qg(Cq Hv Hw Jr Md Up) Jv(dF In Nr Ny Om Uv) Pi(aE cN eC Mg Of Sr) aW(aM Fy Jn Lx Mz Or) Qa(bA bR Fn Kl Lw) Un(Ap Hb Ju Oz Uk) Ni(cT Jj Nr Vo) Iv(Iu Jo Jq Lu) Sr(aZ Jj Kz Up) Kd(aE bA cW Oy) Ny(bP Hu Oa Ug) Oe(Ax dG Mr Nt) Og(Ad dF Ij Kp) aC(Jj Mu Nn Pe) Cv(Cx Kl Uv) Lw(Al dM Hu) Mq(aE dA Ky) Jn(bA Lu Qu) Ri(Ax Kk Pe) cW(Fy Jq Mt) Cw(Jo Kg) Po(Tv Vv) Mu(Oa Uv) Nf(aJ Ji) Is(aE Tv) Qd(bI cT) Jr(aM Kr) Kl(bA dF) Oy(Ad Ji) cN(Ij On) AlPe FaHw FyLu NnQu LydG MtaE InOf RaaA JjOw JqeC KzbA LjdF RfaM} Oy{aJ(As Bn bS Cp Cq Cs Cu Dk Hc Hw Ij In Ir Kp Lh Lx Md Mz Nb Nf On Pb Po Qv Vp) dG(cT Dc Fa Fy Io Jq Jr Kd Ly Me Oe Oi Po Qv Vt) Fr(cN Et Jn Jq Ki Lj Lv Ml My Ns Ok Qe Ri Un) Kx(Bn Cp Cw dF Fb In Iv Kn Lh Nf Nn Ok Qy Ul) aP(In Is Mr Mt Mz Nf On Qv Ra St Ul Up Uv Vp) Lx(aD aM Co Dp Et Ky Li Ly Nn Nt Ul) cN(An Ar Cs Et Js Kf Ky Lh Mr Mu Nn) Fa(Cp Hv Io Jn Jy Kd Kp Kr Rf Ul) Tv(bE Bo

Figure 8 Continued dF Ed Je Mq Oh Qg Qn Qt) Om(bX Im Jn Jq Me Mk My Oh Po Wm) bV(Fy Ly Mp Mt Oh Pg Pi Rb Sr Vt) Po(Co Hw Ir Jt Mk Nt Pk Ql)
cT(dA Ji Jn Nr Pf Ql Rf St) Mu(Bg Im Jl Ki Kk Ms Pi) Id(bO Ed Jn Jr Ms Nn Qy) Jv(Dk Hu Jq Jr Ke Kk Nn) Jd(bM Ji Jr Ky My Pf) Ri(Cp Ji Jn
Ke Lw Pe) Ax(Me Ql Qy St Vt) Et(Lv Nl Pd Pf Qb) No(Jq Lj Lu Mq Qa) Kq(aL Co cZ Dp Nf) bA(bW Kr Ml Qa Qe) Qy(Ij Kn Pk Qv) Ke(aL
dA Fn Hu) Kk(Dk dL Mm Oi) Pf(Dc Jq Kd Sr) Cv(aD Cx Lv) Nn(Me Nh Nw) Ql(aD Kn Lw) Ur(Is Nf Pk) dM(Fp Ut Wm) Ch(Ba Ut) Fy(Ao
Ki) Nb(Qa Wm) Hu(Kd Vt) Tn(bC bE) Oh(Ok Qe) aE(Jl Jn) aW(Kd Kf) BoJq CsNi EdRf FnHw LvbW LwIs MpQv MsVt MwPi NaaA NcUn
IoNw QaPe JiPc SraR QgKp JrdA KiKn OkPd UhPk} Ch{Nn(aD An aP Bo Dk Gl In Jh Lw Lx Mt Oi Qa Vt) Ly(cT Je Ke Ky Mu Nv Ok Om
Pe Pf Qd Vt) Ni(cW dG eC Iv Jk Jp Ky Lj Oh Ow Ur) dA(aJ Ez Fb Ki Kz Mn Nt Ok Qt Qv St) Kx(aD Ef Gl Ke Ml Mt Nb Nv Nw Ow) Pk(Cv
Dk Jv Ky Nw Oh Oi Qa Qv Uf) Nr(aJ Bo Hc Ji Lw Nc Ny Og On) Nf(aD Aw Bg Dc Lh Mt Pd Pg Qa) Qy(dL Gl Id Ij Jl Me Oe Qt Ri) Po(Ba Bo
eC Jj Jv Lx Mu Ny) Rf(aW Dk Jl Jn Nc Ny Pf Uf) Ed(Ax Cv Ef Id Jk Lh Uf) Jy(aP Ax bV Dp Jr Qe Sr) Ql(aW Ba Im Mr Mu Og Qv) dM(Ba Fy
Gl Ji Jk Nt Qd) eC(Hv Hw Ir Iv Md Ml Ph) Et(aW cI cN Iv Ri Tn) Je(aA aD Bo Cw Jp Qx) Fa(Lw Nb Ny Qt Sr) Lu(Cw Fp Iv Lh Qa) Im(aJ Iv
Jh Ki Lx) Kz(Ax bF bQ dG Jp) Ba(bV Ms Mv Oe) Me(Cv Fr Mr Mw) Qv(Fy Is Mw Qe) Jn(bM Db Nw Pf) On(Af bN Dp Pa) bR(Lx Pe Pf Qa)
cT(Fb Jl Mu Qa) Mq(Ky Lx No) Tn(Fn Nj Uh) Kr(Cw Lw Uf) Ri(aJ bZ Mr) aA(aD cW Lx) aW(bQ Ji Pd) Cs(Dp Jh) Ef(aP Li) Fr(Dp Og)
Fy(Hc Na) Nc(Jl Pe) Sr(Ky Qz) Jr(Io Oi) Ut(aK Fn) bQ(In Uv) AxQt DbOm EzcN FbcW FpKy GlTv NoHq LwcZ MaIv MrPf MsJl MuMv
HuKe IdHc IsQc QdOg QeJj KdKq OiPe aMbA} Ed{Oi(aP Ax bA Bc bV Cv Ez Fa Fr Jq Ki Lh Mm Mw Ok Pf Uh Ur) Oe(aJ Cs dA Fb Id Ih Jk
Mr Nr Nv Qa Qe tF) Jv(Bc cT Ma Mr Nf Nt Qe Ri St Tn Uf) Ur(aA aD Jy Lh Mq Mu Nw Ok Qa Ra Rj) cK(cT dF Dk Is Jr Ky Mu Oh Om Ow
Qe) cN(bA bS Cv Dc Iv Jq Kr Ly Og Rh Vt) Nc(Ax dA Hu Jp Jr Jy Nn Po St) Qg(Ad Cw Hw Md Na Oh Pi Rj) Ri(aW Bc Dc dG Ly Ms Mu
Ow) Og(Ax Dk Id Ki Oh Pf Qy Rf) Cv(aA Hc Jn Ql Qn Qz Sr) Vt(aK aV bQ Dp Io Kg Nl) Sr(Hx Iq Iu Iz Jj Ms) Rf(cT Ji Jq Mq Tv Ul) tF(bF
Cs cT dG Jl Ld) Jj(bR Et Ez Pd Qe) Kq(Ao Dp Md Mr Nx) Kr(dF Fa Is Mu Ut) bO(aD Et Id Is Mu) Ms(Jp Lh Nn Ql) Ni(dA Ji St Uh) Jy(bS Hq
Pk Tj) Ki(cT Kn Ml Om) Lx(aM Nj Qz) Qv(dM Jn Pj) Oz(aP Kk Tn) bA(aK Mj Nl) bV(bR Jn Mr) eC(An Cp Qd) Dp(Fr On) Fb(bQ cW) Fy(aW
Hq) Lw(Ow Rh) Ma(Ng Vv) Hu(Et Lv) Io(dM Mu) Jd(Qh Vv) Kx(Co Uf) Nw(aM Ra) aP(bR bS) cT(bE Pk) TjPo FwOn MgIs NlJr IddA TvPj
OmbX UvdJ UtcZ} Ni{Co(Ar Ax bA bV cI Cs Is Lj Me Nj Nk Qb Ri) Jv(aP bA bH bX Jj Jn Jr Kr Ms Nn Po Ql) Kr(aW bW Cv Fr Jl Mq Nr Qe
Uh) Ax(aA aD bR Hf Jo Nj Pc Qu) Po(Hr Iz Jn Jq Kx Mt Qu Ri) No(aV Et Hf Kd Lw Me Mm On) Jr(Iz Lw Lx Og Pc Pf Qg Ur) aW(bM Gl Lx
Ly Mm Nr Pf tF) Mn(dM Hc Im Lj Me Mq Og) Jj(Jl Li Lj Lv Mw Ny Pg) aK(bR dG Lw Oh Ow Rf Ur) bA(aF Bg eC fP My Oz Ri) Qa(Mm Oh
Ok Om On Qg) Qb(Jg Jq Mp Ng Og Oi) Qe(Lx Mu Oh Om Pb Pc) Ao(Et Lx Pe Sr tF) Cs(aM bR Jo Lw Me) Kx(Cx Ji Nw Rf Uh) aJ(eC fP Hf
Kl Ly) cI(Fa Ke Ly Mm Ne) Ng(Bo Mv Un Ur) Kg(Hu Nn Tn tF) Lj(aA Et Mp Ok) Rf(bP bV Oi Ri) cN(aE Cv Jq Nw) Ms(aD bV Mu) Jd(Hc
Ki Mg) On(aA Hq Ns) Et(Jo Mu) Fa(dA Qu) Nr(Qu Ur) Lx(Im Ly) Me(aP Qg) Mp(Mq Ns) Nc(Fr Nn) Nj(Bo Qg) Iz(Kq Ua) Ki(bV Ky) Un(Ko
Pk) Vo(Ke Mm) bO(dG Ji) dM(Cv Rh) eC(Hu Kk) BaSs BgMu DpUe LwaE LyOh NfaP NkdA HcdG SrfP JnKl RiUr NvNw OfOm OgPe
aAaG cWcY} Hc{Fr(As Cq Cu Hv Hw Ir Js Kp Kr Nn Oa Ou Qu Rj Ud Up Vp) Oh(Cw Hv Hw Jq Kd Kp Ly Mu Pi Ql Uk Ul Vt) dG(bN Cw
Hq Io Jj Kk Mp Na Ng Ns Ny Qy Ut) dM(aD Cv In Jt Ko Mu Nb Qd Vt) Cs(aR Jj Ju Kd Lu Mq Uf Ul) dA(bW Jd Jr Mu Mx Rf Uf Ut) Sr(Cv
Dp Hu Je Nl Pf Ri) Ur(Cq Cw Kd Kf Or Tv Vp) Qv(Gl Js Kg Mw Nw Pj) Jv(aD Di Et Fy Jy Lw) Kq(bX cN Co dJ Nr Uc) Oi(AR cN Et Kk Lw)
Pf(Id Jr Kd Kp Ml Mu) bV(Dd Je Oa Or Ow Uh) Nn(Id Ji Ql Uk Un) Mq(aD cK Jd Ny Tv) Uf(Lv Pk Qx Rf Tv) cT(Ad Et Iv Lh Ml) Nr(bW Io
Nw On) Jd(Bg dL Jr Ri) Un(Ih Ii Io Ir) aW(bQ Cu Id Nt) Ax(Ad Up tF) Po(Je Jn Qy) Fa(dF Je Qu) Fy(bW Cv Hb) Tn(cH Mu Qn) Qx(cN Et St)
Jj(Fb It Of) Jr(bH Nc Qg) Kx(Hu Ok Qc) bM(Kd Lv Mu) Wm(dF Ky) Lu(Ky Ok) Lw(aM Jn) Ms(Ml Rf) Jp(Ow Rh) Kr(bA Mx) Ri(cN Pe)
aP(Iv Lh) BabP CodF CvPk FbLx MnaD MrTv NdOn NgIs IdOw QadJ JnJu KgOk KkRf} Kr{Jd(Ad aJ dG Fa Hu Ij In Ir Jq Lj Me My Oa Qe
Ri Vt) Qe(cT Cv dG Ij Jq Ki Ml Nn Rb Ul) dL(Ax eC Jl Mq Nf Nr Oh Ow Pc Pe) Pk(bA Id Jn Mn Mq Nn Oh Ow Ri) Iv(bW Cs Id Jl Kk Ql Ri
Uh) Ax(aA Is Jr Mm Nw Ql Qy) Mq(aP Js Ly Ok Qd Rb Ri) dM(bA Ij Jq Om Pf Qy Vt) Cs(Jn Ki Lx Mx Rb Ul) Nn(Iz Jr Kq Mr Ql Vt) Id(aM
cN dA Et Nf Vo) Ke(Bg cI Ef Iz Of Vo) Kx(aP Jq Mr Ok Ow Po) On(Im Kl Mk Ml Nv Ur) Uf(Js Na Om Or Rj Vp) eC(As Hu Ij Ir Na Up)
Cv(Jr Ml Oa Oh Qb) Lx(It Nf Ow Pi Ud) Uh(Ad Mj Ml Pe Ra) aM(Jn Jr Mn Nw Qg) bV(cA Et Jy Mp) Lw(Ly Mj Rh) Mx(Hu Qy Ur) Is(Ng Oi
Ri) Qa(Oi Ql Ur) Sr(bA Iu Pf) Jj(Mr Nr Po) Jn(aD aW Og) Jr(bO Mu Nc) Ki(Cw Om Ow) Nw(Jq Ow Ra) Oh(Jy Qz Ul) Co(dG Js) Et(Fa Oi)
Fr(dA Kz) Mm(Me Nf) Jl(Iu Iz) Ql(aJ Fa) Ok(cN Kg) Pe(Ng Qu) DkJv NsdG MpQv MraP MuaD TnOz JyaJ OmUr OwVt UncI bAbW}
Ng{Jn(aP aW BA cN cT Is Jp Ma Mn Mw Pc Pf Rh) Pf(Dp Hw Ij In Ir Jo Kz Lu Mm Mz Nv Pc Ql) Im(aW cN Ir Jh Ma Mj Mk Mt Mx Nb Oz
Pa) Nf(aW bZ Fy Id Jr Lv Mn Pk Ri Vp) Sr(aK Ba dM Ki Kz Ly Pk Qy) Mv(Fp Iv Li Mr Na Nt Pd) Kz(Ez Kx Lh Lw Mn Nr Ri) Rf(aP bA cT
Cw dA Id On) Nw(Jo Jt Mi Mm Nb Oi Ok) Qe(aW Iv Jq Me Na Pe) Jg(Hw Li Lu Nr Om On) Kq(Ba dA Jd Ly Mq Ri) Ma(Lh Mw Nu Ql Ri)
Hu(Cs Fa Mn Qb Ri) Jj(Fr Jk Lh Nv Pg) Wm(Ih Jh Jq Pg) Fp(Jh Jt Jy Pg) Nn(aV bA Ow Ur) Mw(aW Mi Nm Ny) Is(Io Mi Mz Nb) Kx(Fa Jy
Oh Ri) Li(Ii Iv Lh Lu) dA(Ji Jl Nr Oh) Ba(bP Qa Qx) Mm(Ml Ok Om) Mq(Nh Pc Ur) Mu(Ir Mi Nb) Qy(Fa Po Rh) Ql(Ax cW Fa) Ow(cN Ny
Pk) Pe(Dp Jq Qz) Lv(Mt Qd) Mn(Ne Qb) Tn(Nk Oz) Jd(aA Ji) Jl(Jh Mz) Jr(Mg Nv) Ri(Ar Qa) AxEz CsIv FrbO NrJv LuOh LwQb IjdM IkJp
JedN OkeC PkaP} Og{Mq(Id Ir Kd Kq Lh Na Nb Nf Nt Pi Qd Ri) Fr(bO Ij In Jq Jv Li Mr Mt Na Nb Nw) Ki(bA dM Et Fa Im Me Mw Nt Ny
Om Oz) Kx(bO bW Et Hu Mm Mx Nf Qe Uf) Oh(Hw Hx Jg Jo Jt Lu Mm Mr Pf) Fp(bV dM Jk Jt Lh Lv Mw Nb) Wm(Iq Jt Me Mt Nb Nx Pa)
Im(Is Iv Lh Li Lu Mp Pe) Et(Hv Hw Ij In Ir Na) Lv(Jg Mn Mw Ny Pf Qd) Ri(Cs Is Jn Pk Ql Rf) dM(aM Lj Ml Oa Po Rf) Mm(Hu Ij Iv Ml Nu)
Nn(Dp In Mz tF) Nf(Id Jc Kc Mn) Hu(Cs Ok Ow Qb) Qe(bO Jn Mz Pa) Jv(Cv Oa Pd Qy) Nw(Ir Jo Jt Kz) Mw(Bg Ih Is) Iv(bA dA Qb) Jr(Ma Pc
Pd) Kq(aL Fn Hq) Li(Io Mt Nt) Ql(aP Fa Ly) aA(Nt Qu Uf) eC(An Jt Kp) Nu(Mp Mt) Ml(cN Jd) Is(Al dA) Qb(Jq Pe) Jg(Jn Nh) Sr(aW Ur)
Ok(My Pf) Un(bM Cv) AxQy BbOm BgOn CoJl LxQz MnNe MpHq IddA HbRf JjJk PebO} Jj{Et(Jo Jq Js Jt Jv Li Lw Lx Mt Nw Pc) Me(aA
Hw Jg Lh Mr Ne Nl Nm Pc Qd Ri) Pk(aV cZ Jn No Nr Oi Qe Qy Un) Mw(Ij Ir Is Iv Lh Ny Pf Pg) Jv(Fy Hf It Iv Ks Ny Ow Qa) Mu(Hw Ir Jo Js
Mz Nt Om) Jq(Li Mr Mv Ne Nn Ny Oh) Lj(Hu Ij Mn Na Ne Om On) Pd(Ir Iv Lh Lw Lx Mz Pc) No(Jl Jn Lh Lw Ok On) Lv(aA Ii Ij Li Ml Mv)
Nh(Jp Lh Om Pf Pg Qd) Is(Jt Kx Lh Mm Mz On) Nn(Jl Lh Nw Ok On) Mr(bR Jn Ok Om Ql) Iv(bO dA Jn Nx Ok) Kz(aD bE Fr Fy Jl) Ri(dA
Im Jn Jr Oz) aA(Li Mn Oz Pe Wm) Mv(Mn Na Ny) Jg(Im Jd Un) Rf(aM dA Ql) Ly(Fb Sr) Mj(Ik Nx) Hu(Na On) Jn(Jo Pe) Nw(Li Nt) Ny(Lh
Lx) Oh(Ok Qa) Un(Jt Kl) bO(Fy Ql) eC(Sr Up) CvCx WmJk FrJi NrdN LwHw MlNx NeIj IkJp ImKi JoPb JrbN KxVt OiOn UvaV bSdA}
Oi{Jr(cZ dA Fr Jd Ki Ma Mn Mw Ne Nt On Pk Rf) Kx(Ax cT dL Fr Id Ji Jy Kk Ly Nw Qd Uf) Im(Co Et Ir Iv Jl Lh Lv Mi Ml Mq Ri) Fp(aW
Co cW Lv Mi Mr Mt Mx Nb Rf) Nn(Fr Ji Jq Js Jv Lh Lw Mt Mz Pk) Qa(aW Fr Jl Jn Jq Kg Mr Mt Pa Pc) Po(Fr Jd Jt Mt Mz On Pe Pk Ri) Pk(aP
bA bW dG Jl Jv Qy Ri) aA(bP Fr Fy Lh Mf Mn Mq Pe) Mu(Hu Lw Pa Qd Ql Ur Wm) Dp(dG Fr Jl Pf Rf) Et(dA Jn Nh Oh Qb) Is(Lw Lx On Pd
Pe) Ax(Mr Ql Qy Ri) Qe(dM Lx Nf Pc) bV(Iv Me No Qy) Ms(Nw Rf Sr) Jd(aW Rh Sr) Jl(Ji Mq Oh) Pe(Co Mm Om) bO(Cs Oh Ow) dM(Nr Qt
Ri) Wm(Jq On) No(aD bN) Jn(Jg Pf) Li(Mq Nh) Ql(aP Iv) cC(Cu Kn) CoFy CsRf LvOn LxNd MrcN HuaM QbPf JicZ SrKg QgUn KqaL
UrdN} eC{Hu(Ad aM An Cq Hv Hx Ij Ir Ji Jn Ke Nf Ny Pe Qa Uv) Ki(Ad An As Hx Ij Ir Md Mt Pb Pe Qa) Pk(bW Cp Cw Fr Hb Pb Qd Rf St)
Ms(Ad Hw Ij In Ir Up Vp) cI(Ad Hw Ij In Ok Pb Up) dM(Dd Ji Js Ml Mz Nb Pb) No(Al Dd Ke Lw Qv Uc) cK(As Ij Is Js Ra Uv) Lu(Ad Cq Cw
Nf Rj) dA(Cs Hv Kd Mz Qa) Cu(aD aE bH Jv) Ly(Kd Ke On Vp) Hw(aP Bo Kk Qv) Id(aJ aP bH dJ) Ir(Fa Jd Jv Qv) Ra(cN Jn Up Ur) Kx(Ad
Cp Ke Pe) Ny(bF Kg Oa Ri) aW(bA Cq Pb Rj) Jd(Cs Cw Rj) Sr(aD aE Na) Qg(Ad aM Kn) Jn(aE aP Fn) Bo(In Kd) Mg(Lw Uc) Mz(Ri Ur)

Figure 8 Continued

Iv(Jv Qv) Qu(Kp Nf) Jq(Bg cX) Ke(Ao Ko) Kg(Bn Hx) Un(Dp Hf) aD(Hv Rj) bA(Nw Pa) AdbP ApaP CsJy DkKl MtbV NcJr UdcN InaJ QtOm JsUr Knbl} No{li(Ad As cP Cu Cw Dc Kd Kp Mq Om On Ra Rj Ud) Cq(cT Id Ji Kn Pi Sr Up Vt) Lw(Bg Im Kd Lu Mq Pk Qz Ua) Ur(aD Af aM Ao dA Dc Tv Um) Fw(Co Id Kd Me Ml Un) Mq(aA Et Jo Me Nn Pc) cZ(Id Ij Kd Kn Pi Qv) De(Cv Ke Om Ra Up) My(Is Jn Jr Ju Lh) Bg(Cv Ji Jy Ml) Tj(Cx dM Ju Me) Hq(Hf Kz Mi On) Oz(cA cN cT Jl) aA(aM Mm Nl Ua) Ad(aD Of Qg) Cp(Kd Ra Rj) Cu(Fy Jq Rb) Me(Jq Ju Ok) Ms(Lj Mm On) Nk(Ao Co Ne) Ji(Kg Pc Up) Qz(cN Iq Vv) Qh(bA Ml Qv) cT(Kg Mg Vv) Al(aD bS) Dc(Fn Uc) Dg(cN Tz) Il(lv Pe) Qg(Id Sr) Vt(Jk Kg) Pb(Lh Pe) FnRa NnMv NsOn LuPc LvOk MdJq MmMu NcaM NjUa UcIj HuOm ToPg HbbN IoaD IuOw QvdA JoPk JtdL bRbW} Jv{Ur(Ax Dc Id Ir Ke Kq Om Pc Ph Ut) Pk(An Ba Cv In Kk Ny On Oz Pf Po) Kx(aW Dc Kd Kn Me Mx Mz Ny Tn) Rf(aM aP aW bA cW Kz Oc Or Uf) Kz(Ax bA bF Hu Id Jp Mu) Nr(aP Jy Lu Mr Oe Ri) Ms(Et Kq Lh Pe Po Qe) Nn(Me Mr Oe Oz Pa) Ly(Fr Je Mu Ow Qa) Qv(dA Oz Pe Po Qd) aW(Et Jl Nf Pe St) dM(Cs Et It Ny Qt) Mr(aE cN Ky Ri) Kq(bN Co Iz Pc) Ar(Dp Id Mu) Ax(Nc Oz Ql) Nf(An Om Qd) Is(aE bP Ir) Jd(Kn Pi St) aP(Dp Hu Ju) dA(Jp Qd Qe) Cs(Et Nc) Fa(Gp Oz) Fn(Jq Qa) Fp(cN Mu) Lw(dE Mq) Tn(Pc St) Iv(aE Ql) Ji(bN cC) Jr(bV Nl) aK(Jq Qa) dN(cT Ke) BaMg PoPa EtbX NcPe HucW TvSt ImRi QbbV KgLh OzbA} Ly{Ki(aD Bc Fb Is Iv Ke Ld Mq Mu Nv Ok Om Pd) Ri(Ar Et Id Kq Lx Mm Mr Nr Oh Pk Qe Rf) Ur(aM Fp Hu Jq Ke Kq Mu On Qa Rm) dM(bN bV bW Lh Ml Ok Om Rh Wm) Kx(aJ cN Cv dA Fa Qy Vt) Ql(bW cT cW dG Ke Oe Pk) Jd(Cs Mm My Oe Qv Uf) Qu(Ba bQ dG Jl Ow Pe) Wm(Ih Iv Lw Mw Mz) Sr(Io Iu Ju Kl Lw) Un(bO Cv Ju Oz Uf) cN(bR Dp Fa Je Kq) Lx(Im Mu Nd Rf) Nw(My Nt On Qv) Mq(Fa Fp Rf) Ne(Ok Om On) Nh(Oh Om Qe) Io(Et Jl Kq) Ju(bA bV Fa) Vo(Id Is Om) Pk(bA bM dG) Mu(cT Et) Rf(Mm Ul) On(Bg Nd) dA(bM Vt) AxUf CoNn CvQx FpOh FrbO MeOk MrbV IvaW JeOw} Nf{Jl(aE Co Et Hu Il Lv Mm Qu Ur) aW(bA bV cN Id Ki Pe Po Uf Vt) Co(aP cN Dk Id Ky Po) Et(Iv Kg Nt Pe Pf Qe) Ms(bP Cv dG Fb Ke Lx) Nw(aD aF aY Mw Ri) Ur(aM dG dL Om Up) bV(bO bW Jr Me Nr) Cv(aD Af aJ Io) Sr(Fw Lx Ug Uk) Qv(aP Fy Qd Qe) Qg(dG Jn Om Pe) Jo(Dc Ke Uf Vt) Kg(Jt Kx Mz Pi) Ki(bQ Je Jn Nn) cN(Qa Qe Qn Rh) Lw(Cx Jp Ky) Ii(Dc On Vt) aJ(cT Jy Mu) Fr(Ao Ug) Iz(Fb Vt) Qy(aD cT) Qu(dG Jn) Ke(bX Cq) Kl(Uf Un) aP(bR Oe) bP(Id Vt) cK(Fa Jd) BoDp CsRi FpMm LuQl LvQe LxMt MeaA TzUn IodA IuSt JeKy JrUg KqbH KxUf OfVp bAbW} bO{Pf(aC Co Id Jq Ky Ml Mq Oc Pc Rf Uv) Po(bW Cv dL Jq Ke Ks Ky Rf Vt) Fa(aA cN Js Kp Na Qa Uf Vp) Mq(cT dG Ke Kk Oh Pe Pk) Jl(Ax bR Cs dM Ms Pk) Rf(aM bW Fr Lx On Ul) aJ(Gl Ij Ki Ld Mt Ra) bA(aP cN Cv Jq Nr Oz) bV(Jq Lh Nn On Uh Vt) Fr(aC Kz Lj Oa) Lx(dL Hu Jq Up) Qa(Iz Ms Of Ug) Jn(dG dM Kx Ur) Jr(Al aM Co Hu) Oh(aP Ki Kx Uv) Cs(dG dM Ri) Nn(aA cW Iz) Kq(aW Iz My) aD(aP Is Nr) Qe(Io Ur) Sr(bB dJ) Kx(dF Et) Nw(aA Li) Pk(Uf Uh) BgJd BoaM CoOn NrJq LvcW MuLj HuaP IrIs IvUr JiQg KgLh RidG PeaW} Me{Jn(Ao bP bV Cv Et Fr Nn Om On Qv) Et(Lu Lw Lx Mq Oh Pc Qa) Fr(Bg Hu Im Ji Ms Nn Ns) On(De Jh Mk Mq Mv Oh Po) aW(dG It Oz Pe Qd Sr St) Nn(Iz Jq Lw Ms My Qu) Mn(Fp Jr Kg Lv Lw Mt) Mm(Ax Lj Lv Pe Qa) Un(Ii Jt Lu Nm Ri) Ur(aP Jl Lu Uv) Po(Is Jr Ms) Lw(Jd Jr Oh) Ki(bA cT Ri) Om(Hu Mq Ns) bV(cA dA Lx) Ms(Jd Oh) Mu(Hu Kx) Is(Ao Jr) Qe(bI Lx) Qv(bE Je) Kq(dM Ii) Ri(aP Ql) Nw(Bb Pc) Ok(Jo Pc) aA(Pf Uf) bA(Fw Oz) bP(Ba Ql) dA(cT Ji) CoKk CsJq CvNr DptF WmPa MhRh MtMw IhSr QgaP RfcN} Mq{Nw(Ir Jn Jr Kl Lj Lw Mm Ns Nx Pz Qa) Et(Im Jn Js Mt Mz On Qa) Im(Fr Lv Mt Mz Om Pc) cK(aD Bg cA Co Ke Ur) Po(Hr Mt Mz On Pc) Qu(bA Jr Kk Ky Nn) Kq(Cp Jg Jt Kg Ki) dA(cF dH Lz Pf Uk) Mu(Dk Ki Lw On) Jq(Kl Md Mm Qa) Oh(Jn Mg Nn Pc) Dc(Ii Jt Ki) Fy(Bb Bg Vo) Is(Ii Kl Pc) Jr(aL Kx Ri) Nn(Na Oe) Lv(Jn Mr) Ma(Kl Ne) Ms(On Ql) Mt(Na Ns) Mz(aK dJ) Kx(Jn Ur) Ri(aE Qv) Rf(aW cN) Un(De Uc) aL(Ji Ny) bA(fP Qg) DpaW LxaA UaHu IktF InOk IzUt KiKy OfUp VtaK PbPf PkdJ} Jd{Bg(Ad Cp Cq Cw In Kd Kp Mi Na Pi Ra Up) Co(aA aD Cw dG Fa In Kq Mt Qe Ra Un) My(aM cT Fa Iv Jr Ki Ml) Qu(Ao bV Iv Oa Ow Qv Ri) Iz(aD dL Jo Kf Oh Uc) Sr(bX Jg Jo Of Vo) Kx(aD aW bM Pc Ql) bP(bR Jn Ky Ml Oe) Kl(aP cT Cv Jr) Ms(Ax dM Rf) Uc(Jq Qa Un) Ki(bV bX dA) Kz(aW Lx Qv) Ri(aD Ax Ua) Pk(bW cK Qg) cT(Mg Vo Vv) Bb(Mu Rf) Cv(Cx Jg) Nc(bV Hu) Jo(bA Qa) aD(aA cZ) aM(dM Kg) AoMr CsOe DeJi DpUr LwSs UaRf HuaW IiIs JgUn QvbX OfPc PabA PcdM} Pk{Co(aP Fb Fr Gp Iv Kq Kz Qc Ql Ri Sr) Ms(bW Et Hu Ji Jr Lx Ow Oz Ri) Kg(Ax bW dG Fa Hu Nw Ok Pe) bA(aM aS bE cZ Ju Kx Qu) cN(bN cL Hq Ky Nd Ns) Lx(aW Cq Nc Pa Ur) Lw(Cs Dp Nd Oz) Qg(dL Ml Qe Qu) Ri(cK dG Fa Mr) Of(bQ bZ Kx Mu) Ur(bW dA Kq Uv) bP(Hu Ji Oz Uf) Cv(cK Kz Qz) Lu(Ji Jn Jr) Iz(aJ aP Uh) dA(Qv Uf Uh) Mm(aK bN) Jl(Ir Vo) aA(bW Et) aP(Kx Qu) AoJy BgMw MuHq JgKq JicZ QycT JotF QlcK NwaF UfaW bWdE} Kx{Kg(bA Cw Et Ij Jq Ok Qe Ra) Qe(aW Co Iu Iz Kl Ms) Ur(bA Id Is Pd Ql) Pc(Ax cT Io Lu Wm) dA(aV Cs Iv Ns Ua) Co(Et Fa Hu Jl) Mu(bS Kl Oe Oz) Qu(bA Iv Pe Sr) Jy(Cs Oz Qv Ri) Ki(aJ Bn Jt Kf) bV(bR Io Ju Rf) Dp(Cs dG Un) Qa(Fn Jo Qv) Kq(aM Kf Pa) Ri(aD Pe Wm) Iv(Io Ms) Je(Bg Kz) Jn(Ks Tz) Jr(Nc Qc) Un(aD aM) Oz(aJ Qy) aA(bW Rh) bA(Nj Nl) AlIs FpIk FrKz MlQg UaHu IzPe SrbP QvRf KeaK NydM aMaQ cWtF} Mu{Oh(Et Hv Hw Im Iv Lh Lw Ok On Pe) Nw(Hv Hw Ir Iv Jn Jq Jr Lw Mw) My(Fr Hv Ij Mi Mn Mr Mt) Oe(bV Is Iv Li Nn Qb Qe) Lv(Ir Jn Lw Mg Pf) Ms(Im Jl Lh Mr Om) Qa(Bg Et Jl Jq On) Jr(Ir Iv Jl Mm) Bg(bX Fa Jn) Pb(Li On Pf) Cs(aF Qg) Fp(dM Iz) Lx(Im Pg) Mg(bA Nn) Ih(Mn Ns) Sr(aF Kl) Jt(Lj Po) Kz(Ax Qv) Pe(Co Pc) BbRf DkMl EtOf MmLj NdPd HuJq HwUr IzKq QuRh aEaM} Dp{Qv(Ad bA Cp Cw dL Hw Ij Ir Kp Lx Na Pi Rh Ud Up) Ur(cW dM Ha Jn Jr Kd Md Nm Nr Nt Qe Ra) bV(cW Jl Ld Ml Mr Nn Nr Om Rh) Fa(Ao Is Iz Kd Kg Kl Qu Uv) Kg(Ij Jt Ke Lw On Po) cN(Ax Iv Jn Ky Kz) Co(bQ Cs Jn Kq) Nn(Ik Iz Kl Mg) aP(Mg Ms Ri Sr) Lu(bA Ky Li) Lx(Ao aW) Jo(Ij Ok) Un(Ii Ug) Pe(aW Iu) bX(Kq Lw) dM(Iv Mr) CsaJ IzJl SrdJ} Ri{Kq(Ao aW Fn Jg Nc Qu Ur) aM(Ax bV Cs Jn Jr Ql Un) Ur(bA In Is Mr Po) dM(Ar Ij Jl Ny Qe) Nc(aP Po Qa Qe) Ki(Iv Oh Pf Tn) Kz(Ax bP Ji Qv) Cs(cN Ms Ql) Iu(Im Qa Sr) Qu(bV Fa Nn) Kl(aP Et Jn) Rf(bA Lw Ql) Oz(aP Ax Po) Qe(Qc Qv) Jo(Is Pe) Uh(Tn Tv) dA(Ax Ky) AoJn CoFa CvCx FpdG LwdE MlKg MsIv MwMy IjOf IzSr QvVt JrbV QlaD OwUn aPbN bRcN} Un{Fn(Ao Io Ir Jo Ow Oz) Ko(bW Cv Jq Ke Oz) Ao(bF cK dN Oz) Bg(bF cO Hu Lw) Kl(bX dM Hb Nc) Oe(aW Kz Nc Oz) Ax(Qc Qh Qu) De(cN dA Lw) Nn(aK Cp Ua) Ii(aM Hu Lu) Qv(aW Co Rh) Qg(Lu Oz Ra) Jo(bR dA Hb) cT(Ir Iu Qh) Cs(Al Db) Lw(Kf Vo) Jt(aA Jy) Ur(dM In) bA(cZ Ki) AdSr BbbF CqKz NldM UaHu IoOz IrIv QcaE JgOn QuaA KgcZ KqbX OfdA bVcA} Po{Pb(Hv Hw Ij Ir Jl Jn Jr Lv Mm Mr Mz Nt Qa) Hu(Im Is Jq Nk Nn Ok Qe) Ns(dA Mp Oh Om On Qe) Ms(Jq Lw Mm Nb Pe) My(Et Lx Mw Na Om) Il(Iv Jl On Pe Qe) Ii(Nn Oh Ok Om) Qa(In Jm Oe) Kg(bR Rf Sr) Co(Nn Ql) Mg(Mn Om) Hq(dA Lx) Im(Lv Lw) Jo(Fr Nn) Nw(Nv Oe) NhNk UaaA InOh IsOe QudA OfOm UrPi} Rf{Kg(As Cp Cu Dc Hv Ij Ir Jn Jo Kd Ok Rj Vp) Co(aP Cs Je Ji Jq Ke Mj Nm Oe Qy Ra Ul) Vo(BA Jr Jy On Sr Uf) Kl(aP bC cN dG Fr Jl) Ao(cW Ju Mp Nn) Iz(Lw Nn Qy Vt) Oz(Ms Oe Ur) aM(cN dJ Lu) Hu(dM Ua) Qv(Ki Ql) cN(Bg Oe) BbJq IdOf IiPe HbaA SrbH QubV QgVt JoKq KiKy PcaW cWdA} Kq{Bb(bG dA Iz Ki Lj Ql Sr Vt) bX(aA aM bF Ji Lu Nm Pg Qv) Ki(Jt Ko My Nx Ur) Iz(bR dA Jn Ur) Jg(Cs De Kg Sr) aK(Cp Dg Ms My) Bg(aA aW bN) Jt(De Ow Ua) Fn(bP Fa) Fp(bW Ef) Ii(Pa Ql) Io(aU Kg) Kz(cI Qg) Vo(Md Vp) aL(Ad Qz) AlUc CxHq DeUr LwKo MrTv MyKf IsKg JeOf SsbH QuaA KlbW bFcI} Lx{Qe(Hq Hu Im Kl Lv Ms My Ns Of) Of(Cq Cw Hv Jo Lw Mz) Pb(Ij Mz Ne Nh Ok Om) My(Hw Je Jq Jr Ns) Im(Jq Lw Mh Na) Ns(Jr Lv Na) Uc(Cw Id Ij) Et(Io Mg) Lv(Mz Nn) Mp(Nd Pg) Nl(Kz Ne) Hq(Ij Mi) Hu(Ji Jr) Jn(Cq Il) Pc(aA Ur) aU(Sr Uv) bR(dA Mr) FwKz MdIn NaNh NdbX JrKl PacT} aA{Io(aD Is Jn Lh Li Oh On Vt) Oe(Cs Fr Ma Ny Pf) Iz(Ef Ji Mw Ql) Jq(bX cX Li Oh) Pc(Jl Li Na) Co(Db Nr) Ne(Nc Nl) Ua(Nr Qy) Hu(Jl Ok) Jg(Lj Pb) Ji(Af Fn) Ki(aD dC) Ql(cT Nl) On(bX Lw) aW(Iv Qe) bP(Fy Ow) CxaD EfMn FwQa MfPb MhMm MlIm SrOz QucW JndC KlLh UfbX} dM{Oz(Cs Jl Jq Lv Lw Mt Ny Oe Pf) Kl(Et Ez Im Is Nr Pe Qt Sr) Nc(Nn Oa Pi Qe) Pa(Et Lj Oa On) bN(Cw Id Pf Uf) bX(Fa Jq Pj St) Pc(Fa Nn Qv) aM(Hu Jy Ql) Co(Is Pe) Fp(Jq Ur) Mr(aW Ow) Iv(aD Nw) Lj(Db Jy) Ny(Bg Of) CsQy FnMl IjOf QaQc JicZ KzcT} Ms{Et(Io Jn Lu Ne Nh Nn Nw Oh On) Ql(Fa Iv Ki Mr Oe Qv) Nw(Ij Iv Jl Nb Pc Qa) Om(Im Jn Qa Qb Qe) dA(Iv Mr Nn Qy Vt) Wm(Jp Lh Qb) Nn(Jn Kl Lv) Qe(aW Im Oh) Ji(aV On Pc) Jr(Fr Mn Mw) Jn(Ju Qu) CoIs FpMp QaOn SrKi KgLh RhdN} Kz{Co(bQ

Figure 8 Continued bV Is Kd Ke Kn) Qu(aP Ax cN Lw Mn) Ur(bV Nw Pf Qe Qy) Iz(Jl Nn Nv On) Jq(Ao bP cl Jo) Ki(Di Oe On Pe) cN(dH Ju Kd Nd) Lu(Nw Ql Vt) Lw(aE Qz Rh) Ji(cZ Qg) Sr(Io Ir) bA(Qy St) BbNw CqOn FrKl FybH IiJl IuQe JebM aJdA} Fp{Mm(Hv Hw Io Ir Iv Jg Jn Ma Mv Mx Nb Pf) Ik(Jy Li Nh Nt) Cv(aP Ky Rh) Nn(Iv Mz Oh) Mn(Hx Lv Pa) Jq(Iz Qe Tz) aD(bV cE Nw) Co(bF Kd) Is(Il Jm) Jp(Lv Pf) Ke(Ii Iz) BbJy DcJo EtMt NtOh LwaW MgdF NkJl StcN JrPc OkUr} Sr{Iz(aK aV Iv Jn Jr Ql) Kl(Nc Nl On Ow Uh) Vo(cK Ji Lw Ma Oz) dA(aD aE dH Mk) Lw(Bb Jg Ko) Kg(bR Nl Oe) aW(Mr Nc Pa) Co(cK Je) Qv(aL Ki) aK(bW cT) bR(aV bH) bX(Bo Oe) AdEt BghQ CxNc EfFr IsJo IvJt QuKi QgJn UkcK OzdJ} Im{Lw(Ir Jn Lv Mr Mt Mz Nw Pa Pe) On(Ii Kl Mk My Nh Of) Nw(Ao Hu Iv Na) Lv(Co Fr Nn) Jr(Is Iv Ok) Io(Li Qe) Jq(Ao Ne) aW(bM cW) cN(dH Nc) CvIu EtLu FrJi NnIz NsMp MnNh HuOm IlQe KgbA KiOe} Kg{Is(As Cu Dc Ir Jo Jq Kd Oe Pe Ud) Fy(Bb Kf Nl Oz Uf) Vt(cT dN Nn Pd Ql) Qy(bA Ji Ml Qa) Nr(aM Iv Ml) Ji(aV Nn) Jn(aW Oz) Jr(bV Ez) Ql(cT Uv) Pe(Et Ki) dN(Ke Qh) MjQa QeRa OhUv} dA{Ur(aM Id Pc Up Vp) Jl(Bg Co Iz Nd) aD(aP Jn Jr Nn) bR(aM Cs Pe Vt) Jo(Is Iv Qa) Ao(Fy Pj) Bg(Pe Pf) Qe(Iz Kl) Qv(Ki Oz) Qg(bA Jr) aW(Is Nw) cN(Nd Oz) AfCv DbKi DgEt FaUa QaOf KlOk QlbV aCfR} Ki{Db(bA cT Ji Nn Pe Qa) Jn(aW bV Ky Oe) bX(aP Jq Ke Pe) Fn(Hw Kd Kn) Qa(Bo dE Qc) Cw(Jo Vo) Oz(bV Qv) Pe(Oe Qg) bR(bQ bV) dN(Fy Kf) CoNn CsJy DeLw NrKy LuJr MldE} Lw{Ko(Ax Oa Ow) bN(Jr Ky Lu) Cx(Hf Nc) Db(aW Ur) Et(Lu Ml) Fn(aM Cs) Uc(bA Jr) Qe(Io Vo) AoJn BbFy NrSs MlMp MtMy JtQl LjtF RhaK UrdE UpcC VoOz} Nn{Kl(bW Je Jq Ql Ul) Ne(Et Hu Lv Ns) Co(Is Iv Jr) Nw(Hu Ii My) Ef(Dc Jy) Nh(Hu Ns) LvJo IktF IzQl JrOe JtOk OfPi OnPb UrfP bRcN} Jn{Co(bZ cI Fa Nc Ur) Nc(Ao bV Ur) Qv(aL Oz Qu) cN(bS cA Ii) Ju(aW cI) Pa(aW bV) AoSt LuQu IoUr IzQy QgaM JyKl OebP OfOn} Jo{Et(Iv Na Nh Pe Wm) Iv(bV cN Qa Qe) dN(In Kn Pe Pi) Is(As Kd Ok) Qa(Lh Om Pe) On(Pd Wm) CxJq QeOk QlbA UvPd} Jr{Co(bQ Db Ld) Ns(Oh Om Qe) Et(Fr Ir) Nh(Mn Nc) Io(Li Mm) Qv(aK cZ) AoJy CvCx WmIn FyIi MpNd NlJl QaQg QtVo LjOn UraD} Ji{Cs(Co cZ Qc) Nx(Et Ok On) Vo(bE Fy Ma) aK(bA Ju) aV(Af Up) bR(cI cZ) bX(Co Tz) BaJg BgJe MyPc QvaU JlOf aLbN} Ur{Tv(Mw Ny) Is(Al Uv) Iv(aD cN) Jq(aF bX) Oz(Hu Nr) Pc(Ax bV) BbNy CvCx FnId NcPi IncN QaaK UtfP VtcZ aLbA} bA{Ql(Mg Qu Vo) Bg(Hu Je) Ny(Bb Hq) Oz(Jy Qu) Pa(Nw Pe) dN(Fw Rg) AfCv MrQy IvaL UhbX aMdJ aVbR} Qa{In(Is Iv Na On) Io(Fr Jl Mm) Ii(Fy Om) Il(Jl On) Qu(Fn Qg) FrOf NsMp QhQg OmPb OzaW} On{Bg(bX cI Cx) Pb(Hq Is Lj) Kl(Ax Dc) EfOa NrVo LvMt MrHq NeNl IoQe JgaF PaPf} Iv{bV(aV Co Nc Oe) In(Ow Ql) Nw(Pb Pg) bP(Hu Lu) cN(cL Ns) FnTv LvJq QlaW} Et{Lu(Lj Pc Qb tF) Io(Ml Oh Pc) AoaV FrKl MvMy QvfP JyVo PaPe} Qg{Cs(Kd Kn Om Pi Ra Vt) Ml(aP bP Of) AxaM TvIs QuPc KebX} aW{Mr(aP bV Oe Ow) Qe(dN Pc) Jl(Db Nc) MlQy MwIz IsJy QdOz aMbF} Co{Nr(Je Mr Qy) Pe(bN Mj Nl) Fy(Lu Nl) dN(Cs Mt) FaPd JeOw} Nw{Io(Jl Pb Pe) Pb(Hw Ij) BaSs WmNv LvHu MlaF MwMy NaPa TvNx} Kl{Uf(Pd Pe Ql) BaIt DkOh FybH LuIs MaJl QdOw QeQv JybV} bR{Is(bV Iu Lu) cN(aM Jy Oz) aJ(bQ Mr) JlbX aDbQ aVdG} Bg{Mw(bN bX cT Fy Ow Rh) Hu(cW Fr Ow) FaQy} dN{Fy(Fn Hq) ApUf BaMg BoHu FrMy HqPg IiJl IzNy KeKf} aD{bQ(aM bZ cA dH) Jy(aF cZ) FybH bXfR} Cv{Cx(aM Ax Ow Pe Tv) BaSs NrVo} Mp{Nd(Hw Mv Pe Qb) Ns(Mr Qe) HwOf} Qv{fP(dF Ma Ok) Ql(aM cK) KebX VtcZ} Hu{Iz(aP Ra) LvMm MgOw UaJl OzbP} Of{Qy(cT Ij) InbF QbOk JqPe UfPi} bV{MrOe QuOz QlPc cTfP cWtF} bX{Ke(aP Fn) FybW QlaP cXfR} cN{Mr(bS Nd) DbOz NrNc PccT} My{Fr(Js Lj) Je(Fa Pf)} Is{AlMg DcIi WmIl IuaM} Jq{Fn(aF Vo) CxIz aFbZ} Oh{LuLv NaIo NcNe VvaK} Qe{FnTv QcQl OmPb} Vo{AxJy BaVt FyUf} Fa{GzaV aEtF} Lv{Io(Jl Li)} Iz{FyPa TnQy} bN{KedJ aJbQ} NkTvSt InQbOk JyaFcT KyaMcK LdcWtF QlaPfP aCbQcY

Constrained panels with 2 analytes, where 1.0E-7 >= 'AUC p-value' > 0. Contains 373 panels of 61,235 total panels evaluated. : No(Aj Ao aW Bg bO Ch Co dI dM dN Dp Ef Hc Io Is Iz Ji Jj Jr Jv Kj Kl Kr Kx Lv Me Mq Ms Mu Nf Ng Ni Ns Nw Og Oi Oy Pk Qu Ri Ua Us Uu Vo) dN(aA Aj bA bN bR cA Ch cT dM Dp eC Gp Hc Jd Jn Jy Kg Kr Kx Kz Ly Me Mq Mr Nf Ni Oe Oy Pk Qg Ql Rf Rh Un Us Uu) aA(aM bJ bM bP bR dI Dp eC Et Fp Im Is Ji Jr Jv Kx Lv Lw Mm Mu Nn Nw Oh Pc Po Qa Qb Qe Uu) Mu(Fp Hw Ji Jj Jr Li Lj Lv Lx Me Ml Mq My Nf Ng Nw Og Oh Oi Oy Pe Po Qa) Kj(Ad Cp Cw Id Ij Ji Jn Jq Jr Kn Kq Lh Lw Ml Ok Om On Pe Pi Pk Qa Sr Un) Jj(Dp Et Fp Im Is Ji Jm Jn Jr Mq Nf Nn Nw Nx Pd Pe Po Qa Qb Qe) Uu(Ba Cv Dk Et Fr Id Is Jd Ji Jl Ke Kq Lw Lx Nn Om On Sr Un) Ng(Et Is Jd Ji Jl Lx Nn Nw Oh Ok Om On Pf Po Qa Qe) Og(Et Is Ji Jl Lx Mq Nn Nw Oh Ok Om On Po Qa Qe) dI(aM Cs In Ir Kx Me Ml Mq Ni Nr Po Qa Rf Sr) Aj(Is It Iv Jd Jn Jr Kq Ni Pe Sr Un) Fp(Et Fr Jl Jq Lw Lx Mm Nn Ok Om On) dM(bR Im Iv Kz Me Mq Nf Ni Oy Pk Us) Un(bX Ch eC Ed Iz Ko Kr Ms Oy Us) Lx(Ed Hc Im Iv Kz Me Mq Oy Qb) Po(Et Mq Ms Ni Nw Oi Oy Pb) Hc(aJ aP bA bV dG Fa Fr Qv) Ji(Im Jr Kr Mq Ms Ni Us) Ch(bQ Fa Hu Jd Nn) Mq(dA Et Mp Nw Oh) Jr(Et Im Kg Nw Qa) Ni(aW cN Kx Nw) Sr(aK bJ bO Jv) Kq(aF Kl Kr Vo) On(Im Lv Oy Us) bV(Dp fP Kz Me) Fa(bO Dp fP) Nf(cN Et Qv) Jd(Bg Ed Jv) Me(dA Ur) Ki(Kx Pk) Nw(Im Ms) Oi(Nn Qa) BaKl DpQv EdRf MpNd KzcN OybA PkeC Constrained panels with 2 analytes, where 1.0E-6 >= 'AUC p-value' > 1.0E-7. Contains 352 panels of 61,235 total panels evaluated. : Jj(Hw Ii Ij Ik Jl Jp Jq Js Kx Kz Lh Li Lj Lv Me Mn Mp Mt Mv Mw Na Nh Ny Oh Ok Om On Pf Pg Qd) aA(aD Ch cW Fr Jg Jl Jn Ki Lh Li Lj Lx Me Mn Mq Nf Ng No Og Ok Om On Ow Pe Pf Pk Ri Un Us Wm) No(Al aM bS Et Fr Ir Iv Jn Jq Ju Lj Lu Lw Mm Nn Ok Om On Pc Qa Qe Qh Qv) Et(Im Io Lj Lu Lv Lx Me Ml Mr Ms Mu Ne Nh Ni Qa Qb Qe) Jr(Ch dI Is Jv Lx Mq Ng Nn Og Oh Oi Ok Qe Ur Us Uu) Po(bO Ch Hu Im Jl Jq Lv Lw Me Mm Ns Ok On Qe) Nw(dN Ed Hu Is Lv Ly Me My Ns Oh Oi Qa Qe Uu) Ed(bV dI dM Fa Ji Jy Kq Kx Lw Ni Sr Vt) Lx(Ir Is Jn Jq Js Lj Lv My Na Ni Qa Qe) Kj(Cu Dc Fy Is Iv Jt Mq Mz Ni Pd Ut Vt) Uu(aP bV Jn Jq Jy Mu Pe Pf Qd Qe Rf) Mq(Im Is Jq Mm Mn Mt Nn Ok Om Qa) Un(bJ Ii Kx Lu Ly Og Oi Qv Ur Vo) Mu(Ih Im Mr Ms Na Ok Pf Qb Qe) Qa(Aj Io Jq Lv Lw Mm Ni Om On) dI(Iv Ji Jn Lj Nn Oa Pi Pk Qe) Me(Fr Mn Mw Nn Oh Ok Om On) dN(Cv Ji Jo Ki Ms Oi Qv Sr) Hc(Ax cT dM Nn Oh Pf Sr) Kq(bJ eC Ef Of Oy Us) Fp(Cv Jg Jp Mn Oh) Nf(aJ bA bV Fa Jl) Ng(Fr Im Li Mw Pe) Ni(aD bV cI Cs Oh) Jd(bP Co Iz Ms Oi) Jn(Ch cN Jv Kg Us) Im(Jq Lw Ok Qe) Jv(Fa Kx Nn Rf) Og(Fr Pe Pf Sr) Oy(aP bV Fr Pf) Pk(AJ cN Ur) Ch(bA Is Sr) Lv(Jq Nn Oh) Oi(Is Kx Oh) On(Kr My Pb) bJ(bA Ji Vt) dM(aM Mr Rf) eC(Dc Ny Vt) Fa(dA Ri) Lw(bN Us) Qe(Nn Oh) AjJi AoRf FyKg IvaW SrUs QvKx RibV UvdA Constrained panels with 2 analytes, where 1.0E-5 >= 'AUC p-value' > 1.0E-6. Contains 666 panels of 61,235 total panels evaluated. : Jj(aA Ed Fr Hc Hu Ih Ir Iv Jk Jo Jt Lx Ma Mj Ml Mm Mz Nb Ne Ni Nl Nm Nt Nu Nv Pk Rf Un Wm) Qe(Aj aW Ch dM Fp Fr Il Is Jq Kj Kr Lv Lw Me Mm Mq Mr Ms Na Nf Nh Ni Oi Ok Om On Pc Pf) Et(Aj Ed Fr Hv Hw Ir Is Iv Jl Jn Jq Js Li Lw Mt Mz Na Nn Nt Nw Oh Oi Om On Pc Pe Pf) Ed(aP bA cN cT Cv dA Fr Hu Id Is Je Jl Jn Jq Ki Kk Nn On Po Qv Qy Ri Uh Ur) Kj(Cq Hv Hw In Ir Jd Jo Js Ke Kf Kr Md Na Nf Nm Nn Po Rj Uc Ud Up Uv Vp) dI(aJ Ax cT Fa Fp Hw Ij Is Jd Jl Js Kq Kz Lh Mj Mr Mz Nf Ny Oh Ok On Ql) Un(Ao aW bA Co dM Fn Jo Jt Jv Kg Kl Mq Nf Ng Ni Nm Oe Oz Pk Qg Rh Ri) Nn(Aj Co Hu Im Jn Jq Kl Kr Lx Mr Ms My Na Ne Nh Ni Ns Oe On Oy Qa) Fp(aP bV cN dM Hx Im Is Jy Lv Ma Mp Mq Mw Ng Og Oi Pc Qd Ur) Qa(bJ Ch Fr Ir Is Iv Jn Kg Me Mt Mz Oh Ok Pc Pe Pf Po Qg Us) Jr(bO eC Fr Hc Jg Jq Kr Lv Lw Ma Mm Ni Ns Om On Pc Pf Po Ri) Aj(Ad bA cT Cw dG Fa Fy Hu Ij Kx Lh Mq Ok On Pd Po Vt) Mu(Hv Ir Is Iv Jl Jn Jq Js Lh Mh Mz Ni Ns Oe Om On Wm) Im(cN Fr Iz Jl Lu Lv Mm Mn Ne Nh Og Oh Oi Om Pd Pf Qd) Ni(aA aP Ax bA Ch Fr Is Jl Li Mn Mp Om On Pf Qb Uu) Sr(bX dA dM Dp eC Iz Kg Ki Kl Kr Ly Ng Oy Qg Qv Vo) Nw(dA Hv Hw Ir Iv Jl Jn Jo Jq Lw Na Ok On Oy Pc Pe) Mq(aJ bA Fr Hc Jp Ki Kx Lv Ma Mw Ng On Pf Rf Us) Kx(bA bV Ch cT dA dM Fa Hc Jd Mr Og Oy Oz Pk) Pe(bJ bO Ch Co dM Jv Lv Lw Mm Oi Om On Pb Po) Lx(Hq Hw Li Ly Mv Mz Ne Nh Ns Oi Pb Pk Us) Is(aW dM Io Jl Kg Lv Lw Me Ms Oe Ok On Po) Uu(bA Cp dF dG Fa Hu Lh Nr Nv Pd Pk Po Uf) Jl(Ch Io Ji Kr

Figure 8 Continued

Lv Me Ms No Ns Oi Oy Us) Jn(aW Co dM Iz Kr Mp Ng Og Oi On Po Ur) Qb(Fr Jq Lv Lw Mm Ms Ng Nh Og Oi Om) Ch(aP Ba bV dM Iv Kq Nr Pf Pk Rf) Po(Fr Hc Hw Ir Iv Jt Lh Mz Pc) Ng(Ba Fa Jg Lv Ma Mv Nt Ny Rf) Jd(bV cT Hc Ly My Nf Og Oy Us) bA(aM aS bR dA Jv Pk Ql Ri Us) Om(Hu Lj Lv Ly Mr Ms Oi Pb) No(aD cA cW Nk Ur Vv Tj) Me(Ax bQ bZ Cs Mm Mp Qv) Kq(Bg Hc Iz Jg Jt Jv Ly) On(Hq Io Lj Ms Nh Ns Oi) Oy(aJ Ax dG Fa Id Kk Tn) bV(bJ dA Iv Ki Nc Pk Rf) Lv(Mp Mt Mw Mx Ny Pf) aA(bW Jq Ma Oe Oi Ql) Mp(Iv Ml Mr Ns Ny) Ki(bQ dA Kz Nf Nr) Rf(cN Co Lu Oi Ri) Og(dM Jg Li Nu Qd) aP(bR bX Dp Nf Pk) Mr(cN Fr Mn Mw) Kr(dG Id Ke Lw) Ok(Jo Lj Ly Of) Ur(It Iv Kz Nf) dA(aD Hc Ji Oi) dM(Ly Oz Ql Ri) eC(Id Kd Mz Pi) Cs(Hc Jv Ri) Jq(bJ dN Lj) Oh(Ms Ne Nh) Us(dG Id Ke) Pk(Co Jv Lw) Fy(bH Co) Mt(Nf Ns) Iv(cN Mw) Oi(Li Pf) aJ(bR Kz) ArJv WmQd FaLy LwbJ MnNh NaNy TnHc JiKg PfbO bRdG

Constrained panels with 2 analytes, where 1.0E-4 >= 'AUC p-value' > 1.0E-5. Contains 1,194 panels of 61,235 total panels evaluated. : Pk(bJ bP bW cK cT Cv dA dG Ed Fa Fn Fr Jd Ji Jl Jn Jr Kg Kr Lu Ly Mm Mq Mr Ms Ni Og Oi On Qe Ql Qv Rf Ri Sr Uf Uh Us) Aj(aP Ba Bc bQ bV Cp Cu dA dF Ef Fp Id Jl Jq Jt Jy Ke Kn Kz Lv Lw Ml Mr Mw Nf Nm Nr Ny Om Pf Qd Ql Rf Tn Ut) Im(aW bV Ch dI Hv Io Ir Is Iv Jn Js Jt Jv Ki Lh Li Me Mi Mj Ml Mr Mt Mx Mz Na Nb Nf Ni Nt Pa Pc Pe) Ed(aD aJ aM Ax Ba Bc bQ cK cW Dc dF Fy Iv Jv Ke Mr Mu Nc Nk Nr Oe Oi Om Pd Pe Pf Qe Ql St Ut tF) Jl(aW bO dM Hc Hv Hw Ir Jn Jq Jr Js Jv Kj Kl Kx Lw Mm Mq Mt Mz Na Nn Oe Oh Ok Om On Pc Pf Qa) Ni(aJ aM bJ bM bR Co cT eC Fa Fp Hc Jd Jg Jn Jp Jq Jv Kr Lj Mm Mw Ny Pe Ql Rf Ri Sr Ur Us) Is(AJ Ao bP bV Co eC Fr Hc Ir Iz Jm Jn Jq Jv Kr Kx Lh Li Mz Nn Oh Om Pc Pe Pf Qv Ri Ur Us) Uu(Ad aJ Ax bQ cN cT Cu dA Dc Fy Iv Jg Jp Kd Kf Kk Kx Ma Mn Mq Oh Ok Ow Pg Qa Ql Ut Vt) bJ(aM Cs cT Cv Dc Id Iv Jr Kd Ke Kk Kn Kx Lv Lx Md Me Ml Mt Mu Mz Ny Om Or Qd Tn Ut Uv) Nn(bO cN dA dM Fr Hv Hw Ir Iv Iz Js Ki Lh Lj Lw Mi Mm Mz Nt Ok Om Pa Pe Pf Qd Qu Us) Jd(aD Ao aW bM bO Cs dA dM Iv Jj Ki Kl Kr Kz Lj Lx Me Mr Nc Oe Oz Qu Qv Ri Ua Ur) Jn(aD bA bP bV eC Fp Fr Hc In Jg Jr Ki Kl Kx Lv Lw Mm Mq Mw Ny Oh Ok Om Qe Qu Ri) Pe(aW eC Fp Fr Hc Il Iz Jq Jr Kg Ki Kr Me Mq Ms Ns Oh Oy Pa Pc Qb Qe Qu Ri Ur Us) dA(aJ aM bR cB cF Ch Cs cT Iv Jj Jv Ky Lj Mr Ms Nf Oa Og Qe Ql Qv Rf Ri Ur Vt) dI(Ad cP CW Dc dM Et Fr Hx Id Jq Jv Kn Lv Ly Na Nb Nt Oi Ra Ri Un Ut Uv Vt) Sr(aA aM aN Ao aW bH cK Co dJ Iu Jo Jr Kx Lu Mg Ms Nf Oi Oz Qu Ri Ug Uk Ur) Lx(aM bR Ch Co Dp Hu Hv Jo Jp Jv Kr Lw Mm Ms Mx Nt Of Oh Ok Om Pf Pg Qd) dM(aC aD bA bQ bV Cs cT Et Ji Jr Jv Jy Lj Ml Nc Nr Ny Oa Ow Pc Po Qa Qt) Fp(Hv Hw Ik Ir Iv Jr Js Jt Lh Ly Me Mi Mr Mt Mv Mx Mz Na Nb Nt Pa Qv) Kj(An As Aw Ax Bn bV Dd Et Ib Kd Kg Kp Lv Mj Mx Nr Pb Ph Ra Rf Tv Ul) Oh(Ch Fr In Ir Iv Jp Jq Jv Kz Lh Lu Lw Mn Na Ns Nt Oe Ok Om On Pf Qd) Us(aP bV Cs cT Cv dL Et Fa Iv Jq Lh Mr Nf Ny Om Pf Pi Po Qe Ql Ut Vt) eC(An Cp Cu Cw Hv Hw Hx Ij In Ir Iv Jq Kn Md Ml Mt Nb Om Qa Rj Up Vp) On(Ap Ch Hc Hu Hv Ii Iv Jh Jo Jq Js Ki Li Mk Mr Mv Na Ne Nv Ok Pf) Og(aP Ax bV Cs Fa Jk Ki Lh Lv Mn Mp Mv Mw Nt Nv Ny Ow Pd Rf Wm) Mr(aA aD aJ aP aW bR bV Ch Jg Jj Jp Jq Jr Lv Lw Mm Mq Qv Ri) Nf(aD aW Ax Ch cT dG Id Jp Kk Kx Ky Lv Mp Mw Ny Qd Rf Uf Vt) Qe(bO Hv Hw Ir Iv Js Jv Kx Lh Li Mi Ml Mt Mz Nt Qa Qv Ri Ur) bA(aD aJ aP bM cK cN Dp Io Iv Jr Ki Kr Kz Ly Me Ng Oz Qu Ur) Kx(aJ aM aP Cs dG Et Iv Ji Jr Jy Lu Ly Ms Pc Po Ri Ur) Lw(Cs Fa Ir Iv Jj Kz Li Lj Me Mp Mq Mt Mu Ny Ok Ur) Ng(aP Ax bQ cT Ij Iv Jk Jp Kq Lj Mn Mp Mt Nv Pd Qd) Ch(aJ Cs cT Et Je Ji Jp Jy Lh Ma Mw Qd Ql Qy Tn) Hc(aD bQ cN dF dL Et Id Ji Jp Kk Ky Ml Mn Rf Un) Qb(Ir Iv Jg Jp Li Ma Me Ml Mn Mp Mt Mx Mz Na Nt) Mq(aD bV Fy Ir Jg Js Kr Li Lj Mz Nh Qu Qv Ur) Lv(Fr Ir Iv Jg Jp Li Lj Mm Mn Mz Ne Nh Qd) Ly(aJ aP bV cN Id Ke Ki Kk Ld Ql Rf Uh Wm) Qv(aM Fa Jr Jv Kz Oz Pc Po Ql Qy Rf Ri Vt) Jj(aM Hv In Jg Jv Mi Mx Nr Oz Pa Pc Ql Ri) Kq(aK Ao Bb bO cl Dp Fn Ii Kg Ki Oi Uc Ur) Kr(aP Ax Cs dL Et Fa It Iv Ow Pf Po Qa Qd) Ny(Bg Hv Hw Iv Me Ml Mt Mx Nh Oi Pc Ri Ur) Mp(Hv Hw Ij In Ir Mi Mj Mt Na Nb Nh Oi) Jq(Cs Iv Li Me Ml Mt Mw Nt Ok Pc Pf Wm) Fr(bO Ih Kz Lj Ms My Na Ne Nh Ns Oi) Jv(aP Ax bQ bV cT Et Hu Iv Nr Pf Po) Om(Jo Li Mg My Na Ne Nh Ns Of Oy Pf) Cs(cN Cv Dp Hu Iv Jy Ki Mu Nw Oi) Me(aP cN Fa Jg Jp Jr Jy Li Na Pf) Mw(Bg Hv Ih Ir Js Mi Ml Mt Mx Na) Ri(aJ aP Ar Ax cN Iv Ji Ki Po Ql) Un(bO Hb Ih Io Ir Mg Nc Ow Qu Rf) Kz(aD Ax dG Id Jr Kk Lu Nw Oi) Oy(cN Cp cT Ke Kn Rf Tv Ut Vt) aM(aJ aP bF bQ bV cT Hu Rf Ur) Mu(Bg cT Mi Mm Mt Nt Pc Qd) Jr(aW cN Co Ir Iv Lh Mz) Ur(Fy In Or Pi Po Qa Ql) aA(aW Fy Ml Na Qu Rf Vt) bQ(aD aW bM bR bV cA Co) Fa(Co Ms Oe Oi Oz Ql) Ki(Ax cT Ky Ml Po Qa) Ok(Et Hu Ms My Oi Pf) Ji(aW bN cl cZ Ko) Lj(Jp Mm Na Nh Oi) Rf(aP cW Ms Oe Oz) bV(aX bR Hu Oi Ql) cN(bR cT Ml Nr Ql) Mt(Iv My Na Oi) aJ(bX Dp Iv Oz) Wm(Ir Jp Mz) Et(Jt Lh Qd) Nh(Jp Li Pf) Qa(aW Fn Lh) cT(bR Hu Qu) fR(bN bR cX) Co(Nr Po) Cv(Cx No) Mm(Ml Nw) Mn(Ms Ne) Pf(Na Ns) cW(Hu tF) BgUt MaNe NcaP TnOz IoJp ItaW JtNw JyaD KebX QlOi VtdJ bNdG Constrained panels with 2 analytes, where 1.0E-3 >= 'AUC p-value' > 1.0E-4. Contains 1,743 panels of 61,235 total panels evaluated. : Aj(aJ An As Aw Ax Bn Cv Dc Dk DL Ez Fb Fr Gl Hw Hx Im In Ir Jk Jp Js Kd Kf Kp Ky Li Lx Ma Md Mt Mu Mx Mz Nt Nv Oa Oh Or Ow Ph Pi Qb Qt Qy Ra Uc Uf Ul Us Uv) Jv(aD aJ Ba bJ cN Cw dF dG Dk Fp Fr Fy Id It Ji Jp Jq Jy Kk Kn Ky Kz Lh Lj Lv Ly Ma Mn Mq Mr Mu Mw Nf Nt Nw Ny Oa Og On Ow Pc Pd Qa Qb Qd Ql Tn Uf Ur Ut Vt) Ch(aM Ar Ax Bc bF bZ cG cN cS Cw dF dG Ed Ef Ez Fb Fp Fr Fy Gl Id Ij Jh Jk Js Ky Kz Li Lv Me Ml Mn Mq Mu Nt Nv Oa Ow Pd Qb Qt Qv St Ua Uf Ut) Ur(AD Ax Cs cT Cu Cw Dc dM Et Fa Hu Hv Hw Id Ij Im Ir Jl Jq Js Kn Lh Lv Lx Ly Ml Mr Mz Nn Nr Oa Oi Om Ow Pc Pd Ri Ud Ul Up Ut Uv Vp Vt) Oi(aJ aM aP Ar Ax bA bJ bQ cN cT dG dM Fb Hc Id Ih Ij Ir Je Jg Jp Ki Kk Ky Lh Ma Mm Mn Mv Mw Nh Nt Nu Nv Oa Ow Pd Qd Qv Qy Ri St Uf) Uu(aM Ar Aw Bc cE Cs Cw dI DL Ef Ez Fb Gl Ij Im Jk Jt Kn Ky Li Lv Ml Mp Mr Mw Mz Nt Ny Oa Or Ou Qt Qy Ri St Tn Uh Ul) Qv(aA aD aP Bc bJ bV cN Cs dI Et Hu Id Im Iv Jl Jn Ki Kk Kq Ky Ly Mp Mu Mw Nc Ni Nn Nr Nw Ny Oa Pe Pf Qa Qb Qd St Uv) Rf(aJ aW bA bC bM bW cK Cs cT Cv dG dL Fa Hv Id In Io Iv Jd Jq Jy Kl Kq Kz Me Ml Nn Ow Pb Qe Ql Sr Tn Tv Uf Ul Us Vt) dA(aV aW Ax bS bU bW cA cC cK cP dF dL Et fR Hu Id Is Jn Jr Kk Kz Ml Mu Nc Ng Ni Nr Oh On Ow Oy Oz Qd Qw Uf Uh Uk Us) Og(aJ aM Ar Ba cN Cv Dk Ed Ez Hu Id Ih Ii Ij Ir Iv Jp Jq Jt Jy Ke Kq Kz Lj Lw Ma Mj Mm Mx Nb Nc Nh Ni Nx Oa Pg Ql) Fa(AD aM Ao aW bV bW Cu Cv Cw dM Id Ij Io Is Iv Iz Jj Kd Kj Kl Kn Ml Na Nw Ow Pc Pi Qu Ra Rh Up Uv Vt) Ri(aD aM cT dG Et Fp Fr Gl Id Im Ir Jl Jy Kk Kq Lj Ly Me Mq Mw Nf Nn Nw Oa Oh On Ow Pf Qa Qb Qd St Tn Ut) Ki(aD aJ aM aP Cu CW Db Dc dF dI Et Fr Fy Hu Id Iv Jy Kn Lw Ms Mw Ny Oa Oh Ow Oy Oz Pf Qe Ql Ra Ut) Jd(aJ aM Ap Ax bW Cq Cu Cw dL Dp Hw Ij Ir Kg Ky Lw Mg Na Oa Oh Ow Pc Pi Qe Ql Qy Rh St Tv Uf Uv Vt) bJ(AD An Ax Cp Cu Cw Ed Hv Hw Ij In Jj Jn Ky Lh Lj Lu Ms Nb Nf Nn Nw Oh Ok Pb Pg Pi Rj Tv Up Vp) Kq(aE aL aM aW bH bP bX Co Cq Cs cZ De dM Hq Jj Jo Kx Kz Me Mg Ms My Nc Nf Nv Oz Pa Pb Pk Qu Ut) bV(aW cA cN Cs cT cW Et In Io Jl Jr Jy Kk Lu Lx Ml Ms Nn Nr Nw Ny Ow Oz Pc Pe Pi Po Qe Qu Sr St) Fr(bR Dp Hv Hw Ij Ir Iv Jq Js Kj Kl Kr Kx Lh Lw Lx Mg Ml Mt Mx Mz Nf Nl Nt Oe Ok Om Pf Qd Us) Me(aJ aW Ba bP cT Cv dF dG Ed Je Jn Kx Lj Lv Ma Mt Mx Nv Ow Pc Pd Qd Ql Rh Sr Uf Uh Us Wm) aM(aW Ax Bo bR cE Cs cU Cv dF dG Fp Is Iv Jn Jr Jy Kr Lw Mr Ms Mu Nn Nr Nw Pe Pk Po Qg Ql) Pf(bR dM Dp Hv Hw Ij Ir Iv Jn Jo Js Jt Kj Kz Lh Lw Mm Mr Mt Mz Nb Nt Pc Pe Pk Qu) Nf(Bo bQ Co Cs Cv dF dL eC Ed Fp Iv Je Jn Jy Ke Kp Kr Li Lw Ne Nt Pk Qb St Wm) Jq(aF bA Cx Jn Jp Kr Kx Kz Lh Lu Lw Ma Md Mi Mn Mp Ms Mx Na Nb Ne Ng Nh Pk Qd) Us(aJ An Ax Ba bQ cN dF Dk eC Hu Hw Hx Ij Ir It Js Jy Kj Kn Nr Nw Oh Ok Or Qd) cT(aD aJ aP aW bP cK Cs cW dG Io Iv Jl Kj Kr Kz Ly Mr Ms Nw Oe Po Qe Sr St Vt) Oy(An bQ Cs Cu Cv CW Dc dF Dk dL Fy Jy Kd Kp Ky Lh Nb Nv Pd Pg Pi Pk Uf) dM(Ar Ax Ba Dp Fy Gl Hu Ij In Lx Ma Mu Nw Oe Oh On Pd Qd Qn Rh St Uh Uv Vt) Mt(Hc Hv Hw Ij Ir Jn Js Li Lj Mi Mj Ml Mn Mr Ms Mx Mz Nb Oh Ok Om Pe Wm) aD(aJ aP Ba Cs dG dI dJ Fp fR Hu Is Iv Jj Jl Jr Kx Mu Nn Ow Pe Ql Sr Un) Mw(aW Hc Hw Ij In Kj Lj Lw Mh Mj Mn Ms Mz Ne Nh Nt On Pa Pc Pd Tv Wm) Kr(dF eC Ij Ir Jy Kk Lh Li Mn Mr Mx Mz Nr Nw Oh Ok Om Or Pi Ut Vt) Kx(Ax bW Co Cv dL Dp Hu Id Ke Lw Ng Nr Nw On Ow Pe Qa Ql Uf Vt

Figure 8 Continued

Wm) Cs(aJ aP bO bR Co dG Io Jj Ju Kj Kz Lu Ly Ms Nc Oe On Pk Ql Vt) Ni(aV bW Cv Dp Id Jk Jt Ky Lh Lv Ma Na Nv Oa Ow Pc Pg Qd Uh Vt) Hc(Ar Ba Ij Jy Li Lu Lw Mr Mx Nr Nt Ok Om Ow Pd Pk Qa Qe Qx Wm) Ed(aW dG Dp Ij Jt Kd Kn Ml Mm Mq Nm Ok Ow Oz Qa Ra Tn Uf Ul) Ly(Ar Ax dG Fb Je Jy Ky Mq Ne Nh Nt Oa Or Ow Qy St Uf Ut Vt) Kj(Bc bQ dG Dk dL Fp Hu Jy Ko Lx Ma Mu Oh Pg Qd Ql Qy Rb Tn) Kz(aW Co Cv dF Et Hu Jl Jn Jy Mn Mu Nn Om On Pe Qe Tn Uf Vt) Lj(bQ Iv Jg Jh Jy Lh Lu Ma Mn Mp Mx Nb Ne Nt Nv Nx Ny Pd Pe) Ny(Ij Ir Jg Js Lx Mi Mj Mm Mr Ms Mz Nb Ne Nl Nt Pa Pd Wm) eC(Ad As Bn Cq Dd Ib It Ji Js Ke Kp Mj Na Pb Ph Ra Uv) Mm(Hu Is Iv Lh Li Mv Ne Ng Nh Nt Oh Ok Om On Pd Qd) Pk(aW Dp Et Hu Is Jy Ke Kk Nc Nn Nr Nw Ow Oz Pe Po) aP(aC aW Hu Io Is Iv Jn Jy Ms Nr Oe Ow Oz Ql Qu Sr) bA(aW bW Co Cv Dc Is Jj Ju Jy Lw Ml Nw Qa Qe Sr Vt) dI(As Aw bR cF Cq Cu Hu Hv Ke Kk Ky Mx Nm Om Oz Qd) Mq(aW Cv Id Iv Ky Lh Mi Ml Mx Na Ns Pi Qd Sr Vt) Mr(bM Co dG Id Ky Lh Li Mz Na Nt Oh Ow Qb Ql Vt) Ng(Ar Ez Hu Ih Je Lh Nb Nh Nu Ow Pg Ql Tn Uf Wm) Lw(Fn Jp Js Lv Ml Mn Mv Na Om On Ow Qd Sr Un) Li(Hv Hw Ij Ir Iv Jn Js Mi Mz Na Nb Nt Pa Pe) Mn(Ih Ir Iv Lu Ml Mv Mz Na Nl Nt Pd Qd Wm) Mp(Hq Jg Js Mh Ms Mx Mz Ne Nl Nt Nu Pa Pc) Oh(cN Hv Hw Ij Jg Jo Js Jt Mi Mz Nb Nm Pc) On(Ao Bg fP Hw Ir Iz Jk Kl Mg Mz Oe Of Qd) Dp(Ax cN dG Id Jl Jy Ky Lu Nn Pe Po Un) Qb(Hv Hw Ij Jn Js Jt Lh Mi Nb Pa Pc Pd) Lv(Ih Js Lh Ma Mi Ml Mv Na Nt Nv Pd) Sr(Bo Io Jj Ju Ky Lx Mu Nc Nl Ow Rh) Jn(aE aJ bM bO Io Ir Iv Lh Pc Pe Vt) Ql(aJ Ax cW Iv Jy Lu Ms Nn Nw Oe Qe) Nh(Jg Lh Ma Mj Mv Na Nv Pc Pd Qd) Im(Ao bW Co Cv Hw Ij In Jo Qu Tv) Vt(aK aV bX Jj Kg Lu Ms Nn Oz Qg) Fp(bW Co cW dF Ij Jo Ky St Uf) Lx(Ao BG dH Jt Mh Pc Pi Qz) Hu(aJ Ax Bg bM cN Iz Mu Qu Ua) Jj(Ez Fb Fy Ha Oa Qy Rm Uv) Kg(Cw Et Js Lh Nn Po Qc Uv) bQ(aJ bF Bg bW bZ cO dH Qu) Ax(cN Ju Jy Nc Nw Oe Qu) Iv(Co Cv cW dG Jp Mz Om) Oz(cN Fy Id Jy Kk Ky St) aW(aJ dF Et Jy Nn Po St) Ms(Ar Jg Lh Nv Oa Ow) Mu(aC cW Jt Oa Pa Rh) Ne(Jg Jp Mv Na Pd Qd) Is(aJ bR Ju Kl Qu Ua) Qe(Co Iz Jo Jt Jy Kl) Om(Ir Js Lh Mz Pc Qd) bO(fR Fy Id Ke Nr Qa) Ao(Et Jl Jy Pe Po) Of(Cw Id Lh Pi Ut) cN(cA cW Ky Nc Rh) Wm(Ih Iq Js Mv) Ml(Jg Jp Nv St) Qa(Bo Co Fw Qu) Jr(aE aJ bM Jt) Kl(dF Et Nr Uf) aA(Cv Iz Rh Uf) dG(cA cL dH Nd) Po(aJ Iz Tj) Fn(Id Ji Pi) Fy(Ii Jo Qu) Nn(Jo Jt Qz) Na(Bo Jp Qd) Jg(Ih Io Qd) Jl(aE bR Iz) Lh(Jo Pb Vo) Oe(aJ Ar Nt) Pe(Ir Mz Qz) fR(aV bX cP) Ba(Ss Vo) Dg(Et Uf) Lu(Oa Ow) Jy(Oa Ow) Ke(aK Ko) Uh(Tn Tv) Pc(Ok Qd) Pd(Ns Pb) bR(cU dF) AfCv BoCu NraJ NtJp MxIj ToNw JiQg RhOr UvdJ

Constrained panels with 2 analytes, where 1.0E-2 >= 'AUC p-value' > 1.0E-3. Contains 2,362 panels of 61,235 total panels evaluated. : Us(AD As Aw Bc bJ Bn Cp Cq Cu Cw Dc Dd Ed Ez Fy Gl Hv Ib Im In Jj Jp Jt Kd Kf Ki Kk Kp Li Lv Ma Md Mj Ml Mm Mn Mp Mu Mw Mz Na Nb Nm Nt Nv Oa Pd Pg Ph Qb Qv Qy Rb Rj Tn Tv Uc Uf Ul Up Ur Uu Uv Vp Wm) Qv(Ad aJ As aW Ax Bn bW cK Cp Cq cT Cu Cv Cw Dc dG Dk dL dM Ez Fr Fy Hv Hw Ij Ir Jq Jt Jy Kd Ke Kf Kn Kp Kr Lh Lx Md Ml Mm Mz Na Nm Nt Oh Ok Om On Ow Pb Pd Pi Pj Ra Rh Rj Uc Ud Uf Ul Up Vp) Ki(Ad Aj An As aW Ba Bn cN Cp Cq Dd Dk dL Hc Hv Hw Ij In Ir Jq Js Jt Kd Kf Kp Kr Lh Lu Md Mj Mu Mx Na Nm Nw Oe Ok Om Pb Pc Pd Ph Pi Rh Rj St Tv Uc Up Ur Uu Vp) Uu(An As bC Bg bJ Bn bW bZ Cq Dd Fp Ha Hv Hw Ib In Ir It Je Jo Js Ko Kp Kr Lj Md Mj Mm Mt Mv Na Nb Nf Nm Nq Oz Pb Pc Ph Pi Pj Qb Ra Rb Rj Ua Uc Up Uv Vp Wm) cN(AD Aj An As Cp Cq Cu Cw Dc Dd Et Fr Hv Hw Id Ij In Ir Jj Js Kd Kn Kr Lh Md Mj Ms Mx Mz Na Nb Ng Nw Ny Oe Ok Om Pb Pi Qd Ra Rj St Uk Up Ur Ut Uv Vp Vt) Ur(aJ An As bJ Bn bV Ch Cp Cq cW Dd dF dG dL Dp Fr Ha Hc Jo Jt Jy Kd Ke Kp Kr Md Mj Ms Mu Na Nm Nw Oh Ok On Oy Oz Pb Pf Qd Ra Rb Rj Tn Tv Uc Wm) Oi(AD An aW Ba Bc bM bW cS Cv cW dF Dk dL Dp Ez Gl Hu Jk Jt Jv Jy Ke Kn Ld Lv Lz Mi Mq Mr Mx Mz Nb Ne Nl Or Pa Pg Pi Rh Tn Uh Up Vp Vt Wm) dA(Ad An Ba Cp Cu Cv Cw Fr Hq Hv Hw Ij Im In Ir Jq Jt Kd Ke Kf Kn Kp Kr Lh Ly Md Mj Mk Mx Mz Na Nb Nd Ns Ny Ok Om Pi Ra Rh Rj St Ua Up Ut Vp) Mr(An As Bn bW Cp Cu Cv Cw Dc dL Hv Hw Ij Ir Iv Jn Jo Js Jt Kd Kn Kz Lj Ma Me Mi Ml Mv Mx Nb Ne Nf Ng Nh Ni Og Pa Pc Pd Pi Qd Rh Uf Up) Kr(Ad Aj An As bJ bP Cp Cu Cw Dc Dk Ed Fy Hw In Jj Jp Js Jt Kf Kg Kn Ko Kp Kx Lj Lv Md Mj Ml Mp Na Nm Nt Nv Oa Pd Ph Qb Rb Rf Tn Ul Vp) Jv(Ad An Aw Bc bF bZ Cv Dc dL Gl Hc Ij In Ir Jh Js Jt Kd Ke Kf Li Lw Md Me Ml Mp Ms Mt Mv Mz Nb Nv Ok Om Or Ou Oz Pg Ph Qt Ri St Uh) aD(Ar Ax aZ bF bV bZ cE cU dF Dk Dp Et Fb Fr Im Je Kq Ky Li Lj Lx Ly Ma Me Mn Mw Nc Nr Nv Nw Ny Oa Oh On Pd Pf Po Qa Qd Qe Qy Rf Uh) aJ(Ad An As Ax Cp Cq Cu Cw Dc Dd Hv Hw Ij In Io Ir Jj Jy Kn Ld Lv Lw Lx Ml Ms Mt Mu Mz Na Nb Ny Om Ow Pb Pd Pe Pi Rh Sr Up Uv Vp Vt) Hc(aM As Aw Bc Cu Cv Dk Fy Hu Ir Iv Je Jh Jq Jt Ke Kf Kn Kp Lh Lj Lv Ma Mu Na Nb Nf Nv Nw Ny Oa Ou Pg Qd Ql Ra Uf Ul Ut Vt) Ri(Aj An aW Ch Cu Cw dF dL Fy Hu Ij In Jq Ke Kn Ky Kz Lh Lu Lw Lx Mn Ms Mu Mz Nc Ng Nr Og Ok Om Or Oy Oz Pc Pd Pi Uf Uh Vt) Ng(Bc bJ CW dF dG Dk Fb Gl Id Ii Ik Jh Jt Jy Kn Lw Mg Mi Mj Ml Mz Na Ne Nf Ni Nl Nr Nx Or Pa Pz Qt Qy Ra Rh St Ut) aM(An Aw Ba bW Cp Dc Dp Et Fr Fy Gl Id Im Jl Jq Kd Ke Kn Kz Lj Ly Ma Me Mq Mt Nf Ny Oe Oh Om On Ow Pd Pf Qd Qe Rh St) bV(Ad As Ax bM Bn bW Cp Cq cS Cu Cv Cw Dk Fr Hv Hw Ij Jj Kd Ld Lw Mn Mt Mu Mx Na Nb Oh Ok Om On Pb Pf Ra Rh Up Ut Vp) Aj(Ar bC bJ bR Cq cS Dd dI Dp Ha Hv Ib Je Jg Jo Kk Lj Mj Mn Mp Mv Na Nb Nw Ou Pb Pg Rb Rj St Tv Ua Ud Uh Up Vp Wm) Ch(aC Ad Aw Bg bJ bM Bo cE CP Dc Dl Dk dL Jq Ke Kk Kn Lu Lw Ly Mp Mt Mv Mz Nb Nw Ny Ok Om Or Ou Pg Qx Uh Vt) Jj(Ad aP As Ax Bn bO Cp Cq cT Cu Cv Cw Dc Dd dF dG dI dM Id Jy Kd Ke Kf Kn Kp Ow Pi Ra Rh Rj Tn Uc Ul Up Ut Vp) Oy(Ad Ar As AW Ba Bc Bn bZ cE Cq cS Dd dI Fb Gl Ib Jg Kf Mi Oa Or Ou Ow Ph Ql Qx Rb Rj St Uc Ud Ul Up Uv Vp) Kg(Ad As Cp Cq Cu Dc Hv Hw Id Ij Ir Jq Jt Kd Ke Kn Kp Lw Mz Na Nf Nr Oh Ok Om On Pb Pd Pf Pi Ra Rj Up Ut Vp) Og(Bc bJ bM bW Cu Cw Fb Hw Ik Jo Kk Kn Lz Me Mi Ml Mt Mz Na Nl Or Pa Pi Qy Ra Rb Rh St Uf Ul Up Ut Vp Vt) Ow(aW Ax bJ Co Cs Cv Fp Fr Fy Id Io Iv Jl Jn Jr Kq Kz Lx Mu Mz Nc Nf Nr Nw Oe Oz Pc Pi Qd Qe Ql St Tv Vt) Mc(Ad As bW Cp Cq Cu Cw Dc dL Fb Id Ih Ir Js Kk Ld Lh Mi Mj Mq Mv Mz Ne Nf Nh Nt Pa Pg Qy St Tv Vt) Kx(Ad aW Cp Cq Cu Cw Dc Fy Hv Hw Ij In Ir Kd Kn Kp Ml Mu Mx Mz Na Ny Ok Om Pb Pi Rf Rh Rj Up Uv Vp) Rf(Ad As Bc Cp Cq Cu Cw Dc Hw Ij Ir Is Ji Jn Jr Js Kd Lh Md Na Om On Or Pe Pi Qa Ra Rj Ud Up Vp) dM(Ad An As Bn Cp Cq Cu Cv Cw Dc Dk Fr Hv Hw Id Jq Kd Ke Kn Ky Lw Mn Mt Na Ok Om Pi Ra Up Vp) Ma(Ao Hv Hw Ih Ij In Ir Iv Jg Jn Js Kl Lw Mi Ml Mm Mt Mx Mz Na Nb Nf Nl Nt Pa Qu Vo Vv Wm) Qd(Ao aW bI bO bR cW Dp Hv Hw Ij Ir Iv Iz Jn Jo Js Jt Kl Lh Mi Mt Mz Nb Nt Pa Pd Pe Rh Tv) aP(Ad An As Ax Bn Cp Cq Cu Cv Cw Dc Hv Hw Id Ij In Kd Kn Ml Na Ny Om Pi Ra Rh Tv Up Uv Vt) Co(Ax cT dF dG Et Fr Gl Hu Ij Je Jl Js Jy Lh Lj Lv Ml Mq Mu Ny Oa Oh On Pd Pf Qb Tn Vt) Mm(Fr Hv Hw Ij In Io Ir Jp Jq Js Jt Kj Kz Lu Mh Mi Mj Mn Mp Mt Mw Mx Mz Na Nb Nf Nv Pg) aW(Ba Bc bR cE cG Cs cU cW dG Fp FR Gl Hu Id Lx Ml Nt Nw Oh On Oz Pd Pf Qb Ql Vt) bM(Ad An Ax cE Cp Cs cT Cu Dc dF dI Dk Im Is Iv Jq Kn Kq Ld Lv Ly Ms Mt Mu Ny Oe Om) bP(Ba Hv Hw Id Ij In Ir Js Kd Ke Kn Md Mz Na Nb Ny Om Pi Ra Rj Uc Ul Up Ut Uv Vp Vt) Kj(Ar Ba bJ dF Ez Fb Gl Ha Im It Jk Jp Li Lj Mn Mp Nb Nt Nv Ny Oa Ou Qt St Uf Uh) Ed(Ad An As Bn bO bW Cp Cq Cu Cw dL Hv Hw Kp Md Na Pb Pi Rb Rh Rj Tv Up Uv Vp) Ni(Dc Fy Ih Ij Ir Iv Js Kz Lz Mi Mj Mq Mt Mv Mz Nb Ne Nh Nl Nt Pa Pd St Uf Wm) dI(An Bn bU cA Cp Cv Dk dL Dp Ib Jo Jt Kd Kf Md Mu Nc Pb Rh Rj Tv Uc Ud Up Vp) Nn(aC Ad An As bW Cp Cq cT Cu Cv Cw Id Kd Kn Kp Ky Pi Ra Rh Rj St Tv Up Uv) Ms(Ba Bc bQ dF dG Dk dL Fb Gl Id Ij Jc Jk Jy Ke Kk Ky Nx Or Pd Pg Qy St Wm) Dp(Ar cT cW dF Et Is Iv Ji Jn Jp Jr Kk Li Lj Nt Nw Oa Oh On Qa Qe Tn) Jg(Hu Hv Hw Ij Ir Iv Jq Js Lw Mg Mi Mt Mx My Mz Na Nf Nl Ns Nt Pc Pd) Rh(Hu Id Is Iv Je Ji Jl Jn Jr Kq Lw Mp Mw Nf Pc Pe Pk Po Qa Qe Vt) Ql(cT Cv dG dL Fp Fr Hu Id Io Ky Kz Lx Mq Mu Nc Nf Om Oz Pf St Vt) Pd(aE Ao Hq Hv Hw Ir Iv Iz Jp Js Kl Kz Ml Mt Na Nb Nf Nt Pa Pc Uk) Qg(As Cq Cu Cw Dc Hv Hw Id Ij Ir Jq Kd Kn Kq Na Nf Pi Ra Rj Up) Lj(bR bW cW Gl Hv Hw Ij In Ir Jn Jo Js Jt Mi Mv Nf Pa Pc Pg Ut) bJ(aC As Bn Cq dL Js Jt Jy Kp Li Mj Mx Na Oa Oe Ph Qb Ra Rb Uc) Nh(Hv Hw Ij In Ir Iv Jn Js Jt Lw Mi Mt Mx Mz Nb Nf Nt Pa Pg) Bo(Ad As Cq Cw Dc Hv Hw Id Ij Jn Kd Kn Pb Pi Ra Rj Tv Up) Cv(aC Ax bQ cT Hu Is Jd Jn Jr Ly Ml Nr

Figure 8 Continued

Pe Po Qa Qe Sr Un) cW(Ar cE cU Fb Im Is Jl Kk Ky Ld Lv Nr Nw Oa Oz Qb St Vt) Jp(Hv Hw Ij In Ir Jn Jo Js Jt Kl Mi Mt Mx Mz Nb Pa Pc)
Lw(Ax Bg cl cT Fy Hf Lh Lu Mh Mx Mz Nb Ne Nt Nv Ug) Ly(aC Ba Bc bQ dF Dk dL Kd Kn Nl Nu Pi Qx Rb Tn Ul) Jy(bF Bg cT Et Im Iv Iz
Jn Ky My Nc Nr Oh Tv Uv Vt) Uf(Ax bA Cs Fy Im Iv Jn Jr Lu Mg Oz Pc Pe Qb Sr Vo) bW(Ax Cs cT Hu Is Iv Jn Jr Kz Lv Nf Nr Pe Po Sr Un)
Nc(Ir Iv Js Jt Lh Mi Mj Ml Mt Mx Mz Nb Nv Pc Pg) Oz(Ar bQ bR cT dF dG Dk Gl Jq Kd Ke Kn Oa Or Ut) Nt(aE Hv Ir Jn Js Mi Ml Mq Mt
Mv Mx Mz Na Pc) Id(aK Ax cK Cs cT dJ Jd Jl Jo Lu Lx Oe Po Qe) Mn(Hv Hw Ij In Js Mh Mi Mj Mx Nb Nf Pa Pc) Qe(Ad Ao As Bn Cw Kn
Pi Qu Ra Rj Up Uv Vt) Jd(Ad As Bn Dc Hv Kd Kn Kp Om Pb Ra Rj Up) Nf(aC An As bR Cp Fy Kd Kn Mx Pa Uh Up) Ky(Hu Io Iv Kk Lu Lx Mu Nc Nr Oa Or Pf) dL(bQ bR Cs cT eC Fa Fp Hu Io Kz Nr Oe) Ax(aC bC bO bR dG Io Lu Mu Om On Qz) St(Al Iv Kz Lu Mq Nc Nl Oe Pk Qa Tv) Kq(bF Cp Dk Md Mq Nb Nq Nx Pg Sr Ua) Nv(Ao Hu Iv Jn Js Kl Mt My Na Ns Pc) Cs(Ad As bC Bn Cp Cu Cw Kd Om Ra) Fy(Ao Bb bX Iz Jf Kl Lu Pa Qz Vo) Lx(An bS cA Cq cT Cu Cw Kn Rj Vp) Qu(Ba Cw dF dG Et Ij Jl Li Mw Tn) Kz(Io Iv Je Ju Kp Nr Oe Ok Qy) Lh(bO eC Iv Iz Kl Li Mt Mz Pc) Ao(Ba Dk Fr Ij Je Jh Nw Ut) Jt(eC Fr Io Jn Jo Li Lv Mq) Oa(bO Fr Hu Io Nc Oe On Ut) Po(Ad Cw Kd Kn Pi Ra Up) Oe(Ba dF dG Gl Qy Sr Wm) Bg(Fr Je Jh Mt Nw Om) Ns(dG Ij Jk Mv Nu Pg) Lu(Ar bR Dk Or Pj Uh) Tn(bL Iz Nc Nk Pc Rg) Ih(Hw Ij In Mi Ml Pc) Of(Ad Cq Dc Kn Up Vp) Vt(Im Jr Mu Nc Qa Sr) aC(Ba cK Dk FR Hu) Bb(Jq Mu Nw On Ut) Wm(Ij Lv Lz Mi Mx) Fn(Ij Jq Ke Kn Om) My(Je Jh Mw Nx Ut) Tv(Et Fa Gl Mu Nw) Io(Ba bQ dF dG Dk) Iz(Et Fr Ij Pf Qa) cT(Fp Ml Qa Uv Vv) Lv(Hw Nb Pa Pc) Mq(Cw Kd Kn Pc) Mx(Ir Mv Nb Nx) Na(Ml Mz Nb Pg) Hu(Cu Fr Jh Kk) Kl(Dk Ij Ok Om) On(aE De Il Nq) bR(bH bZ dJ Ir) eC(Kf Ok Rb Uc) Mg(Ba Ez Ok) Nc(bQ dG Or) Sr(aE Jq Nw) Jo(Fr Li Qb) Oh(An Qz tF) Cw(Jl Vo) Fp(cM Ul) Ml(Jk Pg) Mt(Mv Nu) Mu(Pi Pk) Mz(aK Jn) Ir(Mi Mv) Jq(bN Pa) Li(bO Pc) Vv(Jn Jr) Pf(bS Qz) AlQb MwNl UeOm HxPb ImJu JiaE JlUp KecZ KkPc UkdG UhPe UvaK

Figure 8 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.6E1 | 7.3E1 | 7.7E1 | 1.1E2 | 5.2E1 | 8.9E1 | 2.0E0 | 7.0E0 | 4.4E2 | 4.0E2 | 1475 | 35 | 252 | 35 | 0.58 |
| Ad | ug/mL | 3.4E-2 | 6.2E-2 | 6.8E-2 | 9.1E-2 | 8.7E-2 | 8.4E-2 | 6.8E-4 | 2.7E-4 | 5.4E-1 | 3.5E-1 | 421 | 25 | 165 | 25 | 0.65 |
| Af | ng/mL | 1.1E0 | 4.5E-1 | 1.6E1 | 1.3E1 | 6.2E1 | 4.3E1 | 1.7E-3 | 1.7E-3 | 5.3E2 | 2.2E2 | 421 | 25 | 165 | 25 | 0.46 |
| Aj | ug/mL | 1.8E0 | 3.3E0 | 2.7E0 | 2.8E0 | 2.5E0 | 2.4E0 | 1.5E-3 | 1.8E-3 | 6.1E0 | 6.1E0 | 421 | 25 | 165 | 25 | 0.52 |
| Al | mg/mL | 8.7E-5 | 9.0E-5 | 2.5E-4 | 1.9E-4 | 4.1E-4 | 3.7E-4 | 2.5E-6 | 8.0E-6 | 2.2E-3 | 1.9E-3 | 421 | 25 | 165 | 25 | 0.53 |
| An | U/mL | 4.9E1 | 7.7E1 | 1.6E2 | 2.1E2 | 4.5E2 | 2.7E2 | 9.8E-4 | 8.6E-1 | 5.5E3 | 9.8E2 | 421 | 25 | 165 | 25 | 0.60 |
| Ao | pg/mL | 8.6E1 | 1.2E2 | 5.4E2 | 1.3E2 | 3.6E3 | 1.2E2 | 1.5E0 | 6.1E0 | 3.9E4 | 6.1E2 | 421 | 25 | 165 | 25 | 0.56 |
| Ap | ng/mL | 2.9E1 | 4.6E1 | 4.5E1 | 5.5E1 | 5.0E1 | 4.1E1 | 8.4E-5 | 2.1E0 | 3.3E2 | 1.8E2 | 421 | 25 | 165 | 25 | 0.63 |
| Ar | ng/mL | 8.5E-1 | 1.9E0 | 1.3E1 | 4.2E0 | 2.0E2 | 5.0E0 | 3.4E-3 | 3.4E-3 | 4.1E3 | 2.0E1 | 421 | 25 | 165 | 25 | 0.64 |
| As | ng/mL | 8.7E-3 | 1.2E-2 | 1.3E-2 | 2.0E-2 | 1.7E-2 | 3.2E-2 | 1.7E-3 | 1.7E-3 | 1.3E-1 | 1.2E-1 | 421 | 25 | 165 | 25 | 0.55 |
| Aw | pg/mL | 1.6E1 | 1.7E1 | 1.6E1 | 1.8E1 | 6.0E0 | 6.9E0 | 2.9E-2 | 2.9E-2 | 4.8E1 | 3.8E1 | 421 | 25 | 165 | 25 | 0.58 |
| Ax | ng/mL | 2.0E0 | 4.5E0 | 1.3E1 | 2.1E1 | 5.3E1 | 4.4E1 | 1.9E-2 | 3.9E-2 | 7.7E2 | 2.0E2 | 421 | 25 | 165 | 25 | 0.59 |
| Ba | ng/mL | 5.7E1 | 1.7E2 | 4.1E2 | 7.4E2 | 1.1E3 | 1.7E3 | 2.7E-1 | 6.9E-1 | 8.1E3 | 8.1E3 | 421 | 25 | 165 | 25 | 0.64 |
| Bb | ng/mL | 2.9E0 | 4.9E0 | 6.3E0 | 5.8E0 | 1.5E1 | 4.3E0 | 4.1E-3 | 4.2E-1 | 2.5E2 | 1.6E1 | 421 | 25 | 165 | 25 | 0.60 |
| Bc | ng/mL | 3.4E1 | 7.2E1 | 9.9E1 | 1.2E2 | 1.9E2 | 2.0E2 | 1.1E-1 | 2.4E0 | 1.2E3 | 1.0E3 | 421 | 25 | 165 | 25 | 0.64 |
| Bg | ng/mL | 7.4E-2 | 2.9E-1 | 4.5E0 | 7.3E-1 | 2.1E1 | 1.2E0 | 5.3E-4 | 5.3E-4 | 2.5E2 | 4.8E0 | 421 | 25 | 165 | 25 | 0.61 |
| Bn | ng/mL | 5.6E-2 | 5.6E-2 | 1.2E0 | 1.4E0 | 2.0E0 | 2.4E0 | 5.6E-2 | 5.6E-2 | 9.7E0 | 7.6E0 | 421 | 25 | 165 | 25 | 0.50 |
| Bo | ng/mL | 1.2E1 | 1.7E1 | 1.4E1 | 1.7E1 | 1.9E1 | 1.2E1 | 1.6E-2 | 1.6E-2 | 2.8E2 | 3.6E1 | 421 | 25 | 165 | 25 | 0.60 |
| Ch | uIU/mL | 1.1E0 | 9.8E-1 | 1.9E1 | 6.7E0 | 1.1E2 | 2.1E1 | 3.4E-3 | 1.0E-1 | 1.8E3 | 1.1E2 | 421 | 25 | 165 | 25 | 0.48 |
| Co | pg/mL | 3.6E1 | 6.3E1 | 1.8E2 | 7.9E1 | 9.9E2 | 7.7E1 | 1.5E-1 | 9.1E0 | 1.7E4 | 3.9E2 | 421 | 25 | 165 | 25 | 0.62 |
| Cp | ng/mL | 2.2E1 | 2.4E1 | 2.8E1 | 2.9E1 | 3.2E1 | 2.1E1 | 6.0E-1 | 6.0E-1 | 3.7E2 | 9.9E1 | 421 | 25 | 165 | 25 | 0.57 |
| Cq | ng/mL | 2.8E-2 | 3.9E-2 | 1.4E-1 | 6.6E-2 | 8.8E-1 | 1.1E-1 | 8.0E-4 | 8.0E-4 | 1.7E1 | 4.9E-1 | 421 | 25 | 165 | 25 | 0.54 |
| Cs | ng/mL | 5.3E1 | 1.6E2 | 2.7E2 | 4.6E2 | 8.0E2 | 1.1E3 | 2.7E-2 | 1.5E0 | 1.1E4 | 5.3E3 | 421 | 25 | 165 | 25 | 0.60 |
| Ct | ng/mL | 8.6E-1 | 3.8E-1 | 3.5E1 | 1.7E1 | 1.0E2 | 3.8E1 | 1.1E-4 | 1.5E-2 | 6.2E2 | 1.6E2 | 421 | 25 | 165 | 25 | 0.46 |
| Cu | ng/mL | 2.3E-1 | 3.8E-1 | 4.1E-1 | 3.9E-1 | 7.8E-1 | 2.4E-1 | 9.0E-5 | 1.8E-1 | 9.2E0 | 9.4E-1 | 421 | 25 | 165 | 25 | 0.63 |
| Cv | ng/mL | 4.7E0 | 9.5E0 | 2.2E1 | 3.3E1 | 6.0E1 | 9.2E1 | 1.4E-4 | 1.8E-2 | 5.3E2 | 4.7E2 | 421 | 25 | 165 | 25 | 0.57 |
| Cw | mIU/mL | 3.0E-2 | 3.4E-2 | 3.9E-2 | 3.7E-2 | 3.3E-2 | 2.2E-2 | 8.9E-4 | 1.5E-4 | 2.4E-1 | 9.0E-2 | 421 | 25 | 165 | 25 | 0.52 |
| Cx | ng/mL | 2.6E-1 | 5.6E-2 | 5.8E1 | 6.4E1 | 1.1E2 | 1.3E2 | 9.3E-5 | 9.3E-5 | 3.9E2 | 3.9E2 | 421 | 25 | 165 | 25 | 0.51 |
| Db | ug/mL | 7.5E0 | 6.6E0 | 9.1E0 | 1.4E1 | 8.7E0 | 2.8E1 | 4.5E-1 | 8.5E-1 | 1.0E2 | 1.4E2 | 421 | 25 | 165 | 25 | 0.49 |
| Dc | nmol/L | 1.8E-2 | 1.7E-2 | 5.5E-2 | 2.5E-2 | 1.3E-1 | 2.5E-2 | 5.2E-6 | 3.0E-4 | 1.6E0 | 9.9E-2 | 421 | 25 | 165 | 25 | 0.48 |
| Dd | ug/mL | 7.1E-2 | 3.7E-2 | 1.8E-1 | 1.1E-1 | 2.6E-1 | 2.0E-1 | 8.3E-5 | 4.8E-4 | 1.9E0 | 8.9E-1 | 421 | 25 | 165 | 25 | 0.38 |
| De | ng/mL | 3.4E-3 | 3.4E-3 | 7.6E-2 | 5.8E-2 | 1.4E-1 | 1.1E-1 | 3.4E-3 | 3.4E-3 | 9.2E-1 | 5.0E-1 | 421 | 25 | 165 | 25 | 0.47 |
| Dg | ng/mL | 2.8E1 | 5.7E1 | 4.1E1 | 6.5E1 | 3.9E1 | 4.6E1 | 1.0E-1 | 2.1E0 | 1.9E2 | 1.9E2 | 421 | 25 | 165 | 25 | 0.66 |
| Di | pg/mL | 1.9E0 | 1.3E0 | 2.2E0 | 1.6E0 | 2.0E0 | 1.4E0 | 1.8E-1 | 1.8E-1 | 1.3E1 | 4.0E0 | 421 | 25 | 165 | 25 | 0.43 |
| Dk | uIU/mL | 1.6E-2 | 2.1E-2 | 9.0E-2 | 2.9E-2 | 5.3E-2 | 3.1E-2 | 1.1E-4 | 1.1E-4 | 8.9E0 | 1.4E-1 | 421 | 25 | 165 | 25 | 0.54 |
| Dl | ng/mL | 2.1E2 | 3.2E2 | 3.0E2 | 4.7E2 | 2.8E2 | 4.0E2 | 1.7E0 | 6.4E0 | 1.5E3 | 1.3E3 | 421 | 25 | 165 | 25 | 0.62 |
| Do | ng/ml | 4.7E-1 | 6.3E-1 | 9.5E-1 | 1.1E0 | 2.4E0 | 1.6E0 | 3.6E-2 | 3.6E-2 | 1.9E1 | 4.6E0 | 79 | 7 | 57 | 7 | 0.60 |
| Dp | ng/ml | 2.4E0 | 2.8E0 | 5.2E0 | 4.9E0 | 7.5E0 | 6.1E0 | 3.7E-2 | 2.1E-1 | 4.6E1 | 2.2E1 | 249 | 22 | 162 | 22 | 0.51 |
| Dr | pg/ml | 2.5E1 | 1.7E1 | 5.2E1 | 1.9E1 | 7.1E1 | 2.1E1 | 7.5E-1 | 7.5E-1 | 5.2E2 | 6.0E1 | 154 | 8 | 87 | 8 | 0.34 |
| Dq | Absorbance | 1.7E-3 | 1.7E-3 | 3.0E-2 | 1.7E-3 | 1.3E-1 | 0.0E0 | 1.7E-3 | 1.7E-3 | 8.3E-1 | 1.7E-3 | 77 | 7 | 56 | 7 | 0.36 |
| Dv | pg/ml | 1.0E0 | 7.6E-1 | 1.2E0 | 9.0E-1 | 1.2E0 | 7.4E-1 | 2.2E-2 | 2.2E-2 | 4.7E0 | 2.3E0 | 56 | 7 | 36 | 7 | 0.46 |
| Ef | ng/ml | 1.3E-1 | 1.8E-1 | 8.3E-1 | 7.6E-1 | 1.8E0 | 1.8E0 | 5.7E-4 | 1.3E-3 | 1.0E1 | 8.4E0 | 304 | 23 | 164 | 23 | 0.54 |
| Wm | % | 5.9E-1 | 7.6E-1 | 2.0E1 | 1.3E2 | 1.5E2 | 3.4E2 | 5.4E-2 | 8.5E-2 | 2.4E3 | 1.3E3 | 341 | 25 | 184 | 25 | 0.55 |
| Ed | pg/ml | 5.2E-1 | 5.2E-1 | 5.7E1 | 4.1E1 | 4.6E2 | 8.5E1 | 5.2E-1 | 5.2E-1 | 7.3E3 | 3.5E2 | 249 | 22 | 161 | 22 | 0.49 |
| Tj | pg/mL | 3.7E-1 | 3.7E-1 | 5.9E1 | 7.2E0 | 3.1E2 | 1.2E1 | 3.6E-1 | 3.7E-1 | 3.5E3 | 4.0E1 | 304 | 23 | 167 | 23 | 0.50 |
| Po | pg/ml | 4.8E-1 | 1.9E0 | 8.6E0 | 1.7E1 | 2.5E1 | 4.0E1 | 8.0E-3 | 2.6E-2 | 2.7E2 | 2.2E2 | 690 | 37 | 279 | 37 | 0.58 |
| Em | ng/ml | 2.9E-3 | 2.9E-3 | 5.5E-2 | 1.2E-1 | 1.1E-1 | 2.0E-1 | 1.9E-16 | 1.9E-16 | 6.0E-1 | 4.7E-1 | 190 | 9 | 87 | 9 | 0.55 |
| Et | ng/ml | 1.3E3 | 2.8E3 | 1.5E3 | 2.6E3 | 1.1E3 | 1.4E3 | 7.5E1 | 9.1E1 | 5.0E3 | 5.0E3 | 689 | 37 | 279 | 37 | 0.73 |
| Fa | ng/ml | 3.9E1 | 7.6E1 | 1.2E2 | 8.4E1 | 5.6E2 | 7.1E1 | 3.4E-2 | 2.6E-1 | 8.0E3 | 2.9E2 | 243 | 22 | 159 | 22 | 0.62 |
| Ez | ng/ml | 3.8E0 | 3.7E0 | 1.8E1 | 1.1E1 | 5.5E1 | 1.4E1 | 1.3E-2 | 1.3E-2 | 7.1E2 | 4.6E1 | 249 | 22 | 162 | 22 | 0.50 |
| Fb | ng/ml | 2.5E1 | 2.3E1 | 2.2E1 | 2.3E1 | 1.2E1 | 1.0E1 | 6.6E-1 | 8.1E-1 | 5.7E1 | 4.1E1 | 244 | 22 | 159 | 22 | 0.51 |
| Ex | ng/ml | 7.4E-2 | 1.3E-1 | 2.4E-1 | 2.1E-1 | 7.2E-1 | 2.3E-1 | 3.5E-5 | 1.7E-1 | 8.9E0 | 9.2E-1 | 224 | 17 | 113 | 17 | 0.63 |
| Fn | ng/ml | 2.1E-1 | 2.1E-1 | 6.1E0 | 5.0E0 | 2.7E1 | 7.8E0 | 1.1E-14 | 1.1E-14 | 4.2E2 | 2.6E1 | 249 | 22 | 162 | 22 | 0.50 |

Figure 9

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fp | ng/ml | 1.2E1 | 3.1E1 | 2.3E1 | 4.3E1 | 2.8E1 | 3.6E1 | 6.0E-3 | 2.8E-1 | 1.4E2 | 1.4E2 | 720 | 37 | 280 | 37 | 0.68 |
| Fr | ng/ml | 3.2E4 | 9.6E4 | 1.1E5 | 2.2E5 | 1.7E5 | 2.8E5 | 1.9E2 | 1.2E3 | 9.0E5 | 8.9E5 | 823 | 39 | 284 | 39 | 0.66 |
| Fw | pg/ml | 1.1E0 | 2.9E0 | 6.2E1 | 4.4E1 | 5.0E2 | 1.4E2 | 1.1E-14 | 1.7E-14 | 6.9E3 | 6.3E2 | 304 | 23 | 165 | 23 | 0.54 |
| Fy | ng/ml | 3.5E1 | 4.8E1 | 5.5E1 | 6.0E1 | 5.6E1 | 4.9E1 | 1.2E-1 | 9.7E-1 | 3.3E2 | 2.1E2 | 246 | 22 | 161 | 22 | 0.57 |
| Gc | ng/ml | 9.9E1 | 1.2E2 | 1.5E2 | 1.6E2 | 1.7E2 | 1.4E2 | 6.4E0 | 2.2E1 | 1.2E3 | 4.4E2 | 166 | 8 | 90 | 8 | 0.54 |
| Gn | U/ml | 3.6E-1 | 5.6E-3 | 1.3E0 | 7.6E-2 | 3.1E0 | 1.8E-1 | 1.3E-3 | 1.3E-3 | 3.0E1 | 5.3E-1 | 148 | 8 | 85 | 8 | 0.15 |
| Gl | pg/ml | 7.4E3 | 6.2E3 | 1.1E4 | 8.4E3 | 9.4E3 | 7.0E3 | 9.1E1 | 1.0E3 | 3.4E4 | 2.9E4 | 295 | 23 | 164 | 23 | 0.46 |
| Gp | U/ml | 1.7E0 | 1.8E0 | 4.1E0 | 3.7E0 | 6.6E0 | 5.4E0 | 1.3E-3 | 1.5E-2 | 6.7E1 | 2.1E1 | 306 | 23 | 165 | 23 | 0.47 |
| Gt | ng/ml | 2.2E-3 | 2.2E-3 | 1.3E-1 | 2.2E-3 | 4.5E-1 | 0.0E0 | 2.2E-3 | 2.2E-3 | 3.3E0 | 2.2E-3 | 61 | 7 | 42 | 7 | 0.33 |
| Gw | ng/ml | 5.5E0 | 9.6E0 | 1.6E1 | 1.2E1 | 5.1E1 | 7.8E0 | 8.3E-1 | 3.6E0 | 4.4E2 | 2.2E1 | 79 | 7 | 57 | 7 | 0.67 |
| Gz | ug/ml | 1.4E0 | 1.2E0 | 9.2E0 | 5.4E0 | 3.9E1 | 6.4E0 | 2.9E-16 | 3.8E-3 | 4.8E2 | 2.1E1 | 165 | 16 | 106 | 16 | 0.49 |
| Ha | ng/ml | 2.6E0 | 2.2E0 | 9.9E0 | 3.9E0 | 2.1E1 | 6.4E0 | 1.7E-2 | 1.7E-2 | 1.3E2 | 3.0E1 | 247 | 22 | 161 | 22 | 0.43 |
| Nm | pg/ml | 1.4E4 | 3.1E4 | 3.0E4 | 5.4E4 | 8.2E4 | 8.0E4 | 1.0E-9 | 1.0E-9 | 1.6E6 | 4.4E5 | 693 | 37 | 281 | 37 | 0.63 |
| Nn | pg/ml | 1.5E2 | 4.6E2 | 1.9E3 | 4.3E3 | 8.6E3 | 1.3E4 | 1.0E-9 | 1.0E-9 | 1.0E5 | 6.9E4 | 693 | 37 | 281 | 37 | 0.60 |
| No | pg/ml | 1.4E1 | 3.5E1 | 3.5E1 | 1.0E2 | 1.2E2 | 2.8E2 | 1.0E-9 | 1.0E-9 | 2.5E3 | 1.4E3 | 693 | 37 | 281 | 37 | 0.64 |
| Nq | pg/ml | 1.9E0 | 8.9E-2 | 1.7E1 | 2.8E1 | 7.0E1 | 6.4E1 | 1.0E-9 | 1.0E-9 | 1.2E3 | 2.7E2 | 693 | 37 | 281 | 37 | 0.48 |
| Nr | pg/ml | 6.5E-1 | 4.0E0 | 3.1E1 | 2.5E2 | 2.0E2 | 1.4E3 | 1.0E-9 | 1.0E-9 | 4.1E3 | 8.5E3 | 693 | 37 | 281 | 37 | 0.62 |
| Ns | pg/ml | 1.0E-9 | 1.0E-9 | 9.7E0 | 4.0E0 | 5.6E1 | 2.0E1 | 1.0E-9 | 1.0E-9 | 1.1E3 | 1.2E2 | 693 | 37 | 281 | 37 | 0.51 |
| Nt | pg/ml | 1.0E2 | 1.5E2 | 1.3E2 | 2.0E2 | 1.1E2 | 1.5E2 | 1.0E-9 | 2.6E1 | 1.5E3 | 6.8E2 | 693 | 37 | 281 | 37 | 0.68 |
| Nu | pg/ml | 1.9E1 | 8.8E1 | 5.4E1 | 1.0E2 | 9.4E1 | 1.1E2 | 1.0E-9 | 1.0E-9 | 8.9E2 | 5.8E2 | 693 | 37 | 281 | 37 | 0.66 |
| Lu | pg/ml | 1.0E4 | 1.0E4 | 1.6E4 | 2.0E4 | 4.6E4 | 3.9E4 | 3.5E2 | 1.0E3 | 7.5E5 | 2.3E5 | 695 | 37 | 281 | 37 | 0.50 |
| Lv | pg/ml | 1.0E-9 | 2.5E1 | 1.1E1 | 2.8E1 | 2.1E1 | 3.8E1 | 1.0E-9 | 1.0E-9 | 2.4E2 | 1.9E2 | 695 | 37 | 281 | 37 | 0.66 |
| Lw | pg/ml | 1.0E-9 | 1.0E-9 | 3.7E-1 | 1.0E0 | 4.0E0 | 4.4E0 | 1.0E-9 | 1.0E-9 | 8.0E1 | 2.1E1 | 695 | 37 | 281 | 37 | 0.53 |
| Lx | pg/ml | 1.0E-9 | 1.1E2 | 1.3E2 | 6.3E2 | 4.2E2 | 1.8E3 | 1.0E-9 | 1.0E-9 | 6.2E3 | 1.0E4 | 695 | 37 | 281 | 37 | 0.72 |
| Ly | pg/ml | 1.0E-9 | 1.4E1 | 1.0E1 | 2.0E1 | 2.0E1 | 2.4E1 | 1.0E-9 | 1.0E-9 | 1.6E2 | 8.7E1 | 695 | 37 | 281 | 37 | 0.65 |
| Lz | pg/ml | 1.0E-9 | 1.0E-9 | 4.9E0 | 5.7E0 | 3.4E1 | 3.4E1 | 1.0E-9 | 1.0E-9 | 6.0E2 | 2.1E2 | 695 | 37 | 281 | 37 | 0.48 |
| Ma | pg/ml | 2.7E2 | 3.0E2 | 1.4E3 | 1.5E3 | 3.8E3 | 2.4E3 | 1.0E-9 | 3.0E0 | 6.5E4 | 1.0E4 | 695 | 37 | 281 | 37 | 0.56 |
| Mb | pg/ml | 2.5E1 | 2.9E1 | 3.1E1 | 3.5E1 | 1.6E1 | 1.7E1 | 5.4E0 | 1.6E1 | 2.1E2 | 8.7E1 | 695 | 37 | 281 | 37 | 0.57 |
| Mc | pg/ml | 1.0E-9 | 1.0E-9 | 3.6E-2 | 1.0E-9 | 5.3E-1 | 0.0E0 | 1.0E-9 | 1.0E-9 | 1.3E1 | 1.0E-9 | 695 | 37 | 281 | 37 | 0.49 |
| Md | pg/ml | 1.0E-9 | 1.0E-9 | 5.0E-1 | 2.1E-2 | 4.0E0 | 9.7E-2 | 1.0E-9 | 1.0E-9 | 6.8E1 | 5.5E-1 | 695 | 37 | 281 | 37 | 0.49 |
| Me | pg/ml | 3.2E1 | 2.8E1 | 3.1E1 | 2.9E1 | 2.0E1 | 1.4E1 | 1.0E-9 | 3.2E0 | 3.2E2 | 7.9E1 | 695 | 37 | 281 | 37 | 0.45 |
| Mf | pg/ml | 1.0E-9 | 1.0E-9 | 5.0E-1 | 5.5E-1 | 2.9E0 | 1.6E0 | 1.0E-9 | 1.0E-9 | 5.6E1 | 8.4E0 | 695 | 37 | 281 | 37 | 0.56 |
| Mg | pg/ml | 1.7E0 | 6.4E0 | 7.3E0 | 9.1E0 | 1.2E1 | 1.1E1 | 1.0E-9 | 1.0E-9 | 9.2E1 | 4.0E1 | 695 | 37 | 281 | 37 | 0.60 |
| Mh | pg/ml | 1.0E-9 | 1.0E-9 | 1.5E0 | 1.9E0 | 1.1E1 | 6.7E0 | 1.0E-9 | 1.0E-9 | 1.6E2 | 3.8E1 | 695 | 37 | 281 | 37 | 0.50 |
| Mi | pg/ml | 1.0E-9 | 1.0E-9 | 4.9E-1 | 8.8E0 | 5.8E0 | 2.9E1 | 1.0E-9 | 1.0E-9 | 1.2E2 | 1.6E2 | 695 | 37 | 281 | 37 | 0.57 |
| Mj | pg/ml | 1.0E-9 | 1.0E-9 | 4.8E0 | 1.6E1 | 2.7E1 | 8.9E1 | 1.0E-9 | 1.0E-9 | 4.6E2 | 5.4E2 | 695 | 37 | 281 | 37 | 0.53 |
| Mk | pg/ml | 9.1E-1 | 3.8E0 | 1.5E1 | 1.6E2 | 9.7E1 | 9.1E2 | 1.0E-9 | 1.0E-9 | 1.7E3 | 5.6E3 | 695 | 37 | 281 | 37 | 0.52 |
| Ml | pg/ml | 1.0E-9 | 1.0E-9 | 5.8E0 | 1.3E0 | 8.2E1 | 3.3E0 | 1.0E-9 | 1.0E-9 | 2.1E3 | 1.6E1 | 695 | 37 | 281 | 37 | 0.53 |
| Mm | pg/ml | 5.4E2 | 1.0E3 | 9.2E2 | 1.8E3 | 1.1E3 | 2.0E3 | 1.0E-9 | 1.0E-9 | 7.3E3 | 6.9E3 | 695 | 37 | 281 | 37 | 0.63 |
| Mn | pg/ml | 5.3E0 | 6.7E0 | 1.0E1 | 1.1E1 | 2.4E1 | 1.4E1 | 1.0E-9 | 1.0E-9 | 3.5E2 | 6.6E1 | 695 | 37 | 281 | 37 | 0.56 |
| Mp | pg/ml | 1.0E-9 | 4.8E0 | 8.4E0 | 2.1E1 | 2.9E1 | 4.4E1 | 1.0E-9 | 1.0E-9 | 6.3E2 | 1.8E2 | 694 | 37 | 281 | 37 | 0.59 |
| Mq | pg/ml | 1.0E-9 | 1.0E-9 | 2.8E0 | 7.5E0 | 1.6E1 | 2.9E1 | 1.0E-9 | 1.0E-9 | 2.1E2 | 1.4E2 | 694 | 37 | 281 | 37 | 0.51 |
| Mr | pg/ml | 1.0E-9 | 1.0E-9 | 1.6E1 | 3.8E2 | 7.9E1 | 2.0E3 | 1.0E-9 | 1.0E-9 | 1.4E3 | 1.2E4 | 694 | 37 | 281 | 37 | 0.55 |
| Ms | pg/ml | 4.1E2 | 5.0E2 | 5.6E2 | 5.4E2 | 6.4E2 | 4.9E2 | 1.0E-9 | 1.0E-9 | 5.6E3 | 1.7E3 | 694 | 37 | 281 | 37 | 0.51 |
| Mt | pg/ml | 1.0E-9 | 1.8E0 | 6.8E0 | 9.7E0 | 4.6E1 | 1.8E1 | 1.0E-9 | 1.0E-9 | 8.7E2 | 7.8E1 | 694 | 37 | 281 | 37 | 0.72 |
| Mu | pg/ml | 1.0E-9 | 1.0E-9 | 1.3E0 | 2.2E0 | 1.2E1 | 5.6E0 | 1.0E-9 | 1.0E-9 | 2.3E2 | 2.7E1 | 694 | 37 | 281 | 37 | 0.56 |
| Mv | pg/ml | 1.0E-9 | 1.0E-9 | 6.8E1 | 7.3E1 | 3.3E2 | 1.9E2 | 1.0E-9 | 1.0E-9 | 4.5E3 | 9.3E2 | 694 | 37 | 281 | 37 | 0.54 |
| Mw | pg/ml | 3.2E1 | 6.3E1 | 4.3E2 | 1.0E3 | 2.9E3 | 3.1E3 | 1.0E-9 | 1.0E-9 | 6.2E4 | 1.7E4 | 694 | 37 | 281 | 37 | 0.60 |
| Mx | pg/ml | 1.0E-9 | 1.0E-9 | 2.3E-1 | 2.3E-1 | 1.4E0 | 5.8E-1 | 1.0E-9 | 1.0E-9 | 3.2E1 | 3.0E0 | 694 | 37 | 281 | 37 | 0.56 |
| My | pg/ml | 1.0E-9 | 1.0E-9 | 4.3E2 | 3.5E2 | 2.9E3 | 8.8E2 | 1.0E-9 | 1.0E-9 | 3.9E4 | 4.1E3 | 694 | 37 | 281 | 37 | 0.57 |
| Mz | pg/ml | 1.0E1 | 2.1E1 | 2.4E1 | 4.5E1 | 6.8E1 | 6.3E1 | 1.0E-9 | 1.0E-9 | 1.2E3 | 3.0E2 | 694 | 37 | 281 | 37 | 0.64 |
| Na | pg/ml | 1.0E-9 | 1.0E-9 | 7.7E-1 | 7.8E-1 | 2.9E0 | 2.5E0 | 1.0E-9 | 1.0E-9 | 3.6E1 | 1.1E1 | 694 | 37 | 281 | 37 | 0.51 |
| Nb | pg/ml | 1.9E0 | 2.8E0 | 4.0E0 | 1.1E1 | 1.3E1 | 3.9E1 | 1.0E-9 | 1.0E-9 | 2.3E2 | 2.4E2 | 694 | 37 | 281 | 37 | 0.59 |
| Nc | pg/ml | 3.8E2 | 1.5E2 | 6.2E2 | 2.4E2 | 7.7E2 | 3.4E2 | 1.0E-9 | 1.0E-9 | 9.2E3 | 1.4E3 | 694 | 37 | 281 | 37 | 0.34 |
| Nd | pg/ml | 2.9E1 | 6.8E0 | 2.7E1 | 2.5E1 | 5.0E1 | 3.7E1 | 1.0E-9 | 1.0E-9 | 1.2E3 | 1.4E2 | 694 | 37 | 281 | 37 | 0.40 |
| Ne | pg/ml | 4.7E2 | 2.5E2 | 6.0E2 | 3.1E2 | 5.9E2 | 3.1E2 | 1.0E-9 | 1.0E-9 | 7.0E3 | 1.6E3 | 694 | 37 | 281 | 37 | 0.34 |
| Nf | pg/ml | 1.0E-9 | 1.0E-9 | 3.2E0 | 3.2E0 | 1.0E1 | 1.4E1 | 1.0E-9 | 1.0E-9 | 1.6E2 | 8.2E1 | 694 | 37 | 281 | 37 | 0.42 |

Figure 9 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ng | pg/ml | 2.1E1 | 2.7E1 | 1.3E2 | 1.2E2 | 2.6E2 | 1.7E2 | 1.0E-9 | 1.0E-9 | 2.3E3 | 5.0E2 | 694 | 37 | 281 | 37 | 0.53 |
| Nh | pg/ml | 7.1E1 | 3.3E1 | 9.4E1 | 5.6E1 | 8.6E1 | 5.7E1 | 1.0E-9 | 1.0E-9 | 5.6E2 | 2.1E2 | 694 | 37 | 281 | 37 | 0.34 |
| Ni | pg/ml | 1.0E-9 | 2.5E1 | 7.6E1 | 9.6E1 | 1.2E2 | 1.2E2 | 1.0E-9 | 1.0E-9 | 7.1E2 | 3.9E2 | 694 | 37 | 281 | 37 | 0.55 |
| Nj | pg/ml | 8.2E0 | 2.8E0 | 1.2E1 | 6.7E0 | 1.2E1 | 1.1E1 | 1.0E-9 | 1.0E-9 | 8.3E1 | 5.7E1 | 694 | 37 | 281 | 37 | 0.34 |
| Nk | pg/ml | 1.9E1 | 1.6E1 | 3.4E1 | 2.3E1 | 4.0E1 | 3.2E1 | 1.0E-9 | 1.0E-9 | 2.0E2 | 1.7E2 | 694 | 37 | 281 | 37 | 0.45 |
| Nl | pg/ml | 4.9E1 | 1.6E1 | 6.5E1 | 2.7E1 | 7.2E1 | 2.9E1 | 1.0E-9 | 1.0E-9 | 1.1E3 | 1.0E2 | 694 | 37 | 281 | 37 | 0.31 |
| Tz | pg/ml | 5.2E3 | 8.8E3 | 1.3E4 | 9.3E3 | 6.4E4 | 1.2E4 | 1.0E-9 | 2.3E2 | 1.0E6 | 5.6E4 | 251 | 22 | 160 | 22 | 0.53 |
| Ua | pg/ml | 3.8E3 | 5.4E3 | 2.3E4 | 8.4E3 | 1.4E5 | 1.1E4 | 1.0E-9 | 4.3E2 | 2.1E6 | 4.3E4 | 251 | 22 | 160 | 22 | 0.53 |
| Ub | pg/ml | 5.7E2 | 5.4E2 | 8.6E2 | 8.6E2 | 1.0E3 | 1.2E3 | 1.0E-9 | 3.4E1 | 9.8E3 | 4.9E3 | 251 | 22 | 160 | 22 | 0.47 |
| Ue | pg/ml | 3.0E1 | 2.2E1 | 3.7E1 | 5.2E1 | 3.2E1 | 9.3E1 | 9.8E-2 | 5.1E0 | 3.5E2 | 4.4E2 | 251 | 22 | 160 | 22 | 0.43 |
| Uc | pg/ml | 8.6E2 | 9.6E2 | 1.6E3 | 1.7E3 | 2.7E3 | 1.8E3 | 1.0E-9 | 6.0E1 | 2.9E4 | 7.2E3 | 251 | 22 | 160 | 22 | 0.54 |
| Ud | pg/ml | 1.0E-9 | 1.0E-9 | 1.7E0 | 1.0E0 | 2.5E1 | 0.0E0 | 1.0E-9 | 1.0E-9 | 3.9E2 | 1.0E-9 | 251 | 22 | 160 | 22 | 0.49 |
| Hq | pg/ml | 1.1E0 | 1.9E0 | 1.3E1 | 1.1E1 | 1.8E3 | 4.9E1 | 1.0E-9 | 1.0E-9 | 3.4E4 | 3.0E2 | 691 | 37 | 280 | 37 | 0.55 |
| Hr | pg/ml | 1.3E2 | 9.6E1 | 8.2E2 | 9.6E2 | 1.6E3 | 3.3E3 | 1.0E-9 | 1.0E-9 | 1.4E4 | 1.7E4 | 691 | 37 | 280 | 37 | 0.42 |
| Hu | pg/ml | 7.1E0 | 9.0E0 | 3.0E3 | 1.7E3 | 2.9E4 | 7.8E3 | 1.0E-9 | 1.0E-9 | 6.3E5 | 4.7E4 | 691 | 37 | 280 | 37 | 0.53 |
| Hv | pg/ml | 1.4E0 | 2.6E0 | 3.3E0 | 4.9E0 | 1.2E1 | 1.0E1 | 1.0E-9 | 1.0E-9 | 2.5E2 | 5.9E1 | 691 | 37 | 280 | 37 | 0.65 |
| Hw | pg/ml | 7.1E0 | 3.7E0 | 2.0E1 | 1.1E2 | 8.0E1 | 5.6E2 | 1.0E-9 | 1.0E-9 | 1.7E3 | 3.4E3 | 691 | 37 | 280 | 37 | 0.43 |
| Hx | pg/ml | 8.8E0 | 1.1E1 | 4.4E1 | 7.0E1 | 3.6E2 | 3.2E2 | 1.0E-9 | 1.0E-9 | 9.3E3 | 2.0E3 | 691 | 37 | 280 | 37 | 0.49 |
| Ib | ng/ml | 6.2E-2 | 2.9E-2 | 1.4E0 | 4.5E-1 | 5.0E0 | 1.3E0 | 1.0E-9 | 1.0E-9 | 3.6E1 | 6.1E0 | 241 | 22 | 159 | 22 | 0.42 |
| Ic | U/ml | 2.2E2 | 2.2E2 | 7.3E2 | 1.6E3 | 6.1E3 | 6.2E3 | 2.4E0 | 1.5E0 | 9.3E4 | 3.0E4 | 241 | 22 | 159 | 22 | 0.59 |
| Id | U/ml | 6.4E-1 | 1.2E0 | 1.2E0 | 2.3E0 | 2.0E0 | 4.3E0 | 1.0E-9 | 5.6E-2 | 2.3E1 | 2.1E1 | 241 | 22 | 159 | 22 | 0.65 |
| Tt | pg/ml | 1.6E2 | 1.9E2 | 1.7E2 | 1.9E2 | 5.1E1 | 4.1E1 | 4.3E1 | 1.2E2 | 3.6E2 | 2.6E2 | 231 | 22 | 153 | 22 | 0.62 |
| To | pg/ml | 1.6E0 | 1.9E0 | 1.9E0 | 2.4E0 | 2.4E0 | 1.8E0 | 1.0E-9 | 1.0E-9 | 2.3E1 | 6.3E0 | 242 | 22 | 157 | 22 | 0.62 |
| Tr | pg/ml | 2.8E0 | 4.3E0 | 5.8E0 | 5.8E0 | 2.0E1 | 4.9E0 | 1.0E-9 | 9.5E-2 | 3.1E2 | 2.1E1 | 238 | 22 | 156 | 22 | 0.61 |
| Tn | pg/ml | 2.6E1 | 3.2E1 | 8.0E1 | 4.7E1 | 2.2E2 | 4.9E1 | 2.4E0 | 1.1E1 | 1.8E3 | 2.3E2 | 242 | 22 | 157 | 22 | 0.58 |
| Tv | ng/ml | 1.2E1 | 1.6E1 | 1.9E1 | 2.0E1 | 3.7E1 | 2.1E1 | 1.0E-9 | 1.0E-9 | 4.9E2 | 7.0E1 | 242 | 22 | 157 | 22 | 0.52 |
| Ih | ng/ml | 6.9E1 | 1.8E2 | 2.1E2 | 4.3E2 | 3.7E2 | 7.1E2 | 1.0E-9 | 1.0E-9 | 2.6E3 | 2.9E3 | 694 | 37 | 280 | 37 | 0.58 |
| Ii | ng/ml | 9.0E1 | 1.3E2 | 2.6E2 | 5.3E2 | 7.4E2 | 1.7E3 | 7.3E-1 | 3.5E0 | 1.0E4 | 9.2E3 | 694 | 37 | 280 | 37 | 0.56 |
| Ij | ng/ml | 7.3E1 | 9.9E1 | 1.8E2 | 2.8E2 | 6.4E2 | 1.0E3 | 2.1E0 | 8.7E0 | 6.4E3 | 6.4E3 | 686 | 37 | 279 | 37 | 0.59 |
| Ik | ng/ml | 1.4E1 | 2.4E2 | 9.8E2 | 5.3E2 | 9.3E3 | 8.4E2 | 5.9E-1 | 1.3E0 | 1.2E5 | 4.5E3 | 690 | 37 | 279 | 37 | 0.66 |
| Il | ng/ml | 3.3E2 | 3.1E2 | 1.2E3 | 1.2E3 | 2.7E3 | 2.8E3 | 1.0E-9 | 1.0E-9 | 1.2E4 | 1.2E4 | 680 | 34 | 279 | 34 | 0.48 |
| Im | ng/ml | 1.9E2 | 3.3E2 | 3.4E2 | 6.1E2 | 5.0E2 | 1.1E3 | 1.3E1 | 2.4E1 | 6.0E3 | 6.8E3 | 689 | 37 | 279 | 37 | 0.65 |
| In | ng/ml | 3.9E0 | 3.3E0 | 2.5E1 | 1.0E1 | 1.7E2 | 1.8E1 | 1.0E-9 | 1.0E-9 | 3.9E3 | 7.5E1 | 694 | 37 | 280 | 37 | 0.45 |
| Hb | ng/ml | 2.4E1 | 3.3E1 | 3.2E1 | 4.0E1 | 2.9E1 | 3.3E1 | 4.8E-1 | 1.5E0 | 1.5E2 | 1.1E2 | 248 | 22 | 160 | 22 | 0.57 |
| Hc | ng/ml | 6.7E2 | 5.9E2 | 3.7E3 | 2.2E3 | 1.3E4 | 3.3E3 | 1.0E-9 | 2.6E2 | 1.0E5 | 1.1E4 | 248 | 22 | 160 | 22 | 0.53 |
| Hf | ng/ml | 1.5E2 | 2.7E2 | 3.8E2 | 3.2E2 | 5.3E2 | 3.4E2 | 1.0E-9 | 1.0E-9 | 2.5E3 | 1.3E3 | 248 | 22 | 160 | 22 | 0.53 |
| Io | ng/ml | 7.5E3 | 1.0E4 | 2.4E4 | 5.1E4 | 1.6E5 | 1.3E5 | 1.0E-9 | 2.2E2 | 4.0E6 | 5.5E5 | 687 | 36 | 280 | 36 | 0.57 |
| Ip | ng/ml | 8.7E0 | 1.8E1 | 1.9E1 | 2.7E1 | 2.4E1 | 3.2E1 | 1.0E-9 | 5.6E-3 | 2.6E2 | 1.4E2 | 687 | 36 | 280 | 36 | 0.55 |
| Iq | ug/ml | 9.5E-2 | 3.6E-2 | 4.0E1 | 2.3E1 | 7.3E2 | 1.3E2 | 1.0E-9 | 1.0E-9 | 1.4E4 | 7.5E2 | 687 | 36 | 280 | 36 | 0.45 |
| Ir | ug/ml | 3.3E-1 | 7.7E-1 | 3.8E0 | 4.9E0 | 2.8E1 | 1.9E1 | 1.0E-9 | 1.0E-9 | 5.1E2 | 1.1E2 | 686 | 36 | 280 | 36 | 0.64 |
| Is | ng/ml | 1.4E0 | 2.1E0 | 5.7E0 | 1.4E1 | 2.3E1 | 3.9E1 | 1.0E-9 | 1.0E-9 | 5.5E2 | 2.3E2 | 687 | 36 | 280 | 36 | 0.60 |
| It | ng/ml | 2.0E0 | 2.6E0 | 2.6E1 | 2.5E1 | 1.5E2 | 9.9E1 | 1.0E-9 | 1.0E-9 | 2.8E3 | 5.9E2 | 687 | 36 | 280 | 36 | 0.57 |
| Iu | ng/ml | 2.1E2 | 2.9E2 | 1.4E3 | 2.4E3 | 4.3E3 | 6.7E3 | 1.0E-9 | 1.0E-9 | 2.9E4 | 2.4E4 | 687 | 36 | 280 | 36 | 0.53 |
| Iv | ng/ml | 1.2E1 | 2.6E1 | 6.1E1 | 2.4E2 | 6.1E2 | 1.1E3 | 1.0E-9 | 1.0E-9 | 1.6E4 | 6.4E3 | 686 | 36 | 280 | 36 | 0.64 |
| Iz | ng/ml | 1.4E2 | 2.1E2 | 6.8E2 | 3.4E2 | 4.0E3 | 4.2E2 | 1.5E0 | 9.2E-1 | 6.2E4 | 1.6E3 | 248 | 22 | 160 | 22 | 0.56 |
| Rc | pg/ml | 5.5E3 | 6.1E3 | 7.3E3 | 6.3E3 | 6.0E3 | 3.8E3 | 1.9E2 | 7.5E2 | 3.9E4 | 1.6E4 | 248 | 22 | 160 | 22 | 0.49 |
| Rb | pg/ml | 7.9E-1 | 1.9E0 | 2.6E0 | 3.9E0 | 4.4E0 | 5.4E0 | 1.0E-9 | 1.0E-9 | 4.3E1 | 2.1E1 | 248 | 22 | 160 | 22 | 0.62 |
| Pz | ng/ml | 3.3E3 | 1.0E4 | 6.8E3 | 9.3E3 | 1.8E4 | 1.5E4 | 1.3E1 | 1.5E2 | 2.8E5 | 9.5E4 | 687 | 37 | 278 | 37 | 0.62 |
| Qa | ng/ml | 3.1E3 | 6.6E3 | 5.8E3 | 8.5E3 | 7.1E3 | 6.6E3 | 1.5E2 | 3.8E2 | 5.2E4 | 2.4E4 | 687 | 37 | 278 | 37 | 0.65 |
| Qb | ng/ml | 9.1E1 | 1.4E2 | 2.1E2 | 2.2E2 | 5.2E2 | 2.0E2 | 7.9E-1 | 1.0E1 | 8.3E3 | 6.0E2 | 687 | 37 | 278 | 37 | 0.60 |
| Qc | ng/ml | 2.1E2 | 3.2E2 | 4.4E2 | 4.3E2 | 7.6E2 | 4.3E2 | 1.0E-9 | 6.8E0 | 1.1E4 | 1.6E3 | 687 | 37 | 278 | 37 | 0.55 |
| Qd | ng/ml | 8.7E3 | 1.3E4 | 1.9E4 | 2.2E4 | 8.2E4 | 2.4E4 | 1.5E2 | 9.0E2 | 2.0E6 | 1.2E5 | 687 | 37 | 278 | 37 | 0.63 |
| Qe | ng/ml | 8.0E2 | 1.7E3 | 1.7E3 | 2.6E3 | 4.2E3 | 2.6E3 | 1.0E-9 | 8.2E1 | 9.7E4 | 1.4E4 | 687 | 37 | 278 | 37 | 0.69 |
| Jd | ng/ml | 9.2E-1 | 1.1E0 | 6.7E0 | 2.3E0 | 4.4E1 | 3.9E0 | 1.0E-9 | 1.0E-9 | 6.5E2 | 1.9E1 | 249 | 22 | 162 | 22 | 0.55 |
| Je | ng/ml | 1.0E-9 | 3.9E-1 | 2.3E0 | 1.2E0 | 8.0E0 | 1.5E0 | 1.0E-9 | 1.0E-9 | 8.8E1 | 4.5E0 | 249 | 22 | 162 | 22 | 0.54 |
| Jf | ng/ml | 1.0E-9 | 7.4E-1 | 1.1E0 | 1.7E0 | 2.3E0 | 2.4E0 | 1.0E-9 | 1.0E-9 | 1.2E1 | 8.7E0 | 249 | 22 | 162 | 22 | 0.64 |
| Jg | ng/ml | 4.4E2 | 1.1E3 | 7.3E2 | 1.6E3 | 9.6E2 | 1.6E3 | 1.0E-9 | 2.1E1 | 1.0E4 | 6.8E3 | 691 | 37 | 280 | 37 | 0.70 |

Figure 9 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jh | ng/ml | 2.9E0 | 5.6E0 | 2.4E1 | 4.2E1 | 1.1E2 | 9.4E1 | 1.0E-9 | 1.0E-9 | 1.6E3 | 4.7E2 | 691 | 37 | 280 | 37 | 0.59 |
| Ji | ng/ml | 5.0E1 | 7.4E1 | 7.0E1 | 1.8E2 | 6.9E1 | 3.0E2 | 1.0E-9 | 1.0E1 | 5.3E2 | 1.8E3 | 691 | 37 | 280 | 37 | 0.69 |
| Sr | pg/mL | 3.4E2 | 6.7E2 | 8.1E2 | 1.1E3 | 1.3E3 | 1.1E3 | 1.0E-9 | 1.9E1 | 9.8E3 | 4.1E3 | 239 | 22 | 157 | 22 | 0.64 |
| Ss | pg/mL | 9.2E4 | 1.0E5 | 1.5E5 | 1.3E5 | 1.9E5 | 1.1E5 | 2.7E3 | 1.4E4 | 1.8E6 | 4.7E5 | 239 | 22 | 157 | 22 | 0.53 |
| St | pg/mL | 2.2E7 | 4.6E7 | 4.9E7 | 8.7E7 | 9.0E7 | 1.1E8 | 1.0E-9 | 1.5E6 | 1.2E9 | 4.2E8 | 244 | 22 | 158 | 22 | 0.64 |
| Ra | pg/ml | 1.0E-9 | 2.6E-1 | 6.4E-1 | 5.3E-1 | 1.3E0 | 9.9E-1 | 1.0E-9 | 1.0E-9 | 7.3E0 | 4.1E0 | 248 | 22 | 160 | 22 | 0.57 |
| Qz | pg/ml | 1.1E1 | 4.9E0 | 6.1E1 | 5.2E1 | 1.0E2 | 6.8E1 | 1.0E-9 | 1.0E-9 | 7.1E2 | 2.0E2 | 248 | 22 | 160 | 22 | 0.46 |
| Qy | pg/ml | 4.3E-1 | 6.2E-1 | 1.0E1 | 2.5E1 | 5.7E1 | 1.1E2 | 1.0E-9 | 1.1E-2 | 6.5E2 | 5.1E2 | 248 | 22 | 160 | 22 | 0.58 |
| Qx | pg/ml | 1.0E-9 | 1.0E-9 | 6.8E0 | 8.3E-1 | 5.2E1 | 1.9E0 | 1.0E-9 | 1.0E-9 | 5.8E2 | 7.1E0 | 248 | 22 | 160 | 22 | 0.55 |
| Qw | pg/ml | 1.0E-9 | 1.0E-9 | 2.5E0 | 2.8E-1 | 1.1E1 | 7.2E-1 | 1.0E-9 | 1.0E-9 | 1.2E2 | 2.4E0 | 248 | 22 | 160 | 22 | 0.37 |
| Qv | pg/ml | 2.4E4 | 1.9E4 | 3.4E4 | 3.0E4 | 5.7E4 | 3.4E4 | 1.0E-9 | 6.0E1 | 7.4E5 | 1.4E5 | 248 | 22 | 160 | 22 | 0.45 |
| Qu | pg/ml | 7.7E0 | 1.7E1 | 8.8E1 | 9.1E1 | 1.7E2 | 2.0E2 | 1.0E-9 | 1.0E-9 | 9.8E2 | 9.2E2 | 248 | 22 | 160 | 22 | 0.54 |
| Qt | pg/ml | 1.0E1 | 1.0E-9 | 5.3E1 | 2.6E1 | 1.3E2 | 5.6E1 | 1.0E-9 | 1.0E-9 | 1.0E3 | 1.9E2 | 248 | 22 | 160 | 22 | 0.41 |
| Qh | ng/ml | 1.7E1 | 1.7E1 | 3.6E1 | 3.0E1 | 6.1E1 | 2.9E1 | 1.0E-9 | 3.9E0 | 6.4E2 | 1.1E2 | 248 | 22 | 160 | 22 | 0.54 |
| Qg | ng/ml | 8.5E0 | 6.5E0 | 2.1E1 | 9.6E0 | 7.1E1 | 9.9E0 | 5.1E-2 | 1.4E-1 | 1.0E3 | 4.2E1 | 248 | 22 | 160 | 22 | 0.43 |
| Jj | ng/ml | 6.7E2 | 2.8E2 | 1.9E3 | 8.8E2 | 1.4E4 | 1.9E3 | 2.3E0 | 1.7E1 | 3.4E5 | 1.1E4 | 691 | 37 | 280 | 37 | 0.36 |
| Jk | ng/ml | 3.0E0 | 4.2E0 | 2.2E1 | 3.0E1 | 4.7E1 | 6.9E1 | 1.0E-9 | 1.0E-1 | 3.9E2 | 3.5E2 | 691 | 37 | 280 | 37 | 0.54 |
| Jl | ng/ml | 3.9E-1 | 9.5E-1 | 1.7E0 | 7.2E0 | 4.2E0 | 2.6E1 | 7.6E-4 | 2.9E-3 | 3.2E1 | 1.6E2 | 691 | 37 | 280 | 37 | 0.62 |
| Jm | ng/ml | 1.7E1 | 3.3E1 | 5.2E1 | 5.3E1 | 1.1E2 | 6.4E1 | 1.0E-9 | 7.7E-1 | 1.4E3 | 2.3E2 | 691 | 37 | 280 | 37 | 0.57 |
| Jn | pg/ml | 3.8E-1 | 1.0E0 | 2.4E0 | 2.3E0 | 2.4E1 | 4.8E0 | 1.0E-9 | 1.0E-9 | 6.2E2 | 2.7E1 | 691 | 37 | 280 | 37 | 0.63 |
| Jo | pg/ml | 3.6E3 | 4.7E3 | 4.9E3 | 5.3E3 | 3.9E3 | 6.2E3 | 2.0E1 | 4.9E1 | 2.4E4 | 3.8E4 | 691 | 37 | 280 | 37 | 0.51 |
| Jp | pg/ml | 6.8E4 | 1.0E5 | 7.1E4 | 9.5E4 | 3.6E4 | 3.8E4 | 5.8E2 | 3.5E3 | 3.0E5 | 1.7E5 | 691 | 37 | 280 | 37 | 0.70 |
| Jq | pg/ml | 9.5E1 | 1.1E2 | 1.5E2 | 2.5E2 | 2.2E2 | 6.0E2 | 1.0E0 | 8.1E0 | 4.0E3 | 3.7E3 | 691 | 37 | 280 | 37 | 0.52 |
| Jr | pg/ml | 5.1E0 | 6.1E0 | 3.5E1 | 2.1E1 | 4.1E2 | 4.5E1 | 1.0E-9 | 1.0E-9 | 1.1E4 | 2.0E2 | 691 | 37 | 280 | 37 | 0.59 |
| Js | pg/ml | 1.3E1 | 1.6E1 | 5.2E1 | 3.5E1 | 4.0E2 | 5.9E1 | 1.0E-9 | 1.0E-9 | 9.1E3 | 5.0E2 | 691 | 37 | 280 | 37 | 0.57 |
| Jt | pg/ml | 2.5E3 | 2.9E3 | 3.1E3 | 4.3E3 | 2.3E3 | 5.3E3 | 2.2E1 | 7.7E1 | 2.2E4 | 3.3E4 | 691 | 37 | 280 | 37 | 0.57 |
| Ju | mIU/ml | 8.5E0 | 1.1E1 | 2.0E1 | 1.5E1 | 3.2E1 | 1.3E1 | 6.5E-2 | 6.5E-1 | 2.3E2 | 4.9E1 | 249 | 22 | 162 | 22 | 0.54 |
| Jv | mIU/ml | 1.1E1 | 1.3E1 | 3.5E1 | 2.3E1 | 6.3E1 | 2.4E1 | 1.0E-2 | 1.8E-1 | 4.4E2 | 9.1E1 | 249 | 22 | 162 | 22 | 0.53 |
| Jy | ng/ml | 1.6E-3 | 1.6E-3 | 2.2E-3 | 1.8E-3 | 4.3E-3 | 1.2E-3 | 1.0E-9 | 8.7E-5 | 5.2E-2 | 6.4E-3 | 249 | 22 | 162 | 22 | 0.48 |
| Kc | pg/ml | 2.3E1 | 5.7E1 | 4.1E1 | 7.8E1 | 4.3E1 | 6.9E1 | 1.0E-9 | 1.0E-9 | 1.9E2 | 2.0E2 | 249 | 22 | 160 | 22 | 0.62 |
| Kd | pg/ml | 1.0E-9 | 1.0E-9 | 1.6E2 | 3.7E2 | 5.4E2 | 6.9E2 | 1.0E-9 | 1.0E-9 | 4.8E3 | 2.3E3 | 249 | 22 | 160 | 22 | 0.58 |
| Ke | pg/ml | 1.2E4 | 1.5E4 | 1.4E4 | 1.5E4 | 1.1E4 | 7.7E3 | 3.4E2 | 1.1E3 | 7.0E4 | 3.6E4 | 249 | 22 | 160 | 22 | 0.58 |
| Kf | pg/mL | 6.4E0 | 9.4E0 | 6.8E0 | 9.1E0 | 5.6E0 | 5.1E0 | 1.0E-9 | 1.0E-9 | 2.6E1 | 1.8E1 | 249 | 22 | 160 | 22 | 0.64 |
| Kg | pg/mL | 1.1E3 | 1.4E3 | 1.9E3 | 1.7E3 | 2.6E3 | 1.3E3 | 7.3E1 | 1.3E2 | 2.2E4 | 4.4E3 | 249 | 22 | 160 | 22 | 0.53 |
| Ki | pg/ml | 6.1E1 | 5.2E1 | 7.0E1 | 5.6E1 | 5.2E1 | 3.8E1 | 1.0E-9 | 1.0E-9 | 3.8E2 | 1.4E2 | 248 | 22 | 160 | 22 | 0.43 |
| Kj | pg/ml | 1.0E3 | 1.2E3 | 1.6E3 | 1.5E3 | 1.6E3 | 1.4E3 | 1.4E1 | 3.0E1 | 1.0E4 | 4.5E3 | 249 | 22 | 160 | 22 | 0.49 |
| Kk | pg/ml | 6.9E0 | 9.0E0 | 1.1E1 | 2.0E1 | 1.5E1 | 2.1E1 | 1.0E-9 | 1.0E-9 | 1.6E2 | 6.1E1 | 249 | 22 | 160 | 22 | 0.63 |
| Kl | pg/ml | 2.0E4 | 3.3E4 | 2.7E4 | 3.2E4 | 2.5E4 | 2.4E4 | 1.6E2 | 1.4E3 | 1.6E5 | 1.0E5 | 249 | 22 | 160 | 22 | 0.57 |
| Kn | pg/ml | 2.9E1 | 5.8E1 | 5.8E1 | 9.0E1 | 9.0E1 | 1.1E2 | 1.0E-9 | 1.0E-9 | 7.3E2 | 4.1E2 | 249 | 22 | 160 | 22 | 0.61 |
| Ko | pg/ml | 3.2E2 | 7.4E2 | 4.3E2 | 7.8E2 | 4.4E2 | 6.2E2 | 1.0E-9 | 1.0E-9 | 2.2E3 | 2.4E3 | 249 | 22 | 160 | 22 | 0.69 |
| Kp | pg/ml | 3.0E2 | 3.6E2 | 3.4E2 | 4.4E2 | 2.6E2 | 2.5E2 | 1.0E-9 | 6.4E1 | 1.7E3 | 9.1E2 | 249 | 22 | 160 | 22 | 0.62 |
| Kq | pg/ml | 3.0E2 | 4.7E2 | 4.8E2 | 4.9E2 | 8.7E2 | 2.3E2 | 1.6E0 | 2.5E1 | 9.8E3 | 8.7E2 | 240 | 22 | 154 | 22 | 0.65 |
| Kr | pg/ml | 3.8E-1 | 9.0E-1 | 2.2E0 | 2.6E0 | 4.2E0 | 3.3E0 | 1.0E-9 | 1.0E-9 | 3.5E1 | 9.6E0 | 240 | 22 | 154 | 22 | 0.55 |
| Ks | pg/ml | 1.4E4 | 1.5E4 | 2.0E4 | 1.9E4 | 1.8E4 | 1.7E4 | 5.1E1 | 2.2E2 | 1.1E5 | 5.0E4 | 240 | 22 | 154 | 22 | 0.51 |
| Kx | ng/ml | 1.0E-9 | 1.0E-9 | 6.6E-3 | 5.1E-3 | 1.4E-2 | 6.2E-3 | 1.0E-9 | 1.0E-9 | 1.0E-1 | 1.5E-2 | 247 | 22 | 160 | 22 | 0.51 |
| Ky | ng/ml | 8.5E-2 | 1.1E-1 | 3.5E-1 | 4.5E-1 | 7.8E-1 | 5.9E-1 | 1.0E-9 | 1.0E-9 | 5.4E0 | 2.0E0 | 247 | 22 | 160 | 22 | 0.60 |
| Kz | ng/ml | 1.0E-9 | 1.0E-9 | 3.7E-3 | 1.9E-3 | 5.9E-3 | 2.6E-3 | 1.0E-9 | 1.0E-9 | 3.6E-2 | 6.6E-3 | 247 | 22 | 160 | 22 | 0.46 |
| Ld | pg/ml | 1.0E-9 | 3.7E-1 | 3.6E0 | 2.6E0 | 9.2E0 | 3.8E0 | 1.0E-9 | 1.0E-9 | 8.4E1 | 1.2E1 | 246 | 22 | 159 | 22 | 0.53 |
| Lh | pg/ml | 1.2E4 | 2.1E4 | 2.0E4 | 4.1E4 | 2.5E4 | 7.3E4 | 1.0E-9 | 1.8E2 | 2.6E5 | 4.1E5 | 691 | 37 | 281 | 37 | 0.65 |
| Li | pg/ml | 2.8E3 | 6.6E3 | 1.5E4 | 4.0E4 | 5.9E4 | 1.0E5 | 1.0E-9 | 1.6E1 | 1.3E6 | 5.9E5 | 691 | 37 | 281 | 37 | 0.67 |
| Lj | pg/ml | 2.3E3 | 8.0E3 | 2.1E4 | 3.5E4 | 6.5E4 | 7.3E4 | 1.0E-9 | 8.9E1 | 4.7E5 | 3.5E5 | 691 | 37 | 281 | 37 | 0.65 |
| Rm | ng/ml | 1.9E1 | 3.7E1 | 4.9E1 | 4.5E1 | 7.4E1 | 5.5E1 | 2.2E-1 | 7.0E-1 | 4.0E2 | 2.5E2 | 245 | 21 | 159 | 21 | 0.54 |
| Rh | ng/ml | 1.3E2 | 1.6E2 | 3.6E2 | 3.3E2 | 1.2E3 | 5.3E2 | 3.6E0 | 1.4E1 | 1.7E4 | 2.5E3 | 245 | 21 | 159 | 21 | 0.57 |
| Ri | ng/ml | 1.0E-9 | 4.1E-1 | 4.4E0 | 2.9E0 | 1.6E1 | 4.7E0 | 1.0E-9 | 1.0E-9 | 2.2E2 | 2.0E1 | 246 | 21 | 160 | 21 | 0.54 |
| Rg | ng/ml | 1.0E-9 | 1.0E-9 | 7.1E-2 | 2.1E-3 | 4.2E-1 | 5.1E-3 | 1.0E-9 | 1.0E-9 | 4.6E0 | 2.2E-2 | 245 | 21 | 159 | 21 | 0.53 |
| Rj | ng/ml | 1.0E-9 | 1.0E-9 | 1.6E0 | 3.0E-1 | 6.0E0 | 8.1E-1 | 1.0E-9 | 1.0E-9 | 8.0E1 | 3.2E0 | 246 | 21 | 160 | 21 | 0.44 |
| Rf | ng/ml | 3.7E-1 | 6.0E-1 | 9.8E-1 | 1.6E0 | 1.9E0 | 2.2E0 | 7.8E-3 | 2.2E-2 | 1.5E1 | 7.5E0 | 245 | 21 | 159 | 21 | 0.63 |

Figure 9 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ql | pg/ml | 4.5E0 | 3.1E0 | 1.4E1 | 9.9E0 | 3.1E1 | 1.4E1 | 1.0E-9 | 1.0E-9 | 2.9E2 | 5.9E1 | 249 | 22 | 162 | 22 | 0.48 |
| Qm | pg/ml | 3.9E0 | 7.1E0 | 2.0E1 | 1.7E1 | 3.9E1 | 2.0E1 | 1.0E-9 | 1.0E-9 | 3.6E2 | 5.9E1 | 249 | 22 | 162 | 22 | 0.51 |
| Qn | pg/ml | 6.1E-1 | 5.6E-1 | 6.9E0 | 6.5E0 | 2.2E1 | 2.2E1 | 1.0E-9 | 1.0E-9 | 2.2E2 | 1.0E2 | 249 | 22 | 162 | 22 | 0.41 |
| Nv | pg/ml | 3.8E3 | 9.0E3 | 1.1E4 | 1.8E4 | 4.8E4 | 2.8E4 | 1.0E-9 | 3.9E1 | 1.1E6 | 1.3E5 | 696 | 37 | 281 | 37 | 0.67 |
| Nw | pg/ml | 8.1E3 | 1.7E4 | 1.2E4 | 2.7E4 | 1.7E4 | 3.9E4 | 8.6E1 | 7.3E2 | 2.1E5 | 2.1E5 | 696 | 37 | 281 | 37 | 0.75 |
| Nx | pg/ml | 2.0E2 | 4.7E2 | 3.8E2 | 7.6E2 | 6.6E2 | 7.8E2 | 1.0E-9 | 1.0E-9 | 7.4E3 | 2.8E3 | 696 | 37 | 281 | 37 | 0.67 |
| Ny | pg/ml | 5.5E0 | 1.0E1 | 6.2E0 | 3.9E1 | 9.6E2 | 1.0E2 | 1.0E-9 | 1.0E-9 | 2.5E4 | 6.2E2 | 696 | 37 | 281 | 37 | 0.62 |
| Oa | pg/ml | 1.6E2 | 3.0E2 | 4.0E2 | 5.1E2 | 6.9E2 | 5.8E2 | 1.0E-9 | 1.0E-9 | 4.8E3 | 2.4E3 | 249 | 22 | 162 | 22 | 0.62 |
| Oe | pg/ml | 4.9E1 | 3.5E1 | 2.9E2 | 3.1E2 | 8.1E2 | 8.7E2 | 1.0E-9 | 1.0E-9 | 1.9E4 | 5.1E3 | 688 | 37 | 281 | 37 | 0.48 |
| Of | pg/ml | 1.8E2 | 2.1E2 | 6.4E3 | 5.1E3 | 3.1E4 | 1.6E4 | 1.0E-9 | 1.0E-9 | 6.2E5 | 7.4E4 | 695 | 37 | 281 | 37 | 0.52 |
| Og | pg/ml | 8.4E-2 | 9.0E-2 | 5.3E-1 | 3.9E-1 | 1.7E0 | 1.5E0 | 1.0E-9 | 1.0E-9 | 2.0E1 | 9.0E0 | 695 | 37 | 281 | 37 | 0.46 |
| Oh | pg/ml | 2.4E0 | 3.4E0 | 2.3E1 | 1.9E1 | 1.6E2 | 4.8E1 | 1.0E-9 | 1.0E-9 | 3.5E3 | 2.2E2 | 695 | 37 | 281 | 37 | 0.60 |
| Oi | pg/ml | 2.3E0 | 5.4E0 | 6.1E0 | 1.0E1 | 9.9E0 | 1.2E1 | 1.0E-9 | 1.0E-9 | 8.6E1 | 4.2E1 | 695 | 37 | 281 | 37 | 0.59 |
| Ok | pg/ml | 3.5E2 | 7.6E2 | 5.0E2 | 3.0E3 | 5.2E2 | 1.1E4 | 1.3E1 | 2.2E1 | 5.2E3 | 7.0E4 | 695 | 37 | 281 | 37 | 0.74 |
| Om | pg/ml | 3.8E2 | 6.8E2 | 8.5E2 | 1.7E3 | 2.3E3 | 3.4E3 | 1.0E-9 | 1.0E-9 | 3.6E4 | 1.7E4 | 695 | 37 | 281 | 37 | 0.61 |
| On | pg/ml | 1.6E2 | 3.8E2 | 2.7E2 | 1.1E3 | 4.1E2 | 2.8E3 | 1.0E-9 | 6.1E0 | 4.5E3 | 1.5E4 | 695 | 37 | 281 | 37 | 0.70 |
| Or | pg/ml | 1.2E1 | 1.7E1 | 3.1E1 | 6.6E1 | 6.0E1 | 1.6E2 | 1.0E-9 | 1.0E-9 | 5.0E2 | 7.6E2 | 249 | 22 | 160 | 22 | 0.56 |
| Ow | pg/ml | 3.3E1 | 4.8E1 | 1.2E2 | 1.4E2 | 3.5E2 | 2.3E2 | 1.0E-9 | 1.0E-9 | 3.2E3 | 7.9E2 | 249 | 22 | 160 | 22 | 0.57 |
| Ou | pg/ml | 4.6E2 | 7.9E2 | 8.6E2 | 2.5E3 | 1.3E3 | 3.4E3 | 1.0E-9 | 1.0E-9 | 9.8E3 | 9.6E3 | 249 | 22 | 160 | 22 | 0.61 |
| Ul | ng/ml | 1.0E-9 | 1.0E-9 | 1.2E0 | 5.2E0 | 4.6E0 | 2.2E1 | 1.0E-9 | 1.0E-9 | 3.4E1 | 1.0E2 | 257 | 22 | 164 | 22 | 0.52 |
| Uo | ng/ml | 1.0E-9 | 1.0E-9 | 9.2E-2 | 1.6E-1 | 2.1E-1 | 3.5E-1 | 1.0E-9 | 1.0E-9 | 1.3E0 | 1.5E0 | 257 | 22 | 164 | 22 | 0.51 |
| Uk | ng/ml | 1.0E-9 | 1.0E-9 | 7.8E-3 | 5.4E-3 | 2.7E-2 | 1.2E-2 | 1.0E-9 | 1.0E-9 | 3.2E-1 | 4.2E-2 | 257 | 22 | 164 | 22 | 0.43 |
| Um | ng/ml | 1.0E-9 | 1.0E-9 | 3.7E-1 | 3.5E-1 | 8.5E-1 | 9.7E-1 | 1.0E-9 | 1.0E-9 | 6.8E0 | 4.4E0 | 257 | 22 | 164 | 22 | 0.45 |
| Uf | ng/ml | 5.1E-2 | 1.0E-1 | 1.2E-1 | 2.3E-1 | 1.9E-1 | 5.1E-1 | 1.0E-3 | 1.3E-3 | 1.7E0 | 2.5E0 | 257 | 22 | 164 | 22 | 0.61 |
| Uh | ng/ml | 1.8E0 | 3.2E0 | 2.9E0 | 3.8E0 | 3.2E0 | 3.0E0 | 3.2E-2 | 2.3E-1 | 1.7E1 | 1.2E1 | 257 | 22 | 164 | 22 | 0.63 |
| Un | ng/ml | 1.8E0 | 2.1E0 | 2.1E0 | 2.3E0 | 1.3E0 | 1.3E0 | 2.0E-1 | 1.8E-1 | 8.0E0 | 5.3E0 | 257 | 22 | 164 | 22 | 0.56 |
| Ug | ng/ml | 1.4E1 | 2.2E1 | 2.7E1 | 3.7E1 | 2.8E1 | 4.7E1 | 6.9E-1 | 1.1E0 | 1.8E2 | 2.1E2 | 257 | 22 | 164 | 22 | 0.54 |
| Ur | ng/ml | 1.5E-1 | 2.0E-1 | 7.7E-1 | 8.6E-1 | 5.9E0 | 1.9E0 | 1.0E-9 | 1.0E-9 | 9.3E1 | 7.2E0 | 256 | 22 | 163 | 22 | 0.50 |
| Up | ng/ml | 1.0E-9 | 1.0E-9 | 5.4E-3 | 2.4E-3 | 2.5E-2 | 6.6E-3 | 1.0E-9 | 1.0E-9 | 3.3E-1 | 2.5E-2 | 256 | 22 | 163 | 22 | 0.47 |
| Us | ng/ml | 3.2E-3 | 5.1E-3 | 1.8E-2 | 1.9E-2 | 4.4E-2 | 4.5E-2 | 1.0E-9 | 1.0E-9 | 4.0E-1 | 2.1E-1 | 256 | 22 | 163 | 22 | 0.51 |
| Uv | ng/ml | 3.0E-3 | 2.7E-3 | 1.3E-2 | 1.0E-2 | 4.2E-2 | 3.0E-2 | 1.0E-9 | 1.0E-9 | 4.3E-1 | 1.4E-1 | 256 | 22 | 163 | 22 | 0.48 |
| Ut | ng/ml | 6.6E-1 | 9.1E-1 | 2.9E0 | 1.2E0 | 9.1E0 | 1.3E0 | 1.0E-9 | 1.0E-9 | 7.8E1 | 5.5E0 | 256 | 22 | 163 | 22 | 0.50 |
| Uu | ng/ml | 7.0E0 | 7.8E0 | 7.7E0 | 8.9E0 | 5.0E0 | 6.3E0 | 4.5E-1 | 5.5E-1 | 2.6E1 | 2.2E1 | 256 | 22 | 163 | 22 | 0.54 |
| Vp | ng/ml | 1.0E-9 | 1.0E-9 | 4.0E-1 | 4.9E-3 | 3.6E0 | 2.3E-2 | 1.0E-9 | 1.0E-9 | 5.0E1 | 1.1E-1 | 257 | 22 | 164 | 22 | 0.45 |
| Vt | ng/ml | 6.0E0 | 7.9E0 | 8.4E0 | 1.1E1 | 9.1E0 | 8.8E0 | 4.3E-1 | 9.2E-1 | 8.6E1 | 3.4E1 | 257 | 22 | 164 | 22 | 0.62 |
| Vu | ng/ml | 1.0E-9 | 1.0E-9 | 2.3E0 | 8.2E-1 | 5.6E0 | 1.7E0 | 1.0E-9 | 1.0E-9 | 5.1E1 | 6.2E0 | 253 | 21 | 164 | 21 | 0.45 |
| Vq | ng/ml | 1.6E2 | 4.7E2 | 4.1E3 | 1.2E3 | 4.8E4 | 1.6E3 | 2.0E-1 | 7.9E0 | 6.8E5 | 5.4E3 | 203 | 16 | 135 | 16 | 0.61 |
| Vo | ng/ml | 2.6E1 | 2.5E1 | 2.4E1 | 2.3E1 | 5.4E0 | 6.1E0 | 2.4E0 | 6.7E0 | 4.8E1 | 3.1E1 | 257 | 22 | 164 | 22 | 0.44 |
| Vs | ng/ml | 1.0E-9 | 1.0E-9 | 6.7E0 | 2.5E0 | 2.4E1 | 5.2E0 | 1.0E-9 | 1.0E-9 | 2.3E2 | 1.9E1 | 253 | 21 | 161 | 21 | 0.42 |
| Vv | ng/ml | 2.9E0 | 3.4E0 | 6.1E0 | 9.1E0 | 1.0E1 | 1.7E1 | 1.0E-9 | 1.0E-9 | 8.4E1 | 8.0E1 | 256 | 22 | 164 | 22 | 0.56 |
| Oy | pg/ml | 5.3E-1 | 5.8E-1 | 6.6E0 | 8.7E0 | 3.2E1 | 4.4E1 | 1.0E-9 | 1.0E-9 | 4.0E2 | 2.7E2 | 694 | 37 | 280 | 37 | 0.52 |
| Oz | pg/ml | 1.3E-2 | 2.4E-1 | 3.4E-1 | 3.2E-1 | 1.5E0 | 3.2E-1 | 1.0E-9 | 1.0E-9 | 2.9E1 | 1.0E0 | 694 | 37 | 280 | 37 | 0.61 |
| Pa | pg/ml | 3.8E-1 | 4.5E-1 | 1.5E0 | 9.4E0 | 5.5E0 | 4.8E1 | 1.0E-9 | 2.6E-2 | 8.6E1 | 2.9E2 | 694 | 37 | 280 | 37 | 0.59 |
| Pb | pg/ml | 1.0E-9 | 8.2E-2 | 9.3E-1 | 5.0E0 | 1.9E1 | 3.0E1 | 1.0E-9 | 1.0E-9 | 4.9E2 | 1.8E2 | 694 | 37 | 280 | 37 | 0.59 |
| Pc | pg/ml | 4.7E-2 | 3.2E-1 | 3.7E-1 | 8.6E-1 | 9.4E-1 | 2.1E0 | 1.0E-9 | 1.0E-9 | 1.6E1 | 1.1E1 | 694 | 37 | 280 | 37 | 0.59 |
| Pd | pg/ml | 1.7E0 | 2.8E0 | 5.1E0 | 4.8E0 | 3.3E1 | 5.2E0 | 1.0E-9 | 1.0E-9 | 8.4E2 | 1.9E1 | 694 | 37 | 280 | 37 | 0.60 |
| Pe | pg/ml | 2.0E1 | 3.6E1 | 1.0E2 | 5.0E2 | 3.5E2 | 2.3E3 | 1.0E-9 | 3.7E-1 | 4.7E3 | 1.4E4 | 694 | 37 | 280 | 37 | 0.65 |
| Pf | pg/ml | 1.4E0 | 2.4E0 | 1.1E1 | 1.6E1 | 6.4E1 | 4.1E1 | 1.0E-9 | 1.0E-9 | 1.5E3 | 2.3E2 | 694 | 37 | 280 | 37 | 0.60 |
| Pg | pg/ml | 3.0E0 | 6.4E0 | 4.7E1 | 7.2E1 | 3.8E2 | 3.1E2 | 1.0E-9 | 1.3E-1 | 7.7E3 | 1.9E3 | 694 | 37 | 280 | 37 | 0.63 |
| Ph | ng/ml | 1.7E-1 | 2.3E-1 | 3.2E-1 | 7.2E-1 | 4.5E-1 | 1.1E0 | 1.0E-9 | 1.0E-9 | 2.9E0 | 4.4E0 | 249 | 22 | 160 | 22 | 0.59 |
| Pi | ng/ml | 2.0E-1 | 2.4E-1 | 2.8E-1 | 2.6E-1 | 3.6E-1 | 2.3E-1 | 1.0E-9 | 1.0E-9 | 3.2E0 | 1.0E0 | 249 | 22 | 160 | 22 | 0.53 |
| Pj | ng/mL | 4.8E0 | 7.6E0 | 5.9E0 | 8.3E0 | 4.5E0 | 5.1E0 | 3.8E-2 | 1.6E-1 | 3.1E1 | 1.7E1 | 249 | 22 | 160 | 22 | 0.65 |
| Pk | ng/ml | 8.9E-3 | 9.3E-3 | 1.4E-2 | 1.2E-2 | 2.2E-2 | 1.1E-2 | 1.0E-9 | 1.0E-9 | 2.5E-1 | 3.8E-2 | 249 | 22 | 160 | 22 | 0.50 |
| aA | mg/dL | 8.0E-1 | 1.0E0 | 9.2E-1 | 1.4E0 | 4.7E-1 | 1.0E0 | 2.0E-1 | 4.0E-1 | 4.2E0 | 5.4E0 | 2240 | 57 | 436 | 57 | 0.66 |
| aC | mg/mL | 2.9E0 | 2.5E0 | 3.2E0 | 2.8E0 | 1.4E0 | 1.2E0 | 8.5E-1 | 1.3E0 | 8.9E0 | 6.1E0 | 437 | 26 | 174 | 26 | 0.44 |
| aD | ug/mL | 3.1E0 | 4.8E0 | 4.4E0 | 5.2E0 | 3.9E0 | 3.9E0 | 4.3E-1 | 8.4E-1 | 3.5E1 | 1.7E1 | 437 | 26 | 174 | 26 | 0.55 |
| aE | mg/mL | 5.6E-1 | 5.7E-1 | 5.8E-1 | 5.8E-1 | 1.5E-1 | 1.7E-1 | 2.1E-1 | 2.8E-1 | 1.1E0 | 1.2E0 | 437 | 26 | 174 | 26 | 0.51 |

Figure 9 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aF | ng/mL | 2.1E0 | 2.4E0 | 4.1E0 | 4.0E0 | 6.1E0 | 4.4E0 | 4.3E-3 | 4.3E-3 | 5.0E1 | 1.8E1 | 437 | 26 | 174 | 26 | 0.53 |
| aG | mg/mL | 1.4E-1 | 1.4E-1 | 1.6E-1 | 1.6E-1 | 9.1E-2 | 1.0E-1 | 1.7E-2 | 5.9E-2 | 5.4E-1 | 5.2E-1 | 437 | 26 | 174 | 26 | 0.48 |
| aH | ug/mL | 7.5E1 | 7.8E1 | 8.3E1 | 8.9E1 | 4.4E1 | 5.0E1 | 4.6E0 | 2.5E1 | 2.9E2 | 2.3E2 | 437 | 26 | 174 | 26 | 0.53 |
| aI | ug/mL | 1.9E2 | 1.8E2 | 1.9E2 | 1.9E2 | 6.0E1 | 4.8E1 | 2.8E1 | 9.9E1 | 3.7E2 | 2.7E2 | 437 | 26 | 174 | 26 | 0.48 |
| aJ | ng/mL | 2.4E0 | 3.8E0 | 2.9E0 | 4.8E0 | 2.1E0 | 3.9E0 | 7.6E-1 | 7.8E-1 | 1.7E1 | 1.7E1 | 437 | 26 | 174 | 26 | 0.69 |
| aK | ng/mL | 1.6E0 | 1.0E0 | 2.5E0 | 2.2E0 | 2.7E0 | 2.6E0 | 2.9E-4 | 1.1E-1 | 1.8E1 | 1.1E1 | 437 | 26 | 174 | 26 | 0.44 |
| aL | mg/mL | 8.1E-1 | 8.2E-1 | 8.2E-1 | 8.2E-1 | 2.5E-1 | 2.5E-1 | 1.9E-1 | 4.0E-1 | 1.7E0 | 1.6E0 | 437 | 26 | 174 | 26 | 0.49 |
| aM | U/mL | 2.2E1 | 2.7E1 | 4.5E1 | 4.4E1 | 9.6E1 | 4.2E1 | 4.2E-2 | 4.2E-2 | 1.6E3 | 1.5E2 | 437 | 26 | 174 | 26 | 0.56 |
| aN | U/mL | 1.3E1 | 2.2E1 | 2.0E1 | 2.8E1 | 2.8E1 | 2.5E1 | 2.5E-3 | 2.5E-3 | 3.8E2 | 9.7E1 | 437 | 26 | 174 | 26 | 0.63 |
| aO | pg/mL | 3.1E1 | 5.7E1 | 3.2E2 | 4.4E2 | 8.3E2 | 8.6E2 | 6.0E-2 | 6.0E-2 | 6.6E3 | 3.5E3 | 437 | 26 | 174 | 26 | 0.59 |
| aP | ng/mL | 1.6E0 | 2.0E0 | 2.0E0 | 2.8E0 | 1.8E0 | 2.2E0 | 4.5E-1 | 7.2E-1 | 2.8E1 | 1.1E1 | 437 | 26 | 174 | 26 | 0.62 |
| aQ | ng/mL | 3.0E-1 | 2.6E-1 | 4.7E-1 | 4.5E-1 | 4.8E-1 | 4.9E-1 | 2.0E-4 | 3.9E-2 | 4.0E0 | 1.8E0 | 437 | 26 | 174 | 26 | 0.45 |
| aR | ng/mL | 1.7E0 | 2.1E0 | 2.7E0 | 2.7E0 | 3.3E0 | 2.8E0 | 1.8E-1 | 3.2E-1 | 3.4E1 | 1.4E1 | 437 | 26 | 174 | 26 | 0.53 |
| aS | ng/mL | 2.6E-1 | 3.3E-1 | 6.5E-1 | 6.0E-1 | 1.9E0 | 1.1E0 | 4.2E-3 | 4.2E-3 | 3.3E1 | 5.6E0 | 437 | 26 | 174 | 26 | 0.52 |
| aU | pg/mL | 7.8E1 | 8.0E1 | 1.3E2 | 1.5E2 | 1.5E2 | 1.7E2 | 7.4E-2 | 1.3E1 | 1.3E3 | 6.0E2 | 437 | 26 | 174 | 26 | 0.50 |
| aV | ng/mL | 6.3E-1 | 3.6E-1 | 1.1E0 | 1.0E0 | 2.0E0 | 1.2E0 | 7.6E-4 | 3.1E-2 | 3.3E1 | 4.2E0 | 437 | 26 | 174 | 26 | 0.43 |
| aW | pg/mL | 1.9E1 | 1.7E1 | 2.0E1 | 3.6E1 | 2.0E1 | 8.4E1 | 7.2E-2 | 7.2E-2 | 2.4E2 | 4.5E2 | 437 | 26 | 174 | 26 | 0.54 |
| aX | ng/mL | 9.4E0 | 1.6E1 | 1.5E1 | 2.8E1 | 1.9E1 | 3.4E1 | 3.0E-1 | 2.5E0 | 2.2E2 | 1.4E2 | 437 | 26 | 174 | 26 | 0.62 |
| aY | pg/mL | 5.4E1 | 6.7E1 | 7.7E1 | 8.1E1 | 8.7E1 | 6.0E1 | 4.1E-1 | 4.1E-1 | 1.2E3 | 2.7E2 | 437 | 26 | 174 | 26 | 0.58 |
| aZ | pg/mL | 2.2E2 | 3.7E2 | 5.0E2 | 6.2E2 | 9.8E2 | 8.2E2 | 1.7E0 | 1.7E0 | 8.7E3 | 3.7E3 | 437 | 26 | 174 | 26 | 0.58 |
| bA | ng/mL | 8.0E0 | 2.8E1 | 3.0E1 | 8.9E1 | 7.8E1 | 1.9E2 | 3.0E-2 | 1.4E0 | 9.4E2 | 8.1E2 | 437 | 26 | 174 | 26 | 0.71 |
| bB | ng/mL | 3.1E2 | 2.8E2 | 3.4E2 | 2.9E2 | 1.7E2 | 1.5E2 | 2.1E0 | 5.1E1 | 1.0E3 | 5.5E2 | 437 | 26 | 174 | 26 | 0.43 |
| bC | ng/mL | 3.3E2 | 4.2E2 | 5.6E2 | 8.4E2 | 7.4E2 | 1.1E3 | 9.8E0 | 7.3E1 | 4.7E3 | 4.7E3 | 437 | 26 | 174 | 26 | 0.62 |
| bE | mg/mL | 5.5E0 | 6.1E0 | 5.8E0 | 6.5E0 | 2.0E0 | 2.5E0 | 9.8E-1 | 2.8E0 | 1.3E1 | 1.3E1 | 437 | 26 | 174 | 26 | 0.55 |
| bF | pg/mL | 1.9E1 | 3.2E1 | 1.6E2 | 5.6E1 | 9.8E2 | 6.7E1 | 5.0E-2 | 8.1E0 | 1.1E4 | 3.2E2 | 437 | 26 | 174 | 26 | 0.63 |
| bG | ng/mL | 1.6E0 | 2.0E0 | 2.7E0 | 3.3E0 | 3.3E0 | 3.4E0 | 2.2E-2 | 2.4E-1 | 2.6E1 | 1.3E1 | 437 | 26 | 174 | 26 | 0.56 |
| bH | pg/mL | 5.7E-1 | 5.7E-1 | 4.9E0 | 3.5E0 | 1.6E1 | 5.5E0 | 5.7E-1 | 5.7E-1 | 2.8E2 | 2.1E1 | 437 | 26 | 174 | 26 | 0.48 |
| bI | ng/mL | 4.0E-3 | 4.0E-3 | 6.5E-2 | 6.7E-2 | 1.6E-1 | 1.1E-1 | 4.0E-3 | 4.0E-3 | 1.3E0 | 3.4E-1 | 437 | 26 | 174 | 26 | 0.54 |
| bJ | mg/mL | 2.4E0 | 2.5E0 | 2.7E0 | 2.6E0 | 2.1E0 | 1.7E0 | 2.5E-4 | 2.5E-1 | 1.3E1 | 7.1E0 | 437 | 26 | 174 | 26 | 0.51 |
| bL | pg/mL | 4.0E0 | 2.6E0 | 8.3E0 | 8.1E0 | 1.1E1 | 1.1E1 | 4.6E-2 | 4.6E-2 | 8.0E1 | 4.4E1 | 437 | 26 | 174 | 26 | 0.45 |
| bM | mg/mL | 1.7E0 | 2.2E0 | 2.0E0 | 2.3E0 | 1.4E0 | 1.2E0 | 9.2E-3 | 6.3E-1 | 8.8E0 | 6.1E0 | 437 | 26 | 174 | 26 | 0.61 |
| bN | ng/mL | 4.3E1 | 2.9E1 | 1.4E2 | 6.9E1 | 2.9E2 | 1.2E2 | 1.4E-1 | 1.4E-1 | 1.9E3 | 5.0E2 | 437 | 26 | 174 | 26 | 0.43 |
| bO | ng/mL | 4.0E-2 | 4.0E-2 | 1.0E1 | 1.4E1 | 2.3E1 | 3.9E1 | 4.0E-2 | 4.0E-2 | 1.9E2 | 1.9E2 | 437 | 26 | 174 | 26 | 0.46 |
| bP | mg/mL | 5.3E-1 | 6.1E-1 | 7.6E-1 | 7.4E-1 | 6.8E-1 | 6.0E-1 | 4.9E-2 | 1.4E-1 | 4.8E0 | 2.9E0 | 437 | 26 | 174 | 26 | 0.51 |
| bQ | pg/mL | 1.5E1 | 1.9E1 | 6.4E1 | 2.7E1 | 6.5E2 | 3.0E1 | 1.5E-1 | 1.5E-1 | 1.3E4 | 1.5E2 | 437 | 26 | 174 | 26 | 0.56 |
| bR | ng/mL | 1.2E-2 | 1.2E-2 | 1.4E-1 | 6.5E-2 | 4.6E-1 | 1.0E-1 | 1.2E-2 | 1.2E-2 | 8.7E0 | 3.9E-1 | 437 | 26 | 174 | 26 | 0.41 |
| bS | pg/mL | 9.4E-1 | 9.4E-1 | 7.2E0 | 2.5E0 | 2.9E1 | 5.5E0 | 9.4E-1 | 9.4E-1 | 3.9E2 | 2.1E1 | 437 | 26 | 174 | 26 | 0.47 |
| bU | ng/mL | 1.5E-1 | 3.4E-2 | 2.0E-1 | 1.0E-1 | 3.8E-1 | 1.4E-1 | 1.3E-2 | 1.3E-2 | 6.6E0 | 5.5E-1 | 437 | 26 | 174 | 26 | 0.38 |
| bV | pg/mL | 4.7E2 | 6.2E2 | 5.5E2 | 1.3E3 | 5.8E2 | 3.2E3 | 1.6E2 | 1.5E2 | 1.2E4 | 1.7E4 | 437 | 26 | 174 | 26 | 0.62 |
| bW | pg/mL | 3.2E2 | 3.3E2 | 4.9E2 | 6.4E2 | 4.8E2 | 1.2E3 | 8.4E1 | 1.4E2 | 4.8E3 | 6.4E3 | 437 | 26 | 174 | 26 | 0.50 |
| bX | ng/mL | 1.5E-3 | 2.5E-5 | 2.8E-3 | 1.9E-3 | 3.5E-3 | 2.6E-3 | 2.5E-5 | 2.5E-5 | 2.0E-2 | 8.8E-3 | 437 | 26 | 174 | 26 | 0.43 |
| bZ | pg/mL | 2.3E2 | 3.2E2 | 9.1E2 | 1.0E3 | 4.1E3 | 1.9E3 | 1.5E-1 | 5.9E1 | 5.8E4 | 8.2E3 | 437 | 26 | 174 | 26 | 0.60 |
| cA | pg/mL | 6.0E-1 | 6.0E-1 | 2.8E0 | 1.8E0 | 1.8E1 | 3.3E0 | 6.0E-1 | 6.0E-1 | 3.7E2 | 1.3E1 | 437 | 26 | 174 | 26 | 0.49 |
| cB | ng/mL | 6.0E-2 | 3.5E-2 | 9.3E-2 | 6.3E-2 | 1.0E-1 | 1.1E-1 | 1.7E-3 | 1.7E-3 | 5.7E-1 | 5.5E-1 | 437 | 26 | 174 | 26 | 0.39 |
| cC | pg/mL | 4.6E1 | 3.7E1 | 4.8E1 | 4.0E1 | 4.0E1 | 2.6E1 | 1.0E0 | 1.0E0 | 4.5E2 | 1.1E2 | 437 | 26 | 174 | 26 | 0.43 |
| cD | pg/mL | 5.4E0 | 4.7E0 | 1.5E1 | 1.2E1 | 5.7E1 | 1.9E1 | 3.3E-1 | 3.3E-1 | 7.2E2 | 8.4E1 | 437 | 26 | 174 | 26 | 0.47 |
| cE | pg/mL | 3.2E1 | 5.6E1 | 1.5E2 | 8.7E1 | 4.6E2 | 1.1E2 | 1.2E-1 | 1.2E-1 | 3.8E3 | 4.2E2 | 437 | 26 | 174 | 26 | 0.58 |
| cF | pg/mL | 1.3E1 | 5.3E-1 | 2.1E1 | 1.1E1 | 3.2E1 | 1.8E1 | 5.3E-1 | 5.3E-1 | 2.7E2 | 7.2E1 | 437 | 26 | 174 | 26 | 0.40 |
| cG | pg/mL | 4.3E1 | 7.2E1 | 1.1E2 | 8.4E1 | 5.2E2 | 5.7E1 | 7.8E0 | 7.7E0 | 1.0E4 | 2.4E2 | 437 | 26 | 174 | 26 | 0.65 |
| cH | uIU/mL | 3.1E0 | 1.5E0 | 6.5E0 | 3.8E0 | 1.2E1 | 6.2E0 | 8.6E-3 | 8.6E-3 | 1.6E2 | 2.4E1 | 437 | 26 | 174 | 26 | 0.33 |
| cI | ng/mL | 5.7E0 | 5.3E0 | 1.1E1 | 1.4E1 | 1.5E1 | 2.4E1 | 1.0E-3 | 1.1E-1 | 1.0E2 | 1.2E2 | 437 | 26 | 174 | 26 | 0.50 |
| cJ | ug/mL | 7.0E1 | 4.6E1 | 1.2E2 | 7.0E1 | 1.5E2 | 8.0E1 | 4.0E0 | 7.6E0 | 9.6E2 | 3.9E2 | 437 | 26 | 174 | 26 | 0.40 |
| cK | ng/mL | 3.8E-3 | 3.8E-3 | 5.5E-2 | 3.6E-2 | 1.9E-1 | 8.0E-2 | 3.8E-3 | 3.8E-3 | 1.7E0 | 3.0E-1 | 437 | 26 | 174 | 26 | 0.50 |
| cL | pg/mL | 1.9E2 | 2.7E2 | 3.6E2 | 2.7E2 | 1.3E3 | 1.5E2 | 1.6E1 | 4.1E1 | 2.4E4 | 6.4E2 | 437 | 26 | 174 | 26 | 0.62 |
| cM | pg/mL | 2.8E2 | 2.5E2 | 3.1E2 | 2.5E2 | 2.0E2 | 9.6E1 | 8.7E0 | 6.7E1 | 1.6E3 | 4.7E2 | 437 | 26 | 174 | 26 | 0.42 |
| cN | pg/mL | 1.2E2 | 1.3E2 | 1.3E2 | 1.4E2 | 6.4E1 | 5.0E1 | 3.8E1 | 6.4E1 | 1.1E3 | 2.4E2 | 437 | 26 | 174 | 26 | 0.59 |
| cO | pg/mL | 2.2E2 | 2.5E2 | 3.1E2 | 2.9E2 | 9.3E2 | 1.6E2 | 5.4E1 | 1.1E2 | 1.9E4 | 7.5E2 | 437 | 26 | 174 | 26 | 0.56 |

Figure 9 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cP | ng/mL | 2.5E3 | 2.8E3 | 2.6E3 | 3.0E3 | 9.2E2 | 1.1E3 | 6.2E2 | 1.6E3 | 5.7E3 | 5.9E3 | 437 | 26 | 174 | 26 | 0.59 |
| cQ | ng/mL | 4.3E-2 | 6.3E-2 | 1.3E-1 | 1.9E-1 | 2.4E-1 | 3.1E-1 | 2.0E-3 | 2.0E-3 | 2.2E0 | 1.2E0 | 437 | 26 | 174 | 26 | 0.57 |
| cR | ng/mL | 2.8E2 | 3.8E2 | 4.9E2 | 8.0E2 | 8.0E2 | 1.5E3 | 2.0E1 | 4.0E1 | 8.9E3 | 7.7E3 | 437 | 26 | 174 | 26 | 0.58 |
| cS | ng/mL | 2.6E2 | 3.4E2 | 3.8E2 | 1.3E3 | 3.8E2 | 4.3E3 | 4.1E1 | 9.7E1 | 2.7E3 | 2.2E4 | 437 | 26 | 174 | 26 | 0.58 |
| cT | ng/mL | 2.9E1 | 6.0E1 | 8.3E1 | 1.7E2 | 1.8E2 | 3.8E2 | 3.6E0 | 4.2E0 | 2.1E3 | 1.9E3 | 437 | 26 | 174 | 26 | 0.65 |
| cU | ng/mL | 5.4E1 | 7.0E1 | 7.5E1 | 1.1E2 | 9.9E1 | 1.0E2 | 6.2E0 | 1.2E1 | 1.6E3 | 4.8E2 | 437 | 26 | 174 | 26 | 0.59 |
| cV | ng/mL | 1.7E-1 | 1.7E-1 | 3.8E-1 | 4.7E-1 | 2.3E0 | 1.1E0 | 3.4E-4 | 4.7E-2 | 4.7E1 | 6.0E0 | 437 | 26 | 174 | 26 | 0.54 |
| cW | mIU/mL | 5.3E-2 | 5.6E-2 | 1.5E-1 | 7.7E-2 | 7.2E-1 | 6.5E-2 | 3.7E-4 | 1.1E-2 | 9.7E0 | 2.6E-1 | 437 | 26 | 174 | 26 | 0.52 |
| cX | ng/mL | 9.9E-2 | 1.4E-1 | 1.3E0 | 5.5E-1 | 4.2E0 | 8.8E-1 | 2.3E-4 | 2.3E-4 | 2.8E1 | 3.0E0 | 437 | 26 | 174 | 26 | 0.49 |
| cY | ng/mL | 8.9E0 | 7.4E0 | 1.3E1 | 1.4E1 | 1.3E1 | 1.5E1 | 1.5E-1 | 3.7E-1 | 8.3E1 | 5.4E1 | 437 | 26 | 174 | 26 | 0.48 |
| cZ | ug/mL | 1.5E1 | 1.6E1 | 1.6E1 | 1.6E1 | 7.1E0 | 6.3E0 | 2.3E0 | 6.3E0 | 5.7E1 | 3.6E1 | 437 | 26 | 174 | 26 | 0.52 |
| dA | pg/mL | 3.3E2 | 3.7E2 | 3.8E2 | 4.2E2 | 3.1E2 | 2.1E2 | 9.0E1 | 1.7E2 | 5.8E3 | 8.6E2 | 437 | 26 | 174 | 26 | 0.58 |
| dB | ug/mL | 1.7E1 | 1.8E1 | 1.7E1 | 1.8E1 | 1.6E1 | 9.2E0 | 9.4E-1 | 1.9E0 | 2.5E2 | 4.1E1 | 437 | 26 | 174 | 26 | 0.55 |
| dC | nmol/L | 3.5E1 | 3.6E1 | 3.9E1 | 3.9E1 | 1.8E1 | 2.0E1 | 7.9E0 | 1.3E1 | 1.4E2 | 8.3E1 | 437 | 26 | 174 | 26 | 0.48 |
| dD | ug/mL | 3.7E1 | 3.4E1 | 3.8E1 | 3.6E1 | 1.1E1 | 1.0E1 | 1.3E1 | 1.5E1 | 7.6E1 | 5.8E1 | 437 | 26 | 174 | 26 | 0.44 |
| dE | ng/mL | 4.7E-1 | 6.6E-1 | 6.1E-1 | 8.4E-1 | 7.3E-1 | 7.8E-1 | 8.4E-3 | 8.4E-3 | 7.2E0 | 3.3E0 | 437 | 26 | 174 | 26 | 0.60 |
| dF | ng/mL | 2.2E2 | 3.1E2 | 2.6E2 | 3.6E2 | 1.8E2 | 2.1E2 | 7.5E1 | 8.3E1 | 1.3E3 | 9.7E2 | 437 | 26 | 174 | 26 | 0.67 |
| dG | ng/mL | 1.1E1 | 1.6E1 | 1.4E1 | 1.9E1 | 1.2E1 | 1.2E1 | 2.5E0 | 2.2E0 | 1.8E2 | 6.9E1 | 437 | 26 | 174 | 26 | 0.70 |
| dH | pg/mL | 7.5E0 | 8.6E0 | 1.3E1 | 1.1E1 | 4.0E1 | 8.1E0 | 4.0E-2 | 4.0E-2 | 6.7E2 | 3.5E1 | 437 | 26 | 174 | 26 | 0.58 |
| dI | pg/mL | 4.6E-1 | 4.6E-1 | 2.3E0 | 2.7E0 | 1.6E1 | 8.0E0 | 4.6E-1 | 4.6E-1 | 3.3E2 | 4.1E1 | 437 | 26 | 174 | 26 | 0.48 |
| dJ | ng/mL | 1.9E0 | 1.8E0 | 2.2E0 | 2.0E0 | 1.2E0 | 1.2E0 | 3.2E-2 | 4.0E-1 | 6.9E0 | 4.4E0 | 437 | 26 | 174 | 26 | 0.44 |
| dK | uIU/mL | 1.9E0 | 1.7E0 | 3.1E0 | 4.2E0 | 6.0E0 | 1.1E1 | 2.8E-4 | 3.8E-2 | 7.9E1 | 6.0E1 | 437 | 26 | 174 | 26 | 0.48 |
| dL | | 8.7E2 | 9.9E2 | 1.0E3 | 1.1E3 | 4.9E2 | 3.8E2 | 3.4E2 | 3.3E2 | 3.4E3 | 1.8E3 | 437 | 26 | 174 | 26 | 0.61 |
| dM | pg/mL | 9.6E2 | 1.1E3 | 1.1E3 | 1.8E3 | 8.8E2 | 1.8E3 | 3.5E2 | 3.7E2 | 1.2E4 | 8.3E3 | 437 | 26 | 174 | 26 | 0.65 |
| dN | ug/mL | 9.3E1 | 9.6E1 | 9.9E1 | 1.1E2 | 3.6E1 | 4.2E1 | 2.5E1 | 3.7E1 | 2.8E2 | 2.0E2 | 437 | 26 | 174 | 26 | 0.56 |
| dO | ng/ml | 2.1E1 | 9.3E0 | 4.2E1 | 2.5E1 | 5.9E1 | 3.7E1 | 4.0E-1 | 3.8E0 | 3.7E2 | 1.1E2 | 83 | 8 | 60 | 8 | 0.34 |
| dR | pg/ml | 1.6E3 | 1.3E3 | 2.4E3 | 2.3E3 | 2.4E3 | 2.4E3 | 1.4E2 | 1.9E2 | 1.5E4 | 8.9E3 | 287 | 25 | 167 | 25 | 0.45 |
| dV | pg/ml | 7.0E1 | 6.0E1 | 9.0E1 | 7.2E1 | 5.9E1 | 4.8E1 | 2.1E1 | 3.6E1 | 3.3E2 | 1.9E2 | 61 | 8 | 38 | 8 | 0.35 |
| dX | ng/ml | 8.1E-2 | 7.4E-3 | 1.2E-1 | 1.4E-1 | 1.9E-1 | 2.8E-1 | 2.6E-3 | 2.6E-3 | 1.2E0 | 8.6E-1 | 121 | 9 | 43 | 9 | 0.41 |
| eF | ng/ml | 4.0E0 | 5.6E0 | 4.9E0 | 5.8E0 | 4.2E0 | 2.3E0 | 1.2E0 | 2.6E0 | 4.6E1 | 1.1E1 | 302 | 25 | 168 | 25 | 0.67 |
| eC | pg/ml | 3.1E2 | 2.7E2 | 3.6E2 | 3.2E2 | 2.2E2 | 2.3E2 | 9.9E0 | 1.6E2 | 1.4E3 | 1.2E3 | 231 | 18 | 159 | 18 | 0.41 |
| eD | pg/ml | 2.3E2 | 2.5E2 | 5.8E2 | 2.5E2 | 1.2E3 | 4.7E1 | 5.2E-1 | 1.9E2 | 8.3E3 | 3.4E2 | 197 | 7 | 131 | 7 | 0.57 |
| eM | ng/ml | 3.2E0 | 3.8E0 | 4.9E0 | 8.0E0 | 5.5E0 | 7.4E0 | 3.3E-1 | 1.8E0 | 3.9E1 | 2.5E1 | 155 | 9 | 67 | 9 | 0.66 |
| eP | ng/ml | 3.7E-3 | 3.1E-2 | 6.4E-1 | 7.5E0 | 1.6E0 | 2.2E1 | 3.7E-3 | 3.7E-3 | 1.2E1 | 6.5E1 | 121 | 9 | 43 | 9 | 0.59 |
| eX | ng/ml | 4.0E0 | 1.3E1 | 1.5E1 | 2.1E1 | 2.0E1 | 2.1E1 | 8.6E-4 | 1.8E0 | 7.3E1 | 4.9E1 | 83 | 8 | 60 | 8 | 0.65 |
| fP | ng/ml | 2.4E2 | 2.9E2 | 2.8E2 | 3.9E2 | 1.7E2 | 3.4E2 | 1.8E0 | 1.2E2 | 1.0E3 | 1.6E3 | 276 | 21 | 162 | 21 | 0.61 |
| fR | ng/ml | 1.2E5 | 2.0E5 | 1.7E5 | 2.9E5 | 1.4E5 | 2.2E5 | 3.1E4 | 2.9E4 | 7.7E5 | 8.3E5 | 295 | 17 | 90 | 17 | 0.70 |
| gC | ng/ml | 2.3E2 | 2.3E2 | 2.6E2 | 2.5E2 | 1.3E2 | 8.6E1 | 8.3E1 | 1.7E2 | 1.1E3 | 4.4E2 | 127 | 8 | 74 | 8 | 0.53 |
| gN | U/ml | 3.6E2 | 4.0E2 | 4.4E2 | 5.2E2 | 2.9E2 | 2.6E2 | 1.9E0 | 3.1E2 | 1.3E3 | 9.3E2 | 61 | 8 | 38 | 8 | 0.61 |
| gL | pg/ml | 6.3E4 | 7.9E4 | 7.0E4 | 8.6E4 | 3.1E4 | 3.4E4 | 1.4E4 | 3.1E4 | 2.0E5 | 1.6E5 | 287 | 25 | 167 | 25 | 0.66 |
| gP | U/ml | 2.8E2 | 2.3E2 | 2.9E2 | 2.2E2 | 1.1E2 | 8.2E1 | 1.2E1 | 7.9E1 | 1.1E3 | 3.9E2 | 298 | 25 | 168 | 25 | 0.32 |
| gT | ng/ml | 2.1E1 | 2.0E1 | 2.1E1 | 2.2E1 | 5.0E0 | 4.7E0 | 1.2E1 | 1.7E1 | 3.6E1 | 3.0E1 | 64 | 8 | 44 | 8 | 0.56 |
| gW | ng/ml | 6.8E2 | 5.2E2 | 1.3E3 | 1.4E3 | 1.7E3 | 2.1E3 | 3.1E-1 | 8.3E1 | 9.5E3 | 8.2E3 | 252 | 25 | 157 | 25 | 0.50 |
| tF | pg/mL | 1.4E3 | 1.7E3 | 1.5E4 | 1.0E4 | 4.5E4 | 2.2E4 | 1.2E1 | 1.8E1 | 3.2E5 | 9.4E4 | 231 | 18 | 159 | 18 | 0.52 |
| hA | ng/ml | 2.0E0 | 3.8E0 | 9.2E0 | 8.1E0 | 3.7E1 | 9.1E0 | 1.7E-2 | 5.7E-1 | 3.5E2 | 2.7E1 | 197 | 7 | 131 | 7 | 0.69 |
| nM | pg/ml | 1.0E-9 | 1.0E-9 | 7.9E1 | 1.0E-9 | 9.0E2 | 0.0E0 | 1.0E-9 | 1.0E-9 | 1.0E4 | 1.0E-9 | 131 | 7 | 103 | 7 | 0.49 |
| nN | pg/ml | 1.2E3 | 2.0E3 | 5.1E3 | 2.0E3 | 2.5E4 | 1.0E3 | 1.1E2 | 7.3E2 | 2.7E5 | 3.5E3 | 131 | 7 | 103 | 7 | 0.61 |
| nO | pg/ml | 2.7E1 | 4.4E1 | 4.3E1 | 8.8E1 | 4.2E1 | 8.6E1 | 3.5E0 | 8.1E0 | 2.4E2 | 2.6E2 | 131 | 7 | 103 | 7 | 0.68 |
| nR | pg/ml | 1.3E1 | 6.6E1 | 3.8E1 | 8.6E1 | 8.7E1 | 7.1E1 | 1.0E-9 | 2.9E0 | 8.2E2 | 2.2E2 | 131 | 7 | 103 | 7 | 0.76 |
| nT | pg/ml | 8.5E1 | 6.7E1 | 2.2E2 | 3.4E2 | 8.0E2 | 6.4E2 | 1.0E-9 | 1.0E1 | 6.6E3 | 1.8E3 | 131 | 7 | 103 | 7 | 0.53 |
| nU | pg/ml | 2.9E1 | 7.9E1 | 2.6E2 | 5.0E2 | 1.5E3 | 1.1E3 | 1.0E-9 | 2.9E1 | 1.3E4 | 3.0E3 | 131 | 7 | 103 | 7 | 0.73 |
| lW | pg/ml | 1.0E-9 | 1.0E-9 | 1.3E1 | 1.7E1 | 4.7E1 | 2.9E1 | 1.0E-9 | 1.0E-9 | 3.9E2 | 7.4E1 | 131 | 7 | 103 | 7 | 0.58 |
| lX | pg/ml | 1.0E3 | 5.4E2 | 1.1E3 | 8.0E2 | 5.6E2 | 6.6E2 | 1.2E2 | 3.8E2 | 2.6E3 | 2.3E3 | 131 | 7 | 103 | 7 | 0.32 |
| lY | pg/ml | 2.0E1 | 2.2E1 | 2.3E1 | 2.1E1 | 2.1E1 | 5.7E0 | 1.0E-9 | 1.2E1 | 1.4E2 | 2.8E1 | 131 | 7 | 103 | 7 | 0.52 |
| mE | pg/ml | 1.0E-9 | 1.2E0 | 2.9E0 | 3.5E0 | 8.3E0 | 5.1E0 | 1.0E-9 | 1.0E-9 | 5.8E1 | 1.3E1 | 131 | 7 | 103 | 7 | 0.60 |
| mF | pg/ml | 1.0E-9 | 4.8E0 | 4.0E0 | 4.6E0 | 2.3E1 | 4.6E0 | 1.0E-9 | 1.0E-9 | 2.5E2 | 1.3E1 | 131 | 7 | 103 | 7 | 0.72 |
| mH | pg/ml | 3.6E0 | 1.3E0 | 5.1E0 | 4.8E0 | 6.7E0 | 8.2E0 | 2.3E-1 | 4.2E-1 | 5.3E1 | 2.3E1 | 131 | 7 | 103 | 7 | 0.33 |

Figure 9 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| mI | pg/ml | 1.0E-9 | 2.3E1 | 1.2E1 | 4.4E1 | 2.7E1 | 6.3E1 | 1.0E-9 | 1.0E-9 | 1.8E2 | 1.8E2 | 131 | 7 | 103 | 7 | 0.71 |
| mM | pg/ml | 2.2E1 | 3.5E1 | 6.5E1 | 9.3E1 | 1.5E2 | 1.1E2 | 1.0E-9 | 1.8E0 | 1.1E3 | 2.6E2 | 131 | 7 | 103 | 7 | 0.63 |
| mP | pg/ml | 1.4E1 | 1.7E1 | 1.8E1 | 1.9E1 | 2.3E1 | 9.9E0 | 1.0E-9 | 1.0E1 | 1.9E2 | 3.7E1 | 130 | 7 | 102 | 7 | 0.58 |
| mS | pg/ml | 1.8E3 | 1.7E3 | 2.0E3 | 2.7E3 | 1.6E3 | 1.8E3 | 1.0E-9 | 1.0E3 | 1.3E4 | 5.9E3 | 131 | 7 | 103 | 7 | 0.62 |
| mT | pg/ml | 4.8E1 | 8.5E1 | 1.2E2 | 3.4E2 | 2.1E2 | 7.1E2 | 9.7E0 | 1.4E1 | 1.4E3 | 1.9E3 | 130 | 7 | 102 | 7 | 0.55 |
| mU | pg/ml | 2.2E0 | 2.9E0 | 5.5E0 | 3.3E0 | 2.1E1 | 1.9E0 | 1.0E-9 | 1.5E0 | 2.2E2 | 7.2E0 | 130 | 7 | 102 | 7 | 0.64 |
| mW | pg/ml | 2.3E3 | 2.4E3 | 2.6E3 | 3.7E3 | 1.4E3 | 2.4E3 | 3.1E2 | 1.2E3 | 1.0E4 | 7.0E3 | 130 | 7 | 102 | 7 | 0.61 |
| mY | pg/ml | 5.6E2 | 4.8E2 | 8.6E2 | 9.8E2 | 1.3E3 | 9.0E2 | 1.0E-9 | 1.5E2 | 1.1E4 | 2.4E3 | 131 | 7 | 103 | 7 | 0.53 |
| mZ | pg/ml | 2.2E2 | 6.9E2 | 3.8E2 | 8.7E2 | 4.4E2 | 9.1E2 | 1.0E-9 | 6.6E1 | 3.1E3 | 2.8E3 | 130 | 7 | 102 | 7 | 0.69 |
| nA | pg/ml | 2.0E0 | 4.0E0 | 1.1E1 | 6.7E0 | 4.4E1 | 1.1E1 | 1.0E-9 | 1.0E-9 | 4.4E2 | 3.1E1 | 130 | 7 | 102 | 7 | 0.54 |
| nB | pg/ml | 3.0E2 | 4.1E2 | 3.1E2 | 4.3E2 | 1.5E2 | 1.7E2 | 3.0E1 | 2.5E2 | 8.2E2 | 7.6E2 | 131 | 7 | 103 | 7 | 0.71 |
| nC | pg/ml | 1.0E-9 | 2.8E3 | 3.7E3 | 9.9E4 | 3.2E4 | 2.5E5 | 1.0E-9 | 1.0E-9 | 3.7E5 | 6.7E5 | 131 | 7 | 103 | 7 | 0.75 |
| nD | pg/ml | 8.5E0 | 2.5E1 | 3.5E1 | 4.0E1 | 2.0E2 | 4.8E1 | 1.0E-9 | 8.5E0 | 1.7E3 | 1.5E2 | 130 | 7 | 102 | 7 | 0.84 |
| nF | pg/ml | 1.0E-9 | 1.0E-9 | 5.0E0 | 5.6E0 | 2.6E1 | 1.3E1 | 1.0E-9 | 1.0E-9 | 2.4E2 | 3.6E1 | 131 | 7 | 103 | 7 | 0.57 |
| nH | pg/ml | 3.8E-1 | 3.0E1 | 8.9E1 | 4.3E2 | 8.8E2 | 9.6E2 | 1.0E-9 | 1.0E-9 | 1.0E4 | 2.6E3 | 130 | 7 | 102 | 7 | 0.71 |
| nI | pg/ml | 4.6E1 | 6.6E1 | 1.6E2 | 2.1E2 | 8.4E2 | 4.4E2 | 1.0E-9 | 1.0E-9 | 9.2E3 | 1.2E3 | 131 | 7 | 103 | 7 | 0.56 |
| nJ | pg/ml | 1.7E-1 | 1.0E-9 | 4.1E1 | 2.5E0 | 4.5E2 | 4.9E0 | 1.0E-9 | 1.0E-9 | 5.2E3 | 1.3E1 | 131 | 7 | 103 | 7 | 0.50 |
| nK | pg/ml | 1.0E-9 | 1.6E1 | 5.8E1 | 4.4E1 | 3.4E2 | 8.4E1 | 1.0E-9 | 1.0E-9 | 3.2E3 | 2.3E2 | 130 | 7 | 102 | 7 | 0.64 |
| nL | pg/ml | 1.0E-9 | 7.4E1 | 3.9E2 | 8.6E2 | 3.9E3 | 1.8E3 | 1.0E-9 | 1.0E-9 | 4.5E4 | 4.8E3 | 131 | 7 | 103 | 7 | 0.69 |
| hR | pg/ml | 2.6E4 | 2.5E4 | 2.7E4 | 2.7E4 | 1.1E4 | 9.2E3 | 1.1E1 | 1.2E4 | 5.8E4 | 4.3E4 | 189 | 7 | 129 | 7 | 0.52 |
| hV | pg/ml | 4.4E2 | 2.3E2 | 4.7E2 | 2.4E2 | 2.4E2 | 5.8E1 | 6.8E1 | 1.7E2 | 1.5E3 | 3.6E2 | 189 | 7 | 129 | 7 | 0.16 |
| hW | pg/ml | 1.5E3 | 2.1E3 | 2.0E3 | 2.4E3 | 1.6E3 | 2.0E3 | 2.2E2 | 5.7E2 | 1.0E4 | 6.4E3 | 189 | 7 | 129 | 7 | 0.59 |
| hX | pg/ml | 9.0E2 | 8.2E2 | 1.0E3 | 1.7E3 | 7.8E2 | 2.2E3 | 1.3E2 | 4.6E2 | 8.6E3 | 6.6E3 | 189 | 7 | 129 | 7 | 0.45 |
| iA | pg/ml | 1.4E2 | 2.1E2 | 2.8E2 | 3.5E2 | 6.2E2 | 5.0E2 | 5.8E0 | 8.2E0 | 7.1E3 | 2.2E3 | 231 | 18 | 159 | 18 | 0.63 |
| iB | ng/ml | 4.8E0 | 6.3E0 | 6.0E0 | 9.3E0 | 4.9E0 | 8.4E0 | 3.3E-2 | 1.8E0 | 3.8E1 | 2.6E1 | 197 | 7 | 131 | 7 | 0.62 |
| iC | U/ml | 2.1E-1 | 5.9E-1 | 9.0E-1 | 2.6E0 | 4.6E0 | 4.9E0 | 1.0E-9 | 1.0E-9 | 5.5E1 | 1.4E1 | 197 | 7 | 131 | 7 | 0.73 |
| iH | ng/ml | 1.6E5 | 1.9E5 | 1.5E5 | 1.7E5 | 4.7E4 | 5.1E4 | 5.1E4 | 7.8E4 | 2.7E5 | 2.5E5 | 231 | 18 | 159 | 18 | 0.63 |
| iJ | ng/ml | 5.4E4 | 5.0E4 | 5.5E4 | 5.9E4 | 2.9E4 | 2.0E4 | 5.5E3 | 3.3E4 | 2.5E5 | 9.7E4 | 231 | 18 | 159 | 18 | 0.55 |
| hB | ng/ml | 4.1E-1 | 4.8E-1 | 5.0E-1 | 7.3E-1 | 3.3E-1 | 7.7E-1 | 1.0E-9 | 1.5E-1 | 2.3E0 | 3.4E0 | 231 | 18 | 159 | 18 | 0.58 |
| hC | pg/ml | 3.9E3 | 3.2E3 | 6.8E3 | 7.0E3 | 1.0E4 | 7.5E3 | 1.0E-9 | 1.0E-9 | 1.1E5 | 2.5E4 | 231 | 18 | 159 | 18 | 0.51 |
| hF | ng/ml | 1.0E-9 | 1.0E-9 | 2.1E1 | 1.0E-9 | 2.7E2 | 0.0E0 | 1.0E-9 | 1.0E-9 | 4.0E3 | 1.0E-9 | 231 | 18 | 159 | 18 | 0.49 |
| hG | pg/ml | 6.9E3 | 6.8E3 | 7.4E3 | 8.0E3 | 3.2E3 | 3.7E3 | 2.8E1 | 3.6E3 | 1.9E4 | 1.7E4 | 231 | 18 | 159 | 18 | 0.53 |
| iO | ng/ml | 3.8E5 | 3.4E5 | 4.0E5 | 3.6E5 | 1.8E5 | 1.2E5 | 1.1E4 | 1.4E5 | 1.1E6 | 5.4E5 | 231 | 18 | 159 | 18 | 0.46 |
| iP | ng/ml | 5.0E4 | 4.0E4 | 5.5E4 | 6.1E4 | 5.2E4 | 4.5E4 | 1.0E-9 | 5.6E3 | 5.5E5 | 1.6E5 | 231 | 18 | 159 | 18 | 0.52 |
| iZ | ng/ml | 1.6E3 | 2.0E3 | 1.8E3 | 2.4E3 | 7.8E2 | 1.3E3 | 4.7E2 | 9.8E2 | 5.7E3 | 6.5E3 | 230 | 18 | 158 | 18 | 0.65 |
| rC | pg/ml | 1.6E3 | 1.6E3 | 2.2E3 | 1.6E3 | 2.2E3 | 9.0E2 | 1.0E-9 | 4.8E2 | 1.5E4 | 2.5E3 | 189 | 7 | 128 | 7 | 0.47 |
| rB | pg/ml | 2.4E1 | 7.1E1 | 4.3E1 | 7.3E1 | 8.9E1 | 3.6E1 | 1.0E-9 | 2.6E1 | 9.5E2 | 1.4E2 | 189 | 7 | 128 | 7 | 0.84 |
| jD | ng/ml | 3.1E1 | 4.4E1 | 4.8E1 | 7.5E1 | 6.1E1 | 9.9E1 | 1.0E-9 | 1.0E-9 | 5.1E2 | 2.9E2 | 196 | 7 | 131 | 7 | 0.59 |
| jE | ng/ml | 1.0E-9 | 1.0E-9 | 7.1E0 | 1.1E1 | 1.7E1 | 1.9E1 | 1.0E-9 | 1.0E-9 | 1.2E2 | 4.6E1 | 196 | 7 | 131 | 7 | 0.54 |
| jF | ng/ml | 4.2E1 | 1.0E-9 | 5.7E1 | 2.6E1 | 6.3E1 | 5.0E1 | 1.0E-9 | 1.0E-9 | 3.5E2 | 1.5E2 | 196 | 7 | 131 | 7 | 0.29 |
| jG | ng/ml | 4.6E3 | 6.4E3 | 4.7E3 | 5.4E3 | 2.0E3 | 2.6E3 | 7.6E2 | 6.4E2 | 1.1E4 | 7.9E3 | 197 | 7 | 131 | 7 | 0.63 |
| jH | ng/ml | 7.6E1 | 1.1E2 | 8.5E1 | 9.8E1 | 4.8E1 | 3.3E1 | 1.3E1 | 4.8E1 | 3.3E2 | 1.4E2 | 197 | 7 | 131 | 7 | 0.65 |
| jI | ng/ml | 6.8E1 | 7.7E1 | 7.3E1 | 9.3E1 | 3.3E1 | 5.0E1 | 1.9E1 | 3.8E1 | 2.5E2 | 1.9E2 | 197 | 7 | 131 | 7 | 0.63 |
| rA | pg/ml | 2.6E1 | 1.5E1 | 3.1E1 | 1.6E1 | 2.5E1 | 8.8E0 | 1.0E-9 | 6.9E0 | 2.0E2 | 3.1E1 | 197 | 7 | 131 | 7 | 0.27 |
| qY | pg/ml | 2.6E1 | 7.6E1 | 5.1E1 | 6.5E1 | 6.6E1 | 5.9E1 | 8.7E-1 | 3.3E0 | 5.3E2 | 1.5E2 | 197 | 7 | 131 | 7 | 0.54 |
| qX | pg/ml | 5.9E1 | 6.0E1 | 6.5E1 | 4.9E1 | 4.2E1 | 3.2E1 | 1.0E-9 | 1.0E-9 | 2.1E2 | 8.5E1 | 197 | 7 | 131 | 7 | 0.41 |
| qW | pg/ml | 9.2E0 | 6.3E0 | 1.4E1 | 9.1E0 | 1.6E1 | 1.0E1 | 1.0E-9 | 4.0E-1 | 1.2E2 | 3.1E1 | 197 | 7 | 131 | 7 | 0.39 |
| qV | pg/ml | 2.2E3 | 2.8E3 | 2.9E3 | 4.4E3 | 2.1E3 | 5.7E3 | 1.0E2 | 8.8E2 | 1.1E4 | 1.7E4 | 197 | 7 | 131 | 7 | 0.52 |
| qU | pg/ml | 6.1E1 | 1.4E2 | 1.6E2 | 2.3E2 | 2.8E2 | 3.1E2 | 1.0E-9 | 3.0E1 | 2.1E3 | 9.1E2 | 197 | 7 | 131 | 7 | 0.64 |
| qT | pg/ml | 4.0E1 | 4.3E1 | 6.8E1 | 5.9E1 | 9.8E1 | 5.2E1 | 1.0E-9 | 1.1E1 | 9.0E2 | 1.7E2 | 197 | 7 | 131 | 7 | 0.54 |
| jK | ng/ml | 1.6E3 | 2.0E3 | 1.7E3 | 1.7E3 | 6.5E2 | 9.8E2 | 2.8E2 | 4.7E2 | 4.3E3 | 3.3E3 | 197 | 7 | 131 | 7 | 0.53 |
| jL | ng/ml | 1.9E2 | 2.7E2 | 2.8E2 | 2.6E2 | 2.5E2 | 8.5E1 | 3.6E1 | 1.6E2 | 2.1E3 | 3.9E2 | 197 | 7 | 131 | 7 | 0.62 |
| jM | ng/ml | 7.4E4 | 5.0E4 | 7.8E4 | 6.4E4 | 3.9E4 | 4.6E4 | 3.9E2 | 7.8E3 | 1.9E5 | 1.5E5 | 197 | 7 | 131 | 7 | 0.39 |
| jO | pg/ml | 2.1E5 | 2.0E5 | 2.6E5 | 2.7E5 | 1.5E5 | 1.6E5 | 5.2E4 | 1.2E5 | 1.1E6 | 4.8E5 | 197 | 7 | 131 | 7 | 0.50 |
| jP | pg/ml | 2.2E5 | 2.2E5 | 2.6E5 | 3.5E5 | 1.6E5 | 3.9E5 | 3.6E4 | 1.1E5 | 9.2E5 | 1.2E6 | 197 | 7 | 131 | 7 | 0.49 |
| jQ | pg/ml | 2.7E3 | 1.3E3 | 3.8E3 | 1.9E3 | 3.5E3 | 2.0E3 | 1.0E-9 | 4.6E2 | 1.8E4 | 6.3E3 | 197 | 7 | 131 | 7 | 0.33 |
| jR | pg/ml | 7.7E3 | 3.3E3 | 1.2E4 | 5.8E3 | 1.3E4 | 8.4E3 | 1.0E-9 | 1.0E-9 | 9.0E4 | 2.5E4 | 197 | 7 | 131 | 7 | 0.32 |

Figure 9 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jT | pg/ml | 1.8E5 | 1.7E5 | 1.8E5 | 1.9E5 | 6.6E4 | 8.1E4 | 6.8E4 | 8.9E4 | 4.5E5 | 3.0E5 | 197 | 7 | 131 | 7 | 0.53 |
| jU | mIU/ml | 4.6E0 | 6.2E0 | 1.1E1 | 8.7E0 | 1.7E1 | 7.2E0 | 6.2E-2 | 1.9E-1 | 1.1E2 | 1.7E1 | 197 | 7 | 131 | 7 | 0.55 |
| jV | mIU/ml | 1.5E0 | 1.1E0 | 3.8E0 | 3.7E0 | 6.4E0 | 5.6E0 | 1.7E-3 | 6.9E-4 | 3.5E1 | 1.4E1 | 197 | 7 | 131 | 7 | 0.42 |
| jY | ng/ml | 5.9E-4 | 3.3E-3 | 5.8E-3 | 6.2E-3 | 2.7E-2 | 5.3E-3 | 1.0E-9 | 1.0E-9 | 3.0E-1 | 1.3E-2 | 197 | 7 | 131 | 7 | 0.74 |
| kC | pg/ml | 9.7E1 | 9.7E1 | 1.8E2 | 1.9E2 | 3.8E2 | 2.0E2 | 2.1E1 | 5.9E1 | 3.5E3 | 6.0E2 | 131 | 7 | 103 | 7 | 0.54 |
| kE | pg/ml | 1.3E5 | 1.5E5 | 1.3E5 | 1.5E5 | 3.8E4 | 3.8E4 | 1.2E4 | 9.0E4 | 2.3E5 | 2.0E5 | 131 | 7 | 103 | 7 | 0.60 |
| kF | pg/mL | 6.0E1 | 7.2E1 | 6.8E1 | 7.6E1 | 4.8E1 | 3.1E1 | 2.6E1 | 5.0E1 | 5.1E2 | 1.4E2 | 131 | 7 | 103 | 7 | 0.62 |
| kG | pg/mL | 9.2E3 | 7.1E3 | 1.2E4 | 1.5E4 | 1.4E4 | 1.7E4 | 7.5E2 | 1.1E3 | 1.2E5 | 4.3E4 | 131 | 7 | 103 | 7 | 0.45 |
| kI | pg/ml | 1.8E2 | 1.9E2 | 2.2E2 | 2.9E2 | 1.3E2 | 2.7E2 | 4.4E1 | 9.5E1 | 8.7E2 | 8.7E2 | 131 | 7 | 103 | 7 | 0.52 |
| kK | pg/ml | 1.0E2 | 1.7E2 | 1.6E2 | 2.6E2 | 1.9E2 | 2.5E2 | 6.4E0 | 3.2E1 | 1.6E3 | 6.9E2 | 131 | 7 | 103 | 7 | 0.62 |
| kN | pg/ml | 9.5E2 | 4.4E2 | 2.0E3 | 6.1E3 | 5.2E3 | 1.5E4 | 7.6E1 | 2.9E2 | 5.5E4 | 3.9E4 | 131 | 7 | 103 | 7 | 0.33 |
| kO | pg/ml | 7.2E3 | 9.5E3 | 8.6E3 | 1.1E4 | 1.1E4 | 5.3E3 | 3.4E3 | 5.2E3 | 1.3E5 | 1.7E4 | 131 | 7 | 103 | 7 | 0.63 |
| kP | pg/ml | 6.3E3 | 4.7E3 | 7.5E3 | 5.0E3 | 6.2E3 | 3.1E3 | 8.6E2 | 1.2E3 | 4.8E4 | 9.8E3 | 131 | 7 | 103 | 7 | 0.36 |
| kQ | pg/ml | 4.1E3 | 4.8E3 | 4.9E3 | 5.8E3 | 3.0E3 | 4.6E3 | 5.6E2 | 1.6E3 | 2.5E4 | 2.1E4 | 231 | 18 | 159 | 18 | 0.53 |
| kR | pg/ml | 2.1E1 | 2.1E1 | 3.1E1 | 2.5E1 | 6.9E1 | 1.8E1 | 1.0E-9 | 1.2E0 | 1.0E3 | 7.1E1 | 231 | 18 | 159 | 18 | 0.48 |
| kS | pg/ml | 8.0E2 | 7.0E2 | 9.7E2 | 1.1E3 | 1.0E3 | 1.0E3 | 8.2E1 | 7.9E1 | 1.4E4 | 3.6E3 | 231 | 18 | 159 | 18 | 0.50 |
| rZ | ng/ml | 1.0E-9 | 6.9E-3 | 5.4E-3 | 4.2E-2 | 1.5E-2 | 9.7E-2 | 1.0E-9 | 1.0E-9 | 1.1E-1 | 2.6E-1 | 190 | 7 | 126 | 7 | 0.63 |
| rY | ng/ml | 5.7E-2 | 6.1E-2 | 3.6E-1 | 2.5E0 | 2.3E0 | 6.3E0 | 1.0E-9 | 1.2E-2 | 2.3E1 | 1.7E1 | 190 | 7 | 126 | 7 | 0.61 |
| rX | ng/ml | 1.0E-9 | 1.0E-9 | 6.9E-2 | 2.9E-1 | 4.2E-1 | 7.0E-1 | 1.0E-9 | 1.0E-9 | 3.7E0 | 1.9E0 | 190 | 7 | 126 | 7 | 0.64 |
| lK | pg/ml | 9.9E1 | 1.3E1 | 1.9E2 | 5.9E1 | 3.1E2 | 7.8E1 | 1.0E-9 | 1.0E-9 | 3.3E3 | 2.1E2 | 196 | 7 | 131 | 7 | 0.30 |
| lL | pg/ml | 1.6E3 | 3.2E3 | 2.6E3 | 3.5E3 | 3.7E3 | 2.1E3 | 1.5E1 | 2.1E2 | 4.2E4 | 6.3E3 | 197 | 7 | 131 | 7 | 0.69 |
| lM | pg/ml | 1.1E3 | 1.7E3 | 3.5E3 | 1.9E3 | 7.5E3 | 1.8E3 | 1.2E2 | 2.4E1 | 5.1E4 | 4.9E3 | 197 | 7 | 131 | 7 | 0.46 |
| lN | pg/ml | 1.0E-9 | 1.0E-9 | 4.2E0 | 6.9E0 | 1.5E1 | 1.3E1 | 1.0E-9 | 1.0E-9 | 1.5E2 | 3.5E1 | 197 | 7 | 131 | 7 | 0.56 |
| lO | pg/ml | 1.0E-9 | 1.0E-9 | 1.6E0 | 1.2E1 | 1.1E1 | 3.2E1 | 1.0E-9 | 1.0E-9 | 1.3E2 | 8.4E1 | 196 | 7 | 131 | 7 | 0.56 |
| nW | pg/ml | 1.1E5 | 1.1E5 | 1.1E5 | 1.1E5 | 2.5E4 | 2.8E4 | 5.8E4 | 7.2E4 | 1.8E5 | 1.9E5 | 231 | 18 | 159 | 18 | 0.49 |
| nY | pg/ml | 2.1E3 | 2.1E3 | 2.4E3 | 2.3E3 | 1.6E3 | 1.2E3 | 5.1E2 | 5.4E2 | 1.3E4 | 5.7E3 | 231 | 18 | 159 | 18 | 0.49 |
| oO | pg/ml | 7.8E4 | 1.2E5 | 1.1E5 | 1.3E5 | 9.7E4 | 5.7E4 | 1.5E4 | 5.2E4 | 6.2E5 | 2.3E5 | 123 | 7 | 97 | 7 | 0.67 |
| oP | pg/ml | 1.2E5 | 2.5E5 | 1.4E5 | 2.5E5 | 9.1E4 | 7.1E4 | 2.4E4 | 1.5E5 | 4.5E5 | 3.3E5 | 123 | 7 | 97 | 7 | 0.83 |
| oQ | pg/ml | 2.8E3 | 5.8E3 | 3.5E3 | 7.2E3 | 2.8E3 | 5.8E3 | 9.3E2 | 2.6E3 | 2.1E4 | 2.0E4 | 123 | 7 | 97 | 7 | 0.82 |
| oE | pg/ml | 1.3E2 | 1.4E2 | 3.6E2 | 2.8E2 | 5.4E2 | 3.4E2 | 1.0E-9 | 2.8E0 | 4.7E3 | 1.4E3 | 231 | 18 | 159 | 18 | 0.49 |
| oF | pg/ml | 7.7E3 | 1.2E4 | 2.0E4 | 3.7E4 | 3.6E4 | 5.7E4 | 6.4E1 | 4.8E2 | 2.5E5 | 1.8E5 | 231 | 18 | 159 | 18 | 0.60 |
| oH | pg/ml | 4.4E1 | 4.8E1 | 9.3E1 | 1.1E2 | 1.4E2 | 1.7E2 | 4.2E0 | 1.6E1 | 9.9E2 | 6.3E2 | 231 | 18 | 159 | 18 | 0.53 |
| oK | pg/ml | 7.6E2 | 8.5E2 | 1.8E3 | 4.6E3 | 2.5E3 | 1.2E4 | 5.2E1 | 3.1E2 | 1.8E4 | 5.3E4 | 231 | 18 | 159 | 18 | 0.58 |
| oN | pg/ml | 5.0E2 | 5.6E2 | 7.5E2 | 8.1E2 | 1.4E3 | 1.1E3 | 1.5E2 | 2.4E2 | 1.8E4 | 5.0E3 | 231 | 18 | 159 | 18 | 0.53 |
| pF | pg/ml | 4.5E-1 | 5.5E-1 | 1.0E0 | 1.2E0 | 5.7E0 | 2.3E0 | 1.0E-9 | 1.0E-9 | 8.7E1 | 1.0E1 | 231 | 18 | 159 | 18 | 0.52 |

Analyte panel data:

Unconstrained panels with 3 analytes, where 1.0E-10 >= 'model p-value' > 0. Contains 25 panels of 10,034,416 total panels evaluated. : Et{Jo(Ik Ly Nc Ne Nl) Om(Mt Nc Nl) Jj(Ly Nl) MiHq} Ok{Jo(Ik Lv Ly Nl Om) MiHq MtOm NlJj} Mi{Hq(Lx Mt Nl Nw)} GnKcVo LyOnOy Unconstrained panels with 3 analytes, where 1.0E-9 >= 'model p-value' > 1.0E-10. Contains 188 panels of 10,034,416 total panels evaluated. : Ok{Jo(Et Hw Hx Iq Lx Md Mi Mt Nc Nd Ne Nf Nj Og Oz Pa) Nl(aA Et Hw In Js Jt Lx Md Mi Nf Of Og Om Pa) Om(aA Et Hw Ji Jj Js Jt Lx Mi Nc Ne Nf Pa) Lx(Hw Jt Ly Nd Nf Po) Nc(Hw Jj Js Jt Og) Mt(Hw Jt Nd Nf) Ly(Jj Nf Og) Ne(Hw Jj) Nf(Jt Pa) NdOg JtPa} Et{Nl(aA Hw In Iu Ji Js Jt Lx Ly Md Me Mi Mt Nd Nf Nk Nw Of Og On Pa) Om(aA Fp Ji Jo Lx Ly Mi Ne Nw On Pa) Jo(Fp Lv Lx Mi Mt Nd Nj Nt Pa) Nc(Hw Jj Jt Ly Md Mi Pa) Ly(Lx Md Mi Of Pa) NdPa NeJj OnOy} On{Md(Hq Hw Lx Ly Mt Nc Nd Ne Nf Nl Om Oy) Oy(Hw Ik Lx Mt Nc Nd Ne Nj Nl Om Pa) Om(Jj Lx Mt Nl) Nl(Hq Jj) LxNf LyJj} Nl{Nw(Hw In Jj Js Md Om) Lx(aA Ji Jj Mi) Jj(Jg Mt) JiOg} Om{Lx(aA Jg Ji Mt) Mt(Ji Nw) MdNw JgJj} Mi{Hq(Fp Ik Ji Ly Nc Ne)} Ly{Jj(Jg Lx Mt) MdNw} GnHuRa LxNfJi MdNcNw Unconstrained panels with 3 analytes, where 1.0E-8 >= 'model p-value' > 1.0E-9. Contains 1,188 panels of 10,034,416 total panels evaluated. : Ok{Jo(aA Fp Fr Hq Ih Ii Ij Im In Io Ip Ir Is It Iu Iv Jg Ji Jj Jl Jm Jp Jq Jr Js Jt Lh Lj Lu Lz Ma Mb Mc Me Mf Mg Mk Ml Mm Mn Mp Mq Mr Ms Mu Mx My Na Nb Ng Nh Ni Nk Nn No Nq Nr Ns Nt Nu Nw Nx Ny Oe Of Oi On Oy Pb Pc Pd Pe Pf Pg Qa Qc Qe) Nl(Fp Fr Hq Hr Hu Hv Hx Ih Ii Ij Il Iq It Iu Jg Jh Ji Jk Jl Jm Jn Jp Jq Jr Lj Lv Ly Lz Ma Mc Me Mg Mj Ml Mm Mn Mq Mr Ms Mt Mx My Na Nd Ne Ng Ni Nk Nm Nq Ns Nw Oe On Oz Pb Pc Pd Po Pz Qb Qc Qd Qe) Om(Fp Fr Hq Hr Hu Hv Hx Ih Ik Im In Ip Iq Iu Iv Jg Jh Jk Jl Jm Jn Jp Jq Jr Lh Li Lj Lv Ly Md Mm Mr Nd Nh Nj Nk Nq Nw Of Og On Oz Pb Pc Pe Pg Po Pz Qa Qb Qc Qd Qe) Nc(aA Et Hq Hx Ii Ij In Iq Iu Ji Jk Jq Jr Lv Lx Ly Lz Md Mi Mt Nd Nf Ng Ni Nk Nq Nw Of Oz Pa Pd Po) Nf(aA Et Fp Hw Ik Jg Ji Jj Jl Jr Js Lj Lv Md Mi Mr Nd Ne Nj Nq Nw Of Og On Pb Pc Qe) Jt(aA Et Hw Ik Iq Iv Jg Ji Jj Jl Jp Lv Ly Md Mi Mm Mr Nd Ne Nj Nt Of Og Oz Qe) Mt(Et Fp Hq Ii Ij In Iq Jj Js Lx Ly Md Ne Ng Nj Nq Of Og Oy Oz Pa) Lx(aA Hq Hx Ii Ij In Iq Iu Jj Js Lz Md Ne Nj Nq Of Og Oz Pd) Ne(aA Et Hq In Iq Iu Js Ly Md Mi Nd Of Og Pa) Ly(aA Et Hq Hw In Jp Js Md Mi Of Pa) Jj(Fp Hw Ik Iq Lv Md Nd Nj Oz Pa) Og(Hw Ik Iq Js Lv Md Nj Nq Of Pa) Mi(Hw Iq Js Md Nd Nq Of Pg) Pa(aA Hw Iq Js Md Nd Nj Of) Nd(aA Et Hw Js Md Of) Of(Ik Iq Js Md) Md(Hw On) FpHw MrHq NgJg OnOy} Et{Nl(Fp Fr Hq Hr Hu Hv Hx Ih Ii Ij Ik Im Io Ip Iq Ir Is It Iv Jg Jh Jk Jl Jm Jn Jp Jq Jr Lh Li Lj Lu Lv Lw Lx Lz Ma Mb Mc Mf Mg Mh Mj Mk Ml Mm Mn Mp Mq Mr Ms Mu Mv Mw Mx My Mz

Figure 9 Continued

Na Nb Nc Ne Ng Nh Ni Nj Nm Nn No Nq Nr Ns Nt Nu Nv Nx Ny Oe Oh Oi Oy Oz Pb Pc Pd Pe Pf Pg Po Pz Qa Qb Qc Qd Qe) Nc(aA Fp Fr
Hq Ii Ij Ik Im Iq Iu Jg Ji Jl Jr Js Lj Lv Lx Lz Ma Mc Me Mg Ml Mr Ms Mt Mx My Nd Nf Ng Ni Nj Nk Nq Ns Nw Of Og On Oz Pb Pc Pd Qe)
Om(Fr Hw Ih Ik Im Ip Iq Ir Is Iu Iv Jg Jj Jl Jp Jr Js Jt Lh Lj Lv Md Mk Mr Nd Nf Nh Nj Nk Nt Of Og Oh Oz Pb Pe Qa Qb Qe) Jo(Hw Ih Iq It Iv
Jg Ji Jl Jm Jr Lh Lj Mb Md Mf Mg Mk Mr Nf Nh Nk Nq Nu Nw Oi On Oy Oz Pb Pc Pe Pg Pa Qe) Ly(aA Fp Hq Hw Ih In Iu Jg Ji Jp Jr Js Jt Lj
Lv Mg Mr Mt Nd Ne Nf Ng Nj Nq Nw Og On Pb Qe) Ne(aA Hw In Iq Iu Js Jt Lx Md Mi Mt Nd Nf Of Og On Pa) Mt(Hw Ij In Iq Jj Js Jt Md
Nd Nf Ng Nq Of Og Pa) Lx(Hq Hw Iq Jj Js Jt Md Nd Nf Nj Nq Of Po) Nd(aA Fp Ji Jj Mi Nf Nw Of Og On) Pa(aA Hw Iq Jj Jt Md Nf Nj Of)
Md(Fp Jg Ji Mi Mw Nw On) Nf(Fp Ji Mi Mr Nw On) Jt(Fp Jg Ji Nt Qe) Mi(Iq Nj Nq Pg) Jj(Fp Ik Nj) MrHq NgJg} Nl{Nw(aA Hq Hu Ii Ij Il Iq
Iu Ji Jn Jo Jq Jr Jt Lx Ly Lz Me Mi Mj Ml Mm Ms Mt Mx My Nd Nf Ni Nk Ny Of Og On Oz Pa Pd Po Qb Qc) Lx(Hq Hw In Iu Jg Js Lv Ly Lz
Md Mm Mr Mt Nd Nf Ni Nk Og Om On Pa Po) Ji(aA Hw In Iq Iu Jj Jo Jq Ly Md Me Mi Ml Mm Mt Nd Nf Ni Nk Om Oz Pa) Mi(Hw Jg Jj Ly
Md Mm Mt Nk On Oy Pa Pg) On(Hw In Js Mm Mt Nf Nk Of Og Pa Pg) Jj(aA Fr Lh Mm Pa Qe) Jg(Md Mv Ng Og Om) Pa(aA Mm Mt Nk)
MmaA MtOm} Lx{Ly(aA Hw In Jg Ji Jo Jp Js Md Mi Mm Mt Nc Nf Nw Og Om On Pa Po) Om(Ik Jj Jl Lv Md Mi Mm Mr Nc Ne Nf Nw Pa)
Ji(Hw In Iq Jj Jq Md Nc Nd Ne Nq Og Po) Mi(Hw In Md Nc Nd Ne Nf Nq Pg Po) Nd(aA Jj Mm Mt Nf Nw Og On) Jj(Ik Jg Mt Nc Ne Nj On)
On(Hq Hw Nc Nq Po) Jg(Md Mv Ng Nq) Mr(Hq Nf Oy) Ne(aA Hw In) Nc(Hw Nk) Nw(Md Nf) aA(Nj Nq) MtHw} Nw{Om(aA Hq Hw Ik In
Jg Ji Jj Jo Js Ly Mi Nc Nd Ne Nf Nj Pa Qa Qe) Md(Hw Ik Jg Js Lv Lz Mi Mt Mw Nd Ne Nf Nj Og On Oz Pa) Nc(Hw In Jj Js Ly Mi Nd Nf Nk
Og) Ly(Hw In Jj Jo Js Mi Nf Og) Nd(Jj Mi Mt Nf Og Pa) Nf(Ik Js Mi On Pa) Ne(Hw In Jj Js) Ik(Jj Jo) MiPg MrHq MtHw OnOy} On[Om(Fp
Hw Iq Iu Iv Ji Jo Js Lj Ly Mi Nc Ne Nf Ng Nq Of Pa) Md(Fp Ij Ik Iq Jj Jo Lv Mb Mj Nj Nq Of Og Oz Pa) Oy(Fp Hq Iq Iv Jg Lv Mf Mi Nf Nh
Nq Og Oz Pb) Nf(Fp Hq Ly Mt Nd Pa) Hq(Ly Mi Mt Nc Ne) Jj(Ik Mt Nc Nd Ne) Hw(Ly Mt Nc Ne) Ly(Jo Of) MtNd} Ji{Om(aA Fp Jg Jj Ly
Nc Ne Nf Pa Qe) Ly(aA Jj Md Mt Nc Nf Og Pa) Mt(Hw Jj Jq Md Nd Nf Og) Ne(aA Nf Og Pa) Nd(Nf Og Pa) Nc(Hw Og) Nf(Fp Pa)}
Mt{Om(Fp Jg Jj Jp Lv Mi Mm Mr Pa Qe) Jj(Fp Ik Md Nc Nd Nj Pa) Mi(Ly Md Nd Pg) Pa(Ly Nd) NgJg} Mi{Hq(Ih Iv Jg Jp Nd Nh Nj Nt Nx
Oi Oz Pa Qe) JgOm} Ly{Jg(Md Ng Om) Jj(aX Jp Qe) Gn(bL Rc) aX(bN Nf) bVgP} Jg{Om(Fp Mv Nc Ne Og Pa) MrOy NcJj} Gn{Hu(Um Uo)
IzKc} IkJjPa

Unconstrained panels with 3 analytes, where 1.0E-7 >= 'model p-value' > 1.0E-8. Contains 5,367 panels of 10,034,416 total panels evaluated. :
Ok{Hw(aA Et Fr Hq Hr Hu Hv Hx Ih Ii Ij Ik Im In Io Ip Iq Ir Is It Iu Iv Jg Jh Ji Jk Jl Jm Jn Jp Jq Jr Js Lh Li Lj Lu Lv Lw Lz Ma Mb Mc Me Mf
Mg Mh Mj Mk Ml Mm Mn Mp Mq Mr Ms Mu Mv Mw Mx My Mz Na Nb Ng Nh Ni Nj Nk Nm Nn No Nq Nr Ns Nt Nu Nv Nw Nx Ny Oe Of
Oh Oi On Oy Oz Pb Pc Pd Pe Pf Pg Po Pz Qa Qb Qc Qd Qe) Of(aA Et Fp Fr Hq Hr Hu Hv Hx Ih Ii Ij Im In Ip Ir Is It Iu Iv Jg Jh Ji Jj Jk Jl Jm Jn
Jp Jq Jr Lh Li Lj Lu Lv Lw Lz Ma Mb Mc Me Mf Mg Mh Mj Mk Ml Mm Mn Mp Mq Mr Ms Mu Mv Mw Mx My Mz Na Nb Ng Nh Ni Nj Nk
Nm Nn No Nq Nr Ns Nt Nu Nv Nw Nx Ny Oe Oh Oi On Oy Oz Pb Pc Pd Pe Pf Pg Po Pz Qa Qb Qc Qd Qe) Ly(Fp Fr Hr Hu Hv Hx Ih Ii Ij Ik Il
Im Io Ip Iq Ir Is It Iu Iv Jg Jh Ji Jk Jl Jm Jn Jq Jr Lh Li Lj Lu Lv Lw Lz Ma Mb Mc Me Mf Mg Mh Mj Mk Ml Mm Mn Mp Mq Mr Ms Mu Mv
Mw Mx My Mz Na Nb Nd Ng Nh Ni Nj Nk Nm Nn No Nq Nr Ns Nt Nu Nv Nw Nx Ny Oe Oh Oi On Oy Oz Pb Pc Pd Pe Pf Pg Po Pz Qa Qb
Qc Qd Qe) Ne(Fp Fr Hr Hu Hv Hx Ih Ii Ij Ik Im Io Ip Ir Is It Iv Jg Jh Ji Jk Jl Jm Jn Jp Jq Jr Lh Li Lj Lu Lv Lw Lz Ma Mb Mc Me Mf Mg Mh Mj
Mk Ml Mm Mn Mp Mq Mr Ms Mu Mv Mw Mx My Mz Na Nb Nc Ng Nh Ni Nj Nk Nm Nn No Nq Nr Ns Nt Nu Nv Nw Nx Ny Oe Oh Oi On
Oy Oz Pb Pc Pd Pe Pf Pg Po Pz Qa Qb Qc Qd Qe) Jj(aA Et Fr Hq Hr Hu Hv Hx Ih Ii Ij Im In Io Ip Ir Is It Iu Iv Jg Jh Ji Jk Jl Jm Jn Jp Jq Jr Js Lh
Lj Lu Lw Lz Ma Mb Mc Me Mf Mg Mh Mi Mk Ml Mm Mn Mp Mq Mr Ms Mu Mv Mw Mx My Na Nb Ng Nh Ni Nk Nm Nn No Nq Nr Ns Nt
Nu Nv Nw Nx Ny Oe Og Oh Oi On Oy Pb Pc Pd Pe Pf Pg Pz Qa Qc Qd Qe) Mt(aA Fr Hr Hu Hv Hx Ih Ik Il Im Io Ip Ir Is It Iu Iv Jg Jh Ji Jk Jl
Jm Jn Jp Jq Jr Lh Li Lj Lu Lv Lw Lz Ma Mb Mc Me Mf Mg Mh Mi Mj Mk Ml Mm Mn Mp Mq Mr Ms Mu Mv Mw Mx My Mz Na Nb Nh Ni
Nk Nm Nn No Nr Ns Nt Nu Nv Nw Nx Ny Oe Oh Oi On Pb Pc Pd Pe Pf Pg Po Pz Qa Qb Qc Qd Qe) Lx(Et Fp Fr Hr Hu Hv Ih Ik Il Im Io Ip Ir
Is It Iv Jg Jh Ji Jk Jl Jm Jn Jp Jq Jr Lh Li Lj Lu Lv Lw Ma Mb Mc Me Mf Mg Mh Mi Mj Mk Ml Mm Mn Mp Mq Mr Ms Mu Mv Mw Mx My
Mz Na Nb Ng Nh Ni Nk Nm Nn No Nr Ns Nt Nu Nv Nw Nx Ny Oe Oh Oi On Oy Pa Pb Pc Pe Pf Pg Pz Qa Qb Qc Qd Qe) Nd(Fp Fr Hq Hr Hu
Hv Hx Ih Ii Ij Ik Im In Io Ip Iq Ir Is It Iu Iv Jg Jh Ji Jk Jl Jm Jn Jp Jq Jr Lh Li Lj Lv Lz Ma Mc Me Mf Mg Mj Mk Ml Mm Mn Mp Mq Mr Ms
Mv Mx My Mz Nb Ng Nh Ni Nj Nk Nm Nn No Nq Nr Ns Nt Nu Nv Nw Ny Oe Oh Oi On Oy Oz Pb Pc Pd Pe Pf Pg Po Pz Qa Qb Qc Qd Qe) Jt(Fr Hq
Hr Hu Hv Hx Ih Ii Ij Il Im In Io Ip Ir Is It Iu Jh Jk Jm Jn Jq Jr Js Lh Li Lj Lu Lw Lz Ma Mb Mc Me Mf Mg Mh Mj Mk Ml Mn Mp Mq Ms Mu
Mv Mw Mx My Mz Na Nb Ng Nh Ni Nk Nm Nn No Nq Nr Ns Nu Nv Nw Nx Ny Oe Oh Oi On Oy Pb Pc Pd Pe Pf Pg Po Pz Qa Qb Qc Qd)
Nf(Fr Hq Hr Hu Hv Hx Ih Ii Ij Im In Io Ip Iq Ir Is It Iu Iv Jh Jk Jm Jn Jp Jq Lh Li Lu Lw Lz Ma Mb Mc Me Mf Mg Mh Mj Mk Ml Mm Mn Mp
Mq Ms Mu Mv Mw Mx My Mz Na Nb Ng Nh Ni Nk Nm Nn No Nq Nr Ns Nu Nv Nx Ny Oe Oh Oi On Oy Oz Pd Pe Pf Pg Po Pz Qa Qb Qc Qd)
Nc(Fp Fr Hr Hu Hv Ih Ik Il Im Io Ip Ir Is It Iv Jg Jh Jl Jm Jn Jp Lh Li Lj Lu Lw Ma Mb Mc Me Mf Mg Mh Mj Mk Ml Mm Mn Mp Mq Mr Ms
Mu Mv Mw Mx My Mz Na Nb Nh Nj Nl Nm Nn No Nr Ns Nt Nu Nv Nx Ny Oe Oh Oi On Oy Pb Pc Pe Pf Pg Pz Qa Qb Qc Qd Qe) Og(aA Et
Fp Fr Hq Hr Hu Hv Hx Ih Ii Ij Im In Ip Ir Is It Iu Iv Jg Jh Ji Jk Jl Jm Jn Jp Jq Jr Lh Lj Lz Ma Mb Mc Me Mf Mg Mi Mk Ml Mm Mn Mq Mr Ms Mv
My Na Ng Nh Nk Nm Nn Nr Ns Nt Nu Nv Nw Ny Oi On Oy Oz Pb Pc Pd Pe Pg Po Pz Qa Qb Qc Qd Qe) Pa(Et Fp Hq Hr Hx Ih Ii Ij Ik Im In Ip
Iu Iv Jg Ji Jk Jl Jq Jr Lv Lz Ma Mb Mc Mf Mg Mh Mi Mj Ml Mm Mn Mq Mr Ms Mv Mx My Na Ng Nh Nk Nm Nn Nq Nt Nv Nw Ny Oe Oh
Oy Oz Pd Po Qb Qc) Om(Ii Ij Il Io Ir Is It Lu Lw Lz Ma Mb Mc Me Mf Mg Mh Mj Mk Ml Mn Mp Mq Ms Mu Mv Mw Mx My Mz Na Nb Ng
Ni Nm Nn No Nr Ns Nt Nu Nv Nx Ny Oe Oh Oi Oy Pd Pf) Iq(aA Et Fp Fr Hq Hr Hx Ih Ik Im In Iu Iv Jg Ji Jl Jp Jq Jr Js Lj Lv Md Mg Mm Mr
Ms Ng Nj Nk Nm Nq Nw On Oz Pb Pc Pe Qa Qe) Nl(Ik Im Io Ip Ir Is Iv Lh Li Lu Lw Mb Mf Mh Mk Mp Mu Mv Mw Mz Nb Nh Nj Nn No Nr
Nt Nu Nv Nx Ny Oh Oi Oy Pe Pf Pg Qa) Mi(Et Fp Hx Ih Ii Ij Ik Im In Iu Iv Jk Jq Jr Lv Lz Ma Mb Mc Mg Mj Ml Mn Ms Mv Ng Nh Nj Nk Nm
Ny Oy Oz Pd Pf Po Qc) Js(aA Et Fp Hr Hx Ih Ii Ik Im In Iu Iv Jg Ji Jl Jp Jr Lj Lv Ma Md Mf Mg Mr Ms Ng Nh Nj Nk Nq Nt Nw Oz Pb Pe Qa
Qe) Md(aA Et Fp Fr Hq Hx Ii Ij Ik In Iu Iv Jg Ji Jl Jp Jr Lv Mb Mr Ms Mw Nh Nj Nk Nq Nw Nx Oz Pb Pc Pe Pg Qe) Jo(Hr Hu Hv Il Jh Jk Jn Li
Lw Mh Mj Mv Mw Mz Nm Nv Oh Po Pz Qb Qd) aA(Et Fp Hq Ii Ij Ik Iu Jr Lv Mf Mn Nh Nj Nq Oz) Et(Fp Hq Ik Iu Iv Jr Lj Lv Nh Nj Nk Nq
Oz) Nq(Fp Fr Iu Iv Jg Ji Jl Jp Jr Lv Oz Qe) Nj(Fp Hq Ii In Iu Ji Jp Jq Lv Nw Oz) In(Fp Ih Ik Ji Jl Jr Lv Mr Nk Qe) Hq(Fp Ik Jl Lv Mk Nw On
Oz Pb) Fp(Ii Ij Iu Jq Lz Po) Lv(Ii Ij Iu Jq Ng) Ik(Ii Ij Iu Ng) Mr(Ij Mj Oy) Ji(Ii Jq Oz) Jr(Ii Jq) Oy(Mk Pc) NwOz} Et{Ne(Fp Fr Hq Hr Hu Hv
Hx Ih Ii Ij Ik Im Io Ip Ir Is It Iv Jg Jh Jk Jl Jm Jn Jp Jq Jr Lh Li Lj Lu Lv Lw Lz Ma Mb Mc Me Mf Mg Mh Mj Mk Ml Mm Mn Mp Mq Mr Ms
Mu Mv Mw Mx My Mz Na Nb Nc Ng Nh Ni Nj Nk Nm Nn No Nq Nr Ns Nt Nu Nv Nw Nx Ny Oe Oh Oi Oy Oz Pb Pc Pd Pe Pf Pg Po Pz Qa
Qb Qc Qd Qe) Mt(aA Fp Fr Hq Hr Hu Hv Hx Ih Ii Ik Im Ip Iu Iv Jg Jh Ji Jk Jl Jm Jn Jp Jq Jr Lh Li Lj Lu Lv Lw Lx Lz Ma Mb Mc Me Mf Mg
Mh Mi Mj Mk Ml Mm Mn Mp Mq Mr Ms Mu Mv Mw Mx My Mz Na Nb Nh Ni Nj Nk Nm Nn No Nr Ns Nt Nu Nv Nx Ny Oe Oh Oi On Oy Oz
Pb Pc Pd Pe Pf Pg Po Pz Qb Qc Qd Qe) Ly(aX Dc FR Hr Hu Hv Hx Ii Ij Ik Il Im Io Ip Iq Ir Is It Iv Jh Jk Jl Jm Jn Jq Lh Li Lu Lw Lz Ma Mb Mc
Me Mf Mh Mj Mk Ml Mm Mn Mp Mq Ms Mu Mv Mw Mx My Mz Na Nb Nh Ni Nk Nm Nn No Nr Ns Nt Nu Nv Nx Ny Oe Oh Oi Oy Oz Pc
Pd Pe Pf Pg Po Pz Qa Qb Qc Qd) Lx(aA Fp Fr Hq Hr Hu Hv Hx Ih Ii Ij Ik Im In Ip Iu Iv Jg Jh Ji Jk Jl Jm Jq Jr Lj Lv Lz Ma Mb Mc Me Mf Mg Mi Mj

Oz Qe) Og(aA Fp Hw Ik Iq Iv Jg Jq Md Nh Nj Nt Oz Pa) Md(aA Fp Hw Ik Iq Jg Jp Jq Mi Mw Oz Pa) Pa(aA Hw Ik In Iq Jj Jo Jq Ms Nj) aA(Fp Iq Nj Oz) Mi(Hw Jq Pg) Jg(Jo Jt Ng) Jj(Ik Jq Nj) Iq(Ih Qe) FpHw IkJo} Mt{Jj(aA Fr Hw Hx Ih Ii Ij Im In Iq It Iv Jg Jl Jm Jp Jr Js Jt Lh Li Lj Lv Lw Lz Ma Mb Mc Me Mf Mg Mi Mk Ml Mm Mr Ms Mv My Nb Ne Nf Nh Nk Nm Nq Nr Ns Nt Nu Nx Og Oi Oy Oz Pb Pc Pe Pf Pg Pz Qa Qe) Om(aA Fr Hw Ih Ik Im In Io Ip Iq Ir Is Iu Iv Jl Jq Jr Js Jt Lh Li Lj Lu Lw Ly Ma Md Me Mf Mk Ml Mp Ms Mz Nb Nc Nd Ne Nf Ni Nj Nk Nm No Nq Nr Ns Nt Nu Nv Nx Og Oh Oi Oz Pb Pc Pe Pf Pg Qa Qd) Mi(Fp Hw Hx Ij Ik In Iq Jo Js Ma Ml Ms Nc Ne Nf Nj Nq Of Og Oy Pa Po) Nl(aA Fp Fr Hw In Iu Jg Jp Js Lv Ly Md Me Mm Mr Nd Ne Ni Nk Og) Pa(aA Fp Hw In Iq Js Lv Md Mm Ms Nc Ne Nf Nj Nq Of Og) Ly(aA aX Fp Gn Hw In Jg Jo Jp Lv Md Mm Mr Nc Og) Nd(aA Fp Hw Iu Jg Jl Jp Md Mm Mr Og) Hw(Fp Jl Lv Md Mm Mr Nc Og) Md(Fp Jg Lv Nc Nx Pc) Mr(Hq Ij In Mj Nf Oy) Jg(Mv My Nq Of) Og(Fp Ik Lv Nc) Nq(Jp Mm) Nc(Mm Nk) FpIn MkOy NfaX} Ly{aX(AA aJ aW aZ bA bJ bS cB cC cE cH cM cP cT Db dE dI Fp fR gP Hq Hw Ih Ii In Jg Jk Jo Jp Jq Js Lj Lv Lz Mb Md Mj Mr Mx Na Nd Nj Nk Nr Ns Oe Og Om Ou Oz Pa Pb Pc Pg Po Qe) Gn(aD aG aH aJ aN aO aV bF bN bP bX cF cH dC dJ dL gP Hu Js Jt Kf Kj Kn Mu Ul Um Un Uu Vo) fR(aA BA cP cT Dd De dJ gP Hr Jj Jp Ko Lv Md Mi Na Nf Og Ou Ub) Jj(Fp Fr Ik Im Jl Lh Li Mi Mm Nc Nl Nt Nv Pa Qa) Jp(Fp Hw Jo Lv Md Mi Mm Nc Nd Ne Nf Nl Og Om Pa) Jg(Jh Jo Lj Mi Mv My Nc Nf Nl Of Og Pa) Mi(Fp Md Nc Ne Pa Pg Qe) Aa(Jo Jr Nf Nl Pa) Mm(aA Nc Nl Pa) Nl(aA Fr Pa) DrRc EmKj SrJs PaaA aJgP} Nl{Mi(aA Fp Fr Hx Ij Ik Il Im In Iq Iu Iv Jo Jp Jr Js Lh Lj Lz Ma Mc Me Mh Ml Mx Mz Nd Ne Nf Ni Nj Nt Nx Of Og Om Oz Pb Pc Pd Pf Po Qe) Mm(Fp Fr Hw In Jg Jl Jo Jp Jr Lh Lj Lv Md Mr Nd Nf Ni Nk Of Og Om Pb Qe) Jj(Fp Ik Im Iv Jl Jm Jp Jt Li Lv Mg Mr Mz Nk Nm Nt Nv Nx Oy Pe Pg Pz Qa) Pa(Fr Hw Il In Jg Jp Lh Lv Lz Md Mr Nd Ne Nf Ni Nt Og Om) Jg(aA Hw Il In Jh Jk Jo Jt Lv My Nf Ni Nk Of Oy) aA(Fp Lv Md Me Ni Nk Nx Og Om Qe) Fr(Hw Md Nk Og Om) Jp(Lv Ni Nk Om) Nk(Fp Qe) AaOm MdNx InQe} Jg{Om(aA Hu Hw Ih Im Iq Ir Iu Iv Jl Jo Jr Js Jt Lj Lv Md Mm Mr My Nd Nf Ng Nh Nq Nr Ns Of Oz Pe Qa Qe) Md(Fp Jj Lv Mi Nc Nd Ne Ng Nq Nx Og Pa) Ng(Fp Ik Lv My Nc Nd Ne Nf Oz Pa Qe) Mv(Jj Mi Nc Nd Ne Nf Og Oz Pa) Pa(Jj Jt Nc Nd Nc Nq Of Og) Jj(Fp Ik Nd Ne Nj Nq) Mi(Nc Nd Ne Nq Of) Og(My Nc Nd Ne Nq) My(Nc Ne) FpNf MkOy NcOf} Mi{Hq(Fr Hw Im Iq Ir It Jm Jn Jr Lh Li Lj Lv Mb Mf Mg Mm Mr Nf Nk Nq Nr Nu Nv Om Pb Pc Pe Pf Pg Pz Qa Qd) Nc(Hw Jj Md Mm Nk Pa) Ik(Jj Jo Og Pa) Fp(Md Nf Pg) Ne(Md Pa Pg) Nd(Jp Pa) QeOm} Gn{Kc(Aj Ao Cw Ef Ez Jo Kj Nm Of Rc Uo Uu) Hu(cP Hb Ib Kn Om Ou Ow Qz Rc Ul Vo) Rc(Kk Me Rb) Ra(aV Ld Or) Kk(Um Vo) aV(aU cY) QwVo QvcN} aX{Ou(cE gP Hq Kc Ko Me Mj Nf Om Rb Vq) Nf(bN Lj Lv Nd Nj Pa Qe) Me(Ko Nd Nj Sr Vq) QegP} Jj{Nc(Ik Lh Mg Mm Nt Pa Qe) Ik(Jl Jp Me Mm Og Qe) Pa(Nd Ne Nj Nt) Qe(Nd Ne Om) MmNe} Mm{aA(Nc Nd Ne Om Pa) Nc(Nd Om Pa) Pa(Nd Ne) FpOm IkJo} Em{Kc(Kj Rc Vo) Kj(Me Nx)} Pa{aA(Nd Ne Nj) NcNk IkOg} Ko{fR(Jt Ue)} MdNxaA aVdOgP

Unconstrained panels with 3 analytes, where 1.0E-6 >= 'model p-value' > 1.0E-7. Contains 14,780 panels of 10,034,416 total panels evaluated. : Ok{Ms(aA Et Fp Fr Hq Hr Hu Hv Hx Ih Ii Ij Ik Im In Io Ip Ir Is It Iu Iv Jg Jh Ji Jk Jl Jm Jn Jp Jq Jr Lh Li Lj Lu Lv Lw Lz Ma Mb Mc Me Mf Mg Mh Mj Mk Ml Mm Mn Mp Mq Mr Mu Mv Mw Mx My Mz Na Nb Ng Nh Ni Nj Nk Nm Nn No Nq Nr Ns Nt Nu Nv Nw Nx Ny Oe Oh Oi On Oy Oz Pb Pc Pd Pe Pf Pg Po Pz Qa Qb Qc Qd Qe) Hx(aA Et Fp Fr Hq Hr Hu Hv Ih Ii Ij Ik Im In Io Ip Ir Is It Iu Iv Jg Jh Ji Jk Jl Jn Jp Jq Jr Lh Lj Lu Lv Lw Lz Ma Mb Mc Me Mf Mg Mh Mj Mk Ml Mm Mn Mp Mq Mr Mu Mv Mw Mx My Mz Na Nb Ng Nh Ni Nj Nk Nm Nn Nq Nr Ns Nt Nu Nv Nw Ny Oe Oh Oi On Oy Oz Pb Pc Pd Pe Pf Pg Po Pz Qa Qb Qc Qe) Ji(aA Et Fp Fr Hq Hr Hu Hv Ih Ij Ik Im Io Ip Ir Is It Iu Iv Jg Jh Jk Jl Jm Jn Jp Jr Lh Lj Lu Lv Lw Lz Ma Mb Mc Me Mf Mg Mh Mi Mj Mk Ml Mm Mn Mp Mq Mr Mu Mv Mw Mx My Mz Na Nb Ng Nh Ni Nk Nm Nn No Nr Ns Nt Nu Nv Nw Nx Ny Oe Oh Oi On Oy Pb Pc Pd Pe Pf Pg Po Pz Qa Qb Qc Qd Qe) Oz(Fp Fr Hr Hu Hv Ih Ii Ij Ik Il Im In Io Ip Ir Is It Iu Iv Jg Jh Jk Jl Jm Jn Jp Jq Jr Lh Li Lj Lu Lv Lw Lz Ma Mb Mc Me Mf Mg Mh Mj Mk Ml Mm Mn Mp Mq Mr Mu Mv Mw Mx My Mz Na Nb Ng Nh Ni Nk Nm Nn No Nr Ns Nt Nu Nv Nx Ny Oe Oh Oi On Oy Pb Pc Pd Pe Pf Pg Po Pz Qa Qb Qc Qd Qe) Jq(aA Et Fr Hq Hr Hu Hv Ih Ii Ij Ik Im In Ip Is It Iu Iv Jg Jh Jk Jl Jm Jn Jp Js Lh Lj Lu Lw Lz Ma Mb Mc Md Mc Mf Mg Mh Mj Mk Ml Mm Mn Mp Mq Mr Mu Mv Mw Mx My Mz Na Nb Ng Nh Ni Nk Nm Nn No Nq Nr Ns Nt Nu Nv Nw Nx Ny Oe Oh Oi On Oy Pb Pc Pd Pe Pf Pg Po Pz Qa Qb Qc Qe) Ik(Fp Fr Hr Hu Hv Ih Il Im Ip Ir Is It Iv Jg Jh Jk Jl Jm Jn Jp Jr Lh Li Lj Lu Lv Lw Lz Ma Mb Mc Me Mf Mg Mh Mj Mk Ml Mm Mn Mp Mq Mr Mu Mv Mw Mx My Mz Na Nb Nh Ni Nj Nk Nm Nn No Nq Nr Ns Nt Nu Nv Nw Nx Ny Oe Oh Oi On Oy Pb Pc Pd Pe Pf Pg Po Pz Qa Qb Qc Qd Qe) Lv(Fp Fr Hr Hu Hv Ih Il Im Io Ip Ir Is It Iv Jg Jh Jk Jl Jm Jn Jp Jr Lh Li Lj Lu Lw Lz Ma Mb Mc Me Mf Mg Mh Mj Mk Ml Mm Mn Mp Mq Mr Mu Mv Mw Mx My Mz Na Nb Nh Ni Nk Nm Nn No Nr Ns Nt Nu Nv Nw Nx Ny Oe Oh Oi On Oy Pb Pc Pd Pe Pf Pg Po Pz Qa Qb Qc Qd Qe) Nj(Fr Hr Hu Hv Ih Ij Il Im Io Ip Ir Is It Iv Jg Jh Jk Jl Jm Jn Jr Lh Li Lj Lu Lw Lz Ma Mb Mc Me Mf Mg Mh Mj Mk Ml Mm Mn Mp Mq Mr Mu Mv Mw Mx My Mz Na Nb Ng Nh Ni Nk Nm Nn No Nq Nr Ns Nt Nu Nv Nx Ny Oe Oh Oi On Oy Pb Pc Pd Pe Pf Pg Po Pz Qa Qb Qc Qd Qe) Fp(Fr Hr Hu Hv Ih Il Im Io Ip Ir Is It Iv Jg Jh Jk Jl Jm Jn Jp Jr Lh Li Lj Lu Lw Ma Mb Mc Me Mf Mg Mh Mj Mk Ml Mm Mn Mp Mq Mr Mu Mv Mw Mx My Mz Na Nb Ng Nh Ni Nk Nm Nn No Nr Ns Nt Nu Nv Nw Nx Ny Oe Oh Oi On Oy Pb Pc Pd Pe Pf Pg Pz Qa Qb Qc Qd Qe) aA(Fr Hr Hu Hv Ih Il Im In Io Ip Ir Is It Iv Jg Jh Jk Jl Jm Jn Jp Lh Li Lj Lu Lw Lz Ma Mb Mc Me Mg Mh Mi Mj Mk Ml Mm Mp Mq Mr Mu Mv Mw Mx My Mz Na Nb Ng Ni Nk Nm Nn No Nr Ns Nt Nu Nv Nw Nx Ny Oe Oh Oi On Oy Pb Pc Pd Pe Pf Pg Po Pz Qa Qb Qc Qd Qe) Et(Fr Hr Hu Hv Ih Ii Ij Im In Io Ip Ir Is It Jg Jh Jk Jl Jm Jn Jp Lh Li Lu Lw Lz Ma Mb Mc Me Mf Mg Mh Mj Mk Ml Mm Mn Mp Mq Mr Mu Mv Mw Mx My Mz Na Nb Ng Ni Nm Nn No Nr Ns Nt Nu Nv Nw Nx Ny Oe Oh Oi On Oy Pb Pc Pd Pe Pf Pg Po Pz Qa Qb Qc Qd Qe) Nq(Hq Hr Hu Hv Ih Ii Ij Im In Io Ip Ir Is It Jh Jk Jm Jn Lh Li Lj Lu Lw Lz Ma Mb Mc Me Mf Mg Mh Mj Mk Ml Mm Mn Mp Mq Mr Mu Mv Mw Mx My Mz Na Nb Ng Nh Ni Nk Nm Nn No Nr Ns Nt Nu Nv Nw Nx Ny Oe Oh Oi On Oy Pb Pc Pd Pe Pf Pg Po Pz Qa Qb Qc Qd) Nh(Fr Hq Hr Hu Hv Ih Ii Ij Im In Ip Iq It Iu Iv Jg Jh Jk Jl Jm Jn Jp Jr Lh Li Lj Lu Lz Ma Mb Mc Me Mf Mg Mh Mj Mk Ml Mm Mn Mp Mq Mr Mv Mx My Na Ng Ni Nk Nm Nn Nr Ns Nt Nu Nv Nw Ny Oe Oh Oi On Oy Pb Pc Pd Pe Pf Pg Po Pz Qa Qb Qc Qd Qe) Ii(Fr Hq Hr Hu Hv Ih Ij Im In Ip Iq Ir Is It Iu Iv Jg Jh Jk Jl Jm Jn Jp Lh Li Lj Lu Lz Ma Mb Mc Me Mf Mg Mk Ml Mm Mn Mp Mq Mr Mu Mx My Na Nb Ng Ni Nk Nm Nn Nr Ns Nt Nu Nw Nx Ny Oe Oh Oi On Oy Pb Pc Pd Pe Pf Pg Po Pz Qa Qb Qc Qd Qe) In(Fr Hq Hr Hu Hv Ij Im Ip Ir Is It Iu Iv Jg Jh Jk Jm Jn Jp Lh Li Lj Lu Lw Lz Ma Mb Mc Me Mf Mg Mj Mk Ml Mm Mn Mp Mq Mu Mv Mw Mx My Mz Na Nb Ng Ni Nm Nn No Nr Ns Nt Nu Nw Nx Ny Oe Oh Oi On Oy Pb Pc Pd Pe Pf Pg Po Pz Qa Qb Qc Qd) Iu(Fr Hq Hr Hu Hv Ih Ij Im Ip Ir Is It Iv Jg Jh Jk Jl Jm Jn Jp Jr Lh Lj Lu Lz Ma Mb Mc Me Mf Mg Mk Ml Mm Mn Mp Mq Mr Mv Mw Mx My Na Nb Ng Ni Nk Nm Nn Nr Ns Nt Nu Nv Nw Ny Oe Oh Oi On Oy Pb Pc Pd Pe Pf Pg Po Pz Qa Qb Qc Qe) Nk(Fr Hq Hr Hu Hv Ih Ij Im Ip It Iv Jg Jh Jk Jl Jm Jn Jp Jr Lh Lj Lu Lz Ma Mb Mc Me Mf Mg Mh Mj Mk Ml Mm Mn Mq Mr Mv Mw Mx My Na Nb Ng Ni Nm Nn Ns Nt Nv Nw Ny Oe Oh Oi On Oy Pb Pc Pd Pe Pf Pg Po Pz Qb Qc Qd Qe) Jr(Fr Hq Hr Hu Ih Ij Il Im Ip It Iv Jg Jh Jk Jl Jm Jn Jp Lj Lu Lz Ma Mb Mc Me Mf Mg Mh Mj Mk Ml Mm Mn Mp Mq Mr Mv Mw Mx My Na Ng Ni Nm Nn No Ns Nt Nu Nv Nw Ny Oe Oh Oi On Oy Pb Pc Pd Pe Pf Pg Po Qb Qc Qd Qe) Hq(Fr Hr Hv Ih Ij Im Io Ip Ir Is It Iv Jg Jk Jm Jn Jp Js Lh Li Lj Lu Lz Ma Mb Mc Me Mf Mg Mh Ml Mm Mn Mp Mq Mu Mw Mx My Mz Na Nb Ng Ni Nm Nn Nr Ns Nt Nu Nv Nx Oe Oh Oi Oy Pc Pe Pf Pg Qa Qb Qc Qe) Nw(Hr Hu Hv Ih Ij Il Im Ip Ir It Iv Jg Jh Jk Jl Jn Jp Lh Lj Lz Ma Mb Mc Me Mf Mg Mh Mi Mj Ml Mm Mn Mq Mr Mv Mw Mx My Na Nb Ng Nm No Ns Nt Nu Nv Ny Oe Oh Oi Oy Pb Pc Pd Pe Pf Pg Po Qa Qb Qc Qd Qe) Md(Hr Hu Hv Ih Im Io Ip Ir Is It Jh Jk Jm Jn Lh Li Lj Lu Lw Lz Ma Mc Me Mf Mg Mh Mj Mk Ml Mm Mn Mp Mq Mu Mv Mx My Mz Na Nb Ng Ni Nm Nn No Nr Ns Nt Nu Nv Ny Oe Oh

Figure 9 Continued

Figure 9 Continued

Oe Oy Pb Pc Pd Pe Qa Qb Qe) Qe(Hq Hr Hx Ih Ii Ij Ip Iu Jg Jk Jl Jm Jq Js Lx Lz Ma Mb Mc Mf Mg Mj Ml Mn Mq Ms Mv Mx My Ng Ni Ns Nt Ny Oe Oy Pb Pc Pd Po Qb Qc Qd) Nd(aX Hr Hu Hx Ij It Jh Jk Jm Jq Lu Lw Lz Mb Mf Mh Mj Ml Mn Mq Mu Mv Mw Na Ni Nm Nn No Nv Nx Ny Oe Oh Oi Oy Pf Po Pz Qc Qd) Iu(Fr Hq Hx Ih Im In Ir It Jg Jl Jn Jp Js Lh Ma Mb Mc Mf Mg Mk Ml Ms Mv Mx My Nb Ng Nr Ns Nt Nu Oh Oi Pb Pc Pe Pf Pg Qa Qb) Pb(Hq Hu Hx Ih Ii Ij Im In Ip Ir Is It Jg Jl Js Lz Ma Mb Mc Me Mf Mg Mn Ms Mv My Ng Ns Nt Nu Oy Pd Pe Qa) Ih(Hq Hx Ii Ij Ip It Jg Jl Jq Js Lz Ma Mb Mc Mf Mg Mj Mn Ms Mx My Na Ng Ni Nt Ny Oe Pc Pd Qb Qc) Lx(Hv Il Io Ir Is It Jn Jp Lh Li Lu Lw Mh Mz Nb Nx Oi Pf Pz Qa Qd) Jg(Hq Hu Ii Ij In Jk Jl Js Ma Mb Mc Mf Mg Ms Mu Nm Ns Ny Oy Pc Pd) Jl(Hq Hx Ii Ij In Ip Js Lz Ma Mb Mc Mf Ms Mx My Ng Nt Oy Pd Pg) Nt(Hq Ii Ij In Ip Js Ma Mc Mg Ms Mv My Ng Oe Pc Pd Pe) Ou(aX Bg Co Dk Gl Hq Ii Ij Jo Ly Om Pg Po Ut Vu) Js(Hv Im Jn Jp Mb Mf Mk My Ng Nu Oh Pc Pe Qa) In(Im Is Lh Mf Mk Nb Nu Pc Pe Qa Wm) Ly(Aa Ao Bg bV Dk Gn gP Kg Ut) Mt(Il Io Ir Is It Mz Nx Qa) Ng(Fr Lh Mb Nx Oi Pc Pe Qa) aX(Bg bN cE gP Ii Jo Ma Oe) Pc(Hq Ii Lz Ma Ms Oy Pd) Wm(Hq Ii Ij Mj Om Pg) Dk(Gl gP Jf Or Qy) My(Fr Lh Nb Nx Pc) Qa(Ii Ij Ma Ms Qc) Hq(Lh Mk Mp Nr) Om(bV Dc Gl Il) Mb(Mc Me Ml) Pc(Ms Mv Oy) Fr(Ma Mv) Il(Nc Ne) gP(bV Kk) AaNl GlJo NrLz Mklj MpPd liLh} Lx{Nj(aX Fp Fr Hq Hr Hu Hv Hx Ih Ii Ij Ik Il Im Iq Iv Jg Jh Jk Jl Jm Jn Jp Jq Jr Jt Lh Li Lj Lu Lw Lz Ma Mb Mc Me Mf Mg Mh Mj Mk Ml Mn Mp Mq Ms Mu Mv Mw Mx My Mz Na Nb Nc Ne Ng Nh Ni Nk Nm Nn No Nq Nr Ns Nt Nu Nv Nx Ny Oe Of Oh Oi Oy Oz Pb Pc Pd Pe Pf Pg Pz Qa Qb Qc Qd Qe) Lv(Fp Fr Hq Hr Hu Hv Hx Ih Ii Ij Ik Il Im Ip Iq Iu Iv Jg Jh Jk Jl Jm Jn Jp Jq Jr Jt Lh Li Lj Lu Lw Lz Ma Mb Mc Me Mf Mg Mh Mj Mk Ml Mm Mn Mp Mq Mr Ms Mu Mv Mw Mx My Mz Na Nb Ng Nh Ni Nk Nm Nn No Nr Ns Nt Nu Nv Nw Nx Ny Oe Of Oh Oi Oy Pb Pc Pd Pe Pf Pg Pz Qa Qc Qd Qe) Nq(Fp Fr Hq Hr Hu Hv Hx Ih Ii Ij Ik Im In Io Iq Iu Iv Jh Jk Jm Jn Jo Jq Jr Js Jt Lh Li Lj Lu Lw Lz Ma Mb Mc Me Mf Mg Mh Mj Mk Ml Mn Mp Mq Ms Mu Mv Mw Mx My Mz Na Nb Ng Nh Ni Nk Nm Nn No Nr Ns Nt Nu Nv Nx Ny Oe Of Oh Oi Oy Oz Pb Pc Pd Pe Pf Pg Pz Qa Qb Qc Qd Qe) Ne(Fp Fr Hr Hu Hv Hx Ih Ii Ij Ik Il Im Io Ip Iq Ir Is It Iv Jh Jk Jl Jm Jn Jp Jq Jr Jt Lh Li Lj Lu Lw Ma Mb Mc Me Mf Mg Mh Mj Mk Ml Mn Mp Mq Ms Mu Mv Mw Mx My Mz Na Nb Nc Ng Nh Nm Nn No Nr Ns Nt Nu Nv Nx Ny Oe Of Oh Oi Oy Oz Pb Pc Pd Pe Pf Pg Pz Qa Qb Qc Qd Qe) Mt(Fp Fr Hr Hu Hv Hx Ih Ik Il Im Io Ip Ir Is It Iv Jg Jh Jl Jm Jn Jp Jq Jr Jt Lh Li Lj Lu Lw Lz Ma Mb Mc Me Mf Mg Mh Mj Mk Ml Mm Mn Mp Mq Mu Mv Mw Mx My Mz Na Nb Nh Ni Nk Nm Nn No Nr Ns Nt Nu Nv Nx Ny Oe Oh Oi Oy Pb Pc Pd Pe Pf Pg Pz Qa Qb Qc Qd Qe) Nw(Fp Fr Hq Hr Hu Hv Ih Il Im Ip It Iu Iv Jg Jh Ji Jk Jl Jm Jn Jp Jq Jr Lh Li Lj Lu Lw Ma Mb Mc Me Mf Mg Mh Mj Mk Ml Mm Mn Mp Mq Mr Mu Mv Mw Mx Mz Na Nb Ng Nh Ni Nk Nm Nn No Nr Ns Nu Nv Nx Oe Of Oh Oi On Oy Pa Pb Pc Pd Pe Pf Pg Pz Qa Qb Qc Qd Qe) Nc(Fp Fr Hu Hv Ih Ii Ij Il Im Io Ip Iq Ir Is It Iv Jh Jk Jm Jn Jo Jp Jq Jr Jt Lh Li Lj Lu Lw Ma Mb Mc Me Mf Mg Mh Mj Mk Ml Mn Mp Mq Ms Mu Mv Mw Mx My Mz Na Nb Ng Nh Nm Nn No Nr Ns Nt Nu Nv Nx Ny Oe Of Oh Oi Oy Pc Pd Pe Pf Pg Pz Qa Qc Qd Qe) Po(Fr Hq Hr Hu Hx Ih Ii Ij Im In Iq Iu Iv Jh Jk Jm Jn Jo Jp Jq Jr Js Jt Lh Li Lj Lw Lz Ma Mb Mc Me Mf Mg Mj Mk Ml Mn Mp Mq Ms Mu Mv Mw Mx My Mz Na Nb Ng Ni Nk Nm Nn No Nr Ns Nu Nv Nx Oe Of Og Oh Oi Oy Oz Pb Pc Pd Pe Pf Pg Pz Qa Qb Qc Qd Qe) Md(Fp Fr Hq Hr Hu Hv Hx Ih Ii Ij Im In Iq Iu Iv Jh Jk Jl Jm Jn Jo Jp Jq Jr Js Jt Lh Li Lj Lu Lw Lz Ma Mb Mc Me Mf Mg Mh Mj Mk Ml Mn Mp Mq Ms Mu Mv Mx My Mz Na Ng Ni Nk Nm Nn No Nr Ns Nu Nv Ny Oe Of Oh Oi Oy Pd Pe Pf Pg Pz Qa Qb Qc Qd Qe) Hw(Fp Fr Hr Hu Hv Hx Ii Ij Il Im Io Ip Iq Ir Is It Iv Jh Jk Jm Jn Jo Jp Jq Jr Jt Li Lj Lu Lw Lz Ma Mb Mc Me Mf Mh Mj Mn Mp Mq Ms Mu Mv Mw Mx My Mz Na Nb Ng Ni Nk Nm Nn No Ns Nu Nv Nx Ny Oe Of Oh Oi Oy Pb Pc Pd Pf Pg Pz Qa Qb Qc Qd Qe) aA(Fr Hq Hr Hu Hv Ih Il Il Im Io Ip Ir Is It Iv Jg Jh Jl Jm Jn Jo Jp Jq Lh Li Lj Lu Lw Ma Mb Mc Me Mg Mh Mj Mk Ml Mn Mp Mq Mr Ms Mu Mw Mx My Mz Na Nb Ng Ni Nk Nm Nn No Nr Ns Nt Nu Nv Nx Ny Oe Oh Oi Oy Pd Pe Pf Pg Pz Qa Qb Qc Qd Qe) Ik(Fp Fr Hr Hu Hx Ih Ii Ij Il Iq Iu Jg Jh Jk Jl Jm Jn Jp Jq Jr Js Jt Lh Lj Lu Lw Lz Ma Mc Me Mf Mg Mh Mj Mk Ml Mm Mn Mq Mr Ms Mv Mw Mx My Na Nb Ng Nh Ni Nk Nm Nn No Nr Ns Nt Ny Oe Of Oh Oi Oy Oz Pb Pc Pd Pe Pg Pz Qa Qb Qc Qd Qe) Nf(Hq Hr Hu Hv Ih Ii Ij Im Io Ip Iq Ir Is It Iu Iv Jh Jk Jm Jn Jo Jp Jq Jt Li Lj Lu Lw Lz Ma Mb Mc Me Mf Mg Mh Mj Ml Mn Mp Mq Ms Mu Mv Mw Mx My Mz Na Ng Ni Nk Nm Nn No Ns Nu Nv Nx Ny Oe Oh Oi Oy Pd Pf Pg Pz Qa Qb Qc Qd Qe) Og(Fp Fr Hq Hr Hu Hx Ih Ii Ij Im In Iq Iu Iv Jh Jk Jl Jn Jo Jp Jq Jr Js Jt Lh Lu Lw Lz Ma Mb Mc Mf Mg Mh Mj Mk Ml Mm Mn Mq Ms Mv Mx My Mz Na Nb Ng Nh Ni Nk Nm No Nr Ns Nu Nx Ny Of Oh Oi Oy Oz Pb Pc Pd Pe Pf Pg Qb Qc Qe) On(Fp Fr Hr Hu Hv Ih Im Io Ip Ir Is It Iv Jg Jh Ji Jl Jm Jn Jp Jq Jr Lh Li Lj Lu Lw Ma Mb Mc Me Mf Mg Mh Mj Mk Ml Mm Mn Mp Mq Mr Mu Mw Mx Mz Na Ni Nk Nm Nn No Nr Ns Nt Nu Nx Oe Oh Oi Pb Pc Pd Pe Pf Pz Qa Qc Qd Qe) Mi(Fp Fr Hr Hu Hv Ih Ii Il Im Io Ip Ir Is It Iv Jh Jk Jl Jm Jn Jp Jq Jr Jt Lh Li Lj Lu Lw Mb Mc Me Mf Mg Mk Mm Mn Mp Mq Mr Mu Mw Mx Mz Na Nb Ng Ni Nk Nm Nn No Nr Ns Nt Nu Nv Nx Oe Oh Oi Oy Pc Pe Pz Qa Qb Qc Qd Qe) Pa(Fp Fr Hr Hu Hx Ih Ii Ij Il Im Iq Iu Iv Jg Jk Jl Jm Jo Jp Jq Jr Js Jt Lh Lj Lw Lz Ma Mb Mc Mf Mg Mh Mj Mk Ml Mm Mn Mr Ms Mv Mx My Na Ng Nh Ni Nk No Nr Ns Nt Nu Ny Oe Of Oh Oi Oy Oz Pb Pc Pd Pe Pf Qb Qc Qe) Nd(Hq Hv Ii Ij Il Io Ip Iq Ir Is It Iv Jh Jk Jm Jn Jq Jr Jt Li Lj Lu Mb Mc Mf Mg Mh Mj Mn Mp Mq Ms Mu Mv Mw Mx My Mz Na Nb Ng Nk Nm Nn No Ns Nu Nv Nx Ny Oe Oh Oi Oy Pd Pf Pg Pz Qa Qb Qc Qd) Mr(Fp Hr Hu Hv Ih Ii Il Im It Iu Iv Jg Jk Jm Jo Jp Jq Jr Js Jt Lj Ma Mb Mc Me Mf Mg Mh Mk Ml Mm Mn Ms Mv Mx My Mz Na Nb Ng Nh Ni Nk No Nr Ns Nt Ny Oe Of Oh Oi Oz Pb Pc Pd Pf Pg Qb Qc Qd Qe) Jg(Fp Fr Hq Hr Hu Hx Ih Ii Il Im Iq Iu Jh Jl Jm Jq Jr Lj Lu Lz Ma Mb Mc Me Mf Mg Mj Mk Ml Mm Mn Mp Mq Ms Mu Mw Mx Nh Ni Nk Nm Nn No Nr Ns Nt Nu Nv Ny Oe Oy Oz Pb Pc Pd Pe Pz Qb Qc) In(Fp Fr Hq Hr Hx Ih Ii Ij Im Iq Is Iu Jn Jo Jp Jq Jr Js Jt Lh Lj Lw Lz Ma Mb Mc Mf Mg Mj Mk Ml Mm Mn Mq Ms Mw Mx Mz Nb Ng Ni Nk No Nr Nu Nx Of Oi Oz Pb Pc Pe Pg Qa Qc Qd Qe) Ji(Fr Hu Hv Il Im Io Ip Ir Is It Jh Jl Jm Jn Jp Lh Li Lj Lu Lw Me Mf Mg Mk Mp Mu Mw Mz Na Nb Nk Nm Nn No Nr Nt Nu Nx Oe Oh Oi Pe Pf Pg Pz Qa Qd Qe) Jj(Hq Hr Hu Hv Ii Ij Il Io Ip Ir Is It Iu Jh Jk Jn Jo Jq Li Lj Lu Lw Me Mj Mn Mp Mq Mu Mv Mw Mx My Mz Na Ng Nm Nn No Ns Nv Ny Oe Of Oh Pd Pf Qa Qd) Nh(Fp Hq Hr Hu Hx Ih Ii Ij Iq Iu Jk Jl Jm Jo Jp Jr Js Jt Lz Ma Mc Me Mj Mk Ml Mm Ms Mx Ng Ni Nk Nr Ns Nt Of Oz Pb Pc Pd Pe Qb Qc) Mm(Fp Hq Hr Hx Ih Ii Ij Iq Iu Iv Jk Jl Jm Jr Js Jt Lz Ma Mb Mc Mf Mk Ml Ms Mv My Ng Ni Nk Nr Nt Ny Of Oz Pb Pc Pd Pe Qb Qc) Js(Fp Fr Hx Ih Im Iq Iu Iv Jl Jn Jo Jp Jr Lh Lz Mb Mf Mg Mk Ml Ms Mz Nb Ng Ni Nk No Nr Nt Nu Nx Of Oi Oz Pb Pc Pe Qe) Jl(Hr Hx Ii Ij Il Iq Iu Jk Jo Jr Jt Lz Mb Mf Mj Ml Ms Mx Ng Nt Of Oy Oz Pb Pc Pd Pg Qb Qc) Oz(Fp Hq Hx Ii Il Iq Iu Jo Jp Jr Lh Lz Ma Mk Ml Ms Ng Ni Nr Nt Of Pc Pd Pe Qb Qc Qe) Iq(Fp Fr Hx Ih Im Iu Iv Jo Jp Jr Jt Lh Ly Lz Mk Ml Nb No Nr Nt Of Pb Pc Pe Qe) Nt(Hq Hx Ii Ij Iu Jk Jo Jt Lz Ml Ms Ng Of Pb Qb Qc) Lz(Fp Hx Ih Iu Jo Mf Mj Mk Ms Ng No Nr Of Pb Pe) Hx(Fp Iu Jo Jp Lh Mk Ml Nr Of Pb Pc Pe Qe) Jo(Fp Iv Jt Lh Mf Mg Mk Nr Pb Pc Pe Qe) Iu(Fp Ih Iv Lh Mf Mk Ms Nr Pb Pe Qe) Ly(Aa fR Io Ip Ir Is It) Of(Jp Mg Mk Ml Pb Pc) Nl(Aa Io Ip Ir Is) Ng(Fr Jp Mg Pb) Hq(Fp Mk Nr Pe) Pc(Ms Mv My Oy) Om(Aa Il It) Fp(Jp Ml) Qe(Qb Qc) Jr(Il Iv) MbMl MfJp MkIj liLh OyPe} Nw{Nj(aX Fp Fr Hq Hr Hu Hv Hx Ih Ii Ij Ik Il Im Io Ip Iq Ir Is It Iv Jg Jh Ji Jk Jl Jm Jn Jp Jr Jt Lh Li Lj Lu Lv Lw Lz Ma Mb Mc Me Mf Mg Mh Mj Mk Mm Mn Mp Mq Mr Ms Mu Mv Mw Mx Mz Na Nb Nc Ng Nh Ni Nk Nm Nn No Nq Nr Ns Nt Nu Nv Nx Ny Oe Of Oh Oi On Oy Oz Pb Pc Pd Pe Pf Pg Po Pz Qa Qb Qc Qd Qe) Mt(aA Fp Fr Hq Hr Hu Hv Hx Ih Ik Il Im Io Ip Ir Is It Iv Jg Jh Ji Jk Jl Jm Jn Jp Jr Jt Lh Li Lj Lu Lv Lw Lz Ma Mb Mc Me Mf Mg Mh Mj Mk Mm Mn Mp Mq Mr Ms Mu Mv Mw Mx Mz Na Nb Nh Ni Nk Nm Nn No Nr Ns Nt Nu Nv Nx Oe Oh Oi On Oy Pb Pc Pd Pe Pf Pg Po Pz Qa Qb Qc Qd Qe) Hw(aA Fr Hr Hu Hv Hx Ii Ij Il Im Io Ip Ir Is It Iu Jg Jh Jk Jl Jm Jn Jo Jp Jq Jr Jt Lh Li Lj Lu Lw Lz Ma Mb Mc Me Mf Mg Mh Mj Mk Mm Mn Mp Mq Mr Ms Mu Mv Mw Mx Mz Na Nb Ng Ni Nk Nm Nn No Nr Ns Nt Nu Nv Nx Ny Oe Of Oh Oi Oy Pb Pc Pd Pe Pf Pg Po Pz Qa Qb Qc Qd Qe) Jj(aA Fp Fr Hq Hx Ih Ii Ij Im In Io Ip Ir Is It Iu Jg Jh Ji Jl Jm Jn Jo Jp Jq Jr Js Jt Lh Lj Lz Ma Mb Mc Me Mf Mg Mh Mi Mk Ml Mm Mn Mp Mq Mr Ms Mu Mv Mw Mx My Mz Na Nb Ng Nh Ni Nk Nq Nr Ns Nu

Figure 9 Continued

Nv Nx Ny Of Og Oi On Oy Pb Pc Pd Pe Pf Pg Po Pz Qa Qb Qc Qd Qe) Iq(aA Fp Fr Hq Hr Hu Hv Hx Ih Ii Ij Ik Im In Ir It Iu Iv Jg Jh Ji Jk Jl Jm Jn Jo Jp Jq Jr Js Jt Lh Li Lj Lv Ly Lz Ma Mb Mc Mf Mg Mk Ml Mm Mp Mr Ms Mv Mx My Ng Nh Nk Nq Nr Ns Nt Nv Ny Of Oi On Oy Oz Pb Pc Pd Pe Pf Pg Po Pz Qa Qb Qc Qd Qe) Og(aA Fp Hq Hr Hu Hv Hx Ih Ii Ij Im In Io Ip Ir Is It Iu Iv Jg Jh Ji Jk Jl Jm Jn Jo Jp Jq Jr Jt Lj Lz Ma Mb Mc Mf Mg Mh Mi Mj Mk Ml Mm Mn Mr Ms Mv Mx My Na Ng Nh Nk Nn Nq Nr Ns Nt Nu Nv Ny Of Oi On Oy Pb Pc Pd Pe Pg Po Qa Qb Qc Qd Qe) Pa(Fp Hq Hr Hu Hx Ih Ii Ij Il Im Ip It Iu Iv Jg Jh Ji Jk Jl Jm Jn Jo Jp Jq Jr Jt Lj Lz Ma Mb Mc Mf Mg Mh Mi Mj Ml Mm Mn Mq Mr Ms Mu Mv Mw Mx My Mz Na Ng Nh Ni Nk Nn No Nq Ns Nt Nu Nv Ny Oe Of Oh Oi On Oy Oz Pd Pf Pg Po Qb Qc Qd Qe) Ne(Fp Fr Hr Hu Hv Ih Ik Il Im Io Ip Ir Is It Iv Jg Jh Jk Jl Jm Jn Jp Lh Li Lj Lu Lw Ma Mb Mc Mf Mg Mh Mj Mk Mn Mp Mq Mr Mu Mv Mw Mz Na Nb Nc Ng Nh Ni Nm Nn No Nq Nr Ns Nt Nu Nv Nx Oe Oh Oi Oy Pb Pc Pd Pe Pf Pg Pz Qa Qd Qe) In(aA Fr Hq Hr Hu Hv Hx Ii Im Ip Ir Is It Iu Jg Jh Ji Jk Jl Jm Jn Jo Jp Jq Jr Js Jt Lh Lj Lv Lz Ma Mb Mc Me Mf Mg Mk Ml Mm Mn Mr Ms Mv My Ng Nh Nk Nm Nq Nr Ns Nt Nu Ny Of Oi On Oy Oz Pb Pc Pd Pe Pf Pg Po Pz Qa Qb Qc Qd Qe) Ik(aA Fp Hq Hr Hu Hv Hx Ih Il Ip It Iu Iv Jg Jh Ji Jk Jl Jm Jn Jp Jq Jr Lh Lj Lv Ly Lz Ma Mc Me Mg Mh Mj Mk Ml Mm Mn Mq Mr Ms Mu Mv Mw Mx Ng Nh Nk Nm Nn Nq Ns Nv Ny Oe On Oy Oz Pb Pc Pd Pg Po Pz Qa Qb Qc Qd Qe) Mi(aA Fp Hr Hu Hv Ih Ii Im Ip Ir It Iu Iv Jg Jh Ji Jk Jl Jn Jo Jp Jq Jr Jt Lj Lv Lz Ma Mb Mc Mf Mg Mh Mj Mm Mn Mp Ms Mu Mv Mw Mx My Mz Na Nb Ng Nh Ni Nk Ns Nt Nv Oh Oi Oz Pb Pc Pd Pf Qb Qc Qd Qc) Nf(aX Hq Hr Hu Hv Ii Ij Il Io Ip Ir Is It Jh Jk Jm Jn Jp Li Lu Lw Ma Mb Mc Me Mf Mg Mh Mj Mn Mp Mq Mu Mv Mw Mx My Mz Na Nb Ng Ni Nm Nn No Nr Ns Nu Nv Nx Ny Oe Oh Oy Pd Pf Pg Po Pz Qa Qb Qd) Ly(aX Fp FR Gn Hv Im Io Ip Ir Is It Iv Jk Jl Jm Jn Lh Li Lu Lw Ma Mb Mc Me Mf Mg Mh Mj Mk Mn Mp Mq Mr Mu Mv Mw Mz Na Nb Nh Ni Nk Nm Nn No Nr Ns Nt Nu Nx Oe Oh Oi Pb Pc Pe Pf Pz Qa Qd) Nd(Fr Hr Hv Ij Il Io Ir Is It Jh Jk Jm Jn Lh Li Lu Lw Ma Mb Mc Mf Mg Mh Mj Mk Mn Mp Mq Mu Mw Mx Mz Na Nb Ng Nh Ni Nk Nm Nn No Nq Nr Ns Nt Nu Nv Nx Oc Oh Oi Pb Pc Pd Pe Pf Pg Pz Qb Qc Qd) Js(aA Fp Hq Hu Hx Ih Ii Ij Im It Iu Iv Jg Jh Ji Jl Jo Jp Jq Jr Lj Lv Lz Ma Mb Mc Me Mf Mg Mh Ml Mm Mr Ms Mu Mv Mw My Ng Nh Nk Nq Nr Ns Nt Nu Nv Ny Of Oi On Oy Oz Pb Pc Pd Pe Pg Po Qa Qe) Lv(aA Fp Hq Hr Hu Hx Ih Ii Ij Il Im Iu Iv Jg Jh Ji Jk Jl Jm Jn Jp Jq Jr Jt Lj Lz Ma Mc Me Mh Mj Ml Mm Mr Ms Mu Mv Mx My Ng Nh Nk Nq Ns Nv Ny Of On Oy Oz Pb Pd Pg Po Qb Qc Qd Qe) Oz(Fp Hq Hu Hx Ih Ii Ij Il Im Iu Iv Jg Jh Ji Jl Jo Jp Jq Jr Jt Lj Lz Ma Mc Mh Ml Mm Mn Mr Ms Mv My Ng Nh Nk Nq Ns Nt Nv Ny Of On Oy Pd Po Qb Qc Qe) aA(Fp Hq Hu Hx Ih Ii Ij Il Ir It Iu Iv Ji Jk Jl Jn Jo Jq Jr Jt Lj Lz Ma Mb Mc Mf Ml Mm Mn Ms Mv Mx My Ng Nh Nk Ns Nt Nv Ny Of Oy Pb Pc Pg Po) My(Fp Fr Hx Ii Iu Iv Jh Ji Jl Jo Jq Jr Jt Lz Mb Md Ml Mm Mr Ms Mw Nh Nk Nq Nt Of Oi On Pb Pc Qc Qe) Nq(Fp Fr Hq Hx Ih Ip It Iu Iv Jg Ji Jl Jo Jp Jq Jr Lz Ml Mm Mr Ms Nh Nk Nt Ny Of On Po Qa Qe) Ms(Fp Hq Hx Iu Iv Jg Ji Jo Jr Jt Lz Ma Ml Mm Mr Nh Nk Nt Ny Of On Pb Pc Pd Po Qc Qc) Jo(Fp Hx Ih It Iv Jg Ji Jl Lz Mb Mf Mg Ml Mm Mr Mv Nh Nk Ns Nt Ny Oi On Pb Pc Qe) Nc(Il Im Io Ip Ir Is Lh Li Lu Lw Mb Mf Mp Mu Nb Nh Nm No Nr Nu Nx Oh Oi Pe Pz) Ml(Fp Hq Hx Ii Iu Iv Jg Ji Jq Jr Jt Lj Lz Mb Mr Nh Nk Ns Nt Of Oy Pb Qe) Of(Fp Hq Hx Iu Iv Jg Ji Jl Jr Lz Mg Mm Mr Nh Nt Ny Oi On Qe) Fp(Hq Hx Ii Ij Iu Jg Ji Jq Jr Jt Lz Mm Ny Pd Po Qb Qc) Iv(Hq Hx Ii Ij Iu Ji Jq Jr Jt Lz Mm Mv Ny Oy Po Qb) Ny(Hx Iu Jg Ji Jl Jr Jt Lz Mr Nb Nh Nk Nt Pb) Nh(Hq Hx Ii Ij Iu Ji Jq Jr Jt Lz Mm Po) Ii(aX Hx Ih Jg Ji Jr Mm Nt On Qe) Ji(Hq Hx Ij Iu Jq Jt Mv Nv Po) On(Hx Ij Jq Jt Mv Nb Nv Pg Po) Lz(Hx Ih Jq Lj Mr Mv Nk) Ij(Ih Jg Jl Mk Nt Qe) Md(Il Is Mv Mz Ng) Mm(Hx Jq Jr Jt Nk) Hq(Jl Mk Nt Pb Pe) Iu(Hx Ih Jg Nt Qe) Mr(aX Nb Pe Pg) Jl(Hx Oy Pg Po) Qe(Jt Qb Qc) Jg(Jh Mu Oy) Jq(aX Jr Nk) Om(aX Lu Nx) Hx(Ih Pb) Jr(Ih Il) Jt(Mg Nt) WmPg OuaX OyPc} Mt{Nd(Fr Hq Hr Hu Hv Hx Ih Ii Ij Ik Im In Io Ip Iq Ir Is It Iv Jh Jk Jm Jn Jo Jq Jr Js Jt Lh Li Lj Lu Lv Lw Ly Lz Ma Mb Mc Me Mf Mg Mh Mj Mk Ml Mn Mp Mq Ms Mu Mv Mw Mx My Mz Na Nb Nc Ne Nf Ng Nh Ni Nj Nk Nm Nn No Nq Nr Ns Nt Nu Nv Nx Ny Oe Of Oh Oi Oy Oz Pb Pc Pd Pe Pf Pg Po Pz Qa Qb Qc Qd Qe) Ly(Aa FR Hq Hr Hu Hv Hx Ih Ii Ij Ik Il Im Iq Iu Iv Jh Jk Jl Jm Jn Jq Jr Js Jt Lh Li Lj Lu Lw Lz Ma Mb Mc Me Mf Mg Mh Mj Mk Ml Mn Mp Mq Ms Mu Mv Mw Mx My Mz Na Nb Ne Nf Ng Nh Ni Nj Nk Nm Nn No Nq Nr Ns Nt Nu Nv Nx Ny Oe Of Oh Oi Oy Oz Pb Pc Pd Pe Pf Pg Po Pz Qa Qb Qc Qd Qe) Pa(Fr Hq Hr Hu Hv Hx Ih Ii Ij Ik Il Im Io Ip Ir Is It Iu Iv Jg Jh Jk Jl Jm Jn Jo Jp Jq Jr Jt Lh Li Lj Lu Lw Lz Ma Mb Mc Me Mf Mg Mh Mj Mk Ml Mn Mp Mq Mr Mu Mv Mw Mx My Mz Na Nb Ng Nh Ni Nk Nm Nn No Nr Ns Nt Nu Nv Nx Ny Oe Oh Oi Oy Oz Pb Pc Pd Pe Pf Pg Po Pz Qa Qb Qc Qd Qe) Nl(Hq Hr Hu Hv Hx Ih Ii Ij Ik Il Im Io Ip Iq Ir Is It Iv Jh Jk Jl Jm Jn Jo Jq Jr Jt Lh Li Lj Lu Lw Lz Ma Mb Mc Mf Mg Mh Mj Mk Ml Mn Mp Mq Ms Mu Mv Mw Mx My Mz Na Nb Nc Nf Ng Nh Nj Nm Nn No Nq Nr Ns Nt Nu Nv Nx Ny Oe Of Oh Oi Oy Oz Pb Pc Pd Pe Pf Pg Po Pz Qa Qb Qc Qd Qe) Hw(Fr Hq Hr Hu Hv Ih Ii Ij Ik Im In Ip Iq Iu Iv Jg Jk Jm Jn Jo Jp Jq Jr Js Jt Lh Li Lj Lu Lw Lz Ma Mb Mc Me Mf Mg Mh Mj Mk Ml Mp Mq Ms Mv Mx My Mz Nb Ne Nf Ng Nh Ni Nj Nk Nm Nn No Nq Nr Ns Nt Nu Nv Nx Oe Of Oh Oi Oy Oz Pb Pc Pd Pe Pf Pg Po Pz Qa Qb Qc Qd Qe) On(aA Fr Hr Hu Hv Hx Ih Ii Ik Il Im Io Ip Ir Is It Iu Iv Jg Jh Ji Jk Jl Jm Jn Jp Jq Jr Js Jt Lh Li Lj Lu Lv Lw Lz Ma Mb Mc Me Mf Mg Mh Mi Mj Mk Ml Mm Mn Mp Mq Mr Mu Mw Mx Mz Na Nh Ni Nk Nm Nn No Nr Ns Nt Nu Nv Nx Oe Oh Oi Pb Pc Pd Pe Pf Pz Qa Qb Qc Qd Qe) Mi(Fr Hr Hu Hv Ih Ii Im Io Ip Ir Is It Iu Iv Jg Jh Jk Jl Jm Jn Jp Jq Jr Jt Lh Li Lj Lu Lv Lw Lz Mb Mc Me Mf Mg Mh Mj Mk Mm Mn Mp Mq Mr Mu Mv Mw Mx My Mz Na Nb Ng Nh Ni Nk Nm Nn No Nr Ns Nt Nu Nv Nx Ny Oe Oh Oi Oz Pb Pc Pd Pe Pf Pz Qa Qb Qc Qd Qe) Fp(aA Fr Hq Hr Hu Hx Ih Ii Ij Ik Il Im Iq Iu Iv Jg Jk Jl Jm Jn Jo Jp Jr Js Jt Lh Lu Lv Lw Lz Ma Mc Me Mh Mj Mk Ml Mm Mq Mr Ms Mv Mx My Nc Ne Nf Ng Ni Nj Nk Nm Nq Nr Ns Nt Ny Of Oz Pb Pc Pd Pe Po Qb Qc) Ji(Fr Hr Hu Hv Ih Il Im Io Ip Ir Is It Iv Jg Jh Jl Jm Jn Jp Jr Lh Li Lu Lw Lz Mb Mc Mf Mh Mk Mp Mr Mu Mw Mx Mz Na Nb Nh Ni Nk Nm Nn No Nr Nt Nu Nx Oe Oh Oi Pb Pc Pe Pf Pg Pz Qa Qd Qe) Lv(aA Hq Hr Hu Ih Ii Ij Ik Im In Iq Iu Iv Jg Jk Jl Jo Jp Jq Jr Js Jt Lj Lz Ma Mc Me Mk Ml Mm Mq Mr Ms Mv Mx My Nc Ne Nf Ng Nh Nj Nk Nq Nr Ns Nt Of Oi Oy Oz Pb Pc Pd Pe Pg Qb Qc Qe) Og(aA Fr Hq Hx Ih Im In Iq Iu Iv Jg Jl Jp Jq Jr Js Jt Lh Li Lj Lw Mb Md Mf Mk Ml Mm Mr Ms Nb Ne Nf Nh Nj Nk Nm No Nq Nr Ns Nt Nu Nx Of Oi Oy Oz Pb Pc Pe Pg Qe) Md(aA Fr Hx Ih Ii Ik Im In Iq Iu Iv Jl Jp Jq Jr Js Lh Li Lj Lw Mb Mk Mm Mp Mq Mr Ms Mw Nb Ne Nf Nh Nj No Nq Nr Nt Nu Nv Ny Of Oi Oz Pb Pe Pg Qe) Nc(aA Fr Ih Ik Im In Iq Iu Jg Jk Jl Jm Jo Jp Jr Js Lh Lj Lw Lz Me Mk Ml Mr Ms Ne Nf Ng Ni Nj Nm Nq Nr Ns Nt Of Oz Pb Pc Pe Qb Qe) Om(Aa aX Hq Hr Hu Hv Hx Ii Ij Il It Jh Jk Jm Jn Jo Lz Mb Mc Mg Mh Mj Mn Mq Mu Mv Mw Mx My Na Ng Nh Nn Ny Oe Of Oy Pd Po Pz Qb Qc) Jj(Hq Hr Hu Hv Il Io Ip Ir Is Iu Jh Jk Jn Jo Jq Lu Mh Mj Mn Mp Mq Mu Mw Mx Mz Na Ng Ni Nn No Nv Ny Oe Of Oh Pd Po Qb Qc Qd) Mr(Hx Ii Ik Il Iq Iu Jg Jk Jo Jp Jr Js Lz Me Mh Ml Mm Ms Mx My Ne Ng Nj Nq Ny Of Oz Pc Pe Pg Po) Mm(aA Ih Ij Ik In Iq Iu Jl Jo Jp Jr Js Jt Lj Mb Mk Ms Nc Nf Ng Nj Nr Ns Of Oz Pb Pc) In(Hx Ih Ik Is Iv Jg Jl Jp Jr Lh Lj Mk Nb Ne Nj Nq Nr Nt Nx Oz Pb Pe Qa Qe) Jg(Hu Ij Iq Jh Jk Jo Js Jt Lj Mg Ms Mu Ne Nf Nj Ns Oy Oz) Nq(aA Fr Iu Iv Jl Jr Lh Lj Mk Nf Nj Nr Nt Oz Pe Qe) Jl(Hq Ij Iq Jo Js Ms Ne Nf Nj Of Oy Oz) Jp(Ik Iq Jk Js Ms Ne Nf Ng Nj Ns Of Oz) Qe(Ij Iq Iu Jk Jo Js Nf Nj Of Qb Qc) Iq(aA Ih Jr Lh Lj Mk Nr Pe) Nc(aA Iu Js Me Nf Nk) Nf(Jr Lh Lj Mk Pe) Nj(aA aX Iu Jo Js) Hq(Mk Pb Pe) Jo(Ik Lh Nt) Jr(aA Il Js) Js(Lj Nt) Pc(My Oy) OuaX OzaA} Ji{Nd(Fr Hq Hr Hu Hv Hx Ii Ij Ik Il Im In Io Ip Ir Is It Iv Jh Jk Jl Jm Jn Jr Js Jt Lh Li Lj Lu Lv Lw Lz Ma Mb Mc Me Mf Mg Mh Mj Mk Ml Mn Mp Mq Mr Ms Mu Mv Mw Mx My Mz Na Nb Ng Nh Ni Nj Nk Nm Nn No Nq Nr Ns Nt Nu Nv Nx Ny Oe Of Oh Oi On Oy Pb Pc Pd Pe Pf Pg Po Pz Qa Qb Qc Qd) Ne(Fr Hq Hr Hu Hv Hx Ih Ii Ij Ik Il Im Io Ip Ir Is It Iv Jh Jk Jl Jm Jn Jr Jt Lh Li Lj Lu Lv Lw Lz Ma Mb Mc Mf Mg Mh Mj Mk Mn Mp Mq Mr Ms Mu Mv Mw Mx My Mz Na Nb Nc Ng Nh Ni Nj Nm Nn No Nq Nr Ns Nt Nu Nv Nx Ny Oe Of Oh Oi On Oy Pb Pc Pd Pe Pf Pg Po Pz Qa Qb Qc Qd Qe) Nc(Fr Hq Hr Hu Hv Hx Ih Ii Ij Ik Il Im Io Ip Ir Is It Iv Jh Jk Jl Jm Jn Jr Jt Lh Li Lj Lu Lw Lz Ma Mb Mc Me Mf Mg Mh Mj Mk Mn Mp Mq Mr Mu Mv Mw Mx My Mz Na Nb Ng Nh Nj Nm Nn No Nq Nr Ns Nt Nu Nv Nx Ny Oe Of Oh Oi On Oy Pb Pc Pd Pe Pf Pg Po Pz Qa Qb Qc Qd Qe) Ly(aX FR Gn Hr

Js Jt Lj Lv Ma Mb Mc Mf Mr Ms My Ng Nh Nk Nq Nt Nw Og On Oz Pb Pc Pe Qa Qe) Lx(Fp Hx Ik In Iq Iu Jg Jl Jo Js Lv Lz Md Mm Mr Mt Nh Nj Nq Nt Nw Of Og Oz Pa Pb Pc Po) Nw(aA Fp Hw Hx Ik In Iq Iv Jj Jo Js Lv Mi Ml Ms Mt My Nh Nj Nq Of Og Oz Pa) Mt(Fp Hw Lv Ly Md Mi Mm Mr Nc Nd Ne Og On Pa) Ji(aA Fp Hw Iq Jj Jq Md Nd Nj Og Oz Pa) On(Hw Iq Jj Ly Nc Nd Ne Nf Of) Jg(Jj Ly Md Mv Nc Ng Nl) Nl(aA Fr Jj Jp Pa) Ly(fR Gn Jp Mi) Mi(Hq Nc Ne) Jj(Ik Nt) aX(Nf Ou) MmNc aJgP

Unconstrained panels with 2 analytes, where 1.0E-5 >= 'model p-value' > 1.0E-6. Contains 541 panels of 81,255 total panels evaluated. : Mt(aA Fr Hq Hr Hu Hv Hx Ih Ii Ij Ik Im In Iq Iu Iv Jg Jh Jk Jl Jm Jn Jo Jp Jq Jr Js Jt Lh Li Lj Lu Lw Lz Ma Mb Mc Me Mf Mg Mh Mj Mk Ml Mn Mp Mq Ms Mu Mv Mw Mx My Mz Na Nb Nf Ng Nh Ni Nj Nk Nm Nn No Nq Nr Ns Nt Nu Nv Nx Ny Oe Of Oh Oi Oy Oz Pb Pc Pd Pe Pf Pg Po Pz Qa Qb Qc Qd Qe) Nw(Fr Hq Hr Hu Hv Ih Ii Ij Il Im Io Ip Ir Is It Iu Jg Jh Ji Jk Jl Jm Jn Jp Jq Jr Jt Lh Li Lj Lu Lw Lz Ma Mb Mc Me Mf Mg Mh Mj Mk Mm Mn Mp Mq Mr Mu Mv Mw Mx Mz Na Nb Ng Ni Nk Nm Nn No Nr Ns Nt Nu Nv Ny Oe Oh Oi On Oy Pb Pc Pd Pe Pf Pg Po Pz Qa Qb Qc Qd Qe) Lx(Fr Hq Hr Hu Hv Ih Ii Ij Il Im Io Ip Ir Is It Iv Jh Jk Jm Jn Jp Jq Jr Jt Lh Li Lj Lu Lw Ma Mb Mc Me Mf Mg Mh Mj Mk Ml Mn Mp Mq Ms Mu Mv Mw Mx My Mz Na Nb Ng Ni Nk Nm Nn No Nr Ns Nu Nv Nx Ny Oe Oh Oi Oy Pd Pe Pf Pg Po Pz Qb Qc Qd Qe) Et(aX Fr Hq Hr Hu Hv Hx Ii Ij Im Io Ip Ir Is It Jh Jk Jm Jn Jp Jq Lh Li Lu Lw Lz Me Mg Mh Mj Mk Ml Mm Mn Mp Mq Mu Mv Mw Mx Mz Na Nb Ni Nm Nn No Nr Ns Nu Nv Nx Ny Oe Oh Oi Oy Pd Pf Pg Po Pz Qb Qc Qd) Ji(Fr Hq Hx Ih Ii Ij Ik Im In Ir Iu Iv Jg Jl Jo Jp Jr Js Li Lj Lv Lz Mb Mc Me Mf Mg Mi Ml Mm Mn Mr Ms Mv My Ng Nh Ni Nk Nq Nr Ns Nt Nu Ny Of Oi On Oy Pb Pc Pe Pf Pg Po Qa Qb Qc Qe) On(Fp Hq Hx Ii Ij Ik In Iu Iv Jg Jk Jo Js Jt Lj Lv Mi Mm Ms Mv My Nb Ng Nh Nj Nq Og Oz Pa Pg) Nl(Aa Fp Hw Jl Lh Li Lj Lv Ly Md Me Mr Mz Ni Nk Nt Nv Nx Og Pc Pe Pg Qe) Ok(Il Io Ir Is It Jm Jn Lh Li Lw Mh Mu Mw Mz Nb No Nr Nv Nx Oy Pf Qd) Pa(aA aX Fp Ik Jg Jj Lv Ly Mi Mm Nc Nd Ne Nh Nj Nt) Jg(Fp Hw Jo Jt Lv Mi My Nd Ne Nf Nq Of Og) Ly(AA bV Fr gP Jj Mm Ou Qe) Mi(Fp Ik Jp Nd Nh Nj Nt Om Qe) Jp(Fp Ik Lv Nc Nd Ne Nj Om) aX(Kc Kk Ko Me Nj Ph Rb) Gn(aV Gl Hu Kc Kk Ra) Mm(aA Fp Ik Lv Nd Ne) Nc(aA Fp Fr Jj Lv) Ne(aA Fr Jj) Fp(aA Jj) Qe(Jj Om) Og(Ik Nt) NfOu Unconstrained panels with 2 analytes, where 1.0E-4 >= 'model p-value' > 1.0E-5. Contains 694 panels of 81,255 total panels evaluated. : Nl(Hq Hr Hu Hv Hx Ih Ii Ij Ik Il Im In Io Ip Iq Ir Is It Iu Iv Jh Jk Jm Jn Jo Jq Jr Js Jt Lu Lw Lz Ma Mb Mc Mf Mg Mh Mj Mk Ml Mn Mp Mq Ms Mu Mv Mw Mx My Na Nb Nc Nd Ne Nf Ng Nh Nj Nm Nn No Nq Nr Ns Nu Ny Oe Of Oh Oi Om Oy Oz Pb Pd Pf Po Pz Qa Qb Qc Qd) On(aA aX Fr Hr Hu Hv Ih Il Im Io Ip Ir Is It Jh Jl Jm Jn Jp Jq Jr Lh Li Lu Lw Lz Ma Mb Mc Me Mf Mg Mh Mj Mk Ml Mn Mp Mq Mr Mu Mw Mx Mz Na Ni Nk Nm Nn No Nr Ns Nt Nu Nv Nx Ny Oe Oh Oi Pb Pc Pd Pe Pf Po Pz Qa Qb Qc Qd Qe) Jg(aA aX Fr Hq Hu Hv Hx Ih Ii Ij Ik Im In Iq Iu Iv Jh Jk Jl Jm Jp Jq Jr Js Lh Li Lj Lw Lz Ma Mb Mc Me Mf Mg Mj Mk Ml Mm Mn Mp Mq Mr Ms Mu Mx Mz Nh Ni Nj Nk Nm No Nr Ns Nt Nu Nx Ny Oe Oy Oz Pb Pc Pe Pf Pg Qa Qc Qe) aX(bA Fp gP Hc Hw Ih Ii Ik In Jf Jj Jk Jp Jq Kd Kn Kp Lj Lv Lx Mb Md Mr Mt Nd Nq Nr Nu Nw Oe Og Ok Om Or Oy Oz Pb Pc Qa Qe Qw Qy Rj Sr St Ur Vp Vq) Ly(aJ aP bA bC bE bN cH cJ cS Dc dE dM Dr EM eP Fp Id Ih Im Jf Jl Kc Ko Kp Lh Li Lj Lv Mr Nc Ne Nt Og Pe Ph Qa Sr Tt) Ji(Hr Hu Hv Il Io Ip Is It Jh Jk Jm Jn Jt Lh Lu Lw Ma Mh Mj Mk Mp Mq Mu Mw Mx Mz Na Nb Nm Nn No Nv Nx Oe Oh Pd Pz Qd) Gn(aJ aN Bb bR bU cF CH cN cP Cs Dl dJ dL Ef Em Fw gP Ld Me Og Or Qw Rb Rc Ue Um Uo Vo) Mi(aA Fr Hw Ih Im In Iq Iv Jj Jr Lh Li Lj Lv Mb Md Ml Mm Nf Nq Nv Nx Og Oi Oz Pb Pc Pe Pg Qa) Nf(aJ bA bV cS dM Fp FR Jp Kc Kk Ko Lh Li Lv Mm Mr Nt Pa Pe Qe Sr Ur) Ou(Bg bV cE Et fR gP gW Hq Jk Kc Ko Me Mk Mu Om Ow Pg Qw Rb Ut Vu Tj) Qe(aA Dc Fp gP Hw Ik In Iq Jp Lv Mm Nc Nd Ne Nh Nj Nt Og Pa Qc) Mm(Hw Ih Iv Jj Jl Jp Jr Lh Lj Md Mr Nh Nj Nt Om Oz Pb Pe) Nc(Hw Ik Iv Jl Lh Li Lj Mr Nd Ni Nk Nt Nv Nx Og Om Pe Pg) Pa(bV Fr Hw Im Iq Iv Jl Jp Jr Lh Li Md Mr Nu Nx Og Om Qa) Lv(aA Fp Fr Ih Ik Iv Jj Li Lj Mr Ne Nh Nj Nt Og Om Qa) gP(bA Bc bV cH Dg Dl dM eF Et fR gL Kc Kk Ko Qy Sr Wm) Jj(aA Fr Im Iv Jl Jp Lh Li Mg Nh Nj Nv Nx Pe Pg Qa) Fp(Fr Hw Ik Iv Jl Lh Md Mr Nd Ne Nh Nt Og Om) aA(Ih Ik Jn Jp Jr Lh Lj Nd Nh Nj Nt Nx Om Pe) Et(Ao Bg bV Co Cw Dc Dk Gl Il Jf Kg Ut Wm) Ne(Aa Hw Iv Jl Lh Li Lj Mr Nt Nv Nx Og Pe) Jp(Hw Iq Iv Md Mf Mr Nh Nq Nt Og Oz) Om(Au Fr Im Jl Lh Li Nt Nv Qa St) Nt(Fr Hw In Md Nd Nj Oz) Mt(Aa Il Io Ip Ir Is It) Fr(Ik Iv Nd Nh Nj) Me(bV Gz Hf Sr) Kc(bN bV cS Em) nD(hV nA rA) Ko(bV fR) Nw(Dc Nx) bA(cH cS) AaLx MdNx NdLh aVdO Unconstrained panels with 2 analytes, where 1.0E-3 >= 'model p-value' > 1.0E-4. Contains 2,438 panels of 81,255 total panels evaluated. : Ly(aC AD aE AF aG aH aI Aj aK AL aM AN AO Ap aQ AR AS aU aV AW Ax aY aZ Ba BB Bc bF BG bH bI bJ bL bM Bn BO bP bQ bR bS bU bW bX bZ cA cB cC cD cE cF cG Ch cI cK cL cM cN CO CP CQ cR Cs CT CU CV CW CX cY cZ dA DB dC DD De dF DG dH DI dJ DK DL dN Dp dX Ed EF Ex Ez Fn Fw Fy Gc GL Gp Gz Ha Hb Hc Hf Hw Ib Ic Ie Io Ir Iv Iz Jd Je Jh Jn Jq Jr Jt Ju Jv Jy Kd Ke Kf Ki Kj Kk Kl Kn Kq Kr Ks Kx Ky Kz Ld Lw Ma Md Mk Mp Mz Nd Nf Nh Nj No Nr Nu Nv Nx Oa Oh Om Or Oz Pb Pc Pf Pg Pj Pk Po Pz Qb Qd Qg Qh Ql Qm Qn Qt Qu Qw Qx Qy Qz Ra Rb Rc Rf Rg Rh Rj Ss St Tn To Tr Tv Tz Ua Ub Uc Ud Ue Uf Ug Uh Uk Ul Um Un Uo Up Ur Ut Uu Uv Vo Vp Vq Vs Vt Vu Vv Tj) Gn(AA aC AD aE AF aG aH aI Aj aK AL aM An AO AP aQ AR AS aU AW AX aY aZ BA bB BC bE bF BG bH bI bJ bL bM BN BO bP bQ bS bV bW bX bZ cA cB cC cD cE cG cl cJ cK cL cM CO Cp CQ cR cS CT CU CV CW CX cY cZ dA DB DC DD DE dF DG dH DK Dl dM dN Do Dp Dq DR Ed eF EX Ez Fa Fb Fp FR Gc gL Gp gW Hb Hf Ib Ic Ih Ii Ij Ik Il In Io Iz Jd Jh Jj Jk Jo Js Jt Ju Jv Jy Kd Ke Kf Kg Kj Kl Kn Ks Ky Lj Lu Ma Mf Mg Mh Mn Mq Mr Mu Mv Mw Mz Nb Nf Ng Nj Nk Nl Nm Nx Ny Oa Of Oh Om Ou Oy Oz Pb Pc Ph Qm Qt Qu Qv Qx Qy Qz Rh Ss St Ua Ub Uf Uh Uk Ul Un Up Uu Vv Tj) Ou(Aa aF aH aI aJ aL AO Ar aU AW Ax bA BC bE bF bJ bL bN bQ bR bS bU cF cG CH cl cL cM Co Cp Cq cR CS Ct Cu Cv Cw cY cZ Dc Dd dE Dg Di Dk Dl dM Ex Ez Fp Fr Fw Gl Gz Ha Hc Hu Hw Hx Ib Id Ih Ii Ij In Io Iq It Iz Jd Je Jf Jj Jl Jm Jn Jo Jp Jq Jr Js Jy Kd Kf Ki Kk Kp Kx Kz Li Lj Lu Lw Lx Lz Ma Md Mh Mi Mj Mm Mn Mp Mq Mr Mt Mv Mw My Nd Nj Nk Nn Nq Nr Ns Nu Nv Nw Oe Of Og Oh Ok Oy Oz Pa Pb Pc Pd Pe Pf Ph Pj Po Qe Qg Ql Qm Qn Qt Qx Qy Ra Rf Rg Rh Ri Rj Rm Sr Tn Ua Ug Uk Ul Uo Ur Vp Vq Vs Vt Wm) aX(Aa aJ cH dG dM Dp Ed Ez Fa Fb Fn Fy Gz Ha Hb Hf Hq Hr Hu Hv Hx Ib Ic Id Ij Il Im Iq It Iv Iz Jd Je Jh Ji Jl Jm Jn Jo Jr Js Jt Ju Jv Jy Ke Kf Kg Ki Kj Kl Kq Kr Ks Kx Ky Kz Ld Lh Li Lu Lw Lz Ma Mc Mf Mg Mh Mi Mj Mk Ml Mm Mn Mp Mq Ms Mu Mv Mw Mx My Mz Na Nb Nc Ne Ng Nh Ni Nk Nl Nm Nn No Ns Nt Nv Nx Ny Oa Of Oh Oi Ow Pd Pe Pf Pg Pi Pj Pk Po Pz Qb Qc Qd Qg Qh Ql Qm Qn Qt Qu Qv Qx Qz Ra Rc Rf Rg Rh Ri Rm Ss Tn To Tr Tt Tv Tz Ua Ub Uc Ud Ue Uf Ug Uh Uk Ul Um Un Uo Up Us Ut Uu Uv Vo Vs Vt Vv Wm) Nf(AA Ad AP Ar As aU aW Ax aZ Ba Bb BC bE Bg bJ bN bW bX bZ cF CH cJ cM Co cP cQ cR Cs cT CU Cv Cx dA Db Dc Dd dE dF DG Di Dl eF Fa Fy gL gP Id Ik Im Iv Jf Jl Kd Kf Kn Kp Kq Ky Lj Nc Ne Nh Nv Nx Or Pg Ph Pj Qa Qw Qy Ra Rb Rf St To Tt Ue Uf Ug Uh Uk Ul Vp Vq Vt Vv Wm) Pa(Aa aJ bA cH cS Dc dM fR gP Ha Hq Hr Hu Hv Hx Ih Ii Ij Il In Io Ip Ir Is It Iu Jf Jh Jk Jm Jn Jo Jq Js Jt Kc Ko Lj Lu Lw Lz Ma Mb Mc Me Mf Mg Mh Mj Mk Ml Mn Mp Mq Ms Mu Mv Mw Mx My Mz Na Nb Ng Ni Nk Nm Nn No Nq Nr Ns Nv Ny Oe Of Oh Oi Oy Oz Pb Pc Pd Pe Pf Pg Ph Po Pz Qb Qc Qd Rb Sr) Nt(Hq Hr Hu Hv Hx Ih Ii Ij Ik Il Im Io Ip Iq Ir Is It Iu Iv Jh Jk Jl Jm Jn Jo Jq Jr Js Jt Lh Li Lj Lu Lw Lz Ma Mb Mc Me Mf Mg Mh Mj Mk Ml Mn Mp Mq Mr Ms Mu Mv Mw Mx My Mz Na Nb Ng Nh Ni Nk Nm Nn No Nq Nr Ns Nu Nv Nx Ny Oe Of Oh Oi Oy Pb Pc Pd Pe Pf Pg Po Pz Qa Qb Qc Qd) Fp(Aa Ha Hq Hr Hu Hv Hx Ih Ii Ij Il Im In Io Ip Iq Ir Is It Iu Jh Jk Jm Jn Jo Jq Jr Js Jt Li Lj Lu Lw Lz Ma Mb Mc Me Mf Mg Mh Mj Mk Ml Mn Mp Mq Ms Mu Mv

Figure 9 Continued

Mw Mx My Mz Na Nb Ng Ni Nj Nk Nm Nn No Nq Nr Ns Nu Nv Nx Ny Oe Of Oh Oi Oy Oz Pb Pc Pd Pe Pf Pg Po Pz Qa Qb Qc Qd) Qe(bA bV Fr Ha Hq Hr Hu Hv Hx Ih Ii Ij Il Im Io Ip It Iu Jf Jh Jk Jl Jm Jn Jo Jq Jr Js Jt Kc Lh Li Lj Lu Lw Lz Ma Mb Mc Md Me Mf Mg Mh Mj Mk Ml Mn Mp Mq Mr Ms Mu Mv Mx My Mz Na Nb Ng Ni Nk Nm No Nq Nr Ns Nu Nv Nx Ny Oe Of Oh Oi Oy Oz Pb Pc Pd Pe Pf Pg Qa Qb Qd Vu) Jp(Dc Fr gP Hq Hr Hu Hv Hx Ih Ii Ij Im In Ip Ir Is It Iu Jh Jk Jl Jm Jn Jo Jq Jr Js Jt Kc Lh Li Lj Lu Lw Lz Ma Mb Mc Me Mg Mh Mj Mk Ml Mn Mp Mq Ms Mu Mv Mw Mx My Mz Na Nb Ng Ni Nk Nm Nn No Nr Ns Nu Nv Nx Ny Oe Of Oh Oi Oy Pb Pc Pd Pe Pf Pg Po Pz Qa Qb Qc Qd Vs) Nc(Aa Hq Hr Hu Hv Hx Ih Ii Ij Im In Io Ip Iq Ir Is Iu Jh Jk Jm Jn Jo Jq Jr Js Jt Lu Lw Lz Ma Mb Mc Md Me Mf Mg Mh Mj Mk Ml Mn Mp Mq Ms Mu Mv Mw Mx My Mz Na Nb Ne Ng Nh Nj Nm Nn No Nq Nr Ns Nu Ny Oe Of Oh Oi Oy Oz Pb Pc Pd Pf Po Pz Qa Qb Qc Qd) Ne(Hq Hr Hu Hv Hx Ih Ii Ij Ik Il Im In Io Ip Iq Ir Is It Iu Jh Jk Jm Jn Jo Jq Jr Js Jt Lu Lw Lz Ma Mc Md Me Mf Mg Mh Mj Mk Ml Mp Mq Mu Mv Mw Mx My Mz Nb Nd Ni Nj Nk Nm Nn No Nq Nr Ns Nu Ny Of Oh Oi Om Oy Oz Pb Pc Pd Pf Pg Po Pz Qa Qb Qc Qd) bA(aD aF aG aH aJ aL aN aP aS aU aV aW bB bC bE bF Bg bH bI bJ bL bM bN bO bP bQ bR bS bU bV bW bX bZ cA cB cC cD cE cF cG cJ cL cM cN cP cQ cR CT cU cW cX cY cZ dA Db Dc dE dF dG dH Di dJ dK DL dM Et fR Kc Me Nd Nj Om Wm) Et(Aa Ad Af aH aI aJ Ap Aw Ax Bb bN cE Ch Cp CS Ct Cu Dd De Di dM Ef Ez Fy Ha Hb Hc Ib Iz Jd Je Jv Kc Kd Ke Ki Kj Kk Ko Kp Kq Ks Kz Or Ph Ql Qm Qn Qt Qw Qx Qy Ra Rb Rc Rg Rj Sr Tn To Ua Uc Uk Ul Uo Ur Vo Vp Vs Vu Tj) Mi(Hr Hu Hv Hx Ii Ij Il Io Ip Ir Is It Iu Jh Jk Jl Jm Jn Jo Jq Js Jt Lu Lw Lz Ma Mc Me Mf Mg Mh Mj Mk Mn Mp Mq Mr Ms Mu Mv Mw Mx My Mz Na Nb Ng Ni Nk Nm Nn No Nr Ns Nu Ny Oe Of Oh Oy Pd Pf Po Pz Qb Qc Qd) Mm(Fr Hq Hr Hu Hv Hx Ii Ij Im In Iq Ir Is Iu Jh Jn Jo Jq Js Jt Kc Li Lz Ma Mb Mc Me Mf Mg Mj Mk Ml Mq Ms Mu Mv Mw Mx My Mz Nb Ng Ni Nk No Nq Nr Ns Nu Nv Nx Oe Of Og Oh Oi Oy Pc Pd Pf Pg Po Pz Qa Qb Qd Wm) Lv(bV dM fR Hq Hv Hw Ii Il Im In Io Iq Ir Iu Jh Jl Jm Jn Jo Jq Jr Jt Lh Lw Lz Ma Mc Md Me Mf Mg Mk Ml Mp Mu Mw Mx My Mz Nb Nd Nk Nm Nn No Nq Nr Nu Nv Nx Of Oh Oi Oy Oz Pb Pc Pe Pf Pg Po Pz Qb Qc Qd) gP(aA Ad AP Ar aW Ax Ba Bb Bg Bo cJ Co cR CS Cu Db Dc dF dG Di Dk Fr Hc Id It iZ Jf Jg Kd Kf Kn Kp Kq Lh Lj Lx Me Mt Nd Nj Nw Ok Oy Pc Ph Pj Qa Qd Qw Rb Rj St Uf Uh Ur Tj) aA(aJ cH Fr Hw Il Im Io Ip Iq Ir It Iu Iv Jl Jm Jq Li Lw Mb Md Me Mf Mg Ml Mq Mr Mz Nk Nm Nq Nr Ns Nu Nv Og Oh Oi Oy Oz Pb Pc Pd Pf Pg Po Pz Qa Qb Qd) Ko(Bg bN cS Dc Dd Dk dM Gl gW Ha Hq Hw Ij Io Ip Iq Ir Is It Iu Iv Jf Jk Jo Kc Ma Md Me Mj Mr Mu Om Pg Po Qt Qw Rb Rc Rj Sr Uk Ul Ut Vp Vs Vu Tj) Kc(Aa aJ bC bF bI bJ bL cE cH cJ cM cQ Dc dJ dM Dr dX eF eM eP fR gW Hq Hw Io Iq Jf Lx Md Me Mt Nw Om Qy Ra Sr Vp) Ik(Aa Hv Hw Ih Im In Iu Iv Jl Jo Jr Jt Lh Li Lj Lw Md Me Mk Mr Mz Nd Nh Nj No Nr Nu Nv Nx Of Om Pc Pe Pg Qa Qd) bV(aJ cB cH hC Hq Hw Ih Ii In Jg Jj Kk Lj Lx Mt Na Nd Nj Nr Nw Oe Og Ok Om Oy Pb Pc Pg Ph Qw Qy Rb Sr Wm) Jj(Hw Ih Ii Io Ir Jm Jn Jr Jt Lj Mf Mr Mz Nd Nm Nr Nu Oh Oi Oy Oz Pb Pf Po Pz Qb Qd) Fr(Hw Ih Im Iq Ir Iu Jl Jr Lj Mb Md Mf Mr Mv My Ng Nk Nq Nu Nx Of Og Oz Pe Qa) Me(aJ cS fR Ha Id Jf Kd Kf Ki Kk Kn Kp Kq Kr Ks Ph Pj Qw To Tt Uh Uk Vp Vt Wm) Jg(Bg Dc Hr Il Io Ip Ir Is It Jn Lu Mh Mw Na Nb Nn Nv Oh Oi Pd Po Pz Qb Qd) Nh(Aa Hw Ih Im Iv Jl Jr Lh Li Lj Mr Nv Nx Og Om Pb Pe Pg Qa) Mr(Hq Hw Im Iq Iv Lh Li Lj Nd Nj Og Om Oy Oz Pe Qa Wm) aJ(aW bC bL bN bR bS bU cF cH cJ cM cS cT dF dM Qw Rb) Nj(Aa cS dM fR Im Iv Jl Lh Li Lj Nv Nx Og Pe Pg Qa) Nd(Aa Ih Im Iv Jl Jt Li Lj Nv Nx Og Pe Pg Qa Qd) Lh(Hq Hw Ih In Iq Iu Iv Jo Lj Md Of Og Oz Qa) Om(Dg Ih Iv Jt Lj Md Nx Pe Pg Ph Qd Sr Uh) Hw(Aa Ih Im Iv Jl Li Lj Nv Nx Pe Pg Qa) Wm(bN cS dM hC In Lx Md Mj Ok Pg) Iv(Im Jl Li Lj Nv Nx Og Pb Pe Qa) Nw(Bg cS Dk Gl Ha Ut Vp Vu Tj) nD(kC kP nJ nK nM nT nU oP qX) Iq(Ih Im Jl Li Lj Nv Pe Qa) Og(Im Jl Li Nv Nx Oi Pe Qa) cH(aW cS cT dF dG dM gL) Lx(Bg Dc Gl Ha Qw Ut) Kk(bN cS Dr EM fR) Oz(Aa Ex fR Jl Li Qa) Ok(Bg Dc Dk Gl Ut) dM(bR bU cM cS) fR(cP Pc Qw Rb) Md(Li Nv Pe) In(Ih Pe Qa) Qy(Jk Mu Qw) aV(Dq Dr cP) oP(mF nC rX) Dc(Ad Dg) Jf(Ph Pj) Lj(Ha Nx) Vo(Dg Em) nO(jF rA) AaJr DqFw NqLi HqJl IuQa SrJs cBcS cEdF dGgC nUrA

Unconstrained panels with 2 analytes, where 1.0E-2 >= 'model p-value' > 1.0E-3. Contains 6,210 panels of 81,255 total panels evaluated. :
Kc(aA aC AD aE AF aG aH aI Aj aK aL aM AN AO AP aQ aR AS aU aV AW Ax aY aZ Ba BB Bc bE BG bH bM Bn BO bP bQ bR bS bU bW bX bZ cA cB cC cD cF cG Ch cI cK cL cN CO CP Cq cR Cs CT CU CV CW CX cY cZ dA DB dC DD DE dF DG dH DI DK DL dN Dp dR Ed Ef Ex Ez Fa Fb Fn FP Fr Fw Fy Gc GL Gp Ha Hb HC Hf Hr Hu Hv Hx Ib Ic Id Ih Ii Ij Ik Il Im In Ip Ir Is It Iu Iv Iz Jd Je Jg Jh Ji Jj Jk Jl Jm Jn Jo Jq Jr Js Jt Ju Jv Jy Kd Ke Kf Kg Ki Kj Kk Kl Kn Kp Kq Kr Ks Kx Ky Kz Ld Lh Li Lj Lu Lv Lw Lz Ma Mb Mc Mf Mg Mh Mi Mj Mk Ml Mn Mp Mq Mr Ms Mu Mv Mw Mx My Mz Na Nb Nc Nd Ne Ng Nh Ni Nj Nk Nl Nm Nn No Nq Nr Ns Nt Nu Nv Nx Ny Oa Oe Of Og Oh Oi OK On Or Ow Oy Oz Pb Pc Pd Pe Pf Pg Ph Pi Pj Pk Po Pz Qa Qb Qc Qd Qg Qh Ql Qm Qn Qt Qu Qv Qw Qx Qz Rb Rc Rf Rg Rh Ri Rj Rm Ss St Tn To Tr Tt Tv Tz Ua Ub Uc Ud Ue Uf Ug Uh Um Un Uo Up Ur Us Ut Uu Uv Vo Vs Vt Vu Vv Wm Tj) Ko(aA aC AD aE AF aG aH aI aJ aK AL aM AN AO AP aQ aR AS aU aV AW Ax aY aZ BA BB BC bE bF bG bH bI bJ bL bM Bn BO bP bQ bR bS bU bW bX bZ cA cB cC cD cE cF cG CH cI cJ cK cL cM cN CO CP CQ cR Cs CT CU CV CW CX cY cZ dA DB dC dD DE dF DG dH DI dJ dK DL dN Dp dX Ed EF eM eP Ez Fa Fb Fn FP Fr Fw Fy gL Gn Gp Hb HC Hf Hr Hu Hv Hx Ib Ic Id Ih Ii Ik Il Im In Iz Jd Je Jg Jh Ji Jj Jl Jm Jn Jp Jq Jr Js Jt Ju Jv Jy Kd Ke Kf Kg Ki Kj Kk Kl Kn Kp Kq Kr Ks Kx Ky Kz Ld Lh Li Lj Lu Lv Lw Lx Lz Mb Mc Mf Mg Mh Mi Mk Ml Mm Mn Mp Mq Ms Mt Mv Mw Mx My Mz Na Nb Nc Nd Ne Ng Nh Ni Nj Nk Nl Nm Nn No Nq Nr Ns Nt Nu Nv Nw Nx Ny Oa Oc Of Og Oh Oi OK On Or Ow Oy Oz Pb Pc Pd Pe Pf Ph Pi Pj Pk Pz Qa Qb Qc Qd Qe Qg Qh Ql Qm Qn Qu Qv Qx Qy Qz Ra Rf Rg Rh Ri Rm Ss St Tn To Tr Tt Tv Tz Ua Ub Uc Ud Ue Uf Ug Uh Um Un Uo Up Ur Us Uu Uv Vo Vt Vv Wm) gP(Aa aC aD aE AF aG aH aI Aj aK AL aM AN AO aQ aR AS aU aV Aw aY aZ bB bC bE bF bG bH bI bJ bL bM BN bO bP bQ bR bS bU bW bX bZ cA cB cC cD cE cF cG Ch cI cK cL cM cN cO CP CQ CT cU CV CW CX cY cZ dA dB dC DD DE dF dH dI dJ dK dL dN DO Dp Dq dR Dv Ed Ef eM eP EX Ez Fa Fb Fn FP Fw Fy Gl Gp Gt GW Ha HB Hf Hq Hr Hw Ib Ic Ih Ii Ik Im In Io Iq Iv Iz Jd Je Ji Jj Jk Jl Jm Jq Jr Js Jt Ju Jv Jy Ke Kg Ki Kj Kl Kr Ks Kx Ky Kz Ld Li Lv Lw Lz Ma Mb Md Mf Mg Mj Mk Ml Mm Mn Mq Mr Ms Mu Mv Mw My Mz Na Nc Ne Ng Nh Ni Nk Nl Nm Nn Nq Nr Ns Nt Nu Nv Nx Oa Oe Og Oh Oi Om On Or Ow Oz Pb Pd Pe Pf Pg Pi Pk Po Pz Qb Qc Qg Qh Ql Qm Qn Qr Qu Qv Qx Qz Ra Rc Rf Rg Rh Ri Rm Ss Tn Tr Tt Tv Tz Ua Ub Uc Ud Um Un Uo Up Us Ut Uu Uv Vo Vp Vq Vs Vt Vu Vv) Nf(aC aD aE AF aG aH aI Aj aK AL aM AN aO aQ aR aS aV Aw aY bB bF bG bH bI bL bM BO bP bQ bR bS bU cA cB cC cD cE cG cI cK cL cN cO Cp Cq Ct cV CW cX cY cZ dB dC dD De dH dI dJ DK dL dN Dp dR Ed Ef Ex Fb Fn fP Fw Gl Gp gW Gz Ha HB HC Hf Hw Ib Ic IH Ii Ip Ir IZ Jd Je Jj Jn Jq Jr Jt Ju Jv Jy Ke Kg Ki Kj Kl kQ Kr Ks Kx Kz Ld Lw Mf Mg Mk Mp Mu Mx Mz Nb Nd Nj Nn No Nr Nu Oa Og Oh Oi oK Om Ow Oy Oz Pb Pc PF Pi Pk Po Pz Qb Qd Qg Qh Ql Qm Qn Qt Qu Qv Qx Qz Rc Rg Rh Ri Rj Rm Ss Tn Tr Tt Tv Tz Ua Ub Uc Ud Um Un Uo Up Us Ut Uu Uv Vo Vs Vu Tj) bV(AA aW aX bL bM bN bR bS bU bX cJ cM cP cT Db dE dF DG Di DI dM Ez FP GL Ha Hc Hr Hu Hv Hx Ib Ic Id iH Ij Ik Il Im Iq It iZ Je Jf Jh Ji Jj Jk Jl Jm Jn Jo Jp Jq Jr Js Jt Ju Jv Jy Kd Kf Kg Ki Kn Kp Kq Kz Ld Lh Li Lu Lw Lz Ma Mb Mc Md Mf Mg Mh Mi Mj Mk Ml Mm Mn Mp Mq Mr Ms Mu Mv Mw Mx My Mz Nb Nc Ne Ng Nh Ni Nk Nl Nm Nn No Nq Ns Nt Nu Nv Nx Ny oE Of Oh Oi oK On Or Oz Pd Pe PF Pj Po Pz Qa Qb Qc Qd Qg Qh Ql Qm Qn Qt Qx Qz Ra Rc Rf Rg Ri Rj Ss St Tn To Tr Tt Ua Ue Uf Ug Uh Uk Ul Uo Up Ur Us Ut Vo Vp Vs Vt Vu Vy Tj) Ou(aA aC AD aE Af aG Aj aK Al aM AN AP aQ aR AS aV aY aZ Ba BB bG bH bI bM Bn BO bP bW bX bZ cA cB cC cD cJ cK cN cO cP cQ cT cU cV cW CX dA DB dC dD Dc dF dG dH dI dJ dK dL dN Dp dR Ed EF Em Fa Fb Fn fP Fy gL Gp Hb hC Hf Hr Hv Ic Ik Il Im Ip Ir Is Iu Iv iZ Jg Ji Jj Jt Ju Jv Ke Kg Kj Kl Kn Kq Kr Ks Ky Ld Lh Lv Mb Mc Mf Mg Ml Ms Mx Mz Na Nb Nc Ne Ng Nh Ni Nl Nm No Nt Nx Ny Oa Oi On Or pF Pi Pk Pz

Qc Qd) Qw(Aa Ad AP aU aW Ax bC bE bJ bN bW cE cJ cM Cs dE dF DG Dl Dr dX eF EM eP Ex Fp gL gW HC Hw Id Ih Ik It Jg Jm Jp Kf Kp Kq Lj Mm Mt Nm Nr Oi Ok On Oy Pj Qe Rf Rg Rj St Tr Tt Uh Ul Vq) Jl(Hr Hv Hx Ih Ij Il Im In Io Ip Ir It Iu Jh Jm Jn Jo Jq Jr Js Lj Lw Lz Ma Mb Mc Md Mf Mg Mj Mk Ml Mp Mq Ms Mw Mx My Mz Na Nb Ni Nk Nm Nn Nq Nr Ns Nu Nv Nx Of Oh Oi Oy Pb Pc Pd Pf Pg Po Pz Qb Qd) Ok(Aa Af aH aI Aj Ao aU aW Bb bC bE bF bJ bL bN cE Ch Co Cp cQ Cs Ct Cu Cw Dd DE Di Ef Ez gW Ha Hc Ib Iz Jd Je Kg Kj Kp Kq Qg Ql Qm Qn Qt Qx Qy Ra Rc Rg Rj Tn To Ua Uk Ul Ur Vo Vp Vs Vu Tj) aA(Aa aW aX bB bC bJ bL bM bN bR bS bU cB cF cJ cP cR cU dE dF dG Dl fP hC Hq Hr Hu Hv Hx Ii Ij In Is Jh Jk Jo Js Jt Lu Lz Ma Mc Mh Mj Mk Mn Mp Ms Mu Mv Mw Mx My Na Nb Ng Ni Nn No Ny Oe Of Qc) Ik(Hq Hr Hu Hx Ii Ij Il Io Ip Iq Ir Is It Jh Jk Jm Jn Jq Js Lu Lz Ma Mb Mc Mf Mg Mh Mj Ml Mn Mp Mq Ms Mu Mv Mw Mx My Na Nb Ng Ni Nk Nm Nn Nq Ns Ny Oe Oh Oi Oy Oz Pb Pd Pf Po Pz Qb Qc) Qy(Aa Ao aU aW Ax bC bF Bg bN cE Ch cM Co cR Cs Ct Dc dE Di Dk cP Fp gW Ha hC Hq Hw Ib Id In Io Iq It Iz Jj Jp Js Kp Lj Md Mj Mk Mm Mv Mw Oe Oy Pc Pg Pj Qc Qt St To Ua Ut Vp Vs Vu Tj) Aa(bC dG eF Hq Hv Hx Ih Ij In Iq Ir It iZ Jg Ji Jj Jm Jn Jo Jp Jq Js Jt Lj Lu Lv Lw Lz Ma Mb Md Mf Mj Ml Ms Mw Ni Nk Nq Nr Nt Nu Nx Of Og Oi oK On Oy Pb Pc Pd Pf Pg Qb Qc Qe Ra) Nv(Hq Hr Hu Hx Ih Ii Ij Il Im In Ip Ir Is It Iu Jk Jn Jo Jq Jr Js Jt Lj Lw Lz Mb Mc Mf Mg Mk Ml Mn Mp Ms Mv My Mz Ng Ni Nk No Nq Nr Ns Nu Nx Ny Of Oi Oz Pb Pc Pf Pg Qd) Lj(bC bE bN Dc eF gL Ih Ii Im In Io Ip Ir Iu Jh Jn Jq Jr Jt Kp Lw Lz Mb Md Mf Mg Mk Ml Mp Mu Mz Nb Ni Nk Nn Nq Nr Nu Og Oi Oy Oz Pb Pc Pf Pg Pz Qd Rg Rj Vp Vu Tj) Qe(aH aI Al Ao As aU aW bC bE Bg bL bN cE cF Ch cJ cM Co CQ CT Cu Cw Dd dE Dk fP GL hC Ir Is Kp Kz Mw Nn Po Pz Qg Qh Qn Qt Ra Ua Uk Ur Ut Vo Vp Vs Tj) Nd(aP bC dG eF gL Hv Hw Ii Ij Io Ip Iq Ir Is Iu Jh Jm Jn Jq Jr Lw Ma Md Mg Mj Mk Mp Mq Mu Mw Mx My Mz Nb Nk Nm Nn No Nr Nu Oh Oi Oy Oz Pb Pc Pf Po Pz Qb) hV(eD hA hR hW hX iB iC jD jE jF jG jH jI jK jL jM jO jP jQ jR jT jU jV jY kE lK lL lM lN lO lW mF mI mM mS nO nR nU oP qT qU qV qW qY rA rB rC rX rY rZ) Jj(Dg dX EM eP Hr Hu Hv Hx Ij Ip Iq Is It Iu Jh Jk Jo Jq Kp Lw Lz Ma Mb Mc Md Mj Mk Ml Mp Mq Mu Mv Mw Mx My Nb Ng Ni Nk Nn No Nq Ny Og Pc Pd Qc) oP(eD hR jQ kC kE kF kG kI kK kN kO kP lK lW lX lY mE mH mI mM mP mS mT mU mW mY mZ nA nB nF nH nI nJ nK nL nM nN nO nR nT nU oO oQ qX rA rY rZ) aX(aC Ad An aP Ar As aV aW Ax Ba Bc bF bM bN bR bS bU bX cB cJ cM cP Cs cT Db Dc dF Dg Di DL fP GL hC Io Ip Ir Is Iu iZ oE oF oK Vu) Nx(Dc Dr Ha Ih Im In Io Iq Ir Iu Jn Jo Jr Jt Lw Mb Mf Mg Mk Ml Ms My Mz Ng Nk No Nq Nr Nu Ny Of Oh Oi Oz Pb Pc Pf Pg Pz Qd Ut Vp Vu Tj) dG(aH aW bC bE bF Bg bJ bL bM bN bO bQ bR bS bU bW cB cC cD cE cF cG cJ cL cM cO cP cQ cR cT cX Db dE dF dH dL Dr dV eP Gt Hq In Iq Pc) Kp(Bg bJ bN cE cM Dc Dk GL gW Ha hC Hq Hw Ii In Iq Jk Jp Jq Jr Md Mj Mm Mu Nm Oe Oy Pg Pj Ra Rj To Ul Ur Ut Vo Vp Vs Vu Tj) Ih(Dc eP Ha Il Im Ip Ir Iu Jq Jr Js Jt Lw Lz Mb Md Mf Mg Mk Mp Mz Nb Ni Nk No Nq Nr Nu Og Oh Oi Oz Pb Pc Pf Pg Pz Rm Vp Vu) dF(aC aF aG aH aI aN aW bC bE bF bJ bL bM bN bO bQ bR bS bU bX bZ cD cF cG cI cJ cL cM cO cP cQ cR cT cX dE dH dJ dV eP eX) Jp(Ao Bg bN Ch Co Ct Cw Dd Dk Gl Ha HC Ib Il Io Iz Jd Je Ke Kg Ki Kj Kz Pj Qn Qt Ra Rc Rg Rj Tn Ua Ul Ut Vo Vp Vu Tj) Hw(Ax Ba bC Dg Dl eF fP gL hC Hq Io Iq Ir Jm Jn Jr Jt Mg Mk Mw Mx Mz Nb Nn No Nr Nu Og Oh Oi Oz Pb Pc Pf Pz Qb Qd St) Im(Hv Hx In Ir Iu Jo Jr Js Jt Lw Lz Mb Md Mf Mg Mj Mk Mp Ms Mx Nb Ni Nk No Nq Nr Nu Of Oh Oi Oy Oz Pb Pc Pf Pg) Pg(Ar Ax Dg In Iq Ir Iu Jn Jo Jq Jr Jt Lw Mb Md Mf Mg Mk Mz Nk No Nq Nr Nu Of Og Oh Oi Oz Pb Pc Pz Qd St) Og(bN Dr Em eP Gc Io Ip Iq Ir Jn Jq Jr Jt Mf Mg Mk Mz Nb No Nr Nu Oh Oy Oz Pb Pc Pf Po Pz Qb Qd) Dg(aH Aj Ao AW bC Bg bN cE Ch Co cP Ct Cw Db Dd De Di Dk Gl Ha Ii In Jo Jt Oe Ra Vs Tj) Lv(aP bC bE bN Hr Hu Hx Ij Ip Is It Jk Js Lu Mb Mh Mj Mn Mq Ms Mv Na Ng Ni Ns Ny Oe Pd) hC(cJ eF fP gL hB In It iZ Jg Jq Jr Md Mj Nk oF Or Qg Ql Rm Uf Uh Ul Ur Vp Vq Vs) eP(aK aM aN aW bR bU cB cF cN cP Cs Di dJ dK Dl Fp Hu It Kz Mf Nu Oz Pb Pc Rf) Gt(aK aN aQ aV bC Bo bR bU cB cF cG cL cN cP Cs cY Dd dI dJ Dl dR eF Fw Gp) oQ(eD hR kK lX mF mH mI mM mS mT mZ nC nD nF nK nN nO nT nU oO rA rX rY rZ) St(Dc Dk Dr Gc Gl gW Ha Hq Hx Ii In Iq Jk Js Mj Mu Oe Po Ut Vp Vq Vs Vu) Em(aN aV aW bR cB Fn Hf Ib In Kd Kj Kz Ld Or Pc Qx Qz Ra Ue Uk Uo Ur) Mt(aH aU aW bC bE Bg bL bN cE cF Ch Co Ct Dc Dd dE Dk Gl Ha Ut Vp Vs) Mm(Gl Ha Io Ip It Jk Jm Lu Lw Mh Mn Mp Na Nm Nn Ny Qc Ut Vo Vp Vs) Jr(hB Il Iq Is iZ Jt Lw Md Mg Mk Mz Nr Nu Oi oK Oz Pb Pc Pf Pz Qd) nD(hA hR iB jF jQ jR kF lK lX lY mH mP mU mY mZ nC nF nI nR qW) Dc(Ap Ba BC Cu Dl Fp It Ji Jm Kf Kq Nr On Oy Qd Tt Uh Ur) Jg(aH Aj Ao aU bN Ch Co Ct Cw Dd Dk Ef Gl Iz Ua Ut Vo Vs Vu) Iq(Ax bE cB Cs gL Ir Jn Jt Mk Mp No Nr Oh Pb Pf Pz Qb Qd) bN(AP Ba BC Db Dl eF FP gL In It iZ On Oy Pc) eM(aN aV aW bR bU cB cN cP Cs Fp Ib Mf Oz Pb Pc Qx Rf) Dq(aK aN aQ bC Bo bR cB cF cL cN cP Cs cY dI Dl) rA(kP mF mI mM mZ nC nF nI nK nL nR nT rB rY rZ) Ur(Dk gL gW Ha In It iZ Jk Mj Mu Oy Vp Vu Tj) rZ(jF mM nA nC nF nI nJ nK nM nR nT nU rB) Oy(Bg Gl Ha Pj Ua Uk Ut Vp Vq Vs Vu Tj) On(Bg Co Ct Dk Gl Ha Ua Ut Vp Vs Vu) Oz(dX Ir Jn Jt Mk Mz Nb Nr Nu Pz Qd) bC(Ar Ax Bg Cs cT Db Dd Di Dl Fp Pc) Md(Ax hB Ii Mp Mw Nb Nu Pc Qd Uh) Dl(aW Bg cP Db Dd Dk eX Gl Tj) Dr(bR dJ dL Hu Mz Or Qx Ra Vo) Mu(eF gL Hc Kf Kq Rf Tt Uf Uh) Pb(dX Io Ir Jn Jt Mz Nu Oi Qd) aV(Do DV dX eX GC gN gT) iZ(cJ cM fP Mj Nk oK Ql Vp Vq) It(gL Ha Nc Qg Vp Vs Vu Tj) Pc(aP cT dX eF Ex gL gW Qd) bU(aP aW Bc cJ cT cU dA dE) nC(jF lL mZ nB nJ nL nR nU) In(Ax Is Jt Kf Nu Qd Uh) Vq(gW hB Jn Ky Nl oK Ra) Ha(Ax Cs Id Jm Nr Oa) Ne(Mb Mn Ms Na Ng Oe) Uh(Gl gW Hq Ut Vs Vu) eX(aN bR cB cL Cs dJ) nR(eD lK nK qX rX rY) nU(hR kP lK mH qW qX) mI(kC kP mH mZ qW qX) Ba(Bg Ct Cw Dd Dk) Jk(eF Hc Kf Kq Tt) Vu(Ax Jm Kf Kn oK) nO(jQ jR lK qW qX) hB(bQ cE Mj Vp Vs) Kq(Bg Dk Gl Ut) aP(bL bR cJ cT) dX(aW cB cN Qx) eF(Di iJ Mv Ut) gL(aW cJ dE Io) gW(Id Pj Rh Uk) mM(eD lK rX rY) Ax(Js Rg Vp) Gc(Hu Kj Ue) Nu(Ir Mg Pf) Kf(Dk Jo Vs) fP(aH bE cE) mZ(eD lK nB) rB(jF lK lL) Ad(Dd Dk) Ex(Nl Ue) Qd(Mk Nq) Pj(Jo Ra) cT(bM dE) dV(cB cN) nH(nJ nL) DoFw FpVp NoMc MpHq NcIl TtVs IsJs aWcJ bRcU cLgN dLgC eDlX mFqW mWhR

Constrained panels with 3 analytes, where 1.0E-10 >= 'model p-value' > 0. Contains 25 panels of 10,034,416 total panels evaluated. : Et{Jo(Ik Ly Nc Ne Nl) Om(Mt Nc Nl) Jj(Ly Nl) MiHq} Ok{Jo(Ik Lv Ly Nl Om) MiHq MtOm NlJj} Mi{Hq(Lx Mt Nl Nw)} GnKcVo LyOnOy Constrained panels with 3 analytes, where 1.0E-9 >= 'model p-value' > 1.0E-10. Contains 184 panels of 10,034,416 total panels evaluated. : Ok{Jo(Et Hw Hx Iq Lx Md Mi Mt Nc Nd Ne Nf Nj Og Oz Pa) Nl(aA Et Hw In Js Jt Lx Md Mi Nf Of Og Om Pa) Om(aA Et Ji Jj Js Jt Lx Mi Nc Ne Nf Pa) Lx(Hw Jt Ly Nd Nf Po) Nc(Hw Jj Js Jt Og) Mt(Hw Jt Nd Nf) Ly(Jj Nf Og) Ne(Hw Jj) Nf(Jt Pa) NdOg JtPa} Et{Nl(aA Hw In Iu Ji Js Jt Lx Ly Md Mi Mt Nf Nk Of Og On Pa) Om(aA Fp Ji Jo Lx Ly Mi Ne Nw On Pa) Jo(Fp Lv Lx Mi Mt Nd Nj Nt Pa) Nc(Hw Jj Jt Ly Md Mi Pa) Ly(Lx Md Mi Of Pa) NdPa NeJj OnOy} On{Md(Hq Hw Lx Ly Mt Nc Nd Ne Nf Nl Om Oy) Oy(Hw Ik Lx Mt Nc Nd Ne Nj Nl Om Pa) Om(Jj Lx Mt Nl) Nl(Hq Jj) LxNf LyJj} Nl{Nw(Hw In Jj Js Md Om) Lx(aA Ji Jj Mi) Jj(Jg Mt) JiOg} Om{Lx(aA Jg Ji Mt) Mt(Ji Nw) MdNw JgJj} Mi{Hq(Fp Ik Ji Ly Nc Ne)} Ly{Jj(Jg Lx Mt) MdNw} GnHuRa LxNfJi MdNcNw Constrained panels with 3 analytes, where 1.0E-8 >= 'model p-value' > 1.0E-9. Contains 796 panels of 10,034,416 total panels evaluated. : Ok{Nf(aA Et Fp Hw Ik Ji Jj Jl Jr Js Lj Lv Md Mi Mr Nc Nd Ne Nj Nq Nw Of Og On Pc Qe) Jt(aA Et Fp Hw Ik Iq Jg Ji Jj Jl Jp Lv Ly Md Mi Mm Nd Ne Nj Nt Of Og Qe) Mt(Et Hq Ii Ij In Iq Jj Js Lx Ly Md Nc Ne Ng Nj Nl Nq Of Og Oy Oz Pa) Lx(aA Hq Hx Ii Ij In Iq Iu Jj Js Lz Md Nc Ne Nj Nq Of Og Oz Pd) Nc(aA Et Hq Ii In Iq Iu Jq Ly Md Mi Nd Ni Nk Nw Of Pa) Ly(aA Et Hq Hw In Jp Js Md Mi Ne Nl Of Om Pa) Ne(aA Et Hq In Iq Iu Js Md Mi Nd Of Og Pa) Og(Hw Ik Iq Js Lv Md Nj Nq Of Om Pa) Nd(aA Et Hw Jj Js Md Mi Of Om Pa) Jj(Fp Hw Ik Iq Lv Md Nj Oz Pa) Mi(Hw Iq Js Md Nq Of Pg) Nl(Hq Iq Iu Me Mm Nk Nw) Pa(aA Hw Iq Js Md Nj Of) Jo(Fp Jg Mf Nh Nq) Of(Ik Iq Js Md Om)

Figure 9 Continued

Om(Fp Lv Md Nw) Md(Hw On) FpHw MrHq NgJg OnOy} Et{Jo(Hw Ih Iq Iv Jg Ji Jl Jr Lh Lj Mb Md Mf Mg Mr Nh Nk Nw On Oz Pb Qa Qe) Ne(aA Hw In Iq Iu Ji Js Jt Lx Ly Md Mi Mt Nd Nf Of Og On Pa) Ly(aA Fp Hw In Iu Ji Jp Jr Js Jt Lj Mt Nd Nf Nw Og On) Mt(Hw Ij In Iq Jj Js Jt Md Nc Nd Nf Ng Nq Of Og Pa) Om(Ih Ik Jg Jj Jl Jr Lj Lv Md Mr Nd Nf Nj Qa Qe) Lx(Hq Hw Iq Jj Js Jt Md Nc Nd Nf Nj Nq Of Po) Nc(aA In Iq Iu Ji Js Nd Nf Ni Nk Of Og On) Nd(aA Fp Ji Jj Mi Nf Nw Of Og On) Pa(aA Hw Iq Jj Jt Md Nf Nj Of) Md(Fp Jg Ji Mi Mw Nw On) Nf(Fp Ji Mi Mr Nw On) Jt(Fp Jg Ji Nt Qe) Mi(Iq Nj Nq Pg) Jj(Fp Ik Nj) MrHq NgJg NlIq} Lx{Nl(Hq Hw In Iu Jg Js Lv Ly Lz Md Mm Mr Nd Nf Ni Nk Nw Og Om On Pa Po) Ly(aA Hw In Jg Ji Jo Jp Js Md Mi Mm Mt Nc Nf Nw Og Om On Pa Po) Om(Ik Jj Jl Lv Md Mi Mm Mr Nc Nc Nf Nw Pa) Ji(Hw In Iq Jj Jq Md Nc Nd Ne Nq Og Po) Mi(Hw In Md Nc Nd Ne Nf Nq Pg Po) Nd(aA Jj Mm Mt Nf Nw Og On) Jj(Ik Jg Mt Nc Ne Nj On) On(Hq Hw Nc Nq Po) Jg(Md Mv Ng Nq) Mr(Hq Nf Oy) Nc(aA Hw In) Nc(Hw Nk) Nw(Md Nf) aA(Nj Nq) MtHw} Nw{Md(Hw Ik Jg Js Lv Lz Mi Mt Mw Nd Ne Nf Nj Og On Oz Pa) Nl(aA Iq Iu Jo Jr Ly Lz Mi Ml Mm Nd Nf Nk Og Pa) Om(aA Ik In Jg Ji Jj Js Ly Mi Nc Nd Ne Nf Nj Pa) Nc(Hw In Jj Js Ly Mi Nd Nf Nk Og) Ly(Hw In Jj Jo Js Mi Nf Og) Nd(Jj Mi Mt Nf Og Pa) Nf(Ik Js Mi On Pa) Ne(Hw In Jj Js) Ik(Jj Jo) MiPg MrHq MtHw OnOy} On{Om(Fp Hw Iq Ji Jo Js Lj Ly Mi Nc Ne Nf Ng Nq Of Pa) Md(Fp Ij Ik Iq Jj Jo Lv Mb Mj Nj Nq Of Og Oz Pa) Oy(Fp Hq Iq Iv Jg Lv Mf Mi Nf Nh Nq Oz Pb) Nl(Hw In Js Mi Mm Mt Nf Nk Of Og Pa Pg) Nf(Fp Hq Ly Mt Nd Pa) Hq(Ly Mi Mt Nc Ne) Jj(Ik Mt Nc Nd Ne) Hw(Ly Mt Nc Ne) Ly(Jo Of) MtNd} Ji{Nl(aA Hw In Iq Iu Jj Jo Jq Ly Md Me Mi Ml Mm Mt Nd Nf Ni Nk Om Oz Pa) Om(aA Fp Jg Jj Ly Nc Ne Nf Pa Qe) Ly(aA Jj Md Mt Nc Nf Og Pa) Mt(Hw Jj Jq Md Nd Nf Og) Ne(aA Nf Og Pa) Nd(Nf Og Pa) Nc(Hw Og) Nf(Fp Pa)} Mi{Hq(Ih Iv Jg Jp Nd Nh Nj Nt Nx Oi Oz Pa Qe) Nl(Hw Jg Jj Ly Md Mm Mt Nk Oy Pa Pg) Mt(Ly Md Nd Om Pg) JgOm} Mt{Om(Fp Jg Jj Jp Lv Mm Mr Nl Pa Qe) Jj(Fp Ik Md Nc Nd Nj Pa) Pa(Ly Nd Nl) NgJg} Jg{Om(Fp Ly Mv Nc Ne Nl Og Pa) Nl(Md Mv Ng Og) Ly(Md Ng) MrOy NcJj} Nl{Jj(aA Fr Lh Mm Pa Qe) Pa(aA Mm Nk) MmaA} Ly{Jj(aX Jp Qe) Gn(bL Rc) aX(bN Nf) bVgP} Gn{Hu(Um Uo) IzKc} IkJjPa

Constrained panels with 3 analytes, where 1.0E-7 >= 'model p-value' > 1.0E-8. Contains 1,841 panels of 10,034,416 total panels evaluated. : Lx{Md(aA Hw Ik Jj Lv Mm Mr Mt Mw Nb Nc Nd Ne Nf Nh Nj Nq Nt Nx Og Oz Pa Pb Pc Po) Mi(Et Hx Ij Ik Iq Iu Jj Jo Js Lz Ma Mh Ml Mt Mv My Nh Nj Ny Of Og Oy Oz Pb Pd) On(Hx Ii Ij Il In Iq Iu Jo Js Jt Lv Lz Ms Mt Mv My Nb Ne Ng Nj Ny Of Og Oz Pg) Nf(aA aX Fp Hw Ik Jg Jj Jl Js Lh Lv Mk Mm Mt Nc Ne Nj Nq Pa Pb Pc Pe) Nw(Hw Hx Ii Ij In Iq Jo Js Jt Lz Ms My Nc Ne Nj Nq Ny Og Oz Po) Mt(Et Hq Ij In Iq Iu Ji Jk Jo Js Lv Mr Nc Nj Nq Of Og Pa Po) Lv(aA Hw In Jj Jo Js Ly Nc Nd Ne Nj Nq Og Oz Pa Po Qb) Mr(Hw Hx Ij In Iq Jj Ly Lz Mj Nc Nd Ne Nj Nq Og Pe Po) Po(Fp Hw Ik Jg Jl Mm Nc Nd Ne Nh Nj Nq Nt Pa) Nc(aA Hq In Iu Jg Js Lz Mm Nd Ni Nq Og Pa) Hw(Hq Ik Iu Jg Jj Jl Mm Nd Nh Nj Nq Og Pa) Ji(aA Et Hx Ii Ij Iu Jo Js Jt Ms Nj Of Oz) Ne(Hq Iu Jg Js Ly Lz Mm Nd Nk Og Pa) Jg(Ij In Jk Jo Js Jt My Nd Of Og) Jj(aA Hx Iv Lz Mg Nh Nq Nt Oz Pa) Et(aA Ii Ij In Iu Ng Og Oz Pa) Nj(In Iu Jo Js Mm Og Om Pa) aA(Iq Iu Js Mm Nh Og Oz Pa) Nd(Iu Jl Jp Js Ly Om Pa) Nq(Jl Jp Mm Nt Og Pa) In(Ik Iv Jl Nh Nt Pa) Hq(Ik Jl Pa Pb) Ik(Jo Og Pa) Iu(Ly Om) Og(Nt Pa) MkOy MmJo} Et{Md(aA Hw Ik Iq Iv Jj Jr Jt Lv Mr Nd Nf Nh Nj Nk Nq Nt Nx Of Og Ok Oz Pb Pc Qe) Hw(Fp Hq Ih Ik Ji Jj Jl Jr Jt Lj Lv Mi Mr Nd Nf Nh Nj Nw Og Ok On Qa Qe) Of(aA Fp Ik Iq Iv Jg Ji Jr Lv Mi Mr Nf Nh Nj Nt Nw Ok On Oz Pb Qe) Jj(aA Ih Iq Iv Jg Ji Jr Lj Lv Mi Mr Nf Nh Nk Nq Nt On Oz Pb Qe) Jt(aA Ih Ik Iv Jl Jr Lj Lv Mi Mr Nd Nf Nh Nj Nk Nw On Oz Qa) Mi(Fp Hx Ij Ik In Jr Js Ma Mt My Nh Ny Oy Oz Pa Pd Po) Nf(aA aX Ik Iq Iv Jg Jl Jr Lh Lj Lv Mk Nj Nq Pb Pe Qe) Ji(aA Fp Ii Ij In Iq Iu Jq Js Ms Mt My Nj Nq Og Oz Pa) Iq(aA Fp Ih Jl Jr Lj Mr Nj Nw Og Ok On Pb Qa Qe) Og(aA Fp Ik Iv Jr Lv Nh Nj Nt Nw Ok On Pa) aA(Fp Jo Jr Lj Lv Mt Nh Nj Nq Ok Oz) Nq(Fp Iv Jg Mr Nw Ok On Pa Qe) On(Hq My Nb Ng Nj Ny Oz Pg) Ik(Iu Lj Mg Ng Nw Ok Pa) Fp(In Iu Js Mt Ok Pa) Mr(Ij In Mj Nd Nj Oy) Nw(In Js My Nj Ny Oz) Nd(Ih Iu Jl Lj Qe) Ok(Hq Lv Nj Oz Pa) Mt(Ii Iu Mg Nj) Pa(In Iu Lv Nh) Jg(Jh Mv My) Ly(aX Dc) Nj(Iu Lj) In(Ih Qe) WmJo LvLj MkOy MwMy OmaX} Mt{Nw(Ii Ij In Iq Iu Jj Jo Js Jt Ly Mi Ml Ms My Nc Nf Ng Nj Nq Ny Of Og Oz Pa) Mi(Fp Hw Hx Ij In Iq Jj Jo Js Ma Ml Ms Nc Ne Nf Nj Nq Of Og Oy Pa Po) On(Fp Ij In Iq Jo Ly Ms Mv My Nb Nc Ne Ng Nj Nq Ny Of Og Oz Pa Pg Po) Pa(aA Fp Hw In Iq Ji Js Lv Md Mm Ms Nc Ne Nf Nj Nq Of Og) Ly(aA Fp Gn Hw In Jg Jo Jp Lv Md Mm Mr Nc Nl Og Om) Ji(aA Ii Ij In Iq Iu Jo Js Ms My Nc Ne Nj Nq Of Oz) Nl(aA Hw In Iu Jg Jp Js Lv Md Mm Mr Nd Ne Nk Og) Nd(aA Fp Hw Iu Jg Jl Jp Md Mm Mr Og Om) Hw(Fp Jj Jl Lv Md Mm Mr Nc Og Om) Jj(Iv Jg Lv Mr Ne Nq Nt Oz Qe) Om(aA Jl Jr Lh Lj Md Nc Og Pe) Md(Fp Jg Lv Nc Nx Pc) Mr(Hq Ij In Mj Nf Oy) Jg(Mv My Nq Of) Og(Fp Ik Lv Nc) Nq(Jp Mm) Nc(Mm Nk) Ok(aA Iu) FpIn MkOy NfaX} Ji{Om(Fr Ih Ik Im Iq Iv Jo Jp Jq Js Li Lj Md Mi Ml Mm Ms Nd Nh Nj Nt Og Oz Qa) Ly(Fp Hq Hw Ih In Jg Jo Jp Jq Lj Mi Ml Mm Ms Nd Ne Nj Of Oz Qe) Md(aA Fp Hw Ik Iq Jg Jp Jq Mi Mw Nc Nd Ne Nf Og Ok On Oz Pa) Nd(aA Fp Hw Ih Iq Iu Jg Jj Jo Jp Jq Mi Mm Nc Nc Oz Qe) Nf(aA Hw Ik Iq Iv Jg Lv Mi Mm Mr Nc Nj Nw Og On Oz Qe) Nc(aA In Iq Jg Jj Jo Jq Js Mi Mm Ni Nk Oz Pa) Og(aA Fp Hw Ik Iq Iv Jg Jq Nh Nj Nt Oz Pa) Ne(Hw In Iq Iu Jg Jj Jo Jq Me Mi Mm Oz) Pa(aA Hw Ik In Iq Jj Jo Jq Ms Nj) Ok(Hw Ii In Iq Jq Oz) aA(Fp Iq Nj Oz) Mi(Hw Jq Pg) Jg(Jo Jt Ng) Jj(Ik Jq Nj) Iq(Ih Qe) FpHw IkJo} On{Nf(Hw Ih Ik Im Iq Iv Jg Jj Jr Lj Lv Mf Mi Mm Mv My Nb Nc Ne Ng Nh Nj Nq Nt Of Og Oz Pe Pg Qe) Nl(aA Hx Ii Ij Il Iq Iu Jg Jk Jo Jt Ly Me My Nb Nd Ng Ni Nq Ny Oz Po) Nc(In Iq Js Ly Mi Mm My Nd Ni Nk Of Og Pa Pg) Nd(Hq Hw Iq Iu Jo Mi Mm My Ng Of Og Om Pa) Om(aA In Jg Lv Mm Ms Mv My Nj Ns Nw Og) Hw(Fp Iq Jj Mi My Ng Nj Nq Of Og Pa) Ly(Ii In Jp Js Mi My Ng Og Pa Pg) Md(Hx In Iv Jg Lj Lz Mk Mm Nh) Jj(Fp Hx Iq Iv Lv Nj Nq Oz Pa) Nc(aA In My Of Og Pa Pg) Hq(Fp Mv Nj Nw Ok Oz Pa) Of(Ik Iq Nj Nq Pa) Jo(Ik Lv Nj) NqOg NgJg IqPa NwNy} Nw{Hw(Hq Ih Ik In Iq Jj Js Mi Ml My Nd Nf Nh Nj Og Ok Oz Pa) Mi(Hx Ij Ik In Iq Js Ml Ne Nj Nq Ny Of Oy Po) Ly(aA Hq Iu Ml Mm Ms My Nd Ne Ny Of Ok Pa) Nd(aA In Iu Jo Js Ml Mm Ms My Ne Of Ok) Nj(aA In Iu Jj Jo Js Ml My Nf Og Ok Pa) Nc(aA Iq Iu Jr Lv Lz Ml Mm Ms Ni Pa) Ne(aA Iq Iu Jo Lz Ml Mm Nf Og Ok Pa) Ik(Ii Ij In Js Jt My Of Og Pa) Md(aA Fp Iq Iv Ms Ok Pc) Pa(aA In Iq Jj Js Lv Og) Mr(Hx Ij Mj Nf Oy Po) Lv(Jj Jo Nf Og Om) Jg(Jt Mv My Ng) Jj(Iq Iv Nt Oz) Og(Iq Js Ok Oz) Fp(In Nf Om) Ok(Hq Iq Oz) aA(Nf Nq Oz) In(Ih Iv) Om(Ml Mm) MkOy NfIv} Ok{Mi(Fp Ii Ij Ik In Jj Jq Ma Ml Ms Nj Og Oy Oz Pa Po) Md(aA Fp Hq Ik Iq Jg Jp Jr Js Lv Mw Nj Nq Oz Pc) Js(aA Fp Hw Ik Iq Jj Jr Lv Nh Nj Nk Nq Oz Qe) Hq(aA Fp Hw Ik Iq Jl Lv Mk Nd Nj Oz Pa Pb) aA(Fp Hw Iq Jj Jr Lv Nj Nq Of Og Oz) In(Fp Ih Ik Jl Jr Mr Nj Nk Pa Qe) Pa(Hx Ii Ij Jg Jq Lv Ms Nq Oy) Fp(Ii Ij Iq Iu Lz Nq Og) Iu(Ik Lv Ly Nd Nj) Of(Hw Jg Jj Lv Nj) Iq(Hw Ih Jp Qe) Og(Hx Jj Oi Oz) Nq(Fr Jg Jj) Mm(Nd Ne Nf) Mr(Ij Mj Oy) Ik(Ii Ij Ng) Nd(Jp Ly) Nf(Im Iv) Nj(Hw Jp) Jr(Ii Jq) Oy(Mk Pc) MeNe HxJj} Ly{aX(aA bA cH Db gP Hw Ii In Js Lv Mb Md Mr Na Nd Oe Ou Pa Pb Qe) Gn(aG aV bP bX dC dJ gP Hu Js Jt Kf Kj Kn Mu Ul Um Un Uu Vo) Jj(Fp Fr Ik Im Jl Lh Li Mi Mm Nc Nl Nt Nv Pa Qa) Jp(Fp Hw Jo Lv Md Mi Mm Nc Nd Ne Nf Nl Og Om Pa) Jg(Jh Jo Lj Mi Mv My Nc Nf Nl Of Og Pa) fR(cP Dd De dJ gP Lv Md Na Nf) Mi(Fp Md Nc Ne Pa Pg Qe) Aa(Jo Jr Nf Nl Pa) Mm(aA Nc Nl Pa) Nl(aA Fr Pa) DrRc EmKj SrJs PaaA aJgP} Nl{Jj(Fp Ik Im Iv Jl Jm Jp Jt Li Lv Mg Mr Mz Nk Nm Nt Nv Nx Oy Pe Pg Pz Qa) Jg(aA Hw In Jh Jk Jo Jt Lv Mm My Nf Ni Nk Of Oy Pa) Mi(aA Fp Hx Ij In Jp Lz Ml Nf Ni Of Og Om Pf Po) Mm(Fp Fr Hw In Jo Jp Lv Md Mr Nd Ni Nk Og Om) Pa(Fr Hw Il In Jp Lv Lz Md Ne Nf Ni Og Om) aA(Fp Lv Md Me Ni Nk Nx Og Om Qe) Fr(Hw Md Nk Og Om) Jp(Lv Ni Nk Om) Nk(Fp Qe) AaOm MdNx InQe} Jg{Om(aA Ih Jl Jo Jt Lj Lv Md Mm Mr My Nf Ng Nq Of Qa Qe) Md(Fp Jj Lv Mi Nc Nd Ne Ng Nq Nx Og Pa) Ng(Fp Ik Lv My Nc Nd Ne Nf Oz Pa Qe) Mv(Jj Mi Nc Nd Ne Nf Og Oz Pa) Pa(Jj Jt Nc Nd Ne Nq Of Og) Jj(Fp Ik Nd Ne Nj Nq) Mi(Nc Nd Ne Nq Of) Og(My Nc Nd Ne Nq) My(Nc Ne) FpNf MkOy NcOf} Mi{Hq(Fr Hw Im Iq Jm Jn Jr Lh Li Lj Lv Mb Mf Mg Mm Nf Nr Nu Nv Om Pb Pe Pf Pg Qa) Nc(Hw Jj Md Mm Nk Pa) Ik(Jj Jo Og Pa) Fp(Md Nf Pg) Ne(Md Pa

Figure 9 Continued

Pg) Nd(Jp Pa) QeOm} Gn{Kc(Aj Ao Cw Ef Ez Jo Kj Nm Of Rc Uo Uu) Hu(cP Hb Ib Kn Om Ou Ow Qz Rc Ul Vo) Rc(Kk Me Rb) Ra(aV Ld Or) Kk(Um Vo) aV(aU cY) QwVo QvcN} aX{Ou(cE gP Hq Kc Ko Me Mj Nf Om Rb) Nf(bN Lj Lv Nd Nj Pa Qe) Me(Ko Nd Nj Sr Vq) QegP] Jj{Nc(Ik Lh Mg Mm Nt Pa Qe) Ik(Jl Jp Me Mm Og Qe) Pa(Nd Ne Nj Nt) Qe(Nd Ne Om) MmNe} Mm{aA(Nc Nd Ne Om Pa) Nc(Nd Om Pa) Pa(Nd Ne) FpOm IkJo} Pa{aA(Nd Ne Nj) NcNk IkOg} Em{Kj(Me Nx) RcKc} MdNxaA aVdOgP

Constrained panels with 3 analytes, where 1.0E-6 >= 'model p-value' > 1.0E-7. Contains 2,874 panels of 10,034,416 total panels evaluated. :
Jg{Og(Et Fp Hw Ik Iq Iv Jh Jj Jo Jr Jt Lj Lv Mi Mr Mt Nf Ng Nh Nj Nt Of On Oz Pb Pc Qe) Ly(aA Dc Fp Gn Hu Hw Ih In Iu Jk Jp Js Jt Lv Mm Ms Mu Mw Ne Nq Ny On Oy Oz Qe) Nc(aA Fp Hw In Iq Iu Jh Jk Jo Js Jt Lj Lv Mm Mr Mt Nd Nf Ni Nk Nq Ns On Oy Oz) Pa(aA Fp Hw Ij In Iq Iu Jh Ji Jk Jo Js Lv Lx Mi Ms My Nf Nh Nj On Oy) Md(Hw Ik Iq Iv Jk Jo Jp Jr Jt Lj Mm Mv Nf Nh Nj Of Oz Pb Pc Pe Qe) Jj(aA Hw Ih Iq Iv Jh Ji Jt Lv Mi Mr My Nf Ng Nh Nt Nw Of On Oz Qe) Ne(aA Fp Hw In Iu Jh Jk Jo Js Jt Lj Lv Mm Mt Nd Nf Nq Of On Oy) Mi(Fp Hw Ij In Iq Jk Jo Js Jt Ma Ml My Nf Ng Nh Nj Oy Oz Pg) Mv(aA Fp Hw In Iq Iv Ji Jo Jp Jt Lv Ng Nh Nj Nq Of Ok On Qe) Mt(Hw Ij In Iq Jh Jk Jo Js Jt Lj Mg Ms Nf Nj Ns Oy Oz) My(Fp Hw Iq Ji Lv Nd Nf Nh Nj Nq Nx Of Ok On Oz Pb Qe) Of(Fp Ji Jl Jt Lv Mm Mr Nd Nf Ng Nq Nw On Oz Qe) Ji(Hw Ii Ij In Iq Iu Jq Js Ms Nj Nq Oy Oz) Lx(Hq Ii Il Iq Iu Jh Ms Nj Oy Oz) Ng(Hw Ih Iq Iv Lj Mm Nh Nj Nq Nt) Fp(Hw In Iu Jo Js Jt Nd Nl Nq) Jo(Lv Mm Mr Nd Nq Nw On Qe) Et(Ij In Js Lj Mg Ms Oy) Nf(Lj Lv Mr Nd Nq Pe Qe) Nw(Ii Ij Jh Mu Nq Ny Oy) On(Hq Hw Iq Jt Nd Nq Oz) Ok(Hq Ij Iu Mg Oy Oz) Jt(Lj Lv Mm Mr Qe) Nd(Jh Lj Mm Qe) Nl(Iq Iu Js Lj) Nq(aA Lv Qe) Hq(Hw Mr) Om(aX Jh) Oy(Jl Pe) GnKc} On{Fp(Ii Ij Il In Iq Iu Jk Jo Js Jt Ly Mi Mm My Nb Nc Nd Nc Ng Nq Ny Of Og Oz Pa Pg Po) Pa(aA Hx Ii Ij Ik In Jk Jo Js Jt Lv Mi Mm Ms Mv My Nb Ng Nh Nj Nq Nt Ny Og Pg) Nq(aA Hq Ii In Iq Iv Ji Jo Js Jt Lv Ly Mi Mm Ms My Nc Nd Ne Ng Nj Nw Oz) Ne(Hx Ii Ij Il Iq Iu Jk Jo Jp Js Jt Lj Ly Me Mi Mm Mv Nb Nd Ng Ny Oz) Hq(Hw Ih Ik Iq Iv Ji Lj Lv Mb Mf Mm Mr Ms Mu My Ng Nh Ns Nt Og Pe Qe) Nj(Ii Ij In Iq Iu Ji Jk Jp Js Jt Lj Mi Mm My Nb Ng Ny Og Pg) My(Hx Ik Iq Iv Ji Lv Lz Mb Mj Mm Nh Nw Of Og Ok Oz) Nc(aA Hx Ii Ij Il Iu Jk Jo Jt Lv Mv Nb Ng Ny Oz) Nd(aA Ii In Ji Jk Jp Js Jt Lj Ly Ms Nb Ny Pg Qe) Iq(Ih In Ji Jo Jt Lj Mi Ms Ng Nw Og Pg Qc) Of(Hx In Jj Js Lv Mi Mm Ms Ng Nh Nw Og Oz) Ly(aA Ih Ij Iu Jk Jt Lj Mm Ms Nb Ny Qe) Hw(Ih Ji Jo Jt Lj Ms Mv Nb Nh Oz Pg) Og(Hx Ik Iv Js Lv Ms Ng Nh Nt Oz Pg) Jo(Hx Iv Ji Mb Mf Mi Mm Nh Nt Oz) Nw(Hx Ii Ij Jt Mv Nb Nv Oz Pg Po) Ik(Ii Ij In Jt Mi Nb Ng Pg) Jt(Iv Lj Lv Mm Nf Nt) Pg(Ji Lv Mi Nh Ok Oz) Et(Ij In Iu Lj Mv) Ng(Js Lv Ms Ok Oz) Mt(aA Ii Il Iu) Ji(Ii In Jq Ms) Jj(Mf Ms Nh Nt) Lv(Ii Mv) In(Ih Mi) Ok(Ij Ny) NfJs IiOz} Ly{Gn(Aa Ad Ao Ba Cu Dl Ef Et Fb Fr Hb Ij Ir Iu Iz Jj Jo Ju Jv Ke Kl Kq Ks Li Mw Na Of Om Oz Pc Pj Qn Ra Ss Ue Uf Uh Uk Uo Vt) bV(aZ bJ bN Db Dc dE Et Ha Hw Ii In Jj Jk Js Ko Lv Md Mr Na Nd Nf Oe Ou Pa Pg) Mi(aA Hw Ih Ik Im In Iv Jo Jr Li Lj Ml Mm Nd Nf Nh Nj Nt Of Og Om Oy) gP(bA cH cS dM eF eM Et Jf Jj Jk Jp Js Kc Kk Ko Lj Nf Ou Qe Sr Uk Wm) Jj(AA Ih Io Iv Jn Jr Lj Lv Mg Mr Mz Ne Nr Nx Pe Pf Pg Pz Qd) Pa(Fp Fr Hw Ik Im In Iv Jr Lv Md Nc Nd Ne Nf Nh Nj Nt Og Qe) Mm(Fp Fr Hw Ih Im Jo Jr Lj Lv Md Mr Nd Ne Nf Og Om Qe) aX(eM Ha Kc Kk Ko Kp Ph Ql Rj Ur Vp Wm Tj) Qe(aA Dc Hw In Jp Mt Nc Nf Nl Og Om) Aa(Hw Js Jt Lx Mt Nc Ne Og Om Oz) Jp(aA Dc Ih In Js Lj Ng Nj Nq Of) aA(Fp Ih Jn Jr Lj Lv Nc Ne Og) Ou(Et Hq Jk Js Mu Nf Vu Tj) Et(Ao Bg Dk Kg Ut) Fr(Md Nc Ne Nf Og) Mt(Iu Js Lj Nd Of) Nl(Fp Lh Lv Mr Og) bA(Hq Jk Js Nf) fR(Db dH Lz Oz) Og(Fp Li Nt) Em(Uu Vo) Nf(aJ Lh) DrNk MdNx JsUh} Nw{Lv(aA Et In Iu Js Lx Ml Mm Ms Mv My Nj Of Ok Oz Qb) Mi(Jj Jo Jr Lz Ma Mh Ms Mv My Nb Nh Og Oz Pa Pb Pd) Ml(Fp Ik Iv Jj Js Lx Mb Ms Nh Nq Of Og Oy Oz Pa) Pa(Hq Hx Ii Ij Il Jo Lz Ms My Nh Nq Ny Of Po) aA(Fp Hq Ik In Iq Jj Js Mm Ms Mt My Nh Of Og) Lz(Fp Ih Jo Lj Mr Ms Mv My Nk Ny Of Ok) Js(Fp In Iq Iv Jj Ms My Nh Nk Nq Nt Oz) Ik(Hq Hu Il Iu Jq Ms Mv Ng Ny Ok Oy) Jo(Fp Hx Iv Ji Mg Mm Mr Nh Nt Oz) Og(Fp Hx In Iv Ji My Nh Nq Nt Oi) Ok(Ii Ij In Jq My Nq Ny Oy Po) Nt(Ii Ij In Jt Nq Ny Of) Mr(aX In Nb Ny Of Pe Pg) Iv(Ii Jt My Nq Ny Of) Ji(Ii Iq Jq Ms Ny Oz) Jl(Hq Hx Ij Oy Pg Po) Mm(Fp Jt Ms Nq Of) In(Iq Nh Nk Oz Qe) Jj(Fp Hx Mg Nh Nq) aX(Ii Jq Nf Nj Om) Ih(Ii Ij Iq Jr) Iu(Et Fp Lx Nh) Qe(Ij Jt Qb Qc) Hq(Mk Pb Pe) Of(Lx Nh Oz) Et(Ii Ms) My(Oz Pc) WmPg MkIj MsOz NfNy NjIq NkJq HxPb OyPc} Mt{In(Ih Is Iv Jl Jp Jr Lh Lj Lv Mk Mm Nb Nc Ne Nj Nr Nt Pb Pe Qe) Md(aA Iq Iu Iv Jl Jp Jr Lh Mm Mr Mw Nb Ne Nq Og Oz Pb Qe) Mm(aA Fp Iq Iu Jo Jr Jt Lv Mr Ms Ne Nf Ng Nj Of Og Oz) Og(aA Iq Iv Jl Jp Jr Mr Ne Nj Nq Nt Oi Oz Pb Pc Qe) Mr(Fp Hx Il Iq Iu Jo Lz Nc Ne Nj Nq Of Oz) Qe(Hw Ij Iq Iu Jk Jo Js Nd Nf Nq Of Qb Qc) Fp(aA Iq Iu Jo Js Lv Ml Nc Nf Nq) Jl(Hq Ij Iq Jo Nf Nj Nq Of Oy Oz) Jp(Hw Iq Js Ms Ne Nf Ng Nj Of Oz) Lv(aA Iu Jo Nc Nd Nf Nj Nq) Hw(Hq Lh Lj Mk Ne Nj Pe) Iq(aA Ih Jr Lh Lj Nc Pe) Mi(Iu Mh Mv My Ny Pb) aA(Jr Nc Ne Nj Nq Oz) Nf(Jr Lh Lj Mk Pe) Hq(Mk Pa Pb Pe) Iu(Nc Ne Nj Pa) Nq(Fr Lh Nt) Lx(Il Oy Pg) Jo(Ik Lh Nt) Js(Jr Lj Nt) Nc(Nd Ni) Om(Aa aX) Pc(My Oy) NdLj NjaX IlPa} Ji{Jo(aA Fp Fr Hw Iq Iv Jl Lv Md Mg Mi Mm Mr Ms Nh Nj Nt Og Oz Pb Qe) Mi(Fp Hx Ij Ik In Iq Jj Js Ma Ml Ms Nh Nj Nq Of Og Oy Pa Po) Hw(Ih Ik Iq Iv Jj Jl Jp Jq Lj Mg Ml Mm Mr Ms Nh Nj Oz Qe) Md(Fr Iv Jj Js Lv Mm Mr Ms Nh Nj Nt Pb Pc Qe) In(Fp Ih Ik Iv Lj Lv Mr Nd Nh Nj Nt Oz Qa Qe) Jj(aA Fp Iq Iv Lv Mg Ms Nh Nt Og Oz Qe) Mm(aA Fp Ik Iq Lv Ms Nh Nj Nq Oz Pa) Pa(Fp Ii Iv Js Lv Ml My Nh Nq Nt) Qe(Ii Ij Iu Js Ms Nq Og Qb Qc) Nj(Iq Iu Iv Jp Jq Lv Nt Oz) Ik(aA Iu Jp Jq Me Ms My Of) Og(Ih Js Lv Mr Ms Nq Oi Pb) Iq(Fp Iv Jp Lj Mr Oz Qa) aA(Ih Jq Js Lj Lv Nh Nq) Fp(Iu Ml Nq Oz) Mr(Hq Ij Mj Oy) Iv(Jq Ml Ms Nq) Jq(Ih Jr Oz) Ok(Hq Ij Ms) Nq(Jp Nt) Me(Nd Nh) Ml(Lv Oz) Oy(Mk Pc) WmNf NdLj} Gn{Kc(Aa Ad aG Ap aV Ba Bb Bg Ch Co Cu dJ Dl Gl Hu Ib Ii Ij Im Jh Jt Ke Kf Kg Kl Mg Og Om Pj Qv Ra Ss Uc Ue Uf Ul Um Un) Ra(Aa aJ Ao aZ cF CH Ed Ih Js Jt Ke Kf Kj Kk Kl Kz Md Me Qu Rb Rc Rg St Tr Ue Uf Uh Uk Um Un Uu Vo Vt) Hu(Aa aD aJ aW Bb Fp Gl Hq Hv Jv Kf Nb Nd Nj Ny Og Oz Pc Rb Ue Wm) Qw(Aa Ao Hb Im Iz Jt Ke Kf Kj Kn Rc Ue Uf Ul Un) aV(aK aQ cN Cs dK dR Fw Gl gP Kk Uo) Me(Fb Ju Ke Kf Kn Uf Um Uu Vo) Rc(bR Ex Fw It Ld Og Oh Sr) Gl(bA bR bU cF cP dD Fw) Rb(aG aJ aX cH cN dE dL) Vo(cN dJ Ih It Kf Nj St) Kk(Iz Kf Om Ss Uo) Uo(dJ Jy Ld Nj) aJ(dA Ny) AaFw NjKf OgOr} Jj{Ik(aA Fp Fr Hw Ih Im Io Iv Jm Lh Li Lj Lv Md Mg Mr Mz Ne Nf Nt Nv Nx Om Pe Pg Pz Qa) Qe(aA Fp Hw Hx Iq Iv Lv Md Mg Mi Mm Mr Nf Nh Nj Nq Nt Oi Oz Pa Pb Qb Qc) Nc(aA Fp Fr Im Iv Jl Jp Jt Li Lv Mr Ni Nk Nv Nx Pe Pg Pz Qa) Nt(aA Fp Jm Jp Md Mg Mi Mm Nd Ne Nj Nq Og Om Oz Pb) Pa(aA Fp Im Iv Jl Jp Lh Lv Mg Mi Mm Nh Nx Oi Qa) Ne(aA Fp Fr Jp Lh Li Lv Mg Mi Nv Nx Pz) Fp(aA Iv Jp Lv Mg Mi Mm Nf Nj Om) Nd(Im Jl Jp Lh Mi Mm Nv Qa) Nl(Aa Ii Lj Ma Ni Oi Pb Pc) Nj(aX Fr Jp Lh Mi Mm) Om(Im Jl Lh Nv Qa) Lv(Jp Mm) MdNx MiNh MmaA} aX{Ou(aW Bg bJ bN CH Et Fw Gl Ha Ii Jk Jl Jq Kk Kp Kz Lj Ma Md Mk Mr Mu Mv Ow Pg Ph Po Ql Qw Rj Ul Ur Ut Vp Vs Wm Tj) Nf(aJ Ax bA cH cP Fp gP Hw Ih Js Kc Kk Ko Me Mh Nr Oe Ok Om Pb Ph Qw Sr Ur Vq Wm) Me(bN gP Hf Jf Kc Kk Kp Lv Mb Oe Pb Ph Qw Rj Uk Vp Wm) Ko(bN gP Ha Jk Jo Kc Mj Po Qw Rb Rj Vo Vp) Et(Bg bN cE gP Ii Jo Jt Ma Mr Nd Nj Oc) gP(aJ Jf Kc Kk Ph Qy Rb Rj Sr Ur) Nj(bN In Lv Lx Nk Pa Qe) Qe(bN Ii In Nd Oe Om) Kc(bL bN Jf Mj Rj Vp) Om(Lj Ph Qa St) bN(Kk Ok Ph Rb) Mj(Ph St) AxMr HaLj NdPa PcaA} Nl{Nk(Hw Ih Im Jl Jr Lh Li Lj Lv Md Me Mr Nt Nv Og Pb Pc Pe Pg Qa) Og(Aa Fp Ik Iv Jl Jp Lh Li Lv Mr Nt Nv Nx Oi Pb Pc Pe Qe) In(Aa Fp Fr Ih Is Iv Jl Jp Jt Lh Li Mr Nv Nx Pe Qa) Aa(Hq Hw Ij Jo Js Jt Lx Lz Ma Mj Nf Ni Oz Pa) Qe(Hw Il Iq Iu Js Lv Md Mr Ne Nf Ni Om Qb Qc) Lh(Hq Hw Il Iu Jo Js Md Me Nf Om) Fp(Hw Iu Jp Lv Md Mr Nf Ni Om) Md(Jp Lv Mw Nb Nv Om Pc) Mr(Hq Hw Il Lv Lz Nf Oy) Hw(Im Jl Jp Lv Nv Pe) Fr(aA Iu Lv Mv Nf) Jp(aA Iq Nd) Om(Li Lv Nv) Iu(Mm Pa) aA(Jn Lw) LvMe MiNy} Mi{Ik(Fp Hw In Iq Iu Jp Lj Md Me Mm Nc Nd Nf Nj Of Om Oy Pd Pg Qe) Ne(aA Fp Hw Hx Ij In Iq Jp Lz Ml Mm Nd Nf Nk Of Og Om Oy Qe) Nc(aA Fp Hx In Iq Jp Lv Ml Nd Ni Nt Of Og Om Oy Pg Qe) Fp(Hw Hx In Iq Jp Lz Ml Mm Nd Nj Og Om Oy Pa Po) Md(Jp Lv Mm Nd Nf Nh Nj Nt Nx Pa Qe) Pa(Hw Iq Lv Mm Nf Nh Nj Nt Om Pg) Pg(Jp Lv Nd Nf Nh Nj Nt Nx Qe) Om(Im Iv Jp Lh Mm Nh Nt Qa) Qe(Hw In Iq Nd Nf Nj Nq) Nd(Ih Im Mm Nt) Jp(Hw Iq Nj Nq) Ih(In Iq)

Figure 9 Continued

NtOg LxII MmNj NfLj NhHw} Lx{Mm(Hq Hx Ik In Iq Iu Js Jt Lv Mr Of Oz Pa) Jl(Hx Ij Il Iq Iu Jo Js Lz Md Of Og Oy Oz) Iu(Hx Ik Lv Md Mr Nf Nh Nq Nt Og Pa) Po(Hx Iq Iv Lh Mf Og Oz Pb Pe Qe) In(Fp Ih Is Lh Nb Nq Pb Pe Qe) Js(Ik Iv Md Mr Nh Nq Nt Og Pa) Lz(Fp Mk Nj Nq Nr Pa Pe) Hq(Fp Mk Nh Nj Nr Nt Pe) Mr(Ik Il Jo Lv Oz Pa) Iq(Lv Md Nc Nj Og Pa) Iv(Jo Jr Md Nq Og) Ik(Ij Ng Nq Of) Jo(Lh Mg Nh Nt) Og(Hx Nh Oi Oz) Ml(Fp Lv Mb) Pa(Hx Nh Oy) Pc(Mv My Oy) Nq(Fr Nj) Mg(Ng Of) Qe(Qb Qc) AaOm NtOf NjJp HxPb IiLh} Et{Ou(Bg Co Dk Gl Hq Ii Ij Jo Nf Om Pg Po Ut Vu) In(Ik Is Iv Jl Jr Lj Nh Nk Nt Nu Qa Wm) Nq(Fr Ih Jl Jr Lj Lv Nt Og Oz Pb Qa) Iu(Ih Jr Lj Lv Mr Nh Nk Nt Pe Qa Qe) Nf(Ao Bg bV Ch Dc Dk gP Kg Kk) Wm(Hq Ii Ij Md Mj Mr Pg) Js(Ih Jr Lj Nh Nt Qa Qe) Og(Ih Lj Mr Nk Oz Pb Qe) Dk(Gl gP Jf Or Qy) Hq(Jl Lh Mk Pb Pe) Lz(Lj Mr Nr Pc) Oz(Jr Lj Lv Mr) Ij(Jl Qa Qe) Om(bV Dc Gl) Pc(Mv My Oy) Ng(Fr Nt) Hx(Mr Pb) Qe(Ii Qc) Lj(Ha Pb) gP(bV Kk) DcPa GlJo MeIk NiNk IrIv IsJr JlOy} Pa{Nc(aA Fp Fr Hw Ik In Jp Lh Lv Md Nd Ni Nt Og Om) Ne(Fp Fr Hw In Jp Lv Lz Md Nd Nf Nk Nt Og Om) Mm(Fp Hw Ik Iq Jr Lv Md Nf Nh Nj Nq Nt Om) Nt(aA Hw In Jo Lv Md Nd Nf Nq Og Om) Lv(aA Fp Hw Ik Jp Nd Nf Nj Og Om) Ik(aA Hw In Jo Jp Md Nf Om) aA(Fp Iq Jn Jr Nh Nq Om) Nd(Fp Fr Jp Og Qe) Fp(Md Nf Om) Nf(Lh Mr) Nj(Jp Og) Qe(Iq Om) MdNx JpOm} Mm{Nc(Fp Fr Hw Ik In Jo Jp Jr Lh Lv Md Mr Ni Nk Og Oz Pb Qe) Ne(Fp Hw In Jo Jp Jr Lv Md Mr Nd Nf Og Om) Nd(Fp Ih Jl Jp Lh Lj Mr Og Qe) aA(Fp Ik Jr Lv Md Nh Nj Nq Oz) Om(Ik Jp Jr Lj Lv Mr Qa Qe) Fp(Hw Jo Lv Md Nf) Md(Ik Lv Ok) Ik(Og Ok) LvJo MrNf NjJp OkOz} Ok{Hq(Iv Jr Nh Pe Pg Qe) Mr(Hx Ii Il Lz Pe) Ik(Jp Me Mg Oy) Qe(Ij Il Lz Qc) Jl(Ii Ij Lz Oy) Ih(Ii Ij Il) My(Mw Pc) Nh(In Me) WmNf EmVo LzLj NkJq InIv JpOz} Jp{Om(Fp Ik Lv Nc Ne Nj Nt Qe) Nc(Fp Hw Lv Nd Ni Nk) Nd(Fp Lv Ne Og Qe) Md(Fp Ik Lv Nx) Ik(Jo Ng Og) Lv(Ne Nj) FpNf NeaA NjOg} gP{aJ(Bc bN bV cH cR cS Rb) Me(Kc Kk Ko Ou Sr Wm) bV(Kc Kk Ko Qw Qy Rb) Nf(Qe Sr) Qw(eP Ko) Kc(eM Ou) QbQe KoRj dOfR} aA{Ne(Fp Jn Jq Jr Lv Md Me Nx Og Om Qe) Fp(Lv Nc Nd Nf Og Om) Om(Lh Nc Nt Nx Qe) LvNc NdQe} Nc{Fr(Hw Nd Nk Om) Qe(Hw In Nk Om) Og(Ik Lv Nt) FpNk MdNx HwLh} Nf{Ou(fR Kc Ur Wm) Fp(Fr Lh Mr) fR(cP Nj) DcQe} Qe{Om(Fr Ik Iq Lv Ne) Og(Ik Nd) MdNx NeIn} Me{Dr(Fb Rc) Em(Uu Vo) Sr(Dc Js) fR(Nd Nj)} Ne{Om(Aa Fr) MdNx} Em{Vo(Nx Qw)} Fp{FrOm MdNx} Og{NtNd MrIk} DrRcKc RbOuVu aVcNeP nAnDrX

Constrained panels with 3 analytes, where 1.0E-5 >= 'model p-value' > 1.0E-6. Contains 5,765 panels of 10,034,416 total panels evaluated. :
aX{Et(Ao aW bA Cw Dc Dk Gl Ha Hq Hw Ij In Jf Jj Jk Jq Kc Kg Kj Kk Lj Lv Mb Md Me Mj Nq Oz Pa Pb Pc Pg Ph Ql Qn Qw Rb Rj Tn Ut Uv Vo Vp Vs) Om(AA Ax BA bN cB cH Cs dI Dl Fp Ih Ik Ji Jm Jp Kk Ko Lh Lv Lx Mc Nd Nj Nr Oh Ok On Oy Pa Pb Pc Pe Qb Qy Rb Rj Sr Tt Uh) Qe(aW bA Bg cE Dc Ha Hw Iq Jf Jj Jk Jl Jo Jq Js Kc Kk Lv Ma Me Mj Mp Mr Nq Oz Pa Pb Pc Pg Po Qc Ql Qw Rb Rj Ut Vo Vp Vs) gP(bA Bc Dg Dl dM gL Hc Im Jg Jm Jp Kd Kn Kp Kq Ld Lh Lj Lv Lx Mt Nd Nj Nr Nw Ok On Or Oy Pa Pb Pc Qa Qd Qw St Uh Vp Wm) Rb(aZ bJ cH dE Dr Ha Hw Ii In Jj Jk Jl Kc Kk Kp Lv Lz Mb Md Mj Mr Mu Na Nd Nf Oe Pa Pb Pc Ph Ql Qw Rj Us Vp Wm Tj) Ko(aW bJ cE cM Dc Dk GL Hq Ii In Iq Jf Jj Jl Jq Jt Kd Kj Kk Ma Md Mq Mr Mu Nd Pa Pg Ph Ql Qt Tn Ul Ut Vs Wm Tj) Nw(Bg bJ bN cE cP Dc Dk Ha Hq Hw In Jk Jl Js Lv Lz Ma Mb Md Mj Ms Na Nd Nq Nv Ny Oe Oz Pb Pc Pg Po Ql Rj Vp) Ph(bJ cE cH cM Dk Gl Ha Hq Hw Ii In Jf Jk Jq Jr Kk Ma Mr Mu Nd Nk Pa Pg Ql Qw Qy Rj Ur Ut Vo Vp Vs Wm) Nd(aA aJ Ax bA bN cE cH cP dI dM Fp Ih In Jg Jj Jp Lj Lv Lx Mi Mr Mt Nr Nu Og Ok On Oy Qa) Lj(bA bJ bN cP Dc Hw Ii In Jq Js Lv Lz Me Mj Mr Na Oe Og Oz Pb Pc Pe Pg Po Qw Rj Vp) bN(Fp Ih In Jf Jg Jp Kp Lv Lx Mt Nr Nu Oe Og On Oy Oz Pa Pb Pc Qw Qy Sr St Vp) Lx(Bg cE Ha Hw Ii In Jk Jq Js Lv Ma Me Mj Mr Nq Oe Pb Pc Pg Po Ql Qw Vp) Ok(Bg cE cP Dc Ha Hq Hw Ii In Jk Jo Jq Js Jt Lv Ma Mr Nj Nq Oe Pb Pg Vp) Mt(Bg cE dI Hw Ii In Jk Jq Lv Ma Md Me Mr Ms Nq Oe Oz Pa Pb Pc Qw Wm) Qy(cE cH Dk Hw Ii In Jj Jk Jl Js Kc Kk Mj Mr Mu Nf Qw Rj Vp Wm) Pa(bA Bg bJ cE cP Ha Hw Ii In Jf Kk Lv Me Mr Oe Qw Rj Sr Vp Wm) Kk(cE Ha Hw Ii Jk Jq Ki Md Mj Mr Mu Nm Ql Qw Rj Ur Vp Wm) Me(aC aJ bA Bg cE cP Db dM Fp Hw Ik Jj Nl Nq Oz Pc) Ih(Dc eM Ha Hw Ii In Js Lv Mj Mr Nq Oe Qw Rj Rm Vp) Nj(bA bJ cE cH cP eM Hq Hw Ii Jk Jq Mj Ni Nr Og) Lv(Ax bA Bg cE cK cP dI dM Hw Mr Nr Oy Pb Pc) Qw(Aa bA Jf Kp Nr Oy Rj Sr St Ul Ur Vp Wm) Kc(cE cP dJ eM gL Ha Ii Jk Jq Md Nk Sr Ul) Ax(Ha Ii In Js Lz Mj Oe Pg Rg Rj Vp) St(Dc Dr Ha Ii In Jk Jq Mr Ql Vp) Oe(bA cP Dg Fp Jg Jp Nr On Oy Qa) Nf(fR gL It Jf Kd Kn Or Rj Vp) bA(cH Hq Hw Jk Mr Nq Oz Pb Pc) Gn(bR Kj Ld Ou Qv Rc Ue Vo) Fp(Ha Ii In Mj Mr Pc Po) Wm(Ha Jf Pb Rj Sr Ur) Mj(Aa Hc Kn Kq Sr Ur) Mr(Ar cP Cs Nr On Pb) Ii(Ar Jg Lh Nr On Qa) Jg(Bg cE Jk Vo) Sr(Gl Jq Js Vo) Kn(Jq Jr Ql Vp) Rj(Aa Jf Rf Ur) On(cE Hw Jk Jq) Ha(Nr Oa Pe) In(Jm Nr Qa) Ur(Jj Jk Vp) Vq(Jo Ue Vo) Pc(cE cP Og) Ly(Dr gL) Ou(eP Vu) Pb(cH cP) DgVo NrHw HcJk JiJq JjOy JpcE KpVp} Gn{Kc(Af aJ Al bL cH Cp Ct Dc dE Dg Dk dL Et Fb Fr Fy Hb Hw Ik Il In Is Jd Jk Js Ju Jv Kn Kp Ks Ma Me Mr Mu Mv Ng Nk Nq Ny Ok Or Oy Pz Qm Qt Qu Qy Rb Rh Ua Uh Vq Wm) Kk(Aa Ad Aj aN Ao Ba bL Ch cN Cu Dc Dd dJ dL Ed Ef Ez Fb Fr Gl Hb Ib Ii Ij Ir Jd Jg Jh Jj Jo Js Jt Jv Jy Ke Kj Kl Ks Li Ma Me Nk Nl Ny Of Pj Qt Qu Ue Uf Ul Un Uu) Rb(Aa aD Ao Bb cF Ch cO dG dJ dK Ef Fb Fr Ib Ic Ij Iz Js Jt Ke Kf Kj Kl Kn Ky Mr Mu Na Nk Of Og Om Or Oz Pc Qu Qw Qx Ss Ue Uf Uk Ul Um Un Uo Uu Vo) Qw(Ad aJ aV Bb bL Ch Cu Dl Ef Ez Fb Fy Gl Ib Ii Ij Is Ji Jo Js Jv Kg Kl Ks Me Mg Mw Ng Nm Ny Om Or Pj Pz Qt Ra Uh Um Uo Uu Vq) Vo(aC aJ Al aM cH cI cO Cu Cv DG DL Em Fa Fw Gz Jm Kn Ko Ld Mf Mh Nv Nw Nx Oa Og Ok On Ou Pb Qa Qb Qx Qz Rm Uo Vv) Rc(aJ Ar aV Ax cF cH cN cP Cs Cv dJ dL Fa Ih Jj Jm Jn Kf Ko Lj Mz Nb Nw Nx Oa Oe Ok On Or Ou Pe Qa Qn Qz Rm St Um Uo) Uo(aJ Ax aZ Bg Bn cF CH cI Cx Di dL Dp Ed Em Fb Gl Hf Ih Jj Kc Kj Kx Me Mu Oa Og Or Oy Qu Qx St Uc Uf Uk Un) Me(Aa Ao Bb Ez Hb Ib Ij Iz Jd Jv Jy Kl Ks Om Oz Pc Qu Qx Ss Tz Uc Ul Un) Fw(Ad aG aO Ap Ba Bb bL bR Ch CP Cu Cw dJ Dk Ef Fr gP Ij Kf Ra Uu) bR(Aa aG aJ aN Ap Bb CH cN Cs Cw dJ Ef Em Or Ue) Og(aV cN dJ Fb gP Kf Ld Nj Ny Oz Pc Rg Ue Uf) cH(aN aV cF cP Ez Jy Ld Ny Or Ph Qt Ue Uf Um) Hu(aG aN Ao aV bL cF cN CS dN gP Lu Nl) Kf(cN Cs Ef Ex Fa Kj Ld Mf Nx Oa Qa Uu) Om(aJ dJ Ko Kp Ld Lh Nj Oh Or Ra Sr) aJ(aQ aV bU Dl dJ gP Qt Qu Um) cN(dJ Ef Ez Iz Jo Jt Kj Nm Ny Ue) cF(Aa aV Bb Ch dJ dL Em Or Um) Gl(dL Ih Kp Ky Mf On Pc Um) Ra(aQ aY bP cI Cw Iz Kn Vs) Ld(Aa aG dJ Ij Jv Um Uu) aV(aG Cw Di Do Fp gW Or) dL(Ap gP Ib Ny Qt Qu Um) Ch(bU cP gP Kn Pc Um) dJ(Aa aN Ib Or Qt Um) Aa(It Mf Nj) Kj(Ko Nx On) Uf(Jp Ko Mf) aD(Fp Jy Or) cP(Ap Ef Or) Cs(gP Li) St(Ny Uu) Jt(Ko On) Ke(Ex Jp) Um(Oa Qx) Vv(Ib Ma) FpLi LyUc IhIi QtgP} Ly{bA(aJ aU bE bF Bg bN cE cH cS Ct Db Dc dE Dk Et Hw Hx Ii In Jj Jq Md Mk Mr Na Nd Nv Oe Om Oy Pa Pc Pe Pg Po Wm) Jj(aJ bC bE cH cS dE dM Hw Ii Ij Ir Jk Jm Jt Ma Mp Mw Nf Ng Nh Nj Nm Nn No Nu Ny Og Oh Oi Oy Pb Pc Po Qb) Ou(aJ bF Bg bN cE CH Co cS Ct Dc Dk Ha Hw Kc Ko Lj Md Mj Mk Mr Mv Om Ow Oy Pg Pj Po Qw Qx Uk Ut Vp) Et(aJ aU bF bN cE Ch Co cS Ct Dd DE dM Gl Ha Ib Iz Jd Je Jf Ke Kj Ks Qw Tn Uk Vp Vs Vu Tj) Nf(aA aP Ax bN cH CS Db dE dM Fp Id Im Jl Ko Kp Li Lj Lv Mr Nv Pe Qa Sr Uh Ur) Hw(aJ bN cH cS cT dE dM Fp Fr Ih Im Jf Jl Ko Lh Li Lv Mr Nc Ne Nl Nv Pe Ph Qa Sr) Nc(Fp Ih Im Jl Jr Lh Li Lj Lv Ma Md Mr Mz Ni Nk Nt Nv Og Pb Pc Pe Pg Qa) Md(aA aJ Bo cH dE dM Fp gP Ko Lh Li Lv Nl Nv Om Pc Pe Qe Sr Uh) gP(cR Dk gL Im In Kp Lx Mt Nd Nw Pa Pb Pc Ph Qa Ra Rg Ur Vq) Fr(aA Fp Hq Ih Im Iv Jo Jr Lj Lv Nd Ng Nj Nq Nt Of Om Qe) Js(aJ bN cH cS cT dE Dg dM Fy Id Ko Kp Ph Pj Qe St Tt) Og(bV Ih Ik Im Iv Jl Jr Jt Lh Lj Lv Mr Ne Nv Pe Pf Qa) Qe(bN dE Fp Ha Iq Iu Jo Lv Mr Nd Ne Qb Qc Vu Tj) Om(aA aJ cH Fp Im Jl Lh Li Nv Pa Qa Sr St Tt Uh) Dc(Aa Ad cH Dg Ih Ko Lj Lx Nw Ok Pa Qa Sr Tt) Pa(aJ bE bN cH cS dE Dk dM Ha Ih Mr Vp Tj) aA(dE Im Jq Lh Li Nd Nh Nj Nt Nx Oz Pe Qa) Nl(Dr Im Jl Li Lj Ma Mz Ne Nv Pc Pe Pg) bN(aJ cS Db dE dM In Jg Kc Ko Kp Na Wm) bV(Dr Hf Kc Lz Ph Ql Ur Ut Vp Wm Tj) Lv(Em Fp Ih Im Li Lj Mr Ne Pe Qa) Mm(Ik Iv Jl Lh Li Nj No Of Pb Pe) cH(aJ aZ cS dE Hf Ii In Na Oe Pb) Fp(Aa Ha Im In Iu Jl Mr Ne) aJ(cS Db Ii In Jk Nd Oe Wm) Dk(Aa Jg Jp Ko Nw Sr Tt) Ne(Im Jl Lh Li Lj Mr Pe) Hq(Ba Bo cT dE Lh Mr) Ha(Lj Lx Nw Pe Sr) In(Ih Im Lh Li Qa) Jg(Aj Ao Bg Ct dE) Jo(Dg Im Lh Li Nv) Aa(dE Ih Ij Nj) Em(Nu Tr

Figure 9 Continued

Ul Vp) Sr(Li Jk Mj Mu) eM(aC bE bl Ub) Dr(cN dF Jy) Jk(cT Ko Tt) cS(Kc Ko Wm) dE(dM Jf Wm) Jp(Bg Dd) eP(cL Hu) BaCt TjNw MiHx MrOy MuTt IhRm aUa Uk Vq) Qy(Bg cH gW Jk Lj Mu Wm) dM(cH cS Db Dl gL Qw Wm) eF(Bc Bg cH Dk Dl Dq) cS(bA Bc cH Dl gL) fR(Aw Bc Db Gt Kd)
Dk(Dg Kq Ok) Sr(gW Ii Js) Nw(Jq Rg Rj) cH(bA Bc gL) Wm(gW Qw) BoGt HaLj InQa JpVs UrgW} Nl{Md(Aa Ii Im Iv Jl Jq Jt Li Lj Lw Mp
Mq Mr Mz Ni Nm Nn Nt Og Pb Pe Pg) In(Hw Hx Ii Im Jn Jq Jr Lj Lw Mk Mp Mw Mz Nb Nr Nt Pb Pc Pf Pg Pz Qd) Hw(Hq Ih Iv Jt Li Lj Lw
Me Mg Mk Mp Mw Mz Nt Nx Og Pc Pg Qa Qd) Ni(Ih Im Jl Jt Lh Li Lj Me Mk Mp Mr Nv Og Pc Pc Pg) Iu(Im Jl Jt Li Lj Mr Mz Nt Nv Nx Pe
Pg Pz Qa Qd) Me(Fp Ik Iv Jl Mk Mr Nb Ne Nt Nx Pb Pc Pg) Og(Im Jq Jt Lj Mg Mz Oy Pg Pz) Ne(Ih Im Jl Lj Pe Qa) Lz(Jl Li Lj Nr Pe) Mp(Hq
Oz Pd Pf Pg) Hq(Jl Mk Pb Pe) Iq(Im Lh Li Qa) Js(Is Li No Nv) Ml(Nb No Nx) Jo(Jt Mg Nv) Aa(Il Mt) Mr(Hx Mj) It(Jl Jt) Jr(Is No) Oy(Mk Pc)
FpLh MyNx NkIv HxPb IlJl LjPc} Qe{Iq(aA Fp Fr Hw In Iu Jl Jp Lh Lv Md Mm Mr Nc Nd Ne Og Pb Qc) Hw(Fr Ik Iu Jl Jp Lh Lv Mm Mr Nd
Ne Nh Nj Nt Og Pa Qc) In(bN bV Fp Ik Iv Jl Lh Lv Mm Mr Nd Nh Nj Nt Nx Pa Wm) Og(aA Fp Lv Mm Mr Nc Ne Nh Nj Nt Oi Oz Pa Qc)
Lv(aA Iu Jo Md Mm Nc Nd Ne Pa Qb Qc) Md(Fr Ik Jp Mm Mw Nc Nd Ne Pa Pc) Mm(aA Ik Jo Jt Nj Nq Of Oz Qc) Nc(aA Iu Js Mr Nd Ni Nt
Qb Qc) Nd(Fr Iu Jl Lh Mr Ne Nt Qc) Pa(aA Dc Il Iu Nj Nq Qb Qc) Ne(Fr Iu Js Mr Nk Qb Qc) Dc(bV Jf Kc Me Nw) aA(Ik Nh Nj Nq Oz)
Mr(Hq Il Mj Oy) Nj(Fr Iu Jp) Il(Ji Mt Nw) Nq(Fr Jp) Ik(Iu Jo) Ji(Ml Of) WmMj NtJo LxHq NwNy} Pa{Hw(Fp Fr Ih Im Iv Jl Jp Jr Lh Li Mg
Mr Nd Nh Nj Nv Nx Og Qa) Iq(Fp Fr Ih Ik Im Iv Jl Jp Jr Lh Lv Mr Nc Ne Nh Nt Qa) Nd(Aa Ih Ik Im Io Iv Jl Lh Li Mr Mz Nh Nj Nv Nx Qa)
Og(aA Fp Iv Jl Jp Jr Lh Mg Mm Mr Nh Nx Oi) In(Fp Ih Is Iv Jl Lh Mr Nh Nj Nx Qa Wm) Md(aA Fr Iv Jp Lh Lv Mw Nh Nj Nv) Mr(Fp Hq Ik
Mj Mm Nc Ne Nh Nj Oy) Nj(Fp FR Iv Jl Lh Nk Nt) Jp(Fp Hx Iv Mb Mm Nh Nq) Iv(aA Fr Lv Mm Nh) Fp(Ha Lz Nh) Mm(Jo Mb Of) Ik(Iu Me
Of) Wm(Mj Pg) Fr(Nh Nq) Nt(Il Of) aA(Mf Nx) AaNe HaLj LvNh LzNc HqJl JkKo} Nc{Nk(aA Hw Ih Ik Im Iv Jl Jr Lh Li Lj Lv Mr Nd Nt Nv Nx Og Pb Pc Pe Pg Qa Qd) Ni(aA Fp Fr Jl Jt Lh Li Lj Lv Mr Nt Nv Og Pe) Hw(Fp Im Jl Jt Li Lv Mg Mr Nt Nv Nx Pe Qa) In(Fp Fr Is Jl Lh Li Mr Nt Nv Nx Pe Qa) Og(aA Fp Fr Iv Jl Jp Lh Li Mr Nv Nx Pe) Md(aA Fp Fr Jp Lh Lv Mw Nb Nt Nv Pc) aA(Jn Jp Jr Lh Lj Nd Nt Nx Oz Pe) Mr(Fp Hq Jp Lv Lz Nd Nt Oy) Lh(Fp Hq Iq Iu Jo Js Nd Oz) Fr(Fp Iq Iu Lv Mv Nq Nt) Jp(Ik Iq Nt Oz) Fp(Iu Lv) Mm(Iq Iv) Nd(Jl Li) NtLv} Mm{Mr(Fp Hq Hw Ik Iq Jo Jr Lv Mb Md Nh Nj Nq Og Oy Oz) Nd(Fr Hw Ik Im Iv Jo Jr Li Lv Md Nr Nt Pb Pe Qa) Nj(Fp Fr Hw Ih Jl Jo Jr Lh Lj Lv Md Og Oz Pb Pe) Hw(Ih Ik Jl Jp Jr Lh Lj Lv Nh Nt Pe Qa) Md(Fr Jp Jr Lh Mw Nh Nt Nx Pc Pe) aA(Ih Iq Jn Lj Mb Nt Og Pc Pe) Lv(Ih Ik Jp Lj Nh Of Og Oz) Fp(In Iq Iu Jp Nq Og Oz) Ik(In Iu Jl Jp Lj Ng Of) Jr(Iq Jo Nh Nq Og Oz) Nq(Fr Iv Jp Nt) Ji(In Js Jt Of) Jo(Iv Lh Nh Nt) Iq(Ih Jp Lj) Og(Iv Nh Nt) Jp(Nh Oz) IhIn NwNy} Jp{Ik(aA Fp Hu Hw In Iq Iu Jt Lj Lv Me Mv Nd Ne Nj Nq Of) Nt(Hw In Iq Jo Js Jt Md Nd Ng Nq Of Og Oz) Fp(aA Hw In Iq Js Lv Ml Ne Nj Nq Og) Lv(aA Hw Iq Ji Jo Ng Nh Nq Og Oz) Nd(aA Hw Ih Jl Lj Md Mr Nj Pe) Nj(aA Hw Iq Iu Md Mr Ni Nk) Ne(Hw In Iq Md Ni Nk Og) Mr(Hq Hw Iq Oy) Nh(aA Hw Md Og) Ji(Js Ms Mv My) Nq(aA Fr Iv) Wm(Mj Pg) Md(Mw Pc) HwJl IhIq} Ne{In(Fp Fr Ih Is Jl Jt Lh Li Mr Nt Nv Nx Pe Qa) Og(Aa Fp Fr Ik Iv Jl Lh Li Lv Mr Nt Nv Nx Pe) Hw(Aa Fp Fr Im Jl Lh Li Lv Mr Nv Nx Pe) Aa(Ij Jo Jr Js Jt Lx Ma Mj Oz) Fp(Fr Iu Lh Lv Md Me Mr Nk) Md(Fr Lh Lv Mw Nb Nv Pc) Lv(Fr Li Lj Me Mr) Lh(aA Iu Jo Me) Fr(Iq Iu Nd) aA(Lj Lw Nk) MrHq} Me{Sr(aU Bg bV Cp cS Db Dd dE Dk Ha Hf Hw Jk Kc Kp Kr Mj Mu) bV(Ha Hf Hw Kc Ko Lv Nd Nj Oe Qw Ur Ut Vp) Em(Jf Kg Kl Uc Ue Ur) Hf(aJ bA bN cH cM Jf) Dr(aN Ju Jv Jy) Kc(bA bN cM cS) Ko(bN cS Dc dE) Ha(dE Fp Lj) Ik(aA Lv Og) Nj(aA aJ) Jf(Db dE) fR(Lv Oz) DcKf WmdE MbJi} Og{Ik(aA Fp Fr Hw Ih Iv Jl Lh Li Lj Lv Md No Nr Nt Nx Pe) Fp(Fr Iv Jl Lh Lv Mg Mr Nd Nh Nt Oi) Nt(aA Fr Hw Lv Md Mr Nj Nq Oz Pb) Nd(aA Fr Im Jl Lh Li Mr Nv Pe Qa) Lv(aA Ih Im Iv Li Mr Nh Oi) aA(Nh Nj Nx) FrNj MdNx OzfR} aA{Nd(Ih Im Jn Jr Lh Li Lj Lv Nh Nt Nx Pe Qa) Lv(Ih Ik Jn Jr Lj Md Nh Nj Nt Nx Oz) Nx(Fp Ik In Lj My Nh Nj Ny Oz) Nj(Fp Ik Jn Jr Lj Nt Pe) Jn(Fp Ik Iq Nh Nq Oz) Fp(Md Nh Nq) Nt(Md Nq Oz) Jr(Nh Oz) IkLj} Ji{Mr(Hx Ii Il Lz Nb Nq Ny Of Pe Pg Po) Fr(Ii Mv My Ng Nq Of Oy) Jl(Hq Hx Ii Ij In Oy Pg) Ih(Ii Il Iu Js Nq Qb) Nt(Iu Js Ml Of) Lj(Iu Js Lz Ml) Pb(Ii My Of) Hq(Mk Pe) Qa(Ij Qb) Js(Iv Ms) NrIu MgOf MyPc NiNk} Mt{Aa(Hw Ij Jt Ma Mj Nd Nq Oz) Iv(Ir Jn Jo Jr Js) Lh(Hq Il Iu Ng Of) Pc(Ms Mv Ng Ns) Wm(In Mj Pg) My(Mw Nb Nx) Iu(Jl Lj Nt) Fr(Mv Ng) No(Jr Js) Mp(Hq Pd) Il(Jl Pe) Is(Jr Js) Ny(Nb Pb) NtOf NgIk HxPb OyPe} Fp{Mr(Hq Hw Il In Iq Lv Lz Md Mj Nd Oy Pe) Fr(Hw In Iq Iu Lv Md Nd Nj Nq) In(Is Iv Jl Lh Nt Nx) Md(Lh Lv Mw Nt Pc) Hw(Jl Lh Lv Mg) HaQy LvMl MgJo} Lx{Aa(Hw Ij Js Jt Ma Nd Nq Oz) Wm(Hq In Mj Mr Pg Po) Hq(Iv Lh Lz Oi) Il(Ih Lh Mk Pe) My(Mw Nb) Is(Jr Js) Iv(Ir Jn) Ny(Nb Pb) HaLj NoJr MgJt NiNk} Md{Nx(Fr Hw Ik Iv Jo Li Lv Mr Mw Nd Nh Nj Nt Oz Pb Pc Pe) Fr(Ik Lv Nd Nj Nt) Wm(Nw Ok) Nv(Hw Nd) NtPc LvMw} Ko{bV(bN Dc Dk Gl Ha Ii Jk Jq Jr Js Jt Kc Ma Mj Mu Pg Po Qw Ut Vo Vs) bN(gW Ma Qw) DcJm DrRc JkOy KccS} Nw{Wm(Hx In Js Mj Mr Ny) Dc(Js Nj) Mr(Il Mh) Ih(Il Qb) Qy(Dk Mu) PoPe MkHx JqbV} Fr{Nd(Ih Iu Iv Lj Nt Qa) Nq(Iv Nt) Mr(Hq Oy) Ik(Jo Ng) MkOy HqHw IhIq} Kc{Em(Ha Ju Jv Ul) bV(bL bN dJ Vp) cS(bL bN dJ) DrNk VodX} nD{nA(eD hV oP oQ qW qX rA rY rZ) hV(eD nJ oP) nJqW} In{Nt(Ih Jl Mr Qa) Ik(Ih Jl Mr) Wm(Ok Qa) LvIh MrQa} aV{Dr(aU cY gW) dO(bX cH dJ) gC(aJ dG dM) eP(cY dK)} Wm{Ok(Hq Ij Js Mj Mr Pg)} Hu{eM(Ib Kk Oa) eP(Nu Oa)} Em{Vo(Ph Qz) AxIb UaNx} Mr{Ik(Hq Oy) NjIl NxOy} Jo{Ik(Aa Lh) NtLv VqfP} Ih{Lv(Hw Qb) IbeP} bA{cH(aH cS dM)} dV{cF(dG dL) aJbR} Ha{Lj(Oy Qy)} CsGtcL DrStRa IbKfeP RbOzfR mSnArZ

Constrained panels with 2 analytes, where 1.0E-7 >= 'model p-value' > 0. Contains 80 panels of 81,255 total panels evaluated. : Ok(aA Hw Iq Jj Jo Js Jt Lv Lx Ly Md Mi Mt Nc Nd Ne Nf Nj Nl Of Og Om Pa) Et(Fp Ji Jj Jo Lx Ly Md Mi Mt Nc Nd Nc Nf Nj Nl Of Om Pa) Lx(aA Hw Ji Jj Ly Mi Nc Nd Ne Nf Nl Om On) Nw(Ly Md Nc Nd Ne Nf Nl Om) Ji(Ly Mt Nc Ne Nf Nl Om) Nl(Mi Mm Mt On) Om(Jg Mt On) On(Md Oy) LyaX MtJj Constrained panels with 2 analytes, where 1.0E-6 >= 'model p-value' > 1.0E-7. Contains 124 panels of 81,255 total panels evaluated. : Nw(aA Et Fp Hw Ik In Iq Jj Jo Js Lv Lx Mi Ml Ms Mt My Nj Nq Of Og Ok Oz Pa) Et(aA Hw Ik Iq Iv Jr Jt Lj Lv Mr Nh Nk Nq Og Ok On Oz Qe) Lx(Ik In Iq Iu Jg Js Lv Md Mm Mr Mt Nh Nj Nq Og Oz Pa Po) Mt(Fp Hw Lv Ly Md Mi Mm Mr Nc Nd Ne Og On Pa) Ji(aA Fp Hw Iq Jj Jq Md Nd Nj Og Oz Pa) On(Hw Iq Jj Ly Nc Nd Ne Nf Of) Jg(Jj Ly Md Mv Nc Ng Nl) Nl(aA Fr Jj Jp Pa) Ly(fR Gn Jp Mi) Ok(Fp Hq Nq Oz) Mi(Hq Nc Ne) Jj(Ik Nt) aX(Nf Ou) MmNc aJgP Constrained panels with 2 analytes, where 1.0E-5 >= 'model p-value' > 1.0E-6. Contains 161 panels of 81,255 total panels evaluated. : On(Fp Hq Hx Ii Ik In Jg Jk Jo Js Jt Lj Lv Mi Mm Ms Mv My Nb Ng Nh Nj Nq Og Oz Pa Pg) Nl(Aa Fp Hw Jl Lh Li Lj Lv Ly Md Me Mr Mz Ni Nk Nt Nv Nx Og Pc Pe Pg Qe) Jg(Fp Hw Ji Jo Jt Lv Mi Mt My Nd Ne Nf Nq Of Og Pa) Pa(aA aX Fp Ik Jj Lv Ly Mi Mm Nc Nd Ne Nh Nj Nt) Ji(Ik In Iv Jo Js Lv Mi Mm Ms Nh Nt Qe) Jp(Fp Ik Lv Mi Mt Nc Nd Ne Nj Om) Ly(AA bV Fr gP Jj Mm Ou Qe) Mi(Fp Ik Nd Nh Nj Nt Om Qe) aX(Et Kc Kk Ko Me Nj Ph Rb) Gn(aV Gl Hu Kc Kk Ra) Mm(aA Fp Ik Lv Nd Ne) Mt(aA In Iq Jl Nj Nq) Nc(aA Fp Fr Jj Lv) Ne(aA Fr Jj) Fp(aA Jj) Qe(Jj Om) Og(Ik Nt) NfOu Constrained panels with 2 analytes, where 1.0E-4 >= 'model p-value' > 1.0E-5. Contains 405 panels of 81,255 total panels evaluated. : aX(bA Fp gP Hc Hw Ih Jf Kd Kn Kp Lj Lv Lx Mr Mt Nd Nr Nw Oe Ok Om Or Oy Oz Pb Pc Qe Qw Qy Rj Sr St Ur Vp) Ly(aJ bA bN cH cS Dc dE dM Fp Id Ih Im Jf Jl Kc Ko Kp Lh Li Lj Lv Mr Nc Ne Nt Og Pe Ph Qa Sr) Gn(aJ aN Bb bR bU cF CH cN cP Cs dI dJ dL Ef Em Fw gP Ld Me Og Or Qw Rb Rc Ue Um Uo Vo) Nf(aJ bA bV cS dM Fp FR Jp Kc Kk Ko Lh Li Lv Mi Mm Mr Nt Pa Pe Qe Sr Ur) Mi(aA Hw Ih Im In Iq Iv Jj Jr Lh

Figure 9 Continued

Li Lj Lv Md Ml Mm Nx Oi Oz Pe Pg Qa) Qe(aA Dc Fp gP Hw Ik In Iq Jg Jp Lv Mm Nc Nd Ne Nh Nj Nt Og On Pa Qc) Ou(Bg bV cE Et gP gW Hq Jk Kc Ko Me Mk Mu Om Ow Pg Qw Rb Ut Vu Tj) Mm(Hw Ih Iv Jg Jj Jl Jp Jr Lh Lj Md Mr Nh Nj Nt Om Oz Pb Pe) Nc(Hw Ik Iv Jl Lh Li Lj Mr Nd Ni Nk Nt Nv Nx Og Om Pe Pg) aA(Ih Ik Jg Jj Jn Jp Jr Lh Lj Lv Nd Nh Nj Nt Nx Om On Pe) gP(bA Bc bV cH Dg Dl dM eF Et fR gL Kc Kk Ko Qy Sr Wm) Lv(Fp Fr Ih Ik Iv Jj Li Lj Mr Ne Nh Nj Nt Og Om Qa) Jj(Fr Im Iv Jl Jp Lh Li Mg Nh Nj Nv Nx Pe Pg Qa) Pa(bV Fr Hw Iq Iv Jl Jp Jr Lh Md Mr Nx Og Om Qa) Fp(Fr Hw Ik Iv Jl Lh Md Mr Nd Ne Nh Nt Og Om) Ne(Aa Hw Iv Jl Lh Li Lj Mr Nt Nv Nx Og Pe) Jp(Hw Iq Iv Md Mf Mr Nh Nq Nt Og On Oz) Et(Ao Bg bV Co Cw Dc Dk Gl Jf Kg Ut) Jg(Iq Iu Iv Jh Lj Mr Mu Nh Nj Oy Oz) Om(Aa Fr Im Jl Lh Li Nl Nt Nv Qa St) Nt(Fr Hw In Md Nd Nj On Oz) Fr(Ik Iv Nd Nh Nj) Me(bV Hf Sr) Kc(bN bV cS) nD(hV nA rA) Aa(Lx Mt) bA(cH cS) DcNw MdNx NdLh Nllv KobV NyOn aVdO Constrained panels with 2 analytes, where 1.0E-3 >= 'model p-value' > 1.0E-4. Contains 710 panels of 81,255 total panels evaluated. : gP(aA Ad AP aW Ax Ba cJ cR cS dF dG Fr Id It iZ Jf Jg Jp Kd Kf Kn Kp Kq Lh Lj Lx Me Mt Nd Nf Nj Nw Ok Oy Pa Pc Ph Pj Qa Qd Qw Rb Rj St Uh Ur) Nf(AA aP Ar Ax bN cH cR Cs DG eF gL Id Ik Im Iv Jf Jl Kd Kn Kp Kq Lj Ly Nh Nv Nx Pg Ph Qa Qw Qy Rb St To Uh Vq Vt Wm) Ko(Bg bN cS Dc Dd Dk dM Gl gW Ha Hq Hw Ij Iq Jf Jk Jo Kc Ma Md Me Mj Mr Mu Om Pa Pg Po Qt Qw Rb Rc Ut Vs Vu) Ou(Aa aU bF bN CH Co cS Ct Dk dM Gl Gn Ha Hw Io Jf Kp Lj Ma Md Mj Mr Mv Nw Oy Pa Pj Po Qy Sr Vp Vs) Ly(gL Hf Hw Ik Io Ir Iv Jn Jr Jt Ma Md Mk Mp Mz Nh Nj No Nr Nv Nx Pb Pc Pf Pg Qd Qw Uh Uk) Jj(Gn Hw Ih Ii Io Ir Jm Jn Jr Jt Lj Mf Mr Mz Nd Nm Nr Nu Oh Oi Oy Oz Pb Pf Po Pz Qb Qd) bV(cB cH hC Hq Hw In Kk Lv Lx Mt Na Nd Nj Nw Oe Og Ok Om Oy Pb Pc Ph Qe Qw Qy Rb Sr Wm) Et(aH aI aJ bA bN cE Ch cS dM Ef Ha Jd Kc Qn Qt Qw Ra Rb Rc Rg Tn Vo Vp Vs Vu Tj) Gn(Do eX Fb Fp Ib Iz Jy Kf Kj Ma Mf Mu Mv Nj Ny Oa Om Pc Qt Qu Qx Qz St Uf Uu) Kc(bA bL Dc dJ eF gW Hq Hw Jf Jp Lx Md Me Mm Mt Nw Om Pa Qe Qy Ra Sr Vp) Mr(Hq Hw Ik Im Iq Iv Lh Li Lj Nd Nh Nj Nt Og Om Oy Oz Pe Qa Qe Wm) Iv(aA aX Hw Ik Im Jl Lh Li Lj Nd Nh Nj Nv Nx Og Om Pb Pe Qa Qe) Nh(Aa Hw Ih Im Jl Jr Lh Li Lj Nv Nx Og Om Pb Pe Pg Qa) Nj(Aa bA cS dM Fp fR Im Jl Lh Li Lj Nv Nx Og Pe Pg Qa) aJ(aX bA bC bL bN bR bS bU cH cJ cM cS cT Me Pa Qw Rb) Nd(Aa bA Ih Im Jl Jt Li Lj Lv Nv Nx Og Pe Pg Qa Qd) Hw(Aa Fr Ih Ik Im Jl Lh Li Lj Lv Nv Nx Pe Pg Qa) Om(bA Dg Ih Ik Jt Lj Md Ne Nx Pe Pg Ph Qd Sr Uh) Lh(Hq Ih Ik In Iq Iu Jo Lj Lv Md Of Og Oz Qa) Fr(aA Ih Iq Jr Lj Md Mm Ng Nq Og Oz Qe) Me(bA cS fR Id Ik Jf Kp Ph Qw To Uh Wm) Pa(Aa bA cH cS Dc dM fR Ha Jf Ph Rb Sr) Ik(Aa Ih Jl Jo Li Lj Md Ne Nx Pe Qa) aA(cH Im Jq Li Mf Og Oz Pb Pc Pg Qa) Wm(aX bA bN cS dM hC In Md Mj Pg) Iq(aX Ih Im Jl Li Lj Mm Nv Pe Qa) Qe(bA Ha Il Iu Jf Md Nq Oz Qb Vu) Lv(dM fR Im Jl Md Nv Oz Pb Pe) Jp(Dc Jl Jr Lj Mb Nu Pb Pe Vs) Nw(Bg cS Dk Gl Ha Ut Vp Vu Tj) Og(Im Jl Li Mm Nv Nx Oi Pe Qa) nD(kC kP nJ nK nM nT nU oP qX) Ne(Im Jt Mz Nk Pb Pc Pg Qa) cH(aW aX cS cT dF dG dM gL) Nc(Aa Im Jt Mz Pb Pc Qa) Dc(Ad bA Dg Jg Lx Ok) Mm(Jo Li Mb Nk Nq Qa) dM(aX bA bR bU cM cS) Lx(Bg Gl Ha Qw Ut) Mi(Hx Ij Ny Of Oy) Oz(Aa fR Jl Li Qa) Ok(Bg Dk Gl Ut) Fp(Aa Ha Mg) Nt(Jo Lj Pb) Md(Li Nv Pe) In(Ih Pe Qa) Qy(Jk Mu Qw) aV(Dq Dr eP) bA(bM Db Di) fR(cP Pc Qw) oP(mF nC rX) Jf(Ph Pj) Jg(Bg Mw) Kk(bN cS) Lj(Ha Nx) Vo(Dg Em) aX(dG It) nO(jF rA) AaJr DqFw NqLi HqJl IuQa SrJs cBcS cEdF dGgC nUrA Constrained panels with 2 analytes, where 1.0E-2 >= 'model p-value' > 1.0E-3. Contains 1,522 panels of 81,255 total panels evaluated. : Om(Ad aJ AP Ar Ax Ba Bb BC bE bN cH CS Cu dF dG Dl dM eF fR Fy gL HC Hw Id Ii Ij Io Ip Ir Jd Jf Jh Jj Jm Jn Jq Jr Kf Kk Kl Kp Kq Lw Ma Mg Mk Mp Mu Mw Mx Mz Nb Nf Nj Nm Nn No Nr Nu Ny Og Oh Oi Oz Pb Pc Pf Pj Po Pz Qb Qw Qy Rb Tr Tt Uf Vt Wm) Hw(aJ Ax BA bC cH cS Dg Dl dM eF fP gL hC Hq Io Iq Ir Jf Jm Jn Jr Jt Kp Mg Mk Mw Mx Mz Nb Nd Nf Nj Nn No Nr Nu Og Oh Oi Oz Pb Pc Pf Ph Pz Qb Qd Qy Rb Sr St Wm) Qw(Aa Ad Ap Ax bA bC bN cH cS Dg Dl dM Dr eF Fp gL Hc Id Ih Ik It Jf Jg Jm Jp Kf Kk Kp Kq Lj Mm Mt Nj Nm Nr Nw Oi Ok On Oy Pa Ph Pj Qa Qe Rb Rf Sr St Tr Tt Uh Ul) bN(AP aX Ba BC bV cS Db dF DG Dl dM eF FP gL In It iZ Jf Jg Jp Kp Lj Lv Lx Me Mt Nj Nw Og Ok On Oy Pa Pc Ph Qe Qy Rb Sr) cS(aA aW Bc bR bU cJ cP cT dF DG Dl Fp gL HC Id Ih In iZ Jf Jg Kp Lj Lv Lx Mt Nd Nr Og Ok Oy Pb Pc Ph Qe Qy Rb Rf Sr Ur) hC(aA aJ aX bA cJ dM eF Et fP fR gL hB In It iZ Jf Jq Jr Kc Kk Ko Kp Ly Me Mj Nf Nk Nw oF Or Ou Pa Qe Ql Qy Rb Sr Ur Vp Vs) Dc(Ap Ba Bc cH Cu Dl Fp Ih It Ji Jm Kf Kk Kp Kq Lh Li Lj Me Mt Nj Nr Nx On Oy Ph Qa Qd Qy Sr St Tt Uh Ur Wm) Iq(Aa aJ Ax bA bE bV cB cH Cs dG dM fR gL gP Ir Jn Jr Jt Kk Mk Mp No Nr Nx Oh Pf Pg Ph Pz Qb Qd Sr St Wm) Jf(Aa aU bV cH dE Dg Dl dM gW Ih Io It Je Jk Jm Jp Kp Lj Lx Md Mm Mr Mu Nj Nm Nw Ok Oy Pc Qy Rb Sr St Ug) Nf(fP hB Ih Ii Ir Jj Jn Jq Jr Jt Lw Mg Mk Mp Mz Nb Nd Nj No Nr Nu Og Oh Oi oK Oz Pb Pc Pf Po Pz Qb Qd) Qy(Aa aU Bg CH Dk Fp gW Hq Ib In It Js Kp Lj Lx Mj Mr Mv Nj Nw Oe Oy Pa Ph Qe Qt Sr Ua Ut Vp Vs Vu) Wm(Aa aJ Bg Dk eF eP gL gW Ha Hq Hx Ij It Jj Js Lv Ly Mi Mk Ml Mw My Nb Nv Ny Og Oy Pb Ut Vp Vu Tj) Kk(Aa bC Bg Dk Ex gW Ha Hq In Jd Je Jk Jr Md Mj Mk Mm Mr Mu Nb Nj Nm Ny Oy Pg Pj Po Qx Ut Vp Vu Tj) Nd(aJ aP bC cH dG dM eF fR gL Io Ir Jn Jr Lw Mk Mp Mw Mx Mz Nb No Nr Nu Oh Oi Pb Pc Pf Pz Qb) Og(Aa eP fR Ih Ip Ir Jn Jq Jr Jt Lj Mf Mg Mk Mz Nb No Nr Nu Oh Oy Oz Pb Pc Pf Pg Po Pz Qb Qd) Rb(Aa bA cH dE dM Id Ih Io It Jk Jp Kc Kp Lj Lx Md Mu Nw Ok Oy Pb Pc Ph Pj Qe Sr St Uh Vp) dM(cJ cT Db dF DG Dl In It Jg Kp Li Lj Lx Me Mt Nr Nw Oe Ok Oy Pb Pc Pf Ph Qe Sr) aJ(Aa Db Di Dq dV fP gC Gt Ii In It Js Lv Mt Nj Nq Nw Oe Ok Oy Oz Pc Ph Ua Vp Vs) Ha(Ax bV Cs Dg Id Ih It Jm Jp Kp Li Mm Mt Nr Nx Oa Ok On Oy Pe Ph Qa Sr St Ur) Sr(Bg Dk Gl gW Hq Ii In Jk Kp Md Mj Mr Mu Oy Pc Pg Ph Po Ra Ut Vo Vp Vs Vu) Gt(aK aN aQ aV bA bC Bo bR bU cB cF cG cH cL cN cY Dd dG dI dJ eF Fw gP) Vp(Ax bA bV Fp hB Ih It iZ Jp Kp Lj Lx Mm Mt Nx Ok On Oy Pa Ph Qe St Ur) fR(AW bR bU cB cT Db Dd Di Fp In It Jj Jn Ml Mq Na Nc Ne Nl OE Pb) Vu(Ax Ih It Jg Jm Jp Kc Kf Kn Kp Lj Lx Nx OK On Oy Pa Ph St Uh Ur) Vs(bA Dg hB It Jg Kf Kp Lx Mm Mt Nw Ok On Oy Pa Ph Qe St Tt Uh) Aa(dG eF Ih It Iv iZ Jo Js Jt Lu Lv Ma Nq Oi oK Pc Qe Ra) Dg(aH aW aX Bg bV cP Cw Dd Dk Gl Ii In Jj Jo Jt Oe Pg Ra) Mr(Ar Ax bA Id Ih In Jr Kp Kq Lz Md Nu Nv Nx Pg Ph St Uh) Nj(eF gL gW Ih Jr Jt Mk Mp Mq Mz Nb No Nr Pb Pc Pf Qd) Oz(gP Ih Im Ir Jn Jr Jt Lj Mk Mz Nb Nr Nu Nv Nx Pz Qd) cH(aP Bc cP Dq eF eP fP In Lv Lx Me Mt Oe Oy Pb Pc Ph) nD(hR iB jF jQ jR lK lX lY mH mP mU mY nF nI nR oQ qW) Md(Ax bA hB Ii Im Jl Kp Mp Mw Nb Nu Pc Pg Ph Qa Uh) eP(aK aM bR cF dF dG Di dJ dK Dl gP Hu Ih It Mf Rf) rZ(hV jF mM nA nC nF nI nJ nK nM nR nU oP oQ rA rB) Gl(bA bV Jg Jp Kp Kq Lh Mm Mt On Pa Ph Qe St Uh) In(Ax bA dG Im Is Jl Kf Ko Kp Nv Nx Qd St Uh Ur) Lj(bA bC eF gL Jl Lz Mg Nv Oi Pb Pc Pg Rg Rj Tj) Dk(Ad Ba Dl Jg Jp Kf Kp Kq Lx Mt On Ph St Ur) aX(aA aC aW bM bR bS bU cB cJ cP cT dF Dl iZ) bV(bR bU cJ cT Db Di Dl gL Hc It iZ Kp Rj Ur) gP(eM FP hB Ik Im Ji Jm Lv Mm Nx On Pb Vq) Mu(eF gL Hc Kf Kp Kq Ph Rf St Tt Uf Uh Ur) Jr(hB Is iZ Jl Jt Mg Mk Nu oK Pb Pc Pf Pg) Nw(Ao bA Co Ib Jd Je Ph Qn Qt Qx Rg Rj Tn) Ut(bA cF Jg Jp Kq Mm Mt Nx On Oy Qe St Uh) Dq(aK aQ bC Bo cB cF cL cN cP cY dI Dl) Jk(bA eF Hc Jj Kc Kf Kp Kq Ph St Tt Ur) dG(Bg bL bR bS bU cT Db dH dV Hq Me Pc) Jg(Aj Ao aU Ch Co Ct Cw Ef Iz Ua Vo) Ok(aH Ao cE Ch Co Ct Kg Qn Qt Tn Tj) hV(kE lL lW mF mI mM mS nO nU oP rB) iZ(cJ Et fP Me Mj Nk oK Pa Ql Ur Vq) Em(cB Fn Ib Jj Kj Pc Qz Ue Uo Ur) Pb(Ih Im Ir Jn Jt Mz Nu Oi Qa Qd) rA(mF mI mZ nC nR nT oP oQ rB rY) Jp(Ao Bg Ct Cw Dd Ph Qt Tn Ua) bU(aP aW Bc cJ cT cU dA dE dF) St(Hq Hx Ii Js Mj Oe Pg Po) Jl(Im Lh Li Nv Nx Oy Pe Qa) Ph(aU bC gW Hq Ma Mj Pg Ra) nC(jF lL mZ nB nJ nL nR oQ) oP(cD hR jQ lK lX nU qX rY) Qe(bC Bg cQ Dd Qg Ra Tj) Jj(Ij Mk Mw Mx Ng Nn Pc) Kp(gL gW Hq Lx Mj Pa Pg) bA(Hq Ii It Lv Oe Pc Pg) Ih(Iv Mg Nx Pc Pg Rm) Ur(gL gW It Mj Oy Tj) nR(eD lK nK qX rX rY) mI(kC kP mH mZ qW qX) oQ(eD hR mZ nU rX rY) Bg(Ba Kq Mt On Oy) Dl(aA aW bC cP Dd) Me(aP Ar fP gL Vq) Nx(Dr Im My Ny Tj) Oy(Pj Ua Vq Tj) Pc(aP bC eF gL) Pe(Hq Iu Lh Lz) cJ(aA aP aW gL) nO(jQ jR qW qX) nU(hR lK qW qX) mM(eD lK rX rY) Ax(Js Pg Rg)

Figure 9 Continued

Ba(Ct Cw Dd) Jo(Kf Nv Pj) Ko(cM Ii Mv) On(Co Ct Ua) Pa(gL Rj Tj) bR(aA aP cU) dF(aH bQ dV) eF(Di iJ Mv) fP(aH bE cE) mZ(eD IK nB) hB(bQ cE Mj) Dr(Mz Ra) Lx(Co Tj) Hq(Mp Uh) Im(Iu Nu) Kc(oK Ul) Nv(Nq Of) Vq(Ky oK) Pg(Ar Iv) bC(Fp Lv) cT(bM dE) gW(Uh Uk) nH(nJ nL) AdDd EtiJ GcKj NoMc MmVo IbeM IsJs RaPj LhLi aAdE aPbL cNdV dLgC eDlX mFqW mWhR rBjF

Unconstrained panels with 3 analytes, where 1.0E-10 >= 'AUC p-value' > 0. Contains 7,822 panels of 10,034,416 total panels evaluated. : Gn{Ly(AA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR Ed EF Em Et Ex Ez Fa Fb Fn Fp Fr Fw Fy Gc GL GP gW Gz Ha Hb Hc Hf Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tr Tt Tv Tz Ua Ub Uc Ud Ue Uf Ug Uh Uk Ul Um Un Uo Up Ur Us Ut Uu Uv Vo Vp Vq Vs Vt Vv Wm Tj) Rc(AA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR Ed EF Em Et Ex Ez Fa Fb Fn Fp Fr Fw Fy Gc GL GP gW Gz Ha Hb Hc Hf Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rf Rg Rh Ri Rj Rm Sr Ss St Tn To Tr Tt Tv Tz Ua Ub Uc Ud Ue Uf Ug Uh Uk Ul Um Un Uo Up Ur Us Ut Uu Uv Vo Vp Vq Vs Vt Vv Wm Tj) Ra(AA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR Ed EF Em Et Ex Ez Fa Fb Fn Fp Fr Fw Fy Gc GL GP gW Gz Ha Hb Hc Hf Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Rb Rf Rg Rh Ri Rj Rm Sr Ss St Tn To Tr Tt Tv Tz Ua Ub Uc Ud Ue Uf Ug Uh Uk Ul Um Un Uo Up Ur Us Ut Uu Uv Vo Vp Vq Vs Vt Vv Wm Tj) Hu(AA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS cT CU CV CW CX cY cZ dA DB DC DD DE dF DG dH DI dJ DK DL dM dN Dp Dr Ed Ef Em Et Ex Ez Fa Fb Fn Fp Fr Fw Fy Gc GL GP Gz Ha Hb Hc Hf Hq Hr Hv Hx Ib Ic Id Ih Ii Ij Ik Il Im In Io Ip Iq Ir Is It Iu Iv Iz Jd Je Jf Jg Jh Ji Jj Jk Jl Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Rb Rf Rg Rh Ri Rj Rm Sr Ss St Tn To Tr Tt Tv Tz Ua Ub Uc Ud Ue Uf Ug Uh Uk Ul Um Un Uo Up Ur Us Ut Uu Uv Vo Vp Vq Vs Vt Vv Wm Tj) Vo(aA aC AD aE AF aG aH aI AJ aK AL aM AN AO aP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN cO CP CQ cR CS CT CU CV cW CX cY cZ dA dB DC DD DE dF DG dH DI dJ DK DL dM dN Dp DR Ed EF Em Ex Fa Fb Fn Fp Fr Fw Fy Gc GL GP gW Gz Ha Hb Hc Hf Hq Hr Hv Hw Hx Ib Ic Id Ih Ii Ij Ik Il Im In Io Ip Iq Ir It Iu Iv Iz Jd Je Jf Jg Jh Ji Jj Jl Jm Jn Jo Jp Jq Jr Js Ju Jv Jy Kc Kd Kf Kg Ki Kj Kk Kl Kn Ko Kp Kq Kr Ks Kx Ky Ld Lh Li Lj Lu Lv Lw Lx Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Nj Nk Nl Nm Nn Nq Nr Ns Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qg Qh Ql Qm Qn Qt Qu Qv Qw Qx Qy Qz Rb Rf Rg Rh Ri Rj Rm Sr Tn To Tr Tt Tv Tz Ua Ub Uc Ud Ue Uf Ug Uh Uk Ul Um Un Uo Up Ur Us Ut Uu Uv Vp Vq Vs Vt Vv Tj) Rb(AA aC AD aE AF aG aH aI AJ aK AL aM AN AO AP aQ AR AS aU aV AW aX aY aZ BA BB BC bE bF BG bH bI bJ bL bM bN BO bP bQ bR bS bU bV bW cA cC cD cE cF cG CH cI cJ cK cL cM cN CO CP CQ cR Cs CT CU cV CW cX cY cZ dA dB DC DD DE dF DG dH DI dJ DK DL dM dN Dp DR Ed EF Em Et Ex Ez Fb Fp Fr Fy Gc GL GP gW Gz Ha Hb Hc Hq Hr Hv Hw Hx Ib Ic Ii Ij Ik Il Im In Io Iq Ir Is It Iu Iv Iz Jd Je Jg Jh Ji Jj Jk Jn Jo Js Jt Ju Jv Jy Kc Kd Ke Kf Kg Kj Kk Kl Kn Kq Kr Ks Ky Lh Li Lu Ma Md Me Mf Mg Mk Mm Mq Mr Ms Mt Mu Mv Mw My Na Nb Nd Nf Ng Ni Nk Nl Nm Nn Nq Nr Nt Nu Nv Nx Ny Oa Oe Of Og Oi Ok Om Or Ow Oy Oz Pa Pc Pd Pe Pg Pi Pj Pk Po Pz Qa Qc Qd Qh Ql Qm Qn Qt Qu Qw Qx Qy Qz Rf Rg Rh Rj Sr Ss Tn Tr Tt Tv Tz Ua Ub Uc Ue Uf Ug Uh Uk Ul Um Un Uo Up Ur Ut Uu Vq Vt Wm) Uo(AA aC AD aE aG aH aI AJ aK AL aM AN Ao AP aQ Ar As aU aV AW AX aY aZ Ba BB BC bE bF Bg bJ bL bM BN Bo bP bQ bR bS bU bW bZ cB cC cD cE cF CH cI cK cL cM cN CO CP Cq Cs CT cU Cv CW CX cY dA dD dE dF dG dH DI dJ DK dL dN Dp dR Ed EF Em Ex Ez Fa Fb Fp Fr Fw Fy GL gP gW Gz Hb Hf Hv Ib Ic Id Ih Ii Ij Ik Il Ip Is It Iz Jd Jh Ji Jj Jk Jl Jm Jn Jo Jp Jq Js Jt Jy Kc Kd Ke Kg Kj Kk Kl Ko Ks Kx Kz Ld Li Lj Lu Ma Md Me Mg Mk Ml Mn Mq Mr Ms Mu Mv Mw My Na Nc Nd Ne Ng Nh Nj Nk Nl Nm Nn No Nq Nr Nt Nv Nw Nx Ny Oa Oh Oi Ok Or Ow Oy Oz Pb Pe Pi Pj Po Qd Qe Qg Qm Qt Qu Qv Qw Qx Qy Qz Rf Rh Ri Rm Sr Ss Ua Ub Uc Uf Ug Uh Uk Ul Um Un Up Ut Uu Uv Vp Vq Vt Vv Tj) Om(AA aC AD Af aG aH aI AJ AL aM AN AO aP aQ Ar aS aV AW AX aY aZ bA BB bE bF bJ bM BN bO bP bQ bR bS bU bV bW bX bZ cA cB cC cE cF cG CH cI cK cL cM cN cO cP CQ cR CS cU CV CW CX dA dB dC DD DE dG dH DI dJ dK DL dM Dp Dr eF Em Ex Ez Fa Fb Fn Fp Fw Gc Gl gP gW Gz Hb Hf Hq Hr Hw Ib Ic Id Ih Ij Ik Il Im In Io Ip Is It Iv Iz Jj Jm Jn Jq Jr Ju Jy Kc Ke Kf Kj Kk Kl Kn Ko Kp Kr Ks Kx Ky Ld Lh Lj Lu Lv Lx Ma Me Mf Mg Mh Mm Mn Mp Ms Mt Mx Mz Na Nb Nd Ne Nf Nj Nk Nl Nr Ns Nt Nu Nw Oa Oe Og Oh Oi Ok Or Oz Pa Pb Pc Pd Pe Pf Pg Ph Pi Pj Pk Po Qa Qb Qg Qh Ql Qn Qt Qu Qw Qx Qz Rh Sr Ss St To Tr Tv Ub Ue Uf Uh Up Uu Vv Tj) Me(Aa AD aG aH aN AO Ap aV aX Ba Bb bF Bg bL bR CH Co CP Cw Dc Dg dJ Dl Dp Ed Ef Et Ez Fb Fn Fy Gl gP Gz Ha Hb Hc Hf Ib Ic Id Ii Ij Im Is Iz Jd Je Jf Jg Jh Jj Jk Jo Jt Ju Jv Jy Kd Ke Kf Kg Ki Kj Kk Kl Kn Ko Kp Kq Kr Ks Ky Kz Ma Mn Ms Mu Mv Mw Nd Ng Nm Ny Oa Oe Of Og Or Oy Oz Pc Pj Pz Qg Qh Ql Qm Qn Qt Qu Qv Qw Qx Qy Qz Rf Rg Rh Ri Rj Rm Sr Ss St Tn Tr Tt Tz Ua Ub Uc Ud Ue Uf Ug Uh Uk Ul Um Un Up Ur Us Ut Uu Uv Vp Vq Vs Vt Vv) Qw(Aa Ad Af aG AJ aN AO Ap aR aV aW Ba Bb Bg bL bP bR cF CH Co Cp Ct Cu Cw Dc Dd Dg dJ Dk DL Dp Ed Ef Et Ez Fb Fr Fy Gl gP Hb Hw Ib Ic Ii Ij Ik Il Im In Ir Is Iu Iz Jd Je Jf Jg Jh Ji Jj Jo Jp Jq Js Jt Ju Jv Jy Kd Ke Kf Kg Kj Kl Kn Kq Ks Li Lu Ma Mg Mn Mr Mt Mu Mv Mw Nb Nf Ng Nk Nl Nm Nn Ny Of Og Oi Ok Or Oy Pd Pj Pz Qm Qn Qt Qu Qv Qy Qz Rh Ss Tz Uc Ue Uf Uh Uk Ul Um Un Ut Uu Vq Vt) Um(Aa aD AJ aM AN Ao aU aV Aw AX Bb Bg bP

Figure 9 Continued bR bW cA cE cF CH cl cN cO cP Cs Ct CW dE dG DI dJ dK dL Dp Ef Em Ex Ez Fb Fp Fw Gl gW Hf Hr Hv Ib Id Ih Ij Ik In Iz Jh Ji Jj Jn Jo Ju Jv Jy Kc Kj Kk Kl Kn Ld Lj Ma Mb Mf Mk Mu Mv Nb Nf Nj Nk Nu Nv Nw Nx Oa Og Oh Ok On Or Oy Qa Qd Qe Qt Qu Qv Qx Qy Qz Rf Rm Ss St Ub Uc Ue Uf Uk Uu) Ue(Aa aC aD AF aG aJ aM aN aO aQ aR AS aU aV aX aY aZ bA BC bF bI bJ bL bP bR bU bV bX cD cF CH cJ cM cN cP cR CS cV cX cZ dA dC dE dI dJ dL dM dN Dp Ex Ez Gl Gp gW Hq Ib Ih Ij It Jj Jp Ju Jy Kc Kd Kj Kk Ko Kp Ky Kz Lx Mb Mf Mk Ms Mu Mv Mz Na Nb Nf Nx Ny Oe Og Or Ou Ow Oy Oz Pa Pb Pc Qt Qu Qx Qy Rf Uf Uk Ul Up Ut) Kc(Aa aC AD Af aG aH AJ aN AO Ap aV Ba Bb Bg bL cF Ch Co Cp Ct Cu Cw DC Dd Dg dJ Dk DL Ef Et Ez Gl Hb Hw Ib Ii Ij Ik Il Im In Is Iz Jd Jg Jh Jj Jk Jo Js Jt Ju Jv Kd Ke Kf Kg Kj Kl Kn Kp Ks Lh Li Lu Ma Mg Mn Mt Mu Mv Ng Nm Ny Of Og Oi Ok Or Pj Pz Qm Qt Qu Qv Ss Ua Uc Uf Uh Uk Ul Un Ut Uu Vq Vs Wm) aV(Aa aC aD Af aG aH aJ aK aL aN Ap aQ aU aW aX aY Bb bE Bg bJ Bo bR bU cD cF CH cl cK cN CO cP Cq Cs Cw cY Dc Dd dE dG DI dJ dK dL dM DO Dq dR Ef Em EX Ez Fb Fp Fr Fw Gl GP gW Ib Ic Ii Ij In Io Iz Jj Kf Kk Kl Kn Ma Mf Mk Mu Mv Nb Nd Nx Ny Og Or Pc Qt Qu Qx Qz Uf Uu) cP(Aa aD aJ aN Ao Ap aR aU aX Ba Bb bE bH bL bP bR bU cF CH cl cN Co Cs Ct Cw Dc dE dI dJ DK dM Do Ef Em eX Ez Fb FR Fw Fy Gl GP Hc Ib Ij Ik Iz Jd Jg Jh Jj Jt Ke Kf Kg Kj Kk Kl Kn Ks Ma Mb Mn Mq Mr Mu Mv Mw My Nd Ng Nk Nm Ns Ny Og Or Oy Po Qm Qt Qu Qv Qx Qy Rh Uc Uf Uh) Og(Aa aN Ao Ap aQ As aZ Bb bF bL bU cE cF Ch cN Co CU Cw cY Dc dJ Ef Em Ez Fb Fr Fy Gl gP Hb Hv Ib Ic Ij Im Iz Jd Je Jj Jv Jy Kd Ke Kf Kg Ki Kj Kk Kl Kn Kq Ks Kz Ld Li Ma Mr Mv Nj Nk Nl Ny Or Oz Pc Pi Pj Po Qh Qm Qt Qu Qx Qy Qz Rh Ss Uf Uh Uk Ul Un Up Vq) Aa(aA AD aM aN aO aX bC bR bU cD cF Ch cM cN Cs dA Dl dJ DL dO Ef Et Ex Fa Fp Fw Gc GL gP Gw Ib Ih It Ji Jj Jm Jp Kf Kk Ko Ky Ld Lj Mf Mk Mm Mv Mz Nd Nj Nv Nw Nx Oc Oh Oi Ok On Or Ou Oy Pb Pc Ph Pj Qb Qe Qt Qu Qx Rf Rm Sr St) Qt(aD aG aJ aK aN aP aQ aZ bA Bb bI bJ bL bO bR bV cB cC cE cF CH cI cJ cM cN cO cQ Cs cW dE dG dH dI dJ dL dM dN gL gP Hb Hq Hv Hx Ib Iq Iv Jo Jv Jy Kd Kf Kk Mf Mu Mv Na Nb Nm Ns Ny Oh Or Ou Oy Oz Pa Pc Qx Uk Ul Ut Uu Vv) Ib(aA aG aH al aJ aN aP aQ aR AX aZ bA bH bR bS bV bW cB cC cD cE cF cG CH cI cN cO Cs cW cZ dA dC dE dG dJ dK dL dM Ex gL GP gW Gz Hf Ih Jn Jy Kd Kk Kp Ky Lj Mn Mt Mu My Na Nb Oa Oh Or Ou Pc Ph Qb Qx Sr Vv) cN(aK Ap aQ Bb bL bR bU cE CH Cw cY dl dJ DO Dp Ef eX Ez Fb Gl gP Hb Ii Ij Im Iz Jj Jk Jo Js Jt Jv Kd Ke Kf Kj Kl Kn Ks Mg Mu Mv Mw Ng Nm Ny Of Or Pd Qm Qu Qv Qy Uc Uf Uh Ul Un Uu Vt) Or(aD Af aG aJ aN AO aX Bb bL bN bP bR bU cF CH cM dI dJ dL Dp Ez Gl gP Hb Hw Iq Iz Jh Jj Jv Jy Kd Ke Kf Kj Kk Kl Kn Mf Mg Mu Mv Nb Nm Ny Of Oi Ou Ow Qn Ss Uf Uk Ul Ur Uu) Ny(aD aJ aM aN aP Ar aZ bR bU cF CH cI cJ cL cO CS cW dF dG Di dJ dL Ex Fa Fp Fw gL Hf lp Kk Ky Ld Lj Mf Mu Nb Nj Nu Nv Nw Nx Oa Ok Qa Qb Qd Qe Qu Rf Sr St To) Gl(aA aD aF aJ aM aN aO aR bA BC bL bN bR bU cF cH cM cT dD dI dJ dL Fw Hc It Jj Kd Ko Kp Ky Mf Mv Nb Nd Nx Oe Ou Ow Oy Oz Pa Pb Pc Rf Uk Ul Ur) Kk(Af aG Ao Ap As Ba bL cF Ch Co Cw Dc Dg dJ Dl Ed Ef Ez Hb Ij Im In Iz Jd Jg Jh Jj Jt Jv Kd Ke Kf Kj Kl Kn Ks Ma Ng Nm Of Pj Qu Ss Uf Ul Uu) Kf(aD aJ Al aM Ar AX Ch cI Cs dJ Ex Ez Fa Fp Fw gW Ii It Jm Jp Jy Kl Ko Kq Ld Lj Mf Mk Nj Nm Nv Nx Oa Oh Ok On Qa Qx Rf Sr To Uu) cF(aG aJ aN Ao Ap Bb CH cM Cw dJ dL DO Dq dV Ef Ez gP Gt Gw Hv Ij Iz Jj Jo Jv Jy Kc Kj Kl Ma Mu Mv Nm Qu Qv Uf Uh Ut Uu Wm) Uf(aD aG aJ aP aX bC bL bR cH cO CS dG dJ dL Ex Fa Fp Fw It Jj Jp Kd Ko Lj Mf Nb Nx Oe Oh Ok On Ou Ow Qe Rf Tr Ul) bR(aD Af aG aJ aN Ao Ap aX Bb bL cE Ch cL Co Cw dJ Dk dL Do Ef EX Gc gL gP Gt Hb Ij Jy Kj Kl Kn Nd Qm Qu Ul) dJ(aD aG aJ aN bC dl Do Dp Ef Ez Fy gP Ii In Ij Kj Kl Lj Lu Mf Mn Mv Ng Nj Oa Oe Oz Pc Qu Qy Uc Uh Uk Uu) Kn(aJ Ax aZ bU CH cM Cs dL Ex Fa Fp Fw Hf ld Jj Ko Lj Mf Mz Nw Nx Oa Oh Ou Qb Qu Qz Rf Sr St) Ez(aD aJ aX aZ cH cO DI dL Fw gL gW Hf Ih It Ko Ld Mf Mu Nj Nl Nx Oa Oe Ok On Ou Pc Ph Qx) Nx(Ao Ba Co Cw Ef Fb Ii Ij Im Iz Jd Jo Jt Ke Kg Kj Kl Ks Ng Nm Of Pj Qu Tz Ul Un Ut Uu) Qu(aJ bA bU cH cT dD dL Ex gL gP Hc Jy Kd Mf Nb Oa Oe On Ou Oy Oz Pc Tn Ul Vv) aD(Bb bU cE Cw Dp Ed Fp gP Gt Hb Jn Jy Ke Kg Kj Nf Nl Ou Oz Pa Pc Rg St) Ul(AX Ch Cs Di Ef Ex Fa Fp Fw gW It Ko Ld Lj Mu Mz Nj Oa Oh Qx Rf) gP(aJ Ao As aX Bb bF Bo bP CH Cs Ct cW dL. Do Dq dX Ef eX Fw Gt Wm) Ke(aJ aX cH Cs dL Ex Fa Fp Fw It Jj Jp Ko Lj Nb Nw Oe Oh On Qx) Iz(aJ aX Cs Ex Fa Fw gW It Ko Lj Nb Nd Nj Oe On Pb Pc Qx) Fw(aG aO Ba bL Cw Ef eP eX Hb Ii Ij Im Jt Jv Kj Uu) Cs(aN Cu Fb Hb Ii Ij Jj Jt Jv Kj Kl Li Ma Nm Pj) bU(aG aJ aN Ao Ap Bb Ch Cw dL. Do Ef eX Gt Jj Uu) Nj(aG AO Ch Ef Hb Ij Jj Jv Kl Mv Ng Of Uu) Ex(Hb Ii Ij Im Jd Jt Kl Ks Nm Pj Uh Un Uu) Do(aK aM aO aQ bC bL cA cC cL DI dO) aJ(aG Ap Cw dA dI Fb Jd Mv Mw Nd Nm Un) dL(aO Ap bL Cw Fb Jt Ld Mv Pc Uh Un Wm) Ch(aG aN Jy Nb Nd Ow Oy Oz Pc Qy Qz) Ef(aG aN eX It Ko Nb Nd Oe Oh Ou Pc) Jj(As Bb dE Fp Jy Ky Mf Nl Oz Pc Uh) Kj(aX Fp gW Ih It Ko Mf Nb Oe On Tr) Ld(Af aG Ao Hb In Jv Nm Of Uu) aN(Ax Bb cH Cw dI eX Qv Ut Wm) aX(Dp Hb Ic Jy Kd Kl Qm Qv Uu) Nb(Bb Jd Jh Jy Ma Mu Mv Oy) Ij(Fp Ih It Ko Lj Mf Rf St) Jt(Fa Fp Ih It Ko Oe On Rf) Kl(Fp gW It Ko Lj Oh On) Hb(cH gW Ko Kp Mf Nw) Jy(aG aO cH Gp In Mv) Ou(Co Fb Fy In Ma Uh) Uu(Em Ih It Mu Oe On) Nm(Fa Fp Ko Lj Oa) Ii(Ih Lj Oe On Rm) eX(Ap bX cL Dc dI) Ao(dI Fa Oz Pc) bL(dE dG Dq Mv) Fb(Lj Ow Rf) Mu(Kd Qz Wm) Ng(Ky Nl Qx) Ko(Cw Jo Ks) gW(Jv Uc Uk) Bb(bC dA) Fp(Ks Li) Gp(Uk Vs) Mf(Im Mn) Mv(Hv Qz) In(Oa Rm) It(Cw Jo) Oy(Oz Pc) cH(Jd Vq) AfBn BoGt DpcM DqdI MaVv MrKd MwQz NlaG UcIh SsQx QvaM KsOn LiLj dAdG} Ly{fR(AA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN dX Ed EM eP Et Ex Fn Fp Fr Fw Fy gL gP Gz Ha Hb Hq Hr Hu Hv Hw Hx Ib Ic Ih Ii Ij Ik Il Im In Io Ip Iq Ir Is It Iu Iv Jd Jf Jg Jh Ji Jj Jk Jl Jm Jn Jo Jp Jq Jr Js Jt Ju Kc Kd Kj Kn Ko Kq Ks Ky Lh Li Lj Lu Lv Lw Lx Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Or Ou Ow Oy Oz Pa Pb Pc Pd Pe Pf Pg Ph Po Pz Qa Qb Qc Qd Qe Qg Qh Ql Qw Qx Qy Ra Rf Rg Rj Sr St Tn Tt Tv Ub Ue Uk Uo Up Vp Vq Tj tF) Dr(Aa aC aD Af aG aH aI AJ aK AL aN Ao AP aQ aR AS aU aV aW aX aZ BA Bb BC bE bF BG bH bI bJ bL bM Bn BO bP bQ bR bV bW bX cA cB cC cD cF CH cI cJ cK cL cN CO CP CQ cR Ct CU CW cX cY cZ dA dB DC DD DE dF dG dH DI dJ DK dL dM dN Dp Ed Ef Em Ez Fb Fn Fr Fy Gl GP Gz Ha Hb Hc Hf Hr Hu Hv Hw Ib Ic Ii Ij Ik Il In Io Ip Iq Ir Is Iu Iv Iz Jd Je Jf Jh Jj Jk Jn Jo Js Jt Ju Jv Jy Kd Ke Kf Kg Kj Kl Ko Kp Kq Kr Ks Kx Ky Kz Ld Li Lu Lv Lw Lz Ma Mb Mc Md Me Mh Mi Mj Ml Mn Mp Mq Mr Ms Mu Mv Mw Mx My Mz Na Nb Nc Ne Nf Nh Ni Nj Nk Nl Nm Nq Nr Ns Nu Oa Oe Of Og Oh Oi Om Or Ow Oy Oz Pa Pb Pc Pi Pj Po Pz Qb Qh Ql Qm Qt Qu Qx Qy Qz Ra Rc Rg Rh Ri Rj Ss To Tr Tt Tv Tz Ua Ub Uc Ud Ue Uf Uh Uk Ul Um Un Uo Ur Us Uu Uv Vo Vp Vq Vt Wm Tj) Em(aA Ad aF AJ aK Al aN Ao aP aQ AS aV Ax aY aZ bC Bg bI bJ bL bN BO bR bV bX cA cB cE cF CH cL CO CP cQ Ct CU Cv CW CX cY Db DC Dd DE dG dH dI dJ Dk dL dM dN Dp Ed Ef eM Fb Fn Fw Gc Gl GP Gz Ha Hb Hf Hr Hu Hw Ib Ii Ij Il In Ip Ir Iz Jd Je Jf Jh Jj Jk Jl Jm Jo Jq Jr Js Jt Ju Jv Jy Kc Kd Ke Kg Kj Kk Kl Kn Kq Ks Lh Li Lu Lv Lz Mb Md Mh Mj Mq Mr Mu Mv Mw Mx My Mz Na Nb Nc Ne Nf Ni Nk Nl Nm Nn Nu Ny Of Og Oi Om Oy Oz Pb Pc Pg Ph Po Qh Ql Qm Qn Qu Qx Qz Rc Ri Rm Ss To Tr Tt Tz Ua Ub Uc Ue Uf Ug Uh Uk Ul Um Un Uo Up Ur Uu Uv Vo Vp Vs Vt Vu) eM(aC aD aJ AN Ar aV aX aZ bE Bg bI bJ Bo bQ bR bS bX cF CH cL cM cN cO Cp cS Ct cV Dd dE dF dG Di dJ dK DL Dp eF Et gP Hq Hr Hu Hv Ih Ii In Io Ip Ir It Iu Jh Jj Jn Kc Md Mf Ms Mv Nb Ne Nf Nj Nk Nn No Nq Nu Of Og Oi Ok Oy Ub Uk) eP(aC aJ aM aN Ar aX aZ bC bE cF cG cH cI cL cN cO CP cS DG dJ dL eF Et gP Hu Ih Ii Ir It Iu Jj Jp Md Nb Nn Nu Og Om Qd Qy Ub) dX(aA aC aD aJ aM aN Ar aX bE cL cN cP cS cW Dd dG dJ dL dM dN Et gP Hu Ih It Jj Jp Kj Nu Oi Ok Ub Ue Uk) Gc(Aa AJ aN aQ aS aV bI bL bR bV cF cH cL cY dG dJ dL Dp Ed gP Ii Jj Jo Jt Jy Kj Nk Rc Ub Ue Un Vo) Nw(aX Fr Hq Hr Hw In Jg Jj Jo Jp Js Jt Lj Lx Lz Md Mi Ml Ms Mt Nc Nd Ne Nf Nj Nl Of Og Om Oy Oz Pa Qe) aX(AA aJ aN aQ aZ bA bJ bN bW cB cE Et Ik Im Jj Jq Js Lj Lv Lx Mb Md Mt Nf Nj Ns Ou Pa Pb Qe) Lx(aA Et Hr

Figure 9 Continued

Hw Hx In Jg Jj Jo Jp Js Lv Lz Md Mi Mt Nc Ne Nf Nj Nl Og Ok On Po) Ok(Hw Jj Jo Js Jt Nc Nf Nl Of Og Pa) Et(Jj Jo Jt Mt Nc Ne Nl Of Og Pa) On(Hw Jo Md Nf Ng Of Og Om Oy) Jp(Md Mi Mt Nf Nl Og Pa) Mt(Hw Jj Mi Og Pa) Jg(Jj Jo Of Og) Ji(Nf Og) gP(aJ bV) AaNl} Kc{Em(Aa Ad AJ Al aN Ao Ap aV Ba Bb bL cF Ch Co Cp Ct Cu Cw Dc Dd De Dg dJ Dk DL Ed Ef eM Ez Fy Gl Gz Ha Hb Hu Hw Ib Ii Ij Ik Il Im In Ir Is Iu Iz Jd Jf Jg Jh Jj Jk Jo Jq Js Jt Ju Jv Kd Ke Kf Kg Kj Kl Kn Kp Kq Ks Kx Lh Lu Ma Me Mg Mq Mv Mw Ng Nm Nu Of Og Oi Om Oy Pg Pj Po Pz Qh Qm Qn Rc Rh Ss Tz Ua Uc Ue Uf Uh Uk Ul Um Un Uo Ur Uu Vo Vs Vt Vu) Dr(Aa Ad AJ Ao Ap aV Ba Bb bL cF Ch Co Cp Ct Cu Cv Cw Dc Dd dJ Dk DL Ed Ef Et Ez Fb Fr Fy Gl Hu Hv Ib Ii Ij Il Im In Ir Is Iz Jg Jh Jj Jo Js Jt Ju Jy Kd Ke Kf Kg Kj Kl Kn Kp Ks Kx Me Mu Mv Ng Nl Nm Of Om Oy Pj Pz Qu Qv Ra Rc Ss Ua Ue Uf Uk Ul Un Uo Uu Vo) dX(aL aM aN aS aX bJ bW cH cN Cp Cw dB Dd dG dJ dK DL dN gP Ha Hu Ib Ii It Jh Jj Ki Kj Ko Kp Lj Mb Me Nb Ne Nf Nu Og Oi Om Or Oy Qu Qy Rc Rf To Tv Tz Uk Um Uo Ur Uv Vo Wm) eM(aC aN aV aX bE Bg bl bJ bR CH cN cO CP cV dB Dd dE dG dJ dK dN Dp fR gP Hu Ib Ii It Je Jh Jj Jp Ky Md Nb Og Or Oy Rc Rf To Ub Uo) eP(aK aM aQ aX bJ cG cH cL cN cO Cp Dd dJ dK DL dN Dp Ed gP Ha Hu Ii It Jj Jp Kj Ko Kp Nb Nu Og Om Or Rc Rf Uo Vo) Gc(Aa AJ aV cF Cp dJ dL Hu Iz Jj Jo Jt Kj Of Qv Rc Ue Uu Vo) fR(Me Ou)} Nw{Nf(Fp Fr Hq Hu Hv Hw Hx Ih Ik Im In Iq Ir It Iv Jg Jh Ji Jl Jm Jn Jo Jp Jq Jr Js Jt Lh Li Lj Lu Lv Lx Lz Ma Mb Mc Md Me Mf Mg Mi Ml Mn Mr Ms Mt Na Nc Nd Ne Nh Ni Nj Nk Nl Ns Nt Nu Of Oi Ok Om On Oy Oz Pa Pe Pf Pg Po Pz Qa Qb Qd Qe) Nl(aA Et Hq Hr Hu Hv Hw Hx Ii Ij Ik Il In Iq It Jh Jj Jk Jm Jn Jo Jq Jr Js Jt Lj Lv Lx Lz Mc Md Me Mh Mi Mj Ml Mq Ms Mt Mx My Na Nd Ng Ni Nk Ns Nv Ny Oe Of Og Om Oy Oz Pa Pd Pf Pg Po Qa Qb Qc Qd) Nc(Et Hq Hv Hw Hx Ii Ij Ik In Iq It Jj Jk Jo Jq Jr Js Jt Lj Lv Lz Md Ml Ms Mt Mx My Nd Ni Ns Of Om Oy Pa Pd Po Qb Qc) Md(Fp Hw Hx Ik Iq Iv Jg Js Lv Lx Lz Ms Mt Nd Ne Nj Nk Nt Oi Om Oz Pa Qe) Ik(Hq Hw Ij In Jo Js Jt Lz Nd Nj Of Og Om Oy Pa) Js(Hw Iq Jg Lx Mt Nd Ne Nj Nk Nt Oi Om Qe) Nd(Hq Jg Jo Lz Mi Mt Og Pa Qa Qe) Nj(Hw Il In Jo Jt Mt Om Pa) Om(Iq Jg Mg Mt Ne) Ne(Hw In Jo) Nt(Jo Jt) Hw(Mt Nk) EmVo JtOk OnOy} Ok{Nf(Et Fp Fr Hq Hr Hu Hv Hw Hx Ih Ii Ij Ik Il Im In Io Ip Iq Ir Is It Iv Jg Jh Ji Jj Jk Jl Jm Jn Jo Jp Jq Jr Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Ng Nh Ni Nj Nk Nl Nm Nn No Nq Nr Ns Nt Nv Nx Ny Oe Of Og Oh Oi Om On Oy Oz Pa Pb Pc Pd Pe Pf Pg Po Pz Qa Qb Qc Qd Qe) Jt(Et Fp Hq Hw Hx Ii Ik In Ip Iq It Iv Jg Jm Jo Jq Js Lj Lv Lx Lz Ma Mb Md Mg Mi Ml Mn Mq Mt Nb Nc Nd Ne Nh Ni Nj Nl Nq Nr Ns Nt Of Oi Om Oy Pa Pe Pf Pg Qa Qe) Jo(Et Fp Hw Hx Ik In Iq It Iv Jg Jm Jr Js Lv Lx Ma Mb Md Mf Mt Nc Nd Ne Nh Ni Nj Nk Nl Nq Ns Nt Of Oi Om Oy Oz Pa Pe Pg) Nl(Et Hw In Iq Jj Js Lx Md Mi Of Og Pa) Nc(Hw In Iq Jj Js Md Nd Om) Nd(Hw Jg Js Lx Mt Og Pa) Lx(Hq Hw Js Po) Mt(Hw Js Om) Og(Ik Iq Nq) Ne(Hw Js) EmVo} Me{Dr(aN aV dJ Dp Ed Ez Fb Fy Ha Hb Hc Ib Iz Jd Je Jf Jj Ju Jv Jy Kd Ke Kf Kg Kj Kk Kl Kn Kp Kq Kr Ks Kx Ky Kz Ld Nl Oa Or Ow Oz Pc Ph Pj Pk Qh Qn Qt Qu Qw Qx Qy Qz Ra Rc Ri Ss Tz Ua Ub Uc Ud Ue Uf Ug Uh Uk Ul Um Un Uo Up Ur Us Ut Uu Vo Vs) Em(Dp Ed Ez Fb Fn Fy Ha Hb Hc Hf Ib Ic Iz Jd Je Jf Jj Ju Jv Jy Kd Ke Kf Kg Ki Kj Kk Kl Kn Ko Kp Kq Kr Ks Ky Kz Or Pj Qh Ql Qm Qn Qt Qu Qw Qx Rb Rc Ss Tn Tr Tt Tv Tz Ua Ub Uc Ue Uf Uh Uk Ul Un Uo Up Ur Us Uu Uv Vo Vp Vs Vv) fR(Fa Gz Ha Hb Hf Ib Jf Kd Kj Kk Ko Kq Kr Ks Ky Nd Nj Oa Or Ou Ql Qn Qw Qx Rj To Tv Ub Up Ur Vp Vq) Gc(Fb Iz Jy Kd Kj Kk Or Qu Rc Ub Ue Uk Uu Vo) eP(Dp Fn Ib Kj Ko Nd Rc To Ur) dX(Dp Kj Kk Nd Rc To Ur) aX(Hf Ko Ou Sr Vq) eM(Dp Nd To) EtNl} Et{Nl(aA Fp Fr Hq Hr Hv Hw Hx Ih Ii Ij Ik Im In Ip Iq Is It Iu Iv Jg Ji Jj Jk Jl Jm Jn Jo Jp Jq Jr Js Jt Lj Lu Lv Lx Lz Ma Mb Mc Md Mf Mg Mh Mi Mj Ml Mp Mq Ms Mt Mw Mx Mz Na Nd Nf Ng Nh Ni Nk Nm Nn Nq Ns Nt Ny Oe Of Og Oh Oi Om On Oy Oz Pa Pb Pc Pd Pe Pf Pg Po Pz Qa Qb Qc Qd) Jo(Fp Ik It Iv Jg Jr Lv Lx Mb Md Mt Nc Nd Ne Nf Nj Nq Nt Om Oz Pa Pb Pg Qe) Nc(Hw In Jj Js Jt Lv Lx Md Mt Nd Nf Of Og Om Oz Pa) Mt(Hw Ij Jj Js Jt Nd Ne Nf Nq Of Om Oz Pa) Nf(Jg Ji Jj Jr Lv Lx Ne On Oz Pa) Jj(Ik Lx Nd Ne Nj Oz Pa) Jt(Jg Lx Ne On Pa Qe) Lx(Nd Ne Nq Oz) Pa(Nd Ne Nj Om) Oz(Jg Og) EmVo NdIu NeHw} eP{Hu(aJ Dp Ex Fa Fp Hc Hf Id Ik Jy Kk Ko Kp Kz Ld Mf Nb Nu Oa Ou Pb Qw Qy Ra Rb Rf Sr Wm) Ib(Ad Dg Dl eF Hc Hf Ih It Jn Jp Kf Ko Oa On Vv) aX(Ih Jy Kn Mf Nj Nl Ou Ph Qz Rb Rf) Ko(cF Cw Fb Ha Kc Kj Og Tv Vt) Qw(cL cN eF Nb Nu Rf) Qy(aJ Dp Ex Jj Kk) cF(Fp Jj Lj Oa Rf) Ha(Ih Nx Oa On) Og(Hf Ih Kf Nj) aV(aJ cN dK dM) Nb(Jy Nj) Ii(Ih On) Hf(cN Jj) Rb(bE dK) Jp(Ke Uf) Oz(aZ gP) AfNu FbMf NfKk IrRa IdJ KfVo OubE PcaZ bRcL} nD{hV(eD iC jV jY kC kG kP IL lM lW lY mM mP mS mT nA nF nl nJ nK nT nU oP qT qX rB) nA(eD hR jF jH jM jQ jR kP lK lX mH mM mS nC nR nU oP oQ qW qX rA rX rY rZ) oP(jQ kC kP lX lY mH mP mU nJ nK nM nN nT nU qX rA) rA(eD jD jU jV kC kF kP lY mT mU mY nl nJ) oQ(kC kP mH mU) qX(eD lW rB) qW(mY nJ rB) mH(nJ nK)} gP{Gt(aJ aN aV bA bC Bo cF cH cL cN dG eF fR Fw) fR(DO Dq DV eX gN gT Gw Kd Ko Qx) aJ(DO Dq DV eM eX gC gN gT Gw) Bo(DO Dq Dv eX gN gT Gw) cL(Do Dq DV eX gN gT Gw) Qe(aX bV Ii In Js Qc) aV(dO Dq DV cX gT) dG(dO dV eX gN) Dq(Cs eF Fw) bV(Ko Rj Sr) Gw(aN bC) Qw(dX eM) dL(eX gN) eF(Do Dv) KkeM KodX dFeX} Em{Vo(aZ Dg Dl Ex Hf Ih It Ji Jn Kf Kn Ko Ld Nv Nx Oh On Ou Ph Pz Qa Qw Qz Rb St) Rb(aJ cF Ch Dd dG dL fR Hu Jj) Nx(Ha Ii Jj Kj Ks Ua Ue Uu) aJ(bR Kz Mv Mw Nf Qw Ua) Kk(aV dJ Hu Ke Uf) Ex(Ke Qh Uf) Ib(Ax Hf Ph) Ue(Ko Qw) Jp(Ke Uf) Kj(Ko On) Ou(Gl In) Uo(aZ Qz) aV(dM Qx) HuKd IiOn JjLd OgPh} dX{Ko(Cp Cw Dp Ha Hu Ib Jj Jk Ke Kj Kl Kq Og Om Qy Ue Uk) Hf(cF cN Dc dI Gz Hu Ib Jj Oz Qw Rc Up) cN(Jy Kk Oh Ou Pb Ph Pj Qw Qx Rf Wm) Ib(It Jp Kf Kk Ky) Qw(eF Hv Ky Nu Rf) Ha(Ih Ky Nx On) Hu(Kd Qx Rb) Jj(It Jn Vv) Qy(Kk Ue) Jp(Ke Uf) NfaN IhIi RbbE KfVo KzdL OmeF OzaZ PhaX aVdM} eM{Hu(Fa Fp Gz Ib Jy Kf Kk Ko Kp Ky Oa Ql Qm Qn Qx To Ub Uk Vs) aX(Dp Ed Ih Jy Kn Ko Ld Nj Oa Ou Ph Qz Rb Rf Rm) Ib(aC Hf Ih It Jn Ko Qx) Kk(aC cN dE Dp Jd Jc) Dp(Nx Qx) Rb(aC bE) Jp(Ke Uf) Ko(Uf Uk) aN(Jn Qx) aV(cN dM) PoRf FaNf HaOa QzaZ QweF UraC} aV{dO(aJ bJ bX cF cH cL cO cP cU Dd dF Di dJ Dl Fw) Gt(aJ aN bE cG cL cO dK dM eF fR Fw) Dq(aX bE cN cO cY dK dM Fw) Dr(aU cN cY dM gW Qx) gC(aJ aU cY dG dK dM) dV(aJ cY dG dK dM) gN(aJ cL cN dK dM) Gc(Hu Kk Qx) dK(Dv gT)} Lx{NI(aA Hw In Jj Jk Jo Jp Js Lv Lz Md Mi Nd Nf Ni Nk Og Oz Pa Pb Po Qb) Nd(Hr In Jg Js Lz Md Mi Nf On) Nf(Ik Jg Ji Lv On) Jj(Ik Nc Ne Nj) Lv(In Nc Po) Mt(Hw Js) Ne(Hw In) PoNj NqJg OnOy} Dr{Ra(Hu Ih Jy Kn Mz Ou Ph Qz St) Nx(Gl Ke Kj Rc Uf Un Vo) Hu(aJ Hc Hv Jy Nb Nl) Ib(Hf Jn On Vv) Rb(aJ dE dG dL) Kk(Ke Uf Vo) Ko(Kj Rc Uf) Dq(cL Fw) FwGt MvHv NlaX RcQw QuOn QtVv JpUf JyOg KfVo} fR{Ko(Cw Dg Dl Gl Hb Ib Jf Jo Jt Ke Kj Kl Ks Og Qm Qt Qw Ra Rb Rc Ue Uf Uk Un Up Vo) Nf(aN Nd Nj Nl Qw Rb) Ra(Kk Ph) Ou(Kk Qu) LvoE NjPa RbJp QwVq} Gt{cL{bA Bo bR bU cB cF cP Cs cZ dD dl) aN(Ax bR cB cH Cs dJ Dl eF Fw Gp) Fw(aD bC bL Bo cM Tj) eF(aD bR bU cP dV) Bo(Di Dl) aJ(aK bR) AnaM aDcB cHcN} On{Oy(Fp Hw Ik Lv Mb Nd Ne Nf Nh Nj Nl Nq Om) Nf(Fp Md Nd Om) Hw(Mt Ne Nl) MdNl MtOm} Dq{Fw(aD aN bC bL cF eX Tj) cL(bR Cs dl) aM(cB cF) cN(aK cH) aJbR} Gc{Hu(aJ Jy Ue) Vo(cF Kf Kk) Ib(Jn Vv) Rb(aJ dG) UecF JpUF KjNx} Nf{Ji(Fp Ik Lv Nd Ne Nj Nl Oz Qe) Jp(Ik Lv) DcQe} eD{hV(lW mM mS mT mZ nO nU oP) mT(jQ lX) rA(nO nU)} bR{aJ(dO dV gC gN gT) cL(dO eX gN Gw) dG(dO dV)} oP{mF(kP lK lX mH) nN(nL rX) nUkP mMlK nCnJ} Nl{Jj(Jg Lh Mm Mt Pa) Hw(Jp Mt) JgOg} dV{aJ(cB gC) cF(dG dL) BoaM CscL bLdG cHcN} gC{aJ(bU cP dJ) dG(bU cP) CscL cHcN} mS{rZ(iC nA nK nM nT nU) mFhV} Mt{Hw(Fp Ji Nc) Om(Ji Jj)} cL{dJ(eX gN) gT(cP Cs)} Do{Fw(cA Tj)} Jp{NiNj IkJo} Vq{CtoF VshB} aN{eX(Di dJ)} rA{nOIL mImZ)} IK{nRmT nCIL} RbOuaX aMcBgN Unconstrained panels with 3 analytes, where 1.0E-9 >= 'AUC p-value' > 1.0E-10. Contains 4,732 panels of 10,034,416 total panels evaluated. :
Gn{Om(aK Ap As aU bC BG bH bl bL Bo cD Cp cT Cu cY cZ Db Dc dF Dg Dk dN Ef Et Fr gL Gp Ha Hv Hx Iu Jg Jh Ji Jl Jo Js Jt Jv Kg Ki Kq Lw Lz Mb Mc Md Mi Mj Mk Ml Mr Mu Mv Nc Ng Nh Ni Nm Nv Nx Ny Of On Ou Ow Pz Qc Qd Qm Qv Rf Rm Tn Ud Ug Uk Un Uo Ur Vp Vt Wm) Ue(aA aL Ao aP Bb bE bM bN bO bS bZ cA cC cE cG cl cK cL Cp cQ cT cU Cv DB Dc DD dG dK Ef Fa Fw Fy gL gP Gz Hc Hf

Co cV cX dC Dd dE DG dH Di DK DL Dr Ed Em Fa Fw Gc gL Gz Hb Hc Hw Ij Ik Il Im Is It Je Jf Jg Jh Ju Jv Jy Kd Ko Kp Ky Kz Mg Mq Mw My Na Nb Nd Nf Nk Nm Nq Ns Nu Nx Of Oh Pa Pk Po Pz Qh Qn Qx Qz Rf Rg Sr Ss To Tt Tv Ub Un Us Vs Vt) Or(aA aF aI aL aP aS Ba bB bF bH bM Bn bO bQ bW bZ cA cB cC cD cE cG cI cJ CO cR Cs CU cV CW cY cZ DB DC DD dE dG dH dK Em Ex Fa Fr Fw Gz Hc Hf Hr Hv Id Ii Ik Iv Jg Jo Js Ju Kp Ks Kz Li Lu Lv Mb Md Mk Mq Mr Ms Mw Mz Na Ne Ni Nj Nl Nn Nq Ns Nt Nu Oc Pa Qb Qv Qx Rh Sr Un Up) Ny(Aa aC Ad aE aG aH aK AL An AS aU Ax aY bA BC bH bJ bS bV bW bX cA cB cE cG cM cQ cV Cw dB dH dK Dl dM dN Ef Et Ez Fn Gz Hq Hv Hx Ib Ij Ik Il Is Iv Iz Jh Jm Jn Jp Jq Kl Kn Ko Kq Kr Lu Ma Mb Mx Nd Ne Nh Nk Nl Oe Oh Oi Oy Oz Pc Ph Pj Qx Rh Ss Tv Uk Up Uu) cP(aA aE aF aI Al aM An aP AW bA Bc bF bJ bO bQ bV bZ cA cG cJ cM cO Cq cR cT cU Cv cW Cx cZ dA Db dF Di Dp dX Ed eM Et Fp GC Gt Gw Hx Il Im Iq Ir Iu Jc Ji Jr Js Ju Jv Jy Kc Kd Li Lj Md Mf Ml Ms Nc Ne Nf Ni Nq Nr Oe Oi Pa Pc Pd Pg Pj Pz Ss Ub Ug Uk Ul Vp Vt) bR(aA aE aF aI aK aL aM aO aP aQ Ar Aw Ax aZ bB bC bE bF bI bJ bM BN Bo bS bU bV bW cB cG cJ cK cO Cp CQ cS cT CV cW Cx cY cZ dA Db DD De dF dH Di dK dN DR DV eF eP Fb Fw gN Gw Hv Ii Jf Jo Ju Jv Kc Kk Mf Nj Nk Nm Of Pc Qv Uk Un Up Tj) Aa(aC aE AF Aj aK Ao AS aY aZ Bb bE bF BG bH bI bJ Bo bP bV cA cE cG cI Co Cp cT cW cY cZ Dc Dd DG dK dM eP Fn gT Ha Hc Hq Hv Hx Ir Iu Jd Je Jg Jk Jn Jv Jy Kl Kq Kr Kx Lh Lx Ma Md Mh Mn Mp My Na Nk Nn Nu Pg Pi Qg Qy Tv Uk) Gl(aC aG aH aI Aj aL Ap Ar aU Aw Ax aY bB bE BG bH bI bJ bM bO bQ bS bW bZ cB cE cG cI cJ cK cO cQ cS Ct cU CV Cw cX Dc Dd De dF dH DK dM Dp DR Em Fr gL gP Hv Hx Ib Id Ip Jp Ju Jv Jy Ki Lu Mk Mq Nl Nu Of On Qu Sr To Tr Uu) aV(aF aM aP As Aw Ax aZ Ba bG bI bL bO bP bQ bS bW bX bZ cB cE cJ cL cM cQ cT cU CV cW Cx Db dC dD De dF Dg dH Dl dN eF eP Fa Gc gL Gw Gz Hf Im Iq Je Jg Jk Jo Jv Ky Ld Mn Mq Mr Nf Ng Oa On Oz Pb Qm Ss To Ub Uc Uh Uk Ul Ut Vp Vt Tj) Qu(aG aN aO aP aQ As AX aZ BB bJ bM BO bP bQ cA cC cE Ch cJ cK cL cO cR cS cW dA dE dF dG dR Ez Fp gW Hb Hq Ih It Jn Jv Ko Kp Ky Ld Lj Lu Lx Mh Mr Mu Mv Na Nf Nj Nk Nl Nm Oh Ow Qb Qv Qx Qy Rf Uh Uk Un Vq Vt) Og(Ad Af aG aJ An aO Bg bI bP bS cA cI cJ cL Db Dd dE dI Dl Et Fn Gz Hc Hf Hq Hw Id Ih Il Is Jf Jh Jk Jn Jr Js Kp Kx Ky Lu Mn Ms My Nb Ne No Nq Nx Oe Oi Oy Pa Pf Pk Qd Tt Tv Tz Ub Uc Ug Us Uu Uv) aN(aD aF Aj aK aM Ao aQ aR aW aX bA bC bF Bg Bo bS cA cE cG cJ cM Cp cW cX cY dA DC DE Dg Dk Dp Dr Em Ex Ez Fw Gp Hw Ij Il Jg Jk Jv Jy Kd Kk Lj Mh Mw Nd Ng Nk Nl Nu Ou Ow Oy Uh Un) cF(Ad Aj aK aM aQ As Ba cA cI cN Cp Cs Ct Cu cW cY DC DD Dg Dp eP Ex Fa Fp Fw Gc gN Gp Hb Im It Jd Jf Jg Jt Ju Kf Kg Kn Ks Ky Ld Li Lu Nk Nl Nv Pa Qx Rf Ss Ub Uc Uk Ul) Ez(aC aG aQ Ar AS Ax aY bA Bb bN bO cC cD CS cY dA dF dN Em Ex Fp gP Gz Ib Is Jj Jm Jn Kn Lj Mk Mr Mv Mz Na Nb Nd Ng Nv Nw Oy Oz Pf Pi Qb Qd Rf Rm To Uf Up) Uf(aM Ao aQ Ar As Ax aZ bN Bo bP bQ bV cC Ch cL Cv cX dA dD dE dF dI dK dM Dp gL Gp Hq Hv Ji Jv Jy Kj Kp Ky Lh Lu Lx Mm Mv Nd Nl Oy Oz Pa Qa Qx Qy Tn To Up Vv) cN(AD Af AJ AO As bW bZ cA cG cM Cp Cs Ct dA dD Dg DL Dq DR dX eM fR GC Gw Ik Is Jl Ju Jy Me Mm Mp Nl Nn No Oe Oz Pc Pg Rh Ss Ub Uk Ur) Ch(aO Ap As bA cD cE cM Cs Cw dA Dc dD Do DR eX Hv Ij Ju Ke Kj Ko Kp Kz Ld Mf Mu Mv Na Nf Nk Nm Oa Pa Pb Pi Qn Rf Rg Uh Un Ur Ut Vp Vq Vs Vt Vv) Jj(aE AO Ap aR aW AX bA bC Bg bJ cH Cw dD dL Ex Fw Gp gW Hb Hq Ii It Iz Jd Je Kd Kj Kl Ko Kp Mr Mu Mv Nb Nm Oa Oi Ou Ow Pi Qm Qy Ss Uu Vq) Kf(aS bA Bb Bg bU Cu cW Cx dD DG dI dK Dp Gp Gz Hv Ib Id Ih Ip Iu Iz Jh Jl Jq Jt Lh Mb Mh Mm Mu Mv Mz Nb Nl Nn Nr Of Oi Ou Pb Pe Qb Qe Qg Qy) gP(aH aM aO AP aQ Ar aW aY BA bC bI bJ bM bO cA cB cD cJ cM cS cX cY cZ DD dH dI dK dN Dp dR Dv eM Gc gL gN Iz Kd Kk Kl Mf Mv Ng Nl Uu) Bb(aF aK aM aO aQ AR As AX bA Bc bF bH bL cB cC cD cE cI cY Dd dE dG dK Do Dr eX Fp Ld Lj Lu Mu Mv Ou Ow Oy Oz Pc Ul) Ef(aD aF aK aL Ap aR As aY bA bC bJ bP bW bZ cA cB cC cE cH cL cM Cs Cw cX cY dF dG Di dR Fa Hc Ib Ih Kd Oy Oz Qb Rf Sr St) Om(aE aF aR Ba Bc cJ Co Ct dR Ed Fy Hc Ii Iq Ir Jd Je Jf Jk Jp Kd Kz Li Mq Mw My Nn No Nq Oy Qe Ri Tt Tz Ua Uc Ul Ut Uv Vq) dL(aA aD aF aG Ao aX aY Ba bQ bW cG cH cM Cu Fr Fy Hb Ij Jg Jk Ju Jv Ks Mn Mr Nf Ng Nj Nq Oe Oi Qh Qx Ua Uk Ul Up Ut Uu Vt) Jy(aJ Ao Bg bP cM Cs Cw dI Hq Ii Ij Jh Ju Jv Ke Kg Kl Ky Ma Mb Mk Mn Mq Mw Ng Nm Nq Oa Of Oz Pa Pc Qx Qy To Ua Uh Ul Up) Qw(aE aI aK Al aS Aw bF bJ bU bW bX bZ cA cI cM cU cY De dG Em Gc Ha Hc Hr Iq Jl Ky Mf My Na Nq Nw On Qc Qh Rg Tr Up) Kc(As Aw cE cH Db DE Dp Fb Fr Gc Gp Ha Hf Hv Iq Jf Ji Jq Kq Mq Nf Nk Nq Nt Oe Ow Oz Pa Pd Pg Qd Qh Qy Rh Tt Tz Up) aD(aJ bW cY Dc dl eF Fn Fw gC Ib Ih Ii Ij Jd Jt Kd Lu Mr Mu Mv Mw Mz Nb Ne Ng Of Oy Pg Pi Po Qv Qz Ss Uh Uk Un Uu) Kn(aP Bg bO cR cS dA dD Dl dM gL gW Hv Ih It Jh Ji Jk Jn Jp Jr Mv Nj Nu Nv Oe Ok On Pe Ph Qx To Ua Up Vv) Me(Al aW bP cA cD cE Ct dC dI Em Il In Ir Iu Ji Jq Js Li Mr My Na Nb Nj Nn No Nv Nw Ou Pg Po Qc Wm) Ib(aC As aU aW bC bJ bL bM bP bZ cM cT dB dI dN Fp Hb Hc Hq Mf Mz Ng Nj On Ow Oz Pa Pb St Uh Uk Wm) Kk(AJ aO Bg Cu Dd dE dN Dp Fr Hw Jo Ju Kq Mt Mu Mw Nl Oi Oy Pc Po Qd Qh Qm Qn Rh Ua Uh Uk Un Vq) Kj(aG aM Ar BC bF bU cH cM dE Dl dN Fa Fb Gp Kp Mh Mk Mz Nd Nl Oh Oi Ow Oy Oz Pa Pi Qy Uu) Mv(aG Ao aP As aZ Bn bP Cs dG dI Fp gL Gp Hq Iz Jr Ju Ld Ma Mf Nd Nm Oz Pc Qx Qy Sr Ss Uk Un) Ul(Al An Ar aZ Bg cE dI dK gL Gp Gz Hf Hv Hx Id Iu Iz Jp Ky Ma Mf Nl Nw Oe Ou Oy Qd Qy Ua Uk) Uo(aF bH bX Dc De Dg Et Gc Gp Hq Ir Iv Jg Kq Lh Mb Mh Ni Pa Pd Pg Ph Pz Qa Qb Qc Ql Rg Rj Tr) bU(Aj aX Ba Bg bL cC cI cO Cp Cs Ct Dd dG dI DK Gc Hb Ii Iz Jv Kl Ma Mu Nm Qm Qv Qy Uc Uh) Uu(aC Al aM Ax bE bF dA Dl Fa gL Gp Id Ky Mb Mh Mk Mq Mr Nb Nl Ns Oy Oz Pb Pi Ug Vp) Iz(Ad aG Ar Ax bA Bc cH cM dE dI gL Hf Id Jp Kd Ky Mf Mu My Oh Ok Ou Ow Oz To Tr Vv) Do(aA Ao aR aU aW bA bE bG bH bN bZ cI cM cZ dA DC Dd dE dH DV Em eP gL gT) Ke(aG aM aP Ar cM dE dI dK dM dN Gp gW Ic Io Kd Mf Nv Oa Ok Ou Pb Pc Qb Rf To Tr) cH(Ap As dA Dc Dp Ed Fn In Je Ky Kz Ma Mq Mr Nk Ow Pi Qm Ss Ua Uk Un Up Ut) Kl(aG bC bL cM cT dD dE Fw gL Hf Jm Kd Kp Ky Ld Nb Nd Ou Oy Pa Rf Sr Tr) aX(Ap aQ Ii Ij Jf Jo Ks Lu Mr Nm Ow Pj Qn Qy Ss Ua Uh Uk Ut Vq Vs Vt) Ao(cA Cs Di Fp Fw Hf Lj Ma Mf Mr Mu Nb Oa Oe Oh Oi On Pa Qg Qy Uk) aJ(Ba bW bZ cM Dc dH Di Ij Im In Jk Jv Mu Nf Ng Pc Qm Qv Tz Ua Ut) Cs(Ad aO aQ Ba bF bL dE Dg eP Et Fy Jg Js Ju Ng Oz Pc Pf Ss Un) Cw(aM Ar bL Bo cL cM dD dG dN eX Fp Ld Mf Oh On Ow Oy Oz Pc Qx) Hb(Ar bE bP dI dK Fa Hf Jm Ky Mk Mu Oa Oh On Ow Pc Qa To) Nb(aG Dc Fb Ii Jg Jk Jt Ng Nj Oe Po Qy Uc Uh Uk Un Up) Mf(Ap Ba Em Et Is Jo Jt Ju Ks Mu Ng Nm Pj Un Ut Vq) Nj(Af Ba bL Im Jg Jh Jo Kd Ma Mu Nf Oi Oz Pa Rb Uk) aG(Ap Bn cI Di EX Fb Fp Kd Lj Mu Ne Oa Oh Qg Qx) eX(aK bL Bo bW bZ cA cB cQ Cu dA Dq dR gC Gt Gw) Nm(Ar aS cM dG dI Fw gL Mu Nu Nv Pb Pc Rf Rm) Ij(Ar As bL dI Dp Mu Nu Oc Oh On Pb Pc Qe Rm) Ap(aM bA bC dD dG dN dO eF Ex gL Nx Oe) Rb(Bn bX Fa Ih Jf Ki Nh Ns Pb Qg To Vv) dI(Ad Af An bA cE Ex Gt Ii Kd Ng Of Qv) Ma(Ar bL dD gW Kd Lx Mh Nx Oe Ok St) Pc(Aj aZ Cp Ik In Jh Lj Mn Mu Ss Un) Fb(Ar Dp Ex Fw Kd Ko Oa Oe Qe To) Jv(As Fa Fp gL Ky Mr Nl Oa Oh Qx) Ou(Ba Bg Cp Dk Ii Ik Jo Lh Ng Uc) Mu(As bL Gp Hv Nl Ow Qv Ss Uk) In(Hf Ih It Jn Kd Ky Oz Ph St) Fw(Ad Dc Dk Fr Gt Ks Of Pj) bL(Dc Dd Di Ex Gp Nx Pb Up) gW(Dp Pj Qv Ua Uh Un Ut Wm) Qx(Ed Ii Jo Ks Lu Mg Ut) Ld(aH Aj cD Dd Jg Jo Mg) Oa(Im Jt Ju Ng Of Po Ss) Of(Ex Ko Lj Oe Oh Rm) Ba(bA Ex Fp It On) Dq(aW bN Bo cP Gt) Nx(Dl Fy Is Ju Qm) Un(Fa Fp Jp On Rf) Ng(Fp gL It Vv) Im(Fa Ih Qa Qe) Jh(bC Kd Oy Oz) Jo(Ex Lj Rf Rm) Uk(aZ cI cM Nd) Pj(Fa Fp Ko Lj) Gt(bA cL eF) Ii(Ax Jm Nv) Qv(cM dE dN) Kd(Di Jd Oy) Qm(cM Gp Mb) Uh(Ih Ko Lj) Oz(Aj Bg Cp) aO(dG Nk Nl) Gw(Bo cL) Ss(Em gL) Jt(Ky Oh) Ks(Lj Rf) Ut(Nk Nl) Oy(Aj Pb) dG(cE Wm) AxFy CuEx DbVo DlKo DpbC FpJs JdOe StJu QzgL aUcY} Nw{Iq(Et Fp Fr Hr Hu Hv Hx Ih Ii Ij Im In Io Ip Ir Is It Iv Jh Ji Jj Jk Jl Jm Jn Jp Jq Jr Jt Lh Li Lj Lu Lv Ma Mb Mc Me Mg Mh Mj Mk Mm Mn Mp Mq Mr Ms Mu Mv Mw Mx My Mz Na Nb Ng Nh Ni Nm No Nq Nr Ns Nt Nu Nv Nx Ny Oe Of Oh Oi Ok On Pb Pc Pd Pe Pf Pg Po Pz Qb Qc Qd) Hw(Et Fr Hq Hr Hu Hv Hx Ih Ii Ij Im In Io Ip Is Jh Ji Jj Jk Jl Jn Jo Jp Jq Jt Lh Li Lj Lu Lw Ma Mc Me Mf Mh Mi Mj Mk Ml Mm Mn Mp Mq Mr Ms Mu Mv Mw Mx My Mz Na Nb Ng Ni Nm Nn No Nq Nr Ns Nu Nv Nx Ny Oe Of Og Oh Om On Oy Pb Pc Pd Pe Pf Pg Po Pz Qb Qc Qd) Mt(Et Fr Hr Hu Hv Ih Il Im Io Ip Ir Is It Iu Iv Jg Jh Jk Jl Jm Jn Jp Lh Li Lj Lu Lx Ma Mb Mc Me Mf Mg Mh Mi Mj

Mn My Ng Nh Ni Nq Nt Oz Pa Qe) Nl(Hr Hx Ij Il Jm Jo Jp Jq Jr Jt Lv Mi Ng Nq Ns Ny Pa Qb Qc) Nj(Hw Hx Il In Jj Jk Js Jt Ng Nq Of Og Pa)
Md(Iq Jk Lv Mb Nc Nh Nq Nt Oz) Ne(Ii In Iq Jj Jk Js Of Og) Ik(Hw Ij In Jk Jo Jp Jt Og) Nq(Hw Js Lv Nc Og Pa) Hw(Fp Iq Lv Nh Pa) Of(Hx
Jg Lv Nc) Dr(Rc Vo) Iq(Nc Pa) GcJt LvPa HqOe JjdX} Nl{Jj(Aa Em Fp Fr Hv Ii Il Im In Io Ir It Iv Jl Jm Jn Jr Js Jt Li Lv Lz Ma Mc Md Mh Ml
Mp Mw My Nd Ne Nf Ng Ni Nm Nn No Nq Nr Ns Nv Om Oy Pe Pf Pg Pz Qa Qd) Jp(aA Fp Hq Hr Hv Hx Ik Il Iq It Jg Ji Jk Jm Jr Js Jt Lz Mb
Mc Mc Mf Ml Mp Mx My Mz Na Nd Ng Nm Ns Nx Ny Of Om Pd Pf Qb Qc Qd) Mi(Fp Hw Hx Ik Il In Jg Ji Jn Lj Me Mm Nd Nx Oy Oz Pc
Qe) Jg(aA Hw Il In Iu Ji Jt Md My Ng Nk Om Oy) Ji(Il Iq Jo Jq Lv Me Mq Nd Ni Nk Om Oz) Pa(Aa Fp Fr Hw Il Lv Lz Md Nf Ni Nx Qe)
Aa(Hw Ij Jo Ma Mj Nf Om Oy Oz) Mm(Hw In Jo Md Nf Nk Og Oz) aA(Fp Il Jn Lv Me Nk Nx Og) Fr(Hw Il In Nf Nk) In(Lh Nv Nx Pe)
Og(Gc Lv Nt Nx) Hw(Nv Nx Qe) Lv(Me Nf) Qe(Nf Nk) Kk(Dr Gc) Lh(Il Jo) MdNx MefR HueP} Me{fR(Kl Kp Kz Ml Ne Ph Pj Qg Qh Qt Qu
Qz Ra Rb Rh Ri Ss St Tn Tr Tt Tz Uc Ud Uf Ug Uh Ul Un Ut Uv Vs Vt Vv) Gc(aJ Dd dL Ed Fy Ha Hf Ib Jd Jj Ju Ke Kg Ks Ky Ld Oa Pc Qm
Qw Qx Ra Ur) aX(Fy Id Ik Jf Ju Kf Ki Kk Kn Kp Kq Lv Pb Qg Qh Qw Ra Rf Rj St Tt Vt) Dr(Aa bR Dd dL Fa Fn Hu Nd Qg Qm Rf Rh Rm Sr
To Tv) Em(Fa Id Lv Ou Ph Pi Pk Qv Rf Rg Ri Sr St) cM(Id Jd Ks Pk Qu Qx Rf Ub Uh Ur) Gz(aJ cU Ha Jj Jn Og Oz Ub) eP(Fa Id Oa Or Uk)
Ex(Ha Oz Pc) Sr(Dc Kr Om) Ik(Jj Jp) Hf(bV cH) Vq(dE Ky) dX(Ib Jv) DcKf NfJi NjJp JfdE KkgP} Nf{Ji(Fr Hq Hv Hw Ih Ii In Iq Ir It Iv Jk Jl
Jm Jr Js Lh Lz Mb Mc Mh Mm Mq Mr Ms Mu Mx Mz Nh Ni Nk Nq Nr Ns Nu Of Oh Om Oy Pb Po Pz Qd) fR(Ax cE Cs dD dH gL gP Hq Iq It
Iv Kd Kk Ko Lv Ne Nq oE Pb Pc Qx Ra Up) Jg(Ik Jk Jp Lv Md Mv My Nc Ne Nj Nq Of Om Oz Pa Pe) Jp(Fp Iv Md Mi Nc Ne Nj Nt Nu Nx Pa
Pe Qe) Qe(Fp Fr Ik Jj Li Mi Nd Nt Nx Pa Qc) Lv(uX Mz No Nt Oh Pa Pe Pg Qa) aX(bN Nd Nj Ou Sr Vq) Nx(Fr Li Md Pe) Fp(Fr Lh Mi) Nd(Jl
Mi Nv) gP(eP Kk Sr) Nt(Jj Mi) Ik(Fr Pe) Nv(Lj Md) aN(eM eP) EmFa GcUe} gP{bV(gL Ha Ib Id Jf Jk Kn Kp Kz Ld Nd Ou Qa Ss Tn Uh Ur
Ut Vp) Qe(aJ Dk Ha Hq Ij Jj Jo Kk Mj Oe Om Pc Po Qb Ut Vu) fR(aD aF aH bP dM Dr Gc Or Oz Pc Qw) dL(DO DV eP GT) eM(Cs dG Fa Hu
Mv Pc Qx) eP(aV dG Jj Mv Pc) Dv(bC cN dG Fw) aX(Ou Ph Qy Vq) bA(cH Do Dq eX) Qa(Ii In Jf) Ko(gW Jf Jk) aJ(Bc dX Em) eF(Bg Dk
Gw) Bo(dV gC) Cs(eX gC) Gt(cG Cp) Or(Dr Vq) dO(aK cL) gL(cH dM) DqbC WmKk UeVq JfSr OzdX} nD{nA(hA hW hX iB jG jK jL jY
kE kI IL IM IO IW IY mE mF ml mU mW mZ nB nH nI nJ nK nM nN nO oO qU qY rB rC) hV(hW hX iB jE jF jH jK jL jO jP jQ jR jT jU kE
kF kl IN IO mE mF mH ml nC nO qU qV rC rX rY rZ) qX(jD kG kP IK IY nF nM nO nU) rA(iC kG mP nO nT qT qY rB) qW(jH kC kG IL IW
ml nK) mH(nF nT nU) nK(kP IX mS) oP(kF mF nC) mP(mS oQ) nJ(jQ IX) mMkP mTjQ nFoQ} eP{Hu(Ar Cs Fy Iz Kf Kg Ky Lj Nd Pe Pj Qd
Ql Qm Rc St To Uk Ur Vv) Hf(Gz Ne Om Oz Qw Ra Tv) Kk(cF dN Nu Rc) Ko(aX Kl Kq Uf) aJ(dA gC Kz Qw) cH(aN cN Oz Pb) Nb(bR cF
It) Og(Di Id Ug) cN(aK Qy Rb) Nu(aX cF) Mw(Qa Qd) Ib(Mg Oi) Ih(Oz Tv) Kz(Dg dL) Nx(Dp Ii) Pb(aZ dL) aV(aQ gW) eF(Rb Rc) DrFw
NnQw MfcF QyfR JnaN RfUf UraC PjaX dGgC} Jp{Ik(Hq Hr Hu Hw Ij Iu Ji Jj Jk Lv Lz Mc Mg Mh Mi Mx My Mz Na Nc Nd Ni Nq Of Om
Oy Oz Pd Qe) Nj(Hw Il In Jg Ji Jo Js Lv Mi Mz Nk Ns Og Pa) Nc(In Jj Lv Md Nd Ni Pa) Ne(In Jj Js Lv Md Ni Pa) Lv(Ji Md Oi) Em(Kj Vo)
Nt(Jo Jt) Jg(Nd Nq) RcdX QwfR} Ko{fR(Aa Af aG aX Bb cP Dd Ef Ez Ii Jg Ji Js Ma Mp Nm Nt Oi Pc Pj Ql Qz Rj Tv Ua Ub Uo Us Vs)
dX(bE cN cZ Fb Gl Hf Ii Jt Mj Nu Rc Ua Up Uu Vo) aX(bN Iq Jk Qw Rb) eM(Dp Fb Jh Jj Rc) Ue(Dr Ex Gc Gz) Em(Jt Uf) Gc(Jt Vo) Jk(eF Jf)
DrKe} aV{dO(aD Ax aY Ba BC bL bR cA cB cI cQ cT cZ dE dI dK dL dM dV gL) Dr(aC aX Cs dG dR Hu Nx) Dq(aU bC bJ dG Di) Gc(aJ cY
dM Fp Or) Gt(aP Bo bV cR cY) eX(aU cY dF dM gW) gN(aQ aX dX fR) eM(aJ Kk Qx) Dv(aJ cY) Em(cN Qw) gT(cY dG) DodM QxdX aXgC
dVfR} Jg{Nd(Iu Ji Jj Jo Md Mz Nc Of Og Qa Qe) Of(Fp Ik Nc Ne Ni Nj Nq Nx Pa Qe) Om(Fp Ji Jj Md Mv Nc Og Pa Qe) Nc(Hw Jj Jk Jo Nq
Pa) Ne(Jj Jk Jo Og Pa) Jj(Fp Nq Oz Pa) Og(Fp Mv Nj Nq) Nj(Il Pa) Jt(Fp Qe) EmVo NqPa MdNx MvJo Il0z} eM{Kk(aM bl cF cL Cp dA dB
Dd Di dJ dK Ed Ih Jj Ke Ky Mr Nk Oi Or Po Qu Rc To) Hu(cF Ex Hc Id Kj Kz Ld Nj Pb Qz Rb St Um Ur) Qw(aN bE Ky Rf) aX(Ky Kz Oi Pb)
aN(cH Ih Oh) Jj(cF Ql) aC(Ue Vo) CsPb FpcF NdbE Ihli} Em{Kk(Dd Jh Jy Kf Qt Rc Ue Ul Vo) Vo(Ap cB cF Pj Rf Rm Vv) aJ(bU bW cF dA
Hu Qz) Nx(Gl Iz Jo Uf) Ib(Cs dL Ky) In(Jn Ld Nu) Rb(dE Ii Oz) Qw(Dd fR) Jj(Mf Nu) Og(aN aW) AxQt DlKj NgOu liLd QzKd QxaN KzdL
UkaZ aQdM} Dr{Rb(aP aX bE bI cH dK Io Nk Or Qx Ub) Hu(cN cP Kd Kz Oz Qw Qz Ue) Ra(aQ aZ Ld Nc Ne Nx Oi Pi) Nx(Ii Jj Qu Ue)
Kk(dJ dL Rc) aX(Jy Ph St) Qw(cF Or) ExIb GwaN MaVv MvcN Ihln aJbR cLgN} dX{Hf(aN Ha In Li Ma Ne Pb Pe Rj) Kk(cF Dp Og Qw Um
Uo Vo) cN(Kf Kn Kp Kz Ld Mh) aN(Mv Og Oh Pb Qw) Ib(Oa Vv) Ih(In Oz) Qy(Ex Jj) Pb(Cs dL) aJ(bU dA) NtJj NuOz NjOg HuUr QxdA
KfOm KydJ KzdG LdaX} Gt{aN(aA bA bN cF Co cU cY cZ Dd dR eX gW) cL(Ar Ax bC bL cA cG cH dR Ex) Fw(Al Ch cP cZ dD dI) eF(bC
bL bN Dq) cF(bC cG Dd) aJ(bW dI) cY(aX cN) dG(aK bR) BodJ} Dq{Fw(aG aO aQ aX bM Bo bX bZ cA cL cM cP dK eF) cL(aI Bo cF cH cP
dJ) cF(aJ aN Dd dL) aX(aK aQ cY) Bo(Di Dl) bC(cB Di) bR(dG eF) aDcB aQdM aUcN dIeF} Jj{Nd(Fr Im Iu Md Mh Nc Oz Pa Qa Qe) Nj(In
Iq Iu Jo Lv Md Pa) Ne(In Jj Md Og Om Pa) Ik(In Jj Jo Md Og Pa) Lv(Md Pa) Nc(Jj Jq) Oz(Hw Mi) NtOg} Jj{Nt(Fp Hw Ik Md Nc Nd Ne Oz
Qe) Ne(Ik Iv Jn Lh Mm Nx Qe) Mm(Ik Nc Nj) Gc(Nx Rb) Nc(Ik Pa) NjPa IkOg RbfR} Gc{cF(Hf Hu Or Rc) Vo(aC Hu Ld) aJ(Kz Mv Mw)
Ib(dJ Jy) Og(dJ Ne) AaLd HuHv Ihln HfOm RacY KkUl aNcH} dV{aJ(aI bW cL cP dA dI) dG(aF bU cB dJ eX gC) BoDl TjFw aDdF cBcN
cFcL} oP{mF(nA nL qX rX) nU(IX nN) ml(mZ qX) nH(nC nL) rX(kE nA) nOjF IXnK rZIK} Og{Nt(Fp Ik Jo Lv Md Ne Nj Oz) Ik(Mm Nx Qe)
LvOi MmNj NePa} eX{bR(dG dL Fw) dJ(aJ cG dF) Bo(Di Dl) dA(aJ dG) TjFw cFdL cNdR dGgC} fR{Qx(Ou Qw Qz Ra) Oz(cP Qw Rb)
Nd(cP Jn) RbdJ QwKk OucZ VvoK} gC{dG(aD bL bR dD gW) aJ(cA dA dD gW) dL(cH cL)} rA{nO(hX jV kP IM IY) mT(eD rX rZ) eDmZ
nUIY} aX{Ou(Ha Jl Pg Ut Vu) AaRb NjbN} hV{eD(kE kK mU nR) IL(jV rB) mSqU} Qe{In(Nc Ne Nj) Jo(Ik Nt) NeHw} Pa{Nj(Mi Mm)
In(Ne Nt) NcNk} gN{cL(aM dI) aDcB aJdA cHcN} Hw{Nc(Nv Nx) Ne(Nv Nx)} Gw{aJaP bAcL bReF} Vq{oF(Of Vs) JofP} dO{FwaD aJdA
bRcN} jF{nO(jG mS) mTnC} Nd{MiMz JlOy} eD{mZ(IK IW)} nR{IXmT IKIL} oQ{nNnU mFmH} DoaJbR FpHaOu Unconstrained panels with 3 analytes, where 1.0E-7 >= 'AUC p-value' > 1.0E-8. Contains 21,258 panels of 10,034,416 total panels evaluated. :
Gn{dJ(aA aC aK Al aP aS aU AW Ax bA bE bF bG bH bl bN bO bP bQ bV bW bX bZ cA cC cD cG cK cO Cp CQ cR cS cT CU cW Cx cY cZ
dA DB dD De dF dM dN Dq dR eF Et eX Fn Fr gW Ha Hq Hv Ic Id Io Ip Iq Ir Iu Ji Jl Jm Jo Js Ki Kq Kr Kx Lh Li Lv Lw Lx Lz Mb Mc
Md Mh Mi Mj Mk Ml Mm Mp Ms Mt Mx Mz Ne Nh Ni Nl Nn No Nr Nt Nv Nw Oi Ok On Ou Ow Pe Pg Ph Pi Pj Qa Qc Qd Ql Ri Rj Rm St Tr
Ud Ug Ur Uv Vp Vv Wm Tj) Gl(Ad Af Al An aW Ba Bn Co Cp Cq Cu Cx Db dC Dg Di Dl Do Ed eF eM eX Ez Fb Fn Fy Gc Gp Gz Hb Hf Hr
Ic Ij Ik Il In Io Iq Ir Is Iu Iv Iz Jd Je Jg Jk Jm Jn Jq Jr Js Ke Kj Kl Kn Kq Kr Ks Ld Lh Lj Lw Lx Lz Ma Mb Mc Md Mh Mi Ml Mm Mr Ms Mt
Mw Mx My Mz Nc Ne Ng Nh Ni Nk Nm Nn No Nq Ns Nt Nv Ny Oh Oi Ok Pd Pe Ph Pi Pj Pk Qb Qd Qg Qh Ql Qn Qv Qx Qz Rg Rm Ss Tz
Ua Ub Uc Ud Uf Uh Us Uv Vq Vt Vv Wm Tj) Or(Ad aE aH Aj Al An Ap Ar aU AW Ax Bc bE bG bI Bo bS bV bX cK Cp CQ cS Ct Cv Cx De
dF Dg Di Dk Dl dM DR Ed Et Fn Fp Fy Gc gL Gp gW Ha Hx Ic Il In Io Ir Is Iu Jf Ji Jl Jm Jn Jp Jq Jr Kg Ki Ko Kq Kx Lh Lw Lx Lz Mc Mh Mi
Mj Ml Mm Mp Mx Nc Nh No Nr Nv Nw Oa Oh Ok On Pd Pe Pf Pg Ph Pi Pj Pk Pz Qa Qc Qd Qe Qg Qh Ql Qm Rg Ri Rj St Tn Tr Tt Tv Tz Ub
Uc Ud Ug Uh Us Ut Uv Vs Vt Wm Tj) cF(aC An aO aP AR aS AW aX aZ bB BC bF Bg bH bJ bM bN bO bS bW bX bZ cB cD cG cL CO Cq
cS cU cV cZ dA Db DE dF dH dK Dl dN DR Dv Ed eF Fb Fn Fr Fy gC gL Ha Hf Hr Hw Hx Id Ih Ip Is Je Jl Jm Jn Jp Jr Ko Kp Kr Kz Lh Lj Mb
Mg Mk Mp Mr Ms Mt My Mz Na Ne Nf Nh Ni No Ns Nu Nw Nx Oe Oh Ok Ou Oz Pb Pc Pe Pg Po Pz Qb Qd Qe Qh Rg Rh Ri Rm Sr Tr Tt Tv
Tz Un Us Uv Vq Vs Vt Tj) Ez(Aa Ad aE AF aH aI aK AL AO aR aU bB bC bE bF BG bH bl bL bM Bn bP bQ bS bV bW bX bZ cA cE cG cJ
cK Co Cp cQ cR cU CV Cw CX cZ dB dC dH dK Dl dM Dp Ef Fb Gp Hb Hc Hv Hx Id Ij Iq Iv Iz Jd Jh Ji Jl Jp Js Jv Kd Ke Ki Kl Kq Kx Lh Lu

Tr Um Ut) Ko(bL cL Cp cV Dp Gl Jk Kz Mj Nu Om Tz Ua Uh Un Vo) Kk(aM aV aZ bC cL cN dA dJ Dp Ed Ha Ib Jy Og Po) Hf(aG aM aN aX dl Dp Jk Jr Kn Pb Rc Up Ut Vp) Qw(aX aZ bE cH Dp fR Hv Id It Oa Oe Ub) Ib(cF dJ Ir Jm Kg Ky Nn Oh Qd Rm) Nu(aM cN Ha Hr Kz Mw Pb Qx) Qy(CH eF Fa Rf To Ue) Og(aN eF Jn Jy Ld Pb) Rf(bE cC dI Kz Mw) Pb(aN Cs dJ eF Uk) aV(bE dF dG dR Qx) Rc(Ad Ir Kp) Kz(cN dN Nb) aJ(bU bW Mw) aN(Oh Oz Pc) eF(Kn Oz Vo) lh(Jk Ur) Rb(aC dG) Qz(aZ cN) Kf(Uo Uu) aX(It Rm) cB(aD aM) DgVo MwNb IccP RaaZ OuaL bRdG cLdJ cNcY} fR{Ko(Ad aH Aj Ao Ap As aV aZ bJ cE cG cM Cp cS Cv Dc dE dJ Dk Fy Ha Hu Ij In Iz Jd Jq Jr Jv Kd Kg Kq Ky Kz Lh Li Mm Mn Mq Mr Mu Mv Mx Na Nd Ne Nj Nq Oe Of Pa Pb Pg Pz Qd Qh Qn Qx Qy Ss Tn Tr Tt Ul Ur Ut Vp Vt) Qw(Ex Fp Hc Hu Jh Kd Md Mq Mx Nq Or Ou Pa Pb Ph Qy Ra To Uk) Rb(Hr Iq Jk Jn Ks Ky Md Ml Na Ow Qx Rf) Nj(gL In Jn Kz Mq Na Og Om Oz Qx) Nd(cE It Mn Nc Og Oz Pa Pc Qe) Oz(hC Kk Lv pF Qe Qx tF) Ou(aH aN aX Mr Ra Ut) Qx(As Ib Pc Qt Rc) Kk(Kx Mb Pc Qt Qz) Qz(iZ tF) aV(dO gT) bR(dO dV) DboE GtbU RaUr QtPh JnOm PccP dJeX} aV{dO(Ad aE aF aG aH aI aK Al An aO aP aQ aS aU aW aZ bB bE bG bl bM BN BO bP bQ bS bV bZ cD cE cG Ch cJ Co cR cS cV CW Cx cY dA dB Dc DG Dk dN DR eF Em EX gC GI GT) gN(aM aN aU bE bJ cE cF cG dF dG Di dL gW) Dq(aM aN aQ aY bl cH cR dF Dg Dl) Dr(bE cO Ex Gw Io Qw Ra) Gc(cN dK Gl In Og Ue Vo) Gt(bA bQ cF cH Cs Dd gW) eX(aJ bR cL cN Fw) Dv(aU cN dM Fw) dV(aQ aU cL dF) Gw(aJ aU cY) gC(aP aQ bE) gT(cL cO gW) dX(aN Kk) DodK} Em{Rb(Aj aP bO cB cH cL cQ cW Dc dH dI Gl Hr Jy Mr Mv Nu Oy Pa Pc Qx Up Vp) Vo(Ar Ba dF Fa Gc Im Is Kq Ky Lh Mg Pb Qb) aJ(dI Jk Jy Ld Mu Nx Pc Ue Uf Ur) Kk(aN Kd Ma Mw Nc Nm Om Qh Ss) Nu(Ch Ha Kd Mv Mw Qw Ua) Qz(aH Aj dN In Of Uu) Qw(Gl In Jf Jo Ub Uu) Kj(Ex Oh Ou Ph Qa Rf) Ld(dL Ib Om Ue Uu) Ex(Ma Po Ue) Ii(Dl Kf Ou) aN(bR cF Oh) Gl(bA Ko) Ue(Og Qy) Ib(aA aZ) Hf(Dc Ra) Qx(aQ Ed) Nx(Jt Ke) Ph(Ng Uu) cY(dM Uo) CsQt CtOu HuQy PcaZ cFdL} Og{Nt(aA Hq Hr Hu Hv Hw Hx Ih Ij Im In Io Iq Ir Is It Iu Iv Jh Jk Jl Jm Jn Jq Jr Js Lh Li Lj Lu Lw Lz Ma Mb Mc Mg Mh Mi Mk Ml Mn Mq Mr Ms Mu Mv Mx My Na Nb Nc Ng Nh Ni Nk Nm No Nq Nr Ns Nu Nx Ny Oe Of Oh Oi Om Oy Pb Pc Pd Pe Pf Pg Po Pz Qa Qb Qc Qe) Ik(Fp Iu Lh Li Lj Lv Md Mi Nm No Nv Pe Pz Qd) Nj(eM Jt Mi Nx Qe) Dr(dJ Ld Pi Rb) Ne(Lv Mm Nx) Nd(Nv Qe) GcaN LvMm MdNx NcPa KkeM] nD{qW(hW iC jD jG jM jY kO IK IN lO mE mM mT nB nF nL nN nT nU oP qT qX rA rX) nA(iC jE jO jP jU kC kF kG kK kN kO IN mT mY nF nL) hV(hA jM kK kN IK IX mW mZ nB nR oQ qY) rA(jH jR jY kN IL IM IX mH ml mZ oQ qX) oP(hR iC jR kN ml mM mY mZ nL oO oQ) qX(jU kC kN IL IN mS mT nT qT) nR(kP IK mT mU nl nJ) oQ(lY mM mZ nN nT nU) kP(mP nB nF nl nJ) IX(kC mT nl nM) mH(ml mP mY nB) jQ(kC nK) mTjR mZkN nJjF} dX{Ko(aN bN cL dJ dN gL Iz Jh Ky Lh Md Mw Qu Ss Tr Tz Uf Uh Un Ur Vt) Qx(aN dJ Fw Hv Ib Ih Jy Ky Mz Nu Oh Rc Rf) Kk(aL aM bU Ed Ke Om Or Rc Tv Ur Wm) Hf(Al aM aS cA Jh Lh Mz Na Nh Uo) Qw(aJ Ar Ax Cs Ib Ih Jn To Uk) Pb(aZ cP dJ Ky Nu Uk) Hu(Jf Kj Kz Ld Qy) cN(cY Lj Nu Rb Vv) aN(bR cH Oz Qy) Ib(Jn Kp QI) Ur(aC bE cF) Ha(Ex Rf) Nu(aX Kz) Rc(Jn Kp) Vo(eF Ih) Pc(aZ dJ) aJ(gC Kz) CsOz liNx RbaX QzaZ QyKy OuaL aDcB bRdL cLeX} eM{Kk(bR bU bW cP Cq cT cY De dN GI Hr li lu Jf Jn Ko Li Ms Mz Nb Ng Pb Ph Qw Tn Up) Ko(aZ cF cN Cp Ii Jd Kc KI Ks Mv Mw Tz Ua Uh Up) aX(Fa Hf Id Je Kf Nd Ne Pc St To Tv Uk) Hu(bR Fw Hf Kx Pc Qw Rm Up) Ib(Di Kp Oi Vv) aN(Cs Di Pb Wm) bE(Kz Nj Oa Oz) Rb(bI dF dG) Qx(aZ bU cL) Qw(aJ cN gL) Rf(cF Gl Ns) Fa(aC Gl) Ha(Ih Nx) In(Ih It) Ld(dK Ra) bR(aJ cL) BoDi CsOz PoOa FpHr NsTo HfPb KzaC NxUk aDcB bWdG cHcN] Gt{cL(AA aC aD al aJ aK aQ aU Ba Bc cT Dd dG Di dJ dL dO Dq Dr Fr Gp) Fw(aC aF aG aH aJ Ar aW aX bA bB bM bW bZ CQ Cv Dd eX Gp) aN(al aM aZ bF Bg bV cR Ct dF DG dO Gw) aJ(An aP aQ bZ cA cP cY dR dV gC) eF(aM cA cF Cw dA Dc dD dI dJ) Bo(aK cH cP cY Db Dd dO Gp) cF(aK aM Bc cH dJ Dl dR) dG(aQ cP cY) aD(bA Gp) cB(aM Dd) cN(aK dR) dL(An bR) dM(aQ cY) bFcP} aX{Ou(Aa aH aN bJ bN bQ cE Fw Iq Jk Jr Js Ko Md Mj Nd Nk Om Qy Rm Vp Vs) Rb(bJ bN Ha Im Pa Pb Ph Qe Qy Sr St) Ko(bL cE Ij Jq Md Mj Mq Qt Rj Vo) Qe(Dc Ii Mj Nd Nj Pb Qc) Aa(Jf Kd Nd Qw Vo) Vq(Jo Nc Qw St Ue) Dr(Fn Ih Pi Qz) Nj(Iq Pa) GcUe NrOm NdPa PcaA PhbN bRdO dLgC] oP{mF(eD hR jF jR kG kN kO IY mM mZ nC nF nH nN nO nU oQ) nU(IK lY mM mP mZ nC nH nL oQ rA) IK(hR hX jI kP IL nN nR rY) nL(kN kP mM mP nB nJ nT) mZ(kI kK kO nF nK nO) rX(hV jF jQ qU qY rZ) kP(kC kO ml mM nN) nT(IX nA rA) ml(IX mH mM) eD(jQ rA) nK(mM nN) nOIX nAnI jEjF qYjQ} Pa{Ik(Fp Hw II In Iu Jo Lv Lz Md Mi Mm Ng Of Qe) Nt(aA Fp II Iq Jo Lv Md Mi Nc Nd Ne Ng Of) Nj(aA Fp Fr Hw II In Li Lv Md Ni Nx Qa Qe) Ne(aA Fp Hw II Lv Mi Mm Nk Qe) Nc(Fp Hw In Lv Mm Nd Ni Qe) Nd(Im Mm Nv Qa Qe) Qe(Dc In Qc) Fp(Lv Mi) LvMm JkKo} Dq{Fw(AF aH aJ aK Ao aR bB bU bW cC cD cK cX cY cZ dC Dd dJ dR dV gC GI Gp gW) cL(Aa Ad aK Ar aU Ax bC bL cA cB cY Dd dL dO Ex Fr) bC(bw cF dJ DL) cF(Bc cH dG dJ) eF(bZ cA Ch dC) aJ(aQ bU dI) bE(aK aQ dO) cY(cN dK dM) aN(cH Cs) AdDd cNdR dAdG} Dr{Hu(aN dG Fw Hf Hq Ib Jf Jn Kf Ky Oa Or Pc) Ra(cY DI Jn Kz Or Qb Rb Rm Ue Ug) Nx(Co Ez Fb Jt Mv Or Pj Rb Uk) Rb(lc Jy Ni Rc Ue Ug) In(Ld Ou Qw Rm) Vo(Jn Oi Qw) aJ(dJ Mv Mw) Fw(eX Gw) Ib(aC Ky) Kk(Ue Ul) Ko(Aa Jt) dJ(bC Or) GwcL NkQw HfOm RcKf QxaQ LdUo aNcH} Qe{Nd(Dc Fr Hr In Iu Jo Js Lv Lz Md Mi Mm Mz Nc Nt Nv) Nj(Dc Hw II Jm Jo Js Lv Md Mi Mm Of Qc) Dc(Jf Js Oy Pc Qc Rb) In(Ik Lv Nh Nt Nx Qc) Nc(Hw Iq Lv Nk Qc) Ik(Iu Jm Md Of) FpJo NtJt LvNe MdNx OuVu} Gc{Ue(bE Dp GI In Kk Ld Or Qw Qy Ra Vo) Hu(cP dG dL Ko Nb Nx Ul) Nx(Aa Ii Jo Jt Ks Vo) Rb(Aa cF dM Kj Vo) Kk(dJ dL Iz Jy) Aa(Ko Ky Nj) Ib(Ex Hf Oa) Vo(Hf Qw Qx) Ra(Kj St) Qt(Jn Kd) InJy HfaN QwaJ KjcF KoUf] aJ{gC(aD aK aM aQ bS cH cJ cL cM dI dL dO eX gT) dV(aF aK aQ bA bN Bo cC cN cS cT dD dE dK) bU(cJ Do eX Gw) dO(cF cL dl) bLcJ cBgN dAgT} Mi{Nj(Hq II Im Jm Mm Ni Nq Nr Nx Oi Pz Qa Qd) Nd(Jl Lu Nc No Nt Nv Nx Oy Oz Qa) Nx(Fp Hr Md Of Oz) Oz(Fp Ik Nt) Ne(Fp Hw) IkJo} hV{eD(kC kF kG kO IX lY mE mF mH ml mW mY nA nC nF nH nl nJ nK nL nM nN nT oO) rB(iC jE jG jQ) mS(hR kE) IL(jQ nO) mTqT} eX{cL(Aa cB cP Cs DD DL dV) Fw(aM Ar bL Ch Dd dI dJ) Dl(bR bU cF) aN(Cs Dd dR) bU(dF dL) cB(aD aM) bBcN bCdJ bRdF bWdG dldL} dG{dV(aD aO aY bA bW cA cN cT dA dD dH) gC(aK aQ cA cF cM Cs cY dA dH) gT(bR bU cF dA) bR(gN Gw) bU(dO gN) cFdO} rA{nO(jD jP jY IK IO mE mF ml mP mS mT nN nT nU rB rX rY) mF(jD jH ml nT) nU(kP IK mT) ml(mM rZ) nTkP mTnF} Nd{Nv(Hw II In Iq It Js Lv Md Mz Nc) JI(Hr Lz Md Mj Mq Mz No Nx) Mm(aA Nc) MwMz IuQa} cL{gN(bU cA Cs cY dR) gT(bU cB dD dI dJ) dO(Aa cZ dl) Do(bR Dl) Dv(bR Fw) dV(cB dL)} Ko{Jf(Bg Dc Dk Mq Mu Po Qt Qw) Jk(aZ bL bN cS cU Oy) Qw(bN Rj) CwaZ IqOm} Nx{Lv(In Md Mh Nc Nj Oh) Md(Fp Hw Nc Ne Oz) In(Ih Ne) JI(Hw Hx) NcNi} Nc{Lv(Hw Mp Nt) Nk(Fp Nt) Hw(Pe Qa) In(Nv Pe)} Ne{Mm(aA Hw Lv Oz) Aa(Hw Oz) In(Nv Pe) FpaA} cF{dL(dO Dv gN Gw) DI(DO Dv) DvaN dFdV} cN{dV(aK aU bB cY) gN(aK aU cY) aUgT cHdO} IK{nR(eD iC jO jV IW mF mS) mMIL mZoQ} Jo{Lh(Fp Ik Nj Nt) Ik(Li Mm) FpNt VqhB} aN{Cs(DV gT) Fw(Dv gN gT) cHgC} nO{jF(iC jV mT mZ nA) nArZ qXIL] Nj{II(Lh Lv Nv) Md(Mm Nv)} Ou{Ha(Ar Lj) CtEx RbVu RaVq} bR{dL(dO gN gT) DIDo dOeF] Bo{Dl(Dv gT) DigN ExdV} Fw{dV(aD cA) AIDv] Nv{Md(Iq Nq) IqOm] Vq{CtoK VsiA dRgW} cB{aM(Do gT) aDdO} eD{mPqX mZjF nArZ} mT{mZoQ nArZ hRjF} IW{qW(rY rZ)} AdDdDo LvMmOz nUnAoQ mIqXIL Unconstrained panels with 2 analytes, where 1.0E-7 >= 'AUC p-value' > 0. Contains 207 panels of 81,255 total panels evaluated. : Nw(Et Fp Fr Hq Hr Hv Hw Hx Ij Ik In Io Iq Ir Is It Iv Jg Jl Jn Jo Jp Jq Jr Js Jt Li Lj Lu Lv Ly Lz Ma Mb Mc Md Mf Mg Mh Mi Ml Mn Mq Ms Mt Mx My Na Nc Nd Ne Nf Nh Ni Nj Nk Nl No Ns Nt Nu Ny Of Og Oh Oi Ok Om On Oy Oz Pa Pe Pf Pg Po Pz Qa Qd Qe) Ok(Fp Hq Hr Hw Hx Ii Ij Ik In Iq Jg Jj Jo Js Jt Lv Lx Ly Ma Mb Md Mg Mi Nc Nd Ne Nf Ng Ni Nj Nl Nq Of Og Om Oz Pa) Gn(Aa aN aV bR cP dJ Gl gP Hu Ly Om Or Qt Qw Ra Rb Rc Ue Um Uo Vo) Et(Jj Jo Jr Jt Lv Lx Ly Mt Nc Nd Ne Nf Nj Nl Of Og Om Oz Pa) Lx(Hw Hx Ik Jg Jj Js Lv Ly Nc Nd Ne Nf Nh

Figure 9 Continued

Nj Nl Nq Po) Ly(aX Dr EM FR Jp Mt On) Mt(Fp Hw Jj Lv Nc Nd Nj Nl) On(Nd Nf Om Oy) Jp(Ik Nj Nl) Kc(dX Em) nD(hV nA) NtOg NfJi NlJj aVdO

Unconstrained panels with 2 analytes, where 1.0E-6 >= 'AUC p-value' > 1.0E-7. Contains 306 panels of 81,255 total panels evaluated. : Ok(Fr Hu Hv Ih Il Im Io Ip Ir Is It Iu Iv Jh Ji Jk Jl Jm Jn Jp Jq Jr Lh Li Lj Lu Lw Lz Mc Me Mf Mh Mj Mk Ml Mm Mn Mp Mq Mr Ms Mt Mu Mv Mw Mx My Mz Na Nb Nh Nk Nm Nn No Nr Ns Nt Nu Nv Nx Ny Oe Oh Oi On Oy Pb Pc Pd Pe Pf Pg Po Pz Qa Qb Qc Qd Qe) Nw(aA Hu Ih Ii Il Im Ip Iu Jh Ji Jj Jk Jm Lh Lw Me Mj Mk Mm Mp Mr Mu Mv Mw Mz Nb Ng Nm Nn Nq Nr Nv Nx Oe Pb Pc Pd Qb Qc) Et(Fp Hv Hw Ik In Ip Iq Iu Iv Jg Ji Jp Js Lj Mb Md Mi Nh Nk Nq Nt On Pb Pc Pe Pf Pg Qa Qe) Gn(aD aG aJ Bb bL bU cF Ch cN Cw dI dL Do Ef eX Ez Ib Ij Jy Kc Kn Me Mv Ny Og Qu Uf Ul Uu) Mt(Hx Ii Ik In Iq Ji Jk Jp Js Lj Lx Md Ms Ne Ng Nh Nq Ns Nu Nx Oe Of Og Om Oy Oz Pb Pc Qe) Lx(aA Fp Hr In Ji Jk Jp Lz Ma Mb Md Mf Mn Nb Ni Nr Nt Nu Nx Oe Og On Oz Pb Pc Qc Qe) Nl(AA Fr Jg Ji Lv Mi Mm Nx Og On Pa Qe) Jg(Fp Jj Ly Nc Nd Ne Nf Nj Of Om) On(Fp Hw Ik Iq Lv Nc Ne Nj Nq Of) Ji(Ik Lv Ly Nd Ne Nj Oz) Jp(Lv Mb Nc Nd Ne Nf Nu) Qe(Ly Nd Nf Nj) Jj(Ik Nc Ne Nt) gP(aJ bA dM Ly) oP(mF nD nL) Mi(Ly Nj) Nd(Jl Nv) Kc(eM eP) DqFw LvNx NfPe nOrA nDqW Unconstrained panels with 2 analytes, where 1.0E-5 >= 'AUC p-value' > 1.0E-6. Contains 481 panels of 81,255 total panels evaluated. : Et(aA Fr Hq Hr Hu Hx Ih Ii Ij Im Io Ir Is It Jf Jh Jk Jl Jm Jn Jq Lh Li Lu Lw Lz Ma Mc Me Mf Mg Mh Mj Mk Ml Mm Mn Mp Mq Mr Ms Mu Mv Mw Mx My Mz Na Nb Ng Ni Nm Nn No Nr Ns Nu Nv Nx Ny Oe Oh Oi Ok Oy Pd Po Pz Qb Qc Qd Vo) Gn(Ad Aj An Ao Ap aQ As BA Bg bW cA cB cE cH cI cL cM Cs Cu cY dA Dc Dd dG Di Dp Dq Em Ex Fb Fr Fw Gp Gt Hb Ii Iz Jj Jo Ju Jv Kd Ke Kf Kj Kk Kl Ma Mu Nb Ng Nj Nm Of Pc Qv Ss Uh Uk Up) Mt(aA Hq Hr Hu Hv Ij Il Im It Iu Iv Jg Jm Jn Jo Jr Li Lu Lw Lz Ma Mb Mc Mf Mg Mh Mi Mk Ml Mm Mn Mp Mq Mu Mv Mw Mx My Mz Na Nb Nf Ni Nk Nm No Nt Nv Ny Oh Oi On Pa Pd Pf Pg Po Qa Qb Qc Qd) Lx(Hq Hu Ih Ii Ij Il Im Ip Iq Ir Iv Jh Jl Jn Jo Jr Lh Li Lj Mc Mg Mh Mi Mj Mk Ml Mm Ms Mu Mv Mw Mx My Na Ng Nk Nm Nn No Ny Of Oh Oi Pd Pe Pf Pg Pz Qa Qb Qd) Jg(Hw Ik Iq Iu Iv Ji Jk Jo Jp Jt Lj Lv Md Mv My Nh Ni Nq Nu Og Oz Pa Pb Pc Qa Qe) Ly(Aa aJ Ar bA bV cH dE Gc Id Im Jj Jl Lh Mm Mz Nl No Nv Ny Pa Pe Sr) On(Hx Ii In Iv Jj Jk Jq Js Jt Lj Ma Mb Md Ng Nh Ni Oe Og Oz Pa Pb Pc) Jp(Fp Hw Hx In Iq Iv Ji Jj Jr Js Lj Md Mf Nh Ni Nk Nq Nt Oi Pa Qe) Ji(Fp Hw Hx In Iq Iv Jo Jq Js Mb Md Ms Nc Nh Nt Oi Om Qe) Qe(Dc gP Hw Ik In Iq Jj Jo Lv Nc Ne Nq Nt Nx Qc) Nf(Ar aX Fp FR Lh Li Lv No Nt Nv) Nl(Fp Im Li Lj Mz Nk Nt Nv Pb Pe Qa) Lv(Fp Mm Nc Ne No Nt Oh Pg Qa) gP(Bc bV eF fR gL Kk Ko Sr) oP(lK mZ nF nH nO nU rX) Fp(Jj Mi Nc Ne Nt Pa) Nd(FR Mi Mz Qa) Nj(Fr Li Mm Nv Pa) Gt(aN cL eF Fw) Nc(Mm Nk Nv Pa) aX(Me Nw Ou Rb) nD(kP oQ qX rA) Nt(Jo Oz Pa) Nx(Hw Md Mi) aJ(cJ dV gC) Dq(cL eF) Me(Gz Sr) Ne(Mm Pa) Ik(Og Pa) Ko(fR Jk) Nv(Hw Iq) dG(dV gC) hV(jQ rB) DrKc FweX NhJj QwfR KkeM OkaA nRlK nUoQ rBrA Unconstrained panels with 2 analytes, where 1.0E-4 >= 'AUC p-value' > 1.0E-5. Contains 1,234 panels of 81,255 total panels evaluated. : Gn(aC aE AF aH aI aK aL aM aO aP AR aS AW AX aY aZ bB BC bE bF bG bH bI bJ bM BN BO bP bQ bS bV bX bZ cC cD cG cJ cK CO Cp CQ cR cS CT cU CV cW CX cZ DB dC dD DE dF Dg dH DK Dl dM dN DR Ed eF eP Fp fR Fy GC gL gT GW Hf Hq Hv Hw Hx Id Ik Il Im In Iq It Jd Je Jf Jg Jh Ji Jk Jl Jn Jr Jt Kg Ko Ks Ky Kz Ld Li Lj Lu Mf Mg Mk Mn Mq Mr Ms Mw My Na Nd Nf Nk Nl Nq Nu Nv Nx Oa Oe Ou Ow Oy Oz Pa Pb Pj Qm Qx Qy Rf Rh Sr Ua Ub Uc Un Ut Vq Vs Vt Tj) Jp(Fr gP Hq Hr Hu Hv Ih Ii Ij Im Io Ip Ir Is It Iu Jh Jk Jl Jm Jn Jo Jq Jt Lh Li Lu Lw Lz Ma Mc Me Mg Mh Mi Mj Mk Ml Mn Mp Mq Mr Ms Mu Mv Mw Mx My Mz Na Nb Ng Nm Nn No Nr Ns Nv Nx Ny Oe Of Og Oh Om On Oy Oz Pb Pc Pd Pe Pf Pg Po Pz Qa Qb Qc Qd) Qe(aX Fp Fr Hq Hr Hu Hx Ih Ii Ij Il Im Ip Ir It Iu Iv Jk Jl Jm Jn Jq Jr Js Li Lj Lz Mb Mc Md Me Mf Mg Mh Mi Mj Ml Mm Mn Mp Mq Ms Mu Mw Mx My Mz Na Nb Ng Nh Ni Nk Nm Nn Ns Nu Nv Ny Of Og Oh Oi Om On Oy Oz Pa Pb Pc Pd Pe Pf Pg Qa Qb Qd) Jg(Dc Hq Hr Hu Hv Hx Ih Ii Ij Il Im In Ip Ir It Jh Jl Jm Jn Jq Jr Js Lh Li Lu Lw Lz Ma Mb Mc Me Mf Mg Mh Mi Mj Mk Ml Mm Mn Mp Mq Mr Ms Mu Mw Mx Mz Na Nb Ng Nk Nm Nn No Nr Ns Nt Nv Nx Ny Oe Oh Oi On Oy Pd Pe Pf Pg Po Pz Qb Qc Qd) Nl(Hq Hr Hv Hw Ih Ik Il In Io Ip Iq Ir It Iu Iv Jh Jl Jm Jn Jo Jq Jr Jt Lh Lw Lz Ma Mb Mc Md Me Mf Mg Ml Mn Mp Mq Ms Mu Mw Mx My Na Nb Nd Ne Nf Ni Nj Nm Nn No Nq Nr Ns Nu Ny Of Oh Oi Om Oy Oz Pc Pd Pf Pg Po Pz Qb Qc Qd) On(Fr Hq Hr Hu Hv Ih Ij Il Im Io Ip Ir Is It Iu Jh Ji Jl Jm Jn Jo Jr Lh Li Lu Lw Lz Mc Me Mf Mg Mh Mi Mj Mk Ml Mn Mp Mq Mr Ms Mu Mv Mw Mx My Mz Na Nk Nm Nn No Nr Ns Nt Nu Nv Nx Ny Oh Oi Pd Pe Pf Po Pz Qa Qb Qc Qd) Ji(Fr Hq Hr Hv Ii Ij Il Im Ip Ir It Iu Jh Jj Jl Jm Jr Lh Li Lj Lu Lw Lz Ma Mc Me Mf Mh Mi Mj Mn Mq Mx Mz Na Nb Ng Ni Nk Nn No Nq Nr Ns Nu Ny Of Og Oh Oy Pa Pb Pc Pe Pf Pg Po Pz Qa Qd) Fp(aA Fr Hr Hw Ih Ik Il Im In Io Ip Ir Is Iu Iv Jh Jl Jn Jo Jr Js Lh Li Ly Lz Ma Md Me Mg Mh Ml Mm Mp Mq Mu My Mz Nd Nh Ni Nj Nm Nu Nv Nx Og Oh Oi Oz Pb Pf Pg Pz Qa Qd) Ly(aA Ad aN Ap Ax aZ Ba bC bE bN Bo cG cJ cQ Cs cT Dd dF DG dM dX eF gL Hv Ir Iv Jf Jn Jr Ko Kq Li Lj Lv Ma Mp Mw Nc Ne Nn Nt Nx Oh Ou Pg Pj Qa Qd St Tt Uh Vt) Lv(aX FR Hv Ih Ii Ik Il Im Iv Jj Jl Jm Jn Jr Jt Lh Li Lj Mp Mw Mz Nd Nh Nj Nn Nr Nv Ny Oi Oz Pa Pe Pf Pz Qb Qd) gP(aA aP Ax Ba cH dF DG Dl Et Fr Gt Jf Kc Kp Kq Lx Mt Nf Nw Ok Or Ou Qa Qw Qy Rj Uk Ur Wm) Nt(aA Fr Hw Ik Im In Iq Iu Jl Li Lj Md Mi Nc Nd Ne Ng Nh Nj Ns Oe Of Om Pb Pc Pe Pf Pg Qa) Et(Ao aX bA Bg bV Dc Gl Ha Il Kc Kd Kk Ou Ql Qt Qw Qy Ra Rb Rc Rj Ue Ur Ut Vu Wm) Nx(Hr Ik Il Im In Ir Li Lj Lz Mb Mu Nc Nd Ne Nf Nh Nj Nn Nu Og Oi Oz Pe Pf Pg Qa) Nc(AA Fr Hw Ik Im Jl Jn Jr Li Lj Mi Mp Mz Nd Ni Og Oz Pb Pe Pf Pz Qa Qd) Lx(Aa aX Fr Hv Io Is It Iu Jm Jq Jt Lu Lw Me Mp Mq Mr Mz Ns Nv Om Oy Pa) Ik(aA aX Fr Im Iu Jl Jo Li Lj Md Me Mi Mm Mp Mz Ne Nf Nv Oz Pe Pg Qa Qd) Ne(AA Fr Hw Im Jn Jr Lh Li Lj Me Mi Mp Mz Nk Nv Og Pc Pg Qa Qd) Nw(Ao bA Bg Co Dc Dk Gl Ha Ql Qw Qy Ra Rb Rg Rj Ut Vo Vp Wm Tj) Nj(AA aX fR Im Ij Jl Lh Lj Lw Mu No Og Pc Pe Pg Pz Qa Qd) Mt(Fr Ih Io Ip Ir Is Jh Jl Jq Jt Lh Me Mj Mr Nn Nr Pe Pz) bA(aH aX bC bL bM bR bU cC cD cE cH cJ cM cX dG Me Nf) Ko(aX bL bN Dc Dd Dk Iq Jf Me Mj Nf Om Po Qt Qw) Nv(Hx In Iv Js Lj Mb Md Ng Nh Ni Nq Nu Oi Om Oz) dG(aX bL bN bQ bR bS bU cE cJ cM cT dH Dq Nf) Nd(aA Im Lh Li Mm Mp Mu Mw Nn No Pe Pg Qd) Jj(Iv Jm Jn Jr Lh Mg Mm Nr Pa Pe Pg Qa Qd) Nf(aJ bV Fa Id Jl Kq Lj Nr Nu Pg Qa Sr) aX(aJ Iq Kc Mb Oi Ok Pb Pc Ph Qw Qy Sr) oP(kK kO kP lX mH mI mM nB nC nK nN nT) hV(iC jE jR lL lW mS nU qT qW rZ) Nu(In Jl Jo Li Mz Nn Og Pa Pg) Me(Dr fR Hf Id Jf Kc Kf Ou Vq) Ok(Bg Dc Dk Gl Ha Rb Tn Ut Tj) aJ(bL bN bR bU cM Dq Em Gt) nD(jD mH mM mP mU nF nI nJ) Oz(Aa FR Lh Mi Mm No) fR(bU Pc Qx Ra Rb) Fr(Iv Nh Nq Pc) aV(Dq Dr gN Gt) rB(eD hX jF jK) rA(mF mI nT nU) oQ(mF mS mT mZ) Nh(aA Mi Pa) cH(cJ dF dM) Og(Iv Oi) Pe(In Iq) cL(eX gN) AdDc BoGt DgVo DqbC EmRb GcKc MfLi HwQa HfdX cJdM dLdV eDnR nOjF Unconstrained panels with 2 analytes, where 1.0E-3 >= 'AUC p-value' > 1.0E-4. Contains 2,851 panels of 81,255 total panels evaluated. : Nw(aC AD AF aG aH aI AJ aK AL aM AN aO Ap aQ AR As aU AW Ax aY Ba BB BC bF bH bI bJ bL BN BO bP bQ bS bU bV bX cA cB cC cD cE cF cG CH cI cJ cL cM cN cO CP Cq cR CS CT CU CV CW CX cY cZ dA DB dC DD DE dH Di dK dL dM dN Ed Ez Fa Fn fR Fy Gn Hb Hc Hf Ib Ic Id Iz Jd Je Jf Ju Jv Jy Kd Ke Kf Kg Ki Kk Ko Kp Kq Kr Ks Kx Ld Oa Ou Pk Qg Qh Qm Qn Qt Qu Qv Qx Qz Rc Rf Rh Ri Rm Sr Ss St Tn To Tr Tt Tv Tz Ub Ud Uf Ug Uh Uk Ul Um Un Uo Up Ur Us Uv Vs Vt Vu Vv) gP(AD Af Aj Al An Ao Ap Ar aW aX BB bC bE Bg bJ bM BN BO bR bW bX bZ cG Ch cM cN Co Cp Cq cR CS CT CU CV Cw Cx dA Db Dc DD DE Di Dk dL Ef eM Ez Fa Fb Fp Fw Fy Gp Gw Ha

Figure 9 Continued

Figure 9 Continued

Unconstrained panels with 2 analytes, where 1.0E-2 >= 'AUC p-value' > 1.0E-3. Contains 7,717 panels of 81,255 total panels evaluated. : Ko(aA aC AD aE AF aG aH al AJ aK AL aM AN aO AP aQ AR AS aV AW Ax aY Ba BB BC bE bG bH bI bM Bn BO bP bQ bR bS bU bW bX bZ cA cB cC cD cF cG cI cJ cK cL cN cO CQ Cs cT Cu Cv cW CX cY cZ dA DB dC dD dF DG dH DI dK DL dN Dp dR Ed Ef Ex Ez Fa Fb Fn FP Fr Fw Fy GL Gp gW Gz HB Hc Hf Hr Hu Hv Ic Id Ih Ik Il lm Je Jg Ji Jj Jm Jn Jp Jt Ju Jy Kc Kd Ke Kf Ki Kj Kk Kl Kn Kp Kq Kr Ks Kx Ky Kz Ld Lh Li Lj Lu Lv Lw Lz Ma Mb Mc Mf Mg Mh Mi Ml Mm Mn Mp Mr Ms Mt My Mz Na Nb Nc Nd Ne Ng Nh Ni Nj Nk Nl Nm Nn No Nr Ns Nt Nu Nv Nx Oa Of Oh Oi Ok On Or Ow Oy Oz Pc Pd Pe Pf Ph Pi Pj Pk Pz Qa Qb Qc Qd Qe Qg Qh Qu Qv Qy Qz Rh Ri Sr Ss St To Tr Tt Tz Ub Uc Ud Ue Uf Ug Uh Um Un Uo Up Us Uu Uv Vt Vv Wm) Qe(aC AD aE AF aG aH al aJ aK AL aM AN AO AP aQ AR aS aU aV AW Ax aY aZ Ba BB Bc bE bF bG bH bI bJ bL bM Bn BO bP bQ bR bS bU bW bX bZ cA cB cC cD cE cF cG CH cI cJ cK cL cM cN CO CP CQ cR CS CT cU CV CW CX cY cZ dA DB dC dD De dF DG dH DI dJ dK DL dM dN DO dR dV Ef eP Ex Ez Fa Fb fP fR Fw gL Hb HC Hf Ib Ic Id IZ Jd Je Ju Jv Jy Kd Ke Kf Kg Ki Kj Kk Kn Kp Kq Ks Kx Ky Kz Ld Oa Or Ou pF Ph Pi Pj Pk Qh Ql Qm Qn Qt Qx Qy Qz Rc Rf Rg Ri Rj Rm Sr Ss St Tn To Tt Tv Tz Ua Ub Uc Ud Ue Uf Ug Uh Uk Ul Um Un Up Ur Us Uu Uv Vo Vt Vv) eF(aA aC AD AF aG aH al aJ aK AL aM aN AO AP aQ AR AS aV AW AX aY aZ BA BB bC bF bG bH bI bJ bL bM BN BO bP bQ bR bS bU bV bW bX bZ cA cB cC cD cF cG cI cK cL cN CO CP CQ cR CS CT Cu CV CW CX cZ dA DB dC DD De dF Dg dH dI dK DL dM dN DO dR dV Ef eM eP Ex Fp FR Fw GL Gp GW Ha hC Hq Ib Id Ii iJ In Iq IZ Jf Jj Jl Jp Jq Jr Jy Kd Kp Lx Md Me Mj Mq Mr Mv Mw Na Nj Nq Nw Oe Ok Ou Oy Oz Pa Pb pF Pg Pj Qg Qx Rb Sr Ss Tn Ua Uk Ur Ut Vp Vq Vs Vu Wm Tj) gP(Aa aC aE aF aG aH al aK aL aM aN aO aQ aR AS aU aV Aw aY aZ bF bG bH bI bL bP bQ bS bU cA cB cC cD cE cF cI cJ cK cL cO cP cQ cW cX cY cZ dB DC dH dI dJ dK dN DO Dp Dq DR DV Ed eP EX Fn fP GC GI gW hB Hq Hr Hu Hv Hw Hx IH Ii Ij Il Io Ip Ir Is Iu Iv Iz Jh Jl Jo Jq Jr Js Jt Ju Ke Kg Ki Kj Kr Ks Kx Lu Lw Lz Ma Mc Md Mg Mh Mi Mj Mk Ml Mn Mp Mr Ms Mv Mw Mx My Mz Nb Nc Ne Ng Nh Ni Nk Nl Nm Nn No Nq Nr Ns Nt Nu Nv Ny Of Oi Ow Pd Pe Pg Pi Po Pz Qb Qc Qn Qt Qu Rm Tn Tv Ub Uc Ue Ug Uu Uv Vv) fR(aC AD aE aF aG aH aK Al aM An Ao aP aQ aR aS aV AW Ax aZ Ba bB bC bF hG bH bM bN BO bP bQ bV bW bZ cA cB cC cD cE cF cG cH cI cK cL cM cN cO cQ cR CS CT cU CV cW cX cY dB DC DD dE dF dG dH dI dJ Dk Dl dM dN dO Dq dR dV Et Ex Fa Fr GL Gt HC Hq Hw Hx Ih Ii Ik Il In Ir Is Iv iZ Jg Jj Jk Jo Jq Jr Ke Kf Ky Kz Li Lj Lx Lz Ma Mc Md Mj Mk Mp Mr Ms Mt Mu Mv Mw Mx Na Nh Nk Nn No Nq Ns Nt Nu Nv Nx Ny OE Og Oh Oi oK On Ow Oy Pe PF Qa Qd Qt Qy Qz Rf To Ue Up Vo) aX(aC Ad aK AP aQ Ar As aV Ax Ba Bb Bc bF bM bN bR cB cF cH cJ cK cM cP Cs cT Db Dd Dg Di DL Dp DR Ed eM Fa Fb Fn Fr Fy GI Gt Hb Hc Hf Hq Hr Hu Hv Hx Ic Ii Ij Il In Io Ip Ir Is Iu Iz Jd Je Jh Jl Jn Jo Jr Js Jt Ju Jv Ke Kg Ki Kl Kr Ks Kx Ky Lh Lu Lw Lz Ma Mc Mf Mh Mi Mj Mk Ml Mm Mn Mp Mq Mr Mu Mv Mw .Mx My Na Ng Ni Nn No Nt Nv Ny Oa Of Og Or Ow Pd Pe Pf Pi Pk Po Qc Qd Qh Ql Qn Qt Qu Qv Ra Rc Rf Rg Rh Ss To Tr Tt Tz Ua Ub Uc Ud Ue Uh Uk Ul Um Un Uo Up Ur Ut Uu Uv Vo Vt Vu Vv Wm) Ok(Aa aC AD aE AF aG al aJ aK AL aM AN aO aP aQ AR aS aU aV aW Ax aY aZ Ba bB bC bE bG bH bI bL bM Bn BO bP bQ bR bS bU bV bX bZ cA cB cC cD cF cG cH cI cJ cK cL cM cN cO Cp cQ cR CS cT CU CV cW CX cY cZ dA DB dC dD dE Ef dF DG dH DI dJ dK dL dN Dp DR Ed Ef eP Fa Fb Fn Fr Fy GI Gt Hb Hc Hf Hq Hr Hu iJ Iz Ju Jv Jy Kc Kd Kf Ki Kj Kl Kn Kp Ks Kx Ky Kz Ld Ow pF Ph Pi Pj Pk Qg Qu Qv Qz Rf Rh Ri Ss St Tt Tz Ub Ud Ue Uf Ug Uh Uk Ul Un Uo Up Us Uu Uv Vq Vt Vv) Jp(Aa AD AF aH al aJ Al AN AO Ap AR Aw Ax aZ BA Bb Bc bF bI bJ bL BN Bo bQ bR bS bU bV bX cC cE cF cG CH cJ cM cN cO CP CQ CS Cu CV cW Cx cZ Db Dd DE DG dH Di dJ DL dM dN dX eM Ex Ez Fa Fn Fy gL Gz Ha Hb HC Hf Ib Ic Id Iz Jd Je Ju Jv Jy Kc Kd Ke Kf Kg Ki Kj Kk Kl Kn Kp Kq Kr Kx Ky Kz Ld Oa Or Ou Ow pF Ph Pi Pj Pk Qg Qh Ql Qm Qn Qt Qx Qy Qz Ra Rc Rf Rg Rh Ri Rm Sr St Tn To Tt Tz Ua Ub Ud Ug Uh Uk Ul Uo Up Ur Ut Vo Vs Vu Wm Tj) Art(aG Ah Aq AT Ba Bb Be bF bg bN bU bV cC CH cJ cM cP cQ cR cT Cw Dc Dd dF DG Di dJ Dl dM Dq dX eM Fp GI Gt Ha Hb Hq Hr Hu Hv Hw Hx Id Il Ij Ik Il Im In Io Ip Iq Ir Is Iu Jg Jh Ji Jk Jl Jm Jn Jo Jq Jr Jt Kd Kp Lh Li Lj Lu Lv Lw Lx Lz Ma Mb Mc Md Mf Mg Mh Mi Mj Mk Ml Mm Mn Mp Mq Mt Mv Mw Mx My Mz Na Nb Nc Nd Ng Ni Nj Nk Nm Nn No Nq Nr Ns Nt Nv Nx Ny Oe Of Oh Oi Om On Oy Oz Pa Pb Pc Pd Pe PF Pg Pj Pk Pz Qb Qc Qd Qg Qt Qw Qy Ra Rg Rj Sr Tr Ut Vp Vt Vu Tj) gL(aA AD aE aF aG aH al aJ aK aL aM aN aO aP aQ aR aS aU aV aW aY aZ bA bB BC bE bF bH bI bJ bL bM bN bQ bR bS bU bW bX bZ cA cB cC cE cG cI cJ cK cL cM cN cQ cR Ct cU cV cW cX cY cZ dA dB dC dE dF DG dH DI dJ DK dL dM dR Et Ez FP Fy Ha hB Hq Hw Ib Id Ii Ik In Ip Iq Ir Is Iu Iv Iz Jf Jj Jk Jq Jy Kc Kd Kg Ki Kj Kk Kp Kq Lj Lv Lx Ma Md Me Mj Mk Mr Mu Mv Na Nd Nj Nq Nw Oa Oe Om Oz Pa Pb Pj Ql Qt Qy Ra Rb Rf Sr Tn Tr Ua Ur Uv Vo Vp Vq Vs Vt Vu Wm) aJ(AD aE Af aG aH al Aj aK AL aM An AO Ap aQ aR AS aU aV aW Ax aY Ba Bb Bc bE BG Bn BO bW bZ cA Ch cI cK cL cN CO Cp Cq Cs Ct Cu CV CW CX cY cZ dA DB DC DD dE dG dI DK DI dN Do dR Dv FP Fr gT GW Hq Hw Id Ih Ii Ik In It Iv Jf Jg Jm Jn Kc Lh Li Lj Lv Lx Lz Ma Md Mj Mk Mm Mp Mq Mr Mt Mu Mv Na Nc Nk Nl Nm Nq Nr Ns Nt Nu Oe Oi On Ou Oy Oz Pa Pb Pg Pi Pj Qa Ql Qw Qy Qz Ra Ug Ur Vq Vs Tj) Ly(aD aE AF aG aK aL aM AO aQ aR AS aW aY bF Bg bH bI bO bP bQ bS bU bX cA cB cD cE cF Ch cI cK cL Co Cp Cq Ct Cv CX cY cZ dC De dH DI DK dL dN Dp eC Ed Ez Fa fP Fw GI gW Gz Ha Hb Hq Hu Hx iA Ib iH Il Ip It Iu iZ Jd Je Jm Jy Kd Ke Kj Kr Ks Ky Kz Lu Lz Mb Mc Me Mf Mh Mk Ml Mq Ms Na Nd Ng Ni Nk Ns Oe Of Oi Or Oy Pi Pk Qh Ql Qm Qn Qu Qw Qx Qy Qz Ra Rb Rg Ri Rm Ss Tv Tz Ua Ub Uc Ug Um Un Uo Ur Ut Uu Uv Vp Vs Vv Tj) bA(AA Af Aj Al An Ap Ax Ba Bn Bo Cp Cs Cu Cx De dO Dq dR dV dX EM eP Ex fP Fr Gw Ha hC Hr Hu Hv Hx Id Ih Ij Ik Il Im Ir Is It Iv Jf Jg Jh Ji Jj Jl Jm Jn Jo Jq Jr Js Jt Jy Kc Kz Lh Li Lj Lu Lw Lz Ma Mb Mc Md Mf Mg Mh Mj Mk Ml Mm Mn Mp Mq Ms Mt Mu Mv Mw Mx My Mz Na Nb Nc Ng Nh Ni Nk Nl Nm Nn No Nq Nr Ns Nt Nu Nv Nx Ny Oe Of Og Oh Oi On Pb Pd Pe Pf Pg Pj Po Pz Qa Qb Qc Qd Qy Ra Rj Sr Tn Ua Up Ur Ut Vp Vs Vu Wm Tj) Lj(Aa Ad aH aN Ap As aU Ba Bb BC bE Bg bI bJ bL bN bU bV bX bZ cD cF cG CH cI cL cM cN cP cQ cR cS cV cY dC Dd dE Dg dM eM eP fP GI Hq Hr Hu Hv Hw Hx Ic Id Ih Ii Ij Il In Io Ip Is It Iu Jh Jk Jl Jm Jn Jo Jq Js Jt Kc Kf Kk Kp Kq Kz Lh Lu Lw Ma Mb Mc Md Me Mf Mh Mj Mk Ml Mn Mq Mr Ms Mu Mv Mw Mx My Na Nb Ng Ni Nk Nm Nn No Nq Nr Ns Ny Oe Of Om Or Ou Oy Ps Pd pF Pj Po Pz Qb Qc Qd Qg Ra Sr Uh Um Vp Vt Vu Wm) Jf(Ad al aL AN AP As aU Ax aZ Ba BC bE bJ bN Bo bV cH cJ cM Cs Ct Cu Cv Cx cZ Dc Dd dE dG Di dM eC Em Ex Fp Fy GI Gp Ha Hb hC Hu Hw Ib IH Ik Im In Io Iq It iZ Je Jg Ji Jj Jm Jq Jt Kd Ke Kg Ki Kj Kl Kn Kr Ky Lh Li Lu Lv Lx Md Mg Mh Mk Mq Mr Mt Mu Mv Mz Na Nd Nf Ng No Nr Nu Oa Oh Oi Oy Oz Pa Pb Pc Pd Pe Pf Pz Qa Qb Qd Qg Qt Qw Qx Qy Qz Ra Rb Rh Ri Rj Rm Uc Uf Ug Un Up Uu Vp Vq Vt Vu Vv) cH(Aa aC aD aE aF aG aH al aK AL aM aO aP aQ aR aS aU aY Ba BB BC bF BG bH bl bJ bL bM BO bP bQ bR bS bW cA cB cC cD cE cK cL cM cN CO Cp cR Ct CU cV cW CX cY cZ dA dB DC dD dE Dg dI dJ dK DL dN Do Dr eM cP cX Fp Fr GC Ha hC Hw Hx iA Ih In Iq It Iv iZ Jg Js Kc Kd Kp Ky Lh Li Md Me Mq Mt Nc Nj Nr Nu Nx Oe Oi oK Om Or Ou Oy Oz Pb Pc pF Ph Qx Qy Ra Sr St Uh Vt) dG(Aa Ad Af Aj Al An Ao Ap Aw Ba Bb Bc bE Bn Bo Ch Cp Cq cR Ct Cu Cv Cw Cx Dc Dd De Dg Di DI Do DR dX EM eP Et Ex Fp Fr Gc GI Gp GW Ha hC Hx Ib Ih Ij Ik Il In Iq It Jg Jj Jk Jn Jq Jr Js Kc Lu Lv Lw Lx Lz Ma Mb Mc Md Mj Mk Mn Mp Mq Mr Ms Mt Mu Mv Mw Mx My Na Nb Nc Nd Ne Ni Nj Nm No Nq Nr Ns Nt Nu Nv Nw Nx Ny Og Oh Oi Om Ou Oy Oz Pb Pd Pe Pg Po Qb Qc Ql Rb Ua Ut Vp Vs Tj) Qw(aH al aN AP aS aU aV Ax aY aZ Ba Bb Bc bE bI bJ bM bN Bo bZ cF cG cI cJ cL cM cN cO CQ cR CS cT CU dA Dd dE dF dJ DI dM dX Em eP Ex Fa Fp Fr Hv Ic Ih Ij Ik Im Io It Iv Iz Jd Ji Jj Jm Jn Jt Kc Kd Ke Kf Ki Kk Kl Kn Kp Ky Lh Li Mg Mm Mz Nc Ng Nj Nm No Nu Nv Nx Oa Oi Ou Ow Oy Pa Pb Pd Pe Pf Pj Pz Qa Qd Qg Qu Qy Rb Rh Rj Rm Tn Tr Tt Ua Uf Uh Un Vt Vv) Me(Ad An Ap Ax aZ Ba Bb BC bE bJ bM bN Bo bR bU bX cB cJ cM cN cP cQ CS cT CU Dc Dd dE dF Dg Dl dM Dp Ed EM Ez Fb Fn fP Fr Fw Gc Gp Ha Hb Hc Ib iH Im Ir Iv IZ Je Jj Ju Jv Jy Kg Ki Kj Kx Ky Kz Lv Mm

Nd) Mi(Nd Of) NcNi} oP{mF(hR jF jR nC) jQ(eD qY rX) IK(IL nN rY) ml(IX mH) nA(nI nT) rX(hV qY) eDrA nNkP nJnL jEjF} Dq{Fw(aK Dd dJ) aQ(aJ aV bE) DI(aV bC) bE(aK dO) cL(bL cB) cN(cY dR) BccF aVcH bCdJ cAeF cYdK} Nd{Nv(Hw In Iq Lv Md Nc) Mi(Nc Nt Oy Qa) Mm(aA Nc) JI(Md Mz) IuQa} Gc{Ue(aV Dp Gl In Ld Or Vo) Aa(Ky Nj Rb) Kj(cF Ra Rb) VoaV} Ko{Jf(Bg Dc Dk Mq Mu Po Qt Qw) Jk(bN cS cU Oy) CwaZ QwbN} gC{aJ(aD aK cH cL cM dL dO) dG(aK aQ cA cY dA dH) aPaV} Dr{Ra(aV Jn Kz Or Rm) Rc(Kf Rb) ExaV FwGw NkQw RbJy KccN} Ne{Mm(aA Hw Lv) Aa(Hw Oz) Fp(aA Mi) In(Nv Pe) MiHw} Jo{Ik(Lh Li Mi Mm) Lh(Fp Nj Nt) FpNt VqhB} dV{dG(aO hW cN) aJ(cC dK) BoEx bBcN cFdF cLeX} Nc{Hw(Lv Pe Qa) Nt(Lv Nk) In(Nv Pe) FpNk} eX{cL(cB DD Dl) aN(Dd dR) dJ(bC Fw)} rA{nO(lK mF rY) nU(kP mT) mF(jD jH) mIrZ} dX{Qx(dJ Hv Mz Rc) QyKy VvcN} lL{nO(hV qX) mIqX mMlK hVjQ} Md{Nv(Iq Nj Nq) MmNj} eD{nRlK mPqX mZjF nArZ} Mi{Nj(Hq Mm) NtOz} Ou{Ha(Ar Lj) RbVu} aJ{cJ(bL bU) cFdO} mT{nArZ hRjF hVqT} Vq{CtoK dRgW} aV{gN(bE bJ)} nO{nArZ iCjF} lW{qW(rY rZ)} lK{nRmF mZoQ} LvMmOz IqNvOm nUnAoQ mShRhV

Constrained panels with 3 analytes, where 1.0E-6 >= 'AUC p-value' > 1.0E-7. Contains 5,668 panels of 10,034,416 total panels evaluated. : Ly{Jj(aA aJ cH cS Dg dM Ih Ij Ir Jk Jm Jn Jr Jt Lv Ma Mr Nf Nj Nm Nn No Nu Ny Og Oh Oi Oy Pf Pj Po Sr Tt Ug) Dc(Ap Ar Ax Ba bV Cs Dg dM Fp Fy Ij Ik It Ji Kq Lh Mt Nr On Ou Pa Pe Pf Pz St Uf) bN(aP bA bC cH Db dG dM Hf In Jg Jp Js Kp Lx Nf Nw Oc Ok Ou Qc Sr To Uk Wm) Ha(Ar Ax aZ bV cH Cs Dg Im Jg Jm Jp Ko Kq Lj Lx Nr Oa Ou Pa St Tt Uh) Tt(Bg Cp Hq Ii Js Kj Md Mk Mu Oe Of Oy Pg Qw Ua Uk Ur Ut Vp Vu Tj) Qe(aA Al cS Dd Dk Fp Hf Hw Iq Jf Ld Lv Mr Nd Om Qb Qc Rm Uk Vs Tj) Lj(aA bC bE cS Db dM eF Hf Jf Lv Mm Nc Nf Nl Nv Nx Og Ou Qg Vp Vu) Im(Fp Hw In Iu Jl Jo Js Lh Lv Md Mm Nc Ne Nf Nt Om Ut Vp Vu Tj) Sr(aN Ct dE Dk Hq Ii In Jf Jo Kc Kp Nd Oe Oy Pb Pg Uk Vo Vp Vu) Og(aA bV Ir Iv Jl Jn Jt Mp Mz Nc Ne No Nx Oh Oi Pf Pz Qa Qd) Uh(Bg Cp Dk Hq Hw Jf Jq Mj Mk Mr Nv Oe Oy Pg Qw Ut Vp Vu Tj) Nf(aP Ax Cs Db dM eF Fp gL Ii Ko Lv Mm Mz Nt Nx Ou Pg Qa) Md(dF dM Jl Jr Kq Lh Li Mi Mm Mp Nl No Nx Pa Pe Pg Qa) Js(Ap Ax Ba cH Cs dE Dg dM Fy Kq No Nv Ou Pj Rf Uf) Ko(Bg bV cS Dd dE Hw Jf Mj Mu Oe Om Pg Qw Uk Ut Tj) Nc(aA Fp Jl Jr Lh Li Ma Mz Ni Nk Nt Nv Pe Pg Qa) St(Dk Hq In Jr Mk Mu Nv Ny Oe Pg Qb Ut Vp Vu Tj) Jp(Ao cE Ch Co Ct Db Dd Dk Je Qw Tn Ut Vp Vu Tj) Jg(bF Ct Db Dd De Ef Mu Qw Ua Ut Uu Vp Vu Tj) Jk(aJ Ap Ba cT dF DG Dl Fy gL Kf Kq Ou Qh) Hw(Aa aJ Ba cH cT gL Id Jr Mi Nl Nv Ou Pa) bA(aJ cS Db Je Kc Po Qw Ra Ua Ut Vp Vu Tj) Mm(aA Fp Ih Iv Jl Li Lv Nj Of On Pb Pe) In(aJ Ax dE dM Id Ih Is Lh Nx Pa Pe Qa) Om(Ba cH Dg eF Fr Id Kq Nv Ou Pj Vq) Pa(aJ bE dE dM Ih Ik Iv Mr Nd Nh Nj) Bg(Ap Ba Bo dG eF Ik Kq Nw Ok On) cH(aA aJ aZ Bo cS Db Ii Oc Ou Uk) Aa(Dk Fp Ih Ij Jf Kr Mt Nj Uk) Mi(aA Hx Ih Ik Iv Ml Nd Nh Oy) Ne(Fp Li Lv Mp Nl Nt Nv Pe Qa) Hq(aZ Ba dF DG dM Jl Kq Mp) Vu(dE Fp Id Kf Kn Nr Nw Ok Pb) Jo(Ad Ap Jl Nx Pe Pg Qa Qd) bV(Db Ii Kc Lv Lz Mr Pg Tj) dM(cM dE Ii Lv Na Nd Oe Pb) Dk(Ba dG Id Lx Nw On Uf) Nl(Jl Lh Ma Mz Pc Pe Pg) aA(Fp Fr Nh Nt Nx On Pe) bC(Fp Lv Mb Na Oe Pc Uk) Et(aU cE cS Ke Kg Vs) Id(Hf Jf Mr Uk Vp Tj) Nw(Ao Co cS Jc Qw Qx) dG(bF cE Ii Mk Mr Pg) Iu(Ir Lh Nv Pe Qa) Jf(Je Kc Ki Na Pj) Kq(Mr Mu Nv Pg Ut) Ou(Ct Kc Mk Mu Tj) dE(bL Lv Mt Ra Wm) Oe(aJ Dg Dl Pj) Ok(Ao Ct Qw Vp) Uk(aZ Ik Pj Vq) dF(cE Ii Pg Ut) Ar(Ii Mr Po) Tj(Fp Ik Pb) Nj(Jl Mz Nv) Of(Ba Dg Nv) On(Fp Ih Ut) Bo(Ao bF) Wm(aX aZ) Lv(Pe Qa) Nd(aJ Nv) Lh(Oy Oz) Uf(Mj Mu) Vp(Nr Pb) Pj(Na Pb) AxDd DbLx DgVo FrNg NoMc LzPe MrRf IhJi IkQw ItQg RaaZ JlOz JrPg QlaX PhgP aUaV bEcM} gP{Nf(Ar Ax bA Bc cH dM eF Fp Id Ik Ji Jm Jp Kf Kp Kq Lv Lx Mt Nd Nj Nw Nx Ok Or Oy Pa Pb Ph Qd Qw Qy Rb St Uf Uh Vt) aX(Ax Bc dM Et Gt Hc iZ Jm Jp Kd Kq Ld Lh Lj Lv Lx Me Nj Nr Nw Ok On Oy Pa Pb Pc Qd Qw Uh Wm) Sr(aU Bg cE cS Dc Dk dM Gl Hq Ij Iq Jq Kc Kd Md Mj Mq Oe Ou Pa Pc Po Qw Qy Rb Rj Wm) Jf(aC aU Bc bJ dE dM eF gL gW Im Jk Kn Lj Lx Md Mm Mt Nm Pc Pj Qw Rb St Wm) Nw(aJ Dk fR Gl Ha Ii Jq Jr Js Kk Na Nd Oe Ou Pc Rg Rj Tn Ut Vp Vu Wm Tj) bV(bJ bU cH cM Db Dg Dl dM eF Gt It Ji Kd Lj Lx Mm Ok Om On Pc Qd Vq Vs) Qa(cH Dc Ha Hq Jk Jl Jr Kc Mj Mu Nd Oe Om Pc Pg Rb Ur Ut Vu Tj) Ko(bF Bg bJ Gl Ha Hq Ij Ma Md Mq Mu Nb Ou Po Qy Rb Rg Ul Ut Vu) Qe(aI bN cS gL Hw Me Mq Nj Nq Ou Oy Oz Pa Pb Qw Qy Rg Rj Vs) Kp(aJ Bg bJ cH Dk dM gL gW Ii Jk Kk Md Me Mu Om Rj Ur Wm) aJ(Db Dl Et Id Iq It Jk Kk Lx Mj Mt Nj Nk Ok Pa Pc Vs) eM(cN Dc dL Dp Fp gL Ic Jj Kz Ld Me Nj Pb To Uk) Jp(Bg Dk Gl Ha Ii Jk Kk Nd Rb Rj Ut Vp Vs Wm) Om(cH eF Im Jg Jm Kq Ok On Ou Qd Qy St Uf Uh) bA(aS Bg cR Ct Dg Dl fR Kc Me Nd Qw Rb Wm) Lx(cH Dk Ha Hq Ii In Jk Kc Mu Nd Pc Ut) Kk(Bc Dg Et fP Jv Ki Mt Nm Ok Qw Rj Vs) Vq(Ct gW Jj Ky Me Mq Nc Nl Og Oy Ub Uk) eF(Dl eP Hq Jk Kc Kd Lj Nd Qw Rb Ut Wm) cH(aP aW Bc cS dF dG Kn Mt Pb Pc Rj) Qy(Dk dM gW Hq In Jj Kc Oe Ou Pc) fR(Jn Me Ne Pa Pb Ra Rj To Up Ur) Ou(aU dM Ha Hq Lj Mu Rb Ur Ut) Ii(Et Kf Kq Mt Ok On Qd Uh) dM(cS Dl Kn Nd Pc Qw Rj Ur) Jk(Hc Kq Mt On Or Oy Qh) Et(Jo Oe Or Oz Ut Vo) Me(Nd Pc Ph Uf Uk Wm) Kc(Bc bN cS gW Iq Rj) Dk(Bc Dg Mt Ok Qd) In(Jm Kf Mt Qd St) Ur(Jm Oy Pa Rj Wm) gL(aD bM cR Dg eP) Gt(aM An cY dF) Rb(aP Jj Pa Pc) Oe(Mt Ok On Qd) Bc(Bg bM cS) Dr(aV Gw Qw) Jo(Kq Uf Uh) Rj(Jn Pa Pc) Ok(Jq Jt Ut) dG(bQ cE dH) eP(aM cL Hc) gW(Kd Or Ph) Gw(aD Dc) Qd(Js Pc) Kn(Jr Js) Kq(Bg Mu) BaCt DqaK FpHa MtPc NdPa UfVo aPdV cEeX dKdO} Et{Jf(Ao aX bN Ch Co Cp Ct dE Di Fr Ha Hc Hq Hw Ib Ii Ij In Jd Jq Js Ke Kg Kq Lh Lj Ma Mj Mn Mw Nd Nj Nv Ny Of Oy Pe Ph Qt Qw Rc Rg Tn Ul Vp Vu Tj) Ou(aU aX Ch Cu Iz Jr Jt Kg Ma Md Me Mq Mr Mu Mv Nv Ny Oe Pa Pe Ql Qm Ra Rc Tn Tj) Vo(Ao aX Ch Gl Ha Hq Jd Kc Kp Ma Md Mk Mq Mr Mu Mv Oe Pa Pg Po Qw Rb Rg Sr Vu Tj) Kk(Ao aX Bg Co Dc Ij Jd Jk Jr Jt Md Mk Mn Mu Mv Nv Ny Om Oy Pg Po Qt Ut Tj) Rb(Ao aX Bg Dc Ii Jj Jk Jo Js Md Mj Mk Mr Mu Mv Oe Pa Pb Pg Ut Vu) bA(aH aI aO aX bQ Dc Gl Hq Ii Js Jt Ma Md Me Mr Nq Nv Pa Pg Po Ut) aX(Ao Bg Dc Dk Ij Iq Jk Jq Jt Lj Lv Md Mj Nj Nq Oz Pa Pc Pg) Oe(aJ Ao bF Bg bL bN CH Dc dM Gl Kz Qy Rc Rg Ut) Bg(eF Hc Ii In Jj Js Jt Om Or Oy Oz Pb Pc Ra) Mr(Hq Hw Hx Ij In Iq Iu Lz Md Mj Nq Oy) Nf(Ap aU Co cS Ef iZ Jd Kg Ra Tn Vu Wm) Qy(Dc Ij Jl Mk Mu Mv Of Pg Po Qw Ut Vu) Om(Ao bV Ch Co Ha Or Rg St Ul Ut Vp Vu) Pa(Ao bV Ch Co Dk Ha Kg Qt Rc Vp Tj) Dc(bV Gl Kc Lj Nc Nj Oy Qa Qe) Jo(bJ Gl Hc Kc Ko Or Ph Ra Wm) Dk(Hc Kc Kg Ko Kz Oy Qn Ra) Mi(Hx In Iq My Ny Pd Pg Po) On(In Iq Lj My Nb Ng Ny Pg) Ut(bV eF Ii Me Or Oy Pc Qe) Ji(aA Fp Ij In Jq Ms My) bV(cE Ii Ij Jt Nd Pb Pg) Mj(iJ Kc Or Ra St Wm) Jk(Gl iZ Kc Ko Or Wm) Hq(Hw Lh Mk Pb Pe) Jl(Hw Ij In Iq Oy) Gl(Kp Nd Pc Ur) Me(Ha Qw Vp Vu) Js(Kd Qt Qw Sr) Fp(aA Iq Ok) Ij(Kc Ko Or) In(Is Iv Nu) Vu(Oy Pb Pc) iZ(bN Nv Ql) Wm(Md Pg) My(Nw Pc) Hx(Kd Pb) Iq(Ok Pb) Jg(Jh Ms) aA(Lj Ok) FrNg GnUf MkOy MuOr NdaJ RaKc JriJ JtKp KdVs RgOf NwNy} Nf{Qe(Aa aJ aU bA Bg bN bV Dd Gl Iq Iu Jf Kc Mk Og Om Oz Pc Pe Ut Vp Vs Vu) Li(Fr Hw Iv Jj Jl Jr Lh Md Mm Mr Nc Nd Nh Nj Nq Og Om Pb Pc Pe) Fp(AA bV Hw Ii Iv Jj Jl Mg Mk Mm Nb Nc Ne Nr Pc Pe) Lh(Fr Hw Im Iv Jj Jr Lj Md Mm Nc Ne Nh Nt Om Pa Qa) aX(Ax cP eM Ih It Jf Kc Kk Kn Mh Nr Qw Qy Ur Vp) Nw(aJ aU bN cS dE dM Gl Jf Ou Ul Ur Ut Vu) Ok(aJ Ao aU bA bN bV Gl Jf Ou Qw Rc Vs Vu) Nj(bA bE bN bV dM Jf Jl Lv No Nx Qa Vq) Ik(Aa Im Lj Lv Lw Mr Mz No Og Pc Pg Qa) Nv(Iv Jj Jl Jr Mr Nc Nh Nr Of Oz Pb Pe) Dc(Ad Ar Id Jg Jm Jp Ko Kq Lx Pe Qd) fR(aW cI cQ Cv Fn hC Ow pF Rc Ue tF) Fr(Ih Im Jl Jr Mm Nc Ne Nh Pa Qa) Qw(bV Dr Id Jm Ko Kq Lx Nr Sr Vq) Pe(aA Iq Iv Jj Jl Mr Mt Nc Nh Om) Mm(Jp Jr Lj Mt Ne Nt Nx Oz Pb) Jg(Bg Iq Jl Jt Mk Mr Ng Nr Vo) Lv(bA bV Hw Iv Mi Nb Nh Oi) Nd(bA bV dM Im Nt Om Pg Qa) Lj(aJ bA bE bV dE dM Mi Nl) dG(Bg bN cE Hw Jk Md Nq Oe) Nx(Hw Ih Im Jl Mr Nc Qa) Mc(Ar bA Hf Id Uh Vq) Nl(Im Jl Jt Pc Pg Qa) Jp(Hw Jl Mk Oz Pb Rb) Kq(Bg Dk Js Mu Om Vo) Pa(bA bV Im Jj Nh Qa) Sr(Dd Hw Mu Rb Vo) Aa(Jr Nc Ne Oz) Nt(aA Im Jl Pc) Lx(aJ dE Iu Om) Mi(Iv Oz Qa Qd) Mt(Jl Mk Nr) Id(It Ou Rb) Ko(Dd dE Dk) Om(bA St Uh) On(Nb Og Wm) aJ(bN Nq Oy) Ar(Js Mr) No(Mf Oz) Iv(Jj Jl) Rb(dE Uh) Kc(bN Jf) Vq(Hu iH) bV(bN Pb) DgOe FaUr NuMz HweF OubE UhVo cHdM} Gn{St(aN Ba Bb cF Co Dk Dl Fy Gl Iz Jt Ke Kj Kl Mv Ng Nm Of Uf Ut Uu) Mz(aG Ba Cw Fb Ij Im Iz Kc Kl Ks Mn Mw Ng Nm Uc Uf Uu) On(Ap Bg Co Fb Jk Jo Kg Lh Mv Mw Of Ua Uc Ut) Un(aP Ax Di dK Ji Nj Nv Oe Oh

Figure 9 Continued

Ok Qb Rm) dG(bW Di Fb Ii Jh Jk Jt Mr Mu Nq Qy Uh) Vv(Bg Ct Fb Jd Jo Jt Kg Mg Of Pf Ss) Ih(Ap Ba Bb Co Fb Gl Jk Ks Mv Nm) Qa(Ef Fb Ii Iz Jd Jt Ks Nm Uu) Qb(Cw Hb Ij Iz Jk Ks Uc Uh Uu) Fw(Ma No Nt Oe Pc Qm Qy Ua) Kn(Ef Ij Ik Ma Qt Uh Ul Uu) Nw(Fb Ii Ij Kj Kl Pj Uh Uu) Ok(Ao Ba Co Ii Ij Jd Kj Pj) Ph(Ik Jo Jt Kj Ks Ma Uc Uh) Ax(In Jd Ks Li Mr Oz Pf) Qz(aG Ef Fb Iz Kf Uf Uu) Rm(Dl Jk Ke Ks Pj Qv Uh) Ou(Em Jk Pj Pz Qy Rh Ss) Fp(bR cM cN dl Fb Mu) Qe(Ap Ii Iz Kj Kl Ma) Jm(Fb Im Iz Jt Ks Uf) Kf(Cw Jg Ke Ma Mg Uf) cl(Ii Ij Mw Nl Qm Qv) Em(cB Cs Mu Ng Nu) Mf(aJ dL Js Lu Qx) Ld(Cp Fb Gp Mu Rh) Oa(aX dE Fr Mu Rh) Cw(aK aQ cY Tv) Di(Bo dL Oz Pc) Fa(Cp Fr Js Mr) Ex(In Mr Nn Oz) Hf(Ba Fb Ke Mu) Nx(Po Ss Ua Uk) cO(Ij Jo Mw Qm) Al(Ii Ke Kl) Na(Gp Qv Wm) In(bU Lj Mh) Qx(Nl Qw Up) Jn(Ef Ii Kl) Kk(cN Ir Js) Oi(Ba Of Uc) aQ(aU dK dM) Dl(Jt Kj) Mr(Cs Lj) Nj(Bb Qy) Ic(Jt Mw) Tv(Ij Jk) It(Ib Uh) Li(Oh Rf) aJ(cB dV) cE(Io Wm) cH(Ij Ne) ApcY CvIz PoLx NtNu MgaX MqNb HrHv JsLj KdUh RhcM NvUt OhPf aKdK cBdE dAfR} Qe{In(aX bA bL bN Dc Fp Fr Hw Ih Iq Is Iv Jl Lh Md Mi Mr Nb Nq Nu Oi Om On Oz Pb Rb) aX(bN cE Ha Iq Jk Jl Jo Js Lv Ma Mr Nq Oe Oz Pa Pc Pg Po Qw Vp) Qc(dM Fp Hw Ik Il Iq Ji Lv Md Mi Nd Ne Nh Nt Og Om On Oz Vu) Dc(bC Gl Ii Iq Jg Jp Kc Kf Ko Oe Om Pg Qg Qw Qy Ra Tj) Lv(Hw Iu Jo Md Mi Mm Nq Og Om On Oz Pa Qb) Md(Fp Hw Iq Jg Jj Jp Nc Ne Nh Nq Nt Pa) Ne(aA Il Iq Iu Js Mi Nd Nk Og Om Qb) Nt(Hw Il Iu Js Nc Nq Of Om Oz Qb) Iq(Fp Fr Jj Jp Mi Nd Og Ok On Pa) Ji(Ii Ij Il Iu Jj Ms Nq Og Qb) Jg(Ii Iu Mv My Ng Og Oy Oz) Jj(Fp Iv Mg Mm Nh Oi Om Qb) Me(Ha Ik Kr Qw Ut Vp Vu) Mi(Hq Hx Ik Nc Nq Oy Oz) Hw(Ik Jp Mg Nd Nh Nx Pa) Jf(Gl Jk Kc Mr Mu Ut Vu) Fp(Iu Js Lz Ml Og Qb) Nc(Il Js Ni Og Om Qb) Nj(Fr Iu Nk Om On Qb) Rb(Ha Jk Mj Mr Mu Vu) Pa(Ha Lz Nq Og Qb Vu) On(Ii Jk Jt Ny Po) Ik(Il Js Mm Om) Jp(Hx Js Oz Qb) Nq(Fr Mm Og) Nd(aA Jl Lh) Mg(Jo Of) Mj(Ko Ra) Il(Mt Ok) Jk(Ko Qy) Nx(Jo Of) EmKj HaLj LxHq LzOk MmJt MrNl HxPb IicM OgOi OmfR} On{Fp(Ii Ij Il It Iu Jg Jj Jp Mi My Nc Ne Ny Pa Pg Po) Oz(Hq Ik Jg Jj Jk Jo Jt Lv Mi Mm Nc Ne Ng Nt Og) Ms(Hw In Iq Jk Jo Js Lv Lx Mt Ng Nq Of Og Pa) Lj(Ha Hq Hx Ii Ij Ik In Jk Js Jt Ne Nj Og Po) Pa(Hq Ij Jg Jk Jo Js Jt Mt Nc Ng Nh Nt Og) Jg(Hw Jj Jk Mv My Nc Ng Nj Nq Ny Og) Lx(Ij Il Iu Jo Jt Mt Mv Nb Ng Pg) Mi(Hw Hx Iq Lv Nc Ne Nh Nq Of) Jt(Hx Iq Iv Ji Lv Mb Mm Nq Ns) Md(Hq Hx Jo Lz Mj Mk Mm Of) Mt(Il Iu Jo Mv My Nb Ng Ny) Ik(Hu Il Iu Me My Nb Nj Pg) Js(Ii Iv Ji Mf My Ng Of Og) Nh(Ii Jp Mv My Ny Og Pg) Lv(Iu Jj Mv Ny Pg Qb) Nb(Hw Nd Ne Nj Nl Nt) Nc(Hx Il Iu Jo My Ny) In(Ih Ji Jr Ng Nt Of) Iv(Ij Jj Jk Jo Ny Og) Ne(aA Me Mm Mv Pg) Hq(Hw Iq Ji Nq Pe) Nw(Il Mv Ng Nq Nv) Of(Jj Mm My Ng Og) Jo(Hw Hx Mb Ns) eP(Jd Ks Ma Tv) Ij(Jp Mb Nt) Iq(Ih Jj Jp) Ji(Ii Ng Nq) Nj(Me Mv) Hx(Jj Jp) Oc(Bg Ut) Og(Mb Nx) Ok(My Pg) Om(aA Dc) aX(cE Jk) DrRa PoPe EmUa NtNy MfJj MmNd NiNk HwPg IiJr OuUt} aX{Nw(Bg bJ Dk Ha Hq Hw Ii Iq Jl Lv Ma Mj Mr Nd Nq Nv Ny Oe Om Oz Pc Po Qw Vo) Ko(Dc Dk Ha Ii Jf Jj Jl Jo Jt Kc Kd Om Pa Pg Ph Po Ql Tn Ul Ut Vp Vs Vu) Ou(aW Bg Ch Gl Hq Jq Kc Kk Kp Kz Mk Mr Mu Mv Ow Ph Po Ql Rj Ul Ur Tj) Ok(bN Cw Dc Dk Hw Ii Iq Jk Jq Lv Md Mj Nd Nj Nq Oe Pb Pg) Rb(aZ gL Jk Jl Kc Kp Lv Mb Md Mj Mr Mu Nd Pc Qw Vp) Me(aJ cE Db Fp Iq Jj Lj Lx Nl Nq Oe Om Wm) bN(aJ Ih Jf Kd Lv Mt Nd Nr Oz Pa Pc Qy Vp) Ph(cE Ha Hw Jf Jk Jq Jr Mj Nk Qw Vp Vs) eM(Fp Hu Jj Lj Mb Mv Mw Oz Qb Up) Nj(bJ gL Jj Jk Lv Lx Mt Ni Nk) Lv(bA cE cM gL Lj Pa Pb) Nd(aA bA gL It Lx Qa St) Qy(Bg cE Jk Lj Mv Qw) Jq(Kc Kk Kn Kp Mt Sr) Iq(It Kc Pa Pb Sr) eP(Jn Kr Oi Pb St) Aa(aJ Js Om Rj) gL(Pc Ur Ut Vp) Lx(Ii Pb Pc) aJ(bL bU cJ) Mt(Nq Pb) Sr(Js Qw) St(Mj Om) Kc(Jf Vp) Lj(Ha Pb) GcKj NrHw MbdI JgOm QwRj JkJm JrKn VqVo PabJ} Jg{Md(Fp Hw Ik Iq Iv Jj Jk Jo Jp Jt Lj Lv Ng Nq Of Pb) Lj(Dc Ik In Iq Iu Jk Js Lv Nc Ne Ng Nh Nj Nq Oz) Fp(aA Dc Il In Iq Lv Mi Ml Mm Mu Mv My Ng Oy) Nq(aA Fr Hw Ih Iq Iu Jl Jt Lv Mi Mm My) Jk(Ih Ik Iv Jr Mu My Nh Ns Nt Nu Pe Qa) Oz(Hu Iv Jh Jt Lv Mi Mm Mu Ng Ns Nt Oy) Hw(Ih Iv Jo Jr Lv Mv My Nd Og Pe Qa) Jt(Ih Iv Jj Mm Mv Nh Of Og Pe Qa) Nj(Iu Jh Ji Lv Mi Mr Mv Ng Oy) Og(Iq Jh Jr Mr Mu Mw Oy Pb) Om(aA Bg Dk Jh Jl Mi Mm Mr) Pa(Dc Iu Iv Jh Js Ms Ng Oy) My(Iq Jj Lv Ng Nh Pb Pc) Nc(Jh Mi Mm Mr Ng Ns Oy) In(Ih Ik Mv Nh Nu Pe Qa) Mt(Il Jh Mg Ms Ns Oy) Iu(Iv Ji Lv Nh Ok Pb) Jo(Ih Iq Jh Mf Mm Pe) Mv(Iq Iv Jp Lv Nh) Nd(aA Ih Jl Mr Mu) Ne(aA Hu Jh Mi Mm) Of(aA Jl Mi Mm Mr) Ng(Ik Ji Jj Nt) Iq(Iv Jr Qa) Ji(Jj Jq Ms) Oy(Mk Mr Pc) Ij(Pe Qa) Jj(Ih Mr) Js(Nh Qa) DcMe LvMm LxHq NiNk} Me{Sr(aN aU bN cM Cp Dd Ii In Jf Jl Kc Mk Mr Mv Na Nd Nj Oe Ou Oy Pa Pc Qn Qw Ua Vo Vp Vu Tj) fR(aH aN Db Dd dH Fp hC Iv Jn Mp Na Nc Nh Og Om pF) Hf(aJ bN cS Dc dM Fp Jp Js Ko Lx Nw Ou Pa Ph) Ko(aZ bN bV cM Dc Dd Dk Jf Js Kr Mj Om) Nl(Hw Ik Iv Jl Lh Ne Ni Nt Nx Pb Pg) Jf(Db Je Ki Nj Ok Oy Pa Pb Ph Pj) Ou(aU bJ Kc Mk Mu Om Pj Vq Vu Tj) bA(aH Ha Kc Lv Om Pa Pc Qw Ut) Ik(Dc Jo Lj Mi Nc Ne Ok Qw) Dr(cN cP cY Fp Lv Nb Nh) Nj(aJ bN dE dM Lv Vq) Id(bN cC cM Db Dc Om) Kq(Dc Dk Jk Mu Om Ut) bV(Kc Lv Nd Oz Pb Qw) Ha(Fp Lx Nw Pa Pe) Kr(Aa Lx Nw Ok Pj) bC(Kk Lv Mb Pb Uk) Nd(aJ dE dG dM) Kf(Dk Js Oe Om) bN(Kp To Uk Vt) Dc(Fy Nw Uf) Ne(aA Fp Nt) Om(St Tt Uh) Vq(Jn Ow To) cM(Kk To Vt) dE(Lv Qw Wm) Nh(Ji Ok) DgVo MbJi RaaZ KccS KkLd KpbJ NwVp OkUt} Nw{Qy(Ao Bg Co Dc Ha Ij Jk Js Mj Mr Mv Nv Ny Oe Pg Po Qw Ut Vp Vu) Rj(Ao Bg Ct Dc Dk Hw Hx Je Jo Jr Mk Mu Nj Ny Ut) Ou(Dc Dk Gl Hq Jr Js Mk Mr Mu Nv Ny Pe Po Vp Tj) Dc(Gl It Jf Jm Jq Md Nc Oe Pa Qh Qn Rb) Js(Ao Bb bN Co Dk Gl Ha Rb Sr Ut Vp Tj) Vp(Dk Gl Md Nj Oe Om Oy Pa Qn Rb) aA(In Jj Lv Ms My Nq Of Og Oz) Rb(Ha Md Mj Mr Mu Nv Pg Vu) Om(bA Bg Dd Dk Gl Ha Ut Tj) bA(Ii Jk Jr Nv Ny Pg Ut) Gl(bN Dk Ha Pa Pb Tj) Wm(Hx Md Mj Pg Po) Bg(Hw Nj Oe Oy) Ha(Jm Lj Oy Pa) Dk(Hw Jq Tt) Nj(Ao bN Tj) Ra(Md Mj Mu) Qw(Md Mr Rg) Oe(Ao Rg Tj) Ut(Oy Pa Pb) Po(bV Qn) Ji(Jq Og) Vu(Oy Pa) FpMm MgJj MiPd MrJf MyPc IhIl IibN OzfR aUaV} Jj{Nc(aA Fr Hw Ii Im Jl Jt Li Lj Mi Mr Nm Nu Nv Oi Oy Pb Pc Pf Qa) Fp(aA Fr Im Iv Ji Jp Lh Lv Md Mg Mi Mm Nh Nj Oi Om Pa Pg Pz) Iv(Ji Jp Lh Mf Mg Mm Nd Nh Nj Nr Nx Om Pa Qa) Jp(Hw Jr Md Mf Nd Nh Nq Nr Nu Oi Om Oz Pa) Nh(Ji Jm Jn Jr Lh Mg Mi Mm Nx Oy Pe) Pa(Hw Im Jm Jr Lh Lv Mf Mg Mm Nr Qa) Nj(Ii Jm Jr Jt Lh Mi Nv Nx Pe Pg) Ik(aA Fr Hw Io Jl Li Lv Mg Mr Nv) Em(aV Hf Ih Ky Og Ok Qy Ue) Ne(aA Jl Mr Nu Oh Oi Pb) Ji(Iq Jq Lv Md Ms Om Oz) Nd(Im Lh Nr Pg Qa) Hw(Lh Nr Nv Nx Qa) Oz(Ex fR Lh Mm) Lv(Im Jm Qa) eM(eF Ih) DldX NuMm MgOm NlfR} Nc{Hw(Fp Fr Ik Im Lh Li Mg Mi Mm Mp Nk Nt Pg Pz Qd) Nk(Fr Jr Li Lv Mi Mm Nv Nx Pe Pg Qa Qd) Nd(aA Fr Im Jl Li Mz Nx Pe Pg Qa Qd) Mm(aA Fp In Ji Jp Jr Lv Og Om Oz) Og(Fp Ik Li Lv Mi Nv Nx Oi Pe) In(Fp Is Lh Li Nt Nx Qa Qd) Pa(aA Fr Ik Iq Lz Md Mi Om) aA(Fp Ji Jn Jp Mt Nt Nx) Om(Aa fR Im Lv Nv Nx) Fp(Fr Lv Md Mi Ni) Mi(Ik Ji Jp Nt) Ni(Li Lv Nt Nv) Md(Lv Nt Nv) Mr(Jp Mt) Js(Lh Nv) Oz(Aa Jp) LxHq LzPe MtIu IqNv JkKo JoLh LjNx aHfR} Nl{In(fR Ih Im Iv Jn Jr Jt Lj Mp Mr Mz Nb Pc Pf Pz) Hw(Iv Jl Jt Lj Lw Mg Mp Mw Mz Nk Nt Pc Pg Qd) Md(Im Lh Li Lj Mz Nb Nk Nm Nt Om Pb Pe Pg) Iu(Fp Im Lh Li Nt Nv Nx Pe Pz Qa Qd) Nk(Ih Im Iv Jl Lh Li Lj Pb Pc) Om(Fp fR Im Jl Lh Lv Nv Nx Qa) Ni(Im Lh Lj Mp Nv Og Pe Pg) Og(Im Mg Mr Mz Oy Pc Pz) Mi(Ny Pf Pg Po) Lh(Fp Hq Iq Js) Lz(Li Lj Pc) Mr(Il Lv Mm) fR(cP Mq Na) Ne(Pe Qa) Il(Aa Jl) Js(Li Nv) Nx(Ml My) DrQw MpHq IqQa JoNv} Ko{Jf(bN Co Cp dE Gl Ha Hq Ib Ij Iq Jd Je Ki Ma Md Mj Mr Mv Nv Ny Om Pa Pg Rc Tn Ul Ut Vu Tj) bN(bV Dc Gl gW Ii Ij In It Jo Jq Mq Mu Oe Om Pa Po Qm Qt Rc Vo) Jk(bA bC bV dM Hc Jm Lx Md Mt Om Ou Qy Rb Sr Ul) Qw(bF bV cE cS dM Js Md Qy Rg Ul) Dc(cS Lx Om Ou Oy Pa Rb) Iq(aI aZ cE Kc Pa) Pa(Dd Dk Po Qt) bV(Jt Nq Qt) eM(aC Mu To) Dk(eF Rb) Dr(Ij Mv) Po(aZ cU) cS(Ij Qt) EmIi MueF NbeP OuVu PgdX aUaV bLdE} Jp{Nq(Fp Fr Hw Ih Iq Iv Ji Jr Li Mf Mi Nu Og Pe Qa) Iq(Fp Ih Im Ir Jr Lj Lv Mi Nh Nt Og Pe Qa) Hw(Ih Iv Lj Md Nd Nt Nx Pa Pc Qa) Nd(aA Ih Jl Lj Mm Mr Og Pe) Fp(aA In Js Mi Ml Og Om) Nh(aA In Md Mi Og Om Oz) Mb(Jl Mi Ml Mr Og) Rb(Bg Dc Dk Jk Mu) Nt(Js Mi Of Om) Lv(Jo Mm Ng Oz) Md(Iv Oz Pa Pe) Nu(Ns Og Om) In(Ih Nx Pe) Mf(Iv Mi) Mm(Ik Ne) Hx(Ih Pa) Ji(Js Om) Oz(Mi Ok) DcJm LzLj IkaA IvPa JrOg OfOi OuUt UpdX cFeP} Nj{Mm(Fp Fr Hw Jl Jo Jr Lh Lj Lv Mr Om Oz Pb Pe) Mi(Fp Hx Ij Ik In Iq Lj Lv Md Nd Nt Oy) Pa(Aa aJ Iv Jf Jl Lh Nd Nk Nt Og) fR(aH cE cZ Dd De Jo Lv Ni Pb Pc) Nv(Hw In Iq Jo Lj Of Og Om) Fr(Fp Hw Iu Iv Lj Md Nd) Og(Aa Fp Lh Li No Oi Pe) Md(Li Nb Nx Pe Qa) Dr(Kz Mv Ra Uo) In(Lh Li Pe Qa) Jo(Aa Dg Li Nt) aA(Ji Jr Mt Nx) Lv(Nt Qa) Lx(Aa Om) GcUe MrMt NiLi HqJl HwQa JsLh bNbV cFeP} Ji{Md(Fr Hw Iv Jo Jq Js Ms Mw Nh Og Om Pa Pb Pc) Iv(Hw In Iq Jo Jq Js Ms Nq Og

Figure 9 Continued

Om Pa) Om(Fp Fr Iq Jo Js Mi Nd Nh Og Qa) Hw(Iq Jo Lj Mg Mi Ms Og) Fp(aA Iq Iu Mi Ml Mm) Jq(Ik Jr Ne Og Ok Oz) Pa(Ii In Js Mi Nq Og) Iq(Jo Lj Mi Nd Qa) Ms(Jo Js Og Ok) Mm(Ik Jo Lv) Nh(In Jo Og) Js(Lj Nt Og) aA(Lx Mt Oz) My(Ik Mt) Nd(Ih Lj) In(Lj Qa) Iu(Ne Nt) FrNq MgJo MiIk MIOz HueP cNdX} Ne{Hw(Fp Fr Im Jl Lh Li Lv Mg Mp Nt Pe Pg Qa Qd) Og(AA Fp Ik Iv Jq Jr Jt Li Lj Mi Nv Oi Pe) In(Fp Fr Is Lh Li Mi Mm Nt Pg Qa Qd) Pa(Aa FR Iq Lz Md Nd Om) Mm(Fp Jo Jr Md Mi Nd Ok) Aa(Ij Lx Ma Mj Mt Om) aA(Jn Jr Lh Lv Mt Nx) Md(Fp Li Lv Nt Nv) Nv(Iq Js Nd Om) Fp(Fr Lv Nk) Mi(Hq Iq Nd) Lv(Li Lj) Mt(Iu Mr) Lh(Il Jo) FrNd NtNk HueP LjNx OmfR} eP{Hu(aZ bA cF Cu gL Ih Li Nh Nn Oh Ok Oz Pi Qa) Ib(aC Ba Jt Nr Nx Oe Pj Pz) Nb(Mv Oz Pb Qy Rb Uk) Mf(aC aZ bE cN Qw) Og(aZ Dl It Nt Rm) aV(aU bA cB cF cL) Ih(cF Ih Mw Vo) Rf(aM bU cM Up) Fw(Dp Dq Gt) Rc(Dg It St) cL(cC dI Qy) Di(Bo Qy) Nu(bC dJ) Qw(cF dK) Qu(Dg Dl) aJ(aK dJ) CsLi DpbC GlOu HweF IrOz KzdK PccH cFdL dAdG} Lx{Mm(aA Hw In Iq Jo Js Jt Md Of Om Pa) Mr(Hq Il Iq Jo Js Lz Mj Mt Og Oy) Jl(Hq Iq Jo Js Lz Md Og Oy) Aa(Ij Js Jt Ma Nd Oz) Mi(Ij Jo Md Mv My Oy) Iu(aA Hw Hx Md Nq Og) Hq(Fp Lh Nh Pb Pe) Pa(Hx In Js Lz Md) Po(Kc Kk Ou) Iv(Jo Jr Md) Ha(Lj Ou) Lh(Ii Jo) EmKj GlPb NoJr LzPe MdMw MtIl NbNy OuVu} Nd{Fr(Fp Im Iu Iv Mm Nt Og Pa Qa) fR(cQ Fp Ih Iq Ml Mq Na Oe Pb) Lv(Im Mm Mz Nx Pa Pg Qa) Nv(Fp Iu Jl Jo Lj Mr Om) Im(Fp Iv Mi Nt Nx Og) aA(Fp Jn Lh Nt Nx Pa) Qa(In Md Mm Nt Og) Mi(Fp Md Og Pe) Mm(Og Ok Pe) Iu(Pe Pg Qd) Jl(Hq Hw Og) Nt(Jo Md) Mz(Pf Pg) Nx(Md Og) Pa(Fp Ik) eM(aC Hu) MpHq JoLh} Mt{Mr(Hq Ij Il Iq Lz Mj Of Og Om Oz) Mm(In Iq Jo Jr Md Ms Ng Of) aA(Iq Jr Lv Md Nq Og Oz Pa) Mi(Hq Jo Js Md Ny Pa Pg) Jl(Hq Ij Of Og Oy Oz) Aa(Ij Jt Og Oz) Hq(Hw Pa Pb Pe) Md(Iu Lh Nb) Iv(Ir Jo Js) Pa(Il Iu Js) Pc(Mv My Ns) Fr(Mv Ng) Iq(Jr Pe) Lh(Il Of) NoJs NtOf MyNx NbNy HwbV HxPb OmcH} Em{Ue(aZ bR cR Gl Kn Mv Nu Ou Ph Qz) Vo(Bc dL gL Ic Je Jy Kz Mf) Kj(aJ Ih Mf Nu Oi Qy St) Ib(aJ aP dM Kd Kn Ou) Fn(Kd Og Rb Ur) Ii(Kn Ph Qa Qw) Ok(Ef Iz Ma Qu) aJ(cB In Ke Vp) Nx(Ef Jf Kg) Og(Gl Je Rb) Ur(dL Hu Ih) Dc(Oa Qw) Hf(aV Uo) dL(Jf Pc) DdcF NuQu IlQw InKd IzQz JeUo KgOu KnUu LdUI} Ik{Jo(Aa Fp Fr Im Lj Mz Nt Nv Nx Pe Pz Qa Qd) Og(AA Fr Hw Ih Iv Jl Mr Nr Om) In(Is Jl Lh Mi Mz Nv Nx Pe Qa) Mi(Fp Hq Iu Lj Md Oy) Md(Fr Mm Nv Nx) Iu(Fr Nx Qa Qd) Jl(Hq Om Oy) Nv(Ng Of Om) Pa(aA Iq Om) Of(Mm Qa) HueM} Ok{Jt(Aa aH bF Bg bJ bV cE Co) Js(Ao Bg Cw Dc Rb Tn Ut) Dc(Hw Jf Jo Om Rb) Dk(Jo Ou Qy Rb) aA(Hq Jr Lv Oz) Dr(Ma Qu Rc) Wm(Jk Mj Po) Rb(Jk Mj Mu) Jo(bJ bN Ut) Ou(Ha Hq Pg) Mr(Il Jf) dX(Ef To) BgQy FpLz GlPa MiMs MjRa MmOz MyPc IhIj JeJf OebN} Gt{bU(aN bA cG Dd dG dK dL) aD(aG aN aQ Ar aZ Ba) Dd(Ad bA bC bR Cs) cN(aL bB cB cL Db) dJ(aJ An bC bF) Bo(bR cF cI) aN(bG cC cV) dG(dI dR gC) dK(aQ cY dR) dM(aK dR gW) Cs(bC cF) aJ(dO gW) bR(cG cH) cP(cV fR) eF(aK Al) BndL DbcF DcGw aVdF} Nx{Dr(aN Cu Cw Dd Ij Ir Ju Li Qh Qt Tz) Md(aA Fr Jl Li Lj Mw Nh Nt Pa Pe) Hw(Ih Im In Jr Lv Mi Nh Pa Qa) In(Fp Jl Mi Nh Nu Qa) Mi(Hx Ij Oy) Jl(Hq Of Oy) Lv(Og Om) Jo(Fp Nt) Ou(Ut Vu) CheM NuOg} fR{Oz(Ax bA Cs Fp Gl Iq Jn Lj Mq Og Ra) Qw(aH cE cI Dd Kz OE Om Rg) oE(Jk Mx Oe Qt Qz Vp) Ou(al cE cG hC) Lv(Jn Pa Pc) Db(bU cP) Mj(Qx Rb) Ra(Mx Up) Qy(Jk Qt) Jn(In Iq) dV(aD bU) AwKc DqdO QnhC OgPc PacP} Fp{Mi(Hq Hw Hx Lz Md Mh Ml Nh Og Oy) Md(aA Im Lv Mw Nt Nv Pa Pg) Og(aA Iv Lv Mg Nh Oi Pa) Pa(aA Ha Iq Lz Nh) aA(Jn Nh Om) Nt(In Iu) Qy(Ha Qw) Nv(Hw Iq) FrIu LvMl MgJo IhIn} eM{Hu(aJ Ar cB Cs gL Or Ph Rc Uf Wm) Rf(aC aN cV cZ dI Uf) Gl(It Oa Oi Oz To) eF(Ib Mv Qu To Uf) bE(Dp Ld Mf) Qx(cV Uf) Qu(cF Vv) DicF DpKf ItUf RcJn LdaC OadE UkPb aJbW cNdJ} Dq{aM(An aQ aY Bo bR) cF(aQ cY Db Di dR) aK(aJ bC dK dM) Di(aJ cL Fw) bC(aQ Cs dI) cN(aQ Db dO) Bo(Bc dJ) bE(aU cY) cB(bX cP) cL(aY Dl) cF(bQ Gw) CoaN CqFw bLdL dGdI dKdR} Dr{Gw(bR bU cA cP Dc dJ) aV(aN bR dF Di DL) Rb(bR cN dN Mm Pa) Ra(bR bU dJ Mv Qw) Qw(aZ Dd Hv) Fw(Gl Rc) St(Ib Rc) dG(dJ dV) dL(bR dl) NiKc OhUf cLdJ cNdO} Nt{Jo(Im Li Lj Lv Mg Mi Nv Oz Pb Pe Pg Qa) In(Ih Lj Lv Mi Pe Pg Qa) Mi(Hq Md Nq Om Oy) Lv(Md Om Oz) Pa(Hw Nq Om) Fr(Md Og) Oz(aA Md) NqaA MmOg ImOm} nD{nR(kC IY mY nF nT nU) nJ(jM jR IK mM nC nH) eD(jF jQ jR kP) qW(kF nI qV qY) nU(kP lX) mP(mZ qX) mY(lX oQ) jF(kC oP) lYmH mIkC mMmU nIrZ nKlK qXoQ} oP{eD(iB lX mM mZ nC qX) qX(IK nK rY rZ) IX(qY rY rZ) nC(jF IK iL) hR(iC rX rZ) rA(IK mI) nNnO nTjQ nUnA nJkO iBIK qWrZ} Ou{Vu(Bb Dg Id Kc Kf Li Oy Pa Sr) Dg(Dc Jk Ut Vo) Vq(Hu Oy Qt) Kc(bL bN) Pj(Ha Ut) cM(bE Gl) AdDc ArPo RbaU} Gc{Ue(Aa aZ cZ dE Ib Kj Ny Pc Qt Uk Up) Vo(aZ cI dJ gL Ns Or) Or(Aa Kj) CsUf QwJo QuKd} Pa{Nh(aA Hw In Lv Md Mi Og) Nu(In Lz Md Og) Iq(Im Nv) Og(Lv Oi) HaLj NqMm InQa JfPj VqOy aHbA} Nv{Hw(Iq Lv Md Nh Nq) In(Iq Nq Nu Om) Lv(Md Nq Om) Iq(Lj Mi Og) NqOg MdOm} aJ{bN(bR bU cH cJ) dV(bC bF dF dM) gC(cI cY Dd Di) Mu(Qy Rb) bU(bV cS) cJcM} eX{cL(bA cF cH dF) dJ(aV aW bA bF) Dl(aV dl) DdbC aVcR bAdI dFdR} Vq{hB(cE Ct Kj Mq) oF(Gl Vu) oK(Jo Vs) NgiZ HwpF QwKy KjfP gWkS} dV{bU(cN dK dM) bA(dK dM) cG(cF cN) dG(cH dM) BobC bFcN bRdF} rA{mF(kP IK mS qT) qT(mT nT) rZ(nO rB) nUjD mllM mMIK mZnK} Lv{Md(Mm Pg Qa) In(Ih Qa) Jo(Lh Mm) Om(Im Jl) HwQa LiOg} Kc{Jf(Aa bN Ki Pj) bL(bA bV cS Ra) MueF RabN VsbA} eD{mZ(iB nB nR oQ) nO(jQ jR) mM(jF jQ) nClL} Dg{Vo(bA Dk dN Jo Mj) bA(Dc Dk)} hV{IW(kP mF rZ) mS(qY rZ) mlmM nClL} Ha{Lj(Jm Mm Oy Pc Pj) RbPe} aV{Gw(cO dF) gC(cN dF) DlDo RbaU} cH{dF(aH aW cE dM) aHbA bLdM} IL{nO(jQ jR IK) mFIK mHmI rBjR} Dc{Ad(Og Om) JfKf StOm QyLj} dG{cT(bL bQ cE dH) cLgC} Hw{Nh(Fr Mi) eF(Bg Mu)} Oz{AaOg ExUe MmJr JfPj} ml{mZ(jF kC) qX(mM nR)} dX{Ky(dI Rc) IbUk} Dv{Fw(bW cF)} Gw{AaDd cLcZ} Nu{MgOg IhIn} Kq{DkQy UtgL} nN{nRIK mSoQ} mM{jFjV kPIK} qW{IWrX nIqV} rZ{mTjR nAjE} FrNqIv MiOgOi MuKdeF NhJoLh JfJkKf StOmVu bLcLgN bUdLgC hRiCoQ Constrained panels with 2 analytes, where 1.0E-7 >= 'AUC p-value' > 0. Contains 136 panels of 81,255 total panels evaluated. : Nw(Et Fp Hw Ik In Iq Jo Js Lv Lx Ly Md Mi Ml Ms Mt My Nc Nd Ne Nf Nj Nl Of Og Ok Om Oz Pa) Ok(Fp Hq Hw Iq Jj Jo Js Jt Lv Lx Ly Md Mi Nc Nd Ne Nf Nj Nl Of Og Om Oz Pa) Gn(aN aV bR cP dJ Gl gP Hu Ly Om Or Qt Qw Ra Rb Rc Ue Um Uo Vo) Et(Jj Jo Jr Jt Lv Lx Ly Mt Nc Nd Ne Nf Nj Nl Of Og Om Oz Pa) Lx(Hw Ik Jg Jj Js Lv Ly Nc Nd Ne Nf Nh Nj Nl Nq Po) Mt(Fp Hw Jj Lv Ly Nc Nd Nj Nl) Ly(aX FR Jp On) On(Nd Nf Om Oy) Jp(Ik Nj Nl) nD(hV nA) NtOg NfJi NlJj aVdO Constrained panels with 2 analytes, where 1.0E-6 >= 'AUC p-value' > 1.0E-7. Contains 125 panels of 81,255 total panels evaluated. : Gn(aJ Bb bU cF Ch cN dI dL Do Ef eX Ib Jy Kc Me Mv Ny Og Qu Uf Uu) Et(Fp Hw Ik Iq Iv Ji Lj Md Mi Nh Nk Nq On Qe) Nl(AA Fr Jg Ji Lv Mi Mm Nx Og On Pa Qe) Mt(In Iq Ji Jp Lx Md Ne Nq Og Ok Om) On(Fp Hw Ik Iq Lv Lx Nc Ne Nj Nq Of) Jg(Fp Jj Ly Nc Nd Ne Nf Nj Of Om) Ji(Ik Lv Lx Ly Nd Ne Nj Oz) Jp(Lv Mb Nc Nd Ne Nf Nu) Lx(aA In Md Og Oz) Jj(Ik Nc Ne Nt Nw) Qe(Ly Nd Nf Nj) gP(aJ bA dM Ly) Mi(Ly Nj) Nd(Jl Nv) Nw(aA Nq) nD(oP qW) DqFw NfPe nOrA mFoP Constrained panels with 2 analytes, where 1.0E-5 >= 'AUC p-value' > 1.0E-6. Contains 216 panels of 81,255 total panels evaluated. : Ly(Aa aJ bA bV cH dE Id Im Jj Jl Lh Mm Mz Nl No Nv Pa Pe Sr) Jg(Hw Iq Iu Iv Ji Jo Jt Lj Lv Md Mt Mv My Nh Nq Og Oz Pa Qe) Qe(Dc gP Hw Ik In Iq Ji Jj Jp Lv Nc Ne Nq Nt Qc) On(Hx Ii In Jj Jk Js Jt Lj Md Mt Ng Nh Og Oz Pa) Gn(cH Cs Em Fb Fw Iz Jj Kf Kj Kk Ma Mu Nj Pc) Ji(Fp Hw In Iq Iv Jo Jq Js Md Ms Nc Nh Nt Om) Jp(Fp Hw Iq Iv Jj Jr Lj Md Mf Nh Nq Nt Pa) Nf(Ar aX Fp FR Lh Li Lv No Nt Nv) Fp(Jj Lv Mi Nc Ne Nl Nt Pa) gP(Bc bV eF fR gL Kk Ko Sr) Nl(Li Lj Mz Nk Nt Nv Pe) Mm(Lv Lx Mt Nc Ne Nj) Pa(Ik Mt Nc Ne Nj Nt) Et(aA Jf Mr Ok Vo) Nd(FR Mi Mz Qa) Gt(aN cL eF Fw) Lv(Nc Ne Nt Qa) Nv(Hw Iq Nc Nj) aX(Me Nw Ou Rb) nD(kP oQ qX rA) Mi(Lx Mt Nx) aJ(cJ dV gC) oP(lK nU rX) Nt(Jo Oz) Nj(Fr Li) Nx(Hw Md) aA(Mt Ok) dG(dV gC) rB(hV rA) DqcL LxIq MeSr NcNk NhJj IkOg QwfR JkKo nRIK nUoQ

Figure 9 Continued

Constrained panels with 2 analytes, where 1.0E-4 >= 'AUC p-value' > 1.0E-5. Contains 435 panels of 81,255 total panels evaluated. : gP(aA aP Ax Ba cH dF DG Dl Et Fr Gt Jf Jp Kc Kp Kq Lx Mt Nf Nw Ok Ou Qa Qw Qy Rj Ur Wm) Ly(aA bN dM Fp gL Ir Iv Jf Jn Jr Ko Li Lj Lv Ma Mp Nc Ne Nt Nx Ou Pg Qa Qd Uh) Nj(AA aX Fp fR Im Jj Jl Lh Lj Lv No Nt Nx Og Pc Pe Pg Qa Qd) Nc(AA Fr Hw Ik Im Jl Li Lj Mi Mz Nd Ni Nt Nx Og Pb Pe Qa) Nc(AA Fr Hw Ik Im Lh Li Lj Mi Mz Nk Nt Nv Nx Og Pe Pg Qa) Lv(aX FR Ih Ik Im Iv Jj Jl Lh Li Lj Nd Nh Nv Oz Pa Pe) Et(Ao aX bA Bg bV Dc Gl Ha Kc Ou Qt Qw Ra Rb Rc Ut Vu) Nf(aJ bA bV dG Id Ik Jl Ko Kq Lj Nr Nu Nx Pg Qa Sr) Qe(aX Fp Fr Il Iu Iv Md Mi Mm Nh Og Om On Oz Pa Qb) Nw(Ao bA Bg Co Dc Dk Gl Ha Qw Qy Rb Rg Rj Ut Vp Tj) Fp(aA Fr Gn Hw Ik Iv Jl Lh Md Mg Mm Nd Nh Og) Jj(Iv Ji Jm Jn Jr Lh Mg Mm Nr Pa Pe Pg Qa Qd) aX(aJ bA dG Iq Kc Ko Lx Ok Pb Pc Ph Qw Qy Sr) Nd(aA Im Lh Li Mm Mp Mw No Nt Nx Pe Pg Qd) Ik(aA Fr Jl Jo Li Lj Md Me Mi Mm Nx Pe Qa) Ko(bN Dc Dd Dk Iq Jf Me Mj Om Po Qt Qw) Nt(aA Fr Hw In Lj Md Mi Om On Pb) Nl(Hw Iv Jl Lh Md Mc Ni Om Pc Pg) Jg(Dc Jh Mi Mm Mr Mu Mw Ng On Oy) Oz(Aa FR Jp Lh Mi Mm No Nv Nx) Ok(Bg Dc Dk Gl Ha Rb Tn Ut Tj) Me(bA fR Hf Id Jf Kc Ou Vq) Jp(Jl Mi Mr Og Om On Pb Pe) Nv(In Iv Lj Md Nh Nq Om) On(Hq Jo Mi Ms Mv My Ny) aJ(bL bN bR bU cM Dq Gt) dG(bL bN bR bS bU cT dH) nD(mH mP mU nF nI nJ) Gn(Ld Mf Oa Ou Qx) Lx(Aa Iu Mr Om Pa) Nh(aA Fr Mi Nx Pa) Og(Iv Ji Nu Nx Oi) hV(IL IW mS nU rZ) rA(mF mI nT nU) Nx(Im In Lj) aV(Dq Dr Gt) cH(bA dF dM) Fr(Iv Nq) Mt(Jl Mr) Ji(Mi Pa) Pe(In Iq) fR(bU Pc) jF(nO rB) oP(lX nC) AdDc BoGt DgVo DqbC HwQa bAbM cJdM eDnR mZoQ Constrained panels with 2 analytes, where 1.0E-3 >= 'AUC p-value' > 1.0E-4. Contains 758 panels of 81,255 total panels evaluated. : gP(Ad Ap aW aX cR cS eM Fp Id Ik Im Iq It iZ Jg Ji Jm Kd Kf Kn Lh Lj Lv Me Mm Nd Nj Nx On Oy Oz Pa Pb Pc Ph Pj Qd Rb St Uh Vq) Nf(Aa aP Ax cH Cs Dg dM eF gL Ii Im Ir Iv Jj Kk Kn Ly Mi Mm Mz Nb Nh Nj Pa Pf Pz Qd Qw St To Uh Vq Vt) aX(aA bU dF dM Fp Hw Ih It Iv iZ Jf Kd Kk Kn Kp Lj Mt Nd Nr Oe Om Oy Oz Pa Rj St Vp) Qw(Aa Ad bA bC bV cH Dg Dr eF gL Id Jg Jp Kq Lj Lx Me Mt Nr Ok On Ph Qe Rf Sr St) Jj(Em Fr Ih Ii Ij Im Io Ir Jl Jt Li Lj Mf Mi Nd Ng Nu Nv Nx Oh Oi Oy Oz Pf Pz Qb) Ko(Bg bV cM cS dM Ha Hq Hw Ii Ij In Jo Md Mu Mv Ou Pa Pg Rb Rc Ut Vs Vu) bA(aJ cS Db Dc Di dM Gl Gt Hq Hw Ii In Iq Jk Lv Mr Nd Nj Om Pa Pc Qe Rb) Ly(cS Dc Hf Hw Ih Ik Io Jt Kc Kp Md Mr Nh Nj Nr Og Pb Pc Pf Ph Uk) Lj(aA Dc cF Fr Ha Iq Iv Jf Lz Mg Mi Mm Nd Nh Og Oi Oz Pb Pg Qy Rb) Qe(AA bC Bg bN bV Dd Gl Ha Jf Kc Mr Qg Ra Rb Ut Vp Vs Vu Tj) Et(aJ bN cE Ch Co cS Dk dM Ef iJ iZ Jd Kg Qn Rg Tn Vp Vs Tj) Nj(aJ bN bV dM Hw Ih Iv Jf Jr Jt Mk Mp Mr Mz Nb Nr Pb Pf) Om(eF Fp fR Ik Im Jl Kf Kq Lh Li Nc Ne Nx Pe Pj Qa St Tt) cH(aA aJ aW bV cP cS cT dG Dq eF fP gL Gt Lv Lx Nd Pa Rb) Mm(aA Fr Jf Ji Jp Jr Li Mb Nh Nq Nt Og On Pa Pb Pe Qa) Nd(aJ bV dM eF Io Ir Iv Jn Lw Nb Nu Oh Pa Pf Pz Qb) Hw(dG eF Ih Ik Im Ir Jl Jn Lh Li Nh Nu Pe Qd Sr St) Nw(aJ bN bV cS dM Ib Jd Je Jf Ou Qn Qt Qx Tn Vs Vu) Dc(Ap Ba Dg eF Fp Id Jp Kf Kq Li Lx Mt On Qa Qd) Ok(aH Ao bN cE Ch Co Ct dM Jf Kg Qn Qt Vp Vs Vu) fR(bR cP Db Di Fp Iq It Jn Ml Mq Nc Ne NI Pa Pb) Iv(Ik Im Jl Li Mi Nc Ne Nh Nx Pa Pb Pe Pg Qa) Iq(aJ Fr Im Ir Jl Lh Li Nx Pa Pg Qa Qd Sr) aA(Jg Ji Jn Jp Jr Lh Li Lv Nx On Oz Pa Pe) Nh(Aa Ih Im Jl Jr Lh Li Og Pb Pe Pg Qa) Jf(Aa Dg Dl Jp Kc Kp Nm Ou Ph Pj Sr St) nD(jQ jR kC IK IX IY nK nM nR nT nU) Mr(Ar Fp Ik Kq Lv Nc NI Nt Nv Ou) Rb(aJ dE dM Id Jp Ou Pb Sr St Uh) Og(Aa Im Ir Lh Li Lv Nv Pe Qa Qd) dG(Bg cS Db dM Gt Hq Ii Me Oe Pc) Oz(Im Jl Jn Jr Li Mz Nu Qa Qd) aJ(Aa bC bS cS cT Di Me Pc) eF(Aa dE Di Dk Jk Kc Mu Pc) Gl(Dg Jp Kp Lx Ou Sr Uh) Ha(Fp Kf Kq Lx Nr Oa Pe) Md(Im Lh Li Lv Nu Pe Qa) bV(bU gL Lv Me Pa Pb Pc) Lh(Hq Ik In Jo Nc Of) dF(aH bN bQ bU cE dM) oP(eD hR hV jQ rY rZ) Dk(Ba Jg Jp Kq On) Me(Ar Kp Ph To Uh) Qa(In Iu Mi Pa Pb) Jl(Li Ne Nv Nx Pe) Vu(Kf Kn Nr Ou St) Aa(Ik Jr Lv Mt) Bg(Ad Jg Jp On) Dq(aK aQ cF cY) Gt(bC cB cF cG) Kc(bL bN Ou Ra) Ut(gL Kq Lx On) Pc(gL Jr Nc Ne) mZ(eD mI nB rA) Mi(Li Lv Pe) Ih(Ik In Nx) Jp(Ct Cw Vp) Pb(Ir Ne Nu) dM(bR bU cM) eP(aV cL Rf) nO(hV jQ jR) Dg(Jo Oe) Dr(Fw Ra) Gn(Qz St) Mu(Kq Sr) Nc(Jt Pg) Jg(Cw Vo) Jk(Kf St) Kk(Nm Pj) On(Nb Pg) Vp(Kq Nr) Pe(lu Lz) eD(IX mM) nR(nK rA) mI(mH qX) nC(IL oQ) hV(mF mM) AdOe ArPo BaCt EmUe FrJr NqLi NuIm NcIt InQd JoUh KyVq NvOf NxPa OuPj bUcT cSgL dLgC rBrZ Constrained panels with 2 analytes, where 1.0E-2 >= 'AUC p-value' > 1.0E-3. Contains 1,234 panels of 81,255 total panels evaluated. : Hw(Aa aJ Ar Ba bV cH Cs dF Dg Fr gL Id Iv iZ Jf Jj Jr Kf Kk Kp Kq Lj Lv Mg Mm Mp Mw Mx Mz No Nr Oi Pa Pb Pg Ph Pj Pz Qb Uh) bN(aP aX BC bV Dg Dl dM eF FP gL Id iH It iZ Jf Jg Jp Kf Kk Kp Lj Lv Lx Me Mt Nf Ou Oz Pa Pc Qa Qw Qy Rb Vt Wm) Dg(aH aW aX Bg bV cP cS Cw Dd Dk dM Ha Ii In Iq Jj Jk Js Jt Kj Kk Md Nd Of Og Om Pc Pg Qt Ra Ut Vp Vs) Iq(Aa Ar aX bE bV cB cH Cs dG Dl dM gL Id Ih Io Jn Jr Kf Kk Kq Mi Mm Mp Mz Nn No Nr Oh Pz Qb St Uh) Om(AA Ad Ap Ar Ba cH Cu dF dG Dl gL Id Jj Kk Kl Kp Lj Lv Mm Nh Nj Nu Ou Pg Qb Qd Rb Sr Tr Uh) Vs(Ad aJ bA Bc dG dM eF It iZ Jg Jm Jp Kf Kp Kq Lx Mm Mt Nr On Ou Oy Pa Ph Qa Qy Sr St Tt Uh Vq) Ha(Ar Ax bA bV Cs dG Dl Ex Id It Jg Ji Jm Jn Jp Kp Lh Li Mm Mt Nx On Ou Pa Qa Qd Rf Sr St Uh) Qw(aJ Ap Ax cS Dl dM Fp Ih Ik It Jf Jm Kf Kk Kp Ly Mm Nj Nm Oi Ou Oy Pa Pj Qa Qy Rb Tr Tt Uh) Dc(Ar Bc cH Co Cu Dl Fr Fy Ik Im It Ji Jm Kc Kp Lh Me Nr Nv Nx Pe Pj Pz Rf Sr St Tt Uf Uh) Gl(Ad Ap Ba dF dG eF fR Fy Id Ik Jg Ji Ke Kf Ko Kq Lh Li Mm Mt Nr Nv On Pa Qa St Tt Vq) Nf(aA cR cS Ih Jf Jn Jr Jt Kc Kd Kp Mg Mp Mr Nd Oh Oi Ou Oz Pb Pc Ph Po Qb Qy Rb Wm) Sr(Bg bV cS Dk gW Hq Ii In Jk Js Kc Kp Md Mj Mr Ou Pc Pg Po Qy Ra Ut Vo Vp Vu) Vp(bA Ex Fp Id It iZ Jg Jm Jn Kc Kf Kk Kn Lh Lj Lx Mt Nx On Qa Rb St Uh) Vu(Ad Ar Bb Bc eF It Jg Jm Jp Kc Kp Kq Lh Li Lj Lx Mt Nx On Pa Ph Qy Uh) cH(aP aX Bc eP hC It Me Mt Oe oK Ou Oy Oy Oz Pb Pc Ph Qy Ra) Aa(dG Fp hB It iZ Kd Kk Lu Ma Nd Nq Oi Ou Pa Pc Ra Rb) gL(cJ Di Fp Jk Kp Lj Lv Md Me Mu Nd Nj Oe Oz Pa Ur Wm) Bg(Ap Ba Co dF Fr Ik Kf Kk Lh Li Lx Mt Nr Ou Tt Uh) Jj(aA Ad bC Fr Jk Mk Mw Mx Mz Nm Nn Pb Pc Po Ug) Jk(Ad Ba dG Ex Id Kc Kk Kp Qy Rb Rf Tr Tt Uh) Md(Ar bA dG eF Fr Id iZ Kf Kk Mm No Pg Uh) Mu(Ex Id Kf Kk Kp Ou Qy Rb Rf Tr Tt Uf Uh) Nd(aP BC dG Dl Ih Jr Jt Mk Mx Oi Pb Pc) Jg(Aj Ao Ch Co Ct Ef Ib Iz Qt Ra Rc Ua Uu) Oe(aJ Ap Ar BA bC Cs dF Dl eF fR Kf Rf) aA(bR cJ dE Fr Ih Im Iv Mf Mi Pb Pc Pg Qa) aX(aC bM bR cB cJ cP cT Dl Dr Hc Or Ur Wm) Dd(Ad Ap Ax Ba Bc Dl Dq fR Gt Jp Kf Pj) Kc(bA dJ Hq Jp Ko Lx Mm Mt Nw Pa Qy Rb) Lh(Dk Ih Iu Iv Jl Li Lj Mi Mm Pa Pc Qa) Pb(bC Im Jn Jr Jt Lv Mz No Oi Pj Qd) aJ(Db fP Ii It Lv Mt Nq Ok Oy Oz Pa) eF(hC Hq Ib Ii iJ Mv Nj Nq Rb Ua Wm) iZ(cJ fP hC Jr Me Mj Nk Pa Ql Ur Vq) Dk(Ad Ap Fr Kf Kn Lx Mt Tt Uf Uh) Vo(Ad Ap Dl Em Kf Kl Mm Pz Uf Uh) Pc(aP Ax bC Cs Jn Lj Mz Pj Rb Uh) fR(AW cB cT dV hC Kz Na oE Qt) Ra(Ax Dl eM Fp Id Nm Ph Pj Uh) On(Ao Ch Co Ct Ib Qt Tn Ua Tj) Ou(aU Ch Ct gW Hq Kp Lj Mk Qy) Oz(Ih Ir Jt Mg Mk Nb Nr Oh Pz) eP(aM bR cC dF dG dJ dL gP Ih) Dq(aM Bo cB cN cP dJ Dl dR) Jo(Ad Ap Kf Mg Nv Pj Uf Vq) Pg(Ar bA Cs dG Ih Jr Kf Uh) bU(aP Bc cJ cU dA dE Dl Gt) Rb(Ih It Kp Lx Pa Ph Pj) bC(dE Dl Fp Kk Lj Lv Ph) mF(iB jF jQ IK qW qX rB) Gt(aK aQ bR cN cY dJ) Mj(Id Kf Kk Rf Tt Uh) Mm(Ih Iv Jl Kk Mi Nk) bA(dV hC It Lj Ur Wm) nC(jF mZ nH nL nR rA) qX(nI nO nR nT nU oP) qW(IW mI nI nO nT nU) oQ(eD hR rA rX rY rZ) Tj(Ar Jm Kf Lx Nr) Hq(Ar Ba dF Kf Uh) Ii(Ad Ap ar dF Uh) Jp(Ao Ph Qt Tn Ua) Et(aH aI Cw hC) Id(Jq Nj Po Rj) Qy(Fp Lx Qe Qt) Jl(Im Lj Oy Qa) Jr(Mg Nu Pa Pf) Vq(Dc oK Oy Qt) aP(bL bR bS cJ) eM(Di Dp Ib Uk) fP(bJ gP Lj Me) mZ(IK mW nK nL) nD(hR iB jF mY) Ba(cE Cw Di) Em(cB Kj

Figure 9 Continued

Ur) No(Js Mc Oi) Mq(Ex Nj Uf) Ua(Ad Mt Tt) Ih(Fr Iv Mg) Qg(Jm Lj Qa) Kk(Ib Ny Oy) Rj(Ax Fp Jn) Nx(Dr My Ny) Pj(Hc Or Oy) nR(rX rY rZ) nU(hR jF lK) hC(Nw oF Qe) rA(oP rY rZ) Ap(Cw Qt) Wm(Lv Me) Lx(Co Kp) Mi(Im Oi) Mk(Ly Nu) Jq(Kf Uh) Js(dG Uh) Ko(gW Ma) Uk(Jm Nm) bR(bZ cU) cP(Bc Dl) cT(bM dE) dV(cN dF) gP(cJ hB) mI(hV jQ) jF(mT nT) ArRg DrGw FpbE FrPa GcKj MzNk ImIu QecQ NwPh aVdA cCdE cGeX nOhX mMlK mSjQ nArZ hVkE

Figure 9 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.0E1 | 6.5E1 | 8.2E1 | 7.4E1 | 5.8E1 | 6.9E1 | 1.0E0 | 1.4E1 | 4.8E2 | 2.4E2 | 1777 | 8 | 298 | 8 | 0.43 |
| Po | pg/ml | 6.9E-1 | 1.2E1 | 8.6E0 | 4.2E1 | 2.4E1 | 7.0E1 | 8.0E-3 | 2.6E-2 | 2.7E2 | 2.2E2 | 899 | 9 | 335 | 9 | 0.72 |
| Et | ng/ml | 1.4E3 | 2.4E3 | 1.7E3 | 2.6E3 | 1.2E3 | 1.1E3 | 7.5E1 | 1.4E3 | 5.0E3 | 4.4E3 | 898 | 9 | 335 | 9 | 0.73 |
| Fp | ng/ml | 1.4E1 | 2.5E1 | 2.5E1 | 3.2E1 | 2.9E1 | 2.4E1 | 6.0E-3 | 3.8E0 | 1.4E2 | 6.7E1 | 931 | 9 | 336 | 9 | 0.63 |
| Fr | ng/ml | 3.7E4 | 5.4E5 | 1.2E5 | 4.8E5 | 1.8E5 | 3.0E5 | 1.9E2 | 4.1E4 | 9.0E5 | 8.5E5 | 1043 | 10 | 340 | 10 | 0.87 |
| Nm | pg/ml | 1.4E4 | 3.9E4 | 3.3E4 | 3.6E4 | 8.2E4 | 3.0E4 | 1.0E-9 | 1.4E3 | 1.6E6 | 7.9E4 | 902 | 9 | 337 | 9 | 0.60 |
| Nn | pg/ml | 1.6E2 | 2.0E3 | 1.9E3 | 1.5E4 | 8.2E3 | 2.4E4 | 1.0E-9 | 6.0E1 | 1.0E5 | 6.9E4 | 902 | 9 | 337 | 9 | 0.77 |
| No | pg/ml | 1.6E1 | 6.7E1 | 3.8E1 | 2.4E2 | 1.1E2 | 4.7E2 | 1.0E-9 | 4.7E0 | 2.5E3 | 1.4E3 | 902 | 9 | 337 | 9 | 0.75 |
| Nq | pg/ml | 2.0E0 | 1.0E1 | 2.0E1 | 2.7E1 | 7.6E1 | 4.0E1 | 1.0E-9 | 1.0E-9 | 1.2E3 | 1.1E2 | 902 | 9 | 337 | 9 | 0.69 |
| Nr | pg/ml | 1.2E0 | 1.0E-9 | 2.9E1 | 9.6E2 | 1.8E2 | 2.8E3 | 1.0E-9 | 1.0E-9 | 4.1E3 | 8.5E3 | 902 | 9 | 337 | 9 | 0.47 |
| Ns | pg/ml | 1.0E-9 | 1.0E-9 | 9.2E0 | 1.3E1 | 5.2E1 | 4.0E1 | 1.0E-9 | 1.0E-9 | 1.1E3 | 1.2E2 | 902 | 9 | 337 | 9 | 0.51 |
| Nt | pg/ml | 1.0E2 | 1.4E2 | 1.4E2 | 1.9E2 | 1.2E2 | 2.0E2 | 1.0E-9 | 3.5E1 | 1.7E3 | 6.8E2 | 902 | 9 | 337 | 9 | 0.56 |
| Nu | pg/ml | 2.0E1 | 5.0E1 | 5.5E1 | 1.0E2 | 9.0E1 | 1.8E2 | 1.0E-9 | 1.0E-9 | 8.9E2 | 5.8E2 | 902 | 9 | 337 | 9 | 0.59 |
| Lu | pg/ml | 1.0E4 | 7.8E3 | 1.8E4 | 7.8E3 | 6.2E4 | 6.4E3 | 3.5E2 | 1.0E-9 | 1.3E6 | 2.1E4 | 905 | 9 | 337 | 9 | 0.35 |
| Lv | pg/ml | 1.0E-9 | 3.3E1 | 1.1E1 | 4.2E1 | 2.2E1 | 4.0E1 | 1.0E-9 | 1.0E-9 | 2.6E2 | 1.0E2 | 905 | 9 | 337 | 9 | 0.74 |
| Lw | pg/ml | 1.0E-9 | 1.0E-9 | 3.7E-1 | 1.9E0 | 3.8E0 | 5.6E0 | 1.0E-9 | 1.0E-9 | 8.0E1 | 1.7E1 | 905 | 9 | 337 | 9 | 0.60 |
| Lx | pg/ml | 1.0E-9 | 4.9E2 | 1.7E2 | 1.9E3 | 8.6E2 | 3.2E3 | 1.0E-9 | 6.0E1 | 2.2E4 | 1.0E4 | 905 | 9 | 337 | 9 | 0.89 |
| Ly | pg/ml | 1.0E-9 | 1.0E-9 | 1.0E1 | 6.4E0 | 2.0E1 | 1.4E1 | 1.0E-9 | 1.0E-9 | 1.6E2 | 4.3E1 | 905 | 9 | 337 | 9 | 0.48 |
| Lz | pg/ml | 1.0E-9 | 1.0E-9 | 4.0E0 | 2.4E1 | 3.0E1 | 6.9E1 | 1.0E-9 | 1.0E-9 | 6.0E2 | 2.1E2 | 905 | 9 | 337 | 9 | 0.57 |
| Ma | pg/ml | 2.9E2 | 2.7E3 | 1.4E3 | 3.1E3 | 3.6E3 | 3.0E3 | 1.0E-9 | 5.8E1 | 6.5E4 | 9.5E3 | 905 | 9 | 337 | 9 | 0.74 |
| Mb | pg/ml | 2.5E1 | 2.2E1 | 3.1E1 | 2.7E1 | 1.5E1 | 1.0E1 | 4.1E0 | 1.5E1 | 2.1E2 | 4.3E1 | 905 | 9 | 337 | 9 | 0.42 |
| Mc | pg/ml | 1.0E-9 | 1.0E-9 | 3.8E-2 | 1.0E-9 | 5.7E-1 | 0.0E0 | 1.0E-9 | 1.0E-9 | 1.3E1 | 1.0E-9 | 905 | 9 | 337 | 9 | 0.49 |
| Md | pg/ml | 1.0E-9 | 1.0E-9 | 4.4E-1 | 1.3E0 | 3.6E0 | 3.6E0 | 1.0E-9 | 1.0E-9 | 6.8E1 | 1.1E1 | 905 | 9 | 337 | 9 | 0.57 |
| Me | pg/ml | 3.3E1 | 3.0E1 | 3.2E1 | 3.1E1 | 2.0E1 | 2.2E1 | 1.0E-9 | 3.2E0 | 3.2E2 | 7.9E1 | 905 | 9 | 337 | 9 | 0.43 |
| Mf | pg/ml | 1.0E-9 | 1.0E-9 | 5.4E-1 | 1.0E-9 | 2.9E0 | 0.0E0 | 1.0E-9 | 1.0E-9 | 5.6E1 | 1.0E-9 | 905 | 9 | 337 | 9 | 0.43 |
| Mg | pg/ml | 1.6E0 | 3.6E0 | 7.4E0 | 4.3E0 | 1.2E1 | 4.5E0 | 1.0E-9 | 1.0E-9 | 9.2E1 | 1.3E1 | 905 | 9 | 337 | 9 | 0.51 |
| Mh | pg/ml | 1.0E-9 | 1.0E-9 | 1.3E1 | 4.5E0 | 9.6E0 | 1.2E1 | 1.0E-9 | 1.0E-9 | 1.6E2 | 3.8E1 | 905 | 9 | 337 | 9 | 0.54 |
| Mi | pg/ml | 1.0E-9 | 1.0E-9 | 9.0E-1 | 3.2E1 | 1.2E1 | 5.4E1 | 1.0E-9 | 1.0E-9 | 3.2E2 | 1.6E2 | 905 | 9 | 337 | 9 | 0.71 |
| Mj | pg/ml | 1.0E-9 | 1.0E-9 | 4.5E0 | 6.3E1 | 2.5E1 | 1.8E2 | 1.0E-9 | 1.0E-9 | 4.6E2 | 5.4E2 | 905 | 9 | 337 | 9 | 0.58 |
| Mk | pg/ml | 1.0E0 | 1.0E-9 | 1.3E1 | 6.2E2 | 8.5E1 | 1.9E3 | 1.0E-9 | 1.0E-9 | 1.7E3 | 5.6E3 | 905 | 9 | 337 | 9 | 0.50 |
| Ml | pg/ml | 1.0E-9 | 1.0E-9 | 5.6E0 | 5.7E-1 | 7.5E1 | 1.1E0 | 1.0E-9 | 1.0E-9 | 2.1E3 | 2.8E0 | 905 | 9 | 337 | 9 | 0.52 |
| Mm | pg/ml | 6.1E2 | 1.1E3 | 1.1E3 | 1.7E3 | 1.5E3 | 2.1E3 | 1.0E-9 | 2.0E2 | 1.2E4 | 6.9E3 | 905 | 9 | 337 | 9 | 0.62 |
| Mn | pg/ml | 5.6E0 | 1.2E1 | 1.0E1 | 1.7E1 | 2.3E1 | 1.9E1 | 1.0E-9 | 1.0E-9 | 3.5E2 | 6.6E1 | 905 | 9 | 337 | 9 | 0.73 |
| Mp | pg/ml | 1.0E-9 | 1.7E1 | 1.0E1 | 5.1E1 | 3.4E1 | 6.4E1 | 1.0E-9 | 1.0E-9 | 6.3E2 | 1.8E2 | 904 | 9 | 337 | 9 | 0.70 |
| Mq | pg/ml | 1.0E-9 | 1.0E-9 | 2.9E0 | 1.2E1 | 1.7E1 | 3.5E1 | 1.0E-9 | 1.0E-9 | 2.4E2 | 1.1E2 | 904 | 9 | 337 | 9 | 0.52 |
| Mr | pg/ml | 1.0E-9 | 1.0E-9 | 2.8E1 | 1.3E3 | 1.6E2 | 3.9E3 | 1.0E-9 | 1.0E-9 | 2.2E3 | 1.2E4 | 904 | 9 | 337 | 9 | 0.57 |
| Ms | pg/ml | 4.1E2 | 2.0E2 | 5.6E2 | 3.4E2 | 6.5E2 | 3.0E2 | 1.0E-9 | 1.0E-9 | 5.9E3 | 8.6E2 | 904 | 9 | 337 | 9 | 0.42 |
| Mt | pg/ml | 2.5E-1 | 9.0E0 | 1.1E1 | 2.3E1 | 1.2E2 | 3.2E1 | 1.0E-9 | 1.3E0 | 3.2E3 | 1.0E2 | 904 | 9 | 337 | 9 | 0.87 |
| Mu | pg/ml | 1.0E-9 | 1.4E0 | 1.3E0 | 6.8E0 | 1.0E1 | 9.7E0 | 1.0E-9 | 1.0E-9 | 2.3E2 | 2.7E1 | 904 | 9 | 337 | 9 | 0.72 |
| Mv | pg/ml | 1.0E-9 | 2.6E1 | 7.0E1 | 1.2E2 | 3.2E2 | 2.1E2 | 1.0E-9 | 1.0E-9 | 4.5E3 | 6.2E2 | 904 | 9 | 337 | 9 | 0.72 |
| Mw | pg/ml | 3.8E1 | 1.7E2 | 5.2E2 | 1.4E3 | 3.3E3 | 2.8E3 | 1.0E-9 | 1.0E-9 | 6.2E4 | 8.5E3 | 904 | 9 | 337 | 9 | 0.73 |
| Mx | pg/ml | 1.0E-9 | 1.0E-9 | 2.8E-1 | 4.0E-1 | 1.5E0 | 9.9E-1 | 1.0E-9 | 1.0E-9 | 3.2E1 | 3.0E0 | 904 | 9 | 337 | 9 | 0.63 |
| My | pg/ml | 1.0E-9 | 1.7E1 | 4.7E2 | 4.3E2 | 3.0E3 | 1.1E3 | 1.0E-9 | 1.0E-9 | 3.9E4 | 3.4E3 | 904 | 9 | 337 | 9 | 0.62 |
| Mz | pg/ml | 1.1E1 | 6.3E1 | 3.0E1 | 1.3E2 | 9.9E1 | 1.3E2 | 1.0E-9 | 1.0E0 | 1.9E3 | 3.6E2 | 904 | 9 | 337 | 9 | 0.83 |
| Na | pg/ml | 1.0E-9 | 1.0E-9 | 7.3E-1 | 1.3E0 | 3.0E0 | 3.5E0 | 1.0E-9 | 1.0E-9 | 4.2E1 | 1.1E1 | 904 | 9 | 337 | 9 | 0.52 |
| Nb | pg/ml | 2.0E0 | 2.6E0 | 3.9E0 | 2.9E1 | 1.2E1 | 7.9E1 | 1.0E-9 | 1.0E-9 | 2.3E2 | 2.4E2 | 904 | 9 | 337 | 9 | 0.57 |
| Nc | pg/ml | 3.4E2 | 1.5E2 | 5.6E2 | 3.5E2 | 7.3E2 | 6.7E2 | 1.0E-9 | 1.0E-9 | 9.2E3 | 2.1E3 | 904 | 9 | 337 | 9 | 0.39 |
| Nd | pg/ml | 2.9E1 | 4.1E1 | 2.9E1 | 6.2E1 | 8.3E1 | 5.1E1 | 1.0E-9 | 6.8E0 | 2.1E3 | 1.4E2 | 904 | 9 | 337 | 9 | 0.71 |
| Ne | pg/ml | 4.4E2 | 3.6E2 | 5.8E2 | 4.0E2 | 5.7E2 | 3.1E2 | 1.0E-9 | 1.8E1 | 7.0E3 | 1.1E3 | 904 | 9 | 337 | 9 | 0.43 |
| Nf | pg/ml | 1.0E-9 | 1.0E-9 | 3.0E0 | 9.2E0 | 1.1E1 | 2.7E1 | 1.0E-9 | 1.0E-9 | 1.6E2 | 8.2E1 | 904 | 9 | 337 | 9 | 0.49 |
| Ng | pg/ml | 1.9E1 | 4.4E0 | 1.3E2 | 3.5E1 | 2.5E2 | 7.5E1 | 1.0E-9 | 1.0E-9 | 2.3E3 | 2.3E2 | 904 | 9 | 337 | 9 | 0.38 |
| Nh | pg/ml | 6.9E1 | 3.5E1 | 9.0E1 | 7.0E1 | 8.2E1 | 6.5E1 | 1.0E-9 | 2.2E0 | 5.6E2 | 1.6E2 | 904 | 9 | 337 | 9 | 0.43 |
| Ni | pg/ml | 1.0E-9 | 5.3E1 | 7.3E1 | 8.7E1 | 1.2E2 | 1.1E2 | 1.0E-9 | 1.0E-9 | 1.1E3 | 3.4E2 | 904 | 9 | 337 | 9 | 0.61 |
| Nj | pg/ml | 7.3E0 | 9.0E0 | 1.1E1 | 1.4E1 | 1.2E1 | 1.8E1 | 1.0E-9 | 9.4E-1 | 1.1E2 | 5.7E1 | 904 | 9 | 337 | 9 | 0.55 |

Figure 10

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nk | pg/ml | 1.7E1 | 2.7E1 | 3.3E1 | 2.7E1 | 4.0E1 | 2.1E1 | 1.0E-9 | 1.5E0 | 2.0E2 | 6.6E1 | 904 | 9 | 337 | 9 | 0.55 |
| Nl | pg/ml | 4.6E1 | 3.3E1 | 6.1E1 | 4.1E1 | 6.8E1 | 3.8E1 | 1.0E-9 | 1.0E-9 | 1.1E3 | 1.1E2 | 904 | 9 | 337 | 9 | 0.43 |
| Hq | pg/ml | 1.1E0 | 1.7E0 | 1.0E2 | 3.5E1 | 1.6E3 | 9.8E1 | 1.0E-9 | 1.0E-9 | 3.4E4 | 3.0E2 | 900 | 9 | 336 | 9 | 0.54 |
| Hr | pg/ml | 1.2E2 | 4.5E1 | 7.9E2 | 1.2E3 | 1.6E3 | 3.6E3 | 1.0E-9 | 2.1E1 | 1.7E4 | 1.1E4 | 900 | 9 | 336 | 9 | 0.28 |
| Hu | pg/ml | 5.6E0 | 6.1E0 | 3.0E3 | 3.5E2 | 2.6E4 | 8.0E2 | 1.0E-9 | 1.0E-9 | 6.3E5 | 2.4E3 | 900 | 9 | 336 | 9 | 0.50 |
| Hv | pg/ml | 1.4E0 | 2.3E0 | 4.1E0 | 8.8E0 | 3.2E1 | 1.9E1 | 1.0E-9 | 2.1E-1 | 8.9E2 | 5.9E1 | 900 | 9 | 336 | 9 | 0.67 |
| Hw | pg/ml | 6.5E0 | 2.7E0 | 2.9E1 | 3.9E2 | 3.2E2 | 1.1E3 | 1.0E-9 | 3.2E-1 | 9.4E3 | 3.4E3 | 900 | 9 | 336 | 9 | 0.40 |
| Hx | pg/ml | 8.8E0 | 2.7E1 | 3.9E1 | 2.5E2 | 3.2E2 | 6.4E2 | 1.0E-9 | 7.9E0 | 9.3E3 | 2.0E3 | 900 | 9 | 336 | 9 | 0.76 |
| Ih | ng/ml | 7.2E1 | 2.6E2 | 2.4E2 | 4.0E2 | 4.3E2 | 4.8E2 | 1.0E-9 | 1.0E-9 | 3.6E3 | 1.2E3 | 904 | 9 | 336 | 9 | 0.58 |
| Ii | ng/ml | 9.4E1 | 9.1E1 | 2.5E2 | 1.2E3 | 6.8E2 | 3.0E3 | 1.0E-9 | 7.0E0 | 1.0E4 | 9.2E3 | 903 | 9 | 336 | 9 | 0.54 |
| Ij | ng/ml | 7.7E1 | 1.1E2 | 2.0E2 | 8.9E2 | 9.9E2 | 2.2E3 | 1.0E-9 | 3.5E1 | 2.4E4 | 6.4E3 | 891 | 8 | 334 | 8 | 0.60 |
| Ik | ng/ml | 1.3E1 | 2.8E1 | 8.1E2 | 2.5E2 | 8.2E3 | 4.0E2 | 5.9E-1 | 1.5E0 | 1.2E5 | 1.1E3 | 898 | 8 | 334 | 8 | 0.53 |
| Il | ng/ml | 3.4E2 | 1.9E2 | 1.3E3 | 1.9E3 | 2.8E3 | 4.2E3 | 1.0E-9 | 1.6E1 | 1.3E4 | 1.2E4 | 881 | 8 | 334 | 8 | 0.41 |
| Im | ng/ml | 2.1E2 | 5.5E2 | 3.9E2 | 5.6E2 | 6.0E2 | 3.4E2 | 1.3E1 | 1.8E2 | 6.2E3 | 1.2E3 | 897 | 8 | 335 | 8 | 0.75 |
| In | ng/ml | 3.7E0 | 7.8E-1 | 2.7E1 | 8.6E0 | 2.1E2 | 2.2E1 | 1.0E-9 | 3.1E-2 | 4.5E3 | 6.8E1 | 904 | 9 | 336 | 9 | 0.31 |
| Io | ng/ml | 8.1E3 | 8.4E3 | 2.4E4 | 7.8E4 | 1.5E5 | 1.9E5 | 1.0E-9 | 5.9E3 | 4.0E6 | 5.5E5 | 896 | 8 | 336 | 8 | 0.59 |
| Ip | ng/ml | 9.7E0 | 3.0E1 | 1.9E1 | 3.8E1 | 2.4E1 | 4.7E1 | 1.0E-9 | 5.6E-3 | 2.6E2 | 1.4E2 | 896 | 8 | 336 | 8 | 0.57 |
| Iq | ug/ml | 1.0E-1 | 2.6E-1 | 3.2E1 | 9.5E1 | 6.4E2 | 2.7E2 | 1.0E-9 | 1.0E-9 | 1.4E4 | 7.5E2 | 896 | 8 | 336 | 8 | 0.55 |
| Ir | ug/ml | 3.5E-1 | 2.8E0 | 3.9E0 | 1.9E1 | 2.8E1 | 3.9E1 | 1.0E-9 | 1.9E-1 | 5.1E2 | 1.1E2 | 895 | 8 | 336 | 8 | 0.82 |
| Is | ng/ml | 1.5E0 | 1.6E1 | 6.6E0 | 5.3E1 | 2.3E1 | 8.0E1 | 1.0E-9 | 3.1E0 | 5.5E2 | 2.3E2 | 896 | 8 | 336 | 8 | 0.88 |
| It | ng/ml | 2.0E0 | 1.8E0 | 2.4E1 | 7.9E1 | 1.4E2 | 2.1E2 | 1.0E-9 | 1.0E-9 | 2.8E3 | 5.9E2 | 896 | 8 | 336 | 8 | 0.55 |
| Iu | ng/ml | 2.2E2 | 2.6E2 | 1.4E3 | 3.6E3 | 4.2E3 | 8.4E3 | 1.0E-9 | 1.0E-9 | 2.9E4 | 2.4E4 | 896 | 8 | 336 | 8 | 0.48 |
| Iv | ng/ml | 1.3E1 | 4.1E1 | 6.1E1 | 8.5E2 | 5.5E2 | 2.3E3 | 1.0E-9 | 3.3E0 | 1.6E4 | 6.4E3 | 895 | 8 | 336 | 8 | 0.70 |
| Pz | ng/ml | 3.9E3 | 4.7E3 | 8.3E3 | 6.4E3 | 3.8E4 | 4.8E3 | 1.3E1 | 2.6E2 | 1.0E6 | 1.4E4 | 896 | 9 | 334 | 9 | 0.59 |
| Qa | ng/ml | 3.5E3 | 1.4E4 | 6.5E3 | 1.3E4 | 1.0E4 | 7.4E3 | 1.2E1 | 2.5E3 | 2.2E5 | 2.5E4 | 896 | 9 | 334 | 9 | 0.78 |
| Qb | ng/ml | 9.7E1 | 2.9E2 | 2.1E2 | 3.8E2 | 4.9E2 | 2.8E2 | 7.9E-1 | 8.6E1 | 8.3E3 | 9.1E2 | 896 | 9 | 334 | 9 | 0.77 |
| Qc | ng/ml | 2.3E2 | 4.1E2 | 6.3E2 | 6.3E2 | 5.6E3 | 7.4E2 | 1.0E-9 | 3.8E1 | 1.7E5 | 2.4E3 | 896 | 9 | 334 | 9 | 0.62 |
| Qd | ng/ml | 9.2E3 | 1.1E4 | 1.9E4 | 4.2E4 | 7.3E4 | 6.0E4 | 1.5E2 | 7.9E3 | 2.0E6 | 1.7E5 | 896 | 9 | 334 | 9 | 0.66 |
| Qe | ng/ml | 9.2E2 | 2.3E3 | 1.9E3 | 4.4E3 | 4.7E3 | 4.2E3 | 1.0E-9 | 8.7E2 | 9.7E4 | 1.4E4 | 896 | 9 | 334 | 9 | 0.80 |
| Jg | ng/ml | 5.0E2 | 1.6E3 | 8.3E2 | 2.3E3 | 1.0E3 | 1.8E3 | 1.0E-9 | 2.2E2 | 1.0E4 | 5.4E3 | 900 | 9 | 336 | 9 | 0.79 |
| Jh | ng/ml | 3.0E0 | 2.4E1 | 2.9E1 | 5.6E1 | 1.2E2 | 6.9E1 | 1.0E-9 | 1.0E-9 | 1.6E3 | 2.1E2 | 900 | 9 | 336 | 9 | 0.71 |
| Ji | ng/ml | 5.3E1 | 1.9E2 | 7.9E1 | 2.4E2 | 9.0E1 | 1.7E2 | 1.0E-9 | 5.5E1 | 1.3E3 | 5.9E2 | 900 | 9 | 336 | 9 | 0.86 |
| Jj | ng/ml | 6.1E2 | 8.7E1 | 1.6E3 | 1.8E2 | 1.2E4 | 2.7E2 | 1.5E0 | 1.7E1 | 3.4E5 | 8.7E2 | 900 | 9 | 336 | 9 | 0.14 |
| Jk | ng/ml | 3.0E0 | 4.5E0 | 2.1E1 | 3.6E1 | 4.7E1 | 5.7E1 | 1.0E-9 | 2.2E0 | 3.9E2 | 1.7E2 | 900 | 9 | 336 | 9 | 0.67 |
| Jl | ng/ml | 4.1E-1 | 2.0E1 | 2.6E0 | 2.8E1 | 1.9E1 | 4.9E1 | 7.6E-4 | 9.5E-1 | 5.4E2 | 1.6E2 | 900 | 9 | 336 | 9 | 0.90 |
| Jm | ng/ml | 1.8E1 | 1.5E1 | 5.8E1 | 1.9E1 | 1.3E2 | 1.8E1 | 1.0E-9 | 6.7E-1 | 2.1E3 | 5.1E1 | 900 | 9 | 336 | 9 | 0.41 |
| Jn | pg/ml | 4.0E-1 | 2.0E0 | 3.7E0 | 3.6E0 | 3.8E1 | 3.2E0 | 1.0E-9 | 2.8E-2 | 7.3E2 | 8.9E0 | 899 | 9 | 336 | 9 | 0.80 |
| Jo | pg/ml | 3.6E3 | 1.5E3 | 4.9E3 | 5.7E3 | 5.0E3 | 1.2E4 | 2.0E1 | 7.5E1 | 1.0E5 | 3.8E4 | 900 | 9 | 336 | 9 | 0.29 |
| Jp | pg/ml | 7.0E4 | 1.1E5 | 7.3E4 | 1.3E5 | 3.8E4 | 4.2E4 | 5.8E2 | 8.0E4 | 3.8E5 | 2.2E5 | 900 | 9 | 336 | 9 | 0.86 |
| Jq | pg/ml | 9.6E1 | 6.1E1 | 1.6E2 | 6.2E2 | 3.6E2 | 1.3E3 | 1.0E0 | 3.1E1 | 8.7E3 | 4.1E3 | 900 | 9 | 336 | 9 | 0.53 |
| Jr | pg/ml | 5.3E0 | 4.0E1 | 4.4E1 | 6.2E1 | 4.7E2 | 6.9E1 | 1.0E-9 | 7.7E-1 | 1.1E4 | 1.9E2 | 900 | 9 | 336 | 9 | 0.82 |
| Js | pg/ml | 1.3E1 | 1.9E1 | 5.3E1 | 2.9E1 | 3.8E2 | 2.8E1 | 1.0E-9 | 3.5E0 | 1.0E4 | 9.4E1 | 900 | 9 | 336 | 9 | 0.62 |
| Jt | pg/ml | 2.6E2 | 2.3E3 | 3.2E3 | 5.7E3 | 2.8E3 | 1.0E4 | 2.2E1 | 6.4E2 | 5.2E4 | 3.3E4 | 900 | 9 | 336 | 9 | 0.47 |
| Lh | pg/ml | 1.3E1 | 3.4E4 | 2.2E4 | 9.2E4 | 3.2E4 | 1.3E5 | 1.0E-9 | 5.5E3 | 4.8E5 | 4.1E5 | 900 | 9 | 337 | 9 | 0.79 |
| Li | pg/ml | 3.3E3 | 1.1E4 | 1.7E4 | 8.5E4 | 6.2E4 | 1.9E5 | 1.0E-9 | 3.6E1 | 1.3E6 | 5.9E5 | 900 | 9 | 337 | 9 | 0.64 |
| Lj | pg/ml | 2.8E3 | 8.3E3 | 2.3E4 | 5.9E4 | 6.6E4 | 1.1E5 | 1.0E-9 | 1.0E2 | 5.2E5 | 3.5E5 | 900 | 9 | 337 | 9 | 0.64 |
| Nv | pg/ml | 4.0E3 | 1.4E4 | 1.1E4 | 2.7E4 | 4.3E4 | 3.1E4 | 1.0E-9 | 2.6E3 | 1.1E6 | 8.4E4 | 906 | 9 | 337 | 9 | 0.82 |
| Nw | pg/ml | 8.9E3 | 3.5E4 | 1.3E4 | 5.7E4 | 1.7E4 | 6.0E4 | 8.6E1 | 9.1E3 | 2.1E5 | 1.7E5 | 906 | 9 | 337 | 9 | 0.87 |
| Nx | pg/ml | 2.2E2 | 4.7E2 | 4.1E2 | 7.4E2 | 6.5E2 | 8.1E2 | 1.0E-9 | 1.0E-9 | 7.4E3 | 2.2E3 | 906 | 9 | 337 | 9 | 0.65 |
| Ny | pg/ml | 6.4E0 | 2.3E1 | 5.7E1 | 1.3E2 | 8.5E2 | 2.2E2 | 1.0E-9 | 1.0E-9 | 2.5E4 | 6.2E2 | 906 | 9 | 337 | 9 | 0.72 |
| Oe | pg/ml | 6.8E1 | 1.0E-9 | 2.9E2 | 3.7E2 | 7.5E2 | 5.5E2 | 1.0E-9 | 1.0E-9 | 1.9E4 | 1.6E3 | 897 | 9 | 336 | 9 | 0.49 |
| Of | pg/ml | 1.7E2 | 9.1E1 | 6.1E3 | 8.5E3 | 2.8E4 | 2.4E4 | 1.0E-9 | 7.2E0 | 6.2E5 | 7.4E4 | 905 | 9 | 337 | 9 | 0.47 |
| Og | pg/ml | 8.2E-5 | 5.6E-2 | 4.8E-1 | 9.8E-2 | 1.6E0 | 1.1E-1 | 1.0E-9 | 1.0E-9 | 2.0E1 | 2.7E-1 | 905 | 9 | 337 | 9 | 0.41 |
| Oh | pg/ml | 2.7E0 | 1.0E1 | 2.0E1 | 4.8E1 | 1.5E2 | 7.8E1 | 1.0E-9 | 9.0E-2 | 3.5E3 | 2.2E2 | 905 | 9 | 337 | 9 | 0.74 |
| Oi | pg/ml | 2.6E0 | 5.1E0 | 6.3E0 | 4.3E0 | 9.8E0 | 4.1E0 | 1.0E-9 | 1.0E-9 | 8.6E1 | 1.1E1 | 905 | 9 | 337 | 9 | 0.52 |
| Ok | pg/ml | 3.9E2 | 9.8E2 | 5.6E2 | 1.9E3 | 6.0E2 | 3.0E3 | 1.3E1 | 4.5E2 | 7.8E3 | 9.8E3 | 905 | 9 | 337 | 9 | 0.81 |
| Om | pg/ml | 4.0E2 | 8.0E2 | 8.9E2 | 5.2E3 | 2.7E3 | 7.6E3 | 1.0E-9 | 2.0E2 | 5.1E4 | 2.0E4 | 905 | 9 | 337 | 9 | 0.75 |

Figure 10 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| On | pg/ml | 1.8E2 | 5.3E2 | 3.0E2 | 2.4E3 | 4.2E2 | 4.8E3 | 1.0E-9 | 1.5E2 | 4.5E3 | 1.5E4 | 905 | 9 | 337 | 9 | 0.84 |
| Oy | pg/ml | 4.9E-1 | 3.3E-1 | 5.7E0 | 3.0E1 | 2.9E1 | 9.0E1 | 1.0E-9 | 1.0E-9 | 4.0E2 | 2.7E2 | 904 | 9 | 336 | 9 | 0.42 |
| Oz | pg/ml | 3.1E-3 | 1.1E-1 | 3.1E-1 | 2.1E-1 | 1.3E0 | 2.8E-1 | 1.0E-9 | 1.0E-9 | 2.9E1 | 6.9E-1 | 904 | 9 | 336 | 9 | 0.52 |
| Pa | pg/ml | 3.9E-1 | 1.5E0 | 1.6E0 | 3.6E1 | 6.1E0 | 9.6E1 | 1.0E-9 | 1.7E-1 | 1.0E2 | 2.9E2 | 904 | 9 | 336 | 9 | 0.79 |
| Pb | pg/ml | 1.0E-9 | 6.9E-2 | 8.0E-1 | 2.0E1 | 1.6E1 | 6.0E1 | 1.0E-9 | 1.0E-9 | 4.9E2 | 1.8E2 | 904 | 9 | 336 | 9 | 0.59 |
| Pc | pg/ml | 4.4E-2 | 1.0E0 | 3.6E-1 | 2.4E0 | 8.8E-1 | 3.9E0 | 1.0E-9 | 1.0E-9 | 1.6E1 | 1.1E1 | 904 | 9 | 336 | 9 | 0.68 |
| Pd | pg/ml | 1.9E0 | 2.5E0 | 5.1E0 | 4.0E0 | 2.9E1 | 5.4E0 | 1.0E-9 | 1.0E-9 | 8.4E2 | 1.8E1 | 904 | 9 | 336 | 9 | 0.56 |
| Pe | pg/ml | 2.2E1 | 9.4E1 | 1.2E2 | 1.7E3 | 4.4E2 | 4.7E3 | 1.0E-9 | 1.4E1 | 6.7E3 | 1.4E4 | 904 | 9 | 336 | 9 | 0.75 |
| Pf | pg/ml | 1.6E0 | 1.3E1 | 1.1E1 | 3.6E1 | 6.0E1 | 7.4E1 | 1.0E-9 | 2.8E-1 | 1.5E3 | 2.3E2 | 904 | 9 | 336 | 9 | 0.73 |
| Pg | pg/ml | 3.4E0 | 8.7E0 | 4.3E1 | 2.3E2 | 3.4E2 | 6.2E2 | 1.0E-9 | 1.7E0 | 7.7E3 | 1.9E3 | 904 | 9 | 336 | 9 | 0.68 |
| aA | mg/dL | 8.0E-1 | 1.8E0 | 9.4E-1 | 2.2E0 | 4.9E-1 | 1.4E0 | 2.0E-1 | 6.0E-1 | 4.2E0 | 5.4E0 | 2667 | 20 | 507 | 20 | 0.85 |

Analyte panel data:

Unconstrained panels with 3 analytes, where 1.0E-8 >= 'model p-value' > 0. Contains 376 panels of 287,980 total panels evaluated. : aA{Iu(Et Fp Fr Hq Hr Hu Hv Hw Hx Ih Ii In Io Ip Iq Ir Is It Iv Jg Jh Ji Jj Jk Jl Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Lx(Et Fp Hq Hu Hv Hx Ih In Io Ip Iq Ir Is It Iv Jj Jk Jm Jn Jo Jq Jr Js Jt Li Lz Mf Mj Mk Mn Mp Mr Mt Mx Ne Nf Ng Ni Nk Nl No Nq Nr Nt Ny Oz Pc Pd Pf Po Qd) Jj(Fr Ii Io Ip Iq Ir Is It Iv Jg Ji Jl Jm Jn Jr Js Lh Lv Mf Mg Mi Mn Mt Mv Mx Mz Ni Nj Nk Nm Nv Nw Og Oi Oz Pa Pc Qb Qc) Jl(Ih In Io Ip Iq Ir Is It Iv Jk Jo Js Jt Mj Mt Mx Ng Ni Nk Nr Pd Qd) Nw(Ip Iq Ir Js Mt Mx Qd) Ir(Ji Js Lw Mx Mz) Mx(Is Ji Ok) Ng(Fr Jg Pc) Js(Is Ji Mi) Iq(Fr Mz) MiMj IsJt JiJq} Jj{Is(Fr Ii Iu Jg Jl Js Lh Lu Lx Mf Mi Mk Ml Mr Mt Mx Nd Nn Nv On Pa Pc) Iu(Fr Jl Lh Lx Mi Mt Mz Nn Nv Nw On Pa) Iv(Fr Jl Lh Lx Mi Mt Nd Nn Nv Nw On Pa) Jl(Ii Io Ip Iq Ir It Lh Mm Mx Pa) Io(Fr Lh Lx Mi Mt Nv On Pa) Ir(Fr Lh Lx Mi Nd On Pa) It(Fr Lx Mi Nn On Pa) Ip(Lh Lx Mi Nv On) Mt(Mk Mr Pa) Iq(Lx Mi Pa) Mf(Lh Lx)} Iu{Lx(Ir Is Jl Jm Li Mg Mi Ni Nk Pd Po) Jl(Fr Is Ji Jp Lh Nk Nw Pa Pe) Fr(Ir Is Jr) MtNw NgOn JoLh} Lx{Mi(Hq Ih Pd) Po(Jm Nk) NrJl NgJg} MiNgJg Unconstrained panels with 3 analytes, where 1.0E-7 >= 'model p-value' > 1.0E-8. Contains 2,528 panels of 287,980 total panels evaluated. : aA{Iq(Et Fp Hq Hr Hu Hv Hw Hx Ih Ii In Io Ip Ir Is It Iv Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Is(Et Fp Fr Hq Hr Hu Hv Hw Hx Ih Ii In Io Ip Ir It Iv Jg Jh Ji Jk Jm Jn Jo Jp Jq Jr Lh Li Lj Lu Lv Lw Ly Lz Ma Mb Mc Md Me Mf Mg Mh Mi Mj Mk Ml Mm Mn Mp Mq Mr Ms Mt Mu Mv Mw My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ir(Et Fp Fr Hq Hr Hu Hv Hw Hx Ih Ii In Ip It Iv Jg Jh Jk Jm Jn Jo Jp Jq Jr Js Jt Lh Lj Lv Lw Ma Md Me Mf Mg Mi Mj Mk Ml Mm Mn Mp Mq Mr Ms Mt Mv Mw Mx My Na Nb Nc Nd Ne Nf Ng Nh Ni Nj Nk Nl Nm Nn No Nq Nr Ns Nt Nu Nv Nw Ny Of Og Oh Oi Ok Om On Oy Oz Pa Pb Pc Pd Pe Pf Pg Po Qa Qb Qc Qd Qe) Jl(Et Fp Fr Hq Hr Hu Hv Hw Hx Ii Jg Jh Ji Jm Jn Jp Jq Jr Lh Li Lj Lu Lv Lw Lx Ly Lz Ma Mb Mc Md Me Mf Mg Mh Mi Mk Ml Mm Mn Mp Mq Mr Ms Mu Mv Mw My Mz Na Nb Nc Nd Ne Nf Nh Nj Nl Nm Nn No Nq Ns Nt Nu Nv Nw Nx Ny Oe Of Og Oh Oi Ok Om On Oy Oz Pa Pb Pc Pe Pf Pg Po Pz Qa Qb Qc Qe) Ni(Et Fp Fr Hr Hu Hv Hw Hx Ih In Io Ip It Iv Jg Jh Ji Jk Jm Jn Jo Jp Jq Jr Js Jt Lh Lj Lv Lw Ma Md Me Mf Mg Mi Mj Mk Ml Mm Mn Mp Mq Mr Ms Mt Mv Mw Mx Mz Na Nc Nd Ne Nf Ng Nj Nk Nl Nm Nn No Nq Nr Ns Nu Nv Nw Ny Of Og Oh Oi Ok Om On Oz Pa Pb Pc Pd Pe Pf Pg Po Qa Qb Qc Qd Qe) Jj(Et Fp Hq Hr Hu Hv Hx Ih In Jh Jk Jo Jp Jq Jt Li Lj Lu Lw Ly Lz Ma Mb Mc Md Me Mh Mj Mk Ml Mm Mp Mq Mr Ms Mu Mw My Na Nb Nc Nd Ne Nf Ng Nh Nl Nn No Nq Nr Ns Nt Nu Nv Ny Oe Of Oh Ok Om On Oy Pb Pd Pe Pf Pg Po Pz Qa Qd Qe) Mt(Fp Fr Hq Hu Hv Ih In Io Ip It Iv Jg Jh Ji Jk Jm Jn Jo Jp Jq Jr Js Jt Li Lj Lw Lz Me Mf Mg Mi Mj Mk Ml Mn Mp Mr Ms Mv Mx My Mz Na Nd Ne Nf Ng Nh Nj Nk Nl Nn Nq Nr Nt Nu Ny Of Og Oh Oi Ok On Oz Pa Pc Pd Pf Qa Qd Qe) Lx(Fr Hr Hw Hx Ii Jg Jh Ji Jp Lh Lj Lu Lv Lw Ly Ma Mb Mc Md Me Mg Mh Mi Ml Mm Mq Ms Mu Mv Mw My Mz Na Nb Nc Nd Nh Nj Nm Nn Ns Nu Nv Nw Nx Oe Of Og Oh Oi Ok Om On Oy Pa Pb Pe Pg Pz Qa Qb Qc Qe) Nw(Et Fp Fr Hr Hu Hv Ih In Io It Iv Jh Ji Jk Jm Jn Jo Jq Jr Jt Li Lj Lw Lz Md Me Mf Mh Mj Mk Ml Mn Mp Mr Ms Mv Mz Nd Ne Nf Ng Nj Nk Nl No Nq Nr Nv Ny Of Og Oh Oi Oz Pa Pc Pd Pf Po Qa Qc) Nk(Fr Hu Hx Ih In Io Ip It Iv Jg Jh Ji Jn Jo Jp Jq Jr Js Jt Lh Lv Lw Ma Me Mf Mi Mj Ml Mn Mp Ms Mx Mz Na Nc Nd Nf Ng Nl Nn Nv Og Oh Oi Ok On Oz Pa Pb Pc Pd Pf Qa Qb Qd Qe) Ip(Fr Hu Hx Ih In Jg Ji Jm Jn Jo Jp Jr Js Jt Lh Lv Lw Ly Ma Me Mf Mi Mj Mk Mn Mr Ms Mx Mz Nd Ne Nf Ng Nj Nn Nv Og Ok Om On Oz Pa Pb Pc Pd Pf Qa Qb Qc Qe) Iv(Fr Hu Hv Hx Ih In Jg Ji Jk Jm Jn Jo Jq Jr Js Jt Lw Ly Ma Me Mf Mg Mi Mj Mk Ml Mm Mr Ms Mx Mz Nd Ne Nf Ng Nj Nl Nn Nv Og Oi Ok On Oz Pa Pb Pc Pd Qc Qd) Ng(Et Hx Ih Io It Ji Jn Jp Jq Jr Js Lh Lv Lw Ma Me Mf Mg Mi Mj Ml Mm Mn Mp Mv Mx Mz Nd Ne Nf Nm Nn Nv Of Og Oi Ok Om On Oz Pa Pd Pf Qd Qe) It(Fr Hu Hx Ih In Jg Ji Jm Jn Jo Jr Js Jt Lh Lv Lw Ly Ma Mf Mi Mj Mk Mn Mq Ms Mx Mz Nd Ne Nf Nj Nn Nv Og Ok Om On Oz Pa Pb Pc Pd Qb Qc) Mx(Et Fr Hu Hx Ih Io Jg Jn Jo Jp Jr Lh Lj Lv Lw Ma Me Mi Ml Mn Mq Ms Mz Nd Ne Nm Nn Nv Og Oh Om On Oz Pa Pc Pe Pf Po Qa Qb Qe) Fr(Hu Ih In Io Jh Jk Jm Jn Jo Jq Jr Js Jt Li Mf Mj Ml Mn Ms Mv Mw My Mz Nb Nf Nq Nr Ny Of Og Nd Ne Nf Nj Nq Nr Ny Og Oz Pc Pd Qd) Pc(Hr Hu Hv Ih In Io Jh Jk Jn Jo Jr Js Jt Mf Mj Ml Mn Ms Mv Mw My Mz Nb Nf Nq Nr Ny Of Og Oi Oy Oz Pd Pf) Io(Hu Ih In Jg Ji Jn Jo Jr Js Jt Lw Ma Mf Mi Mj Mk Mn Ms Mz Nd Ne Nf Nj Nn Nv Og On Pa Pb Pd Qc) Jo(Hx Jg Ji Jn Jp Jr Lh Lv Lw Ma Mg Mi Mz Nd Nm Nn Nv Og Ok Om On Pa Pe Pf Pg Qa Qb) Js(Hx Jg Jn Jp Jr Lh Lv Lw Ma Ms Mz Nd Nn Nv Og Oh Ok Om On Pa Pe Pf Qa Qb Qe) Ji(Hv Ih In Jn Jr Jt Me Mf Mj Ml Mn Mz Ne Nf Nr Ny Og Oz Pd Qd) In(Hw Hx Jg Jr Lh Lv Lw Mi Mk Mz Nd Nv Ok On Pa Pb) Jt(Jg Jn Jp Jr Lh Lw Ma Mz Nm Nn Nv Ok Om On Pa Qa) Pd(Jg Jn Jr Lh Lw Mi Mz Nd Nn Nv Og Ok On Pa Pe Pf) Jr(Ih Jn Lw Mf Mj Mn Mz Nf Nr Ok Oz Qd) Lw(Hr Hv Jn Me Mf Ml Na Nf Ny Of) Jg(Hu Ih Jh Jk Mn Mv My Nf Nq Nr) Mz(Ih Jn Jq Mj Mn Nf Nr Oz Qd) On(Hr Jn Jq Mj Mn Nf Nr) Mn(Jp Ma Nd Nn Pa) Nf(Jn Mi Ok Pa) Nq(Mi Mu Nd) Nr(Lh Nv Pa) Mj(Lh Nv Pa) Lv(Me Mf) Nd(Hq Hu) Jq(Ok Om) MiHq MuHu NePa Imlu JnOk OgOz} Jj{Jl(Et Fp Fr Hq Hr Hu Hv Hw Hx Ih Ii In Jg Jh Ji Jk Jm Jn Jo Jp Jq Jr Js Jt Li Lj Lu Lv Lw Lx Ly Lz Ma Mb Mc Md Me Mf Mg Mh Mi Mj Mk Ml Mn Mp Mq Mr Ms Mt Mu Mv Mw My Mz Na Nb Nc Nd Ne Nf Ng Nh Ni Nj Nk Nl Nm Nn

Figure 10 Continued

No Nq Nr Ns Nt Nu Nv Nw Nx Ny Oe Of Og Oh Oi Ok Om On Oy Oz Pb Pc Pd Pe Pf Pg Po Pz Qa Qb Qc Qd Qe) Is(Et Fp Hq Hr Hu Hv Hw Hx Ih In Io Ip Iq Ir It Iv Jh Ji Jk Jm Jn Jo Jp Jq Jr Jt Li Lj Lv Lw Ly Lz Ma Mb Mc Md Me Mg Mh Mj Mm Mn Mp Mq Ms Mu Mv Mw My Mz Na Nb Nc Ne Nf Ng Nh Ni Nj Nk Nl Nm No Nq Nr Ns Nt Nu Nv Nw Nx Ny Oe Of Og Oh Oi Ok Om Oy Oz Pb Pd Pe Pf Pg Po Pz Qa Qb Qc Qd Qe) Lx(Et Fp Fr Hu Hx Ih Ii In Jg Ji Jm Jn Jo Jp Jq Jr Js Jt Lh Li Lu Lv Lw Mb Mc Mg Mh Mi Mj Mk Ml Mm Mn Mp Mq Mr Ms Mt Mv Mx My Mz Nb Nd Ne Ng Ni Nj Nk Nn Nq Nr Nt Nw Ny Oe Og Oi Ok Om On Oy Pa Pc Pd Pe Po Pz Qb Qc Qd) Lh(Et Fp Fr Hr Hu Hv Hx Ih In Iq It Jg Jh Jm Jn Jo Jp Jq Jr Js Jt Li Lv Md Me Mg Mi Mj Mk Ml Mm Mn Mq Mr Ms Mt Mv Mx Mz Na Nd Ne Ng Ni Nj Nk Nm Nn Nq Nr Nw Nx Ny Og Oi On Oz Pa Pc Pd Pe Pz Qa Qb Qd) Mt(Fr Hx Ii In Ip Iq Ir It Jk Jp Jr Js Lu Lv Mf Mi Mj Ml Mm Mn Mv Mx Mz Nb Nd Ne Ni Nk Nr Nv Nw Ny Ok On Oy Pc Pe Pg Po) Ir(Hx Ii Iu Iv Jg Ji Jk Jn Jp Jr Js Lu Ma Mf Mk Ml Mn Mr Mu Mv Mz Nb Nk Nn Nr Nv Nw Om Oy Pb Pc Pe Pg Po) Iv(Hx Ii In Jg Ji Jk Jp Jr Ma Mk Mn Mr Mu Mv Mz No Nr Om Pc Pe Qb Qc Qe) Pa(Fr Ip Jg Ji Jr Js Lv Mf Mi Ml Mv Mx Mz Ni Nk Nn Nv Nw On Pc) Iu(Hx Jg Ji Jk Jp Jr Ma Mn Mu Mv Nd No Ok Om Pe Qa Qb Qe) Nw(Io Ip Iq It Jr Js Mf Mi Mk Ml Mm Mn Mr Mx Nd) Io(Hx Ii Jg Ji Jk Jr Mv Mz Nd Nn Om Pc) On(Et Iq Jr Jt Mf Mi Mm Mn Ni) It(Hx Jg Jk Jr Mz Nd Nv Pc) Ip(Fr Hx Jk Jr Mz Nd Nn) Iq(Fr Mz Nn Nv) Jr(Fr Mi Mk Mr) Mi(Hq In) FrMm MfJi NgJg} Iu{Jl(Et Fp Hq Hr Hu Hv Hw Hx Ih Ii Ij Ik Il In Io Ip Iq Ir It Iv Jg Jh Jk Jm Jn Jo Jq Jr Js Jt Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nl Nm Nn No Nq Nr Ns Nt Nu Nv Nx Ny Oe Of Og Oh Oi Ok Om On Oy Oz Pb Pc Pd Pf Pg Po Pz Qa Qb Qc Qd Qe) Lx(Et Fp Fr Hq Hr Hu Hv Hw Hx Ih Ii In Io Ip Iq It Iv Jg Jh Ji Jk Jn Jo Jp Jq Jr Js Jt Lh Lj Lu Lv Lw Ly Lz Ma Mb Mc Md Me Mf Mh Mj Mk Ml Mm Mn Mp Mq Mr Ms Mt Mu Mv Mw Mx My Mz Na Nb Nc Nd Ne Nf Ng Nh Nj Nl Nm Nn No Nq Nr Ns Nt Nu Nv Nw Nx Ny Oe Of Og Oh Oi Ok Om On Oy Oz Pa Pb Pc Pe Pf Pg Pz Qa Qb Qc Qd Qe) Nw(Fr Hu Hw In Ir Is Iv Jh Ji Jm Jn Jo Jq Jr Js Jt Lh Lu Lv Ly Ma Md Mf Mg Mi Mj Mk Ml Mr Ms Mv Mw Mx My Mz Nd Ng Ni Nk Nq Nr Nv Nx Ny Of Og Oi Ok On Pa Pd Pe Pf Pz Qa Qb Qe) Is(Ji Jm Jp Js Lh Lu Ma Mi Mk Mr Mt Mv Mz Ni Nk Nn Og On Pa Pe) Fr(Hu Hx Ji Jn Lh Mg Mi Mk Mr Mz Ng Nk Nr On Pa Pe Qb) On(Hu Ir Jm Jo Jr Jt Mg Mi Ms My Mz Ni Nk Og Pa) Mi(Hq In Ji Lh Mt Qe) Lh(In Mg Ng) Ji(Nx Pa)} Lx{Nr(Fr Hu Hx In Is Jg Ji Jm Jn Jr Js Lh Li Lu Lv Lw Mf Mg Mi Mj Mk Mm Mn Mp Mr Ms Mt Mv Nb Nd Ne Ng Ni Nj Nk Nw Oi Ok On Pa Pc Pd Pe Po) Jm(Fp Hx Io Ip Iq Ir Is It Iv Jl Jo Jr Js Jt Li Lu Lv Mf Mi Ml Mn Mt Mx Nd Ne Ng Ni Nj Nk Nn On Pa Pc Pd) Po(Hq Hu In Io Ip Iq Ir Is It Iv Jl Jo Jr Js Li Mf Mg Mi Mn Ne Ng Ni Nq Nt Pc Pd) Nk(Hu In Ip Is Jl Jo Jr Js Jt Li Mf Mg Mi Ml Mn Mr Ms My Nc Nd Ng Nq Og Pd) In(Hw Hx Ir Is Iv Jl Li Mk Mr Mt Ni On Pa Pb Pd Pf) Pd(Is Jl Lh Li Mf Mk Mn Mr Nd Ni On Pa Pe) Li(Hq Ir Is Jl Js Mg Mr Ng Ni Nq On) Ng(Fr Jl Mf Mi Mk Ni On Pc) Jo(Hw Mi Mk Mr On Pa) Js(Is Jl Mi Nw) Jt(Is Jl On) NqMi MfNi MkOy} Ng{Jg(Fr Hx Ii Is Ji Jk Jl Jp Jr Lh Lu Mk Mm Mr Mt Mz Nd Nk Nr Nv Nw Om On Oy Pa Pb Pc Pe Pg) Fr(Hx Ii Is Mi Mk Mr Nb On Pa Pb Pc) On(Ip Js Jt Mf Mi Mn Mt Mx Ni Nk) Jl(Mi Nk Pa Pc) Miln MtPc} Mi{In(Hx Ir Is Ji Jl Jn Jr Lh Mt Mz Nq Nw On Qa Qe) Hq(Fr Is Ji Jl Jn Jr Mt Mx Nd Nq Nw) Js(Is Ji Jl Jn Nw) Nq(Fr Jl) Is(Jm Jo) NrJl JoLh NwPd} Jl{Nr(Jp Nk Nw Pa Pe) In(Hw Iv Mr Pa) Jo(Ii Mr Pa Pe) Nk(Jp Mx Pa) Is(Jm Jt) JpJt} Is{Jo(Fr Lh Mr On Pa) Jm(Fr Nd Nw Pa) Fr(Jt Mg) MzJs JtOn} Jo{Lh(Iv Mr Pa) MrNw MxOn} On{Jt(Ir Iv) MxOf}

Unconstrained panels with 3 analytes, where 1.0E-6 >= 'model p-value' > 1.0E-7. Contains 9,435 panels of 287,980 total panels evaluated. :
aA{Pz(Et Fp Fr Hq Hr Hu Hv Hw Hx Ih Ii In Io Ip Ir It Iv Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Qa Qb Qc Qd Qe) Oe(Et Fp Fr Hq Hr Hu Hv Hw Hx Ih Ii In Io Ip Ir It Iv Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Og Oh Oi Ok Om On Oy Oz Pa Pb Pc Pd Pe Pf Pg Po Qa Qb Qc Qd Qe) Lu(Et Fp Fr Hq Hr Hu Hv Hw Hx Ih Ii In Io Ip It Iv Jg Jh Ji Jk Jm Jn Jo Jp Jq Jr Js Jt Lh Li Lj Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Og Oh Oi Ok Om On Oy Oz Pa Pb Pc Pd Pe Pf Pg Po Qa Qb Qc Qd Qe) Mb(Et Fp Fr Hq Hr Hu Hv Hw Hx Ih Ii In Io Ip It Iv Jg Jh Ji Jk Jm Jn Jo Jp Jq Jr Js Jt Lh Li Lj Lv Lw Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Og Oh Oi Ok Om On Oy Oz Pa Pb Pc Pd Pe Pf Pg Po Qa Qb Qc Qd Qe) Mc(Et Fp Fr Hq Hr Hu Hv Hw Hx Ih Ii In Io Ip It Iv Jg Jh Ji Jk Jm Jn Jo Jp Jq Jr Js Jt Lh Li Lj Lv Lw Ly Lz Ma Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Og Oh Oi Ok Om On Oy Oz Pa Pb Pc Pd Pe Pf Pg Po Qa Qb Qc Qd Qe) Ii(Et Fp Fr Hq Hr Hu Hv Hw Hx Ih In Io Ip It Iv Jg Jh Ji Jk Jm Jn Jo Jp Jq Jr Js Jt Lh Li Lj Lv Lw Ly Lz Ma Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Og Oh Oi Ok Om On Oy Oz Pa Pb Pc Pd Pe Pf Pg Po Qa Qb Qc Qd Qe) Nx(Et Fp Fr Hq Hr Hu Hv Hw Hx Ih In Io Ip It Iv Jg Jh Ji Jk Jm Jn Jo Jp Jq Jr Js Jt Lh Li Lj Lv Lw Ly Lz Ma Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Ny Of Og Oh Oi Ok Om On Oy Oz Pa Pb Pc Pd Pe Pf Pg Po Qa Qb Qc Qd Qe) Ns(Et Fp Fr Hq Hr Hu Hv Hw Hx Ih In Io Ip It Iv Jg Jh Ji Jk Jm Jn Jo Jp Jq Jr Js Jt Lh Li Lj Lv Lw Ly Lz Ma Md Me Mf Mg Mh Mi Mj Mk Ml Mm Mn Mp Mq Mr Ms Mt Mu Mv Mw Mx My Mz Na Nb Nc Nd Ne Nf Ng Nh Nj Nk Nl Nm Nn No Nq Nr Nt Nu Nv Nw Ny Of Og Oh Oi Ok Om On Oy Oz Pa Pb Pc Pd Pe Pf Pg Po Qa Qb Qc Qd Qe) Nt(Et Fp Fr Hq Hr Hu Hv Hw Hx Ih In Io Ip It Iv Jg Jh Ji Jk Jm Jn Jo Jp Jq Jr Js Jt Lh Li Lj Lv Lw Ly Lz Ma Md Me Mf Mg Mh Mi Mj Mk Ml Mm Mn Mp Mq Mr Ms Mu Mv Mw Mx My Mz Na Nb Nc Nd Ne Nf Ng Nh Ni Nj Nk Nl Nm Nn No Nq Nr Nu Nv Nw Ny Of Og Oh Oi Ok Om On Oy Oz Pa Pb Pc Pd Pe Pf Pg Po Qa Qb Qc Qd Qe) Mh(Et Fp Fr Hq Hr Hu Hv Hw Hx Ih In Io Ip It Iv Jg Jh Ji Jk Jm Jn Jo Jp Jq Jr Js Jt Lh Li Lj Lv Lw Ly Lz Ma Md Me Mf Mg Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nu Nv Ny Of Og Oh Oi Ok Om On Oy Oz Pa Pb Pc Pd Pe Pf Pg Po Qa Qb Qc Qd Qe) Mw(Et Fp Fr Hq Hr Hu Hv Hw Hx Ih In Io Ip It Iv Jg Jh Ji Jk Jm Jn Jo Jp Jq Jr Js Jt Lh Li Lj Lv Lw Ly Lz Ma Md Me Mf Mg Mi Mj Mk Ml Mm Mn Mp Mq Mr Ms Mt Mu Mv Mx My Mz Na Nb Nc Nd Ne Nf Ng Nh Nj Nk Nl Nm Nn No Nq Nr Nu Nv Nw Ny Of Og Oh Oi Ok Om On Oy Oz Pa Pb Pd Pe Pf Pg Po Qa Qb Qc Qd Qe) Nb(Et Fp Fr Hq Hr Hu Hv Hw Hx Ih In Io Ip It Iv Jg Jh Ji Jk Jm Jn Jo Jp Jq Jr Js Jt Lh Li Lj Lv Lw Ly Lz Ma Md Me Mf Mg Mi Mj Mk Ml Mm Mn Mp Mq Mr Ms Mt Mu Mv Mx My Mz Na Nc Nd Ne Nf Ng Nh Ni Nj Nk Nl Nm Nn No Nq Nr Nu Nv Nw Ny Of Og Oh Oi Ok Om On Oy Oz Pa Pb Pd Pe Pf Pg Po Qa Qb Qc Qd Qe) Nh(Et Fp Fr Hq Hr Hu Hv Hw Hx Ih In Io Ip It Iv Jg Jh Ji Jk Jm Jn Jo Jp Jq Jr Js Jt Lh Li Lj Lv Lw Ly Lz Ma Md Me Mf Mg Mi Mj Mk Ml Mm Mn Mp Mq Mr Ms Mu Mv Mx My Mz Na Nc Nd Ne Nf Ng Ni Nj Nk Nl Nm Nn No Nq Nr Nu Nv Nw Ny Of Og Oh Oi Ok Om On Oy Oz Pa Pb Pc Pd Pe Pf Pg Po Qa Qb Qc Qd Qe) Oy(Et Fp Fr Hq Hr Hu Hv Hw Hx Ih In Io Ip It Iv Jg Jh Ji Jk Jm Jn Jo Jp Jq Jr Js Jt Lh Li Lj Lv Lw Ly Lz Ma Md Me Mf Mg Mi Mj Mk Ml Mm Mn Mp Mq Mr Ms Mt Mu Mv Mx My Mz Na Nc Nd Ne Nf Ng Ni Nj Nk Nl Nm Nn No Nq Nr Nu Nv Nw Ny Of Og Oh Oi Ok Om On Oz Pa Pb Pd Pe Pf Pg Po Qa Qb Qc Qd Qe) No(Et Fp Fr Hq Hr Hu Hv Hw Hx Ih In Io Ip It Iv Jg Jh Ji Jk Jm Jn Jo Jp Jq Jr

Nj Nk Nn Nr Nv Og Ok Om On Oz Pa Pd Pf Qa Qd) Nj(Hu Hx Ih In Jg Ji Jn Jo Jp Jq Jr Js Jt Lh Lv Lw Ma Me Mf Mi Mj Mk Ml Mn Ms Mx
Mz Nd Ne Nf Ng Nk Nn Nr Nv Og Ok Om On Oz Pa Pc Pd Pf Qa Qd) Mk(Hu Hx Ih Jg Ji Jn Jo Jp Jq Jr Js Jt Lh Lv Lw Ma Me Mf Mi Mj Ml
Mn Ms Mx Mz Nd Ne Nf Ng Nk Nn Nr Nv Og Ok Om On Oz Pa Pc Pd Pf Qa Qd) Qa(Fr Hu Hx Ih In Io It Iv Jg Ji Jn Jp Jq Jr Lh Lv Lw Ma Me
Mf Mi Mj Ml Mn Ms Mz Nd Ne Nf Ng Nn Nr Nv Og Ok Om On Oz Pa Pc Pd Pf Qd) Om(Fr Hu Hx Ih In Io Iv Jg Ji Jn Jp Jr Lh Lv Lw Ma Me
Mf Mi Mj Ml Mn Ms Mt Mz Nd Ne Nf Nk Nn Nr Nv Nw Og Ok On Oz Pa Pc Pd Pf Qd) Ml(Fr Hu Hx Ih In Io Ip It Jg Jn Jo Jp Jq Jr Js Jt Lh Lv
Ma Me Mf Mi Mj Mn Ms Mz Nd Ne Nf Nn Nr Nv Og Ok On Oz Pa Pd Pf Qd) Hx(Fr Hu Ih Io Jg Ji Jn Jp Jq Jr Jt Lh Lv Lw Ma Me Mf Mi Mj
Mn Ms Mt Mz Nd Ne Nf Nn Nr Nv Nw Og Ok On Oz Pa Pc Pd Pf Qd) Qd(Hu Ih In Io Ip It Jg Jn Jo Jp Jq Js Jt Lh Lv Lw Ma Me Mf Mi Mj Mn
Ms Mx Nd Ne Nf Nn Nr Nv Og Ok On Oz Pa Pc Pd Pf) Jp(Fr Hu Ih In Io It Iv Jg Ji Jn Jq Jr Lh Lv Lw Ma Me Mf Mi Mj Ms Mz Nd Ne Nf Nn
Nr Nv Nw Og Ok On Oz Pa Pc Pd Pf) Lv(Fr Hu Ih Io Iv Jg Ji Jn Jq Jr Jt Lh Lw Ma Mi Mj Mn Ms Mt Mz Nd Ne Nf Nn Nr Nv Nw Og Ok On
Oz Pa Pc Pd Pf) Mc(Fr Hu Ih In Io It Jg Jn Jo Jq Jr Js Jt Lh Ma Mf Mi Mj Mn Ms Mz Nd Ne Nf Nn Nr Nv Og Ok On Oz Pa Pc Pd Pf) Jq(Hu Ih
In Io Ip It Jg Jn Jo Jr Js Jt Lh Lw Ma Mf Mi Mj Mn Ms Mx Nd Ne Nf Nn Nr Nv Og Oz Pa Pc Pd Pf) Pf(Fr Hu Ih In Io It Iv Jg Ji Jn Jr Jt Lh Lw
Ma Mf Mi Mj Mn Ms Mz Nd Ne Nf Nn Nr Nv Og Ok On Oz Pa) Ma(Fr Hu Ih In Jg Ji Jn Jr Lh Lw Mf Mi Mj Ms Mt Mz Nd Ne Nf Nn Nr Nv
Nw Og Ok On Oz Pa Pc Pd) Ms(Hu Ih In Jg Ji Jn Jo Jr Jt Lh Lw Mf Mi Mj Mn Mz Nd Ne Nf Ng Nn Nr Nv Og Ok On Oz Pa Pd) Ne(Hu Ih In
Jg Jn Jo Jr Js Jt Lh Lw Mf Mi Mj Mn Mz Nd Nf Nk Nn Nr Nv Og Ok On Oz Pc Pd) Nr(Hu Ih In Io Ip It Iv Jn Jo Js Jt Lw Mf Mi Mj Mn Mx Nd
Nf Ng Nk Nn Og Ok Oz Pd) Lh(Fr Hu Ih Io Iv Jg Ji Jn Jr Lw Mf Mi Mn Mt Mz Nd Nf Nn Nv Nw Og Ok On Oz Pa Pc) Hu(Ih In Ji Jn Jo Jr Js Jt
Lw Mf Mi Mj Mn Mz Nf Ng Nn Nv Og Ok On Oz Pa Pd) Nn(Fr Ih In Jg Ji Jn Jr Lw Mf Mi Mj Mz Nd Nf Nv Nw Og Ok On Oz Pa Pc) Mf(Ih In
Jg Jn Jo Js Jt Mi Mj Mn Mx Mz Nd Nf Nv Og Ok On Oz Pa Pd) Mi(Fr Ih Jg Ji Jn Jr Jt Lw Mn Mz Nd Nv Nw Og Ok On Oz Pa Pc) Nv(Fr Ih Jg
Ji Jn Jr Lw Mn Mt Mz Nd Nf Og Ok On Oz Pa Pc) Oz(Ih In Io Jg Jn Jo Js Jt Lw Mj Mn Nd Nf Ok On Pa Pd) Mj(Ih In Jg Jn Jo Js Jt Lw Mn Mx
Nd Nf Og Ok Pd) Nd(Ih Jg Ji Jn Jr Jt Lw Mz Nf Og Ok On Pa Pc) Ih(In Jn Jo Js Jt Lw Mn Nf Og Ok On Pa Pd) Jg(Fr Ji Jn Jr Lw Mz Nw Og Ok
On Pa Pc) Og(In Jn Jr Jt Lw Mn Mz Nf Ok On Pa) Ok(Fr Io Ji Lw Mn Mz Nw On Pa Pc) In(Jn Jo Js Jt Mn Mx Nf Ng Pd) On(Fr Ji Jr Lw Mz
Nw Pa Pc) Mn(Jn Jo Js Jt Lw Nf Pd) Pa(Fr Ji Jn Jr Lw Mz Pc) Jt(Jo Js Mx Nf Ng Pd) Lw(Fr Ji Mz Pc) Nf(Jo Js Mx Pd) Io(Ip Ir It Iv) Il(Iu Jj Lx)
Jo(Js Ng Pd) Fr(Ji Mz) Mx(Js Pd) Ik(Iu Jj) Im(Jj Lx) Ip(It Iv) Ij Iu Itlv JiPc JsPd} Lx{Jo(Et Fp Fr Hq Hr Hu Hv Hx Ih Ii In Io Ip Iq Ir Is It Iv Jg
Jh Ji Jk Jl Jn Jp Jq Jr Js Jt Lh Li Lj Lu Lv Lw Ly Lz Ma Mb Mc Md Me Mf Mg Mh Mj Ml Mm Mn Mp Mq Ms Mt Mu Mv Mw Mx My Mz Na
Nb Nc Nd Ne Nf Ng Nh Ni Nj Nl Nm Nn No Nq Nr Ns Nt Nu Nv Nw Nx Ny Oe Of Og Oh Oi Ok Om Oy Oz Pb Pc Pd Pe Pf Pg Pz Qa Qb Qc
Qd Qe) Li(Et Fp Fr Hr Hu Hv Hw Hx Ih Ii Io Ip Iq It Iv Jg Jh Ji Jk Jn Jp Jq Jr Jt Lh Lj Lu Lv Lw Ly Lz Ma Mb Mc Md Me Mf Mh Mi Mj Mk
Ml Mm Mn Mp Mq Ms Mt Mu Mv Mw Mx My Mz Na Nb Nc Nd Ne Nf Nh Nj Nl Nm Nn No Ns Nt Nu Nv Nw Nx Ny Oe Of Og Oh Oi Ok
Om Oy Oz Pa Pb Pc Pe Pf Pg Pz Qa Qb Qc Qd Qe) Ng(Fp Hq Hr Hu Hv Hw Hx Ih Ii In Io Ip Iq Ir Is It Iv Jh Ji Jk Jn Jp Jq Jr Js Jt Lh Lj Lu Lv
Lw Ly Lz Ma Mb Mc Md Me Mg Mh Mj Ml Mm Mn Mp Mq Mr Ms Mt Mu Mv Mw Mx My Mz Na Nb Nc Nd Ne Nf Nh Nj Nl Nm Nn No Nq
Ns Nu Nv Nw Nx Ny Oe Of Og Oh Oi Ok Om Oy Oz Pa Pb Pd Pe Pf Pg Pz Qa Qd) Pd(Et Fp Fr Hq Hr Hu Hv Hw Hx Ih Ii Io Ip Iq Ir It Iv Jg Jh
Ji Jk Jn Jp Jq Jr Js Jt Lj Lu Lv Lw Ly Lz Ma Mb Mc Md Me Mg Mh Mj Ml Mm Mp Mq Ms Mt Mu Mv Mw Mx My Mz Na Nb Nc Ne Nf Nh
Nj Nl Nm Nn No Nq Ns Nt Nu Nv Nw Nx Ny Oe Of Og Oh Oi Ok Om Oy Oz Pb Pc Pf Pg Pz Qa Qb Qc Qd Qe) In(Et Fp Fr Hq Hr Hu Hv Ih Ii
Io Ip Iq It Jg Jh Ji Jk Jm Jn Jp Jq Jr Js Jt Lh Lj Lu Lv Lw Ly Lz Ma Mb Mc Md Me Mf Mg Mh Mj Ml Mm Mn Mp Mq Ms Mu Mv Mw Mx My
Mz Na Nb Nc Nd Ne Nf Nh Nj Nl Nm Nn No Nq Ns Nt Nu Nv Nw Nx Ny Oe Of Og Oh Oi Ok Om Oy Oz Pc Pe Pg Pz Qa Qb Qc Qd Qe)
Po(Et Fp Fr Hr Hv Hw Hx Ih Ii Il Im Jg Jh Ji Jk Jn Jp Jq Jt Lh Lj Lu Lv Lw Ly Lz Ma Mb Mc Md Me Mh Mj Mk Ml Mm Mp Mq Mr Ms Mt
Mu Mv Mw Mx My Mz Na Nb Nc Nd Nf Nh Nj Nl Nm Nn No Ns Nu Nv Nw Nx Ny Oe Of Og Oh Oi Ok Om On Oy Oz Pa Pb Pc Pf Pg Pz Qa
Qb Qc Qd Qe) Nk(Et Fp Fr Hq Hr Hv Hw Hx Ih Ii Io Iq Ir It Iv Jg Jh Ji Jk Jn Jp Jq Lh Lj Lu Lv Lw Ly Lz Ma Mb Mc Md Me Mh Mj Mk Mm
Mp Mq Mt Mu Mv Mw Mx Mz Na Nb Ne Nf Nh Ni Nj Nl Nm Nn No Ns Nt Nu Nv Nw Nx Ny Oe Of Oh Oi Ok Om On Oy Oz Pb Pc Pe Pf
Pg Pz Qa Qb Qc Qd Qe) Jm(Et Fr Hq Hr Hu Hv Hw Ih Ii Jg Jh Ji Jk Jn Jp Jq Lh Lj Lw Ly Lz Ma Mb Mc Md Me Mg Mh Mj Mk Mm Mp Mq
Mr Ms Mu Mv Mw My Mz Na Nb Nc Nf Nh Nl Nm No Nq Ns Nt Nu Nv Nw Nx Ny Oe Of Og Oh Oi Ok Om Oy Oz Pb Pe Pf Pg Pz Qa Qb Qc
Qd Qe) Ni(Fp Fr Hq Hr Hu Hx Ih Ii Io Ip Ir Is Iv Jg Jh Ji Jk Jl Jn Jp Jr Js Jt Lu Lv Lw Ly Mb Mg Mh Mi Mj Mk Ml Mm Mn Mp Mq Mr Ms Mt
Mv Mw Mx My Mz Nc Nd Ne Nf Nj Nm Nn Nq Nt Nu Nv Nw Nx Ny Oe Of Og Oi Ok On Oy Pa Pc Pe Pz) Nr(Et Fp Hq Hr Hv Hw Ih Ii Io Ip
Iq Ir It Iv Jh Jk Jp Jq Jt Lj Ly Lz Ma Mb Mc Md Me Mh Ml Mq Mu Mw Mx My Mz Na Nc Nf Nh Nl Nm Nn No Nq Ns Nt Nu Nv Nx Ny Oe
Of Og Oh Om Oy Oz Pb Pf Pg Pz Qa Qb Qc Qd Qe) Js(Fp Hr Hu Hw Hx Ih Io Ip Ir It Iv Ji Jn Jp Jq Jr Jt Lh Lu Lv Mf Mg Mj Mk Mn Mr Ms Mt
My Mz Nb Nd Ne Nj No Nq Ny Og On Oy Pa Pb Pc Pe) Jl(Fp Hq Hr Hu Ih Ii Ip Iq Is Jk Jp Mf Mg Mh Mi Mj Mk Ml Mn Mp Mr Ms Mt Mx
My Nd Ne Nj Nq Nt Nu Nv Nx Ny Oe Og Oi Oy Pc Pz Qa) Jj(Hq Hr Hv Hw Ij Il Im Jh Jk Lj Ly Lz Ma Md Me Mu Mw Na Nc Nf Nh Nl Nm
No Ns Nu Nv Nx Of Oh Oz Pb Pf Pg Qa Qe) Mg(Fp Fr Io Ip Iq Ir Is It Iv Jg Ji Jp Lj Lu Mf Mh Mi Mk Ml Mn Mr Mt Mx Nd Ne Nj Nw Om On
Pc) Jt(Fp Fr Hu Hw Io Ip Iq Ir Iv Jg Ji Jp Lh Lw Mf Mh Mi Mj Mk Ml Mn Mr Mt Ne Nw Ok Pa Pc Pe) Mi(Fp Hu Ih Ii Ip Iq Is Jk Mf Mh Mj Mk
Ml Mn Mp Mr Ms Mt Mx Ne Nt Nu Nw Ny Pc) Mf(Fp Hq Hu Ih Ii Iq Is Ji Jk Lv Mk Mn Mr Ms Mt Ne Nq Nw Ny On Oy) Is(Fp Hu Ih Ii Ip Ly
Mj Mk Ml Mr Mx Ne Nq Nx Og) Nw(Fp Hu Ip Mk Ml Mn Mr Ms Mt My Nq Nx Ny Og) On(Hq Hr Hu Ii Jk Mk Mn Ms My Nb Nq Of Oy Pg)
Mk(Hq Io Ip Iq Ir It Iv Mn Of) Mr(Hu Io Ip Iq Ir It Iv Mn Nq) Hu(Fp Fr Jg Lu Mh Mn Ne Pc) Nq(Fp Fr Jg Lj Lu Nd Pc) Mn(Fp Fr Jp Ly Mh
Ne) Hq(Mh Nd Pa Pb Pf) Pc(Jh Ms Mv My Og) Iu(Ij Ik Il Im) Ne(Iq Ml Ms) Ip(Fr Ly Mz) Fp(Jr Ms) Iq(Ly Mz) Mxlv MyJg HrJr HvHw JiNx
PaPe] Jj{On(Fp Fr Hq Hr Hu Hv Hw Hx Ih Ii In Jg Jh Ji Jk Jm Jn Jo Jp Jq Js Li Lj Lu Lv Lw Ly Lz Ma Mb Mc Md Me Mg Mh Mj Mk Ml Mp
Mq Mr Ms Mu Mv Mw Mx My Mz Na Nb Nc Nd Ne Nf Ng Nh Nj Nk Nl Nm Nn No Nq Nr Ns Nt Nu Nv Nw Nx Ny Oe Of Og Oh Oi Ok Om
Oy Oz Pb Pc Pd Pe Pf Pg Po Pz Qa Qb Qc Qd Qe) Nw(Et Fp Fr Hq Hr Hu Hv Hw Hx Ih Ii In Jg Jh Ji Jk Jm Jn Jo Jp Jq Jt Li Lj Lu Lv Lw Ly Lz
Ma Mb Mc Md Me Mg Mh Mj Mp Mq Ms Mu Mv Mw My Mz Na Nb Nc Ne Nf Ng Nh Ni Nj Nk Nl Nm Nn No Nq Nr Ns Nt Nu Nv Nx Ny
Oe Of Og Oh Oi Ok Om Oy Oz Pb Pc Pd Pe Pf Pg Po Pz Qa Qb Qc Qd Qe) Fr(Et Fp Hu Hv Hw Hx Ih Ii In Jg Jh Ji Jk Jm Jn Jo Jp Jq Js Jt Li Lj
Lu Lv Lw Ly Ma Mb Mc Mf Mg Mi Mj Mk Ml Mn Mp Mq Mr Ms Mv Mw Mx My Mz Nb Nd Ne Ng Ni Nj Nk Nl Nm Nn No Nq Nr Nt Nu
Nv Ny Oe Of Og Oh Oi Ok Om Oy Oz Pb Pc Pd Pe Pf Pg Po Pz Qa Qb Qc Qe) Pa(Et Fp Hq Hr Hu Hv Hw Hx Ih Ii In Jh Jk Jm Jn Jo Jp Jq Jt Li
Lj Lu Lw Ly Lz Ma Mb Mc Md Me Mg Mh Mj Mk Mm Mn Mp Mq Mr Ms Mu Mw My Na Nb Nc Nd Ne Nf Ng Nh Nj Nl Nm No Nq Nr Ns
Nt Nu Nx Ny Oe Of Og Oh Oi Ok Om Oy Oz Pb Pd Pe Pf Pg Po Pz Qa Qb Qc Qd Qe) Iv(Et Fp Hq Hr Hu Hv Hw Ih Im Io Ip Iq It Iu Jh Jm Jn
Jo Jq Js Jt Li Lj Lu Lv Lw Ly Lz Mb Mc Md Me Mf Mg Mh Mj Ml Mm Mp Mq Ms Mw Mx My Na Nb Nc Ne Nf Ng Nh Ni Nj Nk Nl Nm Nq
Ns Nt Nu Nx Ny Oe Of Og Oh Oi Ok Oy Oz Pb Pd Pf Pg Po Pz Qa Qd) Ir(Et Fp Hq Hr Hu Hv Hw Ih Ii Io Ip Iq It Jh Jm Jo Jq Jt Li Lj Lv Lw
Ly Lz Mb Mc Md Me Mg Mh Mj Mm Mp Mq Ms Mw Mx My Na Nc Ne Nf Ng Nh Ni Nj Nl Nm No Nq Ns Nt Nu Nx Ny Oe Of Og Oh Oi Ok
Oz Pd Pf Pz Qa Qb Qc Qd Qe) Mi(Et Hv Hx Ih Ii Jg Ji Jk Jm Jn Jo Jp Js Lu Lv Lw Ly Ma Mc Me Mf Mg Mj Mk Ml Mm Mn Mq Mr Mu Mv
Mw Mx My Mz Nb Nd Ne Ng Ni Nj Nk Nl Nm Nn No Nq Nr Nt Nv Nx Of Oh Oi Ok Om Oy Pb Pc Pd Pe Pf Pg Po Qa Qb Qc Qd Qe) Mt(Et
Fp Hq Hr Hu Hv Hw Ih Ij Il Im Jg Jh Ji Jm Jn Jo Jq Jt Li Lj Lw Ly Lz Ma Mb Mc Md Me Mg Mh Mp Mq Ms Mu Mw My Na Nc Nf Ng Nh Nj

Unconstrained panels with 3 analytes, where 1.0E-5 >= 'model p-value' > 1.0E-6. Contains 15,991 panels of 287,980 total panels evaluated. :
Lx{Nj(Et Fp Fr Hq Hr Hu Hv Hw Hx Ih Ii Io Ip Iq Ir Is It Iv Jg Jh Ji Jk Jn Jp Jq Jr Jt Lh Lj Lu Lv Lw Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Nh Nl Nm Nn No Nq Ns Nt Nu Nv Nw Nx Ny Oe Of Og Oh Oi Ok Om On Oy Oz Pa Pb Pc Pe Pf Pg Pz Qa Qb Qc Qd Qe) Jr(Et Fr Hq Hu Hv Hw Hx Ih Ii Io Ip Iq Ir Is It Iv Jg Jh Ji Jk Jl Jn Jp Jq Jt Lh Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nl Nm Nn No Nq Ns Nt Nu Nv Nw Nx Ny Oe Of Og Oh Oi Ok Om On Oy Oz Pa Pb Pc Pe Pf Pg Pz Qa Qb Qc Qd Qe) Hr(Et Fp Fr Hq Hu Hv Hw Hx Ih Ii Io Ip Iq Ir Is It Iv Jg Jh Ji Jk Jn Jp Jq Jt Lh Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nl Nm Nn No Nq Ns Nt Nu Nv Nw Nx Ny Oe Of Og Oh Oi Ok Om Oy Oz Pa Pb Pc Pe Pf Pg Pz Qa Qb Qc Qd Qe) Pa(Et Fp Fr Hu Hv Hw Hx Ih Ii Il Io Ip Iq Ir Is It Iv Jg Jh Ji Jk Jl Jn Jp Jq Lh Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nl Nm Nn No Nq Ns Nt Nu Nv Nw Nx Ny Oe Of Og Oh Oi Ok Om On Oy Oz Pb Pc Pe Pf Pg Pz Qa Qb Qc Qd Qe) Mj(Et Fp Fr Hq Hu Hv Hw Hx Ih Ii Il Io Ip Iq Ir It Iv Jg Jh Ji Jk Jn Jp Jq Lh Lj Lu Lv Lw Ly Lz Ma Mb Mc Md Me Mf Mg Mh Mk Ml Mm Mn Mp Mq Mr Ms Mt Mu Mv Mw Mx My Mz Na Nb Nc Nd Ne Nf Nh Nl Nm Nn No Nq Ns Nt Nu Nv Nw Nx Ny Oe Of Og Oh Oi Ok Om On Oy Oz Pb Pc Pe Pf Pg Pz Qa Qb Qc Qd Qe) Mz(Et Fp Fr Hq Hu Hv Hw Hx Ih Ii Io Ir Is It Iv Jg Jh Ji Jk Jl Jn Jp Jq Jt Lh Lj Lu Lv Lw Ly Lz Ma Mb Mc Md Me Mf Mg Mh Mi Mk Ml Mm Mn Mp Mq Mr Ms Mt Mu Mv Mw Mx My Na Nb Nc Nd Ne Nf Nh Nl Nm Nn No Nq Ns Nt Nu Nv Nw Nx Ny Oe Of Og Oh Oi Ok Om On Oy Oz Pb Pc Pe Pf Pg Pz Qa Qb Qc Qd) Nd(Et Fp Fr Hu Hv Hw Hx Ih Ii Io Ip Iq Ir Is It Iv Jg Jh Ji Jk Jn Jp Jq Jt Lh Lj Lu Lv Lw Ly Lz Ma Mb Mc Md Me Mf Mh Mi Mk Ml Mm Mn Mp Mq Mr Ms Mt Mu Mv Mw Mx My Na Nb Nc Ne Nf Nh Nl Nm Nn No Ns Nt Nu Nv Nw Nx Ny Oe Of Og Oh Oi Ok Om On Oy Oz Pb Pc Pe Pf Pg Pz Qa Qb Qc Qd Qe) Ih(Et Fp Fr Hq Hu Hv Hw Hx Ii Io Ip Iq Ir It Iv Jg Jh Ji Jk Jn Jp Jq Jt Lh Lj Lu Lv Lw Ly Lz Ma Mb Mc Md Me Mg Mh Mk Ml Mm Mn Mp Mq Mr Ms Mt Mu Mv Mw Mx My Na Nb Nc Ne Nf Nh Nl Nm Nn No Nq Ns Nt Nu Nv Nw Nx Ny Oe Of Og Oh Oi Ok Om On Oy Oz Pb Pc Pe Pf Pg Pz Qa Qb Qc Qd Qe) Ii(Et Fp Fr Hq Hu Hv Hw Hx Io Ip Iq Ir It Iv Jg Jh Ji Jk Jn Jp Jq Js Jt Lh Lj Lu Lv Lw Ly Lz Ma Mb Mc Md Me Mg Mh Mk Ml Mm Mn Mp Mq Mr Ms Mt Mu Mv Mw Mx My Na Nb Nc Ne Nf Nh Nl Nm Nn No Nq Ns Nt Nu Nv Nw Nx Ny Oe Of Og Oh Oi Ok Om Oy Oz Pb Pc Pe Pf Pg Pz Qa Qb Qc Qd Qe) Ji(Et Fp Fr Hq Hu Hv Hw Hx Io Ip Iq Ir Is It Iv Jg Jh Jk Jl Jn Jp Jq Lh Lj Lu Lv Lw Ly Lz Ma Mb Mc Md Me Mg Mh Mi Mk Ml Mm Mn Mp Mq Mr Ms Mt Mu Mv Mw Mx My Na Nb Nc Ne Nf Nh Nl Nm Nn No Nq Ns Nt Nu Nv Nw Ny Oe Of Og Oh Oi Ok Om On Oy Oz Pb Pc Pe Pf Pg Pz Qa Qb Qc Qd Qe) Jp(Et Fp Fr Hq Hu Hv Hw Hx Io Ip Iq Ir Is It Iv Jg Jh Jk Jn Jq Lh Lj Lu Lv Lw Ly Lz Ma Mb Mc Md Me Mf Mh Mi Mk Ml Mm Mp Mq Mr Ms Mt Mu Mv Mw Mx My Na Nb Nc Ne Nf Nh Nl Nm Nn No Nq Ns Nt Nu Nv Nw Nx Ny Oe Of Og Oh Oi Ok Om On Oy Oz Pb Pc Pe Pf Pg Pz Qa Qb Qc Qd Qe) Oe(Et Fp Fr Hq Hu Hv Hw Hx Ip Iq Ir Is Iv Jg Jh Jk Jn Jq Js Jt Lh Lj Lu Lv Lw Ly Lz Ma Mb Mc Md Me Mf Mg Mh Mi Mk Ml Mm Mn Mp Mq Mr Ms Mt Mu Mv Mw Mx My Na Nb Nc Ne Nf Nh Nl Nm Nn No Nq Ns Nt Nu Nv Nw Nx Ny Of Og Oh Oi Ok Om On Oy Oz Pb Pc Pe Pf Pg Pz Qa Qd Qe) Og(Et Fp Fr Hq Hu Hv Hw Hx Io Ip Iq Ir It Iv Jg Jh Jk Jn Jq Jt Lh Lj Lu Lv Lw Ly Lz Ma Mb Mc Md Me Mf Mg Mh Mi Mk Ml Mm Mn Mp Mq Mr Ms Mt Mu Mv Mw Mx My Na Nb Nc Ne Nf Nh Nl Nm Nn No Nq Ns Nt Nu Nv Nx Ny Of Oh Oi Ok Om On Oy Oz Pb Pe Pf Pg Pz Qa Qb Qc Qd Qe) Oy(Et Fp Fr Hq Hu Hv Hw Hx Io Ip Iq Ir Is It Iv Jg Jh Jk Jn Jq Jt Lh Lj Lu Lv Lw Ly Lz Ma Mb Mc Md Me Mg Mh Mi Ml Mm Mn Mp Mq Mr Ms Mt Mu Mv Mw Mx My Na Nb Nc Ne Nf Nh Nl Nm Nn No Nq Ns Nt Nu Nv Nw Nx Ny Of Oh Oi Ok Om Oz Pb Pc Pe Pf Pg Pz Qa Qb Qc Qd Qe) Fr(Et Fp Hq Hv Hw Hx Io Iq Ir Is It Iv Jg Jh Jk Jl Jn Jq Js Lh Lj Lu Lv Lw Ly Lz Ma Mb Mc Md Me Mf Mh Mi Mk Ml Mm Mp Mq Mr Ms Mt Mu Mv Mw Mx My Na Nb Nc Ne Nf Nh Nl Nm Nn No Ns Nt Nu Nv Nw Nx Ny Of Oh Oi Ok Om On Oz Pb Pc Pe Pf Pg Pz Qa Qb Qc Qd Qe) Ny(Et Fp Hq Hu Hv Hw Hx Ip Iq Ir Is It Iv Jg Jh Jk Jn Jq Jt Lh Lj Lu Lv Lw Ly Lz Ma Mb Mc Md Me Mg Mh Mk Ml Mm Mn Mp Mq Mr Ms Mt Mu Mv Mw Mx My Na Nb Nc Ne Nf Nh Nl Nm Nn No Nq Ns Nt Nu Nv Nx Of Oh Oi Ok Om On Oz Pb Pc Pe Pf Pg Pz Qa Qb Qc Qd Qe) Mh(Et Fp Hv Hw Hx Io Ip Iq Ir Is It Iv Jg Jh Jk Jn Jq Js Lh Lj Lu Lv Lw Ly Lz Ma Mb Mc Md Me Mf Mk Ml Mm Mp Mq Mr Ms Mt Mu Mv Mw Mx My Na Nb Nc Ne Nf Nh Nl Nm Nn No Nq Ns Nt Nu Nv Nw Nx Of Oh Oi Ok Om On Oz Pb Pc Pe Pf Pg Pz Qa Qb Qc Qd Qe) Ml(Et Fp Hq Hu Hv Hw Hx Io Ip Iq Ir It Iv Jg Jh Jk Jn Jq Js Lh Lj Lu Lv Lw Ly Lz Ma Mb Mc Md Me Mf Mk Mm Mn Mp Mq Mr Ms Mt Mu Mv Mw Mx My Na Nb Nc Nf Nh Nl Nm Nn No Nq Ns Nt Nu Nv Nx Of Oh Oi Ok Om On Oz Pb Pc Pe Pf Pg Pz Qa Qb Qc Qd Qe) Hq(Et Fp Hu Hv Hw Hx Io Ip Iq Ir Is It Iv Jg Jh Jk Jn Jq Js Jt Lh Lj Lu Lv Lw Ly Lz Ma Mb Mc Md Me Mg Mm Mn Mp Mq Mr Ms Mt Mu Mv Mw Mx My Na Nb Nc Ne Nf Nh Nl Nm Nn No Nq Ns Nt Nu Nv Nw Nx Of Oh Oi Ok Om Oz Pc Pe Pg Pz Qa Qb Qc Qd Qe) Iq(Et Fp Hu Hv Hw Hx Io Ip Ir Is It Iv Jg Jh Jk Jn Jq Js Lh Lj Lu Lv Lz Ma Mb Mc Md Me Mm Mn Mp Mq Ms Mt Mu Mv Mw Mx My Na Nb Nc Nf Nh Ni Nl Nm Nn No Nq Ns Nt Nu Nv Nw Nx Of Oh Oi Ok Om On Oz Pb Pc Pe Pf Pg Pz Qa Qb Qc Qd Qe) Ir(Et Fp Hu Hv Hw Hx Ip Is It Iv Jg Jh Jk Jl Jn Jq Lj Lu Lv Lw Ly Lz Ma Mb Mc Md Me Mf Mi Mm Mn Mp Mq Ms Mt Mu Mv Mw Mx My Na Nb Nc Ne Nf Nh Nl Nm Nn No Nq Ns Nt Nu Nv Nw Nx Of Oh Oi Ok Om On Oz Pb Pc Pe Pf Pg Pz Qa Qb Qc Qd) Nu(Fp Hu Hw Hx Io Ip Is It Iv Jg Jh Jk Jn Jq Js Jt Lh Lj Lu Lv Ly Lz Ma Mc Md Mf Mg Mk Mm Mn Mp Mq Mr Ms Mt Mu Mv Mw Mx My Na Nb Nc Ne Nf Nh Nl Nm Nn No Nq Ns Nt Nv Nw Nx Of Oh Oi Ok Om On Oz Pc Pe Pf Pg Pz Qd Qe) Ms(Et Hu Hv Hw Hx Io Ip Is It Iv Jg Jh Jk Jn Jq Jt Lh Lj Lu Lv Lw Ly Lz Ma Mb Mc Md Me Mg Mk Mm Mn Mp Mq Mr Mt Mu Mv Mw Mx My Na Nb Nc Nf Nh Nl Nm Nn No Nq Ns Nt Nv Nx Of Oh Oi Ok Om Oz Pb Pe Pf Pg Pz Qa Qb Qc Qd Qe) Mt(Et Fp Hu Hv Hw Hx Io Ip Is It Iv Jg Jh Jk Jn Jq Lh Lj Lu Lv Lw Ly Lz Ma Mb Mc Md Me Mk Mm Mn Mp Mq Mr Mu Mv Mw Mx My Na Nb Nc Ne Nf Nh Nl Nm Nn No Nq Ns Nt Nv Nx Of Oh Oi Ok Om On Oz Pb Pc Pe Pf Pg Pz Qa Qb Qd) My(Et Fp Hu Hv Hw Hx Io Ip Is It Iv Jh Jk Jn Jq Jt Lh Lj Lu Lv Lw Ly Lz Ma Mb Mc Md Me Mf Mg Mi Mk Mm Mn Mp Mq Mr Mu Mv Mw Mx Na Nb Nc Ne Nf Nh Nl Nm Nn No Nq Ns Nt Nv Nx Oh Oi Ok Om Oz Pb Pe Pf Pg Pz Qa Qd Qe) Pc(Et Fp Hv Hw Hx Il Io Ip Is It Iv Jg Jk Jn Jq Lh Lj Lu Lv Lw Ly Lz Ma Mb Mc Md Me Mf Mk Mm Mn Mp Mq Mr Mu Mw Mx Na Nb Nc Ne Nf Nh Nl Nm Nn No Ns Nt Nv Nw Nx Of Oh Oi Ok Om On Oz Pb Pe Pf Pg Pz Qa Qb Qc Qd Qe) Nc(Et Fp Hv Hw Hx Io Ip It Iv Jg Jh Jk Jn Jq Lh Lj Lu Lv Lw Ly Lz Ma Mb Mc Md Me Mk Mm Mp Mq Mr Mu Mv Mw Mx Na Nb Nc Nf Nh Nl Nm Nn No Nq Ns Nt Nv Nw Nx Of Oh Oi Ok Om On Oz Pb Pe Pf Pg Pz Qa Qb Qc Qd Qe) Ip(Et Fp Hu Hv Hw Hx Io It Iv Jg Jh Jk Jn Jq Lh Lj Lu Lv Lw Lz Ma Mb Mc Md Me Mf Mm Mn Mp Mq Mu Mv Mw Mx Na Nb Nc Nf Nh Nl Nm Nn No Nq Ns Nt Nv Nx Of Oh Oi Ok Om On Oz Pb Pe Pf Pg Pz Qa Qb Qc Qd Qe) Oi(Fp Hu Hw Hx Io Is It Iv Jg Jh Jk Jn Jq Js Jt Lh Lj Lu Lv Lw Ly Lz Ma Mb Mc Md Mf Mg Mi Mk Mm Mn Mp Mq Mr Mu Mv Mw Mx Na Nb Nc Nf Nh Nl Nm Nn No Nq Nt Nv Nw Nx Of Oh Ok Om On Oz Pe Pf Pg Pz Qe) Fp(Et Hv Hw Hx Io It Iv Jg Jh Jk Jn Jq Lh Lj Lu Lv Lw Ly Lz Ma Mb Mc Md Me Mk Mm Mp Mq Mr Mu Mv Mw Mx Na Nb Nc Nf Nh Nl Nm Nn No Ns Nt Nv Nx Of Oh Ok Om On Oz Pb Pe Pf Pg Pz Qa Qb Qc Qd Qe) Nq(Et Hu Hv Hw Hx Io It Iv Jh Jk Jn Jq Jt Lh Lv Lw Ly Lz Ma Mb Mc Md Me Mg Mk Mm Mn Mp Mq Mu Mv Mw Mx Na Nb Nc Nf Nh Nl Nm Nn No Ns Nt Nv Nx Of Oh Ok Om Oz Pb Pe Pf Pg Pz Qa Qb Qc Qd Qe) Nw(Et Hv Hw Hx Io Is It Iv Jg Jh Jk Jl Jn Jq Lh Lj Lu Lv Lw Ly Lz Ma Mb Mc Md Me Mm Mp Mq Mu Mv Mw Mx Na Nb Nc Nf Nh Nl Nm Nn No Ns Nt Nv Of Oh Ok Om On Oz Pb Pe Pf Pg Pz Qa Qb Qc Qd Qe) On(Et Hv Hw Hx Il Io Is It Iv Jg Jh Jl Jn Jq Lh Lj Lu Lv Lw Ly Lz Ma Mb Mc Md Me Mi Mm Mp Mq Mr Mu Mv Mw Mx Na Nc Nf Nh Nl Nm Nn No Ns Nt Nv Nx Oh Ok Om Oz Pb Pe Pf Pz Qa Qb Qc Qd Qe) Hu(Et Hv Hw Hx Io It Iv Jh Jk Jn Jq Lh Lj Lv Lw Ly Lz Ma Mb

Pg Po Qa Qc Qd) Iu(Fp Hq Hr Hu Hw Ih Ij Il Im In Iq Jh Jm Jo Jq Jt Ly Lz Mb Mc Md Me Mf Mg Mh Ml Mq Ms My Na Nc Ne Nf Ng Nh Ni Nk Nl Ns Nt Nu Nx Oe Og Oi Oz Pd Pz Qd) Jr(Fp Hq Hr Hu Hv Hw Ih Ij Ik Il Im In Jh Jm Jo Jq Jt Li Lj Lw Ly Lz Mb Mc Md Me Mh Mn Mp Mq Ms My Na Nc Nf Nh Nj Nl Ns Nt Nu Nx Ny Oe Og Oz Pd Pz Qd) Jk(Et Fp Hu Hv Ih Jm Jo Js Jt Li Lj Lv Lw Ma Mf Mg Mj Mk Ml Mm Mn Mp Mr Ms Mu Nb Ng Ni Nj Nk Nm No Nq Nr Nt Og Oh Oy Pb Pc Pf Pg Po Qa Qc) Mk(Et Fp Hr Hv Im In Jo Jq Js Lj Lv Md Mf Mg Mm Mu Mw My Na Nd Ng Ni Nj Nk Nm No Nq Nt Nu Nx Of Og Oh Pc Pf Pg Po Qc Qd) Mr(Et Fp Hr Hv Im In Jo Jq Js Lv Md Mf Mg Mm Mu Mw My Na Nd Ng Ni Nj Nk Nm No Nq Nt Nu Nx Of Og Oh Pc Pf Pg Po Qc Qd) Pc(Et Fp Hv Im Jq Lj Lv Ma Mc Mf Mj Ml Mm Ms Mu Mw Mx My Nd Ng Ni Nj Nk Nm No Nq Nr Nt Og Oh Pf Pg Po Qa Qc Qd) Iq(Et Fp Hv Ij Jh Js Li Lj Lu Lv Lw Mg Mj Mm Mp Mw Nk Nm Nq Nt Nu Nx Ny Of Oh Oy Pb Pf Pz Qa Qc Qd) Mi(Fp Hr Hu Hw Ik Il Im Jh Jq Jt Li Lj Lz Mb Md Mh Mp Ms Na Nc Nf Nh Ns Nu Ny Oe Og Oz Pz) Nr(Et Im Lv Ma Mf Mg Mm Mu Mw Na Nd Ni Nj Nk Nm No Nq Nt Nx Oh Pf Pg Po Qa Qc Qd) Nd(Et Fp Hv Ik Ma Mg Mm Mu Nb Ne Nl Nm No Nt Nu Of Oh Pf Pg Po Qa Qc Qd) Pg(Jo Lv Ma Mf Mj Ml Mn Mu Mw Nb Ng Ni Nj Nk Nm No Nq Nt Oh Pd Qa Qc) No(Js Lu Lv Ma Mf Mj Ml Mm Mn Mu Nb Ni Nj Nk Nq Of Oy Pb Qa Qc) Fr(Hq Hr Ij Il Im Lz Md Me Mh Mu Na Nc Nf Nh Ns Nx Qd) Lv(Ma Mb Mf Mj Mm Mu Mw Nb Nk Nm Nq Oh Pf Po Qa Qc) Qa(Js Lu Ma Mf Mj Ml Mu Mx Nb Ni Nj Nk Nq Oy Po) Po(Ma Mf Mu Ni Nj Nk Nm Nq Oh Pd Qc) Mu(Ma Mf Mj Nb Nk Nm Nq Oh Pf Qc) Ma(Lu Mf Mj Nb Nj Nk Oy Qc) Oh(Mf Mj Nb Ni Nj Nk Oy Qc) Nb(Mm Nk Nm Nq Pf Qc) Ij(aA Ir Iv Lh On Pa) Ik(Ir Iv Lh Mt On Pa) Il(Ir Iv Lh On Pa) Im(Ir Lh Mj On Pa) Nm(Mj Nj Nq Qc) Mf(Hw Mj) In(Hw Pb) NqMj NkPf} On{Ms(Et Fp Fr Hq Hu Hv Hw Hx Ih Ii In Io Iq Ir Is It Iv Jg Jh Ji Jk Jm Jn Jp Jq Jr Js Lh Li Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nx Ny Oe Of Og Oh Oi Ok Om Oy Oz Pa Pb Pc Pe Pf Pg Po Pz Qa Qb Qc Qd Qe) Jm(Et Fp Fr Hq Hr Hu Hv Hw Hx Ih Ii In Io Jg Jh Ji Jk Jn Jo Jp Jq Jr Js Lh Li Lj Lu Lv Lw Ly Lz Ma Mb Mc Md Me Mf Mg Mh Mj Mk Ml Mm Mp Mq Mr Mt Mu Mv Mw Mx My Mz Na Nb Nc Nd Ne Nf Nh Nj Nk Nl Nm Nn No Nq Nr Ns Nt Nu Nv Nx Ny Oe Of Og Oh Oi Ok Om Oy Oz Pa Pb Pc Pd Pe Pf Pg Po Pz Qa Qb Qc Qd Qe) Mg(Et Fp Fr Hq Hr Hu Hv Hw Hx Ih Ii In Jg Jh Ji Jk Jn Jp Jq Jr Js Lh Li Lj Lu Lv Lw Ly Lz Ma Mb Mc Md Me Mf Mh Mi Mj Mk Ml Mm Mp Mq Mr Mt Mu Mv Mw My Mz Na Nb Nc Nd Ne Nf Nh Nj Nl Nm Nn No Nq Nr Ns Nt Nu Nv Nx Ny Oe Of Og Oh Oi Ok Om Oy Oz Pa Pb Pc Pd Pe Pf Pg Po Pz Qa Qb Qc Qd Qe) Nr(Et Fp Hq Hr Hu Hv Hw Hx Ih Ii In Io Ip Iq Ir Is It Iv Jg Jh Ji Jk Jn Jp Jq Js Lh Li Lj Lu Lv Lw Lz Ma Mb Mc Md Mf Mh Mj Mk Ml Mm Mn Mp Mq Mr Mu Mv Mw Mx My Mz Nb Nc Nd Ne Nf Ni Nj Nk Nl Nm Nn No Nq Ns Nu Nv Nx Ny Oe Of Og Oh Oi Ok Om Oy Oz Pb Pc Pd Pe Pf Pg Pz Qa Qb Qc Qe) In(Et Fp Fr Hq Hr Hu Hv Hx Ih Ii Io Ip Iq It Jg Jh Jk Jn Jp Jq Js Jt Lh Li Lj Lu Lv Lw Ly Lz Ma Mb Mc Md Me Mf Mh Mj Mk Ml Mm Mn Mp Mq Mu Mv Mw My Na Nb Nc Nd Ne Nf Nh Nj Nk Nl Nm Nn No Nq Ns Nt Nu Nv Ny Oe Of Og Oh Oi Ok Om Oy Oz Pb Pc Pd Pe Pf Pg Po Pz Qa Qc Qe) Jt(Et Fp Hq Hr Hv Hw Hx Ih Ii Jg Ji Jk Jo Jq Js Lh Li Lv Lw Ly Lz Ma Mb Mc Md Me Mh Mk Ml Mm Mp Mq Mu Mw Mx Na Nb Nc Nd Ne Nf Nh Nj Nl Nm Nn No Ns Nt Nu Nv Ny Oe Oh Oi Om Oy Oz Pb Pc Pd Pe Pf Pg Po Pz Qa Qb Qc Qd Qe) Jo(Et Fp Hq Hr Hu Hv Ih Im Jh Jk Jq Js Li Lj Lu Lw Ly Lz Mb Mc Md Me Mf Mh Mj Ml Mm Mp Mq Mu Mw My Na Nb Nc Ne Nf Nh Nj Nl No Nq Ns Nt Nu Nx Ny Oe Of Oh Oi Oy Pb Pc Pd Po Pz Qc Qd Qe) Of(Hr Hv Hx Io Ip Iq Ir Is It Iv Jg Ji Jn Jp Jr Js Lh Li Lj Lv Lz Ma Mf Mh Mi Ml Mn Mr Mu Mv Mz Nb Nd Ne Nf Ni Nk Nn Nv Ny Og Oh Oi Om Oz Pa Pb Pc Pd Pe Pf Qb) Mi(Et Fr Hr Hu Hw Ih Ii Io Ip Iq Ir Is It Iv Jh Jk Jn Jp Jq Jr Mf Mh Mj Mk Ml Mn Mp Mr Mt Mv Mx Ny Og Oi Pa Pc Pf Pg Po Pz) Is(Et Fr Hq Hr Hu Hw Ih Ii Ip Iq Jh Jk Jq Jr Js Li Ly Mf Mk Ml Mr Mt Mv Mw Mx My Mz Nb Nd Ne Nf Ni Nj Nk Nm Nq Nv Nx Oe Og Oi Oy Pa Pd Pg Po Pz) Hu(Et Fr Hr Ih Ii Io Ip Iq Ir It Iv Jg Jp Jq Jr Js Li Lu Lv Mf Mk Ml Mm Mn Mt Mu Mv Mx Nd Ne Nj Nk Nm Nn Nx Ny Oe Og Oi Pa Pd Pz Qd) Ni(Et Fr Hr Ih Ii Io Ip Iq Ir It Iv Jh Ji Jk Jp Jr Lj Mf Mk Mn Mr Mt Mv Mw My Mz Nb Nc Nd Nk Nm Nq Nv Nx Ny Oe Og Oi Oy Pa Pd Pz) Nq(Fr Hr Io Ip Iq Ir It Iv Jp Jr Js Lu Mf Mn Mt Mu Mx Nd Ne Nk Nx Ny Oe Og Oi Pa Pc Pd Pz) My(Fr Hr Ih Io Ip Iq Ir It Iv Jg Jp Jr Js Mf Mn Mt Mv Nd Ne Nj Nk Nx Ny Oe Og Oi Pa Pc Pd) Pd(Fr Io Ip Iq Ir It Iv Jh Ji Jp Jr Lh Mf Mj Mn Mr Mt Mz Nd Nk Ny Oe Og Oi Oy Pe Pf) Nk(Fr Hr Ii Ip Iq Ir It Iv Jh Jk Jp Jr Mf Mn Mt Mv Mw Mz Nd Nx Oe Og Oi Oy Pa) Og(Et Fr Hr Ih Io Ip Iq Ir It Iv Jr Js Mf Mn Mt Mx Mz Nb Ne Nj Ny Pa Pc) Mn(Fr Hr Ii Jh Jk Jp Jr Js Mf Mk Mt Mv Mw Mz Nd Ne Nv Nx Oe Oi Pa) Ip(Fr Ii Ir Jh Ji Jk Jp Jr Ly Mf Mk Mv Mw Mz Nd Ne Nx Oi Oy Pa) Hr(Fr Hx Ir Jh Ji Jk Jp Jr Mr Mt Mv Mw Mz Nb Nd Oe Oi Oy Pa) Fr(Hq Iq Ir It Iv Jh Ji Jk Jr Mk Mv Mw Mz Nb Oi Oy Pg) Iq(Ii Ir Jh Jk Jr Ly Mf Mk Mv Mw Mz Nd Nj Nx Oi Pa) Mt(Ih Ii Jh Jk Jr Js Mf Mk Nb Nd Oi Oy Pg) Ir(Ih Ii Jh Jk Js Mf Mk Mx Mz Nb Nd Nx Oi) Jk(Et Io It Iv Jr Mf Mx Nd Pa) Jr(Ih Ii Js Mf Nb Nx Oi) Pa(Hq Ii Js Mk Nb Nx Oy) Mz(Io It Iv Js Mx Nf) Mf(Ii Ji Mv Oe Oi) Mx(Ji Mw Nb Pg) It(Ii Mk Nx Oi) Iu(Ij Ik Il Im) Iv(Ii Mk Nx Oi) Js(Jh Ji Jn Oy) Ng(Ij Ik Il) Mm(Ii Nb) Io(Mk Oi) Ji(Jq Nx) Jp(Nb Oy) NdHq JhPc} Mi{Is(Et Fp Hr Hu Hv Hw Hx Ih Ii Ip Iq Ir It Jg Jh Ji Jk Jn Jp Jq Jr Lh Li Lj Lu Lw Ly Lz Ma Mb Mc Md Me Mf Mg Mh Mj Mk Ml Mm Mn Mp Mq Mr Ms Mt Mu Mv My Mz Na Nc Nd Ne Nf Nh Ni Nj Nl Nm Nn No Nq Ns Nt Nu Nv Nx Ny Of Og Oh Oi Ok Om Oy Oz Pa Pb Pc Pe Pf Pg Po Pz Qa Qb Qc Qd Qe) Jp(Et Fr Hr Hu Hv Hx Ih Ii Io Ip Iq Ir It Iv Jg Jh Ji Jk Jm Jn Jq Jr Lh Li Lu Lv Lw Ma Mc Md Mf Mg Mh Mj Mk Ml Mm Mn Mp Mq Mr Ms Mt Mv Mx My Mz Na Nd Ne Nf Nj Nm Nn Nt Nu Ny Of Og Oh Oi Ok Om Oy Oz Pa Pb Pc Pe Pf Pg Pz Qa Qb Qc Qd Qe) Iu(Et Fp Hr Hu Hv Hw Ih Ii Im Io Ip Iq Jh Jk Jq Js Jt Li Lj Lu Lv Lw Ly Lz Ma Mb Mc Md Me Mf Mg Mh Mj Ml Mm Mn Mp Mq Mr Ms Mu Mw Mx My Na Nb Nc Nd Ne Nf Ng Nh Ni Nj Nl Nm Nq Nr Ns Nt Nu Nx Ny Oe Of Og Oh Oi Oy Oz Pb Pf Pg Po Pz Qd) Jo(Et Fp Hr Hu Hv Hw Ih Iq Jh Jk Jm Jn Jq Jr Js Jt Li Lj Lu Lw Ly Ma Mc Mf Mg Mh Mj Ml Mm Mn Mq Ms Mu Mv Mw Mx My Nb Nd Ne Ng Ni Nj Nk Nl Nm Nn No Nq Nt Nu Nx Of Og Oh Oi Oy Oz Pb Pd Pe Pf Pg Po Pz Qa Qb Qc Qd Qe) Fr(Hu Hx Ih Ii Io Ip Iq Ir It Iv Jh Ji Jk Jn Jr Js Jt Li Lv Lw Ma Mf Mh Mj Mk Ml Mm Mn Mp Mr Ms Mt Mv Mx My Mz Nd Ne Ni Nj Nk Nm Nt Nu Ny Of Og Oi Ok Oy Pa Pc Pz Qe) Hq(Et Hw Il Jh Jk Jm Jq Js Li Lj Ly Lz Mb Mc Md Mg Mh Mj Mk Ml Mm Mp Mr Mu Mw Na Nb Nc Nf Nh Nl Ns Nt Nu Nx Ny Oe Of Oy Pz Qc Qd) Jm(Hx Ii Io Ip Iq It Iv Jg Jn Jr Js Lh Ma Mf Mk Ml Mr Mu Mv Mx Mz Nd Ng Ni Nk Nn Nr Nv Oh Ok Om Pa Pc Pd Pe Pf Po Qa Qb Qe) Ji(Et Fp Hu Ih Ii Io Ip Iq Ir It Iv Jn Jq Jr Jt Mf Mg Mj Mk Ml Mn Ms Mt Mx Nd Ne Nf Ni Nj Nk Nm Nt Nx Ny Og Pa Pc Qa) Mt(Hu Hx Ih Ii Ip Iq Jg Jn Jr Jt Li Lw Mf Mg Mh Mj Mk Ml Mn Mr Ms Mv Mx Mz Nd Ne Ni Nj Nk Nt Ny Og Oi Ok Pa Pc) Pd(Hw Hx Ii Ip Ir It Iv Jg Jn Jr Lh Li Lu Lw Mf Mk Mr Mv Mz Nb Nd Nk Nn No Nr Nv Ok Om Pa Pc Pe Pf Po Qe) Ng(Et Hx Ii Io Ip Ir Iv Jk Jn Jr Ma Mf Mg Mk Mr Mu Mw Mz Nb Nd Ne Nk Nn Nq Nr Of Oi Oy Pa Pb Pf Qa Qe) Nk(Hx Ip Ir Iv Jg Jn Jr Js Lh Mf Mg Mk Ml Mr Mz Nc Nd Ne Nl Nn Nq Nr Nv Ok Om Pa Pc Pe Qb Qe) In(Hr Hu Ih Jq Lu Ly Mb Mc Md Me Mh Mj Mp My Na Nf Nh Ns Nt Nu Ny Oe Oy Pz) Ni(Hx Jg Jn Jr Lh Mf Mk Ml Mr Mz Nc Nd Nn Nq Nr Nv Ok Pa Pc Qe) Jg(Hu Ih Ii Jh Jk Jr Js Jt Mf Mk Ml Mn Ms Mv Mw My Nt Og Pz) Nr(Hx Ir Jn Jr Lh Mk Mv Mz Nn No Nv Ok Om Pa Pc Qa Qb Qe) Nq(Hr Ir Jn Jr Lh Ma Mv Mz Nn Nv Ok Om Pc Pg Qa Qe) Js(Hx Ir Iv Lh Nn No Nv Ok Om Pa Pc Qa Qb Qe) Mz(Io Ip Iq Ir It Iv Jn Jt Mf Ml Mx Pc) Pc(Ip Jr Mf Mg Ms My Og) Ok(Ip Mf Mg Ml Mx Nt) Ir(Jt Mf Mk Ml Mx) Jr(Iq Jn Mf Ml Mx) Qe(Ip Iq Jt Mf) Mg(Lh Nv Om) Pg(Mk Mr Pb) Mi(Jn Om) Jt(Lh Om) NnIp MkOy} Fr{Is(Et Fp Hq Hr Hv Hw Hx Ik Io Iq Ir It Iv Jg Jh Ji Jn Jp Jq Jr Lh Lj Lu Lv Lw Ly Lz Ma Mb Mc Md Me Mh Mj Ml Mm Mn Mp Mq Mr Mu Mw Na Nb Nc Nd Ne Nf Nh Nl Nm Nn No Ns Nt Nu Nv Ny Oe Of Oh Ok Om Oy Oz Pa Pb Pc Pe Pf Pg Po Pz Qa Qb Qc Qd Qe) Mg(Et Fp Hu Hv Hw Hx Ih Ii In Jg Jm Jn Jo Jp Jq Js Jt Lh Lu Lv Lw Ma Mf Mj Mk Ml Mm Mn Mp Mq Mr Ms Mt Mv Mx My Mz Nb Nd Ne Ng Ni Nj Nk Nm Nn No Nq Nr Nv Nx Oe Og Oh Oi Ok Om Oy Pa Pb Pe Pf Pg Po Qa Qb Qc Qe) Ir(Fp Hq Hr Hu Hx Ih Ii In Ip Iq Jh Ji Jk Jn Jp Jr Js Li Lu Lv Lw Ly Mb Mf Mh Mj Mk Ml Mm Mr Ms Mt Mv Mw Mx My Mz

Ok Pa Pe) Ni(Hx Jr Mk Mr Nd Nr Pa Pe) Nk(Jm Jr Mk Mr Nd Nr Pa) Jm(Hx Ir Lh Pa) Pc(Ms My Og) NrPa JrJs LhPd} Pa{Jm(Iq Ir Iv Jg Lh Mu Nk Nn Nv Om) Jg(Jt Mg Ni Nk Nr Pd) Nk(Ir Iv Jr Pd) Ok(Jt Nr Pd) Lh(Nr Pd) NdHq OmPd} Ir{Jm(Lh Ma Mn Mu Mv Nn Nv Pc) Jt(Jg Lh Nn Ok Om) Mg(Jg Om) Nk(Nd Nn) JrJs} Jg{Jt(Jr Mj Mk Mr Nr Ok Pe) Mg(Hx Lh Nd Om) Mk(Of Oy) Jr(Js Nr) HxJm} Lh{Pc(Jm Ms My Og) Jr(Js Nr Pd) NdJm JnJs JtOk} Nn{Jm(Ip It Iv Qe) MkOy JtOk} Mk{Oy(Mu Nv Om) NvOf} Nd{Nk(Iv Nl) LvJm JtOk} Jr{Js(Iv Ok) JtOk} Mg{Om(Iv Pc)} JtOkPc

Unconstrained panels with 2 analytes, where 1.0E-6 >= 'model p-value' > 0. Contains 183 panels of 7,261 total panels evaluated. : aA(Et Fp Fr Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Lx(Fp Hu In Is Iu Jj Jl Jm Jo Js Jt Li Mf Mg Mi Mn Mr Ng Ni Nk Nr Pd Po) Jj(Fr Ir Is Iu Iv Ji Jl Jr Lh Mi Mt Mz Nn Nv Nw On Pa) Iu(Fr Is Ji Jl Lh Nw On) Jl(Jm Jo Jp Ng Nk Nr) Ng(Fr Jg Nw On) Jo(Lh Nw On) Mi(Hq In) Is(Fr Jm) Nw(Jm Js) JtOn Unconstrained panels with 2 analytes, where 1.0E-5 >= 'model p-value' > 1.0E-6. Contains 337 panels of 7,261 total panels evaluated. : Jl(Fp Fr Hq Hr Hu Hv Hw Hx Ih Ii In Io Ip Iq Ir Is It Iv Jg Jh Ji Jk Jn Jq Jr Js Jt Lh Li Lu Lv Lw Ly Ma Mc Mf Mg Mh Mi Mj Mk Ml Mm Mn Mp Mq Mr Ms Mt Mu Mv Mw Mx My Mz Na Nb Nd Ne Nf Nh Ni Nj Nl Nm Nn No Nq Ns Nt Nu Nv Nw Nx Ny Oe Of Og Oi Ok Om On Oy Oz Pa Pb Pc Pd Pe Pf Pg Pz Qa Qb Qe) Lx(Et Fr Hq Hr Hv Hw Hx Ih Ii Io Ip Iq Ir It Iv Jg Jh Ji Jk Jn Jp Jq Jr Lh Lj Lu Lv Lw Ly Lz Ma Mb Mc Md Me Mh Mj Mk Ml Mm Mp Mq Ms Mt Mu Mv Mw Mx My Mz Na Nb Nc Nd Ne Nf Nh Nj Nl Nm Nn No Nq Ns Nt Nu Nv Nw Nx Ny Oe Of Og Oh Oi Ok Om On Oy Oz Pa Pb Pc Pe Pf Pg Pz Qa Qb Qc Qd Qe) Nw(Fp Fr Hq Hu Ih Ii In Io Ip Iq Ir Is It Iv Jh Ji Jk Jn Jp Jq Jr Jt Lu Lv Lw Md Mf Mg Mi Mj Mk Ml Mn Mr Ms Mt Mv Mw Mx My Nd Ne Nf Ni Nj Nk Nq Nr Nx Ny Oe Of Og Oi On Pa Pc Pd Pe Po Pz) Jj(Hx Ii Io Ip Iq It Jg Jk Jn Jp Mk Mr Mu Mv No Nr Ok Om Pc Pe Pg Qa Qb Qe) On(Hr Hu In Ip Iq Ir Is Jk Jm Mg Mi Mn Ms My Ni Nk Nq Nr Of Og Pd) Fr(Hu Ip Ir Iv Ji Jm Jo Jr Mg Mi Mz Nr) Mi(Is Iu Jg Ji Jm Jo Jp Mt Nk Pc Pd) Is(Ji Jo Jp Jt Mz Nd Nk Og) Iu(Ir Mt Mz Nn Pa) Ji(Jo Mf Nd) Mt(Ng Nr) aA(Il Im) InLh Unconstrained panels with 2 analytes, where 1.0E-4 >= 'model p-value' > 1.0E-5. Contains 590 panels of 7,261 total panels evaluated. : Mi(Et Fp Hr Hu Hv Hw Hx Ih Ii Io Ip Iq Ir It Iv Jh Jk Jn Jr Js Jt Lh Li Lj Lu Lv Lw Ly Ma Mb Mc Md Me Mf Mg Mh Mj Mk Ml Mm Mn Mq Mr Ms Mu Mv Mw Mx My Mz Na Nb Nc Nd Ne Nf Ng Nh Ni Nj Nl Nm Nn No Nq Nr Ns Nt Nv Ny Of Og Oh Oi Ok Om Oy Oz Pa Pb Pc Pf Pg Po Pz Qa Qb Qc Qe) On(Et Fp Fr Hq Hv Hw Hx Ih Ii Io It Iv Jg Jh Ji Jn Jp Jq Jr Js Lh Li Lj Lu Lv Lw Ly Lz Ma Mb Mc Md Me Mf Mh Mj Mk Ml Mm Mp Mq Mr Mt Mu Mv Mw Mx Mz Na Nb Nc Nd Ne Nf Nh Nj Nl Nm Nn No Ns Nt Nu Nv Nx Ny Oe Oh Oi Ok Om Oy Oz Pa Pb Pc Pe Pf Pg Po Pz Qa Qb Qc Qd Qe) Fr(Fp Hq Hr Hv Hw Hx Ih Ii In Io Iq It Jg Jh Jk Jn Jp Jq Js Jt Lh Li Lj Lu Lv Lw Lz Mf Mj Mk Ml Mn Mp Mq Mr Ms Mt Mu Mv Mw Mx My Nb Nd Ne Ni Nj Nk Nl Nn No Nq Ns Nv Nx Ny Oe Of Og Oh Oi Ok Om Oy Oz Pa Pb Pc Pd Pe Pf Po Pz Qa Qb Qc Qd Qe) Ji(Fp Hu Hv Hx Ih Ii In Io Ip Iq Ir It Iv Jg Jm Jn Jp Jq Jr Js Jt Lh Lu Lv Ma Mb Me Mg Mj Mk Ml Mn Mr Ms Mt Mu Mv Mx Mz Ne Ng Ni Nj Nk Nm Nn No Nq Nr Nv Nx Ny Oe Og Oi Ok Om Pa Pc Pd Pe Pf Pz Qb Qe) Is(Hu Hv Hw Hx Ih Ii In Ip Iq Ir It Jg Jn Jq Jr Js Lh Li Lu Lv Lw Ly Ma Mb Mf Mg Mj Mk Ml Mn Mp Mr Ms Mt Mu Mv Mx Nb Nc Ne Ng Nh Ni Nj Nl Nm Nn No Nr Nv Nx Oe Oi Ok Om Oy Pa Pb Pc Pd Pe Pf) Nw(Et Hr Hv Hw Hx Jg Lh Li Lj Ly Lz Ma Mb Mc Me Mh Mm Mp Mq Mu Mz Na Nb Nc Nh Nl Nm Nn No Ns Nt Nu Nv Oh Ok Om Oy Oz Pb Pf Pg Qa Qb Qc Qd Qe) Mt(Hu Hx Ih In Ir Jm Jo Jp Jr Js Jt Lh Lv Lw Mf Mg Mj Mk Mr Ms Mz Nd Ni Nk Nn Og Oi Ok Pa Pc Pd Pe) Jj(Et Fp Hv Ij Im Js Lj Lv Lw Ma Mg Mj Mm Mp Mw My Nb Nd Nk Nm Nq Nt Nx Of Oh Oy Pf Po Qc Qd) Jp(Hx Ir Iu Jm Jo Jr Lh Lv Lw Mk Mr Mz Nd Ng Ni Nk Nr Ok Pa Pc Pe) Jl(Et Ij Ik Il Im Lj Lz Mb Md Me Nc Oh Po Qc Qd) Mz(Io Ip Iq It Iv Jg Jo Mk Mr Nk Nn Pa Pc) Iu(Jr Mv No Nv Ok Om Pe Qa Qe) Jo(Ir Jg Nn Nv Ok Om Pa Pe) Pa(In Jg Jm Ni Nk Nr Ok) Ng(Lh Nn Nv Ok Om Pc) Lx(Ij Ik Il Im) Jm(Ir Lh Nn Qe) Mg(Jg Lh Om) In(Iv Pe) Jr(Jg Nk) Lh(Nr Pd) Ok(Jt Nd) aA(Ij Ik) NnIr Unconstrained panels with 2 analytes, where 1.0E-3 >= 'model p-value' > 1.0E-4. Contains 834 panels of 7,261 total panels evaluated. : Jp(Et Fp Hq Hr Hu Hv Hw Ih Ii In Io Ip Iq It Iv Jg Jh Jk Jn Jq Js Jt Li Lj Lu Ly Lz Ma Mb Mc Md Me Mf Mg Mh Mj Ml Mm Mn Mp Mq Ms Mu Mv Mw Mx My Na Nb Nc Ne Nf Nh Nj Nl Nm Nn No Nq Ns Nt Nu Nv Nx Ny Oe Og Oh Oi Om Oy Oz Pb Pd Pe Pf Pg Po Pz Qa Qb Qc Qd Qe) Mz(Et Fp Hr Hu Hv Hw Hx Ih Ii In Jh Jk Jm Jn Jq Jr Js Jt Lh Li Lu Lv Lw Ly Lz Ma Mb Mc Md Me Mf Mg Mj Ml Mm Mn Mp Mq Ms Mu Mv Mw Mx My Na Nb Nc Nd Ne Nf Ng Nh Ni Nj Nl Nm No Nq Nr Ns Nv Nx Ny Oe Og Oh Oi On Om Oy Oz Pb Pd Pe Pf Pg Po Pz Qa Qb Qe) Mt(Et Fp Hq Hr Hv Hw Ii Ik Io Ip Iq It Iv Jg Jh Jk Jn Jq Li Lj Lu Ly Lz Ma Mb Mc Md Me Mh Ml Mm Mn Mp Mq Mu Mv Mw Mx My Na Nb Nc Ne Nf Nh Nj Nl Nm No Nq Ns Nt Nu Nv Nx Ny Oe Of Oh Om Oy Oz Pb Pf Pg Po Pz Qa Qb Qc Qd Qe) Lh(Hq Hr Hu Hv Hx Ih Ii Io Ip Iq Ir It Iv Jn Jq Jr Js Jt Lu Lv Lw Ma Mf Mg Mk Ml Mn Mr Ms Mu Mv Nb Nd Ne Nf Ng Nj Nn No Nq Nv Oe Og Om Oy Oz Pc Pd Pe Qa Qb Qe) Pa(Et Hq Hr Hu Hv Hx Ih Io Ip Iq Ir It Iv Jn Jq Jr Js Jt Lu Lv Lw Ma Mf Mg Mk Ml Mn Mr Ms Mu Mv Nb Nd Ne Nf Ng Nj Nn No Nq Nv Oe Og Om Oy Oz Pc Pd Pe Qa Qb Qe) Jj(Hq Hr Hu Hw Ih Ik Il In Jh Jm Jo Jq Jt Li Lu Ly Lz Mb Mc Md Me Mf Mh Ml Mn Mq Ms Mx Na Nc Ne Nf Ng Nh Ni Nj Nl Ns Nu Ny Oe Og Oi Oz Pb Pd Pz) Ji(Et Hq Hr Hw Ij Ik Il Im Jh Jk Li Lj Lw Ly Lz Mc Md Mh Mm Mp Mq Mw My Na Nb Nc Nf Nh Nl Ns Nt Nu Of Oh Oy Oz Pb Pg Po Qa Qc Qd) Is(Et Fp Hq Hr Ik Il Io Iv Jh Jk Lj Lz Mc Md Me Mh Mm Mq Mw My Na Nf Nq Ns Nt Nu Ny Of Oh Oz Pg Po Pz Qa Qb Qc Qd Qe) Nn(Hu Hv Hx In Io Ip Iq It Iv Jg Jn Jr Lu Lv Lw Mf Mg Mj Mk Mn Mr Ms Nd Ni Nk No Nr Oe Og Oi Om Pc Pe Qe) Jg(Hu Hv Hx Ir Iu Jh Jm Jn Jt Lu Lv Lw Mf Mj Mk Mr Ms Mv My Nd Ni Nk No Nq Nr Og Oi Pc Pe Pz Qa Qb Qe) Om(Hu Hx In Ip Ir Iv Jh Jm Jn Jr Jt Lu Lv Mf Mj Mk Mr Ms My Nd Ni Nk No Nr Of Og Pc Pd Pe Qa Qb Qe) Jr(Et Hx In Ip Iq Ir Iv Jm Jo Js Lu Lv Lw Ma Mf Mk Ml Mr Mu Mv Nd Ng Ni No Nr Nv Og Pc Pe Qe) Fr(Et Ij Ik Il Im Ly Ma Mb Mc Md Me Mh Mm Na Nc Nf Nh Nm Nt Nu Pg) Ir(In Lu Lw Ma Mf Mk Mn Mr Mu Mv Nd Ni Nk No Nr Nv Og Pc Pe) Jo(Et Hx Iv Jn Ma Mj Mk Mr Mu Mv Nb No Nr Pc Pf Pg Po Qa Qe) Iu(Hx Im Iv Jn Ma Mk Mr Mu Nr Oh Pc Pf Po Qb) No(Ip Iq Iv Jm Lv Mk Ng Ni Nk Nr Pc) Nv(Hu Jm Mg Mk Mr Ms Ni Nk Nr Og Pe) Pc(Jm Jn Ma Ms My Nk Og Pe Qa Qe) Mi(Il Im Jq Lz Mp Nu Nx Oe Qd) Mk(In Jn Ma Mu Mv Ng Ni Qa Qe) Mr(In Jn Ma Mu Mv Ng Ni Qa Qe) Pe(Jm Ng Ni Nk Nr Pd Qe) Nr(Ma Mv Ni Qa Qe) Nk(Hx Jn Qa Qb Qe) Nd(Iv Lv Qa Qe) Ng(Ma Mu Mv Qe) Hx(In Jm Ni Og) Nw(Ij Ik Il Im) On(Ij Ik Il Im) Jm(Jn Qa Qb) In(Hw Pb) Malv NiQe JnJs Unconstrained panels with 2 analytes, where 1.0E-2 >= 'model p-value' > 1.0E-3. Contains 1,490 panels of 7,261 total panels evaluated. : Nv(Et Fp Hq Hr Hv Hw Hx Ih Ii In Io Ip Iq It Iv Jg Jh Jk Jn Jq Js Jt Lh Li Lj Lu Lv Lw Ly Lz Ma Mb Mc Md Me Mf Mh Mj Ml Mm Mn Mp Mq Mu Mv Mw Mx My Na Nb Nc Nd Ne Nf Nh Nj Nl Nm Nn No Nq Ns Nt Nu Nx Ny Oe Of Oh Oi Om Oy Oz Pb Pc Pd Pf Pg Po Pz Qa Qb Qc Qd Qe) Qe(Et Fp Hq Hr Hu Hv Hw Hx Ih Ii In Io Ip Iq Ir It Iv Jh Jk Jn Jq Js Jt Li Lj Lu Lv Lw Ly Lz Ma Mb Mc Md Me Mf Mg Mh Mj Ml Mm

Figure 10 Continued

Mn Mp Mq Ms Mu Mv Mw Mx My Na Nb Nc Ne Nf Nh Nj Nl Nm No Nq Ns Nt Nu Nx Ny Oe Of Og Oh Oi Oy Oz Pb Pd Pf Pg Po Pz Qa Qb Qc Qd) No(Et Fp Hq Hr Hu Hv Hw Hx Ih Ii In Io It Jh Jk Jn Jq Js Jt Li Lj Lu Lw Ly Lz Ma Mb Mc Md Me Mf Mg Mh Mj Ml Mm Mn Mp Mq Mr Ms Mu Mv Mw Mx My Na Nb Nc Nd Ne Nf Nh Nj Nl Nm Nq Ns Nt Nu Nx Ny Oe Of Og Oh Oi Oy Oz Pb Pd Pe Pf Pg Po Pz Qa Qb Qc Qd) Pe(Et Fp Hq Hr Hu Hv Hw Hx Ih Ii Il Im Io Ip Iq It Iv Jh Jk Jn Jq Js Jt Lj Lu Lv Lw Ly Ma Mb Md Me Mf Mg Mh Mj Mk Ml Mm Mn Mp Mq Mr Ms Mu Mv Mw Mx My Na Nb Nc Nd Ne Nf Nj Nl Nm Nq Nu Oe Of Og Oh Oi Oy Oz Pf Pg Po Qa Qb Qc Qd) Ir(Et Fp Hq Hr Hu Hv Hw Hx Ih Ii Io Ip Iq It Iv Jh Jk Jn Jq Js Jt Li Lj Lv Ly Lz Mb Mc Md Me Mg Mh Mj Ml Mm Mp Mq Ms Mw Mx My Na Nb Nc Ne Nf Ng Nh Nj Nl Nm Nq Ns Nt Nu Nx Ny Oe Of Oh Oi Oy Oz Pb Pd Pf Pg Po Pz Qa Qb Qc Qd) Mk(Et Fp Hq Hr Hu Hv Hx Ih Ij Ik Il Im Io Ip Iq It Iv Jh Jk Jm Jq Jt Lj Lu Lv Lw Mb Md Me Mf Mg Ml Mm Mn Mp Mq Mr Ms Mw Mx My Na Nc Nd Ne Nf Nj Nk Nl Nm Nq Nr Oe Of Og Oh Oi Oy Oz Pc Pd Pf Pg Po Qb Qc Qd) Mr(Et Fp Hq Hr Hu Hv Hx Ih Ik Il Im Io Ip Iq It Iv Jh Jk Jm Jq Js Jt Lj Lu Lv Lw Mb Md Me Mf Mg Ml Mm Mn Mp Mq Ms Mw Mx My Na Nc Nd Ne Nf Nj Nk Nl Nm Nq Nr Oe Of Og Oh Oi Oy Oz Pc Pd Pf Pg Po Qb Qc Qd) Jr(Fp Hq Hr Hu Hv Hw Ih Ii Im Io It Jh Jk Jn Jq Jt Li Lj Ly Lz Mb Mc Md Me Mg Mh Mj Mm Mn Mp Mq Ms Mw Mx My Na Nb Nc Ne Nf Nh Nj Nl Nm Nq Ns Nt Nu Nx Ny Oe Of Oh Oi Oy Oz Pb Pd Pf Pg Po Pz Qa Qb Qc Qd) Jg(Et Fp Hq Hr Hw Ih Ii Ij Ik Il Im In Io Ip Iq It Iv Jk Jq Js Li Lj Ly Lz Ma Mb Mc Md Me Mh Ml Mm Mn Mp Mq Mu Mw Mx Na Nb Nc Ne Nf Nh Nj Nl Nm Ns Nt Nu Nx Ny Oe Of Oh Om Oy Oz Pb Pd Pf Pg Po Qc Qd) Nn(Et Fp Hq Hr Hw Ih Ii Im Jh Jk Jq Js Jt Li Lj Ly Lz Ma Mb Mc Md Me Mh Ml Mm Mp Mq Mu Mv Mw Mx My Na Nb Nc Ne Nf Nh Nj Nl Nm Nq Ns Nt Nu Nx Ny Of Oh Oy Oz Pb Pd Pf Pg Po Pz Qa Qb Qc Qd) Om(Et Fp Hq Hr Hv Hw Ih Ii Io Iq It Jk Jq Js Li Lj Lw Ly Lz Ma Mb Mc Md Me Mh Ml Mm Mn Mp Mq Mu Mv Mw Mx Na Nb Nc Ne Nf Nh Nj Nl Nm Nq Ns Nt Nu Nx Ny Oe Oh Oi Oy Oz Pb Pf Pg Po Pz Qc Qd) Pc(Et Fp Hu Hv Hw Hx Il Im In Io Ip It Iv Jh Jq Li Lj Lu Lv Lw Lz Mc Mf Mg Mj Ml Mm Mp Mq Mu Mv Mw Mx Nb Nc Nd Ne Nf Ni Nj Nl Nm Nq Nr Ns Oe Of Oh Oi Oy Pb Pf Pg Po Qb Qc Qd) Hx(Et Hr Hu Hv Hw Ih Io Ip Iq It Iv Jn Jq Js Jt Li Lj Lu Lv Lw Ma Mf Mg Mj Ml Mm Mn Mp Ms Mu Mv Mw Mx My Nb Nd Ne Nf Ng Nj Nm Nq Nr Oe Oh Oi Pd Pf Pg Po Qa Qb Qd) Nr(Et Fp Hr Hv Il Im In Ip Iv Jk Jm Jn Jq Js Jt Lu Lv Lw Md Mf Mg Ml Mm Mp Mq Ms Mu Mw Mx My Na Nd Ne Ng Nj Nk Nl Nm Nq Oe Og Oh Pd Pf Pg Po Qb Qc Qd) Ok(Et Fp Hq Hr Hw Ii Ij Ik Il Im Io Iq It Jh Jk Jq Li Lj Ly Lz Mb Mc Md Me Mh Mm Mq Mw Mx My Na Nb Nc Nf Nh Nl Ns Nt Nu Ny Of Oy Oz Pb Pg Po Qc Qd) Mu(Et Fp Hu Hv Ii In Io Ip Iq It Iv Jm Jn Jq Li Lj Lu Lv Lw Lz Ma Mf Mg Mj Mp Ms Mv Mx Nb Nd Ne Ni Nj Nk Nm Nq Oe Og Oh Oi Pf Pg Po Qa Qb Qc Qd) Pa(Fp Hw Ii Ij Ik Il Im Jh Jk Li Lj Ly Lz Mb Mc Md Me Mh Mj Mm Mp Mq Mw Mx My Na Nc Nh Nl Nm Ns Nt Nu Nx Ny Of Oh Oi Pb Pf Pg Po Pz Qc Qd) Qa(Et Hv Ih Ii In Io Ip Iq It Iv Jn Js Jt Li Lu Lv Lw Ma Mf Mg Mj Ml Mn Mp Ms Mv Nb Ne Ng Ni Nj Nq Oe Og Oh Oi Oy Pb Pd Pf Pg Po) Lh(Et Fp Hw Ij Ik Il Im Jh Jk Jq Li Lj Lz Mb Mc Md Me Mh Mm Mp Mq Mw Mx Na Nb Nc Nh Nl Ns Nu Ny Oh Oz Pb Pg Po Qc Qd) Mv(Et Hu Hv Ii Io Ip Iq It Iv Jm Jn Jq Li Lj Lu Lv Lw Ma Mf Mg Mj Mp Ms Mx Nb Nd Ni Nj Nk Oe Og Oh Oi Pf Po Qb Qd) Jn(Et Hv Ih Ii In Ip Iv Jt Li Lu Lv Lw Ma Mf Mg Mj Ml Mp Ms Nb Nd Ne Ng Ni Nj Nq Oe Og Oh Oi Oy Pf Pg Po Qb) Nd(Et Fp Hv Ii Io Ip Iq It Iu Jm Jo Jq Lu Lw Ma Mj Mx Nb Ne Ng Ni Nk Nl Oh Pf Pg Po Qb Qd) Lv(Et Hv Ii Iu Iv Jm Jo Lu Lw Ma Mb Mf Mj Mw Nb Ni Nj Nk Nq Og Oh Pf Po Qb) Iv(Et Jm Js Lu Lw Ly Mb Mf Mg Mj Mn Nb Ng Ni Nj Nk Og Oh Pf Po Qb) Ma(Hv Ii Io Ip Iq It Jm Lu Lw Mf Mg Mj Nb Ni Nk Og Oh Pf Po Qb) Iu(Et Fp Hv Ii Ij Io Jk Lj Lw Mj Mn Mp Mx Nb Nm Ny Pg Qc Qd) Jo(Hv Hw Ii Ij Im Io Ip Jk Jq Jt Lw Mm Mp Mw Nk Nm Nq Oh Qb Qd) Qb(Et Ih In Ip Lu Lw Mf Mj Ms Nb Ne Ng Ni Og Pf Po) Nk(Et Hv Li Lu Lw Mj Mp Mx Nb Nc Oh Pf Pg Po Qd) Mz(Hq Ij Jk Il Im Lj Mh Nt Nu Of Qc Qd) Ng(Et Ii Jk Mj Mp Nb Oh Oy Pb Pf Pg Po) Et(Hv Jm Lu Mf Mg Mj Nb Ni Pf Po) Nb(Im In Jm Ms Ni Of Og Oh Pf) Mj(Il Im Jm Lu Mf Ni Oh Pf) Po(In Jm Mf Mg Ni Og Pd) Jm(Im Jk Mp Oh Pf Pg) Lw(Lu Mf Ni Oh Pf) Mf(Hw Jq Oh Pf) Ij(Is Jp Mi Mt) Ni(Oh Pf Pg) Im(Is Jp Mt) Lu(Oh Pf) Ik(Jp Mi) Il(Jp Mt) AaaA MlPb MsOh OgPf

Unconstrained panels with 2 analytes, where 5.0E-2 >= 'model p-value' > 1.0E-2. Contains 1,335 panels of 7,261 total panels evaluated. : Mj(Fp Hq Hr Hu Hv Hw Ih Ii Ij Ik In Io Ip Iq It Jh Jk Jq Js Jt Li Lj Lw Ly Lz Mb Mc Md Me Mg Mh Mk Ml Mm Mn Mp Mq Mr Ms Mw Mx My Na Nb Nc Ne Nf Nh Nj Nl Nm Nq Nr Ns Nt Nu Nx Ny Oe Of Og Oi Oy Oz Pb Pd Pg Po Pz Qc Qd) Po(Fp Hq Hr Hu Hv Hw Ih Ii Il Im Io Ip Iq It Jh Jk Jq Js Jt Li Lj Lu Lw Ly Lz Mb Mc Md Me Mf Mg Mh Ml Mm Mn Mp Mq Ms Mw Mx My Na Nb Nc Ne Nf Nh Nj Nl Nm Nq Ns Nt Nu Nx Ny Oe Of Oh Oi Oy Oz Pb Pf Pg Pz Qc Qd) Nb(Fp Hq Hr Hu Hv Hw Ih Ii Ij Ik Il Io Ip Iq It Jh Jk Jq Js Jt Li Lj Lu Lw Ly Lz Mb Mc Md Me Mf Mg Mk Ml Mm Mn Mp Mq Mr Mw Mx My Nc Ne Nf Nh Nj Nl Nm Nq Nr Nt Nu Nx Ny Oe Oi Oy Oz Pb Pd Pg Pz Qc Qd) Pf(Fp Hq Hr Hu Hv Hw Ih Ii Ij Im In Io Ip Iq It Jh Jk Jq Js Jt Li Lj Ly Lz Mb Mc Md Me Mg Mh Ml Mm Mn Mp Mq Ms Mw Mx My Na Nc Ne Nf Nh Nj Nl Nm Nq Ns Nt Nu Nx Ny Oe Of Oh Oi Oy Oz Pb Pd Pg Pz Qc Qd) Et(Fp Hq Hr Hu Hw Ih Ii In Io Ip Iq It Jh Jk Jq Js Jt Li Lj Lw Ly Lz Ma Mb Mc Md Me Mh Ml Mm Mn Mp Mq Ms Mw Mx My Na Nc Ne Nf Nh Nj Nl Nm Nq Ns Nt Nu Nx Ny Oe Of Og Oh Oi Oy Oz Pb Pd Pg Pz Qc Qd) Lv(Fp Hq Hr Hu Hw Ih Ij Im In Io Ip Iq It Jh Jk Jq Js Jt Li Lj Ly Lz Mc Md Me Mg Mh Ml Mm Mn Mp Mq Ms Mx My Na Nc Ne Nf Ng Nh Nl Nm Ns Nt Nu Nx Ny Oe Of Oi Oy Oz Pb Pd Pg Pz Qc Qd) Qb(Fp Hq Hr Hu Hv Hw Ii Io Iq It Jh Jk Jq Js Jt Li Lj Ly Lz Mb Mc Md Me Mg Mh Ml Mm Mn Mp Mq Mw Mx My Na Nc Nf Nh Nj Nl Nm Nq Ns Nt Nu Nx Ny Oe Of Oh Oi Oy Oz Pb Pd Pg Pz Qa Qc Qd) Iv(Fp Hq Hr Hu Hv Hw Ih Ii Ik Im Io Ip Iq It Jh Jk Jq Jt Li Lj Lz Mc Md Me Mh Ml Mm Mp Mq Ms Mw Mx My Na Nc Ne Nf Nh Nl Nm Nq Ns Nt Nu Nx Ny Oe Of Oi Oy Oz Pb Pd Pg Pz Qc Qd) Ma(Fp Hq Hr Hu Hw Ih Im In Jh Jk Jq Js Jt Li Lj Ly Lz Mb Mc Md Me Mh Ml Mm Mn Mp Mq Ms Mw Mx My Na Nc Ne Nf Nh Nj Nl Nm Nq Ns Nt Nu Nx Ny Oe Of Oi Oy Oz Pb Pd Pg Pz Qc Qd) Nd(Hq Hr Hu Hw Ih Ij Ik Il Im In Jh Jk Js Jt Li Lj Ly Lz Mb Mc Md Me Mf Mg Mh Ml Mm Mn Mp Mq Ms Mw My Na Nc Nf Nh Nj Nm Nq Ns Nt Nu Nx Ny Oe Of Og Oi Oy Oz Pb Pd Pz Qc) Oh(Fp Hr Hu Hv Hw Ih Ii Im In Io Ip Iq It Jh Jk Jq Js Jt Li Lj Ly Lz Mb Mc Md Mg Ml Mm Mn Mp Mq Mw Mx My Nc Ne Nf Nj Nl Nm Nq Nt Nu Nx Oe Og Oi Oy Oz Pb Pd Pg Qc Qd) Mv(Fp Hq Hr Hu Hw Ih Ij Ik Il Im In Jh Jk Js Jt Ly Lz Mb Mc Md Me Mh Ml Mm Mn Mq Mw My Na Nc Ne Nf Nh Nl Nm Ns Nt Nu Nx Ny Of Oy Oz Pb Pd Pz Qc) Jn(Fp Hq Hr Hu Hw Ij Ik Il Im Io Iq It Jh Jk Jq Lj Ly Lz Mb Mc Md Me Mh Mm Mn Mq Mw Mx My Na Nc Nf Nh Nl Nm Ns Nt Nu Nx Ny Of Oz Pb Pd Pz Qc Qd) Lw(Fp Hv Ih Ii Ij Il Im In Io Ip It Jk Jm Jq Li Lj Lz Md Mg Ml Mm Mp Ms Mw Mx My Nc Ne Ng Nj Nl Nm Nq Oe Og Oi Oy Pb Pd Pg Qc Qd) Qa(Fp Hq Hr Hu Hw Ij Ik Il Im Jh Jk Jq Lj Ly Lz Mb Mc Md Me Mh Mm Mq Mw Mx My Na Nc Nf Nh Nl Nm Ns Nt Nu Nx Ny Of Oz Pz Qc Qd) Mu(Hq Hr Hw Ih Ij Ik Im Jh Jk Js Jt Ly Mb Mc Md Me Mh Ml Mm Mn Mq Mw My Na Nc Nf Nh Nl Ns Nt Nu Nx Ny Of Oy Oz Pb Pd Pz) Iu(Hr Hw Ih Ik Il It Jh Jm Jo Jq Js Jt Li Lu Ly Lz Mb Md Mf Mm Mq Mw My Nc Ne Nf Ng Ni Nj Nk Nl Nq Nt Nu Nx Og Oy Pb Pz) Nr(Hq Hu Hw Ih Ii Ij Ik Io Iq It Jh Li Lj Ly Lz Mb Mc Me Mh Mn Nc Nf Nh Ns Nt Nu Nx Ny Of Oi Oy Oz Pb Pz) Nk(Fp Hw Ih Ii Ij Im Io Ip Jk Jq Js Jt Lj Lz Md Mf Mm Ms Mw My Ne Nf Ng Nl Nm Nq Nt Nu Nx Og Oy Pb Qc) Hx(Fp Hq Ii Ij Ik Il Im Jh Jk Ly Lz Mb Mc Md Me Mh Mq Na Nc Nh Nl Ns Nt Nu Nx Ny Of Oy Oz Pb Pz Qc) Hv(Hw Ii Im In Io Ip Jk Jm Jq Li Lu Mf Mm Mp Ms Mw Mx Ne Ng Ni Nj Nm Nq Og Oy Pb Pg Qd) Jo(Fp Hr It Jh Js Li Lj Lu Lz Md Mf Mg Mx My Nf Ni Nt Nu Nx Ny Of Og Oi Oy Pb Pz Qc) Ii(Im In Ip Jm Jq Lj Lu Mf Mg Mk Mm Mp Mr Ms Mw Mx Ni Nm Nq Oe Og Oi Pc Pg Qd) Pc(Hq Hr Ih Ij Ik Iq Jk Js Jt Ly Mb Md Me Mh Mn Na Nh Nt Nu Nx Ny Oz Pd Pz) Lu(Im Io Ip It Jq Jt Li Lj Mf Mm Mp Mw Mx Ng Ni Nm Nq Pg Qd) Pg(Hq Hu In Ip Jq Mf Mg Ms Mw Mx Ne Nj Nq Og Oi Pd Qd) Jm(Ij Io Ip It Li Lj Mm Mw Mx My Nm Nq Nx Oy Qc Qd) Mk(Hw Js Li Ly Lz Mc Mh Nh Ns Nt Nu Nx Ny Pb Pz) Mr(Hw Ij Li Ly Lz Mc Mh Nh Ns Nt Nu Nx Ny Pb Pz) Ni(Im Jk Li Lj Mf Mm Mp Mw

Figure 10 Continued

Mx Nc Nm Nq Pb Qc Qd) Ng(Ij Im Io Jh Li Mm Mw Mx My Nm Nq Nx Qd) Pe(Ij Ik Li Lz Mc Nh Ns Nt Nx Ny Pb Pz) Og(Ij Im Ip Jk Mw Mx Nq Oy Pb Qd) Mp(Hq Ip Jq Mf Ms Nq Pd Qd) Im(Ih Ir Mf Nj No Nv Om Qe) Mx(Io Ip Mf Mw Nj Nq Oy) Ij(Ir Jr Nn No Nv Om Qe) Ik(Ir Jr Nn No Nv Om Qe) Il(Ir Jr Nn No Nv Om Qe) Nq(Jq Mf Ms Qd) Mn(Io Ip Iq It) Hw(Js Me Ml Pd) Pb(Hq Mg My Ny) Mf(Jt Mw Qd) Jq(In Js Ml) Ms(Mw Oy) Ip(Ly Qd) MgJk MyOy InJt Constrained panels with 3 analytes, where 1.0E-8 >= 'model p-value' > 0. Contains 146 panels of 287,980 total panels evaluated. : aA{Iu(Fr Ir Is Ji Jl Lh Lx Ma Mi Mt Mz Ni Nk Nn Nv Nw On Qa Qb Qe) Lx(In Jj Jo Js Jt Li Mj Mn Mt Mx Ng Ni Nk Nr Pd Po Qd) Jl(Ih In Jj Jk Jo Js Jt Mj Mt Mx Ng Ni Nk Nr Pd Qd) Ir(Ji Js Lw Mz Nw) Mx(Is Ji Nw Ok) Jj(Lh Mg Mt Ni) Js(Is Ji Mi Nw) Ng(Fr Jg Pc) Nw(Mt Qd) MiMj IsJt JiJq} Iu{Lx(Ir Is Jj Jl Jm Li Mg Mi Ni Nk Pd Po) Jl(Fr Is Ji Jj Jp Lh Nk Nw Pa Pe) Jj(Is Lh Nv Nw On Pa) Fr(Ir Is Jr) MtNw NgOn JoLh} Jj{Is(Fr Jg Lu Mf Mi Mk Ml Mr Mt Mx Nd On Pc) Mt(Iv Mk Mr Pa) Jl(Lh Mm Mx Pa) Mf(Lh Lx) Nd(Ir Iv) IrLh} Lx{Mi(Hq In Pd) Po(Jm Nk) NrJl NgJg} MiNgJg Constrained panels with 3 analytes, where 1.0E-7 >= 'model p-value' > 1.0E-8. Contains 479 panels of 287,980 total panels evaluated. : aA{Mt(Jg Ji Js Jt Mi Mx Mz Ng Ni Nk Nr Ok On Pc) Lw(Hr Hv In Jo Js Jt Mf Mx Na Nf Pd) Pc(Jh Jo Js Mv Mx My Nf Ni Nq Of Oy) Jt(Fr Jg Ji Jn Jp Lh Nv Nw Ok On) Js(Fr Jn Jr Lh Mz Nv Ok On Pa) Pd(Ji Mi Nn Nw Ok On Pa) Mx(Fr Jn Jr Mz Nn On) Mi(In Jo Nf Nk Nq) Nw(Jn Jq Jr Nf Ni) Fr(Hu Jo Mn Nr) Jg(Hu Jh Jk Nq) Ji(In Jn Jr Nf) Ng(Mg Nv On) Jo(Lh Mg Nv) Nd(Hq Iq) Jq(Is Om) On(Hr Mn) NqMu NfOk Imlu IrJr} Lx{In(Hw Hx Iv Jj Jl Li Mk Mr Mt Ni Nk On Pa Pb Pf Po) Nk(Jj Jl Jm Jo Jt Li Mf Mg Ms Nd Ng Nr Pd) Li(Hq Jj Jl Jm Js Mg Mr Ng Ni Nq On Pd) Po(Hq Hu Jj Jl Js Ne Ng Ni Nq Nr Pd) Pd(Jl Lh Mf Mk Mr Nd Ni On Pa Pe) Ng(Fr Jl Mf Mi Mk Ni On Pc) Jj(Lh Mi Ml Mm Nd Ni Nj Pa) Jo(Hw Mi Mk Mr On Pa) Mi(Jm Js Nq Nr) Jl(Jm Js Jt) Nr(Mk On) Mf(Jm Ni) Is(Js Jt) MkOy NiJm JsNw JtOn} Iu{Fr(Hu Hx Ji Jn Lh Mg Mi Mk Mr Mz Ng Nk Nr Nw On Pa Pc Qb) On(Hu Ir Is Jm Jo Jr Jt Mg Mi Ms My Mz Ni Nk Og Pa) Nw(Ir Is Jm Js Mg Mi Ml Ms My Ng Nk Nx Og Pd) Is(Jm Js Lh Lu Mi Mt Mv Ni Nk Og Pa Pe) Jj(Ir Ji Jk Jp Jr Mu Nd Ok Pe Qa Qb Qe) Mi(Hq In Ji Jl Lh Mt Qe) Lh(In Mg Ng) Ji(Nx Pa) Jl(Ir Jr)} Jj{Ir(Ii Jg Js Mf Mk Ml Mn Mr Mu Nr Oy Pc) Iv(In Jg Jp Ma Mn Mu Mv Pc Qb Qc Qe) Pa(Fr Jg Ji Jr Js Lh Ml Ni Nk Nw On) Mt(Hx Lh Mf Mi Nd Nr Nw On Pc Pe) On(Et Jr Jt Mf Mi Mm Mn Ni) Jr(Fr Io Lh Mi Mk Mr) Lh(In Jo Jt Ml) Nw(Js Mf Mi Mx) Mi(Hq In) Jl(Nd Nk) FrMm MfJi ItPc} Mi{In(Hx Ir Is Ji Jl Jn Jr Lh Mt Mz Ng Nq Nw On Qa Qe) Hq(Fr Is Ji Jl Jn Jr Mt Mx Nd Nq Nw) Js(Is Ji Jl Jn Nw) Ng(Fr Jl On) Nq(Fr Jl) Is(Jm Jo) NrJl JoLh NwPd} Ng{Jg(Fr Hx Is Jl Jr Lh Lu Mm Mt Nv Nw On Pa) Fr(Hx Ii Is Mk Mr Nb On Pa Pb Pc) On(Js Jt Mf Mn Mt Mx Ni Nk) Jl(Nk Pa Pc) MtPc} Jl{Nr(Jp Nk Nw Pa Pe) In(Hw Iv Mr Pa) Nk(Jp Mx Pa) Jo(Mr Pa Pe) Is(Jm Jt) JpJt} Is{Fr(Jm Jo Jt Mg) Jo(Lh Mr Pa) Jm(Nd Pa) MzJs} Jo{Lh(Iv Mr Pa) MrNw MxOn} On{Jt(Ir Iv) MxOf}

Constrained panels with 3 analytes, where 1.0E-6 >= 'model p-value' > 1.0E-7. Contains 998 panels of 287,980 total panels evaluated. : Jj{Jr(Hx Ii Jg Ji Jk Jp Js Mf Ml Mv Mz Nb Nd Nn Nr Nv Ok Om Pc Pe) Fr(Hx Ii Ji Mf Mi Mk Mr Mz Nd Nj Nr On Pe Qb Qc) Jp(Hx Ii Lv Mi Mk Mr Mv Nb Ni Nk Nr On Pc Pe Qb) Jg(Hx Ii Jn Lv Mi Mk Mm Mr Mz Nd Nr On Pe Qb) Nv(Jo Lv Mf Mi Mk Mm Mn Mr Nd Ng Nj Nk Nr On) Jn(Hx Iu Iv Js Mi Mk Mr Mv Nd Nr On Pc Pe) Pe(Js Mf Ml Mv Mz Nd Nk Nn Pc Qb) Mk(Ji Ma Mv Mz Nn Om Qa Qb Qe) Mr(Ji Ma Mv Mz Nn Om Qa Qb Qe) Iv(Im Js Mf Mw Nm Oh Oy Pf) On(Hr In Ji Jo Mv Mz Nn Qb) Mi(Ji Mf Ml Mz Nq Pc Qe) Nd(Hx Ji Jk Lv Ok Om Qe) Nr(Ji Mv Mz Nn Om Qb) Iu(Lv Mp Nm Oh Pf Qc) Nn(Hx Lv Mm Nk) Mv(Hx Ii Ji Mz) Pc(Mz Ok Om Qb) Lu(Io Ip) Lv(Hx Mz) Nk(Io Qb) MfOm MxJi IiQb} Jl{Jo(Hw Is Ji Jp Lh Lx Mi Mk Mt Mx Nk Nr Nw On Pc Pf Pg) Jt(Fr Ir Ji Lh Mi Mk Mr Nw Ok Om On Pa Pc Pe Pf) Ng(Fr Jp Lu Mk Mr Mt Mx Nd Nw Om On Oy Pb) In(Hx Is Ji Jp Lh Mk Nb Nw Om On Pb Pe) Mx(Is Iv Ji Jp Lx Mg Mi Ni Nw Og On) Js(Ir Is Ji Jn Jp Jr Lh Mz No Nw Pa) Pa(Jm Mg Mj Mk Mn Ne Ni Og Oy Pd) Nw(Ip Jm Ml Mn Ms Mt Nq Og Pd) Ni(Jp Lx Mf Mi Nd Og On Pc) Pd(Ji Jp Lh Mi Nd Pe Pf) Lx(Ih Mn Mr Ne Nq Ny) Pc(Jm Mg Ms My Nq Og) Nk(Jm Ms Nd Pe Pf) Nr(Ji Lh Mt Pf) Fr(Hu Mn Nq) Mi(Jm Mt Nt) Is(Ih Ip Mr) Ji(Ip Jq Mf) Jp(Jm Mn Ny) Nq(Jg Nd) Mk(Of Oy) LyIq NdJm OfOn} Jo{Mi(Fr Hq Hx In Ip Ir It Iu Iv Jg Ji Jp Mk Mr Mt Mz Nr Nv Nw Ok Om On Pa Pc) On(Fr Hw Ji Jp Lh Ma Mk Mn Mr Ms Mt Ni Nv Nw Pa Pe) Is(Hw Lu Lw Mk Mv Mz Nd Nn Nr Nv Og Pc Pe) Fr(Hx Ir Iv Ji Jr Lh Mk Mr Nr Pa Pe) Mk(Ir Ji Lh Ma Mt Mz Nv Nw Ok Om) Mr(Ir Jg Ji Jp Ma Mt Nn Nv Ok Om) Pa(Ir Iu Jg Ji Jp Mt Nk Nv Nw Ok) Lh(In Lw Lx Mf Mj Ml Nr Pc Pe) Pe(Iu Jg Ji Lx Mt Nv Nw) Ir(Iu Nn Nv Om Pc) Nw(Hw Js Ml Mt Nr) Lx(Hq Ni Nr Pc) Nv(Ip Iu Nr) Ji(Hw Nr) OkPc} Nw{Ng(Fr Js Lu Mf Mi Mk Ml Mr Mt Mx Nd Nk On Pa Pc) Js(Fr Jh Ji Jm Jn Jr Mf Ms Mt My Mz Nd Pa) Jt(Fr Is Jp Lx Mi Mk Ml Mr Mt Nr On) Pd(Lh Mk Mr Ms Mt Nd Nk Nr On Pa Pe) Mi(Jm Mj Ml Mt Mx Ni Nk Nq Nr) Mx(Is Iv Jm Md Mg Ms My Ny) In(Hw Iv Mr Nd On Pa Pb Pe) Mt(Fr Lx Mf Nd Nk Nr Og) Ms(Lx Mf Nd Nk Pc) Fr(Mg My Nq Nr) Nd(Jm Ni Nk Nq) Nr(Jr Pa) My(Jg Pc) LxMl LyIq MkOy NkJr IsJq OgPc PaPe} Iu{Pa(Ir Jg Jm Jp Jr Lh Ma Mi Mt Mz Ni Nk Nn Ok Om Oy Pd Qa Qe) Mi(Ir Jg Jm Jn Jp Jr Mv Mz Nk Nn No Nv Ok Om Qa Qb) Lh(Hu Ir Ji Jm Jr Jt Ms Mt Mz Ni Nk Nn Pd Qb Qe) Mt(Ir Ji Jr Mj Mk Mr Mz Ng Nk Nr On Pe Qe) Ji(Ir Jr Lu Mf Mk Mr Ms Mv Nd Nn Nr On) Mz(Ir Jg Lv Ma Mk Mr Mv Nn Pc) Ir(Jp Ma Mv Nd Nn Om Pc) On(In Oi) FrNj NnJr NoNk MgOm NgNv} Lx{On(Hq Hr Ii Jk Mk Ms My Nb Ni Nq Of Oy Pg) Jt(Ir Jg Ji Jp Mf Mi Mk Mr Ok Pa Pc Pe) Js(Ir Ji Jn Jr Mf Mz Ng Pa) Pc(Jh Mg Ms Mv My Nq Og) Mn(Fp Li Mi Mk Mr Ne) Ng(Fp Lu Mr Nd Pa Pb) Hq(Mh Mk Nd Pa Pb Pf) Mg(Fp Fr Jg Mf Mi) Nq(Fr Jg Lu Mf) Ni(Mi Mk Mr Pa) Hu(Fr Jg Mf) Mk(Li Of) Mx(Is Iv) In(Lh Pe) NtMi LyIq MyJg HrJr HvHw JiNx PaPe} Mi{Ng(Hq Is Ji Jp Lh Mt Mv Nv Ok Om Pc) Jp(Hq In Js Jt Ni Nk Nq Nr Pd) On(Hq Jm Js Jt Ni Nq Nr Pd) Fr(Jn Jm Mg Nr Pd) Mt(Jm Js Nq Nr Pd) Is(Jt Mx Nk Nr Pd) Jg(Hq In Mg Nq Nr) Ji(Jm Nq Nr Pd) Hq(Mz Nv Pa) In(Ok Pa Qb) Js(Jr Mz) NqMu IrJm JtOk} Is{Fr(Hu Ih In Ip Js Li Mk Mx Nk Nq Nr Og Oi Pd) Jt(Jg Jp Lh Lw Mk Mr Mz Nn Og Ok Pa) In(Hw Iv Lh Mr On Pa Pb Pe) Jm(Jq Js Lu Mf Mx Og Pc) Nk(Mz Nd Og Pa) Js(Ji Jr Pa) Mx(Ji Mz) Nd(Ng Ni) NrPa MgJg NgPc} On{Jt(Fr Hu Jm Jp Mg Mn Ms Mt My Nk Nq Pa) In(Hw Iv Jr Mr Mt Mx Ni Pa Qb) Ms(Hr Mn Ni Nk Nr Pd) Nr(Fr Jr Mt Pa) Mg(Mn Mx Ni Nk) Ng(Hr Jq Nv) Of(Fr Mk Mt) Mx(My Oy) Ni(Hu Jm) MkOy MnJm PaPd} Fr{Ng(Jr Lh Mn Mt Nd Nk Nr Nv Om Oy Pe) Nr(Ir Ji Jr Mk Mr Pa Pe) Jm(Hx Ir Iv Ji Jr) Mg(Ji Jr Pc) Jt(Ir Iv Ji) Mk(Of Oy) In(Iv Pa) IpJi} Mt{Ng(Mk Mr Nd Oy Pa Pb) In(Hw Iv Mr Pa Pe) Nr(Mk Mr Pa) MkOy MsPc} Ji{In(Hw Iv Mr Pa Pb Pe) Pa(Js Nr Pd) Nd(Jm Ni) MfNi NgPc JrJs} Ng{Pc(Jp Lh Nv Om) MkNv} Mz{Iv(In Js) IrJs} Nd{Jm(Ir Iv)}

Constrained panels with 3 analytes, where 1.0E-5 >= 'model p-value' > 1.0E-6. Contains 2,022 panels of 287,980 total panels evaluated. : Mi{Ng(Et Hx Ii Io Ir Iv Jk Jm Jn Jr Ma Mf Mg Mk Mr Mu Mw Mz Nb Nd Ne Nk Nn Nq Nr Of Oi Oy Pa Pb Pf Qa Qe) Nq(Hr Ir Is Iu Jn Jo Jr Lh Ma Mv Mz Ni Nk Nn Nv Ok Om Pc Pg Qa Qe) Pd(Hw Hx Ir Jg Jn Jr Lh Mk Mr Mz Nb Nn Nv Ok Om Pa Pc Pe Pf Po Qe) Jm(Hx Jg Jn Jp Jr Js Lh Ma Mv Mx Mz Nn Nv Oh Pa Pc Po Qa Qb Qe) Ni(Fr Hx Is Jg Ji Jr Lh Mf Mk Mr Mt Mz Nn Nr Ok Pa Pc Qe) Js(Fr Hx Ir Iv Jg Lh Nn No Nv Ok Om Pa Qa Qb Qe) Nr(Hx Ir Jn Jr Lh Mz Nn Nu Nv Ok Om Pa Pc Qe) Nk(Fr Jg Ji Jo Jr Mt Mz Nc Nn On Pa Pc Qe) Nt(Fr Is Jg Ji Jp Mt Nw Ok On) Jo(Hw Jn Jr Lw Nn Pe Pf Pg Qe) Jt(Fr Ir Jg Ji Lh Mt Mz Om Qe) Ml(Ir Is Ji Jn Jr Mz Ok Om) Mg(Is Ji Lh Mt Nv Ok Om) On(Hr Ii Mn Mx Nb Nf Pg) Jg(Hu Jh Jk Ms Mv My) Mf(Ji Jr Mt Ok Qe) Mx(Ir Ji Jr Mz Ok) Fr(Hu Jr Mn) Mk(Is Oy Pg) Pc(Jr Ms Mz) Mr(Is Pg) Mt(Hu Ne) LyIs NeJl Imlu JiJq PbPg} Jo{Pa(Et Hw In Jm Jn Jr Lv Lw Ma Mk Mm Mr Mu Mv Mz Ni Nm Nn Nr Om Pc Pe Qa Qe) Jp(Fr

Ml Mm Mp Mu Mv Nb Nd Nk Nm No Nx Oh Pf Po Qa Qb Qe) Po(Et li Ip Iu Jk Jn Jt Lv Lw Mj Mm Mu Mv Nb Nd Ni Nm Oh Pd Qa Qb Qd Qe) Lw(Et Hv Ii Im Io Ip Jk Jn Lv Mj Mu Nb Nd Nk Nm Nq Oh Pf Pg Qa Qb Qd) Nd(Et Ii Ik Io Ip Jk Jn Jt Mj Mu Mv Nb Nm Oh Pc Pf Pg Qa Qb Qd Qe) Lv(Et Ii Ip Jk Jn Jt Ma Mf Mj Mm Mw Nk Nm Nq Oh Pf Pg Qa Qb Qe) Jt(Et In Ip Jk Js Ma Mf Ml Mu Mv Nk Nm Oh Pc Pf Pg Qb Qe) Mj(Im Jk Jn Jq Mf Mm Mw Nk Nm No Nq Oh Pc Pf Pg Qa Qb) Ii(Et Io Ip Jk Jn Jr Mm Mu Nk Nm Nq Oh Pf Qb Qd Qe) Nb(Im In Jk Jn Mm Mu My Ng Nk Oh Pg Qb Qd) Pc(Im Jh Jk Jq Lj Mm Mu Mx Ni Nq Oh Pg) Ip(Hv Jk Jn Jq Mn Oh Pf Pg Qb Qc Qd) Mu(Et Jn Nk Nm No Pf Pg Qa Qb Qe) Nk(Hv Jk Li Mp Mv Oh Pf Qb Qd) Et(Iu Jk Jn Lu Mv Pf Pg Qb) Nm(Hv Iu Jk Jn Lu Mv Pf Qb) Ni(Jk Jn Oh Pf Pg Qa Qb) Ma(Hv Jn Lu Qa Qb Qe) Iu(Ij Jk Oh Qc Qd) Pg(Jm Jn Mv Qa Qe) Mv(Qa Qb Qe) Jn(Iv Js Pf) Pb(Ml My Ny) No(Mc Ml) Ng(Jk Oy) LuOh ImPe IvOy} Ng{Oy(Et Hx Im Ir Iu Iv Jn Lv Mf Mp Mw Nd Ni Nk Nm No Nq Oh Pa Pe Pf Pg Po Qa Qb Qd) Pb(Et Hx Im Ir Jn Lv Mg Mm Mp Mw My Nd Ni Nk Nm Nq Oh Pe Pf Pg Po Qb Qd) Nb(Et Hx Im Ir Iu Jn Jr Mm Mp Mw Nd Nk Nm No Nq Oh Pe Pf Po Qa Qb) Mr(Hr Hx Im Iv Lv Mm Mp Mw Nd Ni Nk Nm No Nq Oh Pe Pf Po Qb) Mk(Hx Im Iu Iv Lv Mm Mp Mw Nd Ni Nk Nm Nq Oh Pe Pf Pg Po) Pe(Et Hr Hx Ii Im Ir Jk Jn Jr Lu Mw Nd Ni No Nq Qa Qb) Nd(Et Hx Ii Ik Ip Jn Jr No Nt Oh Pf Pg Po Qa Qb) Hx(Et Ii Jk Jr Lu Lv Mf Mp Ni No Nq Pf Qe) Ii(Et Ir Jk Jn Jr Mp No Nq Pf Qa Qb Qe) Jk(Et In Jr Lw Ma Mf Mj Mp Ne Ni Po) No(Jr Js Lu Lv Ma Mc Ml Mu Ni) Ma(Jn Lu Lw Mf Po Qa Qb Qe) Po(Et Lv Ni Pd Qe) Lu(Et Ir Jn Qe) Mf(Hw Mu Qa Qe) Nk(Pf Pg Qa Qb) Ij(In Iu Mi) Jr(Et Mp Qe) Ir(Mn Mp) Pa(Im Pf) EtMu NiQe IuPg} Jg{Nq(Hx Iu Jm Jn Lh Lu Lv Mp Nb Ni Nn No Nv Og Oi Om Pe Po Qa Qb Qe) Ms(Ir Jn Jp Lv Mj Mk Mr Nb Nd Ni Nk Nn No Oh Ok Pe Qa Qb Qe) Jh(Hx Iu Jm Jn Jq Lh Lu Lv Mk Nd Ni Nk Nn Pe Qa Qb Qe) Og(Ir Iv Jn Jp Lh Lv Mk Mr Mv Ni Nk Nn Pe Qa Qb Qe) Mw(Hx Jm Jr Lu Mj Mk Mr Nb Ni Nn Oi Om Pc Pe Po) My(Ir Iu Jm Jn Jp Lv Mj Nd Ni Nk Nv Om Po Qb Qe) Nk(Hv Iv Jn Lh Lu Mk Mp Mr Mv Oi Pz Qa Qe) Pz(Hu Hx Jn Lh Mj No Ok Pe Qa Qb Qe) Mv(Hx Jm Jn Lh Lv Ni Nn Om Pc Qb) Oi(Hx Ir Jn Lh Mk Nn Pe Qb Qe) Pd(Hw Jq Li Mp Mr Ok Om Po) Ni(Hu Hx Jn Lh Mj No Qb) In(Jn Jq Nb Ok Om Po Qa) Js(Hw Iv Jn Jq Lh No) Mf(Hw Jq Lv Mj Qa) Of(Hx Nb Pb Po) Ml(Hw Jq Pb) Hu(Ir Lv Pc) Jm(Lu Ok Qd) Nm(Hw Jq) Hq(Mp Pb) Hx(Jk Oe) Il(On Pa) Oy(Pc Pe) NtLh LvNd NjIv HvHw JnJq NyPb PaPe}
Pc{Ni(Hu Hx Jh Jm Lh Lj Lw Mg Mj Mu Mv Mx Nd Nq Nv Oh Pe Pf Qa Qb Qe) Mg(Et Hx Im Jk Jn Jq Lv Mu Nd Nk Nm No Oh Pe Pf Po Qa
Qb Qe) Nk(Hu Hx In Iu Iv Jh Jm Lj Mu Mv Mx Nc Nd Nl Nq Oh Pf Qb) Mv(Hu Hx Jh Jm Jn Ma Mu Nn Nq Nv Oi Qa Qb Qe) Il(Hx Ir Iv Jn Lh
Mj Mk Mr Ok Pa Pe Qa Qe) Jm(Et Hv Im Jk Lv Mc Mu Mx Nd Oh Pf Po Qd) Iu(Et It Jq Lj Lv Mj Mn Mx Nd Oh Po Qc) Oi(Et Hx Iv Jn Ma
Mu Nn Nv Om Qa Qb Qe) Nq(Et Hx Ma Mu Nd Nn No Pe Qa Qb Qe) In(Jn Jq Jr Mc No Om Po Qa Qb) Jh(Hx Jn Jq Ma Mu Nn Qa Qb Qe)
Of(Mk Mr Nb Nv Om Pa Pb Pe) Hu(Lh Ma Mc Mu Nv) Oy(Hx Mr Nv Om Pe) Nd(Iv Jn Qa Qe) Mw(Lh Nv Om) Hr(Mr Pa Pe) Jt(Jn Nv Om)
Mf(Jq Lv) Jk(Nv Om) Pa(Hq Nf) MlJq IkIv PdPe} Mk{Oy(Et Hx Im In Ir Jk Jn Jq Lv Nd Nk No Nq Oh Pe Pf Pg Po Qa Qb Qe) Of(Et Hx Im In
Jk Jn Jq Mp Nd No Nq Ny Oh Pa Pe Pf Po Qa Qb Qe) Ni(Hr Hx Im In Ir Iu Ma Mu Mv Nd No Oh Ok Pe Pf) Nk(Hr Im In Ir Iv Jn Ma Mu Mv
Nd Oh Om Pf Po) Hr(Hx Ir Jn Jq Lh Ms Ok Om Pa Pe Qa Qb Qe) In(Et Im Iu Jq Lv Ms Mu Mv Nd Oh Pf Po) Jm(Im Iv Jn Ma Mu Mv Oh Pf Po
Qb) Jt(Et Im Ir Jn Jq Ma Nn No Qa Qe) Og(Ir Iv Jn Mu Mv Nn Nv Om Qb Qe) Ms(Et Hx Jn Mu Mv Nv Oh Ok Qb) Pd(Jq Lh Nn No Nv Ok Om
Pe Pf) Il(Im Mi Nn Nv Pa Qa Qb Qe) Iu(Iv Jk Jq Lv Mn Nd Nm Qd) Mg(Ma Mu Mv Nn Nv) My(Mv Nn Nv Om) Mf(Jq Lv) Mv(Hu Ir) EtNd
NfJq QaJs JkNv} Nk{Nd(Et Fp Hv Hx Lu Ma Mj Mr Mu Mv Mx Nc Nh Ni Nu Oh Pf Pg Po Qd) Mv(Hu Hv Hx Iv Jm Jn Li Lv Mg Mj Mp Mr
Ms Nc No Qb Qe) Mu(Iv Jm Jn Li Lj Lv Mg Mj Mr Ms Og Pf Qb Qe) Po(Hu In Iv Jm Mg Ml Mr Ms My Nc Of Og Pd) Iu(Ij Im Iv Jk Mp Nb
Oh Pg Qc Qd) Hx(Mg Mp Ms Nc Nl Ok Pf Qb Qe) Iv(Lu Ly Ma Mn Mp Og Oh Pf Qb) Lu(Et Jn Lv Oh Qa Qb Qe) Mr(Hr Jn Ma Oh Om Pf)
Pe(Hr Nv Pf Qa Qb Qe) Jn(Jm Js Mf Mp No) Om(Ir Ms No Qb Qe) Mf(Lv Ok Qb) Mp(Hv Nc Nl) Jm(Jk Oh Pg) In(Nb Pb) Qe(Nv Og) NoJs
LvPf MaHv MlLh MsOh QbLi JtNv} Jm{Nd(Et Hv Ik Im Ip Jk Ma Mv Mx Nl No Oh Pf Pg Po Qd) Qb(Jn Jr Lv Lw Mj Mp Mr Mv Nb Ne Ni
No Oy Pe Pf Po) Mu(Et Ii Jn Lv Ma Mj Mp Mr No Oh Ok Pf Pg Po Qa) Mv(Ii Jn Lv Lw Mj Mp Mr Nb Oh Pe Pg Po Qa) Iv(Et Iu Jk Jn Mn Mp
Mr Og Oh Pf Pg Po Qc) Jn(Hx Ip Js Lu Lv Ma Mp Mr Oy Pg) Po(Et Iu Lv Ma Mr Ni Oh Pe) Ma(Hv Ii Lv Mr Nb Oh Qa) Jr(Mf Ml Mp No Pe
Qa) Mr(Hr Im Oh Pf) Lv(No Oh Pf) Ni(No Oh Pg) Iu(Jk Oh Pg) Hx(Mp Pf) Pe(Hr Mf) EtLu QaOy} Ni{Nd(Et Hv Hx Ii Ma Mj Mr Mu Mv Mx
Nc Ne No Nv Oh Pe Pf Po Qa Qb Qd) Pe(Hr Hx Ir Jn Ma Mf Mr Mu Mv Nv Oh Pd Qa Qb Qe) Mf(Hw Hx Ir Jn Lv Mj Nn No Om Pf Qa Qb
Qe) Mr(Hr Hx Im Ir Iu Ma Mu Mv No Oh Ok Om Pf) Hx(Ir Jr Ma Mu Mv Nn Og Pf Qe) Mv(Jn Jr Lw Mj Qb Qe) Nv(Hu Jr Mg Ms My Og)
No(Jr Js Mc Ml Qe) Qb(Lu Lw Ma Mj Mu) Lh(Js Ms Nn Nt) Mu(Jn Jr Mj) Iu(Jk Mn Oh) Lu(Jn Ok) In(Nb Po) Qe(Jr Og) NnHu MaJr JnJs}
Iu{Nd(Et Fp Ii Ij Ip Jk Jq Lj Mj Mn Mr Mx Nb Nm Oh Pf Pg Po Qc Qd) Lv(Et Ii Jk Lj Lu Mb Mf Mj Mn Mr Nb Oh Pf Qc) Nb(Et In Jk Jn Lj
Mn Ms Nm Og Oh Pf Qc Qd) Mn(Ii Jk Lu Lw Mj Mr Mu Mx Pf Pg Qc) Po(Et Im In Iv Mj Oh Pd Qd) Qc(Ii Lw Mj Mp Mu Mx Pf) Et(Iv Lu Mj
Mx Oh Pf) Mr(Hr Iv Jk Nm Qd) Lu(Im Nm Oh Qd) Mj(Jk Mf Oh Pg) Mu(Lj Pf Qd) Ii(Mx Pf Qd) Im(Jp Og Oh) Mg(Jk Pg) Iv(Oh Pf) Og(Ij Jk)
MfHw} In{Nb(Hx Im Jq Lv Ma Mu Mv Nd Nn No Nv Oh Ok Om Pe Pf Po) Mj(Hx Im Mf Ml Mu Nn Nv Ok Om Qa Qe) Ir(Ii Jr Lu Lv Lw Mn
Mu Mv No Ok Po) Nv(Hu It Jn Jr Nd No Ok Po Qa Qe) Om(It Jn Lu Nn No Ok Po Qa Qb Qe) Qa(Ii Jr Lw Mu Nd Nn Po) Qe(Ii Jq Jr Nn No Ok
Po) Jn(Ii Mu Nd Nn Ok Po) No(Ii Lu Mc Nd Qb) Hx(Im Oh Pf Po) Jr(Ii Lw Mu) Ok(Jq Mv Qb) Pb(Et Im Nd) Po(Pd Qb) Mz(Ij Lw) It(Nd Nn)
ImPe} Pa{Pe(Et Hq Hr Ir Jn Jq Lh Lv Ma Mu Mv No Nv Om Qa Qe) Hq(Hr Hx Js Lv Ma Mf Mp Mv Pb Qa Qb Qe) Il(Im Ir Jn Lh Mi Mr Mv
Nn Nv Qa Qb Qe) Hr(Hx Jq Mu Ne Nn Nq Nt Om Pg Qb Qe) Nf(Hx Jq Mu Mv Nv Ok Om) Jt(Et Jn Jq Ma No Qa Qe) Js(Ma Nn No Nv Qb Qe)
Mu(Hu Ms Of Og Oy) Mv(Hu Mg Of Og Oy) Nv(Jk Ms My Of Og) Nn(Mg Mn Oy) Ma(Mg Mn Oy) Pd(Pf Qb Qe) Jq(Mx Of) Og(Hx Qe) NtLh
LyIq MwMy} Pd{Pe(Et Hr Hw Hx Ir Jn Jq Lu Lw Ma Mr Mu Mv No Oh Pb Pf Po Qa Qb Qe) Om(Hw Hx Jn Li Lu Mj Mp Mr No Og Ok Pf Po
Qa Qe) Ok(Hx Ir Jn Lu Ma Mp Mr Mv Nv Pf Qa Qb) Po(Et Ir Jr Ma Mp Mz Nn Pf Qa Qc) Nn(Hw Iv Jn Li Mj No Pb) Mp(Hx Ir Jp Jr Mz No
Nv) Mr(Jq Mv No Nv Pf Qa) Nv(Hw Li Mj Nd Pb) Jr(Hw Li Pb) Pf(Hx Ir Nd) Lw(Ir Mz) NoPb LvNd MjLh MzLi} Js{Ir(Iv Jn Jq Lu Lv Lw Mj
Mn Mp Mu Nb No Nv Oh Pb Pe Pf Po) No(Hx Jq Lh Lv Ma Mu Mv Nd Nv Oh Ok Om Qa Qb Qe) Jn(Hw Hx Iv Lv Mp Mu Mv Nb Nv Ok Om
Po) Qa(Hw Ih Iv Mj Mr Nb Nd Ok Om Pb Pe) Iv(Jq Ma Mu Mv Nv Om Qb Qe) Jq(Lh Mr Nn Ok Pe) Nv(Hu Hw Mj Pb Pe) Hw(Nn Om Qe)
Pb(Jp Nn Qe) PoJp HuLh HxOm QbPe} Mf{Lv(Hw Hx Ir Jn Jq Lw Ma Mj Mr Mu Mv No Nv Oh Om Pe Pf Qa Qe) Hw(Hr Jn Jq Jr Ma Mu Mv
Nn Nv Qa Qb Qe) Lw(Ir Iv Jn Jr Mv No Nv Qa Qe) Mu(Ir Iv Jn Jr Mj My Qa Qe) Qa(Ih Ma Mj Mr Om Pe) Ma(Ir Iv Jr Mj) Pe(Jn Jq Jr Mz)
Mv(Ir Jr Mj) Qe(Jq Jr Om) Nn(Hu Og) MjNv MrJq HqLh HxOg} Jt{Ir(Et Hx Ii Jh Jr Lv Lw Mr Nq Pe Pf Qe) Nv(Hu Jn Jr Lw Mj Mz No Pe Qa
Qe) No(Hx Lv Lw Mr Mu Nn Pe Qc) Mr(Et Im Jn Jq Ma Qa Qe) Pe(Et Jn Ma Nn Om Qa Qe) Jn(Et Ma Mu Mv Nn) Om(Hu Mj Nd Nn Og)
Mz(Ii Pf Qe) Et(Jr Nn) Ma(Iv Qa) NnMj} Mg{Ma(Hx Ii Jn Lw Mr Mu Mv Nb Nd Nv Oy Pb Pe Po Qe) Mv(Et Hx Ii Jn Lv Lw Mr Nb Nd Nv Pb
Pe Qe) Mu(Et Hx Jn Lv Mr Nb Nd Pb Pe Qb Qe) Ir(Et Hx Lw Mn Mp Pb) Nd(Et Hx Ip Lv Nv) Nn(Hx Lv Mr Pb) Nv(Mr Pb Pe) Et(Hx Lu)
LvHx JrPb} Lh{Hq(Hv Jn Me Ml Mp Mx Na Nm) Nq(Mu Mx Na Nd Nf Nn Nv) Nt(Jr Mv Mz Nd Nn Ok Qe) Hu(Hr Ma Mu Mx Nf Nn Nv)
Of(Mr Nb Ne Pb) Nn(Ii Og Oi) Ih(Ir Qc) MlNe MrHr MyPb IiIr JkNv NxOm} Og{Mu(Hx Ii Ir Iv Jn Mj Mr Nb Pe Qe) Mr(Ir Iv Jn Mv Nn Nv
Qb Qe) Mv(Hx Ii Ir Iv Lw Nb Qe) Hx(Jr Ma Nv Ok Qe) Ir(Lw Pb Pe) Qe(Nb Nv Pe) Nv(Hu Pe) Om(Jh Ms) Oy(Jr Mz) LwIv} Ml{Pb(Hr Ir Jn
Jp Jq Jr Nn Nv Qa Qe) Jr(Hw Hx Lv Lw Ma Mv Nb No) Iv(Jp Ma Mv Nv Qa) No(Jp Nn Om Qe) Mz(Hw Mj Nb Ok) Nn(Hw Hx) Ir(Jq Om)
HrHx HwJp QaOm JqOk} Nv{Mr(Hr Jk Ms My Of) Nn(Mv My Nq Oi) Ms(Jr Nb Nd Pe) Of(Nb Ok Pb Pe) Nd(Hu Mn Nq) Mx(Iv Mj) My(Nb
Pb) Hu(Mu Mv) NqNb HqPb IvJn} Pb{My(Jr Ma Mu Mv Mz Nn Om) Hq(Jp Jr Ma Mz Nn) Ny(Jp Jr Mz Nn Om) Hx(Jp Jr Mz Nn) Of(Mt Nn

Figure 10 Continued

Ok Om)} Mr{Hr(Hx Jn Jq Mu Mv Ok Qa Qb Qe) Of(Jq Ma Mu Mv Nn) Ms(Mu Mv Om) Il(Is Qa Qe) EtNd MvHu NfJq} Om{Of(Hx Lu Nb Ok Pe) Nn(Mv My Nq Oi) Lu(Jh My Nq) Hu(Jq Jr) NmIr MpHq MsQc HrPe HvHw} Jn{Hw(Hv Jp Jr Mz) Iv(Jp Ma Mv Qa) Mx(Mj Ok Pe) Lv(Lu Nd) Mu(Ms Nd) Jq(Ir Ok) NnOi} Mv{Hu(Hx Ir Iv Jp Lv Mu Nd Ok Pe) Of(Nb Ok Pe) Ms(Hx Nb) NdIv} Ms{Mu(Hx Mj Nb Qb Qe) Nb(Jr Ma Nn Qe) NnHx NoQe JrOy} Hw{Hv(Ir Jp Jr Nn) Mz(Jr Me Na) Mt(Jr Nm) MeJr IjJj} Mx{Qa(Is Mj Ok Pe) Mj(Ir Jr) Nolv MzOk JrPe} Nd{Et(Lu Mn) Lv(Hq Qe) Iv(Ly Ma) NnMn MiMy MuHu} Nn{Nb(My Nq Of) Lu(Hu Nq) Oi(Mn No)} Hx{Hr(Ok Pe) Hu(Ma Mu) Ny(Mt Mz) IhQe} Mi{Nt(Et Ma Oh Pf) Ne(My Nf)} Ir{Lu(Ma Mn) Ly(Iq Mp) Mnlh IvJr} Nb{Of(Ma Mu Ok)} Jr{EtLu MyOy IvQa} LyMulv MjIlIs MyJp Hu Hv Hw Hx Ih Ii Ij Ik Il Im In Io Ip Is It Iu Iv Jg Jh Ji Jj Jk Jl Jm Jn Jo Jp Jq Jr Js Jt Lh Li Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Og Oh Oi Ok Om On Oy Oz Pa Pb Pc Pd Pe Pf Pg Pz Qa Qb Qc Qd Qe) Is(aA Et Fp Fr Hq Hr Hu Hv Hw Hx Ih Ii Ij Ik Il Im In Io Ip It Iv Jg Jh Ji Jj Jk Jl Jm Jn Jo Jp Jq Jr Js Jt Lh Li Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Og Oh Oi Ok Om On Oy Oz Pa Pb Pc Pd Pe Pf Pg Pz Qa Qb Qc Qd Qe) Iu(aA Et Fp Fr Hq Hr Hu Hv Hw Hx Ih Ii Ij Ik Il Im In Io Ip It Iv Jg Jh Ji Jj Jk Jl Jm Jn Jo Jp Jq Jr Js Jt Lh Li Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Og Oh Oi Ok Om On Oy Oz Pa Pb Pc Pd Pe Pf Pg Pz Qa Qb Qc Qd Qe) Jj(aA Et Fp Fr Hq Hr Hu Hv Hw Hx Ih Ii Ij Ik Il Im In Io Ip It Iv Jg Jh Ji Jk Jl Jm Jn Jo Jp Jq Jr Js Jt Lh Li Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Mu Mv Mw Mx My Mz Na Nb Nc Nd Ne Nf Nh Nj Nl Nm Nn No Nq Ns Nt Nu Nv Nw Nx Ny Oe Of Og Oh Oi Ok Om On Oy Oz Pa Pb Pc Pd Pe Pf Pg Pz Qa Qb Qc Qd Qe) Jk(aA Et Fp Fr Hq Hr Hu Hv Hw Hx Ih Ii Ij Ik Il Im In Io Ip It Iv Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Og Oh Oi Ok Om On Oy Oz Pa Pb Pc Pd Pe Pf Pg Pz Qa Qb Qc Qd Qe) Jm(aA Et Fp Fr Hq Hr Hu Hv Hw Hx Ih Ii Ij Ik Il Im In Io Ip It Iv Jg Jh Ji Jk Jn Jo Jp Jq Jr Js Jt Lh Li Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Og Oh Oi Ok Om On Oy Oz Pa Pb Pc Pd Pe Pf Pg Pz Qa Qb Qc Qd Qe) Li(aA Et Fp Fr Hq Hr Hu Hv Hw Hx Ih Ii Ij Ik Il Im In Io Ip It Iv Jg Jh Ji Jk Jn Jo Jp Jq Jr Js Jt Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Og Oh Oi Ok Om On Oy Oz Pa Pb Pc Pd Pe Pf Pg Pz Qa Qb Qc Qd Qe) Og(aA Et Fp Fr Hq Hr Hu Hv Hw Hx Ih Ii Ij Ik Il Im In Io Ip It Iv Jg Jh Ji Jk Jn Jo Jp Jq Jr Js Jt Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pd Pe Pf Pg Pz Qa Qb Qc Qd Qe) aA(Et Fp Fr Hq Hr Hu Hv Hw Hx Ih Ii Ij Ik Il Im In Io Ip It Iv Jg Jh Ji Jk Jn Jo Jp Jq Jr Js Jt Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pd Pe Pf Pg Pz Qa Qb Qc Qd Qe) Js(Et Fp Fr Hq Hr Hu Hv Hw Hx Ih Ii Ij Ik Il Im Io Ip It Iv Jg Jh Ji Jk Jn Jo Jp Jq Jr Jt Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pd Pe Pf Pg Pz Qa Qb Qc Qd Qe) Jt(Et Fp Fr Hq Hr Hu Hv Hw Hx Ih Ii Ij Ik Il Im Io Ip It Iv Jg Jh Ji Jk Jn Jo Jp Jq Jr Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pd Pe Pf Pg Pz Qa Qb Qc Qd Qe) Pd(Et Fp Fr Hq Hr Hu Hv Hw Hx Ih Ii Ij Ik Il Im Io Ip It Iv Jg Jh Ji Jk Jn Jo Jp Jq Jr Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pe Pf Pg Pz Qa Qb Qc Qd Qe) Io(Et Fp Fr Hq Hr Hu Hv Hw Hx Ih Ii Ik Il In Ip It Iv Jg Jh Ji Jk Jn Jo Jp Jq Jr Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pe Pf Pg Pz Qa Qb Qc Qd Qe) Ip(Et Fp Fr Hq Hr Hu Hv Hw Hx Ih Ii Ik Il In It Iv Jg Jh Ji Jk Jn Jo Jp Jq Jr Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pe Pf Pg Pz Qa Qb Qc Qd Qe) It(Et Fp Fr Hq Hr Hu Hv Hw Hx Ih Ii Ik Il In Iv Jg Jh Ji Jk Jn Jo Jp Jq Jr Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pe Pf Pg Pz Qa Qb Qc Qd Qe) Iv(Et Fp Fr Hq Hr Hu Hv Hw Hx Ih Ii Ik Il In Jg Jh Ji Jk Jn Jo Jp Jq Jr Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pe Pf Pg Pz Qa Qb Qc Qd Qe) Jo(Et Fp Fr Hu Hv Hw Hx Ih Ii Ij Ik Il Im Jg Jh Ji Jk Jn Jo Nd Ne Nf Nh Nj Nl Nm Nn No Nq Ns Nt Nu Nv Nw Nx Ny Oe Of Oh Oi Ok Om On Oy Oz Pa Pb Pc Pe Pf Pg Pz Qa Qb Qc Qd Qe) Ny(Et Fp Fr Hq Hr Hu Hv Hw Hx Ih Ii Ij Ik Il Im Jg Jh Ji Jk Jn Jp Jq Jr Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Oe Of Oh Oi Ok Om On Oy Oz Pa Pc Pe Pf Pg Pz Qa Qb Qc Qd Qe) Fr(Et Fp Hq Hr Hu Hv Hw Hx Ih Ii Il In Jg Jh Ji Jk Jn Jp Jq Jr Lh Lj Lu Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Oe Of Oh Oi Ok Om On Oy Oz Pa Pb Pc Pe Pf Pg Pz Qa Qb Qc Qd Qe) Lu(Et Fp Hq Hr Hu Hv Hw Hx Ih Ii Il In Jg Jh Ji Jk Jn Jp Jq Jr Lh Lj Lv Lw Ly Lz Ma Mb Mc Md Me Mf Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Oe Of Oh Oi Ok Om On Oy Oz Pa Pb Pc Pe Pf Pg Pz Qa Qb Qc Qd Qe) Mf(Et Fp Hq Hr Hu Hv Hw Hx Ih Ii Il Im Jg Jh Ji Jk Jn Jp Jq Jr Lh Lj Lv Lw Ly Lz Ma Mb Mc Md Me Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Oe Of Oh Oi Ok Om On Oy Oz Pa Pb Pc Pe Pf Pg Pz Qa Qb Qc Qd Qe) Jg(Et Fp Hq Hr Hu Hv Hw Hx Ih Ii Il In Jh Ji Jk Jn Jp Jq Jr Lh Lj Lv Lw Ly Lz Ma Mb Mc Md Me Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Oe Of Oh Oi Ok Om On Oy Oz Pa Pb Pc Pe Pf Pg Pz Qa Qb Qc Qd Qe) Ji(Et Fp Hq Hr Hu Hv Hw Hx Ih Ii Il In Jh Jk Jn Jp Jq Jr Lh Lj Lv Lw Ly Lz Ma Mb Mc Md Me Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Oe Of Oh Oi Ok Om On Oy Oz Pa Pb Pc Pe Pf Pg Pz Qa Qb Qc Qd Qe) Fp(Et Hq Hr Hu Hv Hw Hx Ih Ii Il Jh Jk Jn Jp Jq Jr Lh Lj Lv Lw Ly Lz Ma Mb Mc Md Me Mg Mh Mi Mj Mk Ml Mm Mp Mq Mr Mt Mu Mv Mw Mx My Mz Na Nb Nc Nd Ne Nf Nh Nj Nl Nm Nn No Nq Ns Nt Nu Nv Nw Nx Oe Of Oh Oi Ok Om On Oy Oz Pa Pb Pc Pe Pf Pg Pz Qa Qb Qc Qd Qe) Nq(Et Hq Hr Hu Hv Hw Hx Ih Ii Il In Jh Jk Jn Jp Jq Jr Lh Lj Lv Lw Ly Lz Ma Mb Mc Md Me Mg Mh Mi Mj Mk Ml Mm Mp Mq Mr Mt Mu Mv Mw Mx My Mz Na Nb Nc Nd Ne Nf Nh Nj Nl Nm Nn No Ns Nt Nu Nv Nw Nx Oe Of Oh Oi Ok On Oy Oz Pa Pb Pc Pe Pf Pg Pz Qa Qb Qc Qd Qe) Lv(Et Hq Hr Hu Hv Hw Hx Ih Ii Il In Jh Jk Jn Jp Jq Jr Lh Lj Lw Ly Lz Ma Mb Mc Md Me Mg Mh Mi Mj Mk Ml Mm Mp Mq Mr Mt Mu Mv Mw Mx My Mz Na Nb Nc Nd Ne Nf Nh Nj Nl Nm Nn No Ns Nt Nu Nv Nw Nx Oe Of Oh Oi Ok On Oy Oz Pa Pb Pc Pe Pf Pg Pz Qa Qb Qc Qd Qe) Mg(Et Hq Hr Hu Hv Hw Hx Ih Ii Il Jh Jk Jn Jp Jq Jr Lh Lj Lw Ly Lz Ma Mb Mc Md Me Mh Mi Mj Mk Ml Mm Mp Mq Mr Mt Mu Mv Mw Mx My Mz Na Nb Nc Nd Ne Nf Nh Nj Nl Nm Nn No Ns Nt Nu Nv Nw Nx Oe Of Oh Oi Ok Om On Oy Oz Pa Pb Pc Pe Pf Pg Pz Qa Qb Qc Qd Qe) Mj(Et Hq Hr Hu Hv Hw Hx Ih Ii Il Jh Jk Jn Jp Jq Jr Lh Lj Lw Ly Lz Ma Mb Mc Md Me Mh Mi Mk Ml Mm Mp Mq Mr Mt Mu Mv Mw Mx My Mz Na Nb Nc Nd Ne Nf Nh Nj Nl Nm Nn No Ns Nt Nu Nv Nw Nx Oe Of Oh Oi Ok Om On Oy Oz Pa Pb Pc Pe Pf Pg Pz Qa Qb Qc Qd Qe) Mp(Et Hq Hr Hu Hv Hw Hx Ih Ii Il Jh Jk Jn Jp Jq Jr Lh Lj Lw Ly Lz Ma Mb Mc Md Me Mh Mi Mk Ml Mm Mq Mr Mt Mu Mv Mw Mx My

Mv Mw My Mz Na Nb Nc Nd Nf Nh Ni Nl Nm Nn No Nr Nt Nu Nv Nx Ny Oe Of Og Oh Oi Ok Om On Oy Oz Pa Pb Pc Pe Pf Pg Po Qa Qb Qc Qd Qe) Ir(Et Fp Fr Hq Hr Hv Hw Hx Ii Ik Il Jg Jh Ji Jn Jq Lh Li Lj Lu Lv Lw Ly Lz Ma Mb Mc Md Me Mg Mi Mj Mk Ml Mm Mp Mr Mt Mu Mv Mw My Mz Na Nb Nc Nd Nf Nh Ni Nl Nm Nn No Nr Ns Nt Nu Nv Nx Ny Oe Of Og Oh Oi Ok Om On Oy Oz Pa Pb Pc Pe Pf Pg Po Qa Qb Qc Qd Qe) Ji(Et Fp Fr Hq Hr Hv Hw Hx Ii Il Jg Jh Jn Jq Lh Li Lj Lu Lv Lw Ly Lz Ma Mb Mc Md Me Mg Mh Mi Mj Mk Ml Mm Mp Mq Mt Mu Mv Mw My Mz Na Nb Nc Nd Nf Nh Ni Nl Nm Nn No Nr Ns Nt Nu Nv Nx Ny Oe Of Og Oh Oi Ok Om On Oy Oz Pa Pb Pc Pe Pf Pg Po Qa Qb Qc Qd Qe) Ni(Et Fp Fr Hq Hr Hv Hw Hx Ii Jg Jh Jn Jq Lh Li Lj Lu Lv Lw Ly Lz Ma Mb Mc Md Me Mg Mh Mi Mj Mk Ml Mm Mp Mr Mt Mu Mv Mw My Mz Na Nb Nc Nd Nf Nh Nl Nm Nn No Nr Ns Nt Nu Nv Nx Ny Oe Of Oh Oi Ok Om On Oy Oz Pa Pb Pc Pe Pf Pg Po Qa Qb Qc Qd Qe) Ny(Et Fp Fr Hq Hr Hv Hw Hx Ii Ik Il Jh Jn Jq Li Lj Lu Lv Lw Ly Lz Ma Mb Mc Md Me Mg Mh Mi Mj Mk Ml Mm Mp Mq Mr Mt Mu Mv Mw My Mz Na Nb Nc Nd Nf Nh Nl Nm Nn No Nr Ns Nt Nu Nv Oe Of Oh Oi Ok Om On Oy Oz Pa Pb Pc Pe Pf Pg Po Qa Qb Qc Qd Qe) Nr(Et Fp Fr Hq Hr Hv Hw Hx Ii Il Jg Jh Jn Jq Lh Li Lj Lu Lv Lw Ly Lz Ma Mb Mc Md Me Mg Mh Mk Ml Mm Mp Mq Mr Mt Mu Mv Mw My Mz Na Nb Nc Nd Nf Nh Nl Nm Nn No Ns Nt Nu Nv Nx Oe Of Og Oh Oi Ok On Oy Oz Pa Pb Pc Pe Pf Pg Qa Qb Qc Qd Qe) Jn(Et Fp Fr Hq Hr Hv Hw Hx Ii Il Jg Jh Jq Li Lj Lu Lv Lw Ly Lz Ma Mb Mc Md Me Mg Mh Mj Ml Mm Mp Mq Mr Mt Mu Mv Mw My Na Nb Nc Nd Nf Nh Nl Nm Nn No Ns Nt Nu Nv Nx Oe Of Og Oh Oi Ok Om On Oy Oz Pa Pb Pc Pf Pg Po Qa Qb Qc Qd Qe) My(Et Fp Fr Hq Hr Hv Hw Hx Ii Il Jg Jh Jq Li Lj Lu Lv Lw Ly Lz Mb Mc Md Me Mg Mh Mi Mj Mk Ml Mm Mp Mr Mt Mu Mv Mw Mz Na Nb Nc Nd Nf Nh Nl Nm Nn No Ns Nt Nu Nv Oe Of Oh Oi Ok Om On Oy Oz Pa Pb Pc Pe Pf Pg Po Qa Qb Qc Qd Qe) Nl(Et Fp Fr Hq Hr Hv Hw Hx Ii Il Jh Jq Lh Li Lj Lu Lv Lw Ly Lz Mb Mc Md Me Mg Mh Mi Mj Mk Ml Mm Mp Mr Mt Mu Mv Mw Mz Na Nb Nc Nd Nf Nh Nm Nn No Ns Nt Nu Nv Oe Of Oh Oi Ok Om On Oy Oz Pa Pb Pc Pe Pf Pg Po Qa Qb Qc Qd Qe) Hr(Et Fp Fr Hq Hv Hw Hx Ii Il Jh Jq Li Lj Lu Lv Lw Ly Lz Mb Mc Md Me Mg Mh Mi Mj Mk Ml Mm Mp Mr Mt Mu Mv Mw Mz Na Nb Nc Nd Nf Nh Nm Nn No Ns Nt Nu Nv Nx Oe Of Oh Oi Ok Om On Oy Oz Pa Pb Pc Pe Pf Pg Po Qa Qb Qc Qd Qe) Jh(Et Fp Fr Hq Hv Hw Hx Ii Ij Il Jg Jq Lh Li Lj Lu Lv Lw Lz Ma Mb Mc Md Me Mg Mi Mj Mk Ml Mm Mp Mr Mt Mu Mv Mw Mz Na Nb Nc Nd Nf Nh Nm No Ns Nt Nu Nv Oe Of Og Oh Oi Ok Om On Oz Pa Pb Pc Pe Pf Pg Po Qa Qb Qc Qd Qe) On(Et Fp Hq Hv Hw Hx Ii Ij Jg Jq Lh Li Lj Lu Lv Lw Ly Lz Mb Mc Md Me Mg Mh Mi Mj Ml Mm Mp Mq Mt Mu Mv Mw Na Nb Nc Nd Nf Nh Nm Nn No Ns Nu Nv Oe Of Og Oh Oi Ok Om Oy Oz Pa Pb Pc Pe Pf Pg Po Qa Qb Qc Qd Qe) Mt(Et Fp Fr Hq Hv Hw Hx Ii Ij Il Im Jq Li Lj Lv Lw Ly Lz Mb Mc Md Me Mg Mh Mj Mk Ml Mm Mp Mq Mr Mv Mw Mz Na Nb Nc Nd Nf Nh Nm No Ns Nt Nu Nv Nx Oe Of Og Oh Ok Om Oy Oz Pa Pc Pe Pf Pg Po Qa Qb Qc Qd Qe) Nh(Et Fp Hq Hv Hw Hx Ii Il Jg Jq Li Lj Lu Lv Lw Ly Lz Mb Mc Md Me Mg Mh Mi Mj Mk Ml Mm Mp Mu Mv Mw Mz Na Nb Nc Nd Nf Nm No Ns Nt Nu Nv Oe Of Oh Oi Ok Om Oy Oz Pa Pb Pc Pe Pf Pg Po Qa Qb Qc Qd Qe) Pa(Et Fp Fr Hq Hv Hw Hx Ii Il Jg Jq Lh Li Lj Lu Lv Lw Ly Lz Mb Mc Md Me Mg Mh Mi Mj Ml Mm Mp Mu Mv Mw Mz Na Nb Nd Nf Nm Nn No Nt Nu Nv Oe Of Og Oh Oi Ok Om Oy Oz Pb Pc Pe Pf Pg Qa Qb Qc Qd Qe) Ml(Et Fp Fr Hq Hv Hw Hx Ii Il Jq Li Lj Lu Lv Lw Ly Lz Mb Mc Md Me Mg Mh Mi Mj Mk Mm Mp Mr Mt Mu Mv Mw Na Nb Nc Nd Nf Nm No Nt Nu Nv Oe Of Oh Oi Ok Om On Oy Oz Pb Pc Pe Pf Pg Po Qa Qb Qc Qd Qe) Of(Et Fp Fr Hq Hv Hw Hx Ii Jg Jq Li Lj Lu Lv Lw Ly Lz Mb Mc Md Me Mg Mi Mj Mk Mm Mp Mr Mu Mv Mw Mz Na Nb Nc Nd Nf Nm No Nt Nu Nv Oe Oh Oi Ok Om Oy Oz Pb Pc Pe Pf Pg Po Qa Qb Qc Qd Qe) Mm(Et Fp Fr Hq Hv Hw Hx Ii Il Jg Jq Li Lj Lv Lw Lz Mb Mc Md Me Mg Mi Mj Mk Mp Mr Mv Mw Mz Na Nb Nc Nd Nf Nm No Nt Nu Nv Oe Og Oh Oi Ok Om Oy Oz Pb Pc Pe Pf Pg Po Qa Qb Qc Qd Qe) Fp(Et Fr Hq Hv Hw Hx Ii Jq Li Lj Lu Lv Lw Ly Mb Mc Md Me Mg Mh Mi Mj Mk Mp Mq Mr Mv Mw Mz Na Nb Nc Nd Nf Nm Nn No Nt Nu Nv Oe Oh Oi Ok Om Oy Oz Pc Pe Pf Pg Po Qa Qb Qd Qe) Mp(Et Fr Hq Hv Hw Hx Ii Il Jq Li Lj Lv Lw Ly Lz Mb Mc Md Me Mg Mh Mi Mk Mr Mw Mz Na Nb Nc Nd Nf Nm Nn No Nt Nu Nv Oe Oh Oi Ok Om Oy Oz Pb Pe Pf Pg Po Qa Qb Qc Qd Qe) Qd(Et Fr Hq Hv Hw Hx Ii Il Im Jq Lh Li Lj Lv Lw Ly Lz Mb Mc Md Me Mg Mi Mj Mk Mr Mv Mw Mz Na Nb Nc Nd Nf Nm No Nt Nu Nv Oe Oh Oi Ok Om Oy Oz Pb Pc Pe Pf Pg Po Qb Qe) Pc(Et Fr Hq Hv Hw Hx Ii Il Jg Jq Li Lj Lu Lv Ly Lz Mb Mc Md Me Mi Mj Mk Mr Mu Mv Mw Na Nb Nc Nd Nm Nn No Nt Nu Nv Oe Og Oh Ok Om Oy Oz Pb Pe Pf Pg Qa Qb Qc Qe) Hq(Et Fr Hv Hw Hx Ii Il Jq Lh Li Lj Lv Lw Lz Mb Mc Md Me Mg Mi Mj Mk Mr Mu Mw Na Nb Nc Nf Nm No Nt Nu Nv Oe Oh Oi Ok Om Oy Oz Pb Pe Pf Pg Po Qa Qb Qc Qe) Nu(Et Fr Hv Hw Hx Ii Il Jg Jq Li Lj Lv Lw Lz Mb Mc Md Me Mg Mj Mk Mr Mu Mv Mw Na Nb Nc Nd Nf Nm No Nt Nu Nv Oe Oh Oi Ok Oy Oz Pe Pf Pg Po Qa Qb Qc Qe) Hv(Et Fr Hw Hx Ii Il Jq Li Lj Lv Lw Lz Mb Mc Md Me Mg Mi Mj Mk Mr Mu Mv Mw Mz Na Nb Nc Nd Nf Nm Nt Nv Oe Oh Oi Ok Om Oy Oz Pb Pe Pf Qa Qb Qc Qe) Ok(Et Hw Hx Ii Il Li Lj Lu Lv Lw Lz Mb Mc Md Me Mg Mi Mj Mk Mu Mv Mw Na Nb Nc Nd Nf Nm Nn No Ns Nv Oe Oh Oi Om Oy Oz Pb Pe Pg Po Qa Qb Qc Qe) Mg(Et Fr Hw Hx Ii Jq Li Lj Lv Lw Ly Lz Mb Mc Md Me Mh Mi Mj Mk Mr Mv Mw Mz Na Nb Nc Nf Nm No Ns Nt Oe Oh Oi Oz Pe Pf Pg Po Qa Qb Qc Qe) Mj(Fr Hw Hx Ii Ij Ik Il Im Jg Jq Lh Lj Lu Lv Lw Ly Lz Ma Mb Mc Md Mi Mk Mr Mu Mv Mz Nb Nd Nn No Ns Nv Oh Om Pb Pe Pf Pg Po Qb Qc Qe) Mw(Et Fr Hw Hx Ii Il Jq Li Lj Lv Lw Lz Mb Mc Md Me Mi Mk Mr Mu Mv Mz Na Nb Nc Nd Nf Nm No Nt Oe Oh Oi Om Oy Oz Pb Pe Pf Pg Po Qa Qb Qc Qe) Nd(Et Fr Hw Hx Ii Jg Jq Lh Li Lj Lu Lv Lw Lz Ma Mb Mc Md Me Mi Mu Mv Na Nb Nf Nm Nn No Ns Nv Oe Og Oh Oi Oy Pb Pe Pf Qa Qb Qe) Nv(Et Fr Hw Hx Ii Il Jq Li Lj Lv Lw Lz Mb Mc Md Me Mi Mk Mr Mz Na Nb Nc Nf Nm No Nt Oe Oh Oi Om Oz Pe Pf Pg Po Qa Qb) Mc(Et Hw Hx Ii Il Jq Li Lj Lv Lw Lz Mb Md Me Mi Mu Mz Na Nb Nc Nf Nm Nn No Nt Oe Og Oh Oi Om Oy Oz Pb Pe Po Qa Qb) Li(Et Fr Hw Hx Ii Jg Jq Li Lv Lw Mb Md Me Mi Mk Mr Mu Na Nb Nc Nf Nm Nn Nt Oe Oh Oi Om Oy Oz Pe Pf Po Qa Qb Qe) Oe(Et Fr Hw Hx Lj Lv Lw Ly Lz Mb Md Me Mi Mz Na Nc Nf Nm Nn No Nt Og Oh Oi Om Oy Oz Pb Pe Pf Po Qa Qb Qe) Mi(Hw Hx Il Lj Lu Lv Lw Lz Mb Md Me Mq Mv Mz Na Nb Nc Nm Nn No Ns Og Oh Om Oy Pb Pe Pg Qa Qb Qc Qe) Hw(Et Hx Ii Jq Lj Lv Lw Mb Md Mk Mr Mz Na Nb Nc Nf No Nt Oh Oi Om Oy Oz Pb Pe Pf Pg Po Qb Qe) Og(Et Fr Hx Ii Jg Lh Lu Lv Ma Md Me Mk Mu Mv Na Nb Nf Nn Nx Om Oy Pb Pe Pf Pg Po Qa Qb Qc) Qa(Et Fr Hx Ii Jq Lv Mb Md Me Mk Mr Mv Na Nc Nf Nm Nt Oh Oi Om Oy Oz Pe Pf Pg Po Qe) Lv(Hx Lj Lu Lz Mb Md Me Mk Mv Mz Nb Nc Nf Nm No Nt Oh Om Oy Pb Pe Qb Qc Qe) Nf(Et Fr Jq Lj Lz Mb Md Me Mr Mv Mz Na Nc Nm No Nt Oh Oy Oz Pe Pf Qb Qe) Nt(Et Fr Hx Ii Jq Lj Mb Md Me Na Nc Nm No Oh Oi Oy Oz Pf Po Qb Qc) Qb(Et Hx Ii Il Jq Lj Lw Mb Md Me Mz Na Nc Nm Oh Om Pb Pe Po Qc) Om(Et Hx Ii Il Jq Lu Lw Mb Md Me Mv Na Nm Nn Oi Oz Pe Pg Qe) Oy(Et Ii Jq Lj Lw Mb Md Me Mk Mr Mz Na Nc Nm Oh Oz Pb Po Qe) Oi(Et Fr Il Jq Lj Mb Md Me Na Nc Nm No Oh Oz Pe Pf Qe) Ii(Et Hx Il Jq Mb Md Me Mh Mz Na Nm No Oh Pb Po) Nm(Et Fr Jq Lj Mb Md Me Na No Oh Pe Pf Qe) Il(Et Hx Mb Md Me Mh Mr Mz Nb Oh Pe Qc Qe) Na(Et Fr Jq Lz Mb Md Me Mz Nc No Oh Po) Md(Et Jq Lj Mb Me Mk Mr Oh Oz Pb) Me(Et Jq Mb Mz Nc Oh Oz Pb Pe) Mv(Fr Hx Lu Nb Nn Pb Pe Pf Pg) Mz(Et Fr Hx Jg Pe Pf Pg) Jq(Et Lj Mb Nc Oh Pb Qc) Mk(Fr Lj Lz Mb Mh Nb) Mr(Hx Mh Nb Oz Pg) Oh(Et Lz Mb Pb Qc) Lj(Et No Pe Pf) Pe(Lz Pf Pg) Et(Hx Mb) Oz(Lu Mb) Pb(Hx Mh) LhPg] Jj(Lv(aA Et Fp Fr Hq Hr Hu Hv Hw Hx Ih Ii Ij Ik Il Im In Io Ip Iq Ir Is It Iu Iv Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Io(aA Et Fp Fr Hq Hr Hu Hv Hw Hx Ih Ii Ij Ik Il Im In Ip Iq Ir Is It Iu Iv Jg Jh Ji Jk Jm Jn Jo Jp Jq Jr Js Jt Lh Li Lj Lu Lv Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ip(aA Et Fp Fr Hq Hr Hu Hv Hw Hx Ih Ii Ij Ik Il Im In Iq Ir Is It Iu Iv Jg Jh Ji Jk Jm Jn Jo Jp Jq Jr Js Jt Lh Li Lj

Nt Pe Pf Qb Qd) Pf(Hv Lu Ly Mp Nc Ng Nl Oi) Lu(Jm Mp Nl Nn Nt) Ng(Hv Jk Lz Nl Of) Hv(Jk Nn Nt Of) Nc(Im Nt Om) Oi(Im Qb Qd)
Nn(Li Ny) Hr(Mk Mr) LyIm NlJk NyOm} Is{Fr(aA Et Fp Hq Hr Hu Hv Hw Hx Ih Ii Ij Ik Il Im In Io Ip Iq Ir It Iu Iv Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ng(aA Et Fp Hq Hr Hu Hv Hw Hx Ih Ii Ij Ik Il Im In Io Ip Iq Ir It Iu Iv Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ni(aA Et Fp Hq Hr Hu Hv Hw Hx Ih Ii Ij Ik Il Im In Io Ip Iq Ir It Iu Iv Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jo(aA Et Fp Hq Hr Hu Hv Hw Hx Ih Ii Ij Ik Il Im In Io Ip Iq Ir It Iu Iv Jg Jh Ji Jk Jm Jn Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jt(aA Et Fp Hq Hr Hu Hv Hw Hx Ih Ii Ij Ik Il Im In Io Ip Iq Ir It Iu Iv Jg Jh Ji Jk Jm Jn Jp Jq Jr Js Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Og(aA Et Fp Hq Hr Hu Hv Hw Hx Ih Ii Ij Ik Il Im In Io Ip Iq Ir It Iu Iv Jg Jh Ji Jk Jm Jn Jp Jq Jr Js Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe) aA(Et Fp Hq Hr Hu Hv Hw Hx Ih Ii Ij Ik Il Im In Io Ip Iq Ir It Iu Iv Jg Jh Ji Jk Jm Jn Jp Jq Jr Js Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe) Jm(Et Fp Hq Hr Hu Hv Hw Hx Ih Ii Ij Ik Im In Io Ip Iq Ir It Iu Iv Jg Jh Ji Jk Jn Jp Jq Jr Js Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe) Lu(Et Fp Hq Hr Hu Hv Hw Hx Ih Ii Ik Il In Io Ip Iq Ir It Iu Iv Jg Jh Ji Jk Jn Jp Jq Jr Js Lh Li Lj Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Nh Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe) Mz(Et Fp Hq Hr Hu Hv Hw Hx Ih Ii Ij Il Im In Io Ip Iq Ir It Iu Iv Jg Jh Ji Jk Jn Jp Jq Jr Js Lh Li Lj Lv Lw Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Nh Nj Nk Nl Nm Nn No Nq Ns Nt Nu Nv Nw Nx Ny Oe Of Oh Oi Ok Om On Oy Oz Pa Pb Pc Pd Pe Pf Pg Po Pz Qa Qb Qc Qd Qe) Ms(Et Fp Hq Hr Hu Hv Hw Hx Ih Ii Il In Io Ip Iq Ir It Iu Iv Jg Jh Ji Jk Jn Jp Jq Jr Js Lh Li Lj Lv Lw Ly Lz Ma Mb Mc Md Me Mf Mg Mh Mi Mj Mk Ml Mm Mn Mp Mq Mr Mt Mu Mv Mw Mx My Na Nb Nc Nd Ne Nf Nh Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe) Nk(Et Fp Hq Hr Hu Hv Hw Hx Ih Ii Ik In Io Ip Iq Ir It Iu Iv Jg Jh Ji Jk Jn Jp Jq Jr Js Lh Li Lj Lv Lw Ly Lz Ma Mb Mc Md Me Mf Mg Mh Mi Mj Mk Ml Mm Mn Mp Mq Mr Mt Mu Mv Mw Mx My Na Nb Nc Nd Ne Nf Nh Nj Nl Nm Nn No Nq Ns Nt Nu Nv Nw Nx Ny Oe Of Oh Oi Ok Om On Oy Oz Pa Pb Pc Pd Pe Pf Pg Po Pz Qa Qb Qc Qd Qe) In(Et Fp Hq Hr Hu Hv Hw Hx Ii Ij Io Ip Iq Ir It Iu Iv Jh Ji Jk Jn Jp Jq Jr Js Lh Li Lj Lv Lw Ly Lz Ma Mc Md Me Mf Mg Mh Mi Mj Mk Ml Mm Mn Mp Mq Mr Mt Mu Mv Mw Mx My Na Nb Nc Nd Ne Nf Nh Nj Nl Nm No Nq Nr Ns Nt Nu Nv Nw Nx Ny Oe Of Oh Oi Ok On Oy Oz Pa Pb Pc Pd Pe Pf Pg Po Pz Qa Qb Qc Qd Qe) Nw(Et Fp Hq Hr Hv Hw Hx Ih Ii Il Io Ip Iq Ir It Iu Iv Jg Jh Ji Jk Jn Jp Jq Jr Js Lh Li Lj Lv Lw Ly Lz Ma Mc Md Me Mf Mg Mh Mi Mj Ml Mm Mn Mp Mq Mr Mt Mu Mv Mw Mx My Na Nb Nc Nd Ne Nf Nh Nl Nm Nn No Nq Ns Nt Nu Nv Nx Ny Oe Of Oh Oi Ok Om On Oy Oz Pa Pb Pc Pd Pe Pf Pg Po Pz Qa Qb Qc Qd Qe) Ji(Et Fp Hq Hr Hu Hv Hw Hx Ii Io Ip Iq It Iu Iv Jg Jh Jk Jn Jp Jq Js Lh Li Lj Lv Lw Ly Lz Ma Mb Mc Md Me Mf Mg Mh Mi Mj Ml Mm Mn Mp Mq Mr Mt Mu Mv Mw Mx My Na Nb Nc Nd Ne Nf Nh Nl Nm Nn No Nq Ns Nt Nu Nv Nx Ny Oe Of Oh Oi Ok Om On Oy Oz Pa Pb Pc Pd Pe Pf Pg Po Pz Qa Qb Qc Qd Qe) Mg(Et Fp Hq Hu Hv Hw Hx Ii Io Ip Iq Ir It Iu Iv Jg Jh Jk Jn Jp Jq Jr Js Lh Li Lj Lv Lw Ly Lz Ma Mc Md Me Mf Mh Mi Mj Mk Ml Mm Mn Mp Mq Mr Mt Mu Mv Mw Mx My Na Nb Nc Nd Ne Nf Nh Nj Nl Nm Nn No Nq Ns Nt Nu Nv Nx Ny Oe Of Oh Oi Ok On Oz Pa Pb Pc Pd Pe Pf Pg Po Pz Qb Qc Qd Qe) Mt(Et Fp Hr Hu Hv Hw Hx Ih Ii Il Io Ip Iq It Iu Iv Jg Jh Jk Jp Jq Js Lh Li Lj Lv Lw Ly Lz Ma Mb Mc Md Me Mf Mh Mi Mj Mm Mn Mp Mq Mr Mu Mv Mw Mx My Na Nc Nd Ne Nf Nh Nj Nl Nm Nn Nq Nr Ns Nt Nu Nv Nx Ny Oe Of Oh Oi Ok On Oy Oz Pa Pb Pc Pd Pe Pf Pg Po Qb Qc Qd Qe) Mi(Fp Hq Hr Hu Hv Hw Hx Ih Ii Il Io Iq Ir It Iu Iv Jg Jh Jk Jn Jp Jq Jr Js Lh Li Lj Lv Lw Lz Ma Mb Mc Md Me Mf Mj Ml Mm Mn Mp Mq Mv Mw Mx Na Nb Nd Ne Nf Nj Nl Nm No Ns Nu Nv Nx Ny Oe Of Oh Oi Ok On Oy Oz Pa Pb Pc Pd Pe Pf Pg Po Pz Qb Qc Qd Qe) Mv(Et Fp Hq Hr Hu Hv Hw Hx Ih Ii Ik Il Ip Iq Ir It Iu Jh Jk Jn Jp Jq Jr Js Lh Li Lv Lw Ly Ma Mb Mc Md Me Mf Mh Mj Mk Ml Mm Mn Mp Mu Mw Mx Na Nc Nd Ne Nf Nh Nj Nl Nm No Nq Nr Nt Nu Nv Nx Ny Oe Of Oh Oi Ok Pa Pb Pd Pg Po Pz Qa Qb Qc Qd Qe) Ma(Fp Hq Hr Hu Hv Hw Hx Ih Ii Ik Ip Iq It Iu Iv Jg Jh Jk Jn Jp Jq Jr Js Lh Li Lv Ly Mb Mc Md Me Mf Mh Mj Ml Mm Mp Mq Mu Mx My Na Nd Ne Nf Nh Nj Nl Nm No Nq Nr Ns Nt Nu Nv Nx Ny Oe Of Oh Oi Ok On Pa Pb Pc Pd Pz Qc Qd Qe) On(Fp Hr Hu Hv Hw Ii Il Io Ip Iq Ir It Iu Iv Jh Jk Jn Jp Jq Jr Js Lh Li Lv Ly Mc Md Mf Mh Mj Ml Mm Mn Mp Mq My Na Nb Nd Ne Nl Nm Nq Ns Nt Nu Nv Nx Ny Oe Of Oi Ok Oy Oz Pa Pb Pc Pd Pe Pf Pg Po Qb Qc Qd) Pa(Et Fp Hq Hr Hv Hw Hx Ih Ii Ip Iq It Iu Jg Jh Jk Jn Jp Jq Jr Js Lh Li Lj Lv Lw Ly Lz Mc Mf Mh Mj Ml Mn Mp Mq Mu Mx My Na Nd Ne Nl Nm Nq Nt Nu Nv Nx Ny Oe Of Oi Ok Oy Oz Pb Pc Pd Pf Pg Po Qb Qd) Jr(Et Fp Hr Hv Hw Hx Ih Ii Il Ip Iq Ir It Iu Jg Jh Jk Jn Jp Jq Js Lh Li Lv Lw Ly Mc Me Mf Mh Mj Mk Ml Mn Mp Mu Mx My Na Nd Ne Nf Nh Nl Nm Nn Nq Nt Nu Nv Nx Ny Oi Ok Pb Pc Pd Qb Qd Qe) Js(Et Hu Hv Hw Hx Ip Iq Ir Iu Iv Jg Jp Lh Li Lv Lw Ly Mc Mf Mj Mk Mm Mn Mp Mr Mu My Nb Nd Ne Nj Nm Nn No Nq Nr Nv Nx Ny Oe Oi Ok Oz Pb Pc Pd Pe Pf Pg Po Qa Qc Qe) Nx(Et Hq Hr Hu Hv Hw Ih Ii Il Ip Iq It Iu Jg Jh Jn Jp Jq Lh Lv Lw Ly Mb Mf Ml Mn Mp Mu Mx My Nc Nd Ne Nf Nh Nl Nm Nn No Nq Nv Oe Oi Ok Om Pb Pc Pd Pf Pz Qd) Jp(Fp Hr Hu Hv Hw Hx Ii Ip Iq It Iu Jg Jk Jn Jq Lh Li Lv Ly Mc Mf Mh Mj Ml Mm Mn Mu Mx Na Nd Ne Nf Nl Nm Nq Nt Nu Nv Ny Oe Oi Pb Pc Pd Pf Po Qd Qe) Mf(Et Hv Hx Ii Il Ip Iq It Iu Iv Jg Jh Lh Lv Lw Ly Ml Mn Mu Mx My Na Nd Ne Nl Nm Nn Nu Nv Ny Oe Oi Ok Pb Pc Pd Pf Pg Qa Qc Qe) Nd(Et Hr Hv Hw Hx Ii Iq It Iu Iv Jg Jh Jn Jq Lh Li Lv Me Mm Mn Mu Mx My Nf Nl Nm Nu Nv Ny Oe Of Oi Ok Pf Qc Qe) Lh(Hu Hw Ih Ii Il Ip Iq Iu Jk Jq Li Lv Ly Mj Ml Mx My Ne Nj Nl Nm Nr Nu Oe Of Oi Oz Pb Pc Pd Pz Qd) Pd(Et Hw Hx Iq Jg Jh Li Lv Lw Mk Mn Mp Mr Mu Ne Nn Nq Nr Nv Oe Oi Ok Pb Pc Pe Pf Po Qe) Oi(Et Hv Hw Hx Ip Iq Iu Iv Jg Jh Jq Lv Ml Mn Mu Mx Ne Nl Nm Nq Nv Ok Pe Pf Qc Qe) Iq(Hx Ii Ip Jg Jq Ly Mn Mu Mx Ne Nh Nj Nl Nm Nn No Nq Nv Oe Pf Qe) Iu(Et Hx Ir Jg Jh Jq Lv Ly Mn Mu Ne Nn Nq Nv Oe Pe Pf Qa Qc Qe) Jg(Hu Ii Il Ip Jh Jk Jq Li Ly Mw Mx My Ne Nm Nq Of Pz) Nm(Et Lv Lw Mn Mu Ne Nn Nq Nv Oe Ok Pc) Jq(Il Ip Lv Mn Mu Ne Nv Oe Om) Oe(Ii Ly Mx Ne Nv Ok Pc) Mu(Jk Li Ne Nu) Pc(Il My Of Oy) Lv(Ii Ly Ne) Nv(Ii My Ne) Mk(Hr Oy) Qe(Ip Ne) NnLi MrHr MxQa} Nw{Ni(aA Et Fp Fr Hq Hr Hu Hv Hw Hx Ih Ii Ij Il In Io Ip Iq Ir It Iu Iv Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv

Figure 10 Continued

Mw Mx My Mz Na Nb Nc Nd Ne Nf Ng Nh Nj Nk Nl Nm Nn No Nq Nr Ns Nt Nu Nv Nx Ny Oe Of Og Oh Oi Ok Om On Oy Oz Pa Pb Pc Pd
Pe Pf Pg Po Pz Qa Qb Qc Qd Qe) Iq(aA Et Fp Fr Hq Hr Hu Hv Hw Hx Ih Ii Ij Il Im In Io Ip Ir It Iu Iv Jg Jh Ji Jk Jm Jn Jo Jp Jq Jr Js Jt Lh Li Lj
Lu Lv Lw Ly Lz Ma Mc Md Me Mf Mg Mh Mi Mj Ml Mm Mn Mp Mq Mr Ms Mt Mu Mv Mw Mx My Mz Na Nb Nc Nd Ne Nf Ng Nh Nj Nk
Nl Nm Nn No Nq Ns Nt Nu Nv Nx Ny Oe Of Og Oh Oi Ok Om On Oy Oz Pa Pb Pc Pd Pe Pf Pg Po Pz Qa Qb Qc Qd Qe) Mn(aA Et Fp Fr Hq
Hr Hu Hv Hw Hx Ih Ii Il In Io Ip Ir It Iu Iv Jg Jh Ji Jk Jm Jn Jo Jp Jq Jr Js Jt Lh Li Lj Lu Lv Lw Ly Lz Ma Mb Mc Md Me Mf Mg Mh Mi Mj
Mk Ml Mm Mp Mq Mr Ms Mt Mu Mv Mw Mx My Mz Na Nb Nc Nd Ne Nf Ng Nh Nk Nl Nm Nn No Nq Ns Nt Nu Nv Nx Ny Oe Of Og Oh Oi
Ok Om On Oy Oz Pa Pb Pc Pd Pe Pf Pg Po Pz Qa Qb Qc Qd Qe) Ip(aA Et Fp Fr Hq Hr Hu Hv Hw Hx Ih Ii In Io Ir It Iu Iv Jg Jh Ji Jk Jm Jn Jo
Jp Jq Jr Js Jt Lh Li Lj Lu Lv Lw Ly Lz Ma Mb Mc Md Me Mf Mg Mh Mi Mj Ml Mm Mp Mq Mr Ms Mt Mu Mv Mw Mx My Mz Na Nb Nc Nd
Ne Nf Ng Nh Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe)
Ir(aA Et Fp Fr Hq Hr Hv Hw Hx Ih Ii Il Im In Io It Iu Iv Jg Jh Ji Jk Jm Jn Jo Jp Jq Jr Js Jt Lh Li Lj Lu Lv Lw Ly Lz Ma Mc Md Me Mf Mg Mh
Mi Mj Ml Mm Mp Mq Mr Ms Mt Mu Mv Mw Mx My Mz Na Nb Nc Nd Ne Nf Ng Nh Nj Nk Nl Nm Nn No Nq Ns Nt Nu Nv Nx Ny Oe Of Og
Oh Oi Ok Om On Oy Oz Pa Pb Pc Pd Pe Pf Pg Po Pz Qa Qb Qc Qd Qe) Ms(aA Et Fp Fr Hq Hr Hu Hv Hw Hx Ih Ii In Io It Iu Iv Jg Jh Ji Jk Jm
Jn Jo Jp Jq Jr Js Jt Lh Li Lj Lu Lv Lw Lz Ma Mc Md Me Mf Mg Mh Mi Mj Mk Ml Mm Mp Mq Mr Mt Mu Mv Mw Mx My Mz Na Nb Nc Nd
Ne Nf Ng Nh Nj Nk Nl Nm No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe)
Jt(aA Et Fp Fr Hq Hr Hu Hv Hw Hx Ih Ii In Io It Iu Iv Jg Jh Ji Jk Jm Jn Jp Jq Jr Js Lh Li Lj Lu Lv Lw Lz Ma Mc Md Me Mf Mg Mh Mi Mj Mk
Ml Mm Mp Mq Mr Mt Mu Mv Mw Mx My Mz Na Nb Nc Ne Nf Ng Nh Nj Nk Nl Nm Nn No Nq Nr Ns Nt Nu Nv Nx Ny Oe Of Og Oh Oi Ok
Om On Oy Oz Pa Pb Pc Pd Pe Pf Pg Po Pz Qa Qb Qc Qd Qe) Ng(aA Et Fp Fr Hq Hr Hv Hw Hx Ih Ii In Io Ir Iu Iv Jg Jh Ji Jk Jm Jn Jo Jp Jq Jr Js
Lh Li Lj Lu Lv Lw Lz Ma Mc Md Me Mf Mg Mh Mi Mj Mk Ml Mm Mp Mq Mr Mt Mu Mv Mw Mx My Mz Na Nb Nc Ne Nf Nj Nk Nl Nm
Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Iu(aA Et Fp Fr Hq Hr Hu
Hv Hw Hx Ih Ii In Io It Iv Jg Jh Ji Jk Jm Jn Jo Jp Jq Jr Js Lh Li Lu Lv Lw Ly Lz Ma Mc Md Me Mf Mg Mh Mi Mj Mk Ml Mm Mp Mq Mr Mt
Mw Mx My Mz Na Nb Nc Nd Ne Nf Nh Nj Nk Nm Nn No Nq Nr Ns Nt Nu Nv Nx Ny Oe Of Og Oh Oi Ok Om On Oy Oz Pa Pb Pc Pd Pe Pf
Pg Po Pz Qa Qb Qc Qd Qe) It(aA Et Fp Fr Hq Hr Hv Hw Hx Ih Ii Im Io Iv Jg Jh Ji Jk Jm Jn Jo Jp Jq Jr Js Lh Li Lj Lu Lv Lw Ly Lz Ma Mc Md
Me Mf Mg Mh Mi Mj Ml Mm Mp Mq Mt Mu Mw Mx My Mz Na Nb Nc Nd Ne Nf Nh Nk Nl Nm Nn No Nq Ns Nt Nu Nv Nx Ny Oe Of Og
Oh Oi Ok Om On Oy Oz Pa Pb Pc Pd Pe Pf Pg Po Pz Qa Qb Qc Qd Qe) Iv(aA Et Fp Fr Hq Hr Hv Hw Hx Ii Il In Io Jg Jh Ji Jk Jm Jn Jo Jp Jq Jr
Js Lh Li Lu Lv Lw Ly Lz Ma Mc Md Me Mf Mg Mh Mi Ml Mm Mp Mq Mt Mu Mv Mw Mx My Mz Na Nb Nd Ne Nf Nh Nj Nk Nl Nm Nn No
Nq Ns Nt Nu Nv Nx Ny Oe Of Og Oh Oi Ok Om On Oz Pa Pb Pc Pd Pe Pf Pg Po Pz Qa Qb Qd Qe) Io(aA Et Fp Fr Hq Hr Hv Hw Hx Ii In Jg Jh
Ji Jk Jm Jn Jo Jp Jq Jr Js Lh Li Lu Lv Lw Ly Lz Ma Mc Md Me Mf Mg Mh Mi Mj Ml Mm Mp Mq Mt Mu Mw Mx My Mz Na Nb Nd Ne Nf Nh
Nk Nl Nm Nn No Nq Ns Nt Nu Nv Nx Ny Oe Of Og Oh Oi Ok Om On Oz Pa Pb Pc Pd Pe Pf Pg Po Pz Qa Qb Qd Qe) Oe(aA Et Fp Fr Hq Hr
Hu Hv Hw Hx Ih Ii In Jg Jh Ji Jk Jn Jo Jp Jq Jr Js Lh Li Lj Lu Lv Lw Lz Ma Mc Md Me Mf Mg Mh Mi Mj Mk Mm Mp Mq Mr Mt Mu Mx My
Mz Na Nb Nc Ne Nf Nj Nk Nl Nm No Ns Nt Nu Nv Nx Ny Of Oh Ok Om On Oy Oz Pa Pb Pc Pd Pe Pf Pg Po Pz Qa Qb Qc Qd Qe) Lu(Et Fp
Fr Hq Hr Hu Hv Hw Hx Ii In Jg Jh Ji Jk Jn Jo Jp Jq Jr Js Lh Li Lv Lz Ma Mc Md Me Mf Mh Mj Ml Mp Mq Mt Mv Mw Mx My Na Nb Nc
Ne Nj Nk Nl Nm No Nq Nr Ns Nt Nu Nv Nx Ny Of Og Oh Om Oz Pa Pb Pc Pd Pf Pg Po Pz Qa Qc Qd Qe) Fr(aA Et Fp Hq Hr Hu Hv Hw Ih Ii
In Jh Ji Jk Jn Jo Jp Jq Jr Js Li Lv Lz Ma Mc Me Mf Mh Mi Mj Ml Mm Mp Mt Mv Mw Mx My Na Nc Ne Nf Nj Nk Nl Nm Nn Nq Nr Nt Nu Nv
Ny Of Og Oh Oi Om On Oz Pc Pd Pf Pz Qa Qc Qd Qe) Nk(aA Et Fp Hq Hr Hu Hv Hw Hx Ii In Jg Jh Ji Jm Jn Jo Jp Jq Jr Js Lh Lv Ma Md Me
Mf Mg Mh Mi Ml Mm Mt Mu Mx My Mz Nc Ne Nf Nh Nj Nm Nr Nt Nv Nx Ny Of Og Oi Om Oy Oz Pa Pc Pd Pf Pg Po Pz Qa Qb Qd Qe)
Jo(aA Fp Hu Hv Hw Hx Ii In Jg Ji Jk Jp Jq Jr Js Lh Li Lv Ma Md Mf Mg Mh Mi Mj Mk Mq Mr Mv Mx My Nb Nc Ne Nf Nm Nr Ns Nx Ny Of
Og Oi Ok On Oz Pa Pc Pd Pe Pf Pg Pz Qe) Js(aA Et Hu Hv Hw Hx In Jg Jh Ji Jn Jp Jq Jr Lh Lv Ma Md Mf Mg Mi Mj Mk Mm Mq Mr Mt Mw
My Nb Nc Ne Nm No Nr Ns Nv Nx Ny Of Og On Oy Pa Pb Pd Pe Pf Pz Qa Qb Qe) Mf(aA Fp Hq Hv Ii In Jg Jh Ji Jp Jq Jr Lh Li Lv Ma Mc Md
Mg Mh Mi Mt Mx My Nc Ne Nf Nm Ns Nv Nx Ny Of Og Oz Pa Pd Pf Po Pz Qa Qe) Jr(Fp Hq Hr Hv Ii In Jg Jm Jn Jp Jq Li Lj Lv Md Mh Ml
Mp Mq Mx Na Ne Nf Nj Nr Nt Nv Nx Of Oi Oz Pc Pd Po Pz Qd) aA(Fp Hr Hv Ii In Jg Jk Jq Lj Lv Lz Md Mj Mp Mt Mx My Nf Nq Nr Nv Ny
Of Og Oz Pa Pc Pd Qd) In(Hv Hw Hx Jg Jn Jq Lh Lv Mi Mk Mr Mt Mv Mx Nb Nr Nx Ny Og On Pa Pb Pe Qa Qe) Nx(Fp Hu Hv Hx Jh Ji Jp
Lv Ml Mt My Nq Nr Nv Of Og On Pa Pd Pz) Jq(Fp Hv Hx Jg Ji Jn Jp Lv Mi Mt Mx Ne Nm Og Pa Pd Pz Qe) Lv(Et Fp Hu Jg Jm Jp Li Mg Mp
Mt My Nd Og Pd Pz) Ny(Jm Jp Ly Md Mg Ml Mw Mx My Nv Of Og Pd Pz Qe) Mi(Fp Hq Hu Jk Li Mj Mp Mx Og Oz Pc Pz) Jg(Hu Jh Li Mt
My Nm Nv Of Og Pd Pz) Mv(Hu Jh Jk My Nr Nv Og Pd) Qe(Fp Jm Mt Mx Og Pd) Pd(Hv Jn Lh Og Pa) Mt(Jn Ml Nq Nr) Mx(Jn Md My)
Og(Hx My Pa) MkOy MpJp MrHr] aA{Iq(Et Fp Fr Hq Hr Hu Hv Hw Hx Ih Ii Ij Ik Il Im In Io Ip Ir It Iu Iv Jg Jh Ji Jk Jm Jn Jo Jp Jq Jr Js Jt Lh
Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf
Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe)
Ir(Et Fp Fr Hq Hr Hu Hv Hw Hx Ih Ii Ij Ik Il Im In Io Ip It Iu Iv Jg Jh Ji Jk Jm Jn Jo Jp Jq Jr Js Jt Lh Li Lj Lu Lv Lw Ly Lz Ma Mb Mc Md Me
Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns
Nt Nu Nv Nx Ny Oe Of Og Oh Oi Ok Om On Oy Oz Pa Pb Pc Pd Pe Pf Pg Po Pz Qa Qb Qc Qd Qe) It(Et Fp Fr Hq Hr Hu Hv Hw Hx Ih Ii Ij Ik
Il Im In Io Ip Iu Iv Jg Jh Ji Jk Jm Jn Jo Jp Jq Jr Js Jt Lh Li Lj Lu Lv Lw Ly Lz Ma Mb Mc Md Me Mf Mh Mi Mj Mk Ml Mm Mn Mp Mq Mr
Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On
Oy Oz Pa Pb Pc Pd Pe Pf Pg Po Pz Qa Qb Qc Qd Qe) Iu(Et Fp Fr Hq Hr Hu Hv Hw Hx Ih Ii Ij Ik Il Im In Io Ip Iv Jg Jh Ji Jk Jm Jn Jo Jp Jq Jr Js
Jt Lh Li Lj Lu Lv Ly Lz Ma Mb Mc Md Me Mf Mg Mh Mi Mj Mk Ml Mm Mn Mp Mq Mr Ms Mt Mu Mv Mw Mx My Mz Na Nb Nc Nd
Ne Nf Ng Nh Ni Nj Nk Nl Nm Nn No Nq Nr Ns Nl Nu Nv Nx Ny Oe Of Og Oh Oi Ok Om On Oy Oz Pa Pb Pc Pd Pe Pf Pg Po Pz Qa Qb Qc
Qd Qe) Iv(Et Fp Fr Hq Hr Hu Hv Hw Hx Ih Ii Ij Ik Il Im In Io Ip Jg Jh Ji Jk Jm Jn Jo Jp Jq Jr Js Jt Lh Li Lj Lu Lv Lw Ly Lz Ma Mb Mc Md Me
Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns
Nt Nu Nv Nx Ny Oe Of Og Oh Oi Ok Om On Oy Oz Pa Pb Pc Pd Pe Pf Pg Po Pz Qa Qb Qc Qd Qe) Ni(Et Fp Fr Hq Hr Hu Hv Hw Hx Ih Ii Ij Il
Im In Io Ip Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt
Mu Mv Mw Mx My Mz Na Nb Nc Nd Ne Nf Ng Nh Nj Nk Nl Nm Nn No Nq Nr Ns Nt Nu Nv Nx Ny Oe Of Og Oh Oi Ok Om On Oy Oz Pa
Pc Pd Pe Pf Pg Po Pz Qa Qb Qc Qd Qe) Io(Et Fp Fr Hq Hr Hu Hv Hw Hx Ih Ii Ij Ik Il Im In Ip Jg Jh Ji Jk Jm Jn Jo Jp Jq Jr Js Jt Lh Li Lj Lu Lv
Lw Ly Lz Ma Mb Mc Md Me Mf Mg Mh Mi Mj Mk Ml Mm Mn Mp Mq Mr Ms Mt Mu Mv Mw Mx My Mz Na Nb Nd Ne Nf Ng Nh Nj Nk Nl
Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Mn(Et Fp Fr Hq Hr
Hu Hv Hw Hx Ih Ii Il Im In Ip Jg Jh Ji Jk Jm Jn Jo Jp Jq Jr Js Jt Lh Li Lj Lu Lv Lw Ly Lz Ma Mb Mc Md Me Mf Mg Mh Mi Mj Mk Ml Mm
Mp Mq Mr Ms Mt Mu Mv Mw Mx My Mz Na Nb Nc Nd Ne Nf Ng Nh Nk Nl Nm Nn No Nq Nr Ns Nt Nu Nv Nx Ny Oe Of Og Oh Oi Ok Om
On Oy Oz Pa Pb Pc Pd Pe Pf Pg Po Pz Qa Qb Qc Qd Qe) Ip(Et Fp Fr Hq Hr Hu Hv Hw Hx Ih Ii Ik Il Im In Jg Jh Ji Jk Jm Jn Jo Jp Jq Jr Js Jt Lh

Mx Nf Nl Nn Ny Ok Pf Qe) Ii(Et Hv Hx Ip Ir Iv Jh Mn Nn No Nq Ok Pf Pg Qc Qe) Mv(Im Io Iv Lj Lz Mq Mr My Nb Ns Om Oy Oz Pe Pf)
Nn(Fp Hw In Ip Jk Mi Mx Nf Nt Nu Ny Pb Po) Mx(Hv Hx Iv Mj Mn Mr Nr Ok Pe Pf Qe) Ip(Et Hx Jh Lw Mi Mn Nl Nq Ok Pb Pf) Nl(Hv Hx Ir
Mk Mr Nr Ok Qe) Mg(Hr Ih Il Mb Om Oy Qa) Mi(Et Ij Mk My Nc Nh Om) Il(In Jm Mj Mr Nk Pe) Li(Lw Mn No Ok Pe Pf) Nw(Hu Ij Im Mb
Nj) In(Ih Ik Mb Om) Nk(Ij Im Nr) Of(Mk Mr Pb) Nq(Ih Nu) Lu(Ij Im) Ms(Ik Im) Mz(Ik Nr) Hr(Hx Pe) Hw(Hx Ok) NtOk NuPe MwMy HqPb
QdQe) Nw{Og(Et Fp Hq Hr Hu Hv Hw Ii Jh Jk Jm Jn Jp Jr Lh Li Lj Lz Ma Mc Md Mg Mh Mj Mk Ml Mm Mq Mr Mu Mw Mx Mz Na Nb Nc
Ne Nf Nj Nl Nm No Nq Nr Nt Nu Nv Of Oh Ok On Oy Oz Pb Pc Pe Pf Pg Po Pz Qa Qb Qc Qd) Jq(Et Hq Hr Hu Hw Ii Jh Jk Jm Lh Li Lw Lz
Ma Mc Md Me Mg Mh Mj Ml Mm Mp Mq Mr Mu Mw My Mz Na Nb Nc Nf Nh Nj Nl No Nq Nr Ns Nt Nu Nv Nx Ny Of Oh Oi Ok Om On Oz
Pb Pc Pe Pf Pg Po Qa Qb Qc Qd) Nx(aA Et Fr Hq Hr Hw Ii Jg Jk Jm Jn Lh Li Lj Lz Ma Mc Md Me Mg Mh Mi Mj Mk Mm Mp Mq Mr Mv Mw
Mx Na Nb Nc Ne Nf Nj Nl Nm No Ns Nt Nu Ny Oh Oi Oy Oz Pc Pe Pf Pg Po Qa Qb Qc Qd Qe) Pd(Et Fp Hq Hu Hw Hx Ii In Jh Jk Jm Jp Li
Lw Lz Ma Mc Md Mg Mh Mi Mj Mk Ml Mm Mq Mr Mu Mx My Na Nb Nc Ne Nj Nm No Nr Ns Nv Of Ok On Oy Oz Pb Pc Pe Pf Pg Po Pz
Qa Qb Qd) Mf(Et Hr Hu Hw Hx Ih Il Jk Jm Jn Lj Lw Ly Lz Me Mj Mk Ml Mm Mp Mq Mr Mu Mv Mw Mz Na Nb Nh Nj Nl Nn No Nq Nr Nt
Nu Oh Oi Ok Om On Oy Pb Pc Pe Pg Qb Qc Qd) Lv(Hq Hr Hv Hw Hx Ii Jh Lh Ma Mc Me Mh Mi Mj Ml Mm Mq Mu Mv Mx Mz Na Nc Ne
Nf Nj Nl Nm Nq Ns Nt Nu Nv Of Oh Oi Om Oz Pa Pb Pc Pf Pg Po Qb Qd Qe) Jr(aA Et Hu Hw Hx Ih Jh Jk Lh Lw Lz Ma Mc Me Mi Mj Mm
Mu Mv Mw Mz Nb Nc Nd Nh Nl Nm Nn No Nq Ns Nu Ny Oh Ok Om On Oy Pa Pb Pe Pf Pg Qa Qb Qc Qe) Jg(Et Fp Fr Hq Hr Hv Hx Ii Jk Jp
Lh Mc Md Mg Mh Mi Mm Mq Mw Mx Mz Na Nb Nc Ne Nj Nl Nq Nr Ns Nt Nu Ny Oi Om Oz Pa Pb Pf Pg Po Qa Qd Qe) aA(Hq Hw Hx Ih Jh
Jm Jn Jp Lh Li Lu Lw Ma Mc Me Mg Mh Mi Mq Mu Mv Mw Mz Na Nb Nd Nl Nm Nn No Nt Nu Oh Ok Om On Oy Pe Pf Pg Po Qb Qe) In(Et
Fp Hu Ii Jh Jk Jp Li Lj Lw Lz Ma Mc Md Mg Mj Ml Mm Mu Mw My Nc Ne Nf Nj Nm Ns Nv Of Ok Om Oz Pc Pf Pg Po Pz Qb) Jo(Et
Hq Hr Ih Ik Jh Jm Jn Jt Lj Lw Ly Lz Mc Me Ml Mm Mp Mu Mw Mz Na Nh Nj Nl No Nq Nt Nu Nv Oh Om Oy Pb Po Qa Qb Qc Qd) Js(Fp Hq
Hr Ih Ii Jm Li Lj Lw Lz Mc Me Mh Ml Mp Mu Mv Mx Mz Na Nf Nh Nj Nl Nn Nq Nt Nu Oh Oi Ok Om Oz Pc Pg Po Qc Qd) Nk(Ih Jk Li Lj
Lw Ly Lz Mb Mc Mj Mk Mp Mq Mr Mv Mw Na Nb Nd Nl Nn No Nq Ns Nu Oh Ok On Pb Pc Qc) Mi(Hr Hv Hw Ii Jh Jp Lj Lu Lz Mg Mh
Mm Mv Mw My Ne Nf Nl Nm Nu Nv Ny Of Pa Pf Pg Po Qb Qd Qe) Fr(Hx Il Jm Lh Lw Ly Mb Md Mg Mq Mu Mz Nb Nd Nh No Ns Ok Oy
Pa Pb Pe Pg Po Qb) Mx(Et Fp Hv Hw Jh Jm Jp Lh Mg Mj Mk Mr Nc Ne Nj Nm Nr Ns Nv Of On Pa Pe Qa) Pz(Fp Hq Hv Hx Ii Jm Jp Lh Li Md
Mg Mu Nc Ne Nf Nm On Oz Pa Pc Pf Qa Qb Qe) Qe(Et Hr Hv Ii Jp Li Mg Mm Mp Ne Nm Nr Of Oz Pa Qa Qb Qc Qd) Lu(Ih Il Jm Lj Mg Mm Mu
Mz Nf Nh Nn Oi Ok On Oy Pe Qb) Jp(Et Fp Hv Ii Jm Li Mg Mm My Ne Nj Nm Nv Of Oi Oz Qd) Fp(Et Hv Ii Lh Mg My Ne Nm Of Oz Pa Pc
Pf Qa) Oe(Il Im Jm Ly Mb Ml Mv Mw Nd Nh Nn Nq Nr Oi) Mv(Io It Iu Jm Mg Ml Mw Nf Nq Ny Of Oi) Pa(Hq Hr Jm Li Mp Ne Nf Nr Nv Pe)
Ng(Hu Ij Ik Il Im Ly Mb Nd Nh) Iv(Ih Lj Mb Mj Mr Nc Nr Oy Qc) Io(Ih Il Lj Mr Nc Nj Oy Qc) Of(Hv Hx Lh Mk Mr On Pb Pc) Nr(Ip Iq Ir It
Lh Mn Qa) Hv(Ii Jm Li My Ne Nv) Im(Ip Iu Jt Mn Ms Ni) Mb(Iq Ir Iu Jt Ms) Ij(Ip Ir It Jt Mn) Nq(Jm Mg My Ny) It(Hu Il Mr Nj) Mk(Hr Ip Nf)
Ne(Nc Oz Qa) Hx(Ii Jm Nv) Iu(Lj Mu Nl) Jt(Il Ly Nd) Mp(On Pc) Ms(Ly Nn) Hq(Mr Pb) Hr(On Pe) Ip(Ik Il) Qa(Jm Li) Jn(Ml Ny) Lh(Ii Nv) MnNj MwMy HuIr} Jp{Ms(Et Fp Hq Hu Hv Hw Hx Ih Ii In Io Ip Iq Iv Jh Jk Jq Jt Lh Li Lj Lw Ly Ma Mb Mc Md Me Mh Mj Mk Ml Mn Mr Mu Mv Mw My Mz Na Nc Nd Nf Nh Nl No Nq Nr Ns Nt Nv Nx Oe Of Oi Ok Om Oy Oz Pa Pb Pe Pf Po Pz Qa Qb Qc Qd Qe) Ir(Et Hr Hu Hv Hw Hx Ii Il Io It Iv Jg Jh Jk Jn Jq Lh Lj Lw Ly Lz Ma Mc Md Me Mh Mj Mk Ml Mm Mn Mp Mq Mr Mu Mw Na Nb Nf Nh No Nq Nr Ns Nt Nv Of Ok Oz Pe Pf Pg Po Pz Qa Qh Qc Qe) Jr(Et Hq Hr Hv Hw Hx Ii Jh Jn Jq Lj Lw Ly Lz Ma Mc Md Me Mh Mj Mk Ml Mm Mp Mq Mr Mu Mw Mz Nb Nc Nd Nf Nh Nm No Nt Nu Nv Of Oh Ok On Oy Oz Pa Pb Pe Pf Pg Po Qa Qb Qc) Og(Et Hq Hw Hx Ih In Ip Jh Jo Jq Li Lj Lu Ly Mc Mh Mi Mj Mk Ml Mm Mp Mq Mr Mw Mx My Na Ne Nf Nh Nj Nl Nm No Nr Ns Nt Nx Ny Oe Of Ok On Oz Pa Pd Pe Pf Pg Pz Qa Qb Qe) Lv(Et Fp Hq Hu Hv Hw Hx Ih It Iv Jh Jk Lh Ma Mc Md Me Mh Mi Ml Mm Mn Mq Mu Mv Mx My Mz Na Nh Nj Nm No Nq Ns Nt Nv Nx Ny Of Oi Ok Oz Pa Pb Pc Pf Pg Pz Qa Qb Qc Qd) Lu(Hq Hv Hx Ih In Io Ip Iv Jh Jk Jn Js Lw Mc Mg Mk Ml Mm Mp Mq Mr Mu Mv My Mz Na Nd Ne Nj Nl Nq Ns Nv Ny Oe Of Oi On Oz Pa Pb Pd Pf Po Pz Qa Qb Qc Qe) Jo(Et Fp Hq Hu Ih Ij Ik Jh Jk Js Lj Ma Mc Me Mf Mh Ml Mm Mq Mu Mw Mx Na Ne Nh Nj Nl Nm Nv Ny Oe Oi Om Oz Pd Pz Qd) Jm(Fp Hu Hv Hw In Io It Jg Js Lh Ly Ma Mc Mf Mg Ml Mm My Ne Nj Nl Nq Ns Nv Oe Oi Ok On Oz Pa Pf Pz Qb Qc) Mi(Fr Hv Hx Ii Io Iq Jg Jq Ly Lz Mf Mg Mm Mn Mp Mv Mx My Mz Na Ne Nl Nm Ny Of Ok Pa Pc Pd Po Pz Qd) Fr(Fp Hq Hw Il Jg Lj Lw Lz Mb Md Mg Mj Mp Nd Nn No Ns Nu Nx Oh Oi On Pc Pf Qa Qb Qc Qd) Jn(Et Hu Iq Jg Jk Js Lh Lw Mf Mn Mp Mu Mv My Nc Nf Nj Nm Nq Ny Of Oi On Oz Pd Qa Qd Qe) Jt(Fp Hu Hv In Io Iu Jg Js Lj Ly Lz Mf Mg Mh Mp Na Ne Nj Nn Nq Ns Oh Om Pg Qa Qb) Qe(Et Fp Hu Ih Iq Lh Li Mf Mn Mv Mx My Ne Nj Nm Nr Nx Ny Oe On Pc Pd Qc) aA(Et Hw Ih Il Ma Mb Ml Mq Mz Nd Nh Nn Nt Nu Nv Oh Om On Oy Pb Po Qa Qb) Mg(Hu Hx In Io Jg Js Lh Mf Mv My Ne Nq Oe Ok Oz Pf Pz Qa) Js(Iu Mf Ml Mv Oe Ok On Pa Pb Pc Pe Qa Qb) Nk(Ik Il Im Lj Lz Nd Nn No Nu Oh Om) In(Hw It Mf Mj Mr Mv Nb Ok Pc Qa Qb) Iu(Jg Jh Mf Mn Mw Ne Oe Pe Pf Qb Qc) Qa(Ih Iq Mf Mn Ne Ny Oe Pd Pz Qd) Lh(Ih Iq Jk Mn Ne Nq Of Oz Pz) On(Hq Ii Io It Iv Mn Ny Oe Oy) Pc(Iv Jg Mf My Ne Nx Ny Oy Pd) Ok(Et Ip Mn Nm Nx Ny Oe Pd) Pa(Hq Hr Io It Iv Mp Ny Of) Hx(Ip Iq Mf Mn Ne Oe Pd) Jg(Hu Ih Iq It Jh My Nq) Mv(Ip It Mf Mn Ne Nr) Ni(Ij Ik Il Im Iq) Nd(Iq It Iv Mn) Nv(Iq Mn Ny Oe) Ma(Iq It Mn) Of(Mk Mr Pb) Mf(Ne Oe) Hr(Mk Mr) Qb(Iq Ny) MzOe NeNy HqPb IpNx IvPd} Fr{Io(Fp Hq Hr Hv Ii Ik In Iq It Iv Jh Jk Jq Js Lh Lj Lv Lw Ma Mb Mc Md Mh Mi Mj Mk Ml Mm Mn Mp Mr Mu Mv Mx My Na Nc Nf Nh Ni Nl Nm Nn No Nt Nv Oe Of Oh Ok Om Oy Oz Pa Pb Pc Pd Pe Pf Qa Qc Qe) Iq(Et Fp Hq Hr Hw Ii In Iv Jg Jh Jq Js Lh Lu Lv Lw Lz Ma Mc Md Me Mh Mi Mj Mk Ml Mp Mr Mu Mv My Na Nb Nc Nf Nh Ni Nl Nn Nr Ns Nt Nv Nx Ny Oe Of Oh Ok Om Oy Oz Pb Pc Pe Pf Pg Po Qd) Iv(Et Hq Hv Hw Ii It Jg Jn Jq Lh Lj Lu Lv Lz Ma Mc Md Me Mh Mi Mj Ml Mm Mn Mp Mr Mu Na Nb Nc Nf Nh Nl Nn No Nq Nv Nx Ny Oe Oh Om Oy Oz Pb Pc Pf Pg Po Qa Qc Qd Qe) Nk(Et Hr Hw Ii In Js Lh Li Lw Ma Mb Mc Md Me Mh Mi Mj Mk Ml Mp Mq Mr Mx Nb Nh Nj Nm Nn No Ns Nt Ny Oe Of Oi Ok Om On Oz Pb Pc Pc Pg Po) Ih(Fp Hr Hw In Jg Jk Jq Js Lh Md Mi Mk Ml Mp Mq Mr Mw Mx Mz Nc Nd Ne Nj Nl No Ns Ny Oe Of Oh Oi Ok Om On Oy Oz Pa Pb Pc Pd Pe Pf) It(Et Fp Hq Hw Jg Jq Lh Lu Lz Ma Mc Md Me Mh Mj Mm Mr Mu Mw Mx Na Nb Nc Nf Nh Nl No Ns Nt Nx Ny Oe Oh Oy Oz Pe Pf Pg Po Qc Qd) Hu(Hq Hr Hw Jk Jq Lh Lj Lv Lw Lz Mc Me Mi Mj Mk Mr Mu My Mz Na Nb Nd Nh Ni Nj No Nq Nt Nv Of Oh Oy Oz Pc Pd Pg Po) Jn(Hx Ii Im Jg Jq Lh Li Lu Lw Ly Lz Mb Mg Mh Mi Mk Mm Ms Mu Mz Nb Nh Nm Nn No Nu Oe Oi On Oz Pb Pc Pf Pg Qe) Pz(Hv In Jm Js Lh Lv Lw Mi Mk Ml Mp Mq Mr Ms Mw Mz Nd Ne Ni Nj Nl Nm Nn Ny Og Om On Pa Pb Pc Pd Pf Qa Qb) Jr(Hv In Jg Jh Jk Lh Lu Lv Lw Mb Mg Mi Mj Mk Ml Mr Mv Mx My Nb Nf Ni Nq Of Og Oi Oy Pa Pd Pe) Nq(Ii In Ir Jg Jk Jo Js Md Mk Ml Mr Mu Mw Ne Nf Ng Nl Nr Ns Ok Om Pb Pc Po) Mz(Fp Hr Hx In Jm Jt Li Me Mg Ml Na Nd Ne Nj Nm Ny Og Pc Pd Qa) Ok(Et Hq Hv In Jk Jm Lv Mg Mm Ms Mv Nc Nd Ni Nj Nl Ny Oe Og Pd) Jt(Hv Hw Ii Jm Lh Lv Mf Mi Mj Mk Mr Nb No Nr Om Pa Pc Pe Qe) Jk(Hv Ii Ir Jq Js Md Ml Mp Nb Nc Nd Nl Nr Om Pb Pc Pe Po) Mn(Ik Jg Lu Lz Mh Mj Mu Nb Nh Ns Nt Nx Ny Oe Po Qc Qd) Mf(Hv Hx In Jh Lv Mv My Nd Ne Nj Nl Ny Of Oi On) Jm(Js Li Md Ml Mp Nc Nd Ne Nj Ny Oe Om On Pc Qe) Mq(Hv Jh Ml Mp Mv Mw Mx My Nc Nf Nl Nv Of Qe) aA(Il Li Ly Mb Mk Mm Nc Nh Nj Nu Oi Pb) Hv(In Jh Js Mv My Nf Of Og Pd) On(Hq Jh Ms Mw Nb Nf Ni Pd Pg) Jo(Ij Il Im Mm Mv Og Pf Qc) Nd(Jh Lv Mg Ms Ny Oe Og) Ng(Et Hr Ik Lu Mv Na Nf) Of(Ii Mr Nb Nc Nr Pa Pc) My(Md Mk Nc Pb Pc) In(Lh Mv Nb Nl Nr) Ip(Ij Il Im Ns Nx) Om(Mg Ms Ny Og) Nr(Im Lj Qc) Nc(Jh Mv Pd) Ir(Il Mh Pd) Ms(Jh Nj) LvNj MdMv MiJh MpPd MrHr NeNl HxOg} aA{Oz(Hq Hr Hv Hw Ii Im Jh Jk Jm Jo Lj Lu Lw Ly Lz Mb Mc Md Mh Ml Mp Mu Mv Mx My Na Nb Nc Nd Ne Nf Nl No Nq

Figure 10 Continued

Nr Ns Nu Nv Nx Ny Oe Of Om Oy Pa Pb Pc Pd Pe Pg Po Pz Qb Qd) Ng(Fp Hq Hr Hv Hw Ii Ik Jh Jm Jn Jo Jr Js Li Lj Lu Lz Mc Md Me Mh Mi Mk Ml Mp Mq Mr Mu Na Nb Ne Nf Nh Nl No Nr Nu Nx Ny Oh Oy Pb Pd Po Pz Qc Qd) Qe(Fp Hq Hv Hw Hx Ih Ii Jh Jm Jn Jo Jr Jt Lj Lw Lz Mc Md Me Mh Ml Mm Mp Mu Mw My Na Nb Nd Ne Nf Nl No Nq Ny Of Og Ok Om Pa Pc Pd Pe Pg Pz Qa Qc) Nk(Fp Hq Hw Ih Ii Im Jk Jm Js Jt Li Lj Lu Ly Lz Mb Mc Md Ml Mp Mq Mu Mx My Na Nb Nd Nf Nh No Nq Nt Nu Nx Ny Of Oh Oy Pb Pd Pz Qc Qd) Ok(Et Fp Hq Hw Hx Il Jm Lh Lj Lu Lz Mc Md Mg Ml Mu Mv Mw Mz Nb Nd Ne Nl Nm Nn Ns Nt Nu Nv Nx Oh Oi Om Pe Pf Pg Pz Qa Qb Qc) Lv(Hu Hw Jn Jr Lh Lj Lu Lz Mc Mq Mu Mv Nb Nc Ne Nj Nl Nm Nn No Ns Nu Nv Og Oh Om Oy Pc Pe Pf Po Qa Qb) In(Hu Hv Im Jq Lw Ly Mf Mk Mp Mr Ms Mv Mw Mz Nc Nn Nr Nt Nv Oe Of Og Oi Om Pb Pd Pe Pf Po Qb) Pa(Et Hr Hu Jk Jo Jq Js Lw Ma Me Mf Mi Mm Mx Mz Nd Nm Nq Nr Oe Of Og On Pc Qd) Ms(Hr Hu Hx Jk Jq Js Lu Lw Ly Lz Ma Mh Mi Ml Mx Nd Ne Nf Nl Oe Og Pe Qb Qd) Jr(Hr Hv Jk Jm Jo Jt Lz Mh Mu Mw Mx My Na Ne Nf Nl Nq Of Oi Pb Pd Qc Qd) Lh(Hq Hv Ii Jm Jt Lz Me Mh Ml Mm Mp My Na Ne Nf Nl No Nt Ny Og Pg Pz Qc) Mf(Hu Hv Hx Jn Js Lw Ly Ma Mi Mj Mw Mz Nr Nv Ny Oe Og On Pc Pf Qb) Pc(Et Hr Jh Jq Js Ly Mm Mv Mw Mx My Mz Nd Nf Nm Nq Ny Of Oy Pz) Mj(Fp Hu Im Jq Lw Ly Ma Me Mv Mw Nb Nd Nn Nr Og Oi Om Pe Po) Hu(Et Hr Hx Jq Js Ma Mi Mv Mw Mx My Mz Nr Nv Og Pg Qa) Jk(Et Hx Jn Lw Mi Mm Mu Mw Nm Nq Nv Om Pf Pg Qa) Js(Hv Hx Im Jn Lw Mg Mi Mw Mz Nc Nq Nv Oe Pe Qb) On(Ii Jh Jo Md Mx My Nq Nr Nv Ny Of Og Pd Pz Qd) Nr(Hx Im Jq Ma Ml Mw Mz Nc Nm Oe Oi Pf Pg) Mm(Hr Jo Lz Mi Mp My Nf Nq Of Og Pd Pz Qd) Et(Hr Jo Lz Me Mi Na Nq Of Og Pd Pz Qd) Jq(Hv Hx Lw Mg Mi Mw Mz Nn Nv Pf Po Qb) Oe(Hx Me Mw Mz Nn Nq Nv Om Pf Po Qb) Nm(Hr Hx Ii Mi Mx My Nq Of Og Qd) Hr(Hx Jn Lw Mg Mk Mr Qa) Jg(Ij Il Im Mk Mr Nj) Me(Jn Mg Mz Ny Qa) Ip(Ij Mb Mk My Nj) Nq(Jo Mg Mi Pf) Mp(Lw Mi Nn Qa) Mg(My Of Pz) Mn(Ij Ik Nj) Mz(Ma Mx Nd) Jn(Ii Jo Of) Qa(Pd Qd) Oi(Lw Og) Pf(Mx Qd) MiHq NcIo NeNl NiIk JoPg} On{Jo(Fp Hq Ih Ii Ik Jh Jk Jm Jq Js Jt Li Lu Lw Lz Mb Mc Md Mh Mj Ml Mm Mq Mu Mv Mw Na Nb Nc Nh Nj Nl Nn No Nq Nr Nt Nu Nx Og Oh Oi Om Oy Pb Pc Pd Po Pz Qb Qc Qd) Nk(Et Fp Hq Hv Hw Jg Jh Jk Js Lh Li Ma Mc Md Me Mi Ml Mm Mq Mr Mx Na Ne Nf Nh Nj Nl Nm Nn Nq Nr Ns Nt Nv Nx Oi Ok Om Oz Pb Pc Pe Pf Pg Po Pz Qb Qc Qd) Iq(Fp Hq Hr Hv Hw Ip It Iv Lh Lj Lv Lw Mb Mc Md Me Mh Ml Mn Mp Mq Mr Mw Mx Na Nc Nh Nj Nl No Nq Ns Nt Nv Nx Ny Oe Oh Ok Om Oz Pb Pc Pe Pf Pg Po Qc) Iv(Et Fp Hq Hx Io Jh Jk Jn Lh Lv Ly Mc Md Mj Ml Mm Mp Mq Mr Mx Nb Nc Nh Nj Nl Nn Nq Ns Nu Nv Ny Oe Oy Pc Pe Pf Qa Qb Qc Qd Qe) Mn(Et Hq Hr Hv Hw Hx It Jh Lh Li Lv Ly Md Mi Mj Mm Mp Mq Mw Mx Nl Nn Nq Ns Nt Nv Ny Oe Ok Oy Pc Pf Pg Pz Qa Qb) It(Et Fp Hq Hv Hw Hx Jh Jn Lh Lv Mj Mm Mp Mq Mx Na Nb Nc Nl Nn Ns Nt Nv Oc Oy Pc Pf Pg Qb Qc Qd Qe) Jt(Hv Hx Jh Jk Jm Js Lh Lj Mf Mp Mv Mw My Mz Nd Ne Nj Nm Nq Nx Ny Oe Of Og Pa Pd Pf Qa Qe) Hr(Et Ih Li Lw Lz Mg Ml Mq Mu Mw Mz Nb Ne Nj Nm Nq Nt Nu Nv Oe Pa Pc Pe Pz Qb Qd) Jr(Fp Hq Hu Jg Jh Jk Li Lu Lv Ma Mg Mj Mp Mx My Mz Nd Ne Nf Nr Nx Of Oi Oy Pa Po) Og(Hu Hx Ii In Jg Jk Jm Jn Jq Js Lh Lu Lv Mf Mp Mx My Ne Nq Oe Of Pa Pd Qe) Ny(Hu Jh Jk Jm Jn Jq Js Lh Mg Mi My Nd Ne Nj Nx Oi Pa Pd Qa Qb Qe) Oy(Hq Hw Hx Jn Li Lz Mc Mj Mp Ms Mu Mv Nf No Of Pg Pz Qa Qd) Ip(In Iu Jh Jn Jq Js Lh Mf Mm Mp My Ne Nj Nq Nx Pa Pz Qc) Io(Hx Jh Jk Jn Js Lh Lv Ly Mi Mm Nd Ne Oe Po Qa Qe) Of(Hq Ik Js Lu Lv Ma Mf Mp Mr Na Nf No Nv Oe Pb Pg) Ms(Ih Li Ly Mb Mr Mz Nc Nh Nu Nx Ok Om Po) Ir(Il Jg Lj Mi Mu Mv Mw My Nf No Nq Nr Pz) Iu(Fp Il Im Jg Lj Lz Mj Mr Mu Mv Nf Nl Qd) Oe(Hu Jk Jm Jn Jq Js Mf Mg Mp Ne Qe) Lv(Hu Ii Jk Jm Js Mf Mg Nd) Mg(In Jq Js Lh Mf Ne Pa) Ii(Hx Jn Lu Mf Mi Mp) Js(Hu Lh Pa Pg Qa Qe) Jn(Jm Jq Mf Nx Pd) Hq(Hx Jg Lh Qa) Lu(In Jk Nq) Qc(Jm Nf Pg) Jg(Jh Pg Pz) Mi(Jk Mj) Ni(Ij Mk) In(Ma Pf) Lh(Nf Pg) MfJm PaPd} Iu{Pa(Fp Hr Hv Hw Ih Ii Il Io Ip Jk Jq Li Lj Lw Ly Lz Mc Md Me Mj Ml Mm Mq Mu Nb Nd Nf Nh Nj Nm Nn No Ns Nt Nu Nx Oi Oz Pb Pc Pe Pf Pg Pz Qb Qd) Nv(Hq Hw Ih Iq Jg Jh Li Lw Ly Mc Md Me Mj Mk Ml Mn Mr Mu Mw Mx Na Nb Nf Nh Nj Nq Nr Nt Ny Oi Oy Oz Pb Pc Pe Pf Pg Pz Qc) Qa(Et Ii In Io Iv Jh Jn Jo Js Li Ly Lz Mg Mj Mk Ml Mr Mu Mw Nb Ng Ni Nr Og Oi Ok Oy Pb Pc Pe Pf Po Qe) Qe(Et Hq It Iv Jq Js Lv Ly Mg Ml Mu Mw Mx Nd Nj Nq Oe Oi Ok Oz Pf Qc) Ma(Et Hr Hv Io Ip Lw Me Mf Mh Mp Mw Nf Nk Nt Nu Pb Pf Pg Qc) Pe(Fp Hx In Iv Jg Jh Jm Jn Li Lv Mf Mg Mi Ms Ng Nq Qc) Jn(Et Iv Jk Mf Mj Mn Mw Ni Nn Oe Og Pc Qc Qd) Jr(Fp Ik Il Im Ip Jq Lj Mb Mm Nc Nx Pb) Hx(Jh Lv Mg Mn Ms Mu Nn Nq Oe Qc) Mv(Io It Jg Jm Lz Mu Om Pc Pf) Mz(Ij Il Im Ip Mm Nl Oh Om Pb) Nn(Jm Jo Mg Ms Ng Nk) Ir(Im Ip Oh Om Pb Po) Ok(Mg Ms Ni Nx Og) Ij(In Jt Ng Nk) Jo(Nk No Nq Pc) Lu(Ih Js Mm) No(Ms Og) Mi(Jh Qc) MgJg MnNi NkQb} Jr{Nk(Et Hq Hr Hv Hw Ih Jm Jn Jo Jq Lh Lv Ly Md Me Mg Ml Ms Mu Mx Na Nl Nn Nq Ns Nx Ny Oe Of Oi Om Pd Pg Pz Qa Qb Qc) Ir(Fp Hr Hu Hv Hw Il Ip It Lj Mc Md Me Mj Mn Mq Ms Mu Mv My Na Nf Nh Nj Nm Ns Nt Nu Oe Oi Ok Pa Pb Po Pz Qd) Mz(Jg Jn Jo Jq Lu Lv Ml Ms Mv Mx Nd Ne Ng Nq Nx Oe Og Pd) Iq(Et Ik Il Jg Jh Jo Lh Mj Mr Nb Nq Om Pb Pe Pg Po Qa Qe) Js(Et Lh Lw Mf Mn Mp Ms Nd Ng Nn Nv Oe Pf Pg Po Qa Qb Qe) It(Hx Jg Jm Jo Mf Mk Mn Mu Nf Ng Ni Oi Pa Po Qe) Iv(Hr Ih Mg Mn Mu Ne Nf Nl Oi Ok Pa Po) Ni(Hx Ip Li Lw Mf Mk Mp Nn No Po Qe) Mn(In Io Mf Mp Ms Mv Nn Og Ok Pa) Ip(Lv Lw Mf Mv Mx Nd Nn Og Pa Pd) Jg(Ih In Jh Jm Mf Mg My Nd Nq Nr) Ok(Io Jm Lu Mf Mg Nr Nx Og Pd) Pc(Jm Jn Jo Jt Mi Ne Of Pd) Io(Mf Mp Mu Mx Oe Pa Pd) In(Lw Nb Nr Nv Po Qe) Jm(Ma Mv Nv Og Pa Qa) Mi(Hq Hr Hu Jk Mf) Ng(Et Lw Nn Om Qe) Jo(Et Hw Nv Pg Qe) Ma(Ih Mf Nd) Lh(Ih Jt Nd) LvPd MsNd} Ir{Nd(Et Hr Hv Hw Hx Ih Ip It Iv Jg Jn Mc Md Me Mf Mg Ml Mq Mw Mx My Na Nc Nf Nh Nj Nl No Ns Nx Ny Oi Ok Oz Pa Pb Pd Pf Pg Pz Qa Qc Qd Qe) Jm(Hq Hr Hu Hw Ii Io Ip Iv Jg Jk Jq Lh Lw Ly Mc Me Mi Ml Mm Na Ne Nf Nh Ni Nl No Oe Of Oh Oi Om Pd Pe Pg Qd) Jt(Hv Hw Ii Jq Js Li Lz Mc Me Mj Mr Mv Nb Nf Ng Nh Nl Nr Ny Of Og Pb Pd Pe Pf Qa Qb Qe) Ih(Hq Hr Hv Hw Hx It Jg Jh Li Lw Mc Me Mg Mh Ml Mn Mp Mu Mx Na Nl Pf Po Qc) Nk(Hx Ma Md Mf Mg Mi Mn Mp Nn Og Om Pc) Ng(Et Hx Jk Js Ma Mf Mv Ne No Ns) In(Hv Mf Mg Mn Nj Nn No Ns Nx) Nv(Ip Js Mf Ms My Nj Og Oi) Mi(Ip Mg Mj Nm Ok Pc) Mq(Js Ma Mf Mp Ne) Ip(Lv Lw Ma Ok) Og(Nj Nn Ok Pa) Mg(Jg Nn Pa) Om(Lu Ms Ni) Mp(Hq Js) Nj(Iq Lh) Ok(Nm Pd) Pa(Js Ni) Pc(Il Pd) NoIq NrMv} Jo{Qe(Fp Hr Hv Hx Ih In Jn Js Jt Lj Ly Mh Ml Mm Mr Ms Mu Mx My Na Ng Nj Nm Of Oi Om Pz) Lv(Fp Hw Ih Ii Lw Lz Mh Mi Mk Mx My Nf Nk Nu Of Om Oy Pc Pe Po Qd) Iv(Hq Hr Hu Ih Iq Jq Lz Mc Mh Ms Mx My Na Nc Nh Nl Ns Nu Pd) Qa(Ii It Jt Mj Mk Mr Nb Nk Nr Oy Pa Pe Pg Po) Ip(Fp Ih Js Lw Mj Mm Nb Nk Nm Nr Pc) Et(Hx Ii Lw Mj Nb Pc Pe Pf Po) Mi(In Ly My Mz Nv Of Oi Pa Pg) Jg(Hq Im Ma Md Mw Nc Nd Oe Qc) Mm(Hw Ii Mr Ok Oy Pc Pe Po) Nq(Hx Mj Mk Nr Pa Pe Pg) Ok(Ij Im Lj Nd Nv Oh Om) Ma(Hx It Mk Mr Nr Pa) Io(Ij Li Mj Nb No Om) Pf(Hx Iq Mk Pa Pc Pg) Nm(Hw Lu Oy Pg Po) Jn(Mu Om Pa Pg Po) Hx(Mg Mv Pa Pg) It(Mn Mu No Pg) Mz(Hw Mk Mr) Iq(Ij Om Pc) Nn(Mn Mr) Nv(Ng Pc) Pe(Mg Mn) NdIk HwPa} Ok{Jt(Et Fp Hw Ih Ii Ij Ik Il Jh Li Lj Lw Ly Lz Mb Md Me Mh Mj Mk Mm Mp Mq Mr Na Nc Nf Nl No Nr Ns Nt Nu Of Og Om Oy Pc Qc) Mi(Fp Hx Iv Jh Jk Lu Mg Mn Mp Mq Mx Ni Nk Nm Nu Oe Of Og Oz Pc Qd) Ni(Hv Ih In Jm Jn Mf Mg Mz Nk Nm Oe Pa Pd Pz) In(Hq Hr Hv Hw Iq Jn Mr Mv Nb Nv Of Pd Qe) Ng(Ij Ik Il Im Ly Ma Mb Mz Nd Nn No) Ip(Hx Lu Lv Nk Nv Nx Oe Oi Pa Qa Qe) Mg(Io Iq It Iv Lv Mn Nk Oe) Oe(Jm Jn Mf Nd Nj Nm Pd) Jm(Iv Lv Ms Mv Qa) Pa(Iq Js Nk Pd) Ms(Mf Nd Nk) Lu(Iq Mn) Nd(Iq Iv) NrMv MkOy MnMz PzJg JsLh} Ng{Nv(Hq Hr Hu Ih Lj Ly Ma Mb Md Mh Mu Mx Mz Na Nc Nd Nh Nl Ns Nt Nu Nx Og Oi Om Qb Qd) Jg(Hr Ij Io Iv Jh Jt Lu Lv Lz Me Mk Mm Mr Ms My Nc Nq Nu Oy Oz Pb Pz Qc) Lh(Hx Ii Ip Iv Jk Js Jt Mi Mk Mn Mr Nb Ne Ni Oy Oz Pa Pb Pe Pf Qe) Nn(Io Ip Iq It Iv Lu Mn Nk Pc) Qe(Ih Jh Mf Mi Mv Ne Nj Po) Om(Hx Iv Lu Ma Ms My Nk Qa) Mz(Lv Ma Mi Mv Nk Pf) Pa(Io Ip Iq It Mv Ni) Pc(Im Jk Ma Mv Qa) Mv(Hv Pb) Nk(Hx Qa) Iv(In Ma) NoIp} Jn{Lv(Hr Hu Hv Ii Il It Jh Jm Js Jt Li Lw Md Mh Mj Mk Ml Ms Na Nb Nm Ny Og Oz Pb Po Pz Qc Qd) Pc(Fp Hr Hv Hw Ii Jm Mc Mh Ml Mu Nh Nx Ny Oy) Mi(Jq Lu Mg Ms Mu Mv Nc Nr Nu Nv Pa) Jg(Hu Ih Ms My Ni Nk Nq Og) Lw(Jm Jt My Ne Nm Nx) Mv(Hu Ih In Jm Mf Ni) Ni(Mu Mz Nn Nv) Nk(Nn Nv Pa) Lh(Js Jt Nr) Po(Il Pd) Mu(Ih Ne) In(Nb Nr) Iq(Nv Pa) NnJs MpPd QaJm JqOm} Mz{Nk(Hv Hx Jk Lh Lu Lv Ma Mf Mn Ms Mu Ni Nn Nv Oe Og Pe Pf Pg Qa Qb Qe) Ip(Hu Ih Ij Il Mb

Figure 10 Continued

Mw Ns Nu Pz Qd) Io(Fp Hu Ih Ik Il Im Mb Ns) It(Fp Hu Ih Ik Il Im Mb Ns) Mf(Jg Js Ma Mi Mv Ni) Mi(Hq Js Ms Ni Pa) Iq(Fp Ij Ik Il Im)
Ni(Jg Lv Nv Qe) In(Hx Lh Mk Pe) Iv(Ij Il Im Nr) Jm(Jg Ma Pa Qe) Lh(Js Jt Nr) Mn(Mu Pf) JsPa} Nv{Nk(Hu Hv In Jh Jm Js Jt Lv Mg My Ni
Nm Oe Of Og Pc Pd Qe) Iq(Ip Js Lu Mf Mi Ms My Ne Ni Nj Nm Oi Pa Pd) Mn(Js Jt Mf Ms Nd Ni Oi Pc Pd) Ip(Ii Js Lv Mf My Nq Pd Qe) It(Js
Jt Lv Mf Ms Nd Ni Oi) In(Io Lh Lv Mf Mj Ny Pc) Ni(Hu Iv Jm Lv Nd Pc) Io(Mf Ms Og) Iv(Ms Og Pd) Jm(Lv Ny Qe) Mi(Js Mj) LvJs MfNy
PzJg} Qe{Jm(Et Fp Hq Hv Hw Hx Ii Jg Jq Li Lw Ly Mc Md Mc Mg Mq Ms Mv Mx Nc Nh Nj Nl Ns Nx Ny Oe Om Oz Pa Pc Pd Pg Po Qa Qb Qd) Nk(Lv Mf Mi Mq Pa Pz) In(Ih Ii Ip Mp Pc) Mi(Jt Mj Nj Pz) Nd(Iv Lv Mn Ni) Ni(Ip Mf Om) LvIp IhLh IoJt} In{Lh(Hw Hx Ih Io Ip Iq It Jk Jq Lv Md Mi Mr My Nc Nq Ns Of Om Pa Po Pz Qa) Iv(Hr Hw Jg Mr Nd Om Pb Qc) Qb(Hw Mk Mr Pa Pb Pe) Hx(Ip Jg Nr) Mi(Im Pa) Qa(Nb Nr) HrPa} Nd{Iv(Iq Js Lh Lu Mi Og Pa Qa) Lv(Hx Im Nk Pf Qa) Iq(Ma Pa Pe Qb) Mv(Io It) Ni(Nk Nl) Ip(Lh Ma) ItQa PzJg JtLh} Jt{Lh(Ih Io Ip Iv Jg Om) Jg(Hx Nn No Oh) Pa(Ip Iq It Nk) NnIq MaIv IoPe} Jm{Qa(Ih Lv Mf Nk) Mv(Ip Iq Iv) Ma(Ip It) Hx(Iq Iv) Pa(Io Ip) NnIt} Pa{Nk(Io It Mn) Ni(Ip Iv) Hr(Mq Ns) Iq(Nj Pd) IpOg} Iv{Nn(Li Mg) Ma(Ih Nj) Og(No Om) NjLh} Nk{Hx(Ip Jg) NnNc MsOm IpQb PzJg} Mi{Hr(Hu Pc) Qa(Ih Ip)} Lh{Ih(Ms Qa) NjIq PzJg} Hx{MaIp NiOm PzJg} Pc{HrPe IpQa} NoIqOg MaMgIt PzQbJg

Unconstrained panels with 3 analytes, where 4.1E-7 >= 'AUC p-value' > 1.0E-7. Contains 9,319 panels of 287,980 total panels evaluated. : Mt{Ne(Et Hq Hr Hw Ii Jk Jq Jt Lh Li Lu Ly Lz Ma Mc Md Me Mh Mj Mk Mm Mq Mr Mu Mv Mw Na Nb Nf Nj Nl Nm No Ns Nt Nv Of Ok Oz Pa Pb Pf Pg Po Qb Qc) Pz(Hq Hw Hx Ih Ii Io It Jh Jk Jn Jo Jq Li Lu Lz Ma Mc Md Me Mh Mm Mq Mw Mx Na Nc Nf Nj Nl No Ns Nt Nv Nw Ny Of On Oz Pb Pf Pg Po Qa) Nq(Hq Hw Ih Ii Jh Jk Jn Jq Jt Li Lj Ly Lz Mc Me Mj Mk Mm Mp Mq Mr Mw Na Nc Nf Nh Nl Nm No Ns Nv Of Ok Oz Pa Pe Pf Pg Qa Qb Qc Qd) Oi(Et Fp Jg Jq Lh Li Ly Lz Mb Mc Md Me Mi Mj Mk Mm Mq Mr Mv Na Nb Nc Nf Nh Nl Nm No Ns Nt Nu Nw Oy Oz Pa Pb Pe Pf Pg Po Qb Qc Qd) Ih(Hq Hr Hv Hw Io It Jh Jk Li Lw Ma Mc Md Me Mh Mj Mk Ml Mp Mq Mr Mu Mx Nb Nc Nj Nm No Nr Nt Nv Of On Oz Pa Pb Pe Pf Pg) Nx(Fp Fr Hq Hw Hx Jg Jo Jq Li Ly Lz Mb Mc Md Me Mh Mj Mk Mm Mq Mr Mv Mw Na Nc Nf Nl Nm No Ns Nt Of Oz Pa Pb Pf Po Qa Qb) Jh(Fp Hq Hv Hw Hx Jk Jn Lu Lw Ma Mc Mh Mj Mk Ml Mp Mr Mu Mv Mx Na Nj Nl Ns Nt Nu Nv Of Ok On Oz Pa Pb Pc Pf Pg Po Qa) My(Et Hq Hr Ii Jk Jq Jt Lh Li Lj Ly Lz Md Me Mm Mq Mu Mv Nc Nf Nm Ns Nu Nv Nw Of On Oy Oz Pf Pg Po Qa Qb Qc Qd) Qe(Et Hw Hx Jg Jq Lh Li Lu Ly Lz Mc Md Me Mh Mj Mk Mm Mr Mv Mw Na Nc Nf Nh No Nt Nu Oh Ok Oz Pa Pb Pe Pg Po Qb) Mx(Hq Hr Ii Io Jn Jo Js Jt Li Lu Lz Ma Mc Md Me Mm Mp Mu Nc Nf Nj Nl Ns Nt Nv Pb Pc Pd Pf Pg Po Qa Qb) Hx(Fp Hq Hv Jn Li Lu Lw Ly Ma Mc Me Mh Mk Mp Mu Mw Nf Nh Nm Nt Nu Nv Nw Ok On Oz Pa Pg Po Qa Qb Qc Qd) It(Fp Hw Jk Jn Jq Lu Mc Md Me Mh Ml Mm Mq Mv Mw Na Nb Nf Nj Nl Nn Ns Nt Nu Ny Of Oz Pf Pg Po Qb Qd) Hv(Fp Hq Hr Io Ip Jk Jn Lu Lw Ma Mc Mh Mk Ml Mq Mw Na Nj Nl Ns Nt Nu Nv Nw Of On Oz Pa Qa) Jk(Fp Hq Hu Hw Io Jn Li Lw Ma Mc Mh Mj Mk Ml Mp Mr Mv Nb Nf Nj No Ns Ok Pa Pb Pf Po Qa) Hu(Et Hr Ii Il Jq Lh Li Ly Lz Mb Mj Mk Mp Mr Mw Nb Nc Nn No Ok Oy Pa Pb Pe Pg Po) Jn(Fp Hq Io Jt Lh Ma Mc Md Me Mh Ml Mp Mq Mw Na Nf Nj Nl Nm Ns Nt Nv Of Pf Po) Ml(Hq Is Iv Lh Lu Lw Ma Mc Mk Mp Mr Mw Nj Nl Ns Nt Of Om On Pa Pb Pf Qa) Jg(Hq Hr Ii Jt Lh Lw Mc Md Me Mk Mn Mp Mr Nb Nh Nl Nt Nv Oe Of Ok Pa Qc) Nw(Et Fp Hq Ii Ji Jm Jr Lh Li Md Mg Mh Na Nm Nv Og Oy Oz Pa Pf Pg Po Qd) Ny(Hr Ii Io Jq Lh Lj Lu Lz Mj Mm Mq Mr Mv No Nu Oh Om Oy Pb Pe Pg Qc Qd) On(aA Et Il Lz Ma Mc Md Mj Mm Mp Nj Ns Nt Nv Ok Oz Pa Pb Pc Pf Qa Qd) Io(Fp Hr Ip Li Lu Mc Md Me Mh Mj Mp Mv Mw Nt Nu Oc Of Pb Qb Qc) Ok(Fp Hw Il Jq Li Lw Mh Mk Mm Mr Mz Na Nf Nj Nl Nm Nt Nu Nv Pa) Hr(Hq Hw Li Lu Lw Lz Mc Mg Mh Mj Mm Mp Na Nb No Ns Pb Po) Fr(Im Jr Lj Lu Lz Ma Mp Mr Mz Oy Pa Po Qa Qb Qc Qd) Ip(Hq Hw Il Lh Lz Mk Mp Mr Mu Nc Nn Ns Oy Pf Pg Po) Lw(Hq Hw Il Jq Mc Md Mh Mp Mw Na Nf Nl Nt Pc Pg) Pd(Fp Ij Jq Lj Ly Mb Md Mq Nh Nn Oy Qc Qd) Mn(Et Il Lj Mm Mv Nc Nh Nm No Oy Pg Qd) Mp(Fp Hq Jt Lu Ma Mh Na Nl Nm Ns Nt Of) Mr(Hw Il Lj Mh Na Nb Nf Nl Nu Nv Pa Pg) Lh(Hq Hw Ir Lv Md Me Mi Na Nj Oe Og Pg) Om(Iq Ir Jp Jr Lv Md Mf Mg Mz Nd Oe Og) Pc(aA Ij Ly Lz Ma Mv Mw Nf Pf Qa Qb Qd) Mk(Fp Hw Lz Mh Mj Na Nb Nf Nt Nv Pf) Jt(Mg Mu Nj Nm Ns Oe Oh Oz Pg Qa Qb) Pa(aA Hw Il Lj Lu Mh Mj Nb Nu Nv Pf) Iv(Et Hq Ir Li Lj Mb Mv Nc Nn Pf) Js(Ij Il Im Jq Lj Mb Nn Nu Oy Qd) Mi(Ij Jp Ly Mb Mu Nh Nt Oy Qb) Of(Hw Ii Lu Ma Mj Nj No Ns Po) Il(Ji Jr Ms Nb Nd Og Pb Pe) Fp(Hw Li Ns Pb Pf Po Qa) Oy(Iq Ir Jr Mf Mg Mz Oe) Lu(Ma Mb Me Mw Nn Qb) Im(Ir Is Jp Lv Lx Ni) In(Jq Mb Md Nh No Oh) Jo(Md Mq Nh Nl Oh Qc) Og(Mb Mu Nb Nn Oh Pb) Pe(Hq Hw Na Nf Nl Nu) Nt(Hw Mj Nb No Po) Mf(Lj Nn Nu Oh Qd) Oe(Ly Ma Mh Mu Nn) Nj(Ma Na Ns Qa) Ij(Is Lv Lx Ms) Ik(aA Jm Lx Ni) No(Ir Na Nl) Mz(aA Ii Li) Nm(Ma Ns) Nr(Mh Nl) Mg(Ii Nb) Hq(Ir Pg) Iq(Oh Qd) Ji(aA Mb) NnIr NuMu LvMq MaJl MhNb MjNl NaHw IiNv IuOh JrLi} Jj{Pe(Hq Hr Hu Hw Ih Ii Im Jh Jk Jm Jo Jq Li Lj Lw Lz Ma Mc Md Me Mj Mk Ml Mp Mq Mr Na Nb Nc Nf Nh Nj Nr Ns Nu Ny Oh Om Oy Oz Pb Pd Pf Po Pz Qd) Mz(Et Fp Hq Hr Hu Hw Ih Ik Jh Jm Jn Jo Jq Jt Li Lj Lw Lz Mb Mc Md Me Mh Mm Mp Mq Mu Mx Na Nf Nh Nl Nn Ns Nu Nx Om Oy Oz Pb Pd Pz Qb Qc Qd) Qb(Fp Hq Hr Hu Hw Ih Ii In Jh Jm Jo Jq Jt Li Lj Lw Lz Ma Mc Md Me Mh Mp Mq Mx Na Nb Nf Nh Nj Ns Nu Nx Og Om Oy Oz Pd Po Pz Qa Qc Qd) Pc(Hq Hu Hw Ih Ii In Jo Jq Jt Lz Ma Md Me Mj Mk Mp Mr Ms My Na Nb Nc Ne Nf Nj Nn Nr Ns Nu Om Oz Pb Pd Po Pz) Mn(Hq Hu In Jh Jm Jo Jq Lw Ly Lz Mc Me Mh Ml Mq Ms Na Nc Ne Nf Ng Nh Ni Nk Nl Ns Nt Oe Og Oh Oi Oy Pd Pz) Mp(Fp Hq Hu Hw Jo Jq Js Jt Li Lw Ly Lz Mb Md Me Mh Mj Ml Mq Mu Na Nc Nf Nh Ns Nu Nx Oe Oh Oi Oy Oz Pd) Im(Et Fr Il In Jk Jt Li Lu Lw Lz Mi Mj Mk Ml Mm Mr Nb Ne Nl Nm No Nr Nt Nu Nw Of Ok On Oy Oz Pa Pf Qa) Ii(Hr Hu Hw Ik In Jo Jq Js Mc Mj Mk Ml Mq Mr Mu Mx Na Nb Ne Nf Nj Nr Ns Nu Of Og Oy Oz Pd Qc Qd) Qd(Hq Hr Hu Ih Jh Jm Jo Jq Jt Li Lw Lz Mc Mh Mq Mx Na Nb Nd Nf Nj Ns Nu Nx Og Oy Pd Po) Nr(Hq Hu Hw Ih In Jo Jq Jt Li Ly Lz Ma Mc Md Me Mh Mj Mk Ml Mr Nb Nf Nu Og Oy Oz Pd) Hv(Hq Hr Hu Hw Ij Il Jh Jo Js Ly Lz Mb Me Ml Mq Mx Na Nc Nd Nf Nj Nu Oe Og Oz Pd Qc) Of(Hq Hr Hu Hw Ih In Jq Jt Li Lw Ly Lz Ma Mb Mc Md Mj Mx Na Nb Nd Nf Ns Nu Oz Pd Po) Nt(Fp Hr Hw Ih Jh Jt Li Lw Lz Md Me Mh Mu Mx Nf Nj Ns Nu Nx Om Oy Pd Pz Qc) Ma(Et Hw In Jk Jt Li Lu Ly Mj Mk Mr Mv Nb Nc Nh Ni Nj Nu Oi Ok Om Oy Po) Nl(Hr Hu Ih Ij Il In Jo Lw Lz Mc Me Mh Ml Mu Mx Nd Ne Nf Nn Nu Oy Pb Pz) Lu(Fp Hu Ih Jo Mb Mc Me Mh Ml Mq Mx Na Nc Nf Nj Ns Nx Oe Oz Po Pz) Mj(Hq Hr Hu Hw In Jo Js Li Lz Mc Me Mh Mk Ml Mr Na Nb Nc Og Oz Pd) Ne(Hw Ih Ij In Jo Jt Li Lz Mh Ml Nd Nf Nh Nj Nn Nu Om Oy Pb Po) Mk(Hq Hu Hw Ih Jo Jq Jt Ly Lz Mc Me Mh Ml Nu Og Om Oz Pd Pz) Nb(Hq Hr Hu Hw Jo Js Ly Mc Md Me Mh Ml Mr My Na Nf Og Oz Pd) Jk(Fp Hq Hr Ih Jm Li Lw Lz Mb Md Mh Mx Nu Nx Oi Om Pb Po Qc) Mr(Hq Hu Hw Ih Jo Jq Jt Ly Lz Mc Me Mh Ml Og Oy Oz Pd) Nh(Hr Ih In Jm Jo Jt Lw Lz Mh Ml Nd Nf Nj Nu Oy Po) Pb(aA Hq Hw Ly Mc Me Mh Mi Ml Mv Na Nc Nm Ny Oz Qa) Mf(Hq Hu Ih Ij In Jt Me Mh Mu Mx Nf Ni No Po Qc) Nc(Hw Ih Il In Li Lz Mh Mu Mx Nf Nu Oy Po) Jm(Hq Hr Hu In Jq Lz Mc Me Mh Mu Mv Nd Oz) Ly(Hq Ih Ij In Jo Lz Nd Nf Nv Oy Po Pz) Ng(Hr Ih In Mc Md Na Nd Ns Oi Oy Oz Pd) Et(Ij Il Jo Js Lj Md Mh Ms Mu Nx Qc) Om(Hu Ik Js Jt Mi Ml Mm Mq On Oz Pz) Nn(Ik Ji Mb Mi Mw Nv Og Oi Pf Qa) Nq(Ij Il Lj Mb Mi Ms Nd Ny Og Pz) No(aA Hx Mc Mg Ml Mv My Nd Pg) Mm(aA Ij Il Mq Nd Nj Ns Nx Og) Pf(Fp Hr Mb Md Mu Mx Nx Ny Qc) Po(In Js Ml Mx Na Nf Oe Oz) Nk(Il Js Mc Nd Nx Oe Oh Oz) Ij(Hx Ji Nw On Oz Pa Pg Qa) Oi(Hu In Mc Md Nu Oy Oz Pd) Mg(Jh Js Lj Mv Nx Og Oh) Mi(Fp Hr Lj Nx Oe Pz Qc) Hw(Hq Hu Jo Js Ml Na Oz) Qc(aA Fr Mv My Nm Qa) Ni(Fp Hq Jq Js Lj) Lw(Hu Mc Mu Pz) Mv(Ik Jo Mb Og) Nd(Ji Mw My Oh) Jt(Mb Nf Og Oz) Li(Hq In Mc Oz) Oy(Jo Mc Ms Pz) aA(Hu Ih Lj Ns) Nm(Jo Js Ms) Ml(Lz Mh Nu) Il(Hx Pa Qa) Mw(Lj Ms) Ik(Js Nv) LzMc MhPz HuJh JgLj OeOh} Nw{Pz(Et Hr Hu Hw Jh Jk Jn Lj Lw Lz Ma Mc Me Mh Mj Mk Ml Mm Mp Mq Mr Mx My Mz Na Nb Nd Nh Nj Nl Nn No Nr Ns Nt Nu Nv Of Oh Oi Ok Om Pb Pe Pg Po Qc Qd) Qe(Hq Hu Hw Hx Ih Il Jh Ji Jk Jn Lh Lj Lw Lz Ma Mc Md Me Mh Mj Ml Mq

Figure 10 Continued

Mr My Mz Na Nb Nc Nf Nh Nj Nl No Ns Nt Nu Nv Oh Oi Om On Pb Pc Pe Pf Pg Po Qc) Jp(Hq Hr Hu Hw Hx Ih Jh Jk Jn Lh Lw Lz Ma Mc
Md Me Mh Mj Mk Ml Mq Mr Mw Mz Na Nc Nf Nl No Nq Nr Ns Nt Nu Oh Ok Om On Pa Pb Pc Pe Pf Pg Po Qa Qb Qc) Hv(Et Hq Hr Hu Hx
Jh Ji Jk Jn Lh Lz Ma Mc Md Me Mg Mh Mj Ml Mm Mq Mw Mz Na Nb Nc Nf Nj Nl Nm Nq Nr Ns Nt Nu Ny Oh Oi Oz Pb Pc Pf Pg Po Qa Qb
Qd) Fp(Hq Hr Hu Hw Hx Jh Ji Jk Jm Jn Li Lw Lz Ma Mc Md Me Mh Mj Mk Mm Mp Mr Mz Na Nb Nc Nf Nj Nl No Ns Nt Nv Ny Oi Om On
Oy Pb Pe Pg Po Qb Qd) Ne(aA Et Hq Hr Hu Hx Ii Jh Ji Jm Jn Lh Li Ma Mc Md Me Mg Mh Ml Mm Mu My Mz Na Nb Nf Nh Nj Nm Ns Nt Nv
Ny Of Oi On Pb Pc Pf Pg Po Qb Qd) Mx(Hq Hr Hu Hx Ii Jk Li Lw Lz Ma Mc Me Mh Ml Mm Mp Mq Mv Mz Na Nb Nf Nh Nl No Nt Nu Oi
Ok Om Oy Oz Pb Pc Pf Pg Po Qb Qc Qd) Mg(Et Hq Hr Hx Jh Ji Jk Jm Jn Jr Lh Li Lj Lz Ma Mc Md Mh Ml Mw My Na Nf Nj Nl Nm Nr Nv Of
On Oz Pf Po Qb) Li(Et Hq Hr Ii Ji Jm Lh Ma Mc Md Mk Ml Mq Mu My Nc Nf Nj Nl Nm Nn Ns Nt Nv Ny Of Oi On Oz Pc Pf Pg Qb) Pa(Hu
Hw Ji Jn Lj Lz Ma Mc Md Mj Ml Mm Mq My Mz Nd Nj Nm No Ns Nu Of Oh Oi Om On Oy Pc Pg Qa Qb Qd) My(Et Hq Hr Hx Jh Ji Jk Jm Jn
Jr Lh Lj Lz Ma Mc Md Mh Mm Mr Mu Na Nb Nf Nj Nl Nm Oz Pc Pf) Mi(Hx Ih Il Ji Jn Lh Lw Ma Mc Md Me Ml Mq Mz Na Nb Nc Nd No Nr
Ns Oh Ok Om On Oy Pb Pe) Of(Et Hq Hr Hw Jh Ji Jk Jm Jn Lj Lz Ma Mc Md Mh Mj Mm Mu Na Nb Nf Nj Nm Oy Oz Pe Pf Po) Jg(Hw Ih Il Ji
Jm Jn Lw Lz Ma Me Mj Ml Mp Mr Mu Mv Nd Nf Nh No Oh Ok On Oy Pe Qb Qc) Nv(Et Hq Hr Ji Jk Jn Lj Lz Ma Mc Mk Mm Mu Mw Na Nc
Nf Nj Nm On Oz Pc Pf Pg Qa) Oz(Et Hq Hr Hx Ii Jh Ji Jm Lh Ma Mc Mh Mk Mm Mq Mr Mu Nj Nm Ns Nt Pc Po Qa) Jm(Hr In Ji Lj Lz Ma
Mc Md Mh Ml Mw Nc Nf Nj Nm Nr Nu On Pf Pg Qb Qd) Lv(Ih Jk Jn Lj Lw Ly Lz Md Mw Nb Nh Nn No Nr Ny Ok On Oy Pe Qa Qc) Ii(Et
Hq Hr Jh Ji Jn Ma Mc Md Ml Mm Nc Nj Nm Nu Oi On Pc Pf Qa Qb) In(Ih Me Mh Mp Mq Mz Na Nl Nn No Nq Nt Nu Oh Oi Oy Qc Qd)
Pd(Hr Ih Ly Me Mp Mw Mz Nf Nh Nl Nn Nq Nt Nu Oh Oi Om Qc) Nm(Hq Jh Ji Lh Ma Md Ml Mq Nc Nf Ny Pc Pf Po Qa) Hx(Hq Hr Jh Md
Mh Ml Nc Nf Nr Nt Pg Po) Nx(Ih Il Lw Ly Mu Mz Nd Nh Nn Ok Om Pb) Qa(aA Et Hr Jn Ml Mm Nj Nt Oi Pc Qd) Lh(Et Hq Jh Jk Mh Mp Na
Ny Oi Pg Po) Og(Ih Lw Me Mp Nd Nh Nn Ns Oe Oi Om) aA(Il Ly Mb Ml Mm Nc Ns Oi Pb Qc) Nf(Et Hq Hr Hu Jh Mr Nj On Pf) Ij(Fr Iu Iv Jo
Lu Lx Ms Nk Oe) Il(Iu Jo Jq Jr Js Ms Mv Nk) Im(Fr Io It Iv Jo Lu Lx Nk) Mb(Io It Jo Jr Js Lu Mf) Mk(Hq Iq Ir Is It Nu Pg) Mr(Fr Jl Jr Mp Nu
Oy Pg) Ik(Iq Ir Iu Jl Jt Mn Ni) Jq(Ih Lj Ly Mv Nd Nn Oy) Md(Et Jn Lj Mv Pf Po) Ny(Et Lz Nj On Pb Pc) Nd(Jo Js Lu Mf Mp) Nr(Io Is Ma Pf)
Hu(Io Iv Mh Mu) On(Hq Nu Oy Pg) Ly(Jr Js Lu) Mp(Lw Ml Pe) Nc(Jn Ml Nj) Et(Mh Mq) Ma(Ji Pc) Jk(Js Mu) FrLj NnJo MhJh MqJi OyPc}
Ji{Mv(aA Et Hq Hv Hw Ih Jg Jn Jp Lh Li Lu Lw Lz Mc Md Me Mh Mj Mk Mm Mq Mr Mw Mz Na Nb Nc Nd Nj Nl Nm No Ns Nt Nu Nv Nx
Oh Oi Ok Om Oy Pb Pe Pf Pg Po Qa Qb Qc Qd) Og(Fp Hq Hr Hw Ii Jh Jk Jn Jt Li Lj Lw Lz Mc Md Me Mg Mh Mk Ml Mm Mp Mq Mr Mx
My Mz Na Nb Nc Nd Nl Nm No Nr Ns Nt Nu Nv Of Oh Ok Oy Oz Pb Pd Pe Pg Po Qb Qc Qd) Jr(aA Et Hq Hv Hw Ih Jh Jk Jn Lh Li Lj Lw Ly
Lz Mc Md Me Mh Mj Mk Mm Mp Mr Mu Mw Na Nb Nc Nj Nl Nm Nn No Ns Nt Nu Nv Oh On Oy Pb Pe Pg Po Qa Qb Qc Qd) Qe(aA Et Hq
Hr Hu Hv Hw Hx Ih Jg Jh Jk Jn Lh Li Lw Ma Mc Md Me Mh Ml Mm Mp Mq Mw My Na Nf Nj Nm Nr Nt Nu Nx Of Oh Oi On Oy Oz Pa Pf
Pg Qa Qb Qc) Lu(aA Et Fp Hq Hr Hv Hw Jh Jk Jn Lh Lj Ma Mc Md Mg Mh Mq Mr Mu Mw My Mz Na Nc Nl Nm Nn No Ns Nu Nv Ny Oh Oi
Om On Oy Pb Pe Pf Pg Qa Qb Qc Qd) Js(Fp Hq Ii Jh Jk Jm Li Lj Lw Lz Mc Md Me Mh Ml Mp Mq Mw Mx My Mz Na Nd Nf Nj Nm Ns Nt
Nu Of Oi Om Oy Oz Pd Pg Qc Qd) Jp(Hr Ih Jn Lj Lw Ly Lz Mb Me Mh Ml Mp Mr Mu Mz Nb Nc Nd Nh Nl No Nr Ns Nt Oh Ok Om On
Oy Pb Pe Pg Po Qa Qb Qc) Oe(Et Fp Hq Hw Ii Jk Jn Li Lj Lw Lz Mb Mc Md Mh Mj Mm Mp Na Nb Nd Nf Nl Nn No Ns Nt Nu Nx Of Oh Oy
Pb Po Qa Qc Qd) In(Fp Hq Hu Jh Jk Li Lw Lz Ma Mc Md Me Mg Mh Ml Mp Mu Mx Mz Na Ne Nf Nl Nm Nt Nu Ny Of Om Oy Oz Pd Qb Qc
Qd) Jg(Fp Hq Hr Hv Hw Ii Jk Jn Lh Lv Mc Me Mg Ml Mm Mp Mw Mx Mz Na Nc Nd Nr Nt Nu Nv On Oy Oz Pa Pb Pc Pf Qc Qd) Jt(Fp Hq Hr
Ih Ii Jh Jk Lj Lz Mb Mc Md Mg Mh Mm Mp Mx Mz Na Nf Nh Nl No Ns Nu Nx Oh Oy Oz Pb Pd Qb Qc Qd) aA(Hq Hw Ih Jm Jn Lh Lj Lw
Mb Mc Md Mg Ml Mq Mu Mw Mz Nb Nd Nn No Nu Oh Oi Ok Om On Pb Pe Pf Pg Qb Qc) Nq(Et Hq Hr Hw Hx Ih Jh Jk Jn Lw Mc Md Mh
Ml Mm Mw Mz Na Nc Ne Nf Nl Nt Nu Oi Ok Pe Pf Pg Qd) Lv(Fp Hr Jh Lh Lw Mb Mc Me Mi Ml Mq Mr Mw Mz Nc Ne Nm Nx Of Oi Ok Oz
Pc Pe Pf Qb) Hx(Fp Hq Hr Hu Hw Jk Lh Ma Mc Mc Mg Mj Ml Mq My Na Nc Nf Nm Nv Of Oi Oz Pa Pc Pf) Nx(Hu Hv Jh Lh Ma Me Mg Ml
Mq Mw My Mz Nb Nd Nj Nn Nv Of Oh Ok Oz Pc Pd Pe Pg) Jq(Et Hw Ih Ii Lj Lw Lz Mb Mj Mk Mq Mr Mz Nb Nf Nn No Oh Ok Oy Pb Pe Po
Qd) Pa(Fp Hq Hu Ii Jk Jm Li Ma Mg Mi My Mz Na Ne Nf Nm Of Pc) Mi(Fp Hr Ii Jh Jk Li Mm Mx My Ne Nf Of Ok Pc Pd) Ny(Im Jn Lj Ly Lz
Mb Md Mh Mm Nf Nh Ns Oh Oy) Mg(Hv Ma Mw Mx My Ne Oi Ok On Oz Pf Qa) Io(Et Ik Lj Lz Mb Mu Nh Nj No Oh Om Qa) Pz(Hv Ii Lh
Ma Ml Mx Ne On Oz Pc Pd Pf) Jm(Fp Hv Ma Mw Mx Mz Ok On Oz Pf Pg) Mx(Hv Jn Lh Nr On Pc Pe Pf Qa) Jo(Ij Ik Il Ly Mb Mu Nd Nh
Om) Pd(Hv Jn Lh Ma My Ne Oz Pc Pf) Ip(Ih Ik Jk Mj Nh No Oh Om) Qa(Ii It Iv Ml Ne Nr Pc Qd) Ng(Ih Il Im Ly Mb Nh No) Ik(It Iu Iv Jl Ms
Ni) Im(Ir Is Iu Lx Mn Nk) Ij(Fr Iq Is Lx Ms) Iv(Et Lw No Nr Oh) Of(Lh Mk Mr Nb Pb) Pc(Hv Lh My Ne Oy) Nk(Il Mb Nd Oh) Ii(Hv Lh Mw
Ok) It(Ih Nj Oh Om) Ma(Hu Mp Nr) Ne(Hv Nc Oz) Iu(Lj Oh Om) On(Hq Nf Oy) Mn(Ih Om) Li(Nn Pf) FpPf FrLj NrIs MfIl MpNd MyHu
HrPe} Is{Ii(Fp Hq Hw Io Iu Jn Li Lj Lw Lz Mc Md Me Mh Mj Mk Ml Mm Mp Mq Mr Mw Mx My Na Nb Nc Nf Nh Nl Ns Nt Ny Of Oh Om
Oy Oz Pb Pe Po Pz Qa Qb Qd) Nv(Et Fp Hq Hu Hv Hx Ih Il Io Ir It Iv Jh Lj Lz Mc Md Me Mh Mj Mm Mn Mp Mq Mr Mw Na Nc Nh Nn No
Ns Oh Ok Oy Oz Pb Pe Pf Pg Qb Qc Qe) Lv(Et Hq Hr Hv Io Ir Iv Jk Jn Li Lj Lw Lz Mc Md Mh Mj Mk Mm Mp Mq Mr Mw Na Nb Nh Nj
Nn No Nq Ns Ny Of Ok Oz Pb Pe Pf Pg Po Qa Qc Qd) Nm(Fp Hq Hu Hw Il Io Ip Ir Iv Jk Jq Lj Lz Mc Md Me Mh Mj Mk Mm Mp Mr Mw My
Na Nb Nc Nf Nh Ns Nt Nu Ny Of Oh Om Oz Pe Pz Qb Qd) Mn(Et Hq Hr Hu Hv Hw Hx Ih It Jh Jk Jn Lw Mc Me Mh Mj Ml Mm Mp Mq My
Na Nf Nl Nn Nq Nt Nu Ny Of Ok Oy Oz Pb Pf Qb Qc Qd Qe) Ly(Fp Hq Hr Hu Ih Il Io Ip Ir Jh Jk Jn Lw Lz Mc Md Me Mh Mk Mm Mp Mq
Mw My Na Nc Nd Nh No Nq Ns Nt Of Oz Qb Qc Qd) Ne(Fp Hq Ih Ir It Jk Lj Li Lj Lz Mc Md Me Mj Mk Mm Mq Mr Mw Na Nb Nc Nh Nl No
Nq Ns Nt Of Oh Oy Oz Pe Po Pz Qa Qd) Ok(Et Fp Hq Hr Hx It Jh Jk Jn Lw Mc Md Me Mh Ml Mm Mp Mq Mr My Nh Nn No Nq Nu Ny Of
Oz Pb Pe Pf Po Pz Qb Qd) Qe(Et Fp Hr Hu Hv Hw Hx Ih Il It Jh Jk Jn Li Lw Mc Me Mh Mj Ml Mp Mq My Na Nf Nh Nq Nt Nu Ny Pb Pf Pz
Qb) Hx(Et Hv Il It Iv Jk Jn Li Lw Mc Md Me Mh Mj Ml Mp Mq My Na Nf Nn No Nq Nt Nu Of Pf Pg Qb) Pc(Et Fp Hq Io It Jh Jk Jn Lw Lz
Md Me Ml Mp Mq Mr Na Nb Nh Nn No Ns Oh Oz Pb Pg Po Qd) Mu(Hu Ih Il Io Ir Iv Lz Me Md Me Mq My Na Nb Nh Ns Of Oh Oy
Oz Pe Pf Pg Qa Qb) Jq(Hq Im Io Ir Jk Li Lj Lz Mj Mk Mm Mr Mw Nb Nc Nf Nj Nq Ns Of Oh Oy Oz Pd Pe Pz Qd) Nn(Hr Hu Hv Ih Ir It Iv Jg
Jn Mc Mh Mj Ml Mm Mq My Na Nh Nl Of Oh Oi Of Pz Qb Qd) Nl(Et Hr Hu Hw Iv Jh Lw Mc Me Mj Ml Mp Mx My Nb Nf No Ny Pb Pe Pf
Pg Po Qc) Oe(Ih Io Li Lj Lz Mb Md Mm Mw Nb Nc Nh Ns Of Oh Oi Om Oy Pe Pg Po Pz Qa Qb) Ip(Fp Hr Hu Hv Hw It Iu Iv Jk Jn Mc Me Ml
Mp Mx My Na Nj Nu Pg Pz Qc Qd) Mx(Et Hq Hr Hu Hw Ir Jh Lw Mc Mk Ml My Nb Nj Ny Oz Pb Pd Po Qb Qc) Nq(Fp Hq Hu Hw Il Jk Mc
Mj Mq My Nd Nf Nt Ny Pz Qd) Pf(Fp Hq Hu Jk Md Mh Mq Nc Nh Ns Nt Nu Oy Oz Pz Qd) Hv(Et Hr It Jh Jn Li Mh Ml My Na Nf Nu Pb Qc)
Lw(Hw Iq It Iu Ml Mm My Nf Nt Nu Of Pe Qc) Jg(Io Lj Lz Mr Nb Nc No Ns Oh Oz Pe Pg Po) Hw(Et Hr It Jh Mc Mp Nu Pb Pf Qc Qd) Iu(Li
Lj Mb Mk Mp Mr Nb Nr Nu Om Po) Jh(Hu Ih Li Ml My Nf Nu Ny) Mk(Hq Il It Jp Nf Nu Pa) Oi(Ih Il Mb Nc Nj Oh Om) Pf(Fp Ih Ml Nu Ny
Pb Qd) Nr(Il Jp Jr Mf Mg On) Mr(Hq Iq It Mi Nf Nu) No(Nt Nu Ny Pb Po) Nd(Hq Hu Nc Nt Om) Ij(Js Ma Mg Ms Mv) Im(In Ma Mg Mi Pa)
Iq(Ih Il Li Om Po) Ir(Il It Jn Ml Qd) Ik(Jp Lh Mf Mg) Qa(Ih Mi Ml Qd) Js(Il Oh Qb) Pb(Hr It Nf) Pe(Fp Ml Of) Lh(Mq Oy) EtLi MhMi MlNf
NbOf NjJn QcQd} aA{Mm(Et Fp Hq Hv Hw Hx Ii Jh Jn Lj Lu Lw Mc Md Me Mh Ml Mu Mv Mw Mz Na Nb Ne Nl Nm No Ns Nt Nu Nx Ny
Oh Oi Ok Oy Pe Pf Pg Po Qa) Et(Fp Hq Hv Hw Hx Ii Jh Jm Jn Jr Jt Lh Lj Lu Lw Mc Md Mh Ml Mp Mu Mw My Nb Nd Ne Nf Nl No Nt Ny Oi
Pe Pf Pg Qb Qc Qe) Jr(Fp Hq Hu Hw Ih Ii Jh Jn Lh Lj Lu Ly Mb Mc Md Mg Ml Mp Ms Mz Nb No Ns Nt Nu Nx Ny Oh On Oy Pa Pc Pe Pf Pg

Om(Iv Jq Lu Mf Nk Og) Fr(Fp Lj Ms Ns Qc) Im(Iu Jm Mi Ng On) Nk(Nc Oh Pf Po) Hr(Hw Lw Mr Mu) Ik(aA Ji Nd Nw) Ng(Oh Pf Pg) Iu(Ih Pf Qd) Iv(Jm Mi Og) Mn(Iq It) Jj(Nx Ny) On(Ij Mk) AaaA LuNd MiHu MuPc JmOh

Unconstrained panels with 2 analytes, where 1.0E-2 >= 'AUC p-value' > 1.0E-3. Contains 1,113 panels of 7,261 total panels evaluated. : No(Et Fp Hq Hr Hu Hv Hw Hx Ih In Jh Jk Jn Jq Js Lh Li Lj Lu Lv Lw Ly Lz Ma Mb Mc Md Me Mf Mg Mh Mi Mj Mk Ml Mm Mp Mq Mr Mu Mv Mw Mx My Na Nb Nc Nd Ne Nf Nh Nj Nl Nm Nn Nq Nr Ns Nt Nu Nv Nx Ny Oe Of Oh Oi Om Oz Pb Pc Pd Pe Pf Pg Po Pz Qa Qb Qc Qd) Qb(Fp Hq Hr Hu Hv Hw Ih Ii Im Io Ip It Iv Jh Jk Jq Js Jt Li Lj Lu Lw Ly Lz Mb Mc Md Me Mg Mh Mj Mk Ml Mm Mn Mp Mq Mr Ms Mu Mw Mx My Na Nb Nc Nf Nh Nj Nl Nm Nn Nq Nr Ns Nt Nu Nx Ny Oe Of Og Oh Oi Om Oy Oz Pa Pb Pd Pe Pf Pg Po Pz Qa Qc Qd) Hx(Et Fp Hq Hr Hu Hv Hw Ih Ii Il Im Io Ip Iq It Iv Jh Jk Jq Js Li Lj Lu Lw Ly Lz Mb Mc Md Me Mg Mh Mj Mk Ml Mm Mn Mp Mq Mr Mw Mx My Na Nb Nc Ne Nf Nh Nj Nl Nm Nq Nr Ns Nt Nu Nx Ny Oe Of Oh Oi Oy Oz Pb Pd Pe Pf Pg Po Pz Qc Qd) Om(Et Fp Hq Hr Hu Hv Hw Ii Im In Io Ip Iq It Iu Jh Jk Jm Js Jt Li Lj Lv Lw Mc Md Me Mg Mh Mi Mj Mk Ml Mm Mn Mp Mq Mr Mu Mw Mx My Na Nb Nd Ne Nf Nh Nj Nl Nm Nn Nq Ns Nv Nx Ny Oe Of Oh Oi Oy Oz Pb Pc Pd Pe Pf Pg Po Pz Qc Qd) Ma(Et Fp Hq Hr Hu Hw Ih Ii In Iq Jk Jq Js Li Lj Lu Lv Lw Ly Lz Mb Md Me Mf Mh Mi Mj Mk Ml Mn Mp Mq Mr Ms Mu Mv Mw Mx My Nb Nc Ne Nf Ni Nj Nl Nm Nn Nq Nr Nt Nu Nx Of Og Oh Oi Oy Pb Pc Pe Pf Pg Po Pz Qc Qd) Nn(Et Fp Hq Hr Hw Ih Ii Il Im Jh Jk Jq Js Li Lj Lw Ly Lz Mb Mc Md Me Mh Mi Mj Mk Ml Mm Mp Mq Mr Mu Mv Mw Mx My Na Nb Nc Ne Nf Nh Nl Nm Nq Ns Nt Nu Nx Ny Of Oh Oi Oy Oz Pb Pc Pd Pe Pf Pg Po Pz Qc Qd) Qa(Fp Hq Hr Hu Hw Ii Ij Ik Il Im Jh Jk Jq Li Lj Lw Ly Lz Mb Mc Me Mh Mj Mk Mm Mr Mw Mx My Na Nb Nc Nf Nh Nl Nm Nq Nr Ns Nt Nu Nx Ny Of Oh Oy Oz Pa Pb Pe Pf Pg Qc Qd) Jg(Fp Hq Hr Hw Ii Ij Ik Il Im Io Ip Iq It Jh Js Li Lj Lw Ly Lz Mb Mc Me Mh Mj Mk Ml Mm Mn Mr Mu Mv Mw Na Nb Nc Nf Nh Nl Nr Ns Nt Nu Nx Oz Pb Pc Pe Qc Qd) Lh(Et Fp Hq Hw Ij Ik Il Im Jh Jq Js Li Lj Lu Ly Lz Mb Mc Md Me Mh Mj Mk Mm Mr Mw Mx Na Nb Nc Nh Nm Ns Nu Nx Oh Oy Pb Pd Pe Pg Po Qc Qd) Jn(Et Fp Hu Ii Ij Ik Il Im Io Ip Iq It Iv Jh Jk Jo Jt Lj Ly Mb Md Mh Mm Mn Mq Mr Mw Mx Nb Nf Nl Nm Nr Nt Nu Of Oh Oy Pe Pf Pg Qc Qd) Pa(Fp Hq Hw Ii Ij Ik Il Im Jh Jq Lj Ly Mb Me Mh Mj Mk Ml Mm Mr Mw Mx Nb Nc Nf Nh Nm Ns Nt Nu Nx Ny Oh Oi Oy Oz Pb Pe Pf Pg Po Qc Qd) Mv(Et Fp Ih Il Im Io Ip Iq Iv Jq Li Lj Lv Mb Md Mf Mg Mi Ml Mm Mq Ms Mu Mw Mx Nc Ni Nj Nk Nl Of Og Pb Pe Pf Pg Po Pz Qd) Im(Hu Hv Ih Ii Il In Ir Jo Js Jt Li Lu Lv Lw Mf Mg Ml Mp Mq Ms Mu Nc Nd Ne Ni Nj Nk Nq Nv Nx Oe Og Oz Pb Pc Pd Po Qe) Lv(Et Fp Hq Hu Hw Ih Iv Jk Jq Lj Lu Mb Md Me Mf Mg Mh Mi Mp Mq Ms Mu My Na Ne Ni Nm Nq Ns Oh Pb Pc Po Pz) Nd(Fp Hv Io Ip It Jh Jk Jm Jq Js Lj Mi Ml Mn Ms Mu Mw Mx Ne Ng Nk Nl Nm Nt Ny Og Oh Pf Pg Po Qc Qd) Pe(Fp Hu Ih Io It Iv Js Li Lu Lw Lz Mb Mc Md Mg Mi Ml Mn Mq Mu Ne Ng Nh Nj Ns Oe Of Oi Pc Pd Po Pz) Oh(Et Hv In Io Ip Iq It Iu Iv Jo Js Lu Mf Mg Mi Ml Mn Mp Ms Mu Nc Ne Nf Nj Nq Oe Og Oi Pd) Pf(Et Fp Hv Ih In Iq Iv Jm Lu Md Mf Mg Mi Mn Mp Mq Ms Mu My Ne Nj Nq Oe Og Oi Pc Pd Po) Mu(Hu Hv Ii In It Iu Iv Md Mf Mh Mq Mr Ms Mw Nc Ng Ni Nk Nl Nq Nr Nt Pb Pg Po Pz) Et(Hv Ih In Iv Jm Jt Lu Lw Mf Mg Mp Mq Ms Mx Ne Nj Nk Nq Oe Oi Pc Po) Po(Hr Ip It Iu Iv Jm Jo Lu Mf Mx Ng Nj Og Pb Pc Pg) Mi(Hv It Jm Jt Lu Mf Mq Ms Nc Ng Nj Nk Oe Pb Pz) Jo(Hr Hv Jk Li Lz Mg Mp Mw Mx My Nf Nk Nt Pb Pz) In(Hw Ii Lw Lz Mh Mj Mk Mp Mx Na Nb Ny Pb Pg) Iv(Jh Ly Mf Mg Mn Mp Mq Ms Ng Ni Nj Nk Nq Pc) Mp(Ih Jm Mf Mw Nb Ng Ni Nk Nr Og) Pc(Hr Ih Ij Il It Jk Lu Mx Ng Ni) Mw(Hu Iu Jm Mf Ng Ni Nk Pz) Ng(Ij Li My Nq Nu Qd) Nk(Fp Hv Jk Nl Pg Qd) Qe(Ij Ik Jh Lz Nu Oy) Ni(Hv Jk Lj Nq Qd) Jh(Iq Iu Md Mf Mq) Jm(Jk Js Pg Qc Qd) Mn(Jo Ip Mf Pd) Hr(Li Mj Nr Oy) Ij(Ir Jr Ok) Iu(Jk Pg Qc) Ms(Jk Nx) Mx(Nc Pg) Ik(Nv On) Ny(Iq Mf) Og(Hv Jk) NuIr IIO

Figure 10 Continued

Mg Ms My Mz Of Og Oy Pa) Hr(aA Hu Jh Jr Mi Ms My Of Og Oy) Js(aA Ir Ji Jn Jr Ms Oy) Of(Jg Jp Mk Mv) Ms(Ji Nr Pd) Ji(Jq Nx) Oy(Mk Mx) LvPg LyIq MyJg JrPd} Ji{Js(aA Hx Ir Iv Jn Jp Jr Lh Lu Mf Mi Ms No Nw Pa Pe) Ms(Jg Jp Mf Mk Ml Mx Nd Nj Nk Nr Pa Pc) Ni(Jp Jq Mf Mi Mk Ml Mr Nd Nr Pa) Jq(aA Jm Jr Mi Nk Nr Nw Pa) Nk(Jp Jr Lu Mf Mi Pa) Mf(Jm Mi Nx) Mx(aA Ir Iv) Mv(Jm Nr) Ir(aA Pd) Jp(Jm Nx) MkOy MnNd HxOg IpPa PzJg} Jr{Nk(Hx Jg Jp Js Mf Mv Mz Nd Nv Nw Ok Pa Pc Qe) Js(aA Ir Iv Jg Jp Lv Ma Mi Mz Nw Ok Pa Pc) Ni(Jg Jp Mi Mz Nd Nv Ok Om Pa Pc) Jm(Ip Ir Jp Mz Qe) Nr(Jp Lh Mv Nw) Lv(Mf Nd) Mx(Iv Nw) Mz(Iv Mf) Ir(aA Jn) Jg(Hu Pz)} Jp{Nk(Hx Ir Jm Lh Lu Lv Mg Mi Mk Mr Mz Nr Pa Pe) Ni(Hx Ir Lh Lw Mi Mk Mr Mz Nd Nr Pa Pe) Jm(Hx Ir Iv Jn Lv Qa Qe) Js(Ir Lh Mi) Lv(Mg Nd) Ms(Jg Pc) NrLh MiHq MkOy MnPa MvHu NdIr PzJg} Nw{Js(aA Jh Jn Mf Mi Ms My Pa) Mx(aA Iv Md Mi Ms My Ny) aA(Ir Jq Nf Ni Pd Qd) Ms(Mf Nd Nk Pc Pd) Mi(Hq Mj Ni Nk) Ni(Mk Nd Pa) Pd(Lh Nk Pa) My(Jg Mf) LyIq MkOy MnNd MrHr JgJh} Ir{Jm(Hx Ma Mn Mp Mv Nd Nn Nv Ok Pc Qe) Nd(Iq Js Ni Nk Pc) Mz(aA Iv Jn Js) Mg(Ma Mn Mp) Pd(Mp Po) aA(Js Lw) NkNv IhLh} Jn{Mi(Hq Js Ml Pd) Mf(Lv Lw Mu) Nk(Mu Mv Pc) Nd(Lv Ni) Jg(Jm Pz) Pc(Il Ni) NrMv MzIv} aA{Jg(Hu Jh Jk Nq) Ok(Js Mx Nf Pd) Mi(Mj Nk) NqMu NdIq NiPc JqOm JsLh} Iv{Nd(Jm Ma Mv Ni Nk) Ma(Jm Mg) Mz(Js Mx) JsNv} Nk{Mz(Jg Mi Mv Pa) MsNv QeJm} Ok{Mi(Js Mf Pd) NrLu LvMf NdNi} Pz{Jg(Mz Pa Qa Qe)} Nv{LvMf MkOy} NrMvQe HrPaPc

Constrained panels with 3 analytes, where 1.0E-7 >= 'AUC p-value' > 1.0E-8. Contains 809 panels of 287,980 total panels evaluated. : Jo{Qa(Ii Iu Mj Mk Mr Nb Nk Nr Pa Pe Pg Po) Et(Hx Ii Jr Lw Mj Nb Pc Pe Pf Po) Lv(Hw Ii Lw Mk Nk Om Pc Pe Po) Mm(Hw Ii Mr Pc Pe Po) Jr(Hw Mz Nk Pc Pg Qe) Nv(Ji Jp Mi Ng Ok Pc) Ma(Hx Mk Mr Nr Pa) Nm(Hw Lu Pg Po) Mi(In Mz Pa Pg) Ip(Js Lw Nk Pc) Jn(Mu Pa Pg Po) Nn(Iu Mr Mt) Nq(Mj Mk Nr) Mz(Hw Mk Mr) Nd(Ik Jg Ok) Qe(Jt Mr Mu) Pf(Hx Mk Pc) Iu(Nk No) Nw(Ml Mt) Om(Jp Ok) LuJi LxHq MvHx HwPa JjOn} Jj{Nd(Et Jk Ma Mg Mv Nm Ok Pf Pg Qa Qb) Mz(Fr Jg Mi Mk Mr Mv Nr On Pc Pe) Pc(Im Jk Mc Mi Ng Nt Pe Qb) Nv(Mi Mk Mm Mr Nj Nr On) Qb(Mk Mr Mv Nr On Pe) Mf(Hv Hw Mj Nx Om) Nk(Fp Li Mp No Oy) Nj(Et Jk Mw Nm) Mm(Fr Ni Nm) Jk(Mk Mr Nr) Et(Lu On) Mv(Ii Pe) In(Hw Pb) Js(No Pe) Pf(Mk Nb) NnHx MaIi MiMl MjMx MtNw MwQc NiOh} Jr{Jg(In Jh Jm Mf Mg My Nd Nq Nr) Ni(Fr Hx Mf Mk Nn No Qe) Jm(Ma Mv Nv Ok Pa Pc Qa) Js(Lh Lw Nd Nn Nv Qa Qe) Fr(Mg Mi Mv Nq Pd) In(Lw Nb Nr Nv Qe) Ji(Is Ml Mx Nr Pd) Ok(Mf Mg Nr Pd) Mi(Hq Mf Pc) Ng(Et Nn Qe) Nk(Lh Mu Nn) Jp(Mk Mr Pa) Mt(Is Iv) Mz(Jn Ml) Iu(Im Ip) Lh(Jt Nd) Nw(aA Ny) On(Nf Nr) MaMf MxaA} Jt{Fr(Lh Lv Mi Mj Mk Mr Mz Nr Om Pa Pc Pe) Ji(aA Lu Mi Mj Mk Mr Nd Nn Nr Pc Pe) Ok(Lw Mj Mk Mr No Nr Om Pc) Ir(Ii Mr Mv Nr Pe Pf Qe) Lh(aA Iv Jg Jn Mz Om) Jp(Jg Nn Om Qa Qb) Mt(Mz Nn No Om) On(Jm My Nq Pa) Jg(Hx No Oh) LwJn MaIv MiQe NkNv} Iu{Nn(Hx Jm Jn Mg Ms Ng Nk Pa) Qa(Mk Mr Nr Ok Pc Pe) Nv(Mj Mk Mr Nr Oi Pe) Hx(Lv Mg Ms Mu) Qe(Mu Nd Ok Pf) Ji(Mk Mr Nr On) Jn(Mj Ni Pc) Jp(Pe Pf Qb) Lu(Js Mm) Mg(Jg Ok) Mv(Jm Pc) Mz(Im Om) Nk(Ij Qb) Pe(Jg Jm) MnNi MuPa NgIj IrOm} In{Iv(Hw Jg Mr Nd Ng Om Pb) Lh(Fr Hw Mi Mr Mz Pa Qa) Ok(Hw Jn Mr Mv Nb Nv Qe) Qb(Hw Mk Mr Pa Pb Pe) Nr(Fr Hx Jn Qa) Nb(Fr Jn Jp Qa) Mz(Hx Mk Pe) Ir(Mn Nn No) Mj(Ji Nv) Is(Jg Nn) Jp(Hw Mr) LwaA MiPa HxJg IiQe} Nk{Ir(Hx Ma Mn Mp Nn Om Pc) Mz(Lh Lu Mu Nn Qb Qe) Fr(Mi Mk Mr No On) Nd(Jp Lv Ni Nw) Nv(Hu Jm Mg Qe) Nn(Jn Nc Ng) Jg(Hx Jn Pz) On(Jh Mi Nq) No(Jp Mt) Ng(Hx Qa) Ok(Mg Pa) MiQe MsOm QaJm} Ng{Lh(Js Mi Mk Mr Oy Pa Pb) Ji(Mi Mu Nd Nj Nn Pb) Pc(Im Jk Ma Mv Nn Qa) Ma(Ir Iv Mz Ok) Mv(Mz Pa Pb Qe) Lu(Jg Nn Om) Nd(Nv Nw Ok) Qe(Mf Mi Po) NnOk MiMz MmJg MuNv} Jm{Qe(Fr Hx Jg Mv Mz Nv Om Pa Pc) Jp(Jg Lh Nv Ok Pa Qb) Fr(Mz Nd On Pc) Ir(Jg Mi No Om) Mv(Iv Jn Ok) Lv(Jn Nv) Mz(Jg Pa) Nw(Js Mx) LuJi MfQa MtPe NdJl NiNv JnPc} Mt{Mg(Mk Mr Nn Pa Pb Pe) Mi(Hu Jl Ne Nq Nw Pd) Mf(Hw Mj Pe) Nb(Ms My On) Pc(Hu Jh Nq) Nr(Mz No) Is(Ir Jn) NnMs MjMx MlMz MvJg MyPb IvJn JkOn PaPe} Js{Ji(Hw Mj Mk Mr Nr Nx Pb) aA(Jn Lw Mi Mz Nv Pa Pc) Mz(Lh Mf Mi Nw Pa) Jn(Jp Lh Lv Nn) Pa(Ir Jp Ok On) Ir(Mp Nv) MiNv NdIv JpPb OfOn} Fr{On(Ms Mw Nb Ni Pd) Mg(Ji Nd Nw Om) Of(Mr Nb Nr Pa) My(Mk Pb Pc) Hu(Lh Mi Pc) Pd(Ir Mz Ok) Nq(Mk Pc) Jk(Nr Pe) LvMf HxOg} Nw{Mx(Mg Mj Mr Nr Nx Og Pa) Pd(Mi Mk Mr Nr On Pe) Pa(Hq Nf Nr Pe) Of(Mk Mr On) Jn(aA Ny) NqMf MkNf HqPb HrOn OgPc} Jg{Jn(Ms My Ni Nq Og) Pz(Hx Lh Ok Qb) Ji(Hu Jh My Og) Mg(Ir Jl Jp) Jp(Hu My) MwJl MzNi} Is{Mx(Mj Mr Nr Ok On Pe) Mk(Lh Mi Of) Il(Mj Mr Pa) Pa(Mr Pe) NrMz NtLh MgOm NdPd OiPc} Jp{Mg(Hx Lh Mv Ok) Ms(Hx Mk Nr Om) Nr(Ir Qe) MiPd MkOf MnNd MyPc HqPb HxOg OnOy} aA{Pc(Jh Mv Mx My Nf Nq Of Oy) Lw(Hr Mf) Mx(Mz On) Ji(Nf Pd) NqMi OnPd} Ni{Nd(Nl Nv Qe) Jn(Mu Mv Nn) Mf(Mz Qe) Mi(Mz Ok) Nv(Hu Pc) JlOg OkPa} Ji{Pd(Hx Lu Mv Pa) Nr(Lh Lu Mf) NnMs LuMl MgMv MiHq NxPa OgPc} On{Hr(Mg Mw Mz Nq Pa) Mn(Jh Mi Nq) Pd(Og Pa) MiIi OfPb} Ir{Nd(Mg Ne Pd) NnOg NrMv MnIh IlPc OkPd} Jl{Mg(Nd Om Pc) Mk(Il Pa) NrMi NdPd OiPc} Mi{Ok(Mg Mx) NrJn NtLx MzHq} Jn{Pd(Mp Po) LvOg} Ok{NrMv MkOy PaPd} Nd{LvQe MnNv} Lh{NrMz IhQe} Pc{LxMv HrPe}

Constrained panels with 3 analytes, where 1.0E-6 >= 'AUC p-value' > 1.0E-7. Contains 1,097 panels of 287,980 total panels evaluated. : Jo{Pa(Im In Jm Lw Mk Mr Mu Mv Mz Nv Om Pc Pe Pg Qb) Mv(Et Hw Jn Jr Lv Mj Mk Mr Mz Nr Pc Pe Pg) Ma(Hw Ii Iu Jr Jt Mj Nb Ok Pc Pe Po Qe) Pf(Hw Ii Iu Jn Lw Mj Mr Mz Nb Ni Nr Pe) Pg(Et Iu Jm Lv Mj Mk Mr Mz Nb Nr Pc Pe) Nk(Hw Io Mj Mk Mr Mz Nn Nr Pc Qb) Jr(Hx Js Lw Mj Nb Nn Nr Om Pe) Nv(aA Jt Lw Mj Mk Ni Nr On Pe) Pc(aA Hx Im Jk Mi Mz Pe Qb Qd) Mr(Hx Jn Lv Mi Ni Om Pe Qb) Mk(Im Jn Mi Om Pe Qb Qd) Hw(Im Mi Nn Om Pe Qa Qb) Lv(Ij Jk Mu Mz Nn Qb) Lw(aA Hx Nm Nq Qa) Mz(Hx Jp Mj Nr Ok) Mi(aA Hq Nr Pe) Ip(Ii Jt Lu Qc) Et(Jt Mu Qb) Nn(Hx Ji Jp) Nr(Im Qb) Nd(Ji Qc) Ni(Ij No) Hx(Mu Om) Ii(Io Nq) NmJt LuMm MfJj MjIm NgOm IoOy IuJg IvJs} Ng{Ma(Hx Ii Iu Jr Lh Mi Mk Mr Nb Oy Pa Pb Pe Po Qc) Mz(Ii Lu Mk Mr Mu Nb Nn Nr Oy Pa Pb Pc Pe) Qe(Hx Ii Mk Mr Mu Nb Nd Ni Nr Oy Pa Pb Pe) Jr(Hx Jk Mi Mk Mp Mr Mu Nb Nd Nr Oy Pa Pe) Hx(Et In Lv Mp Mv Ni Nn Pc Pf) Qa(Ii Mi Mk Mr Nb Nr Oy Pa Po) Ir(Mk Mr Mu Nb Nr Oy Pa Pe) Et(Jk Mi Mk Mu Nb Pc) Mv(Lh Mi Mp Nn Oy Pe) Lh(Lu Mu Mx Na) Nn(Mf Ni) No(Lv Ni) Mi(Jg Jn) Nk(Pe Qb) Iv(Mn Mp) Om(Mf Og) Pc(Pa Pe) NdJp IiIm JjOy JkJm JnPf} Iu{Jp(Mj Mk Mr Mu Mx Nb Nd Nr Ok Pc Po) Qb(Hx Jg Jm Jn Mi Ni Nv Ok) Mv(Hu Mj Mk Mr Nb Nk Nr) Hx(Et Im Iv No Ok Pf) Mi(In Jg Nk Nn No) Qe(Mk Mr Nr Pc Po) Jn(Mk Mr Nb Nr Pf) Lu(Jg Lv Mw Qd) Nv(Hu Nd No Ok) Nn(Iv Ok Pe) Ij(Jm Mg Og) Om(Jr Pa Qa) Lv(Mn Pf) Ma(Mu Oh) Nk(Iv Ok) Qc(Mn Pf) Jm(Iv No) Pe(Ok Pc)} Jj{Nd(Fp Ji Mu Nb Ne Nl No Nt Nu Of Oh Pc Pe Po Qc Qd) Qc(Fr Mk Mr Nb Nm Nr Pc Pe Po) Ma(Mk Mr Nb Nr Ok Pc Pe) Nn(Mk Mm Mr Nr On Pe) Ml(Hv Hw No Pb Pe) Im(Mj Mk Mr Nb Nr) Mf(Jq Jt No Po) Om(Mk Mr Nr Pc) Hw(Hv Js Na) Qb(Ii Mu Nb) Pb(Hq My Ny) Pc(Ms My) NoMc NqMi MmNj MuIi NkOh JsJt} Fr{Pd(Hw Lh Mi Mj Mk Mr Nd Nr Om Pa Pb Pe Po) Pa(Hq Jk Jm Mg Ms My Nf Ni Pe) Mr(Jk Jm Mg Ms My Ni) Pc(Jh Mg Ms Mv Mw Og) Mi(Hq Jm Js Mg Ni) Mk(Jk Jm Mg Ms Ni) Hx(Hu Jk Ni Nq) Nr(Jm My Ni) Nq(Mz Nd) My(Nb Om) Jh(Jg Om) Jm(Qa Qb) Pb(Hq Mg) NoJs LwJt MfHw MsNb MtMz NcNk NiPe IqIr JkLh OgOn} Jr{Js(Hw Jm Jn Mj Mk Mr Mu Mv Ni No Nr Om Pb Pe) Jm(Hx Lh Mf Mi Mp Nd Nn Qb) Nr(Ir Is Ma Ni Nk Pa Qe) Ni(Lh Ml Mr Mu Mv Pe) Mf(Lh Lw Mu Mv Qe) Nk(Lu Mi Mk Mr No) Ml(Iv Jg Ma Ok) Ms(Jg Nv Om) Mi(Mx Pd) Mk(Hr Oy) In(Ii Nn) Jg(Mv Mw) Ok(Nd Pc) On(Nb Pg) MrHr IvJn JiaA JtNv OgOm PaPd} Mz{Ni(Lh Mk Mr Mv Nd Nn Nr Pa Pc Pe) Js(Hx Jg Ji Jp Lv Mv Nn Nv On Pf) Mv(In Jm Mg Ml Ms Nr Pd) Nk(Mk Mr Nd No Nr Pc) Jg(In Mg Ms My Nr Og) Jm(Hx Jp Lu Lv Nv) Jt(Ji Jp Nn Ok Pf) Mi(Mx Pc Pd) Lv(Mf Nd) Mk(Hr Oy) In(Nb Nr) Ji(Mx Pd) MfLh MtaA PdPf} In{Pa(Hw Im Jg Ma Mk Mr Mv Nn Oh Pb) Im(Hw Hx Mj Mk Mr Pb Pe) Ok(Jq Mj Nr Pc Qa Qb) Jg(Hw Mi Mr Pb Pe) Po(Iv Lv Nv Qa) Nn(Hw Jn Mr Pb) Nr(Lh Lv Qb) Ir(Lv Lw Mv) Qe(Mj Nv Om) Nb(Hx Qb) Qa(Ii Pc) Nv(Hu Jn) LxPf MpIt MxOn NdNw NiHx QbPc LhPe} Pa{Ni(Hr Jg Jn Mf Mi Nr

Figure 10 Continued

Pc) Jm(Jg Ji Mv Nk Nv Ok On) Ji(Hq Mg Ml Nf Nr) On(Hq Ii Jk Of) Nr(Is Jp Lh) Hr(Hq Hx Pg) Nw(Mh Of Pg) Pd(aA Jp Nk) Mk(Is Oy)
Mt(Hu Il) Iq(Ir Ly) Jt(Et Lh) Ok(Mf Mg) MaMn NkJg JnJs} Jm{Jp(Mi Mk Mp Mr Nr Pc Pe) Hx(Jg Lv Ma Nk Nv Ok) Jn(Js Ma Nk Nv Qb)
Qe(Lh Mk Mr Nd) Iv(Mn Mp Oh) Qa(Jg Nv Pc) Qb(Lv Nk Ok) Lu(Ir Ok) Ji(Jg Ml) Lh(Jt Nr) Mulr} Ji{Pd(Hw Lh Mi Mj Mk Mr Nr Ok On Pe)
Mx(Mi Mj Mr Nr On Pe) Mg(Jg Lu Mi Pc) Js(Nd Nj Nn) Nr(Is Jp) Ml(Hx Nx) Of(Mk Nb) aA(Jn Mt) NnOg MyPc NdNk NvNx} Nk{Nd(Jn Lh
Mv Nv Qa Qe) Qe(Hx Jg Mv Om Pc) Mf(Jn Ok Qa Qb) Ir(Jg Lh Mu Mv) Nv(Mk Mr Nr Pe) Ok(Hx Lu Qb) Ms(Jg Lh) Malv MpJn HxQb QaJg
JtLh} Ni{Nd(Et Hx Jg Lh Lv Mv Ne Om Pe Qa) Nv(Mg Mk Mr Ms My Nr Og Pe) Hx(Jg Mi Qe) Ok(Lu Nn Pc) Mf(Ir Om) Qe(Mi Pc) Jn(Mk
Mr) Mnlr} Jp{Nr(Hx Is Jn Lv Qa) Pd(Hw Lh Mp Pe Po) Mg(Mu Nb Nv Pc) Js(Hw Iv No Po) Nn(Mn Ms) Nb(Ms On) Jg(Mv Og) Jt(No Nv)
Pc(Jh Og) MfHw HuLh} Mt{Ml(Hw Hx Is Iv Pb) On(aA Il My Nq) Pc(aA Mv Oi) Nt(Lh Mi) Hu(Lh Nn) Hx(Ny Pb) Nw(Og Pd) NqNb MgOm
MkIl HwJn JgJt NyPb} Ir{Js(Mi Mn Nn No Om Po) Nd(Hq Ly Nn) Om(Mf Nm Pd) Nr(Lh Ma) Mg(Et Mv) Pd(Mi Nn) NqJt Lylq MaMf MkOy
MvHu MyPc} Jt{Qe(Et Jg Lh Nv Om) Jg(Mi Nd Ok Om) Jn(aA Nn Om) Lh(Mf Mi Pc) On(aA Mg Mi) Iv(Mn Om) QaOm NvaA} Nw{Nd(Js
My Pd) On(Nb Nf Oy) Pc(Jh My Oy) Mi(Ml Nr) Mr(Nf Po) Mx(Hu Mv) MdJn MkNb HvHw HxPb} Ok{Pd(Hx Lh Lu Mv Po) Mg(Jg Lu Mv)
Mv(Hu Of) NoJs LuMf MkOf MnNd HrHx} On{Mx(Hu Mg Of Pg) My(Js Mv Pc) Mi(Hq Js) Mk(Lx Mn) Pd(Lh Pe) MsNf} Jg{Jn(Jh Js Mv
Nr) Pz(Hu No Pe) Mg(Hx Nv) MvHu MyNv} Is{Nn(Hu Ih Oi) Ly(Mi Nd) MiMr MkIl NdHq HvHw JhPc} Qe{Mf(Lv Mi) Js(Mi No) Om(Ms
Og) Pd(Mp Po) NrLh MkOy} Nv{Of(Mk Mr Pb Pc) NoJs MiHq MrHr MsNd MxIv} aA{Lw(Hv Mx Na Nf Pd) Mx(Jn Nn) MiNf} Jn{Js(Lu Mu
Pc) NrLv MyPc} Nr{Mv(Hx Lh) MgLh} Mf{MsOm IhQa} Nd{Iv(Mg Pd)} Hr{Hx(Mk Mr)} NJILh MsOgOm MvHuPc Constrained panels with 3 analytes, where 1.0E-5 >= 'AUC p-value' > 1.0E-6. Contains 1,219 panels of 287,980 total panels evaluated. :
Jo{Nk(Ii Ij Jk Jt Li Lw Mp Mu Mv Nb No Nq Oy Qd) Pe(Hx Im In Jk Jm Jn Lw Mz Nd Nn Nr Om Qb) Mr(Im In Jk Mg Mu Mw No Nq Oh Po
Qd) Nn(Mi Mj Mk Mz Nb Ng Nr Ok Pa) Mv(Ii Jt Lw Nb Nd Nm Po Qa Qb) Lw(Im Ma Mi Mz Pg Qb Qd) Hx(In Jm Mj Mk Nd No Nr) Om(Iu
Lu Mi Nr Og Pc Pf) Mu(Iu Jr Mz Pf Pg Qa) Jn(Et Hw Ip Mj Nb Nr) Lv(Ma Mb Mw No Oh) Mz(Ii Lu Ma Nb Oy) Nd(Et Ip Jr Pg Qa) Qb(Ii Jt
Mj Nb Po) Jk(Et Mk Nr Pa) Jr(Ii Ni Nm No) Ip(Jq Oh Oy) Qd(Nb Nr Po) Nm(Ij Pf) Ma(Hv Pg) Mk(Mw No) Ni(Io Qa) Im(Ii Nb) Jt(Pf Pg) EtLu
NrPa MwHw} Ng{Jk(Hx Ii Iu Ma Mf Mj Mk Mp Mr Nb Ne Nr Oy Pa Pb Pe Po) Et(Ii Iv Jn Lu Mj Mp Mr Nd Nr Oy Pa Pb Pe Pf Po Qb) Nn(Ii
Jm Lh Mi Mk Mr Nb Nd Nr Om Oy Pa Pb Pe) Jn(Ii Lh Lu Ma Mk Mr Nb Nd Nr Oy Pa Pe) Im(Lw Mj Mk Mr Nb Nr Oy Pa Pe) Pa(Hr Lu Lv
Mk Mr Nb Om Oy) Nk(Mv No Oh Pf Pg Po) Hx(Mf Mi Mu Nd No Nq) Lh(Hv Me Ml Nm Pd) Pc(My No Nq Om Qb) Mi(Ir Mg Oh Oi) Mv(Ii
Mf Mr Mu) Nd(Ma Mz Pf Qa) Pb(Ir Jj Jr Qa) Lu(Ir Mm Qe) Om(Mr Nr Oy) No(Jr Ma) Lv(Mw Pf) Mf(Pf Qa) NrMa MkHr NbIn IiJr QaPe}
In{Mr(Et Hr Lv Ma Mv No Oh Om Pe Pf Po) Mz(Ii Lu Lw Mj Mu Nn Nv Ok Oy Pc) Hx(Ma Mj Mv Nk Nn No Oh Om Pf Po) Pe(Hw Ma Mf
Mk Mv Ni Nn Oh Om Pb) Hw(Et Lv Ma Mv No Oh Om Po) Om(Jn Jr Mk Ok Pa Pb Qa) Po(It Ni Nk Pa Pc Qb) Mk(Et Jg Lv Ma Nn) Nd(Ji Lh
Nv Ok Qa) Pb(Et Ma Mv No Oh) Nb(Im Jg Lv Pa) Qa(Jg Jr Mj Nv) Qe(Ij Jq Nn No) Ii(Im Jn Qb) It(Ma Mn Nn) Nr(Im Jg) Mj(Jn Qb) Mu(Ir Jr)
Ij(Ir Jr) Iv(Iu Pc) Ok(Jg Nn) JjJt} Nr{Mz(Jm Jp Jr Js Jt Lu Lv Mi Ms Pd) Qe(Jn Jt Lu Lv Mi Ni Nk Nv Ok Pa) Jn(Js Lu Mu Ni Nn Nv Og Pa Pc)
Jr(Et Hx Lv Mi Nd Nn Nv Pf Qa) Jp(Iv Jg Mi Nv Oh Pe Pf Qb) Pa(Ir Jg Mv Nk Ok On Qa) Nv(Ir Jm Jt Ms Og Pd) Nn(Ir Is Iu Ji Lh) Hx(Hr Iu
Jg Ma Ok) Mv(Pe Qa Qb) Nk(Ir Pe Qa) Ji(Nd Pe Pf) Ok(Mi Ni Pd) Mn(Ir On) Im(Iu Jt) Is(Mi Nd) Jg(Jt Pz) Jj(Mu Oh) NoNi LuIr QaJm}
Jg{Nk(Hu Hv Iu Iv Lh Lu Mi Nd Ne Pe Qb) Pa(Hu Jh Jk Js Mg Ms Of Og Oy Pd) Hx(Hu Iu Lh Mi Ms No Og Pe Qb) Jt(Iv Lv Mj Mk Mr Mz Pe Qa
Qb) Hx(Hu Jh Jk Ms My Nq Of Og) Mg(Et Iv Nd Nn Om) Hu(Ir Lh Mi Mz Nd) Jm(Nd Ok Pe Qb) Lv(Iu Mf Nd) Ms(Lh Nd Ok) Nq(Mz Nv)
Iv(Iu Nj) Jr(Og Oi) MfQa MjPz MkOy MwNv MzJh JkLh JnOi OfPb} Mz{Js(Hw Lu Mj Mk Mr Ms Mu Nb No Ok Pb Pc Pe Po Qe) Jt(Ii Lw Mi
Mj Mk Mr Mv Nv Om Pa Pc Pe Qe) Pd(Lh Li Lu Mk Mp Mr Nn Ok On Pa Pc Pe Po) Ms(Mk Mr Mu Nb Nn Om Oy Pa Pc) Jm(Mi Mk Mr Mu
Nd Nn Pc) Mf(Hw Lw Ok Pe) Ml(Lh Lu Lv Mi) Qg(Om Oy Pc) Mk(Jp Of) On(Mx Nf) MrHr HqPb} Jm{Jn(Hx Ip Iv Lu Mi Mu Nd Nn Pg)
Qa(Ma Mk Mr Mv Nd Om Oy) Nn(Hx Ji Jp Nk Pa Qe) Pc(Hx Iv Ji Lh Nv Ok) Nd(Ji Jp Lh Lv Nw) Jr(Ml Mu No Om Pe) Fr(Lh Lv Nk Pe) Iv(Et
Og Po Qc) Nv(Hu Mi Mk Mr) Pa(Lh Lv Ma Ni) Qb(Ma Mv Ni) Mi(Nw Qe) Mu(Ok Qe) Hx(Mp Mv) MfLh HrOn JpOm} Nk{Hx(Mg Mp Ms
Mv Nc Nd Nl Nn Og Pc Pf) Nd(Nc Ne Nl Nn Ok Pe Qb) Qe(Lu Mk Mr Mu No Og Pe) Iu(Im Jk Pf Pg Po Qd) Qa(Lu Mk Mr Pc Pe) Qb(Iv Lu
Mv Om Pc) Nn(Hu Mg Ms Ok) Iv(Mu Mv Og) Jn(Js Lu Mk) Fr(Mg Ms) No(Jt Nv) Mf(Lh Pe) Nc(Mp Po) MgLh MkIr OkPc} Nv{Jt(Hu Mi Mj
Mk Mr No Pa Pc Pe) Js(Hu Hw Jn Mj Pa Pb Pe Qa) Og(Hu Hx Pa Pc Qe) Pd(Hw Mi Mj Mk Ok) Mg(Ma Mi Mv Ok) Ms(Mk Mr Pa Pc) Of(Nb
Ok Pa Pe) Mf(Hw Lw Mj) Hq(Pa Pb) Hu(Mu Mv) Iv(Jn Ml) Pc(My Oy) NdNw NfPa IuLj JkLh} Ni{Mf(Hx Jn Lh Nn No Pe Pf Qa Qb) Nd(Hv
Nc Nn No Pf Pg Qb Qd) Pc(Hx Ir Lh Mi No Qa Qb) Nn(Hu Hx Ir Ms Pa) Qe(Mk Mr Mv No Pe) Hx(Ir Mu Og Pf) Mk(Ok Qa) Jn(Js Pe) Pa(Pd
Qa) MaJr MnIv MrOk MsLh} Iu{Im(Jp Mj Mk Mr Nb Og Pa Pc) Et(Iv Lv Mu Nd Pf Qb) Lv(Mf Mw Mx Nd Qc) No(Mk Nn Pc Qb) Mn(Mu
Mx Pf Qb) Nd(Hx Iv Jn Ok) Om(Ms Og Qe) Hx(Mk Mr) Iv(Mu Pf) Jn(Ip Po) LuLw MiHq MvOg QbPf JpOh} Pc{Jr(Ma Mg Ms My Nd Og)
Nq(Is Ji Jn Jp Nw) Mg(Ir Jn Lh Ok) Ms(Jn Lh Ok) Oi(Fr Ji Jp) Ir(Ma Og) Jj(No Oh) Jn(Mv Og) Lh(My Of) MrHr NdIv HuJp Illm JhJi OfOk
OnOy} Pd{Ok(Mk Mp Mr Nn Pe Qb) Po(Ji Jj Jr Qa) Nn(aA Iv Ji Jn) Ir(Hw Li Lw Pb) Mi(aA On Qe) Mp(Iv Jr Qa) Fr(Hx Qb) Nd(Ji Lv) Jr(Lh
Li) Pa(Ma Mv) HwJj QeOm} Js{Jn(Hw Hx Mj Mk Mp Mr Mv Nb Nd No Ok Pb Pe Po) Qa(Ih Lh Mi Nd No Om) Lh(Fr Ir Nd Qb Qe) Fr(Hw Jq
Pb) Ir(Jq Lv) Jr(Lu Nb) QePa} Jt{Im(Mj Mk Mr Pa Pc) Qe(Mk Mr No Pa Pe) Lh(Lw Mj Mk Mr Pe) Et(Iv Jr Nn) Qa(Mk Pa Pe) LwaA MlIj
MuJn IrJh JrOm} Mf{Lv(Hx Ir Nn Oh Om Pa Pe Pf Qa) Ir(Lh Lw Mu Mv) Jr(Hw Nn Om Pe) Ma(Iv Jn) Qe(Lw Om) Lh(Mg Ms) NnOk QaOm}
Mg{Nd(Ji Lh Ma Mv Nw Ok) Nn(Ji Jp Ok) Mu(Ir Jn Ok) Hx(Fr Ir) Jn(Ma Mv) Jp(Om Pb) Lwlr MnIv LhOm} Mk{Hr(Ir Ok Oy Pa Qe) Jj(Mu
No Oh) Oy(Jn Lh Qa) FrHx NnIs MaJr MsOk MvIr IlNw QeOf JnOg} Fr{Hx(Mv My Of Pb) Nt(Lh Mi) Ml(Hw Pb) Pa(Il Oy) NnMv MwNb
HvHw QbJk NyPb} Nd{Hq(aA Iv Lv) Et(Lu Mn) Nq(Lh Nw) Hu(Lh Mv) Jj(Ii Im) NnMn LyIv MtNw} Ml{Jr(Lv Lw Mi Mv) Jp(Hw No Pb)
Mi(Ji Ok) NoMt IhQa JjJq} Jj{Mr(Mu No Oh) Mu(Mj Qc) Hw(Ij Mc) PoNj NbOh QcOy} Pa{Nw(Il Po) On(Nf Pg) NnMn MsOm HqOk HrQe HxOg JiPe} Mt{Hw(Hv Jr Me Nm) Nn(Mv Nq Oi) MiaA HuOm} Jp{My(On Oy Pb) Hw(Hv Jn) Pb(Hx Ny) NnHu IvJn} Ir{Lu(Ma Mn) NnOi LyMp MiMx MvOg IiLh IvJr} Hx{Og(Jr Ok Om Qe) HrPe IhQe JiPb} Mi{On(Mx Nf Pg) Nt(Is Jl) NqNw} Mr{Hr(Ok Qe) MaJr JnOg} Hu{Lu(Nn Om) Mv(Iv Om)} Pb{HqJr IsOy JiNy OfOk} Ms{Nn(Jr Ok) MuJn} Mu{NqLh JnOg} My{On(Mx Nf)} Iv{LvNj MvIk} PoNwPe LxHqLj NbOfOk HvHwJi Constrained panels with 3 analytes, where 1.0E-4 >= 'AUC p-value' > 1.0E-5. Contains 1,362 panels of 287,980 total panels evaluated. :
Ng{Qb(Ii Lu Lv Lw Ma Mi Mj Mk Mp Mr Mu Nb Nd Nq Nr Oy Pa Pb Pe Po) Nq(Ii Iv Lv Mk Mp Mr Nr Oh Oy Pa Pb Pe Pf Po) Pb(Hx Im In Jn Mg Mw No Oh Om Pa Pe Pf Po) No(Ii Lu Mi Mk Mr Mu Nb Nd Oy Pa Pe) Pf(Ii Lu Mi Mk Mr Nb Ni Nr Oy Pa) Nd(Ip Jk Lu Mx Nt Oh Om Pa Pg) Hx(Ii Lu Mk Mr Nb Nr Oy Pa Pe) Oh(Ii Lu Mf Mj Mk Mr Nb Oy) Pc(Hr Ii Lu Mk Mr Mw Nb Oy) Mw(Mk Mr Nb Nr Oy Pa) Lv(Mb Mu My Oy Pc) Ma(Lu Lw Mf Mu Qa) Mi(In Io Iv Jk Om) Ni(Io Jk Pc Pg Po) Mv(Lw Mk Nb Nr) In(Ij Jk Mk Mr) Lu(Im Nm Qa) Om(Iu Mk Mu) Mf(Pg Qd) Jh(Io Iv) Jk(Jo Lw) Pc(Jo Mu) MpMy NkQd IuPg QaLh} Jg{My(Ir Iu Jm Lh Mg Mi Mk Mr Nd Ni Nk Nn Om Pa Pb Pc Po Qb Qe) Ms(Hu Ir Mi Mj Mk Mr Nb Nn No Nr Oh Pc Pe Qa Qb Qe) Mg(Hu Lh Lv Ma Mi Mk Mr No Nq Pb Pc Pe Po) Nr(Hv Ir Iu Lu Ni Nk Nn No Oh Pe Qa Qe) Jm(Hu Iv Lu Lv Mi Mp Oh Pc Po) Og(Ir Iv Lh Nk Nn Pe Qa Qb Qe) Jh(Jq Lh Mi Ni Nn Om Qa Qe) Nq(Lh Mp Ni Nn No Qa

Figure 10 Continued

Figure 10 Continued

Mb Mj Mk Mr Oh) Qd(Ii Mk Mr Mu Nb Po) Mr(Et Iv Mn Pf) Oh(Et Iv Mu Ni) Ii(Mn Pf Qc) Lj(Jk Mu Om) Lu(Ip Mp) Mj(Et Pg) Nb(Ms Pf)
Om(Mi Qb) MkPf NiQc} Pa{Hr(Il Jq Js Ne Nn Nq Nt Om Pe) Hq(Lh Lv Ma Mp Nn Om Pb Qb) Mu(Hu Js Mg Ms Og Oy) Nn(Mg Ms Nf Oy)
Il(Ir Jn Nv) Om(Hu Of Oy) Pe(Lh Mv Qe) Ma(Mg Oy) Nf(Hx Lh) Js(Mi Qb) NoJt MkOf MvOy QeOg JkNv} Mk{Of(Et Im Mv Mw No Oh Pe
Pf Qb) Oy(Et Jk Lv Mv Nd No Oh Pg Po) Ms(Et Hr Jn Nn Qb) Jt(Et Jn Nm No Om) Og(Iv Nn Om Qb Qe) Ni(Im Mu Mv) Mg(Ma Nn) Il(Nv
Qe) EtNd MvHu HrOm JkNv} Ma{Mg(Ii Lu Lv Lw Mr Mu Mv Nb Oy Pb Pe Qa Qb) Ni(Ii Lw Mj Nb Qb) Mf(Hw Jq Lw Mj) Hu(Hx Lh Mu)
Iv(Jn Ml Mx) Jt(Jn Nb Qa) No(Js Ms) Hq(Mp Pb) Of(Mr Nb) IiOg} Ml{Qa(Hw Hx Iv Jq Nb No Om Pb) Jn(Hw Hx Mj Nb No Pb Po) Qe(Hw
Hx Iv Jq No Pb) No(Mv Ni Nv) Nv(Hw Hx) MzOm NbJr HqLh IrPb IvOh JqOk} Js{Qb(Hw Jq Mi Mj Nb Pb Pe Po) No(Hx Lv Mv Nd Nn Oh)
Im(Hw Hx Mj Nb Pb Pe) Iv(Hr Hx Mi Mn) Nn(Hw Mi Pb) Qa(Jq Lw) Lulr HxPe} Ni{Mu(Mf Mr Pe Pf Qb) Lw(Im Lu Nq Pg) Mf(Fp Lj Qd)
Mr(Im Mi Mv) Nq(Ii Nl) Nb(Et Oh) Jk(Mg Og) NtLh LuMm LvMw MbIv MsOh MvPe Iilm} Om{Jt(Hu Mi Mj Mr Nd No Pe) Of(Mr Nb Ok
Pb Pe) Hu(Jq Jr Mf Nn) Lu(Jh My Nq) Mg(Jq Nd Og) Hr(Mr Pe) Og(Jh Nd) NnMy LhNx} Jn{Iv(Ir Mx Qa Qe) Jq(Ir Ok Qa Qe) Ms(Nb No Oy)
Hw(Hv Mf Nv) Jt(Et Mr Pe) Og(Nb Oy Pb) NtMi MxPe HqLh HxPb} Og{Qb(Ii Lw Mr Mu Nb Pb Po) Iv(Lv Lw Mr Mu Pb) Qe(Mr Mu Nb Pe)
Mu(Hx Ir) Qa(Ii Nb) NnMr} Et{Jt(Lw Mj Mr Mv Nb Pe Po) Mg(Hx Jk Lu Lv Po) Ms(Ii Nb No Oh Oy) Mf(Hv Lw) MrNd} Nn{Mg(Lv Mi Mr
Pb) Lh(Hu Ii Nq Oi) Of(Mr Nb Pb) Ms(Mr Nb) Nv(Nq Oi) MfHw MvJp HqPb OiOk} Mf{Lv(Hw Iv Jq Mu Mv) Qb(Hw Jq Lw Mj) Qa(Hw Mr) Jq(Hx Pf) LwIv MuHu} Pb{My(Jr Lh Mz Qe) Mg(Jr Qa Qe) Hq(Hx Qa Qb) Hx(Jr Qe) Ny(Jr Qe) LhOf} Ms{Qb(Mu Nb No Oy) Qa(Nb No Oy) Hx(Mu Mv) Qe(Nb Oy) IrOy} Mi{Nq(Jr Lh Mz Nv Ok Qe) Nt(Ji Mz On Qe) NdHq} Hq{Lh(Hv Me Mx Na) Lx(Nj Nl) Mp(Hx Pe) NdOn} Mg{Mv(Ii Lw Pe) Mu(Hx Qe) Iv(Lw Mp) NdHx} Nv{Nb(Mw Nq) Hw(Hv Me) Jk(Mr On) HxNy} Iv{Ly(Lu Mp Mu) Qa(Ir Jr) MxPe} Of{Nb(Hx Mv Qa Qb) Mv(Mr Pe)} Jr{NtLh MeHw MyOy HxNy IrJq} Jt{No(Lw Mr Pe) NmMr MmPe} Qe{Il(Mj Mr) NtLh HvHw} Lv{MbPf MeJq MvHu} Mx{Qa(Mj Pe)} Mz{NtLh MeHw} Hr{HuLh HxNy} Jq{Ok(Na Ny)} LuLwQb MvHuPe NdOnPg HvHwIr Constrained panels with 2 analytes, where 1.0E-6 >= 'AUC p-value' > 0. Contains 228 panels of 7,261 total panels evaluated. : Jj(aA Et Fr Hv Hx Ii Im Io Ir Is Iu Iv Jg Ji Jk Jl Jn Jp Jr Lh Lv Lx Mg Mi Mj Mk Mm Mp Mr Mt Mv Mw Mz Nb Nk Nm Nq Nr Nt Nv Nw Ok Om On Oy Pa Pc Pe Pf Pg Po Qa Qb Qd Qe) Mt(aA Is Iu Ji Jm Jo Jp Jr Mg Mi Mk Mz Nd Ng Ni Nk Nr Nw On Pa) Lx(aA In Iu Jl Jm Jo Js Jt Li Mf Mg Mi Ng Ni Nk Nr Pd Po) Is(Fr In Iu Jm Jo Jp Js Jt Lu Mi Mz Nd Ng Ni Nk Nn Og Pa) Jp(Fr Hx Ir Iu Ji Jl Jm Jo Jr Lh Lv Mi Ng Ni Nk Pc) Nw(In Iu Jl Jm Jo Js Jt Mi Ml Ms My Ng Nk Og Pd) Fr(aA Hu Ir Iu Ji Jn Jo Jr Mn Mz Ng Nk Nq Nr) Jl(aA In Iu Jm Jo Mi Ms Ng Ni Nk Nr Og Pa) Iu(aA Ir Ji Jr Lh Mz Nv On Pa Qa Qe) Ji(Jo Jq Jt Mf Mi Ms Ni Nk Nx Pa) On(Hr Jo Jt Mn Ms Ng Ni Nk Og Oy) Jo(Ir Iv Jg Lh Ok Qe) Ng(Jg Lh Nv Ok) Jr(Mi Mz Nk Pc) Jn(Lv Mu Pc) Ok(In Jt Mi) Nk(Mz Nv) Ir(Jm Nd) NiaA HrPa InLh QeJm Constrained panels with 2 analytes, where 1.0E-5 >= 'AUC p-value' > 1.0E-6. Contains 86 panels of 7,261 total panels evaluated. : On(Fr Hu In Ji Jk Jm Mg My Of Pd Pg) Jr(Jg Js Ma Mf Nd Ni Nv Ok Pa) Fr(Jm Lv Mg Mi Mk Mr Pa) Mz(Jg Jm Jp Lh Lu Mi Mv) Jj(Ij Ma Mu Nd Nn No Qc) Jo(Hx Ip Lv Mi Nv Pa Pg) Jp(Mk Mr Nr Ok Pa Pe) Iu(Hx Jn Ma No Pe) Nk(Ir Jn Pa Qe) Jm(Ji Nv Ok Qa) Nr(Ji Lh Nw) Ni(Nv Pa Qe) Mt(Mr Pe) Nd(Iv Ji) Nv(Ms Og) Ok(Lu Mg) MaIr MvJn NgQe HxIn IhIs Constrained panels with 2 analytes, where 1.0E-4 >= 'AUC p-value' > 1.0E-5. Contains 90 panels of 7,261 total panels evaluated. : Mz(Jo Js Lv Mk Mr Nn Nr Pa Pc) Iu(Ij Iv Jg Lu Mi Mn Mv Nn Ok) Jg(Hx Ir Jn Mg Ni Nk Pa Qe) Jo(Et Jr Nn Om Pc Pf Qa) Ng(Hx Jk Mv Nn Om Pa) Nk(Hx Lh Nn Ok Qa Qb) Jr(Jm Lh Mu Mv Nn Qe) Nd(Lv Nv Ok Qa Qe) Ir(Mn Nn Om Pc) Jm(Hx Jn Lh Pa) On(Mi Nb Nq Nr) Ni(Hx Nn No) In(Iv Pa Pe) Qe(Mi Om Pc) Mf(Lh Ok) Nv(Hu Mg) Pa(Ok Pd) NrIs MaIv MiPc MsOm JjOh JnJs JtLh Constrained panels with 2 analytes, where 1.0E-3 >= 'AUC p-value' > 1.0E-4. Contains 141 panels of 7,261 total panels evaluated. : Jo(Hw Ii Ij Io Jt Lw Ma Mj Mk Mm Mr Mu Mv Nb Nm No Nq Nr Oy Pe Qb Qd) Jg(Hu Jm Jt Lv Mi My Nd Nq Og Oi) Ma(Hv Hx Jm Jn Mg Nd Ng Nk Qb) Ni(Jn Mi Nd Oh Pf Pg Po Qa Qb) Nn(Jm Lv Mg Ms Nr Og Ok Pa) Pe(Jm Jr Mf Nd Nk Nr Nv Qe) Mr(Hr In Ir Jr Nv Qe) Mv(Hu Hx Ir Jm Nd Qe) Nk(Lv Nc No Oh Pf Po) Iu(Et Im Lv Pf Qb Qd) Pa(Lh Lv Mu Nr Om Pc) Mk(Ir Jn Jr Nv Qe) Hx(Lv Mu Nd Og Pc) Jm(Im Iv No Oh Qb) Nr(Ir Jr Nv Qe) Ng(Et No Pf Pg) In(Ij Mi Po Qa) Pc(Mu Ok Qa Qb) Nd(Et Jn Qb) Om(Jr Mf Og) Lu(Ir Jn) Mu(Ir Qe) LvPf MfQa MgLh IvOg Constrained panels with 2 analytes, where 1.0E-2 >= 'AUC p-value' > 1.0E-3. Contains 143 panels of 7,261 total panels evaluated. : Nk(Et Hv Im Iv Jk Jo Mi Mp Mu Mv Nd Nl Pg Qd) Ng(Ij Mp Mu Mw My Nd Nq Pc Pe Po Qd) Jm(Et Jk Mi Mp Mw Om Pf Pg Po Qc Qd) Jo(Hv Im Jk Jn Li Mp Mw Mx Oh Po) Pe(Jg Jn Ma Mu Mv Nn Pc Pd Qa Qb) Iu(Jh Jk Mu Mw Oh Om Pg Po Qc) Nr(Hx Jg Jn Ma Mu No Qa Qb) Lv(Lu Ma Mb Mf Mu Mv No Pc) Mk(In Jg Ma Nn No Qa Qb) Mr(Jg Jn Ma Mu Nn Qa Qb) Nd(Hv Mu Oh Om Pf Po Qd) Ni(Hv Jk Mp Mv Mw Nq Pc) Ma(Lw Mj Nb Pc) Qb(Lw Mj Mu Pa) Lu(Et Im Oh) Mf(Oh Pf Po) Mv(Iv Jg Mg) In(Hw Nb Pb) Pa(Hq Nf Qa) Pc(Iv No Pf) Js(Lh No) Om(Hu Mg) MnIv JgJh JkOg LhPd Constrained panels with 2 analytes, where 5.0E-2 >= 'AUC p-value' > 1.0E-2. Contains 68 panels of 7,261 total panels evaluated. : Nd(Iu Jo Mj Mk Mr Nb Nr Pc) Ng(Ii Io Mm Mr Nb Nm Oy Pb) Iu(Fp Hv Io Lj Mx Nq Ny) Jm(Ij Li Lj Mu Mx Pc) Lu(Iv Lw Mm Nk Nm) Et(Mj Mk Mr Nb) Mv(Lw Mj Mk Mr) Ni(Lw Mj Mx Pe) Nr(Lv Mi Om) Mg(Jk Mu Pc) Hq(Mi Mp Pg) Lv(Mj Nb) Mf(Mx Qd) Mu(Mk Og) Nk(Lj Pc) NtLh LwIv MpPd MsPc JoJq

Figure 10 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.5E1 | 9.0E1 | 7.6E1 | 1.1E2 | 5.2E1 | 8.7E1 | 2.0E0 | 7.0E0 | 4.0E2 | 4.0E2 | 1392 | 32 | 230 | 32 | 0.63 |
| Ad | ug/mL | 3.4E-2 | 6.4E-2 | 6.5E-2 | 9.7E-2 | 8.4E-2 | 8.3E-2 | 6.8E-4 | 2.7E-4 | 5.4E-1 | 3.5E-1 | 357 | 25 | 135 | 25 | 0.68 |
| Af | ng/mL | 1.0E0 | 4.5E-1 | 1.4E1 | 1.3E1 | 6.0E1 | 4.3E1 | 1.7E-3 | 1.7E-3 | 5.3E2 | 2.2E2 | 357 | 25 | 135 | 25 | 0.46 |
| Aj | ug/mL | 1.8E0 | 3.3E0 | 2.7E0 | 2.9E0 | 2.5E0 | 2.3E0 | 1.5E-3 | 1.8E-3 | 6.1E0 | 6.1E0 | 357 | 25 | 135 | 25 | 0.51 |
| Al | mg/mL | 8.7E-5 | 9.0E-5 | 2.5E-4 | 1.9E-4 | 4.1E-4 | 3.7E-4 | 2.5E-6 | 8.0E-6 | 1.9E-3 | 1.9E-3 | 357 | 25 | 135 | 25 | 0.52 |
| An | U/mL | 4.9E1 | 6.9E1 | 1.6E2 | 2.0E2 | 4.6E2 | 2.7E2 | 9.8E-4 | 8.6E-1 | 5.5E3 | 9.8E2 | 357 | 25 | 135 | 25 | 0.59 |
| Ao | pg/mL | 8.5E1 | 1.1E2 | 6.0E2 | 1.3E2 | 3.9E3 | 1.2E2 | 2.8E0 | 6.1E0 | 3.9E4 | 6.1E2 | 357 | 25 | 135 | 25 | 0.55 |
| Ap | ng/mL | 3.1E1 | 5.0E1 | 4.2E1 | 6.2E1 | 4.3E1 | 4.5E1 | 8.4E-5 | 2.1E0 | 2.9E2 | 1.8E2 | 357 | 25 | 135 | 25 | 0.67 |
| Ar | ng/mL | 8.5E-1 | 1.5E0 | 1.5E1 | 4.0E0 | 2.2E2 | 5.1E0 | 3.4E-3 | 5.7E-2 | 4.1E3 | 2.0E1 | 357 | 25 | 135 | 25 | 0.62 |
| As | ng/mL | 9.5E-3 | 1.0E-2 | 1.3E-2 | 2.0E-2 | 1.8E-2 | 3.2E-2 | 1.7E-3 | 1.7E-3 | 1.3E-1 | 1.2E-1 | 357 | 25 | 135 | 25 | 0.51 |
| Aw | pg/mL | 1.6E1 | 1.7E1 | 1.6E1 | 1.7E1 | 5.9E0 | 6.7E0 | 2.9E-2 | 2.9E-2 | 4.8E1 | 3.8E1 | 357 | 25 | 135 | 25 | 0.57 |
| Ax | ng/mL | 2.2E0 | 4.5E0 | 1.4E1 | 2.1E1 | 5.8E1 | 4.4E1 | 1.3E-2 | 3.9E-2 | 7.7E2 | 2.0E2 | 357 | 25 | 135 | 25 | 0.57 |
| Ba | ng/mL | 6.2E1 | 1.7E2 | 4.2E2 | 4.9E2 | 1.2E3 | 6.8E2 | 3.7E-1 | 6.9E-1 | 8.1E3 | 3.0E3 | 357 | 25 | 135 | 25 | 0.63 |
| Bb | ng/mL | 2.8E0 | 5.2E0 | 6.1E0 | 6.1E0 | 1.5E1 | 4.2E0 | 4.1E-3 | 5.5E-1 | 2.5E2 | 1.6E1 | 357 | 25 | 135 | 25 | 0.64 |
| Bc | ng/mL | 3.4E1 | 7.2E1 | 1.0E2 | 1.5E2 | 1.9E2 | 2.6E2 | 1.1E-1 | 2.4E0 | 1.2E3 | 1.0E3 | 357 | 25 | 135 | 25 | 0.64 |
| Bg | ng/mL | 7.7E-2 | 2.9E-1 | 4.0E0 | 6.7E-1 | 1.9E1 | 1.1E0 | 5.3E-4 | 5.3E-4 | 2.5E2 | 4.8E0 | 357 | 25 | 135 | 25 | 0.60 |
| Bn | ng/mL | 5.6E-2 | 5.6E-2 | 1.1E0 | 1.4E0 | 1.9E0 | 2.4E0 | 5.6E-2 | 5.6E-2 | 9.7E0 | 7.6E0 | 357 | 25 | 135 | 25 | 0.51 |
| Bo | ng/mL | 1.2E1 | 1.7E1 | 1.4E1 | 1.7E1 | 2.0E1 | 1.2E1 | 1.6E-2 | 1.6E-2 | 2.8E2 | 3.6E1 | 357 | 25 | 135 | 25 | 0.59 |
| Ch | uIU/mL | 1.2E0 | 8.5E-1 | 2.1E1 | 5.3E0 | 1.1E2 | 1.6E1 | 3.4E-3 | 1.0E-1 | 1.8E3 | 8.0E1 | 357 | 25 | 135 | 25 | 0.44 |
| Co | pg/mL | 3.8E1 | 5.5E1 | 1.8E2 | 7.6E1 | 1.1E3 | 7.7E1 | 1.5E-1 | 9.1E0 | 1.7E4 | 3.9E2 | 357 | 25 | 135 | 25 | 0.59 |
| Cp | ng/mL | 2.2E1 | 2.3E1 | 2.8E1 | 2.7E1 | 3.3E1 | 2.0E1 | 6.0E-1 | 6.0E-1 | 3.7E2 | 9.9E1 | 357 | 25 | 135 | 25 | 0.55 |
| Cq | ng/mL | 2.8E-2 | 3.4E-2 | 1.5E-1 | 6.5E-2 | 9.5E-1 | 1.1E-1 | 8.0E-4 | 8.0E-4 | 1.7E1 | 4.9E-1 | 357 | 25 | 135 | 25 | 0.53 |
| Cs | ng/mL | 6.6E1 | 1.6E2 | 3.0E2 | 4.5E2 | 8.6E2 | 1.1E3 | 2.7E-2 | 1.5E0 | 1.1E4 | 5.3E3 | 357 | 25 | 135 | 25 | 0.57 |
| Ct | ng/mL | 8.9E-1 | 3.3E-1 | 4.0E1 | 1.7E1 | 1.1E2 | 3.9E1 | 1.1E-4 | 1.5E-2 | 6.2E2 | 1.6E2 | 357 | 25 | 135 | 25 | 0.43 |
| Cu | ng/mL | 2.4E-1 | 3.8E-1 | 4.0E-1 | 4.0E-1 | 7.0E-1 | 2.4E-1 | 9.6E-3 | 1.8E-2 | 9.2E0 | 9.9E-1 | 357 | 25 | 135 | 25 | 0.63 |
| Cv | ng/mL | 4.1E0 | 1.2E1 | 1.8E1 | 3.8E1 | 4.9E1 | 9.3E1 | 1.4E-4 | 1.8E-2 | 5.3E2 | 4.7E2 | 357 | 25 | 135 | 25 | 0.62 |
| Cw | mIU/mL | 3.0E-2 | 4.0E-2 | 3.8E-2 | 4.0E-2 | 3.2E-2 | 2.9E-2 | 8.9E-4 | 1.5E-4 | 2.4E-1 | 1.3E-1 | 357 | 25 | 135 | 25 | 0.54 |
| Cx | ng/mL | 1.5E-1 | 4.6E-2 | 5.1E1 | 6.4E1 | 9.9E1 | 1.3E2 | 9.3E-5 | 9.3E-5 | 3.9E2 | 3.9E2 | 357 | 25 | 135 | 25 | 0.50 |
| Db | ug/mL | 7.2E0 | 6.8E0 | 8.6E0 | 1.4E1 | 7.3E0 | 2.8E1 | 4.5E-1 | 8.5E-1 | 5.9E1 | 1.4E2 | 357 | 25 | 135 | 25 | 0.52 |
| Dc | nmol/L | 1.9E-2 | 1.7E-2 | 5.7E-2 | 2.5E-2 | 1.4E-1 | 2.4E-2 | 5.2E-6 | 3.0E-4 | 1.6E0 | 9.9E-2 | 357 | 25 | 135 | 25 | 0.47 |
| Dd | ug/mL | 6.9E-2 | 4.2E-2 | 1.8E-1 | 1.2E-1 | 2.7E-1 | 2.0E-1 | 1.9E-4 | 4.8E-4 | 1.9E0 | 8.9E-1 | 357 | 25 | 135 | 25 | 0.41 |
| De | ng/mL | 3.4E-3 | 3.4E-3 | 7.8E-2 | 5.8E-2 | 1.4E-1 | 1.1E-1 | 3.4E-3 | 3.4E-3 | 9.2E-1 | 5.0E-1 | 357 | 25 | 135 | 25 | 0.47 |
| Dg | ng/mL | 2.9E1 | 6.6E1 | 4.2E1 | 7.0E1 | 3.8E1 | 4.6E1 | 1.0E-1 | 2.1E0 | 1.9E2 | 1.9E2 | 357 | 25 | 135 | 25 | 0.69 |
| Di | pg/mL | 2.0E0 | 1.3E0 | 2.2E0 | 1.5E0 | 2.0E0 | 1.4E0 | 1.8E-1 | 1.8E-1 | 1.3E1 | 4.0E0 | 357 | 25 | 135 | 25 | 0.39 |
| Dk | uIU/mL | 1.7E-2 | 1.9E-2 | 9.6E-2 | 2.5E-2 | 5.7E-1 | 2.1E-2 | 1.1E-4 | 1.1E-4 | 8.9E0 | 9.0E-2 | 357 | 25 | 135 | 25 | 0.50 |
| Dl | ng/mL | 2.3E2 | 4.3E2 | 3.1E2 | 5.1E2 | 2.8E2 | 4.0E2 | 1.7E0 | 6.4E0 | 1.5E3 | 1.3E3 | 357 | 25 | 135 | 25 | 0.65 |
| Do | ng/ml | 4.7E-1 | 6.3E-1 | 1.1E0 | 1.1E0 | 2.7E0 | 1.6E0 | 3.6E-2 | 3.6E-2 | 1.9E1 | 4.6E0 | 62 | 7 | 44 | 7 | 0.57 |
| Dp | ng/ml | 2.3E0 | 2.4E0 | 5.1E0 | 4.7E0 | 7.9E0 | 6.1E0 | 3.7E-3 | 3.7E-3 | 4.6E1 | 2.2E1 | 217 | 22 | 135 | 22 | 0.50 |
| Dr | pg/ml | 2.1E1 | 1.7E1 | 4.7E1 | 1.9E1 | 7.1E1 | 2.1E1 | 7.5E-1 | 7.5E-1 | 5.2E2 | 6.0E1 | 125 | 8 | 71 | 8 | 0.38 |
| Dq | Absorbance | 1.7E-3 | 1.7E-3 | 3.2E-2 | 1.7E-3 | 1.4E-1 | 0.0E0 | 1.7E-3 | 1.7E-3 | 8.3E-1 | 1.7E-3 | 60 | 7 | 43 | 7 | 0.39 |
| Dv | pg/ml | 1.1E0 | 7.6E-1 | 1.2E0 | 9.0E-1 | 1.2E0 | 7.4E-1 | 2.2E-2 | 2.2E-2 | 4.5E0 | 2.3E0 | 42 | 7 | 25 | 7 | 0.46 |
| Ef | ng/ml | 1.5E-1 | 1.8E-1 | 8.1E-1 | 7.9E-1 | 1.6E0 | 1.8E0 | 5.7E-4 | 1.3E-3 | 9.5E0 | 8.4E0 | 261 | 23 | 134 | 23 | 0.53 |
| Wm | % | 4.9E-1 | 7.6E-1 | 2.3E1 | 1.3E2 | 1.6E2 | 3.4E2 | 5.4E-2 | 8.5E-2 | 2.4E3 | 1.3E3 | 283 | 25 | 151 | 25 | 0.57 |
| Ed | pg/ml | 5.2E-1 | 5.2E-1 | 6.3E1 | 4.3E1 | 5.0E2 | 8.4E1 | 5.2E-1 | 5.2E-1 | 7.3E3 | 3.5E2 | 217 | 22 | 134 | 22 | 0.50 |
| Tj | pg/mL | 3.7E-1 | 3.7E-1 | 6.8E1 | 7.2E0 | 3.3E2 | 1.2E1 | 3.6E-1 | 3.7E-1 | 3.5E3 | 4.0E1 | 258 | 23 | 136 | 23 | 0.50 |
| Po | pg/ml | 6.7E-1 | 1.6E0 | 9.1E0 | 1.6E1 | 2.5E1 | 4.1E1 | 8.0E-3 | 2.6E-2 | 2.7E2 | 2.2E2 | 580 | 35 | 207 | 35 | 0.55 |
| Em | ng/ml | 9.2E-3 | 2.9E-3 | 6.7E-2 | 1.2E-1 | 1.2E-1 | 2.0E-1 | 1.9E-16 | 2.9E-3 | 6.0E-1 | 4.7E-1 | 149 | 9 | 71 | 9 | 0.52 |
| Et | ng/ml | 1.3E3 | 3.0E3 | 1.6E3 | 2.7E3 | 1.1E3 | 1.4E3 | 7.7E1 | 9.1E1 | 5.0E3 | 5.0E3 | 579 | 35 | 207 | 35 | 0.73 |
| Fa | ng/ml | 4.0E1 | 7.5E1 | 1.3E2 | 8.2E1 | 6.0E2 | 7.2E1 | 3.4E-2 | 2.6E-1 | 8.0E3 | 2.9E2 | 212 | 22 | 133 | 22 | 0.60 |
| Ez | ng/ml | 5.0E0 | 3.9E0 | 2.0E1 | 1.1E1 | 5.9E1 | 1.4E1 | 1.3E-2 | 1.3E-2 | 7.1E2 | 4.6E1 | 217 | 22 | 135 | 22 | 0.50 |
| Fb | ng/ml | 2.5E1 | 2.3E1 | 2.3E1 | 2.3E1 | 1.1E1 | 1.1E1 | 6.6E-1 | 8.1E-1 | 5.7E1 | 4.1E1 | 213 | 22 | 133 | 22 | 0.47 |
| Ex | ng/ml | 7.8E-2 | 1.2E-1 | 2.5E-1 | 1.9E-1 | 7.6E-1 | 2.3E-1 | 3.5E-5 | 1.7E-4 | 8.9E0 | 9.2E-1 | 190 | 17 | 89 | 17 | 0.58 |
| Fn | ng/ml | 2.1E-1 | 2.1E-1 | 6.3E0 | 4.8E0 | 2.9E1 | 7.8E0 | 1.1E-14 | 1.1E-14 | 4.2E2 | 2.6E1 | 217 | 22 | 135 | 22 | 0.49 |

Figure 11

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fp | ng/ml | 1.2E1 | 3.3E1 | 2.4E1 | 4.4E1 | 2.8E1 | 3.7E1 | 6.0E-3 | 2.8E-1 | 1.4E2 | 1.4E2 | 606 | 35 | 209 | 35 | 0.68 |
| Fr | ng/ml | 3.3E4 | 9.6E4 | 1.1E5 | 2.1E5 | 1.7E5 | 2.7E5 | 1.9E2 | 1.2E3 | 9.0E5 | 8.9E5 | 686 | 38 | 210 | 38 | 0.65 |
| Fw | pg/ml | 8.5E-1 | 2.9E0 | 7.0E1 | 4.4E1 | 5.4E2 | 1.4E2 | 1.1E-14 | 1.7E-14 | 6.9E3 | 6.3E2 | 259 | 23 | 135 | 23 | 0.53 |
| Fy | ng/ml | 3.5E1 | 4.3E1 | 5.5E1 | 5.7E1 | 5.7E1 | 5.0E1 | 1.2E-1 | 9.7E-1 | 3.3E2 | 2.1E2 | 216 | 22 | 134 | 22 | 0.55 |
| Gc | ng/ml | 9.2E1 | 1.2E2 | 1.4E2 | 1.6E2 | 1.7E2 | 1.4E2 | 6.4E0 | 2.2E1 | 1.2E3 | 4.4E2 | 134 | 8 | 72 | 8 | 0.55 |
| Gn | U/ml | 3.6E-1 | 5.6E-3 | 1.3E0 | 7.6E-2 | 3.3E0 | 1.8E-1 | 1.3E-3 | 1.3E-3 | 3.0E1 | 5.3E-1 | 119 | 8 | 69 | 8 | 0.14 |
| Gl | pg/ml | 7.8E3 | 6.2E3 | 1.1E4 | 8.3E3 | 9.4E3 | 6.2E3 | 9.1E1 | 1.0E3 | 3.3E4 | 2.3E4 | 252 | 23 | 135 | 23 | 0.46 |
| Gp | U/ml | 1.5E0 | 1.8E0 | 4.0E0 | 3.6E0 | 6.8E0 | 5.4E0 | 1.3E-3 | 1.5E-2 | 6.7E1 | 2.1E1 | 261 | 23 | 135 | 23 | 0.47 |
| Gt | ng/ml | 2.2E-3 | 2.2E-3 | 1.3E-1 | 2.2E-3 | 5.0E-1 | 0.0E0 | 2.2E-3 | 2.2E-3 | 3.3E0 | 2.2E-3 | 47 | 7 | 31 | 7 | 0.36 |
| Gw | ng/ml | 4.9E0 | 9.6E0 | 8.0E0 | 1.2E1 | 1.3E1 | 7.8E0 | 8.3E-1 | 3.6E0 | 9.3E1 | 2.2E1 | 62 | 7 | 44 | 7 | 0.72 |
| Gz | ug/ml | 1.4E0 | 1.2E0 | 9.7E0 | 5.4E0 | 4.2E1 | 6.4E0 | 2.9E-16 | 1.2E-1 | 4.8E2 | 2.1E1 | 143 | 16 | 86 | 16 | 0.51 |
| Ha | ng/ml | 2.7E0 | 2.2E0 | 9.9E0 | 3.9E0 | 2.1E1 | 6.5E0 | 1.7E-2 | 1.7E-2 | 1.3E2 | 3.0E1 | 215 | 22 | 134 | 22 | 0.42 |
| Nm | pg/ml | 1.6E4 | 3.3E4 | 3.2E4 | 5.9E4 | 8.8E4 | 8.2E4 | 1.0E-9 | 1.0E-9 | 1.6E6 | 4.4E5 | 583 | 35 | 209 | 35 | 0.63 |
| Nn | pg/ml | 1.5E2 | 3.2E2 | 2.2E3 | 4.5E3 | 9.4E3 | 1.3E4 | 1.0E-9 | 1.0E-9 | 1.0E5 | 6.9E4 | 583 | 35 | 209 | 35 | 0.59 |
| No | pg/ml | 1.5E1 | 2.8E1 | 3.7E1 | 1.0E2 | 1.3E2 | 2.9E2 | 1.0E-9 | 1.0E-9 | 2.5E3 | 1.4E3 | 583 | 35 | 209 | 35 | 0.63 |
| Nq | pg/ml | 2.0E0 | 8.9E-2 | 1.9E1 | 2.8E1 | 7.6E1 | 6.5E1 | 1.0E-9 | 1.0E-9 | 1.2E3 | 2.7E2 | 583 | 35 | 209 | 35 | 0.48 |
| Nr | pg/ml | 8.8E-1 | 4.6E0 | 3.3E1 | 2.6E2 | 2.1E2 | 1.4E3 | 1.0E-9 | 1.0E-9 | 4.1E3 | 8.5E3 | 583 | 35 | 209 | 35 | 0.63 |
| Ns | pg/ml | 1.0E-9 | 1.0E-9 | 1.1E1 | 8.0E-1 | 6.1E1 | 2.9E0 | 1.0E-9 | 1.0E-9 | 1.1E3 | 1.6E1 | 583 | 35 | 209 | 35 | 0.50 |
| Nt | pg/ml | 1.0E2 | 1.6E2 | 1.4E2 | 2.2E2 | 1.1E2 | 1.5E2 | 1.0E-9 | 2.6E1 | 1.5E3 | 6.8E2 | 583 | 35 | 209 | 35 | 0.70 |
| Nu | pg/ml | 2.3E1 | 1.0E2 | 5.7E1 | 1.1E2 | 9.5E1 | 1.1E2 | 1.0E-9 | 1.0E-9 | 8.9E2 | 5.8E2 | 583 | 35 | 209 | 35 | 0.69 |
| Lu | pg/ml | 1.0E4 | 1.0E4 | 1.7E4 | 2.0E4 | 4.7E4 | 4.0E4 | 3.5E2 | 1.6E3 | 7.5E5 | 2.3E5 | 585 | 35 | 209 | 35 | 0.50 |
| Lv | pg/ml | 1.0E-9 | 2.1E1 | 1.1E1 | 2.9E1 | 2.1E1 | 4.0E1 | 1.0E-9 | 1.0E-9 | 2.4E2 | 1.9E2 | 585 | 35 | 209 | 35 | 0.66 |
| Lw | pg/ml | 1.0E-9 | 1.0E-9 | 4.0E-1 | 1.1E0 | 4.3E0 | 4.5E0 | 1.0E-9 | 1.0E-9 | 8.0E1 | 2.1E1 | 585 | 35 | 209 | 35 | 0.53 |
| Lx | pg/ml | 1.0E-9 | 9.2E1 | 1.5E2 | 5.8E2 | 4.5E2 | 1.8E3 | 1.0E-9 | 1.0E-9 | 6.2E3 | 1.0E4 | 585 | 35 | 209 | 35 | 0.69 |
| Ly | pg/ml | 1.0E-9 | 1.5E1 | 1.0E1 | 2.2E1 | 2.0E1 | 2.5E1 | 1.0E-9 | 1.0E-9 | 1.6E2 | 8.7E1 | 585 | 35 | 209 | 35 | 0.67 |
| Lz | pg/ml | 1.0E-9 | 1.0E-9 | 4.9E0 | 6.0E0 | 3.6E1 | 3.5E1 | 1.0E-9 | 1.0E-9 | 6.0E2 | 2.1E2 | 585 | 35 | 209 | 35 | 0.49 |
| Ma | pg/ml | 3.1E2 | 3.0E2 | 1.3E3 | 1.3E3 | 3.8E3 | 2.4E3 | 1.0E-9 | 3.0E0 | 6.5E4 | 1.0E4 | 585 | 35 | 209 | 35 | 0.54 |
| Mb | pg/ml | 2.5E1 | 2.9E1 | 3.1E1 | 3.6E1 | 1.6E1 | 1.7E1 | 5.4E0 | 1.6E1 | 2.1E2 | 8.7E1 | 585 | 35 | 209 | 35 | 0.58 |
| Mc | pg/ml | 1.0E-9 | 1.0E-9 | 4.2E-2 | 1.0E-9 | 5.8E-1 | 0.0E0 | 1.0E-9 | 1.0E-9 | 1.3E1 | 1.0E-9 | 585 | 35 | 209 | 35 | 0.49 |
| Md | pg/ml | 1.0E-9 | 1.0E-9 | 4.8E-1 | 6.3E-3 | 3.3E0 | 3.8E-2 | 1.0E-9 | 1.0E-9 | 6.5E1 | 2.2E-1 | 585 | 35 | 209 | 35 | 0.47 |
| Me | pg/ml | 3.2E1 | 2.7E1 | 3.1E1 | 2.9E1 | 2.0E1 | 1.4E1 | 1.0E-9 | 3.2E0 | 3.2E2 | 7.9E1 | 585 | 35 | 209 | 35 | 0.45 |
| Mf | pg/ml | 1.0E-9 | 1.0E-9 | 5.2E-1 | 5.8E-1 | 3.1E0 | 1.6E0 | 1.0E-9 | 1.0E-9 | 5.6E1 | 8.4E0 | 585 | 35 | 209 | 35 | 0.56 |
| Mg | pg/ml | 2.0E0 | 6.5E0 | 7.7E0 | 9.7E0 | 1.3E1 | 1.1E1 | 1.0E-9 | 1.0E-9 | 9.2E1 | 4.0E1 | 585 | 35 | 209 | 35 | 0.60 |
| Mh | pg/ml | 1.0E-9 | 1.0E-9 | 1.5E0 | 2.0E0 | 1.1E1 | 6.9E0 | 1.0E-9 | 1.0E-9 | 1.6E2 | 3.8E1 | 585 | 35 | 209 | 35 | 0.50 |
| Mi | pg/ml | 1.0E-9 | 1.0E-9 | 5.9E-1 | 8.6E0 | 6.3E0 | 3.0E1 | 1.0E-9 | 1.0E-9 | 1.2E2 | 1.6E2 | 585 | 35 | 209 | 35 | 0.56 |
| Mj | pg/ml | 1.0E-9 | 1.0E-9 | 4.8E0 | 1.7E1 | 2.7E1 | 9.2E1 | 1.0E-9 | 1.0E-9 | 4.6E2 | 5.4E2 | 585 | 35 | 209 | 35 | 0.52 |
| Mk | pg/ml | 5.3E-1 | 8.4E-1 | 1.8E1 | 1.6E2 | 1.1E2 | 9.4E2 | 1.0E-9 | 1.0E-9 | 1.7E3 | 5.6E3 | 585 | 35 | 209 | 35 | 0.50 |
| Ml | pg/ml | 1.0E-9 | 1.0E-9 | 6.3E0 | 1.3E0 | 9.0E1 | 3.4E0 | 1.0E-9 | 1.0E-9 | 2.1E3 | 1.6E1 | 585 | 35 | 209 | 35 | 0.55 |
| Mm | pg/ml | 5.9E2 | 1.2E3 | 9.8E2 | 1.9E3 | 1.1E3 | 2.0E3 | 1.0E-9 | 1.0E-9 | 7.3E3 | 6.9E3 | 585 | 35 | 209 | 35 | 0.63 |
| Mn | pg/ml | 5.4E0 | 6.7E0 | 1.1E1 | 1.1E1 | 2.6E1 | 1.4E1 | 1.0E-9 | 1.0E-9 | 3.5E2 | 6.6E1 | 585 | 35 | 209 | 35 | 0.56 |
| Mp | pg/ml | 1.0E-9 | 3.3E0 | 9.2E0 | 1.9E1 | 3.2E1 | 4.4E1 | 1.0E-9 | 1.0E-9 | 6.3E2 | 1.8E2 | 584 | 35 | 209 | 35 | 0.57 |
| Mq | pg/ml | 1.0E-9 | 1.0E-9 | 2.9E0 | 4.8E0 | 1.7E1 | 2.4E1 | 1.0E-9 | 1.0E-9 | 2.1E2 | 1.4E2 | 584 | 35 | 209 | 35 | 0.50 |
| Mr | pg/ml | 1.0E-9 | 1.0E-9 | 1.9E1 | 4.0E2 | 8.5E1 | 2.0E3 | 1.0E-9 | 1.0E-9 | 1.4E3 | 1.2E4 | 584 | 35 | 209 | 35 | 0.55 |
| Ms | pg/ml | 4.1E2 | 6.1E2 | 5.6E2 | 5.6E2 | 6.5E2 | 4.9E2 | 1.0E-9 | 1.0E-9 | 5.6E3 | 1.7E3 | 584 | 35 | 209 | 35 | 0.53 |
| Mt | pg/ml | 2.2E-1 | 1.8E0 | 7.4E0 | 9.7E0 | 5.0E1 | 1.9E1 | 1.0E-9 | 1.0E-9 | 8.7E2 | 7.8E1 | 584 | 35 | 209 | 35 | 0.71 |
| Mu | pg/ml | 1.0E-9 | 1.0E-9 | 1.6E0 | 1.8E0 | 1.3E1 | 5.1E0 | 1.0E-9 | 1.0E-9 | 2.3E2 | 2.7E1 | 584 | 35 | 209 | 35 | 0.56 |
| Mv | pg/ml | 1.0E-9 | 1.0E-9 | 7.6E1 | 5.7E1 | 3.6E2 | 1.8E2 | 1.0E-9 | 1.0E-9 | 4.5E3 | 9.3E2 | 584 | 35 | 209 | 35 | 0.51 |
| Mw | pg/ml | 3.4E1 | 5.4E1 | 4.8E2 | 9.8E2 | 3.1E3 | 3.2E3 | 1.0E-9 | 1.0E-9 | 6.2E4 | 1.7E4 | 584 | 35 | 209 | 35 | 0.58 |
| Mx | pg/ml | 1.0E-9 | 1.0E-9 | 2.5E-1 | 2.4E-1 | 1.5E0 | 5.9E-1 | 1.0E-9 | 1.0E-9 | 3.2E1 | 3.0E0 | 584 | 35 | 209 | 35 | 0.56 |
| My | pg/ml | 1.0E-9 | 1.0E-9 | 4.7E2 | 3.5E2 | 3.1E3 | 9.1E2 | 1.0E-9 | 1.0E-9 | 3.9E4 | 4.1E3 | 584 | 35 | 209 | 35 | 0.56 |
| Mz | pg/ml | 1.0E1 | 2.0E1 | 2.5E1 | 3.9E1 | 7.2E1 | 4.7E1 | 1.0E-9 | 1.0E-9 | 1.2E3 | 2.0E2 | 584 | 35 | 209 | 35 | 0.63 |
| Na | pg/ml | 1.0E-9 | 1.0E-9 | 7.4E-1 | 8.3E-1 | 3.0E0 | 2.6E0 | 1.0E-9 | 1.0E-9 | 3.6E1 | 1.1E1 | 584 | 35 | 209 | 35 | 0.52 |
| Nb | pg/ml | 1.9E0 | 3.0E0 | 4.2E0 | 1.2E1 | 1.4E1 | 4.0E1 | 1.0E-9 | 1.0E-9 | 2.3E2 | 2.4E2 | 584 | 35 | 209 | 35 | 0.62 |
| Nc | pg/ml | 4.0E2 | 1.9E2 | 6.3E2 | 2.7E2 | 7.9E2 | 3.5E2 | 1.0E-9 | 1.0E-9 | 9.2E3 | 1.4E3 | 584 | 35 | 209 | 35 | 0.35 |
| Nd | pg/ml | 2.9E1 | 4.4E0 | 2.7E1 | 2.2E1 | 5.4E1 | 3.3E1 | 1.0E-9 | 1.0E-9 | 1.2E3 | 1.4E2 | 584 | 35 | 209 | 35 | 0.37 |
| Ne | pg/ml | 4.7E2 | 2.5E2 | 6.1E2 | 3.1E2 | 6.0E2 | 3.2E2 | 1.0E-9 | 1.0E-9 | 7.0E3 | 1.6E3 | 584 | 35 | 209 | 35 | 0.33 |
| Nf | pg/ml | 1.0E-9 | 1.0E-9 | 3.0E0 | 3.4E0 | 1.1E1 | 1.4E1 | 1.0E-9 | 1.0E-9 | 1.6E2 | 8.2E1 | 584 | 35 | 209 | 35 | 0.43 |

Figure 11 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ng | pg/ml | 3.6E1 | 5.8E1 | 1.4E2 | 1.3E2 | 2.6E2 | 1.7E2 | 1.0E-9 | 1.0E-9 | 2.3E3 | 5.0E2 | 584 | 35 | 209 | 35 | 0.53 |
| Nh | pg/ml | 7.1E1 | 3.3E1 | 9.5E1 | 5.0E1 | 8.8E1 | 5.2E1 | 1.0E-9 | 1.0E-9 | 5.6E2 | 2.1E2 | 584 | 35 | 209 | 35 | 0.32 |
| Ni | pg/ml | 1.0E-9 | 2.3E1 | 7.8E1 | 1.0E2 | 1.2E2 | 1.4E2 | 1.0E-9 | 1.0E-9 | 7.1E2 | 5.5E2 | 584 | 35 | 209 | 35 | 0.54 |
| Nj | pg/ml | 7.9E0 | 2.8E0 | 1.1E1 | 5.5E0 | 1.2E1 | 6.3E0 | 1.0E-9 | 1.0E-9 | 8.3E1 | 2.3E1 | 584 | 35 | 209 | 35 | 0.34 |
| Nk | pg/ml | 2.0E1 | 1.6E1 | 3.5E1 | 2.5E1 | 4.0E1 | 3.4E1 | 1.0E-9 | 1.0E-9 | 2.0E2 | 1.7E2 | 584 | 35 | 209 | 35 | 0.45 |
| Nl | pg/ml | 4.9E1 | 1.6E1 | 6.6E1 | 2.6E1 | 7.4E1 | 2.7E1 | 1.0E-9 | 1.0E-9 | 1.1E3 | 9.1E1 | 584 | 35 | 209 | 35 | 0.30 |
| Tz | pg/ml | 5.3E3 | 8.8E3 | 1.4E4 | 9.3E3 | 6.9E4 | 1.2E4 | 1.0E-9 | 2.3E2 | 1.0E6 | 5.6E4 | 219 | 22 | 133 | 22 | 0.52 |
| Ua | pg/ml | 3.9E3 | 5.6E3 | 1.6E4 | 8.4E3 | 2.9E4 | 1.1E4 | 1.0E-9 | 4.3E2 | 1.9E5 | 4.3E4 | 219 | 22 | 133 | 22 | 0.51 |
| Ub | pg/ml | 5.7E2 | 5.7E2 | 8.5E2 | 8.8E2 | 1.1E3 | 1.2E3 | 1.0E-9 | 3.4E1 | 9.8E3 | 4.9E3 | 219 | 22 | 133 | 22 | 0.49 |
| Ue | pg/ml | 2.9E1 | 2.2E1 | 3.6E1 | 5.3E1 | 3.2E1 | 9.3E1 | 9.8E-2 | 5.1E0 | 3.5E2 | 4.4E2 | 219 | 22 | 133 | 22 | 0.45 |
| Uc | pg/ml | 9.2E2 | 1.0E3 | 1.7E3 | 1.8E3 | 2.9E3 | 1.8E3 | 1.0E-9 | 6.0E1 | 2.9E4 | 7.2E3 | 219 | 22 | 133 | 22 | 0.54 |
| Ud | pg/ml | 1.0E-9 | 1.0E-9 | 1.9E0 | 1.0E-9 | 2.6E1 | 0.0E0 | 1.0E-9 | 1.0E-9 | 3.9E2 | 1.0E-9 | 219 | 22 | 133 | 22 | 0.49 |
| Hq | pg/ml | 1.1E0 | 1.9E0 | 1.5E2 | 1.1E1 | 2.0E3 | 5.0E1 | 1.0E-9 | 1.0E-9 | 3.4E4 | 3.0E2 | 581 | 35 | 208 | 35 | 0.55 |
| Hr | pg/ml | 1.3E2 | 1.1E2 | 8.0E2 | 1.0E3 | 1.6E3 | 3.4E3 | 1.0E-9 | 1.0E-9 | 1.4E4 | 1.7E4 | 581 | 35 | 208 | 35 | 0.45 |
| Hu | pg/ml | 1.1E1 | 1.2E1 | 3.2E3 | 1.7E3 | 3.1E4 | 8.0E3 | 1.0E-9 | 1.0E-9 | 6.3E5 | 4.7E4 | 581 | 35 | 208 | 35 | 0.51 |
| Hv | pg/ml | 1.5E0 | 3.0E0 | 3.4E0 | 5.0E0 | 1.2E1 | 1.0E1 | 1.0E-9 | 1.0E-9 | 2.5E2 | 5.9E1 | 581 | 35 | 208 | 35 | 0.64 |
| Hw | pg/ml | 7.0E0 | 3.7E0 | 2.2E1 | 1.1E2 | 8.6E1 | 5.8E2 | 1.0E-9 | 1.0E-9 | 1.7E3 | 3.4E3 | 581 | 35 | 208 | 35 | 0.42 |
| Hx | pg/ml | 9.6E0 | 1.0E1 | 4.7E1 | 7.3E1 | 4.0E2 | 3.3E2 | 1.0E-9 | 1.0E-9 | 9.3E3 | 2.0E3 | 581 | 35 | 208 | 35 | 0.47 |
| Ib | ng/ml | 6.7E-2 | 3.1E-2 | 2.3E0 | 4.5E-1 | 7.8E0 | 1.3E0 | 1.0E-9 | 1.0E-9 | 5.3E1 | 6.1E0 | 210 | 22 | 132 | 22 | 0.42 |
| Ic | U/ml | 2.2E2 | 2.2E2 | 8.1E2 | 2.1E3 | 6.5E3 | 6.6E3 | 2.4E0 | 1.5E0 | 9.3E4 | 3.0E4 | 210 | 22 | 132 | 22 | 0.60 |
| Id | U/ml | 6.5E-1 | 1.2E0 | 1.2E0 | 2.3E0 | 2.0E0 | 4.3E0 | 1.0E-9 | 5.6E-2 | 2.3E1 | 2.1E1 | 210 | 22 | 132 | 22 | 0.67 |
| Tt | pg/ml | 1.7E2 | 1.8E2 | 1.7E2 | 1.8E2 | 5.1E1 | 4.0E1 | 4.3E1 | 1.2E2 | 3.6E2 | 2.6E2 | 202 | 22 | 127 | 22 | 0.58 |
| To | pg/ml | 1.6E0 | 1.9E0 | 1.9E0 | 2.2E0 | 2.0E0 | 1.8E0 | 1.0E-9 | 1.0E-9 | 1.0E1 | 6.3E0 | 211 | 22 | 130 | 22 | 0.58 |
| Tr | pg/ml | 3.0E0 | 4.3E0 | 6.2E0 | 5.8E0 | 2.2E1 | 5.1E0 | 1.0E-9 | 9.5E-2 | 3.1E2 | 2.1E1 | 207 | 22 | 129 | 22 | 0.58 |
| Tn | pg/ml | 2.9E1 | 3.2E1 | 7.5E1 | 4.6E1 | 2.0E2 | 4.8E1 | 2.4E0 | 1.1E1 | 1.8E3 | 2.3E2 | 211 | 22 | 130 | 22 | 0.55 |
| Tv | ng/ml | 1.2E1 | 1.6E1 | 2.0E1 | 2.0E1 | 3.9E1 | 2.1E1 | 1.0E-9 | 1.0E-9 | 4.9E2 | 7.0E1 | 211 | 22 | 130 | 22 | 0.51 |
| Ih | ng/ml | 7.5E1 | 1.8E2 | 2.1E2 | 4.4E2 | 3.6E2 | 7.2E2 | 1.0E-9 | 1.0E-9 | 2.6E3 | 2.9E3 | 584 | 35 | 208 | 35 | 0.58 |
| Ii | ng/ml | 9.8E1 | 1.3E2 | 2.7E2 | 5.4E2 | 7.6E2 | 1.7E3 | 7.3E-1 | 3.5E0 | 1.0E4 | 9.2E3 | 584 | 35 | 208 | 35 | 0.54 |
| Ij | ng/ml | 7.6E1 | 1.0E2 | 1.9E2 | 2.9E2 | 6.3E2 | 1.1E3 | 2.1E0 | 8.7E0 | 6.4E3 | 6.4E3 | 579 | 35 | 207 | 35 | 0.59 |
| Ik | ng/ml | 1.4E1 | 2.8E2 | 1.1E3 | 5.6E2 | 1.0E4 | 8.5E2 | 5.9E-1 | 1.3E0 | 1.2E5 | 4.5E3 | 581 | 35 | 207 | 35 | 0.68 |
| Il | ng/ml | 3.4E2 | 3.8E2 | 1.3E3 | 1.3E3 | 2.7E3 | 2.9E3 | 1.0E-9 | 1.0E-9 | 1.2E4 | 1.2E4 | 574 | 32 | 207 | 32 | 0.50 |
| Im | ng/ml | 2.0E2 | 3.7E2 | 3.5E2 | 6.3E2 | 5.2E2 | 1.1E3 | 1.3E1 | 2.4E1 | 6.0E3 | 6.8E3 | 581 | 35 | 207 | 35 | 0.64 |
| In | ng/ml | 3.9E0 | 4.7E0 | 2.5E1 | 1.1E1 | 1.8E2 | 1.9E1 | 1.0E-9 | 1.0E-9 | 3.9E3 | 7.5E1 | 584 | 35 | 208 | 35 | 0.49 |
| Hb | ng/ml | 2.4E1 | 3.7E1 | 3.2E1 | 4.2E1 | 2.9E1 | 3.3E1 | 4.8E-1 | 1.5E0 | 1.4E2 | 1.1E2 | 217 | 22 | 134 | 22 | 0.59 |
| Hc | pg/ml | 7.6E2 | 5.8E2 | 4.0E3 | 2.4E3 | 1.4E4 | 3.6E3 | 1.0E-9 | 2.6E2 | 1.0E5 | 1.1E4 | 217 | 22 | 134 | 22 | 0.50 |
| Hf | ng/ml | 1.5E2 | 2.2E2 | 4.1E2 | 3.1E2 | 5.8E2 | 3.4E2 | 1.0E-9 | 1.0E-9 | 3.2E3 | 1.3E3 | 217 | 22 | 134 | 22 | 0.51 |
| Io | ng/ml | 8.4E3 | 8.5E3 | 2.7E4 | 5.1E4 | 1.8E5 | 1.3E5 | 1.0E-9 | 2.2E2 | 4.0E6 | 5.5E5 | 578 | 35 | 208 | 35 | 0.54 |
| Ip | ng/ml | 1.0E1 | 2.5E1 | 1.9E1 | 3.0E1 | 2.4E1 | 3.3E1 | 1.0E-9 | 1.2E-2 | 2.6E2 | 1.4E2 | 578 | 35 | 208 | 35 | 0.58 |
| Iq | ug/ml | 9.8E-2 | 3.0E-2 | 2.4E1 | 2.4E1 | 5.7E2 | 1.3E2 | 1.0E-9 | 1.0E-9 | 1.4E4 | 7.5E2 | 578 | 35 | 208 | 35 | 0.44 |
| Ir | ug/ml | 3.4E-1 | 7.7E-1 | 2.7E0 | 5.0E0 | 1.7E1 | 1.9E1 | 1.0E-9 | 1.0E-9 | 2.4E2 | 1.1E2 | 577 | 35 | 208 | 35 | 0.63 |
| Is | ng/ml | 1.5E0 | 1.9E0 | 5.4E0 | 1.4E1 | 1.1E1 | 4.0E1 | 1.0E-9 | 1.0E-9 | 8.8E1 | 2.3E2 | 578 | 35 | 208 | 35 | 0.59 |
| It | ng/ml | 1.9E0 | 3.9E0 | 2.2E1 | 2.6E1 | 1.5E2 | 1.0E2 | 1.0E-9 | 1.0E-9 | 2.8E3 | 5.9E2 | 578 | 35 | 208 | 35 | 0.59 |
| Iu | ng/ml | 2.2E2 | 2.6E2 | 1.3E3 | 2.5E3 | 4.0E3 | 6.8E3 | 1.0E-9 | 1.0E-9 | 2.9E4 | 2.4E4 | 578 | 35 | 208 | 35 | 0.52 |
| Iv | ng/ml | 1.4E1 | 3.0E1 | 4.1E1 | 2.5E2 | 1.0E2 | 1.1E3 | 1.0E-9 | 1.0E-9 | 1.6E3 | 6.4E3 | 577 | 35 | 208 | 35 | 0.63 |
| Iz | ng/ml | 1.5E2 | 2.1E2 | 7.3E2 | 3.6E2 | 4.3E3 | 4.2E2 | 1.5E0 | 9.2E-1 | 6.2E4 | 1.6E3 | 217 | 22 | 134 | 22 | 0.55 |
| Rc | pg/ml | 5.7E3 | 6.1E3 | 7.2E3 | 6.3E3 | 5.4E3 | 3.8E3 | 1.9E2 | 7.5E2 | 2.3E4 | 1.6E4 | 216 | 22 | 133 | 22 | 0.49 |
| Rb | pg/ml | 7.6E-1 | 1.9E0 | 2.7E0 | 4.0E0 | 4.5E0 | 5.4E0 | 1.0E-9 | 1.0E-9 | 4.3E1 | 2.1E1 | 216 | 22 | 133 | 22 | 0.62 |
| Pz | ng/ml | 3.7E3 | 1.0E4 | 7.4E3 | 9.6E3 | 1.9E4 | 1.6E4 | 1.3E1 | 1.5E2 | 2.8E5 | 9.5E4 | 577 | 35 | 206 | 35 | 0.60 |
| Qa | ng/ml | 3.2E3 | 6.6E3 | 6.1E3 | 8.5E3 | 7.4E3 | 6.8E3 | 1.5E2 | 3.8E2 | 5.2E4 | 2.4E4 | 577 | 35 | 206 | 35 | 0.64 |
| Qb | ng/ml | 9.9E1 | 1.3E2 | 2.2E2 | 2.2E2 | 5.2E2 | 2.0E2 | 7.9E-1 | 1.0E1 | 8.3E3 | 6.0E2 | 577 | 35 | 206 | 35 | 0.57 |
| Qc | ng/ml | 2.5E2 | 3.2E2 | 4.7E2 | 4.3E2 | 8.0E2 | 4.3E2 | 1.0E-9 | 6.8E0 | 1.1E4 | 1.6E3 | 577 | 35 | 206 | 35 | 0.53 |
| Qd | ng/ml | 1.0E4 | 1.3E4 | 2.3E4 | 2.3E4 | 9.4E4 | 2.5E4 | 2.4E2 | 9.0E2 | 2.0E6 | 1.2E5 | 577 | 35 | 206 | 35 | 0.59 |
| Qe | ng/ml | 8.8E2 | 1.7E3 | 1.9E3 | 2.7E3 | 4.6E3 | 2.7E3 | 7.6E0 | 8.2E1 | 9.7E4 | 1.4E4 | 577 | 35 | 206 | 35 | 0.67 |
| Jd | ng/ml | 9.6E-1 | 1.1E0 | 7.2E0 | 3.8E0 | 4.7E1 | 7.7E0 | 1.0E-9 | 1.0E-9 | 6.5E2 | 3.3E1 | 217 | 22 | 135 | 22 | 0.55 |
| Je | ng/ml | 1.0E-9 | 3.9E-1 | 2.5E0 | 1.7E0 | 8.5E0 | 2.8E0 | 1.0E-9 | 1.0E-9 | 8.8E1 | 1.1E1 | 217 | 22 | 135 | 22 | 0.55 |
| Jf | ng/ml | 1.0E-9 | 7.4E-1 | 1.2E0 | 1.7E0 | 2.4E0 | 2.5E0 | 1.0E-9 | 1.0E-9 | 1.2E1 | 9.2E0 | 217 | 22 | 135 | 22 | 0.64 |
| Jg | ng/ml | 4.7E2 | 1.1E3 | 7.6E2 | 1.6E3 | 9.6E2 | 1.6E3 | 1.0E-9 | 2.1E1 | 1.0E4 | 6.8E3 | 581 | 35 | 208 | 35 | 0.69 |

Figure 11 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jh | ng/ml | 3.1E0 | 6.7E0 | 2.6E1 | 4.2E1 | 1.1E2 | 9.6E1 | 1.0E-9 | 1.0E-9 | 1.6E3 | 4.7E2 | 581 | 35 | 208 | 35 | 0.60 |
| Ji | ng/ml | 5.0E1 | 7.4E1 | 7.1E1 | 1.7E2 | 7.0E1 | 3.1E2 | 1.0E-9 | 1.0E-9 | 5.3E2 | 1.8E3 | 581 | 35 | 208 | 35 | 0.67 |
| Sr | pg/mL | 3.5E2 | 7.0E2 | 8.5E2 | 1.2E3 | 1.3E3 | 1.1E3 | 1.0E-9 | 1.9E1 | 9.8E3 | 4.1E3 | 207 | 22 | 130 | 22 | 0.64 |
| Ss | pg/mL | 1.2E5 | 1.0E5 | 1.6E5 | 1.3E5 | 2.0E5 | 1.1E5 | 2.7E3 | 1.4E4 | 1.8E6 | 4.7E5 | 207 | 22 | 130 | 22 | 0.50 |
| St | pg/mL | 2.5E7 | 5.1E7 | 5.5E7 | 8.6E7 | 9.9E7 | 1.1E8 | 1.0E-9 | 1.5E6 | 1.2E9 | 4.2E8 | 212 | 22 | 131 | 22 | 0.61 |
| Ra | pg/ml | 1.0E-9 | 1.0E-9 | 6.4E-1 | 6.5E-1 | 1.3E0 | 1.2E0 | 1.0E-9 | 1.0E-9 | 7.3E0 | 4.1E0 | 216 | 22 | 133 | 22 | 0.56 |
| Qz | pg/ml | 1.0E1 | 2.0E1 | 6.0E1 | 5.4E1 | 1.0E2 | 6.7E1 | 1.0E-9 | 1.0E-9 | 7.1E2 | 2.0E2 | 216 | 22 | 133 | 22 | 0.49 |
| Qy | pg/ml | 4.6E-1 | 5.0E-1 | 1.5E1 | 2.5E1 | 7.2E1 | 1.1E2 | 1.0E-9 | 1.1E-2 | 6.5E2 | 5.1E2 | 216 | 22 | 133 | 22 | 0.54 |
| Qx | pg/ml | 1.0E-9 | 1.0E-9 | 7.6E0 | 1.2E0 | 5.5E1 | 2.3E0 | 1.0E-9 | 1.0E-9 | 5.8E2 | 7.3E0 | 216 | 22 | 133 | 22 | 0.57 |
| Qw | pg/ml | 4.5E-2 | 1.0E-9 | 2.2E0 | 2.8E-1 | 8.8E0 | 7.2E-1 | 1.0E-9 | 1.0E-9 | 8.6E1 | 2.4E0 | 216 | 22 | 133 | 22 | 0.36 |
| Qv | pg/ml | 2.2E4 | 1.9E4 | 3.5E4 | 3.1E4 | 6.4E4 | 3.3E4 | 1.0E-9 | 6.0E1 | 7.4E5 | 1.4E5 | 216 | 22 | 133 | 22 | 0.48 |
| Qu | pg/ml | 1.2E1 | 1.7E1 | 8.9E1 | 9.1E1 | 1.7E2 | 2.0E2 | 1.0E-9 | 1.0E-9 | 9.8E2 | 9.2E2 | 216 | 22 | 133 | 22 | 0.52 |
| Qt | pg/ml | 1.2E1 | 5.9E-1 | 5.7E1 | 2.7E1 | 1.4E2 | 5.5E1 | 1.0E-9 | 1.0E-9 | 1.0E3 | 1.9E2 | 216 | 22 | 133 | 22 | 0.41 |
| Qh | ng/ml | 1.7E1 | 1.5E1 | 3.7E1 | 2.9E1 | 6.3E1 | 2.9E1 | 1.0E-9 | 3.9E0 | 6.4E2 | 1.1E2 | 216 | 22 | 133 | 22 | 0.52 |
| Qg | ng/ml | 7.9E0 | 6.5E0 | 2.0E1 | 1.0E1 | 7.5E1 | 9.9E1 | 5.1E-2 | 1.4E-1 | 1.0E3 | 4.2E1 | 216 | 22 | 133 | 22 | 0.46 |
| Jj | ng/ml | 7.5E2 | 3.0E2 | 2.2E3 | 9.1E2 | 1.5E4 | 1.9E3 | 1.7E1 | 1.7E1 | 3.4E5 | 1.1E4 | 581 | 35 | 208 | 35 | 0.34 |
| Jk | ng/ml | 3.3E0 | 3.9E0 | 2.4E1 | 3.0E1 | 4.9E1 | 7.0E1 | 1.0E-9 | 1.0E-1 | 3.9E2 | 3.5E2 | 581 | 35 | 208 | 35 | 0.51 |
| Jl | ng/ml | 4.4E-1 | 8.5E-1 | 1.8E0 | 6.8E0 | 4.3E0 | 2.6E1 | 7.6E-4 | 2.9E-3 | 3.2E1 | 1.6E2 | 581 | 35 | 208 | 35 | 0.58 |
| Jm | ng/ml | 1.9E1 | 3.2E1 | 5.2E1 | 5.5E1 | 9.7E1 | 6.5E1 | 1.0E-9 | 8.3E-1 | 1.0E3 | 2.3E2 | 581 | 35 | 208 | 35 | 0.57 |
| Jn | pg/ml | 4.0E-1 | 7.6E-1 | 1.7E0 | 2.4E0 | 5.8E0 | 4.9E0 | 1.0E-9 | 1.0E-9 | 6.2E1 | 2.7E1 | 581 | 35 | 208 | 35 | 0.60 |
| Jo | pg/ml | 4.0E3 | 4.8E3 | 5.1E3 | 5.6E3 | 3.9E3 | 6.2E3 | 4.2E1 | 4.9E1 | 2.4E4 | 3.8E4 | 581 | 35 | 208 | 35 | 0.51 |
| Jp | pg/ml | 7.0E4 | 1.0E5 | 7.3E4 | 9.5E4 | 3.4E4 | 3.9E4 | 2.1E3 | 3.5E3 | 2.1E5 | 1.7E5 | 581 | 35 | 208 | 35 | 0.68 |
| Jq | pg/ml | 9.5E1 | 1.1E2 | 1.5E2 | 5.5E2 | 2.2E2 | 6.1E2 | 2.6E0 | 8.1E0 | 4.0E3 | 3.7E3 | 581 | 35 | 208 | 35 | 0.52 |
| Jr | pg/ml | 5.2E0 | 5.6E0 | 2.2E1 | 2.0E1 | 1.0E2 | 4.6E1 | 1.0E-9 | 1.0E-9 | 1.9E3 | 2.0E2 | 581 | 35 | 208 | 35 | 0.56 |
| Js | pg/ml | 1.3E1 | 1.6E1 | 4.2E1 | 3.6E1 | 1.5E2 | 9.8E1 | 1.0E-9 | 1.0E-9 | 2.0E3 | 5.9E2 | 581 | 35 | 208 | 35 | 0.56 |
| Jt | pg/ml | 2.7E3 | 3.8E3 | 3.2E3 | 4.6E3 | 2.2E3 | 5.4E3 | 1.5E2 | 7.7E1 | 1.3E4 | 3.3E4 | 581 | 35 | 208 | 35 | 0.59 |
| Ju | mIU/ml | 9.0E0 | 9.6E0 | 2.1E1 | 1.4E1 | 3.3E1 | 1.3E1 | 6.5E-2 | 6.5E-1 | 2.3E2 | 4.9E1 | 217 | 22 | 135 | 22 | 0.53 |
| Jv | mIU/ml | 1.2E1 | 1.3E1 | 3.7E1 | 2.3E1 | 6.6E1 | 2.3E1 | 1.0E-2 | 1.8E-1 | 4.4E2 | 9.1E1 | 217 | 22 | 135 | 22 | 0.52 |
| Jy | ng/ml | 1.6E-3 | 1.5E-3 | 2.3E-3 | 1.8E-3 | 4.6E-3 | 1.3E-3 | 1.7E-4 | 8.7E-5 | 5.2E-2 | 6.4E-3 | 217 | 22 | 135 | 22 | 0.47 |
| Kc | pg/ml | 2.3E1 | 5.7E1 | 4.0E1 | 7.8E1 | 4.3E1 | 6.9E1 | 1.0E-9 | 1.0E-9 | 1.9E2 | 2.0E2 | 218 | 22 | 134 | 22 | 0.62 |
| Kd | pg/ml | 1.0E-9 | 1.0E-9 | 2.0E2 | 3.7E2 | 6.0E2 | 6.9E2 | 1.0E-9 | 1.0E-9 | 4.8E3 | 2.3E3 | 218 | 22 | 134 | 22 | 0.57 |
| Ke | pg/ml | 1.3E4 | 1.6E4 | 1.4E4 | 1.6E4 | 1.1E4 | 7.7E3 | 3.4E2 | 1.1E3 | 7.0E4 | 3.6E4 | 218 | 22 | 134 | 22 | 0.59 |
| Kf | pg/mL | 6.7E0 | 9.4E0 | 7.3E0 | 9.2E0 | 5.9E0 | 5.0E0 | 1.0E-9 | 1.0E-9 | 2.7E1 | 1.8E1 | 218 | 22 | 134 | 22 | 0.63 |
| Kg | pg/ml | 1.2E3 | 1.4E3 | 2.0E3 | 1.6E3 | 2.4E3 | 1.3E3 | 7.3E1 | 1.3E2 | 1.7E4 | 4.4E3 | 218 | 22 | 134 | 22 | 0.50 |
| Ki | pg/ml | 5.9E1 | 5.2E1 | 7.0E1 | 5.7E1 | 5.5E1 | 3.7E1 | 1.0E-9 | 1.0E-9 | 3.8E2 | 1.4E2 | 217 | 22 | 134 | 22 | 0.44 |
| Kj | pg/ml | 1.1E3 | 1.2E3 | 1.7E3 | 1.5E3 | 1.7E3 | 1.3E3 | 1.4E1 | 3.0E1 | 1.0E4 | 4.5E3 | 218 | 22 | 134 | 22 | 0.47 |
| Kk | pg/ml | 6.8E0 | 9.0E0 | 1.1E1 | 2.0E1 | 1.6E1 | 2.0E1 | 1.0E-9 | 1.0E-9 | 1.6E2 | 6.1E1 | 218 | 22 | 134 | 22 | 0.66 |
| Kl | pg/ml | 2.1E4 | 3.3E4 | 2.9E4 | 3.3E4 | 2.6E4 | 2.4E4 | 1.6E2 | 1.4E3 | 1.6E5 | 1.0E5 | 218 | 22 | 134 | 22 | 0.56 |
| Kn | pg/ml | 3.0E1 | 5.5E1 | 6.2E1 | 8.5E1 | 9.5E1 | 1.1E2 | 1.0E-9 | 1.0E-9 | 7.3E2 | 4.1E2 | 218 | 22 | 134 | 22 | 0.55 |
| Ko | pg/ml | 3.4E2 | 7.4E2 | 4.6E2 | 8.1E2 | 4.5E2 | 5.9E2 | 1.0E-9 | 4.2E1 | 2.2E3 | 2.4E3 | 218 | 22 | 134 | 22 | 0.70 |
| Kp | pg/ml | 3.4E2 | 3.3E2 | 3.5E2 | 4.2E2 | 2.7E2 | 2.4E2 | 1.0E-9 | 6.4E1 | 1.7E3 | 9.1E2 | 218 | 22 | 134 | 22 | 0.57 |
| Kq | pg/ml | 3.2E2 | 4.7E2 | 5.1E2 | 5.0E2 | 9.1E2 | 2.4E2 | 1.6E0 | 2.5E1 | 9.8E3 | 8.7E2 | 209 | 22 | 128 | 22 | 0.65 |
| Kr | pg/ml | 5.6E-1 | 9.0E-1 | 2.7E0 | 2.6E0 | 5.2E0 | 3.3E0 | 1.0E-9 | 1.0E-9 | 3.9E1 | 9.6E0 | 209 | 22 | 128 | 22 | 0.53 |
| Ks | pg/ml | 1.4E4 | 1.5E4 | 2.1E4 | 2.0E4 | 1.9E4 | 1.7E4 | 5.1E1 | 2.2E2 | 1.1E5 | 5.0E4 | 209 | 22 | 128 | 22 | 0.51 |
| Kx | ng/ml | 1.0E-9 | 1.0E-9 | 7.1E-3 | 5.1E-3 | 1.4E-2 | 6.2E-3 | 1.0E-9 | 1.0E-9 | 1.0E-1 | 1.5E-2 | 214 | 22 | 133 | 22 | 0.50 |
| Ky | ng/ml | 1.0E-1 | 1.1E-1 | 3.8E-1 | 7.2E-1 | 8.3E-1 | 1.4E0 | 1.0E-9 | 1.0E-9 | 5.4E0 | 6.3E0 | 214 | 22 | 133 | 22 | 0.59 |
| Kz | ng/ml | 1.0E-9 | 1.0E-9 | 3.4E-3 | 1.7E-3 | 5.7E-3 | 2.4E-3 | 1.0E-9 | 1.0E-9 | 3.6E-2 | 6.6E-3 | 214 | 22 | 133 | 22 | 0.47 |
| Ld | pg/ml | 1.0E-9 | 3.7E-1 | 3.7E0 | 2.6E0 | 9.6E0 | 3.8E0 | 1.0E-9 | 1.0E-9 | 8.4E1 | 1.2E1 | 216 | 22 | 133 | 22 | 0.53 |
| Lh | pg/ml | 1.3E4 | 2.2E4 | 2.1E4 | 4.1E4 | 2.7E4 | 7.3E4 | 1.0E-9 | 1.8E2 | 2.6E5 | 4.1E5 | 580 | 35 | 209 | 35 | 0.64 |
| Li | pg/ml | 3.1E3 | 6.6E3 | 1.5E4 | 4.2E4 | 3.9E4 | 1.0E5 | 1.0E-9 | 1.6E1 | 3.6E5 | 5.9E5 | 580 | 35 | 209 | 35 | 0.66 |
| Lj | pg/ml | 2.4E3 | 8.0E3 | 2.1E4 | 3.6E4 | 6.5E4 | 7.4E4 | 1.0E-9 | 2.9E1 | 4.7E5 | 3.5E5 | 580 | 35 | 209 | 35 | 0.65 |
| Rm | ng/ml | 1.9E1 | 3.7E1 | 5.1E1 | 4.4E1 | 7.7E1 | 5.5E1 | 2.2E-1 | 7.0E-1 | 4.0E2 | 2.5E2 | 213 | 21 | 132 | 21 | 0.54 |
| Rh | ng/ml | 1.3E2 | 1.6E2 | 2.8E2 | 3.1E2 | 5.0E2 | 5.2E2 | 4.7E0 | 1.4E1 | 3.8E3 | 2.5E3 | 213 | 21 | 132 | 21 | 0.58 |
| Ri | ng/ml | 1.0E-9 | 1.3E0 | 4.3E0 | 3.1E0 | 1.7E1 | 4.6E0 | 1.0E-9 | 1.0E-9 | 2.2E2 | 2.0E1 | 214 | 21 | 133 | 21 | 0.59 |
| Rg | ng/ml | 1.0E-9 | 1.0E-9 | 6.8E-2 | 2.1E-3 | 3.9E-1 | 5.1E-3 | 1.0E-9 | 1.0E-9 | 3.3E0 | 2.2E-2 | 213 | 21 | 132 | 21 | 0.53 |
| Rj | ng/ml | 1.0E-9 | 1.0E-9 | 1.6E0 | 3.0E-1 | 6.3E0 | 8.1E-1 | 1.0E-9 | 1.0E-9 | 8.0E1 | 3.2E0 | 214 | 21 | 133 | 21 | 0.44 |
| Rf | ng/ml | 3.7E-1 | 6.0E-1 | 1.0E0 | 1.6E0 | 1.9E0 | 2.2E0 | 7.8E-3 | 3.8E-2 | 1.5E1 | 7.5E0 | 213 | 21 | 132 | 21 | 0.63 |

Figure 11 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ql | pg/ml | 5.5E0 | 4.5E0 | 1.5E1 | 1.1E1 | 3.2E1 | 1.5E1 | 1.0E-9 | 1.0E-9 | 2.9E2 | 5.9E1 | 217 | 22 | 135 | 22 | 0.51 |
| Qm | pg/ml | 4.4E0 | 1.4E1 | 2.0E1 | 1.9E1 | 4.0E1 | 1.9E1 | 1.0E-9 | 1.0E-9 | 3.6E2 | 5.9E1 | 217 | 22 | 135 | 22 | 0.56 |
| Qn | pg/ml | 6.1E-1 | 5.6E-1 | 5.8E0 | 6.5E0 | 1.9E1 | 2.2E1 | 1.0E-9 | 1.0E-9 | 2.2E2 | 1.0E2 | 217 | 22 | 135 | 22 | 0.44 |
| Nv | pg/ml | 4.0E3 | 7.9E3 | 1.2E4 | 1.8E4 | 5.2E4 | 2.9E4 | 1.0E-9 | 3.9E1 | 1.1E6 | 1.3E5 | 585 | 35 | 209 | 35 | 0.66 |
| Nw | pg/ml | 8.5E3 | 1.7E4 | 1.3E4 | 2.7E4 | 1.8E4 | 3.9E4 | 8.6E1 | 7.3E2 | 2.1E5 | 2.1E5 | 585 | 35 | 209 | 35 | 0.74 |
| Nx | pg/ml | 2.2E2 | 5.2E2 | 4.1E2 | 8.2E2 | 6.9E2 | 8.1E2 | 1.0E-9 | 1.0E-9 | 7.4E3 | 2.8E3 | 585 | 35 | 209 | 35 | 0.69 |
| Ny | pg/ml | 5.7E0 | 1.6E1 | 7.2E1 | 4.1E1 | 1.0E3 | 1.1E2 | 1.0E-9 | 1.0E-9 | 2.5E4 | 6.2E2 | 585 | 35 | 209 | 35 | 0.64 |
| Oa | pg/ml | 1.6E2 | 3.0E2 | 4.1E2 | 5.1E2 | 7.0E2 | 5.8E2 | 1.0E-9 | 1.0E-9 | 4.8E3 | 2.4E3 | 217 | 22 | 135 | 22 | 0.61 |
| Oe | pg/ml | 9.1E1 | 3.5E1 | 3.1E2 | 3.0E2 | 8.7E2 | 8.9E2 | 1.0E-9 | 1.0E-9 | 1.9E4 | 5.1E3 | 580 | 35 | 209 | 35 | 0.45 |
| Of | pg/ml | 2.3E2 | 3.2E2 | 7.1E3 | 5.4E3 | 3.3E4 | 1.7E4 | 1.0E-9 | 1.0E-9 | 6.2E5 | 7.4E4 | 585 | 35 | 209 | 35 | 0.51 |
| Og | pg/ml | 9.2E-2 | 9.0E-2 | 9.9E-1 | 4.1E-1 | 5.8E0 | 1.5E0 | 1.0E-9 | 1.0E-9 | 8.3E1 | 9.0E0 | 585 | 35 | 209 | 35 | 0.44 |
| Oh | pg/ml | 2.4E0 | 3.4E0 | 2.5E1 | 2.0E1 | 1.7E2 | 4.9E1 | 1.0E-9 | 1.0E-9 | 3.5E3 | 2.2E2 | 585 | 35 | 209 | 35 | 0.60 |
| Oi | pg/ml | 2.8E0 | 5.6E0 | 6.5E0 | 1.0E1 | 1.0E1 | 1.2E1 | 1.0E-9 | 1.0E-9 | 8.6E1 | 4.2E1 | 585 | 35 | 209 | 35 | 0.57 |
| Ok | pg/ml | 3.9E2 | 8.2E2 | 5.2E2 | 3.2E3 | 5.0E2 | 1.2E4 | 1.3E1 | 2.2E1 | 5.2E3 | 7.0E4 | 585 | 35 | 209 | 35 | 0.73 |
| Om | pg/ml | 3.8E2 | 6.8E2 | 9.0E2 | 1.7E3 | 2.5E3 | 3.5E3 | 1.0E-9 | 1.0E-9 | 3.6E4 | 1.7E4 | 585 | 35 | 209 | 35 | 0.60 |
| On | pg/ml | 1.8E2 | 3.7E2 | 2.9E2 | 1.1E3 | 4.3E2 | 2.9E3 | 8.4E-1 | 6.1E0 | 4.5E3 | 1.5E4 | 585 | 35 | 209 | 35 | 0.68 |
| Or | pg/ml | 1.4E1 | 1.7E1 | 3.4E1 | 5.7E1 | 6.3E1 | 1.6E2 | 1.0E-9 | 1.0E-9 | 5.0E2 | 7.6E2 | 218 | 22 | 134 | 22 | 0.54 |
| Ow | pg/ml | 3.3E1 | 2.6E1 | 1.1E2 | 1.3E2 | 3.1E2 | 2.3E2 | 1.0E-9 | 1.0E-9 | 2.7E3 | 7.9E2 | 218 | 22 | 134 | 22 | 0.54 |
| Ou | pg/ml | 4.7E2 | 7.2E2 | 8.8E2 | 2.1E3 | 1.3E3 | 3.1E3 | 1.0E-9 | 1.0E-9 | 9.8E3 | 9.3E3 | 218 | 22 | 134 | 22 | 0.57 |
| Ul | ng/ml | 1.0E-9 | 1.0E-9 | 1.4E0 | 5.2E0 | 4.7E0 | 2.2E1 | 1.0E-9 | 1.0E-9 | 3.4E1 | 1.0E2 | 224 | 22 | 137 | 22 | 0.51 |
| Uo | ng/ml | 1.0E-9 | 1.0E-9 | 1.1E-1 | 1.6E-1 | 2.7E-1 | 3.5E-1 | 1.0E-9 | 1.0E-9 | 2.6E0 | 1.5E0 | 224 | 22 | 137 | 22 | 0.52 |
| Uk | ng/ml | 1.0E-9 | 1.0E-9 | 8.7E-3 | 5.4E-3 | 2.9E-2 | 1.2E-2 | 1.0E-9 | 1.0E-9 | 3.2E-1 | 4.2E-2 | 224 | 22 | 137 | 22 | 0.42 |
| Um | ng/ml | 1.0E-9 | 1.0E-9 | 4.2E-1 | 3.5E-1 | 1.0E0 | 9.7E-1 | 1.0E-9 | 1.0E-9 | 7.2E0 | 4.4E0 | 224 | 22 | 137 | 22 | 0.45 |
| Uf | ng/ml | 5.3E-2 | 9.7E-2 | 1.5E-1 | 2.3E-1 | 2.7E-1 | 5.1E-1 | 1.0E-3 | 1.3E-3 | 2.1E0 | 2.5E0 | 224 | 22 | 137 | 22 | 0.59 |
| Uh | ng/ml | 1.9E0 | 3.3E0 | 2.9E0 | 3.9E0 | 3.1E0 | 3.0E0 | 3.2E-2 | 2.3E-1 | 1.7E1 | 1.2E1 | 224 | 22 | 137 | 22 | 0.64 |
| Un | ng/ml | 1.9E0 | 2.1E0 | 2.1E0 | 2.4E0 | 1.3E0 | 1.4E0 | 2.0E-1 | 1.8E-1 | 8.0E0 | 6.4E0 | 224 | 22 | 137 | 22 | 0.56 |
| Ug | ng/ml | 1.4E1 | 1.9E1 | 2.8E1 | 3.5E1 | 2.9E1 | 4.7E1 | 6.9E-1 | 1.1E0 | 1.8E2 | 2.1E2 | 224 | 22 | 137 | 22 | 0.51 |
| Ur | ng/ml | 1.5E-1 | 1.2E-1 | 8.5E-1 | 8.4E-1 | 6.3E0 | 1.9E0 | 1.0E-9 | 1.0E-9 | 9.3E1 | 7.2E0 | 223 | 22 | 136 | 22 | 0.46 |
| Up | ng/ml | 1.0E-9 | 1.0E-9 | 6.0E-3 | 2.1E-3 | 2.6E-2 | 6.6E-3 | 1.0E-9 | 1.0E-9 | 3.3E-1 | 2.5E-2 | 223 | 22 | 136 | 22 | 0.44 |
| Us | ng/ml | 4.3E-3 | 4.5E-3 | 1.9E-2 | 1.8E-2 | 4.6E-2 | 4.5E-2 | 1.0E-9 | 1.0E-9 | 4.0E-1 | 2.1E-1 | 223 | 22 | 136 | 22 | 0.49 |
| Uv | ng/ml | 3.2E-3 | 2.5E-3 | 1.3E-2 | 1.0E-2 | 3.9E-2 | 3.0E-2 | 1.0E-9 | 1.0E-9 | 4.3E-1 | 1.4E-1 | 223 | 22 | 136 | 22 | 0.46 |
| Ut | ng/ml | 7.6E-1 | 9.1E-1 | 3.2E0 | 1.1E0 | 9.7E0 | 1.3E0 | 1.0E-9 | 1.0E-9 | 7.8E1 | 5.3E0 | 223 | 22 | 136 | 22 | 0.47 |
| Uu | ng/ml | 7.2E0 | 8.8E0 | 7.8E0 | 8.9E0 | 4.8E0 | 6.3E0 | 5.7E-1 | 5.5E-1 | 2.6E1 | 2.2E1 | 223 | 22 | 136 | 22 | 0.54 |
| Vp | ng/ml | 1.0E-9 | 1.0E-9 | 4.6E-1 | 4.9E-3 | 3.8E0 | 2.3E-2 | 1.0E-9 | 1.0E-9 | 5.0E1 | 1.1E-1 | 224 | 22 | 137 | 22 | 0.44 |
| Vt | ng/ml | 6.1E0 | 7.9E0 | 8.3E0 | 1.1E1 | 9.3E0 | 9.3E0 | 4.3E-1 | 7.7E-1 | 8.6E1 | 3.4E1 | 224 | 22 | 137 | 22 | 0.62 |
| Vu | ng/ml | 1.0E-9 | 1.0E-9 | 2.9E0 | 9.0E-1 | 7.5E0 | 1.7E0 | 1.0E-9 | 1.0E-9 | 7.1E1 | 6.2E0 | 219 | 21 | 137 | 21 | 0.45 |
| Vq | ng/ml | 1.5E2 | 6.0E2 | 6.3E2 | 1.2E3 | 1.4E3 | 1.6E3 | 2.0E-1 | 7.9E0 | 1.1E4 | 5.4E3 | 175 | 16 | 115 | 16 | 0.63 |
| Vo | ng/ml | 2.6E1 | 2.5E1 | 2.5E1 | 2.3E1 | 5.1E0 | 6.1E0 | 2.5E0 | 6.7E0 | 4.8E1 | 3.1E1 | 224 | 22 | 137 | 22 | 0.43 |
| Vs | ng/ml | 2.6E-1 | 1.0E-9 | 7.3E0 | 2.5E0 | 2.6E1 | 5.2E0 | 1.0E-9 | 1.0E-9 | 2.3E2 | 1.9E1 | 218 | 21 | 135 | 21 | 0.41 |
| Vv | ng/ml | 3.3E0 | 4.8E0 | 6.3E0 | 9.3E0 | 1.0E1 | 1.7E1 | 1.0E-9 | 1.0E-9 | 8.4E1 | 8.0E1 | 223 | 22 | 137 | 22 | 0.56 |
| Oy | pg/ml | 5.5E-1 | 5.8E-1 | 7.3E0 | 9.1E0 | 3.5E1 | 4.6E1 | 1.0E-9 | 1.0E-9 | 4.0E2 | 2.7E2 | 584 | 35 | 208 | 35 | 0.52 |
| Oz | pg/ml | 1.3E-2 | 2.4E-1 | 3.5E-1 | 3.1E-1 | 1.6E0 | 3.1E-1 | 1.0E-9 | 1.0E-9 | 2.9E1 | 1.0E0 | 584 | 35 | 208 | 35 | 0.61 |
| Pa | pg/ml | 3.9E-1 | 3.8E-1 | 1.5E0 | 9.8E0 | 5.8E0 | 4.9E1 | 1.0E-9 | 2.6E-2 | 8.6E1 | 2.9E2 | 584 | 35 | 208 | 35 | 0.56 |
| Pb | pg/ml | 1.0E-9 | 8.2E-2 | 1.1E0 | 5.3E0 | 2.0E1 | 3.0E1 | 1.0E-9 | 1.0E-9 | 4.9E2 | 1.8E2 | 584 | 35 | 208 | 35 | 0.59 |
| Pc | pg/ml | 4.9E-2 | 3.5E-1 | 3.8E-1 | 8.8E-1 | 1.0E0 | 2.1E0 | 1.0E-9 | 1.0E-9 | 1.6E1 | 1.1E1 | 584 | 35 | 208 | 35 | 0.59 |
| Pd | pg/ml | 1.8E0 | 3.0E0 | 5.5E0 | 5.1E0 | 3.6E1 | 5.3E0 | 1.0E-9 | 1.0E-9 | 8.4E2 | 1.9E1 | 584 | 35 | 208 | 35 | 0.61 |
| Pe | pg/ml | 2.1E1 | 3.6E1 | 1.1E2 | 5.3E2 | 3.7E2 | 2.4E3 | 1.0E-9 | 3.7E-1 | 4.7E3 | 1.4E4 | 584 | 35 | 208 | 35 | 0.64 |
| Pf | pg/ml | 1.5E0 | 2.5E0 | 1.1E1 | 1.6E1 | 6.6E1 | 4.2E1 | 1.0E-9 | 1.0E-9 | 1.5E3 | 2.3E2 | 584 | 35 | 208 | 35 | 0.60 |
| Pg | pg/ml | 3.3E0 | 6.2E0 | 5.4E1 | 7.6E1 | 4.2E2 | 3.2E2 | 1.0E-9 | 1.3E-1 | 7.7E3 | 1.9E3 | 584 | 35 | 208 | 35 | 0.61 |
| Ph | ng/ml | 1.6E-1 | 2.3E-1 | 3.3E-1 | 7.1E-1 | 4.9E-1 | 1.1E0 | 1.0E-9 | 1.0E-9 | 3.1E0 | 4.4E0 | 218 | 22 | 134 | 22 | 0.57 |
| Pi | ng/ml | 1.9E-1 | 2.2E-1 | 2.8E-1 | 2.5E-1 | 3.7E-1 | 2.3E-1 | 1.0E-9 | 1.0E-9 | 3.2E0 | 1.0E0 | 218 | 22 | 134 | 22 | 0.52 |
| Pj | ng/mL | 5.2E0 | 8.1E0 | 6.1E0 | 8.5E0 | 4.7E0 | 5.0E0 | 3.8E-2 | 1.6E-1 | 3.1E1 | 1.7E1 | 218 | 22 | 134 | 22 | 0.66 |
| Pk | ng/ml | 8.9E-3 | 1.1E-2 | 1.4E-2 | 1.2E-2 | 2.2E-2 | 1.1E-2 | 1.0E-9 | 1.0E-9 | 2.5E-1 | 3.8E-2 | 218 | 22 | 134 | 22 | 0.51 |
| aA | mg/dL | 8.0E-1 | 1.0E0 | 9.1E-1 | 1.3E0 | 4.4E-1 | 9.1E-1 | 2.0E-1 | 4.0E-1 | 4.2E0 | 5.4E0 | 1815 | 49 | 323 | 49 | 0.64 |
| aC | mg/mL | 2.8E0 | 2.5E0 | 3.1E0 | 2.9E0 | 1.3E0 | 1.3E0 | 8.5E-1 | 1.3E0 | 8.2E0 | 6.3E0 | 363 | 26 | 141 | 26 | 0.46 |
| aD | ug/mL | 3.1E0 | 4.8E0 | 4.3E0 | 5.3E0 | 3.5E0 | 3.8E0 | 8.5E-1 | 8.4E-1 | 3.1E1 | 1.7E1 | 363 | 26 | 141 | 26 | 0.57 |
| aE | mg/mL | 5.7E-1 | 5.6E-1 | 5.8E-1 | 5.7E-1 | 1.5E-1 | 1.6E-1 | 2.1E-1 | 2.8E-1 | 1.1E0 | 1.2E0 | 363 | 26 | 141 | 26 | 0.47 |

Figure 11 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aF | ng/mL | 2.1E0 | 2.6E0 | 4.1E0 | 4.1E0 | 6.1E0 | 4.3E0 | 4.3E-3 | 4.3E-3 | 5.0E1 | 1.5E1 | 363 | 26 | 141 | 26 | 0.53 |
| aG | mg/mL | 1.4E-1 | 1.4E-1 | 1.6E-1 | 1.6E-1 | 8.4E-2 | 1.0E-1 | 5.0E-2 | 6.6E-2 | 5.0E-1 | 5.2E-1 | 363 | 26 | 141 | 26 | 0.47 |
| aH | ug/mL | 7.5E1 | 8.2E1 | 8.1E1 | 9.1E1 | 4.2E1 | 5.0E1 | 9.6E0 | 2.5E1 | 2.9E2 | 2.3E2 | 363 | 26 | 141 | 26 | 0.56 |
| aI | ug/mL | 1.9E2 | 1.9E2 | 1.9E2 | 1.9E2 | 6.0E1 | 4.6E1 | 4.7E1 | 1.2E2 | 3.7E2 | 2.7E2 | 363 | 26 | 141 | 26 | 0.52 |
| aJ | ug/mL | 2.4E0 | 3.8E0 | 3.0E0 | 4.8E0 | 2.2E0 | 3.9E0 | 9.0E-1 | 7.8E-1 | 1.7E1 | 1.7E1 | 363 | 26 | 141 | 26 | 0.69 |
| aK | ng/mL | 1.6E0 | 8.9E-1 | 2.5E0 | 1.7E0 | 2.7E0 | 1.8E0 | 2.9E-4 | 8.8E-2 | 1.8E1 | 7.4E0 | 363 | 26 | 141 | 26 | 0.40 |
| aL | mg/mL | 7.9E-1 | 8.5E-1 | 8.0E-1 | 8.3E-1 | 2.4E-1 | 2.5E-1 | 2.2E-1 | 4.0E-1 | 1.7E0 | 1.6E0 | 363 | 26 | 141 | 26 | 0.53 |
| aM | U/mL | 2.2E1 | 3.3E1 | 4.4E1 | 5.9E1 | 1.0E2 | 8.0E1 | 4.2E-2 | 4.2E-2 | 1.6E3 | 4.0E2 | 363 | 26 | 141 | 26 | 0.60 |
| aN | U/mL | 1.4E1 | 2.5E1 | 2.1E1 | 2.9E1 | 3.0E1 | 2.5E1 | 2.5E-3 | 2.5E-3 | 3.8E2 | 9.7E1 | 363 | 26 | 141 | 26 | 0.64 |
| aO | pg/mL | 3.5E1 | 4.8E1 | 3.4E2 | 4.6E2 | 8.8E2 | 8.3E2 | 6.0E-2 | 6.0E-2 | 6.6E3 | 3.5E3 | 363 | 26 | 141 | 26 | 0.57 |
| aP | ng/mL | 1.6E0 | 2.0E0 | 2.0E0 | 2.7E0 | 1.2E0 | 2.2E0 | 5.4E-1 | 7.2E-1 | 7.0E0 | 1.1E1 | 363 | 26 | 141 | 26 | 0.62 |
| aQ | ng/mL | 3.0E-1 | 2.2E-1 | 4.6E-1 | 3.6E-1 | 4.9E-1 | 3.8E-1 | 2.0E-4 | 3.9E-2 | 4.0E0 | 1.7E0 | 363 | 26 | 141 | 26 | 0.41 |
| aR | ng/mL | 1.8E0 | 2.3E0 | 2.9E0 | 2.9E0 | 3.5E0 | 2.8E0 | 1.8E-1 | 4.9E-1 | 3.4E1 | 1.4E1 | 363 | 26 | 141 | 26 | 0.54 |
| aS | ng/mL | 2.7E-1 | 3.6E-1 | 7.2E-1 | 6.3E-1 | 2.0E0 | 1.1E0 | 4.2E-3 | 4.2E-3 | 3.3E1 | 5.6E0 | 363 | 26 | 141 | 26 | 0.52 |
| aU | pg/mL | 7.8E1 | 6.8E1 | 1.3E2 | 1.2E2 | 1.5E2 | 1.4E2 | 7.4E-2 | 1.1E1 | 1.3E3 | 6.0E2 | 363 | 26 | 141 | 26 | 0.46 |
| aV | ng/mL | 6.3E-1 | 3.2E-1 | 1.1E0 | 8.2E-1 | 2.1E0 | 1.0E0 | 7.6E-4 | 3.1E-2 | 3.3E1 | 4.2E0 | 363 | 26 | 141 | 26 | 0.39 |
| aW | pg/mL | 1.9E1 | 1.9E1 | 2.0E1 | 3.8E1 | 2.1E1 | 8.4E1 | 7.2E-2 | 7.2E-2 | 2.4E2 | 4.5E2 | 363 | 26 | 141 | 26 | 0.56 |
| aX | ng/mL | 9.5E0 | 1.1E1 | 1.4E1 | 2.0E1 | 1.4E1 | 2.3E1 | 3.0E-1 | 2.5E0 | 8.0E1 | 1.1E2 | 363 | 26 | 141 | 26 | 0.57 |
| aY | pg/mL | 6.0E1 | 6.5E1 | 8.0E1 | 7.8E1 | 9.2E1 | 6.0E1 | 4.1E-1 | 4.1E-1 | 1.2E3 | 2.7E2 | 363 | 26 | 141 | 26 | 0.54 |
| aZ | pg/mL | 2.2E2 | 3.7E2 | 5.2E2 | 5.8E2 | 1.0E3 | 8.0E2 | 1.7E0 | 1.7E0 | 1.2E4 | 3.7E3 | 363 | 26 | 141 | 26 | 0.57 |
| bA | ng/mL | 8.5E0 | 2.8E1 | 3.0E1 | 6.0E1 | 7.7E1 | 1.2E2 | 3.0E-2 | 1.4E0 | 9.4E2 | 6.2E2 | 363 | 26 | 141 | 26 | 0.69 |
| bB | ng/mL | 3.0E2 | 2.9E2 | 3.2E2 | 3.1E2 | 1.6E2 | 1.6E2 | 1.6E1 | 5.1E1 | 1.0E3 | 6.1E2 | 363 | 26 | 141 | 26 | 0.49 |
| bC | ng/mL | 3.3E2 | 4.2E2 | 5.7E2 | 8.0E2 | 7.3E2 | 1.1E3 | 2.7E1 | 7.3E1 | 4.7E3 | 4.7E3 | 363 | 26 | 141 | 26 | 0.60 |
| bE | mg/mL | 5.4E0 | 6.1E0 | 5.7E0 | 6.3E0 | 1.9E0 | 2.4E0 | 1.4E0 | 2.8E0 | 1.3E1 | 1.3E1 | 363 | 26 | 141 | 26 | 0.56 |
| bF | pg/mL | 2.0E1 | 3.3E1 | 1.8E2 | 5.4E1 | 1.1E3 | 6.4E1 | 5.0E-2 | 8.1E0 | 1.1E4 | 3.2E2 | 363 | 26 | 141 | 26 | 0.63 |
| bG | ng/mL | 1.6E0 | 2.0E0 | 2.8E0 | 3.2E0 | 3.4E0 | 3.1E0 | 2.2E-2 | 2.4E-1 | 2.6E1 | 1.0E1 | 363 | 26 | 141 | 26 | 0.55 |
| bH | pg/mL | 5.7E-1 | 5.7E-1 | 5.2E0 | 4.0E0 | 1.7E1 | 6.0E0 | 5.7E-1 | 5.7E-1 | 2.8E2 | 2.1E1 | 363 | 26 | 141 | 26 | 0.50 |
| bI | ng/mL | 4.0E-3 | 4.0E-3 | 7.0E-2 | 9.5E-2 | 1.7E-1 | 1.3E-1 | 4.0E-3 | 4.0E-3 | 1.3E0 | 3.4E-1 | 363 | 26 | 141 | 26 | 0.57 |
| bJ | mg/mL | 2.2E0 | 2.6E0 | 2.5E0 | 2.8E0 | 1.9E0 | 1.7E0 | 2.5E-4 | 2.5E-1 | 1.3E1 | 7.1E0 | 363 | 26 | 141 | 26 | 0.56 |
| bL | pg/mL | 4.1E0 | 2.6E0 | 8.4E0 | 7.9E0 | 1.0E1 | 1.1E1 | 4.6E-2 | 4.6E-2 | 4.9E1 | 4.4E1 | 363 | 26 | 141 | 26 | 0.46 |
| bM | mg/mL | 1.7E0 | 2.1E0 | 2.1E0 | 2.3E0 | 1.4E0 | 1.3E0 | 9.2E-3 | 6.3E-1 | 7.9E0 | 6.1E0 | 363 | 26 | 141 | 26 | 0.58 |
| bN | ng/mL | 4.7E1 | 2.8E1 | 1.3E2 | 7.0E1 | 2.7E2 | 1.2E2 | 1.4E-1 | 1.4E-1 | 1.9E3 | 5.0E2 | 363 | 26 | 141 | 26 | 0.41 |
| bO | ng/mL | 4.0E-2 | 4.0E-2 | 9.2E0 | 1.4E1 | 2.1E1 | 3.9E1 | 4.0E-2 | 4.0E-2 | 1.9E2 | 1.9E2 | 363 | 26 | 141 | 26 | 0.47 |
| bP | mg/mL | 5.1E-1 | 5.2E-1 | 7.3E-1 | 7.3E-1 | 6.6E-1 | 6.0E-1 | 8.2E-2 | 1.4E-1 | 4.8E0 | 2.9E0 | 363 | 26 | 141 | 26 | 0.52 |
| bQ | pg/mL | 1.5E1 | 1.9E1 | 7.0E1 | 2.6E1 | 7.1E2 | 3.0E1 | 1.5E-1 | 1.5E-1 | 1.3E4 | 1.5E2 | 363 | 26 | 141 | 26 | 0.55 |
| bR | ng/mL | 1.2E-2 | 1.2E-2 | 1.4E-1 | 6.2E-2 | 5.0E-1 | 1.0E-1 | 1.2E-2 | 1.2E-2 | 8.7E0 | 3.9E-1 | 363 | 26 | 141 | 26 | 0.41 |
| bS | pg/mL | 9.4E-1 | 9.4E-1 | 7.8E0 | 4.3E0 | 3.1E1 | 1.1E1 | 9.4E-1 | 9.4E-1 | 3.9E2 | 4.8E1 | 363 | 26 | 141 | 26 | 0.49 |
| bU | ng/mL | 1.3E-2 | 1.3E-2 | 2.1E-1 | 9.3E-2 | 4.1E-1 | 1.3E-1 | 1.3E-2 | 1.3E-2 | 6.6E0 | 5.5E-1 | 363 | 26 | 141 | 26 | 0.37 |
| bV | pg/mL | 4.7E2 | 5.7E2 | 5.3E2 | 6.3E2 | 2.4E2 | 3.3E2 | 1.7E2 | 1.5E2 | 1.6E3 | 1.6E3 | 363 | 26 | 141 | 26 | 0.59 |
| bW | pg/mL | 3.4E2 | 3.3E2 | 4.9E2 | 6.3E2 | 5.0E2 | 1.2E3 | 8.4E1 | 1.4E2 | 4.8E3 | 6.4E3 | 363 | 26 | 141 | 26 | 0.50 |
| bX | ng/mL | 1.5E-3 | 2.5E-5 | 2.8E-3 | 2.0E-3 | 3.4E-3 | 2.6E-3 | 2.5E-5 | 2.5E-5 | 2.0E-2 | 8.8E-3 | 363 | 26 | 141 | 26 | 0.45 |
| bZ | pg/mL | 2.4E2 | 2.7E2 | 9.1E2 | 4.4E2 | 4.3E3 | 4.5E2 | 1.5E-1 | 5.9E1 | 5.8E4 | 1.7E3 | 363 | 26 | 141 | 26 | 0.55 |
| cA | pg/mL | 6.0E-1 | 6.0E-1 | 3.0E0 | 1.3E0 | 2.0E1 | 2.5E0 | 6.0E-1 | 6.0E-1 | 3.7E2 | 1.1E1 | 363 | 26 | 141 | 26 | 0.47 |
| cB | pg/mL | 5.4E-2 | 3.3E-2 | 8.6E-2 | 4.3E-2 | 1.0E-1 | 3.6E-2 | 1.7E-3 | 1.7E-3 | 5.7E-1 | 1.2E-1 | 363 | 26 | 141 | 26 | 0.39 |
| cC | pg/mL | 4.6E1 | 3.5E1 | 4.9E1 | 3.6E1 | 4.2E1 | 2.6E1 | 1.0E0 | 1.0E0 | 4.5E2 | 1.1E2 | 363 | 26 | 141 | 26 | 0.40 |
| cD | pg/mL | 5.2E0 | 4.7E0 | 1.3E1 | 1.1E1 | 3.9E1 | 1.8E1 | 3.3E-1 | 3.3E-1 | 4.8E2 | 8.4E1 | 363 | 26 | 141 | 26 | 0.46 |
| cE | pg/mL | 3.2E1 | 4.0E1 | 1.5E2 | 7.8E1 | 4.8E2 | 1.0E2 | 1.2E-1 | 1.2E-1 | 3.8E3 | 4.2E2 | 363 | 26 | 141 | 26 | 0.55 |
| cF | pg/mL | 1.2E1 | 5.3E-1 | 2.1E1 | 1.1E1 | 3.4E1 | 1.8E1 | 5.3E-1 | 5.3E-1 | 2.7E2 | 7.2E1 | 363 | 26 | 141 | 26 | 0.41 |
| cG | pg/mL | 4.3E1 | 6.4E1 | 1.1E2 | 7.4E1 | 5.7E2 | 4.3E1 | 7.8E0 | 7.7E0 | 1.0E4 | 2.0E2 | 363 | 26 | 141 | 26 | 0.63 |
| cH | uIU/mL | 3.1E0 | 1.4E0 | 6.7E0 | 3.2E0 | 1.3E1 | 5.4E0 | 8.6E-3 | 8.6E-3 | 1.6E2 | 2.4E1 | 363 | 26 | 141 | 26 | 0.31 |
| cI | ng/mL | 5.6E0 | 4.7E0 | 1.1E1 | 1.4E1 | 1.5E1 | 2.4E1 | 1.0E-3 | 1.1E-1 | 9.4E1 | 1.2E2 | 363 | 26 | 141 | 26 | 0.50 |
| cJ | ug/mL | 6.5E1 | 4.6E1 | 1.2E2 | 7.4E1 | 1.5E2 | 8.3E1 | 4.0E0 | 7.6E0 | 9.6E2 | 3.9E2 | 363 | 26 | 141 | 26 | 0.43 |
| cK | ng/mL | 3.8E-3 | 3.8E-3 | 5.9E-2 | 1.5E-2 | 2.0E-1 | 4.0E-2 | 3.8E-3 | 3.8E-3 | 1.7E0 | 1.6E-1 | 363 | 26 | 141 | 26 | 0.46 |
| cL | pg/mL | 1.9E2 | 2.2E2 | 4.0E2 | 2.5E2 | 1.5E3 | 1.5E2 | 1.6E1 | 4.1E1 | 2.4E4 | 6.4E2 | 363 | 26 | 141 | 26 | 0.56 |
| cM | pg/mL | 2.8E2 | 2.4E2 | 3.1E2 | 2.4E2 | 2.1E2 | 9.0E1 | 8.7E0 | 6.7E1 | 1.6E3 | 4.7E2 | 363 | 26 | 141 | 26 | 0.39 |
| cN | pg/mL | 1.2E2 | 1.3E2 | 1.3E2 | 1.4E2 | 7.0E1 | 4.9E1 | 3.8E1 | 6.4E1 | 1.1E3 | 2.4E2 | 363 | 26 | 141 | 26 | 0.58 |
| cO | pg/mL | 2.2E2 | 2.5E2 | 3.3E2 | 2.7E2 | 1.0E3 | 1.5E2 | 5.4E1 | 1.1E2 | 1.9E4 | 7.5E2 | 363 | 26 | 141 | 26 | 0.54 |

Figure 11 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cP | ng/mL | 2.6E3 | 2.8E3 | 2.6E3 | 3.1E3 | 9.4E2 | 1.3E3 | 6.2E2 | 1.6E3 | 5.7E3 | 7.3E3 | 363 | 26 | 141 | 26 | 0.59 |
| cQ | ng/mL | 4.9E-2 | 6.3E-2 | 1.2E-1 | 1.9E-1 | 2.3E-1 | 3.1E-1 | 2.0E-3 | 2.0E-3 | 2.2E0 | 1.2E0 | 363 | 26 | 141 | 26 | 0.57 |
| cR | ng/mL | 2.8E2 | 4.3E2 | 4.3E2 | 8.1E2 | 6.0E2 | 1.5E3 | 2.0E1 | 4.0E1 | 7.7E3 | 7.7E3 | 363 | 26 | 141 | 26 | 0.61 |
| cS | ng/mL | 2.6E2 | 3.0E2 | 3.7E2 | 3.9E2 | 3.7E2 | 2.8E2 | 4.7E1 | 9.7E1 | 2.7E3 | 1.2E3 | 363 | 26 | 141 | 26 | 0.55 |
| cT | ng/mL | 3.1E1 | 5.6E1 | 8.6E1 | 1.0E2 | 1.9E2 | 1.5E2 | 4.6E0 | 4.2E0 | 2.1E3 | 6.5E2 | 363 | 26 | 141 | 26 | 0.63 |
| cU | ng/mL | 5.3E1 | 5.8E1 | 7.7E1 | 8.9E1 | 1.1E2 | 9.4E1 | 6.2E0 | 1.2E1 | 1.6E3 | 4.8E2 | 363 | 26 | 141 | 26 | 0.53 |
| cV | ng/mL | 1.7E-1 | 1.7E-1 | 4.2E-1 | 2.7E-1 | 2.5E0 | 2.6E-1 | 3.4E-4 | 4.7E-2 | 4.7E1 | 1.2E0 | 363 | 26 | 141 | 26 | 0.53 |
| cW | mIU/mL | 5.3E-2 | 5.6E-2 | 1.6E-1 | 7.6E-2 | 7.9E-1 | 6.3E-2 | 3.7E-4 | 1.1E-2 | 9.7E0 | 2.6E-1 | 363 | 26 | 141 | 26 | 0.52 |
| cX | ng/mL | 1.0E-1 | 3.1E-2 | 1.4E0 | 7.6E-1 | 4.5E0 | 1.5E0 | 2.3E-4 | 2.3E-4 | 2.8E1 | 6.9E0 | 363 | 26 | 141 | 26 | 0.47 |
| cY | ng/mL | 8.8E0 | 7.1E0 | 1.3E1 | 1.2E1 | 1.4E1 | 1.3E1 | 1.5E-1 | 3.1E-1 | 8.3E1 | 5.4E1 | 363 | 26 | 141 | 26 | 0.45 |
| cZ | ug/mL | 1.4E1 | 1.5E1 | 1.5E1 | 1.6E1 | 6.1E0 | 6.3E0 | 2.7E0 | 6.3E0 | 3.9E1 | 3.6E1 | 363 | 26 | 141 | 26 | 0.53 |
| dA | pg/mL | 3.3E2 | 3.7E2 | 3.7E2 | 3.9E2 | 3.3E2 | 1.7E2 | 9.0E1 | 1.7E2 | 5.8E3 | 8.2E2 | 363 | 26 | 141 | 26 | 0.56 |
| dB | ug/mL | 1.7E1 | 1.8E1 | 1.8E1 | 1.7E1 | 1.8E1 | 9.2E0 | 9.4E-1 | 1.9E0 | 2.5E2 | 4.1E1 | 363 | 26 | 141 | 26 | 0.53 |
| dC | nmol/L | 3.5E1 | 3.6E1 | 4.0E1 | 3.9E1 | 1.9E1 | 2.0E1 | 9.1E0 | 1.3E1 | 1.4E2 | 8.3E1 | 363 | 26 | 141 | 26 | 0.48 |
| dD | ug/mL | 3.6E1 | 3.3E1 | 3.7E1 | 3.5E1 | 1.1E1 | 9.6E0 | 1.3E1 | 1.5E1 | 7.6E1 | 5.8E1 | 363 | 26 | 141 | 26 | 0.43 |
| dE | ng/mL | 4.7E-1 | 5.4E-1 | 6.1E-1 | 7.8E-1 | 7.4E-1 | 7.7E-1 | 8.4E-3 | 8.4E-3 | 7.2E0 | 3.3E0 | 363 | 26 | 141 | 26 | 0.58 |
| dF | ng/mL | 2.2E2 | 3.1E2 | 2.7E2 | 3.5E2 | 1.8E2 | 2.0E2 | 7.5E1 | 8.3E1 | 1.3E3 | 8.6E2 | 363 | 26 | 141 | 26 | 0.67 |
| dG | ng/mL | 1.1E1 | 1.6E1 | 1.4E1 | 1.9E1 | 1.3E1 | 1.2E1 | 3.1E0 | 2.2E0 | 1.8E2 | 6.9E1 | 363 | 26 | 141 | 26 | 0.69 |
| dH | pg/mL | 7.5E0 | 7.8E0 | 1.3E1 | 1.1E1 | 4.1E1 | 8.0E0 | 4.0E-2 | 4.0E-2 | 6.7E2 | 3.5E1 | 363 | 26 | 141 | 26 | 0.56 |
| dI | pg/mL | 4.6E-1 | 4.6E-1 | 2.5E0 | 1.1E0 | 1.8E1 | 2.0E0 | 4.6E-1 | 4.6E-1 | 3.3E2 | 8.8E0 | 363 | 26 | 141 | 26 | 0.46 |
| dJ | ng/mL | 1.9E0 | 1.3E0 | 2.2E0 | 1.8E0 | 1.2E0 | 1.1E0 | 3.2E-2 | 4.0E-1 | 6.9E0 | 4.0E0 | 363 | 26 | 141 | 26 | 0.39 |
| dK | uIU/mL | 1.9E0 | 1.6E0 | 3.2E0 | 4.1E0 | 6.5E0 | 1.1E1 | 2.8E-4 | 3.8E-2 | 7.9E1 | 6.0E1 | 363 | 26 | 141 | 26 | 0.45 |
| dL | ng/mL | 8.8E2 | 1.1E3 | 1.0E3 | 1.1E3 | 4.9E2 | 3.8E2 | 3.4E2 | 3.3E2 | 3.4E3 | 1.8E3 | 363 | 26 | 141 | 26 | 0.61 |
| dM | pg/mL | 9.7E2 | 1.1E3 | 1.2E3 | 1.8E3 | 9.3E2 | 1.8E3 | 3.9E2 | 3.7E2 | 1.2E4 | 8.3E3 | 363 | 26 | 141 | 26 | 0.64 |
| dN | ug/mL | 9.4E1 | 9.6E1 | 9.9E1 | 1.1E2 | 3.4E1 | 4.2E1 | 2.5E1 | 3.7E1 | 2.4E2 | 2.0E2 | 363 | 26 | 141 | 26 | 0.56 |
| dO | ng/ml | 2.3E1 | 9.3E0 | 4.6E1 | 2.5E1 | 6.5E1 | 3.7E1 | 4.0E-1 | 3.8E0 | 3.7E2 | 1.1E2 | 65 | 8 | 47 | 8 | 0.31 |
| dR | pg/ml | 1.6E3 | 1.3E3 | 2.4E3 | 2.0E3 | 2.5E3 | 2.1E3 | 1.4E2 | 1.9E2 | 1.5E4 | 8.9E3 | 245 | 25 | 138 | 25 | 0.44 |
| dV | pg/ml | 7.1E1 | 6.0E1 | 9.0E1 | 7.2E1 | 5.5E1 | 4.8E1 | 3.4E1 | 3.6E1 | 2.7E2 | 1.9E2 | 46 | 8 | 27 | 8 | 0.34 |
| dX | ng/ml | 3.4E-2 | 7.4E-3 | 1.2E-1 | 1.4E-1 | 2.0E-1 | 2.8E-1 | 2.6E-3 | 2.6E-3 | 1.2E0 | 8.6E-1 | 92 | 9 | 30 | 9 | 0.43 |
| eF | ng/ml | 4.1E0 | 5.6E0 | 4.6E0 | 5.6E0 | 2.2E0 | 2.1E0 | 1.4E0 | 2.6E0 | 1.8E1 | 1.1E1 | 257 | 25 | 138 | 25 | 0.67 |
| eC | pg/ml | 3.1E2 | 2.7E2 | 3.7E2 | 3.3E2 | 2.2E2 | 2.3E2 | 4.5E1 | 1.6E2 | 1.4E3 | 1.2E3 | 203 | 18 | 135 | 18 | 0.42 |
| eM | ng/ml | 3.5E0 | 3.8E0 | 4.7E0 | 8.0E0 | 4.4E0 | 7.4E0 | 7.6E-1 | 1.8E0 | 2.4E1 | 2.5E1 | 122 | 9 | 50 | 9 | 0.65 |
| eP | ng/ml | 3.7E-3 | 3.1E-2 | 7.3E-1 | 7.5E0 | 1.8E0 | 2.2E1 | 3.7E-3 | 3.7E-3 | 1.2E1 | 6.5E1 | 92 | 9 | 30 | 9 | 0.57 |
| eX | ng/ml | 4.7E1 | 1.3E1 | 1.6E1 | 2.1E1 | 2.1E1 | 2.1E1 | 8.6E-4 | 1.8E0 | 7.3E1 | 4.9E1 | 65 | 8 | 47 | 8 | 0.63 |
| fP | ng/ml | 2.5E2 | 2.9E2 | 2.9E2 | 3.3E2 | 1.7E2 | 2.1E2 | 1.8E0 | 1.2E2 | 1.0E3 | 9.6E2 | 240 | 21 | 137 | 21 | 0.56 |
| fR | ng/ml | 1.2E5 | 2.0E5 | 1.7E5 | 2.6E5 | 1.4E5 | 1.9E5 | 3.1E4 | 2.9E4 | 7.2E5 | 8.3E5 | 236 | 17 | 68 | 17 | 0.69 |
| gC | ng/ml | 2.3E2 | 2.3E2 | 2.5E2 | 2.5E2 | 1.0E2 | 8.6E1 | 8.3E1 | 1.7E2 | 6.4E2 | 4.4E2 | 103 | 8 | 58 | 8 | 0.53 |
| gN | U/ml | 3.6E2 | 4.0E2 | 4.7E2 | 5.2E2 | 3.0E2 | 2.6E2 | 3.5E1 | 3.1E2 | 1.3E3 | 9.3E2 | 46 | 8 | 27 | 8 | 0.60 |
| gL | pg/ml | 6.3E4 | 7.9E4 | 6.9E4 | 8.7E4 | 2.8E4 | 3.2E4 | 1.1E4 | 3.8E4 | 1.8E5 | 1.6E5 | 245 | 25 | 138 | 25 | 0.67 |
| gP | U/ml | 2.8E2 | 2.3E2 | 2.8E2 | 2.3E2 | 1.1E2 | 8.4E1 | 1.2E1 | 7.9E1 | 1.1E3 | 3.9E2 | 253 | 25 | 138 | 25 | 0.34 |
| gT | ng/ml | 2.1E1 | 2.0E1 | 2.1E1 | 2.2E1 | 4.5E0 | 4.7E0 | 1.2E1 | 1.7E1 | 3.3E1 | 3.0E1 | 49 | 8 | 33 | 8 | 0.54 |
| gW | ng/ml | 5.7E2 | 5.2E2 | 1.2E3 | 1.2E3 | 1.7E3 | 2.0E3 | 3.1E-1 | 8.3E1 | 9.5E3 | 8.2E3 | 213 | 25 | 129 | 25 | 0.50 |
| tF | pg/mL | 1.5E3 | 1.5E3 | 1.6E4 | 1.0E4 | 4.7E4 | 2.2E4 | 1.2E1 | 1.8E1 | 3.2E5 | 9.4E4 | 203 | 18 | 135 | 18 | 0.51 |
| iA | pg/ml | 1.5E2 | 2.0E2 | 3.0E2 | 3.5E2 | 6.6E2 | 5.0E2 | 1.1E1 | 8.2E0 | 7.1E3 | 2.2E3 | 203 | 18 | 135 | 18 | 0.60 |
| iH | ng/ml | 1.6E5 | 1.9E5 | 1.5E5 | 1.7E5 | 4.7E4 | 5.2E4 | 5.1E4 | 7.8E4 | 2.7E5 | 2.5E5 | 203 | 18 | 135 | 18 | 0.63 |
| iJ | ng/ml | 5.3E4 | 5.1E4 | 5.5E4 | 5.8E4 | 3.0E4 | 2.2E4 | 7.7E3 | 2.3E4 | 2.5E5 | 9.7E4 | 203 | 18 | 135 | 18 | 0.55 |
| hB | ng/ml | 4.3E-1 | 4.6E-1 | 5.4E-1 | 5.8E-1 | 4.1E-1 | 4.4E-1 | 1.2E-1 | 1.5E-1 | 3.0E0 | 2.0E0 | 203 | 18 | 135 | 18 | 0.52 |
| hC | pg/ml | 4.1E3 | 3.2E3 | 7.1E3 | 6.8E3 | 1.0E4 | 7.2E3 | 1.0E-9 | 1.0E-9 | 1.1E5 | 2.5E4 | 203 | 18 | 135 | 18 | 0.49 |
| hF | ng/ml | 1.0E-9 | 1.0E-9 | 2.4E1 | 1.0E-9 | 2.9E2 | 0.0E0 | 1.0E-9 | 1.0E-9 | 4.0E3 | 1.0E-9 | 203 | 18 | 135 | 18 | 0.49 |
| hG | pg/ml | 7.0E3 | 6.7E3 | 7.7E3 | 8.2E3 | 3.3E3 | 3.9E3 | 1.7E3 | 3.6E3 | 2.0E4 | 1.7E4 | 203 | 18 | 135 | 18 | 0.51 |
| iO | ng/ml | 3.8E5 | 3.5E5 | 4.0E5 | 3.6E5 | 1.8E5 | 1.2E5 | 8.3E4 | 1.4E5 | 1.1E6 | 5.4E5 | 203 | 18 | 135 | 18 | 0.46 |
| iP | ng/ml | 5.1E4 | 4.7E4 | 5.7E4 | 6.3E4 | 5.5E4 | 4.5E4 | 2.4E3 | 5.6E3 | 5.5E5 | 1.6E5 | 203 | 18 | 135 | 18 | 0.52 |
| iZ | ng/ml | 1.6E3 | 2.0E3 | 1.8E3 | 2.4E3 | 7.6E2 | 1.3E3 | 4.7E2 | 9.8E2 | 5.7E3 | 6.5E3 | 201 | 18 | 133 | 18 | 0.67 |
| kQ | ng/ml | 4.3E3 | 4.8E3 | 5.0E3 | 6.0E3 | 2.9E3 | 4.8E3 | 5.6E2 | 1.6E3 | 2.5E4 | 2.1E4 | 203 | 18 | 135 | 18 | 0.51 |
| kR | pg/ml | 2.3E1 | 2.2E1 | 3.3E1 | 2.4E1 | 7.3E1 | 1.9E1 | 1.0E-9 | 1.2E0 | 1.0E3 | 7.1E1 | 203 | 18 | 135 | 18 | 0.44 |
| kS | pg/ml | 8.0E2 | 7.0E2 | 9.6E2 | 9.7E2 | 1.1E3 | 8.1E2 | 8.2E1 | 7.9E1 | 1.4E4 | 2.9E3 | 203 | 18 | 135 | 18 | 0.47 |
| nW | pg/ml | 1.1E5 | 1.1E5 | 1.1E5 | 1.2E5 | 2.5E4 | 3.6E4 | 5.8E4 | 7.2E4 | 1.8E5 | 2.3E5 | 203 | 18 | 135 | 18 | 0.49 |

Figure 11 Continued

| Code | Units | Median | | Average | | Standard Deviation | | Minimum | | Maximum | | Number of Samples | | Number of Patients | | AUC |
|------|-------|--------|--|---------|--|--------------------|--|---------|--|---------|--|-------------------|--|--------------------|--|-----|
| | | NonDis | Dis | NonDis | Dis | NonDis | Dis | NonDis | Dis | NonDis | Dis | NonDis | Dis | NonDis | Dis | |
| nY | pg/ml | 2.1E3 | 2.1E3 | 2.4E3 | 2.4E3 | 1.6E3 | 1.4E3 | 5.1E2 | 5.4E2 | 1.3E4 | 5.8E3 | 203 | 18 | 135 | 18 | 0.51 |
| oE | pg/ml | 1.5E2 | 1.5E2 | 3.8E2 | 4.7E2 | 5.5E2 | 8.7E2 | 1.0E-9 | 2.0E1 | 4.7E3 | 3.7E3 | 203 | 18 | 135 | 18 | 0.51 |
| oF | pg/ml | 8.5E3 | 1.6E4 | 2.2E4 | 3.1E4 | 3.6E4 | 4.4E4 | 6.4E1 | 4.8E2 | 2.5E5 | 1.8E5 | 203 | 18 | 135 | 18 | 0.58 |
| oH | pg/ml | 4.1E1 | 4.6E1 | 9.4E1 | 1.0E2 | 1.4E2 | 1.7E2 | 4.2E0 | 9.1E0 | 9.9E2 | 6.3E2 | 203 | 18 | 135 | 18 | 0.51 |
| oK | pg/ml | 7.6E2 | 7.8E2 | 1.9E3 | 1.7E3 | 2.6E3 | 2.0E3 | 5.2E1 | 3.1E2 | 1.8E4 | 7.9E3 | 203 | 18 | 135 | 18 | 0.55 |
| oN | pg/ml | 5.1E2 | 5.6E2 | 7.9E2 | 6.0E2 | 1.5E3 | 2.9E2 | 1.5E2 | 2.4E2 | 1.8E4 | 1.2E3 | 203 | 18 | 135 | 18 | 0.52 |
| pF | pg/ml | 4.8E-1 | 4.1E-1 | 1.1E0 | 1.0E0 | 6.1E0 | 2.3E0 | 1.0E-9 | 1.0E-9 | 8.7E1 | 1.0E1 | 203 | 18 | 135 | 18 | 0.44 |

Analyte panel data:

Unconstrained panels with 3 analytes, where 1.0E-9 >= 'model p-value' > 0. Contains 134 panels of 9,935,646 total panels evaluated. : Et{Nl(Hq Hw Ii In Iq Iu Ji Jj Jk Jo Jr Js Jt Lv Lx Ly Lz Ma Mc Md Me Mg Mi Mj Mm Mq Mr Mt Mx Nd Nf Ng Ni Nk Nq Ns Of Og Ok Om On Pa Pb Pd Po Qb) Om(Fp Ih Ik Iv Ji Jj Jo Jr Lx Ly Md Mi Mr Mt Nc Nd Ne Nh Nj Nt Ok On Pa) Nd(Jj Jo Lx Ly Md Mt Nc Of Ok Pa) Ly(Jj Jo Js Md Nc Of Pa) Md(Jg Mt Mw Nc Ne Nj) Jo(Ik Lv Nc Ne Nj Nt) Nj(Jj Of Pa) MiHq NeJj} Ok{Nl(Hq Jj Jo Js Md Om) Jo(Ik Ly Nd Nj Om) Om(Jj Js Lx Mt) Md(Ly Nd Nj) PoLx} Md{Nl(Jg Nw On) Ly(Jg Nw) JgOm} Gn{Kc(Iz Uu Vo) HuRa aVaX} MiNlHq Unconstrained panels with 3 analytes, where 1.0E-8 >= 'model p-value' > 1.0E-9. Contains 668 panels of 9,935,646 total panels evaluated. : Et{Om(aA Fr Hq Hr Hu Hv Hw Hx Ii Ij Im In Io Ip Iq Ir Is It Iu Jg Jh Jk Jl Jm Jn Jp Jq Js Jt Lh Li Lj Lu Lv Lw Lz Ma Mb Mc Me Mf Mg Mh Mj Mk Ml Mm Mn Mp Mq Ms Mu Mv Mw Mx My Mz Na Nb Nf Ng Ni Nk Nm Nn No Nq Nr Ns Nu Nv Nw Nx Ny Oe Of Og Oh Oi Oy Oz Pb Pc Pd Pe Pf Pg Po Pz Qa Qb Qc Qd Qe) Nl(aA Fp Fr Hr Hu Hv Hx Ih Ij Ik Il Im Io Ip Ir Is It Iv Jg Jh Jl Jm Jn Jp Jq Lh Li Lj Lu Lw Mb Mf Mh Mk Ml Mn Mp Ms Mu Mv Mw My Mz Na Nb Nc Ne Nh Nj Nm Nn No Nt Nu Nv Nw Nx Ny Oe Oh Oi Oy Oz Pc Pe Pf Pg Pz Qa Qc Qd Qe) Ly(Dc Dk Fp fR Hq Hr Hu Hw Hx Ih Ii Ij Ik Im In Iq Is Iu Iv Jg Jh Ji Jk Jp Jr Jt Li Lj Lv Lx Ma Mc Mg Mi Mk Mm Mq Mr Ms Mt Mv Mx My Ne Nf Ng Nh Nj Nk Nm Nq Ns Nt Nw Ny Oe Og Oi Ok On Oy Oz Pb Pc Pd Pe Pg Qe) Nd(aA Fp Hw Ih Ik Im Iq Is Iu Iv Jg Ji Jl Jr Js Jt Li Lj Lv Ma Mc Me Mg Mi Mk Mm Mr Mv My Ne Nf Nh Nj Nq Nr Ns Nt Nu Nw Og Oi On Oz Pb Pe Qa Qe) Nj(Fp Hq Hw Ih Ii Il In Iq Iu Iv Jg Ji Jk Jp Jr Js Jt Lj Lv Lx Mc Mg Mi Mm Mq Mr Mt My Ne Nf Ng Ni Nm Nq Ns Nw Og Ok On Oz Pb Pc Pd Pe) Md(Fp Hw Ik Iq Iv Ji Jj Jo Jr Js Lv Lx Mi Nb Nh Nt Nu Nw Nx Of Ok On Oz Pa Pb Pc) Jo(Fp Ih Iq Iv Ji Jr Lx Mf Mg Mi Mr Mt Nh Ns Ok On Oz Pa Pb) Ne(Hw Ii In Iq Iu Jt Jk Js Jt Lx Mi Nf Ns Of Og Ok Pa) Nc(Hw Iq Iu Jj Js Jt Mi Ni Ns Of Og Ok Pa) Mt(Hw Iq Jj Js Jt Nq Ns Of) Ik(Jj Jt Of) Nf(Ok On) Nh(Jj Of) PoLx NtJt MvJg IqOk} Ok{Nl(Hu Hw Hx Ii Il In Iq It Iu Jk Jr Jt Lx Ly Lz Me Mi Mm Mq Mt Nd Nf Ni Nk Nm Ns Nw Of Og Oy Oz Pa Po Qb Qc Qd) Om(Fp Hq Hr Hw Hx Ik Iq Jg Jh Ji Jr Jt Lj Ly Md Nc Nd Ne Nf Nj Of Pa Qe) Md(Fp Hw Ik Iq Jg Jo Js Lv Lx Mt Mw Nc Ne Nf Nh Nw Nx Of Og Oz Pa) Nd(Hq Iu Jj Js Lx Ly Mm Mt Nc Nf Of Og Pa) Nj(Hq Il Iu Jj Jp Js Lx Mt Nf Of Og Pa) Ly(Hq Jj Js Lx Mq Mt Nc Nf Of Og Pa) Ne(Hq Jj Jo Js Nf Of) Mt(Hq Hw Iq Js Nf) Nc(Hq Jj Jo Js Of) Nf(Fp Js Lx Pa) Jo(Iq Lv Oz Pa) LxIq MiHq IkJj} Md{Jg(Fp Lx Mt Nd Ne Nh Nj Nw Og) Nw(Ik Js Mt Nc Nd Ne Nj Om) On(Ly Mt Nd Ne Nj Om) Nl(Ji Lx Mi Mm Nx) Ly(Jp Lx)} Nl{Jj(Jg Ji Lx Ly Mm Mt Nw On Pa) Om(Jg Ji Lx Mm Nw) Nw(In Js Mm) Jg(Mv Ng) On(Hq Oy) PoLx MmPa JiOg} Ly{Jj(Jg Jp Lx Mm Mt Pa) fR(Jk Mj) Nf Oz) Jg(Mv My Ng) PoLx GnRc MiHq JsNw OnOy} Gn{Kc(Cw Jo Kf Nm Rc) Hu(Om Qz) aV(aU cY)} Lx{Jj(Ik Nd Nj) Jg(Mv Om) MiHq JiOm} Jg{Mv(Nd Ne Og Om) JjOm} Mi{Hq(Ik Mt Nj)} Nw{Js(Nj Om) MtOm} On{Oy(Nd Nj)} EmKcVo MtJiOm IkJjPa Unconstrained panels with 3 analytes, where 1.0E-7 >= 'model p-value' > 1.0E-8. Contains 2,576 panels of 9,935,646 total panels evaluated. : Et{Nc(aA Fp Fr Hq Hr Hu Hv Hx Ih Ii Ij Ik Im In Io Ip Iq Jr Ls It Iv Jg Jh Ji Jk Jl Jm Jn Jp Jq Jr Lh Li Lj Lu Lv Lw Lx Lz Ma Mb Mc Me Mf Mg Mh Mj Mk Ml Mm Mn Mp Mq Mr Ms Mt Mu Mv Mw Mx My Mz Na Nb Nc Nf Ng Nh Nk Nm Nn No Nq Nr Nt Nu Nv Nw Nx Ny Oe Oh Oi On Oy Oz Pb Pc Pd Pe Pf Pg Po Pz Qa Qb Qc Qd Qe) Jo(aA Dc Dk Fr Gl Hq Hr Hu Hv Hw Hx Ii Ij Im In Ip Ir Is It Iu Jg Jh Jj Jk Jl Jm Jn Jp Jq Js Jt Kk Lh Li Lj Lu Lw Lz Ma Mb Mc Me Mh Mj Mk Ml Mm Mn Mp Mq Ms Mu Mv Mw Mx My Mz Na Nb Nf Ng Ni Nk Nm Nn No Nq Nr Nu Nv Nw Nx Ny Oe Of Og Oh Oi Ou Oy Pc Pd Pe Pf Pg Po Pz Qa Qb Qc Qd Qe Wm) Ne(aA Fp Fr Hq Hr Hu Hv Hx Ih Ij Ik Im Io Ip Ir Is It Iv Jg Jh Jl Jm Jn Jp Jq Jr Lh Li Lj Lu Lv Lw Lz Ma Mb Mc Me Mf Mg Mh Mj Mk Ml Mm Mn Mp Mq Mr Ms Mt Mu Mv Mw Mx My Mz Na Nb Ng Nh Ni Nk Nm Nn No Nq Nr Nt Nu Nv Nw Nx Ny Oe Oh Oi On Oy Oz Pb Pc Pd Pe Pf Pg Po Pz Qa Qb Qc Qd Qe) Md(aA Fr Hq Hr Hu Hv Hx Ih Ii Ij Im In Io Ip Ir Is It Iu Jh Jk Jl Jm Jn Jp Jq Jt Lh Li Lj Lu Lw Lz Ma Mb Mc Me Mf Mg Mh Mj Mk Ml Mm Mn Mp Mq Mr Ms Mu Mv Mx My Mz Na Nf Ng Ni Nk Nm Nn No Nq Nr Ns Nv Ny Oe Og Oh Oi Oy Pd Pe Pf Pg Po Pz Qa Qb Qc Qd Qe) Nj(aA Fr Hr Hu Hv Hx Ij Ik Im Io Ip Ir Is It Jh Jl Jm Jn Jq Lh Li Lu Lw Lz Ma Mb Me Mf Mh Mj Mk Ml Mn Mp Ms Mu Mv Mw Mx Mz Na Nb Nh Nk Nn No Nr Nt Nu Nv Nx Ny Oe Oh Oi Oy Pf Pg Po Pz Qa Qb Qc Qd Qe) Nd(Fr Hq Hr Hu Hv Hx Ii Ij In Io Ip Ir It Jh Jk Jm Jn Jp Jq Lh Lu Lw Lz Mb Mf Mh Mj Ml Mn Mp Mq Ms Mu Mw Mx Mz Na Nb Ng Ni Nk Nm Nn No Nv Nx Ny Oe Oh Oy Pc Pd Pf Pg Po Pz Qb Qc Qd) Mt(Fp Fr Hq Hx Ih Ii Ij Ik In Iu Iv Ji Jk Jl Jq Jr Lj Lv Lx Ma Mb Mc Mg Mi Mj Mm Mq Mr Ms Mv Nf Ng Nh Nm Nt Nv Oe Og Oi Ok On Oy Oz Pa Pb Pd Po) Ly(aA Ao Bg Ch Fr Hv Il Io Ip Ir It Jl Jm Jn Jq Lh Lu Lw Lz Mb Me Mf Mh Mj Ml Mn Mp Mu Mw Mz Na Nb Ni Nn No Nr Nu Nv Nx Oh Pf Po Pz Qa Qb Qc Qd) Of(Fp Hw Hx Ih Im Iq Is Iv Jg Jh Ji Jj Jl Jr Js Jt Li Lj Lv Lx Mb Mc Mf Mg Mi Mk Mr Nf Nk Nq Nr Ns Nt Nu Nw Nx Oi Ok On Oz Pa Pb Pc Pe Pg Qa Qe) Nh(Fp Hq Hw Hx Ih Ii Ij Ik In Iq Iu Iv Ji Jk Jr Js Jt Lj Lv Lx Ma Mc Mg Mi Mm Mq Mr Mv My Nf Ng Nq Ns Og Ok On Oz Pa Pb Pd) Ik(Fp Hq Hu Hw Ih Ii Ij In Iq Iu Iv Ji Jk Js Lj Lv Lx Ma Me Mg Mi Mq Mr Mv My Nf Ng Nm Nq Ns Og Oi Ok Oz Pa Pd Po) Iq(Fp Hw Ih Im Is Iv Jg Ji Jj Jl Jr Js Jt Li Lj Lv Lx Mi Mr Nf Nk Nq Ns Nt Og On Oz Pa Pb Pe Qa Qe) Nf(Ao Bg Dc Dk Fp Hw Ih Is Iv Jg Ji Jj Jl Jr Js Jt Lj Lv Lx Mi Mk Mr Nq Ns Nt Nw Oz Pa Pb Pc) Fp(Dc Hw Ii In Iu Jj Js Jt Lv Ma Mi Mj Mq Mr Nq Ns Og Ok Oz Pa Po) Jj(Hw Hx Ih Iv Jr Js Lv Lx Mf Mr Nk Nq Ns Nt Nu Oi Ok Oz Pa Pb) Lx(Hq Hw Hx Ii In Iu Jk Js Jt Lv Mr Mv Ng Nq Ns Ok Oz) Hw(Hq Ih Iv Ji Jr Jt Lj Lv Mi Mr Ns Nt Ok On Oz Pa) Jt(Ih Iv Jg Ji Jr Lj Lv Mi Mr Ok On Oz Pa Qe) Ns(Jg Ji Jr Js Lv Nt Nu Ok On Oz Pa Pb Pc) Nq(Ih Iv Jg Ji Jr Lv Mi Mr Nt Ok On Pa) Js(Ih Ji Jr Lj Lv Mi Mr Nt Nw Ok Oz Pa) Ok(Hq Hx Ii Lv Mq My Og Oz Pa) Oz(Ih Iv Ji Lv Mi Mr Nt On) Pa(Dc Dk Hx Ii Lv Nt Og) Gl(Dc Dk Jf Om Ur) Nt(Ii In Iu Ng Og) Oy(Iv Mk Mr On) Dk(Jf Om Pb) Hq(Iv Mr On) Dc(Jf Om) Jg(My Ng) Pg(Mi Wm) BgOm LvOg MjMr IhIn IjIv JfUt} Ok{Nd(aA Fp Fr Hr Hu Hv Hw Hx Ih Ii Ij Ik Il Im In Io Ip Iq Ir Is It Iv Jg Jh Ji Jk Jl Jm Jn Jp Jq Jr Jt Lh Li Lj Lu Lv Lz Ma Mc Me Mf Mg Mh Mi Mj Mk Ml Mn Mq Mr Ms Mv Mw Mx My Mz Nb Ne Ng Nh Ni Nj Nk Nm Nn No Nq Nr Ns Nt Nu Nv Nw Nx Ny Oe Oh Oi On Oy Oz Pb Pc Pd Pe Pf Pg Po Pz Qa Qb Qc Qd Qe) Nj(aA Fr Hr Hu Hw Hx Ih Ii Ij Ik Im In Ip Iq Ir Is It Iv Jg Jh Ji Jk Jl Jm Jn Jp Jq Jr Jt Lh Li Lj Lu Lv Lz Ma Mc Me Mf Mg Mh Mi Mj Mk Ml Mn Mq Mr Ms Mv Mw Mx My Mz Nb Ne Ng Nh Ni Nj Nk Nm Nn No Nq Nr Ns Nt Nu Nv Nw Nx Ny Oe Oh Oi On Oy Oz Pb Pc Pd Pe Pf Pg Po Pz Qa Qb Qc Qd Qe) Nj(aA Fr Hr Hu Hw Hx Ih Ii Ij Ik Im In Ip Iq Ir Is It Iv Jg Jh Ji

Figure 11 Continued

Jk Jl Jm Jn Jq Jr Jt Lh Lj Lu Lv Ly Lz Ma Mc Me Mg Mh Mi Mj Mk Ml Mm Mn Mq Mr Ms Mv Mx My Mz Nb Nc Ne Ng Nh Ni Nk Nl Nm
Nn Nq Nr Ns Nt Nu Nv Nw Nx Ny Oe Oi On Oy Oz Pb Pc Pd Pe Pg Po Pz Qa Qb Qc Qd Qe) Om(aA Fr Hu Hv Ih li Ij Im In Io Ip Ir Is It Iu Iv
Jk Jl Jm Jn Jp Jq Lh Li Lu Lv Lw Lz Ma Mb Mc Me Mf Mg Mh Mi Mj Mk Ml Mm Mn Mp Mq Mr Ms Mu Mv Mw Mx My Mz Na Nb Ng Nh
Ni Nk Nm Nn No Nq Nr Ns Nt Nu Nv Nw Nx Ny Oe Og Oh Oi On Oy Oz Pb Pc Pd Pe Pf Pg Po Pz Qa Qb Qc Qd) Md(aA Fr Hq Hr Hu Hx Ih
Ii Ij Im In Ir It Iu Iv Jh Ji Jj Jk Jm Jn Jp Jq Jr Jt Lh Li Lj Lw Lz Ma Mb Mc Me Mf Mg Mh Mi Mj Mk Ml Mm Mn Mq Ms Mv Mx Na Nb Ni Nk
Nm Nn No Nq Nr Ns Nt Nu Nv Oe Oh Oi On Oy Pb Pc Pd Pe Pf Pg Po Qa Qc Qd Qe) Nl(aA Fp Fr Hr Hv Ih Ij Ik Im Io Ip Ir Is Iv Jg Jh Ji Jl Jm
Jn Jp Jq Lh Li Lj Lu Lv Lw Ma Mb Mc Mf Mg Mh Mj Mk Ml Mn Mp Mr Ms Mu Mv Mw Mx My Mz Na Nb Nc Ne Ng Nh Nn No Nq Nr Nt
Nu Nv Nx Ny Oe Oh Oi On Pb Pc Pd Pe Pf Pg Pz Qa Qe) Ly(Fp Hr Hu Hw Hx Ih Ii Ij Ik Il Im In Iq It Iu Iv Jg Jh Ji Jk Jp Jq Jr Jt Lj Lv Lz Mi
Mm Mr Ms My Nc Ng Nh Nm Nq Nr Ns Nw Nx Ny Oe Oy Oz Pb Pc Pd Pg Po Qc Qe) Nf(Hq Hw Hx Ih Ik Im Iq Iu Iv Jg Ji Jj Jm Jo Jp Jr Jt Lj
Lv Mf Mi Mm Mq Mr My Nc Nh Nq Nr Ns Nt Nu Nw Nx Of Og Oi On Oz Pb Pe Pg Qc Qe) Jo(Fp Hw Hx Ih Ip It Iv Jg Ji Jl Jm Jr Js Lx Mb Mf
Mg Mi Mk Mm Mq Mr Ms Mt Nh Nk No Nq Nr Ns Nt Nx Of Og Oi On Oy Pb Pc Pe Pg) Ne(aA Fp Hr Hu Hw Hx Ii In Iq Ir It Iu Iv Jg Jk Jp Jq
Jr Jt Lx Lz Me Mi Mm Mq Mt My Nm Ns Nw Ny Og Oy Oz Pa Po Qb Qc Qd) Mt(Fp Hx Ii Ij Ik In Iu Jh Jj Jk Jq Jr Jt Lv Lx Mj Mq Ms Mv My
Nc Ng Nh Nq Ns Nv Ny Of Og Oy Oz Pa Pd Pg Po Qb) Nc(Fp Hw Hx Ii Ij In Iq Iu Jg Jk Jq Jr Jt Lv Lx Lz Mi Mm Mq Ni Nk Nm Nq Ns Og Oy
Oz Pa Po Qb Qc Qd) Lx(Hq Hw Hx Ii Ij Ik In Iu Jj Jk Jr Js Jt Lv Lz Mq Mv My Ng Nh Nq Ns Ny Of Og Oy Oz Qc) Js(Fp Hw Hx Ih Ik Iq Iv Jj
Jr Lj Lv Mi Mq Nh Nk Nq Ns Nt Nw Of Og Oz Pa) Iq(Fp Hq Hw Ih Ik Jg Jj Jp Jr Jt Lj Mq Nh Of Og Oz Pa) Of(Hq Hw Hx Ik Jg Jj Jt Lv Nh Nt
Og Oi Oz Pa) Hq(Fp Hw Ik Iv Lv Nh Nr Og Oz Pa Pb) Jj(Fp Hw Hx Lv Nh Nq Nt Oz Pa) Og(Hw Hx Ik Jt Lv Nh Nt Oz Pa) Mq(Fp Ik Nh Oz)
Pa(Hw Ik Jt Nh) Jg(Jt Mv Ng) NhHw IkJt} Nl{Nw(aA Hq Hr Hu Hv Hw Hx Ii Ij Il Iq It Iu Iv Jg Jh Ji Jk Jl Jm Jn Jo Jq Jr Jt Lv Lx Ly Lz Mc Me
Mi Mj Mk Ml Mq Mr Ms Mt Mv Mx My Mz Nd Ne Nf Ni Nj Nk Nq Ns Nv Ny Of Og Oi On Oy Oz Pa Pb Pd Pg Po Qa Qb Qc Qd) Mm(aA Fp
Hq Hw Ih Ik In Iq Is Iu Iv Jg Ji Jk Jo Jp Jr Js Lj Lv Lx Ly Mi Mq Mr Mt Nd Nf Ni Nk Nq Nr Ns Of Og On Oz Pb Pc Pd Pe) Lx(aA Hu Hw Hx
In Iq Iu Iv Jg Ji Jk Jr Js Lv Ly Lz Mi Mj Mr Nd Nf Ni Nk Ns Of Og On Pa Qb Qc) Jj(aA Fp Fr Ik Im Ip Iv Jm Jp Jt Lh Lv Md Mg Mi Mr Mz Nd
Nk Nt Nu Nv Nx Pb Pe Pg Pz Qe) Ji(aA Hw Il In Iq Iu Jg Jk Jo Jp Jq Js Ly Me Ml Mq Mt Nd Nf Ni Nk Ns Of Oz Pa Qb) On(Hw In Iq Jk Ly
Me Mt Nd Nf Nk Ns Of Og Om Pa Pg) Jg(Hw In Jh Jk Ly Mi My Nd Nk Nq Ns Of Og Oy Pa) Mi(Ly Nk Oy Pa Pg) Md(Jp Mt Nb Pa) Ly(Aa Jp
Pa) Nk(Jp Pa) Om(Jp Mt) OgPa} Ly{fR(aD Af Al aY Ba bN bS bW cE cH cM cP cQ Db Dc Dd De dH dl dJ dM gP Hr Hu Hv Hx Ii Ik Io Ip Iq
It Jj Jl Jp Jr Js Lv Lz Md Ml Mp Mx Na Nb Nd Ne Nj Og Pb Pc) Lx(Hw In Iu Iv Jg Ji Jk Jo Jp Js Lv Mi Mm Mr Mt Nc Nd Ne Nf Nj Ns Of Og
Om On Pa) Jj(Fp Ih Ik Im Ji Lh Mg Nc Ne Nr Nt Nw Nx On Qe) Gn(aD aG bL bP bX dC dJ Fb Hu Kf Kn Ul Um Un) Ji(Jp Md Mm Mt Nc Ne
Nf Og Om Pa) Jp(Js Mm Nc Nd Ne Nj Og Om Pa) Nw(In Jo Mm Nc Nd Nf Og Om) Mm(Md Mt Nc Nd Ne Pa) Jg(Jh Of Og Om Oy Pa) Aa(Jo
Jr Js Pa) On(Hq Nf Of Om) Md(Mi Mt Nx) Mt(Og Om) Js(bN Ko) DrRc aXbN} Md{Nw(Fp Hw Hx Iq Iv Jh Ji Jj Jr Lv Lx Lz Mb Mi Mm Mr
Ms Mw Nb Nf Nh Nk Nq Nt Nx Of Og Oi On Oz Pa Pb Pc Qd) Jg(Hw Ih Ik Iq Iv Ji Jj Jk Lj Lv Mi Mm Mv Nc Nf Ng Nq Nt Nu Nx Of On Oz
Pa Pb Pc) On(Fp Hq Hw Ij Ik Iq Jj Lv Lx Mb Mj Mm Nc Nf Nh Nq Of Og Oy Oz Pa) Lx(Ik Ji Jj Lv Mi Mm Mt Nc Nd Ne Nh Nj Nx Om Pc Po)
Mt(Ji Jj Mi Nd Nx Om Pa) Mm(Fp Ik Ne Nj) Ji(Nd Ne Om) Jj(Ik Nt Nx) FpNx MiNe NjJp} Om{Jg(Fp Ih Iq Is Iv Ji Lv Mi Mm Mr Mt My Nc
Ne Ng Nh Nj Ns Nw Of Og On Pa) Nw(Hq Hw Hx Ih Ik Jh Ji Jj Jo Jr Lx Mm Nc Nd Ne Nf Nh Nj Ns Nt Pa Qe) Lx(aA Ik Iv Jj Js Lv Mi Mm
Mr Mt Nc Nd Ne Nh Nj Nt On Po) Mt(Fp Iv Jj Jp Lv Mi Mm Mr Nd Ns Nt On Pa) Ji(Fp Ik Jj Mm Nc Nd Ne Nf Nh Nj Nt) On(Iq Jj Js Ne Nj Ns
Oy) Mm(Fp Ik Ne) Jj(Ik Nt) NjJp} Lx{Po(Ik Jg Ji Lv Mi Mr Nc Nd Ne Nh Nj Nt Nw On) Nd(aA Iu Jg Ji Js Lv Mi Mm Mr Mt Nw Og On) Nj(Il
Iu Jg Ji Jp Js Mi Mm Mr Nw Og On Pa) Jj(Mt Nc Ne Nh Nt) Nf(Ji On) MrHq NgJg OnOy} Gn{Kc(Ao Ef Ez Ii Im Jt Kj Kl Of Uc Ue) aV(aD aJ
aQ cN dM dR Fw Kk Qx) Hu(aD cP Kn Ow Um Uo Vo) Kk(Ke Kf Rc Vo) Qw(Ke Vo) MeRc} Jg{Mv(Hw Iq Jj Lv Mt Nc Nf Nh Nj Nq Nw Of
Oz Pa) Ng(Mt Nd Ne Nj Oz) My(Nd Ne Nj Og) Jj(Nc Nd Ne Nj) Oy(Mk Mr On) Nj(Il Og) MiHq NdOg} Jj{Ik(Ji Jp Me Mi Mm Mr Mt Nw Og
On Qe) Nj(Jp Mm Mt Nw On Pa) Nd(Mm Mt Nt Nw On) Ne(Ji Mm Nw) Nt(Mt Pa) MtPa NcNw} Nd{Nw(Js Mm Mt Nc Nj Og Pa) Mt(Ji Mm
Og On Pa) Mm(Ji On Pa) Ji(Og Pa) MefR MiHq} Nj{Nw(Hw Il Iu Jo Mm Og Pa) Mm(Jp On Pa) Ji(Jp Og Pa) On(Hq Il) JpPa} Mi{Hq(Fp Nc
Ne Nh Nt Nw Nx Pa)} On{Oy(Ik Iq Mt Nc Ne Nh Oz) FpNf} Js{Nw(Mt Nc Ne Nf) KobN} Em{aV(dM Qx) MeKj RcKc} aX{aV(Dr eP)
IheM} Ji{Og(Ik Ne)} Kc{Vo(Dr Gc)}

Unconstrained panels with 3 analytes, where 1.0E-6 >= 'model p-value' > 1.0E-7. Contains 9,079 panels of 9,935,646 total panels evaluated. :
Et{Pa(aA Bg Fr Gl Hq Hr Hu Hv Ih Ij Im In Io Ip Ir Is It Iu Iv Jg Jh Ji Jk Jl Jm Jn Jp Jq Jr Kg Lh Li Lj Lu Lv Lx Lz Ma Mb Mc Me Mf Mg Mh
Mi Mj Mk Ml Mm Mn Mp Mq Mr Ms Mu Mv Mw Mx My Mz Na Nb Ng Ni Nk Nm Nn No Nr Nu Nv Nw Nx Ny Oe Oh Oi On Oy Oz Pb Pc
Pd Pe Pf Pg Po Pz Qa Qb Qc Qd Qe Ut) Lv(aA Dc Dk Fr Hq Hr Hu Hv Hx Ih Ii Ij Im In Io Ip Ir Is It Iu Iv Jg Jh Ji Jk Jl Jm Jn Jp Jq Jr Lh Li Lj
Lu Lw Lz Ma Mb Mc Me Mf Mg Mh Mi Mj Mk Ml Mm Mn Mp Mq Mr Ms Mu Mv Mw Mx My Mz Na Nb Ng Ni Nk Nm Nn No Nr Nt Nu Nv
Nw Nx Ny Oe Oh Oi On Oy Pb Pc Pd Pe Pf Pg Po Pz Qa Qb Qc Qd Qe) Js(aA Bg Dc Dk Fr Gl Hq Hr Hu Hv Hw Hx Ii Ij Im In Io Ip Ir Is It Iu
Iv Jg Jh Jk Jl Jm Jn Jp Jq Jt Ko Lh Li Lu Lw Lz Ma Mb Mc Me Mf Mg Mh Mj Mk Ml Mm Mn Mp Mq Ms Mu Mv Mw Mx My Mz Na Nb Ng
Ni Nk Nm Nn No Nq Nr Nu Nv Nx Ny Oe Oh Oi On Oy Pb Pc Pd Pe Pf Pg Po Pz Qa Qb Qc Qd Qe Wm) Jr(aA Dc Dk Fp Hq Hr Hu Hx Ih
Ii Ij Ik Il Im In Ip Is Iu Iv iZ Jg Jh Ji Jk Jl Jm Jn Jp Jq Li Lj Lu Lw Lx Lz Ma Mb Mc Me Mf Mg Mh Mi Mj Mk Ml Mm Mn Mp Mq Mr Ms Mu
Mv Mw Mx My Mz Na Nb Ng Ni Nk Nm Nn No Nr Nt Nu Nv Nw Nx Ny Oe Og Oh Oi Ok On Oy Oz Pb Pc Pd Pe Pg Po Qb Qc Qd Qe) Nf(aA
bN Ch Co Cw Di Fr Gl Hq Hr Hu Hv Hx Ii Ij Im In Io Ip Ir It Iu Jf Jh Jk Jm Jn Jp Jq Kg Kj Kk Lh Li Lu Lw Lz Ma Mb Mc Me Mf Mg Mh Mj
Ml Mm Mn Mp Mq Ms Mu Mv Mw Mx My Mz Na Nb Ng Ni Nk Nm Nn No Nr Nu Nv Nx Ny Oe Og Oh Oi Ou Oy Pc Pd Pf Pg Po Pz Qa Qb
Qc Qd Qe Ut Vo Wm) Jt(aA Bg Dc Dk Fr Gl Hq Hr Hu Hv Hx Ii Ij Im In Io Ip Ir Is It Iu Jh Jj Jk Jl Jm Jn Jp Jq Ko Lh Li Lu Lw Lz Ma Mb Mc
Me Mf Mg Mh Mj Mk Ml Mm Mn Mp Mq Ms Mu Mv Mw Mx My Mz Na Nb Ng Ni Nk Nm Nn No Nq Nr Ns Nu Nv Nw Nx Ny Oe Og Oh Oi
Oy Pb Pc Pd Pe Pf Pg Po Pz Qa Qb Qc Qd Wm) Nt(Fp Fr Hq Hr Hu Hv Hx Ih Ij Ik Im Io Ip Ir Is It Iv Jg Jh Ji Jk Jl Jm Jn Jp Jq Lh Li Lj Lu Lw
Lx Lz Ma Mb Mc Me Mf Mg Mh Mi Mj Mk Ml Mm Mn Mp Mq Mr Ms Mu Mv Mw Mx My Mz Na Nb Nh Ni Nk Nm Nn No Nr Nu Nv Nw
Nx Ny Oe Oh Oi Ok On Oy Pb Pc Pd Pe Pf Pg Po Pz Qa Qb Qc Qd Qe) Oz(aA Dc Dk Fr Hq Hr Hu Hv Hx Ii Ij Im In Io Ip Ir Is It Iu Jg Jh Jk Jl
Jm Jn Jp Jq Lh Li Lj Lu Lw Lz Ma Mb Mc Me Mf Mg Mh Mj Mk Ml Mm Mn Mp Mq Ms Mu Mv Mw Mx My Mz Na Nb Ng Ni Nk Nm Nn
No Nq Nr Nu Nv Nw Nx Ny Oe Og Oh Oi Oy Pb Pc Pd Pe Pf Pg Po Pz Qa Qb Qc Qd Qe) Ns(aA Dc Fr Hq Hr Hu Hv Hx Ih Ii Ij Im In Io Ip Ir Is
It Iu Iv Jh Ji Jl Jm Jn Jp Jq Lh Li Lj Lu Lw Lz Ma Mb Mc Me Mf Mg Mh Mi Mj Mk Ml Mm Mn Mp Mq Mr Ms Mu Mv Mw Mx My Mz Na
Nb Ng Ni Nk Nm Nn No Nq Nr Nv Nw Nx Ny Oe Og Oh Oi Oy Pd Pe Pf Pg Po Pz Qa Qb Qc Qd Qe) Jj(aA Dc Dk Fr Gl Hq Hr Hu Hv Ii Ij Im
In Io Ip Ir Is It Iu Jg Jh Ji Jk Jl Jm Jn Jp Jq Lh Li Lj Lu Lw Lz Ma Mb Mc Me Mg Mh Mi Mj Mk Ml Mm Mn Mp Mq Ms Mu Mv Mw Mx My
Mz Na Nb Ng Ni Nm Nn No Nr Nv Nw Nx Ny Oe Og Oh On Oy Pc Pd Pe Pf Pg Po Pz Qa Qb Qc Qd Qe Ut Wm) Hw(Dc Dk Fr Hr Hu Hv Hx
Ii Ij Im In Io Ip Ir Is It Iu Jg Jh Jk Jl Jm Jn Jp Jq Lh Li Lu Lw Lz Ma Mb Mc Me Mf Mg Mh Mj Mk Ml Mm Mn Mp Mq Ms Mu Mv Mw Mx
My Mz Na Nb Ng Ni Nk Nm Nn No Nq Nr Nu Nv Nw Nx Ny Oe Og Oh Oi Oy Pb Pc Pd Pe Pf Pg Po Pz Qa Qb Qc Qd Qe) Ok(aA Fr Hr Hu Hv

Og Om) Og(Ik Nd Nh) AaNd} aV{aX(eM eX GC gT) dM(dX eM eP) dO(cL cO gP) Dr(aC Qx) GcQx cNeP} Ko{bN(Dk Gl Ma Oe Om Wm)
Js(Di Dk gP Om) fR(Ib Ue) RiOm} Og{Nt(Ik Lv Nd Nj Om Oz) AaNd MrIk} Me{Dr(Fb Jy) Em(Uu Vo) GcJy HfbN OzfR} cL{bA(dO eX gT)
dD(gT Gw) bUdO} Kk{Vo(Dr Gc) HueM} Aa{Om(Nd Nj)} Em{QwVo KjNx} Mr{FpMj NjIl} eP{QwgP aXcY} dOfRgP

Unconstrained panels with 2 analytes, where 1.0E-7 >= 'model p-value' > 0. Contains 36 panels of 77,685 total panels evaluated. : Et(Fp Ik Iq Jj
Jo Ly Md Mt Nc Nd Ne Nh Nj Nl Of Om) Ok(Jo Js Lx Ly Md Mt Nc Nd Ne Nf Nj Nl Of Om) Nl(Ji Lx Mm Nw) LyfR MdNw Unconstrained panels with 2 analytes, where 1.0E-6 >= 'model p-value' > 1.0E-7. Contains 110 panels of 77,685 total panels evaluated. : Et(Dc
Dk Hq Hw Hx Ih Ii Im In Iu Iv Jg Ji Jl Jr Js Jt Li Lj Lv Lx Ma Mb Mc Mf Mi Mk Ml Mq Mr Ms Mv My Nf Ng Nk Nq Ns Nt Nu Nw Oe Og Ok
On Oz Pa Pb Pc Pe Qe) Ok(Fp Hq Hw Hx Ii Ik Iq Iu Jj Jt Lv Mq Nh Nq Ns Nt Og Oz Pa) Lx(Jj Ly Md Nd Ne Nj Om Po) Nl(Jg Jj Jp Mi Mt On
Pa) Nw(Js Ly Nc Nd Ne Nj Om) Ji(Ly Nd Ne Om) Mt(Jj Nd Om) Jg(Md Mv Om) On(Md Om Oy) Jj(Ik Nt) Jp(Ly Nj) GnaV Unconstrained panels with 2 analytes, where 1.0E-5 >= 'model p-value' > 1.0E-6. Contains 313 panels of 77,685 total panels evaluated. : Ok(aA
Fr Hr Hu Hv Ih Ij Il Im In Io Ip Ir Is It Iv Jg Jh Ji Jk Jl Jm Jn Jp Jq Jr Lh Li Lj Lu Lw Lz Ma Mb Mc Me Mf Mg Mh Mi Mj Mk Ml Mm Mn Mp
Mr Ms Mu Mv Mw Mx My Mz Na Nb Ng Ni Nk Nm Nn No Nr Nu Nv Nw Nx Ny Oe Oh Oi On Oy Pb Pc Pd Pe Pf Pg Po Pz Qa Qb Qc Qd Qe)
Et(aA Bg Ch Fr Gl Hr Hu Hv Ij Io Ip Ir Is It Jh Jk Jm Jn Jp Jq Kg Lh Lu Lw Lz Me Mg Mh Mj Mm Mn Mp Mu Mw Mx Mz Na Nb Ni Nm Nn
No Nr Nv Nx Ny Oh Oi Oy Pd Pf Pg Po Pz Qa Qb Qc Qd Ut Wm) Lx(aA Fp Hw Hx Ik In Iq Iu Iv Jg Ji Js Lv Mi Mm Mr Mt Nc Nf Nh Nq Ns
Nt Nw Of Og On Oz Pa) Nl(AA Fp Fr Hw Ip Is Iv Jt Lh Lv Ly Md Mr Nk Ns Nt Nx Og Om Pc Pe Qe) Mt(Fp Hw Iq Iv Jg Ji Js Lv Ly Md Mi
Mm Mr Nc Ne Nj Ns Nt Nw Og On Pa) Nw(Hw Hx Ik In Iq Jj Lv Mm My Nf Nh Nq Ns Nt Of Og Oz Pa) Ly(Aa aX bN cH Dc Gn gP Jg Jj Mi
Mm On Pa) Ji(Fp Ik Iq Jj Md Nc Nf Nh Nj Nt Og Oz Pa) Jg(Jj My Nc Nd Ne Ng Nj Ns Of Og) Mm(Fp Ik Lv Nc Nd Ne Nh Nj Om) On(Jj Nc
Nd Ne Nf Nh Nj) Gn(Fw Hu Kc Kk Ra) Pa(Ne Nh Nj Nt) Jj(Ne Nh Nj) Nt(Og Om) Mi(Hq Nj) Nd(Aa Jp) Ik(Jp Og) MdNx KcbN aJgP Unconstrained panels with 2 analytes, where 1.0E-4 >= 'model p-value' > 1.0E-5. Contains 862 panels of 77,685 total panels evaluated. : Ly(aA
aC AD aE AF aG aH aI AJ aK AL aM aN AO AP aQ AR As aU aV AW Ax aY aZ BA BB BC bE bF BG bH bI bJ bL bM Bn BO bQ bR bS bU
bV bW bX bZ cA cB cC cD cE cF cG Ch cI cJ cK cL cM cN CO CP CQ cR CS CT CU CV cW CX cY cZ dA DB dC DD DE dF DG dH DI dJ
DK DL dM dN Dr EM Ex Fp Fr Hf Id Ih Ik Im Is Iv Jf Jr Jt Kc Ko Lh Li Lj Lv Md Mr Nc Ne Nh Nj Nt Nx Og Ou Pe Qa Qe Sr Uk Ur Tj)
Nw(aA Dc Dk Fp Fr Hq Hr Hu Hv Ih Ii Ij Il Im Io Ip Ir Is It Iu Iv Jg Jh Ji Jk Jl Jm Jn Jo Jp Jq Jr Jt Lh Li Lj Lu Lw Lz Ma Mb Mc Me Mf Mg
Mh Mi Mj Mk Ml Mn Mp Mq Mr Ms Mu Mv Mw Mx Mz Na Nb Ng Ni Nk Nm Nn No Nr Nu Nv Nx Ny Oe Oh Oi On Oy Pb Pc Pd Pe Pf Pg
Po Pz Qa Qb Qc Qd Qe) Mt(aA Fr Hq Hr Hu Hv Hx Ih Ii Ij Ik Im In Io Ip Ir Is It Iu Jh Jk Jl Jm Jn Jo Jp Jq Jr Jt Lh Li Lj Lu Lw Lz Ma Mb Mc
Me Mf Mg Mh Mj Mk Ml Mn Mp Mq Ms Mu Mv Mw Mx My Mz Na Nb Nf Ng Nh Ni Nk Nm Nn No Nq Nr Nu Nv Nx Ny Oe Of Oh Oi Oy
Oz Pb Pc Pd Pe Pf Pg Po Pz Qa Qb Qc Qd Qe) Nl(Hq Hr Hu Hv Hx Ih Ii Ij Ik Il Im In Io Iq Ir It Iu Jh Jk Jl Jm Jn Jo Jq Jr Js Li Lj Lu Lw Lz Ma
Mb Mc Me Mf Mg Mh Mj Mk Ml Mn Mp Mq Ms Mu Mv Mw Mx My Mz Na Nb Nc Nd Ne Nf Ng Nh Ni Nj Nm Nn No Nq Nr Nu Nv Ny Oe
Of Oh Oi Oy Oz Pb Pd Pf Pg Po Pz Qa Qb Qc Qd) Lx(Fr Hq Hr Hu Hv Ih Ii Ij Im Io Ip Ir Is It Jh Jk Jl Jm Jn Jo Jp Jq Jr Jt Lh Li Lj Lu Lw Lz
Ma Mb Mc Me Mf Mg Mh Mj Mk Ml Mn Mp Mq Ms Mu Mv Mw Mx My Mz Na Nb Ng Ni Nk Nm Nn No Nr Nu Nv Nx Ny Oe Oh Oi Oy Pb
Pc Pd Pe Pf Pg Pz Qa Qb Qc Qd Qe) Ji(aA Hq Hw Hx Ih Ii Im In Iu Iv Jg Jo Jp Jq Jr Js Li Lj Lv Mb Mc Mf Mg Mi Ml Mm Mq Mr Ms Mv My
Ni Nq Nr Ns Nu Nx Ny Of Oi On Oy Pb Pc Pe Pg Po Qa Qc Qe) Et(Af aI Aj Ao Aw Bb bN cE Co Cp Ct Cu Cw Dd De Di Ef gP Ha Hc Ib Il Iz
Jf Kc Ke Kj Kk Ko Ks Ou Qt Qw Rg Tn Uk Ur Vo Vp Vs Vu Tj) Gn(aD aJ aK aN aX bR bU cF CH cI cN cP Cs cY dG dI dJ dL Ef Em Gl gP
Ld Me Og Qw Qx Rb Rc Uo Vo) Nt(Fp Hw Ik In Iq Iu Iv Jg Jp Js Lv Md Mi Mm Mr Nc Nd Ne Nf Nh Nj Nq Ns Of On Oz Pb) Jg(Fp Hw Ih Ik
Iq Iu Iv Jh Jk Jo Js Lj Lv Mi Mm Mr Mu Mw Nf Nh Nq Nu On Oy Oz Pa) Jj(Fp Im Iv Jm Jp Jt Lh Li Lv Mg Mm Mr Nc Nd Nr Nu Nx Pa Pc Qa
Qe) On(Fp Hq Hw Ih Ik Iq Jk Js Lj Lv Mm Mv My Nq Ns Nx Of Og Oz Pa) Ko(Bg bN Dc Dk fR Gl gP Jf Jk Js Ma Me Mj Mv Nf Om Qw Ut
Vs) Nj(AA Fp Fr Il Is Iv Jl Jt Lh Li Lj Lv Mr Nx Og Pe Qe) Mm(aA Hw Ih Iq Iv Jp Jr Lj Md Mi Mr Nf Ns Oz Pa Pb) Ne(AA Fp Fr Iv Jp Jt Lh
Lv Md Mi Mr Nx Og Om Qe) Om(Aa Fp Ik Im Jp Lh Li Lv Mi Nh Pa Qa Qe) Fp(Jp Lv Md Mi Mr Nc Nd Nf Nh Og Pa) Lv(Ih Ik Iv Jp Md Nc
Nd Nh Og Pa) Pa(Ik Iq Iv Jp Mi Nc Nd Nx) Nh(aA Jp Md Mi Mr Og Qe) Mi(Ik Md Nc Nd) Kc(dJ Dr Em gP) Nd(Ih Mr Qe) Jp(Iq Md Nc)
cH(aA bA gL) Dc(Ad Dg) Dk(Dg Ok) bN(aJ Wm) DqeF MrIk IqQe KkgP OzfR aVdO Unconstrained panels with 2 analytes, where 1.0E-3 >= 'model p-value' > 1.0E-4. Contains 1,976 panels of 77,685 total panels evaluated. :
Gn(aA aC Ad aE AF aG aH aI Aj AL aM An AO AP aQ AR AS aU AW Ax aY aZ BA BB BC bE bF BG bH bI bJ bL bM BN BO bP bQ bS
bV bW bX bZ cA cB cC cD cE cG cJ cK cL cM CO Cp CQ cR cS CT CU CV CW CX cZ dA DB DC DD DE dF Dg dH Di DK Dl dM dN dO
Dp DR eF EX Ez Fb Fp FR GC gL Gp GW Hf Ib Ic Ih Ij In Iz Jh Jj Jk Js Jt Ju Jv Jy Kd Ke Kf Kj Kl Ky Lj Lu Ma Mf Mn Mr Mu Mv Mw Mz
Nb Ng Nj Nk Nl Nm Nw Nx Ny Oa Oh Oi Ok Om Or Ou Oy Oz Pc Qb Qt Qu Qy Qz Ss St Ue Uf Uk Ul Um Un Uu Tj) Ly(An aS bP Cw Dp
dX Ed EF eP Ez Fn Fw Fy Gc GL Gp Gz Ha Hb HC Hq Hr Hw Ib Ic Ii Il In Io Ip Iq Ir Iu Iz Jd Je Jh Jl Jn Jq Js Ju Jv Jy Kd Kf Kg Ki Kj Kk Kp
Kq Kr Ks Kx Ky Kz Ld Lw Ma Mb Mf Mg Mj Mk Ml Mp Mu Mw Mx Mz Nb Nd Nf Nk Nm Nn No Nr Ns Nu Nv Ny Oa Of Oh Oi Om Or Oy
Oz Pb Pc Pd Pf Pg Ph Pi Pj Po Pz Qb Qd Qg Qh Ql Qm Qn Qt Qu Qv Qw Qx Qy Qz Ra Rb Rc Rf Rg Rh Ri Rj Ss St Tn To Tr Tt Tv Tz Ua Ub
Uc Ud Ue Uf Ug Uh Ul Um Un Uo Up Us Ut Uu Uv Vo Vp Vq Vs Vt Vu Vv) Ko(Af aH aI Aj aL Ao AW aX aZ bC bE bF bJ bL bZ cE cG CH
cM Co Cp CQ Ct Cu Cw Db Dd DE DI dJ dM Ef Ez Fb Fr Fw Fy gL Ha Hc Hf Hq Hu Hw Hx Ib Ic Id Ii Ij In Io Iq Is It Iz Jj Jl Jo Jp Jq Jr Jt Ju
Jv Kc Kc Kg Ki Kj Kp Kq Kr Ks Kz Ld Lh Lj Lx Md Mk Mm Mn Mp Mq Mr Mu Mw Mx Na Nb Nd Nj Nn Nq Nr Ns Nu Nv Ny Oe Of Og Ou
Oy Oz Pa Pb Pc Pe Pg Ph Po Pz Qb Qc Qd Qh Ql Qm Qn Qt Qu Qx Qy Ra Rb Rc Rf Rg Ri Rj Rm Sr Ss Tn Tr Tt Tv Ua Uk Ul Up Ur Uu Vo
Vp Vu Wm Tj) Et(Aa Ad aF aG aH aJ AL AN aO Ap Ar As aU aV aW AX aZ BA bB BC bE bF bJ bL Bn Bo bQ bV bZ cF cG cH cI cK cM
CQ Cs Cv Cx cZ dA Db dE Dg dI dJ Dl dM dN Dp Ed Ez Fa Fb Fn Fw Fy gL Gp Hb hC Hf Ic Id iZ Jd Je Ju Jv Jy Kd Kf Ki Kl Kn Kp Kq Kr
Kx Ky Kz Ld Oa Or Ow Ph Pi Pj Pk Qg Qh Ql Qm Qn Qu Qv Qx Qy Qz Ra Rb Rc Rf Rh Ri Rj Rm Sr Ss St To Tr Tt Tv Tz Ua Ub Uc Ud Ue
Uf Ug Uh Ul Um Un Uo Up Us Uu Uv Vt Vv) Nh(Aa Fr Hq Hr Hu Hv Hw Hx Ih Ii Ik Im In Io Ip Iq Ir Is It Iu Iv Jh Jk Jl Jm Jn Jo Jq Jr Js Jt Lh
Li Lj Lu Lw Ma Mc Me Mf Mg Mj Mk Ml Mn Mp Mu Mw Mx My Mz Nb Nc Nd Ne Nf Ni Nj Nk Nm Nn No Nr Ns Nu Nv Nx Ny Of Oh Oi
Oy Oz Pb Pc Pd Pe Pf Pg Po Pz Qa Qb Qc Qd) Nt(aA Fr Hq Hr Hu Hv Hx Ih Ii Ij Il Im Io Ip Ir Is It Jh Jk Jl Jm Jn Jo Jq Jr Jt Lh Li Lj Lu Lw Lz
Ma Mb Mc Me Mf Mg Mh Mj Mk Ml Mn Mp Mq Ms Mu Mv Mw Mx My Mz Na Nb Ng Ni Nk Nm Nn No Nr Nu Nv Nx Ny Oe Oh Oi Oy Pc
Pd Pe Pf Pg Po Pz Qa Qb Qc Qd Qe) Mm(Fr Hq Hr Hu Hv Hx Ii Ij Im In Ip Ir Is It Iu Jh Jk Jl Jm Jn Jo Jq Js Jt Lh Li Lw Lz Ma Mb Mc Me Mf
Mg Mj Mk Ml Mn Mp Mq Ms Mu Mv Mw Mx My Mz Na Nb Ng Ni Nk Nm No Nq Nr Nu Nv Nx Oe Of Og Oh Oi Oy Pc Pd Pe Pf Pg Po Pz
Qa Qb Qc Qd Qe Wm) Ne(Hq Hr Hu Hw Hx Ih Ii Ik Im In Io Ip Iq Ir Is It Iu Jh Jl Jm Jn Jq Jr Js Li Lj Lu Lw Lz Ma Mc Me Mf Mg Mj Mk Ml
Mn Mp Mu Mw Mx My Mz Nb Nc Nd Nf Ni Nj Nk Nm Nn No Nr Ns Nu Nv Ny Of Oh Oi Oy Oz Pb Pc Pd Pe Pf Pg Po Pz Qa Qb Qc Qd)

Figure 11 Continued

Jg(aA Dc Dk Fr Hq Hr Hu Hv Hx Ii Ij Il Im In Io Ip Ir Is It Jl Jm Jn Jp Jq Jr Jt Lh Li Lu Lw Lz Ma Mb Mc Me Mf Mg Mh Mj Mk Ml Mn Mp Mq Ms Mx Mz Na Nb Ni Nk Nm Nn No Nr Nv Nx Ny Oe Oh Oi Pb Pc Pd Pe Pf Pg Po Pz Qa Qb Qc Qd Qe) Fp(AA Fr Ha Hq Hr Hw Hx Ih Ii Ik Il Im In Io Ip Iq Ir Is Iu Iv Jh Jl Jo Jq Jr Js Jt Lh Li Lw Lz Mc Me Mf Mg Mh Mj Mk Ml Mp Mq Mu Mx Mz Nb Ni Nk Nm Nn No Nq Nr Ns Nu Nv Nx Of Oh Oi Oy Oz Pb Pc Pd Pe Pf Pg Pz Qa Qb Qc Qe) On(aA Fr Hr Hu Hx Ii Ij Il Im In Ip Ir It Iu Iv Jh Jl Jm Jn Jo Jp Jq Jr Jt Lh Li Lz Ma Mb Mc Me Mf Mg Mi Mj Mk Ml Mn Mq Mr Ms Mu Mw Mx Mz Nb Ng Ni Nk Nr Nu Nv Ny Oe Oh Oi Pb Pc Pd Pe Pf Pg Po Pz Qa Qb Qc Qe) Lv(aA Fr Hq Hw Hx Il Im Io Ip Iq Ir Is It Iu Jh Jl Jm Jn Jr Js Jt Lh Li Lj Lw Mc Me Mf Mg Mi Mk Ml Mr Mz Nb Nf Nk Nm No Nq Nr Ns Nu Nv Nx Ny Of Oh Oi Oy Oz Pb Pc Pd Pe Pf Pg Pz Qa Qb Qc Qd Qe) Nj(bN Hw Ih Ii Ik Im In Io Ip Iq Ir Iu Jh Jm Jn Jq Jr Lw Ma Md Me Mg Mj Mk Mp Mu Mw Mx My Mz Nb Nc Nd Nf Ni Nk Nm Nn No Nr Ns Nu Nv Ny Oh Oi Om Oy Oz Pb Pc Pd Pf Pg Po Pz Qa Qb Qd) Kc(Aa aH al aV aX aY aZ bA bF Bg bl bJ bL bZ cA cE cG cH cL cM cP cQ Db Dc Dd DI Dk dM dX eM eP fR Gc Hq Iq Jf Jk Md Me Mj Mu Mv Nf Nr Nu Om Ou Pa Qw Sr Ur Vp Vu) Ik(AA Fr Hu Hw Ih Il Im In Io Ip Iq Is Iu Iv Jl Jo Jq Jr Jt Lh Li Lj Lw Md Me Mj Mk Mz Nb Nc Nd Nf No Nr Ns Nu Nv Nx Of Oz Pb Pc Pe Pg Pz Qa Qe) Pa(AA bN Fr Hw Hx Ih Im In Ip Ir Is Iu Jf Jh Jl Jr Jt Lh Li Lj Lw Mb Md Mf Mg Mk Mr Mx Mz Nb Nf Ni Nq Nr Ns Nu Nv Of Og Oh Oi Pc Pe Pz Qa Qc Rb) Ji(Fr Hr Hu Hv Ij Il Io Ip Ir Is It Jh Jk Jl Jm Jn Jt Lh Lu Lw Lz Ma Me Mh Mj Mk Mn Mp Mu Mw Mx Mz Na Nb Ng Nk Nm Nn No Nv Oe Oh Pd Pf Pz Qb Qd) Nc(AA Fr Hw Ih Im Ip Iq Is Iv Jh Jl Jr Jt Lh Li Lj Lw Md Mg Mk Mr Mz Nb Nd Ni Nk No Nr Ns Nu Nv Nx Og Om Oz Pb Pc Pe Pf Pg Pz Qa Qe) Jp(aA Dc Dk Gl gP Hw Hx Ih Im Ip Is Iv Jl Jr Js Lh Lj Lw Mb Mf Mi Mk Mr Mv Nf Ng Ni Nk Nq Nr Ns Nu Nx Of Og Oi Oz Pb Pc Pe Pg Qe Ut) Jj(aA Fr Hw Ih Ii Ij Ip Ir Is It Jh Jl Jn Jr Lj Md Mf Mi Mk Mx Mz Nn Nv Oh Oi Om Oy Oz Pb Pc Pd Pf Pg Pz Qb Wm) Nf(Aa aJ Ar aX bN cH Dg fR gP Id Iv Jf Jt Kk Lh Li Mi Mr Nx Ou Pe Ph Qe Qw Rb Sr Uh Ur Vq) Om(aA Ap bN cH Dg DI Fr Id Ih Is Iv Jh Jl Jt Lj Md Mr Nr Nu Nv Nx Ou Pe Pg Ph Sr St Uh) gP(AP Ar bA Bb Bc cH Dg DI dM eF fR gL iZ Jf Kp Me Nd Nw Ok Ou Qw Qy Rb Sr Ur Wm) Nd(aA aX bN Dg FR Hw Im Ip Is Iv Jl Jt Lh Li Lj Lw Nr Nu Nv Nx Og Pe Pg Qa) bN(aA Ap bA cH DG DI gL It Kk Kp Me Mt Nw Ok Ou Pc Ph Qe Qw Rb) Mi(Hw Hx Ih Im In Iq Iv Jr Li Lj Ns Nu Nx Of Og Oy Oz Pe Pg Qe) Me(Gz Hf Id Jf Ki Kk Kp Kr Ou Ph Qw Sr Ur Vp Vq Wm) Dg(al Ao aW Bg cE CH Co Ct Db Dd De Di Jk Vo) aA(aD aJ aV aX bA bR bU cB cM dE dJ Jr Nx) Md(Lh Li Mr Mw Nb Nu Nv Pc Pe Pg Qe Wm) aJ(Aa aV bA bL bR bU cB cH cM Db dJ) Wm(Aa gL hC In Mj Mr Nm Ok pF Pg) Nx(Dc Ha Ih Iv Mr My Og Qe Ut Vu) cH(aP aW cB cP cR Db dF dG dM eF) Iq(Ih Im Jt Lh Li Mr Pe Qa) Kk(Aa dJ Dr EM fR Gc Mj) Dc(Ap Dl It Lx Ok Qe Sr) Nw(Bg Gl Ha Ut Vp Vu Tj) cL(dO Dq eX gN GT Gw) fR(Db dO Ou Pc Qw Qx Rb) Qe(Hw Mr Nq Og Oz Qc) bA(bU bZ cB cT Db dM) Aa(Jf Jr Lx Mt Oz) Ou(aX Bg Hq Jk Mu) Mr(Hw Iv Og Oz) aV(Dr eP eX Gc) Dk(Ad Ap Dl) Lx(Gl Ha Il) Jf(It Ph Pj) Og(Iv Jt Nu) Ok(Bg Gl Ut) Oz(Ih Iv Lh) aX(Mj Qw Vq) Em(Qx Vo) Hw(Ih Pe) Sr(Jk Js) Qy(Jk Mu) eF(DV) iZ(hC Jr) BaCt DdGw HaLj MtIl ItUr cMdM cNdO dJgL

Unconstrained panels with 2 analytes, where 1.0E-2 >= 'model p-value' > 1.0E-3. Contains 5,434 panels of 77,685 total panels evaluated. :
Kc(aA aC AD aE AF aG aJ aK AL aM AN aO AP aQ AR AS aU AW Ax Ba BB BC bE bG bH bM Bn BO bP bQ bR bS bU bV bW bX cB cC cD cF Ch cI cJ cK cN CO Cp Cq cR CS CT CU CV CW CX cY cZ dA dB dC dD DE dF DG dH dK DL dN Dp dR Ed EF Ex Ez Fa Fb Fn Fp Fr Fw Fy GL Gp gW Gz Ha Hb HC Hf Hr Hu Hv Hw Hx Ib Ic Id Ih Ii Ij Ik Il Im In Io Ip Ir Is It Iu Iv Iz Jd Je Jg Jh Ji Jj Jl Jm Jn Jo Jp Jq Jr Js Jt Ju Jv Jy Kd Ke Kf Kg Ki Kj Kk Kl Kn Kp Kq Kr Ks Kx Ky Kz Ld Lh Li Lj Lu Lv Lw Lx Lz Ma Mb Mc Mf Mg Mh Mi Mk Ml Mm Mn Mp Mq Mr Ms Mt Mw Mx My Mz Na Nb Nc Nd Ne Ng Nh Ni Nj Nk Nl Nm Nn No Nq Ns Nt Nv Nw Nx Ny Oa Oe Of Og Oh Oi Ok On Or Ow Oy Oz Pb Pc Pd Pe PF Pg Ph Pi Pj Pk Po Pz Qa Qb Qc Qd Qe Qg Qh Ql Qm Qn Qt Qu Qv Qx Qy Qz Ra Rb Rc Rf Rg Rh Ri Rj Rm Ss St Tn To Tr Tt Tv Tz Ua Ub Uc Ud Ue Uf Ug Uh Uk Ul Um Un Uo Up Us Ut Uu Uv Vo Vq Vs Vt Vv Wm Tj) Nf(aA AD AF aG aH aI Aj aK AL aM AN AO AP aQ aR AS aU aV AW Ax aY aZ BA BB BC bE bF BG bH bI bJ bL bM Bn BO bQ bR bS bU bV bW bX bZ cA cB cC cD cE cF cG Ch cI cJ cK cL cM cN CO CP CQ cR CS cT CU CV CW CX cY cZ dA DB DC DD DE dF dG dH dI dJ dK DL dM dN Ed eF Ex Ez Fa Fr Fy GL Gn Gz Ha Hb HC Hf Hw Ib Ic Ih Ii Im Ip Is IZ Jd Je Jj Jl Jr Ju Jv Jy Kd Ke Kf Kg Ki Kj Kl Kn Kp Kq Kr Ks Kx Ky Kz Ld Lj Lw Mk Nb Nc Nd Nr Nu Nv Oa Om Or Pb Pc pF Pg Pj Qa Qg Qh Ql Qm Qn Qt Qu Qx Qy Ra Rc Rf Rg Rh Ri Rj Rm Ss St Tn To Tr Tt Tv Tz Ua Ub Uc Ud Ue Uf Ug Uk Ul Um Un Up Ut Uu Uv Vo Vp Vs Vt Vu Vv Wm Tj) Ko(AA aC AD aE aF aG aJ aK Al aM AN aO AP aQ AR AS aU aV Ax aY BA BB Bc bG bH bI bM Bn BO bP bQ bR bS bU bV bW cA cB cC cD cE cF cI cJ cK cL cN cO cP cR CS cT cU CV cW CX cY cZ dA dB dC dD dF DG dH dK DL dN Dp dR dX Ed eF eM eP Ex Fa Fn Fp Gn Gp gW Gz Hb hC Hr Hv Ih iJ Ik Il Im Ip Ir Iu Iv iZ Jd Je Jg Jh Ji Jm Jn Jy Kd Kf Kk Kl Kn Kx Ky Li Lu Lv Lw Lz Mb Mc Mf Mg Mh Mi Ml Ms Mt My Mz Nc Ne Ng Nh Ni Nk Nl Nm No Nt Nw Nx Oa Oh Oi Ok ON Or Ow Pd PF Pi Pj Pk Qa Qe Qg Qv Qz Rh St To Tz Ub Uc Ud Ue Uf Ug Uh Um Un Uo Us Uv Vq Vt Vv) gP(AA AD AF Aj Al An Ao As aV AW AX Ba bC bE Bg bJ bM BN Bo bR bU bV bW cB cE Ch cJ cM cN Co CP CQ cR Cs CT Cu Cv Cw Cx Db Dc Dd DE dF dG DI dJ Dk dL Ed Ef eM Ez Fp Fr Fw Fy Gl Gp Gt Gw Ha Hb Hc Hq Ic Id Ik Im In Io Iq It Jd Je Jg Ji Jj Jk Jm Ju Jv Jy Kd Ke Kf Ki Kl Kn Kq Kx Ky Kz Ld Lh Lj Lv Lx Md Mm Mt Mu Mv Nj Nr Nu Nx Oe Oh Om On Or Oy Oz Pa Pb Pc Pf Pn Pj Qa Qd Qe Qg Qh Ql Qt Qx Ra Rf Rg Ri Rj St Tr Ua Ud Ue Uf Uh Uk Ul Un Up Us Ut Uv Vp Vq Vs Vt Vu Vv Tj) Gn(Do Dq DV Ed eM eP Et Fa Fn Fy gN GT Gz Ha Hb Hc Hq Hr Hv Hw Hx Id Ii Ik Il Im Io Ip Iq Ir Is It Iu Iv Jd Je Jf Jg Ji Jl Jm Jn Jo Jp Jq Jr Kg Ki Kn Kp Kq Kr Ks Kx Kz Lh Li Lv Lw Lx Lz Mb Mc Md Mg Mh Mi Mj Mk Ml Mm Mp Mq Ms Mt Mx My Na Nc Nd Ne Nh Ni Nn No Nq Nr Ns Nt Nu Nv Oe Of On Ow Pa Pb Pd Pe Pf Pg Ph Pi Pj Pk Po Pz Qa Qc Qd Qe Qg Qh Ql Qm Qn Qv Rf Rg Rh Ri Rj Rm Sr Tn To Tr Tt Tv Tz Ua Ub Uc Ud Ug Uh Up Ur Us Ut Uv Vp Vq Vs Vt Vv Wm) Dg(AA aC AD AF aG aH AJ aK AL aM AN aO AP aQ Ar As aV Aw AX aY aZ BA BB BC bE bF bI bJ bL bM Bn BO bQ bR bS bU bV bW bX bZ cA cB cC cD cF cG cI cJ cK cL cM cO CP CQ cR CS cT Cu Cv CW CX cY cZ dE dF dH dI dJ dK DL dM Ef Ez Fr GL Ha hC Hq Hw Ii In Iq It iZ Jf Jj Jl Jo Js Kg Kj Kk Kp Ma Md Me Mj Mk Mp Mr Mu Mv Nj Nw Oe Of Ou Oy Pa Pb Pc Pg Po Qt Qw Rb Ss Ua Uk Ur Ut Vp Vs Vu Tj) Nd(aC Ad aH aI aJ aL aN AP Ar As aU aV aW Ax aZ BA Bb BC bE bF Bg bH bI bJ bL bR bU bV bW bZ cB cE cF CH cI cJ cL cM cN cO cP cQ Cs CT Cv cY cZ dA Db Dc Dd dE dF dG DI dJ Dk DL dM eF gL Hq Hr Hv Id Ii Ij Il Io Iq Ir It Iu Jf Jh Jk Jm Jn Jo Jq Jr Js Lu Ma Mc Md Me Mf Mg Mj Mk Ml Mn Mp Mq Mu Mv Mw Mx My Mz Nb Ni Nk Nm Nn No Nq Ns Ny Of Oh Oi Om Ou Oy Oz Pb Pc Pd PF Ph Po Pz Qb Qc Qd Rb Sr) Om(Ad aJ aP Ar As aV AX BA Bb Bc bE Bg bI bJ bV cB cH cM cP cQ Cs Cu Cv Db Dc Dd dF dG DI dJ dM eF Ex fR Fy gL Hb HC Hw Ic Ii Ij Io Ip Iq Ir Iu Jd Jf Jm Jn Jq Jr Ke Kf Kk Kl Kp Kq Ky Kz Lw Ma Mf Mg Mj Mk Mp Mu Mw Mx Mz Nb Nm Nn No Ns Ny Og Oh Oi Oy Oz Pb Pc Pd PF Pj Po Pz Qb Qc Qd Ql Qm Qw Qx Qy Rb Rf Rg Rh Ri Rj Rm Tn To Tr Tt Tz Uc Ue Uf Ug Uk Ul Un Ur Uu Vp Vq Vs Vt Vv Wm Tj) Me(aJ aP Ar aW aX aZ bA Bg bJ bV cB cH cM cP Db Dc dE dJ Dk dM Dp Dr Ed Ef Ex Ez Fa Fb Fn fR Fw Fy GL Gp Ha Hb HC Ib Ic Iv IZ Jd Je Jj Jp Ju Jv Jy Kd Ke Kf Kg Kj Kl Kn Kq Ks Kx Ky Kz Ld Ly Mi Mr Nc Nx Oa Or Ow Pa pF Pi Pj Pk Qe Qg Qh Ql Qm Qn Qt Qu Qv Qx Qy Qz Ra Rb Rc Rf Rg Rh Ri Rj Ss St Tn To Tr Tt Tv Tz Ua Ub Uc Ud Ue Uf Ug Uh Uk Ul Um Un Uo Up Us Ut Uu Uv Vo Vs Vt Vu Vv Tj) cH(Aa aC AD aE aF aG aH aI aK aL aM aN aO Ap aQ AR aS aU aV aX aY aZ Ba BB BC bE bF bG bH bI bJ bL bM bO bP bQ bR bS bU bV bW bX bZ cA cC cD cE cF cG cI cJ cK cL cM cN cO cQ cS cT cU CV cW cX cY cZ dA dB DC DD dE dH DI dJ DK DL dN dR eP FR Gt hC Id In Iq It iZ Jf Jj Jk Jp Kk Lv Lx Md Mt Nj Nu Nw Nx Oe Ok Ou Oy Oz Pa Pb Pc Ph Qw Qx Qy Rb Ur Wm) aA(Aa aC Ad aE

Is Jh Jl Jr Js Jt Lw Mf Mg Mk Nb Ns Nv Og Oi Oz Pb Pg Qa Rg Rj Vp Tj) Og(Dr Em eP Fr Hw Im Ip Iq Ir Is Jh Jl Jr Mf Mg Mk Nb No Nr Nv Oh Oi Oy Oz Pb Pf Pg Pz Qa) Ap(aH aI Aj Ao aW Bg bU cE Ch cM Co cP Ct Cw Db Dd Di dM Gl Iq Jk Mu Mv Ut Vo Vs Vu) Dc(Ba Bb Bc Cv eF Fp Gw hC Id Ji Jm Jt Kf Kp Kq Mm Mt Nr On Oy Pj Qa Qx Qy Rf St Uh) It(Ar aX Bg Ch Ct Dd dJ Dk Fp Gl Ha hC Ib Ic Id Jv Kj Kz Qx Qy Uk Ut Vo Vp Vs Vu Tj) dF(aD aH aI aV aW bF bJ bQ bR bU bZ cB cE cG cK cL cM Db dH Di dJ dM dO dV eP eX) Qa(Fr Hw Hx In Ip Is Iu Jk Jl Jr Js Jt Lw Mf Mg Mk Nq Nr Ns Of Oz Pb Pg Qb Qc) aX(bU cB dO Dr cM cP Id Iq Jg Jk Kp Lx Mt Mu Mv Nr Oe Oy Oz Pb Qx Qy Rj Vo Vs) dM(Ad aK aQ aV bL bR bU cB cC cF cJ cK cP cQ cR cT Db dE dG Di dJ dO dX EM) Fp(eM Hu Hv Ij Jk Jm Jn Lu Ma Mb Mn Ms Mv Mw My Na Ng Ny Oe Po Qd Vp) Im(Fr Hw Hx In Ip Is Iu Jl Jr Js Jt Lw Mf Mk Nb Nq Nr Ns Of Oz Pb Pg) dG(aV aW bL bR bU bZ cB cE cF cK cL cM cP cR Db dH Di dJ dO dV eP gC) Nr(Bg Dk Gl Ha hC Hw Iq Is Jl Jt Ns Oz Pb pF Ut Vo Vp Vs Vu Tj) On(Bg Dk Gl Ha Hv Io Is Lu Lw Mh Mp Na Nm Nn No Qd Ut Vp Vs Vu) eP(aD aK aM aW bR cB cF cN cP cY dJ eF Hu Ib Kz Mf Oz Pb Qx Qy) iZ(aZ bE bJ bL bQ bU cJ cM cN Db dK Ex Gz Hx Mj Nk pF Vp Vq Vs) Id(Dk Gl Ha In Jk Kp Mj Mm Mu Mv Oe Po Qy Ri Rj Ut Vp Vu Tj) eM(aD aN aV bR cN Cs dJ Ib Jy Kf Kz Ld Oa Oz Pb Qx Qz Rf Uk) Iq(Ar bJ Fr hC Hw Ir Is Jh Jl Jr Kp Mg Mk No Nv Pb Pf Pg) cB(aD aN aP aV aW BC bJ bU bV cM cP cR dA Db dE Di dJ) Kp(Bg Dk Gl Ha Jk Lx Mj Mm Mu Mv Nm pF Ut Vo Vp Vs Vu) eF(Bg cE Ch cM Ct Db dE Di Dk dO gN Gt Gw Jk Mu Mv) Lx(Bg Ch Co Ct Db Di Dk Ib Qt Ua Ut Vp Vs Vu Tj) Qy(Bg cE Ch dJ Dk hC Hq Ib Mj Mk Mv Ua Ut Vp Vu) Jt(Fr Hw Hx In Iu Jo Jr Mb Mf Nq Ns Of Oz Pb Pg) Vq(Ct hC Jk Jn Jo kS Ky Mq Mv Oy pF Ra Ri Uk Vs) aP(aK aV aW bL bR bU cC cK cM cP cR dJ dO dV Mu) Ne(Hv Ij Il Jk Jo Mb Mh Mq Ms Mv Na Ng Nq Oe) Oz(dX Ex Fr Hw Ip Ir Is Jl Jr Lw Mk Nb Nv Pg) aV(aU cR dA Do Dq DV dX Em gC gN GT Gw) Oy(Bg Ch Ct dJ Dk Gl Ha Ua Ut Vp Vs Vu Tj) hC(cJ Fw Hx In Jr Mj Nk Ri Rm Uh Up Vp Vs) Mm(Bg Gl Ha Io Lu Mh Nn Ny Ut Vo Vp Vs) Nh(Ij Il Lz Mb Mh Mq Ms Mv Na Ng Nq Oe) Jk(Ad Ar Ba Bb bV Hc Kf Kq Qx Rf St Uh) Fr(Hw Is Jl Jr Mb Mf Mv Nq Ns Of Pb) Em(aN aW bR Kd Kj Ld Or Ue Uk Uo) Gt(aK aN Bo bR cF cG cN cY Dd Fw) Is(Hw In Jr Mb Mf Mg Nq Ns Pb Pg) Uh(Bg Dk Gl Ha Mj Mu Mv Ut Vs Vu) Ar(Ha Hq Ma Mj Mu Mv Pg Po Vu) Jg(Bg Ch Ct Ef Gl Ut Vo Vs Vu) Jr(Hw Il Ip Jl kQ Ns Pb pF Pg) bU(aW Bc bV cP cR dA Db dE Di) Dq(aK aQ bC cF cN cP cY Fw) Qx(Bg cE Dr dX Gc Mu Mv Vs) Ad(Aj Bg Ch Ct Db Dd Di) Dk(Ba Bb Ji Kf Kq Mt St) Gw(aD aN bC cN cP Db Dr) Nm(Bg Ri Uk Vo Vs Vu Tj) Jl(Hq Hw Mb Mf Ns Pb Pg) Kq(Bg Gl Mu Mv Ut Vo) Nv(Hw Hx Js Nq Ns Of) pF(Hx Mj Nk Ri Vp Vs) Di(aW Ba Bb bC cP) St(Dr Mj Mu Vs Vu) dV(bF cE cG cL cN) eX(aK cE cY dJ dR) Gc(Hu Kj Ue Vo) Mt(Bg Ch Gl Ut) Hw(Ip Mg Mk Pg) Rf(Mj Mu Oe Vs) cP(Bc cM cR Db) dO(bQ cE cR dL) dX(aD aW Ib Pb) Dr(Hu Ld Ra) cL(Do Dv gC) Ba(Bg Ch) Bb(Mv Vu) Ex(Up Vo) Ha(Ax Oa) Kf(Vs Vu) Ri(gW Ic) Pg(Nq Ns) bV(cM Mj) cG(gN gT) DbbC DoFw GlJi MuHc JoPj PbdJ aKgN bEcM

Constrained panels with 3 analytes, where 1.0E-9 >= 'model p-value' > 0. Contains 106 panels of 9,935,646 total panels evaluated. : Et{Om(Fp Ih Ik Iv Ji Jj Jo Jr Lx Ly Md Mi Mr Mt Nc Nd Ne Nh Nj Nl Nt Ok On Pa) Nl(Hw In Iq Iu Jj Jo Js Jt Ly Md Mi Nd Nk Ns Of Og Ok Pa) Nd(Jj Jo Lx Ly Md Mt Nc Of Ok Pa) Ly(Jj Jo Js Md Nc Of Pa) Md(Jg Mt Mw Nc Ne Nj) Jo(Ik Lv Nc Ne Nj Nt) Nj(Jj Of Pa) MiHq NeJj} Ok{Nl(Hq Jj Jo Js Md Om) Jo(Ik Ly Nd Nj Om) Om(Jj Js Lx Mt) Md(Ly Nd Nj) PoLx} Md{Nl(Jg Nw On) Ly(Jg Nw) JgOm} Gn{Kc(Uu Vo) HuRa aVaX} MiNlHq Constrained panels with 3 analytes, where 1.0E-8 >= 'model p-value' > 1.0E-9. Contains 348 panels of 9,935,646 total panels evaluated. : Et{Md(Fp Hw Ik Iq Iv Ji Jj Jo Jr Js Lv Lx Mi Nb Nh Nt Nu Nw Nx Of Ok On Oz Pa Pb Pc) Jo(Fp Ih Iq Iv Ji Jr Lx Mf Mg Mi Mr Mt Nh Ns Ok On Oz Pa Pb) Ly(Dc Dk Hw Ih Iu Jt Lj Lx Mi Mt Nc Nf Nj Ns Og Ok) Nd(aA Fp Ih Iu Ji Js Jt Lj Mi Mr Ne Nf Nj Ns Og On) Ne(Hw Iq Iu Js Jt Mi Ns Of Og Ok Pa) Nc(Hw Iq Iu Jj Js Jt Ns Of Ok Pa) Mt(Hw Iq Jj Js Jt Nj Nq Ns Of) Om(aA Iq Jg Js Lj Lv Ns Qa Qe) Nj(Iu Js Jt Lx Mi Mr Og Ok) Ik(Jj Jt Of) Nf(Ok On) Nh(Jj Of) PoLx NtJt MvJg NlaA IqOk} Ok{Md(Fp Hw Ik Iq Jg Jo Js Lv Lx Mt Mw Nc Ne Nf Nh Nw Nx Of Og Om Oz Pa) Nl(Hw In Iq Iu Jk Jt Lx Ly Me Mm Mq Mt Nd Nf Nk Of Og Pa) Nd(Hq Iu Jj Js Lx Ly Mm Mt Nc Nf Of Og Om Pa) Ly(Hq Jj Js Lx Mq Mt Nc Nf Of Og Om Pa) Nj(Hq Iu Jj Jp Js Lx Mt Nf Of Og Om Pa) Om(Fp Hq Ik Iq Jg Nc Ne Nf Of Pa) Ne(Hq Jj Jo Js Nf Of) Mt(Hq Hw Iq Js Nf) Nc(Hq Jj Jo Js Of) Nf(Fp Js Lx Pa) Jo(Iq Lv Oz Pa) LxIq MiHq IkJj} Md{Jg(Fp Lx Mt Nd Ne Nh Nj Nw Og) Nw(Ik Js Mt Nc Nd Ne Nj Om) On(Ly Mt Nd Ne Nj Om) Nl(Ji Lx Mi Mm Nx) Ly(Jp Lx)} Nl{Jj(Jg Ji Lx Ly Mm Mt Nw On Pa) Om(Jg Ji Lx Mm Nw) Nw(In Js Mm) Jg(Mv Ng) On(Hq Oy) PoLx MmPa JiOg} Ly{Jj(Jg Jp Lx Mm Mt Pa) Jg(Mv My Ng) PoLx GnRc MiHq JsNw OnOy} Om{Jg(Jj Lx Mv) Mt(Ji Nw) GnHu LxJi JsNw} Gn{Kc(Cw Kf Nm) aV(aU cY) HuQz} Lx{Jj(Ik Nd Nj) MiHq MvJg} Mi{Hq(Ik Mt Nj)} Mv{Jg(Nd Ne Og)} Nj{JsNw OnOy} NdOnOy IkJjPa Constrained panels with 3 analytes, where 1.0E-7 >= 'model p-value' > 1.0E-8. Contains 1,118 panels of 9,935,646 total panels evaluated. : Et{Nf(Ao Bg Dc Dk Fp Hw Ih Ik Iv Jg Ji Jj Jr Js Jt Lv Lx Mi Mr Mt Nh Nt Nw Of Pa Pb) Ns(Fp Hw Ik Iq Jg Ji Jj Jr Js Lv Lx Nh Nt Nu Of Ok On Oz Pa Pb Pc) Hw(Fp Hq Ih Ik Iv Ji Jj Jo Jr Jt Lj Lv Lx Mi Mr Nh Nt Ok On Pa) Jt(Fp Ih Iv Jg Ji Jr Lj Lv Lx Md Mi Mr Nh Ok On Oz Pa Qe) Ok(Fp Hq Hx Ii Ik Jj Js Lv Lx Mq Mt Nh Nq Of Og Oz Pa) Iq(Fp Ih Ik Iv Ji Jj Jr Lj Lv Lx Mi Mr Nh Of On Pa) Js(Fp Ih Ik Ji Jr Lj Lv Lx Mi Mr Nh Nt Nw Oz Pa) Nq(Fp Ih Iv Jg Ji Jj Jr Lv Lx Mi Mr Nt On Pa) Jj(Fp Hx Ih Iv Jr Lv Lx Mr Nt Nu Oz Pa Pb) Of(Fp Iv Jg Lv Lx Mi Mr Nt On Oz Pa Pb) Jo(aA Dc Dk Gl Hx Jg Kk Mb Nu Ou) Ik(Ii Iu Lj Lx Mg Mi Ng Og Pa) Oz(Ih Iv Ji Lv Lx Mi Mr Nt On) Fp(Dc In Iu Mq Mt Pa Po) Nt(Ii In Iu Ng Og Pa) Mt(Ii Iu Jk Mv Ng Pa) Dk(Gl Jf Om Pa Pb) Lx(Hq Hx Ii Iu Nh) aA(Ly Md Nc Ne Nj) Dc(Gl Jf Om Pa) Mr(Hq Md Mj Oy) Nh(Iu Mi Og Pa) Gl(Jf Om Ur) Ly(Ao Bg Ch) Iv(Hq Ij Oy) Lv(Og Pa) Jg(My Ng) On(Hq Oy) Pg(Mi Wm) BgOm MbMd MkOy IhIn JfUt} Ok{Lx(Hq Hw Hx Ii Ij Ik Iu Jj Jk Jo Js Jt Mq Mv Nc Ne Nh Nq Of Og Oz) Iq(Fp Hq Ih Ik Jg Jj Jp Js Jt Lj Mq Nc Nd Nc Nf Nh Nj Of Og Oz Pa) Mt(Ii Ij In Iu Jj Jk Jo Jt Mq Mv Nc Ne Ng Nq Ns Of Og Oy Oz Pa) Nf(Hq Hw Ik Im Iv Jo Jt Mi Mq Mr Nc Nh Nw Of On Oz Pb) Js(Fp Hw Ih Ik Jj Jo Jr Lv Nh Nq Nt Of Og Oz Pa) Ly(Fp Hw Ih Im Iu Jk Jp Jt Mm Ne Nh Nj Oy Oz) Og(Hq Hw Hx Ik Jo Jt Lv Nc Ne Nh Nt Of Oz Pa) Hq(Fp Hw Ik Iv Lv Md Nh Nr Of Oz Pa Pb) Nc(Hw Ii In Iu Jk Jt Mm Mq Ns Oz Pa) Ne(Hw Ii In Iu Jk Me Mm Mq Nd Ns Pa) Jj(Fp Hw Hx Lv Md Nh Nq Nt Oz Pa) Om(aA Im Lv Mm Mq Nh Nr Ns Nw Oi) Jo(Fp Hw Hx Mf Nh Nq Ns Nt Pb) Nd(Fp Hw Ih Jp Me Mq Nj) Of(Hx Ik Jg Lv Nh Oz Pa) Nj(Hw Jt Me Mm Mq Oz) Md(Hx Jt Mi Mm Nt) Mq(Fp Ik Nh Oz) Pa(Hw Ik Jt Nh) Jg(Jt Mv Ng) NhHw IkJt} Nl{Jj(Fp Fr Ik Im Iv Jm Jp Jt Lh Lv Md Mg Mi Mr Nk Nt Nu Nv Nx Pb Pe Pg Pz Qe) On(Hw In Iq Jk Lx Ly Me Mm Mt Nd Nf Nk Ns Of Og Om Pa Pg) Jg(Hw In Jh Jk Lx Ly Mi Mm My Nd Nk Nq Ns Of Og Oy Pa) Mm(aA Fp Hw Iu Ji Lv Lx Ly Mi Mr Nd Ni Nk Ns Og) Ji(Hw In Iq Iu Lx Ly Me Mt Nd Nf Nk Ns Oz Pa) Nw(Hw Iu Jk Jr Ly Ml Nd Nf Nk Ns Of Og Pa Po) Lx(Hw In Iu Jk Js Lv Ly Mi Nd Nk Ns Og) Mi(Ly Nk Oy Pa Pg) Md(Jp Mt Nb Pa) Ly(Aa Jp Pa) Nk(Jp Pa) Om(Jp Mt) OgPa} Lx{Ly(Hw In Iu Jg Ji Jp Js Lv Mi Mm Mr Nc Nd Ne Nf Nj Ns Of Og Om On Pa) Om(aA Ik Iv Jj Js Lv Md Mi Mm Mr Mt Nc Nd Ne Nh Nj Nt Nw On Po) Md(Ik Ji Jj Lv Mi Mm Mt Nc Nd Ne Nh Nj Nw Nx On Pc Po) Po(Ik Jg Ji Lv Mi Mr Nc Nd Ne Nh Nj Nt Nw On) Nd(aA Iu Jg Ji Js Lv Mi Mm Mr Mt Nw Og On) Nj(Iu Jg Ji Jp Js Mi Mm Mr Nw Og On Pa) Jj(Mt Nc Ne Nh Nt) Nf(Ji On) MrHq NgJg OnOy} Ly{Jj(Fp Ih Ik Im Ji Lh Mg Nc Ne Nr Nt Nw Nx On Qe) Gn(aD aG bL bP bX dC dJ Fb Hu Kf Kn Ul Um Un) Ji(Jp Md Mm Mt Nc Ne Nf Og Om Pa) Jp(Js Mm Nc Nd Ne Nj Og Om Pa) Nw(In Jo Mm Nc Nd Nf Og Om) Mm(Md Mt Nc Nd Ne Pa) Jg(Jh Of Og Om Oy Pa) Aa(Jo Jr Js Pa) On(Hq Nf Of Om) Md(Mi Mt Nx) Mt(Og Om) Js(bN Ko) DrRc aXbN fRgP} Md{Jg(Hw Ik Iq Iv Ji Jj

Figure 11 Continued

Jk Lv Mi Mm Mv Nc Nf Ng Nq Nt Nu Nx Of On Oz Pa Pb) On(Fp Hq Hw Ij Ik Iq Jj Lv Mb Mj Mm Nc Nf Nh Nq Nw Of Og Oy Oz Pa) Nw(Fp Hw Iq Iv Lv Lz Mi Mm Mw Nh Nt Nx Og Oz Pa) Mt(Ji Jj Mi Nd Nx Om Pa) Mm(Fp Ik Ne Nj) Ji(Nd Ne Om) Jj(Ik Nt Nx) FpNx MiNe NjJp} Om{Jg(Fp Ih Iq Iv Ji Lv Mi Mm Mr Mt My Nc Ne Ng Nh Nj Ns Nw Of Og On Pa) Mt(Fp Iv Jj Jp Lv Mi Mm Mr Nd Ns Nt On Pa) Nw(Ih Ik Jj Mm Nc Nd Ne Nf Nh Nj Ns Nt Pa) Ji(Fp Ik Jj Mm Nc Nd Ne Nf Nh Nj Nt) On(Iq Jj Js Ne Nj Ns Oy) Mm(Fp Ik Ne) Jj(Ik Nt) NjJp} Jj{Ik(Ji Jp Me Mi Mm Mr Mt Nw Og On Qe) Nj(Jg Jp Mm Mt Nw On Pa) Nd(Jg Mm Mt Nt Nw On) Ne(Jg Ji Mm Nw) Nt(Mt Pa) Nc(Jg Nw) MtPa MvJg} Gn{aV(aD aJ aQ cN dM dR Fw Kk Qx) Kc(Ao Ef Ez Im Jt Kl Of Uc) Hu(aD cP Kn Ow Um Uo Vo) Kk(Ke Kf Rc Vo) Qw(Ke Vo) McRc} Jg{Mv(Hw Iq Lv Mt Nc Nf Nh Nj Nq Nw Of Oz Pa) Ng(Mt Nd Ne Nj Oz) My(Nd Ne Nj Og) Oy(Mk Mr On) Og(Nd Nj) MiHq} Nd{Nw(Js Mm Mt Nc Nj Og Pa) Mt(Ji Mm Og On Pa) Mm(Ji On Pa) Ji(Og Pa) MiHq} Nj{Nw(Hw Iu Mm Og Pa) Mm(Jp On Pa) Ji(Jp Og Pa) HqOn JpPa} Mi{Hq(Fp Nc Ne Nh Nt Nw Nx Pa)} On{Oy(Ik Iq Mt Nc Ne Nh Oz) FpNf} Js{Nw(Mt Nc Ne Nf) KobN} aX{aV(Dr eP) IheM} Ji{Og(Ik Ne)} EmMeKj

Constrained panels with 3 analytes, where 1.0E-6 >= 'model p-value' > 1.0E-7. Contains 2,333 panels of 9,935,646 total panels evaluated. :
Ly{Jj(AA aX bN cH Fr gP Hw Ii Io Ir Is Iv Jh Jl Jm Jn Jr Jt Li Lj Lv Md Mi Mr Mz Nd Nh Nj Nn Nu Nv Ny Og Oh Oz Pb Pc Pe Pf Pg Pz Qa) Gn(Aa Ad Ao aV cF cH Cp Cu Dl Et Fr gP Hb Ij Ir Iz Jg Js Jt Ju Ke Kj Kl Kq Ks Li Mt Mu Mw Nn Oa Of Om Pc Pj Qn Uf Uh Uu Vo) Jg(Bg Dc Dk Fp Hu Hw Ih Im In Iu Ji Jk Jo Js Lj Lv Mi Mm Ms Mt Mu Mw Nc Nd Ne Nf Nh Nj Nq Ns Ny On Oz) Mm(aA Fp Hw Ih Ik Im Is Iv Jo Jr Lj Lv Mi Mr Nf Nh Nj Ns Of Og Om On Oz Pb Qe) Pa(aA bN Dc Dk Hw Ih Ik Im Iv Lv Md Mi Mt Nc Nd Ne Nf Nh Nj Nt Nw Og Om On) bN(aJ aZ bV Db Dc dE Dk Et In Jk Kc Mb Md Mj Mu Na Nf Oe Om Oz Pb Pc Wm) Js(aJ Ap Ar AX bA bV cH cM Db dE Dg Dl gP Ji Mt On Sr) Nw(aA Dc Dk Hq Hw Ih Iu Mi Ml Ms Mt My Ne Nj Ns Ny Of) On(Fp Hw Ih Jk Jo Jp Lj Mt My Nc Nd Ne Nh Nj Og Oz Pg) Nl(aA Fp Fr Im Iv Jt Lh Lj Lv Md Mr Mt Nk Og Pc Qe) Jp(Dc Dk Fp Hw Ih Jk Jo Lv Mi Mt Nf Ng Nh Ns Of) Aa(Fp Hw Ih Lx Md Mt Nc Nd Ne Nf Nj Og Om Oz) Et(al aO aX bF cE Co Cp Ct Cw Dd De gP Kg Ut) Ji(aA Hw Ih In Jo Jq Lj Nd Nh Nj Of Oz) Dc(Ad cH Dg Fp Ih Ik It Jt Nr Oy Qe) Mt(Hw Ih Iu Lv Mi Mr Nd Ns Of) Jk(aJ aX bA bV cH dE Dg gP) Md(Fp Mw Nb Nv Pc) Og(Fp Ih Ik Nt Qe) cH(aZ Db gP Om Pb) Mi(Nc Ne Pg) aJ(gP Mj Mu) aX(eM Mj Mu) Dk(Ko Ok) Dr(Nk Uf) EmUu LxaA aUaV cLeM} Et{Dk(aI bN gP Iq Jj Js Jt Kc Kk Ko Ks Nd Nw Oe Or Ou Oy Oz Pc Qx Qy Ra Ur Ut Vo) Dc(Ax bN Id Js Kc Kk Ko Lj Me Nd Nj Oe Or Ou Oy Pb Pc Qh Qx Rb St Vo Wm) Gl(Bg bN Dd Jj Jk Jl Js Jt Kg Kj Kk Md Mj Mv Nd Nf Oe Ou Pa Pb Pc Uk Vo) Om(aI Ao bN cE Ch Co Cw Dd Di dN Ha Jf Kg Kk Ko Ou Rg Ul Ut Vp Vs) aA(Fp Hx Ik Iq Jj Jr Js Jt Lv Lx Nf Nh Nq Ns Of Oz Pa) Wm(Hq Hx Ij In Jk Js Jt Md Mj Mk Mr Nf Oy) Jf(Ao Bg Ch Co Jk Jo Kg Mr Mu Mv Nf Nv Pg) Ut(Jj Jo Kk Me Nf Oe Ou Pa Pb Qx Ur Vo) Bg(Js Jt Kk Nd Oe Ou Pa Pb Pc) Nf(bN Ch Co Cw Kg Kj Kk Ou Vo) Ii(Ih Iv Jg Ji Mi Mr Nw On Qe) Jo(aI bJ bN Kc Ko Qy Rb Ul) Kg(Kc Me Mj Oe Ou Oy Pa Pb) Mi(Hx In Ma Mb Ns Oy Pd) Og(Hx Jg Ji Mr Nu On Pb) Hq(Jl Mk Ou Pa Pb Pe) Jv(Hx In Js Lz Mj Ns) Jt(Is Ko Li Ns Nu Nw) Mv(Kk Nw On Ou Pc) My(Mw Nb Nw On Pc) Mr(Hx Ij In Lz) Js(Ko Nq Nu Qe) Oe(Ao bN Ch Cw) Nd(Ao Ch Cw) Hx(Ih Ji On) Jg(Jh Mu Oy) Jk(Kc Kk Ou) Lj(Ha Lv Oz) Ny(Nb Nw On) Pg(Kk On Ou) Ih(Iu Ns) Oy(Jl Pc) Pb(Co Cw) bN(aI Ma) GnKc NqOz NuIn MbMc MjKk MuPc NiNk QcQe JiJq JriZ} Lx{On(Hq Hw Hx Ii Ik In Iq Jj Jk Js Mt Mv My Nc Ne Nh Nq Ns Of Og Oz Pg) Po(Fp Hw Hx Iq Is Iv Jj Jl Js Lh Li Mf Mk Mm Mt Nq Nx Oz Pa Pb Pe) Ji(Hw Hx Ii Ik In Iq Iu Jj Jk Jq Js Mt Nc Ne Nh Nq Ns Of Og Oz) Hw(Hq Ik Iv Jg Jj Lv Md Mi Mm Mr Mt Nc Nd Ne Nh Nj Nt Nw) Lv(Ik Iq Jj Js Mm Mt Nc Ne Nf Nh Nj Nq Ns Og Oz Qb) Md(aA Fp Hx Iq Iv Jp Js Mr Mw Nb Nf Nq Nt Og Oz Pa) Mi(Hx Ik In Iq Js Nc Ne Nf Nh Nq Of Oy Oz Pg) Jg(Iq Jh Jj Jk Js My Nc Ne Nf Nq Ns Of Og Oy) Mr(Hx Ij In Iq Jj Js Mj Nc Ne Nf Nh Nq Oy) Ik(Hu In Iu Jk Jo Js Mm Nf Nq Ns Of Og Pa) Nh(In Iq Iu Jk Js Mm Nf Ns Of Og Pa) Nc(In Iq Iu Js Mm Nd Ni Nk Ns Og) Jj(Hx Iq Iv Js Mg Mm Nq Nx Oz Pa) Mt(In Iq Jk Js Nj Nq Ns Of Og) Nd(Aa Iv Jp Ne Nf Nj Ns Nt Pa) Ne(In Iq Iu Jk Js Mm Ns Og) Iv(Hq Ij In Iq Mj Nf Nj) Nt(In Iu Jk Js Nq Og) Mm(Hx Iq Js Nf Nq Ns) Nf(Js Nw Om Pa) Iq(Js Nw Om Pa) Nw(Hx Js) aA(Nj Nq) NsOm MkOy} Mt{Md(Fp Hw Ik Iq Iv Jp Jr Js Lh Lv Mm Mr Mw Nb Nc Nc Nh Nj Nt Nv Ny Og Oz Pb Pc) Ji(Hw Ii In Iq Iu Jj Jk Jq Js Mv Nc Ne Nf Nj Nq Ns Of Og Oz Pa) On(Hq Hw In Iq Jj Jk Js Mv My Nc Ne Nf Nj Nq Ns Of Og Oz Pa Pg) Jj(Fp Hw Iq Iv Jg Js Lv Mm Mr Nc Ne Nh Nq Ns Nx Oz) Nd(Fp Hw Ih Iu Iv Jg Jl Jp Js Lv Mi Mr Nl Ns) Nj(Hw Iu Iv Jg Jp Js Lv Mi Mm Mr Nw Og Om Pa) Nl(Hw In Iu Jp Js Lv Mi Mr Nk Ns Og Pa) Nw(Hw Ii In Iq Jk My Nf Nq Ns Ny Of Og) Mm(Fp Hw Iq Js Lv Nc Ne Nq Ns Pa) Pa(Hw In Iq Js Lv Nq Ns Og) Mr(Hq Hw In Iq Mj Oy) Og(Fp Ik Jg Lv Nt Om) Mi(Hw In Iq Of Pg) Js(Fp Jp Lv Nt Om) Jg(My Nq Ns Of) Om(AA Jr Jt) Iv(Hw Ij In) Ns(Lv Pc) FpIn LvHw IqJp} Gn{Kc(Aa aD aG Aj Ap aV Ba Co Cu Dg Dl Hb Ij Is Jg Jk Ke Kg Kn Mg Pj Qv Ra Ss Uf Ul Um Un Uo) Hu(Aa aJ aV aW cF Hb Hv Ib Kf Kk Lu Nb Nd Ny Og Ou Rb Rc Ue Ul Wm) Ra(aJ aV cF cH Ke Kf Kj Ld Md Me Or Qu Rc Tr Ue Uk Um Un Uu Vo Vt) aV(aC aK aP CH cO Cs dG Di dJ dK dL Gl gW Qz Rc) Qw(Ao Hb Im Iz Kf Kn Rc Ue Ul Un) Kk(Cu Iz Jt Om Ss Uf Um Uo Uu) Me(Fb Ju Kf Kn Uf Um Vo) Rc(Fa It Ko Ld Mz Rb) aD(aQ bR cY Fw Ld Rb) Vo(aC cN It Kf Qx) Rb(aJ aX cH dL) Uo(cI dJ Ld) aJ(bR dA) aX(aQ cY) AaFw ChbU QvcN OgOr cLdO} Mm{Nd(aA Fp Hw Ih Ik Im Iq Is Iv Jg Jl Jp Jr Lh Li Lj Lv Md Mi Mr Nc Ne Nh Nj Nr Ns Nt Og Om Pe Qe) Om(aA Ih Im Is Iv Jj Jp Jr Lh Li Lj Lv Md Mi Mr Nc Nh Nj Nt On Pa Pe Qa Qe) Nj(aA Fp Ih Is Iu Iv Jg Ji Jo Jr Li Lj Lv Mi Mr Ne Og Oz Pb) Ne(aA Fp Hw Iq Iv Jg Ji Lv Mi Mr Ns Nw Og On Pa) Nc(Fp Hw Ik Jg Ji Jj Lv Md Mr Ni Ns Nw On Pa) Ok(Fp Hx Ik Iq Jt Lv Mq Nq Ns Oz) Md(Ji Lv Mi Mw Nb Nh Nt Nx Pa) Ik(Jo Ns Nw Of Og Pa) Jj(Fp Lv Nh Nt Pa) Nf(Fp Ji Nw On) Pa(Fp Lv Nh) MiHq NgJg NhJi JsNw OnOy} Nl{Md(aA Fp Fr Ii Iv Jq Jt Lh Lv Mp Mr Mw Nk Nt Nv Og Om Pc Pe Pg Qe) Nk(aA Fp Fr Ih Is Iv Jt Lh Li Lj Lv Me Mr Nt Og Om Pe Pg Qe) Om(AA Fp Fr Im Is Iv Jh Jt Lh Li Lv Mi Mr Nt Pa Pe Qe) Og(aA Fp Fr Ik Iv Jp Jt Lh Lv Mi Mr Nt Nx Pb Pc Qe) Mi(Fp Hw Hx Ij In Jp Lz Me Ml Nd Ni Ns Of Po) Pa(AA Hw In Iq Jp Lv Nd Ns Nt) Jp(Hw In Iq Js Lv Nd Ni Ns) Jg(Hu Iq Me Mw Nf) Ns(aA Fr Lv Pc) In(Iv Jt Nt Qe) On(Ii Jo Js Oz) Aa(Js Ma Oz) Lv(aA Me Mr) Fr(Jk Mv) Mr(Hq Mj) aA(Me Nx)} Ok{Pa(Fp Hx Ii In Iu Jk Lv Mq Nq Ns Nt Oy Po) Jg(Hx Ii Iu Jh Jj Jk Mq My Nq Ny Og Oy) Fp(Hw Ii In Iu Jk Jt Nq Og Oz Po) Nt(Hq Ii In Iu Jk Jt Mq Nq Ns Oz) Oy(Ik Lv Mi Mk Mr Nr Nw On Pb Pc) Nq(aA Hw Ih Jp Mi Nr Nw Og) Ik(Hu Hw Ii Ij Iu Jk Me Ng) Nw(Hw Hx Ii My Ns Ny Po) Mi(Ii Ij In Jk Pg Po) Ih(Hw Ii In Jk Jr Oz) Iv(Hx Ij In Jk Mj Mq) Mr(Hq Hx Ii Ij Mj) Nh(Iu Jk Jt Me Oz) Ns(Iu Oi Oz Pc) Mq(Hw Lv Nr Og) Jt(aA Hx Lv Oz) Iu(Hx Lv Nr) Jk(Nk Pb) Jq(Ji Jr) Nx(Jj Og) EmVo NrNg LzLj HxJp ImIq OgOi} Jj{Nj(Fp Fr Im Iv Ji Jl Jm Jt Lh Li Mg Mi Mr Nr Nt Nv Nx Pe Pg Pz Qa Qe) Jg(Fp Ih Ik Iq Iv Lv Mr My Nh Nq Ns Nt Nu Of Og Oz Pa) Ne(Fp Ik Jm Jp Jt Lh Lv Mg Mi Mr Nt Nx On Pa Qe) Ik(Hu Ih Iv Jl Jm Jt Lj Nc Ns Nt Nx) Nd(Im Ji Jm Jp Jt Lh Nv Nx Pa Qe) Nc(Fp Ji Lh Mg Nt Nx On Pa) Nh(Ji Mg Nt Nw Nx On Pa) Nw(Hx Js Lv Nt Oz Pa) Om(Im Jm Lh Nv Qe) Pa(Fp Ji Lv Mg Nx) Nt(Nq Og Oz Pb) On(Nq Oy Oz) Ji(Md Oz) FpMg} Nw{Ik(Hu Hw Ii Ij In Iu Jk Jo Js Mv My Nf Ns Of Og Pa Po) Nf(Fp Hw Jg Ji Lv Mi Mr Nc Nd Ne Nj Nt On Oz Pa) Js(Dk Fp Hw Ih Iq Mv My Nh Nq Ns Nt Ny Og Oz Pa) Nd(aA Hw Ih In Iu Mi Ml My Ne Ns Of) Ne(Hw In Iq Iu Jk Ml Ns Of Og Pa) Nc(Hw In Iq Iu Jk Ml Ns Og) Mr(Hq Hx Mj Oy Po) Mi(Nj Om Pg Po) Nh(Hw In Og Pa) Hw(Hq Ih Pa) In(Ih Nj Nt) Wm(Mj Pg) Iq(Ih Pa) Iv(Hx Ij) Jg(My Ng) Om(aA Lv) NtOg NjOf OnOy} Ji{Md(Fp Hw Ik Iq Iv Jp Lv Mi Mw Nc Nf Nh Nj Nt Og On Oz Pa Pb Pc) Nd(aA Fp Hw Ih Iq Iu Jg Jp Jq Lj Nc Ne Nf Nh Nj Ns Nt Oz) Om(aA Ih Im Iq Jp Js Lj Mi Mr Nr Ns Og On Oz Pa Qa Qe) Nf(Fp Ih Ik Iv Jg Mr Nc Ne Nh Nj Nt Og On Oz Pa) Ne(Hw In Iq Iu Me Ns Oz Pa) Nc(Hw Iq Ni Ns Og Oz Pa) Nh(Hw Og Oz Pa) Nj(Iq Iu Jq Oz) Og(Jg Nt Oz) Iq(Ih Pa) MiHq MyJg IkJo} On{Nj(Fp Hw Ij Iq Iu Jg Jk Jo Jp Js Lj Me Mv My Nd Nf Ns Of Og Oz Pa Pg) Nd(Fp Hq Hw Ih Jk Jp Lj Mv My Nc Ne Nf Ns Of

Figure 11 Continued

Og Om Pa) Om(Fp Ih Ik Im Jk Lv Mv Nc Nf Ng Nh Nq Nt Of Oz Pa) Oy(Fp Hq Hw Hx Lv Mf Mq Nf Nq Nt Nx Pa Pb) Ne(Hq Hw Iq Jk Nf Ns Of Og Pa) Nf(Hq Ik Jg Nc Nh Nt Oz Pa) Md(Hx Iv Mf Ml Nt Nx) Hq(Fp Mi Nc Nh) Og(Ik Nh Nt)} Jg{Ng(Fp Ih Ik Iq Iv Lj Lv My Nc Nf Nh Ns Nt Nx Og Pa) My(Fp Iq Jk Lv Nc Nh Nq Nx Of Oz Pa) Nd(Ih Jh Lj Mi Mu Nc Ne Ns Of Oy Pa) Nj(Jh Jk Lj Mi Mu Nf Ns Of Oy Pa) Ne(Jh Jk Mu Nq Ns Of Og Oy Pa) Og(Ik Jh Nc Nh Nq Ns Nt Pa) Om(aA Jh Lj Mu Mw Nq Oy) Mv(Fp Ik In Iv) Nc(Jk Ns Of) Pa(Iq Of Oy) Nh(Ns Of) FpNf IvOy} Md{Nx(aA Hw Ik Jp Lv Mi Mw Nb Nc Nd Ne Nh Nj Nt Og Om Oz Pa Pc Qe) Mi(Fp Ik Nc Nd Nh Nj Nt) Jp(Fp Ik Lv Nd Nc Nh Nt) Pa(Fp Ik Ne Nh Nj Nt) Nb(Nc Ne Nh Nj) Og(Ik Nt) FpMw} Mi{Hq(Ih Iv Jp Jr Lv Mf Nf Nr Oi Om Oz Pb Pe Pg Qe) Pg(Fp Ne Nj Nt) Om(Fp Ik Nt) Nj(Jp Pa) NdJp IkOg} Jp{Nd(Fp Iq Lv Ne Nj Ns Nt Og Pa) Nj(Iq Js Lv Ni Nk Og) Om(Fp Ik Lv Ne Nh Nt) Ik(Ng Og)} Pa{Nj(AA Iv Lv Mr Nt Og Om) Nt(In Nd Og Om) Og(Ik Nd Nh) AaNd} bN{Kc(Dc dJ Jf Ko Me Mj Nf Wm) Ko(Dk Gl Ma Oe Om Wm) MeHf} Og{Nt(Ik Lv Nd Nj Om Oz) AaNd GcKc MrIk} aV{dO(cL cO gP) DraC aXgT cNeP} Me{Dr(Fb Jy) Em(Uu Vo) GcJy} Ko{Js(Di Dk gP Om) RiOm} Kc{dX(Ib Vo) DrRc} Aa{Om(Nd Nj)} Em{QwVo KjNx} cP{QwgP aXcY} FpMjMr GwcLdD HuKkeM dOfRgP

Constrained panels with 3 analytes, where 1.0E-5 >= 'model p-value' > 1.0E-6. Contains 5,229 panels of 9,935,646 total panels evaluated. : Ly{Md(aJ Ar aX aZ bA Bo cH cM Db Dc dE Dg Fr gP Id Ih Ii Ik Im Is Iv Jl Jq Jr Jt Ko Lh Li Lj Lv Mp Mr Nc Ne Nh No Nt Ny Og Om Pe Pg Qa Qe Sr) Dk(Aa aJ Ap Ar aX bA Bb bJ Bo cH cM Db Dg Dl Fp gP Ih Ik Im It Jj Jt Lx Mb Mm Nf Ng Nr Nx On Oy Oz Pb Pc Pf Qe) Dc(Aa aJ Ap Ar AX bA bV Db dE dJ Dl Id Im Jj Jm Jr Kc Ko Lj Lx Mb Mm Nf Nm Nx Ny Ok Pb Pe Pf Qa Sr Wm) gP(aX bA bJ bN bV Db dI dM Dr eM gL Hf In Jf Jp Kc Kk Ko Kp Mb Mu Na Nd Nf Pa Pc Rg Ri Sr Uk Up Ur Wm) Db(Aa aJ aX Bg bL bV cE Ch Ct Dd Dl dJ Fp Hq Hw Ik Jj Jk Lj Lx Mb Mj Mu Mv Nd Nf Nr Nu Om Pg) Og(aA Fr Im Is Iv Jh Jl Jq Jr Jt Lh Li Lj Lv Mi Mr Nc Nd Ne Nh Nj No Nr Nx Pb Pc Pe Pf Qa) Om(aJ bJ cM Dd Dg dJ Dl Fp Fr Id Ih Im Is Jt Ko Lh Li Lj Lv Mi Mr Ne Nt Pe Qa Qe Qm Sr St) Ko(Bg bN Cp Ha Hf Hq Jf Jj Jk Jl Jo Ma Mj Mr Mu Mv Nf Oe Of Pg Uk Ut Vu Tj) Mi(Fp Hw Hx Ih Ik Im In Iv Jr Lj Nd Nf Nh Nj Nt Nx Ny Of On Oy Pb Qe) Et(bZ Ef Ha Hf Ib Iz Jf Ke Kj Kr Ks Ou Qt Tn Uk Ur Vo Vp Vs Vu Tj) cH(aX bJ cI dE Hf Hw Hx Ii In Jl Jr Mj Mk Mu Na Nd Nf Oe Pa Pc Pg) Ih(aA Fp Fr Hw In Js Lv Mr Nc Nd Ne Nf Nh Nj Nl Nt Nx Oz Pb Pc) bA(Bg cE CT Hq Hv Hw Hx Jl Ma Mj Mk Mr Mu Mv Nd Nf Pe Pg Po) dJ(aJ aX aZ bJ cC dE Hv Hw Ii In Jl Kc Mb Mr Na Oe Pb Pc Pg) Bg(Ap Bo cM Dg Ik It Jh Jp Lx Mm Nm Nr Nw Ok Oy Oz Pa Pb) Nc(aA Fp Fr Hw Im Is Iv Jt Lh Li Lj Lv Mr Ns Nt Pc Pe Qe) Ne(aA Fp Fr Im Is Iv Jt Lh Li Lj Lv Mr Nt Ny Pc Pe Qe) Nf(aJ aX aZ dE Fp Fr Id Im Is Iv Jt Lh Li Mr Pe Qe Sr) Js(Fp gL Hf Id Im Jf Kc Kp Nt Ou Ph Pj Qe St Uh Uk Ur) aZ(Aa bJ cE cM Ct dI Hq Hw Jj Jk Mj Mu Mv Nd Pg) Dd(Dg Ik It Jp Na Nd Nr Oe Oy Oz Pa Pb Pc) bV(cM Dr Jl Jr Mj Mr Mu Mv Na Nd Oe Pg Po) cE(aJ aP aX dE dF Jg Jp Kc Mb Nr Oz Pa Pb) bJ(Aa aN aV aX Ct Hw Mu Mv Oe Oz Pa Pb) dE(Aa bL dI Hq Hx Ii Jj Mj Mu Mv Nd Pg) Lv(aA Fp Im Li Lj Mr Nh Nj Nt On Qe) Mr(Ar Ax Fp Hq Hw Im Nd Nh Nj Oy) Jk(Ap Ba Dl Id Jf Kc Ou Ph Sr Tt) aX(Aa cM Dr Jl Mb Mv Nd Oe Pa Pc) Dg(Hq Jl Jo Mj Mu Mv Oe Of Pg) Nt(Im In Lj Nd Nj Ns Of Oz Pb) On(Ii Ij Im Iu Mv Ng Nq Ns Ny) Nh(aA Fp Fr Im Iv Jt Lj Qe) Nj(aA Fr Im Is Iv Jt Lj Qe) aJ(Aa cM Hx Jl Mv Nd Oe Pg) Ct(Ba Ik It Jg Jp Nr Oy) Mj(aP Ar Ax Id Kc Ph Sr) Mu(aP Bo cM dG Jf Ou Sr) Pa(Fp Ha In Nx Vp Vu Tj) bN(Hf Kk Kp Ou Ph Uk) Nd(Fr Im Jt Pe Qe) Jp(aI Ao Ch Cp Di) aA(Fp Jg Jr Mt Nx) Qe(In Iu Of Qc) Ar(Pe Pg Po) Bo(Hq Mv Pg) Ch(Ik Jg Oy) Im(Hw Iu Of) cM(Aa aI Pg) Ap(Jo Mv) Di(Mb Pb) Dl(Jl Oe) Dr(cN Qu) Em(Tr Vp) Fp(Fr Ha) Gn(Ra Vt) Nl(Ny Pe) Jf(Hf Kc) Jg(Ao Cp) Lj(Fr Ha) Uk(Aa Vq) aU(aK cY) eP(cL Hu) TjPb MbdI MvaP OzaI aCcM} Et{Jf(Af Ba Bb Cp Ct Cw Dd De Di Ef Fa Fr gP Ha Hc Hq Hw Ib Ii Ij In Iz Jd Je Jl Jq Js Kc Ke Kj Kq Ks Lh Ma Md Me Mj Mk Mn Mq Mw My Na Nd Nq Ny Oe Of On Oy Pe Po Qt Rg Tn Vp Vs Vu Tj) bN(aH aJ aL AO aX bF Bg bV cE Ch cI Co Ct cZ gP Hq Hx Ii Ij In Iq Jj Jk Jl Jq Jr Js Jt Kc Ke Kg Kk Lh Md Me Mj Mn Mq Mr Mu Mv Mw Na Nd Nj Nq Nv Ny Of Oz Pa Pb Pc Pg Po Ut Vo Wm) Vo(Ao aX Bg Ch Co Cp Ct Cw De Di dN Em Gn Ha Hq Hx Ib Jk Jl Kc Kg Ko Kp Ma Md Mj Mk Mn Mr Mu Mv Nd Nv Oe Ou Oy Pg Po Rg Ri Vu Tj) Kk(aI Ao cE Ch Co Cp Ct De Fr gP Ha Hq Hx Ib Ii Ij Jl Jr Jt Kg Lh Ma Md Mk Mn Mr Mu Mw Nq Nv Oy Pe Po Qt Vp Vs Vu Tj) Ou(Ao cE Ch Co Cp Ct Cw De Ef Ha Ib Ii Ij Iz Jl Jt Kj Ma Md Mj Mk Mn Mr Mu Nq Nv Oe Of On Oy Po Qt Qw Tn Vs Vu Tj) Kc(Ao Bg cE Ch Co Cp Cw De Di gP Ha Hq Hx Ii Ij Jl Jr Js Jt Kj Ma Md Mj Mk Mr Mu Mv Nv Oe Pg Po Ut Vp Vu) aI(Ao aV cM Dc Gl gP Ii In Iq Jj Jk Jl Js Jt Kg Kj Ma Md Mj Mr Mv Nd Nf Oe Pb Pc Pg Po Ur Ut) Ao(gP Ha Hc Hu Hw Hx Ii In Iq Jj Jl Jr Js Jt Ko Md Me Mj Oy Pa Pb Pc Pg Qy Ra Rb Ur) Ch(gP Ha Hx Ii In Iq Jj Jl Jr Js Jt Ko Kr Ks Md Mj Oy Oz Pa Pb Pc Pg Qx Qy Ra Ur) Kg(Af bJ cE Db gP Ha Hx Jl Jr Js Jt Ko Md Mn Mr Mv Nd Oz Pc Pg Qy Rb Ut) Cw(Hf Hx Ii In Jj Jl Js Jt Ks Mb Md Mj Mn Mr Na Oy Oz Pa Pc) Ko(Bg Co Cp Ef Gl Hq Ii Ij Jk Kj Ma Md Mj Mu Mv Oe Pg Po Ut) gP(aJ aX Bg cE Dc Gl Ii Jk Jo Ma Md Mv Nd Nf Oe Om Pc Pg Ut) Wm(Hw Iq Jl Jr Lh Ml Mq Mw My Nb Nq Nv Ny Of Pb Pe Po Pz) Oe(aH aX bF cE Co Cp Dd De Di Ha Ib Kc Qt Rg Tn Ul Tj) Bg(bA Ha Hu Iq Jj Jr Ks Me Mj Oy Oz Pg Qx Qy Ra Ur) Ut(aA aJ aX aZ bA dM gL iZ Js Jt Nd Nx Oy Pc Qy Ul) Co(Hu In Iq Jh Jj Jl Js Jt Mj Nd Oy Oz Pa Pc Ur) aX(cE Dc Dk eM Gl Jk Jo Ma Mj Mv Nd Nf Om Pg) Mr(Ar Ax Cs Id Kj Qw Qx Ri Uk Ul Ur Uv) Mv(aJ bA bJ gL Ha Ks Qx Qy Ra Uk Ur) Nd(aO aZ bA bF cE Cp Dd dM Kj Qw Tj) Gl(aA aZ bA bJ bV cM dE gL iZ Vu) Jt(Aa aO Ax cE Cp De Di Ib Rg Tj) Ur(Cp Di Ij Ke Ma Mn Mu Pg Po Rg) Kj(Hx Md Me Mj Oy Pa Po Rg Ul) cE(bA Dc Ii Iq Jj Js Nf Pb Pc) Jk(aJ bA bV Or Qy Ra Rb) Js(Ax Cp Ct Dc Di Ib Sr) Vu(Io iZ Jo Nf Om Pa Pb) Dk(aA aH bA bJ dM iZ) Me(Ef Ha Hf Kr Ks Vp) Dc(aH aO bA bV cH) Nf(aH aJ aZ Ef Vs) Pa(Ct Ef Ha Vs Tj) Ma(bA Ha Ph Qx) Mj(aJ Ax iZ Ra) Mu(Qx Qy Ra Rb) Cs(Jr Pe Pg) Di(Ii Jl Pc) Jo(aZ gL Vq) Rg(Jj Of Qw) iZ(Hx Jl Nv) Ax(Jr Pg) Cp(Pb Pc) Ct(Oy Pb) Ha(Fp Oa) Om(cH gL) ArPo NqaJ MdRb MnVs QxPg JjKe aUaV} Gn{aD(aJ aK Ax bA bU cB cF CH cM Cs Di dJ dL Dq Ez Gl Hf Ih Ij Iz Jh Jj Js Jt Jy Ke Kf Kj Kk Lu Me Mw Mz Nj Nm Nu Ny Oi Or Ou Qv Qw Qz Rc Rm St Uc Uf Vo) Kc(Af aJ aO Aw bF bL bN bP cH De dJ Dk dL Ed Fb Fr Fy Gc Gl Ik Jd Js Jv Kp Ks Lu Me Mn Mt Mu Ng Nk Nn Ny Oe Oi Ok Pz Rb Rh Uh Vq Vs Vt Wm) Kk(Aa Ad aG Ao aQ Ba cY dJ DL Ed Ef Ez Fb Fr Gl Hb Ii Ij Im Jd Jg Jh Js Kj Kl Kn Ks Li Ma Nm Ny Of Pj Qu Ra Rh Uc Ul Un) Vo(aJ Al aM aX bE cH cI Cu Dg dJ dL Fw Gz Ih Jm Jo Ko Ld Mf Nj Nv Nw Nx Ok On Ou Qa Rb Rm St Vv) Uo(aJ aV Bn CH Cx Di Dp Em Fb Fw Gl Hf Ih Jy Kj Me Mu Nj Oa Or Qw Qx Ra Rb Rc St Ue Uk Un) Rc(aJ Al aX Bc bR cF cH cN Cs dJ Ex Fw Kf Kq Lj Nb Nw Nx Oa Og Oh Ok On Ou Qz Sr St Um) Qw(Aa Ad aV Bb Cu Dl Ef Ez Fy Gl Ii Ij Jo Js Jt Kg Kj Kl Lu Nm Ny Om Pj Uf Um Uu) Rb(aG bE cF cJ cN cO dE dG dK Fb Js Kf Kn Mu Na Nk Om Oz Pc Qx Ra Ul Um Uu) Me(Aa Ao aX CH Hb Ij Iz Jv Ke Kl Ks Om Oz Pc Qu Ss Tz Uc Ul Un) Ra(Aa Ao aQ aY aZ bP Ch cI Ed Fw Ih Js Jt Kl Kn Kz Lu Rg St Uf Uh) aJ(aK aQ bU Ch cI cM cY Dl dJ Ef gP Ld Ny Qu Wm) cH(aK aN bR bU cF cN cP cY Fw Ld Nj Ny Ph Qt Ue Um) bR(Aa aX Bb Ch cN dG dJ dL Ef Gl Or Ue) Fw(aG Ao Ba bL Ch dJ Dl Ef Gl Kf) aV(fR Ic In Io Mb Mk Og Or To Ue) Ch(bC cF cM cN cP dG dL Um) Om(dJ Ko Ld Lh Nj Oh Or) cF(aM Di dL Ef Gl Or Um) cN(dJ dO Ef Hu Kj Ny) Gl(bA bU cP dD Um) Kf(Ex It Ko Ld Nj) dJ(aN bC Ib Lu Um) Kj(Ko Nx On Qx) Ld(Aa aG aX Jv) dL(bU cM Ef Wm) Um(Oa Qx Uk) cP(aX Ef Gw) Aa(It Nj) Ue(Nx Og) EfbU HuaG SsQx QuOu NxUn OgOz aKaX} Jg{Fp(Hw In Iq Iu Jh Jk Jo Js Lv Mi Ml Mq Mu Mw Nc Nd Ne Nh Nj Nq Ns Ny Of Og Oy Oz Pa Po) Nq(Ih Iq Iu Iv Jh Ji Lj Lv Mi Mm Mr Mu Nc Nd Nf Ng Nh Nj Ns Nt Nw Of On Oy Oz Pa) Iq(Ih Iv Jh Ji Jr Lj Lv Mi Mm Mr Mt Mu Nc Nd Ne Nh Nj Ns Nt Of Og On Oy Qe) Nf(Ih Ik Iv Jh Jj Lj Lv Mi Mm Mr Mt My Nc Nd Ne Nh Ns Nt Nu Og Oz Pa Pe) Oz(Ih Jh Ji Jk Lj Lv Lx Mi Mm Mt Mu Nc Nd Ne Nh Nj Ns Nt Of Og On Oy) Nd(AA Hu Im Iu Iv Jk Jo Jp Lv Mr Mw Nh Nj Nt Nu On Pe Qe) Og(Hu Hw Ih Iv Js Lj Lv Mi Mr Mu Mw Nu Nx Of On Oy Pb Pc) Ns(Hw Ih Ik Iu Iv Ji Jk Lj Lv Mm Nt Nu Nw Of On Pa Pc) Nc(Hw In Iu Jh Ji Js Lj Lv Mi Mt Mu Mw Ni Nk On Oy Pa) Nh(Hw In Iu Jh Jk Jo Js Lj Lv Mi Mm Mt Mu Mw Oy Pa) Oy(Hw Ik Ji

Figure 11 Continued

Figure 11 Continued

Vu) Dr(Ao Co Cu Ez Fy Ij Me Uf Uo) gP(cE cL Jf Jk Me Mj Mv Nf Rj) Em(cH Ha Ju Jv Vp) Mj(aJ aX) DcDg GcdL MecE NxUt aUaV aXeM} Jp{Nt(Fp Hw In Iq Jk Js Lv Mv Nc Ne Nf Ng Nh Nq Ns Of Oz) Ik(Hu Hw Iq Iu Ji Jk Jo Js Lv Mv Nc Nd Ne Nf Nq Ns Of) Fp(Hw In Iq Js Lv Ml Nc Ne Nf Nh Nq Ns) Lv(Hw Iq Mv Nc Ne Nf Nh Nq Ns Oz) Nd(AA Ih Iv Js Mr Nc Nh Nu) Nc(Hw Iq Ni Nk Ns) Ne(Hw Iq Js Nk Ns) Nh(Hw Iq Js Ns) Ji(Hw Iq Js Nq) Lx(Jk Mv Nq) Wm(Mj Pg) AaNj IhIq} Lx{Iv(Hx Iu Jo Jr Js Lz Nq Ns Of Oy Oz) Nf(AA Fp Hw Hx Jl Mk Nq Nt Pe) Mr(Ii Ik Il Iu Lz Ns Of Oz Pe) aA(Hx Ik Iq Iu Jk Js Mv Ns Oz) In(Fp Ih Is Jl Nu Pb Pe) Ns(Iu Js Nt Oz Pe) Hq(Ik Jl Mk Pb Pe) Js(Aa Fp Hx Nq) Wm(Mj Pg Po) Nt(Iq Of Oz) Mg(Jk Jo Of) Pc(Mv My Oy) Lz(Nr Pe) Hw(Jl Nq) Hx(Iu Pb) Ik(Iq Ng) AaNj NoJr IhQb IiNx} Ji{Iq(Fp Ik Iv Jq Js Lj Mr Nf Nh Nt Oz Qe) Jq(Hw Ih Ik Iv Js Lv Nc Ns Nt Nx Oz) Nt(Hw In Iu Jo Js Nq Ns Of Oz) Fp(Hw In Js Ml Mq Ns Oz) Ih(Hw In Js Lv Nq Oz Qb) Ns(aA Ik Iv Js Nh Oz) Ik(Hw In Iu Me Of) Mr(Hq Hw Mj Oy) Nf(Js Lv Pb Wm) Iv(Hw Ij In Nq) Jo(Lv Mg Oz) Nq(aA Qe) Nc(Js Nk) NhIn JsLj} Me{Dr(Iz Ju Jv Ke Kf Kn Rc) Nd(Aa aJ aX aZ bN dE) gP(Hf Jf Kk Sr Ur Wm) Jf(Db dE Em Hf) Sr(bN Dc Dk Js) bN(Kk Kp Wm) Em(Kl Uc) Lv(Ne Nh) Hf(cH cM) MrNj NeaA VqaX} Nt{Nd(aA Fp Fr Ih Iu Lv Mr Nc Ns Pe) In(Fp Ih Iv Mr Nc Ne) Lv(Nc Ne Nj Ns Oz) Mr(Hq Nf Nj Oy) Ns(Nc Ne Pc) Nj(Fr Iu) NcNk NeIu} Ok{Wm(Hq Hx In Mj Mr Nf Pg) Dk(gP Jo Js Nf) aA(Hx Jk Ns) Dc(Gl Nf) Em(Ii Kj) Mr(In Pe) Qe(Qc Qd) Js(Bg bN) Pc(Mv My) NfbN NgOi IiNx aXeM} Nj{Aa(Jo Jr Js Ma Nf Ni Oz) Lv(aA Fp Iv Jt Lj Mr Qe) Mr(Fp Hq Mj Nf Oy Qe) Fr(Lj Mv) Qe(Iq Iu) aA(Jr Nx) NfLh aXeM} gP{aJ(Bc bL bN bR bU cH cM Db Dg dJ Qw Rb) Wm(Kk Nf Ur) Qw(dX eM Kk) Dg(Dc Dk) Nf(Kk Sr) fR(aD Db) DqeF cHgL} Fp{Mr(Hq In Nd Nf Oy Pe) Lv(Nc Nd Ne Nf Nh) Nf(Aa Dc Iv Lh) aA(Nd Ne) AaJs HaNx NcNk} Aa{Nd(Ih Jo Jr Js Ma Mw Nc Nf Oz) Ne(Hw Js Ma Oz) aJ(bN cM) NfJr IkJo} aX{cM(cY Ed It Jy Mf Ou Ph) Dr(Rb St) Ou(eP Mj) aK(eP eX) cY(eX gT) dO(aJ Fw)} aV{eP(aJ aU bE cY dF dK) dO(bX cH cP Di eF) fR(gN gT) DraU GwcL dGgC} cL{bR(Dq eP eX) dO(aJ cN fR) Gw(BC) CsdV DvbC QweM cPgT dIcP} bN{Wm(hC Kk Nf Ph Qw Qx) Dg(Dc Vo) Kk(Ki Nf) aJ(cM Db)} Nx{Wm(Mr Pg) Em(Ha Vo) aA(Nd Ne) DcNf DrUf HaLj MrOy OuUt} Lv{Nc(Iv Mr Nk Ns) Ne(aA Mr Ns) Ih(Nd Qb) MrNf} fR{Oz(Ax cP Hu Nf) Mj(Qw Qx) Nf(Nd Qw) DbcP aDdO} eF{Dq(aD aM bX cP) dV(aD Af aM cP)} Hu{eP(Oa Rb Rf) eM(Ib Oa) QxdX} Mr{Hq(Ik Ne Nh) Ik(Nf Oy)} Dg{Dc(Db Di Gl) DkVo} Em{dM(aQ cY) QwKj VoPh} Ne{aA(Jq Nd Ns) InIv} Ib{Kf(eM eP) IheM KkdX} Kk{Nf(Ki Wm) KidJ} bR{aJ(dO dV) dGdV} Nd{IhaA IqQc} dX{UeQy QxUf} DoFwcA DrStRa aDcBdV cFdGdO cNcYeP

Constrained panels with 3 analytes, where 1.0E-4 >= 'model p-value' > 1.0E-5. Contains 11,585 panels of 9,935,646 total panels evaluated. :
Gn{Kf(Aa aJ Al AX cH cN Cs Cx dJ dL Ef Ez Fa Fp Hf Ih Iz Ji Jl Jm Jn Jp Jt Kj Kl Ky Lj Mf Mz Nv Nw Nx Oa Og Oh Ok On Or Ou Qa Qb Qd Qe Qx Rm Sr St To Ue Uf Uu) Rc(aM Ar Ax aZ Bb bU cI cP Cv Cx Dk DL Et Fp Id Ih Ji Jj Jm Jn Jp Jq Kn Kp Ky Lh Ma Mf Mm Ne Nj Nn Nr Nv Oe Or Ow Pe Qa Qb Qe Qn Qx Rm To Tr Up Ur Vv) Vo(Ad Af aV bR bU cO Cv Cx dG Di Dl Em Ex Fa Hf Hq Id Ip Is Ji Jl Jn Jp Jq Kn Kp Kq Ky Lh Mh Mm Mu Mz Oa Oe Og Oh Oi Oy Pb Pc Pg Ph Pz Qb Qd Qe Qz Tr Ug) cN(aK aQ bU cI cY dD dI Dp Ez Fb Ib Ic Ii Ij Iz Jd Jh Jj Jk Jo Js Jt Ke Kl Ld Me Mg Mu Mv Mw Nf Ng Nm Og Om Or Oy Pd Qt Qy Uc Ue Uf Uk Um Un Uu Vs Vt) Qw(aJ Ap aR Ba bL bP cF CH Co Cp Dc Dg dL Dp Fb Ib Ir Is Jd Je Jg Ji Jv Kq Ks Mg Mr Mw Ng Nk Og Or Oy Pz Qt Qu Qx Qy Rb Ss Uh Uk Vq Vt) Um(aJ AX bP bR cI Cs dI dL Dp Ef Em Ex Fb Fp Fw gW Hf Ib Ih In Jj Jn Kj Ld Mf Mu Mv Mz Nf Nj Nw Nx Ny Og Or Qa Qu Qy Qz St Ub Ue Uf Vp) Mf(Aa aJ Ao aX bR Ch dJ Ef Em Ez Fb Gl Hb Ii Ij Im Iz Jj Jo Jt Ke Kj Kl Ks Mn Mw Ng Nm Ny Of Om Oy Qt Qu Qx Ue Uf Un Uu) Qx(Aa aD aJ aK Ao aQ cA Ch cK dJ dL Ed Ez Gl Ib Iz Jt Jy Ke Ld Lu Ml Mr Ng Nj Nm Ny Og Om Or Ue Uf Uk Ul Un Up Uu) Me(aG aJ aV Ba Bb bF Bg bO cD Cp Cw dJ Dl Ef Gl gP Ii Im Jg Jh Jj Jk Js Jt Ld Lu Mu Mv Mw Nd Of Og Oi Oy Pd) Om(aJ Al aV AX Bn cH Cs dG dL Em Ex Fa Fp Fw Ih Jl Jm Jn Kp Ky Lj Mm Mn Nv Nw Nx Oa Og Pe Qa Qb Sr St Up) aX(bU cB cH Cs dD dI dJ dL dO Dp Ef Ez Ic Ih Iz Jj Jt Jy Ke Kj Kn Lu Nj Nm Ny Oa Og Qv Qz Ue Uf Un Uu Wm) Ld(Af Bb Ch Co Cp dJ dL Em Ez Fb Gl Gp Ib Ij Ik In Iz Js Jt Ju Kn Ny Og Or Qt Qu Qz Rh Ue Ul Uu) Kj(aC bR bU cF cP cR dE dJ dL Em Fw Ih It Jm Mh Mz Nj Nv Nw Oe Og Ok Ou Ph Qa Qb Rb Rm St Vv) Aa(aN aQ bC bU cB cF Cs Di dJ Dl Ih Ji Jm Ko Ky Mz Nw Nx Og Oi Ok Ou Ph Qa Qb Rb Rm St Uo) Uf(aJ bR cF cH cO cP cR Cs dG dJ dL Ex Fw It Jp Ko Nb Nw Nx Oa Og Oh Ok On Ou Qa Rb St Uo) Fw(eP Fb Ij Im Iz Jj Js Jt Ju Jv Jy Ke Kl Kn Ks Mu Nt Ny Oi Pc Pj Qu Ue Ul Un Uu) Nj(Af aJ Ao bR Ch dJ dL Ef Ez Gl Ij Iz Jj Jt Jv Kl Mv Nb Ng Ny Of Og Oz Pc Ut Uu) cF(Bb cI cM Cw dI dJ Em Ez Ib Ij In Iz Jh Jj Mu Mv Ny Og Oy Qg Qu Qv Ue Uo Ut Wm) St(Ba CH Ef Ez Fb Gl Gp Ib Ii Ij Im Iz Jt Kl Kn Ma Mn Ny Qt Qu Uc Ue Un Uu) Nx(Ao Ba Cw Ef Fb Gl Ii Ij Iz Jo Jt Ju Jv Ke Kl Ks Ng Of Qu Tz Ua Ut Uu Vt) cH(aQ As Bo dI Ez Fn Ib Ih Jy Ke Kn Nk Nl Nm Og Oi Or Oz Pc Qu Qz Uk Ul Wm) cP(aJ Ao Ap aR Bb bF Co Cp Cs Ct dE DK fR Ib Ij Iz Ma Mu Mv Or Qt Qu Ue) Uo(aQ Ax aZ bC Bg bM bP cY dL Ed Hv Kn Kx Kz Og Ou Oy Pi Ub Vp) dL(dI dJ Ez Fb gP Ib Jt Ke Kl Nm Ny Qt Qu Qv Qz Ue Uh Un Uu) Gl(Hq Ih Kn Kp Ky Mn Mu Nb Oa Og Ok On Ou Oy Oz Pc Vv) dJ(cL dG dI Ez fR In Mn Ny Oa Og Or Qn Qt Qu Ue Uu Wm) Uu(Al aV bR bU Em Ih It Jm Ko Mz Oe On Ou Qb Rm) Ue(aC aM cI Ih Jm Mu Nb Nv Nw On Ou Rb Rm Vv) Qt(aJ aP aV cI cO dG gP Jn Oh Ou Oy Oz Pc Vv) Og(aJ cI Em Fb gP Jj Kn Ny Oi Oy Pc Rb Rg Un) dG(aK aO aQ bU cM cY dA Dl Ef Ny Qu Wm) Ib(aJ bR cI dE Ex Hc Jn Oa Oh On Ou Vv) Ch(aK aQ cY Ih Kn Nd Ou Oy Oz Pc Ul) Cs(aK aN aQ cI cM cU cY dI gP Ke Li) Ny(aP bE cO gW Ih Ky Mu Oa Ok Qa Qb) bR(aG aN cL Cw dE fR Hv Jy Kl Lu Wm) bU(Aj aM Ao Bb cI Ct dE fR Jj Or Qu) Fb(aJ aV Mz Nw Oa Oe Ou Qa Qb Qe) aD(Gw Oa Pi Qb Qg Qu Ug Uk Un Wm) Jt(Ih It Ko Nw Ok On Ou Qa Rm) aJ(aR Ez Ke Kn Mv Mw Nm Qv Un) Wm(aC aN aV bE cT dE Mu Na) Rb(Ao Iz Ju Jv Ky Oy Uk Un) Qu(cI gL Jn Oa Ok On Tn Vv) aK(aP aU Di dK dM Ef fR gW) cY(aP aU Di dK dM Ef Em gW) aN(aM Ax Bb cI dD Di Gw) aQ(aP aU Bb dE dK dM gW) Ih(Ef Ez Ii Ij Mn Uc) Ke(Ex Jp Ko Nw On Qa) aV(DO Fp Jj Nu Uk) Iz(It Nv Oa On Ou) Ok(Ap Ba Ef Ij Ma) Un(Ex Fa Mz Nw On) Di(Bo dE fR Ul) Ez(cI cO It Vv) Ou(Co Ef Kl Or) Mu(Hv Nb Qz) In(It Oa Rm) Qv(aC aM bE) Jj(dE Ky Nl) cB(aG Bb Cw) fR(dA Em gP) Ef(Bc It) Ma(Ax Vv) Hv(Mv Uk) Li(Fp Lj) Oa(Mr Po) Or(dI gP) dE(cM dI) AfBn CwbC DcGw DocA ExJs MzUl KlKo KnNw aPdA cWgP dRgW} Ly{Ut(aJ aP aX aZ bA Bo bV cM Db dE Dg Fp Id Ih Ik Im It Jf Jg Jp Kc Kk Kp Kq Lh Lx Mb Mm Nm Nr Nw Nx Ny Ok On Ou Oy Pa Pb Pc Pf Ph Qe Qm Sr St Tt Uh Wm) Tj(Ar aZ bA bV Db dE Dg Ed Fp Fw Hf Id Ih Ik It Jf Jg Jp Jr Kc Kk Kp Lj Lx Nm Nr Nw Nx Ok Ou Oy Oz Pc Ph Qe Ri Sr Uh Ur Wm) Om(aA gL Hw Ik Io Ip Ir Iv Jf Jh Jl Jq Jr Kc Kp Lw Mk Mz Nc Nh No Nr Nv Nx Ny Oh Ou Pc Pf Pg Ph Pz Qd Ri Tt Uh Uk Ur Vp Vq) Ha(aJ Ar AX aZ bA bV cH dE Dg Hf Id Ih Ik It Jg Jp Jr Kc Kp Lx Mm Nr Nw Nx Oa Ok Ou Oy Pb Pe Pf Ph Qe Ri Sr Uh Wm) Hw(Fr gL Id Ir Is Iv Jf Jh Jl Jr Jt Kp Lh Li Lj Lw Md Mk Nd Nf Nh No Nr Nv Ny Og Ou Oz Pc Pe Pf Pg Ph Qa Qe Ri Sr Uk) Ou(Aa aX Bg bJ bZ cE cH cM Co Ct Dc Dd dI Dk Hf Hq Jj Jl Ma Md Mj Mk Mr Mv Nf Ow Oy Pg Po Qw Ri Uk Ur Vp Vs Vu) Ri(aJ Db Dc dE Dk Hf Id In It Jf Jj Jk Jp Js Ki Ko Md Mj Mr Mu Na Nd Nf Nm Oe Of Pa Pb Pc Qw Sr Uk Ur Vp) Vu(Ap Ar bA Db dE Fp Hf Id Ih Ik Im It Jg Jp Kc Kp Lx Mb Na Nm Nr Nw Nx Ok Oy Pb Pf Ph Qe Sr Uh Ur Vt Wm) Jf(Aa aX Bg cH cM Db Dc dE Dk Hv Id It Jj Jl Kp Ld Mb Md Mj Mr Mv Na Nf Nm Pa Pb Pg Ph Pj Qw Vp) Sr(aN Bg Ch Cp Ct Db Dd Di Dk Hq In Jj Jl Jo Kj Ma Mk Mr Mv Nd Oe Of Oy Pg Po Qw Uk Vo Vp Vs) Nf(gL Hf Ii Ir Jh Jl Jq Jr Kc Kk Kp Lj Lw Mk Nb No Nr Nv Nx Ny Pb Pc Pf Pg Qa Uh Uk Ur Vq) Vp(bA cH Db dE Fp Hf Id Ih It Jp Kc Kk Ko Kp Lj Lx Mb Na Nr Nw Oy Pb Ph Qc Uk Wm) Md(aA gL Hf Hx Ir Jh Kc Kk Kp Lw Mk Nd Nj Nm Nn Nr Oz Pb Pf Ph Po Uh Uk Ur Wm) Ur(Aa aI aX aZ Bg cH Db Dc dE Di Dk Hf It Jk Kc Ko Kp Mj Mr Mu Mv Nm Oy Pa) Ph(Bg bJ bZ cE Db Dc dI dJ Dk Hq Hx Jl Jr Ma Mk Mp Mr Mu Mv Mx Nd Pg Qw) Mr(aA Dg Hx Id Ik In Iv Jr Kk Kp Li Lj Mj Nx Oz Qa Qe Rf Uh Uk Wm) Nd(aA Is Iv Jh Jl Lh Li Lj Lw Mk No Nr Nu Nv Nx Ny Pc Pf Pg Qa) Hf(Aa Bg cM Dc Dd Di dJ Dk Hq Id It Jj Jk Me Mj

Figure 11 Continued

Figure 11 Continued pF Qw Sr Ur Vp) Mi(aA Fr Hx In Iq Iv Jh Jm Jr Jt Lv Mf Mg Ml Nf Ns Nu Nv Ny Of Oh Oi Oy Oz Pb Pe Pg Pz) Md(Fr Hw Ih Im Iq Is Iv Jr Jt Lh Li Lj Lv Mr Mw Nd Nu Of Og Oi Oy Oz Pc Pe Pg Qa Sr) Nf(Aa Ad aJ Ap Ar bN cH Dg Dl Fr Id Im Is Iv Jt Kc Kk Kq Lh Li Mr Nv Ou Pe Qe Sr Uh) Ih(AA Fp Fr Ip Iq Is Iv Jh Jl Jt Lh Li Mg Mr Nd Ne Nh Nj Nu Nv Oz Pa Pb Pe Pg) Jg(Aw aX Bg bN CH Cw Db Dd Di dJ Gl gP Ib Jf Kc Ou Qt Qw Rb Vo Vp Vs Vu) Iv(AA Fr In Is Jh Jl Jm Jr Jt Lh Li Lj Mg Mr Nd Nv Oh Oi Oz Pe Pg Pz) Mr(Fr Hq Iq Jh Jm Jr Lh Li Lj Mg Nd Nv Ny Og Oh Oi Oz Pa Pe Pg Pz) Aa(Jf Ji Js Kc Kk Lu Lv Ma Mw Nh Ns Nt Nu Ou Oz Pa Qy Rb Sr Wm) Ne(Ik Ip Jh Jl Jm Jq Jr Lj Lw Mg Mk Mz Nb Ns Ny Og Oh Pc Pg Pz) Nj(Hw Ip Jh Jl Jm Jq Jr Lj Lw Mg Mk Mp Mz Nb No Ny Oh Pc Pg Pz) Sr(bN Dc Dd Di Gl gP Ha Iq Jf Jk Js Kc Mj Mu Mv Ou Pa Qw Vp) Ok(Bg bJ cH cQ Dc Dd Di dJ Dk Gl gP Ha Jf Ou Ut Vp Vs Vu Tj) Nw(Bg bJ bN cH cQ Dd Di dJ Gl gP Ib Ic Jf Ou Ut Vs Vu) Me(bN cH Hf Ic Id Ik Jf Kc Kk Kp Ou Ph Qm Tt Uh Vp) Nh(Ik Ip Is Jh Jl Jq Jr Lj Lw Ns Nv Ny Og Oh Pg Qa) Lh(gP Hq Im Iq Is Jh Li Lj Nd Ns Nu Og Oz Pe Qa Qe) aA(Ik Im Ip Jn Jq Jr Li Lj Nd Ns Nv Pe Pg Pz Qa Qe) Dg(bN Dc Dd Dk Jf Jk Jo Js Ma Mt Mv Nd Oe Qw Vo) On(Bg bN Ch Dc Di Dk Gl Ha Tn Ut Vp Vs Vu Tj) Jt(Fr Im Iq Jh Jr Lj Nd Ns Og Oz Pe Pg Qa) Pa(Fr Ip Iq Is Jh Jl Jr Li Mg Nu Nv Oh Oi) bN(Ap aX It Jm Kk Kp Lx Mm Mt Oh Qa Qe) Ik(Jl Lw Mk Mz No Ns Nv Ny Oh Pe Pg) Im(Fr Is Jl Js Li Mk Ns Nu Og Oz Pe) Lj(Fr Ha Ip Iq Is Jh Mg Nd Nv Pc Pg) Lv(Jl Mg Ns Nu Nv Ny Og Oh Oi Pg) Kc(bL cH cM Dl Jf Jm Mt Ou Vp) Nd(cH Fr Is Jl Li Nv Pe Pg Qa) cH(bA gL Kk Mt Oh Oy Qe Qy) Dc(Ad Ji Jp Lx Mt Qa Qe) Jf(Ap Dl It Mm Nm Ph Pj) Ou(fR Hq Ic Id Mm Rb Ri) Fr(Iq Is Jl Jr Ns Nu) Jh(Is Nu Pe Pg Qa Qe) Ns(Li Nv Pe Qa Qe) gP(Kk Mt Oh Qe Qy) Iq(Jl Li Nv Pe) Jm(Al Dd Ur Vu) Ap(Bg Jk Mv) Ha(Fp Lx Pe) Mg(Is Pe Qa) It(Dd Ur Vp) Nv(Js Li Og) Mk(Fp Qa) Is(Oh Oz) Kk(dJ Ex) fR(Oz Qw) MtaX InQa QcQe KyVq LiOg} Nf{Nx(AA aJ Bg bN Ch Dd Dk Fp Gl gP Ha Id Ik Iv Jf Jg Jj Jp Kc Kk Lh Lj Lv Mi Mm Mr Nd Ne Nh Nj Nt Ou Pa Qe Qw Rg Ur Ut Vp Vq Vs Vu) bN(aJ AP Ar aX Bb bV cB DG Fp gL Id Ik It Jg Jm Jp Kp Lx Me Mm Mt Nd Nj Nr Nu Nw Oh Ou Oy Oz Pa Pb Pc Ph Qa Qe Qw Rb Sr Ur) Kc(Aa Bg bL cE cM Dc Dd Di Dk Id It Jf Jk Jp Js Kz Lx Me Mj Mu Mv Nr Nw Ok Ou Pa Sr Ue Ur Vp Wm) Kk(Aa aZ cE Dc Dg dJ Fw Id It Jf Jk Jp Js Kz Lx Mm Mt Mu Mv Nm Nr Nw Ok Ou Pa Pj Qw Sr Uh Ur) gP(aJ Ar Dg fR Id It Jf Jp Kp Kq Lh Lx Nd Nj Nw Ok Ou Ph Pj Qe Qw Qy Rb Ri Rj St Uh Ur Vq Vt) Mr(Ar Hw Ih Im Iq Iv Jj Jp Jr Lh Li Lj Md Mf Mj Nc Nd Ne Nh Nu Nv Og Oi Oz Pe Pg Qa Qe) Nd(aJ AP Ar aX aZ bA cH dE DG dM Fp Fr Im Is Iv Jl Jt Lh Li Mi Nv Pe Qe) Pa(AA aJ cH Dc Fr Hw Ih Im Is Iv Jf Jl Jp Jr Jt Lh Li Mk Nb Nu Pe Qe Rb Sr) Wm(Aa aJ aZ bA bJ Dc dE dM fR Fw gL Jf Jq Kn Kp Lx Nm Ou Ph Qw Ri Sr Uh Ur) Ou(aX Bg bJ fR Id It Jf Jk Lx Me Mk Mu Mv Nw Ok Pj Qw Rb Ri Sr Ur Vs) Mi(Hw Ih Im Iv Jj Jp Jr Lh Li Lj Lv Mf Ns Nu Oi Oz Pe Pg Qa Qe) Mm(aA Hw Im Is Jl Jp Lh Li Lj Mk Nb Nq Nr Ns Nu Oz Pb Pc Qe) Dc(Ad Ar Dg Id Ih It Jg Jm Jp Kq Lj Lx Nr On Oy Qe Sr St) Lv(FR Hw Ih Ik Im Is Iv Jl Jt Lh Li Lj Nu Pe Qa Qe) Fp(aA Db Fr Ha Hw Ii Ik Is Jl Jt Mk Nh Nt Og Pc Pe) Lh(Hw Ih Ik Iq Iv Jg Jj Jp Md Nc Nc Nh Nt Og Oz Qe) Ok(aI aJ Ao aX Bg cE CH Gl Jf Kg Qw Ri Ur Ut Vs) fR(aD cP cQ Cv Db Hq It Jr Ml Mv Nj Nq Pb Pc Um Up) Jg(AA Bg Dk Im Iq Jk Jl Jr Js Mu Oy Pb Qe) Sr(Bg Dd Dk Jf Jk Js Me Mu Mv Oe Qw Ri Ur Vo) Ik(Aa Fr Hw Ih Is Iv Jl Jt Li Lj Nr Pe Qe) Nw(aX aZ Bg bJ Gl Ha Jf Ur Ut Vp Vs Vu) aJ(It Jk Mu Mv Nj Nq Pc Qw Rb Ur Vq) Aa(Jm Js Lu Ma Mt Nc Ne Nh Oi Oz) Dg(Bg Dk Jf Jk Js Ma Mv Oe Qw Vo) Lx(aX Bg Db Dk Gl Qw Ur Ut) Js(Ad Ap Ar Id Kq Pj St Uh) Vq(aP aX dE Jn Ky Qw Ra Uk) Iv(Jj Jp Ne Nh Nj Nt Qe) It(Dd Id Jf Qw Ur Vo) Jj(Jl Jt Li Nv Pe Ur) Nh(Fr Is Jl Jt Pe) Jp(Bg Dk Mf Nu Pb) Nt(Fr Pb Pc Pe) Id(Me Rb Ri Ur) Jf(Fw Ph Pj Ur) Dk(Ar Kq On) Md(Nb Nv Pe) Ne(Is Jl Jt) Nj(Jl Jt Nb) Qw(aX Nr Rf) Ap(Bg Mv) Mt(Jl Mk) Ur(gL Ri) ArMa AxRg EmLd HaLj MeHf MjaX MvJd KqVo PbcH} Nd{Og(aA FR Hw Ip Iv Jh Jl Jq Li Lj Lw Mg Mk Mz Nb Nc Ne Nh Nj No Nr Nu Nv Nx Oi Pb Pc Pe Pf Pg Pz Qa) Nc(aA Fp Fr Ih Im Ip Is Iv Jl Jt Lh Li Lj Lv Lw Md Mr Mz Ni Nk Nr Ns Nu Nv Nx Pc Pe Pg Pz Qa Qe) Mr(Fr Hq Hw Ih Ik Im Iq Iv Lh Li Lj Lv Md Mj Ne Nh Nr Nu Nv Nx Oy Oz Pe Qa Qe) Im(aA Fp Fr Hw Iq Is Iu Iv Jl Js Jt Lh Li Lv Md Mk Ne Nh Nj Nr Ns Nu Nx Pe) Nx(bN Dc Fp Fr gP Hw Ih In Is Iv Jl Jt Lh Li Lj Lv My Ne Nh Ns Nu Pe Qe) Mi(aA Hw Hx Ij In Iq Iv Jt Lh Li Lv Ml Nr Nu Ny Of Oi Oy Oz Pb Pe Qa) Ne(Fp Fr Ih Ip Is Iv Jl Jt Lh Li Lj Lw Me Mz Ns Nu Nv Pe Pg Qe) Md(aA Fr Ih Ii Is Iv Jl Jt Li Lj Lv No Nu Ny Pc Pe Pg Qa Qe) Nh(aA Fp Fr Ih Is Iv Jl Jt Lh Li Lj Lw Me Mz Ns Nu Pe Pg Qe) Jj(Ij Io Ir Jh Jr Lw Mf Mk Mu Mx Nb Nn Oh Oy Oz Pb Pf Qb Qd) Ih(Fp Fr Hw In Ip Iq Iu Iv Jl Jt Lh Li Lw Nj Nu Pc Pe) Iv(Fp Fr Hq Ik Li Lj Lv Me Nr Nu Nv Oz Pe Pg Qa Qe) Lh(aA Fp Hq Hw Iq Iu Jo Js Lj Lv Nj Ns Nu Of Oz Qe) aA(Jn Jq Jr Li Lj Lv Lw Nj Ns Nu Pe Qe) Me(Ar bA cH cM Db Dc Dg Fp gP Ik Sr) Jp(aI Bg bN CH Dc Dd Di Dk gP) Jt(Fp Hw Iq Iu Lv Nj Ns Nu Oz Pe) Pa(aJ aX bA bN cH Dc Dg dM gP) Fr(Fp Ik Iq Lj Lv Nj Ns Nu) Is(Fp Hw Ik Iq Lj Nj Nu Oz) Pe(Hq Hw Iq Iu Lv Nj Ns Nu) bN(aJ aX It Lx Mm Nr Nw Ok) Qe(Fp Iu Js Lv Nj Ns Qc) Li(Ik Iq Iu Lv Nj Ns Nu) Dc(Dg It Lx Mm Nw Ok) fR(cP Iq Ou Oz Pc Qw) Qa(Hw Iq Iu Lv Nj) Jl(Fp Ik Lj Nj Nu) Nv(Hw Iq Iu Nj Ns) gP(aJ dM Nw Ok Rb) Lj(Ik Iq Lv Pc) Nu(Fp Lv Ns) Mj(aJ aX dG) Nw(Dk Gl Vp) Ok(Bg Dk Gl) Dg(Jk Jo) ApMv FpMk NrLv NsPc HueP aUaV aXeM} Kc{Dc(Aa Ad Ar bI bL cE cH cL cP Di Dl eF Fp Fy gP Hb Id Ih It Jf Jg Ji Jm Jp Jt Kq Lj Lx Md Me Mm Mt Mu Mv Nm Nr Nu Nw Nx Ok On Ou Oy Pa Pj Qe Qh Qy Rb Rf Sr St Uc Wm) Jf(Aa Bg bL cE cM Db Di Dk gW Ha Hq Hw Ib Io Iq It Jk Ki Md Me Mj Mu Mv Nm Nr Nu Pa Pg Pj Qw Ul Ut Vp Vs Vu Tj) Jk(Aa aX bA bI cM cP Dg eF Hb Id Ih It Jg Jm Jp Lx Md Me Mm Mt Mw Nr Nu Nw Nx Ok On Ou Oy Pa Qe Qy Sr Ul Wm) Mv(Aa aJ Ap bA bJ bL cM cP Db Dd Dg eF gL Hb Jg Jh Jp Lx Md Me Mm Mt Nr Nw Nx Ok Ou Oy Pa Qy Sr Ur Vp) Dr(aD aG Ap bR Cv dI Dk Ed Fr Hb Hv Hx Ic Im Jd Jh Jy Kp Mr Mu Ni Nj Nk Nl Nx Pz Qt Qu Ss) Gc(aJ aP bI bO bV cH cR dG dK dM dN In Io Jq Jy Mf Mm Nk Nl Nu Nx Ok Qx St Ug) gP(aJ Bg bJ bL cA cQ Di Dk gW Iq Kx Md Mu Nu Nx Qw Qy Rb Sr Ur Vs Vu Wm) Mj(Dg eF Fp fR gW hC It Jp Lx Me Mt Nr Nw Nx Ok Ou Pa Qe Rf Sr) cE(aX aZ bA bI cM dF eF gL Ha Iq Md Nu Ou Pa Qw Qy Ur Vp) Dk(Aa bI cP Dg eF Hb Jg Jp Lx Me Nw Nx Ok On Ou Pa Qy) Mu(aJ aX bA bI cM cP eF gL Jp Md Me Nr Nx Ou Pa Qy) bL(Aw Db Dd dE Di Jl Jr Ki Md Nu Ou Oy Qy Vp Vu Wm) Me(Bg cM Db Dd Js Md Nr Pa Ur Vp) Aa(cM Di Jo Js Ma Md Ou Pa) Nx(Ha Md Nv Pg Po Vp Vu Tj) dJ(gL gW Qb Qw Qy Up Ut Vs) Ou(Bg cL Hq Mk Ut Vu Tj) Vp(bA bI cL cM Di Nw Pa) Em(dI dN Lh Mr Vt) Ha(cH Fp Lj Lx Nw) cM(aI Di Gl Jr Nu) Nw(Pg Po Ut Vu) cQ(cH Di Kx Md) Bg(eF Jp Qy) Jr(bA bI cH) Ut(bA bI Jp) Vu(cK cP Pa) Aw(cA dI) Di(gL Ur) Po(Lj Lx) Md(cA cL) aU(aK cY) bN(hC pF) dX(dB Nm) DbdI DgVo GlbA SrJs QycL KxaZ VqVs aVgW} gP{Kk(aI aJ Bg bJ bN cA cE cH Dc Dg dJ eM gW Jk Jr Jv Ki Kp Ma Md Mj Mu Mv Nm Nu Nw Nx Pa Pj Qy Rb Rj Sr Ur Ut Vs) Nw(aJ Bg bJ cH Dc Dk Gl Ha Hq Jk Jl Jq Jr Js Ma Md Mj Mr Mu Mv Oe Pc Pg Po Qw Rg Rj Ur Ut Vp Vs Vu Wm Tj) Wm(aJ aX bJ bN dM eF gL gW Ha Iq Jf Jk Jp Kp Mq Mt Ok Ou Pa Ph Po Qw Qy Rb Rg Ri Rj Sr) Qw(aX bA bN bV cH Dg dM fR gL Jf Jp Kp Mc Mt Nu Nx Ok Ph Qe Qy Sr Ul Ur) Dg(aI aW bF Bg bJ bN cE CH Co Ct Db dM GL Jk Jo Ur Vo Tj) aJ(Aa Bb Di Dl dO Gt Jf Kp Mc Mj Mv Nx Ou Pa Pj Qy Rj Sr Ur Vs) Rb(aX bV cH dM fR gL In iZ Jf Jj Jk Jp Kp Na Ou Pa Pc Uk Ur) Nx(Bg Dc Dk Ha Hq Jk Md Mr Mu Mv Nv Pg Po Rg Ut Vu Tj) Ur(aX cH Di Dl dM fR gW It Jm Kp Nm Ou Oy Pa Qy Rj Sr) Bc(Bg bJ bM bN bV cE CH Ct Dc dI dJ Dk dM eF fR) Ok(Ao Bg bN cE cH Dc Gl Hq Jk Jo Js Mv Oe Po Ut Vs) Sr(aX bN Dc Gl gW Ha Ii Jk Js Md Mu Mv Pc Vo Vs) fR(Ad AW bP Cw Di dJ dM dV gL gN Gt Me Oz Pc) Qy(aX Bg cE CH Ct Dk Jf Jj Jk Mu Mv Vs Vu) gL(aD bM bN bZ cE Ch cL Di dJ Dl dM Vs) Mc(aX cH Db Kp Oy Pc Rg Ri Rj Uk Vq) Ap(Ao Bg bN cE CH Dc Dk dM Mv) Jp(Bg Dk Gl Ha Mu Mv Rg Ut Vs) eF(Bg CH Ct Db Dc Di Dk Dl) cH(aA aP aW bA Bb Db dM) Dl(bN bV Dc Dk dM) Qe(Dc Mj Qb) aX(Jf Ou Vs) Dk(Kq On) Gw(cL Dd) dO(aP dG) eP(aV Oz) iZ(bJ hC) AdDc BaCt BoGt DbdM PoLx GlLh HaLj MqVq QxeM KfVs KpbN dLeX} Me{Sr(aN aX aZ Bg cE cM Cp Db Dd dE Ha Hf Hw Jf Jj Jk Jl Kj Kp Md Mj Mk Mr Mu Mv Oe Of Oy Pg Qw Ur Ut Vo Vp Vu) Hf(aJ aX bA Bg Dc Dd dJ Dk dM Fp gL Hq Id It Jj Jk Js Lx Md Mj Mk Mu Mv Nw Ou Pa Qw Ri Ur Vp Vs Vu) Ik(AA Bg bN Dc Dk Fp Hw Is Iu Iv Jg Jl Jo Lh Li Lj Lv Md Mk Mr Nc Ne Nh Nj Nr Ns Nt Of Pe Qw) Dc(Ad Dg Fp Fy Id It Jf Jg Jp Kf Kk Kp Nr Ok Ou Pa Ph Pj Qe Qh Qm Tt Uh Ur Wm) bN(aJ aX bV cB Db Id Ki

Jk{Qy(It Nr Oy) Oy(Rb St)} Nl{No(Mc Ml) Mp(Oz Pd)} Mj{hC(Nr Nu Qe)} It{Js(Rb Ur) GlUr} cM{aA(bR cB) cBdM} Po{Lj(Ar dG)} Gc{UecF IbJn} Mv{ApUr QybA} dX{HuKd IbKp} BaCtDi DkDlcP DoFwaD NrJrpF aNdJeX

Constrained panels with 2 analytes, where 1.0E-7 >= 'model p-value' > 0. Contains 35 panels of 77,685 total panels evaluated. : Et(Fp Ik Iq Jj Jo Ly Md Mt Nc Nd Ne Nh Nj Nl Of Om) Ok(Jo Js Lx Ly Md Mt Nc Nd Ne Nf Nj Nl Of Om) Nl(Ji Lx Mm Nw) MdNw Constrained panels with 2 analytes, where 1.0E-6 >= 'model p-value' > 1.0E-7. Contains 75 panels of 77,685 total panels evaluated. : Et(Dc Dk Hw Ih Ji Jr Js Jt Lv Lx Mi Nf Nq Ns Nt Ok Oz Pa) Ok(Fp Hq Hw Hx Ik Iq Jj Jt Lv Mq Nh Nq Ns Nt Og Oz Pa) Lx(Jj Ly Md Nd Ne Nj Om Po) Nl(Jg Jj Jp Mi Mt On Pa) Nw(Js Ly Nc Nd Ne Nj Om) Ji(Ly Nd Ne Om) Mt(Jj Nd Om) Jg(Md Mv Om) On(Md Om Oy) Jj(Ik Nt) Jp(Ly Nj) GnaV Constrained panels with 2 analytes, where 1.0E-5 >= 'model p-value' > 1.0E-6. Contains 166 panels of 77,685 total panels evaluated. : Lx(aA Hw Hx Ik Iq Iv Jg Ji Js Lv Mi Mm Mr Mt Nc Nf Nh Nq Ns Nt Nw Og On Oz Pa) Mt(Fp Hw Iq Iv Jg Ji Js Lv Ly Md Mi Mm Mr Nc Ne Nj Ns Nt Nw Og On Pa) Nl(AA Fp Fr Iv Jt Lh Lv Ly Md Mr Nk Ns Nt Nx Og Om Pc Pe Qe) Nw(Hw Hx Ik In Iq Jj Lv Mm My Nf Nh Nq Ns Nt Of Og Oz Pa) Ly(Aa aX bN cH Dc Gn gP Jg Jj Mi Mm On Pa) Ji(Fp Ik Iq Jj Md Nc Nf Nh Nj Nt Og Oz Pa) Jg(Jj My Nc Nd Ne Ng Nj Ns Of Og) Mm(Fp Ik Lv Nc Nd Ne Nh Nj Om) On(Jj Nc Nd Ne Nf Nh Nj) Et(aA Bg Ch Gl Kg Ut) Gn(Fw Hu Kc Kk Ra) Pa(Ne Nh Nj Nt) Jj(Ne Nh Nj) Nt(Og Om) Mi(Hq Nj) Nd(Aa Jp) Ik(Jp Og) MdNx KcbN aJgP Constrained panels with 2 analytes, where 1.0E-4 >= 'model p-value' > 1.0E-5. Contains 339 panels of 77,685 total panels evaluated. : Ly(aA aJ Db Dk Fp Fr Hf Id Ih Ik Im Is Iv Jf Jr Jt Kc Ko Lh Li Lj Lv Md Mr Nc Ne Nh Nj Nt Nx Og Ou Pe Qa Qe Sr Uk Ur) Et(aI Ao bN cE Co Cp Ct Cw De Di Ef gP Ha Ib Jf Kc Ke Kj Ks Ou Qt Qw Rg Tn Ur Vo Vp Vs Vu Tj) Jg(Fp Hw Ih Ik Iq Iu Iv Jh Ji Jk Jo Js Lj Lv Mi Mm Mr Mu Mw Nf Nh Nq Nt On Oy Oz Pa) Gn(aD aJ aX bR bU cF CH cN cP Cs dG dI dJ dL Ef Gl Ld Me Og Qw Qx Rb Rc Uo Vo) Jj(Fp Im Iv Jm Jp Jt Lh Li Lv Mg Mm Mr Nc Nd Nr Nu Nx Pa Pe Qa Qe) On(Fp Hq Hw Ih Ik Iq Jk Js Lj Lv Mm Mv My Nq Ns Nt Nx Of Og Oz Pa) Mm(aA Hw Ih Iq Iv Ji Jp Jr Lj Md Mi Mr Nf Ns Nt Oz Pa Pb) Nj(AA Fp Fr Is Iv Jl Jt Lh Li Lj Lv Mr Nt Nx Og Pe Qe) Ko(Bg bN Dc Dk Gl gP Jf Jk Js Ma Me Mj Mv Nf Om Qw Ut Vs) Ne(AA Fp Fr Iv Jp Jt Lh Lv Md Mi Mr Nt Nx Og Om Qe) Lv(Fp Ih Ik Iv Ji Jp Md Nc Nd Nh Nt Og Om Pa) Fp(Jp Md Mi Mr Nc Nd Nf Nh Nt Og Om Pa) Nt(In Jp Js Md Mi Nc Nd Nh Ns Oz Pb) Om(Aa Ik Im Jp Lh Li Mi Nh Pa Qa Qe) Nh(aA Jp Md Mi Mr Mt Og Qe) Ji(Hw Ih Iv Jo Jq Js Nq Ns) Pa(Ik Iq Iv Jp Mi Nc Nd Nx) Mi(Ik Md Nc Nd) Mt(aA Jp Nq Oz) Dc(Ad Dg Nw) Dk(Dg Nw Ok) Nd(Ih Mr Qe) Jp(Iq Md Nc) cH(aA bA gL) Kc(dJ gP) bN(aJ Wm) DqeF MrIk IqQe KkgP OzfR aVdO Constrained panels with 2 analytes, where 1.0E-3 >= 'model p-value' > 1.0E-4. Contains 630 panels of 77,685 total panels evaluated. : Ko(aI aX aZ cE Ch Cp Di dM Ha Hq In Jj Jl Jo Jr Kc Kg Kj Md Mk Mr Mu Oe Of Ou Pa Pg Po Qc Qt Rb Ri Ua Ur Vo Vp Vu Tj) Nf(Aa aJ Ar aX bN cH Dg fR gP Id Ik Iv Jf Jp Jt Kc Kk Lh Li Lv Ly Mi Mr Nx Ou Pa Pe Ph Qe Qw Rb Sr Uh Ur Vq) Om(aA Ap bN cH Dg Dl Fr Gn Id Ih Is Iv Jh Jj Jl Jt Kc Lj Ly Md Mr Nc Nj Nr Nu Nv Nx Ou Pe Pg Ph Sr St Uh) Nd(aA aX bN Dg FR gP Hw Im Ip Is Iv Jl Jt Lh Li Lj Lw Ly Nc Ne Nh Nr Nu Nv Nx Og Pe Pg Qa) Jj(aA Fr Gn Hw Ih Ii Ij Ip Ir Is Jh Jl Jr Lj Md Mf Mi Mk Nv Oh Oi Oy Oz Pb Pd Pf Pg Pz Wm) Nc(AA Fr Hw Ih Ik Im Ip Is Iv Jl Jt Lh Li Lj Md Mr Ni Nk Ns Nu Nx Og Pb Pe Pg Qe) Kc(Aa Bg bL cE cM Dc Dd Di Dk Hq Iq Jf Jk Md Me Mj Mu Mv Nr Nu Ou Pa Qw Sr Ur Vp Vu) gP(AP Ar bA Bb Bc cH Dg Dl dM eF fR gL iZ Jf Jp Kp Me Nw Ok Ou Qw Qy Rb Sr Ur Wm) bN(aA Ap bA cH DG Dl gL It Kk Kp Me Mt Nj Nw Ok Ou Pa Pc Ph Qe Qw Rb) Mi(Hw Hx Ih Im In Iq Iv Jp Jr Li Lj Lv Ns Nu Nx Of Og Oy Oz Pg Qc) Ly(gL hC Hw Ir Jh Jl Kp Lw No Nr Nv Oz Pb Pc Pf Pg Ph Ri Vp) Ik(AA Fp Fr Ih Is Iv Jl Lh Li Lj Md Me Ne Nj Ns Nx Pe Qe) Jp(Dc Dk Gl Hw Hx Ih Iv Js Mb Mf Mr Nq Ns Nu Nx Og On Oz Ut) Nj(Gn Hw Ih Im Ip Jr Md Mk Nb Nh Nr Nu Nv Pb Pc Pg Qa) Gn(Fb Gw Jy Kf Kj Mf Oa Or Ou Qu St Ue Uf Um Uu) Nx(aA Dc Fp Ha Ih Iv Lv Mm Mr My Nh Og Qc Ut Vu) Dg(aI aW Bg cE CH Co Ct Db Dd Di Jk Vo) Md(Lh Li Mr Mw Nb Nu Nv Pa Pc Pe Pg Qe Wm) Me(Hf Id Jf Kp Ou Ph Qw Sr Ur Vp Vq Wm) aA(aX bA bR bU cB cM Fp Jg Jr Lv Nt Pa) Aa(aJ Fp Jf Jr Kk Lx Mt Nh Oz Pa Wm) Qe(Dc Hw Lv Mm Mr Nq Og On Oz Pa Qc) cH(aJ aP aW cB cP cR Db dF dG dM eF) Nh(Fr Hw Ih Iv Jt Lh Li Lj Ns Pe) Lv(Im Is Li Lj Mr Nr Nu Oz Pe) On(Hx Ii Iv Jo Mb Mf Ng Nu Pg) Et(aH aO aX bF cG gL hC iZ) Mm(Is Jl Li Mb Nq Nu Og Pe) Iq(Ih Im Jt Lh Li Mr Pe Qa) Pa(Hw Ih Jf Jr Mr Nu Og Rb) aJ(bA bL bR bU cB cM Db dJ) Dc(Ap Dl It Jg Lx Ok Sr) Wm(gL hC In Mj Mr pF Pg) Nw(Bg Gl Ha Ut Vp Vu Tj) Ne(Im Is Li Lj Ns Pe) Ou(aX Bg Hq Jk Mu) Dk(Ad Ap Dl Jg) Mr(Hw Iv Og Oz) bA(bU cB cT Db) Ha(Fp Lj Lx) Iv(Fp Og Oz) Jf(It Ph Pj) Ok(Bg Gl Ut) fR(Db dO Pc) Mj(aX Kk) Hw(Ih Pe) Sr(Jk Js) Qy(Jk Mu) Og(Jt Nu) Oz(Ih Lh) dJ(gL Kk) iZ(hC Jr) BaCt DdGw GlLx ItUr QwaX aVeP cMdM cNdO dVeF Constrained panels with 2 analytes, where 1.0E-2 >= 'model p-value' > 1.0E-3. Contains 1,561 panels of 77,685 total panels evaluated. : Om(Ad aJ Ar AX BA Bb bJ dJ eF fR gL gP hC Hw Ic Ij Ip Ir Jd Jf Jm Jq Jr Kk Kp Kq Lw Mg Mk Mu Mx Mz Nb Nd Nn No Ny Og Oh Oi Oz Pb Pc PF Pj Pz Qb Qd Qw Qx Qy Rb Rf Ri Tr Tt Ue Ur Vq Wm) Dg(aA aH aJ bA cP Cw dM Ez GL Ha Hq Ii In Iq iZ Jf Jj Jl Jo Js Kg Kj Kk Kp Ma Md Me Mj Mk Mp Mr Mu Mv Nj Oe Of Oy Pc Pg Po Qt Qw Ss Ua Uk Ur Ut Vp Vs Vu Tj) Aa(aP aV aW aX bA bC bN bV cB cH cM cP Dc dF dG Di Dk dM eF gL hC Hw Ih Iq It Iv iZ Jg Js Kd Lu Lv Ma Mb Mf Nr Ns Nt Nx Og Oi Ou Pc pF Qw Qy Rb Rj Uk) Md(aA Ar cH Fr gL hC Id Ih Ii Im Ip Is Iv iZ Jf Jh Jl Jq Jr Jt Kk Kp Lj Lw Mg Mk Mp Nd No Nr Ny Og Oi Ou Oz Pb PF Ph Po Qa Rb Sr Uh) bN(Ad aP aV aW aX Bb BC bU bV cB cR Db dF Di dM eF hC Ic Id iH Ik Iq iZ Jf Jg Jp Kf Lv Lx Mm Nh Nr Nu Nx Oe Oh Oy Oz Pb Qx Qy Sr Ur) Dc(Ba Bb Bc cH Cv eF Fp Gw Id Ih Ik Ji Jm Jt Kf Kk Kp Kq Lh Lj Me Mm Mt Nj Nr Nu On Ou Oy Pa Pc Ph Pj Qa Qx Qy Rb Rf St Uh Ur Wm) cH(Ap aZ Bb Bc Di Dl eP fR Gt hC Id In Iq It iZ Jf Jj Jk Jp Lv Lx Me Mt Nd Nj Nu Nw Oe Ok Ou Oy Oz Pa Pb Pc Ph Qw Qx Qy Rb Ur) Kk(Ao aX Bg cE cM Dk Ex gW Ha hC Hq Hx Ib Ij In Iq Jk Jl Jr Js Ld Mk Mm Mr Mu Mv Mw Nm Oy pF Pg Pj Po Qw Ut Vp Vu Tj) Ur(aX bC bE Di Dl GL gW hC Id Ih iZ Jf Jk Jm Kp Lx Mj Mm Mr Mu Mv Nm Nr Nw Ok Ou Oy Pa pF Qw Rb Sr Ug Vp Vu Wm) aX(dO eM eP Iq It Iv Jf Jj Jk Jp Kp Lv Lx Me Mt Mu Mv Nj Nr Nu Nw Nx Oe Ok Pa Pc Ph Qe Qx Qy Rb Rj Sr Vo Vs Wm) Jf(Bg cM dE Dl gL gW hC Hw Ic Io Jk Jp Kp Lx Mj Mm Mr Mu Mv Nm Nr Nw Ok Ou Oy Pc pF Qw Qy Rb Rf Ri Sr Vp) Og(aA eP Fr Hw Ih Im Ip Iq Ir Is Jh Jl Jr Lh Li Lj Mf Mg Mk Nb No Nr Nv Oh Oi Oy Oz Pb Pc Pe Pf Pg Pz Qa) gP(aA bU bV cB dG eM Fr Gt Ic Id Ik It Jg Lh Lj Lv Lx Mm Mt Nj Nr Nu Nx On Oy Oz Pa Pc Ph Qa Qe Rj Vq Vs) Nf(Ap bA cB cP Fr gL hC Hw Ih Ii Im Ip Is iZ Jl Jr Kp Kq Lj Lw Mk Nb Nr Nu Nv Pb Pc pF Pg Qa Rf Ri Wm) Qw(aJ bA bV Dl Fp gL Id Ih It Jg Jp Kp Lx Mm Mt Nm Nr Nu Nw Oi Ok On Ou Oy Pa Ph Qy Rb Rf Ri Sr St Ul) Vs(aJ Ap bA gL hC It iZ Jg Jp Kc Kf Kp Lx Mm Nm Nr Nw Nx Ok On Ou Oy Pa pF Ph Qe Qx Rf Sr St Uh Vq) Ou(cE cM Ct dI Dk Gl gW Ha Id It Ma Mj Mk Mr Mv Nw Ok Ow Oy Pa Pg Pj Po Rb Ri Sr Ut Vp Vu Tj) Wm(bA Bg cM dJ Dk dM Ha Hq Hw Hx Ij Iq Jk Js Lv Mk Ml Mw My Nb Nv Ny Oy Pb Ut Vp Vu Tj) Sr(Bg Ch Di Dk Gl Ha hC Hq Hw Ib In Iq Jj Mj Mr Mu Mv Nd Oe Pa pF Pg Po Rb Ut Vo Vp Vu) Iq(aJ Ap Ar bA FR Hw Ir Is Iv Jh Jl Jr Kp Lj Mg Mk No Nr Nu Nv Nx Pb Pf Pg Ph) Rb(aJ aZ dE hC Id Io It iZ Jj Jk Jp Kp Lx Mj Mr Mu Mv Nd Nm Ok Pb Pc Ph Pj Uk Vp) Bg(Ad Ap Ba eF Ik Jg Jp Kp Kq Lx Me

Figure 11 Continued

Mm Mt Nm Nr Nx On Oy Pa Ph Qe Qx Qy Uh) Nu(aA cM Db Fr hC Hw Ic Ih Im Is Iv Jl Jr Lh Lj Mr Ns Nx Oz Pb Pe pF Qe) Jk(Ad aJ Ap Ar
BA Bb bV Dl eF fR gL Hc Id Kf Kp Kq Ph Qx Rf St Uh Vq) Vu(Ap Ar Bb gL Id Ih It Jg Jp Kf Kp Lx Nm Nr Ok On Oy Pa Ph Qe Qy St Uh)
Dk(BA Bb eF Id It Ji Kf Kp Kq Lx Mt Nr Nx On Oy Pa Ph Qe Qy St Uh) Iv(aA Fr Hq Hw Hx Ih Im In Is Jl Jt Lh Li Lj Mf Mj Ns Oy Pb Pe Qa
Qe) Di(aA Ad aJ Ap aW BA Bb bC bU cB cP dF dG dM eF fR gL Jp Ph) Nd(aJ Ar bA Bb dJ dM eF gL Id Jh Mk Mx Mz Nb No Pc Pf Ph Pz)
Vp(Fp hC Id It iZ Jp Kp Lj Lx Mm Nr Nx Ok On Oy Pa pF Ph Qe Qy) Gl(Ap bA fR Id It Jg Ji Kp Kq Lh Mm Mt Nr On Oy Pa Ph Qe Uh)
Mr(Ar Ax gL Hq Id Ih Im Jr Kq Li Lj Mf Mj Oy Pe Ph Qa Rf Uh) Hw(Fr gL Im Ip Is Jl Jr Jt Lh Li Lj Mg Mk Nr Nv Nx Oz Pg Qa) Ut(Ap gL Id
It Jg Kp Kq Lh Lx Mm Mt Nr On Oy Pa Ph Qe Qy Uh) aA(Ad Bc Db Dl hC Ih Jn Jq Lh Li Lj Mf Mi Ns Oz Pc Pe pF Qe) Ha(Ar Ax Id Ih It Jp
Kp Mm Nr Oa Ok On Oy Pa Pe Ph Qe Uh) fR(AD aK aM aQ aV aW cB cP Cv dV hC Lv Me Mj Ml Oe Pa) Oz(aJ Fr Im Ir Is Jl Jr Jt Li Lj Lw
Mk Nb Nr Nv Nx Qa) Ns(Fr Im Is Jl Jr Jt Lh Li Nr Nv Nx Pc Pe Pg Qa Qe) Mu(aJ AP Ar bA eF gL Hc Id Kp Kq Ph Qx Rf St Uh) hC(aJ bA cJ
Fw gL In It Jj Jr Kc Ko Mj Nk Nr Nw Ri) pF(Et gL iZ Jr Kc Ko Kp Ly Me Mj Nk Nr Nw Pa Ri Vq) Mv(aJ Ap Ar bA Bb eF gL Id Kp Kq Ph Qx
Qy Uh Vq) Dl(aJ aW bA bC bI bU cB cP Db dM eP gL Oe Vo) dG(bR bU bZ cB cE cL cM Db dH dO dV cP gC) dJ(aP dF dM eM eP It Lv Nj
Oy Pb Pc Ph Qy) Mj(aJ Ar bV gL Id iZ Kp Ph Qy Rf St Uh) Nx(Co Dr Ib In Is Jl Lh Li Lj Ny Pe Tj) Ok(aH al Ao cE Ch Co Ct Ib Kg Qt Tn Tj)
dM(Ad aK Ap aV bR bU cB cP Db dO Lv Nj) Me(aJ Ar bA bV cB Db Dr gL iZ Ri Uk) Jp(aH al cE Ch Ct Ib Qt Ri Tn Ua Tj) dF(aH bF bU bZ
cE cG cM Db dO dV eP) Ap(aH al Ao aW cE Ch Co Ct Cw Vo) aJ(Ad Bb bC dO dV dV Lv Nq Oe Pa Pc) Nw(Ao bJ cE Co Ib Qt Qx Rj Tn) Vq(Ct
iZ Jo kS Ky Mq Oy Ra Uk) Pb(Ih Im Is Jr Jt Lj Mi Nr Qa) Ph(bJ cE dl Hq It Ma Mk Pa Pg) Id(In Kp Oe Po Qy Ri Rj Tj) Vo(Gc It Jg Kp Kq
Mm Nm Nr) aP(aV bL bR bU cB cM dO dV) Ar(Hq Ma Nj Pc Pe Pg Po) Ch(Ad Ba eF gL Jg Oy Qy) Db(bC bU cB cP eF Gw iZ) Lj(Fr Lh Mg
Pc Rg Rj Tj) Pa(bA bJ gL iZ Ri Rj Tj) eM(Ib Jy Kz Oa Qz Rf Uk) Gt(aN Bo bR cF Dd Fw) It(Dd gL Ic Kj Uk Tj) Qy(cE Hq Ib Jj Mk Ua)
cM(bE bV cB cP eF iZ) eP(aK aM cF cY Hu Mf) Ct(Ad bA eF Jg Oy) Mi(Mf Ml Ny Oi Qa) Ih(Fr In Lh Pc Rm) Nq(Fr Li Nv Qa) Lh(Hq Iu Js
Of) bU(aW Bc cR dE) gL(Lv Nj Oe Pc) iZ(bJ Hx Ly Nk) Tj(Lx Nr Oy) Gw(aD aN Dr) Nm(Kp Ri Uk) aV(aU cR dA) Bc(cB cP) Dq(cF Fw)
Fr(Jr Of) Im(Li Pc) Jj(Kp Pj) Js(Nv Qe) Ri(gW Ic) bA(Lv Pc) cR(cB cP) dV(bF cN) AdDd EfJg GcKj MfJl UaOy HqPe IpJr QxcE JoPj RfOe
NvOf bQdO dEeF

Unconstrained panels with 3 analytes, where 1.0E-9 >= 'AUC p-value' > 0. Contains 11,981 panels of 9,935,646 total panels evaluated. :
Gn{aD(AA aC Ad aE AF aG aH al AJ aK AL aM AN AO AP aQ AR AS aU aV aW AX aY aZ BA BB BC bE bF BG bH bI bJ bL bM BN BO
bP bQ bR bS bU bV bW bX bZ cA cB cC cD cE cF cG CH cI cJ cK cL cM cN CO CP CQ cR CS CT CU CV CW CX cY cZ dA DB DC DD
DE dF DG dH DI dJ DK DL dM dN DO Dp DQ DR DV dX Ed EF EM eP Et EX Ez Fa Fb Fn Fp FR Fw Fy GC GL gN GP GT GW Gz Ha Hb
Hc Hf Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Ky Kc Kd Ke Kf
Kg Ki Kj Kk Kl Kn Ko Kp Kq Kr Ks Kx Ky Kz Ld Lh Li Lj Lu Lv Lw Lx Ly Lz Ma Mb Mc Md Me Mf Mg Mh Mi Mj Mk Ml Mm Mn Mp Mq
Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi
Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf
Rg Rh Ri Rm Sr Ss St To Tr Tv Ua Ub Uc Ue Uf Ug Uh Uk Ul Um Un Uo Us Ut Uu Uv Vo Vp Vq Vs Vt Vv Wm Tj) Ly(AA aC Ad aE AF aG aH
al AJ aK AL aM AN AO AP aQ AR AS aU aV AW AX aY aZ BA BB BC bE bF BG bH bI bJ bL bM BN BO bP bQ bR bS bU bV bW bX bZ
cA cB cC cD cE cF cG CH cI cJ cK cL cM cN CO CP CQ cR CS CT CU CV CW CX cY cZ dA DB DC DD DE dF DG dH DI dJ DK DL dM
dN Dp DR Ed EF Em Et Ex Ez Fa Fb Fn Fp Fr Fw Fy Gc GL GP gW Gz Ha Hb Hc Hf Hq Hr Hu Hv Hw Hx Ib Ic Id Ih Ii Ij Ik Il Im In Io Ip Iq
Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj
Lu Lv Lw Lx Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh
Ni Nj Nk Nl Nm Nn No Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po
Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tr Tt Tv Tz Ua Ub Uc Ud Ue Uf
Ug Uh Uk Ul Um Un Uo Up Ur Us Ut Uu Uv Vo Vp Vq Vs Vt Vv Wm Tj) Hu(AA aC Ad aE AF aG aH al AJ aK AL aM AN AO AP aQ AR
AS aU aV AW AX aY aZ BA BB BC bE bF BG bH bI bJ bL bM BN BO bP bQ bR bS bU bV bW bX bZ cA cB cC cD cE cF cG CH cI cJ cK
cL cM cN CO CP CQ cR CS CT CU CV CW CX cY cZ dA DB DC DD DE dF DG dH DI dJ DK DL dM dN Dp DR Ed EF Em Et Ex Ez Fa Fb
Fn Fp Fr Fw Fy Gc GL GP gW Gz Ha Hb Hc Hf Hq Hr Hv Hw Hx Ib Ic Id Ih Ii Ij Ik Il Im In Io Ip Iq Ir Is It Iu Iv Iz Jd Je Jf Jg Jh Ji Jj Jk Jl Jm
Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Lz Ma Mb Mc Md Me Mf
Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt
Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm
Qn Qt Qu Qv Qw Qx Qy Qz Ra Rb Rc Rf Rg Rh Ri Rj Rm Sr Ss St Tn To Tr Tt Tv Tz Ua Ub Uc Ud Ue Uf Ug Uh Uk Ul Um Un Uo Up Ur Us
Ut Uu Uv Vo Vp Vq Vs Vt Vv Wm Tj) Rc(AA aC Ad aE AF aH al AJ aK AL aM AN AO AP aQ AR AS aU aV AW AX aY aZ BA BB BC bE
bF BG bH bI bJ bL bM BN BO bP bQ bR bS bU bV bW bX bZ cA cB cC cD cE cF cG CH cI cJ cK cL cM cN CO CP CQ cR CS CT CU CV
CW CX cY cZ dA DB DC DD DE dF DG dH DI dJ DK DL dM dN Dp DR Ed EF Em Et Ex Ez Fa Fb Fn Fp Fr Fw Fy Gc GL GP gW Gz Ha
Hb Hc Hf Hq Hr Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf
Kg Ki Kj Kk Kl Kn Ko Kp Kq Kr Ks Kx Ky Kz Ld Lh Li Lj Lu Lv Lw Lx Lz Ma Mb Mc Md Me Mf Mg Mh Mi Mj Mk Ml Mm Mn Mp Mq
Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi
Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rf
Rg Rh Ri Rj Rm Sr Ss St Tn To Tr Tt Tv Tz Ua Ub Uc Ud Ue Uf Ug Uh Uk Ul Um Un Uo Up Ur Us Ut Uu Uv Vo Vp Vq Vs Vt Vv Wm Tj)
Ra(AA aC Ad aE AF aG aH al AJ aK AL aM AN AO AP aQ AR AS aU aV AW AX aY aZ BA BB BC bE bF BG bH bI bJ bL bM BN BO bP
bQ bR bS bU bV bW bX bZ cA cB cC cD cE cF cG CH cI cJ cK cL cM cN CO CP CQ cR CS CT CU CV CW CX cY cZ dA DB DC DD DE
dF DG dH DI dJ DK DL dM dN Dp DR Ed EF Em Et Ex Ez Fa Fb Fn Fp Fr Fw Fy Gc GL GP gW Gz Ha Hb Hc Hf Hq Hr Hv Hw Hx Ib Ic Id
Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr
Ks Kx Ky Ld Lh Li Lj Lu Lv Lw Lx Lz Ma Mb Mc Me Mf Mg Mh Mi Mj Mk Ml Mm Mn Mp Mq Mr Ms Mt Mu Mv Mw Mx My Mz Na Nb
Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Oz Pa Pb Pc Pd Pe
Pf Pg Ph Pi Pj Pk Po Pz Qa Qb Qc Qd Qe Qg Qh Ql Qm Qn Qt Qu Qv Qw Qx Qy Qz Rb Rf Rg Rh Ri Rj Rm Sr Ss St Tn To Tr Tt Tv Tz Ua Ub
Uc Ud Ue Uf Ug Uh Ul Um Un Uo Up Ur Us Ut Uu Uv Vo Vp Vq Vs Vt Vv Wm Tj) Vo(AA aC Ad aE AF aG aH al AJ aK AL aM AN AO AP
aQ AR AS aU aV AW AX aY aZ BA BB BC bE bF BG bH bI bJ bL bM BN BO bP bQ bR bS bU bV bW bX bZ cA cB cC cD cE cF cG CH cI
cJ cK cL cM cN CO CP CQ cR CS CT CU CV CW CX cY cZ dA dB DC DD DE dF DG dH DI dJ DK DL dM dN Dp DR Ed EF Em Et Ex Ez
Fa Fb Fn Fp Fr Fw Fy Gc GL GP gW Gz Ha Hc Hf Hq Hv Hw Hx Ib Ic Id Ih Ii Ij Ik Il Im In Io Ip Iq Ir Is It Iu Iv Iz Jd Je Jf Jg Jh Ji Jj Jk Jl
Jm Jn Jo Jp Jq Jr Js Jt Ju Jy Kc Kd Ke Kf Kg Ki Kj Kk Kl Kn Ko Kp Kq Kr Ks Kx Ky Kz Ld Lh Li Lj Lu Lv Lw Lx Lz Ma Mb Mc Md Me Mf

Dr FR) Do(aA Ap aQ Ax Bo cT dF dG Di dR Dv Gp Tj) dV(aA aD aP cC cU dl dN gP) Dv(aA aQ Ax Cu dG Dr Gp) bR(dX gC) eP(bA Kk) bUgC} Nl{Jj(aA dX Em Fp Fr Hu Ii Ij Il Im Io Ip Ir It Iv Jg Jm Jn Jr Jt Li Lv Lz Ma Mc Mg Mh Mi Ml Mn Mp My Nb Nd Ne Ni Nk Nm Nn Nr Ns Nv Nx Ny Om On Oy Pb Pe Pg Pz Qa Qd Qe) Jp(Hw Ik In Iq Jk Jo Js Lv Mi Mt Nd Nf Nj Nk Ns Of Og Pa) Mm(Hw In Iq Jk Lv Mt Nd Nf Ni Nk Ns Oi Om Oz Pb) Pa(AA Fp Il In Jg Ji Lv Md Mi Mt Nk) Og(Aa Ik Ji Lv Md Mi Mt On) Md(Fp Ji Lv Mt Nx) Aa(Ma Nf Om Oz) Jg(Mv Nd Nf Om) On(Hq Jk Nf Om) Dr(aX Kk Ra) Mt(Lv Ns Om) Ji(Hw In Nf) LvMe HwNx} fR{Ko(aD Af cG cP Cw Dd Dg Di dJ Ez Ha Hb Li Mv Nd Nf Ng Nm Nt Om Or Pc Qd Ql Rj Ss To Tt Tv Ua Uc Uh Ut Uu) Me(Ez Kl Kp Kz Ld Lv Ph Pi Pj Pk Qt Qu Qv Rf Ss Tz Ua Uc Ue Uf Uk Um Uo Us Uv Vv) Qw(cG cl Dd dH Ef eP Hu Iq Jh Jp Md Mj Mx Nd Nq Oz Pa Pc Qy Rb Uk) Qx(Ar As Ax Mx Nd Nu Om Ow Qt Ra Rb Ss Vp) dO(aM bL bX cF cM cN Em) Rb(dJ Md Mj Nd Nf Ou) Oz(cE Kk Nd Nf Nj) Nd(cP It Og) Nf(iZ Nj Pc) dV(aK bC dR) gP(aD bP Db) gT(aQ cY) EmKk MxiZ HueP KfVo bRgN} aV{dO(AF Aj aO Ap aS bB bO bP bR bS cA cC cD cl cJ cK cM Co CQ Cu cW Cx cZ Db dC dD De dl Dk dN dV EX Fr Gc Gp) eX(aM bA bC bR cG cU cV Dd dH Di dJ dL dN) Gw(An Ba Bo cF cH cS dA dF dK dN Fw gP) Gc(aP aQ bQ cH Dc dE dL Me Rc Ue) Gt(aN aP bJ bV cF cR cY gP) gN(aD aN bC bJ cF dN Fw gP) Do(aJ cF cR cY dG dK gW) Dr(aP cO dR Fw In) dV(aM dF Di dN dR) Dv(bC cF Dg gP) Dq(dG gP gW) dX(aD aU Kk) eP(aC cO) gT(aM Fw) EmcN KoOm gCgP} eP{Me(Fa Gz Hb Jd Je Kf Kg Ki Kl Kp Qn Qw Qx Wm) Hu(cF Fa Ju Jy Ky Nj On Ow Ph Pi Pk Qd Vv) Qw(aA aX cF cO dB Fw Hf It Iv Vv) aX(Ko Kz Ld Mb Nc Ne Ng Oh Pj) Qy(aA aJ gP Je Ke Mf Nj Qx) Kk(bC Dc Ib Mr Or Ou Vp) eF(dJ dO Kz Rb Rc) Ko(Rc Tv Uf Uk) cF(Ji Jp Mf Oz) Ib(Nv Oh Ou) Hf(aM Js Og) Kz(dB Md Ue) Nb(bR Nj) Kf(Og Uu) Rf(bC Ju) Nx(li Uk) On(Kj Ur) Oz(cH Nu) DgKn FwJj MfdJ MwQa IrRa RcJg QxOu OgOi OyPb PcgP aJbR cGdO cHcN} Me{Dr(aX bU cH Dd dL Em Hf Hu Mn Mu Nb Nx Pa Qg Qz Sr Tr Ug Ut) Gc(aJ Dd Ow Ph Pj Qy Rb Ri Ss Tr Tt Tz Ug Un Uo Us Vq) Em(Ef Fa Lv Ou Oz Qv Ra Rg Rh Rj Sr St To Ud Wm) dX(Dp Fa Fp Kd Ke Kn Oa Rf) Gz(aJ cM dA Ha Jk Uk Ur) Ex(Kj Ri Ur) Nd(aX Jg) Js(Ko Sr) bN(Hf Ko) NjJp lkJj JfdE} eF{dV(Aa aJ aK Al Ao aP bA Bn bR cE Ch Co Cq CS Ct Dd dF dG DR Dv Ex Gp) Dq(aC aH Ao aU bA bE Bo Ch cM dl) Dv(aG Bc bU dA dC dD dL dO) Do(aD bL Ch cY Dc Dd gP) gN(aK bL bX cY Dd dJ dL) Gt(aD aM bC bU Dd) Gw(aM bL bR) dX(Om Qw) gT(aM Dd) aDeX} Nj{Jp(Hw Hx Ik In Iq Jg Jj Jo Js Lv Mf Mi Mm Mz Nd Nf Nk Nq Ns Nt Nu Nx Og Pa) On(Hq Hw Jj Jk Js Md Nf Of Om) Jg(Il Jk Md Nf Ni Of Om Pa) Mm(Jj Lv Md Mt Og Qe) Mt(Hw Lv Mi Og) Pa(Aa Jj Lv Nt) Ji(Md Nf Og) Aa(Nf Og) NtJj LvIl MdNx cNdX} dX{Qx(cY dB Dd dl gL Hf Mw Or Pj Qh Qw) Ko(Cp Fb Gl Hf Jk Kj Og Rc Uh Vt) Kk(cN Fw Iv Kf Og Or Ow Vo) cN(cY Kz Ld Oh Ou Ph Rf) Qw(aA Ih It Jn Ub) Hf(Ne Pb Pe Vp) Pb(aZ dJ Oy) Ha(Oa Rf) Ib(Jp Ky) Jj(Mg Us) Kz(dG dN) aZ(aD Qz) UedJ HuOa QyUr KfdN aJbR} Em{Vo(aZ Ba Hf Kp Lh Ng Nu Pj Pz Qa) Rb(Ch dM fl In Nf Ub Ue Uk Uu) Kk(Dd Hu Jj Jy Kd Qt Ss Ul) Qw(aZ Il Jf Jo) Ib(Ax Ld Ph) Nx(Iz Jo Jt) Gl(Ko Ou) Jp(Ke Kj) Uf(Ex Ko) aJ(Ha Kz) Ihli InJn QzJj QxcY LdUo aNcH aQdM} Nt{Og(Hq Hw Hx In Iq Iu Jg Jh Jk Jo Js Ma Mi Ml Mt Mx Nc Ne Nf Nh Nk Nq Ns Nx Of Oi Om Oy Pb Pc Qc) Jj(Hw Ik Md Mt Nd Ne Nf Nq Ns Om Oz) Nd(Iu Jp Mt Pa) Nf(Ji Jp Lv Pa) MdJp InPa} Dr{Rb(aP aX cQ dA dK Hu Ic Io) Nx(Fb Ii Ir Iz Li Mv Pj Ra) Hu(dL Jn Qw Qz Ue) Vo(Hf Ih Ld On Qw) Ra(aQ cF Fn Jy) Kk(Ir Kf Qt Rc) aX(Jy Ou Ph Pi) Gw(dJ dL) Qw(gP Jj) gP(Dk Jo) ExVo GzKj JfJk} Gw{aD(aG aN aU Ba Dc Fw) Dd(cF cV cY Dq Gt) aN(aK bN dL gP) bC(dD dO Fw gP) cN(aU cH cY dR) dL(aQ bL) aXdD} Ik{Jp(Jj Jo Js Mk Ng Ns Of Og Om Pa) Jj(Md Mm Nc Ne Og Qe) Og(Md Mi On Pa) Nf(Ji Mi) On(Of Om) MdPa} Gt{cF(aJ bC cH Di dJ Dl dR) aN(Ax Bo cB cH dJ Dl) Fw(bC cA Dd dl) cH(Aw gP) BoaK aMcB cYdK dGgP} Dq{Fw(aK bM bU CH cP dR) bC(aH aU bW cB cF Co dL) cF(aJ dR gP) cY(dK dM) BoaM aDaK aQdM} eX{Fw(aD Al aM aN bR cM) aK(aD cE cF dM) cB(aM dJ) cF(dG Dl) cN(bB cH) gP(Aw dG) AdDd DiaN cEcY cGdJ} dO{cN(aM Ar bB bF Cv) aD(aD bA cY dG) aX(Ar cG dl) aJ(cE dl) bC(dF dG) DlcF FwcA aNaP aOdG} On{Nd(Hq Js Lz Md Mz Ns Og) Oy(Fp Hw Mb Ne Nf Nh Nq) Md(Nf Nh) NfOm} Md{Nx(Fp Hw Lv Nf Og Oz) Jp(Ne Nh Nu) NdNv JiOz} gN{cN(aU cH cY) cF(aM dG) dL(bR gP) aKcG aOdG aQaX cYdM} gT{FwcA aDaK aJgP aMcF aUaX cEcP cNdR cYdM} Do{aK(bC cN) FwbC aJbU aUaX cHcN} Ji{Nf Po Qd Qe Qg Ql Qv Rg Rh Ri Rj To Tt Tv Ua Ub Uc Ud Uh Un Uv Vq Vt Wm) aN(aA aC Ad aE aF al Aj aL An AP Ar AS aU Aw aY Ba Bc bF Bg bH bI bJ bL bM Bn bO bQ bS bV bW bZ cA cB cC cD cE cI cJ cK cL CO Cp CQ cS Ct Cu Cv cW CX cZ dA DB DC De dF DG dH dK dM dN Dp Dq Dr Em Ez Fr GC gP Gt gW Hb Ij Il Jg Jm Jn Jv Jy Kd Ld Lj Mf Mh Mn Mv Nd Ng Nj Nk Nl Nu Nx Oe Ow Oy Pc Qu Uf Un) Aa(aE AF al Aj aK Al An Ao aP AS aY aZ Ba Bb bE bF BG bH bI bJ Bn Bo bP bQ bS bV bW bZ cA cB cE cG cl cJ CO Cp cQ Ct cU CW cX cZ dB DC Dd DK dM eF Fb Fn gT Gz Hc Hq Hv Hx Ij Io Ir Is Iu Iv Jd Je Jg Jl Jn Jq Jr Jv Kn Kp Kq Kr Kx Lh Lx Md Mg Mh Mn Mp Mq Ms My Na Nk Nn Ns Pg Qg Qy Rg Tv Ua Uf Ug Uk Up Tj) Or(aA aE aF aH al AL aP Ar aS aW bB bF Bg bH bI bM bO bQ bS bV bW bZ cA cC cD cE cG cJ cK cO cR CS CU cV CW CX cZ DB DC DD dF dG dH dK dM dN dR Em Fa Fr gW Gz Hc Hf Hr Hv Id Ik Jf Jg Jm Js Kp Ks Kz Lh Lj Lu Lx Ma Md Mh Mk Mq Mr Ms Mw Mz Na Nc Ni Nl Nn Nq Ns Nt Nu Nv Pf Qb Qu Qv Rf Rh Rj Sr Un Up) Jj(aA al aK aL aM AP aQ aU Aw Ax bB bG bH bW bX bZ cA cC cD cI cJ cK CO Cp cS cT CW cY cZ Dd dG dH Di dK dM Ed Em Ex gL gP Ha Hb Hr Ih Il Iq Iv Iz Jd Je Jh Jk Jm Jn Jt Jv Kj Kl Ko Kp Mb Md Mq Ms Mw Mz Na Nb Nc Ne Ng Nt Nu Nv Oa Ok On Pa Pg Ph Pj Qa Qb Qg Qm Qv Qy Rm St To Tv Ub Uc Ug Uk Up Vs Vv) bU(aA aC Ad aE aF aH al Al An aO aQ aS aU Ax aY aZ bA Bc bE bG bH bI bJ bL bM bN bP bQ bW bX bZ cA cB cD cE cG cJ cM CQ cS cT CU CX cZ DB DC dD De dF Dg dH Di Dl dN Dp DR DV eF eM Ex Fw gC gL gP gW Ii Il Im In Iz Jg Jk Jt Ju Jv Kc Ke Kk Lu Ma Mn Mq Mr Mu Nb Ng Oe Qm Qx Qy Ss Uh Ut Tj) dL(Ad Aj aK aL An aP Ar aU AW Ax bA bB Bc bE bI bJ bM bO bP bQ bV cB cC cG cI cJ cO CQ cR CS cT cU cV cW CX cY cZ DB dD De Di dK dM Dp DR Em Ex Fw gL Gw Hb Hc Hw Ik Im Je Jo Ko Kq Kr Kz Mg Mp Mq Nd Nf Nl No Ns Nt Nx Oa Oe Of Ow Oy Pa Pb Pi Qg Qh Qm Qn Rg Ss To Tz Ua Uu Vp Vt Tj) Ny(aE aF aG aH Aj aK aL Ao aR aW aY bA BB bC bF Bg bI bJ bL bM bN bQ cB cD cK Cp cQ cT CU cV Cw cX cY cZ dB dC Dg dR Ez Gc gP Ha Hq Hv Hx Ib Ij Ik Il Io Iq Iu Iv Iz Jh Jq Jr Jv Kf Kl Kn Lh Lu Lx Ma Mj Mk Mm Mp Mt Na Nd Ng Nh Nk Nl No Om Oy Oz Pc Pg Ph Pz Qc Qh Rh Ss Tz Uf Um Up Ur Uu Vs Tj) cN(aA aE aF aG AL AR aS aU Aw Ax aY aZ bA BC bE Bg bH bJ bM Bn bS bW bX bZ cA cB cK cL cQ cR Cs cT cU CX cZ dA dB DC Dd DE DG Di DV Ed eF eP Et Fr Fw gW Hf Ik Io Iq Iu Jd Ju Kc Kg Ky Ld Li Lj Md Mf Mm Ms Nd Ne Nf Nj Nl Nn Oa Ou Ow Pa Pb Pk Pz Qc Ql Qx Rg Ub Us) Og(aA aC Af aG aH An aO aP aR aW aY bA bB bC Bg bH bI bJ bM bN bS bW cA cJ cO Cq CT Db DG dK Et Fa Fp Fw gL Hc Hf Hq Hw Id Ih Il Ir Is Iv Jf Jm Jn Jp Jr Js Kp Lh Lx Mf Mg Mj Ml Mp Mq Ms Mx Na Nb Nc Nq Nv On Ow Pa Pb Pg Pk Qd Ql Rf Ri Rj Rm Sr St Ua Ub Uc Ug Us Uu Uv Vp Vv) Qw(aF al AL aM aP Ar aU Aw bA bC bE bH bI bJ Bn BO bS bX bZ cL cQ cR Cs cT cU cW Cx cZ dB dF Di dK dM dR eF Em Ex Gp gW Hc Hq Hx Id Io Ip It Jl Kc Kr Ld Lv Md Mh Mk Mm My Na Nc Ni Nj No Nq Ns Nt Nu Nw Oa Pa Pb Pe Pf Pk Qe Qg Qh Ql Qx Rf Ri Sr Tn Tr Tt Ug Ur Uv Vs) cM(aA aE aG aK aO aP Ar aU Ax aY aZ BA bC bE BG bI bJ bL Bn bO bP bS bV bW cA cB cC cD cE cI cL Co Cp cR Cu cV cW CX cY dA DB dC DD dF dH Di dK Dl dM dN Do DR Em eP Fb FR Fy Gc gL gP Hb Ib Ii Iz Jt Jy Ke Lu Mf Mn Mv Nb Ng Nk Nl Qm Qv Qx Ss Uf Un) dl(aA Ad aH aK Al An aO Ap AR aS Aw Ax aZ bB bF Bg bJ bL bM Bn Bo bQ bV bW bX bZ cA cB cC cE cJ cO CQ cS CT Cu CV cW cX cY dA DC Dd De dF Di DK Dl dO DR dX eF eM GC gN gP gW Hb Hv Hw Ib Ij Iz Jt Jy Ke Kf Kj Kk Mf Mv Nb Ng Nj Nm Of Pc Qv Ss Uf Tj) Ez(aE aG Al aO aQ aR AS aU aW bA Bb bE Bg bI bN bQ bV bZ cA cC cD cE cG cJ cK cL cR cU Cv cY cZ dA dD dI dN Dp Ef Fp gP Id Ji Jm Jp Js Jy Kd Ki Kn Lh Lx Mh Mk Mr Mv My Mz Na Nb Nk Nr Nw Oz Pa Pb Pe Pf Pi Qa Qb Qe Qu Sr Tn Tr Uf Ug Uk Up Uu) Um(aC Ad Af aG aK aL aO Ap aR aY Ba bG bH bI bJ bN Bo bQ Cq cT cX cZ Db Dg Dk Fr Fy Gc gL Gz Ha Hc Hq Hw Ii Ip Je Jg Jk Jr Jt Kf Kp Kx Li Lv Lw Lz Mc Md Mh Mi Mm Ms My Na Nc Nd Ne Nm Nt Of Oi Om Ow Pa Pc Pd Pg Pi Pk Qm Ri Tt Ua Ug Uh Up Ut Vq Vs Vt) cH(aH aJ Ap AR Ax Ba bF Bg Bo cB cC cL Cs Ct Cu Cw Dc Dd dG Di Dl eX Fp Fy gL Ha Hc Hv Hw Hx Id Iv Iz Jg Jk Jm Ju Ki Kk Ko Kp Kq Lj Lv Ma Md Mg Mn Mp Mq My Mz Nb Ne Nf Ng Ni Nq Nv Oa Oe Of Oh On Pa Pk Pz Qb Qh Qm Qv Qx Rf Rg Rm Ub Uc Ug Ur Vt) Ef(Ad aE Af aH al Aj aL An Ap Ar aS aU AW aY Ba bB bE bG bM BN bO bS bV bW bX bZ cD cE cJ cK cO Cp CQ Ct CU Cv Cw Cx cZ DB DC De Dg dH Di Dk Dl dM DO Dr eF Em eP Fr Gc Gp gW Hq Ib Ih Jn Ok Ow Oz Rf Rm Sr St Uu Vv) Me(aC aE aF al aK aL aP aQ AR aS aU Aw aY bB bI bJ bM Bn Bo bQ bS bW bZ cA cB cG cI cL cQ cR cS cT cU cV CX dA dB dD dF dH dM eF Ex Fw Hq Hv Hx In Io Ip It Jp Lx Md Mh Mj Mk Mm Mp Mq Mx Nf Ni Ns Nw Ow Pb Pe Pg Pi Pk Qd) aJ(aA Ad AF An aS aW aY BA bF Bg bH bI bJ bM Bo bS bW bZ cA cC cE cG cJ cK cL Co Cp CT Cu cY Dc Dd DE Dg Dk Dl dM dO Dr eF Ex Fr Fw Gc Gp Ha Hw Ii Ij Je Jh Jt Jy Kj Kz Ld Mr Nf Ng Nj Nq Nx Ow Oy Oz Qm Qv Ss) Qu(aG al aP aQ As aU Ax aY aZ Bb Bc bF bI bJ bL bO cA cC cG cL cS CV cW cX cY dA dB dE Fp Hv Ib Ih Is It Jp Kn Kp Ky Ld Lj Lu Lx Mh Mn Mr Mu Mz Na Ng Nj Nk Nl Nm Nv Nw Oh Ow Pd Qa Qb Qe Qv Qy Rf Sr To Uk Up Ut Vt) Ao(aA aC Ad aF aG Al aO aQ Ar AS Ax aZ Ba bG bJ bL BN Bo bP bV cA cB cO Cs cT cW dA dB DD dE dF Di Dk dM dO Dr eF Em Fp Gc Hf Id Jm Jn Jy Kp Ky Lh Lj Mg Mu Mv Nb Nu Nv Oa Ok Ou Pa Pb Ph Pi Qy Rm Uk Vv Tj) aV(Et Fn Hc Hq Hr Hw Hx Id Ip Iu Iv Jf Ji Jl Jm Jn Jo Jq Jr Js Kd Ki Kp Kq Kx Ky Lh Li Lv Lw Lx Lz Mc Mg Mi Ml Mp Mz Na Ni Nn No Nq Nr Ns Nt Nv Of Oh Pa Pd Pe Pg Ph Pj Po Pz Qc Qe Qg Qh Qn Rh Tn Tt Ud Un Us Vq) Ul(aA Al aZ Bc bE cE cR cS Cu Cv cW dD dG dK Dp Em Et Gp Gz Ha Hv Hx Ib Id Ih Im Ip Is Iz Ji Jl Jm Jn Jp Jq Kf Kp Kq Kr Ky Ma Mb Mj Mn Mv Mx Nd Nh Nl Nq Ok On Oy Pe Pg Ph Pj Qa Qb Qc Qe Rm St Uk Vv) Kc(aL An aQ aZ bA bG bI bJ bM BO bV bX cA cC cD cG cT cW cX dA dE dG Dr Gz Hr Id Ih It Je Jr Jy Ki Ko Kr Ky Mb Md Mh Mj My Na Nb Nf Nj Ns On Ou Pe Ph Qa Qe Qz Rg Sr St Tv Ub Us Uv Vv) bR(aC aL aO AR aU Aw aY bA bG bH bO bQ bW bX cC cD cG cK cR cS cT cU Cv cZ dC De dH dM Ed eF Fb fR gC gN Hw Im In Jg Jh Jn Jt Kg Kk Ks Ky Mr Mu Nb Nx Oe Ou Oy Oz Pb Qx Ss Ua) Kf(aA Af aH al aQ aS aY aZ BA BB Bc Bn bP cB cG cL cO cS Cv Dc dD dH DK Dl eF Gc Gp Gz Ip Iu Iz Jn Jo Jt Kj Kn Kr Kx Mb Mh Mu Nd Ng Nl No Nr Of Oi Ow Pg Ph Qg Tv Vv) Ib(aC aF aG aH aK aL aO aQ As aU aW bA Bc bF bG bH bL bM bP bS bW bX cA cD cG cK cR cS cT cU cV cZ dB dC dF dH dM dN Fb Fp Fw Hq It Lx Mf Mh Oe Ok Ow Pa Pb Qe St Uk Ur Wm) gP(Ad aG aK aP aQ Ar aY BA BC Bg bI bL bM BO bS bV cA cB cE cL cO cR Cv Cw cX cY dA Db Dc DD dK dM dN Dp dR dX eM fR GC gL Gp Iq Jh Kd Kk Kl Mf Mv Ng Nl Qx Uu) Uu(Ad Af Aj Al An Ar As aW Ax bC bE Bg bM cI cT Cx dA Di Dp Fb Hf Hv Ip Jh Jk Jl Jm Jp Ju Mf Mh Mq Mr Mw Nb Ne Nk Nl Nv Oa Oh Ok Oz Pa Pb Pi Qg Qy Rg Sr To Tr Uk Vp Vv) Om(aF aL Ap aR bG cA cD cJ Co Ct Dc dR Fy Hc Hv Ii Iq Ir Je Jf Js Kd Kg Ki Li Lw Lz Ma Mc Md Mi Mq Mr Ms Mv Mw Ni Nm Nq Qv Rf Ri Tn Tt Ua Uc Uk Un Uo Ur Ut Vp Vq Vs) Uf(Ar As Ax aZ Bc bN Bo bP bQ bV bZ cL Cv cX dA dD dE dF dK dM dN Dp Gp Hf Hq Hv Jv Kj Kp Ky Lh Lu Lx Mm Nl Oa Oy Oz Pa Pc Qa Qh Rm Tn To Tp Ut Vv) aG(aA Af aK aM aP aQ As bA Bn cL cO Cs cY dH DO Dp Dq dR EX Fp fR gL Ih Ij Jm Ke Kj Kl Kx Lj Ma Mf Mn Mu Nb Ne Nk Nv Oa Oh Oi Ok On Oy Qb Qv) Jy(Af aW Bb Bg bP Cp Cw dE Dp Hq Ii Ij Ik In Iz Jd Jh Ju Jv Ke Kg Kl Kn Ky Lu Ma Mf Mk Mn Mq Mw Nm Nq Oa Of Oz Pa Pc Qy Rg Ss Ua Uc Up) aM(aA Ad Aj aK An aO Ap aQ aY aZ BA bC Bg bJ BO cB cC cL Cs cU cY dA Db Dc dD dG DV Fb Fw Gc gW Ii Ij Jo Js Ke Mg Ng Oz Pc Vt) Kj(aC Ad Ar aU aW bA Bb bC bE bP cD cO cS dG Di dK Em Fa Fb Gp Hf Hq Io Jm Ld Lx Mh Mk Mr Nd Nl Nu Oa Oh Oi Ow Oz Pa Qb Qd Rm To) Fw(aF aK aQ aR aW bC bF Bo cA cD cE cG cl Co dA DC Dd dE dO Dq dR DV dX Gc gN GT GW In Jo Kd Mw Ng Pc Ss Uk Un Ut) eX(Af An Ap aQ aR AS Aw Ax Ba BB Bg BN bS cA cC cD cE cG cI CO Cu Cw cX cY dA De dF Dg Di dK Dl dN Dq dV eF Em gL) Kn(aA aQ cS Cv dD dG dK dM gL gW Hv Ic In Io Ip Iv Jh Ji Jl Jm Jp Jq Jr Kr Lx Mb Mm Mt Mv Ne Nj Nr Nu Oe Oi Pb Rm To Up Vv) Bb(Af aK aO Ar As Ax bF bH bL Bn Bo cB cC cI cL Cv Cx cY DD dE dG dK dN dO dR eF Ex Gp It Ko Lj Mu Nj Ou Ow Oz Pc) Kk(aH al aR Bg bO bP Ct dC DE Dk Dp Gc Hv Ik Iq Iu Jf Ji Jr Kx Lh Mn Mr Mu Mv Mw Nf Nk Nn Nv Nw Oa Ok Ow Oy Oz) Mf(Ba bF bP Cp Dc Dl Et Fr Fy Ii Il In Jd Jh Jk Jo Js Kg Kl Li Mg Mu Nq Oy Pd Pj Po Qc Qv Qx Qz Rh Uc Uk Vq) bL(aP cI cO Cs cW Dc Dd Ex Fa Gp

Hu Hw Hx Ik Iq Iv Jk Lj Md Me Nd Nf Ni Nk Nt Oz Qe) Ji(aA Fp Hq Il Iq Iu Jk Jo Me Mq Nd Ni Nk Ns Of Om Oz Pc) On(Hw Hx Ii Ij Il In Iq Js Nd Nk Ns Of) Qe(Hw In Iq Md Nd Nf Nk Ns Qb) Nt(In Iq Iu Md Me Nd Nk) Md(Fr Li Nb Nk Nm Pe) Nx(aA Fp In Iq Iu Ns) Me(fR Ik Nk) Hw(Fr Im Nv) eP(Hu Kc Qy) Fp(Il Ns) Gc(aX Hu) Qx(dX fR) EmKk FrNk InPe JkNv JoLh} Kc{eP(aC Af aI AJ An aQ Ar aU Aw aY bF bN
bO bZ cB cC cJ cM Cq Cs CT cU Cv cW Cx cZ dG Dk dX eM Fp FR Fw Gp Gz Hc Hf Id Ij Il In Iq Ir Is Iv Jg Jh Ji Jn Jr Jt Ki Ko Ks Ky Kz Lj
Lv Mh Mk Mu Nc Ni Nn No Nq Nr Nv Nx Of On Ou Pb Pd Pf Pg Ph Qb Qc Qd Qe Qu Rb Rm Sr St Tt Tv Ua Ug Uv Vs) Dr(aD An AR As aX
aY aZ bC bH bI bJ BN bP bV cD cE cH cN cQ cW Cx cY dB dM Fa gP Gz Ha Hq Hr Ic It Je Ky Lv Lw Lz Mb Mc Md Mh Mi Mj Mk Mn My
Na Nb Nc Ne No Nq Ns Nx Oa Pa Pb Pd Pg Qd Qm Qn Qx Qz Rg Rm Sr Tn Ub Uh Ut Vp Tj) Em(aD aH aP Ar As aZ bC bH bI bJ BN bO bP
bV bZ cA cE cM cP cR cX Db dE dG dM Ex Fa Fn Hq Hv Hx Jp Kr Ld Lj Lz Mh Ml Mp Ms My Mz Na Nc Nd Nj Nk Ns Nt Oz Pa Pb Pc Pf
Qa Qg Qw Qx Rb Rf Rg St Tv Uv) Gc(aA An aR AS Bc bE bM Bn bX cM Cs cV cX dA dF dN Fa Fn Gz Hf Hq Hw Je Jr Ki Kk Ko Kp Kz Lh
Lv Mb Md Mf Mh Mn Mw Mz Na Nj No Oh Or Ow Oz Pa Pc Pd Pg Ph Pk Po Qa Qb Qg Ri Sr Tz Uh Us Ut Vp Vt Tj) dX(Ad AJ Ao Aw bC
bH Bo bP bZ cJ Cu Dg Ef Fw Fy Gp gW Hc Ik Je Ji Jl Jo Jp Jr Jy Kn Ks Kz Li Ma Mg Mh Ml Mp Mt My Nd Nh Nk Nn No Nt Oz Pa Pf Qa Qn
Qt Sr Tn Ub Uc Ug Ut) eM(aL Ap aQ Aw bH Bn CT cW dC Ex Fa Hc In Iv Kd Kg Ks Ng Nv Of Oz Pa Pi Pz Qc Qt Qu Rb Tt Tv Ua Ut) dJ(bN
Db Me Rg Rj Rm) fR(Af Ko Qw Qx) bN(Ko Nf) MecM JfgP} Mt{Nd(FR Hq Hr Hu Hv Hx In Ip Iu Iv Jh Jl Jo Js Li Lj Lw Mc Mf Ml Mp Mq
Mu Mv Mz Nb Nc Ng Nj Nm Nn No Ns Nu Nv Nx Oe Of Om Oy Oz Pa Pc Pg Po Pz Qd Qe) Jj(Fp Hq Hr Hu Hx In Iq Ir It Iv Jg Ji Jm Jp Jr Js
Lj Lv Ma Mc Me Mf Mg Mh Ml Mm Mq Ms Mu Mv My Mz Nf Nh Ni Nk Nq Nu Nx Og Oi Pb Pf Pg Qe) Fp(Hq Hx Im In Iu Jh Jk Jo Jr Lj Lv
Lz Mb Mh Mi Ml Ne Nf Ni Nj Nn Nq Ns Nx Oe Of Og Oh Oi Om Oy Oz Pa Qd) Nj(Aa Il Im In Ip Iu Iv Jg Ji Jk Js Li Lj Lw Md Me Nf Ng Nk
Nm No Ns Nt Nx Of Oi Om On Oz Pa Pb Pc Qe) Hw(Ih Ii Ik Im Is Iv Jg Jr Lh Li Lj Lv Lw Md Mf Mi Mk Mm Mr Mv Nb Nm No Nq Nr Nt Og
Pa Pb Pc Pe Pz Qe) Om(AA Hu Ik Im Ip Js Jt Ko Li Lj Lu Lw Md Mg Mi Mp Nb Nc Ne Nh Nt Nx Og Oi Oz Pb Qe) Md(Ik In Iq Jg Ji Jk Js Lj
Lv Ma Mf Ms Nc Ne Nt Nu Oe Of Og Pa Pb Pc Pe Qd) Js(Ik Jp Jr Lj Mm Nh Nm Nq Ns Nt Qe) Lv(Hq In Nc Ne Nf Nq Nt Og Oy Oz) Nq(Jg Ji
Jp Mi Mm Nx Pa) Jp(Hx Ik Iq Nf Nh Ns) Jg(Jk Mv Of Og Oz) In(Iv Ji Nt Nx) Jk(Ji Ko Nt Pa) Og(Ne Ns Nu Oi) Oy(Iv Mk Pc) Nu(Hq Of) Nf(Ji
On) Iq(Ji Pa) EmVo NtOf MiOz IkPa KkeM OeOn} Ko{fR(Aa aG aH aV aX bN cE Dc De Dk Ed Ef Fb Fy gL Ic Ii Io Is IZ Je Jg Ji Jl Jp Jq Ju
Jv Kg Kr Ky Lh Lu Mb Md Mf Mk Mx Na No Nq Oa Ou Pa Pb Qa Qh Qn Qt Qy Qz Rg Ri Tn Tr Ub Us Vp Vs Vt) bN(aL bC bF Bg cE cM Co
Cp Di Ez Fy gP Ha Hc Hq Hx Ib Ii Ij In Iz Jf Jq Jt Ju Jv Kg Md Mj Mk Mn Mr Mu Mw Na Nv On Pa Pc Pg Po Ql Qm Qt Rc Ue Ut Vo Wm Tj)
Js(aZ bF Bg bI bL bZ Ch CP Dc Id Iq It Jf Jk Ma Md Nf Pa Qw Rf Ri Rj) Dc(Di Gl It Jf Jm Lj Md Me Nf Og Pa Qw Rb Rf Ri Rj Sr) Om(aK bI
bJ Di Dk dN Gl Ic Jf Jk Ma Me Nf Qw Rg Rj Vs) Jf(Bg Cp dE Di Dk gP Md Mr Mu Mv Nf Pg Qw Ri Ut) eM(aC aV bE Cp Ha Jh Kl Mu Og Tz
Ua Up Vt) gP(Jj Jk Jt Kj Ma Oe Of Qw Ri Ur Vo) eP(aV bL Gl Ii Jj Kl Kq Qu Tz) dX(cP Dp Md Mj Qy Tz Ua Ur) Qw(aI cE Dk Rg Ri Vs)
Pa(Dk Gl Jk Kj Vs) Ur(Bg Di Gl Mv) Em(Ii Jj Uu) Gc(Aa Uf Vo) Jk(Nx Rj Sr) Ri(Cp Dk Vs) aZ(Cp Ut Vs) Gl(Dd Dr) Vo(dN Gz) MdOg
MeaX JrpF VsdE aUaV} eM{Kk(Aa aD aE aI aJ An aP aR Ax aY bB Bc bF Bg bH bJ bL bO bS bZ cE cI cJ cK Co cR cT Cv cW Cx Db dC dD
dH dL dM Em Fn fR Gp Hc Hf Hq Hv Hw Ic Ij Im Ip Iq Ji Jk Jn Jo Ju Jv Ki Kj Kl Kr Kx Lh Lu Lw Mb Mc Mi Mn My Na Nd Nh No Nq Nt On
Pz Qc Qd Qe Ql Qm Qz Rb Ri Rj Sr Tn To Tr Tt Tv Tz Uc Ud Ur Us Vs) Me(aX Ed Iz Jf Jv Kl Ky Nj Pj Qh Qv Ra Rb Rc Ri Rm St Tr Tt Uf Ul
Um Un Up Us Uu Uv Vo Vp Vt Wm) Qw(aJ aZ bA bI cN cO dB fR Hv Jj Jy Ld Nn Nu Nv Nx Oi Qx Vv) aX(Gp Id Ik Jg Kr Kx Lh Mb Nh Nu
Pc Pi Ql Tv Ub Uk) Hu(cF Dp eF Ex Hc Id Jy Kp Qz Rb Uf Ur) Qx(aQ bE cV dA Gl Kz Mw Nu Po Uf) cL(cA cF Cs dI dJ Dq dV gN Qy)
Pb(cF Dg dJ gP Jp Oy) Ld(gP Ic Nb Og Ra) bE(Nj Oa Oz Ph Ue) eF(Ch dO Pc Rb Uf) aC(Jy Or Rf Vo) gP(aJ Kz Oz Ql) Ib(Di Jp Nn) Gl(Fa Oi)
Ih(Ha Ii) Nx(Mw Po) Og(Kf Oi) aN(Nf Oh) aV(dK dR) FbNv FpcM NbNj QtVv KzdB PccF aJbR cHcN} cL{eX(aD aF An aO aW aX aZ Bb
bF bG bH bI bM bN bP bW cD cI cJ cO cQ Ct Cv dC dE Di DK dO Fw Gp Gt gW) Dq(aE aH AJ Al Ao aR BB bE bF bH bO bQ bS bV cA cC
Ch cI cK cR Ct CV dN Ef fR) Gt(aC aD Af aH AJ As Bb bN bO bX cA Ch cK cS Ct CV CW Dd dG Dk dX EF Ex) dO(Aa aE aG aH Ao aR aW
bE bP bW cI CW dA dC dE Di Dl Do Ef gL GW Tj) gN(aD aH aN aP aZ bB bF Bg bS cC cI cS cT cV dC dG Di DV dX eF Tj) gT(aD aH Ax
bB bE bO bQ bS bV cA cC cK cS Cu cW Di dN Dv dX Gc Gp) Gw(aN Ap AX bM cD cF cI cN Cp Cu Cv dA DB Di gC Gp gW) Do(aD bB bL
bO cF cS Cu dB dL EF Ex Fw Gc) Dv(aJ aU bH bN bX cC dB dF Dl Ef gL Tj) eP(aM aV cA cC cF dL Hc Mv Og Oz Pc) dV(aL aQ Ar Ax Bo
cS Cu Ex GC) gC(aJ aK aM Ar bA cA dB dI Fw) EmRb KkdX} Jg{Nd(Fp Hq Hu Hv Hw Ih Il In Iq Ir Iu Iv Jh Ji Jj Jn Jo Jp Js Lj Lv Mb Mc Mf
Mg Mh Mi Ml Mm Mq Mu Mw Na Nc Ne Nh Ni Nj Nn Nt Nu Nv Nx Ny Oh Oi Om On Oy Oz Pb Pd Pe Pf Pg Pz Qa) Om(Dc Dk Fp Hu Ih Ik
Im Iq Ir Iu Ji Jk Jm Jp Js Lj Lv Ma Me Mf Ml Mu Nb Nf Ni Nq Ns Nt Nu Of Oh Oy Oz Pa Pb Pc Pe Pg Qa Qe) Of(Fp Iq Ji Jk Lj Lv Ma Md Mf
My Nc Nf Ni Nq Ns Nt Nu Nx Og Oz Pa Pc Qa Qe) Nf(Ih Ik Iv Ji Jk Jp Lj Lv Mf Mu My Ne Nh Nq Ns Nt Nu Og Oz Pa Pe Qe) Nj(Im Iq Iu Iv
Jj Jo Lv Me Mm Mv My Ns Nu Oz Pb Pc Qe) Md(Fp Ik Iq Ji Jk Lv Ml Nc Ng Nh Nq Nx Oi Pa) Ne(Hw Iq Iu Jp Lv Me My Ns Pa) Og(Fp Mu
Mw My Nh Nq Ns Nu Nx) Mv(Jk Jo Nc Nh Nq Oi Oz Pa) Jj(Ik Nc Nh Nq Nt Oz Pa) Jk(Iv Nc Nh Ns Oz Pa Qa) Nh(Hw Iq Ns Pa) Nq(Jp Mm
Pa) Oz(Fp Il Mm) Ik(Jp Pa) Iq(Nc Pa) EmVo FpJo OnOy} Nt{Og(Fr Hr Hu Hv Ih Ii Ij Il Im Io Ip Ir Is It Iv Ji Jl Jm Jn Jp Jq Jr Jt Lh Li Lj Lu Lw
Lz Mb Mc Me Mf Mg Mh Mj Mk Mm Mn Mp Mq Mr Ms Mu Mv Mw My Mz Na Nb Ng Ni Nm Nn No Nr Nu Nv Ny Oe Oh On Pd Pe Pf Pg
Po Pz Qa Qb Qd Qe) Jj(Fp Hq Hr Hu Hx Ij Im In Iq Ir It Iv Jh Ji Jk Jm Jo Jp Jr Js Lh Lj Lu Lv Lz Ma Mb Mc Me Mf Mh Ml Mm Mn Mq Ms
Mv Mx My Mz Na Nc Ng Nh Ni No Nr Nx Ny Oe Of Oi Oy Pb Pd Pe Pf Pg Po Pz Qa Qb Qc Qd Qe) Jp(Hw Hx Ii Ik In Iq Jk Jo Js Jt Lv Ne Ng
Nq Ns Of Om Oz Pa) Pa(Fp Ii Il Iq Iu Jk Jo Lv Md Ne Ng Nh Ns Of Oi Om Po) Nd(Il Im In Ji Jo Lv Md Mi Mm Nc Nf Ns Qa Qe) Md(Fp Ji Lv
Ne Nf Nj Nx On Oz Pb) Nf(Fp Lj Mi Nx On Oz Pb Pc Qe) Lv(Il Im Nc Ne Nj Oz) Nj(Il Iu Mi Mm) Oz(Fp Il Iu Ji) On(Of Om Oy) Pb(Il Jo)}
Nj{Jp(AA Fp Fr Hq Hr Hu Hv Ih Ii Ij Im Io Ip Ir Is It Iu Iv Jh Ji Jk Jl Jm Jn Jq Jr Jt Lh Li Lj Lu Lw Lz Ma Mb Mc Mg Mh Mj Mk Ml Mn Mp
Mq Mr Ms Mu Mv Mw Mx My Na Nb Nc Ne Ng Nh Nm Nn No Nr Nv Ny Oe Of Oh Oi Om On Oy Oz Pb Pc Pd Pe Pf Pg Po Pz Qa Qb Qc Qd
Qe) Mm(aA Fp Hq Hw Ik Im Ip Iq Iu Iv Ji Jo Jr Js Lj Ma Me Mf Mi Mn Mq Mu Mw Mz Nd Ne Nf Nh Ni Nk Ns Nu Nv Of Oh Om On Oy Oz
Pb Pg Qa) Jj(Aa Fr Ik Il Ji Jm Jr Jt Lh Ne Nr Nx Og Qe) Pa(aA Fp Il Ip Iq Ji Md Mi Nx Og On Qe) On(Hx Ii Ij Il Iu Ng Nq Og Oz) Ji(Hw Il Iu
Jo Me Om Oz) Qe(Il Js Lv Md Mi Og) Aa(Jo Jr Om Oz) Nx(Il Iu Lv Og) Mi(Im Nf Og) dX(gL Qx) fR(cP Ni) DrMv FrNf GcMe MdNb IlLh
JtOg} eP{Qy(aX bE cH cI cP dI EF Fa Ha Ib Id Jd Jn Ju Kf Ki Nf Or Ou Qz Rf To Uk) Hu(Ar cS dL Dp eF Fw Fy Ha Ib Ir Jp Kg Ki Kn Nh Nv
Og Oz Rm Tv Ul Um) Qw(bE cH Dg Dp Ih Jj Ky Md Mn Nf Oi On Qd Uk) Me(Ed Ez Fp Hc Ic Id Jf Jv Kr Kz Oa Pb Rf) Ib(Ap Iz Jm Jt Kp Nm
Nx Ph Pz Ql Rf Tn Us) Hf(cN dI Dp Gz Jk Jr Li Mb Om Oz Pb Vp) Kk(aM Bc cC cN cP Ed Fw Mj Mq Mw Ue Uo) Kz(aC Ad bE bU cC cF cG
cH cN dG Nb Rf) aV(aD bA bR cF cG dA dE gP) Jj(gP Hc Ik Nu On Qm) Og(Di Id Ld Pb Ug) eF(aD aM Om Ut Wm) Ha(Nu Oh Qd Rf) aX(Ji
Oi Rm Ug) Nu(Af Bn cF) Rb(aC cN dE) aZ(aD Qz Uk) Ih(cS Oz) Hc(Nf Oy) Jy(bC gL) Kf(cF Rc) Kn(Dl St) Pb(cH Dd) dV(cG dG) DgVo
DqFw WmaC EdQx GlOz NbIt IiNv LjcF RfdI NxUt OuaL UrbE aDaG aMcB bAcC fRgP} fR{Qw(aH aI Al aN aR bN cE cQ CW Db Dc Gl
Ha Hr Ih Ip Iu Jf Jj Kd Ks Ma Mb Ml Mq Mr My Nu Oc Om Or Ou Ph Qz Ra Rc Rf Rg To Uf Uo Vo Tj) Me(Ex Ik Iq Ml Pb Qg Qz Ra Rb Rh
Rm Sr St Tn Tr Tt Ud Ug Uh Ul Un Uu Vs Vt Wm Tj) Qx(aE aI bO bQ Cq Cu dH dl Fp Jp Lj Lv Ma Md Mj Mq Mu Nx Oh Pa Pc Rf Up Vo
Vs) Nf(cE cP gL gP Hq Jr Kd Lv Pb Ra Up) Oz(Ar cP Fp Gl gP Hu Iq Jp Lv On Qe) Nd(aV cQ cY Kk Mv Nu Nx On Ou Pc) Kk(Hu Jp Kx Mb
Mj Mv Om Pc Vo) gP(aF aH Aw Bc cE dM gC gW Pc) Rb(aY Iq Jj Ks Mv Na Up Ut) dO(bA Bn dl dV gT) Lv(iZ Pc) aK(eX gT) aV(Dr Gc)

Figure 11 Continued dJ(dV gN) dR(eX Gw) DbiZ DqbC GlOn HcQt RaPh QydX PccE cYdV} aV{Gw(Af AL aM aO aY bA Bb bI bR bS bZ cB cC cG Ch cK Cq Cs
cU cV cW dE Dg dH dI dJ Dq dR Ex GC) dO(aE aG aH al aK aL Ao AR As AW aZ Bb bF bG bH bL bM bN Bo cB Cv Cw Do Dq Dr dX Em
gC Gl Tj) Gc(Aa aD aK aN Bb bZ cF cH cK Cs dF Do Dq dR EF Fp In Og Or Qw Qz To Vo) eX(aA Ad aF aO Ba bF bL bU cB cD cK dI Dl)
Dq(aC aD aM aQ aU bJ Bo bV dF dH dN) gN(aC aU bF bQ bV cK dF dX gW) Gt(aC bQ cH Dd DG Di gW) Dv(aC aU bV cK dA dF) gC(aC
aD aQ cH dE dR) gT(bV cF dA dN dR gW) Dr(Cs eF Ic Qw Ra) Em(aX bE dN Ky) dX(aN bE cS dN) Do(aU Dg gP) dV(cF Dg)} dX{Qx(aK
aM bC bR cG Dp Em It Jd Kr Ld Ma Mr Mx Nc Ng Oe Oi On Qv Rb Ug) Kk(bC bI cP Dp Ed gP Ih Kn Md Om Po Tv Ue Ul Uo Ur Wm)
Me(Ez Fy Gz Hc Hf Id Jf Kf Kg Ki Kq Ks Qm Qw Uk) Ib(Ax Ex Fy Id Ng Nv On Pj Sr Ue) Hf(Al aM aN cA Dp Ii Jk Na Nh Rc Rj) Jj(Ik
Kg Ks Ne Nu Pb Pj Ql Qy) Qw(aX Ba dG Fw gL Hv Nn To) Kz(bE bU cJ cP dB dJ eF) Qy(cF eF Ex Ky Ld Nx) Hu(Fy Ha Ky Nd Pb) cN(aK
cH dO Kp Rb) Kf(Ha Ii Om Uu) Pb(aN cP dL gP) Rb(aC aX Uk) Nx(Hr Nd Uk) eF(aD dO Jy) Nf(aN Ql) Rc(Ap Ne) Qd(Ha Jk) Oz(Ih Nu)
Pc(aZ gP) aJ(bU bW) WmbE FpcF liNv JnaN KjOn Or

Figure 11 Continued

Ky(Dp In Lu Mb Mg) Om(My Rj Ud Uv Vt) aK(aP Ct cY dK dN) dO(bJ Bn bQ bX cO) Cu(Ar cW Fa Rf) Di(Bo In Lu Nd) Em(aO aZ cB Nu) Gp(Bc Qm Uc Un) Jk(dN Ih It St) Ko(Cp Kg Li Mg) Pa(Bg Dp Jh Qy) Bn(aP bV dF) Co(cW Ih St) Dc(bN dR Hf) Uh(Ih Lx Mz) aO(dF dM Nk) cY(bE dK dN) Ax(Ct Li) Bo(Dv gN) Dp(aZ Mb) Fp(Oz Pj) Lu(aC Nd) Mw(My Ok) Jh(bJ dN) Sr(Mg Un) aR(aP cO) dA(bQ gC) gT(Aw bN) CpOw CtcT DgIt DkeF WmaU FaJs GccR NqdN NtNu MbPh MrJf NcNl NiNk UcHv HwaZ IkOz lqbF LjUn RfPj VvPf aWcB cCdX cWdR} Et{Dk(aA aJ bA Bc bL bN Bo Ch Ct Cu Dc Dd Dg Di Ef Ez Fb Ha Hf Hr Hw Ib Id Ih Ii Ij Ik In Iv iZ Jd Je Jk Jl Jp Ju Jv Jy Ke Ki Kl Ld Lu Lv Lx Mf Mm Mn Mq Mr Mt Mu Mv Mx My Na Ne Nh Nm Nn Nr Ns Nx Ny Oa Oh On Ow Pd Pe Pf Ph Po Qh Ql Qm Qn Qt Qv Qz Rg Ss Tz Ud Uh Up) Vo(Af Al An Bb Bc bF Bo cH Cp Cq Cs Ct Cv Cx De Dg dN Ex Fa GP Gz Hc Hf Ih Ik In Iv Iz Jd Je Jq Jr Js Kf Ki Kl Kn Kx Ky Ld Lj Lz Mb Mf Mg Mn Mp Mw My Ni Nj Nk Nq Nr Ns Ny Of Oh Oy Pc Pe Ph Pi Pj Pk Pz Qt Qw Qx Ra Rf Rh Rm Ss Ul Uo Uu) Ly(Aa aC aD aE aK aM aP aS aY bC bE bG bI bM bO bS bU cA cD cF cJ cN cQ cR cS cT cU cV cW cX cY cZ dC dD dF dG dK Ed Fw Gp Hc Ic Jd Ju Jv Jy Ki Kl Kn Oa Ph Pj Qg Qm Qn Qu Qv Qy Qz Ra Rc Rg To Ua Ud Ug Ul Um Uu Vv) Jo(Ad Af Aj Al An Ao Ap As Aw BA Bb Bc Bn Bo cH Co Cp Cq Cs Ct Cu Cv Cx Db Dd dE Dg Di Dl Dp Ef Ez Fa Fn Fw Fy GP Gz Hb Il Jd Jc Ju Jv Jy Ke Kj Kl Kx Ky Pi Pj Pk Qh Qm Qn Ra Rc Ss St Ub Up Uu Uv Vq Vt Vv) Mb(Bg Cw Dc Fp Fr Hq Hr Hu Hx Im In Io Iq Ir Is It Iv Jf Jh Ji Jk Jl Jm Jn Jp Jq Lh Lu Lw Lz Ma Me Mf Mh Mi Mj Mk Mn Mp Mr Ms Mu Mw Mx My Mz Na Nb Ni Nn No Nr Nu Ny Oe Oh Oy Pd Pe Pf Po Pz Qa Qb Qc Qd Qe Ut) Om(Af AJ aK Ar aV Ax Ba Bc bF bL Bn Bo bZ cE cG Cp Cs cZ De Ef Ez Fa Fb Fw Fy Gp Hb Hc Hf Ib Id Iz Jd Je Jy Kf Ki Kq Kx Ky Ld Ow Pi Pj Pk Qg Qh Ql Qm Qv Qw Ra Rc Rh Rm Sr Tr Tt Tz Ub Uc Ud Ue Un Uo Up Uv) Gl(aA Af aJ Ao Bb bJ bV Ch cM cP Ct Db Di Hc Hq Hr Hw Ii Ij In It Jn Jp Ju Jv Kc Kd Kj Kn Kz Lu Lv Lw Ma Mc Mk Mm Mp Mq Mr Mt Nw Oh Or Ou Pd Pf Ph Po Qt Qw Rb Rj Uc Ug Up Us Ut Vp Tj) Iu(Fr Hq Hr Hu Hv Hx Ii Ij Im In Io Ir Is It Iv Jh Ji Jk Jl Jn Jp Jq Js Lj Lu Lw Lz Mc Mg Mi Mk Mn Mp Mr Mu Mv Mw Mx My Mz Na Nb Ng Ni Nm No Nw Ny Oe On Oy Pd Pf Po Pz Qa Qb Qc Qd Qe) Nt(Hu Hv Hx Ih Io Ip Ir It Iv Jg Jh Jl Jm Jq Lh Lj Lu Lw Lz Ma Mc Me Mf Mh Mi Mj Mk Ml Mn Mp Ms Mu Mv Mw My Mz Nb Ni Nn No Nr Nu Nv Nx Ny Oh Ok On Oy Pf Pg Po Pz Qa Qb Qc Qd Qe Ut) Nf(aD An aO Ap As Aw aX Ba Bc bF bL Bn bV bZ cB cG Cq Cs Cu Cv Cw Cx DE dM Ed Ez GP Hb Hc Ib Ju Jv Kl Ky Kz Ld Ow Ql Qt Qy Ra Rc Sr Ss Tn To Uf Uk Ul Un Us Vp Vu Tj) Lv(Bg Dc Fr Hu Hv Hx Il Io Iq Ir Is It Iv Jh Ji Jl Jm Jn Lh Li Lu Lw Lz Me Mh Mi Mj Mk Mr Ms Mu Mw Mz Na Nb Ni Nn Nr Nu Nv Ny Oh Ok On Pd Pe Pf Pg Po Pz Qa Qc Qd Qe Ut) Og(aA Dc Fr Hr Hu Hv Ij In Io Is Ji Jk Jl Jn Jp Jq Lh Li Lu Lw Lz Mg Mh Mi Mj Mk Mp Mq Ms Mu Mw Mx My Mz Na Nb Ng Nn No Nr Nv Ny Oe Oh Pd Pe Pf Po Pz Qb Qd Ut) Jf(Af Aj Co Cu Cw Dd Di Dl Fb gP Hw Hx Ib In Iq Jj Jq Kd Ki Kk Kl Kn Kq Kr Ks Kz Ld Ma Na Nj Ny Or Oy Pd Ph Ql Qt Qw Qy Rc Rf Rg Rh Rm Ss Tn Uo Ur Vp Tj) Pb(bF bJ bL cE De Dl Ha Hr Hw Ih Ij Im In Iq Ir It Jq Ke Kj Lz Ma Mc Mf Mg Mj Ml Mm Mn Mq Mu Mx My Ni Nk Nm Nu Nw Nx Oe Oy Pc Pd Pe Po Qa Qc Qe Qt Tn Vp) Ik(Fr Hu Hx Io Ip Ir Is It Iv Jh Ji Jl Jm Jn Jq Lh Li Lw Ma Mh Mj Ml Mp Mr Mu Mv Mw Nb Ni Nn No Nr Nu Nv Ny Oh On Pe Pf Pg Po Pz Qb Qc Qd) Fp(Hq Hr Hx Ih Ij Im In Iq Ir It Jk Jl Jp Lz Mc Me Mf Mg Mh Mi Mj Ml Mn Mv Mx My Mz Na Ng Ni Nk Nn No Nu Oe Oh Oy Pd Pf Po Qc Qd Qe) Js(aI Ar bJ Co Fr Hq Hr Hu Hx Ii In Iv Ji Jm Jn Lz Ma Mc Mg Mn Mq Mv Mw My Mz Ng Ni Nm Nr Oe Ok On Oy Pd Pf Pz Qb Qc Qt Ri Rj Sr Tj) Pc(bL Co Dl gP Hq Hr Hw Ih Ij Im In Iq Ir Jk Ke Kg Lz Ma Mc Mf Mg Mj Ml Mm Mq Mv Mx Ng Ni Nk Ns Nu Nw Oe Oh Ok Oy Pd Po Qe Ri Vu) Ns(Fr Hq Hr Hv Ih Ii Im In Ir It Jh Ji Jm Jn Jp Lu Lz Ma Mc Me Mg Mi Ml Mm Mq Mu Mv Mw Ni Oe Oh Oi Ok On Oy Pd Pf Pz Qa Qc) Nd(aG aH AJ AL Ap As aV Ba BB bC bF bH bX bZ cC cE cG cH Cp cT Cu cZ Dd dE Dg dJ Ha Il Kg Ou Qw Ra Rb Ri Ur Tj) Nw(Dc Hr Im Ir It Iv Jg Jk Jl Jq Lx Lz Ma Mc Me Mf Mg Mh Mj Mn Mp Mx Mz Na Ng Ni Nk No Nu Nx Oi Pd Pe Po Qa Qc Qe) Ut(aA Af aJ Ao aZ bN Bo Dd Hc Hf Hx In Io Iq Jr Ko Kp Ks Kz Lu Ma Md Mj Nm Nr Or Ow Ph Qe Ra Rc Rj Ue Uk Ul) Nq(Dc Hq Hu Hv Hx Ij Io Ip Jq Kk Lh Lu Lw Lz Ma Mg Mh Mj Mk Mn Mp Ms Mv My Na Ng Nn Nv Ny Oy Pd Po Qc Qd) Dc(Ao Ax Bg bN CH Cs Hr Hx Id Iv iZ Jm Jr Kj Kz Lx Ma Mf Mj Mk Mt Nl Nr Nx Or Qa Ql Qx Ue) Jg(Hq Hr Hx Ih Im In Ir Jp Ma Mc Mg Mk Ml Mm Mn Mq Mu Mx Ni Nk Nm Nu Nv Nx Oe Oy Pd Pe Po) Kk(aO bL cE Ch Cp Cu Dc gP Ha Ib Kc Kg Kq Ma Me Mq Mr Mw Ny Oe Oy Pe Un Vp Tj) Mj(Ar Bg bN Ch Hf Id Ih Iv Ju Jv Kg Kp Ks Mr Oa Or Ph Pj Rb Sr Uk Ul Uu Uv) Iv(Ii Ij Im Jk Jq Jr Lj Lx Mc Mg Mm Mq Ms Mv Ng Nk Nm Nu Oi Ok Pe Qe) Ur(Co Cp Cw Fr gP Hq Jr Jt Me Mk Mr Mu Nv Oe Pa Po Qt Rg Rj Un Vu Tj) Jt(Ao Bc bJ Co Ib Id Io Ip Jq Kc Kd Kp Mm Ms Nv Or Rb Vu Wm Tj) Lj(Hx Ii Ij In Jk Lz Me Mf Mm Mn Mq Mx Na Ng Ni Nm No Oi Pe Po) Bg(bA bN Hc Hx Ii Iq Jl Jr Kc Kj Ko Ks Md Me Nj Qw Rb Ri Rj) Iq(Im Jh Ji Jm Jn Jp Me Mf Mg Mm Mq Nm Oh Oi Ok Pf Pg Qb) Jk(aJ bN bV Dl Hc Ih iZ Kj Kp Nk Qa Qe Qn Qx Rc Ri Rj Ul) Jr(aA Ip Is It Jh Ji Jl Jn Kc Kd Lh Li Lw Mk Mr Mw Nr Ou) Hw(Im Ir Jm Jn Mf Mm Mq Nu Nx Oh Ok On Pg Qa Qc Ri) Ii(bJ Ch Ir Is Ji Jm Mf Mi Ml Mr Nk Nu Oi On Qa Qe) Oe(aJ bA Bb bF cE cH Cs Cw Ih Kz Nx Qt Rh Rm Uo Tj) Ou(Ch Cu Dl Hx Ij Kg Kj Me Mu Nv Pe Ql Qu Rb Tn Tj) Kc(Ao bL Cp Cw Hx Ij Jl Kg Md Nv Pg Po Qt Ri Vu) Pa(aA bN Ch Co Cu Cw Dl Ha Il Iz Kc Qt Ri Vp Tj) Md(Ao bN Ch Ip Kd Ko Lh Mp Qx Rb Ri Rj Wm) Nx(Hx Ih Ij Im In Mg Ml Mm Nk Nm Oi Pe Pg) Lx(aA Hv Is Ji Jm Jn Li Lu Lw Mr Nr Pe) Jl(aJ Ao bA Ch Ih Kj Ko Pj Qy Rb Rc Ri) Pg(bA bN Ch Kd Kj Ko Mm Nk Nm Qx Rb) Jj(aI Ao Ch Co Cw Em Il Ke Qt Rg) Nm(Ih Im Mf Ml Mq Mv Nk Ok Pe) bN(aH aI Ao cE Ch Kj Ko Nj Oz) Po(Ar Ih iZ Kd Ko Oa Ri Ue) Mv(aJ bA iZ Kj Kp Qx Rb Rj) Nk(In Mf Mm Mq Mx Oi Pd Pe) Ao(Hc Kd Ko Of Sr Ul Tj) Ri(Hq Ij Kj Ks Mn Qw Uu) Ch(Hx Kd Of Oy Qx Qy) Mf(Ih Im Jp Mg Mm Oi) Qe(Hr Ij In Mq Ng Qc) Vu(Io iZ Oy Oz Qx Qy) Ko(Hx Kg Kj Ma Mk) iZ(fR gP Pe pF Vp) Mu(aJ Kd Qx Qy) Of(aA Ip Qy Rg) Mk(Qy Rb Wm) Hq(Mi Ok On) Kd(Ij Ke Kg) Oz(bL Co Dl) Mt(aA Il) Hx(Kj Wm) Ih(Oi Qc) Qa(In Qc) Qw(fR Mr) Kg(Me Oy) Rj(Ct Kj) Pe(Mq Pd) pF(aI Io) DrRa MwMy IjOk IzOy RbKs bAcE} Nw{Nh(Fr Hu Hv Ii Im Io Ip Ir Is Iu Jh Ji Jl Jm Jn Jp Lh Li Lj Lu Ma Mb Mc Me Mf Mg Mh Mi Mj Ml Mn Mp Mr Ms Mu Mv Mz Na Nb Ng Ni Nm Nn No Nq Nr Nu Nv Nx Ny Oe Oh Oi Ok On Pb Pc Pd Pe Pf Pz Qc Qe) Lz(Fr Hr Hu Hv Im In Io Ir Is Ji Jj Jl Jm Jp Jq Jr Jt Lh Li Lj Lu Lv Ma Mb Mc Me Mf Mg Mh Mi Mk Ml Mn Mp Mq Mu Mv Mx My Mz Na Ni Nm No Nq Nr Nv Nx Oe Og Oh On Oy Pb Pd Pe Po Pz Qa Qb) Nk(Fr Hu Hv Ij Im Io Ip Ir Is Iv Jg Jh Ji Jl Jm Jn Jp Jq Lh Li Lj Lv Lx Mb Me Mf Mg Mi Mk Ml Mn Mp Mr Mu Mv Mz Nm Nn Nq Nr Nu Nv Nx Oe Og Oh Oi Ok On Oz Pb Pd Pe Pf Pg Pz Qa Qc Qe) Hq(aA Fr Hr Hu Hv Ih Ii Ij Im In Io Ip Is Jh Ji Jj Jl Jm Jn Jp Jq Jr Jt Lh Li Lj Lu Lw Mf Mh Mj Ml Mn Mp Ms Mu Mv Mx My Mz Nb Ng Nm Nv Nx Ny Oe Og Oh Oi Oy Pc Po Pz Qb Qc) Pa(Dc Ha Hr Hu Hv Ih Ij Im Io Ir It Jh Ji Jk Jl Jn Jp Lh Li Lj Lx Ma Me Mf Mh Mi Mk Ml Mn Mp Mr Ms Mu Mx Mz Nb Ng Nm Nn No Nu Nx Oe Og Oh Pb Pd Pg Po Pz Qa Qb Qc Qe Vp) Hx(aA Bg Dc Di Dk Fr Gl Hu Hv Ii Ij Im Io Ip Is iZ Jh Ji Jl Jm Jn Jt Lh Li Lj Lu Lw Ma Me Mj Mk Mm Mn Mp Ms Mu Mw Mx Mz Nb Ng Nm No Nq Nr Oe On Pc Pd Pz Qb Qc Rj Wm) Oy(Bg Fr Ha Hr Hu Hv Im In Ir Is Ji Jl Jm Jp Jq Jr Lh Li Lj Lu Lv Lx Ma Mc Me Mf Mh Mj Ml Mq Ms My Na Ni No Nq Nr Nu Nx Ny Of Og Oh Pb Pc Pe Pf Pg Po Pz Qa Qb Qd) Oz(Fr Hr Hu Hv Im Io Ip Ir Iu Jh Ji Jk Jl Jm Jn Jp Jr Lh Li Lu Lv Mb Me Mf Mi Mn Mp Ms Mu Mw Mx Mz Na Nb Ng Nm Nn No Nr Nu Oe Oh Oi Ok Pb Pc Pd Pf Pg Pz Qa Qc) Fp(Fr Hr Hu Hv Ih Ii Io Ip Ir Is Iu Jh Ji Jj Jm Jn Jp Jq Lh Li Lu Lw Lx Ma Me Mj Mk Mn Mp Mr Ms Mu Mx Mz Nb Nq Nr Nu Nv Oe Oi On Pb Pc Pd Pe Po Pz Qa Qb Qc) Jo(Fr Hr Hu Hv Ii Ij Im Io Ip Ir Jh Jj Jk Jl Jn Jp Jq Jt Lh Li Lj Lu Lw Ma Me Mh Mj Mk Ml Mm Mn Mp Mu Mv Mx My Mz Nb Ng Nm Nn Nv Ny Oe Og Oh Pg Po Pz Qc) Iv(Hr Hv Ii Im Io Jh Jj Jk Jm Jn Jp Lh Li Lj Lv Lx Ma Mc Mf Mg Mh Mi Mk Ml Mn Mp Mv My Mz Nb Ni Nm No Nu Nv Ny Oe Og Oh On Pb Pc Pd Pe Pf Pz Qa Qb Qe) Ns(Fr Hu Ih Ii Ij Im Io Ip Is Jh Ji Jk Jl Jn Lh Li Lu Lw Me Mh Mj Mk Mn Mq Mr Mu Mv Mx My Mz Na Nb Ng Nm No Nv Nx Ny Oe Oh On Pb Pd Pf Pg Po Pz Qc) It(Dk Hu Hv Ii Ij Il Im Ir Jj Jm Jn Jp Jq Lh Li Lj Lx Ma Mb Mc Mg Mh Mi Mj Ml Mq Mx My Na Ng Ni No Nq Ny Oe Og Oh On Pe Pf Pg Po Pz Qa Qb Qe Ut Vp) Oi(Hr Hu Hv Ii Ij Im Io Jg Ji Jj Jl Jm Jn

Ji Jk Jn Jq Jr Lu Lw Ma Mc Me Mf Mg Mh Mi Mp Mu Mv Mx Mz Na Nb Nk Nm No Oe On Oz Pb Pd Pf Pz Qb Qc Qd) Og(Fr Hu Hv Ih Im Io Ip Ir Iu Jg Ji Jn Lh Li Lu Lw Lz Me Mg Mh Mi Mk Ml Mq Mr Ms Mu Mw My Mz Nk Nn Nv Ny Oe On Pb Pd Pf Pg Pz Qa Qe) Ng(Hu Hv Im Io Ip Ir It Jk Jm Jn Jq Jr Lw Ma Mf Mh Ml Mn Mp Mu Mw Mx Mz Nb Nk Nm No Nu Nx Ny Oh Oi On Oy Oz Pb Pc Pz Qb Qc Qd) Iv(Hr Ik Il Im Iq Ir Is Jk Jl Jm Jq Lv Lx Ma Mb Mc Mg Mh Ml Mn Mp Mq Mt Mx My Mz Nb Nc Ni Nm Ny Oe Oh Oi Oz Pc Pe Qc Qd) Ns(Hr Ij Im Ir Iu Jk Jm Jq Jr Lv Lz Ma Mb Mc Mg Mh Mi Mj Ml Mn Mz Na Ni Nk Nm No Nt Oe Oh Pb Pd Pe Pf Pg Qb Qc Qd Qe) Hx(aA Dk Fr Io Ip Is Iu Ji Jl Jn Jq Lh Li Lu Lv Lw Mi Mk Mp Mr Mu Mv Mw Nb Nk No Nt Nu Nv On Oy Pb Pc Pz Qb) Mg(Hr Hw Ij It Jm Lv Lx Lz Ma Mb Mc Mh Mj Ml Mn Mp Mx Mz Na Ni No Nt Oh Oz Pc Pe Pf Pg Qb Qc Qd) Hr(Ij It Jk Jq Lv Lz Ma Mc Me Mh Mj Ml Mm Mn Mp Mv Mx Mz Na Nk No Nt Oh Pb Pc Pd Pe Pg Qc Qd) Oy(Fr Io Ip Ir Is Jh Jm Jn Jq Lh Lw Lz Me Mf Mi Mj Mk Ml Mp Mq Mr Mz Nb Nk Nt Ny Oe Oh Qb) Pa(Dk Fp Fr Io Ip Ir Iu Jg Jm Jn Jp Mc Mi Ml Mn Mq Ms Mw Nb Nk Nn No Ny Oe Pc Pd Pe Pg Pz) Mb(Hu Im Ir Iu Jk Jq Mc Me Mj Mn Mq Mx My Na Nb Ni Nm No Nt Ny Oe Oh Pe Pf Pg Qb Qc Qd) Mt(Im Ir Jm Jn Li Lj Mc Me Mk Ml Mp Ms Mw My Mz Nb Nk Nr Nt Nu Oh Pb Pc Pe Pf Qa Qb Qe) Of(Em Fr Hu Im Io Ip Is Iu Jh Jl Jn Lh Li Lw Me Mi Mk Mr Ms Mu Mw Nm Nn Oe On Pc Pd Rj) Lx(Fr Hv Im Jg Jh Ji Jm Jp Jq Lu Lw Mf Mi Mk Ml Mr Ms Mu Mw Nu Nx On Pz Qa Qb Qe) Jk(Fp Ih Im Ir Jg Jm Lv Ma Mc Mf Mm Mn Mq Na Ni Nk No Nu Nx Oi Pd Pe Pf Pg Qa Qc) Lv(Ij Im It Iu Jp Jr Lh Lz Ma Mc Mh Mj Ml Mn Mx Nk Nm Nt Oe Oh Oi Qb Qc Qd) Ik(Fp Ir Is Ji Jr Lj Mj Mr Ms Mx Na Nb Nn No Ny Oh On Pd Pg Qd Qe) Oz(eP Fp Iu Jg Ji Jq Lz Mc Mf Mh Mi Mj Mp Na Nc Ni No Nr Nu Oe Oh) Ma(Ij Il Im Ir It Jq Mc Mn Na Ni No Oh Pd Pe Pf Pg Qc Qd) Mn(Ij Ir Mh Mj Mq Na Ni No Nq Nv Ny Pb Pe Pf Pg Qc Qd) Nt(Ij Im Iq It Jp Lh Lz Mq Mx Na Nm No Oe Pb Pc Qd) Ni(Ij Lj Mc Mh Ml Mx Mz Na No Nv Oh Pe Pf Qc Qd) Nc(Ir Jg Ji Lz Mh Mi Mq Mr No Nx Ny On Pc Pd) Ij(Im Iq Ir Lz Mi Mk Ml Mr Mv Nv Oh Pe Pf Pg) Mj(Dc Dk Ih Ir Jr Mc Ml Pc Pe Pf Pg Wm) Ne(Fp Ih Jh Lj Mk Mm Mu Mv Nr Nu Nx Pb) Nf(Ao bJ bN Ch Co Cw Di Rb Ri Tn Ut Vo) Om(aA dN eP Fp Gc Im Is Ji Lh Nm Oh Oi) dX(Ez Jd Jt Jy Kk Ks Qw Ra Ue Uf Ur Wm) Lz(Hv Iq Lh Mc Mh Mi Mu Nv Pc Pg Qb) Na(Im Ir Mh Ml No Nv Oh Pe Pf Qc Qd) Hw(Dk eP Fp Il Jm Ms Nm Nr Oi Qe) Js(aA aH bL cE Co gP Il Ko Ut) Nq(Is Lh Li Mk Mm Mr Ms Qe) Iq(Im Is Jg Jp Ms Nn Nr Pg) It(Dc Im Mc Mh Ml Pe Pf Pg) Qd(Ir Mf Ml Mm Nu Pe Pg Qa) fR(Gl Jo Jt Mp Pc Qx Rb Vo) Em(Iz Jf Ke Kl) Qc(Ml Mm Ny Oe) Jg(Iu Mu Mv Nv) Lh(Im Ir Pf Pg) eP(Hu Nd Nm Qy) Dc(Jf Jr Md) Dk(Jo Pb Pg) Dr(Jt Kj Qt) Fp(Iu Mq Nj) Pe(Mp Mr No) bN(Gl Jo Oe) Md(aA Ms) Mh(Ml Pf) Mw(Nv Ny) Nj(Ih Jh) Im(Jl No) Pc(Jq Oi) AaNl BgJr GlUr GzVo HaLj NuJl MeKr MmOe MpPg MyIu NdPb KneM} Mt{Nl(aA Fr Hq Hr Hv Hx Ih Ij Ik Il Im Io Ir Is It Iv Jh Jl Jm Jn Jo Jq Jr Jt Li Lu Lw Lz Ma Mb Mc Mf Mg Mh Mj Ml Mn Mp Mq Ms Mu Mv Mx My Mz Na Nc Nf Nh Nj Nn No Nq Nt Nu Nv Ny Oe Pd Pf Pg Po Pz Qa Qb Qc Qd) Fp(Hr Ih Ii Ij Ik Il Io Ip Iq Ir It Iv Jg Ji Jl Jm Jn Jp Li Lw Lx Ma Mc Me Mf Mj Mk Mn Mq Mr Ms Mu Mv Mw Mx My Mz Na Nb Nc Ng Nh Nm No Nr Nt Nu Nv Ny On Pb Pd Pe Pf Pg Po Pz Qa Qb Qc) Jj(Fr Hv Ih Ii Ij Im Io Ip Is Iu Jh Jk Jl Jn Jo Jq Jt Lh Li Lu Lw Lz Mb Mi Mj Mk Mn Mp Mr Mw Mx Na Nb Ng Nm Nn No Nr Nv Ny Oe Of Oh On Oy Pc Pd Pe Po Pz Qa Qb Qc Qd) Nd(AA Ih Ij Ik Il Io Iq Is It Jk Jn Jq Jr Jt Lh Lz Ma Mb Me Mg Mh Mj Mk Mr Ms Mw Mx My Na Ne Nf Nh Ni Nr Ny Oh Oi Pb Pd Pe Pf Qa Qb) Nj(Fr Hq Hu Ii Ij Ik Io Iq It Jl Jq Jr Jt Lh Lu Ma Mg Mk Mp Mq Mr Mv Mz Nb Ni Nn Nq Nr Nu Nv Oy Pe Pf Pg Qa Qb Qc) Hw(Fr Hu Ij In Io Ip Iq Ir Jk Jl Jn Lz Mb Mc Me Mg Mj Ml Mp Mu Mx Ni Nn Ns Nv Oh Oz Pf Pg Po Qa Qd) Lv(Hu Hx Ij Il Iu Ji Jk Jo Jp Js Lj Lu Me Mf Mh Mm Mq Mv Nh Ns Oe Of Oi Pa Pg Qb Qd) Md(Hv Iu Iv Jo Jr Mb Mg Mk Ml Mm Mv Mx My Na Nb Ng Ni Nm Ns Oh On Qb Qc Qe) Om(Fr Hr Hx Ih In Iq Iv Jm Jq Jr Me Mh Ml Mq Ni No Nq Ns Nv Ny Pa Pc Pe Pg) Lx(Fr Hq Hu Jo Jq Ma Ms Mv Nf Ng Ni Ns Nt Nu Oe Oi Oz Pb Pc Qb) Nu(Hx Ij Il It Iu Jk Jo Jp Mx Nf Nq Ns Oh Oy Pa Pd Po) Js(Hx Ip Iq Ir Iv Jg Mf Ms Mv Nc Ne Nx Og Oi On Oz Pb) Nh(Hu Im In Ip Jg Jk Lu Ni Nk Ns Of Og Oi On Pa Pc) Iq(Ih Im In Iv Jg Mf Mi Mm Nc Ne No Ns Nt On) Jp(Ii Ij In Jk Jl Ma Mb Mf Mv Nc Ne Nt Oz Qc) Nq(Fr In Iv Lw Ml Nb No Ns Nt Og On Oz Pb) Ns(Hx Ik Jg Nc Ne Nt Nx Oz Pb) Jk(Ik Ip Li Mi Mm Ne Nm Oi On) Nt(Ii Iu Jo Nf Ng Oi Oz Pa) Ji(Hx Ii Jo Jq Ms Of Oz) Og(Lj Ms Nc Nm Nx Pa Pc) Ik(In Iu Jo Of Oi) Jg(Ii Ne Nf Ng Oe) Nc(Ni Nk Oi Pa) Hx(Iv Mf Mv On) Oy(Mi Mr Nb Nr) Oz(Lj Mm Mv On) In(Ih Lj Nc) Oc(Iv Mi Mk) Nx(Nf Ng) eM(aX Ib) MiMv MjIv NeIp IiPa OfOi} Nl{Og(Hq Hr Ih Ii Ij Il In Io Iq Ir Is It Iu Jk Jl Jn Js Lj Lu Ma Mb Mc Me Mk Ml Mn Mp Mq Mr Mu Mw Mx Mz Nc Ng Nh Ni Nj Nn Nq Nr Nu Ny Oe Oh Om Oy Oz Pc Pd Po Pz Qa Qb Qc) Lv(Aa Hq Hr Hv Hx Ih Ik Iq Ir Is Jh Jk Jo Jr Js Jt Lh Li Lu Lz Ma Mb Mc Mf Mg Mi Ml Mn Mp Mu Mv Mw Mx Na Nc Ne Nh Ni Nm Nv Ny Of Oh Oy Pb Pc Pd Pe Pf Po Qb Qc Qd) Ji(Aa Hr Hu Hx Ii Ij Ik Im Is It Iv Jg Jm Jq Jr Js Li Lj Lz Mc Mf Mh Mj Mk Ml Ms Mv Mx My Mz Na Nb Nc Ne Ng Nj Nt Nu Nx Ny Oe Oi On Oy Pb Pd Pe Pg Po Qb Qc Qd Qe) Pa(Fr Hv Hx Ih Im Io Ir Is Iv Jh Jl Jn Jo Jq Jt Lh Li Lu Lw Ma Mb Mc Mf Mg Mh Mj Ml Mp Mv Na Nc Ne No Nq Nv Ny Oe Of Oh Oi Om Oz Pb Pc Pd Pf Pg Po Pz Qd) Aa(Fp Hr Hu Hv Ii Is It Iu Iv Jg Jh Jl Jn Jp Jq Lj Lu Lw Mc Mi Mk Mm Mp Mr Ms Mv Mw Mx Nc Ng Nk Nm No Nq Nr Nu Nx Pb Pc Pe Pg Pz Qa Qb Qc Qd Qe) Jg(aA Hq Hr Hx Ii Ij Im Ip It Jh Jm Jr Js Lj Lu Lz Ma Mc Mf Mg Mh Mi Mk Ml Mq Mu Mx Mz Nb Nq Nt Nv Nx Ny Oe On Pb Pc Pe Pg Qb Qc Qe) Mi(aA Fr Hr Ij In It Jm Jn Jo Js Lh Li Lu Lz Mb Mf Mz Nc Nm Nr Ns Nu Nx Of Oi Om Oy Pc Pz Qa) Fp(aA Fr Hw Im In Ip Iu Lw Lz Me Mh Ml Mp My Mz Nb Ni Nk Nm No Nt On Oz Pg Qe) Nx(Hq Hr Hu Il Jk Jm Jo Lj Me Ml Nd Ne Nf Ng Ni Nk Of Om Oz) Nt(Hw Il Jk Lj Nf Ni Ns Of Oi Om Oz Pb Qe) Md(aA Ik Im Ip Jt Lh Lj Mz Ni Nv Om Pg Qa) Qe(Ik Il Iu Jk Jm Jr Js Me Ni Of Om Qc) On(It Jo Lj Lz Me Mv My Ni Ny Oz Pg Po) Nk(aA Ih Im Jr Mp Nb Nv Pe Pg Qa) Fr(Il In Iq Jk Mv Nd Nf Ni Ns) Mm(Ij Il Is Jt Lh Li Mg Mj) Lh(Il In Iu Jk Js Of) Nd(aA Im Ip Me Nv) Li(Hw Il In Nf Ns) Me(aA Gc Ip) Hw(Ip Pe Qa) In(Is Nv Qa) Jp(Jl Mr) Nv(Iq Js) aA(Hu Ns) NfPc IkIu IlJr ImOm KobN OzfR aXdX} Lx{Ik(aA Fp Fr Hv Hx Ih Il Io Ip Iq Ir Is It Iv Jh Ji Jl Jn Jq Li Lj Lu Lw Ma Mb Me Mf Mg Mh Mn Mp Mr Mu Mw Mx Na Nb Ni Nk Nm No Nr Nu Nv Nx Ny On Oy Pb Pc Pd Pe Pf Pg Pz Qa Qd Qe) Nh(Fr Hv Ih Il Io Ip Ir Is It Iv Jh Jl Jm Jq Li Lj Lw Mb Mc Mg Mh Mk Mm Mn Mp Ms Mu Mw Mz Na Nb Ne Ni Nm Nn No Nr Nu Nv Ny Oh Om Oy Pe Pf Pg Pz Qe) Nc(Hq Hr Hv Ij Im It Iu Jh Ji Jn Jo Jp Lw Ma Mb Mc Mf Mg Mi Mj Ml Mm Mq Mv Mw Mx Na Nm No Nu Nv Nx Ny Oe Oh Oi Om On Pa Pb Pd Pf Pg Pz Qa Qb Qd) Lv(Fp Ih Ii Im Ip Ir It Jh Ji Jn Jq Jt Lj Lu Mb Mc Me Mg Mh Mi Mj Mm Ms Mu Mw Mx My Na Nb Ng Ni No Nr Nv Nx Oe Om On Pa Pb Pd Pg Pz Qe) Nt(Fp Hq Hr Ij Il Im It Jm Jp Jr Lz Ma Mb Mf Mh Mi Mk Ml Mp Mq Ms Mv Mx My Na Ni Nn No Ny Oe Oh Om Oy Pd Pg Qb Qc Qd) Jj(Hr Hv Ii Io Ip Ir Is Iu Jl Jo Jq Jt Lh Li Lj Lu Lw Mi Mk Mn Ms Mw Nb Nm Nn Nr Of On Oy Pe) Po(cH Fr Hu Hv Ii Im Io Ip Iu Jm Jn Jo Kc Mj Mu Mv Mw My Na Nm Nv Qb Qd) Ne(Fr Ih Io Ir Is Iv Jl Jt Lh Mk Mn Mp Mr Mu Mz Nr Om Oy Pe Pz Qe) Nu(Fr Hr Ii Ij Iu Jr Lz Mn Mx Nn Nx Oh Oy Pb Pf Qb Qc Qd) Nd(Ih Ii Io Iq Jk Jq Jt Lh Lj Me Mn Ng Nk Nv Pa Qb Qc Qe) Hx(Fp Hu Hw Ii Im In Jh Jo Jp Lz Mg Mv Nf Ni Nx Oe On Oz) Jg(Hq In Iu Jr Jt Ma Mb Mf Mn Mp Mw Ni Nn No Nv Oi Pc Qc) Js(Aa Hr Iq Ir It Iv Jp Jr Mg Nk Oe Og Pc Pz Qa Qe) Oz(AA Fp Hw In Iq Jk Jo Jp Mi Mv Ni Nq Og On Qc) Nf(Aa Iv Jp Lh Ma Mb Md Mf Mg Mi Nb Nq Nr) Nq(Fr Im In Iv Jh Mi Ni Nx Og Qa Qe) Md(Hr In Jk Ma Mg Mm Nk Nr Pc) Hw(Ih Iv Jp Mf Ni Oi On Pb) Og(aA Ji Mb Nk Nx Oi Qc) Jk(aA Mg Nx Oi Pb) Ji(Ii In Of Qc) Iq(Jp Nk On) Nx(Jq Oe) DcKo GcKc MfQc NbOe HqOn IvOy QwfR OfOi} Ko{fR(aI aK aN AO aZ Bb bC Bg bJ bP bS bU cF cH cM Co Cp cQ Cu Cv cY dE dM Fa Hc Hq Hr Hv Hw Hx Ir Jm Jn Jy Kd Kf Kx Kz Ml Mm Mn Mq Mr Mu Mw Ni Nr Nu Oe Oh Pg Pi Pj Qc Qe Qg Qv Rm St Tz Ud Ul Uv Vv Tj tF) bN(Af aI aZ Ba bZ cG CH cN Ct Cw DE dJ Ef Fa Fr gW Hu Ic Iq Ir Is It Jj Jl Jn Jy Ki Kl Kp Lh Mq My Nb Nd Nj Nn Nq Ns Ny Of Og Or Pe Qc Qh Qu Ra Rb Rg Ri Rj Ss Tr Tt Uc Un Vp Vs Vt Vu) Js(aC aI aK Ao aV aX bJ bU bX cA cD cE cH cM cQ Ct Cw dE dM dN Gl Hu Ip Iz Mk Mu Oe Og Ou Oy Rb Rg Rh Rm Sr Ua Uk Ul Vs) Dc(Ad Ax Bg CH Cv Dk Fp gP Hr Hw Il Ip Iq Jj Jk Jp Kj Kr Ma Mj Mu Mv Nm Nr Nx Oe Oy Qe Qh Ql Qy Rh Ua Uk Ul Ut Vs) Om(aX Bg bP bZ Ch Cp cQ cS cX cY dC dJ Gz Ha Hq Hu Ii

Dr) Vq(Nf Or Qw) dO(aK aP bF) Bo(Dv gC) Gt(cB Cs) cH(bA Qy) BcbV DocF DvcW HaLj NfSr KqVo dGgC} Nt{Pa(Hq Hw Hx Ik Im Ji Jm Js Jt Lz Mi Nc Ni Nq Oe Oz Pd) Nf(Fr Im Ip Li Ne Ns Nv Of Oi Pf Pg Qa) Lv(Fp In Iu Jo Ng Nh Ns Of Oi Om Qe) Oz(Im In Iq Jo Mi Mm Nc Ne Ns Of Oi) Md(Im In Iq Nc Nh Of Pc Qe) Qe(In Iq Jk Jo Js Of) Fp(Il Iu Jo Ns Oi) Im(Iq Jk Of Om) Nc(In Iq Nk) Ne(Hw In Iq) Nh(Hw In Iq) Jk(On Qa) IuPb JoLh OgaA} dX{Kk(aC aL aM cC cM Cx Dc Dl Jd Jy Kz Mq Mr Nm Uf) Qx(Ba bX cO Dl Hv Jr Kp Ow Pb Pd Vv) Hf(aS bR Ex Jn Md Qh To Uo) Qw(aO bA bV cO cP Cs dB dN) Ib(Ar eF Hc Kz Qd) Qy(cN dM Fa Jy Ki) Pb(bE Dd Nu) Ph(aD In Rc) Ha(Nv Oh) Ue(Hc Pa) Jy(dN gL) Kz(aJ gW) Ld(aD dN) On(Ur Vo) Oz(aN cF) dJ(Hc Pc) dM(uK cY) PoNx NuaX MhcN HuKn InJn OhaN UkPj dGdO} Dq{eF(aE aF aP Ar aS aZ bJ bO bZ cB cE cG cJ cR cS Ct CU dF Dg Di DK Dl Ef eX Fr gC GT) Fw(al aR As aU Ax aY bN cG Cq cR cT cZ dB dC dE Dk dN dO dV Ef Ex Fr Gl Gp) bC(An aQ aZ Bg Cs DD dF Di Gp GW) cF(AD cG cH dO) aK(aJ dN) dG(aO dR) BoDi CsaN aXcP cEcY} Em{Rb(aA Aj bE bV cB cH dI dJ dK gW Ju Mv Or Qw Ug) Kk(aJ Cu Jh Mv Mw Nm Ny Om Qh) Vo(aC Bc cF dF gL Mg Ql Qx Sr) Nu(Ch In Jk Kd Oz Pc) Ue(cF cR Ld Ou) Qz(AJ In Om) Qw(dL Dp Or Rc) Kj(Ex Oh Ph Rf) Nx(Ke Kg Tt) Nf(Fa Ld) aJ(bW Pc) dO(aX eF) AxQt CtOu HaNv IbKy QxKe LdcW UocY aNbR} On{Om(Dk Fp Hq Hr Hw In Jk Ma Mv My Nb Ng Ni Nq Nu Oz Pa Pc Po) Oy(Hx Ii Iu Ji Jt Lz Ma Mj Nc Nr Ns Nx Of Pd Pe Pf) Nf(Hx Iv Lj Lv Ml Mr Mv Ne Oz Pe) Md(Jk Ml Nu Nx Oz) Ne(Hw Ii Js Of) Dr(Hu Qt Ra) Hw(Iq Nq Ns) Ik(Ii Ij Jo) Oe(Nu Nx Oi) Nh(Hx Js) GcIb NqJs LvOf NcJk} dV{dG(aC aI aR bF bJ cA cD cG cN cR cW cX cY dA dN dR gW) aJ(aU bC bL cE cP cS dA Dl dN dO) eF(aG bN cU cY cZ Db Dg Dl Gc Tj) aX(Ar cB Dg Dl Ex gW) aP(aK aQ cF cS eX) cG(aY cA cN cY eX) bF(aD dL dN) Fw(aM bC) bQ(bU eX) cF(Ad Dl) dF(aF aM) dK(aQ cY) BoDi CsbC cBcN cSdM} Ik{Og(Aa Hr Hu Hw Im Io Is Jh Jl Jn Jq Mg Mh Ml Mp Mr Nb Ne Nf Nh Nu Nx Oi Om Oz Pb Pc Pe Pg Po Qa Qb Qd) Pa(Hw Im In Iq Ji Jk Jm Jo Lv Mi Mz Ng Ns Om Po) Iu(Fp Ji Mm Nx Qe) Nf(Fr Lh Li Lv) Mi(Hq Oy) Qe(Jo Js) Ji(Of Oz) MmOi ImOm JoLh} Nx{Md(aA Hr Im In Iq Iu Iv Jh Jk Jo Lj Lz Mb Ml Mq Mu Mw My Nb Ng Nn Nq Ns Nv Of Oi Oy Pd Pe Pf Pg Qa Qe) Dr(Cu dJ Ef Kg Ma Ny Or Ul) Nf(Ar Fp Ji Qe Ri) Gc(Ha Pj Tz) Nu(In Jo Of) Dc(Lj Qe) Fp(Oz Pa) Mi(Of Oy) Nc(Hw Lv) MzJs NeOg NhHw JriZ} Dr{Rb(aC dF dJ In Jy Mm Mr Ni Og Ub Vo) Hu(cN dG eF Hq Ld Oy Pa Qx Vv) Qw(aJ In Jo Jy Kj Mr Nf Uf) Gw(aK bR cN cY) Kk(dJ Jo Li Nc) Ra(Dl Oi Or) Ib(aC Ex) In(Ou Rm) Ld(aJ dL) Vo(Dg Jn) aX(dO Qz) MvaJ UecF HfOm RcKf OgdJ aNcH} Gc{Ue(aZ cN cZ dJ Kj Kz Ns Ny Or Qt Qx) Vo(aX Dg gL Gz It Ji Oz Pc) Kk(cF dJ Jo Jt Kd) Hu(dG dL Kj Rc) Hf(Ib Mv Oz Pc) Rb(dE Io Jo Qx) Kj(aC dJ Ra) Og(aN Ne) InJn QxcV QtKd KfUu KzaJ LddL aXdR} Gw{Dd(Bg Bn cA cC cQ Cs eX Fr) bC(aJ An cK cU dA Dg Dl eF) aD(Ap Bg bR dL) Bc(Al Bo) Ct(bA dR) Gt(Dc Fw) aN(bL eF) aQ(cN dG) aX(bE dO) dL(bU cY) GpcN aGeF aJdH aKcS aMcB bAcH bRdG dNdR} dO{aX(As Aw Bb Bo Cv Dd De DL Ex) eF(aK Bc bX cR Dc dI dJ dL) bC(Ap Bo Ch cN cR Dc Dg) dG(aQ cC cM cT cY) aJ(Bn bW cI dJ) cN(Ad aI) dM(bU cY) CsaN DgcF aDaK} Nf{Ji(Fr Iq Jr Js Mb Mm Mq Mu Nk Nq Nr Om Oy Pb Pd Qa) Lv(Im Li Mm Nc Ne Ny Oh Qa) Fp(Fr Pa Qc) Id(Dc It Rb) Nu(Nv Pa) Kq(Dk Vo) Vq(aX Hu) ArIt NhPa} eX{Fw(aX cH Dc eF Gl Gp) Dl(aN aX bC Bo) aN(Ax Ba Dd) bC(aK Dd dJ) cY(aP dG dL) dF(aU bU dJ) eF(bU Dc dR) Dg(aX cF) dI(dG dL) BgbR BoDi aKcR bAcI cTdL} Ne{Mm(Hw Iq Jr Ns Pb Pc) Og(Aa Fp Jq Jt Md Mi) Qe(Hw In Iq Lv) Ji(Mq Ns Oz Pa) Md(Lv Nb Pa) Pa(aA In) AaOm FpLv HwNv} Gt{Fw(Al aW CQ Cv cZ dR Ex Gp) aN(cG cP dI) bC(Dd dJ dR) aK(aJ bE) aM(An cG) eF(bL cF) BoDb DdcB bFcP cGcY dKdR dMgW} gT{cG(aN aQ bR dR) dG(aO bU cY dR) aD(aZ dR Fw) aJ(aK bU) aM(aQ Fw) cY(bQ eF) aKbC dLeF} Fp{Md(Ji Nc Nv Ny Oz Pa Qe) Og(Jh Lv Mg Pa) Oz(Il Ji Mi) Pa(Lv Nc Nh) LvIl} Vq{Vs(hG iA kS nW oE oF pF) Hu(Jf Uk) Qw(aJ Ky) CtiZ NcaX HwpF RaUk VofP cYgW} Nh{Pa(Hu Im Iq Ji Lv Mm Ns) Md(Nv Pe Qe) Oz(Ji Mm) HwNv InQe} gN{Bo(Di Dl) aJ(aQ cB) aK(bC cE) aM(aW bA) cG(bR cY) CseF bCdJ cYdK} Do{cE(aK cP cY) Fw(aM aN) bC(cF cG) dK(cY dR) eF(Bc dA) aKbE} Dc{Ad(Ar Ax Cv Dk) It(Ar Rb) DgVo GlLh QcQe} Md{Lv(Nc Pg Qe) Ji(Ml Nc) Nv(Hw Nq) MmOz} Vo{Dg(aI cE Jk Mj Mv) Kk(Ex Pj) GzSt} aJ{bU(bL bZ cH) gC(aK cA gW) AabL bNbR} Dv{cG(aD cF) TjFw aUaX cEcY dNeF} Oz{Ji(Hw Jo Lv Mm Ns) NuMm} Aa{iZ(Hx Jr Js) RbaX} Pa{Nu(Hw Ns Og) LvMm} cH{NrOm aAaZ aWdF dLgC} Nc{Hw(Lv Nv) IqQe} Jr{pF(Fr Kq Sr)} aX{gC(aU Fw) OuVs} Ha{GziZ NoLj} Jf{Jk(Dg Kf)} dG{bZcT cYgC} ExKkKx GlUhUr LvMmOm MjIdIt KqUtgL

Unconstrained panels with 2 analytes, where 1.0E-7 >= 'AUC p-value' > 0. Contains 91 panels of 77,685 total panels evaluated. : Gn(aD aN aV bR bU Ch cP dJ dL Ef Gl Hu Ly Om Qt Ra Rb Rc Ue Um Uo Vo) Et(Jj Jo Jr Jt Lx Ly Md Mt Nc Nd Ne Nf Nh Nj Nl Of Om Oz Pa) Ok(Hw Iq Jo Js Jt Ly Md Nc Nd Nf Nj Nl Nq Om) Nw(Hw Ik Iq Js Ly Md Nc Nd Ne Nf Nj Nl Om) Ly(Dr EM fR Jg Jp Lx Mt) Nl(Jj Jp Lx Mm) Kc(Dr dX eM) Nt(Jj Og) Lx(Nd Nj) dO(aV cL) NjJp KkeM Unconstrained panels with 2 analytes, where 1.0E-6 >= 'AUC p-value' > 1.0E-7. Contains 214 panels of 77,685 total panels evaluated. : Nw(Et Fp Hq Hr Hv Hx In Ir It Iv Jg Jj Jo Jp Jq Jr Jt Lj Lv Lx Lz Ma Mb Mc Mf Mg Mh Mi Mj Ml Mq Mt Mv Mx My Na Nh Ni Nk No Nq Nr Ns Nt Nu Ny Of Og Oh Oi Ok On Oy Oz Pa Pb Pe Pf Pg Po Pz Qa Qb Qd Qe) Ok(Hq Hr Hx Ii Ij Ik In Iv Jj Jk Jq Lv Lx Lz Ma Mb Mg Mj Mn Mp Mt Na Ne Ng Nh Ni No Ns Of Og Oh Oy Oz Pa Pc Pe Po Qc Qd) Et(Dk Fp Gl Hw Ii Ik Iq Iu Iv Jg Js Lj Lv Mb Nk Nm Nq Ns Nt Nx Og Pb Pc Vo) Gn(Aa aJ aM Ao aX Bb cF cH cI cM cN dI EX Fw gP Jj Kc Me Og Or Qu Qw Ul) Lx(Ik Jg Jj Lv Nc Ne Nh Nt Po) Ly(aX bN cH Fr Gc gP Jj On Pa) Mt(Fp Hw Hx Jj Md Nd Nj Nl Nq) Nl(Aa Fp Jg Ji Lv Og Pa) Nd(Jg Mi Nt Nv On) cL(Dq eX gN gT) Ik(Jj Jp Og) Jg(Nj Of Om) Kc(Em eP Gc) Dq(eF Fw) Ne(Jj Jp) Nh(Jj Jp) MdNx MmNj NfJi dGdV Unconstrained panels with 2 analytes, where 1.0E-5 >= 'AUC p-value' > 1.0E-6. Contains 499 panels of 77,685 total panels evaluated. : Et(aA Bg Ch Dc Fr Hq Hr Hu Hv Hx Ih Ij Im In Io Ip Ir Is It Jf Jh Ji Jk Jl Jm Jn Jp Jq Kk Lh Li Lu Lw Lz Ma Mc Me Mf Mg Mh Mi Mj Mk Ml Mm Mn Mp Mq Mr Ms Mu Mv Mw Mx My Mz Na Nb Ng Ni Nn No Nr Nu Nv Ny Oe Oh Oi Ok On Oy Pd Pe Pf Pg Po Pz Qa Qb Qc Qd Qe Ri Ur Ut) Gn(aG Aj aK Al An aP aQ Ar AS aZ bA BC bL BN Bo bP cA cB cE cG cL cO Cs Ct CW cY dA DD dE dF dG Di dK DO Dq eF Em Ez gL Gp gT GW Hb Ib Ij Iz Ju Jv Jy Kd Kf Kj Kk Kl Kn Lu Mf Mn Mu Mv Nb Ng Nj Nm Nx Ny Ss Uf Uk Uu) Ok(Dc Dk Fp Fr Hu Hv Il Im Io Ip Ir Is It Iu Jg Ji Jl Jm Jn Jp Jr Lh Li Lj Lu Lw Mc Me Mf Mh Mi Mk Ml Mq Mr Ms Mu Mv Mw Mx My Mz Nb Nk Nm Nn Nr Nt Nu Nv Nx Ny Oe On Pb Pd Pf Pg Pz Qa Qb Qe) Nw(aA Dc Dk Fr Hu Ih Ii Ij Il Im Io Ip Is Iu Jh Ji Jk Jl Jm Jn Lh Li Lu Lw Me Mk Mm Mn Mp Mr Ms Mu Mw Mz Nb Ng Nm Nn Nv Nx Oe Pc Pd Qc) Ly(Aa aJ aN Ar aZ bA bJ Db Dc Dd dE dJ Hv Id Im Ir Ji Lh Li Lj Mi Mm Mz Nc Nl No Nt Nv Nx Ny Pe Pg Qe Sr) Mt(Ik In Iq Jg Ji Jk Jp Js Lj Lv Lx Mf Ms Mv Nc Ne Nh Ns Nt Nu Nx Ny Oe Of Og Om Oy Oz Pb Pc Qd) Nl(aA Fr Ik Im Ip Li Lj Md Mi Nb Nk Nm Ns Nt Nv Nx On Pc Pe Qa Qe) Lx(Fp Hr Hw Hx Iq Ji Jk Js Mb Md Mf Nf Ni Nq Nu Og Oz Pb Pc Qc) Nt(Fp In Iq Jo Jp Lv Md Nc Ne Nf Nh Nj Of Oz Pa Pb) Jg(Fp Ik Iq Iv Jj Jk Md Mv Nc Ne Nf Nh Nq Ns Nu Og) Nj(Aa Fp Fr Ji Jj Lv Mi Nv Nx On Pa Qe) Nd(Aa FR Im Ji Jl Jp Mm Mu Qa Qe) Ko(bN Dc Dk fR Jf Jk Js Om Qw) Fp(Ik Im Lv Md Ne Nh Nx Og) Lv(Ji Jp Nc Ne Nh Nx On) Jp(Mb Md Nc Nf Nq Nu) On(Hw Iq Nf Nq Om Oy) fR(dO gP Qw Qx) Gw(aV cL Dd) Ne(Ji Mm Og) Ik(Mm Pa Qe) Fw(eX Gt) Me(Dr Gz) Nh(Ji Pa) aJ(bU dO) aV(eX Gc) cL(eM Gt) gP(gL Kk) AdDc NuPa NcJj HwNx JiOz cHdM Unconstrained panels with 2 analytes, where 1.0E-4 >= 'AUC p-value' > 1.0E-5. Contains 1,089 panels of 77,685 total panels evaluated. : Gn(aA aC Ad aE AF aH aI aL aO Ap aR aU AW Ax aY Ba bB bE bF BG bH bI bJ bM bO bQ bS bV bW bX bZ cC cD cJ cK Co Cp CQ cR cS cT CU

Figure 11 Continued

CV CX cZ DB DC De Dg dH Dk Dl dM dN Dp DR dX Ed eM eP Fa Fb FR GC gN Gt Hq Hv Hw Id Ii Il Im Iq It Jd Jf Jg Jh Ji Jk Jm Jo Jr Jt Ke Kg Ko Ks Ky Ld Lh Li Ma Mg Mq Mr Mw Na Nd Nf Nk Nl Nq Nu Oa Oe Of Oh Ou Ow Oy Oz Pa Pb Pc Qd Qv Qx Qy Rf Sr Ua Uc Uh Up Ut Wm Tj) Nl(Hq Hr Hu Hv Hw Hx Ih Ij Il In Io Iq Ir Is It Iu Iv Jh Jk Jl Jm Jn Jq Jr Js Jt Lh Lu Lw Lz Ma Mb Mc Me Mf Mg Ml Mn Mp Mq Ms Mu Mv Mw Mx My Mz Na Nc Nd Ne Nf Ng Nh Ni Nj Nn No Nq Nr Nu Ny Of Oh Oi Om Oy Oz Pb Pd Pf Pg Po Pz Qb Qc Qd) Nt(aA Fr Hq Hr Hu Hw Hx Ih Ij Ik Il Im Io Ip Ir It Iu Iv Jg Ji Jk Jl Jm Jr Js Lj Lu Lw Lz Ma Mb Mc Me Mf Mh Mi Ml Mm Mn Mp Mq Ms Mu Mv Mx My Mz Na Ng Ni Nk Nn Nq Ns Nu Nv Nx Ny Oe Oh Oi Om On Oy Pc Pd Pe Pf Pg Po Pz Qa Qb Qc Qd Qe) Ly(aA Ad Af aH al Ap aV Ax Ba Bb bE bL Bo bR bV cE cJ cM cP cQ Cs Ct DG Di Dk Dl dM dX Ex Fp gL Gz Ic Ih Ik Is Iv Jf Jh Jl Jn Jr Ko Lv Lw Ma Md Mn Mp Mu Mw Nb Ne Nh Nj Nm Nn Nr Nu Og Oh Oz Pc Pf Pj Pz Qa Qb Qd Rf Uh Vq) Mt(aA Fr Hq Hr Hu Hv Ih Ii Ij Il Im Ip Ir It Iu Iv Jh Jm Jn Jo Jr Li Lu Lw Lz Ma Mb Mc Me Mg Mh Mi Mj Mk Ml Mm Mn Mp Mq Mr Mu Mw Mx My Mz Na Nb Nf Ng Ni Nk Nm Nn No Nr Nv Oh Oi On Pa Pd Pe Pf Pg Po Qa Qb Qc Qe) Et(Af al Aj Ao bA Bb bJ bL bN cE cH Co Ct Cw Db Dd De Di Dl Ef gP Ha Hc Hf Ib Id Il IZ Jv Kc Kd Ke Kg Kj Kl Kn Ko Kp Kr Ks Kz Or Ou pF Ph Ql Qt Qw Qy Ra Rb Rc Rj Tn Uc Ue Uk Ul Un Up Uu Uv Vp Vu Wm Tj) Jg(Hq Hr Hu Hw Hx Ih Ii Ij Im In Ip Ir It Iu Ji Jo Jp Jr Js Jt Lj Lu Lv Lz Ma Mb Mc Me Mf Mg Ml Mn Mq Ms Mu Mw My Mz Nb Ni Nk Nx Ny Oe Oh Oi Oy Oz Pa Pb Pc Pd Pe Pf Pg Qa Qe) Lx(aA Ii Ij Im In Ip Ir It Iv Jh Jn Jo Jp Jr Lj Lz Ma Mc Mg Mh Mj Mm Mn Mp Mq Mv Mw Nb Ng Nk Nr Ns Nx Oe Of Oi On Pf Pg Qb Qe) Nh(Hu Hw Ih Ik Im In Ip Iq Jh Jn Jr Jt Lh Li Lj Md Me Mg Mi Mm Nd Nk Nm No Ns Nu Nv Nx Og Oh Oi On Oy Pb Pe Pf Pg Pz Qa Qe) Fp(Fr Hw Hx Il Ip Ir Iu Iv Jh Ji Jj Jo Jp Lh Lz Mg Mh Mi Ml Mu Mw Mz Nc Nd Nf Ni Ns Nu Nv Oh Om On Oz Pa Pd Pg Qa Qe) Nu(Hr Hv Hw Im In Ir Ji Jj Jl Jn Jo Li Lv Md Mh Mi My Mz Nf Nj Nk Nn Nv Nx Oe Of Og Oh On Oy Oz Pf Pg Qe) Ko(Bg Ch Cp Dd Di eM Gl gP Ha Iq Jo Jr Kj Ma Me Mj Mk Mu Mv Nf Oe Og Pg Po Ri Rj Ua Uk Ur Ut Vo Vs Vu) Ik(Fr Im Ip Iu Ji Jl Jo Li Lj Lv Lw Md Me Mi Mz Nc Ne Nf Nj Nm Ns Nv Nx Of Oh On Oz Pc Pe Pg Pz Qa) Lv(Hv Ih Il Im Iv Jj Jn Lh Li Lj Mm Nd Nf No Nr Nv Ny Oh Oz Pa Pe Pg Qa Qe) Jp(Hw Hx Iq It Iv Ji Jj Jr Js Lj Mf Ni Nk Nr Ns Nx Oi Oz Pa Pc Pd Pe Qc) Ne(AA Fr Hw Im Ip Iq Jr Li Lj Md Me Mi Nd Nv Nx On Pa Pe Qa Qe) Nw(Ao Bg Co Di Gl Ha Ib pF Ql Rg Ri Rj Sr Ut Vo Vp Vu Wm Tj) Nx(Hr In Jj Js Lj Mi Mq Mz Nb Nc Nd Nf Nm Ns Og On Oz Pc Qe) Nj(aA Im Ip Jr Jt Lh Li Lj Lw No Og Oz Pb Pc Pe Pg Pz Qa) Ok(aA Bg Co Cw Gl Ha Ih Jh Kg Mm Oi Tn Ut Vu Tj) Nd(aA Jh Lh Li Lw Mw Mz Nb Nn No Nr Ny Pe Pg) On(Hx Jj Jk Js Md Mj Ml Na Nc Ns Oe Of Oz Pc) aJ(Aa bL bN bR cH cJ cM Dg dJ Dq dV Em gC gP) Ji(Hw Hx Iq Iv Jj Jo Js Md Mq Nc Nq Om) Jj(Iv Jm Jn Jr Lh Mm Nr Pa Pe Qa Qe) Nf(Ar FR Id Lh Li No Nv Pe Qe) gP(bA Bc cH Dg dM eF Jf Kc Qw Ur) cH(aA aW bA bU cQ dF dG gL) Qe(Dc Hw In Iq Md Nc Qc) aV(Dq Dr eP gC gN GT) dG(bU cA cM cT dH dO gC) Dg(bA Dc Di Dk Vo) Me(Hf Id Jf Sr Vq) dV(cG cL dL eF fR) Nc(Li Mm Nk Og) Kc(bL bN cM dJ) bA(aH bU cC cM) eF(DO Dv Gt) Gw(bC Dr Fw) Nv(Hw Iq Om) Oz(Aa Fr Mm) cL(Do eP gC) fR(Kk Pc Rb) Ad(Ct Dk) dO(aX cN) DqbC EmRb GtaN MmPb HfdX JfPj QyeP cGgN

Unconstrained panels with 2 analytes, where 1.0E-3 >= 'AUC p-value' > 1.0E-4. Contains 2,672 panels of 77,685 total panels evaluated. : Ko(AF aH al Aj Al aM aN AO aR aV aW aX aZ bB Bc bF bH bl bJ bL bO bQ bU bZ cA cC cD cE cG cH cl cM Co cP cQ Ct Cu Cv Cw cZ dC DE dH dl dJ Dl dM dN dX Ef eP Ez Fa Fb Fr Fy gL Hb Hc Hf Hq Hu Hw Hx Ib Ic Id Ii Ij In Ip Ir Is It Iu Iz Jd Jh Jj Jl Jp Jq Jt Ju Jv Jy Kc Ke Kg Ki Kk Kl Kp Kq Kr Ks Ky Kz Lh Li Lj Lv Lx Md Mn Mp Mq Mr Ms Mw Mx My Na Nb Nd Ng Nk Nm No Nq Nt Nu Nv Nw Ny Of Oi Ok On Ow Oy Oz Pa Pb Pc Pe pF Pj Pz Qa Qb Qc Qd Qh Ql Qm Qn Qt Qu Qx Ra Rb Rc Rf Rg Rh Rm Sr Ss Tn Tr Tt Tv Ub Uc Ue Uf Uh Ul Um Un Up Uu Uv Vp Vt Tj) Et(Aa aC AD aE aF aG aH aJ aK AL aM AN aO AP aQ AR AS aU aV AW AX aY aZ Ba bB BC bE bF bH bI bM Bn BO bP bQ bR bS bU bV bW bX bZ cA cB cC cD cF cG cl cJ cK cL cM cN cO CP CQ CS CU CV cW CX cY cZ dA dB dD dE dF DG dH dl dJ dL dM dN Dp Ed eF Ez Fa Fb Fn Fw Fy gL Gn Gp Hb Ic iJ Jd Je Ju Jy Kf Ki Kq Kx Ky Ld Oa oE Ow Pi Pj Pk Qg Qh Qm Qn Qu Qv Qx Qz Rf Rg Rh Rm Sr Ss St To Tr Tt Tv Tz Ua Ub Ud Uf Ug Uh Um Uo Us Vs Vt Vv) Nw(AD AF aG aH al Aj aK Al aM AN aO Ap AR As aV AW AX aY BA BB BC bF bI bJ bL BN BO bQ bS bU bZ cA cB cC cE cF cG CH cI cK cL cM cO CP CQ CS Ct Cu Cv CW Cx dA Db DD DE dH dI dJ dK dM dN Dp Ed eF Ez Fa Fn Fw Fy gL Gn gP Hb Hc Hf Ic Id Jd Je Jf Ju Jv Jy Kd Ke Kf Kg Ki Kk Kp Kq Kr Ks Kx Ld Oa Ou Qg Qh Qm Qn Qt Qu Qv Qw Qx Qy Qz Ra Rb Rc Rf Rh Rm Ss Tn Tr Tt Tv Tz Ub Ud Uf Uh Uk Ul Um Un Uo Up Ur Uv Vs Vt Vv) Ly(aC aD aF aG Aj aK AL aM An AO aP aQ As aU bB BC bF BG bH bI bM Bn bQ bU bX bZ cB cC cF Ch cK cN Co Cp Cq cS cT CU Cv CW CX cY cZ dA dB dC dD De dF dI dK dL dN Ed eF eP Gp Ha Hf Hq Hr Hw Ii Ij In Io Ip iZ Jk Jm Jo Jq Jt Ju Kc Ki Kk Kp Kq Kr Ky Ld Lu Lz Mc Me Mf Mg Mj Mk Ml Mr Ms Mv Mx My Na Nf Nk Ns Oe Of Ou Pb Pd Ph Po Qc Qm Qw Rh Ri St Tt Uf Uk Ur Us Ut Vp Vs Vt Vu) Gn(DV Fn Fp Fy Gz Ha Hc Hf Hr Hx Ic Ih Ik In Io Ip Ir Is Iv Je Jl Jn Jp Jq Js Ki Kp Kr Kx Kz Lj Lv Lw Lx Mb Mc Md Mh Mi Mj Mk Ml Mm Mp Ms Mt Mx My Mz Nc Ne Nh Ni Nn No Nr Ns Nt Nv Oi Ok On Pd Pe Pf Pg Ph Pi Pj Pk Po Pz Qa Qb Qc Qe Qg Qh Ql Qm Qn Qz Rg Rh Ri Rj Rm St Tn To Tr Tt Tv Tz Ub Ud Ug Un Ur Us Uv Vp Vq Vs Vt Vv) Jp(aA al Bg Dc Dk FR Gl gP Hq Hr Hu Hv Ih Ii Ij Im In Io Ip Ir Is Iu Jf Jh Jk Jl Jm Jn Jo Jq Jt Lh Li Lu Lw Lz Ma Mc Me Mg Mh Mi Mj Mk Ml Mm Mn Mp Mq Mr Ms Mu Mv Mw Mx My Mz Na Nb Ng Nm Nn No Nv Ny Oe Of Og Oh Om On Oy Pb Pf Pg Po Pz Qa Qb Qd Qe Qw Rb Ri Ut) Ok(Aa aD aG aH al Al AN Ao Ap Ar As Aw aX Ba Bb Bc bF bJ bL bN bQ bZ cE cG CH cM CP Cq Ct Cu Cv Cx Db Dd De Dl Dl dN Ef Ez fR Fy gP Ib Ic Id Je Jf Kk Kq Kr pF Qh Ql Qt Qw Qx Ra Rb Rg Ri Rj Rm Sr Tr Tz Ua Ue Um Up Ur Vo Vp Vs Wm) Ne(Hq Hr Hu Hv Hx Ih Ij Il In Io Ir Is It Iu Iv Jh Jk Jl Jm Jn Jq Js Jt Lh Lu Lw Lz Ma Mb Mc Mf Mg Mh Ml Mn Mp Mq Mu Mv Mw Mx My Mz Na Nb Nc Nf Ng Nh Ni Nj Nk Nm Nn No Nq Nr Ns Nu Ny Oe Of Oh Oi Om Oy Oz Pb Pc Pd Pf Pg Po Pz Qb Qc Qd) Qe(Fr Gl gP Ha Hq Hr Hu Hx Ii Ij Il Im Ip Ir It Iu Iv Ji Jk Jl Jm Jo Jr Js Li Lj Lz Mb Mc Me Mf Mg Mh Mi Mj Ml Mm Mn Mp Mq Ms Mv Mw Mx My Mz Nb Ng Ni Nk Nm Nn No Nq Nr Ns Nv Ny Of Og Oh Oi Om On Oy Oz Pa Pb Pc Pd Pe Pf Pg Po Pz Qa Qb Qd) Ik(AA Dc Hq Hr Hu Hv Hw Hx Ih Ii Ij Il In Io Iq Ir Is It Iv Jh Jk Jm Jn Jq Jr Js Jt Lh Lu Lz Ma Mb Mc Mf Mg Mh Mj Mk Ml Mn Mp Mq Mr Ms Mu Mv Mw Mx My Na Nb Nd Ng Ni Nk Nn No Nq Nr Nu Ny Oe Oi Om Oy Pb Pd Pf Po Qb Qc Qd) Nx(aA aN Bg cE cH Ct Dc Dk Fr gP Ha Hq Hu Hv Hx Ij Il Im Ir It Iu Iv Jh Ji Jk Jl Jn Jr Lh Li Lu Lw Lz Mc Mf Mg Mh Mk Ml Mm Mn Mp Mr Ms Mu Mv Mx My Na Ng Ni Nk Nn No Nr Ny Oa Of Pb Pd Pe Pg Po Pz Qa Qb Qd Ql Qw Ut Vp) Ji(aA Fr Hq Hr Hu Hv Ii Ij Il Im In Ir Is It Iu Jh Jk Jl Jq Jr Jt Lh Li Lj Lu Lw Lz Ma Mb Mc Mf Mh Mi Mj Mm Mn Mp Ms Mv Mx Mz Na Nb Ng Nk Nm Nn No Nr Ns Ny Of Og Oh Oi On Oy Pa Pb Pc Pd Pe Pf Pg Po Pz Qa Qd) bA(Aa Ad aE aF aJ aK aL aM aN Ap aQ aV aW aX aZ BB bC bE bF bH bl bJ bL bM bN bQ bR bS bX bZ cA cB cD cE cF cG cJ cK cL cO cQ cR cT cU Cv cX Db dE dF dG dH Dl dJ Dk dL dM dV eX fR Gw Me Nd Nf Om Pc Qw) Fp(aA Dc gP Ha Hq Hr Hv Ih Ii Ij In Io Iq Is It Jk Jl Jm Jn Jq Jr Js Jt Li Lj Lw Ma Mb Mc Me Mf Mj Mk Mm Mn Mp Mq Mr Ms Mv Mx My Na Nb Ng Nk Nm Nn No Nq Nr Ny Oe Of Oi Oy Pb Pc Pe Pf Po Pz Qb Qc Qd) Nh(AA Fr Hq Hr Hv Hx Ii Ij Il Io Ir Is It Iu Iv Jk Jl Jm Jo Jq Js Lu Lw Lz Ma Mb Mc Mf Mh Mj Mk Ml Mn Mp Mq Mr Ms Mu Mv Mw Mx My Mz Na Nb Nc Nf Ng Ni Nj Nn Nq Nr Ny Oe Of Om Oz Pc Pd Po Qb Qc Qd) cH(Aa aE aH al aL aM aN aP aQ aZ Bb bC bE bF bG bl bJ bN bS bV bX cA cB cC cD cE cF cG cl cJ cK cM cP cS cT cW cZ dC dE Dg dH dJ dK dN eF fP Gt Gw Iq Jr Lv Nd Nf Nj Nr Nu Om Oz Pa Pb Pc Qw Qx Rb) Nu(aA Ar dI Em FR Hq Hu Hx Ih Ij Il Io Is Iu Iv Jh Jk Jm Jq Js Lj Lu Lw Lz Ma Mc Me Mg Mk Ml Mm Mn Mp Ms Mu Mv Mw Mx Na Nb Nc Nd Ng Ni Nm No Nq Nr Ns Ny Om Pb Pc Pd Pe Po Pz Qa Qb Qc Qd) Nj(bN fR Hw Ih Ii Ij Il In Io Iq Ir Is It Iu Iv Jf Jh Jl Jm Jn Jo Jq Js Lu Ma Md Me Mf Mg Mj Mk Mn Mp Mq Mr Mu Mw Mx My Mz Nb Nc Nd Nf Ni Nk Nm Nn Nq Nr Ns Ny Of Oh Oi

Figure 11 Continued

Oy Pd Pf Po Qb Qd) dG(AA aD aF aK aN aO aQ aV aW aX aY aZ bF Bg bH bI bJ bL bN bQ bR bS bW bX bZ cB cC cE cF cG cJ cK cL cO cP
cV cW cX cY dF dI dJ DK dL dM Dq eX gL gN gP gT Gw Mj Nd Nf Pc Qw) Lv(Aa aX FR gP Hr Hu Hx Ii Ij Io Ip Ir Is It Jl Jm Jq Jr Jt Lu Ma
Mb Mc Md Mf Mg Mh Mi Mk Ml Mn Mp Mq Mr Mv Mw Mx Mz Nb Nk Nm Nn Nq Oe Og Oi Oy Pd Pf Po Pz Qd) On(Dk Hq Hr Hu Ii Ij Im
In Ip Ir Is Iv Jf Jg Jl Jo Jq Jt Lh Li Lj Lw Lz Ma Mb Mc Mf Mg Mi Mk Mn Mp Mq Mr Ms Mu Mv Mz Ng Nm Nn No Nr Ny Og Pb Pd Pe Qb
Qc Qw Ut) Jj(aA Dg Em Fr gP Hx Ih Ii Ij Im Io Ir Is It Jh Jt Li Lj Md Mf Mg Ml Mr Mw Mx Mz Nd Nf Ng Nk Nn No Nv Ny Og Oh Oi Om Oy
Oz Pb Pc Pf Pg Pj Pz Qb Qc Qd Rb Rf) Lx(Aa Dc Fr Gl gP Ha Hq Hu Hv Ih Il Io Is Iu Jl Jm Jq Jt Kc Lh Li Lu Lw Me Mi Mk Ml Mr Ms Mu
Mx My Mz Na Nm Nn No Nv Ny Oh Om Oy Pa Pd Pe Pz Qa Qd Ut) Dg(aC aD Af aH Aj aN Ao Ar aV aW Bc Bg bL bN bU cB cE Ch cM Co
cP Cs Ct Cv Cw Db Dd dM eF GL Ha Iq Jf Jk Jo Kj Kk Nd Nf Oe Of Om Qw Ri) gP(aA Ad AP Ar Ax Ba Bb bV cB Dc Dk Dl eM Fr Gt Gw Id
iZ Kp Kq Ky Me Mt Nd Nf Om Oy Pa Pb Pc Ph Qx Qy Rb Ri Rj Sr Uh Uk Un Vo Wm) Nc(AA Fr Hw Im Ip Iq Is Iv Jh Jn Jq Jr Jt Lj Lw Md
Mf Mg Mi Mp Mz Nb Nd Ni Nm No Ns Nv Ny Oh Oi Oz Pa Pb Pc Pd Pe Pf Pg Pz Qa) Jg(aA Bg Dc Dk Fr Gl Hv Il Io Is Jh Jl Jm Jn Jq Lh Li
Lw Mh Mi Mj Mk Mm Mp Mr Mx Na Ng Nm Nn No Nr Nv pF Po Pz Qb Qc Qd Qw Vo) aJ(aA aF aK aN aQ aV aX aZ bI bJ bX bZ cA cC cE
cF cK cP cQ cT dF dH DI Dr dX EX fR Gc gL gN GT Gw Nf Pc) Nd(Ap Ar aX Bb Bc Ih Ij Ip Ir Is Iv Jn Jt Lj Mg Mp Mv Mx Nf Nm Nq Og
Oh Pa Pd Pf Po Pz Qb Qd Rb) Me(Ar aX bN Ex fR Fy Gc Ic Kc Kf Kk Kp Kq Kr Ks Ky Ld Pj Qm Qw Rf Ri Uh Uk Ur Vp Vt) Nv(Hq Hx Ii In
Iv Jk Js Lj Mb Md Mf Ml Mv Ng Ni Nm Nq Ns Of Og Oi Oz Pc Pd Pe Qb Ut) Li(Hw Hx Ih In Iq Ir Iv Jk Js Mb Md Mf Mq Mv Mz Ng Ni Nq
Ns Nt Of Og Om Oz Pa) eF(Aw Bb Bc Bg bU Ch cJ cM Cp Dc Di dJ Dk eM eX gL gN gT Gw Hw Jk Kc Om Qw) gL(aX bC bL bN bR bU bZ
cB cE cM Ct dJ fR Jf Jk Mu Mv Nf Om Pc Qw Ut Vs) Nf(Aa aN Ap Fa Lm Ip Is Iv Kk Kq Lj Mm Nb Nr Ny Pg Pj Qa Sr Uh) Id(Dc dl Ha Ic It
Jf Jk Js Md Mj Mq Mr pF Po Qw Rb Rf Ri Rj Vo) Qw(Aa aN aX bJ bN bV Dr eM eP It Jf Kc Kq Mm Nr Pj Rf Sr Vq) Nt(Hv Ii Is Jh Jn Jq Jt Lh
Mg Mj Mk Mr Mw Nb Nm No Nr) Jf(Aa Ap Ar Bb Di Dl It Kc Kf Kk Kq Mm Nm Nr Ph Rf Sr) fR(AD aM bR bU cP Db dH Di dJ Iq Kd Oz Pb
Ra) Aa(aD aV aX iZ Jr Kc Kk Mt Og Om Pc Rb Ur Vo) Mm(Iq Ir Jr Lj Mb Md Nq Og Om Pa Pc Ur) Ad(Al Ao Ar Bg Ch Co De Di Jk Oe Om)
Ap(aD aH cE Ch Dc Di Dk Gl Mv pF Vo) Nr(Dc Ha Ib Md Mi Og Oz Ut Vp Vs Vu) Kk(bI dJ dX eP Md Mu Mv Nm Pj Ra Vp) Mt(aN Dc Io Is
Jl Jq Jt Lh Pz Wm) Im(Hw Iq Iv Lj Md Nq Ns Om Oz Pe) Kq(Dc Dk Ha Mu Mv Om pF Ut Vo Vp) Ar(Ha Ic It Ma Mr Mv Pc pF Po) Iv(Fr Hw
In Lj Mg Og Pb Pg Pz) aV(bE dM Do DV dX EM Kc) dF(aH aN bN bU cA cE cM dV eX) Lj(Dc Ha Md Mi Mz Oi Oz Pd) Pj(Ha Jo Js Oe Og
Om Ur Vo) Gw(aD aK aM aN Bc bR dL) Nl(Ii Jo Mh Mj Mk Mr Oe) Kc(bI bJ cP Iq Ra Ri Vs) Lh(Gl Iq Jo Md Of Og Oz) Pe(Ha Hw In Iq Md
Og Oz) Rb(aX Dr Ic It Pb Sr) Gt(bC Bo cF cG dR) Hw(Ih Ir Is Qa Sr) Om(Hb Kf Qa St Uh) Oz(aN bN Mi Nm No) bU(aA aP bV cR dM) Og(Ir
Jt Nm Oi) Pc(aX bN dJ Fr) dM(bL bR cJ cM) Dc(It Kf Sr) Gc(Hf Ue Vo) Md(Fr Ny Qa) Iq(aX Pg Qa) Pb(dX eM eP) cG(dO eP gT) eX(aK dL
dR) iZ(bN Ex Vq) pF(Bb Sr Uf) Ba(Ct Dk) Dl(bN Ct) Do(bC Fw) Dq(cF dL) Dv(bC cL) Em(aN Ld) Gl(Sr Uh) Ha(It Kf) Nm(Nb Ur) Qx(dX
eM) aA(bR Jr) aX(It Ou) DrRa FrNq HxJl QaQc JkKf OiUr UhVo aKgN aNbF cBcM cNdV cVeM

Unconstrained panels with 2 analytes, where 1.0E-2 >= 'AUC p-value' > 1.0E-3. Contains 7,185 panels of 77,685 total panels evaluated. : gP(Aa
aD AF Aj aK Al aM AN AO aQ As aU aV AW aX aZ bB bC bE bF Bg bH bI bJ bL bM BN BO bP bQ bR bS bU bW bX bZ cA cD cE cF cG
Ch cI cJ cK cL cM cN CO CP CQ cR CS CT CU CV CW CX cY dA Db DD DE dF dH DI dJ dK dL dN dO Dp Dq DR Ed Ef eX Ez Fa Fb Fn
Fw Fy GC Gl Gp gW Ha Hb Hc Hf Hq Hr Hx Ib Ic iH Ii Ij Ik Il Im In Ip Iq Is It Iv Iz Jd Je Jg Jh Ji Jk Jl Jm Jn Jo Jq Jr Js Jt Ju Jv Jy Kd Ke Kf
Kg Ki Kj Kl Kn Kr Ks Kx Kz Ld Lh Li Lj Lw Lz Ma Mb Md Mf Mg Mi Mj Mk Ml Mm Mp Mq Mv Mw Mx My Mz Na Nc Ne Nh
Ni Nj Nk Nq Nr Ns Nu Nv Ny Oa Oe Og Oh Oi On Or Ou Ow Oz Pd Pc Pf Pg Pi Pj Pk Po Pz Qa Qb Qc Qd Qg Qh Ql Qm Qn Qt Qu Qv Qz Ra
Rc Rf Rg Rh Rm Ss St Tn To Tr Tt Tv Tz Ua Ub Uc Ud Ue Uf Ug Ul Um Uo Up Us Ut Uu Uv Vp Vq Vs Vt Vu Vv Tj) Id(Aa AD Af aG aH aI
AJ AL AN Ao AP AR aU aV AW aX BA BB BC bE bF Bg bH bI bJ bM BN bO bQ bV bZ cC cD cE cF cG CH cI cL cM Co CP Cq cR Cs Ct
CU CV cW CX dA DB Dd DE dF Dg dH Di DK Dl dM Ed eF Ez Fa Fn Fp Fr Fy GL gW Hb Hc Hf Hq Hr Hu Hv Hw Hx Ib Ii Ij Ik Il In Io Ip Iq
Ir Is Iv Iz Jd Jg Ji Jj Jl Jm Jn Jo Jp Jq Jr Jt Jv Kc Kd Kg Ki Kj Kk Kl Kp Kq Kr Ks Kx Ky Ld Lh Li Lj Lv Lw Lx Lz Ma Mb Mc Mf Mh Mi Mk
Ml Mm Mp Mt Mu Mv Mw Mx My Mz Nb Nd Ng Ni Nj Nk Nm Nn No Nq Nr Ns Nt Nu Nv Nx Ny Oe Of Og Oh Oi Om On Or Ou Ow Oy Oz
Pa Pb Pc Pd Pe Pf Pg Ph Pi Pj Pk Pz Qa Qc Qd Qe Qg Qh Ql Qm Qt Qx Qy Ra Rc Rg Rh Rm Sr Ss St Tn To Tr Tv Tz Ua Ub Uc Ud Ue Uf Uh
Uk Ul Um Un Uo Up Ur Us Ut Uv Vp Vs Vt Vu Wm Tj) gL(AA aC AD aE AF aG aH aI aK aL aM aN AO AP aQ aR aS aU aV aW Ax aY aZ
bA BB Bc bE bF BG bH bI bJ bM Bn bO bP bQ bS bV bW bX cA cC cD cF cG Ch cI cJ cK cL cN CO CP CQ cR CS cT cU CV cW cX cY cZ
dA DB DC DD dE dF dH DI DK DL dM dN dR eM Ez FP Fr Fy Gl gW Ha Hb Hf Hq Hw Ib Ic Ii Ij Ik Il In Ip Iq It IZ Jj Jl Jo Jp Jq Jr Js Jy Kc
Kd Kf Kg Ki Kj Kk Kn Kp Kq Kr Ks Kx Ky Ld Lh Lj Lv Lx Ma Md Me Mj Mk Mm Mn Mq Mr Mw Na Nc Nd Nj Nm Nn Nq Nr Ns Nu Nv
Nx Oe Og Oh Ok Ou Oy Oz Pa Pb Pd PF Pg Pj Qc Qe Qg Ql Qn Qt Qx Qy Ra Rb Rc Rf Rg Ri Sr Ss St Tn To Tr Tt Tv Tz Ua Uf Uh Uk Um
Un Up Ur Uv Vo Vp Vq Vt Vu Wm) Dg(AA Ad aE aF aG aI aK AL aM An aO AP aQ aR AS aU Aw AX aY aZ Ba BB bC bE bF bG bH bI bJ
bM Bn BO bP bQ bR bS bV bW bX bZ cA cC cD cE cF cG cI cJ cK cL cN cO Cp CQ cR cS cT CU cV cW CX cY cZ dA dB dC dD DE dF dG dH
dI dJ dK DL dN dO Dq dV Ef eM eX Fp FR Fw Gp Gt Gw Hw Hx Ic Ii Ij Ik In It Iv iZ Jl Jp Jr Js Jt Kc Kd Kg Ko Kr Ks Lj Lv Lx Ma Mb Md
Me Mj Ml Mp Mq Mt Mu Mv Na Ni Nj Nq Nr Nu Nw Nx Og Oi Ok Or Ou Oz Pa Pb Pc pF Pg Ph Po Qd Qe Ql Qt Qx Qy Ra Rb Rc Rf Rj
Sr Uc Uk Um Up Ur Ut Uv Vp Vs Tj) cH(aC AD AF aG Aj aK Al AO Ap AR AS aU aV AX aY Ba bB Bc Bg bH bL bM Bn BO bP bQ bR bW
bZ Ch cL cN CO Cp Cq cR Cs Ct CU CV CX cY dA DB Dc dD dI Dk DL Do Dq DR eM eP eX FR GC Gl gW Ha hB HC Hf Hq Hr Hw Hx IH
iJ Ik Im In Ip Ir It Iv iZ Jf Jg Ji Jj Jk Jl Jm Jn Jp Jq Js Kc Kd Kg Ki Kk Kp kR Ky Ld Lh Lj Lw Lx Lz Ma Mb Mc Md Me Mh Mi Mj Ml Mn Mp
Mq Mr Ms Mt Mu Mv Mx Mz Na Nh Nl Nm Ns Nt nW Ny Oe Oi On Ou Oy Pd Pe pF Pg Ph Pj Po Pz Qa Qb Qe Qt Qy Ra Ri Sr Uh Uk Um Ur
Vo Vp Vt Tj) Ad(AA aC aD aE AF aG aH aI AJ aK aL aM AN aO AP aQ aR AS aU aV AW AX aY aZ Ba BB BC bE bF bG bH bI bJ bM BN
BO bP bQ bR bS bU bX bZ cA cB cC cD cE cF cG cI cJ cK cL cM cN cO cP CQ cR CS cT CU CV CW CX cZ dA DB dC DD dE dF dG dH dI
dJ dK DL dM dN DO Dq Dv EF eM eX Fp Fr Gl Gt Gw Ha Hq Hw Ic Ii In Iq It Jf Jj Jl Jo Jp Js Kc Kj Kk Ko Lx Ma Md Me Mj Mk Mr Mu Mv
Nd Nf Nr Nu Nx Of Og Ok Oy Pb Pc Pg Qt Qw Rb Ua Up Ur Ut Vo Vs Vu Tj) Ar(AA aJ Ap aV BA Bb BC bI bN bU cC Ch cM cP Dc dF dG
DI Dl dM eF Gl Hb Hc Hq Hr Hu Hv Hw Hx Ib Ii Ij Ik Il Im In Io Ip Iq Ir Is Iu Iv Jg Jh Ji Jj Jk Jl Jm Jo Jp Jr Js Jt Ju Jv Kg Kk Ko Kp Kq Ky Kz
Lh Li Lj Lu Lv Lw Lx Lz Mc Md Mf Mg Mh Mi Mj Mk Mm Mn Mp Mq Ms Mt Mu Mw Mx My Mz Nb Nc Ng Nh Ni Nj Nl Nm Nn No Nr Ns
Nt Nv Nx Ny Oe Of Og Oh Oi Om On Ou Oy Oz Pa Pb Pd Pe Pf Pg Pj Pk Qc Qd Qe Qg Qt Qw Qy Ra Rb Rg Ri Rj Sr Ss Tn Tr Tz Ue Uh
Uk Ur Ut Vo Vp Vt Vu Tj) Qw(aC Af aH aI aJ aL aM AP aU aV Ax aZ Ba BB BC bE bH bI bL Bo cE cF cI cJ cM cN cO cP CQ cR Cs cT Cu
Cv cZ dA DC Dd dE dF Di dJ DL dM dX Ef Em Ex Fa Fp Fr Ha Hb Hw Hx Ic Ij Ik Im Ip Iq Iv Jd Jh Ji Jj Jm Jn Js Jt Kd Ke Kf Ki Kk Kl Kp Ky
Lh Li Lj Lv Lx Md Mg Mj Mr Mt Mu Mv Mw Mz Nd Nf Ng Nj Nl Nm Nn No Nt Nu Nv Ny Oa Og Oh Oi Om Ou Oy Pa Pb Pc Pd Pe Pf Ph Pz
Qa Qc Qd Qe Qm Qu Qx Qy Rb Rh Ri Rj Rm St To Tr Tt Uc Uf Uh Uk Ul Uu Vo Vp Vs Vt Wm) fR(aA aE AF aG aH aK Al AN AP aQ aR aS
aU aV AW Ax aZ Ba bB BC bF BG bJ bN Bo bP bQ bS bW bX bZ cA cB cC cD cE cF cG Ch cI cJ cK cL cM cN cO cQ cR CS cT cU CV cW
cX cY Dc DD DE dF dG dJ Dk DL dM dN Dq eF eM Et eX Fp Fr Gl gN GT GW HC Hq Hr Ih Ii Ik In Is It iZ Jj Jk Jn Jo Jr Kc Kf Ky Kz Ld Lj

Figure 11 Continued bR bU bZ cA cD cE cF Ch cJ Cp cQ Ct Cw cY Db Dc Dd DE DI Dk dM gW Ha Hb Hq Hu Ic It Jk Kg Ki Ma Mk Mm Mt Mu Mv Nf Ni Nm Nu Oe Og On Ou Pb pF Po Qc Qe Qt Rf Rj Uh Uk Ur Ut Vo Vp Vq Vt Vu Tj) Fr(aA aH al bC Bg bN bU cB cC cF cT Dc DI Dk dM Gw Hq Hr Hv Hw Hx Ih Ii Ij In Iq Ir It Iu Jm Jn Jr Js Lh Li Lz Ma Mb Mc Mf Mh Ml Mm Mn Mu Mv Mw My Mz Na Nb Ni Nm Nn No Ns Nv Ny Oe Of Og Oh Oi Om On Oy Pb Pd PF Pg Pz) Lh(aA aX Bg Dc Dk Ha Hq Hr Hw Hx Ii Ij Il In Ir Is Iu Iv Jh Jk Jl Jr Js Jt Li Lw Lz Mb Mc Mf Mg Mh Mi Mk Mm Mn Mp Mq Ms Mv Mx Mz Na Nh Nc Nm Nn No Nq Ns Nu Nv Ny Oe Oh Oi Om Oy Pb Pc Pd Pf Pg Qc Qe Qx Ut Vo Vp Vs Vu) Nv(Bg Dc Dk eM Gl Ha Hr Hu Hv Ih Ij Il Io Ip Ir Is It Iu Jh Ji Jl Jm Jn Jo Jq Jr Jt Kq Li Lu Lw Lz Ma Mc Mg Mh Mi Mj Mk Mm Mn Mp Mq Mr Ms Mu Mw Mx My Mz Na Nb Nk Nn No Ny Oe Oh On Oy Pa Pb Pf Pg Po Pz Qc Qd Vp Vu) Mm(aA bN Gl Ha Hq Hr Hu Hw Hx Ih In Ip Is It Iu Iv Jh Jk Jm Jn Js Kd Kj Li Lu Lz Ma Mc Mf Mg Mh Mi Ml Mn Mp Mq Ms Mu Mv Mw Mz Nb Ng Ni Nk Nn Ns Ny Of Oh Oi On Oy Pd Pf Pg Pz Qb Qc Qd Qx Ri Uk Up Vo Vs) Nf(aA aP aV AX aZ Ba Bb Bc bJ bN Bo bV Co Cs Cu Cv Dd Di dJ DL dM Ex Hb Hv IH Ii Ij Ir It iZ Jl Jm Jt Ke Kf Ky Mb Mg Mi Mr Mz,Nc Nm Nn Oa Oh Oz Pa Pc Pd Pf Po Pz Qd Rf Ri St To Uf Vq Vt) Li(aA Bg Ch Dc Ha Hq Hr Hu Hv Ii Ij Il Io Ip Is It Iu Jh Jl Jm Jn Jo Jq Jr Jt Lu Lw Lz Ma Mc Mg Mh Mi Mj Mk Ml Mn Mp Mr Ms Mu Mv Mw Mx My Na Nb Nk Nm Nn No Ny Oe Oh Oy Pb Pc Pd pF Pg Po Qb Qc Qd Ut) iZ(aA aE aH aL aY aZ Bb Bc bJ bL bO bQ bR bU bX bZ cE cJ cM cQ Cv cW dE Di DK dL dN eC Gz Hb hC Hw Hx Il Jr Ki kR Md Mj Mk Mu Nk Nm Nu nW nY Ou Oy Pa Pc pF Qc Ri Ue Ur Ut Vp Vs Vt Vu tF) Pc(aA aD aH al aL aN aP aV Ax aZ Bb BC bE bJ bL bM bU bV cB cF cJ cM cN cP cQ cR Cs CT dA DD dE Di DL dM eM Ir Iv Jh Jn Jr Kq Lv Mg Mi Mz Nm No Ny Oa Og Oh Oi Pg Qt) Nm(aA aN Ch Dd Ez Ha Hq Hr Hv Hx Ic Ih In Ir It Iv Jh Jl Jr Kd Kj Lw Mc Md Mf Mi Ml Mp Mu Mv Mz Ng Nn No Ns Ny Oe Oh Pb Pd Pf Pg Pz Qx Ra Rc Rf Ri Rj St Uk Um Ut Uv Vo) Nu(aE aH aN aV AX aZ Bb Bc bG bI bJ bN Bo bP bR bV cA cB cF Ch cJ cM cQ Cs cT Cv Dc Dd dJ DI Dr dX eP Ex Gz Ii Ip Iq It Jr Jt Kd Kq Mb Mf Mj Mq Mr Oi pF Rf Uh Vp Wm) Iv(aA aX Hr Ih Il Ip Iq Ir Jh Jk Jl Jm Jn Jo Jr Js Jt Lu Lw Lz Ma Mb Mc Md Mf Mh Mi Mj Ml Mn Mp Ms Mu Mv Mw Mx Mz Nb Ni Nk Nn No Nq Ns Ny Of Oh Oy Oz Pa Pd Pf Qb Qd) On(aA Ao aX Bg Ch Co Ct Dc Ef Gl Ha Hv Ib Ic Ih Io It Iu Iz Jh Jm Jn Jr Kg Kj Lu Mh Mw Mx My Nb Ni Nk Oh Oi Pa Pf Pg Po Pz Qd Qt Rj Tn Ua Ur Vo Vp Vs Vt Vu Wm Tj) aX(aA Ba Bb Bc bU cT Dl dM Dr dV eM Gt Gw Ha Hc Ik Jg Kd Kn Kp Kq Kz Ld Lx Mb Md Mg Mt Mz Nc Ne Nh Nj Nk Oh Oi Oz Pa Pb Ph Qe Qx Qy Ri Rj St Uk Ur Vo Vp Vq Vs) bN(aA aP Ba Bb BC bV cB Ct Db dE Di dM FP Gl Ic IH Ik It Jg Kf Ki Kp Ky Lv Lx Ml Mt Ne Nh Nl Oe Om Or Ou Oy Pa Pb Qe Qx Qy Ra Ri St Uk Ur Vo Vt Wm) DI(aA aC Af aH Aj aN Ao aV aZ Bb BC Bg bl bL bU bX cB cD Ch cM cP cQ Cv Cw Db Dc Dd Di Dk dM eM eX Gl Gw Ha Iq Jk Kd Kj Nj Oe Om Qt Ra Ri Ur Ut Vo Vs) Nc(Hq Hr Hu Hv Hx Ih Ii Ij Il In Io Ir It Iu Jk Jl Jm Jo Js Lu Lz Ma Mb Mc Mh Mj Mk Ml Mn Mq Mr Ms Mu Mv Mw Mx My Na Ng Nn Nq Oe Of Om Oy Po Qb Qc Qd) Qe(aA aH al Al aV Bb Bg cM Ct Cu Dd Di dJ Dk Hv Ic Ih Io Is Jh Jn Jq Jt Kg Kj Lu Lw Ma Mk Mr Mu Na No Oe pF Qh Ra Ri Uk Up Ur Ut Vo Vp Vs Vu Wm Tj) Kq(al Ao bF Bg cE Ch Co De DI Gl Gn Hq Hw Ib Ic Ij In Iq Jk Jl Jr Js Kd Kg Ma Md Mj Mk Mq Mr Mw Ny Oe Of Oy Pg Po Qd Qt Qx Ra Rj Tn Ua Vs Vu Tj) dJ(aA aP Bb Bc bE bU bV cB cT dM dN Dq Dr eM eP eX GC Gt Gw Hw Ik In Iq It Jg Kd Lv Lx Mt Mu Mv Nj Oe Og Om Oy Oz Pa Pb Ph Qx Qy Rj Ur Vs Wm) Lx(aH al aN aO aV Bb Bc Bg bl bJ bL Bn bZ cE Ch cM Cp cQ Ct Cw Dd De DI Dk Fb Ib Ic Ky Ou pF Qg Qt Ri Ua Uh Uk Vo Vp Vq Vs Vt Vu Wm Tj) Oz(aA al aP aZ bJ bV dM dX eP Ex Hv Ih Ii Ij Il Ip Ir Is It Jh Jl Jm Jn Jq Jr Jt Lw Md Mf Mg Mp Mr Mw Mx Mz Nb Nn Ny Oh Oi Pg Po Pz Qb Qd) Lv(aA aH al aN aV aZ bC bH bl bJ bR bV cF cK cQ cZ Dd dl dM Hq Hw In Iq Iu Jh Jk Jo Lw Lz Mj Ms Mu My Na Ng Ni Ns Of Om Pb pF Qb Qc Wm) Uh(al Bg Ch Dc Di Dk Ha hC Hq Hw Ii In Iq Jk Jo Js Kg Kj Ma Md Mj Mk Mr Mu Mv Oe Of Og Ou Pb pF Pg Qx Ra Rf Rj Up Ur Ut Vp Vs Vu Tj) Bb(aD Ao aP aV Ba BC Bg bl bU Ch cM Co cP cR Dc Dd De Di Dk dM Gl Ic Iq It Jk Ma Mt Mu Mv Nj Oe Og Om Qx Ra Rj Ur Ut Vo Vu Tj) Bc(aA aH al aL aN As aV aZ bB bC bE Bg bl bJ bU bX cB cC cE Ch cK cM cP cR Cs Ct Dc Dd Di Dk dM Dq eX Gl gW Ic Iq Nj Ut Vs Vu) bU(aD aK aM aN aQ aV aW Ax aZ Ba bC bE bF bH bI cB cG cJ cN cP CT cY dA Dc dE Di dL dO Dq dV eM Fp Gt Gw Iq It) dM(aD aH aK aM aQ aZ bC bF bl bM bV bW bX bZ cA cB cC cD cE cF cK cP cQ cT cY dE DI dO dV hC Jg Jk Mt Nj pF Vs) Rf(aV cM Ct Dc Dk dX eM eP Gl Ha Ic In It Jk Jl Jr Js Ma Mj Mq Mr Mu Mv Oe Of Pb Po Qx Qy Ri Rj Uk Ur Vo Vq Vs) Ir(Hq Hr Hx In Ip Iq Jh Jk Jl Jt Lz Mc Md Mf Mg Mh Ml Mx Mz Nb Ng Ni No Nq Of Oi Pb Pd Pg Pz Qb Qc) Kf(Bg Ch Ct Dd Dk dX eM Gl Hq Hw Ic Jl Jo Jr Js Kg Md Mj Mk Mu Mv Oe Og Pg Qt Rc Ri Ur Ut Vo Vp Vs Vu) Vq(aV Bg Ct De Ef Et Gl Hu Ic iH Jk Jn Jo Kj kS Ky Mq Mv Nl OE Og Om Or Oy pF Qt Ra Rc Ri Uk Vo Vs) Gw(al Al An aQ aU bB Bg bL BO cA cB cF cG Ch cI cM cN cP Cq Cs CV cY Db Dc dD dl Dq dR Gp Gt) It(aD aH Al aN cJ cM cN Ct Dd DI Gl Ib Il Kd Mi Og Qg Qt Qx Ra Ri Rj Uk Um Up Ur Vo Vp Vs Vt Vu) Jg(aH Ij Ao aZ bL cE Ch Co cQ Ct Cw Dd DI Ef Ha Ic Iz Jv Kj Qt Qx Ra Rc Rj Ua Ur Ut Uu Vp Vu Wm) Nj(al aV bC bE bJ bL bV cM cP Dc dl eM Hq Hr Hu Hv Hx Jk Lz Mb Mc Mh Ml Ms Mv Na Ng Oe Om Qc) Iq(aN aV Ax aZ bC bE bJ bR bV cB cF cJ cM dL Ih Ij Ip Is Jl Jt Mi Mp Nb No Oh Pa Pz Qd St Vt) Mt(aH al Al As aV aZ Bg bJ bR cF Ch cM Ct Cv Dd DI Dk Gl Ha Ib Qt Qx Ra Ri Ut Vp Vs Vt Vu) Pb(al aN aV bC bI bJ bL bV Ct Hv Ij Jh Jl Jr Jt Md Mg Mp Mw Mz Nb Nn No Ny Oh Pg Pz Qd) aA(aH aM aV aZ bC bJ bL bM bW cB cF cJ cM dE DI dL Hw Hx Jn Md Mf Ns Og Oi Om Pa Vt) eM(aD Af aM AN bR cB cC cE cF cN Cs cY Dd dL Fa Hu Ib Jy Kz Ld Ns Oa Or Qy Qz Ra Uk) Et(bG cR cT dC dK dR eC fP gW hB hC hF hG iA iH iO iP kQ kR kS nW nY oF oH oK oN tF) St(Dc Di Dk Fw Gl Ha Hw Hx Ic In Jk Jr Mj Mk Mr Mu Mv Oe Of Pg Qb Ut Vo Vp Vs Vu Tj) aN(Af Al aM aP Ba bR cF cG CO cQ cR Cu Di DO Dq Dr dX eX Gc Ih Up Wm) Ji(Dc Dk Gl Ha Ih Io Ip Jm Jn Mg Mk Ml Mr Mu Mw My Ni Oe Qb Qc Vo) Og(bJ Ih Ij Ip Jh Jm Jn Jr Mb Mg Nk No Oh Pa Pd Pf Pg Pz Qb Qd Vt) dO(aD aK aM aP bC bE bF bI bR cE cF cR cS cV dl dK dL dR Fw gN Gt) Ba(aH Ao As aW bC bF Bg bL cE Ch cM Co Cv Dc Di Gl Jk Mu Mv Om) Pg(Hw Ih In Ip Jh Jr Mb Md Mf Mg Ml Mz Nb Ni Nq Of Oh Oi Om Pz) cB(aD aH aM aP aV bV cP cQ dA dE Di cl dL Dq dV dX Em eP eX GT) cM(aP bC bE bV cC cF cN cT dA Di dL Gl iH Ik Ou Ph Qx Ur Vs) Fp(al bl cF Ch cP cQ Cs Dd dl Hu Ic Lu pF Qy Ri Ur Vp) aV(aP bC bV cC cF cN cT cU dA Di dN Gl Kp Oi Om Qx Rj) Mz(Hr Hv Hx Ih Lz Md Mf Mg Mi Ml Mw Ny Oi Pd Pf Pz) Hw(bJ Fa Jh Jl Jn Jr Mf Mg Mx Nb No Ny Oh Ph Qd Ri) dV(al aK aM aP aQ bF Bo bQ bR cE cF cS cY dR Fw) Dr(aK aQ cF cL cY dL Fw Hf Hu Jy Ld Nl Or Qx Ue) Ic(al Ax Di Gl Jm Mk Oi Om Ph Qc Ri Ut Vo Vs Vt) Dc(bC Bg Cu Cv Fy Jm Jt Kp Oa Oi Pz Qh Tt Uf) No(Ha Hq Hx Kd Lz Mb Md Mf Mh Mi Nb Nq Ny Vp) Ur(al bC bE Di Em Gl Jm Jt Ki Tr Tt Ug Uu Vt) dL(bR cF cQ cT Di Do dX Em eP GC gN GT) Hv(Hq Il Lw Lz Mc Md Mg Mh Mi Ml Mu Oe Vp) Pa(bJ Gl Ih Jr Mb Mf Mg Nq Oi Ri Vs Vu) eX(aM aQ aU Bg bR cE cF cG cN cV cY Dd) Nb(Hq Hr Hx Jh Jl Md Mg Mi Mp Oe Of) Vo(dC Em Ex Gz Hb Jt Ke Kl Kp Oi Pz) cT(aM aP bC bl cC cF cQ cR dE dl Gt) Dq(aK aM aQ Bo cE cG cN cY Dd dR) Ha(Ax Ex Ih Jm Jt Oa Oi Qd Vt) Ik(aL bE Bg Ch Ct Dl Dk Gl) Ny(Hq Hu Lu Lw Lz Mc Mf Mq Pd) bC(aP Bg Ch cQ Db Dd Di Gl Qx) eP(aK aM cC cY dR Fw Hf Kz Ld) Vs(iH Kp Oi Ou Oy Ph Qx Tt) pF(Ax bE Cv Jr Nk Pz Ql Vt) Gt(aK aQ cN cV cY DD) Ne(Em Ii Jo Mj Mk Mr Ms) Jk(Co Iz Ph Qy Tn Tt Ua) cG(aW bZ cA cE cO Do Dv) dX(aD cL Ib Ih Kp Ph Qy) gT(aK aM Bo cE cY dR Fw) Ri(dE Ex gW Jn Ky Wm) Oi(aH bL cQ Ip Kj Oe) Om(bJ cQ dC Kl Md Tt) Vt(bJ Kp Mr Mu Qy Rj) Pd(Hr Jh Md Mf Oh Pz) Di(bF cP Cu Cv Kd) Dv(aK cF cY dR Fw) Em(Dd Hf Kd Kj Ue) Gc(cL Hu Kj Or Rc) Mb(Ip Is Jt Mi Mx) Hx(Ih Mx Nn Oh Ph) aP(aQ bR cE cJ cK) cC(aZ bV cN Db dE) Do(aK cF cY dR) Mf(Is Jn Mi Pf) Mg(Ih Md Of Oh) Qx(bL cJ Mv Qt) Jl(Hr Nq Oe Oy) Jt(Jr Kd Md Of) Ou(bE bJ Hb Mr) gN(aM cY dR Fw) Ch(Bg Cp Iz) Gl(cP Ke Kp) Mi(Jn Nq Pz) Jm(Al Ct Vu) Oa(dl Mr Mu) Uk(aZ Ex Jn) Pf(Ip Ni Pz) bl(Ax Bo Cv) bR(aM cR dE) Cu(aH Dk) Ih(In Oe) Jh(Md Nq) Vu(bJ Kn) Ph(Mv Qt) aK(aU gC) CtOy CvDd WmbJ ExUp FwgC Gnlu MuUf MxOe Nklp ljOf Inls PzOh KeUt aMbF cJcR

Figure 11 Continued

Constrained panels with 3 analytes, where 1.0E-9 >= 'AUC p-value' > 0. Contains 3,266 panels of 9,935,646 total panels evaluated. : Gn{Rc(aD aJ Al aM Ar aV AX aZ Bb Bc bR bU cF cH cI cN cP Cs Cv Cx dJ Dk DL Et Ex Fa Fp Fw Hu Id Ih It Ji Jj Jm Jn Jp Jq Kf Kk Kn Ko Kp Kq Ky Ld Lh Lj Ly Ma Me Mf Mm Mz Nb Ne Nj Nm Nr Nv Nw Nx Oa Oe Og Oh Ok On Or Ou Ow Pe Qa Qb Qe Qn Qw Qx Qz Ra Rb Rm Sr St To Tr Um Uo Up Ur Vv) Vo(aC AD Af aJ Al aM aV aX bE bR bU cH cI cN cO Cu Cv Cx DG Di dJ DL Em Et Ex Fa Fw Gz Hf Hq Hu Id Ih Ip Is It Ji Jl Jm Jn Jo Jp Jq Kc Kf Kk Kn Ko Kp Kq Ky Ld Lh Ly Me Mf Mh Mm Mu Mz Nj Nv Nw Nx Oa Oe Og Oh Oi Ok On Ou Oy Pb Pc Pg Ph Pz Qa Qb Qd Qw Qx Qz Ra Rb Rm Tr Ug Vv) Kc(Aa aD Af aG AJ AO Ap aV Aw Ba bF bL bN bP cH Co Cu Cw De Dg dJ Dk DL Ed Ef Et Ez Fb Fy Gc Gl Hb Ij Ik Im Is Jd Jg Jk Js Jt Jv Ke Kf Kg Kl Kn Kp Ks Lu Me Mg Mn Mt Mu Ng Nk Nm Nn Ny Oe Of Oi Ok Pj Pz Qv Ra Rb Rh Ss Uc Uf Uh Ul Um Un Uo Uu Vq Vs Vt Wm) Qw(Aa AD aJ Ao Ap aR aV Ba Bb bL bP cF CH Co Cp Cu Dc Dg DL Dp Ef Ez Fb Fy Gl Hb Ib Ii Ij Im Ir Is Iz Jd Je Jg Ji Jo Js Jt Jv Ke Kf Kg Kj Kl Kn Kq Ks Lu Mg Mr Mw Ng Nk Nm Ny Og Om Or Oy Pj Pz Qt Qu Qy Rb Ss Ue Uf Uh Uk Ul Um Un Uo Uu Vq Vt) aD(aJ aK aQ aV Ax bA bR bU cB cF CH cM Cs cY Di dJ dL Dq Ez Fw Gl Gw Hf Hu Ih Ij Iz Jh Jj Js Jt Jy Kc Kf Kj Kk Ld Lu Ly Me Mw Mz Nj Nm Nu Ny Oa Oi Or Ou Pi Qb Qg Qu Qv Qx Qz Rb Rm St Ue Uf Ug Uk Un Wm) Me(Aa aG aJ Ao aV aX Ba Bb bF Bg cD CH cN Cp Cw dJ Dl Ef Fb Gl gP Hb li Ij Im Iz Jg Jh Jj Jk Jt Ju Jv Ke Kf Kl Kn Ks Ld Lu Mu Mv Mw Nd Of Og Oi Om Oy Oz Pc Pd Qu Ra Ss Tz Uc Uf Ul Um Un Uo) Kf(Aa aJ Al Ar AX cH cN Cs dG Di dJ dL Ex Fa Fp Fw gL gW Hf Hu Ih Ii It Ji Jm Jp Kk Kl Ko Kq Ky Ld Lh Lj Ly Mf Nj Nm Nv Nw Nx Oa Oe Og Oh Ok Om On Or Pe Qa Qb Qd Qx Ra Rb Rf Rm Sr To Uu) Om(aJ Al aV AX Bn bR cH cl cN cP Cs Cx dG dJ dL Em Ex Fa Fp Fw Hf Hu Ih Jl Jm Jn Kk Ko Kp Ky Ld Lh Lj Ly Mf Mm Mn Mz Nj Nr Nv Nw Nx Oa Og Oh Ok Or Ou Pe Qa Qb Qg Qx Qz Rb Rm Sr St Tr) Um(aJ AX bP bR cF CH cl cN Cs dI dJ dL Dp Ef Em Ex Fb Fp Fw Gl gW Hf Hu Ib Ih In Jj Jn Kj Kk Ld Ly Mf Mu Mv Mz Nf Nj Nw Nx Oa Og Or Qa Qu Qx Qy Qz Ra Rb St Ub Ue Uf Uk Vp) cN(aK aQ aV bR bU CH cY dD dI dJ dO Dp Ef Ez Fb Hu Ib Ic Ii Ij Iz Jj Jk Jo Js Jt Ke Kj Kl Mg Mu Mv Mw Ng Nm Ny Og Or Oy Pd Qt Qv Qy Rb Uc Ue Uf Ul Un Uu Vs Vt) Uo(Aa aJ aQ aV Ax aZ bC Bg bM Bn bP cF CH cl Cx cY Di dJ dL Dp Ed Em Fb Fw Gl Hf Hu Hv Ih Jy Kj Kk Kx Kz Ld Mu Nj Oa Or Oy Pi Qx Ra Rb St Ub Ue Uf Uk Un Vp) Ly(Aa Ad aG Ao aV bL bP bX cF cH Cp Cu dC dJ Dl Et Fb Fr gP Hb Hu Ij Ir Iz Jg Js Jt Ju Ke Kj Kl Kn Kq Ks Li Mt Mu Mw Nn Oa Of Pc Pj Qn Ra Uf Uh Ul Un Uu Vt) cP(aJ Ao Ap aR aX Bb CH Co Cs Ct dE DK Ef fR Fy Gl Gw Hu Ib Ij Ik In Iz Jd Jg Jh Ke Kg Kj Kl Ma Mb Mu Mv Mw My Nk Or Oy Qt Qu Qy Rh Uc Ue Uf Uh) Kk(Aa Ad aG Ao aQ aV Ba Cu cY dJ DL Ed Ef Ez Fb Gl Hb Hu Ii Ij Im Iz Jd Jg Jh Jt Kc Kj Kl Kn Ks Li Ma Nm Ny Of Pj Qu Ra Rh Ss Ue Uf Ul Un Uu) aV(aC aJ aK aP aQ aU aX CH cO Cs cY dG Di dJ dK dL dM DO dR Fb Fp fR Fw Gl gW Hu Ic In Io Jj Mb Mk Nu Og Or Qt Qx Qz Ra To Ue Uk Uu Wm) Nx(Aa Ao Ba Co Cp Cw Dl Et Ez Fb Gl Hb Ib Ii Ij Im Iz Jd Jk Jo Js Jt Ju Jv Ke Kg Kj Kl Kn Ks Lu Ng Nm Ny Of Oy Pj Qu Tz Ue Uf Ul Un Ut Uu) aa(aN bC bR bU cF Cs Di dJ Dl Fp Fw Gw Hu Ih It Ji Jm Jp Ko Ky Ld Lj Mf Mz Nj Nw Og Oh Oi Ok On Ou Ph Pj Qb Qx Ra Rb Rf Rm Sr St) cl·(aM Bb CH cl cM Cw DI dJ dL Ef Em Ez Gl Hu Ib Ij In Iz Jh Jj Ju Kj Mu Mv Ny Og Or Oy Qg Qt Qu Qv Ra Rb Ue Uf Ut Uu Wm) Rb(aG aJ Ao aX bE cH cJ cO dE dG dK dL Fb Hu Iz Js Ju Jv Kj Kn Ky Mu Na Nk Og Oy Oz Pc Qx Ra Ue Uf Uk Ul Un Uu) Ra(aJ Ao aQ aY aZ bP CH cl Ed Fw Hu Ih Js Jt Ke Kj Kl Kn Ld Lu Or Qu Rg St Tr Ue Uf Uh Un Uu Vt) bR(aG aJ aN aX Bb CH cL Cw dE dG dJ dL Ef Gl Hv Ib Ij Jy Ke Kj Kl Kn Lu Mf Or Qu Ue Uf Ul Uu Wm) Fw(aG Ao Ba bL CH dJ DI Ef eP Ez Gl Hb li Ij Im Iz Jj Jt Ju Jv Kc Kj Kl Kn Ny Ue Uf Ul Uu) dJ(aJ aN aX bC cL dG dl dL Do Ez Ib In Kj Ld Lu Mf Mn Nj Ny Oa Og Or Qn Qt Qu Ue Uf Uu Wm) cH(aN aQ As bU dI Ez Ih Ih Jy Ke Kn Ld Nj Nk Nl Ny Og Or Pc Ph Qt Qu Qz Ue Uf Uk Ul Wm) aX(aK aQ bU cY dD dI dL dO Dp Ef Ez Ic Iz Jj Jy Ke Kj Lu Mf Nm Ny Og Qv Ue Uf Uu Wm) Ny(aJ aP cO dG dL Fa Fp gW Hu Ip It Ky Ld Mf Nj Nw Oa Og Ok Qa Qb Qe Qx Rm St) Uf(aJ cO cR Cs dG dL Ex Fa Fp It Ji Jp Kd Ko Mf Nb Nj Oe Og Oh Ok On Ou Qe Rf) Ib(aJ Ax aZ cI cO Cs dE dG dL Ex Hc Hu Jn Kd Ky Ld Lj Oa Oh Ou Qx Sr Vv) Qt(aJ aP cl cM cO Cs dF dG dL gP Hq Jn Kd Mf Mu Oh Ou Oy Oz Pa Pc Vv) Ez(aJ cO gW Ih It Jn Kp Ky Ld Mf Nj Oa Ok On Ou Pc Ph Qx St Vv) dL(bU Ch cM dl Ef Fb gP Jk Jt Ke Kl Ld Mv Nq Qu Qz Ue Uh Un Wm) Kn(aJ Ax Ch Cs Ex Fa Hu Ld Lj Mz Nw Oa Og Ok On Ou Qb Qz St) Ul(Ax bU Ch Cs Di Ef Ex Fp Hu Ld Lj Mz Nj Nw Oa Oe Qu Qx To) Ke(aJ cR Cs Ex Fa Fp It Jp Ko Lj Mb Nb Nw Oe Oh On Qx Sr) Mf(Ch Ef Fb Gl Hb Ij Im Jj Jv Kj Ks Ma Mn Mw Qu Ue Un) Nj(Ao Ch Ef Gl Ij Iz Jj Jt Jv Kj Kl Mv Ng Of Og Ut Uu) aJ(aK aR bU Ch cM dA dI Ef Fb gP Hu Mv Mw Qu Un Wm) Og(Em Fb Gl gP Hu Jj Kj Ld Or Oz Pc Qx Rg Ue Un) Ou(Ch Co Ef Fb Fy Gl Hu In Jj Ma Mb Mn Or Qu Ue) Qu(bU Ex gL Hc Jn Kd Nb Oa On Oy Pc Tn Vv) Jt(Cs Ex Fa Fp Ih It Ko Oe Ok On Qx Rf Rm) Ue(aC aM Hu Ih Ld Mu Nb Nw On Qx Rm Vv) bU(Ao Bb Ch Ct dE Ef Gl Jj Kj Kl Or Uu) Ld(Af aG Bb Ch Ij Iz Ju Jv Or Qz Uu) Wm(aC aN bE cA cT dE dG Hu Mu Na) Ch(aQ bC cM cY dG Nd Oy Oz Pc) Nb(Bb Ef Gl Hu Jd Jh Kj Mu Oy) lt(Ef Ij In Iz Jo Kj Kl Of Uu) Qx(Ao Ed Iz Kj Lu Ng Nm Ss Uu) Ko(Cw Ef Hb Iz Kj Kl Ks Nm Uu) Hu(aG aW Hb Hv Lu Nd Ow Qz) aN(aM Ax Bb Cs dD dO Gw Qv) Gl(bA dD Kp Ky Oy Oz Pc) Ih(li Ij In Jo Kj Uc Uu) Oe(Cw Ef Fb Iz Kj Oi Uu) Cs(aK cU Fb gP Li Ma) Ex(Iz Jd Kl Ks Uh Un) Jj(Bb dE Ky Mu Nl Pc) On(Iz Kj Kl Ks Uu) Ef(aK Bc cY Oh) Mu(Hv Kd My Qz) Do(aK cA Tj) Mv(cI Hv Jy) Qz(aZ bP cE) Kl(Oh Oy Vv) Rm(Ii In Nm) Uk(cI Gp Hv) aM(Mr Qv Un) cM(dE dG Dp) gW(aQ cY dR) Fa(Iz Nm) Fb(Lj Rf) Fp(Ij Li) St(Ij Mn) Kj(dE Vv) Or(dI gP) Oy(Oz Pc) dG(aO dA) dO(cL dN) AfBn ApOk BabA DdGw EmUu GpGz MaVv MrKd HbNw IzPb LiLj aUcY cWgP dEdI} Et{Jo(Fp lh Ik Iv Jg Ji Jr Kk Lv Lx Ly Mb Md Mf Mt Nc Nd Ne Nh Nj Nl Ns Nt Nu Ok Om On Oz Pa Pb) Ly(Ao Bg bN Ch Ct Dc Dk Ih Iu Jj Js Jt Lj Lx Md Mt Nc Nd Ne Nf Nj Nl Ns Of Og Om Pa Ut) Nd(Dk Iu Jj Js Jt Lj Lx Md Mt Nc Ne Nf Nj Nl Ns Of Og Pa) Om(Dc Dk Gl Ik Jg Jj Jr Lv Lx Md Mt Nc Ne Nh Nj Nl Nt Pa) Nf(Ao Dk Ik Jg Jj Jr Kk Lv Lx Mt Nh Nt Of Ok On Pa Vo) Nl(aA Hw In Iq Iu Jj Js Jt Md Mi Nk Ns Of Og Ok Pa) Md(Ik Jj Jr Jt Lv Lx Mt Nc Ne Nh Nj Of Oz Pa) Nj(Iu Jj Js Jt Lx Mi Mr Mt Nt Of Og Ok Pa) Ne(Hw Iq Iu Jj Js Jt Ns Of Og Pa) Mt(Hw li Jj Jk Js Jt Nq Ns Of) Nc(Hw Iq Iu Jj Js Jt Ns Of Pa) Oz(Jj Js Jt Lv Lx Nq Ns Nt Of) Pa(Dk Ik Jj Jt Nh Nq Of) Lx(Jj Js Jt Nq Po) Ik(lu Jj Jt Of Og) Dk(Jf Pb Vo) Gl(Jf Pb Ur) Ut(Jf Kk Pb) Em(Kj Vo) Nq(Jg Jj) Nt(Jj Jt) Jr(iZ Jt) aX(eM cP) LvOg NhOf HxiZ KneP} Ok{Nf(Fp Hq Hw Ik Im Iq Iv Jo Js Jt Lx Ly Md Mi Mq Mr Mt Nc Nd Ne Nh Nj Nl Nw Of Om On Oz Pa Pb) Jo(Hw Hx Ik Iq Js Lv Ly Md Mf Mt Nc Nd Ne Nh Nj Nl Nq Ns Nt Om Oz Pa) Ly(Dk Hq Hw Iu Jj Js Jt Lx Md Mt Nc Ne Nl Of Og Om Pa) Nl(Hq Hw In Iq Iu Jj Jk Js Jt Lx Md Nd Of Og Om Pa) Md(Hw Ik Jj Js Jt Lx Nd Nc Nh Nj Nw Og Om Pa) Js(Hw Ik Iq Lx Mt Nc Nd Ne Nh Nj Nq Om Pa) Nj(Hq Hw Iu Jj Jt Lx Of Og Om) dX(cN Hb Jj Kn Kq Ma Rc Sr Ut) Nd(Hq Hw Lx Mt Nc Of Og Pa) Jt(Em Ik Jg Lx Mt Nc Nt Pa) Em(li Kg Kj Vo) Hw(Mt Nc Ne Nh) eP(aX Kn Qt) Ne(Hq Jj) Ik(Of Og) Iq(Nc Og) Om(Hq Mt) eM(aX Qu) PoLx GclbJ eP{Hu(aJ Ex Fp Hc Ik Kf Kk Ko Kp Kr Kz Ly Mf Nb Nu Nx Oa Or Ou Pb Pj Ql Qm Qy Ra Rb Rf Sr St To Uk Wm) Ib(Ad Ba dB Dg Di dJ Dl Ef Hw Ih It Kf Kg Mg Ng Nn Oe Oi On Pj Rm Vv) aX(aK aQ aV cY dR lh It Iv Jy Kn Mf Nl Nu Nx Ou Qz Rf) aV(aJ aP aQ aU bE cN cY dF dG dK eF fR gW) Qy(cF cL dJ Dp Jy Kz Ly Nx Qw Rc Uf) cF(Fp Jj Jy Ko Ly Nb Oa Pb Rf) cL(bR dI dJ Ly Qw) Rc(Ad Ap Dg) Ko(Fb Un Vt) gP(Ly Oz Pb) Nb(Jy Qw) Ih(li Og) Rf(cC Uf) Nx(Un Vt) bE(Ou Wm) cN(aK cY) eF(Jy Kn) LycH NjOg HcdJ RbdK} Ly{Nw(Hq Hw Iu Jj Jo Js Md Mt Nc Ne Nf Nj Nl Of Og Om Pa) Jj(aX aZ bN dE gP Jg Lx Mm Mt Nc Nl Nt Pa) Dr(aX bV cN gP Ib Kf Mv Nj Nk Qu Rc Uf) Lx(Hw Jg Jp Js Lv Md Nc Ne Nl Og Po) Jp(Js Md Mi Mt Nf Nj Nl Og Pa) Jg(Dc Jo Md Ne Nl Of Og Pa) bN(aX Db dE Jk Js Na Oz Pc) Dc(Ad cH Fp It Pb Qe) eM(aC aX bE cL gP Nk) Nl(Aa Ji Mi Mm Pa) Og(Aa Ji Mt Nt On) Jk(aZ bA cH Dg) Em(Tr Uu Vp) Md(Mt Nv On) gP(aJ hV fR) Js(aX Ko) On(Jo Oy) cH(Nd Pb) AaaX GcJt MmPa MtHw NadJ Nfld aAdX} Nw{Md(Fp Hw Ik Iq Iv Jg Js Lv Lz Mt Nc Nd Ne Nh Nj Nl Nt Nx Og Om Oz Pa) Nl(Hw In Iu Jj Jk Jr Js Ml Nd Nf Nk Ns Of Og Om Pa Po) Nf(Fp Hw Ik Jg Js Lx Mr Nc Nd Ne Nj Nl Nt Om Oz Pa) Nj(Hw In lu Jj Js Lx Mi Mm Mt Nd Of Og Om Pa) Nd(Hw Js Mi Ml Mt Nc Ns Og Pa) Js(Ik Iq Mt Nc Ne Nt

Figure 11 Continued

Om) Ik(Hw Jo Of Og Om) Nc(Hw Iq Ns Om) Om(Jg Mt Ne) Nt(Jo Og) Hw(Mt Ne) ExVo aXeM} Dr{Kc(aG Ao Ap bR Co Cu Cv dJ Dk Ed Ez Fr Fy Hb Hv Ij Im Jd Jh Jy Kp Me Mu Nk Nl Pz Qt Qu Rc Ss Uf Uo) Me(aN aV bR cF dJ Fb Iz Ju Jv Jy Ke Kf Kl Kn Nd Nj Nl Oy Oz Pc Ra Rc) Gw(aD aM aV bC cL cP Dc Dd) Nx(aV Gl Ib Ke Qu Rc Uf) Rb(bE bl cR dE dM Nk) Ra(Ih Kn Ld Mz Ph St) aV(aC aQ aU aX bE cN) Qw(Dc Or Rc) Ko(Hu Rc Uf) On(Ib Qu Uf) Ih(aX In) HucP QtVv} eM{aX(aK aQ cY Dp Ed Ih Ir Is It Iv Ji Jy Kc Kk Kn Ko Ld Mf Ne Nj Nl Nx Oa Oi Ou Pb Ph Qb Qw Qz Rb Rf Rm St) Hu(Fa Fp Gz Ib Jf Kf Kk Ko Kz Ld Oa Ql Qn Qw Qx Rf To Ub Ue Uk Vs) Ib(aC dB Hf Ih It Jl Jn Kf Nx Oi On Ql) aC(Dp Oa Qw Ue Ur) Ko(Fb Qu Uf Uk) bE(Jy Ou Qw Rf) gP(Kk Or Qw Qx) cL(bR Dv Qw) Me(Ub Uk) Kk(aN Pk) Rf(cF Ns) Nx(Dp Ue) RaaZ} dO{aV(Ba bJ bV bX cF cH cL cO cP cX Dd Di dJ Dl eF Fw gP) aX(aJ aP Ax Bc bR dF DG Dq fR Fw) fR(aD aN bC bR bU cL dJ gP) aJ(aD bR bU cF cL gP) dG(bL bR bU cF gP) cN(bR cH cL Db) aD(dF Fw) bC(cE Dq) cL(aP Dv)} dV{aD(aG Ap Ba bQ cB dF DG eF fR) dG(aO bC bL bR cF cL cP gP) eF(Af aM bL cN cP cR dL dN) bC(aP Bo cE dF Dg) cL(aJ bV Cs dL) fR(bR bU cP gP) aJ(aI bR) aX(Ba Fw) cH(cN dF) aUaV cFdL} dX{Qx(cF cN cP Cq Dc dJ dL Fw gP Hu Ih Iv Ke Li Me Po Rc Uf) Hu(Hc Kd Ko Ou Ph) Ib(Kc Kk Kp Ld) cN(Hf Jy Pj Wm) Jp(Rc Uf) Kc(dB Nm) Ko(gP Oy) Ky(dJ Ha) UeQy IccP IhIi QwgP JjVv} Gw{Dd(aD aN aQ aV aX BC bL bR bU cL eF) cL(aC aV BC dD dL dR gP) aN(aM aV BC cH cY dR) aD(aK aQ cB Dg dR Gp) aV(bJ Cu cX Dc) Dc(bC bU) DbcN aJaP aMcB bCdJ} Em{Me(Jf Kj Kl Ss Tr Tt Uc Uu Vo) Kc(cH Ha Ju Jv Lh Mr Vp Vt) Vo(Dl eF Nx Ou Ph Qw Qz St) Nx(Ha Kj Ua Ue Uu) Qw(Dc Kj Uu) Uo(aV Qz) aJ(Mw Ua) ExKe InOu JjLd OgPh} Lx{Nl(Hw In Iu Jj Jk Js Lv Md Mi Nd Nk Ns Og Po) Po(Ik Jg Lv Nc Nd Ne Nh Nj Nt) Nj(Jj Jp Js Lv Md Mm) Md(Ik Nd Ne Nh) Jj(Ik Ne Nh) Mt(Js Nd) Jg(Nd Nq)} Gc{Kc(aJ aP bI bO bV cH cR dG dJ dK dL dM In Io Jq Jy Mm Nk Nl Nu Og Qx Ug) Vo(aC cF Hu Ld Nj) Me(Jy Ql Qx) Ue(cF Ld) IbJn JtOn UkaV} cL{Dv(aI aL aM Ar bC cG Co cP Cs cZ dD DL dR Ex Fr Fw Gl) Dq(bL bR cF dI eF) gN(aM bL cA dJ Fw) GtcH bReX cPgT gCgW} Nl{Jj(Ik Ji Jp Lh Md Mm Mt Nt Pa) Md(Jg Jp Mm On) Og(Jg Mm Nt Pa) Jg(Jk Of) MmPa MtHw NiJp OnOy} Dq{Fw(aD aM aN aV bC bR cF Tj) eF(aD aM aV bX cP dC dJ gP) cF(aK Db Dd Dl) aMcB aXgW} Gt{gP(aJ aN bA Bo cF cN fR Fw) Fw(aD aM aN bR cM Tj) Bo(Di Dl) cN(cH Gp) CsaN DdcF aVcE} Og{Nt(Fp Ik Jj Lv Md Nd Nj Oz Pa) Jg(Ik Nd Nj) AaNd MmIk} fR{gP(gL gN Kd Qw Rb) Nd(Hu Nf) Qw(Nf Up) aV(gN gT) bUgN} Mt{Nd(Hw Jg Jp Md) Fp(Hw Md) Nj(Jj Jp) Om(Jg Jj) MdNx} aX{eX(aK cY dR) gT(aV cY Fw) DodR MeVq} aV{gT(bE cE dH dK) aCeX dGgC} On{Oy(Ik Nd Nj Om) NdNf} Jp{Md(Ik Nj) NfIk NiNj} dG{bR(gN gT) bUgN cPgC} Vq{Vs(iH iZ) NfiH} Pa{Jj(Ik Nt) MmNj} aJ{gN(bR bU) dJgC} Do{Fw(aD cA)} Me{Hf(cH cM)} Js{Ko(bN gP)} eX{aNdJ dLgP} MvJgOm

Constrained panels with 3 analytes, where 1.0E-8 >= 'AUC p-value' > 1.0E-9. Contains 1,749 panels of 9,935,646 total panels evaluated. :
Gn{Kf(Ao bE Cx Ef Em Et Ez Jl Mm Mz Ou Qe St Tr) Mf(Ao Co Cw Em Is Iz Jt Ke Mv Ng Nm Of Ut) Nb(Bg Cp Cw Ib Iz Kn Ma Mv Mw Nj Nl Qt Uc) Cs(aQ cI cM cY dI Iz Jy Ks Oz Pc Qu Un) Ou(Ba Bg Ct Cw Ii Ju Kj Kl Ny Uc Uo) Pc(bR dL Ef Ib Ik Iz Kj Kl Lj Mb Nj) Qu(cI cN cO dG Fw Hf Jy Ok Oz St) Oa(Aa Ef Fb Gl Ij In Iz Kl Li Ma) Ib(aP bQ bU Ih Jm Mt On Oy Qb) Un(aX bR cP Fa Jp Ko Mz On Rf) Qx(aJ aQ Ch dJ dL Jy Or Uf) bU(Aj aM cI dG Fb fR Jh Oy) cH(aK aX cY Fn Nm Oi Oz St) Aa(aQ Ar Ax Et Mu Qa Vv) Ez(aC cI dL Hq Nv Oy Rm) Nj(Af bR Cw dL Kd Oz Uk) Ih(Ao Ch Ju Kn Mn Ny Uf) cP(bF Cp Hc Mq Mr Rg Ut) Ke(aP dK dM Io Ky Ok) Oh(aN Fb Ii Ij Jt Ks) Fa(Ao Ef Hb Ij Uu) Ex(Fb Ij Li Ma Qt) Mu(Gl Gp Jy Ny Ul) Im(Ok Qa Qe Rm St) Kn(aM aP aZ Di Uo) Nx(bP Li Mn Mw Uh) Og(aJ cI Oi Oy Uo) On(Ao Ba Ef Gl Ny) Uf(Lj Nv Nw Sr Tr) bR(Ii Nk Nl Qm Qv) Fw(Fb Ks Oi Pj) Nm(aJ dL It Ky) Ue(cI Jm Nv St) Iz(Fp Kd Nv Oy) Kj(dL Ky Mz Oy) Ul(cM dI Hf Up) Uu(aC Oi Rm Ug) cN(cI Jh Ss Uk) Di(aJ aN Kd) It(Ba Cw Ii) Qe(Fb Om Vo) Qt(Ld Lj Mh) Jt(aX Ky Ld) Ko(Fb Ij Uh) Oe(Ba Kl Of) Ef(dG Oy) Fr(Kc Kk) Gl(Hq Mn) Mc(bO Js) St(Ju Vo) Ny(bE Vv) Om(Ow Up) aG(cB Hf) aJ(aQ cI) aK(Ch gW) bC(Ao Cw) dO(bE dK) BbaQ DcGw FpKs GpJy MbOz MvKd NaHv NgKy IjRf InJn HbSr QzbF QvdL JsKk aPdA cEcL dGdI} Ly{Et(aI aO aX bF bZ cE Co Cp Cw Dd De Hw Jf Kr Mi Ok Ur Vo Vu Tj) Jg(Bg Dk Im Iu Lj Mm Mt Mv My Nc Nd Nf Ng Nh Nj Ns Om Oy Oz) Jp(Bg Dc Dk Hw Ji Jj Jo Lv Mm Nc Nd Ne Ng Nh Ns Of Ok On) cH(aZ Db dE gP Hf Hx Jl Jr Js Md Mu Na Nf Oe Om Pa Pc) Dc(Ar bN Dg Id Ik Im Jj Lj Lx Nr Nw Ok Pa Pe Qa Sr) Lx(AA In Iu Ji Mi Mm Nd Nf Nj Ns Of On Pa) Jj(Aa Ik Im Iv Ji Ne Nh Nj Nr Nx On Qa Qe) aX(cE cM dJ gP Jk Jl Mb Md Mj Mu Nf Pa Pc) Nw(Dk Ih In Mi Ml Mm Ms My Nd Ns Ny) Pa(Aa bN Im Ji Lv Md Mi Mt Nt Og On) bN(aJ aZ bV In Kc Ko Mb Mu Oe Pb) Md(aJ Ar bA Id Ji Mm Nl Ny Qe) Mt(Iu Js Mi Mm Nl Ns Of Om) gP(bA Db Dk Jk Js Na Pc Ur) Aa(Jo Jr Nc Ne Nf Nj Oz) Ok(Im Jk Mq Nh Nj Oy Oz) Js(Ar bA dE Id On Sr) Mm(Nc Ne Nj Og Oz) Nl(Fr Lv Og On Qe) bA(Hq Hw Mk Mu Nd) Mi(Im Nc Nj Og) Mj(aJ Ar Id Sr) Jk(Ba Db dE Dl) On(Hq Nf Of Om) Dk(Ik Im Ko) Ji(Jo Nf Oz) dJ(aZ Db Pb) Ar(Mr Po) Mu(aJ dE) Og(Fr Li) Om(bJ Ko) DbdI DdIt DgOf FpHa NdaJ NfaZ UkVq} Et{Om(Ao Bg Ch Co Dd Fp Ih Js Kk Ko Lj Nd Ns Ok On Ou Qa Qc Ut) Md(Fp Hw Iq Iv Jf Jg Js Kk Mb Mw Nb Nt Nw Nx On Pb Vo) Nf(Bg bN Ch Dc Fp Gl Ih Iv Jf Ji Js Jt Mi Mr Nw Ou Pb) Jo(aA bJ bN Dc Hw Hx Iq Jf Kc Ko Mg Mi Mr Ou Qy Ul Ut) Vo(Bg Ch Dc Gl Hx Jf Kp Mj Mv Oe Ou Pa Pb Pg Ri Ut) Jj(Fp Gl Hw Hx Ih Iq Jr Lv Nh Ns Nu Ok Pb) Jt(Dk Fp Ih Jg Ko Lj Lv Nh Ns Nu Nw Ok Qe) Dk(Js Kc Kk Ko Or Ou Oy Oz Pc Qy Ur) Nd(aA Bg Dc Fp Gl Ih Ji Mi Mr Ok On) Pa(Dc Fp Gl Hw Iq Js Lv Mt Ns Nt Ut) Lx(Hw Hx Ii Ik Iq Iu Nh Ns Of) Js(Bg Ik Jr Ko Nh Nq Nt Nw Ut) Oz(Bg Ih Iv Ji Lj Mi Mr Ok On) Jf(Bg Ch Dc Jk Jl Mr Mu Pg) Kk(Bg Dc Jk Mj Mk Mv) Of(Fp Jg Lv Ns Nt Pb) Mt(Fp Iq Iu Mv Ng) Nh(Hw Iq Iu Ns Og) Ut(iZ Ou Oy Qx Ur) Gl(bN Dc Oe Pc) Nq(Ih Jr Lv Nt) Ne(aA Mi Ok) Jr(Hw Iq Ns) Og(Jg Nt Pb) Bg(Pb Ur) Me(Hf Kr) Ik(Mg Ns) Jk(Ou Qy) NtIi MjiZ NcOk NjaA RceP OebN OnOy OuPg} Ok{Lx(Hq Hw Hx Ii Iq Jj Jk Jo Ne Nq Of Og Om Oz) Jj(Hw Hx Ik Iq Js Mt Nc Nd Nq Nt Om Oz Pa) Of(Hq Hx Iq Jg Js Lv Md Mt Nc Ne Nh Oz Pa) Mt(Hq Ii Ij In Jk Md Nj Nl Nq Oy) Ne(Ii In Iq Iu Jk Nd Ns Og Om Pa) Og(Hw Hx Jo Js Lv Nc Nh Nq Nt) Om(Ik Iq Jg Nc Nd Nh Ns Nw Pa) Md(Hq Iq Lv Mw Nc Nt Nx Oz) Pa(Hq Hw Hx Ii Nj Nq Oy Po) Nc(Hq Ii In Jk Ns) Ik(Hq Hw Ii Ij Oy) Jt(Hx Iq Lv Nh Oz) Nd(Iu Me Mq Nj) Js(Dk Lv Nt Oz) Em(Ng Ue Uu) Nj(Iq Jp Mm) Nl(Me Mq Nk) Hq(Nh Oz) Hw(Nq Nw) Jo(Fp Pb) dX(Fb Ny) DkNf PoNw GcKc NgJg cFeP} Lx{Po(Fp Hw Hx Iv Ji Jj Js Li Md Mi Mt Nw Nx On Oz Pa Pb Pe) Nd(AA Jj Js Mi Mm Nc Ne Nf Nj Ns Nt Nw Og On) Ne(Hw In Iq Jg Jk Js Lv Mi Mm Ns Og) Nj(AA Hw Iu Jg Ji Mi Mt Og On Pa) Md(Hx Jg Jj Lv Mt Nc Nt Nw Nx) Jj(Hx Lv Mt Nc Nq Nt Oz Pa) Nh(Hw In Jk Js Of Og) Ik(Iu Jk Jo Js Nf Og) Jg(Jk Mv Nf Nl Of Oz) Nl(Ji Mm Om On) Nf(Ji Lv On) Mt(Hw Jk) Nw(Hx Js) NtOg LvNc} Nw{Ik(Hq Hu Ii Ij In Iq Iu Jj Jk Ms My Ng Ns Pa Po) Js(Bg Dk Fp Hw Ih Mv My Nh Nq Ns Ny Oz Pa) Nt(Hw Ii In Iq Jj Ns Of Om Oz Po) Ne(In Iq Jj Jk Ml Nd Ns Of Og Pa) Nd(aA Ih In Iu Mm My Of Om) Nf(Iv Ji Lv Mi Mt Nh Ny On) Nc(In Jj Jk Ml Og) Md(Mi Mm Mw On) Mt(Iq Nq Ns Oz) Om(Lv Nh Ns Pa) Hw(Nh Ns Pa) Jg(Jt Mv Of) Mj(Iv Mr) Iq(Oz Pa) pF(Jr Ql) LvJo MaMi MmNl HxIv OnOy} Nl{Jj(Fp Fr Im Iv Jg Jm Jt Lv Mg Mi Nk Nv Nx On Pb Pe Pg Pz Qe) Jp(Hw In Iq Js Lv Mi Mt Nd Nk Ns Og Pa) Pa(AA In Jg Ji Lv Md Mi Mt Nk) Og(Aa Ik Ji Lv Md Mi Mt On) Mm(Hw Lv Nd Ni Nk Ns Om) Md(Fp Ji Lv Mt Nx) Aa(Ma Nf Om Oz) Jg(Mv Nd Nf Om) On(Hq Jk Nf Om) Mt(Lv Ns Om) Ji(Hw In Nf) LvMe HwNx} Nj{Jp(Iq Jj Js Lv Mi Mm Nd Nk Og Pa) On(Hq Hw Jj Jk Js Md Nf Of Om) Jg(Jk Md Nf Of Om Pa) Mm(Jj Lv Md Mt Og) Mt(Hw Lv Mi Og) Pa(Aa Jj Lv Nt) Nf(Aa fR Ji) Md(Ji Nx) Og(Aa Ji) eP(Hu Nb) NtJj cNdX} Nd{Jg(Im Jk Md Mv My Nf Ns Of Pa Qe) Mt(Fp Ji Jj Lv Mi Mm Og On) On(Hq Js Md Ns Og) fR(cP It Og Oz Qw) Nt(Iu Jj Jp Pa) Ji(Nf Og) Pa(Aa Mm) aX(eM Me) MdNv bEeM} eP{cF(Hu Ji Jp Mf Oz Qw) Hu(fR On Qd Vv) Ib(Nv Oh Ou) aX(Nc Ng Oh) Mf(dJ Qy) Rc(eF Jg) Rf(bC Ju) Og(Kf Oi) aV(aC cO) cH(cN Oz) DgKn FwJj MdKz MwQa NbbR IrRa QwVv PcgP dJeF} Jj{Ik(Jp Md Me Mm Mt Nc Nc Nt Og Qe) Mt(Hw Md Nc Ne Ns Nt Oz Pa) Ne(Jg Ji Jp Mm Nt Pa) Nt(Md Nq Om Oz) Jg(Mv Om) eM(cF Ql)

Figure 11 Continued

EmQz MgdX NhPa} Ko{bN(aX Dc Dk Gl Jk Jo Jr Ke Kj Ma Me Mv Nf Oe Om Qw Tn Ua) Js(Di Dk Me Mv Om) Om(Dc Dd gP Ri) eM(cF gP Rc) gP(Dk Jo) DrKe JfJk} eM{aX(Dl dR Hf Nv Oh On Qa Qe Ue) Hu(Ky Or Up) Nx(Fb Uk Vt) Fa(aC gP) aV(eX fR) bE(Kz Wm) FpcF UbQw UeQy IbVv QxcC JybS LdaC PcgP dJeF} Dr{Me(aX cH dL Mu Nb Nx Pa) Nx(Fb Iz Li Mv Pj Ra) Rb(aP aX dK) Kc(dI Hx Mr) aV(cO dR Fw) Gw(dJ dL) RacF QwgP PiaX} dV{aX(aJ bA dF dG dL) aP(bL bU cL eF) aJ(bU cB eF) dG(bU cT eF) bC(dL fR) bF(cN cP) cF(dF Dg) eX(cE dF) FwaD bQbR bUdM} Md{Nx(Fp Hw Lv Nf Og Oz) Jg(Ne Nf Og Om Oz) Jp(Mt Ne Nh Nt Nu) Mt(Nh Oz) Ik(Og Pa) On(Nf Nh) fR(Qw Rb) JiOz} fR{Qw(cG cI Dd dH Iq Mj Mx Oz Pa) dO(bX cF cM cN) gP(aD bP Db) Nf(Oz Pc) Rb(dJ Mj) OzcE bRgN} Og{Nt(Jg Js Mt Nc Ne Nh Nq Ns Om Pb Pc) Ik(Jp Mi Mt On Pa) Jg(Mv Ne Om) LvOi} Gt{aN(aV Ax Bo cB cH dJ Dl) cF(cH Di dJ) Dd(Fw Gw) cH(Aw gP) FwbC dGgP} Mt{Hw(Ji Jp Nc Ne Nh On) Om(Ji Jp Lv Mm On) Js(Fp Ji) NuIn OnOy} Em{Vo(Hf Ng Pj) Jp(Ke Kj) Kc(dI dN) AxIb ExUf IhIi IzNx RbUu JfQw aQdM} Nf{Ji(Ik Lv Ne Nt Oz) Nt(Jp Pa) Mi(Ik Nx) Jg(Fp Mv) On(Om Oy) GcUe} dO{cN(aM Ar bB bF Cv) aX(Ar cG dI) aJ(cE dI) dG(aD aO) aNaP bCdF} Gw{aD(aG aN aU Ba Dc) aN(aK bN dL gP) bC(dD gP) bLdL} Jg{Om(Mw My Nc Ne Nh) Ne(Jk Mv Of) Of(Mv Nh)} Ik{Jp(Jo Js Ng Ns Of Om Pa) On(Of Om)} Dq{Fw(aK CH cP dR) BoaM CheF cFdR} dX{Qx(dB Dd gL Qh) cN(Oh Ou Ph Rf)} eX{dJ(aV cB cG) cE(aK cY) AlFw AwgP DiaN} Gc{Vo(cI Ns Rb) aV(Rc Ue) QuKd} On{Oy(Fp Hw Ne Nh Nq)} Dv{cL(aA Ax Cu dG)} Me{bN(Hf Kc) JfdE SrJs} Jf{Kc(bN dJ)} DoFwbC NtInPa VqVshB bUdGgC cHgLgP

Constrained panels with 3 analytes, where 1.0E-7 >= 'AUC p-value' > 1.0E-8. Contains 2,934 panels of 9,935,646 total panels evaluated. : Ly{gP(bJ bN dI dM Et gL Hf In Jf Jp Kc Kk Ko Mb Md Mu Nd Nf Pa Ri Sr Uk Up Vq Wm) Jj(cH Db Dk Fp Fr Ih Ii Io Jh Jm Jt Ko Lh Li Lj Md Mi Mr Mz Nu Nv Pe Pg Pz) Jg(Aj Ao cE Ch Cp Ct Dd Fp Hu Hw Ih In Jh Ji Jk Js Mi Ms Mu Mw Nq Ny) bA(bF Bg cE CT Dc Dk Ex Hx Ii Jl Ma Mj Mr Mv Nf Nv Pe Pg Po) Md(Aa aZ bN Bo cM Db dE Im Ir Mi Mp Nc Nt Nx Pe Pg Sr Uh) Dc(Ap AX bV Db dE Dl Jm Jr Jt Kf Ko Ny Oy Pf Qh Tt) Mm(Fp Ih Ik Im Ji Jo Jr Lj Lv Nd Nf Nh Of Ok Pb Qe) On(Dk Hw Ij Im Iu Jk Mi Mt My Nc Nd Ne Ng Nq Oz Pg) Et(aA Ef Ha Hf Ib Iz Ke Kg Kj Ks Ou Qt Tn Uk Vp) Og(Fp Ik Im Ir Lh Lj Lv Nc Ne No Nv Nx Pe Pg Qe) Dk(Aa Ap Ar aX Bb bN cH Dg Kq Lx Nr Pa Pb) Om(Aa bN Dd Dg dJ Dl Jp Lx Qm Sr Tt Uh) aZ(Aa bJ cE cM dI Hq Hw Mj Mu Nd Pg Uk) Jk(aJ Ap bV eF Hf Id Jp Ko Sr Tn Tt) Pa(Dd Fp Ik In Iv Nc Ne Nf Nh Nj Nx) Fr(Im Iv Lj Nc Nd Ne Nf Nj Ns Of) Mi(Fp Ih Ik Lj Nd Ne Nf Nt Nx Qe) dE(Aa dI dJ Hq Hx Jf Mj Mv Nd Nf) Db(Aa aX Dd Hw Ik Nd Nf Nr Nu) Nl(aA Fp Im Jt Lh Lj Nk Pc Pe) Js(Aa Ap bV cM Dg Dl Qe St Uh) Ko(Ch Cp Jf Kj Mj Qw Ri Uk Ut) cH(aX bJ cI Hw Ii In Mj Mk Pg) Sr(Ha Hw Mk Mr Mu Mv Nf Of) dJ(aJ bE cC In Kc Mb Oe Pc) Ct(Ba bJ It Jp Nr Oy Qe) Nw(aA Ao Bg Ha Ut Vp Tj) Ok(Ao Bg Ch Fp Ih Nd Ut) Pb(Bg bJ cE Dd Di Ut Tj) aX(bJ Ha Mv Nd Oe Ou Ur) Id(Ha Mr Of Po Ri Uk) Mt(Ih Ji Lv Mr Nd) Jp(aI cE Di Fp Ih) aJ(Aa cE Hx Mv Nf) bN(Hf Mj Nf Uk Wm) bV(cM Jl Mj Na Nd) Ar(Lx Nv Pe Pg) Bo(bF Hq Mu Mv) Nc(Ji Lv Nt Qe) cM(aI bE Mb Mu) Ne(Ji Lv Qe) Pe(Ha Iu Nf) bJ(Hw Mu Mv) Ap(Mv Of) Dd(Na Nd) Dg(Jo Oe) Nr(Ha Vp) Ik(Bg Ch) Ji(Nj Of) aU(aV cY) AaNd DiMb DlOe ExKk LvIm LxMr NfUh IuQe VqOy OzaI cEdG} Et{Vo(aI Ao bN cE Co Cw Di Fr Ha Hq Ib Ii Ij Jk Jl Kc Kg Ko Ma Me Mk Mq Mr Mu Nd Nv Po Rg Tn Vp Vu Tj) Jf(aI Ao bN Ct Fr Ha Hq Ii Ij Je Jr Js Jt Kc Kc Kg Lh Me Mj Mk Mq Mv Nd Nv Oe Om Pa Po Ul Vu) Gl(aZ bA Bg Dd dE Dk gL iZ Jk Jl Jo Js Jt Kk Ko Md Mj Mv Uk) Om(aA aI bN cH Cw Di dN gP Ha Iq Iv Ji Kg Mi Mr Rg Ul Vp Vu) Js(Ao bN Ch Dc Fp Ih iZ Kc Kk Lj Lv Ns Nu Ou Qe Qw Rb Ur) Jt(aA Bg bN Ch Di Hw Is Iv Ji Kk Li Mi Mr On Ou Ut) Kk(Ao bN Co Hq Hx Ij Jl Jr Mn Mu Nv Pg Po Qt Vu) Oe(aI Ao Bg bL Ch Co Dc Di Dk Ko Ou Rg Ul Ut) Nf(aA aI aJ aZ cE Co Ef Hw iZ Kg Kj Ut Wm) Dc(Fp Kc Ko Lj Me Nj Ou Oy Pb Pc Qh Rb) Nd(aI Ao aX aZ bA bN Ch Co Cw dM Kj Ut) Ur(aI Ao Ch Di Hx Ij Ke Ma Md Mn Mv Pg) Pb(aI Ao bZ Ch Co Cw Kg Ns Rb Vu Tj) Ok(Ii Ik Lx Md Mt Nh Nq Of Og Pa) Ou(Bg Ha Hq Jl Md Mj Mk Mv Po Vu) Dk(gP Iq Jj Jo Ks Nw Qx Ra Ut) Pc(aI Ao Bg bN cE Ch Cw Md Ut) Ns(Fp Hw Iq Iv Jg Lv Nt Nu) Mj(aJ iJ Kc Kj Ko pF Ra Wm) Nq(aA Fp Iv Ji Mi Mr On) Jj(aA Bg bN Iv Mr Rb Ut) Md(aA Ji Kj Mi Mr Nu) Mv(bJ bN Jg Kc Ko Qy) Hw(Fp Ih Ik Lj Lv Nt) Ii(bN Em Ih Ik Jg Nw) Jk(bA Kc Ko Or Rb Wm) Of(Iq Iv Mi Mr On) Ut(bA gL Kc Me Qy) Oz(aA aI cE Ch Cw) Pa(Ao Bg Kg Kj Vu) Ik(Iq Lj Mi Ng) Jo(aI aZ Rb Vu) Og(Hx Mr Nu On) Oy(Ao Bg Ct Kj) bN(aX iZ Kc Ma) Nt(In Iu Ng) Ih(In Iq Iu) Lj(Ha Iq Lv) eM(Fb Kn Uf) Ao(Hx Qy) Bg(Qx Qy) Fp(Iu Mq) Me(Kj Ks) Nh(aA Mi) Jg(My Ng) Ri(In Mr) iZ(Jl Nv) WmPg EmUu MbMc NcaA NiNk HxKd JrpF} Gn{Ok(aG Ao Ba Cw Ef Gl Hb Ib Ii Kl Ma Ul Uu) Mf(dI Ib Ii Jo Kg Kl Mg Oy Pj Qx Uk Uu) Ih(aG Ef Im Iz Jv Kl Ng Nm Qt Qu Qv Ul) Kf(Ba Iz Jn Jo Jt Kj Ng Of Oi Qg Ue Vv) Rm(Ao Ef Ij Iz Jo Ju Kj Kl Mn Ng Uc Uf) Oa(aG Ao Ha Im Jt Jy Ke Po Qt Ss Uf Uu) Ou(Ao Bb Ij Iz Jt Ke Mu Ng Oy Po Rh Un) Vv(Ao Ef Fy Gl Ii Ik Jt Ng Nm Uf Uu) On(Cw Fb Ij Im Jd Ng Qt Uc Uh Ut) St(Ch Ef Ib Ik Jg Jj Qt Uc Ul) Ke(cO dG Ic Ji Kd Mm Nj Nv Pe) Qb(aG Fb Ii Im Jk Kj Mn) Jm(Ez Ii Ij Jt Kj Kl Uu) Oh(aG Ba In Iz Ma Of Uu) Aa(cB cJ Fn Jn Kn Ug) Ax(Fy Iz Ma Qt Qu Uf) Ld(aJ aX cN Co Gl Qu) fR(bR cM dA dJ dO gP) Fa(Cp Fb Im Jv Kj) Nb(Ij Qy Ss Ua Uh) In(bU Cs Fw Is Nl) Js(aM Cs Ex Fp Ko) Jt(Ji Nv Oi Qd Qe) Nw(Ez Im Qt Qu Un) Nx(aN dL Mv Qt Vt) Uu(Al Cx dL Mh Nv) dG(aK aQ Kl Mv Mw) Ma(cO Hf Kd Lj) Qa(Ez Hb Qu Uf) Qx(aK Gl Qw Uk) Un(Fp Fw It Mb) Oy(Bg Jh Kd Ss) aJ(cY dO Nj Qv) aX(cB Cs Nj Qz) dM(aK aQ dA dO) Dp(Fb Oz Pc) Em(Kj Lu Ss) Mw(aP cO cR) Nk(cM Kd Ut) Hf(Iz Qt Uf) Qe(Ez Ib Ij) Kn(Ez Oe Qu) Ny(Na Pc Um) Oi(aG Ju Jv) aN(cI Lj Mh) bP(To Uf Uk) bU(Iz Qm Ss) dE(aQ Qv Qz) Ef(Jn Oz) Po(Cs Ex) Fb(bR Mz) Gp(Na Up) Mn(Mz Ph) It(Ib Pj) Jd(cN Oe) Kj(aC Mh) Kl(Kp Ky) Ko(Ii Pj) Ul(Mv Uk) cP(Ic Ua) AlIz AoJn BbcB BocH CwdF CxJv DodO FwPc MmUf MucI NfcN HvcA IjOe IqgP JhKd QzKy QvgW QuaP JuPh JycM LjOz VtaM aKaU} Jg{Nd(Fp Hu Ih Iq Iu Iv Jh Ji Jj Jo Jp Lj Lv Mi Mm Mu Mw Nc Ne Nh Nj Nt Nu On Oy Oz Pe) Nf(Ih Ik Iv Ji Jk Lj Lv Mu My Ne Nh Nq Ns Nt Nu Og Oz Pa Pe Qe) Lx(Fr Hw Hx Ii Ij Iq Jj Jo Js My Nc Ng Ns Og Om) Md(Fp Ik Iq Ji Jk Lv Mt Nc Ng Nh Nq Nx Of Ok Pa) Of(Fp Iq Ji Lv Mt My Nc Nq Ns Nt Og Om Oz Pa) Om(Dc Dk Fp Ih Iq Ji Lj Lv Mu Nq Ns Oy Pa) Nl(Hu Hw In Iq Me Mm Mw My Ng Nk Ns Oy) Nj(Iq Iu Jj Lv Mm Mt Mv My Ns Oz) Nw(Ii Ij Jk Jo Mu My Nq Ns Nv Oy) Og(Fp Mt Mu Mw My Nh Nq Ns Nu Nx) Jj(Ik Mt Nc Nh Nq Nt Oz Pa) Jk(Iv Mt Nc Nh Ns Oz Pa Qa) Ne(Hw Iq Iu Lv My Ns Pa) Mv(Mt Nc Nh Nq Oz Pa) Nq(Mm Mt Ok Pa) Nh(Hw Iq Ns Pa) Oz(Fp Mm Mt) Iq(Nc Pa) Ok(Ii Oy) FpJo MtHw IkPa OnOy} Nw{Pa(Hq Hx Ii In Jj Lv Mt Mv My Nh Nq Ns Nt Of) Lx(Hw Ii Ik Iq Jk Mv Nq Ns Of Og Om Oz) Js(bN Co Dc Di Gl Jj Ko Mm Og Rj Ut Tj) Ns(In Iq Iv Jj Lv Ml Nh Og Ok Oz) Mt(Ii Ij In Iu Jk Ms Mv Of Og) Jj(Hw Hx Iq Lv Nd Nh Nq Om Oz) Dc(Gl It Jm Md Nd Nf Om Oy) Hq(Hw Iv Mi Mr On Pb Pe) Hx(Ih Mi Mr Of Og Ok Pb) Om(aA Dk Ih Mi Mm Vp Tj) Oy(Dk Iv Mi Mk Mr Ok Ut) In(Fp Ih Iv Lv Nh Nu) Og(Fp Iq Lv Nh Nq Oz) Nt(Jk Ml Mv My Nq) Mm(Ik Iq Ne Nf Oz) Rj(Bg Md Nv Of Ut) Dk(Jr Mj Nf Qy) Hw(Ih Iv My Oz) Of(Lv Ml Nh Oz) Mr(Lz Po Ri) Ih(Iq Jr Mj) Ik(Mi Mv Ny) Iv(Ij Nq Po) Ok(Ii Nq Ny) Gl(bN Jl) Ml(Fp Lv) My(Nh Oz) Iq(Mi Nh) Iu(Nc Ne) Pg(Ou Ri) BgNf EmUf MgJo MvQy IjOn JriZ RgVo} Mt{Md(Hw Ik Iq Ji Js Lv Nc Nc Nj Nt Og Om Pa Pb Pc) Js(Jj Jp Jr Lj Mm Nd Nh Nj Nl Nq Ns Nt Om Qe) Ok(Iq Iu Mq Mv Nc Ne Ng Ns Og Oz Pa) Om(AA Fp Jt Ko Lx Mi Nd Nj Nt Og) Fp(In Iu Jj Mi Nf Nq Ns Og Pa) Hw(Ih Iv Lv Mi Mm Mr Nt Og Pa) Nq(Ji Jj Jp Lv Lx Mi Mm Pa) Nj(Aa Iu Iv Ji Ns On Pa) Nl(In Iu Ji Mi Nd Nk On) Jj(Iq Iv Ji Lv Mm Nh Nx) Lx(Hx In Iq Lv Of Og) Nd(Iu Iv Jl Ns Pa) In(Iv Ji Nt Nx) Jk(Ji Ko Nt Pa) Jp(Ik Iq Nh Ns) Og(Lv Ne Ns Oi) Oy(Iv Mk Pc) Nf(Ji On) Iq(Ji Pa) NtOf LvNc MiOz} Ko{bN(aL bC Bg Cp Di gP Ha Hq Hx Ii Ij In Iz Jf Jq Jt Ju Jv Kc Md Mj Mk Mn Mr Mu Na Nv Pa Pc Pg Po Ut Vo Wm) Jf(Bg Cp Dc dE Di Dk gP Js Md Mr Mu Mv Nf Om Pg Qw Ri Ut) Js(Bg Ch Dc Id Iq It Jk Ma Md Nf Pa Qw Rj) Dc(Di Gl Jm Md Me Nf Pa Qw Rb Ri Sr) gP(Jj Jk Jt Kj Ma Oe Of Qw Ri Ur Vo) Om(bJ Di Dk Gl Jk Ma Me Nf Qw Vs) Qw(aI cE Dk Ri Vs) Pa(Dk Gl Jk Kj Vs) Ur(Bg Di Gl Mv) Ri(Cp Dk Vs) aZ(Cp Ut Vs) eM(aC bE Kl) Jk(Nx Sr) DdGl MdOg MeaX JrpF VsdE aUaV}

Figure 11 Continued

Lx{Ik(Hu Hw In Lv Mi Mm Ng Nq Ns Of Ok Om Pa) Nt(Hw In Iq Iu Jk Js Nf Nq Ns Of Oz Pa) Ji(Hw Hx Iq Jj Jk Js Md Nd Ne Nh Nq Oz) Md(Fp Hw Iq Jp Js Nb Nq Og On Oz) Po(Iq Is Jl Lh Mf Mk Mm Mr Nq) Lv(Hw Js Nd Nh Nq Ns Og Oz Qb) Nc(Hw In Iq Js Ni Nk Ns Og Ok) Jj(Hw Iq Iv Js Mg Mm Mr Nx Om) Nh(Iq Iu Mi Nf Ns Ok On Pa) Nq(aA Jp Js Mm On) Nd(Hw Iu Iv Jp Mr) Hx(aA Iv Js Og) Ok(Ij Iu Mq Mv) Nj(Iv Mr Om) Fp(Js Nf) Ne(Iu On) In(Iv Nu) AaNl MgOf MjIv MmOz NfJs OnOy} Nl{Og(aA Fp Fr Ip Iv Jh Jq Jt Lh Nd Nk Ns Nx Oi Pe Qe) On(Hw Ii In Iq Js Mm Nd Nk Ns Of Pa) Aa(Hw Ij Jj Jo Js Md Mj Nd Ni Ns) Mi(Fp Hq Hw Hx Md Me Mm Nd Ni Nk) Ji(Iq Iu Me Mm Nd Nk Ns Om Oz) Md(Fr Li Nb Nk Nm Nt Pe Qe) Qe(Hw In Iq Nd Nk Ns Qb) Nt(In Iu Me Nk Pa) Mm(aA Fp Iu Mr Ok) Ns(Fp Lv Nx Pa) Hw(Fr Im Nv Pa) Lv(aA Nk Om) Me(Ik Nk) In(Nx Pe) Jj(Mr Nu) Pa(Iq Nd) eP(Hu Qy) FrNk JkNv JoLh JpOm NxaA} Ok{Pa(Ik In Iq Jk Lv Nc Nh Ns Nt Og) Js(aI Bg bN Cw Dc Fp Gl Ih Jr) Og(eP Fp Hq Jt Nx Of Oi Oz) Nd(Dc Dk Fp Ih Iq Jp Mm) Nh(Iq Iu Jj Jk Me Mq Oz) Nt(Hq Ii In Iu Jk Oz) Om(Dc Dk Lv Mq Nr Of) Ik(Iu Jk Me Mq Ng) Nq(aA Ih Jp Mi) Hq(Hw Iq Iv Lv) Oz(Iq Mm Nj Ns) Md(Fp Hx Mi) Mq(Hw Nc Nj) Nf(Bg Dc Wm) Iv(Hx Ij Mj) Jt(aA Fp Mm) Oy(Lv On Pc) Me(Ne Nj) Ih(Hw In) Iu(Nc Nr) Jj(Lv Nx) Jo(bJ gP) dX(St Up) DkJr GcIn MjMr QdQe QzeM UneP} On{Nd(Hw Ii Iq Iu Jj Jk Jo Ng Nu Nx Of Om) Om(Iq Jj Js Lv Md Nc Ne Nh Ns Nt) Md(Fp Hw Ik Lv Ne Nq Nt Oy) Nf(Fp Hw Ik Js Nh Nt Nx Of) Nj(Ii Ij Iu Jp Mm Og Oz Pa) Oy(Iq Jj Lv Nt Oz Pa) Ik(Hq Jj Jk Js Ng) Ne(Hq Jj Jk Og) Nh(Hq Hw Jk Of) Nt(Of Og) WmJk NcHw HxOf} Jj{Ne(Fp Im Jm Jt Lh Lv Md Mg Mz Nd Nj Nv Nx Om Pe Pg Pz Qe) Nj(Aa Fr Ji Jm Jt Lh Nr Nx Og Qe) Ik(Hu Ih Iv Ji Jm Jt Lj Ns Nx Om) Nc(Ji Jp Lh Nd Nt Nx Pa) Nh(Ji Jm Md Mm Nt Nx Om) Nd(Aa Mm Nr Pa) Em(Mf Nu Ou) Nt(Mm Pb) MdNx JiOz KgdX} Jp{Nt(Hw In Iq Jk Jo Js Lv Ne Ng Nq Ns Of Og Om Oz) Ik(Hu Hw Iq Iu Ji Jk Lv Mi Mv Nc Nd Ne Nq) Md(Fp Iq Lv Mb Mf Nc Nd Nx) Ne(Hw Iq Js Lv Nd Ns Pa) Nc(Hw Lv Nd Ni) Nf(Fp Lv Nu Nx) Nh(Hw Ns Pa) Nj(Aa Ji Om) Nd(Aa Nu) HueP} eP{Hu(Ar cS dL eF Fw Ib Ir Nh Nv Og Oz Tv) Ib(Ap Iz Jm Jt Pz Us) Qy(cH cI dI Jn Nf Or) aV(aD bA bR cF cL gP) Og(Di Id Ug) aM(cB cL eF) Wm(aC eF) Nb(It Kz) Kf(cF Rc) Kn(Dl St) cC(bA cL) DqFw JybC KzcG RfdI OiaX UteF PbcH cFcL fRgP} Nj{Mm(aA Fp Iu Iv Ji Jo Jr Lj Mi Nd Ne Om Oz Pb) Pa(aA Fp Ji Md Mi Og) Qe(Js Lv Md Mi Og) Aa(Jo Jr Om Oz) Nt(Iu Lv Md Mi) Ji(Iu Om Oz) Og(Jt Mi Nx) Nb(eM Md) DrMv MiNf NifR IuNx bEeM dXgL} fR{Qw(aH aI bN cE Db Gl Ha Ks Mr Om Uo) Nf(cE cP gP Hq Jr Kd Lv Pb Up) Oz(cP Gl gP Hu Iq Lv) gP(aF Aw Bc dM Pc) Nd(aV cQ Ou Pc) Rb(aY Mv Ut) Me(Iq Ml) Pc(cE Lv) MjQx dJdV} Md{Nt(Fp Ji Lv Nd Ne Nx Oz Pa Pb) Nx(Ik Mi Nc Nd Ne Nh Om Pa) Fp(Ik Lv Nb Ne Nh Og) Ji(Ik Lv Nd Ne Nf Nh) Mm(Ik Lv Nc) Nh(Nb Pa) Nv(Iq Nf) NuPa NdNy IkQe} Me{Hf(aX dJ gP Id It Jf) Nd(Aa aZ bA bN dE) Sr(aX Dc Ha Mj Om) Dr(cN cP cY Fw) aX(Jf Ou Qw) Dc(Id Kf) Kc(cM dJ) Vq(dE Ky) gP(Kk Ur) DbJf GcOu LvNe IdbN IkOg QmOm} eM{Hu(cF Jy Kp Qz Ur) aC(Jy Or Rf Vo) gP(Kz Ld Oz Pb) aX(Gp Mb Pc) bE(Oa Ph Ue) cL(dI dJ Qy) Gl(Fa Oi) Ih(Ha Ii) Og(Kf Oi) Uf(eF Qx) CheF DiIb FbNv SrKk RaLd QtVv KzdB} Gw{aN(Al aQ aU bR cP dD dJ Dr Fr) aD(Ar Bc Co Db dD Dl gP) Dc(aK aM Bc dR Fw gP) bC(Al cH dL dV Gp) Dd(Ad gP) AlbU AnaM BcDr CqFw DbcF GtcH aXdL} Nf{Lv(Fp Ih Lh Nx Pe Qe) Nt(Fp Mi Nx Pb Pe) Ji(Fp Iv Nc Nh Pa) Nd(Aa Mi Nv) Ik(Mm Pa Qe) Fp(Lh Mi) Nx(Li Lj) DcQe DgVo KcbN KkgP} Nd{Mm(aA Ik Lv Nc Ne Nt Og Qe) Ji(Iu Nc Ne Nt Oz Pa) Nt(Lv Mi Nc Ns) Nu(Im Og) Mi(Nx Oy) AaOz JsNv} Og{Ik(Fp Ih Iv Ji Jt Li Lj Lv Nc No Ns Qe) Ne(Ji Lv Mm Pa) Nt(Ji Mm) Nh(Fp Pa) EmUe LvMm} gP{Kk(Jk Mv Nm Nx Om Wm) Gt(aX bC Cp cW Dd) Qe(Jf Qc) Ur(Gl Wm) eF(Bg Dc) DgVo RbaJ JfKc QwbV cNdO} dV{aX(aP Ax Bo cG Gp) aJ(aD bF cF cG) bR(aP cN dF) dG(bA cB cH) FwcA GccL aDaP bCbF bUdF cReX} Dr{Nx(Co Cw Ez Js Ju Kc Qt) Ra(Jn Qb Rm) Qw(Dd Gl Nk) aX(Fn Mz St) Kc(aD Ic) RbOr} Gc{Vo(aV aZ Nv Or Pb Ue Uk Up) Aa(Hu Ld) Ue(Gl In) Kc(dN Mf) Kj(aX cF) StQx QwJo} Pa{Nt(Iq Iu Jk Lv Ne Nh Ns Of Om Po) Ne(Fp Lv Mm) Ik(Iu Mm Of) Nh(Hw In)} dO{cN(aD dG eF Fw) aJ(bC cC dA) aX(bA bU Cw) dG(bW dI gC) aP(bC bU) aNcR} Em{Qw(Ad Ii Nu) Kj(Dl Ou) ExQh HaNu IbOu IiLd RbVp JfNx RfVo UoaZ cYdM} Gt{aN(aJ aK bQ bR cF cT Ex) Fw(CH cP) Bo(cH Gp)} Ne{Ji(Hw In Iq Om) Aa(Hw Oz) Lv(Mm Nt) HwNx RcdX} eX{dR(aN cE cR dK dM) aQ(cE cR) DdcV FwdJ cRcY} Dq{Fw(aQ bZ cY Dd) Bo(BC Dl) aQ(aV dK)} dX{Ib(Id Sr Ue) Qx(Ma Oe) QyKy KfOm KpcN OrdJ} Ik{Mm(Jo Of Om) QeOf JiJo} aJ{bN(bU cH) AacM DgbL MvVq} dJ{Kc(bN Db Rj Rm) dGgC} Dc{Ad(Ch Di Om) IdIt} Hw{Nh(Im Ji Qe) NcJi} Oz{Nt(Ji Lv) LvMm IqJi} Dg{Vo(Dk dN hC)} gC{dG(cH dD) aXdL} Dv{cL(dB dF)} cG{gN(bU cF)} ArJrpF NtLvNc RiVqiZ

Constrained panels with 3 analytes, where 1.0E-6 >= 'AUC p-value' > 1.0E-7. Contains 5,350 panels of 9,935,646 total panels evaluated. :
Et{Jf(Af aU Ba Bb cE Co Cp Cw Dd DE Di Ef Em Fa gP Hc Hw Hx Ib In Iq Iz Jd Jq Kj Kq Ks Ma Mn Mw My Na Nb Nq Ny Of On Oy Pd Pe pF Qt Qw Rg Tn Vp Tj) Kk(Af aI aO bF bZ cE Ch Cp Ct Cu Cw De Di Fr gP Ha Hw Ib Ii In Jd Jq Ke Kg Kq Ld Lh Lx Ma Mq Mr Mw Mx My Nb Nq Ny Oy Pe Qc Qw Qx Rc Tn Vp Tj) bN(aH aI aJ Ao bF Bg cE Ch Co Ct Dc Dk Hq Hx Ij In Jk Jl Jr Ke Kj Lh Md Me Mj Mk Mr Mu Na Nj Nq Nv Of Oz Pa Pb Pg Po Tn Ut Uv) Kc(Af Ao Bg bL Ch Co Cp Cw De Di Ha Hx Ii Ij Jl Jr Jt Ke Kg Ma Md Mk Mq Mu Nv Oe Of Pg Po Qt Ur Vp Vs Vu Tj) Ko(Ao Bg Ch Cp Ha Hq Hx Ii Ij Iz Jl Jr Ke Kg Kj Ma Md Mk Mq Mu Nq Nt Nv Of Pg Po Qt Qw Ut Vu) Ou(Ao Ch Co Cu Ez Gl Hx Ii Ij Iz Jr Ke Kg Kj Ma Me Mq Mr Mu Nd Nn Nv Ny Pe Ql Qt Tn Ur Tj) Ur(Co Cp Cw Fr gP Hc Hq Jr Lh Me Mk Mq Mr Mu Mw Nd Nq Nv Ny Pa Pe Po Qt Ra Rc Rg Tn Vu) Oe(aJ aO aX bF bQ bV cE cG cH Cw Dd De gL gP Ha Je Ke Kg Kj Kz Qt Tn Vp Vu Tj) Jt(aI Ao Ax bF cE Co Cp Cw Em Ha Ib Id Kg Kp Qt Rb Rg Sr Ul Vp Vu Wm Tj) Js(aA aI bF cE Co Ct Cw Di Ha Ib Iv Ji Kg Mi Mr Ok Qt Sr Tn Vp Vu Tj) Pb(aH aL aO Bb bF bL bQ cE cG cH Ct De Di Ha Hq Ib Iz Ke Kj Qt Tn Vp) Pa(aA cE Ch Co Ct Cu Cw Dd Di Ef Ha Hq Ib Iz Ke Qt Qw Tn Vp Tj) Vo(Af aX bF cH cM Cp Ct De dN gP Mn Mw Ny Of Oy Pe Qt Ul) Ch(cP Ha Hx Ii Iq Jj Jl Jr Kr Ks Md Mj Oy Pg Qx Qy Ra) Nd(aO bF cE Cp Dd gP Ha Ib Ke Kg Qt Qw Ra Rb Vp Vu Tj) Pc(aH aO bF bZ Co Ct Dd Di gP Ke Kg Mv My Ns Oy Qt Vu) iZ(Dc Dk dN gP Ha Io Jk Md Mu Mv Pe pF Pg Po Tn Vp Vu) Mr(Hq Hw Hx Ii Ij Iq Kj Lz Mj Oy Qw Qx Ul Uv Wm) Jl(aJ Ao bA bV cH Cw Di Hq Kg Kj Or Oy pF Rb Rc) bA(aH aI aO Bg cE Dc Dk Hx Ma Mv Nq Nv Pg Po) Ao(aI bJ gP Hc Ii Jj Md Me Mj Pg Qx Rb Ul) Iv(Hq Hw Hx Ii Ij In Iq Lz Mj Oy) Ut(aA aJ aZ bJ bV dE dM gP Kg Ul) Bg(bJ Ha Iq Jr Ks Me Mj Pg Ra) Gl(aA aX bJ bV cM gP Kg Kj Vu) Rb(Ii Kj Ks Md Mk Mu Na Of Vu) Jj(aI cE Co Cw gP Ke Qt Rg Ul) Oy(Aj Co Ef Iz Jg Kg Mi Mk Vu) Mv(aJ gL Ha Ks On Qx Ra Uk) Hq(Hw Lx Mi Mk Ok On Pe Wm) Jk(aI aJ aX bJ bV cH gL Ra) Mj(aI Ax bV Co Kg Or Ph) Hx(aA Aj Ih Kj Ok Or Wm) Dc(Ax cH Id Or Qx St) Ns(aA Ih Ji Mi Ok On) Ii(bJ Ji Mi On pF Qe) Iq(Fp Ji Lv Mi Ok On) Kj(aI bJ Ha Po Rg Ul) Me(Ha Kg Vp Vu Tj) Mu(aJ Jg Qx Qy Ra) Nf(aH aX Cw gP Vu) Of(aA bJ Ke Rg Ul) Oz(aH bF bZ Co Kg) Po(Ar Fp Id Qx) Hw(Ji Mi Ok On) Qy(Co Kg Qt Vu) Qw(aI Md Rg Ul) Jo(aX gL gP Vq) Jr(aA Ax cH iJ) Om(aX cE gL Vs) pF(aI Kg Ql Ri) Dk(aA aI bJ) Wm(Ij Md Mk) Fp(Ha In Ok) Qx(cE Pg Vu) Cw(Hf Mb) Nq(aJ gL) My(Mw Nw) Io(iJ Vu) Ok(Lv Mq) Vs(Kd Ly) aA(Ik Lx) bL(aJ dE) AxPg EmUe HaOa NtRi NuIn MbMi MdKg MkRa NaQt QcQe JgJh JiOg NwNy UpaI aUaV} Ly{Sr(aN Bg Ch Cp Ct Db Dd Di Dk Hq In Jj Jl Jo Ma Nd Oe Oy Pg Po Qw Ri Uk Ut Vo Vp) Ko(aI aX aZ Bg cE Ha Hf Hq Jo Kg Ld Ma Md Mr Mu Mv Na Nf Oe Of Pg Ua Ur Vs Vu) Db(aJ Bg bL bV cE Ch Ct Di Dk Fp Hq Id Jf Lj Lx Mb Mj Mu Mv Om Pg Uk Vu) Dk(aJ bJ Bo cM Dl Fp gL Id It Jt Kc Mb Mm Nx Oy Oz Pc Pf Qe St Tt Uh) Md(Dc Dg Fp Fr gL Jf Jl Jr Li Lj Lv Mw Nb Ne Nh Nm Nn No Nr Og Om Qa) Jj(aA Hf Hw Ir Is Jl Jn Jr Kp Lv Mg Nd Nn Ny Og Oh Oz Pc Pf Pj Ri Wm) Im(Hw In Iu Iv Jo Js Lh Mr Nc Nd Ne Nf Nh Nj Nt Nx Of Om Ut Vu) Dc(Aa aJ dJ eF Fy Hf Ih Jf Kc Kk Mb Mm Nf Nm Nx Rf Ri St Uh) Id(Bg Hf Hw In Jf Jl Jr Kp Mu Mv Na Oe Om Pg Ut Vp Vu Tj) Og(Ih Is Iv Jh Jl Jq Jr Jt Mr Nh Nj Nr Ny Oh Oi Pf Pz Qa) Ha(Ar aZ bA cH Dg Hf It Jg Kc Lj Lx Oa Ok Pa Qe Uh) Uh(Bg Cp Hq Ii Jk Jo Mj Mk Mr Mu Mv Of Pg Ut Vu) Dd(Dg Fp Hf Ik Jp Jr Kc Nr Oe Oy Oz Pc Vq) Qe(Bg Hw In Jk Lv Nd Nf Nh Nj Of Qc Ut Vp) On(Fp Ih Ii Jg Lj Lv Mm Mv Nh Nj Ns Ny Ut) Dg(Bg Ct Hq Ii Jl Ma

Dr(Qt Ra) Iq(Js Of) eM(Fb Qu) DcId GcIb HaLj NuHq RcdX JjPa OgOi} Me{Sr(aN Bg bN cE cM Db Dk Hf Hw Jk Jl Kp Md Mk Mr Mu Mv Nf Oe Of pF Pg Ur Ut Vo Vp) Hf(aJ bA Bg Dc Dd Dk dM Fp Hq Jj Jk Js Lx Md Mj Mk Mu Mv Nf Om Pa Ri Ur Vp) fR(cE cP cQ Db hC Jk Jr Mp Nf Nq Oe pF) Id(cM Db Js Kr Md Mj Nf Oe Om Pb Ur) Jf(Dc Dk It Jk Kc Mu Na Pa Pj) Vq(Bg cM Ef Jk Jn Mv Oy Ri Uk) bN(Ki Kk Kp Nj Oz Pc Qw Uk Wm) NI(aA Fp Hw Ni Ns Pb Pc Pg) Ik(aX Bg Dc Iu Ji Nc Ne Nh) dE(Ha Qw Ur Ut Vs Wm) Kk(cE cM dJ Ld Mu) Dr(Fp Ih Lv Mf) Kr(Aa Dg Lx Pj) aX(Lv Uk Ur Vo) Dc(Ad Kc Qh) Dk(Kf Kq) Lv(Nh Nj) Mi(Ne Nj) aZ(Uk Ut) DgVo DiUr FpNh HaPa NeJi JkKf JsPj OmUh} Jj{Nj(aA Fp Hw Ih Ii Im Ip Is Iv Jl Li Lj Lv Md Mg Mi Mk Mr Mz Nb Nh Nu Nv Oi Oy Oz Pb Pc Pe Pg Pz Qa) Nc(Fp Ih Im Ip Iv Jm Jt Lv Md Mg Mm Ni Nk Nr Ns Nu Nv Om Oz Pb Pe Pg Pz Qa Qe) Nh(Fp Ih Im Iv Jp Jt Lh Lv Mg Mi Mr Nu Pb Pe Pg Pz Qe) Pa(Fp Iv Ji Jp Jr Lv Mf Mg Mm Nr Nu Nx) Nr(Iv Ji Jp Mf Mm Nu Nx Om Oz) Ne(Fr Ih Iv Li Mi Mr Nu Oi Pb) Md(Fp Ji Jp Mm Nu Qe) Nx(Ex Fp Jp Mm Nf Qe) Ji(Hw Hx Lv Nf Om) Mm(Jr Lv Nu Oz) Ik(Aa Jl Mi Mr) Qe(Hx Lv Nq Oz) eM(aX Ih Oi Vv) Jp(Lv Mf Nu) dX(dJ Dl Jm) Em(Og Ph) Om(Jm Mg) AaOz MrMt HwQa} Nf{fR(aD cG cQ Db It Iv Ml Mv Nl Nq Oe Ou pF Rc Um Vo) Ik(Aa Fp Fr Is Jl Lh Li Lj Lv Lw No Nv Nx) Lx(AA Hx Iv Md Mi Mm Mr Mt Nq Pe) Lv(Im Iv Jl Jt Li Lj Mm Mr Pa Qa) Jp(Ih Iv Jr Js Lh Mf Mi Pa Pe) Nx(aJ Dc Fp Id Is Kk Nb Pa Qe) Ji(Ih Iq Js Mm Mr Og Om Pb) Fp(Dc Fr Is Md Mm Mr Pa) Nu(Fr Jl Mi Nv Pa Qe) Nt(Fr Iv Lh Mm Pc) Id(Dc It Js Rb Ri) Vq(aJ aX Hu iZ Ky) Pe(Hw Md Mi Mm Nh) Qe(Md Mi Mm Qc) Kq(Dc Dk Om Vo) Lh(Md Mt Nj Nl) Aa(Jr Ne Oz) Iv(Fr Li Mt) Nv(Hw Li Om) Dc(Ad Ar) Nr(Qw Vp) Mm(Pa Pb) Kc(cM dJ) DgOe DrQw EmLd MdLi MiMt UhVo cLeP} Mt{Mi(Hx Ij Ik In Iq Js Lv Md Mv Nc Ne Nh Ns Of Og Oy) In(Ih Ik Is Jr Lh Lj Mr Nb Nc Ne Nh Pa Pb Pe) Iq(Fp Ih Iv Jl Js Li Lj Lv Mm Mr Nc Ns Og Pe) Og(Iv Ji Js Mm Nc Nh Nq Oz Pa Pb Pc) Iv(Hq Hx Ij Js Md Mj Nq Om Oz) Pa(Ji Js Lv Mm Ne Nh Ns Nt Om) Ns(Hw Lv Lx Nc Ne Nt Om) Mm(Fp Ik Lv Md Nc Ne Oz) Ji(Ii Iu Jq Nc Ne Of Oz) Jp(Jk Mv Nc Ne Ng Of Oz) Mr(Fp Nj Nl Nq Oy) Md(Jr Nb Nv Ny) Ik(Iu Jk Ng Of) Nq(Ih Li Nt) Js(Lv Nc Ne) Om(cH Dc Jr) Nt(Iu Oz) Lx(Hq Iu) Mv(Fr Pc) Qb(Lv Qe) Jk(Ih Qe) AaOz DcIt MkHq NcNk NjaA HwJl} Md{Fp(Fr Iv Jh Ji Lh Mg Mi Mw Nc Nj Nv Ny Om Oz Pa Pg) Nl(aA Im Ip Jq Jt Lh Lw Mp Mw Ni No Nv Om Pb Pc Pg) Nj(Aa Fr Im Lh Li Lv Mi Nu Nv Om Pe Qa) Nh(Im Li Lv Mm Mw Nt Nv Og Pe Pg Qe) Ik(Fr Lj Lv Mi Mp Nc Nv Om Pe Pg) Ne(Li Lv Nb Nm Nv Og Pa Pe Qe) Jp(Hw Hx Iv Ji Jr Nq Oi Oz Pa) Nx(aA Iq Iv Mw Nb Pc Pe Qe) Nt(Mi Mm Nc Om Pc Pe) Lv(Nc Nv Pe Pg Qa Qe) Nu(Im Nv Pe Pg Qe) Lx(aA Iv Mm Pc) Nv(Hw Nq Om Oz) Mm(Nc Oz Pb) Ji(Iq Nc) ArpF DgVo IdRb KcdJ} Nl{In(Fp Ih Im Is Iv Jt Lh Li Lj Mi Nv Pg Qa) Nk(AA Fp Ih Is Iv Jt Lh Li Lj Pe Pg) Hw(Fp Ih Ip Is Jt Lh Li Lj Pe Pg) Iu(Fp Fr Ik Im Jt Lh Li Nv Pe Qe) Om(aA Fr Im Lh Mi Nt Nv Nx Pa Qe) Ns(aA Fr Mi Nt Pc Pe) Mi(Ij Lz Ml Of Oy) Iq(Fr Im Jt Lh Li) Og(Is Jl Mr Pb Pc) Js(Im Lh Nv Qe) Ni(Li Lj Pc) Jk(Fr Lh Qe) aA(Fp Lw) DrQw FrMv LvMr MyNx QcQe LhOf} eP{Hu(aN Cs Cu It Ji Jr Lj Nt Oh Pe Qa Qz Ri) cF(aM dL Ib Lv Nj Nx Pj Rb Rc) cL(bU bZ cB cH Cs Ma Mq Pa) Ib(aC aG Fw Ir Jl Jy St) Qy(bW cA Di Ji Mr Pb) Nb(Mv Mw Oz Pb) Ih(aD Jk Kn Tv) aV(cH cS Di Fw) aX(aU dF gW Vv) eF(aK cY Dd Og) Rc(Dl Ir Pj) Rf(Mw Ns Qh) aZ(Kn Og Ra) aJ(aK cY) aM(bA bR) AdUf BoDi DlQu DpNx FbMf FwGt HaRm NsOu TvOi KfcC KzdK} Lx{Og(aA Iq Iv Ji Js Nq Ns Oz Pa Pc) Mi(Hw Hx Iq Js Lv Nc Nq Oz) Iv(Hq Hw Ij Iq Js Nq Oy Oz) Ji(Ii Ik In Iu Jq Nc Of Om) Mm(Hx Iq Js Lv Nc Nh) Om(Lv Nc Ne Nh Nt Po) Mr(Hw Ik Nc Ne Nh) Iq(aA Ik Js Lv Pa) Po(cH Id Kc Kk) Aa(Js Ma Oz) Jk(aA Jp Mg) Dc(Ad Kc) Nq(Hw Pa) Ns(Js Oz) Ik(aA Hq) In(Fp Ih) Oy(Mk Pc) GlPb HaLj MgJo NcIu IiNx OzaA} Nj{Og(Fp Fr Ik Im Ip Iv Lh Li Lv Nh No Nv Oi Pe) Nt(aA Fr In Js Ns Om Oz Pb) Mi(Fp Hq Iv Lj Ni Nx Om Oz) Lv(Fp Fr Ih Iv Jt Lj Pe) Qe(In Iq Iu Iv Nk Om Qc) Nv(Hw Iu Jk Js Of Om) Fr(Fp Iu Iv Mv Pa) Aa(Gc Js Ma Ni) Mm(Ih Is Li Mr) aA(Fp Jr Lh Nx) Iu(Jt Lh) Ji(Iq Jq) Nx(Hw Lj) cM(cF Kz) fR(cQ Mp) DrKc NiLi IvPa RcdX} eM{aX(aU Bc Dd dF Dg Fp Lj Lv Pe Qd) bE(Fa Fb Ib Ki Kn Ld Mf Or) cF(Dc Dd Di Ef Gl Ib Qu Rc) Gl(Jy Oe Rf Vv) Kz(aC fR Rf Ue) cF(Hb Hf Jy Oa) Hu(bR Rc Wm) Ib(Hw Qd Rm) aN(Di Hf Ih) cL(bZ cB cC) Ns(Qx To) Mf(Fb Qz) Kf(Rc Uf) Rf(cV dI) Oa(Mr Po) Vv(Ma Qu) aC(Uu Wm) bW(aJ dG) ChNx DifR QndB UkcM aDaG bCdO cNdJ} Nt{In(Fp Ih Ji Lj Nc Ne Nh Ns Pb Pe Qe) Ns(Fp Iu Lv Nc Ne Nh Oz Pb) Pa(aA Hw Ji Js Mm Nc Nq) Om(Fp Im Ji Lv Ne Qe) Js(Fp Im Lj Pb Qe) Mi(Fp Hq Ne Oz) Nc(Hw Jp Nk Oz) Nh(Hw Iu Jp Lv) Iq(Im Ji Lj Qe) Iu(Fp Ik Ne) Jk(Im Qa Qe) Of(Ji Nx Pb) Mm(Lv Oz) Jo(Ji Lh) Jp(Fp Mv) NeNk QcQe OgaA OyPc} Og{Ne(Aa Fp Ik Jh Jp Jq Jt Li Mi Ns Nx Oi Pe Qe) Nh(Ik Ji Jp Jt Lj Lv Mm Nx Oi Pe) Fp(Iv Lv Mg Mi Nc Nx Oi Pa) Ik(AA Is Jl Mr Nr Om) Lv(Ji Jp Jt Li Nc Qe) Nu(Mg Nx Pa) Nc(Ji Nx Pa) Oz(Aa Ji Mm) Em(Fn Je) Oi(Ji Pa) MiNx} Kc{dJ(Aw aZ Dc Dk In Jk Jr Js Kg Mq Nu Oe Om Ul Vp Tj) bN(Aw bI dI Ic Jr Mj Mu Oe Qw Ra Vp) Jf(Aa bL cM Dc Di Iq Jk Ki Mu Pj) Nx(Dc Gc Ha Jk) Gc(gW St) Mv(bJ eF) cM(bI Nu) AaVo DbbL DrNi VseF} Jp{Nc(Fp Iq Js Nk Ns Nx Om Pa) Nh(Fp Iq Js Lv Mi Of Om) Nq(Iv Js Lv Mf Nu Pa) Nu(Hw Hx In Js Ns) Dc(Gl It Jm Rb) Nc(Fp Mi Nk Om) Mf(Hw Iq Js) Hx(Fp Iv Ji) Lv(Fp Pa) Iq(Ji Pa) Rb(Bg Mu) DdGl MjIv MmIk} dV{fR(Ad aM bA cB cF cG cH cI cL dF) aJ(bC cC cE cR dA dN) aX(Ar cB cL Dg Ex) bF(aD bA dG dL dN) dM(cL cP cS dG) cF(Ad aP cR) cG(aY cS eX) bC(Cs Fw) bQ(bU eX) bR(cO cR) dF(aF cM) dG(bW gC) aPeX} Ik{Pa(Hw In Iq Ji Jo Lv Mi Nc Ns Om) Qe(Hw In Iu Jk Jo Ns Om) Mi(Fp Hq Iu Jo Oy) Mm(Hw Iu Lv Ng Ns) Ji(Hw In Iu Of Om) Aa(Jo Om Oz) Nx(Iu Jo Of) Im(Of Om) Jl(Hq Oy) FpIu JoLh NvOf} Nx{Dr(aN Ba bL cF Cu Fy Ij Jh Ma Or Qh) Mi(Fp Hx Mv Of Oy Oz) Dc(Ar Fp Lj Qe) Em(Ke Kg Kl Tt) In(Ne Nh Nu Oz) Hw(Nc Nh Nu) FpMq HaLj NsOz NeaA JriZ} dO{aX(Ap bF Bo cB cN Cv DD dL eF Fr) cN(Ad aI Bc bO bU dF dI dM) aN(cE dM Gt) bC(Ch cR Dd) dG(cC cE cR) aJ(bL bX) aK(cF eF) AdfR BcbE bRcS bUdM} Dg{Vo(aI Bg bN bZ cE Dc Di Gl Jf Jk Jo Ma Mj Mu Mv Qw Ri) Jk(Jf Kk Om Ou Qx) Dc(bA Db Jf Om) Ri(Oe Om Qw) Dk(aJ bA) GlUr MaOm JoPb aJbN} Ne{Hw(Im Ip Li Mi Mm Nv Pa Qa Qe) Mm(aA Fp Iq Ji Ns Om) Pa(AA In Iq Ji Mi) Fp(Lv Mi Ns) Ji(Iu Ns Oz) Aa(Ma Om) In(Pe Qe) Iq(Mi Qe) NsLv} Em{Qz(Aj dN In Om Uu) Kj(Mf Oh Ph Rf) Vo(Bc gL Je Pb) Nu(In Pc Ua) Ue(cR Ou Ph) Ur(aJ Fn Hu) Uo(cY Jc) Ph(Jf Uu) aV(To Uk) AjQw AxQt HaNv IiOu} fR{Oz(aG aH Aw Ax Cs Cw hC Oh pF Ra) Rb(bN De Hu Lz) Pc(cP cQ Iq Mj) Db(Bo bU cP) Mj(Ou Ra) Qw(hC Pg) pF(Lv Ql) GwaD HuKd QdQx QyJk QuOu} Nh{Pa(aA Fp Iq Ji Lv Mi Mm Ns Om) Qe(In Iq Jk Js Of Qc) Ji(In Iq Om Oz) Nv(Hw Js Of Om) Hw(Ih Pe) Lh(Jo Of) AaOz LvMm ImOm InPe} Dc{Ad(aI Aj Dk Fp Gw Id Lj Pa) Qe(Jf Mj Oy Qc Rb) It(Ar Jf Rb) Gw(cH Gt) Kf(Jf Om) GlLh NrOm} Aa{iZ(cM Hx Jf Jr Js pF) aX(aJ Jf Qw Rb Rj) Oz(Fp Jr Ma Om) Kk(Js Om) aJ(bL bU) GcKy NcOm} Dr{Rb(aC cN dI dJ Mm Mr) Qw(In Mr Qt Uf) aV(Dl Ex Mm) Ra(Oi Or) cN(Gw Mv) FwGl RcKf} Gt{aN(aA bN cG cP dI dR eX) Fw(Al bZ Cq cY Gp) Dd(bC cB cC) BoDb GpcF aMcC dMgW} Vq{iZ(Ct Jk Mv Oe Qt Ua) gW(aK aV cY) Uk(Hu Ra) Oy(gL Pa) MqiH MvgL HwpF JohB VoaX VskS} Gc{Ue(aZ Dp Ha Kj Na Ny Or Qt) Kj(aC dJ Hu Or Ra) Vo(dJ gL Pc) CsUf HuRc} cH{dF(aH aI aW bN) bA(aH aL cT) dM(aZ bU cQ) aJ(bU gC) GwcP NrOm QyJk aAaZ bNgL dLgC} Nc{Lv(Fp Iv Mm Ns Nu Pa) Hw(Fp Nv Qe) Ji(Iq Ni Oz) Pa(Fp Mm Nk) MmOz IqQe} Gw{aD(aJ aW bC Bg cG dL) aN(aI Cs dG) Bc(Al Ct) ChbC CtbA DbDd} Fp{Lv(Mi Mm Pa) Im(Hw Js Om) Oz(Ji Mi Mm) Iv(Hx Mj) JiJs JoLh} Kk{Ex(Kx Om Qw Vo) Mm(Jk Mj) Ki(bN dJ) OmdJ VoPj} pF{Jr(Ax Fr Kq Nr Qe Sr) Ar(Mj Vu) SrQl} Dq{Di(Bo eF) Fw(Cq Gp) CsbC aKdN aMcE dKdR} Mm{Lv(Ih Om Pa) GlUr HaLj NqPa JiOz} aJ{bN(bR cM Db) Rb(Mj Mu) bLbR cMgC} dX{To(Di Hu) Qx(aR Up) AdRc UvcP VvcN} eX{aN(aK Bc Dd Dl) aK(bR cR) cEdJ} Ha{NmiZ NrOm IdIt RbPe LjPj} Nu{Pa(Hw In Ns) MiOz IhIn} Jf{Ap(Bg Mv) JkKf OzPj} Ji{Oz(Jo Ns Om) LvJo} Ut{gL(Kq Pa Qe) KqVo} Gl{Ur(Sr Uh) PagL} Om{Nr(Vp Vu) IqNv} dG{gC(cY dA) bZcT} Dv{cL(aD cW)} It{ArPo MjId} Rb{OuaX aUaV} gN{FwbF bCdJ} iZ{BbJr NmRi} LvIhIn OuVsaX VoOyPj

Constrained panels with 2 analytes, where 1.0E-7 >= 'AUC p-value' > 0. Contains 80 panels of 77,685 total panels evaluated. : Gn(aD aV bR bU Ch cP dJ dL Ef Gl Hu Ly Om Ra Rb Rc Ue Um Uo Vo) Et(Jj Jo Jr Jt Lx Ly Md Mt Nc Nd Ne Nf Nh Nj Nl Of Om Oz Pa) Ok(Hw Iq Jo Js Jt Ly

Figure 11 Continued

Md Nc Nd Nf Nj Nl Nq Om) Nw(Hw Ik Iq Js Ly Md Nc Nd Ne Nf Nj Nl Om) Lx(Ly Nd Nj Nl) Ly(Jg Jp Mt) Nl(Jj Jp Mm) Nt(Jj Og) NjJp aVdO

Constrained panels with 2 analytes, where 1.0E-6 >= 'AUC p-value' > 1.0E-7. Contains 108 panels of 77,685 total panels evaluated. : Nw(Hx In Jj Lv Lx Mt My Nh Nq Ns Nt Of Og Oz Pa) Gn(aJ aX cF cH cN dl Fw Jj Kc Me Og Or Qu Qw) Ok(Hq Hx Ik Ij Lv Lx Mt Ne Nh Ns Of Og Oz Pa) Et(Dk Fp Gl Hw Ik Iq Js Lv Nq Ns Nt Vo) Lx(Ik Jg Jj Lv Nc Ne Nh Nt Po) Ly(aX bN cH Fr gP Jj On Pa) Mt(Fp Hw Jj Md Nd Nj Nl Nq) Nl(Aa Fp Jg Ji Lv Og Pa) Nd(Jg Mi Nt Nv On) Ik(Jj Jp Og) Jg(Nj Of Om) Dq(eF Fw) Ne(Jj Jp) Nh(Jj Jp) MdNx MmNj NfJi dGdV Constrained panels with 2 analytes, where 1.0E-5 >= 'AUC p-value' > 1.0E-6. Contains 196 panels of 77,685 total panels evaluated. : Ly(Aa aJ Db Dc Id Im Ir Ji Lh Li Lj Mi Mm Nc Nl No Nt Nv Nx Pe Pg Qe Sr) Jg(Fp Ik Iq Iv Jj Jk Md Mt Mv Nc Ne Nf Nh Nq Ns Og) Nt(Fp In Jp Lv Md Mt Nc Ne Nh Nj Nl Ok Oz Pa Pb) Mt(Iq Ji Jp Js Lv Lx Nc Ne Nh Ns Og Om Oz) Nj(Aa Fp Fr Gn Ji Jj Lv Mi Nv Nx On Pa Qe) Et(aA Bg Ch Dc Ih Jf Ji Mi Ok Ur Ut) Nl(aA Fr Md Mi Nk Ns Nx On Pc Pe Qe) Gn(Cs dG Gw Jy Kf Kj Kk Mf Uf Uu) Lx(Hw Hx Iq Ji Js Md Nf Nq Og Oz) Nd(Aa FR Im Ji Jl Jp Mm Qa Qe) Fp(Ik Lv Md Ne Nh Nx Og Ok) Ko(bN Dc Dk Jf Jk Js Om Qw) Lv(Ji Jp Nc Ne Nh Nx On) Jp(Mb Md Nc Nf Nq Nu) On(Hw Iq Nf Nq Om Oy) Dc(Ad Nw Ok) Mm(Ik Ne Nw) Ji(Ne Nh Oz) Pa(Ik Nh Nu) gP(fR gL Kk) Dk(Nw Ok) aJ(bU dO) DdGw DrMe FwGt MqOk NcJj NeOg HwNx IkQe cHdM dOfR Constrained panels with 2 analytes, where 1.0E-4 >= 'AUC p-value' > 1.0E-5. Contains 392 panels of 77,685 total panels evaluated. : Ko(Bg Ch Cp Di Gl gP Ha Jo Jr Kj Ly Ma Me Mj Mk Mu Mv Nf Oe Pg Po Ri Ua Ur Ut Vo Vs Vu) Et(aI Ao bN cE Co Ct Cw De Di Ef gP Ha Ib iZ Kc Ke Kg Kj Ks Ou pF Qt Qw Tn Vp Vu Tj) Ly(aA Dk Fp gL Ih Ik Is Iv Jf Jh Jl Jr Lv Lw Md Ne Nh Nj Nr Og Oz Pc Pf Qa) On(Fp Hx Ik Jj Jk Js Lx Md Mt Nc Ne Nh Ns Nt Nu Nx Of Oz) Lv(Ih Ik Im Iv Jg Jj Li Lj Mm Nd Nf Nr Nu Oz Pa Pe Qe) Nj(aA Ik Im Ip Jr Jt Lh Li Lj Nu Og Pb Pc Pe Pg Qa) Nx(Ik In Jj Jp Lj Mi Nc Nd Ne Nf Nh Ns Nu Og Oz Qe) Nd(aA Fp Jh Lh Li Lw Mz Nb Ne Nh No Nr Pe Pg) Jg(Hw Ih Iu Ji Jo Js Lj Mu Mw My Nt Oy Oz Pa) Jj(Fp Iv Ji Jm Jp Jr Lh Mm Nr Nu Pa Pe Qa Qe) Nf(Ar Fp FR Id Ik Lh Li No Nu Nv Pe Qe) Nh(Hw Ih Jt Lh Li Lj Md Mi Mm Ns Og Pe Qe) Ne(AA Fr Ik Im Li Lj Md Mi Pa Pe Qe) Ji(Fp Hw Ik Iq Iv Jo Js Md Nc Nq Nt Om) Nw(Ao Bg Co Gl Ha Ib pF Rj Ut Vp Vu Tj) gP(aJ bA Bc cH Dg dM eF Jf Kc Qw Ur) Ik(Fr Jl Li Lj Md Me Mi Nc Ns Pe) Jp(Fp Hw Hx Iq Iv Js Mf Ns Oz Pa) Ok(Bg Co Gl Ha Kg Tn Ut Vu Tj) aJ(Aa bL bN bR cH cM Dg dJ dV) Nu(Hw Im Jl Md Mi Og Oz Qe) Nt(aA Js Mi Mm Ns Om) Mt(aA Iv Mi Mm Mr Pa) Nc(Fp Li Mm Nk Og Qe) cH(aA aW bA dF dG gL) Dg(bA Dc Di Dk Vo) Gn(Fb Ld Oa Ou Qx) Me(Hf Id Jf Sr Vq) Qe(Dc Hw Iq Md Qc) dG(bU cM dH dO gC) Fp(Iv Mi Om Pa) Lx(aA Iv Mm Ns) Nl(Iv Jt Lh Om) Kc(bL bN cM dJ) Nv(Hw Iq Om) Oz(Aa Fr Mm) Ad(Ct Dk) dO(aX cN) dV(eF fR) eP(aV cL) DrGw GtaN MmPb JfPj PcfR bAbU Constrained panels with 2 analytes, where 1.0E-3 >= 'AUC p-value' > 1.0E-4. Contains 684 panels of 77,685 total panels evaluated. : gP(aA AP Ar Bb bV cB dG Dl eM Fr Gt Id iZ Jp Kp Lv Lx Me Mt Nd Nf Nw Nx Ok Om Oy Pa Pc Ph Qe Qy Rb Rj Sr Wm) Jj(aA Dg Fr Ih Ii Ij Im Ir Is Jh Jt Ko Li Lj Md Mf Mg Mr Nd Nv Oh Oi Om Oy Oz Pb Pf Pg Pj Pz Rb Rf) Dg(aH aW Bg bN cE CH Co cP Ct Cw Db Dd dM GL Ha Iq Jf Jk Jo Kj Kk Nd Nf Oe Of Om Qw) cH(Aa aP aZ Bb bN cB cP eF Gt Gw Iq Lv Nd Nf Nj Nu Nw Ok Om Oz Pa Pb Pc Qw Qx Rb) Aa(aV aX bA dG Ik iZ Jf Jr Kc Kk Lv Lx Mt Nc Nf Nh Og Om Pc Qw Rb) Mm(Fp Iq Jf Jg Ji Jp Jr Lj Mb Md Nf Nq Nu Nx Og Om Pa Qe Qw Ur) Ko(aI aX aZ cE dM Hq In Jl Kc Kg Md Mr Of Pa pF Qc Qt Rb Vp Tj) Nc(aA Fr Hw Im Ip Is Iv Jt Lj Md Mi Nd Ni Ns Nu Pa Pb Pe Pg) Nf(aJ Ap bA gL Im Ip Is Iv Kk Kq Lj Ly Nb Nr Pg Qa Sr Uh) Qw(aX bA bN bV gL Id It Jf Jg Jp Kc Me Nr Nw Ok On Rf Sr) Om(Ad bA eF gL Ik Im Jp Kq Li Lx Ne Nh Nu Pj Qa Qe St Uh) Nd(Ar aX bA Bb Ih Ip Is Iv Jt Lj Mx Nu Og Pa Pf Pz Rb) Nx(aA Bg cE Ct Dc Dk Ha Iv Jl Lh Li Mr My Ny Pe Ut Vp) Dc(Ap eF Fp Id Ik It Jg Jp Kf Kq Lj Lx Mt Nr Sr) Iv(Fr Hw Ik Im In Li Lj Ne Nh Nj Nu Og On Pb Qe) Ok(aH aI Ao aX bN cE Ch Ct Ib Jf Qt Rb Ur Vp Vs) Ly(Hf Hw iZ Jt Kc Kp Mr Ou Pb Ph Ri Uk Ur Vp) Md(Fr Id Im Kk Lh Li Lj Lv Nj Nr Nv Ny Pe Qa) On(Dk Hq Ii Jg Jo Jp Lj Mb Mf Mv Ng Og Qe Ut) Jp(aI Bg Dk Gl Ih Jf Mi Mr Og Rb Ri Ut) Ha(Ar Fp Id It Kf Kq Lj Lx Nr Pe Qe) Me(Ar aX bA bN fR Kc Kp Ri Uk Ur Vp) Nw(aX bJ bN cE Jf Ou Qt Qx Tn Ur Vs) Og(Ir Ji Jt Lh Li Lv Nr Nv Oi Pe Qe) Mr(Ar Fp Id Ik Jg Lv Lx Nh Nj Nl) Oz(bN fR Im Lh Li Lj Mi Nr Nv Qe) gL(bN dJ Et Jf Jk Mu Mv Pc Ut Vs) Ap(aH cE Ch Di Dk Gl Mv pF Vo) Nj(bN Hw Ih Is Jl Mk Nb Nh Nr) Iq(aX fR Im Kc Lh Li Pe Pg Qa) Et(aH aO aX bF cG Cp Rg Vs) Nu(aA Fr Ih Is Lj Ns Pb Pe) Hw(Ih Im Ir Is Li Pe Qa Sr) Jf(Dl It Kc Nm Nr Ph Rf Sr) Jg(aA Bg Dk Gl Jh Mi Ng Vo) bA(aJ bN cB cT Db Di Dk Pc) dG(bN bR bZ cB cE cL Dk Mj) fR(AD aM cP Db Di Lv) Ns(Im Ji Li Nc Nv Qe) Id(Jk Mj Po Rb Ri Rj) Kk(dJ Mu Mv Nm Pj Vp) Kq(Dk Mu Mv Ut Vo Vp) aA(bR bU Fp Ik Jr Nh) dF(aH bN bU cE cM dV) eF(Bg Ch cM Di Dk Jk) Ad(Bg Ch Di Jk Oe) Gl(Lh Lx Qe Sr Uh) Pc(aJ Ar aX bN dJ) Nq(Fr Li Nv Qe) Nr(Ut Vp Vs Vu) Mi(Lj Lv Lx Qe) Rb(aX It Pb Sr) dM(aV bR bU cM) Ar(Ma Mv Po) Gw(aD aN dL) Ne(Is Jt Lh) Ik(Ih Is Lh) Js(Nv Pj Qe) Vo(Gc Pj Uh) Pa(Ji Lx Qe) aX(It Lv Ou) Ba(Ct Dk) Gt(Bo cF) Nv(Of Ut) bN(Dl iZ) bU(aP cR) pF(Bb Sr) DiaJ DqcF FrNh GnSt NmUr LvIs LxUt JiJq JkKf JoPj KcVs LhOf VqiZ aVbE cBcM cGeP cNdV Constrained panels with 2 analytes, where 1.0E-2 >= 'AUC p-value' > 1.0E-3. Contains 1,271 panels of 77,685 total panels evaluated. : bN(AA Ad AP Bb BC bV cB Db Di dM eF Ic Id iH Ik It Jf Jg Jp Kf Kk Kp Lv Lx Mm Mt Nd Nf Nh Nr Nu Nx Oe Om Ou Oy Pa Pb Qe Qx Qy Rb Sr Ur Wm) Aa(aP aW bC bV cB cM cP Dc dF Di Dk dM eF Fp gL Hw Iq It Iv Jg Js Kd Lu Ma Mb Mf Nr Ns Nt Nx Oi Ou Pa pF Qy Rj Uk) Vs(Ad aJ aX bA Bc Dg Dl dM eF gP Ic Id It iZ Jp Kf Kk Kp Kq Lh Lx Mm Mt Nx On Ou Oy Pa Ph Qe Qx Rf Sr St Tt Uh Vq) Dc(Ar Ba Bb Bc cH Cu Cv Dl Fr Fy Gw Ji Jm Jt Kc Kk Kp Lh Li Me Nj Nu Nv On Pe Pj Pz Qa Qh Rb Rf St Tt Uf Uh) Kk(aX Bg cE cM Di Dk Ex Gl Ha Hx Ib Ic Iq Jk Jr Ld Mj Mk Ml Mm Mw My Nd Nq Om Oy pF Po Qw Ut Vu Tj) Gl(Ad Ar aV BA Bh dF eF fR Ic Id Ik It Ji Ke Kf Kp Kq Mm Mt Nr Nv Nx On Pa Pj Rf St Ur Vq) Iq(aJ Ap Ar bA Bb Dl Fr Id Ih Ip Ir Is Iv Jl Jt Kq Lj Mi Nb No Nr Nu Nx Oh Pa Pz Qd Sr St Uh) cH(Ap Bc cR Db Dl eP fR Ha hC Id In It iZ Jf Jj Jk Jp Kp Lx Md Me Mt Oe Ou Oy pF Ph Qy Ur Vo) Sr(aX Bg Ch Di dJ Dk Ha Hq Ib In Jj Jk Js Kc Md Mj Mr Mu Mv Nd Oe Om Pg Po Ur Ut Vo Vp Vu) Ap(aI Ao aW Bg Co Ct Cw dM Ha Hq Hw Ib Ii Jj Jk Jo Kg Kj Ma Mj Mu Oe Of Om Pg Qt Ut) Dg(aA aI Ii In iZ Jl Js Kg Ma Md Me Mj Mk Mp Mu Mv Nj Pc Pg Po Qt Uk Ur Ut Vp Tj) Jf(aX cM dE gW hC Hw Ic Io Jk Kp Lx Md Mj Mr Mu Mv Nf Ou Oy Pa Pc pF Qy Rb Ri Vp) Om(aA Ar Ba Bb bJ dJ Dl FR Ic Id Lh Lj Lv Md Nc Nj Nr Nx Pe Pg Qw Rb Tt Vq) Uh(aI Bg Ch Di Dk Ha Hq In Jj Jk Jo Js Ma Md Mj Mr Mu Mv Nd Oe Pg Ut Vp Vu Tj) Vu(Ad Ar Bb Bc gL Id It iZ Jg Jm Jp Kc Kf Kn Kq Lh Lj Lx Mt Nx On Pa Qe St) aA(Ad aX bA Bc cB cM Di Dl Iv Jn Lh Li Lj Lv Md Mf Mm Ns Og Oz Pa Pc Pe Qe) Vq(Ct De Ef gP Hu Jj Jk Jo Kj kS Ky Mq Mv Nf oE Og Or Oy pF Qt Ra Uk Vo) aX(Ad Bb dV eM Iv Jj Jp Kp Lx Mt Nf Nj Nr Nu Nx Pa Ph Qe Qx Qy Rj Ur Vo) Rb(aJ aZ dE iZ Jk Lx Md Mj Mr Mu Mv Nf Nm Ou Pa Pc Pj Qw Uk Ur Vp) Dk(Bb Bc Cu Dl Fr Id Ik iZ Ji Kc Kf Lh Lx Mt Nr Nv Pj Qe Rf St) Hw(Ad bJ Fr gL Jh Jj Jl Jr Lh Lj Mf Mg Mm Mx Nb Nd No Nr Oh Pg) bA(Ct Dl Ha Hq It Jk Lv Ma Md Mr Mu Mv Oe Oz Pa Pg Ut Vp Wm) iZ(Bb bJ cM hC Hx Il Jr Md Me Mj Mu Nf Nk Pa pF Ri Ur Ut Vp) Qw(aJ Dl Fp Kp Lx Mt Nf Nm Nu Oi Ou Oy Pa Ph Qy Ri St Ul) dJ(aP bE dF dM eM eP It Lv Nd Nj Oe Oy Oz Pb Ph Qy Rj Wm) fR(aK aQ aV aW cB Cv eM hC Jk Kz Mj Ml Mq Mv Na Oe Pa Rc) Ad(aJ aW Dd dM Hq In Jj Jo Js Kj Ma Mj Mu Mv Pg Ut Vo) Di(aV Ba Bb BC bU cB cM cP dF dG dM gL Ic Jp Kc Ur) Kq(Bg Ch Hq Ib Jk Jl Jr Ma Md Mj Mr Oy Pg Po Qt Ua Tj) On(Bg

Figure 11 Continued

Ch Co Ct gP Ha Ib Ih Mm My Pa Pg Qt Tn Ua Vp Tj) Ar(Hq Jk Jl Js Md Mj Mu Nj Oe Pe Pg Rg Rj Ut Vp Tj) Jg(aH cE Ch Ct Cw Ef gP Ha Iz Kj Qt Rc Ua Ut Uu Vp) St(Ha Hx In Jk Jr Mj Mr Mu Mv Nd Oc Pg Qb Ut Vp Tj) Og(Fr Ih Im Ip Jh Jr Lj Mg No Oh Pa Pc Pf Pg Pz Qa) aJ(Bb bC cB Db Dl Lv Me Mj Mu Mv Nd Nq Nx Oe Oz pF) gL(Ch Dl Hq It Lv Md Me Mj Mr Nd Nj Oe Pa pF Ur Wm) Nf(Ih Ii Ir Jl Jt Kc Mg Mi Mr Pa Pc Pf Po Rf Ri) Id(cM gW In Jr Kp Mu Mv Nd Oe Ou Qy Ur Ut Vp Tj) Iv(Ih Jl Jt Lh Md Mf Mi Mj Mm Ns Oy Oz Pa Pe Qa) eF(Ct Db dE hC Hq Ib Mj Mu Mv Nd Oe pF Ua Ut) Dl(bC bI bU cB cP Db dM eM Ha Jk Oe Ur Vo) Kc(Bg cE Dd Hq Jk Mu Mv Nr Nu Ou pF Ur Vp) Lh(Bg gP Ha Hq Iu Js Lj Nc Ns Nu Ut Vo Vp) Rf(eM Ha In Jk Jl Ma Mj Mr Mu Mv Oc Of Rj) Oz(gP Ih Ir Is Jl Jr Jt Lw Md Mr Nb Qa) Bb(Bg cM Jj Jk Ma Mu Mv Oe Ut Vo Tj) Nr(Bg dM gP hC Ns Pb pF Ua Ur Vo Tj) Mm(gP Ha Ih Is Kj Li Mi Ns Pe Uk Vo) Jp(aH cE Ch Ct Ha Ib Qt Tn Ua Vp Tj) Kf(Bg Hq Jl Jo Kg Mj Mu Mv Pg Ut Vo) Nx(Ao bF Cq Dr Ib Ih Is Jd Pa Qt Tj) Md(Ir Jh Jt Mg Nb Nd Nm No Pb Pg) Mr(Im Li Lj Nc Nd Ne Nu Ou Pe Qe) Jj(hC Ip Jl Kp Mi Mk Pd Qy Ug Wm) dM(aK cB cP dO dV hC Jk Lv Nd Nj) Lj(bJ cP Fr gP Mg Pb Pc Qy Vp) dG(Db eP Jk Jl Mu Mv Nq Pg Tj) eM(cB dL Fa Ib Jy Kz Oa Qz Uk) Ha(Ax Ih Ji Jm Jt Mt Oa Vt) gP(bU Ic Ik It Nj Nu Ou Qa) Ba(aW Bg cE Ch Jk Mu Mv) Pj(Dd Jk Nd Ou Oy Pb Uk) cM(aP Bc bE bV cF Nu Ou) eP(aK aM cC cY dF dL dR) Jr(Fr Nu Pa Pb Pc pF) Ur(bC bE Em It Jm Ug) Vp(Fp It Lx Mt Nu Qe) Bg(Fr Ik Lx Mt Qe) Me(bV cB Ou pF Ph) Ih(Fr In Ji Nc Pa) Ri(gW Ic Mt Nm Pa) Vo(It Kl Kp Nm Pz) aP(aV bR cB dO dV) dF(bF bZ cG dO Nq) Mi(Im Li Mf Qa) Nd(Ly Mk Pc pF) Bc(bU cB cP) Ct(Ik Jm Oy) Db(bC cC Gw) Dd(Cv Gt It) Ns(Fr Pe Qa) Im(Li Pb Pc) Qe(aI Ut Tj) Jk(Ph Qy Tt) Uk(aZ It Nm) Ch(Ik Nm) Gw(Al dD) No(Mf Pc) Mv(Ph Qx) Qa(Nq Pb) Of(Fr Mg) Ou(Ko Ok) Ut(Ke Mt) bU(aW dE) hC(Et Nw) pF(Nk Nu) BoDq WmLv TjLx GcKj MuUf NcJl JtPb PabJ aKaU aVdA bFdV cCdE dKdO

Figure 11 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.4E1 | 7.2E1 | 7.5E1 | 9.0E1 | 5.1E1 | 6.1E1 | 2.0E0 | 1.0E1 | 4.4E2 | 2.7E2 | 965 | 60 | 171 | 60 | 0.58 |
| Ad | ug/mL | 2.5E-2 | 9.1E-2 | 5.8E-2 | 1.1E-1 | 7.7E-2 | 1.0E-1 | 6.8E-4 | 1.9E-3 | 3.7E-1 | 3.6E-1 | 255 | 48 | 103 | 48 | 0.67 |
| Af | ng/mL | 9.2E-1 | 1.3E0 | 1.8E1 | 2.9E1 | 7.2E1 | 7.8E1 | 1.7E-3 | 1.7E-3 | 5.3E2 | 4.0E2 | 255 | 48 | 103 | 48 | 0.57 |
| Aj | ug/mL | 1.4E0 | 4.8E0 | 2.6E0 | 3.5E0 | 2.4E0 | 2.6E0 | 1.5E-3 | 4.0E-3 | 6.1E0 | 6.1E0 | 255 | 48 | 103 | 48 | 0.59 |
| Al | mg/mL | 9.0E-5 | 1.2E-4 | 2.5E-4 | 2.5E-4 | 4.2E-4 | 4.0E-4 | 2.5E-6 | 9.0E-6 | 1.9E-3 | 1.9E-3 | 255 | 48 | 103 | 48 | 0.54 |
| An | U/mL | 4.0E1 | 7.2E1 | 1.5E2 | 2.5E2 | 4.7E2 | 4.8E2 | 9.8E-4 | 7.7E-1 | 5.5E3 | 3.0E3 | 255 | 48 | 103 | 48 | 0.64 |
| Ao | pg/mL | 8.5E1 | 1.1E2 | 2.1E2 | 2.3E2 | 1.0E3 | 5.4E2 | 1.5E0 | 1.2E1 | 1.6E4 | 3.8E3 | 255 | 48 | 103 | 48 | 0.60 |
| Ap | ng/mL | 2.7E1 | 4.5E1 | 4.3E1 | 5.9E1 | 5.0E1 | 5.1E1 | 9.9E-1 | 8.4E-5 | 3.3E2 | 2.5E2 | 255 | 48 | 103 | 48 | 0.64 |
| Ar | ng/mL | 6.5E-1 | 1.3E0 | 2.0E0 | 4.6E0 | 4.1E0 | 7.8E0 | 3.4E-3 | 3.4E-3 | 4.3E1 | 2.9E1 | 255 | 48 | 103 | 48 | 0.61 |
| As | ng/mL | 8.7E-3 | 7.3E-3 | 1.2E-2 | 1.4E-2 | 1.6E-2 | 2.2E-2 | 1.7E-3 | 1.7E-3 | 1.1E-1 | 1.2E-1 | 255 | 48 | 103 | 48 | 0.49 |
| Aw | pg/mL | 1.6E1 | 1.7E1 | 1.6E1 | 1.8E1 | 5.4E0 | 5.8E0 | 3.5E0 | 9.4E0 | 3.3E1 | 3.8E1 | 255 | 48 | 103 | 48 | 0.63 |
| Ax | ng/mL | 2.1E0 | 2.3E0 | 8.2E0 | 1.2E1 | 1.8E1 | 2.3E1 | 1.9E-2 | 4.9E-2 | 1.5E2 | 1.3E2 | 255 | 48 | 103 | 48 | 0.56 |
| Ba | ng/mL | 3.7E1 | 1.7E2 | 2.8E2 | 5.7E2 | 7.3E2 | 1.0E3 | 3.7E-1 | 2.7E-1 | 8.1E3 | 4.5E3 | 255 | 48 | 103 | 48 | 0.65 |
| Bb | ng/mL | 2.6E0 | 4.8E0 | 5.3E0 | 6.4E0 | 8.5E0 | 5.4E0 | 4.1E-3 | 4.1E-3 | 6.6E1 | 2.0E1 | 255 | 48 | 103 | 48 | 0.62 |
| Bc | ng/mL | 3.3E1 | 4.3E1 | 9.7E1 | 1.0E2 | 1.8E2 | 2.0E2 | 1.1E-1 | 2.2E-1 | 1.0E3 | 1.0E3 | 255 | 48 | 103 | 48 | 0.53 |
| Bg | ng/mL | 6.4E-2 | 2.9E-1 | 4.4E0 | 1.7E0 | 2.2E1 | 3.8E0 | 5.3E-4 | 5.3E-4 | 2.5E2 | 2.1E1 | 255 | 48 | 103 | 48 | 0.62 |
| Bn | ng/mL | 5.6E-2 | 4.2E-1 | 8.5E-1 | 2.1E0 | 1.6E0 | 2.6E0 | 5.6E-2 | 5.6E-2 | 8.5E0 | 7.6E0 | 255 | 48 | 103 | 48 | 0.62 |
| Bo | ng/mL | 1.1E1 | 1.4E1 | 1.3E1 | 1.6E1 | 9.6E0 | 1.4E1 | 1.6E-2 | 1.6E-2 | 7.4E1 | 4.6E1 | 255 | 48 | 103 | 48 | 0.55 |
| Ch | uIU/mL | 9.0E-1 | 1.9E0 | 6.5E0 | 1.9E1 | 2.1E1 | 4.2E1 | 3.4E-3 | 3.4E-3 | 2.3E2 | 1.9E2 | 255 | 48 | 103 | 48 | 0.62 |
| Co | pg/mL | 3.1E1 | 3.9E1 | 9.1E1 | 1.2E2 | 2.1E2 | 3.0E2 | 3.9E0 | 1.5E-1 | 1.9E3 | 2.1E3 | 255 | 48 | 103 | 48 | 0.60 |
| Cp | ng/mL | 1.9E1 | 2.8E1 | 2.5E1 | 3.6E1 | 2.5E1 | 2.9E1 | 6.0E-1 | 6.0E-1 | 2.9E2 | 1.9E2 | 255 | 48 | 103 | 48 | 0.70 |
| Cq | ng/mL | 2.4E-2 | 3.1E-2 | 1.6E-1 | 6.1E-2 | 1.1E0 | 9.4E-2 | 8.0E-4 | 8.0E-4 | 1.7E1 | 5.2E-1 | 255 | 48 | 103 | 48 | 0.57 |
| Cs | ng/mL | 4.5E1 | 7.7E1 | 2.1E2 | 2.9E2 | 4.0E2 | 5.4E2 | 2.7E-2 | 1.3E0 | 2.9E3 | 3.0E3 | 255 | 48 | 103 | 48 | 0.55 |
| Ct | ng/mL | 1.2E0 | 7.6E-1 | 2.6E1 | 3.8E1 | 8.2E1 | 9.8E1 | 1.1E-4 | 1.1E-4 | 6.2E2 | 4.7E2 | 255 | 48 | 103 | 48 | 0.50 |
| Cu | ng/mL | 2.1E-1 | 3.0E-1 | 4.2E-1 | 3.5E-1 | 9.2E-1 | 2.1E-1 | 9.6E-3 | 9.0E-5 | 9.2E0 | 8.6E-1 | 255 | 48 | 103 | 48 | 0.60 |
| Cv | ng/mL | 4.6E0 | 9.4E0 | 2.4E1 | 3.1E1 | 7.0E1 | 6.3E1 | 5.6E-3 | 2.6E-2 | 5.3E2 | 3.1E2 | 255 | 48 | 103 | 48 | 0.58 |
| Cw | mIU/mL | 2.8E-2 | 3.2E-2 | 3.8E-2 | 4.1E-2 | 3.0E-2 | 2.9E-2 | 2.3E-3 | 4.8E-3 | 1.9E-1 | 1.4E-1 | 255 | 48 | 103 | 48 | 0.54 |
| Cx | ng/mL | 1.8E-1 | 4.2E-1 | 5.4E1 | 9.6E1 | 1.0E2 | 1.3E2 | 9.3E-5 | 9.3E-5 | 3.9E2 | 3.9E2 | 255 | 48 | 103 | 48 | 0.56 |
| Db | ug/mL | 8.2E0 | 6.8E0 | 9.4E0 | 8.0E0 | 8.8E0 | 7.4E0 | 5.3E-1 | 5.0E-1 | 1.0E2 | 3.6E1 | 255 | 48 | 103 | 48 | 0.43 |
| Dc | nmol/L | 1.8E-2 | 2.8E-2 | 5.7E-2 | 5.9E-2 | 1.3E-1 | 8.4E-2 | 5.2E-6 | 3.0E-4 | 1.2E0 | 4.0E-1 | 255 | 48 | 103 | 48 | 0.56 |
| Dd | ug/mL | 6.9E-2 | 9.0E-2 | 1.8E-1 | 2.4E-1 | 2.6E-1 | 3.8E-1 | 1.9E-4 | 8.3E-5 | 1.6E0 | 1.9E0 | 255 | 48 | 103 | 48 | 0.52 |
| De | ng/mL | 3.4E-3 | 3.4E-3 | 5.6E-2 | 1.1E-1 | 1.1E-1 | 1.5E-1 | 3.4E-3 | 3.4E-3 | 5.9E-1 | 6.2E-1 | 255 | 48 | 103 | 48 | 0.60 |
| Dg | ng/mL | 2.5E1 | 5.0E1 | 3.9E1 | 6.3E1 | 3.8E1 | 5.0E1 | 2.8E-1 | 1.0E-1 | 1.9E2 | 1.9E2 | 255 | 48 | 103 | 48 | 0.64 |
| Di | pg/mL | 1.6E0 | 1.7E0 | 2.0E0 | 2.5E0 | 1.8E0 | 2.3E0 | 1.8E-1 | 1.8E-1 | 1.3E1 | 7.8E0 | 255 | 48 | 103 | 48 | 0.54 |
| Dk | uIU/mL | 1.4E-2 | 2.5E-2 | 9.3E-2 | 4.4E-2 | 6.3E-1 | 6.2E-2 | 1.1E-4 | 1.1E-4 | 8.9E0 | 3.4E-1 | 255 | 48 | 103 | 48 | 0.61 |
| Dl | ng/mL | 2.0E2 | 3.4E2 | 2.7E2 | 4.4E2 | 2.4E2 | 3.5E2 | 3.1E0 | 2.5E0 | 1.4E3 | 1.3E3 | 255 | 48 | 103 | 48 | 0.64 |
| Do | ng/ml | 4.7E-1 | 9.5E-1 | 1.1E0 | 9.0E-1 | 2.9E0 | 1.1E0 | 3.6E-2 | 3.6E-2 | 1.9E1 | 3.7E0 | 55 | 11 | 37 | 11 | 0.58 |
| Dp | ng/ml | 2.5E0 | 2.2E0 | 4.9E0 | 5.3E0 | 6.8E0 | 7.0E0 | 3.7E-3 | 5.3E-3 | 4.3E1 | 3.5E1 | 122 | 47 | 99 | 47 | 0.49 |
| Dr | pg/ml | 3.4E1 | 1.3E1 | 5.7E1 | 3.5E1 | 6.6E1 | 4.7E1 | 7.5E-1 | 7.5E-1 | 2.9E2 | 1.6E2 | 99 | 25 | 50 | 25 | 0.39 |
| Dq | Absorbance | 1.7E-3 | 1.7E-3 | 4.1E-2 | 2.5E-3 | 1.5E-1 | 2.6E-3 | 1.7E-3 | 1.7E-3 | 8.3E-1 | 1.1E-2 | 55 | 11 | 37 | 11 | 0.38 |
| Du | pg/ml | 4.2E1 | 1.2E0 | 5.0E2 | 1.7E3 | 1.3E3 | 6.0E3 | 1.2E0 | 1.2E0 | 7.0E3 | 2.6E4 | 53 | 19 | 42 | 19 | 0.46 |
| Ef | ng/ml | 9.5E-2 | 3.1E-1 | 6.9E-1 | 1.7E0 | 1.7E0 | 1.9E0 | 5.7E-4 | 5.7E-4 | 1.0E1 | 8.6E0 | 165 | 48 | 102 | 48 | 0.62 |
| Wm | % | 8.2E-1 | 8.0E-1 | 3.0E1 | 5.4E1 | 1.9E2 | 2.1E2 | 5.4E-2 | 8.5E-2 | 2.4E3 | 9.6E2 | 204 | 53 | 119 | 53 | 0.51 |
| Ed | pg/ml | 5.2E-1 | 5.2E-1 | 9.3E1 | 1.7E1 | 6.6E2 | 4.0E1 | 5.2E-1 | 5.2E-1 | 7.3E3 | 1.6E2 | 122 | 47 | 98 | 47 | 0.38 |
| Yf | ng/mL | 1.6E1 | 1.8E1 | 1.4E2 | 3.4E1 | 8.4E2 | 3.5E1 | 2.9E-1 | 2.2E0 | 6.6E3 | 1.2E2 | 61 | 19 | 50 | 19 | 0.53 |
| Tj | pg/mL | 3.7E-1 | 3.7E-1 | 7.6E1 | 5.0E0 | 3.7E2 | 1.2E1 | 3.6E-1 | 3.6E-1 | 3.5E3 | 5.2E1 | 165 | 49 | 103 | 49 | 0.40 |
| Po | pg/ml | 1.3E-1 | 2.5E0 | 8.0E0 | 1.1E1 | 2.7E1 | 2.8E1 | 8.0E-3 | 2.6E-2 | 2.7E2 | 2.2E2 | 359 | 75 | 189 | 75 | 0.61 |
| Ti | ug/mL | 2.8E0 | 5.2E0 | 4.1E0 | 5.7E0 | 3.7E0 | 4.9E0 | 1.2E-1 | 8.7E-3 | 1.6E1 | 1.7E1 | 86 | 32 | 69 | 32 | 0.58 |
| Em | ng/ml | 2.9E-3 | 6.1E-3 | 5.3E-2 | 4.5E-2 | 1.1E-1 | 9.6E-2 | 2.8E-16 | 1.9E-16 | 5.4E-1 | 4.7E-1 | 123 | 26 | 51 | 26 | 0.48 |
| Et | ng/ml | 1.0E3 | 2.1E3 | 1.3E3 | 2.2E3 | 1.0E3 | 1.3E3 | 7.5E1 | 1.5E2 | 4.9E3 | 5.0E3 | 359 | 75 | 189 | 75 | 0.69 |
| Eq | pg/ml | 1.3E2 | 2.5E2 | 2.7E2 | 3.4E2 | 3.8E2 | 4.3E2 | 1.0E0 | 1.0E0 | 1.8E3 | 1.8E3 | 53 | 19 | 42 | 19 | 0.56 |
| Th | ug/mL | 1.1E0 | 1.1E0 | 1.5E0 | 1.5E0 | 1.6E0 | 1.0E0 | 2.6E-3 | 6.5E-2 | 1.2E1 | 4.6E0 | 86 | 32 | 69 | 32 | 0.54 |
| Fa | ng/ml | 3.9E1 | 4.2E1 | 1.2E2 | 8.1E1 | 7.3E2 | 1.3E2 | 3.4E-2 | 2.6E-1 | 8.0E3 | 7.5E2 | 120 | 47 | 98 | 47 | 0.56 |

Figure 12

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ez | ng/ml | 3.7E0 | 7.0E0 | 1.6E1 | 3.3E1 | 3.9E1 | 1.1E2 | 1.3E-2 | 1.3E-2 | 3.0E2 | 7.1E2 | 122 | 47 | 99 | 47 | 0.57 |
| Fb | ng/ml | 2.3E1 | 2.6E1 | 2.1E1 | 2.4E1 | 1.2E1 | 1.1E1 | 1.0E0 | 5.9E-1 | 5.7E1 | 4.0E1 | 120 | 47 | 98 | 47 | 0.57 |
| Ex | ng/ml | 6.0E-2 | 8.2E-2 | 2.4E-1 | 1.3E-1 | 8.4E-1 | 1.5E-1 | 3.5E-5 | 1.5E-4 | 8.9E0 | 5.5E-1 | 126 | 33 | 69 | 33 | 0.55 |
| Fc | pg/ml | 2.2E-1 | 2.2E-1 | 2.9E2 | 9.5E-1 | 2.0E3 | 3.2E0 | 2.2E-1 | 2.2E-1 | 1.5E4 | 1.4E1 | 53 | 19 | 42 | 19 | 0.41 |
| Fd | pg/ml | 2.9E1 | 9.8E-1 | 9.7E2 | 8.2E2 | 4.6E3 | 2.0E3 | 9.8E-1 | 9.8E-1 | 3.3E4 | 8.2E3 | 53 | 19 | 42 | 19 | 0.47 |
| Fi | pg/ml | 2.5E-1 | 2.5E-1 | 3.3E2 | 5.5E0 | 1.9E3 | 2.3E1 | 2.5E-1 | 2.5E-1 | 1.4E4 | 1.0E2 | 53 | 19 | 42 | 19 | 0.40 |
| Fn | ng/ml | 2.1E-1 | 2.1E-1 | 8.5E0 | 2.7E0 | 3.8E1 | 4.9E0 | 1.1E-14 | 2.1E-1 | 4.2E2 | 2.1E1 | 122 | 47 | 99 | 47 | 0.45 |
| Fp | ng/ml | 9.4E0 | 2.1E1 | 2.0E1 | 3.7E1 | 2.6E1 | 3.6E1 | 6.0E-3 | 2.8E-1 | 1.4E2 | 1.2E2 | 380 | 76 | 189 | 76 | 0.64 |
| Fr | ng/ml | 2.5E4 | 5.0E4 | 9.9E4 | 1.6E5 | 1.7E5 | 2.2E5 | 6.4E2 | 7.8E2 | 8.4E5 | 8.5E5 | 464 | 78 | 193 | 78 | 0.63 |
| Fw | pg/ml | 7.1E-1 | 3.9E-1 | 1.0E2 | 8.9E0 | 6.7E2 | 2.0E1 | 1.1E-14 | 1.7E-14 | 6.9E3 | 1.1E2 | 167 | 48 | 103 | 48 | 0.46 |
| Fy | ng/ml | 3.1E1 | 4.4E1 | 4.9E1 | 7.0E1 | 5.5E1 | 6.1E1 | 1.2E-1 | 2.7E0 | 3.3E2 | 2.1E2 | 121 | 46 | 98 | 46 | 0.62 |
| Gh | pg/ml | 2.3E0 | 1.1E1 | 2.5E1 | 1.0E2 | 5.0E1 | 3.0E2 | 2.9E-2 | 2.9E-2 | 2.7E2 | 1.2E3 | 53 | 18 | 42 | 18 | 0.54 |
| Gb | % | 3.2E1 | 3.9E1 | 4.3E1 | 4.4E1 | 3.9E1 | 3.2E1 | 2.7E0 | 4.6E0 | 2.3E2 | 1.0E2 | 53 | 19 | 41 | 19 | 0.52 |
| Gc | ng/ml | 9.9E1 | 7.7E1 | 1.4E2 | 1.7E2 | 1.4E2 | 2.1E2 | 6.4E0 | 9.7E0 | 7.9E2 | 9.2E2 | 104 | 27 | 52 | 27 | 0.49 |
| Gd | ng/ml | 2.9E1 | 2.8E1 | 3.0E1 | 3.2E1 | 1.6E1 | 2.1E1 | 5.4E0 | 6.3E0 | 8.1E1 | 8.1E1 | 119 | 24 | 50 | 24 | 0.50 |
| Gn | U/ml | 5.0E-1 | 1.8E-1 | 1.7E0 | 8.6E-1 | 3.7E0 | 2.4E0 | 1.3E-3 | 1.3E-3 | 3.0E1 | 1.2E1 | 95 | 25 | 50 | 25 | 0.38 |
| Gl | pg/ml | 6.1E3 | 1.0E4 | 9.8E3 | 1.2E4 | 9.0E3 | 9.0E3 | 2.3E2 | 6.3E2 | 3.4E4 | 3.3E4 | 162 | 48 | 102 | 48 | 0.60 |
| Gp | U/ml | 1.8E0 | 1.1E0 | 4.4E0 | 4.5E0 | 7.6E0 | 8.5E0 | 1.3E-3 | 1.3E-3 | 6.7E1 | 4.8E1 | 167 | 48 | 103 | 48 | 0.45 |
| Gt | pg/ml | 2.2E-3 | 2.2E-3 | 9.4E-2 | 1.3E-2 | 2.1E-1 | 1.9E-2 | 2.2E-3 | 2.2E-3 | 1.1E0 | 5.0E-2 | 48 | 7 | 31 | 7 | 0.43 |
| Gw | ng/ml | 6.7E0 | 5.7E0 | 2.0E1 | 7.6E0 | 6.1E1 | 6.9E0 | 8.3E-1 | 8.3E-1 | 4.4E2 | 2.6E1 | 55 | 11 | 37 | 11 | 0.49 |
| Gz | ug/ml | 1.2E0 | 1.0E0 | 1.1E1 | 5.5E0 | 5.3E1 | 6.2E0 | 2.9E-16 | 1.3E-1 | 4.8E2 | 2.1E1 | 81 | 31 | 64 | 31 | 0.50 |
| Ha | ng/ml | 2.7E0 | 2.6E0 | 8.4E0 | 7.5E0 | 1.9E1 | 1.3E1 | 1.7E-2 | 1.7E-2 | 1.0E2 | 6.7E1 | 120 | 47 | 98 | 47 | 0.50 |
| Nm | pg/ml | 1.2E4 | 2.6E4 | 2.4E4 | 3.9E4 | 4.9E4 | 4.4E4 | 1.0E-9 | 1.0E-9 | 7.8E5 | 1.9E5 | 358 | 75 | 190 | 75 | 0.62 |
| Nn | pg/ml | 1.3E2 | 2.0E2 | 2.5E3 | 2.3E3 | 1.1E4 | 9.3E3 | 1.0E-9 | 1.0E-9 | 1.0E5 | 6.9E4 | 358 | 75 | 190 | 75 | 0.58 |
| No | pg/ml | 1.3E1 | 2.4E1 | 2.7E1 | 5.2E1 | 5.9E1 | 1.7E2 | 1.0E-9 | 2.4E-1 | 5.9E2 | 1.4E3 | 358 | 75 | 190 | 75 | 0.59 |
| Nq | pg/ml | 2.2E0 | 1.4E0 | 2.1E1 | 1.6E1 | 8.4E1 | 4.1E1 | 1.0E-9 | 1.0E-9 | 1.2E3 | 2.6E2 | 358 | 75 | 190 | 75 | 0.48 |
| Nr | pg/ml | 4.7E-1 | 1.7E0 | 1.6E1 | 1.3E2 | 7.0E1 | 9.9E2 | 1.0E-9 | 1.0E-9 | 9.8E2 | 8.5E3 | 358 | 75 | 190 | 75 | 0.58 |
| Ns | pg/ml | 1.0E-9 | 1.0E-9 | 8.9E0 | 3.3E0 | 4.5E1 | 1.8E1 | 1.0E-9 | 1.0E-9 | 6.8E2 | 1.2E2 | 358 | 75 | 190 | 75 | 0.48 |
| Nt | pg/ml | 9.4E1 | 1.5E2 | 1.2E2 | 1.7E2 | 9.2E1 | 1.1E2 | 1.0E-9 | 1.5E1 | 5.9E2 | 6.8E2 | 358 | 75 | 190 | 75 | 0.66 |
| Nu | pg/ml | 1.7E1 | 2.8E1 | 4.9E1 | 7.2E1 | 8.8E1 | 9.8E1 | 1.0E-9 | 1.0E-9 | 8.9E2 | 5.8E2 | 358 | 75 | 190 | 75 | 0.60 |
| Lu | pg/ml | 1.0E4 | 1.0E4 | 1.5E4 | 1.1E4 | 3.2E4 | 1.1E4 | 6.7E2 | 7.1E2 | 3.9E5 | 8.4E4 | 360 | 76 | 190 | 76 | 0.50 |
| Lv | pg/ml | 1.0E-9 | 1.0E-9 | 1.1E1 | 1.8E1 | 2.2E1 | 3.0E1 | 1.0E-9 | 1.0E-9 | 2.4E2 | 1.6E2 | 360 | 76 | 190 | 76 | 0.56 |
| Lw | pg/ml | 1.0E-9 | 1.0E-9 | 1.4E-1 | 4.2E-1 | 1.8E0 | 2.5E0 | 1.0E-9 | 1.0E-9 | 3.2E1 | 1.7E1 | 360 | 76 | 190 | 76 | 0.51 |
| Lx | pg/ml | 1.0E-9 | 1.1E1 | 1.1E2 | 2.9E2 | 4.2E2 | 1.2E3 | 1.0E-9 | 1.0E-9 | 6.2E3 | 1.0E4 | 360 | 76 | 190 | 76 | 0.60 |
| Ly | pg/ml | 1.0E-9 | 1.0E-9 | 9.1E0 | 1.7E1 | 1.8E1 | 2.6E1 | 1.0E-9 | 1.0E-9 | 1.2E2 | 1.2E2 | 360 | 76 | 190 | 76 | 0.56 |
| Lz | pg/ml | 1.0E-9 | 1.0E-9 | 2.9E0 | 3.3E0 | 2.4E1 | 2.4E1 | 1.0E-9 | 1.0E-9 | 4.3E2 | 2.1E2 | 360 | 76 | 190 | 76 | 0.49 |
| Ma | pg/ml | 2.4E2 | 4.0E2 | 1.5E3 | 1.1E3 | 4.7E3 | 1.9E3 | 1.0E-9 | 1.0E-9 | 6.5E4 | 9.5E3 | 360 | 76 | 190 | 76 | 0.56 |
| Mb | pg/ml | 2.5E1 | 2.9E1 | 3.1E1 | 3.7E1 | 1.4E1 | 1.8E1 | 5.4E0 | 1.4E1 | 9.3E1 | 8.7E1 | 360 | 76 | 190 | 76 | 0.61 |
| Mc | pg/ml | 1.0E-9 | 1.0E-9 | 1.7E-2 | 1.0E-9 | 2.3E-1 | 0.0E0 | 1.0E-9 | 1.0E-9 | 4.0E0 | 1.0E-9 | 360 | 76 | 190 | 76 | 0.50 |
| Md | pg/ml | 1.0E-9 | 1.0E-9 | 6.2E-1 | 5.8E-1 | 5.2E0 | 2.6E0 | 1.0E-9 | 1.0E-9 | 6.8E1 | 1.6E1 | 360 | 76 | 190 | 76 | 0.50 |
| Me | pg/ml | 3.2E1 | 2.5E1 | 2.9E1 | 2.5E1 | 1.6E1 | 1.8E1 | 1.0E-9 | 6.1E-1 | 1.2E2 | 7.9E1 | 360 | 76 | 190 | 76 | 0.41 |
| Mf | pg/ml | 1.0E-9 | 1.0E-9 | 3.7E-1 | 5.3E-1 | 1.6E0 | 1.7E0 | 1.0E-9 | 1.0E-9 | 2.0E1 | 8.4E0 | 360 | 76 | 190 | 76 | 0.54 |
| Mg | pg/ml | 1.9E0 | 3.1E0 | 6.4E0 | 1.0E1 | 1.1E1 | 1.3E1 | 1.0E-9 | 1.0E-9 | 8.8E1 | 5.9E1 | 360 | 76 | 190 | 76 | 0.58 |
| Mh | pg/ml | 1.0E-9 | 1.0E-9 | 1.1E0 | 1.3E0 | 8.4E0 | 5.6E0 | 1.0E-9 | 1.0E-9 | 1.1E2 | 3.8E1 | 360 | 76 | 190 | 76 | 0.49 |
| Mi | pg/ml | 1.0E-9 | 1.0E-9 | 6.9E-1 | 3.1E0 | 7.1E0 | 1.9E1 | 1.0E-9 | 1.0E-9 | 1.2E2 | 1.6E2 | 360 | 76 | 190 | 76 | 0.51 |
| Mj | pg/ml | 1.0E-9 | 1.0E-9 | 5.2E0 | 1.0E1 | 3.1E1 | 6.3E1 | 1.0E-9 | 1.0E-9 | 4.6E2 | 5.4E2 | 360 | 76 | 190 | 76 | 0.52 |
| Mk | pg/ml | 6.5E-1 | 3.5E0 | 1.6E1 | 8.0E1 | 9.9E1 | 6.4E2 | 1.0E-9 | 1.0E-9 | 1.7E3 | 5.6E3 | 360 | 76 | 190 | 76 | 0.53 |
| Ml | pg/ml | 1.0E-9 | 1.0E-9 | 9.1E0 | 1.1E0 | 1.1E2 | 2.9E0 | 1.0E-9 | 1.0E-9 | 2.1E3 | 1.6E1 | 360 | 76 | 190 | 76 | 0.52 |
| Mm | pg/ml | 4.0E2 | 8.0E2 | 8.0E2 | 1.3E3 | 9.7E2 | 1.5E3 | 1.0E-9 | 1.0E-9 | 6.0E3 | 6.9E3 | 360 | 76 | 190 | 76 | 0.61 |
| Mn | pg/ml | 4.8E0 | 5.2E0 | 1.0E1 | 1.1E1 | 2.5E1 | 1.8E1 | 1.0E-9 | 1.0E-9 | 3.5E2 | 1.3E2 | 360 | 76 | 190 | 76 | 0.54 |
| Mp | pg/ml | 1.0E-9 | 1.0E-9 | 9.7E0 | 9.9E0 | 2.2E1 | 2.7E1 | 1.0E-9 | 1.0E-9 | 1.8E2 | 1.8E2 | 360 | 76 | 190 | 76 | 0.51 |
| Mq | pg/ml | 1.0E-9 | 1.0E-9 | 2.8E0 | 4.7E0 | 1.7E1 | 1.7E1 | 1.0E-9 | 1.0E-9 | 2.1E2 | 1.1E2 | 360 | 76 | 190 | 76 | 0.53 |
| Mr | pg/ml | 1.0E-9 | 1.0E-9 | 1.4E1 | 1.7E2 | 8.7E1 | 1.4E3 | 1.0E-9 | 1.0E-9 | 1.4E3 | 1.2E4 | 360 | 76 | 190 | 76 | 0.54 |
| Ms | pg/ml | 3.8E2 | 4.2E2 | 5.6E2 | 5.6E2 | 7.1E2 | 5.4E2 | 1.0E-9 | 1.0E-9 | 5.6E3 | 2.2E3 | 360 | 76 | 190 | 76 | 0.52 |
| Mt | pg/ml | 1.0E-9 | 1.3E0 | 1.1E1 | 4.8E1 | 6.3E1 | 1.2E2 | 1.0E-9 | 1.0E-9 | 8.7E2 | 7.8E2 | 360 | 76 | 190 | 76 | 0.62 |
| Mu | pg/ml | 1.0E-9 | 1.0E-9 | 1.5E0 | 1.1E0 | 1.0E1 | 3.7E0 | 1.0E-9 | 1.0E-9 | 9.9E1 | 2.7E1 | 360 | 76 | 190 | 76 | 0.57 |
| Mv | pg/ml | 1.0E-9 | 1.0E-9 | 8.2E1 | 8.5E1 | 4.2E2 | 3.2E2 | 1.0E-9 | 1.0E-9 | 4.5E3 | 2.5E3 | 360 | 76 | 190 | 76 | 0.57 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Mw | pg/ml | 2.5E1 | 4.3E1 | 5.8E2 | 4.1E2 | 3.9E3 | 1.2E3 | 1.0E-9 | 1.0E-9 | 6.2E4 | 8.5E3 | 360 | 76 | 190 | 76 | 0.58 |
| Mx | pg/ml | 1.0E-9 | 1.0E-9 | 1.8E-1 | 1.7E-1 | 8.2E-1 | 4.9E-1 | 1.0E-9 | 1.0E-9 | 9.2E0 | 3.0E0 | 360 | 76 | 190 | 76 | 0.53 |
| My | pg/ml | 1.0E-9 | 1.0E-9 | 5.6E2 | 2.8E2 | 3.5E3 | 8.2E2 | 1.0E-9 | 1.0E-9 | 3.9E4 | 4.6E3 | 360 | 76 | 190 | 76 | 0.53 |
| Mz | pg/ml | 8.5E0 | 1.5E1 | 2.1E1 | 3.1E1 | 5.9E1 | 4.9E1 | 1.0E-9 | 1.0E-9 | 8.4E2 | 3.0E2 | 360 | 76 | 190 | 76 | 0.62 |
| Na | pg/ml | 1.0E-9 | 1.0E-9 | 5.7E-1 | 9.1E-1 | 1.8E0 | 2.7E0 | 1.0E-9 | 1.0E-9 | 7.8E0 | 1.6E1 | 360 | 76 | 190 | 76 | 0.55 |
| Nb | pg/ml | 1.8E0 | 2.1E0 | 4.6E0 | 6.2E0 | 1.6E1 | 2.7E1 | 1.0E-9 | 1.0E-9 | 2.3E2 | 2.4E2 | 360 | 76 | 190 | 76 | 0.53 |
| Nc | pg/ml | 4.5E2 | 1.7E2 | 6.7E2 | 3.7E2 | 8.4E2 | 4.8E2 | 1.0E-9 | 1.0E-9 | 9.2E3 | 2.1E3 | 360 | 76 | 190 | 76 | 0.39 |
| Nd | pg/ml | 3.1E1 | 6.5E0 | 2.6E1 | 1.9E1 | 2.0E1 | 2.8E1 | 1.0E-9 | 1.0E-9 | 8.4E1 | 1.4E2 | 360 | 76 | 190 | 76 | 0.37 |
| Ne | pg/ml | 4.9E2 | 2.8E2 | 6.3E2 | 4.1E2 | 6.4E2 | 4.1E2 | 1.0E-9 | 1.0E-9 | 7.0E3 | 1.7E3 | 360 | 76 | 190 | 76 | 0.39 |
| Nf | pg/ml | 1.0E-9 | 1.0E-9 | 2.9E0 | 2.7E0 | 8.8E0 | 1.1E1 | 1.0E-9 | 1.0E-9 | 8.2E1 | 8.2E1 | 360 | 76 | 190 | 76 | 0.47 |
| Ng | pg/ml | 2.1E1 | 6.7E1 | 1.1E2 | 1.3E2 | 2.3E2 | 2.0E2 | 1.0E-9 | 1.0E-9 | 1.6E3 | 1.2E3 | 360 | 76 | 190 | 76 | 0.55 |
| Nh | pg/ml | 7.7E1 | 4.2E1 | 9.8E1 | 6.0E1 | 8.7E1 | 6.1E1 | 1.0E-9 | 1.0E-9 | 5.6E2 | 3.4E2 | 360 | 76 | 190 | 76 | 0.35 |
| Ni | pg/ml | 4.5E0 | 7.1E0 | 7.4E1 | 7.8E1 | 1.1E2 | 1.2E2 | 1.0E-9 | 1.0E-9 | 7.1E2 | 5.7E2 | 360 | 76 | 190 | 76 | 0.51 |
| Nj | pg/ml | 9.0E0 | 3.5E0 | 1.2E1 | 7.9E0 | 1.2E1 | 9.9E0 | 1.0E-9 | 1.0E-9 | 8.3E1 | 5.7E1 | 360 | 76 | 190 | 76 | 0.37 |
| Nk | pg/ml | 2.2E1 | 1.7E1 | 3.6E1 | 2.9E1 | 4.0E1 | 3.3E1 | 1.0E-9 | 1.0E-9 | 1.8E2 | 1.7E2 | 360 | 76 | 190 | 76 | 0.48 |
| Nl | pg/ml | 5.2E1 | 2.6E1 | 7.0E1 | 4.1E1 | 8.2E1 | 4.1E1 | 1.0E-9 | 1.0E-9 | 1.1E3 | 1.9E2 | 360 | 76 | 190 | 76 | 0.37 |
| Hl | pg/ml | 1.3E1 | 1.3E1 | 4.5E1 | 3.3E1 | 7.9E1 | 5.5E1 | 1.0E-9 | 1.0E-9 | 3.5E2 | 2.3E2 | 53 | 19 | 42 | 19 | 0.49 |
| Ho | pg/ml | 1.5E1 | 1.8E1 | 3.2E1 | 2.3E1 | 9.6E1 | 1.2E1 | 1.0E-9 | 8.1E0 | 7.0E2 | 6.0E1 | 53 | 19 | 42 | 19 | 0.63 |
| Hp | ng/ml | 1.7E0 | 1.9E0 | 7.2E1 | 2.8E2 | 2.4E2 | 4.2E2 | 1.0E-9 | 4.2E-1 | 8.9E2 | 8.9E2 | 53 | 19 | 42 | 19 | 0.54 |
| Tz | pg/ml | 3.7E3 | 4.4E3 | 7.5E3 | 3.5E4 | 1.1E4 | 1.5E5 | 7.4E1 | 1.5E2 | 8.8E4 | 1.0E6 | 124 | 47 | 98 | 47 | 0.61 |
| Ua | pg/ml | 3.5E3 | 4.8E3 | 3.0E4 | 1.6E4 | 1.9E5 | 3.0E4 | 3.5E2 | 3.2E2 | 2.1E6 | 1.8E5 | 124 | 47 | 98 | 47 | 0.58 |
| Ub | pg/ml | 5.8E2 | 6.7E2 | 8.7E2 | 1.0E3 | 1.2E3 | 1.1E3 | 1.0E-9 | 1.9E1 | 9.8E3 | 6.4E3 | 124 | 47 | 98 | 47 | 0.56 |
| Ue | pg/ml | 3.1E1 | 3.2E1 | 3.5E1 | 4.2E1 | 2.4E1 | 2.9E1 | 4.2E0 | 7.7E0 | 1.2E2 | 1.6E2 | 124 | 47 | 98 | 47 | 0.58 |
| Uc | pg/ml | 7.8E2 | 1.3E3 | 1.6E3 | 2.1E3 | 3.3E3 | 2.3E3 | 3.3E1 | 1.4E1 | 2.9E4 | 9.2E3 | 124 | 47 | 98 | 47 | 0.60 |
| Ud | pg/ml | 1.0E-9 | 1.0E-9 | 3.4E0 | 1.0E-9 | 3.5E1 | 0.0E0 | 1.0E-9 | 1.0E-9 | 3.9E2 | 1.0E-9 | 124 | 47 | 98 | 47 | 0.49 |
| Hq | pg/ml | 1.1E0 | 1.3E0 | 1.1E1 | 1.1E1 | 5.9E1 | 4.4E1 | 1.0E-9 | 1.0E-9 | 9.5E2 | 3.0E2 | 360 | 75 | 190 | 75 | 0.50 |
| Hr | pg/ml | 1.3E2 | 1.3E2 | 8.3E2 | 6.7E2 | 1.6E3 | 1.5E3 | 1.0E-9 | 1.0E-9 | 1.2E4 | 1.1E4 | 360 | 75 | 190 | 75 | 0.49 |
| Hu | pg/ml | 7.9E0 | 2.1E1 | 3.5E3 | 1.8E3 | 3.5E4 | 6.6E3 | 1.0E-9 | 1.0E-9 | 6.3E5 | 4.7E4 | 360 | 75 | 190 | 75 | 0.58 |
| Hv | pg/ml | 1.3E0 | 1.6E0 | 3.4E0 | 4.3E0 | 1.5E1 | 1.2E1 | 1.0E-9 | 1.0E-9 | 2.5E2 | 8.4E1 | 360 | 75 | 190 | 75 | 0.58 |
| Hw | pg/ml | 7.2E0 | 6.2E0 | 2.5E1 | 5.8E1 | 1.1E2 | 4.0E2 | 1.0E-9 | 1.0E-9 | 1.7E3 | 3.4E3 | 360 | 75 | 190 | 75 | 0.46 |
| Hx | pg/ml | 7.2E0 | 1.2E1 | 6.0E1 | 4.8E1 | 5.0E2 | 2.3E2 | 1.0E-9 | 1.0E-9 | 9.3E3 | 2.0E3 | 360 | 75 | 190 | 75 | 0.57 |
| Ib | ng/ml | 6.9E-2 | 6.7E-2 | 6.9E-1 | 2.4E0 | 3.0E0 | 8.4E0 | 1.0E-9 | 1.0E-9 | 3.0E1 | 5.2E1 | 122 | 45 | 99 | 45 | 0.53 |
| Ic | U/ml | 2.2E2 | 2.2E2 | 3.1E2 | 3.6E2 | 1.4E3 | 6.6E2 | 2.9E0 | 1.1E1 | 1.5E4 | 4.2E3 | 122 | 45 | 99 | 45 | 0.60 |
| Id | U/ml | 6.2E-1 | 8.9E-1 | 1.0E0 | 1.9E0 | 1.2E0 | 3.7E0 | 1.0E-9 | 1.0E-9 | 6.9E0 | 2.1E1 | 122 | 45 | 99 | 45 | 0.58 |
| Tt | pg/ml | 1.6E2 | 1.7E2 | 1.6E2 | 1.8E2 | 4.4E1 | 4.9E1 | 8.0E1 | 9.9E1 | 3.0E2 | 2.8E2 | 114 | 46 | 92 | 46 | 0.61 |
| To | pg/ml | 1.6E0 | 1.6E0 | 1.9E0 | 1.7E0 | 2.6E0 | 1.6E0 | 1.0E-9 | 1.0E-9 | 2.3E1 | 5.5E0 | 119 | 46 | 95 | 46 | 0.49 |
| Tr | pg/ml | 2.8E0 | 3.9E0 | 4.1E0 | 5.8E0 | 4.7E0 | 5.8E0 | 3.5E-2 | 1.0E-9 | 2.9E1 | 2.6E1 | 118 | 46 | 94 | 46 | 0.59 |
| Tn | pg/ml | 2.1E1 | 2.9E1 | 5.9E1 | 4.5E1 | 1.5E2 | 5.4E1 | 2.6E0 | 8.3E0 | 1.5E3 | 3.1E2 | 119 | 46 | 95 | 46 | 0.57 |
| Tv | ng/ml | 1.2E1 | 1.2E1 | 2.0E1 | 1.8E1 | 4.8E1 | 2.3E1 | 1.0E-9 | 1.0E-9 | 4.9E2 | 1.3E2 | 119 | 46 | 95 | 46 | 0.51 |
| Ih | ng/ml | 5.7E1 | 1.1E2 | 2.0E2 | 2.6E2 | 3.6E2 | 4.5E2 | 1.0E-9 | 1.0E-9 | 2.5E3 | 2.8E3 | 360 | 76 | 190 | 76 | 0.57 |
| Ii | ng/ml | 7.0E1 | 1.0E2 | 2.7E2 | 3.3E2 | 8.1E2 | 1.1E3 | 7.5E-1 | 2.9E0 | 8.4E3 | 9.2E3 | 360 | 76 | 190 | 76 | 0.57 |
| Ij | ng/ml | 7.0E1 | 8.5E1 | 2.0E2 | 2.3E2 | 7.3E2 | 7.6E2 | 2.1E0 | 4.7E0 | 6.4E3 | 6.4E3 | 358 | 75 | 190 | 75 | 0.57 |
| Ik | ng/ml | 1.2E1 | 2.4E2 | 9.2E2 | 6.9E2 | 9.2E3 | 1.3E3 | 5.9E-1 | 1.3E0 | 1.2E5 | 9.7E3 | 358 | 76 | 190 | 76 | 0.67 |
| Il | ng/ml | 3.3E2 | 5.5E2 | 1.4E3 | 1.3E3 | 3.0E3 | 2.7E3 | 1.0E-9 | 1.0E-9 | 1.2E4 | 1.2E4 | 354 | 75 | 190 | 75 | 0.52 |
| Im | ng/ml | 1.9E2 | 2.3E2 | 3.0E2 | 5.2E2 | 3.4E2 | 8.6E2 | 1.3E1 | 2.7E1 | 3.1E3 | 5.6E3 | 357 | 76 | 190 | 76 | 0.58 |
| In | ng/ml | 4.2E0 | 4.7E0 | 3.6E1 | 1.1E1 | 2.3E2 | 1.7E1 | 1.0E-9 | 1.0E-9 | 3.9E3 | 8.4E1 | 360 | 76 | 190 | 76 | 0.52 |
| Hb | ng/ml | 2.0E1 | 2.8E1 | 2.7E1 | 3.8E1 | 2.6E1 | 3.8E1 | 1.1E0 | 3.3E0 | 1.5E2 | 2.1E2 | 120 | 47 | 98 | 47 | 0.60 |
| Hc | pg/ml | 6.1E2 | 7.5E2 | 2.2E3 | 4.4E3 | 4.9E3 | 1.5E4 | 1.0E-9 | 1.0E-9 | 3.6E4 | 1.0E5 | 120 | 47 | 98 | 47 | 0.56 |
| Hf | ng/ml | 1.2E2 | 1.3E2 | 3.6E2 | 3.3E2 | 5.3E2 | 4.6E2 | 1.0E-9 | 1.0E-9 | 2.5E3 | 2.2E3 | 120 | 47 | 98 | 47 | 0.53 |
| Io | ng/ml | 6.9E3 | 7.8E3 | 1.7E4 | 2.1E4 | 5.1E4 | 6.5E4 | 6.6E0 | 6.2E1 | 8.8E5 | 5.5E5 | 357 | 75 | 189 | 75 | 0.54 |
| Ip | ng/ml | 8.1E0 | 1.4E1 | 1.8E1 | 2.3E1 | 2.7E1 | 2.6E1 | 1.0E-9 | 5.6E-3 | 2.6E2 | 1.4E2 | 357 | 75 | 189 | 75 | 0.54 |
| Iq | ug/ml | 9.1E-2 | 4.6E-2 | 3.9E1 | 1.1E1 | 7.2E2 | 8.7E1 | 1.0E-9 | 1.0E-9 | 1.4E4 | 7.5E2 | 357 | 75 | 189 | 75 | 0.45 |
| Ir | ug/ml | 2.9E-1 | 3.6E-1 | 4.4E0 | 2.8E0 | 3.3E1 | 1.3E1 | 1.0E-9 | 1.0E-9 | 5.1E2 | 1.1E2 | 356 | 75 | 189 | 75 | 0.57 |
| Is | ng/ml | 1.3E0 | 2.1E0 | 6.4E0 | 9.0E0 | 3.1E1 | 2.8E1 | 1.0E-9 | 1.0E-9 | 5.5E2 | 2.3E2 | 357 | 75 | 189 | 75 | 0.57 |
| It | ng/ml | 1.9E0 | 1.9E0 | 2.6E1 | 2.3E1 | 1.3E2 | 1.1E2 | 1.0E-9 | 1.0E-9 | 1.2E3 | 7.7E2 | 357 | 75 | 189 | 75 | 0.51 |
| Iu | ng/ml | 1.9E2 | 1.6E3 | 1.6E3 | 1.6E3 | 5.0E3 | 5.0E3 | 1.0E-9 | 1.0E-9 | 2.9E4 | 2.4E4 | 357 | 75 | 189 | 75 | 0.48 |
| Iv | ng/ml | 1.1E1 | 2.0E1 | 8.5E1 | 1.3E2 | 8.5E2 | 7.4E2 | 1.0E-9 | 1.0E-9 | 1.6E4 | 6.4E3 | 357 | 75 | 189 | 75 | 0.60 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Iz | ng/ml | 1.2E2 | 3.1E2 | 4.2E2 | 4.6E2 | 9.7E2 | 4.9E2 | 1.5E0 | 8.7E0 | 8.4E3 | 2.3E3 | 120 | 47 | 98 | 47 | 0.61 |
| Yg | pg/ml | 2.5E2 | 6.7E2 | 5.7E3 | 1.5E3 | 8.6E2 | 2.8E3 | 1.0E-9 | 4.1E1 | 4.2E3 | 1.2E4 | 51 | 18 | 41 | 18 | 0.65 |
| Yh | pg/ml | 2.6E2 | 2.9E2 | 5.6E2 | 4.2E2 | 1.1E3 | 3.5E2 | 1.0E-9 | 1.0E-9 | 7.8E3 | 1.0E3 | 51 | 18 | 41 | 18 | 0.52 |
| Yi | pg/ml | 2.7E2 | 4.3E2 | 5.7E2 | 4.3E2 | 1.1E3 | 4.2E2 | 1.0E-9 | 1.0E-9 | 7.6E3 | 1.8E3 | 51 | 18 | 41 | 18 | 0.52 |
| Yk | U/ml | 1.0E-9 | 1.0E-9 | 9.9E-2 | 3.1E-2 | 2.9E-1 | 9.4E-2 | 1.0E-9 | 1.0E-9 | 1.5E0 | 3.6E-1 | 51 | 18 | 41 | 18 | 0.47 |
| Yj | pg/ml | 1.9E2 | 1.2E2 | 4.2E2 | 3.9E2 | 5.7E2 | 9.4E2 | 9.7E0 | 1.7E1 | 3.2E3 | 4.1E3 | 51 | 18 | 41 | 18 | 0.38 |
| Yd | ng/ml | 2.0E-1 | 1.5E-1 | 3.2E-1 | 2.9E-1 | 3.8E-1 | 2.5E-1 | 6.6E-3 | 7.9E-3 | 1.8E0 | 9.6E-1 | 55 | 19 | 44 | 19 | 0.52 |
| Wb | pg/ml | 3.1E4 | 3.1E4 | 3.4E4 | 4.6E4 | 1.8E4 | 3.8E4 | 2.2E3 | 1.0E1 | 8.5E4 | 1.6E5 | 55 | 18 | 44 | 18 | 0.55 |
| Vz | pg/ml | 3.6E0 | 2.3E0 | 5.6E0 | 2.4E0 | 6.6E0 | 1.9E0 | 1.0E-9 | 1.0E-9 | 4.0E1 | 7.6E0 | 55 | 18 | 44 | 18 | 0.31 |
| Si | ng/ml | 9.1E-1 | 8.2E-1 | 1.7E0 | 2.7E0 | 2.2E0 | 3.8E0 | 2.0E-2 | 7.8E-2 | 1.0E1 | 1.3E1 | 53 | 19 | 42 | 19 | 0.57 |
| Sf | mIU/mL | 1.1E1 | 1.4E1 | 4.8E1 | 2.2E1 | 1.1E2 | 3.4E1 | 8.1E-2 | 2.0E-1 | 7.2E2 | 1.5E2 | 53 | 19 | 42 | 19 | 0.50 |
| Sh | mIU/mL | 7.7E0 | 9.0E0 | 4.1E1 | 2.6E1 | 1.1E2 | 4.3E1 | 2.9E-2 | 1.3E-1 | 5.9E2 | 1.8E2 | 53 | 19 | 42 | 19 | 0.51 |
| Sj | ng/ml | 4.0E-1 | 3.8E-1 | 4.0E-1 | 3.9E-1 | 9.0E-2 | 1.3E-1 | 1.9E-1 | 1.1E-1 | 5.7E-1 | 6.2E-1 | 53 | 19 | 42 | 19 | 0.48 |
| Rc | pg/ml | 5.0E3 | 6.9E3 | 6.4E3 | 8.6E3 | 5.0E3 | 6.2E3 | 1.9E2 | 1.1E3 | 3.0E4 | 2.3E4 | 122 | 47 | 98 | 47 | 0.59 |
| Rb | pg/ml | 7.5E-1 | 1.1E0 | 2.4E0 | 3.1E0 | 3.6E0 | 4.4E0 | 1.0E-9 | 1.0E-9 | 1.6E1 | 2.1E1 | 122 | 47 | 98 | 47 | 0.54 |
| Zq | 2.6ng/ml | 1.6E2 | 2.0E2 | 2.5E2 | 4.0E2 | 2.5E2 | 3.6E2 | 8.3E0 | 6.9E1 | 9.7E2 | 9.7E2 | 52 | 19 | 41 | 19 | 0.64 |
| Zw | 2.5ng/ml | 4.3E0 | 3.8E0 | 1.0E1 | 9.1E0 | 1.4E1 | 1.2E1 | 6.3E-2 | 3.5E-1 | 5.9E1 | 4.6E1 | 55 | 19 | 44 | 19 | 0.47 |
| Zx | 2.3mU/ml | 1.1E-1 | 9.5E-2 | 4.0E-1 | 3.2E-1 | 1.6E0 | 6.6E-1 | 4.1E-2 | 5.6E-2 | 1.2E1 | 3.0E0 | 55 | 19 | 44 | 19 | 0.53 |
| Pz | ng/ml | 3.1E3 | 5.7E3 | 6.1E3 | 2.1E4 | 9.7E3 | 1.2E5 | 1.3E1 | 3.6E1 | 9.5E4 | 1.0E6 | 358 | 75 | 189 | 75 | 0.56 |
| Qa | ng/ml | 2.7E3 | 4.5E3 | 5.9E3 | 6.7E3 | 8.0E3 | 6.2E3 | 1.5E2 | 3.4E2 | 5.2E4 | 2.7E4 | 358 | 75 | 189 | 75 | 0.62 |
| Qb | ng/ml | 8.3E1 | 1.3E2 | 2.5E2 | 1.7E2 | 7.0E2 | 1.6E2 | 7.9E-1 | 1.0E1 | 8.3E3 | 7.2E2 | 358 | 75 | 189 | 75 | 0.57 |
| Qc | ng/ml | 1.9E2 | 3.2E2 | 4.7E2 | 4.4E2 | 9.5E2 | 4.8E2 | 8.1E-1 | 1.1E1 | 1.1E4 | 3.1E3 | 358 | 75 | 189 | 75 | 0.56 |
| Qd | ng/ml | 7.9E3 | 1.2E4 | 2.2E4 | 2.0E4 | 1.1E5 | 2.5E4 | 1.5E2 | 9.8E2 | 2.0E6 | 1.5E5 | 358 | 75 | 189 | 75 | 0.60 |
| Qe | ng/ml | 6.9E2 | 1.3E3 | 1.9E3 | 2.0E3 | 5.6E3 | 2.4E3 | 1.0E-9 | 6.8E1 | 9.7E4 | 1.4E4 | 358 | 75 | 189 | 75 | 0.62 |
| Jd | ng/ml | 4.3E-1 | 2.1E0 | 7.5E0 | 4.4E0 | 5.9E1 | 1.1E1 | 1.0E-9 | 1.0E-9 | 6.5E2 | 7.3E1 | 122 | 47 | 99 | 47 | 0.69 |
| Je | ng/ml | 1.0E-9 | 2.9E-1 | 1.4E0 | 1.4E0 | 5.4E0 | 2.1E0 | 1.0E-9 | 1.0E-9 | 5.6E1 | 7.0E0 | 122 | 47 | 99 | 47 | 0.59 |
| Jf | ng/ml | 1.0E-9 | 1.0E-9 | 7.4E-1 | 1.2E0 | 1.9E0 | 2.4E0 | 1.0E-9 | 1.0E-9 | 1.2E1 | 9.6E0 | 122 | 47 | 99 | 47 | 0.55 |
| Jg | ng/ml | 3.7E2 | 8.0E2 | 6.8E2 | 1.2E3 | 1.0E3 | 1.1E3 | 5.8E0 | 1.1E1 | 1.0E4 | 5.4E3 | 360 | 75 | 190 | 75 | 0.67 |
| Jh | ng/ml | 2.3E0 | 5.5E0 | 2.4E1 | 3.6E1 | 9.5E1 | 8.8E1 | 1.0E-9 | 1.0E-9 | 1.2E3 | 4.7E2 | 360 | 75 | 190 | 75 | 0.60 |
| Ji | ng/ml | 4.6E1 | 7.0E1 | 6.6E1 | 1.1E2 | 7.0E1 | 1.0E2 | 1.1E0 | 8.3E0 | 5.3E2 | 5.9E2 | 360 | 75 | 190 | 75 | 0.67 |
| Sr | pg/mL | 3.2E2 | 4.9E2 | 7.5E2 | 8.9E2 | 1.3E3 | 1.1E3 | 1.0E-9 | 1.0E-9 | 9.8E3 | 5.1E3 | 121 | 45 | 98 | 45 | 0.58 |
| Ss | pg/mL | 6.2E4 | 2.0E5 | 1.2E5 | 1.7E5 | 1.4E5 | 1.3E5 | 9.5E3 | 6.5E3 | 7.1E5 | 5.3E5 | 121 | 45 | 98 | 45 | 0.62 |
| St | pg/mL | 1.7E7 | 2.9E7 | 4.0E7 | 4.8E7 | 5.3E7 | 6.0E7 | 7.8E5 | 1.1E6 | 4.1E8 | 2.9E8 | 119 | 47 | 96 | 47 | 0.57 |
| Wc | ng/ml | 1.0E-9 | 1.2E-2 | 6.2E-2 | 5.3E-2 | 1.6E-1 | 8.4E-2 | 1.0E-9 | 1.0E-9 | 9.8E-1 | 2.8E-1 | 55 | 19 | 43 | 19 | 0.55 |
| Wd | ng/ml | 8.8E0 | 1.7E1 | 2.5E1 | 7.0E1 | 7.8E1 | 1.8E2 | 1.0E-9 | 5.0E-1 | 5.4E2 | 7.9E2 | 55 | 19 | 43 | 19 | 0.62 |
| We | ng/ml | 2.6E-1 | 7.7E-1 | 6.0E-1 | 8.9E-1 | 9.0E-1 | 1.0E0 | 1.0E-9 | 1.0E-9 | 3.9E0 | 3.5E0 | 55 | 19 | 43 | 19 | 0.58 |
| Wg | ng/ml | 1.0E-9 | 1.0E-9 | 2.9E-4 | 1.0E-9 | 2.2E-3 | 0.0E0 | 1.0E-9 | 1.0E-9 | 1.6E-2 | 1.0E-9 | 55 | 19 | 43 | 19 | 0.49 |
| Wh | ng/ml | 8.7E-3 | 1.5E-2 | 3.4E-2 | 1.9E-1 | 1.1E-1 | 5.6E-1 | 1.0E-9 | 1.0E-9 | 7.6E-1 | 2.5E0 | 55 | 19 | 43 | 19 | 0.59 |
| Wf | ng/ml | 1.0E-9 | 1.0E-9 | 2.0E-1 | 2.2E-1 | 6.5E-1 | 5.9E-1 | 1.0E-9 | 1.0E-9 | 4.6E0 | 2.4E0 | 55 | 19 | 43 | 19 | 0.45 |
| Ra | pg/ml | 1.0E-9 | 1.0E-9 | 6.8E-1 | 2.7E-1 | 1.3E0 | 7.4E-1 | 1.0E-9 | 1.0E-9 | 7.3E0 | 2.6E0 | 122 | 47 | 98 | 47 | 0.43 |
| Qz | pg/ml | 1.1E1 | 1.3E1 | 7.1E1 | 5.0E1 | 1.1E2 | 6.4E1 | 1.0E-9 | 1.0E-9 | 7.1E2 | 2.2E2 | 122 | 47 | 98 | 47 | 0.48 |
| Qy | pg/ml | 3.9E-1 | 5.4E-1 | 3.6E0 | 2.7E1 | 1.6E1 | 1.0E2 | 1.0E-9 | 1.0E-9 | 1.6E2 | 5.1E2 | 122 | 47 | 98 | 47 | 0.56 |
| Qx | pg/ml | 1.0E-9 | 1.0E-9 | 5.6E0 | 5.2E-1 | 4.9E1 | 2.0E0 | 1.0E-9 | 1.0E-9 | 5.4E2 | 9.4E0 | 122 | 47 | 98 | 47 | 0.48 |
| Qw | pg/ml | 9.0E-2 | 1.0E-9 | 2.2E0 | 2.6E0 | 1.1E1 | 1.3E1 | 1.0E-9 | 1.0E-9 | 1.2E2 | 8.6E1 | 122 | 47 | 98 | 47 | 0.48 |
| Qv | pg/ml | 2.8E4 | 2.1E4 | 3.9E4 | 2.9E4 | 7.4E4 | 3.6E4 | 1.2E3 | 1.1E3 | 7.4E5 | 2.3E5 | 122 | 47 | 98 | 47 | 0.41 |
| Qu | pg/ml | 1.7E0 | 2.2E1 | 8.6E1 | 1.1E2 | 1.8E2 | 2.0E2 | 1.0E-9 | 1.0E-9 | 8.0E2 | 9.2E2 | 122 | 47 | 98 | 47 | 0.58 |
| Qt | pg/ml | 9.9E0 | 1.3E1 | 3.6E1 | 7.2E1 | 7.7E1 | 1.5E2 | 1.0E-9 | 1.0E-9 | 4.1E2 | 7.0E2 | 122 | 47 | 98 | 47 | 0.57 |
| Qh | ng/ml | 1.3E1 | 1.7E1 | 3.5E1 | 3.4E1 | 7.0E1 | 4.7E1 | 1.2E-1 | 1.4E0 | 6.4E2 | 2.6E2 | 122 | 47 | 98 | 47 | 0.57 |
| Qg | ng/ml | 9.0E0 | 7.0E0 | 1.7E1 | 1.5E1 | 2.5E1 | 3.2E1 | 1.5E-1 | 1.3E-1 | 1.8E2 | 2.2E2 | 122 | 47 | 98 | 47 | 0.43 |
| Jj | ng/ml | 7.1E2 | 5.7E2 | 2.7E3 | 1.1E3 | 1.9E4 | 1.7E3 | 2.3E0 | 4.9E0 | 3.4E5 | 1.1E4 | 360 | 75 | 190 | 75 | 0.43 |
| Jk | ng/ml | 3.0E0 | 3.8E0 | 2.1E1 | 2.6E1 | 4.6E1 | 4.9E1 | 1.0E-9 | 1.2E-1 | 2.8E2 | 2.7E2 | 360 | 75 | 190 | 75 | 0.55 |
| Jl | ng/ml | 3.4E-1 | 6.6E-1 | 1.9E0 | 4.5E0 | 4.7E1 | 1.8E1 | 7.6E-4 | 1.1E-3 | 3.2E1 | 1.6E2 | 360 | 75 | 190 | 75 | 0.60 |
| Jm | ng/ml | 1.5E1 | 2.0E1 | 5.3E1 | 5.7E1 | 1.2E2 | 9.1E1 | 1.0E-9 | 4.1E-1 | 1.4E3 | 6.1E2 | 360 | 75 | 190 | 75 | 0.55 |
| Jn | pg/ml | 3.2E-1 | 4.2E-1 | 3.2E0 | 1.4E0 | 3.3E1 | 3.5E0 | 1.0E-9 | 1.0E-9 | 6.2E2 | 2.7E1 | 360 | 75 | 190 | 75 | 0.57 |
| Jo | pg/ml | 3.5E3 | 4.2E3 | 4.8E3 | 5.8E3 | 3.9E3 | 5.5E3 | 2.0E1 | 7.5E1 | 2.0E4 | 3.8E4 | 360 | 75 | 190 | 75 | 0.55 |
| Jp | pg/ml | 6.3E4 | 8.3E4 | 6.6E4 | 8.5E4 | 3.7E4 | 3.9E4 | 5.8E2 | 2.8E3 | 3.0E5 | 2.1E5 | 360 | 75 | 190 | 75 | 0.65 |
| Jq | pg/ml | 9.1E1 | 1.1E2 | 1.4E2 | 2.0E2 | 1.8E2 | 4.8E2 | 1.0E0 | 5.4E0 | 2.0E3 | 4.0E3 | 360 | 75 | 190 | 75 | 0.55 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jr | pg/ml | 3.3E0 | 6.7E0 | 4.5E1 | 1.6E1 | 5.6E2 | 3.5E1 | 1.0E-9 | 1.0E-9 | 1.1E4 | 2.0E2 | 360 | 75 | 190 | 75 | 0.58 |
| Js | pg/ml | 1.2E1 | 1.4E1 | 6.5E1 | 2.6E1 | 5.4E2 | 6.9E1 | 1.0E-9 | 1.0E-9 | 1.0E4 | 5.9E2 | 360 | 75 | 190 | 75 | 0.54 |
| Jt | pg/ml | 2.2E3 | 3.3E3 | 2.8E3 | 3.9E3 | 2.2E3 | 4.0E3 | 2.2E1 | 2.6E2 | 2.2E4 | 3.3E4 | 360 | 75 | 190 | 75 | 0.61 |
| Xa | pg/ml | 1.0E-9 | 4.8E0 | 7.0E0 | 1.8E1 | 1.5E1 | 2.7E1 | 1.0E-9 | 1.0E-9 | 7.6E1 | 9.9E1 | 55 | 18 | 44 | 18 | 0.63 |
| Ye | pg/ml | 1.0E-9 | 1.0E-9 | 3.9E0 | 2.5E1 | 1.3E1 | 8.2E1 | 1.0E-9 | 1.0E-9 | 6.9E1 | 3.5E2 | 55 | 18 | 44 | 18 | 0.52 |
| Tm | pg/ml | 1.0E-9 | 1.0E-9 | 2.4E0 | 9.2E0 | 4.8E0 | 1.9E1 | 1.0E-9 | 1.0E-9 | 1.8E1 | 6.8E1 | 55 | 18 | 44 | 18 | 0.59 |
| Tl | pg/ml | 1.1E-1 | 4.7E-1 | 2.3E-1 | 4.0E-1 | 3.6E-1 | 3.5E-1 | 1.0E-9 | 1.0E-9 | 1.8E0 | 1.2E0 | 55 | 18 | 44 | 18 | 0.66 |
| Ju | mIU/ml | 7.2E0 | 1.1E1 | 2.0E1 | 2.0E1 | 3.4E1 | 3.2E1 | 6.5E-2 | 1.5E-1 | 2.3E2 | 2.0E2 | 122 | 47 | 99 | 47 | 0.58 |
| Jv | mIU/ml | 9.3E0 | 1.6E1 | 3.1E1 | 3.2E1 | 6.1E1 | 5.6E1 | 1.0E-2 | 8.2E-2 | 4.4E2 | 3.4E2 | 122 | 47 | 99 | 47 | 0.55 |
| Jy | ng/ml | 1.7E-3 | 1.6E-3 | 2.3E-3 | 1.7E-3 | 4.7E-3 | 8.5E-4 | 1.0E-9 | 1.0E-9 | 5.2E-2 | 3.8E-3 | 122 | 47 | 99 | 47 | 0.47 |
| Kc | pg/ml | 2.1E1 | 3.9E1 | 3.9E1 | 5.8E1 | 4.4E1 | 5.1E1 | 1.0E-9 | 1.0E-9 | 1.7E2 | 1.8E2 | 121 | 46 | 98 | 46 | 0.67 |
| Kd | pg/ml | 1.0E-9 | 1.0E-9 | 1.9E2 | 2.4E2 | 6.7E2 | 5.7E2 | 1.0E-9 | 1.0E-9 | 4.8E3 | 2.3E3 | 121 | 46 | 98 | 46 | 0.52 |
| Ke | pg/ml | 9.5E3 | 1.6E4 | 1.3E4 | 1.7E4 | 9.6E3 | 1.0E4 | 3.4E2 | 5.8E2 | 5.9E4 | 5.6E4 | 121 | 46 | 98 | 46 | 0.63 |
| Kf | pg/mL | 5.5E0 | 9.4E0 | 6.3E0 | 8.7E0 | 5.7E0 | 5.0E0 | 1.0E-9 | 1.0E-9 | 2.6E1 | 2.4E1 | 121 | 46 | 98 | 46 | 0.66 |
| Kg | pg/mL | 9.9E2 | 1.6E3 | 1.7E3 | 2.2E3 | 2.4E3 | 2.2E3 | 7.7E1 | 1.4E2 | 2.2E4 | 1.1E4 | 121 | 46 | 98 | 46 | 0.60 |
| Ki | pg/ml | 6.5E1 | 5.6E1 | 7.2E1 | 6.5E1 | 5.2E1 | 3.0E1 | 1.0E-9 | 1.0E-9 | 2.9E2 | 1.2E2 | 121 | 45 | 98 | 45 | 0.48 |
| Kj | pg/ml | 9.3E2 | 1.5E3 | 1.5E3 | 1.8E3 | 1.6E3 | 1.5E3 | 6.6E1 | 1.1E2 | 1.0E4 | 6.1E3 | 121 | 46 | 98 | 46 | 0.61 |
| Kk | pg/ml | 6.8E0 | 7.0E0 | 1.2E1 | 1.2E1 | 1.8E1 | 1.5E1 | 1.0E-9 | 1.0E-9 | 1.6E2 | 6.1E1 | 121 | 46 | 98 | 46 | 0.52 |
| Kl | pg/ml | 1.7E4 | 3.4E4 | 2.4E4 | 3.8E4 | 2.3E4 | 3.1E4 | 3.5E2 | 2.1E2 | 1.1E5 | 1.6E5 | 121 | 46 | 98 | 46 | 0.64 |
| Kn | pg/ml | 1.5E1 | 4.1E1 | 5.4E1 | 6.2E1 | 1.1E2 | 8.1E1 | 1.0E-9 | 1.0E-9 | 7.3E2 | 4.7E2 | 121 | 46 | 98 | 46 | 0.62 |
| Ko | pg/ml | 3.0E2 | 5.7E2 | 3.9E2 | 6.3E2 | 4.0E2 | 6.1E2 | 1.0E-9 | 1.0E-9 | 1.8E3 | 2.4E3 | 121 | 46 | 98 | 46 | 0.61 |
| Kp | pg/ml | 2.7E2 | 3.6E2 | 3.2E2 | 4.1E2 | 2.9E2 | 2.4E2 | 1.0E-9 | 1.0E-9 | 1.7E3 | 9.1E2 | 121 | 46 | 98 | 46 | 0.62 |
| Kq | pg/ml | 2.8E2 | 3.9E2 | 4.2E2 | 4.8E2 | 9.3E2 | 3.8E2 | 5.1E0 | 7.0E0 | 9.8E3 | 2.1E3 | 117 | 47 | 95 | 47 | 0.63 |
| Kr | pg/ml | 3.6E-1 | 2.5E-1 | 2.4E0 | 2.4E0 | 4.8E0 | 3.5E0 | 1.0E-9 | 1.0E-9 | 3.5E1 | 1.2E1 | 117 | 47 | 95 | 47 | 0.53 |
| Ks | pg/ml | 1.5E4 | 1.1E4 | 2.0E4 | 2.0E4 | 1.9E4 | 1.8E4 | 3.8E2 | 2.7E2 | 1.1E5 | 5.0E4 | 117 | 47 | 95 | 47 | 0.49 |
| Ps | ng/ml | 1.4E2 | 1.9E2 | 5.2E2 | 5.2E2 | 1.6E3 | 7.5E2 | 1.6E0 | 4.1E-1 | 9.0E3 | 2.9E3 | 53 | 19 | 41 | 19 | 0.60 |
| Kx | ng/ml | 1.0E-9 | 3.4E-3 | 4.4E-3 | 6.4E-3 | 8.5E-3 | 9.2E-3 | 1.0E-9 | 1.0E-9 | 5.1E-2 | 4.4E-2 | 120 | 47 | 98 | 47 | 0.58 |
| Ky | ng/ml | 7.7E-2 | 1.1E-1 | 3.2E-1 | 3.2E-1 | 6.9E-1 | 5.1E-1 | 1.0E-9 | 1.0E-9 | 5.1E0 | 2.4E0 | 120 | 47 | 98 | 47 | 0.52 |
| Kz | ng/ml | 1.0E-9 | 1.0E-9 | 4.7E-3 | 2.6E-3 | 6.8E-3 | 5.1E-3 | 1.0E-9 | 1.0E-9 | 3.6E-2 | 1.4E-2 | 120 | 47 | 98 | 47 | 0.42 |
| Rz | ng/ml | 1.4E-1 | 5.6E-1 | 8.8E-1 | 1.2E0 | 1.5E0 | 1.6E0 | 3.6E-3 | 1.8E-2 | 6.7E0 | 4.7E0 | 53 | 19 | 42 | 19 | 0.63 |
| Ry | ng/ml | 1.6E-2 | 1.6E-2 | 1.9E-2 | 2.1E-2 | 1.8E-2 | 1.7E-2 | 1.0E-9 | 1.0E-9 | 1.0E-1 | 6.5E-2 | 53 | 19 | 42 | 19 | 0.57 |
| Rx | ng/ml | 3.5E-5 | 3.5E-5 | 2.1E-3 | 1.0E-3 | 3.8E-3 | 1.6E-3 | 1.0E-9 | 1.0E-9 | 2.0E-2 | 4.7E-3 | 53 | 19 | 42 | 19 | 0.47 |
| Ld | pg/ml | 1.0E-9 | 1.0E-9 | 3.6E0 | 1.8E0 | 9.5E0 | 2.9E0 | 1.0E-9 | 1.0E-9 | 6.9E1 | 1.2E1 | 119 | 46 | 97 | 46 | 0.47 |
| Lh | pg/ml | 1.0E4 | 1.4E4 | 1.8E4 | 2.8E4 | 2.6E4 | 4.9E4 | 1.0E-9 | 1.8E2 | 2.6E5 | 4.1E5 | 359 | 75 | 190 | 75 | 0.63 |
| Li | pg/ml | 2.5E3 | 5.7E3 | 1.3E4 | 2.4E4 | 7.2E4 | 7.2E4 | 1.0E-9 | 1.7E2 | 1.3E6 | 5.9E5 | 359 | 75 | 190 | 75 | 0.64 |
| Lj | pg/ml | 1.7E3 | 4.4E3 | 1.4E4 | 2.7E4 | 5.1E4 | 7.7E4 | 1.0E-9 | 4.1E1 | 4.4E5 | 4.7E5 | 359 | 75 | 190 | 75 | 0.61 |
| Lp | pg/ml | 9.4E0 | 5.7E0 | 5.6E1 | 8.1E1 | 1.6E2 | 1.9E2 | 1.0E-9 | 1.0E-9 | 1.1E3 | 7.7E2 | 53 | 19 | 42 | 19 | 0.48 |
| Lt | pg/ml | 1.0E-9 | 1.0E-9 | 2.6E0 | 1.8E0 | 9.6E0 | 6.0E0 | 1.0E-9 | 1.0E-9 | 6.0E1 | 2.5E1 | 53 | 19 | 42 | 19 | 0.50 |
| Rv | ng/ml | 2.2E-4 | 9.8E-4 | 1.1E-3 | 1.1E-3 | 1.8E-3 | 1.2E-3 | 1.0E-9 | 1.0E-9 | 9.2E-3 | 5.0E-3 | 53 | 19 | 41 | 19 | 0.56 |
| Ru | ng/ml | 1.0E-9 | 1.0E-9 | 8.1E-3 | 2.3E-2 | 4.5E-2 | 8.8E-2 | 1.0E-9 | 1.0E-9 | 3.1E-1 | 3.8E-1 | 53 | 19 | 41 | 19 | 0.53 |
| Rt | ng/ml | 6.2E-2 | 4.0E-2 | 9.3E-2 | 1.1E-1 | 1.1E-1 | 1.6E-1 | 1.6E-3 | 1.0E-3 | 4.5E-1 | 5.6E-1 | 53 | 19 | 41 | 19 | 0.46 |
| Yl | pg/ml | 1.4E1 | 7.9E0 | 1.9E1 | 1.0E1 | 1.7E1 | 1.5E1 | 1.0E-9 | 1.0E-9 | 6.5E1 | 6.6E1 | 55 | 19 | 44 | 19 | 0.30 |
| Rm | ng/ml | 1.6E1 | 1.7E1 | 5.2E1 | 3.8E1 | 8.3E1 | 5.3E1 | 2.2E-1 | 1.3E0 | 4.0E2 | 2.5E2 | 121 | 46 | 97 | 46 | 0.50 |
| Rh | ng/ml | 1.3E2 | 1.5E2 | 4.7E2 | 2.8E2 | 1.6E3 | 3.5E2 | 4.7E0 | 3.6E0 | 1.7E4 | 2.0E3 | 121 | 46 | 97 | 46 | 0.53 |
| Ri | ng/ml | 1.0E-9 | 1.0E-9 | 4.3E0 | 3.5E0 | 1.0E1 | 7.8E0 | 1.0E-9 | 1.0E-9 | 7.4E1 | 4.5E1 | 122 | 46 | 98 | 46 | 0.48 |
| Rg | ng/ml | 1.0E-9 | 1.0E-9 | 3.2E-2 | 1.9E-2 | 2.6E-1 | 1.0E-1 | 1.0E-9 | 1.0E-9 | 2.7E0 | 6.8E-1 | 121 | 46 | 97 | 46 | 0.55 |
| Rj | ng/ml | 1.0E-9 | 1.0E-9 | 1.8E0 | 9.4E-1 | 7.6E0 | 1.6E0 | 1.0E-9 | 1.0E-9 | 8.0E1 | 6.3E0 | 122 | 46 | 98 | 46 | 0.52 |
| Rf | ng/ml | 3.4E-1 | 5.7E-1 | 8.0E-1 | 1.4E0 | 1.5E0 | 2.2E0 | 7.8E-3 | 1.8E-2 | 1.4E1 | 1.2E1 | 121 | 46 | 97 | 46 | 0.61 |
| Ql | pg/ml | 5.0E0 | 4.5E0 | 1.1E1 | 1.6E1 | 1.7E1 | 3.0E1 | 1.0E-9 | 1.0E-9 | 1.2E2 | 1.8E2 | 122 | 47 | 99 | 47 | 0.51 |
| Qm | pg/ml | 1.7E0 | 9.6E0 | 2.0E1 | 2.5E1 | 4.4E1 | 3.6E1 | 1.0E-9 | 1.0E-9 | 3.6E2 | 1.7E2 | 122 | 47 | 99 | 47 | 0.59 |
| Qn | pg/ml | 6.1E-1 | 1.4E0 | 7.2E0 | 1.1E1 | 2.4E1 | 3.6E1 | 1.0E-9 | 1.0E-9 | 2.2E2 | 2.4E2 | 122 | 47 | 99 | 47 | 0.54 |
| Nv | pg/ml | 3.0E3 | 4.7E3 | 1.1E4 | 1.2E4 | 5.8E4 | 1.9E4 | 8.4E1 | 1.1E6 | 1.1E5 | | 362 | 76 | 190 | 76 | 0.63 |
| Nw | pg/ml | 7.1E3 | 1.4E4 | 1.2E4 | 1.6E4 | 2.1E4 | 1.8E4 | 8.6E2 | 5.7E2 | 2.1E5 | 1.4E5 | 362 | 76 | 190 | 76 | 0.66 |
| Nx | pg/ml | 1.2E2 | 2.4E2 | 3.6E2 | 5.7E2 | 6.8E2 | 7.2E2 | 1.0E-9 | 1.0E-9 | 7.4E3 | 2.6E3 | 362 | 76 | 190 | 76 | 0.63 |
| Ny | pg/ml | 5.2E0 | 9.6E0 | 9.8E1 | 2.8E1 | 1.3E3 | 8.6E1 | 1.0E-9 | 1.0E-9 | 2.5E4 | 6.2E2 | 362 | 76 | 190 | 76 | 0.55 |
| Oa | pg/ml | 1.6E2 | 2.5E2 | 4.0E2 | 3.7E2 | 7.6E2 | 4.4E2 | 1.0E-9 | 1.0E-9 | 4.8E3 | 2.3E3 | 122 | 47 | 99 | 47 | 0.56 |
| Op | pg/ml | 4.1E5 | 4.0E5 | 3.9E5 | 4.1E5 | 1.6E5 | 1.5E5 | 3.3E4 | 1.1E5 | 7.3E5 | 6.6E5 | 53 | 19 | 42 | 19 | 0.54 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Wn | ng/ml | 1.2E1 | 1.7E1 | 9.2E1 | 5.2E1 | 3.0E2 | 1.1E2 | 2.2E0 | 8.9E-1 | 1.8E3 | 4.9E2 | 35 | 17 | 29 | 17 | 0.55 |
| Tk | ng/ml | 1.3E2 | 1.6E2 | 3.8E2 | 2.5E2 | 7.3E2 | 2.8E2 | 1.9E1 | 2.2E1 | 4.2E3 | 1.2E3 | 37 | 17 | 30 | 17 | 0.50 |
| Oe | pg/ml | 1.1E1 | 4.3E1 | 2.3E2 | 3.6E2 | 3.7E2 | 7.8E2 | 1.0E-9 | 1.0E-9 | 2.7E3 | 5.1E3 | 357 | 76 | 190 | 76 | 0.52 |
| Of | pg/ml | 1.6E2 | 3.4E2 | 4.0E3 | 1.4E4 | 1.5E4 | 7.2E4 | 1.0E-9 | 1.0E-9 | 1.8E5 | 6.2E5 | 360 | 76 | 190 | 76 | 0.53 |
| Og | pg/ml | 8.4E-2 | 1.0E-1 | 5.8E-1 | 7.1E-1 | 1.9E0 | 1.8E0 | 1.0E-9 | 1.0E-9 | 2.0E1 | 1.0E1 | 360 | 76 | 190 | 76 | 0.55 |
| Oh | pg/ml | 1.9E0 | 3.2E2 | 2.2E1 | 1.0E1 | 1.2E2 | 3.4E1 | 1.0E-9 | 1.2E-2 | 1.4E3 | 2.2E2 | 360 | 76 | 190 | 76 | 0.60 |
| Oi | pg/ml | 2.0E0 | 4.4E0 | 6.3E0 | 8.5E0 | 1.1E1 | 1.0E1 | 1.0E-9 | 1.0E-9 | 8.6E1 | 4.1E1 | 360 | 76 | 190 | 76 | 0.59 |
| Ok | pg/ml | 2.9E2 | 5.4E2 | 3.9E2 | 8.3E2 | 3.7E2 | 1.2E3 | 1.3E1 | 4.0E1 | 2.8E3 | 9.8E3 | 360 | 76 | 190 | 76 | 0.70 |
| Om | pg/ml | 3.6E2 | 5.6E2 | 7.4E2 | 1.6E3 | 2.0E3 | 4.6E3 | 1.0E-9 | 1.0E-9 | 3.0E4 | 3.6E4 | 360 | 76 | 190 | 76 | 0.62 |
| On | pg/ml | 1.3E2 | 2.2E2 | 2.5E2 | 5.3E2 | 4.5E2 | 1.7E3 | 1.0E-9 | 7.2E0 | 4.5E3 | 1.5E4 | 360 | 76 | 190 | 76 | 0.65 |
| Or | pg/ml | 1.0E1 | 1.3E1 | 2.9E1 | 4.2E1 | 6.1E1 | 1.2E2 | 1.0E-9 | 1.0E-9 | 5.0E2 | 7.6E2 | 120 | 47 | 98 | 47 | 0.49 |
| Ow | pg/ml | 2.7E1 | 4.1E1 | 9.9E1 | 1.5E2 | 2.9E2 | 4.8E2 | 1.0E-9 | 1.0E-9 | 2.3E3 | 3.2E3 | 120 | 47 | 98 | 47 | 0.57 |
| Ou | pg/ml | 5.0E2 | 5.6E2 | 8.2E2 | 1.2E3 | 1.2E3 | 2.0E3 | 3.5E1 | 1.0E-9 | 9.4E3 | 9.3E3 | 120 | 47 | 98 | 47 | 0.56 |
| Ul | ng/ml | 1.0E-9 | 1.0E-9 | 1.2E0 | 8.5E-1 | 4.3E0 | 3.9E0 | 1.0E-9 | 1.0E-9 | 2.9E1 | 2.4E1 | 131 | 47 | 102 | 47 | 0.48 |
| Uo | ng/ml | 1.0E-9 | 1.0E-9 | 1.0E-1 | 7.5E-2 | 2.3E-1 | 1.9E-1 | 1.0E-9 | 1.0E-9 | 1.3E0 | 8.5E-1 | 131 | 47 | 102 | 47 | 0.46 |
| Uk | ng/ml | 1.0E-9 | 1.0E-9 | 4.7E-3 | 1.0E-2 | 1.1E-2 | 2.2E-2 | 1.0E-9 | 1.0E-9 | 9.9E-2 | 1.1E-1 | 131 | 47 | 102 | 47 | 0.52 |
| Um | ng/ml | 1.0E-9 | 1.0E-9 | 4.0E-1 | 2.0E-1 | 9.8E-1 | 3.3E-1 | 1.0E-9 | 1.0E-9 | 6.8E0 | 1.3E0 | 131 | 47 | 102 | 47 | 0.50 |
| Uf | ng/ml | 4.1E-2 | 1.0E-1 | 1.0E-1 | 1.9E-1 | 1.4E-1 | 3.7E-1 | 2.7E-3 | 1.1E-3 | 7.0E-1 | 2.5E0 | 131 | 47 | 102 | 47 | 0.65 |
| Uh | ng/ml | 1.6E0 | 2.2E0 | 2.7E0 | 4.0E0 | 2.7E0 | 4.5E0 | 3.2E-2 | 6.0E-2 | 1.5E1 | 1.7E1 | 131 | 47 | 102 | 47 | 0.57 |
| Un | ng/ml | 1.7E0 | 2.5E0 | 2.0E0 | 2.6E0 | 1.3E0 | 1.3E0 | 2.0E-1 | 5.4E-1 | 7.0E0 | 5.6E0 | 131 | 47 | 102 | 47 | 0.66 |
| Ug | ng/ml | 1.5E1 | 2.3E1 | 2.7E1 | 3.7E1 | 2.7E1 | 4.4E1 | 6.9E-1 | 1.1E0 | 1.3E2 | 2.1E2 | 131 | 47 | 102 | 47 | 0.53 |
| Ur | ng/ml | 1.7E-1 | 9.6E-2 | 1.2E0 | 5.7E-1 | 8.2E0 | 1.3E0 | 1.0E-9 | 1.0E-9 | 9.3E1 | 7.2E0 | 131 | 47 | 102 | 47 | 0.43 |
| Up | ng/ml | 1.0E-9 | 1.0E-9 | 6.9E-3 | 4.3E-3 | 3.2E-2 | 1.1E-2 | 1.0E-9 | 1.0E-9 | 3.3E-1 | 6.0E-2 | 131 | 47 | 102 | 47 | 0.54 |
| Us | ng/ml | 2.6E-3 | 6.6E-3 | 2.0E-2 | 1.8E-2 | 5.4E-2 | 2.5E-2 | 1.0E-9 | 1.0E-9 | 4.0E-1 | 1.0E-1 | 131 | 47 | 102 | 47 | 0.54 |
| Uv | ng/ml | 3.5E-3 | 2.8E-3 | 1.3E-2 | 6.9E-3 | 4.0E-2 | 1.2E-2 | 1.0E-9 | 1.0E-9 | 3.5E-1 | 7.1E-2 | 131 | 47 | 102 | 47 | 0.48 |
| Ut | ng/ml | 5.0E-1 | 6.3E-1 | 2.3E0 | 1.8E0 | 8.5E0 | 2.7E0 | 1.0E-9 | 1.0E-9 | 7.2E1 | 1.1E1 | 131 | 47 | 102 | 47 | 0.56 |
| Uu | ng/ml | 6.3E0 | 8.7E0 | 7.3E0 | 9.3E0 | 4.7E0 | 5.7E0 | 8.1E-1 | 4.5E-1 | 2.4E1 | 2.1E1 | 131 | 47 | 102 | 47 | 0.60 |
| Uw | ng/ml | 2.0E0 | 3.2E0 | 3.1E0 | 2.9E0 | 5.0E0 | 2.1E0 | 1.0E-9 | 2.0E-1 | 3.7E1 | 7.1E0 | 62 | 19 | 50 | 19 | 0.58 |
| Vb | ng/ml | 1.1E0 | 9.0E-1 | 1.1E0 | 1.0E0 | 4.3E-1 | 4.8E-1 | 2.5E-1 | 2.8E-1 | 2.5E0 | 1.9E0 | 62 | 19 | 50 | 19 | 0.45 |
| Vc | ng/ml | 1.0E-9 | 1.0E-9 | 1.4E-2 | 1.0E-9 | 8.4E-2 | 0.0E0 | 1.0E-9 | 1.0E-9 | 6.5E-1 | 1.0E-9 | 62 | 19 | 50 | 19 | 0.47 |
| Uy | ng/ml | 1.3E0 | 9.5E-1 | 4.1E0 | 2.3E0 | 9.0E0 | 3.7E0 | 5.3E-2 | 3.1E-2 | 5.1E1 | 1.6E1 | 62 | 19 | 50 | 19 | 0.43 |
| Uz | ng/ml | 1.0E-9 | 1.0E-9 | 7.1E-3 | 1.0E-9 | 5.5E-2 | 0.0E0 | 1.0E-9 | 1.0E-9 | 4.4E-1 | 1.0E-9 | 62 | 19 | 50 | 19 | 0.48 |
| Ux | ng/ml | 1.2E2 | 1.8E2 | 1.7E2 | 2.3E2 | 1.4E2 | 1.5E2 | 5.8E0 | 4.9E1 | 4.8E2 | 5.3E2 | 62 | 19 | 50 | 19 | 0.63 |
| Va | ng/ml | 1.8E1 | 1.0E1 | 2.5E1 | 2.2E1 | 2.6E1 | 3.0E1 | 1.2E-1 | 8.1E-1 | 1.2E2 | 1.2E2 | 62 | 19 | 50 | 19 | 0.42 |
| Vh | ng/ml | 5.2E-3 | 7.8E-3 | 1.3E-2 | 1.6E-2 | 1.8E-2 | 2.0E-2 | 1.0E-9 | 5.2E-4 | 1.2E-1 | 7.6E-2 | 62 | 19 | 50 | 19 | 0.54 |
| Vi | ng/ml | 2.5E-3 | 5.7E-3 | 2.3E-1 | 1.3E-2 | 1.7E0 | 2.0E-2 | 1.0E-9 | 9.0E-5 | 1.4E1 | 7.5E-2 | 62 | 19 | 50 | 19 | 0.60 |
| Vj | ng/ml | 1.9E1 | 5.3E1 | 1.6E2 | 5.3E2 | 6.8E2 | 2.0E3 | 3.2E0 | 6.5E0 | 5.2E3 | 8.4E3 | 62 | 18 | 50 | 18 | 0.66 |
| Vp | ng/ml | 1.0E-9 | 1.0E-9 | 6.8E-1 | 3.3E-2 | 5.0E0 | 1.7E-1 | 1.0E-9 | 1.0E-9 | 5.0E1 | 1.2E0 | 131 | 47 | 102 | 47 | 0.46 |
| Vt | ng/ml | 6.1E0 | 7.6E0 | 8.2E0 | 1.1E1 | 6.9E0 | 1.2E1 | 6.0E-1 | 8.8E-1 | 3.2E1 | 6.5E1 | 131 | 47 | 102 | 47 | 0.56 |
| Vu | ng/ml | 1.0E-9 | 1.0E-9 | 1.9E0 | 1.8E0 | 5.4E0 | 4.0E0 | 1.0E-9 | 1.0E-9 | 5.1E1 | 2.1E1 | 130 | 47 | 102 | 47 | 0.50 |
| Vq | ng/ml | 1.5E2 | 4.3E2 | 7.5E3 | 1.1E3 | 6.7E4 | 2.2E3 | 2.0E-1 | 9.0E-1 | 6.8E5 | 1.1E4 | 102 | 31 | 82 | 31 | 0.57 |
| Vo | ng/ml | 2.6E1 | 2.6E1 | 2.5E1 | 2.5E1 | 4.3E0 | 4.6E0 | 1.1E1 | 2.4E0 | 3.5E1 | 3.4E1 | 131 | 47 | 102 | 47 | 0.52 |
| Vs | ng/ml | 1.0E-9 | 1.6E0 | 6.0E0 | 4.6E0 | 2.6E1 | 8.3E0 | 1.0E-9 | 1.0E-9 | 2.3E2 | 4.2E1 | 127 | 45 | 99 | 45 | 0.59 |
| Vv | ng/ml | 2.2E0 | 4.1E0 | 5.7E0 | 6.1E0 | 1.0E1 | 6.9E0 | 1.0E-9 | 1.0E-9 | 8.1E1 | 2.8E1 | 130 | 47 | 102 | 47 | 0.57 |
| Vw | ng/ml | 3.4E1 | 4.1E1 | 3.3E1 | 4.1E1 | 1.7E1 | 1.7E1 | 3.1E0 | 9.9E0 | 6.7E1 | 7.0E1 | 62 | 19 | 50 | 19 | 0.62 |
| Oy | pg/ml | 5.4E-1 | 6.8E-1 | 7.9E0 | 7.3E0 | 3.9E1 | 3.2E1 | 1.0E-9 | 1.0E-9 | 4.0E2 | 2.7E2 | 360 | 76 | 190 | 76 | 0.56 |
| Oz | pg/ml | 1.4E-3 | 2.2E-1 | 2.3E-1 | 3.9E-1 | 3.8E-1 | 7.5E-1 | 1.0E-9 | 1.0E-9 | 2.6E0 | 5.8E0 | 360 | 76 | 190 | 76 | 0.60 |
| Pa | pg/ml | 3.3E-1 | 4.1E-1 | 1.3E0 | 4.8E0 | 5.6E0 | 3.4E1 | 1.0E-9 | 1.0E-9 | 8.6E1 | 2.9E2 | 360 | 76 | 190 | 76 | 0.57 |
| Pb | pg/ml | 1.0E-9 | 3.3E-2 | 1.6E0 | 2.5E0 | 2.6E1 | 2.1E1 | 1.0E-9 | 1.0E-9 | 4.9E2 | 1.8E2 | 360 | 76 | 190 | 76 | 0.56 |
| Pc | pg/ml | 2.4E-2 | 3.6E-1 | 4.2E-1 | 6.3E-1 | 1.2E0 | 1.5E0 | 1.0E-9 | 1.0E-9 | 1.6E1 | 1.1E1 | 360 | 76 | 190 | 76 | 0.60 |
| Pd | pg/ml | 1.7E0 | 2.7E0 | 3.7E0 | 4.7E0 | 8.5E0 | 5.5E0 | 1.0E-9 | 1.0E-9 | 9.4E1 | 2.7E1 | 360 | 76 | 190 | 76 | 0.62 |
| Pe | pg/ml | 1.7E1 | 3.1E1 | 8.8E1 | 2.7E2 | 3.4E2 | 1.6E3 | 1.0E-9 | 1.0E-9 | 4.7E3 | 1.4E4 | 360 | 76 | 190 | 76 | 0.63 |
| Pf | pg/ml | 1.2E0 | 2.6E0 | 8.1E0 | 1.0E1 | 3.9E1 | 3.1E1 | 1.0E-9 | 1.0E-9 | 4.8E2 | 2.3E2 | 360 | 76 | 190 | 76 | 0.62 |
| Pg | pg/ml | 2.9E0 | 5.0E0 | 3.5E1 | 4.3E1 | 1.9E2 | 2.2E2 | 1.0E-9 | 1.0E-9 | 3.2E3 | 1.9E3 | 360 | 76 | 190 | 76 | 0.58 |
| Ph | ng/ml | 1.5E-1 | 2.5E-1 | 2.6E0 | 4.5E-1 | 3.0E-1 | 6.1E-1 | 1.0E-9 | 1.0E-9 | 1.6E0 | 2.8E0 | 120 | 47 | 98 | 47 | 0.60 |
| Pi | ng/ml | 2.0E-1 | 1.9E-1 | 2.7E-1 | 2.3E-1 | 4.1E-1 | 2.0E-1 | 1.0E-9 | 1.0E-9 | 3.2E0 | 9.7E-1 | 120 | 47 | 98 | 47 | 0.50 |
| Pj | ng/mL | 4.5E0 | 7.0E0 | 5.1E0 | 8.7E0 | 3.3E0 | 6.4E0 | 3.8E-2 | 3.8E-1 | 1.6E1 | 2.5E1 | 120 | 47 | 98 | 47 | 0.65 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Pk | ng/ml | 8.1E-3 | 6.5E-3 | 1.2E-2 | 9.4E-3 | 1.2E-2 | 1.2E-2 | 1.0E-9 | 1.0E-9 | 5.9E-2 | 7.0E-2 | 120 | 47 | 98 | 47 | 0.44 |
| aA | mg/dL | 8.0E-1 | 9.8E-1 | 9.1E-1 | 1.2E0 | 4.4E-1 | 8.9E-1 | 3.0E-1 | 2.6E-1 | 4.1E0 | 5.4E0 | 1529 | 110 | 315 | 110 | 0.59 |
| aC | mg/mL | 3.2E0 | 2.4E0 | 3.4E0 | 2.6E0 | 1.5E0 | 9.9E-1 | 1.1E0 | 1.3E0 | 8.9E0 | 5.5E0 | 262 | 51 | 110 | 51 | 0.33 |
| aD | ug/mL | 3.1E0 | 3.6E0 | 4.5E0 | 4.9E0 | 4.0E0 | 3.8E0 | 4.3E-1 | 8.4E-1 | 3.5E1 | 2.0E1 | 262 | 51 | 110 | 51 | 0.56 |
| aE | mg/mL | 5.8E-1 | 5.3E-1 | 5.8E-1 | 5.4E-1 | 1.4E-1 | 1.4E-1 | 2.1E-1 | 3.1E-1 | 1.1E0 | 1.2E0 | 262 | 51 | 110 | 51 | 0.40 |
| aF | ng/mL | 2.0E0 | 1.6E0 | 4.1E0 | 3.6E0 | 6.5E0 | 4.5E0 | 4.3E-3 | 4.3E-3 | 5.0E1 | 1.8E1 | 262 | 51 | 110 | 51 | 0.45 |
| aG | mg/mL | 1.3E-1 | 1.4E-1 | 1.6E-1 | 1.5E-1 | 9.4E-2 | 8.2E-2 | 1.7E-2 | 5.8E-2 | 5.4E-1 | 3.8E-1 | 262 | 51 | 110 | 51 | 0.51 |
| aH | ug/mL | 7.0E1 | 8.0E1 | 7.8E1 | 9.1E1 | 3.8E1 | 5.1E1 | 4.6E0 | 1.1E1 | 2.7E2 | 2.6E2 | 262 | 51 | 110 | 51 | 0.57 |
| aI | ug/mL | 1.9E2 | 2.0E2 | 1.9E2 | 1.9E2 | 6.0E1 | 5.5E1 | 2.8E1 | 4.8E1 | 3.7E2 | 3.0E2 | 262 | 51 | 110 | 51 | 0.51 |
| aJ | ng/mL | 2.4E0 | 2.6E0 | 2.9E0 | 3.7E0 | 1.9E0 | 3.1E0 | 8.5E-1 | 7.6E-1 | 1.2E1 | 1.6E1 | 262 | 51 | 110 | 51 | 0.57 |
| aK | ng/mL | 1.8E0 | 1.6E0 | 2.7E0 | 1.9E0 | 2.8E0 | 1.7E0 | 2.8E-2 | 2.9E-4 | 1.8E1 | 7.0E0 | 262 | 51 | 110 | 51 | 0.43 |
| aL | mg/mL | 8.3E-1 | 8.0E-1 | 8.4E-1 | 8.2E-1 | 2.7E-1 | 2.4E-1 | 1.9E-1 | 3.0E-1 | 1.7E0 | 1.5E0 | 262 | 51 | 110 | 51 | 0.47 |
| aM | U/mL | 1.9E1 | 3.0E1 | 4.2E1 | 4.2E1 | 1.1E2 | 3.9E1 | 4.2E-2 | 4.2E-2 | 1.6E3 | 1.5E2 | 262 | 51 | 110 | 51 | 0.59 |
| aN | U/mL | 9.3E0 | 1.8E1 | 1.4E1 | 2.8E1 | 1.5E1 | 3.0E1 | 2.5E-3 | 2.5E-3 | 9.8E1 | 1.1E2 | 262 | 51 | 110 | 51 | 0.67 |
| aO | pg/mL | 2.9E1 | 5.1E1 | 3.0E2 | 4.5E2 | 8.5E2 | 9.7E2 | 6.0E-2 | 6.0E-2 | 6.6E3 | 3.6E3 | 262 | 51 | 110 | 51 | 0.56 |
| aP | ng/mL | 1.7E0 | 1.7E0 | 2.1E0 | 2.2E0 | 2.1E0 | 1.5E0 | 4.5E-1 | 7.5E-1 | 2.8E1 | 6.5E0 | 262 | 51 | 110 | 51 | 0.53 |
| aQ | ng/mL | 3.2E-1 | 2.9E-1 | 4.9E-1 | 4.1E-1 | 5.0E-1 | 3.5E-1 | 1.9E-2 | 2.5E-2 | 4.0E0 | 1.3E0 | 262 | 51 | 110 | 51 | 0.45 |
| aR | ng/mL | 1.7E0 | 2.1E0 | 2.3E0 | 3.6E0 | 2.3E0 | 4.9E0 | 1.8E-1 | 4.5E-1 | 2.1E1 | 3.0E1 | 262 | 51 | 110 | 51 | 0.59 |
| aS | ng/mL | 2.4E-1 | 3.0E-1 | 6.5E-1 | 5.1E-1 | 2.3E0 | 8.9E-1 | 4.2E-3 | 4.2E-3 | 3.3E1 | 6.1E0 | 262 | 51 | 110 | 51 | 0.55 |
| aU | pg/mL | 8.7E1 | 7.7E1 | 1.4E2 | 1.0E2 | 1.6E2 | 9.9E1 | 7.4E-2 | 7.4E-2 | 1.3E3 | 4.8E2 | 262 | 51 | 110 | 51 | 0.42 |
| aV | ng/mL | 7.0E-1 | 6.1E-1 | 1.1E0 | 8.5E-1 | 1.2E0 | 8.5E-1 | 2.2E-2 | 3.8E-2 | 8.7E0 | 4.2E0 | 262 | 51 | 110 | 51 | 0.44 |
| aW | pg/mL | 1.7E1 | 2.2E1 | 1.9E1 | 2.8E1 | 2.4E1 | 6.0E1 | 7.2E-2 | 7.2E-2 | 2.4E2 | 4.5E2 | 262 | 51 | 110 | 51 | 0.61 |
| aX | ng/mL | 1.0E1 | 7.9E0 | 1.6E1 | 1.2E1 | 2.2E1 | 1.0E1 | 3.0E-1 | 1.4E0 | 2.2E2 | 4.6E1 | 262 | 51 | 110 | 51 | 0.46 |
| aY | pg/mL | 5.3E1 | 6.5E1 | 7.3E1 | 8.3E1 | 7.0E1 | 7.1E1 | 4.1E-1 | 4.1E-1 | 4.4E2 | 3.7E2 | 262 | 51 | 110 | 51 | 0.57 |
| aZ | pg/mL | 2.3E2 | 1.9E2 | 4.4E2 | 3.7E2 | 5.6E2 | 8.4E2 | 1.7E0 | 1.7E0 | 3.4E3 | 5.9E3 | 262 | 51 | 110 | 51 | 0.44 |
| bA | ng/mL | 6.8E0 | 1.2E1 | 2.4E1 | 4.5E1 | 6.9E1 | 9.6E1 | 3.0E-2 | 3.0E-2 | 7.1E2 | 6.2E2 | 262 | 51 | 110 | 51 | 0.60 |
| bB | ng/mL | 3.1E2 | 3.1E2 | 3.4E2 | 3.2E2 | 1.6E2 | 1.8E2 | 2.1E0 | 2.3E1 | 7.4E2 | 7.6E2 | 262 | 51 | 110 | 51 | 0.47 |
| bC | ng/mL | 3.4E2 | 4.1E2 | 5.2E2 | 8.0E2 | 6.0E2 | 1.1E3 | 2.7E1 | 9.8E0 | 4.0E3 | 4.7E3 | 262 | 51 | 110 | 51 | 0.57 |
| bE | mg/mL | 5.8E0 | 5.3E0 | 6.1E0 | 6.1E0 | 2.0E0 | 2.3E0 | 9.8E-1 | 1.4E0 | 1.2E1 | 1.2E1 | 262 | 51 | 110 | 51 | 0.48 |
| bF | pg/mL | 1.9E1 | 2.5E1 | 5.7E1 | 9.4E1 | 2.6E2 | 3.1E2 | 5.0E-2 | 2.1E0 | 3.3E3 | 2.2E3 | 262 | 51 | 110 | 51 | 0.59 |
| bG | ng/mL | 1.7E0 | 1.3E0 | 2.9E0 | 2.5E0 | 3.3E0 | 3.0E0 | 2.2E-2 | 2.4E-1 | 2.3E1 | 1.5E1 | 262 | 51 | 110 | 51 | 0.45 |
| bH | pg/mL | 5.7E-1 | 5.7E-1 | 5.1E0 | 2.5E0 | 1.8E1 | 4.8E0 | 5.7E-1 | 5.7E-1 | 2.8E2 | 2.2E1 | 262 | 51 | 110 | 51 | 0.42 |
| bI | ng/mL | 4.0E-3 | 4.0E-3 | 6.0E-2 | 4.6E-2 | 1.5E-1 | 1.1E-1 | 4.0E-3 | 4.0E-3 | 1.3E0 | 4.5E-1 | 262 | 51 | 110 | 51 | 0.49 |
| bJ | mg/mL | 2.6E0 | 2.1E0 | 3.0E0 | 2.5E0 | 2.2E0 | 2.0E0 | 2.5E-4 | 2.5E-4 | 1.3E1 | 1.0E1 | 262 | 51 | 110 | 51 | 0.44 |
| bL | pg/mL | 4.1E0 | 2.4E0 | 8.5E0 | 5.7E0 | 1.1E1 | 7.5E0 | 4.6E-2 | 4.6E-2 | 8.0E1 | 2.7E1 | 262 | 51 | 110 | 51 | 0.39 |
| bM | mg/mL | 1.5E0 | 2.0E0 | 1.9E0 | 2.5E0 | 1.3E0 | 1.4E0 | 9.2E-3 | 4.1E-1 | 8.8E0 | 6.3E0 | 262 | 51 | 110 | 51 | 0.65 |
| bN | ng/mL | 3.1E1 | 5.4E1 | 1.3E2 | 1.1E2 | 3.1E2 | 1.9E2 | 1.4E-1 | 1.4E-1 | 1.9E3 | 1.2E3 | 262 | 51 | 110 | 51 | 0.55 |
| bO | ng/mL | 4.0E-2 | 4.0E-2 | 1.1E1 | 1.3E1 | 2.4E1 | 3.2E1 | 4.0E-2 | 4.0E-2 | 1.9E2 | 1.9E2 | 262 | 51 | 110 | 51 | 0.49 |
| bP | mg/mL | 6.3E-1 | 4.9E-1 | 8.5E-1 | 7.1E-1 | 7.0E-1 | 6.5E-1 | 4.9E-2 | 1.3E-1 | 3.8E0 | 3.1E0 | 262 | 51 | 110 | 51 | 0.43 |
| bQ | pg/mL | 1.5E1 | 1.6E1 | 2.7E1 | 2.2E1 | 5.0E1 | 3.1E1 | 1.5E-1 | 1.5E-1 | 4.8E2 | 2.2E2 | 262 | 51 | 110 | 51 | 0.49 |
| bR | ng/mL | 1.2E-2 | 1.2E-2 | 1.3E-1 | 9.3E-2 | 2.5E-1 | 1.8E-1 | 1.2E-2 | 1.2E-2 | 3.4E0 | 1.2E0 | 262 | 51 | 110 | 51 | 0.44 |
| bS | pg/mL | 9.4E-1 | 9.4E-1 | 7.8E0 | 3.8E0 | 2.7E1 | 1.1E1 | 9.4E-1 | 9.4E-1 | 3.4E2 | 5.4E1 | 262 | 51 | 110 | 51 | 0.46 |
| bU | ng/mL | 1.6E-1 | 1.3E-2 | 2.1E-1 | 1.5E-1 | 2.3E-1 | 2.7E-1 | 1.3E-2 | 1.3E-2 | 1.8E0 | 1.7E0 | 262 | 51 | 110 | 51 | 0.37 |
| bV | pg/mL | 4.7E2 | 4.5E2 | 5.7E2 | 6.0E2 | 7.2E2 | 4.6E2 | 1.6E2 | 1.7E2 | 1.2E4 | 3.1E3 | 262 | 51 | 110 | 51 | 0.52 |
| bW | pg/mL | 3.5E2 | 3.5E2 | 5.2E2 | 5.9E2 | 4.8E2 | 9.0E2 | 1.1E2 | 9.2E1 | 3.4E3 | 6.4E3 | 262 | 51 | 110 | 51 | 0.51 |
| bX | ng/mL | 1.8E-3 | 2.5E-5 | 3.0E-3 | 1.9E-3 | 3.7E-3 | 2.8E-3 | 2.5E-5 | 2.5E-5 | 2.0E-2 | 1.1E-2 | 262 | 51 | 110 | 51 | 0.42 |
| bZ | pg/mL | 2.5E2 | 2.5E2 | 8.0E2 | 4.7E2 | 3.3E3 | 6.1E2 | 1.5E-1 | 1.5E-1 | 4.4E4 | 2.7E3 | 262 | 51 | 110 | 51 | 0.49 |
| cA | pg/mL | 6.0E-1 | 6.0E-1 | 2.0E0 | 1.4E0 | 3.5E0 | 2.5E0 | 6.0E-1 | 6.0E-1 | 1.5E1 | 1.0E1 | 262 | 51 | 110 | 51 | 0.48 |
| cB | ng/mL | 6.7E-2 | 4.0E-2 | 9.8E-2 | 7.4E-2 | 1.0E-1 | 1.0E-1 | 1.7E-3 | 1.7E-3 | 5.4E-1 | 5.3E-1 | 262 | 51 | 110 | 51 | 0.39 |
| cC | pg/mL | 4.6E1 | 3.6E1 | 4.9E1 | 3.6E1 | 3.6E1 | 3.0E1 | 1.0E0 | 1.0E0 | 3.7E2 | 1.4E2 | 262 | 51 | 110 | 51 | 0.38 |
| cD | pg/mL | 6.1E0 | 3.4E0 | 1.3E1 | 1.2E1 | 5.9E1 | 2.4E1 | 3.3E-1 | 3.3E-1 | 7.2E2 | 1.4E2 | 262 | 51 | 110 | 51 | 0.39 |
| cE | pg/mL | 3.1E1 | 3.9E1 | 1.1E2 | 1.3E2 | 2.8E2 | 4.4E2 | 1.2E-1 | 1.2E-1 | 3.1E3 | 3.1E3 | 262 | 51 | 110 | 51 | 0.50 |
| cF | pg/mL | 1.4E1 | 9.4E0 | 2.3E1 | 1.7E1 | 3.2E1 | 3.2E1 | 5.3E-1 | 5.3E-1 | 2.2E2 | 2.2E2 | 262 | 51 | 110 | 51 | 0.43 |
| cG | pg/mL | 4.2E1 | 4.9E1 | 6.7E1 | 1.1E2 | 9.1E1 | 2.4E2 | 9.6E0 | 1.1E1 | 1.1E3 | 1.6E3 | 262 | 51 | 110 | 51 | 0.56 |
| cH | uIU/mL | 2.8E0 | 3.2E0 | 5.6E0 | 7.0E0 | 8.3E0 | 1.1E1 | 8.6E-3 | 8.6E-3 | 8.7E1 | 5.2E1 | 262 | 51 | 110 | 51 | 0.51 |
| cI | ng/mL | 5.5E0 | 6.0E0 | 1.1E1 | 1.6E1 | 1.4E1 | 2.3E1 | 1.0E-3 | 7.1E-2 | 1.0E2 | 1.2E2 | 262 | 51 | 110 | 51 | 0.51 |
| cJ | ug/mL | 7.0E1 | 5.7E1 | 1.2E2 | 1.3E2 | 1.4E2 | 1.7E2 | 4.0E0 | 1.1E1 | 9.6E2 | 6.9E2 | 262 | 51 | 110 | 51 | 0.49 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cK | ng/mL | 3.8E-3 | 3.8E-3 | 6.9E-2 | 8.3E-3 | 2.1E-1 | 2.4E-2 | 3.8E-3 | 3.8E-3 | 1.7E0 | 1.6E-1 | 262 | 51 | 110 | 51 | 0.42 |
| cL | pg/mL | 1.9E2 | 2.0E2 | 2.7E2 | 3.6E2 | 4.7E2 | 8.2E2 | 2.5E1 | 1.6E1 | 7.1E3 | 5.8E3 | 262 | 51 | 110 | 51 | 0.50 |
| cM | pg/mL | 2.8E2 | 2.5E2 | 3.1E2 | 2.9E2 | 1.8E2 | 2.2E2 | 2.5E1 | 3.3E1 | 1.2E3 | 1.5E3 | 262 | 51 | 110 | 51 | 0.44 |
| cN | pg/mL | 1.2E2 | 1.2E2 | 1.2E2 | 1.4E2 | 4.2E1 | 5.0E1 | 3.8E1 | 4.3E1 | 3.0E2 | 2.7E2 | 262 | 51 | 110 | 51 | 0.59 |
| cO | pg/mL | 2.3E2 | 2.1E2 | 2.9E2 | 2.4E2 | 2.0E2 | 1.1E2 | 5.4E1 | 6.1E1 | 1.7E3 | 6.3E2 | 262 | 51 | 110 | 51 | 0.44 |
| cP | ng/mL | 2.4E3 | 2.8E3 | 2.5E3 | 2.8E3 | 8.7E2 | 9.2E2 | 6.2E2 | 1.5E3 | 5.7E3 | 5.5E3 | 262 | 51 | 110 | 51 | 0.61 |
| cQ | ng/mL | 3.9E-2 | 5.9E-2 | 1.2E-1 | 1.4E-1 | 2.1E-1 | 2.4E-1 | 2.0E-3 | 2.0E-3 | 1.5E0 | 1.4E0 | 262 | 51 | 110 | 51 | 0.56 |
| cR | ng/mL | 3.2E2 | 3.2E2 | 5.4E2 | 4.7E2 | 8.7E2 | 4.4E2 | 2.3E1 | 3.0E1 | 8.9E3 | 2.3E3 | 262 | 51 | 110 | 51 | 0.51 |
| cS | ng/mL | 2.5E2 | 2.5E2 | 4.2E2 | 4.1E2 | 4.6E2 | 4.2E2 | 4.1E1 | 7.0E1 | 2.7E3 | 2.6E3 | 262 | 51 | 110 | 51 | 0.50 |
| cT | ng/mL | 2.7E1 | 3.4E1 | 6.4E1 | 1.0E2 | 1.3E2 | 1.7E2 | 4.6E0 | 6.9E0 | 1.7E3 | 7.4E2 | 262 | 51 | 110 | 51 | 0.59 |
| cU | ng/mL | 5.6E1 | 5.4E1 | 7.3E1 | 6.6E1 | 6.8E1 | 4.6E1 | 9.2E0 | 1.4E1 | 7.7E2 | 2.7E2 | 262 | 51 | 110 | 51 | 0.49 |
| cV | ng/mL | 1.6E-1 | 1.8E-1 | 4.4E-1 | 2.5E-1 | 2.9E0 | 3.1E-1 | 2.5E-2 | 3.7E-2 | 4.7E1 | 2.0E0 | 262 | 51 | 110 | 51 | 0.49 |
| cW | mIU/mL | 5.1E-2 | 4.9E-2 | 2.0E-1 | 6.8E-2 | 9.3E-1 | 6.0E-2 | 3.7E-4 | 1.0E-2 | 9.7E0 | 2.7E-1 | 262 | 51 | 110 | 51 | 0.48 |
| cX | ng/mL | 9.7E-2 | 1.8E-1 | 1.3E0 | 1.3E0 | 4.3E0 | 3.3E0 | 2.3E-4 | 2.3E-4 | 2.8E1 | 2.2E1 | 262 | 51 | 110 | 51 | 0.54 |
| cY | ng/mL | 9.9E0 | 7.8E0 | 1.4E1 | 1.1E1 | 1.3E1 | 8.8E0 | 2.5E-1 | 1.5E-1 | 8.3E1 | 3.2E1 | 262 | 51 | 110 | 51 | 0.45 |
| cZ | ug/mL | 1.5E1 | 1.6E1 | 1.6E1 | 1.6E1 | 7.5E0 | 7.3E0 | 2.3E0 | 3.1E0 | 5.7E1 | 3.7E1 | 262 | 51 | 110 | 51 | 0.52 |
| dA | pg/mL | 3.3E2 | 3.3E2 | 3.6E2 | 3.7E2 | 1.8E2 | 1.6E2 | 9.0E1 | 1.3E2 | 1.3E3 | 8.2E2 | 262 | 51 | 110 | 51 | 0.51 |
| dB | ug/mL | 1.7E1 | 1.5E1 | 1.9E1 | 1.5E1 | 2.0E1 | 1.2E1 | 2.1E0 | 1.8E0 | 2.5E2 | 4.1E1 | 262 | 51 | 110 | 51 | 0.45 |
| dC | nmol/L | 3.5E1 | 3.7E1 | 4.0E1 | 3.9E1 | 1.9E1 | 1.6E1 | 7.9E0 | 1.5E1 | 1.4E2 | 8.7E1 | 262 | 51 | 110 | 51 | 0.50 |
| dD | ug/mL | 3.8E1 | 3.7E1 | 3.9E1 | 3.7E1 | 1.1E1 | 1.0E1 | 1.3E1 | 1.3E1 | 7.6E1 | 5.7E1 | 262 | 51 | 110 | 51 | 0.44 |
| dE | ng/mL | 5.1E-1 | 8.4E-3 | 6.9E-1 | 4.0E-1 | 8.1E-1 | 6.4E-1 | 8.4E-3 | 8.4E-3 | 7.2E0 | 3.3E0 | 262 | 51 | 110 | 51 | 0.34 |
| dF | ng/mL | 2.1E2 | 2.5E2 | 2.6E2 | 2.7E2 | 1.8E2 | 1.4E2 | 7.5E1 | 8.6E1 | 1.2E3 | 6.6E2 | 262 | 51 | 110 | 51 | 0.55 |
| dG | ng/mL | 1.1E1 | 1.3E1 | 1.4E1 | 1.5E1 | 1.0E1 | 7.8E0 | 2.5E0 | 3.3E0 | 8.1E1 | 3.4E1 | 262 | 51 | 110 | 51 | 0.58 |
| dH | pg/mL | 7.5E0 | 7.5E0 | 1.2E1 | 9.9E0 | 2.8E1 | 9.2E0 | 4.0E-2 | 4.0E-2 | 3.1E2 | 5.0E1 | 262 | 51 | 110 | 51 | 0.50 |
| dI | pg/mL | 4.6E-1 | 4.6E-1 | 1.9E0 | 8.6E-1 | 4.8E0 | 1.1E0 | 4.6E-1 | 4.6E-1 | 4.2E1 | 6.0E0 | 262 | 51 | 110 | 51 | 0.46 |
| dJ | ng/mL | 1.9E0 | 2.2E0 | 2.2E0 | 2.2E0 | 1.1E0 | 1.1E0 | 3.2E-2 | 4.9E-1 | 5.9E0 | 5.1E0 | 262 | 51 | 110 | 51 | 0.52 |
| dK | uIU/mL | 2.0E0 | 1.6E0 | 2.6E0 | 2.7E0 | 2.6E0 | 3.7E0 | 2.8E-4 | 3.8E-2 | 1.6E1 | 2.1E1 | 262 | 51 | 110 | 51 | 0.47 |
| dL | ng/mL | 8.9E2 | 9.4E2 | 1.0E3 | 1.1E3 | 5.0E2 | 5.2E2 | 3.4E2 | 4.7E2 | 3.4E3 | 3.3E3 | 262 | 51 | 110 | 51 | 0.56 |
| dM | pg/mL | 9.7E2 | 1.1E3 | 1.2E3 | 1.3E3 | 1.0E3 | 1.2E3 | 3.5E2 | 4.2E2 | 1.2E4 | 8.3E3 | 262 | 51 | 110 | 51 | 0.53 |
| dN | ug/mL | 9.0E1 | 9.8E1 | 9.9E1 | 1.1E2 | 3.7E1 | 3.7E1 | 2.5E1 | 3.7E1 | 2.8E2 | 2.1E2 | 262 | 51 | 110 | 51 | 0.57 |
| dO | ng/ml | 2.5E1 | 1.5E1 | 4.4E1 | 2.4E1 | 6.0E1 | 2.6E1 | 4.0E-1 | 4.6E0 | 3.7E2 | 7.9E1 | 58 | 11 | 38 | 11 | 0.39 |
| dR | pg/ml | 1.8E3 | 1.7E3 | 2.5E3 | 2.1E3 | 2.4E3 | 1.7E3 | 1.9E2 | 1.7E2 | 1.5E4 | 8.1E3 | 150 | 50 | 104 | 50 | 0.47 |
| dU | pg/ml | 9.1E3 | 1.9E4 | 1.2E4 | 2.3E4 | 1.1E4 | 1.2E4 | 2.5E3 | 6.7E3 | 5.3E4 | 3.8E4 | 27 | 8 | 26 | 8 | 0.80 |
| dV | pg/ml | 7.0E1 | 1.0E2 | 8.9E1 | 2.0E2 | 6.1E1 | 2.8E2 | 2.1E1 | 3.8E1 | 3.3E2 | 8.9E2 | 48 | 8 | 27 | 8 | 0.62 |
| dX | ng/ml | 5.2E-2 | 5.2E-2 | 1.1E-1 | 2.2E-1 | 1.5E-1 | 3.8E-1 | 2.6E-3 | 2.6E-3 | 7.4E-1 | 9.4E-1 | 89 | 9 | 31 | 9 | 0.46 |
| eF | ng/ml | 4.0E0 | 4.6E0 | 5.2E0 | 5.1E0 | 5.6E0 | 2.3E0 | 1.2E0 | 1.6E0 | 4.6E1 | 1.2E1 | 158 | 51 | 105 | 51 | 0.59 |
| eC | pg/ml | 3.0E2 | 3.1E2 | 3.7E2 | 3.4E2 | 2.5E2 | 1.5E2 | 9.9E0 | 5.1E1 | 1.4E3 | 6.2E2 | 105 | 45 | 97 | 45 | 0.51 |
| eD | pg/ml | 2.3E2 | 2.2E2 | 7.6E2 | 3.0E2 | 1.5E3 | 2.8E2 | 5.2E-1 | 5.2E-1 | 8.3E3 | 1.4E3 | 81 | 37 | 74 | 37 | 0.47 |
| eM | ng/ml | 3.2E0 | 4.2E0 | 4.3E0 | 7.3E0 | 4.2E0 | 6.8E0 | 7.6E-1 | 9.0E-1 | 2.7E1 | 2.5E1 | 110 | 17 | 44 | 17 | 0.64 |
| eP | ng/ml | 3.7E-3 | 4.5E-1 | 8.1E-1 | 7.8E0 | 1.9E0 | 2.1E1 | 3.7E-3 | 3.7E-3 | 1.2E1 | 6.5E1 | 89 | 9 | 31 | 9 | 0.66 |
| eT | ng/ml | 2.8E2 | 2.4E2 | 6.0E2 | 3.9E2 | 6.5E2 | 4.5E2 | 1.0E2 | 1.2E2 | 2.5E3 | 1.9E3 | 55 | 16 | 54 | 16 | 0.44 |
| eQ | pg/ml | 1.0E0 | 1.0E0 | 1.2E2 | 5.8E0 | 3.3E2 | 1.4E1 | 1.0E0 | 1.0E0 | 1.6E3 | 4.0E1 | 27 | 8 | 26 | 8 | 0.38 |
| fA | ng/ml | 2.0E2 | 1.7E2 | 4.4E2 | 2.2E2 | 4.9E2 | 1.5E2 | 2.6E1 | 6.8E1 | 1.5E3 | 4.7E2 | 27 | 8 | 26 | 8 | 0.48 |
| eZ | ng/ml | 5.4E1 | 5.2E1 | 6.2E1 | 5.6E1 | 2.5E1 | 2.3E1 | 2.3E1 | 2.5E1 | 1.2E2 | 1.1E2 | 55 | 16 | 54 | 16 | 0.45 |
| fB | ng/ml | 6.0E2 | 7.0E2 | 6.8E2 | 8.5E2 | 2.9E2 | 3.9E2 | 1.6E2 | 4.4E2 | 1.3E3 | 1.5E3 | 28 | 8 | 27 | 8 | 0.62 |
| eX | ng/ml | 5.0E0 | 3.3E0 | 1.7E1 | 9.8E0 | 2.2E1 | 1.2E1 | 8.6E-4 | 3.3E-1 | 7.3E1 | 3.4E1 | 58 | 11 | 38 | 11 | 0.42 |
| fN | ng/ml | 2.1E-1 | 2.1E-1 | 3.9E0 | 1.4E0 | 9.2E0 | 2.8E0 | 2.1E-1 | 2.1E-1 | 5.4E1 | 8.9E0 | 55 | 16 | 54 | 16 | 0.42 |
| fP | ng/ml | 2.3E2 | 2.9E2 | 2.5E2 | 3.2E2 | 1.4E2 | 1.8E2 | 8.4E0 | 2.7E1 | 1.0E3 | 8.7E2 | 140 | 48 | 100 | 48 | 0.61 |
| fR | ng/ml | 1.2E5 | 1.4E5 | 1.7E5 | 2.2E5 | 1.3E5 | 1.8E5 | 3.1E4 | 3.6E4 | 7.7E5 | 7.2E5 | 202 | 27 | 60 | 27 | 0.58 |
| fY | ng/ml | 2.6E2 | 3.2E2 | 2.5E2 | 2.7E2 | 9.4E1 | 1.3E2 | 6.5E1 | 4.2E1 | 4.7E2 | 4.5E2 | 55 | 16 | 54 | 16 | 0.59 |
| gC | ng/ml | 2.3E2 | 2.4E2 | 2.7E2 | 2.7E2 | 1.4E2 | 1.3E2 | 1.2E2 | 1.3E2 | 1.1E3 | 5.9E2 | 84 | 19 | 49 | 19 | 0.51 |
| gN | U/ml | 3.7E2 | 4.6E2 | 4.5E2 | 5.4E2 | 3.1E2 | 3.3E2 | 1.9E0 | 1.2E2 | 1.3E3 | 9.2E2 | 48 | 8 | 27 | 8 | 0.59 |
| gL | pg/ml | 6.3E4 | 6.5E4 | 7.0E4 | 7.2E4 | 3.5E4 | 2.8E4 | 1.4E4 | 3.1E4 | 2.0E5 | 1.6E5 | 150 | 50 | 104 | 50 | 0.54 |
| gP | U/ml | 2.7E2 | 3.0E2 | 2.8E2 | 3.0E2 | 9.5E1 | 1.3E2 | 8.5E1 | 7.1E1 | 8.0E2 | 8.5E2 | 157 | 51 | 105 | 51 | 0.57 |
| gT | ng/ml | 2.0E1 | 2.3E1 | 2.0E1 | 2.4E1 | 5.0E0 | 5.1E0 | 1.2E1 | 1.8E1 | 3.6E1 | 3.2E1 | 49 | 8 | 31 | 8 | 0.72 |
| gW | ng/ml | 8.5E2 | 5.5E2 | 1.5E3 | 9.1E2 | 1.9E3 | 1.0E3 | 3.7E1 | 2.3E0 | 9.5E3 | 4.3E3 | 130 | 43 | 96 | 43 | 0.40 |
| gV | ng/ml | 2.1E1 | 1.7E1 | 2.2E1 | 2.3E1 | 7.5E0 | 9.8E0 | 2.9E-3 | 1.4E1 | 3.9E1 | 3.9E1 | 77 | 8 | 19 | 8 | 0.46 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| tF | pg/mL | 1.6E3 | 9.0E2 | 2.0E4 | 7.3E3 | 5.4E4 | 1.8E4 | 1.2E1 | 1.8E1 | 3.2E5 | 9.4E4 | 105 | 45 | 97 | 45 | 0.45 |
| gZ | ug/ml | 8.0E-1 | 1.0E0 | 5.4E1 | 5.2E1 | 1.2E2 | 1.3E2 | 8.7E-2 | 1.1E-1 | 4.1E2 | 3.8E2 | 27 | 8 | 26 | 8 | 0.56 |
| hA | ng/ml | 2.1E0 | 2.1E0 | 7.1E0 | 8.1E0 | 2.4E1 | 2.1E1 | 1.7E-2 | 1.7E-2 | 1.6E2 | 1.0E2 | 81 | 37 | 74 | 37 | 0.52 |
| nM | pg/ml | 1.0E-9 | 1.0E-9 | 1.9E2 | 1.0E-9 | 1.4E3 | 0.0E0 | 1.0E-9 | 1.0E-9 | 1.0E4 | 1.0E-9 | 53 | 29 | 51 | 29 | 0.48 |
| nN | pg/ml | 1.0E3 | 1.8E3 | 1.8E3 | 2.5E3 | 2.6E3 | 2.7E3 | 1.1E2 | 1.2E2 | 1.7E4 | 1.3E4 | 53 | 29 | 51 | 29 | 0.62 |
| nO | pg/ml | 3.2E1 | 3.1E1 | 4.9E1 | 5.0E1 | 4.9E1 | 5.2E1 | 5.5E0 | 3.5E0 | 2.4E2 | 2.4E2 | 53 | 29 | 51 | 29 | 0.48 |
| nR | pg/ml | 1.3E1 | 1.9E1 | 2.9E1 | 6.9E1 | 4.6E1 | 1.5E2 | 1.0E-9 | 5.5E-1 | 2.6E2 | 7.1E2 | 53 | 29 | 51 | 29 | 0.59 |
| nT | pg/ml | 1.1E2 | 8.5E1 | 3.7E2 | 1.5E2 | 1.2E3 | 3.2E2 | 1.0E-9 | 1.0E-9 | 6.6E3 | 1.8E3 | 53 | 29 | 51 | 29 | 0.46 |
| nU | pg/ml | 1.4E1 | 3.1E1 | 5.3E2 | 1.7E2 | 2.3E3 | 5.4E2 | 1.0E-9 | 1.0E-9 | 1.3E4 | 3.0E3 | 53 | 29 | 51 | 29 | 0.58 |
| lW | pg/ml | 1.0E-9 | 1.0E-9 | 1.5E1 | 4.2E0 | 5.5E1 | 1.1E1 | 1.0E-9 | 1.0E-9 | 3.9E2 | 4.2E1 | 53 | 29 | 51 | 29 | 0.45 |
| lX | pg/ml | 1.1E3 | 9.9E2 | 1.1E3 | 1.0E3 | 5.5E2 | 5.5E2 | 2.3E2 | 1.2E2 | 2.6E3 | 2.3E3 | 53 | 29 | 51 | 29 | 0.47 |
| lY | pg/ml | 1.8E1 | 2.4E1 | 2.2E1 | 2.6E1 | 2.3E1 | 1.7E1 | 1.0E-9 | 5.4E0 | 1.4E2 | 9.6E1 | 53 | 29 | 51 | 29 | 0.62 |
| mE | pg/ml | 1.0E-9 | 1.0E-9 | 3.6E0 | 1.1E0 | 1.0E1 | 2.1E0 | 1.0E-9 | 1.0E-9 | 5.8E1 | 8.9E0 | 53 | 29 | 51 | 29 | 0.48 |
| mF | pg/ml | 1.0E-9 | 1.0E-9 | 1.8E0 | 1.1E0 | 3.3E0 | 1.9E0 | 1.0E-9 | 1.0E-9 | 1.5E1 | 6.1E0 | 53 | 29 | 51 | 29 | 0.47 |
| mH | pg/ml | 4.4E0 | 3.0E0 | 5.6E0 | 3.8E0 | 5.2E0 | 2.7E0 | 2.3E-1 | 3.2E-1 | 3.2E1 | 1.1E1 | 53 | 29 | 51 | 29 | 0.41 |
| mI | pg/ml | 1.0E-9 | 1.0E-9 | 1.4E1 | 9.4E0 | 3.1E1 | 1.6E1 | 1.0E-9 | 1.0E-9 | 1.6E2 | 7.8E1 | 53 | 29 | 51 | 29 | 0.50 |
| mM | pg/ml | 1.8E1 | 2.8E1 | 4.3E1 | 5.4E1 | 5.9E1 | 7.6E1 | 1.0E-9 | 1.0E-9 | 2.3E2 | 2.9E2 | 53 | 29 | 51 | 29 | 0.55 |
| mP | pg/ml | 1.4E1 | 1.5E1 | 1.8E1 | 1.5E1 | 2.2E1 | 8.9E0 | 1.0E-9 | 1.0E-9 | 1.5E2 | 3.7E1 | 52 | 29 | 50 | 29 | 0.48 |
| mS | pg/ml | 1.8E3 | 1.7E3 | 2.1E3 | 2.0E3 | 2.3E3 | 1.2E3 | 1.0E-9 | 1.0E-9 | 1.3E4 | 5.9E3 | 53 | 29 | 51 | 29 | 0.52 |
| mT | pg/ml | 5.3E1 | 5.2E1 | 1.5E2 | 1.4E2 | 2.8E2 | 3.5E2 | 9.7E0 | 1.6E1 | 1.4E3 | 1.9E3 | 52 | 29 | 50 | 29 | 0.51 |
| mU | pg/ml | 2.5E0 | 2.7E0 | 4.1E0 | 2.9E0 | 8.7E0 | 2.1E0 | 1.0E-9 | 1.9E-1 | 5.8E1 | 1.1E1 | 52 | 29 | 50 | 29 | 0.54 |
| mW | pg/ml | 2.0E3 | 2.4E3 | 2.6E3 | 3.0E3 | 1.7E3 | 1.5E3 | 3.1E2 | 6.7E2 | 1.0E4 | 7.0E3 | 52 | 29 | 50 | 29 | 0.60 |
| mY | pg/ml | 4.8E2 | 6.4E2 | 9.9E2 | 8.2E2 | 1.8E3 | 6.3E2 | 1.0E-9 | 2.1E2 | 1.1E4 | 2.7E3 | 53 | 29 | 51 | 29 | 0.59 |
| mZ | pg/ml | 1.8E2 | 4.4E2 | 3.1E2 | 4.8E2 | 2.9E2 | 3.8E2 | 1.0E-9 | 5.3E1 | 1.2E3 | 1.7E3 | 52 | 29 | 50 | 29 | 0.66 |
| nA | pg/ml | 1.3E0 | 2.0E0 | 1.6E0 | 6.1E0 | 6.7E1 | 1.3E1 | 1.0E-9 | 1.0E-9 | 4.4E2 | 6.2E1 | 52 | 29 | 50 | 29 | 0.55 |
| nB | pg/ml | 2.9E2 | 3.3E2 | 3.0E2 | 3.7E2 | 1.6E2 | 1.4E2 | 3.0E1 | 1.4E2 | 7.0E2 | 7.2E2 | 53 | 29 | 51 | 29 | 0.65 |
| nC | pg/ml | 1.0E-9 | 1.0E-9 | 8.3E3 | 5.4E4 | 5.0E4 | 2.8E5 | 1.0E-9 | 1.0E-9 | 3.7E5 | 1.5E6 | 53 | 29 | 51 | 29 | 0.50 |
| nD | pg/ml | 6.7E0 | 8.5E0 | 7.2E1 | 1.3E1 | 3.2E2 | 2.7E1 | 1.0E-9 | 1.0E-9 | 1.7E3 | 1.5E2 | 52 | 29 | 50 | 29 | 0.50 |
| nF | pg/ml | 1.0E-9 | 1.0E-9 | 7.7E0 | 2.3E0 | 3.9E1 | 7.6E0 | 1.0E-9 | 1.0E-9 | 2.4E2 | 3.6E1 | 53 | 29 | 51 | 29 | 0.51 |
| nH | pg/ml | 3.8E-1 | 3.0E-2 | 2.1E2 | 1.1E2 | 1.4E3 | 4.9E2 | 1.0E-9 | 1.0E-9 | 1.0E4 | 2.6E3 | 52 | 29 | 50 | 29 | 0.51 |
| nI | pg/ml | 4.6E1 | 4.6E1 | 2.9E2 | 9.7E1 | 1.3E3 | 2.2E1 | 1.0E-9 | 1.0E-9 | 9.2E3 | 1.2E3 | 53 | 29 | 51 | 29 | 0.50 |
| nJ | pg/ml | 1.0E-9 | 5.9E-2 | 1.0E2 | 1.5E0 | 7.1E2 | 3.7E0 | 1.0E-9 | 1.0E-9 | 5.2E3 | 1.6E1 | 53 | 29 | 51 | 29 | 0.52 |
| nK | pg/ml | 1.0E-9 | 3.1E0 | 1.2E2 | 2.7E1 | 5.4E2 | 5.8E1 | 1.0E-9 | 1.0E-9 | 3.2E3 | 2.3E2 | 52 | 29 | 50 | 29 | 0.56 |
| nL | pg/ml | 1.0E-9 | 1.0E-9 | 9.2E2 | 2.6E2 | 6.1E3 | 9.8E2 | 1.0E-9 | 1.0E-9 | 4.5E4 | 5.2E3 | 53 | 29 | 51 | 29 | 0.49 |
| hL | pg/ml | 1.8E4 | 2.1E4 | 2.4E4 | 2.4E4 | 2.2E4 | 1.3E4 | 1.0E-9 | 5.7E3 | 1.4E5 | 4.6E4 | 55 | 16 | 54 | 16 | 0.57 |
| hO | pg/ml | 1.6E4 | 1.6E4 | 1.7E4 | 1.7E4 | 3.2E3 | 3.8E3 | 1.1E4 | 1.1E4 | 2.8E4 | 2.6E4 | 55 | 16 | 54 | 16 | 0.48 |
| hP | ng/ml | 4.4E5 | 4.4E5 | 3.5E5 | 4.3E5 | 1.8E5 | 2.9E5 | 2.3E4 | 1.7E4 | 9.0E5 | 1.1E6 | 55 | 16 | 54 | 16 | 0.56 |
| wJ | pg/ml | 1.5E5 | 1.8E5 | 1.6E5 | 1.9E5 | 6.9E4 | 1.2E5 | 3.2E4 | 6.0E4 | 3.1E5 | 5.1E5 | 54 | 13 | 53 | 13 | 0.56 |
| wK | pg/ml | 3.4E4 | 2.9E4 | 4.2E4 | 4.5E4 | 2.5E4 | 3.5E4 | 5.2E3 | 9.2E3 | 1.1E5 | 1.4E5 | 54 | 13 | 53 | 13 | 0.50 |
| wL | pg/ml | 5.8E0 | 7.9E-1 | 5.6E1 | 4.4E0 | 1.3E2 | 7.5E0 | 1.0E-9 | 1.0E-9 | 8.4E2 | 2.6E1 | 54 | 13 | 53 | 13 | 0.33 |
| wP | pg/ml | 2.8E4 | 2.2E4 | 4.2E4 | 5.0E4 | 4.0E4 | 8.1E4 | 1.1E3 | 2.9E3 | 1.6E5 | 3.0E5 | 54 | 13 | 53 | 13 | 0.43 |
| wQ | pg/ml | 3.5E1 | 3.9E1 | 6.3E1 | 5.9E1 | 7.8E1 | 8.1E1 | 1.0E-9 | 1.0E-9 | 3.7E2 | 3.0E2 | 54 | 13 | 53 | 13 | 0.49 |
| hR | pg/ml | 2.9E4 | 2.4E4 | 3.0E4 | 2.4E4 | 1.2E4 | 8.9E3 | 1.8E3 | 3.6E3 | 5.8E4 | 4.1E4 | 79 | 36 | 72 | 36 | 0.34 |
| hV | pg/ml | 4.7E2 | 3.5E2 | 5.1E2 | 4.1E2 | 2.5E2 | 2.1E2 | 1.3E2 | 6.8E1 | 1.5E3 | 8.2E2 | 79 | 36 | 72 | 36 | 0.38 |
| hW | pg/ml | 1.5E3 | 1.4E3 | 1.8E3 | 2.2E3 | 9.5E2 | 2.1E3 | 5.7E2 | 2.2E2 | 4.8E3 | 1.0E4 | 79 | 36 | 72 | 36 | 0.50 |
| hX | pg/ml | 9.3E2 | 8.7E2 | 1.1E3 | 1.0E3 | 1.0E3 | 7.8E2 | 3.6E2 | 2.3E2 | 8.6E3 | 4.9E3 | 79 | 36 | 72 | 36 | 0.44 |
| iA | pg/ml | 1.4E2 | 1.6E2 | 4.0E2 | 2.3E2 | 9.0E2 | 3.3E2 | 1.1E1 | 5.8E0 | 7.1E3 | 2.2E3 | 105 | 45 | 97 | 45 | 0.50 |
| iB | ng/ml | 4.9E0 | 4.3E0 | 6.3E0 | 5.8E0 | 4.7E0 | 5.0E0 | 3.7E-2 | 4.5E-2 | 1.9E1 | 2.0E1 | 81 | 37 | 74 | 37 | 0.47 |
| iC | U/ml | 2.2E-1 | 2.0E-1 | 4.4E-1 | 7.7E-1 | 8.3E-1 | 2.1E0 | 1.0E-9 | 1.0E-9 | 6.4E0 | 1.2E1 | 81 | 37 | 74 | 37 | 0.52 |
| tQ | pg/ml | 1.1E3 | 1.0E3 | 1.2E3 | 1.2E3 | 5.3E2 | 5.3E2 | 2.8E2 | 6.4E2 | 2.5E3 | 2.5E3 | 53 | 12 | 52 | 12 | 0.47 |
| tT | pg/ml | 1.7E1 | 1.4E1 | 1.8E1 | 1.9E1 | 9.7E0 | 1.5E1 | 7.4E0 | 9.0E0 | 6.9E1 | 6.1E1 | 53 | 12 | 52 | 12 | 0.45 |
| tS | pg/ml | 1.1E0 | 8.5E-1 | 1.4E0 | 8.5E-1 | 1.4E0 | 6.1E-1 | 1.0E-9 | 1.0E-9 | 8.5E0 | 1.9E0 | 53 | 12 | 52 | 12 | 0.38 |
| tX | pg/ml | 8.6E-1 | 8.7E-1 | 1.1E0 | 8.3E-1 | 8.6E-1 | 4.5E-1 | 2.5E-2 | 7.6E-2 | 4.4E0 | 1.5E0 | 53 | 12 | 52 | 12 | 0.45 |
| tO | pg/ml | 3.9E0 | 4.2E0 | 4.7E0 | 4.2E0 | 3.1E0 | 2.7E0 | 1.0E-9 | 8.6E-1 | 1.4E1 | 9.0E0 | 53 | 12 | 52 | 12 | 0.47 |
| tR | pg/ml | 2.2E-1 | 1.2E-1 | 2.9E-1 | 1.7E-1 | 2.9E-1 | 1.6E-1 | 1.0E-9 | 1.0E-9 | 1.5E0 | 5.0E-1 | 53 | 12 | 52 | 12 | 0.38 |
| tU | pg/ml | 8.7E0 | 1.0E1 | 1.1E1 | 1.1E1 | 7.1E0 | 6.4E0 | 1.6E0 | 3.6E0 | 3.1E1 | 2.7E1 | 53 | 12 | 52 | 12 | 0.52 |
| tN | pg/ml | 1.7E1 | 1.7E1 | 2.1E1 | 1.9E1 | 1.4E1 | 1.1E1 | 1.0E-9 | 6.0E0 | 8.0E1 | 4.2E1 | 53 | 12 | 52 | 12 | 0.46 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| tV | ng/ml | 4.2E2 | 6.2E2 | 5.3E2 | 6.1E2 | 5.0E2 | 3.4E2 | 1.5E2 | 1.5E2 | 2.9E3 | 1.1E3 | 54 | 13 | 53 | 13 | 0.60 |
| iH | ng/ml | 1.5E5 | 1.5E5 | 1.5E5 | 1.5E5 | 4.4E4 | 5.1E4 | 7.1E4 | 7.2E4 | 2.4E5 | 2.6E5 | 105 | 45 | 97 | 45 | 0.52 |
| iJ | ng/ml | 5.1E4 | 5.0E4 | 5.2E4 | 5.2E4 | 2.2E4 | 2.1E4 | 5.5E3 | 8.0E3 | 1.0E5 | 9.7E4 | 105 | 45 | 97 | 45 | 0.50 |
| hB | ng/ml | 4.4E-1 | 3.7E-1 | 5.0E-1 | 4.6E-1 | 3.2E-1 | 2.7E-1 | 1.0E-9 | 1.2E-1 | 1.7E0 | 1.3E0 | 105 | 45 | 97 | 45 | 0.46 |
| hC | pg/ml | 3.7E3 | 4.1E3 | 5.7E3 | 7.3E3 | 7.5E3 | 7.8E3 | 1.0E-9 | 1.0E-9 | 5.5E4 | 3.0E4 | 105 | 45 | 97 | 45 | 0.57 |
| hF | ng/ml | 1.0E-9 | 1.0E-9 | 4.7E1 | 2.3E-1 | 4.0E2 | 1.4E0 | 1.0E-9 | 1.0E-9 | 4.0E3 | 9.6E0 | 105 | 45 | 97 | 45 | 0.50 |
| hG | ng/ml | 7.0E3 | 6.9E3 | 7.3E3 | 7.7E3 | 3.1E3 | 3.5E3 | 2.8E1 | 3.3E3 | 1.8E4 | 1.9E4 | 105 | 45 | 97 | 45 | 0.52 |
| iO | ng/ml | 3.8E5 | 3.2E5 | 4.1E5 | 3.6E5 | 1.9E5 | 1.8E5 | 1.1E4 | 8.3E4 | 1.1E6 | 9.0E5 | 105 | 45 | 97 | 45 | 0.43 |
| iP | ng/ml | 6.0E4 | 5.0E4 | 5.5E4 | 5.2E4 | 3.2E4 | 3.2E4 | 1.0E-9 | 2.4E3 | 2.5E5 | 1.5E5 | 105 | 45 | 97 | 45 | 0.47 |
| iZ | ng/ml | 1.6E3 | 1.6E3 | 1.8E3 | 2.0E3 | 7.5E2 | 1.2E3 | 4.7E2 | 8.8E2 | 5.1E3 | 6.5E3 | 105 | 45 | 97 | 45 | 0.54 |
| yH | pg/ml | 1.1E3 | 1.3E3 | 1.9E3 | 1.0E4 | 2.9E3 | 3.3E4 | 1.0E-9 | 1.6E2 | 1.5E4 | 1.2E5 | 54 | 14 | 53 | 14 | 0.51 |
| yK | U/ml | 1.9E1 | 3.7E1 | 4.8E1 | 5.8E1 | 8.2E1 | 6.9E1 | 1.0E-9 | 1.0E-9 | 3.8E2 | 2.5E2 | 54 | 14 | 53 | 14 | 0.61 |
| yJ | pg/ml | 3.4E4 | 5.3E4 | 4.6E4 | 5.6E4 | 3.4E4 | 3.3E4 | 1.7E3 | 1.7E4 | 1.6E5 | 1.1E5 | 54 | 14 | 53 | 14 | 0.59 |
| yD | ng/ml | 1.5E-2 | 1.4E-2 | 1.5E-2 | 1.4E-2 | 6.9E-3 | 4.7E-3 | 1.0E-9 | 7.6E-3 | 4.3E-2 | 2.2E-2 | 54 | 13 | 53 | 13 | 0.48 |
| jB | ng/ml | 2.8E5 | 2.3E5 | 2.8E5 | 2.7E5 | 9.6E4 | 1.7E5 | 5.7E4 | 1.2E5 | 4.7E5 | 6.2E5 | 27 | 8 | 26 | 8 | 0.40 |
| wB | pg/ml | 8.1E3 | 6.1E3 | 9.5E3 | 9.4E3 | 7.2E3 | 8.6E3 | 1.7E3 | 2.5E3 | 4.1E4 | 3.4E4 | 54 | 13 | 53 | 13 | 0.47 |
| pY | pg/ml | 6.0E0 | 5.7E0 | 1.1E1 | 6.6E0 | 2.6E1 | 3.0E0 | 2.1E0 | 2.6E0 | 2.0E2 | 1.2E1 | 55 | 16 | 54 | 16 | 0.51 |
| rC | pg/ml | 1.9E3 | 1.3E3 | 2.3E3 | 2.2E3 | 2.2E3 | 2.5E3 | 9.3E1 | 6.6E1 | 1.5E4 | 1.5E4 | 78 | 37 | 72 | 37 | 0.48 |
| rB | pg/ml | 2.2E1 | 2.9E1 | 4.6E1 | 4.2E1 | 1.2E2 | 5.1E1 | 1.0E-9 | 1.0E-9 | 9.5E2 | 2.9E2 | 78 | 37 | 72 | 37 | 0.60 |
| zG | 2.5ng/ml | 2.2E-1 | 1.1E-1 | 4.8E-1 | 3.7E-1 | 7.5E-1 | 8.6E-1 | 1.0E-9 | 1.0E-9 | 4.4E0 | 3.3E0 | 54 | 14 | 53 | 14 | 0.36 |
| zH | 2.3mU/ml | 1.1E-1 | 9.8E-2 | 1.2E-1 | 9.3E-2 | 6.9E-2 | 3.1E-2 | 1.0E-2 | 1.6E-2 | 4.4E-1 | 1.3E-1 | 54 | 14 | 53 | 14 | 0.41 |
| zI | 2.6ng/ml | 1.9E0 | 1.6E0 | 3.4E0 | 3.3E0 | 3.6E0 | 4.0E0 | 6.3E-1 | 5.4E-1 | 1.6E1 | 1.6E1 | 54 | 14 | 53 | 14 | 0.45 |
| qA | ng/ml | 1.1E7 | 8.7E6 | 1.3E7 | 1.0E7 | 7.4E6 | 5.2E6 | 3.7E6 | 2.0E6 | 3.7E7 | 2.4E7 | 55 | 16 | 54 | 16 | 0.41 |
| qB | ng/ml | 6.1E5 | 5.7E5 | 8.3E5 | 7.1E5 | 5.9E5 | 5.0E5 | 2.1E5 | 2.3E5 | 2.9E6 | 2.2E6 | 55 | 16 | 54 | 16 | 0.44 |
| qC | ng/ml | 4.5E5 | 3.6E5 | 9.1E5 | 3.6E5 | 1.3E6 | 2.9E5 | 2.0E4 | 3.4E5 | 7.1E6 | 9.3E5 | 55 | 16 | 54 | 16 | 0.37 |
| qD | ng/ml | 1.6E7 | 1.5E7 | 2.0E7 | 1.6E7 | 1.0E7 | 8.0E6 | 1.2E6 | 4.9E6 | 5.2E7 | 4.2E7 | 55 | 16 | 54 | 16 | 0.38 |
| jD | ng/ml | 2.0E1 | 4.1E1 | 4.1E1 | 5.3E1 | 7.0E1 | 5.5E1 | 1.0E-9 | 1.0E-9 | 5.1E2 | 2.9E2 | 81 | 37 | 74 | 37 | 0.61 |
| jE | ng/ml | 1.0E-9 | 1.0E-9 | 8.5E0 | 7.9E0 | 2.1E1 | 1.6E1 | 1.0E-9 | 1.0E-9 | 1.2E2 | 5.6E1 | 81 | 37 | 74 | 37 | 0.51 |
| jF | ng/ml | 4.9E1 | 3.7E1 | 5.8E1 | 5.0E1 | 5.8E1 | 6.1E1 | 1.0E-9 | 1.0E-9 | 2.5E2 | 1.8E2 | 81 | 37 | 74 | 37 | 0.43 |
| jG | ng/ml | 4.4E3 | 4.9E3 | 4.4E3 | 4.7E3 | 1.9E3 | 1.7E3 | 7.6E2 | 6.0E2 | 8.9E3 | 7.9E3 | 81 | 37 | 74 | 37 | 0.55 |
| jH | ng/ml | 7.6E1 | 8.2E1 | 8.6E1 | 9.3E1 | 4.9E1 | 5.9E1 | 1.9E1 | 2.5E1 | 2.8E2 | 3.3E2 | 81 | 37 | 74 | 37 | 0.53 |
| jI | ng/ml | 6.3E1 | 7.5E1 | 6.9E1 | 7.7E1 | 3.5E1 | 3.1E1 | 1.9E1 | 3.5E1 | 2.5E2 | 1.9E2 | 81 | 37 | 74 | 37 | 0.61 |
| sK | pg/mL | 3.7E3 | 3.9E3 | 4.0E3 | 4.1E3 | 1.3E3 | 1.3E3 | 1.7E3 | 1.1E3 | 8.0E3 | 6.1E3 | 54 | 15 | 53 | 15 | 0.57 |
| sM | pg/mL | 7.3E4 | 7.7E4 | 7.5E4 | 7.9E4 | 2.1E4 | 2.2E4 | 3.3E4 | 3.9E4 | 1.5E5 | 1.2E5 | 54 | 15 | 53 | 15 | 0.57 |
| sO | pg/mL | 3.0E8 | 3.0E8 | 3.0E8 | 2.8E8 | 9.2E7 | 1.2E8 | 7.9E7 | 9.1E7 | 4.9E8 | 4.9E8 | 54 | 15 | 53 | 15 | 0.46 |
| wC | ng/ml | 1.6E0 | 1.7E0 | 2.2E0 | 1.9E0 | 2.3E0 | 1.0E0 | 2.5E-1 | 5.9E-1 | 1.5E1 | 3.7E0 | 54 | 13 | 53 | 13 | 0.54 |
| wD | ng/ml | 1.6E1 | 2.0E1 | 7.3E1 | 2.5E1 | 2.9E2 | 2.1E1 | 2.1E0 | 6.0E0 | 2.1E3 | 7.2E1 | 54 | 13 | 53 | 13 | 0.55 |
| wE | ng/ml | 4.9E1 | 4.9E1 | 5.3E1 | 4.8E1 | 2.5E1 | 1.3E1 | 7.0E0 | 3.0E1 | 1.4E2 | 7.2E1 | 54 | 13 | 53 | 13 | 0.44 |
| wG | ng/ml | 8.2E-2 | 1.0E-9 | 1.2E-1 | 5.1E-2 | 1.5E-1 | 8.6E-2 | 1.0E-9 | 1.0E-9 | 7.1E-1 | 2.8E-1 | 54 | 13 | 53 | 13 | 0.35 |
| wH | ng/ml | 1.9E-2 | 3.0E-3 | 1.6E-1 | 2.8E-2 | 4.9E-1 | 5.3E-2 | 1.0E-9 | 1.0E-9 | 2.9E0 | 1.7E-1 | 54 | 13 | 53 | 13 | 0.35 |
| wF | ng/ml | 1.7E-1 | 9.7E-3 | 2.5E0 | 1.6E-1 | 9.9E0 | 3.1E-1 | 1.0E-9 | 1.0E-9 | 5.7E1 | 1.1E0 | 54 | 13 | 53 | 13 | 0.36 |
| rA | pg/ml | 2.4E1 | 2.3E1 | 3.0E1 | 3.0E1 | 2.7E1 | 2.0E1 | 1.0E-9 | 4.2E0 | 2.0E2 | 8.5E1 | 80 | 38 | 74 | 38 | 0.52 |
| qZ | pg/ml | 4.3E1 | 4.0E1 | 1.9E2 | 7.3E2 | 1.2E3 | 2.6E3 | 2.8E-4 | 4.8E-2 | 1.0E4 | 1.0E4 | 71 | 29 | 68 | 29 | 0.47 |
| qY | pg/ml | 2.9E1 | 2.8E1 | 5.1E1 | 5.5E1 | 7.4E1 | 5.5E1 | 8.7E-1 | 3.3E0 | 5.3E2 | 2.2E2 | 80 | 38 | 74 | 38 | 0.55 |
| qX | pg/ml | 5.4E1 | 6.0E1 | 6.0E1 | 6.7E1 | 3.8E1 | 4.4E1 | 1.0E-9 | 1.0E-9 | 1.8E2 | 2.1E2 | 80 | 38 | 74 | 38 | 0.54 |
| qW | pg/ml | 9.7E0 | 9.1E0 | 1.5E1 | 1.4E1 | 2.0E1 | 1.6E1 | 1.0E-9 | 1.0E-9 | 1.2E2 | 8.1E1 | 80 | 38 | 74 | 38 | 0.50 |
| qV | pg/ml | 2.2E3 | 2.2E3 | 2.8E3 | 3.1E3 | 2.0E3 | 3.0E3 | 2.3E2 | 5.6E2 | 8.5E3 | 1.7E4 | 80 | 38 | 74 | 38 | 0.49 |
| qU | pg/ml | 5.5E1 | 5.5E1 | 1.7E2 | 9.3E1 | 2.6E2 | 1.1E2 | 1.0E-9 | 1.0E-9 | 1.4E3 | 4.7E2 | 80 | 38 | 74 | 38 | 0.45 |
| qT | pg/ml | 3.7E1 | 4.7E1 | 6.5E1 | 6.1E1 | 1.2E2 | 4.9E1 | 1.0E-9 | 1.0E-9 | 9.0E2 | 2.0E2 | 80 | 38 | 74 | 38 | 0.59 |
| qI | ng/ml | 5.4E4 | 7.6E4 | 6.2E4 | 6.7E4 | 3.1E4 | 3.0E4 | 1.1E4 | 5.9E3 | 1.6E5 | 1.0E5 | 54 | 17 | 54 | 17 | 0.59 |
| qH | ng/ml | 6.6E4 | 6.7E4 | 7.2E4 | 6.6E4 | 3.8E4 | 4.5E4 | 1.5E4 | 7.6E3 | 1.8E5 | 1.6E5 | 54 | 17 | 54 | 17 | 0.44 |
| qG | ng/ml | 1.8E5 | 2.2E5 | 1.9E5 | 2.0E5 | 5.9E4 | 8.8E4 | 5.8E4 | 1.7E4 | 3.3E5 | 3.1E5 | 54 | 17 | 54 | 17 | 0.59 |
| jK | ng/ml | 1.6E3 | 1.8E3 | 1.7E3 | 1.8E3 | 5.3E2 | 7.7E2 | 5.5E2 | 6.4E2 | 3.5E3 | 4.0E3 | 81 | 37 | 74 | 37 | 0.54 |
| jL | ng/ml | 1.7E2 | 2.5E2 | 2.5E2 | 3.5E2 | 1.9E2 | 3.6E2 | 3.6E1 | 4.8E1 | 9.6E2 | 2.1E3 | 81 | 37 | 74 | 37 | 0.61 |
| jM | ng/ml | 7.1E4 | 6.4E4 | 7.3E4 | 7.5E4 | 4.0E4 | 4.1E4 | 3.9E2 | 1.1E3 | 1.9E5 | 1.7E5 | 81 | 37 | 74 | 37 | 0.52 |
| jO | pg/ml | 2.1E5 | 2.2E5 | 2.7E5 | 2.5E5 | 1.7E5 | 1.3E5 | 5.2E4 | 7.7E4 | 1.1E6 | 6.4E5 | 81 | 37 | 74 | 37 | 0.49 |
| jP | pg/ml | 2.2E5 | 2.1E5 | 2.5E5 | 2.3E5 | 1.5E5 | 1.5E5 | 3.6E4 | 5.8E4 | 9.1E5 | 7.2E5 | 81 | 37 | 74 | 37 | 0.45 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jQ | pg/ml | 2.8E3 | 2.8E3 | 3.7E3 | 3.7E3 | 3.1E3 | 3.3E3 | 4.2E1 | 1.4E2 | 1.3E4 | 1.4E4 | 81 | 37 | 74 | 37 | 0.48 |
| jR | pg/ml | 8.6E3 | 5.9E3 | 1.3E4 | 1.0E4 | 1.3E4 | 9.4E3 | 1.0E-9 | 1.0E-9 | 6.8E4 | 3.0E4 | 81 | 37 | 74 | 37 | 0.46 |
| jT | pg/ml | 1.7E5 | 1.7E5 | 1.7E5 | 1.9E5 | 6.3E4 | 7.9E4 | 6.8E4 | 7.9E4 | 3.9E5 | 3.8E5 | 81 | 37 | 74 | 37 | 0.55 |
| xA | pg/ml | 3.9E0 | 4.7E0 | 1.5E1 | 7.5E0 | 5.4E1 | 1.0E1 | 1.0E-9 | 1.0E-9 | 3.9E2 | 3.0E1 | 54 | 14 | 53 | 14 | 0.50 |
| yE | pg/ml | 7.9E1 | 7.2E1 | 8.3E1 | 8.7E1 | 4.4E1 | 3.5E1 | 1.8E1 | 5.2E1 | 3.0E2 | 1.5E2 | 54 | 14 | 53 | 14 | 0.55 |
| tM | pg/ml | 3.9E1 | 3.5E1 | 4.2E1 | 3.9E1 | 2.1E1 | 1.6E1 | 1.0E-9 | 2.2E1 | 1.0E2 | 6.4E1 | 54 | 14 | 53 | 14 | 0.46 |
| tL | pg/ml | 1.0E-9 | 1.0E-9 | 6.9E0 | 1.9E-1 | 3.6E1 | 5.7E-1 | 1.0E-9 | 1.0E-9 | 2.6E2 | 2.1E0 | 54 | 14 | 53 | 14 | 0.44 |
| jU | mIU/ml | 3.5E0 | 4.8E0 | 1.0E1 | 7.8E0 | 1.8E1 | 1.1E1 | 8.9E-2 | 6.2E-2 | 8.1E1 | 6.7E1 | 81 | 37 | 74 | 37 | 0.52 |
| jV | mIU/ml | 1.5E0 | 1.2E0 | 3.4E0 | 3.3E0 | 5.5E0 | 5.9E0 | 3.4E-2 | 6.9E-4 | 3.1E1 | 2.6E1 | 81 | 37 | 74 | 37 | 0.44 |
| jY | ng/ml | 7.4E-4 | 7.6E-4 | 9.8E-3 | 3.7E-3 | 4.1E-2 | 6.7E-3 | 1.0E-9 | 1.0E-9 | 3.0E-1 | 2.7E-2 | 81 | 37 | 74 | 37 | 0.50 |
| kC | pg/ml | 9.7E1 | 8.9E1 | 2.3E2 | 1.3E2 | 5.6E2 | 1.2E2 | 2.9E1 | 2.1E1 | 3.5E3 | 6.8E2 | 53 | 29 | 51 | 29 | 0.49 |
| kE | pg/ml | 1.2E5 | 1.3E5 | 1.3E5 | 1.3E5 | 3.2E4 | 4.4E4 | 4.1E4 | 4.1E4 | 2.0E5 | 2.1E5 | 53 | 29 | 51 | 29 | 0.55 |
| kF | pg/mL | 6.0E1 | 6.6E1 | 7.4E1 | 6.5E1 | 7.1E1 | 2.1E1 | 2.7E1 | 2.8E1 | 5.1E2 | 1.2E2 | 53 | 29 | 51 | 29 | 0.54 |
| kG | pg/mL | 8.5E3 | 1.0E4 | 9.4E3 | 1.6E4 | 7.8E3 | 1.8E4 | 7.5E2 | 1.1E3 | 4.3E4 | 9.1E4 | 53 | 29 | 51 | 29 | 0.61 |
| kI | pg/ml | 2.0E2 | 1.9E2 | 2.4E2 | 1.9E2 | 1.5E2 | 7.8E1 | 7.9E1 | 5.4E1 | 8.7E2 | 4.2E2 | 53 | 29 | 51 | 29 | 0.39 |
| kK | pg/ml | 1.0E2 | 9.8E1 | 1.6E2 | 1.6E2 | 1.9E2 | 1.7E2 | 6.4E0 | 2.9E1 | 1.2E3 | 6.9E2 | 53 | 29 | 51 | 29 | 0.48 |
| kN | pg/ml | 9.2E2 | 8.1E2 | 1.4E3 | 1.2E3 | 1.9E3 | 1.3E3 | 2.4E2 | 1.2E2 | 1.3E4 | 6.3E3 | 53 | 29 | 51 | 29 | 0.45 |
| kO | pg/ml | 7.7E3 | 7.1E3 | 1.0E4 | 8.2E3 | 1.8E4 | 3.9E3 | 3.7E3 | 3.4E3 | 1.3E5 | 1.9E4 | 53 | 29 | 51 | 29 | 0.46 |
| kP | pg/ml | 4.8E3 | 5.4E3 | 6.8E3 | 8.5E3 | 6.1E3 | 9.2E3 | 8.6E2 | 1.4E3 | 3.3E4 | 4.8E4 | 53 | 29 | 51 | 29 | 0.57 |
| kQ | pg/ml | 4.2E3 | 4.4E3 | 4.9E3 | 5.3E3 | 2.6E3 | 3.4E3 | 5.6E2 | 1.3E2 | 1.4E4 | 1.8E4 | 105 | 45 | 97 | 45 | 0.50 |
| kR | pg/ml | 2.0E1 | 2.0E1 | 3.6E1 | 2.2E1 | 1.0E2 | 1.4E1 | 1.0E-9 | 1.4E-1 | 1.0E3 | 6.9E1 | 105 | 45 | 97 | 45 | 0.48 |
| kS | pg/ml | 7.6E2 | 9.7E2 | 8.9E2 | 1.4E3 | 5.2E2 | 2.1E3 | 1.3E2 | 2.1E2 | 3.2E3 | 1.4E4 | 105 | 45 | 97 | 45 | 0.59 |
| pS | ng/ml | 1.8E5 | 2.6E5 | 2.1E5 | 2.6E5 | 9.0E4 | 8.6E4 | 9.7E4 | 1.4E5 | 5.0E5 | 3.6E5 | 54 | 15 | 53 | 15 | 0.68 |
| rZ | ng/ml | 1.0E-9 | 1.0E-9 | 7.1E-3 | 1.0E-2 | 2.0E-2 | 4.4E-2 | 1.0E-9 | 1.0E-9 | 1.1E-1 | 2.6E-1 | 78 | 35 | 71 | 35 | 0.46 |
| rY | ng/ml | 5.3E-2 | 6.1E-2 | 2.2E-1 | 5.6E-1 | 8.1E-1 | 2.8E0 | 1.0E-9 | 1.0E-9 | 6.3E0 | 1.7E1 | 78 | 35 | 71 | 35 | 0.51 |
| rX | ng/ml | 1.0E-9 | 1.0E-9 | 8.4E-2 | 5.8E-2 | 4.4E-1 | 3.2E-1 | 1.0E-9 | 1.0E-9 | 3.7E0 | 1.9E0 | 78 | 35 | 71 | 35 | 0.47 |
| lK | pg/ml | 7.5E1 | 1.6E2 | 1.6E2 | 2.5E2 | 1.9E2 | 5.4E2 | 1.0E-9 | 1.0E-9 | 7.4E2 | 3.3E3 | 81 | 37 | 74 | 37 | 0.54 |
| lL | pg/ml | 1.7E3 | 1.8E3 | 2.7E3 | 2.3E3 | 3.0E3 | 2.1E3 | 7.5E1 | 1.5E1 | 1.9E4 | 7.2E3 | 81 | 37 | 74 | 37 | 0.47 |
| lM | pg/ml | 1.1E3 | 1.3E3 | 2.2E3 | 3.7E3 | 3.0E3 | 7.1E3 | 1.3E2 | 2.2E2 | 1.6E4 | 3.4E4 | 81 | 37 | 74 | 37 | 0.56 |
| lN | pg/ml | 1.0E-9 | 1.0E-9 | 6.9E0 | 2.8E0 | 2.2E1 | 3.7E0 | 1.0E-9 | 1.0E-9 | 1.5E2 | 1.2E1 | 81 | 37 | 74 | 37 | 0.52 |
| lO | pg/ml | 1.0E-9 | 1.0E-9 | 5.0E-1 | 3.2E0 | 4.5E0 | 1.5E1 | 1.0E-9 | 1.0E-9 | 4.0E1 | 8.4E1 | 81 | 37 | 74 | 37 | 0.52 |
| zA | ng/ml | 1.9E7 | 1.9E7 | 1.9E7 | 1.9E7 | 6.6E6 | 6.0E6 | 6.7E6 | 6.7E6 | 3.4E7 | 2.8E7 | 50 | 12 | 49 | 12 | 0.50 |
| rW | ng/ml | 1.7E-2 | 3.7E-2 | 2.7E-2 | 4.3E-2 | 3.2E-2 | 4.4E-2 | 1.0E-9 | 1.0E-9 | 1.7E-1 | 1.8E-1 | 54 | 16 | 54 | 16 | 0.63 |
| rV | ng/ml | 1.0E-9 | 1.0E-9 | 1.2E-2 | 2.5E-3 | 4.0E-2 | 7.4E-3 | 1.0E-9 | 1.0E-9 | 2.2E-1 | 2.9E-2 | 54 | 16 | 54 | 16 | 0.47 |
| rU | ng/ml | 1.1E-1 | 5.5E-2 | 1.8E-1 | 9.3E-2 | 2.7E-1 | 9.5E-2 | 1.0E-9 | 1.0E-9 | 1.4E0 | 3.6E-1 | 54 | 16 | 54 | 16 | 0.42 |
| rT | ng/ml | 6.5E0 | 5.4E0 | 6.8E0 | 5.5E0 | 4.2E0 | 2.0E0 | 7.3E-1 | 1.1E0 | 2.1E1 | 1.1E1 | 54 | 16 | 54 | 16 | 0.40 |
| rS | ng/ml | 3.5E0 | 3.6E0 | 5.8E0 | 4.3E0 | 6.6E0 | 2.6E0 | 7.6E-1 | 3.9E-1 | 3.8E1 | 9.4E0 | 54 | 16 | 54 | 16 | 0.49 |
| sC | pg/mL | 5.8E3 | 1.2E4 | 9.5E3 | 1.5E4 | 8.6E3 | 1.2E4 | 1.7E3 | 2.5E3 | 4.4E4 | 4.2E4 | 54 | 15 | 53 | 15 | 0.65 |
| yL | pg/ml | 3.2E1 | 2.6E1 | 3.9E1 | 2.8E1 | 2.8E1 | 1.1E1 | 5.6E0 | 1.6E1 | 1.8E2 | 4.5E1 | 52 | 13 | 51 | 13 | 0.38 |
| rP | pg/ml | 9.5E1 | 1.5E2 | 1.6E2 | 2.3E2 | 2.2E2 | 2.1E2 | 1.0E-9 | 1.0E-9 | 1.2E3 | 5.0E2 | 54 | 16 | 54 | 16 | 0.60 |
| rQ | ng/ml | 1.0E-9 | 1.0E-9 | 3.6E0 | 8.4E0 | 1.6E1 | 1.8E1 | 1.0E-9 | 1.0E-9 | 8.9E1 | 5.6E1 | 54 | 16 | 54 | 16 | 0.58 |
| rO | ng/ml | 2.5E-2 | 3.8E-2 | 4.8E-2 | 4.5E-2 | 8.5E-2 | 3.7E-2 | 1.0E-9 | 1.0E-9 | 4.4E-1 | 9.6E-2 | 54 | 16 | 54 | 16 | 0.58 |
| rR | ng/ml | 3.9E0 | 1.3E1 | 2.3E1 | 1.9E1 | 6.8E1 | 1.9E1 | 1.0E-9 | 1.0E-9 | 4.5E2 | 6.6E1 | 54 | 16 | 54 | 16 | 0.63 |
| rN | ng/ml | 6.6E-1 | 5.2E-1 | 7.4E-1 | 6.5E-1 | 4.4E-1 | 4.8E-1 | 5.1E-2 | 1.5E-1 | 2.1E0 | 2.2E0 | 54 | 16 | 54 | 16 | 0.41 |
| qO | pg/ml | 9.8E3 | 1.5E4 | 1.3E4 | 1.7E4 | 9.6E3 | 1.4E4 | 2.2E3 | 1.1E3 | 4.6E4 | 4.5E4 | 55 | 15 | 54 | 15 | 0.56 |
| qP | pg/ml | 3.6E2 | 5.3E2 | 4.4E2 | 5.5E2 | 3.0E2 | 3.9E2 | 1.0E-9 | 1.1E2 | 1.5E3 | 1.5E3 | 55 | 15 | 54 | 15 | 0.58 |
| qQ | pg/ml | 1.5E1 | 1.5E1 | 1.7E1 | 1.6E1 | 3.8E1 | 2.7E1 | 1.0E-9 | 1.0E-9 | 2.8E2 | 9.9E1 | 55 | 15 | 54 | 15 | 0.46 |
| nW | pg/ml | 1.1E5 | 1.1E5 | 1.1E5 | 1.1E5 | 2.4E4 | 2.4E4 | 5.8E4 | 5.9E4 | 1.8E5 | 1.5E5 | 105 | 45 | 97 | 45 | 0.45 |
| nY | pg/ml | 1.9E3 | 2.1E3 | 2.2E3 | 2.5E3 | 1.4E3 | 2.0E3 | 6.5E2 | 9.8E2 | 9.9E3 | 1.3E4 | 105 | 45 | 97 | 45 | 0.53 |
| oO | pg/ml | 7.5E4 | 8.8E4 | 1.0E5 | 1.3E5 | 1.1E5 | 8.8E4 | 1.5E4 | 3.5E4 | 6.2E5 | 3.3E5 | 51 | 28 | 49 | 28 | 0.62 |
| oP | pg/ml | 1.1E5 | 1.6E5 | 1.3E5 | 1.8E5 | 7.7E4 | 1.2E5 | 2.4E4 | 4.8E4 | 3.6E5 | 4.6E5 | 51 | 28 | 49 | 28 | 0.66 |
| oQ | pg/ml | 2.5E3 | 3.9E3 | 2.9E3 | 4.4E3 | 1.7E3 | 2.9E3 | 9.3E2 | 1.7E3 | 1.0E4 | 1.4E4 | 51 | 28 | 49 | 28 | 0.67 |
| oE | pg/ml | 1.8E2 | 1.3E2 | 4.0E2 | 4.0E2 | 6.0E2 | 5.2E2 | 1.0E-9 | 1.0E-9 | 4.7E3 | 1.9E3 | 105 | 45 | 97 | 45 | 0.48 |
| oF | pg/ml | 7.4E3 | 8.0E3 | 1.7E4 | 2.6E4 | 3.0E4 | 4.9E4 | 6.4E1 | 6.9E2 | 1.7E5 | 2.3E5 | 105 | 45 | 97 | 45 | 0.53 |
| oH | pg/ml | 4.4E1 | 4.9E1 | 9.5E1 | 7.7E1 | 1.5E2 | 7.2E1 | 4.2E0 | 6.2E0 | 8.6E2 | 3.2E2 | 105 | 45 | 97 | 45 | 0.54 |
| oK | pg/ml | 6.4E2 | 6.6E2 | 2.0E3 | 1.6E3 | 3.1E3 | 1.9E3 | 5.2E1 | 1.4E2 | 1.8E4 | 7.2E3 | 105 | 45 | 97 | 45 | 0.53 |
| oN | pg/ml | 4.9E2 | 4.6E2 | 7.8E2 | 5.3E2 | 1.8E3 | 2.2E2 | 1.5E2 | 2.0E2 | 1.8E4 | 1.0E3 | 105 | 45 | 97 | 45 | 0.51 |

Figure 12 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| oW | pg/ml | 2.1E2 | 2.5E2 | 4.8E2 | 2.6E2 | 1.1E3 | 1.5E2 | 7.7E1 | 8.5E1 | 6.0E3 | 5.4E2 | 27 | 8 | 26 | 8 | 0.51 |
| oT | pg/ml | 3.5E2 | 3.8E2 | 3.6E2 | 3.9E2 | 1.8E2 | 1.5E2 | 9.9E1 | 1.9E2 | 7.8E2 | 7.1E2 | 27 | 8 | 26 | 8 | 0.55 |
| oV | pg/ml | 1.4E2 | 1.0E2 | 2.1E2 | 1.3E2 | 2.3E2 | 7.0E1 | 1.0E-9 | 5.8E1 | 9.9E2 | 2.2E2 | 27 | 8 | 26 | 8 | 0.46 |
| oD | pg/ml | 1.7E4 | 1.8E4 | 1.9E4 | 1.9E4 | 8.2E3 | 6.7E3 | 9.3E3 | 1.2E4 | 4.6E4 | 3.3E4 | 27 | 8 | 26 | 8 | 0.54 |
| uL | ng/ml | 3.6E1 | 4.4E1 | 4.4E1 | 4.4E1 | 3.0E1 | 2.1E1 | 1.0E-9 | 1.5E1 | 1.6E2 | 8.6E1 | 52 | 15 | 51 | 15 | 0.54 |
| uO | ng/ml | 3.0E-1 | 1.3E0 | 7.8E-1 | 1.3E0 | 1.4E0 | 1.5E0 | 1.0E-9 | 1.0E-9 | 9.3E0 | 5.4E0 | 52 | 15 | 51 | 15 | 0.67 |
| uM | ng/ml | 6.4E-1 | 8.2E-1 | 1.1E0 | 8.6E-1 | 2.2E0 | 5.3E-1 | 1.0E-9 | 1.0E-9 | 1.3E1 | 2.2E0 | 52 | 15 | 51 | 15 | 0.57 |
| uI | ng/ml | 7.7E-2 | 9.6E-2 | 1.4E-1 | 1.4E-1 | 1.9E-1 | 1.6E-1 | 1.6E-2 | 3.7E-2 | 1.1E0 | 6.6E-1 | 52 | 15 | 51 | 15 | 0.52 |
| uN | ng/ml | 1.5E1 | 1.2E1 | 1.7E1 | 1.4E1 | 6.7E0 | 6.4E0 | 7.7E0 | 6.3E0 | 4.1E1 | 3.0E1 | 52 | 15 | 51 | 15 | 0.38 |
| uG | ng/ml | 2.1E1 | 1.8E1 | 2.5E1 | 2.0E1 | 1.4E1 | 9.9E0 | 7.6E0 | 6.9E0 | 6.9E1 | 4.0E1 | 52 | 15 | 51 | 15 | 0.40 |
| uR | ng/ml | 2.3E0 | 3.7E0 | 3.9E0 | 3.6E0 | 8.6E0 | 2.0E0 | 9.9E-1 | 8.1E-1 | 6.4E1 | 8.0E0 | 54 | 14 | 53 | 14 | 0.64 |
| uP | ng/ml | 2.2E0 | 2.1E0 | 2.5E0 | 2.4E0 | 1.3E0 | 1.2E0 | 1.1E0 | 1.5E0 | 9.1E0 | 6.2E0 | 54 | 14 | 53 | 14 | 0.51 |
| uV | ng/ml | 2.3E-4 | 7.6E-3 | 1.6E-2 | 1.8E-2 | 4.0E-2 | 2.6E-2 | 1.0E-9 | 1.0E-9 | 2.0E-1 | 7.6E-2 | 54 | 14 | 53 | 14 | 0.56 |
| uT | ng/ml | 5.8E1 | 5.8E1 | 8.3E1 | 7.0E1 | 9.2E1 | 5.6E1 | 1.2E1 | 8.7E0 | 5.8E2 | 2.0E2 | 54 | 14 | 53 | 14 | 0.47 |
| uU | ng/ml | 1.7E0 | 2.0E0 | 2.0E0 | 1.9E0 | 1.2E0 | 9.1E-1 | 5.2E-1 | 6.9E-1 | 5.6E0 | 3.6E0 | 54 | 14 | 53 | 14 | 0.51 |
| uW | ng/ml | 7.2E0 | 7.3E0 | 7.6E0 | 7.5E0 | 2.9E0 | 2.8E0 | 4.0E0 | 3.5E0 | 2.2E1 | 1.5E1 | 52 | 15 | 51 | 15 | 0.49 |
| vB | ng/ml | 2.6E0 | 2.9E0 | 2.7E0 | 3.1E0 | 1.2E0 | 1.5E0 | 6.9E-1 | 9.9E-1 | 5.6E0 | 6.1E0 | 52 | 15 | 51 | 15 | 0.58 |
| vC | ng/ml | 1.0E-9 | 1.0E-9 | 3.0E-3 | 3.5E-3 | 2.0E-2 | 1.3E-2 | 1.0E-9 | 1.0E-9 | 1.4E-1 | 5.1E-2 | 52 | 15 | 51 | 15 | 0.55 |
| uY | ng/ml | 7.4E-1 | 9.0E-1 | 1.2E0 | 1.1E0 | 1.1E0 | 8.2E-1 | 8.7E-2 | 1.8E-1 | 4.9E0 | 2.6E0 | 52 | 15 | 51 | 15 | 0.52 |
| uZ | ng/ml | 5.8E-1 | 5.7E-1 | 8.2E-1 | 7.4E-1 | 1.1E0 | 3.9E-1 | 4.7E-2 | 1.2E-1 | 7.2E0 | 1.4E0 | 52 | 15 | 51 | 15 | 0.56 |
| uX | ng/ml | 1.1E1 | 1.3E1 | 1.3E1 | 1.3E1 | 7.2E0 | 7.0E0 | 4.0E0 | 3.7E0 | 3.3E1 | 2.7E1 | 52 | 15 | 51 | 15 | 0.54 |
| vA | ng/ml | 7.4E-1 | 6.8E-2 | 8.6E-2 | 7.7E-2 | 5.8E-2 | 4.2E-2 | 2.4E-2 | 1.7E-2 | 3.0E-1 | 1.6E-1 | 52 | 15 | 51 | 15 | 0.46 |
| vH | ng/ml | 1.2E-1 | 1.1E-1 | 1.6E-1 | 1.1E-1 | 1.4E-1 | 7.0E-2 | 1.5E-2 | 9.9E-3 | 8.0E-1 | 2.4E-1 | 54 | 15 | 53 | 15 | 0.44 |
| vI | ng/ml | 1.4E0 | 2.1E0 | 1.7E0 | 2.6E0 | 1.1E0 | 2.7E0 | 6.2E-3 | 4.2E-3 | 4.5E0 | 1.0E1 | 54 | 15 | 53 | 15 | 0.57 |
| vP | ng/ml | 4.3E2 | 7.3E2 | 5.1E2 | 6.7E2 | 3.9E2 | 5.0E2 | 7.0E1 | 4.0E1 | 2.0E3 | 1.6E3 | 54 | 14 | 53 | 14 | 0.60 |
| vT | ng/ml | 7.7E1 | 8.1E1 | 1.1E2 | 7.5E1 | 1.2E2 | 2.4E1 | 3.7E1 | 2.4E1 | 6.9E2 | 1.0E2 | 54 | 14 | 53 | 14 | 0.44 |
| vU | ng/ml | 1.0E-9 | 1.0E-9 | 2.3E1 | 7.2E0 | 3.5E1 | 1.6E1 | 1.0E-9 | 1.0E-9 | 1.3E2 | 4.7E1 | 54 | 14 | 53 | 14 | 0.38 |
| vQ | ng/ml | 3.5E2 | 3.7E2 | 3.6E2 | 3.9E2 | 1.5E2 | 8.4E1 | 6.7E1 | 3.0E2 | 8.1E2 | 5.5E2 | 54 | 14 | 53 | 14 | 0.59 |
| vO | ng/ml | 1.7E3 | 1.9E3 | 1.8E3 | 1.9E3 | 4.5E2 | 3.9E2 | 1.0E3 | 1.2E3 | 3.0E3 | 2.5E3 | 54 | 14 | 53 | 14 | 0.61 |
| vS | ng/ml | 1.3E3 | 1.1E3 | 1.3E3 | 9.8E2 | 3.6E2 | 4.7E2 | 1.0E-9 | 1.0E-9 | 1.8E3 | 1.5E3 | 54 | 14 | 53 | 14 | 0.28 |
| vV | ng/ml | 9.7E2 | 1.2E3 | 1.4E3 | 2.1E3 | 1.6E3 | 2.9E3 | 1.1E2 | 2.1E1 | 1.1E4 | 1.1E4 | 54 | 14 | 53 | 14 | 0.55 |
| vW | ng/ml | 1.4E2 | 1.2E2 | 1.8E2 | 1.9E2 | 1.4E2 | 1.2E2 | 4.3E1 | 7.1E1 | 6.7E2 | 4.0E2 | 54 | 14 | 53 | 14 | 0.55 |
| pF | pg/ml | 5.1E-1 | 6.1E-1 | 6.9E-1 | 9.3E-1 | 9.9E-1 | 1.5E0 | 1.0E-9 | 1.0E-9 | 9.4E0 | 1.0E1 | 105 | 45 | 97 | 45 | 0.57 |
| pH | ng/ml | 8.9E0 | 1.1E1 | 9.4E0 | 1.4E1 | 4.5E0 | 1.2E1 | 3.4E0 | 4.7E0 | 1.8E1 | 4.2E1 | 27 | 8 | 26 | 8 | 0.60 |
| pI | ng/ml | 7.0E1 | 8.4E1 | 7.0E1 | 8.5E1 | 3.2E1 | 2.5E1 | 2.6E1 | 5.6E1 | 1.5E2 | 1.2E2 | 27 | 8 | 26 | 8 | 0.64 |
| pK | ng/ml | 4.6E-1 | 5.1E-1 | 5.2E-1 | 6.3E-1 | 2.9E-1 | 3.7E-1 | 2.3E-1 | 2.6E-1 | 1.6E0 | 1.4E0 | 27 | 8 | 26 | 8 | 0.61 |

Analyte panel data:

Unconstrained panels with 3 analytes, where 1.0E-10 >= 'model p-value' > 0. Contains 55 panels of 36,603,637 total panels evaluated. :
Ok{Ik(Hr Hw Hx Ii Ij Il In Jj Jo Ma Ml Nf Ng Nk Of Qb) In(Fp Ma Mb Nc Ne Nh Nj Nl Nx) Nk(Fp Nc Ne Nh Nj Nl) MbMl} Et{Ik(In Jj Jo Ma Ng Nk Nq Of Qb) In(Fp Nc Nh Nl) Nk(Fp Nc Nl) Qb(Fp Nl) MaMb} Fp{Nk(Nc Nl)} Ik{MzIn JjOh}

Unconstrained panels with 3 analytes, where 1.0E-9 >= 'model p-value' > 1.0E-10. Contains 466 panels of 36,603,637 total panels evaluated. :
Ok{Ik(aA Et Fp Hq Ih Iq Ir It Iu Iv Jn Jp Js Lh Ly Lz Mb Md Mg Mh Mj Mk Mp Ms Mt Mu Mv Mw Mx My Nb Nc Nd Ne Nh Nj Nl Nm Nn No Nq Ns Nv Nx Ny Oe Og Oh Om Oy Oz Pa Pb Pc Pd Pe Pf Pg Po Pz Qa Qd Qe) Ma(Et Fp Hr Hw Hx Ii Il Jj Lz Mb Mj Mt Nc Nd Ne Nf Nh Nj Nk Nl Nx Of Oh Oz Pc Pd Pf) In(Et Hw Il Im Iv Ji Ly Lz Me Mt Mu Mz Na Nd Ng Nk Nn Nt Oe Of Oh Oz Pc Pd Pf) Mb(Et Fp Hw Ii Ij Il Jj Ly Lz Mh Mj Mt Na Nc Nf Ng Nk Nl Nx Of Oh Pg Qb) Fp(Hr Hw Hx Ii Il Jj Lz Mj Ml Nd Nf Of Pc Pe Pg Po Qb) Ii(Et Im Ji Ly Mt Mu Nc Nd Ne Nh Nj Nl Nx Oh Pc Pd) Nc(Hr Hw Hx Il Jj Lz Mj Ml Nf Nx Of Pc Pg Qb) Nl(Hr Hw Hx Il Jj Lz Mj Ml Nf Ng Of Pc Qb) Nh(Hr Hw Hx Il Jj Mj Ml Of Pc Pg Qb) Of(Hx Ly Ml Nd Ne Nj Nk Nx Oz Pc) Hw(Jj Ly Ml Nc Nn Nx Oh) Nd(Jj Ml Nf Ng Nk Oh) Jj(Hx Ly Nj Nx Pc) Nx(Il Nf Nk) MlNj NkOh jGuN} Et{Ik(Fp Hr Hw Ii Ij Il Iu Js Lj Ly Mb Mg Ml Mp Mt Mu Mv Mw My Nc Nf Nj Nl Nn No Ns Ny Oh Oi Oy Oz Pa Pc Pz Qa Qe) Mb(Fp Hv Hw In Jj Jo Lj Ly Ml Mt Na Nc Ng Nk Nl Nq Ns Nx Of Oh Oz Pc Qb) Fp(Hr Hw Hx Il Jj Jn Js Ma Ml Mt Mx Nc Nl Nq Oz Pc Qa Qe) Nl(Hw Il Jj Js Ma Ml Mt Ng Nq Ns Of Oh Oz Pc Qa) Nc(Hw Jj Js Ma Mt Nq Nx Oz Pc Qb) In(Lj Ly Ma Ne Nj Nt Nx Oh Oz Pc) Ma(Jj Nc Nh Nx Oz Pc Qb) Qb(Lj Ne Nh Nx Oh Pc) Nk(Ne Nh Nj) Jj(Ly Nj Nx) Nq(Jg Pc) NxOf} Ik{Jj(Fp Jg Ji Jp Lh Li Lj Mm Nk Nn No Nv Nw Nx On Pd Qe) Nk(Fp Jp Nc Nl Oh) In(Ji Jp Nw Oh On) NgJp} Nk{Nl(Im Jg Ji Jp Li Mt Nn No Nv Nw Nx Oh On Pd Pf) Nc(Jg Ji Li Nx) FpMt} aN{dE(Ad Ba Bn cB Ch Cp De Dg Dl Fp Ji Nx Oy Pc Pd Pe Pf) PjzG} Pj{iP(uN vU vW zG tL) zI(An iO oF) iC(pS vU) zH(gW IK) QdvU bMsC fPuN jOpS} Fp{In(Jg Ji Mt Nx On)} BbfNqY OrUfpS Unconstrained panels with 3 analytes, where 1.0E-8 >= 'model p-value' > 1.0E-9. Contains 2,872 panels of 36,603,637 total panels evaluated. :
Ok{Nl(aA Et Fp Fr Hq Hu Hv Ih Ij Im Io Ip Iq Ir It Iu Iv Jg Ji Jl Jn Jo Jp Jr Js Lh Li Lu Lw Lx Ly Mc Md Me Mf Mg Mh Mi Mk Mm Mn Mp Mq Mr Ms Mt Mu Mv Mw Mx My Mz Na Nb Nc Nd Ne Nh Ni Nj Nm Nn No Nq Ns Nv Nw Nx Ny Oe Og Oh Oi Om On Oy Oz Pa Pb Pd

Nj(Jp Mt Oh On) Nh(Ji Oh) NeJi} In{Fp(Im Jp Mg Mm Mz Nc Nh Nl Nv Nw Oe Oh Om) Nl(Jg Ji Jt Li Nw On) Ji(Li Nc Ne Nh Nt) On(Mb Nh) MzNj} Aa{Ng(sO uG uI uM uP uR uT uV uZ vB vO vT zG tM) Jh(uP uR vO zG) Mt(Mb Me Nx) Nx(Jg Me) Of(tM tL) bEvV} Pj{pS(aX bP qU) rZ(Fw iP Js) Qv(Fw Tj) iC(qI rT) jO(rS sC) iPuZ} aC{dE(Ad Ba Bn Cp De Dl) Ad(aL Bn bQ cW) BabQ} Jg{My(Fp Mb Nx Pc) Nq(Fp Nx Pc) Jj(Fp Nx)} Fp{Ji(Jj Ml Qb) QbOn JjNx} Jj{Nx(Nc Nt Oh)} dE{Bn(cB cP) DlcP} Bb{dBvC fNsC} Mb{MlJi OfOn} Ng{MnwH NdwF} ApqUpS IidJwF JpcZtR

Unconstrained panels with 3 analytes, where 1.0E-7 >= 'model p-value' > 1.0E-8. Contains 8,531 panels of 36,603,637 total panels evaluated. : Ok{Po(Fr Hq Hr Hu Hv Ih Ii Ij Il Im Io Ip Iq Ir It Iu Iv Jg Jh Jk Jl Jm Jn Jo Jp Jq Jr Js Jt Lh Li Lj Lu Lv Lw Lx Lz Mc Md Me Mf Mg Mh Mi Mj Mk Ml Mm Mn Mp Mq Mr Ms Mv Mw Mx My Mz Na Nb Nf Ng Ni Nk Nm No Nq Nr Ns Nt Nu Nv Nw Ny Oe Og Oi Om On Oy Pa Pb Pe Pg Pz Qa Qb Qc Qd Qe) Iq(aA Fr Hq Hu Hv Hx Ih Ij Il Im Io Ip Ir Is It Iu Iv Jg Ji Jl Jn Jo Jp Jr Js Lh Li Lj Lu Lv Lw Lx Ly Lz Mc Md Me Mf Mg Mh Mi Mj Mk Mm Mn Mp Mq Mr Ms Mt Mu Mv Mw Mx My Mz Na Nb Ne Ng Ni Nj Nm No Nq Nr Ns Nt Nu Nv Nw Ny Oe Og Oi Om On Oy Pa Pb Pe Pf Pg Pz Qa Qb Qc) Lz(aA Et Fr Hq Hr Hu Hv Ih Im Io Ip Ir Is It Iu Iv Jg Jh Ji Jk Jl Jm Jn Jo Jp Jq Jr Js Jt Lh Li Lj Lu Lv Lw Lx Mc Md Me Mf Mg Mh Mi Mj Mk Mm Mn Mq Mr Ms Mu Mv Mw Mx My Mz Na Nb Ng Ni Nm Nn No Nq Nr Ns Nt Nu Nv Nw Ny Oe Og Oi Om On Oy Pa Pb Pe Pz Qa Qc Qd Qe) Pc(aA Et Fr Hq Hr Hu Hv Ih Ij Im Io Ip Ir Is It Iu Iv Jg Ji Jn Jo Jp Jq Jr Js Lh Li Lj Lu Lv Lw Lx Mc Md Me Mf Mg Mh Mi Mj Mk Ml Mm Mn Mp Mq Mr Ms Mu Mv Mw Mx My Mz Na Nb Nf Ng Ni Nn No Nq Nr Ns Nt Nu Nv Nw Ny Oe Og Oi Om On Oy Pa Pb Pg Pz Qa Qb Qd Qe) Me(AA Et Fr Hq Hu Hv Ih Il Im Io Ip Ir Is It Iu Iv Jg Ji Jl Jm Jn Jo Jp Jq Jr Js Jt Lh Li Lj Lu Lv Lw Lx Mc Md Mf Mg Mh Mi Mk Mm Mn Mq Mr Ms Mu Mv Mw Mx My Mz Na Nb Ne Ni Nm Nn No Nq Ns Nt Nu Nv Nw Oe Og Oi Om On Oy Pa Pb Pd Pf Pz Qa Qc Qd Qe) Ji(Et Fr Hq Hu Hv Ih Im Io Ip Ir Is It Iu Iv Jg Jh Jk Jl Jm Jn Jo Jp Jr Jt Li Lj Lu Lv Lw Lx Mc Md Mf Mg Mh Mi Mk Mm Mn Mq Mr Ms Mu Mv Mw Mx My Mz Na Ne Ng Ni Nm Nn No Nq Nr Ns Nt Nu Nv Nw Nx Ny Oe Og Oh Oi Om On Oy Pa Pb Pd Pf Pz Qa Qc Qd Qe) Ij(Fr Hq Hu Hv Hx Ih Il Im Io Ip Ir It Iu Iv Jg Jh Jj Jk Jn Jo Jp Jq Jr Js Lh Li Lj Lu Lv Lw Lx Mc Md Mf Mg Mh Mi Mk Ml Mm Mn Mp Mq Mr Ms Mv Mw Mx My Mz Na Nb Ng Ni Nn No Nq Nr Ns Nt Nu Nv Nw Ny Og Oi Om On Oy Pa Pb Pg Pz Qa Qb Qc Qd Qe) Pf(aA Et Fr Hq Hu Hv Ih Im Io Ip Ir Is It Iu Iv Jg Jh Jk Jl Jm Jn Jo Jp Jq Jr Js Jt Lh Li Lj Lu Lv Lw Lx Mc Md Mf Mg Mh Mi Mk Mm Mn Mq Mr Ms Mu Mv Mw Mx My Mz Na Ni Nm Nn No Nq Nr Ns Nt Nu Nv Nw Ny Oe Og Oi Om On Pa Pb Pz Qa Qc Qd Qe) Ml(Fr Hq Hv Ih Im Io Ip Ir Is It Iu Iv Jg Jh Jk Jl Jm Jn Jo Jp Jq Jr Js Jt Lh Li Lj Lu Lv Lw Lx Mc Md Mf Mg Mh Mi Mj Mk Mm Mn Mq Mr Ms Mv Mw Mx My Mz Na Nb Ni Nm No Nq Nr Ns Nt Nu Nv Nw Ny Oe Og Oi Om On Oy Pa Pb Pz Qa Qc Qd Qe) Pd(aA Fr Hq Hu Hv Ih Im Io Ip Ir Is It Iu Iv Jg Jh Jk Jl Jm Jn Jo Jp Jq Jr Jt Lh Li Lj Lu Lv Lw Lx Mc Md Mf Mg Mh Mi Mk Mm Mn Mq Mr Ms Mu Mv Mw Mx My Mz Na Ni Nm Nn No Nq Nr Ns Nt Nu Nv Nw Ny Oe Og Oi Om On Pb Pz Qa Qc Qd Qe) Pg(aA aN Fr Hq Hu Hv Ih Io Ip Ir Is It Iu Iv Jh Jk Jl Jm Jn Jo Jp Jq Jr Js Jt Lh Li Lj Lv Lw Lx Mc Md Mf Mg Mh Mi Mj Mk Mm Mn Mp Mq Mr Ms Mv Mw Mx My Mz Na Nb Ng Ni Nm No Nq Nr Ns Nt Nu Nv Ny Og Oi Pa Pb Pz Qa Qb Qc Qd Qe) Il(aA Fr Hq Hu Hv Ih Io Ip Ir Is It Iu Iv Jg Jh Jk Jl Jm Jn Jo Jp Jq Jr Js Jt Lh Li Lj Lu Lv Lw Lx Mc Md Mf Mg Mh Mi Mk Mm Mn Mq Mr Ms Mv Mw Mx My Mz Ni Nm No Nq Nr Ns Nt Nu Nv Ny Og Oi Om On Oy Pa Pb Pz Qa Qb Qc Qd Qe) Mt(aA Fr Hq Hu Hv Ih Im Io Ip Ir Is It Iu Iv Jg Jh Jk Jl Jm Jn Jo Jp Jq Jr Jt Lh Li Lj Lu Lv Lw Lx Mc Md Mf Mg Mh Mi Mk Mm Mn Mq Mr Ms Mv Mw Mx Mz Na Ni Nm Nn No Nr Ns Nt Nu Nv Nw Ny Oe Og Oi On Pa Pb Pz Qa Qc Qd Qe) Mj(aA Fr Hq Hu Hv Ih Io Ip Ir Is It Iu Iv Jg Jh Jk Jl Jm Jn Jo Jp Jq Jr Js Jt Lh Li Lj Lv Lw Lx Mc Md Mf Mg Mh Mi Mk Mm Mn Mq Mr Ms Mv Mw Mx My Mz Nb Ni Nm No Nq Nr Ns Nt Nu Nv Nw Ny Og Oi Om On Pb Pz Qa Qc Qd Qe) Ng(Fr Hq Hv Ih Io Ip Ir Is It Iu Iv Jh Jk Jl Jm Jn Jo Jp Jq Jr Jt Lh Li Lj Lv Lw Lx Mc Md Mf Mg Mh Mi Mk Mm Mn Mq Mr Ms Mv Mw Mx My Mz Nb Ni Nm Nn No Nq Nr Ns Nt Nu Nv Nw Ny Oe Og Oi Om On Oy Pa Pb Pz Qa Qc Qd Qe) Mp(aA Fr Hq Hu Hv Ih Im Io Ip Ir It Iu Iv Jg Jn Jo Jp Jr Js Lh Li Lj Lu Lv Lw Lx Mc Md Mf Mg Mh Mi Mk Mm Mn Mq Mr Ms Mv Mw Mx My Mz Na Nb Ni Nm No Nq Nr Ns Nt Nu Nv Nw Ny Oe Og Oi Om On Oy Pa Pb Pz Qa Qb Qd Qe) Oh(aA Fr Hq Hu Hv Ih Im Io Ip Ir Is It Iv Jg Jh Jk Jl Jm Jn Jo Jp Jq Jr Jt Lh Li Lj Lu Lv Lw Lx Mc Md Mf Mg Mh Mi Mk Mm Mn Mq Mr Ms Mu Mv Mx Mz Na Ni Nm Nn No Nr Ns Nt Nu Nv Nw Oe Og Oi Om On Pb Pz Qa Qc Qd Qe) Qb(aA Fr Hq Hu Hv Ih Ii Io Ip Ir Is It Iu Iv Jh Jk Jl Jm Jn Jo Jp Jq Js Jt Lh Lu Lv Lw Lx Mc Md Mf Mg Mh Mi Mk Mm Mn Mq Mr Ms Mv Mw Mx My Mz Na Nb Ni Nm No Nq Nr Ns Nu Nv Nw Ny Oe Og Oi Om Oy Pa Pb Pz Qc Qd) Oz(aA dX Fr Hq Hu Hv Ih Io Ip Ir Is It Iv Jg Jh Jk Jl Jm Jn Jo Jp Jq Jr Jt Lh Li Lj Lv Lw Lx Mc Md Mf Mg Mh Mi Mk Mm Mn Mq Mr Ms Mv Mw Mx My Mz Ni Nm No Nq Nr Ns Nt Nu Nv Nw Ny Og Oi Om On Pb Pz Qa Qc Qd Qe) Et(Fr Hq Hu Hv Ih Im Io Ip Ir Is It Iu Iv Jg Jh Jk Jl Jm Jn Jp Jq Jr Jt Li Lj Lu Lv Lw Lx Mc Md Mf Mg Mh Mi Mk Mm Mn Mq Mr Ms Mu Mv Mx Mz Na Ni Nm Nn No Nr Nt Nu Nv Nw Oe Og Oi Om On Pa Pb Pz Qa Qc Qd Qe) Mu(Fr Hq Hu Hv Ih Im Io Ip Ir Is It Iu Iv Jg Jh Jk Jl Jn Jo Jq Jr Js Li Lj Lu Lv Lw Lx Mc Md Mf Mg Mh Mi Mk Mm Mn Mq Mr Ms Mv Mx Mz Na Ni Nm Nn No Ns Nt Nu Nv Nw Ny Oe Og Oi Om On Pa Pb Pz Qa Qc Qd Qe) Nb(Fr Hq Hu Hx Ih Im Ip Ir It Iu Iv Jg Jh Jj Jo Jp Jr Js Lh Li Lj Lu Lv Lw Lx Mc Md Mf Mg Mh Mi Mk Mm Mn Mq Mr Ms Mv Mw Mx My Mz Na Nf Ni Nn No Nq Ns Nt Nu Nv Nw Ny Oe Og Oi Om On Oy Pa Pb Pz Qd Qe) Ne(aA Fr Hq Hu Hv Ih Io Ip Is It Iv Jg Jh Jk Jl Jm Jn Jo Jp Jq Jr Jt Lh Li Lj Lu Lv Lw Lx Mc Md Mf Mg Mh Mi Mk Mm Mn Mq Mr Ms Mv Mz Na Nh Ni Nm No Nq Nr Ns Nt Nu Nv Nw Og Oi Om On Pb Pz Qc Qd Qe) Nf(aA Fr Hq Hv Ih Io Ip Ir Is It Iu Iv Jg Jh Jk Jl Jm Jn Jo Jp Jq Jt Lh Li Lj Lv Lw Lx Mc Md Mf Mg Mh Mi Mk Mm Mn Mq Mr Ms Mv Mw Mx My Mz Ni Nm No Nr Ns Nt Nu Nv Ny Og Oi Om On Pb Pz Qa Qc Qd Qe) Nn(Hq Hu Hv Ih Im Io Ir It Iu Iv Jg Jk Jl Jm Jn Jo Jp Jq Jr Js Jt Lh Li Lj Lu Lv Lx Mc Md Mf Mg Mh Mk Mn Mr Ms Mv Mw Mx My Na Nm No Nr Ns Nt Nu Nv Nw Nx Ny Oe Om On Oy Pa Pb Pz Qa Qc Qd Qe) Hr(aA Fr Hq Hv Ih Io Ip Ir Is It Iu Iv Jg Jh Jk Jl Jm Jn Jo Jp Jq Jt Lh Li Lv Lw Lx Mc Md Mf Mg Mh Mi Mk Mm Mn Mq Mr Ms Mv Mw Mx My Mz Ni Nm No Nr Ns Nu Nv Nw Og Oi Om On Pa Pb Qa Qc Qd Qe) Ly(aA aN Fr Hq Hu Hv Ih Io Ip Ir Is It Iv Jg Jh Jk Jl Jm Jn Jq Jr Jt Lh Li Lj Lv Lw Lx Mc Md Mf Mg Mh Mi Mk Mm Mn Mq Mr Ms Mv Mz Na Ni Nm No Nq Nr Nt Nu Nv Nw Og Oi Om On Pz Qa Qc Qd Qe) Im(Hq Hu Ih Io Ip Ir Is It Iu Iv Jg Jl Jn Jo Jp Jq Jr Js Jt Lh Li Lu Lv Lx Mc Md Mf Mg Mh Mk Mm Mn Mq Mr Ms Mv Mw Mx My Mz Na Ni Nm No Nq Ns Nt Nv Nw Ny Oe Oi Om On Oy Pa Pb Pz Qa Qd Qe) Js(Fr Hq Hu Hv Hx Ih Ii Io Ir Iu Iv Jg Jn Jo Jp Jq Jr Jt Lh Li Lj Lu Lv Mc Mf Mg Mk Mm Mn Ms Mv Mw Mx My Mz Na Nk Nm No Nq Nr Ns Nt Nu Nv Nw Ny Oe Oi Om On Oy Pa Pb Pz Qa Qd Qe) Pa(Fr Hq Hu Ih Ip Ir It Iu Iv Jg Jo Jp Jr Lh Li Lj Lu Lv Lw Lx Mc Md Mf Mg Mh Mi Mk Mm Mn Mq Mr Ms Mv Mw Mx My Mz Na Ni No Nq Ns Nt Nu Nv Nw Ny Oe Og Oi Om On Oy Pb Pz Qe) Hx(aA Fr Hq Hv Ih Io Ip Ir Is It Iu Iv Jh Jk Jl Jm Jn Jq Jt Lh Li Lj Lv Lw Lx Mc Md Mf Mg Mh Mi Mk Mm Mn Mq Mr Ms Mv Mw Mx My Ni No Nr Ns Nu Nv Ny Og Oi Pb Qa Qc Qd Qe) Pc(Fr Hq Hv Ih Io Ip Ir Is It Iv Jh Jk Jl Jm Jn Jp Jq Jr Jt Lh Li Lj Lv Lw Lx Mc Md Mf Mg Mh Mi Mm Mn Mq Mr Mv Mx Mz Ni Nm No Nr Ns Nt Nu Nw Og Oi Om On Pz Qa Qc Qd Qe) Nk(aA Fr Hq Hv Ih Io Ip Is It Iu Jh Jk Jl Jm Jn Jo Jp Jq Jt Lh Li Lv Lw Lx Mc Md Mg Mh Mi Mk Mm Mn Mq Mr Mv Mx Mz Ni Nm No Nr Ns Nu Nv Nw Og Oi Om On Pz Qa Qc Qd Qe) Nx(AA Fr Hq Hu Hv Ih Io Ip Is It Iv Jg Jh Jk Jl Jm Jn Jp Jr Jt Li Lj Lv Lw Lx Mc Md Mf Mh Mi Mk Mm Mn Mq Mr Mv Mz Ni Nm No Nr Nt Nu Nw Og Oi On Pz Qa Qc Qd Qe) Nj(Fr Hq Hu Hv Io Ip Is It Iv Jg Jh Jk Jl Jm Jn Jq Jr Jt Lh Li Lj Lv Lw Lx Mc Md Mf Mg Mi Mm Mn Mq Mr Ms Mv Ni Nm No Nq Nr Ns Nt Nu Nv Og Oi Om Pz Qa Qc Qd Qe) Oy(Fr Hq Hu Ih Ir It Iu Iv Jh Jn Jo Jp Jr Lh Li Lu Lv Lx Mc Mf Mg Mh Mk Mm Mn Mr Ms Mv Mw Mx My Mz Na No Nq Ns Nt Nu Nv Nw Ny Oe Og Oi Om On Pb Pz

Oy Oz Pa Pc Pd Pf) Ne(Im Jp Li Mt Nn No Nt Nv Nw Nx Oh On Pf) Nh(Im Jp Li Mt Nn No Nt Nv Nw Nx On Pd Pf) Nj(Fr Im Li Nn Nt Nv Nw Nx Pf Qa) Mb(Jp Li Mt Nw Oh On) Nx(Jj Mt)} aC{Ad(aF aH aI Aj aM An Ao Ap AR aS AW aY bB bC bE Bg bH bl bL bM bN BO bP bU bZ cB cC cE cG CH cI cJ cK cN CO CP Cq Ct Cu cX cZ dB Dc dD De dG dH Dl dJ dK Dl Fr) Cp(aH aM aR Bg bH bl bL Bn bQ bU bZ cK cO Cq dB Dg Dl) Dl(aH AR Aw bE bL Bn Bo cB Ch cN cP cW dB De Di) Dg(aH aR bL Bn bQ Ch cO dB dE) dB(Ao Ar Aw Ba Bn Bo Ch De) dE(An Ao Ap Ar Aw Bo Ch Fr) Or(tN tS tU tX wF wH wL) tR(Fw Hb Kd Ou Ow Pi) Bn(Ap aR Ba cB Ch) tS(Hb Kg Ld) wF(Fb Ki Pk) Ba(aH bZ) AawG ApbL KgtQ} Aa{Ef(sK sM sO uL uO uP uR uT uU uV uX uY vA vB vI vO vP vS vU vV vW yH yJ yK zG zI tM) Nx(Fp Hu Hw Ir Iv Jj Jp Jr Mb Mp Mv Nc Nd Ne Nh Nj Nl Of Oy Oz Pc Pd Pe Qe) Ng(Mt sC tV uN vC vS vU wC wD wE wF wG wH wI wL wP yD yK yL zH yE tL) Mt(Fp Hu Hw In Jr Ma Mj Mp Nd Nh Nj Ns Of Pa Pc Pd) eF(uR wG wH yD) Jh(vU wG yL) zG(Ba Iz Jd) Ap(sC vC) Bb(sC vC) On(Mb Me) iJ(wF wG) vU(Ch Jd) aMuR bEwB} Vq{qI(aH aU aV bC bE bM bP bQ bU bW bZ cJ cM cV cY dH dJ dL dN dR eF iA Jd Je Jf Jj Jp Ju Jv Lu Mg Mm Nb Ng Nt nW Nx Oe Og Oi oN Qd qW qX qY rB Rf Rh Ub) qH(aH bQ cE cO cV cY dF iA Jd Nn No oN qY Ul Uo Vs Tj) qG(cV cY dF iA Jd Jv oN) qZ(iA Jd oN) FnqU} In{Fp(Fr Ii Ij Jt Lh Li Ly Mu Mv Mw Ne Nj Nn Nt Of Oi Oy Oz Pc Pd Pf Qa) Nh(Jt Lh Li Mt Mz Nn No Nv Nw Nx Oh) Nl(eX Im Lh Mt Mz Nn Nv Nx Oh) Nw(Ly Mb Nc Ne Nj Nt Nx) Mt(Im Mb Nj Nt Nx Pc) Li(Nc Ne Nj Nt Nx) On(Nc Nd Ne Nj) Nt(Im Mz Nx) Jt(Nc Ne Tz) Nx(Mz Nc) MbOh YggW} tR{Pi(Ad Al aQ Aw Ba bE Bg Ch Cp Ct dA dB Dc Dk Ef Ez Iz Jd jB jF Jh jK Kl Mg Ng Of Oy pS qD Qh Ql Uc Uf Uk uR VO Vv wG yJ) pS(Ap Ar As Ba Bb Cs Cu Cw De Dg Fa Gl Hb Kk Kn Ko Kp Ph) cR(Al Dd) jG(Mg Vv) Aoal AplK ChaX KgcZ VoqB} dE{Bn(Ad An AR Aw aY Ba bF bM Bo bU Ch cK cN cO Cp Dl) cP(Ad An Ar Aw Ba Bo Ch Cp De Dg) aR(Cp Nx Oy Pc Pd Pf) De(cB cK cO Pb Pc) cK(Ad Cp Dl Im) Pc(Ar Fp Nx) Ad(Bg Of) Cp(Bg cO) aY(An Fp) ArOy NxPb} Jj{Nx(Im Iv Jt Lh Li Lj Ly Mb Mm Mt Ne Nh Nj Nl Nn No Nr Nu On Oy Oz Pc Pd Pf Pz Qa Qe) On(Fp Ly Mb Nd Nj Nl) Oh(Fp Mb Nh Nl Nt) FpMt NtPd NlLh} Mb{On(Fp Hw Ly Ma Ml Mt Mw My Na Nc Ng Nl Nq Ns Oh Oz Qb) Oh(Fp Jp Ly Ml Mm Mt Nl Nw Nx Pd) Mt(Fp Ml Nw Nx) Fp(Jp Mm) Ly(Jp Nw) DoNl MlNw} Fp{Nx(Il Ml Mm Mt Nc Nl Oh Oz Pc Qb) Mt(Js Ml Om On Oz Pc Qb) Qb(Jp Mm Nw Oh) MlNw} tS{Pi(Ad dA Ef jE Of Qh uR) Bb(Ha rW) Ef(cR wF) AduN AlcR BaaL MgjG LddB VoqB} dX{Pb(bN cQ dD eM Gl Ne Nh Tj) Oz(cM Ne Nh Nj Pe) Pc(Ne Nh)} wF{Mn(Ap Dg Hb Ij) Ng(cJ Jk) Ij(rR wB) Ri(Ad Uc) BbtM MgdJ ImrR KnqB OrcF} Bb{wK(al aL) iZ(pS sC) IvrW wLqY qUpS IKvH sCnW} Or{Ch(tV wC wD wK wP) eF(wH wL) NgwD IjpS} On{Qb(Nc Nh Nj Nl) Of(Nd Nj Nl) NdOy} Mg{jG(tN tO tQ tT tU tX) dJwL} eP{Pb(Bn cQ De Di Fr Nf) OzbN} Ap{Mn(tV wB wC) FwwB QupS} Ng{wD(Bg Ld) NdwL QdwH cHwP} Vo{qB(tT tU tX wH)} Nl{Qb(Li Nw) MlNw} Kp{Rx(gL oK) VjgW} Tj{ArOy IlpQv} Kg{dJwQ tQIK} Pc{DoNr TlgW} BncBdB GwNjIj MtNxPc NhQbLi YgPkgW UnfNjG Unconstrained panels with 2 analytes, where 1.0E-8 >= 'model p-value' > 0. Contains 52 panels of 196,694 total panels evaluated. : Ok(Et Fp Hr Hw Hx Ii Ik Il In Jj Ly Lz Ma Mb Mj Ml Nc Nd Ne Nf Ng Nh Nj Nk Nl Nx Of Oh Oz Pc Pd Pg Qb) Et(Fp Hw Ik In Ly Ma Mb Nc Nd Ne Nh Nj Nl Nq Nx Oz Pc Qb) IkJj Unconstrained panels with 2 analytes, where 1.0E-7 >= 'model p-value' > 1.0E-8. Contains 146 panels of 196,694 total panels evaluated. : Ok(aA Fr Hq Hu Ih Ij Im Io Ip Iq Ir It Iu Iv Jg Ji Jl Jn Jo Jp Jr Js Lh Li Lj Lu Lv Lw Lx Mc Md Me Mf Mg Mh Mi Mk Mm Mn Mp Mq Mr Ms Mt Mu Mv Mw Mx My Mz Na Nb Ni Nm Nn No Nq Ns Nt Nu Nv Nw Ny Oe Og Oi Om On Oy Pa Pb Pe Pf Po Pz Qa Qd Qe) Et(Hq Hr Hu Hx Ii Il Im Iq Iu Iv Jg Ji Jj Jn Jo Jr Js Li Lj Lu Mc Me Mf Ml Mp Ms Mt Mu Mv Mw Mx My Na Nf Ng Nk Nn No Nr Ns Nt Ny Oe Of Oh Om Oy Pa Pd Pf Pz Qa Qd) aN(Bn bU cC Cp dE Ji) Ik(Ji Jp Nk Nw Oh) Nk(Fp Nl) AdaC InJi Unconstrained panels with 2 analytes, where 1.0E-6 >= 'model p-value' > 1.0E-7. Contains 204 panels of 196,694 total panels evaluated. : Et(aA Fr Hv Ih Ij Io Ip Ir Is It Jh Jk Jl Jm Jp Jq Jt Lh Lv Lw Lx Lz Md Mg Mh Mi Mj Mk Mm Mn Mq Mr Mz Nb Ni Nm Nu Nv Nw Og Oi On Pb Pe Pg Po Qc Qe) Ji(dE Fp Hw Hx Jj Jq Js Li Ly Mb Ml Ms Mt My Nc Nd Ne Nh Nj Nk Nl Nq Ns Nt Nx Of Oh Oz Pc Pd Pf Qb) aN(aC Ad Ar Aw Ba bM cB Ch cK dB Dg Dl Fp Ik Jg Jt Lh Ly Mg Nd Nh Nm Nw Nx Ok Oy Pc Pd Pf Pj) Ik(AA Fp Fr Hw Im In Jg Lh Li Lj Ml Mm Mt Nc Nn No Nx On Oz Pa Pc Pd Pf Qb Qe) Jg(aH dE Fp In Jj Mb Mt Mu Mw My Nc Ng Nh Nl Nq Of Oz Pc Tj) Ok(Hv Is Jh Jk Jm Jq Jt Nr Qc) aC(Ao Aw Ba Bn Ch Cp Dg Dl) Nx(Aa Fp Jj Mt Nc Nh Nl) Fp(In Mm Mt Oh On) Pj(pS Qv Qy rZ Tj) dE(Ad Bn Cp De Dl) Mb(Mt Nw Oh On) Nk(Nc Nh) Nl(Nw On) AaMt NtUj Unconstrained panels with 2 analytes, where 1.0E-5 >= 'model p-value' > 1.0E-6. Contains 595 panels of 196,694 total panels evaluated. : Ik(Ar dE Hq Hr Hu Hv Hx Ih Ii Ij Il Io Iq Ir Is It Iu Iv Jh Jk Jl Jm Jn Jo Jq Jr Js Jt Lu Lv Lw Lx Ly Lz Ma Mb Mc Md Me Mf Mg Mh Mi Mj Mk Mn Mp Mq Mr Ms Mu Mv Mw Mx My Mz Na Nb Nd Ne Nf Ng Nh Ni Nj Nl Nm Nq Nr Ns Nt Nu Nv Ny Oe Of Og Oi Om Oy Pb Pe Pg Po Pz Qa Qc Qd) Ji(AA Fr Hq Hr Hu Hv Ih Ii Ij Il Im Io Ip Iq Ir Is It Iu Iv Jg Jh Jk Jl Jm Jn Jo Jp Jr Jt Lh Lj Lu Lv Lw Lx Lz Ma Me Md Me Mf Mg Mh Mi Mj Mk Mm Mn Mp Mq Mr Mu Mv Mw Mx Mz Na Nb Nf Ng Ni Nm Nn No Nr Ns Nt Nu Nv Ny Oe Of Og Oh Oi Om On Oy Pa Pb Pe Pg Pz Qa Qc Qd Qe Tj) aN(Aa aE Af Aj Ao Ap aR Ax bA Bb bC bF bH Bo bS bX cG cN Co cP cT Cx Db Dd De Dl Et Fr Gl Ih Ii Im In Is Jd Jh Jl Jp Jr Li Mb Mh Ml Mm Mp Mr Ms Mt Mv Mw Mz Nc Ne Nf Ng Nj Nk Nl Nn No Nr Nt Nv Of Og Oh Oi Om On Oz Pa Pb Pe Pg Pz Un Tj) Pj(Ar cE De Ed Fn Fw Hu In iP Jd Jg JO Js Ks Lv Ma Mp Nn Ns Of Oy Pf Pg Qb Qt Ra rB Rg Rh Ri rP TR Tz Ud Um Un Ur Uv vH Vo Vs vU wG zH zI) Jg(Aa aC Aj aR aY Bg bQ bZ cE cK Cu Fw Hw Hx iA Il Im Io Iq Iu Iv Jr Js Li Lj Ly Ma Me Ml Ms Nd Ne Nj Nk Ns Nt Nx Oh Oy Pa Pd Pf Qb) dE(aC aJ aM An AR AW aY Ba bF bM Bo cB Ch cK cN cP Dg Et Fp Fr Im Jp Jt Lh Mt Nd Nh Nl Nm Nv Nw Nx Oh Ok On Oy Pb Pc Pd Pe Pf) Fp(aA Fr Im Jj Jp Lh Ly Mb Mg Ml Mu Nc Ne Nh Nj Nl Nn Nt Nw Oe Of Oy Oz Pc Pd Pf Qb) Nx(aA Hw Il Im In Jp Li Lj Ly Mb Mm Ne Nj Nk Nn No Nt Nw Of Oh On Oz Pc Pd Pf) Mt(Hw Im In Jj Li Ly Nc Nd Nh Nj Nk Nl Nt Nw Oh Oz Pc Pd Pf Qb) Nw(Hw Hx In Ly Ml My Nc Nd Ne Nh Nj Nk Nt Oz Pc Pd Pf Qb) Li(Hw In Jj Ly Mb Nc Nd Ne Nh Nj Nk Nl Nt Oz Pc Qb) Nh(Aa In Jp Lh Mm Nn No Oh On Pc Pd Pf) Nl(Aa Fr Jp Lh Mm Nn No Nt Oh Pd Pf) On(Hw In Jj Ly Nc Nd Ne Nj Of Oz Qb) Bn(Ad aR Ba bU cB cK Cp dB Dl) aC(Aj An Ap Ar bE dB Dd De) Mb(Aa Fr Jp Lh Mm Nn No Nv) Aa(Et Me Nc Ok vO) Nt(In Jp Nk Oz Pc) Nj(Ar Jp Nk Nn Oh) Tj(Ad Jd Jt Ok) Vq{qI rP rR rT) Nd(Ad Ar Jp) dB(Ar cB Cp) Ng(wF wH) Jj(Lh Oh) AdOf CpcK DoEz FwJt LyJp NeNk IjwF VznA OhOz UtdU PbeP Unconstrained panels with 2 analytes, where 1.0E-4 >= 'model p-value' > 1.0E-5. Contains 1,819 panels of 196,694 total panels evaluated. : Pj(aC Ad Af aG aH al aI AJ Al aM An Ao AP aR As aV AW Ax aY BA Bb BC BG bI bL BN Bo bQ bV bX bZ cD Ch cI cK cM cN CO CP CQ Cs CT Cu Cv CW Cx dA DB Dc DD dE Dg DI DK Dl Dp dR EF Et Ez Fa Fb FP Fr Fy GL GP gW HA HB HC HF hG Hq HR Hv Hw Hx iA Ib IH Ii IJ Ik iI Im IO Ip Iq Ir Is It Iu Iv IZ Jc Jf Jh Ji Jj Jk Jl Jm Jn JP Jq Jr Jt Ju Jv Jy Kc Kd Ke Kf Kg Ki Kj Kk Kl Kn Ko Kp KQ KR kS Kx Ky Kz Ld Lh Li Lj Lu Lw Lx Ly Lz Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm No Nq Nr Nt Nu Nv NW Nx Ny Oa OE Og OH Oi OK Om ON Or Ou Ow Oz Pa Pb Pc Pd Pe Ph Pi Pk Po Pz Qa Qc Qd Qe Qg Qh QI Qm Qn QU Qw Qx qY Qz Rb Rc Rf Rj Rm rN rQ rR rS rT rU rV rW rX rY sC sK sM sO Ss St TN TO tQ tS TT tU TV tX Ua

Figure 12 Continued

Ub Uc Ue Uf UG Uh uI Uk UL uM uN UO UP Us UT Uu uW uX uY uZ vA vB vC vI vO VP VT Vu Vv wB wC wD wE wF wH wJ wK wL
wP wQ yD yJ yK zG yE tL xA Tk Wn Wm Ti tF) aN(aD aF aG aH aI aJ aK AL aM An aO aP aQ AS aU aV aW aX aY aZ bB Bc bE BG bI bJ
bL bN bO bP bQ bR bV bW bZ cA cD cE cF cH cI cJ cL cM cO CQ cR CS Ct CU CV cW cX cY cZ dA DC dD dF dG dH dJ DK dL dM dN
Ed Ef Em fP fR Fw Hq Hr Hu Hv Hw Hx Ic Ij Il Io Ip Iq Ir It Iu Iv Jj Jk Jm Jn Jo Jq Js Kc Kf Kl Ko Lj Lu Lv Lw Lx Lz Ma Mc Md Me Mf Mi
Mj Mk Mn Mq Mu Mx My Na Nb Ni Nq Ns Nu Ny Oe Po Qa Qb Qc Qd Qe Ra Rc Uk Wm) dE(Aa aD Af aH Aj aK Al AO AP aQ As aU aV
Ax bA BB BC Bg bH bI bJ bN bP bQ bR bU bV bX cC cF cG cI cL CO CQ Cs CT Cu Cv CW CX cY DB Dc DD dF dG DI dJ Dk dL dN Ef GI
Hq Hr Hu Hv Hw Hx Ih Ii Ij Il In Io Ip Iq Ir Is It Iu Iv Jd Jh Jk Jl Jm Jn Jq Jr Js Kc Kf Ko Kp Li Lj Lw Lx Ly Lz Ma Mb Mc Mf Mg Mh Mi MI
Mm Mp Mq Mv Mw Mx Mz Nb Nc Ne Ng Nj Nk Nn No Nr Ns Nt Nu Of Og Oi Om Oz Pa Pg Po Pz Qa Qe Tz Un Tk Tj) Jg(aA aF aG aI An
aO Ar BC bH bI bL bM Bn bX cI CO cP CQ dB Dc dF DG dH dI Dk Ed cF Fr gP hB Hq Hr Hu Hv Ih Ii IJ IP Ir Is It Jd Jh Jk Jl Jm Jn Jo Jp Jq Jt
Jy kR kS Ld Lh Lu Lv Lw Lx Lz Mc Md Mf Mg Mh Mi Mj Mk Mm Mn Mp Mq Mr Mv Mx Mz Na Nb Nf Ni Nm Nn No Nr Nu Nv NW Ny Oe
oF Og Oi Om ON Pb Pe Pg Po pS Pz Qa Qc Qd Qe Qh Qx Qz Ra Uu Vp Vs wF wH wL) Nx(Ar cK Fr Hq Hr Hu Hv Hx Ih Ii Ij Io Iq Ir Is It Iu
Iv Jh Jk Jl Jm Jn Jo Jq Jr Js Jt Lh Lu Lv Lw Lx Lz Ma Mc Md Me Mf Mg Mh Mi Mj Mk Ml Mn Mp Mq Mr Ms Mu Mv Mw Mx My Mz Na Nb
Nd Nf Ng Ni Nm Nq Nr Ns Nu Nv Ny Oe Og Oi Om Oy Pa Pb Pe Pg Po Pz Qa Qb Qc Qd Qe) Mt(bQ Fr Hq Hr Hu Hx Ih Ii Ij Il Iq Ir It Iu Iv JI
Jn Jp Jq Jr Js Jt Lh Lj Lu Lv Lw Lx Lz Ma Mc Md Me Mf Mg Mh Mi Mj Mk Ml Mm Mn Mp Mq Mr Ms Mu Mv Mw Mx My Mz Na Nb Nc Nf
Ng Ni Nm Nn No Nq Nr Ns Nu Nv Ny Oe Of Og Oi Om On Oy Pa Pb Pe Pg Po Pz Qa Qc Qe) Fp(Aa cK Hq Hr Hu Hw Hx Ih Ii Ij Il Iq Ir It Iu
Iv Jh JI Jn Jq Jr Js Jt Li Lu Lv Lw Lx Lz Ma Mc Md Me Mf Mh Mi Mj Mk Mn Mp Mq Mr Ms Mv Mw Mx My Mz Na Nb Nd Nf Ng Ni Nm No
Nq Nr Ns Nu Nv Ny Og Oi Om Pa Pb Pe Pg Pz Qa Qc Qd Qe Tj) Nw(Aa cK Fr Hq Hr Hu Ih Ii Ij Il Im Iq Ir Iv Jj Jn Jp Jr Js Li Lj Lu Lv Lz Ma
Mc Md Me Mf Mg Mh Mm Mp Mr Ms Mu Mv Mw Mx Na Nb Nf Ng Nn No Nq Ns Nu Nv Ny Oe Of Oh Oi Om On Oy Pa Pb Pe Pg Po Pz Tj)
aC(aE Af aH aJ Al aM aO aR As aW Ax aY bA Bb BC bF Bg bH bM bL bM Bo bQ bU bX cB cC cG cI cK cN CO cP Cq Cs CT Cu Cv CW Cx cZ
Db Dc DI Dk dN Et FR Ik Ji Jt Nm) Li(Aa Hq Hr Hu Hx II Im Iq Ir Iu Iv Jn Jp Jr Js Lh Lu Lv Lz Ma Mc Ml Mm Ms Mu Mw Mx My Mz Na Nf
Nn No Nq Ns Nu Oe Of Oh Om On Oy Pa Pd Pf Po Pz Qa Qc Qd Qe) Nh(aA Ar Fr Hw Il Im Ir Iv Jh Jj Jr Js Jt Lj Lx Ly Mb Mg Ml Mu Mv Mw
Mz Na Nj Nm Nr Nt Nu Nv Oe Of Oi Om Oy Oz Pa Pe Po Pz Qb Qe) Bn(aF aH Aj aK An aQ Ar As aU Aw aY bC bF bH bL bM Bo bQ bX bZ
cC cG Ch cN cO cP Cq cT CX Dg dH dI Dq Ik Nd Oy) Ad(Aa aH Aj An AR Bg bL bM bQ bU bZ cB Ch cK cO CP Cq Ct Cu DB Dc Fr Fw Ik
In Js Ma Mp Nj Pc Pg pS) Nt(AA Fr Hw Il Im Ir Js Lh Lj Ly Mb Ml Mm Mu Mw Mz Na Nc Ne Nj Nn No Ns Nv Of Oh Om On Oy Pa Pd Pf Pz
Qb) Nl(aA Ar Hw II Im In Ir Iv Jj Jt Lj Lx Ly Mb Mg Ml Mu Mv Mw Mz Nm Nu Nv Oe Of Om Oy Oz Pa Pc Pe Po Pz Qb Qe) On(Aa Fw Hx Ii
Il Im Iq Iv Jr Js Lj Ma Me Ml Mm Mp Ms Mu Mv Mw My Ng Nk Nn Nq Ns Oh Oy Pc Pd Pf wF Tj) Ar(bU cK cO Dl Ed Jd Ji Jt Ly Mg Mh Nc
Nm Nn Nr Og Oh Ok Oy Pc Pd Pf Pg Tj) Cp(aH aK aR Bg bH bM bQ bU bZ cB cO cP Cq Dg Dl dU cF Fw Ik Nd Pg Tj) Oh(Aa cK Ed Hw II
Im In Iv Jp Lh Ly Me Mm Nc Nd Ne Nk Oy Pc Pd Pf Tj) Aa(bM Fr Hu Ir Iv Jp Jr Lh Nd Ne Nj Pd Pe Pf Po Qa Qe Un uR) Lh(aA dU Fw Hw In
Ly Nc Nd Ne Nj Nk Of Oz Pc Pd Pf Qb Tj) Jd(bQ Cu Ed Fw Hq Js Mm Nk Nn Ns Of Pd Pf Pg Ra Tz Uk) cK(Aw Ba dB De Dg DI Et Ik Im Ji
Jt Nd Nm Ok Oy Pd Pf) Mb(aA Im Jl Jt Lj Ly Mu Mw Mz Nc No Oy Pd Pf Qa Qe) Jp(Hw Hx Il Im In Iv Lj Me Nc Ne Nk Ns Oz Pc Pd Pf)
Mm(Ed Hw Iv Lj Ly Nc Nd Ne Nj Nn Oz Pc Pd Pf Tj) dB(aJ An aR AW Ba bM Bo Ch De Dg DI Nd pS vS) Nn(Hw Im Iv Jj Ly Nc Nd Ne Nk
Oz Pc Pd Pf) Bb(fN pS qG qH qI qO qP qZ rV rW sC wF) Dl(aH An Aw Bo Ch cP Db Fw Ik Nd Nj Tj) Tj(Ba Dg Et Kf Nm Oy Pd Pc Pf Tz
Un) Nj(aA Ba De Dg dU Fr Im No Nv Pd Pf) Nc(Fr Im Jt No Nv Oy Oz Pc Pd Pf) Nd(Ao aR Ba De Dg dl Dk Fr No Nv) Ji(aH aR aY bL bQ bZ
cE cP Fw hR) Vq(qG qH qZ rN rO rQ rS rU rV rW) Tz(Fw hR hV jF jR Js IL qC qU) Jt(Cq Cu Ed iA In pS Rm Vs wF) Ok(aH bQ bZ cE Fw qZ
rQ rR rV) Nv(Hw In Jj Ne Nk Oz Pc Qb) Ik(An aR bQ Cx De dI Ip) Im(Fw Ly Nk Oz Pc Pd Pf) wF(Ap cW Dg Jh Mg Mv Uc) Ba(aH bQ bZ hB
kS oN) Ng(uW wB wG wJ wL wP) Pd(aA aR dU Jj Ly Ne) Et(aH cE Fw iA Wn) Fr(Ly Ne Oz Pc) Pf(Jj Ly Ne Nk) Fw(Kf Oy Un) Gn(Ch De
gW) No(Ed Ly Ne) Qa(In Nk Qb) Dg(An cO) Ij(wH wL) Jk(Fc Fi) nA(Yl Tl) ChgW LyaR MwdU NePc IvaA VznB QbQe JnlY KeeM OrpS
UfoT OzeP PbdX PitR aWfR cWvU

Unconstrained panels with 2 analytes, where 1.0E-3 >= 'model p-value' > 1.0E-4. Contains 4,562 panels of 196,694 total panels evaluated. :
Jd(Ad Af aH Aj Al An Ao Ap aR As Aw Ax aY Ba Bb Bc Bg bI Bn Bo bZ cE Ch cK CO Cp Cq Cs Ct Cv Cw Cx Db Dc Dd De Dg Dl Dk Dl
Dp dU Et Ez Fb Fn Fp Fr Fy Gl Ha Hr Hu Hv Hw Hx iA Ib Ic Id Ih Ii Ij Ik Il Im In Ir Is It Iv Iz Je Jf Jh Ji Jj Jk Jl Jm Jn Jo Jp Jq Jr Jt Ju Jv Jy Kc
Kf Kg Ki Kj Kl Kn Ko Kp Ks Kz Ld Lh Li Lj Lu Lv Lw Lx Ly Lz Ma Mb Mc Md Me Mf Mg Mh Mi Mj Mk Ml Mn Mp Mq Mr Ms Mt Mu Mv
Mw Mx My Mz Na Nb Nc Nd Ne Nf Ng Nh Ni Nj NI Nm No Nq Nr Nt Nu Nv Nw Nx Ny Oa Oe Og Oh Oi Ok Om On Ou Oy Oz Pa Pb Pc Pe
Ph Pi Pk Po pS Pz Qa Qb Qc Qd Qe QG QH qI QI Qm Qn Qt Qu Qv Qw Qx Qy QZ Rb Rc Rf Rg Rh Ri Rj Rm rN rO rP rQ rR rS rT rU rV rW
Tn Tr Tt Ua Ub Uc Ud Ue Uf Ug Uh UI UM Un UO Up Ur Us Ut Uu Uv uW uX VC vH Vo Vp Vs Vt VU Vv wF wG zH Tk Wn Wm) Jg(AD
aE Af aJ aK AL aM Ao AP aQ AS aU aV AW AX aZ BA BB bE bF bG bJ bN BO bP bR bS hU bV bW cA cB cC cD cF cG CH cJ cL cM cN
Cp cR CS CT cU CV CW CX cY cZ dA Db dC DD Dc Di dJ dK DL dM dN dR dU eC Ef eT Ex Ez Fb Fi FN fP Fy gL Ha hC hF hG hR Ib Ic Id
iH iO IZ Je Jf Kc Kf Kn KQ Ks Kz nY oE oH oK Ou pF Ph Pi qA qC qG qH qI qO qP qQ Qu Qv Qw Qy qZ Rf Rg Rh Rm rN rO rP rQ rR rS rT
rU rV rW sC sO TN TR Tv Tz Ua Ub Uc Ud Ue Uf UG Uh Uk UI UM Un UO Up Ur Us UT uU Uv uW uX vC vH Vo vP Vt VU Vv wB wC
wD wG wJ wK wP wQ yD yJ zA zH tM tF) Ad(AF aG aI aJ aK Al aM Ao Ap aQ As aU aV AW AX aY BA Bb BC bE bF bH bI bJ bN BO bP
bS bW bX cA cC cD cE cF cG cH cI cL cM cN Co cQ cR cS cT cU CV CW CX cY DD De Dg dH Dl DK Dl dR Ed eF FP GL gP gW hB Hq
Hr Hv Hx Hx iA Ic Ii iJ Il Io Ip Iq It Ji Jk Jo KS Ly Mb Mc Mh Mi Mj Ml Mr Mt Na Nc Ne Nf Ng Nh Nk NI Nn No Nq Nr Ns Nw Nx Ny Oe
Og Oh Ok Om oN Ou Oy Oz Pa Pb Pd Pe Pf Pz Qa Qb qC Qd qH qQ Qv Qy qZ Ra Rm rP rV sC Tn Tz Un Ur Uv vH Vo Vp wF zH Wn tF)
Cp(Aa aD aE AF aG AJ aL aM An Ao Ap aQ Ar AS aU aV AW AX aY aZ BA Bb bC bE bF bI bJ bL bN BO bP bR bS bW bX cA cC cD cE cF
cG CH cI cL cM cN Co cQ cR CS CT CU CV CW CX cY cZ Db Dc dH DI DK dL dR Ed eM Et FP Fr gL Gn gP gW Hq Hr Hw Hx iA
In Ir Ji Js Jt kS Ly Ma Mj Mm Mp Nc Nh Nj Nk Nl Nm Nn Nq Nr Ns Nx Ny Of Og Oh Ok Oy Oz Pa Pc Pd Pf wF) Ar(aF aH Aj aK An aR aU
aV Aw aY Ba bH bL bM bQ bZ cB cC Ch cP Db De Dg dl Ef Et Fw Gl gW Hq Hr Hv Hw Ic Ih Ii Ij Il Im In Io Ip Iq Ir Is It Iu Iv Iz Jp Js Kl Ko
Kz Lh Lu Lv Lw Lx Lz Ma Mb Mc Md Me Mf Mi Mj Mk Ml Mm Mn Mp Mq Mr Ms Mt Mu Mv Mw Mx My Mz Na Nb Ne Nf Ng Ni Nk No
Nq Ns Nt Nv Nw Ny Oe Of Oi Om On Ou Oz Pa Pb Pe Ph Pk Po pS Pz Qb Qy Rc Rg Tz Ue Ug Un) Pj(AA aD aE aF aK aL aO aQ aS aU aX
aZ bB bE bF bH bJ bM bO bP bR bS bU bW cA cB cC cF cG cH cJ cL cR cS cU cV cX cY cZ dC dF dG dH dJ dL dM dN dU eC eD eT fN hO
hP hV hW hX iB IC Id jD jE jF jG jH jI jK jL jM jQ jR jT jU jV jY IK IL IM IN IO nY oF pF qA qC qD qG qH qI qO qP qQ qT qV qW qX qZ
rA rC rO Sr uR uU uV vQ vS vV vW yH yL zA tM Th) Tz(aF Ap aR aY bC bI bQ cK cN cO Cq Cu Dg dI DI ED Et fN fY hA hP Hu HW hX
iB IC Ln jD jE jG jH JI jK jL jM jO JP jQ JT jU jV jY Kc Kl Ko Ld IK IM IN IO Mh Mj MI Mm Nf Nk Nm Nn No Nr Ok Oy Pd Pf Pg Ph Pi pS
qA qB qD qG qH qI qO qT qV qW qX QY qZ RA rB rC Rm rP rQ rR rS rT rU rV rW rZ sC Uf Um Un uO Ur Vp vU wF wG) dB(Af Aj aK Al
aM AO AP aQ As aU aV Ax aY bA Bb BC bF Bg bH bI bJ bR bU bX cC cG cl cN CO cP Cq Cs CT Cu Cv Cw Cx Db Dc DD DI dJ Dk Et Fp

Figure 12 Continued

Figure 12 Continued lW mE mF mU mY mZ nA nB nD nF nH nJ nK nL nN oO oP oQ) Nv(dU Fw Hx Il Iq Iv Js Lj Me Ml Ms Mu Mw My Na Nf No Nq Ns Ny Of Oy Pz) Oy(An aR bQ cO Cx De DI Fc Gl Iv Jj Kf Kl Ko Ld Lj Nk Ou Ph Ur Vc) An(aK aR aU aV Aw aY bH bU cB cC Ch cN cO cP De dl gW Mg Mt Nm) Fr(Hw Hx Il In Iq Ir Iv Jj Jr Lj Ma Me Ml My Nk Nq Ns Of Pz Qb) Ch(aH aK aR bH bQ bU cO cP Db DR eF Em eP Fw Gc kS Mp wH) Mt(aA aH aR bZ cE cO De dI Fw Hv Io Ip Is Jh Jk Jm Jo Qd) dU(Ij Iv Jf Jv Ke Ld Lx Mn Mx nD No Nr Pe Ph Qm Qn Rg) Ap(fP hB iA iJ iP kS Ma oK pS tR uT wB wH wL zH xA) Aw(aH aK aR Bg bH bL bQ bU bZ cB cN cO cP Cx Db dl) Fi(Fb gL Ha Hf Hp Hu Ib Ij Ir Kc Ko Kp Pe Tn Ut Yg) Fw(De Fy Kc Ke Kl Ko Kq Mg Nm No Pe Ph Qe rZ Uc Uf) aR(bH bU cB cC Db Kz Mg Mp Nb Nf Nm Of Og Pa Pe) bQ(bA bF cT Fy Ic Kc Ke Kf Kl Ko Kp Nm Ph Ss Uf) Jj(li Ir Iv Jl Jm Lj Mu No Nr Nu Po Qa Qd Qe) pS(Al Dc Fy Gl Ij Il Ke Kg Kq Ma Mg Ny Uf Ti) Nk(Hu Ir Iv Jl Lj Lx Mu No Nr Pe Ph Po Qe) Kc(aY dl Em Fc Gb Gd Gn Ru Uy Va Vc Vz Wf) Ko(aY bZ cE eM Ex Fn Gb Lv Ou Pg Ra Tn Tm) Nm(aH aY bZ cE cO cP De Di Fn Qy Ra Ur) In(Ir Iv Jl Kf Lj Lx Mz nK No Om Po Qe) wL(cJ cM Jh Kg Kn Mg Mv Om qU Uc Vo Vs) bU(aJ aM aW aY bF cG cI cN cP cT De) qU(bG dI Fn Ii iP Kg Kp Mz Vq vS Ti) Hw(Ir Iv Jl Lj Mu Mw No Po Qa Qe) wH(Jh Kg Mg Mv Mw Of Om Pz Vo Vs) Fc(Fb gL Hu Ib Jh Kp Mw Qw Qz) Af(Do Dq dV eM eP Gn gT Gw) Mz(eD hR hV Iv jE jY rB Vp) Lj(Hu Iv Mg Mu Mv Of Om Qb) Yl(Ib kK kN ml nB nR qX rA) Uf(cE fA iA iP Mp oN pl uT) De(aK bH cB cO cP Db Hr) Vz(Fb gL Hu Ib kK nR Qt) Kf(cE iA Js kS oN Qb Rm) Kl(aH cE Cu Js Mp Of Ra) Kp(aY Em Rx Wf Ye Tm Yf) Bo(Db Do Dq eM gC Gw) Hp(cQ Mh Pk Qv Ri Rm) Om(hR lY My nK qZ rZ) cB(Db Dq Dr Em Ex Gn) hV(lY Ms mU Mv nA qX) Nf(lY nK Ye Tm Xa) Iv(Ir Mu No Nu Pa) Rc(iP kS oN qO qP) Jk(Fd Ho Ps Rx Yf) Kg(tQ tR tS vH wB) cM(aF aW dX eP Jr) gL(Si Vc Vw Wd Yg) hR(jl jL Ms Mv Po) Dr(cP gW Hu qT) aA(Ir Jr Pe Po) cJ(vS vU wG yL) jD(Uw Vh Vj Wc) Al(tR vH vU) Em(cP gW Hu) No(Hu Hx Mu) Ma(tR tS tX) aY(Ic MP) bB(eP GT) nD(fB hC pH) nK(It Ml Na) Gd(cP Hu) Mv(jT rZ) Ii(qZ rB) Ij(wD zA) Wn(Dd Lu) Of(Iz Kj) Or(sC yJ) cH(sC vS) eQ(Hc Rb) fR(cO gW) nN(jR jT) iP(Fy Yg) qT(Vc Wc) rX(rQ rW) oQ(kl lY) BggN CtGn DbcP PoQb GhIb GcQv GwPk NuIr MsqZ IcQy HfYe WdiZ TmnA KePg LdtR VqiO aEvQ aHbF aVdV cRtX dIrQ fAfP

Constrained panels with 3 analytes, where 1.0E-10 >= 'model p-value' > 0. Contains 55 panels of 36,603,637 total panels evaluated. : Ok{Ik(Hr Hw Hx Ii Ij Il In Jj Jo Ma Ml Nf Ng Nk Of Qb) In(Fp Ma Mb Nc Ne Nh Nj Nl Nx) Nk(Fp Nc Ne Nh Nj Nl) MbMl} Et{Ik(In Jj Jo Ma Ng Nk Nq Of Qb) In(Fp Nc Nh Nl) Nk(Fp Nc Nl) Qb(Fp Nl) MaMb} Fp{Nk(Nc Nl)} Ik{MzIn JjOh}

Constrained panels with 3 analytes, where 1.0E-9 >= 'model p-value' > 1.0E-10. Contains 389 panels of 36,603,637 total panels evaluated. : Ok{Ma(Et Fp Hr Hw Hx Ii Il Jj Lz Mb Mj Mt Nc Nd Ne Nf Nh Nj Nk Nl Nx Of Oh Oz Pc Pd Pf) In(Et Hw Im Iv Ji Ly Lz Me Mt Mu Mz Nd Ng Nk Nn Nt Oe Of Oh Oz Pc Pd Pf) Mb(Et Hw Ii Jj Ly Lz Mh Mj Mt Na Nc Nf Ng Nk Nl Nx Of Oh Pg Qb) Ii(Et Fp Im Ji Ly Mt Mu Nc Nd Ne Nh Nj Nl Nx Oh Pc Pd) Fp(Hr Hw Hx Il Jj Lz Mj Ml Nf Of Pc Pe Pg Po Qb) Nc(Hr Hw Hx Il Jj Lz Mj Ml Nf Nx Of Pc Pg Qb) Nl(Hr Hw Hx Il Jj Lz Mj Ml Nf Ng Of Pc Qb) Ik(It Iu Mg Mj Mt Nb Nm Nq Oh Oy Pg Po) Nh(Hr Hw Hx Il Jj Mj Ml Of Pc Pg Qb) Of(Hx Ly Ml Nd Ne Nj Nk Nx Oz Pc) Hw(Jj Ly Ml Ne Nn Nx Oh) Nd(Jj Ml Nf Ng Nk Oh) Jj(Hx Ly Nj Nx Pc) Nx(Il Nf Nk) MlNj NkOh jGuN} Et{Mb(Fp In Jj Jo Lj Ly Ml Mt Na Nc Ng Nk Nl Nq Nx Of Oh Oz Pc Qb) Ik(Hw Ii Ij Il Iu Js Lj Mg Mt Mu Mw My Nc Nf Nl Ns Oh Oy Oz Pc) Fp(Hr Hw Hx Il Jj Jn Js Ma Ml Mt Mx Nc Nl Nq Oz Pc Qa Qe) Nl(Hw Il Jj Js Ma Ml Mt Ng Nq Of Oh Oz Pc Qa) Nc(Hw Jj Js Ma Mt Nq Nx Oz Pc Qb) In(Lj Ly Ma Ne Nj Nt Nx Oh Oz Pc) Ma(Jj Ne Nh Nx Oz Pc Qb) Qb(Lj Ne Nh Nx Oh Pc) Nk(Ne Nh Nj) Jj(Ly Nj Nx) Nq(Jg Pc) NxOf} Ik{Jj(Fp Jg Ji Jp Lh Li Lj Mm Nk Nn No Nv Nw Nx On Pd Qe) Nk(Fp Jp Nc Nl Oh) In(Ji Jp Nw Oh On) NgJp} Nk{Nl(Im Jg Ji Jp Li Mt Nn No Nv Nw Nx Oh On Pd Pf) Nc(Jg Ji Li Nx) FpMt} aN{dE(Ad Ba Bn cB Ch Cp De Dg Dl Fp Ji Nx Oy Pc Pd Pe Pf) PjzG} Pj{iP(uN vU vW zG tL) zI(An iO oF) iC(pS vU) zH(gW lK) QdvU bMsC fPuN jOpS} Fp{In(Jg Ji Mt Nx On)} BbfNqY OrUfpS Constrained panels with 3 analytes, where 1.0E-8 >= 'model p-value' > 1.0E-9. Contains 1,073 panels of 36,603,637 total panels evaluated. : Ok{Et(Hw Hx Ij Il Iq Jj Jo Js Lh Ly Mj Ml Mp Mt Nb Nc Nd Ne Nf Ng Nh Nj Nk Nl Nq Nx Oh Oy Oz Pc Pg Po Qb) Oh(Fp Hr Hx Ij Il Iq Iu Jj Js Ly Lz Me Mj Ml Mp Mt Nc Ne Nf Nh Nj Nl Nq Ny Of Oz Pc Pd Pe Pg Po Qb) Hx(Hr Hu Hw Ii Im In Ji Jo Ly Lz Mb Me Mj Ml Mt Mu Nd Nc Nf Ng Nj Nk Nm Nn Nx Oz Pc Pd Pf Qb) Mt(Fp Hw Ij Il Ji Js Lz Me Mj Ml Mp Mu Nb Nc Ng Nh Nk Nq Nx Om Oy Pc Pd Pe Pf Pg Po Qb) Qb(Im Ji Jj Jr Li Lj Ly Lz Ma Me Ml Mu Ne Ng Nj Nk Nn Nt Nx Of Oz Pc Pd Pf Qa Qe) Oz(Fp Hr Ii Il Ji Jj Js Ly Lz Me Mj Ml Nc Ne Nf Ng Nh Nk Nl Nn Nx Pg) Pd(Hr Hw Ij Il Iq Jj Js Lz Mj Ml Mp Nb Nc Ne Nf Ng Nk Nl Of Pe Pg Po) Pc(Hr Hw Il Iq Jo Ly Mb Me Mj Ml Mp Na Nd Ne Nf Ng Nj Nk Nx Pg Po) Nn(Hr Ii Il Iq Jj Ly Ma Mb Mj Ml Mp Nd Nf Nj Nk Nq Of Pg Po) Nx(Fp Hr Ij Iq Jo Js Ly Mj Ml Mp Ne Ng Nh Nj Nl Ny Pg Po) Nk(Hw Ii Il Iq Iv Ji Lj Ly Me Mj Ml Mp Ms Nf Ng Nt Pf) Fp(Ij Iq Ir It Iu Jn Js Lh Ly Mx Nb Nc Ng No Qa Qe) Mu(Hr Hw Ij Lh Ma Mj Mp Mw My Nb Nf Nq Of Oy Pg Po) Ne(Hr Il Ir Iu Jj Js Ly Lz Mj Ml Nf Ng Pe Pg Po) Ji(Hw Ij Il Jj Jq Js Lh Ma Ml Mp Nb Of Pg Po) Pf(Hr Ii Ij Il Ly Lz Mj Ml Mp Nf Ng Pe Pg Po) Ng(Hu Hw Jg Js Lu Ly Ma Me Ml Nc Nh Nj) Nj(aA Hr Hw Il Iu Jo Js Lz Mj Nf Pg) Jj(In Jg Lz Me Mj Ml Mp Na Nf Nq Of) Ly(Hr Il Lz Ma Me Mj Ml Nc Nf Pg) Nh(Ij Ir Iu Js Lz Nf Pe Po Qa) Jg(Ii In Ma Mw My Nq Of Oy Pg) Hw(Hr Ii Me Mj Nd Nf Nm Of) Ml(Hr Hu Il Iq Ma Me Nf) Nl(Ir Iu Js Pe Pg Po Qa) Nc(Ir Iu Js Nd Pe Po) Me(Ij Mp Nf Ny Pg) Lz(Ii Mp Of Pg) Mj(Il Nf Of) Hr(Mb Nd Nq) Hu(Ii In Ma) Ii(Oe On) In(Ir Pz) Of(Nf On) MaIq MbJo NdJp RiwB OmPg aNdE iArR jGpS} Et{Nq(Hu Hw In Jh Ji Jj Li Lj Lu Ly Me Mt Mu Nd Ne Nh Nj Nk Nn Nt Nx Of Oh Om Oz Pd Pf Qb) Mt(Hw In Jg Ji Jj Li Lu Ly Ma Mc Mu Ne Nh Nj Nk Nn Nw Nx Of Oh Om Oz Pc Pd Pf Qb) Of(Fp Hx Jg Ji Lj Ly Ma My Nc Nd Ne Nh Nj Nk Nn Ns Nt Oh Oz Pc Pd Pf Qb) Oh(Hw Hx Ii Il Iq Jj Js Ly Ma Mp My Nd Ne Nh Nj Nk Ns Ny Oz Pc) Nx(Fp Hw Ii Il Jo Js Ly Mp My Ne Ng Nh Nj Nk Nl Ns Ny Oz Pc) Qb(Hw Im Ir Iv Ji Jr Li Ly Nd Nj Nn Nt Oz Pd Pf Qa Qe) Ly(Fp Hw Jo Js Lj Ma Mc Nc Ne Ng Nh Nj Nk Oz Pc) Jj(Hw Hx Iv Lj Mp Nd Ne Nh Nn Nt Oz Pc Pd Pf) Ma(Hw Il Li Lj My Nd Nf Nj Nk Ns Nt Pd Pf) Pc(Hw Lj Mp Mu Mw My Na Nd Ne Nh Nj Ns Oy) In(Ir Iv Ji Jr Li Me Mz Na Nd Nk Pd Pf) Ne(Hw Il Iu Js Ml Ng Ns Oz Qa) Nh(Hw Il Js Ml My Ng Ns Oz Qa) Nj(Hw Hx Il Iu Jo Js Ng Oz) Fp(Ij Iu Mj My Ns Qd) Nk(Hw Jr Lj Nd Nt Oz) Nd(Hw Jo Lj Ng) Jg(Mu Mw My Ng) Nc(Il Ns Qa) Hw(Lj Nn Oz) Mp(Nr Oz) Js(Lj Oz) aA(Ik Mb) MyOm NlIu QaLj aNdE} Ik{Jj(Fr Hv Im Ir Jl Jm Jt Ml Mt Mz Nc Nj Nt Nu Oe Oy Pa Pc Pf Pz Qa Qc) Nk(Im Ji Li Lj Mm Mt Nh Nj Nn No Nw On Pa Pf Qa) In(Fp Im Jt Lh Li Lj Lx Mm Mt Nn No Nv Om Qa Qe) Jp(Hw Il Jk Ma Mt Mu Mv Mw My Nq Ns Of Qb) Ji(Hw Ii Jo Jq Ml My Ng Nq Of Qb) Nw(Il Ml Mt Mw My Ng Nq Ny Of Qb) On(Mw My Ng Of Oy) Jg(Mw My Ng Nq) Oh(Of Qb) MlMz aNdE} aN{dE(aJ Ao Ar Aw bF bM Bo bU cC cG cK cN cP cT Hu Ih Ii Im Jg Jh Jp Jr Jt Lh Mb Mg Mm Mt Mw Mz Nc Nd Ne Nh Nj Nl Nm Nn No Nr Nv Nw Oh On Oz Pb) Cp(aC bH bM Bn bQ bU cB cC cO dB Dl) aC(Ad Ao Aw Ba Bn cC Ch Dg Dl) Ji(bQ bX cK Js Mp Pg) Bn(bU cB Ch dB Dl) Ad(bM bU cB) Dl(bU cB dB) Ch(bH dB) FpaE JgbQ PjtL cBdB} Nk{Nl(Fr Ir Iv Jl Jr Jt Lh Lj Mm Mu Mv Mw Mz Nj Nt Oe Of Om Oy Oz Pa Pc Pe Pg Po Qa Qe) Nc(Im Jp Mt Nn Nt Nv Nw Oh On Pd Pf) Fp(Jg Ji Jp Mm Ne Nh Nj Nx Oh On) Nj(Jp Mt Oh On) Nh(Ji Oh) NeJi} In{Fp(Im Jp Mg Mm Mz Nc Nh Nl Nv Nw Oe Oh Om) Nl(Jg Ji Jt Li Nw On) Ji(Li Nc Ne Nh Nt) On(Mb Nh) MzNj} Aa{Ng(sO uG uI uM uP uR uT uV uZ vB vO vT zG tM) Jh(uP uR vO zG) Me(Mt Nx) Of(tM tL) MbMt bEvV} Pj{pS(aX bP qU) rZ(Fw iP Js) Qv(Fw Tj) iC(qI rT) jO(rS sC) iPuZ} aC{dE(Ad Ba Bn Cp De Dl) Ad(aL Bn bQ cW) BabQ}

Figure 12 Continued

Jg{My(Fp Mb Nx Pc) Nq(Fp Nx Pc) Jj(Fp Nx)} Fp{Ji(Jj Ml Qb) QbOn JjNx} Jj{Nx(Nc Nt Oh)} dE{Bn(cB cP) DlcP} Bb{dBvC fNsC} Mb{MlJi OfOn} Ng{MnwH NdwF} ApqUpS IidJwF JpcZtR

Constrained panels with 3 analytes, where 1.0E-7 >= 'model p-value' > 1.0E-8. Contains 2,182 panels of 36,603,637 total panels evaluated. : aN{cK(Ad Aw Ba Bn bU cB cC Ch Cp Dg Dl Fp Ik Im Jg Lh Ly Mm Nh Nm Nw Nx Ok Oy Pd Pf) Jg(aH aY Bg bI bX bZ cE Cu dI Ik Io Js Ly Ma Mp Nd Nh Nn Ns Nx Of Pc Pg Tj) Ji(aH bC bZ cB cE Ch cZ dB In Jq Ly Ma Ml Nd Nf Nn Ny Oy Pc Qb Tj) Nx(aE bQ bX cN cO cQ dB dI Ik Ly Ml Mp Nf Nh Oh Oy Pc Pd Pf Pg) Ar(aC Ad aE bM Bn bU cB cC Ch dB Dl Ly Nc Nd Nh Nj Oy Pc) bM(aE Ao Aw Ba bF Bn bP bU cB cC Ch cT dB De Dg Dl Tj) cC(Ad aE Ao Aw Ba bF Bn bP cB cG Ch cT De Dg Dl Fp) dB(aC Ad Ao Aw Ba bF Bo bU cT De Dg Fp Ik Nh Pc Pd) Bn(Ad aE aF aR Aw Ba bC bH bX cO Dg dI Fp) Pd(bQ cO cQ Ly Ma Mp Nd Nh Nn Nr Oh Pg Tj) bU(aC aE Ao Aw Ba bF cB cG Ch cN cT De Dg) Fp(Ao bC bH bX cB Ch cO dI Ly Mg Nh Tj) Ad(Bg bH bL bQ bX Ch cO cT cW Fr Of) Cp(aE Bg bS bX bZ Cq Ly Pc Pg) cB(Aa aC Ao Aw Ba Ch Db De Dg) Tj(Jt Lh Nw Ok On Oy Pj Tz) bQ(Ba bF Dg Ik Lh Nh Nw Ok) Dl(Aw bH bX Ch cP cT cW) Ly(Ba Ch Ik Nw Ok Pc Pf) aC(Aj Ap bE Co Dd DE) Nd(Ao Lh Mm Nw Ok Oy) Pj(Qv rZ Tz uZ wG wL) Dg(bH bZ Ch cO Fr) Ik(dI Mm Nm Nw Pc) Pg(Jt Lh Nw Ok Pe) dE(bA Gl Ns Nt Po) Ba(bH bZ cO dI) Nh(aE Nm Oy Pc) Ch(Bg bX Db) Lh(Js Mp Nn) Aa(Aw De) Jt(Js Qb) Ok(cE rV) Pc(De Nw) AwbH NmMa MgMp TzIc} Pj{tR(aI aK An aQ aU bE Ch cM cR cT cY Fp Fw Gl Jd jE JF Jj Jk jQ Jr Kk lK Mr Mx Ng pS rW sC Up Vo yK Wm) rZ(An aX bP bZ cH cT Cu hB iC It jP Kr Ks Me Mm Mp Oe Pc pS Pz Qa Qd Qe Ug Uo) Qv(Bn bQ cE Ch Cu De Ed Fn Hu iP Jd Js Ma Ml Ns Og Oy Pg Pk Qy Rh Tz Vs) pS(An aV bM dA dB dI gL Gp hO jE jH kR Ky lL Mp Nc Or Qh Qz Ub) tS(An aQ bE Ch dA Ef Jd jE Jf Jk lK Mx sC Ss Up Vo) wG(aS cM dJ dL hB iA iP Kk Mn Pk qB qU Ri vT vW xA) tX(An bE cM cR cT dA jE Jr Kk lK Mx rW Up Vo yK) tN(An Ba Ch Cp cR Ct dA Ef Ik Jd Ng Of Vo) Tj(Ar De Fa Fn Hu Jd Jg Oh Oy Pf Qy Tz) iP(Ba Bo Ch hR jD jO Kr lL qU rB uW wL) tQ(An aW Ch cR dA Ef Jd Jk jO Ng Of) jO(Ly Me qH rP rQ rV uN vO vU yJ) uN(iA rB uT wJ wP) dA(wE wH wK wQ) tU(An Ch Jd Vo) Tz(Fw In Js) iC(rQ uW xA) tT(Ch Jd Ri) rB(qA qD vC) zH(An bE jE) wP(kQ lK) tO(cR Vo) jD(vH wL) AnuT ApJd CuJg MpyJ JrJs bMvU bPvH jErP jGrV qXjP sCvA} Jg{Nq(Hw Im In Iv Ji Jj Li Ly Mb Me Mt Mw My Nc Nd Ne Ng Nh Nj Nk Nl Nn Nt Nw Of Oh Om Oz Pd Pf Qb) Mw(Fp Hw In Ji Jj Ly Ma Mb Me Mt Mz Nc Nd Ne Ng Nh Nj Nk Nl Nn Nw Nx Of Oh Om On Oz Pc Pd Pf) My(Hw Hx In Ji Jj Ly Ma Me Mt Nc Nd Ne Ng Nh Nj Nk Nl Nn Nw Of Oh Om Oz Pd Pf Qb) Ng(Fp In Ly Ma Mb Mt Mu Nc Nd Ne Nh Nj Nk Nl Nx Oh Oz Pc Pd) dE(aG aH Aj aR aY Bg bI bQ cE cK Ma Mp Nd Nx Of Pb Pc) Jj(Ji Ly Ma Mb Nc Nd Ne Nh Nj Nl Nt Oh Oz Pc Pd) Mt(Fp Ik Ji Mb Mz Nc Ne Nh Nl Nx Oh Ok Pd) In(Ik Ji Lj Mu Mz Nc Ne Nh Nj Nx Pc Tz) Of(aH Fp Ik Ly Nc Nh Nk Nl Nx Oh Oz Pc) Mu(Fp Ik Ji Mb Nh Nl Nx Ok Pc) Fp(Hw Js Ml Oz Pc Qb) Ok(Ij Il Lh Mp Nb Ny) Nk(Ik Ne Nh Nj Oz) Pc(aH cE Nc Nl Tj) bQ(Ar Ik Nd Nx Tj) Tz(Cu Fw Js Tj) Oy(Et Ik Nl Nx) aH(Ma Nd Nn Ns) aY(bZ Ma Mp) cE(Nd Nn Nx) Aa(Ma Me) Bg(Nd Tj) Et(Io Mv) Pi(tR wG) MbOh NlQb} Ji{Jj(Hw Hx Im Jq Li Ly Mb Ml Ms Mt Nc Nd Ne Nh Nj Nk Nl Nt Nx Oh Oy Oz Pc Pd Pf Qb) Jq(Et Fp Hw Im In Ly Ma Mb Ml Mt My Nc Ne Nh Nj Nk Nl Nx Oh Oz Pc Pd Pf Qb) Fp(Hr Hw Hx Ii Il Jn Js Mb Ms Mt Mw Mx My Nc Nh Nl Nq Ns Ny Oz Pc Qa) In(Hw Im Ir Iv Lj Ly Mb Ms Mt Mz Nd Nj Nx Oe Of Oh Oy Oz Pc Pd Pf Qa) Qb(Hw Im Li Lj Mb Ml Ms Mt Nc Ne Nh Nj Nl Nt Oh Oz Pc Pd Pf Qa Qc) Hw(Im Li Ly Mb Ml Nc Ne Nh Nj Nk Nl Oh Oz Pc Pd Pf) Nk(Im Lj Mb Ms Mt Nd Nj Nt Oz Pd Pf) Ik(aA Iu Js Ma Ms Mt Mw Nf Ns Oh Oz) Et(Ii Ml Mp Ms Mu Mw My Ns Ny) Mb(Li Ly Mt Nc Oh Oz Pd Pf) Ml(Ms Nc Ne Nh Nj Nl Oz Pf) dE(aR aY cE cK cP Mp Pb Pc) Nl(Js Ms Oh Oz Pc Pd Pf) Ok(Iq Jo My Nq Ny Oy) Nc(Js Oz Pc Pd Pf) Oz(Im Ms Nh Oh) Pf(Ma Ms Mt Of) Nh(Js Pc) MsOh MtOm MyOf} Ik{In(aA Fr Hv Ih Ir Is Jl Jq Mi Mj Mr Mw Na Nc Nh Nk Nl Nr Nt Nx Oe Pa Pc Pd Pe Pf Po Pz Qb Qc Qd) No(aA Hw Ma Ml Mm Mt Nc Ng Nl Nq Ns Nx Of Oh Oz Pc Pd Qb) Oh(aA Fp Hw Il Iu Jp Mb Ml Mm Mt Ng Ns Nw Oz Pa Pc Pd) On(Fp Hw Ii Ij Il Jk Ma Mb Ms Mt Mu Nb Nq Ns Oz Pg Qb) Mm(aA Fp Hw Il Jo Lj Ma Mt Ng Nq Nx Of Oz Pc Qb) Nk(aA Hv Il Ir Jl Lh Ne Ng Nt Nv Nx Of Oz Pd Qe) Nw(Hw Ii Iu Js Ma Ms Mu Nc Nf Ns Oy Oz Pc) Mt(AA Fp Mz Ng Nn Of Om Pc Qb) Nn(Fp Hw Ml Ng Ns Of Oz Qb) Jp(Aa Fp Iu Js Lj Ml Oy Oz) Qb(Fp Im Li Lj Pa Qa Qe) aA(Fp Ng Nx Oz Pa Pc Pd) Li(Hw Nf Ng Nq Of Pc) Fp(Ml Nx Pc) Ng(Fr Lh) Nx(Il Of) Pi(tR tS) LxPg MyOm LhOf aRdE} Nk{Nc(Fr Hu Ir Iv Jl Jr Jt Lh Lj Lx Mb Mg Mm Mu Mv Mw Mz Nh Nj No Oe Of Oy Oz Pa Pc Pe Pg Po Pz Qa Qd Qe) Fp(Im In Ir Iv Jj Ly Mb Ml Mu Mv Nn Nt Nv Nw Oe Oy Oz Pc Pd Pf) Ne(Im Jp Li Mt Nn No Nt Nv Nw Nx Oh On Pf) Nh(Im Jp Li Mt Nn No Nt Nv Nw Nx On Pd Pf) Nj(Fr Im Li Nn Nt Nv Nw Nx Pf Qa) Et(Il Iv Me Mp My Pf) Mb(Jp Li Mt Nw Oh On) Nl(aA Jj Pz Qd) Nx(Jj Mt) NmOk} aC{Cp(Ad aH aM aR Bg bH bI bL Bn bQ bU bZ cO Cq dB Dg Dl) Dl(aH AR Aw bE bL Bn Bo cB Ch cN cP cW dB De Di) Ad(aH aI AR bE bL cB Ch cN cO Cq Cu cZ dB) Dg(aH aR bL Bn bQ Ch cO dB dE) dB(Ao Ar Aw Ba Bn Bo Ch De) Or(tN tS tU tX wF wH wL) dE(An Ao Ap Ar Aw Bo Ch) tR(Fw Hb Kd Ou Ow Pi) Bn(Ap aR Ba cB Ch) tS(Hb Kg Ld) wF(Fb Ki Pk) Ba(aH bZ) AawG ApbL KgtQ} Et{aA(Fp Iv Ly Ma Mt Nd Nj Nq Nx Oz Pc Pd) Js(Iv Jn Jr Li Mt Ns Nt Pd Pf) Pg(Lx Mi Mk Mr Nr On Pa Pe) Mp(Mr Mt Mu Nn On Pd Pf) Ng(Hu Mu Nn Nt Oh Pd Pf) Ii(Mk Mr Mt Nn Nr On Pa) Lj(Hx Il Iq Jn Jr Ml Ny) Nt(Il Jo Ml Ns) Me(Ml My Nf Oh) Hx(Il Mr Nr Pb) Ny(Ir Li Nn Om) Mu(Mw My Oy) Nb(Mr Nr On) Jr(Il Ml Nf) Mw(Of Om) Li(Il Of) PoLx GpWn NnIq MrNf MyPf IuOh OnOy cEdE} Aa{Ef(sK sM sO uL uO uP uR uT uU uV uX uY vA vB vI vO vP vS vU vV vW yH yJ yK zG zI tM) Ng(Mt tV uN vC vS wC wD wE wF wG wH wJ wL wP yD yL zH yE tL) Mt(Fp Hu Hw In Jr Ma Mj Mp Nd Nh Nj Ns Of Pa Pc Pd) Nx(Hu Ir Iv Jr Ne Of Qe) eF(uR wG wH yD) Jh(vU wG yL) zG(Ba Iz Jd) Ap(sC vC) Bb(sC vC) iJ(wF wG) vU(Ch Jd) MeOn OkeP aMuR bEwB} Ok{Nn(Ij Js Lh Lz Mt Nb Ng Ny Oh Oy Pe) jG(qZ rN rO rP rR rS rV sC yJ) Ng(Hu Jh Jp Js Lu Me Pf) Mt(Hu Iq Ir Iu Lh Lu) Me(Iq Jo Js Nb Po) iA(rP rQ rW sC zI) Mu(Ir Js Ny Oh) Hu(Ij Nb Oy Pg) Tj(bQ cE Tz) Nm(Ly Nd Pd) No(aA Im) Ns(Iu Jo) Nt(Js Pg) Lu(Mw My) Ir(Im Qb) Jh(My Oy) Pf(Iq Js) cJ(rV wH) dX(Bo Oz) PoLi MlIo NbOm HxaA IuPz IvQb} Vq{qI(aH aU aV bC bE bM bP bQ bU bW bZ cJ cM cV cY dH dJ dL dN dR eF iA Jd Je Jf Jj Jp Ju Jv Lu Mg Mm Nb Ng Nt nW Nx Oe Og Oi oN Qd qW qX qY rB Rf Rh Ub) qH(aH bQ cE cO cV cY dF iA Jd Nn No oN qY Ul Uo Vs Tj) qG(cV cY dF iA Jd Jv oN) qZ(iA Jd oN) FnqU} In{Fp(Fr Ii Ij Jt Lh Li Ly Mu Mv Mw Ne Nj Nn Nt Of Oi Oy Oz Pc Pd Pf Qa) Nh(Jt Lh Li Mt Mz Nn No Nv Nw Nx Oh) Nl(eX Im Lh Mt Mz Nn Nv Nx Oh) Nw(Ly Mb Nc Ne Nj Nt Nx) Mt(Im Mb Nj Nt Nx Pc) Li(Nc Ne Nj Nt Nx) On(Nc Nd Ne Nj) Nt(Im Mz Nx) Jt(Nc Ne Tz) Nx(Mz Nc) MbOh YggW} tR{Pi(Ad Al aQ Aw Ba bE Bg Ch Cp Ct dA dB Dc Dk Ef Ez Iz Jd jE jF Jh jK Kl Mg Ng Of Oy pS qD Qh Ql Uc Uf Uk uR VO Vv wG yJ) pS(Ap Ar As Ba Bb Cs Cu Cw De Dg Fa Gl Hb Kk Kn Ko Kp Ph) cR(Al Dd) AoaI AplK ChaX KgcZ VoqB VvjG} dE{Bn(Ad An AR Aw aY Ba bM Bo Ch cK cN cO Cp Dl) cP(Ad An Ar Aw Ba Bo Ch Cp De Dg) aR(Cp Nx Oy Pc Pd Pf) De(cB cK cO Pb Pc) cK(Ad Cp Dl Im) Pc(Ar Fp Nx) Ad(Bg Of) Cp(Bg cO) aY(An Fp) ArOy NxPb} Jj{Nx(Im Iv Jt Lh Li Lj Ly Mb Mm Mt Ne Nh Nj Nl Nn No Nr Nu On Oy Oz Pc Pd Pf Pz Qa Qe) On(Fp Ly Mb Nd Nj Nl) Oh(Fp Mb Nh Nl Nt) FpMt NtPd NlLh} Mb{On(Fp Hw Ly Ma Ml Mt Mw My Na Nc Ng Nl Nq Ns Oh Oz Qb) Oh(Fp Jp Ly Ml Mm Mt Nl Nw Nx Pd) Mt(Fp Ml Nw Nx) Fp(Jp Mm) Ly(Jp Nw) DoNl MlNw} Fp{Nx(Ml Mm Mt Nc Nl Oh Oz Pc Qb) Mt(Js Ml Om On Oz Pc Qb) Qb(Jp Mm Nw Oh) MlNw} tS{Pi(Ad dA Ef jE Of Qh uR) Bb(Ha rW) Ef(cR wF) AduN AlcR BaaL LddB VoqB} dX{Pb(bN cQ dD eM Gl Ne Nh Tj) Oz(eM Ne Nh Nj Pe) Pc(Ne Nh)} wF{Mn(Ap Dg Hb Ij) Ng(cJ Jk) Ij(rR wB) Ri(Ad Uc) BbtM MgdJ ImrR KnqB OreF} Bb{wK(aI aL) iZ(pS sC) IvrW wLqY qUpS lKvH sCnW} Or{Ch(tV wC wD wK wP) eF(wH wL) NgwD IjpS} On{Qb(Nc Nh Nj Nl) Of(Nd Nj Nl) NdOy} eP{Pb(Bn cQ De Di Fr Nf) OzbN} Ap{Mn(tV

Figure 12 Continued wB wC) FwwB QupS} Mg{jG(tO tT tU tX) dJwL} Ng{wD(Bg Ld) NdwL QdwH cHwP} Vo{qB(tT tU tX wH)} NI{Qb(Li Nw) MINw}
Kp{Rx(gL oK) VjgW} Tj{ArOy HpQv} Kg{dJwQ tQIK} BncBdB DoNrPe GwNjIj M

Figure 12 Continued

Nq Ny Oz Pc Pd Qb) Nn(Jj Ly Ml Mt Nc Nh Nk Nl Pd) Aa(Fr Ir Nc Nv Pd Pz Qa Qe) Mt(Hw Jj Lj No Pc Pd Qb) On(Il Lj Mu Nb Nh Oy Pd)
Nk(Jl Lh Nh Nv Qa) Ml(Fr Lh Mz Nv) Fr(Ly Nl) Jj(Lh Nv) aA(Lh Pd) LyIm QbNv} Nk{Nh(aA Fr Hw Ir Iv Jj Jl Jr Jt Lh Lj Mm Mu Mw Nj Oe
Of Oy Oz Pa Pc Pe Po Qa Qe) Nj(aA Ad Ar Ir Jl Jr Jt Lh Lj Lx Mm Mu Mv Mw Ne No Oy Pa Pd Pe Po Qe) Ne(Fr Iv Jl Jr Jt Lh Lj Mm Mu Mw
Oe Oy Oz Pa Pc Pd Pe Po Qa Qe) Mt(Hw Im Ir Iv Jj Jr Li Lj Ly Ms Nd Nn Nt Nw Oh Oz Pc Pd Pf) Nt(Im Jj Jp Li Lj Nn Nw Oh Oz Pa Pc Pd
Pf) Li(Hw Jj Ly Nd Oz Pc Pd) Nd(Jp Nv Nw Oh On) Nc(Aa Ar Hw Qc) Oz(Im Nw Oh On) Ly(Jp Nw) Nl(Aa Ar) TjJt OfOn} Bb{sC(cH Fa Fb
Fw Ha Hq hR Hu hV iJ Il Iz IL Mh Mk Mp Mr Nb Nd Ni Nq Or Ow Oy Pc PF Pi Pk qA qB QU Qw qY To Ua Ue ul) pS(eD Fy Ha hR Ic Il jR
jY IL Mr Nb Nd Ni nW Or Ou Ow Qu Tj Ti Th) rW(Fb gP gW iA Ic Io jE Md Mr Nb Nq Nt Pa Pi Pk qY rB Tz) gW(rP tS tV tX yD zA) rP(iA
Pi qY Tz wF) vH(Fy jE jQ Mr Nd) vP(cH iZ Mr Ti Th) iZ(sO uY vU) wF(Ri rR yE) qY(eT qB vU) Nb(uG vC) tM(eD qD) rN(Ml Mr) TiyK
HawH NnuU dRyD fNjG rBvC IKzA nWvU} On{Of(Aa Hx Ly Mp Mt Mw My Nc Ne Nh Nq Ns Nt Oz Pc Pd Pf Qb) Nl(Hw Hx fl Js Ly Mt
My Ng Nq Ns Oh Oy Oz Pc Pd Pf Qa) Jj(Hw Hx Mp Mt My Nc Ne Nh Nq Ns Nt Oh Oz Pc Pd Pf Qb) Nd(Hw Mt Mu Mw My Nb Nc Ng Nq Ns
Oh Oz Pc Pd Pg Qb) Nj(Hw Ii Il Mt My Ng Nq Ns Oh Oy Oz Pc Pd Pf) Nh(Hw Il Js Mt My Nq Ns Oy Oz Pc Pd) Qb(Li Lj Ne Nt Oz Pd Qe)
Nc(Hw Mt Ns Oz Pc Pd) Tj(Ar bQ Nq Pc) Hw(Ly Ne Ns) Ar(Fw Pg) Oz(Ly Mt) eP(Ld Ph) FiQv PbdX} Nw{Nh(Hw Il Jj Js Ly Ml Mt Mw My
Nq Oh Oz Pc Pd Pf Qb) Nl(Hw Il Jj Jn Js Ly Ml Mt My Nq Ns Oh Oz Pc Pd Pf) Nc(Hw Il Jj Js Ly Ml Mt My Nd Oz Pc Pd Pf Qb) Nj(Jj Js Ly Ml
Mt My Oh Oz Pc Pd Pf Qb) Mt(Ly Nd Ne Of Om Oz Pc Pd Qb) Nd(Jj Ml My Oh Oz Pc Pd Pf) Qb(Im Li Ne Nt Oz Qa Qe) Ly(Im Jj Ml My Oz
Pc) Oz(Im Ml My Ne Oh) Tj(Cp Jd Tz) Pc(Mw My Ne) Jj(Nt Pd) AaMe MlNe MyOf} Jj{Nt(Im Ir Jm Jp Lh Li Ly Ml Mm Mt Nc Nh Nj Nl Nn
Nv Oy Oz Pa Pc Pf) Mt(Im Lh Li Ly Nc Nd Nh Nj Nl Nn Oh Oz Pc Pd) Oh(Im Iv Lh Li Ly Nc Nd Ne Nj Oy Oz Pc Pd) Li(Hx Ly Nc Nd Ne Nh
Nj Nl Oz Pc Pd) Lh(Ly Nc Nd Ne Nh Nj Oz Pc Pd) Nn(Ly Nc Nd Nh Nj Nl Pd) Nl(Fr Jt Nc Nv Pd Pf) Ly(Im Jp Nv Qe) Nh(No Nv Pd) Nj(Jp
Nv Pd) NcPd NdNv} Tj{Ok(aH An Ar bM bZ cK cO Cp dl Fa Fn Gp Jd Jt Ma Nh Oh Or Ou Oy Pa Pc Pd Pf Pg Qv Rh) Jt(Ar bQ Fn Jd Js Ma
Mp Nh Oe Of Oh Oy Pa Pb Pc Pf Qb Qv Qy Ra Rm Tz Ur) Jd(Ad Ar Ax Cs Dl Mm Nm No Oh Oy Pa Pd Pe Pf Tz Uk) Tz(Ad Ar Et Kc Kf Mm
Nm Oy Pf) Ad(Ar Fa Of Oy Pa Pc Qv) Ar(Dl Pd Pf) Kf(bQ cE dl) BabQ FaOy MwnR HpRm} Aa{Me(Fr Ir Jm Jp Li Mm Nm Nv Oh Oy Pd Pz
Qa Qe) Ch(tV wB wC wD wE wF wG wH wJ wK wL wP wQ) wG(Ad Aw Cp Ef fP Iz Jd Tr) bE(uU uX vO vP vU yE) Ng(tN tO tS tU tX)
Nh(Iv Jr Nm Oy Pd) Jh(tN uG uN vW wL) Nd(Fr Jp Oh Qe) Vs(wD wF wH wL) eF(uV vC wF yK) Ef(wE wH yL) Mt(Io Ir Iv) Nc(Ir Iv Pd)
Pd(Jr Nl) wE(Aw Vo) qH(kQ rX) NnaY MgtX IluN OfuM OkuR UutV vCvO} Nl{Oh(Hw Il Iu Jp Js Li Ly Mm Mt Oz Pc Pd Pf Qb) Nn(Hw Js
Ly Ml Mt Oz Pc Pd Pf Qb) Mt(Hw Js Ml Om Oz Pc Pd Pf Qb) Li(Hw Il Js Ml Oz Pc Pd Qa) Qb(Fr Im Jp Lh Nv Qa Qe) Jp(Hw Ly Oz Pc Pd)
Pd(aA Mm No) Pc(Fr No) ArbQ NreX HwLh PbdX eQfP} Bn{cB(Ad aH An aR bH bL bQ cK cO CP Dl) Cp(aH aR bH bQ bU bZ cK cO Cq
dB) Ad(aH Aj aR bQ bZ cK cO Cq) Dl(An Ar Bo Ch cK cP Cq dB) dB(An AR Bo Ch cK cO) aR(bH bU Ch cK cO) Ba(aH bQ bZ cO) Ar(cK
cO) AnbU ChbH JsJt bFbQ} Ok{iA(pS sK sO uO vB wF wG yJ) rR(cH Ed Fw Nu Or rV Vp tF) dX(Ex Kz Ld Or Ou Pb) jG(tR tS uO uT vU
wF) rQ(bP dl rB rX tF) Fw(Ar Im Oy Tz) cJ(rU uM wL) pS(jY Or Ql) cE(cK Nd) eP(Ex Or) qB(rB sC) wH(cM Kk) rV(aH iP) ArPg NsaA
RiwF aVrP fYqU tFsO} Nh{Oh(Hw Il Jp Js Li Ly Mt Oz Pc Pd Qb) Qb(Jp Lh Mt Nn No Nv Qa Qe) Li(Hw Il Js Ml Oz Pc Pd Qa) Jp(Hw Js Ly
Oz Pc Pd) Mt(Hw Om Oz Pc Pd) Nn(Hw Oz Pc Pd) No(Hw Oz Pc Pd) Ar(bQ Pg) CuJt PdaA} Ar{Nd(Ad bQ bZ cO dB dl Dl Mh Mm Oy)
Nj(Ad bQ Mh Nm Oy Pc Pg) Pg(Ad Cp Jt Nm Oy Pd) Fw(Im Jd Jt Mg Oy) bQ(Ad Ba Ly Mg Mt) ad(Ma Of Oh) cK(dB Nn Oh) cO(dB Ly Oy)
OhOy cBdB} Ti{iA(pS rO rU rW sC ul uN uO vB vl) dJ(sC ul uR vO yH yJ yK tL) pS(bM jG Nu Pc qA qU vQ) yK(Ne Or Pc qA) yJ(jG qU
vW) uN(cJ jG Ks) vl(jG rB) QdvP PcxA fYzH qArZ} wF{Ng(al As bA bX cC cH jV Mn Nj Nq Nt Ow qB Ri rR uV vU) Ij(iP kR Mh Oi qB)
Ri(Et Jt Mm) rR(Qm Qt Vs) Mg(bU bX) Jp(iA Ow) cW(eF qT) BoqB ImhC JtaW KgdJ KnjG bHdB} Jt{Fw(iA Im Jd Oh Oy Pc Qv Qy rZ Tz)
cH(pS sC sO vH vP) Tz(Cu Js Mj Pg) sC(bM iA qB Qd) cK(Js Pg Qb) Cu(Nd Nj) iA(aW rW) EdOf MpaY HwTr LdvH OrpS dJyD qBqY}
Mt{Pc(Hw Im Li Ly Ma My Nc Nd Nj Nq Nt Oh Qb) Qb(Im Li Lj Nn Nt Oh Oz Pc Pd Qe) Nt(Im Jp Oh Qa Qe) Qe(Nc Ne)} dB{Cp(aR Bg cB
cK cO) cB(An aR De Dl) vC(Or Qu Rc) BgCh DeCo dJvS} pS{Or(Ap Ic Il Jp Lx Mm) qU(Cw Kf) IL(Mm Uf) FybU GptR IjjG IlqA} Tz{Js(hR
hV Jd jF jR Mm rC) Me(hV jR) cH(sC wG) HfqU} tR{Pi(eF gP hC hG nY oF oK Qu Vs) rP(Al Dd) BaNn} dX{Pb(bA dF dM Fa gP Nc) Ld(Dl
Pd) MyKx HbeM KsPc} Ba{bQ(cN cP Ct kS Nd Of) nD(fB pH) kKpH} Ly{Jp(Im Me Oh Oz Pc Pd) Oz(Im Oh) LiPc} Qv{Hp(Fc Fi Mh Pk Ri)
Kc(Fc Fi) YgiP} Cp{Bg(cK cO Dl) aR(bQ cO) CqDl eMnD} Ap{iA(rW vC) MnwE QusC JvwB fNjG} Nc{Li(Hw Oz Pc) Oh(Oz Pd)}
Nf{Hp(gL tF) nD(gC iP) YggL} Im{Ed(ql rP rR xA) OhOz} Or{Jd(wG yD) DcvU DkyD TrzA} Tl{Hv(eC hB) FngL MvnW} Lh{oT(dJ gZ
nH) MpaY} aA{Pd(Iv Jr Nt) IvPc} tS{uN(Hb Ph) VsPi cMrC} jG{Un(rW vC) IiqZ RizA} wH{ChNd MgMp MnKq Ufal} Dc{Wn(iB jP oN)}
Em{Bo(gP gW) bMcP} Ao{KeeM altQ} Ef{VbdR tTiZ} Th{Nu(yH tL)} Hw{Li(Ne Pc)} Jr{gL(Fi Rx)} Kn{MnwL qBwC} Oh{NtOz NdJp}
gW{ChGn KpRu} zA{RclK KgdA} vU{AlbM JdqU} NmMpaY MgtXqB NakGrY KebCeM RimliP aWcOfR Constrained panels with 2 analytes, where 1.0E-8 >= 'model p-value' > 0. Contains 52 panels of 196,694 total panels evaluated. : Ok(Et Fp Hr
Hw Hx Ii Ik Il In Jj Ly Lz Ma Mb Mj Ml Nc Nd Ne Nf Ng Nh Nj Nk Nl Nx Of Oh Oz Pc Pd Pg Qb) Et(Fp Hw Ik In Ly Ma Mb Nc Nd Ne Nh
Nj Nl Nq Nx Oz Pc Qb) IkJj Constrained panels with 2 analytes, where 1.0E-7 >= 'model p-value' > 1.0E-8. Contains 35 panels of 196,694 total panels evaluated. : Et(Hx Il Jj
Js Lj Mp Mt My Nk Ns Of Oh) Ok(Iq Ji Me Mt Nn Pe Pf Po) aN(Bn bU cC Cp dE Ji) Ik(Ji Jp Nk Nw Oh) Nk(Fp Nl) AdaC InJi Constrained panels with 2 analytes, where 1.0E-6 >= 'model p-value' > 1.0E-7. Contains 145 panels of 196,694 total panels evaluated. : Ji(dE Fp
Hw Hx Jj Jq Js Li Ly Mb Ml Ms Mt My Nc Nd Ne Nh Nj Nk Nl Nq Ns Nt Nx Of Oh Oz Pc Pd Pf Qb) aN(aC Ad Ar Aw Ba bM cB Ch cK dB
Dg Dl Fp tk Jg Jt Lh Ly Mg Nd Nh Nm Nw Nx Ok Oy Pc Pd Pf Pj) Ik(AA Fp Fr Hw Im In Jg Lh Li Lj Ml Mm Mt Nc Nn No Nx On Oz Pa Pc
Pd Pf) Jg(aH dE Fp In Jj Mb Mt Mu Mw My Nc Ng Nh Nl Nq Of Oz Pc Tj) aC(Ao Aw Ba Bn Ch Cp Dg Dl) Fp(In Mm Mt Nx Oh On) Nx(Jj
Mt Nc Nh Nl) Pj(pS Qv Qy rZ Tj) dE(Ad Bn Cp De Dl) Mb(Mt Nw Oh On) Nk(Nc Nh) Nl(Nw On) AaMt EtaA NtJj Constrained panels with 2 analytes, where 1.0E-5 >= 'model p-value' > 1.0E-6. Contains 360 panels of 196,694 total panels evaluated. : aN(Aa
aE Ao bC bF bH bS bX cT Db De dl Et Ih Is Jd Jh Jl Jp Mm Mt Mw Nc Ne Ng Nj Nl Nn No Nr Nt Nv Of Og Oh Om On Oz Pb Pe Tz Un Tj)
dE(aC aJ aM An AR AW aY Ba bF bM Bo cB Ch cK cN cP Dg Et Fp Ik Im Jp Jt Lh Mt Nd Nh Nl Nm Nv Nw Nx Oh Ok On Oy Pb Pc Pd Pe
Pf) Jg(Aa aC Aj aR aY Bg bQ bZ cE cK Cu Fw Hw Hx iA Io Iu Lj Ly Ma Me Nd Ne Nj Nk Ns Nx Oh Oy Pd Pf Pj Qb) Pj(Ar cE De Fn Fw Hu

Nv(Hx Il Iq Iv Js Lj Me Ml Mw My Nq Ns Of) wL(Ap cJ cM cW Jh Kn Mg Mv Om qU Uc Vo Vs) Ch(aH aK bH bU cO cP Db eP Fp kS Mp
wH) Nm(aH aY Bn bZ cE cO cP Di Fn Qy Ra Ur) In(Ir Iv Jl Kf Lj Lx Mz nK No Om Po Qe) Ko(aY bZ cE Fn Gb Lv Ou Pg Ra Tn Tm) wH(Ap
Jh Mg Mv Mw Of Om On Pz Vo Vs) Bb(kS rU uG uO uW vC vH vP wK zH) Fc(Fb gL Hu Ib Jh Kc Kp Mw Qw Qz) Hw(Ir Iv Jl Lj Mu Mw No
Po Qa Qe) bU(aJ aM aW aY bF cG cI cN cP cT) hR(Ik jI jL Jp Ms Mv Mz Nw Om Po) qU(bG dI Fn Ii iP Kg Kp Mz Vq vS) Ap(hB iJ kS Ma tR
uT wB zH xA) Fp(aF aY bC bH Bn bZ cO dI) Ik(aH aY bL bZ cE cO Dq kS) Vz(Fb gL Hu Ib Kc kK nR Qt) Jp(iA Iq Ir Nq Qb Ra Rm Vp)
Lj(Hu Iv Mg Mu Mv Of Om Qb) Yl(Ib kK kN mI nB nR qX rA) Mz(eD hV Iv jE jY rB Vp) Nh(aH Bn bZ cE cO Cx dI) Kl(aH cE Cu Js Mp Of
Ra) Nw(aH bZ cE cO iA rB Vp) Oh(aA Hu Iq Ir Mu Pa Qb) Uf(cE fA iA iP Mp oN uT) nK(It Jn Ml Na Nf Om On) Mt(aH Bn bZ cE cO dI)
Hp(cQ Mh Pk Qv Ri Rm) Tl(gL iZ kI mY nB nJ) Kc(aY dI Gb Va Vc Wf) Kf(cE Js kS oN Qb Rm) hV(lY Ms mU Mv nA qX) Af(dV eM eP Gn
gT) Iv(Ir Mu No Nu Pa) Jk(Fd Ho Ps Rx Yf) On(aH bZ cO Cq Cu) gL(Si Vc Vw Wd Yg) tR(Al cW Kg Ld Ma) jD(Pj Uw Vh Vj Wc) Bn(Gn
Mg Nl Pa) Nf(lY Ye Tm Xa) Jn(kG nB oP oQ) Kp(aY Rx Ye Yf) Om(lY My qZ rZ) Db(Bo cB cP) No(Hu Hx Mu) Ng(uT vU zH) Rc(iP kS oN)
aA(Ir Jr Po) aY(Ic MP) cJ(vS vU wG) qT(Dr Vc Wc) Al(vH vU) Ma(tS tX) Mv(jT rZ) Of(Iz Kj) Or(sC yJ) cH(sC vS) eM(Jr Nt) eQ(Hc Rb)
nN(jR jT) nD(hC pH) iP(Fy Yg) rX(rQ rW) oQ(kI lY) BggN CtGn DrcP PoQb EmgW GcQv GwPk NuIr MsqZ IcQy IirB IjwD HfYe WdiZ TmnA KePg KgvH VqiO aEvQ aHbF aVdV bBeP cOfR cRtX cWvS dIrQ fAfP

Unconstrained panels with 3 analytes, where 0.0E0 >= 'AUC p-value' > 0. Contains 50,000 panels of 36,603,637 total panels evaluated. : Pj{pS(AA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp dR eC ED EF ET EZ Fa Fb FN FP Fr Fw FY GL GP gW HA HB HC HF hG hL hO hP Hq HR Hu HV HW HX iA IB Ic Id IH Ii IJ Ik Il Im In IO IP Iq Ir Is It Iu Iv IZ JD JE JF JG JH JI Jj JK JL JM Jn Jo JP JQ JR Js JT JU JV JY Kc Kd Ke Kf Kg Ki Kj Kk Kl Kn Ko Kp KQ KR KS Kx Ky Kz Ld Lh Li Lj lK lL lM lN lO Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pk Po pY Pz QA QB QC QD Qe QG QH qI Ql Qm Qn qO qP qQ QT QU QV QW QX QY QZ RA RB RC Rf Rg Rh Ri Rj Rm rN rO rP rQ rR rS rT rU rV rW rX rY rZ sC sK sM sO Sr Ss St TN TO tQ TR tS TT tU TV tX Tz Ua Ub Uc Ud Ue Uf UG Uh uI Uk UL UM UN UO UP UR Us UT UU UV uW uX uY uZ vA vB vC vH vI VO VP vQ VS VT VU VV vW wB wC wD wE wF wG wH wJ wK wL wP wQ yD yH yJ yK yL zA zG zH zI yE tM tL xA Wm Tj Ti Th tF) wG(AA aC AD aE AF aG aH aI AJ aK AL aM AN AO AP aQ AR As aU aV AW AX aY aZ BA BB BC bE bF BG bH bI bJ bL bM BN BO bP bQ bR bS bU bV bW bX bZ cA cB cC cD cE cF cG CH cI cJ cK cL cN CO CP CQ cR CS CT CU CV CW CX cY cZ DB DC DD DE dF DG dH DI DK DI dM dN Dp dR eC ED EF ET EZ Fa Fb FN FP Fr Fw FY GL GP gW HA Hb HC HF hG hL hO hP Hq HR Hu HV HW HX IB IC Id IH Ii IJ Ik Il Im In IO IP Iq Ir Is It Iu Iv IZ JD JE JF JG JH JI Jj JK JL JM Jn JO JP JQ JR Js JT JU JV JY Kc Kd Ke Kf Kg Ki Kj Kl Kn Ko Kp KQ KR KS Kx Ky Kz Ld Lh Li Lj lK lL lM lN lO Lu Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Po pY Pz QA Qb QC QD Qe QG QH qI Ql Qm Qn qO qP qQ QT Qu QV QW QX QY QZ RA RB RC Rf Rg Rh Rj Rm rN rO rP rQ rR rS rT rU rV rW rX rY rZ sC sK sM sO Sr Ss St TN TO tQ TR tS TT tU TV tX Tz Ua Ub Uc Ud Ue Uf UG Uh uI Uk UL UM UN UO UP UR Us UT UU UV uW uX uY uZ vA vB vC vH vI VO VP vQ VS Vt VU VV vW wB wC wD wE wF wH wJ wK wL wP wQ yD yH yJ yK yL zA zG zH zI yE tM tL Wm Tj Ti Th tF) tR(aA aC AD aE AF aG aH AJ AL aM aN AO AP AR AS aU aV AW AX aY aZ BA BB BC bF BG bH bI bJ bL bM BN BO bP bQ bR bS bU bV bW bX bZ cA cB cC cD cE cF cG CH cI cJ cK cL cN CO CP CQ CS Ct CU CV CW CX cZ DB DC DD DE dF DG dH DI dJ DK DL dM dN Dp dR eC ED EF ET EZ Fa Fb FN FP Fr FY gL GP HA HB HC HF hG hL hO hP Hq HR Hu HV HW HX iA IB IC Id IH Ii IJ Ik Il Im In IO Ip Iq Ir Is It Iu Iv IZ JD JE Jf JG JH JI jK JL JM Jn JO JP Jq JR Js JT JU JV JY Kc Kd Ke Kf Kg Kj Kl Kn Ko Kp KQ KR KS Kx Ky Kz Ld Lh Li Lj lK lL lM lN lO Lu Lv Lw Lx Ly Lz Ma Mb Mc Md Me Mf Mg Mh Mi Mj Mk Ml Mm Mn Mp Mq Ms Mt Mu Mv Mw My Mz Na Nb Nc Nd Ne Nf Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pk Po pY Pz QA QB QC QD Qe QG QH qI Ql Qm Qn qO qP qQ QT QU QV QW QX QY QZ RA RB rC Rf Rh Ri Rj Rm rN rO rP rQ rR rS rT rU rV rW rX rY rZ sK sM sO Sr Ss St TN TO tQ Tr tS TT tU TV tX Tz Ua Ub Uc Ud Uf UG Uh uI Uk UL UM Un UO UP UR Us UT Uu UV uW uX uY uZ vA vB vC vH vI VO VP vQ VS VT VU VV vW wB wC wD wE wF wH wJ wK wL wP wQ yD yH yJ zG zH zI yE tM tL xA Tj Th tF) tS(aC AD aE Af aG aI Aj aK AL aM aN AO aR AS aU aV Aw aY aZ BA bB bC bE bF bH bI bL bM BN BO bP bR bS bV bW bX bZ cA cB cC cE cF cG cH cI cK cM cN cO CP cQ cR CS CT CU CV CW CX cY DB Dc dD dE dF DI dJ DK DI dN dR eC ED eF ET eZ Fb fN FP Fr Fw FY GL Gp gW Ha hB HC HF hG hL hO hP Hq Hr Hv HW Hx iA IB IC Id iH Ii IJ Ik Il IO IP Iq Ir It Iu IZ jD Je jF JG JH Jj jK JM JO jQ Jr Js JT JU JV JY Kd Kg Kj Kk Kl Kn Ko kQ kR Kx Kz Ld Lh Li Lj lL lM lN lO Lu Lv Lw Ly Lz Ma Mb Mc Md Me Mf Mg Mh Mi Ml Mn Mp Mq Mr Ms Mt Mw Mz Na Nd Ne Nf Ng Nh Nk Nl Nm Nn No Nq Nr Ns Nu Nv NW Nx NY Oa OE OF Og OH Oi oK Om oN Ou Ow Oy Oz Pa Pb Pc pF Pg Ph Pi Pk pY Pz QA QB Qc qD Qe QH qI Ql Qm Qn qO qP QU qV QW QX QY Qz RA RB Rf Rg Rh Ri Rj rO rP rQ rR rS rT rU rV rW rX rY rZ sM Sr TN TO tQ Tr tT tU Tv Ua Ub Uc Ud Uf uG Uh uI Uk UL UM uN UO UP UR Us UT Uu UV uW uX uY uZ vB vH vI vO VP VS vT VU VV vW wD wE wF wH wJ wK wL wQ yD yH yJ yK zG zH zI tM tL xA Wm Tj Th tF) tN(aC AD aE Af aG aI Aj aK aM aN AO AP aQ AR AS aU aV AW AX aY aZ bA Bb BC bE bF Bg bJ bM BN bO bP bQ bR bX cA cB cC cE cF cG cH cI cJ cK cL cM CO cP Cq Cs cT Cv CW CX DB Dc dE dF DG dH DI dJ DK dL dR eC ED EF cT EZ Fa fN FP Fr Fw Fy gL GP gW HA HB HC HF hG hL hP Hr Hu Hv Hw iA IB iC Id iH Ii IJ Il Im IO iP Iq Ir Iu IZ jD JE JF JG Jh Ji JK Jl jM jO jP jQ JR Js JT Ju JV jY Kc Kd Ke Kf Kg Kj Kk Kl Kn Kq KR kS Kx Kz Ld Li Lj lK lL lM lO Lu Lw Lx Ly Lz Mc Md Mf Mg Mh Mi Ml Mm Mn Mp Mq Mr Ms Mt Mu Mv Mw Mx My Mz Nb Nf Ng Ni Nm Nn Nq Nr NW Nx NY Oa OE oF Og oH Oi OK Om ON Or Ow Oy Oz Pa Pb Pc Pe PF Pg Ph Pi Pk Po qA qB qC QD QG QH Ql Qn QT QU QV QW qX Qy QZ Ra rB Rg Ri Rj Rm rO rP rS rT rV rW rX rY sC sK sO Sr Ss Tn tO tQ Tr Tv tX Ua Ub Uc Ud Uc Ug Uh uL UM uN Uo Up UR Us Ut uV uW uZ vA vB vC vH vI Vp Vs vT VU VV vW wB wD wE wF wJ wK wL wQ yH yJ yK zG zI yE tL xA Wm Tj Th) wF(aC AD aE Af aG aI Aj aK AN Ao Ap aQ Ar aS aU aV AW aX aY Ba BB bE bF bM BN BO bP bR bS bU bV bX cB cC cD cF cG Ch cJ cM CO Cp cR Cs CT Cv CW Cx cY DB Dc dD dE dF Dg dH DI dJ DK dL dM dN dR eC Ed EF Fb fN fP Fw gL GP gW hA hB HC HF hG hO hP HR Hu HV hW Hx iA Ib iC iH Ii Ij Ik Il Im Io iP iZ JD JE JF JG JH Ji Jj Jk Jl jM jO JP Jq JR Js jT jV Kd Kf Kg Ki Kj Kk Kl Kn KQ KR KS Ky Ld lK lL Lv Lx Ly Ma Md Mf Mg Mh Mn Mp Mq Mr Ms Mt Mv Mw Mx My Na Nd Ng Ni Nj Nl Nm Nq Nr Nt Nu Nv NW nY Oa OE OF oH Oi oK ON Or Oy Pa Pd Pe PF Pk Po pY qA QB Qc Qg QH Ql Qn qQ QT QU QV qW QY QZ Ra RB RC Rf Rh Ri Rm rO rP rR rS rV rW rZ sK Ss tO Tr TT Tv tX Tz Uc Uk uL uN UP uY vA vB vC vH vI Vo Vp Vs vT vU Vv vW wD wL wP wQ yK zG zH zI tL xA Tj tF) tT(aC AD aE AF aG aH aI Aj aK aM AN AO AP aQ Ar aS aU aV AW aX aZ BA bE bF BG bI bM bN BO bP bQ bS bX bZ cB cC cE cG cH cI cL cM Co CP cR Cs CT cU Cv CW Cx cY dB Dc dE dH DI dJ DK dL dR eC ED EF

Figure 12 Continued

Figure 12 Continued kC kK kN Lu lW Ma mF ml Mj mP mT Ne Ni nR oW Oy Pa pH Qw Ss St Vu) Fy(aA aL cB cG Co cT cZ Db fB Hc Hv Ib Iq iZ kK Lv Ma Mh
Ni Oy Pa Pf Pk Qe Ss St Vo) Nr(Ao bC bU bV bZ cQ Hc Ib Id Jj jC kK KN kR IX Mh mY ND nJ oN Pk Qz Rb St Vu) Nv(aY Ba cQ cZ dR eF
Hc Id Iq kC kK KN lW IX Ma mT mW Oe Oh oN oT Pa St Uk Vu Vv) Pe(bC bU cK cO Hc Ib kC kK kN Mh Mm mY Mz Na ND Ne nJ Nk Oe
Og oN Pk Qz Rb St) Ke(Ao Ba Bb bJ Bn bZ cB cJ cQ CX Gp hF Iz kN lW Ma mF Mk mT nH Nk Oe oO Qw) Pa(Ad Ao Ap Ba Dg Dl Ef Hc Ij
Im Iz Jg Jh Jo Jp Kf Kg Ko Mh Mm Ok Pz Qz Tn Tt) Iv(aY cl cX dE Fb Fw Hc Ib Id kK Mm mP mY Mz Na nD nJ nN Pk Qy St Us Vu) Oe(Ax
bB Bg De Fp Ha Ju kE Ki Lz Mm Mn nD Ql Rb Tt Ua Uc Ug Uu Uv) Ao(Ez Gl Ki Kp Kx Nd Or Qe Qh Qv Rm St Ub Ul Um Ur Uv Vo Vp Tj)
Im(aY bC cK Fb Fn Hc Ib Id Iq kC kK lW mY ND nJ Qz Rb St Ua) Ha(aY bZ cQ cX eF Hc Iq kC kF kN Lv lW mP nD oN Pf Qe Qg St) Cx(Ef
Hc Hf Kf Kn Pi Qg Qu Rb Tz Uc Ud Uh Uk Um Ur Vv Tj) aY(Ih li Iz Jg Jo Kf Kg Ko Kq Ks Nh Ok Qc Qh Tn Tz Ua Vs) Qz(Ar bB bE Bn cQ
DE dH eC Mf Ml mU nA Ne pH Tz Vp) Mk(aH bB bL cl Hc Ij Jg Ju mF Mt nD Nq Qg Rf Ua Tj) Ss(bN Ef Io Jg Jp kE Kl Ko Kq Ml Mn nA nC
Ng pH Uc) cX(bE Hf Ih Ir Is Iu Mm Nt Nu Po Qa Qh Rm Sr Uh Vs) Fa(bZ cK eF Hc iA Id Lu lW Mh Mr Ni oN oW Oy Vu) Iq(Dk Dl Ij Io Ir It
Je Jp Kf Ko Kq Nh Tz Uh Un) Qw(aH bA cB cF cQ Hc Ip Ju kS Mn Ni Nq Oy Qg Tj) mT(Ax Fp Je Jg Kn Kq Ks Lj Oa Ok Rf Tr Ua Vs Vv)
lW(Gl Hf lj Io Jg Ju Ks Nh Nq Oa Tz Ua Vs Tj) St(Ax Co Dc Dk hC Ij Ir Is Jp Oa Ok Qh Vs) Qg(aC As Ax Bc cB cJ Cv Dc Di eF In Nm pH)
Ni(Ad Ap Dg Je Jg Kq Oa Ok Qh Tz Uc Un) cQ(Fb Fn Fp Kf Ko Nu Oa Ql Rf Uh Uv Vp) Tz(cW Db Hv kK Lv Mq nD Nk Oy Uk) Ir(cO Hc Ib
Id kK mY ND oN Rb) Tj(aR Bc bZ cl cM Kg Mm nD) Mn(aK bE eC Ic Id IX mP oW) Ij(Bc kK nD Or Oy pF Qb Rm) Rb(Ax bN DE dH eQ Gl
ml) Vu(Ax Cs De It Lj Oa Og Qh) Lv(Gl Ju Oa Or Qh Ua Vs) Hc(Ax De eC eQ Ez Fp It) Uk(Bc cl cM eF Iu Kg pH) Ib(hB hC It Jo pH Ua)
Ju(aK As bE Ml Ri Un) Oy(dC Hf Je Qh Sr Uh) nD(Dp Jh mZ Qh Um Vs) oW(Kf Ko Ow Qc Qd Uc) Ng(aK eC Hf Sr Un) Nk(Jg Kf Oa Tn Un)
Ri(Bc bJ cG eC ml) Ok(aC aL cW cZ nL) eF(Dp Ef Kl Ue Um) Ax(Mh Ne Oa Pf) Ua(bG cB eC Ml) Hv(Ef Gl Kg Qu) Id(bB cN It nA) Jo(Hq
Hw Vo Vv) Bc(Dp Je Un) Nq(aR kN Mh) Tt(cN hG Ml) Jg(bE Fp mP) Sr(ml nA Or) Kg(aK aW cB) Uh(bZ Jj kN) Ur(Ad Cv Jp) Vs(bF cB mF)
pH(Iz Kn Uu) Db(kP Or) Gl(kK Lu) Nt(ml nL) Mh(Ar Cs) bZ(Oa Qh) eQ(Ky Vo) gL(Tn Tr) AdaA ApnL BaFp MeOr MmnA MrkK UemF
Udlu ItQl KjcN KncB KomP KscG LjbC Usml aQdN} Vq{ql(aA aC AD aE AF aG al aJ aK AL aM aN AO AP aQ AR AS aV AW AX aY aZ
BA BB bF BG bH bl bJ bL BN BO bP bQ bR bS bU bV bW bX cA cB cC cD cE cF cG CH cl cK cL cN CO CP CQ cR CS CT CU cV CW cX
cZ dA DB DC DD DE dF DG dH DI DK DL dM Dp eC Ed Ef Et Ez Fa Fn FP Fr Fw Fy GL GP gW Ha HB HC HF hG Hq Hr Hu Hv Hw Hx Ib
Ic Id IH Ii IJ Ik Il Im In IO IP Iq Ir Is It Iu Iv IZ Jg Jh Ji Jj Jk Jl Jm Jn Jo Jq Jr Js Jt Ju Jv Jy Kc Kd Ke Kf Kg Ki Kj Kk Kl Kn Ko Kp KQ KR KS
Kx Ky Kz Ld Lh Li Lj Lv Lw Lx Ly Lz Ma Mb Mc Md Me Mf Mh Mi Mj Mk Ml Mn Mp Mq Mr Ms Mt Mu Mv Mw Mx My Mz Na Nc Nd Ne
Nf Ng Nh Ni Nj Nk Nl Nm Nn No Nq Nr Ns Nu Nv Nw NY Oa OE OF Og OH Oi OK Om On Or Ou Ow Oy Oz Pa Pb Pc Pd Pe PF Pg Ph Pi
Po Pz Qa Qb Qc Qd Qe QG QH Ql Qm Qn QT QU QV QW Qw Qx QY QZ RA Rb RC Rg Ri Rj Rm rN rO rQ rR rS rT rU rV rW Sr Ss St Tn To Tr
Tt Tv Tz Ua Uc Ud Ue Uf Ug Uh Uk Ul Um Un Uo Up Ur Us Ut Uu Uv Vo Vp Vs Vt Vu Vv Wm Tj tF) rS(aC AD aE aF aG al aJ aK AL aM
aN AO AP AR aS aU aV AW AX aY aZ BA Bb Bc bE bF BG bH bl bJ bL bM bN BO bP bQ bR bS bU bV bW bX bZ cA cB cC cD cE cF cG
CH cl cK cL cM cN CO CP cQ cR CS CT CU cV Cw CX cZ dA DB DC DD dF DG dH dl dJ DK DL dN Dp dR eC Ed eF Et Ez Fb Fn FP Fr
Fw Fy gL gP gW Ha HB HC hF hG Hq Hr Hu Hv Hw Hx Ib Ic Id IH Ii IJ Ik Il Im In Io iP Iq Ir Is It Iu Iv iZ Je Jf Jg Jh Ji Jj Jk Jl Jm Jn Jo Jp Jq
Jr Js Jt Ju Jv Jy Kc Kf Kg Ki Kj Kk Kl Ko Kp KQ KR KS Kx Kz Lh Li Lj Lu Lv Lw Lx Ly Lz Ma Mb Mc Md Me Mf Mg Mh Mi Mj Mk Ml
Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa
OE OF OH Oi OK Om On Ou Oy Oz Pa Pb Pc Pd Pe PF Pg Pi Pk Po Pz Qa Qb Qc Qd Qe QG QH Ql Qm Qn QT QU QV QW Qx QY QZ RA
RB RC Rf Rg Rh Ri Rj Rm rN rO rP rQ rR rT rU rV rW Sr Ss St Tn To Tr Tt Tv Tz Ua Ub Uc Ud Ue Uf Ug Uh Uk Ul Um Un Uo Up Ur Us Ut
Uu Uv Vo Vp Vs Vt Vu Vv Wm Tj tF) qH(Aa aC AD aE AF aG al aJ aK AL aM AN Ao AP aQ aR AS aU aV AW aX aY aZ BA BB BC bE
bF BG bH bl bJ bL bM BN BO bP bR bS bU bV bW bX bZ cA cB cC cD cF cG CH cl cJ cK cL cM cN Co cP cQ cR cS cT cU CV CW cX cZ
dA dB dC DD DE dG dH DI dJ DK DL dM dN Dp dR eC Ed eF Et Ez Fb Fn FP Fr Fy gL gP Ha HB HC hF hG Hq Hr Hu Hv Hw Hx iA Ib Ic
Id Ih Ii Ij Ik Il Im In IO IP Iq Iv iZ Jd Je Jf Jg Jh Ji Jj Jk Jl Jm Jn Jp Jq Jr Js Jt Ju Jv Jy Kc Kd Ke Kf Kg Kk Kl Kn Ko KQ KR kS Kx Ld Lh Li Lj
Lu Lv Lw Lx Ly Lz Ma Mb Mc Md Me Mg Mh Mi Mk Ml Mm Mn Mp Mq Mr Ms Mt Mu Mv Mw My Mz Nb Nc Nd Ne Nf Ng Nh Ni Nj Nk
Nl Nm Nq Nr Ns Nt Nu Nv NW Nx Ny OE OF Og Oh Oi OK Om On Ou Oy Oz Pa Pb Pc Pd Pe Pf Pg Pi Po Qa Qb Qc Qd Qe QG Qh Ql Qm
Qn QT QU QV QW QX Qy qZ RA RB Rc Rf Rg Rh Ri Rj Rm rN rO rP rQ rR rT rU rV rW Sr Ss Tr Tt Tv Tz Qb Uc Ud Ue Uf Ug Uh Uk Ul
Um Un Uo Up Ur Us Ut Uu Uv Vo Vp Vt Vu Vv Wm tF) rR(aA aC aD aF aG aH al AJ aK AL aM aN AO AP aQ aR AS aU aV aW aY aZ Ba
bB Bc bE bF bG bH bl bJ bL BN bO bP bQ bR bU bV bX bZ cA cB cC cE cF cG cl cJ cK cL cM cN CO CP cR CS CT CU cV CX cY cZ DB
DC DD DE dG dH DI dJ DK DL dN Dp dR eC Ed EF Et Ez Fa Fb FP Fr Fw Fy GL gP Ha HB HC hG Hq Hr Hu Hv Hw Hx Ib Id IH Ii Ij Ik Il
Im In Io iP Iq Ir Is Iu Iz Jf Jh Ji Jj Jk Jl Jm Jn Jo Jp Jq Jr Js Jt Ju Jv Jy Kc Kd Ke Kf Kg Kj Kk Kn Ko KQ KR Ks Ky Kz Lh Li Lj Lv Lw Lx Ly Lz
Ma Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm Nn No
Nq Nr Ns Nt Nu Nv nV Nx Ny Oa OE oF Og Oh OK Om On Or Ou Oy Pa Pb Pc Pd Pe Pf Pg Pi Po Pz Qa Qb Qc Qd Qe QG Qh Ql Qm Qn
QT qV QW QX QY QZ RA RB RC Rg Rh Ri Rj Rm rN rO rP rQ rR rT rU rV rW Sr Ss St Tn To Tt Tv Tz Ua Uc Ud Ue Uf Ug Uh Uk Um Un
Uo Up Ur Ut Uu Uv Vo Vp Vt Vu Vv Wm) rP(aA AD aE AF aG aH al AJ aK AL aN aO AP aQ aR aU aV AW aX aY aZ bB bE bF bG bH bJ
bL bN BO bP bQ bR bU bV bW bZ cA cD cE cF cG Ch cl cJ cK cL cN CO CP cS CT CU Cv CW cZ dA DB DC DD De dF DG dH DI dK dN
Dp eC Ed EF Ez Fa Fb FP Fr Fw Fy Gl Gp gW Ha HB HC HF hG Hq Hv Hw Hx Ib Ic Id IH Ii IJ Il In IO IP Ir Is Iu Iz Jg Jh Ji Jj Jl Jm Jn Jo Jp
Jr Js Ju Jv Jy Kc Kd Kf Kg Ki Kj Kl Kn Ko Kp KQ KR KS Ky Kz Ld Lh Li Lj Lu Lv Lw Lx Ly Lz Mb Mc Md Me Mf Mg Mh Mi Mj Ml Mm
Mn Mp Mq Mr Ms Mt Mu Mv Mw Mx My Na Nb Nc Nd Ne Nf Nh Ni Nj Nk Nl Nm Nn Nq Nr Ns Nt Nu Nv NW Nx nY Oa oE oF OH Oi OK
On Or Ou Ow Oy Pa Pb Pc Pd Pe PF Pg Ph Pi Pk Po Qa Qb Qc Qd Qe QG Ql Qm Qn QT Qu QV QW QX Qy QZ rA RB RC Rf Rg Rh Ri Rj
Rm rN rO rQ rT rU rV rW Sr St Tn To Tt Tv Tz Ua Uc Ud Ue Uf Ug Uh Uk Um Un Uo Up Ur Us Ut Vo Vp Vt Vu Vv Tj) rT(aA aD aE aG aH
al AJ aK AL AN aO Ap aQ aR aS aU aV AW aX aY aZ BA bB Bc bE bF bG bl bJ bM Bn bO bP bQ bR bS bU bV bW bZ cB cD cE cH cl cJ
cL CO cP CQ cR CS CT CU cV CW Cx cY cZ dA dC dD DE dF DG dH Di dJ Dk DL dM dN Dp dR Et Fb Fn FP Fr Fy Gl GP gW Ha HB Hc
hG Hq Hr Hu Hv Hw Hx iA Ib Ih Ii IJ Ik Il Im In iO Ip Iq Iv iZ Jd Je Jf Jh Ji Ij Jk Jm Jn Jq Jr Js Jt Ju Jv Jy Kc Kf Kg Kj Kk Kl Kn Ko Kp kQ kR
Kx Ld Lh Lj Lu Lv Lx Ly Me Mg Mj Mk Mm Mn Mp Mq Mr Ms Mt Mu Mv Mw Mx My Mz Na Nb Nc Nd Ne Nf Ng Nh Ni Nj Nk Nl Nm Nn
Nq Nr Nt Nu Nv Nx NY Oa OE Of Og Oh Oi OK Om On Ou Ow Oy Oz Pa Pb Pc Pd Pe PF Ph Pi Pk Po Pz Qa Qb Qc Qe QG Qm Qn QT QU
qV qW qX QY QZ RA RB RC Rf Rg Rh Ri Rj rN rO rQ rU rV Sr Ss St Tn Tr Tt Tv Tz Ua Uc Uf Ug Uh Uk Um Un Up Ur Us Ut Uu Vo Vs Vt
Vu Vv Wm Tj tF) rU(aC AD aE aG aH AJ aK Al aM aN AO aP aQ AR aS aU aV AW aX aZ bB BC bE bG bl bJ bL bM BN bO bP bQ bR bS
bU bV bW bX bZ cA cB cC cD cE cG Cll cl cJ cK cL cM cN CO Cp Cq CT CU cV CW cY dA dC DG dH dl dJ dK DL dM dN Dp dR eC Ed
eF Et Ez Fa Fb Fn FP Fr Fy gW hB hC hF hG Hq Hu Hx Ib Ic Id IH li IJ Ik Il Im In IP Ir It Iu Iv iZ Je Jf Jg Jh Ji Jj Jk Jl Jm Jn Jo Jp Jq Jr Js Jt Ju
Jv Jy Kc Kl Ko Kp kQ KR KS Kx Lh Li Lj Lu Lw Ly Lz Ma Mb Mc Md Me Mf Mg Mh Mi Mj Mk Ml Mm Mn Mp Mr Ms Mt Mv Mw Mx My
Mz Nb Nc Nd Ne Ng Nh Ni Nl Nm Nn No Nr Ns Nt Nu Nv nW Nx NY Oa OE OF Oh OK Om ON Oy Oz Pa Pb Pc PF Pg Pk Pz Qa Qb Qc Qd

RA rB Ri rN rP rQ rR rS rU rW Ss Tn Tt Tv Tz Ua Ul Uo Up Vt Vv yH zA tM Wm Tj Ti) Jp(aC aD al aN aN Ao aS aW Bg bH bI bM Bn bS bX cC cH cL Co cW Cx cZ dD dJ Dl Dp dR eC Ed eF Ez FN fP Fw Fy gL gP gW Ha hB hC hF hG Hu iA Ib Ic iH iJ iO iP lZ Jd Je Jf jG jO Jv Jy Kd Kf Ki Ko kQ kR kS Ky Ld Mv My nW nY oE OF oH oK oN Or Ow pF Pi qA qB QG Qh Ql Qm Qn QU Qv Qw Qx Qy Ra Rb Rc Rg Rh Ri Rj rR Sr Ss Tn Tt Tv Tz Ua Ub Uc Ud Ue Ug Uk Ul Um Un Uo Up Ur Us Ut Uu Vo Vp Vs Vt Vu Vv Tj tF) Ti(aC Ad al Al An aO Ap aV Aw Ba bE bM Ch cJ Co CP CW dB Dc dE dJ DK dL dM dR eC EF fP gL gW HB hC hF hG hP Ib iC iH Ii iJ Im iO iP iZ JD Jh Jn Kc Kg Ko Kq kR KS Ky Lv Mf Mh Ms Mv Nb Ne Nq nW nY oF Oi Om ON Pc pF Po qB Qh QT qU Rc Rj rZ tN tO Tr tS Tt tU Tv Tz Uc Ug Um Uu vH vl VS vT tL) Ap(Aa aC al aQ aS aW aX bJ bM cH cM cR cZ dJ dL dN eT fN Fr gW hC Hq Hv iA iZ jE jG Jj Ki Kk Kn kQ kS 1K Md Mn Nb Nd Nn Nt Nv nW nY Oe Or Ou Pi pS qA qB Qu Ri rN rR rW Tn tR tS Up uT vC vH vT vU vW wB wL zl tM tL xA) aC(Aa Ad Af An Ao Ar As Aw Ba Bg Bo Ch Co Cp Cv Cw Cx Db Dg Di Dk Dl Ed Ef Fw Gl Gp Hb Hc Hf Hr Im Iz jK Jt Kc Kd Ke Kf Kg Kj Kk Kl Kn Ko Kp Kq Kr Ks Kx Ky Kz Mh Mn Oi Or Ou Ow Pa Ph Pi Ql Rb Ri Rj Tv Ut) rR(Ao Ar Aw Ba Ch Co Cp Cw Dg Dk Dp Ed Ef Et Gl Hc Ib Ii Im Jd Je Jh Ji Jt Ju Jv Kc Ke Kg Kk Kn Kq Ld Lh Me Mh Mm Mq Mt Mv Mw Oa Ok Om On Oy Pc Pe Po Qm Qt Qz Rc Ri Rj Tt Tv Ub Uc Uf Uh Un Ut Vo Vs Vv Tj) Im(aX bl bJ bS cL cR dB dl dK dR eC Ed eF fP Fw gL gP gW hB hC hF hG hP iA iH iJ iO iP iZ jG Kn kQ KR kS nW nY oE oF oH oK oN pF Pk qU qW QX Ri Tr Uu Vo Vp Vu Vv Tj tF) Ri(Ad Al Ar bL bO Cp Cv cW Dg Dk Ef Et Fy hC hG Ib Ii Iz Jd jG Jh Ji Jo Jt Kg Kj Kl Kn Kq Lu Mg Mm Mq Mv Mx Nm nY oE oF Ok Om oN Pz qU TR Tt Tv Tz Uc Ug Un Vo Vs Vt yL) Aa(Ar Aw bE Bg cG Cp cR Dc Dg dH EF fP Hu Hw lk Il iO Iz Jd Jh Kg Kn Lj 1M Mg Mv Mw My Nq Oa oF Om On Oy Po Qt Uc Uf Uu Vo Vv) Dg(al aL aS aW bM cH cM cR Di dJ dL Fb iA Il jG jO Js Ki Kk 1K IN Md Mn Nv nW Or Pk pS qA qB tR tS uT vC vH vT vU vW wL tL xA) Kg(al aN bJ bM bS bX cM dJ gL hC hP iA iC iO jG IN Md Mh Mn Mp Nn Nv nW nY Oe Ow qB Ql tQ tS vC vT vU vW tL xA) Kn(aH al aN bB bM bS CH cM cW dF dJ Hb iA Ik Iz jG jO Kk Mn Nt nY Or Pk pS qB qU tR tS uM Un uT Uu vH vT vW) Mg(aA aN As bS bU bX cC cJ cM cW dA dJ hP iC iP jG jV Ld lL Mn Mp Nk Nq Nt Or Ql qT tQ Tv uY vU wJ) qB(Ao Ar Aw Ba Bo Co Cu Cw De Dk Et Ib Jd Ji Jt Ke Kj Kq Mm Oa Ok Pc Po Qm Qt Uc Uf Uh Un Vo Vs Vv) Or(Ad Ao Aw bW Ch CP cU Dc Dk EF Et Ik Il Iz Jd Jh jV Ms Mt Nm Of OK pS sC Uf Un Vs Vv) Ad(aD As aW bN cC cH cJ Fn Il jT JU JV Ld lL Mn Nd Nn Pc pS tS vH vT vU Vv tL) Ok(al aV bB cJ cM dA dF dJ DL eT gW hC hR iA iJ iP jE jF jG jO Ky IN nW qA Ql rQ) Mn(Co CW De Gl Jt Ke Kj Kl Ko Kq Ma Mv Om Pf Pz Qm Qt Rc Rj Uc Uf Un Vo) tS(Ao Aw Ba Bg Ch Co Cp Ct Cw Dc Dd De Dk Iz Jd Kc Ke Kl Kq Ql Rj Vo) Dl(Ar aS Bo cH Cw Di dJ Fw Nd Pc qA rP tR tV Ur vH Vo vU wL xA) li(aN aW bS bX cM dA hC hG hP iA iC iJ iO iP jG kR oH qA qC Ql) Jt(aS aW cC cH cR dJ fN iA iP JV Ki kQ pS qA Qd qT Ur vU) jG(Ao Ch Ef Et Il Jh Ji Kc Kf Mt On Qt Uc Ue Uf Uh Un Vs Vv) Uc(aN aW cH cJ dJ hP Ki lL Nd Nq Ow Qb Ql Tv uT vS vU) Nd(Dc Dd Ik Iz Jd Qh Qt St Tr Tv Un Up Vo Vs Vv) Vt(aV Ba Ch dA hP iA Js kR Mh Oi Pk pS qA Ql vU) cH(Al Ed Il Jd Kl Mh Og Oi Pc Pd Ql Tz Vo Vv) cW(aF AO Ar bH bZ dA eF Kf On qT Uu vT vU) Un(aI aV dA dJ iA iP jE jO Jr Kk Ql vT tL) Vs(aN As bA dJ Nn Nq Nt qG qH UT vS vU) vH(Aj Ao Aw Ch Cp Dk Ef Iz Ke Kf Kj Kq Uf) Ld(bN Hb Kj Ne Nu Pc qT qU qX St Tr tF) Dk(aS aW It lL lN Nn Oe Ql tR vS vU) Il(aN Cv Ed hP Kl Kq lL Pk qA qI Rj) Et(aI aV cM dA dJ dL iA jO qA Ql) Ji(aN bS cM dA dJ hP lL Ql Rj Uu) Vv(iP jD Ke Kj Ko Ky Lu Pk qA vT) pS(Ar Bo Cw Gl Kf Kj Ph Qg Ql Rj) Ch(As aX bL Jk Ki Nn Nq Pc Tz) Vo(bU bX cC dJ iP rZ tR vU wJ) Uf(aI cJ fN iA Md qA uT vT) Cw(cZ dB lK nW nY Tz Ug) Kj(As aW cJ JV Ki vU) Cp(As aX bL Nn Tz vS) Hb(cM kQ Md qU Uu tL) dJ(Ik Jo Mm Pd Qt Ue) iA(Ke Kf Nm Pc Qm Ub) Dc(bH Jv Rj vC vU) Tz(cP dA Di pY Rj) aI(Ao Jd Ke Kq Mm) jV(Ju Jv Pk St Tr) hP(Ih Is Jo Ms) Ao(lN nW rN) Aw(aX Ki vS) Ef(As Nn vS) Mm(bB cM dA) Jd(bS Je qT) Jh(Ki vC vS) Kk(cL Pc Pd) Rj(dB Ms qU) Ql(Bc Mq Tv) On(lL Nt zA) Ar(nW nY) Bo(dB Ms) Fw(Kc qU) Nu(Fn Jv) Ly(hC nY) Md(fP qT) Ub(Ki vT) Tr(jU lL) Jo(cC iP) Uu(Kd Pi) Pd(aN dA) tR(Cu Pi) vU(Al Kl) BauT EdqT GlnW NmqA MqdA HwaN IkjT RccZ PzaW QtqG KplK KqlN OibN UgpY PacM PchB bHdB} Yl{kK(aC aE AF aK aL aM AN Ao aU aV bA bB bE BG bH bI bJ bM Bn bO bU cA cB cC cD cI cK cL cM cN cO cP cQ cR cT Cw Cx dA dB Dd De dH DI dN Dr Du Ed Ef Ex Fa Fc Fi Fp Fr Fw Fy Gc Gl Gn GP Gz Ha Hb hG Hl Hp Hq Hr Hu Hw Hx Ih Ii Ij Ik Il Im In IO IP Iq Ir Is It Iu Iv Iz Jg Jh Jl Jm Jn Jo Jq Jr Jy Kc Kd KE kG kI Kj KN KO kP kQ kR Ky Kz Ld Lh Li Lj Lp Lt Lv Lw LX LY Lz Ma Mc Md mE Mf Mg MH Mi Mj Mk MM Mn MP Mq Mr MS Mt Mu mW Mx MY Mz NA Nc nD NF Ng NH nI NJ Nk Nl nM Nn NO NR Ns nT Nu Nv Nw Nx NY Oe OF Oh Oi OK Om oN Ow Oy Oz Pa Pb Pd Pe PF Pg Ph Pi Pk Pz Qa Qb Qc Qd Qe Qg Qh Ql Qn Qt Qu Qv Qw Qx Qy Ra Rb Rc Rh Rv Ry Si Sr Ss To Tv Tz Ua Ub Uc Ud Ue Uf Ug Uh Uk Ul Un Up Ur Ut Uu Uy Uz Vc Vh Vj Vp Vu Vv Vz Wb Wc Wd We Wf Wg Wh Yd Yg Yi Yj Yk Ye Tm Wm Tj tF Yf) nA(Ad aI Aj aK Al Ao Ap aS aV aZ BA Bc bE bH bI bP bR bS bV bX bZ cB cC Ch cK Co cQ CS Cw dA dD dF dI dL dM Dr eC Ed Em Eq Ex Fb Fc Fd Fi Fn FP Fy Gd Gh Gl gP Gz hC hF Hl Ho Hq Hu Hw Hx iA Id Ii Ij Il In IO iP Iq Iu Iv iZ Jd Jf Ji Jm Jn Jp Js Jt Kc Kd Kc KF Kg Ki Kj kN kO kP KR KS Kx Ky Kz Ld Li Lj Lp Lt Lw LX LY Lz Ma Mc Md ME Mf Mg Ml Mj Ml MM MP Mq Mr Ms mT MU mW Mx My Na nB Nd Ne NF Ng NH nI Nj nK nM NN NO Nr Ns Nt nU Nv Nx Oc Of OH Oi Om oO oP Or Ou Ow Oz Pa Pb Pe PF Pg Pi Pk Po Ps Pz Qa Qc Qd Qg Ql Qu Qv Qw Qx Qz Ra Rb Rc Rj Rm Rt Ru Rx Rz Sj St Tn To Tt Tz Ua Ub Ud Ue Ug Uk Ul Um Uo Up Us Ut Uu Uz Vb Vc Vo Vp Vu Vv We Wf Wg Wh Yg Yh Yi Yj Yk Zw Ye Xa Wm Th Yf) kN(aA aH aM Ar aS AW Bb bC bE bG bH bJ bM bN Bo bQ bU bW bX bZ Ch cM cO cS cU CV cZ DB dE dF dK dN Dp Dr Du Em Et Ex Fr Gb gL GP Gz Hb hF Hp Hr Hu Hv Ib iH iO iP Iq Ir Iz Je Jf Jj Jk Jm Jn Jo Jp Jq Jr Ju Jv kI Kj Kn Kx Ky Lt Lv lW Lx lY Ma Mb mE MF Mg Mh mI Ml mM Mq Mr mS Mv mY MZ nB Nc Nd Ne nF Ng nI Nj NK Nl Nm Nn No Nq NR Nt Nu Nx Ny oE Ok oQ Oy Pf Pg Pk Qa Qb Qn Qt Qu Qw Qz Rc Rj Rx Sf St To Tz Ud Ue Uf Uh Um Uo Us Uy Vi Vj Vo Vs Vz Wb Wd We Wf Yd Zx Tm Xa Wm) nB(aH aI aN Ao aP aV aZ Bb bF bG bH bM bQ bR bU bZ cB cF cH cX cY cZ dB DC dD Dk dL Dp DR Et Ex Fn fP Fr Gd gL Hb Hq Hu Hw Ib Id Ih Ij Il Im iO iP Iq Ir iZ Ji Jk Jn Jo Jq Jr Js Jt Jy KE kG Kr Lv lX Mb mE Mg mI Mj Ml MM Mp Mq Ms Mv Mz Nb nC Nd Nf Ng nI nJ Nm Nr nT Nw Nx Ny oE Of Oi Oy Oz Pc Pe Pk Ps Qa Qb Qc Qd Qe Qv Qz Ru Sr St Ua Uh Vs Wd Wf Yd Yi Yk Zw Zx Tm Wm Ti tF Yf) nR(aC aG aI Ao Ar Aw Ax aZ BA bC bE Bg bH bJ bN bS bU bW cA cM cN Co Cs CU Cx cZ Dc dF dG dH dN eC Em Ex Fd fP Fw gL Ha Hc hG Hu Hx iA Ih Ik Il Im Ir Iv IZ Je Jj Jk Jm Jn Jq Jr Ju kI Ko kP Ks Kx Lh Lj Lv Mb Me Mg Mj Ml Mq mT Mv Mw Mx Nf Nj Nl Nn NO Nq Nr Nv NY Oa Og Om Oy Pg Pi Pk Ps Ql Qt Qy Qz Rm Sf To Tv Tz Uc Ue Uf Uh Un Us Ut Vh Vw Wc Wd Wh Yd Yg Yh Yj Yk Tm Xa) rA(aA Et Hu Hx Ih Ik Il In Io Ir Is It Iu Ji Jk Jl Jm Jn Jo Jp Jq Jr Js Jt Lh Lj Lu Ly Mg Mh Mk Ml Mm Mn Mr Ms Mu Mv Mz Nb Nc Nd Ne Nf Ng Ni Nj Nk Nl Nm Nr Nu Nv Nw Nx Ny Oe Og Oh Oi Ok Oy Pb Pd Pe Pf Pg Po Qa Qb Qe qU qW qY rB Tz Ua Uc Wc We Wh Yd Yh Yi Yj Zw Zx Ye Tm Wm) mI(aE aI An Ao aY Bb bC bF bH bJ bU cM cU cZ Et Gb gL Gz Hb Hc Ho Hu iO iP Jg Ji Jn Jq Jr Ju Jv Ke Kn Kz Ma mF Mg Ml MM mP Nf Nn Ny oN Or Oy Pa Ph Pi Pk Qz Rj Sf Sr To Tz Uh Vj Vs Wd Wh Yd Yk Wm Tj Ti) qT(Fr Hu Hw Ii Iq Iv Jj Jk Jp Jr Lh Lj Lu Ly Ma Mh Mj Mk Ml Mq Mr Mv Mx Nd Nf Nk Nl Nm Nn Nr Ns Nt Nu Og Oh Ok On Oy Oz Pa Pb Pd Pe Pz Qd Qe qU qW qX rC Ua Uc Wb We Wf Yg Yj Zq Ye) qX(Et Hq Hu Ik In Jg Jh Ji Jl Jp Jr Lw Ly Lz Mc Md Mh Mi Ml Mn Mp Mq Mr Mx My Na Nc Ni Nj Nl No Nt Nw Oe Og Oy Oz Pb Pf Qc Qe qU qW rB Tz Ua Ud Ue Wc Wf Wg Wh Yd Yk Zx Xa) nN(aE aI Aj Ao Ax aY aZ Ba bC bH bJ bN bW Ch cM cR Cs cU cZ Dd dH dK Du eC Et gL Ha Hx Jn Jr Jv kO mM mP Mq Nf nK Nn Ny Oy Pf Ph Pi Pk Qz Rj Sr Tz Uh Us Vi Vj Wm) qW(Hu Ii Im Io Ip Is Iv Ji Jk Jm Jn Jp Jr Jt Lu Lz Mt Mu Na Nb Nf Nr Ns Nu Nw Nx Ny Of Og Ok Oy Oz Pa Pb Pd Po Pz Qc qU rB Ua Ue Wb Wf Wh Yd Yg Zx Xa) nK(aI Ao aZ bH bJ bL cB cF cM cQ cU cX cZ dA dB gL gP Hc Hu Ib iO IZ Jj Jn Mb Mg Mm Nn oK oN Oy Pi Pk Sr Uh Wc Yk Tj) mP(aH Ao aZ bG bJ bZ cH cQ Cs cU dB dF dK dL Em Ex

Figure 12 Continued gP Gz Hv kC Kx Ma Ml Mp Ms Mz nD Nn Nu Oh Pk Qa Qb Ql Rx Ry St Wm) mM(aE Ao bH bJ cA cM cQ cU cX dK Ed Hc iO Je Jn Kn Mg Mm Mw Mz Nd Nn Nq oK oN Pi Pk Rg Uh Vh Vs Yg Yj Wm Tj) mY(An Ao bF bH cM Ct cU cX Et gL Hu iO Jn Jr Ju Ma Mg Mq Mz Nn No Ny oN Oy Pc Pk Qz Sf Sr Uh Vj Yk Wm) kP(Ao bJ bL bU cQ cU Cw Et Ex gP Hb Ik iO Jj Jn Jp Jr Mz Nn nT Ny Ok Oy Oz Pc Pk Rc Sr St Uh Vj Wm) bJ(kC kE kF kG kI kO lW lY mE mF mH mS mT mU mW mZ nC nD nF nH nJ nL nM nO nT nU oQ) cU(kE kF kG kI lW lY mE mF mH mS mT mU mW mZ nC nD nF nH nI nJ nL nM nO nT nU oO oQ) Uh(kC kE kF kI kO lW lX lY mE mF mH mT mU mW mZ nC nD nF nH nI nL nM nO nT nU oQ) Pk(kC kE kF kG kO lW lX lY mE mF mH mS mT mW mZ nC nD nF nH nI nJ nL nM nT nU oO) Nn(kE kF kG kI kO lW lX lY mE mF mH mS mZ nC nF nI nJ nL nM nO nT nU) Ny(kC kF kG kI kO mE mF mH mU mW nC nF nH nJ nL nM nO nT nU oP oQ) Ao(kC kF lW lY mE mF mH mS mU mW nD nH nI nJ nL nO nT oO oP oQ) Mg(kC kE kF kG lW lX lY mF mW nC nH nI nJ nL nM nU oO oP oQ) cM(kC kF kG lW lY mE mH mS mT mU mW nC nD nH nJ nL nT nU) mZ(aI aZ Ba Bg cT dB Ef Hu Ib Ik iO Jn Kn Mm Nc oN Pi Qu) kO(aZ bH bZ cQ cX dL Et Ex iP Kn lX Ma Mm Nr Qb St Vh Vt) nT(aE aY bF bH gL Hc Ho Jq Jr Kn Mq Sr Tz Vj Vs Wh Wm) nJ(An Ba BG Ch Cs gP Hu Ik Jj Jn Mb Pi Rj Sr Yk Wm) kI(aI Bb Et gP Hb Jr Kn Ma Mm Mz oN Rv Si St Vh Vj) mE(An bH bU gL iO Jn Jr Ju Mq Pi Qz Sr Tz Vj Wm) kC(aE An bH bU cQ dK Et Gb Jr Mq nY Sf Sr Tz Vj) qV(Ik Io Iq Jh Ji Nd Nr Nw Og Oi Oy Oz Pa Pc) kF(aE Aj An bE bU cZ Em gP Hb Hu Vj Yk Wm) rB(Ik Iq Iv Nf Nr Ns Og Oz Pa Pc Pd Qc) aI(lW lX lY mF mH mS nC nD nH nL) jD(Hv Jg Jp jY lL Mr Nd Nf Ni Oe) lX(Bo cR Di Dp oN Rj Tz Us Wm) lY(aZ bF Jn Jr Mm Mq oN Vh Yk) nD(aZ Et iO iP Jn Kn Rg Vh Tj) nH(bU dR Jr Pi Sr Vh Vj Yk Wm) qU(Ih Ik Iq Jh Jm Ms Nf Nr Qc) rC(Ik Iq Jn Nf Og Oy Pc) kG(aZ dK Hb Kx Sr Yk Wm) Ji(hA hV iC jF jL lM) nU(bH Jn Ju Mq Sf Wm) mW(aZ bQ Jn Vj Yk Wm) Kn(kE mS nF oO oP) mF(Jn Mm Sr St Yk) nL(Bb bU Jr Vj Wm) hV(Jn Mt Mz Nd Nt) qY(Ik Iq Jh Nr Og) oQ(Et Ex Kk Qb Qe) mS(Cw Mm oN St) rZ(Ub Wc Wd Yd) mT(dR Ma St) nC(bU Vh Wm) Wc(jT rX) Kp(gL gW) lW(bU Jr) mH(dR Rx) oO(Et Wm) ManO NdhX NfjI RgoP aZnI} Bb{sC(aG aH aJ aS Bc Bg bJ bM bX bZ cH cK dG Dk Dp dR eC ED EF ET EZ Fa Fb FN FP Fr Fw FY GL GP gW HA HB HC HF hG hL hO hP Hq HR Hu HV HW HX iA IB IC Id IH Ii IJ Ik Il Im In IO IP Ir Is It Iu Iv IZ JD JE JF JG JH JI Jj JK JL JM Jn JO JP JQ JR Js JT JU JV JY Kc Kd Ke Kf Kg Ki Kj Kk Kl Kn Ko Kp KQ KR KS Kx Ky Kz Ld Lh Li Lj lK lL lM lN lO Lu Lv Lw Lx Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pk Po pY Pz QA QB QC QD Qe QG QH qI Ql Qm Qn qO qP qQ QT QU QV QW QX QY QZ RA RB RC Rf Rg Rh Ri Rj Rm Sr Ss St Tn To Tr tS Tt Tv Tz Ua Ub Uc Ud Ue Uf Ug Uh uI Uk Ul Um Un Uo Up Ur Us Ut Uu Uv uW vA vH Vo Vp Vs VT Vu Vv wB Tj Ti tF) pS(Aa aJ aN Bg cH cK dB dI Dp dR eC ED EF ET EZ Fa Fb FN FP Fw FY Gl Gp gW HA hB HC HF hG hL hO hP Hq HR Hu HV HW HX iA IB IC Id IH Ii Ij Ik Il Im IO IP Iq Ir It Iu Iv IZ JD JE JF JG JH jI Jj JK JL jM Jn JO jP JQ JR JT JU JV JY Kc Kd Ke Kf Kg Kj Kk Kl Kn Ko Kp KQ KR KS Kx Ky Kz Ld Lh Li Lj lK lL lM lN lO Lu Lv Lw Lx Ly Lz Ma Mb Mc Md Me Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv NW Nx NY Oa OE OF Og OH Oi OK Om ON Or Ou Ow Oy Pa Pb Pc Pd Pg Ph Pi Pk Po pY Pz QA QB QC QD Qe QG qH qI Ql Qn qO qP qQ QT QU QV QW QX QY QZ Ra RB RC Rf Rg Rh Ri Rj Rm rX Sr Ss St Tn To tQ Tr Tt tV Tz Ua Ub Uc Ud Ue Uf Ug Uh Uk Ul Um Un Uo Up Ur Ut Uu Uv Vo Vp Vu Vv wH wK Tj tF) wH(cR dR eD eF fN FP Fw fY gW Ha Hq Hv Ii Ik iZ Jd jE JF Jj jM jQ Js JV Kd Kk Kn Ko kQ KR Ld Lj lK Lx Mg Mk Ml Mn Mr Ms Mt Mx Nd Ne Ng Nh Ni Nl Nn No Nt Nw OE Oi OK Or Ou Ow Oz Pe Pi Pk QA qB Qd Qe qG Qh qI qO qP Qt Qw QY Ra Rc Ri rW Tr Tz Up Vo Vs Vv tM Ti) rW(dR eD eT eZ Fb fN fY gP gW hA hL hO hP HR hV hW hX iA iB IC Io Iq Is It Iu Iv jD jE jF jG jH jI jK jL jM jO jP jQ jR jT jU jY kS lK lL lM lN lO Md Mk Ml Mm Mr Nb Ne Nq Nt Nu Nx oE Pa Pb Pc Pi pY qA qB qC qD Ql qO qP qQ qY rB Rh tR tS tX Tz vH Vt wB wG wK yD zH yE tM Th) wK(aC aQ cH Co cZ dR eZ fN Fw fY gL gW Ha Hq Ik iZ jE Jf Jj jV Kk Kn kQ kR Ld lK lN Mn Mr Ms Mx Ng Nn No pF Pi qB qG qI qO qP qX qY Ri rR sO Up vC Tj tF) tM(dR ED Fa fN Fw Ha iZ jE jF jG jM Jq Js jU Ko Kz Lj lK Ml Mr Na Nb Nd Nf Ni Nn No nW Ou Ow Pg qA qB qC qD qQ qY Ri Rm Tt Ub Um Vu wL Tj Th) lK(rP rQ rS rT sK sM tN tO tQ tR tS tT tU tV uI uL uM uO uR uU uV vA vC vH vO vQ vS vU wB wC wD wE wG wJ wL wP wQ yD yK zA yE) yD(Aa cR dR Ed eT Fw fY gW Ha Ik iZ jG jQ jR jV Ki kS Lx Mn Mr Ni Nn nW Or Ou Pi qA qB qO qP Qt Up Vu Ti) wB(aC cR cU fP Fw fY gW Ha Hq Ik jQ jV Kn kQ Ld lM Mg Mn Mr Mt Nd Ni Ok Pi qO qP QY Ra Ri Up Vo Vv Ti) vH(cH cU dB fN Fw Fy gW iB In iZ JD jE JF jH jQ jY Kk Mr Ms Mw Nd nW qD Qh qO qP qY Um Up Uv) Mr(qI rN rP rT sO tV uG uL uM uN uO uT uU uW uX uY uZ vC vP vU wC wD wE wL wP yJ zH zI yE xA) tV(aI dR fY gW Ha hC Hq Ik iZ Jj jQ Lx Mn Ni Nn No nW Or Pg Pi qA qO qP qY Ri Up Vo Vv Ti) Do(Dp Hb Hf Ju Jv Kd Ke Kl Ko Kq Kr Kx Ky Nj Ou Pi Pk Ql Qt Qu Qz Rg Rh Tr Uh Uk Vt Vu) wL(aC cR dR fY gW Ha Hq Ik iZ jE Jj jQ jV Kn Lx Mn Ni Nn Pg Pi qA qP Qt Ri Up Vo Vv Ti) iZ(sO tN tO tQ tR tS tT tU tX uM uO uP uT uX uY vB vC vI vP vU wD wE wJ wP wQ yK xA) qY(eT eZ fN fY hL hO hP pY qA qB qC qD rP sM tR uG uL uM uU uW vU wG wP) vP(cH Ed fN Fw Fy Ha Hq iH Ip Ir Is jR Kf Kz Lv Ml Nd Ni nW Ok Pi Um Ti) vC(Aa aG cJ dB Ef Fb Mk Mm My Na Nb nW Ow Pc Pi qQ Qu Qw rB Rf Uu wP) Ti(rN rP rQ sO tN tO tQ tR tS tT tU tX uG uX vV wC wD wE wJ wP yK) gW(rN rP rQ rU tN tO tQ tR tT tU uU vU wC wD wE wG wJ wP wQ zA zH) Ha(tN tO tQ tR tT tU tX uG uT uU vU wC wD wE wG wJ wP wQ yJ) Pi(rP rQ rR rT tN tR tS tT uG vU wD wE wG wJ wP wQ) uU(Fa fN Fw Ic Jd Jv Mv Ni Nn nW Ow qO qP Qx Qy Rj) fY(tO tQ tR tS tT tU vV wC wD wE wG wJ wP wQ zA) qP(rB rS rT tR tS tT uI uL uO wC wE wG wJ zA) vU(eT iH jF jG Na Nb Ni Nn nW nY Ow Oz Up) cR(tN tO tQ tR tS tT tX wD wG wJ wP zA) Ik(Dq rP tO tQ tR tS tT tX wC wD wQ) Vz(kF kI mT mU nA nB nF nR nT oO oQ) tS(aC aQ aU cU cY jQ Mn qO rP uN) Nb(uG uM uO uW uX wG wP yK yE) qO(qU rB rS tR uI uL wC wE zA) Mn(tU tX wC wD wE wJ wP wQ) dR(rN rO rQ rT rU rV wE wQ) wG(Aa aS jQ Ki Ou Ow Tz) jT(mF mM mS nF nJ nN nR) Ed(eQ fA fB oT oV pK) tR(aC aI Hq jQ Nn rP) uM(jG Ld Ml Na nW rB) wD(aC Jj jQ Ng Up) jP(lY mI mM nI nN) xA(Al dB Ni nW Th) kI(Gn Lh Op Sh Yj) uG(Ki Ml Ou Ow Tz) cU(uT uW uX zH) wP(Aa aC Ki Ou) qH(cY Ex Gz iA) Qu(Dq eX Gw) nA(Gn Yh Tm) jQ(tU wQ zA) rP(iA Rh tX) nW(vI vS zG) uT(Fy Ip Ni) Th(rN rR) Gz(qI qZ) Up(uW wC) Pb(dX eP) cF(eT fN) cY(rV zA) dB(uI uX) eD(nF nO) jF(uL vS) oT(Lh Uf) uN(Aa Rf) vB(Nt rB) AluW DqKi EmqT ExqG GwPk MlrN HqwQ KleX RznO OpmI OkeP OwyJ aIwJ eTrR nRlN mMjL jGyE} Aa{wG(aG Aj Al aM An AO Ap AR AS aV BA bE bF Bg Bn Bo bP bQ bR bZ cB cE cF cG cH cL cN CO cP CQ cR Cs CT Cv Cw Cx dA dB Dc Dd De Dg dH DI dJ Dk DL dM dR eC Ef Ez Fb Fn fP Fr Fy GL GP gW hA HB HC hF hG Hu hW iA IB Ic Id iH IJ Ik Il iO iP iZ Je Jg jH Jk jT jY Kc Ke Kf Kg Ki Kj Kk Kl Kn Ko Kp KQ KR KS Ky Lj lK lM Mg Mt Mv Mw My Ng Nq nW nY Oa oE OF oH Oi oK Om oN Or Ou Ow Oy Oz PF Ph Pi Pk pY qA qB qG QH Ql Qt QU QX Qy Qz RC Rg rP rS sO Ss Tr Tt Uf Ug Uh Ul Un Up uR Us Ut Uu Uv VO Vp vQ Vs Vt Vv tF) vO(aC Ad aM aO aS Aw aZ Ba Bc bE bF Bg bR bW cB cE cG CH cL CP cR dB dE dI dJ Dk dM eF ET FP Fw hA Hb Hc Hu Hx IJ Ik Il Im iO It Iz Jd JE Jg Jk Jo jV Ke kQ kR Kx Lj lM Me Mf Mg Mm Mp Mq Mr Mt Mv Mw Mx My Nc Nd Ng Ni Nk Ny Oa OF Ok Om On Oy qA qH qI qU Qx Qy Rg rP rS rT rX sC Ss Tr tV Uc Uf Uh uM uN Ut Uu vC Vo Vs Vt vU zG tL) uR(aC Ad aE Aj aM AO AP Aw aZ Bc bE bF Bg bN bW cG CH cL cM cO Cp cR dB Dg dH dI Dk eF ET Fb fP hA Hc Hq Hr Hu HX Ib Ih IJ Ik Il Im Iz JD Jg Jk Jo Jp Jt jV Kc Ki kQ Lh lM Md Me Mf Mg Mk Mm Mq Mr Ms Mt Mu Mv Mw My Mz Nj Nk Nr Of Og Ok Om On Oy pS pY Qc qH Qt QU Qx Qy Ss tR Uc Uf Ut Uu vC Vo Vs Vt vU zG Ti) uN(aC Ad Aj aN Ap Ba Bc bE bF Bg bL cG CH Cp Cw dA Dc Dg dH DL dM dR eC EF fP Fr hB hC hF hP hR Hu iA iH IJ Il Im iO iP IZ Jd Jg Jh Jk Jt jY Kc Kl kQ kR Ky Md Mg Mt Ng Nr oE OF Og oH Oi oK Om ON Oy PF Ph Po Pz qH QT Ra Rc

Figure 12 Continued rT Ss Uf Un Ur Uu Vo Vs Vt Ti tF) Jh(pS qH rO rP rQ rR rS rT rU rV rW sC sK sM sO tO tQ tR tS tT tU tV tX uG ul uL uM uO uT uU uV uW
uX uY uZ vA vB vC vH vl vP vQ vS vT vU vV vW wB wC wD wE wH wJ wK wL wP wQ yD yH yJ yK zA zG zH zl yE tM tL xA) Ik(Dq pS
qH rS rT sC sK sM sO tN tO tQ tR tT tU tV tX ul uL uM uO uP uT uU uV uX uY vA vC vl vP vQ vS vT vU vW wB wC wD wE wH wJ wK
wP wQ yD yH yJ yK zG zH zl tL xA) eF(pS sC sK sM sO tV uG ul uL uM uO uP uT uU uV uW uX uY uZ vA vB vC vH vl vP vQ vS vT vU
vV vW wB wC wD wE wH wJ wK wL wP wQ yD yH yJ yK yL zG zH zl yE tM tL xA) vC(aC Aj Ao Ar Aw Ba bE bF Bg cG Ch Co Cp Cw
Dc dE Dg dH Ef hA Hc Hu IJ Il Iz Jd Jg Kc Kg Mg Mt Mu Mv Mw My Ng Nq Nr OF Og Om Oy qH Qt rS Tt Uf Vo Vs) aC(sK sM sO tV uG
uL uM uO uP uT uU uV uW uX uZ vB vH vl vP vQ vS vT vW wB wC wD wE wH wJ wK wL wP wQ yD yH yJ yK zG zH zl yE tM tL
xA) Jd(pS rW sC sK sM sO tV uG uL uM uO uP uT uW uX uY uZ vA vB vl vP vQ vS vT vW wB wC wD wE wH wJ wK wL wP wQ yD yH
yJ yK zH zl yE tM xA) Ng(pS sC sK sM tN tQ tR tS tT tX uL uM uO uU uW uX uY vA vB vH vl vP vQ vS vU vV vW wB wD wE wK wQ yH
yJ yK yL zA zG zH zl yE tL xA) bE(pS sC sK sO tV uG ul uL uM uO uP uT uU uV uW uX uY uZ vA vB vH vl vP vQ vS vT vU vW wD wJ
wP yD yH yJ yK zG zH zl yE tM tL xA) Cp(pS rW sC sK tV uG ul uL uM uP uU uV uW uY uZ vA vB vH vS vT vU vW wC wD wE wH wJ
wK wL wP yD yH yJ yK zG zH zl tM tL xA) Vo(pS sC sK tV ul uL uM uP uU uV uW uX uZ vA vB vH vP vQ vS vT vU vV vW wB wD
wH wJ wK wL wQ yD yH yK yL zG zl yE tM tL xA) qH(Bc fN hO hP hX iB IC iH jD jE jF jG jK jU jV kQ IL lM lN IN pS pY qB rX rY rZ uG
uV uX uY vB vU vW wK yJ yK xA Ti Th) Ch(pS sK sM sO uG uI uL uM uO uP uT uU uV uW uX uZ vA vB vH vI vP vQ vS vT vV vW yD yH yJ yK yL zG zH zI yE tM tL xA) Iz(pS sC sK sM sO uG uM uP uT uU uV uW uX uZ vB vH vI vP vQ vS vT vU vW wE wH wQ yD yH yJ yK zI xA) vU(Ad Aj Aw Ba Bg Ct Dc Dd Dk Hu Ib IJ iO Jg Jk Kl Mg Mv My OF Om Oy Pz Ss Tr Ua Uc Uf Uu) cG(pS sC uI uL uM uO uP uT uV uX uY uZ vA vB vH vI vQ vS vT vV wE wH wJ yD yH yK zG zH tL xA) Jg(pS sC sO tN uG uI uP uU uV uX vA vB vH vS vT vW wL yD yH yJ yK zG zH zI yE tM tL) nA(Dr Du Em Eq Fc Fi Gc Gh Hp Lp Lt Op Rt Rz Sh Ux Uz Va Vb Vc Vh Vi Vw Vz Yd Tm Yf) Ef(pS sC sK tV uG uI uM uW uY uZ vH vQ vT wB wD wH wJ wP wQ zG zH yE tL xA) Oy(sC tN tR tS tT tU tV tX uP uT vB vP vQ vV wB wC wD wH wJ wL wQ yD zA zG) Mg(pS sC tN tO tQ tR tS tT tU uM uO uT uU vB vW wE wH wL yK yL zG yE xA) sC(Aj Ao Ar Aw Ba Bg Hc Hu IJ Il Mu Mv Mw My Of Om Qt Tt Uf Vs) Aw(sK sO tV uP uV wB wC wD wH wJ wK wL wP wQ yD yK) Of(pS tQ tR tS uP uU uV uZ vQ wC wD wH yL zG zH xA) pS(Ad Aj Ap bF Ic IJ Il Ma Mm Nr Ny Pz Qt Uf) Mt(tN tR tV uG uT uV vB vQ vS wC wL zG xA) Ba(sK sM uG uP vA vB vS vW wD wH yD zG) iJ(sO uP uV vB vP vQ wH wL yD yL zG zI) Il(uM uT uZ vQ vS wH wL yJ zA tM tL) Ok(dO dX eX Gw rQ rR rU rV vB vI vQ) Ij(sO uP uZ vB vS wH wL yJ zG tL) Ap(uG wH yD yH yJ yK zG xA) Uf(eQ uV vB vP wE zG zI tL) Uu(sK sO tV uT uX wB wQ zI) Vs(uM uZ vS wC wE wP tM tL) tV(Aj Al Ct Og Oi Qh Ss) lM(rN rQ rR rS vB wE wH) uP(aE Hu Mv My Om Qy Uc) Ms(uU uX vP vV wB) zG(Ad Jk Om Pz Qu) Ti(rP vI yJ tL) Uc(vQ wL yL tL) wB(aQ Dd gW Jk) wE(bF Di Hu Kn) Dq(bB Qu Un) wH(bF Kn Nq) rS(gW jE jQ) Th(rP yJ) Ip(Tk Wn) Qt(yD yK) Pb(dX eP) cR(sK uV) mM(Du Yg) sO(Im Jk) kQ(qG qI) oF(uG yK) uX(Dd Ss) vH(Dk Qy) vP(Bg gW) AduZ AjrT DctL DgwL DoNj EdjB NrvQ MatR YjoO VznB RcyD RgeQ TkdE bBdV iOuV yJjV rXrP} nA{Vz(aA aC AD AF aG aJ aK AL An Ao AP Ar AS Aw AX BC Bg bI bJ bN bP bU bW bX bZ cB cF Ch cI cJ cL Co Cp Cq CS Ct Cu CV Cw Cx Db Dc Dd DE DG dH dI Dk DL dN Ed Em Fi Fn fP fR Fw Fy Gb Gd gL Ha hB HF hG Hq Hv Hx iA Ij In IO iP Jh Jj Jk Jn Jq Js Jv Jy KC kI kK Kn Ko Kx Lj Lt Lu Mb mE mF mI Mj Mk Ml MM Mp Mr mS Mu mY nB Nd NF Ng nH NI nJ NK nL Nn Nt nW oE Of Oh oK ON Or Ow Pb Pc Pd Pk Pz Qa Qb Qd Qh Qt Qv Qw Qz Rf Rj Rm Ru Rx Rz Sh Si Ss Tv Ua Ub Uc Ud Uf Ug Uo Ur Us Ut Uw Ux Uy Vb Vi Vs Vu Wf Yd Yi Zq Zw Xa Wm Ti) Tm(AD Af aH Al An Ao Ap aQ AR As aV Aw Ax Ba Bc Bg bH Bn BO bR cF Ch cL Cp Cq CS Cu Cv Cw Cx dA DB Dc Dd De Dg dI DK DL dN Du eC Ex Fb Fi fP Fr Gb Gh gL Gp HB hG Ho Hp Hq Ib Id Ik iZ Jd Jn Jr Ju KC kI Kk Ko Kp kR kS Kz Lt lW MH mI Ml mM Mq mS Mt mY Mz Na nC Nf Nt nU Oa oE oF Og oK oN oO oQ Pf Qn Qv Qz Rh Ri Rx Sf Ss St To Uf Um Uo Ur Ut Ux Vb Vj Vp Vs We Wf Ye Wm Th) Yj(aF aG aI aK aO Ar AS aX bH bN bO cB cC cK Cq cV cW Cx DB Dd De Dg dI dK Dl dN Dp Dr Ef Ex Fc Fd Fi Gh Gp Gz Ha hB HC HF Ho Hp Ic iO Iq Ir Iz Jd Jn Ju Jv KC kK Kp KQ KR Kz Lp Lt Lu lW Lx mH Mk Ml Mq mY Mz Nf nO NT Nv Oa oF oN Or Oz Pc Pk Ps Qg Qn Qt Qv Rg Rz Sf Sj St Tr Uh Uk Um Un Uo Ur Uu Ux Vh Vp Vs Vt Vu Yi) Gn(Aj Al An Ap Ar As Aw Ba BC bE Bg Bn Bo Ch Co Cp CS Ct Cu Cw cX Db Dc Dd De Di Dk Dl dN Em Fb fP gL Gp Hp Hu Jn Jr KC Kp Ky Kz Lt Lv mI mM Mq Na Nf nJ nO Nt nU Ny oP Pc Qv Ri Rx To Uo Vp Vs) Fi(Ba Cq Cu dI dK Ez Fb Fr Gh GL hB Hc hG Ij Ik Io Jd Je Jg Jn Jp Jr Kl Ko Kq Lh Me Mg mI Mq mS Mw mY Na Nh Nr nT Nv ON OP Oy Pg Qv Rz Tn Tr Uf Um Vp Vs Zq Xa) Yh(Ad aQ Ar aV Ba bO bR cK Co cR cX DB Dl dK Dp Fd fP Gh hB Hc Hf Ik Js Kc Kl Ko kS Ky Kz Lt Lu mM nB Nh nU oE Oz Pc Qv Ri Rx To Tr Uf Um Un Vp Vt Ye) Mq(Dr Du Em Fc Fd Gb Gc Gh Hl Ho Hp Lp Lt Op Ps Rt Ru Rx Ry Rz Sf Sh Si Sj Uw Ux Uy Uz Va Vb Vc Vi Vj Vw Wc Wd We Yd Ye Yf) Qv(Du Em Eq Fc Gb Gc Hl Ho Hp Lp Ps Ru Rx Ry Rz Sf Sh Si Uw Ux Uy Uz Vb Vc Vi Vw Wc Wd We Wf Wg Wh Yg Yi Yk Zq Zx Ye Xa) Hl(As aV bO Ch cR DB dK dN Fb fP Gh gL gP Jh KC Ki kK Kp kR Kz Lt Lv mH mI Ml mM mP mW Na oN oP To Um Vb Vp) mI(Dr Du Eq Fc Fd Gc Gd Gh Ho Hp Lp Lt Op Ps Rt Ru Rv Ry Rz Sf Sh Si Sj Uw Ux Uy Uz Va Vb Vc Vh Vi Vj Wc Ye Yf) Kp(Dr Du Em Fc Gb Gc Gd Gh Ho Rt Ru Rx Rz Sh Si Sj Uy Uz Va Vb Vc Vh Vw Wb Wc We Wf Wg Wh Yd Yi Zw Zx Ye Yf) fP(Du Em Eq Fc Fd Gb Gc Gh Ho Hp Lp Lt Op Ps Rt Rv Rx Ry Sh Ux Uy Va Vj Wc Wd We Wf Wh Yd Yi Zw Xa Yf) gL(Dr Du Em Eq Fd Gb Gc Ho Hp Lp Lt Op Ps Rt Rv Rx Ry Sf Sh Ux Vb Vh Vj Wc Wd We Wf Wh Yk Zx Ye Xa Yf) nT(Dr Du Eq Fc Fd Gc Ho Hp Ps Rt Rv Rx Ry Rz Sf Sh Si Sj Uw Ux Uz Va Vb Vc Vh Vi Wc Wf Yg Yi Yk Ye Yf) mW(Du Eq Fc Fd Gb Gc Gh Hp Lp Lt Op Ps Rt Ru Rx Ry Sh Si Sj Uw Uz Va Vc Vi Vw We Ye) aX(eD gW iC jD jE jF jG jI jK jL jM jO jP jQ jR jT jU jY lK lL lM lO qT qV qW rA) Fb(Eq Fc Gb Gc Ho Op Rt Ru Ry Rz Si Uy Va Vb Vh Vi Vw Wb We Zx Xa Yf) Kz(Dr Du Em Fd Gh Ho Hp Lp Op Ps Rx Sh Sj Va Vi Vj Yg Yi Zq Zw Ye Xa) hC(eD iB iC jD jG jI jK jL jM jP jQ jR jT jU lL lO qT qV qX qY rA) Gh(aC Ba Cv cZ Hu Ib Ik Iz kC kK Kn Mb Mm Nq oP Pc Qe Qw Um Wd) Hu(Du Eq Hp Lp Lt Op Ps Ru Rv Sh Sj Uw Ux Vb Vi Vj Vw Wh Ye) Pc(Dr Du Fd Gb Ho Hp Lp Op Ps Rx Rz Uw Ux Va Vi Vj Yi Ye) Fd(Ha Jk Jr Me Ml Nf Nq Nt Nv oP Pg Rg Um Vs Yg) Em(bJ bP cQ dA dK kC Ki Mg Na Qw Rf Um Ut Tj) Nf(Dr Gb Gc Hp Op Ps Rx Va Vh Vi Vw Wd Zw Ye) Op(Aj Ap Co cR Cv De Dg Dk Dl In kC kK oP) Ye(bO cR dK dN Ef Ib kC Ko Ni Nq Nt Wc) Rz(Ad Al Ap Dg Hb Ji kC kK Kq Ok Qc Tj) Lt(bJ bP cQ Je Mb Ni Nq Qw Ub Um Ur Xa) Ml(Dr Hp Rt Sf Si Va Vb Vh Vj We Yf) Vp(Fc Gb Gc Gd Uy Va Vh Wc Wd Yg Zx) Zw(dK Ef Hc Hf Iz Jd Jn Kc Ko Ri) Xa(Af Al cR Dd Kc kK nO Qn Rg To) Um(Fc Gb Ru Rx Sj Uw Ux Vw Yi Yk) Va(bO cR Iz Jr kC mT Na Qn Qw) cW(eD iC jE jL jT jU qV qW qX) Si(Ez Ik Jd Jh Jn Kl Ko Tr) Vj(Ad In Je Jq Jr Js Kc St) Gc(Ba cR Cu Ik Ko Na Tr) Vb(Ef Jn kC Kl mE Nq) oP(Dr Hp Lp Rt Ru Uy) Na(Fc Gb Uy Vh Wc) Ho(Jd Jr kC Nt Ri) In(Ps Uw Ux Vh Vw) Wd(Dd dK iZ mH oN) We(Bo Ic Jd Mb Nq) Qw(Rv Ry Sf Uw Ux) iP(eD jL jP lN qT) Tj(Rv Uw Vw Wb) Yg(Al Dd kK lW) Zq(cR cV Hb St) Jr(Lp Ru Sh Uy) Rx(Kn Nc Oz Tv) Rt(cR Jk oQ Vs) nO(Dr Gb Rv Vw) Hp(Ax Cp Cs) Yi(Ar cR Vs) Wc(aV Ik Ki) Jn(Ps Sf Vw) Vh(Ic Jd Vs) cE(jI jY lN) Dr(Qn Wm) Eq(kC Tr) Fc(dD Tr) Yk(Jd oF) Sh(As kC) Pz(Ux Vw) Ps(Fr Nq) Uf(fA oT) aY(eD jT) tF(jL jT) oK(gW qX) AlWb BoYd YfoF GbJe HceQ KcLp RuQn NxjP VsfR aCeD dMlL eFlN} Do{Nl(aN aW aZ BN cQ De dG dK dN Dp Em Ez Fa Fb Fn Fr Ha Hb Hf Ib Ic Id Ih In Io Is Iz Jd Jf Jk Jn Jo Jr Js Jv Jy Kd Ke Kf Kg Ki Kn Ko Kp Kr Ks Ky Kz Ly Ma Mf Mu Mv Mw Nc Nd Nh Ni Nj Nk Nn No Nq Nr Nx Oa Oe Or Oz Pa Pb Pc Ph Pi Pk Qa Qg Qh Qm Qn Qt Qu Qv Qw Ra Rc Rf Ri Rj Rm Sr St Tn To Tr Tv Tz Ua Ub Uc Ud Ue Uf Ug Uk Ul Um Un Uo Us Ut Uv Vp Vs Vt Vu Vv) Ez(aA aC aD aE aF aG aH aI aJ aK aL aM aN AO aP aQ aR aS aU aV aW aX aY aZ bA bB bC bE bF BG bH bI bJ bL bM bN bO bP bQ

Figure 12 Continued bR bS bU bV bW bX bZ cA cB cC cD cE cF cG CH cI cJ cK cL cM cN cO cP cR cS cT cU cV cW cX cY cZ dA dB dC dD DE dG dH dI dJ dK
dL dM dN dO DR Ef eX fR gC gL gP gW Gz Id Iz Jh Lw My Nc Nh Qh Tn To Tr Tt) Ur(Af aK aU bP cE Ch cN Db Di Dk dN Dp Dr Em Fn fP
GP Hc Hq Hr Hv Id Ij In Io Iq Iz Jh Jn Ju Jy Ke Ki Kn Kp Kq Lh Lj Ma Mf Mg Mh Mx Nb Nc Ne Nj Nu Nx Oa Oi Ou Ow Oy Oz Ph Pi Pk Qd
Qm Qx Qz Ra Rc Ri Rm Sr Ss Tn Tr Uf Uh Up Uv Vo Vp Vv Tj) Ug(aO Ar aS aW aZ Bg Bn bP bX cB Ch Cq De dN Dr Ed Fa Fn Fw GL Gw
Gz Ha Hf Hq Hu Ib Ii Ik Iv Jd Je Ji Jl Jn Jr Js Jy Kd Ke Kf Kl Kn Ko Kq Kr Ks Kx Ky Kz Ld Mg My Nm Nn Nr Nt Nx Oe Ow Pa Pb Pd Ph Ql
Qm Qn Qu Rf Tt Tz) Pk(aD aE Aj An Ax Bc bM bX cB cG Cs cV cZ dC DD dF Ex Gw Il In Iz Ji Jl Jr Jv Jy Kj Kx Ky Lv Lx Md Mf Mj Mm
Mn Mp Ms Mv My Nc Ng Nh Ni Nj Nv Nw Of Og Ok Ou Pe Pg Qg Qn Qu Ss Tn Tr Tv Ub Uh Vs Vu Tj) Pi(Aj aW aZ Ba Bc bG bJ bN cC cF
cM cV dC dK Gw Hb Hv In Jf Jl Jq Js Jv Jy Ke Kf Kj Lu Mf Mn Ms Nh Nw Of Ok Ou Pf Qn Qu Rc Rj Tr Tv Ub Uh Un Wm Tj) Jy(Aj An aQ
aU Bg bN bR cF cJ Cq Cw Fb Fp Fr Hf Hu Hv Jg Jj Jn Jp Jv Kj Kl Kq Ld Lj Mb Me Ng Nr Oa Oe Of Om Oz Pa Pc Qz Rc Sr Uc Up Vo Vt)
Hf(aG aH aI Aj aM An bB bP cD cG Ct dC dD DG dL Ed Gp Hc Hv Il Im Iq Ji Kf Kq Kr Ky Kz Mn Mp Mq Nc Ni Nn Nq On Pd Po Qe Qh Rb
Us) Hv(Ed Fa Fb Fn Fy Ha Hc Ic Id Jc Jf Ju Kf Kg Kl Kn Ko Kp Kq Kr Ks Kx Ky Kz Ld Mb Nd Nj Ou Ow Ph Ql Qm Qn Qu Rh Uf Uv) aZ(Dp
Fa Fn Ju Jv Kd Kg Kj Kp Kr Ky Nd Nj Ou Ow Ph Qg Qn Qt Qx Qz Rc Rf Rh Ri Ss Ub Uc Uf Uk Um Uo Up Uu Vo Vs Vv) Ct(Dp Ed Fb Gz
Hb Ik Iz Jd Je Ju Jv Kc Ke Ki Kj Kq Kr Ks Kx Ky Kz Ld Nd Nj Ou Ql Qn Tn To Tv Ua Vs) Vo(aH aY bB bX cG cI Dg Ed Et Fn Hc Ik Jl Ke Ki
Kl Kq Kr Ne Nh Nj Nk Ok Or Ou Pf Pg Qu Uc Un) Jj(Ed Fb Fy Ib Ic Id Iz Jd Je Ju Jv Kd Kg Ki Kj Kl Ko Kp Kr Ks Kx Kz Oa Ou Ow Ph Ql
Qu Uv) Aj(Dp Fa Fb Fn Gz Hc Ik Jd Je Jv Kc Kg Ko Kq Kr Ks Kx Ky Kz Ld Nd Oa Or Ou Ow Ql Qm) Ow(An Bc bH cA Co dI Hc Jl Jo Kg
Kk Kp Mv Nc Nd Ne Nh Ni Nj Nk Nr Om Ph Qn Qv Rb) Nj(Bc bN bR Cu Dd dR Em fP Gd gL Gp Ij Io Jr Ma Mf Nc Nd Om Oz Pb Pc Pf Up)
Of(Ed Fa Fn Fy Hb Hc Ib Iz Je Jf Ju Jv Kc Kf Kj Kn Ko Kr Ky Kz Nd Or Qm Qn) dC(Ed Fn Hc Ic Id Iz Je Jf Kc Kk Kn Kp Kq Kr Kx Kz Ld
Nd Or Ou Ph Qn Qu Un) An(Ed Fa Fb Hb Hc Iz Kf Kg Kj Kp Kq Kr Ks Kx Ky Kz Ld Oa Ou Ph Ql Qn) Ju(Bc bJ bO cM Cp Cx dB Ii Kn Mx
Nk Nm Nr Om Or Ph Qn Qz Ra Ss Ub Vp) Nd(aC Bc bM Dp Gn Ji Ke Ko Kq Kr Mj Ng Nh Nk Ok Om Ou Pf Pg Un) Jl(Fa Fb Jv Ke Kj Kl Ld
Qz Rc Ri Sr Ss Tv Ua Uc Uh Ut Uv Vv) Bc(Dp Kd Ko Kq Kr Ks Kx Ph Qh Qz Tn Tr Uh Um Uo Uv Vt Vu) Ou(cC Co CV Db Ip Iv Kj Mv Ne
Ni Nk Nm Ph Qv Rb Rc Vv) Ke(aQ cO Cu Dg Dl Fy Jo Lj Ma Ng Nm Nr Rc Ss Up Uu Vv) Jv(Aw cM Dr Ii Jq Kn Lv Ni Nk Nm Nr Om Qh Qu
Uv) Uv(aG aM aY cV Mp Mq Nk Nn Ok Pg Qn Un Us) Dp(Af cM cO Fn Id Mz Ne Nk Qz Rm Ss Vp) Rc(Ad aH aM bB cW gC Jg Kl Ko Nk
Ph Tn) Qu(aE cO Cp Em Fy Ir Kj Mf Om Qx Up Vv) Kj(Aw bB Is Jg Kl Kr Mp Nh Ni Ok On) Jo(Fy Hb Jf Kf Ki Kl Kp Kq Un) Up(aG aH bB
Bo cG Gp Ne Nh Ph) cV(Fn Jf Or Qm Qz Ra Rm Ut Vp) Qx(aG aH bB cC cG Ne Nh Ph) Nr(bM Gn Hb Kf Ne Nh Ri) Mf(bX cB Ed Hc Kg Nh
Ph) Nk(Kc Ld Ue Ut Vs) Ss(eX Fa Jf Kg Ne) Or(bN cA Dq In Pf) Vv(Ex Kf Mp Nh Un) Ph(aQ Cu dR gL Om) Ap(Hb Kq Kr Ky) Fy(aH cF Et
Lv) Qz(dF Ip Jf Ne) Kg(dB Om Pb Qy) Ma(Hc Kr Ok) Nh(Kq Ld Uu) Iv(Kl Kr Kx) Qn(cM Nm Qh) bN(Hc Ra Rb) cO(Ji Ky Un) Bo(Fb fP)
Em(Qy Uo) Ne(Ut Uu) Im(Ed Un) Kq(aH gL) Oa(Cs Fp) Om(Fa Uh) Uf(Jh Nu) aY(Qh Tn) NmKf MbOk NgHc JrRm KlaH RiaP bBfP}
Vz{nB(aC AF aI Aj AI aM aN aO aP Ar AS Aw AX BA bB Bc bE BG bH bI bJ bL BN BO bU bV bW cB cE cI cJ cM cN cQ CS Ct CV cX cZ
DE dF dG dH dI dK dM dN Dr Du eC Ed Ef Em Et Ex Fd Fn fP Fr Fw Fy Gb Gc gP Ha HB hC HF HI Hp Hq Hr Hu Hv Hw Hx Ib IH IJ Ik Il
Im iO Ip Ir It Iu Iz Jg Ji Jm Jo Jp Jq Jt Ju Jy kC kG kI Kl kP KQ KR KS Kx Ld Lh Lj Lp Lt Lu lW Lx 1Y Mb ME Mg Mh ml Mk Ml Mm Mq Mr
mS MT mU mY MZ Nb nC ND NH NI nJ Nk nL Nn nO Nq NR Nt NU Nv Nx nY Oa OE OF Og Ok On Op Ou Oy Pb Pf Pg Po Ps Pz Qa Qc
Qd Qh Ql Qt Qv Qw Rf Rt Rv Rx Rz Sf Sh Ss Tr Tt Tv Tz Ua Ub Uc Ue Uf Uk Ul Um Uo Ur Us Uv Uw Ux Uy Vh Vo Vt Vu Vv Vw Wb Wd
Wf Wh Yh Yk Zq Zw Zx Ye Th tF Yf) nR(aC Ad aE aJ AI aM Ap Ar AS Ax Ba BC Bg bI bJ Bn cA Ch cK cN Co Cp Cq cR Cs Ct Cu Cv Cw
Cx Dc Dd Dg dH DI DK DL dN Dp eC Em fP gL Gp hB hF Ho Hq Hr Hu Hw Hx iA Ih Ik Il Im In Io Ir Is It Iu Je Jk Jl Jm Jn Jo Jr Js Jt Ju Jv Kc
kK kO kP Ks Ky Lh Lj Lt Lu Lv Lw Lx Ly Lz Ma Mc Md Me Mf Mg MI Mj Ml MM Mn mP Mq Ms Mu Mv Mw Mx MY Na nC NF NJ nK
nL NM No Nq Nr Ns Nu nW Nx nY Of Og oH Oi Om Or Oy Pd Pe Pg Ph Pi Pk Po Ps Qa Qb Ql Qm Qn Qy Qz Rj Rx Sf Tz Ua Uc Ud Uf Uo
Up Ur Uw Ux Uy Va Vw Wb We Wg Wh Yd Yi Yk Xa Ti Yf) kK(An Ao Aw aY aZ bG bJ bN Bo bU bV cP cR cU cW DB dC Di Dp Ed Em
Fy gP Gz Hq Hw Il iP iZ Jt kE kI Kq Ky Lx Ma Mf Mg Mh mI Ml Mr mS Mw mY Nf Nh nJ nK Nn Nu Ny Of Og Ow Pi Qm Rj Rx Tn To Tz
Ud Ue Up Us Uy Vj Wb Yh Yk Zq Ye) nK(aH aI Aj aM An Aw Bc bF bH Bo bU cJ cM Cq cZ Db Di Dp gL gP Hc Hw Ib Iz Jj Jq Jr Ju kO kS
Ky Lt Mf Mg Ml mM mP Mq nI NN Nq Oy Pk Qm Rg Rj Ry Sf Sr To Tv Ue Un Up Us Va Vj Wc Wd Wf Wh Wm Tj) nJ(aM Aw aY aZ Ba bB
BC bF BG Bo bU cM Cq Cs Cu cZ Db Di Dp gL gP Hu Hw Ik Jn Jr Ju kl kS Ky Lt Mf Mg mM mP Mq Nx Ny OF Qg Qn Rg Ri Rj Sf To Ub
Us Vj Vs Wd Yk Wm) mM(aE aZ bH bJ Bo bU bZ cM cQ dK Du Ed Ex Hq Hw iO iP Iq Jq Jr Kf kP lX Mg mP Mz Nn Nq Nu nY pF Qe Rg Rj
Sf Tr Tz Up Us Uy Vs Wb Yg Yk Yf) mP(aA aH aI aO Ar Aw aZ bI Bo Cp cR Cv Db dl Hq Hw iP Kx Ky Ma mI MI Nn NT Nu Ow Qn Qy Rj Rx
Ur Us Xa Th) Nf(eD gW hA hR Hv hX iB jD jE jF jG jH jI jK jL jM jO jP jQ jR jU jY jY kN IK IL IN IO ml qU qX rA rB) Mg(kC kE kF kG kI
kN kO kP IW IX IY mE mF mH ml mI mS mW mY mZ nC nF nH nI nL nM nN nU oO oQ) Wm(kC kE kI kN kO kP IW IY mE mH mI mS mT
mU nC nF nH nI nL nM nN nO nT oQ) Rj(kC kE kF kO kP IW IY mE mF ml mS mU mW mY nC nD nH nI nL nN nO nT nU oO) Db(kE kN
kP IW IX IY mE mF mH mS mT mU nC nD nH nI nL nN nO nT nU Ol oO oQ) Dp(kF kG kI kN kO kP IW IX IY mE mF mS mT mU mW mY mZ
nC nN nO nT nU oQ) kP(aN Aw aZ Bo bU cM Cw Ik Ky Nn Nx Ny Pk Qu Rc Sr Uh Us Vj Yk) oO(AI aM Aw Ax Bn Bo Co Cs Cv Cx Dc Dd
De Di Du Hp Mr Pf Us Yk) mY(aZ bJ cU Et Hu Hw Jr Ky Mq NN No Ny Pc Pk Qg St Uh Vh) mI(Ao aY bU cM Cq Cw gL Gz iP Jn Jr mF Mq
Ny Or Pc Yd Yk) Yk(kC kO IY mE mF mH mT mW mZ nC nD nH nL nN nT nU) Us(gL kC kF kI kN IW IY mF mS mU mZ nC nD nN nO oP)
mZ(Aw aZ Bo dB Di Ed Ef Hc Ik iP Iz Jh Jq) Vj(kC kF kG kI kN kO mE mF mT nD nH nN) qT(Hw Hx Ii Jn Lj Nu Pe qY rB rC Tz Wc) Pk(kC
kE kG kl kN kO mE nC nH nI oQ) bU(kN IY mE mH mS mU nF nH nL nT nU) nN(Ao cM cR Di Du eC Jv Pf Ph To) kO(aA aO cM cR iP Ms
Mz Nn No Sf) jD(Hu Hv jE Jg IL Mr Ni Oe Wc) kN(Bo cR Di Jv Ky Qn Rc Rx To) lY(al cM Ju Mq Sf To Tz) nH(Ao Aw aZ bJ Bo gP Ml)
kF(Ao bE Bo cZ Di gP Rg) gL(bN Ch Dc Kc nT Qt) nU(aZ Bo cM Di Ju Sf) mF(aM Ao Aw Cq gP To) Tz(hV jY kC kG qX) nO(bJ cM Ju Mq Sf) nT(Ao Jn Ju Mq Sf) mE(Ao cM Di Hw Jn) Wc(hV iB rX rZ) Bo(lX nD nL) Di(mS mT nL) Ji(hA iC lM) cR(mS mT oQ) gW(Jp Ke Mn) lW(Aw cM To) mW(Ky Qu Sr) iP(Hu mU nD) jV(iB Nc Nj) kI(aI Ma Rv) Nd(hV hX) Pc(qU rC) NchV NjhX JmjE JrrA aOoQ aZkC cMnD mHnY} eQ{Hc(Ad Af aH AJ AL aM An Ao AP aQ aR As aV Aw AX aZ Ba bC BN Bo bS bU bV bX cA cB cD cE cF cG Ch cI cM cN Co cP Cq cR Cs Ct Cu CV Cw CX cZ Db Dc dD DE Dg dH Di dJ Dk Dl dN Dp dR eM Et Ez Fa Fn FP gC GL gP Ha hB hF hG Hr Hv Hw Hx iA Ic IH Ii IJ Ik Il Im iO Iq Ir Is Iu Iv Iz Jd Jj Jl Jm Jn Jr Jt Jv KC KF kG Kj kK Kl kN KO Kq Kr Ky Ld Lh Li Lj Lu lW Lx Ly Mb ME MF Mg Mh Mj Mk Ml mM MP Mr mS MT Mv MW Mx MY MZ nB Nc ND Nf NH nI nJ NK Nm Nn NO Nr nU Nw Nx Ny Oa Of Og Oh Oi OK On oO Or Ou oV OW Oy Pa Pb Pe Pf PH Pi Pk Qb Qc Qd Qe Qh Qn Qt Qv Qw Qy Qz Ra Rb Rf Rg Rj Ss St Tr Tz Ub Ud Uf Uk Un Uo Up Ur Ut Uu Uv Vt Wm Tj) Ed(Ad Af Aj aK aL Ao Ap Ar As Bc bE BN Bo bV cB cF Ch cI Co CP Cq cR Cs Ct CV Cx cZ Db Dc Dd De Dg Di dL dM dN Dp dR fB fP gP gZ hB hF Hr Ib iO Iq Jr KC kG kK Kp Li Lx Mf Mk Ml mM Mq Mw mZ nC nD nJ Nm Nr Nu nW Ny Oa oO oP oV PF Pz Ql Ri To Ub Uc Ue Uf Uk Uo Ur Us Wm) Mw(aM bC Dp Ef Ez Fa Fb Fn Fw Fy Gl Hb Hf Ic Id Jd Jf Ju Jv Jy Kd Ke Kf Ki Kj kK Kl Kn Ko Kp Kq Kx Ky Lx nD Nt Oa Or Ou Ow Ph Pk Qg Ql Qm Qt Qu Qw Qx Qy Qz Ra Rc Rf Rg Rh Rj Rm Sr Ss St Tn To Tr Tt Tv Tz Ua Ub Uc Ud Ue Ug Uh Uk Ul Um Un Uo Up Ur Ut Uu Uv Vo Vp Vs Vt Vu Vv) Ao(Dp Ef Ez Fa Fb Fn Fw Fy Gp Ha Hb Iz Jd Je Jf Jv Jy Kc Kd Ke Kf Ki Kj

Figure 12 Continued

RjUk} pK{Ba(Ke Lx) Mw(Ju Ki) To(Jp Nq) BcJv CvUr GpJp} cH{Uc(uT vS vU) Dc(vS xA) RmvS Unzl PdsC} mU{cE(hA jl IN) bJ{Gh Ye)
ArYi EmYk NalK} rA{Dr(Aw bR cQ) EmbR NkZq UbYg ZxJm bPoP} oQ{dM(hA lN rX) Yf(Qb Zw) YgQb VbdR cQIN} al{Dg(wC wD)
Ke(tQ tU) wB(Ri Ub) IczH} aN{Co(dV gT) Jo(uZ vT) Pd(uN uZ) lirV} IK{Rc(wC yD) vH(lm Uh) NanH UbmF KetQ} Ar{Yi(kE mP nC nL
nO) YhnH} mS{Gn(Cw Ny) CqHI CxHp FinH ToTm} jI{cE(mE nH nL) ZxJm cMnU eFnI} qV{Dr(bR cP) Gc(bR Kc) Zw(li Oz)} rY{It(kO
mF nL nU) bPmE nlhB} vU{Nn(Kj Uc) Ug(qC qD) DkjM KjbM} lj{Pg(tO tQ tT tU tX)} Hb{aL(tO tQ tT) cMwD tUuN} nO{Yg(Uh Vi Yd)
Vw(Mm Ny)} Vb{MqnC UenH IzdR bJmE} Ph{uN(tU tX wB) NymP} bM{Gt(bB bJ) GpgT ImsC} jB{BaLx CvUr HceC QzbE} IN{DinF
cElW dMkE hGoP} Dg{Mn(wJ yD) NvwQ} Lu{UbvH KkvB RitV} Kc{Gd(iB jM) FckE} mF{ToTm YgJs cSrX} iA{rW(li Kf Un)}
qY{Dr(bR cP) GcbR} oP{YfZw YebJ cGrZ} Cp{Nn(vS wD)} Vv{oE(tN tQ)} bB{DegT MmyJ} bP{nF(jM rX)} cJ{NmxA aVdV} IW{UeTm
KzRx} iB{MkZq JmYe} jU{CunC UpkO} BatVnW BgbEgT CvdEvC DctQuN FiUanL GnTolX MePsnU MsQgwP MtWflM HpIniO IztTiZ YhaZnH PzdAwK JhKiwB UlUxjO UnVhjK PfcZtX Unconstrained panels with 2 analytes, where 1.0E-8 >= 'AUC p-value' > 0. Contains 316 panels of 196,694 total panels evaluated. : Ok(dX eP Fp Hr Hu Hw Hx Ii Ij Ik Il In Iv Jj Jo Js Lu Lz Ma Mb Mc Mf Mg Mj Mk Mn Mp Mt Mu Mv Mw Mx My Na Nb Nc Nd Ne Nf Ng Nh Nj Nk Nl Nm Nq Nt Nv Nx Ny Of Oh Om Oy Oz Pa Pc Pd Pe Pf Pg Qb rQ rR) dU(Cp Ed Et Fa Fy Ij Ik Im Jd Jf Jg Ji Jt Jv Ke Ko Ld Lh Li Lx Mw Mx Nc Nj No Nq Nr Nv Nx Oa On Pd Pc Pj Qh Qm Qn Rg Tv Uf Uk Up Ut Vs) Pj(jO pS rP rZ sC sO tN tO tQ tR tS tT tU tV tX uN uW vA vH vI vU wB wD wF wG wH wJ wL wP wQ yD yJ zH zI tL xA) Et(Fp Hu Hx Ik In Iv Jg Ji Jj Jr Ma Mb Me Ms Mt Nc Nd Ne Nh Nj Nk Nl Nq Nt Nx Oh Oz Pb Pc Pd Pf Qb) Tl(dR gL gP hC iZ jD kC kI kP mY nA nB nJ oF) Vq(qG qH qI qZ rN rO rP rQ rR rS rT rU rV rW) jD(Uw Ux Va Vc Vh Vj Vw Wc Wd Zq Zw Zx) wF(Ad Ap Bb cW Dg Ij Jg Jh Kg Mg Ng Ti) Yl(kK kN mI nA nB nR qT qW qX rA) Do(Ju Jy Nd Nj Nl Or Ow Pk Ur) Ng(uT wB wG wH wJ wL) Ik(dE Dq Ji Jj Jp Nw) Vz(kK mP nB nJ nR) Uf(eQ fA oT pI) aC(Ad Cp Dg Dl) qT(Dr Vc Wc Yd) Bb(pS sC wK) Jg(dE pS wH) aN(cC dE Ji) Aa(uR vO) Dq(Fy Nj) Gw(Nj Pk) Mb(Ji Nw) Nk(Nc Nl) Wc(iB jT) Kg(tR wG) Pb(dX eP) ApuT CpdE EdjB IjwH HceQ YjqX JtpS XalK TmnA JycX VwiC OzeP PitR dBvS fAfP Unconstrained panels with 2 analytes, where 1.0E-7 >= 'AUC p-value' > 1.0E-8. Contains 281 panels of 196,694 total panels evaluated. : Et(Hq Hr Hv Hw Ih Ii Ij Il Im Io Iq Ir Jh Jl Jm Jo Jp Jq Js Jt Lh Li Lj Lu Lv Lw Lx Ly Lz Mc Md Mf Mh Mi Mk Ml Mm Mn Mp Mq Mr Mu Mv Mw Mx My Mz Na Nb Nf Ng Ni Nm Nn No Nr Ns Nu Nv Nw Ny Oe Of Og Ok Om On Oy Pa Pe Pg Po Pz Qa Qc Qd Qe wG) Ok(aA cE dU Fr Hq Hv Ih Im Io Ip Iq Ir Is It Iu Jg Jh Ji Jk Jl Jm Jn Jp Jq Jr Jt Lh Li Lj Lv Lw Lx Ly Mc Md Mh Mi Ml Mm Mq Mr Ms Mz Ni Nn Ns Nu Nw Oe Og Oi On Pb Po pS Pz Qa Qc Qd Qe) Ik(AA aN Fp In Jg Li Lj Mm Mt Nk Nn No Nx Oh On Pa Pf) Jg(aH aN Fp iA Ji Nc Ng Nh Nj Nl Nx Oz Pc wL) Ji(dE In Nc Nd Nh Nj Nl Nt Oz Pc Pd Pf) Pj(uG uL uM uO uT uX vC wE wK yK zG) dU(Ha Ir Iv Je Nd Nl Ph Qw Rm Un) wF(Ch Dk Dl Jd Jt Kn Mv Uc Uf Un) Jp(Mb Nd Nh Nj Nl) aC(Ao Ap Aw Ba Bn) Ng(tR uW vA wP) Uf(fB jB oV pK) pS(Ad dB Or Ti) Bb(rW vH tM) Nh(Nk Nw Nx) aN(bU Cp Pd) Aa(Mt uN) Do(Pi Ug) Ed(eQ vS) Fp(Mt On) Mb(dE On) Mg(wH wL) Nj(dO Nw) Ij(uT wL) Vz(mM nN) Lh(nK oT) Yl(mP nN) jD(Wf Tm) vU(cW dB) AdzH ApwB TjJd MvwH YjnA JnlY TlnK KeeM NwPf PbdE gCnD Unconstrained panels with 2 analytes, where 1.0E-6 >= 'AUC p-value' > 1.0E-7. Contains 462 panels of 196,694 total panels evaluated. : Jg(aC Aj Bg bQ bZ cE cO Cu Il In Iq Iu Iv Jj Js Lj Ma Mb Me Ml My Nd Ne Nk Nq Ns Nt Nw Of Pa Pd Pe Pf Qb rQ rR sC sO vH wB) Ik(Ar Fr Hw Il Im Ir Iu Jo Jr Lh Lx Ml Mw Mz Na Nc Ne Nf Ng Nh Nl Nm Ns Nt Nu Nv Oe Om Oy Oz Pc Pd Pe Pg Po Qa Qc Qd Qe) Ji(Aa Fp HR Hu Hw Hx Il Iv Jj Jq Js Li Lu Ma Me Ml Mp Ms Mt Mw My Ne Nf Nk Nm Nq Ns Nu Nx Ny Oe Oi Oy Qb) dE(aC Ad aJ An AR Aw Ba bM Bn cP De Dg Dl Et Fp Jp Jr Jt Mt Nh Nv Nw Nx Ok Oy Oz Pc Pd Pe Pf Un) dU(Dp Fp Gl Hc Ib Ih Ii Jo Jr Kz Lj Mn Mt Mv My Mz Nt Nu Pa Qc Qd Qe Qg Qz Ri Sr Tz Ua Ud Uh) Nw(aN Fp Hx In Iv Me Mg Mp Mt Nc Nd Ne Nl Ns Nt Nx Oe Oy Oz Pc Pd) wF(Ao Cp Cw dB Dc Ef Et Hb Im Kj Om On Ri Ub Vo Vs Vt Vv) Et(AA Fr Ip Is It Iu Jk Jn Mg Mj Oi wH Wn) Pj(hR rB rT rV rW sM uI uP uZ vB vO vP wC Wn) Cp(aF aH aU Bg bZ cK cO Cq Cu Dk eM Fw Tj) Nt(Fp In Jj Jp Li Mt Ns Nx Oz Pa Pc Pd Pf) Nh(Aa aN Fp In Lh Li Mt Nv On Pc Pd Pf) Ng(pS sO tN tU vH vS wC wD wK zA zH) aN(Ad bM Bn cB Ch Lh Ly Mg Nm Nx Oy) Tl(iH iP kQ lW mF nU nW nY oE qU) wH(Ap Bb Ch Jh Ma Ok On Pf Uf Vo) Nj(eX Fr Li Mt Nk Nx On Pf) Ok(Aa No Nr qZ rN rO rP rV) Nl(dO Dq Fr Gw Li Nx On) dB(uO uY vC vI vO wL zH) Do(Dp Hf Jv Mb Ou Uv) Fp(Jp Mu Nx Oz Pc Pd) Nd(Li Mt Nx Oh On Pf) aC(Aj An Ar Ch De Jt) Mb(Gw Li Mt Nv Oh) Jp(Nc Ne Nx Pc Pd) Yl(kC kF nJ nK qV) tR(Al Ch cW Ld Ma) Ad(In Of tS vH) Bb(rV uG uW vC) Vz(gL mI nK qT) Nc(Li Nx On) Oz(dX Li Nx) Pc(Li Mt Nx) gL(Fi Wd Yg) wG(Aa cW Tz) Dq(bM Ki) Me(Aa On) Yj(kK rA) Wc(hR hV) Uf(oW pH) eQ(Lx Uk) wL(Kg Kn) jD(Uz Yf) qT(Vh Zq) pS(Ar Im) AlvU AowB ApzH BggN BnbU TitQ FwKf LyeP NeNk YgiP JnnK JtiA LhlY VqqU aVdV cWwE nAhV qZoQ Unconstrained panels with 2 analytes, where 1.0E-5 >= 'AUC p-value' > 1.0E-6. Contains 1,347 panels of 196,694 total panels evaluated. : Jg(Aa aF aG aR aY bH bM Bn bX cK Co Cq Dg dH Dk eF Fr Fw hB Hq Hr Hu Hv Hw Hx Ih Ii IJ Im Io IP Ir Is It Jh Jk Jl Jm Jn Jo Jp Jq Jr Jt kS Ld Lh Li Lu Lv Lw Lx Ly Lz Mc Md Mf Mg Mh Mi Mj Mk Mm Mn Mp Mq Mr Ms Mt Mu Mv Mw Mx Mz Na Nb Nf Ni Nm Nn No Nr Nu Nv Ny Oe Og OH Oi Om ON Pb Pg Po Pz Qa Qc Qd Qe qH Ra rP rT rW Tn tR tV Tz uO uT UU uW uX Vo vP wD wG wK wQ yD zA zH tM Tj) Ik(Ad Af Aj Al An Ao Ap aR Ax Ba Bb Bn Bo bQ bZ Ch Cp Cq Cs Ct Cu Cv Db Dg DI Dl eM Fw Hq Hr Hu Hv Hx Ih Ii Ij Io Ip Iq Is It Iv Jh Jk Jl Jm Jn Jq Js Jt Lu Lv Lw Ly Lz Ma Mb Mc Md Me Mf Mg Mh Mi Mj Mk Mn Mp Mq Mr Ms Mu Mv Mx My Nb Nd Ni Nj nK Nq Nr Ny Of Og Oi Pb Pz Qb tN Tj) Nw(dU Fr Hq Hr Hu Hv Hw Ih Ii Ij Il Im Io Ip Ir Is It Iu Jh Ji Jj Jl Jm Jn Jo Jp Jq Jr Js Jt Lh Li Lj Lu Lv Lw Lx Ly Lz Ma Mc Md Mf Mh Mi Mj Mk Ml Mm Mn Mq Mr Ms Mu Mv Mw Mx My Mz Na Nb Nf Ng Ni Nk Nm No Nq Nr Nu Nv Ny Of Og Oh Oi Om On Pa Pb Pe Pg Pz Qa Qb Qc Qd Qe) Cp(Ad aE aG aK Al aM Ao AP aQ AR AS aV AW AX aY aZ Bb BC bE bH bI bJ bL bM Bn BO bP bQ bS bU bV bX cA cC cE CH cI cJ cL cM Co cP cR cS Ct cU cV CW cX cY cZ dA DB DC Dd dF Dg dH DI dJ dK Dl dM dN eQ Fr gL Of Pg) Ji(aA aC aH bQ bZ cE Ed eM Fr Hq Hv Ih Ii Ij Im Io Ip Iq Ir Is It Iu Jh Jk Jl Jm Jn Jo Jp Jr Jt Lh Lj Lv Lw Lx Ly Lz Mc Md Mf Mg Mh Mi Mj Mk Mm Mn Mq Mr Mu Mv Mx Mz Na Nb Ng Ni Nn No Nr Nv Of Og Oh Om On Pa Pb Pe Pg Po Pz Qa Qc Qd Qe qU rZ wF Tj) dU(Aa bH dN Ef Ez Fb Fn Hb Hf Id Io Is Jp Ju Kd Kf Kg Kj Kk Kn Kp Kq Ks Kx Mp Ng Nh Nn Oe oP Or Ou Ow Oy Pf pH Pi Pk Qa Ql Qt Qx Ra Rb Rf Rj To Tr Tt Ub Uc Ue Ug Ul Um Uo Uu Uv Vp Tj) dE(Aj aM aW Ax aY bA bF Bo bU cB Ch cK cN cQ Cs cT Cx Ef Fr Gl Hv Ir Is It Kc Ko Kp Lh Li Lj Lx Ly Me Mg Mh Mz Nc Nd Ne Ng Nl Nr Nt Oi On Pa Po vS Wn) Nt(aA aN eM eQ Fr Hr Hu Hw Ih Il Im Iu Jq Jr Js Lh Lj Lv Ly Mb Ml Mu Mx Nc Nd Ne Nf Ng Nh Nj Nk Nl Nn Nv Of Oh Om On Oy Pb Pe Pg Po Qa Qb Qe) aN(aC aE Ar aU Aw aY Ba bC bH bS bX cG cN De Dg Dl Ef Et Fp Ih Jd Jl Jt Ml Ms Mt Mv Mz Ne Ng Nj Nl Nn Nv Og Oi Ok Om On Pc Tz Un Tj) dB(aC bM sK sM sO tN tR tS tU tX uG uI uL uM uN uP uT uU uV uW uX uZ vA vB vH vQ vT vW wE wG yH yJ yK yL zI yE tM tL xA) Fp(Fr Hu Hx In Iv Js Lh Li Lv Ly Mb Me Mf Mg Mh Mm Mv Mw Mz Nc Nd Ne Nf Nj Nl Nn Nv Oe Of Oh Oi Om Oy Pa Pb Pf Qa Qe) aC(Af Al aM aR Ax Bb BC bE Bg bM Bo bU cB cC cG cN Co Cv Cw Cx Db Dc Dd Di Dk dN Et FR Gw wL) Nh(Ad Fr Hw Il Im Js Jt Lj Lx Mb Mg Mm Mu Mw Ne Nj Nm Nn No Ns Oh Om

Figure 12 Continued

Oy Oz Pa Qb Qe) Jp(Hw Hx iA In Io Iq Iv Jd Ly Me Mg Mp Ms Mt Mu Mw My Nm Nq Ns Of Og Oy Oz Pe Pf Qb wF) Pj(cE iP Jd jP qU
Qv qY rN rQ rR rS rU rY sK uR uU uV uY VS vT vV vW yH yE tM Tk) On(Hr Hw In Iv Jj Lj Ly Ma Mp Mt Mw My Ne Nk Nq Ns Nx Of Oz
Pc Pd Pe Pf Qb Tj) wF(Aw Fy Ii Iz Ke Kf Mw My Nm Ok Or Oy Pf Po Qh Ql Rc Rj Tv Tz Uk Uu Vu) Jd(Ad Ar Bg Ed eQ Fw Hq Hw Iv Jt Lv
Ml Mz Nq pS Ra rW Tz Vp Wn) Ad(Aj An AW bM Bo bQ cB cO cP Dc kS Nd Nj qZ tR uW Tj) NI(Aa eX In Lh Mm Mt Mw Nm Nn Nv Oh
Oy Oz Pc Pd Pf) Nd(AA Dq Fr Gw Im Jt Lh Mm Nn No Nv Oy Pd Pe) Ng(sC tO tQ tS tT tV tX uM uO vI vU wE wQ yD yL) Nx(Aa Fr Hw Jj
Jt Li Lj Mb Me Mt Ne nK Pd Pe Pf) Ok(aH bQ bZ Dq qH rS rT rW sC uO wB wJ wL zH Tj) Tl(eC hB hG kF kK kR kS ml mW oK oN pF rA)
pS(Aa Ap Dg Et Fy Ic Ij Ke Kg Mm Ny Pz Ur) Nj(Jt Lh Mu Mz Nm Nn Nv Oh Oy Pa Pd Pe) Li(Fi Hx In Ly Me Mt Ne Nf Nk Ns Pd Qb)
cW(sC tS tV uM vS vT vW wB wH wL yD zA) Bb(qH ql qP qZ rP rQ rR vP vU wL yK) Kc(Fc Fi Fw Gc Gd Ld Uy Va Vz Yl Tj) Aa(Jr Mb Ne
qH tV Un uO vC vQ zG) Jt(cE Qv tR tS tX vH wG wP zH Wn) wH(Aw Ba Cw Kg Kn Om Pz Rc Uu Vs) Yl(gL jD kG lX mE mM mY nT nU)
Vz(kC kl kO mF mH mS mY nT) Kg(tN tO tQ tS tT tU vU wB) Lh(iA Jj Mb nB Nc Oz Pc pl) Do(bM Ez Iz Kj Ky Ph Vo) Ed(Ar fB gZ No ql
rR Un) Mt(Jj Lj Me Nc Ne Oz Pd) jD(Uy Vb Vi We Wg Yd Ye) Uf(cE Fw gZ oD uT Tj) Ba(bQ bZ cO iA Tj) Ti(rQ tU yJ yK zH) Et(cE iA rQ
uO wL) Nv(In Nc Ne nK Oz) wG(Ij Kn Mg Or Pi) Fr(Mb Nc Oz Pc) Kp(Fc Ru Rx Yd) gL(Fc Si Vc Vw) nA(Fi Gn Hl Yh) nD(cM iP pl Tj)
hV(IY mU nU Wd) Ap(sC tR xA) Bn(bH bM cB) Ch(Gn tS wP) Mg(tQ vA wP) Ne(dX Pd Pf) Tz(hR IL qU) Yj(mM nR qT) Qa(Mb Nk Qb)
Kf(Dq kI Tj) Ux(iC lL lM) eM(eP fP Hc) eQ(Iz Rb Ua) Ma(tS tX) Mz(hA qZ) Nc(Pd Pf) Wc(jM lM) Qu(eX Gw) Kn(tR Tj) Or(sC yJ) Un(Fw
iA) Vo(wJ wL) Pe(eP In) bM(Gn gT) nR(Vs Th) lY(jQ jR) nB(rB rC) kl(Ry Tm) vS(cH Jh) ArPc BggT BoDb CttR DgcO DlcP EftS YflL
EmqT FcHc GtbB LyPf MbMm HpQv UcwL IjwB ImqZ YgiZ SfnT ZqgW QbQe JkVb XanO OhOz aEvQ nNjR

Unconstrained panels with 2 analytes, where 1.0E-4 >= 'AUC p-value' > 1.0E-5. Contains 2,985 panels of 196,694 total panels evaluated. : Jg(aA AD Af AL An AO AP Ar AS aV AW AX aZ Ba Bb BC bE bF bG bI bJ bL Bo bS bU bW cA cG CH cI cJ cL cM cN CP cQ Cs Ct cU Cv CW CX cZ dA DB DC DD De dF dG DI dJ Dl dM dR eC Ed Ef eT EZ Fi FN fP Fy gL gP hC hF hG Ib Ic iH iO iZ Jd Jf Jv Jy Kf Ki Kn Kp kQ KR Kx Kz nK nW nY oE oF oK Ou Oy pF qC qG qI qO qP qQ Qu Qv Qw Qx Qy Qz Rg Rh Ri Rm rN rO rS rU rV tN tO tQ Tr tS tU Ua Ub Uc Ud Ue Uf uG Uh uI UL uM UN Ur UV uZ vC Vp vS vU Vv wC wE wJ wP yJ yK zI tF) aN(Aa aD Af aG aH AJ aK Al aM Ao AP aR aS aV aW bA Bc bF BG bI bJ bL bO bQ bR bZ cE cF cI cK cL cM CO cP cQ cR Ct cU cW CX cY dA DB DD dF dG DI dK dN Ed Em FR Gl Hq Hu Hv Hw Ii Il Im In Io Is It Iu Iv Jh Jm Jn Jp Jq Jr Kc Kf Lu Lv Lw Lz Ma Mb Me Mf Mh Mi Mj Mk Mm Mq Mr Mu Mw My Na Nb Nc Nd Nf Nk No Nr Ns Ny Oe Of Oh Oz Pa Pb Pe Pf Pj Pz Qe Yl) Jd(Af Al Ap Ax Ba Bb bC Bn bQ cE Ch Cq Cs Cv Cw Cx Db Dd DE DI Dk Dl eM Et Fp Hr Hv Hx iA Ik Il In It Iu Jh Ji Jk Jn Js Jv Kc Kf Ki Kj Kn Kp Ld Lh Ly Ma Mg Mh Mi Mj Mk Mm Mp Mr Mt Mv Mw Mx My Na Nb Nc Nd Nf Ng Nh Nk Nl Nm Nn Nr Ns Nv Nw Ny Oe Oh Ok Om Oz Pa Pc Pd Pg qI Qm Qt Qv Qx Rh rN rQ rT Ua Ud Uf Ug Uk Ul Un uO Up Ur Uv VS wG wH Tk) dE(Aa aD Af aH aK Al AO AP aQ aV aZ BB BC bH bI bJ bR cC cF cI cM CO Cq Ct Cu Cv Cw cY dD dF dG Di dJ Dk dL dN Fw Fy Hq Hr Hu Hw Ic Ih Ii Ij Im Ip Iq Iv Jh Jk Jl Jm Jn Jq Js Ke Kf kG Kl kP Lu Lz Ma Mf Mj Mk Ml Mp Mq Ms Mv Mw Mx Nb Nf Ni Nj Nm Nn No Nq Ns Nu Of Og Oh Om Pg Ph pS Pz Qa Qc Qd Qe Rc Rf Rg sC Tz Uf Uh Vs Vt Tk Tj) Ad(Aa aF aH aJ aK aM Ao Ap AR As aU aV Ax aY BA Bb Bc Bg bH bJ bL bP bU bX bZ cE cG Ch cK cN Co CQ Cs Ct Cu cV Cw Dd Di dR dU Ed eM FP Fr GL gP gT Hr Hv Hw iA Ip Iu Ji Jo Js Ma Me Mh Mp Nc Ne Ng Nl Nn Nw Nx Oh Oy Oz Pb Pc Pd Qb qG qH qI qQ Qv rO rP rR rT rU rV rW sC sO tX Un Ur uT vC vS vU wC wH wL wP zI xA Wn) Ik(aC aE aF aG aH aI aK aM aP aQ AS aU aV AW aX aY Bc bE BG bH bI bJ bL bM bN bP bR bS bU bV bW bX cA cB cE cG cH cI cJ cK cL cM cN CO cP cQ cT cU cV CW CX cY dB DC DD De dF dH dJ DK dM dN dR eF Ex fN fP gC Gd gL gP hB hR iA kS oN pS qH Qv rQ tR tX Ur Uv wH wJ) dU(Ao Ap Ax Ba bE bN cF De dG dH dL eC Gp hB hC Hu Ic Ip Iq Iu Jh Jm Jn Jq Js Jy kE Ki kK Kl kP Kr Ky Lu Ly Lz Ma Mb Md mE mF Mg Mh Mk Ml MM Mq Mr Ms mT mZ Na Nb nD Ne Nf Ni nK nL Nm Ns Ny OF Og Oh Oi Om Pb Pg Po Pz Qb Qu Qv Qy Rh St Tn Ur Us Vo Vt Vu Vv Wm) Jp(Aa aC bZ Ed Fr Fw Hq Hr Hu Hv Ih Ii Ij Il Im Ip Ir Is It Iu Jh Jj Jk Jl Jm Jn Jo Jq Jr Js Jt Lh Li Lj Lu Lv Lw Lx Lz Ma Mc Md Mf Mh Mi Mj Mk Ml Mm Mn Mq Mr Mv Mx Mz Na Nb Nf Ng Ni NK Nn No Nr Nu Nv Ny Oe Oh Oi Om On Pa Pb Pg Po Pz Qa Qc Qd Qe Ra Tz Ub Tj) Cp(AA aD Af aI AJ aL An aO BA bB bF bG bN bR bW cB cD cF cG cN cQ Cs cT Cv Cx dD De dG dL dR Ed eF Et Ex Fp gC Gn gP Hr Hw Hx In Ir Ji Js Jt kI Lv Ly Ma Mh Mj Mm Mp Mr My Nc Ne Nh Nj Nk Nl Nn Nq Nr Ns Nu Ny Oe Og Oh Ok oV Oy Pa Pc Pd pS Qb vS wH) On(Aa bZ cE cO Cu Ed eQ Fr Fw Hq Hu Hv Hx iA Ih Ii Ij Il Im Io Iq Ir It Iu Jh Jk Jl Jn Jo Jq Jr Js Jt Lh Li Lu Lv Lw Lx Lz Mc Mf Mg Mh Mi Mj Mk Ml Mm Mn Mq Mr Ms Mu Mv Mx Mz Na Nb Nf Ng nK Nm Nn No Nr Nu Ny Oe Og Oh Oi Om Oy Pa Pb Pg Po Pz Qa Qd Qe) Nh(aA An AR Ba Hq Hr Hu Hv Hx Ih Ii Ij Io Ip Iq Ir Is It Iu Iv Jh Jj Jk Jl Jm Jn Jo Jq Jr Lu Lv Lw Ly Lz Ma Mc Md Me Mf Mh Mi Mj Mk Ml Mn Mp Mq Mr Ms Mv Mx My Mz Na Nb Nc Nd Nf Ng Ni Nl Nq Nr Nu Ny Oe Of Og Oi Pb Pg Po Pz Qa Qc Qd) Jt(aF aH An aR bQ bX bZ cK cO Cu dR Ed eM FP Fw gL gP hR Iv Je Jj Jy kS Li Mb Mt Nc Ne nK Nl Nt oK oN Oz Pc Pf Qy Qz Ra rP rT rW sC sM sO tN tO tQ tT tU tV uM UN uO uT UV vC vI Vo vQ vT vU wC wD wE wH wJ wL wQ yD zA tL xA Tj) aC(aE aF aJ aK aL aO aP aQ AS aU aV aW aX aY bA bB bF bG bH bI bL bP bQ bR bS bV bW bX bZ cF cH cI cK cL cO cP Cq cR Cs CT Cu cW cZ dF dG dH dI dJ dL dM Do Dq Ef Fp Gn Kc Lh Mg Ng Nm Ok Pd wF wH wP Tj) Fp(AA aF bH bL bZ Ch dB Ed Hq Hv Hw Ih Ii Il Im Ip Iq Ir Jh Jj Jk Jl Jm Jo Jq Lj Lu Lw Lx Lz Ma Mc Md Mi Mk Ml Mn Mp Mq Mr Ms Mx My Na Nb Ng Ni Nk Nm Nq Nr Ns Nu Ny Og Pe Pg Po Pz Qb Qc Tj) Li(Aa Ed Hq Hr Hu Hv Hw Ii Il Iq Iv Jj Jk Jn Jr Js Lh Lu Lv Lz Ma Mf Mg Mh Ml Mm Mp Mq Ms Mu Mw Mx My Mz Na Nb Ng Nm No Nq Nu Nv Ny Oe Of Og Oh Oi Om Oy Pa Pb Pc Pf Pg Po pS Pz Qa Qd Qe) Nt(Aa aH Hq Hv Hx Ii Ij Io Ip Iq Ir Is It Iv Jh Jk Jl Jm Jn Jo Lu Lw Lx Lz Ma Mc Md Me Mf Mg Mh Mi Mj Mk Mm Mn Mp Mq Mr Ms Mv Mw My Mz Na Nb Ni nK Nm No Nq Nr Nu Ny Oe Og Oi Pz Qc Qd) Ji(aF aG An aR Ba Bc bH bL Bn Bo bX Ch cI cK cN cO cP CQ Cu dB De dH DI dJ dR eD eF fP Fw gL gP gW hV iA jO lL lY nK qW qX qY qZ RA rB Rm Ur Vp) wF(Aa aF Aj Al bE Bg cM cO Ct Cv cZ dA dH Ed Fr Gl Hq Ib Il Je Jo Kc Kl Kq Ld Ma Mh Mm Mn Ms Nv Of Og Oi Pa Pc Pd Pk Pz Qt Qy Rm St To Tr Tt Ue Ug Um) Mt(An Ar bQ bZ cE cO Ed eQ Hu Hw In Iq It Iu Iv Jk Jr Js Lh Lv LY Mm Mp Ms Mu Na Ng NK Nm Nq Nv Of Og Oi Pa Pb Pc Pf Po Qe Tj) Nx(cK Hr Hu Il In Iv Jh Jl Jr Js Lh Lx lY Ml Mm Mp Mu Mv Mw Mz nA nB Nf Nk Nm No Ns Nu Nv Oh Oi oP oQ Pa Pb pI Po Qa Qd Qe) Aa(aU aY Ba bM Bo Fr Hu Ir Is Iv Lh Nc Nj Nr Nw Pc Pd Pe Pf Po Qa Qe sC sK sO tR uI uP uT vA vB vI vP vU vW wB wH yH yK) Ed(aG aH Ax aY Ba cE Cs Dg Dl Et Ic Im Ju Ke Kf Kn Lh Mm Mz Nn Nv Nw Oh Ok Pa Pd Pe Pj pS Qa Qe Qv Rf St Tz Uf uO vU tM) Pj(aR bQ Ch cN DI dR eM eQ Fn gL hA hP Hu iA iZ jD Je Jf Js Kr Ks Lv Ma Mp Nu Oy Pb Pc Qy rO rX Tz Un Uv vQ yL zA) Nj(aA Ap Ba Dg Dl Hw Ih Im In Iv Jh Jl Lj Lv Lx Mb Mg Mm Mq Mv Mw Na Nb Ng Nl No Nr Nu Oi Om Oz Pc Pg Po Qa Qd Qe) Nl(aA Hu Hw Ij Il Im Iv Jj Jl Js Lj Lv Lx Ly Mb Mg Ml Mq Mu Mv Mz Nc No Ns Nu Oe Oi Om Pa Pe Pg Po Qa Qb Qd Qe) Bb(cK eT fN kS qC qG qO qQ rN rS rT rU sO tS tV uI uL uM uN uO uT uU vB vI vS wB wC wD wP yD yJ zH xA) Mz(cK eD hR hV iA iC Iv jH jO Js jT jV Kf lL Ly Mb Mu Nc Nd Ne nK Nm Ns Oz Pc Pd Pe Pf qU qV qX rA Tj) Nd(aR Ba Dg Hw Ih Ii Ij Io Jl Jm Lj Mg Mh Mi Mp Mu Mw My Nc Nf Ng Nm Nr Ny Om Pa Pg Pz Qa Qc Qd Qe) Lh(aA cE eM eQ Fw hB Hr Hu Hx In Iv jB Jr Js Me Mm Ms Mu Mv nA Ne Nf Nk Ns oN Oy Pd Pf qU rZ Tj) Et(aH bZ cK eT Fn fP Fw hR iP jP Kn Kz Ld Qv qY qZ Ra rZ sC sO tN tR tX Uh uX vH wB wJ zH Tj) Ok(aF aG An aR bG cK cO eM Fw hR iA Kn Ld Pk qG qI Ra rU rZ sO tR uL uM uV uX vP wG yJ Wm) pS(Al Ao cH CW Dc Dl Fw Gl Hb Ii Il Iz Kf Kj Kl

Figure 12 Continued

Figure 12 Continued cO(bM Fp Ji Jr Ju Kq Oz Qe) Bc(Hc Kd Kl Kq Ly Oz Vv) Nj(aN aY cF Gp Nb Oi Pb) Kf(cL Dk Gp Ij Jq Nr Pz) Et(dH Hf Jp Ko Kq Rc) Nk(aN Hc Jd Oz Qy Rb) Or(Ar Bn Hv Id Mg Qm) Pi(aG Ar Hu Jo Ns Vv) Fn(Bn gL Hv Nv Oh) Kl(Bg Dc Dd Ng Pz) aY(Ib Qg Qv Rb Vs) Mg(Ct Hf Kj Uv) Nl(Dp Kj Rh Uf) Iz(Bg cL Dd Ng) Rc(Ad Dg Mm Pd) Kp(cQ Gp Jr Nx) Pb(bH cK Fp Hv) Pk(aG Ar Hu Oh) Di(Kq Kx Ky) Fb(Jt Mm Tt) Nr(Ha Id Nx) Ua(cL Dd Ma) Jf(Hv Nv Uk) aN(Hq Jh Mk) bM(aW eM Qg) Bn(Af bJ) Gp(Kc Kk) Nc(Hf Sr) Jg(Dc Uu) Ss(Fr Ks) Ju(aS bO) Kq(aQ Jt) Rm(Ha Nv) eM(bB bN) AdUu AjKj CtKs FpOz MaPe MmQg NgIb HvPh HxJy JidH QvaM JpKe KkaP NxdE UfgL VvcL} Ed{vS(aC Ad AL An Ap Ar Aw bE CH Cp Cq dB Dc Dd dJ Ef fN Hw Hx Ih Ii Ij Im Ip Is It Jd Jg Jh Ji Jt Kf Kg Kj Kk Ld Lu Lx Ly Mp Mq Nd Ng Nr Or Pa Pe Pi Po Qb Qh qT qU Rg Rm rR rZ sC Sr Tz Uc Ul Uu Vs Vt Wm) jB(aC Ad aI aM aQ aU Bc bN Co Cq Cv Dd dI dJ Et Ez Fa FP Fr gC gZ Ih iJ Jd Je Jm Jq Jr Ke Kk Lh LX Mm mP mU Mw ND Ne Ng Nh Nl Ns Nx oH Ph Po Qa Qc Qm Rf Sr Uc Uf Ul Ur) gZ(aK aW bE bN Ch cO cR cS cW cY dC Ez fA Ha hF Ih Ij Jd Je kG kO kP Lh Lv Lx Mk Ml Mq Nb nD Ne Ng nL nO Nv nY Oa oT Pa Ql Qm Qn Ri Rm St Uk Un Vs Vu tF) rR(aO Ap Ar Ba Ch Cw dI Et Hx Ic Ii Ij Il Im Jd Jg Ji Jt Kf Lh Lx Mm Mz No Nv Nw Po Qm rX Sr St tT vU zH) fB(aA Bc cC Cq dI hF iZ Jf Ki ND Ne Nh Nl Ns nT nY Om Ph Qm Uc Ue Ul Vs) uO(aC Al cH Dd Ii Ij Il Ji Lx Mg Mq Ms Mz Nd Ng Pa Pd Pe Po Qh Rm Sr Uc Vv) vU(Al Ap Dc Dd Ii Ip Is It Jt Kf Kg Ki Kj Lu Mz Ng Pa Pi Qh qT qU rZ Ug) oT(Ad Ar Ax Ch Cq Cs Cx Et Fa hB Ik Im Iv kO Li Mh Nr Pf Po Uf) xA(Al Ap Dc Ic Ih Ii Ij Il Im Ip It Jp Jt Pa Qa Qe) uM(Al Ap Ar Dc Ih Ii In Ip Ji Jm Ms Qh Rm rX Tz) pK(aW Ch Cq Ct Cv cW Dc Di fP Gp nO To Uk Ur Tj) zH(Ad Ap Ar cH Dc Ij Im It Jt Ng Vt tM) tM(cP dB Dk Ij Il Jg Ng qD qU rX Sr) Ij(qI rO sK sO uT vA vP wB wJ) oV(Cq cS fP Ki kO Nc To Us) uT(Ad Ap Im Jg Jt Lx Ng Po) vA(Ih Jo Jt Kg Mg Ng Un Vv) wJ(Et Jp Kg Ng Vv) qI(Dc Il Im Nr Sr) pH(bC kK Kp Kz Nf) wB(Ap Jg Jp Ng) rW(Ar Jg Pe qT) oD(Ct Mw Tv Uf) vT(Al Ih Ip Pa) Fc(kI mM mY) eM(aK Jt nD) gC(kG kK nD) wP(aC Kf Ng) oW(Ct Db dN) vQ(Nd Pa rZ) Il(rO sK) Im(rP uL) Lp(kK mM) dB(uI vC) fA(Cq Cv) eX(aC Hv) sO(Jg Po) rS(Mz Pi) AdvH ThnR SfnO SrrO KgvW cHyJ nDiP} Yj{mM(aC aD aH An aP Ar aU aV aY aZ bB BG bH bI bJ cA cB cH cI cM cR Cs cY dB dI dR EF Em Et Fc Fr Gb Hc Hq Hv Hw Ib Id Il iO iP Je Jj Jk Kj Kk Kn Ky Ld Lp Lx lY MF Mg Ml Ms Mt Mv Mw Mz nC nJ Nm Nn No Nq nR NU Ny oE Of Oi oO Pc Pd pF Pk Qe Qz Rg Rj Rx Sh Sr To Ua Ue Uf Uh Ul Uu Vo Vs Wd Yg Yk Zx Th Yf) gW(Ad Al Dl fR Ha Ho Hu Im Ir Is Iz Jg Jl Jp Jt Ke Kf Kl Kn Kp Kx Mg Mn Ng Oy Ps Qa Qb Qt Qz St Tt Ua Uc Vs We Yg) kK(aG aH aN As Ax aZ bG bN bU bZ cL cR Cs dB Fc Ik Il Jf kI Kn nK No nR Nx Ny oH Ph Qn Qu Rc St Tv Uh Ul Vi tF) nR(bE cR cS cZ dR Em fP Gn Gp Ha hF Hp Hr Hu Ju Jv Kc kP Lt Lv Mf Ml Ny oH oK Qn Rg Sf To Ue Uo Ur Vs) rA(Hq Hu Ih Iq Ir It Iv Jn Jq Jt Ma Mf Mp Mr Mu Mx Nc Ni Nk Nm Nn Nu Oi Pb Pd Qe Tz Wc Wd Yd Zx) qW(Hu Ii Ik Il Io Ip Iv Jh Ji Jn Jp Jq Lv Mf Mt Mu Nb Nf Nx Ny Oz Pb Tz Zx) kI(Ap Ar Bc cR cZ Dc Dg Dk Dl Dp Et Gn gP Ha Kn Kq Ma Ny Qu Rc Si Sr St Wm) qX(Hq Hu Il Jh Ji Jn Jt Mg Mz Nc Nd Nf Ni Nk Nl Nu Nx Pb Qd Tz Wd Yd Yg) qV(Ii Ik Io Lv Mk Mu Nd Oz Pa qT qU Wc Zx) qT(Hw Ip Jt Mg Mt Nn Nr Pa Wf Zq Zw) oO(bC cR Em Gp Hp nD Rg To Uo Ur Wm) kF(Ao Ar Ax Bg Cs GP Qn Rg Ur) mH(An Ao Ar aU Ax Cs dR oH Sr) qU(Ik Io It Js Lv Ms Nn Nr Oh) nN(cS Em Gp Hp Nf oH Or Ur) mS(Cs Dg Dp gP Rg St To Tv) nT(Ao cR dR oH Or Pk Vs) lW(Ar Ky No Ny Pk Sr Wm) oQ(bC bE Hb Rg Sr Wm Yf) mF(Cs Dp gP Pc Rg Wm) mZ(Ef Ib Ik Qn Rj Ut) nK(Cs Hu Kj Kr Qn Vs) lX(Aw Bo Dp Rg To) rC(Hv Iq Jn Pc Tz) mI(cR Nf Or To) nU(Ax Cs gP) lY(Dp Rg To) kE(Kj Rj Vi) kN(aH Mf To) Wm(nI oP) nO(Qz Rj) nC(Mg Pk) nJ(Ax Cs) ChiP EfgP RckP NymY VimE bZkO cRoP} jT{nN(Ad Aj Ap Ba Bg bL bP bQ bZ cI Co Cp Cq Cs Cu Cw dH gL hB Hq iA Ir Is It Iu Iv Jn Jq jR Mv Mx Na Nj Nr Nx Oe Og Ua Ub Uc) nJ(Aj Ap Aw Ba Co Cp Cs CW cZ Di Hq Jn Js kR Lh Li Lx Mp Mz Nr Nx Oe On Pd Qa Tz Ub Uc Uk Um Vo) mI(Ad An Ap Aw Bg Bn bZ Co Cp Cq Cu Cw Cx cZ Dc dE Dk hB Na Tz Ua Ub Uc Uh Um Vo) nL(Af Ap Aw Bn Cp Cq Cw cZ Hq Jn kR Lh Lx Mp Mz Nr Oe On Pd Qa Tz Ub Um Vo) kG(Cu cZ Hq Hw Ir Jm kR Ly Ms Mv Mw Nn Oe Pd Pz Qa Ug Ur) nR(Aj Bo cG Cv Di Ir Jj Jn Jq Lh Ly Mv Na Nj No Nr Po) lY(Fr Ir It Ji JQ jR Lh Mv Na Nj No Nx Oe Om On Pz) kO(Al Aw Cs Dd Hq Jn kR Lh Lx Mp Mz Nr Oe On Pd Qa Ua) Wc(aA Et Hv hW Ji jL Jm jU jV Lz Mf Nd Nf Nj Of Pa) nO(Ap Aw bB Bn bQ cR Cs Cu Cw Cx gP kR Tz Ug Uk Vv) nU(aL Aw aY bB cG Co Cs CW Cx gP kR On Tz Vo tF) mM(aM aP aX bA bE bU cU dF dG eC eF kQ Um Vo tF) kF(aY aZ cG dB Ir Is Iu Jj Ml Mv Na Ni Nj Nr Oe) lW(aM aO bE bZ cU cW dB dC dF dM eF fP hB kQ) nC(Af Aw aY Bn bX Co Cp Cs Cw Di kR Tz Ub Vo) mU(aY aZ bP bZ cR dK dM gL gW hB Mv Na pF) nH(cR Jn Jq kR Lh Lx Mp Mz No Nr On Qa) kP(aK Ao As bE bJ bN bZ Cu dM dN eC eF) nF(Aj Ap Ba Bo bP Di gL pF Uc Um) mZ(cG Ir Mv Na Nj Nr Oe tF) nI(bZ Cu hB Iu Na Nj Ub Um) Ex(Ad Ba Ef Ik Jg Qt Un) nT(Aw Co Cx kR On Tz Vo) mF(Aj Ap Bn Di Jn Mp Mz) kN(Ap Ch Di Mn On Ug Uk) Wd(Hv Jg jU jV Mf Nf) kI(Ar Bn Ch cW Uo Vo) Zx(Iu Ji Jj jV Of) nB(Na Nj Tz Ur Vv) nK(cW It Iu Iv Na) Zw(Jg Ji Jn Jp) kE(Bg Cq Cu Dc) Wh(Hv Jp Nf) mS(Ug Uh Um) mT(Lh Mv Na) nD(kR Mz On) kK(Af Bn Nj) Cu(mH mY) Ng(wB wP) AdvH FwIm NjoP IkwQ ZqOe JdwB NxoQ UvVh VbVs UxVu VwiC cGmE fRjR} Et{Ik(aA Hw Ii Ij Il In Iu Jj Jo Js Lj Ma Mg Mt Mu Mw My Nc Nf Ng Nk Nl Nq Ns Of Oh Oy Oz Pc Qb) vU(aL bB cE cJ cW cY dB dE dF dJ dL eT hC iA iC iP jG jM nW pY qB qU rQ tF) Pc(Fp In Jj Ly Ma Mb Mp Mt Mu Mw My Na Nc Nd Ne Nh Nj Nl Nq Nx Oh Oy Qb) Wn(aH aL aO Ba Bg cG Cu Dd dE Dg eC Gp hA Hc iB Ke Kq Mt pF Tn Ub Wm) Mb(aA Fp In Jj Jo Lj Ly Ma Ml Mt Na Nc Ng Nk Nl Nq Nx Of Oh Oz Qb) vH(Al AN aU cH Dd dJ Fw iC iP Iv jH jP Kk Kn Ld lK Or Ou rB rQ) Nh(Hw Il In Jj Js Ma Ml Mt My Ng Nk Nq Ns Nx Of Oh Oz Qa Qb) Nl(Fp Hw Il In Iu Jj Js Ma Ml Mt Ng Nk Nq Nx Of Oh Oz Qa Qb) Ne(Hw Il In Jj Js Ma Ml Mt Ng Nk Nq Ns Nx Oh Oz Qa Qb) wB(aN bU cH cM dA dJ Fw Hu Ld Md Mv My qD Qn Rc Ri) Nc(Fp Hw Il In Jj Js Ma Mt Nk Nq Ns Nx Oz Qa Qb) Oz(Fp In Jj Js Ly Ma Mp Mt Nj Nk Nq Nx Oh Qb) rQ(aN dJ eT iA iC jO qA qB qQ rX rY vC zH) Nd(aA Hw In Jj Jo Ma Ng Nk Nq Oh Qb) Nj(Hx In Jj Jo Js Ma Mt Nk Nx Qb) sC(aN bB bU cH dN iA iC Md Or qB) In(Fp Iv Li Me Nk Nq Nt Nx Pf) wJ(aV cR cW Md Mn qA Ql Ri uN) jG(fN qZ rP rR rS rW vC vO zI) Me(Ml Mt My Nf Nk Nq Oh) Nx(Jj Jo Ma Mt Ng Nk Qb) Pf(Js Ma Mt My Nk Nq Qb) tN(cJ cR cZ iA Md oE Ri) Nt(Jj Js Ma Nk Nq Qb) tX(aL aU cR cZ dJ yK) zI(aN bL cH dJ iA tF) oT(bU gZ kN mW nD Rg) uX(aN bU dA Md rB) dE(aN cE Pb vC) eT(Ld Md qU rX) vP(aN bU cH dJ) Gw(Hf Ug Vo) Hx(Fp Jj Oh) Tk(dH iA Uh) cJ(uG uR vC) eX(Qx Up Vo) rB(mT qA qB) qU(Gc iP qQ) uO(cH iP Md) Gz(qG qH) Mt(Jj Lu) Io(dO Jg) Ri(dO wP) Ql(tO tU) Or(yD yJ) dA(uT zA) dJ(qG uT) iA(rW vC) qB(rP sO) jP(mT rW) rX(qA rR) pI(Mw Rg) EffB FigL FwrZ NqOh MpJj QaQb WeqT VsnR aCwP aNuG aUzH bUvC cWwE dLtO rRqQ} Ap{uT(Af aN AS aU Ax Bc bL bM bP cH Co Cq Cs cT CU Cv cW cX dB DE dJ eD Fa fN Fp Fr Fw Ha hO Hq Hr Hw Hx Id Ii Ij Im In jG jH jM Jn Jq Js jY Kk Ld Lj lK Lw Lx Md Mk Mq Mx Mz Na Nb Nf Nn No Nr Ns Nt Nu Nv nW Ny Oa Oe On Or Ou Ow Pa Pe Pg Po qA QB qC QD Ql Qm Qn qT QU rB Ri Rj rO rR rV rW rX sC Sr Tn Ub Uf Um uN uO uZ vC Vp Vu yJ yK zH tM tL Tj tF) wB(aC aD Af aN Ao aS aW bF bL bM bN bP bX cH cL cM cR cT Cv cX dA dJ eD Fa fN Fw hO Hq Id Ik Jn Jq JV Kn kQ Ld Lx Md Mx Nb Nk Nn No Nt Nv Ny Oa Oe Ou Ow Pg Po qA qC qD qG Ql Qm Qn Qu Ri rR rW rX Tn Ub Uf vC Vp Vu tL xA Tj tF) xA(Bc bL bM cH cJ Cu cW cY dB DE Fa Fw hC jG jP Ld Mm Nb Nn Nt Nv nW Ny Oc Ql Qm Qn QU rB Ri rV Ub vH wD zH Tj tF) zH(aC aH aI aL aS aU bL bM cR cY cZ dJ Fr lK Nn rR rW sO vC vH tM) qA(qU qY rB rN rP rR rT rW rX sC sO vH vP vU wJ) sC(aS bM fN iA iJ jO Mh Or qB QU vT) vU(bL bM dG hC iZ Mx Na nW qB qC QU) rW(fN hO iA Iv jG jM jO qB qC Tz uI) vP(aN bM cH fN Fr Fw qB qC QD Qu) zI(aN bJ bL cH Nn Ow Pi Qd Qu Tn) wQ(gW Mn Nv Oe Ou Ql Qm) qB(qX qY rB rP rR sO tM) jG(fN rP uM vA vC wD) qU(eZ fY qO qP vH vS) oW(Jd Kq Nt Um Ur Tj) sO(Fw oE qC Qu Tj) lK(qH rP uI vH wJ) wD(aS cH Kk Ql) tM(bM hO qC qD) vC(iA Pc Qu rB) Fw(rZ uM wJ) Mn(tU tV wE) aN(uG uU vB) fN(rB rN rR) yJ(Or Ow Qu) yD(iA nW Or) uI(cY qO qP) Ex(hP rZ) Gw(Ko Qu) Nt(vB vQ) St(fB pH) Rz(nB nJ) cR(tN tX) dJ(tX wK) qY(hO qD) qX(kG nB) rP(gW Tz) uX(Ou Th) HawJ IduU IzfB YggL KkwP KzeM OzdX aCdE aVdV eZrB zGnW wCrR

Figure 12 Continued qPuL} vU{Al(AN aS bL bM bP bS bX cH cW dJ Fw Hx Ik In Jd Jg Ld Lu Ni Nk Nu Oa Or Pc QA qB qC QD qU Rc rX Tr Ub Uf uN vH Vp yJ zH xA) Kg(bB bL bM Co Cu cW cX dJ Fw hC iA iC jG Js Mx Na Nn nW Pg pY Pz qA qB qC QD QU Qz rX Vp Tj tF) qU(Ad An Ao Ba cH cW dB Dk Dp Fw Fy Ic Ik Jd Jt Kf Ld Lu Ma Nd Ng Ni Pi Qg Tr Ub Um Uo Ur) cW(Ad aN aS bM cH dI dJ Ik Jd Jg Mg Mh Mx Ng Nm Nr oF oK qD rS rX Uf uN wE tF) Jt(bL bM cJ cX dE dJ iA iZ jG Ld nW Or qA QB qC QD QI rB Ri Vp zH tF) Ad(bL bM bP Hx iA jG Ld Lu Md Nn Nv nW Ny Or Pc Pg qA qD rB Ri Tz zH) bM(Dc Im Ip Is It Jo Jp Kf Kj Ld Ma Mg Ng Nm Pi Uf Ug Uk Vt) jG(Cp Dg Dk Fy Ib Ii Ij Jg Ke Kf Lh Mg Ng Nm Nr Of Uc Uf Un) bL(CH Dc Ii Ij Jd Jg Kj Lu Ma Ng Nm Of Uc Uk) qC(Cv Dc Ih Ii In Ip Is Ji Ms Nm Tz Uc Ug) Jd(aC bB hC Je jM Ki Nn Nu nW Ug Uk uN) qD(Cv Ih Ip Is It Jo Kj Nm Tz Uc Ug Uk) Or(cV dB Dc Dd Dk Ef Mz Of Qh Sr Uc) Uf(bB bQ cE cJ dG dL iA Mx oN Tz uT) nW(Ao Ba Ch Cp Cw Dk Ef Im Jg Kj Pi) Lu(aC dE Dk Fw Ng Of Tz Ub Ue tF) dB(cH dJ Ki Ma Mx Nn Pc Pz Rc rX) cH(Ih Jm Mj Pd Qh Tz Uc Ug) cJ(aC Ik Jg Jo Nm Pz Uc) Dc(Fw Ld Nn qA QB) Tz(aN jH Nu Nx Qn Ub) Nm(aN iA oN qA tF) Ip(aN aS cX qA qB) Dk(jM Ld Nn Pc) Ng(dG Jk jM Mk) Uc(Fw Nn Nu Ql) Cv(cX Md Qn) Jg(aJ aL dG) Ug(cX rX yJ) Fw(Dd Qh) Nn(Ef Kj) Ii(dE dJ) Jo(aN qB) Uk(yJ Th) Pi(gL iC) bB(Fy Tr) MaMx MzVp UbaC lnqA lsqB PzzH K

Pd Qm Rb) ql(Al Dc Dd Og Qw) qH(Dl Jp Ke Mz Nm) qC(jY Qz Ri) IL(Jh Ri) RcqG dArX hPhX} nU{eD(aL Ar Aw Vt) Hu(Fi Lp Rx) Yi(cR Nf Rg) cM(jI Ue Yh) jH(cW dL oE) Aw(jV qX) hC(jL lL) CsGn DilN MePs HpRg YkPz StRz RxPc UnjL aDrY aWqW cWqV cZjU tFrC} Nf{tF(Du Fd Hp Ps Vj Vw Wb Yg Yi) oK(Rz Ux Vw Yg Yi) Hp(cQ iO Rm) Wh(iA jU lM) oE(Du Yg Yi) Yf(mU nF) qX(Yh Yi) YgaR ZxlM UpkO ValX} Kg{tO(aS dL Mn Oe Ql) tQ(aI aL Jr vC) zA(cM dA Mx Uu) Mp(rR rZ zH) rB(qC vC vS) Th(uX xA) bM(sC uY) AnyL AooD NnvW HqvA bLvT dJwJ dLtT} dV{aV(aA Af Aj Al aZ Bg bH bM bQ bU Ch cJ Co CV De Em) Af(aL aM bE dD) Bn(aL bE bU Co) aK(aZ De) CobB EfdD bQcY} Tm{rA(Hu Il Jr No Nx Pd Ua) lL(Jp Mr Nc Ni Nu Om) qX(Il Jn Mg Nx) lW(Rx Ue Wm) Pc(iB rC) hX(Nd Nj) qW(Il Jh) YgrZ JmjE dRnF} kO{jH(bA bG bQ dL Ji Jn Jq Lh Nj Nx) Jn(jI jQ jR) qX(aU aV Jq) jR(Af aU) WmGn GhHu NirY JirA UnjL UpjU UteD cGrC cSqW cWqV} Ch{bL(uM uT vP vT zH tM xA) tN(Nb Ou Ow) uT(Mm Nm Nn) Fi(hC oF) Gd(iB jM) Gn(iA tF) GtbB LuvB KiwC VbdR aIwK aJtU bMwQ tQuN} Wn{Dc(aH bB cR dF dG dR eC lB jI kS lK nW oK oN) Fy(jK rX rZ) Lu(Nh Th) qY(aZ iH) WmhX MmdF UbhA VojE PiiB} jB{bE(Ji Jr Ki Nb Nx Qz Rh Rj Ut) Lh(cU Hc Qb Qe Vu) Rg(Ic Id Lv Pk) Jp(Ki Rj St) Hc(eC fP) AlQz SsPd NxdN} nF{Bg(jH jI lK lM qW rA) bP(jK jM rC rX) qW(aY dC Uh) Wm(Dr Yh) eD(Ar Vt) jH(Aj Uc) DilN YfQb VbdR cGrC cWjU hCjV} oD{Ao(Kf Kr Ks St Tn Ug Ur) bU(Lx Nu Qt Rg) Al(Hc Nc Qz) Jf(cR fP Mq) Nt(Aw bC) Pk(cR fP) BaEz DpMw QgbC RjUk} Lu{vB(Ax Jv Kk Ql Rc Ri) Vp(rZ sC vS) vC(Ou Ow Qn) Ha(vS tL) aS(sC uN) rX(Ow Ra) FyuL RitV UruN VvvQ bLuO bMsC} Gn{tF(Aj Ao Ba Bg Cp De Hp Jr) kR(Al Ao Ba Bg Cp Hp) iA(An Ao Ba Dc) BapF CpiO HpoE TolX KfgP} mU{jH(bA bQ dM eF hB) cE(hA lN qV) Hl(Du Rg) Yk(Em Qn) cR(Wf Yg) dM(jI qW) lK(bQ Na) DrWm GhbJ IurB JrRx cZeD} lL{Wh(Jm lM Ma Nj Of) Yf(hW jY Ut Vs) Wf(Fr Jh Jp Mt) Yd(Mr Ni Nj) We(Hv jI) BnyJ NiZx UcsC VcjI UxhR} tN{cR(Aw Cp De Dg Dk Hb Im Mm) Ou(Aw Ba Ef Mg) cL(Ar Ne Th) Mg(Iv Ow) Pi(dA jY) CpOw EfNb} Ji{In(Mb Nc Nh Nl Nt) hR(Ly Me Wf) jV(Wf Yd Zx) rX(rQ rR) LyeD MbMl MpaY WejY WhhX bLuM rBqC} oQ{dM(hA jE jL lN rB rX) eD(aX bF iO Nx) Qb(Yg Yf) aD(lM rZ) dR(jH rY) InJn YiRg cGjH cQlN} cW{wE(Dg eF On Un) zA(cJ dJ uM vT) xA(Ic Il Kf) aM(uO vT) tV(dA vT) NrtO aSsC lXjR rXvS} wK{Pz(cM dA dJ Ri) Ef(bS bX dJ) Ri(Mq Mx Uu) dA(Al Mx Uk) Uu(cJ sM) MgbU UcdJ} lX{eD(aW cM Cv It oN Vt) Hu(Gh Rx) Rg(Yh Yi) IzVb RxPc LtcQ bGjV bQlN bZjH} wJ{cR(Kl Kq Rc Tt Uc) Ql(Ao Uc) uN(Mg Ph) AlbS NmaS MnKe TrRi KnQn KqLd VobM} rB{qC(Dg Ii Il Ke) Dk(vQ tM) vS(Ef Kj) BauW CpGc LvYi MgeT IiqD ImqZ YdPc VcVp} pK{Ef(Iq Je Pa) Nq(Jr mP St) Jp(Gp To Ur) BaHv BcJv CoLh DkSt EzHc NyVs UkcI} Th{xA(Cw Kn Ma Nm Ql) rR(Kp Nu Pc) dL(vT tL) MauT KnuX QluP UyqX} Ld{Nm(uT vT xA) wQ(Dg Ez Vs) Il(uP yK) DkzA UcvS QhyD KquT UnjO UgwD} Fi{Kc(cQ Hf Ut) Kp(aY hC Nj) aY(Im Jk) gP(Jp Mn) BahC CsOy WmlW} Wh{jV(Fr Hu Jn Jp Nq) iB(Ms Of) NjhR HuqW HvgP IhlK JmjE JplM} aI{zA(Hb Kf Ri Ub) Ao(tQ tU) Dg(wC wD) Ke(tQ tU) MatO IczH RcyD} mP{Ny(Ph Ut Vs) hC(hA jK jL) aY(bH lN) cZ(jE jY) JrRx bQlK cSqW} Zx{Ip(eD jM jU qY) Nj(hR hX qV) Iu(hR qV) JmjI NvlM OeqV} We{Hv(jE jF jV jY) No(qX rA) Pd(qX rA) NjhX HuqW PajI PcrC} Ye{Jm(iB jE lK) Hu(qW qX) qY(Jh Pd) NjjV HvgP IpjI IzeF PcrC} cJ{Uc(tV uR vQ yL) vC(Lh Mm Un) BauW NmxA TrtV KquG bEzH} tO{Ma(aH Md Mn uT) Pf(cZ Pi) DpQg NrQl IclK RajV JoaS VtdJ} wD{Vt(aS dL Pk Ql) Vs(dJ Nd rR) cM(Hb Vo) dA(Ii Mq) AlNd} Hp{iO(Bo In Kp Vj) Pk(aY cQ Ip) In(kR Ux) Rm(Mh Mn)} Im{yJ(dJ nW Ow) qZ(Ms Pc) uW(Ub Vp) MhzH VuzA bMsC iArV} Uv{Vb(eD hR jO rC) qY(Uw Va Vh) Ux(hR jR) iB(Uw Vh)} Al{Ax(vT xA) vC(aS zH) NdsC OauM UrzI bZwQ tQuN rXuW} Gd{iB(Hu Iz Kc) jE(eD Io Ko) BatF NilN QweD KcjM} yD{Rc(aL cZ lK Pi qY rR) EzdJ UbcM KibE KliA} vS{Kj(bL bM Nn rX) Ef(Mp nW) rX(aE Cp) AjRg UcdJ} uN{tQ(Ar Dc Dd Hb Kc) ArRf KftT UrrR PhtU} Ba{nW(qZ tV uW zG) Pc(sO uT) ItuW VbtF} Dk{Nn(uT zH tM) zA(jV Kn) zGnW qDtM qPuI} Em{Kc(oK pF) bR(qX rA) DeqV HupF bJlW dIqW} Yg{rA(Mf Nu Ub) NuqX MsrC NjqY InoE cUoN} Wf{Mt(hR jU jV lM) hR(Hu Po) jV(Jn Nb)} Un{Vh(jE jK jU) qD(uG tM) rX(rQ rR) UwjE} wQ{Dg(Mn Nv) Ef(bM iA) Uu(Ou Pi) PddJ PibM} Bg{gN(aZ bB bM BN) Cp(cK cO)} Nm{iA(rQ rR sC yJ) Ri(uT xA) cTuT} Nd{Dc(sC tL) Tt(rR rV) MzIn TvrV StsC} Kp{Fc(cN Nj) Rx(oK Yd) YfNj LhVi RuoK} Vs{Vb(dR jH) NnuT UxjO VhjQ VihR tTqC} bL{Uc(uM uO vT) uM(Iz Kl) MgrZ KjvT} Mm{bB(sC uO yJ xA) sO(Kk qD)} Jr{Rx(oE tF) rC(Yh Yi) RugP VjtF} Vt{wC(dL Pk Ql) FcKc VajV qDtM} lW{Wm(Dr Hl Rt) YkcP KzRx cElN} tV{Mz(Aj dA) Kq(cM dA) DlaS KlnW} In{Nl(Jp Nw On) Nh(Jp Mz)} Ip{Wb(jF jY) YdjE QgtU UrzI} Ux{jO(jE Ul) lM(iB Vp) VvjF} zA{Rh(iA nW) FydA UlcM UuiA} vC{Pc(Cv Dc Kl) CvQn DczH} Gc{rC(cP lt) KcqV cRqX} Ms{NizH UruT aSwE vPvV} Yh{qV(Nt Oz) UbrY HunY} bM{Pi(tT vO) DcxA JpsC} Ao{uI(qO qP) MauT} Gt{BncG aZbA bFcZ} Mb{FpOn LyJp MlNw} Ii{OwyJ aSrV dAzH} Yd{MrjR NjhX JmjE} Tk{PhlK aFbB aJrX} Uw{qY(Up Us) jFjO} Vb{dR(Ef Iz Jk)} qD{tM(Il Rc) KesO} Cp{Nn(uT uV)} Dl{rX(rR uW)} Dr{rA(Aw Qy)} Mg{MpsC VuvA} Ub{YirY KfuI} Vw{PzkS UsqY} aZ{gN(Af Co)} gP{HvSi JpRu} tU{MnHb KqaL} xA{CqDc KfPc} ArsCnW DgdJwC YfhRjY FbKyVa FyhUuL MrWbhW IcdAuU IlqCtM YiOzqV KetQlK UgUrzI

Constrained panels with 3 analytes, where 8.3E-10 >= 'AUC p-value' > 1.0E-10. Contains 8,251 panels of 36,603,637 total panels evaluated. : wF{jG(Ar Ba cR Fr Hc Ib Jf Kk Mn Mq Tv Vo Tj) Ld(Ar hP It Iv Iz Kl Mm Nm Or Pk tR Ug) aI(Aj Ch Cp Cu eF Jo Nq Pd Rc Tr Vs Vv) aN(Ct Ef Fy Ih Jm Og Pc Po Qt Ue Ug Un) Kk(Ao bL Jd Ji Kd Ke Lv Nd qT St Tr) Qt(aD Kr lN Lu Nt Ph rN sK vI vS) Ri(Af Ba bF Dd Gl hA jM Ko Nv Pi) Ql(bM Ed Jd Kj Md Og qA Qv rB Ue) Or(Ba Bg Co dH dI hP Mh Tr tV tL) Je(dA Ed Hc hP Iz Ke Mh Pk qC) Jh(aD As cR dD Ph rQ rW Tz Ut) Cp(cR It nY Ph Pi Ug uM Ut) Tv(Ch fN lL Ms Nt On pY qB) Oi(Db Fr Ii Jo Mw Of Ok pY) Om(aH As bS cZ eT rQ sK uM) pS(Dc Fr Hu Ly Mm Mu Mw Pa) vT(Ao Fy Jf Jo Kf Nm Ok Ue) Dd(bF Hc Hu Mn My Pk qA) Ef(bH bN cH cR eT Iu Ph) Mh(bB Cw dF Jo lL lN Nu) Nd(Bg Ke Kl Ms Og Ok On) Tz(Bo dJ Iz Po Vs Vv tL) Im(Mn Nj Nm Nq On wC wE) It(aE Hc Kl Mu Mw pY qI) bS(Aw Jo Mq Mv On Qh Uk) cJ(Fy Lh Of Oy Pc Pf Qm) Ba(aX Mz rN sO Ug Uu) Mm(bU dI dK Ki Mn Uu) Ke(bU dA iC lK lN Mp) Rj(jT lK lL Mq rV rW) Ph(dA Jd qA qT uN Vs) cM(aF Gl Nw Qm Uh vS) Al(bH dA fN Jd Js) Ao(cH hC Ik nY tR) Aw(eT jV Nb Pi Ug) Co(bL cZ hC lL wB) Nm(An bU Ly Md My) Ub(aW Jv Kp Nl qT) Hb(bP jU Jv Nv Ny) Kf(aU aV dA dI qA) Ki(Aj cL Kn Ne rR) Ok(Mn Pa vW wB wJ) Pk(aM Ih Mz Rm vH) qB(Dc Fy Jf Qe Ut) vU(Aj De Of Oy Rc) Aa(aG dM Up wD) Cw(dI Jd Ji Na) Po(cW rN rW Uu) Gl(Md Mx Qh Ug) Ue(bU lL Mn vC) Ik(cW dK Nu qG) Iz(Kp Nn Ua Ul) Kc(lK nW vH tL) Kq(cR Oe rZ vC) aW(Aj Bg Jm Ug) cH(Jm Jo Rm Tr) dJ(In Mj Pe Uk) hP(Ip Jm Me On) pY(In Rm St Um) vS(aE Fr Nq Qh) Bo(cL iH Og) Ch(bA Ji Mz) Et(Jr Mu yH) Ms(bH Hu Mw) Mv(bL rN rW) Ib(aD aL lL) Kr(Mq Mw Pe) Lh(bU lL lN) Nw(bX iC lL) Vv(cC dL vW) Pi(iC qT rB) Af(cR tL) Ar(dD hC) Dc(bX Me) De(nW vH) Ed(jV Mz) Tj(dH Rc) Fy(dI iC) Nr(bN qT) Md(aX Cv) Mn(Of St) My(Il vC) Uc(tR Ut) Hu(Ii Mz) Tt(Ow vI) Jf(cP Pc) Kd(lN rZ) Kj(Ow vC) Og(tR wD) Uf(cZ wP) Ug(jV qT) Vo(uT vW) aF(aE bL) bE(dB Fb) qU(Mq Qg) rQ(Me On) BgNn DbPc DlMp FaJi NqrR NtcL NubL IiyH IlOf IncP HcvH RcyD SsUu StjU QhVt JojO JvKl KgqA KpbP OauT OhVs UnaS PelK aCiP cZdH} Ok{Qb(Fp Im Ir Iv Ji Jj Jr Li Lj Ma Mt Mu Ng Nk Nt Nx Oh Pd) Jj(Et Fp Hw In Jg Ji Ly Ma Mj Ml Ne Nq Nx Of Oz Pc Pd) Oh(Hw Hx Ij Iq Js Lz Ma Mj Mt Mu Ne Nf Nq Ny Of Pd Pg) Nk(Et Fp Hw Il Iq Iv Ji Lj Mj Ml Ms Mt Ng Nn Nt) zH(aC bL cM Dd dJ Ed iC Ik Mn Ou Ql Uh vP wB) pS(aJ bL bM cB cD cH dB Hx Il tR uO vQ vT tL) Fp(Ii Ij Js Lz Ma Mj Ml Nb Ng Nx Of Oz Pe) Nn(Hx Ii In Ma Nb Ng Nj Nq Ny Oz rP rS rV) wJ(bM bN bP dE Id Md Mg Nr Nu Pe Vo Vp yJ) Mt(Hu Hw Hx Ij Lu Ma Mj Mp Nb Ng Nq Pg) Nx(Et Hr Hw Ij Il Jo Js Mj Ng Ny Of Pg) Ma(Et Hr Hu In Jg Lz Mj Ml Ng Pc) sC(aI bL bW cH Cu dJ dL jM nW Qm) Hx(Et Hr Hu Im Ji Lz Ml rN wB) In(Et Hu Hw Im Ir Jg Ji Lz Mz) Pd(Hr Il Iq Js Ml Nm Pe Pg Po) Nq(Et Hr Hu Jh Me Mu Pf wH) Ly(Me Nc Ne Nf Of Oz Pc Pf) Nj(aA Et Hr Il Iu Ml Ng Pg) wB(bF bN Cp Fr Js Mu Uf uR) uO(aQ bM dF jM Js lK Nt Pg) vH(bP cB cH jM Ko rQ rR Ub) Ii(Et Hu Hw Jg

Figure 12 Continued

Nx Oh Oz Pc Qb) wF(Ad Ap Bb cW Dg Ij Jg Jh Kg Mg Ng Ti) Yl(kK kN ml nA nB nR qT qW qX rA) Pj(jO pS rP rZ tR vU wG zH zl) Tl(gL iZ kl mY nA nB nJ) Ik(dE Dq Ji Jj Jp Nw) Vq(ql qZ rP rR rT) Do(Jy Nd Pk Ur) Ng(uT wH wJ wL) Vz(kK mP nB nR) aC(Ad Cp Dg Dl) jD(Uw Vh Vj Wc) qT(Dr Vc Wc Yd) Bb(pS sC wK) Jg(dE pS wH) aN(cC dE Ji) Aa(uR vO) Mb(Ji Nw) Nk(Nc Nl) Uf(fA oT) Pb(dX eP) tR(Kg Pi) ApuT CpdE DqFy EdjB GwPk IjwH HceQ YjqX WcjT JtpS XalK TmnA VwiC OzeP dBvS fAfP

Constrained panels with 2 analytes, where 1.0E-7 >= 'AUC p-value' > 1.0E-8. Contains 130 panels of 196,694 total panels evaluated. : Ik(AA aN Fp In Jg Li Lj Mm Mt Nk Nn No Nx Oh On Pa Pf) Jg(aH aN Fp iA Nc Ng Nh Nj Nl Nx Oz Pc wL) Ji(dE In Nc Nd Nh Nj Nl Nt Ok Oz Pc Pd Pf) Et(Hw Il Js Lj Ly Mp My Ns Of Ok wG) wF(Ch Dk Dl Jd Jt Kn Mv Uc Uf Un) Ok(cE dU Iq Ly Ml Nn Po pS) Jp(Mb Nd Nh Nj Nl) aC(Ao Ap Aw Ba Bn) dU(Ir Iv Nd Nl Ph) pS(Ad dB Or Ti) Nh(Nk Nw Nx) aN(bU Cp Pd) Aa(Mt uN) Bb(rW vH) Do(Pi Ug) Ed(eQ vS) Fp(Mt On) Mb(dE On) Mg(wH wL) Lh(nK oT) Nw(Nj Pf) vU(cW dB) AdzH ApwB TjJd MvwH NguW IjwL YjnA VzmM JnlY KeeM YlmP PbdE Constrained panels with 2 analytes, where 1.0E-6 >= 'AUC p-value' > 1.0E-7. Contains 283 panels of 196,694 total panels evaluated. : dE(aC Ad aJ An AR Aw Ba bM Bn cP Dc Dg Dl Et Fp Jp Jr Jt Mt Nh Nv Nw Nx Ok Oy Oz Pc Pd Pe Pf Un) Jg(aC Aj Bg bQ bZ cE cO Cu In Iu Jj Lj Ma Mb Me My Nd Ne Nk Nq Ns Of Pd Pf Qb rQ sC) Ji(Fp hR Hw Hx Jj Jq Js Li Ml Ms Mt My Nc Nk Nq Ns Nx Qb) wF(Ao Cp Cw dB Dc Ef Et Hb Im Kj Om On Ri Vo Vs Vt Vv) Nw(aN Fp Hx In Iv Mt Nc Nd Ne Nl Ns Nt Nx Oz Pc Pd) Ik(Ar Fr Hw Il Im Lh Ml Mz Nc Nl Oz Pc Pd) Nt(Fp In Jj Jp Li Mt Nx Oz Pa Pc Pd Pf) Nh(Aa aN Fp In Lh Li Mt Nv On Pc Pd Pf) aN(Ad bM Bn cB Ch Lh Ly Mg Nm Nx Oy) Cp(aH Bg bZ cK cO Cq Cu Dk Fw Tj) wH(Ap Ch Et Jh Ma Ok On Pf Uf Vo) Nj(Fr Li Mt Nk Nx On Pf) Fp(Jp Mu Nx Oz Pc Pd) Mb(Do Gw Li Mt Nv Oh) aC(Aj An Ar Ch De Jt) Nd(Li Mt Oh On Pf) Jp(Nc Ne Nx Pc Pd) tR(Al Ch cW Ld Ma) Bb(rV uG uW vC) Nl(Fr Li Nx On) gL(Fi Vz Wd Yg) Ad(In Of vH) Nc(Li Nx On) Pc(Li Mt Nx) pS(Ar Im Ng) Aa(Me wG) Et(aA Wn) Yj(kK rA) Vz(nK qT) Ok(rP rV) Oz(Li Nx) Pj(hR rB) dU(Jr Mn) eQ(Lx Uk) wL(dB Kn) zH(Ap Ng) qU(Vq Tl) AlvU AowB BggN BnbU DoDp DqKi FwKf McOn NeNk TzwG YgiP ZqqT JnnK JtiA LhlY aVdV nAhV Constrained panels with 2 analytes, where 1.0E-5 >= 'AUC p-value' > 1.0E-6. Contains 553 panels of 196,694 total panels evaluated. : aN(aC aE Ar Aw Ba bC bH bS bX Dc Dg Dl Ef Et Fp Ih Jd Jl Jt Mt Nc Ng Nj Nl Nn Nt Nv Og Ok Om On Pc Tz Un Tj) Jg(Aa aG aR aY bM Bn cK Co Cq dH Dk Fw hB Hw Hx iJ Io kS Ld Ly Mt Mu Mw Oh oN Ra rP Tn Tz Uu Vo Tj) dE(aM aW aY bA bF Bo bU cB Ch cK cN cT Gl Kc Ko Kp Lh Mg Nc Nd Nl Nr Nt Oi On Pa vS) On(Hw In Iv Jj Lj Ly Mp Mt Mw My Ne Nk Nq Ns Nt Nx Of Oz Pc Pd Pf Qb Tj) Nh(Ad Fr Hw Il Im Jt Lj Mb Mm Mu Mw Nn No Nt Oh Om Oy Oz Pa Qb) Cp(Ad aK AR aV aY bH bJ bL bM Bn bQ bU cP dB Dg Dl Of Pg) Fp(Fr In Iv Js Lh Li Ly Mb Mg Mm Nc Ne Nj Nl Nn Of Oh Oy Pf) wF(Aw Ii Iz Ji Ke Kf Mw My Nm Ok Or Oy Pf Po Rc Rj Tz Uu) Nt(eM eQ Fr Hw Im Lh Mb Ml Nc Ne Nj Nk Nl Nn Oh Qb) Nd(AA Ad Dq Fr Im Jt Lh Mm Nn No Nv Oy Pd Pe) Nl(Aa In Lh Mm Mt Mw Nm Nn Nv Oh Oy Oz Pc Pd Pf) Ji(aC aH bQ bZ cE Ed eM Iq Ly Of Oh qU rZ Tj) Jp(Hw Hx iA In Iq Iv Ly Me Mt Nq Ns Oz Pf Qb) Ad(Aj An aW bM bQ cB cO cP Ik kS Nj uW Tj) Li(Fi Hx In Ly Mc Mt Ne Nf Nk Nw Nx Pd Qb) aC(aM aR bC bE bM bU cB cC cN dB Dd Et wL) pS(Ap Dg Et Fy Ic Ij Jd Ke Kg Mm Ny Pz Ur) Nj(Jt Lh Mu Mz Nm Nn Nv Oh Oy Pa Pd Pe) Nw(Hw Jj Js Ly Ml Mu Mw My Nk Nq Oh Qb) Jd(Ar Ed eQ Fw Hq Lv Pj Ra Tz Vp) Ik(aR Bn bQ bZ dI Fw nK Of Tj) Nx(Hw Jj Lj Mb Mt Ne nK Pd Pf) Ok(aH bQ bZ Dq wB wJ wL zH Tj) Aa(dU Jr Mb Ne qH tV Un vC) Kc(Fc Fi Fw Ld Va Vz Tj) Lh(iA Jj Mb nB Nc Oz Pc) wH(Aw Ba Cw Om Pz Uu Vs) Mt(Jj Lj Nc Ne Oz Pd) Pj(cE iP jP qU Qv Vs) Ba(bQ bZ cO iA Tj) Et(cE iA rQ uO wL) Jt(cE Qv tR zH Wn) Nv(In Nc Ne nK Oz) gL(Fc Si Vc Vw Yl) Tj(Kf Kn nD Uf) Ti(rQ yJ yK zH) Fr(Mb Nc Oz Pc) hV(lY mU nU Wd) wG(Ij Mg Or Pi) Bn(bH bM cB) Ed(Ar No Un) Gn(bM Ch nA) Qa(Mb Nk Qb) Uf(cE Fw uT) Ux(iC lL lM) Pf(Ly Nc Ne) dU(bH oP pH) eQ(Iz Rb Ua) nR(Vs Yj Th) wL(cW Uc Vo) Ap(tR xA) Do(Ez Vo) Fc(Hc Kp) Ma(tS tX) Tz(hR lL) Or(sC yJ) Un(Fw iA) Pd(Nc Ne) Pe(eP In) lY(jQ jR) nA(Hl Yh) nD(cM iP) kl(Ry Tm) vU(Kg Ng) vS(cH cW) ArPc BbvP BggT BoDb ChtS CttR DgcO DlcP YflL MbMm HpQv ImqZ YgiZ YjmM SfnT QbQe QueX XanO KpRx OhOz aEvQ bMdB nNjR nBrB Constrained panels with 2 analytes, where 1.0E-4 >= 'AUC p-value' > 1.0E-5. Contains 1,164 panels of 196,694 total panels evaluated. : Ed(Ad aH aN Ax aY Ba cE Cp Cs Dg Dl Et Fp Ic Im Jg Jp Jt Ju Ke Kf Kn Lh Li Mm Nn Nv Nw Oh Ok On Pd Pe pS Qe Qv Rf Tz Uf uO vU wF tM) Ad(aH aK AR Bg bH bL bU bZ cE cK cN Cq Ct Cu dU gT Hr Hw iA Jo Js Ma Mp Nc Nl Nn Nx Oh Oy Pc Pd Qb Qv rP rV Un Ur) Cp(Aa cB Et Gn Hr Hw Hx In Ir Js kl Ly Ma Mj Mm Mp Nh Nj Nk Nl Nn Nq Nr Ns Ny Oh Ok Oy Pa Pc Pd pS wH) wF(aC aF Aj Al bE cM cO cZ dA dH Fr Hq Il Jo Kc Kl Kq Ld Ma Mh Mm Ms Of Og Oi Pa Pc Pd Pz Qt Ug) Tj(aC An Ch Dg Dl Et Fp Fr Fy Jp Jt Kl Kq Lh Mg Mt Mz Nv Nw Oh Oi Oy Pa Ph pS Rz Tt Tz Un) Nj(AA Ap Ba dE Dg Dl Im In Iv Jl Lj Lx Mb Mg Mm Mv Mw Na No Nr Nu Om Oz Pc Po Qa Qd Qe) Pc(Aa Bn De Dl Im Iv Jl Jt Lj Mm Mz Nc Ne Nm Nn Nu Nv Oh Om Pd Pe Pf Pj Po pS Qa Qe) dE(Aa cl Fy Ic Im Jd Jh Ke Kf kG Kl kP Mp Nm No Ns Oh Ph pS Rc Rf Rg sC Tz Uh Vs Vt) aN(Aa Ao bF cK DB dl Is Jh Jp Kc Kf Mm Mw Nc Nd No Nr Of Oh Oz Pb Pe Pf Pj Yl) Mb(aA Iv Jl Jt Lj Lx Ly Mu Mz Na Nc Ne Nl Nm Nn No Om Oy Pd Pe Pf Po Qd Qe) Oz(Dq Im Iv Jl Jt Lj Lx Ly Mm Mw Mz Nc Ne Nm Nn No Nu Om Pe Pf Po Qa Qd Qe) Aa(aU aY bM Bo Fp Fr Hu Ir Is Iv Jp Lh Li Nc Nr Nt On Pd Pe Pf Po Qa Qe) Ji(An aR bH bL Bn bX cK cO cP Cu dB dl eD Fw hV iA lY nK Ra rB Rm Ur Vp) Jt(aH An aR bQ bZ cK cO Cu eM Fw Iv Jj kS Nc Ne Nl Pf Qy Ra vU wL tL) Ba(aH An Ar Bg bL bM Bn cE cK Ct Cu Db dU Fi Fw hB kS Mp Nd Nh Of) Jg(Ar bL dB Dc dl Fi FN Ic Jd Jy nK Ou Oy qC Qx Qz Rm Ur Vp Vv) wH(aC aO bE dH Dk EF Fr Hu Ii Im Ke Kq Mw My Of Oy Po Tt Uc Un) Nd(aR Dg Ii Jl Lj Mg Mi Mu Mw Mz Nm Nr Om Pa Pg Pz Qa Qc Qd Qe) pS(Al Ao Cw Dc Gl Ii Ik Il Kj Kl Kq Li Lu Ma Mg Ph Rc Rf Ub Uf) Jd(bQ cE dl iA In Js Ld Mm Mp Nk Nm Nn Ns Oh Pa Pd Pg Uk wG) Nv(Fi Fw Hw Hx Iv Jj Js Ly Me Mm Mw My Nk Nq Ns Pd Pf Qb) Pj(bQ cN dl eM eQ Fn hA Hu jD Js Ks Lv Ma Mp Oy Qy Tz Uv) Lh(aA aC cE Fw hB Hx In Iv Mm nA Ne Nk oN Pd Pf qU rZ) Fr(fA Fc Fi Hw Hx In Iv Ly Ma Me Ne Nk Ns Pd Pf Yl) Nl(aA Hw Im Iv Jj Lj Ly Mg Mu Mv Mz No Oe Om Pa Qe) Jp(aC bZ Fw Im Ir Jj Li Lj Mm NK Nn Oh Ra Tz Ub) Kf(bQ bZ cE cO Cu dl In Js Mp Nk Nn Pg Qb Qv Rm Vp) On(bZ cE cO Cu eQ Fw Hx iA Il Iq Ms Mu nK Oh Oy) Un(bQ bZ cE dl Hr Hw jG jO Mp Nk Nn oN Pg Ra wL) Pd(aC Hu hV iA Iv Jj Lj Lx Mu Mw Mz nB Nk Qa Qe) An(aM aY bH bM bU cK cP Dg Dl gW Mt Nh Nm Ok) Ik(aC aH aY bL cE cK cO Cx dB De fN hR kS Ur) Nx(cK Il In Iv lY Mm nA nB Nk No Oh oP oQ pI) Et(aH bZ cK eT Fn Fw hR jP Qv qY rZ vH zH) Fp(aA aC aF bH bZ Ch dB Hw Im Jj Ml Nk Qb) Mt(Ar bQ bZ cE cO eQ Hw In Iv LY Nk Pf) Mz(eD hR hV iA Iv Ly Mu Nc Ne Nh Pe Pf qU) dU(Ao Ap Ax cF De hB mE mF mT mZ nD nL oF) Yl(aR cQ Fb Hu Ib Iz Jk Mu rB Ss Ua Wd) Uf(bQ bZ Hq iA jO Js kl Mp nR Pg rZ Tz) bM(aE aW bA bF bU cN cT Dg Dl Em eX Tl) Nc(Hw Jj Lj Mm Nm Nn Nn Oh Oy Pe Qe) Ne(Hw In Jj Mm Mw Nm Nn No Oh Oy Pe) Ok(aC aG aR cK cO Fw hR iA Ld Ra rZ) aC(bH bL cK dl Ef Gn Mg Ng Nm wP) wL(Ap cM dH Ii Im Kj Om Rc Uu Ti) wG(cJ Hb Ii Im Jh Nm Om Pz Rh Vt) Aw(aK Bn bU cK cO Db Dg Dl kl) Fi(aY Fb Hc Hf Kp Oi Oy Pf Tn) Ly(aR hR Nh Nn Oh Pa Pe Po Qa) Kc(bL bZ cK dB Gb Ns Vc Wf) Kp(bQ bZ cE cO dl oN Ye Yf) Li(Hw Iq Jj Js Ml Mm Nq Oh) tR(Dd Dg Dk Im Iz Jo Mm Pz) Ar(bU cK cO Mg Mh Nh Oy) Nw(aH bZ cE cK hR Iq Ra) Bn(aH aR bL Bo cK cP) Dg(bU bZ cK cP Js Mp) Dl(bL bU cB cO Mp Qv) Vz(aR bN Fb Hu Mg Pk) hV(mM nl Tz Ux Vw Tl) Bb(fN kS rU uO zH) Fc(Ch Fb Hu kK mY) Nh(aR Iv Jj Ml Of) Kl(aH cE Cu fB Of)

Figure 12 Continued tS(Iz jK Ld oE Pi) iP(Fy Rc Vw Wd Xa) jR(fR mI nA nB nI) kI(fP Ky oQ Rg Rv) Fw(Ke Oy rZ St) Mg(Lj uW vU wJ) Mm(Hu Me Nt Pf) Nk(Lj Pe Pf Qe) li(hR qU rB zH) Om(hR lY nK rZ) iZ(Sj Ux Vw Wd) jI(hR kG lY mZ) Al(vC vH zH) Hp(In Pk Rm) Tz(jF jO Js) Hw(Pe Pf Qa) Jj(Nm Qa Qe) Jn(kG nB oQ) Kg(qU rZ vH) Vq(iO qY rZ) aR(bU cC Oy) aY(bU mP nD) eQ(Je Ko Qv) gT(Af aV Ch) nN(jQ jT qY) iC(Vj Zq Tl) Ap(kS zI) Bo(dB Em) De(cO Gn) Ti(rP uN) Nt(aH nK) Ng(cO fN) Ij(wD zH) In(Qa Qe) Pe(Mu Qb) cB(aH dB) cE(Ke Ko) cH(vU tL) eP(aV bB) lY(Nf rY) nD(iO pH) iA(Ss Uc) uW(Dc Qh) EfVb YfjY GcQv GngW GteM NmJr LuvI LxoT MqhR MwpI HqTt ImzH HcfB ItnK IvPf YgmM ZqjE WdlM VjgL bUcN dDdX mPrB nAjQ qUvS

Constrained panels with 2 analytes, where 1.0E-3 >= 'AUC p-value' > 1.0E-4. Contains 2,317 panels of 196,694 total panels evaluated. : Tj(Aj Ao AR Aw Ax aY bM Co Cs Dk Ef Gl Hb Ho Ih Ii Ij Im It Iz Ke Kg Kj Ko Kp Kx Li Lx Mm Mw Ng Nh Nm Nn No Nr Nx Oz Pc Pd Pe Pf Pg Pj pK Po Qa qC Qd Qe Rf sC Ss St Uc Uw Ux Vi Vj Vs Vw Zq XA) Aa(aC aJ aK aM An aQ AR aV Aw aZ bB bC bF Bg bH Bn bU cB cC cG Ch cY dG dI eF fP hR Ih Jd Jm kS Lx Mm Mv Nm Nn Nv Oh Oy Oz Pa Pg Qv rS Uf Vs Vt) Fw(Ad Ch Dg Dl Dq Fp Fy Gl Hb Ib Ii Im Iz Kg Kj Kl Kn Ko Kp Kq Li Mg Mm Mt Mw Nh Nm Nt Nw Nx Oh Oi Pa Pc Pd Pe Pf Ph Pj Qa Qe qU sC Ss Tr Tt Tz) Pd(aA aH An AR Ba Bn bQ bZ cE cK cQ Db De eD hR Hw Ic Il Im In Ir Je Jt LY Mm Nn No Nu Oh Oz Pf pS qU qY qZ Ra rB Rm Un Ur Vz wH wL zH) Un(aH AR aY cK cO Cu dB eD FN hR Ic In iP jP Js jY Ld Nm No Ns Oy Pf qA QB qC qU Qv QY rB rP rV rW rZ Tz Ur uW Vp wG zH) Jt(Ar aY bL Bn cP CQ dB Dc dH dI eQ FN Hr Hu hV Hw Ic In Ir Ld Lj Me Mu Of Oh Oy qA qC Qh qU Rm rV rZ Tn Tv Tz Ub Uc Ur Vp) Ba(aK aR aX bH bU cB cN cP dB dI Fc Fp Hr Hw Ic In Js Ly Ma Nc Nk Nl Nn Ns Nx Oh Pc Pf Pg pS Ra Rf rZ tR tS Tz uT uW Vz wB wF) Dl(aH aK Ar aU aV aY bH Bn Bo bZ Ch cK cN Cq cT DB De dU eM gW Hr Ic In Js kS Mt Nc Nd Nh Nl Nn Nx Of Qb qC Ra vH vQ wL zH) Ch(aK An Ar aU aY bH bL bM cK cO cP Db Dg Ed Fi gW Hb Hw Id Kc Ly Mm Mp Nd Nj Nl Nn Nw Nx Of Oh Oz Pc Pg rP Ur uT vH Vz) aR(aE Aw bH bL bM bX cB cK DB Ed Et Fi Fp Ic Jd Kf Kz Lh Mg Mp Mt Nb Nf Ng Nj Nl Nm Nt Nw Nx On Pa Pc Pe Pf Tz Uu) Ar(aF aH aK aU bH bL bM Bn bQ bZ cB cC cP dB Dg gW Hq Ic Ji Kf Ly Nc Nd Nj Nl Nn Nr Nx Og Ok Pg Pj Ra rZ Ss Tz) Pc(aA aC An Ap aY cK cN cO cP Cx DB Dg Dk Do eM Hu Ir Jh Jj Jr Lx Ly Mb Mg Mu Mv Mw Na Nd No Nr Qd qZ Vz wH) Uf(aH aN cO Cu Fn hB Hu iJ iP Kz Lv Ma Nn nO Of Oh oK oN oQ Oy Qy Ra Ur uW vP vU wB wG wJ wL wP zI xA Wn) Ly(aA aC Ad Aw Bo cK cO cP De DI eM Gl Hu hV Im Ir Iv Jh Jj Jl Lh Lj Lx Mv Mw Nc Ne Nj No Nx Pg Qe) Fi(aJ cG cP cQ Cu dN Hu Jk Jp Jr Kf Kl Ko Mg Mn Mt No Nq Nt On Pg Ps Qv Qy Rz Ss Tz Ua Vs Yg Zq Xa) Dc(aF aK bH bM bU bZ cB cC cK cP DB Ed Fp Hr Hw Kc Kf Mt Nc Nd Ne Nh Nj Nl Nx Ok Oz Pb Pj Ur) Et(An aY bH bL Bn bQ cO cP Cu dB dI Dq eD eM hV Ic jF jO jT kS lY Ou pI qC qU Qy rB Tn Tz Ur vU) Ed(bQ bV cK cN dE dI Fy Gl Ih Ik Kc Kl Ko Lv Mg Mw Nh Nm Nr Oi Oy Pf Ph Po Qm Ra Tt uM vQ wL) hR(aC Bb bP dB Dd dE Fn hW Jg jL Jp Ld Lh Mn Ms Mv Ng No Nx On Or Pf Po pS qC qU Ra Rc Uk yJ) An(aH Aj aK aU Aw bC Bn cB cC cG cN cO dB dI Gl Lh Mg Nk Nl Nn No Ns Nv Nx Oh On Oy Pa Pf) Yl(aJ aY bN bX cN cP dN EF Jg Jl Jp Kf Kl Li Mh Nj Pk Qt Qy Qz Rz Ut Wb Yg Ye Tm Xa) Tz(Ad Ap aY Dg dI Hw Ik In jR Kc Kl Mj Mm nD Nf nT Ok Ph qA qC qD Qg Rm rW Ur Va vU) Jj(Fr Hu Ii Ir Iv Jl Jm Lj Mb Mg Mm Mu Mw Mz Nd Nj Nn Nr Nu Oh Oy Oz Pe Pf Po Pz Qd) aH(Aw bF cC cT Dg Fp Ic Jd Jp Ke Kf Ko Kp Lh Mg Mt Nh Nr Nv Nx Oi On Oy Pe Pf Pj Ss) Bn(Ad bX cO dB Dg dI Fp Gl gT gW Hw Jp Kc kI Mb Mt Nc Nd Nh Nl Nw Ok On Oy Oz Pb) wL(aE cH cZ Dc dE Dg Dk Jh Ji Jo Kc Kf Kq lK Nm oE Og Oi On Po Pz rR Tr Vs Vt) wF(aE aL aO aQ aV bL cH Co cR Dd dI Hu Hw jG jK jM lK Mq Mu Nq OE rQ rR vS) Mb(Ad DB Dq Ex Hv Ii Im Ir Jm Mg Ml Mv Mw Nk Nr Nu Oe Of Oz Pa Pg Pz Qc) Ok(bC bL cP Cu cW DB dH dI eD eT Gw Ic jP Ks pI qU QY rB Rh Tn Uv vH) Ad(DB dV eP Fn gW Ic jO jP Ks Ld Nk Nr Ns Pf Pg qA qC Qy Ra Rm tL) Nw(aC aF bL bQ cO cP cQ Cu dB dI hV iA Ld lY nB pI qU Qx QY rB Vp) aN(cT fP Fy Hb Hp Ic Iz Ke Kl Ko Kp Kz Ph Ra Rc Ss Ue Uk Uu vB Vz Tl) cK(aM Ap aW aY bC bM bU cB cC cP Fp Jd Kp Lh Mg Mt Ng Nm Nt On Pe Pj) wH(Ao cH cO Iq Iz Jo Kf Kj Kk Kp lM Mm Mt Nq Qh Qm Qt Ra Ri Vt Vv Ti) vU(aC aE aL bL Cv Dc Ef Fy Jh Lu Ma Nm Om Or Pi Pz qU Rc Ub Uc Ug Uk) bQ(Aw bA bF cB Dg Fp Fy Ic Jp Kc Ke Kl Lh Mg Ng Nh Nt Nv On Rc Ss) Fc(aJ Ef Hf Iz Jg Jh Jl kC kI mI Mn MW Nq Nv Pf Qy Qz Tn Vs) Nc(aA Cx Dg eQ Hu Il Im In Ir Iv Lx Mg Mu Mv Mw Nu Om Pa Po Pz) vS(aC aE bE bF bL dI dJ jG Kz lM Ma Or qA qC qD rX uO vI yH tF) Nk(aC cP Iv Iz Jl Kc Ke Kl Me Mm Nd Nn Oh Ph Po Qb Qd Qh Tt) Im(aC fN Fr iA Lh Mm Ne Nx Pa Pf qA qB qD qU rU rV uN yJ Tl) Lj(Fr Hu Hw In Iv Me Mm Mu Mv Mw Ne Nn Nu Nv Oe Of Om Oy Qb) cO(Aj Ap bF bM Fp fR Jd Jp Kc Kl Ko Lh Nh Nm Nt Nv Oy Pj tX) zH(bE Cv Dc Dk Fy Ic Ik Il Jd Ji Jo Kj Ma Mg Ms Nm Pz Uu Vt) Vz(aY cB cP cQ dN Ef Ib Iz Jg Jk Qt Qv Rz Ua Vs Wd Wh Tl) Ra(Ap Cp dE Fr jO Kc Ke Kf Kl Kp Kq Lh Li Nm Nv Nx On tR) wG(aS Fy Ip Iz Jo Ke Kj Mm Mv Nu On Oy Rc rR St Tr Ub Ug) Dg(aK aX bH bL cB cE cN Cu Db dI dU Ic Nh Nl Nx Qv vH) Hw(Ih Iv Jl Kf Lh Mv Mw Nm Nn Nr Oh Om Po Qd Qe Tt Uc) Jg(eM Ex Gb hV Kq lY Pi Pj Qh qY qZ rZ Tv Ut Vb Vs Vu) bZ(Aw Ef Jd Ke Kl Ko Lh Mg Ng Nh Nt Nv Nx Oi Pf Ph Pj) dB(aJ Aw bA bF bU cN cP cT dU Kp Mt nD Nh Nl Pb Pe qC) Nd(Ao Ap Ax Cp Ir Jh Jr Lx Mk Mr Mv Na Nu Oe Of Po) Jp(bH bL cE Fn hB jP Ld lY nB oN pI Qy Rm rZ Tn Vp) pS(bL Dd Jo Mh Nm Nn Nr qC Qh Qt Qx Uc Uh Ul Uu Vo) Ne(aA Dk Il Ir Iv Lx Mg Mu Nu Oe Om Pa Po Pz Qe) Kf(Cq Gd Hq Hr Kc kS Mj Ns Of Oh oN Ou Qy tR vH) On(aC bL dH eM cP jP kI Ks Ld lL lY oN qU rB rZ) bU(aJ aM Ao aW bF cG cI cP cT Db dV kI mE nD nT) Aw(aU aV Bg bH bL bM cC cN cP Cx dI Fp tS vH) Mz(Hu hX In jE jP Jr jY Mg Ml Of Om Pa rB Vp) Ke(Cu hA iA iP Js Lv Mp Nn oN Pg qC sO Tn vH) Lh(bH cP cQ Cu Iq mT nF Of Oh Qb qY rB Rm Vp) lY(Fr Ir jH Jq Lx mH Mn Mw mZ Na Nt Nv oO oQ) qU(Al bG Cw Fn Gl Hf iP Jq Kj Kp Nv Om Qm sC) Mm(aC Fn Hx Il Ir Iv Jr Nn No Oh Oy pI Qv) cE(Kc Li Ng Nh Nm Nt Nv Nx Pe Pf Ss Ur Uu) iA(Dc eQ Iz Kc Kl Kp Mg Mw Ng Nv Uu Vq Vs) Ap(hB iJ Js Ma Mp Nl rP rV rW rZ Tn vH) Cp(fA gZ Hq kS Nm nT Nx Pf qY Rm rW vH) Oz(aA Hu Ir Jh Jr Mg Mr Mu Mv Na Nr Pz) aC(Jh Mt Mw Nh Nr Ns Nt Nv Nx Oy Pe uO) aY(bL cB FP Hp Ic Ji Kc Kp Mp Nh Tl) cP(Ao bM cC Cx Db Dr Fp Nh Nm Nx Oy Yk) Rc(fN Ic jT kS Lv oN rW sC uT uW yD) Of(Iz Jd Kg Kj Nj Nl Nv Nx Pj Ss tR) bL(aJ aM cB cN Mt Nh Nx Oi Oy Pe sC) dE(cG cM Fn fP iZ kS lL Pj Qm rR Ur) hV(cY Ik Is jL jQ Me Ms Mv mY nK qX) tS(aL aV bE cM Ct Dc Dd Dk jQ lK lM) No(Fp Hu Iv Kc Kl Me Mu nK Nq Pf) Zq(Hb iP iZ jF lL Nf Qn Qv Vq Ti) Ji(jF jP Kz Ld nB pI qC Qv Qy rW) Ao(bM eM Nj Qv rR rZ uT vH zI) Fr(Ex Il Iq Ir Jr mT Nq Oh Qb) Nm(Fn In Kn Lv Me Om Qv tR vT) Kl(eM Fn Js Lv Mp Ns Oy Pg vH) eQ(Ld Li Mw Nf Nl oF oO Ri Uc) gT(aK aU bN cJ Co cY dR Ef Gp) kI(bH cF cS dL Em gL hC Kp oF) Dq(aV bN cY dR Gn Nx Pb Qn) Ti(iP Pj rV rZ vH vI vP tL) Kc(dI Ik Kn Lv Mw Ou Qy Tm) Pf(aA Il In Jd Mu Nu Oh Pj) tR(Dc Dp Hb Ic Kk Nr Oi Ql) Ml(kG Kn nK Nv pI Pj Po) Mt(aG dH dI Nn Ns Oh Qb) Nj(dI Dk Hu Ir Jr Oe Pz) Iv(aA In Mu Nu Oh Oy Pa) Qa(Hu Hx Il Iq Js Oy qA) Kq(Cu eT Js Ld Lv Mp Pg) Om(nB Nq Nu Qd qZ rQ rW) eM(bM cJ Hf Iz Kz Lx Uc) jR(kG mM mP mU mZ nK nU) rZ(Gl Hb Ic Kp Mg Ng Vo) Fy(Hq Lv Mh Pg Qv uL) Me(Mw Nn Oh Oy qA Qd) Nv(Cu Il Iq nB pI qZ) aA(Lv Mf Nu Nx Po Qe) nD(aU aV bG bP gL hC) rB(Hb Kg Kj kO nH nJ) jQ(kG mI mU nI nK nU) Dc(fN qA rV vC vH) Ms(jF kG Nn qZ uM) Nf(nK Po Yg Tm Xa) Hp(cQ Du Hf iO iZ) Hu(Jl Pa Pe Po Qe) Qv(Kg Kj Si Uc Yg) Tl(Cs Fb jI Li Qy) Kp(bI cN Js Pg Ub) Pj(Ib In Jo Oh Pg) cB(aM Cx Db dX eP) dI(FP Nh Nt sC) dU(Af aQ Cq Cu mP) rW(Cv Cw Or rX Vs) Gn(bX Ct Or tF) Ij(Gw pI qC yJ) Iz(fB Lv Va Vb) Jd(bI Fn oN Oy) Tm(cQ Ko nB Pk) Vj(iP iZ Ky tF) Pe(Il Mw Nu Pz) bM(bC bP Db dD) cN(cC Db Kj Nx) dV(aK Bg Co cY) mZ(bH jD oP oQ) kK(hC Lp pH Vs) sC(aE cH Pz Rf) vH(Dk Ef Kj lK) Gl(Db jG qY) Nn(Hx Iq Nx) Mu(Nu Oh Qe) Ng(eT kS qC) Nl(Cx Dk Ir) In(Jl Po Qd) Wd(lL nJ rX) Ld(jO lL qA) Pk(Yg Ye Xa) gW(Em Ps Yj) nT(gL hC Yk) nB(Jq oP Yi) iZ(Vi Wh Zx) kG(hA oP Ue) kP(aQ cM Uy) uO(Lu Mq Uk) Fb(Ru Vc) Fp(bC Di) Lv(Ko Ph) Ma(Gw uT) Mg(kS Uy) Hx(Jl Qe) Ic(cQ yJ)

Figure 12 Continued

Ih(qA Rm) Ii(eD rV) Qb(Jl Qd) Jh(Nq wB) Kg(Js rP) Rf(qC uN) Qn(Vi Xa) Uh(rQ rR) Vb(Ib Qz) Ux(iP Vq) aW(bH bX) cC(bA bF) cH(vP yL) fN(Cw Dk) nR(jT Qm) mM(Du jH) mP(hC pI) BbjT BgeP CxNh EffB PoqA EmnA FnjO GhfP LuyH MhKn HcVc HfYe IqOh SfmI QeOy QtxA JnoP JqqZ KjVa LioT NxcQ UwiC VhqY VqiP VswD VvuW PbfR aOuT bCpH cJuN cRtX dAyL mSjH qCjL

Figure 12 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.0E1 | 6.1E1 | 8.1E1 | 8.6E1 | 5.8E1 | 7.3E1 | 1.0E0 | 1.0E1 | 4.8E2 | 2.6E2 | 1595 | 20 | 266 | 20 | 0.49 |
| Ad | ug/mL | 3.8E-2 | 2.3E-2 | 9.4E-2 | 4.8E-2 | 4.1E-1 | 4.3E-2 | 2.7E-4 | 1.9E-3 | 8.5E0 | 1.3E-1 | 447 | 16 | 170 | 16 | 0.45 |
| Af | ng/mL | 1.2E0 | 4.7E-1 | 1.8E1 | 4.3E0 | 6.7E1 | 7.4E0 | 1.7E-3 | 1.7E-3 | 5.3E2 | 2.2E1 | 447 | 16 | 170 | 16 | 0.40 |
| Aj | ug/mL | 1.4E0 | 4.6E-1 | 2.6E0 | 2.5E0 | 2.4E0 | 2.8E0 | 1.5E-3 | 9.3E-3 | 6.1E0 | 6.1E0 | 447 | 16 | 170 | 16 | 0.45 |
| Al | mg/mL | 8.7E-5 | 1.1E-4 | 2.5E-4 | 1.0E-4 | 4.1E-4 | 4.6E-5 | 2.3E-6 | 9.5E-6 | 1.9E-3 | 1.9E-4 | 447 | 16 | 170 | 16 | 0.51 |
| An | U/mL | 4.8E1 | 1.6E2 | 1.8E2 | 2.1E2 | 5.5E2 | 2.0E2 | 9.8E-4 | 1.3E1 | 7.8E3 | 6.1E2 | 447 | 16 | 170 | 16 | 0.66 |
| Ao | pg/mL | 9.2E1 | 1.1E2 | 5.1E2 | 2.1E2 | 3.5E3 | 2.9E2 | 1.5E0 | 2.5E1 | 3.9E4 | 1.2E3 | 447 | 16 | 170 | 16 | 0.56 |
| Ap | ng/mL | 3.3E1 | 3.8E1 | 4.7E1 | 4.0E1 | 5.0E1 | 2.8E1 | 8.4E-5 | 3.2E0 | 3.3E2 | 9.5E1 | 447 | 16 | 170 | 16 | 0.51 |
| Ar | ng/mL | 9.5E-1 | 1.5E0 | 1.2E1 | 3.8E0 | 1.9E2 | 5.6E0 | 3.4E-3 | 3.4E-3 | 4.1E3 | 2.1E1 | 447 | 16 | 170 | 16 | 0.56 |
| As | ng/mL | 8.7E-3 | 4.5E-3 | 1.6E-2 | 8.0E-3 | 6.1E-2 | 8.4E-3 | 1.7E-3 | 1.7E-3 | 1.2E0 | 3.3E-2 | 447 | 16 | 170 | 16 | 0.42 |
| Aw | pg/mL | 1.6E1 | 1.8E1 | 1.6E1 | 1.9E1 | 6.4E0 | 4.8E0 | 2.9E-2 | 1.2E1 | 5.1E1 | 3.0E1 | 447 | 16 | 170 | 16 | 0.66 |
| Ax | ng/mL | 2.1E0 | 4.1E0 | 1.6E1 | 2.6E1 | 6.3E1 | 7.1E1 | 1.2E-2 | 1.7E-1 | 7.7E2 | 2.9E2 | 447 | 16 | 170 | 16 | 0.57 |
| Ba | ng/mL | 6.1E1 | 1.6E2 | 4.1E2 | 1.4E3 | 1.1E3 | 2.7E3 | 3.7E-1 | 2.7E-1 | 8.1E3 | 8.1E3 | 447 | 16 | 170 | 16 | 0.61 |
| Bb | ng/mL | 3.4E0 | 2.5E0 | 6.8E0 | 7.4E0 | 1.4E1 | 1.2E1 | 4.1E-3 | 4.1E-3 | 2.5E2 | 4.9E1 | 447 | 16 | 170 | 16 | 0.48 |
| Bc | ng/mL | 3.8E1 | 5.5E1 | 1.1E2 | 1.2E2 | 2.0E2 | 1.8E2 | 1.1E-1 | 4.3E-1 | 1.2E3 | 6.9E2 | 447 | 16 | 170 | 16 | 0.52 |
| Bg | ng/mL | 7.7E-2 | 5.4E-1 | 5.4E0 | 2.9E0 | 5.4E0 | 5.3E0 | 5.3E-4 | 5.3E-4 | 4.4E2 | 2.1E1 | 447 | 16 | 170 | 16 | 0.58 |
| Bn | ng/mL | 5.6E-2 | 1.1E-1 | 1.3E0 | 1.1E0 | 3.3E0 | 2.0E0 | 5.6E-2 | 5.6E-2 | 5.8E1 | 7.0E0 | 447 | 16 | 170 | 16 | 0.51 |
| Bo | ng/mL | 1.2E1 | 8.8E0 | 1.4E1 | 1.5E1 | 1.9E1 | 1.5E1 | 1.6E-2 | 1.6E-2 | 2.8E2 | 4.8E1 | 447 | 16 | 170 | 16 | 0.49 |
| Ch | uIU/mL | 9.7E-1 | 1.3E0 | 1.7E1 | 1.7E1 | 1.0E2 | 3.3E1 | 3.4E-3 | 3.4E-3 | 1.8E3 | 9.8E1 | 447 | 16 | 170 | 16 | 0.50 |
| Co | pg/mL | 3.8E1 | 3.4E1 | 1.8E2 | 1.8E2 | 9.6E2 | 5.1E2 | 1.5E-1 | 1.5E-1 | 1.7E4 | 2.1E3 | 447 | 16 | 170 | 16 | 0.51 |
| Cp | ng/mL | 2.1E1 | 3.0E1 | 3.0E1 | 3.6E1 | 6.7E1 | 1.7E1 | 6.0E-1 | 1.4E1 | 1.3E3 | 7.7E1 | 447 | 16 | 170 | 16 | 0.73 |
| Cq | ng/mL | 2.8E-2 | 3.1E-2 | 2.5E-1 | 8.1E-2 | 2.5E0 | 1.3E-1 | 8.0E-4 | 8.0E-4 | 4.9E1 | 5.2E-1 | 447 | 16 | 170 | 16 | 0.56 |
| Cs | ng/mL | 5.9E1 | 7.7E1 | 3.2E2 | 6.6E2 | 1.2E3 | 1.3E3 | 2.7E-2 | 3.6E0 | 1.8E4 | 5.1E3 | 447 | 16 | 170 | 16 | 0.54 |
| Ct | ng/mL | 6.1E-1 | 1.9E-1 | 3.2E1 | 6.7E1 | 9.9E1 | 1.6E2 | 1.1E-4 | 1.1E-4 | 6.2E2 | 4.7E2 | 447 | 16 | 170 | 16 | 0.48 |
| Cu | ng/mL | 2.4E-1 | 3.0E-1 | 5.5E-1 | 4.3E-1 | 3.2E0 | 5.5E-1 | 9.6E-3 | 9.0E-5 | 6.6E1 | 2.3E0 | 447 | 16 | 170 | 16 | 0.52 |
| Cv | ng/mL | 5.8E0 | 3.5E0 | 2.8E1 | 8.3E0 | 6.9E1 | 1.3E1 | 1.4E-4 | 1.4E-4 | 5.3E2 | 4.3E1 | 447 | 16 | 170 | 16 | 0.39 |
| Cw | mIU/mL | 3.0E-2 | 2.8E-2 | 5.4E-2 | 3.3E-2 | 3.2E-2 | 2.4E-2 | 1.5E-4 | 4.8E-3 | 6.8E0 | 9.2E-2 | 447 | 16 | 170 | 16 | 0.46 |
| Cx | ng/mL | 4.6E-1 | 2.4E-2 | 6.0E1 | 4.7E1 | 1.1E2 | 1.0E2 | 9.3E-5 | 9.3E-5 | 3.9E2 | 2.8E2 | 447 | 16 | 170 | 16 | 0.42 |
| Db | ug/mL | 7.6E0 | 6.7E0 | 9.6E0 | 7.8E0 | 1.1E1 | 6.5E0 | 4.5E-1 | 4.8E-1 | 1.4E2 | 2.3E1 | 447 | 16 | 170 | 16 | 0.45 |
| Dc | nmol/L | 1.9E-2 | 1.7E-2 | 8.6E-2 | 5.7E-2 | 6.7E-1 | 1.0E-1 | 5.2E-6 | 6.0E-4 | 1.4E1 | 4.0E-1 | 447 | 16 | 170 | 16 | 0.53 |
| Dd | ug/mL | 7.8E-2 | 6.2E-2 | 1.9E-1 | 8.0E-2 | 3.1E-1 | 7.7E-2 | 1.9E-4 | 8.3E-5 | 3.6E0 | 2.5E-1 | 447 | 16 | 170 | 16 | 0.41 |
| De | ng/mL | 3.4E-3 | 3.4E-3 | 7.6E-2 | 1.0E-1 | 1.5E-1 | 1.5E-1 | 3.4E-3 | 3.4E-3 | 9.2E-1 | 4.7E-1 | 447 | 16 | 170 | 16 | 0.55 |
| Dg | ng/mL | 3.4E1 | 3.6E1 | 4.6E1 | 3.3E1 | 4.1E1 | 2.6E1 | 1.0E-1 | 9.3E-1 | 1.9E2 | 7.5E1 | 447 | 16 | 170 | 16 | 0.42 |
| Di | pg/mL | 1.9E0 | 1.7E0 | 2.2E0 | 2.8E0 | 2.1E0 | 3.7E0 | 1.8E-1 | 1.8E-1 | 1.3E1 | 1.6E1 | 447 | 16 | 170 | 16 | 0.51 |
| Dk | uIU/mL | 1.6E-2 | 3.2E-2 | 8.7E-2 | 4.9E-2 | 5.1E-1 | 4.5E-2 | 1.1E-4 | 1.1E-4 | 8.9E0 | 1.4E-1 | 447 | 16 | 170 | 16 | 0.61 |
| Dl | ng/mL | 2.4E2 | 1.8E2 | 3.2E2 | 2.5E2 | 2.9E2 | 2.5E2 | 2.5E0 | 4.0E0 | 1.6E3 | 9.0E2 | 447 | 16 | 170 | 16 | 0.43 |
| Dp | ng/ml | 2.5E0 | 7.9E-1 | 6.4E0 | 3.1E0 | 1.5E1 | 5.8E0 | 3.7E-3 | 5.3E-3 | 2.0E2 | 1.9E1 | 262 | 14 | 160 | 14 | 0.31 |
| Dr | pg/ml | 2.9E1 | 7.8E0 | 1.2E2 | 3.6E1 | 8.3E2 | 4.7E1 | 7.5E-1 | 7.5E-1 | 1.0E4 | 1.2E2 | 158 | 9 | 91 | 9 | 0.40 |
| Ef | ng/ml | 1.3E-1 | 4.4E-1 | 8.6E-1 | 1.7E0 | 1.9E0 | 2.9E0 | 5.7E-4 | 5.7E-4 | 1.0E1 | 1.1E1 | 325 | 16 | 167 | 16 | 0.57 |
| Wm | % | 7.2E-1 | 1.3E0 | 3.2E1 | 1.2E2 | 1.8E2 | 3.4E2 | 5.4E-2 | 8.5E-2 | 2.4E3 | 1.3E3 | 353 | 19 | 182 | 19 | 0.56 |
| Ed | pg/ml | 5.2E-1 | 5.2E-1 | 5.9E1 | 4.1E1 | 4.5E2 | 6.6E1 | 5.2E-1 | 5.2E-1 | 7.3E3 | 1.6E2 | 262 | 14 | 159 | 14 | 0.49 |
| Tj | pg/mL | 3.7E-1 | 3.7E-1 | 5.6E1 | 4.5E0 | 3.0E2 | 1.1E1 | 3.6E-1 | 3.7E-1 | 3.5E3 | 4.2E1 | 323 | 15 | 169 | 15 | 0.40 |
| Po | pg/ml | 5.4E-1 | 2.6E0 | 8.9E0 | 1.8E1 | 2.6E1 | 4.2E1 | 8.0E-3 | 2.6E-2 | 2.7E2 | 2.2E2 | 755 | 29 | 295 | 29 | 0.61 |
| Ti | ug/mL | 3.6E0 | 1.4E0 | 5.0E0 | 2.4E0 | 4.2E0 | 2.5E0 | 1.2E-1 | 8.7E-3 | 1.8E1 | 6.7E0 | 152 | 10 | 114 | 10 | 0.29 |
| Em | ng/ml | 2.9E-3 | 2.9E-3 | 7.8E-2 | 2.1E-2 | 1.9E-1 | 4.7E-2 | 1.9E-16 | 2.8E-16 | 1.9E0 | 1.3E-1 | 204 | 8 | 91 | 8 | 0.30 |
| Et | ng/ml | 1.4E3 | 1.5E3 | 1.7E3 | 1.8E3 | 1.2E3 | 1.4E3 | 7.5E1 | 1.5E2 | 5.0E3 | 5.0E3 | 754 | 29 | 295 | 29 | 0.50 |
| Th | ug/mL | 1.1E0 | 6.8E-1 | 1.6E0 | 1.4E0 | 1.6E0 | 1.3E0 | 2.6E-3 | 6.5E-2 | 1.2E1 | 3.5E0 | 152 | 10 | 114 | 10 | 0.44 |
| Fa | ng/ml | 4.0E1 | 4.9E1 | 1.3E2 | 5.2E1 | 5.6E2 | 3.5E1 | 3.4E-2 | 2.0E0 | 8.0E3 | 1.0E2 | 261 | 14 | 158 | 14 | 0.50 |
| Ez | ng/ml | 3.8E0 | 6.5E0 | 1.5E1 | 6.7E1 | 3.2E1 | 1.9E2 | 1.3E-2 | 1.3E-2 | 3.0E2 | 7.1E2 | 262 | 14 | 160 | 14 | 0.57 |
| Fb | ng/ml | 2.5E1 | 2.8E1 | 2.2E1 | 2.2E1 | 1.1E1 | 1.4E1 | 5.9E-1 | 1.0E0 | 5.7E1 | 3.9E1 | 262 | 14 | 158 | 14 | 0.53 |
| Ex | ng/ml | 7.8E-2 | 1.2E-1 | 2.2E-1 | 4.2E-1 | 6.9E-1 | 8.8E-1 | 3.5E-5 | 1.5E-4 | 8.9E0 | 3.1E0 | 245 | 12 | 117 | 12 | 0.53 |
| Fn | ng/ml | 2.1E-1 | 2.1E-1 | 5.9E0 | 3.2E-1 | 2.7E1 | 3.9E-1 | 1.1E-14 | 2.1E-1 | 4.2E2 | 1.7E0 | 262 | 14 | 160 | 14 | 0.31 |
| Fp | ng/ml | 1.3E1 | 1.4E1 | 2.5E1 | 3.4E1 | 2.8E1 | 3.4E1 | 6.0E-3 | 2.8E-1 | 1.4E2 | 1.0E2 | 787 | 30 | 296 | 30 | 0.57 |
| Fr | ng/ml | 3.5E4 | 1.1E5 | 1.1E5 | 2.7E5 | 1.7E5 | 3.0E5 | 1.9E2 | 7.8E2 | 9.0E5 | 8.9E5 | 890 | 31 | 300 | 31 | 0.63 |

Figure 13

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fw | pg/ml | 1.1E0 | 5.3E0 | 6.2E1 | 1.6E1 | 4.8E2 | 2.9E1 | 1.1E-14 | 1.2E-1 | 6.9E3 | 1.1E2 | 325 | 16 | 168 | 16 | 0.61 |
| Fy | ng/ml | 3.8E1 | 3.1E1 | 6.0E1 | 4.7E1 | 7.3E1 | 4.6E1 | 1.2E-1 | 3.8E0 | 6.5E2 | 1.5E2 | 260 | 13 | 159 | 13 | 0.47 |
| Gc | ng/ml | 1.1E2 | 4.0E1 | 1.7E2 | 5.3E1 | 1.8E2 | 6.1E1 | 6.4E0 | 9.7E0 | 1.2E3 | 2.2E2 | 169 | 10 | 94 | 10 | 0.19 |
| Gd | ng/ml | 3.1E1 | 1.5E1 | 3.3E1 | 1.9E1 | 1.7E1 | 1.2E1 | 5.0E0 | 8.0E0 | 8.1E1 | 4.5E1 | 189 | 8 | 83 | 8 | 0.24 |
| Gn | U/ml | 2.8E-1 | 3.8E-1 | 2.1E0 | 4.1E-1 | 9.6E0 | 4.7E-1 | 1.3E-3 | 5.6E-3 | 1.1E2 | 1.3E0 | 152 | 9 | 89 | 9 | 0.38 |
| Gl | | 7.1E3 | 1.6E4 | 1.1E4 | 1.4E4 | 9.1E3 | 1.0E4 | 9.1E1 | 6.3E2 | 3.4E4 | 2.8E4 | 316 | 16 | 166 | 16 | 0.59 |
| Gp | U/ml | 1.5E0 | 9.3E-1 | 4.1E0 | 3.6E0 | 7.0E0 | 6.2E0 | 1.3E-3 | 1.5E-2 | 6.7E1 | 2.0E1 | 327 | 16 | 168 | 16 | 0.44 |
| Gz | ug/ml | 1.4E0 | 8.7E-1 | 8.9E0 | 3.8E0 | 3.7E1 | 4.7E0 | 2.9E-16 | 3.8E-3 | 4.8E2 | 1.1E1 | 181 | 9 | 106 | 9 | 0.42 |
| Ha | ng/ml | 2.3E0 | 4.3E0 | 9.5E0 | 7.4E0 | 2.1E1 | 9.3E0 | 6.4E-3 | 2.8E-1 | 1.3E2 | 3.2E1 | 260 | 14 | 159 | 14 | 0.60 |
| Nm | pg/ml | 1.5E4 | 8.9E3 | 3.4E4 | 3.4E4 | 8.7E4 | 8.2E4 | 1.0E-9 | 1.0E-9 | 1.6E6 | 4.4E5 | 758 | 29 | 297 | 29 | 0.43 |
| Nn | pg/ml | 1.5E2 | 5.2E2 | 1.7E3 | 5.1E3 | 7.6E3 | 1.4E4 | 1.0E-9 | 3.0E0 | 1.0E5 | 6.9E4 | 758 | 29 | 297 | 29 | 0.64 |
| No | pg/ml | 1.5E1 | 2.8E1 | 3.9E1 | 1.2E2 | 1.2E2 | 3.1E2 | 1.0E-9 | 2.4E-1 | 2.5E3 | 1.4E3 | 758 | 29 | 297 | 29 | 0.55 |
| Nq | pg/ml | 1.7E0 | 4.5E0 | 1.7E1 | 2.9E1 | 6.8E1 | 5.9E1 | 1.0E-9 | 1.0E-9 | 1.2E3 | 2.7E2 | 758 | 29 | 297 | 29 | 0.59 |
| Nr | pg/ml | 9.7E-1 | 3.5E-1 | 3.1E1 | 3.0E2 | 1.9E2 | 1.6E3 | 1.0E-9 | 1.0E-9 | 4.1E3 | 8.5E3 | 758 | 29 | 297 | 29 | 0.46 |
| Ns | pg/ml | 1.0E-9 | 1.0E-9 | 7.1E0 | 4.4E0 | 3.5E1 | 2.2E1 | 1.0E-9 | 1.0E-9 | 6.8E2 | 1.2E2 | 758 | 29 | 297 | 29 | 0.50 |
| Nt | pg/ml | 1.0E2 | 1.4E2 | 1.3E2 | 1.8E2 | 1.1E2 | 1.5E2 | 1.0E-9 | 1.5E1 | 1.7E3 | 6.8E2 | 758 | 29 | 297 | 29 | 0.58 |
| Nu | pg/ml | 2.0E1 | 1.2E1 | 5.3E1 | 1.0E2 | 8.9E1 | 1.5E2 | 1.0E-9 | 1.0E-9 | 8.9E2 | 5.8E2 | 758 | 29 | 297 | 29 | 0.55 |
| Lu | pg/ml | 1.0E4 | 1.0E4 | 1.8E4 | 9.9E3 | 6.5E4 | 1.1E4 | 3.5E2 | 1.3E3 | 1.3E6 | 6.1E4 | 761 | 29 | 297 | 29 | 0.43 |
| Lv | pg/ml | 1.0E-9 | 1.0E-9 | 1.1E1 | 2.8E1 | 2.1E1 | 4.6E1 | 1.0E-9 | 1.0E-9 | 2.4E2 | 1.9E2 | 761 | 29 | 297 | 29 | 0.59 |
| Lw | pg/ml | 1.0E-9 | 1.0E-9 | 4.3E-1 | 1.3E0 | 4.1E0 | 4.9E0 | 1.0E-9 | 1.0E-9 | 8.0E1 | 2.1E1 | 761 | 29 | 297 | 29 | 0.54 |
| Lx | pg/ml | 1.0E-9 | 6.5E1 | 1.8E2 | 7.4E2 | 9.3E2 | 2.0E3 | 1.0E-9 | 1.0E-9 | 2.2E4 | 1.0E4 | 761 | 29 | 297 | 29 | 0.61 |
| Ly | pg/ml | 1.0E-9 | 1.0E-9 | 1.0E1 | 1.0E1 | 2.0E1 | 1.7E1 | 1.0E-9 | 1.0E-9 | 1.2E2 | 5.8E1 | 761 | 29 | 297 | 29 | 0.52 |
| Lz | pg/ml | 1.0E-9 | 1.0E-9 | 4.0E0 | 7.6E0 | 3.2E1 | 3.9E1 | 1.0E-9 | 1.0E-9 | 6.0E2 | 2.1E2 | 761 | 29 | 297 | 29 | 0.50 |
| Ma | pg/ml | 2.9E2 | 2.0E2 | 1.3E3 | 9.9E2 | 3.6E3 | 2.0E3 | 1.0E-9 | 1.0E-9 | 6.5E4 | 9.5E3 | 761 | 29 | 297 | 29 | 0.45 |
| Mb | pg/ml | 2.5E1 | 2.5E1 | 3.1E1 | 3.2E1 | 1.5E1 | 1.5E1 | 4.1E0 | 1.8E1 | 2.1E2 | 6.9E1 | 761 | 29 | 297 | 29 | 0.53 |
| Mc | pg/ml | 1.0E-9 | 1.0E-9 | 4.3E-2 | 1.0E-2 | 6.1E-1 | 0.0E0 | 1.0E-9 | 1.0E-9 | 1.3E1 | 1.0E-9 | 761 | 29 | 297 | 29 | 0.49 |
| Md | pg/ml | 1.0E-9 | 1.0E-9 | 4.5E-1 | 2.8E-1 | 3.9E0 | 1.4E0 | 1.0E-9 | 1.0E-9 | 6.8E1 | 7.4E0 | 761 | 29 | 297 | 29 | 0.52 |
| Me | pg/ml | 3.3E1 | 2.6E1 | 3.2E1 | 2.6E1 | 2.0E1 | 1.8E1 | 1.0E-9 | 7.9E-1 | 3.2E2 | 7.9E1 | 761 | 29 | 297 | 29 | 0.36 |
| Mf | pg/ml | 1.0E-9 | 1.0E-9 | 5.0E-1 | 2.2E-2 | 2.8E0 | 1.0E-1 | 1.0E-9 | 1.0E-9 | 5.6E1 | 5.3E-1 | 761 | 29 | 297 | 29 | 0.46 |
| Mg | pg/ml | 1.6E0 | 6.7E-1 | 7.0E0 | 4.7E0 | 1.2E1 | 7.1E0 | 1.0E-9 | 1.0E-9 | 9.2E1 | 2.7E1 | 761 | 29 | 297 | 29 | 0.47 |
| Mh | pg/ml | 1.0E-9 | 1.0E-9 | 1.5E0 | 1.5E0 | 1.0E1 | 7.0E0 | 1.0E-9 | 1.0E-9 | 1.6E2 | 3.8E1 | 761 | 29 | 297 | 29 | 0.54 |
| Mi | pg/ml | 1.0E-9 | 1.0E-9 | 9.4E-1 | 1.0E1 | 1.3E1 | 3.2E1 | 1.0E-9 | 1.0E-9 | 3.2E2 | 1.6E2 | 761 | 29 | 297 | 29 | 0.58 |
| Mj | pg/ml | 1.0E-9 | 1.0E-9 | 4.7E0 | 2.0E1 | 2.7E1 | 1.0E2 | 1.0E-9 | 1.0E-9 | 4.6E2 | 5.4E2 | 761 | 29 | 297 | 29 | 0.51 |
| Mk | pg/ml | 2.8E-1 | 2.2E0 | 1.4E1 | 2.0E2 | 9.2E1 | 1.0E3 | 1.0E-9 | 1.0E-9 | 1.7E3 | 5.6E3 | 761 | 29 | 297 | 29 | 0.54 |
| Ml | pg/ml | 1.0E-9 | 1.0E-9 | 6.0E0 | 3.5E-1 | 8.1E1 | 1.3E0 | 1.0E-9 | 1.0E-9 | 2.1E3 | 6.6E0 | 761 | 29 | 297 | 29 | 0.45 |
| Mm | pg/ml | 6.1E2 | 4.0E2 | 1.1E3 | 1.3E3 | 1.4E3 | 2.1E3 | 1.0E-9 | 1.0E-9 | 1.2E4 | 7.7E3 | 761 | 29 | 297 | 29 | 0.45 |
| Mn | pg/ml | 5.4E0 | 4.9E0 | 1.0E1 | 1.0E1 | 2.0E1 | 1.3E1 | 1.0E-9 | 1.0E-9 | 3.5E2 | 6.6E1 | 761 | 29 | 297 | 29 | 0.50 |
| Mp | pg/ml | 1.0E-9 | 4.4E0 | 1.0E1 | 2.8E1 | 3.6E1 | 5.6E1 | 1.0E-9 | 1.0E-9 | 6.3E2 | 1.8E2 | 760 | 29 | 297 | 29 | 0.57 |
| Mq | pg/ml | 1.0E-9 | 1.0E-9 | 2.8E0 | 9.7E0 | 1.6E1 | 3.3E1 | 1.0E-9 | 1.0E-9 | 2.1E2 | 1.4E2 | 760 | 29 | 297 | 29 | 0.54 |
| Mr | pg/ml | 1.0E-9 | 1.0E-9 | 3.2E1 | 4.1E2 | 1.8E2 | 2.2E3 | 1.0E-9 | 1.0E-9 | 2.2E3 | 1.2E4 | 760 | 29 | 297 | 29 | 0.57 |
| Ms | pg/ml | 4.1E2 | 5.3E2 | 5.6E2 | 6.0E2 | 6.6E2 | 5.3E2 | 1.0E-9 | 1.0E-9 | 5.9E3 | 2.2E3 | 760 | 29 | 297 | 29 | 0.55 |
| Mt | pg/ml | 2.4E-1 | 1.3E0 | 7.3E0 | 1.5E1 | 4.5E1 | 4.7E1 | 1.0E-9 | 1.0E-9 | 8.7E2 | 2.5E2 | 760 | 29 | 297 | 29 | 0.61 |
| Mu | pg/ml | 1.0E-9 | 1.0E-9 | 9.0E-1 | 2.5E0 | 7.0E0 | 5.4E0 | 1.0E-9 | 1.0E-9 | 9.9E1 | 2.7E1 | 760 | 29 | 297 | 29 | 0.66 |
| Mv | pg/ml | 1.0E-9 | 3.2E0 | 5.8E1 | 1.1E2 | 3.1E2 | 2.2E2 | 1.0E-9 | 1.0E-9 | 4.5E3 | 9.3E2 | 760 | 29 | 297 | 29 | 0.66 |
| Mw | pg/ml | 3.8E1 | 1.2E2 | 4.0E2 | 1.3E3 | 2.8E3 | 3.5E3 | 1.0E-9 | 1.0E-9 | 6.2E4 | 1.7E4 | 760 | 29 | 297 | 29 | 0.63 |
| Mx | pg/ml | 1.0E-9 | 1.0E-9 | 2.2E-1 | 5.4E-1 | 9.1E-1 | 1.3E0 | 1.0E-9 | 1.0E-9 | 9.6E0 | 6.3E0 | 760 | 29 | 297 | 29 | 0.61 |
| My | pg/ml | 1.0E-9 | 1.8E1 | 3.9E2 | 3.8E2 | 2.7E3 | 9.6E2 | 1.0E-9 | 1.0E-9 | 3.9E4 | 4.1E3 | 760 | 29 | 297 | 29 | 0.62 |
| Mz | pg/ml | 1.1E1 | 2.3E1 | 2.6E1 | 5.4E1 | 7.9E1 | 7.5E1 | 1.0E-9 | 1.0E-9 | 1.3E3 | 3.0E2 | 760 | 29 | 297 | 29 | 0.61 |
| Na | pg/ml | 1.0E-9 | 1.0E-9 | 7.4E-1 | 9.9E-1 | 3.2E0 | 2.5E0 | 1.0E-9 | 1.0E-9 | 4.2E1 | 1.1E1 | 760 | 29 | 297 | 29 | 0.56 |
| Nb | pg/ml | 1.9E0 | 2.8E0 | 4.0E0 | 1.2E1 | 1.3E1 | 4.4E1 | 1.0E-9 | 1.0E-9 | 2.3E2 | 2.4E2 | 760 | 29 | 297 | 29 | 0.58 |
| Nc | pg/ml | 3.4E2 | 1.7E2 | 5.8E2 | 3.9E2 | 7.5E2 | 4.9E2 | 1.0E-9 | 1.0E-9 | 9.2E3 | 1.8E3 | 760 | 29 | 297 | 29 | 0.45 |
| Nd | pg/ml | 2.9E1 | 1.3E1 | 3.0E1 | 3.2E1 | 9.0E1 | 4.0E1 | 1.0E-9 | 1.0E-9 | 2.1E3 | 1.4E2 | 760 | 29 | 297 | 29 | 0.48 |
| Ne | pg/ml | 4.5E2 | 3.1E2 | 5.9E2 | 4.1E2 | 5.9E2 | 3.3E2 | 1.0E-9 | 1.0E-9 | 7.0E3 | 1.3E3 | 760 | 29 | 297 | 29 | 0.42 |
| Nf | pg/ml | 1.0E-9 | 1.0E-9 | 2.9E0 | 5.0E0 | 1.1E1 | 1.6E1 | 1.0E-9 | 1.0E-9 | 1.6E2 | 8.2E1 | 760 | 29 | 297 | 29 | 0.52 |
| Ng | pg/ml | 1.9E1 | 5.3E0 | 1.1E2 | 8.5E1 | 2.2E2 | 1.5E2 | 1.0E-9 | 1.0E-9 | 1.6E3 | 6.6E2 | 760 | 29 | 297 | 29 | 0.45 |
| Nh | pg/ml | 6.9E1 | 5.0E1 | 9.2E1 | 7.0E1 | 8.3E1 | 7.1E1 | 1.0E-9 | 2.2E0 | 5.6E2 | 3.4E2 | 760 | 29 | 297 | 29 | 0.41 |
| Ni | pg/ml | 1.0E-9 | 2.3E1 | 7.2E1 | 9.9E1 | 1.2E2 | 1.5E2 | 1.0E-9 | 1.0E-9 | 1.1E3 | 5.5E2 | 760 | 29 | 297 | 29 | 0.55 |

Figure 13 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nj | pg/ml | 7.3E0 | 8.4E0 | 1.1E1 | 1.1E1 | 1.2E1 | 1.2E1 | 1.0E-9 | 1.0E-9 | 8.3E1 | 5.7E1 | 760 | 29 | 297 | 29 | 0.51 |
| Nk | pg/ml | 1.8E1 | 1.7E1 | 3.4E1 | 2.6E1 | 4.0E1 | 3.3E1 | 1.0E-9 | 1.0E-9 | 2.0E2 | 1.7E2 | 760 | 29 | 297 | 29 | 0.49 |
| Nl | pg/ml | 4.6E1 | 3.4E1 | 6.2E1 | 4.0E1 | 7.0E1 | 3.1E1 | 1.0E-9 | 1.0E-9 | 1.1E3 | 1.4E2 | 760 | 29 | 297 | 29 | 0.43 |
| Tz | pg/ml | 4.6E3 | 6.4E3 | 1.3E4 | 1.2E4 | 6.3E4 | 1.5E4 | 1.0E-9 | 6.5E2 | 1.0E6 | 5.2E4 | 264 | 14 | 159 | 14 | 0.56 |
| Ua | pg/ml | 3.7E3 | 5.6E3 | 2.0E4 | 3.9E4 | 1.3E5 | 5.8E4 | 1.0E-9 | 3.2E2 | 2.1E6 | 1.8E5 | 264 | 14 | 159 | 14 | 0.60 |
| Ub | pg/ml | 5.7E2 | 3.7E2 | 8.7E2 | 5.7E2 | 1.1E3 | 6.1E2 | 1.0E-9 | 3.9E1 | 9.8E3 | 2.4E3 | 264 | 14 | 159 | 14 | 0.41 |
| Ue | pg/ml | 3.1E1 | 2.1E1 | 4.0E1 | 1.9E1 | 4.0E1 | 6.6E0 | 9.8E-2 | 8.4E0 | 4.4E2 | 2.9E1 | 264 | 14 | 159 | 14 | 0.29 |
| Uc | pg/ml | 9.2E2 | 8.2E2 | 2.0E3 | 1.0E3 | 4.4E3 | 9.6E2 | 1.0E-9 | 1.4E1 | 5.7E4 | 3.1E3 | 264 | 14 | 159 | 14 | 0.43 |
| Ud | pg/ml | 1.0E-9 | 1.0E-9 | 1.8E0 | 3.4E-1 | 2.4E1 | 1.3E0 | 1.0E-9 | 1.0E-9 | 3.9E2 | 4.8E0 | 264 | 14 | 159 | 14 | 0.53 |
| Hq | pg/ml | 1.0E0 | 1.0E0 | 1.2E2 | 1.4E1 | 1.8E3 | 5.5E1 | 1.0E-9 | 1.0E-9 | 3.4E4 | 3.0E2 | 756 | 29 | 296 | 29 | 0.50 |
| Hr | pg/ml | 1.1E2 | 9.4E1 | 8.0E2 | 8.5E2 | 1.7E3 | 2.1E3 | 1.0E-9 | 2.2E1 | 1.7E4 | 1.1E4 | 756 | 29 | 296 | 29 | 0.50 |
| Hu | pg/ml | 5.1E0 | 8.8E1 | 2.6E3 | 1.3E3 | 2.6E4 | 2.5E3 | 1.0E-9 | 1.0E-9 | 6.3E5 | 8.8E3 | 756 | 29 | 296 | 29 | 0.60 |
| Hv | pg/ml | 1.3E0 | 2.3E0 | 4.2E0 | 7.6E0 | 3.4E1 | 1.8E1 | 1.0E-9 | 1.0E-9 | 8.9E2 | 8.4E1 | 756 | 29 | 296 | 29 | 0.64 |
| Hw | pg/ml | 6.6E0 | 4.0E0 | 3.1E1 | 1.3E2 | 3.5E2 | 6.4E2 | 1.0E-9 | 5.3E-1 | 9.4E3 | 3.4E3 | 756 | 29 | 296 | 29 | 0.44 |
| Hx | pg/ml | 8.3E0 | 1.4E1 | 4.0E1 | 9.6E1 | 3.5E2 | 3.6E2 | 1.0E-9 | 1.0E-9 | 9.3E3 | 2.0E3 | 756 | 29 | 296 | 29 | 0.64 |
| Ib | ng/ml | 4.9E-2 | 7.4E-2 | 1.2E0 | 6.1E0 | 5.3E0 | 1.5E1 | 1.0E-9 | 1.0E-9 | 5.6E1 | 5.2E1 | 259 | 12 | 159 | 12 | 0.55 |
| Ic | U/ml | 2.2E2 | 9.3E1 | 1.1E3 | 1.5E2 | 7.3E3 | 1.4E2 | 1.5E0 | 9.2E0 | 9.3E4 | 3.9E2 | 259 | 12 | 159 | 12 | 0.38 |
| Id | U/ml | 6.8E-1 | 8.3E-1 | 3.0E0 | 9.4E-1 | 2.7E1 | 9.0E-1 | 1.0E-9 | 5.1E-2 | 4.3E2 | 3.4E0 | 259 | 12 | 159 | 12 | 0.46 |
| Tt | pg/ml | 1.6E2 | 1.5E2 | 1.7E2 | 1.6E2 | 5.4E1 | 4.2E1 | 4.3E1 | 1.1E2 | 4.4E2 | 2.3E2 | 246 | 13 | 153 | 13 | 0.43 |
| To | pg/ml | 1.6E0 | 1.8E0 | 1.9E0 | 3.0E0 | 2.3E0 | 2.9E0 | 1.0E-9 | 1.0E-9 | 2.3E1 | 1.0E1 | 254 | 13 | 156 | 13 | 0.61 |
| Tr | pg/ml | 3.3E0 | 1.7E0 | 6.6E0 | 2.6E0 | 2.1E1 | 2.5E0 | 1.0E-9 | 1.0E-9 | 3.1E2 | 8.4E0 | 251 | 13 | 155 | 13 | 0.35 |
| Tn | pg/ml | 2.8E1 | 2.1E1 | 8.2E1 | 5.6E1 | 2.5E2 | 6.8E1 | 2.4E0 | 6.8E0 | 2.3E3 | 2.2E2 | 254 | 13 | 156 | 13 | 0.46 |
| Tv | pg/ml | 1.2E1 | 9.8E0 | 5.2E1 | 1.1E1 | 4.5E2 | 1.2E1 | 1.0E-9 | 1.0E-9 | 7.1E3 | 4.0E1 | 254 | 13 | 156 | 13 | 0.39 |
| Ih | ng/ml | 6.8E1 | 6.4E1 | 2.4E2 | 1.9E2 | 4.3E2 | 3.1E2 | 1.0E-9 | 1.0E-9 | 3.6E3 | 1.2E3 | 760 | 29 | 296 | 29 | 0.51 |
| Ii | ng/ml | 9.1E1 | 5.7E1 | 2.4E2 | 4.6E2 | 6.3E2 | 1.7E3 | 1.0E-9 | 2.9E0 | 8.4E3 | 9.2E3 | 760 | 28 | 296 | 28 | 0.46 |
| Ij | ng/ml | 7.6E1 | 8.5E1 | 2.0E2 | 3.6E2 | 1.1E3 | 1.2E3 | 1.0E-9 | 4.7E0 | 2.4E4 | 6.4E3 | 750 | 27 | 294 | 27 | 0.54 |
| Ik | ng/ml | 1.1E1 | 2.1E1 | 9.1E2 | 4.1E2 | 8.9E3 | 5.5E2 | 5.9E-1 | 1.3E0 | 1.2E5 | 1.5E3 | 755 | 28 | 294 | 28 | 0.60 |
| Il | ng/ml | 3.2E2 | 2.2E1 | 1.3E3 | 8.4E2 | 2.8E3 | 2.3E3 | 1.0E-9 | 1.0E-9 | 1.3E4 | 1.2E4 | 744 | 28 | 295 | 28 | 0.41 |
| Im | ng/ml | 2.1E2 | 2.2E2 | 3.7E2 | 7.5E2 | 5.3E2 | 1.5E3 | 1.3E1 | 2.7E1 | 5.8E3 | 6.8E3 | 754 | 28 | 295 | 28 | 0.52 |
| In | ng/ml | 3.6E0 | 2.8E0 | 3.0E1 | 7.3E0 | 2.3E2 | 1.4E1 | 1.0E-9 | 1.0E-9 | 4.5E3 | 6.8E1 | 760 | 29 | 296 | 29 | 0.43 |
| Hb | ng/ml | 2.6E1 | 1.3E1 | 3.7E1 | 2.5E1 | 3.5E1 | 3.1E1 | 6.2E-1 | 3.3E0 | 2.1E2 | 1.2E2 | 264 | 14 | 159 | 14 | 0.37 |
| Hc | pg/ml | 6.3E2 | 8.7E2 | 3.4E3 | 4.9E3 | 1.3E4 | 7.0E3 | 1.0E-9 | 1.0E-9 | 1.0E5 | 1.9E4 | 264 | 14 | 159 | 14 | 0.60 |
| Hf | ng/ml | 1.5E2 | 1.7E2 | 3.5E2 | 3.0E2 | 4.9E2 | 4.2E2 | 1.0E-9 | 1.0E-9 | 2.5E3 | 1.5E3 | 264 | 14 | 159 | 14 | 0.49 |
| Io | ng/ml | 8.2E3 | 7.2E3 | 2.6E4 | 3.1E4 | 1.6E5 | 1.0E5 | 1.0E-9 | 6.2E1 | 4.0E6 | 5.5E5 | 752 | 28 | 296 | 28 | 0.47 |
| Ip | ng/ml | 8.8E0 | 1.5E1 | 1.9E1 | 2.6E1 | 2.4E1 | 3.4E1 | 1.0E-9 | 1.0E-9 | 2.6E2 | 1.4E2 | 752 | 28 | 296 | 28 | 0.51 |
| Iq | ug/ml | 9.6E-2 | 1.2E-1 | 1.9E1 | 2.7E1 | 5.0E2 | 1.4E2 | 1.0E-9 | 1.0E-9 | 1.4E4 | 7.5E2 | 752 | 28 | 296 | 28 | 0.48 |
| Ir | ug/ml | 3.4E-1 | 3.8E-1 | 3.7E0 | 5.3E0 | 2.7E1 | 2.2E1 | 1.0E-9 | 5.7E-2 | 5.1E2 | 1.1E2 | 751 | 28 | 296 | 28 | 0.55 |
| Is | ng/ml | 1.4E0 | 2.7E0 | 6.2E0 | 1.9E1 | 2.4E1 | 4.4E1 | 1.0E-9 | 2.9E-2 | 5.5E2 | 2.3E2 | 752 | 28 | 296 | 28 | 0.63 |
| It | ng/ml | 2.0E0 | 9.6E-1 | 2.4E1 | 2.6E1 | 1.4E2 | 1.1E2 | 1.0E-9 | 1.0E-9 | 2.8E3 | 5.9E2 | 752 | 28 | 296 | 28 | 0.41 |
| Iu | ng/ml | 2.2E2 | 9.5E1 | 1.5E3 | 1.1E3 | 4.3E3 | 4.5E3 | 1.0E-9 | 1.0E-9 | 2.9E4 | 2.4E4 | 752 | 28 | 296 | 28 | 0.38 |
| Iv | ng/ml | 1.2E1 | 1.8E1 | 6.5E1 | 2.6E2 | 6.0E2 | 1.2E3 | 1.0E-9 | 1.0E-9 | 1.6E4 | 6.4E3 | 751 | 28 | 296 | 28 | 0.59 |
| Iz | ng/ml | 1.4E2 | 5.7E2 | 6.3E2 | 5.6E2 | 3.9E3 | 5.0E2 | 9.2E-1 | 1.8E1 | 6.2E4 | 1.2E3 | 264 | 14 | 159 | 14 | 0.60 |
| Rc | pg/ml | 6.1E3 | 4.3E3 | 7.3E3 | 7.5E3 | 5.5E3 | 7.4E3 | 1.9E2 | 1.1E3 | 3.0E4 | 2.9E4 | 261 | 14 | 159 | 14 | 0.46 |
| Rb | pg/ml | 8.6E-1 | 1.6E0 | 2.8E0 | 2.0E0 | 5.5E0 | 2.0E0 | 1.0E-9 | 1.0E-9 | 5.6E1 | 6.0E0 | 261 | 14 | 159 | 14 | 0.53 |
| Pz | ng/ml | 4.4E3 | 1.8E3 | 8.3E3 | 4.2E3 | 4.0E4 | 4.2E3 | 1.3E1 | 3.6E1 | 1.0E6 | 1.4E4 | 753 | 29 | 295 | 29 | 0.42 |
| Qa | ng/ml | 3.4E3 | 5.3E3 | 6.3E3 | 8.3E3 | 1.1E4 | 7.8E3 | 1.2E1 | 3.4E2 | 2.2E5 | 2.8E4 | 753 | 29 | 295 | 29 | 0.61 |
| Qb | ng/ml | 8.7E1 | 1.5E2 | 2.1E2 | 2.0E2 | 5.0E2 | 1.7E2 | 7.9E-1 | 1.1E1 | 8.3E3 | 6.0E2 | 753 | 29 | 295 | 29 | 0.63 |
| Qc | ng/ml | 2.1E2 | 3.6E2 | 4.4E2 | 4.6E2 | 7.6E2 | 5.9E2 | 1.0E-9 | 2.7E1 | 1.1E4 | 3.1E3 | 753 | 29 | 295 | 29 | 0.57 |
| Qd | ng/ml | 8.9E3 | 1.1E4 | 1.9E4 | 2.4E4 | 7.8E4 | 3.4E4 | 1.5E2 | 9.8E2 | 2.0E6 | 1.5E5 | 753 | 29 | 295 | 29 | 0.56 |
| Qe | ng/ml | 9.1E2 | 9.5E2 | 1.8E3 | 2.1E3 | 4.0E3 | 2.8E3 | 1.0E-9 | 6.8E1 | 9.7E4 | 1.4E4 | 753 | 29 | 295 | 29 | 0.55 |
| Jd | ng/ml | 9.0E-1 | 3.1E0 | 6.6E0 | 3.8E0 | 4.3E1 | 4.3E0 | 1.0E-9 | 1.0E-9 | 6.5E2 | 1.5E1 | 262 | 14 | 160 | 14 | 0.67 |
| Je | ng/ml | 1.0E-9 | 1.7E0 | 2.1E0 | 2.3E0 | 7.8E0 | 2.8E0 | 1.0E-9 | 1.0E-9 | 8.8E1 | 9.9E0 | 262 | 14 | 160 | 14 | 0.65 |
| Jf | ng/ml | 1.0E-9 | 1.3E-1 | 1.0E0 | 1.5E0 | 2.2E0 | 2.4E0 | 1.0E-9 | 1.0E-9 | 1.2E1 | 8.7E0 | 262 | 14 | 160 | 14 | 0.59 |
| Jg | ng/ml | 5.0E2 | 6.1E2 | 7.7E2 | 1.5E3 | 9.2E2 | 1.8E3 | 1.0E-9 | 1.1E1 | 1.0E4 | 6.8E3 | 756 | 29 | 296 | 29 | 0.58 |
| Jh | ng/ml | 2.8E0 | 7.8E0 | 2.4E1 | 4.5E1 | 1.1E2 | 6.8E1 | 1.0E-9 | 1.0E-9 | 1.6E3 | 2.4E2 | 756 | 29 | 296 | 29 | 0.62 |
| Ji | ng/ml | 5.2E1 | 6.2E1 | 7.7E1 | 1.8E2 | 8.9E1 | 3.4E2 | 1.0E-9 | 8.3E0 | 1.3E3 | 1.8E3 | 756 | 29 | 296 | 29 | 0.61 |
| Sr | pg/mL | 3.9E2 | 2.5E2 | 9.8E2 | 1.2E3 | 1.8E3 | 1.8E3 | 1.0E-9 | 1.0E-9 | 2.1E4 | 4.6E3 | 259 | 12 | 159 | 12 | 0.46 |

Figure 13 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ss | pg/mL | 9.4E4 | 2.0E5 | 1.5E5 | 1.5E5 | 1.9E5 | 8.8E4 | 2.7E3 | 6.5E3 | 1.8E6 | 2.5E5 | 259 | 12 | 159 | 12 | 0.58 |
| St | pg/mL | 2.6E7 | 2.8E7 | 4.8E7 | 5.5E7 | 6.1E7 | 7.0E7 | 1.0E-9 | 3.4E6 | 5.4E8 | 2.6E8 | 257 | 14 | 157 | 14 | 0.50 |
| Ra | pg/ml | 1.0E-9 | 1.0E-9 | 8.4E-1 | 4.5E-1 | 4.1E0 | 9.3E-1 | 1.0E-9 | 1.0E-9 | 6.4E1 | 2.6E0 | 261 | 14 | 159 | 14 | 0.48 |
| Qz | pg/ml | 1.0E1 | 1.5E1 | 6.0E1 | 7.3E1 | 9.9E1 | 8.4E1 | 1.0E-9 | 1.0E-9 | 7.1E2 | 2.0E2 | 261 | 14 | 159 | 14 | 0.58 |
| Qy | pg/ml | 4.4E-1 | 6.8E-1 | 9.8E0 | 5.0E1 | 5.8E1 | 1.4E2 | 1.0E-9 | 1.0E-9 | 6.5E2 | 5.1E2 | 261 | 14 | 159 | 14 | 0.61 |
| Qx | pg/ml | 1.0E-9 | 1.0E-9 | 6.6E0 | 5.1E-1 | 5.1E1 | 1.9E0 | 1.0E-9 | 1.0E-9 | 5.8E2 | 7.1E0 | 261 | 14 | 159 | 14 | 0.47 |
| Qw | pg/ml | 1.0E-9 | 7.8E-1 | 1.9E0 | 7.1E0 | 9.3E0 | 2.3E1 | 1.0E-9 | 1.0E-9 | 1.2E2 | 8.6E1 | 261 | 14 | 159 | 14 | 0.59 |
| Qv | pg/ml | 2.3E4 | 1.0E4 | 3.6E4 | 2.0E4 | 7.8E4 | 2.0E4 | 6.0E1 | 1.0E-9 | 9.4E5 | 5.1E4 | 261 | 14 | 159 | 14 | 0.38 |
| Qu | pg/ml | 7.8E0 | 2.3E1 | 8.6E1 | 8.7E1 | 1.8E2 | 1.3E2 | 1.0E-9 | 1.0E-9 | 9.8E2 | 4.2E2 | 261 | 14 | 159 | 14 | 0.55 |
| Qt | pg/ml | 1.0E1 | 1.2E1 | 5.0E1 | 8.0E1 | 1.3E2 | 1.5E2 | 1.0E-9 | 1.0E-9 | 1.0E3 | 5.1E2 | 261 | 14 | 159 | 14 | 0.57 |
| Qh | ng/ml | 1.6E1 | 3.1E1 | 3.8E1 | 3.6E1 | 6.6E1 | 3.1E1 | 1.0E-9 | 3.6E0 | 6.4E2 | 1.1E2 | 261 | 14 | 159 | 14 | 0.59 |
| Qg | ng/ml | 7.8E0 | 1.2E1 | 1.6E1 | 2.5E1 | 2.6E1 | 3.6E1 | 5.1E-2 | 3.9E0 | 2.2E2 | 1.4E2 | 261 | 14 | 159 | 14 | 0.67 |
| Jj | ng/ml | 6.3E2 | 2.6E2 | 1.8E3 | 7.6E3 | 1.3E4 | 1.5E3 | 1.5E0 | 4.9E0 | 3.4E5 | 7.7E3 | 756 | 29 | 296 | 29 | 0.33 |
| Jk | ng/ml | 3.0E0 | 4.5E0 | 1.9E1 | 4.2E1 | 4.1E1 | 7.8E1 | 1.0E-9 | 1.1E-1 | 2.8E2 | 3.5E2 | 756 | 29 | 296 | 29 | 0.58 |
| Jl | ng/ml | 3.8E-1 | 1.1E0 | 1.8E0 | 2.7E1 | 4.6E0 | 1.0E2 | 7.6E-4 | 1.1E-3 | 4.0E1 | 5.4E2 | 756 | 29 | 296 | 29 | 0.64 |
| Jm | ng/ml | 1.6E1 | 1.9E1 | 5.9E1 | 2.9E1 | 1.4E2 | 3.5E1 | 1.0E-9 | 7.7E-1 | 2.1E3 | 1.3E2 | 756 | 29 | 296 | 29 | 0.49 |
| Jn | pg/ml | 4.0E-1 | 4.0E-1 | 3.2E0 | 1.7E0 | 3.2E1 | 3.0E0 | 1.0E-9 | 1.0E-9 | 6.2E2 | 1.2E1 | 755 | 29 | 296 | 29 | 0.53 |
| Jo | pg/ml | 3.6E3 | 2.3E3 | 5.0E3 | 4.4E3 | 5.3E3 | 7.1E3 | 2.0E1 | 7.5E1 | 1.0E5 | 3.8E4 | 756 | 29 | 296 | 29 | 0.37 |
| Jp | pg/ml | 6.9E4 | 9.0E4 | 7.2E4 | 8.7E4 | 3.8E4 | 4.3E4 | 5.8E2 | 2.8E3 | 3.8E5 | 1.7E5 | 756 | 29 | 296 | 29 | 0.62 |
| Jq | pg/ml | 9.4E1 | 6.5E1 | 1.6E2 | 3.9E2 | 3.5E2 | 9.7E2 | 1.0E0 | 5.4E0 | 8.7E3 | 4.0E3 | 756 | 29 | 296 | 29 | 0.48 |
| Jr | pg/ml | 5.2E0 | 6.7E0 | 4.0E1 | 2.5E1 | 4.4E2 | 4.2E1 | 1.0E-9 | 1.0E-9 | 1.1E4 | 1.9E2 | 756 | 29 | 296 | 29 | 0.60 |
| Js | pg/ml | 1.3E1 | 1.2E1 | 5.5E1 | 2.0E1 | 4.0E2 | 2.3E1 | 1.0E-9 | 1.0E-9 | 1.0E4 | 9.4E1 | 756 | 29 | 296 | 29 | 0.49 |
| Jt | pg/ml | 2.7E3 | 2.0E3 | 3.3E3 | 3.4E3 | 2.8E3 | 5.9E3 | 2.2E1 | 2.6E2 | 5.2E4 | 3.3E4 | 756 | 29 | 296 | 29 | 0.41 |
| Ju | mIU/ml | 9.1E0 | 1.2E1 | 2.0E1 | 1.6E1 | 3.1E1 | 1.9E1 | 4.8E-2 | 1.5E-1 | 2.3E2 | 7.1E1 | 262 | 14 | 160 | 14 | 0.50 |
| Jv | mIU/ml | 1.3E1 | 2.0E1 | 3.3E1 | 3.1E1 | 5.7E1 | 4.2E1 | 1.0E-2 | 2.1E-1 | 4.4E2 | 1.5E2 | 262 | 14 | 160 | 14 | 0.51 |
| Jy | ng/ml | 1.6E-3 | 1.7E-3 | 2.3E-3 | 2.2E-3 | 4.2E-3 | 1.4E-3 | 1.0E-9 | 1.0E-9 | 5.2E-2 | 4.8E-3 | 262 | 14 | 160 | 14 | 0.57 |
| Kc | pg/ml | 2.6E1 | 2.1E1 | 4.5E1 | 5.0E1 | 4.8E1 | 5.5E1 | 1.0E-9 | 1.0E-9 | 2.7E2 | 1.7E2 | 264 | 14 | 159 | 14 | 0.50 |
| Kd | pg/ml | 1.0E-9 | 1.0E-9 | 3.3E2 | 1.0E-9 | 2.4E3 | 0.0E0 | 1.0E-9 | 1.0E-9 | 3.8E4 | 1.0E-9 | 264 | 14 | 159 | 14 | 0.41 |
| Ke | pg/ml | 1.3E4 | 9.7E3 | 1.6E4 | 1.3E4 | 2.2E4 | 9.6E3 | 3.4E2 | 3.2E5 | 3.3E4 | | 264 | 14 | 159 | 14 | 0.45 |
| Kf | pg/mL | 7.4E0 | 7.4E0 | 7.8E0 | 6.7E0 | 7.4E0 | 5.3E0 | 1.0E-9 | 1.0E-9 | 7.8E1 | 1.7E1 | 264 | 14 | 159 | 14 | 0.48 |
| Kg | pg/mL | 1.2E3 | 6.4E2 | 2.0E3 | 8.8E2 | 2.9E3 | 7.2E2 | 7.7E1 | 1.6E2 | 2.7E4 | 2.5E3 | 264 | 14 | 159 | 14 | 0.33 |
| Ki | pg/ml | 5.9E1 | 7.1E1 | 6.8E1 | 6.9E1 | 5.2E1 | 3.0E1 | 1.0E-9 | 1.3E1 | 3.8E2 | 1.1E2 | 263 | 14 | 159 | 14 | 0.57 |
| Kj | pg/ml | 9.8E2 | 8.4E2 | 1.7E3 | 1.0E3 | 1.9E3 | 8.0E2 | 3.0E1 | 1.2E2 | 1.5E4 | 2.8E3 | 264 | 14 | 159 | 14 | 0.42 |
| Kk | pg/ml | 6.8E0 | 8.8E0 | 1.2E1 | 1.3E1 | 1.6E1 | 1.5E1 | 1.0E-9 | 1.0E-9 | 1.6E2 | 5.5E1 | 264 | 14 | 159 | 14 | 0.52 |
| Kl | pg/ml | 2.1E4 | 2.1E4 | 2.8E4 | 2.6E4 | 2.6E4 | 2.2E4 | 2.3E2 | 2.1E2 | 1.6E5 | 5.7E4 | 264 | 14 | 159 | 14 | 0.47 |
| Kn | pg/ml | 3.0E1 | 2.9E1 | 8.1E1 | 3.7E1 | 3.1E2 | 4.4E1 | 1.0E-9 | 1.0E-9 | 4.9E3 | 1.7E2 | 264 | 14 | 159 | 14 | 0.48 |
| Ko | pg/ml | 4.1E2 | 5.2E1 | 5.2E2 | 2.6E2 | 5.2E2 | 4.0E2 | 1.0E-9 | 1.0E-9 | 4.1E3 | 1.4E3 | 264 | 14 | 159 | 14 | 0.31 |
| Kp | pg/ml | 3.4E2 | 3.4E2 | 4.1E2 | 4.0E2 | 8.4E2 | 3.1E2 | 1.3E4 | 9.4E2 | 264 | | 14 | 159 | 14 | 0.53 | |
| Kq | pg/ml | 3.2E2 | 2.8E2 | 1.1E3 | 4.7E2 | 9.9E3 | 5.5E2 | 5.1E0 | 7.0E0 | 1.6E5 | 1.7E3 | 257 | 14 | 154 | 14 | 0.44 |
| Kr | pg/ml | 5.6E-1 | 1.0E-9 | 4.0E0 | 3.7E-1 | 2.6E1 | 9.6E-1 | 1.0E-9 | 1.0E-9 | 4.2E2 | 3.4E0 | 257 | 14 | 154 | 14 | 0.31 |
| Ks | pg/ml | 1.4E4 | 4.2E3 | 2.0E4 | 1.0E4 | 1.9E4 | 1.2E4 | 2.2E2 | 1.1E3 | 1.1E5 | 4.0E4 | 257 | 14 | 154 | 14 | 0.31 |
| Kx | ng/ml | 1.0E-9 | 1.0E-9 | 6.9E-3 | 2.9E-3 | 1.4E-2 | 4.8E-3 | 1.0E-9 | 1.0E-9 | 1.0E-1 | 1.4E-2 | 263 | 13 | 159 | 13 | 0.45 |
| Ky | ng/ml | 9.8E-2 | 5.2E-2 | 3.8E-1 | 2.2E-1 | 8.4E-1 | 3.2E-1 | 1.0E-9 | 1.0E-9 | 6.4E0 | 9.0E-1 | 263 | 14 | 159 | 14 | 0.42 |
| Kz | ng/ml | 1.0E-9 | 1.0E-9 | 3.7E-3 | 3.4E-3 | 5.8E-3 | 6.0E-3 | 1.0E-9 | 1.0E-9 | 3.6E-2 | 1.4E-2 | 263 | 14 | 159 | 14 | 0.46 |
| Ld | pg/ml | 1.0E-9 | 1.0E-9 | 3.7E0 | 1.7E0 | 9.2E0 | 3.2E0 | 1.0E-9 | 1.0E-9 | 8.4E1 | 7.3E0 | 264 | 13 | 158 | 13 | 0.42 |
| Lh | pg/ml | 1.3E4 | 1.4E4 | 2.1E4 | 3.7E4 | 3.3E4 | 7.5E4 | 1.0E-9 | 1.8E2 | 4.8E5 | 4.1E5 | 756 | 29 | 297 | 29 | 0.58 |
| Li | pg/ml | 3.2E3 | 5.8E3 | 1.7E4 | 3.8E4 | 6.6E4 | 1.1E5 | 1.0E-9 | 1.7E2 | 1.3E6 | 5.9E5 | 756 | 29 | 297 | 29 | 0.58 |
| Lj | pg/ml | 2.9E3 | 4.4E3 | 2.4E4 | 2.0E4 | 6.8E4 | 6.4E4 | 1.0E-9 | 8.9E1 | 5.2E5 | 3.5E5 | 756 | 29 | 297 | 29 | 0.51 |
| Rm | ng/ml | 1.9E1 | 1.2E1 | 5.2E1 | 3.2E1 | 8.4E1 | 3.8E1 | 2.2E-1 | 3.0E0 | 6.5E2 | 1.3E2 | 256 | 14 | 158 | 14 | 0.46 |
| Rh | ng/ml | 1.3E2 | 7.4E1 | 4.0E2 | 1.5E2 | 1.4E3 | 1.8E2 | 4.7E0 | 3.6E0 | 1.7E4 | 5.5E2 | 256 | 14 | 158 | 14 | 0.36 |
| Ri | ng/ml | 1.0E-9 | 1.0E-9 | 4.4E0 | 2.6E0 | 1.6E1 | 5.5E0 | 1.0E-9 | 1.0E-9 | 2.2E2 | 2.0E1 | 257 | 14 | 159 | 14 | 0.48 |
| Rg | ng/ml | 1.0E-9 | 1.0E-9 | 5.0E-2 | 2.2E-3 | 3.0E-1 | 4.7E-3 | 1.0E-9 | 1.0E-9 | 3.0E0 | 1.4E-2 | 256 | 14 | 158 | 14 | 0.53 |
| Rj | ng/ml | 1.0E-9 | 1.0E-9 | 2.4E0 | 6.9E-1 | 1.8E1 | 1.7E0 | 1.0E-9 | 1.0E-9 | 2.7E2 | 6.3E0 | 257 | 14 | 159 | 14 | 0.46 |
| Rf | ng/ml | 4.1E-1 | 6.1E-1 | 1.0E0 | 1.7E0 | 1.8E0 | 1.7E0 | 7.8E-3 | 2.2E-2 | 1.5E1 | 3.9E0 | 256 | 14 | 158 | 14 | 0.60 |
| Ql | pg/ml | 4.5E0 | 1.2E1 | 1.3E1 | 1.6E1 | 2.4E1 | 2.2E1 | 1.0E-9 | 1.0E-9 | 1.8E2 | 6.7E1 | 262 | 14 | 160 | 14 | 0.55 |
| Qm | pg/ml | 4.1E0 | 1.0E-9 | 2.2E1 | 1.9E1 | 4.0E1 | 3.3E1 | 1.0E-9 | 1.0E-9 | 3.6E2 | 1.2E2 | 262 | 14 | 160 | 14 | 0.45 |
| Qn | pg/ml | 6.1E-1 | 8.5E-1 | 7.4E0 | 4.8E0 | 2.4E1 | 9.4E0 | 1.0E-9 | 1.0E-9 | 2.4E2 | 3.3E1 | 262 | 14 | 160 | 14 | 0.53 |

Figure 13 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nv | pg/ml | 3.8E3 | 6.6E3 | 1.0E4 | 1.9E4 | 4.5E4 | 3.0E4 | 1.0E-9 | 8.4E1 | 1.1E6 | 1.3E5 | 762 | 29 | 297 | 29 | 0.62 |
| Nw | pg/ml | 8.8E3 | 1.3E4 | 1.3E4 | 2.9E4 | 1.7E4 | 4.5E4 | 8.6E1 | 5.7E2 | 2.1E5 | 2.1E5 | 762 | 29 | 297 | 29 | 0.60 |
| Nx | pg/ml | 2.2E2 | 2.6E2 | 4.1E2 | 5.8E2 | 6.6E2 | 7.5E2 | 1.0E-9 | 1.0E-9 | 7.4E3 | 2.8E3 | 762 | 29 | 297 | 29 | 0.59 |
| Ny | pg/ml | 6.0E0 | 7.6E0 | 6.1E1 | 4.8E1 | 9.2E2 | 1.2E2 | 1.0E-9 | 1.0E-9 | 2.5E4 | 6.2E2 | 762 | 29 | 297 | 29 | 0.54 |
| Oa | pg/ml | 1.8E2 | 2.4E2 | 4.4E2 | 4.0E2 | 7.4E2 | 4.0E2 | 1.0E-9 | 9.8E-1 | 4.8E3 | 1.1E3 | 262 | 14 | 160 | 14 | 0.55 |
| Oe | pg/ml | 4.2E1 | 3.7E1 | 2.7E2 | 2.6E2 | 7.9E2 | 4.4E2 | 1.0E-9 | 1.0E-9 | 1.9E4 | 1.6E3 | 755 | 29 | 296 | 29 | 0.49 |
| Of | pg/ml | 1.6E2 | 8.9E1 | 5.3E3 | 6.7E3 | 2.9E4 | 1.9E4 | 1.0E-9 | 1.0E-9 | 6.2E5 | 7.6E4 | 761 | 29 | 297 | 29 | 0.45 |
| Og | pg/ml | 7.9E-2 | 1.0E-1 | 4.6E-1 | 5.0E-1 | 1.5E0 | 1.2E0 | 1.0E-9 | 1.0E-9 | 2.0E1 | 5.0E0 | 761 | 29 | 297 | 29 | 0.55 |
| Oh | pg/ml | 2.5E0 | 3.3E0 | 2.0E1 | 1.6E1 | 1.5E2 | 4.4E1 | 1.0E-9 | 1.2E-2 | 3.5E3 | 2.2E2 | 761 | 29 | 297 | 29 | 0.58 |
| Oi | pg/ml | 2.4E0 | 3.0E0 | 5.9E0 | 7.0E0 | 9.6E0 | 9.4E0 | 1.0E-9 | 1.0E-9 | 8.6E1 | 2.8E1 | 761 | 29 | 297 | 29 | 0.53 |
| Ok | pg/ml | 3.9E2 | 5.0E2 | 5.3E2 | 3.3E3 | 5.7E2 | 1.3E4 | 1.3E1 | 4.0E1 | 7.8E3 | 7.0E4 | 761 | 29 | 297 | 29 | 0.54 |
| Om | pg/ml | 3.8E2 | 4.4E2 | 8.2E2 | 3.1E3 | 2.6E3 | 7.4E3 | 1.0E-9 | 1.0E-9 | 5.1E4 | 3.6E4 | 761 | 29 | 297 | 29 | 0.60 |
| On | pg/ml | 1.8E2 | 3.0E2 | 2.8E2 | 1.3E3 | 4.2E2 | 3.2E3 | 1.0E-9 | 7.2E0 | 4.5E3 | 1.5E4 | 761 | 29 | 297 | 29 | 0.59 |
| Or | pg/ml | 1.4E1 | 2.2E1 | 3.5E1 | 4.4E1 | 6.7E1 | 8.7E1 | 1.0E-9 | 1.0E-9 | 5.1E2 | 3.4E2 | 265 | 14 | 159 | 14 | 0.53 |
| Ow | pg/ml | 3.3E1 | 4.5E1 | 1.5E2 | 2.6E2 | 5.7E2 | 8.5E2 | 1.0E-9 | 1.0E-9 | 8.1E3 | 3.2E3 | 265 | 14 | 159 | 14 | 0.45 |
| Ou | pg/ml | 5.1E2 | 6.8E2 | 9.5E2 | 1.5E3 | 1.5E3 | 2.2E3 | 1.0E-9 | 1.0E-9 | 9.8E3 | 8.1E3 | 265 | 14 | 159 | 14 | 0.57 |
| Ul | ng/ml | 1.0E-9 | 1.0E-9 | 1.8E0 | 1.7E0 | 8.3E0 | 6.5E0 | 1.0E-9 | 1.0E-9 | 1.0E2 | 2.4E1 | 270 | 14 | 163 | 14 | 0.49 |
| Uo | ng/ml | 1.0E-9 | 1.0E-9 | 9.7E-2 | 3.8E-2 | 2.2E-1 | 1.2E-1 | 1.0E-9 | 1.0E-9 | 1.5E0 | 4.6E-1 | 270 | 14 | 163 | 14 | 0.42 |
| Uk | ng/ml | 1.0E-9 | 1.0E-9 | 8.5E-3 | 5.0E-5 | 2.7E-2 | 1.3E-4 | 1.0E-9 | 1.0E-9 | 3.2E-1 | 4.4E-4 | 270 | 14 | 163 | 14 | 0.32 |
| Um | ng/ml | 1.0E-9 | 1.0E-9 | 4.2E-1 | 1.5E-1 | 9.1E-1 | 2.6E-1 | 1.0E-9 | 1.0E-9 | 6.8E0 | 8.4E-1 | 270 | 14 | 163 | 14 | 0.44 |
| Uf | ng/ml | 6.5E-2 | 5.4E-2 | 1.8E-1 | 1.2E-1 | 6.4E-1 | 1.4E-1 | 1.3E-3 | 1.1E-3 | 8.6E0 | 4.2E-1 | 270 | 14 | 163 | 14 | 0.49 |
| Uh | ng/ml | 2.1E0 | 1.3E0 | 3.4E0 | 1.8E0 | 3.7E0 | 1.7E0 | 1.3E-2 | 6.0E-2 | 2.1E1 | 5.3E0 | 270 | 14 | 163 | 14 | 0.37 |
| Un | ng/ml | 1.9E0 | 2.1E0 | 2.2E0 | 2.5E0 | 1.9E0 | 1.7E0 | 1.3E-1 | 5.4E-1 | 2.5E1 | 5.6E0 | 270 | 14 | 163 | 14 | 0.55 |
| Ug | ng/ml | 1.5E1 | 8.9E0 | 2.9E1 | 1.8E1 | 3.2E1 | 2.0E1 | 6.9E-1 | 1.3E0 | 2.1E2 | 6.2E1 | 270 | 14 | 163 | 14 | 0.38 |
| Ur | ng/ml | 1.5E-1 | 9.7E-2 | 8.9E-1 | 2.8E-1 | 5.8E0 | 4.9E-1 | 1.0E-9 | 1.0E-9 | 9.3E1 | 1.8E0 | 269 | 14 | 162 | 14 | 0.44 |
| Up | ng/ml | 1.0E-9 | 1.0E-9 | 1.4E-2 | 3.9E-3 | 1.5E-1 | 9.0E-3 | 1.0E-9 | 1.0E-9 | 2.4E0 | 3.3E-2 | 269 | 14 | 162 | 14 | 0.56 |
| Us | ng/ml | 2.9E-3 | 6.3E-3 | 2.6E-2 | 1.3E-2 | 1.1E-1 | 1.8E-2 | 1.0E-9 | 1.0E-9 | 1.7E0 | 6.2E-2 | 269 | 14 | 162 | 14 | 0.56 |
| Uv | ng/ml | 3.1E-3 | 2.6E-3 | 1.4E-2 | 3.8E-3 | 4.7E-2 | 3.6E-3 | 1.0E-9 | 1.0E-9 | 4.3E-1 | 1.3E-2 | 269 | 14 | 162 | 14 | 0.49 |
| Ut | ng/ml | 6.6E-1 | 4.9E-1 | 2.9E0 | 1.9E0 | 9.6E0 | 2.7E0 | 1.0E-9 | 1.0E-9 | 7.8E1 | 7.8E0 | 269 | 14 | 162 | 14 | 0.48 |
| Uu | ng/ml | 7.1E0 | 8.8E0 | 7.9E0 | 8.9E0 | 5.6E0 | 5.9E0 | 5.5E-1 | 4.5E-1 | 4.0E1 | 1.9E1 | 269 | 14 | 162 | 14 | 0.55 |
| Vp | ng/ml | 1.0E-9 | 1.0E-9 | 5.6E-1 | 9.3E-1 | 4.6E0 | 3.1E-1 | 1.0E-9 | 1.0E-9 | 5.0E1 | 1.2E0 | 270 | 14 | 163 | 14 | 0.54 |
| Vt | ng/ml | 6.8E0 | 3.9E0 | 9.9E0 | 6.5E0 | 1.3E1 | 6.0E0 | 4.3E-1 | 8.8E-1 | 1.6E2 | 1.9E1 | 270 | 14 | 163 | 14 | 0.37 |
| Vu | ng/ml | 1.0E-9 | 1.0E-9 | 2.1E0 | 2.2E0 | 5.4E0 | 3.7E0 | 1.0E-9 | 1.0E-9 | 5.1E1 | 1.4E1 | 264 | 14 | 162 | 14 | 0.54 |
| Vq | ng/ml | 2.7E2 | 1.5E2 | 4.3E3 | 9.3E2 | 4.8E4 | 2.1E3 | 2.0E-1 | 6.5E0 | 6.8E5 | 7.1E3 | 201 | 11 | 131 | 11 | 0.48 |
| Vo | ng/ml | 2.6E1 | 2.5E1 | 2.5E1 | 2.3E1 | 4.7E0 | 6.9E0 | 6.7E0 | 2.4E0 | 3.5E1 | 2.8E1 | 270 | 14 | 163 | 14 | 0.43 |
| Vs | ng/ml | 1.0E-9 | 1.3E0 | 8.3E0 | 4.6E0 | 3.7E1 | 5.4E0 | 1.0E-9 | 1.0E-9 | 4.5E2 | 1.5E1 | 260 | 14 | 159 | 14 | 0.57 |
| Vv | ng/ml | 2.9E0 | 4.0E0 | 5.8E0 | 5.2E0 | 9.7E0 | 6.2E0 | 1.0E-9 | 1.0E-9 | 8.4E1 | 2.1E1 | 268 | 14 | 162 | 14 | 0.49 |
| Oy | pg/ml | 4.9E-1 | 4.4E-1 | 5.9E0 | 1.3E1 | 3.1E1 | 5.1E1 | 1.0E-9 | 1.0E-9 | 4.0E2 | 2.7E2 | 760 | 29 | 296 | 29 | 0.49 |
| Oz | pg/ml | 1.4E-3 | 1.0E-9 | 3.2E-1 | 2.1E-1 | 1.4E0 | 2.5E-1 | 1.0E-9 | 1.0E-9 | 2.9E1 | 6.9E-1 | 760 | 29 | 296 | 29 | 0.51 |
| Pa | pg/ml | 3.8E-1 | 4.1E-1 | 1.7E0 | 1.1E1 | 6.5E0 | 5.4E1 | 1.0E-9 | 1.0E-9 | 1.0E2 | 2.9E2 | 760 | 29 | 296 | 29 | 0.51 |
| Pb | pg/ml | 1.0E-9 | 1.0E-9 | 9.0E-1 | 6.3E0 | 1.8E1 | 3.3E1 | 1.0E-9 | 1.0E-9 | 4.9E2 | 1.8E2 | 760 | 29 | 296 | 29 | 0.55 |
| Pc | pg/ml | 4.2E-2 | 2.3E-1 | 3.6E-1 | 9.5E-1 | 9.3E-1 | 2.3E0 | 1.0E-9 | 1.0E-9 | 1.6E1 | 1.1E1 | 760 | 29 | 296 | 29 | 0.57 |
| Pd | pg/ml | 1.9E0 | 1.5E0 | 5.4E0 | 2.8E0 | 3.2E1 | 4.1E0 | 1.0E-9 | 1.0E-9 | 8.4E2 | 1.8E1 | 760 | 29 | 296 | 29 | 0.46 |
| Pe | pg/ml | 2.1E1 | 2.3E1 | 1.2E2 | 5.6E2 | 4.8E2 | 2.6E3 | 1.0E-9 | 1.0E-9 | 6.7E3 | 1.4E4 | 760 | 29 | 296 | 29 | 0.51 |
| Pf | pg/ml | 1.6E0 | 2.0E0 | 1.2E1 | 1.2E1 | 6.3E1 | 4.2E1 | 1.0E-9 | 1.0E-9 | 1.5E3 | 2.3E2 | 760 | 29 | 296 | 29 | 0.51 |
| Pg | pg/ml | 3.3E0 | 6.2E0 | 4.8E1 | 7.3E1 | 3.7E2 | 3.5E2 | 1.0E-9 | 1.0E-9 | 7.7E3 | 1.9E3 | 760 | 29 | 296 | 29 | 0.55 |
| Ph | ng/ml | 1.8E-1 | 1.0E-1 | 3.5E-1 | 3.3E-1 | 5.7E-1 | 4.6E-1 | 1.0E-9 | 1.0E-9 | 5.4E0 | 1.6E0 | 265 | 14 | 159 | 14 | 0.45 |
| Pi | ng/ml | 2.0E-1 | 1.4E-1 | 5.8E-1 | 1.9E-1 | 5.0E0 | 1.8E-1 | 1.0E-9 | 1.0E-9 | 8.2E1 | 5.3E-1 | 265 | 14 | 159 | 14 | 0.41 |
| Pj | ng/mL | 5.7E0 | 2.6E0 | 6.4E0 | 5.4E0 | 4.5E0 | 6.7E0 | 3.8E-2 | 3.8E-1 | 3.1E1 | 2.5E1 | 265 | 14 | 159 | 14 | 0.34 |
| Pk | ng/ml | 8.8E-3 | 2.3E-3 | 1.8E-2 | 8.7E-3 | 9.4E-2 | 1.2E-2 | 1.0E-9 | 1.0E-9 | 1.5E0 | 3.1E-2 | 265 | 14 | 159 | 14 | 0.38 |
| aA | mg/dL | 8.0E-1 | 1.5E0 | 9.0E-1 | 1.9E0 | 4.3E-1 | 1.1E0 | 2.0E-1 | 4.9E-1 | 4.1E0 | 5.4E0 | 2356 | 48 | 452 | 48 | 0.82 |
| aC | mg/mL | 2.9E0 | 2.4E0 | 3.2E0 | 2.7E0 | 1.4E0 | 1.4E0 | 7.7E-1 | 1.2E0 | 8.9E0 | 6.7E0 | 466 | 18 | 180 | 18 | 0.39 |
| aD | ug/mL | 3.2E0 | 2.9E0 | 4.5E0 | 4.5E0 | 4.0E0 | 3.9E0 | 4.3E-1 | 1.1E0 | 3.5E1 | 1.7E1 | 466 | 18 | 180 | 18 | 0.49 |
| aE | mg/mL | 5.6E-1 | 5.1E-1 | 5.7E-1 | 5.7E-1 | 1.5E-1 | 1.6E-1 | 1.8E-1 | 3.8E-1 | 1.1E0 | 9.6E-1 | 466 | 18 | 180 | 18 | 0.45 |
| aF | ng/mL | 2.2E0 | 2.1E0 | 3.8E0 | 4.5E0 | 5.4E0 | 5.1E0 | 4.3E-3 | 3.4E-1 | 5.0E1 | 1.6E1 | 466 | 18 | 180 | 18 | 0.51 |
| aG | mg/mL | 1.3E-1 | 1.2E-1 | 1.5E-1 | 1.7E-1 | 8.7E-2 | 1.1E-1 | 1.7E-2 | 5.4E-2 | 5.4E-1 | 4.3E-1 | 466 | 18 | 180 | 18 | 0.51 |
| aH | ug/mL | 7.5E1 | 7.0E1 | 8.0E1 | 9.1E1 | 4.3E1 | 5.2E1 | 4.6E0 | 3.4E1 | 2.9E2 | 2.1E2 | 466 | 18 | 180 | 18 | 0.54 |

Figure 13 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aI | ug/mL | 1.9E2 | 1.9E2 | 1.9E2 | 1.9E2 | 6.0E1 | 5.3E1 | 2.8E1 | 9.3E1 | 3.7E2 | 3.0E2 | 466 | 18 | 180 | 18 | 0.50 |
| aJ | ug/mL | 2.4E0 | 4.9E0 | 3.0E0 | 6.0E0 | 2.0E0 | 4.3E0 | 7.3E-1 | 7.6E-1 | 1.7E1 | 1.6E1 | 466 | 18 | 180 | 18 | 0.74 |
| aK | ng/mL | 1.5E0 | 1.5E0 | 2.4E0 | 2.5E0 | 2.6E0 | 2.8E0 | 2.9E-4 | 1.0E-1 | 1.8E1 | 1.1E1 | 466 | 18 | 180 | 18 | 0.52 |
| aL | mg/mL | 8.0E-1 | 7.8E-1 | 8.1E-1 | 8.0E-1 | 2.7E-1 | 2.2E-1 | 1.9E-1 | 4.9E-1 | 1.7E0 | 1.3E0 | 466 | 18 | 180 | 18 | 0.48 |
| aM | U/mL | 2.2E1 | 2.4E1 | 5.1E1 | 3.1E1 | 1.1E2 | 2.4E1 | 4.2E-2 | 5.2E0 | 1.6E3 | 9.5E1 | 466 | 18 | 180 | 18 | 0.51 |
| aN | U/mL | 1.3E1 | 1.7E1 | 2.0E1 | 2.5E1 | 2.6E1 | 2.7E1 | 2.5E-3 | 4.5E0 | 3.3E2 | 9.9E1 | 466 | 18 | 180 | 18 | 0.58 |
| aO | pg/mL | 2.6E1 | 7.8E1 | 2.8E2 | 6.3E2 | 7.5E2 | 1.3E3 | 6.0E-2 | 6.0E-2 | 6.6E3 | 3.6E3 | 466 | 18 | 180 | 18 | 0.60 |
| aP | ng/mL | 1.6E0 | 2.9E0 | 2.0E0 | 3.4E0 | 1.8E0 | 1.9E0 | 4.5E-1 | 9.6E-1 | 2.8E1 | 6.7E0 | 466 | 18 | 180 | 18 | 0.75 |
| aQ | ng/mL | 2.9E-1 | 3.0E-1 | 4.4E-1 | 5.2E-1 | 4.6E-1 | 4.9E-1 | 2.0E-1 | 6.9E-2 | 4.0E0 | 1.8E0 | 466 | 18 | 180 | 18 | 0.55 |
| aR | ng/mL | 1.8E0 | 1.7E0 | 2.8E0 | 3.1E0 | 3.3E0 | 4.1E0 | 1.8E-1 | 2.5E-1 | 3.4E1 | 1.7E1 | 466 | 18 | 180 | 18 | 0.48 |
| aS | ng/mL | 2.6E-1 | 3.1E-1 | 6.4E-1 | 8.0E-1 | 1.8E0 | 2.0E0 | 4.2E-3 | 4.2E-3 | 3.3E1 | 8.7E0 | 466 | 18 | 180 | 18 | 0.53 |
| aU | pg/mL | 7.5E1 | 8.3E1 | 1.3E2 | 1.3E2 | 1.5E2 | 1.5E2 | 7.4E-2 | 7.4E-2 | 1.3E3 | 6.0E2 | 466 | 18 | 180 | 18 | 0.51 |
| aV | ng/mL | 6.1E-1 | 7.4E-1 | 1.1E0 | 7.8E-1 | 2.0E0 | 5.6E-1 | 7.6E-4 | 5.0E-2 | 3.3E1 | 2.0E0 | 466 | 18 | 180 | 18 | 0.51 |
| aW | pg/mL | 1.8E1 | 2.1E1 | 1.9E1 | 2.7E1 | 1.9E1 | 3.1E1 | 7.2E-2 | 7.2E-2 | 2.4E2 | 1.5E2 | 466 | 18 | 180 | 18 | 0.59 |
| aX | ng/mL | 9.8E0 | 1.2E1 | 1.5E1 | 4.4E1 | 1.9E1 | 7.8E1 | 3.0E-1 | 2.7E0 | 2.2E2 | 2.9E2 | 466 | 18 | 180 | 18 | 0.59 |
| aY | pg/mL | 6.0E1 | 5.2E1 | 7.7E1 | 7.0E1 | 8.6E1 | 4.5E1 | 4.1E-1 | 2.5E1 | 1.2E3 | 2.0E2 | 466 | 18 | 180 | 18 | 0.51 |
| aZ | pg/mL | 2.3E2 | 1.4E2 | 4.9E2 | 2.0E3 | 9.2E2 | 7.9E3 | 1.7E0 | 1.7E0 | 1.2E4 | 3.4E4 | 466 | 18 | 180 | 18 | 0.39 |
| bA | ng/mL | 8.4E0 | 4.7E1 | 3.5E1 | 1.8E2 | 1.0E2 | 3.3E2 | 3.0E-2 | 3.0E-2 | 9.4E2 | 1.3E3 | 466 | 18 | 180 | 18 | 0.70 |
| bB | ng/mL | 3.0E2 | 3.4E2 | 3.1E2 | 3.6E2 | 1.6E2 | 1.9E2 | 2.1E0 | 1.1E2 | 8.2E2 | 7.6E2 | 466 | 18 | 180 | 18 | 0.56 |
| bC | ng/mL | 3.5E2 | 5.8E2 | 6.2E2 | 9.1E2 | 8.2E2 | 1.0E3 | 2.7E1 | 9.8E0 | 4.7E3 | 4.0E3 | 466 | 18 | 180 | 18 | 0.57 |
| bE | mg/mL | 5.6E0 | 6.4E0 | 5.8E0 | 6.6E0 | 2.1E0 | 2.5E0 | 9.8E-1 | 2.9E0 | 1.3E1 | 1.2E1 | 466 | 18 | 180 | 18 | 0.58 |
| bF | pg/mL | 2.1E1 | 2.4E1 | 1.6E2 | 5.0E1 | 9.3E2 | 6.8E1 | 5.0E-2 | 2.1E0 | 1.1E4 | 3.0E2 | 466 | 18 | 180 | 18 | 0.54 |
| bG | ng/mL | 1.6E0 | 1.7E0 | 2.7E0 | 1.5E0 | 3.2E0 | 9.3E-1 | 2.2E-1 | 3.5E-1 | 2.3E1 | 3.3E0 | 466 | 18 | 180 | 18 | 0.44 |
| bH | pg/mL | 5.7E-1 | 5.7E-1 | 5.0E0 | 5.0E0 | 1.5E1 | 7.5E0 | 5.7E-1 | 5.7E-1 | 2.8E2 | 2.2E1 | 466 | 18 | 180 | 18 | 0.51 |
| bI | ng/mL | 4.0E-3 | 4.0E-3 | 6.5E-2 | 6.4E-2 | 1.6E-1 | 1.9E-1 | 4.0E-3 | 4.0E-3 | 1.3E0 | 7.7E-1 | 466 | 18 | 180 | 18 | 0.47 |
| bJ | mg/mL | 2.4E0 | 1.9E0 | 2.7E0 | 2.7E0 | 2.1E0 | 2.3E0 | 2.5E-4 | 2.5E-4 | 1.3E1 | 8.3E0 | 466 | 18 | 180 | 18 | 0.47 |
| bL | pg/mL | 3.7E0 | 5.3E0 | 8.4E0 | 6.4E0 | 1.1E1 | 7.1E0 | 4.6E-2 | 4.6E-2 | 8.0E1 | 2.5E1 | 466 | 18 | 180 | 18 | 0.46 |
| bM | mg/mL | 1.8E0 | 1.6E0 | 2.1E0 | 1.9E0 | 1.4E0 | 1.1E0 | 9.2E-3 | 5.0E-1 | 8.8E0 | 5.1E0 | 466 | 18 | 180 | 18 | 0.48 |
| bN | ng/mL | 4.6E1 | 2.5E1 | 1.3E2 | 9.5E1 | 2.8E2 | 1.9E2 | 1.4E-1 | 1.4E-1 | 1.9E3 | 7.7E2 | 466 | 18 | 180 | 18 | 0.38 |
| bO | ng/mL | 4.0E-2 | 1.8E0 | 1.1E1 | 9.5E0 | 2.5E1 | 2.3E1 | 4.0E-2 | 4.0E-2 | 2.0E2 | 1.0E2 | 466 | 18 | 180 | 18 | 0.54 |
| bP | mg/mL | 5.4E-1 | 6.9E-1 | 7.7E-1 | 8.8E-1 | 6.9E-1 | 6.2E-1 | 4.9E-2 | 1.9E-1 | 4.8E0 | 2.2E0 | 466 | 18 | 180 | 18 | 0.57 |
| bQ | pg/mL | 1.6E1 | 1.5E1 | 6.2E1 | 3.4E1 | 6.3E2 | 5.2E1 | 1.5E-1 | 1.5E-1 | 1.3E4 | 2.2E2 | 466 | 18 | 180 | 18 | 0.50 |
| bR | ng/mL | 1.2E-2 | 1.2E-2 | 1.3E-1 | 1.4E-1 | 4.5E-1 | 2.8E-1 | 1.2E-2 | 1.2E-2 | 8.7E0 | 1.2E0 | 466 | 18 | 180 | 18 | 0.50 |
| bS | pg/mL | 9.4E-1 | 9.4E-1 | 7.1E0 | 3.9E0 | 2.8E1 | 1.2E1 | 9.4E-1 | 9.4E-1 | 3.9E2 | 5.4E1 | 466 | 18 | 180 | 18 | 0.46 |
| bU | ng/mL | 1.2E-1 | 1.4E-1 | 2.0E-1 | 2.6E-1 | 3.7E-1 | 4.0E-1 | 1.3E-2 | 1.3E-2 | 6.6E0 | 1.7E0 | 466 | 18 | 180 | 18 | 0.52 |
| bV | pg/mL | 4.6E2 | 6.3E2 | 5.5E2 | 1.6E3 | 5.8E2 | 3.8E3 | 1.5E2 | 1.7E2 | 1.2E4 | 1.7E4 | 466 | 18 | 180 | 18 | 0.67 |
| bW | pg/mL | 3.4E2 | 4.1E2 | 6.4E2 | 6.4E2 | 1.7E3 | 9.6E2 | 8.4E1 | 9.2E1 | 2.5E4 | 4.4E3 | 466 | 18 | 180 | 18 | 0.53 |
| bX | ng/mL | 6.9E-4 | 2.5E-5 | 2.7E-3 | 1.6E-3 | 3.4E-3 | 3.4E-3 | 2.5E-5 | 2.5E-5 | 2.0E-2 | 1.1E-2 | 466 | 18 | 180 | 18 | 0.38 |
| bZ | pg/mL | 2.3E2 | 3.8E2 | 8.5E2 | 1.2E3 | 4.0E3 | 1.9E3 | 1.5E-1 | 1.5E-1 | 5.8E4 | 8.2E3 | 466 | 18 | 180 | 18 | 0.63 |
| cA | pg/mL | 6.0E-1 | 6.0E-1 | 2.8E0 | 2.3E0 | 1.8E1 | 4.0E1 | 6.0E-1 | 6.0E-1 | 3.7E2 | 1.3E1 | 466 | 18 | 180 | 18 | 0.52 |
| cB | ng/mL | 5.7E-2 | 5.8E-2 | 9.0E-2 | 1.2E-1 | 1.0E-1 | 1.7E-1 | 1.7E-3 | 1.7E-3 | 5.7E-1 | 5.5E-1 | 466 | 18 | 180 | 18 | 0.51 |
| cC | pg/mL | 4.6E1 | 4.4E1 | 4.8E1 | 4.5E1 | 4.0E1 | 3.4E1 | 1.0E0 | 1.0E0 | 4.5E2 | 1.4E2 | 466 | 18 | 180 | 18 | 0.47 |
| cD | pg/mL | 5.6E0 | 3.7E0 | 1.3E1 | 9.8E0 | 4.9E1 | 1.8E1 | 3.3E-1 | 3.3E-1 | 7.2E2 | 6.9E1 | 466 | 18 | 180 | 18 | 0.40 |
| cE | pg/mL | 3.7E1 | 5.3E1 | 1.7E2 | 7.7E1 | 4.8E2 | 9.0E1 | 1.2E-1 | 1.2E-1 | 3.8E3 | 3.1E2 | 466 | 18 | 180 | 18 | 0.49 |
| cF | pg/mL | 1.3E1 | 6.6E0 | 2.0E1 | 2.4E1 | 3.0E1 | 5.0E1 | 5.3E-1 | 5.3E-1 | 2.7E2 | 2.2E2 | 466 | 18 | 180 | 18 | 0.47 |
| cG | pg/mL | 4.5E1 | 7.0E1 | 1.1E2 | 9.7E1 | 5.1E2 | 1.3E2 | 6.4E0 | 1.1E1 | 1.0E4 | 5.5E2 | 466 | 18 | 180 | 18 | 0.54 |
| cH | uIU/mL | 2.8E0 | 2.2E0 | 5.8E0 | 5.5E0 | 1.1E1 | 6.8E0 | 8.6E-3 | 2.5E-1 | 1.6E2 | 2.0E1 | 466 | 18 | 180 | 18 | 0.45 |
| cI | ng/mL | 5.5E0 | 1.0E1 | 1.1E1 | 3.1E1 | 1.5E1 | 4.7E1 | 1.0E-3 | 7.1E-2 | 1.2E2 | 1.9E2 | 466 | 18 | 180 | 18 | 0.65 |
| cJ | ug/mL | 5.6E1 | 8.9E1 | 1.1E2 | 1.5E2 | 1.4E2 | 1.6E2 | 4.0E0 | 6.5E0 | 9.6E2 | 6.2E2 | 466 | 18 | 180 | 18 | 0.61 |
| cK | ng/mL | 3.8E-3 | 3.8E-3 | 5.1E-2 | 2.0E-2 | 1.8E-1 | 6.9E-2 | 3.8E-3 | 3.8E-3 | 1.7E0 | 3.0E-1 | 466 | 18 | 180 | 18 | 0.45 |
| cL | pg/mL | 2.0E2 | 2.1E2 | 3.7E2 | 2.8E2 | 1.3E3 | 2.7E2 | 1.6E1 | 4.8E1 | 2.4E4 | 1.2E3 | 466 | 18 | 180 | 18 | 0.51 |
| cM | pg/mL | 2.6E2 | 2.2E2 | 2.9E2 | 2.7E2 | 2.0E2 | 1.6E2 | 8.7E0 | 4.0E1 | 1.6E3 | 5.3E2 | 466 | 18 | 180 | 18 | 0.47 |
| cN | pg/mL | 1.2E2 | 1.5E2 | 1.3E2 | 1.5E2 | 6.5E1 | 5.8E1 | 3.8E1 | 4.6E1 | 1.1E3 | 2.8E2 | 466 | 18 | 180 | 18 | 0.67 |
| cO | pg/mL | 2.3E2 | 2.0E2 | 3.2E2 | 2.5E2 | 9.0E2 | 1.9E2 | 5.4E1 | 6.1E1 | 1.9E4 | 8.8E2 | 466 | 18 | 180 | 18 | 0.42 |
| cP | ng/mL | 2.5E3 | 2.8E3 | 2.6E3 | 2.9E3 | 9.1E2 | 1.1E3 | 6.2E2 | 1.7E3 | 5.7E3 | 5.1E3 | 466 | 18 | 180 | 18 | 0.58 |
| cQ | ng/mL | 5.3E-2 | 8.3E-2 | 1.5E-1 | 1.5E-1 | 3.0E-1 | 1.9E-1 | 2.0E-3 | 2.0E-3 | 2.2E0 | 7.3E-1 | 466 | 18 | 180 | 18 | 0.54 |
| cR | ng/mL | 3.0E2 | 3.3E2 | 5.2E2 | 8.6E2 | 8.2E2 | 1.8E3 | 2.0E1 | 9.5E1 | 8.9E3 | 7.7E3 | 466 | 18 | 180 | 18 | 0.55 |

Figure 13 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cS | ng/mL | 2.5E2 | 4.8E2 | 4.0E2 | 1.9E3 | 4.0E2 | 5.2E3 | 4.1E1 | 8.1E1 | 2.7E3 | 2.2E4 | 466 | 18 | 180 | 18 | 0.62 |
| cT | ng/mL | 3.3E1 | 6.3E1 | 8.4E1 | 2.7E2 | 1.9E2 | 4.6E2 | 3.7E0 | 8.0E0 | 2.1E3 | 1.9E3 | 466 | 18 | 180 | 18 | 0.65 |
| cU | ng/mL | 5.3E1 | 6.5E1 | 7.6E1 | 1.0E2 | 1.0E2 | 1.2E2 | 5.4E0 | 1.6E1 | 1.6E3 | 5.1E2 | 466 | 18 | 180 | 18 | 0.61 |
| cV | ng/mL | 1.8E-1 | 2.1E-1 | 4.0E-1 | 5.2E-1 | 2.2E0 | 1.4E0 | 2.5E-2 | 4.1E-2 | 4.7E1 | 6.0E0 | 466 | 18 | 180 | 18 | 0.53 |
| cW | mIU/mL | 5.3E-2 | 6.0E-2 | 1.5E-1 | 6.3E-2 | 7.0E-1 | 4.3E-2 | 3.7E-4 | 1.0E-2 | 9.7E0 | 1.6E-1 | 466 | 18 | 180 | 18 | 0.47 |
| cX | ng/mL | 1.1E-1 | 6.9E-2 | 1.2E0 | 1.6E0 | 3.8E0 | 5.1E0 | 2.3E-4 | 2.3E-4 | 2.8E1 | 2.2E1 | 466 | 18 | 180 | 18 | 0.52 |
| cY | ng/mL | 8.6E0 | 7.9E0 | 1.3E1 | 1.2E1 | 1.3E1 | 1.3E1 | 1.5E-1 | 3.1E-1 | 8.3E1 | 5.2E1 | 466 | 18 | 180 | 18 | 0.49 |
| cZ | ug/mL | 1.5E1 | 1.6E1 | 1.6E1 | 1.8E1 | 7.4E0 | 7.6E0 | 2.3E0 | 1.1E1 | 5.7E1 | 4.3E1 | 466 | 18 | 180 | 18 | 0.61 |
| dA | pg/mL | 3.2E2 | 3.8E2 | 3.7E2 | 4.5E2 | 3.1E2 | 1.9E2 | 9.0E1 | 2.1E2 | 5.8E3 | 7.7E2 | 466 | 18 | 180 | 18 | 0.63 |
| dB | ug/mL | 1.7E1 | 2.2E1 | 1.8E1 | 1.8E1 | 1.6E1 | 1.1E1 | 9.4E-1 | 2.6E0 | 2.5E2 | 4.0E1 | 466 | 18 | 180 | 18 | 0.57 |
| dC | nmol/L | 3.5E1 | 3.2E1 | 3.8E1 | 3.9E1 | 1.8E1 | 2.1E1 | 7.6E0 | 1.5E1 | 1.4E2 | 8.7E1 | 466 | 18 | 180 | 18 | 0.47 |
| dD | ug/mL | 3.6E1 | 3.3E1 | 3.7E1 | 3.6E1 | 1.1E1 | 1.1E1 | 1.3E1 | 2.3E1 | 7.6E1 | 6.4E1 | 466 | 18 | 180 | 18 | 0.45 |
| dE | ng/mL | 4.8E-1 | 4.3E-1 | 6.1E-1 | 5.8E-1 | 7.0E-1 | 8.3E-1 | 8.4E-3 | 8.4E-3 | 7.2E0 | 3.3E0 | 466 | 18 | 180 | 18 | 0.45 |
| dF | ng/mL | 2.3E2 | 3.0E2 | 2.8E2 | 3.1E2 | 1.9E2 | 1.4E2 | 5.6E1 | 8.6E1 | 1.3E3 | 4.9E2 | 466 | 18 | 180 | 18 | 0.61 |
| dG | ng/mL | 1.1E1 | 1.7E1 | 1.5E1 | 1.9E1 | 1.4E1 | 9.1E0 | 2.2E0 | 3.3E0 | 1.8E2 | 3.3E1 | 466 | 18 | 180 | 18 | 0.67 |
| dH | pg/mL | 7.5E0 | 1.0E1 | 1.3E1 | 1.2E1 | 3.9E1 | 9.3E0 | 4.0E-2 | 4.0E-2 | 6.7E2 | 3.6E1 | 466 | 18 | 180 | 18 | 0.58 |
| dI | pg/mL | 4.6E-1 | 4.6E-1 | 2.3E0 | 3.9E0 | 1.6E1 | 9.4E0 | 4.6E-1 | 4.6E-1 | 3.3E2 | 4.1E1 | 466 | 18 | 180 | 18 | 0.60 |
| dJ | ng/mL | 1.9E0 | 2.5E0 | 2.2E0 | 2.3E0 | 1.1E0 | 1.1E0 | 3.2E-2 | 4.9E-1 | 6.9E0 | 4.4E0 | 466 | 18 | 180 | 18 | 0.56 |
| dK | uIU/mL | 1.9E0 | 2.1E0 | 3.1E0 | 2.7E0 | 6.5E0 | 3.6E0 | 2.8E-4 | 4.0E-2 | 7.9E1 | 1.6E1 | 466 | 18 | 180 | 18 | 0.50 |
| dL | ng/mL | 8.8E2 | 9.9E2 | 1.0E3 | 1.1E3 | 5.9E2 | 3.4E2 | 2.6E2 | 4.9E2 | 4.8E3 | 1.6E3 | 466 | 18 | 180 | 18 | 0.58 |
| dM | pg/mL | 9.5E2 | 1.4E3 | 1.2E3 | 2.1E3 | 1.4E3 | 1.6E3 | 3.4E2 | 4.7E2 | 1.6E4 | 7.2E3 | 466 | 18 | 180 | 18 | 0.73 |
| dN | ug/mL | 9.4E1 | 1.0E2 | 1.0E2 | 1.2E2 | 4.1E1 | 4.1E1 | 1.6E1 | 6.7E1 | 3.3E2 | 2.2E2 | 466 | 18 | 180 | 18 | 0.62 |
| dR | pg/ml | 1.6E3 | 1.6E3 | 2.4E3 | 2.2E3 | 2.4E3 | 1.8E3 | 1.4E2 | 2.9E2 | 1.5E4 | 8.2E3 | 312 | 17 | 171 | 17 | 0.54 |
| eF | ng/ml | 4.1E0 | 6.3E0 | 5.0E0 | 6.3E0 | 4.2E0 | 3.1E0 | 1.2E0 | 1.6E0 | 4.6E1 | 1.2E1 | 324 | 18 | 172 | 18 | 0.67 |
| eC | pg/ml | 3.0E2 | 3.0E2 | 3.8E2 | 3.2E2 | 2.9E2 | 1.6E2 | 9.9E0 | 5.1E1 | 2.0E3 | 6.1E2 | 246 | 13 | 160 | 13 | 0.47 |
| eD | pg/ml | 2.1E2 | 2.1E2 | 5.0E2 | 2.1E2 | 1.1E3 | 1.6E2 | 5.2E-1 | 2.8E1 | 8.3E3 | 6.3E2 | 196 | 12 | 131 | 12 | 0.43 |
| eM | ng/ml | 3.4E0 | 1.2E1 | 4.7E0 | 1.3E1 | 4.7E0 | 1.0E1 | 6.9E-1 | 2.5E0 | 2.7E1 | 3.2E1 | 176 | 7 | 70 | 7 | 0.81 |
| fP | ng/ml | 2.6E2 | 3.6E2 | 2.9E2 | 4.3E2 | 1.7E2 | 4.0E2 | 8.4E0 | 2.7E1 | 1.0E3 | 1.6E3 | 298 | 16 | 163 | 16 | 0.58 |
| fR | ng/ml | 1.3E5 | 2.9E5 | 1.8E5 | 3.3E5 | 1.5E5 | 2.1E5 | 2.9E4 | 6.1E4 | 8.3E5 | 7.2E5 | 320 | 11 | 97 | 11 | 0.73 |
| gC | ng/ml | 2.3E2 | 2.8E2 | 2.6E2 | 2.9E2 | 1.3E2 | 1.3E2 | 8.3E1 | 1.7E2 | 1.1E3 | 5.9E2 | 135 | 8 | 79 | 8 | 0.61 |
| gL | pg/ml | 6.4E4 | 7.4E4 | 7.0E4 | 8.7E4 | 2.9E4 | 4.3E4 | 1.4E4 | 3.1E4 | 2.0E5 | 1.6E5 | 312 | 17 | 171 | 17 | 0.62 |
| gP | U/ml | 2.7E2 | 2.7E2 | 2.7E2 | 3.1E2 | 9.4E1 | 1.6E2 | 1.2E1 | 7.1E1 | 8.0E2 | 8.5E2 | 320 | 18 | 172 | 18 | 0.56 |
| gW | ng/ml | 6.1E2 | 8.5E2 | 1.3E3 | 1.2E3 | 1.7E3 | 1.3E3 | 3.1E-1 | 1.1E2 | 9.5E3 | 5.1E3 | 273 | 16 | 163 | 16 | 0.57 |
| tF | pg/mL | 1.5E3 | 1.6E3 | 1.2E4 | 4.0E3 | 3.8E4 | 5.0E3 | 1.2E1 | 1.8E1 | 3.2E5 | 1.5E4 | 246 | 13 | 160 | 13 | 0.56 |
| hA | ng/ml | 2.1E0 | 2.9E0 | 9.9E0 | 3.7E0 | 3.7E1 | 4.2E0 | 1.7E-2 | 5.7E-1 | 3.5E2 | 1.5E1 | 197 | 12 | 131 | 12 | 0.53 |
| nM | pg/ml | 1.0E-9 | 1.0E-9 | 7.7E1 | 1.0E-9 | 8.9E2 | 0.0E0 | 1.0E-9 | 1.0E-9 | 1.0E4 | 1.0E-9 | 133 | 10 | 101 | 10 | 0.49 |
| nN | pg/ml | 1.2E3 | 1.2E3 | 4.2E3 | 1.4E3 | 2.3E4 | 9.1E2 | 1.1E2 | 1.2E2 | 2.7E5 | 2.9E3 | 133 | 10 | 101 | 10 | 0.48 |
| nO | pg/ml | 2.6E1 | 3.2E1 | 4.5E1 | 4.7E1 | 5.3E1 | 4.1E1 | 3.5E0 | 1.1E1 | 3.1E2 | 1.3E2 | 133 | 10 | 101 | 10 | 0.54 |
| nR | pg/ml | 1.5E1 | 2.7E1 | 3.2E1 | 1.1E2 | 4.5E1 | 2.2E2 | 1.0E-9 | 5.5E-1 | 2.6E2 | 7.1E2 | 133 | 10 | 101 | 10 | 0.57 |
| nT | pg/ml | 8.0E1 | 8.8E1 | 2.0E2 | 2.7E2 | 7.9E2 | 5.3E2 | 1.0E-9 | 2.9E1 | 6.6E3 | 1.8E3 | 133 | 10 | 101 | 10 | 0.58 |
| nU | pg/ml | 2.9E1 | 6.7E1 | 2.5E2 | 3.7E2 | 1.4E3 | 9.2E2 | 1.0E-9 | 1.0E-9 | 1.3E4 | 3.0E3 | 133 | 10 | 101 | 10 | 0.63 |
| lW | pg/ml | 1.0E-9 | 1.0E-9 | 1.4E1 | 1.1E1 | 4.9E1 | 1.7E1 | 1.0E-9 | 1.0E-9 | 3.9E2 | 4.2E1 | 133 | 10 | 101 | 10 | 0.56 |
| lX | pg/ml | 9.5E2 | 9.9E2 | 1.0E3 | 1.1E3 | 5.8E2 | 5.6E2 | 1.2E2 | 3.5E2 | 2.6E3 | 2.3E3 | 133 | 10 | 101 | 10 | 0.56 |
| lY | pg/ml | 1.9E1 | 2.3E1 | 2.2E1 | 2.8E1 | 1.9E1 | 2.6E1 | 1.0E-9 | 5.4E0 | 1.4E2 | 9.6E1 | 133 | 10 | 101 | 10 | 0.56 |
| mE | pg/ml | 1.0E-9 | 6.0E-1 | 2.9E0 | 1.1E0 | 8.5E0 | 1.2E0 | 1.0E-9 | 1.0E-9 | 5.8E1 | 2.9E0 | 133 | 10 | 101 | 10 | 0.52 |
| mF | pg/ml | 1.0E-9 | 1.0E-9 | 2.4E0 | 1.1E0 | 9.4E0 | 2.0E0 | 1.0E-9 | 1.0E-9 | 1.1E2 | 6.1E0 | 133 | 10 | 101 | 10 | 0.46 |
| mH | pg/ml | 3.6E0 | 2.7E0 | 5.3E0 | 3.1E0 | 6.6E0 | 2.2E0 | 2.3E-1 | 4.0E-1 | 5.3E1 | 8.2E0 | 133 | 10 | 101 | 10 | 0.41 |
| mI | pg/ml | 1.0E-9 | 1.8E0 | 1.5E1 | 7.3E0 | 3.1E1 | 9.6E0 | 1.0E-9 | 1.0E-9 | 1.8E2 | 2.7E1 | 133 | 10 | 101 | 10 | 0.50 |
| mM | pg/ml | 2.2E1 | 4.0E1 | 6.9E1 | 4.7E1 | 1.3E2 | 4.4E1 | 1.0E-9 | 1.8E0 | 9.8E2 | 1.5E2 | 133 | 10 | 101 | 10 | 0.58 |
| mP | pg/ml | 1.4E1 | 1.4E1 | 1.8E1 | 1.7E1 | 2.2E1 | 1.3E1 | 1.0E-9 | 1.0E-9 | 1.9E2 | 3.7E1 | 132 | 10 | 100 | 10 | 0.55 |
| mS | pg/ml | 1.6E3 | 1.8E3 | 1.8E3 | 2.4E3 | 1.6E3 | 1.7E3 | 1.0E-9 | 7.9E2 | 1.3E4 | 5.9E3 | 133 | 10 | 101 | 10 | 0.59 |
| mT | pg/ml | 5.4E1 | 8.0E1 | 1.3E2 | 2.5E2 | 2.2E2 | 5.9E2 | 9.7E0 | 2.1E1 | 1.4E3 | 1.9E3 | 132 | 10 | 100 | 10 | 0.53 |
| mU | pg/ml | 2.2E0 | 3.0E0 | 4.0E0 | 3.3E0 | 8.3E0 | 2.0E0 | 1.0E-9 | 1.0E-9 | 6.8E1 | 7.2E0 | 132 | 10 | 100 | 10 | 0.63 |
| mW | pg/ml | 2.3E3 | 3.9E3 | 2.7E3 | 3.5E3 | 2.1E3 | 1.8E3 | 1.0E-9 | 6.7E2 | 1.8E4 | 7.0E3 | 132 | 10 | 100 | 10 | 0.67 |
| mY | pg/ml | 5.5E2 | 7.3E2 | 8.5E2 | 9.6E2 | 1.3E3 | 9.0E2 | 1.0E-9 | 6.1E1 | 1.1E4 | 2.7E3 | 133 | 10 | 101 | 10 | 0.56 |
| mZ | pg/ml | 1.7E2 | 5.8E2 | 2.9E2 | 6.3E2 | 3.0E2 | 4.5E2 | 1.0E-9 | 9.2E1 | 1.5E3 | 1.7E3 | 132 | 10 | 100 | 10 | 0.77 |
| nA | pg/ml | 1.6E0 | 4.3E0 | 1.0E1 | 7.2E0 | 4.3E1 | 9.4E0 | 1.0E-9 | 1.0E-9 | 4.4E2 | 3.1E1 | 132 | 10 | 100 | 10 | 0.62 |

Figure 13 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nB | pg/ml | 3.1E2 | 4.1E2 | 3.2E2 | 4.2E2 | 1.7E2 | 1.6E2 | 3.0E1 | 2.2E2 | 9.1E2 | 7.2E2 | 133 | 10 | 101 | 10 | 0.68 |
| nC | pg/ml | 1.0E-9 | 1.0E-9 | 2.5E4 | 3.8E3 | 1.5E5 | 7.7E3 | 1.0E-9 | 1.0E-9 | 1.5E6 | 2.0E4 | 133 | 10 | 101 | 10 | 0.47 |
| nD | pg/ml | 7.9E0 | 1.0E1 | 3.6E1 | 2.4E1 | 2.0E2 | 4.4E1 | 1.0E-9 | 1.0E-9 | 1.7E3 | 1.5E2 | 132 | 10 | 100 | 10 | 0.55 |
| nF | pg/ml | 1.0E-9 | 1.0E-9 | 4.5E0 | 3.6E0 | 2.5E1 | 1.1E1 | 1.0E-9 | 1.0E-9 | 2.4E2 | 3.6E1 | 133 | 10 | 101 | 10 | 0.48 |
| nH | pg/ml | 1.0E0 | 1.0E-9 | 2.2E2 | 5.5E1 | 1.3E3 | 1.1E2 | 1.0E-9 | 1.0E-9 | 1.0E4 | 2.9E2 | 132 | 10 | 100 | 10 | 0.43 |
| nI | pg/ml | 3.0E1 | 9.2E1 | 1.5E2 | 1.8E2 | 8.3E2 | 3.6E2 | 1.0E-9 | 1.0E-9 | 9.2E3 | 1.2E3 | 133 | 10 | 101 | 10 | 0.61 |
| nJ | pg/ml | 5.9E-2 | 7.4E-1 | 4.1E1 | 3.5E0 | 4.5E2 | 5.9E0 | 1.0E-9 | 1.0E-9 | 5.2E3 | 1.6E1 | 133 | 10 | 101 | 10 | 0.61 |
| nK | pg/ml | 1.0E-9 | 7.9E0 | 5.6E1 | 5.4E1 | 3.4E2 | 9.2E1 | 1.0E-9 | 1.0E-9 | 3.2E3 | 2.3E2 | 132 | 10 | 100 | 10 | 0.56 |
| nL | pg/ml | 1.0E-9 | 1.0E-9 | 5.9E2 | 2.0E2 | 4.1E3 | 4.3E2 | 1.0E-9 | 1.0E-9 | 4.5E4 | 1.2E3 | 133 | 10 | 101 | 10 | 0.50 |
| hR | pg/ml | 2.6E4 | 2.4E4 | 2.7E4 | 2.3E4 | 1.1E4 | 7.1E3 | 1.0E-9 | 1.2E4 | 5.8E4 | 3.9E4 | 187 | 12 | 127 | 12 | 0.38 |
| hV | pg/ml | 4.4E2 | 3.7E2 | 4.6E2 | 4.2E2 | 2.4E2 | 1.9E2 | 1.0E-9 | 1.9E2 | 1.5E3 | 7.8E2 | 187 | 12 | 127 | 12 | 0.45 |
| hW | pg/ml | 1.6E3 | 1.3E3 | 2.1E3 | 2.1E3 | 3.0E3 | 2.7E3 | 1.0E-9 | 5.7E2 | 4.0E4 | 1.0E4 | 187 | 12 | 127 | 12 | 0.43 |
| hX | pg/ml | 9.0E2 | 9.1E2 | 1.0E3 | 1.2E3 | 7.3E2 | 1.2E3 | 2.5E0 | 4.6E2 | 8.6E3 | 4.9E3 | 187 | 12 | 127 | 12 | 0.51 |
| iA | pg/ml | 1.5E2 | 1.4E2 | 3.0E2 | 1.6E2 | 6.1E2 | 1.2E2 | 8.2E0 | 5.8E0 | 7.1E3 | 4.5E2 | 246 | 13 | 160 | 13 | 0.43 |
| iB | ng/ml | 4.8E0 | 5.6E0 | 6.1E0 | 7.4E0 | 5.0E0 | 5.5E0 | 3.3E-2 | 2.3E0 | 2.6E1 | 2.0E1 | 197 | 12 | 131 | 12 | 0.57 |
| iC | U/ml | 2.3E-1 | 2.0E-1 | 1.1E0 | 3.8E-1 | 4.8E0 | 6.5E-1 | 1.0E-9 | 1.0E-9 | 5.5E1 | 2.4E0 | 197 | 12 | 131 | 12 | 0.41 |
| iH | ng/ml | 1.6E5 | 1.8E5 | 1.6E5 | 1.6E5 | 4.8E4 | 5.4E4 | 2.9E3 | 7.2E4 | 2.7E5 | 2.6E5 | 246 | 13 | 160 | 13 | 0.51 |
| iJ | ng/ml | 4.9E4 | 6.0E4 | 5.2E4 | 6.0E4 | 2.6E4 | 1.8E4 | 1.8E3 | 3.4E4 | 2.5E5 | 9.5E4 | 246 | 13 | 160 | 13 | 0.63 |
| hB | ng/ml | 4.5E-1 | 5.0E-1 | 5.6E-1 | 7.5E-1 | 4.5E-1 | 8.6E-1 | 1.0E-9 | 2.2E-1 | 3.2E0 | 3.4E0 | 246 | 13 | 160 | 13 | 0.54 |
| hC | pg/ml | 3.8E3 | 4.2E3 | 6.8E3 | 6.8E3 | 8.7E3 | 6.9E3 | 1.0E-9 | 1.7E2 | 5.7E4 | 2.5E4 | 246 | 13 | 160 | 13 | 0.53 |
| hF | ng/ml | 1.0E-9 | 1.0E-9 | 2.0E1 | 1.0E-9 | 2.6E2 | 0.0E0 | 1.0E-9 | 1.0E-9 | 4.0E3 | 1.0E-9 | 246 | 13 | 160 | 13 | 0.49 |
| hG | pg/ml | 6.8E3 | 7.3E3 | 7.2E3 | 9.5E3 | 3.0E3 | 5.0E3 | 2.8E1 | 3.4E3 | 2.0E4 | 1.9E4 | 246 | 13 | 160 | 13 | 0.63 |
| iO | ng/ml | 3.7E5 | 2.7E5 | 3.9E5 | 3.3E5 | 1.8E5 | 2.0E5 | 1.1E4 | 1.3E5 | 1.1E6 | 9.0E5 | 246 | 13 | 160 | 13 | 0.35 |
| iP | ng/ml | 4.8E4 | 3.7E4 | 5.6E4 | 4.2E4 | 5.6E4 | 3.0E4 | 1.0E-9 | 5.2E3 | 5.7E5 | 1.2E5 | 246 | 13 | 160 | 13 | 0.40 |
| iZ | ng/ml | 1.6E3 | 2.2E3 | 1.8E3 | 2.8E3 | 7.4E2 | 1.6E3 | 4.7E2 | 9.8E2 | 5.1E3 | 6.5E3 | 247 | 13 | 160 | 13 | 0.71 |
| rC | pg/ml | 1.7E3 | 1.3E3 | 2.1E3 | 2.7E3 | 1.8E3 | 3.8E3 | 1.0E-9 | 7.3E2 | 1.5E4 | 1.5E4 | 187 | 12 | 127 | 12 | 0.51 |
| rB | pg/ml | 2.6E1 | 2.4E1 | 4.6E1 | 5.2E1 | 8.9E1 | 7.9E1 | 1.0E-9 | 1.0E-9 | 9.5E2 | 2.9E2 | 187 | 12 | 127 | 12 | 0.49 |
| jD | ng/ml | 3.2E1 | 3.7E1 | 4.9E1 | 4.5E1 | 6.3E1 | 4.3E1 | 1.0E-9 | 1.0E-9 | 5.1E2 | 1.4E2 | 196 | 12 | 131 | 12 | 0.50 |
| jE | ng/ml | 1.0E-9 | 1.0E-9 | 6.9E0 | 5.6E0 | 1.6E1 | 1.4E1 | 1.0E-9 | 1.0E-9 | 1.2E2 | 4.6E1 | 196 | 12 | 131 | 12 | 0.50 |
| jF | ng/ml | 3.9E1 | 2.8E1 | 5.2E1 | 4.7E1 | 5.8E1 | 5.8E1 | 1.0E-9 | 1.0E-9 | 3.5E2 | 1.6E2 | 196 | 12 | 131 | 12 | 0.48 |
| jG | ng/ml | 4.2E3 | 6.4E3 | 4.3E3 | 6.0E3 | 1.9E3 | 1.7E3 | 6.0E2 | 3.0E3 | 9.6E3 | 7.9E3 | 197 | 12 | 131 | 12 | 0.76 |
| jH | ng/ml | 7.4E1 | 1.0E2 | 8.4E1 | 1.1E2 | 5.1E1 | 5.1E1 | 1.3E1 | 4.8E1 | 4.3E2 | 2.5E2 | 197 | 12 | 131 | 12 | 0.71 |
| jI | ng/ml | 6.8E1 | 7.5E1 | 7.6E1 | 7.8E1 | 4.1E1 | 3.9E1 | 1.9E1 | 3.5E1 | 4.4E2 | 1.9E2 | 197 | 12 | 131 | 12 | 0.52 |
| rA | pg/ml | 2.6E1 | 3.0E1 | 3.1E1 | 3.1E1 | 2.4E1 | 1.8E1 | 1.0E-9 | 7.5E0 | 2.0E2 | 6.5E1 | 197 | 12 | 131 | 12 | 0.53 |
| qZ | pg/ml | 4.4E1 | 4.0E-3 | 5.4E2 | 3.4E1 | 2.1E3 | 6.1E1 | 1.0E-9 | 5.8E-4 | 1.0E4 | 1.9E2 | 152 | 9 | 115 | 9 | 0.30 |
| qY | pg/ml | 2.6E1 | 3.7E1 | 5.0E1 | 5.8E1 | 6.4E1 | 5.8E1 | 8.7E-1 | 1.1E1 | 5.3E2 | 1.8E2 | 197 | 12 | 131 | 12 | 0.58 |
| qX | pg/ml | 6.0E1 | 7.3E1 | 6.7E1 | 7.4E1 | 4.7E1 | 3.0E1 | 1.0E-9 | 2.3E1 | 2.5E2 | 1.3E2 | 197 | 12 | 131 | 12 | 0.61 |
| qW | pg/ml | 8.8E0 | 1.1E1 | 1.3E1 | 2.2E1 | 1.5E1 | 2.2E1 | 1.0E-9 | 4.0E-1 | 1.2E2 | 8.1E1 | 197 | 12 | 131 | 12 | 0.63 |
| qV | pg/ml | 2.2E3 | 2.7E3 | 2.8E3 | 4.1E3 | 2.1E3 | 4.4E3 | 1.7E2 | 6.1E2 | 9.6E3 | 1.7E4 | 197 | 12 | 131 | 12 | 0.58 |
| qU | pg/ml | 6.4E1 | 4.0E1 | 1.8E2 | 7.1E1 | 2.8E2 | 7.7E1 | 1.0E-9 | 1.0E-9 | 2.1E3 | 2.7E2 | 197 | 12 | 131 | 12 | 0.39 |
| qT | pg/ml | 4.1E1 | 5.0E1 | 7.6E1 | 5.3E1 | 1.1E2 | 2.5E1 | 1.0E-9 | 1.1E1 | 9.0E2 | 8.8E1 | 197 | 12 | 131 | 12 | 0.53 |
| jK | ng/ml | 1.6E3 | 1.6E3 | 1.7E3 | 1.8E3 | 6.6E2 | 8.8E2 | 2.8E2 | 6.4E2 | 4.3E3 | 3.5E3 | 197 | 12 | 131 | 12 | 0.49 |
| jL | ng/ml | 2.0E2 | 2.5E2 | 3.0E2 | 2.8E2 | 3.0E2 | 1.9E2 | 3.5E1 | 4.8E1 | 2.1E3 | 7.9E2 | 197 | 12 | 131 | 12 | 0.56 |
| jM | ng/ml | 7.0E4 | 9.0E4 | 7.5E4 | 8.4E4 | 3.9E4 | 4.5E4 | 3.9E2 | 7.8E3 | 1.9E5 | 1.5E5 | 197 | 12 | 131 | 12 | 0.58 |
| jO | pg/ml | 2.1E5 | 2.3E5 | 2.6E5 | 2.5E5 | 1.5E5 | 1.5E5 | 5.2E4 | 1.1E5 | 1.1E6 | 6.4E5 | 197 | 12 | 131 | 12 | 0.49 |
| jP | pg/ml | 2.3E5 | 1.9E5 | 2.7E5 | 1.7E5 | 1.9E5 | 7.6E4 | 3.6E4 | 5.8E4 | 1.9E6 | 3.4E5 | 197 | 12 | 131 | 12 | 0.31 |
| jQ | pg/ml | 2.5E3 | 3.3E3 | 3.5E3 | 4.0E3 | 3.3E3 | 3.0E3 | 1.0E-9 | 5.5E2 | 1.8E4 | 1.1E4 | 197 | 12 | 131 | 12 | 0.58 |
| jR | pg/ml | 5.9E3 | 8.1E3 | 1.1E4 | 1.0E4 | 1.3E4 | 8.0E3 | 1.0E-9 | 1.3E3 | 9.0E4 | 2.5E4 | 197 | 12 | 131 | 12 | 0.54 |
| jT | pg/ml | 1.7E5 | 1.8E5 | 1.7E5 | 2.0E5 | 6.2E4 | 7.4E4 | 6.8E4 | 1.1E5 | 3.9E5 | 3.3E5 | 197 | 12 | 131 | 12 | 0.60 |
| jU | mIU/ml | 4.3E0 | 3.7E0 | 1.0E1 | 6.5E0 | 1.7E1 | 5.7E0 | 4.2E-2 | 1.9E-1 | 1.1E2 | 1.6E1 | 197 | 12 | 131 | 12 | 0.50 |
| jV | mIU/ml | 1.3E0 | 2.1E0 | 3.3E0 | 4.9E0 | 5.7E0 | 6.8E0 | 1.7E-3 | 6.9E-4 | 3.3E1 | 2.1E1 | 197 | 12 | 131 | 12 | 0.57 |
| jY | ng/ml | 7.3E-4 | 1.5E-3 | 6.3E-3 | 5.3E-3 | 2.8E-2 | 7.8E-3 | 1.0E-9 | 1.0E-9 | 3.0E-1 | 2.7E-2 | 197 | 12 | 131 | 12 | 0.60 |
| kC | pg/ml | 9.7E1 | 1.0E2 | 1.9E2 | 1.7E2 | 4.3E2 | 1.9E2 | 2.1E1 | 5.2E1 | 3.5E3 | 6.8E2 | 133 | 10 | 101 | 10 | 0.51 |
| kE | pg/ml | 1.3E5 | 1.2E5 | 1.3E5 | 1.3E5 | 4.0E4 | 4.0E4 | 1.2E4 | 5.5E4 | 2.3E5 | 1.9E5 | 133 | 10 | 101 | 10 | 0.49 |
| kF | pg/mL | 6.1E1 | 7.3E1 | 6.9E1 | 7.5E1 | 4.9E1 | 2.1E1 | 2.6E1 | 5.0E1 | 5.1E2 | 1.2E2 | 133 | 10 | 101 | 10 | 0.65 |
| kG | pg/mL | 9.1E3 | 8.8E3 | 1.2E4 | 1.6E4 | 1.3E4 | 2.6E4 | 7.5E2 | 4.6E3 | 1.2E5 | 9.1E4 | 133 | 10 | 101 | 10 | 0.50 |
| kI | pg/ml | 1.9E2 | 1.9E2 | 2.2E2 | 1.9E2 | 1.4E2 | 9.0E1 | 4.4E1 | 5.4E1 | 8.7E2 | 3.6E2 | 133 | 10 | 101 | 10 | 0.47 |

Figure 13 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| kK | pg/ml | 1.0E2 | 1.0E2 | 1.5E2 | 2.4E2 | 1.6E2 | 2.5E2 | 6.4E0 | 3.2E1 | 1.2E3 | 6.9E2 | 133 | 10 | 101 | 10 | 0.51 |
| kN | pg/ml | 9.9E2 | 6.5E2 | 1.5E3 | 9.0E2 | 2.2E3 | 9.2E2 | 7.6E1 | 1.2E2 | 1.7E4 | 3.3E3 | 133 | 10 | 101 | 10 | 0.34 |
| kO | pg/ml | 7.1E3 | 7.8E3 | 9.6E3 | 9.1E3 | 1.7E4 | 4.4E3 | 3.4E3 | 5.2E3 | 1.5E5 | 1.8E4 | 133 | 10 | 101 | 10 | 0.58 |
| kP | pg/ml | 5.8E3 | 5.8E3 | 7.2E3 | 6.2E3 | 6.2E3 | 2.7E3 | 8.6E2 | 2.3E3 | 4.8E4 | 1.2E4 | 133 | 10 | 101 | 10 | 0.49 |
| kQ | pg/ml | 4.1E3 | 4.5E3 | 5.2E3 | 4.9E3 | 3.8E3 | 2.4E3 | 5.6E2 | 1.3E3 | 2.5E4 | 1.0E4 | 246 | 13 | 160 | 13 | 0.53 |
| kR | pg/ml | 2.1E1 | 1.7E1 | 3.0E1 | 2.0E1 | 6.8E1 | 1.3E1 | 1.0E-9 | 1.8E0 | 1.0E3 | 5.7E1 | 246 | 13 | 160 | 13 | 0.42 |
| kS | pg/ml | 7.8E2 | 1.1E3 | 9.2E2 | 2.3E3 | 6.5E2 | 3.7E3 | 7.9E1 | 3.4E2 | 4.8E3 | 1.4E4 | 246 | 13 | 160 | 13 | 0.71 |
| rZ | ng/ml | 1.0E-9 | 1.0E-9 | 5.8E-3 | 2.6E-2 | 1.5E-2 | 7.8E-2 | 1.0E-9 | 1.0E-9 | 1.1E-1 | 2.6E-1 | 187 | 11 | 127 | 11 | 0.44 |
| rY | ng/ml | 6.1E-2 | 4.1E-2 | 1.4E-1 | 1.6E0 | 5.3E-1 | 5.0E0 | 1.0E-9 | 1.0E-9 | 6.3E0 | 1.7E1 | 187 | 11 | 127 | 11 | 0.42 |
| rX | ng/ml | 1.0E-9 | 1.0E-9 | 4.0E-2 | 1.7E-1 | 2.9E-1 | 5.6E-1 | 1.0E-9 | 1.0E-9 | 3.7E0 | 1.9E0 | 187 | 11 | 127 | 11 | 0.53 |
| lK | pg/ml | 7.9E1 | 1.3E2 | 1.7E2 | 1.3E2 | 3.1E2 | 1.3E2 | 1.0E-9 | 1.0E-9 | 3.3E3 | 3.3E2 | 196 | 12 | 131 | 12 | 0.49 |
| lL | pg/ml | 1.5E3 | 3.3E3 | 2.1E3 | 3.6E3 | 2.3E3 | 2.0E3 | 1.5E1 | 8.7E2 | 1.9E4 | 7.2E3 | 197 | 12 | 131 | 12 | 0.76 |
| lM | pg/ml | 1.1E3 | 1.4E3 | 3.6E3 | 4.0E3 | 7.0E3 | 9.4E3 | 1.3E2 | 3.5E2 | 4.4E4 | 3.4E4 | 197 | 12 | 131 | 12 | 0.53 |
| lN | pg/ml | 1.0E-9 | 1.0E-9 | 4.3E0 | 3.0E0 | 1.5E1 | 4.7E0 | 1.0E-9 | 1.0E-9 | 1.5E2 | 1.2E1 | 197 | 12 | 131 | 12 | 0.52 |
| lO | pg/ml | 1.0E-9 | 1.0E-9 | 1.8E0 | 7.0E0 | 1.4E1 | 2.4E1 | 1.0E-9 | 1.0E-9 | 1.4E2 | 8.4E1 | 196 | 12 | 131 | 12 | 0.53 |
| nW | pg/ml | 1.1E5 | 1.1E5 | 1.1E5 | 1.1E5 | 2.6E4 | 3.6E4 | 3.6E4 | 5.9E4 | 2.0E5 | 1.9E5 | 246 | 13 | 160 | 13 | 0.52 |
| nY | pg/ml | 2.0E3 | 1.9E3 | 2.3E3 | 3.3E3 | 1.3E3 | 3.3E3 | 5.1E2 | 1.0E3 | 9.9E3 | 1.3E4 | 246 | 13 | 160 | 13 | 0.54 |
| oO | pg/ml | 8.7E4 | 1.3E5 | 1.2E5 | 1.5E5 | 9.5E4 | 9.1E4 | 3.3E3 | 3.5E3 | 6.2E5 | 3.3E5 | 123 | 10 | 96 | 10 | 0.63 |
| oP | pg/ml | 1.2E5 | 1.7E5 | 1.4E5 | 2.1E5 | 8.2E4 | 1.1E5 | 2.4E4 | 1.0E5 | 4.5E5 | 4.2E5 | 123 | 10 | 96 | 10 | 0.71 |
| oQ | pg/ml | 2.9E3 | 4.1E3 | 3.8E3 | 4.3E3 | 3.0E3 | 1.6E3 | 7.7E2 | 2.1E3 | 2.0E4 | 6.7E3 | 123 | 10 | 96 | 10 | 0.66 |
| oE | pg/ml | 1.3E2 | 3.4E2 | 3.9E2 | 5.0E2 | 5.8E2 | 5.1E2 | 1.0E-9 | 2.8E0 | 4.7E3 | 1.8E3 | 246 | 13 | 160 | 13 | 0.62 |
| oF | pg/ml | 8.0E3 | 1.3E4 | 2.1E4 | 4.2E4 | 3.3E4 | 7.3E4 | 6.4E1 | 6.9E2 | 1.7E5 | 2.3E5 | 246 | 13 | 160 | 13 | 0.57 |
| oH | pg/ml | 4.0E1 | 9.3E1 | 9.3E1 | 1.1E2 | 1.5E2 | 8.5E1 | 4.3E-1 | 1.9E1 | 9.9E2 | 3.2E2 | 246 | 13 | 160 | 13 | 0.69 |
| oK | pg/ml | 8.5E2 | 6.6E2 | 2.0E3 | 1.1E3 | 3.0E3 | 8.3E2 | 5.2E1 | 1.4E2 | 2.5E4 | 2.4E3 | 246 | 13 | 160 | 13 | 0.49 |
| oN | pg/ml | 5.1E2 | 5.6E2 | 7.6E2 | 5.2E2 | 1.4E3 | 2.2E2 | 1.1E2 | 2.0E2 | 1.8E4 | 8.0E2 | 246 | 13 | 160 | 13 | 0.48 |
| pF | pg/ml | 5.1E-1 | 5.0E-1 | 1.1E0 | 1.4E0 | 5.6E0 | 2.6E0 | 1.0E-9 | 3.1E-1 | 8.7E1 | 1.0E1 | 246 | 13 | 160 | 13 | 0.59 |

Analyte panel data:

Unconstrained panels with 3 analytes, where 1.0E-10 >= 'model p-value' > 0. Contains 2 panels of 10,943,034 total panels evaluated. : Gc{Oe(Ql Qn)}

Unconstrained panels with 3 analytes, where 1.0E-9 >= 'model p-value' > 1.0E-10. Contains 96 panels of 10,943,034 total panels evaluated. : aA{Js(Fr Ik Ir Is Iu Iv Jg Ji Jk Jq Lv Lw Mi Mn Mu Mv Mx Mz Nl Nn No Nw Ok On Pd Po Pz Qb Qc) Ok(Ih Il In Ir Is It Iu Jt Md Mn Mt Pd Pz) Iu(Fr Jg Jk Md Mv Ng Nw On Pd Pz) Jg(Il In Jt Md Mn Mt Ng Nr Pz) Md(Jk Mq Mu Mw Nw Om On) Nw(Il Ir Jt Mt Pd Pz) Ik(In Ng Nr Pz) On(Ir Jt Mt Pd) Lw(In Ir Pd) Ih(Ir Pd Qb) Jk(Il In Mt) Nn(Jt Mn) MiPd} GcMyOe GdMmHu Unconstrained panels with 3 analytes, where 1.0E-8 >= 'model p-value' > 1.0E-9. Contains 1,538 panels of 10,943,034 total panels evaluated. : aA{Iu(Et Fp Hq Hr Hu Hv Hw Hx Ih Ii Ij Ik Il Im In Io Ip Iq Ir Is It Iv Jh Ji Jj Jl Jm Jn Jo Jp Jq Jr Jt Lh Li Lj Lu Lv Lw Lx Ly Lz Ma Mb Mc Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Om On Oy Oz Pa Pb Pc Pe Pf Pg Po Qa Qb Qc Qd Qe) Ok(Et Fp Fr Hq Hr Hv Hw Hx Ii Ij Ik Im Io Ip Iq Iv Jg Ji Jj Jk Jm Jn Jo Jp Jq Jr Jt Lh Li Lj Lu Lv Lw Lx Ly Lz Ma Mb Mc Me Mf Mg Mh Mi Mj Mk Ml Mm Mp Mr Ms Mu Mv Mw Mx Mz Na Nb Nc Nd Ne Nf Ng Nh Ni Nj Nk Nl Nm Nn No Nq Nr Ns Nt Nu Nv Nx Ny Oe Of Og Oh Oi Om On Oy Oz Pa Pb Pc Pe Pf Pg Po Qa Qb Qc Qd Qe) Il(Et Fp Fr Hr Hv Hw Hx Ih Ij Ik In Io Ip Iq Ir Is It Iv Ji Jl Jm Jn Jo Jr Js Jt Lh Li Lj Lv Lw Lx Lz Ma Mb Mc Md Me Mf Mg Mh Mi Mj Mk Ml Mn Mq Mr Ms Mt Mu Mv Mw Mx My Mz Na Nb Nc Nd Ne Nf Ng Nh Ni Nk Nl Nm Nn No Nr Ns Nt Nu Nv Nx Ny Og Oh Oi Om On Oy Oz Pa Pb Pc Pd Pe Pf Pg Po Pz Qa Qb Qc) Mn(Fp Fr Hq Hr Hv Hw Hx Ih Ii Ij Ik Im In Ir It Ji Jj Jk Jl Jm Jn Jo Jr Jt Lh Li Lj Lu Lv Lw Lx Lz Ma Mb Mc Md Me Mf Mg Mh Mi Mj Mk Ml Mq Mr Ms Mt Mu Mv Mw Mx My Mz Na Nb Nc Nd Ne Nf Ng Nh Ni Nk Nl Nm No Nq Nr Ns Nt Nu Nv Nw Nx Ny Og Oh Oi On Oy Oz Pa Pb Pc Pd Pe Pf Pg Po Pz Qa Qb Qc) Js(Et Fp Hq Hr Hu Hv Hw Hx Ih Ii Ij Im In Io Ip Iq It Jh Jj Jl Jm Jn Jo Jp Jr Jt Lh Li Lj Lu Lx Ly Lz Ma Mb Mc Md Me Mf Mg Mh Mj Mk Ml Mm Mp Mq Mr Ms Mt Mw My Na Nb Nc Nd Ne Nf Ng Nh Ni Nj Nk Nm Nq Nr Ns Nt Nu Nv Nx Ny Oe Of Og Oh Oi Om On Oy Oz Pa Pb Pc Pe Pf Pg Qa Qd Qe) Ih(Fp Fr Hq Hr Hv Hw Hx Ij Ik Im In Io Ip Iq Is It Iv Jg Ji Jj Jk Jl Jm Jn Jo Jr Jt Lh Li Lv Lw Lz Ma Mb Mc Md Me Mf Mg Mh Mi Mk Ml Mq Mr Mt Mu Mv Mw Mx My Na Nc Nd Ne Ng Nh Ni Nk Nl Nn No Nr Ns Nt Nu Nv Nw Nx Ny Of Og Oh Oi On Oy Oz Pa Pb Pc Pe Pf Pg Po Pz Qa Qc) Ir(cO Et Fp Fr Hq Hr Hv Hw Ij Ik Im In Io Is It Iv Jg Ji Jj Jk Jl Jm Jn Jo Jq Jr Jt Lv Lz Ma Mb Md Me Mf Mg Mh Mi Mk Ml Mq Mr Mt Mu Mv Mw Mx Mz Nb Nc Nd Ne Ng Nh Ni Nk Nl Nn Nr Ns Nu Nx Ny Oh Om Oy Pb Pc Pd Pe Pg Po Pz Qa Qb Qc) Md(Et Fp Fr Hr Hw Hx Ij Ik Im In Io Ip Iq Is It Iv Jh Ji Jj Jm Jq Jr Jt Lh Lj Lv Lw Lz Ma Mb Me Mf Mh Mi Mk Ml Mr Mv Mx My Mz Nb Nc Ne Ng Nh Ni Nk Nl Nm Nn No Nr Nu Nv Nx Ny Oh Oi Oy Oz Pa Pb Pc Pd Pe Pf Pg Po Pz Qb Qc) In(Fp Fr Hr Hv Hw Hx Ij Im Io Ip Iq Is It Iv Ji Jl Jm Jq Jr Jt Lh Lj Lv Lx Lz Ma Mb Me Mf Mi Mk Mq Mr Mu Mv Mw Mx Mz Nc Ne Nf Ng Nh Ni Nk Nl Nn Nr Ns Nt Nu Nv Nw Nx Ny Oh Om On Oy Pb Pc Pd Pe Pg Po Pz Qb Qc) Pd(Et Fp Fr Hq Hr Hw Ii Ij Ik Im Io Ip Iq Is It Iv Jg Ji Jj Jk Jm Jn Jo Jq Jr Jt Lh Lj Lv Lz Ma Mf Mg Mj Ml Mq Mr Mt Mu Mv Mw Mx Mz Ne Ng Ni Nk Nl Nn Nr Nx Ny Oh Om Oy Pb Pc Pe Pf Pg Po Pz Qa Qc Qe) Pz(Fr Hq Hv Hw Ij Im Io Ip Iq Is It Iv Ji Jj Jk Jl Jm Jn Jo Jr Jt Lh Li Lj Lv Lw Lz Ma Mb Mf Ml Mq Mr Mt Mu Mv Mw Na Nd Ne Nf Ng Nh Ni Nk Nl Nn Nr Nv Nx Ny Oh Oi On Pc Pe Pf Pg Po Qa Qb Qc) Jt(Fp Fr Hq Hr Hx Ik Io Ip Iq Is It Iv Ji Jk Jl Jm Jq Jr Lh Li Lv Lw Lz Mb Mf Mg Mi Ml Mq Mr Mt Mu Mv Mw Mx My Ne Ng Nh Ni Nk Nl No Nr Nt Nu Nv Nx Oh Oi Om Oy Pb Pc Pe Pg Po Qb Qc Qd) Nw(Et Hq Hw Hx Ii Ij Ik Im Io Ip Iq Is It Iv Jm Jn Jo Jq Jr Lh Lj Lx Lz Ma Mb Mf Mg Mh Mj Ml Mx Na Nb Ne Nf Ng

Figure 13 Continued

Nk Nl Nm Nq Nr Nx Ny Oh Pa Pe Pf Pg Po Qa Qc) On(Et Hq Hw Ii Ij Ik Im Io Ip Iq Is It Iv Jm Jn Jo Jq Jr Lh Lj Lx Lz Ma Mb Mf Mg Mh Mj Ml Mp Mr Mx Na Nb Nf Ng Nk Nl Nm No Nr Ny Oh Om Pa Pe Pf Pg Po Qa Qe) Ik(Et Fr Hq Hv Hw Ii Ij Im Io Is It Iv Jg Jj Jk Jm Jn Jo Jr Lh Lj Lw Lz Ma Mf Mg Mh Mj Ml Mq Mt Mx Na Ne Nf Nk Nl Nm Nt Ny Of Oh Pc Pe Pf Pg Qa Qe) It(Et Fp Fr Hq Hr Ij Im Iv Jg Ji Jk Jl Jm Jo Lv Lw Lz Ma Mf Mg Mh Ml Mq Mt Mu Mv Mw Mx Nc Nd Ne Ng Ni Nk Nl Nn Nr Om Pb Pc Pg Po Qc) Jg(Et Hq Hw Ii Ij Im Io Iq Is Iv Jh Jm Jn Jo Jr Lh Lj Lz Ma Mb Mf Mg Mj Ml My Na Nb Nf Nk Nl Nm Nq Ny Of Oh Oy Pe Pf Pg Po Qa Qe) Nr(Fp Fr Is Iv Ji Jk Jm Li Lv Lw Lz Ma Mb Mf Mi Ml Mq Mr Mt Mu Mv Mx Nc Ne Ng Nh Ni Nk Nl Nn Nx Oh Oi Oy Pc Pg Po Qb Qc) Mt(Fr Hr Ij Io Ip Iq Is Iv Ji Lv Lw Lz Ma Mf Mi Mq Mr Mu Mv Mw Ng Ni Nk Nl Nn Nv Om Pc Pg Po Qc) Ng(Fr Ij Io Ip Iq Is Iv Jk Jr Lv Lz Ma Mb Mf Mg Ml Mu Mv Ni Nk Nl Nn Nx Oi Pc Pg Qc) Nl(Fr Ij Io Ip Iq Is Iv Jk Lv Lz Ma Mb Mf Mi Ml Mu Mv Nc Ne Nh Nk Nn Ny Qc) Jk(Hq Ii Ij Io Iq Is Iv Jj Jm Jo Lh Lz Ma Mf Mg Ml Nk Nq Ny Pe Pf Pg Po) Lz(Fr Ij Io Ip Iq Is Iv Lv Ma Mb Mf Mi Ml Mu Mv Nk Nn Pc Qc) Ij(Fr Io Iq Is Iv Ji Jq Lv Lw Ma Mf Mq Mv Ni Nk Om Pc Pg) Iv(cO Fr Ji Jo Lv Lw Ma Mf Ml Mq Mu Mv Nc Nk Pc Pg Qc) Is(Fr Ji Jo Lv Lw Ma Mf Mi Mq Mu Mv Nk Pc Qc) Mf(Io Ip Lv Ma Mb Mu Mv Nk Nn Pc Pg Qc) Lv(Hw Jn Jo Jr Lh Ml Ny Pe Pg Qa) Qc(Et Io Iq Jo Ma Ml Nk Ny Qa Qe) Lw(Hw Jn Jo Jr Ml Na Ny Qa) Mu(Io Jo Ma Mg Ml Nk Ny Pg) Fr(Et Jo Lh Ma Mg Pf Pg) Ji(Et Jn Jo Jr Ml Ny Qa) Mv(Io Jo Ma Mg Nk Ny) Nn(Et Ma Ny Pg) Mi(Hq Jo Lh Pg) Mq(Jo Jr Ml Ny) Nk(Ma Mb Ml Nc) Mw(My Ny) Jq(Jr Ml) Om(Jo Ny) cO(cS Ko) LiPf PcPg aJdG cEcS} Gc{Oe(Ao Cp Fn Iv Je Jg Ji Kk Kr Mm Ms Mu Oz Qy Rh Vq} MmMy} NnMnJj aJcSdG

Unconstrained panels with 3 analytes, where 1.0E-7 >= 'model p-value' > 1.0E-8. Contains 5,683 panels of 10,943,034 total panels evaluated. : aA{Of(Et Fp Fr Hq Hr Hu Hv Hw Hx Ii Ij Il Im In Io Ip Iq Ir Is It Iv Jh Ji Jj Jk Jl Jm Jn Jo Jp Jq Jr Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Og Oh Oi Om On Oy Oz Pa Pb Pc Pd Pe Pf Pg Po Pz Qa Qb Qc Qe) Oz(Et Fp Fr Hq Hr Hu Hv Hw Hx Ii Ij Ik Im In Io Ip Iq Ir Is It Iv Jg Jh Ji Jj Jk Jl Jm Jn Jo Jp Jq Jr Jt Lh Li Lj Lu Lv Lw Lx Ly Lz Ma Mb Mc Me Mf Mg Mh Mi Mj Mk Ml Mm Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Og Oh Oi Om On Oy Pa Pb Pc Pd Pe Pf Pg Po Pz Qa Qb Qc Qd Qe) Ns(Et Fp Fr Hq Hr Hu Hv Hw Hx Ii Ij Ik Im Io Ip Iq Is It Iv Jg Jh Ji Jj Jk Jl Jm Jn Jo Jp Jq Jr Jt Lh Li Lj Lu Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nc Nd Ne Nf Ng Nh Ni Nj Nk Nl Nm Nn No Nq Nr Nt Nu Nv Nw Nx Ny Oe Og Oh Oi Om On Oy Pa Pb Pc Pd Pe Pf Pg Po Pz Qa Qb Qc Qd Qe) Nd(Et Fp Fr Hq Hr Hu Hv Hw Hx Ii Ij Ik Im In Io Ip Iq Is Iv Jg Jh Ji Jj Jk Jl Jm Jn Jo Jp Jq Jr Jt Lh Li Lj Lu Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nc Ne Nf Ng Nh Ni Nj Nk Nl Nm Nn No Nq Nr Nt Nu Nv Nw Nx Ny Oe Og Oh Oi Om On Oy Pa Pb Pc Pd Pe Pf Pg Po Qa Qb Qc Qd Qe) Qc(Et Fp Fr Hq Hr Hu Hv Hw Hx Ih Ii Ij Il Im In Io Ip Iq Ir Is It Iv Jh Ji Jj Jk Jl Jm Jn Jo Jp Jq Jr Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Ne Nf Ng Nh Ni Nj Nk Nl Nm Nn No Nq Nr Nt Nu Nv Nx Ny Oe Og Oh Oi Om On Oy Pa Pb Pc Pe Pf Pg Po Pz Qa Qb Qd) Nm(cO Et Fp Fr Hq Hr Hu Hv Hw Hx Ih Ii Ij Im In Io Ip Iq Ir Is It Iv Jh Ji Jj Jk Jl Jm Jn Jo Jp Jq Jr Jt Lh Li Lj Lu Lv Lw Lx Ly Lz Ma Mb Mc Me Mf Mg Mh Mi Mj Mk Ml Mm Mp Mq Mr Ms Mt Mu Mv Mw Mx My Mz Na Nb Nc Ne Nf Ng Nh Ni Nj Nk Nl Nn No Nq Nr Nt Nu Nv Nx Ny Oe Og Oh Oi Om Oy Pa Pb Pc Pd Pe Pf Pg Po Pz Qa Qb Qc) Me(Et Fp Fr Hq Hr Hu Hv Hw Hx Ii Ij Ik Im Io Ip Iq Is Iv Jg Jh Ji Jj Jk Jl Jm Jn Jo Jp Jq Jr Jt Lh Li Lj Lu Lv Lw Lx Ly Lz Ma Mb Mc Mf Mg Mh Mi Mj Mk Ml Mm Mp Mq Mr Ms Mt Mu Mv Mw Mx My Mz Na Nb Nc Ne Nf Ng Nh Ni Nj Nk Nl Nn No Nq Nr Nt Nu Nv Nw Nx Ny Oe Og Oh Oi Om On Oy Pa Pb Pc Pd Pe Pf Pg Po Pz Qa Qb Qc Qd) Mj(Et Fp Fr Hq Hr Hu Hv Hw Hx Ih Ii Ij Im In Io Ip Iq Ir Is It Iv Jh Ji Jj Jk Jl Jm Jn Jo Jp Jq Jr Jt Lh Li Lj Lu Lv Lw Lx Ly Lz Ma Mb Mc Md Mf Mg Mh Mi Mk Ml Mm Mp Mq Mr Ms Mt Mu Mv Mw Mx My Mz Na Nb Nc Ne Nf Ng Nh Ni Nj Nk Nl Nn No Nq Nr Nt Nu Nv Nx Ny Oe Og Oh Oi Om Oy Pa Pb Pc Pe Pf Pg Po Pz Qa Qb Qc Qd) Hv(Et Fp Fr Hq Hr Hu Hw Hx Ii Ij Im Io Ip Iq Is It Iv Jg Jh Ji Jj Jk Jl Jm Jn Jo Jp Jq Jr Jt Lh Li Lj Lu Lv Lw Lx Ly Lz Ma Mb Mc Md Mf Mg Mh Mi Mk Ml Mm Mp Mq Mr Ms Mt Mu Mv Mw Mx My Mz Na Nb Nc Ne Nf Ng Nh Ni Nj Nk Nl Nn No Nq Nr Nt Nu Nv Nw Nx Ny Oe Og Oh Oi Om On Oy Pa Pb Pc Pd Pe Pf Pg Po Qa Qb Qc Qd) Ii(Et Fp Fr Hq Hr Hu Hw Hx Ih Ij Il Im In Io Ip Iq Ir Is It Iv Jh Ji Jj Jl Jm Jn Jo Jp Jq Jr Jt Lh Li Lj Lu Lv Lw Lx Ly Lz Ma Mb Mc Md Mf Mg Mi Mk Ml Mm Mp Mq Mr Ms Mt Mu Mv Mw Mx My Mz Na Nb Nc Ne Nf Ng Nh Ni Nj Nk Nl Nn No Nq Nr Nt Nu Nv Nx Ny Oe Og Oh Oi Om Oy Pa Pb Pc Pe Pf Pg Po Pz Qa Qb Qc Qd) Jj(Et Fp Fr Hq Hr Hu Hw Hx Ij Il Im In Io Ip Iq Is It Iv Jg Jh Ji Jl Jm Jn Jo Jp Jq Jr Jt Lh Li Lj Lu Lv Lw Lx Ly Lz Ma Mb Mc Mf Mg Mh Mi Mk Ml Mm Mp Mq Mr Ms Mt Mu Mv Mw Mx My Mz Na Nb Nc Ne Nf Ng Nh Ni Nj Nk Nl Nn No Nq Nr Nt Nu Nv Nw Nx Ny Oe Og Oh Oi Om On Oy Pa Pb Pc Pd Pe Pf Pg Po Qa Qb Qc Qd) Mh(Et Fp Fr Hq Hr Hu Hw Hx Ij Im In Io Ip Iq Is It Iv Jg Jh Ji Jk Jl Jm Jn Jo Jp Jq Jr Jt Lh Li Lj Lu Lv Lw Lx Ly Lz Ma Mb Mc Mf Mg Mi Mk Ml Mm Mp Mq Mr Ms Mt Mu Mv Mw Mx My Mz Nb Nc Ne Nf Ng Nh Ni Nj Nk Nl Nn No Nq Nr Nt Nu Nv Nx Ny Oe Og Oh Oi Om Oy Pa Pb Pc Pd Pe Pf Pg Po Pz Qa Qb Qc Qd) Na(cO Et Fp Fr Hq Hr Hu Hw Hx Ij Im In Io Ip Iq Ir Is It Iv Jh Ji Jk Jl Jm Jn Jo Jp Jq Jr Jt Lh Li Lj Lu Lv Lx Ly Lz Ma Mb Mc Md Mf Mg Mi Mk Ml Mm Mp Mq Mr Ms Mt Mu Mv Mw Mx My Mz Nb Nc Ne Nf Ng Nh Ni Nj Nk Nl Nn No Nq Nr Nt Nu Nv Nx Ny Oe Og Oh Oi Om Oy Pa Pb Pc Pd Pe Pf Pg Po Qa Qb Qc Qd) Nf(Et Fp Fr Hq Hr Hu Hw Hx Ih Ij Im Io Ip Iq Ir Is It Iv Jh Ji Jk Jl Jm Jn Jo Jp Jq Jr Jt Lh Li Lj Lu Lv Lw Lx Ly Lz Ma Mb Mc Md Mf Mg Mi Mk Ml Mm Mp Mq Mr Ms Mt Mu Mv Mw Mx My Mz Nb Nc Ne Ng Nh Ni Nj Nk Nl Nn No Nq Nr Nt Nu Nv Nx Ny Oe Og Oh Oi Om Oy Pa Pb Pc Pd Pe Pf Pg Po Qa Qb Qc Qd) Oi(Et Fp Fr Hq Hr Hu Hw Hx Ij Ik Im In Io Ip Iq Ir Is It Iv Jg Jh Ji Jk Jl Jm Jn Jo Jp Jq Jr Lh Li Lj Lu Lv Lw Lx Ly Lz Ma Mb Mc Mf Mg Mi Mk Ml Mm Mp Mq Mr Ms Mt Mu Mv Mw Mx My Mz Nb Nc Ne Nh Ni Nj Nk Nl Nn No Nq Nt Nu Nv Nw Nx Ny Oe Og Oh Om On Oy Pa Pb Pc Pd Pe Pf Pg Po Qa Qb Qc Qd) Pa(Et Fp Fr Hq Hr Hu Hw Hx Ij Ik Im In Io Ip Iq Ir Is It Iv Jg Ji Jk Jl Jm Jn Jo Jp Jq Jr Jt Ko Lh Li Lj Lu Lv Lw Lx Ly Lz Ma Mb Mc Mf Mg Mi Mk Ml Mm Mp Mq Mr Ms Mt Mu Mv Mw Mx My Mz Nb Nc Ne Ng Nh Ni Nj Nk Nl Nn No Nq Nr Nt Nu Nv Nx Ny Og Oh Om Oy Pb Pc Pd Pe Pf Pg Po Pz Qa Qb Qc Qd) Pb(cO Et Fp Fr Hq Hr Hu Hw Hx Ij Ik Im Io Ip Iq Is Iv Jg Jh Ji Jk Jl Jm Jn Jo Jp Jq Jr Lh Li Lj Lu Lv Lw Lx Ly Lz Ma Mb Mc Mf Mg Mi Mk Ml Mm Mp Mq Mr Ms Mt Mu Mv Mw Mx My Mz Nb Nc Ne Ng Nh Ni Nj Nk Nl Nn No Nq Nr Nt Nu Nv Nw Nx Ny Oe Og Oh Om On Oy Pe Pf Pg Po Pz Qa Qb Qc Qd) Lx(Et Fp Fr Hq Hr Hu Hw Hx Ih Ij Ik Im Io Ip Iq Ir Is It Iv Jg Ji Jk Jl Jm Jn Jo Jq Jr Jt Lh Li Lj Lu Lv Ly Lz Ma Mb Mc Md Mf Mg Mi Mk Ml Mm Mp Mq Mr Ms Mt Mu Mv Mw Mx My Mz Nb Nc Ne Ng Nh Ni Nj Nk Nl Nn No Nq Nr Nt Nu Nv Nw Nx Ny Og Oh Om Oy Pc Pd Pe Pf Pg Po Pz Qa Qb Qc) Hr(Et Fp Fr Hq Hu Hw Hx Ij Ik Im Io Ip Iq Is Iv Jg Jh Ji Jk Jl Jm Jn Jo Jp Jq Jr Lh Li Lj Lu Lv Lw Ly Lz Ma Mb Mc Mf Mg Mi Mk Ml Mm Mp Mq Mr Ms Mu Mv Mw Mx My Mz Nb Nc Ne Ng Nh Ni Nj Nk Nl Nn No Nq Nr Nt Nu Nv Nw Nx Ny Oe Og Oh Om On Oy Pc Pe Pf Pg Po Pz Qa Qb Qc Qd) Lj(Et Fp Fr Hq Hu Hw Hx Ih Ij Im Io Ip Iq Ir Is It Iv Jh Ji Jk Jl Jm Jn Jo Jp Jq Jr Jt Lh Li Lu Lv Lw Ly Lz Ma Mb Mc Mf Mg Mi Mk Ml Mm Mp Mq Mr Ms Mt Mu Mv Mw Mx My Mz Nb Nc Ne Ng Nh Ni Nj Nk Nl Nn No Nq Nr Nt Nu Nv Nx Ny Oe Og Oh Om Oy Pc Pe Pf Pg Po Qa Qb Qc Qd) Mc(Et Fp Fr Hq Hw Hx Ij Ik Im In Io Ip Iq Ir Is It Iv Jg Ji Jk Jm Jn Jo Jq Jr Jt Lh Lu Lv Lw Ly Lz Ma Mb Md Mf Mg Mi Mk Ml Mm Mp Mq Mr Ms Mt Mu Mv Mw Mx My Mz Nb Nc Ne Ng Nh Ni Nj Nk Nl Nn Nq Nr Nt Nu Nv Nw Nx Ny Og Oh Om On Oy Pc Pd Pe Pf Pg Po Pz Qa Qb Qc) Mr(cO Et Fp Fr Hq Hu Hw Hx Ij Ik Im Io Ip Iq Is It Iv Jg Jh Ji Jk Jl Jm

Figure 13 Continued

Figure 13 Continued

Pg Pz Qc) Li(cO Fr Ij Ik In Io Ir Is It Iv Jg Ji Jk Jo Jr Lv Lw Lz Ma Md Mf Ml Mq Mt Mu Mv Ng Nk Nl Nw Ny On Pc Pd Pg Qc) Oy(Cu Fp Fr Ij Ik Io Is It It Iv Ji Jk Jo Jr Ko Lv Lw Lz Ma Mf Ml Mq Mt Mu Mv Ng Nk Nl Nw Ny On Pc Pg Pz Qb Qc) Jl(Fr Ij Ik Io Is Iv Jg Ji Jk Jo Jr Lv Lw Lz Ma Md Mf Ml Mq Mt Mu Mv Ng Nk Nl Nr Nw Ny Ok On Pc Pd Pg Qc) Qb(Fp Fr Ij Ik Io Is It Iv Jg Ji Jk Jo Jr Lv Lw Lz Ma Mf Ml Mq Mt Mu Mv Ng Nk Nl Nw Ny On Pc Pd Pg Qc) Nv(Fr Ij Ik Io Ir Is It Iv Jg Ji Jk Jo Jr Lv Lw Lz Ma Mf Ml Mq Mu Mv Ng Nk Nl Nr Nw Ny On Pc Pd Pg Qc) Fp(Fr Ij Ik Io Is Iv Jg Ji Jk Jo Jr Lv Lw Lz Ma Mf Ml Mq Mt Mu Mv Ng Nk Nl Nw Ny On Pc Pg Pz Qc) cO(aX cl Cv cW cZ Fn Ij In Io Is It Iu Jo Jr Js Jt Kd Kq Kr Lw Ma Md Ml Mn Mt Nr Ny On Pd Pg Uk) cS(aG aH al aL aM aP aY bB bG bL bN bO bQ bW cG cl cJ cK cV cW cZ dF dG dH dL eF) Jr(Fr Ij Io Is It Iv Jk Jo Lz Ma Mf Ml Mt Mu Mv Nk Nl Nr Ny Pc Pg Qc) Mq(Fr Io Jg Ji Jk Lv Lw Lz Ma Mf Mu Mv Ng Nk Nl Nw Ok On Pc Pg Qc) Ji(Fr Ik Io Jg Jk Lv Lw Lz Ma Mf Mu Mv Ng Nk Nl Nw On Pc Pg Qc) Ko(Af aK An aU bV cB cC Cp Cu Cx dK Fa Fn Jd Jg Ju Kd Ky Uk Up) Lw(Fr Io Jg Jk Lv Lz Ma Mf Mu Mv Ng Nk Nl Nw On Pc Pg Qc) Ny(Fr Ij Io Is It Iv Jo Jt Lz Ma Mf Ml Mt Ng Nk Nr Pc Pg) Jo(Ij In Io Jt Lz Ma Md Mf Ml Mt Ng Nk Nl Nr Pc Pg) Io(Cu Cw Fr Is It Iv Lv Ma Ml Mn Nk Nr Pc Pg) Pc(Fr Jg Jk Lv Ma Ml Mu Mv Nk Nl Nw On Qc) Cu(Fn Ik Ir Is It Iu Iv Iz Kd Ky Uu) Fr(Jg Jk Lv Mf Ml Mu Mv Nk Nw On Qc) Lv(Ik Jg Jk Ma Mu Mv Nk Nw On Qc) Mv(Ik Jg Jk Ml Mu Nw On Pg Qc) Qc(Ij Ik Jg Jk Mu Nw On Pg) Ml(Ij In Is Ma Mf Mt Pg) Mu(Ij Ik Jg Jk Nw On) bN(bG bQ cE cl cW fP) Pg(Is Lz Ma Nk Nl) Is(It Iv Mn) Jg(Jk Nw On) fP(cG cJ Ky) Af(Iu Kd) Mt(In Md) Ij(Jt Nr) Jk(Nw On) Kq(bV cB) FnKy MaJt Mnlv NwOn aYcl bGbV} Gc{Oe(Ad Af Aj Al An Ap Ar As Aw Ax Ba Bb Bc Bg Bn Bo Ch Co Cq Cs Ct Cu Cv Cw Cx Db Dc Dd De Dg Di Dk Dl Ed Ef Et Ex Ez Fp Fr Fw Gl Gp Gz Ha Hb Hc Hf Hq Hr Hu Hv Hw Hx Ib Ic Ih Ii Ij Ik Il Im In Io Ip Iq Ir Is It Iu Iz Jd Jf Jh Jj Jk Jl Jm Jn Jo Jp Jq Jr Js Jt Ju Jy Kc Kd Kf Kn Ko Kp Ks Kx Ky Ld Lh Li Lj Lu Lv Lw Lx Ly Lz Ma Mb Mc Md Me Mf Mg Mh Mi Mj Mk Ml Mn Mp Mq Mr Mt Mv Mw Mx Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Pa Pb Pc Pd Pe Pf Pg Ph Pi Pj Pk Po Pz Qa Qb Qc Qd Qe Qg Qh Qm Qt Qv Qw Qx Rb Rf Rg Ri Sr St Tz Ua Ub Uc Ud Ue Uk Ul Un Uo Ur Ut Uu Uv Vo Vp Vs Vt Vu Vv Wm Tj) My(Ko Ma Nr Rc Ue) Mm(Ao Hc Ou) Cs(Ba Ct) CtEx WmMu} Gd{Hu(Ap As Jt Ke Kj Mt Pj Ue Vs) Mm(Dg Hc Jl Jp Lh My On) OeVt} aJ{dG(aX bG bL bM bN bV cl cO dE dI) cO(cl cS dL) cSdL} Mv{Pd(Ji Nw Ok On) Jl(Jj Jo Jt) Jo(Ok On) Jt(Ok On) EmMm PzJj} Mu{Jj(Jl Mf Mn Pz) Ok(Jo Jt Pd) On(Jo Pd) EmMm OmPd} Mm{Em(Hu Jl Nv) Gn(Ao Hu Nv) Dr(Hu Nv)} Nn{Jt(Jl Ok On) JoOn} Em{Hu(Nm Pj)} Pd{MiOm PzNw} JtOnPg Unconstrained panels with 3 analytes, where 1.0E-6 >= 'model p-value' > 1.0E-7. Contains 2,572 panels of 10,943,034 total panels evaluated. : aA{Ko(aC AD aG AJ AL aM aN Ao AP aQ Ar As aV Aw AX aY aZ Ba Bb BC BG bI bL BN BO bQ bR bU bW cE cF cG CH cJ cL Co CQ cR CS Ct Cv CW cX cY Db Dc Dd DE dF DG dH Di dJ Dk DL Dp dR Ed EF Et Ez Fb FP Fr Fw Fy GL GP gW Ha Hb Hc Hf Hq Hr Hu Hv Hw Hx Ih Ii Ij Ik Il In Io Ip Iq Ir Is It Iu Iv Iz Je Jf Jh Ji Jj Jk Jl Jm Jn Jo Jp Jq Jr Js Jt Jv Jy Kc Ke Kf Kg Ki Kj Kk Kl Kn Kp Kq Kr Ks Kz Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw My Mz Na Nb Nc Nd Ne Nf Ng Nh Ni Nj Nk Nl Nm Nn Nr Ns Nt Nu Nv Nw Nx Ny Oa Oe Of Og Oh Oi Ok Om On Or Ou Ow Oz Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm St To Tr Tv Tz Ua Ub Uc Ud Ue Uf Ug Uh Ul Um Un Uo Ur Us Ut Uu Uv Vo Vp Vs Vt Vu Vv) Cu(An Ao cO Cp cS Cv Dk Dp Ed Et Ez Fa Fb Fp Fy Ha Hb Hc Hf Hq Hr Hu Hv Hw Hx Ib Ih Ii Ij Il Im In Jd Je Jf Jg Jh Ji Jj Jk Jl Jn Jo Jp Jq Jr Js Jt Ju Jv Jy Kc Ke Kf Kg Ki Kj Kk Kl Kn Kp Kq Kr Ks Kz Ld Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm St To Tr Tv Tz Ua Ub Uc Ud Ue Uf Ug Uh Uk Ul Um Un Uo Up Ur Us Ut Uv Vo Vp Vs Vt Vu Vv) cO(AD Af aH al aJ aK aL aM aN Ao aP aQ AS aV aY aZ bB bE bG bI bL BN bO bQ bU bV bX cB cE cJ CQ cR cU Cw Cx cY Dc Dd dF dG dH dI dJ dL dM Fa FP Hr Hv Hx Ii Ik Il Ip Jh Ji Jm Jp Ke Kf Kg Kj Kn Kp Ky Lh Lj Lv Lx Ly Lz Mb Mc Mf Mg Mi Mj Mk Mm Mq Mu Mv Mw Mx My Nb Nc Nd Ne Nf Ng Nh Ni Nk Nl No Ns Nt Nv Nx Oe Oi Ok Oy Pa Pc Pf Ph Pi Pk Po Pz Qa Qb Qc Qe Qx Ra Rb Rj Tr Uc Ud Ue Uo Up Us Ut Uv Vp Vs Vt Vu Vv) Fn(Ad Af An Ap Bb Bc Bo bV bW cB cE Cv Cw Cx Dg dH Dl Ed Et Fa Fb Fp Hv Io Ir Iu Iv Jo Jp Jq Jy Kd Ke Kf Kg Kl Kq Kr Ks Ma Md Mf Mg Mm Mn Mp Mt Ng Nl Nm Ny Oh Ok Om On Ow Oy Pd Pf Pg Pk Pz Qa Qd Qe Rg Rh Tr Tv Uf Uh Uk Up Uv Vo Vt Tj) cS(aC aD aE aF aJ aK AN aO Ap aQ aR aS aU aV aW aX aZ bA bC bE bF bH bI bJ bM bP bR bS bU bV bX bZ cA cB cC cD cF cH cL cM cN cP cQ cR cT cU Cv Cw cX cY dA dB dC dD dE Dg dI dJ dK dM dN dR Et Fa FP gL hB Kd Kq Ky Mp Mt oK Pd Pk) bN(aC aD aG aH al aJ aK aL aM aN aO aP aQ aS aU aV aX aY aZ bB bE bF bI bL bO bP bS bU bV bW bX cB cG cJ cK cQ cR cU cY cZ dC dE dF dG dH dJ dL dM dR eF gL) bG(aC aD aG aH al aJ aK aL aM aN aQ aS aV aX aY aZ bB bE bI bL bO bQ bS bU bW bX cB cE cl cJ cQ cR cU cW cY cZ dC dE dF dG dI dJ dK dL dM dR eF fP gL) cW(aC aG aH aJ aK aL aM aN aO aP aQ aS aW aX aY aZ bI bL bO bP bQ bS bU bV bW bX cB cE cG cJ cK cl cQ cR cU cZ dC dE dF dG dH dL dM fP) Kd(AN As Bb Bu bV cB Cw Cx Dg Ed Et Fa Fb Hv Hx Io Iu Iv Jp Kl Kq Kr Ks Ky Ma Mf Mm Mn Ok On Oy Pa Pd Pk Qd Rh Tr Uh Uk Up Ur Vo) cl(aC aD aE aH aI aJ aK aL aM aN aP aQ aR aS aX aZ bB bE bF bI bL bO bQ bS bV bW bX cE cG cJ cQ cV cZ dA dE dF dG dH dL dN eF fP) aY(aC aG aH aJ aK aL aM aN aP aQ aS aW aX aY aZ bB bE bI bL bO bQ bS bU bV bX cB cE cJ cN cQ cR cU cZ dC dE dF dG dH dL dM fP) Ky(Af aK As Bb Bn bV cB cC Cv Cw Et Fa Fb Fy Io Ip Iq Ir Is It Iu Iv Jq Kq Kr Ks Md Mm Mp Mt Pd Rb Tr Ue Uk Uv Vt) Af(Ed Et Fa Fb Io Iq Ir Is It Iv Kq Kr Lx Ma Md Mf Mn Mp Mt Nn Nr Oh On Pd Pf Pg Pk Qb Qd Qe Tr Tv Uk Uo Uv) Qd(bV Fp Hu Hx Jh Jl Jp Jq Li Lu Lx Ly Mc Mk Mm Mp Ms My Mz Nb Nj Nm No Nq Nt Nu Nv Oe Of Og Om Oy Pa Uk) Jh(Fp Hu Hx Jl Jp Jq Li Lu Lx Ly Mc Mk Mm Mp Ms My Mz Nh Nj No Nq Nt Nu Nv Oe Og Om Oy Pa Qb) Oe(Fp Hu Hx Jl Jp Jq Li Lu Lx Ly Mc Mk Mm Mp Ms My Mz Nb Nj No Nq Nt Nu Nv Og Om Oy Pa Qb) fP(aG aH aK aL aM aN aO aQ aU aW bB bI bL bM bO bQ bV bW bZ cB cF cQ dC dF dG dH dL gW) Kq(aK AN Ao aU bW cC cJ Fa Io Ip Iq Ir Is It Iu Iv Iz Jd Kp Nn No Nq Oi Oy Pk Uk Up) Jp(bV Fp Hu Jl Jq Li Lu Lx Ly Mc Mk Mm Mp Ms My Mz Nb Nj No Nq Nt Nu Nv Og Om Oy Uk) dG(aC aK aL aM aN aP aQ aS aX aZ bE bL bQ bS bU bV bX cE cJ cN cQ cR cU cZ dE dH dM) Li(bV Fp Hu Hx Jl Jq Lu Ly Mc Mk Mm Mp Ms My Mz Nb Nh Nj No Nq Nt Nu Nv Og Oy Qb) Fa(An Bb Bo bV cB Fb Ha Io Ip Iq Ir Is It Iu Iv Kr Mm Mn Oy Pk Po Qg Tr Uk Up) No(Fp Hu Hx Jl Jq Lu Ly Mc Mk Mm Mp Ms My Mz Nb Nj Nq Nt Nu Nv Og Oy Qb) Iu(Ad An Ap As Bb Bc Bo bW cE cG cJ Cv Cw Cx dF Dg Fb Kr Pk Qg Tr Uh Uk) Mp(aN As Bb Bo bV Cx Hu Jl Jq Lu Ly Mm Ms My Nj Nq Nt Nu Nv Qb Up) cE(aL aM aN aX bE bL bO bV bX bZ cJ cQ cR cU cZ dL dM Io Ir Is Iv) Hu(Fp Jl Jq Lu Ly Mc Mk Mm Ms My Mz Nb Nj Nq Nt Nu Nv Og Qb) Cw(Cp Fb Hq Ip Iq Ir Is It Iv Kr Mc Mf Mm Mn Mv Oy Pa Pd) Jl(Fp Lu Ly Mc Mk Mm Ms My Mz Nh Nj Nq Nt Nu Nv Og Oy Qb) bV(aP bL bQ cK cZ dH dL eF Et hB Ma Mt On Pd Pg Pk Qe Tr) Uk(Bb Bo Ed Et Fb Io Kr Mm Mn Oy Pd Qe Qg Tr Uh Up Ur) Nj(Fp Hx Jq Lu Ly Mk Mm Ms My Mz Nq Nu Nv Og Oy Qb) Bo(Cv Et Iq Ir Is It Iv Jo Jq Kr Mn Mt On Pd) Ly(Fp Hx Jq Lu Mk Mm Ms My Mz Nu Nv Og Oy Qb) bQ(aM aN aQ aX cJ cR cU cZ dI dL dR gL) dH(aH aK aL aM aX bB bE cJ cZ dI dL Io) My(Fp Hx Jq Lu Mk Mm Ms Nu Nv Oy Qb) Tr(cB Iq Ir It Iv Jd Jq Kz Mn Up Tj) Nv(Fp Hx Lu Mk Mm Ms Nu Og Oy Qb) Io(Ad As Ax Bc cG cJ CV dF) aX(aC aP bL bW cG cJ cQ dL eF) cZ(aC aN aP bL bS bW bX cJ cQ) Bb(Iq Ir Is It Iv Mt Oy Pd) Lu(Hx Jq Mk Mm Ms Mz Nu Qb) Up(As Et Jq Kr Mt On Pd Qe) dL(aC aJ aM aN bL bS bX cQ) Iv(Ap bW cG cJ Dg Fb Uh) Mm(Jq Mk

Figure 13 Continued

Ms Nt Nu Pk) Ir(Ap bW cG cJ Dg Fb) Et(AN Ao As Jd) It(Ap bW cJ Dg Fb) Kr(cB Cx Fb Oy Pk) Cp(Ad Cv Mt On) Gc(Ax Cs Em Of) Ms(Hx Mk Nu Qb) Jq(Mz Nb Nu Tv) As(Cv Ma Mn) Iq(Ap cJ Dg) Is(Ap Dg Fb) An(Cv Mt) Ma(Ba kS) aC(aL bE) aM(aN bL) bW(oH Pk) bX(cB cJ) AoOn CvMn MkQb MvjP aKbL aLaN bScJ cBeF} Gc{Oe(Dp Dr Em Fa Fb Fy Gd Gn Id Jv Ke Kg Ki Kj Kl Kq Kz Qu Qz Ra Rc Rj Rm Ss Tn To Tr Tt Tv Uf Ug Uh Um Up Us) My(Ad Al Ap Ar Bb Bo Co Ct Cw Dg Et Ii Jt Ke Kx Lx Mt Mu Nm No Om Pd Pe Pf Pg Pj Po Rh Uh Uv) Hc(Ad Cw Dg Et Iv Jt Kg Ma Mg Na Oz Pc Pd Rh Ub Ue Wm) Mm(Cp Ef Fw Ii Iz Jg Ji Mu Mv Mx Nn Nv On) Mu(Ba Bo Ct Em Hr Ly Mk Of Oi Rb) Cs(Ao Ar As Cp Dk Ef Fr) Hu(Dr Em Fy Gd Gn Ow) Ct(Ax Jl Mw Mx Nb) Wm(Ib Jl Mw Qy) Ex(Ao As Cp Ef) Ax(As Ba Ef) Ib(Me Ou Rb) Qy(Ly Me Rb) Em(Ef Fr) Of(Jo Nb) LyMw MkJl OuVt} Jj{Mu(Et Fr Hv Hx In Io Ip Iq Ir Is It Iu Iv Jg Jk Jm Jo Jr Js Jt Lv Ma Mc Me Mg Mi Mk Ml Mm Mr Mv Mx Nc Ne Ng Nk Nl Nm Nn Nr Nu Nw Nx Ny Oh Ok Om On Pa Pd Qb Qc) Mv(Ih Ik Il In Io Ip Iq Ir Is It Iu Iv Jk Jo Js Jt Lj Lv Ma Me Mf Mg Mi Mk Ml Mn Mr Mx Ne Ng Nk Nl Nm Nn Nr Nu Nw Nx Ny Oh Ok On Pa Pd Qc) Jl(Ir Is Iu Jg Jk Jt Lv Mf Mn Nl Nn Nx Oh Ok Pd Pf Pz Qb Qc) On(Iu Jt Mf Mn Nn Pd Pf Pg Pz) Nn(Et Jt Ma Mf Nm Pz) Fr(Mf Mn Pz) Jk(Jt Mn Pz) MiHq PzJg OmPd} aJ{dG(aC aD aE aF aG aH aI aK AL aM AN aO aP aQ aR aS aU aV AW aY aZ BA bB bC bE bF bH bI bJ bO bP bQ bR bS bU bW bX bZ cA cB cC cD cE cF cG cH cJ cK cL cM cN CP CQ cR cT cU cV cW cX cY cZ dA dB dC DD dF dH dJ dK dL dM dN dF eM fP Fw Iu Pk) dL(aC aN aX bG bL bN bQ bS bV bX cE cI cK cW dE dH dK) cS(bG bL bN bO bW cE cI cJ cK cW dH) bN(bG bL cE cI cO cW cZ dH) cO(aD aX aZ bG bM cW cZ) bG(aX bA bV cI cT) cI(aX bL bM) aXdH} Jo{Mu(Fr Ip Ir Is Ji Jl Jq Lv Mf Mi Mk Mr Mv Nk Nn Nr Nw Om Pa Pe) On(Fr Ik Ir Is Iu Iv Jl Jq Jt Mn Mx Nl Nx Pd Pg Pz) Mv(Ir Is Ji Lv Mi Mk Mr Mx Nk Nn Nw Om) Ok(Fr Is Jg Jk Jl Nn Pd) Nn(Ji Jl Lv Mi Mn) Jl(Fr Ji Jq Om) Fr(Is Lv) Tr(Iz Nq) EmHu MdOm MiHq MlNw} Mm{Gd(Ao Ap Ba Cp Cu Dl Ef Is Iz Jg Ji Mv Nn Nw Oe Ok Ou Po Ua Uu) Em(Ao Ap Ba Fr Hc Iz Jp Lh Li Lx Mw My Nn Oe On Po Qy Ua) Dr(Ao Ba Hc Iz Jl Mv My Oe) Gn(Ef Hc Ib Iz My Oe On Ou) JhfR} Pd{On(Fr In Ir Is Iu Jl Jt Mi Mn Mx Mz Ne Nl Nn Nt Nu Om Pg Po Pz) Ok(Fr Jk Jl Jt Mi Nn Om) Om(Fr Jl Md Mv Mx My) Mi(Fr Hq Mu Mv Nw) Mu(Ji Jl Jq Nw) Mv(Jl Lv Lx) Nw(In Js Ml) Gd(Hc Hu) Jl(Ji Jq) FrPz NqKo} Jt{On(Fr In Ir Is Iu Iv Jg Ji Jl Jq Mf Mu Mx My Nl Oh Oy Qa) Jl(Fr Is Jg Ji Jq Mu Nv Ok) Nn(Fr Is Ji Mn Mu Nw) Is(Fr Mu Mv Ok) Em(Hu Mu) Ji(Mu Mv) Nw(In Ml) Ok(Fr Jg) MiHq} Mu{Mg(Fr Jg Mi Mv Nw Ok On) Pz(Fr Jl Nn Nw Ok On) In(Is Jl Mi Nw On) Em(Cw Et Nm) Uk(Kq Ny Pg) Md(Ko Wm) ExQv NmOk NnMn MiHq MvNg IbUt IsJm IuJl} Gd{Hu(Ad Ar Bb Co Dg Et Ij Iu Jd Ko Ma Mg On Rh Ub Uc Uh) Hc(Ap Bb Co Ij Mg) Oe(Pj Qw Rh) AoPj UaJf} Mv{Mg(Ji Jl Nw Ok On) In(Is Jl Mi Nw On) Ng(Jg Jl Nk On) Pz(Jl Nw Ok On) NmOk NnMn NrkO MiHq IuJl} Nn{Mn(Fr Jl Mi Ok On) Pz(Fr Jl Ok On) Nm(Jl On) InJl} cO{aP(cI cW Et Fn Kr Tr Uk) Uk(bA cT) BacS} Pz{Fr(Is Jl Mg) Nw(In Ml) MiHq NgJg OnPg} Hu{Cw(Dr Em Gn) Pj(Dr Gn)} Mn{FrMg NqTr OnPg} Em{PoPj NmHc} Mi{Hq(Iu Lu)} In{Jl(Jq Om)} CwJhfR TiRfPk NmOnPg rBqZlL

Unconstrained panels with 3 analytes, where 1.0E-5 >= 'model p-value' > 1.0E-6. Contains 14,317 panels of 10,943,034 total panels evaluated. : aA{Kq(aC AD aE aF aG aH aI AJ AL aM aO AP aQ AR AS aV AW AX aY aZ BA BB BC bE bF BG bH bI bJ bL bM BN BO bP bQ bR bS bU bX bZ cA cD cE cF cG CH cI cK cL cM cN Co CP CQ cR Cs CT cU CV CW CX cY cZ dA DB DC DD DE dF DG dH DI dJ DK DL dM dN Dp Ed EF Et Ez Fb FP FR Fw Fy Gc GL GP gW Ha Hb Hc Hf Hq Hr Hu Hv Hw Hx Ib Ih Ii Ij Ik Il Im In Je Jf Jg Jh Ji Jj Jk Jl Jm Jn Jo Jp Jq Jr Js Jt Ju Jv Jy Kc Ke Kf Kg Ki Kj Kk Kl Kn Kr Ks Kz Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nr Ns Nt Nu Nv Nw Nx Ny Oa Oe Of Og Oh Ok Om On Or Ou Ow Oz Pa Pb Pc Pd Pe Pf Pg Ph Pi Pj Po Pz Qa Qb Qc Qd Qe Qg Qh Ql Qm Qn Qt Qu Qv Qw Qx Qy Qz Ra Rb Rc Rf Rg Rh Ri Rj Rm St Tr Tv Tz Ua Ub Uc Ud Ue Uf Ug Uh Ul Um Un Uo Ur Us Ut Uu Uv Vo Vp Vs Vt Vu Vv Wm Tj) Kr(Ad aG Aj aK Al AN Ao Ap aQ Ar As aU aV Aw AX aY aZ Ba Bb Bc Bg bI bJ Bn bR bU bV bW cC cE cF cG Ch cJ Co Cp Cq CS Ct Cv cY Db Dc Dd De dF Dg dH Di dJ DK Dl Dp dR Ed EF Et Ex Ez FP Fr Fw Fy GL Gp gW Gz Ha Hb Hc Hf Hq Hr Hu Hv Hw Hx Ih Ii Ij Ik Il Im In Io Ip Iq Ir Is It Iv Iz Jd Je Jf Jg Jh Ji Jj Jk Jl Jm Jn Jo Jp Jq Jr Js Jt Ju Jv Jy Kc Ke Kf Kg Ki Kj Kk Kl Kn Kp Ks Kz Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oz Pa Pb Pc Pd Pe Pf Pg Ph Pi Pj Po Pz Qa Qb Qc Qd Qe Qg Qh Ql Qm Qn Qt Qu Qv Qw Qx Qy Qz Ra Rb Rc Rf Rg Rh Ri Rj Rm St Tr Tv Tz Ua Ub Uc Ud Ue Uf Ug Uh Ul Um Un Uo Ur Us Ut Uu Uv Vo Vp Vs Vt Vu Vv Wm Tj) Uk(AD aG Aj aK Al aM AN Ao Ap aQ Ar As aU aV Aw AX aY Ba Bc Bg bl bM BN bO bQ bR bU bV bW cB cC cE cF cG Ch cJ Co Cp Cq CS Ct Cv CW Cx cY Db Dc Dd De dF DG dH DI dJ DK DL dN Dp dR EF Ez FP Fr Fw Fy GL Gp Ha Hb Hc Hf Hq Hr Hu Hv Hw Hx Ih Ii Ij Ik Il Im In Ip Iq Ir Is It Iv Iz Jd Je Jf Jg Jh Ji Jj Jk Jl Jm Jn Jo Jq Jr Js Jt Ju Jv Jy Kc Ke Kf Kg Ki Kj Kk Kl Kn Kp Ks Kz Lh Li Lj Lu Lv Lw Lx Ly Lz Ma Mb Mc Md Me Mf Mg Mh Mi Mj Mk Ml Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om ON Or Ou Ow Oz Pa Pb Pc Pe Pf Pg Ph Pi Pj Pk Po Pz Qa Qb Qc Qh Ql Qm Qn Qt Qu Qv Qw Qx Qy Qz Ra Rb Rc Rf Rg Rh Ri Rj Rm St Tn Tv Tz Ua Ub Uc Ud Ue Uf Ug Ul Um Un Uo Us Ut Uu Uv Vo Vp Vs Vt Vu Vv Wm Tj) Kd(aC AD aG Aj aK Al Ao Ap aQ Ar aS aU aV AW AX aY aZ Ba BC Bg bI bJ bM BN bO bQ bR bU bW bZ cA cC cE cF cG Ch cJ cL Co Cp CQ cR Cs Ct CV cW cX cY Db Dc Dd DE dF dG dH DI dJ DK Dl dN Dp EF Ez FP Fr Fw Fy GL Gp Ha Hb Hc Hf Hq Hr Hu Hw Ih Ii Ij Ik Il Im In Ip Iq Ir Is It Iz Jd Je Jf Jg Jh Ji Jj Jk Jl Jm Jn Jo Jq Jr Js Jt Ju Jv Jy Kc Ke Kf Kg Ki Kj Kk Kn Kp Kz Ld Lh Li Lj Lu Lv Lw Lx Ly Lz Mb Mc Md Me Mg Mh Mi Mj Mk Ml Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Om Or Ou Ow Oz Pb Pc Pe Pf Pg Ph Pi Pj Po Pz Qa Qb Qc Qe Qg Qh Ql Qm Qn Qt Qu Qv Qw Qx Qy Qz Ra Rb Rc Rf Rg Ri Rj Rm St Tn Tv Tz Ua Ub Uc Ud Ue Uf Ug Ul Um Un Uo Us Ut Uu Uv Vp Vs Vt Vu Vv Wm Tj) Ky(AD Aj Al aM AN Ao Ap aQ Ar aU aV Aw AX aY Ba Bc Bg bI bM BO bU bW cE cF cG Ch cJ Co Cp CQ cR Cs Ct cW Cx cY Db Dc Dd De dF DG dH Dl dJ DK DL dN Dp dR Ed EF Ez Fp Fr Fw GL Gp Ha Hb Hc Hf Hq Hr Hu Hv Hw Hx Ih Ii Ij Ik Il Im In Iz Jd Je Jf Jg Jh Ji Jj Jk Jl Jm Jn Jo Jp Jr Js Jt Ju Jv Jy Kc Ke Kf Kg Ki Kj Kk Kl Kn Kp kS Kz Lh Li Lj Lu Lv Lw Lx Ly Lz Ma Mb Mc Me Mf Mg Mh Mi Mj Mk Ml Mn Mq Mr Ms Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Oz Pa Pb Pc Pe Pf Pg Ph Pi Pj Pk Po Pz Qa Qb Qc Qd Qe Qg Qh Ql Qm Qn Qt Qu Qv Qw Qx Qy Qz Ra Rc Rf Rg Rh Ri Rj Rm St Tn To Tt Tv Tz Ua Ub Uc Ud Uf Ug Uh Ul Um Un Uo Up Ur Us Ut Uu Vo Vp Vs Vu Vv Wm Tj Ti) Fa(Ad Aj aK Al aN Ao Ap Ar As aU Aw Ax Ba Bc Bg Bn bW cC cE cF Ch cJ Co Cp Cq Cs Ct Cv Cw Cx Db Dc Dd De Dg dH Di Dk Dl Dp Ed Ef Et Ez FP Fr Fw Fy GL Gp Hb Hc Hf Hq Hr Hu Hv Hw Hx Ih Ii Ij Ik Il Im In Iz Jd Je Jf Jg Jh Ji Jj Jk Jl Jm Jn Jo Jp Jq Jr Js Jt Ju Jv Jy Kc Ke Kf Kg Ki Kj Kk Kl Kn Kp Ks Kz Lh Li Lj Lu Lv Lw Lx Ly Lz Ma Mb Mc Md Me Mf Mg Mh Mi Mj Mk Ml Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oz Pa Pb Pc Pd Pe Pf Pg Ph Pi Pj Pz Qa Qb Qc Qd Qe Qh Ql Qm Qn Qt Qu Qv Qw Qx Qy Qz Ra Rb Rc Rf Rg Rh Ri Rj Rm St Tn To Tt Tv Tz Ua Ub Uc Ud Ue Uf Ug Uh Ul Um Un Uo Ur Us Ut Uu Uv Vo Vp Vs Vt Vu Vv Wm Tj) Fn(aC aD aE aG aH Aj aK AL aM aN Ao aQ Ar As aU aV AW AX aY aZ Ba bB bF Bg bI bJ bL bM BN bO bQ bR bU bZ cA cC cF cG Ch cJ cL Co Cp CQ CS Ct cW cX cY Db Dc Dd DE dF dG DI dJ DK dL dN Dp dR EF Ez fP Fr Fw Fy GL GP Ha Hb Hc Hf Hq Hr Hu Hw Hx iA Ih Ii Ij Ik Il Im In Ip Iq Is It Iz Jd Je Jf Jg Jh Ji Jj Jk Jl Jm Jn Jr Js Jt Ju Jv Kc Ki Kj

Figure 13 Continued dR gL Iq It Jo Jt Kg Li Lx Ma Md Nr Oh Ok Om Pf Pg Qa Qd Qe Tv Uv) aL(aD aE aF aG aI aJ aO aP aQ aR aS aU aV aW aZ bA bC bF bH bI bJ bM bP bQ bR bS bU bX bZ cA cC cD cF cG cH cK cL cM cN cP cR cT cU cV cX cY cZ dA dB dC dD dE dI dJ dK dM dN gL) Ma(aD Aj Al An Ao Ap aQ Ar aU Aw aY aZ Bc Bg bI BN bU bZ cC cG Ch Co Cp Cq Cs Ct cW Db Dc De Dl dJ DK Dl dN Ed Ez Gc Jd Jy Ke Kg Kn Ks Pi Qg Qw Qy Rb Rh Ue Uv Vt Tj) cZ(aD aE aF aG aI aJ An aO aQ aR aS aU aV aW aZ bA bC bF bH bI bJ bM bP bR bU bZ cA cC cD cF cG cH cK cL cM cN cP cR cT CU cV cX cY dA dB dC dD dE dI dJ dK dM dN fR gL Ko) Iq(aG Aj Al An Ao Ar aU Aw Ba Bc Bg Bn bZ cC cG Ch Co Cp Cq Cs Ct cV Db Dc De Di Dk Dl Ed Ef Ex Fy Gc Ha Hb Jy Ke Kf Kg Kj Kl Ks Ow Qg Qw Rg Rh Uc Ue Uf Uo Ur Uv Vo Vt Tj) Qe(Aj Al An Ao Ap aQ Ar aU Aw aZ Ba Bc Bg Bn cC Co Cp Cq Cs Ct cY Dc De dJ DK Dl Dp Ef Ez Fw gL Ha Jd jK Ju Jy Kg Kl Ks Qg Qh qU Qw Qy Rb Rf Rg Rh Tv Ue Uo Uv Vo Vt Tj) bQ(aC aD aE aF aG aI aJ aO aP aR aS aU aV aW aZ bA bC bF bH bI bJ bM bP bR bS bU bX bZ cA cC cD cF cG cH cK cL cM cN cP cT cV cX cY dA dB dC dD dE dJ dK dM dN gP gW kS) Ko(Aa aE aF aI aO aR aS aW bA bF bH bJ bM bP bS bX bZ cA cD cI cK cM cN cP cT cU cV dA dB dC dD dI dM dN hB hG iA Ib Id iJ iO iP kS Kx Ld nY oH oK oN pF Tn To Tt tF) It(aG Aj Al An Ao Ar Aw Ba Bc Bg Bn bZ cC cG Ch Co Cp Cq Cs Ct cV Db Dc De Di Dk Dl Ed Ef Fy Ha Hb Jy Ke Kg Kl Ks Kz Ow Qg Qw Rg Rh Uc Uc Uf Ur Uv Vo Vt Wm Tj) An(Al aY aZ Cq Hw Ii Ij In Ji Jn Jo Jp Jr Js Jt Ke Lh Lj Lw Lx Md Mf Mj Ml Mq Mr Mz Na Nb Nm Nn No Nr Nx Ny Oh Ok Om Oy Pb Pc Pf Pg Po Pz Qa Qb Qd Tv Uv) Ap(Ao aY BN Cq Cu Dc Ed Hw Ii Ij In Ip Jn Jo Jr Js Jt Lw Lx Md Mf Mi Mj Ml Mq Mr Mz Na Nb Nf Nm Nn No Nr Nx Ny Oh Oi Ok Om Oy Pb Pe Pf Pg Po Qa Qd Tj) Gc(Ed Ex Hc Hf Hq Hr Hv Hw Ib Ic Ii Ik Iz Jh Jk Jl Kc Kp Mg Mk Ms Mu Mv Mw My Nb Nc Nd Nc Nf Nn Nw Og Oi Ou Ow Oy Oz Pb Pc Qz Ri Ua Um Ur Uu Wm Tj) aY(aD aE aF aI aO aR aU aV bA bC bF bH bJ bM bP bR bZ cA cC cD cF cG cH cK cL cM cP cT Cu cV cX cY dA dB dD dI dJ dK dN dR gL gP kS oH) Mf(aU Bc Bg Bn cC cG Co Cp Cq Cs Dc dJ Dl dR Ed Fy gL Hb jG Jy Ke Kf Kg Kl Kn Kp KS Pi Qg Rb Rh Tv Uc Ue Uo Uv Vo Vt Vv Wm Tj) aQ(aC aD aE aG aI aJ aO aP aR aS aU aV aW aZ bA bF bI bM bP bS bU bX bZ cD cG cK cL cR cT cV cX cY dA dC dE dI dM dN iP kS oN Qd) bN(aE aF Al aR aW bA bC bH bJ bM bR bZ cA cC cD cF cH cL cM cN cP cT Cu cV cX dA dB dD dI dK dN gP gW iA iJ iP kR kS Ny oH oK oN) Md(Aj Al Ao Ar aU Aw Ba Bc Bg Bn bU cC cG Co Cp Cs Ct Dc dI dJ Dl Ed gL Hb Jy Ke Kg Kl Ks Ow Qg Rg Rh Ue Uf Ur Uv Vo Vt Wm Tj) Pg(Aj Al Ao Ar aU Aw Ba Bc Bg Bn bU cC Ch Co Cp Cq Cs Ct Db Dc De Dl dJ Dk Dl Ed Fy gL Ha Jd Jy Kl Ks Qg Rh Ue Uf Uo Ur Vo) cI(aF aG aO aU aV aW bA bC bH bJ bM bP bR bU bZ cA cC cD cF cH cK cL cM cN cP cR cT cU cX cY dB dC dD dI dJ dK dM dR gL gP gW) Oh(Aj Al Ao Ar aU Aw Ba Bc Bg Bn cC Ch Co Cp Cq Cs Ct Db Dc De Di dJ DK Dl Ed Ef gL Ha Jd Jy Kl Ks Qg Rh Tv Ue Uo Vo Tj) Ok(Al Ao Aw Ba Bc Bg Bn Ch Co Cp Cq Cs Ct Db Dc Di dJ DK Ed Ez Ha Iz Jd Je Jy Kg Kp Kz Pj Qg Qy Tn To Tv Ue Uo Uu Uv Tj) Oy(Al Bc Bg bI Bn Co Cp Cq Cs Ct Dc Dk Dl Fw Fy Ke Kf Kg Kj Kl Kn Kp Ks Pi Qx Rb Rj Rm Tv Uc Ue Us Ut Uv Vp Vs Vt Vu Vv Tj) aI(aC aD aE aG aJ aO aP aR aS aV aW aZ bA bF bI bM bP bS bU bX cD cF cG cK cL cR cT cU cV cW cX cY dA dC dE dI dJ dM dN fR) bX(aC aD aG aJ aO aP aR aS aU aV aW aZ bA bF bI bJ bM bS bU bZ cA cF cG cK cL cR cT cU cV cY dC dD dE dI dJ dM dN dR gL) cW(aD aE aF aR aU aV bA bC bF bH bJ bM bR bZ cA cC cF cH cM cN cP cT cV cX cY dA dB dD dI dJ dK dN dR gL gP gW iP kS oH) Qd(Al Ao aU aZ Ba Bc bI Bn cC Co Cp Cq Cs Ct cY Dc dJ DK Dp Ed Ef Ez Jd Jy Kg Qg Qw Qy Rf Rg Rh Ue Uo Uv Vt Tj) bG(aE aF aO aP aR aU aW bA bC bF bH bJ bM bP bR bZ cA cC cD cF cG cH cK cL cM cN cP cT cV cX dA dB dD dN gP gW) Nr(aG Al Ao Ar aU Aw Ba Bc Bg Bn bU cC cG Co Cp Cs Ct Dc dJ Dk Dl Ed gL Ha Jy Ke Kl Ks Qg Qw Rh Uf Ur Vo Wm) aP(aC aD aG aJ aO aS aU aV aW aZ bC bI bJ bS bU cA cD cG cL cN cR cU cV cX cY dC dE dI dJ dM dN dR gL gW) Cu(Aj Al Ar Aw aZ Ba Bc Bg Bn Ch Co Cq Cs Ct Db Dc De Di Dl Ef Fr Gl Ic Id Kx Sr Ss Tn Tt Wm Tj) Ke(Ao Cp Ed Ez Hx Ih Ip Iz Jd Jg Ju Jy Kg Kl Kp Ks Lu Lv Mr Mv Mx My Nl Nn No Nq Oi Pa Tv Uo Tj) aD(aC aG aJ aO aS aU aV aW aZ bC bF bI bP bS bU bZ cD cG cK cL cR cU cV cX cY dC dE dJ dM dN gL) cG(aC aE aG aJ aS aV aW aZ bA bC bI bS bU cD cK cN cR cT cU cX cY dC dE dI dJ dM Ip kS Mr Nn) bS(aC aG aJ aO aS aU aV aW aZ bI bJ bR bU cA cF cR cU cV cY dC dE dI dJ dM dN dR eM gL) Bc(Ed Ii In Ip Jo Jp Js Jt Lj Lw Lx Ml Mr Mz Nl Nm Nn Ny Oi Om Pa Pc Pe Pf Po Pz Qa) Tv(aU bU cC cF gL Ha Ii Jm Jo Jp Kl Ks Mr Mx Nm Nq Nx Om Pz Qg Qw Qy Rh Ul Ur Vo Tj) Ed(aU Bn cC Dl Fy Hb Ip Jo Jp Kg Kl Ks Mg Nm Om Pf Pz Rb Rh Uc Ue Uf Uv Vo Vt) Pf(Al Ao aU Aw Ba Bn cC Co Cp Cs Ct Dc dI dJ dK Dl Ha Jy Kl Ks Qg Rh Vo Tj) Dl(Ii Ik In Ip Jd Jo Js Lw Lx Ml Mr Mx Mz Nd Nh Nl Nn Ny Oi Om Pa Pe) Ip(Bg Bn Co Cp Cq Cs cV Dc Ex Fy Kf Kg Kj Kl Ks Uc Ue Uf Uv Vt Tj) Jp(Al Ao Ba Bn cC Co Cp Cq Cs Dc dJ Dk Jd Jy Kg Rb Uc Ue Uo Uv Tj) cR(aC aG aJ aO aR aS aV aZ bF bI bU bZ cK cL cT cV cX cY dC dE dN) Kl(Ao Bn cC In Iz Jd Kg Kn Lw Ml Mr Nq Oi Om Pe Pi Uu Uv Tj) Ct(Ii In Jo Js Jt Kg Lw Lx Mg Ml Mr Mz Nm Nn Nx Om Qa) Uv(Fy Jd Jy Ks Mx Nl Pa Pz Qg Rh Uf Uo Ur Us Vo Vt Tj) Dc(Hv Hw Jm Jo Me Mv Mx Nh Nk Nl Nm Ns Ny Pa Pc Pz) Co(Ik Jo Jt Lw Lx Mb Ml Mq Mr Mv Nn Oi Om Pc) Tj(Fy Jo Jy Nm Om Pa Pz Qg Rh Tn Ue Uf Vo) aJ(aC aG aO aS aZ bI bM cT cV dC dE dN gL) Ks(Bn Jd Jm Jy Kg Lw Lx Ml Nl Oi Om Uo) aZ(aC aG Al aO aR aS aV bI cY dE dI dN) Cp(Cq Ii Jo Jt Lx Nn Ny Om Pa Pz Uc) Bn(Lj Lx Nl Nm Nn Ns Ny Pa Pz) Qg(Jo Kg Om Qa Qb Uc Ue Uo Vt) Jy(Fy Ii Jo Kg Mg Nx Om Pz Vt) aU(Jt Li Lx Nn No Ny Qa Qb Uo) bI(aC aG aV cT dE dM dR gL Ny) cC(Ez Kz Ld Mr Nn Ny Ow Qb Uo) Ex(Je Mr Mu Ne Oe Oi Ou Ua) Uf(Ez gW Jd Ml Nn Nq Oi Uo) aS(aC aG aO cK cT dC dE dN) Ao(Al Jo Jt Nn Nv Om Pz) Cs(Jo Mg Mx Ny Om Pa Pz) dN(aG cU dE dM gL kS oH) Ue(Lj Mv Nl Pz Qw Rg) dJ(dE Ez Li Lx Nn Ny) gL(Lw Ml Nn Om Ow Qx) Aa(Jg Jk Me Mk Pz) Cq(Nl Nm Ny Pa Pz) Fy(Hx Lv Ow Qx Rh) Uc(Hv Mv Mx Pa Ur) Jo(Ar Aw Jd Uo Ur) aG(aE aR dE dI dM) bU(bF bR cK cL dA) kS(hC iA iP oK oN) Om(Al Aw Jd Je) Lx(Ba dK Vo) Kg(Pa Pz Ur) Vt(Oi Pa Uo) oH(bM oK oN) aV(cK dA) cY(cK dE) dR(bM dA) gW(iA iP) oN(aO bZ) EzHb MqQw MwjP IbUt IzPz KfPa RhUo NycF cVfR dEdI} Gc{My(Af Ao As Aw Ax Ba Bc Ch Cp Cs Cu Cv Cx Dd De Di Dl Ed Ef Ez Fn Fp Fw Gl Gp Hb Hc Hf Hr Hu Hv Hw Ib Ij Ik Il Im Io Ip Ir Is Iu Iv Iz Jd Jh Ji Jj Jk Jl Jm Jn Jo Jp Kd Kg Kk Kl Kn Kq Kr Ky Ld Lh Li Lu Ly Lz Mb Me Mf Mg Mh Mi Mj Mk Ml Mn Mq Mr Ms Mv Mw Mx Mz Na Nb Nc Nd Ne Nf Ng Ni Nj Nk Nl Nn Nq Ns Nt Nw Nx Of Og Oh Oi Ok On Or Ou Ow Oy Oz Pb Pc Pi Pk Pz Qa Qd Qe Qg Qm Qv Qx Qy Rb Rg Ri Tn Tr Tz Ua Ub Uf Un Ur Vo Vp Vq Vs Vt Wm Tj) Hc(Af Aj Al Ap Ar As Ba Bb Bc Bo Ch Co Cs Ct Cu Cv Cx Dd De Dp Ez Fb Fn Fp Fr Fw Gd Gp Ha Hb Hf Hr Hv Hx Ib Ic Ih Ii Ij Il Ip Iq Jd Je Jf Jl Jn Jo Jy Kd Ke Kf Kj Kk Kl Ko Kp Kq Kr Kx Ld Lj Lu Lx Ly Me Mf Mi Mk Ml Mn Mr Ms Mt Mu Mv Mw Mx Nb Nc Ne Nf Ng Ni Nl Nm Nn No Nr Nu Nv Nw Oa Of Oi Om Or Ou Ow Oy Pb Pe Pf Pg Pj Pk Po Pz Qg Ql Qm Qt Qu Qv Qy Rb Rc Rf Ri Ss Tr Tz Ua Uc Ud Uf Uh Uk Uv Vo Vp Vt Vv Tj) Mu(Af Ao Ap As Aw Ax Bb Bc Ch Cp Cs Cu Cv Cw Cx Db De Dg Di Ed Et Fw Gl Gp Hf Hq Hv Hw Hx Ib Ih Ii Ik Il Im In Io Ip Iu Iv Je Jg Ji Jj Jk Jl Jr Jt Jy Kc Kd Kq Kr Kx Ky Kz Ld Lj Lx Lz Ma Me Mf Mh Mj Ml Mn Mp Mr Ms Mt Mw Mx Mz Na Nb Nc Nd Ne Nf Ng Nh Ni Nj Nk Nl Nm Nn Nq Nt Nu Nv Nw Nx Og Oh Ok Om On Ou Ow Oy Pa Pb Pd Pf Pg Pk Po Qa Qd Qc Ql Qt Qv Qx Qy Rc Ri Tn To Tr Tt Tv Ub Ue Uf Uk Uo Uu Vo) Ib(Ad As Ba Bn Cp Cq Ct Cv Cw Dc Em Ez Fn Fw Gn Hf Id Ij In Ip Ir It Iv Je Ji Jl Jn Jr Js Jt Jy Kd Kn Kr Lw Lx Ly Md Mi Mk Ml Mm Mv Mx Nn Nw Nx Ny Of Ow Pd Pi Pk Qg Qv Qy Ra Ri Ue Vt Vu Vv) Ou(Ap Ar As Bb Bc Bo Ct Cv Cw De Dg Et Hb Il Ip Iv Jl Ke Kr Kx Ly Ma Mg Mk Ml Mw Na Nm Of Og Pd Pf Pg Pj Qv Qy Rh Tr Ua Ue Uf Uh Us Uv Vp Wm) Cs(Ad Af Aj Al An Ap Aw AX bA Bb Bc Bg Bn Bo bS Ch cK Co Cq cT Cu Cv Cw Cx Db Dc Dd De Dg Di Dl Dr Em Ex Fw Gl Gn Gp) Mm(Ap Ba Co Ct Dg Dk Ez Fr Gl Ik Is Jd Je Jh Jk Jl Jp Lh Li Lx Mw Ng No Nt Nw Of Og Ok Oy Pe Pf Pg Po Qu Qy St Tz Ua Uu) Ct(Em Fr Il Im Ip Is Je Ji Jr Lj Lx Ly Mi Mq Mr Mv Na Ni Nn Nt Nu Nw Oa Ow Qt Qv Qy Rb Rf Ri Tz Ub Vp Wm Tj) Qy(Ba Bo Em Fp Hf Hr Hv Ip Je Jr Jy Ky Kz Mk Mx Na Nn Nv Nw Nx Of Og Ow Pk Qt Qv To Tr Ue) Mw(Ba Bo Em Hf Hr Ip Jy Kq Ma Me Mk Mt Nn Nw Nx Of Og Oi Ow Pk Qv Rb Tr Ue) Ex(aE Af Aj Al Ap Ax Ba Bg Bo

Figure 13 Continued

Figure 13 Continued

Kk Kn Kp kS Kz Lh Li Lj Lu Lv Lw Lx Ly Lz Mb Mc Me Mh Mi Mj Mk Ml Mq Mr Ms Mu Mv Mw Mx My Mz Na Nb Nc Nd Ne Nf Nh Ni Nj Nk Nn No Nq Nr Ns Nt Nu Nv Nw Nx Oa Oe Of Og Oi oN On Or Ou Oz Pa Pb Pc Pe Ph Pj Po Qb Qc Qg Qh Ql Qm Qn Qt Qu Qv Qw Qx Qy Qz Ra Rb Rc Rf Ri Rj Rm St Tn To Tt Tz Ua Ub Uc Ud Ue Ug Ul Um Un Uo Ur Us Ut Uu Vp Vs Vu Vv Wm) Tr(AD aK Al AN Ao aQ Ar As aU Aw AX Ba Bb Bc Bg Bn bO bR bU cC cE cF cG cJ Co Cp Cq CS Ct Cv Cw Cx Dc Dd De Dg dI dJ Dl Dp Ed Ef El Et Ex Ez Fp Fr Fw Fy gL Ha Hb Hq Hr Hv Hw Hx Ih Ii Ij Ik Il Im In Io Ip Is Iz Je Jf Jh Ji Jk Jm Jn Jo Jp Jr Js Jt Ju Jv Ke Kf Kg Kj Kk Kn Kp Ks Kx Lh Li Lj Lu Lv Lw Lx Lz Ma Mb Md Me Mf Mg Mh Mi Mj Ml Mm Mp Mq Mr Mt Mv Mx Mz Na Nb Nc Nd Ne Nf Ng Nk Nl Nm Nn No Nq Nr Ns Nt Nu Nv Nx Ny Oa Oe Of Oh Oi Ok Om On Or Ow Oy Pa Pb Pc Pd Pe Pf Pg Ph Pi Pj Pk Po Pz Qa Qb Qd Qe Qg Qh Ql Qm Qn Qt Qw Qx Qy Ra Rb Rf Rg Rh Rj Rm Tn To Tv Ua Ub Uc Ud Ue Uf Ug Uh Ul Um Un Uo Ur Us Ut Uu Uv Vo Vp Vs Vt Vu Vv Wm) Af(Al An Ao Ap As Aw aZ Ba bN Bo cE Cp cS Ct Cu Cv Cw cZ Dd DG Dk dL Dp EF Ez Fw Fy Ha Hb Hc Hf Hq Hr Hu Hv Hw Hx Ih Ii Ij Ik Il Im In Ip Iz Jd Je Jf Jg Jh Ji Jj Jk Jl Jm Jn Jo Jp Jq Jr Js Jt Ju Jv Jy Kc Ke Kf Kg Ki Kj Kk Kl Kn Kp Ks Kz Lh Li Lj Lu Lv Lw Ly Lz Mb Mc Me Mg Mh Mi Mj Mk Ml Mm Mq Mr Ms Mu Mv Mw Mx My Mz Na Nb Nc Nd Ne Nf Ng Nh Ni Nj Nk Nl Nm No Nq Ns Nt Nu Nv Nw Nx Ny Oa Oe Of Og Oi Ok Om Or Ou Ow Oy Oz Pa Pb Pc Pe Ph Pi Pj Po Pz Qa Qc Qg Qh Ql Qm Qn Qt Qu Qv Qw Qx Qy Qz Ra Rb Rc Rf Rg Rh Ri Rj Rm St Tn To Tt Tz Ua Ub Uc Ud Ue Uf Ug Uh Ul Um Un Up Ur Us Ut Uu Vo Vp Vs Vt Vu Vv Tj) Cv(aC Ad aG Aj Al aN AO Ap Ar Aw AX aY aZ Ba Bb BC Bg bI BN bU bV bW cB cE Ch cJ Co Cq cR Cs Ct Cw Cx cZ Db Dc Dd De DG dH Di Dk DL Ed Ef Et Fb Fr Fw Fy GL Gp Hb Hq Hr Hu Hv Hw Hx Ih Ii Ij Ik Il Im In Ip Iq Ir Is It Iv Jd Je Jg Jh Ji Jj Jk Jl Jm Jn Jo Jp Jq Jr Js Jt Jy Ke Kl Ks Lh Li Lj Lu Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Ow Oy Oz Pa Pb Pd Pe Pf Pg Pk Po Pz Qa Qb Qc Qd Qe Qg Qw Rh Tv Ue Uf Uh Uo Up Ur Vo Tj) Cw(An Ao Ap As Aw aX aZ Ct Cu Cx Dp Ed Et Ez FP Fy Ha Hb Hc Hf Hr Hu Hv Hw Hx Ih Ii Ij Ik Il Im In Iz Jd Je Jf Jg Jh Ji Jj Jk Jl Jm Jn Jo Jp Jq Jr Js Jt Ju Jv Jy Kc Ke Kf Kg Ki Kj Kk Kl Kn Kp Ks Kz Lh Li Lj Lu Lv Lw Lx Ly Lz Ma Mb Mc Md Me Mf Mg Mh Mi Mj Mk Ml Mp Mq Mr Ms Mt Mu Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oz Pb Pc Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm St Tv Tz Ua Ub Uc Ud Ue Uf Ug Uh Ul Um Un Uo Up Ur Us Ut Uu Uv Vo Vp Vt) Bb(An Ao cO Cp cS Cu Cx dG Dp Ed Et Ez Fb Fp Hb Hc Hf Hq Hr Hu Hv Hw Hx Ih Ii Ij Ik Il Im In Io Ip Iz Jd Je Jg Jh Ji Jj Jk Jl Jm Jn Jo Jp Jq Jr Js Jt Ju Jv Jy Ke Kf Kg Kj Kk Kl Kn Kp Ks Kz Lh Li Lj Lu Lv Lw Lx Ly Lz Ma Mb Mc Md Me Mf Mg Mh Mi Mj Mk Ml Mm Mn Mq Mr Ms Mu Mv Mw Mx Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ow Oz Pa Pb Pc Pe Pf Pg Ph Pi Pj Pk Po Pz Qa Qb Qc Qd Qe Qg Qw Qx Qy Ra Rb Rf Rg Rh Rj Tn Tv Tz Ua Ub Uc Ud Ue Uh Uo Up Ur Us Ut Uu Uv Vp Vs Vt Vu Vv) bV(aC aD aE aG aH aI aJ aK aL aM aN aO Ap aQ aR aS aU aV aW aX aZ bA bB bC bE bF bI bJ bM bO bP bS bU bW bX bZ cA cB cD cF cG cJ cL cM cN cQ cR cT CU cV cX cY dA dB dC dD dE dF dI dJ dK dM dN eC Fb Fy gL hC Hv Hw Hx iA Ii IJ Il In iP Jg Jh Ji Jn Jo Jq Jr Js Jt Jy Ke Kf Kg Kj Kl Kn Kp kQ kR KS Kz Lh Lj Lv Lw Lx Lz Mb Md Me Mf Mg Mi Mj Ml Mm Mn Mq Mr Mu Mw Mx Mz Na Nb Nc Nd Nf Ng Nh Nk Nl Nm Nn No Nr Ns Nt Nv NW Nx Ny Oe OH Oi OK Om oN Oy Pa Pb Pc Pe Pf Pi Po Pz Qa Qb Qg Rj Tv Uc Ue Uf Uh Us Ut Uv Vo Vp Vs Vt Vu Vv) As(Al An Ao Ap Aw aZ Bo cE Cp cS Cu Cx DG Ed Ez Fb Fp Fy Hb Hq Hr Hu Hv Hw Hx Ib Ih Ii Ij Ik Il Im In Ip Iq Ir Is It Iv Jd Je Jg Jh Ji Jj Jk Jl Jm Jn Jo Jp Jq Jr Js Jt Ju Jv Ke Kg Kl KS Kz Lh Li Lj Lu Lv Lw Lx Ly Lz Mb Mc Md Me Mf Mg Mh Mi Mj Mk Ml Mm Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Ow Oy Oz Pa Pb Pc Pd Pe Pf Pg Pk Po Pz Qa Qb Qc Qd Qe Qg Qy Rc Rg Rh Tv Ue Uf Uh Uo Ur Us Uv Vo Vt) Iu(aD aE aG aH aI aJ aK AL aM aN Ao aQ Ar aS aU aV Aw Ax aY aZ BA bB bC Bg bI bL BN bO bQ bU bZ cB cC cF Ch cK cL Co Cp Cq cR CS Ct cV cW cX cY cZ Db Dc DD DE dG dH Di dJ DK DL dN Dp Ed EF Ex Ez fP Fw Fy GL Gp Ha Hb Hc Hf iA Iz Jd Je Jf Ju Jv Jy Kc Ke Kf Kg Ki Kj Kk Kl Kn Kp Ks Kz Oa Or Ou Ow Ph Pi Pj Qh Ql Qm Qn Qt Qu Qv Qw Qx Qy Qz Ra Rb Rc Rf Rg Rh Ri Rj Rm St Tv Tz Ua Ub Uc Ud Ue Uf Ug Ul Um Un Uo Up Ur Us Ut Uu Uv Vo Vp Vs Vt Vu Vv Wm Tj) cO(aC aE aF aG Aj Al An aO Ap AR aU AW Ax BA BC bF Bg bH bJ bM Bo bP bR bS bW bZ cA cC cD cF cG CH cK cL cM cN Co CP Cs CT cV cX dA DB dC dD DE Dg Di DK Dl dN Dp dR Ed EF Ez Fb Fr Fw Fy gL gP gW Ha Hb Hc Hf Hq Hu Ih Im Iz Jd Je Jf Jg Jj Jk Jl Ju Jv Jy Kc Ki Kk Kl KS Kx Kz Ld Lu Mc Mh Ms Nj Nq Nu Nw Oa Of Og oH Or Ou Ow Oz Pj Qg Qh Ql Qm Qn Qt Qu Qv Qw Qy Qz Rc Rf Rg Rh Ri Rm St Tn Tt Tv Tz Ua Ub Uf Ug Uh Ul Um Un Ur Uu Vo Wm) Pk(AD aG aK Al AN Ap aQ Ar aU aV AX aY Ba BC bI bJ BN BO bQ bU cB cC cE cF cG cJ Co Cp Cq Cs Ct cW Cx cY Dc Dd dF DG dH dJ dK DL dN Ed Et Fb Fr Gc gL Ha Hb Hq Ii Ij Im In Io Ip Iq Ir Is It Iv Jd Ji Jo Jp Jq Js Jt Jy Ke Kf Kg Kj Kk Kl Kn Kp Ks Lj Lv Lw Lx Ma Md Me Mf Mg Ml Mn Mp Mq Mr Mt Mv Mz Na Ng Nk Nl Nm Nr Nv Nw Nx Ny Oh Oi Ok Om On Oy Pa Pb Pc Pd Pe Pf Pg Ph Pj Pz Qa Qb Qd Qe Qg Qw Qy Rb Rh Tv Uc Ue Uf Uh Uo Up Uv Vo Vs Vt Tj Ti) Dg(Al An Ao Ap Aw aX aY Ba bN Cp Cu Cx Dd Dk Ed Et Ez Fb Hq Hr Hv Hw Hx Ih Ii Ij Ik Il Im In Io Ip Iz Jd Jg Jh Ji Jk Jm Jn Jo Jp Jq Jr Js Jt Jy Ke Kg Kn Kp Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nv Nw Nx Ny Oe Of Og Oh Oi Ok Om On Or Oy Oz Pa Pb Pc Pd Pe Pf Pg Pi Po Qa Qb Qd Qe Qx Ra Rb Rj Tv Uc Ud Ue Uo Up Us Ut Uu Uv Vp Vs Vt Vu Vv) Pd(Aa aC Ad aG Aj aK Al AN Ao Ap aQ Ar aU aV Aw AX aZ Ba Bc Bg bI BN bO bU bW cB cC cE cF cG Ch cJ Co Cp Cq cR Cs Ct Cx cY Db Dc Dd De dG dH Di dJ DK DL Dp Ed EF Ez Fb fP Fw Fy GL Gp Ha Hb Hc Hf Ib Iz Jd Je Jf Ju Jv Jy Kc Ke Kf Kg Ki Kj Kk Kl Kn Kp Ks Kz Oa Or Ou Ow Ph Pi Pj Qg Qh Ql Qm Qn Qt Qu Qv Qw Qx Qy Qz Ra Rb Rc Rf Rg Rh Ri Rj Rm St Tv Tz Ua Ub Uc Ud Ue Uf Ug Uh Ul Um Un Uo Ur Us Ut Uu Uv Vo Vp Vs Vt Vu Vv Tj) cB(aC aD aG aH aI aJ aK aL aM aN aP aQ aS aV aW aX aZ bB bE bI bL bO bQ bS bW cD cE cG cI cJ cK cQ cR cT cU cZ dC dE dF dG dH dL dM dR eC Ed eM Et Ez Fb Fy gL Hb iA IJ Ik In iP Je Jo Jp Jq Js Jt Jy Kc Ke Kf Kg Kj KS Li Kn Kp kQ kR KS Kz Li Lw Lx Ma Md Mf Ml Mm Mn Mp Mr Mt Mz Nd Nh Nn Nr Ny Oa OH OK Om ON Ow Oy Pf Pg Pi Qa Qd Qe Qg Qw Qx Ra Rb Rj Rm Tv Uc Ud Ue Uf Uh Uo Up Us Ut Uv Vo Vp Vs Vt Vu Vv) Et(AD Aj aK Al Ap aQ Ar aU Aw AX aZ Ba Bc Bg bI bJ BN bO bW cC cE cF Ch cJ Co Cp Cq cR Cs Ct Cx Db Dc Dd DE dH Di dJ DK Dl Dp Ed Ef Ex Ez Fb fP Fw Fy Gl Gp Ha Hb Hc Hf Ib Iz Je Jf Ju Jv Jy Kc Ke Kf Kg Ki Kj Kk Kl Kn Kp Ks Kz Oa Or Ou Ow Ph Pi Pj Qg Qh Ql Qm Qn Qt Qu Qv Qw Qx Qy Qz Ra Rb Rc Rf Rg Rh Ri Rj Rm St Tv Tz Ua Ub Uc Ud Ue Uf Ug Uh Ul Um Un Uo Ur Us Ut Uu Uv Vo Vp Vs Vt Vu Vv Tj) cS(Ad Aj Al Ao Ar Aw Ax Ba Bc Bg Bn Bo Ch Co Cp Cq Cs Ct Cx Db Dc Dd De Di Dk Dl Fb Fr Fy gP gW hC Hv Hw iA Ii IJ Il In iP Iq Ir Is It Iv Ji Jn Jo Jp Jq Jr Js Jt Jy Ke Kf Kg Kj Kl Kn kQ kR KS Kz Lh Li Lj Lv Lw Lx Ma Mb Md Mf Mg Mi Mj Ml Mm Mn Mq Mr Mw Mx Mz Na Nb Nd Nf Ng Nl Nm Nn No Nr Nv nW Nx Ny Oe OH Ok Om ON Oy Pb Pe Pf Pg Po Pz Qa Qb Qd Qe Qg Uc Ue Uf Uh Ut Uv Vo Vt Vv) Fb(AD aK An aQ aU Ax Bc Bn bU cC cE cJ Co Cp Cq Cs Cx Dc Dd dJ DL Ed Ez Fw Hv Hw iI Ij In Io Ip Iq Jd Ji Jn Jo Jq Jr Js Jt Ke Kf Kg Kj Kk Kn Kp Ks Lh Li Lj Lv Lw Lx Ma Md Me Mf Mg Mi Mj Ml Mm Mn Mp Mq Mr Mt Mz Na Nb Nf Nk Nl Nm Nn No Nr Nv Nx Ny Oa Oe Oh Oi Ok Om On Or Oy Pb Pc Pe Pf Pg Ph Pi Po Pz Qa Qb Qd Qe Qg Qx Ra Rb Rh Rj Uc Ud Ue Uh Uo Up Us Ut Uv Vp Vs Vt Vu Vv Tj) Iv(aC Ad aE aG aH Aj aK Al AN Ao Ar aU Aw Ax aZ Ba BC Bg bI bL BN bO bQ bZ cC cF Ch cL Co Cp Cq cR Cs Ct cV Cx Db Dc Dd DE dF dG dH Di dJ DK Dl Dp Ed EF Ex Ez fP Fw Fy gL Gp Ha Hb Hc Hf Iz Jd Je Jf Ju Jy Kc Ke Kf Kg Ki Kj Kk Kl Kn Kp Ks Kz Oa oK Or Ou Ow Ph Pi Pj Qg Qm Qn Qw Qy Qz Ra Rb Rc Rf Rg Rh Tv Uc Ue

Ch Co cT Cu Cv Cx Dc De Dk Em Fr Fw Gl Gp) Ax(AJ Ao Ar aX bA Bg Bo bP cK Co Cp cT Dc Di Dk Em Fr Fw Gl) Of(Aj As Ba Bb Fr Il Ip Je Jj Jl Lx Mv Mx Nn Qt Qv Rb Ub Vo Wm) Ua(Bb Cu Cw Em Ip Je Jl Ly Ma Me Ng Oi Ow Qv Rb Ue Vo Wm) Jl(Ba Bo Ed Em Hr Jy Kq Ly Nn Og Oi Ow Oy Qv Rb Ue) Ba(Em Il Ly Ma Mk Na Nb Nn Og Oi Qv Ub Wm Tj) Ef(Et Il Ip Kl Ly Ma Ng Ow Pd Qv Ue Vo Wm Tj) Em(Ao As Bg Cp Cu De Dk Fb Gl Lx Mx) Nn(As Bo Je Ly Ma Mk Ml Nb Rb Rh Wm) Cp(Et Ma Pd Pg Pj Rh Ue Wm Tj) Nb(As Hr Jy Mk Ms Nw Og To Tr) Iz(Bb Cw Ip Ng Pd Qv Rb Ue Vo) Wm(Fr Je Jk Mv Nv Qt) Mv(Bo Ly Ma Og Ue) Ao(Pd Pj Ue Tj) Fr(Cu Ly Og Tj) Mx(As Hr Mk Og) Jg(Bb Cw Et Pd) Jk(Ip Jf Qv Rb) Po(Ly Rb) Mi(Og Oi) Mk(As Nw) Hu(Vq Vs) FyRh GzJh LyQt UeOn JiPj NwVt UuVo} Jj{On(Et Fp Fr Hq Hr Hu Hv Hw Hx Ih Ik Il Im In Io Ip Iq Ir Is It Iv Jg Jh Ji Jk Jl Jm Jn Jo Jp Jq Jr Js Lh Li Lj Lu Lv Lw Lx Ly Lz Ma Mb Mc Md Me Mg Mh Mi Mj Mk Ml Mm Mp Mr Ms Mt Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om Oy Oz Pa Pb Pc Pe Po Qa Qb Qc Qe) Nn(Fp Fr Hq Hr Hu Hv Hw Hx Ih Ik Im In Io Ip Iq Ir Is It Iu Iv Jg Ji Jk Jm Jn Jo Jp Jq Jr Js Lh Lj Lu Lv Lw Lx Ly Lz Mb Mc Md Me Mg Mh Mi Mj Mk Ml Mm Mp Mq Mr Mt Mw Mx My Mz Na Nb Nc Nd Ne Nf Ng Nh Ni Nj Nk Nl No Nr Ns Nt Nu Nw Nx Ny Of Og Oh Oi Ok Om Oy Oz Pa Pb Pc Pd Pe Pf Po Qb Qc) Jl(Et Fp Fr Hq Hr Hu Hv Hw Hx Ih Ik Im In Io Ip Iq It Iv Jh Ji Jm Jn Jo Jp Jq Jr Js Lh Li Lj Lu Lw Lx Ly Lz Ma Mb Mc Md Me Mg Mh Mi Mj Mk Ml Mm Mp Mq Mr Ms Mt Mw Mx My Mz Na Nb Nc Nd Ne Nf Ng Nh Ni Nj Nk Nm No Nq Nr Ns Nt Nu Nv Nw Ny Oe Of Og Oi Om Oy Oz Pa Pb Pc Pe Pg Po Qa Qd Qe) Mv(Et Fp Fr Hq Hr Hu Hv Hw Hx Ii Ij Im Jg Jh Ji Jm Jn Jp Jq Jr Lh Li Lu Lw Lx Ly Lz Mb Mc Md Mh Mj Mm Mp Mq Ms Mt Mw My Mz Na Nb Nc Nd Nf Nh Ni Nj No Nq Ns Nt Nv Oe Of Og Oi Om Oy Oz Pb Pc Pe Pf Pg Po Qa Qb Qd Qe) Mu(Fp Hq Hr Hu Hw Ih Ii Ik Il Im Jh Ji Jn Jp Jq Lh Li Lj Lu Lw Lx Ly Lz Mb Md Mh Mj Mp Mq Ms Mt Mw My Mz Na Nb Nd Nf Nh Ni Nj No Nq Ns Nt Nv Oe Of Og Oi Oy Oz Pb Pc Pe Pf Pg Po Qa Qd Qe) Fr(Et Hv Hx Ik Ln Io Ip Ir Is It Iv Jg Jk Jm Jo Jr Js Jt Lv Ma Me Mg Mi Mk Ml Mm Mr Mx Na Nc Ne Ng Nh Nk Nl Nm Nr Nt Nu Nx Ny Og Oh Ok Om Pd Pf Qb Qc) Jk(Hv Ik Im In Ip Ir Is It Iv Jg Ji Jm Jo Jr Js Lh Lv Ma Mc Mf Mg Mi Mk Ml Mr Mx Nc Ne Ng Nh Nk Nl Nm Nr Nt Nu Nw Nx Oh Ok Om Pd Po Qa Qb Qc) Is(Et Ih Ik In Ip Ir It Jg Jm Jo Js Jt Lu Lv Ma Me Mf Mi Mk Ml Mn Mr Mx Nk Nl Nm Nt Nu Nw Oh Ok Pa Pd Pz Qc) Ik(Hv Hx Im Jg Jo Lv Mf Mi Mk Ml Mn Mr My Nk Nr Nw Oh Ok Om Pa Pc Pd Pz Qb Qc) Jg(Et Ir Jo Jt Lv Ma Me Mf Mg Mi Ml Mn Mx My Ne Ng Nk Nl Nu Nx Oh Pd Qb Qc) Mf(Ir Ji Lv Mi Mx Nu Nv Nw Nx Oh Ok Po Qb) Mn(Ji Lh Lv Mi Nv Nw Oh Ok Po Qa Qb Qc) Pz(Ji Lh Lv Mi Nv Nw Oh Ok Po Qa Qb) Ok(Ir Jo Jt Lu Ml Mx Nl Nm Oh Pd) Mi(Ir Js Ma Me Ml Nl Nx Oh Pd) Nw(In Ir Js Ml Nl Ny Oh Pd) Ml(Ir Lv Mx Om Qb) Lv(Ir Mx Oh) Qb(Ih Me Nk) Ji(Et Jt Nm) Om(In Js Md) Ir(Mx Oh) Jt(Lh Nv) EtNv MeOh NkNl} aJ{cO(aC aE aF aG aH al aK aL aM AN aO aP aQ aR aS aU aV AW aY BA bB bC bE bF bH bl bJ bL bO bP bQ bR bS bU bV bW bX bZ cA cB cC cD cE cF cG cH cJ cK cL cM cN CP cQ cR cT cU CV cX cY dA dB dC dD dE dF dH dI dJ dK dM dN Ed Et Ez Fn fP Io Iq Ir Iu Iv Ko Kr kS Ma Mk Mn Mv Mx My Pk Tr Uk) bN(aC aD aE aF aG aH aI aK aL aM aN aO aP aQ aR aS aU aV aW aX aY aZ bA bB bC bE bF bH bI bJ bM bO bP bQ bR bS bU bV bW bX bZ cA cB cC cD cF cG cH cJ cK cL cM cN cP cQ cR cT cU cV cX cY dA dB dC dD dE dF dI dJ dK dM dN dR fP gL iA kS) cI(aC aD aE aF aG aH aI aK aL aM aN aO aP aQ aR aS aU aV aW aY aZ bA bB bC bE bF bH bI bJ bO bP bQ bR bS bU bV bW bX bZ cA cB cC cD cE cF cG cH cJ cK cL cM cN cP cQ cR cT cU cV cW cX cY cZ dA dB dC dD dE dF dH dI dJ dK dM dN) cS(aC aD aE aF aG aH aI aK aL aM AN aO aP aQ aR aS aU aV aW aX aY aZ bA bB bC bE bF bH bI bJ bM bP bQ bR bS bU bV bX bZ cA cB cC cD cF cG cH cL cM cN cP cQ cR cT cU cV cX cY cZ dA dB dC dD dE dF Dg dI dJ dK dM dN dR hB iA) dL(aD aE aF aG aH al aK aL aM aO aP aQ aR aS aU aV aW aY aZ bA bB bC bE bF bH bI bJ bM bO bP bR bU bW bZ cA cB cC cD cF cG cH cJ cL cM cN cP cQ cR cT cU cV cX cY cZ dA dB dC dD dF dI dJ dM dN dR fP gL Iu Ko kS) dG(Ad Af Aj Ao Ap Ar As Ax Bb Bc Bg Bn Bo Ch Co Cs Ct Cu Cv Cw Cx Db Dc De Dg Di Dk Dl dR Ef Ez Fn FR GL GP gW Io Ip Iq Ir Is It Iv Kd Ko Kq Kr kS Ky Ma Mn Mr My Ow Tr Tv Uk Up Tj) bG(aC aD aE aG aH aM aN aP aR aW aY aZ bB bl bJ bL bM bO bQ bS bU bW bX bZ cB cE cJ cK cP cR cU cW cZ dC dE dH dI dK dM dR gL) cW(aC aN aX aZ bA bL bM bO bV cB cE cJ cM cT cZ dH iA kS) bM(aC bL bO bX cJ cK cZ dE fP iA iP kQ KR kS oN) aX(aC aM aP bL bO bQ bS bW cE cG cJ cK dE) bV(aM aP bL bO cE cK cZ dH Et hB iA Ko) bL(aZ bA bO cB cE cJ cT cZ dH dI) dH(cJ cT cZ Io Iu Ko Kr Pk) kS(bQ bW cB iA Ma oN) cZ(aC bA bW cE cT) Ko(Ba cB Cp iA) Kr(cB cF Pk) bA(cE cJ dF) cT(cE cJ dF) fP(cJ iA oN) iA(aD Iu) TrcB bOcE} Jo{On(Et Fp Hq Hr Hu Hv Hw Hx Ih Il Im In Io Ip Iq It Jg Jh Ji Jk Jm Jn Jp Jr Js Lh Li Lj Lu Lv Lw Lx Ly Lz Ma Mb Mc Md Me Mf Mg Mh Mi Mj Mk Ml Mm Mp Mq Mr Ms Mt Mw My Mz Na Nb Nc Nd Ne Nf Ng Nh Ni Nj Nk Nm No Nq Nr Ns Nt Nu Nv Nw Ny Oe Of Og Oh Oi Ok Om Oy Oz Pa Pb Pc Pe Pf Po Qa Qb Qc Qd Qe) Mu(Em Et Fp Hq Hr Hu Hv Hw Hx Ih Im In Io Iq It Iu Iv Jg Jh Jk Jm Jn Jp Jr Js Jt Lh Li Lj Lu Lw Lx Ly Lz Ma Mb Mc Md Me Mg Mh Mj Ml Mm Mn Mp Mq Ms Mt Mw Mx My Mz Na Nb Nc Nd Ne Nf Ng Nh Ni Nj Nl Nm No Nq Ns Nt Nu Nv Nx Ny Oe Of Og Oh Oi Oy Oz Pa Pb Pc Pd Pf Pg Po Pz Qa Qb Qc Qd Qe Tr) Ok(Et Fp Hr Hu Hv Hx Ih Ik Im In Io Ip Iq Ir It Iu Iv Jh Ji Jm Jn Jp Jq Jr Js Jt Lh Li Lj Lu Lv Lx Ly Lz Ma Mb Mc Me Mf Mg Mi Mk Ml Mn Mp Mr Ms Mt Mw Mx My Mz Na Nb Nc Ne Nh Ni Nk Nl Nm Nq Nt Nu Nv Nw Og Oh Oi Om Pc Pf Po Pz Qa Qb Qc Qd) Mv(Fn Fp Fr Hq Hr Hu Hv Hw Hx Ih Il In Io Ip Iq It Iu Iv Jg Jk Jm Jq Jr Js Lh Li Lj Lw Lx Ly Ma Mb Mc Me Mf Mg Mj Ml Mn Mp Mq MZ Na Nb Nc Ne Nf Ng Nh Ni Nl No Nr Ns Nt Nu Nv Nx Ny Og Oh Pa Pb Pc Pd Pe Po Pz Qa Qb Qc Qd Tr) Fr(Hv Hw Hx Ik Ip Iq Ir Iv Jg Ji Jm Jq Jr Js Lw Ly Ma Mb Mc Mf Mg Mi Mk Ml Mn Mr Mx Na Ne Ng Nh Nk Nl Nn Nr Nt Nu Nw Nx Oh Om Pa Pd Pe Pz Qb Qc) Jl(Hu In Ip Ir Is It Iu Iv Jg Jk Js Lh Lj Lv Mf Mi Mn Mx My Nk Nl Nt Nv Nw Nx Oh Pd Po Pz Qb Qc) Nn(Ik Ip Ir Is Iv Jg Jq Lh Ma Me Mf Mk Mr Mx Nb Nk Nl Nm Nr Nt Nu Nw Nx Om Pa Pe Pz Tr) Jg(Ir Is Ji Jq Lv Mi Mx My Ng Nk Nu Om Pz) Nw(In Ir Js Lv Md Mi Mt My Ny Pd Pz) Is(Ji Jk Jm Lv Mi Mk Mr Om Tr) Nq(Fn Ko Kr Tn To Tt Tv Th) Tr(aP Cp Jd Jk Lh Mx Ua) Ml(Ik Ir Ji Jk Nv Nx) Fn(Cp Hv Iz My Po) Ji(Ir Jk Lv Mk Mn) Ti(Al Ao Pk) Lv(Ir Jk Nv) Om(In Ml Po) Em(Hc Ua) Iz(Cu To) GdHu MnNv aPcO} Mu{Mg(Hx In Io Ip Iq Ir Is It Iu Iv Ji Jl Jm Jq Js Jt Lv Lx Mf Mk Ml Mn Mr Ne Ng Nk Nl Nn Nr Nt Oh Om Pa Pb Pc Pd Pz) Ng(Fr Hx In Ip Ir Is It Iv Jg Ji Jl Jm Js Lv Mf Mi Mk Ml Mn Mr Nk Nl Nn Nw Oh Ok Om On Pa Pd Pz Qc) Pz(Hx In Ir Is Jg Ji Jm Jp Li Lv Mf Mi Mk Ml Mn Mr Mv Mx Nk Nr Nu Oh Om Pa Pd Qa Qb Qc Qd) In(Hv Hw Hx Ir Iv Ji Jq Jt Lv Lx Mf Mj Mk Mn Mr Mv Mx Mz Nb Nn Nr Nu Ok Om Pa Pb Pe) Jt(Fr Hx Ir Jg Jm Jq Lv Mf Mi Mk Mr Mv Mx Nk No Nr Nv Nw Oh Om Pa Pe Qa Qc) Pd(bV Fn Fr Hw Ir Is Kq Lh Li Lv Lx Mf Mk Mn Mp Mr Mv Nk Nn Nr Nt Nu Pa Pe) Jl(Et Hq Ih Il Ip It Jm Js Lj Lv Ma Mf Mh Ml Mn Nk Nl Nm Nr Of Oh Pf Pg) Jm(Fr Hx Ir Ji Lv Mf Mi Mn Mv Mx Nn Nw Ok On Qb Qc) Uk(CO Cu Dk Ex Jd Kd Md My Nq Nv Tv Uc Ut Vs) Em(Ad As Bb Dc Gd Iu Kf Ma Om Pj Qe Uc Ue) On(Et Il Iu Js Mf Mn My Nm Nr Oy Pf Pg Po) Ex(Bb bV cS Et fP Hb Ip Iu Ma Nm Tr Ue) Pg(Cu Fn Ko Kq Ky Pk Qv Tr Ue Wm) Md(Cu Fn Kq Kr Om Pk Qv Tr Ue) Mn(Fr Ji Lv Mf Mi Nk Nw Ok) Js(Is Ji Jq Mi No Nw Ok) Gd(Hu Jy Kd Kq Mm Oe) Tj(Iu Ko Ma Tr Ue) Mf(Ji Lv Mi Nk Ok) Ml(Is Jq Mi Nw) Nm(Is Ji Nn) Ma(Kq kS Mi) Mm(Dr fR Gn) Tr(Nv Ny Om) Iu(cO Cu Mr) Et(Ji Ok) Fn(Dk Kq) Nk(Mi Nl) Nw(My Ny) Om(To Tv) CoMp MrKo llPa aPcO} On{Jt(Et Fp Hq Hr Hu Hv Hw Hx Ih Ik Il Im Io Ip Iq It Jh Jk Jm Jn Jp Jr Js Lh Li Lj Lu Lv Lw Lx Ly Lz Ma Mb Mc Md Me Mg Mh Mi Mj Mk Ml Mm Mn Mp Mq Mr Ms Mt Mw Mz Na Nb Nc Nd Ne Nf Ng Nh Ni Nj Nk Nm No Nq Nr Ns Nt Nu Nv Nw Nx Ny Oe Of Og Oi Ok Om Oz Pa Pb Pc Pe Pf Po Pz Qb Qc Qd Qe) Pd(Et Fp Hq Hr Hu Hv Hw Hx Ih Ik Il Im Io Ip Iq It Iv Jg Jh Ji Jk Jm Jn Jp Jq Jr Js Lh Li Lj Lu Lv Lw Lx Ly Lz Ma Mb Mc Md Me Mf Mg Mh Mj Mk Ml Mm Mp Mq Mr Ms Mt Mw My Na Nb Nc Nd Nf Ng Nh Ni Nj Nk Nm No Nq Nr Ns Nv Nw Nx Ny Oe Of Og Oh Oi Ok Oy Oz Pa Pb Pc Pe Pf Qa Qb Qc Qd Qe) Pz(Fr Hq Hv Il In Ir Is Iu Iv Jg Ji Jl Jm Jp Lu Mf Mg Mi Ml Mn Mt Mx My Nb Ne Ng Nk Nl Nu Nv Nx Oh Oy Pf Po Qa Qb Qc) Pg(Et Hv In Ip Ir Is Iu Jl Jm Js Lj Lu Lv Ma Mb Me Mf Mg Mi Ml Mm Mv Mx

Rg Rh Ri Rj Rm St Tn To Tt Tz Ua Ub Ud Ug Ul Um Un Uo Up Ur Us Ut Uu Vp Vu Vv Tj) aJ(aC aD aE aG aH al aM aN aO aP aQ aR aW aX aY aZ bA bB bE bF bl bM bO bQ bS bU bV bW bX cB cD cE cF cG cH cJ cK cL cP cR cT cU cZ dA dC dE dF dH dI dK dM iA Ko kS) Gc(Ef Em Fr Ik Is Iz Je Jg Jk Jl Li Lx Mk Mm Mv Mx Nb Nn Nv Nw Of Og On Po Qt Qy Rb Ua) Jj(Ik Im Ir Iv Ji Jr Lh Lv Mf Mi Mk Mr Mx My Nl Nt Nu Nv Nw Nx Oh Ok Om Pa Po Qa Qb Qc) Mu(Ex Fr Gd In Ji Jm Js Jt Lv Mf Mi Ml Mn Nk Nm Nr Nw Ok On Pd) Jl(Fr In Jg Ji Jm Js Jt Lj Lv Mf Mn Ng Nk Nl Nn Nw Ok On Pd Pz) Mv(Il In Ji Jm Jt Lv Mf Mg Mi Mn Nk Ok On Pd Pz Ue Uk) On(Il In Iu Jm Js Mf Mg Mn Mx Nb Ng Nm Nn Oy Pf) aP(aM bG bL bN cE cI cO cS cW dG dL) Fr(Jm Jt Ma Mf Mn Ng Nm Pd) Jo(Cp Is Jg Ji Lv Mi Nn Nw) Uk(bA cT Ez Fn Mx Ua Ue) Nw(In Js Ml Pd Pz) cS(An bA cI cT dM) Jg(Jt Mg Ng Pz) Ti(Na Pk Sr) Gd(Hc Hu Ua) Nn(Jt Nm Pz) Nq(Ko Kr Tr) Pd(Ji Mi Om) bV(iZ Kr Pk) Em(Mm Pj) Is(In Jt) Ok(Nm Pz) eM(cN cT) FnUe GzUa MdOm MmfR ltmZ JiJt aXcI bNiZ Unconstrained panels with 2 analytes, where 1.0E-3 >= 'model p-value' > 1.0E-4. Contains 1,498 panels of 94,547 total panels evaluated. : Gc(aJ Ao As aX Ba Bb Co Cp cS CT Dc Dk Dp Ed Et Ez Fa Fb Fn Fw Fy Gl Ha Hf Hq Hr Hu Hv Hw Hx Ic Ih Ii Ij Il Im In Io Ip Iq Ir It Iu Iv Jd Jf Jh Ji Jj Jm Jn Jo Jp Jq Jr Js Jt Ju Jv Jy Kc Kd Kf Ki Kj Kk Kl Kn Kp Kr Ks Kx Ky Kz Ld Lh Lj Lu Lv Lw Ly Lz Ma Mb Mc Md Me Mf Mg Mh Mi Mj Ml Mn Mp Mq Mr Ms Mt Mz Na Nc Nd Ne Nf Ng Nh Ni Nj Nk Nl Nm No Nq Nr Ns Nt Nu Nx Ny Oa Oh Oi Ok Om Or Ow Oy Oz Pa Pb Pc Pd Pe Pf Pg Ph Pj Pk Pz Qa Qb Qc Qd Qe Qg Qh Ql Qn Qu Qv Qw Qx Qz Rf Rh Ri Sr Ss St Tr Tz Ub Ud Ue Ug Uk Ul Um Un Ur Ut Uu Uv Vo Vp Vq Vs Vt Vu Vv Wm Tj) Mu(Co Dr Em Et Fp Gn Hq Hr Hu Hv Hw Hx Ih Ii Il Im Io Ip Iq Ir Is It Iu Iv Jg Jh Jk Jn Jp Jq Jr Kq Lh Li Lj Lu Lw Lx Ly Lz Ma Mb Mc Md Me Mh Mj Mk Mm Mp Mq Mr Ms Mt Mv Mw Mx My Mz Na Nb Nc Nd Ne Nf Nh Ni Nj Nl Nn No Nq Ns Nt Nu Nv Nx Ny Oe Of Og Oh Oi Om Oy Oz Pa Pb Pc Pe Pf Pg Po Qa Qb Qc Qd Qe Ue Uk Tj) On(Et Fp Fr Hq Hr Hu Hv Hw Hx Ih Ii Ij Ik Im Io Ip Iq Ir Is It Iv Jg Jh Ji Jk Jn Jp Jq Jr Lh Li Lj Lu Lv Lw Lx Ly Lz Ma Mb Mc Md Me Mh Mi Mj Mk Ml Mm Mp Mq Mr Ms Mt Mw My Mz Na Nc Nd Ne Nf Nh Ni Nj Nk Nl No Nq Nr Ns Nt Nu Nv Nw Nx Ny Oe Of Og Oh Oi Ok Om Oz Pa Pb Pc Pe Po Qa Qb Qc Qd Qe) Jl(Et Fp Gd Hq Hr Hu Hv Hw Hx Ih Il Io Ip Iq Ir Is It Iv Jh Jk Jn Jp Jq Jr Lh Li Lu Lw Lx Ly Lz Ma Mb Mc Md Me Mg Mh Mi Mj Mk Ml Mm Mp Mq Mr Ms Mt Mw Mx My Mz Na Nb Nc Nd Ne Nf Nh Ni Nj Nm No Nq Nr Ns Nt Nu Nv Nx Ny Oe Of Og Oh Oi Om Oy Oz Pa Pb Pc Pe Pf Pg Po Qa Qb Qc Qd Qe Uk) Fr(cS Et Fp Hq Hu Hv Hx Ih Il Im In Io Ip Iq Ir Is It Iu Iv Jg Jh Ji Jp Jq Jr Js Lj Lu Lv Lw Ly Mb Mc Md Me Mh Mi Mj Mk Ml Mm Mq Mr Mv Mx My Mz Na Nb Nc Nd Ne Nh Ni Nj Nk Nl Nn No Nq Nr Ns Nu Nw Nx Ny Oe Of Og Oh Ok Om Oy Oz Pa Pc Pe Pf Pg Po Qb Qc Ti) Jj(Et Fp Hq Hr Hu Hv Hw Hx Ih Ii Ij Il In Io Ip Iq It Iu Jh Jm Jn Jo Jp Jq Js Jt Li Lj Lu Lw Lx Ly Lz Ma Mb Mc Md Me Mg Mh Mj Ml Mm Mn Mp Mq Ms Mt Mw Mz Na Nb Nc Nd Ne Nf Ng Nh Ni Nj Nk Nm No Nq Nr Ns Ny Oe Of Og Oi Oy Oz Pb Pc Pd Pe Pf Pg Pz Qd Qe) Mv(bV cO Cw Et Fn Gd Hq Hu Hv Hx Ih Im Io Ip Iq Ir Is It Iu Iv Jg jP Jq Jr Js Kg Ko Kr Lj Lu Lw Lx Ma Mc Me Mj Mk Ml Mm Mp Mq Mr Mx My MZ Na Nb Nc Ne Nh Ni Nj nK Nl Nm Nn No Nv Nx Ny Oe Of Oh Om Oy Oz Pa Pc Pe Pf Pg Qv) Uk(aJ An aP aX Ba bR bU bV cB cF cJ cO Cp cS Ct Cu dA dI dJ Et gP Hv Hx Ib Ih Im Iu Iz Jd Je Jk Jo Jq Jy Kc Kd Kg Ko Kr KS Ky Md Mf Mi Ml Mm Mn My Nb Nh Nk Nl Nm Nn Nq Oe Og Oi Pd Pk Qg Qh Qv Qw Qy Rh To Tr Ud Uh Up Us Vt Ti) aP(aC aD aE aG aH aI aL AN aO aR aV aW aX aY aZ bA bB bC bE bF bI bM bO bP bQ bS bV bW bX bZ cB cC cD cG cJ cK cL cP cR cT cZ dD dE dF dH dI dK dM dN Et Fn fP iA iJ Jo jP Kd Ko Kr kS Mm Mp nW oK oN Pd Pk Tr Tv) aJ(aF aK aL An aS aU aV Aw Ba bC bH bJ bP bR bZ cA cC cM cN Cp cQ Cu CV cX cY dB dD Dg dJ dN dR eC eF eM Et Fn fP fR gL gP gW hC iJ iP Iu kQ KR Mf Mn Mp nW oK oN Pd Pk Tr Tv) Ti(aA An Ao Bo Db Di Dk Dp Ed Ez Fn Hx Ib Ic Id Ih Jd Ji Jn Jo Jp Jv Kn Ks Ky Ld Lh Lx Ly Mf Mg Mx My Nk Nn Nq Nw Oe Oi Pd Pj Qg Qv Qz Rf Ss To Tr Tv Tz Ue Ul Un Uv Tj) Fn(Ad Al An aX BA bV cB cO cT Cu Cv Dg Et Ez Hx Ib Im Iu Jo Jq Kd Kg Ko Kr KS Ky Md Mf Mg Mi Ml Mm Mn Mx My Nl Nm Nq Pd Pk Qg Qv Qy Rh Tr Tv Uh Vo Vt) aA(Dr EM Ex Gp Gz hB hF hG hW Ib IC Id iH iO iZ jE jl jP kN Kx IL mP mZ nD nN nR nY oE oF pF rB Sr Ss Wm Th tF) Ok(Et Hv Hx Ih Il Im In Ip Ir Is It Iu Iv Jg Jk Jm Jr Js Lu Ma Me Mf Mg Mi Ml Mn Mx My Ne Ng Nk Nl Nn Nw Oh Pc) Mi(Hv In Ip Ir Is Jg Ji Jk Jm Js Jt Lu Lv Ma Me Mf Mg Ml Mn Mx Ne Ng Nk Nl Nm Nn Nr Nw Oh Pc Pz) bA(aX aZ bG bN bV bX cE cI cJ cZ(aD aR dR eM Et fP gL Kq Kr Ma Pd Pf Pk Tr Tv Uc Ue Uv) iZ(aD aK aM aQ aX aZ bG bN bS bX cB cI cP cY cZ dD dM) Ji(Et In Js Lu Mf Mg Ml Mn Nm Pz) kS(bN bQ cB Hb hG Hx jP Ma Mf rB) Gd(Ct Ef Iz Lu Mm Oe Qw Qy Uu) Mx(cO Jg Kr Ks Mf Nk Pz) Is(Jm Js Mf Ml Ng Nm Pz) cI(bN bX cN cO cT dM fR) iC(jH IL qV qZ rY rZ) Et(Ba Cp fR Ib Jd) cB(Ez hG Kr Pk Tr) IL(jG jP Mf nU qZ) Nq(Kg Ks Tv Uh) Jg(In Jm Mn My) dM(bG bN cJ fP) Ba(Ma Pd Uh) Em(Lu Nm Qy) Lv(Mf Ml Pz) Om(In Js Ml) cT(Kq Pk Uv) fR(aG aH cP) Cp(Ad Pd) Lx(Hq In) Mm(Gn Ib) Iu(kK qZ) Pz(Nv oP) jG(jH qZ) jP(cQ oE) EzcC ExUa NoJs MffP MycO NkNl HxiA IbPd TrJd IzKg JknK JtNv Unconstrained panels with 2 analytes, where 1.0E-2 >= 'model p-value' > 1.0E-3. Contains 5,637 panels of 94,547 total panels evaluated. : bV(Aa aC AD aE AF aG aH aI aK AL aM AN aO aQ aR aS aU aV AW aX aY aZ Ba bB bC bE bF bH bI bJ bL bM bN bO bP bQ bR bS bU bW bZ cA cB cC cD cE cF cG cH cJ cL cM cN CP cQ cR cS cT CU CV CW cX cY cZ dA dB dC DD dE dF DG dH dI dJ dK dL dN Dp dR eC Ed EF eM Ez Fa Fb FP Fy Gc gL gP Gz Ha HB HC HF hG Hq Hr Hu Hv Hw Hx Ib Ic IH Ii IJ Ik In iO iP Iz Jd Je Jf Jg Jh Ji Jj Jk Jl Jm Jn Jp Jq Jr Js Jt Ju Jv Jy Kc Ke Kf Ki Kj Kk Kl Kn Kp KQ kR Ks Kx Kz Lh Li Lj Lu Lv Lw Lx Ly Lz Mb Mc Md Me Mg Mh Mi Mj Mk Ml Mn Mp Mq Mr Ms Mt Mu Mw My Mz Na Nb Nc Nd Ne Nf Ng Nh Ni Nj Nk Nl Nm Nn No Nq Nr Ns Nt Nu Nv NW Nx Ny Oa OE OF Og OH Oi OK Om ON Ou Ow Oy Oz Pa Pb Pc Pe PF Pg Ph Pi Pj Po Pz Qa Qb Qc Qd Qe Qh Ql Qm Qn Qt Qu Qv Qw Qx Qy Qz Ra Rb Rc Rf Rg Rh Ri Rj Rm St Tn To Tt Tv Tz Ua Ub Uc Ud Uf Ug Uh Ul Um Un Uo Up Ur Us Ut Uu Uv Vo Vp Vs Vt Vu Vv Wm Tj tF) Uk(aC AD aE AF aG aH aI Aj aK AL aM aN AO Ap aQ AR AS aU aV AW Ax aY aZ BB BC bE bF BG bH bI bJ bL bM BN BO bP bQ bS bW bX bZ cA cC cD cE cG CH cI cK cL cM cN Co cP CQ cR Cs cU CV CW CX cY cZ DB DC DD DE dF DG dH DI dK DL dM dN Dp dR eC Ed EF Em Fa Fb FP Fr Fw Fy Gd GL Gp gW Ha HB HC HF hG Hq Hr Hu Hw iA Ic Id iH Ii IJ Ik Il In IO IP Iq Ir Is It Iv iZ Jf Jg Jh Ji Jj Jm Jn Jp Jr Js Jt Ju Jv Ke Kf Ki Kj Kk Kl Kn Kp KQ kR Ks Kz Ld Lh Li Lj Lu Lv Lw Lx Ly Lz Ma Mb Mc Me Mg Mh Mj Mk Mp Mq Mr Ms Mt Mw Mz Na Nc Nd Ne Nf Ng Ni Nj No Nr Ns Nt Nu Nv NW Nx NY Oa oE OF OH OK Om ON Or Ou Ow Oy Oz Pa Pb Pc Pe PF Pg Ph Pi Pj Po Pz Qa Qb Qc Qd Qe Ql Qm Qn Qt Qu Qx Qz Ra Rb Rc Rf Rg Ri Rj Rm Sr Ss St Tn Tt Tv Tz Ua Ub Uc Uf Ug Ul Um Un Uo Ur Ut Uu Uv Vo Vp Vq Vs Vu Vv Wm Tj Th tF) Fn(aC aD aE Af Aj aK aM aN AO Ap aQ AR AS aU AW Ax aZ BB Bc bF BG bI bJ bL bM BN BO bP bR bU bW cC cD cE cF cG CH cJ cL cN Co CP Cq cR CS Ct cV CW CX cZ dA Db Dc Dd DE dH DI dJ DK DI dM Dp Ed EF Fa Fb FP Fr Fw Fy Gd GL GP gW Ha Hb Hc Hf hG Hq Hr Hu Hv Hw iA Ic Id Ih Ii IJ Ik Il In Io IP Iq Ir Is It Iv IZ Jd Je Jf Jg Jh Ji Jj Jk Jl Jm Jn Jp Jr Js Jt Ju Jv Jy Kc Ke Kf Ki Kj Kk Kl Kn Kp Kq Kx Kz Ld Lh Li Lj Lu Lv Lw Lx Ly Lz Ma Mb Mc Me Mh Mj Mk Mp Mq Mr Ms Mt Mu Mw Mz Na Nb Nc Nd Ne Nf Ng Nh Ni Nj Nk Nn No Nr Ns Nt Nu Nv Nw Nx NY Oa OE OF Og OH Oi OK Om On Or Ou Ow Oy Oz Pa Pb Pc Pe Pf Pg Ph Pi Pj Po Pz Qa Qb Qc Qd Qe Qh Ql Qm Qn Qt Qu

Of Og Oi Om Oy Oz Pa Pb Pe Pf Pg Po Qa Qb Qc Qd Qe) cT(aH AN aQ aS aZ bB bE bF bG bI bN bP bQ bX cB cE cJ cN cO Cv cZ dA Dd dI Dp Dr Et Ez Fa Fb fP fR Fy gC Gn Gz Ha Ic Id Im Iu Jd Jq Jr Jy Kd Kg Ko Ks Ma Mf Mn Pd Pf Pg Po Qg Qw Qx Rb Rh Tr Tv Uc Uh Uo Ur Ut Vo Vp Vs Vt Vu Vv Tj) Jg(Ad Dg Et Hq Hu Hv Hx Ih Ii Ik Il Im Ip Iq Ir Is It Iu Iv Jh jP Jq Jr Js Kg Ko Lu Lw Lx Ma Mc Md Me Mf Mh Mj Mk Ml Mm Mp Mq Mr Ms Mz Na Nb Nc Ne Nh Ni Nk Nl Nm No Nq Nr Ns Nt Nu Nx Ny Of Oh Om Oy Pa Pd Pe Po Qa Qb Qc qZ) aA(eD gC Gn hA hR hV hX iB jD jF jH jK jL jM jO jQ jR jT jU jV jY kC kE kF kG kI kK kO kP IK IM IN IO IW IX IY mE mF mH mI mM mS mT mU mW mY nA nB nC nF nH nI nJ nK nL nM nO nT nU oO oP oQ qT qU qV qW qX qY qZ rA rZ Vq) Ok(Fp Hq Hr Hu Hw Ii Ij Ik Io Iq Jd Jh Jn Jp Jq Lh Li Lj Lw Lx Ly Lz Mb Mc Md Mh Mj Mk Mm Mp Mq Mr Ms Mt Mw Mz Na Nb Nc Nd Nf Nh Ni Nj No Nq Nr Ns Nt Nu Nv Nx Ny Oc Of Og Oi Om Oy Oz Pa Pb Pe Pf Pg Po Qa Qb Qc Qd Qe) Gc(Ad Af Aj Al An Ap Ar Aw aZ BC Bg bH bI Bn Bo bP bR bW bX cB cF Ch cK cN cP Cq Cu Cv Cw Cx cZ Db Dd De Dg Di Dl dN Dr eF Fp fR gL Gn Gp Gz Hb Id Ke Kg Ko Kq Pi Qm Ra Rc Rg Rj Rm Tn To Tt Tv Uc Uf Uh Uo Up Us) eM(aC aD aE aF aG aH aI aK aL aM aN aO aQ aR aS aU aV aW aY aZ bB bC bE bF bH bI bJ bL bM bO bP bQ bR bU bW bZ cA cC cD cE cF cG cH cI cK cL cM cO cQ cR cU cV cW cX dA dB dC dE dF dG dH dI dJ dK dL dN dR eF gC gL gP) Mf(An Ba cO Ez hB hG Hv iA iJ Ik Il Im iP Ir Iv Jd Je jG jH Jk jP Jq Jr jY Kd Kg Ko Ks Ky Ll Lw Lx Me Mk Mr My Ne nK Nl NR Nt Nu Nv Nx nY oE OH Om Pa Pc Pe Pk Po Qa Qb Qg Qv Rf Rh Tr Wm) Pk(aD aK aM aN aO aQ aS aU aW aZ Ba bI bJ bN bR bU cC cE cF cJ cN cO cR CV cZ dA dE dH dI dJ dK Et Ez fP gP hG Hv iA iJ Im Iu Jd Kd Kg Ko Ks Mm Mu My Nm Nq nY oH Pd Qg Qv Rh Tr Vt) Iu(An Ba cJ cO Cp Ez Ha hG iA IB Is Iz Jd jG jH jP jV jY Kd kF Kg Ks Ky lL Mk mM Mr mS nB nI nK nR nT nU nY oE oP Pa Qg QT qU QV qW qX Qy rA rB rC Rf rY rZ Tr Ua Vt Wm) cB(bX Cp Dp Fb Ha Hb Ib Ic Id Im Iz Jd Je Jr Jy Kc Kd Kg Ki Kj Kn Ko Kp Kq Ks Kx Ky Ld My Nd Nh nY oE oF Ou Pi Qg Qh Qw Qy Rf Rh Sr Ss To Tv Ua Ud Uh Uo Up Vo Vt) jG(aZ eD Fr hA hR hV HX iB iC Il iO jD jF jI Jj JK jL jM Jn jO jP jQ jR jT jU jV jY IK IM IN IO Ml Mp nB Nj NI nR nU oE Oy qT qU qV qW qX qY rB rX rY rZ) IL(eD Fr hA hR hV Hx iB Iv jH Jj Jn jO jQ jR jT jU jY kF kG kK kN kO IK mE Mg mH MI mM Mp mS mT Mw mY nA nB nI NJ nK NL nR nT oP oQ Pz qU qV rB rY) Is(Et Hq Hv Hx Ih Il Im Ip Iq Ir It Jk Jn Jq Jr Kg Lu Lw Lx Ma Me Mg Mk Mm Mn Mp Mq Mr My Na Nb Nc Ne Ni Nk Nl No Nr Nu Ny Of Oh Om Pa Pc Pd Pe Qb) Im(aN aZ Bb cJ cO Cu Cv Dd Dg Ez fP gW Hv Ik Il In Jk Jl Jm Js Jt Kd Kg Ko Ks Lu Lw Mk Mn Mr Nb Ng Nk Nm Nr Nu Om Pa Pc Pz Qv Rh Tr Tv Uh Vt) Qv(An As Ba Bb Cu Cv Em Et Ez Hx Ih Ih Iz Jd Je Jk Jl Jq Jy Kd Kg Ko Ks Ky Md Mg MI Mm Mn Mu My Nl Nq Oe Oi Pd Qg Qw Qy Rh Tr Tv Ua Uh Vt) fR(aC aI aM aN aO aW aZ Ba bB bG bH bL bN bO bP bQ bS bU bW cE cG cH cJ cK cN cO cR cV cW cX cZ dC dF dH dL dR Jh Ma Mu Oe Pj Tr Ua) Ba(Ad Al AN aZ bI bN cE cO Cv cZ Dd Dg Ez Fy Hb Jq Jt Kd Kg Kl Ko Kq Ks Ky Md Mg Mn Nm Pf Pg Pg Rh Tr Tv Uc Uv Vo Vt) Ez(Ad As aU bU cJ cO Cu Cv Dd Dg dJ Et fP gW Hb hG iA Je Jq Jt Kd Kg Ko Ks Mg Mm Mn Nm Nq Pd Pz Qg Rh Tr Uh Vo Vt) Fr(Ad aZ cO Dg Dr Em Gn IIr Hw Ii Ij Ik Jk Jn jP Kg Lh Li Lx Lz Mp Ms Mt Mw Nf Nt Nv Oi Pb Qa Qd Qe Tr) Pd(An Aw fP gP Ha hG Iz Jd Je Jk Jq Kd Lh Lx Mk Mp Mr Nt Nu Nv Ou Pa Pe Po Qg Qh Qt Qw Qy Rf Rh Ua Un) iC(aZ bN cJ cL cQ eD gP hA hR hV hX iB iO iP jP jT jY kK nR nU nY oE oH oP qT qU qW qX qY rA rB rC rX) Jt(Cp Em Ib Ik Ir Iz Jd Jk Jp Lh Li Lx Mk Mr My nK NR Nu Oh Om Pa Pc Po Qa Qb Qd qZ Ua) Nq(cO Cu Dg Fa Fb Fy Hb iA Jy Kd Ke Kf Kj Kl Kn Kq Ky Pj Qg Rh Tn Tt Uc Uf Uv Vo Vt Wm) Pz(Ik Ir Iz Jd Jk Jp kF kK Lh Li Lx Mk Mr Mt My Nb nK NR Nu Oh Om Pa Po Qa Qb Qd Ua) Kg(Ao Cp Ct Em fP Ha Hc hG Hx Ib Jd Je Jk Jl Kd Lh Mu My Oe Oi Po Qg Qh Qy Tr Tz Ua Un) jP(aE aF aO aQ aZ bN cJ dE gP gW Hx iB iO iP jH Jj Mp Ms Mw Nj nR nY oF oH qU rB rY) Cp(Af Al As aZ Bb bN bU cE cJ cO Cu Cv Cw cZ Dd Dg dI Dl gC Jq Ko Mg Mn Nm Tr Uc) Om(Hv Ib Ij Ik Il Ir Jk Jm Jn Jr Lu Mg Mk Mn Mr My Ne Ng Nk NI Nm Nr Nu Ny Oh Pc) Ks(Ct Ha Hx Ih Iz Jd Je Jk Jl Kd Ml Mu My Na Oe Po Qg Qy To Tr Ua Us Uv Th) nK(Hx Ih Ir It Iv Jr Js Lj Mj Mn Ms Mw Ne Nf Ng Nj Nr Nx Og Oy Qa Qd Qe) Et(An Ao Aw Dk Dp Em fP GI Ha hG Ic Iz Je Kd Ou Qw Qy Rf Sr Ss Ua Un) Mu(Ao aZ Bb bF cE cO Cq Cu Cv Dg Dk Ij Ik Kd Ko Qx Tr Tv Uc Ut Vs Vu) Ib(As Cu Dr Em Gn Hb Jq Kd Ke Ko Md Mg Nm Pg Pj Rh Tr Tv Uc Ut Vs Vt) In(Hw Hx Ir Iv Jk Jq Lh Mk Mr Mz Nb NR Nt Nu Nv Pa Pb Pe Po Qa Qb) cO(cAn Aw cN dG FP hG Hx Ih Jl Jr Kd Ma Mj Mr Nb Nh Nu Po Qg) Mn(An Hx Iz Jd Jk Jp Li Mk Mr My No Nr Nv Oh Pa Po Qa Qb Ua) hG(aZ bN cJ Cw fP gP Hx Iv Kd Ko Ky Ma oH Ow Pf Qw Qx Rh Tr) Nk(Hv Ir Jk Mk Mr Nc Ne No Nr Nu Nv Oh Pa Po Qa Qb) Jd(Ad Bb Cu Cv Dg Jq Kd Ko Ma Mg Mm Nm Qg Rh Uh Vt) nR(Ir It Iv jH jT IK IO Ma Mj Nd Nf Nj rX rY rZ) Em(As Ct Hc Hu Hx Jf Jl Mg Mk Mw Oe Rh Ua Vt) Tr(Aw bU dA Dp Hx Iz Je Jl Kx Ky My No Rf Ua) fP(An aW bG bN cE cJ cN Hx Kd Ky oN Ow Qg Rh) kK(Ir It Iv jH Jk Js Lj Mk Ms Mw Nf Nj Qe) My(Ad Cu Cv Dg Jm Kd Kj Ko Mk Ng Uh Vt) Ua(Ad Cu Dg Dr Gn Kj Ko Mg Nm Uc Vo Vq) bN(An Aw aZ bG bX cN cZ dA dG dN gL oH) rB(aD aI aO bH bM cJ dE iP oE oF qZ rY) Hx(Fy iJ Ik iP Kd Ko nY oH oK oN Uh) It(kF kN kO lY mM mS nB nI nT nU oP) Ir(Il Jm kF Lu Mk mS Ng nI Nm oP) jH(aZ cJ cQ mE mM mS nB Nj nT nU) qZ(Hv Lj lO Ml Mr Ms Qd Qe rY rZ) Dr(cN Hc Hu Lu Mm Oe Pj Qy) Kd(An Hv Je Jl Nm Qg Rh Vo) Ko(Aa An Iz Je Jl Kx No Qy) Gn(cN Hc Hu Lu Oc Pj Qy) Ng(Ik Jk Mk Mr Nv Oh Po) lI(Jk Mj Mk Mr Nr Pa Pe) Mg(Aw Ct Iz Jk Nv Qy) Jm(Jk Nv Oh Po Qa Qb) Jq(Jn Jr Js Md Mk Ml) nI(Iv Jk Ms Mw Nf Og) oP(Iv mH Mj mM nN Og) An(aZ Cv cZ Dd gL) Cu(Iz Jl Lh Li Nh) Nm(Iz Lh Nv Oh Po) Pj(Ex Ic Id Sr Ss) qW(aF aO bM iP oE) Aw(Ad aZ cE Dd) Mm(Ic Id Sr Ss) Qg(Al Dp Je Vt) Jl(iA Ii Ij Ik) Dg(Ap Iz Nh) Ma(hB oF oH) qU(nU rY rZ) Mk(Hv Oh) Ml(Nb No) Nj(jY kN) Hc(Ex Gz) Iz(Ad Kj) aC(bE cZ) aZ(nY pF) bG(cN dG) bX(dA dI) iP(hX iB) DcDd DkMw WmJj LxNd MjnJ NcNl NfkF IvnU JrcJ aVdA bMqX mMrY iOjM

Constrained panels with 3 analytes, where 1.0E-10 >= 'model p-value' > 0. Contains 2 panels of 10,943,034 total panels evaluated. : Gc{Oe(Ql Qn)}

Constrained panels with 3 analytes, where 1.0E-9 >= 'model p-value' > 1.0E-10. Contains 78 panels of 10,943,034 total panels evaluated. : aA{Js(Fr Ir Jg Ji Jk Lv Lw Mi Mu Mz Nl Nw Ok On Pd Po Qb Qc) Jg(Il In Iu Jt Md Mn Mt Ng Nr Pz) Ok(Ih In Ir Iu Jt Md Mn Mt Pd Pz) Nw(Il Ir Iu Jt Md Mt Pd Pz) Md(Jk Mq Mu Mw Om On) On(Ir Iu Jt Mt Pd) Ik(In Ng Nr Pz) Jk(Il In Iu Mt) Pd(Ih Iu Lw Mi) Nn(Jt Mn) Lw(In Ir) Ih(Ir Qb) FrIu} GcMyOe GdMmHu Constrained panels with 3 analytes, where 1.0E-8 >= 'model p-value' > 1.0E-9. Contains 210 panels of 10,943,034 total panels evaluated. : aA{On(Et Ih Ii Il In Is It Iv Jo Jr Lh Lz Ma Mn Nr Ny Oh Pe Pf Pg Po Pz Qe) Pd(Fr Ik Il In Ir Jg Ji Jk Jo Jt Lv Lz Md Mq Mt Mu Mv Ng Nl Nr Om) Nw(Et Ih In Jo Jr Lh Lz Ma Ml Mn Nr Ny Pg Po Qe) Lv(In Ir Jn Jo Jr Jt Lh Md Mf Ml Mt Ny Pz Qa) Lw(Hw Ij Jt Jn Jo Jr Jt Md Ml Mt Na Ny Qa) Ji(Et In Ir Is Jn Jo Jr Jt Md Ml Mt Ny Qa) Jk(Hq Ih Ir Jm Jo Jt Lh Lz Mg Ng Nl Nr Pg) Jg(Et Ih Ir Jo Lh Ma Mg Ny Pg) Pz(Fr In Md Mt Mu Mv Nn Qc) Fr(Et Il Jt Mg Mt Nr) Nn(Et Il Ma Md Nr Ny) Mu(In Jt Mt Ng Nk Nr) Qc(Ih Ir Jt Mn Ng Nr) Mi(Hq In Mt Pg) Mv(Il Jt Ng Nr) Mw(In Mt My Ny) Nl(Ih Nc Nk Nr) Ok(Et Jo Jq Nm) cO(cS Ir Iv Ko) Md(Mn Nv Pc) Ik(Jo Jt Mf) Mn(Ih In) Mq(Jr Mt) MtPc NyOm aJdG cEcS} Gc{Oe(Au Cp Fn Iv Je Jg Ji Kk Kr Mm Ms Mu Oz Qy Rh) MmMy} CwGdHu NnMnJj aJcSdG Constrained panels with 3 analytes, where 1.0E-7 >= 'model p-value' > 1.0E-8. Contains 196 panels of 10,943,034 total panels evaluated. : aA{cO(aX cI Cv cW cZ Et Fn Hw Ij In Iq Is It Iu Jn Jo Jq Jr Js Jt Kd Kq Kr Li Lw Ma Md Ml Mn Mp Mr Mt Mz Na Nm Nn Nr Ny Oh Om On

Figure 13 Continued

Pb Pd Pe Pg Qd Uk) cS(aH aI aL aP aY bB bG bL bN bO bQ bW cG cI cJ cK cV cW cZ dF dG dH dL eF) Ko(Af aK An aU bV cB cC Cp Cu Cx dK Fa Fn Jd Jg Ju Ky Nq Oy Uk Up) Cu(Fn Ik Iz Kd Ky Oy Uu) bN(bG bQ cE cI cW fP) fP(cG cJ Ky) Af(Iu Kd) Lw(Hv Nf) Kq(bV cB) FnKy GcOe MuMy aYcI bGbV} Gc{Oe(Ha Ib Jf Rf Vt Wm) My(Ko Ma Nr Rc Ue) Cs(Ba Ct) CtEx WmMu} aJ{dG(aX bG bL bM bN bV cI cO dE dI) cO(cI cS dL) cSdL} Mv{Pd(Ji Nw Ok On) Jl(Jj Jo Jt) Jo(Ok On) Jt(Ok On) EmMm PzJj} Gd{Hu(Ap As Jt Ke Kj Mt Pj Ue Vs) Mm(Dg On) OeVt} Mu{Jj(Jl Mf Mn Pz) Ok(Jo Jt Pd) On(Jo Pd) EmMm OmPd} Nn{Jt(Jl Ok On) JoOn} Em{Hu(Nm Pj) MmJl} Gn{Mm(Ao Hu)} Pd{MiOm PzNw} JtOnPg

Constrained panels with 3 analytes, where 1.0E-6 >= 'model p-value' > 1.0E-7. Contains 915 panels of 10,943,034 total panels evaluated. :
aA{cO(aL aM As aY bE bG bN bQ cQ Cu Cx Dd dG dL Fa fP Hv Ii Ji Ke Kf Kg Kj Kn Kp Ky Lh Mf Mi Mj Mq Nb Nf No Nx Ok Pf Pi Pk Po Qa Qe Qx Ra Rb Rj Tr Uc Ud Ue Uo Up Us Ut Uv Vp Vs Vt) Ky(Af aK As Bb Bn bV cB cC cS Cv Cw Et Fa Fb Iv Jq Kd Kq Kr Ks Md Mm Mp Mt Pd Rb Tr Ue Uk Uv Vt) Fn(Af Bb Bo bV bW cB cE Cw Dg dH Et Fa Fb Kd Kl Kq Mf Mm Mn On Pd Pk Qe Tr Tv Uh Uk) Af(Ed Fa Fb Ir Kq Kr Ma Md Mp Mt Nr Oh On Pd Pg Pk Qb Qd Qe Tr Tv Uk Uo Uv) bV(aP bL bQ cE cK dG dH eF Et Fa hB Jp Kd Li Ma Mp Mt On Pd Pg Pk Qd Qe Tr) cS(An Ap cQ Cu Cv Cw Dg Et Fa hB Kd Ko Kq Mp Mt oK Pd Pk) Up(As Cu Et Fa Jq Kd Kq Kr Mp Mt On Pd Qe Tr Uk) aX(aC aP bG bL bQ bW cE cG cI cJ cQ dG dH eF) Bo(Iq Ir Is It Iu Iv Jo Jq Kr Mn On Pd Uk) Ko(aN aQ aV aZ bN bW cE cJ cY dJ gW Tr) Kq(aK aN aU bW cC cJ Jd Kd Nn Nq Oy Uk) dH(aH aK aL aM bB bE bN cJ cZ dI dL Io) aN(aL aY cW cZ dG dL Et fP Kd Mp) Iu(As Bb bW cE cJ Dg Fb Qg Uh) cI(bG bQ cE cW cZ dF dG dL eF) Cu(An Ao Cp Dk Fy Hv Ib Uv) Fa(An cB Ha Oy Pk Po Tr Uk) Tr(cB Jd Jq Kd Mn Uk Tj) Io(Bc cE cG cJ CV dF) bG(aY cJ cW cZ dG dL fP) bN(aH aL aY bL cZ dG eF) Kd(Bb cB Fb Mm Oy Uk) bW(fP Ir It Iv oH Pk) Ap(Iq Ir Is It Iv) Kr(cB Cw Fb Oy Pk) Uk(Et Mm Mn Oy Uh) fP(bQ cB cE dF dG) Bb(Mp Mt Oy) Cp(Ad Cw On) Gc(Ax Cs Of) Ma(As Ba kS) aC(aL bE cZ) bX(cB cJ dL) cE(bE cR dM) Ao(Et On) Cw(Fb Oy) Dg(Ir Iv) Mn(As Cv) bQ(cR dL) dG(aP dM) AnMt EtJd FbIr MmPk MvjP IvUh aJdL aKbL bScJ} Gc{My(Ad Al Ap Ar Bb Bo Co Ct Cw Dg Et Ii Jt Ke Kx Lx Mt Mu Nm No Om Pd Pe Pf Pg Pj Po Rh Uh Uv) Hc(Ad Cw Dg Et Iv Kg Ma Mg Na Oz Pc Pd Rh Ub Ue Wm) Mu(Ba Bo Ct Em Hr Ly Mk Mm Of Oi Rb) Cs(Ao As Cp Dk Ef Fr) Mm(Fw Ii Jg Ji Mx On) Ct(Ax Jl Mw Mx Nb) Wm(Ib Jl Mw Qy) Ex(Ao As Cp Ef) Ax(As Ba Ef) Ib(Me Ou Rb) Qy(Ly Me Rb) Of(Jo Nb) EmFr LyMw MkJl HuOw OuVt} On{Pd(Fr In Ir Is Iu Jj Jl Jo Jt Mi Mn Mx Mz Ne Nl Nn Nt Nu Om Pg Po Pz) Jt(Fr In Ir Is Iu Jg Ji Jj Jl Jq Mf Mu Mx My Nl Oh Oy Qa) Jo(Fr Ik Ir Is Jl Jq Mn Mx Nl Nx Pg Pz) Jj(Iu Mf Mn Mu Mv Nn Pf Pg Pz) Mv(In Mg Ng Pz) Nn(Mn Nm Pz) Mu(In Mg Pz) Pg(Mn Nm Pz) GdHu GnMm} Mu{Jo(Fr Ip Ir Is Ji Jl Jq Lv Mf Mi Mk Mr Mv Nk Nn Nr Nw Om Pa Pe) Mg(Fr Jg Jj Mi Mv Nw Ok) Jt(Em Is Ji Jj Jl Nn) Pd(Ji Jj Jl Jq Mi Nw) Pz(Fr Jl Nn Nw Ok) In(Is Jl Mi Nw) Em(Cw Et Nm) Uk(Kq Ny Pg) Nn(Jj Mn) Mv(Jj Ng) ExQv NmOk MdKo MiHq IbUt IsJm IuJl} aJ{cS(bG bL bN bO bW cE cI cJ cK cW dH) bN(bG bL cE cI cO cW cZ dH dL) dG(Al An Aw Ba Cp eM fP Iu Pk) bG(aX bA bV cI cO cT dL) cO(aD aX aZ bM cW cZ) dL(aC bL bS cE cI dE) cI(aX bL bM) aXdH} Mv{Jo(Ir Is Ji Jj Lv Mi Mk Mr Mx Nk Nn Nw Om) Jj(Ik Jt Ma Mf Mg Ml Mn Nn Pd) Jl(In Iu Mg Ng Pd Pz) Pd(Lv Lx Mi Om) Mg(Ji Nw Ok) In(Is Mi Nw) Ng(Jg Nk) Pz(Nw Ok) Jt(Is Ji) DrMm NmOk NnMn NrkO MiHq} Jl{Jj(Iu Jk Jt Lv Mf Mn Nn Nx Oh Pf Pz Qc) Jt(Fr Is Jg Ji Jq Nv Ok) Jo(Fr Ji Jq Nn Ok Om) Nn(In Mn Nm Pz) Pd(Ji Jq Ok Om) In(Jq Om) FrPz} Gd{Hu(Ad Ar Bb Co Dg Et Ij Iu Jd Ko Ma Mg Pd Rh Ub Uc Uh) Hc(Ap Bb Co Ij Mg Pd) Mm(Ap Cu Dl Ef Uu) Oe(Pj Qw Rh) AoPj UaJf} Nn{Jj(Et Jt Ma Mf Nm Pz) Mn(Fr Jo Jt Mi Ok) Jo(Ji Lv Mi Ok) Jt(Fr Is Ji Nw) Pz(Fr Ok) OkPd} Pd{Ok(Fr Jk Jo Jt Mi Om) Om(Fr Jj Md Mx My) Nw(In Js Mi Ml) Fr(Mi Pz) NqKo MiHq} Jo{Ok(Fr Is Jg Jk) Fr(Is Lv) Tr(Iz Nq) EmHu MdOm MiHq MlNw} cO{aP(cI cW Et Fn Kr Tr Uk) Uk(bA cT) BacS} Pz{Fr(Is Jj Mg) Jg(Jj Ng) Nw(In Ml) MiHq JjJk} Em{Mm(Jp Lx Mw Po Qy Ua) PoPj NmHc} Jt{Ok(Fr Is Jg) Nw(In Ml) FrIs MiHq JjJk} Mn{Fr(Jj Mg) NqTr JjJk} Mi{Hq(Iu Jj Lu)} CwJhfR TiRfPk FrMfJj GnMmIb rBqZlL Constrained panels with 3 analytes, where 1.0E-5 >= 'model p-value' > 1.0E-6. Contains 3,243 panels of 10,943,034 total panels evaluated. : aA{Up(Ad Ax Bn Cp Cq Cs Cw Dc Dd dL Hw Ii In Ji Jo Jr Js Jt Ke Kf Kg Kj Kn Lh Lw Lx Mj Mq Mr Mz Nm Nn No Nr Nt Nx Ny Oh Om Pe Pf Pg Pi Po Qa Qb Qd Qh Rb Rm Tv Uc Ue Us Ut Uv Vs Tj) bV(Ap cG Cu Cv Fb iA iJ Jo Jq Jt Ke Kf Kg Kj Kl Kn Kr Ks Kz Lx Md Mg Mm Mn Nm Nn Nr Ny Oh OK Om oN Pf Qa Tv Uc Ue Uf Uh Uk Ut Uv Vt) Bo(Fy Hv Hw Ii Ij In Ji Jn Jr Js Jt Kg Kj Kn Lh Lw Mb Md Mj Ml Mq Mr Mz Na Nb Nf Nm Nr Nx Ny Oh Om Pb Pe Pg Pi Pk Qa Ra Rb Ue Uv) cS(Fb Fn iA iJ Ir It Iv Jo Jp Jq Ke Kg Kl Kr Ks Kz Li Ma Md Mm Mn Nn Ny Oh Ok ON Pf Pg Qa Qd Qe Tr Uf Uh Uk Ut Uv Vt) bW(aJ Et Fa Ij Jo Jq Jt Kd Kg Kn Kr kS Ky Li Lj Lx Ma Md Mn Mp Mt Nn Nr Ny Oh Om On Pd Pf Pg Pi Qd Qe Ue Uk Uv) aN(aD Fa Fn Iq Ir Is It Iu Iv Jo Jq Jt Kg Kr Li Lx Ma Md Mn Mt Nr Oh Ok Om On Pd Pf Pg Pk Qa Qd Qe Tr Tv Uv) aK(aP Ed Et Ez Fa Fb Fn iA Io iP Ir Iu Jp Kd Kr KS Ma Mn Mp Mt Nn Nr oK ON Pd Pk Qa Qd Qe Tr Tv Uk) aU(Ed Fa Fb Fn Ir Iu Iv Jt Kd Kr Ky Ma Md Mf Mp Mt Nn Nr Oh On Pd Pf Pg Pk Qa Qb Qd Qe Tr Tv Uk Uo) Oy(Ad As Ax Bc bI Cp Cq Cs Dc Dd dG DL Fw Gc Ke Kf Kj Kl Kn Kp Pi Pk Rj Rm Tv Uc Ut Vs Vt Tj) Fb(AD aQ As Ax Bn bU cB cC cJ Cv Cx dJ dL Jo Jq Kg Md Ml Mt Oh Ok Om On Pg Pi Pk Uv Tj) cC(Ed Et Ez Fa Fn Iu Jp Kd Kr Ma Mn Mp Mt Nr Ny Ow Pd Pk Qd Qe Tr Tv Uk Uo) fP(Cw Et Fa iA Ke Kq Li Ma Md Mm Mn Mp Mt Nn Oh oK ON Ow Pd Pf Qe Ut) dJ(Et Ez Jp Kq Kr Ky Ma Mf Mn Mp Mt Nn Nr Ny On Pf Pg Pk Qd Qe Tr Uk) gL(bE cZ Fn Jq Kq Kr Lw Md Mf Ml Mp Nr Om Pd Pg Pk Qe Qx Tr Tv Uk) kS(aQ As aY bN bQ cB cG cJ cO cW dF dN Fn hC iA iP Ko Ky Mf oK oN) Gc(Ex Hc Hf Hq Hr Ib Ic Ii Jk Kc Kp Mk Nd Og Oi Ou Ow Qz Um Uu) Tr(aD aQ aX bO bR bU cE cF cG cJ Cw Cx dI Jo Kp Kr Ok Pd Pk) aX(An Ap Cu Cv Cw Dg Et iA iP Jp Kq Ky Ma oK oN Qd) Io(aD aH aM aY bB bI bQ cQ cW cZ dG dL dN Kg Uv) Pk(As cB cE cG cJ DG dH Kl Ok On Qd Uh Vt Ti) dK(Et Iu Iv Kq Kr Lx Ma Mn Mp Oh Ok On Pf Qd Qe) Ed(Bc Cv Cx Dg Jp Kg Kl Ks Mg Pz Rh Uf Vo Vt) Ma(aD aM aQ bI bN bZ cB cJ cW dG dI dL Jd) Ky(aY bI cE cJ dG dH dL Jo Qe Rh Tv Vo Ti) Uk(aQ bU cB cE cG cJ dF dG dH dI dL oN) Mn(aD bI bN bU cB cJ cW dG dH dL Tv) aQ(aP bL bS cK dH iP Kr oN Qd Qe) aZ(Af As Cu Cv Cx Fn Kr On Qd Qe) An(Ad As cE Cw cZ Dd dG dL Qe) Dg(Ao Ap bN Ik Iz Jd Md Nr Oi) Tv(As bU cB cF cO Cx Ke Mm Uh) Af(Ao Aw bN cZ dG dL eF Tj) Uh(As Bn Ir Md Ml Nn Nr Oi) cB(eM Et Jy Mp Mt Pd Ue Uo) cJ(Fn Kd Kr Mt Pd pF Qd Ue) dH(dF gW Iu Kr Md Mt Pd Ue) oH(aY bM bN cO cW dN oK oN) aG(aD Iq Ir Is It Iv Nr) cE(Aw Ba Cv Kd Kr Mt Nn) Kl(Iv Iz Jd Ml Oi Uu) bN(Al Ap Cu Cv iP Mt) dI(Md Mp Mt Pd Pf Pg) Fn(cG dF dG iA oN) Ex(Je Oi Ou Ua) Iu(bI bO cV iA) Iv(bO bZ oK Qg) Jd(Ke Ok On Uf) Ap(As Dd Tj) Aw(Ad Cu Cw) Cp(As Cq Dd) Cv(aC aY dG) Ib(Kq Pd Ut) Qe(cY jK qU) Qg(Iq It Qa) bU(bS Md Nr) bZ(Ir Is oN) cO(Kx Ld Tn) gW(aP iA iP) Ao(Ad Cw) Cu(aY Dc) Tj(Cx Jy) Mm(Ax Uv) Qd(bI cY) Jo(Ct Jy) Kr(bR cF) On(bI Iz) bX(aI dF) eM(bL bS) iP(cQ cW) AsJp EzHb HaPd MfjG MwjP KdcF KoiA OiUf aJaP aOoN dGfR} Gc{Ou(Ap Ar As Bc Bo Ct Cw Et Hb Il Ip Jl Kr Kx Ma Mk Ml Mu Mw Na Nm Og Pd Pf Pg Qv Qy Rh Tr Ua Ue Uf Us Uv Vp Wm) Ib(Ad As Ba Ct Cv Em Gn Hc In Ip It Iv Je Jr Jt Kd Kr Ly Mk Ml Mu Mv Mx My Nn Nw Ow Pd Pi Pk Qg Qv Qy Vt) Ct(Fr Il Im Ip Je Jr Lx Mi Mr Mv Na Nn Nt Nu Nw Oa Ow Qt Qv Qy Rb Rf Ri Tz Ub Vp Wm) Of(Aj As Ba Bb Fr Il Ip Je Jj Jl Lx Mm Mv Mw Mx Nn Qt Qv Qy Rb Ub Vo Wm) Hc(Al Ap Bb Co Ip Jl Jo Ke Kl Ms Mu My Nc Nr Om Pf Pg Rb Tr Uf Uv Vt) Qy(Ba Bo Em Fp Hf Hr Hv Ip Jr Jy Mx Na Nw Nx Og Ow Qt Qv Tr Ue) My(Af Bc Fw Hb Il Kg Kq Mg Mk Nb Ow Pk Qm Tn Tr Ua Uf Vt Wm) Mw(Bo Em Hf Hr Ip Jy Kq Ma Me Og Oi Ow Pk Qv Rb Tr Ue) Ua(Bb Cu Cw Ip Je Jl Ly Ma Me Ng Oi Ow Qv Rb Ue Vo Wm) Mm(Ap Dg Ik Li Lx Ng No Nt Og Ok Pe Pf Po Qu St Uu) Ba(Ex Il Jl Ly Ma Mk Na Nb Nn Og Oi Qv Ub Wm) Ef(Et Il Ip Kl Ly Ma Ng Ow Pd Qv Ue Vo Wm) Mu(Hf Hv Je Jy Kc Kd Kq Kz Og Ow Pk Qv Tr) Jl(Bo Ed Em Hr Jy Kq Ly Og Oi

Figure 13 Continued

Ow Qv Rb Ue) Ax(aJ Ao aX bA bP cK Cp cT Dk Em Fr) Nn(As Bo Je Ly Ma Mk Ml Nb Rb Rh Wm) Em(As Cs Cu Dk Ex Fb Gl Lx Mx)
Cp(Et Ma Pd Pg Pj Rh Uc Wm) Nb(As Hr Jy Mk Ms Nw Og Tr) Iz(Bb Ip Ng Pd Qv Rb Ue Vo) Wm(Fr Je Jk Mv Nv Qt) Cs(aX bA bS cK cT)
Mv(Bo Ly Ma Og Ue) Ex(aE cT De Dk) Mx(As Hr Mk Og) Jg(Bb Cw Et Pd) Jk(Ip Jf Qv Rb) Ao(Pd Pj Ue) Fr(Cu Ly Og) Po(Ly Rb) Mi(Og
Oi) Mk(As Nw) FyRh LyQt UeOn JiPj NwVt UuVo} Mu{In(Hv Hw Hx Ir Iv Ji Jq Jt Lv Lx Mf Mg Mj Mk Mn Mr Mv Mx Mz Nb Ng Nn Nr
Nu Ok Om Pa Pb Pe Pz) Pd(bV Fn Fr Hw Is Kq Lh Li Lv Lx Mf Mk Mn Mp Mr Mv Ng Nk Nn Nr Nt Nu Pa Pe Pz) Jt(Fr Hx Ir Jg Jm Jq Lv Mf
Mi Mk Mr Mv Mx Nk No Nr Nv Nw Oh Om Pa Qa Qc) Pz(Ir Is Jg Ji Jm Lv Mf Mg Mi Mk Mr Mv Mx Ng Nk Oh Qa Qb Qc Qd) Jm(Fr Hx Ir Jl
Lv Mf Mi Mn Mv Mx Ng Nn Nw Ok On Qb Qc) Uk(CO Cu Dk Ex Jd Kd Md My Nq Nv Tv Uc Ut Vs) Em(Ad As Bb Dc Gd Iu Jo Kf Ma Om
Pj Qe Uc Ue) Jl(Et Il Js Mf Mg Mn Ng Nk Nl Nm Nr Ok Pf Pg) On(Et Il Iu Js Mf Mn My Ng Nm Nr Oy Pf Pg Po) Ex(bV cS Et fP Hb Ip Iu Ma
Nm Tr Ue) Mn(Fr Ji Jo Lv Mf Mg Mi Ng Nk Nw Ok) Md(Cu Fn Kq Kr Om Pk Qv Tr Ue) Ng(Fr Jg Lv Mf Mi Ml Nk Nn Ok) Pg(Cu Fn Ko Kq
Ky Pk Qv Tr Ue) Mg(Is Ji Js Lv Mf Nk Nn Om) Js(Is Ji Jq Mi No Nw Ok) Tj(Iu Ko Ma Tr Ue) Gd(Hu Jy Kd Kq Oe) Mf(Ji Lv Mi Nk Ok) Ml(Is
Jq Mi Nw) Nm(Is Ji Nn) Ma(Kq kS Mi) Iu(cO Cu Mr) Et(Ji Ok) Fn(Dk Kq) Nk(Mi Nl) Tr(Nv Ny) Im(Jj Jo) Nw(My Ny) CoMp MrKo TvOm
IlPa JgJo} Mv{Pd(Fn Fr Hw Is Jq Lh Lw Mk Mp Mr Mx Mz Ng Nk Nn Nr Nt Nu Pa Pe Pz Uk) Pz(Il Ir Is Jg Ji Jm Jo Lv Mf Mg Mi Mk Ml Mr
Mx Ng Nk Nn Nu) Jl(Et Hq Ih Il Jm Js Lj Ma Mf Ml Mn Nk Nl Nm Nr Ok Pf Pg) Jt(Fr Il Ir Jg Jq Lv Mf Mi Mk Mr Mx Nk Nn Nr Nu Nw Om
Pa) Mg(Fr In Is Jg jP Js Lj Lv Mf Mi Mk Ml Mn mZ Nk Nn Om) Jo(Fn Fr Il Jg Jq Lh Lw Mn mZ Ng Nr Nu Nx Pa Pe Tr) On(Et Il Iu Jm Js Ma
Mf Mn My Nm Nr Oy Pf Pg Po) In(Hw Hx Iv Ji Jq Lx Mr Mx Mz Ng Ok Om Pb) Ng(Il Jk Jm Lv Mf Mk Ml Mn Mr Nn Ok) Uk(cB CO Et Fn
Iu Ue Uh) Jm(Ir Is Mi Mx Nw Ok) mZ(Jh Ma Nf Nj Nq Nr) Mn(Ji Lv Mi Nw Ok) nK(Jh Ma Nf Nq Nr) Nm(Em Is Ji Nn) Js(Is Ji Mi Nw)
bV(cO Cw Et iA) Mf(Lv Ok Ue) Ml(Ji Mi Nw) Il(Mk Mr Pa) Et(Ji Ok) Ma(kS Mi) Nw(My Ny) cO(aJ aP) EmPj NrMx MjnJ Mrlu NkNl UeKy
jPIL} Jj{Jk(Ik Im Ir Is Jo Lv Ma Mf Mi Mx Ng Nk Nl Nn Nu Nx Oh Ok Pd Qc) Ik(Fr Hv Hx Im Is Jl Mf Mi Mk Ml Mr Nn Oh On Pa Pz Qb Qc)
Mf(Ir Is Jg Ji Lv Mi Mx Nu Nv Nw Nx Oh Ok Po Qb) Mn(Is Jg Ji Lh Lv Mi Nv Nw Oh Ok Po Qa Qb Qc) Ml(Fr Ir Is Jg Lv Mi Mx Nn Nw Ok
Om Qb) Pz(Is Ji Lh Lv Mi Nv Nw Oh Ok Po Qa Qb) Mi(Is Jg Js Me Nl Nn Nx Oh Pd) Jg(Jo Jt Mg Mx Ng Nl Nu Oh) Nn(Jo Js Lv Me Mx Nl
Ok) Fr(Et Jt Ma Mg Nl Pd) Is(Et In Ir Js Jt Nm) Nw(In Js Nl Ny Oh Pd) Ok(Jt Lu Nl Nm Oh Pd) Et(Ji Jl Nv) Lv(Ir Mx Oh) Qb(Ih Me Nk) Jt(Ji
Lh Nv) Om(In Js Md) On(Im Jo Nl) NmJi MeOh NkNl ImJl} Pd{Nw(Fr Is Jk Jl Jo Jt Li Lv Lx Md Mn Mp Mt Mw Mx My Ne Nl Nn Nq Nt Nu
Nv Ny Oh Ok Om) Om(Hu Ik In Ir Is Iv Ji Jo Lv Lx Mg Mn Mp Mr Ne Ng Nl Nn Nt Nu Oh Oy Po Pz Qa Qb) Fr(Hw Ir Is Ji Jl Jq Jt Lv Lx Mf
Mk Mn Mr Mx Ng Nl Nm Nn Nr Nt Nu Pa Pe) Ok(Hv Is Jg Lu Mf Mn Mr Mx My Ne Nl Nm Oh Po Pz Qb) Mi(Is Jg Ji Jk Jl Jq Mf Mx Nd Nn
Nt Nu Nv) Fn(aP BA bV Cp Mx My Nq Uk) Jl(In Is Iu Jg Jk Lv Nn Pz) On(Ik Il Im Oh) Ji(Jk Lu Nn) Pk(bA bV cT) Nq(Kr Tr) Lx(Hq Nd)
Mx(bV Uk) aP(bW cO) Balb GdUa NnMn bVcO} aJ{cO(aM Aw Ba bV Ed Et Ez Fn fP Io Iu Ko Kr kS Ma Mk Mn Mx Pk Tr Uk) dG(Ez Fn Iv
Kd Ko Kq Kr kS Ky Ma Mn Mr My Ow Tr Tv Uk Up) bM(aC bG bL bX cS cW cZ dE fP iA iP kQ KR kS) bV(aM aP bL bO cE cI cK cW cZ
dH Et hB iA Ko) aX(aC aM bL bO bQ bS bW cE cG cJ cK cW) dH(cI cJ cT cW Io Iu Ko Kr Pk) kS(bN bQ bW cB cW dL iA Ma oN) iA(aD bN
cS cW fP Iu Ko) cS(An cT cZ Dg hB) Ko(Ba cB Cp dL) bA(cE cJ cW dF) bG(bL bO bW cJ) cT(cE cJ cW dF) Kr(cB cF Pk) cZ(aC bL bW)
bO(cE cI) fP(cJ oN) TrcB IudL aRcl} Jo{Nn(Fr Is Jg Jq Ma Me Mf Mk Mr Mx Nk Nl Nm Nr Nu Nw Om Pa Pe Pz Tr) Fr(Hw Ik Ir Ji Jq Mf
Mi Mk Mn Mx Nk Nl Nu Nx Om Pz) Jl(In Ir Is Iu Jg Jk Lj Lv Nk Nl Nv Nw Nx Po Pz) Jg(Ir Is Ji Jq Lv Mi Mx My Ng Nk Nu Om Pz) Nw(In Ir
Is Js Lv Md Mi Mt My Ny Pz) Is(Ji Jk Jm Lv Mi Mk Mr Om Tr) Ok(Ik Im Ir Jt Mn Mx Nx Om Po) Tr(aP Cp Jd Jk Lh Mx Ua) Fn(Cp Hv Iz My
Nq Po) Mi(Ik Ir Ji Jk Nv Nx) Ji(Ir Jk Lv Mk Mn) Ti(Al Ao Pk) Nq(Ko Kr Th) Lv(Ir Jk Nv) Em(Hc Ua) Om(In Ml) On(Il Im) Culz GdHu
MnNv} Jl{Jt(Em In Ir Iu Jk Jp Lh Li Lv Lx Mx My Nk Nl Nw Nx Oh Om Po Qa Qb Qc) In(Fr Ir Is Iu Jg Ji Jk Lv Mn Mx Mz Nl Nt Nw Ok On
Po Pz Qb) Pz(Is Iu Jg Ji Jp Lv My Nk Nv Nw Ok On Pg) Js(Fr Is Iu Ji Jn Jq Lv Nn Nw Ok Om On Qb) Nn(Et Iu Jm Ma Mf Mm Ng Nr) Iu(Fr
Lv Mf Ml Nk Ok On) Fr(Et Mg Mn Ng) Ok(Lu Mf Mn Nm) Ji(Et Mn Nm) Pg(Mi Nw On) Em(Nm Pj) Jg(Mg Ng) Jq(Ir Ml) Om(Md Ny) LvMf
MnOn NkNl} Gd{Hu(Al Ao Aw Bc Bo Cp Fa Fy Hb Il Ip Iq Jf Jh Jm Kd Kg Kx Lu Lx Mf Mr My Ng Nm Nq Oe Om Or Ow Pf Qu Qv Uf Un
Ur Vt) Hc(Ao Ar As Cw Dg Et Jd Ke Kg Lu Mt My Oa Om Pc Rh Ub Ue Uh) Mm(Dc Fw Ha Ii Ij Ik Im No Of Qu St Tz Uc) Oe(Ic Je Jf Kr Qv
Uh Uv) Ua(Cw Il Kc Qv) Pj(Nv On Po Uu) Iz(Kc Qv) PoVt IbKd} Nn{Jt(Im Jg Jm Jq Lv Mf Mi Mk Ml Mr Mx My Nk Nl No Nr Nu Om Pa
Pe) Mn(In Ji Jm Js Lv Mf Mg Ml Mm Ng Nk Nm Nr Nw Pz Tr Uk) Nm(Fr In Is Ji Jm Lv Mf Mi Mx Nk Nw Ok) Pz(Is Jg Ji Jm Lv Mf Mi Mx
Nk Nw) On(Et Il In Iu Jm Ma Mg Ng) Et(Fn Fr Ji Ok Uk) In(Is Lx Mi Nw) Js(Is Mi Nw) DpTr MiHq MmUk} aP{cO(aM aX Ba bG bL bN Cp
cS Cv cZ dG dL Iu Jy Kd Ko Ky Mf Mm Pk Ue Vt) iA(cB Fn Hx Iu Jy Ko Ky Ma Mf Pk Qx Tr Uk Ut) bL(aM bG bN cE cI cS cZ dG dL) cl(aX
bG bN cE cS cW dG dL) bG(aX bA bN bW cS cT) cS(bN bW cE cK dL) Tr(cB dG oN) bN(cE dH) bW(cW Ko) AndG KrcB
aCcZ aXdH bAcW bVhB cEcT} Fr{Pz(Ir Ji Jm Lv Ma Mf Ml Mn Mx Ng Nk Nl Nu Nw Ok On Qa Qb Qc) Jt(Ir Ji Jq Lv Ma Mf Mg Mr Mx Nk Nl Nr Nu Nw Om Qc) Mg(Is Jg Lv Mf Ml Nk Nm Ok Om On) Mn(Jm Ma Mf Ng Ok On) Is(In Jm Js Nm) Ng(Jg Jk Mf) Em(Et Pj) Nm(Ji Ok) Mi(Hq Ma) EtJi MxJs NkNl cOcS jPlL} Uk{Fn(cO Et Ez Mf Mn Mx My Pk Rh Tr Ua Ue Uh) Mx(cO Et Kd Ko Kr Mn Tr Ua Uh Vt) Ba(cO Cu Et Ko Ma Ue Uh) bA(bU cB cE Ko Ma Pk) cT(bU cB cE cJ Ma Pk) Ez(cC cO dJ Et Kd) Nq(Et Ko Mn Tr Uh) Cp(Et Ko Uh) Ua(Cu Mn Ue) bV(cJ cO iA) TiPk cNcO} On{In(Hv Ir Is Iu Mf Mg Mi Mn Mx Mz Nc Nl Pz Qb) Iu(Il Mf Mg Mn Mx My Ng Nl Nm Oy Pg Pz) Pz(Il Is Mf Mx My Nb Nl Oh Oy Qa) Jt(Ik Il Im Jk Jp Nv Qc) Pg(Et Lu Mf Mg Mi Pf) Mg(Jk Lu Mf Mn) Pf(My Oy) NgJk NkNl IlIm} Em{Pj(Dl Fb Hc Iz Ji Li Lx Mw Mx My Nq Nt Nw Oe Qy Tz Ua) Mm(Dl Fb Ib Jk Mj Mx Ng No Nq Nt Qd Qt Tz Uf) Qy(Ad Bb Co Cw Dg Et Jt Nm Ue) Mw(Bb Cw Et Nm Om Ue) Hu(Ap Bb Kg Kj Mg) Ua(Cw Kg Kj Nm) BbHc PoNm} Nw{Pz(Hq Hx Is Js Lv Md Mf Mg Mh Mt My Nl Ny Pb Pg) Js(Et Jt Mf Mg Mi Mn Mx My mZ Nm) In(Et Jk Lu Mf Mi Ml Mn Nl Nm) Ml(Et Mf Mi Mn Nm) Jt(Is Md My Ny Ok) Ti(Pf Pk) Ny(Et Mn) ItmZ} Nq{Ko(Ad Cu Cw Dg Et Fn Im Kd Kg Kr Ma Mf Mg Mn Qg Tr Ue) Kr(Af Bb Cu Cw Et Mg Mn Tr Ue) Tr(Et Iu Jq Kg Ks Ky Mg) Fn(Cu Dg Et Mn Ue) EtKd MnUe} Pk{Ti(AN Bo Dp Hx Jv Kn Ky Mg Mx Na Qv Tz Ue) bV(BA cE cO iA Im Kr Mm Qg) bA(Fn Kq Tr Ue Uv) cT(Fn Ue)} Jt{Ok(Im Ir Ji Jk Jp Lx Mf Mi Mw Mx My Nk Nv Nx Oh Po Qa Qb Qc) Jg(Is Ji Mi Mx My Ng) Is(Ji Jm Mi) MdOm} cS{cI(bA bN cJ cK cN cO cT dM) bA(bG cE cJ cK cO Cu) cO(An Aw cN Cp) Ba(cE Cw Dg) Cp(Ad Cw) cT(cE cJ) MmIb cKdM} Mi{Hq(In Jk Js Mf Mn Nm) Om(In Js Ml) Is(In Js) Jg(Mg Pz) Pg(Mk Pb)} cB{bA(Fn Kq Kr Tr Ue) cT(Fn Kq Ue Uv) hG(Fn Kr Tr) BaUe MxKr cNeM} aX{cO(An Aw Ba cI Cp) Cp(cE Cu Cw) aC(cI Cu Cv) AnaZ bAcE bNcI} Jg{Ng(Jk Mf Mn Nm) Pz(Mg Mx My Ok) Et(bV fR gW) MakS} Ue{Cu(Ba Iz Ua) Fn(Ky Mf My) Ky(Ba cT) cO(bA cT) MdMw} bV{cO(Et Fn Kr Mx) iA(Hx Ky Mf) Kr(cF cJ) EtMx TrbA} Mm{fR(aZ Ba Mg Oe) Gn(Dk Of Vs) IbIv} Fn{Et(Cp My) Ma(bA cT) cO(bA cN)} Jk{Nr(mZ nK) MjnJ IsJm ItmZ NynK} Ma{kS(Ba Im Mw) MwmZ} Is{Js(Iu Mx) Ok(Nm Pz)} eM{cT(aS bN) cY(aK cN)} Ti{TjNa MfRf MgIz} Ua{CwGn ExfP GzTr} Om{Md(Mg Pz) MxIn} fR{CwIz EtJh} mZ{HxIt jGjH} BbGzHc CoMwKd LxHqPf bAcJfP bNiZkS rBjGqZ Constrained panels with 2 analytes, where 1.0E-7 >= 'model p-value' > 0. Contains 10 panels of 94,547 total panels evaluated. : aA(Ih In Iu Js Jt Md Mn Ok Pz) GcOe

Figure 13 Continued

Constrained panels with 2 analytes, where 1.0E-6 >= 'model p-value' > 1.0E-7. Contains 22 panels of 94,547 total panels evaluated. : aA(aY bG bN bQ cE cI cO cS Cv cW cZ dG dL Fn Kd Ko Kq Uk) Jj(Mu Mv) aJ(dG dL)

Constrained panels with 2 analytes, where 1.0E-5 >= 'model p-value' > 1.0E-6. Contains 72 panels of 94,547 total panels evaluated. : aA(Af aL aM Ap bL cJ cQ Cu Cx dH eF Fa Fb Ke Kg Kr Ks Ky Pk Tr Tv Uc Ue Uh Uv Vt) Gc(Ax Cs Ex Hc Ib Mu Mw My Ou) Jj(Fr Is Jg Jk Jl Nn On) aJ(bG bL bN cI cO cS cW) Jo(Fr Jl Mu Mv Ok On) Mu(Jl Mg Ng Pz) On(Jt Pd Pg Pz) Fr(Mg Pz) Mv(Jl Ng) Ok(Jt Pd) NnMn MiHq IuJl Constrained panels with 2 analytes, where 1.0E-4 >= 'model p-value' > 1.0E-5. Contains 212 panels of 94,547 total panels evaluated. : Gc(aA Ef Em Fr Ik Is Iz Je Jg Jk Jl Li Lx Mk Mv Mx Nb Nn Nv Nw Of Og On Po Qt Qy Rb Ua) Jj(Ik Im Ir Iv Ji Jr Lh Lv Mf Mi Mk Mr Mx My Nl Nt Nu Nv Nw Nx Oh Ok Om Pa Po Qa Qb Qc) Mv(Il In Ji Jm Jt Lv Mf Mg Mi Mn Nk Ok On Pd Pz Ue Uk) Mu(Ex Gd In Ji Jm Jt Lv Mf Mi Mn Nk Nm Nw Ok On Pd) Jl(Fr In Ji Js Jt Lj Lv Mf Mn Nk Nl Nn Ok On Pd Pz) On(Il In Iu Jm Mf Mg Mn Ng Nm Nn Oy) aP(aM bG bL bN cE cI cO cS cW dG dL) aJ(aX bM bO bW cE cJ cZ iA Ko kS) Fr(Jm Jt Ma Mf Mn Ng Nm Pd) Jo(Cp Is Jg Ji Lv Mi Nn Nw) Uk(bA cT Ez Fn Mx Ua Ue) aA(iP jG kS oH oK oN) Nw(In Js Ml Pd Pz) cS(An bA cl cT dM) Jg(Jt Mg Ng Pz) Gd(Hc Hu Ua) Nn(Jt Nm Pz) Nq(Ko Kr Tr) Pd(Ji Mi Om) bV(iZ Kr Pk) Ti(Na Pk) Em(Mm Pj) Is(In Jt) Ok(Nm Pz) eM(cN cT) FnUe MdOm MmfR ltmZ JiJt aXcI bNiZ Constrained panels with 2 analytes, where 1.0E-3 >= 'model p-value' > 1.0E-4. Contains 543 panels of 94,547 total panels evaluated. : Fn(aJ aP aX BA bV cB cO cT Cu Dg Et Ez Ib Im Iu Jo Jq Kd Kg Kr KS Ky Mf Mg Mn Mv Mx My Nm Nq Pd Pk Qv Rh Tr Tv Uh) Uk(aJ aP aX Ba bR bU bV cB cF cJ cO cS Ct dA dI dJ Et Ib Im Kd Kr kS Ky Mf Mi Mn Mu My Nq Og Pk Qg Qv Rh Tr Ud Uh Ti) bV(bA bG bN bX cI cK cO dM Et iA Il Im Jo Kd Kg Ko kS Ky Ma Mf Mm Mv Mx nY Pd Qg Tr Ue) Ue(BA cB Cp cT Ez Ib Iz Jd Je Kd Kr Ky Mf Mu Mx My Nl Nq Pk Qw Qy Ua Tj) aP(An bA bQ bW cZ dH Et iA iJ Jo jP Kd Ko Kr kS Mm Mp nW oK oN Pd Pk Tr Tv) Gc(aJ Ao aX Ba Co Cp cS CT Fw Gl Ha Jd Mi Oi Qg Qv Ri Tz Ur Uu Vp Wm) mZ(aA iC Ir Iu Iv jG jH Jk Js Lj IL Ma Mf Mk Ms Mv Mw Nd Nf Nj Og oP Qe) Nn(Et In Iu Ji Jm Js Ko Lu Lv Ma Mf Mg Mi Ml Mm Mx Ng Nk Nr Nw Ok Pd) bA(aX bG bN bX cE cI cJ cZ dM eM Et Kq Kr Ma Pd Pf Pk Tr Tv Uc Uv) Ti(aA An Db Dp Ez Hx Ib Jo Jv Kn Ky Mf Mg Mx Nq Nw Qz Rf Tz Tj) Jo(Ba Ct Ez Ib Ik Ir Iz Jd Jk Lh Mk Mr Mx Nv Nx Om Pa Po Ua) Mv(cO Cw Gd jP Kg Ko Kr Ma Ml Mx nK Nm Nr Nw Qv) aJ(An eM Et iP Iu Kr Mf Mn Mp nW oN Pd Pk Tr Tv) aX(aC AN aZ bG bN bX cO Cp cT Cu dM eM Pk Tr) Mi(In Jg Jm Js Jt Ma Mf Mg Ml Mn Nk Nw Ok Pz) Nw(Et Jm Jt Lv Md Mf Mg Mn Mt My Ng Nk Nm) cS(aN aW aZ Ba bN cJ cK cN cO Cp eM iZ Pk) aA(EM hW iC jI jP kN Kx IL nD nN rB) kS(bN bQ cB Hb hG Hx iZ jP Ma Mf rB) Ji(Et In Js Lu Mf Mg Ml Mn Nm Pz) Ok(Fr Im In Js Lu Mf Mg Ml Mn Ng) eM(bG bS bX cB cl cP cY cZ dM) Gd(Ct Ef Iz Jl Oe Qw Qy Uu) Mx(cO Fr Jg Kr Ks Mf Nk Pz) Is(Jm Js Mf Ml Ng Nm Pz) Et(Ba Cp FR Ib Jd) Mu(Co Dr Em Gn Kq Tj) Jj(Jm Me Ne Nr Pc Pe) cB(Ez hG iZ Kr Pk Tr) cI(bN bX cN cT dM fR) iC(jH IL qV qZ rY rZ) Fr(Il In Lv Ml Nr) IL(jG jP Mf nU qZ) Nq(Kg Ks Tv Uh) Jg(In Jm Mn My) Ba(Ma Pd Uh) Lv(Mf Ml Pz) Om(In Js Ml) cT(Kq Pk Uv) dM(bG bN cJ) fR(aG aH cP) iZ(bM cO fP) Cp(Ad Pd) Em(Lu Nm) Lx(Hq In) Ib(Mm Pd) Iu(kK qZ) Pz(Nv oP) jP(cQ oE) EzcC NoJs MffP MycO NkNl HxiA TrJd IlJl ImOn IzKg JknK JtNv jGjH Constrained panels with 2 analytes, where 1.0E-2 >= 'model p-value' > 1.0E-3. Contains 1,326 panels of 94,547 total panels evaluated. : Mf(An aP aX BA cS cT Ez hG Hv Ik Il Im Ir Iv iZ Jd JG jH Jk jP Jq Jr jY Kd Ko Kr Ky Md Mv Ne Nl NR Nt Nu Nv Nx OH Om Pa Pc Pe Pk Po Qa Qb Qg Qv Tr) Jo(aJ An Ao Aw aX bA cS cT Dc Ef Em fP Fy gP Ha Hv Hx Im Ip Iv Jp Jq Kd Kr Li Lw Lx Mj Mp Mt My Nb Ne Nk Nl No NR Nt Nu Oh Pc Pe Pk Qa Qb Qc Qd Qg Qh Qv Qy Un Us Wm) Ez(Ad aJ aK As aU aX BA bU bV cJ cO cS cT Cu Cv Dd Dg dJ Et fP gW Hb hG iA Im Iu iZ Je Jq Jt Kd Kg Ko Kr Ks Mg Mm Mn Nm Pd Pk Pz Qg Qv Rh Tr Uh Vo Vt) Im(aN aX aZ Bb cB cJ cO cS cT Cu Cv Dd Dg fP Il Jg Ji Jk Jl Jm Jt Kd Kg Ko Kr KS Lv Mk Mn Mr Nk Nr Nu Nw Om Pc Pk Pz Qv Rh Tr Tv Uh Vt) Mx(Al aX aZ Ba Bb cB cE cJ cS cT Cu Cv Dd Dg fP iA In Is Jm Js Jt Kd Kg Ko Lv Mk Ml Mn Om Pc Pd Pi Pj Pk Qv Rh Rm Tr Tv Uc Uh Vo Vt Tj) Ba(Ad Al An aZ bV cE cO Cv cZ Dd Dg Fy Gd Hb Iu Jq Jt Kd Kg Kl Ko Kq Kr Ks Ky Md Mg Mn Nm Pf Pg Pk Pz Qg Qv Rh Tr Tv Uc Uv Vo Vt) Iu(An aP bA cJ Cp cT hG iA Ib Is IZ Jd jG jP Kd kF Kr kS Ky IL Mk Mr nI nK nR nU nY oE oP Pa Pk Qg Qv Qy Rf rY Ua Ue Wm) Mv(Ad Al Ap aX aZ Bb cB cE cJ Co cS Cu Cv Dd Dg fP iA jG jH jT Kd Kj kK Ks Ky IL nI nT nU Pk Qg Rh rY Tr Tv Uc Uh Vo Vt) Pd(An Aw aX cS cT dM fP gP Ha hG Is Iz Jd Je Jg Jk Jq Kd kS Lh Lv Lx Mp Nt Nu Nv Pa Pe Pk Po Qg Qh Qt Qv Qy Rf Ua Un) Kr(aX aZ bU cF cJ cO cS cT Db dM Dp Em fP hG Hx Ib iZ Jd Je Jl kS Mi Mu My Na Nn Nu Oe Pk Qv Qy Ua Un) Jt(Cp Em Ib Ik Ir Iz Jd Jk Jp Lh Li Lv Lx Mk Mr My NR Nu Oh Om Pa Pe Po Qa Qb Qd Ua) Kd(aJ An aX bA cB cO cS cT Et fP hG Hv Hx Ib iZ Jd Je Jl Kg KS Mu My Nq Pk Qg Qv Rh) Gd(Cp Dc Em Fp Fr Ib Ik Il Je Jk Mk Mw My Nn Nv Of Og Po Qg Qv Qz Rh Ri Tz Ug Vp Vt) Mn(An aP bA bV Cp cT Hx Is Iz Jd Jk Jp Li Lv Mk Mr My No Nr Nv Oh Om Pa Po Qa Qb Ua) Pz(Ik Ir Iz Jd Jk Jp kF kK Lh Li Lx Mk Mr Mt My Nb NR Nu Oh Om Pa Po Qa Qb Qd Ua) Pk(bU cO Cv Et fP gP hG Hv iA iJ iZ Jd Kg Ko KS Mm Mu My Nm Nq nY oH Qg Qv Rh Vt) Tr(Aw bU Cp cS cT dA dM Dp FR hG Hx Ib IZ Jc Jl kS Mu My Nn No Qv Rf Ua) Kg(Ao aP aX bA Cp cS CT Em fP Ha Hc hG Hx Ib Jd Je Jk Mu My Nn Po Qg Qy Ua) Ks(aP bV cS CT Ha Hx Ih Iz Jd Je Jk Jl Ml Mu My Na Nn Oe Po Qg Qy Ua Us Uv) In(Hw Hx Ir Iv Jk Jq Lh Mk Mr Mz Nb NR Nt Nu Nv Pa Pb Pe Po Qa Qb) Cp(Af Al As aZ Bb bN bV cE cO Cu Cv Cw cZ Dd Dg Dl Jq Ko Mg Nm Uc) aP(Al Cu Cv Dg Fa Fb Gc iC Io Kq Ky Ma Oh Pf Pg Ue Uh Uv Vt Ti) bA(bQ cO Cv Dd Fa Fy Gc iA iJ Kn Ko Ky oH oN Pg Tn Ut Vs Tj) cT(An bG bN cl cE cJ Cv cZ Dd Et Fa Ko Ma Pf Tv Uc Ut Vs Tj) jP(aJ aZ Fr Hx iB iZ JG jH Jj Lv Mp Mw Nj oF oH qU rB rY) Mu(Ao aZ Bb bF cE cO Cq Cu Cv Dg Dk Ko Qx Tv Uc Ut Vs Vu) Nk(Hv Ir Is Jg Jk Mk Mr Nc Ne No Nr Nu Nv Oh Pa Po Qa Qb) hG(aZ bN cJ cS Et Fn fP gP Ko Ky Ma oH Ow Pf Qw Rh Ue Uk) Nq(Cu Dg Hb iA Ke Kj Kl Kq Ky Qg Qv Rh Tt Uc Uf Vo Vt) iC(aJ aZ bN cJ cL cQ gP iO iZ jG kK kS nR nY oE oH oP) Et(An Ao Aw aX cS Dk Em fP Gl Iz Je Qv Qy Rf Ua Un) Ib(As Cu Dr Em Gn Jq Ke Ko Md Mg Om Pg Tv Uc Ut Vs) Jd(Ad Bb Cu Cv Dg Jq Ko Ma Mg Mm Nm Ok Qg Rh Uh Vt) Il(Ir Is Jg Jk Lv Mi Mj Mk Mr Nn Nr Nw Om Pa Pe) fP(An aW bG bN cl cJ cO Fn Hx Ky oN Ow Qg Rh Ue) aJ(Io jG Kq Ky Ma Md Mm Ny Qd Qe Qg Ue Uh Uv) nR(Ir It Iv jH jT IL IO Ma Mj Nd Nf Nj rY rZ) jG(Fr Hx iO iZ Jj kS Lv Mp nB Nj nU oE rB) Ko(An Hx IZ Je Jg Jl My No Qv Qy Ua) cO(Aw cN dG dM Fr Jl Jr kS Mr Nh Qg Ue) Ir(Is Jm kF kK Lu mS Ng nl nK Nm oP) bN(Aw aZ bG bX cN cZ dA dG dN gL oH) IL(eD Fr Jj Lv Ml nB NJ nT qU rB) Mg(Aw Ct Em Is Iz Jk Nv Om Qy Ua) My(Ad cB Cu Cv Dg Jm Kj Ng Uh Vt) Ue(aX aZ cJ cS dE Em gP kS Qt Us) kK(It Iv Jk Js Lj Mk Mw Nf Nj Qe) Gc(hC bX cK cN cP dN eF Fp fR) qZ(aA Hv Lj Ml Mr Ms Qd Qe rB) Ng(Ik Jk Lv Mk Nv Oh Om Po) Ua(Ad Cu Dg Kj Nm Qv Uc Vo) fR(aX bB cE cK cV cZ Ma Pj) Em(As Fr Hx Jl Mw Uk Vt) Is(Ih Ip It Jn Jr Lu Lv) rB(aF aO bM cJ iP oE rY) An(aZ bV cZ Dd dM gL) Cu(Iz Jl Lh Li Nh Nn) Dg(Ap Fr Iz Jg Nh Nn) Nm(Iz Jg Lh Nv Oh Po) Qg(Al cS Dp Je Qv Vt) Jm(Jk Nv Oh Po Qa Qb) Jr(aX cB cJ cS Jq Om) nI(Iv Jk Ms Mw Nf Og) It(kF kN nK nU oP) aZ(Aw Fn Fr nY pF) cB(bX Nd Nh nY oF) jH(cJ cQ mM nT nU) qW(aF aO bM kS oE) Ad(Aw Fr Iz Jg) Ma(aX hB iZ oF) Ml(Jg Jq Nb No) Hx(iJ Ik iP Uh) bV(cE cZ Uh Vt) qU(aA nU rY rZ) kS(Ky Md nY Rh) oP(Iv Ml mM Og) Fn(bU cS iZ) Nn(li Uh Vt) Jq(Jn Js Md) nK(Iv Mw Qe) iA(dM Jl Uk) Aw(cE Dd) Ti(aN cJ) Lv(Jg IO) Nj(jY kN) Ji(Aa Mm) Ky(aX iZ) Om(Jn Ny) aC(bE cZ) bG(cN dG) bX(dA dI) cS(nY oE) DcDd DkMw LxNd MjnJ NcNl NfkF NhaX IvnU lzKj OwiZ aVdA cIgL dMiJ mMrY hXiP iOjM

Figure 13 Continued

Unconstrained panels with 3 analytes, where 1.0E-10 >= 'AUC p-value' > 0. Contains 5,411 panels of 10,943,034 total panels evaluated. :
Gc{My(aA Ad Af Aj Al An Ao Ap Ar As Aw Ax Ba Bb Bc Bg Bn Bo Ch Co Cp Cq Cs Ct Cu Cv Cw Cx Db Dc Dd De Dg Di Dk Dl Dp Dr Ed
Ef Em Et Ex Ez Fa Fb Fn Fp Fr Fw Fy Gd Gl Gn Gp Gz Ha Hb Hc Hf Hq Hr Hu Hv Hw Hx Ib Ic Id Ih Ii Ij Ik Il Im In Io Ip Iq Ir Is It Iu Iv Iz Jd
Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Ly
Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl Nm
Nn No Nq Nr Ns Nt Nu Nv Nw Nx Ny Oa Oe Of Og Oh Oi Ok Om On Or Ou Ow Oy Oz Pa Pb Pc Pd Pe Pf Pg Ph Pi Pj Pk Po Pz Qa Qb Qc Qd
Qe Qg Qh Ql Qm Qn Qt Qu Qv Qw Qx Qy Qz Ra Rb Rc Rf Rg Rh Ri Rj Rm Sr Ss St Tn To Tr Tt Tv Tz Ua Ub Uc Ud Ue Uf Ug Uh Uk Ul Um
Un Uo Up Ur Us Ut Uu Uv Vo Vp Vq Vs Vt Vu Vv Wm Tj) Hc(aA Ad Af Aj Al An Ao Ap Ar As Aw Ax Ba Bb Bc Bg Bn Bo Ch Co Cp Cq
Cs Ct Cu Cv Cw Cx Db Dc Dd De Dg Di Dk Dl Dp Dr Ed Ef Em Et Ex Ez Fa Fb Fn Fp Fr Fw Fy Gd Gl Gn Gp Gz Ha Hb Hf Hq Hr Hu Hv Hw
Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko
Kp Kq Kr Ks Kx Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw
Mx Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Ou Ow Oy Oz
Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn
To Tr Tt Tv Tz Ua Ub Uc Ud Ue Uf Ug Uh Uk Ul Um Un Uo Up Ur Us Ut Uu Uv Vo Vp Vq Vs Vt Vu Vv Wm Tj) Oe(aA Ad Af Aj Al An Ao
Ap Ar As Aw Ax Ba Bb Bc Bg Bn Bo Ch Co Cp Cq Cs Ct Cu Cv Cw Cx Db Dc Dd De Dg Di Dk Dl Dp Dr Ed Ef Em Et Ex Ez Fa Fb Fn Fp Fr
Fw Fy Gd Gl Gn Gp Gz Ha Hb Hf Hq Hr Hu Hv Hw Hx Ib Ic Id Ih Ii Ij Ik Il Im In Io Ip Iq Ir Is It Iu Iv Iz Jd Je Jf Jg Jh Ji Jj Jk Jl Jm Jn Jo Jp Jq
Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Ly Lz Ma Mb Mc Md Me Mf Mg Mh
Mi Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv Nw Nx
Ny Oa Of Og Oh Oi Ok Om On Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw
Qx Qy Qz Ra Rb Rc Rf Rg Rh Ri Rj Rm Sr Ss St Tn To Tr Tt Tv Tz Ua Ub Uc Ud Ue Uf Ug Uh Uk Ul Um Un Uo Up Ur Us Ut Uu Uv Vo Vp
Vq Vs Vt Vu Vv Wm Tj) Nn(aA Ad Af Aj Al An Ao Ap Ar As Aw Ba Bb Bc Bg Bn Bo Ch Co Cp Cq Cs Ct Cu Cv Cw Cx Db Dc Dd De Dg Di
Dk Dl Dp Dr Ef Em Et Ez Fa Fb Fn Fp Fr Fw Fy Gl Gn Gp Gz Ha Hb Hf Hq Hr Hu Hv Hw Hx Ib Ic Id Ih Ii Ij Ik Il Im In Io Ip Iq Ir Is It Iu Iv Iz
Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx
Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl
Nm No Nq Nr Ns Nt Nu Nv Nw Nx Ny Oa Of Og Oh Oi Ok Om On Or Ou Ow Oy Oz Pa Pb Pc Pd Pe Pf Pg Ph Pj Pk Po Pz Qa Qb Qc Qd Qe
Qg Qh Ql Qm Qn Qu Qv Qw Qx Qy Qz Ra Rb Rc Rf Rh Ri Rj Rm Sr Ss St Tn To Tr Tz Ub Uc Ud Ue Uf Uh Uk Ul Um Un Uo Up Ur Ut Uu
Uv Vo Vp Vt Vv Wm Tj) aA(Af aG Ax Cs Dp Ed Em Et Ex Ez Fa Fb Fn Gz Ha Hb Hf Hq Hr Hu Hv Hw Hx Ib Ic Id Ih Ii Ij Ik Il Im In Io Ip Iq
Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj
Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh
Ni Nj Nk Nl Nm No Nq Nr Ns Nt Nu Nv Nw Nx Ny Oa Of Og Oh Oi Ok Om On Or Ou Ow Oy Oz Pa Pb Pc Pd Pe Pf Pg Ph Pi Pj Pk Po Pz Qa
Qb Qc Qd Qe Qg Qh Ql Qm Qn Qu Qv Qw Qx Qy Qz Ra Rb Rc Rf Rg Rh Ri Rj Rm Sr St Tz Ua Ub Uc Ud Ue Uf Ug Uh Uk Ul Um Un Uo Up
Ur Us Ut Uu Vo Vq Vs Vt Vu Vv Wm Tj) Ou(Af Aj Al Ao Ap As Aw Bb Bc Bo Ch Co Cp Cq Cs Ct Cv Cw Cx Db Dc Dd De Di Dk Dp Ef Et
Ez Fn Fp Fr Gl Gp Gz Ha Hb Hf Hq Hu Hv Hw Hx Ib Ic Id Ih Ik Il Im In Ip Iq Is It Iu Iv Iz Je Jf Jg Jh Jk Jl Jm Jn Jo Jq Jr Kc Kd Ke Kg Ki Kj
Kk Kp Kr Ks Kx Ky Kz Li Lj Lu Lv Lw Ly Lz Ma Mb Mc Md Me Mf Mg Mh Mi Mk Ml Mm Mn Mq Ms Mu Mv Mw Mx Na Nb Nc Nd Ne
Ng Nh Ni Nk Nl Nm Nq Ns Nu Nv Nw Nx Ny Oa Of Og Oi Ok Om On Or Ow Oy Oz Pb Pc Pd Pf Pg Ph Pi Pj Qa Qb Qc Qd Qg Ql Qt Qv Qw
Qy Qz Rb Rf Rg Rh Ri St To Tr Tz Ua Ub Ue Uf Uh Uk Uo Up Ur Us Ut Uu Uv Vo Vp Vq Vt Vv Wm Tj) Ao(Ax Cs Dp Em Et Ex Fa Fn Fy
Gz Ha Hf Hq Hu Hv Hw Hx Ib Ih Ii Ij Il Im Io Ip Iq Is It Iu Iv Jd Je Jf Jg Jh Ji Jl Jm Jo Jp Jq Jr Js Jt Ju Kc Kd Ke Kg Ki Kj Kk Kr Kx Ky Kz Lh
Lj Lv Lx Ly Lz Ma Mb Md Me Mf Mg Mi Mj Mk Ml Mm Mn Mp Mr Ms Mu Mw Mx Mz Na Nb Nc Ne Ng Nh Ni Nk Nl Nm Nq Nr Ns Nt Nu
Nv Nw Nx Ny Oa Of Og Oh Oi Om On Or Ow Pb Pc Pd Pf Pg Ph Pi Pj Pk Po Pz Qa Qb Qc Qd Qe Ql Qv Qx Rb Rf Rh Ri Ub Ue Ug Uh Uo Uv
Vo Vt Wm Tj) Fw(Ax Cs Dp Em Et Ez Fa Fb Fn Fy Ha Hb Hf Hu Hw Ib Ic Id Ik Io Ir Iu Jd Je Jf Jg Jh Ji Jv Jy Kc Kd Ke Kf Ki Kj Kk Kl Ko Kq
Kr Ks Kx Ky Kz Lh Li Ly Lz Ma Me Mj Mk Ml Mm Mn Mr Ms Mt Mu Na Nc Nd Ne Nf Ng Nh Nj No Nr Ns Nu Nx Ny Oa Of Og Oi Or Ow
Oy Pc Pd Pg Ph Pj Pk Qg Qh Ql Qm Qn Qu Qv Qx Qy Qz Rb Rf Rg Rh Ri Rj Rm Sr Ss St Tn Tr Ua Ud Ue Uf Ug Uh Uk Ul Um Un Uo
Ur Us Uu Uv Vq Vt Vu Vv Wm Tj) Cp(Ax Cs Dp Em Et Ex Fn Gz Ha Hb Hf Hq Hr Hv Hw Ib Ic Id Ih Ik Il Im In Io Ip Iq Is Iu Iv Je Jf Jg Jl Jm
Jo Jr Js Kc Kd Ke Kk Kp Kx Ky Kz Li Lj Lu Ly Lz Ma Mb Md Me Mf Mk Ml Mm Mn Ms Mt Mu Mx Mz Na Nb Nc Nd Ne Ng Nh Ni Nk Nm
Nq Nr Ns Nu Nv Nw Nx Ny Oa Og Oh Oi Om On Ow Pc Pd Pf Pg Pj Qb Qg Qv Qz Rb Rf Rh Ri Tr Ub Ue Uh Uo Ur Us Vo Vv Wm Tj)
On(Ad Af Ap As Bb Bc Bo Ct Cu Cv Cw Dg Dr Em Et Fa Fb Fn Gd Gp Gz Ha Hb Hf Hw Ib Io Iu Jm Jt Kc Kd Ke Kf Kj Kk Kl Kp Kq Kr Kx
Kz Ly Ma Md Mf Mk Mm Mx Na Nb Nc Ne Ng Ni Nl Nm Ns Nu Og Oi Ow Pd Pg Ph Pj Pk Po Qa Qg Qv Qx Rb Rc Rh Ri Ue Uh Un Uo Uv
Vo Vt Vv Wm) Mm(Ad Aj Al Ap As Ax Ba Co Ct Dc De Dg Dk Ef Ex Fp Fr Fy Gl Ha Hw Ih Ii Ik Is Iz Je Jf Jg Jh Ji Jk Jl Jm Jp Kf Lh Li Lx
Mj Mq Ms Mt Mu Mv Mw Mx Na Nb Ng No Nr Nt Nu Nv Nw Nx Of Og Oi Ok Oy Pe Pf Pg Ph Po Qb Qd Qg Qh Qu Qy Rb Rf St Ua Un Uu
Vv) Mx(Af Aj As Ba Bb Bo Ct Cx De Dr Ed Ef Em Ez Fb Ha Hr Hv Hw Hx Ib Ii Ik Iz Jd Je Jg Ji Jj Jk Jn Jy Kc Kd Kr Ld Ly Ma Mg Mk Nb Nc
Nd Ne Nf Nj Nk Nv Nw Of Og Oi Ok Ow Oy Pc Pi Pk Qg Qy Rb Ri St Tn To Tr Tt Tv Ua Ul Um Uu Wm) Of(Aj As Ba Ct Cv Db De Ex Fp
Gn Gz Hf Hv Ib Ih Il Ip Iq Is Iv Je Jf Jg Ji Jj Jl Jo Jp Kc Kg Lu Lx Ly Me Mf Mr Ms Mu Mw Na Nb Nc Ng Nm No Nq Nt Nu Nv Nw Nx Oh Oi
Om Oz Pc Pd Pe Pj Qb Qv Qy Rb Rf Rh Ri St Ub Ue Vo Vt Wm) Mu(Af Ap As Ba Bc Bo Ct Cv Cx Em Fb Fy Hf Hr Hv Hw Ib Io Ip Iv Je Jf Ji
Jt Jy Kc Kd Kq Kr Ks Kz Ld Ly Ma Me Mk Ms Mw Na Nb Nc Nd Nt Nw Nx Og Oi Ok Pa Pd Pk Qt Qv Qx Qy Rb Rc Tn To Tr Tt Tv Ue Uk
Uu Wm) Na(As Ba Bo Co Ct Ed Ef Em Ez Fn Fy Hr Hv Ii Ik Is Iz Jd Je Jg Ji Kc Kf Kk Ld Ly Mg Mi Mk Ms Mv Nb Nc Nd Nf Ni Nj Nv Nw
Nx Og Oi Ok Ow Pf Ph Qg Qy Rb Ri St Tn To Tv Ua Ue Ul Uu Vv) Ib(Ad As Ax Ba Cv Em Ez Fn Fp Gn Gz Hf Hv Il In Ip Iv Jd Je Jf Jg Ji Jr
Jt Kc Kd Kr Kz Lx Ly Me Mk Ml Ms Nc Ng Nq Nr Nt Nu Nw Nx Oi Ow Pd Pi Pk Po Qg Qt Qv Qy Rb Rf Ri To Ue Vv Wm) Cs(Ad aE Af Aj
Al An AP Ar As Aw Ax BA Bb Bc Bg bH bI Bn Bo bP bV bZ Ch cK cN Co Cq cS CT Cu Cv Cw Cx Db Dc Dd De Dg Dl Dk Dl Dr Ef Em Ex
Fr GL Gn Gp Jg Ji) Oi(As Ax Ba Bg Ef Ez Fp Fr Ha Ii Ik Im Is Iz Je Jf Jg Ji Jl Lh Li Lx Mi Ml Mq Mr Ms Mv Mw Nb Nc Ni Nq Nr Nu Nv Nw
Nx Oz Pc Pd Pe Pf Po Qb Ql Rb Rf Rh St Ua Ud Uu Vv) Ue(As Ba Cq De Dk Ef Fn Fr Fy Ha Ih Ii Ik Is Iz Jd Je Jg Jh Ji Jk Jl Kk Lh Lx Mj Mq
Mr Mv Mw Nb Nq Nt Nv Nw Oa Oy Pf Qg Ql Qn Qt Qw Qy Ri St Tz Ua Ur Uu Vp Vu Vv) Rb(Al As Ct Dc De Dk Ef Fn Fr Ha Hw Ih Ii Ik Im
Is Iz Jg Jk Jl Jm Jp Lh Li Lx Mj Mk Mq Mv Mw Nq Nu Nv Og Pf Pk Po Qa Qb Qg Qh Qt Qw Qy Rf Ri St Tz Ua Uo Ur Vp) Wm(Ba Co Ct De
Dk Ef Fp Fr Ha Ih Ik Im Is Iz Jd Je Jg Jk Jl Kk Lh Li Lu Mj Mq Mv Mw Nb Nq Nv Pe Pf Po Qa Qh Ql Qt Qw Qy Rf Sr St Tn Tz Ua Vp Vs Vt
Vu Vv) Ly(As Ba Dc De Dk Ef Fp Fr Gl Ha Hu Ih Ii Ik Im Is Iz Jg Ji Jk Jl Jp Lh Li Lu Lx Mq Mv Mw Nb Nq Nu Nv Pf Po Qa Qg Qh Qt Qw
Qy Rf Rh Ri St Tz Ua Uu Vp Vv) Nu(Aj As Ba Bo Co Ct Dc De Ed Ef Em Ez Gl Hr Hv Hw Hx Ii Ik Is Iz Jg Ji Jk Kc Kf Kj Ma Mk Ms Nb Nc
Nf Ng Nj Nv Nw Nx Og Oy Pf Po Tr Ua Ug Um Uu Vq) Ji(As Ax Bo Ct Cu Cw Dr Et Gn Gp Hb Hf Hw Ih Il Io Iq Je Jo Ke Kk Lx Ma Me Mf

Figure 13 Continued

Figure 13 Continued dL hB iP kQ nW oK) rB(cI cW) jG(aZ iO) bNiC) Ma{bV(Ex Gz iA) kS(Iz Mv Ua) BaRf GzUa MwkF JhfR} oP{Pz(Iu Mj nK Nr Nw Og Oi) NwOk} iA{bV(Hx Ky Mf Nq Uk) Mvlu KoaP} qZ{rB(hA Hv jG IL Ms) IL(iC jG)} aJ{dG(lu Ko Th) dH(Io Iu Up)} fR{Cw(Hc Iz Jh) Et(Hc Jg Jh)} Gz{Bb(Hc Iz) EtHc UaTv} aP{bW(Ko Pd) TvoN bNiC} Th{Nq(Jo Mg) AoJo} Mv{NrkO MgjP UkcO} Aa{Ko(bV Nq)} Ex{EtMy UafP} bN{iC(iZ kS)} jH{cQjP nUqU} IL{FrjP nAIK} AITiJo CpDlgC JjqUjY Unconstrained panels with 3 analytes, where 1.0E-9 >= 'AUC p-value' > 1.0E-10. Contains 3,009 panels of 10,943,034 total panels evaluated. :
Gc{On(Al An Ar Aw Ba Bg Ch Co Cs Db Dd Di Dl Dp Ex Fp Fw Fy Gn Hq Hu Hv Ih Ii Ij Ik Il In Ip Iq Ir Is It Iv Jd Je Jf Jg Jh Ji Jj Jn Jo Jp Jr Js Jv Ko Ky Ld Lh Li Lv Lw Lz Mb Mc Me Mg Mh Mi Mj Ml Mn Mp Mr Mt Mu Mz Nd Nh Nk No Nq Nr Nt Nw Nx Of Oh Om Oy Pa Pb Pc Pe Pf Pi Pz Qc Qd Qe Qm Qu Qz Ra Rf Rg Rm Sr Ss Tr Ub Ud Uf Uk Ut Vq Tj) Mx(Ad Al Ap Ar Bc Bg Cu Dc Di Dk Et Fa Fn Fy Gl Gn Gp Hb Hf Hu Ic Ij Io Ir Iu Iv Jf Jh Jm Jt Kf Kj Ko Kq Ky Kz Lh Lu Lz Md Mh Mi Mn Mr Mt Mu Mv Ng Nh Ni Nl No Nq Nr Ns Nx Ny Om Pa Pb Pd Pe Pg Ph Pj Po Qe Qn Qx Qz Ue Uh Uk Ur) Cp(aA Ed Fa Fb Hu Hx Ij It Iz Jd Jh Jj Jk Jn Jp Jq Jt Ju Jy Kf Kg Ki Kj Kl Kq Kr Ks Ld Lh Lv Lw Lx Mc Mg Mh Mi Mj Mq Mr Mv Mw Nf Nl No Nt Of Or Oy Oz Pa Pb Pe Ph Pk Po Pz Qa Qc Qd Qe Qn Qw Ra Rc Rj St To Tz Uf Uk Ut Uv Vt) Fw(Ed Ex Gz Hq Hr Hv Ih Ii Ij Il In Is Iv Iz Jj Jm Jn Jp Jq Jr Jt Ju Ky Kn Kp Ld Lj Lv Lw Mb Mc Md Mf Mh Mi Mp Mv Mw Nb Ni Nl Nm Nq Nt Nw Oh Ok Om Oz Pa Pb Pc Pf Pi Pz Qa Qb Qc Qd Qt Qw To Tv Tz Uc Up Vo Vp Vs) Ib(Ar Bn Bo Cq Cs Ct Cw Db Dc Ex Fr Fy Gd Ha Hw Hx Ii Ij Ir It Iz Jl Js Ke Kk Ky Ld Li Lj Lw Ma Md Mi Mm Mv Nb Ne Ni Nv Ny Oa Og Oh Om Or Ql Qx Qz Ra St Ud Um Vo Vt Vu) Ao(Ez Fb Hb Hr Id Ik In Ir Jj Jn Jv Jy Kf Kl Kn Kp Ks Ld Li Lu Lw Mc Mh Mq Mt Mv Nd Nj No Ok Oy Pa Pe Qg Qh Qn Qw Qy Qz Ra Rc Rg Rm Sr St Tz Ua Ud Uf Uk Ut Vp Vq Vv) Ji(Ap Aw Bb Bc Bn Db Dk Em Ex Fn Fr Gd Gz Hu Hv Im Ip Is Iu Jd Jg Jl Jm Jp Jq Jr Kx Lj Md Mk Ml Mn Mq Ms Mw Nd Ne Ng Ny Ou Oy Pa Pc Pf Qa Qb Qc Qd Qy Rb Rf Ua Uv Wm) Of(Bb Bc Bo Cs Cw Dd Fn Fr Fy Gp Hu Hx Im Iu Jh Jm Js Jy Kj Kk Kz Lh Li Lz Ma Mb Mg Mj Ml Mq Mv Mz Ne Nf Nh Nl Ns Ny Oa Or Pb Pg Po Qg Qh Qn Qx Uk Un Ur Vp) Ou(Ad An Ba Bg Bn Dg Fa Hr li Ij Io Jd Jj Jp Js Ju Jv Jy Kf Kl Ld Lh Lx Mp Nf Nj Nt Pa Pe Pk Po Pz Qe Qh Qm Qn Qu Qx Ra Rc Rj Rm Ss Uc Ud Ug Ul Um Un Vs Vu) Rb(Aj Ap Ax Ba Bo Cq Dp Fb Fp Gl Hu Il Ir Jd Jf Jh Jj Kd Ki Kr Ky Lu Mf Mg Mn Ms Nb Nc Ne Ng Nk Ns Nw Oa Oh Oy Oz Pe Pg Qd Qu Rh Ue Ut Uu Uv Vq Vu Vv Wm) Nv(Al Ar Bo Cs Cw Fa Fn Fp Gp Hw Il Io Iq Is Jd Jf Jo Jp Jy Kc Kf Kl Kr Ky Lv Md Mf Mg Mi Ml Nc Nd Ne Nl Nm No Nt Nx Pg Po Qg Qy Qz Rf Rh Ua Uv Vt Vv) Na(Af Aj Al Ap De Dk Fr Gl Ha Hf Hw Hx Jf Jh Jk Jl Jn Jq Jy Kx Lh Li Lv Mh Mr Mw Ne Nh Nl Nr Nt Oa Om Or Oy Pe Pg Pk Po Qn Tr Tt Ud Um Vq Vs Vt) Mu(Ax Bb Cs Cw De Ed Et Fn Gd Gn Ha Hx Ii Il Iu Jg Jr Kk Kx Ky Lj Lx Mp Nf Ng Nh Ni Nk Nm Nq Nr Nu Oa Oh Om Ow Pb Po Qe Ri Ua Ub Uf Uo Vo Vt) Jg(Aw Ch Cu Cv Db Di Dk Ex Fn Gd Ih Im Iq Is Jl Jo Jp Kd Kl Kx Ky Ma Mg Mk Mn Nd Ne Nh Nl Nt Nw Oa Oh Om Pc Pg Pk Pz Qg Qx Qz Uh Vo Vv) As(Fy Hu Hw Hx Ih Ik In Ip Is Iv Iz Jh Jn Jq Js Jy Kf Kp Lu Mj Ml Mq Mr Mv Mw Nc Nd Ne Nf Nh No Nq Ok Ow Pd Pf Qa Ql Rf Rh Tv Uk Uu) Nu(Al Cq Cx Db Ha Hq Hu Ih Jd Je Jh Jj Jm Jp Jq Js Jy Kr Ks Lh Li Lz Mg Mr Mt Mv Mw Nd Ne Nr Ny Ok Ow Ph Qd Qg Ri St Tn Tv Vs Vv) Po(Af Al Ap Ba Bb Bn Bo Ct Cw Gp Hr Hv Hw Ih Io Is Iu Iv Jn Kq Kz Ld Lz Ma Mz Nd Ng Nk Oh Pf Pg Ph Qg Qz Rh Ue Uv) Ax(An Aw aX Bb Bc bH bI Bn bR bS bX cB cI Cu Cv Cw Db Dd dE Dg Dl Dl dM dN Ik Jc Jk Kk Nn Og Pj Pk Ri Vt Tj) Nt(Aj Ba Co Dc Ef Fy Ha Hu Hv Ih Ii Ik Is Jd Jm Kc Li Ly Mk Mr Mw Nb Nd Nj Oi Pd Pg Qg Rh Ri Tr Vq) Lx(Aj Bb Cx Dc Ef Et Ha Hf Io Is Iv Jd Jf Jh Kf Kk Kr Md Me Mw Nc Nh Nr Nw Nx Oy Pj Qg St To Uo Wm) Ue(Aj Co Fp Gl Hu Hw Im Ir Jm Kl Li Ms Nc Ne Ng Nr Ny Oh Pe Qa Qm Qu Qz Rf Rm Sr Ug Un Ut Vs) Mm(Cq Cs Dl Ez Hf Hq Ha Il Im Jd Kc Kk Ks Ko Lu Ly Mk Mp Mr Nh Nq Oa Oh Qa Qe Ql Qz Ri Ss Tn) Oi(Ct De Dk Em Hv Ih Kf Lj Lu Lv Lz Mf Mj Mk Ne Nf No Ny Oa Oh Qc Qg Qn Qt Qy To Tz Vs Vt) Ri(Fp Hr Hv Il Is Je Jk Kc Lh Li Ms Mv Nb Nw Nx Oa Oh Pe Qg Qy Qz Rh Tn To Ua Uu Vt Vu) Nq(Ba Dr Ed Ez Fn Fp Fy Hf Hr Hw Jf Ju Jv Kd Kq Kr Kz Mk Ms Nh Nw Ow Qg Tv Ul Um) Jd(Ba Ct Fp Fy Hf Hv Ih Je Jl Kd Kr Li Lj Ma Ml Nb Ne No Pf Pk Qv Rf St Ub Ur Vt) Je(Bc Cv Cx De Dk Et Fp Fr Hr Iv Kc Ky Lu Ly Me Mi Mr Mt Nb Nx Oh Tz Ur Ut Vu) Nw(Fn Fy Gd Hb Hw Iu Jk Kc Kd Ly Mk Mr Ms Mv Mw Nc Ni Om Qw Qx Qz Ua Vo Vp Wm) Jl(Cv Ed Fb Fn Gz Hv Ii Ip Jf Ky Ld Ma Mp Nc Nd Ni Nm Oy Ph Rc Tn Tv Ul Vt) Ba(Dp Fn Gz Ha Ih Kl Ma Me Mq Nc Ng Nm Nx Om Ow Qa Qd Qg Qw Tz Ur Us Vp) Ex(Ad Af aJ Al An Aw Bn cB Ch cI cK cN cS Cv dB dE Dg Di Dl fR gL Gp Nn) Nb(Aj Al Fn Fr Gl Ha Hf Iz Jf Jk Jm Ks Ml Nc Nd Oa Oh Oy Pf Qv St Uu) Ua(Ct Dr Fn Fp Gn Gp Gz Ha Il Io Jf Kc Kr Mr Nn Nx Oa Og Qg Qt Rf Uf) Ly(Al Bg Co Ct Jf Jh Jy Mi Mj Nc Or Pe Qb Qd Qu Sr Ud Un Ur Vs Vu) Hf(Al Bo Co Ct Dc Dk Hr Hu Ih Kf Mi Oh Oy Rf St Un Ur Uv Vq Vu) Cs(aM aX bJ bR bS bX cB cl cP dE dJ dM dN fR Ii Ik Iz Ms Uu) Qy(Cv De Fb Hx Ip Jf Kq Ky Ld Lu Ms Mw Ni Nr Oz Pa Pk Vp Vt) Ef(Ez Ij Iu Jf Jp Kc Kk Mn Mr Nc Nx Og Pd Pk Pz Ql Qx Ub) Wm(Cq Fn Fy Gl Ii Jh Jm Jp Kf Kl Qb Qc Qd Qg Rh Ur Ut Uu) Kc(Fb Fr Ha Ii Il Im Is Jp Ms Mv Oz Pc Pf Qb Qg Qv Rh) Ow(Dk Fp Ha Hw Hx Ii Ik Is Iz Lu No Nr Oa Ok Qb Rh Un) Ct(Dp Fb Fy Ha Hv Js Mj Mp Mv Pc Pf Ql Qt Qz Tz Vp) Mw(Cv Fb Gz Hv Ii Il Iv Kq Ky Ms Nd Nj Pa Pk Tr Tv) Li(Et Hv Jp Jr Kr Me Mk Mr Ms Nd Nx Pd Pg Ql Uf Vt) Fr(cO dR Fb Fy gL Gn Hr Hw Jy Kl Me Ms Pd Qv Uf) Kk(Dc Fp Ha Ik Iz Jf Ky Ms Ns Oh Pe Pf Uu Uv) II(Al De Hw Hx Ik Iz Mi Mv Nc Nj Oy Qg St) Og(Ha Im Jf Lh Lj Mq Nc No Oz Pc Pf Vt Vv) Nn(Ed Gd Pi Qt Rg Tt Tv Ug Us Vq Vs Vu) Nx(De Ih Ii Ik Jy Mq Ne Pf Qg Rf Rh Vt) Fy(Fp Ip Jf Lh Mb Me Nm Oa St Uu Vt) Mk(Jf Lj Mj Ml Mq Pe Qa Qg Ql Ub Vv) Iz(Bo Et Ez Gp Iv Mr Ql Tr Vt Vv) Rf(Aj De Hv Jk Jy Me Nf Nj Oy Tn) Ms(Bb Fp Ih Jf Oa Ph Pj Pk Qg) Ik(Cu Cw Em Gp Ip Mc Mr Om Qv) Is(Bc Cu Gp Gz Iq Iv Jy Om Vv) Pf(Bc Fn Jf Ma Nc Ng Oh Om Vt) Jk(Bc Cu Fp Jf Ng Ql To Vo) Bo(Fb Fn Ih Im Mj Mq Nr) Qv(Ha Lh Qt St Tn Uu Vu) aA(aO aZ Bb Cx Qt Ss Uv) Em(Gn Im Kn No Qt Tz) Me(Kd Oa Qw Ur Uu Vv) Jf(De Fn Kd Mv Nc Uv) Lh(Dr Et Gd Jp Ke Pj) Hw(Dp Oa Qg Rh Ub) Ql(Fa Gd Io Iv Kd) Uu(Cu Ip Qg Ub Vt) Tj(aJ aP Co Gl) Ha(Fn Ky Nd Pk) Mr(Aj De Nj Oy) Ii(Db Nc Ng Rh) St(Kd Mf Pd Rh) Vt(Al Pe Tz Un) Fp(Hr Hx Nm) Mv(De Kz Vo) Ip(Aj Co Tz) Nm(Tn Tz) Nc(De Pg) To(Qt Vp) Tr(Dp Fb) Jp(Dr Vo) Kr(Hv Oh) Rh(Oh Un) Pd(Co Vs) EtOk MqHr NeNh OmPe} aA{Ko(AD aE aF aH aI aL Ap AR aS Ax bA bB bC bH bP bS bX cD cG CH cK cP Cq CT cU CW cZ dA DB DC dD DE dF dI dM dN Dp EF Ez fP GP Ha hB Hu Ih Ik Iq Is Jg Jh Ji Jk Jl Jp Js Jt Jy Ke Kf Lh Li Lj Lw Mb Mh Mi Mj Ml Ms Mw Mx Mz Na Nd Nj Nt Nu Nv Nw Oa Of oH Ok Om On Or Pd Pe Ph Pi Qa Qb Qc Qg Qh Ql Qm Qn Qu Qv Qx Qy Qz Rc Rg Rh Ri Rj Rm Tz Ua Ub Uc Ud Uf Ug Un Us Ut Uv Vo Vp Vs Vt Vu Vv tF) Af(An aY bN cB Cp Et Fw Ha Hb Hf Jd Jf Js Ju Jv Jy Kq Ky Lx Lz Md Mm Mt Nc Nh Nl Nn Ns Oa Oh On Oy Pd Pf Pg Pz Qa Qb Qc Qd Ql Qm Qx Rg Rj Rm St Uc Ud Ue Uo Us Ut Uv Vu Tj Ti Th) Pz(Ed Fn Ih Ik Io Iq Ir It Iv Jj Jk Js kN Ky Lv Lw Lz Ma Mi Mm Mn Ng Nh Ni Nr Nw Nx Oh Ok On Pb Pc) Nr(Fr Ih Io Iq Ir Is It Iv Jm Js Jt Lv Lz Ma Mb Md Mk Mn Mr My Mw Nc Nh Nj Nx Oh Oy Pb Pd) Iu(Bo cE Cw dF Et Hr iA Ih Io Jj Jk Js Kl Ks Lv Mb Md Mi Mv Nd Ni Nl Nn Ns Pb Pc Pd) Jt(Fr Hr Ih Ik Jg Jn Jr Js Lh Lv Lz Mf Mi Mm Mn Mu My Ni Nw Oh Ok On Pg Qb Up) Ma(bN cB Cx Fn fR Io Ip Iq Ir It Iv Js kN Mf mZ Oh Up) Ih(Ik Ip Iq It Jr Lv Mb Mn Ne Ng Nh Ni Nn Oh Pd Pg) Qd(aX aZ bI bN cB cV Fn Je Ju Kd Kp Ky Ld Pk Uo) Ng(Ik Io Ip Iq Is Iv Jk Js Lz Mg Mn Mv Nn Pd) Io(Bb Bo bZ cE Il Jj Js Kl Mv Nn oN Pb Uh) Js(Ir Jn Jr Lv Mn Mr Ne Ni Nl Oh Pd Pg) bN(aH aK aN aY bI bV cB cS Cu Cv fP gL) Iv(Bb Bo cO Cx Dg dH Il In Ks Tr) Ky(aK Bb cO cS Cu Et gL Ue Uk) Fn(cB cO Dg Et On Pd Qc Uh) Up(Et Kd Kr Lx Mp Mt On Tv) eM(aL bI bQ cB cM cZ dD dR) Ir(Bb Bo cJ cO Cx Dg Kl) Pk(Et Ip Is Kr Mm On) Iq(Bb cJ cO Dg Kl) It(cJ cO Kl mZ Uh) Is(cJ cO Dg Kl) Kq(cA cC Nq Uk) On(Ed Je Kp Tv) Uk(dH Qe Uh) cS(cJ cO Kl) Bb(Ed Jd) Th(Mz Om) Mn(Jj Mf) aX(cO Kl) DgEd NnNy LvMj MkkN TrbV KrcB} Gd{Ua(Af An Ao Cp Cs Cu Di Dp Ef Gp Ha Ic Ii Ir Iv Iz Jd Je Jg Ji Jj Jk Jp Ju Jv Kl Kq Kz Ld Li Me Ml Mr Ms Ne Nh Nk Nl Nn

Uk(Bb cJ Cx Ed Et Fa Fn gL Mm ON) Ed(Cu Cx Et gL Hb Kl Kr Ok Uh) Nn(Et Im In Jp Lj Mb Mj Mm Ni) Tr(aQ bU cF cS Fn gL gW Jq Th) eM(aR bE bO bP cX cY dB dC dH) Bb(Gz Is Je Jv Kd Mm Mp My) Fn(Bo Cu Cw Kl Ok Qa Tv) Is(Bo Cx dH Et Ks Pb Uh) Nl(In Lj Lz Ne Ni Nk) Dg(cS Iz Kd Oy Th) On(aX Iz Jd Ju Uo) Et(An cO Kd Tv) Nu(qU qW rB rZ) Lv(In Md Pd Pf) Qe(Cx kN qU Tv) bV(cJ Ks Ok Uh) Th(Ad Mm Ph) Mb(In Jj Mf) Ny(Fr Mu Mv) cS(bQ Ks Uh) Cx(Kr Mp) Tv(Ex Ok) Ik(In Jj) Jk(mZ Ni) cB(Kl Ut) gL(Kk Mf) AaMk BoTi GdGl MjPd HbfR KrcO OkkN UoUh} Gd{Ua(Ar Ba Bg Bn Bo Cq Cv Db Dc Dd De Dk Dr Ed Em Ez Fr Fw Fy Gn Hv Id Ih Ik Im In Io Is Jh Jl Jn Jr Js Jy Kj Kk Ko Lu Lw Lx Lz Ma Mc Md Mh Mi Mj Mk Mp Mq Mu Mv Mw Mx Mz Nc Ni No Nq Nr Ns Nt Nx Of Oh On Ou Ow Oz Pa Pe Ph Pi Pk Po Qb Qg Ql Qn Qx Ra Rf Rj Sr St Tz Ud Ug Um Un Uo Ur Vp Vu) Oe(Ap Bc Cx De Dg Em Fp Gl Hw Hx Im Iv Ks Li Mb Mc Mp Ms Mt Mw Mx Nc Nf Nh Nm Nu Nv Nx Og) Mm(As Ax Ex Hf Hq Ir Jf Kj Kk Mk Mn Na Ne Nl Nq Nu Og Oh Ow Pi Qg Rb Ri Sr Uf Ur Vq Vu) Uu(Ap As Bc Ib Jf Ke Kg Lu Mg Na Nu Oa Pc Qv Qy Qz Rh Ub Uh) Pj(Ax Ct Cx Fy Je Jk Ke Ks Mb Mk Oa Om Ql Qw Qz Ss Uv) Mu(Bo Ik Iz Kr Ma Mf Og Qt Qy Ug Uk Uo Ut Vt Wm) Qy(Ba Iu Ly Ma Mq Ni Nr Nt Of Oi Qt Qw Ul) Ib(Bn Gn Id Iv Je Jf Kc Ke Kr Md Ml) Mv(Et Kc Kx Ky Mf Or Qv Qz Ri Uf) Vt(Ao Hw Ii Jf Lh Nn Nv Oa Qg Uv) My(Ed Fn Iz Lu Oa Qz Rc Tz Uk) Hc(Ct Dc Em Jy Kn Mq Nj Rb) Iz(Cv Hb Jo Kd Mf Na Nu Qz) Po(Cw Iu Jt Kr Mt Ue Uh) Lu(Bo Fy Hw Of Qw Ug Us) Rh(Bo Dc Mf Oi Pi Ug Um) Ef(Cw Il Ke Pd Qw Uh) Et(Ba Lh Nn Ql St) Fr(Ap Cw Jt Kx Ue) Nv(Fa Jt Kf Kr Ri) Qw(Hw Hx Mk Ue) Tz(Ct Hb Nm) Il(Ba Ez Ik) Jl(Hb Ky Ur) Ue(Of Qt) Je(Kd Mw) AoKg BaUf CtJf CwJg FwKr MfIk HbLi JkKc JoOf} mZ{It(Fp Hq Hr Hu Ih Io Iv Jh Jq Jr Js Jt kE kG Li Lu Lv Lw LY Lz Mc Md ME Mg Ml Mj Ml Mn Mp Mq Mr mS Mu mW MY Mz NA Nb NC Nd NH Nl nJ nK nL nM Nq NR Ns nT nU Ny Of On oO oQ Pc Pd Pf Qd Qe) Iu(Hu Ii Il Iv Jj Jm kN mE Mk Ms mU Mv Ne Ng nK nN Oz Pc Qb) Mk(Ih Iv Jt kK Ma mE Mf Mj mT Nd Nf Nr Qe) Nj(Mf Mj mM Mv Mz Nf nN oP Po) Ma(Fr Jp Lj Mu Ng Nv Om) Mv(Jo Mj Ng Nq Pg Pz) Qe(Hx Lx nK Nx Pa Po) Jk(Mf Mj Nf Pg) Iv(Nx Og Po) Js(Hx Nv Pa) Mj(nJ Og) Pz(Ng oP) Qd(Ms Nv) Ok(Jp Om) IL(jT nU) MfNf MzOm JtNw iCjY jGjH} Ti{Pk(Ad Af aG Aj aK aP Ar As aY aZ Bg BN bQ bU bW cC cE cK cL cO Cp Cq Db Dg Di Dk Dl Ed Ez Fr Gp Hc Hf Hq Hu Hv Hw iA Ii Ij Iq Ir Is Iv Jh Ji Jl Jm Jt Kd Kj Kk Kp Kq Kr Ks Li Lv Lw Lx Ly Md Mj Ml Mm Mp Mt Mu Mw Nf Ng Ni Nm No Nq Ns Nu Nx Oe Of Og Or Ou Ow Oy Pa Pe Pg Po Pz Qa Qh Ql Qn Qt Qv Qw Rb Rc Rm St Tr Tv Un Uo Us Ut Vp Vq Vt) Hx(Jo Ks Ow Tv) Sr(Ky Mm Tr Uh) An(Jo Uk Tj) Dp(Bo Ed) Ib(Ky Ph) Ss(Mm Tr) TvKn JoLh} Mm{fR(aO As Ax BA Bb bQ cK cN cO cR cT Cv cX dJ dL Et Hf Hv Hw Ih Jk Jl Jm Jn Js Kc Ly Ms Mv Ng Nh Nn Nu Nv Nw Of Oh Oy Oz Pd Pk) Em(Aj Ax Ex Ez Fy Gn Hw Ib Ir Jc Jf Ko Mg Mp Na Oa Qe Qg Qw Qz Ri Sr St Ub Vs Vv) Gn(Cq Fb Je Kf Kn Lx Mx Nc Ng No Nq Nt Og Qd Qg Ql Qt Qw Qz) Dr(Co Ct Dk Fb Ha Hw Ib Ik Jm Mw Ng Qb Qy) Ss(bV Io Is Iu Th) Ib(bV Is Iv) Sr(bV Is) aP(dH Ko) NqTr TvaJ JgqZ PibV} eM{cN(aC aD aE aF aH aI aJ aO aP aW aZ bA bF bO bV bW bZ cE cF cH cI cM cU dA dC dD dE dG dJ dK dL dM eF gP) aJ(aR bC bG bN cK cR cY dD dE dL) bC(bL bN bS cS cT cY dD eF gC) dM(aQ aR aU bI bO bS cS dR) dD(cY dR gC) bN(bG dE) aPbL blgC cBcZ cYdR} Em{Pj(Ad Ap Dc Dk Ef Gl Ib Ik Is Jf Jk Jn Ke Ko Ld Lj Mk Mn Mt Nb Oa Oi Pe Pf Pk Qw Qz St Uv Tj) Hu(Aj Ii Iu Mf Ok Pz Qv Ub Uk) Ua(Il It Jf Jo Jt Ky Ub Vv) Nm(Ct Lx Mw Qw) Hc(As Ch Dg Kg) Oe(Bb Kg Lu) Po(Et Uh) Fr(Kf Ok) Jl(Jt Kf) CxMu WmQy EtFb MgIz MwKy} Tr{Nq(Ad Af Bb Cu Dg iA Ii Il Io Is Ko Ky Mp Mr Nk Nm Ok Pf Tv Uk Th) aP(bF bM cJ dG dN Dp Et Fn Ok Tj) dM(dH Et Iv Jo kS Ny Rj Uh) Jo(Ao bV Dk Fn fR Jm) Dp(bV Cp dA Jd) fR(bF cJ Pk Uh) bV(Fn iA Mx) Gz(dA Ua) aJ(cB kS)} aP{cO(cW Fn Kd Kr Ky Mf Mv Pd Pk) Et(bJ Bo dE dH Ky Nh Uk) Ko(Ba cJ dH Ky oK Pd Pk) dH(Fn Mf Pk Ue Vu) iA(Ma Mf Tv Uk Ut) dG(Ky Pk Uk) dL(Bo dE Ky) oN(Jy Tn Th) Fn(bW Pd) BoPd KdbW KqoK UkcJ aMbQ} aJ{dH(Fn Ir Is It Mr Tv Ue Uk Th) dG(An Aw Bo Cp fR Ip Ir Tv) Ko(Aa An bM bW cJ) Tv(cB Ex Up) Kq(bM Ed Ip) bN(dL iC Th) aC(bM dL) cJ(bV Th) cO(cS Kr) iA(Iu Iv) kS(bQ kQ) BoMn DlEd QeUp} Dr{Hu(Ch Iu Jm Kf Kj Kl Mg Pd Pk Qv Ub Uh) Hc(Bo Cw Et Kg) Ua(Dg It Jt) Oe(Bo It Lu) Et(Jl My) Fr(Jt Kq) Pj(Ba Iz) BoQy} oE{qW(aE aY aZ bH bL cP cX dI iJ kR qT qU rB) jP(aQ aZ bJ cX iP jG iL) bCjM bGjG cJiC cWrA iPjQ rBkQ} Nq{Kr(Bo Cu Cw Ko Pd Tn) Et(Jy Kd Tt Tv Uk) Jo(Fn Jy Tn To Tt) Uh(Fn Tv Uk) Dg(Fn Kd) cO(Ue Uk) NrnK IuiA} Gn{Hu(Ch Jf Jm Kf Kl Ko Qv Ub) Pj(Hx Lh On) Dg(Oe Po) Et(Nv Oe) My(Ko Rc) Ua(It Wm) Kq(Mu Mw) ApHc BoLu bAdB} Pz{oP(Fr Ik Il In Iq Iv Jp kC Lh Ly mH Mr Ms Mu nB nN Nx Oh Pg) Mv(Jj kF Nn Nw) MskF} Mv{Iu(cE cG cO Cw Qg) Ma(Jj kK oH) cO(bV cN Ue) Fn(Mn Pd) CuUk NrkF MjkO MnJj UeKy} Et{Jg(gW Ic Kd Sr Uk) fR(Bo bW Oe Uu) Fn(Cp Lh Mx) Uk(Cp Lh) GzJl MxJd MyVq} bV{iA(Fn Ib Jl Jo Kd Li Mx Oi Pd Qx Uv) Ky(Aa cO iJ) cO(Fn Pk) UkcJ} Ma{Ba(bI cQ kS Na) kS(Cp Hc Jh) fR(Hc Ib) GzdM MwkK PkbA} Uk{cO(Fn Iz Jk Jl Ua) Cp(Om Uh) CuIz FnRh MuKq MxKo UpbA} Cp{Cw(aX cS) Fn(Jo Pd) AdgC ThJo UeKy} Pk{Aa(cT kS To) bA(Ko Rh) BafR HxiP} qZ{rB(jR jT lM) Hv(Ir Pe) Hrlu jGqT} jP{cQ(aF bJ iP kR) kS(aE iZ) FrLi} Gz{Bb(Ba Bg) Ua(Kf Ko) Hc(Ad Kr)} jH{nU(mM nH) IL(nB nJ) bNiC nRjl} Dg{Jg(Ap Fn Kd Tj) IzcB} Jo{Th(Al Fr Tz) FnHv IuIz} IL{IK(nB nJ nT) nUjT} Fn{MyPd cNcO dHdM} Ue{CuIz MyKy dHdM} Hx{ThKs KoiZ} Hc{BbEx KefR} iC{kS(bC bW)} EzcCgW UaUffR ItNwkN JjjGjY NvNykK aCcZdM aFbMqW Unconstrained panels with 3 analytes, where 1.0E-7 >= 'AUC p-value' > 1.0E-8. Contains 10,667 panels of 10,943,034 total panels evaluated. : Gc{Ax(aF aG aH aI aK aL aN aO aQ AR aS aV aW aY bC bE bF bL bN bQ bU bW bZ cA cC cD cF cG cH cL cM cO cQ cR cU cW cX cY cZ dA dD dF dH dK dL Dp Ed Fa Fp Hr Hu Hv Hx Ic Id Ih Ii Im Io Iq Is Jh Jj Jl Jn Jp Jr Js Jv Jy Kd Ki Kj Kl Kn Kq Ks Kx Ky Li Lj Lu Lv Lx Lz Ma Mb Md Mf Mg Mh Mi Mj Mr Mz Nf Nh Ni Nk Nl Nr Ns Nv Nw Nx Ny Oh Ok Pb Pc Pg Po Qb Qd Qh Ql Qn Qt Qu Qw Qx Sr Ss Uc Ue Ug Uk Um Un Ur Vo Vp Vq Vs Vu) Jf(Af Aj An Ar Bb Bg Ch Co Cq Cs Cu Cv Cw Db Dc Dk Dr Ed Em Et Ex Fa Fp Fr Gd Gl Ha Hq Hx Ic Ih Ij Ik Il In Iq Ir Iv Iz Jh Jj Jn Jo Jp Jr Js Jt Ju Jv Jy Ke Kf Kg Ki Kj Kl Kn Ko Ks Kx Ky Kz Lh Lu Lv Lw Lz Ma Mc Md Mg Mh Mi Mj Mn Mq Mt Mz Nd Nf Ng Nj Nm No Nr Nt Nw Ny Oa Ok Oz Pa Pb Pc Pe Pg Ph Pi Pj Qa Qd Qe Ql Qm Qn Qu Qv Qw Qz Ra Rc Rf Rh St Tz Uc Ud Uh Uk Ul Um Un Uo Vs Vu Vv) Jd(Ad Aj Al An Ar Aw Bg Bn Co Cq Cv Cx Db Dd Dg Di Dp Ed Ef Et Ex Ez Fa Fb Gd Gl Gz Hb Hu Ic Id Ij In Io Ip Iq It Jj Jk Jn Jo Jp Jq Jr Jt Ju Jv Jy Ke Kg Kj Kl Kn Kp Kq Ks Kx Kz Ld Lv Lw Lz Mc Md Mg Mh Mj Mn Mp Mq Mt Mz Nh Nj Nk Nm Nr Nx Ny Ok Oy Pi Pz Qa Qb Qc Qe Qh Qm Qu Qz Ra Rc Rg Rj Rm Sr Ss To Uc Uf Ug Uh Uk Ul Um Uo Up Us Ut Uu Vo Vu Tj) Jl(Ad Al Ap Ar Aw Bg Bn Ch Co Cq Cw Dc Dd Dg Di Dl Dp Ef Et Ex Fa Fp Fr Gl Gp Hq Hu Ic Ij In Ir Is Iz Jh Jj Jk Jm Jo Jp Jr Js Ju Jv Ke Kf Kg Ki Kj Ks Kl Kn Ko Kp Lh Lj Lu Lw Lx Lz Mb Mc Md Mf Mh Mi Ml Mn Mq Mr Mv Mw Mz Ne Nl Nq Nt Nu Ny Oa Or Pd Pe Pf Pi Pj Pz Qa Qb Qc Qd Qg Ql Qn Qu Qx Qz Rf Rg Rh St Ua Ub Ug Uh Uk Um Un Us Ut Uv Vq Vv Tj) Ii(Ad Aj An Ap Bb Bn Ch Cq Cu Cw Cx Dc Dd De Di Dl Dp Dr Ef Et Ex Ez Fb Gp Hq Hu Hw Hx Ic Ij Ik In Io Iu Iv Jh Ji Jj Jk Jn Jp Jr Ke Kj Kl Kp Kr Ks Kx Ky Kz Ld Li Lj Lu Lw Lx Mb Mc Mg Mh Mj Mk Mp Mq Ms Mv Mz Nd Nf Nh Ni Nk Nr Nw Oa Ok Oy Oz Pc Pf Ph Pk Po Pz Qa Qb Qc Qe Qg Qh Ql Qn Qt Qu Qw Qx Ra Rg Sr Tz Ud Ug Uh Ur Ut Vp Vq Vv) Nw(Af An Ap Ar Aw Bb Bg Bn Bo Ch Cv Cw Db Dc Dd Di Dl Ed Ez Fb Gl Gp Gz Hq Hv Hx Ic Ij In Io Ip Iq Ir It Iz Jj Jn Jo Jp Jr Js Jy Ke Kf Ki Kj Kl Ko Kp Kq Ky Kz Lh Lv Lw Lz Mb Mc Mg Mh Mi Mj Ml Mn Mp Mt Mz Nd Nf Nh Nj Nl No Nr Ns Oh Pa Pc Pe Pg Ph Pi Po Pz Qa Qb Qd Qe Ql Qn Qu Ra Rc Rg Sr Ss Tr Tz Ub Ud Uf Um Us Ut Vq Vu Vv Tj) Jk(Af Aj Al An Ap Aw Ba Ct Cx Db De Dg Dk Dl Dp Dr Ef Em Fa Fn Fr Gn Hb Hq Hr Hu Hv Hw Hx Ic Ih Ij Ik Im Iq It Iu Iv Jg Jh Ji Jp Jq Jr Jt Ju Jv Jy Kd Ke Kf Ki Kp Kr Ky Ld Li Lz Mf Mi Mk Mn Mq Mt Mv Mw Mz Ne Nf Nh Nj Nl Nm No Nq Ns Of Oh Or Oy Oz Pb Pc Pd Pe Pf Pg Ph Pi Pj Pk Po Qc Qg Qh Qm Qu Qw Qx Qy Qz Rg Uh Uo Ut Uv) Ef(Aj Dp Fa Fn Fy Hr Hu Hv Hx Ic Id Ih Ik Im In Ir Is It Jg Jh Ji Jn Jq Jr Jt Ju Jv Kc Kg Ki Kj Kn Kp Kr Ks Lh Li Lu Lv Lw Lz Mb Mc Md Mf Mg Mh Mi Mj Mk Mp Mq Ms Mv Mw Mz Nf Nj No Nq Nr Ns Nv Oa Of Oh Ok On Or Oy Oz Pa Pb Pc Pe Pf Pg Ph Pi Qa Qb Qc Qd Qe Qg Qm Qn Qu Qw Qy Rc Rg Rh Rj Rm To Tz Uh Um Ur Vq) Pf(Aj An Ba Bb Bn Ch Cq Cv Cx Dc Dd De Dg Di Dk Dl Dp Ex Fp Fr Fy Hb Hq Hr Hu Ic Ih Ij Ik Im Io Ir Is Jg Jh Jj Jm Jn Jp Jq Jt Ju Kd Ke Kl Kp Kx Ky Kz Lj Lu Lw Lx Mb Mc Md Mf Mh Mi Ml Mp Mq Ms Mt Mv Mw Nd Nf Ni Nj Nk No Nr Of Ok Oy Oz Pa Pb Pc Pe Pj Pk Pz Qa Qc Qd Qe Qg Qn Qu Qx Qy To Ua Ub Uf Uk Uo Us) Ua(Ad Af Aj Al Ap Ar Aw Bg Bo Co Cq Cx Db Dc De Dg Ed Et Ex Gl Hb Hq Hu Hv Hx Ic Id Ih Ij Ir Iv Jg Jh Jn Jo Js Ju Jv Jy Kd Ke Ki Kj Ko Kp Ks Kx Ky Kz Lh Li Lj Lv Lz Mb Md Mf Mi Mj Mk Mn Ms Mt Nd Ne Nh Nj Nm Nq Nr Ns Ny Oh Oy Oz Pb Pc Pe Pg Ph Pj Qd Qe Qu Qw Rc Rj Ss St Tn Tz Uh Ul Uo Ur Us Ut Vt) Ly(Ad Af An Bb Bc Bo Ch Cs Cu Cv Cw Cx Db Di Ed Et Fa Hb Hf Hr Hv Hx Ic Io Ip Iq It Iu Iv Jj Jm Jn Jr Js Ju Jv Kc Ke Kf Kg Kk Kl Kn Kp Ks Ky Kz Ld Lj Lv Lz Ma Md Me Mf Mg Ml Mn Mz Nf Ng Ni Nj Nk Nl Ok Oy Pd Ph Pi Pk Pz Qc Qe Ql Qm Qn Qz Ra Rb Rc Rj Ss Tn Ub Uc Ue Uf Ug Uh Uk Um Uo Us Vo Wm Tj) Is(Ad Aj Al An Bg Bo Ch Co Cq Cw Dc Dd De Dg Dl Ed Ex Ez Fa Fb Fy Gl Hb Hq Hu Ic Ih Ij Ik In Ir Jh Jj Jm Jn Jp Jq Jr Js Ju Jv Kd Kf Ko Kp Ks Ky Lh Lj Lv Lw Lz Mc Md Mg Mh Mi Mj Mt Mv Ne Nf Ni Nl No Nq Nr Ns Ny Oa Oz Pa Pb Pc Pe Ph Pi Pj Pz Qd Qe Qg Qm Qn Qx Qz Rc Rf Rh St Tn Tr Ub Um Uo Uv Vt) St(Af Aj Al Ap Ba Bo Cs Cu Cv De Dg Dk Dr Ed Em Et Ex Ez Fb Fn Fp Fr Gn Gz Hb Hr Hu Hv Hx Ih Io Iq Je Jg Jh Jm Ju Jv Kc Ke Kf Ki Kj Kk Kp Kq Kx Kv Kz Li Lj Lz Mb Mk Mr Mw Mz Nc Ng Nh Ni Nr Ns Nt Nv Nx Ny Oa Oh Pb Pc Pg Ph Po Qa Qb Ql Qn Qu Qw Qx Qy Rc Rf To Tr Ub Uc Ug Uh Uo Ur Us Uu Vo Vv) Li(Aj Al Ar Aw Bn Co Cq Cv Db Dc Dd Dg Dl Dp Ed Ex Ez Fr Gl Gz Hq Ic Id In Iq Ir It Jj Jm Jo Ju Kf Kg Ki Kj Kp Ks Kx Mb Mg Mh Mj Mp Mq Mv Nh Nj Nk Nm No Nq Ny Oa Ok Or Oz Pc Pe Pi Pz Qa Qb Qd Qh Qm Qu Ra Rc Rm Sr Ss Tn Tv Tz Ub Uc Ud Ug Uh Uk Ul Un Up Ur Us Uu Uv Vp Vq) Nb(Ad Af An Ap Ar Bb Bn Ch Cq Cu Cv Cw Db Dc Di Dl Dp Ez Fb Hq Id Ij Io Iq Ir Jh Jj Jn Jo Jr Js Jt Kf Ki Kj Kk Kl Kq Kx Kz Lu Lv Lw Lz Mb Mc Mg Mh Mi Mj Mn Mp Mw Mz Ng Nr Ny Om Or Oz Pa Pb Pc Pe Pg Pi Pk Pz Qa Qb Qc Qd Qh Ql Qn Qt Qu Ra Rh Ub Uk Ul Un Up Uv Vp Vt Vu Vv) Il(Af Bc Bg Ch Cq Cu Cx Fn Gd Ha Hf Hq Ij Im In Io Ir It Iv Jm Jn Jp Js Jt Jv Kf Ki Ko Kr Lj Lv Lw Lz Ma Mc Md Mf Mh Mj Mp Mq Mr Mt Mz Na Ng Nh Ni Nk Nl No Nr Ns Nt Ny Oa Oh Om Or Oz Pb Pd Pe Ph Pj Qa Qc Qd Qu Qx Qz Rf Ss To Tr Tv Tz Ub Ud Ue Ul Um Un Vp Vt Vu) Nx(Ad Af Aj An Ap Bb Bc Bn Bo Co Cq Cs Cv Cx Di Fy Gl Hf Hu Hv Hx Ij In Io Ip Iq Ir It Iu Iv Iz Jj Jm Jn Jo Jq Jr Js Jt Kk Kr Lv Lz Ma Mb Md Me Mg Mh Mj Mk Mn Mp Mt Mz Nd Nf Ng Nh Ni Nl Nm Nr Ny Og Ok Oy Pb Pg Ph Pz Qa Qb Qc Ql Qu Rb Sr Tz Ub Un Ur Uu Uv Vu Wm Tj) Rf(Ap Bb Bc Bg Cu Cs Cx Dp Dr Et Ez Fn Fr Fy Gl Gp Ha Hb Hu Ih Iu Iv Jj Jm Jn Kf Ki Kk Kl Ks Kx Ky Kz Ld Lj Lx Lz Ma Mf Mg Mh Ml Mu Mv Mx Mz Ne Ng Nh Nk Nl Nq Nu Oh Ok Pb Pd Pg Ph Pj Pk Qc Qg Qh Qm Qn Qu Qx Qz Rc Rh Ss To Ug Uh Um Un Uo Ur Us Uv Vo Vq Vs Vt Vv) De(aA Dp Ez Fb Ha Hq Hr Hu Hv Hx Ik Im In Iq It Iu Iz Jh Jn Js Jt Ju Jv Kc Kd Kg Kk Kr Ky Kz Ld Lh Lj Lu Lv Lz Ma Md Mf Mg Mj Ml Mn Mp Mq Mt Mz Nd Ne Nf Ng Nh Nj Nk Nl Nm Ns Nv Ny Oa Og Om Oz Pb Pc Pe Pg Ph Pj Pk Qa Qb Qc Qd Qe Ql Qw Qx Rj To Ud Uk Vo Vp Vu) Mw(Ad Aj Ap Aw Bc Cu Cw Cx Dg Di Dl Et Ez Fp Gd Gl Gp Ha Hb Hq Ih Ij In Iq Ir Iu Iz Jh Jj Jm Jn Jp Js Ke Kf Kk Kl Ko Kp Kr Ks Kx Lj Lw Lz Mc Md Mf Mi Mj Ml Mn Mp Mq Mt Mv Mz Nk Nq Nr Ns Oa Om Pb Pc Pd Pe Pg Pj Pz Qa Qd Qe Qg Ql Qm Qx Rg Ub Uk Um Uo Ut Uu) Nt(Af An Ap Ar Bb Bc Bn Cs Cu Ed Et Ex Ez Fp Fr Gl Gn Gp Hq Im In Io Ir Iv Iz Jj Jn Jq Jr Js Jv Jy Kf Ki Kl Kn Ks Ld Lj Lu Lv Lw Mb Mc Md Mh Mi Mj Mp Mv Mz Ng Nk Ns Ny Oh Pa Pb Pc Pe Ph Pk Pz Qa Qb Qh Ql Qt Qu Qx Qz Sr Tz Uc Ug Uh Um Un Ut Uu Vs Vu Vv) Fr(aC Af aH Aj Ao aY aZ bB bI bL Bo bQ bS cB cI cJ cK cV Cx DG dH Dp Fn Ha Hb Ih Ik Iq Iu Iz Jh Jm Jn Jo Jr Jt Jv Kd Ke Kf Ko Kx Ky Ld Lz Mg Mi Ml Mn Mq Mu Mv Mz Ne Nh Nk Nl Nm No Nr Ns Om Pb Pg Qa Qe Qg Qm Qw Rc Tn Tr Tt Ub Ul Um Uo Uu Uv Vt) Lx(Ad Al Bg Ch Co Cq Cv Cw Db Dd Dg Di Dl Dp Ex Fp Fw Gd Gn Ic Id Ij In Ip Ir It Jm Jo Jq Jt Ju Jv Kg Kl Kn Ko Kp Kx Ky Lv Lw Mb Mc Mg Mi Mj Mq Ms Ng Nl Nm Ok On Oz Pc Pe Pi Po Qb Ql Qm Qt Qu Qv Qw Ra Rg Rj Rm Sr Ss Tz Ub Uc Up Vp Vq Vs Vu Vv) Ue(Ad An Ch Cs Cu Cw Dg Di Dl Dp Et Ez Fa Fb Gp Hb Hf Hq Hr Hx Ij In Ip It Iv Jj Jn Jr Jv Ki Kj Ko Kq Kx Ld Lj Lw Lz Ma Mb Mc Md Me Mf Mh Mk Mn Mt Mz Nd Nh Ni Ns Og Om Or Pb Ph Pi Pj Pz Qc Qe Qh Qx Ra Rc Ss Tt Ub Uc Uh Uk Ul Um Up Vq Wm) Fp(aA Cs Hq Ih Ij Im In Io Ir Iu Iv Jh Jm Jq Jr Jt Jy Kf Kj Kq Ld Lh Lw Lz Mc Md Mf Mg Mh Mj Ml Mn Mp Mq Mr Mt Mz Nd Ne Nh Nk Nl No Nr Ns Nu Ny Pa Pc Pd Pe Pg Ph Pj Pk Qa Qb Qc Qd Qe Qh Qm Qu Qv Rh Tn To Uk Ul Um Us Uu Vo Vv) Je(Ad An Ap Ar Bg Ch Co Cq Dd Dl Dp Ex Fa Gd Hu Im In Iq Ir It Jh Jn Jq Jr Js Ju Jv Ke Kf Kg Kn Ko Kp Ks Lv Lw Lz Ma Mc Md Mg Mn Mp Pj Ns Ny Ok Om Pb Pe Pg Pj Pz Qa Qd Qe Ql Qm Qn Qw Rj Sr Ss Uc Uf Ug Uk Ul Vv) Iz(Af Ao Aw Ba Bg Bn Ch Ct Cx Dd Dg Dl Dp Dr Fy Gn Hb Hv Hw Id Ij Iu Jg Ji Jn Ke Kf Kg Ki Kj Kp Kr Kx Ky Ld Lj Mf Mg Mk Ml Mn Mq Mt Nc Nd Nv Ny Oh On Oz Pc Pg Ph Pk Po Pz Qd Qe Qm Qn Qw Qz Rc Ss To Tz Uh Ur Ut Uv Vq) Nr(Ba Bb Bc Cu Dl Dr Et Ez Fa Fn Hb Hr Hu Hv Id Ih Ij Jg Ji Jm Jr Ju Jv Jy Ke Ki Kn Kq Ks Kz Lu Lz Mb Mg Mi Ms Nd Nf Nh Ni Nj Nk Nl Ns Ny Oa Om Oy Pb Pd Pg Ph Qd Qg Ql Qn Qu Qx Qz Rc Rh Tv Uc Uh Uk Um Ur Uv Vp Vu) Ha(Af Cs Cu Cv Db Dc Dk Em Et Ex Ez Gd Gn Gp Hu Hw Hx Ih Ik Im Ip Iq Ji Jj Jp Jr Jy Kd Kf Ki Kl Kp Kq Kr Ld Lh Lj Lu Ma Mf Mq Ms Mz Ne Ng Nj Nk Nl Oa Om Oy Pa Pb Pz Qh Ql Qm Qt Qw Qx Qz Rh Rj To Uh Uu Uv Vs Vv) Ri(Af Aj Al Ap As Bc Bg Bn Ch Cq Cv Db Dc Dp Ez Fb Fy Gl Ik Ip Ir It Iv Jh Jn Jr Jy Kd Kn Ld Lj Ma Mf Mi Mp Mz Nh Nj Nl Nm Ny Og Om Or Ow Oy Oz Pc Pd Pg Pj Pz Ql Qv Rm Sr Ss Tr Ub Uc Ud Uh Ul Um Ut Uv Vq Vs Wm) Pe(Aj An Aw Ba Bg Bn Ch Cs Cv Db Dc Di Dk Dr Et Fa Fn Fy Hr Hv Hx Ij In Io Ip Iu Jg Jh Jj Jm Jn Jq Jr Js Kp Kx Ky Ld Lu Lz Md Mf Ms Mu Mv Mz Nd Ne Nf Ng Nh Ni Nk Nl Ns Ny Oy Pa Pb Pg Pj Po Qc Qg Qh Qz Rh Uo) Lh(Af Ap Ba Bn Ch Ct Cv Db Dg Di Dl Dp Gz Hb Hq Hr Hu Hv Ih Ij Ik Ip Iu Jg Jh Jn Jo Jt Kc Kf Ko Kr Kz Lj Lw Lz Mc Md Mf Mk Ms Mv Mz Ne Nh Nk Nl Nq Ns Ny Oh Ok Pa Pb Pc Ph Pz Qg Qm Qy Qz Rc Uf Uh Uo Uv Vt Vv) Mk(Af An Ar Bb Bc Co Ct Cv Cx Db Dp Em Gp Hw In Io Ip Ir Iu Iv Jh Jj Jp Js Kc Kd Kf Kg Ki Kr Lu Lv Lz Ma Me Mf Mg Ms Mt Mz Ne Nh Nk Nl Ny Om Or Oy Oz Pc Pd Ph Pk Qc Qe Qx Rh Rm Ud Un Ut Vo Vu Wm) Mu(Ad An Ar Bg Bn Ch Co Dc Dd Dk Dl Dp Ex Fa Hu Ic Id Ih Ir It Jq Jv Ke Kf Kg Ki Kj Kn Ko Kp Lu Lv Lw Mb Mc Md Mf Mg Mi Ml Mq Mv Ns Oz Pg Pi Pj Qg Qh Qn Qu Qy Rj Rm Sr Uc Ug Uh Un Us Uv Vp Vq Tj) Nq(Aj Bb Bc Cs Cu Dc Dp Fa Gd Gl Gp Id Ih Im Ir Jh Jm Jn Jq Jr Kf Kg Kj Kp Kx Ky Lj Lu Ma Me Ml Mq Mz Ne Ni Nj Nl Oh Ok Om Or Oy Pd Pi Qm Qv Qw Qy Qz Ra Rh Ub Uc Ug Uh Uk Un Ut Uu Vq Vt Vv)) Hf(An Ar Cw Cx Dg Di Dl Dp Em Fa Fb Ir Iu Iv Jq Jy Kc Kd Ki Kj Kk Kn Kp Kx Lj Lu Lv Lz Ma Mb Me Mf Mg Mh Mj Ml Mr Mz Ng Nh Ni Nl Ns Ny Oz Pd Pg Qc Qd Qe Qn Qu Qz Sr Ss Tv Uc Ud Uf Ug Uh Ul Um Un Uo Up Ur Ut Vp Vq Vu Tj) Ik(Ad Af Al Ap Bc Bo Cx Dk Dl Ex Fn Fy Gd Gn Gz Hq Hr Hv Hx Ih Ij Im Io Iu Jg Ji Jj Jm Jn Jp Jr Kz Ld Lu Lz Ma Mb Mf Mg Mi Ml Mq Mv Mz Ne Nh Nl No Nv Of Oy Pg Pj Pk Qg Qx Qz Rh Uk Vt Vv) Qy(Ad Af Ap Aw Cq Cu Cw Cx Dl Dp Ex Ez Fy Gl Gp Hb Ic Ij Io Iu Jm Jn Jo Js Kf Kk Kl Kr Ks Kx Ma Ml Mq Mt Mv Mz Ne Nh Nk Nm Ok Pd Pj Qa Qd Qe Qx Qz Rg Ub Uf Uk Um Uo Ur Ut Uu Uv Vo Vq) Ms(Bc Cu Dc Dk Dr Gd Gp Hr Hu Hv Hw Jg Jm Jp Ju Jv Kd Ke Kg Ki Kn Ko Kq Kr Ks Ld Lj Lu Lv Me Mf Mj Mp Nd Nh Ni Nk Nl Nv Ny Oh Ok Or Oy Pd Pg Pi Qa Qd Ql Qm Qt Qv Qx Tr Tz Ub Ur) Oi(Af Ap Ar Bc Bn Bo Cv Cw Db Dg Dp Ed Et Ex Fa Fb Fn Fy Ic Iq Iu Jh Jn Jo Jt Ki Kl Kp Ks Ld Mb Me Mg Mh Mn Mt Nd Ng Nj Nk Nm Og Ow Ph Pz Qu Qv Qw Qx Qz Sr Ss Ub Uc Ul Um Uv Wm Tj) Po(Ad Aw Co Db Ez Fa Fb Fw Gz Hb Ic Id Ir It Jh Jj Ju Ke Kg Kj Ks Ky Mg Mj Mt No Oa Or Oz Pc Pi Qh Qn Qu Ra Rc Rg Rj Rm Sr Ss Tv Uc Ud Uf Ug Uh Ul Um Un Uo Up Ur Ut Vp Vq Vu Tj) Nu(Ad Ap Cs Cu Cv Cw Dd Dg Dp Dr Et Ex Fa Hb Ic Id In Io Iq Jo Ju Ke Kg Ko Kx Ky Kz Ld Lu Nh Ni Nk Nm No Or Oz Pi Qb Qe Qm Qn Qt Qw Qx Qz Ra Rc Rg Rj Sr Ss Uc Ud Uk Uo Us Ut Tj) Ba(Et Ez Fa Hq Hr Hx Ic Id Ij Iq Ir It Iu Iv Jj Jq Jr Jt Jv Jy Ke Kf Kg Kn Ko Kp Ks Kx Kz Ld Lu Lv Mb Mj Mp Mt Nf Ni Nj Ok Oy Ph Pi Qc Qe Ra Rc Rg Rh Rj Rm Uc Ud Uk Um Un Uu) Ct(Gz Hq Hu Hw Hx Id In Io Ir It Iu Jn Jv Kc Kd Kg Ki Kj Kl Kn Ko Kr Ky Lu Lz Ma

Figure 13 Continued

Mb Me Mg Mz Nd Ne Nj Nk Nl Nm Ns Ny Og Om Pd Pg Ph Pj Pk Qc Qm Qn Qx Rh Rm Ud Un Ur Vo Vu Vv) Cs(aC aF aG al aK aL aN aO aQ aS aU aV aY bC bF bN bO bQ bW cA cC cE cH cL cM cQ cU cW cY dC dF dK dL Ez Fy Gd gW Hr Hw Jh Kf Kr Lu Mq Mr Na Nc Nf Ni Ok Oy Qt Qu Tz Vt Vv) Nc(Al Ap Bg Bo Ch Cq Cv Cx Dc Dk Dp Ex Fb Fy Gl Hr Hu Hv Hx Ih Im Ip Jh Jp Jr Kk Ks Kz Lu Me Mj Ml Mq Nd Nk Nl Oa Ok Oy Pj Qa Qg Ql Qt Qu Qv Qw Qz Tz Ur Vt Vv) Jg(Aj Al Co Cx Dd Ez Fa Gl Ic Id It Iv Jh Jt Ju Jy Kg Kn Ks Ld Lu Mt Nf Ni Nj No Ok Or Oz Ph Pi Qb Qh Qt Qu Ra Rg Rj Rm Sr Ss Tz Uc Ud Uf Ug Um Up Ur Us Uv Vp Tj) Ih(Al An Ap Co Db Dc Et Ez Fn Gz Hx It Jh Jr Ki Kk Kp Kr Kx Ky Lz Ma Mf Ml Mr Mt Mz Nd Ne Ng Nh Nl Nm No Ns Oh Ok Ow Pg Ph Pj Qn Tn Tr Tt Tv Uk Ul Uu Uv Vo Vv) Kc(Al Co Db Dc Dg Dl Em Ex Ez Fn Fy Gl Hu Hw Ij Ip Ir Jm Kf Kl Lj Mf Mi Mn Mp Mq Nd Ns Ny Oa Ok Or Oy Pd Pj Qd Qe Qu Qw Rb Sr Ub Uc Ud Ur Ut Uu Vp Vs Vu Vv) Ib(Aw Bg Ch Dg Di Dp Et Gl Jo Jp Kj Kp Ks Kx Lu Mc Mh Mn Mp Mq Mr Mz Nh Oz Pa Pb Pz Qb Qc Qd Qe Qm Qn Qu Qw Rc Ss Tn Tr Tt Tv Uc Uf Ug Uh Ur Us Ut Vs Tj) As(Cp Dp Et Ez Fa Fb Gz Hb Ic Id Ij Io Iq Iu Jt Ju Jv Kd Kg Ki Kl Ko Kq Kr Ks Ky Kz Lv Mb Mg Mt Pb Pj Pk Qh Qm Qt Qv Qx Sr Ss Ub Uc Um Ut Uv Vo Vq Vs) Wm(Al Ap Bo Dc Dg Dp Em Ex Hq Hr Hu Hv Hx Io Iu Jy Kd Ki Kn Kp Kr Ks Kx Ky Lj Lv Me Mf Mh Ml Mr Mz Ne Nf Nj Nl Ny Og Ok Or Pc Ph Pj Pz Qe Uc Ud Uk Un) Tz(Af Bb Co Dr Ez Fb Fn Fy Gn Hw Hx Ic Id Io Ir Iu Ji Jp Jt Jy Ko Kr Kz Ld Ma Mf Ml Mt Mx Nf Nj Nk Nv Oh On Oy Ph Pj Pk Qg Rc Tv Uk Ul Uu Uv) Mv(Aj Ap Cx Dr Fn Fy Gd Gn Gz Hx Ip Jh Jm Jn Ju Jy Kd Kk Ky Ld Lz Mi Ml Mq Mr Ne Nf Nj Nk Oh Ok Or Oy Pa Ph Qg Qt Qv Qw To Tv Um Uo Ur Us Ut) Rb(Af An Aw Bn Ch Cv Cw Db Di Ez Gd Gz Hb Io Ip Jo Jq Ke Kq Ks Ld Lj Lv Mb Mh Mt Mz Nd Nh Ow Pi Qc Ql Qm Qn Qx Rg Rm Tn To Tr Ud Ug Ul Tj) Na(Ar Bn Dl Dr Et Fb Gd Gn Gp Ij Io Ip Iu Jp Ju Kd Ky Ma Mf Mj Ml Mp Mt Pa Pc Pz Qb Qt Qz Rc Rh Rj Rm Sr Ss Ub Uc Uf Uh Uo Us Ut Vo Vp) Mr(Al Ap Ch Co Cq Cx Dg Dk Gl Hu Hx Iv Jh Jp Jy Kk Lz Ma Me Mf Mh Ml Mz Nf Ng Nh Nk No Nv Pg Ph Pj Qb Qu Rh Tn To Tr Tt Un Uu Vs Vv) Og(Al An Ar Bg Co Cx Ez Fy Gl Gp Hv Hw In Io Iu Iv Jm Jo Jp Jy Kd Ma Me Mf Mg Mp Mt Ne Nf Ng Nj Ny Oh Ok Om Or Qc Qd Qw Rh Ud Uk Un) Ex(aC aD aH aP aW aX aY bE bJ bQ bU cD cE cF cJ cU cW cX cZ dC dD dG dH dI dM dN dR eF Ez Fy Kd Kr Nv Oy Ph Pj Pk Qg Tr Ur Vt) Hw(An Fn Gd Gz Hu Ic Io Jh Jj Jp Jr Jv Kd Kf Kg Kl Kp Kr Kz Lj Lu Mj Ml Ne Om Pd Ph Pj Qa Qb Qd Qe Qh Qv Qx Sr Ud Un Uu Vu) Vv(Bb Db Em Fn Gp Hr Hv Hx Io Ip Iv Jm Kd Kk Kq Kr Ky Kz Lj Ml Mx Mz Nd Nh Ni Nm Oa Oh Om Pd Ph Pj Qg Qm Qz Rc To Uo Us Vt) Ji(Ad Ar Bg Co Dd Ez Fa Fb Gl Hq Id Ir Js Jv Ks Ky Mh Mt Nj No Oa Ok Or Qh Qn Qt Ra Rc Rg Rm Sr Ub Uc Up Us Uu Vq Vu Tj) Qg(Aj Bc Dc Dk Dp Em Ez Hr Hu Hv Im Jp Jy Kp Kr Kx Kz Lj Lu Ma Mf Mn Mz Nm No Oa Ow Pd Ph Pj Qn Qu Qw Tr Ub Uk Ul Uo) Qz(Aj Al Cx Dc Dr Ez Fn Gl Hq Hx Jh Jm Jr Jy Ld Lu Me Nd Nf Ni Oa Oh Ok Om Ow Ph Pj Pk Ql Rh Tr Tv Ub Um Ur Uu Vq) Kk(Bg Co Ez Fb Fn Gl Gz Hu Hv Hx Ij Iu Jh Jm Jy Kj Kz Lu Mb Me Mf Mz Nd Nh Ni Nk Oa Oy Pg Ph Pk Qb Qv Tn Ub Vq Vt) Fy(Al Bc Bg Bo Cv Dc Fa Fn Hv Id Ij It Iu Iv Jo Jy Kd Kf Kx Ma Mz Nd Nj Nk Oh Ok Or Oy Oz Pd Pi Qd Ss Un Us Uv) Mm(Aw Cx Dp Ed Gp Hr Iu Jq Jr Jy Ke Kj Kq Ks Lj Me Mi Mn Mz Nd Ne Nj Nk Nm Ow Pk Qv Rm Sr To Uc Ug Uv Vp) Nv(Dc Hr Id It Ju Kn Kp Kz Nf Nj Oa Qa Qc Qn Qu Qw Ra Rc Rg Rj Rm Sr Ss Tr Uk Ul Um Un Up Us Uu Vq Vs Vu) Uu(Ao Bb Cv Dp Dr Em Et Gn Gp Im Jo Kd Ke Ki Kj Kr Lj Ma Ml Ni Oh Pk Qa Ql Qt Qx Rh Uh Uk Ur Vq) aA(aC Ad Aj An Ao Ar Aw Bc Bg bL Bn Bo bR bS cO cP Cq cR CV Cw cX DC Dd dG dH Di Dk Fw Gl) Co(dN Hv Im Kd Kr Lj Lz Ma Md Me Mf Ml Mz Ne Ng Nl Nm Ns Ny Of Oh Om Ow Pc Pg Pj Uk Vo Vt) Oa(Aj Bo Cu Gl Hr Hx Iu Jh Kf Kq Kz Lu Lz Ma Mf Nd Nf Nk Ns Oy Pa Pd Ph Pk Ql Qv To Vo Vs) Vt(Cx Ed Fn Gl Hq Hr Hv Hx Ir Jm Jp Jy Kj Ks Lj Me Nh No Pg Ph Pk Qb Qh Tn To Ug Um Ur) Im(Af Aj Cu Cv Ed Ez Fn Gl Gp Gz Hx Iv Jn Jt Jy Ma Mg Ml Nd Nh Oh Ow Oy Pd Pg Pj Pk) Of(Ar Dr Ed Hb Ir Kd Kl Ko Kq Ks Ky Mi Ow Pk Qa Qd Qu Ra Rc Ss Uf Ul Um Uo Up Ut Tj) Fn(Al Dc Dk Hr Hv Jh Jp Kd Lj Lu Mf Mq Nh Ni Pg Ph Pk Qa Qn Qv Qw Rh Ur Vp) Me(Bg Dc Dp Hu Ic Ki Kj Kr Ks Ky Lu Mj Or Ph Pj Qb Qh Qu Ub Uk Uv Vq Vu) Qt(Bb Ed Et Fb Gp Gz Hq Hx Iv Ky Ld Ma Mx Nd Oh Pa Ph Pk Rc Tn Tr Tt Ul) Lu(Bb Cu Cx Ip Jh Kz Lj Ma Nd Nh No Oh Ok Om Qx Vo) Ub(Dc Ed Ez Hu Jy Mx Nf Oy Ph Qh Tn Tr Ug Ul Vs) Qb(Bb Cu Dr Gd Gn Kq Kz Ma Nd Om Ph Pj Pk Qx Uo) Ql(Al Bc Ed Gl Ip Iq Ir It Jm Mt Mx Ni Ph Uv Vs) Vo(Ap Bg Dg Dl Fb Gl Jm Ok Pz Qa Qh Ss To Uc Vu) Nh(Al Ir Jh Jr Mf Mi Ml Nl No Oh Om Oy Pd Un) Kd(Ch Cq Ez Hx Jm Kp Mn Mz Ny Ok Qa Qh Uc Un) Jp(Cu Gp Hr Ko Kq Ld Nf Pd Ph Pj Pk Qx Uf) Oh(Aj Al Dc Ma Ml Ne Nf Oy Pj Pk Qn Ur Vp) Cp(Af Al cK Cx Dd Gn Pi Tn Ud Ul Un Up) Vp(Gz Ip Jy Ky Kz Ld Mx Ph Pk Tr Tv Ul) Dc(Fw Gd Gz Jr Ni Nm Pd Pj Pk Qn Uk) Ok(Bb Bc Cv Cw Dr Gn Gp Iq Ml Om Pk) Kr(Al Cq Hx Jm Jr Ny Qd Uc Un) Pd(Aj Al Ap Gl Jh Ph Qu Tn Un) Hr(Cv Jh Jy Mj Mp Ni Pj Sr) Ao(Ed Tn Tr Tv Um Us Vs) Fb(Hx Jy Kq Ld Ma Nf Tv) Gl(Gz Jo Ml Nd Ng Ni Om) To(Dp Ki Mj On Qa Qw Ur) Aj(Jj Jo Jr Lj Mi Ng) Gz(Al Hq Qd Qh Ur Vu) Ma(Cq Ij Mj No Qd Qu) Mx(It Rg Sr Ss Un Up) Tn(Cw Et Jo Ou Pj Uv) Ip(Al Cx Hx Nj Oy Pg) Nf(Cv Dp Lj Mj Qw) Jy(Dp Mj Qw Tt Tv) Un(Bc Nm Ph Pj Qx) Gn(Hx Mz Ny Ur) No(Dr Pj Qn Qx) Ni(Hu Nk Oy Qw) Qd(Bb Kq Om Pk) Qu(Ad Et Lj Pj) On(Tt Tv Um Vs) Ou(Dr Fw Ko Tv) Ez(Kg Kz Qw) Mi(In Jm Ur) Mz(Md Pk Ra) Tr(Ko Mt Qa) Lj(Bg Oy Qh) Ph(Mb Mf Pj) aJ(bI cE cO) Al(Fw Om) Cq(Kz Pk) Ng(Bg Vs) Hx(Jh Qw) Jm(Jr Qn) aP(aZ cK) ApOm BbQh FwJo GpgL M

Figure 13 Continued

Ct Cu CV cW Cx cY cZ Dc Dd DE dF dJ dK dR Ef Et Fa Fb GL Hb Hr Ik In Io Ip Iu Iz Jg Jk Jp Jq Js Jy Kc Ke Kf Kl Ko Kx Kz Lu Lz Ma Mb Mc Me Mh Mi Mn Mq Ms Mv Mz Nc Nd Nj Nr Nt Nv Nw Ny Oa oH Oi Ok Om On Pb Pc Pf Ph Pi Pj Qd Qe Qm Qu Ra Ri Rj Tn To Tt Ua Ub Uc Ud Uf Ug Uh Um Up Ur Uu Vo Vs Vu Vv Wm Th) bA(Aa aQ aZ cB cC iA Je Kd Kr Mf Mm My Pd Pf Tr Uk) My(aU aZ bV cC cO dA iJ Ue Uk) aJ(cO dG dH dL Iv Kr Mm Tv Th) Ue(Cp Fn Jd Je Mv Rh) bV(cJ Fn Gz Je Pd Uk) Ba(aQ aZ cB cC cY) aP(bW Et Fb Kr Rh) cT(aU cB Fn Rh Uk) fR(Hc Mv Oe Tv Ua) Aa(aX bZ fP) Em(Fb Hu Lu) Mv(cB cO Pd) Th(Jo nY) Nq(Et Tr) Im(Ko kS) Rh(Fn Uk) GnHu MmdM MuKq HxoH} Mm{fR(aC aD Af Al aM An Ao Ap aR aS AW aY bI bJ bL bO bR bU bZ cF cG cI cM Co Cq Ct CU cW Db Dc dF Dg dH DI Dl dN Hr Hu Hx Ij Ik Il Io Iq Ir Is Jj Jo Jq Jt Kp Ky Kz Lh Lj Lv Lw Lz Mc Md Me Mf Mk Ml Mn Mr Mt Mu Mw My Na Nb Nd Nf Nj Nk Nl No Ns Ny Ok Om Ou Pa Pb Pe Pf Qb Qe Tr Tz Ua Uu Wm) Gn(Aj Bo Dd Hq Hr Im Jf Jn Jo Jr Kj Kl Ks Mg Mq Ms Mz Nb Nf Nh Nj Nr Oi Or Ph Pz Qa Rf Ss Uc Ue Ur Ut Vp Vq Vu) Em(Ad An Bc Cw De Gp Io Jj Ld Lv Mk Oh Or Pj Pz Qc Qu Ut Vp Vq) Dr(As Dc De Dl Fy Je Ke Kf Kl Ms Mt Mx Nh No Oy Qg Qu Uc Un) aP(dG Fn Kd Kr Ky Tn Tr Uk) Ib(cB cS Ir It Iu Jg) Nq(Kr Tv Ue Uk) Ss(Iq Ir It Iv) Sr(Iu Iv Th) bV(cO gW iJ) Is(Ic Id) Uk(Mx Oe) PzoP VqkS} aP{Tr(aD aR bL bQ bR cC cF cW Ex Fa hC Hq Hv Ii iP Jq Kd Ko Ks Mp Nj Ny Of Oh oK Pf Uh Uk) cO(aM aX bG bL bN cS dL Hx Jt Kq Ma Mk Mp Mz Nl Oh Qd Qg Rh Tv Ua Ue) dH(Fb Hb Hx Io Je Jf Jr Kd Kn Kq Kr Ks Ma Mp My Nh Ow Pd Qg Uh Up Vt) Et(aC aN Ao aZ bW Cp dG dL Ed Fb Fn iA Jd Jy Kd Up) Ko(Aa An aZ bA Bo bQ dL Im iP Kx Mf oN pF Uk) bW(aJ aX cZ Fa Kn Kr Ky Mn Pg Qg Tv Ut) dL(aC An bN cJ Fb Kq Pd Ue Uv) iA(Cv Ed Fn Hx Iv Mp Qe Qx) Uk(bM Bo Fn Ky oK oN Qe) dG(An Cp Kd Mf Pd Tv Ue) cJ(aX cS iC Kd Kr Tv) Bo(Jo Kd Kr Ks oN) eM(aJ bC bN bS dD) Kq(An BA Mf) Ky(Fb Kr oK Pd) Dg(An Cp Jg) bQ(aR cT cW) jP(cQ hB iP) Fn(Fb Ma) aC(cW cZ) AnQd CpCw MakS QeQg bNcW} aJ{dG(aC Af bN cO cS Fn Fw Gl Io Is It Iv Kq Kr Mr My Ue) dH(eM Iq Jr Kd Kq Kr Ly Ma Mn My Nh Qe Tr Us) Kq(An aZ cS Hx Iq It Iu Kd kS My Up) cO(aX cW dL Ed Et Fn Iu Mk Mv Tv Uk) eM(aX aY bB bl bO cM cT cV dB dM dR) bM(iP Iu kQ Kr kS oH Tr Ue Uk Up) Ko(aZ BA Cp iP Kx My Uk Up) Ed(Af Bb Cu Et iP Pz Ue Ti) cJ(aX dL fP Iu Tv) Up(dL Et Qa Uk) kS(jP Ky Ma Qe) Th(Dg Jo Ow) Tr(aQ Iu Ny) Tv(dL Gz Ok) aC(aR aY cZ) bN(cW dE) jP(aF hX) Bolv ExOu IsiA IudL KyfP bCbW} Nq{Tr(An Ax bV cB CO cS Cw Ez Fa Fy Gz Hq In Je Jf Js Kj Kl Kn Kq kS Kx Kz Ma Mf Ml Mt My Nr OH Pg Ph Pi Pz Qd Qe Qm Qn Rm Ue Ul Um Up Vo Tj) Kr(Af Bb cJ Dg Et Ex Kq Ky Ma Mg Na Qg Tv Ue Uf) Et(An Fb Jd Je Kl Ko Ks Ky Pi Pj Tn Ue Un) Tv(Ad Bb Dg Fn iA Mg Ok Pd Pz Ue) Fn(Ad Bb Cw Ko Ma Mg Pz Ue) Th(Ad Dg Kg Ks Nm Pd Ue) Ko(Cw Kg Ml Mx My Qg Uk) Ue(Bo Cu iA Kd Pd Uk) Uk(Cu Dg Kq Ok) iA(cH Ma Mf) Ti(Cw Mg) MakS bVcO} Em{Pj(An Cs Ct Cu De Dp Ex Fn Ha Ih Ii Ij Im Ip Ir Jd Je Ki Kj Ks Mf Mj Nc Nd Ng Nh Ny Oh Om Pg Pi Qg Qh Qt Qv Qy Rh Us) Hu(Al Ij Il It Kc Kr Ky Mz Oe Om Ph Uc Ug Vv) Ua(Af As Aw Bo Dg Di Ij Kf Kj Lj Qv) Nm(As Cu Fy Il Im Jk Mu Nt Qy Uu) As(Ct Je Jk Po Rh Ue) Oe(Et Jo Jt Kf Ub Uh) Qy(Cw Et Jt Ky Ue) Fb(Dg Kf Mz Uh) Et(Li Lx Mw) Fr(Ad Jt Kq) Mu(Bb Cw Kf) Po(Ok Vt) Mw(Cw Jt) Ue(Hc Iz) BbMv BoVt CtJo DgEf MgHc JlUh} bV{iA(As Dp Fa Hb Hr Id Ih Il Je Jf Jp Jq Jr Jv Kj Ko Ks Lh Lw Lx Lz Md Mg Mv Na Ne Nm Nr Oh Ow Oz Pa Pb Pf Pg Ph Pi Qe Qg Qw Qz Rg Rj Sr Ss Tz Ua Ud Ue Um Us Uu Vu Vv) cO(Et Fp Hx Im Jl Jr Kd Kr Ma Me Mf Mj Mr Mu Mx Nh Nm Po Tr Tz) Tr(Aa An bB bF Cp dK Hv Il oN Pd Pi) Ex(Et Kf Ni Oe Pj Uf) Fn(cE cJ Ma Pd) Uk(cE cV iJ Qg) Ky(cE iZ nY) cJ(Kr Pd Ue) Mv(cE cG) BbGz MfiJ PdcV} Mv{Pz(Hv Ir Ji Jp Jr Mg Ml Mu Mx Nk Nv Oh Ok Qa Qb) cO(aX cS dA dI dJ dK dM Io Iq Mn Pd) Mg(Io Iu Jj jV kF IL Mn Ng nI Nr) Uk(Af cE cJ dJ Fn iA Iu Ky oH Up) Iu(An cJ Cu Dg iJ jP Ue) Jj(Hq lv Jt Ng Nl Ny Pd) Ma(fR Gz Kd Ng nK pF) jP(Hx iB jH jT jY rX) Ue(cB Cu Mn Ny) nI(Mf Mj Nf Ny) Ng(Is Iv Mn) Jo(Ir Tr) Jt(Nk Nw) AnMn BbGz MzJs KykS OfkO} eM{cN(aG aM aN bH bJ bR bU cG cO cP cQ cW dF dJ} dM(aH aL aY bE cA cM cT cV cX cZ dB) bN(aX bA bE bl bL bS cM cY cZ dN) bC(aH aK aW aZ bP cA cD dl dR) cS(aS bL bS cB dD) cY(aL bE cM cZ) bS(cM dD gC) bE(aC cK) cT(cX gC) aXcB} Uk{Fn(Cp Dp Mf My Nb Og Qg Qy Ue Uh) Cp(cJ cO Dg Ko Ky Mn Pd Ue) cO(BA cN Mu Mx My Tz) Et(Iz Jd My Nn Un) Mx(Af Bo Io Mz Uh) Ko(BA cN Im) Uh(Jd Ji Lh My) iA(Iz Jl Un) Ba(Cu Ma) My(cJ Ue) Up(cT Qw) dM(cJ dH) EzdJ MfoH MnUa MuTv Uelz bAcE} Tr{dM(bU Db dL Hv iO iP Iu Jq Kd Ko Mh Nf Ok Pz Qm) Dp(Ba Dk Ez Iq Ir Is It Iu Iv Mw My Nn) Mx(Fn Io Iq Ir Is It Iu Iv Jo) Jo(dA Ih Ik Jg Jk Jl Li Mw) fR(bO cD Et Ua) Kg(Fn Jd) DkMn TiIb ExdA cBhG} Pz{oP(Ii Im It Jg Ji Jj Jl Jn kF kG kK Lj Lv Lx IY Lz Md Mk mM Mn mS Mw Mx mY nI Nj Nk nL Nt Nv Ny Oe Om On Pa Pf) Ms(kC mM nN qZ) Ue(Cp Iz) NnMu JjJk JpnR OgoQ kFkN} Gn{Pj(Cp Fr Iz Jl Mz Of Ua) Hu(Co It Jo Kg Ky Or) Ua(Ap Jf Kl Pd Uc) Dg(Ef Iz Jl My) Hc(Aj Ke Kj Rh) Fr(Ap Jt Kq) My(Jt Ue Uh) Ib(DI It Jf) Po(Cw Jt) Ue(Ef Mw) Oe(aC Uh) Bblz BoVt WmLu EtLh NvUh} oE{qW(aM aO aU bC bO bP cG cJ cL dF dG dM iH kS) iP(iC jG jM jR IL qT qU) cW(jG qT qU qV qX qY) jG(aS cX hB kQ oK) jP(aE bE bG jM oH) nW(qV rA rB) aZ(iC jM) bMrB bWjM qVoK} Et{fR(aE Ao bJ cJ Cp cR cU dE dH Hf Ik Iu Ji Jy Kz Nh Nx Tz) Fn(Jd My Nn Nw Un) Mx(Cp Ko Tv Ue) Jg(Bb Ex Id Ss) Gz(My Tn Ua) Ue(Cp Jd Un) Cplu DrUa ExHc JdUn JlcO LhcB} Fn{Jo(Ao Iz Jd My Nn Pg Qy Tt) Ue(Cp Je Ky Mf Mx My Tj) My(Ad Dg Ks Mg Uh) Pd(Jd Li Nn Pg Po) dM(Bb cO dG Ma) Jl(cO Dg) CpMg DbKr DpHv HxiP bAcO bNiZ cHiA} Dr{Hu(As Co Ij Ko Mf Ng Or Rv Uf Vv) Bo(Ez Jl Mu Nb Po Ua Vt) Pj(Hx Jp Li Nn On Ua) Hc(Ap Ke Kj Pd Rh) Ue(Ef Fr Qy) ApFr LuKy NgUa IbJf OeUf} Ma{Ba(aC cL Dp fR Hr Il Iu Mr Mu Mx Qd) Ib(cB iA kS oH) bA(bI Cp Mr Mx) fR(bL Oe Uu) kS(Hx Jk Pg) Gz(Bg Hc) cT(Mr Rf) ExUa MfMu NwnR aOoH} Ti{Sr(An Bo Di Hx Mz Ph Ri) Jo(Cp Dc Ii Iz Nn Tz) Hx(An Ib Ky Ny) Na(Ks Ky Tv) Mg(Jv Lh) Ks(Mx Rf) AnLh DiIb MfNw IdKy} jP{kS(bC bJ cI cL hB iC jU IL) cQ(bX dG gL hX iO jT) Fr(Iu Mf Nj Qe) iZ(aF bN) IL(nJ qZ) MsJj aQoF bXiP hXoH} Ue{Cp(Cu Cw Fa Iu Jo Kd Ko Mn Pd Pg Tj) Iz(cO Jo Mn) Ba(Cu Ky) Ko(Mx My) EdiZ UacO JeLd KykS LhUh} qZ{rB(hV HW HX iC jD jE jI jY IO) jG(qU qW qY rC) Hv(Fp Lj) Iu(Io Nf) qW(IL Ms) rCIL} IL{jH(mM mS mY nA nI nK) IK(kF kG nF nI) nB(jT mH qT) mM(jT rX) nJ(hX rC) IuqU nRjT nUmH} Ko{Mx(BA Im Kr Tj) Im(bI dE Jd Qv) iZ(bM bN iA Ju) Aa(bA iO oF) Jo(Cp Iz) MyVq} Iu{Cp(Ad Cw Pd) Mu(cO Kq Qg) iA(Hx Iz Jl) oP(nN Nx Og) Mx(Kr Pj) HxqU JnjG KyiZ OykF} Th{Jo(Is Jd Jl Mx Nn Oe Po Qc Qg) AoKg BaMg MxKs} Gz{Hc(Cw Dg Ke Kg Mg) Bb(Jg Jk Tn) Ua(Bo Kr Uc) QyKr} fR{Jh(Ad Ap Bb Kq) Hc(Ad Bb Pj) Pj(cJ Oe) CwEz} kS{bQ(cN dM iC jL) Ky(Hx Im) iC(cG cL) VqPj aUqW} Ex{Ua(dR Ip Qv) Mu(fP Qv) ImgW JlfP} bN{iC(hX iB jT jY) iZ(bM Tn Tv)} jH{nU(jG jl nC) qU(nB nT) cQiP iOjG} Cp{aD(aC An aZ) CxgC aCcZ aXcO} qW{aF(cO oN) aO(fP hB) oFoK} Nw{PokN NnJt QekF OkkK} dM{cS(cJ cO) MfiA JrdH} iZ{Bolv EdKr bMgW iOjG} Dg{Jg(Bb oH Qg)} Ib{cB(Bb Pj) MuUt} Iz{Jo(To Tv Up)} Nr{PooP JknK} Jj{MnJk MsqT} iO{jG(iJ jT)} NnMxJt MfqUrX MwItmH HxgWiA JiOkoP UpPdbA cIcTgC Unconstrained panels with 2 analytes, where 1.0E-7 >= 'AUC p-value' > 0. Contains 63 panels of 94,547 total panels evaluated. : Gc(aA Ax Cs Ex Hc Ib Ii Il Is Jd Je Jf Jg Ji Jl Lh Li Lx Mu Mw My Na Nb Nn Nt Nu Nv Nw Oc Of Oi On Ou Pf Po Rb Ue) aA(Af bN Fr Ih Il Io Iq Ir It Iu Js Jt Ko Ma Mn Ng Ni Nr Pz) Gd(Hc Hu Ua) TiPk ItmZ cNeM Unconstrained panels with 2 analytes, where 1.0E-6 >= 'AUC p-value' > 1.0E-7. Contains 113 panels of 94,547 total panels evaluated. : aA(Aa eM Et Hq Hr Hw Ii Ij Ik Im In Ip Is Iv Jj Jk Jm Jn Jo Jp Jq Jr Kq Lj Lu Lv Lw Lz Mb Mc Md Mf Mh Mi Mj Mk Mm Mr Mt Mu Mv Mw Mx My Ne Nh Nk Nl Nm Nn No Ns Nu Nx Ny Oe Oh Om Oz Pb Pc Pd Pe Pf Pg Qd Qc) Gc(Cp Em Fr Fw Fy Ha Hf Hw Ih Ik Im Iz Jk Jp Kc Kf Ly Mk Mm Mq Mr Ms Mv Nh Nq Nr Nx Og Pe Qg Qy Rf Ri St Tz Ua Vv Wm) eM(bC dM) GdOe NqTr MmfR IumZ PzoP jGqZ

Figure 13 Continued

Unconstrained panels with 2 analytes, where 1.0E-5 >= 'AUC p-value' > 1.0E-6. Contains 183 panels of 94,547 total panels evaluated. : Gc(aJ Ao Ar Ez Fb Fn Hr Hv Hx Ip Jh Jm Jr Kk Lj Lu Me Mi Mj Ml Mp Nc Nd Ne Nf Ni Nj Nk Nl No Oa Oh Ok Oy Pg Ph Pj Qa Qb Qd Qh Ql Qn Qt Qu Qv Qw Qz Rh Tn To Un Ur Uu Vp Vs Vt Vu Tj) aA(aK aQ Bb bV cJ cO Cx Dg Fn Fp fR gL Hu Hv Hx Jg Jh Ji Jl Kl Kr Ks Ky Lh Li Lx Ly Me Mg Ml Mp Mq Ms Mz Na Nb Nc Nd Nf Nj Nq Nt Nv Nw Of Og Oi Ok On Oy Pa Pk Po Qa Qb Uh Uk) mZ(Iv jH Jk Js Lj IL Ma Mf Mk Nf Nj Ok Qe) aP(bL bO bQ bW cJ cO cW dL Et Tr) Mv(Iu Jj Jo Mg Ng Of Pz) Gd(Mm Pj Po Qw Qy Rh) aJ(aC cJ cO dG eM Kq) jP(cQ kS IL oE) Em(Mm Pj) Ma(Ba Mu) Tr(dM Dp) Jt(Jg Nw) eM(bN dD) oE(jG qW) AdCp FnJo GnMm MuPz IkJj IuJl PkbA cOdM nUjH Unconstrained panels with 2 analytes, where 1.0E-4 >= 'AUC p-value' > 1.0E-5. Contains 431 panels of 94,547 total panels evaluated. : Gc(AP As Ba Bb bX Co Cq cS Ct Dc De Di Dk dN Dp Ed Et Fa Fp Gl Gz Hb Hq Hu Ic Id Ij In Io Iq Ir It Iu Iv Jj Jn Jo Jq Js Jt Ju Jv Jy Kd Ke Kg Ki Kj Kl Kn Ko Kp Kq Kr Ks Kx Ky Kz Ld Lv Lw Lz Ma Mb Mc Md Mf Mg Mh Mn Mt Mz Ng Nm Ns Ny Om Or Ow Oz Pa Pb Pc Pd Pi Pk Pz Qc Qe Qm Qx Ra Rg Rj Rm Sr Ss Tr Tv Ub Uc Ud Ug Uh Uk Ul Um Uo Us Ut Uv Vo Vq) aA(aC Ad aG aH AL AN aO Ap aR AS aU aV Aw aX aY bB bF BG bl bL BO bQ bW bX bZ cB cD cG cK cL cN cQ cR cS CU Cv CW cX cY cZ Dd dE dF dH dl dJ DL dM dR Ed Fa Fb Gd Gn gW Hb jG Kd kN kS Qc Tr Tv Ue Uf Th) aP(aC aE Af aH aM AN aQ aR aW aY bA bB bF bG bM bN Bo bV bZ cl cL cT cX cZ dB dE dF DG dH dM Fb Fn jP Ko Kq Ky Pd Tv Uk) mZ(Et Fr Hx iC Ih In Ir jG Jm Jt Mj Mn Ms Mv Mz Ng Nm Nr Nw Nx Oe Og Om Oy Pa Qd qT qU qW) Mv(cO Gd Hv Hx Ij Il Io Jm jP Js Jt kO Ma Mn Nm Nr Ny Pf Ue) aJ(aM AN aQ aR aY bG bL bM bN Bo bV bW dE dH dL Ko Tv) Gd(Ef Fr Ib Ik Il Iz Je Jf Lu Mu My Qt Tz Uu Vt) Mu(Hv Io Iu Jj Jt Me Nm Nr Of Pf) Ue(Cp Fn Iz Je Mr Mx My Nq Pk Uk) dM(aC bG bL bN cE cJ Et Fn Kq Ma) eM(aS aX bA bE cB cM cS cY cZ gC) IL(iC Iu jG Mf nB nJ nT nU qZ) Jj(Is Iv Jk Nl Nn Nt Nv Nx) Cp(Cw Dd Dg Et Jo Pd Uk) Fn(Dp Kg Ks Ma Pd Uk) Nq(iA Ko Kr Ks Tv Uh) Ti(An Ib Sr Tv) Pz(Fr Jg Nn Nv) bV(cO Pd Pk Tr) iZ(bM bN jP Ko) Mm(Ib Sr Ss) Jt(Fr Nn On) Em(Hu Lu) Et(fR Jd) Nm(Nn Om) Iu(kF qZ) Jo(Is Iz) Ko(Im Mx) rB(aF oE) DrHu FrjP GnLu MabA QgUk JlcO RhPk iCkS jGjH Unconstrained panels with 2 analytes, where 1.0E-3 >= 'AUC p-value' > 1.0E-4. Contains 1,399 panels of 94,547 total panels evaluated. : mZ(aA Fp hA Hq HR Hu Hv Hw hX iB Ii Ij Ik Il Im Io Ip Iq Is jF Jg Jh Jl Jj jK JL Jn Jo JP JQ JR jT jU jY kN Lh Li IK IM IO Lu Lv Lw LX Ly Lz Mb Mc Md Me Mg MH MI MI MM MP Mq Mr Mt Mu MW Mx My Na NB NC ND Ne Nh Ni NK Nl NN No Nq nR Ns NT Nu Nv Ny Of Oh Oi On oP oQ Oz Pb Pc Pd Pe Pf Pg Po Pz Qa Qb Qc qX qY rX rY rZ) aP(aA AD aF aG al Aj aK AL aO Ap AS aU aV Aw aX aZ Ba Bb bC bE Bg bH bI bJ Bn bP bR bS bU bX cA cB cC cD cE cF cG CH cK cM cN Co CP CQ cR cS Ct CU CV Cw Cx cY dA Db dC DD dl dJ DK Dl dN dR eF eM Fa fP Fw GL gP iA iP Iu Jo Jt Kd Kg Kl Kn Kr Ks Ma Mf Mm Mp Mt Nd nW Oh OK ON Pf Pg Pk Qd Qe Rh Tn Ue Uf Uh Ut Uv Tj) aA(aD aE aF al AJ aM Ao Ar aW Ax aZ BA bC bE bH bJ bM Bn bP bR bS bU cA cC cE cF CH cl cM Co CP Cq Cs CT cV dA DB DC dD De dG Di DK dN Dr eF Em Ex fP Fw Fy gC Gl GP iP Je Jf Kc Ke Kf Kg Kn Kx Kz Ld IL ml nC nN Oa oH oN oP Ow Pi Pj Qh Ql Qm qW rB Rc Rh Rm St Uc Uo Uv Vo Vt Vv Wm Tj Ti) aJ(aD aE aF aG aH aK AL aO aS aU aV aW aX aZ bA Bb bC bE bH bI bJ bO bP bQ bR bS bU bX bZ cA cB cC cD cE cF cG cH cl cK cL cM cN Cp cQ cR cS cT CU Cv CW cX cY cZ dA dB dC dD dF Dg dl dJ dK Dl dM dN Ed eF Et Fb Fn fP fR gL gP iP lu jP kQ Kr kS Ma Mn Pk Pz Qd Tr Uc Uk Up Th) dM(aD aE aF aG aH al aK aL aM AN aO aQ aR aS aU aV aW aX aY bA bC bF bH bI bJ bM bO bQ bR bS bU bV bW bX bZ cA cC cD cG cH cl cK cL cM Cp cQ cS cT cU cV cW cX cY cZ dB dC dD dE dF dH dK dL dN dR eF fP Gc gL gP iA iP Jo Ko kQ Kr kS Mm nW oE oK oN Pk Ue Uf Uh Uk) Uk(Af An Ba Bg bM Bo bU bV cJ cN cO dA dJ Dk Dp Ef Et Gd gW Hc Hu Hv Hx iA Ik iP Iz Jd Je Jk Jl Jo Ko Kr kS Ky Mm Mu Mv Mw Mx My Nb Nq Oe Og oH Oi Qh Qw Qy Rh Ua Uh Up Vt Ti) Uc(An Ao As aZ Ba bV cJ cO dE Dp Ef Et Ez Fr Gd Gl Ik Iu Jd Jg Jl Jo Kd Kg Ko Kr kS Ky Ld Mf Mm Mu Na Ne Nk Nl Oe Oi Pd Po Qg Qt Qy Rf Rh Tz Ua Un Up Us Uu Uv Vt Tj Ti) Cp(aC aE Af AI AN Ap aQ As aU aZ bA bF bI bM bN bU bV bW bZ cA cC cD cE cF cJ cL cM cO cU Cv CX cY cZ dC dF dH DK Dl Fn gC Gd Iu Ko Kr Ma Mg Mm Mn Nm Om Tr) Gc(Ad aE Af Aj Al aM An Aw aX aZ bA BC Bg bI Bn Bo bP bR bV bZ cB cF cG Ch cK cN cP cT Cu Cv Cw Cx Db Dd Dg Dl DF fR Gd gL Gn GP Rc Tt Uf Up) Mv(Ad Af An cC cE cG cJ Co Cu Cw Dg Et Fn Hu Ii Ip Iq It Jh Jk Jr Kg Ko kS Me Mf Ml Mm Mr Mu Mx Mz Na nl Nl Nq Oe Oy Pc Pd Pg Pi Pk Qb Uc Uh Vo) Fn(An Bb bV cJ cO Cv dA Dg Et Gd Hb Hc Hu Hv Hx Il Jd Je Jl Jq Ko Kr Mf Mg Ml Mm Mn Mu Mx My Nb Nd Nm Nq Pj Pk Qg Qv Qy Rh Tr Tv Ug Uh Vt) Jo(Al An Ao Aw bV Dc Dk Fr Ha Ib Ip Ir Jd Jg Ji Jy Kd Kn Ko Kr Ky Mu Nn Nt Nw Ok Om On Pk Qb Qg Qh Qy Tn To Tr Tt Tv Tz Un Up Us Uv Ti Th) Jj(Fr Hu Hv Hx Ip Ir JG Ji Jm Jp Jr Lh Li IL Lu Me Mf Ml Mn Ms Mt Mw Mx My Na Nc Ne Nh Nk Nq Nu Og Oh Oi Ok Qa Qb Qc Qd Qe) Gd(Ao Ba Cq Ct Dc De Dk Fb Fw Gl Ha Hx Jg Jl Jy Kd Ke Kr Li Mf Mk Mw Nn Nv Oa Or Ou Pi Qg Ql Qz Rb Ri Ss Ug Ul Ur Uv Vp Vu) Mu(cO Cw Et Hx Ip Is It jP Js Ko Kq Lj Mf Mg Ml Mm Mn Mr Nd Ng Nl Nq Nx Ny Oe Pb Pc Pd Qb Qe Tn Tv) eM(aE aL aQ aR aU aW bG bI bL bO bP bS bV bX cA cK cL cP cQ cT cV cX dB dE dF dG dN dR eF gL gP) IL(eD hA hR hX iB jH jM jT jU kG IK Lv mH Ml mM mS nA nl nK NL qU) bA(bN bQ bR bU bX bZ cE cG cJ cL cO dE DR Gn Ko oH Om Pi Tr) Mx(Bb cO Dg Dl Hb It Iu Jt Kq Kr Ks Nr Pj Pz Rm Tr Tv Uh Ti) Kr(Dp Hu Hx Jd Je Lx Mm My Nb Nn Nu Oi Pf Pg Po Qv Qy) jG(eD hA Hx iC iO Iu Jn jP jT jU jY kS Lv Mf qT qU rB) jH(cJ iP Iu jP kN mE MM mS nA nB nR nT oP) fR(aC aH cE cl cJ cK cO cP cV dR Ma Pk Tr) Ti(Bo Cw Dp Hx Ic Id Ks Ky Mg Na Ny Ss) bV(An bG bN Et Ex Hb iA Ky Ma Mm Ng Qg) Fr(Dg Io Jm Js Ma Me Ng Nm Nr Pd) Nq(cO Dg Hb Ke Kg Kl Kq Tt Uc Uf) Jd(Bb Hb Kg Ko Ks Ma Mg Nm Pd Tr) Jt(Is Ji Jp Nt Nu Nv Ok Om Qa Qb) kS(bQ hA iZ jE Ky IM Ma Mf Pk rB) Hx(iA iJ iP Jl jP Ks Lv Me oH) Pz(Is Ji Jl Jp kF Lh Nw Qa Qb) Mm(Ba Dr Ic Id Jl jY Nn Om) Pk(aU bU cB cT dA dJ gP My) jP(aF aZ iO iP Mp Ms Nj oH) Et(An Aw Ba Is Iz Ji Un) Nm(An Em Is Ji Jl Mz On) Ma(cT Ib Is Jl Mz Nn Om) Iu(Mi Om On oP Qg qU Wm) cO(Aw Ba dG Iz My Po Ua) Gn(cN Hc Hu Ib Pj Rh) Mf(Hv Is Me Nn oH Qb) bN(Aw cl dA fP gL iC) qZ(Hv iC Lj Ms Qe rB) My(Ad Dg Ko Ks Uh) It(kF kK kN mS oP) iZ(aD bH cH cJ Ed) An(aX cS cZ Dd) Dr(Hc Jf Lu Pj) Nn(Ks Mn Ng Ny) cN(bG cl cS Ko) Dg(Iz Jg Lh) Mn(Ba Om Qg) Ua(Cu Em Gz) Tr(dA oH Rf) Io(Jl Mz Om) Pd(Ha Iz Nw) oE(iC jM jQ) Dp(Ko Th) Nk(Nl Qb) Is(Jm Ng) Jl(iA Na) Pj(Ib Ic) qW(aO oF) kF(Ir Nf) AsEm AwaZ BaKo Culz ThKs ExJe LuNw MiHv MzJs NjjY IvoP QbJm QyUt JknI LhUh UniA cBrB gCgL nUqU Unconstrained panels with 2 analytes, where 1.0E-2 >= 'AUC p-value' > 1.0E-3. Contains 5,597 panels of 94,547 total panels evaluated. : Ue(Aa AD aE Af Aj aK Al aM Ap aQ AR aU AW AX bA Bb Bc BG bL bM BN BO bR bU cB cC cE cF Ch cN Co Cq Cs CT Cu Cv Cw CX cZ dA Db Dc Dd De Dg dH Dl dJ DK DL Dr Ed Em Fa Fb Fp fR Fw Fy Gn Gp gW Ha Hb Hc Hf Hq Hr Hu Hv Hw Hx iA Ib Ic Id Ih Ii Ij Il Im In IO IP Iq Ir Is It Iv iZ Jf Jh Ji Jj Jk Jm Jn Jp Jq Jr Js Jt Ju Jv Jy Kc Ke Kf Ki Kj Kk Kl Kn Kp Kq Ks Kx Kz Lh Li Lj Lu Lv Lw Lx Ly Lz Ma Mb Mc Md Me Mg Mh Mi Mj Mk Ml Mn Mp Mq Ms Mt Mw Mz Nb Nc Nd Nf Ng Nh Ni Nm Nn No Nr Ns Nt Nu Nv Nw Nx Ny Oa OH Og OH Ok Om On Or Ou Ow Oy Oz Pa Pb Pc Pe Pf Pg Ph Pi Pj Pz Qa Qb Qc Qd Qe Qh Ql Qm Qn Qu Qv Qw Qx Qz Ra Rb Rc Rg Rj Rj Rm Sr Ss St Tn To Tr Tv Ub Uc Ud Uf Ug Uh Ul Um Uo Ur Ut Vo Vp Vs Vu Vv Wm Th) aP(Aa aJ Ao Ar Ax Bc Cs Dc De Di Dp eC Ed Ef Ex Ez Fp FR Fy gC Gp gW Gz Ha Hb HC HF Hq Hr Hu Hv Hw Hx IH Ii IJ Ik Il In IO Ip Iq Ir Is It Iv IZ Jd Je Jf JG Jh Ji Jj Jk Jl Jm Jn Jp Jq Jr Js Ju Jv Jy Kc Ke Kf Ki Kj Kk Kp kQ kS Kx Kz Lh Li Lj Lu Lv Lw Lx Ly Lz Mb Mc Md Me Mg Mh Mi Mj Mk Ml Mn Mq Mr Ms Mu Mv Mw Mx My Mz Na Nb Nc Ne Nf Ng Nh Ni Nj Nk Nl Nm Nn No Nq Nr Ns Nt Nv Nw Nx Ny Oa OE Of Og oH Oi Om Or Ow Oy Oz Pa Pb Pc Pe pF Ph Pi Pj Po

Figure 13 Continued kK kN Ky Lh Lw Lx Me mH Mk mM mS mU mW mY Mz NB nl NN No nR nY oE oH oQ Ou Pb Pe Qh Ql QT qW qX Qy rA Rf Tr Tz Ua Vt)
kS(aC aD aE aI aK aM An AS aW aZ Ba bE bF bG bO bW cE cG cH cI cJ cM cN cO cU cZ dA dE dG dR eD gP gW Hb Hc hG hR hW hX iJ
jD jF jH jK jM jO jQ jT jU jY Kd kR Kx lO oE oH oK oN Pd pF Qg qU qW Qz Tr Tz Ua Us Vq Wm) jH(aZ bM cQ Et fP iA iC In iO Ir Iv jl
kC kE kF kI kK kO kP Lj Lv lW lX lY MF mH mI mP Ms MT mU MW mY nC nD nF nH nI NJ nK NL NM nN nO Nr Nt Nu nW oE Og oH
Ok oO oQ Oy Pa Pz Qd Qe qU qW qZ rB) An(Aa aC Ad Al aM AO aQ As Aw aZ Ba bC bE bG bN bU bX bZ cA cE cI cJ cN cO CT cU Cv Cx
dA dG DI dJ Dl eF fP Fr GL gW Hb hG iJ Ik Il Jq Js Jt Kd Kg Lu Mf Mg Mn Nh Nk Nq oH Pd Pj Pz Qg Rh Tr Tv Uh) Aw(aC Ad Af aG aH aK
Al aM aN aO aQ aR As aW aY bB bC bF bG bI bJ BO bQ bS bU bW bX bZ cC cE cF cG cH cI cL cM cN cP cS cT CV Cw cX cZ dC Dd dE
dF Dg dH dI dJ dK dL dN iJ Jq Kg Ma Mg Mm Mn Nm Pd Tr) Dp(Ad Af Ax Ba Bb Bo Ch Cs CT Cv Cx Dg Et Ii In Io Iq Ir It Iv Jd Je Jq Js Jt
Jy Kd Kg Ky Lj Ma Md Mf Mg Mk MI Mm Mn Mp Mq Mz Nk NI Nm Nq Nr Ok Om Ou Pa Pd Pz Qg Qn Qv Rm Tn To Tt Uh Ul Um Vv Tj)
jG(aZ cQ Et Fr hR hV hW hX iB Il Io iP Ir Iv jD jE jF Jh jl jK JL jM jO jQ jR jV kG IK IM IN IO Ly Lz Ma Mg MI Mn Mp nB Nc Nj Nk NI Nn
No Nr nU Oh Oy Pd Pg Po Pz Qc qV qW qX qY rA rC rX rY rZ) Gc(aC aD aF aG aH al aK aL aN aO aQ aR aS aU aV aW aY bB bE bF bG bH
bJ bL bM bN bO bQ bS bU bW cA cC cD cE cH cI cJ cL cM cO cQ cR cU cV cW cX cY cZ dA dB dC dD dE dF dG dH dI dJ dK dL DR)
cJ(aX bC bX cI cN cS cT dG dI dN eD EF eM Ez FP Fr gL Ha hG hR Hv hW hX IB iC Ik Im Is Iz JD JE jF Jg Jl Jr jT jY Kd Kg Lh Lu Lx Mn
Mr Nb Nh Ni Nq Nt Nu oH Ou Po Qg Tv Ua Un) Hv(bU cF cZ dA dI Fr Hq Il In Io Iq Is Iv Ji Jk Jl Jm Jp Jr Js Lv Lw Lx Lz Mc Md Me MI Mm
Mq Mt Mw Mz Na Nb Ng Ni Nm Nn No Ns Nv Nw Ny Oe Of Oh Om On Pb Pd Pf Pg Qa Qb Tr) Et(Ao Ap cN cT dA Dc DK Ef Ez Fr Fw Gl
Gn Ha hG Ib Ic Id Je Jg Jp kF kK Kn Mz Nn Nw Om On oP Ou Qb Qg Qh Ql Qn Qt Qu Qv Qy qZ Rf Rh Sr Ss St To Tz Ua Uo Us Uu Vq)
Me(Aa cO Hq Hw Ih Il In Io Is Iv Ji Jk Jl Jm Jn Jp Jq Jr Js Lv Lw Lx Ma Mc Mg Mi Mk MI Mn Mp Mq Mz Na Nb Ng Nk Nm Nn No Nw Nx
Ny Of Oh Om On Pb Pc Pd Pf Pg Pz Qb) Kg(AO As Ba Bo bU cB cC Ct Cx dA Dk Ez fP Fr Ha Hc Ib Ih Ik Is Iv Iz Je Jm Jr Kd Kn Ky Ld Ml
Mn Na Nb Nh Nm Nn Oc Oi Pg Po Qg Qh Qy Rf To Tr Tz Up Us Uv Th) Nn(Cw Dg Hb Hq Ih Ii Ik Il In Io Ip Iq Is It Iv Jm Jp Jr Js Ky Lj Lu
Lv Ly Mb Mg Mh MI Mz Na Nc Ne Nh Ni Nk NI Nr Nt Nu Nw Nx Of Oh Pd Pj Qb Tr Uh) Qg(aK Al aW aZ bN bR bU cC cO cR cS cT Cv dA
Dg dI dJ gW hG In Io Iq It Iv Jd Je Jq Kd Kx Ma Mf Mg MI Nm Nq Oi Pd Pz Qv Tr Tv Ug Um Uo Uv Vt) Mf(cN cO Ez Fr Ha hG iA iJ Ik iO
iP Iz Jd Je Ji Jl Jp Jr jV jY kF Li Lx Mt mU Mw Mz Nv Nw Nx oE Oh Om Po Qa Qh Qy qZ Rf Rh To Ua Wm) Nm(Ba Ez Ha Hc Ih Ic Ir Iz Je
Jf Jg Jh Jp Jr jY Kd Ke kF kK Ld Lx Mi Mp Mt Mw No Nv Nw Oh Ok oP Ph Po Qa Qb Qy Rf To Tv Tz Un Us) Jl(cE Co Cu Dg Fy Hr Il In It
Iv Jt Kd Kl Kq Ky Lj Lz Mc Mh Mj Ml Mn Mr Ms Mz Nd Ng Nr Nx Ny Of Og Pa Pc Pe Pf Pg Qb Tv Uc Uh Vv) eM(aC aD aF aG aH al aK
aM aN aO aV aY aZ bB bF bH bJ bM bQ bR bU bW bZ cC cD cE cF cG cH cl cI cO cR cU cW dA dC dH dl dJ dK dL) qZ(Fp hA Hr hW hX iB
Io Ip Ir Iv jD jE Jg jl jK jL jO jR JT IK IN IO Lv Lx Ma MI Mm Mt No Nr Nu Of Pc Pd Pe Pf Qd qU qW rX) mZ(eD hV hW jD jE jM jO jV kC
kE kF kG kI kK kO kP IN IW IY mE mF mS mT mU mY nA nF nH nI nJ nL nM nO nU oO qV rA rB rC) Nq(Ad Af Ap Bb Co Cu Cw Dl Em
Fa Fb Fy iJ Je Kd Kf Kj Kn Ky Nh nl oH Pi Pj Pz Qm Qv Rh Rm Tn Ug Ut Uv Vo Vt Vv Wm Th) Fr(aC Af bN cO Cv dJ Dr Em Gn Hq iA Il In
Ip Iq Is Iv Jr Ky Lu Lv Mb Mg Mm Mn Na Nc Ne Nh Ni NI Ny Of Qb Tr Tv Uc) Mm(aO bZ cS Cv Ex Ez Hc hG Is Jd Je jF Jh Ji Jp Kd Kl Lx
Mi Mt Mw No Nv Nw Nx Oa On Pi Qb Qv Qy To Tv Ub Un Vq) Pz(Ba cT iB Ik Ir Iz Jd Jh jY kK kN Li Lu Lv Lw Lx Mi Mp Mt nB No nR Nt
Nu Oh Ok Om On oO oQ Pc Po Qc Qd Ss Ua) oH(aF aM aO aV aW aZ Ba bG bM bW cH cO cT dD GL hG hX iA iJ Iz jT Kd kR Ma Mp Ne
NI oE oK Ow pF Po To Tv Us) Is(cO Dg Hq Ih Ii Il Io Ip Iq Ir It Iv Jg Jk Jn Js Lj Lu Mg Ml Mn Na Nb Nc Ne Nh Nk NI Nr Nt Nu Ny Of Pd
Qc) cN(aC aF aM aO aQ aU aV aX bC bN bX cD cE cF cK cM cO cR cT cU cZ dA dD dG dI dK dN DR eF fP gL Gz Tv) Ma(aO bC bZ cS Ez
Hc hG Ic Je Ji Jp jY Kd kF Lx Mi Mt Mw nR Nv oE Oh On oP Ou Qa Qb Qw Qy Rf Ss To Uo) Pd(Ba dA dJ Dk Ez Gl Hc Ib Je Jg Ji jY Ld No
Nv Ok Om On oP Pj Po Qh Qh Qu Qy Rf Rh Ss Ua Un Us) cO(aX cS cT dF Di Ef Fp Gl Ha Ih Ik Im Jg Jk Jr Lh Lu Lx Mj Mr Nb Nh Nu Nv Oi
Pe Pg Qh To Tz) Mn(Bg cT DK Ef Ez GI Hc Iz Jd Jp Mz Nv On oP Pj Po Qa Qb Qt Qv Qw Qy Tr Tz Ua Uh Vt) Jt(Em Gn Ib Ik Im Ip Ir Jd Je
kF Lh Li Lv Lw Lx Mi Mt Mz nB No Oh oP Po Qc Qd Ss Un) It(kC kO IY mE mF mH mM mT mU mW mY NA nB nl nJ nK nN nR nT nU
Nv oO oQ) dG(aC aF aM aN aO aR aY bC bF bG bN bW bX cE cI cK cS cT cZ dH dL dR gL iA) oP(In Ir Js mH ml Mj Mk mM mP mW nB
nD Nf NJ nN Nr nT Nw Nx Og Pf Qe) Ba(aC aZ bF bN cE Dg Em Hb iA iJ Kl Ky Mg Om On Pi Tr Uc Uh Up Vo Tj) Jd(Ad Af Cv Cw Dg Dl
Ic li Jq Kd Ld Md Ml Ny Ok Ow Pj Qm Rh Uh Vo Vt) iP(eD hW hX iB jD jE jF jl jM jQ jR jT jV jY IN qT qU qW qX qY rA rB) Lv(hA hR
hV iB iC jF jK Jp jT jV jY Mg Mz Nv Nw Om Qb qU rA rB rC) Tr(bU cB dK Ez II Iz Je Jg Kn Ld Li Lx MI Mt Mw Nb Nu Oi Po Qy Ss)
Nw(Aa Ik Io Iv Jk Jr Js kN Lj Mb Mg MI Na Ne Nh NI Nr Qb Qc Uh) cT(aM aN bB bG bN bX cE cI cU cZ dI gC Jq Kq Mr Ny Pi Uh Vo)
Qb(Ih Ii Ik Il In Io Ji Jk Js Mg Mi Ml Mz Na Nc Ne Ng Om) kF(iC Ih In Iv Jk Lj Mj Mr Ms Mw Nd Nj Nr Nu Og Pf Qd Qe) oE(eD hA hV hX
Io Iv jl jK jO jR jV IN qT qV qX qY rA Th) Je(Ad As Bb bR bU cC cF Dg dJ dK Em Ic Kd Ld Mg Pj Uh) Jp(iA Ik Io Iv Jk Js Mb Mg Ml Na Ne
Ng Nh Nk Nl Nt) Ji(Aa Hb Ik Io Iv Jk Jq Js Lu Mb Mg Na Nb Nh Nl) dA(aV bG bL bX dE Jr Jy Kd Kq Ky Nh Ow Tt Tv Up) Ng(Hu Ik Jh Jk Li
Lu Mw nl Nl Nt Nv Qa Qc Qd) aZ(cl Fw hG hX iB iC jE jM jV Ni pF qU qW) nB(iC lh Ir Iv jL kN Lj mP nD Nj nN Pf Qe qU) Dg(Ez Gl Ik
Im Li Lx Nh Nu Oi Po Qy Rf Ua) Il(Ct dK Hu Ik Iv Jh Jk jY Kd Mw Nv Nx Om) Iz(Ad Af Aj bU cE Co Cw iA iJ Kl Ky Mg Vo) bN(Al aN aO
bX cZ Dd dN EF Fw hG Jg Nt) Ms(jV jY IW mM mT mW nJ nK nN qU qW rB) Om(li Ik Iv Jq Js Mb Mg Na Ne Nh Of Qa) Em(Bg Fb Hc Jk
Oe Po Rh Ri Ub Vt Tj) Ky(Cv fP gL hB hG Nb nW Qy Rh Ua Vt) Tv(bU cB dK lm Jq Mj Nb Pj Qt Rh) On(li Ik Jq Js Lj Lu Mb Na Ne Nh)
bX(aC aN aX cB cl cS cZ dI gL Gn) iC(bC cL cQ hC iB iO kK Mp mY Nj) qW(aD aE aF aM bH bM bW dE dI oK) Iv(Jh jY kN mU mW Mz
Nv oO oQ) Pj(Ex Ez Gz Id Jg Kd Sr Ss Vq) cI(aC aN aO aR bL cS dE dI eF) Ir(kK mM mS mU mW mY oO oQ) Jk(Jm kO Mz Na Nh nK Of
Po) Rh(Bb Dr hG Ic Kd Oe Oi Ss) Mg(Ez Jg jY Nv Po Qh Rf) Nj(hX iB jK jT jY kN mM) Ua(cE Co Cw Ex Gn Kl Ny) Qa(In Jm Js Ml Ne Nk
Nr) Uh(Jg Li Lx Po Rf Un Uo) Mw(mT Na nl Ny Of Tj) Mz(Ik Jh Mb Nh Oi Pc) jY(cE cQ NI Nr Ok Pf) Ez(bU cC dJ gW Hb) Gn(cS Ct dB eF
Vt) Nk(Nc Ne Nh Nv Po) Ib(bU cB gW Hb iA) Jg(Ad Cw Dl Nr Uc) Js(kK No Nv Oh Po) bM(nY qT qX rA rB) iJ(cH Gl iO Jv Us) Aa(bC Ik
Nt To) Lx(Lz Nd Oy Pb) Hc(Co Ex Gz Ld) Pi(Hu Im Qv Qy) aC(aX bE cZ Ef) bG(bZ dF eF gL) cQ(eD hX jT jV) nU(iB jL lK qT) mW(kN Mj
Nf nR) nl(Lj Mk Ok Oy) iA(Lh Oi Ss Us) hG(aQ cB iO Ow) Dr(Oe Or Vt) Nb(Bo Kd Tj) Ik(Ad Af Cv) Hb(Lh Ou Un) Jq(Rf To Tz) Nv(li In
Nc) aN(bE cZ gL) bU(Fw Gl Qy) cC(Ef Rf Sr) cE(dF eF Gl) nT(jR kN qU) rB(aD aE Mp) oQ(Mj Og Qe) Po(Jm Ml) Nu(Bb Nr) Hu(Kd Mi)
Ic(gW Qy) Jr(dJ Jm) Ok(kK Un) cS(aW cK) eF(dR gL) nR(jT lK) hX(bC hB) iO(bW jM) kN(lK mM) AfTo DcDd MjmU MphA MtPb NaJh
NcNl NeNh QwUp OgoO Owdl OudJ a

Figure 13 Continued

Qg Uk) KgiA} Pz{oP(Ir Nf) NwnR} lL{lK(mM nU) qZqU} Et{NtfR MxUk} Ma{MvkF RfbA} DgDrHc FnPkbA NrMvnK UaKqfR QbQeqZ JkNynI NwOknR aFcEqW

Constrained panels with 3 analytes, where 1.0E-8 >= 'AUC p-value' > 1.0E-9. Contains 934 panels of 10,943,034 total panels evaluated. : Gc{Vt(Dc Ef Hw Ih Je Jg Kf Lx Oa Ok Ql St) Rh(Ax Dc Em Fr Iz Jg Lh Li Lx Pf Qg) Qv(Ct Dk Gl Im Mq Nw Po Qg Ur Vp) Hr(Dk Dp Fb Im Mv Qt Qw Ub Vp) Ow(Ct Dc Jk Mk Mv Mw Qy Rf Tr) Em(Mq Mv Oa Pf Qw Ri Ub Vp) Ma(Ii Iz Ms Mw Pe St Vv) Tz(As Cu Kd Ke Nb Of Og) Ue(Bg Dc Kf Mi Nx Oi Uv) Vp(As Hw Jd Me Nv Og Oi) Ip(Dc Gl Jh Og Qt Ur) Bo(Li Lu Nt Rf Ub) Wm(As Ez Hw Mi Oy) Mk(Ba Ly Mi Nv Ur) Nb(Iv Kd Kr Pd Ua) Tr(Je Jg Li Mj Po) Ri(Cs Kk Lu Ur Vv) Uv(Ba Ii Nt Of St) Fr(cE Ed Mt Pk) Ua(Ba Lx Of Uk) Ub(Aj De Ik Jk) Jg(Ad Ke Nm Rc) Qt(Hv Jy Of Og) Oi(Jy Or Uk Ur) Pj(Ef Ha Kf St) aA(bI cB cE Co) Bb(Ik Is Iz) Ez(Ly Me Ur) Mi(Ct De Hw) Nf(Hf Im Je) Kq(Ba Iz Lh) Uu(Cw Om Pd) Pk(Kf Mv Nr) As(Jk Ur) Cp(Ad Ko) Fy(Il Rb) Me(Mq Qg) Ml(Nt Nu) Mm(Kl Ut) Na(Kr Lz) Nc(Is Ms) Hw(Hv Or) Ii(Kg Pg) Ql(Md Og) Nv(Iu Ns) Nw(De Oy) Pd(Ha Pe) gL(bN bR) ApIz ArOu BcSt CsOg DccI EdRf ExbX FnHx NmOk MrNi HuQx HbJe IsJt JrKd aJaZ cKdN} aA{Up(As Ji Ke Kq No Nr Nt Oh Om Pf Qa Ue) Pk(aU cC cJ cO cS DG dH dJ Fb Fn kS) Tr(Af aQ bU cF cS Fn gL Jq Ky Mn) Js(Fr Jg Jk Lw Mi Mu Nw On Qb) Fn(Bo Cu Cw Kl Kq Mn Tv Uk) bN(AL bG bQ cW dG dH Ti) Mn(Bo cO dH In Md Ok On) Ky(aU aX cC Fb Qe Tv Vo) Iu(Fb Fr Nw Ok On Qg) Qd(aK aN aQ aU cO kN) Uk(cJ Et Fa gL Mm oN) Jt(Ji Jk Lw Mv Qc) Kq(aN gL Kd Nn Oy) Bo(Iq Is It Ti) Lv(In Ir Md Pd) Ma(cO Jg On oP) cS(bQ Dg Ks Uh) Ed(Cx gL Kl) Nr(Jg Mu On) Il(Jk Mv Pd) Ir(Fb Pd Uh) bV(Ks Ok Uh) Af(Fa Fb) Bb(Kd Mp) Et(cO Nn) Nu(rB rZ) Ng(Jg Mu) Ih(Jk Ok) In(Ik Pz) Io(bI cG) Iz(Dg On) Qe(kN qU) ApIv ExTv MdPz MfgL NkNl JdOn JkmZ KrcO dHeM} Gd{Uu(Ap As Bc Jf Ke Kg Lu Mg Qv Rh Ub Uh) Ua(Bo Em Jl Jy Kj Ko Ma Mx Of Qg) Vt(Ao Hw Ii Lh Mu Nn Nv Oa Qg Uv) Mv(Et Kc Ky Mf Or Qv Ri Uf) Mu(Bo Kr Ma Mf Uk Uo Wm) Qw(Ef Hw Hx Lu Pj Qy Ue) Iz(Cv Hb Jo Kd Mf Na) Rh(Bo Dc Mf Oi Pi Ug) Ef(Cw Il Ke Pd Uh) Po(Cw Kr Mt Ue Uh) Et(Ba Lh Nn Ql St) Mm(Kj Kk Ri Ur) Ib(Je Jf Kc Ke) Nv(Fa Kf Kr Ri) Fr(Ap Cw Kx) Tz(Ct Hb Nm) Il(Ba Ez Ik) Qy(Iu Ma Of) Oe(Em Me Nf) Lu(Of Ug) Hb(Jl Li) Pj(Ks Uv) AoKg BaUf CtJf CwJg FwKr MfIk MyRc UeQt JeKd JkKc JlKy} aP{Tr(bF cJ dG dN Dp Et Fn Ok Tj) cO(cW Fn Kd Kr Ky Mf Mv Pd Pk) Ko(Ba cJ dH Ky Mm oK Pd Pk) Et(bJ Bo dE dH Uk) iA(Ma Mf Tv Uk Ut) dH(Fn Mf Pk Ue) dG(Ky Pk Uk) Fn(bW Pd) dL(dE Ky) BoPd JyoN KdbW KqoK UkcJ aMbQ bLeM} mZ{Mk(Iv Ma mE Mf Mj Nd Nf Qe) Mv(Iu Jo Mj Ng Nj Nq Pg Pz) Qe(Hx Lx nK Nx Pa Po) Ma(Jp Lj Mu Nv Om) Iu(Hu Ms Ng nK) Mj(Jk nJ Og) Js(Hx Nv Pa) Mf(Jk Nf) Iv(Nx Og) Pz(Ng oP) Ok(Jp Om) lL(jT nU) MzOm NjoP QdNv JkPg JtNw iCjY jGjH} Em{Pj(Ap Dk Ef Gl Ib Ik Is Jk Ke Lj Oa Pe Pf Qw Uv Tj) Mm(Ex Fy Ib Jf Ko Mp Na Oa Qg Qw Qz Ri Sr Ub) Nm(Ct Lx Mw Qw) Ua(Il Jo Ub) Po(Et Uh) Fr(Kf Ok) Hc(Dg Kg) Jl(Jt Kf) Oe(Bb Kg) EtFb MgIz HuIi} aJ{dH(Fn Mr Tv Ue Uk Th) Ko(Aa An bM bW cJ) Tv(cB dG Mm Up) eM(bG cK cR cY) dG(An Aw Cp) kS(bQ kQ Tr) aC(bM dL) bN(dL iC) cO(cS Kr) iA(Iu Iv) BoMn DlEd TrcB QeUp KqbM} Nq{Tr(Ad Af Bb Cu Dg iA Ii Il Ko Ky Mm Nk Nm Ok Pf Tv Uk) Kr(Bo Cu Cw Ko Pd Tn) Fn(Dg Jo Uh) Uk(cO Et Uh) Kd(Dg Et) NmK UecO TvUh IuiA JoJy} Mv{Iu(cE cG cO Cw Qg) Pz(Jj kF Nn Nw) Ma(Jj kK oH) cO(bV cN Ue) Fn(Mn Pd) CuUk NrkF MjkO MnJj UeKy} Ti{Pk(aG bN cO Qv) An(Jo Uk Tj) Hx(Jo Ks Tv) Dp(Bo Ed) Sr(Mm Tr) IbPh TvKn JoLh} Tr{Dp(bV Cp dA Jd) Jo(Ao Dk fR Jm) bV(Fn iA Mx) fR(bF cJ Uh) Gz(dA Ua)} Uk{cO(Fn Iz Jk Jl Ua) Cp(Et Om Uh) Et(Jg Lh) CuIz FnRh MuKq MxKo UpbA bVcJ} oE{qW(aY aZ cP cX iJ rB) jP(aQ aZ bJ cX iP lL) bCjM cJiC rBkQ} Mm{fR(Ba cT Jk Js Of) Gn(Kn Og Ql Qw) Ib(Dr Iv) JgqZ} Fn{Cp(Et Jo Pd) Et(Lh Mx) bV(cO iA) DgJg MyPd HvJo cNcO} eM{dM(aQ aU bS dR) cY(dD dR) bGbN cBcZ cIcN} Et{fR(Bo bW Oe Uu) Jg(gW Kd) MxJd} Pz{oP(Iv Mr Ms Mu nN Nx) MskF} bV{iA(Mx Pd Qx Uv) Ky(cO iJ) PkcO} Ma{kS(Ba Cp Hc Jh) MwkK PkbA} Dg{Jg(Ap Kd Tj) PoGn IzcB} jH{nU(mM nH) bNiC nRjI nJlL} jP{cQ(aF iP kR) FrLi iZkS} Ue{Ky(Cp My) CuIz dHdM} Gn{ApHc MyRc UbHu} lK{lL(nB nJ nT)} Bo{Dr(Hc Oe)} Cp{Cw(aX cS)} Hv{qZ(Ir Pe)} Hx{KoiZ PkiP} Jo{ThTz IuIz} EzcCgW UaUffR ItNwkN JjjGjY KoPkbA NvNykK aCcZdM aFbMqW bCiCkS Constrained panels with 3 analytes, where 1.0E-7 >= 'AUC p-value' > 1.0E-8. Contains 1,630 panels of 10,943,034 total panels evaluated. : aA{Up(Ad Ax Cs Cu Cw Dc dL Fa In Jo Jq Js Kf Kn Oa Pg Po Qh Rb Rm Tr Uc Ut Uv Vs) Ky(As bI bW cE Cv dG dH dL Fa Kd Mm Mp Mt Pd Uv Vt) bN(Ap bL cZ Dg eF Fb Ij iP jP kS Mn Mt oH Ue Vo) cO(aY bG Cx Kd Kq Md Mf Mp Nn Nr Oh On Qe Ue) Pd(Ik In Jo Lw Lz Md Mi Mu Mv Nl Om On) Uk(aQ Bo cB cE dG dJ iA Kd Mn Oy) Pk(aK aN Bo bV bW gL iA Kl Ok Tr) cJ(aX bG bS Fn fP Kq Kr Mn Qd Ue) cS(Ap bO cG Cw Et Fb Ma Mm Ok Qe) Lv(Jn Jo Jr Lh Mf Ml Mt Ny Qa) On(Ao bI Bo Cp Ih Il Ir It Iv) Et(aK aN aX bV cB Fr Jd Nw) Kr(aQ Bo bR cC dH dJ Fb oN) Fn(bW dH Fa Fb gL Mf Mm) Md(Dg Jk Lw Mu Mw Nn Pc) Tr(aK aU aX Cx Jd Jo oH) Qd(cC cY dJ dK kS oP qZ) Qe(An bV gL jK kS mZ rZ) Tv(cB cC cF Cx Oy Uh) Iu(aN As bO bW cC Jg) Kq(aK aU dJ dK Jd kS) eM(aP aY cK cV dG eF) Ap(Dg Iq Ir Is It) Mn(aN bW Jg Nw Qc) In(Jk Lw Mi Mu Mw) Io(aH bQ cV Kg Uv) bV(Dg Fb Ma Mm Uf) Af(Ao aP dG dL) Bo(Gn Jo Jq Oh) Ed(aU cC Ks Uf) Ir(bZ Jk Lw Nw) Js(Ji Mz Ok Po) cB(Fa Kd Ue Uo) Cu(Iz Kd Oy) Fb(aX Cx gW) Ex(Je Oi Ou) Nr(Dg Nw Qc) Ma(aN aX Nw) Ih(Jg Nw Qb) Ik(Dg Jo Mf) Jk(Jm Lz Nl) Kl(Iz Oy Uu) kS(bQ Hb Mf) Gc(bR cV) Mm(Kd qZ) Mt(Pc Pz) Ue(aQ dH) Il(Fr Nn) Iv(bZ oK) Qc(Ng Pz) Ok(Jq mM) AsEm BbOy ThcG LwIt MkmZ MpgL NcNl IsbZ JjrZ JtqU UhaX aCcZ bQcR bWoH gWiP nNkN rBqZ} Gd{Rh(Ao As Ba Ef Fw Gl Hx Je Kd Ky Lh Nv Oa Pf Qg Qw Ri) Qw(Ao Bo Et Iz Jy Ky Mv Nw Og Po Qg Qv Tz Ug Uv) Jl(Bo Ct Ed Ik Iz Jy Kr Kx Kz Mp Qv Ug Uu) Vt(Aj As Dd Fr Ha Ik Ji Mk Mv Oi On Ou Ri) Ct(Fb Ip Kc Kg Mu Oe Or Qv Ua) Qy(Ap As Aw Em Hb Jf Pd Rb Ur) Po(Dg Il Ma Nm Pg Qv Uf Uv) Ef(Ap Dg Mf Oa Ub Ur Wm) Hb(Ao Is Jg Nn Nv Ou Ql) Pj(Aj Cu Dg Ik Kj Qu Ug) Mv(Ap As Cw Pd Uh Um) Iz(As Kx Lu Ng Uh Wm) Uu(Bb Dg Ip Kc Ma Ur) Ao(Et Il Ke Lu Ue) Mf(Ha Nv Qz Tz Vp) My(Dg Ik Mt Ub Uf) Of(Fb Oe Tz Uh Vp) Fr(Ke Ky Mt Uh) Kr(Li Mx Nn Ny) Nv(Ap Dg Kd Ky) Bo(Fb Oe Qt) Et(Ik Is Tz) Ue(Dk Is Tz) Ib(Ad Fn Kg) Il(Aj Hw Jk) Jf(Hw Nn Uv) Qv(Gl Jk Mu) Lu(Ha Ik) Mm(Ks Mg) Mw(Kq Ur) Je(Nc Oa) Jg(Ap Dg) Ke(Lh Mu) Uh(Ba On) BbUa DcGc EmFb NqUg MkOe TzOg HxRi JhKc QzPd} Gc{Vt(Fr Gl Hr Hv Ik Is Jp Lh Nb Pg Ua) Uv(Fy Ha Iz Jg Nb Ql Rh Tn Vs) Ub(Dc Ed Hu Kc Kk Nf Oi Oy) Qv(Ez Hr Hw Mv Oy Qw Ri Vs) Rh(Ef Gl Ha Ik Pe Pg Uu) Pk(De Ik Mz Of Oh Pf Vp) Kd(Cq Hw Hx Na Ny Qa) Kr(Cq Cs Hw Hx Jr Ny) Ow(Bg Fb Gl Of Ur Vp) Pd(Al Ap Dk Fy Jh Kf) Vo(Bg Dk Gl Oa Uc) Ef(Aj Jt Mg Rc) Em(Dp Jk Mk Qg) Ma(Ax Co Mj Nq) Mm(Hr Sr Uc Ug) St(Ap Kx Rc Uh) Jy(Fb Mv Ri Vp) Og(Or Ud Uk Wm) Bb(Nt Ok Uu) Fr(cK cV Tr) Mi(Bo Of Ur) Tn(Cw Et Jo) Ii(Ke Nr Uh) Oy(Ip Ly Pc) Cp(As cK) Wm(Mk Ud) Fn(Hv Vp) Nt(Ap Uh) Me(Hu Vu) Nb(Ra Uk) Tz(Qg Uu) Tr(Is Nv) Ql(Bc Mt) Pe(Pg Pj) aP(aZ cK) AlIp BgIl TjHx EzQw GnNy GpgL MfMs MlPf MvUr UaJl UdHw HuKk TvVp IvVv IzKg JgJt UnPj aJbI cEeF cOcS} aP{Tr(aD aR bL bR cW Hq iP Jq Kd Ko Ks Mp Nj Of oK Uh Uk) bW(aX cZ Et Fa Kn Kr Ky Mn Pg Pk Qg Tv) Ko(Aa An aZ bA dL Im iP Mf oN pF Uk) Uk(bM Bo Fn Ky Mm oK oN Qe) cO(aM aX bG bL bN cS dL Ue) Et(aN aZ Cp dG Fn Kd Pk) Kr(Bo cJ dH Ky Mm Pk) dG(An Cp Kd Mf Mm Pd) dL(aC An Fb Pd Ue Uv) cJ(aX cS iC Kd Tv) Fb(dH Fn Ky Pk) iA(Cv Fn Hx Qx) An(Dg Kq Qd) Bo(Jo Kd Ks) jP(cQ hB iP) Cp(Cw Dg) Fn(Ma Mm) Kd(dH Mm) Kq(BA) aC(cW cZ) eM(aJ bS) DgJg MakS KyoK PddH bNcW bQcT} aJ{cO(aX cW dG dL Ed Et Fn Iu Mk Mv Pk Uk) dG(bN cS Fn Iv Kq Kr Mr My Pk) Ko(aZ BA Cp iP My Uk Up) bM(iP Iu kQ Kr kS Tr Ue Uk) dH(eM Kd Kq Kr Mn My Pk Tr) Ed(Af Cu Et iP Pz Ue Ti) Pk(dL Iv Kr Mm Tv Ti) Up(dL Et Qa Uk) cJ(aX fP Iu Tv) kS(jP Ky Ma Qe) Kq(An aZ cS) Th(Dg Ow) Tv(dL Ok) jP(aF hX) BoIv ExOu TrNy IudL KyfP aCcZ bCbW bNcW cVeM} mZ{Jk(Ih In Iv Jg Jm Js Li Nj nK Ny Pz Qe) Og(Ih Ir Jm Js Jt Mz Nf Nm oP Qd Qe) Mv(Ij Jh Mn Of Ok Oy) Qe(Jp Ms Mw Nv oP Qb) Js(Nf Nx Om oP Oy

Figure 13 Continued

Po) Nw(Ih Iu Lj Ma Nj Qa) Qd(Jp Mw nK Om oP) Ok(Fr Nv Nx On oP) Nr(Mu Mw Nq Nv) Ma(Hx Lv mF Nd) Mf(Lj mM Ms nN) Mk(Lj nK nU oP) Jt(Fr Ms Om) jH(iC mI qU) Nj(mU Ng) Pa(Iv Lj) nU(iC jG) NmMs NfHu} Nq{Tr(bV cB CO cS Cw Ez In Kj kS Ma Mf oH Pi Pk Pz Ue) Ue(Bo Cu Et Fn iA Kd Kr Mm Pd Tv Uk Th) Kr(Af Bb cJ Dg Et Ky Ma Mg Mm Qg Tv) Ko(Cw Et Fn Kg Ml Mx My Qg Uk) Fn(Ad Bb Cw Ma Mg Pz Tv) Uk(Cu Dg Kq Mm Ok) Et(An Jd Pk Un) Th(Dg Kg Nm) iA(cH Ma Mf) Ti(Cw Mg) Tv(Bb Mm) MakS} Mv{Pz(Ir Ji Mg Ml Mu Mx Nk Nv Oh Ok Qa Qb) cO(aX cS dA dl dJ dK dM Mn Pd Pk) Uk(Af cE cJ dJ Fn iA Iu Ky oH) Iu(An cJ Cu Dg iJ jP Ue) jP(Hx iB jH jT jY rX) Mg(Jj kF IL Mn nI) Ue(cB Cu Mn Ny Pk) Jt(Jj Nk Nw) bV(cE cG iA) nl(Mf Mj Nf) Ma(Kd nK) Mn(An Ng) Jo(Ir Tr) Pd(Jj Pk) BbEm MzJs PkcB} Em{Nm(As Cu Fy Il Im Jk Mu Nt Qy Uu) Pj(Cu Ha Im Je Ng Om Qt Qy) As(Je Jk Po Rh Ua Ue) Et(Li Lx Mw Oc Qy) Mm(Gp Jj Ut Vp) Jt(Fr Mw Oe Qy) Kf(Fb Mu Oe Ua) Cw(Mu Mw Qy) Hu(Il Kc Om) Uh(Fb Jl Oe) Jo(Ct Oe) AdFr BbMu DgFb PoOk MgHc UaKj UeQy} Uk{Cp(cJ cO Dg Ko Ky Mn Pd Ue) cO(BA cN Mu Mx My Tz) Uh(Fn Jd Ji Lh Mx My) Et(Iz Jd My Nn Un) Fn(Mf My Qg Ue) Ko(BA cN Im) Pk(bA bV cT Rh) bV(cE cV Qg) iA(Iz Jl Un) Ba(Cu Ma) My(cJ Ue) EzdJ MfoH MmMx MnUa MuTv UeIz UpcT bAcE cJdM} Fn{My(Ad Dg Et Jo Ks Mg Ue Uh) Ue(Cp Ky Mf Mx Pk Tj) Jo(Ao Iz Jd Nn Pg Qy) Pd(bV Jd Li Nn Pg Po) Et(Jd Nn Nw Un) bV(cE cJ Ma Pk) cO(bA dM Jl) Pk(cT Rh) CpMg DbKr DgJl DpHv MxTr HxiP bNiZ cHiA} Ue{Cp(Cu Cw Et Fa Iu Jo Kd Ko Mn Pd Pg Pk Pz Tj) Iz(cO Jo Mn Pz) Et(Jd Mx Un) Pk(Jd Jc My) Ba(Cu Ky) Ko(Mx My) EdiZ UacO JeLd KykS LhUh bVcJ} Tr{Jo(Ih Jg Jk Jl Li Mw Mx) Dp(Ba Ez Mw My Nn) fR(bO cD Et Mm Ua) bV(An cO Cp Il) DkMn MxIu JdKg PkbA bUdM cBhG} Pk{bA(cB cC iA Kd Kr Mf Mm Pd Pf) My(cC cO iJ) Ba(aZ cB) Im(Ko kS) bV(cJ Pd) TiNw MuKq HxoH cBcT} fR{Et(aE cJ Cp cU dE Hf Ik Ji Tz) Mm(Aw Kp My Ou Tz Uu Wm) Ma(Ba bL Oe) CwEz PjcJ} Iu{Cp(Ad Cw Et Pd) Mu(cO Kq Qg) iA(Hx Iz Jl) oP(nN Nx Og) qU(Hx lL) FrjP MxKr JnjG KyiZ OykF} bV{cO(Et Im Kd Kr Ma Mu Mx) Ky(cE iZ nY) iA(Qw Us Uu) Ex(Ni Oe) Pd(cJ cV) MfiJ KrcJ} Ti{Jo(Cp Dc Ii Nn Tz) Na(Ks Ky Tv) Hx(An Ib Ky) Mg(Jv Lh) Ks(Mx Rf) DiIb MfNw} Gn{Mm(Jn Mg Mz Nf Ph Qa Uc Ut Vp) Ib(It Jf) CwPo DgEf MzPj NvUh} eM{bS(bN cM cS dD) cY(bE bN cM cZ) bE(aC cK) bL(bN cS) cB(aX cS) cTcX} jP{Fr(Mf Nj Qe) kS(bJ cL lL) cQ(hX iO) oE(bG oH) MsJj aQoF bNiZ nJlL hXoH} Ko{Mx(BA Im) iZ(bM bN Ju) Aa(iO oF) Im(Jd Qv) Jo(Cp lz)} qW{oE(aM cG cJ dF dG dM kS) aF(cO oN) aO(fP hB) oFoK} Ma{kS(Hx Jk Pg) Mx(BA) IbcB RfcT NwnR aOoH} Pz{Ms(kC qZ) kF(kN oP) NnMu JjJk JpnR LjoP OgoQ} jH{nU(jG jI nC) qU(nB nT) cQiP nAIL iOjG} Et{Mx(Cp Tv) Jg(Bb Ex) JdUn JlcO LhcB} Dr{Bo(Jl Mu Po Ua) ApHc IbJf} Ib{cB(Bb Mm Pj) MmcS MuUt} dM{cS(cJ cO) MfiA JrdH bQkS} qZ{rB(Hx iC lO) Hv(Fp Lj)} oE{cW(qV qX) iC(aZ iP) bMrB} Cp{Ad(An aZ) aCcZ aXcO} Ex{Mu(fP Qv) ImgW JlfP} Nw{PokN NnJt QekF OkkK} kS{Ky(Hx Im) bQcN cLiC} Dg{Jg(Bb oH Qg)} Jo{Th(Jl Qc) IzUp} iO{jG(iJ iZ jT)} lL{mM(jT rX) nRjT} Gz{Hc(Ke Kg)} Nr{PooP JknK} Jj{MnJk MsqT} iZ{BoIv bMgW} NnMxJt MwltmH JiOkoP UpPdbA Constrained panels with 3 analytes, where 1.0E-6 >= 'AUC p-value' > 1.0E-7. Contains 3,117 panels of 10,943,034 total panels evaluated. : aA{cO(aM As cI Cv cW cZ Dd Fa Hv Hw Ii Ij In Ji Jn Jo Jq Jr Js Jt Ke Kf Kg Kn Lh Li Lw Mi Mj Ml Mq Mr Mt Mz Na Nb Nf Nm No Nx Ny Ok Om Pb Pd Pe Pf Pg Pi Po Qa Qx Rb Uc Uo Ut Uv) Up(Bn Cp Cq Dd dG Ii Jr Kg Kx Lh Li Lw Mj Mq Mr Mz Nm Nn Nx Ny Pe Pi Tn Us) bV(Ap bG bL bQ cE cG cK Cu Cw eM Fa hB Jp Jt Ke Kf Kr Mn On Pd Qa) On(aN dJ Fb Ii In Is Jo Jr kS Lh Lz Md Mt Ny Pe Pf Pg Po Qe) cS(aH aI aL An aY bB bL bW cE cK Cu cZ dF Fa Jp Ke Pd Qa Uf) Ky(aY Bn cJ Cw dJ iA Jo Jq Ks Md oH oK Rb Rh) Pd(Bo cB cJ dH Fr gL Jg Ji Jk Mq Mt Nw Ok Tr) Ma(aK aQ As aU Ba bI bZ cC cJ cW dI dJ Jd) Lw(Hv Hw Ij Jn Jo Jr Ml Mt Na Nf Ny Qa) An(Ad As aX bI cE Cu Cw Dd dG Mt) Fb(As cB Cw Jo Jq Kd Ld Oh Om Tj) Md(dH gL Jg Ji Mq Nv Nw Ok Om Uh) Tr(bO bR dI Fa Kp Kr kS Ok oN Uk) Qe(aK aN aQ aU cC cY dJ Nw oH oP) Kr(aK aN aU aZ cE cF Cw dK Oy) Mt(Bb Fr Jg Jk Mi Mu Mw Ok) Tv(aN As aU bU cJ cY gL Ke) Iv(aG aN bO bW kN Qg qU rZ) Et(Ao cC dJ dK Jg Ji Ok) Fn(aK aU aZ cC dG Kd oN) Io(aY Bc Cv dF dG dL dN) Ir(aN bW Jg Ji kN Ok Qc) Nw(Il In Jo Jr Lh Lz Ny) Uk(aK aU bU cC dF dL kS) Uh(As bI Bn Nn Nr Oi Pk) Mn(aK As bU Cv dJ kS) aX(aC bW Cw Dg dH Uf) gL(Jy Li Nr Qx Rb Ue) Bo(Em Ii Mb Om Ue) Ed(aK Jp Mg Vo Vt) Iu(bI cV jG kN rZ) Pk(As cE Fa fP Vt) Mp(aK aN cB cC) Jg(Il In Jo Ny) Ji(In Is Jn Jo) Jk(Hq Jo Lh Pg) Kd(aK cC cF cJ) Ok(In Jd Jo Nm) aQ(bL bS cK dH) jG(iO Jj Mf Oh) oN(bZ dR gW kS) Af(cZ eF oK) Cw(Aw Cp Oy) Dg(Ao Jd Oi) Qd(bW qU rZ) Ny(bW Mw Om) aC(aL bE Cv) aZ(Cu Cx Ue) bN(cE Gc Uf) mZ(Lj Mv Og) Mi(Hq Pg) Qa(Qg rZ) Qc(Ih Js) bQ(cI fP) bX(cJ Gc) cC(Ow Uo) dH(Dd gW) eM(bG dA) iA(gW Mf) oH(aY bM) AdCp ApGn AwcE AxMm CuUv DbGd DlOy EmGp FrMg MqJr MuNk MwMy PznR JsrZ KlbI KqbW KsaK nNoP nUqU mPkN} aP{bW(bG bL bO bQ cS cW Iu Jo Kg Kq Ks Md Mf Mp Mt nW oH oN Tr Uh Uk Uv) Tv(Af An aZ bF bN bO bZ cB cE cG dF dH dL dN Et iP Ky Ok Uh) Ko(bN bO cG Cp cT Cv cW dE Fn iJ Jg Kd Kr Kz Md Mp My Nq Tj) dL(Al aN Ap bG bL bX cE cI cS Fn Io Iu Kd Ma Md Pk) Ky(aM bM cJ cT Cu cW Dg Fn iJ iP Jo Kd kS Ue Ti) Tr(aM aX aZ bV cE Cu iA Il Je Kr Mf nW Pk) Pd(aM bM bN cJ Cp Fb Ju Kd Pk Uk Up) bL(aM bG bO bQ cI cS cW cZ dG dH Gc) cJ(bG Fb Fn fP Iu jP Mp Pk Ue Ti) Et(Ba bO cB dK Jg Ji Jr Mf Mr) cO(Ba cI Cp Cv cZ Iu Jy Mm Vt) bN(aM bG bQ cI cZ dH Fb jP) An(aR aZ Cu Cv dH On Qe) Bo(Fn Ii Iv Kg Mn Oh oK) Uk(bO bU dN Fa Kd Pk Uh) Fn(cB DG Mf Pk Uh) dH(cW Im Iu Jy Mr Mx) jP(cW cX hX jG jM oE) oK(bM Iu Mf Mm Mp Ow) Fb(cW dN Kr Mf oN) Kq(aM aZ cT dN pF) bQ(aX bA cS kS Pk) Gc(bI bR bX cB) Ma(BA cT nW) Kr(bJ cB cF dN) bM(iP Ue Uf Uv) cE(aM cT cW) iA(Jy Nq Ow) Cp(Ad Ap) Dg(Aw Iz) Ed(iJ Ti) Pk(cB Kd) aC(bE Cv) bG(aM cW) dG(Mi Mp) eM(cB cK) CuIz TicG ThiJ MmRg JoJy aRcI hXhB} Gd{Vt(Ax Ba Dl Ef Fp Gl Is Je Jp Kj Li Mw Nt Og Pe Pf Qt Qy Ug Vu Wm) Jl(Ap Dg Em It Iu Kc Kd Mf Of Pd Qz Ri Uh Uk) Rh(Cp Fy Ib Ii Ik Is Jk Li Mg Mk Mv Og Qz Ss) Tz(As Bo Em Ib It Jk Jt Kc Ke Kr Qv Qz Ri) Kr(Ba Cq Dc Hv Hw Hx Is Jk Mj Nq Ql) Jf(Aj Ao As Hx Ik Is Li Mw Oy Ri) Mf(Ao Is Li Nn Oa Of Qg Ur Uv) As(Ik Jy Mu My Of Qt Qz Ss) Et(Fw Ib Im Ji Nw Ou Pe Qt) Iz(Ad Bb Bo Dg Iu Ke Kg Pc) Je(Bc Bo Cw Jk Mt Pd Qg Vp) Qv(Aj Fr Is Jh Nv Of Qt Ug) Po(Ap Fa Lx Mk Og Ow Rb) Mu(Bc Iu Kc Mt Pd Qa Qe) Ib(Cw Kn Ko Mt Qw Uc Ut) Hb(Cp Hx Jk Jp Mw Of Qt) Uu(Bo Kj Kx Or Pf Qg Uf) Qy(Ij Ke Ko Lu Mt Qg) Ef(Ip Iu Kg Lu Mg) Kc(Aj Fr Nv Of Qw) Uh(Dc Is Lh Li Nn) Cw(Cp Ik Lh My) Ue(Cp Dc Hw Ik) Jy(Fr Mw Nq Qt) Of(Fp Or Pd Rb) Pj(Al Cp Ih Pz) Ba(Dg Ur Wm) Bo(Fr Mv Nq) Nn(Ke Ky Uf) Hw(Qg Rb Uk) Il(Em Vo Vu) Qw(Jk Nv Ri) Aj(Nu Ub) Fp(Ct Gc) Mv(Dg Ma) Kd(Fr Mw) Ke(Hx Jp) Nv(Mp Tj) AoPd ApMy FnUr MkOa HfQg RbJk KyVp LhUf} Uk{Nq(Af Bb Bo cE cJ Cw dH Fn Io Jo Ke Kl Kr Ky Mn Pd Pz Qe Qg Rh Tv) Mv(bR bU cB cF Cw Et gW iP Ko kS Ma Mn Ny Pd Pk Qg Ue Uh) cJ(aJ Aw aX BA cN cT dA Ez Fn Ib Iz Je Mu Mx Po Qg) Cp(Ad Af Ap cF Cu Cw dH Fa Jo Jq Kd Ma Mm Ok Pf) Ue(Ba cO Ef Ez Jd Kd Ky Mx Nl Oe Pk Ua Us Uv Tj) Fn(bV cB dE Et Ez iA iP Kr Mm Mx Pd Pk Ua) Mx(dH Kr Ky Lj Mn Og Qe Rm Tr Tv Vt Ti) Ky(BA bV Ez fP kS Mu My Nn Ti) cO(Aw aX cT dA dM Ez Pk Po Qg Qh) Et(An bV Ez Ji Jl Oe Po Rf Tz) Mn(Ef Iz Jk Jl Oe Qg Qh Qy) Ko(An Ih iZ Jd Mu My Nn No) bV(cG dF dH Mm oN Pd Tr) oH(bW Hx Ow Pk Tr Us Th) iA(BA dM Hx Ib) Ez(aK bU cC Hb) My(cF Dg Pz Qg) Jd(Kr Nm Qg Tr) Jo(Ct Ik Iz Jm) Uh(Jg Nn Po Un) Pk(bU cB Mu Ua) Mm(Hx Jl Oi) Kr(bR Nn Qy) aJ(Bo dG Ed) cE(Ba cT Iz) iP(Hx Ib Us) Cu(Jl Ua) Tr(dM Dp) Qg(Iu Mf) iZ(bM Ed) DgJg TiNa EmOe MabA UaNy IkPd IzPz} Fn{Nq(Af Ap cO Cu Dl Fb iA Jq Jt Kg Kl Kq Kr Ks Mf Mm Mn Nr Ok Pf Rh Uc Uf Vo) Jo(Ct Ha Hx Ik Jg Jk Jl Ky Mf Mu Mv Mx Oe Of Pk Po Qg Ua Us Uv) Pd(BA Ha Hx Iz Jg Jl Lx Mu Mx Oe Oi Pe Pf Pk Qy Ua Ue Un) Et(An Ba bV dM Hx Iz Jg Ji Jl Jp Li Lx Mv Oe Pk Po) Mv(cB cO Cu Cw Dg Iu Ky Ma Mf Ng Pk Ue Vo) Mx(Bb Dg Jq Js Jt Ko Kr Ks Pz Rm Tv Uh) Ue(aD aZ cJ dE Iu Iz Jd Kd Nl Oi Ua) My(Bb cO Cw Jq Jt Kg Ko Nm Pk Pz) aJ(bM Bo iA Ko Kq Ma Pk Tr Tv) Cp(Ad Cw Dg Kg Nm Om Uh) Pk(aX aZ cB cO Mm Qv Qy) Ba(cO Cu Cw Dg Ko Ma) Jd(Dg Kg Ma Mg Tr Uh) bA(cF iA

Figure 13 Continued

Ko Ky Ma) bV(cG Cw fP Ky Mg) dM(bW cJ iA Mm Uh) Mu(Cw Iu Kq Tv) Iz(Cu Dg Mn Ng) Mm(Ib Oe Tv) Hx(Dg iA Ks) Cu(Jl Ua) Nn(Kr Ma) Mf(iJ Rh) Tr(dA Nb) Kg(Hv Qy) Ko(Im iZ) Lh(Dg Uh) AlQg AnTi MnUa TvRh KsUs bNfP cHiJ cOcT} Ue{Cp(Af Ax aZ cJ cO Dc Dd Dg dH Jq Kg Kr Ks Ld Mf Mg Mm Nl Nr Pf Pi Tr Uh) Nq(Ax Bb cJ Cw Dg dH Fa Jo Ko Ky Lj Mf Mn Nl Oh Pk Pz Qe Uh Tj) Iz(cB cJ Co Cw Dd Dg Et Iu Kd Kl Ky Mf Ng Pd Pk Tj) Mv(cJ Cw Je Jo Kd Ko Ma Nk Pd Pi Tj) Mx(cO dH Iu Kd Kr Ky Lj Mm Nl Qe Tv) Pk(BA bV cT Ik Kd Mu Nl Nn Qy Ua) Tj(Ba Em Jd Je Jg My Nn Ti) cO(aJ Ba bV cN dM Jl Mu My) Jd(Fa Ko Kr Ky Qg Tr Uh) My(cJ Cu Jo Kd Nl Pd) Em(Fb Fr Jl Mu Mw) Mr(Ax Kd Kr Lj Mf) Ky(bV Fr Mu Qt Ua) Ba(cJ Iu Ko) Cu(Jl Lh Ua) Kd(Je Jl Us) dM(aZ cJ iA) Ao(Jo Ti) Ib(cB Gn) Un(Mm Uh) AsJe PoKr EtLh MnUa IkPd ImKo HcLd IuRf PzJg aXcJ} Mv{Pz(Il In Is Jl Jm Jo Mf Mi Mk Mr Ng nK Nr Nu On oP Qc Qd) Jo(Bo Em Is Jj Jy Ky Mn Ng Nk Nn Nw Ok Om) cO(Ad bU cB cC Dd gW Kd Ko Ma Mf Mg Ny oH) Iu(Ad Jl kF Kg Ks Ky Mk Mr Rf Tr Uh Vo) mZ(Hq Hu Ir Iv Jt mH My nI nK Pd) Jt(Ir Is Ji Mx Nn Nu Ok On) jP(hX Jj Lv Ma Mf Of Pd rY) Ma(bA iA Mf Mi Ml Mu) Mn(cJ Co Cw Hx Qg Tr) Mg(Js Ko Ky Ml nK) Ng(Jm Mf Ml Nn Pd) nI(Hu Jh Nq Nr Of) Jj(Ik Mf Ml Nn) cB(iA Tr Tv Uc) cS(cE cG cJ iA) Em(As Cw Et) Ko(aJ iZ Mx) Pd(Jd Ky Nw) Mf(iA iJ) Nk(Nc Nl) Js(Hv Mx) AnEt BoDr CwfR DpTr ExfP NmOk PkbU bVcJ dMiA iJkS} aJ{Tv(An bU bW cE Et iP Kd Ko Ky Mn Mp Mr Ny Qg Tr Uh) Ko(Aw Bo cT dE Ed Im Kp Kr kS Mf Pk) cO(aM Aw bG bM bV fP Io Kd Mn Tr Th) dG(Al Ba bM bV dE dI Kd Ma Mn Ow Tr) Kq(aM aX bA cB Cp dE Ez Iz Jg Mf) kS(Bo bW Dg Hb Kn Ow Qd Ut) Kr(bJ Bo cB cJ Ed Ky Up) Tr(bU bV Jo Jq Ks Up) bM(Io Kd kR Ma Pk Th) bW(aX bG cS Iu Mn Th) bN(bG cE cI dH iA) cJ(bG bS iC Io jP) Dg(Ap Cp Ed Iu) dH(Jy Ky Mf Qg) Ed(iJ Jp Uh) Gc(bX cK Cp) Up(Jo Mn Mp) Pk(Et Fb iA) Th(bI iA) Iu(Bo Qg) bL(cS dL) bV(Fb iA) jP(cQ iP) CuIz EzQd IvKy aCbE bXeM cEcT dEdL iOjG} Nq{Ko(As Ba cJ Co Cu Dg Fb Hx iA Jj Kd Kj Ks Ky Ma Mf Mm Mn Nl Pk Rf Uh) Tr(aX aZ Ba bF bU cF cJ Dd dI iO iP Jd Jt Mx Qg Uc Ti) Kr(Ad cO Em iA Iu Jo Kl Ks Mn Mx Om Pk Pz Uh) Kd(Ad Bb Cu Cw Jo Ma Mm Pd Pz Tt Uh) Tv(Af cJ Ke Kl Ma Qg) Uh(Em Jy Ks Pd Pz) iA(bA dM fP Hx Pk) Em(Et Kf Nm) Dg(Nh Pk) Et(Cp Qg) Th(iJ Kj) Jy(Pd Pz) Kq(BA) Ks(Bo Cw) CuRh TiNy HaPd NrkF MmPk IuQg JoKy} Gc{Ny(Id In Ir Md Ml Pi Pk Ra Tv) Uv(Co No Pe Pf Pg Vo Vu) Tr(Dk Ef Lh Sr Tn Vv) Vp(Kd Kr Md Ml Pi Uu) Cp(bP bX cP Ct Cw) Jr(Lw Md Pi Ra) Vt(Dk Ez Vq Vu) Mi(Hr Oy Qv) Tn(Ma Mg Tj) bX(cI Fr gL) fR(aG aH cE) Ao(Af dN) Bb(cK Im) Em(Qv Ur) No(Nr Rh) Ip(Ed Qh) Jn(Kd Tv) Ok(Pd Uh) Ow(Ez Qt) Vu(Bc Kd) aZ(bC eF) cB(cI gL) AdUu AjVo CoRh CtFr CwSt DcDd DeFy FwcK GlcI NrLh MeVs MmVq NeQl NfKz TzPd IiJt JsKr JyOa KxOi bAcE} mZ{Js(Lx Ms nK nR nU Oe On) Mz(Fr Jp Mw Nn Nv oP) Jt(Jp Mu Mw Nv Oy Pa) Nm(Mu Ng Nw oP Oy) Qd(Jk Mu On Oy Pa) Ms(Ih Jm Mj Mk) Lj(Hx Jk nK oP) Nw(Ir Iv Lh Mf) Ok(Hx Ng nU Pa) nR(Jo Mf Mj Pz) jH(jI nC nH nL) jG(hA nB qT) oP(Mn nN Nr) Mw(Nf Pg) Qb(Ih Qa) Jk(Jj nI) nU(jL Jn) qT(nL qU) NrPa ManK MfNg MjOe MuPz NdOg HxPb} Tr{Jo(Ap Aw Ba Cq Ef Fr Ij Lh Lx Pg Qh Ss Ua Uf Un Uu) Dp(Aw cS fR Hx Ih Je Mn Mx Qg Qy Uv Ti) fR(aF cB Cw dA Kg Nb Nj Oe Qy) Mx(aX cB cS Jd Jq Kr Ks Ti) bV(bU cB cE cG cJ Jd Pk Rf) Jd(Jq Ks Pd Pk Ti) Cp(Iu Iv Kg Ks) dM(cJ cO Ez Kp) Kg(Nn Qy) Pk(dA hB) cB(bA Lx) TiHx IuRf cFkS} Em{Nm(Cp Gl Ik Je Jg Jh Kn Lh Mj Mx My Ng Nn Of On Ou Qt) Mu(Ad As Hb Kq Kx Ma Mk Qe Uc) As(Ef Gl Jt Ub Vt) Et(Je Jl Jp Lh Mx) Ua(Ap Bb Kg Ug Uh) Po(Dg Ii Mg) Hc(Ap Dc Kj) Jo(Ef Iz Of) Jt(Fb Ib Qw) Lx(Ok Uh) Mm(Mi Vu) Oe(Ad Mg) Pj(Bg Qd) BaDg DdHu TjLu FbOk FrHb QyQv JkKg JlKe} Pk{My(Ad aK aN bJ bU cB cJ Dg dJ Pd) bA(aK bU cO dJ Et gP Iv Pg Uv Vs) bV(cC cE cV Et gP Kd Kr Qg) cT(aK bU cO dJ Iv Mm Pd) Ba(aK bF bI cO Rh) Mu(aZ cO Ko Om Pd) Nn(Ko Mm Rh) Hx(iA iJ kS) cO(dA dM Jl) Cp(Et Pd) Kr(dM Jd) Rh(hG Im) iA(dM fP) EtLh NoKo OgfR aXgP} Mx{Et(Ao Ap Aw Ba bV cS Iz Je Kd Kr Ks To Un) Jt(Fr Is Jg Jp Nw Om On) Ko(As Kd Md Mf Nl Nn Pd) Iu(cJ Dg iA Ks Uh Vt) Pz(Fr Iz Mu Nn Nv) Kr(cB cF cJ cO Ks) bV(cJ Cu Dg dH Kq) Ti(Jo Ky Mf Tj) Tv(Mm Pj Uh) Cu(Iz Ua) Ma(Jd kS) BbJd DgIz MmKd IvPj} Pz{Mu(Ir Is Jg Ji Jj Mf Nk Nv Oh Ok On Qa Qb) Fr(Ir jP kN Ma Nk Nl Nn Qb) Jg(Dg Im Is Nn Nv Qb) Nn(Ik Jj My Nl) kN(Jp Ms nK Nw) oP(Ih Is mT nR) kF(Iu Nf Ng) Ms(nK oQ) Ik(Jj Jp) Iz(Jo Pd) jY(jG qU) MwnR MyPc NkNv IsJm nNoQ} Iu{Cp(As cJ Kg Mg Mm Nm Om) qZ(Hv Hx Mm Ms Pa rB) kF(Jk kN Mw Nx Pb) Jl(cO Js Mf Ml) Iz(Dg iJ Pd) jG(Hx jH Mp) qU(jY Lv Ms) jP(Hx Mp Mw) oP(mM nK Po) Mu(cJ Cu) iZ(Bo dH) BacJ NmOn NnKs MflL MwcO HqrB IbiA IhoE IsJn JkkK LhUh ParZ} Ti{Jo(Dk Ed Ez Ih It Jd Ji Jm Jv Ke Kn Nw Pg Rf) Cw(Ao Fr Ib Jp Ke Nn Nw Tz) Mg(An Ao Ba Ed Ez Hx Jd) Ky(An Ez Fr Nw Rf Tj) An(Ao Ib Mf Nw) Dp(Di Hx Mf) Tj(Hx Na) Nw(Mm Uh) AoKs EdFp MfRf NaHx TzIb TvUv} Cp{Ad(aN As bN bV cE cO cS) Et(An As dM Iq Jo Mf Pd) Dg(As aZ bV Dd dM Gn) Jo(As Jq Jy Kd Ky) Pd(bV cJ cO Mn Nm) Ko(Im iZ Mg) cS(cE cJ cO) Cw(As fR) Dd(Af bN) bV(cE cO) MgIr aXcJ} Ko{iZ(An Ba bV cH Im Jv Mf My Ow Up Us Uv) Im(bV cJ Hx kS Mk Oe Oi) Nn(Jo Kg Ky Pd) Aa(cN eF kS) Ba(Dp Ma Oi) Jo(Ao Jg Lh) cO(bV cN Jl) bA(Ma Up) GnIb MdMu JdKg} jP{lL(aF cQ Hx iB iO jG Jj Mf Ms Nl nU oF qU) oE(cI cJ cU gW iZ jQ kS) hX(cI gW iP) kS(aQ iP jQ) Fr(Hx Pf) jG(hA iO) oF(gW jQ) MfMs MpHx aEcQ aFaZ bMiZ} Ma{kS(Aw bA cT Dc Ez hG Im Is Jg Lh Mu Mw Nn No Rf Uu) Ba(cO Jd Kd Mn My) bA(aO bZ Ed My) Mw(kN nI) Jd(Ez Mf) fR(cR Of) MuOh IrkF IzoH JlKd RfhG} bV{cJ(Et Fb iZ Jr Kd Ky Mm Qg) cO(An Il Iq Jo Kg Ks Mn) Pd(Ha Ky Nh Oy Qg Tz) cE(An Kd Mf Qg) Ex(Jh Mu) Kr(cB Ky) iA(Im Vt) BoJo EtJr QgcG KyoE bMiZ} Jg{Dg(aZ Dc Dd Iq Ir Jd Kq kS Md Mg Mn My Nh Om Pi Qx Tv Vs) Et(An Dc Dd Kl Qv Uc Tj) Jt(Is Mf Nk Nn Nu Om Qa) qZ(Qc qW) CwfR} eM{bS(aX bA bE cA cZ) cK(aX cM cS cZ dD) cY(aV cS dN) bA(bG bP) bL(aX gL) cP(cB cZ) aKdR bEcT bGdM bNbX cScV} Et{fR(cO cT Ef Iz Jr Nc Of Ou) Lh(An cO Cu Jd Kd Vo) Jd(An Jl My) Ib(cB My) dM(An aZ) MfUn MsqZ} Jt{Nn(Fr Jj Mu Nu Ok On) Nw(Ir kK Mf Pd Qa) Jj(Is Jk Nv) Mu(Is Om) FrIr GnVp GzHc NtkK} cO{Jl(cC Cv Kr Pd) aX(An Aw Ba dM) Iz(Ad Mg Pd) cS(An Aw Ba) dM(cJ Jr Kr) MycN qWoE} jH{nU(iB iC nA nN nR) cJ(aE iC oE) qU(Jj nA nJ) cQ(bM fP) nR(lL oQ) mM(jG oP) nTmI nBjG} Jo{Th(An Ha Pe Qa Qt Rf To Uv) Iz(Cu Jy Kd Ky Mn Pd) Nn(Ky Up) MsmM UaUp} kS{iZ(bM kQ Ky) Hb(hG Hx) bA(bQ Ky) bW(dM rB) jG(iO oE) qW(bM cU) MfiJ bQjD iCoE} Gn{Mu(Bo Mk Rc Wm) Pj(Hv Ib Ok) Po(Ap Uh) DgGl NmMm MkJl HbOu} Hx{iA(aX bA cS dM Mf Oi Us) MfiP IkJj ItmM QeqZ OwoH} rB{aF(aZ bM cE dI qW) qZ(Lj Oy rY rZ) oE(aM cE)} It{kN(kF Mw nK Qb) mH(mU Qb) mT(Jk Nv) NtkK OgoP} Jj{Ik(Jk Mf Ml Nn Qc) Nn(Mn Nm) Nk(Jk Nl) qUlL} dM{cJ(aX bG fP Kr) cE(bX cT) KrcF UpPd bNcI bWoH} Iz{Cu(Mf Mg Pd) Mn(Mg Mm) iJ(Co Mf) DgcS KlcB} bA{Ky(iA iJ) cJ(cS fP) AaMn AwcE bNcI gWiP} qW{aF(aZ dI iA) aO(aZ oK oN) iAoE hBoF} Dr{Bo(Mw Nn Vp) Pj(Mz Ok) MkMu MmHv} fR{BaKq BoKg CwUu EzMm TvOe aCcZ cEcT} Jk{Ny(nK nT nU) Nr(kF kO) MjkO} iZ{bM(aK cS dR oH) JybN KyfP} Mf{iA(Jl Un) oH(cT Hv) UsiJ} Mu{Ex(gW Ip Mn) TvOf JdKq} Qe{qZ(Ms Nl Qa) nK(Mw Qb)} cB{Kr(hG oE) BaKl UaTv IbtF} iC{bN(aZ cQ iO oF) cLoE} Gz{Hc(Ap Kj Nl Uc)} Nw{Js(kK kN) OkkF PdkN} iO{jG(cE cL nY) iJlL} Mm{BaIb GlMn MwTv} An{CuUa KyfP} Nm{NnNk MskF} Mj{nJ(Ms oP)} kN{MnnK jTlL} oE{bMqV jGoH} AfNnKr AwaCcZ BaKyfP MrHvqZ UpPdcT bWhGoH nTjRlL nUnBqU

Constrained panels with 3 analytes, where 1.0E-5 >= 'AUC p-value' > 1.0E-6. Contains 6,289 panels of 10,943,034 total panels evaluated. : Uk{Cp(Ao As Bb bF Bo bR cB cE Co Iu Ke Kg Kq Ks Md Mg Nm On Pg Qg Rh Tr Uc) My(bR bU cB cC cE Cu dH dJ iA iJ Iu Jo Kd Kg Kr Ma Mg Mn Og oN Pd Tr Vt) Et(aJ Ao Aw Ba cN Ef Fr Hx Ib Ih Ik Je Jk Kn Li Lx Mu Oi Pk Qy Ua Uu) aP(aD aM aR bN bR cB cE cF Cu cW dF Dg iP Jy Kr Md Mf Pf Qg Tv Up) cO(aD bZ dJ Ef Fr hG Ib Ih Im iZ Je Jg Jr kS Mi Mj Nn oH Oy Ud Un) Ba(bF Bo bR bU cB cF cG Cw dH dJ Fn iJ Iu Kl Mm Mn Oi Pk Qg Uh) Mu(Af aR cE Cu Dg dH dJ Ir Iu Iv Jo Ma Mn Ny Pi Qg Ue Uh) Iz(Af cB Co Cw Dg iJ iP Iu Kd Kl Ko Kr oH Ok Pd Rh Uh Vo) Ko(Aa Aw cT Dk Ez Hx Jg Jl Oe Oi Po Qh Qt Qy Rf Tz Ua) bA(Bo bR bU cB cF Cu Cw dF dH Ed Fn iP Kq oN Qg Uh)

Figure 13 Continued cJ(aD aK cS dl dJ fP Im Jg Jk Jr Kd Ou Pk Ua Ue Up) iA(aJ aK Aw cH cN Ez Iu kS Mx oH Oi Oy Pk Up Us Uu) Nn(Bb Cw Dg Jo Ks Ma Mf
Mm Mn Ok Pd Pk Rh Tr Vt) Kr(bU cB cF Db Hv Hx Jl Ky Mv Na Nu Oe Rh Uc Us) Ez(As aU bR cB cE cF Dg gW Mf Mm Mn Pd Rh Uh)
Nq(Ad Ap Co Fa Iu Jt Kd Kg Ks Ma Pf Pk Vt Th) Mx(Ax cB Cu dL Fa Iu Iv Jq Kd Ks Pk Qy Ua) Jo(Ao Ha Hv Ih Jd Mv Oe Of Po Qy Up Us)
Kd(bV Fn Hv Hx Jl Mv Nb Oe Og Qg Qy Rh) Uh(Aw bV cT Hx Je Jl Jp Nv Oi Qh Qy) Fn(bR bU Ib Iu Ky Md Mi Mn Qv Tr) Ua(Co Dg Em Iu Kl Ky Mf oH Pz Vo) Jd(Bb Dg Ks Ky Ma Mm Ok Pd Rh Vt) Mv(Ad Dg Kg Mf Mg Pf Rh Tr Tv) Qg(cS Ct dI Gd Ib Je Pk Qv Vt) oH(An bM bN cT Iv Jv Ky oK oN) bU(bV cT fP gP Ib Jc Tr Up) Ue(aD bO Ib Mf Mi Qw Qy) aA(bV bW cG cS dI iP oK) kS(cC dJ Hb Hx Ma Mf Us) Ky(aJ cT dA dI Im Rh) Pd(Ha Jk Jl Pg Po Qh) bV(BO bR cF Cu iP) Aw(Bo cE Cw Dg Tr) Ti(Db Ed Hx Jv Tz) Rh(hG Hx Mf Oe Oi) Ib(cB dJ gW Mm) Tr(dA Jl Qy Rf) Ks(Ih Oe Us Uv) Og(Mf Mi Pk Ud) aJ(aD dL Iv Tv) cT(bR cB cF dJ) gP(aR bM bO Pk) Gc(Hv Hx Ut) Gd(Dc Ug Ur) Iu(Oe Rf Tz) Jl(cE Jq Nm) Ok(Jg Lh Un) Up(aX dA iZ) Vt(Oc To Un) iJ(iO Mf Th) hG(bM cB iP) Ct(Kg Pk) Ef(Cu Ma) Mm(cN Qy) Mn(Im Tz) Je(bR cF) Oi(Mi Ud) BbDk IvOe JgcE SsKl QyKg UviP PkaX bNiZ dAdE} aA{kS(As Ax aY bW cJ cO Cs Cu Cv Cw dN Et Fa Fn gW hC iP Kd Ke Kk Kn Kr Ld Li Lx Md Mp Oh oK Om Ow Pd Pf Ue Ut) gL(Ij In Jn Jo Jq Jr Js Jt Kg Kn Lw Mq Mr Mz Nb Ny Om Pb Pe Pg Pi Qa Ra Rj Uc Ud Up Us Uv Vp) aN(aL aY cW cZ dG dL Ed Fa Fn Iq Is It Jp Jt Kd Li No Nr Oh Ok Pd Pf Qb Tr Ti) cO(aL bE bQ cQ Cu dG dL fP Kj Kp Kx Ld Ra Rj Tr Tv Ud Up Us Vp Vs Vt Ti) Fb(Ad aK aQ aU Ax bI Bn bU cC cJ Cv dK Kg Kx Md Mt Ok Pg Pi Uv) Bo(Dr Fy Gd In Ji Js Jt Kg Kn Md Mj Mr Mz Nm Nr Nx Pg Pi Qa) cS(bG cI cQ CV dG dH dL Fn hB Jo Kr Kz Li Mn Mp Oh oN Vt) bV(dG dH Fn iA Jo Kd Kz Li Mp Nm Oh oN Tn Tt Tv Uc Ue Vt) bW(aJ Et Fa It Jq Kd Kr Lj Nr On Pd Pi Qe qW rB Tv Uc) Oy(Ad As bI Dc Dd Fa Kd Kf Pk rB Rm Uc) aX(Ap bG bL cG cI cQ Cu iA Jp Ke Kz oN) jP(aZ cQ dR iO jG lL Lv Mf Ms Ng Nm) aK(bL Fa Io Iu Mt Nr On Pd Qa Tv) aU(Iu Jt Kd Mp Nr Oh On Pd Ue Uo) cC(Ez Fa Kx Mn Mt Nr Ny Pd Tr Th) jG(aZ Iv Jt lL Lv Nm Nx qU rB) oN(Af aQ fP Hx Jy Kd oH Pk Rh) Up(dF Hw iA Kj Ph Tt Un Tj) cE(Ba bE cI cR Cv dM Fn Kd) dJ(Kl Mp Nr Ny Pf Tr Tv Uh) rZ(Ih Ip It Jt Lv Mf Nt Ok) Cu(Aw aY Cp Dc Fy Ik Uu) Mn(bI cB cW dG dK dL Tv) Ma(aD aM dG dK dL nR) Mt(cB cJ dH Ji Mq Nw) lo(aD aM bB cQ cW cZ) qU(Et Iu Jn lL Lv Mf) As(Ap aZ Cp iA Jp) Ed(aG Bc Cv Kg Rh) Tj(Ap bU Cx Em Tr) Kl(aD aM Jd Ml Oi) aQ(aP iP Mf Tv Uv) dL(aJ An bQ bX oH) rB(Hq Iv kQ lL Lv) Tr(aD cJ Cw Kd) Ji(Jr Ml Ny Qa) dH(aH aL cJ dI) dK(Iu Iv Qa Qe) gW(aP Mm oK Uv) iA(Af Fn Hx Kd) oH(cP cW dN oK) Ct(Em Gc Gd) Jg(Lh Mg Pg) Kq(fP Ib oK) Nw(Ml Pg Po) On(aZ Et Oh) aG(Iq Ir Is) dG(aJ aP fR) iJ(Iu Iv Ky) Ap(bI Dd) Cp(Cq Dd) Ti(bZ Hx) Fn(cG dF) Nu(hW jI) Mm(fP Uv) Tv(aV bO) Qe(aZ nR) Qg(Iq It) Jy(cB Jo) Ok(jK nR) Uh(aD Ml) aY(bG cI) bU(bS Nr) bX(cB eM) cJ(iC pF) dI(Mp Pd) mZ(Ng nN) qZ(Iu Js) AdAw AnFa CvaZ EzHb LzUc MgJk UebO QdfP JdKe JtjK KroK OgkN UfbI PkcG aSeM bGcZ bMqW bPgC dRiP nDoP} Fn{My(Af Ap bU cC cF cJ Cu Ii Iu Js Kj Kr Ky Mf Mn Nl Ok Om Tr Tv Uc Vo Vt) aP(An aZ bF bO bU cE cF cT Cu Cv CW dE dF iP Jo Kd Kr Md Mp oN Tv Uv) Cp(Af Ap Bb cJ CO Cu Ii Jq Kj Ko Ks Ma Mm Mn Ng Pf Pz Tr Uc Vo) Mv(Ad Af aZ Bb bU cF cJ Dd Jq Kg Ko Ks Mg Ml Ny Pi Pz Tr Uh) Pd(aJ aO aZ cB cN cT dE dK Ez fP Fr Ib Im kS Lh Mf Qt Qv Wm) aJ(aD bW cB cJ Cu Cv Cw Dg Et Fb iP Iu Jo Ky Mf Mm Qe Ue) Nq(cJ Co Dd Hb Iu Ke Kf Kj Ky Mt Ng Nl Nm On Pk Qg Vt) Hx(Bb cO Cu Iu Jq Kg Ko Kr kS Md Mg Mm Mn Pk Uh Vo Tj) Jd(Ad Bb Cv Cw Dl Hb Jq Kr Ks Mm Mn Nm Ok Pz Qg Vt) Uh(An BA bV cT Iz Ji Jl Jp Mu Nn Nv Nw Po Tv Un) Ba(Ad Bb bU Jo Kg Kl Ky Mg Mn Pk Pz Qm Ue Vo) Kr(aZ bU cB dE dM Dp Iu Kg Mf Na Oe Pk Qv Rh) bA(aZ bU cB cE cJ Cu Cw Dg Mf Mn Pf Tr Tv Vo) bV(Bb Bo bU cB Cu cV dE Dg Jo Kg Mf Mm Qg Ue) Nn(Bb Cw Dg Jq Kg Ko Ks Mf Mg Mm Mn Nm Tr) Mu(cO Cu Ir Jq Ks Ky Mg Ny Pi Pz Tr Ue) Mx(cO Iu Kg Mf Mm Mn Nm Ok Pk Qv Rh Vt) Et(cN dE Ez Fr Ib Im Mf Nv Qy Rf Ua) Ky(Dp Ez fP Iu iZ Kg kS Nl Qv Qy Vt) Jo(aZ cB cS cT Ez Ib Im Lh Nl Ti) Ks(Hv Im Iu Jl Na Oe Oi Po Qy Uv) Mg(cT Ef Ez Iz Mf Oe Oi Pk Ti) Dg(Fr Jp Li Oe Pk Po Qy Ua) Tv(bU cN dK dM Im Jq Nm Ua) Jl(iA Jq Kl Ko Mm Mn Nm Pz) Kg(aZ cB Ct Ez Iz Oe Pk Po) cT(bU cB cE cF cJ Cw Jq Ma) Ue(cB cO Ez Ib kS Qw Qy) Iu(iA iZ OE Qg Rf) Rh(An hG Kd Nl Oe Oi) Pk(cS gP iA kS Nm Tr) Mf(aZ cO hG iZ kS) Ua(Cw Kl Ng Pz Vo) Iz(Cw Kl Nm Pz Vo) Jg(Ad Bb Cw Ok Pz) Nb(Ko Md Mm Tj) Un(Jt Nm Ok Vt) An(Jq Ko Nm) Tr(Ez Mn Qv) cN(bW cJ Ko) cO(aX dA iZ) dM(aZ Cu iP) Bo(Gd iZ) Mm(Ne Oi) Qy(Mn Nm) bN(hG iP) cB(hG oE) kS(Hb Ma) CoHc CuFr EzcC HvJq aXcJ dAdE} Ue{Mx(Al As Ax aZ bM cB cJ Cu Fa Lz Md Mf Mn Nk Oh Pd Pf Pg Pi Pk Rg Rm Tr Ua Vt Tj) Cp(Ad As Bb cB cE Co Ii In Iv Jt Kn Lx Lz Ma Md Mt Nk Nm Ok Po Rh Rm Tv Uc) Ky(aJ aZ bA cT Ez fP Ib Im Iu iZ Je Jg Kd Kr Mf Ni Nk Nl Nn Qw Qy Un Uu Ti) Iz(Ad Aj Al aQ aZ bO dE Fa iA Jj Jq Kg Ko Kr Ks Mg Mm Nk Nl Nm Ok Pg Vo) Kd(aJ Ao aP aZ Ba Ez Iu Jd Jg Mf Mu Mw Nb Nl Nn Oe Oi Qt Ua Un Tj) Tj(Ao Fy Hx Ik Im Jl Lh Mr Mu Mw Nb Nl Oe Oi Po Ua Us Uu) Jd(Ax cJ Cu Dg Iu Jo Jq Kg Ks Ld Ma Mf Mm My Nl Nm Pd Ti) Nq(As aZ bM cE dE dL Em Iu Jq Kg Ks Ma Nk Pf Pg Qg Ti) Mv(aQ As aZ Co dE Et Fa gW Kr Ks Lz Mf Ml Nl Om Pg) Pd(Ao dM Fr Ha Je Jg Jl Mr Nn Pe Pg Po Rf Tz Un Us) Kr(dM Ik Je Jl My Na Nl Nn No Oe Oi Pk Ua Un Us) My(An As bM bU cF dH Ib Iu Mf Ne Nk Qy Um) Pk(aJ aP aX aZ cB cO Ez Im kS Mf Qw Rf Us) Ba(aZ Bo cB cE Cw Et Kl Ma Mn Na Nl Oi) cJ(aJ Aw bA cS cT Ib Je Lh Mu Mw Ua Un) cO(Aw aX bA cT dA EF Fr Jg Mr Qt Un) Et(An Ao Aw Ib Ik Je Jg Ji Jl Nn) Mu(Cu Ex Iu Iv Ko Kq Pi Pz Tv Vu) Mf(Ik Je kS Oi Rf Ua Un Us Uv) Mm(Ao Ib Ik Ji Jl Lh Nn Oi Ua) Iu(Ih Im Nl Nn Oe Qg Qt Qy Ua) aP(aD aR aZ Bo cB cW dE dN Nl) Je(aZ Ez Ib Ks Nl Pg Qg Qy) Mn(Ao Ef Jg Jl Po Qt Uu) Ko(Jg Jl Lh Nn No Tz Ua) Cu(Ef Fr Hx Jg Us Uv) Mr(Fa Jo Lz Pf Qy) Ua(Cw Jj Nk Nl Pz) Us(iA Jo Kg kS Nl) aJ(aD Bo cB dL kS) bA(aZ cB cE Ed Ma) Em(Ql Qt Ri Tz) Un(As bM Nm Vt) Ao(Dd Kg Ks) Gd(Lh Ou Uv) Nn(Cw Jo Nl) Hx(iA iP kS) Ik(Jo Kg Nk) Qg(Al bV Um) bM(dM gW iZ) cT(cB cF Up) Ez(As cC) Jg(Dd Uh) Jl(Fa iA) aD(An aZ) kS(cF Hc) DgLh DrVs EdTi PoOh MlLd NhNl IbiO PzUu JiUh JoUv RhOi aXdE bVcV cBoE cEdM dHfR} aP{An(bG bL bN bO cE cS CW cZ Fa Fb Iu Jo Jt Kd Ma Mm Mn Mp Mt Oh Ok oN Pd Pf Qa Tr) Ky(aD aX aZ bA bV cB cE dF dN fP Il Iu Jy Kg Ks Md Mp oN Pf Uv Vt) Fb(aD aM aR aX aZ bA bF bL bU bV cB cS cT Md Mp Pf Pg Qg Uh) Kd(aZ cB cE Cu CW Dg dN Jo Kr Ks Mf Mp oK Tv Uh Uv) cT(bB bG bO cJ CW dF Dg Et Mp On Pd Pf Pk Qe Uf Uh) Kr(aR aZ bR bU cE cG Cv Cw dE dF Et iP oK oN Pd Up) Ko(aD aM aR bL bV cB cE cL dF dG Je Jo Mv Mx Uv) Cp(aH Al As Bb bQ cE Cq Cu Dd dF dH Dk Kq On) bN(Al Ap bA bL cE Cu Cv Cw DG Jo Mp Tr Uh) Pd(aD Aw aZ Ba bO bV cB Ez Ik Mr Mv oK) cJ(Aw bA bS cK dH Io Jr Ma Md Mf Mn Uv) cS(aH aM bB bG bO cG cK CW Dg Et Tr) dL(bS cK Cv dH Jo Kg Ks Mf Mg Mp Rh Uh) Bo(iA iJ Il Iu Md Mg Ok Pg Qe Uv Ti) Tv(bU Fa iJ Mp Mr Nj Nm Pk Qe Qg Tr) aZ(jG jP Jt Ks Mp Ok ON Qd Qc) bA(aM aY bG cW Et Mp Qd Qe Uf) dG(Al aM Aw Ba bG cO Cv Iu Je) Kq(aX bV cB Im Io Jg Mu Mv) Pk(Ba Dg dN iP Iv Mf Mp Qg) Et(Aa Aw aX bV Mx oK oN) Tr(cG dF dI Io Kp Mn Up) bW(Cv dH iC kS Mm oK Ti) Mp(aM Ba bO dE Md Mv) Dg(aR Ez Ik My Uu) Mf(Cu iJ iP oN Uh) aM(cI dH Kl Ma Uh) cW(aN bS cI iA Ma) kS(bM Hb Lx oN Qe) aC(aX aY bB bG) bL(aX bV cE Ma) dE(Jt Ma Mm Qe) iP(Ed Hx Tn Ut) Aw(bQ cE Cw) Ti(cO dF dH) Iu(hB oN Qg) Jy(cB dF oK) bG(bV cI eM) bM(iJ Kg Rh) fP(bQ cO iC) jP(aD iC nW) Cw(aX Jg) Mm(Ik Nd) Iz(Kl On) Qe(Jr Up) Uh(aD dN) bV(cK hB) cB(cK Ks) oK(bH Cv) oN(Hx Ow) BaUf CuUa EzcC IvQg JgOn JoUp KlUu aNcZ aRiA aXcG bOcE cLiC dHeM iOjG} Mv{Jo(cO Fr Ik Il Jd Jg Ji Jl Jq jY Kd Lh Lv Lw Mi Mk Mr Mu Mx Nr Nu Nx On Pa Pe Qg Th) Mg(cB Cu Il In Is Jd Je Ji Jl Kd kK kS Kz Lj Lv Mf Mi Mk Mu Nk Nn Nw Om Pi Pk Tr) Mn(aC Ad aJ aN aZ bU cB Hv iA iJ Il In Jd Je Jm Kd kK Kr Ky Mf Mu nI Nk Nn Pd Pk) Jt(An Fr Il Jl Lh Lv Lw Mf Mi Mk Ml Mr Mu nK Nr Oh Om Pa Pe Qa) cB(Ad Af Bb cJ Cu Cw Dg Et Fb iJ Kd Kg Ko Kq Kr Ks Ma oE Pd) Nr(Hv Il Ir Iu Ji Jl kG Mf Mr Mu Mx Nl Nn Nu Nw Oh Pf) Pd(cJ dI Ha Is Je Ji kS Lv Lx Mz oH Ok Om On Pz Qg Tr) Pk(aK aU aX bJ bV cJ Co cS Dg Et iA iP Kd Ma Mm oH Rh) cO(Af BA Bb cF cJ cT Et iJ Il Kg Kr kS Mx Qg) Ng(Gd Ik Il In Jl Kr Lv Mk Mr Mu Nk Ok On) Ma(An aZ Ba cS Il Jl lY Nk Nn Oh Vo) Nm(Il Is Ji Jl kF Mf Mx Nk Nn) Cu(An bV Hx Kd Mf Mx Nh Qv) Iu(Ap aZ Co jG Kd Kr Mx Pa)

Figure 13 Continued

Dg(An bV cS Kd Kz Mx Nh) iA(aJ aX bR bU gW Hx oH) Ko(An aZ Im Jj Kd Kg) Ky(Ad Co Il Kg oH Vo) Ny(Co Ir Ji mW Nn Tr) Tv(bU cF cJ Mm Mx) Pz(Im jH kK Lv nI) Cw(bV cS Kd Ks) Tr(bU Jq Mx oH) Il(Jl Mk Mr Pa) Em(Ap Om Uh) Jj(Jl Mu On) Jm(Ir Is Qb) Js(Ji No On) nI(Om On Oy) jP(Hq Pg rZ) oH(bW Mf Mp) Ad(An Jd) Co(An Oi) Et(fR Jd) Kr(Af bR) Of(jY lL) Vo(Kd Mf) aX(cE cJ) gW(iP Ks) BoKg GdRb MmPi MzIn NeNk HbkS IrkF JlPf KqdM PgkO aZcC cGdI cJcR mTmW qUrX} Gd{Et(Cp Cu Dc Dg Dl Fy Ha Jd Kl Nh No Nt Oa Of Ok Om Pf Pz Qz Ss Uc Uv) Hb(Dc Dk Dl Fb Fw Fy Gl Im Ji Kl Mx No Nw Pe Uv Vu Vv) Vt(Cu Dk Em Fb Fw Im Iu Jg Jk Lx Mx Pg Pz Qb Ql Qz Un) Mf(Ba Dc Fb Fp Hw Hx Il Jg Jk Lh Ms Mx Nh Nt Ug Vu) Pd(Ba De Fr Gl Ha Jg Kl Lh Nn On Oy Qt Tz Uv Vs) Mw(Il Jd Ke Ko Lu Ma Oa Qv Rh Uc) Ef(Ad Cs Gc It Kj Ma Nm Rc Uc) Qt(Ap Cw Dg Jf Kc Kd Oa Rh Ur) Bo(Il My Nn Po Ql Qz Ss Vp) Ib(Cp Em Mq Oa Om Qg Rb Ug) Jl(Fa Ir Ma Mt Oy Qa Qe Qy) Uh(Ha Je Jg Jk Jp Nt Ou Qy) Uu(Ad Al Ar Iq It Iu Jt Nm) Po(Ct Em It Jy Kc Ko Of) Jf(Ba Bg Dc Og Ss Tz Vu) Qw(Aj Dl Fy Jp Lh On Qz) Qg(Ct Il Mk Nv Of Qz Tz) Ke(Ba Cp Dc Hw Is Jg Of) Cw(Cu Gl Kl Li Nn Ou) Qv(Ao Ba Ez Hw Je Vp) Kc(Ao Ba Ez Gl Hw Ug) Rh(Em Ez Fb Ha Oy Qy) Ri(Em Jy Nq Of Rb Vu) Nv(It Ko Mt Nc Pg Um) Ap(Ba Ik Lh Nn On) Mk(As Iz Kd Mx My) Il(Bg Nf Og Oy Ss) Kr(As Ha Lh Ou Vp) Ik(Dg Jt Mg Nm) Qy(Ar Jd Ub Uc) Og(Nu Oa Ql Ub) Ug(Fb Ip Nu Qz) Vp(Em Hx Jy Ra) Ct(Mg Mx My) Nf(Hf Ky Nt) Iz(It Mg Rc) Kd(Ao Hw Ur) Ko(Li Nn On) Dc(Jt Ur) Dg(Li On) Em(Fr Qz) Fb(Ul Um) Ha(Ky Nm) Ip(Jk Of) Jg(Bb Bc) AjWm AsHx BaOr BgFp CqKy DkGc DlJt TjHw FrMa GnUr LuIs MyJk UbOy UcPj RaJr QzJy LiUm OnUn} aJ{Pk(aD bV cB cJ cT Cu cW fP Io iP Iu Kd Kq kS Mn Mp Pd Tr) bM(bG bL bX cS dE Et fP iA jI jP Ky Mn Mp Ny Pd Uv) bV(An bG bL bO bW cK Dg dH Et Ko Ma nW Qd Qe Tv) Tv(aD Af bN bO cF cG Cv cW Jq Kr Pf Qe Ul) Et(An Ao Bo Cp dE Jd Jg Ji Lh Mr My Pj) cS(An bG bN bO cK Cu Cw dH dL Fb Ko Tr) kS(bL cJ dH dL dN Ed Kd Kr Lx Mf Mp) Th(Af cG cL iJ Jq Mn Mp Mq Ny On) cO(aD Ba cI cZ Ef Ez Jy Ky Ma Qg) An(aZ bN cE Dg dL Iu Qa Qd Qe) Up(Jq Kd Kg Mm On Pd Pf Qd Uh) Cp(Ad Bb cE cJ Cu Cw dH Dl) Kq(aD Ba cF cT dL Md Mr) dG(aX bG bL cI Ez Fb Ky) dH(aM Aw aX cW dI Ez Mx) iA(aD Cv fP Hx Mf Nq Ow) Bo(Io Jo Kd Ks Qa Ti) Tr(aD bR cF cJ Kd Mn) Ko(cB Ez Iz Jg Nq Uu) Kr(bR bW cE cF iP Mm) dL(Al bG bS cE Ic Mr) Ed(bJ cE Cv Jo Ks) bW(cW cZ fP Io oH) cJ(bA cT Kd Mn Mp) Ma(aD BA Kd) bN(bL Cu cZ jP) Iu(cV Ky Uh) Qd(aZ dE My) bG(bL bO cT) cI(aR bL eM) Dg(Iz Jg) Kd(Cu Mm) bQ(cT fP) jP(aD aZ) AfAw ExJe GcbR MnMy MrQe IvQg PzUu aCaX hXiP} Jo{Tr(Bg Ez Fb Hx Ji Jp Kf Kl Nb No Nv Oi Pe Qa Qc Rf Rm St Tt Uc Uv) Ti(Ap Dd Fy Is Jg Jl Jp Jt Lx Ms Nv Oi Pj Qa Qz Rm Un Uu Uv) Iz(Ad As Bb cO Dg Et Kl Kr Mg Mm Mr My Ng Qg Vo) Ct(An Cp Ih Ik Jd Jg Jr Mx My Nh Pk Qg) Jy(Ao dM Ib Ik Jd Jl Li Mu Nn Po Qy Ua) Is(Fr Jg Jk Jm Ky Mu Nk Nn Nt Ok On) Kd(Ao Ha Hv Hx Ih Ik Jd Nn Pg Po Qy) Cp(Af Bb bV cO cS Ik Kr Mn Qg) Ky(Ao Aw bV fP Ha Li Mu Pg To) Pk(Ao cT Ha Li Mu My Nn Po Qy) Qg(bV cT Jd Nn Nq Oi Uo) Us(Aw Ik Jd Mu Nn Pg Po) Ao(Et Hb Ik Kr Nh Up) Ko(Dk Ih Jd Jl No Tz) Em(Fr Gl Ib Ik) Nn(Ik Kr Me Nk) Nk(Fr Mu Qb) Qy(Ih Iu Jr) An(bV Nq) Po(Ed Kr) Th(Fp Qw) Mr(Tt Ua) Ik(Om oP) Pz(Fr Jg) Jd(Ha Kr) Up(cT dM) AwNh BofR DgJg TjHx EtUn MabA MuIr JjJk JlcO LhUh NxoP bVcV} Nq{Tv(bF cB cE Ch Cw Im Kd Ko Ky Mr Mu Mx Nm Pj Pk Rh Vo) Kr(bR bU cB cE cF Ch Co Db iJ Jq Kd Kg Mf Ng Pf Rh Vo) Kd(Ap cO Dl Hb Kg Kl Kq Ks Mg Mn Ng Ok Rh Uc Uf) Uh(Ad Bb Cu Iu Jj Kg Kj Kl Mf Mg Mm Mn Mx Uc Uo) iA(aX cN cS dK Jl Jy Kg kS Mn oE Rh Th) Ko(Ad An cE cO Em iZ Nn Pf Qv Rh Uc) Ks(Ad Bb Cu Iu Ma Mf Mg Mm Mn Pf Pz) Dg(Em Ez Jd Jg Jy Ky My Nd Qg Ti) Ti(Bo Ch Co Ky Ma Ow Pd Qw) Qg(cO Cu Ma Mn Pd Pz Uc) Tr(bO bR cE cZ Hb Rg) Kg(Bb Bo Cu Jy Ma Mn) Pk(Ad cO Mg Ok Pz Rh) Kq(cT Im Iu Mf Mx) Th(Dc Il Om Pz) Ez(Cu Mm Pd Pz) Kl(Ba Iu Jg Mf) Bb(Em Jy Nh) Et(Aw Ba cO) Ma(BA Jd) Ok(An Jy Un) Bo(Dr Mn) Mm(Jy Uc) AdNd AfTt AnJt CwEm NrkO MfiJ IuVt RhPd} Et{Jg(aN Ao bA Bg bV CO Cq cS Cu Dk Jd Ks Ld Pi Qg Qx Tv Um Un Ur Vp Vs) Cp(aN bV cO cS Cu Dc dK Dp Gn Ii In Ir Jd Jq Kd Kr Md Mg Ml Pg Rf Tj) An(Ao bV fP Ik Is Iz Ji Jl Li Mx Nn Nv Oi Po Un) Jd(Ba bV dM Ez Hx Im Ji Kd Kr Mf Mn Nn Qg To Tr) Un(As Ba Dp Hx Je Kd Kg Kr Ml Nn Pd Pk To Vt) Mx(aX aZ cO cT Ez fP fR Ib Pk Qy) Ba(Cu fR Ib My Na Nh Oi Pk) Lh(aZ dE dK Kg Kr oN Qv Tj) Iz(cB cO gW Iu Jj Mn My) bV(dE Ih Nh Nn Qg Rf Tz) fR(bA Ez Je Nb Qy Ua) Ji(Aw dM Em Nn oP) Pk(cT Im Li Nn St) My(Aw Gl Kd Kr) Ib(Gn Je Jr Ou) Jj(Is Jl Nn Nv) dM(Ao Ez Jr Nh) Em(As Nb Nu) Mu(Ex Is) Hx(hG kS) Nw(Js mZ) AsSs PoJe NnKr IsJm QtgW JpmZ UshG} Iu{Mu(cE cG Co cV dH Em iA Jl Jy Kd Ks Ky oE Pi Tr Tv) Qg(Ba Cp Dp hG Im Iz Jd Mf Mx My Nn oE Qy Ua Vt) Iz(Ad cE cJ cO Cu Kl Ks Mg oE) jG(Fr jP jY lL Lv Mf Mw Nj Oy) Ba(cE Kl Ks Ky Mn Nm Uh Vt) Cp(Af Bb cG Dg Jq Jt Ks Mn) Jl(cJ Dg In Kd Nn Ok On Pz) iA(bA bV dM iZ Jk Mw oE Ua) cJ(bA dM hG iZ Mw oE Po) Ky(Fr Mx My Nn nY oE) lL(Fr Hx Jj Jn Lv Mp) jP(iB Jh Lv Ms Oy) Ua(cO Cu iJ Pd) Tr(Fr Jd Lx Nn) Is(Jr Lx Ml Mr) Kr(Ih Jd Nn Oe) Ks(Ih Im Nv Oe) iZ(An bM bN cO) kF(Hu Hx Og Oz) oP(Ik Jn kC nI) Nm(Ez Rf Tz) Mw(cE cG cV) Mx(As cO cV) bA(cE cO Pk) qU(jH Mf Mp) oE(iJ Im Tz) Mr(Qa Qb) Hx(mM Wm) Jk(kO nI) Pd(Ha Qy) qZ(Lj rC) PoEm MfjY MkQb MprB NjmM ImKo JtOn OyjH bWhG cEcT} Tr{Dp(aX cB Fr Im Iz Jk Jl Jq Jr Mr Mu Nb Nk Oa Oe oH Oi Pk Po Qv Rf Ua Un) bV(Aw aZ BA bO bR cF cZ Ez fP iZ Jg kS Ky Mr Oe Qg) Mx(Ba bU dI Ez Ii In Kd Kg Mn Pd Pi Pk Uh Tj) Jd(Cv dA dM Ii Il Kr Mg Mn Nm Ny Ok Qg Uh) bU(Aw Ba Cp Ez Hv Ib Iz kS Lx My) dM(aD bO cB cS Il Mf Nj oN Up Tj) Pk(aX Ba Cp cT dI Mu My Rf) fR(aZ bL dH Hv Mh Nu Pd) Cp(Ii Iq Ir Jq Mg Pd) Nn(Jq Ks Mn Ny Pd) dA(An cO Ez Il Tj) Kg(Ao Dk Is Jm) Ks(Is Lx Qy Rf) bA(aK bI oH Up) Ti(Dk Jv Lh) cB(Aw Ib iZ) kS(Jg Ua Uu) Mn(Qh Qy) Jl(cO Jq) Rf(cS dI) iZ(bN Jv) BaCu BgGc LxKr MuIv UaNy HxoH IthG} Pz{Fr(Ik Is jG Ji Jj Jm lL Lv Mf Ml Mn mT Mu Nu Nw Ok Pd Qa Qc) Jg(Cw Il Ji Jj Jl Mf Mg Ml Mx My Ng Nk Nl Nu Oh Qa Qc Qd Uh) Nn(Il Im Is Ji Jl Jm Lv Ma Mf Mi Ml Mn Nk Nm Nw Ok Om On) Mu(In Jl Jm Lv Mg Mi Mk Mr Ng Nw Pd Qc Qd) Nv(Ik In Is Jj Jl Jm Lv Mf Mi Mn My nR Pd) Mx(Ba Is Jd Jp My Pc Qb Ua) Qb(Ik Jj Jm Jp Lv Nk Om) kF(Ih Ir Jk Mj nR Og Oy) Qa(Jj Jm Lv Nk Nw) Is(In Ij Mf Nk) Iz(iJ Kg Mg My) Nw(Ik In mZ Pd) kK(Jk Mk Ms) My(Mi Pk) Ji(Jk Lu) Jp(Lv mZ) oQ(Mj Nf) NtJj LxnR NgnK OemZ OyjH} Jt{Jg(Il Im Ir Ji Jj Jl Jq Mg Ml Mu No Nv Nw Oh Qc Qd qZ) Mx(An bV Cp Ir Jd Ji Jk Li Mf Mi Mu My Nv Oh Ok Pc) Nw(Fr Ik Im In Is Jk Jp Js kF Ml Mu Nk Nl nR Nu Oh) Nn(Ik Is Ji Jl Jm Lv Mf Mi Mk Mn My Nk Nl No Om) Fr(Im Is Ji Jj Jq Ma Mf Nk Nl Nu Ok Om Pd) Mu(Hx Ir Ji Jq Mf Nk Nv Oh Ok On Qa) Om(Ik Ir Jp Md My nK Nu Qa Qb Qc) Ok(Im Is Jp My Qa Qb Qc) Is(In Ir Jm Nu On) Jp(Ik Ji My Nt Nu) On(Ir Pg Qa Qc) My(Ji Mi Pk) Em(Il Qt) Nk(Nv Qb) nK(Mw oP) CpPd NuQb MfJi NgmZ JjLh JlcO} Pk{Ba(aX bU bV cE cJ cS gP iA Ko Mm Nm Pd) bA(bV cE cF cJ cS Fb gW iP Kq oH Pe) cT(cC cJ gP Jq Kd Ko Kr Ma Mf Pf Uv) bV(Bo bW cB cG Dg dH Fb iJ Rf) Mm(aX cS iZ Jd Jl Mu Mx My) Pd(dA fR Ha Jd Jg Li Nn Po) Mu(Co Dk Md Mr Nv Ut Tj) Rh(iA iJ Jd Kd Mx My nY) Kr(cB Cp gP Mx My Nn) Im(aZ cB cO iA iP) My(iA Js Mg Nm) Ko(cN iZ Jl Mx) cB(Cp Fw Ha Jr) cC(Ez Fw gP Rf) cO(aX Cp cS Fw) cJ(aX dM Je) fR(bL cR Pj) iA(hB iZ Jl) Iv(iZ nY) Jd(Bb Ma) DgJg EzdJ NmHx MfbU MxPj RfcS} Cp{Pd(Ad Bb bU cB cS Cw dA Dg dI dM Ha Hb Ik Io Jq Kd Ko Kr Ks Ky Ma Mg Nh Qv) Dg(aX BN Cq cS Cw Iq Ir Iv Kd Kr Md) Cw(Af aZ cZ Gn Kd Kr Mf Mn Om) Mg(Ct Iq Iv Jq Kd Kr Mn Tv Ti) cO(As cN cZ Dd dI dM Ko Mf Om) Ad(aX dM fR Gn Ma Mf Mn Tj) Ko(aZ Dp Kg Kx Mf Mx) As(Al Ap aZ bN Dd) Om(Ba Kd Kr Mf Nm) aX(aC cE Co Gc) aZ(Af Al bN Dd) Kr(cF Jq Ky) cS(cG Co Gc) Dd(Ap cE) cJ(bV dI) AlbN ExPj GccZ MaoF MfMn KqdM bAcE} bV{Pd(Aw bO dE Ih Ik Je Jr Kd Mr Rf) Qg(Al Cu Je Kd Ky Kz Mf Mm Qc) cE(Aw dM Ef Il Im Iq Kg Kr Mx) cJ(cK hG Il Im kR Ma Mf Mu Rf) cO(Aw aX Ba cN dM Ef My Rh) Dg(Ez Ih Im Iz Jd Jg Ky) Mx(Bb bW Fb Ma Qd Qe Uf) Hx(hB iJ iP oN Uh) Cu(Im Jr Ky Tz) Ma(An bA Jd kS) Kq(An Im Mu Rf) cG(Je Kg My Ou) Bo(Il Kg Mg) Ky(cV Il oK) iA(dM iZ Jg) iJ(aE Qx Rh) Gc(aZ bX) bN(cI iZ) AnMf CwJg EzKl ExJr KoRf KrcF LhUh OwoE aCcZ bQkS bSeM bWoH cKdM} Em{Nm(Ao De Ha Hx Ii Is Jp Li Lu Nh Ny Pe Pf Qz Rf Ri Sr Ut) Bb(Fr Il Iz Lx Mw My Nb Po Qy) Mu(Dg Ok Om On Qa Rm Ua Uh Wm) As(Fr Ha Jf Kg Mg Nb Oe) Ap(Fb Fr Iz Jl Oe Po) Cw(Jg Lh Li Oe Uu) Ua(Dc Jm Kc Mx Pd) Kg(Ct Ib Iz Of Po) Hc(Kc Kf Ug Uh) Qy(Ad Co Dg Ub) Oe(Dg Kc

Figure 13 Continued

Kj Ug) Po(Ad Ke Pd) Jl(Dg Mk Rm) Nv(Kf Ok Uh) Uh(Li My) CtMg FbRc FrMz LuHx LxKf MwOm HbOu JkKj LhOk RiVt} Ko{lm(AN aZ bA cB cO cS cT Ez iO Iz Je Jg Kd Mf Ml Mu My) Mx(An cC cT Ez Hx Iz Jd Je Jg Kg Ml My Qv Qy) Ba(aZ bI cJ cO Cu gP Hx Jd My Qv Tj) iZ(cB cO cS hG Jg kS Ky Lh Uu) bA(aZ cJ cO Mf Pd Pf Uv Tj) Nn(An Kr Ks Mf Mg My) Mu(Kd My Ny Pg Qx Tj) Pd(Iz Jd Jl No Pe) No(cJ Kg Ks) Mg(Iz Jd Jg) Hx(iP Kg) Lh(cJ Kg) AaaX DpcT NuKr MdMw MfJd MybU UaJj JlcJ aZdM} Ti{Mg(Al Dk Fr Jp Lx Mx Ng Nw Oe Oi Rf Tz Uu) Nw(aN cJ Ed iA Ks Lx Pd Pf Qz Tj) Lh(cJ Co Ks Ky Ma Ny Pd Tn Tj) Hx(aN cJ dK Ez Jv Mf Mx Rf) An(aE dK Dp Ed Na Ny Qz) Cw(Ap Iz Jd Ji Jv Rf Un) Ky(Ao Ji Kn Mf Nn To Tz) Ks(Ih Jn Jp Nn Tz Uv) Mx(cJ Jv Pd Tv Ul) Tz(Ch Jq Kg Ny) Ed(Cs Kg Rf) Ib(Om Pd Ut) Jv(Na Pd) Rf(Pd Pi) AoKg DpTj EzPh NnOw NgIz ToNy TvIh iAoE} Ma{bA(cC cJ cO Ex Ez Fr iA Ik iP Jq Kd Kr Mu Pd Qt Qw Uv) Ba(aO bU bZ cJ cS Ez iA iJ Jq Kr Ld Qg Qw) kS(Aa Ao cC Fy Ih Jv Ky Oy Qh Qt Qw St Us) Mu(Gn Is Kq Mi Nn Ok On) Fr(Cv Jj jP Kd Mi Nm) Nn(Jj Kr Mf Mm Nk) cT(An Aw bZ Mx) fR(bW cJ cK Ik) oP(nI Nx Og) oF(dM Jk Ua) Mw(nK nR) Ib(bU hB) Iz(cB iA) Jd(Kd Kr) Jj(Jk Nv) Jl(cO iA) bZ(iZ oE) MsmM IvkF NwkN bMiZ} Jj{Mf(Is Iv Jk lL Nl Nn Nt Nv Nx Qb) Ml(Ir Is Jg Nn Nt Qa Qb Qc) Mn(Fr Is Mu My Nv Qb Qc Ua) Ik(Fr Hv Im Is Mk Oh On Qb) Nl(Fr Jk My Nc Ne Nn Qc) Jk(Ir Is Mx Nn Nx Pd) jG(Hx jF jH Mp Oy) Nn(Js Me Mu Mx) Nk(Nc Ne Qb) Nm(Is Nv) Ms(qU qZ) Iz(Dg gW) CuUa FrjP MeHv MuPd IbgW JmjH NvNy} Kr{Jd(Bb cJ Cv Cw Jq Kd Kg Ky Mf Mg Mn Mx Na Nm Pd Qg Uh) Nn(Bb Cu Cw Jq Kg Ky Mf Mm Mn Mx Pd) cB(bA cN dM Iz Lh Oe) Mx(aZ bR bU Kd) Dg(Jg Lh Li) Mf(bR Hx oH) Up(bA cT dM) cF(bA Je My) Jg(Cw Uh) Ky(iZ Li) bM(gW iZ) cJ(bA Un) CuJl PoPd GcJn MuKq MyKs NgIz HxiJ bUdE cNcO} Gc{cK(Ao bI cN Co cP Dc eF fR GL) cP(Bb bI bP bX cI Di Fw) aZ(aX bA cI cN dM fR) Jn(Lw Md Pi Ra) cI(bI bR cN eF) Cq(Pi Ra Tv) Ct(Co Ef Gn) Fw(As bC bS) Vp(Id Lw Ra) bX(Co cS dN) De(Af Cx) bI(eF fR) bP(Ar Gl) bR(cS dN) cE(Ba cN) AdVs IdJr KdUt NyUp UhPe aCaX aYeF cFgL} Hx{iA(cB cH dK fP hB hG Il iZ Kg KS Mx oH Oy) kS(As bQ cC cJ iJ Kg Mf Ow Pd Uh) iP(hG Jq Kd Kg Md) qZ(Ir Lj Pd Pe Qd) iZ(bN dH Ky Ow) jP(iB jG Mw Nl) oH(bW cO Ky Qe) iJ(Ks Mf Th) Cu(Iz Ua) It(nI nK) Kd(Ks Mm) fP(cJ Ky) jG(jH jY) BoDr NrmZ MnMu bAoN} Dg{Jg(aK Ao As Bg cB cJ CO Cq cS Cu cZ dI Dk Ez Hr Hw Ik In Iv Jq Kg Ks Ld Ml Mr Mt Mw Nv Nx Ny Oi Pg Uc Ur Vp) Iz(aX Kd Mf Mg My Pd Qv) Mx(Ap Ba cS Kd Nn) Gn(Ao Cu Ib Ou) My(Gl Ik Nn) Ba(Jd Qg) ExHc NhNl JlcO LhcB} dM{iA(aZ bN cH cJ Ez Iz Jl Jv kQ Qt Qx Uu) cJ(aC bN bX Jr Kd kS) cO(cT cZ fP Kd My) Kq(An aZ Iz Jr) aC(aX bE bG cE) Mm(Kd Kp Tv) bN(bG cZ fP) cE(bA cS Gl) bW(fP pF) cC(eM Ez) cS(bL cK) dH(Im Nh) iJ(bM iO) oN(aO kS) CuIz bGjP bQfP bXeM} Mf{oH(An aO BA Kd Ow Us) iJ(BA Ez Gl My Un) lL(Fr jG jK Jn jY Nj) jP(iB jY Mp Mu Om) Jd(Bb Kd Mn Nm) Ba(cO iA kS) bA(cO iA kS) Nn(Mn Nm) Mu(Kq Mn) cB(hG oE) cC(Ez kS) fP(An Ky) jG(Jn jY) CuUa MxcO LhiA OgoP bNiZ} Pd{Iz(cB Kl kS Mn Ng Nm Vo) Ik(Ba cJ Nw Om On) Mu(Is Mz Ok Om) Nl(Fr Nw Om) Jd(Ha My Po) cO(cN Pg Po) kS(Ba Pg Ua) Ez(cC dJ) Mr(Om Ua) Nw(Jk Ne) dA(Nh Up) qZ(Hr Ms) AnfP BaCu EdbA HacJ MpjP MyQy NgmZ JliA LhUh OgoP bWfR nKkN} mZ{Ng(Io Ir Jm Mu nN) Nv(Lj Ny Pg Qa) Nw(Jl mM Nr Po) nR(iC In jH Nm) Mu(Mj Ny Pg) iC(hA nB oP) Nr(Hu Om) Mn(Fr On) Ms(Ir nK) Mw(Mj Ny) Is(Jn Js) mM(hA jH) NmlY NoLx NdJs ImY IvnK nOjH mIqT mPnB nLrX jDjG jQjR} jP{iB(aQ aZ iP Mp Ms Nj) jG(aF Fr jH jO Mp oF) Fr(jH jY Lv Ms) oF(aZ dR jR oH) Mp(Nj Nl qU) aF(bJ dE oE) lL(iC Jn Mw) Ms(jH rY) LvjY MgNg OkOm aDiZ aEjT aQaV cJjH cLdG dRhX} cO{Jl(Ad Ba Bb cJ cS dA dJ Il Jq Kd Kq Mm Mn Uc) Mx(aX cS cT My) bA(aX Nh oH Qg) cN(Aw cS Jr) Iz(Kj oH) cT(Mn Qg) AdJg FrcS MkIm UaKs OefR aXdG bNiZ qWkS} iC{kS(bJ cE cJ cQ jD nY) oE(bC cE cQ cX iO oH) nR(jH jT jY lK rX) lL(jG jH kG qU) bN(aN nY oH) iO(cL iJ jT) bCoF cLhX cQjT jGjH qZqV rXoP} It{kN(Jn Jp kC mS Nv Nx Og Po) oP(Jn mH mM nN Nx) Jk(kF kK kO mH) mM(Ii Ms Pa) nK(Mw nH Qb) kF(Ii Jn Nx) kK(Nv Qb) DrIb IkoO OmmH} bA{oH(bM bW cJ Ky oN) Ky(aK fP iP) cE(aX bG cS) cJ(aX bG Mn) eM(bX cB cV) Cu(Ed Iz) Tv(bU cF) bQ(cS fP) ExJe MxKq VobI aCcZ bNfP kSoN} Mu{Tv(Ao Co Ex Kq Om Tj) Ex(bW cS Cv Je) Kq(An Kd Oi Un) Nr(Mr Nl Nn) Bo(Iq Iv) Nm(Is Ok) Nk(Nc Nl) Js(Ji Om) CwIv DrWm GnHb} Mx{Tv(cB Jq Js Ok Qy Ul) Nn(Js Nm Nr) Kd(Js Ks Pj) cJ(aX cS fP) Kq(aX cS) fP(iA Ky) BaOn ToOk IsJn IvoE IzKl QyUt QgRm JsOm} eM{bG(cM cS cT cY dF) dN(bL bS cB cK) aU(bE dD) aX(cR cV) bS(dF gL) cS(cP dH) aCcZ aRcM bBcY bCbX bNbP cDdD cTcV} kS{iZ(bN bQ bW hA oN) Ky(cC gP hG nY) qW(aM bW cE oK) Hb(Ao Ba cC) hA(iO oE) BaiJ CoHc OwcN UscC bMrB bQhG} jH{cQ(aZ cE cJ iA iO nW) jG(kK lL nR rB) nH(hA nT rX) cJ(aZ iO) nR(mM qU) NtJg hAoQ nNoP lXjR nBjL nWoE} Ba{Cu(Ha Kd Kg Ky Ld Mg Rh Uh) Ib(On Ut) Tv(cB cF) BoKs CoiJ MgKl MmOi MncJ VobI aCcZ cEcS} fR{Cw(Ib Je Oe Of Og Ou) bW(aX bC cS Oe Pj Qg) cJ(cK Hb Jc Oe) MmQm KygL PjaZ aHcK} Nm{Nn(Is Jm Ml Mn Ng Nl Nw) Is(Fr In Jg Jm Nk) Kd(Jd My) kK(Nt Nw) MmqZ MsmM OgoP} qW{aO(bH bM cE dE dF dI iP qU) aF(aR bF cG cL dF dH iP) oF(bH bM dI) bHbM} Iz{Mn(Ad cJ Co Kg Qg) Kg(Cu iA Kl Kq) cB(Ad Aj Bb Ng) Mg(iA Kl) CoVo CuMy} lL{nT(hV jK kG qU) iO(cE cG) jG(eD kG) rX(kG nR) MgNg NljY ParB nBjl nFnl nJjK hXkN} oE{qV(bW dL dN hB oN) jQ(bM bW hB nW) rB(aR bW kR) IbcB IvQg hBqX iOjM} Qe{kF(Lx Nv Nx Po) Nw(kK nR oP) nK(kN Nv oP) qZ(Hv rB) LxkK NvnI UpiZ} Ib{Mm(gW Im Je Kd Md Oe Rf) Gn(Ap Qg Wm) MyUt HbiA bWoH iJiO} iZ{bM(aU cB gP rB) bN(fP jG Kd) Up(dH Tv) cJ(cS fP) KycS UsdH bWgW} qZ{Hv(Js Ml Qd) Jg(Li Nr Qd) Lj(Ms rC) rB(Ip Lv) qU(rY rZ) QdrC} oP{Og(Ir Iv Mj Nf) Nw(Nr Po Qd) nK(Mn Ok Qd) PoIv NrLx IrNx} Gn{Bo(Hc Mw) Cw(Of Ou) Wm(Mw Vp) ApJl PoKe HbJe} kN{Nw(In Iv Jl Mj Pf) nK(Js Lj Pf Qd)} Mn{Nn(Mm Nk) Ua(Mm Qg) Uh(Jd Lh) cJ(cT Jr)} iA{Jl(bN cS Cv Iv Ks) KyfP OicH aFrB} Cu{Lh(Rh Ua Uh) Jl(Kd To) MyUa HcLd} Hc{Gz(As Ok Vt) Ex(Qv Ub) LdiJ} Nv{Nr(mT nK) Ny(nK nU) MjnJ QdnI} rB{aF(cV dE) LvMs NjjY aDiP bMqX} An{aC(aX cZ) TvbU bNfP cJcS} Dr{Bo(My Ou) MmMz MyRc OeUl} Mw{NrkF MjnJ TvbF QdnK NykK} Jk{nI(Mj Nf) IrkF IsJm NykK} cT{cE(Aw aX cS) KgUp cJcS} nU{qU(jT lK mH) IkIv nBjL} jG{aZ(iO oF) jY(Il Lv) nRjT} Nn{Ng(Ik Lu) ExJe NkNl} fP{Ky(Im Kg) OwcN bNcI} Ad{My(Ik Jd) AwaZ} Mm{NbTo KdOe KpgW} Ir{kF(Jn Nx) MsmM} aC{aXcJ bEcI cZdG} nR{PoIv JsNw mHjT} hX{bWoH dFdG iJiO} Aw{cS(cJ Cw)} Tv{ImcJ LhUh} Qg{AlUo JdJq} bN{ToiP cIgL} qU{MsIp nTnB} kK{NrNt JpOk} BbVqgP DpHvKd EzJecC ExJgPj FrNkNl MyKyiJ QdNwkF QvLhUh RhOwhG cQiOjT

Constrained panels with 2 analytes, where 1.0E-7 >= 'AUC p-value' > 0. Contains 43 panels of 94,547 total panels evaluated. : Gc(aA Ax Cs Ex Hc Ib Is Jd Je Jg Jl Li Lx Mu Mw Mx My Nb Nn Nv Nw Oe Of Oi On Ou Po Rb) aA(Af bN Ih Iu Js Jt Ko Mn Pz) Gd(Hc Hu Ua) TiPk ItmZ cNeM Constrained panels with 2 analytes, where 1.0E-6 >= 'AUC p-value' > 1.0E-7. Contains 27 panels of 94,547 total panels evaluated. : Gc(Cp Em Fr Fw Ha Ik Iz Jk Mk Mv Og Qg Qy Ri Tz Ua Wm) aA(eM In Kq Md) GdOe NqTr MmfR IumZ PzoP dMeM Constrained panels with 2 analytes, where 1.0E-5 >= 'AUC p-value' > 1.0E-6. Contains 74 panels of 94,547 total panels evaluated. : mZ(Iv jH Jk Js Lj lL Ma Mf Mk Nf Nj Qe) aA(cJ cO Cx Fn Kr Ks Ky Ok Pk Uh Uk) Gc(aJ Ao Mi Qt Qv Ur Uu Vp) aP(bL bQ bW cO cW dL Et Tr) Mv(Jj Jo Mg Ng Pz) aJ(cJ cO dG eM Kq) Gd(Po Qw Qy Rh) jP(cQ kS lL oE) Em(Mm Pj) Tr(dM Dp) Jt(Jg Nw) oE(jG qW) AdCp BaMa FnJo MuPz IkJj IuJl PkbA cOdM nUjH Constrained panels with 2 analytes, where 1.0E-4 >= 'AUC p-value' > 1.0E-5. Contains 181 panels of 94,547 total panels evaluated. : aA(aL Ap aY bG bL bQ cQ cS Cu Cv cW cZ dH dL Fa Fb jG Kd kN kS Tr Tv Ue) aP(aM An bA bG bN cI cZ DG dH Fb Fn Gc jP Ko Kq Ky Pd Tv Uk)

Figure 13 Continued

Gd(Ef Fr Ib Ik Il Iz Je Mu Mv My Tz Uu Vt) Mv(cO Il Jm jP Jt Ma Mn mZ Nm Nr Ue) Ue(Cp Fn Iz Je Mx My Nq Pk Uk) Jj(Is Iv Jk Mu Nl Nn Nt Nv Nx) aJ(An bG bL bM bN bW dL Ko Tv) IL(iC Iu jG Mf nB nJ nT nU qZ) Gc(Ba bX Co cS Ct dN Fp Gl) Cp(Cw Dd Dg Et Jo Pd) Nq(iA Ko Kr Ks Tv Uh) eM(aX bA cB cS cY cZ) mZ(iC Ir jG Ms Og) Fn(Kg Ks Pd Uk) Pz(Fr Jg Nn Nv) Jt(Fr Mu Nn On) bV(cO Pd Pk Tr) dM(bG bN cJ Et) iZ(bM bN jP Ko) Ti(An Ib) Et(fR Jd) Nm(Mu Nn) Iu(kF qZ) Jo(Is Iz) Ko(Im Mx) rB(aF oE) EmLu FrjP MabA MmIb QgUk JlcO RhPk iCkS jGjH

Constrained panels with 2 analytes, where 1.0E-3 >= 'AUC p-value' > 1.0E-4. Contains 504 panels of 94,547 total panels evaluated. : Jo(An Ao aP Aw bV Dc dM Fr Ha Ib Ip Ir Jd Jg Ji Kd Kr Mu Nn Nt Nw Ok Om On Pk Qb Qg Qh Qy Un Us Ti) aP(Al cE cS Cu Cv Fa iA Iu Kd Kg Kr Ks Ma Mf Mm Mp nW Oh oK oN Pf Pg Pk Ue Uh Uv) Uk(aJ Ba bU bV cJ cO dA dJ Et iA Kr kS Ky Mu Mv Mx My Nq Og Rh Ua Uh Ti) Ue(aJ aZ Ba bV cJ cO dE Ez Iu Jd Kd Kr kS Ky Mf Mu Nl Qt Qy Ua Us Tj) Cp(Af Al As aZ bN bV cE cO Cv cZ Dl Gd Iu Ko Ma Mg Mm Mn Nm Om Tr) Fn(aJ bV cO Dg Et Jq Kr Mf Mg Mn Mv Mx My Nm Nq Pk Qv Rh Tr Tv Uh) Jj(Fr Ir JG Ji Jm Jr Lh lL Me Mf Mx My Ne Nu Oh Ok Qa Qb Qc) aA(aM cE cI dG eF Em iP Ke Kg Kx lL mZ nN oH oN rB Uc Uv Vt Ti) Mv(Ad cE cJ Co Cu Cw Dg Kg Ko Mf Ml Mx nI Pd Pk Uc Uh Vo) aJ(aX bO cE cI cS cW cZ Et iP Iu jP Kr kS Ma Mn Pk Qd Tr) Gd(Ba Ct Dc Jl Mk Mw Nn Nv Qg Qz Ri Ug Vp) Mx(Bb cO Dg Jt Kr Ks Pj Pz Rm Tr Tv Uh Ti) Jd(Bb Hb Kg Ko Kr Ks Ma Mg Nm Pd Tr) bA(bN bQ bX cE cJ cO dM Gc Ko oH Tr) Mu(cO Cw Ko Kq Mf Mg Mn Ng Pd Tv) Jt(Is Ji Jp Nt Nu Nv Ok Om Qa Qb) bV(An bG bN dM Et iA Ky Ma Mm Qg) Gc(aX bC cK cN cP cT EF fR) Nq(Dg Hb Ke Kg Kl Kq Tt Uc Uf) Hx(iA iJ iP jG jP Kr Ks Me Ti) Pz(Is Ji Jl Jp kF Lh Nw Qa Qb) Mf(Hv Is jG kS Me Nn oH Qb) My(Ad cO Dg Ko Kr Ks Pk Uh) fR(aH cE cI cK cP cV Ma Tr) An(aX cS cZ Dd dM Et Nm) Fr(Dg Jm Ma Ng Nm Nr Pd) Kr(dM Dp Je Nn Nu Qv Qy) jG(iC iO Iu jP kS Lv rB) bN(Aw cI dA fP gL iC) qZ(Hv iC Lj Ms Qe rB) kS(bQ iZ Ky Ma Pk rB) Ba(cO Et Ko Mm Mn) Nn(Ks Ma Mm Mn Ng) dM(aX cI cS iA Ko) eM(bG bS bX cP cT) jH(cJ jP mM nR nT) Ti(Dp Ky Mg Na) Et(Aw Iz Ji Un) Nm(Em Is Ji On) It(kF kK kN oP) Iu(On oP Qg Wm) Pk(bU cB cT gP) jP(aZ Mp Nj oH) lL(eD Lv Ml qU) Dg(Iz Jg Lh) Tr(dA oH Rf) Pd(Ha Iz Nw) cN(bG cI cS) mZ(Mw Nd oP) Aw(aZ cO) Cu(Iz Ua) Mn(Om Qg) Nk(Nl Qb) Is(Jm Ng) qW(aO oF) kF(Ir Nf) AsEm GnIb MacT MzJs NjjY IvoP QbJm JknI JliA LhUh cOdG nUqU iCoE Constrained panels with 2 analytes, where 1.0E-2 >= 'AUC p-value' > 1.0E-3. Contains 1,013 panels of 94,547 total panels evaluated. : Jo(aJ BA cS CT Ef Ez Fy Hv Hx Ik Iv Jk Jl Jp Jq Lh Li Lv Lw Mi Mj Mk Mp Mr Mt Mx My Nb Ne Nk Nl No NR Nu Nv Nx Oh Pa Pc Pe Po Qa Qc Qv Ua) Mf(aJ An bA bV dM Ez Fr hG Ik iZ Jd jH Ji Jl jP Jr jY Ko Kr Li Lx My Nv Nw Nx Oh Om Pk Po Qa Qg qZ Uk Ti) Pz(Ba Cp Hx Ik Ir Iz Jd jY kK kN Li Lv Lw Lx Mi Mp Mt My nB No nR Nt Nu Oh Ok Om On oQ Pc Po Qc Qd Ua) Mv(Ap aZ Bb cB Cv Dd iA iJ In iP jH Ji Jl jY Kd Kj Kr Ks Ky lL Lv Mi Nk Nw oH Ok Qg Qv Tr Tv) Pd(aJ An Aw BA dA dM Ez Ib Is Je Jg Ji jY kS Nn Nv Ok Om On Pk Po Qb Qg Qh Qy Rf Ua Un) Pk(aX Ba cO cS Cv Et fP hG Hx iA iJ iZ Jd Kg Ko Kr Ks Mm Mu Mx Nm Nq oH Qg Qv Uk Vt) Jt(An Cp Em Hx Ib Ik Im Ir Jd Jl kF Lh Li Lv Lw Lx Mi Mt My No Oh oP Po Qc Qd Un) Iu(An BA cJ cT Fn fR hG iA IZ Jd jP kK Kr Ky Mk nI Nn nR nY oE Qy Rf Ua) Mu(aZ Bb cE cJ Co Dg Em Ex In Ji Jl Jm Kd Kr Ks Lv Mi Nk Nw Tr Uc Uh Ut) My(An Bb bU cJ Co Cu Cw iA iJ Il Jm Kd Kg Kj Me Mn Ng Nl Qg Tr Tv Uc Vt) Nn(Cw Dg Et Hb Ii Il In Jm Js Kg Ko Lu Lv Mg Ml Mx Nk Nr Nw Pj Tr Uh) Ks(aZ Ba bV CT dA Ez Ha Ih Im Iz Je Jl Kd Ml Na Oe Po Qg Qy Us Uv) Mn(An aP bA bV cT Ez Fr Is Iz Jd Jl Jp Nv On Po Qa Qb Qy Tr Ua Uk) Ko(An aZ bV cT Ez Fr hG Hx Ib Ih Iz Jg Jl Li Lx No Oe Qv Qy Rf) Kr(aZ BA bU bV cB cF cJ cS cT Db Ez Ib iZ Jl kS Na Oe Ua Un) Nm(Ba Ez Ir Iz Je Jg Jp kF Lx Mp Nv Nw Oh Ok Po Qa Qg Rf Un) Kd(aJ An bV cJ dM Fn Hx iZ Jd Je Jl Kg kS Mx Nq Qg Rh Uk) Ba(An aZ cE Dg Fn Hb iA iJ Kg Kl Ky Mg Tr Uc Uh Vo Tj) bA(aX bG cI cZ Dd Et Fn iA iJ Kq Ky oN Tv Ue Uk Uv Vs) Cp(aX Bb cS Cu Ii Jq Kg Kj Md Ng Ok On Pf Pg Uc Tj) Mx(aZ bV cJ Cu Cv iA In Is Js Kg Pc Pi Qv Rh Uc Vt) Jd(Ad Af Cv Cw Dg Dl Ic Jq Mm Ok Pj Qg Rh Uh Vo Vt) Ez(bU cC cJ Dg dJ Et Fn gW Hb Kg Mg Mm Tr Uk Ti) Jj(Im Jl jP Lv Mi Mk Mr Nr Nw Om On Pa Pc Pe Po) Fr(bN cO Cv Em Et Il In jG lL Lv Mg Tr Tv Uc) Nq(Ad Bb Co Cu Cw iJ Kj Ky Qg Qv Rh Vo Vt Ti) cT(An bG bN bX cE cI cJ cZ Et Fn Kq oH Ue Uk) Dg(Aw Gl Ik Im Je Jl Li Nh Nu Oi Po Qy Ua) Kg(Ao bV Ct fP Ha Hc Hx Ib Iz Je Po Qg Qy) hG(aZ bN cB cJ Et Fn kS Ky Ma oH Ow Rh Uk) Ti(aN aP cJ Db dK Jv Kn Nw Qz Rf Tz Tj) Tr(An Aw bU cB Hx Iz Je kS Li Lx Qy Uk) Ng(Ik Jk Jp Li Mw Nl Nt Nv Qa Qb Qc) Is(Ih Il Ip Ir It Jn Js Lu Mg Ml Nk) Uh(aJ An bV Dp fR Hx Je Jg Jl Po Un) cO(aX cN cS Im iZ Jr kS Mr Nh oH Qg) Et(Ao Dk Gl Ib Je Nw Qv Qy Rf Ua) Fn(aZ bU cB cS Cu fP Ib iZ kS Ky) Aw(Ad Af Al As cE Cw Dd Ma Mg) Qg(aJ Al cS Dp Je Jq Qv Um Vt) Js(Ji kK No Nv Nw Om Po Qa Qb) Uk(aX bR cB cF cS Ct dI Ib Qv) cJ(cS dG fP iC Im Je Jr Mr Nh) Hx(Ik In Jm kS Ml Nk Rh Vo) Iz(Ad Aj Co Cw iJ Kl Mg Vo) aJ(iA Io Ky Mp nW Ny Qe Uv) oP(Ir Mj mM Nf Nr Nx Og Qe) Jl(cE Cu Il In Lj Tv Uc) bV(bX cE cI cK cZ iZ kS) jP(aA iB Jk Lv Mw oF qU) Gd(Em Fp Jk Of Og Qv) Ma(bZ iZ kF Mi nR Qy) Mg(Je Jg Ji Nv Nw Om) Nk(Jp Nc Ne Nv Po Qa) bN(aN bX cN cZ dG dN) fR(aG aX bB cZ Kq Pj) iC(aZ cL cQ iO jH kK) An(aZ fP gL oH Rh) Ml(Me Nw Po Qa qZ) Ue(aX cB Em Ib Qw) aP(iJ Io jG kS Vt) bX(aX cB cI dA dI) dG(bG cE cZ dL iA) iZ(cB cS fP Ky Ow) jH(cQ Mw Nr oH qU) qW(aF bH bM dI kS) Nj(jG kN lL mM) Ir(kK mS nB qZ) Je(Ad As Bb Mm) kF(Ih Lj Mj Qe) Me(Hv Jp Lw) Ua(Co Cw Kl) Tv(dA Im Nb) Il(Jk Om Qb) In(Nv Qa Qb) It(nK nR nU) Jg(Ad Cw Uc) Ji(Aa Lu Mm) Jm(Jk Po Qa) aA(nD oK qU) aC(aX bE cZ) bG(dA eF gL) cS(aW cI cK) nB(jG Qe qU) iJ(dM iO Us) rB(bM iP lL) Em(Ub Vt) Nl(jY Nc) Ky(Dp fP) Nw(Aa Lv) cE(dF eF) nR(jT lL) nT(kN qU) iA(Jp Us) jG(Mp nU) oH(bM bW) AdIk CoHc DcDd NrQa LxNd MmQy MsjV MwnI TzJq IhQb HbkS IvjY QdqZ JknK RhOi OkUn aEjT aNcZ aVdA aZpF cIeM hXiP iOjM Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.2E1 | 7.6E1 | 7.3E1 | 9.2E1 | 5.0E1 | 5.8E1 | 2.0E0 | 1.0E1 | 2.9E2 | 2.7E2 | 936 | 59 | 159 | 59 | 0.61 |
| Ad | ug/mL | 2.4E-2 | 1.1E-1 | 5.2E-2 | 1.2E-1 | 7.0E-2 | 1.0E-1 | 6.8E-4 | 3.3E-3 | 3.7E-1 | 3.6E-1 | 218 | 46 | 87 | 46 | 0.74 |
| Af | ng/mL | 8.9E-1 | 1.3E0 | 1.6E1 | 3.0E1 | 7.0E1 | 8.0E1 | 1.7E-3 | 1.7E-3 | 5.3E2 | 4.0E2 | 218 | 46 | 87 | 46 | 0.58 |
| Aj | ng/mL | 1.4E0 | 4.6E0 | 2.6E0 | 3.6E0 | 2.4E0 | 2.4E0 | 1.5E-3 | 4.0E-3 | 6.1E0 | 6.1E0 | 218 | 46 | 87 | 46 | 0.60 |
| Al | mg/mL | 8.8E-5 | 1.2E-4 | 2.5E-4 | 2.7E-4 | 4.2E-4 | 4.1E-4 | 2.5E-6 | 9.0E-6 | 1.9E-3 | 1.9E-3 | 218 | 46 | 87 | 46 | 0.56 |
| An | U/mL | 4.1E1 | 6.9E1 | 1.8E2 | 2.3E2 | 5.5E2 | 4.9E2 | 9.8E-4 | 7.7E-1 | 5.5E3 | 3.0E3 | 218 | 46 | 87 | 46 | 0.61 |
| Ao | pg/mL | 8.1E1 | 1.1E2 | 2.3E2 | 2.3E2 | 1.1E3 | 5.5E2 | 2.8E0 | 1.2E1 | 1.6E4 | 3.8E3 | 218 | 46 | 87 | 46 | 0.61 |
| Ap | ng/mL | 2.6E1 | 5.8E1 | 3.6E1 | 6.7E1 | 3.2E1 | 5.0E1 | 9.9E-1 | 8.4E-5 | 1.7E2 | 2.5E2 | 218 | 46 | 87 | 46 | 0.73 |
| Ar | ng/mL | 6.3E-1 | 1.5E0 | 2.3E0 | 5.0E0 | 4.7E0 | 7.6E0 | 3.4E-3 | 3.4E-3 | 4.3E1 | 2.9E1 | 218 | 46 | 87 | 46 | 0.64 |
| As | ng/mL | 8.6E-3 | 9.8E-3 | 1.3E-2 | 1.5E-2 | 1.7E-2 | 2.2E-2 | 1.7E-3 | 1.7E-3 | 1.1E-1 | 1.2E-1 | 218 | 46 | 87 | 46 | 0.51 |
| Aw | pg/mL | 1.5E1 | 1.8E1 | 1.6E1 | 1.8E1 | 4.9E0 | 6.0E0 | 5.0E0 | 9.4E0 | 3.2E1 | 3.8E1 | 218 | 46 | 87 | 46 | 0.64 |
| Ax | ng/mL | 2.2E0 | 3.3E0 | 9.2E0 | 1.7E1 | 1.9E1 | 3.6E1 | 1.9E-2 | 4.9E-2 | 1.5E2 | 2.0E2 | 218 | 46 | 87 | 46 | 0.57 |
| Ba | ng/mL | 4.2E1 | 2.1E2 | 3.5E2 | 6.2E2 | 9.5E2 | 1.0E3 | 3.7E-1 | 5.5E0 | 8.1E3 | 4.5E3 | 218 | 46 | 87 | 46 | 0.69 |
| Bb | ng/mL | 2.3E0 | 5.4E0 | 4.8E0 | 6.6E0 | 8.2E0 | 5.2E0 | 4.1E-3 | 4.1E-1 | 6.6E1 | 2.0E1 | 218 | 46 | 87 | 46 | 0.67 |
| Bc | ng/mL | 3.2E1 | 5.0E1 | 9.6E1 | 1.2E2 | 1.8E2 | 2.0E2 | 1.1E-1 | 2.2E-1 | 1.0E3 | 1.0E3 | 218 | 46 | 87 | 46 | 0.59 |
| Bg | ng/mL | 7.1E-2 | 4.0E-1 | 3.4E0 | 1.5E0 | 2.1E1 | 2.7E0 | 5.3E-4 | 5.3E-4 | 2.5E2 | 1.3E1 | 218 | 46 | 87 | 46 | 0.67 |
| Bn | ng/mL | 5.6E-2 | 9.7E-2 | 8.6E-1 | 2.0E0 | 1.6E0 | 2.6E0 | 5.6E-2 | 5.6E-2 | 9.7E0 | 7.6E0 | 218 | 46 | 87 | 46 | 0.59 |
| Bo | ng/mL | 1.1E1 | 1.6E1 | 1.2E1 | 1.7E1 | 8.8E0 | 1.4E1 | 1.6E-2 | 1.6E-2 | 4.4E1 | 4.6E1 | 218 | 46 | 87 | 46 | 0.58 |
| Ch | uIU/mL | 1.1E0 | 2.3E0 | 7.6E0 | 2.0E1 | 2.3E1 | 4.2E1 | 3.4E-3 | 1.0E-1 | 2.1E2 | 1.9E2 | 218 | 46 | 87 | 46 | 0.62 |
| Co | pg/mL | 3.0E1 | 5.8E1 | 8.0E1 | 1.3E2 | 2.0E2 | 3.1E2 | 3.9E0 | 6.3E0 | 1.9E3 | 2.1E3 | 218 | 46 | 87 | 46 | 0.64 |
| Cp | ng/mL | 2.0E1 | 2.8E1 | 2.4E1 | 3.6E1 | 2.5E1 | 2.9E1 | 6.0E-1 | 6.0E-1 | 2.9E2 | 1.9E2 | 218 | 46 | 87 | 46 | 0.70 |
| Cq | ng/mL | 2.4E-2 | 3.7E-2 | 1.7E-1 | 6.0E-2 | 1.2E0 | 7.6E-2 | 8.0E-4 | 8.0E-4 | 1.7E1 | 4.0E-1 | 218 | 46 | 87 | 46 | 0.60 |
| Cs | ng/mL | 6.0E1 | 8.5E1 | 2.4E2 | 3.8E2 | 4.4E2 | 9.0E2 | 3.9E-1 | 1.3E0 | 2.9E3 | 5.3E3 | 218 | 46 | 87 | 46 | 0.55 |
| Ct | ng/mL | 1.2E0 | 9.7E-1 | 3.1E1 | 3.0E1 | 9.4E1 | 7.7E1 | 6.2E-3 | 2.7E-2 | 6.2E2 | 4.7E2 | 218 | 46 | 87 | 46 | 0.50 |
| Cu | ng/mL | 2.1E-1 | 3.4E-1 | 4.2E-1 | 4.0E-1 | 8.2E-1 | 2.3E-1 | 9.6E-3 | 8.1E-2 | 9.2E0 | 9.4E-1 | 218 | 46 | 87 | 46 | 0.65 |
| Cv | ng/mL | 3.9E0 | 1.1E1 | 1.6E1 | 3.5E1 | 5.3E1 | 6.5E1 | 5.6E-3 | 2.6E-2 | 5.3E2 | 3.1E2 | 218 | 46 | 87 | 46 | 0.62 |
| Cw | mIU/mL | 2.7E-2 | 3.8E-2 | 3.4E-2 | 4.6E-2 | 2.4E-2 | 3.1E-2 | 2.3E-3 | 7.9E-3 | 1.4E-1 | 1.4E-1 | 218 | 46 | 87 | 46 | 0.62 |
| Cx | ng/mL | 1.7E-1 | 4.2E-1 | 5.1E1 | 9.1E1 | 1.0E2 | 1.3E2 | 9.3E-5 | 9.3E-5 | 3.9E2 | 3.9E2 | 218 | 46 | 87 | 46 | 0.56 |
| Db | ug/mL | 7.3E0 | 6.7E0 | 8.3E0 | 7.8E0 | 5.7E0 | 7.2E0 | 5.0E-1 | 8.3E-1 | 3.9E1 | 3.6E1 | 218 | 46 | 87 | 46 | 0.46 |
| Dc | nmol/L | 1.8E-2 | 3.3E-2 | 5.7E-2 | 6.0E-2 | 1.4E-1 | 8.6E-2 | 5.2E-6 | 3.0E-4 | 1.2E0 | 4.0E-1 | 218 | 46 | 87 | 46 | 0.57 |
| Dd | ug/mL | 6.8E-2 | 5.6E-2 | 1.7E-1 | 2.4E-1 | 2.6E-1 | 3.9E-1 | 1.9E-4 | 1.1E-3 | 1.6E0 | 1.9E0 | 218 | 46 | 87 | 46 | 0.51 |
| De | ng/mL | 3.4E-3 | 3.4E-3 | 6.0E-2 | 1.0E-1 | 1.1E-1 | 1.4E-1 | 3.4E-3 | 3.4E-3 | 5.9E-1 | 6.2E-1 | 218 | 46 | 87 | 46 | 0.58 |
| Dg | ng/mL | 2.5E1 | 6.9E1 | 3.7E1 | 7.1E1 | 3.4E1 | 4.8E1 | 2.4E-1 | 1.0E-1 | 1.9E2 | 1.9E2 | 218 | 46 | 87 | 46 | 0.73 |
| Di | ng/mL | 1.7E0 | 2.1E0 | 2.0E0 | 2.4E0 | 1.8E0 | 2.3E0 | 1.8E-1 | 1.8E-1 | 1.3E1 | 7.8E0 | 218 | 46 | 87 | 46 | 0.54 |
| Dk | uIU/mL | 1.5E-2 | 2.6E-2 | 1.0E-1 | 4.4E-2 | 6.8E-1 | 6.2E-2 | 1.1E-4 | 1.1E-4 | 8.9E0 | 3.4E-1 | 218 | 46 | 87 | 46 | 0.63 |
| Dl | ng/mL | 2.1E2 | 4.1E2 | 2.7E2 | 5.1E2 | 2.4E2 | 3.7E2 | 1.7E0 | 2.5E0 | 1.4E3 | 1.3E3 | 218 | 46 | 87 | 46 | 0.70 |
| Do | ng/ml | 5.9E-1 | 6.3E-1 | 1.3E0 | 8.9E-1 | 3.2E0 | 1.0E0 | 3.6E-2 | 3.6E-2 | 1.9E1 | 3.7E0 | 42 | 11 | 28 | 11 | 0.53 |
| Dp | ng/ml | 2.4E0 | 2.5E0 | 4.5E0 | 5.1E0 | 6.6E0 | 6.7E0 | 3.7E-3 | 3.7E-3 | 4.3E1 | 3.5E1 | 111 | 44 | 86 | 44 | 0.52 |
| Dr | pg/ml | 2.2E1 | 1.3E1 | 4.6E1 | 3.2E1 | 6.4E1 | 4.4E1 | 7.5E-1 | 7.5E-1 | 2.9E2 | 1.6E2 | 78 | 22 | 39 | 22 | 0.45 |
| Dq | Absorbance | 1.7E-3 | 1.7E-3 | 4.4E-2 | 1.7E-1 | 1.7E-1 | 0.0E0 | 1.7E-3 | 1.7E-3 | 8.3E-1 | 1.7E-1 | 42 | 11 | 28 | 11 | 0.38 |
| Du | pg/ml | 2.7E1 | 1.2E0 | 5.5E2 | 1.9E3 | 1.3E3 | 6.8E3 | 1.2E0 | 1.2E0 | 7.0E3 | 2.6E4 | 45 | 15 | 35 | 15 | 0.42 |
| Dv | pg/ml | 1.0E0 | 1.3E0 | 1.2E0 | 1.1E0 | 1.3E0 | 9.1E-1 | 2.2E-2 | 2.2E-2 | 4.5E0 | 2.3E0 | 33 | 7 | 18 | 7 | 0.54 |
| Ef | ng/mL | 9.5E-2 | 4.4E-1 | 5.6E-1 | 1.2E0 | 1.3E0 | 2.0E0 | 5.7E-4 | 1.3E-3 | 9.4E0 | 8.6E0 | 143 | 45 | 86 | 45 | 0.67 |
| Wm | % | 7.0E-1 | 6.2E-1 | 3.4E1 | 6.1E1 | 2.1E2 | 2.3E2 | 8.5E-2 | 8.5E-2 | 2.4E3 | 9.6E2 | 173 | 47 | 101 | 47 | 0.53 |
| Ed | pg/ml | 7.1E0 | 5.2E-1 | 1.0E2 | 2.8E1 | 6.9E2 | 6.8E1 | 5.2E-1 | 5.2E-1 | 7.3E3 | 3.5E2 | 111 | 44 | 85 | 44 | 0.38 |
| Yf | ng/mL | 1.7E1 | 1.4E1 | 1.6E2 | 2.8E1 | 9.1E2 | 3.2E1 | 2.9E-1 | 2.2E0 | 6.6E3 | 1.2E2 | 52 | 15 | 41 | 15 | 0.49 |
| Tj | pg/ml | 3.7E-1 | 3.7E-1 | 8.9E1 | 8.4E0 | 4.0E2 | 2.4E1 | 3.6E-1 | 3.6E-1 | 3.5E3 | 1.5E2 | 141 | 46 | 86 | 46 | 0.41 |
| Po | pg/ml | 2.6E-1 | 2.6E0 | 7.7E0 | 1.2E1 | 2.5E1 | 3.0E1 | 8.0E-3 | 2.6E-2 | 2.7E2 | 2.2E2 | 316 | 65 | 135 | 65 | 0.62 |
| Ti | ug/mL | 2.5E0 | 5.9E0 | 3.7E0 | 6.3E0 | 3.4E0 | 5.1E0 | 1.2E-1 | 1.9E-1 | 1.5E1 | 1.7E1 | 77 | 26 | 61 | 26 | 0.65 |
| Em | ng/ml | 2.9E-3 | 2.9E-3 | 6.8E-2 | 4.4E-2 | 1.2E-1 | 9.9E-2 | 2.8E-16 | 1.9E-16 | 5.4E-1 | 4.7E-1 | 93 | 23 | 40 | 23 | 0.45 |
| Et | ng/ml | 1.1E3 | 2.5E3 | 1.4E3 | 2.5E3 | 1.0E3 | 1.2E3 | 7.7E1 | 1.8E2 | 4.2E3 | 5.0E3 | 316 | 65 | 135 | 65 | 0.75 |
| Eq | pg/ml | 1.3E2 | 2.5E2 | 3.0E2 | 3.7E2 | 3.9E2 | 4.8E2 | 1.0E0 | 1.0E0 | 1.8E3 | 1.8E3 | 45 | 15 | 35 | 15 | 0.54 |
| Th | ug/mL | 1.1E0 | 1.4E0 | 1.6E0 | 1.6E0 | 1.7E0 | 9.7E-1 | 2.6E-3 | 5.6E-1 | 1.2E1 | 4.6E0 | 77 | 26 | 61 | 26 | 0.59 |

Figure 14

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fa | ng/ml | 4.0E1 | 5.2E1 | 1.4E2 | 9.9E1 | 7.9E2 | 1.4E2 | 3.4E-2 | 2.6E-1 | 8.0E3 | 7.5E2 | 109 | 44 | 86 | 44 | 0.60 |
| Ez | ng/ml | 5.0E0 | 9.2E0 | 2.4E1 | 2.3E1 | 7.6E1 | 4.5E1 | 1.3E-2 | 1.3E-2 | 7.1E2 | 2.4E2 | 111 | 44 | 86 | 44 | 0.57 |
| Fb | ng/ml | 2.3E1 | 2.7E1 | 2.2E1 | 2.5E1 | 1.2E1 | 8.7E0 | 1.0E0 | 5.9E-1 | 5.7E1 | 4.0E1 | 109 | 44 | 86 | 44 | 0.59 |
| Ex | ng/ml | 6.2E-2 | 1.1E-1 | 2.6E-1 | 1.8E-1 | 9.1E-1 | 2.1E-1 | 3.5E-5 | 1.7E-4 | 8.9E0 | 9.2E-1 | 102 | 31 | 53 | 31 | 0.61 |
| Fc | pg/ml | 2.2E-1 | 2.2E-1 | 3.3E2 | 2.2E-1 | 2.2E3 | 0.0E0 | 2.2E-1 | 2.2E-1 | 1.5E4 | 2.2E-1 | 45 | 15 | 35 | 15 | 0.37 |
| Fd | pg/ml | 9.8E-1 | 9.8E-1 | 1.0E3 | 8.1E2 | 4.9E3 | 2.1E3 | 4.5E-1 | 9.8E-1 | 3.3E4 | 8.2E3 | 45 | 15 | 35 | 15 | 0.49 |
| Fi | pg/ml | 2.5E-1 | 2.5E-1 | 3.5E2 | 6.9E0 | 2.1E3 | 2.6E1 | 2.5E-1 | 2.5E-1 | 1.4E4 | 1.0E2 | 45 | 15 | 35 | 15 | 0.42 |
| Fn | ng/ml | 2.1E-1 | 2.1E-1 | 9.2E0 | 3.6E0 | 4.0E1 | 5.7E0 | 1.1E-14 | 1.1E-14 | 4.2E2 | 2.1E1 | 111 | 44 | 86 | 44 | 0.46 |
| Fp | ng/ml | 1.0E1 | 3.0E1 | 2.1E1 | 4.1E1 | 2.7E1 | 3.7E1 | 6.0E-3 | 6.6E-1 | 1.4E2 | 1.4E2 | 333 | 66 | 136 | 66 | 0.68 |
| Fr | ng/ml | 2.5E4 | 7.1E4 | 9.7E4 | 1.7E5 | 1.7E5 | 2.2E5 | 6.4E2 | 2.1E3 | 8.4E5 | 8.5E5 | 398 | 69 | 137 | 69 | 0.68 |
| Fw | pg/ml | 8.5E-1 | 1.2E-1 | 1.1E2 | 2.5E1 | 7.2E2 | 9.9E1 | 1.1E-14 | 1.7E-14 | 6.9E3 | 6.3E2 | 144 | 45 | 87 | 45 | 0.46 |
| Fy | ng/ml | 3.1E1 | 4.9E1 | 4.9E1 | 7.4E1 | 5.5E1 | 6.4E1 | 1.8E-1 | 1.2E-1 | 3.3E2 | 2.1E2 | 110 | 44 | 85 | 44 | 0.63 |
| Gh | pg/ml | 2.3E0 | 8.4E0 | 6.2E1 | 1.3E2 | 2.7E2 | 3.3E2 | 2.9E-2 | 2.9E-2 | 1.8E3 | 1.2E3 | 45 | 14 | 35 | 14 | 0.51 |
| Gb | % | 3.3E1 | 4.0E1 | 4.1E1 | 5.0E1 | 3.6E1 | 3.3E1 | 3.1E0 | 5.9E0 | 1.9E2 | 1.0E2 | 45 | 15 | 34 | 15 | 0.59 |
| Gc | ng/ml | 8.4E1 | 1.6E2 | 1.1E2 | 2.1E2 | 1.1E2 | 2.1E2 | 6.4E0 | 1.8E1 | 7.3E2 | 9.2E2 | 82 | 23 | 40 | 23 | 0.67 |
| Gd | ng/ml | 3.1E1 | 2.9E1 | 3.1E1 | 3.4E1 | 1.5E1 | 2.2E1 | 5.4E0 | 6.3E0 | 6.9E1 | 8.1E1 | 95 | 20 | 40 | 20 | 0.51 |
| Gn | U/ml | 5.1E-1 | 1.0E-1 | 1.8E0 | 8.1E-1 | 4.1E0 | 2.5E0 | 1.3E-3 | 1.3E-3 | 3.0E1 | 1.2E1 | 74 | 22 | 39 | 22 | 0.30 |
| Gl | pg/ml | 6.0E3 | 1.0E4 | 9.8E3 | 1.2E4 | 9.0E3 | 8.7E3 | 2.3E2 | 1.0E3 | 3.2E4 | 3.3E4 | 140 | 45 | 87 | 45 | 0.62 |
| Gp | U/ml | 1.8E0 | 1.1E0 | 4.4E0 | 3.9E0 | 8.0E0 | 8.2E0 | 1.3E-3 | 1.3E-3 | 6.7E1 | 4.8E1 | 144 | 45 | 87 | 45 | 0.44 |
| Gt | ng/ml | 2.2E-3 | 2.2E-3 | 7.7E-2 | 5.8E-3 | 2.1E-1 | 1.0E-2 | 2.2E-3 | 2.2E-3 | 1.1E0 | 3.1E-2 | 36 | 8 | 22 | 8 | 0.40 |
| Gw | ng/ml | 3.9E0 | 7.8E0 | 8.5E0 | 8.6E0 | 1.5E1 | 6.4E0 | 8.3E-1 | 8.3E-1 | 9.3E1 | 2.2E1 | 42 | 11 | 28 | 11 | 0.61 |
| Gz | ug/ml | 1.2E0 | 1.0E0 | 1.2E1 | 5.0E0 | 5.8E1 | 6.3E0 | 2.9E-16 | 1.3E-1 | 4.8E2 | 2.1E1 | 69 | 29 | 52 | 29 | 0.51 |
| Ha | ng/ml | 2.7E0 | 2.8E0 | 9.0E0 | 6.7E0 | 2.0E1 | 1.3E1 | 1.7E-2 | 1.7E-2 | 1.0E2 | 6.7E1 | 109 | 44 | 85 | 44 | 0.49 |
| Nm | pg/ml | 1.4E4 | 3.1E4 | 2.6E4 | 4.6E4 | 5.1E4 | 4.6E4 | 1.0E-9 | 1.0E-9 | 7.8E5 | 1.9E5 | 315 | 65 | 136 | 65 | 0.66 |
| Nn | pg/ml | 1.2E2 | 2.4E2 | 2.7E3 | 2.6E3 | 1.1E4 | 1.0E4 | 1.0E-9 | 1.0E-9 | 1.0E5 | 6.9E4 | 315 | 65 | 136 | 65 | 0.60 |
| No | pg/ml | 1.4E1 | 2.9E1 | 2.7E1 | 5.6E1 | 5.7E1 | 1.8E2 | 1.0E-9 | 3.2E-1 | 5.9E2 | 1.4E3 | 315 | 65 | 136 | 65 | 0.62 |
| Nq | pg/ml | 2.8E0 | 1.7E0 | 2.2E1 | 1.7E1 | 8.9E1 | 4.4E1 | 1.0E-9 | 1.0E-9 | 1.2E3 | 2.6E2 | 315 | 65 | 136 | 65 | 0.48 |
| Nr | pg/ml | 6.0E-1 | 2.5E0 | 1.4E1 | 1.5E2 | 6.9E1 | 1.1E3 | 1.0E-9 | 1.0E-9 | 9.8E2 | 8.5E3 | 315 | 65 | 136 | 65 | 0.63 |
| Ns | pg/ml | 1.0E-9 | 1.0E-9 | 1.3E1 | 3.2E0 | 7.8E1 | 1.6E1 | 1.0E-9 | 1.0E-9 | 1.1E3 | 1.0E2 | 315 | 65 | 136 | 65 | 0.49 |
| Nt | pg/ml | 9.9E1 | 1.6E2 | 1.4E2 | 1.8E2 | 1.3E2 | 1.1E2 | 1.5E1 | 4.7E1 | 1.5E3 | 6.8E2 | 315 | 65 | 136 | 65 | 0.68 |
| Nu | pg/ml | 2.0E1 | 4.4E1 | 5.2E1 | 8.6E1 | 8.8E1 | 1.1E2 | 1.0E-9 | 1.0E-9 | 8.9E2 | 5.8E2 | 315 | 65 | 136 | 65 | 0.62 |
| Lu | pg/ml | 1.0E4 | 1.0E4 | 1.6E4 | 1.2E4 | 4.2E4 | 1.5E4 | 6.7E2 | 7.1E2 | 5.6E5 | 9.6E4 | 317 | 66 | 136 | 66 | 0.50 |
| Lv | pg/ml | 1.0E-9 | 6.8E0 | 1.1E1 | 2.1E1 | 2.2E1 | 3.2E1 | 1.0E-9 | 1.0E-9 | 2.4E2 | 1.6E2 | 317 | 66 | 136 | 66 | 0.59 |
| Lw | pg/ml | 1.0E-9 | 1.0E-9 | 1.3E-1 | 4.8E-1 | 1.8E0 | 2.7E0 | 1.0E-9 | 1.0E-9 | 3.2E1 | 1.7E1 | 317 | 66 | 136 | 66 | 0.52 |
| Lx | pg/ml | 1.0E-9 | 5.5E1 | 1.2E2 | 3.1E2 | 4.3E2 | 1.2E3 | 1.0E-9 | 1.0E-9 | 6.2E3 | 1.0E4 | 317 | 66 | 136 | 66 | 0.64 |
| Ly | pg/ml | 1.0E-9 | 1.0E-9 | 9.2E0 | 2.1E1 | 1.8E1 | 3.2E1 | 1.0E-9 | 1.0E-9 | 1.2E2 | 1.6E2 | 317 | 66 | 136 | 66 | 0.58 |
| Lz | pg/ml | 1.0E-9 | 1.0E-9 | 2.5E0 | 6.5E0 | 2.5E1 | 3.5E1 | 1.0E-9 | 1.0E-9 | 4.3E2 | 2.1E2 | 317 | 66 | 136 | 66 | 0.51 |
| Ma | pg/ml | 2.7E2 | 4.7E2 | 1.4E3 | 1.3E3 | 4.6E3 | 2.0E3 | 1.0E-9 | 1.4E1 | 6.5E4 | 9.5E3 | 317 | 66 | 136 | 66 | 0.59 |
| Mb | pg/ml | 2.5E1 | 3.0E1 | 3.0E1 | 3.8E1 | 1.3E1 | 1.8E1 | 5.4E0 | 1.4E1 | 6.9E1 | 8.7E1 | 317 | 66 | 136 | 66 | 0.62 |
| Mc | pg/ml | 1.0E-9 | 1.0E-9 | 2.0E-2 | 1.0E-9 | 2.5E-1 | 0.0E0 | 1.0E-9 | 1.0E-9 | 4.0E0 | 1.0E-9 | 317 | 66 | 136 | 66 | 0.50 |
| Md | pg/ml | 1.0E-9 | 1.0E-9 | 5.0E-1 | 8.7E-1 | 4.0E0 | 3.2E0 | 1.0E-9 | 1.0E-9 | 6.5E1 | 1.6E1 | 317 | 66 | 136 | 66 | 0.51 |
| Me | pg/ml | 3.2E1 | 2.5E1 | 2.9E1 | 2.5E1 | 1.6E1 | 1.7E1 | 1.0E-9 | 6.1E-1 | 1.2E2 | 7.9E1 | 317 | 66 | 136 | 66 | 0.41 |
| Mf | pg/ml | 1.0E-9 | 1.0E-9 | 3.8E-1 | 6.5E-1 | 1.7E0 | 1.8E0 | 1.0E-9 | 1.0E-9 | 2.0E1 | 8.4E0 | 317 | 66 | 136 | 66 | 0.56 |
| Mg | pg/ml | 2.2E0 | 7.8E0 | 7.3E0 | 1.2E1 | 1.2E1 | 1.4E1 | 1.0E-9 | 1.0E-9 | 8.8E1 | 5.9E1 | 317 | 66 | 136 | 66 | 0.62 |
| Mh | pg/ml | 1.0E-9 | 1.0E-9 | 9.0E-1 | 1.7E0 | 8.0E0 | 6.1E0 | 1.0E-9 | 1.0E-9 | 1.1E2 | 3.8E1 | 317 | 66 | 136 | 66 | 0.51 |
| Mi | pg/ml | 1.0E-9 | 1.0E-9 | 7.8E-1 | 3.6E0 | 7.5E0 | 2.1E1 | 1.0E-9 | 1.0E-9 | 1.2E2 | 1.6E2 | 317 | 66 | 136 | 66 | 0.51 |
| Mj | pg/ml | 1.0E-9 | 1.0E-9 | 4.6E0 | 1.1E1 | 2.8E1 | 6.8E1 | 1.0E-9 | 1.0E-9 | 4.6E2 | 5.4E2 | 317 | 66 | 136 | 66 | 0.54 |
| Mk | pg/ml | 1.0E-9 | 4.8E0 | 1.7E1 | 9.4E1 | 1.1E2 | 6.8E2 | 1.0E-9 | 1.0E-9 | 1.7E3 | 5.6E3 | 317 | 66 | 136 | 66 | 0.55 |
| Ml | pg/ml | 1.0E-9 | 1.0E-9 | 9.5E0 | 1.3E0 | 1.2E2 | 3.3E0 | 1.0E-9 | 1.0E-9 | 2.1E3 | 1.6E1 | 317 | 66 | 136 | 66 | 0.55 |
| Mm | pg/ml | 4.6E2 | 9.2E2 | 8.4E2 | 1.5E3 | 9.7E2 | 1.6E3 | 1.0E-9 | 1.3E1 | 6.0E3 | 6.9E3 | 317 | 66 | 136 | 66 | 0.65 |
| Mn | pg/ml | 4.9E0 | 6.7E0 | 1.0E1 | 1.2E1 | 2.6E1 | 1.9E1 | 1.0E-9 | 1.0E-9 | 3.5E2 | 1.3E2 | 317 | 66 | 136 | 66 | 0.57 |
| Mp | pg/ml | 1.0E-9 | 1.0E-9 | 1.0E1 | 1.0E1 | 2.3E1 | 2.7E1 | 1.0E-9 | 1.0E-9 | 1.8E2 | 1.8E2 | 317 | 66 | 136 | 66 | 0.51 |
| Mq | pg/ml | 1.0E-9 | 1.0E-9 | 2.9E0 | 5.3E0 | 1.8E1 | 1.9E1 | 1.0E-9 | 1.0E-9 | 2.1E2 | 1.2E2 | 317 | 66 | 136 | 66 | 0.53 |
| Mr | pg/ml | 1.0E-9 | 1.0E-9 | 1.6E1 | 1.9E2 | 9.3E1 | 1.5E3 | 1.0E-9 | 1.0E-9 | 1.4E3 | 1.2E4 | 317 | 66 | 136 | 66 | 0.54 |
| Ms | pg/ml | 4.0E2 | 4.5E2 | 5.5E2 | 5.4E2 | 7.0E2 | 5.0E2 | 1.0E-9 | 1.0E-9 | 5.6E3 | 2.2E3 | 317 | 66 | 136 | 66 | 0.52 |
| Mt | pg/ml | 1.0E-9 | 2.0E0 | 1.1E1 | 5.7E0 | 6.7E1 | 1.3E1 | 1.0E-9 | 1.0E-9 | 8.7E2 | 7.8E1 | 317 | 66 | 136 | 66 | 0.69 |
| Mu | pg/ml | 1.0E-9 | 1.0E-9 | 1.7E0 | 1.2E0 | 1.1E1 | 3.9E0 | 1.0E-9 | 1.0E-9 | 9.9E1 | 2.7E1 | 317 | 66 | 136 | 66 | 0.58 |

Figure 14 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Mv | pg/ml | 1.0E-9 | 1.0E-9 | 9.5E1 | 8.7E1 | 4.5E2 | 3.4E2 | 1.0E-9 | 1.0E-9 | 4.5E3 | 2.5E3 | 317 | 66 | 136 | 66 | 0.56 |
| Mw | pg/ml | 2.3E1 | 4.5E1 | 6.3E2 | 4.3E2 | 4.1E3 | 1.3E3 | 1.0E-9 | 1.0E-9 | 6.2E4 | 8.5E3 | 317 | 66 | 136 | 66 | 0.61 |
| Mx | pg/ml | 1.0E-9 | 1.0E-9 | 2.1E-1 | 1.5E-1 | 8.3E-1 | 4.9E-1 | 1.0E-9 | 1.0E-9 | 7.4E0 | 3.0E0 | 317 | 66 | 136 | 66 | 0.52 |
| My | pg/ml | 1.0E-9 | 1.0E-9 | 6.1E2 | 3.0E2 | 3.7E3 | 8.7E2 | 1.0E-9 | 1.0E-9 | 3.9E4 | 4.6E3 | 317 | 66 | 136 | 66 | 0.55 |
| Mz | pg/ml | 9.2E0 | 1.7E1 | 2.3E1 | 3.1E1 | 6.3E1 | 3.8E1 | 1.0E-9 | 1.0E-9 | 8.4E2 | 2.0E2 | 317 | 66 | 136 | 66 | 0.66 |
| Na | pg/ml | 1.0E-9 | 1.0E-9 | 5.3E-1 | 8.0E-1 | 1.7E0 | 2.7E0 | 1.0E-9 | 1.0E-9 | 9.6E0 | 1.6E1 | 317 | 66 | 136 | 66 | 0.53 |
| Nb | pg/ml | 1.9E0 | 2.2E0 | 4.9E0 | 6.8E0 | 1.7E1 | 2.9E1 | 1.0E-9 | 1.0E-9 | 2.3E2 | 2.4E2 | 317 | 66 | 136 | 66 | 0.54 |
| Nc | pg/ml | 4.8E2 | 1.6E2 | 7.1E2 | 3.1E2 | 8.7E2 | 4.3E2 | 1.0E-9 | 1.0E-9 | 9.2E3 | 2.1E3 | 317 | 66 | 136 | 66 | 0.33 |
| Nd | pg/ml | 3.0E1 | 6.0E0 | 2.6E1 | 1.8E1 | 2.0E1 | 2.6E1 | 1.0E-9 | 1.0E-9 | 8.4E1 | 1.4E2 | 317 | 66 | 136 | 66 | 0.35 |
| Ne | pg/ml | 5.2E2 | 2.5E2 | 6.7E2 | 3.8E2 | 6.7E2 | 4.1E2 | 1.0E-9 | 1.0E-9 | 7.0E3 | 1.7E3 | 317 | 66 | 136 | 66 | 0.34 |
| Nf | pg/ml | 1.0E-9 | 1.0E-9 | 2.8E0 | 2.7E0 | 8.7E0 | 1.1E1 | 1.0E-9 | 1.0E-9 | 8.2E1 | 8.2E1 | 317 | 66 | 136 | 66 | 0.45 |
| Ng | pg/ml | 3.8E1 | 8.1E1 | 1.5E2 | 1.6E2 | 2.9E2 | 2.1E2 | 1.0E-9 | 1.0E-9 | 2.3E3 | 1.2E3 | 317 | 66 | 136 | 66 | 0.57 |
| Nh | pg/ml | 7.7E1 | 3.4E1 | 1.0E2 | 4.9E1 | 9.1E1 | 4.8E1 | 1.0E-9 | 1.0E-9 | 5.6E2 | 2.2E2 | 317 | 66 | 136 | 66 | 0.30 |
| Ni | pg/ml | 4.5E0 | 7.1E0 | 8.0E1 | 8.6E1 | 1.3E2 | 1.3E2 | 1.0E-9 | 1.0E-9 | 7.1E2 | 5.7E2 | 317 | 66 | 136 | 66 | 0.51 |
| Nj | pg/ml | 8.9E0 | 2.8E0 | 1.2E1 | 6.2E0 | 1.2E1 | 7.3E0 | 1.0E-9 | 1.0E-9 | 8.3E1 | 2.9E1 | 317 | 66 | 136 | 66 | 0.33 |
| Nk | pg/ml | 2.4E1 | 1.6E1 | 3.7E1 | 2.8E1 | 4.1E1 | 3.1E1 | 1.0E-9 | 1.0E-9 | 2.0E2 | 1.2E2 | 317 | 66 | 136 | 66 | 0.47 |
| Nl | pg/ml | 5.6E1 | 1.8E1 | 7.3E1 | 3.7E1 | 8.5E1 | 4.1E1 | 1.0E-9 | 1.0E-9 | 1.1E3 | 1.9E2 | 317 | 66 | 136 | 66 | 0.33 |
| Hl | pg/ml | 1.2E1 | 2.1E1 | 5.0E1 | 3.9E1 | 8.5E1 | 6.1E1 | 1.0E-9 | 1.0E-9 | 3.5E2 | 2.3E2 | 45 | 15 | 35 | 15 | 0.50 |
| Ho | pg/ml | 1.5E1 | 1.8E1 | 3.4E1 | 2.3E1 | 1.0E2 | 1.4E1 | 1.0E-9 | 8.1E0 | 7.0E2 | 6.0E1 | 45 | 15 | 35 | 15 | 0.62 |
| Hp | ng/ml | 1.7E0 | 1.9E0 | 6.4E1 | 3.0E2 | 2.2E2 | 4.3E2 | 1.0E-9 | 4.2E-1 | 8.9E2 | 8.9E2 | 45 | 15 | 35 | 15 | 0.54 |
| Tz | pg/ml | 4.8E3 | 7.1E3 | 8.4E3 | 3.7E3 | 1.2E4 | 1.5E5 | 7.4E1 | 1.5E2 | 8.8E4 | 1.0E6 | 113 | 44 | 84 | 44 | 0.60 |
| Ua | pg/ml | 3.8E3 | 5.0E3 | 1.3E4 | 1.4E4 | 2.5E4 | 2.9E4 | 3.5E2 | 1.0E3 | 1.4E5 | 1.9E5 | 113 | 44 | 84 | 44 | 0.60 |
| Ub | pg/ml | 5.3E2 | 6.6E2 | 7.9E2 | 1.0E3 | 1.2E3 | 1.2E3 | 1.0E-9 | 1.9E1 | 9.8E3 | 6.4E3 | 113 | 44 | 84 | 44 | 0.60 |
| Ue | pg/ml | 3.0E1 | 3.7E1 | 3.2E1 | 5.2E1 | 1.9E1 | 5.5E1 | 4.2E0 | 7.7E0 | 9.5E1 | 3.5E2 | 113 | 44 | 84 | 44 | 0.64 |
| Uc | pg/ml | 8.9E2 | 1.5E3 | 1.8E3 | 2.3E3 | 3.4E3 | 2.3E3 | 6.1E-1 | 9.2E1 | 2.9E4 | 9.2E3 | 113 | 44 | 84 | 44 | 0.62 |
| Ud | pg/ml | 1.0E-9 | 1.0E-9 | 3.7E1 | 1.0E-9 | 3.7E1 | 0.0E0 | 1.0E-9 | 1.0E-9 | 3.9E2 | 1.0E-9 | 113 | 44 | 84 | 44 | 0.49 |
| Hq | pg/ml | 1.1E0 | 1.7E0 | 1.2E1 | 1.2E1 | 6.3E1 | 4.6E1 | 1.0E-9 | 1.0E-9 | 9.5E2 | 3.0E2 | 317 | 65 | 136 | 65 | 0.52 |
| Hr | pg/ml | 1.3E2 | 1.1E2 | 8.2E2 | 6.1E2 | 1.5E3 | 1.6E3 | 1.0E-9 | 1.0E-9 | 9.7E3 | 1.1E4 | 317 | 65 | 136 | 65 | 0.47 |
| Hu | pg/ml | 1.4E1 | 1.9E1 | 3.5E2 | 1.7E3 | 3.7E4 | 6.9E3 | 1.0E-9 | 1.0E-9 | 6.3E5 | 4.7E4 | 317 | 65 | 136 | 65 | 0.57 |
| Hv | pg/ml | 1.3E0 | 1.7E0 | 3.6E0 | 3.7E0 | 1.5E1 | 8.0E0 | 1.0E-9 | 1.0E-9 | 2.5E2 | 5.9E1 | 317 | 65 | 136 | 65 | 0.58 |
| Hw | pg/ml | 6.8E0 | 8.4E0 | 2.7E1 | 6.8E1 | 1.1E2 | 4.2E2 | 1.0E-9 | 1.0E-9 | 1.7E3 | 3.4E3 | 317 | 65 | 136 | 65 | 0.47 |
| Hx | pg/ml | 8.3E0 | 1.3E1 | 6.7E1 | 5.1E1 | 5.3E2 | 2.4E2 | 1.0E-9 | 1.0E-9 | 9.3E3 | 2.1E3 | 317 | 65 | 136 | 65 | 0.56 |
| Ib | ng/ml | 6.6E-2 | 7.8E-2 | 7.9E-1 | 1.9E0 | 3.4E0 | 6.5E0 | 1.0E-9 | 1.0E-9 | 3.0E1 | 3.9E1 | 109 | 43 | 85 | 43 | 0.56 |
| Ic | U/ml | 2.2E2 | 2.2E2 | 3.3E2 | 3.8E2 | 1.5E3 | 6.7E2 | 2.9E0 | 1.2E1 | 1.5E4 | 4.2E3 | 109 | 43 | 85 | 43 | 0.63 |
| Id | U/ml | 6.2E-1 | 1.0E0 | 1.1E0 | 2.1E0 | 1.3E0 | 3.8E0 | 1.0E-9 | 1.0E-9 | 7.2E0 | 2.1E1 | 109 | 43 | 85 | 43 | 0.60 |
| Tt | pg/ml | 1.6E2 | 1.8E2 | 1.7E2 | 1.8E2 | 4.3E1 | 4.8E1 | 8.0E1 | 9.9E1 | 3.0E2 | 2.8E2 | 101 | 44 | 78 | 44 | 0.62 |
| To | pg/ml | 1.6E0 | 1.6E0 | 1.7E0 | 1.9E0 | 1.8E0 | 1.8E0 | 1.0E-9 | 1.0E-9 | 7.1E0 | 7.1E0 | 108 | 44 | 81 | 44 | 0.54 |
| Tr | pg/ml | 2.8E0 | 4.4E0 | 4.0E0 | 6.2E0 | 4.2E0 | 5.8E0 | 3.5E-2 | 4.1E-1 | 2.4E1 | 2.6E1 | 106 | 44 | 80 | 44 | 0.63 |
| Tn | pg/ml | 2.5E1 | 3.3E1 | 4.8E1 | 5.0E1 | 7.0E1 | 5.5E1 | 2.6E0 | 8.7E0 | 3.7E2 | 3.1E2 | 108 | 44 | 81 | 44 | 0.61 |
| Tv | ng/ml | 1.1E1 | 1.3E1 | 2.0E1 | 2.0E1 | 5.0E1 | 2.4E1 | 1.0E-9 | 1.0E-9 | 4.9E2 | 1.3E2 | 108 | 44 | 81 | 44 | 0.53 |
| Ih | pg/ml | 6.8E1 | 1.2E2 | 1.9E2 | 3.3E2 | 3.2E2 | 5.7E2 | 1.0E-9 | 1.0E-9 | 2.5E3 | 2.9E3 | 317 | 66 | 136 | 66 | 0.61 |
| Ii | ng/ml | 8.1E1 | 1.1E2 | 2.9E2 | 5.1E2 | 8.2E2 | 1.7E3 | 7.5E-1 | 7.5E0 | 8.4E3 | 1.0E4 | 317 | 66 | 136 | 66 | 0.59 |
| Ij | ng/ml | 7.2E1 | 9.1E1 | 2.1E2 | 2.5E2 | 7.5E2 | 8.1E2 | 2.1E0 | 1.9E1 | 6.4E3 | 6.4E3 | 317 | 65 | 136 | 65 | 0.60 |
| Ik | ng/ml | 1.1E1 | 2.7E2 | 1.0E3 | 7.6E2 | 9.8E3 | 1.3E3 | 5.9E-1 | 1.6E0 | 1.2E5 | 9.7E3 | 316 | 66 | 136 | 66 | 0.70 |
| Il | ng/ml | 3.8E2 | 5.9E2 | 1.5E3 | 1.4E3 | 3.1E3 | 2.8E3 | 1.0E-9 | 1.0E-9 | 1.2E4 | 1.2E4 | 314 | 64 | 136 | 64 | 0.52 |
| Im | ng/ml | 1.9E2 | 2.7E2 | 3.1E2 | 5.6E2 | 3.5E2 | 8.4E2 | 1.3E1 | 6.4E1 | 3.1E3 | 5.6E3 | 316 | 66 | 136 | 66 | 0.64 |
| In | ng/ml | 4.2E0 | 5.0E0 | 3.5E1 | 1.2E1 | 2.4E2 | 1.8E1 | 1.0E-9 | 1.0E-9 | 3.9E3 | 8.4E1 | 317 | 66 | 136 | 66 | 0.52 |
| Hb | ng/ml | 2.0E1 | 2.9E1 | 2.6E1 | 3.8E1 | 2.4E1 | 3.6E1 | 1.1E0 | 5.2E0 | 1.3E2 | 2.1E2 | 110 | 44 | 86 | 44 | 0.65 |
| Hc | ng/ml | 6.9E2 | 9.0E2 | 2.0E3 | 4.3E3 | 4.7E3 | 1.5E4 | 1.0E-9 | 1.0E-9 | 3.6E4 | 1.0E5 | 110 | 44 | 86 | 44 | 0.58 |
| Hf | ng/ml | 1.4E2 | 1.9E2 | 4.0E2 | 4.0E2 | 5.5E2 | 5.2E2 | 1.0E-9 | 1.0E-9 | 2.5E3 | 2.2E3 | 110 | 44 | 86 | 44 | 0.53 |
| Io | ng/ml | 8.4E3 | 8.2E3 | 1.8E4 | 2.2E4 | 5.5E4 | 6.9E4 | 6.6E1 | 3.2E2 | 8.8E5 | 5.5E5 | 315 | 65 | 135 | 65 | 0.54 |
| Ip | ng/ml | 9.7E0 | 2.3E1 | 1.9E1 | 2.5E1 | 2.6E1 | 2.6E1 | 1.0E-9 | 4.1E-2 | 2.6E2 | 1.4E2 | 315 | 65 | 135 | 65 | 0.57 |
| Iq | ug/ml | 1.1E-1 | 3.0E-2 | 4.4E1 | 1.3E1 | 7.7E2 | 9.4E1 | 1.0E-9 | 1.0E-9 | 1.4E4 | 7.5E2 | 315 | 65 | 135 | 65 | 0.44 |
| Ir | ug/ml | 3.2E-1 | 4.7E-1 | 3.2E0 | 3.2E0 | 2.1E1 | 1.4E1 | 1.0E-9 | 1.0E-9 | 2.4E2 | 1.1E2 | 314 | 65 | 135 | 65 | 0.60 |
| Is | ng/ml | 1.4E0 | 2.5E0 | 5.6E0 | 9.8E0 | 1.2E1 | 3.0E1 | 1.0E-9 | 1.0E-9 | 8.8E1 | 2.3E2 | 315 | 65 | 135 | 65 | 0.58 |
| It | ng/ml | 2.0E0 | 2.7E0 | 2.2E1 | 2.8E1 | 1.1E2 | 1.2E2 | 1.0E-9 | 1.0E-9 | 1.2E3 | 7.7E2 | 315 | 65 | 135 | 65 | 0.53 |
| Iu | ng/ml | 2.1E2 | 2.6E2 | 1.5E3 | 1.8E3 | 4.8E3 | 5.4E3 | 1.0E-9 | 1.0E-9 | 2.9E4 | 2.4E4 | 315 | 65 | 135 | 65 | 0.50 |

Figure 14 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Iv | ng/ml | 1.3E1 | 2.6E1 | 4.7E1 | 1.5E2 | 1.3E2 | 8.0E2 | 1.0E-9 | 1.0E-9 | 1.6E3 | 6.4E3 | 315 | 65 | 135 | 65 | 0.61 |
| Iz | ng/ml | 1.3E2 | 3.1E2 | 4.0E2 | 5.2E2 | 9.6E2 | 6.8E2 | 1.5E0 | 8.7E0 | 8.4E3 | 3.6E3 | 110 | 44 | 86 | 44 | 0.64 |
| Yg | pg/ml | 2.5E2 | 5.2E2 | 1.6E3 | 1.4E3 | 7.4E3 | 3.1E3 | 1.0E-9 | 4.1E1 | 5.0E4 | 1.2E4 | 45 | 14 | 35 | 14 | 0.62 |
| Yh | pg/ml | 2.1E2 | 2.9E2 | 5.1E2 | 4.1E2 | 1.2E3 | 3.8E2 | 1.0E-9 | 1.0E-9 | 7.8E3 | 1.0E3 | 45 | 14 | 35 | 14 | 0.55 |
| Yi | pg/ml | 2.2E2 | 4.4E2 | 5.6E2 | 3.6E2 | 1.2E3 | 2.7E2 | 1.0E-9 | 1.0E-9 | 7.6E3 | 8.7E2 | 45 | 14 | 35 | 14 | 0.53 |
| Yk | U/ml | 1.0E-9 | 1.0E-9 | 1.8E-1 | 4.0E-2 | 5.3E-1 | 1.1E-1 | 1.0E-9 | 1.0E-9 | 3.0E0 | 3.6E-1 | 45 | 14 | 35 | 14 | 0.46 |
| Yj | pg/ml | 1.7E2 | 1.2E2 | 3.9E2 | 4.7E2 | 5.6E2 | 1.1E3 | 1.0E-9 | 1.7E1 | 3.2E3 | 4.1E3 | 45 | 14 | 35 | 14 | 0.44 |
| Yd | ng/ml | 2.0E-1 | 1.4E-1 | 3.1E-1 | 2.4E-1 | 4.0E-1 | 2.0E-1 | 6.6E-3 | 4.2E-2 | 1.8E0 | 6.0E-1 | 47 | 15 | 37 | 15 | 0.52 |
| Wb | pg/ml | 3.0E4 | 2.9E4 | 3.4E4 | 3.5E4 | 1.8E4 | 2.0E4 | 2.2E3 | 1.0E4 | 8.5E4 | 8.5E4 | 47 | 15 | 37 | 15 | 0.50 |
| Vz | pg/ml | 3.2E0 | 2.3E0 | 4.9E0 | 2.2E0 | 5.8E0 | 1.9E0 | 1.0E-9 | 1.0E-9 | 2.9E1 | 7.6E0 | 47 | 15 | 37 | 15 | 0.34 |
| Si | ng/ml | 8.0E-1 | 1.4E0 | 1.5E0 | 3.3E0 | 2.2E0 | 4.2E0 | 1.9E-2 | 7.8E-2 | 1.0E1 | 1.3E1 | 45 | 15 | 35 | 15 | 0.65 |
| Sf | mIU/mL | 1.2E1 | 1.2E1 | 5.4E1 | 2.3E1 | 1.2E2 | 3.7E1 | 8.1E-2 | 1.1E0 | 7.2E2 | 1.5E2 | 45 | 15 | 35 | 15 | 0.48 |
| Sh | mIU/mL | 1.3E1 | 9.0E0 | 5.2E1 | 2.0E1 | 1.2E2 | 2.3E1 | 2.9E-2 | 1.3E-1 | 5.9E2 | 7.5E1 | 45 | 15 | 35 | 15 | 0.47 |
| Sj | ng/ml | 4.4E-1 | 3.8E-1 | 4.2E-1 | 3.8E-1 | 8.5E-2 | 1.4E-1 | 2.5E-1 | 1.1E-1 | 6.1E-1 | 6.2E-1 | 45 | 15 | 35 | 15 | 0.39 |
| Rc | pg/ml | 5.2E3 | 7.2E3 | 6.3E3 | 9.1E3 | 4.4E3 | 6.5E3 | 1.9E2 | 1.4E3 | 2.2E4 | 2.3E4 | 111 | 44 | 84 | 44 | 0.61 |
| Rb | pg/ml | 7.6E-1 | 1.1E0 | 2.5E0 | 3.3E0 | 3.6E0 | 4.6E0 | 1.0E-9 | 1.0E-9 | 1.6E1 | 2.1E1 | 111 | 44 | 84 | 44 | 0.55 |
| Zq | 2.6ng/ml | 1.5E2 | 3.5E2 | 2.0E2 | 4.6E2 | 1.5E2 | 3.8E2 | 8.3E0 | 6.9E1 | 5.2E2 | 9.7E2 | 44 | 15 | 34 | 15 | 0.71 |
| Zw | 2.5ng/ml | 3.6E0 | 3.8E0 | 1.0E1 | 8.9E0 | 1.5E1 | 1.2E1 | 6.3E-2 | 3.5E-1 | 5.9E1 | 4.6E1 | 47 | 15 | 37 | 15 | 0.48 |
| Zx | 2.3mU/ml | 1.0E-1 | 9.5E-2 | 3.0E-1 | 1.8E-1 | 5.9E-1 | 1.6E-1 | 4.1E-2 | 5.6E-2 | 3.0E0 | 5.5E-1 | 47 | 15 | 37 | 15 | 0.51 |
| Pz | ng/ml | 3.3E3 | 1.0E4 | 7.5E3 | 2.5E4 | 1.9E4 | 1.3E5 | 1.3E1 | 3.5E2 | 2.8E5 | 1.0E6 | 314 | 65 | 134 | 65 | 0.61 |
| Qa | ng/ml | 2.8E3 | 4.6E3 | 6.2E3 | 7.4E3 | 8.3E3 | 5.8E3 | 1.5E2 | 9.5E2 | 5.2E4 | 2.3E4 | 314 | 65 | 134 | 65 | 0.65 |
| Qb | ng/ml | 1.0E2 | 1.3E2 | 2.6E2 | 1.9E2 | 6.8E2 | 1.8E2 | 7.9E-1 | 1.0E1 | 8.3E3 | 7.2E2 | 314 | 65 | 134 | 65 | 0.56 |
| Qc | ng/ml | 2.5E2 | 3.4E2 | 5.2E2 | 4.5E2 | 1.0E3 | 4.0E2 | 8.1E-1 | 1.1E1 | 1.1E4 | 1.6E3 | 314 | 65 | 134 | 65 | 0.56 |
| Qd | ng/ml | 9.5E3 | 1.4E4 | 2.8E4 | 2.2E4 | 1.3E5 | 2.4E4 | 2.4E2 | 2.7E3 | 2.0E6 | 1.2E5 | 314 | 65 | 134 | 65 | 0.62 |
| Qe | ng/ml | 7.8E2 | 1.6E3 | 2.0E3 | 2.3E3 | 5.9E3 | 2.5E3 | 7.6E0 | 2.5E2 | 9.7E4 | 1.4E4 | 314 | 65 | 134 | 65 | 0.66 |
| Jd | ng/ml | 3.6E-1 | 2.5E0 | 7.1E0 | 4.6E0 | 6.2E1 | 1.1E1 | 1.0E-9 | 1.0E-9 | 6.5E2 | 7.3E1 | 111 | 44 | 86 | 44 | 0.73 |
| Je | ng/ml | 1.0E-9 | 6.1E-1 | 1.4E0 | 1.6E0 | 5.6E0 | 2.1E0 | 1.0E-9 | 1.0E-9 | 5.6E1 | 7.0E0 | 111 | 44 | 86 | 44 | 0.63 |
| Jf | ng/ml | 1.0E-9 | 1.0E-9 | 8.1E-1 | 1.4E0 | 2.1E0 | 2.5E0 | 1.0E-9 | 1.0E-9 | 1.2E1 | 9.6E0 | 111 | 44 | 86 | 44 | 0.58 |
| Jg | ng/ml | 3.7E2 | 1.2E3 | 7.2E2 | 1.4E3 | 1.1E3 | 1.2E3 | 5.8E0 | 4.0E1 | 1.0E4 | 5.4E3 | 317 | 65 | 136 | 65 | 0.72 |
| Jh | ng/ml | 2.3E0 | 7.7E0 | 2.5E1 | 3.9E1 | 1.0E2 | 9.3E1 | 1.0E-9 | 1.0E-9 | 1.2E3 | 4.7E2 | 317 | 65 | 136 | 65 | 0.62 |
| Ji | ng/ml | 4.6E1 | 7.9E1 | 6.7E1 | 1.2E2 | 6.9E1 | 1.0E2 | 1.1E0 | 1.3E1 | 5.3E2 | 5.9E2 | 317 | 65 | 136 | 65 | 0.71 |
| Sr | pg/mL | 3.0E2 | 6.4E2 | 7.6E2 | 1.0E3 | 1.3E3 | 1.1E3 | 1.0E-9 | 1.0E-9 | 9.8E3 | 5.1E3 | 106 | 42 | 82 | 42 | 0.64 |
| Ss | pg/mL | 7.6E4 | 2.0E5 | 1.3E5 | 1.9E5 | 1.3E5 | 1.5E5 | 9.5E3 | 1.4E4 | 6.7E5 | 6.8E5 | 106 | 42 | 82 | 42 | 0.63 |
| St | pg/mL | 2.2E7 | 3.6E7 | 4.7E7 | 6.5E7 | 6.0E7 | 9.0E7 | 7.8E5 | 1.1E6 | 4.1E8 | 4.2E8 | 108 | 44 | 82 | 44 | 0.58 |
| Wc | ng/ml | 1.0E-9 | 2.6E-2 | 5.2E-2 | 6.4E-2 | 1.5E-1 | 9.1E-2 | 1.0E-9 | 1.0E-9 | 9.8E-1 | 2.8E-1 | 47 | 15 | 36 | 15 | 0.59 |
| Wd | ng/ml | 8.9E0 | 9.9E0 | 1.8E1 | 7.6E1 | 4.3E1 | 2.0E2 | 1.0E-9 | 7.8E-1 | 2.9E2 | 7.9E2 | 47 | 15 | 36 | 15 | 0.59 |
| We | ng/ml | 3.5E-1 | 4.7E-1 | 6.9E-1 | 8.1E-1 | 9.7E-1 | 1.0E0 | 1.0E-9 | 1.0E-9 | 3.9E0 | 3.5E0 | 47 | 15 | 36 | 15 | 0.54 |
| Wg | ng/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 47 | 15 | 36 | 15 | 0.50 |
| Wh | ng/ml | 8.7E-3 | 8.7E-3 | 1.9E-2 | 2.0E-1 | 5.1E-2 | 6.3E-1 | 1.0E-9 | 1.0E-9 | 3.5E-1 | 2.5E0 | 47 | 15 | 36 | 15 | 0.56 |
| Wf | ng/ml | 1.0E-9 | 1.0E-9 | 1.4E-1 | 2.2E-1 | 2.6E-1 | 6.3E-1 | 1.0E-9 | 1.0E-9 | 1.1E0 | 2.4E0 | 47 | 15 | 36 | 15 | 0.42 |
| Ra | pg/ml | 1.0E-9 | 1.0E-9 | 7.5E-1 | 2.4E-1 | 1.4E0 | 6.7E-1 | 1.0E-9 | 1.0E-9 | 7.3E0 | 2.6E0 | 111 | 44 | 84 | 44 | 0.42 |
| Qz | pg/ml | 1.1E1 | 9.6E0 | 6.9E1 | 3.7E1 | 1.1E2 | 5.5E1 | 1.0E-9 | 1.0E-9 | 7.1E2 | 2.2E2 | 111 | 44 | 84 | 44 | 0.43 |
| Qy | pg/ml | 4.1E-1 | 5.7E-1 | 2.9E0 | 1.6E1 | 1.5E1 | 7.7E1 | 1.0E-9 | 1.0E-9 | 1.6E2 | 5.1E2 | 111 | 44 | 84 | 44 | 0.57 |
| Qx | pg/ml | 1.0E-9 | 1.0E-9 | 6.4E0 | 4.1E-1 | 5.1E1 | 1.8E0 | 1.0E-9 | 1.0E-9 | 5.4E2 | 9.4E0 | 111 | 44 | 84 | 44 | 0.46 |
| Qw | pg/ml | 1.8E-1 | 1.0E-9 | 1.4E0 | 1.3E0 | 3.7E0 | 4.1E0 | 1.0E-9 | 1.0E-9 | 3.0E1 | 2.7E1 | 111 | 44 | 84 | 44 | 0.44 |
| Qv | pg/ml | 2.3E4 | 2.5E4 | 3.7E4 | 3.5E4 | 7.7E4 | 4.1E4 | 1.2E3 | 1.1E3 | 7.4E5 | 2.3E5 | 111 | 44 | 84 | 44 | 0.49 |
| Qu | pg/ml | 5.1E0 | 2.6E1 | 7.9E1 | 1.1E2 | 1.7E2 | 2.0E2 | 1.0E-9 | 1.0E-9 | 8.0E2 | 9.2E2 | 111 | 44 | 84 | 44 | 0.60 |
| Qt | pg/ml | 1.2E1 | 1.2E1 | 3.0E1 | 7.4E1 | 5.9E1 | 1.5E2 | 1.0E-9 | 1.0E-9 | 3.8E2 | 7.0E2 | 111 | 44 | 84 | 44 | 0.57 |
| Qh | ng/ml | 1.5E1 | 1.7E1 | 3.7E1 | 3.4E1 | 7.2E1 | 4.8E1 | 1.2E-1 | 1.4E0 | 6.4E2 | 2.6E2 | 111 | 44 | 84 | 44 | 0.54 |
| Qg | ng/ml | 8.9E0 | 6.3E0 | 2.6E1 | 1.3E1 | 1.0E2 | 3.3E1 | 1.5E-1 | 1.3E-1 | 1.0E3 | 2.2E2 | 111 | 44 | 84 | 44 | 0.39 |
| Jj | ng/ml | 8.4E2 | 5.2E2 | 2.9E3 | 1.0E3 | 2.0E4 | 1.6E3 | 2.0E1 | 1.7E1 | 3.4E5 | 1.1E4 | 317 | 65 | 136 | 65 | 0.41 |
| Jk | ng/ml | 3.3E0 | 3.8E0 | 2.4E1 | 2.5E1 | 5.0E1 | 4.8E1 | 1.0E-9 | 1.2E-1 | 2.8E2 | 2.7E2 | 317 | 65 | 136 | 65 | 0.55 |
| Jl | ng/ml | 3.7E-1 | 8.2E-1 | 1.9E0 | 4.9E0 | 4.7E0 | 2.0E1 | 7.6E-4 | 1.6E-2 | 3.2E1 | 1.6E2 | 317 | 65 | 136 | 65 | 0.63 |
| Jm | ng/ml | 1.9E1 | 3.3E1 | 5.1E1 | 6.4E1 | 9.4E1 | 9.7E1 | 1.0E-9 | 4.1E-1 | 1.0E3 | 6.1E2 | 317 | 65 | 136 | 65 | 0.55 |
| Jn | pg/ml | 3.8E-1 | 7.7E-1 | 1.9E0 | 1.6E0 | 7.0E0 | 3.6E0 | 1.0E-9 | 1.0E-9 | 6.2E1 | 2.7E1 | 317 | 65 | 136 | 65 | 0.60 |
| Jo | pg/ml | 4.0E3 | 5.0E3 | 5.0E3 | 6.4E3 | 3.7E3 | 5.7E3 | 4.2E1 | 4.8E2 | 2.0E4 | 3.8E4 | 317 | 65 | 136 | 65 | 0.57 |
| Jp | pg/ml | 6.6E4 | 8.9E4 | 7.0E4 | 9.0E4 | 3.4E4 | 3.7E4 | 2.1E3 | 1.4E4 | 2.1E5 | 2.1E5 | 317 | 65 | 136 | 65 | 0.66 |

Figure 14 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jq | pg/ml | 9.2E1 | 1.1E2 | 1.4E2 | 2.2E2 | 1.6E2 | 5.1E2 | 2.6E0 | 8.1E0 | 1.1E3 | 4.0E3 | 317 | 65 | 136 | 65 | 0.56 |
| Jr | pg/ml | 3.8E0 | 7.0E0 | 1.8E1 | 1.8E1 | 6.6E1 | 3.7E1 | 1.0E-9 | 1.0E-9 | 7.9E2 | 2.0E2 | 317 | 65 | 136 | 65 | 0.58 |
| Js | pg/ml | 1.3E1 | 1.5E1 | 4.5E1 | 2.8E1 | 1.5E2 | 7.3E1 | 1.0E-9 | 2.6E0 | 1.6E3 | 5.9E2 | 317 | 65 | 136 | 65 | 0.55 |
| Jt | pg/ml | 2.4E3 | 3.8E3 | 3.0E3 | 4.4E3 | 2.1E3 | 4.2E3 | 1.5E2 | 6.4E2 | 1.2E4 | 3.3E4 | 317 | 65 | 136 | 65 | 0.64 |
| Xa | pg/ml | 1.0E-9 | 7.0E-1 | 9.8E0 | 1.2E1 | 2.1E1 | 2.0E1 | 1.0E-9 | 1.0E-9 | 9.6E1 | 6.4E1 | 47 | 14 | 37 | 14 | 0.54 |
| Yc | pg/ml | 1.0E-9 | 1.0E-9 | 3.0E0 | 5.4E0 | 1.0E1 | 1.2E1 | 1.0E-9 | 1.0E-9 | 6.9E1 | 4.1E1 | 47 | 14 | 37 | 14 | 0.47 |
| Tm | pg/ml | 1.0E-9 | 1.0E-9 | 3.2E0 | 1.8E0 | 5.4E0 | 3.6E0 | 1.0E-9 | 1.0E-9 | 1.8E1 | 8.4E0 | 47 | 14 | 37 | 14 | 0.45 |
| Tl | pg/ml | 1.1E-1 | 4.7E-1 | 2.7E-1 | 4.2E-1 | 3.8E-1 | 3.5E-1 | 1.0E-9 | 1.0E-9 | 1.8E0 | 1.2E0 | 47 | 14 | 37 | 14 | 0.65 |
| Ju | mIU/ml | 7.2E0 | 1.2E1 | 2.2E1 | 1.9E1 | 3.6E1 | 3.2E1 | 6.5E-2 | 3.4E-1 | 2.3E2 | 2.0E2 | 111 | 44 | 86 | 44 | 0.57 |
| Jv | mIU/ml | 1.1E1 | 1.6E1 | 3.9E1 | 3.0E1 | 7.4E1 | 5.4E1 | 1.0E-2 | 8.2E-2 | 4.4E2 | 3.4E2 | 111 | 44 | 86 | 44 | 0.53 |
| Jy | ng/ml | 1.5E-3 | 1.6E-3 | 2.3E-3 | 1.6E-3 | 4.9E-3 | 6.9E-4 | 1.7E-4 | 4.5E-4 | 5.2E-2 | 3.7E-3 | 111 | 44 | 86 | 44 | 0.46 |
| Kc | pg/ml | 2.1E1 | 4.3E1 | 3.5E1 | 6.3E1 | 4.0E1 | 5.3E1 | 1.0E-9 | 1.0E-9 | 1.7E2 | 1.8E2 | 111 | 43 | 86 | 43 | 0.70 |
| Kd | pg/ml | 1.0E-9 | 1.0E-9 | 2.4E2 | 2.9E2 | 7.3E2 | 6.1E2 | 1.0E-9 | 1.0E-9 | 4.8E3 | 2.3E3 | 111 | 43 | 86 | 43 | 0.53 |
| Ke | pg/ml | 9.6E3 | 1.6E4 | 1.3E4 | 1.8E4 | 9.5E3 | 1.0E4 | 3.4E2 | 2.9E3 | 5.9E4 | 5.6E4 | 111 | 43 | 86 | 43 | 0.66 |
| Kf | pg/mL | 5.9E0 | 9.5E0 | 6.5E0 | 9.6E0 | 5.7E0 | 4.7E0 | 1.0E-9 | 2.2E-1 | 2.6E1 | 2.4E1 | 111 | 43 | 86 | 43 | 0.70 |
| Kg | pg/mL | 9.9E2 | 1.8E3 | 1.5E3 | 2.5E3 | 1.5E3 | 2.3E3 | 7.3E1 | 1.4E2 | 8.4E3 | 1.1E4 | 111 | 43 | 86 | 43 | 0.65 |
| Ki | pg/ml | 6.4E1 | 5.6E1 | 7.2E1 | 6.7E1 | 5.2E1 | 4.5E1 | 1.0E-9 | 1.0E-9 | 2.9E2 | 2.8E2 | 111 | 42 | 86 | 42 | 0.47 |
| Kj | pg/ml | 9.3E2 | 1.5E3 | 1.5E3 | 2.0E3 | 1.7E3 | 1.5E3 | 1.4E1 | 1.1E2 | 1.0E4 | 6.1E3 | 111 | 43 | 86 | 43 | 0.63 |
| Kk | pg/ml | 6.9E0 | 7.1E0 | 1.1E1 | 1.4E1 | 1.8E1 | 1.6E1 | 1.0E-9 | 1.0E-9 | 1.6E2 | 6.1E1 | 111 | 43 | 86 | 43 | 0.53 |
| Kl | pg/ml | 1.8E4 | 4.5E4 | 2.5E4 | 4.2E4 | 2.2E4 | 3.2E4 | 1.6E2 | 2.7E3 | 1.1E5 | 1.6E5 | 111 | 43 | 86 | 43 | 0.68 |
| Kn | pg/ml | 1.5E1 | 5.7E1 | 5.8E1 | 8.6E1 | 1.1E2 | 1.1E2 | 1.0E-9 | 1.0E-9 | 7.3E2 | 4.7E2 | 111 | 43 | 86 | 43 | 0.64 |
| Ko | pg/ml | 3.0E2 | 7.0E2 | 3.9E2 | 7.3E2 | 4.0E2 | 6.1E2 | 1.0E-9 | 1.0E-9 | 1.8E3 | 2.4E3 | 111 | 43 | 86 | 43 | 0.67 |
| Kp | pg/ml | 3.2E2 | 3.6E2 | 3.4E2 | 4.2E2 | 3.0E2 | 2.5E2 | 1.0E-9 | 1.0E-9 | 1.7E3 | 9.1E2 | 111 | 43 | 86 | 43 | 0.61 |
| Kq | pg/ml | 2.8E2 | 5.0E2 | 4.2E2 | 5.6E2 | 9.7E2 | 3.9E2 | 5.1E0 | 1.1E2 | 9.8E3 | 2.1E3 | 106 | 44 | 82 | 44 | 0.71 |
| Kr | pg/ml | 5.0E-1 | 2.0E0 | 2.5E0 | 3.0E0 | 4.9E0 | 3.5E0 | 1.0E-9 | 1.0E-9 | 3.5E1 | 1.2E1 | 106 | 44 | 82 | 44 | 0.58 |
| Ks | pg/ml | 1.5E4 | 1.5E4 | 2.1E4 | 2.1E4 | 2.0E4 | 1.7E4 | 3.8E2 | 2.7E2 | 1.1E5 | 5.0E4 | 106 | 44 | 82 | 44 | 0.53 |
| Ps | ng/ml | 1.4E2 | 1.9E2 | 4.3E2 | 5.3E2 | 1.2E3 | 8.2E2 | 6.9E0 | 1.7E1 | 8.3E3 | 2.9E3 | 45 | 15 | 34 | 15 | 0.56 |
| Kx | ng/ml | 1.0E-9 | 7.4E-3 | 4.6E-3 | 8.4E-3 | 8.6E-3 | 9.9E-3 | 1.0E-9 | 1.0E-9 | 5.1E-2 | 4.4E-2 | 110 | 44 | 86 | 44 | 0.64 |
| Ky | ng/ml | 1.0E-1 | 1.3E-1 | 3.5E-1 | 3.7E-1 | 7.1E-1 | 5.5E-1 | 1.0E-9 | 1.0E-9 | 5.1E0 | 2.4E0 | 110 | 44 | 86 | 44 | 0.54 |
| Kz | ng/ml | 1.0E-9 | 1.0E-9 | 3.7E-3 | 2.3E-3 | 6.3E-3 | 4.7E-3 | 1.0E-9 | 1.0E-9 | 3.6E-2 | 1.4E-2 | 110 | 44 | 86 | 44 | 0.45 |
| Rz | ng/ml | 1.4E-1 | 5.6E-1 | 6.0E-1 | 1.4E0 | 1.0E0 | 1.7E0 | 3.6E-3 | 5.7E-2 | 4.4E0 | 4.7E0 | 45 | 15 | 35 | 15 | 0.69 |
| Ry | ng/ml | 1.6E-2 | 2.0E-2 | 1.8E-2 | 2.5E-2 | 2.0E-2 | 1.7E-2 | 1.0E-9 | 1.0E-9 | 1.0E-1 | 6.5E-2 | 45 | 15 | 35 | 15 | 0.65 |
| Rx | ng/ml | 1.0E-9 | 3.5E-5 | 2.6E-3 | 9.5E-4 | 4.4E-3 | 1.6E-3 | 1.0E-9 | 1.0E-9 | 2.0E-2 | 4.7E-3 | 45 | 15 | 35 | 15 | 0.46 |
| Ld | pg/ml | 1.0E-9 | 1.0E-9 | 4.0E0 | 2.6E0 | 9.9E0 | 4.7E0 | 1.0E-9 | 1.0E-9 | 6.9E1 | 2.5E1 | 108 | 44 | 85 | 44 | 0.50 |
| Lh | pg/ml | 1.1E4 | 2.3E4 | 2.0E4 | 3.4E4 | 2.9E4 | 5.3E4 | 1.0E-9 | 1.8E3 | 2.6E5 | 4.1E5 | 315 | 65 | 136 | 65 | 0.67 |
| Li | pg/ml | 2.6E3 | 6.7E3 | 8.5E3 | 2.9E4 | 2.3E4 | 7.8E4 | 1.0E-9 | 3.6E1 | 2.9E5 | 5.9E5 | 315 | 65 | 136 | 65 | 0.68 |
| Lj | pg/ml | 1.8E3 | 5.0E3 | 1.1E4 | 3.4E4 | 4.2E4 | 8.4E4 | 1.4E1 | 4.1E1 | 4.4E5 | 4.7E5 | 315 | 65 | 136 | 65 | 0.65 |
| Lp | pg/ml | 9.4E0 | 4.0E0 | 3.1E1 | 8.3E1 | 5.7E1 | 2.2E2 | 1.0E-9 | 1.0E-9 | 2.4E2 | 7.7E2 | 45 | 15 | 35 | 15 | 0.41 |
| Lt | pg/ml | 1.0E-9 | 1.0E-9 | 2.6E0 | 2.2E0 | 1.0E1 | 6.7E0 | 1.0E-9 | 1.0E-9 | 6.0E1 | 2.5E1 | 45 | 15 | 35 | 15 | 0.52 |
| Rv | ng/ml | 5.0E-4 | 5.0E-4 | 8.5E-4 | 6.9E-4 | 1.1E-3 | 7.4E-4 | 1.0E-9 | 1.0E-9 | 5.9E-3 | 2.2E-3 | 45 | 15 | 34 | 15 | 0.49 |
| Ru | ng/ml | 1.0E-9 | 1.0E-9 | 9.6E-3 | 3.0E-2 | 4.9E-2 | 9.9E-2 | 1.0E-9 | 1.0E-9 | 3.1E-1 | 3.8E-1 | 45 | 15 | 34 | 15 | 0.54 |
| Rt | ng/ml | 6.8E-2 | 3.2E-2 | 9.0E-2 | 1.2E-1 | 1.1E-1 | 1.8E-1 | 1.6E-3 | 1.0E-3 | 4.5E-1 | 5.6E-1 | 45 | 15 | 34 | 15 | 0.45 |
| Yl | pg/ml | 1.1E1 | 6.4E0 | 1.8E1 | 9.4E0 | 1.9E1 | 1.6E1 | 1.0E-9 | 1.0E-9 | 1.1E2 | 6.6E1 | 47 | 15 | 37 | 15 | 0.31 |
| Rm | ng/ml | 1.7E1 | 2.1E1 | 5.8E1 | 5.1E1 | 8.8E1 | 6.9E1 | 2.2E-1 | 1.3E0 | 4.0E2 | 2.5E2 | 110 | 43 | 83 | 43 | 0.53 |
| Rh | ng/ml | 1.4E2 | 2.0E2 | 2.9E2 | 3.5E2 | 5.7E2 | 4.9E2 | 4.7E0 | 4.3E1 | 3.8E3 | 2.5E3 | 110 | 43 | 83 | 43 | 0.58 |
| Ri | ng/ml | 1.0E-9 | 1.0E-9 | 3.9E0 | 3.5E0 | 9.2E0 | 8.0E0 | 1.0E-9 | 1.0E-9 | 7.4E1 | 4.5E1 | 111 | 43 | 84 | 43 | 0.46 |
| Rg | ng/ml | 1.0E-9 | 1.0E-9 | 2.7E-2 | 2.0E-2 | 2.6E-1 | 1.0E-1 | 1.0E-9 | 1.0E-9 | 2.7E0 | 6.8E-1 | 110 | 43 | 83 | 43 | 0.56 |
| Rj | ng/ml | 1.0E-9 | 1.0E-9 | 1.7E0 | 1.3E0 | 7.9E0 | 3.8E0 | 1.0E-9 | 1.0E-9 | 8.0E1 | 2.4E1 | 111 | 43 | 84 | 43 | 0.53 |
| Rf | ng/ml | 3.6E-1 | 5.7E-1 | 8.3E-1 | 1.4E0 | 1.6E0 | 2.4E0 | 7.8E-3 | 1.8E-2 | 1.4E1 | 1.2E1 | 110 | 43 | 83 | 43 | 0.62 |
| Ql | pg/ml | 7.3E0 | 7.8E0 | 1.4E1 | 2.0E1 | 3.1E1 | 3.7E1 | 1.0E-9 | 1.0E-9 | 2.9E2 | 1.8E2 | 111 | 44 | 86 | 44 | 0.54 |
| Qm | pg/ml | 1.7E0 | 1.6E1 | 1.9E1 | 2.6E1 | 4.4E1 | 3.7E1 | 1.0E-9 | 1.0E-9 | 3.6E2 | 1.7E2 | 111 | 44 | 86 | 44 | 0.61 |
| Qn | pg/ml | 6.1E-1 | 1.4E0 | 7.5E0 | 1.0E1 | 2.6E1 | 3.7E1 | 1.0E-9 | 1.0E-9 | 2.2E2 | 2.4E2 | 111 | 44 | 86 | 44 | 0.55 |
| Nv | pg/ml | 3.5E3 | 6.2E3 | 1.3E4 | 1.5E4 | 6.3E4 | 2.2E4 | 1.0E-9 | 4.9E2 | 1.1E6 | 1.1E5 | 318 | 66 | 136 | 66 | 0.66 |
| Nw | pg/ml | 7.4E3 | 1.6E4 | 1.2E4 | 1.8E4 | 2.2E4 | 1.8E4 | 8.6E1 | 2.6E3 | 2.1E5 | 1.4E5 | 318 | 66 | 136 | 66 | 0.71 |
| Nx | pg/ml | 1.7E2 | 2.6E2 | 3.9E2 | 6.5E2 | 7.1E2 | 7.6E2 | 1.0E-9 | 1.0E-9 | 7.4E3 | 2.6E3 | 318 | 66 | 136 | 66 | 0.65 |
| Ny | pg/ml | 4.7E0 | 1.0E1 | 1.1E2 | 3.2E1 | 1.4E3 | 9.2E1 | 1.0E-9 | 1.0E-9 | 2.5E4 | 6.2E2 | 318 | 66 | 136 | 66 | 0.60 |
| Oa | pg/ml | 1.6E2 | 2.8E2 | 4.4E2 | 4.4E2 | 8.0E2 | 5.5E2 | 1.0E-9 | 1.0E-9 | 4.8E3 | 2.4E3 | 111 | 44 | 86 | 44 | 0.56 |

Figure 14 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Op | pg/ml | 3.3E5 | 4.0E5 | 3.7E5 | 4.2E5 | 1.6E5 | 1.5E5 | 3.3E4 | 1.1E5 | 7.3E5 | 6.6E5 | 45 | 15 | 35 | 15 | 0.61 |
| Wn | ng/ml | 1.2E1 | 2.4E1 | 9.7E1 | 7.5E1 | 3.1E2 | 1.3E2 | 2.5E0 | 4.4E0 | 1.8E3 | 4.9E2 | 33 | 17 | 27 | 17 | 0.63 |
| Tk | ng/ml | 2.0E2 | 1.8E2 | 4.3E2 | 2.7E2 | 7.4E2 | 2.7E2 | 2.4E1 | 3.0E1 | 4.2E3 | 1.2E3 | 36 | 16 | 29 | 16 | 0.49 |
| Oe | pg/ml | 9.7E1 | 5.1E1 | 2.7E2 | 3.6E2 | 4.2E2 | 8.1E2 | 1.0E-9 | 1.0E-9 | 2.7E3 | 5.1E3 | 314 | 66 | 136 | 66 | 0.49 |
| Of | pg/ml | 2.1E2 | 5.7E2 | 5.6E3 | 1.6E4 | 1.8E4 | 7.7E4 | 1.0E-9 | 1.0E-9 | 1.8E5 | 6.2E5 | 317 | 66 | 136 | 66 | 0.55 |
| Og | pg/ml | 9.4E-2 | 1.1E-1 | 7.2E-1 | 1.9E0 | 2.2E0 | 9.8E0 | 1.0E-9 | 1.0E-9 | 2.0E1 | 7.9E1 | 317 | 66 | 136 | 66 | 0.54 |
| Oh | pg/ml | 2.0E0 | 3.8E0 | 2.5E1 | 1.4E1 | 1.2E2 | 4.2E1 | 1.0E-9 | 9.0E-2 | 1.4E3 | 2.2E2 | 317 | 66 | 136 | 66 | 0.63 |
| Oi | pg/ml | 2.9E0 | 5.2E0 | 7.2E0 | 9.7E0 | 1.1E1 | 1.1E1 | 1.0E-9 | 1.0E-9 | 8.6E1 | 4.2E1 | 317 | 66 | 136 | 66 | 0.59 |
| Ok | pg/ml | 3.2E2 | 7.2E2 | 4.3E2 | 9.6E2 | 3.9E2 | 1.2E3 | 1.3E1 | 7.1E1 | 3.1E3 | 9.8E3 | 317 | 66 | 136 | 66 | 0.75 |
| Om | pg/ml | 3.6E2 | 6.6E2 | 7.6E2 | 1.8E3 | 2.1E3 | 4.9E3 | 1.0E-9 | 1.0E-9 | 3.0E4 | 3.6E4 | 317 | 66 | 136 | 66 | 0.67 |
| On | pg/ml | 1.4E2 | 2.7E2 | 2.8E2 | 5.9E2 | 4.8E2 | 1.8E3 | 8.4E-1 | 2.7E1 | 4.5E3 | 1.5E4 | 317 | 66 | 136 | 66 | 0.68 |
| Or | pg/ml | 1.0E1 | 1.4E1 | 3.1E1 | 4.9E1 | 6.4E1 | 1.3E2 | 1.0E-9 | 1.0E-9 | 5.0E2 | 7.6E2 | 110 | 44 | 86 | 44 | 0.51 |
| Ow | pg/ml | 2.8E1 | 4.8E1 | 1.0E2 | 9.7E1 | 3.0E2 | 1.4E2 | 1.0E-9 | 1.0E-9 | 2.3E3 | 7.7E2 | 110 | 44 | 86 | 44 | 0.63 |
| Ou | pg/ml | 4.4E2 | 6.8E2 | 8.4E2 | 1.8E3 | 1.2E3 | 2.7E3 | 1.0E-9 | 1.0E-9 | 9.4E3 | 9.6E3 | 110 | 44 | 86 | 44 | 0.58 |
| Ul | ng/ml | 1.0E-9 | 1.0E-9 | 1.1E0 | 1.1E0 | 3.7E0 | 5.3E0 | 1.0E-9 | 1.0E-9 | 2.2E1 | 3.4E1 | 119 | 44 | 88 | 44 | 0.48 |
| Uo | ng/ml | 1.0E-9 | 1.0E-9 | 1.1E-1 | 7.0E-2 | 2.4E-1 | 1.8E-1 | 1.0E-9 | 1.0E-9 | 1.3E0 | 8.5E-1 | 119 | 44 | 88 | 44 | 0.46 |
| Uk | ng/ml | 1.0E-9 | 1.0E-9 | 4.8E-3 | 1.1E-2 | 1.2E-2 | 2.2E-2 | 1.0E-9 | 1.0E-9 | 9.9E-2 | 1.1E-1 | 119 | 44 | 88 | 44 | 0.53 |
| Um | ng/ml | 1.0E-9 | 1.0E-9 | 3.8E-1 | 1.7E-1 | 9.8E-1 | 3.2E-1 | 1.0E-9 | 1.0E-9 | 6.8E0 | 1.3E0 | 119 | 44 | 88 | 44 | 0.48 |
| Uf | ng/ml | 4.5E-2 | 1.1E-1 | 9.4E-2 | 1.9E-1 | 1.2E-1 | 3.7E-1 | 2.8E-3 | 8.3E-3 | 6.6E-1 | 2.5E0 | 119 | 44 | 88 | 44 | 0.69 |
| Uh | ng/ml | 1.8E0 | 3.0E0 | 2.5E0 | 4.6E0 | 2.3E0 | 4.5E0 | 3.2E-2 | 3.0E-1 | 1.1E1 | 1.7E1 | 119 | 44 | 88 | 44 | 0.65 |
| Un | ng/ml | 1.6E0 | 2.6E0 | 1.9E0 | 2.8E0 | 1.2E0 | 1.2E0 | 2.0E-1 | 7.4E-1 | 7.0E0 | 5.6E0 | 119 | 44 | 88 | 44 | 0.70 |
| Ug | ng/ml | 1.4E1 | 2.5E1 | 2.7E1 | 4.0E1 | 2.7E1 | 4.6E1 | 6.9E-1 | 1.1E0 | 1.3E2 | 2.1E2 | 119 | 44 | 88 | 44 | 0.56 |
| Ur | ng/ml | 1.6E-1 | 1.1E-1 | 1.2E0 | 5.7E-1 | 8.6E0 | 1.3E0 | 1.0E-9 | 1.0E-9 | 9.3E1 | 7.2E0 | 119 | 44 | 88 | 44 | 0.45 |
| Up | ng/ml | 1.0E-9 | 1.0E-9 | 7.5E-3 | 6.4E-3 | 3.4E-2 | 1.8E-2 | 1.0E-9 | 1.0E-9 | 3.3E-1 | 9.5E-2 | 119 | 44 | 88 | 44 | 0.53 |
| Us | ng/ml | 4.4E-3 | 5.9E-3 | 2.1E-2 | 1.7E-2 | 5.6E-2 | 2.5E-2 | 1.0E-9 | 1.0E-9 | 4.0E-1 | 1.0E-1 | 119 | 44 | 88 | 44 | 0.51 |
| Uv | ng/ml | 3.2E-3 | 3.9E-3 | 1.2E-2 | 1.0E-2 | 3.1E-2 | 2.2E-2 | 1.0E-9 | 1.0E-9 | 2.3E-1 | 1.3E-1 | 119 | 44 | 88 | 44 | 0.52 |
| Ut | ng/ml | 5.3E-1 | 9.5E-1 | 2.3E0 | 2.2E0 | 8.9E0 | 2.9E0 | 1.0E-9 | 1.0E-9 | 7.2E1 | 1.2E1 | 119 | 44 | 88 | 44 | 0.62 |
| Uu | ng/ml | 6.9E0 | 8.4E0 | 7.8E0 | 9.5E0 | 5.1E0 | 5.7E0 | 8.1E-1 | 6.0E-1 | 2.6E1 | 2.2E1 | 119 | 44 | 88 | 44 | 0.59 |
| Uw | ng/ml | 1.8E0 | 1.9E0 | 2.9E0 | 3.0E0 | 5.2E0 | 2.3E0 | 1.0E-9 | 2.0E-1 | 3.7E1 | 7.1E0 | 53 | 15 | 42 | 15 | 0.59 |
| Vb | ng/ml | 1.0E0 | 9.6E-1 | 1.0E0 | 1.0E0 | 4.2E-1 | 4.4E-1 | 2.1E-1 | 4.2E-1 | 2.5E0 | 1.8E0 | 53 | 15 | 42 | 15 | 0.46 |
| Vc | ng/ml | 1.0E-9 | 1.0E-9 | 2.3E-3 | 1.0E-9 | 1.5E-2 | 0.0E0 | 1.0E-9 | 1.0E-9 | 1.1E-1 | 1.0E-9 | 53 | 15 | 42 | 15 | 0.47 |
| Uy | ng/ml | 1.0E0 | 9.5E-1 | 2.9E0 | 2.5E0 | 6.6E0 | 4.1E0 | 5.3E-2 | 3.1E-2 | 3.5E1 | 1.6E1 | 53 | 15 | 42 | 15 | 0.46 |
| Uz | ng/ml | 1.0E-9 | 1.0E-9 | 8.3E-3 | 1.0E-9 | 6.0E-2 | 0.0E0 | 1.0E-9 | 1.0E-9 | 4.4E-1 | 1.0E-9 | 53 | 15 | 42 | 15 | 0.48 |
| Ux | ng/ml | 1.2E2 | 2.5E2 | 1.6E2 | 2.5E2 | 1.3E2 | 1.6E2 | 5.8E0 | 5.8E1 | 4.6E2 | 5.3E2 | 53 | 15 | 42 | 15 | 0.68 |
| Va | ng/ml | 1.6E1 | 1.4E1 | 2.3E1 | 2.6E1 | 2.5E1 | 3.2E1 | 3.1E-1 | 1.5E0 | 1.2E2 | 1.2E2 | 53 | 15 | 42 | 15 | 0.49 |
| Vh | ng/ml | 4.4E-3 | 1.1E-2 | 1.1E-2 | 1.8E-2 | 1.9E-2 | 2.1E-2 | 1.0E-9 | 5.2E-4 | 1.2E-1 | 7.6E-2 | 53 | 15 | 42 | 15 | 0.63 |
| Vi | ng/ml | 2.4E-3 | 3.9E-3 | 2.6E-1 | 1.4E-2 | 1.9E0 | 2.3E-2 | 1.0E-9 | 9.0E-5 | 1.4E1 | 7.5E-2 | 53 | 15 | 42 | 15 | 0.58 |
| Vj | ng/ml | 2.2E1 | 5.7E1 | 1.8E2 | 6.6E2 | 7.4E2 | 2.2E3 | 3.2E0 | 9.7E0 | 5.2E3 | 8.4E3 | 53 | 14 | 42 | 14 | 0.67 |
| Vp | ng/ml | 1.0E-9 | 1.0E-9 | 7.4E-1 | 1.1E-2 | 5.2E0 | 4.5E-2 | 1.0E-9 | 1.0E-9 | 5.0E1 | 2.6E-1 | 119 | 44 | 88 | 44 | 0.44 |
| Vt | ng/ml | 6.1E0 | 7.9E0 | 7.6E0 | 1.1E1 | 6.1E0 | 1.2E1 | 6.0E-1 | 1.1E0 | 3.2E1 | 6.5E1 | 119 | 44 | 88 | 44 | 0.60 |
| Vu | ng/ml | 1.0E-9 | 1.0E-9 | 2.3E0 | 2.0E0 | 6.0E0 | 4.1E0 | 1.0E-9 | 1.0E-9 | 5.1E1 | 2.1E1 | 118 | 43 | 88 | 43 | 0.50 |
| Vq | ng/ml | 1.2E2 | 5.8E2 | 5.5E2 | 1.3E3 | 1.2E3 | 2.3E3 | 2.0E-1 | 9.0E-1 | 1.0E4 | 1.1E4 | 94 | 28 | 72 | 28 | 0.63 |
| Vo | ng/ml | 2.6E1 | 2.6E1 | 2.5E1 | 2.5E1 | 4.9E0 | 3.2E0 | 2.5E0 | 1.5E1 | 3.5E1 | 3.4E1 | 119 | 44 | 88 | 44 | 0.52 |
| Vs | ng/ml | 1.0E-9 | 1.4E0 | 6.5E0 | 4.5E0 | 2.7E1 | 8.5E0 | 1.0E-9 | 1.0E-9 | 2.3E2 | 4.2E1 | 116 | 41 | 86 | 41 | 0.57 |
| Vv | ng/ml | 2.7E0 | 4.5E0 | 6.0E0 | 8.1E0 | 1.0E1 | 1.3E1 | 1.0E-9 | 1.0E-9 | 8.1E1 | 8.0E1 | 118 | 44 | 88 | 44 | 0.59 |
| Vw | ng/ml | 3.3E1 | 4.3E1 | 3.1E1 | 4.4E1 | 1.7E1 | 1.6E1 | 2.5E0 | 1.8E1 | 6.7E1 | 7.0E1 | 53 | 15 | 42 | 15 | 0.70 |
| Oy | pg/ml | 5.5E-1 | 6.8E-1 | 8.7E0 | 7.4E0 | 4.2E1 | 3.4E1 | 1.0E-9 | 1.0E-9 | 4.0E2 | 2.7E2 | 317 | 66 | 136 | 66 | 0.57 |
| Oz | pg/ml | 4.5E-3 | 2.0E-1 | 2.2E-1 | 4.0E-1 | 3.7E-1 | 7.9E-1 | 1.0E-9 | 1.0E-9 | 2.6E0 | 5.8E0 | 317 | 66 | 136 | 66 | 0.61 |
| Pa | pg/ml | 3.4E-1 | 4.2E-1 | 1.3E0 | 5.4E0 | 5.8E0 | 3.6E1 | 1.0E-9 | 1.0E-9 | 8.6E1 | 2.9E2 | 317 | 66 | 136 | 66 | 0.58 |
| Pb | pg/ml | 1.0E-9 | 3.3E-2 | 1.8E0 | 2.9E0 | 2.7E1 | 2.2E1 | 1.0E-9 | 1.0E-9 | 4.9E2 | 1.8E2 | 317 | 66 | 136 | 66 | 0.56 |
| Pc | pg/ml | 4.4E-2 | 3.6E-1 | 4.3E-1 | 6.5E-1 | 1.3E0 | 1.6E0 | 1.0E-9 | 1.0E-9 | 1.6E1 | 1.1E1 | 317 | 66 | 136 | 66 | 0.60 |
| Pd | pg/ml | 1.8E0 | 3.1E0 | 3.8E0 | 5.3E0 | 8.2E0 | 5.7E0 | 1.0E-9 | 1.2E-1 | 9.4E1 | 2.7E1 | 317 | 66 | 136 | 66 | 0.65 |
| Pe | pg/ml | 1.8E1 | 3.6E1 | 8.9E1 | 3.0E2 | 3.5E2 | 1.7E3 | 1.0E-9 | 1.0E-9 | 4.7E3 | 1.4E4 | 317 | 66 | 136 | 66 | 0.68 |
| Pf | pg/ml | 1.2E0 | 2.7E0 | 6.2E0 | 1.2E1 | 2.6E1 | 3.4E1 | 1.0E-9 | 8.1E-2 | 3.3E2 | 2.3E2 | 317 | 66 | 136 | 66 | 0.66 |
| Pg | pg/ml | 3.2E0 | 4.7E0 | 4.0E1 | 5.0E1 | 2.1E2 | 2.3E2 | 1.0E-9 | 2.7E-1 | 3.2E3 | 1.9E3 | 317 | 66 | 136 | 66 | 0.58 |
| Ph | ng/ml | 1.4E-1 | 2.5E-1 | 2.7E-1 | 5.7E-1 | 3.5E-1 | 8.9E-1 | 1.0E-9 | 1.0E-9 | 2.2E0 | 4.4E0 | 110 | 44 | 86 | 44 | 0.61 |
| Pi | ng/ml | 1.9E-1 | 2.1E-1 | 2.8E-1 | 2.6E-1 | 4.4E-1 | 2.3E-1 | 1.0E-9 | 1.0E-9 | 3.2E0 | 1.0E0 | 110 | 44 | 86 | 44 | 0.53 |

Figure 14 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Pj | ng/mL | 4.4E0 | 7.9E0 | 5.1E0 | 9.3E0 | 3.3E0 | 6.2E0 | 3.8E-2 | 9.9E-1 | 1.6E1 | 2.5E1 | 110 | 44 | 86 | 44 | 0.70 |
| Pk | ng/ml | 8.1E-3 | 7.1E-3 | 1.1E-2 | 1.0E-2 | 1.2E-2 | 1.3E-2 | 1.0E-9 | 1.0E-9 | 5.9E-2 | 7.0E-2 | 110 | 44 | 86 | 44 | 0.48 |
| aA | mg/dL | 8.0E-1 | 9.2E-1 | 9.2E-1 | 1.1E0 | 4.3E-1 | 7.6E-1 | 3.0E-1 | 2.6E-1 | 4.2E0 | 5.4E0 | 1242 | 95 | 226 | 95 | 0.55 |
| aC | mg/mL | 3.1E0 | 2.5E0 | 3.3E0 | 2.8E0 | 1.4E0 | 1.1E0 | 1.1E0 | 1.3E0 | 8.2E0 | 6.3E0 | 221 | 50 | 91 | 50 | 0.39 |
| aD | ug/mL | 2.9E0 | 4.2E0 | 4.1E0 | 5.3E0 | 3.2E0 | 3.9E0 | 8.5E-1 | 8.4E-1 | 2.8E1 | 2.0E1 | 221 | 50 | 91 | 50 | 0.61 |
| aE | mg/mL | 5.8E-1 | 5.5E-1 | 5.8E-1 | 5.6E-1 | 1.5E-1 | 1.4E-1 | 2.1E-1 | 3.1E-1 | 1.1E0 | 1.2E0 | 221 | 50 | 91 | 50 | 0.44 |
| aF | ng/mL | 2.1E0 | 1.6E0 | 4.4E0 | 3.6E0 | 7.0E0 | 4.5E0 | 4.3E-3 | 4.3E-3 | 5.0E1 | 1.8E1 | 221 | 50 | 91 | 50 | 0.45 |
| aG | mg/mL | 1.3E-1 | 1.4E-1 | 1.5E-1 | 1.5E-1 | 7.8E-2 | 8.4E-2 | 5.0E-2 | 5.8E-2 | 5.0E-1 | 4.0E-1 | 221 | 50 | 91 | 50 | 0.49 |
| aH | ug/mL | 6.8E1 | 8.0E1 | 7.8E1 | 8.8E1 | 3.5E1 | 5.2E1 | 1.5E1 | 1.1E1 | 2.7E2 | 2.6E2 | 221 | 50 | 91 | 50 | 0.54 |
| aI | ug/mL | 1.8E2 | 1.9E2 | 1.9E2 | 1.9E2 | 6.0E1 | 5.5E1 | 5.8E1 | 4.8E1 | 3.7E2 | 2.8E2 | 221 | 50 | 91 | 50 | 0.51 |
| aJ | ug/mL | 2.5E0 | 3.0E0 | 3.0E0 | 3.8E0 | 1.9E0 | 2.9E0 | 9.0E-1 | 1.0E0 | 1.2E1 | 1.5E1 | 221 | 50 | 91 | 50 | 0.59 |
| aK | ng/mL | 1.8E0 | 1.2E0 | 2.7E0 | 1.7E0 | 2.7E0 | 1.5E0 | 8.4E-2 | 2.9E-4 | 1.8E1 | 5.7E0 | 221 | 50 | 91 | 50 | 0.38 |
| aL | mg/mL | 8.1E-1 | 8.0E-1 | 8.3E-1 | 8.0E-1 | 2.4E-1 | 2.2E-1 | 3.0E-1 | 1.0E0 | 1.6E0 | 1.5E0 | 221 | 50 | 91 | 50 | 0.47 |
| aM | U/mL | 1.9E1 | 3.9E1 | 3.7E1 | 5.8E1 | 1.1E2 | 6.5E1 | 4.2E-2 | 4.2E-2 | 1.6E3 | 4.0E2 | 221 | 50 | 91 | 50 | 0.68 |
| aN | U/mL | 1.0E1 | 1.8E1 | 1.8E1 | 2.6E1 | 2.1E1 | 2.7E1 | 2.5E-3 | 2.5E-3 | 1.3E2 | 1.1E2 | 221 | 50 | 91 | 50 | 0.61 |
| aO | pg/mL | 3.9E1 | 7.3E1 | 3.7E2 | 4.5E2 | 9.9E2 | 8.7E2 | 6.0E-2 | 2.1E0 | 6.6E3 | 3.6E3 | 221 | 50 | 91 | 50 | 0.56 |
| aP | ng/mL | 1.7E0 | 1.7E0 | 1.9E0 | 2.2E0 | 1.1E0 | 1.5E0 | 5.4E-1 | 7.5E-1 | 6.6E0 | 6.5E0 | 221 | 50 | 91 | 50 | 0.54 |
| aQ | ng/mL | 3.2E-1 | 2.2E-1 | 5.0E-1 | 3.4E-1 | 5.2E-1 | 3.1E-1 | 1.9E-2 | 2.5E-2 | 4.0E0 | 1.3E0 | 221 | 50 | 91 | 50 | 0.38 |
| aR | ng/mL | 1.6E0 | 2.3E0 | 2.4E0 | 3.9E0 | 2.5E0 | 4.9E0 | 1.8E-1 | 6.2E-1 | 2.1E1 | 3.0E1 | 221 | 50 | 91 | 50 | 0.64 |
| aS | ng/mL | 2.4E-1 | 3.3E-1 | 7.8E-1 | 5.6E-1 | 2.5E0 | 9.1E-1 | 4.2E-3 | 4.2E-3 | 3.3E1 | 6.1E0 | 221 | 50 | 91 | 50 | 0.55 |
| aU | pg/mL | 8.8E1 | 6.1E1 | 1.4E2 | 8.6E1 | 1.6E2 | 8.7E1 | 7.4E0 | 7.4E-2 | 1.3E3 | 4.8E2 | 221 | 50 | 91 | 50 | 0.37 |
| aV | ng/mL | 7.3E-1 | 4.6E-1 | 1.1E0 | 7.6E-1 | 1.1E0 | 8.5E-1 | 3.1E-2 | 3.8E-2 | 8.7E0 | 4.2E0 | 221 | 50 | 91 | 50 | 0.38 |
| aW | pg/mL | 1.7E1 | 2.3E1 | 2.0E1 | 3.0E1 | 2.6E1 | 6.1E1 | 7.2E-2 | 7.2E-2 | 2.4E2 | 4.5E2 | 221 | 50 | 91 | 50 | 0.61 |
| aX | ng/mL | 1.0E1 | 9.5E0 | 1.3E1 | 1.3E1 | 1.2E1 | 1.1E1 | 3.0E-1 | 1.4E0 | 6.7E1 | 4.6E1 | 221 | 50 | 91 | 50 | 0.49 |
| aY | pg/mL | 5.0E1 | 7.2E1 | 7.2E1 | 9.0E1 | 7.1E1 | 7.0E1 | 4.1E-1 | 4.1E-1 | 4.4E2 | 3.7E2 | 221 | 50 | 91 | 50 | 0.62 |
| aZ | pg/mL | 2.2E2 | 2.4E2 | 4.8E2 | 4.8E2 | 7.2E2 | 9.0E2 | 1.7E0 | 1.7E0 | 5.4E3 | 5.9E3 | 221 | 50 | 91 | 50 | 0.49 |
| bA | ng/mL | 8.0E0 | 1.3E1 | 2.6E1 | 4.7E1 | 6.2E1 | 9.7E1 | 3.0E-2 | 3.0E-2 | 7.1E2 | 6.2E2 | 221 | 50 | 91 | 50 | 0.62 |
| bB | ng/mL | 3.1E2 | 3.0E2 | 3.4E2 | 3.0E2 | 1.6E2 | 1.7E2 | 1.6E1 | 2.3E1 | 1.0E3 | 7.2E2 | 221 | 50 | 91 | 50 | 0.45 |
| bC | ng/mL | 3.5E2 | 4.1E2 | 5.1E2 | 7.8E2 | 5.3E2 | 1.1E3 | 2.7E1 | 4.6E1 | 4.0E3 | 4.7E3 | 221 | 50 | 91 | 50 | 0.57 |
| bE | mg/mL | 5.6E0 | 5.4E0 | 5.9E0 | 6.0E0 | 1.7E0 | 2.3E0 | 1.9E0 | 1.4E0 | 1.3E1 | 1.2E1 | 221 | 50 | 91 | 50 | 0.50 |
| bF | pg/mL | 2.0E1 | 2.6E1 | 8.6E1 | 9.2E1 | 4.4E2 | 3.1E2 | 5.0E-2 | 2.8E0 | 5.0E3 | 2.2E3 | 221 | 50 | 91 | 50 | 0.59 |
| bG | ng/mL | 1.8E0 | 1.3E0 | 3.0E0 | 2.9E0 | 3.7E0 | 3.4E0 | 2.2E-2 | 2.4E-1 | 2.6E1 | 1.5E1 | 221 | 50 | 91 | 50 | 0.45 |
| bH | pg/mL | 5.7E-1 | 5.7E-1 | 5.4E0 | 3.0E0 | 2.0E1 | 5.1E0 | 5.7E-1 | 5.7E-1 | 2.8E2 | 2.2E1 | 221 | 50 | 91 | 50 | 0.45 |
| bI | ng/mL | 4.0E-3 | 4.0E-3 | 6.8E-2 | 5.5E-2 | 1.7E-1 | 1.1E-1 | 4.0E-3 | 4.0E-3 | 1.3E0 | 4.5E-1 | 221 | 50 | 91 | 50 | 0.50 |
| bJ | mg/mL | 2.2E0 | 2.1E0 | 2.5E0 | 2.5E0 | 1.9E0 | 2.0E0 | 2.5E-4 | 2.5E-4 | 1.3E1 | 1.0E1 | 221 | 50 | 91 | 50 | 0.49 |
| bL | pg/mL | 4.1E0 | 2.9E0 | 7.8E0 | 6.2E0 | 9.3E0 | 7.7E0 | 4.6E-2 | 4.6E-2 | 4.9E1 | 2.7E1 | 221 | 50 | 91 | 50 | 0.43 |
| bM | mg/mL | 1.5E0 | 2.2E0 | 1.8E0 | 2.5E0 | 1.2E0 | 1.4E0 | 9.2E-3 | 4.1E-1 | 7.1E0 | 6.3E0 | 221 | 50 | 91 | 50 | 0.67 |
| bN | ng/mL | 3.2E1 | 5.9E1 | 1.1E2 | 1.1E2 | 2.6E2 | 1.8E2 | 9.7E-1 | 5.9E-1 | 1.9E3 | 1.2E3 | 221 | 50 | 91 | 50 | 0.56 |
| bO | ng/mL | 4.0E-2 | 4.0E-2 | 1.1E1 | 1.0E1 | 2.4E1 | 2.9E1 | 4.0E-2 | 4.0E-2 | 1.9E2 | 1.9E2 | 221 | 50 | 91 | 50 | 0.44 |
| bP | mg/mL | 5.6E-1 | 5.0E-1 | 7.9E-1 | 7.4E-1 | 6.6E-1 | 6.9E-1 | 8.2E-1 | 1.3E-1 | 3.8E0 | 3.1E0 | 221 | 50 | 91 | 50 | 0.47 |
| bQ | pg/mL | 1.4E1 | 1.8E1 | 2.4E1 | 2.1E1 | 3.5E1 | 1.6E1 | 1.5E-1 | 1.5E-1 | 3.2E2 | 6.6E1 | 221 | 50 | 91 | 50 | 0.53 |
| bR | ng/mL | 1.2E-2 | 1.2E-2 | 1.4E-1 | 7.0E-2 | 2.8E-1 | 9.7E-2 | 1.2E-2 | 1.2E-2 | 3.4E0 | 3.9E-1 | 221 | 50 | 91 | 50 | 0.42 |
| bS | pg/mL | 9.4E-1 | 9.4E-1 | 8.1E0 | 4.4E0 | 2.9E1 | 1.1E1 | 9.4E-1 | 9.4E-1 | 3.4E2 | 5.9E1 | 221 | 50 | 91 | 50 | 0.48 |
| bU | ng/mL | 1.6E-1 | 1.3E-2 | 2.1E-1 | 1.0E-1 | 2.6E-1 | 1.3E-1 | 1.3E-2 | 1.3E-2 | 1.8E0 | 5.7E-1 | 221 | 50 | 91 | 50 | 0.36 |
| bV | pg/mL | 4.7E2 | 4.7E2 | 5.3E2 | 6.0E2 | 2.5E2 | 4.4E2 | 1.7E2 | 2.5E2 | 1.6E3 | 3.1E3 | 221 | 50 | 91 | 50 | 0.53 |
| bW | pg/mL | 3.5E2 | 3.9E2 | 4.7E2 | 6.1E2 | 4.2E2 | 9.1E2 | 1.1E2 | 1.2E2 | 3.4E3 | 6.4E3 | 221 | 50 | 91 | 50 | 0.54 |
| bX | ng/mL | 3.1E-3 | 2.5E-5 | 3.2E-3 | 1.9E-3 | 3.8E-3 | 2.6E-3 | 2.5E-5 | 2.5E-5 | 2.0E-2 | 8.8E-3 | 221 | 50 | 91 | 50 | 0.41 |
| bZ | pg/mL | 2.5E2 | 2.5E2 | 7.5E2 | 5.0E2 | 3.2E3 | 8.4E2 | 1.5E-1 | 2.4E1 | 4.4E4 | 5.6E3 | 221 | 50 | 91 | 50 | 0.51 |
| cA | pg/mL | 6.0E-1 | 6.0E-1 | 1.9E0 | 1.3E0 | 3.4E0 | 2.3E0 | 6.0E-1 | 6.0E-1 | 1.4E1 | 1.0E1 | 221 | 50 | 91 | 50 | 0.47 |
| cB | ng/mL | 6.0E-2 | 3.4E-2 | 9.0E-2 | 5.8E-2 | 1.0E-1 | 7.2E-2 | 1.7E-3 | 1.7E-3 | 5.4E-1 | 3.0E-1 | 221 | 50 | 91 | 50 | 0.39 |
| cC | pg/mL | 4.6E1 | 3.3E1 | 4.9E1 | 3.3E1 | 3.9E1 | 2.7E1 | 1.0E0 | 1.0E0 | 3.7E2 | 1.1E2 | 221 | 50 | 91 | 50 | 0.37 |
| cD | ng/mL | 6.1E0 | 4.0E0 | 1.3E1 | 1.2E1 | 4.0E1 | 2.3E1 | 3.3E-1 | 3.3E-1 | 4.8E2 | 1.4E2 | 221 | 50 | 91 | 50 | 0.43 |
| cE | pg/mL | 3.1E1 | 4.2E1 | 9.3E1 | 1.4E2 | 2.7E2 | 4.4E2 | 1.5E0 | 1.2E-1 | 3.1E3 | 3.1E3 | 221 | 50 | 91 | 50 | 0.56 |
| cF | pg/mL | 1.3E1 | 9.4E0 | 2.4E1 | 1.2E1 | 3.6E1 | 1.5E1 | 5.3E-1 | 5.3E-1 | 2.2E2 | 7.2E1 | 221 | 50 | 91 | 50 | 0.42 |
| cG | pg/mL | 4.2E1 | 5.6E1 | 6.4E1 | 1.2E2 | 8.8E1 | 2.4E2 | 1.1E1 | 1.5E1 | 1.1E3 | 1.6E3 | 221 | 50 | 91 | 50 | 0.63 |
| cH | uIU/mL | 2.9E0 | 3.7E0 | 6.0E0 | 7.1E0 | 8.9E0 | 1.1E1 | 8.6E-3 | 8.6E-3 | 8.7E1 | 5.2E1 | 221 | 50 | 91 | 50 | 0.51 |
| cI | ng/mL | 6.0E0 | 4.7E0 | 1.1E1 | 1.4E1 | 1.3E1 | 2.3E1 | 1.0E-3 | 8.0E-2 | 9.4E1 | 1.2E2 | 221 | 50 | 91 | 50 | 0.47 |

Figure 14 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cJ | ug/mL | 7.2E1 | 4.9E1 | 1.2E2 | 9.5E1 | 1.5E2 | 1.4E2 | 4.0E0 | 1.1E1 | 9.6E2 | 6.9E2 | 221 | 50 | 91 | 50 | 0.42 |
| cK | ng/mL | 3.8E-3 | 3.8E-3 | 7.5E-2 | 8.4E-3 | 2.2E-1 | 2.4E-2 | 3.8E-3 | 3.8E-3 | 1.7E0 | 1.6E-1 | 221 | 50 | 91 | 50 | 0.42 |
| cL | pg/mL | 1.9E2 | 2.0E2 | 2.7E2 | 3.7E2 | 5.1E2 | 8.3E2 | 2.5E1 | 1.6E1 | 7.1E3 | 5.8E3 | 221 | 50 | 91 | 50 | 0.53 |
| cM | pg/mL | 2.9E2 | 2.6E2 | 3.2E2 | 2.9E2 | 1.8E2 | 2.1E2 | 3.7E1 | 3.3E1 | 1.2E3 | 1.5E3 | 221 | 50 | 91 | 50 | 0.43 |
| cN | pg/mL | 1.2E2 | 1.2E2 | 1.2E2 | 1.4E2 | 4.4E1 | 4.8E1 | 3.8E1 | 4.3E1 | 2.7E2 | 2.7E2 | 221 | 50 | 91 | 50 | 0.57 |
| cO | pg/mL | 2.3E2 | 2.4E2 | 2.8E2 | 2.5E2 | 2.0E2 | 1.1E2 | 5.4E1 | 1.0E2 | 1.7E3 | 6.3E2 | 221 | 50 | 91 | 50 | 0.50 |
| cP | ng/mL | 2.4E3 | 2.9E3 | 2.5E3 | 3.0E3 | 8.9E2 | 9.9E2 | 6.2E2 | 1.5E3 | 5.7E3 | 5.9E3 | 221 | 50 | 91 | 50 | 0.65 |
| cQ | ng/mL | 4.0E-2 | 6.4E-2 | 1.1E-1 | 1.4E-1 | 1.8E-1 | 2.5E-1 | 2.0E-3 | 2.0E-3 | 1.2E0 | 1.4E0 | 221 | 50 | 91 | 50 | 0.57 |
| cR | ng/mL | 2.8E2 | 3.8E2 | 4.3E2 | 6.7E2 | 4.6E2 | 1.1E3 | 2.3E1 | 3.0E1 | 3.8E3 | 7.7E3 | 221 | 50 | 91 | 50 | 0.59 |
| cS | ng/mL | 2.4E2 | 2.9E2 | 3.9E2 | 4.5E2 | 4.2E2 | 5.2E2 | 5.3E1 | 7.0E1 | 2.7E3 | 2.6E3 | 221 | 50 | 91 | 50 | 0.55 |
| cT | ng/mL | 2.8E1 | 3.7E1 | 7.4E1 | 1.0E2 | 1.5E2 | 1.6E2 | 4.6E0 | 6.9E0 | 1.7E3 | 7.4E2 | 221 | 50 | 91 | 50 | 0.58 |
| cU | ng/mL | 5.5E1 | 5.8E1 | 7.4E1 | 7.2E1 | 7.2E1 | 5.3E1 | 1.0E1 | 1.4E1 | 7.7E2 | 2.7E2 | 221 | 50 | 91 | 50 | 0.51 |
| cV | ng/mL | 1.7E-1 | 1.9E-1 | 4.9E-1 | 2.8E-1 | 3.2E0 | 3.1E-1 | 3.4E-4 | 3.7E-2 | 4.7E1 | 2.0E0 | 221 | 50 | 91 | 50 | 0.53 |
| cW | mIU/mL | 4.6E-2 | 5.5E-2 | 2.2E-1 | 8.1E-2 | 1.0E0 | 7.1E-2 | 3.7E-4 | 1.0E-2 | 9.7E0 | 2.9E-1 | 221 | 50 | 91 | 50 | 0.56 |
| cX | ng/mL | 1.1E-1 | 1.8E-1 | 1.8E0 | 8.7E-1 | 5.4E0 | 1.6E0 | 2.3E-4 | 2.3E-4 | 2.8E1 | 8.5E0 | 221 | 50 | 91 | 50 | 0.52 |
| cY | ng/mL | 1.0E1 | 7.2E0 | 1.4E1 | 9.8E0 | 1.4E1 | 8.4E0 | 4.4E-1 | 1.5E-1 | 8.3E1 | 3.2E1 | 221 | 50 | 91 | 50 | 0.39 |
| cZ | ug/mL | 1.4E1 | 1.5E1 | 1.5E1 | 1.6E1 | 5.8E0 | 7.6E0 | 5.3E0 | 3.1E0 | 3.9E1 | 3.7E1 | 221 | 50 | 91 | 50 | 0.52 |
| dA | pg/mL | 3.3E2 | 3.3E2 | 3.6E2 | 3.6E2 | 1.6E2 | 1.6E2 | 9.0E1 | 1.3E2 | 1.3E3 | 8.2E2 | 221 | 50 | 91 | 50 | 0.51 |
| dB | ug/mL | 1.7E1 | 1.6E1 | 1.9E1 | 1.5E1 | 2.1E1 | 1.0E1 | 1.9E0 | 1.8E0 | 2.5E2 | 4.1E1 | 221 | 50 | 91 | 50 | 0.44 |
| dC | nmol/L | 3.4E1 | 3.7E1 | 4.1E1 | 3.9E1 | 2.0E1 | 1.9E1 | 9.1E0 | 1.9E1 | 1.4E2 | 8.3E1 | 221 | 50 | 91 | 50 | 0.50 |
| dD | ug/mL | 3.7E1 | 3.4E1 | 3.8E1 | 3.6E1 | 1.0E1 | 1.1E1 | 1.3E1 | 1.3E1 | 7.6E1 | 5.7E1 | 221 | 50 | 91 | 50 | 0.44 |
| dE | ng/mL | 4.8E-1 | 2.7E-1 | 6.7E-1 | 4.6E-1 | 8.3E-1 | 6.4E-1 | 8.4E-3 | 8.4E-3 | 7.2E0 | 3.3E0 | 221 | 50 | 91 | 50 | 0.40 |
| dF | ng/mL | 2.1E2 | 2.6E2 | 2.6E2 | 3.1E2 | 1.8E2 | 1.8E2 | 7.5E1 | 1.0E2 | 1.2E3 | 9.7E2 | 221 | 50 | 91 | 50 | 0.60 |
| dG | ng/mL | 1.1E1 | 1.4E1 | 1.3E1 | 1.6E1 | 8.4E0 | 7.3E0 | 3.1E0 | 6.4E0 | 6.4E1 | 3.4E1 | 221 | 50 | 91 | 50 | 0.61 |
| dH | pg/mL | 7.5E0 | 7.9E0 | 1.2E1 | 9.9E0 | 2.4E1 | 8.6E0 | 4.0E-2 | 4.0E-2 | 3.1E2 | 5.0E1 | 221 | 50 | 91 | 50 | 0.52 |
| dI | pg/mL | 4.6E-1 | 4.6E-1 | 1.9E0 | 7.9E-1 | 4.4E0 | 1.1E0 | 4.6E-1 | 4.6E-1 | 3.4E1 | 6.0E0 | 221 | 50 | 91 | 50 | 0.44 |
| dJ | ng/mL | 1.9E0 | 1.9E0 | 2.1E0 | 2.0E0 | 1.1E0 | 1.1E0 | 3.2E-2 | 4.0E-1 | 5.9E0 | 5.1E0 | 221 | 50 | 91 | 50 | 0.48 |
| dK | uIU/mL | 2.0E0 | 1.6E0 | 2.7E0 | 2.4E0 | 2.9E0 | 3.2E0 | 2.8E-4 | 3.8E-2 | 1.6E1 | 2.1E1 | 221 | 50 | 91 | 50 | 0.46 |
| dL | ng/mL | 8.8E2 | 1.0E3 | 1.0E3 | 1.1E3 | 4.8E2 | 5.2E2 | 3.4E2 | 4.7E2 | 3.4E3 | 3.3E3 | 221 | 50 | 91 | 50 | 0.60 |
| dM | pg/mL | 9.7E2 | 1.1E3 | 1.2E3 | 1.4E3 | 1.1E3 | 1.2E3 | 4.4E2 | 4.2E2 | 1.2E4 | 8.3E3 | 221 | 50 | 91 | 50 | 0.54 |
| dN | ug/mL | 9.0E1 | 1.0E2 | 9.7E1 | 1.0E2 | 3.4E1 | 3.8E1 | 2.5E1 | 3.7E1 | 2.4E2 | 2.1E2 | 221 | 50 | 91 | 50 | 0.58 |
| dO | ng/ml | 2.8E1 | 9.0E0 | 4.9E1 | 2.0E1 | 6.6E1 | 2.5E1 | 6.1E0 | 3.8E0 | 3.7E2 | 7.9E1 | 44 | 13 | 29 | 13 | 0.25 |
| dR | pg/ml | 1.6E3 | 1.6E3 | 2.5E3 | 1.9E3 | 2.6E3 | 1.7E3 | 1.9E2 | 1.7E2 | 1.5E4 | 8.1E3 | 131 | 47 | 88 | 47 | 0.44 |
| dQ | Absorbance | 5.2E-1 | 2.1E-1 | 6.2E-1 | 2.7E-1 | 5.0E-1 | 1.7E-1 | 7.9E-2 | 1.2E-1 | 2.5E0 | 6.5E-1 | 28 | 7 | 18 | 7 | 0.24 |
| dU | pg/ml | 8.8E3 | 1.8E4 | 1.3E4 | 2.1E4 | 1.2E4 | 1.2E4 | 2.5E3 | 6.7E3 | 5.3E4 | 3.8E4 | 28 | 7 | 26 | 7 | 0.76 |
| dV | pg/ml | 7.2E1 | 6.8E1 | 9.0E1 | 1.7E2 | 5.5E1 | 2.6E2 | 3.4E1 | 3.6E1 | 2.7E2 | 8.9E2 | 35 | 10 | 18 | 10 | 0.49 |
| dX | ng/ml | 3.4E-2 | 7.4E-3 | 9.5E-2 | 1.8E-1 | 1.5E-1 | 3.5E-1 | 2.6E-3 | 2.6E-3 | 7.4E-1 | 9.4E-1 | 65 | 11 | 21 | 11 | 0.43 |
| eF | ng/ml | 4.0E0 | 4.6E0 | 4.6E0 | 5.2E0 | 2.6E0 | 2.3E0 | 1.5E0 | 2.0E0 | 1.8E1 | 1.2E1 | 138 | 48 | 88 | 48 | 0.61 |
| eC | pg/ml | 3.1E2 | 3.0E2 | 3.8E2 | 3.2E2 | 2.5E2 | 1.4E2 | 4.5E1 | 5.1E1 | 1.4E3 | 6.2E2 | 100 | 39 | 86 | 39 | 0.45 |
| eD | pg/ml | 2.3E2 | 2.3E2 | 7.7E2 | 5.0E2 | 1.4E3 | 1.0E3 | 5.2E-1 | 5.2E-1 | 6.8E3 | 5.5E3 | 77 | 29 | 64 | 29 | 0.51 |
| eM | ng/ml | 3.6E0 | 4.1E0 | 4.4E0 | 6.7E0 | 3.5E0 | 6.2E0 | 8.1E-1 | 9.0E-1 | 2.2E1 | 2.5E1 | 87 | 18 | 34 | 18 | 0.61 |
| eP | ng/ml | 3.7E-3 | 1.2E-1 | 1.0E0 | 6.3E0 | 2.1E0 | 1.9E1 | 3.7E-3 | 3.7E-3 | 1.2E1 | 6.5E1 | 65 | 11 | 21 | 11 | 0.53 |
| eT | ng/ml | 2.7E2 | 2.7E2 | 5.6E2 | 4.5E2 | 6.1E2 | 4.8E2 | 1.0E2 | 1.6E2 | 2.5E3 | 1.9E3 | 51 | 13 | 49 | 13 | 0.54 |
| eQ | pg/ml | 1.0E0 | 1.0E0 | 1.1E2 | 6.5E0 | 3.2E2 | 1.5E1 | 1.0E0 | 1.0E0 | 1.6E3 | 4.0E1 | 28 | 7 | 26 | 7 | 0.40 |
| fA | ng/ml | 2.2E2 | 1.5E2 | 4.0E2 | 2.1E2 | 4.6E2 | 1.5E2 | 2.6E1 | 6.8E1 | 1.5E3 | 4.7E2 | 28 | 7 | 26 | 7 | 0.46 |
| eZ | ng/ml | 6.1E1 | 5.4E1 | 6.4E1 | 5.8E1 | 2.6E1 | 2.4E1 | 2.3E1 | 2.5E1 | 1.2E2 | 1.1E2 | 51 | 13 | 49 | 13 | 0.45 |
| fB | ng/ml | 6.1E2 | 6.5E2 | 6.8E2 | 8.7E2 | 2.8E2 | 4.2E2 | 1.6E2 | 4.4E2 | 1.3E3 | 1.5E3 | 28 | 7 | 26 | 7 | 0.61 |
| eX | ng/ml | 6.0E0 | 3.3E0 | 1.9E1 | 1.2E1 | 2.3E1 | 1.5E1 | 8.6E-4 | 3.3E-1 | 7.3E1 | 4.9E1 | 44 | 13 | 29 | 13 | 0.44 |
| fN | ng/ml | 2.1E-1 | 2.1E-1 | 2.7E0 | 1.7E0 | 5.8E0 | 3.1E0 | 2.1E-1 | 2.1E-1 | 3.2E1 | 8.9E0 | 51 | 13 | 49 | 13 | 0.45 |
| fP | ng/ml | 2.3E2 | 2.9E2 | 2.7E2 | 3.1E2 | 1.7E2 | 1.6E2 | 8.4E0 | 4.8E1 | 1.0E3 | 8.6E2 | 127 | 43 | 88 | 43 | 0.60 |
| fR | ng/ml | 1.3E5 | 1.6E5 | 1.6E5 | 2.3E5 | 1.1E5 | 1.7E5 | 3.1E4 | 3.6E4 | 6.1E5 | 6.9E5 | 162 | 28 | 44 | 28 | 0.62 |
| fY | ng/ml | 2.5E2 | 2.7E2 | 2.4E2 | 2.6E2 | 8.9E1 | 1.4E2 | 6.5E1 | 4.2E1 | 4.2E2 | 4.5E2 | 51 | 13 | 49 | 13 | 0.54 |
| gC | ng/ml | 2.3E2 | 2.3E2 | 2.5E2 | 2.7E2 | 9.4E1 | 1.2E2 | 1.2E2 | 1.3E2 | 6.4E2 | 5.9E2 | 71 | 20 | 39 | 20 | 0.52 |
| gN | U/ml | 3.5E2 | 4.7E2 | 4.8E2 | 5.2E2 | 3.2E2 | 2.9E2 | 3.5E1 | 1.2E2 | 1.3E3 | 9.2E2 | 35 | 10 | 18 | 10 | 0.57 |
| gL | pg/ml | 6.1E4 | 6.9E4 | 6.8E4 | 7.7E4 | 2.9E4 | 3.0E4 | 2.2E4 | 3.8E4 | 1.8E5 | 1.6E5 | 131 | 47 | 88 | 47 | 0.59 |
| gP | U/ml | 2.5E2 | 2.8E2 | 2.6E2 | 2.8E2 | 7.9E1 | 1.1E2 | 8.5E1 | 8.6E1 | 5.3E2 | 6.5E2 | 137 | 48 | 88 | 48 | 0.57 |

Figure 14 Continued

| Code | Units | Median | | Average | | Standard Deviation | | Minimum | | Maximum | | Number of Samples | | Number of Patients | | AUC |
|------|-------|--------|------|---------|------|--------|------|---------|------|---------|------|--------|-----|--------|-----|------|
|      |       | NonDis | Dis  | NonDis  | Dis  | NonDis | Dis  | NonDis  | Dis  | NonDis  | Dis  | NonDis | Dis | NonDis | Dis |      |
| gT   | ng/ml | 2.0E1  | 2.3E1| 2.0E1   | 2.4E1| 4.1E0  | 5.1E0| 1.2E1   | 1.7E1| 2.9E1   | 3.2E1| 36     | 10  | 22     | 10  | 0.68 |
| gW   | ng/ml | 7.0E2  | 4.1E2| 1.5E3   | 7.9E2| 1.9E3  | 9.5E2| 3.7E1   | 2.3E0| 9.5E3   | 4.3E3| 109    | 41  | 79     | 41  | 0.39 |
| gV   | ng/ml | 2.0E1  | 1.6E1| 2.1E1   | 1.5E1| 6.7E0  | 7.5E0| 1.0E1   | 8.1E-2| 3.9E1  | 2.5E1| 59     | 7   | 15     | 7   | 0.29 |
| tF   | pg/mL | 2.6E3  | 9.0E2| 2.2E4   | 1.4E4| 5.6E4  | 4.1E4| 1.2E1   | 1.8E1| 3.2E5   | 2.3E5| 100    | 39  | 86     | 39  | 0.41 |
| gZ   | ug/ml | 8.9E-1 | 9.5E-1| 4.5E1  | 5.8E1| 1.1E2  | 1.4E2| 8.7E-2  | 1.1E-1| 4.1E2  | 3.8E2| 28     | 7   | 26     | 7   | 0.52 |
| hA   | ng/ml | 2.3E0  | 2.4E0| 7.4E0   | 9.7E0| 2.4E1  | 2.4E1| 1.7E-2  | 1.7E-2| 1.6E2  | 1.0E2| 77     | 29  | 64     | 29  | 0.51 |
| nM   | pg/ml | 1.0E-9 | 1.0E-9| 1.9E2  | 1.0E-9| 1.4E3 | 0.0E0| 1.0E-9  | 1.0E-9| 1.0E4  | 1.0E-9| 54    | 23  | 47     | 23  | 0.48 |
| nN   | pg/ml | 1.1E3  | 1.9E3| 2.1E3   | 2.7E3| 2.7E3  | 2.9E3| 1.1E2   | 1.9E2| 1.7E4   | 1.3E4| 54     | 23  | 47     | 23  | 0.58 |
| nO   | pg/ml | 3.1E1  | 2.9E1| 4.5E1   | 4.6E1| 4.7E1  | 5.3E1| 5.5E0   | 3.5E0| 2.4E2   | 2.4E2| 54     | 23  | 47     | 23  | 0.48 |
| nR   | pg/ml | 1.6E1  | 2.0E1| 4.5E1   | 5.6E1| 7.3E1  | 9.5E1| 1.0E-9  | 1.7E0| 3.6E2   | 4.2E2| 54     | 23  | 47     | 23  | 0.56 |
| nT   | pg/ml | 8.5E1  | 8.0E1| 3.5E2   | 8.8E1| 1.2E3  | 6.2E1| 1.0E-9  | 1.0E-9| 6.6E3  | 2.0E2| 54     | 23  | 47     | 23  | 0.48 |
| nU   | pg/ml | 2.9E1  | 2.9E1| 5.1E2   | 6.4E1| 2.2E3  | 6.8E1| 1.0E-9  | 1.0E-9| 1.3E4  | 2.2E2| 54     | 23  | 47     | 23  | 0.56 |
| lW   | pg/ml | 1.0E-9 | 1.0E-9| 1.6E1  | 6.1E-1| 5.5E1 | 2.0E0| 1.0E-9  | 1.0E-9| 3.9E2  | 8.1E0| 54     | 23  | 47     | 23  | 0.36 |
| lX   | pg/ml | 9.5E2  | 9.6E2| 9.2E2   | 1.0E3| 4.4E2  | 5.5E2| 2.3E2   | 1.2E2| 1.9E3   | 2.1E3| 54     | 23  | 47     | 23  | 0.54 |
| lY   | pg/ml | 1.7E1  | 2.4E1| 2.2E1   | 2.4E1| 2.5E1  | 1.2E1| 1.0E-9  | 5.4E0| 1.4E2   | 4.4E1| 54     | 23  | 47     | 23  | 0.63 |
| mE   | pg/ml | 1.0E-9 | 1.0E-9| 3.3E0  | 1.4E0| 1.0E1  | 3.4E0| 1.0E-9  | 1.0E-9| 5.8E1  | 1.3E1| 54     | 23  | 47     | 23  | 0.49 |
| mF   | pg/ml | 1.0E-9 | 1.0E-9| 1.4E0  | 1.5E0| 3.0E0  | 3.1E0| 1.0E-9  | 1.0E-9| 1.5E1  | 1.3E1| 54     | 23  | 47     | 23  | 0.54 |
| mH   | pg/ml | 3.6E0  | 2.9E0| 4.9E0   | 3.7E0| 5.0E0  | 2.8E0| 2.3E-1  | 3.2E-1| 3.2E1  | 1.1E1| 54     | 23  | 47     | 23  | 0.45 |
| mI   | pg/ml | 1.0E-9 | 1.0E-9| 1.2E1   | 8.8E0| 3.1E1 | 1.7E1| 1.0E-9  | 1.0E-9| 1.6E2  | 7.8E1| 54     | 23  | 47     | 23  | 0.53 |
| mM   | pg/ml | 3.0E1  | 1.2E1| 5.2E1   | 5.6E1| 5.9E1  | 8.1E1| 1.0E-9  | 1.0E-9| 2.3E2  | 2.9E2| 54     | 23  | 47     | 23  | 0.48 |
| mP   | pg/ml | 1.5E1  | 1.4E1| 2.0E1   | 1.3E1| 2.2E1  | 7.0E0| 1.0E-9  | 1.0E-9| 1.5E2  | 2.9E1| 53     | 23  | 46     | 23  | 0.40 |
| mS   | pg/ml | 1.8E3  | 1.7E3| 2.2E3   | 1.8E3| 2.2E3  | 8.3E2| 1.0E-9  | 1.0E-9| 1.3E4  | 3.9E3| 54     | 23  | 47     | 23  | 0.45 |
| mT   | pg/ml | 5.0E1  | 5.9E1| 1.2E2   | 8.3E1| 2.2E2  | 6.1E1| 1.0E1   | 1.6E1| 1.4E3   | 2.8E2| 53     | 23  | 46     | 23  | 0.54 |
| mU   | pg/ml | 2.5E0  | 2.5E0| 4.2E0   | 2.7E0| 8.5E0  | 2.0E0| 1.0E-9  | 1.9E-1| 5.8E1  | 1.1E1| 53     | 23  | 46     | 23  | 0.48 |
| mW   | pg/ml | 2.5E3  | 2.4E3| 2.7E3   | 2.8E3| 1.7E3  | 1.3E3| 4.3E2   | 7.7E2| 1.0E4   | 5.7E3| 53     | 23  | 46     | 23  | 0.53 |
| mY   | pg/ml | 4.7E2  | 6.2E2| 1.0E3   | 7.7E2| 1.8E3  | 5.2E2| 1.0E-9  | 2.1E2| 1.1E4   | 2.2E3| 54     | 23  | 47     | 23  | 0.58 |
| mZ   | pg/ml | 2.6E2  | 3.4E2| 5.0E2   | 5.2E2| 6.0E2  | 5.8E2| 2.1E1   | 5.3E1| 3.1E3   | 2.8E3| 53     | 23  | 46     | 23  | 0.53 |
| nA   | pg/ml | 1.3E0  | 1.5E0| 1.6E1   | 4.8E0| 6.6E1  | 1.3E1| 1.0E-9  | 1.0E-9| 4.4E2  | 6.2E1| 53     | 23  | 46     | 23  | 0.48 |
| nB   | pg/ml | 2.6E2  | 3.2E2| 3.1E2   | 3.4E2| 1.6E2  | 1.2E2| 3.0E1   | 1.4E2| 7.2E2   | 6.4E2| 54     | 23  | 47     | 23  | 0.60 |
| nC   | pg/ml | 1.0E-9 | 1.0E-9| 8.7E3  | 6.7E4| 5.0E4  | 3.2E5| 1.0E-9  | 1.0E-9| 3.7E5  | 1.5E6| 54     | 23  | 47     | 23  | 0.49 |
| nD   | pg/ml | 7.2E0  | 7.9E0| 7.0E1   | 8.1E0| 3.1E2  | 7.8E0| 1.0E-9  | 1.0E-9| 1.7E3  | 2.9E1| 53     | 23  | 46     | 23  | 0.46 |
| nF   | pg/ml | 1.0E-9 | 1.0E-9| 9.5E0  | 1.3E0| 4.0E1  | 4.7E0| 1.0E-9  | 1.0E-9| 2.4E2  | 2.1E1| 54     | 23  | 47     | 23  | 0.49 |
| nH   | pg/ml | 3.0E-2 | 3.7E-1| 2.1E2  | 1.2E2| 1.4E3  | 5.5E2| 1.0E-9  | 1.0E-9| 1.0E4  | 2.6E3| 53     | 23  | 46     | 23  | 0.51 |
| nI   | pg/ml | 4.6E1  | 2.8E0| 2.9E2   | 5.0E1| 1.3E3  | 6.4E1| 1.0E-9  | 1.0E-9| 9.2E3  | 1.9E2| 54     | 23  | 47     | 23  | 0.46 |
| nJ   | pg/ml | 1.7E-1 | 1.0E-9| 9.9E1  | 5.2E-1| 7.0E2 | 8.5E-1| 1.0E-9 | 1.0E-9| 5.2E3  | 2.4E0| 54     | 23  | 47     | 23  | 0.41 |
| nK   | pg/ml | 1.0E-9 | 1.0E-9| 1.2E2  | 1.0E1| 5.4E2  | 1.8E1| 1.0E-9  | 1.0E-9| 3.2E3  | 6.4E1| 53     | 23  | 46     | 23  | 0.55 |
| nL   | pg/ml | 1.0E-9 | 1.0E-9| 9.3E2  | 2.4E2| 6.1E3  | 1.1E3| 1.0E-9  | 1.0E-9| 4.5E4  | 5.2E3| 54     | 23  | 47     | 23  | 0.45 |
| hL   | pg/ml | 1.7E4  | 2.6E4| 2.3E4   | 2.6E4| 2.2E4  | 1.2E4| 2.6E3   | 5.7E3| 1.4E5   | 4.6E4| 51     | 13  | 49     | 13  | 0.64 |
| hO   | pg/ml | 1.6E4  | 1.6E4| 1.7E4   | 1.8E4| 3.2E3  | 4.4E3| 1.1E4   | 1.4E4| 2.8E4   | 2.6E4| 51     | 13  | 49     | 13  | 0.59 |
| hP   | ng/ml | 4.4E5  | 4.4E5| 3.7E5   | 4.5E5| 1.7E5  | 2.7E5| 2.8E4   | 1.7E4| 9.0E5   | 1.1E6| 51     | 13  | 49     | 13  | 0.57 |
| wJ   | pg/ml | 1.5E5  | 1.6E5| 1.6E5   | 1.9E5| 8.7E4  | 1.2E5| 2.8E4   | 6.0E4| 4.0E5   | 5.1E5| 48     | 12  | 44     | 12  | 0.56 |
| wK   | pg/ml | 3.4E4  | 2.7E4| 4.3E4   | 4.1E4| 2.7E4  | 3.6E4| 5.2E3   | 9.2E3| 1.2E5   | 1.4E5| 48     | 12  | 44     | 12  | 0.45 |
| wL   | pg/ml | 6.5E0  | 1.7E0| 7.0E1   | 2.5E1| 1.5E2  | 7.1E1| 1.0E-9  | 1.0E-9| 8.4E2  | 2.5E2| 48     | 12  | 44     | 12  | 0.35 |
| wP   | pg/ml | 2.8E4  | 3.1E4| 4.3E4   | 5.7E4| 4.3E4  | 8.2E4| 2.8E3   | 2.9E3| 1.6E5   | 3.0E5| 48     | 12  | 44     | 12  | 0.50 |
| wQ   | pg/ml | 3.4E1  | 4.1E1| 6.0E1   | 6.1E1| 7.7E1  | 8.5E1| 1.0E-9  | 1.0E-9| 3.7E2  | 3.0E2| 48     | 12  | 44     | 12  | 0.50 |
| hR   | pg/ml | 2.7E4  | 2.6E4| 3.0E4   | 2.5E4| 1.1E4  | 9.7E3| 1.8E3   | 3.6E3| 5.8E4   | 4.1E4| 75     | 28  | 62     | 28  | 0.39 |
| hV   | pg/ml | 4.4E2  | 3.2E2| 4.7E2   | 4.1E2| 2.4E2  | 2.2E2| 1.3E2   | 6.8E1| 1.5E3   | 8.2E2| 75     | 28  | 62     | 28  | 0.43 |
| hW   | pg/ml | 1.6E3  | 1.7E3| 2.1E3   | 2.4E3| 1.6E3  | 1.9E3| 5.7E2   | 2.2E2| 1.0E4   | 6.7E3| 75     | 28  | 62     | 28  | 0.51 |
| hX   | pg/ml | 9.6E2  | 8.9E2| 1.2E3   | 1.1E3| 1.1E3  | 1.1E3| 4.8E2   | 2.3E2| 8.6E3   | 6.6E3| 75     | 28  | 62     | 28  | 0.43 |
| iA   | pg/ml | 1.7E2  | 1.6E2| 4.2E2   | 2.5E2| 9.2E2  | 3.4E2| 1.8E1   | 1.2E1| 7.1E3   | 2.2E3| 100    | 39  | 86     | 39  | 0.50 |
| iB   | ng/ml | 5.4E0  | 3.7E0| 6.7E0   | 5.0E0| 4.7E0  | 4.6E0| 2.5E-1  | 4.5E-2| 2.0E1  | 1.9E1| 77     | 29  | 64     | 29  | 0.36 |
| iC   | U/ml  | 2.4E-1 | 2.0E-1| 5.0E-1 | 8.9E-1| 8.7E-1| 2.3E0| 1.0E-9  | 1.0E-9| 6.4E0  | 1.2E1| 77     | 29  | 64     | 29  | 0.52 |
| tQ   | pg/ml | 1.1E3  | 1.0E3| 1.2E3   | 1.1E3| 5.5E2  | 5.3E2| 2.8E2   | 6.4E2| 2.5E3   | 2.5E3| 46     | 12  | 43     | 12  | 0.42 |
| tT   | pg/ml | 1.5E1  | 1.3E1| 1.7E1   | 1.8E1| 7.4E0  | 1.5E1| 7.4E0   | 7.9E0| 3.9E1   | 6.1E1| 46     | 12  | 43     | 12  | 0.42 |
| tS   | pg/ml | 1.0E0  | 8.6E-1| 1.1E0  | 8.9E-1| 8.6E-1| 6.3E-1| 1.0E-9 | 1.0E-9| 4.0E0  | 1.9E0| 46     | 12  | 43     | 12  | 0.45 |
| tX   | pg/ml | 8.1E-1 | 8.7E-1| 9.5E-1 | 7.8E-1| 7.0E-1| 4.0E-1| 2.5E-2 | 7.6E-2| 3.3E0  | 1.3E0| 46     | 12  | 43     | 12  | 0.47 |
| tO   | pg/ml | 4.0E0  | 3.8E0| 4.4E0   | 4.0E0| 2.5E0  | 2.6E0| 1.0E-9  | 8.6E-1| 1.1E1  | 9.0E0| 46     | 12  | 43     | 12  | 0.45 |

Figure 14 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| tR | pg/ml | 2.1E-1 | 1.2E-1 | 2.5E-1 | 1.5E-1 | 2.1E-1 | 1.2E-1 | 1.0E-9 | 1.0E-9 | 9.1E-1 | 3.4E-1 | 46 | 12 | 43 | 12 | 0.37 |
| tU | pg/ml | 9.0E0 | 9.2E0 | 1.1E1 | 1.0E1 | 6.9E0 | 6.2E0 | 1.6E0 | 3.6E0 | 3.1E1 | 2.7E1 | 46 | 12 | 43 | 12 | 0.50 |
| tN | pg/ml | 1.7E1 | 1.5E1 | 1.9E1 | 1.7E1 | 1.0E1 | 9.9E0 | 1.0E-9 | 6.0E0 | 5.4E1 | 4.2E1 | 46 | 12 | 43 | 12 | 0.42 |
| tV | ng/ml | 3.7E2 | 6.6E2 | 4.8E2 | 6.5E2 | 4.0E2 | 3.4E2 | 6.6E1 | 1.5E2 | 2.6E3 | 1.1E3 | 48 | 12 | 44 | 12 | 0.66 |
| iH | ng/ml | 1.5E5 | 1.5E5 | 1.5E5 | 1.5E5 | 4.3E4 | 5.0E4 | 7.1E4 | 7.4E4 | 2.4E5 | 2.5E5 | 100 | 39 | 86 | 39 | 0.54 |
| iJ | ng/ml | 5.1E4 | 4.9E4 | 5.3E4 | 5.0E4 | 2.0E4 | 2.1E4 | 8.7E3 | 8.0E3 | 1.2E5 | 9.7E4 | 100 | 39 | 86 | 39 | 0.46 |
| hB | ng/ml | 4.3E-1 | 3.7E-1 | 5.2E-1 | 4.9E-1 | 3.5E-1 | 3.4E-1 | 1.2E-1 | 1.2E-1 | 1.9E0 | 1.6E0 | 100 | 39 | 86 | 39 | 0.47 |
| hC | pg/ml | 3.6E3 | 4.2E3 | 5.9E3 | 8.2E3 | 7.5E3 | 8.9E3 | 1.0E-9 | 1.0E-9 | 5.5E4 | 3.4E4 | 100 | 39 | 86 | 39 | 0.59 |
| hF | ng/ml | 1.0E-9 | 1.0E-9 | 4.9E1 | 2.6E-1 | 4.1E2 | 1.5E0 | 1.0E-9 | 1.0E-9 | 4.0E3 | 9.6E0 | 100 | 39 | 86 | 39 | 0.51 |
| hG | pg/ml | 7.4E3 | 7.8E3 | 7.8E3 | 7.8E3 | 2.9E3 | 3.5E3 | 1.7E3 | 3.3E3 | 1.8E4 | 1.9E4 | 100 | 39 | 86 | 39 | 0.48 |
| iO | ng/ml | 4.1E5 | 3.4E5 | 4.2E5 | 3.8E5 | 2.0E5 | 1.8E5 | 1.1E5 | 8.3E4 | 1.1E6 | 9.0E5 | 100 | 39 | 86 | 39 | 0.44 |
| iP | ng/ml | 6.1E4 | 5.7E4 | 5.5E4 | 5.6E4 | 3.1E4 | 3.3E4 | 5.8E3 | 2.4E3 | 2.5E5 | 1.5E5 | 100 | 39 | 86 | 39 | 0.50 |
| iZ | ng/ml | 1.7E3 | 1.6E3 | 1.8E3 | 2.0E3 | 6.8E2 | 1.1E3 | 4.7E2 | 8.8E2 | 3.5E3 | 6.5E3 | 100 | 39 | 86 | 39 | 0.51 |
| yH | pg/ml | 1.2E3 | 1.5E3 | 2.0E3 | 1.2E3 | 3.0E3 | 3.5E4 | 1.0E-9 | 1.6E2 | 1.5E4 | 1.2E5 | 48 | 12 | 44 | 12 | 0.53 |
| yK | U/ml | 1.8E1 | 3.2E1 | 4.9E1 | 5.2E1 | 8.5E1 | 6.9E1 | 1.0E-9 | 1.0E-9 | 3.8E2 | 2.5E2 | 48 | 12 | 44 | 12 | 0.58 |
| yJ | pg/ml | 3.6E4 | 5.0E4 | 4.7E4 | 5.3E4 | 3.5E4 | 3.2E4 | 1.7E3 | 1.7E4 | 1.6E5 | 1.1E5 | 48 | 12 | 44 | 12 | 0.57 |
| yD | ng/ml | 1.5E-2 | 1.4E-2 | 1.5E-2 | 1.4E-2 | 5.8E-3 | 4.7E-3 | 1.0E-9 | 7.6E-3 | 2.9E-2 | 2.2E-2 | 48 | 12 | 44 | 12 | 0.48 |
| jB | ng/ml | 2.6E5 | 2.4E5 | 2.7E5 | 2.8E5 | 8.8E4 | 1.8E5 | 5.7E4 | 1.2E5 | 4.1E5 | 6.2E5 | 28 | 7 | 26 | 7 | 0.43 |
| wB | pg/ml | 8.8E3 | 6.5E3 | 9.8E3 | 9.2E3 | 7.3E3 | 8.7E3 | 1.7E3 | 2.5E3 | 4.1E4 | 3.4E4 | 48 | 12 | 44 | 12 | 0.44 |
| pY | pg/ml | 6.0E0 | 6.3E0 | 1.1E1 | 7.1E0 | 2.7E1 | 3.4E0 | 2.1E0 | 2.6E0 | 2.0E2 | 1.4E1 | 51 | 13 | 49 | 13 | 0.53 |
| rC | pg/ml | 1.9E3 | 1.2E3 | 2.6E3 | 1.9E3 | 2.8E3 | 1.4E3 | 1.0E2 | 6.6E1 | 1.5E4 | 5.3E3 | 72 | 29 | 59 | 29 | 0.45 |
| rB | pg/ml | 2.2E1 | 3.0E1 | 5.5E1 | 3.8E1 | 1.4E2 | 2.8E1 | 1.0E-9 | 1.0E-9 | 9.5E2 | 1.4E2 | 72 | 29 | 59 | 29 | 0.62 |
| zG | 2.5ng/ml | 2.0E-1 | 1.6E-1 | 4.5E-1 | 4.2E-1 | 7.8E-1 | 9.3E-1 | 1.0E-9 | 1.0E-9 | 4.4E0 | 3.3E0 | 48 | 12 | 44 | 12 | 0.42 |
| zH | 2.3mU/ml | 1.1E-1 | 9.8E-2 | 1.2E-1 | 1.0E-1 | 6.9E-2 | 1.7E-2 | 1.0E-2 | 6.3E-2 | 4.4E-1 | 1.3E-1 | 48 | 12 | 44 | 12 | 0.48 |
| zI | 2.6ng/ml | 1.8E0 | 2.6E0 | 3.2E0 | 4.0E0 | 3.3E0 | 4.2E0 | 6.1E-1 | 9.5E-1 | 1.5E1 | 1.6E1 | 48 | 12 | 44 | 12 | 0.54 |
| qA | ng/ml | 1.0E7 | 8.6E6 | 1.1E7 | 9.0E6 | 7.3E6 | 3.9E6 | 3.7E6 | 2.0E6 | 3.7E7 | 1.6E7 | 51 | 13 | 49 | 13 | 0.43 |
| qB | ng/ml | 6.3E5 | 5.5E5 | 8.3E5 | 6.4E5 | 5.8E5 | 3.4E5 | 2.1E5 | 2.3E5 | 2.9E6 | 1.4E6 | 51 | 13 | 49 | 13 | 0.42 |
| qC | ng/ml | 4.8E5 | 2.8E5 | 8.2E5 | 5.4E5 | 1.2E6 | 9.1E5 | 2.0E4 | 3.4E3 | 7.1E6 | 3.4E6 | 51 | 13 | 49 | 13 | 0.35 |
| qD | ng/ml | 1.6E7 | 1.3E7 | 1.9E7 | 1.5E7 | 9.4E6 | 5.5E6 | 4.9E6 | 4.9E6 | 5.2E7 | 2.8E7 | 51 | 13 | 49 | 13 | 0.37 |
| jD | ng/ml | 2.2E1 | 4.8E1 | 4.4E1 | 5.6E1 | 7.2E1 | 5.6E1 | 1.0E-9 | 1.0E-9 | 5.1E2 | 2.9E2 | 77 | 29 | 64 | 29 | 0.64 |
| jE | ng/ml | 1.0E-9 | 1.0E-9 | 8.0E0 | 8.5E0 | 2.1E1 | 1.6E1 | 1.0E-9 | 1.0E-9 | 1.2E2 | 5.6E1 | 77 | 29 | 64 | 29 | 0.53 |
| jF | ng/ml | 3.5E1 | 3.7E1 | 5.0E1 | 5.0E1 | 5.8E1 | 6.1E1 | 1.0E-9 | 1.0E-9 | 2.5E2 | 1.8E2 | 77 | 29 | 64 | 29 | 0.48 |
| jG | ng/ml | 4.5E3 | 4.7E3 | 4.6E3 | 4.4E3 | 1.9E3 | 1.6E3 | 7.6E2 | 6.0E2 | 9.5E3 | 7.5E3 | 77 | 29 | 64 | 29 | 0.49 |
| jH | ng/ml | 7.9E1 | 7.4E1 | 8.6E1 | 8.6E1 | 4.5E1 | 5.8E1 | 1.9E1 | 2.5E1 | 2.3E2 | 3.3E2 | 77 | 29 | 64 | 29 | 0.47 |
| jI | ng/ml | 6.9E1 | 7.7E1 | 7.4E1 | 8.1E1 | 3.4E1 | 3.3E1 | 2.8E1 | 3.9E1 | 2.5E2 | 1.9E2 | 77 | 29 | 64 | 29 | 0.58 |
| sK | pg/mL | 4.2E3 | 3.9E3 | 4.3E3 | 4.2E3 | 1.6E3 | 1.5E3 | 1.7E3 | 1.1E3 | 9.2E3 | 6.1E3 | 49 | 13 | 45 | 13 | 0.51 |
| sM | pg/mL | 8.0E4 | 8.5E4 | 7.9E4 | 8.1E4 | 2.4E4 | 2.5E4 | 3.3E4 | 3.9E4 | 1.5E5 | 1.3E5 | 49 | 13 | 45 | 13 | 0.55 |
| sO | pg/mL | 2.8E8 | 2.4E8 | 2.9E8 | 2.4E8 | 9.9E7 | 9.8E7 | 7.9E7 | 9.1E7 | 4.9E8 | 3.9E8 | 49 | 13 | 45 | 13 | 0.39 |
| wC | ng/ml | 1.6E0 | 1.7E0 | 2.1E0 | 1.9E0 | 2.2E0 | 9.9E-1 | 2.5E-1 | 5.9E-1 | 1.5E1 | 3.7E0 | 48 | 12 | 44 | 12 | 0.53 |
| wD | ng/ml | 2.0E1 | 2.1E1 | 8.1E1 | 2.7E1 | 3.1E2 | 2.1E1 | 2.8E0 | 6.0E0 | 2.1E3 | 7.2E1 | 48 | 12 | 44 | 12 | 0.56 |
| wE | ng/ml | 5.0E1 | 5.0E1 | 5.4E1 | 4.8E1 | 2.4E1 | 1.3E1 | 7.0E0 | 3.0E1 | 1.4E2 | 7.2E1 | 48 | 12 | 44 | 12 | 0.43 |
| wG | ng/ml | 9.6E-2 | 1.1E-2 | 1.3E-1 | 5.0E-2 | 1.3E-1 | 7.4E-2 | 1.0E-9 | 1.0E-9 | 4.8E-1 | 2.1E-1 | 48 | 12 | 44 | 12 | 0.34 |
| wH | ng/ml | 2.3E-2 | 9.1E-3 | 2.1E-1 | 5.0E-2 | 5.5E-1 | 8.1E-2 | 1.0E-9 | 1.0E-9 | 2.9E0 | 2.4E-1 | 48 | 12 | 44 | 12 | 0.37 |
| wF | ng/ml | 2.1E-1 | 4.5E-2 | 2.9E0 | 2.3E-1 | 1.0E1 | 3.7E-1 | 1.0E-9 | 1.0E-9 | 5.7E1 | 1.1E0 | 48 | 12 | 44 | 12 | 0.36 |
| rA | pg/ml | 2.4E1 | 2.2E1 | 2.7E1 | 3.1E1 | 2.2E1 | 2.5E1 | 1.0E-9 | 4.2E0 | 1.2E2 | 9.4E1 | 74 | 30 | 61 | 30 | 0.53 |
| qZ | pg/ml | 4.3E1 | 4.2E1 | 2.1E2 | 9.5E2 | 1.3E3 | 2.9E3 | 2.8E-4 | 4.8E-4 | 1.0E4 | 1.0E4 | 63 | 22 | 54 | 22 | 0.50 |
| qY | pg/ml | 2.1E1 | 2.7E1 | 4.6E1 | 5.7E1 | 7.5E1 | 6.1E1 | 8.7E-1 | 3.3E0 | 5.3E2 | 2.3E2 | 74 | 30 | 61 | 30 | 0.58 |
| qX | pg/ml | 5.1E1 | 5.3E1 | 5.9E1 | 6.5E1 | 3.9E1 | 4.9E1 | 1.0E-9 | 1.0E-9 | 1.8E2 | 2.1E2 | 74 | 30 | 61 | 30 | 0.50 |
| qW | pg/ml | 9.4E0 | 8.1E0 | 1.2E1 | 1.1E1 | 1.3E1 | 1.1E1 | 1.0E-9 | 1.0E-9 | 7.1E1 | 5.1E1 | 74 | 30 | 61 | 30 | 0.48 |
| qV | pg/ml | 2.1E3 | 2.0E3 | 2.7E3 | 2.8E3 | 1.9E3 | 2.0E3 | 2.3E2 | 5.6E2 | 8.5E3 | 8.2E3 | 74 | 30 | 61 | 30 | 0.50 |
| qU | pg/ml | 4.5E1 | 6.2E1 | 1.3E2 | 1.2E2 | 2.2E2 | 1.6E2 | 1.0E-9 | 1.0E-9 | 1.4E3 | 7.3E2 | 74 | 30 | 61 | 30 | 0.54 |
| qT | pg/ml | 3.8E1 | 4.4E1 | 6.4E1 | 6.4E1 | 1.2E2 | 5.5E1 | 1.0E-9 | 1.0E-9 | 9.0E2 | 2.0E2 | 74 | 30 | 61 | 30 | 0.57 |
| qI | ng/ml | 5.8E4 | 8.1E4 | 6.4E4 | 7.3E4 | 3.2E4 | 3.1E4 | 5.4E3 | 5.9E3 | 1.6E5 | 1.0E5 | 48 | 14 | 46 | 14 | 0.64 |
| qH | ng/ml | 6.5E4 | 4.6E4 | 7.3E4 | 5.3E4 | 3.9E4 | 3.6E4 | 1.0E4 | 7.6E3 | 1.8E5 | 1.2E5 | 48 | 14 | 46 | 14 | 0.35 |
| qG | ng/ml | 1.8E5 | 2.4E5 | 1.9E5 | 2.1E5 | 6.2E4 | 9.9E4 | 3.1E4 | 1.7E4 | 3.3E5 | 3.1E5 | 48 | 14 | 46 | 14 | 0.60 |
| jK | ng/ml | 1.6E3 | 1.8E3 | 1.7E3 | 1.9E3 | 5.7E2 | 7.7E2 | 5.5E2 | 7.2E2 | 4.1E3 | 4.0E3 | 77 | 29 | 64 | 29 | 0.58 |
| jL | ng/ml | 1.8E2 | 2.5E2 | 2.6E2 | 3.6E2 | 1.9E2 | 4.0E2 | 3.6E1 | 4.9E1 | 7.9E2 | 2.1E3 | 77 | 29 | 64 | 29 | 0.60 |

Figure 14 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jM | ng/ml | 7.1E4 | 6.3E4 | 7.0E4 | 7.3E4 | 3.4E4 | 4.2E4 | 3.9E2 | 1.1E3 | 1.5E5 | 1.7E5 | 77 | 29 | 64 | 29 | 0.52 |
| jO | pg/ml | 2.2E5 | 2.3E5 | 2.8E5 | 2.5E5 | 1.5E5 | 1.2E5 | 5.2E4 | 7.7E4 | 7.7E5 | 5.2E5 | 77 | 29 | 64 | 29 | 0.47 |
| jP | pg/ml | 2.3E5 | 2.5E5 | 2.6E5 | 2.9E5 | 1.5E5 | 2.4E5 | 7.0E4 | 7.4E4 | 9.1E5 | 1.2E6 | 77 | 29 | 64 | 29 | 0.50 |
| jQ | pg/ml | 2.5E3 | 2.7E3 | 3.0E3 | 3.5E3 | 2.3E3 | 3.4E3 | 4.2E1 | 1.4E2 | 1.2E4 | 1.4E4 | 77 | 29 | 64 | 29 | 0.50 |
| jR | pg/ml | 6.5E3 | 5.9E3 | 9.5E3 | 9.6E3 | 9.9E3 | 9.6E3 | 1.0E-9 | 1.0E-9 | 5.5E4 | 3.0E4 | 77 | 29 | 64 | 29 | 0.49 |
| jT | pg/ml | 1.6E5 | 1.7E5 | 1.7E5 | 1.9E5 | 6.9E4 | 8.1E4 | 6.8E4 | 7.9E4 | 4.5E5 | 3.8E5 | 77 | 29 | 64 | 29 | 0.53 |
| xA | pg/ml | 3.9E0 | 4.7E0 | 1.7E1 | 7.5E0 | 5.7E1 | 1.1E1 | 1.0E-9 | 1.0E-9 | 3.9E2 | 3.0E1 | 48 | 12 | 44 | 12 | 0.47 |
| yE | pg/ml | 7.8E1 | 7.2E1 | 8.2E1 | 8.2E1 | 4.9E1 | 2.9E1 | 6.4E0 | 5.2E1 | 3.0E2 | 1.3E2 | 48 | 12 | 44 | 12 | 0.53 |
| tM | pg/ml | 4.3E1 | 3.5E1 | 4.3E1 | 3.7E1 | 2.0E1 | 1.4E1 | 1.0E-9 | 2.2E1 | 1.0E2 | 6.3E1 | 48 | 12 | 44 | 12 | 0.39 |
| tL | pg/ml | 1.0E-9 | 1.0E-9 | 7.8E0 | 3.1E-1 | 3.8E1 | 6.6E-1 | 1.0E-9 | 1.0E-9 | 2.6E2 | 2.1E0 | 48 | 12 | 44 | 12 | 0.49 |
| jU | mIU/ml | 3.8E0 | 5.5E0 | 1.0E1 | 8.8E0 | 1.7E1 | 1.3E1 | 8.9E-2 | 6.2E-2 | 8.1E1 | 6.7E1 | 77 | 29 | 64 | 29 | 0.55 |
| jV | mIU/ml | 1.6E0 | 1.1E0 | 3.5E0 | 2.4E0 | 5.4E0 | 5.1E0 | 2.1E-2 | 1.7E-3 | 3.1E1 | 2.6E1 | 77 | 29 | 64 | 29 | 0.36 |
| jY | ng/ml | 9.7E-4 | 7.6E-4 | 1.1E-2 | 3.0E-3 | 4.2E-2 | 5.7E-3 | 1.0E-9 | 1.0E-9 | 3.0E-1 | 2.4E-2 | 77 | 29 | 64 | 29 | 0.46 |
| kC | pg/ml | 9.7E1 | 8.8E1 | 2.4E2 | 1.0E2 | 5.6E2 | 4.8E1 | 2.1E1 | 2.1E1 | 3.5E3 | 2.5E2 | 54 | 23 | 47 | 23 | 0.46 |
| kE | pg/ml | 1.3E5 | 1.4E5 | 1.3E5 | 1.4E5 | 3.3E4 | 4.6E4 | 4.1E4 | 4.1E4 | 2.0E5 | 2.1E5 | 54 | 23 | 47 | 23 | 0.54 |
| kF | pg/mL | 6.6E1 | 6.5E1 | 8.0E1 | 6.2E1 | 7.0E1 | 1.8E1 | 3.2E1 | 2.8E1 | 5.1E2 | 9.3E1 | 54 | 23 | 47 | 23 | 0.42 |
| kG | pg/mL | 9.1E3 | 1.1E4 | 1.2E4 | 1.5E4 | 1.4E4 | 1.2E4 | 7.5E2 | 1.1E3 | 9.1E4 | 5.0E4 | 54 | 23 | 47 | 23 | 0.57 |
| kI | pg/ml | 2.2E2 | 1.7E2 | 2.4E2 | 1.8E2 | 1.4E2 | 7.1E1 | 5.4E1 | 7.2E1 | 8.7E2 | 4.2E2 | 54 | 23 | 47 | 23 | 0.32 |
| kK | pg/ml | 1.2E2 | 8.5E1 | 1.7E2 | 1.3E2 | 1.8E2 | 2.2E1 | 2.2E1 | 2.9E1 | 1.2E3 | 5.1E2 | 54 | 23 | 47 | 23 | 0.38 |
| kN | pg/ml | 1.0E3 | 1.0E3 | 1.5E3 | 2.9E3 | 1.9E3 | 8.0E3 | 2.1E2 | 2.3E2 | 1.3E4 | 3.9E4 | 54 | 23 | 47 | 23 | 0.51 |
| kO | pg/ml | 7.7E3 | 6.9E3 | 1.1E4 | 7.6E3 | 1.8E4 | 3.4E3 | 4.0E3 | 3.4E3 | 1.3E5 | 1.9E4 | 54 | 23 | 47 | 23 | 0.41 |
| kP | pg/ml | 5.4E3 | 5.4E3 | 6.7E3 | 8.9E3 | 5.5E3 | 1.0F4 | 8.6E2 | 1.4E3 | 3.3E4 | 4.8E4 | 54 | 23 | 47 | 23 | 0.54 |
| kQ | pg/ml | 4.3E3 | 5.2E3 | 4.9E3 | 5.6E3 | 2.3E3 | 3.5E3 | 5.6E2 | 1.8E3 | 1.2E4 | 1.8E4 | 100 | 39 | 86 | 39 | 0.52 |
| kR | pg/ml | 2.4E1 | 2.1E1 | 4.0E1 | 2.3E1 | 1.0E2 | 1.4E1 | 1.0E-9 | 1.4E-1 | 1.0E3 | 6.9E1 | 100 | 39 | 86 | 39 | 0.43 |
| kS | pg/ml | 7.7E2 | 9.1E2 | 9.9E2 | 1.1E3 | 1.4E3 | 8.5E2 | 8.2E1 | 2.1E2 | 1.4E4 | 4.1E3 | 100 | 39 | 86 | 39 | 0.56 |
| pS | ng/ml | 2.0E5 | 2.5E5 | 2.2E5 | 2.4E5 | 9.5E4 | 7.9E4 | 7.5E4 | 1.4E5 | 5.0E5 | 3.6E5 | 49 | 13 | 45 | 13 | 0.62 |
| rZ | ng/ml | 1.2E-3 | 1.0E-9 | 7.9E-3 | 3.9E-3 | 2.1E-2 | 7.1E-3 | 1.0E-9 | 1.0E-9 | 1.1E-1 | 3.0E-2 | 73 | 28 | 58 | 28 | 0.45 |
| rY | ng/ml | 5.4E-2 | 6.1E-2 | 2.5E-1 | 9.1E-1 | 8.3E-1 | 4.4E0 | 1.0E-9 | 1.0E-9 | 6.3E0 | 2.3E1 | 73 | 28 | 58 | 28 | 0.52 |
| rX | ng/ml | 1.0E-9 | 1.0E-9 | 9.2E-2 | 1.1E-1 | 4.5E-1 | 5.6E-1 | 1.0E-9 | 1.0E-9 | 3.7E0 | 3.0E0 | 73 | 28 | 58 | 28 | 0.45 |
| lK | pg/ml | 7.1E1 | 1.8E2 | 1.4E2 | 2.9E2 | 1.8E2 | 6.0E2 | 1.0E-9 | 1.0E-9 | 7.0E2 | 3.3E3 | 77 | 29 | 64 | 29 | 0.61 |
| lL | pg/ml | 1.8E3 | 1.4E3 | 3.4E3 | 2.2E3 | 5.5E3 | 2.2E3 | 7.5E1 | 1.5E1 | 4.2E4 | 6.9E3 | 77 | 29 | 64 | 29 | 0.41 |
| lM | pg/ml | 1.0E3 | 1.3E3 | 3.3E3 | 3.3E3 | 7.5E3 | 5.6E3 | 3.9E1 | 2.4E1 | 5.1E4 | 2.9E4 | 77 | 29 | 64 | 29 | 0.53 |
| lN | pg/ml | 1.0E-9 | 4.8E-1 | 7.3E0 | 3.4E0 | 2.2E1 | 5.1E0 | 1.0E-9 | 1.0E-9 | 1.5E2 | 2.4E1 | 77 | 29 | 64 | 29 | 0.53 |
| lO | pg/ml | 1.0E-9 | 1.0E-9 | 5.2E-1 | 1.2E0 | 4.6E0 | 6.2E0 | 1.0E-9 | 1.0E-9 | 4.0E1 | 3.4E1 | 77 | 29 | 64 | 29 | 0.51 |
| zA | ng/ml | 1.9E7 | 2.0E7 | 2.0E7 | 1.9E7 | 6.8E6 | 6.3E6 | 6.7E6 | 6.7E6 | 3.6E7 | 2.8E7 | 44 | 11 | 40 | 11 | 0.52 |
| rW | ng/ml | 1.3E-2 | 3.0E-2 | 2.4E-2 | 5.2E-2 | 3.1E-2 | 5.9E-2 | 1.0E-9 | 1.0E-9 | 1.7E-1 | 1.8E-1 | 49 | 13 | 46 | 13 | 0.65 |
| rV | ng/ml | 1.0E-9 | 1.0E-9 | 9.2E-3 | 2.6E-3 | 3.7E-2 | 8.1E-3 | 1.0E-9 | 1.0E-9 | 2.2E-1 | 2.9E-2 | 49 | 13 | 46 | 13 | 0.48 |
| rU | ng/ml | 9.5E-2 | 5.5E-2 | 1.4E-1 | 1.1E-1 | 2.3E-1 | 1.2E-1 | 1.0E-9 | 1.0E-9 | 1.4E0 | 3.6E-1 | 49 | 13 | 46 | 13 | 0.49 |
| rT | ng/ml | 6.7E0 | 5.0E0 | 6.8E0 | 5.6E0 | 4.1E0 | 1.8E0 | 7.5E-1 | 3.7E0 | 2.1E1 | 1.1E1 | 49 | 13 | 46 | 13 | 0.41 |
| rS | ng/ml | 3.4E0 | 3.5E0 | 5.6E0 | 3.9E0 | 6.8E0 | 2.5E0 | 1.0E0 | 3.9E-1 | 3.8E1 | 8.4E0 | 49 | 13 | 46 | 13 | 0.46 |
| sC | pg/mL | 5.6E3 | 1.3E4 | 8.5E3 | 1.8E4 | 7.1E3 | 1.4E4 | 1.7E3 | 2.5E3 | 3.2E4 | 4.4E4 | 49 | 13 | 45 | 13 | 0.70 |
| yL | pg/ml | 3.4E1 | 3.3E1 | 4.2E1 | 3.2E1 | 2.8E1 | 1.7E1 | 5.6E0 | 1.6E1 | 1.8E2 | 7.3E1 | 47 | 11 | 43 | 11 | 0.38 |
| rP | ng/ml | 7.7E1 | 3.2E2 | 1.7E2 | 3.1E2 | 2.3E2 | 1.9E2 | 1.0E-9 | 6.5E1 | 1.2E3 | 5.0E2 | 49 | 13 | 46 | 13 | 0.76 |
| rQ | ng/ml | 1.0E-9 | 1.0E-9 | 3.4E0 | 1.9E1 | 1.5E1 | 4.7E1 | 1.0E-9 | 1.0E-9 | 8.9E1 | 1.7E2 | 49 | 13 | 46 | 13 | 0.61 |
| rO | ng/ml | 2.5E-2 | 5.0E-2 | 3.9E-2 | 5.2E-2 | 7.1E-2 | 3.9E-2 | 1.0E-9 | 1.0E-9 | 4.4E-1 | 1.2E-1 | 49 | 13 | 46 | 13 | 0.66 |
| rR | ng/ml | 3.9E0 | 1.3E1 | 2.2E1 | 2.5E1 | 6.6E1 | 3.1E1 | 1.0E-9 | 1.0E-9 | 4.5E2 | 1.1E2 | 49 | 13 | 46 | 13 | 0.68 |
| rN | ng/ml | 6.4E-1 | 5.1E-1 | 7.0E-1 | 6.9E-1 | 3.8E-1 | 5.2E-1 | 5.1E-2 | 3.1E-1 | 2.1E0 | 2.2E0 | 49 | 13 | 46 | 13 | 0.41 |
| qO | pg/ml | 9.7E3 | 1.3E4 | 1.2E4 | 1.6E4 | 8.2E3 | 1.4E4 | 2.2E3 | 1.1E3 | 3.9E4 | 4.5E4 | 50 | 13 | 47 | 13 | 0.53 |
| qP | pg/ml | 3.6E2 | 4.1E2 | 3.9E2 | 5.3E2 | 2.5E2 | 4.1E2 | 1.0E-9 | 1.1E2 | 1.1E3 | 1.5E3 | 50 | 13 | 47 | 13 | 0.57 |
| qQ | pg/ml | 3.1E0 | 1.5E1 | 1.5E1 | 1.9E1 | 4.0E1 | 2.8E1 | 1.0E-9 | 1.0E-9 | 2.8E2 | 9.9E1 | 50 | 13 | 47 | 13 | 0.57 |
| nW | pg/ml | 1.1E5 | 1.1E5 | 1.1E5 | 1.1E5 | 2.5E4 | 2.5E4 | 5.8E4 | 7.9E4 | 1.8E5 | 1.9E5 | 100 | 39 | 86 | 39 | 0.49 |
| nY | pg/ml | 1.9E3 | 2.4E3 | 2.3E3 | 2.5E3 | 1.4E3 | 1.2E3 | 6.5E2 | 9.8E2 | 9.9E3 | 5.9E3 | 100 | 39 | 86 | 39 | 0.56 |
| oO | pg/ml | 8.2E4 | 8.8E4 | 1.2E5 | 1.2E5 | 1.1E5 | 8.5E4 | 4.0E4 | 3.8E4 | 6.2E5 | 3.1E5 | 52 | 22 | 45 | 22 | 0.54 |
| oP | pg/ml | 1.3E5 | 1.6E5 | 1.4E5 | 1.7E5 | 8.4E4 | 1.1E5 | 4.8E4 | 4.8E4 | 3.5E5 | 4.6E5 | 52 | 22 | 45 | 22 | 0.57 |
| oQ | pg/ml | 3.0E3 | 3.5E3 | 3.2E3 | 4.4E3 | 1.6E3 | 3.1E3 | 1.1E3 | 1.7E3 | 1.0E4 | 1.4E4 | 52 | 22 | 45 | 22 | 0.58 |
| oE | pg/ml | 2.1E2 | 1.1E2 | 4.6E2 | 3.5E2 | 6.4E2 | 4.9E2 | 1.0E-9 | 1.0E-9 | 4.7E3 | 1.9E3 | 100 | 39 | 86 | 39 | 0.43 |
| oF | pg/ml | 8.6E3 | 7.6E3 | 2.0E4 | 2.6E4 | 3.3E4 | 4.8E4 | 6.4E1 | 7.7E2 | 2.3E5 | 1.8E5 | 100 | 39 | 86 | 39 | 0.48 |

Figure 14 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| oH | pg/ml | 4.2E1 | 4.6E1 | 9.3E1 | 7.3E1 | 1.5E2 | 6.7E1 | 4.2E0 | 6.2E0 | 8.6E2 | 2.9E2 | 100 | 39 | 86 | 39 | 0.54 |
| oK | pg/ml | 6.2E2 | 9.5E2 | 1.9E3 | 3.1E3 | 3.2E3 | 8.4E3 | 5.2E1 | 2.3E2 | 1.8E4 | 5.3E4 | 100 | 39 | 86 | 39 | 0.58 |
| oN | pg/ml | 4.7E2 | 5.1E2 | 8.0E2 | 6.7E2 | 1.9E3 | 7.5E2 | 1.5E2 | 2.6E2 | 1.8E4 | 5.0E3 | 100 | 39 | 86 | 39 | 0.56 |
| oW | pg/ml | 2.0E2 | 2.8E2 | 4.7E2 | 2.7E2 | 1.1E3 | 1.6E2 | 7.7E1 | 8.5E1 | 6.0E3 | 5.4E2 | 28 | 7 | 26 | 7 | 0.54 |
| oT | pg/ml | 3.1E2 | 3.7E2 | 3.5E2 | 3.8E2 | 1.8E2 | 1.6E2 | 9.9E1 | 1.9E2 | 7.8E2 | 7.1E2 | 28 | 7 | 26 | 7 | 0.56 |
| oV | pg/ml | 1.4E2 | 1.1E2 | 2.4E2 | 1.4E2 | 3.2E2 | 7.3E1 | 1.0E-9 | 5.8E1 | 1.4E3 | 2.2E2 | 28 | 7 | 26 | 7 | 0.51 |
| oD | pg/ml | 1.6E4 | 1.8E4 | 1.8E4 | 2.0E4 | 8.1E3 | 6.9E3 | 8.7E3 | 1.2E4 | 4.6E4 | 3.3E4 | 28 | 7 | 26 | 7 | 0.61 |
| uL | ng/ml | 3.8E1 | 3.9E1 | 4.1E1 | 4.2E1 | 2.4E1 | 2.2E1 | 1.0E-9 | 1.5E1 | 1.6E2 | 8.6E1 | 48 | 13 | 44 | 13 | 0.51 |
| uO | ng/ml | 3.5E-1 | 1.3E0 | 8.5E-1 | 1.4E0 | 1.5E0 | 1.5E0 | 1.0E-9 | 1.0E-9 | 9.3E0 | 5.4E0 | 48 | 13 | 44 | 13 | 0.64 |
| uM | ng/ml | 6.3E-1 | 7.9E-1 | 1.2E0 | 8.1E-1 | 2.3E0 | 5.4E-1 | 1.0E-9 | 1.0E-9 | 1.3E1 | 2.2E0 | 48 | 13 | 44 | 13 | 0.54 |
| uI | ng/ml | 6.5E-2 | 1.0E-1 | 1.3E-1 | 1.5E-1 | 1.9E-1 | 1.7E-1 | 1.6E-2 | 3.7E-2 | 1.1E0 | 6.6E-1 | 48 | 13 | 44 | 13 | 0.61 |
| uN | ng/ml | 1.5E1 | 1.2E1 | 1.6E1 | 1.5E1 | 6.5E0 | 7.2E0 | 7.8E0 | 6.3E0 | 4.1E1 | 3.0E1 | 48 | 13 | 44 | 13 | 0.40 |
| uG | ng/ml | 2.2E1 | 1.8E1 | 2.5E1 | 2.1E1 | 1.3E1 | 9.8E0 | 9.8E0 | 7.5E0 | 6.9E1 | 3.9E1 | 48 | 13 | 44 | 13 | 0.39 |
| uR | ng/ml | 2.3E0 | 4.0E0 | 4.2E0 | 4.0E0 | 9.1E0 | 1.9E0 | 9.9E-1 | 9.8E-1 | 6.4E1 | 8.0E0 | 48 | 12 | 44 | 12 | 0.71 |
| uP | ng/ml | 1.8E0 | 2.3E0 | 2.2E0 | 2.7E0 | 1.3E0 | 1.2E0 | 1.1E0 | 1.6E0 | 9.1E0 | 6.2E0 | 48 | 12 | 44 | 12 | 0.70 |
| uV | ng/ml | 1.0E-9 | 7.6E-3 | 1.1E-2 | 2.2E-2 | 3.3E-2 | 2.8E-2 | 1.0E-9 | 1.0E-9 | 2.0E-1 | 7.6E-2 | 48 | 12 | 44 | 12 | 0.63 |
| uT | ng/ml | 6.2E1 | 6.0E1 | 8.8E1 | 7.8E1 | 9.6E1 | 5.6E1 | 1.2E1 | 2.0E1 | 5.8E2 | 2.0E2 | 48 | 12 | 44 | 12 | 0.50 |
| uU | ng/ml | 1.6E0 | 2.0E0 | 2.0E0 | 1.8E0 | 1.1E0 | 7.3E-1 | 6.0E-1 | 8.6E-1 | 5.4E0 | 3.0E0 | 48 | 12 | 44 | 12 | 0.50 |
| uW | ng/ml | 7.5E0 | 7.3E0 | 7.9E0 | 7.5E0 | 2.8E0 | 2.9E0 | 4.0E0 | 3.5E0 | 2.2E1 | 1.5E1 | 48 | 13 | 44 | 13 | 0.45 |
| vB | ng/ml | 2.7E0 | 3.1E0 | 2.7E0 | 3.2E0 | 1.3E0 | 1.5E0 | 5.9E-1 | 9.9E-1 | 5.6E0 | 6.1E0 | 48 | 13 | 44 | 13 | 0.60 |
| vC | ng/ml | 1.0E-9 | 1.0E-9 | 7.5E-3 | 4.0E-3 | 3.5E-2 | 1.4E-2 | 1.0E-9 | 1.0E-9 | 2.0E-1 | 5.1E-2 | 48 | 13 | 44 | 13 | 0.54 |
| uY | ng/ml | 8.3E-1 | 7.8E-1 | 1.3E0 | 9.4E-1 | 1.2E0 | 7.5E-1 | 8.7E-2 | 1.8E-1 | 4.9E0 | 2.6E0 | 48 | 13 | 44 | 13 | 0.41 |
| uZ | ng/ml | 5.9E-1 | 5.1E-1 | 8.8E-1 | 6.4E-1 | 1.1E0 | 3.7E-1 | 1.4E-1 | 1.2E-1 | 7.2E0 | 1.4E0 | 48 | 13 | 44 | 13 | 0.46 |
| uX | ng/ml | 1.1E1 | 1.3E1 | 1.2E1 | 1.4E1 | 6.7E0 | 7.2E0 | 3.6E0 | 3.7E0 | 3.3E1 | 2.7E1 | 48 | 13 | 44 | 13 | 0.58 |
| vA | ng/ml | 6.8E-2 | 6.9E-2 | 8.5E-2 | 8.3E-2 | 5.8E-2 | 4.2E-2 | 2.5E-2 | 1.7E-2 | 3.0E-1 | 1.6E-1 | 48 | 13 | 44 | 13 | 0.53 |
| vH | ng/ml | 1.2E-1 | 1.5E-1 | 1.7E-1 | 1.4E-1 | 1.6E-1 | 8.1E-2 | 1.5E-2 | 9.9E-3 | 8.0E-1 | 2.8E-1 | 49 | 13 | 45 | 13 | 0.48 |
| vI | ng/ml | 1.8E0 | 2.1E0 | 1.9E0 | 2.4E0 | 1.2E0 | 2.9E0 | 6.2E-3 | 4.2E-3 | 5.1E0 | 1.0E1 | 49 | 13 | 45 | 13 | 0.46 |
| vP | ng/ml | 3.8E2 | 5.5E2 | 4.4E2 | 5.7E2 | 3.2E2 | 4.5E2 | 7.0E1 | 4.0E1 | 1.5E3 | 1.3E3 | 48 | 12 | 44 | 12 | 0.57 |
| vT | ng/ml | 7.7E1 | 8.2E1 | 1.2E2 | 7.5E1 | 1.2E2 | 2.6E1 | 4.1E1 | 2.4E1 | 6.9E2 | 1.0E2 | 48 | 12 | 44 | 12 | 0.44 |
| vU | ng/ml | 1.0E-9 | 1.0E-9 | 2.3E1 | 1.3E1 | 3.2E1 | 2.1E1 | 1.0E-9 | 1.0E-9 | 1.0E2 | 5.0E1 | 48 | 12 | 44 | 12 | 0.43 |
| vQ | ng/ml | 3.4E2 | 4.1E2 | 3.4E2 | 4.1E2 | 1.3E2 | 8.4E1 | 6.7E1 | 3.0E2 | 7.0E2 | 5.5E2 | 48 | 12 | 44 | 12 | 0.68 |
| vO | ng/ml | 1.7E3 | 1.9E3 | 1.8E3 | 1.9E3 | 4.6E2 | 4.3E2 | 1.0E3 | 1.2E3 | 3.0E3 | 2.5E3 | 48 | 12 | 44 | 12 | 0.60 |
| vS | ng/ml | 1.3E3 | 1.1E3 | 1.3E3 | 9.9E2 | 3.5E2 | 5.2E2 | 1.0E-9 | 1.0E-9 | 1.8E3 | 1.5E3 | 48 | 12 | 44 | 12 | 0.31 |
| vV | ng/ml | 8.4E2 | 1.0E3 | 1.1E3 | 2.1E3 | 9.9E2 | 3.1E3 | 1.1E2 | 2.1E1 | 5.0E3 | 1.1E4 | 48 | 12 | 44 | 12 | 0.53 |
| vW | ng/ml | 1.5E2 | 1.9E2 | 1.7E2 | 2.1E2 | 1.3E2 | 1.2E2 | 4.3E1 | 7.1E1 | 6.7E2 | 4.0E2 | 48 | 12 | 44 | 12 | 0.61 |
| pF | pg/ml | 5.0E-1 | 6.6E-1 | 6.8E-1 | 9.7E-1 | 1.0E0 | 1.6E0 | 1.0E-9 | 1.0E-9 | 9.4E0 | 1.0E1 | 100 | 39 | 86 | 39 | 0.59 |
| pH | ng/ml | 7.3E0 | 1.2E1 | 8.6E0 | 1.5E1 | 4.0E0 | 1.3E1 | 3.4E0 | 4.7E0 | 1.8E1 | 4.2E1 | 28 | 7 | 26 | 7 | 0.66 |
| pI | ng/ml | 7.1E1 | 9.7E1 | 7.0E1 | 8.7E1 | 3.2E1 | 2.6E1 | 2.6E1 | 5.6E1 | 1.5E2 | 1.2E2 | 28 | 7 | 26 | 7 | 0.67 |
| pK | ng/ml | 4.5E-1 | 6.1E-1 | 5.0E-1 | 6.9E-1 | 2.9E-1 | 3.6E-1 | 2.0E-1 | 3.6E-1 | 1.6E0 | 1.4E0 | 28 | 7 | 26 | 7 | 0.69 |

Analyte panel data:

Unconstrained panels with 3 analytes, where 1.0E-10 >= 'model p-value' > 0. Contains 10,049 panels of 37,261,550 total panels evaluated. :
Ok{Mb(AA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe) Nj(AA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe) Ik(aA Et Fp Fr Hq Hr Hu Hv Hw Hx Ih Ii Ij Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe rQ) Nd(Aa Et Fp Fr Hq Hr Hu Hv Hw Hx Ih Ii Ij Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Ne Nf Ng Nh Ni Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe) Js(bM Et Fp Fr Hq Fr Hu Hv Hw Hx Ih Ii Ij Il Im In Io Ip Iq Ir Is It Iu Iv Jg Jh Ji Jj Jk Jl Jm Jn Jo Jp Jq Jr Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Ne Nf Ng Nh Ni Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe) Et(Fp Fr Hq Hr Hu Hv Hw Hx Ih Ii Ij Il Im In Io Ip Iq Ir Is It Iu Iv Jg Jh Ji Jj Jk Jl Jm Jn Jo Jp Jq Jr Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Ne Nf Ng Nh Ni Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe) Fp(Fr Hq Hr Hu Hv Hw Hx Ih Ii Ij Il Im In Io Ip Iq Ir Is It

Lx Mj Mk Ms Mv Nb Ng Nn Nv Ny On Pa Pb Pg Po Qa Qc Qd) Ms(Hr Hu Ih Im Jk Jn Jo Lh Lv Mc Mv Mz Nb Ng Nn Nu Nv Nw Ny Pa Pg Pz Qa Qc Qd) Hu(Hq Hr Ii Ij Il Io Iu Jh Jk Jn Jo Mc Md Mv Ng Nn Nv Ny Oi Pa Pg Qa Qc Qd) Mv(Hr Ih Im Io Iu Jn Jo Lh Lu Lv Nb Ng Nn Nw Om On Pa Pb Qa Qc Qd) Ng(Hr Ih Im Jh Jn Jo Lh Lu Lv Nb Nn Nw Om On Pa Pz Qa Qc Qd) Nn(Ih Im Jn Jo Lh Lu Lv Nb Nw Pa Qc Qd Qe) Pg(Iv Lx Mh Mi Mk Mr Nb No Nw Om On Pa) Nb(Hr Il Jk Jo Mk Mr Nv Ny Qa Qc) Qc(Hr Ih Im Jo Lv Nw Pa Qa Qe) Nv(Ih Im Lh Lu Lv Nw Om On Pa) Hr(Ih Im Iv Mr No Nu Pa) Jk(Ih Im Lv Nw On Pa) Jo(Ih Im Lh Lv Nm Pa) Qa(Ih Im Pa Qe) Lz(Il Im Qd) Ii(Ih Im Lh) Il(Nw Qe) Ny(Nw Om) Aaio MhHq} Jg{Nh(Fp Hr Hu Hv Hw Hx Ij Ik Il Im In Iq Iu Jh Ji Jj Jk Jn Jr Js Li Lj Ly Ma Mb Md Ml Mm Mp Ms Mt Mu Mv Mw Mx My Nc Nd Nf Ng Nj Nk Nn Nq Ns Nv Nw Nx Ny Oe Of Oh Oi Oy Oz Pa Pc Pd Pe Pf Pg Po Pz Qa Qb Qc Qd) Nc(Fp Hr Hw Hx Ij Ik Il In Iq Iu Jh Ji Jj Jk Jn Js Li Lj Ly Ma Mb Ml Mm Mp Ms Mt Mu Mv Mw Mx My Nd Ng Ni Nj Nk Nn Nq Ns Nv Nw Nx Ny Oe Of Oh Oy Oz Pc Pd Pe Pf Qa Qb Qc Qd) Nj(Fp Hw Hx Ij Il In Iu Ji Jj Jk Js Li Lj Ly Mb Mm Mt Mu Mv Mw My Ng Nk Nq Ns Nw Nx Oe Of Oh Oy Oz Pa Pc Pd Pe Pf Qb) Ng(Fp Hx Ik In Io Iq Ji Jk Js Ly Mb Mt Mu Mv Mw My Nd Ne Nk Nl Nq Nx Of Oh Oz Pa Pc Pd Pe Pf Qb) Nl(Fp Hw Hx Ij Il In Iu Ji Jj Jk Js Ly Mb Mt Mu Mw Mx My Nk Nq Ns Oe Of Oy Oz Pc Pf Qb) Of(Fp Hx Ik In Ji Jk Lj Ly Mb Mt Mu Mv Mw My Nd Ne Nq Ns Nx Oh Oy Oz Pc Pd Pe Pf) Fp(Hx Ij Il In Jj Jk Js Ly Mb Mt Mw My Nk Nq Ns Oe Oz Qb) Hx(Ji Jj Jk Lj Ly Mb Mt My Ne Nq Nw Oe Oz Pe Pf) Jk(Ik Ji Li Lj Ly Mt Ne Nx Oh Oz Pc Pe Pf) Nq(Ik Ji Ly Mb Mt Ne Nw Oz Pc Pf) My(Ik Ji Ly Mb Mt Nd Ne Nw Oz Pc) Mw(Ik Ji Mt Ne Nw Nx Oz Pc Pf) Ly(In Jj Mb Ne Ns Oe Oz Pf) Mb(In Ji Lj Mm Mt Ns Pf) Ne(In Jj Mt Nk Ns Qb) Lj(In Js Nd Oz Pc Qb) In(Ik Ji Mt Pe) Oz(Mt Mv Ns) Pc(Mu Mv Oy) Jj(Ik Nd) LiOy} Ji{Nh(Fp Hr Hw Hx Ik Il In Iu Jj Jk Jn Jq Jr Js Li Ly Mb Ml Mp Ms Mt Mu Mw Mx My Nf Nj Nk Nn Nq Ns Nv Ny Oe Of Oy Oz Pc Pd Pf Pg Qa Qb Qc Qd) Ik(Hw Hx Il In Jj Jk Jo Jq Js Lj Mm Ms Mt Mu Mw Mx My Nc Nf Ng Nj Nk Nq Ns Oe Of Oy Pf Qa Qb) Nc(Hw Hx In Jj Jq Js Mb Ms Mt Mx Nk Oe Oz Pf Qb) Pf(Hw Hx In Js Ly Mb Mp Ms Nd Nj Nl Nq Qb) Mb(Hx In Jq Ly Ml Mm Mt Nj Qb) In(Fp Hx Mt Ne Nj Nl Nt Pe) Qb(Fp Lj Mt Ne Nj Nl Qe) Hx(Fp Li Ms Mt Nj Nl) Js(Ad bM Mt Nj Nl) Mt(Ms Nj) Nk(Nj Nl)} Nw{Ik(Hw Hx Ij Il In Jj Jk Js Ly Mb Md Ml Mm Mp Ms Mt Mu Mv Mw Mx My Nb Nc Nf Ng Nh Nj Nk Nl Nn Nq Ns Nv Ny Oe Of Oy Oz Pf Pg Po Qa Qb) Nj(Hx Il In Js Ly Mb Ml Mm Ms Mt Mu Mw Mx My Nh Nk Nq Nv Ny Oy Oz Pd Pf Pg Qb) Nh(Hx Il In Jn Js Ly Mb Ml Mt Mw Mx My Nk Nq Nv Ny Oz Pf Qb) Nc(Hx In Js Ly Mb Mt Mw Mx My Nd Nk Nq Nv Ny Oz Pf Qb) Mb(In Js Ly Ml Mm Mt Mw My Nl Nq Ny Pf) Nl(Hx In Js Mt Mx Nk Qb) In(Fp Mt Nd Ne) NdPf} Nk{Nc(Fp Fr Ik Im Jp Jt Lh Li Mb Mm Mt Mw Nv Nx On Pd Pe Pf Pz Qe) Nh(Fp Ik Jp Lh Li Mt Mw Nj Nx On Pd Pe Pf) Nl(Fp Fr Ik Jp Li Mt Mw On Pe Pf) Nj(Fr Ik Jp Li Mt On Pe Pf) Mt(Fp Ik Mb) NePf} Mt{Mb(Fp In Jp Li Ly Ml Mm Nc Nh Nj Nx Og Oh On Pc Pd Pf) In(Fp Ik Nc Nh Nj Nl Nx Pe Pf) Fp(Il Js Mx Nj Qb) Nh(Js Pc Pf Qb) Qb(Lj Qe) NjPf IkJj} Ik{Jp(Il In Jj Jk Lj Ly Mv Mw My Nc Ng Nh Nj Nq Oy Qb) Jj(Lh Li Lj Mm Mw Oh On Pf Pz Qe) In(Li Mm Mz On Pe) On(Jk Ng Of) QbQe} Nh{In(Fp Jp Jt Lh Li Mw Nv On Pe Pf) Qb(Lh Li On Pe Pf Qe) Pf(Js Ly Nx) Mb(Jp On) HxJp JsLi} On{Mb(In Ly My Nc Nj Of Qb) In(Fp Nc Nj Nl) Qb(Nc Nj)} Nj{Jp(Hx Ly Pf) MmPf NgvI InLi} Nc{LyPf InLi QbQe} Mb{LyJp MmPf} AdJsOf Unconstrained panels with 3 analytes, where 1.0E-9 >= 'model p-value' > 1.0E-10. Contains 8,190 panels of 37,261,550 total panels evaluated. : Et{Ip(Fr Hq Hr Hu Hv Ih Ii Ij Il Im Io Ir Is It Iu Iv Jh Ji Jj Jk Jl Jm Jn Jo Jp Jq Jr Jt Lh Li Lu Lv Lw Lx Lz Ma Mc Md Me Mg Mh Mi Mj Mk Mm Mn Mr Ms Mu Mv Mw Mx Mz Na Nb Ng Ni Nk Nm Nn No Nr Nt Nu Nv Nw Ny Oe Og Oh Oi Om On Oy Pa Pb Pd Pg Po Pz Qa Qc Qd Qe) Mm(Fr Hq Hr Hu Hv Ih Ii Ij Il Im Io Ir Is It Iu Iv Jh Ji Jj Jk Jl Jm Jn Jo Jp Jq Jt Lh Li Lu Lv Lw Lx Lz Ma Mc Md Me Mg Mh Mi Mj Mk Mn Mq Mr Ms Mu Mv Mw Mx Mz Na Nb Ng Ni Nk Nm Nn No Nr Nt Nu Nv Nw Ny Og Oh Oi Om On Oy Pa Pb Pd Pg Po Pz Qa Qc Qd Qe) Ni(Fr Hq Hr Hu Hv Ih Ii Ij Il Im Io Ir Is It Iu Iv Jh Ji Jj Jk Jl Jm Jn Jo Jp Jq Jr Jt Lh Lu Lv Lw Lx Lz Ma Mc Md Me Mg Mh Mi Mj Mk Mn Mq Mr Ms Mu Mv Mw Mx Mz Na Nb Ng Nm Nn No Nr Nt Nu Nv Nw Ny Oe Og Oh Oi Om On Oy Pa Pb Pd Pg Po Pz Qa Qc Qd Qe) Mq(Fr Hq Hr Hu Hv Ih Ii Ij Il Im Io Ir Is Iu Iv Jh Ji Jj Jk Jl Jm Jn Jo Jp Jq Jt Lh Lu Lv Lw Lx Lz Ma Mc Md Me Mg Mh Mi Mj Mk Mn Mr Ms Mu Mv Mw Mx Mz Na Nb Ng Nk Nm Nn No Nr Nt Nu Nv Nw Ny Oe Og Oh Oi Om On Oy Pa Pb Pd Pg Po Pz Qa Qc Qd Qe) Is(Fr Hq Hr Hu Hv Ih Ii Ij Il Im Io Ir It Iu Iv Jh Ji Jj Jk Jl Jm Jn Jo Jp Jq Jt Lh Lu Lv Lw Lx Lz Ma Mc Md Me Mg Mh Mi Mj Mk Mn Mr Ms Mu Mv Mw Mx Mz Na Nb Ng Nk Nm Nn No Nr Nt Nu Nv Nw Ny Oe Og Oh Oi Om On Oy Pa Pb Pd Pg Po Pz Qa Qc Qd Qe) It(Fr Hq Hr Hu Hv Ih Ii Ij Il Im Io Ir Iu Iv Jh Ji Jj Jk Jl Jn Jo Jq Jr Js Jt Lh Li Lu Lv Lw Lz Ma Mc Md Me Mg Mh Mi Ml Mk Mn Mr Ms Mu Mv Mw Mx Mz Na Nb Ng Nk Nm Nn No Nr Nt Nu Nv Nw Ny Oe Og Oh Oi Om On Oy Pa Pb Pd Pg Po Pz Qa Qc Qd Qe) Jm(Fr Hq Hr Hu Hv Ih Ii Ij Il Im Io Ir Iu Iv Jh Ji Jj Jk Jl Jn Jo Jp Jq Jt Lh Lu Lv Lw Lx Lz Ma Mc Md Me Mg Mh Mi Mj Mk Mn Mr Ms Mu Mv Mw Mx Mz Na Nb Ng Nk Nm Nn No Nr Nt Nu Nv Nw Ny Oe Og Oh Oi Om On Oy Pa Pb Pg Po Pz Qa Qc Qd Qe) Jp(Fr Hq Hr Hu Hv Ih Ii Ij Il Im Io Ir Iu Iv Jh Ji Jj Jk Jl Jn Jo Jq Jt Lh Lu Lv Lw Lx Lz Ma Mc Md Me Mg Mh Mi Mj Mk Mn Mr Ms Mu Mv Mw Mx My Mz Na Nb Ng Nk Nm Nn No Nr Nt Nu Nv Nw Ny Og Oh Oi Om On Oy Pa Pb Pd Pg Po Pz Qa Qc Qd Qe) Mj(Aa Fr Hq Hr Hu Hv Ih Ii Ij Il Im Io Ir Iu Iv Jh Ji Jj Jk Jl Jn Jo Jq Jt Lh Lu Lv Lw Lx Lz Ma Mc Md Me Mg Mh Mi Mk Mn Mr Ms Mu Mv Mw Mz Na Nb Ng Nk Nm Nn No Nt Nu Nv Nw Ny Oe Og Oh Oi Om On Oy Pa Pb Pg Po Pz Qa Qc Qd Qe) Ir(Fr Hq Hr Hu Hv Ih Ii Ij Il Im Io Iu Iv Jh Ji Jk Jl Jn Jo Jq Jr Jt Lh Lu Lv Lw Lx Lz Ma Mc Md Me Mg Mh Mi Mk Mn Mr Ms Mu Mv Mw Mz Na Nb Ng Nk Nm Nn No Nr Nt Nu Nv Nw Ny Og Oh Oi Om On Oy Pa Pb Pd Pg Po Pz Qa Qc Qd Qe) Ij(Fr Hq Hr Hv Ih Ii Im Io Iu Iv Jh Jj Jk Jl Jn Jo Jq Js Jt Lh Lu Lv Lw Lx Lz Ma Mc Md Mg Mh Mi Mk Mn Mr Ms Mu Mv Mw Mx My Mz Na Nb Nf Ng Nk Nm Nn No Ns Nu Nv Nw Ny Oe Og Oh Oi Om On Oy Pa Pb Pg Po Pz Qa Qc Qd Qe) Jl(Aa Fr Hq Hr Hu Hv Ih Ii Il Im Io Iu Iv Jh Ji Jj Jk Jn Jo Jq Jt Lh Lu Lv Lw Lx Lz Ma Mc Md Me Mg Mh Mi Mk Mn Mr Ms Mu Mv Mw Mz Na Nb Ng Nk Nm Nn No Nt Nu Nv Nw Ny Oe Og Oh Oi Om On Pa Pb Pg Po Pz Qa Qc Qd Qe) Jq(Fr Hq Hr Hu Hv Ih Ii Il Im Io Iu Iv Jh Jj Jk Jn Jo Jt Lh Lu Lv Lw Lx Lz Ma Mc Md Me Mg Mh Mi Mk Mn Mr Ms Mu Mv Mw Mx Mz Na Nb Ng Nk Nm Nn No Nr Nt Nu Nv Nw Ny Og Oh Oi Om On Oy Pa Pb Pg Po Pz Qa Qc Qd Qe) Lz(Fr Hq Hr Hu Hv Ih Ii Io Iu Iv Jh Ji Jj Jk Jn Jo Jr Jt Lh Lu Lv Lw Lx Ma Mc Md Me Mg Mh Mi Mk Mn Mr Ms Mu Mv Mw Mx Mz Na Nb Ng Nk Nm Nn No Nt Nu Nv Nw Ny Og Oh Oi Om On Oy Pa Pb Pd Pg Po Pz Qa Qc Qe) Mg(Fr Hq Hr Hu Hv Ih Ii Il Im Io Iu Iv Jh Ji Jj Jk Jn Jo Jt Lh Lu Lv Lw Lx Ma Mc Md Me Mh Mi Mk Mn Mr Ms Mu Mv Mw Mz Na Nb Ng Nk Nm Nn No Nr Nu Nv Nw Ny Og Oh Oi Om On Oy Pa Pb Pg Po Pz Qa Qc Qd Qe) Na(Fr Hq Hr Hu Hv Ih Ii Il Im Io Iu Iv Jh Ji Jk Jn Jo Jt Lh Lu Lv Lw Lx Ma Mc Md Me Mh Mi Mk Mn Mr Ms Mu Mv Mw Mz Nb Ng Nk Nm Nn No Nr Nt Nu Nv Nw Ny Og Oh Oi Om On Oy Pa Pb Pg Po Pz Qa Qc Qd Qe) Nm(Fr Hq Hr Hu Hv Ih Ii Il Im Io Iu Iv Jh Ji Jj Jk Jn Jt Lh Li Lu Lv Lw Lx Mc Md Me Mh Mi Mk Mn Mr Ms Mu Mv Mw Mx Mz Nb Ng Nn No Nr Nt Nu Nv Nw Ny Og Oh Oi Om On Oy Pa Pb Pg Po Pz Qa Qc Qd Qe) Lw(Fr Hq Hr Hu Hv Ih Ii Il Im Io Iu Iv Jh Ji Jj Jk Jn Jo Jt Lh Lu Lv Lx Ma Mc Md Mh Mi Mk Mn Mr Ms Mv Mw Mx Mz Nb Ng Nk Nn No Nr Nt Nu Nv Nw Ny Og Oh Oi Om On Pa Pb Pg Po Pz Qa Qc Qd Qe) Jt(Fr Hq Hr Hu Hv Ih Ii Il Im Io Iu Iv Jh Jj Jk Jn Jo Lh Lu Lv Lx Ma Mc Md Me Mh Mi Mk Mn Mr Ms Mu Mv Mw Mx Mz Nb Ng Nk Nn No Nr Nu Nv Nw Ny Og Oh Oi Om On Pa Pb Pg Po Pz Qa Qc Qd Qe) Lx(Fr Hq Hr Hu Hv Ih Ii Il Im Io Iu Iv Jh Ji Jj Jk Jn Jo Lh Lu Lv Ma Mc Md Me Mh Mi Mk Mn Mr Ms Mv Mz Nb Ng Nk Nn No Nt Nu Nv Nw Ny Og Oh Oi Om On Pa Pb Pd Po Pz Qa Qc Qd Qe) Mh(Fr Hr Hu Hv Ih Ii Il Im Io Iu Iv Jh Ji Jj Jk Jn Jo Lh Li Lu Lv Ma Mc Md Me Mi Mk Mn Mr Ms Mv Mz Nb Ng Nk Nn No Nr Nt Nu Nv Nw Ny Og Oh Oi Om On Pa Pb Po Pz Qa Qc Qd Qe) Mk(Fr Hq Hr Hu Hv Ih Ii Il Im Io Iu Iv Jh Ji Jj Jk Jn Jo Jr Lh Lu Lv Ma Mc Md Me Mi Mn Mr Ms Mv Mz Ng Nk Nn No Nt Nu Nv Nw Ny Og Oh Oi Om On Pa Pb Pd Po Pz Qa Qc Qd Qe)

Lv Lx Ma Md Mf Mg Mh Mj Mm Mn Mu Mv Nb Nr Nv Nw Nx Og Oh Oi Om On Pa Pb Pz Qa) Nr(Fr Hq Ih Il Im Io Ir Is Iu Jg Ji Jr Li Lj Lu
Lv Lx Md Mf Mg Mh Mj Ml Mm Mn Mu Mv Nv Nw Nx Og Oi Om On Pa Pb Pz) Mh(Fr Hq Ih Ij Im Io Ir Is Iu Jg Ji Jk Jn Jr Jt Li Lj Lu Lv Lx
Md Mg Mj Mm Mu Mv Nq Ns Nw Oi Om On Pa Pb Pz Qa) Pz(Fr Hq Ih Ij Il Im Io Ir Is Ji Jr Li Lu Lv Lx Ma Md Mg Mj Mm Mn Mu Mv Nb
Nv Nw Ny Og Oi Om On Oy Pa Pb Pg) Fr(Hq Ih Ij Il Im Io Ir Is Iu Ji Jn Jr Jt Li Lj Lv Lx Md Mg Mj Mm Mn Mu Mv Ns Nw Oi Om On Pa Pb
Qa Qc) Lx(Hq Ih Il Im Io Ir Is Iu Ji Jk Jn Jr Jt Li Lj Lu Lv Md Mg Mj Mm Mu Mv Nq Ns Nw Oi Om On Pa Pb Qa) Hq(Ih Ij Il Io Ir Is Iu Ji Li
Lv Ma Md Mg Mj Mm Mn Mu Mv Mw My Nv Nw Ny Oi Om On Oy Pa Pb Pg Qa) Is(Ih Ij Il Jl Jk Jn Jt Li Lj Lu Lv Md Mg Mj Mm Mn Mu
Mv Nq Ns Nv Nw Oi Om On Pa Pb Qa Qc Qd) On(Ih Il Io Ir Iu Ji Jk Jn Jr Jt Li Lj Lv Md Mg Mj Mm Mu Mv Nq Ns Nv Nw Oi Om Pa Pb Qa
Qc) Oi(Ih Ij Io Ir Iu Ji Jk Jn Jr Jt Li Lj Lu Lv Md Mg Mj Mm Mu Mv Nq Ns Nw Om Pa Pb Qa) Md(Ih Ij Il Ji Jk Jn Jr Jt Li Lj Lv Mg Mj Mm
Mu Mv Nq Ns Nv Nw Om Pa Pb Qa Qc) Mj(Ih Ij Il Io Ir Iu Ji Jk Jn Jr Jt Lv Mg Mm Mu Mv Nq Ns Nw Om Pa Pb Qa Qc) Ih(Im Io Ir Iu Jg Ji Jr
Jt Li Lj Lu Lv Mg Mm Mu Mv Nb Nq Ns Nw Om Pa Pb) Mm(Il Im Io Ir Iu Jg Ji Jn Jr Li Lj Lu Lv Mg Mv Ns Nw Om Pa Pb Qa) Pb(Io Ir Iu Ji
Jk Jn Jr Jt Li Lj Lv Mg Mu Mv Nq Ns Nw Om Pa Qa) Js(Ad aH aI Ap aY Bc Bn bQ bX cK cW Dd dE Kf Kj Pj Tz Uk) Om(Im Io Ir Iu Jg Ji Jn
Jr Jt Li Lj Lu Lv Mg Ns Pa Qa) Ji(Im Io Ir Iu Jg Jr Li Lu Lv Mf Mg Mn Mv Og Pa) Li(Io Iu Lj Lu Lv Mf Mg Mu Mv Nw Og Pa) Io(Jk Jn Jr Jt
Mg Nq Ns Nw Qa) aA(Fp Hx Ly Mp Nc Nd Nh Nl Of) Qa(fj Il Ir Iu Jn Mv Nv Nw) Jt(Ij Il Ir Iu Lv Mg Mv Nw) Mv(Ij Lj Mg Ns Nw) Il(Ij Jk Jn
Ns Qc) Jr(Ir Iu Lu Lv Pa) Aa(Me Mp Of Pc) Nw(Ir Jn Lj Ns) Pa(Lj Lv Mg) Ir(Ij Jn) sC(jG qB) MgLj JnNv KkvB} Jg{Nl(Fr Hq Hr Hu Hv Ih Ii
Ik Im Io Iq Is It Iv Jh Jl Jm Jn Jo Jp Jq Jr Jt Lh Li Lj Lu Lv Lw Lx Lz Ma Mc Md Me Mf Mg Mh Mi Mj Mk Ml Mm Mn Mp Mq Mr Ms Mv Mz
Na Nb Nc Nd Ne Nf Nh Ni Nj Nm Nn No Nr Nt Nu Nv Nw Nx Ny Og Oh Oi Om On Pa Pb Pd Pe Pg Po Pz Qa Qc Qd Qe) Of(Fr Hq Hr Hu Hv
Hw Ih Ii Ij Il Im Io Ip Iq Ir Is It Iu Iv Jh Jj Jl Jm Jn Jo Jp Jq Jr Js Jt Lh Li Lu Lv Lw Lx Lz Ma Mc Md Me Mf Mg Mh Mj Mk Ml Mm Mn Mp
Mq Mr Ms Mx Mz Na Nb Nf Ni Nk Nm Nn No Nr Nt Nu Nv Nw Ny Oe Og Oi Om On Pa Pb Pg Po Pz Qa Qb Qc Qd Qe) Ng(Fr Hq Hr Hu Hv
Hw Ih Ii Ij Il Im Ip Ir Is It Iu Iv Jh Jj Jl Jm Jn Jo Jp Jq Jr Jt Lh Li Lj Lu Lv Lw Lx Lz Ma Mc Md Me Mf Mg Mh Mi Mj Mk Ml Mm Mn Mp Mq
Mr Ms Mx Mz Na Nb Nf Ni Nm Nn No Nr Ns Nt Nu Nv Nw Ny Oe Og Oi Om On Oy Pb Pg Po Pz Qa Qc Qd Qe) Nj(Aa Fr Hq Hr Hu Hv Ih Ii
Ik Im Io Ip Iq Ir Is It Iv Jh Jl Jm Jn Jo Jp Jq Jr Jt Lh Lu Lv Lw Lx Lz Ma Mc Md Me Mf Mg Mh Mi Mj Mk Ml Mn Mp Mq Mr Ms Mx Mz Na
Nb Nd Ne Nf Ni Nm Nn No Nr Nt Nu Nv Ny Og Oi Om On Pb Pg Po Pz Qa Qc Qd Qe) Mb(Hq Hr Hu Hv Hw Ij Ik Il Im Iq Is It Iu Jh Jj Jk Jl Jn
Jo Jp Jq Js Lh Li Lx Ma Mc Md Mg Ml Mn Mp Mr Ms Mu Mv Mw Mx Mz Na Nb Nd Ne Nf Nk Nn Nr Nv Nw Nx Ny Oe Og Oh Oi On Oy Oz
Pa Pc Pd Pe Pg Po Pz Qa Qb Qc Qd Qe) Nc(Fr Hq Hu Hv Ih Ii Im Io Ip Ir Is It Iv Jl Jm Jo Jp Jq Jr Jt Lh Lu Lv Lw Lx Lz Mc Md Me Mf Mg Mh
Mi Mj Mk Mn Mq Mr Mz Na Nb Ne Nf Nm No Nr Nt Nu Og Oi Om On Pa Pb Pg Po Pz Qe) Oz(Hq Hu Hw Ij Ik Il Im In Iq Iu Jh Ji Jj Jr Js Li
Ma Me Mf Ml Mm Mn Mp Ms Mu Mx Mz Nd Ne Nf Nk Nn Nr Nt Nv Nw Nx Ny Oe Oh Oi Oy Pc Pd Pe Pf Pz Qc Qd Qe) Jk(Hw Ih Ij Im
In Io Iq Ir Iu Iv Jj Jl Jp Jr Js Lh Lv Lx Ma Me Mf Ml Mm Mr Ms Mu Mv Mw My Nd Nk Nq Nr Ns Nt Nu Nw Oe Og Om On Oy Pa Pd Pg Po
Pz Qa Qb Qe) Nh(Fr Hq Ih Ii Io Ip Ir Is It Iv Jl Jm Jo Jp Jq Jt Lh Lu Lv Lw Lx Lz Mc Me Mf Mg Mh Mi Mj Mk Mn Mq Mr Mz Na Nb Ne Ni
Nm No Nr Nt Nu Og Om On Pb Qe) Hx(Hu Hw Ih Ij Ik Il Im In Iq Iu Jh Jp Jr Js Lh Li Lx Ma Me Ml Mm Mp Mr Ms Mu Mv Mw Mz Nd Nf
Nk Nn No Nr Ns Nx Ny Oh Oi Oy Pa Pc Pd Pz Qa Qb Qe) Fp(Hq Hr Hu Hv Hw Ii Ik Iq Iu Jh Ji Jn Jr Ma Md Me Mf Ml Mm Mn Mp Ms Mu
Mv Mx Nb Nd Ne Nf Nn Nv Nx Ny Og Oh Oi Oy Pc Pd Pf Pg Po Qa Qc Qd Qe) Ly(Hu Hw Ii Ij Ik Il Im Iu Jh Ji Jo Jr Js Li Lj Md Me Mg Ml
Mm Ms Mt Mu Mv Mw Mx Nd Nf Nk Nn No Nr Nv Nw Nx Ny Oh Oi Oy Pa Pc Pd Pe Qb Qe) Ne(Hr Hu Hw Ij Ik Il Iq Iu Jh Ji Jn Js Li Lj Ma
Ml Mm Mp Ms Mu Mv Mx Nd Nf Nn Nv Nw Nx Ny Oe Oh Oy Pa Pc Pd Pe Pf Qa Qc Qd) Nq(Hw Il Im In Io Iq Iu Jj Jr Js Lh Li Lj Lx Me Mf
Ml Mm Ms Mu Mv Mw My Nd Nk Nr Ns Nx Oe Oh Om Oy Pa Pd Pe Qb Qe) Nd(Aa Hw Ij Im In Iq Iu Jj Jp Js Li Mm Mr Mt Mu Mv Mw Nf
Nk No Nr Ns Nw Nx Oe Oh Oi Oy Pa Pc Pd Pe Pf Qb) Mt(Hw Ij Ik Il Iq Jh Ji Jj Js Li Lj Me Mp Ms Mu Mv Nk Nn Ns Nv Nw Nx Oe Om Oy
Pc Pd Pe Pf Qb) In(Ih Im Iq Jr Li Me Mf Ml Mm Mr Mu Mv Mw My Mz Nk Ns Nt Nu Nw Nx Oe Oh Pc Pa Pc Pd Pf Qa Qe) Lj(Hw Ij Ik Il Io
Iq Iu Ji Jj Jn Jr Ma Me Ms Mw Mx My Nf Nk Ns Nx Ny Oe Oy Pd Pf Qa Qc Qd) My(Hw Io Iq Iu Jj Jr Li Ma Me Ml Mm Ms Nk Ns Nx Oe Oh
Om Pa Pd Pe Pf Qb) Ji(Hw Ii Ij Ik Il Iq Jj Jq Js Mp Ms Mu Mv Nf Nn Ns Nv Ny Oe Oy Pc Pf Qb) Pf(Hw Ij Ik Il Iq Iu Jj Js Ma Mp Mu Mv Nf
Nk Ns Nx Oe Oy Pc Qb) Ik(Hw Ij Il Iu Jh Js Li Mm Mu Mv Nf Nk Ns Nw Oe Oy Pc Qb) Pc(Hw Ij Il Iq Jh Jj Js Mp Ms Nf Nn Ns Nv Nx Ny Oe
Qb) Mw(Hw Io Iq Iu Jj Lh Li Me Nr Ns Oe Oh Om Pa Pd Pe) Nx(Hw Ij Il Jj Js Ms Mu Mv Nf Ns Oe Oy Qb) Oy(Iq Jj Me Mk Mr Nr Nw Oe On
Pa Pd Pe) Mv(Io Iq Jj Js Li Me Nw Oe Om Pd Pe) Mu(Io Iq Iu Jj Me Nw Oe Pd Pe) Ns(Iq Iu Jj Js Me Oe) Nw(Il Js Nv Ny) Pe(Ij Il Js Qb) Iq(Jj
Oe Pd) Li(Il Mp Pg) Nb(Mr Nr) Qb(Qa Qe) Jj(Mf Pd) OeOh} Ji{Nc(Fp Fr Hq Hr Hu Hv Ih Ii Ij Il Im Iq Is It Iu Jh Jk Jm Jo Jp Jr Jt Lh Li Lj
Lu Lv Lw Lx Ly Lz Ma Mc Md Me Mf Mg Mi Mj Mk Ml Mm Mn Mp Mr Mu Mv Mw My Mz Na Nb Nd Ne Nf Ng Nh Ni Nj Nl Nm Nn No
Nq Nr Ns Nt Nu Nv Nw Nx Ny Of Og Oh Oi Om On Oy Pa Pb Pc Pd Pe Pg Po Pz Qa Qc Qd Qe) Ik(Fp Fr Hq Hr Hu Hv Ih Ii Ij Im Iq Is It Iu Jh
Jm Jn Jp Jr Lh Li Lu Lv Lw Lx Ly Lz Ma Mb Mc Md Mf Mg Mh Mi Mj Mk Ml Mn Mp Mq Mr Mv Mz Na Nb Nd Ne Ni Nl Nm Nn No Nr Nt
Nu Nv Nw Nx Ny Og Oh Oi Om On Oz Pa Pb Pc Pd Pe Pg Po Pz Qc Qd Qe) Mb(Aa Fp Fr Hq Hr Hw Ii Ij Il Im Iq Is It Iu Jj Jk Jn Jo Jp Jr Js Li
Lj Ma Mc Md Mh Mp Ms Mu Mv Mw Mx My Nb Nd Ne Nf Ng Nk Nl Nm Nn No Nq Nr Ns Nu Nv Nw Nx Ny Oe Of Og Oh On Oy Oz Pa Pc
Pd Pe Pg Po Pz Qa Qc Qd Qe) Nh(Fr Hq Hu Hv Ih Ii Ij Im Io Ip Iq Ir Is It Iv Jh Jl Jm Jo Jp Jt Lh Lj Lu Lv Lw Lx Lz Ma Mc Md Me Mf Mg Mh
Mi Mj Mk Mm Mn Mq Mr Mv Mz Na Nb Nd Ne Ng Ni Nl Nm No Nr Nt Nu Nw Nx Og Oh Oi Om On Pa Pb Pe Po Pz Qe) Nj(Fp Fr Hr Hw Ii
Il Im Is Iu Jj Jn Jo Jp Jq Li Lj Ly Ma Ml Mm Mp Ms Mu Mw Mx My Nb Nd Ne Nf Ni Nl Nm Nn No Nq Nr Ns Nu Nv Nw Nx Ny Oe Of Og
Oh On Oy Oz Pa Pc Pd Pe Pg Po Pz Qa Qc Qd Qe) Hx(Fr Hr Hw Il Im Iu Jj Jo Jp Jq Js Lj Ly Ml Mm Mp Mu Mv Mw Mx My Nd Ne Nf Ng Nk
Nn No Nq Nr Ns Nw Nx Ny Oe Of Og Oh On Oy Oz Pc Pd Pe Pg Po Pz Qa Qb Qc Qe) Nl(Fp Fr Hr Hw Il Im Iu Jj Jn Jq Li Lj Ly Ml Mm Mp
Ms Mt Mu Mw Mx My Nd Nf Nn No Nq Ns Nv Nx Ny Oe Of Oy Oz Pc Pd Pe Pg Pz Qa Qc Qd Qe) Pf(Fp Hq Hr Ii Ij Il Im Iq Iu Jj Jk Jn Jo Jq
Jr Lj Ma Ml Mt Mu Mv Mw Mx My Ne Nf Ng Nk Nn Ns Nv Nx Ny Oe Of Oh Oy Oz Pc Pg Po Qa Qc Qd) Mt(Fp Hw Ii Il Jj Jk Jn Jq Lj Ly Ml
Mp Mu Mv Mw Mx My Nd Ne Nf Ng Nk Nn Nq Ns Nv Ny Oe Of Og Oy Oz Pc Pg Qa Qc) Fp(Hr Hw Il Jj Jn Jq Js Ly Ml Ms Mw Mx My Nd
Ne Nf Nk Nq Ns Nv Ny Oe Oz Qa Qc) Nd(Aa Fr Hw Il Im In Jj Jp Jq Js Li Lj Mm Ms Mw My Nk Nr Ns Oz Pd Pe Qb Qe) Ne(Hw Il Iu Jj Jn Jq
Js Li Ly Mp Ms Mw Mx My Nk Nq Ns Oe Oz Pd Qa) In(Hw Ih Im Jq Li Lj Ly Mp Ms Mw Nr Nu Nx Oz Pc Pd Qa Qe) Ms(Hw Il Js Li Ly Mw
My Nq Oz Pc Pd Qb) Js(aY Bo bX Ch cK cP Dg Li Lj Nt Pe) Qb(Ih Im Jq Li Nt Oz Pc Pd Pe Qa) Oz(Il Im Jq Li Lj Ly Mw) Jq(Il Im Lj Ly Nx)
Li(Hw Il Mp Nq Pg) Ly(Hw Jj) Lj(Hw Mx)} Nw{Nj(Fp Fr Hq Hr Hv Hw Ih Ii Ij Im Io Iq Ir Is It Iu Iv Jh Jj Jk Jn Jp Jq Jr Jt Li Lj Lu Lv Lw Lx
Lz Ma Mc Md Me Mf Mg Mh Mi Mj Mk Mn Mp Mq Mr Mv Mz Na Nb Nc Nd Ne Nf Ng Ni Nl Nm Nn No Nr Ns Nu Nx Oe Of Og Oh Oi Om
On Pa Pb Pc Pe Po Pz Qa Qc Qd Qe) Ik(Fp Fr Hq Hr Hu Hv Ih Ii Im Iq Ir Is It Iu Jh Jm Jn Jo Jp Jq Jr Lh Li Lj Lu Lv Lw Lx Lz Ma Mc Me Mf
Mg Mh Mi Mj Mk Mn Mq Mr Mz Na Nd Ne Ni Nm No Nr Nt Nu Nv Og Oh On Pa Pb Pc Pd Pe Pz Qc Qd Qe) Nh(Fp Hr Hv Hw Ii Ij Im
Iu Jj Jk Jr Li Lj Ma Mc Md Mf Mm Mp Ms Mu Mv Mz Nb Nc Nd Ne Nf Ng Nl Nm Nn Ns Nx Oe Of Og Oh Oy Pa Pc Pd Pe Pg Po Pz Qa Qc
Qd Qe) Mb(Fp Fr Hw Hx Ij Il Im Jn Li Lj Ma Mc Md Mh Mp Ms Mu Mv Mx Mz Na Nb Nd Ne Nf Ng Nk Ns Nv Nx Oe Of Og Oh On Oy Oz
Pc Pd Pe Pg Po Pz Qb Qd) Nc(Fp Hr Hv Hw Ij Il Im Iu Jj Jk Jn Jr Li Mc Md Mf Ml Mm Mp Ms Mu Mv Mz Nb Nf Ni Nn Ns Nx Oe Of Og Oh
Oy Pc Pd Pe Pg Po Pz Qa Qc Qd) Nl(Fp Hw Il Jn Ly Ml Ms Mu Mw My Mz Nd Nq Nv Nx Ny Oe Oy Oz Pc Pd Pf Pg Qa) Hx(Fp Im In Js Li Ly

Ii Ij Il Im Iq Iu Jj Jk Jn Jp Jr Js Jt Lh Li Lu Lv Lw Lz Ma Mc Md Me Mf Mi Mj Mk Ml Mm Mn Mp Mq Mr Mu Mv Mw Mx Mz Na Nb Ne Nf Ng Nk Nm Nn Nq Ns Nt Nv Nw Ny Of Og Oh Oi Om On Oy Oz Pa Pb Pd Pe Pg Pz Qa Qc Qe) In(Fr Hu Hw Hx Ii Ip Iq Ir Is It Iu Iv Jj Jl Jo Jp Jq Jr Lu Lv Lw Lx Lz Ma Mc Md Me Mf Mg Mh Mi Mj Mk Ml Mn Mp Mq Mr Mu Mv Mw Mx My Mz Na Nb Nf Ng Nk Nm Nn No Nq Nr Ns Nu Nv Ny Oe Of Oi Oy Pa Pb Pg Po Pz Qa Qb Qd Qe) Nh(Fr Hq Hr Hu Hv Ih Ii Ij Io Ip Iq Ir Is It Iu Iv Jh Jl Jm Jo Jq Jr Jt Lu Lv Lw Lx Lz Ma Mc Md Me Mf Mg Mh Mi Mj Mk Ml Mn Mp Mq Mr Mu Mv Mz Na Nb Nf Ng Ni Nl Nn Nq Nr Nt Nu Nv Ny Oi Oy Pa Pb Pg Po Pz Qc Qd Qe) Nl(Fr Hr Hw Hx Ih Il Im Iu Jj Jk Jn Jp Jr Jt Lh Li Lj Lv Lw Ly Ma Mc Md Mf Mi Mk Ml Mm Mp Mr Ms Mu Mv Mw Mx My Mz Nb Nd Ne Ng Ni Nm Nn No Nq Nr Ns Nv Ny Oe Of Og Oh Om On Oy Oz Pa Pd Pe Pz Qa Qd Qe) Ik(Aa Fr Hq Hr Hu Hv Ih Ii Io Ip Iq Ir Is It Iv Jh Jl Jm Jn Jo Jq Jr Jt Lh Lu Lv Lw Lx Lz Mc Md Me Mf Mg Mh Mi Mj Mk Ml Mn Mp Mq Mr Na Nb Ne Nf Ni Nm Nn Nr Nt Nu Nv Ny Oi Om Pa Pb Pg Po Pz Qc Qd Qe) Fp(Aa Fr Hq Hr Hu Hv Ih Ii Io Ip Iq Ir Is It Iu Iv Jh Jl Jm Jo Jp Jq Jt Lh Li Lj Lu Lv Lw Lx Lz Mc Me Mg Mh Mi Mk Mn Mq Mr Na Nb Ni Nm Nn No Nr Nt Nu Oi Om On Pa Pb Pe Po Pz Qd Qe) Nd(Fr Hw Hx Im Iq Iu Iv Jj Jl Js Jt Lh Lj Lv Lw Lx Ly Ma Mi Mj Mk Ml Mp Mr Ms Mw Mx My Mz Na Ne Nm Nn No Nr Ns Nv Oe Of Og Oh Om On Oy Oz Pa Pd Pe Qb Qe) Oz(Hw Hx Il Jj Jk Jp Jr Js Jt Lh Li Lj Lv Ly Ma Me Mf Mk Ml Mm Mp Mr Ms Mu Mv Mw Mx My Mz Ne Ng Nm Nq Nr Ns Nt Oe Of Og Oh Om On Oy Pa Pd Pe Qb) Nw(Fr Hw Ii Ij Il Im Iq Jj Jk Jn Jr Li Lj Ma Md Me Mf Mg Ml Mm Mp Mv Mx Mz Nb Nf Ng Nk Nn Ns Nt Ny Oe Of Og Om Oy Pe Pg Po Qa Qc) Hx(Fr Hw Ih Im Iu Jk Jr Js Jt Lh Lv Ly Mr Ms Mw My Mz Ne Nk Nm Nn No Nq Nr Ns Nt Nv Oe Of Og Oh On Pa Pb Pd Pe Pz Qb Qe) Li(Hw Im Iq Jj Jn Jr Ly Mj Mp Ms Mu Mv Mw Mx My Ne Nf Ng Nk Nq Ns Oe Of Oy Pd Pg Po Qa Qc Qd) Nk(Hw Ih Im Jj Jr Js Lv Ly Me Mf Ml Mm Mp Mu Mv Mw My Ng Nq Nt Oe Of Og Oh Oy Pd Pe) Lj(Hw Il Iq Jj Jk Jn Jp Jr Ly Mm Ms Mx Ne Nq Ns Oe Of Og Oh Pd Qa Qc Qd) Ly(Hw Im Jj Jp Js Me Mm Ms Mw Mx Ne No Ns Oe Of Og Oh On Pd Pe Qb) Ms(Hw Im Jj Jn Jp Js Lh Mf Mm Mx My Ne Nm Ns Oe Og Oh Pd Pe Qb) Qb(Hw Ih Jj Jp Jr Jt Lh Lv Mm Ne Nm Nn Ns Nt Og Oh On Pd Qa) Js(Ad Hw Ih Im Jj Jp Jr Jt Lh Lv Ml Mm Ne Ns Nt Og Oh Pd Qe) Hw(Im Jj Jp Jr Jt Lh Mm Mw Ne Nm Ns Og Oh On Pd Pe) Jj(Im Jt Lh Mf Mm Ne Nm Ns Nt Og Oh Pd Pe) Pd(Il Iq Jk Mp Mw Mx My Ne Nq Oe Of Og) Mb(aA Hq Hu Jh Jm Jo Jq Nt Nu Po) Oe(Aa Im Jt Lh Mm Ne Nt Og Oh Pe) Of(Ad Jt Lh Mm Nm Og On) Ne(Jp Mm Mx Ns Og Oh) Jk(Im Jp Jt Lh Og On) My(Jp Lh Og Om On) Nq(Jp Lh Mm On) Pe(Il Jn Mx Qa) Aa(Me Mp Ok) Mm(Mp Og) On(Oy Pg) aA(Et Ok) MkOy MwOm QaQe PjyK} Nh{Lh(Fp Fr Hq Hu Hv Ih Ii Ij Il Im Iq Is It Jh Jk Jl Jm Jn Jo Jp Jq Jr Jt Lj Lu Lv Lw Lx Ly Lz Ma Mc Md Me Mf Mg Mh Mi Mj Mk Ml Mm Mn Mp Mq Mr Ms Mu Mv Mw My Mz Na Nb Nc Nd Ne Nf Ng Ni Nl Nm Nn No Nq Nr Ns Nt Nu Nv Nw Nx Ny Og Oh Oi Om On Oy Pa Pb Pe Pg Po Pz Qc Qd Qe) Jp(Fr Hq Hr Hu Hv Ih Ij Il Im Iq Ir Is It Iu Iv Jh Jj Jm Jn Jq Jr Jt Lj Lu Lv Lw Lx Ma Mc Md Mf Mg Mi Mk Ml Mm Mn Mp Mr Ms Mu Mv Mw My Mz Na Nb Nc Nd Ne Nf Ng Ni Nl Nm Nn No Nq Nr Ns Nt Nu Nv Nw Ny Oe Of Og Oh Om On Oy Pa Pe Pg Po Pz Qc Qd Qe) Nx(Hr Hv Hw Hx Ih Ii Ik Il Im Is Iu Jh Jk Jl Jn Jq Jr Jt Lj Lu Lv Lw Lx Ly Lz Ma Mc Md Me Mf Mg Mh Mi Mj Mk Ml Mn Mp Mq Mr Ms Mu Mv My Mz Na Nb Nc Nd Ne Nf Ng Ni Nj Nl Nm Nn Nq Nr Ns Nt Nu Nv Ny Oe Of Og Oh Oi Om Oy Pa Pb Pg Pz Qa Qb Qc Qd Qe) Li(Fp Fr Hq Hu Ih Ii Ij Im Io Ip Iq Ir Is It Iu Iv Jh Jl Jm Jo Jq Jt Lj Lu Lv Lw Lx Lz Ma Mc Md Me Mf Mg Mh Mi Mj Mk Mn Mp Mq Mr Ms Mu Mv My Mz Na Nb Nc Nd Ne Ng Ni Nl Nm Nn No Nr Nt Nu Nv Ny Og Oh Oi Om On Oy Pa Pb Pe Pg Po Pz Qe) Nk(Hr Hu Hv Hw Hx Ii Ij In Ir Iu Iv Jh Jj Jk Jl Jm Jn Jo Jq Jr Js Lu Lv Lw Ly Lz Ma Mc Md Me Mf Mg Mh Mi Mj Mk Ml Mn Mp Mq Mr Ms Mu Mv Mx My Mz Na Nb Nd Ne Nf Ng Ni Nl Nm Nq Ns Nu Ny Oe Of Og Oi Om Pb Pg Po Qb Qc Qd) On(Fr Hq Hu Hv Ii Ij Im Iq Is It Iu Jh Jl Jm Jn Jq Jr Lj Lv Lw Lx Ma Mc Md Mf Mj Ml Mm Ms Mv Mz Na Nb Nc Nd Ne Nf Ng Ni Nl Nm Nn No Nr Nt Nv Nw Ny Og Oh Oi Om Pa Pe Pg Po Pz Qc Qd Qe) Fp(Fr Hr Hw Hx Ik Il Im Jh Jj Jn Jq Jr Jt Lv Lx Ly Ma Mb Mg Mh Mi Mk Ml Mn Mr Mu My Mz Na Nb Nc Nd Ne Nf Nj Nm Nn No Ns Nv Ny Oe Of Og Oh Om Oy Oz Pa Pc Pd Pe Pz Qa Qc Qd Qe) Pf(Hq Hu Hv Ih Ii Ij Io Ip Iq Ir Is It Iv Jh Jl Jm Jo Lj Lu Lw Lx Lz Mc Md Me Mf Mg Mi Mj Mk Mn Mq Mr Ms Mu Mv Nb Ng Ni Nl Nr Nt Nu Nv Ny Og Oi Pa Pb Pe Pg Po Qe) Mm(Fr Hr Hu Im Iu Jh Jj Jn Jq Jr Js Jt Lj Lv Lx Ly Mf Mp Ms Mw Mx Mz Na Nb Nc Nd Ne Nj Nm Nn No Nq Nr Ns Nt Oe Of Og Oh Om Oy Oz Pa Pd Pe Pz Qa Qc Qe) Pd(Fr Hr Hw Hx Ik Im Iu Jh Jn Jq Jr Jt Lj Lv Lx Ly Ma Mb Ml Mu Mx My Mz Na Nc Ne Nf Nj Nm Nn No Nq Nr Ns Nt Nv Oe Of Oh Om Oz Pa Pc Pe Pz Qa Qc) Mw(Fr Hr Il Im Iu Jj Jk Jn Jq Jr Jt Lj Lv Lx Ma Mf Ml Mp Ms Mx My Mz Na Nc Nd Ne Nf Nj Nm Nn No Nq Ns Oe Of Oh Om Oy Pa Pe Pz Qa Qc Qd) Nw(Fr Hq Hu Ih Io Ip Iq Ir Is It Iv Jh Jl Jm Jo Jq Jt Lu Lv Lw Lx Lz Me Mg Mh Mi Mj Mk Mn Mq Mr Na Ni No Nr Nt Nu Oi Om Pb) Ik(Hw Il Im Iu Jq Js Jt Lj Lv Lx Ly Ma Mx Mz Na Ne Nj Nm Nn Nr Ns Nv Of Oh Om Oy Oz Pa Pc Pe Pz Qa Qb Qc Qd Qe) Fr(Hr Hw Hx Il Im Jj Jk Jn Js Lj Ly Mf Ml Mu Mx My Nc Nd Ne Nj Nm No Nq Ns Oe Of Oh Oy Oz Pc Pe Qa Qb) Pe(Hr Hw Hx Il Im Iu Jj Jn Jr Jt Ly Ma Mb Ml Mz Ne Nf Nj Nm Nn No Ns Oe Oh Oz Pc Qc Qd) In(Ih Ii Ij Jl Jq Ly Ma Mb Mg Mu Mz Nm Nr Nt Ny Of Oy Oz Pa Pc Pg Po Qd) Mb(Im Jt Lj Lx Ly Ma Mz Nm Nn No Nv Oh Om Oy Pa Pz Qe) Jt(Hr Hw Hx Iu Jn Ly Mx Nj Ns Oe Of Oh Oz Pc Qa Qd) Js(Ad Dg Im Lj Lx Ma Nm Nn Nv Oh Om Pa Pz Qa Qe) No(Hw Hx Jj Jn Ly Mx Nj Nm Ns Oy Oz Pc Qa Qb) Oh(Hw Hx Im Jj Ly Mx Nj Oe Oz Pa Pc Qb) Nn(Hw Hx Jj Ly Mx Nj Ns Oz Pc Qb) Qe(Hw Hx Jj Jn Ly Mx Oz Pc Qc) Qb(Jl Lj Lx Nm Nr Oy Pa Pz) Jj(Im Ly Mg Nm Nr Nv Oy Pz) Pc(Im Lj Lx Ly Ma Mz Nm Nv) Lj(Hw Jn Ly Mg Mx Oz) Im(Hw Hx Nj Oz Qa) Nv(Hw Hx Mx Oz Qa) Ly(Lx Ma Nm Pa) Nm(Hw Of) Lx(Hx Mx) Om(My Oz) AaOk AdOf MzOz} Ik{Pf(Fp Fr Hq Hr Hu Hv Hw Hx Ih Ij Il Im Iq Is It Iu Jk Jl Jm Jn Jo Jq Jr Js Jt Lh Li Lj Lu Lv Lw Lx Lz Ma Mb Mc Md Me Mf Mh Mi Mj Mk Ml Mn Mp Mq Mr Ms Mu Mv Mw Mx My Na Nb Nd Ne Nf Ng Ni Nm Nn No Nq Nr Ns Nt Nv Nx Ny Oe Og Oh Oi Om On Oy Oz Pa Pb Pc Pd Pe Pg Po Pz Qa Qc Qd Qe) Jj(Hq Hr Hu Hv Hw Hx Ih Ii Ij Il In Io Ip Iq Ir Is It Iu Iv Jh Jk Jm Jn Jo Jq Jr Js Lu Lv Lw Lz Ma Mb Mc Md Me Mf Mg Mh Mi Mj Mk Ml Mn Mp Mq Mr Ms Mu Mv Mx My Na Nb Nd Ne Nf Ng Ni Nq Nt Nu Ny Oe Of Og Oi Om Oy Oz Pb Pc Pg Po Qb) Mm(Fr Hq Hr Hu Hv Ih Ii Il Im Io Ip Iq Ir Is It Iu Iv Jh Jl Jm Jn Jq Jr Jt Lh Lu Lv Lw Lx Lz Mc Md Me Mf Mg Mh Mi Mj Mk Ml Mn Mq Mr Ms Mu Mv Mw Mx Na Nb Nd Ne Nf Ni Nm Nr Nt Nu Nv Ny Og Oi Om On Pa Pb Pd Pg Po Qc Qd) Li(Fp Fr Hq Hu Hv Hw Hx Ij Im Iq Is It Iu Jh Jm Jn Jo Jq Jr Js Lh Lj Lv Lx Ly Ma Mb Mc Md Mh Ml Mp Ms Mu Mv Mw Mx My Mz Nb Nd Ne Ng Nl Nm Nn No Nq Nr Ns Nt Nv Nx Ny Oe Oh Oi Om On Oz Pa Pc Pd Pe Pg Po Pz Qa Qc Qd Qe) Jp(Fr Hq Hr Hu Hv Ih Ii Im Io Ip Ir Is It Iv Jl Jm Jn Jo Jq Jr Jt Lh Lu Lv Lw Lx Lz Mc Md Me Mf Mg Mh Mi Mj Mk Ml Mn Mq Mr Na Nb Nd Ni Nm Nr Nt Nu Og Oi Om On Pa Pb Pg Po) Lh(Fp Hr Hw Hx Ii Ij Im Iu Jo Js Lj Ly Mb Ml Mp Ms Mu Mv Mw Mx My Ne Nf Nj Nk Nl Nn No Nq Ns Nv Nx Ny Oh Oy Oz Pc Pd Pe Pz Qa Qc Qd Qe) On(Fp Hr Hu Hw Hx Ii Im Iu Jh Jn Jo Js Lj Ly Ma Mp Ms Mx Mz Nb Nd Ne Nf Nl Nn No Nv Nx Ny Oh Oi Oz Pc Pd Pe Pg Pz Qa Qc Qd Qe) Lj(Fr Hr Hw Il Im Jn Js Ly Mw Mx Mz Nc Nf Nj Nl Nm Nn No Ns Nx Oe Of Oh Om Oz Pa Pc Pd Pz Qa Qc Qd Qe) No(Fp Hw Hx Ij Il Jk Js Ly Mw My Mz Ne Nf Nj Nl Nq Ns Nx Oe Of Oh Oz Pc Pd Pe Pz Qa Qb Qd Qe) Qe(Fp Hr Hw Ij Iu Jk Js Ly Mw Mx My Nc Nf Ng Nj Nl Nq Ns Nx Oe Oh Oy Oz Pc Pd Qa Qc Qd) Nc(Fp Hw Im In Jt Lx Ly Ma Mw Mz Nm Nn Ns Nv Nx Oh Om Oz Pa Pc Pd Pe Pz Qa Qb Qd) Fr(Fp Hw Il In Ly Mb Mu Mv Mw My Ng Nj Nk Nl Nq Ns Nx Oe Of Oy Oz Pc Qb) Oh(Fp Hw Il Im Iu Js Ly Mb Mw Nf Nj Nl Ns Nx Oe Of Oz Pa Pc Pd Pe Qb) Mw(Fp Hw Il Jk Ly Mb Nf Ng Nj Nk Nl Ns Nx Oe Of Oz Pc Pd Pe Qb) Pe(Hr Hw Ij Jk Js Ly Mx My Mz Nf Nj Nl Ns Nx Of Oz Pc Qa) Fp(Il Im Js Ly Mx Mz Nf Nj Nl Ns Nx Oz Pa Pc Pd Pz Qb) Nk(Ih Jl Lx Ly Mz Ne Nn Nr Nv Nx Oz Pa Pd Pz Qd) In(Ih Jt Nj Nl Nn Nr Nx Om Pa Pd Pz Qd) Im(Hw Il Ly Nj Ns Nx Of Oz Pc Qb) Qb(Jl Lx Mz Nj Nn Nv Pa Qa) Nx(Il Mz Nj Nl Ns Of Oz) Of(Ad Nm Nn Nv Pz Qa) Nw(Io Ip Iv Jl Jt) Nv(Il Jk Ng Nq) Lx(Il Nj Pg) Et(Cu dE) Mz(Nj Nl) Qa(Il Js) AaOk MyOm PjsC} Nw{Nd(Aa Fr Hq Hr Hv Hw Ih Ii Ij Il Iq Ir Iu Iv Jh Jj Jk Jl Jn Jp Jr Jt Lh Lj Lu Lv Lw Lx Ly Lz Ma Mc Md Me Mf Mg Mh Mi Mj Mk Mn Mp

Figure 14 Continued

Mq Mr Mv Mx Mz Na Nb Ne Nf Ng Ni Nk Nm Nn No Nq Nr Ns Nt Nu Nv Nx Ny Oe Of Og Oh Oi Om On Oy Pa Pb Pc Pe Pg Po Pz Qa Qb
Qc Qd Qe) Nl(Fr Hq Hr Hu Hv Ih Ii Ij Im Io Iq Ir Is It Iu Iv Jh Jj Jk Jl Jm Jo Jp Jq Jr Jt Lh Li Lj Lu Lv Lw Lx Lz Ma Mc Md Me Mf Mg Mh Mi
Mj Mk Mm Mn Mp Mq Mr Mv Na Nb Nc Ne Nf Ng Ni Nm Nn No Nr Ns Nt Nu Of Og Oh Oi Om On Pa Pb Pe Po Pz Qc Qd Qe) Hx(Fr Hq Hr
Hu Hw Ih Ij Il Iu Jh Jj Jk Jn Jp Jr Jt Lh Lj Lx Ma Mc Md Me Mf Mh Mk Mp Mr Ms Mv Mx Mz Nb Nf Ng Nk Nn No Nr Ns Nt Nv Nx Oe Of
Og Oh On Oy Pa Pb Pc Pd Pe Pg Po Pz Qa Qb Qc Qd Qe) Mb(Aa Hq Hr Hu Hv Ih Ii Io Ip Iq Ir Is It Iu Iv Jh Jj Jk Jl Jm Jo Jp Jq Jr Jt Lh Lu Lv
Lw Lx Lz Me Mf Mg Mi Mj Mk Mn Mq Mr Ni Nm Nn No Nr Nt Nu Oi Om Pa Pb Qa Qc Qe) Nc(Fr Hq Hu Ih Ii Io Ip Iq Ir Is It Iv Jh Jl Jm Jo
Jp Jq Jt Lh Lj Lu Lv Lw Lx Lz Ma Me Mg Mh Mi Mj Mk Mn Mq Mr Na Ne Ng Nm No Nr Nt Nu Oi Om On Pa Pb Qe) Ne(Fp Hr Hv Hw Ij Il
Im In Jj Jk Jn Jr Li Lj Md Mf Ml Mm Mp Ms Mu Mv Mz Nb Nf Nn Nq Ns Nv Nx Ny Oe Of Og Oh Oy Oz Pc Pd Pe Pg Po Qa Qc Qd) Pf(Fp Fr
Hq Hr Hw Ij Im Iq Jk Jn Jr Ma Md Me Mf Ml Mm Ms Mu Mv Mx Mz Nb Nf Ng Nk Nn Ns Nv Nx Ny Oe Of Oh Oy Oz Pc Pg Po Qa Qc Qd)
In(Hw Il Iq Ir Iv Jr Li Lj Lv Mc Me Mf Mg Ml Mm Mp Mq Ms Mu Mv Mw My Nb Nf Nn Nq Nr Ns Nu Oe Of Og Oh Oy Pa Pc Pz Qa Qb Qe)
Ly(Fp Hw Ij Il Im Jj Js Li Lj Md Me Ml Mm Mp Mu Mv Mw Mx Nb Nf Nk Nq Ns Nv Nx Ny Oe Of Og Oh Oy Pc Pd Pe Pg Qb) My(Hu Hw
Im Jh Jn Jr Js Li Lu Lv Ma Me Mf Mg Ml Mm Mp Ms Mu Mw Mx Nb Nk Nr Nt Oe Og Oh Om On Oy Pe Qb Qc Qd) Fp(Hw Ij Im Jn Jr Md Ml
Mm Mp Ms Mu Mv Mz Nb Nf Nk Nq Ns Nx Oe Og Oy Oz Pc Pd Pg Po Qa Qc) Oz(Il Im Js Li Lj Ml Mm Mp Ms Mu Mv Mw Mx Nk Nq Nt
Nv Nx Ny Oh Oy Pg Qb) Mw(Hw Im Js Li Me Mf Mm Mp Mu Mx Nk Nx Oe Of Og Oy Pc Pd Pe Qb) Js(Ad Ih Li Lj Mp Ms Mu Mv Nk Nn
Nq Nr Ns Nt Nx Oy Pd Pe) Nx(Il Jj Mp Ms Mu Nf Nq Of Oy Pc Pg Qb) Pd(Il Ml Mp Ms Mu Mv Nq Nv Ny Oy Pg Qb) Qb(Ih Im Li Lj Nk Nq
Nt Pe Qa) Nj(Aa Hu Ip Jl Jm Jo Lh Nt) Pc(Ms Mu Nq Nv Ny Oy) Nq(Hw Li Me Of) Pg(Li Mi Mr Nr) Ny(Me Om Pe) Il(Li Pe) AaEt PoLi
MmMp MrNb MuMx} Nj{Jp(Aa Fr Hq Hr Hu Hv Ih Ii Ij Il Io Ip Iq Ir Is It Iu Iv Jh Jj Jk Jl Jm Jn Jo Jq Jr Jt Lh Lu Lv Lw Lx Lz Ma Mc Md
Me Mf Mg Mh Mi Mj Mk Ml Mn Mp Mq Mr Ms Mu Mv Mx My Mz Na Nb Nc Nd Ne Nf Ng Nl Nm Nn No Nq Nr Ns Nt Nu Nv Ny Oe Of Og
Oi Om On Oy Oz Pa Pb Pg Po Pz Qa Qc Qd Qe) Pf(Aa Fp Hq Hr Hw Hx Ih Ii Iq Ir Is It Iu Iv Jj Jk Jl Jn Jq Jr Js Jt Lj Lu Lv Lx Lz Ma Mb
Mc Md Me Mf Mg Mh Mi Mk Ml Mn Mp Mq Mr Ms Mu Mv Mx My Na Nb Nc Nd Ne Nf Ng Ni Nl Nm Nn No Nq Nr Ns Nt Nv Ny Oe Of Og
Oi Om Oy Oz Pa Pb Pc Pd Pe Pg Po Pz Qa Qb Qc Qd Qe) Li(Fp Fr Hq Hr Hu Hv Hw Ih Ii Ij Im Iq Is It Iu Jk Jl Jm Jn Jq Jr Jt Lh Lj Lv Lw Lx Lz
Ma Mb Mc Me Mf Mg Mh Mi Ml Mp Mq Mr Ms Mu Mv Mx My Mz Na Nb Nc Nd Ne Nf Ng Ni Nl Nm Nn No Nq Nr Ns Nt Nu Nv Ny Oe Of
Og Oh Om On Oy Oz Pa Pd Pe Pg Po Pz Qa Qc Qd Qe) On(Aa Fr Hq Hu Hv Ih Ii Ij Im Io Iq Is It Iu Jh Jm Jn Jo Jq Jr Jt Lh Lj Lu Lv Lw Lx Lz
Ma Mc Md Me Mf Mg Mh Mi Mj Mk Ml Mn Mq Mr Ms Mu Mv Mx Mz Na Nb Nc Nd Ne Nf Ng Ni Nl Nm Nn No Nr Nt Nu Nv Nx Ny Og Oh
Oi Om Pa Pb Pe Pg Po Pz Qa Qc Qd Qe) Fr(Aa Fp Hx Il Im In Iu Jj Jk Js Jt Lh Lj Ly Mb Mm Mw Mx My Mz Nc Nl Nq Nx Of Oh Oz Pc Pd Pe
Qb) Mm(Aa Hu Hx Im In Jj Jr Jt Lh Lj Ly Mw Mz Nc Nn No Nr Nv Oh Om Oz Pa Pc Pd Pe Qe) Lh(Fp Hr Hw Hx Il Im Iu Js Lj Ly Mb Mw
Mx Nc Nf Nx Oe Of Oz Pc Pd Pe Qb Qc) Mw(Aa Fp Il Im In Jj Lj Ly Mb Nx Oh Oz Pc Pd Pe) Nk(Ad Jt Lj Lx Mu Nn No Nr Nt Nx Oh Pd)
Nx(Aa Fp Il Im Jj Jt Nc No Pd Pe Qe) Js(Ad Ap Dg Nv Pe Pj) Im(Fp In Jj Ly Qb) Et(Bo Ch Cq Cu) In(Ad Fp Qa Qe) Jj(Jt Nv Pd Qe) Qb(Nv Pe
Qa) Oh(Fp Pd) Ok(Cq Cu) Pe(Il Ly) AaQe EfvS HrJt} Nc{Pf(Fr Hq Hr Hv Hx Ih Ii Il Im Iq Ir It Iu Iv Jj Jk Jn Jq Jr Jt Li Lj Lu Lv Lw Lx Lz Ma
Mc Md Me Mf Mg Mh Mi Mj Mk Ml Mn Mp Mq Mr Ms Mu Mv Mw Mx My Na Nb Nd Ne Nf Ng Ni Nl Nm Nn No Nq Nr Ns Nt Nu Nv Ny
Oe Of Og Oh Oi Om Oy Oz Pa Pb Pd Pe Pg Pz Qa Qc Qd Qe) Nk(Hu Hv Hw Hx Ii Ij In Ip Is Iv Jh Jj Jk Jm Jn Jo Jq Js Lu Lv Lw Lz Mc Md Me
Mf Mh Mi Mj Mk Ml Mn Mp Mq Mr Ms Mv Mx My Mz Na Nd Ne Nf Ng Ni Nq Ns Nu Oe Of Og Oi Om Pa Pb Qb Qc) Li(Fp Hr Hv Il Im Iq
Iu Jj Jk Jn Jp Jr Jt Lh Lv Mg Ml Mm Mp Ms Mw Mx My Mz Nb Nd Nf Ni Nm Nn No Nq Ns Nt Oe Of Oh On Oy Oz Pd Pe Po Pz Qc Qd Qe)
Nx(Hw Il Im Js Jt Lh Lj Lx Ly Ma Mb Mw Mx Mz Nb Ni Nm Nn No Nr Ns Nv Oe Of Oh Om On Oy Oz Pa Pd Pe Pz Qb Qe) On(Fp Hr Ij Il Jj
Jn Js Mf Mm Mp Ms Mu Mv Mw Mx My Ng Ni Nn Nq Ns Nv Oe Of Oy Pc Pd Pe Pg Qa Qc) Lh(Fp Hr Hw Hx Iu Jk Jn Jp Ly Mm Ms Mx My
Nd Nq Ns Oe Of Oz Pc Pd Pe Qa Qc Qd) Fp(Fr Jp Js Jt Ly Mb Mg Mw Mx Nm Oh Oz Pc Pd Pz Qb) Mm(Fr Hw Hx In Jj Jp Ly Nd Oz Pc Pd Pe
Qb) Fr(Hx In Jk Js Ly Nd Oz Pc Pd Qb) Jt(Hw Hx Jj Js Ly Mb Oz Pc Qb) Jp(Hw In Js Nd Oz Pc Pd Qb) Mb(Im Nv Oh Pd Pe Pz Qe) Mw(Hw
In Ly Oz Pc Pd) Js(Ad Dg Nv Pe Pj) In(Im Pd Pz Qe) Qb(Im Nv Pe Qa) Ly(Im Pe Qe) Jj(Pd Pz) AaOk AdOf QaQe} Et{Aa(Fr Hq Hr Hv Ih Ii Ij
Im Ip Iq Ir Is It Iu Iv Jh Jj Jk Jm Jn Jo Jp Jq Jr Jt Lh Li Lj Lv Lw Lx Lz Mc Md Mg Mh Mk Mm Mn Mq Mr Mu Mv Mw My Mz Na Nb Ni Nk Nm
Nn No Nr Nt Nu Nv Og Oh Oi Om On Oy Pb Pe Pg Po Pz Qe) Js(aA aF aH aI Aj aK Al An Ap AR Ax Ba Bc Bg Bn Bo bQ bX cE Ch CP Cq
Cs Cu Cv Cw dB Dc Dd dE Dl Ef Fa Fn Fw Gl Gp Jd Je Jf Kc Ke Kg Kl Kn Ko Kq Ks Ky Kz Oa Or Ou Ph Pj Qt Qz Ra Rg Ri Ue Vt Wm Tj)
Nd(Ad Af aH aI Aj Al An Ao Ap Ar As Aw Ax aY Ba Bb Bc Bg Bn Bo Ch Co Cp Cq Cs Ct Cu Cv Cw Cx Db Dc Dd DE Dg Di Dk Dl) aA(Hw
Ih Il In Iq Iv Jj Jk Lj Lv Ma Me Mf Ml Ms Mu Mv Mw Mx My Nb Nf Nk Nn Nq Ns Nt Oe Of Ok Oy Pd Pe Pf Qb Qd) Fw(Jd Je Jf Kj Kq
Kx Ou Pj Qt Qz Ri Tz Ue Uk Un Vp) dE(aH aI aR bM cI cK cP cQ Hx Mp Na Oe Pb Pc) Pg(aY bM Je Kf Kx Wm) It(Jm Jp Lx Mj Mq) Tj(aY
Io Mx Na) Mp(aH aR bM Kx) Kf(In Mx Qb) aH(cK Mb Oe) Ad(Oe Of) Ue(Ks Na) aY(al bZ) cK(aF aO) BoLy WmHx NnbM MqIp IjIl JdVp}
Mb{On(aA Fr Hq Hr Hu Hv Ih Ii Im Io Ip Ir Is It Iu Iv Jh Jl Jm Jn Jo Jp Jq Jr Jt Lh Li Lu Lv Lw Lx Lz Ma Mc Md Me Mf Mg Mh Mi Mj Mk
Mn Mq Mr Mx Mz Na Nb Ni Nm Nn No Nr Nt Nu Og Oi Om Pa Pb Pc Pe Po Qa Qc Qe) Mm(AA Hv Hw Hx Ih Im In Jj Jl Jt Lx Mp Mr Mu
Mz Na Ne Nk Nl Nn No Nr Nt Nv Oe Of Og Om Oy Oz Pa Pc Pd Pz Qa Qb Qe) Li(Fp Hw Hx Il Im In Iq Jj Jn Js Lh Mh Ml Mw Mx Mz Ne Nf
Nk Nl Nq Ns Nx Oh Oz Pc Pd Pf Pz Qa Qb Qc Qd Qe) Lh(Fp Hw Hx Im In Jj Jp Js Lj Ly Ml Mw My Ne Nf Nk Nl Nx Oe Of Oh Pd Pf Pz Qb
Qc Qd) Jp(Im In Iq Js Ml Mw My Na Nd Ne Nk Ns Nt Of Oh Oz Pc Pd Pe Pz Qa Qb Qc Qd Qe) Pf(Fp Fr Im Jt Ml Mw Mz Na Ne Nk Nl Nv Oh
Pz) Fr(Fp Lj Ml Mw Ne Nl Nx Oh Pd) Mw(Fp Lj Ne Nl Nx Oh Pd Pe) Nx(Aa Fp Oh Pd Pe) Ly(Nv Oh Pe Qe) Fp(Nk Oh) In(Nv Pe) AdOf
NkNl QbQe OhPd OkdE} Nl{Pf(Fp Fr Hr Hw Hx Il Im Iq Iu Jj Jk Jn Jq Jr Jt Lh Li Lv Lx Ma Mg Mh Ml Mp Mw Mx My Mz Na Nb Nd Ne Nf
Ni Nm Nn No Ns Nt Nv Oe Of Og Oh Om Oy Oz Pc Pd Pz Qa Qc Qd Qe) Nk(Ih Ii Ij Ir Iv Jh Jj Jr Ly Ma Mg Mu Mv My Mz Nb Nm Nr Nt Nu
Ny Oe Of Og Om Oy Oz Pa Pc Pg Po Pz Qd) On(Fp Hr Hw Ij Il Iu Jj Jn Js Ly Mp Ms Mu Mw Mx My Nd Ng Nq Ns Nv Nx Oe Of Oy Oz Pc Pd
Qa) Li(Hw Hx Il Ij Jk Jn Jp Jr Lh Ly Mm Mw Mx Nd Ns Nx Oz Pc Pd Qa Qc Qd) Lh(Fp Hw Hx Il Iu Js Ly Mx Oe Of Oz Pc Pd Qb) Jp(Fp Hw
In Js Mm Nd Nx Oz Pc Pd Pe Qb) Fr(Fp Hx In Jk Js Ly Nx Pc Pd Qb) Mm(Fp Hx In Jj Ly Nx Pc Pd Pe) Mw(Fp Hw In Ly Nx Oz Pc Pd) In(Fp
Im Nx Pd Qe) Nx(Fp Jj Pd Pe) Qb(Im Nv Pe) Ad(Js Of) Jj(Jt Pd) AaOk FpPd LyIm QaQe JsPe} Ad{Of(Ap AR Bg bM Bn Bo bQ bX cK cQ Cu
Cx Dc dE Di Dk Dl Ed Hr Hw Hx Il Ip Iq It Iu Iv Jn Jr Lz Ma Mf Mg Mj Mk Ml Mp Mr Ms Mw Mx Na Nb Ne Nk Nx Ny Oe Og Ok On Oz Pc
Pd Pj Qa Qb Qc Ue Vp) Bo(aH aK aM Ao Ap AR aU Bb bQ bU bX cC Co cP Ct Cw Cx DB Dc Dd Dg Di Dk Dl Js Tj) Aj(aK Ap aR aU Bg bM
bU cG cK Cq Ct Cu cY Dc dE Dg Dk Dl Js Tj) Ct(aH aK aM Ap AR Aw aY Ba Bn bU bX CP Cq Cu Dc dE Dl) bM(aK aM aN aR aU aY Bn
cG cN Cq cR Cu cY Dc dE Js) Js(bX Hv Io Jr Lh Mm Nd Nv On Pc Pd Pj Qe Un) aM(aC aK aR aU aV Bn bU bX cK cY Dc dE) aR(aK aU Bn
bU bX cC cN cW cY dE) aK(aH cN dE dJ) Bn(Cq Cu Dc) dE(aJ aY cP) Cq(Aw Cp) Jv(vP zG) jV(vB zH) TjOk} Pj{Js(bX Ch Dg Ih Jd Je Jn Jp
Jr Kf Kl Ko Kq Mg Mw Mz Nv Oh Ou Pd Pf Ph Qa Tz Un Ut) bE(uP uT uU uV vO vP vQ vS vT vU vV vW yH yJ yK zG zH zI yE tM tL
xA) yK(Ap Ar cB dH Gl Ii Jp Kc Kn kQ Lh Lx Mq Po qT Rg Ri Ue uU) kQ(qG qH rQ ul uW uX vP vQ vU zl tM) vT(Aj cB jE lK lN Ra Ri rR
sC Vo) xA(aD cB cM Ms Mw Ra Ri Vo) Jd(aY bX Dk In Qx Vp yE) yH(aC cB dA Uu Vo Vs) Di(uO uR vH vP vU) jE(uN vP vV zH yE)
Ue(Bo Na uG uN) Vo(uT vQ vU vW) cM(uV vO vW zI) IK(uY vP vV zH) aC(sM uG uU) aU(rS rV yE) jF(qH vP vV) sC(Aw dA Qz) Bo(Je

Figure 14 Continued

Og) Ng(vI yE) Ss(Of uW) Uu(uY vB) cB(vC yJ) uN(Hw Ph) TjKq PovC FarW FwMw IcaY RcbX QbQe JeRa KlOf UtPg gWyE} Ok{Js(AA aC aD AF aG Aj aK Al aM An AO AR As aU aV Aw Ax Ba Bb bC BG bH bN Bo bU bZ cC cE cF cG CH cL CO CP CQ cR CS Ct Cu Cv Cw Cx cZ DB Dc De dF Dg Dl DK DL Ef Fw Gl Gp Jd Je Ke Kg Kl Kn Ko Kr Kx Ra Rh Tn Ue Uf Un Up Ur Ut Wm Tj) aA(Hw Ii Il In Iq Jj Jo Jr Lv Me Mf Ms Ne Ng Nk Oe Oh Oz Pc Pd Pe Pf Qb Qd) Aa(Fp Hw Hx Il In Io Jr Ly Mi Ms Mx Ne Nf Ng Nx Oe Oz Pd Pf Qd) Tj(Ap bM Bn Bo Ii Md Mr Mx Na Of Pd Ue) dE(aR cQ Hx Mp Na Oe Of Pc) Nd(Ap Bn Bo Cu) bM(Mp Nn Pg) cM(rP rQ uY) NmIv QdrQ KkvQ PgaH qBrA jGrW} Pf{Ly(Fp Fr Hw Hx Ih Il Jj Jn Js Jt Lh Li Lj Lv Lw Lx Ma Md Me Ml Mp Ms Mu Mw Mx My Mz Na Nd Nf Ng Nk Nm Nn No Nq Nr Ns Nt Nv Ny Oe Of Og Oh Om On Oy Oz Pc Pd Qb Qe) Nx(Fp Hw Hx Il Im In Jj Jk Jp Js Ma Mm Mp Nd Ne Nf Ng Nk Of Oz Pc Qb) Ne(Fp Hw Im In Jp Js Lh Li Mm Mw Mz On Pc Qb) Lh(Hw Hx In Jj Js Nd Of Qb) On(Fp Hx In Jk Mp Nq Of Qb) Mm(Fp Hw Hx In Ma Mp Of) Nd(Aa Im Li Mw Nk Oh) Fp(Jp Js Mx Nk Qb) Nt(In Js) Hx(Jp Li) ImIn QbQe} On{Nd(Fp Hw Hx Ii Ij Il Im Iu Jk Jp Js Li Lj Ly Mm Ms Mu Mv Mw My Ne Nf Ng Nk Nq Ns Nx Oe Oy Oz Pc Pd Pe Qb) Hx(Fp In Jj Jk Li Lj Ly Mp Mu Mw My Ne Ng Nq Ns Oe Oy Oz) Fp(Hw Il Jk Js Ly Mw Mx My Ne Nk Nv Oe Of Oy Oz) Ly(Hw In Jj Ne Ns Oe Of Oz) Ne(Hw Jj Jk Nk Of Oz) Js(Bg Bn Dd Dg Uk) Qb(Lj Of Pe Qe) In(Lj Nt Pe) Of(Nx Oz)} Li{Ly(Hw Hx Im In Jj Jp Js Mm Nd Ne Nf Ns Nx Oe Oz Pc) Nx(Hx Il In Jj Jk Nd Ne Nf Of Oz Pc Qb) Nd(Im In Jj Jp Lh Mm Mw Nk Pc Qb) Ne(Hw Hx Jj Jk Js Mx Oz Pc Qa Qb) Hx(Im In Jj Jp Lh Mm Mw Oz Pc) In(Fp Im Lh Nt Pc Pd) Qb(Fp Pc Qe)} Fp{Mm(Hw Hx Jj Js Ly Mp Mx Nd Ne Nf Nk Nx Oe Oz Pc Pd Qb) In(Fr Jt Ly Mg Ne Nt Nv Oh Om Pd Pz) Jp(Js Ly Mx Nd Ne Nk Nx Oz Qb Qc) Nx(Il Jj Mw Mx Ne Nk Oz Pc Pd) Im(Ly Nk Oz Qb) Lh(Hx Jj Js Qb) Mw(Ly Oz) NkPd QbQe} Jp{Nd(Hx Lj Ly Mm Mw Nr Nx Oh Pd Pe) Ly(Hx Im Lj Ne Nx Oz Pd Pe) Hx(Lj Mm Ne Nx Pd Pe) Ne(Nk Nx) cZtR} Aa{Ng(sO uG uM uP uR uT uZ vB vO vT zG tM) Nd(Fr Im Lh Mm Mw Nx Qe) JhuP} Pe{In(Lh Ly Mm Nd Ne Nt Nx) Mm(Hx Ly Nd Qb) Nx(Il Jj Js Qb) Ne(Nk Qb) NtJs NdNk QbQe} Dl{Bo(aK aU bM Bn cP Cq Db) cP(aK aR bU Cq) aK(aR dE) CpCq} Ne{Nk(Im Lh Mw Nv Nx Pd) In(Jt Lh Nv) Jj(Lh Nx) MmNx QbLh} fR{aM(aK aQ aV cY) aW(aQ aU cY) gW(bB bU cM) Bo(aQ cY) aVbC} Js{Lh(Kf Ko Ph Ra Uk) Dg(Jn Jr Nd) Kf(Kq Mm Mz) MzKq} Jj{Nx(Lh Ly Mm Nr Pd Qe) Lh(Hx Ly Nd) ApvQ} Ly{Im(Hw In Oe Oz Pc) QbQe} dV{aV(Aj Dd) BccY DeaK} Ap{vQ(aC lK) cZvV} Dg{BnBo aKaR cPdE} Mm{Nd(Fr Lj Nx)} Qb{Qe(Nt Nx Pd)} Ng{aLwP bLuW} Ii{FwrR QlwF} DkjVvQ MgjGqH MwNxOz UfcZwP

Unconstrained panels with 3 analytes, where 8.4E-8 >= 'model p-value' > 1.0E-8. Contains 21,956 panels of 37,261,550 total panels evaluated. : Ji{Js(Aa aD aE aG aI aJ aL aO aP aQ aS aW aX aZ bA bB bC bE bF bG bH bI bJ bL bN bO bP bR bS bV bW bZ cA cB cD cE cF cG cH cI cJ cL cM cN cO cT cU cV cW cX cY cZ dA dC dD dF dG dH dJ dK dL dM dN dR Ed eF Ez Fn fP Fw Fy GL GP gW Hq Hv Ic Ii Ij Io Ip Ir Is It Iu Iz Jf Jh Jk Jl Jm Jo Jp Jt Ju Jv Kc Kg Kk Kl Kn Kq Kr Kx Kz Ld Lh Lu Lv Lw Lx Lz Ma Mc Md Mf Mg Mh Mi Mj Mk Mn Mq Mr Mx Mz Na Nb Ni Nm Nu Nv Ny Oa Og Oi Om On Or Ou Ow Pa Pb Pg Pk Po Qg Qh Ql Qn Qt Qu Qv Qw Qy Rb Ri Rj Rm Ss St Tn To Tr Tt Tv Ua Ub Ud Ug Uh Ul Um Un Uo Up Ur Us Ut Uu Uv Vo Vp Vt Vu Vv) Iq(Fr Hq Hr Hu Hv Ih Ii Ij Il Io Ip Ir Is It Iu Iv Jh Jk Jl Jm Jn Jo Jp Jr Jt Lh Lu Lv Lw Lx Ly Lz Ma Mc Md Me Mf Mg Mh Mi Mj Mk Ml Mn Mp Mq Mr Mu Mv Mw Mx Mz Na Nb Nf Ng Ni Nk Nm Nn No Nq Nr Ns Nt Nu Nv Nw Nx Ny Oe Of Og Oh Oi Om On Oy Pa Pb Pc Pg Po Pz Qa Qc Qd Qe) Nf(Aa Fr Hq Hr Hu Hv Ih Ii Ij Il Io Ip Ir Is It Iu Iv Jh Jj Jk Jl Jm Jn Jo Jp Jr Jt Lh Lu Lv Lw Lx Lz Ma Mc Md Me Mf Mg Mh Mi Mj Mk Ml Mm Mn Mp Mq Mr Mu Mv Mz Na Nb Ng Ni Nk Nm Nn No Nq Nr Ns Nt Nu Nv Nw Ny Oe Of Og Oh Oi Om On Oy Pa Pb Pg Po Pz Qa Qd) Ny(Fr Hq Hr Hu Hv Ih Ii Il Im Ir Is It Iu Iv Jh Jk Jl Jm Jn Jo Jp Jr Jt Lh Lu Lv Lw Lx Lz Ma Mc Md Me Mf Mg Mh Mi Mj Mk Ml Mm Mn Mp Mr Mu Mv Mw Mx My Mz Nb Ng Ni Nk Nm Nn No Nq Nr Ns Nt Nu Nv Nw Nx Oe Of Og Oh Oi On Oy Pa Pb Pg Po Pz Qa Qc Qd Qe) Pg(Ad aH AR aY Bo bX Ch cK cP dE dI Fr Hq Hr Hu Ih Ii Il Im Ir Is Iu Jh Jk Jl Jn Jo Jp Jr Jt Lh Lu Lv Lz Ma Mc Md Me Mf Mg Mh Mj Mk Ml Mm Mp Mu Mv Mw Mx My Mz Nb Ng Nk Nm Nn Nq Ns Nt Nu Nv Nw Nx Oe Of Og Oh Om Oy Pb Po Pz Qa Qc Qd Qe Ut) Oy(Fr Hq Hr Hu Hv Ih Ii Ij Il Im Io Ir Is It Iu Iv Jh Jk Jl Jm Jn Jo Jp Jr Jt Lh Lu Lv Lw Lx Lz Ma Mc Md Me Mf Mg Mh Mi Mj Ml Mm Mn Mp Mq Mr Mu Mv Mx Mz Na Nb Ng Ni Nk Nm Nn No Ns Nt Nu Nv Nw Nx Oe Of Og Oh Oi Om Pa Pb Po Pz Qa Qc Qd) Mp(aR bM Bo bU bX Ch cP dE Dg dI Hq Hr Hu Hv Ih Ii Ij Io Ip Ir Is It Iu Iv Jh Jk Jl Jm Jn Jo Jp Jr Jt Lh Lu Lv Lw Lx Lz Ma Mc Md Me Mf Mg Mh Mi Mj Mn Mq Mu Mv Mz Na Nb Ng Ni Nk Nm Nn No Nq Nu Nv Nw Of Og Oi Om Pa Pb Po Pz Qa Qd) Oe(Aa dE Fr Hq Hr Hu Hv Ih Ii Ij Il Io Ir Is It Iu Iv Jh Jj Jk Jl Jm Jn Jo Jp Jr Jt Lh Lu Lv Lw Lx Lz Ma Mc Md Me Mf Mg Mh Mi Mj Mk Ml Mm Mn Mq Mr Mv Mz Na Nb Ng Ni Nk Nm Nn No Ns Nu Nv Nw Of Og Oh Oi Om On Pa Pb Po Pz Qa Qc Qd) Ns(Fr Hq Hr Hu Hv Ih Ii Ij Il Io Ip Ir Is It Iu Iv Jh Jk Jl Jm Jn Jo Jp Jr Jt Lh Lu Lv Lw Lx Lz Ma Mc Md Me Mf Mg Mh Mi Mj Mk Mm Mn Mq Mr Mu Mv Mz Na Nb Ng Ni Nk Nm Nn No Nq Nr Nt Nu Nv Nw Og Oh Oi Om On Pa Pb Po Pz Qa Qd) Nx(Aa Fr Hq Hr Hu Hv Ih Ij Im Io Is It Iu Iv Jh Jk Jl Jm Jn Jo Jp Jr Jt Lh Lu Lv Lw Lx Lz Ma Mc Md Me Mf Mg Mh Mi Mj Mk Ml Mm Mn Mq Mr Mv Mz Na Nb Ng Ni Nk Nm Nn No Nr Nt Nu Nv Nw Og Oh Oi Om On Pa Pb Pe Po Pz Qa Qc Qd Qe) Mx(Aa Fr Hq Hr Hu Hv Ih Ii Ij Im Ir Is It Iu Iv Jh Jk Jl Jm Jn Jo Jp Jr Jt Lh Lu Lv Lw Lx Lz Ma Mc Md Me Mf Mg Mh Mi Mj Mk Ml Mm Mn Mq Mr Mz Na Nb Ng Ni Nk Nm Nn No Nr Nu Nv Nw Of Og Oh Oi Om On Pa Pb Po Pz Qa Qc Qd Tj) Mu(Hq Hr Hu Hv Ih Ii Ij Il Im Io Ip Ir Is It Iu Iv Jh Jl Jm Jn Jo Jp Jr Jt Lh Lj Lu Lv Lw Lx Lz Ma Mc Md Me Mf Mg Mh Mi Mj Mk Ml Mn Mq Mr Mv Mz Na Nb Ng Ni Nk Nm Nn No Nr Nt Nu Nv Of Og Oh Oi Om On Pa Pb Po Pz Qa Qd) Pc(dE Fr Hq Hr Hu Hv Ih Ii Ij Io Ip Ir Is It Iu Iv Jh Jk Jl Jm Jn Jo Jp Jr Jt Lh Lu Lv Lw Lx Lz Ma Mc Md Me Mf Mg Mh Mi Mj Mk Ml Mm Mn Mq Mr Mz Na Nb Ng Ni Nk Nm No Nr Nt Nu Nw Og Oh Oi Om On Pa Pb Po Pz Qa Qd) Il(Fr Hq Hr Hu Hv Ih Ii Ij Io Ip Ir Is It Iu Iv Jh Jj Jk Jl Jm Jn Jo Jp Jt Lh Lu Lv Lw Lx Ma Mc Md Me Mf Mg Mh Mi Mj Mk Ml Mm Mn Mq Mr Mv My Mz Na Nb Ng Ni Nk Nm Nn No Nu Nv Nw Of Oh Oi Om On Pa Pb Po Pz Qd) Qc(Aa bX Fr Hq Hr Hu Hv Ih Ii Ij Im Ir Is Iu Iv Jh Jk Jl Jm Jn Jo Jp Jr Jt Lh Lu Lv Lx Lz Ma Mc Md Me Mf Mg Mi Ml Mm Mn Mr Mv Mz Na Nb Ng Ni Nk Nm Nn No Nr Nt Nu Nv Nw Of Og Oh Oi Om On Pa Pb Po Pz Qa Qd) Jj(Fr Hq Hr Hu Hv Ih Ii Ij Io Ip Ir Is It Iu Iv Jh Jk Jl Jm Jn Jo Jp Jr Jt Lh Lu Lv Lw Lx Lz Ma Mc Md Me Mf Mg Mh Mi Mj Mk Mn Mq Mr Mz Na Nb Ng Ni Nk Nm Nn No Nu Nv Nw Of Oh Oi Om On Pa Pb Po Qa Qd) Pe(Fr Hq Hu Hv Ih Ij Im Io Ir Is It Iu Iv Jh Jl Jm Jo Jp Jr Jt Lh Li Lj Lu Lv Lw Lx Lz Ma Mc Md Me Mf Mg Mh Mi Mj Mk Mm Mn Mq Mr Mz Na Nb Ng Ni Nm Nn No Nr Nt Nu Nw Og Oh Oi Om On Pa Pb Pd Pz Qd Qe) Ml(Fr Hq Hr Hu Hv Ih Ii Im Ir Is Iu Iv Jh Jk Jm Jn Jo Jp Jr Lu Lv Lx Lz Ma Mc Md Mc Mf Mg Mh Mi Mm Mn Mr Mv Mw Mz Nb Ng Ni Nk Nm Nn No Nq Nr Nt Nu Nv Nw Of Og Oh Oi Om On Pa Po Pz Qa Qd Qe) Nn(aY bM bX cP Fr Hq Hr Hu Hv Ih Ii Im It Iu Iv Jh Jk Jn Jo Jp Jr Jt Lj Lu Lv Lw Lx Ma Me Mf Mk Mm Mn Mr Mv Mw My Mz Nb Ng Nk No Nq Nr Nt Nu Nv Nw Of Og Oh Om On Pa Pb Po Pz Qa Qd Qe) Mm(Fr Hq Hr Hu Hv Ih Ii Ij Im Ir Is Iu Iv Jh Jk Jm Jn Jo Jp Jr Lh Li Lu Lv Lz Ma Mc Md Me Mf Mi Mn Mr Mv Mz Nb Ng Ni Nk Nm No Nr Nt Nu Nv Nw Of Og Oh Om Pa Pb Po Pz Qa Qd Qe) Mw(Hq Hr Hv Ih Ij Io Ip Ir Is It Iu Iv Jh Jl Jm Jn Jo Jp Jr Jt Lh Lu Lv Lw Lx Lz Ma Mc Md Mf Mg Mh Mi Mj Mk Mn Mq Mr Mv Mz Na Nb Ni Nk Nm No Nu Nv Og Oh Oi Pa Pb Po Pz Qa Qd) Lj(Fr Hq Hv Ih Ij Im Io Ip Ir Is It Iu Iv Jh Jk Jl Jm Jo Jp Jt Lh Li Lu Lv Lw Lx Lz Ma Mc Md Mf Mg Mh Mi Mj Mk Mn Mq Mr Mv Mz Na Nb Ng Ni Nm No Nr Nt Nu Nw Oi Om On Pa Pb Qe) Pd(Aa Fr Hu Hv Ih Io Ip Ir Is It Iv Jh Jl Jm Jp Jr Jt Lh Lu Lv Lw Lx Lz Ma Mc Md Me Mf Mg Mh Mi Mj Mk Mn Mq Mr Mz Na Nb Ni Nm No Nr Nt Nu Nw Og Oh Oi Om On Pa Pb Pz Qa Qd Qe) Nq(Hq Hr Hv Ih Ii Ij Io Ip Ir Is It Iu Iv Jk Jl Jm Jn Jo Jp Jr Jt Lh Lv Lw Lx Lz Ma Mc Md Mf Mg Mh Mi Mj Mk Mn Mq Mr My Mz Na Nb Ng Ni Nk Nm No Nu Nv Og Oh Oi Om Pa Pb Po) Of(Aa Ad Fr Hq Hr Hu Hv Ih Ii Ij Im Ir Is Iu Iv Jh Jk Jl Jn Jp Jr Jt

Ma Ml Mp Mu Mv Ng Nm Nn Nv Ny Oy Pa Pg Pz Qa Qc Qd) Jt(Hr Hv Ii Ij Il Iq Iu Jn Jr Lv Ml Mp Mu Mv Nf Ng Nn Nv Ny Oy Pg Qa Qc Qd)
Pc(aA Hq Hr Hv Io Ip Ir Is It Iv Jh Jl Jm Jo Jq Lx Mg Mh Ni No Nr Nu Po Qd) Lv(Il Iq Iu Jn Jr Ma Me Ml Mp Mu Mv Mz Ng Nm Nn Nv Ny
Oy Pg Pz Qa Qc) Nm(Ii Il Iq Iu Jn Jr Ma Me Ml Mp Mu Mv Nf Ng Nn Nr Oy Qa Qc Qd) Mp(Fr Iv Jl Jr Lw Lx Ma Me Mi Mk Ml Mr Mz Nn Nr
Om On Pa Qe) Il(In Ir Jr Lw Lx Lz Mj Mk Ml Mr Mz Nr Nv Om On Pa Qe) On(Ii Ij Iq Jn Ma Me Ml Mu Mv Nb Nf Ng Nn Nv Ny Qa) Oy(Iv Jl
Jr Lw Lx Me Mi Ml Mr Mu Mz Ng Nr Om Pa Qe) Nc(Hq Io Ir Is Iv Jh Jl Jm Jo Jq Nu Po) Iq(Ir Jr Ma Ml Mr Mz Nn No Nr Pa Qe) Nx(Hv Io Ip
Ir It Iv Jh Jl Jo Nu Po) Mu(Jr Lw Me Mk Ml Mv Mz Ng Om Qe) In(Hq Hr Hv Ij Io Jh Jm Jn Ni Qc) Ml(Jn Jr Md Me Mv Ng Ny Om) Pg(Iv Lx
Mi Mk Mr Nr Om Pa) Jr(Jn Mv Nf Ng Nn Qa Qd) Pf(Io Ip Jh Jl Jo Jq Nu) Mr(Hr Ij Nb Nf Ny) Ng(Fr Hu Mg Mz Om) Nr(Hr Ij Nb Nf) aA(Fp Ik
Nh Nj) Me(Mv Mz Pa) Qe(Jn Qc Qd) Cu(Et Ok) Mk(Ij Nb) Mv(Fr Om) Ih(Jn Qa) Pj(Na vC) DqNj TjOk EtdE NoJn MiHq QaQd NyOm} Ik{Fp(aA Hq Hr Hu Hv Hw Hx Ih Ii Ij Io Iq Ir Is It Iu Iv Jh Jk Jl Jm Jn Jo Jq Jr Jt Lj Lu Lv Lw Lx Lz Ma Mb Mc Md Me Mf Mg Mh Mi Mj Mk Ml Mn Mp Mq Mr Ms Mu Mv My Na Nb Nd Ne Ng Ni Nm Nn Nq Nr Nt Nu Nv Ny Oe Of Og Oi Om Oy Pb Pe Pg Po Qa Qc Qd) Fr(Hq Hr Hu Hv Hx Ih Ii Ij Im Iq Is It Iu Jh Jl Jm Jn Jo Jq Jr Js Jt Lh Lu Lv Lw Lx Lz Ma Mc Md Me Mf Mg Mh Mi Mj Mk Ml Mn Mp Mq Mr Ms Mx Mz Na Nb Nd Ne Nf Ni Nm Nn No Nr Nt Nu Nv Ny Og Oh Oi Om On Pa Pb Pd Pe Pg Po Pz Qa Qc Qd Qe) Nx(Aa Hr Hu Hv Hw Hx Ih Ii Ij Is Iu Jh Jk Jl Jm Jn Jo Jq Jr Js Jt Lu Lv Lw Lx Ly Lz Ma Mb Mc Md Me Mf Mg Mh Mi Mj Mk Ml Mn Mp Mq Mr Ms Mu Mv Mx My Na Nd Ne Nf Ng Nm Nn Nq Nr Nt Nu Nv Ny Oe Og Oi Om Oy Pa Pc Pd Pg Po Pz Qa Qb Qc Qd) Nk(Hq Hr Hu Hv Hw Hx Ii Ij Il In Io Ir Is Iu Iv Jh Jk Jm Jn Jo Jq Jr Js Jt Lu Lv Lw Lz Ma Mb Mc Md Me Mf Mg Mh Mi Mj Mk Ml Mn Mp Mq Mr Ms Mu Mv Mx My Na Nb Nd Nf Ng Ni Nm Nq Ns Nt Nu Ny Oe Of Og Oi Om Oy Pb Pc Pg Po Qb Qc rS uL) Nc(Hq Hr Hu Hv Hx Ih Ii Ij Il Io Ip Iq Ir Is It Iu Iv Jh Jk Jl Jm Jn Jo Jq Jr Js Lu Lv Lw Lz Mb Mc Md Me Mf Mg Mh Mi Mj Mk Ml Mn Mp Mq Mr Ms Mu Mv Mx My Na Nb Nd Ne Nf Ng Nh Ni Nj Nl Nq Nr Nt Nu Ny Oe Of Og Oi Oy Pb Pg Po Qc) Oh(Hq Hr Hu Hv Hx Ih Ii Ij Ip Iq Ir Is It Iv Jh Jk Jl Jm Jn Jo Jq Jr Jt Lu Lv Lw Lx Lz Ma Mc Md Me Mf Mg Mh Mi Mj Mk Ml Mn Mp Mq Mr Ms Mu Mv Mx My Mz Na Nb Nd Ne Ng Ni Nm Nn Nq Nr Nt Nu Nv Ny Og Oi Om Oy Pb Pg Po Pz Qa Qc Qd) Pe(Hq Hu Hv Hx Ih Ii Im Iq Is It Iu Jh Jl Jm Jn Jo Jq Jr Jt Lj Lu Lv Lw Lx Lz Ma Mb Mc Md Me Mf Mg Mh Mi Mj Mk Ml Mn Mp Mq Mr Ms Mu Mv Na Nb Nd Ne Ng Ni Nm Nn Nq Nr Nt Nu Nv Ny Oe Og Oi Om Oy Pa Pb Pd Pg Po Pz Qc Qd Qe) Mw(Hq Hr Hu Hv Hx Ih Ii Ij Im Iq Is Iu Jh Jl Jm Jn Jo Jq Jr Js Jt Lu Lv Lw Lx Lz Ma Mc Md Me Mf Mg Mh Mi Mj Mk Ml Mn Mp Mq Mr Ms Mu Mv Mx My Mz Na Nb Nd Ne Ni Nm Nn Nq Nr Nt Nu Nv Ny Og Oi Om Oy Pa Pb Pg Pz Qa Qc Qd) No(Hq Hr Hu Hv Ih Ii Im Ip Iq Ir Is It Iu Jh Jl Jm Jn Jo Jq Jr Jt Lu Lv Lw Lx Lz Ma Mb Mc Md Me Mf Mg Mh Mi Mj Mk Ml Mn Mp Mq Mr Ms Mu Mv Mx Na Nb Nd Ng Ni Nm Nn Nr Nt Nu Nv Ny Og Oi Om Oy Pa Pb Pg Po Qc) Lj(Hq Hu Hv Hx Ih Ii Ij Io Ip Iq Ir Is It Iu Iv Jh Jk Jl Jm Jo Jq Jr Jt Lu Lv Lw Lx Lz Ma Mb Mc Md Me Mf Mg Mh Mi Mj Mk Ml Mn Mp Mq Mr Ms Mu Mv My Na Nb Nd Ne Ng Ni Nq Nr Nt Nu Nv Ny Og Oi Oy Pb Pg Po) Qe(Aa Hq Hu Hv Hx Ih Ii Im Iq Is It Iv Jh Jl Jm Jn Jo Jq Jr Jt Lu Lv Lw Lx Lz Ma Mb Mc Md Me Mf Mg Mh Mi Mj Mk Ml Mn Mp Mq Mr Ms Mu Mv Mz Na Nb Nd Ne Ni Nm Nn Nr Nt Nu Nv Ny Og Oi Om Pa Pb Pg Po Pz) Im(Hr Hu Hv Hx Ij Iq Is It Iu Jk Jl Jm Jn Jo Jr Js Jt Lv Lw Lx Lz Ma Mb Mc Mf Mi Mj Mk Ml Mr Ms Mu Mv Mx My Mz Na Nd Ne Nf Ng Nl Nm Nn Nq Nr Nt Nu Nv Ny Oe Og Om Oy Pa Pd Pg Pz Qa Qc Qd) Nh(Hq Hr Hu Hv Hx Ih Ii Ij Io Ip Iq Ir Is It Iv Jh Jk Jl Jm Jn Jo Jr Lu Lw Lz Mb Mc Md Me Mf Mg Mh Mi Mj Mk Ml Mn Mp Mq Mr Ms Mu Mv My Nb Nd Nf Ng Ni Nl Nq Nt Nu Ny Oe Og Oi Pb Pg Po) Mz(Hr Hv Hw Hx Ij Il Iu Jk Jl Jn Jq Jr Js Jt Lh Lv Lw Lx Ly Lz Ma Mb Mi Mj Ml Mr Ms Mu Mv Mx My Na Nd Ne Nf Ng Nm Nn Nq Nr Ns Nt Nu Nv Oe Of Og Om Oy Oz Pa Pc Pd Pg Pz Qa Qc Qd) Lh(Hq Hu Hv Ih Io Ip Iq Ir Is It Iv Jh Jl Jm Jn Jq Jr Jt Lu Lv Lw Lx Lz Ma Mc Md Me Mf Mg Mh Mi Mj Mk Mn Mq Mr Na Nb Nd Ni Nm Nr Nt Nu Og Oi Om On Pa Pb Pg Po) Lx(Hr Hw Hx Ij Iu Jk Jn Js Lv Lw Ly Lz Ma Mb Mc Ml Mp Mr Ms Mu Mv Mx My Na Nb Nd Ne Nf Ng Nl Nm Nn Nq Nr Ns Ny Oe Of Og Om On Oy Oz Pa Pc Pd Pz Qa Qc Qd) Nn(Hr Hu Hw Hx Ij Il Iq Iu Jk Jl Jq Js Jt Lv Lw Ly Lz Ma Mb Ml Mr Ms Mu Mv Mx My Na Ne Nf Ng Nj Nl Nm Nq Nr Ns Nv Oe Om Oy Oz Pa Pc Pd Pz Qa Qc Qd) Pd(Hr Hw Ij Il Iu Jk Jl Jn Jq Js Jt Lv Lw Ly Lz Ma Mb Ml Mr Mu Mv Mx My Na Ne Nf Ng Nj Nl Nm Nq Nr Ns Nt Nv Oe Of Om Oy Oz Pa Pc Pz Qa Qb Qc Qd) Nj(Aa Hr Hv Hw Ij Il Iu Jk Jl Jq Js Jt Lv Lw Ly Lz Ma Mb Mi Mj Mk Mr Mu Mx Na Ne Nf Nl Nm Nr Ns Nt Nu Nv Of Om Oy Oz Pa Pc Pg Pz Qa Qc Qd) On(Aa Cu Hq Hv Ih Io Ip Iq Ir Is It Iv Jl Jm Jq Jr Jt Lu Lv Lw Lz Mc Md Me Mf Mg Mh Mi Mj Mk Ml Mn Mq Mr Na Ni Nm Nr Nt Nu Og Om Pa Pb Po) In(Hv Ii Ij Il Io Ir Is Iv Jn Jq Jr Lv Lw Ly Lz Ma Md Mi Mj Mk Mq Mr Mu Na Ne Nm Ns Nt Nu Ny Of Oy Oz Pb Pc Pg Po Qb Qc) Qa(Hr Hw Hx Ij Iu Jk Jl Jm Jn Jq Jt Lv Ly Lz Ma Mb Ml Mu Mv Mx My Ne Nf Ng Nl Nm Nq Nr Ns Nv Oe Oi Om Oy Oz Pa Pc Qc Qd) Pz(Hr Hw Ij Il Iu Jk Jl Jq Js Jt Lv Ly Lz Mb Mx My Ne Nf Ng Nl Nm Nq Nr Ns Nv Oe Oi Om Oy Oz Pa Pc Qb) Pa(Hr Hw Ij Il Iu Jk Jl Js Jt Lv Ly Ma Mb Mx My Ne Nf Ng Nl Nm Nq Nr Ns Nt Nv Oe Of Om Oy Qc Qd) Et(Ad aF aH aI Aj An aO Ap Ar As aY Bg bM Bn Bo bQ bZ cE cK Cq Ct Dc Dd Dg Dk Fw Tj) Nv(Hr Hw Hx Ij Iu Jn Js Ly Mb Ms Mu Mv Mx My Ne Nf Nl Nm Ns Ny Oe Oy Oz Pc Qc Qd) Jl(Hr Hw Hx Ij Il Iu Jk Js Li Ly Mb Mx My Nf Ng Nl Nq Ns Oe Of Oy Oz Pc Qc Qd) Jt(Hr Hw Hx Ij Il Iu Jk Js Li Ly Mb Mx Ne Nf Ng Nl Ns Oe Of Oy Oz Pc Qb Qd) Kn(tN tO tQ tR tS tT tU tV tX wB wC wD wE wF wG wH wJ wK wL wP wQ yD yK) Li(Ih Ii Io Ip Ir Iv Lu Lw Lz Me Mf Mg Mi Mj Mk Mn Mq Mr Na Ni Nu Og Pb) Nl(Hw Il Iu Jq Js Lv Ly Ma Mx Na Nm Nr Ns Of Om Oy Oz Pc Qb Qc Qd) Nr(Hr Hw Hx Ij Il Iu Jk Js Ly My Nf Ng Ns Oe Of Oy Oz Pc Qb) Ns(Hw Iu Jq Lv Lw Ly Ma Ne Nf Nm Of Om Oz Pc Qb Qc Qd) Ly(Hw Il Lz Ma Mb Na Ne Nm Of Om Oz Pc Qb Qd) Qb(Ih Jq Lv Ne Nm Nt Of Om Oz Pc Pg Qd) Om(Hx Ij Il Jk Ml Mu Mv Nq Ny Oy Oz) Qd(Hw Il Iu Jk Js Nf Oe Of Oz Pc) Pf(Ii Io Ip Ir Iv Jh Mg Nu) Nm(Aa Hw Iu Ne Nf Oz) Il(Lv Lw Oz Pc Qc) Ok(Aj Ct Cu dE Tj) Aa(Jj Jp Mm Nw) Js(Ad Dg Jr Pj) aA(Jj Jp Mm Nw) Mi(Hx Ij Pg) Qc(Nf Of Oz) Ma(Ne Of) Oz(Lz Nt) Pj(Je Ue) dE(aR Jp) tV(eD Kc) rW(Kq qO) rQ(Ic Mm) DgOf MkOy NePc cHsC} Nh{Nn(Fr Hq Hr Hu Hv Ih Ii Ij Il Im Ip Iq Is It Iu Iv Jh Jk Jl Jm Jn Jo Jq Jr Jt Lj Lu Lv Lw Lx Lz Ma Mc Md Me Mf Mg Mh Mi Mj Mk Ml Mn Mp Mq Mr Ms Mu Mv My Mz Na Nb Nc Nd Ne Nf Ng Ni Nl Nm No Nq Nr Nt Nu Nv Ny Oe Of Og Oh Oi Om Oy Pa Pb Pg Po Pz Qa Qc Qd Qe) Oh(Hq Hr Hu Hv Ih Ii Ij Il Ip Iq Ir Is It Iu Iv Jh Jk Jl Jm Jn Jo Jq Jr Lj Lu Lv Lw Lx Lz Ma Mc Md Me Mf Mg Mh Mi Mj Mk Ml Mn Mp Mq Mr Ms Mu Mv My Mz Na Nb Nc Nd Ne Nf Ng Ni Nl Nm No Nq Nr Ns Nt Nu Nv Ny Of Og Oi Om Oy Pb Pg Po Pz Qa Qc Qd Qe) No(Hq Hr Hu Hv Ih Ii Ij Il Im Ip Iq Ir Is It Iu Iv Jh Jk Jl Jm Jo Jq Jr Jt Lj Lu Lv Lw Lx Lz Ma Mc Md Me Mf Mg Mh Mi Mj Mk Ml Mn Mp Mq Mr Ms Mu Mv My Mz Na Nb Nc Nd Ne Nf Ng Ni Nl Nq Nr Nt Nu Nv Ny Oe Of Og Oi Om Pa Pb Pg Po Pz Qc Qd Qe) Jt(Fr Hq Hu Hv Ih Ii Ij Il Im Io Ip Iq Ir Is It Iv Jh Jk Jl Jm Jo Jq Jr Lj Lu Lv Lw Lx Lz Ma Mc Md Me Mf Mg Mh Mi Mj Mk Ml Mn Mp Mq Mr Ms Mu Mv My Mz Na Nb Nc Nd Ne Nf Ng Ni Nl Nm Nq Nr Nt Nu Nv Ny Og Oi Om On Oy Pa Pb Pg Po Pz Qc Qe) Pc(Aa Hr Hu Hw Hx Ih Ii Ij Il Io Ir Iu Iv Jh Jj Jl Jm Jn Jq Jr Js Lu Lv Lw Lz Mb Mc Md Me Mf Mg Mh Mi Mj Mk Ml Mn Mp Mq Mr Ms Mu Mv Mx My Na Nb Nc Nd Ne Nf Ng Ni Nj Nl Nq Nr Ns Nt Nu Ny Oe Of Og Oi Om Oy Oz Pa Pb Pg Po Pz Qa Qb Qc Qd) Pe(Hq Hu Hv Ih Ii Ij Io Ip Iq Ir Is It Iv Jh Jk Jl Jm Jo Jq Lj Lu Lv Lw Lx Lz Mc Md Me Mf Mg Mh Mi Mj Mk Mn Mp Mq Mr Ms Mu Mv My Na Nb Nc Nd Ng Ni Nl Nq Nr Nt Nu Nv Ny Of Og Oi Om Oy Pa Pb Pg Po Pz Qe) Im(Hq Hr Hu Hv Il Iq It Iu Iv Jh Jk Jn Jq Jr Lj Lu Lv Lw Lx Lz Ma Mc Mf Mg Mi Mj Mk Ml Mn Mp Mr Ms Mu Mv Mx My Mz Na Nb Nc Nd Ne Nf Ng Ni Nl Nm Nq Nr Ns Nt Nu Nv Ny Oe Of Og Om Oy Pa Pg Pz Qc Qd Qe) Fr(Hq Hu Hv Ih Ii Ij Io Ip Iq Ir Is It Iu Iv Jh Jl Jm Jo Jq Jr Lu Lv Lw Lx Lz Ma Mc Md Me Mg Mh Mi Mj Mk Mn Mp Mq Mr Ms Mv Mz Na Nb Nf Ng Ni Nl Nr Nt Nu Nv Ny Og Oi Om Pa Pb Pg Po Pz Qc Qd Qe) Nm(Aa Hr Hv Hx Ih Iq Iu Iv Jh Jk Jl Jn Jq Jr Lj Lu Lv Lw Lx Ma Mf Mg Mi Mk Ml Mn Mp Mr Ms Mu Mv Mx My Mz Na Nb Nc Nd Ne Nf Ng Nj Nq Nr Ns Nt Nu Nv Ny Oe Og Om Oy Oz Pa Pg Po Pz Qa Qc Qd Qe) In(Ad Hq Hr

Figure 14 Continued

Hu Hv Hw Hx Io Ip Ir Is It Iu Iv Jh Jj Jk Jm Jn Jo Jr Js Lu Lv Lw Lz Mc Md Me Mf Mh Mi Mj Mk Ml Mn Mp Mq Mr Ms Mv Mx My Na Nb Nc Nd Ne Nf Ng Ni Nj Nl Nq Ns Nu Oe Og Oi Pb Qb Qc) Ly(Hr Hw Hx Ih Ii Ij Il Ir Iu Jh Jl Jn Jq Jr Js Lv Lw Md Mg Mi Mk Ml Mn Mr Ms Mu Mv Mx Mz Na Nb Nc Nd Ne Nf Nj Nq Nr Ns Nt Nu Nv Ny Oe Of Og Om Oy Oz Pb Pg Po Pz Qa Qb Qd) Lx(Hr Hv Hw Il Iu Jh Jj Jk Jn Jq Jr Lj Lv Lw Ma Mc Mf Mg Mi Mk Ml Mp Mr Ms Mu My Mz Na Nb Nc Nd Ne Nf Nj Nq Nr Ns Nt Nv Ny Oe Of Og Om Oy Oz Pa Pg Pz Qa Qc Qd Qe) Pd(Hq Hu Hv Ih Ii Ij Il Io Ip Iq Ir Is It Iv Jk Jl Jm Jo Lu Lw Lz Mc Md Me Mf Mg Mh Mi Mj Mk Mn Mp Mq Mr Ms Mv Nb Nd Ng Ni Nl Nu Ny Og Oi Oy Pb Pg Po Qc Qd) Qe(Hr Hu Hv Il Iq Iu Jh Jk Jq Jr Lj Lv Lw Ma Mc Mf Mg Mi Ml Mn Mp Mr Ms Mu Mw My Mz Na Nb Nc Nd Ne Nf Nj Nq Nr Ns Nt Nu Nv Ny Oe Of Og Om Oy Pa Pz Qd) Mm(Hq Hv Ih Ii Ij Il Io Ip Iq Ir Is It Iv Jk Jl Jm Jo Lu Lw Lz Ma Mc Md Me Mg Mh Mi Mj Mk Ml Mn Mq Mr Mu Mv My Nf Ng Ni Nl Nu Nv Ny Oi Pb Pg Po Qd) Mb(Aa Hv Hw Ih Ii Ij Iu Jh Jj Jl Jq Js Lv Lw Me Mg Mh Mi Mk Ml Mn Mr Mu Mv Mx My Na Nb Nc Ne Nf Nj Nr Ns Nt Nu Ny Oe Of Og Oz Pg Po Qa Qb Qc Qd) Mw(Hq Hu Hv Ih Ii Ij Io Ip Iq Ir Is It Iv Jh Jl Jm Jo Lu Lw Lz Mc Md Me Mg Mh Mi Mj Mk Mn Mq Mr Mu Mv Nb Ng Ni Nl Nr Nt Nu Nv Ny Og Oi Pb Pg Po) Pa(Hr Hw Hx Il Iu Jh Jj Jn Jq Jr Lj Lv Ma Mf Mg Mi Ml Mr Ms Mu Mx My Mz Na Nb Nc Nd Ne Nf Nj Nr Ns Nt Nv Oe Of Og Om Oy Oz Pz Qa Qc Qd) Fp(Hq Hu Hv Ih Ii Ij Io Ip Iq Ir Is It Iu Iv Jk Jl Jm Jo Lj Lu Lw Lz Mc Md Me Mf Mj Mp Mq Ms Mv Ng Ni Nl Nq Nr Nt Nu Oi Pb Pg Po) Oz(Hw Hx Ih Ii Il Iu Jh Jj Jl Jq Jr Js Lv Lw Ma Mg Mi Mk Ml Mr Mu Mv Mx Na Nb Nc Ne Nj Nr Ns Nt Nu Ny Of Og Oy Pg Po Pz Qa Qb Qd) Lj(Hr Hu Hv Hx Il Iu Jh Jj Jq Jr Lv Ma Mh Mi Ml Mn Mu Mv Mz Na Nb Nc Nd Ne Nf Nj Nr Ns Nt Nu Nv Oe Of Og Om Oy Pg Pz Qa Qc Qd) Jj(Hw Hx Ih Ii Ip Ir Iv Jh Jl Jm Jo Jq Jr Js Lv Ma Mf Ml Mn Mu Mx Mz Na Nb Nc Nj Ns Nt Nu Ny Of Og Om Pg Po Qa Qb Qc Qd) Nv(Hr Hv Il Iu Jk Jn Jr Lv Ma Md Mf Ml Mp Ms Mu Mv My Mz Nc Nd Ne Nf Nj Nq Nr Ns Ny Oe Of Og Om Oy Pg Pz Qc Qd) Ma(Hw Hx Iu Jh Jn Jq Jr Lv Mf Mg Ml Mu Mx Mz Na Nb Nc Nd Ne Nj Nq Nr Ns Nt Oe Of Og Om Oy Pz Qa Qb Qc Qd) Mz(Hw Hx Iu Jh Jn Jq Jr Js Lv Mf Mg Ml Ms Mu Mx Na Nb Nc Nd Ne Nj Nr Ns Nt Oe Of Og Om Oy Pg Pz Qb) Oy(Hr Hw Hx Ij Iu Jk Jn Jq Js Lv Mg Ml Mx My Na Nb Nc Ne Nf Nj Nr Ns Nt Oe Of Om Pz Qa) Js(Hw Ih Ii Ij Jh Jl Jn Jq Jr Lv Mg Mi Mu Na Nj Nr Ns Nt Ny Oe Of Pg Pj Po Qc Qd) Pz(Hr Hw Hx Iu Jk Jn Jq Jr Lv Mg Ml Mx Na Nc Ne Nf Nj Nq Nr Ns Oe Of Om Qa Qd) Qb(Hw Ih Ii Ij Iv Jh Jq Jr Lv Mg Mq Mu Na Nc Nj Ns Nt Ny Of Om Pg Po Qc Qd) Om(Hr Hw Hx Ij Jk Jn Lv Mf Ml Mu Mv Mx Nc Ne Nf Nj Nq Nr Ns Nt Ny Pg) Hw(Ih Ii Jh Jl Jq Lv Mg Mu Na Nj Nr Ns Nt Ny Of Pg Po Qa Qd) On(Ih Io Ip Ir Iv Jo Lu Lz Me Mg Mh Mi Mk Mn Mq Mr Nu Pb) Mx(Jh Jl Jq Lv Mg Mi Mr Mu Na Nj Nr Nt Of Pg Po Qa Qd) Nx(Aa Hq Hu Ij Io Ip Iq Ir It Iv Jm Jo Po) Jp(Ii Io Ip Jl Jo Lz Me Mh Mj Mq Oi Pb) Nr(Hr Hx Iu Jn Lv Mg Ne Nj Ns Oe Qa) Nj(Aa Lv Mg Mu Na Nb Ne Nt Of Qa) Mg(Hr Hx Iu Jk Nc Ne Ns Of) Nk(Hq Il Io Ip Iq Is It) Hx(Jh Jl Mi Mr Pb Qa) Ns(Jh Jq Mu Nt Of) Ok(Cu dE Do Gw Tj) Et(Cu dE Fw Tj) Lh(Io Ip Ir Iv) Nt(Jn Oe) Qa(Jn Qd) AaNd MuJk MyJh NcNe UePj) Nw[Nq(Fr Hq Hr Hu Hv Ih Ii Il Im Iq Ir Iu Iv Jh Jj Jk Jn Jo Jp Jq Jr Jt Lh Lj Lu Lv Lw Lx Lz Ma Mc Md Mf Mg Mh Mi Mj Mk Ml Mm Mn Mp Mq Mr Ms Mu Mv Mw Mx My Mz Na Nb Nf Nk Nm Nn No Nr Ns Nt Nu Nv Ny Oe Og Oh Oi Om On Oy Pa Pb Pc Pg Po Pz Qa Qc Qd Qe) Mw(Fr Hq Hr Hu Hv Ih Ii Il Io Iq Ir It Iu Iv Jh Jj Jk Jl Jm Jn Jo Jp Jq Jr Jt Lh Lj Lu Lv Lw Lx Lz Ma Mc Md Mg Mh Mi Mj Mk Ml Mn Mq Mr Ms Mv Mz Na Nb Nf Ng Ni Nm Nn No Nr Ns Nt Nu Nv Ny Oh Oi Om On Pa Pb Pg Po Pz Qa Qc Qd Qe) Js(bM Dg Dl Fr Hq Hr Hu Hv Hw Ii Ij Il Im In Iq Ir Iv Jh Jj Jk Jn Jo Jp Jq Jr Jt Kf Lh Lu Lv Lx Lz Ma Mc Md Me Mf Mg Mj Mk Ml Mm Mn Mq Mr Mz Na Nb Nf Ng Nm No Nu Nv Ny Oe Of Og Oh On Pa Pc Pg Pj Po Pz Qa Qb Qc Qd Qe) Oz(Fr Hq Hr Hu Hv Hw Ih Ii Ij Iq Ir It Iu Iv Jh Jj Jk Jn Jp Jq Jr Jt Lh Lu Lv Lw Lx Lz Ma Mc Md Me Mf Mg Mh Mi Mj Mk Mn Mq Mr Mz Na Nb Nf Ng Ni Nm Nn No Nr Ns Nu Oe Of Og Oi On On Pa Pb Pc Pd Pe Po Pz Qa Qc Qd Qe) Fp(Fr Hq Hr Hu Hv Ih Ii Io Ip Iq Ir Is It Iu Iv Jh Jj Jk Jl Jm Jo Jp Jq Jt Lh Li Lj Lu Lv Lw Lx Lz Ma Mc Me Mf Mg Mh Mi Mj Mk Mn Mq Mr Na Ng Ni Nm Nn No Nr Nt Nu Of Oh Oi Om On Pa Pb Pe Pz Qd Qe) Ly(Fr Hq Hr Hu Hv Ih Ii Io Ip Iq Ir Is It Iu Iv Jh Jk Jl Jm Jn Jo Jp Jq Jr Jt Lh Lu Lv Lw Lx Lz Ma Mc Mf Mg Mh Mi Mj Mk Mn Mq Mr Mz Na Ng Ni Nm Nn No Nr Nt Nu Oi Om On Pa Pb Po Pz Qa Qc Qd Qe) My(Fr Hq Hr Hv Ih Ii Ij Il Io Ip Iq Ir Is It Iu Iv Jj Jk Jl Jm Jo Jp Jq Jt Lh Lu Lw Lx Lz Mc Md Mh Mi Mj Mk Mn Mq Mr Mv Mz Na Nf Ng Ni Nm Nn No Nr Ns Nt Oe Of Og Oh On Oy Pa Pb Pg Po Pz Qa Qe) Ny(Fr Hu Hw Ih Ii Il Im In Iq Ir Iv Jj Jr Li Lj Lu Lv Lx Ma Mc Md Mf Mg Mi Mk Ml Mm Mn Mp Mr Ms Mu Mv Mx Nb Nf Ng Nk Nn Nr Ns Nt Nx Oe Of Og Oh On Oy Pa Pb Pz Qb Qc Qd Qe) Pf(Hu Hv Ih Ii Io Ip Ir Is It Iu Iv Jh Jj Jl Jm Jo Jp Jq Jt Lh Li Lj Lu Lv Lw Lx Lz Mc Mg Mh Mi Mj Mk Mn Mq Mr Na Ni Nm No Nr Nt Nu Og Oi Om On Pa Pb Pd Pe Pz Qe) Ne(Fr Hq Hu Ih Ii Io Ip Iq Ir Is It Iv Jh Jl Jm Jo Jp Jq Jt Lh Lu Lv Lw Lx Lz Ma Mc Me Mg Mh Mi Mj Mk Mn Mq Mr Na Ng Ni Nm No Nr Nt Nu Oi Om On Pa Pb Pz Qe) In(Fr Hq Hr Hu Hv Ii Ij Io Ip Is It Iu Jh Jj Jk Jl Jm Jn Jo Jp Jq Jt Lh Lu Lw Lx Lz Ma Md Mh Mi Mj Mk Mn Mr Mx Mz Na Nc Nd Me Mf Mg Ml Nn Nr Ns Nf Oe Of Og Oh On Oy Pe Pg Pz Qb Qc Qd) Mu(Fr Hu Hv Hw Ih Il Im Iq Iv Jj Jk Jn Jr Li Lu Lv Ma Me Mf Mg Ml Mm Mp Ms Mv Mz Nb Nf Nk Nr Nt Nv Oe Of Og Oh Om On Ov Pa Pe Pg Pz Qb Qc Qd Qe) Ms(Hq Hw Ih Il Im Iq Jn Jr Li Lj Lv Ma Me Mf Mg Mh Ml Mm Mp Mv Mx Mz Nb Nf Nk Nr Nt Nv Oe Of Og Oh On Oy Pa Pb Pe Pg Po Pz Qb Qc Qd) Nx(Hq Hr Hw Ii Ij Im Iq Jk Jn Jq Li Lj Lu Lv Ma Mc Md Me Mf Ml Mm Mv Mx Mz Nb Ng Nk Nn Nr Ns Nt Nv Oe Og Oh Pa Pb Pd Pe Po Qc) Pd(Hq Hr Hw Ii Ij Im Iq Iu Jj Jk Jn Jr Li Lj Ma Mc Md Me Mf Mm Mx Mz Nb Nf Ng Nk Nn Ns Nt Oe Of Og Oh Pb Pc Po Qa Qc Qd) Nv(Hw Ih Il Im Iq Ir Iv Jr Li Lj Lu Lv Ma Me Mf Ml Mm Mp Mv Mx Mz Nb Nf Nk Nt Oe Of Og Oh On Oy Pe Pg Pz Qb Qe) Qb(Hq Hw Ir Iv Jr Lv Lx Md Me Mf Ml Mm Mp Mv Mx Mz Nb Nf Nn Nr Ns Nu Oe Of Og Oh On Oy Pa Pc Pg Po Pz) Oy(Hw Il Im Jn Li Lv Ma Me Mf Mk Ml Mm Mp Mr Mv Mx Mz Nb Nk Nr Nt Oe Of Og Oh On Pe Pg Qc Qd) Hx(Hv Ii Io Ip Iq Ir Is It Iv Jl Jm Jo Jq Lu Lv Lw Lz Mg Mi Mj Mn Mq Na Ni Nm Nu Oi Om) Pc(Hw Ij Il Im Li Lj Md Mf Ml Mm Mp Mv Mx Mz Nb Nf Ng Nk Nn Ns Nt Oe Of Oh Pe Pg Po) Pg(Hw Il Im Iv Jl Lj Lx Me Mf Mk Mm Mp Mx Nk No Ns Nt Oe Of Og Oh Om On Pa Pb Pe) Ml(Hw Il Im Iq Jj Jk Li Lj Me Mf Mm Mp Mv Mx Nf Ng Nk Nn Ns Nt Oe Of Og Oh Pe) Li(Hq Hr Hw Iq Jj Jk Jn Jr Mj Mp Mv Mx Nb Nf Ng Nn Ns Oe Of Qa Qc Qd) Il(Hw Ih Im Jr Lj Lv Me Mf Mp Mx Mz Nk Nr Nt Of Og Oh On Qe) Mv(Hw Im Jn Jr Me Mf Mg Mm Mp Mx Mz Nk Nt Oe Of Og Oh Pe) Hw(Ih Im Lj Mf Mm Mp Mx Nf Nk Nr Ns Nt Og Oh Pe) Lj(Iq Jn Jr Me Mm Mx Nf Nk Ns Oe Po Qa Qc Qd) Mp(Im Jn Me Mf Mx Mz Nb Nk Nt Oe Oh On Pe) Pe(Ij Jk Jn Jr Mm Mx Mz Nb Nf Oe Po Qa) Nt(Ij Jj Jk Jn Mx Nb Ns Oe Of Po) Mx(Me Mf Mm Nf Ng Nk Ns Oe Pz) Nd(Ad Hu Io Ip Is It Jm Jo Jq) Nb(Iv Me Mk Nk Nr Oe On Pa) Im(Iq Jj Jk Mf Nf Ns Oe Of) Mm(Iq Me Mf Nf Nn Ns Oe) Nf(Jn Jr Me Mf Pz) Ok(AA eP Tj) Ns(Jn Mz Nk) aA(Et Mb Nj) Ad(Of Tj) Po(Me Nk) Mf(Oe Of) Qe(Qa Qc) Jk(Og On) Melj NaPj NkJn NIlp OeOh] Pj(Js(aF aJ Al aM An Ap Ar aV Ax Ba bM Bo bU cN Co CP cQ CS Cu Cw dF dI DI Ef Fa Fb Fn Fr GL Hv Ib Ic Ii Im Io Ir Is Iv Iz Jf Jh Jk Jl Jt Jy Kc Ke Kg Kj Kn Kr Ks Kx Li Mj Mm Mq Mu My Na Ne Ng Nl Nn No Og Om Or Oy Pc Pe Qb Qd Qh Ql Qt Qu Qv Qx Qy Qz Ra Rc Rg Ri Rm Ss St Tn Tt Tv Ua Uc Ue Uf Uh Uk Uo Ur Us Uv Vs Vt Vu Vv Wm) Jd(aF aH al aK aM An aO Ap aR aS aV bC bF Bg bl bM Bn Bo bQ bU bZ cA cE cF cH cK cN cP CQ Cu CW Dc dE dH Dl dJ Et Fw Hb Hx Io Ie Jf Jv Jy Kf Ks Ma Mp Mw Mx Na Nt Ny Oe Of Og Ou Pg pS Qb Qz Ra Rc rP rQ rW tN tQ tR tS tT Ue uG uM uN uO Uv uW uX uZ vC vI Tj) sC(Aa aC Ad Af Ao Ap Ar aS aW bA Bb bF bM Bo cF cH Co cR cT Cw Cx dE Di Gp Hc Hu iA Ib Ii Ij Il Iq Iz JE Jh Jk jO Ki Kj Kk kQ Md Mg Mn Mp Mg Mv Mw My Ny Of oH Om Pb Pd Ph Pi qB qD Qh QT qW qY RC Rg rP rV tR tS Tt Ue vA vH Vu wL wP tL) vC(Aw Bb bP cM Co Cp Ct Cw Dc Di Ef Fa Fr Gl HC Hq Hw Io Jh Kc Ke Kl Ko KQ Ky Lh Lx Mp Mq Mw Ng Nr Om On Oy Pc Pd Pe Ph Qt Ra Rc Rg rQ rR rV Ua Ub Un uO Ut Uu Vo Vs Vu wL) Ue(aM aR aY bX Ch cN cP cQ Cw Et Fn Fw Ih In Je Jf Jp Jy Kc Kf Kr Ks Mb Mw Mx Nc Ne Nj Nl Oe Of Og Ok Ou Pc Pd Pf Ph Qv Qz Ra Rc Rg rP Un Us Uv Vs Tj) Je(Ad An Ap aY bX Ch Cu Cw Dg Di Et Fw Hw In Io Jv Jy Kf Ks Kx Mb Mw Mx Na Nj Oe Of Og Ou Pc Pd Pf Pg Qt Qv Qx Qz Rc Rg Ri Um Un Us Uv Vp wE Tj) Na(Ad Ap Ar Ba

Ar AW aY Bg bH bQ bU bX cC cF cG cK cN cP cR Cu cW cZ Dc dJ Dk Dl) Tj(Ap Ar aY Bg Cu Cw Dc Dd Dl Ii In Io Kc Kx Lh Ma Mb Md Mm Mx Na Nj Oe Pc Th) bX(aC aH aJ aN aQ Ar aV AW aY cF cG cK cN cP cR Cu cW cY Dc dJ Dl In Oe) Nd(Ar Cu Hr Hw In Io Jp Lh Ly Ma Mm Mp Mw Mx Na Nk Oe Ok On Pc Pd Pg Qb) cY(aF aH al aL aY Bg bH bQ bU cC cG cK cN cP cR Cu cW cZ dB Dc dJ Dl) Cu(Ap Ar aV Aw Ax Bg bU cC cK Cp Cs Dc Dd Dg Di Dk Dl Nj Ok Pc) cP(aC aF aH aV aY Bg bH bQ bU bZ cC cG cK cN cR Dc Dk Dl) Dc(Ao Ap Ar Aw Ax Bg bU cK cN Cp Cs Cx De Dg Dk Dl) aV(aF aH al aY Bg bH bQ bU cC cG cN cW dA dB dJ fR) In(cK Io Ly Ma Nc Ne Nl Ok On Pc Pd Un) Nj(Hr Hx Mx Na Oe Ok Pc Pg Qb) Bg(Ap Ar Aw cG Cp Dg Di Dl) Dk(Ap Ar Aw Cp Dd Dg Di Dl) bU(aC aH aJ aN aY cG cK cN) tV(bN cR Id Jv Nn Nt Pg Ql) Fw(Kc Kf Kx Ou Qz Ra Uh) cK(aF aH aY cC cF cG cN) aY(aQ cF cN cR cW) cG(aH bQ bZ cC dH) Dl(Ar Aw Cp Di) Jv(pS sC tR vH) Pg(Kx Ok Pc Pd) cN(aC bQ cC cF) Ly(Mb Na Oe) Nk(Nc Nl) aC(cR vB) aQ(aH cC) jV(wC wD) GwOk Hrlo QbQe aNcC} Ok{Tj(AF aH al Aj Al An Ao Ar As Aw Ax aY Ba Bb Bc Bg bQ bX bZ cE Ch Co Cp CQ Cs Ct Cu Cv Cw Cx Db Dc Dd De Dg Dl Dk Dl Ef Fp Fr Fw Gl Gp Hw Hx Ih Ij Il Im In Io Ip Ir Is It Iu Iv Jd Jn Jt Kc Kf Kx Lh Lu Lv Lw Lx Ly Lz Ma Mb Me Mf Mg Mh Mi Mj Mk Ml Mm Mn Mp Mq Ms Mu Mv Mw My Mz Nb Nc Nd Ne Nf Ng Ni Nj Nk Nl Nn No Nq Nt Nv Nx Ny Oe Og Oh Oi Om On Or Oy Oz Pa Pb Pc Pe Pf Pg Qc Qe Qz Ra Tz Un) Js(aE aJ aL aN aP aQ aS aW aX aZ bA bB bE bF bl bJ bL bO bP bR bS bV bW cA cB cD cI cJ cM cN cT cU cV cX cY dA dC dD dG dH dJ dM dN Dp dR Ed eF Ez Fa Fb Fn Fy gL gP gW Ha Hb Hc Hf Ib Ic Id Iz Jf Ju Jv Jy Kc Kd Ki Kk Kp Kq Ks Ky Kz Ld Oa Or Ou Ow Ph Pi Pk Qg Qh Ql Qm Qn Qt Qu Qv Qw Qx Qy Qz Rb Rc Rf Rg Ri Rj Rm rQ rR St To Tr Tt Tv Ua Ub Uc Ud Ug Uh Ul Um Uo Us Uu Uv Vo Vp Vt Vu Vv) Aa(eP Fr Hq Hr Hu Hv Ih Ii Ij Im Ip Iq Ir Is It Iu Iv Jh Jj Jk Jl Jm Jn Jo Jp Jq Jt Lh Lj Lu Lv Lw Lx Lz Ma Mc Md Mf Mg Mh Mj Mk Ml Mm Mn Mq Mr Mu Mv Mw My Mz Na Nb Ni Nk Nm Nn No Nq Nr Ns Nt Nu Nv Ny Og Oh Oi Om On Oy Pa Pb Pe Pg Po Pz Qa Qb Qc Qe) aA(Fr Hq Hr Hv Ih Ij Im Io Ip Ir Is It Iu Iv Jk Jm Jn Jq Jt Li Lj Lu Lw Lx Lz Ma Mc Md Mg Mh Mi Mj Mk Ml Mm Mn Mq Mr Mu Mv Mw Mx My Mz Na Nb Nf Ni Nn Nq Nr Ns Nt Nv Nx Ny Og Oi Om On Oy Pa Pb Pg Po Pz Qa Qc Qe) dE(aD aE aG aH al aN aQ aX aY aZ bM Bo bQ bX bZ cE cl cK cN cP cR cW cZ dl dJ Hq Hw Ij Il In Io Ip Is Jn Ma Me Mj Mr Mx Nc Nd Ne Nj Nl Nn Nx Ny Oh Pb Pg Qb Qc Qd) Nd(Af aH al Aj Al An Ao AR As Aw Ax Ba Bb Bc Bg bQ bZ Ch Co Cp CQ Cs Ct Cv CW Cx Db Dc Dd De Dg Di Dk Dl Do Dq dX eP Gw) Nj(Aj An Ao Ap Ar As Aw Ax Bb Bc Bg Bn Bo Ch Cp Cs Ct Cw Cx Dc Dd De Dg Di Dk Dl Do Dq eP Gw) Cu(Ap bM Bn Bo Ch cK Cp cQ Di Hr Hx Kf Lh Ly Mb Mg Mp Mw Nc Ne Nl Oe Of On Pc Pd Ra Uc Ut) Pg(aG al Aj Ap AR aY Bc Bn Bo bQ bX bZ cE cK CP cQ cW Dl Kx) eP(aM aV Bb Bc bM Bo bP bZ cK Co cP Dk Fr Ij Lu Ma Mb Mv Mw Mz Oe Of) Gw(Bg Bo Ch Cp Db Di Ii Ij Im Mb Ml Mr Ms My Ne Of Og Om) dX(aV Bc bM Bo bZ cK Co cP Db Ir Ma Mb Mv Mw Oe Of Oz) Mp(aF aH al aM aR aY bC Bo bQ bX cK cP CQ cW dl) cK(aF aH al aR aY bZ cW Hq Hx In Na Nn Of Qb) aH(bZ Hq Hx In Mb Nn Oc Of Oh Qb) Of(al Bn bZ Ch Di Do Dq Ue) rQ(aL aU dJ Hx Mr Vp) Nn(aR aY bX cP cW) cM(rV rW sC ul uW) jG(qZ rN rP sK tR) Fw(Kf Pd Ra Ue) Hq(aY bM bX cL) In(al bM Bn bZ) aR(bX bZ cW Ly) qB(qY rP rW vB) Do(Bo Mb Nl) vQ(Gp Jr IK) Hx(bX rR) Oe(Bn cW) bM(Oh Qb) BbrP BoLy UeLd QgrR QlvB aLvT eZrO iArW} Nc{Lh(Fr Hq Hu Hv Ih Ii Ij Il Im Io Ip Iq Ir Is It Iv Jh Jl Jm Jo Jq Jr Jt Lj Lu Lv Lw Lx Lz Ma Mc Md Me Mf Mg Mh Mi Mj Mk Ml Mn Mp Mq Mr Mu Mv Mw Mz Na Nb Ne Nf Ng Ni Nl Nm Nn No Nr Nt Nu Nv Ny Og Oh Oi Om On Oy Pa Pb Pg Po Pz Qe) Fr(Hr Hu Hv Hw Ih Il Im Iq Iu Iv Jj Jn Jp Jq Jr Jt Li Lj Lv Lx Ma Mc Me Mf Mg Ml Mp Mq Mr Ms Mu Mv Mw Mx My Mz Na Nb Ne Nf Ng Ni Nl Nm Nn No Nq Nr Ns Nt Nu Nv Ny Oe Of Og Oh Om On Oy Pa Pe Pg Pz Qa Qc Qd Qe) Nx(Aa Hq Hr Hu Hv Hx Ih Ii Ij Io Ip Iq Ir Is It Iu Iv Jh Jk Jl Jm Jn Jo Jq Jr Lu Lv Lw Lz Mc Md Me Mf Mg Mh Mi Mj Mk Ml Mn Mp Mq Mr Ms Mu Mv My Na Nd Ne Nf Ng Nl Nq Nt Nu Ny Og Oi Pb Pg Po Qa Qc Qd) On(Hq Hu Hv Ih Ii Im Io Ip Iq Ir Is It Iv Jh Jl Jm Jo Jp Jq Jr Jt Lj Lu Lv Lw Lx Lz Ma Mc Md Me Mg Mh Mi Mj Mk Ml Mn Mq Mr Mz Na Nb Ne Nf Nl Nm No Nr Nt Nu Ny Og Oh Oi Om Pa Pb Po Pz Qd Qe) Mm(Hr Hu Im Iq Ir Iu Iv Jh Jl Jn Jq Jr Js Jt Lj Lu Lv Lx Ma Mc Me Mf Mg Mi Mk Ml Mp Mr Ms Mu Mv Mw Mx My Mz Na Nb Ni Nl Nm Nn No Nr Ns Nt Nu Nv Oe Of Og Oh Om Oy Pa Pg Po Pz Qa Qc Qd Qe) Fp(Hr Hu Hw Hx Ih Ii Il Im Iu Jh Jj Jn Jr Lv Lw Lx Ma Mc Md Mf Mh Mi Mk Ml Mq Mr Ms Mu Mv My Mz Na Nb Nd Ne Nf Ng Ni Nj Nn No Nr Ns Nt Nu Nv Ny Oe Of Og Oi Om Oy Pa Pe Pg Po Pz Qa Qc Qd Qe) Jp(Hr Hu Hv Im Iq Ir Iu Iv Jj Jk Jn Jr Jt Lj Lv Lx Ma Mc Me Mf Mg Ml Mp Mr Ms Mu Mv Mw Mx My Mz Na Nb Ng Ni Nl Nm Nn No Nq Nr Ns Nt Nu Nv Ny Oe Of Og Oh Om On Oy Pa Pe Po Pz Qa Qc Qd Qe) Li(Hq Hu Ih Ii Ij Io Ip Ir Is It Iv Jh Jl Jm Jo Jq Lj Lu Lw Lx Lz Ma Mc Md Me Mf Mh Mi Mj Mk Ml Mn Mq Mr Mu Mv Na Ne Ng Nl Nr Nu Nv Ny Og Oi Om Pa Pb Pg) Pd(Hw Hx Im Iu Jh Jn Js Jt Lj Lv Lx Ly Ma Mu Mx Mz Nb Ni Nj Nm Nn No Nr Ns Nt Nv Of Oh Om Oz Pc Pe Pz Qb Qe) Jt(Hr Im Iq It Iu Jk Jn Lj Lv Mw Mx Mz Nd Ni Nj Nm No Ns Oe Of Oh Pe Pz Qa Qc Qd Qe) Pe(Hw Hx Il Im Ij Jn Jr Ma Mg Mw Mx Mz Nd Ni Nj Nm Oh Oz Pc Pz Qa) Mb(Ii Jl Lj Lx Ly Ma Mg Mu Mz Nm Nn No Om Oy Qa) Mw(Hx Im Jj Js Lj Lv Mz Nd Ni Nj Nm Nt Oh Pz Qb) Pc(Im Lj Lx Ly Ma Mz Nm No Nr Nt Nv Oh Pz Qe) Ly(Jj Lj Lx Ma Mz Nm Nn No Nv Oh Oz Pz) In(Ii Jl Lj Lx Mz Nm Nn No Nt Oh Om Qa) Oz(dX Im Lx Mz Nm No Nt Nv Oh Pz Qe) Pf(Hu Ij Io Ip Is Jh Jl Jm Jo Po) Nv(Hw Hx Jj Jn Mx Nd Nj Nz Qe) Js(Dl Im Kq Lj Lx Nt Pz Qe) Nk(Hq Hr Il Io Iq It Iu) Hx(Im Lx Nn No Pz Qe) Jj(Im Nm Nn Nt Oh Qe) Hw(Im Nm Oh Pz Qe) Qb(Jl Lj Lx Oh Pz) Nm(Lj Lx Qe) Im(Nd Nj) Pz(Lj Oh) MgLj QcQe PbdX} Nl{Lh(Fr Hq Hr Hu Hv Ih Ii Ij Im Iq It Jh Jk Jm Jn Jo Jp Jq Jr Jt Lj Lu Lv Lw Lx Ma Mc Md Me Mf Mg Mi Mj Mk Ml Mm Mp Mr Ms Mu Mv Mw My Mz Na Nb Nd Ne Nf Ng Ni Nj Nm Nn No Nq Nr Ns Nt Nu Nv Nx Ny Og Oh Oi Om On Oy Pa Pb Pc Pg Po Pz Qa Qc Qd Qe) Li(Fp Fr Hq Hr Hu Hv Ih Ii Ij Im Iq Ir Is It Iu Iv Jh Jl Jm Jo Jq Jt Lj Lu Lv Lw Lx Lz Ma Mc Md Me Mf Mg Mh Mi Mj Mk Ml Mm Mp Mq Mr Ms Mu Mv My Mz Na Nb Ne Nf Ng Ni Nm Nn No Nq Nr Ns Nt Nu Nv Ny Oe Of Og Oh Oi Om On Oy Pa Pb Pe Pg Po Pz Qe) Jp(Fr Hq Hr Hu Hv Ih Il Im Iq It Iu Iv Jh Jj Jk Jn Jq Jr Jt Lj Lu Lv Lw Lx Ma Mc Me Mf Mg Mi Mk Ml Mp Mr Ms Mu Mv Mw Mx My Mz Na Nb Ne Nf Ng Ni Nm Nn No Nq Nr Ns Nt Nu Nv Ny Oe Of Og Oh Om On Oy Pa Pg Po Pz Qa Qc Qd Qe) On(Fr Hq Hu Hv Ih Ii Im Io Iq Ir Is It Iv Jh Jl Jm Jo Jq Jr Jt Lj Lu Lv Lw Lx Lz Ma Mc Md Me Mf Mg Mh Mi Mj Mk Ml Mm Mn Mq Mr Mv Mz Na Nb Ne Nf Ni Nm Nn No Nr Nt Nu Ny Og Oh Oi Om Pa Pb Pe Pg Po Pz Qc Qd Qe) Nk(Hq Hr Hu Hv Hw Hx Il In Io Ip Iq Is It Iu Jk Jm Jn Jo Jq Js Lu Lv Lw Lz Mc Md Me Mf Mh Mi Mj Mk Ml Mn Mp Mq Mr Ms Mx Na Nd Ne Nf Ng Ni Nq Ns Oi Pb Qb Qc) Fr(Hr Hw Il Im Iu Jj Jn Jq Jr Jt Lj Lv Ma Mf Ml Mm Mp Ms Mu Mv Mw Mx My Mz Nb Nd Ne Nf Ng Nm No Nq Ns Nt Nv Oe Of Oh Om Oy Oz Pa Pe Pz Qa Qc Qd) Pf(Hq Hu Hv Ih Ii Ij Io Ip Ir Is It Iv Jh Jl Jm Jo Lj Lu Lw Lz Mc Md Me Mf Mi Mj Mk Mn Mq Mr Ms Mu Mv Mg Nq Nu Ny Oi Pa Pb Pe Pg Po) Nx(Aa Hw Il Im Js Jt Lj Lv Lx Ly Ma Mb Mi Mx Mz Nb Nf Nj Nm Nn No Nr Ns Nt Nv Oe Of Oh Om Oy Oz Pa Pc Pz Qb Qe) Mm(Hr Hu Hw Im Iu Jr Js Jt Lj Lv Lx Mw Mx Mz Nb Nd Nj Nm Nn No Nr Ns Nt Nv Oe Of Og Oh Om Oy Oz Pa Pz Qb Qe) Fp(Hw Il Im Jj Jn Js Jt Lx Ly Ma Mb Mg Ml Mu Mx Mz Nb Nj Nm Nn No Nv Of Og Oh Om Oy Oz Pa Pc Pe Pz Qb) Mw(Hx Il Im Jj Jn Js Jt Lj Lv Mx Mz Nb Nd Nj Nm Ns Oe Of Oh Om Oy Pa Pe Pz Qb) Pd(Hw Im Iu Jn Js Jt Lj Lx Ly Ma Mb Mx Mz Nm Nn No Nr Nt Nv Oh Om Pc Qb Qe) Jt(Hr Hw Hx Iu Jn Js Ly Mb Mx Nj Oe Of Oh Oz Pc Pe Qb) In(Do Dq Gw Ii Jl Lj Lx Mz Nn No Nr Nt Oh Om Pz Qa) Pe(Hw Hx Il Im Jj Jn Ly Mb Mx Mz Nj Nm Oh Oz Pc Qa) Mb(Do Im Lx Ly Nn No Nv Oh Pz Qe) Nv(Hw Hx Jj Jn Js Ly Mx Oz Pc) Ly(Lx Ma Nn No Oh Qe) Im(Hw Hx Jj Js Oz Pc) Qe(Hx Jj Js Pc Qc) Oh(Hw Jj Oz Pc Qb) No(Hx Js Pc) Qb(Lj Lx Qa) Jj(Nm Nn Pz) dX(Oz Pb Pc) Do(Mv Nd) DgJs MzPc} Pf{Nx(Aa Fr Hq Hr Hu Hv Ih Ii Ij Io Ip Iq Ir Is It Iu Iv Jh Jl Jm Jn Jo Jq Jr Jt Lh Li Lj Lu Lv Lw Lx Lz Mc Md Me Mf Mg Mh Mi Mj Mk Ml Mn Mq Mr Ms Mu Mv Mw Mx My Mz Na Nb Ni Nm Nn No Nq Nr Ns Nt Nu Nv Ny Og Oh Oi Om On Oy Pa Pb Pd Pe Pg Po Pz Qa Qc Qd Qe) Mb(Aa Hq Hv Hw Hx Ih Ii Ij Il In Io Ip Iq Ir Is It Iu Iv Jj Jl Jn Jq Js Lj Lu Lv Lw Lx Lz Ma Mc Md Me Mf Mg Mh Mi Mj Mk Ml Mn Mq Mr Ms Mu Mv Mw Mx My Mz Na Nb Ni Nm Nn No Nq Nr Ns Nt Nu Nv Ny Oe Og Oh Oi Om On Oy Pa Pb Pd Pe Pg Po Pz Qa Qc Qd Qe) Mb(Aa Hq Hv Hw Hx Ih Ii Ij Il In Io Ip Iq Ir Is It Iu Iv Jj Jl Jn Jq Js Lj Lu Lv Lw Lx Lz Ma Mc Md Me Mf Mg Mh Mi Mj Mk Mn Mp Mq Mr Ms Mu Mv Mx My Nb Nd Nf Ng

On Pd) Li(Hx In Ly Nd Ne Nx Oz Pc) Nc(Fr Jp Jt Mm Mw Pd Pe) Nj(lm Jt Mm Mw Nv Nx Pe) Mb(Fr Lh Mw Nv Nx Pf) Nd(Jp Lh On Pf) Ok(aA Cu dE Tj) Pj(Jd Je Js sC) Et(cK dE Tj) Pf(Lh Mm Ne) Bo(Dg Dl) Ly(Im Jp) On(Hx Ne) DlcP Vqql Unconstrained panels with 2 analytes, where 1.0E-6 >= 'model p-value' > 1.0E-7. Contains 793 panels of 197,786 total panels evaluated. : Pj(Ad Ap Ar Bo bX Ch cP cQ Cw Di Et Fr Fw In Io Jf Jg Jp Jy Kc Kf Kl Ko Kq Ks Kx Lh Mp Mw Mx Na Nc Nj Nn Og Ok On Ou Pc Pd Pf Pg pS Qb Qe Qt Qu Qv Qx Qy Qz Ra Rc Rg Ri rP rV Ss Tz Ua Ud Ue Uf Uh uL Um UN uO Us Uv uY uZ vB vC vH vl Vp Vs Vt Vu yK Tj) Ik(Aa Hq Hr Hu Hv Hw Hx Ih Ii Ij Il Io Ip Iq Ir Is It Iu Iv Jh Jk Jm Jn Jo Jq Jr Js Lu Lv Lw Lz Ma Mb Mc Md Me Mf Mg Mh Mi Mj Mk Ml Mn Mp Mq Mr Ms Mu Mv Mx My Na Nb Nd Ne Nf Ng Ni Nm Nq Nt Nu Ny Oe Of Og Oi Om Oy Pb Pc Pg Po Qc) Nh(Aa Hq Hr Hu Hv Hx Ih Ii Ij Il Io Ip Iq Ir Is It Iu Iv Jh Jk Jl Jm Jn Jo Jq Jr Lu Lv Lw Lz Mc Md Me Mf Mh Mi Mj Mk Ml Mn Mp Mq Mr Ms Mu Mv My Na Nb Nc Nd Ne Nf Ng Ni Nl Nq Ns Nu Ny Oe Of Og Oi Pb Pg Po Qa Qc Qd) Nw(Fr Hq Hr Hu Hv Ih Ii Ij Im Iq Ir Iu Iv Jh Jj Jk Jn Jp Jq Jr Lh Lu Lv Lw Lx Ma Mc Md Me Mg Mh Mi Mj Mk Mm Mn Mq Mr Mz Na Nb Nf Ng Nk Nm Nr Ns Nt Nu Nv Ny Oe Of Og Oh On Pa Pb Pe Po Pz Qa Qc Qd Qe) Et(Ad aF aH aI AR aY Bg bM Bn Bo bX bZ cE Ch Cp Cq Cu Dd Dk Ed Ef Fn Fw Gl Gp Ha Ic Jd Je Jf Jv Kc Kf Kj Kl Kn Ko Ks Kx Kz Ld Ou Ph Pi Qt Qx Qz Ra Rc Rg Ri Rm Ub Ue Uk Un Vp Vs Vu) Ad(aC AF aH aJ Al AN Ao Ap aQ As aV AW Ax aY BA Bb BC bH bQ bU bZ cA cB cC cF cG Ch cK cN Co Cp cR Cs Cv CW Cx DB Dd De Dl dL Fr Hr In Nj Oe Pc Pg) Pf(Fr Hw Hx Il Im In Iq Iv Jj Jp Js Jt Li Lj Lv Lx Ma Me Mf Ml Mp Mw Mz Nf Nk Nm Nr Nt Nv Of Oh Om On Oz Pc Pd Pz Qb Qe) Mt(Fr Hq Hr Hu Hv Ii Ij Io Ip Is It Jh Jl Jm Jo Jq Lu Lx Lz Mg Mh Mi Mj Mn Mq Na Ni Nu Oi Pb Po Qc Qd) Fp(Fr Il Im Jj Js Jt Li Lx Ma Mb Mg Ml Mu Mw Mx Mz Nd Ne Nf Nm Nn Nt Nv Og Oh Oy Oz Pc Pd Pe Pz Qb) Li(Hw Il Im Iq Jj Jk Jp Js Lh Lv Me Mm Mw Mx My Nf Nk Nq Ns Nt Oe Of On Pd Pe Pz Qb Qc Qd) Dg(Aj aK An Ap AR aU aV Aw Bg bM Bn cK CP Cq Ct Cu cY dE Di Dk Dl Js Nd Nj Tj) Ji(AA aR Bo bX cK dE Io Ip It Jl Lh Lw Mg Mh Mj Mk Mq Na Oi Om Tj) Nx(Aa Fr Il Im Jj Jp Lh Lj Lx Ly Mm Mw Ne Nr Nt On Oz Pc Pd Pe Qe) Dl(aK Ap AR aU aV Aw bM Bn bU bX Ch Cp Cq cY dB dE Di) Nc(Im Lj Lx Ly Ma Mb Mz Nm Nn No Nt Nv Oh Oz Pc Pz Qe) Nl(Im Jt Lj Lx Ly Ma Mz Nm Nn No Nv Oh Pc Pe Pz Qe) Ok(aH aI Ap aR Bn Bo bZ cK CQ Fw GT Ra Ue) On(Hw In Jj Jk Lj Ly Mw My Nq Ns Of Oy Oz Pd Qb) Nj(Aa Ap Lj Lx Mz Nk Nn No Nr Oh Pd Pz Qa Qe) Mb(Aa Im Jl Jt Lj Lx Ly Oh Pd Pe Qa Qe) Jg(Aa aH Aj aR aY Bg bM bX cK Cu Tj) Lh(Hw Hx In Jj Lj Ly Ne Nf Oz Pc Pd) Nd(Aa Ap Fr Im Mm Mw Nv Pe) Ne(Fr Jp Jt Mm Mw Nk Pd Pe) Ap(aK bM Bn cK cP dE) Ly(Fr Mm Mw Pe Qe) Jp(Hx Lj Nt Pd) Pe(In Js Mm Qb) fR(aK aV cY) Nt(Mm Pd) Js(Kf Kq) Ko(dX eP) BbcP BodB TjKq FwKf MmLj QbQe KlOf Unconstrained panels with 2 analytes, where 1.0E-5 >= 'model p-value' > 1.0E-6. Contains 1,610 panels of 197,786 total panels evaluated. : Pj(aA aD AF aH aI AJ aK Al aM AN AO aP aQ aR AS aU aV AW AX aY Ba Bb BC bE BG bI bJ bM BN bQ bU bZ cA cC cE cF cG cH cI cK cL cM cN Co Cp Cq cR CS Ct Cu Cv cW Cx cY cZ dA DB Dc DD DE DG dI dJ Dk Dl dM Dp dR Ed EF Ez Fa Fb Fn Fp Fy GL Gp Ha Hb Hc Hf Hq Hr Hu Hv Hw Hx Ib Ic Id Ih Ii Ij Ik Il Im Ip Iq Ir Is It Iu Iv Iz Jh Ji Jj Jk Jl Jm Jn Jo Jq Jr Jt Ju Jv Kd Ke Kg Ki Kj Kk Kn Kp kQ Kr Ky Kz Ld Li Lj Lu Lv Lw Lx Ly Lz Ma Mb Mc Md Me Mf Mg Mh Mi Mj Mk Ml Mm Mn Mq Mr Ms Mt Mu Mv My Mz Nb Nd Ne Nf Ng Nh Ni Nk Nl Nm No Nq Nr Ns Nt Nu Nv Nw Nx Ny Oa Oc Of Oh Oi Om Or Ow Oy Oz Pa Pb Pe Ph Pi Pk Po Pz Qa Qc Qd Qg QH Ql Qm Qn Qw Rb Rf Rh Rj Rm rN rO rQ rR rS rT rU rW sK sM sO Sr St Tn To TR Tt TV Ub Uc UG uI Uk Ul uM Uo UP UR UT UU uV uW uX vA VO vP vQ vS vT vU VV vW wH wL yH yJ yL zG zH zI yE tM tL xA Tk Wm) Et(aC aD Af aG Aj aK AL aM AN AO Ap aQ As aU aV AW Ax Ba Bb BC bF bG bH bL bQ bR bU cC cF cG cH cI cN CO cP cQ cR Cs Ct CV CW Cx cY cZ DB Dc De dF DG dH DI dJ Dl dN Dp eF Ez Fa Fb Fy gP Hb Hc Hf Ib Id Iz Ju Jy Kd Ke Kg Ki Kk Kp Kq Kr Ky Oa Or Ow Pk Qg Qh Ql Qm Qn Qu Qv Qw Qy Rb Rf Rh Rj Sr St Tn To Tr Tt Tv Tz Ua Uc Ud Uf Ug Uh Ul Um Uo Up Ur Us Ut Uu Uv Vo Vt Vv Wm) Ad(AA aD aE aG aI aL aO aP aS aX aZ bB bE bF bG bI bJ bL bN bO bP bR bS bV bW cD cE cH cI cJ cL cM cO cQ cS cT cU cV cX cZ dA dC dD dF dG dH dJ dK dM dN Ef Fp Fw Gl Gp Hq Hw Hx Ic Ij Ik Il Io Ip It Jg Ji Jk Jn Jr Kc Kf Kx Ly Lz Ma Mb Mj Mm Mp Mr Ms Mt Mw Mx Na Nb Nc Ne Nf Nh Nk Nl Nn Nw Nx Ny Og Oh Ok Oz Pb Pd Pf Qa Qb Qc Qz Ra Ue Uh Un Vp) Ok(aC aD AF aG Aj aK AL aM AN AO Ar As aU Aw Ax aY Ba Bb BC BG bH bL bM bQ bU bX cC cE Ch cI cN CO CP cR Cs Ct Cv CW Cx cY cZ DB Dc Dd De Dg dH DI dJ Dk Dl dQ dV Ef eM Gl gN GP Gw Jd Kf Ks Kx Ld Ou Qx QZ Rm rP rQ Tn Ub Um Un Vp) Jg(aA aC aD aF aG aI aK aM An AO Ap Ar As aU aV Ba Bb BC bG bH bL Bn Bo bQ bR bU bZ cA cC cE cF cG Ch cI cP CQ cR Ct Cx cY cZ dB Dc DG dH DI Dk Dl Fw Ic Jv Kc Kf Kx Qw Qx Qz Ra Ub Ue Un Uu Vp Vt) Li(Fr Hq Hr Hu Hv Ih Ii Ij Io Ip Ir Is It Iu Iv Jh Jl Jm Jn Jo Jq Jr Jt Lj Lu Lw Lx Lz Ma Mc Md Mf Mg Mh Mi Mj Mk Ml Mn Mp Mq Mr Ms Mu Mv Mz Na Nb Ng Ni Nm Nn No Nr Nu Nv Ny Og Oh Oi Om Oy Pa Pb Pg Po Qa Qe) Fp(Hq Hr Hu Hv Hw Hx Ih Ii Ij Io Ip Iq Ir Is It Iu Iv Jh Jk Jl Jm Jn Jo Jq Jr Lj Lu Lv Lw Lz Mc Md Me Mf Mh Mi Mj Mk Mn Mp Mq Mr Ms Mv My Na Nb Ng Ni No Nq Nr Ns Nu Ny Oe Of Oi Om Pa Pb Pg Po Qa Qc Qd Qe) Pf(Aa Hq Hr Hu Hv Ih Ii Ij Io Ip Ir Is It Iu Jh Jk Jl Jm Jn Jo Jq Jr Lu Lw Lz Mc Md Mg Mh Mi Mj Mk Mn Mq Mr Ms Mu Mv Mx My Na Nb Ng Ni Nn No Nq Ns Nu Ny Oe Og Oi Oy Pa Pb Pe Pg Po Qa Qc Qd) Dg(Aa aC aD AF aH aI Al aM aN AO aQ As aW Ax aY BA Bb BC bH bQ bU bX bZ cC cF cG Ch cN CO cQ cR Cs Cv CW Cx DB Dc Dd De dH dI Fr Fw Hr Ik Jd Ji Mp Oe Pc) Nx(Hr Hu Hw Hx Ih In Iq Ir Iv Jh Jl Jr Js Jt Lv Lw Lz Ma Me Mf Mg Mi Mj Mk Ml Mp Mr Ms Mu Mv Mx My Mz Nb Nd Nf Nk Nm Nn No Ns Nu Nv Oe Of Og Oh Om Oy Pa Pg Po Pz Qa Qb) Ap(aC aD AF aH Aj aM An Ao aQ AR aU aV Aw Ax aY Ba Bb Bc Bg Bo bU bX bZ cC cF Ch Co Cp Cq Cs Ct Cu Cv Cx cY DB Dc De Di Dk Ik Jd Ji Js Kf Ly Nl Ue Tj) Dl(aC AF aH Aj Al aM AN Ao aQ As aW Ax aY BA Bb BC Bg cB cC cF cG cK cN Co cQ Cs Ct Cu Cv Cw Cx Db Dc Dd De dF Dk Fr Hr Ik Ji Js Nd Nj Tj) Lh(dE Hr Hu Ii Il Im Iq Iu Iv Jk Jp Jr Js Lv Me Mf Ml Mm Mp Ms Mu Mv Mw Mx My Ng Nk Nn Nq Nr Ns Nt Ny Oe Of Oh On Oy Pe Pg Pz Qb Qc Qd Qe Ue Vp Tj) Ji(aF aH aI aK aM aN Ar aY Bc Bg bM Bn bQ bU bZ Ch cI cN cP CQ Cs Cu dB Dc dI Dk Ed Fw Kf Qx Qz Ra Rc Rm Ub Ue Vp) Nc(Aa Hu Hw Hx Ih Ii In Ir Iv Jh Jj Jl Jo Jr Js Lv Mf Mg Mu Mv Nb Nd Ni Nj Nr Ns Nu Ny Of Om Oy Pa Pg Po Qa Qb Qd) Nl(Aa Hw Ih Ii Ij In Ir Iv Jh Jj Jl Jq Js Lv Mb Mg Mu Mv Nb Nj Nr Ns Nt Nu Ny Of Om Oy Oz Pa Pg Po Qa Qb Qd) On(Aa Cq Cu dE Hr Ii Ij Il Im Iq Jr Js Me Mf Ml Mm Mp Ms Mu Mv Nf Ng Nk Nn Nt Nv Ny Oe Oh Pc Pe Pg Tj) Mm(cK dE Ed Fr Hu Hw Hx Im Jd Je Jj Jp Jr Kc Kf Kl Me Nr Oh Ou Oz Pc Pd Qe Rc rR Ue Tj) Nj(Ar Bb Ih Ii Il Ir Iv Jh Jj Jl Ly Ma Mb Mg Mu Mv Nb Ne Nm Nt Om Oy Oz Pa Pc Pg Po Qd) Kf(aY bX cR dE Ed In Jd Ko Nk Nn Of Pg Qb Qz Ra Ub Ue Un Vp Tj) Ne(Im Lj Lx Ly Ma Mb Mz Nm Nn No Nr Nt Nv Oh Oy Oz Pc Pz Qe) Nw(aR cK dE Io Ip Is It Jl Jm Jo Jt Lz Ni No Oi Om Tj) Pe(Fr Hw Hx Il Im Jj Jn Jp Mw Mx Nf Nk Nm Nt Oh Oz Pc) Nt(Fr Im In Jj Js Lj Ly Mb Mw Nk Oh Oz Pa Pc Qe) Ly(aR Bo Jt Lj Lx Nn No Nr Nv Oh Pd Qa) Pd(Fr Im Jj Jt Lj Lx Mw Nd Nr Oh Qe) Mb(Ii Mu Mz Nm Nn No Nr Oy Pz) Nd(Ba Bb Cw Jt Lj Lx No Oh Qe) Jp(dE Hw Im Iq Mf Nr Oz Pc Ue) Oz(Fr Im Jt Lj Mw Nv Oh Qe) aK(Ar Aw Ba Bb Bn Bo Cp dV) Ko(dE EM fR Gc Js Mw) Un(dE Fw Js Na Ue Vp Tj) Hx(Fr Im Lx Mw Nv Qe) Ba(aM bM Bn Ct dE) Bb(aM aU bM bU rP) Ik(aA AR Bn dE) Im(Hw In Jj Pc Qb) Kq(Cu Fw Mj Pg Ra) Lj(Fr Mg Mu Mw Pc) Ng(sC uO uW vQ) Jt(aR dE Vp Tj) Aa(bM Bo Qe) Mt(aA aR dE) Jd(Ue Vp Tj) Kc(dX Em Gn) Vq(qG qH qZ) aV(dO dV eX) fR(aQ Bo gW) Bn(bU cP) Fr(Mf Pc) Nv(In Jj) Uf(Fw Js) bB(dO Dq) CpaM MwPc NhaA IcaY YjlL QaQb YlnA aRbU bMcP cYdV

Figure 14 Continued

Unconstrained panels with 2 analytes, where 1.0E-4 >= 'model p-value' > 1.0E-5. Contains 3,198 panels of 197,786 total panels evaluated. :
Ji(aC aD aE Af aG AJ AL An AO aP aQ AS aU aV AW AX aZ BA BB bC bE bF bG bH bI bJ bL bN bO bP bR bS bV bW cA cB cC cD cE cF
cG cH cJ cL cM CO Cp cR cS CT cU CV CW cX cY cZ dA Db dC DD De dF dG dH Di dJ dK dL dM dN dR EF eM Fn GL GP gW Ha Ic Jd
Je Jf Jv Jy Kc Kl Ko Kx Ld Ou Ph Pi Qg Qh Qt Qu Qv Qw Qy Rb Rf Rg Rh Ri Rj Ss St Tn To Tr Tt Tv Tz Ua Uc Ud Uf Ug Uh Uk Ul Um Un
Uo Up Ur Us Ut Uu Uv Vo Vs Vt Vu Wm) Ok(aE aJ aP aQ aS aV aW aX aZ bA bB bE bF bI bJ bN bO bP bR bS bV bW cA cB cD cF cG cH
cJ cL cM cS cT cU cV cX dA dC dD dF dG dK dL dM dN DO Dp Dq dR dX Ed eF eP eX Ez Fa Fb Fn Fy gC gL gW Ha Hb Hc Hf Ib Ic Id Iz
Je Jf Ju Jv Jy Kc Kd Ke Kg Ki Kj Kk Kl Kn Ko Kp Kq Kr Ky Kz Oa Or Ow Ph Pi Pk QG Qh qI QI Qm Qn Qt Qu Qv Qw Qy Rb Rc Rf Rg Rh
Ri Rj rR rV rW sC Sr Ss St To Tr Tt Tv Tz Ua Uc Ud Uf Ug Uh Uk Ul Uo Up UR Us Ut Uu Uv vB Vo vQ Vs Vt Vu Vv Wm) Jg(aE Af aJ AL
aN aP aQ aS AW AX aZ bA bB bE bF bI bJ bN bO bP bS bV bW cB cD cH cJ cL cM cN CO Cp CS cT cU CV CW cX dA Db dC DD De dF dJ
dK dL dM dN Dp Ed EF Ez Fa Fb Fn Fy Gl GP Ha Hb Hc Hf Ib Id Iz Jd Je Jf Ju Jy Kd Ke Kg Ki Kj Kk Kl Kn Ko Kp Kq Ks Kz Ld Oa Or Ou
Ow Ph Pi Pk Qg Qh Ql Qm Qn Qt Qu Qv Qy Rb Rc Rf Rg Rh Ri Rj Rm rP rW sC Sr Ss St Tn To Tr Tv Tz Ua Uc Ud Uf Ug Uh Uk Ul Um Uo
Up Ur Us Ut Uv Vo Vs Vu Vv Wm) Ap(Aa aE aG al aJ AL aN aO aP AS aW aX aZ bA bB bC bE bF bG bH bI bJ bL bN bO bP bQ bR bS bV
bW cA cB cC cD cE cG cH cI cJ cL cM cN cO cQ cR cS cT cU cV CW cX cZ dA dC DD dF dG dH dI dJ dK dL dM dN Ed Ef Fp Fr Fw Gl GP Hq
Hr Hv Hw Hx Ic In Io Ip Iv Je Jf Jp Jv Jy Kc Kl Ko Kq Kx Lh Ma Mb Mg Mm Mp Mt Na Nc Ne Nh Nm Nn Nq Nw Nx Oe Of Oh On Ou Oz Pc
Pd Pg Ph Qx Qz Ra rP rW Tn Tr Tt Tz Uh Uk Um Un vC Vp vQ Vt) Ad(dR Ed eF Fa Fn fR gL gP gW Ha Hb Hf Hu Hv Ib Id Ih Ii Im Iq Ir Is Iu
Iv Jd Je Jf Jh Jj Jl Jm Jo Jp Jq Jt Ju Jv Jy Kn Ko Kq Ks Kz Ld Lh Li Lj Lw Lx Mc Md Me Mf Mg Mh Mi Mk Ml Mn Mq Mu Mv My Mz
Ng Ni Nm No Nq Nr Ns Nt Nu Nv Oi Om On Ou Oy Pa Pe Ph Pi Pk Po pS Pz Qa Qb Qd Qe Qg Qh Qt Qv Qw Qx Qy Rc Rg Rm rP rW sC Sr Ss Tn To
tV Tz Ub Uc Ud Uf Ug Uk Um Uo Up Ur Us Uu Uv vH Vo Vs Vt Vu Vv) Mm(Aa aH AR Bn Bo CP cQ DI Dp Fn Fy Ha Hb Hf Hr Ib Ic Ih Il In
Iq Ir Iv Iz Jf Jh Jl Jn Jq Js Jt Jv Jy Kd Ke Kg Ki Kj Kk Kn Ko Kp Kq Kr Ks Kx Kz Ld Lv Lx Mf Mk Ml Mp Mr Ms Mu Mw Mz Nb Nf Nk Nm
Nn No Nq Ns Nu Nv Oa Oe Of Og Om Or Oy Pa Pg Ph Pk Po pS Pz Qa Qb Qd QG Ql Qm Qt Qu Qx Qy Qz Ra Rf Rg Rh Ri Rj Rm rP rQ rW
sC Tr tV Tz Ub Ud Uf Uh Uk Um Un Ur Us Uv vH Vp vQ Vs Vt Vu yH) Kf(aF aH al aM AR Bb Bg Bn Bo bQ bU bZ cC cE cF cN cP cQ Ct
Cu Cx dB Dg dI DI Ha Hq Hr Hv Hw Hx Ic Id Ik Je Jf Jj Jk Jn Jp Jr Jt Jv Jy Kc Ke Kg Kl Kq Kx Ld Lh Ly Mb Mg Mi Mj Mp Mr Ms Mt Mw
Mx Na Nd Nf Ng Nm No Nq Ns Nw Nx Ny Oe Oh On Ou Oy Pc Pd Pf Ph Pi Pk Qa Qc Qe Qg Qh Qt Qw Qx Qy Rc Rf Rg Ri Rm Tn To Tr Tt
Tv Tz Ud Uf Uh Uk Um Ur Vt Vu Vv) Dg(aE aG aJ aL aP aS aX aZ bB bE bF bG bI bJ bL bN bO bP bR bS bV bW cA cB cD cE cH cI cJ cL
cM cS cT cU cV cX cZ dA dC dD dF dG dJ dK dL dM dN Ed Ef Fp Gl Gp Ha Hq Hw Hx Ic Il In Io Je Jf Jp Jv Jy Kc Ko Kq Kx Ly Ma Mb Mg
Mt Mw Mx Na Nc Ne Nh Nk Nl Nn Nw Nx Of Oh On Ou Pd Pg Ph Qb Qx Qz Ra Rc Tz Ue Uh Um Un Ur Vp) Dl(AA aD aE aG al aJ aL aO
aP aS aX aZ bB bE bF bG bH bI bJ bL bN bO bP bQ bR bS bV bW bZ cA cD cE cH cI cJ cL cM cO cR cS cT cU cV cW cX cZ dA dC dD dG
dH dI dJ dK dL dM dN Ed Ef fR Fw Gl Gp Hw Hx Ic In Jd Je Jp Kc Ko Kq Lh Ly Mb Mg Mp Mt Mw Na Nc Ne Nh Nk Nl Nm Nn Nw Nx Oe
Of On Pc Pd Pg Qb Ra Ue Uf Uh Un Vp) Pj(Aa aC aE aG aL aZ bA bB bF bH bL bO bP bR bS bV bW cB cD cJ cO cT cU cV cX dC dF dH dK
dL dN dU eC eM fN fP fY gP gW hB hC hF hG hP iA iB iH iJ iO iP iZ jV kR kS nW nY oE oF oH oK oN pF qA qB qD qG ql qO qZ rX rY rZ
tN tO tQ tS tT tU tX wB wC wD wE wF wG wJ wK wP wQ yD Wn Ti Th tF) Un(Aa aF AR aY Bg Bn Bo bX Ch cP CQ cR Cu Cw dI Ed Fa Fn
Ha Hq Hr Hv Hw Hx Ic Ik In Jd Je Jf Jl Jn Jp Jr Jt Jy Kc Kg Kl Kn Ko Kq Kx Kz Ld Lh Ly Mg Mj Mp Mr Ms Mw Mx Nf Nk Nm Nn Nq Ns
Ny Of Og Ou Pc Pd Pf Pg Ph Pk qA Qb Qc qD Qg Ql Qt Qx Qz Ra Rc Tz Ub Uf Uh Uk Um Ur Us Vu) Jp(Aa aH AR aY Bn bX cK Ed Fr Hr
Hu Ic Ih In Ir Iu Iv Jd Jh Jj Jk Jl Jn Jo Jq Jr Js Jt Kc Kx Lu Lv Lw Lx Ma Mc Me Mg Ml Mp Mq Mr Ms Mu Mv Mw Mx My Mz Na Nb Nf Ng
Nk Nm Nn No Nq Ns Nu Nv Ny Oe Of Og Oh Om On Oy Pa Pg Po Pz Qa Qb Qc Qd Qe Qx QZ Ra Ub Vp Tj) On(AR Bg Bn Bo bX cK Ct Cx
Dk Ed Fr Fw Hq Hu Hv Ih Io Ip Ir Is It Iu Iv Jd Jh Jl Jm Jn Jo Jq Jt Kc Ld Lu Lv Lw Lx Lz Ma Mc Md Mg Mh Mi Mj Mk Mn Mq Mr Mx Mz
Na Nb Ni Nm No Nr Nu Og Oi Om Pa Pb Po Pz Qa Qc Qd Qe Qx Qz Ra Rm Ub Ue Vp) Pe(Aa Hq Hr Hu Hv Ih Ii Ij Iq Ir It Iu Iv Jh Jk Jl Jm Jo
Jq Jr Jt Lj Lu Lv Lw Lx Lz Ma Mc Md Me Mf Mg Mh Mi Mj Mk Ml Mn Mp Mq Mr Ms Mu Mv My Mz Na Nb Ng Ni Nn No Nq Nr Ns Nu Nv
Ny Oe Of Og Oi Om Oy Pa Pb Pd Pg Po Pz Qa Qc Qd Qe) Pd(Aa aR Bn cK dE Fw Hq Hr Hu Hw Hx Ih Ij Il In Iq Ir Iu Iv Jd Jh Jk Jl Jn Jo Jq Jr
Js Ko Lv Lw Ma Me Mf Mg Mk Ml Mp Mq Mr Ms Mu Mx My Mz Na Nb Nf Nk Nm Nn No Nq Ns Nu Nv Ny Oe Of Og Om Oy Oz Pa Pc Po
Pz Qa Qb Qd qZ rP Tj) Lh(AA aH aR aY bX cK cP Cu Ed Fr Fw Ha Hq Hv Ih Ij Io Ip Ir Is It Jd Jh Jl Jm Jn Jo Jq Jt Kc Ko Ld Lu Lw Lx Lz Ma
Mc Md Mg Mh Mi Mj Mk Mn Mq Mr Mz Na Nb Ni Nm No Nu Nv Og Oi Om Pa Pb Po Qa Qc Qg Qx Qz Ra Rc Rm Ub Um Ur) Nj(aA Ao aR Ba
Bn Bo Ch Co Cp Cw dE Dk Do Dq Gw Hr Hu Hv Hw Hx Ij In Io Ip Iq Is It Iu Jk Jm Jn Jo Jq Jr Js Lu Lv Lw Lz Mc Mo Md Me Mf Mh Mi Mj Mk
Ml Mn Mp Mq Mr Ms Mx My Na Nd Nf Ng Ni Nq Ns Nu Ny Oe Of Og Oi Pb Qb Qc) Nt(Aa Hr Hu Hv Hw Hx Ih Ii Ij Il Ip Iq Ir It Iu Iv Jh Jk Jl
Jn Jo Jq Jr Jt Lv Lw Lx Ma Mc Me Mf Mg Mi Mk Ml Mp Mq Mr Ms Mu Mv Mx My Mz Na Nb Nd Nf Ng Nm Nn No Nq Nr Ns Nv Ny Oe Of
Og Om Oy Pb Pg Po Pz Qa Qb Qc Qd) Ko(aF aH al aK aM aR aY bC bG bQ bU bX bZ cE cH cN cP CQ cR Cu dH dl Dr Ed Ex Fc Fn Fw Gb
gC Gd Gn Ic Ik In Jd Je Kq Kx Mg Na Nb Nc Ne Nh Nk Nl Of Ou Pg Ps Qb Qx Qz Ra Ru Sf Sh Tz Ub Ue Uf Uh Vp Yd Tj) Kq(aF aH al aL
aM AR aX aY Bg Bn Bo bQ bX cN Cq cR cW Dc dE dI Dk Ed Hq Hw Hx Ic Ij In Iv Jd Jn Jr Jy Kc Kx Kz Ld Mg Ml Mp Mr Mt Mw Mx My
Na Nb Nk Nn Nq Nv Ny Of Pc Po Qx Qz Ub Ue Vp) Fr(Aa aK bM Bn cP dB dE Hr Hu Hw Ih Il Im In Iq Ir Iv Jj Jk Jq Jr Js Jt Lv Lx Ma Me Ml
Mp Ms Mu Mv Mw My Mz Nf Ng Nk Nm Nn No Nq Nr Ns Nu Oe Of Oh Oy Pa Pz Qa Qb Qc Qe Tj) Ng(Nc Nl Nx pS rP rQ rW sK sM sO tN
tR tV uG uI uL uM uN uP uR uT uU uV uX uY uZ vA vB vC vH vI vS vT vU wB wC wD wF wH wJ wK wL wP wQ yJ yK yL zA zH tM tL
xA) Nl(AR dE Hq Hr Hu Hv Hx Il Io Ip Iq Is It Iu Jk Jm Jn Jo Jr Lu Lw Lz Mc Md Me Mf Mh Mi Mj Mk Ml Mn Mp Mq Mr Ms Mx My Na Nc
Nd Ne Nf Ni Nq Oe Og Oi Pb Qc) Jd(dF aM AR aY Bb Bg bM Bn Bo bQ bX Ch Cq Cu Cw Cx dE dI Ed Fw Hq Hx Ic In Jn Js Jt Kc Kg Kl Ly
Mg Mw Mx Nk Nm Nn Of Ou Pg Ph Qe Qx Qz Ra rP Uf Ug Uh Uk) Et(aE aJ aP aS aX aZ bA bB bE bI bJ bN bO bP bS bV bW cA cB cD cJ
cL cM cS cT cU cV cX dA dC dD dK dL dM dR eM fP gL gW hB iA iP oE oF qB qZ rQ Ss uR vQ Wn) Jh(aY Bo bX cK cP CQ Cu Dc Ed eM Fw
Ha Hr Hw Hx Im In Iq Je Jj Kc Lj Lv Lx Me Mw Nf Nr Oe Of Oh Pc Qc Qx QZ Ra rP sC Ub Ue vQ Vs) Nc(Hq Hr Hv Ij Il Io Ip Iq Is It Iu Jk
Jm Jn Jq Lu Lw Lz Mc Md Me Mh Mi Mj Mk Ml Mn Mp Mq Mr Ms Mx My Na Ne Nf Nq Oe Og Oi Pb Qc) Ne(Aa Hu Hw Hx Ih Ii Ij In Ir Iv
Jh Jj Jl Jo Jq Jr Js Lv Lw Mf Mg Mi Mk Mr Mu Mv Mx Nb Nd Ns Nu Ny Of Og Om Pa Pg Po Qa Qb Qd) Mb(aA Ex fR Hv Ih Ij Io Ir Is Iv Jh Jj
Jo Jq Lw Ma Mg Mi Mk Ml Mr Mv My Na Nk Nu Oe Of Om Oz Pa Pc Pg Po Qc Qd) Ik(AF aM Ao Ax aY Ba Bb Bg bM Bo bX Ch cK Co CP
CQ cR Ct Cu Cv Cw Cx dB Dd De dI Dk Dq Kc rQ rW Ue) Nx(aA aR bX cK cP cQ dE Hq Hv Ii Ij Io Ip Is It Iu Jk Jm Jn Jo Jq Lu Mc Md Mh
Mn Mq Na Ni Nq Ny Oi Pb Qc Qd) Ly(aN Ar Ba Bb Ch cK CP cQ Cw dE dI Ih Ij Jl Ma Me Mu Mv Mz Nm Om Oy Oz Pa Pc Pg Po Pz
Qd) Im(dE Hu Il Iq Iv Jr Js Lj Lv Lx Lz Me Mf Ml Ms Mw Nf Nk Nm Nn Nr Ns Nu Nv Oe Of Oh Oy Pa Pz Qe qZ rP) cP(Aa Af aK aM AR aU
Aw Ba Bo bU cC cG cK Co Cp cR Cu Cv Cw Cx dE dI Dk fR Gd Gn Kc Nd Nm Nw Ue) Lj(Hu Hw Hx In Jh Jj Jl Js Lv Lx Ma Me Mf Mv Mz
Nf Nk Nm Nn No Nr Nu Nv Of Og Oh Om Oy Pz Qb Qe) bM(aK aM aN aQ aR aU aV Aw aY bA bB bF Bg Bn Bo bP bU cC cG cK Cp cR cT
cY dB dD dE dF Nw Tj) Mw(Aa aR dE Ed Hw Ic Il In Je Jj Kc Kl Lv Lx Me Mf Ml Nm Nr Nv Oh Ph Qe Ue Uh Vp Vt Tj) Nd(Ao AR Ax aY
Bn Ch Co Cp cQ Cv dB DE dI Dk fR Jl Ma Mz Nn Nr Om Pa Po Pz Qa) aR(Aa aK aQ aU Aw Ba Bb Bn cC cK Cp cY dB dE Ef Kc Kl Mg Mz

Figure 14 Continued

Nh Nm Nv Om Pc Pf Ue) dE(aM Aw Bb Bg Bn Bo Cp Cu Cw Fp Jh Kc Mg Mz Nh Nm Nr Nv Om Pb Pc Pf Qe Uh Tk) Ba(aD aH aQ Ar aU aV Aw aY Bb Bg Bo bU bX cC cK cN Cp Cq Cx cY dB dI Js Tj) Nw(AA aD aF aH aN aY Bo bQ bX bZ CQ Cu dB dI Ld Qx qZ Ra Vp) Kc(aM aY bU bX cQ cR dB dI Fc Fw Gd Kl Mg Ue Uf Uh Vp Wf Tj) Aa(aJ aM Aw aY Cp Fp Hu Ir Iv Jr Li Lx Me Nm Nr Pc Qa vO) Bn(aM aQ aU aV Bb Bo bX cC cG Ch cK Co Cp Cw cY dB Mg Mt) Nv(Hw Iq Jk Js Me Mf My Nf Nk Nq Nr Ns Oe Of Oh Pc Qb Tj) Uf(Hq Ic Je Kx Mp Mx Nn Of Ou Pg Ra Ue Uh Um uT uW Vp Tj) Qe(Hu Hw Il In Iq Jj Js Mf Nf Nk Nr Oh Pc Qa Qc Ue Tj) aK(Af aM Ao Ax aY bU Ch Co cR Cu Cw Dd De Dk dO eX gT) Ue(Ar aY Cw Ic Ih Je Ke Kl Kx Nh Ou Ph Qz Uh Ur) Bb(aV aY Bo bX cC cF cG cK cY dB Mt rW sC Tj) Lx(Hw In Jj Js Lv Mf Mz Nk Nm Og Oh Oz Pc Qb) Bo(aU bU cC Db dO Dq Ef Em Gc Mg Mt Nm) Cp(aQ aU aV aY bU bX cC cK Cq cY dB Pg) Nr(Hw Hx In Jj Lv Nk Nm Oh Oz Pc) Mt(aH Ar bQ bX bZ cK cR Cu dB dI) Kl(Aj aY bX Fw Ic Js Kx Ra rW Tj) cY(Ar Aw cC dO Dq Dv dX eP eX gT) aU(aM Ar Aw aY bU cR Cw eX fR) Qa(Hw Hx In Jj Js Nk Oz Pc) Ke(eM Fw Js Pg Ra rW vH Tj) Oh(Hw Hx Jj Lv Mf Oy Pc Pz) aV(Aw Dq Dv dX eP gN gT Gw) cK(aM Aw aY bU cC cG Mg Nm) Ar(aM bU cC dB Mg Nm) Jl(Hx In Jj Oz Pc Qb) Cw(dB gW rW tV Tj) Nm(aY bX cQ Jj Tj) Mg(Ct Uh uO vQ Tj) Kg(Fw Js Of vH vQ) bB(Do dQ eP eX Gw) bU(aM aN Aw aY cG) dO(aH cG dD fR Gn) Nn(Hx Jj Oz Pc) Uh(aY Fw Js Vp) fR(aM aW Cv Mz) No(Hx Oz Pc) Ic(qI rR rW) Ii(qZ wF Tj) Om(My rP wF) aQ(aM cC dB) gW(Ex Gc Gn) Aw(aM dB) Pz(Jj Oz) Ut(dU Pg) Pb(dX eP) aA(Fp Pf) gV(aD cW) rP(dB rR) CoTj DdtV DqaH EdaY MzOz YilL VznA ZqbZ JeRa VwiP dRgT

Unconstrained panels with 2 analytes, where 1.0E-3 >= 'model p-value' > 1.0E-4. Contains 8,101 panels of 197,786 total panels evaluated. : Ko(AA aC aD aE Af aG AJ AL AN AO aP aQ Ar AS aU aV AW AX aZ BA BB Bc bE bF Bg bH bI bJ bL bM BN BO bP bR bS bV bW cA cB cC cD cF cG Ch cI cJ cK cL cM CO Cp CS CT cU CV CW CX cY cZ dA DB DC DD De dF dG Di dJ DK dL dM dN Do Dp Dq Du Ef eX Ez Fa Fb Fd Fi Fp Fr Fy Gl Gp Gw Gz Ha Hb Hc Hf Ho Hp Hq Hr Hu Hv Hw Hx Ib Id Ih Ii Ij Il Im Io Ip Iq Ir Is It Iu Iv Iz Jf Jh Jj Jk Jl Jm Jn Jo Jp Jq Jr Jt Ju Jv Jy Kc Kd Ke Kg Ki Kj Kk Kl Kn Kp Kr Ks Ky Kz Ld Li Lj Lp Lu Lv Lw Lx Ly Lz Ma Mb Mc Md Me Mf Mh Mi Mj Mk Ml Mn Mp Mq Mr Ms Mt Mu Mv Mx My Mz Nd Nf Ng Ni Nj Nm Nn No Nq Nr Ns Nt Nu Nv Nw Nx Ny Oa Oe Og Oh Oi Om On Op Or Ow Oy Oz Pa Pb Pc Pe Pf Ph Pi Pk Po Pz Qa Qc Qd Qe Qg Qh Ql Qm Qn Qt Qu Qv Qw Qy Rb Rc Rf Rg Rh Ri Rj Rm Rt Rv rW Rx Ry Sr Ss St Tn To Tr Tt Tv Ua Uc Ud Ug Uk Ul Um Uo Up Ur Us Ut Uu Uv Uw Ux Uy Uz Va Vb Vc Vh Vi Vo Vs Vt Vu Vv Vw Vz Wc Wd We Wf Wg Wh Yh Yi Yl Zq Zw Zx Ye Tm Tl Xa Wm Yf) Jd(Aa aC aD aE Af aG aH aI AJ aK AL AN AO aP aQ AS aU aV AW AX aZ BA bB BC bE bF bG bH bI bJ bL bN bO bP bR bS bU bV bW bZ cA cB cC cD cE cF cG cH cI cJ cK cL cM cN CO CP cQ cR CS CT cU CV cW cX cY cZ dA DB DC DD De dF dG dH Di dJ DK dL dM dN Dp Ef Ez Fa Fb Fc Fn Fp Fr Fy Gl Gp Ha Hb Hc Hf Hr Hu Hv Hw Ib Id Ih Ii Ij Ik Il Im Io Ip Iq Ir Is It Iu Iv Iz Je Jf Jh Jj Jk Jl Jm Jo Jq Jr Ju Jv Jy Kd Ke Ki Kj Kk Kn Kp Kr Ks Kx Ky Kz Ld Li Lj Lu Lv Lw Lx Lz Ma Mb Mc Md Me Mf Mh Mi Mj Mk Ml Mn Mp Mq Mr Ms Mt Mu Mv My Mz Na Nb Nc Nd Ne Nf Ng Nh Ni Nj Nl No Nq Nr Ns Nt Nu Nv Nw Nx Ny Oa Oe oF Og Oh Oi Om Or Ow Oy Oz Pa Pb Pc Pe Pf Pi Pk Po Pz Qa Qb Qc Qd QG QH qI Ql Qm Qn Qt Qu Qv Qw Qy qZ Rb Rc Rf Rg Rh Ri Rj Rm rQ rT rU rV rW sC Sr Ss St Tn To TR Tt Tv Tz Ua Ub Uc Ud UL Um UO UP UR Us Ut Uu UV uW uY uZ vC vH Vo vQ Vs Vt Vu Vv Wn Wm Ti Th) Kq(Aa aC aD aE Af aG AJ aK Al AN AO aP aQ AS aU aV AW Ax aZ BA BB BC bE bF bG bH bI bJ bL bM bN bO bP bR bS bU bV bW bZ cA cB cC cD cE cF cG CH cI cJ cK cL cM CO CP cQ CS CT cU CV Cw CX cY cZ dA DB dC DD De dF dG dH Di dJ dK dL dM dN Dp dR EF eP Ez Fa Fb Fn Fp Fr Fy GL GP gW Ha Hb Hc Hf Hr Hu Hv Ib Id Ih Ii Ik Il Im Io Ip Iq Ir Is It Iu Iz Je Jf Jh Ji Jj Jk Jl Jm Jo Jp Jq Jt Ju Jv Kd Ke Kg Ki Kj Kk Kl Kn Kp Kr Ks Ky Lh Li Lj Lu Lv Lw Lx Ly Lz Ma Mb Mc Md Me Mf Mh Mi Mk Mn Mq Ms Mu Mv Mz Nc Nd Ne Nf Ng Nh Ni Nj Nl Nm No Nr Ns Nt Nu Nw Nx Oa Oe Og Oh Oi Om On Or Ou Ow Oy Oz Pa Pb Pd Pe Pf Ph Pi Pk pS Pz Qa Qb Qc Qd QG QH qI Ql Qm Qn Qt Qw Qy qZ Rb Rc Rf Rg Rh Rm rO rP rR rW Tn Tr Tt Tv Tz Ud Uf UG Uh Uk Ul Um Uo Ur Us Ut vH Vs Vt Vu Vv Wm) Un(aA aC aD aE Af aG aH aI AJ aK AL aM AN AO aP aQ AS aU aV AW AX aZ BA BB BC bE bF bG bH bI bJ bL bM bN bO bP bQ bR bS bU bV bW bZ cA cB cC cD cE cF cG cH cI cJ cK cL cM cN CO Cp CS CT cU CV cW CX cY cZ dA DB DC DD De dF dG dH Di dJ DK dL dM dN Dp dR EF eM Ex Ez Fb Fc Fi Fp Fr Fy Gc GL Gn GP Gz HB Hc Hf Hu iA IB Id Ih Ii Ij Il Im Io Ip Iq Ir Is It Iu Iv Iz Jh Jj Jk Jm Jo Jq Ju Jv Kd Ke Ki Kj Kk Kp KR Ks Ky Li Lj Lu Lv Lw Lx Lz Ma Mb Mc Md Me Mf Mh Mi Mk Ml Mn Mq Mt Mu Mv My Mz Nb Nc Nd Ne Ng Nh Ni Nj Nl No Nr Nt Nu Nv Nw Nx Oa Oe oF Oh Oi Om On Or Ow Oy Oz Pa Pb Pe Pi Po Pz Qa qB qC Qd Qe Qh Qm Qn Qu Qv Qw Qy Rb Rf Rg Rh Ri Rj Rm rP rV rW Sr Ss St Tn To Tr Tt Tv Ua Uc Ud Ug Ul Uo Up Ut Uu Uv Vo vQ Vs Vt Vv Wm Ti) Uf(Aa AF aH aI aM An Ap AR Ax aY Bb Bg Bn Bo bQ bX bZ cE Ch cN CP CQ cR Ct Cu Cv Cw Cx Dd DE Dg DI Dk Ed Ef Ez Fa Fn Fp Fr Fy Gc Gl Gp Ha HB Hc Hf Hr Hu Hv Hw Hx iA Ib Id Ih Ii Ij Ik Il Im In Io IP Iq Ir Is It Iu Iv Iz Jf Jh Jj Jk Jl Jm Jn Jo Jp Jq Jr Jt Jv Jy Kd Ke Kg Ki Kj Kk Kl Kn Kp kR Ky Kz Ld Lh Li Lj Lu Lv Lw Lx Ly Lz Ma Mb Mc Md Me Mf Mg Mh Mi Mj Mk Ml Mn Mq Mr Ms Mt Mu Mv Mw My Mz Na Nb Nc Nd Ne Nf Ng Nh Ni Nj Nk Nl Nm No Nq Nr Ns Nt Nu Nv Nw Nx Ny Oa Oe oF Og OH Oi Om On Or Ow Oy Oz Pa Pb Pc Pd Pe Pf Ph Pi Pk Po pS Pz Qa QB Qc Qd Qe Qg Qh Ql Qm Qt Qu Qv Qw Qx Qy Qz Rb Rc Rf Rg Rh Ri Rj Rm sC Ss Tn To Tr Tt Tv Tz Ua Ub Uc Ud Ug Uk Ul Uo Up Ur Us Ut Uu Uv vA vH vI Vo vP vQ VS VT VU Vv wP xA Tk Wn Wm) Kf(Aa aC aD aE Af aG AJ aK AL AN AO aP aQ AS aU aV AW AX aZ BA bB BC bE bF bG bH bI bJ bL bM bN bO bP bR bS bV bW cA cB cD cG CH cI cJ cK cL cM CO Cp CS cT cU CV CW cX cY cZ dA Db DC DD De dF dG dH Di dJ DK dL dM dN Dp dR dX EF eM eP Ez Fa Fb Fn FP FR Fy GL Gn GP gW HB Hc HF hG Hu iA IB Ih Ii Ij Il Im Io IP Iq Ir Is It Iu Iv Iz Jh Jl Jm Jo Jq Ju jV Kd Ki Kj Kk Kn Kp kQ KR KS Ky Kz Li Lj Lu Lv Lw Lx Lz Ma Mc Md Me Mf Mh Mk Ml Mn Mq Mu Mv My Mz Nb Nc Ne Nh Ni Nj Nl Nr Nt Nu Nv Oa oE oF Og oH Oi Om oN Or Ow Oz Pa Pb Pe Po Ps Pz Qd Ql Qm Qn Qu Qv Rb Rh Rj rW Sr Ss St Ua Uc Ug Ul Uo Up Us Ut Uu Uv Vo vQ Vs Wm) Jt(Aa aC aD AF aG aH aI Aj aK aM AN aO Ap aQ Ar As aU aV AW Ax Ba Bb BC BG bH bL bM Bn bQ bR bS bU bZ cA cC cE cF cG Ch cI cN cO Cp cR Cs Ct Cv Cw Cx cY cZ DB Dd De Dg dH DI Dk Dl dR dU EF eP Fn gC GL gP Hq Hu Hv iA Ib Ic Id Ih Ij Il Ir It Iu Iv Jf Jh Jk Jl Jn Jo Jq Jr Js Ju Jv Jy Kg Ki Kl Kx Ld Lu Lw Ma Mc Mf Mg Mi Mk Ml Mp Mq Mr Ms Mu Mv Mx My Mz Na Nb Ng Nk Nm Nn No Nq Ns Nu Nv Ny Oa Og Om Ou Oy Pa Pb Pg Ph Pi Po pS Pz Qa QB Qc Qd QG QH qI Qt Qu Qv Qw Qy Rb Rc Rf Rg Rh Ri Rj Rm rQ rR rT rV rW sK Sr Ss St Tn To Tr Tv Tz Ua Uc Ud Ug Uh Uk UL UM uN UO UP UR Us Ut Uu Uv uW uY uZ vB vC vH vI Vo Vt Vu Vv yH tL Tk Wn) Ap(aA Dp dR eF eM Ez Fa Fb Fn Fy gL Gn gW Ha Hb Hc Hf Hu Ib Id Ih Ii Ij Il Im Iq Ir Is It Iu Iz Jh Jj Jk Jl Jm Jn Jo Jq Jr Ju Kd Ke Kg Ki Kj Kk Kn Kp Kr Ks Ky Kz Ld Li Lj Lu Lv Lw Lx Lz Mc Md Me Mf Mh Mi Mj Mk Ml Mn Mq Mr Ms Mu Mv Mw Mx My Mz Nb Nf Ng Ni Nk No Nr Ns Nt Nu Nv Ny Oa Og Oi Om Or Ow Oy Pa Pb Pe Pf Pi Pk Po pS Pz QA QB Qc Qd Qe QG QH qI Ql Qm Qn qP Qt Qu Qv Qw Qy qZ Rb Rc Rf Rg Rh Ri Rj Rm rN rO rQ rR rS rT rU rV sC sK sM sO Sr Ss St To tR tS TV Ua Ub Uc Ud UG uI UL uM uN UO UP UR Us UT UU UV uW uX uY uZ vA vB vH vI VO vP vS vT VU VV vW wB wC wD wF wH wK wL yH yJ yK yL zG zH zI Zq yE tM tL xA Wm Ti) Mm(aA aC aD AF aG aI aK aM AN aO aQ aU aV Aw Ax aY Ba Bb bH bL bM bQ bU bX bZ cE cF Ch cI cN cO Cq cR Cu Cw Cx cY dB Dd De Dg dH DI Dk Ef Ez Fa Fb Fi Fw Gl GP Hc Hq Hv iA Id Ii Ij Io Ip Is It Iu Jk Jm Jo Ju Ky Lu Lw Lz Ma Mc Md Mg Mh Mi Mj Mn Mq Mv Mx My Na Ng Ni Ny Oi Ow Pb Pi qB Qc QH qI Qn Qv Qw qZ Rb rN rO rS rT rU rV sK sM sO Sr Ss St TN TO tQ tR tS TT tU Tv tX Ua Uc UG uI UL uM uN UO UP uR UT UU uV uW uX uY uZ vA vB vC vI VO vP vS vT vU VV vW wB wC wD wE wF wG wH wJ wL wP wQ yD yJ yK zG zH zI yE tM tL xA Tk Wn Wm Ti Th) Kc(Aa aC aD aE aF aG aH aI aJ aK aL AN AO aP aQ

Constrained panels with 3 analytes, where 1.0E-9 >= 'model p-value' > 1.0E-10. Contains 1,855 panels of 37,261,550 total panels evaluated. :
Jg{ln(Hx Ih Im Iq Jk Jr Li Me Mf Ml Mm Mr Mu Mv My Mz Nd Nk Nq Ns Nt Nu Nw Nx Oe Oh Oy Oz Pa Pc Pd Pf Qa Qe) Mt(Hw Ij Ik Il Iq
Jh Ji Jj Js Li Lj Ly Me Mp Ms Mu Mv Nd Nk Nn Ns Nv Nw Nx Oe Om Oy Pc Pd Pe Pf Qb) Lj(Hw Ij Ik Il Io Iq Iu Ji Jj Jn Ly Me Mw Mx My
Ne Nf Ng Nk Nl Nq Ns Nx Oe Oy Pd Pf Qa Qc Qd) Nd(Fp Hx Iu Ji Jk Li Ly Mm Mu Mv Mw Nj Nk Nq Nr Ns Nw Nx Oe Oh Oy Oz Pa Pc Pd
Pe Pf) Oy(Fp Hx Ik Iq Ji Jj Jk Ly Mb Me Mk Mr Ne Ng Nq Nr Nw Nx Oe On Oz Pa Pd Pe Pf) Pc(Fp Hw Hx Ij Ik Il Iq Jh Ji Jj Js Ly Mb Mp Ms
Ne Nf Nn Ns Nv Nx Ny Oe Pf Qb) Mv(Fp Hx Ik Io Iq Ji Jj Jk Js Li Ly Mb Me Ne Nl Nq Nw Nx Oe Om Pd Pe Pf) Mu(Fp Hx Ik Io Iq Iu Ji Jj Jk
Ly Mb Me Ne Nq Nw Nx Oe Oz Pd Pe Pf) Mw(Hw Hx Io Iq Iu Jj Jk Lh Li Ly Mb Me Nq Nr Ns Oe Oh Om Pd Pe) Ji(Hw Ii Ij Il Iq Jj Jq Js Ly
Mp Ms Ne Nf Nn Ns Nv Ny Oe Oz Qb) Pf(Fp Hw Ij Ik Il Iq Iu Jj Js Ma Mp My Ne Nf Nk Ns Nx Oe Oz Qb) Nx(Hw Hx Ij Il Jj Js Ly Mb Ms
My Ne Nf Nl Nq Ns Oe Oz Qb) Ik(Hw Ij Il Iu Jh Js Li Ly Mm Nf Nj Nk Ns Oe Oz Qb) My(Hw Io Iq Iu Jj Jk Li Me Ml Nq Oe Oh Om Pd Pe)
Mb(Iq Jj Jk Js Li Ml Ne Nk Nw Oe Oh Oz Pd Pe) Fp(Hw Iq Jn Ml Ms Mx Ne Nf Nv Ny Qa Qc Qd) Nq(Io Iq Iu Jj Jk Li Me Mm Oe Oh Om Pd
Pe) Jk(Im Io Iq Me Nk Ns Nw Oe Pa Pd Qa Qe) Ly(Hw Im Js Li Me Ms Nf Pd Pe) Ne(Hw Ij Il Iq Iu Js Mx Oe Oz) Hx(Il Im Iu Li Mm Ns Oh
Pd) Oz(Il Im Iq Jh Jj Ma Oe Qb) Ns(Iq Iu Jj Js Me Oe) Il(Li Ng Nw Of Pe) Iq(Jj Oe Of Pd) Nl(Jn Nj Pd) Qb(Pe Qa Qe) Js(Nw Of Pe) Mf(Jj Of)
Nb(Mr Nr) Ng(Jh Nn) Li(Mp Pg) Nw(Nv Ny) IjPe JjPd OeOh} Ji{Mt(Fp Hw Ii Il Jj Jk Jq Lj Ly Mp Mu Mv Mw Mx My Nd Ne Ng Nk Nl Nn
Nq Ns Nv Ny Oe Of Oy Oz Pc Pf Pg Qa) Pf(Ii Il Iq Iu Jj Jk Jq Ma Ml Mu Mv Mw Mx My Ne Nf Ng Nn Ns Nv Ny Oe Of Oy Oz Pg Qc) Fp(Hr
Hw Il Jj Jn Jq Js Ly Ml Ms Mw Mx My Nd Ne Nf Nk Nq Ns Nv Ny Oe Oz Qa Qc) Ne(Hw Hx Il Iu Jj Jn Jq Js Li Ly Mb Mp Ms Mw Mx My Nj
Nk Nq Ns Oe Oz Pd) Nd(Fr Hw Hx Im In Jj Jp Jq Js Li Lj Mm Ms Mw My Nj Nk Ns Oz Pd Pe Qb) In(Hw Ih Im Jq Li Lj Ly Mp Ms Mw Nr Nu
Nx Oz Pc Pd Qa Qe) Nj(Fr Hw Im Iu Jj Jp Jq Li Lj Mm Ms Mw Mx Nl Oz Pd) Hx(Im Iu Jj Jq Js Lj Mm Mp Mw My Oe Oz Pd Pe Qb) Mb(Hw
Jj Js Li Lj Ms Mw My Nf Nk Nl Nq Ns Pd) Nl(Hw Ik Iu Jj Jn Jq Li Ms Mx My Oe Oz Pd) Js(aY Bo bX Ch cK cP Dg Li Lj Ms Nt Pe) Qb(Ih Im
Jq Li Ms Nt Oz Pc Pd Pe Qa) Ms(Hw Li Ly Mw My Nq Oz Pc Pd) Nc(Iu Jn Li Ly My Ns Pc Pd) Ik(Ii Is Iu Li Mp Mv Oz) Li(Hw Il Mp Nq Oz
Pg) Jq(Im Lj Ly Nx Oz) Oz(Im Lj Ly Mw) Ly(Hw Jj) Lj(Hw Mx) IrOk} Nh{On(Fp Hr Hw Hx Ik Il Jj Jk Js Ly Mp Mt Mu Mw Mx My Nj Nq
Ns Nx Oe Of Oy Oz Pc Pd Pf Qa) Li(Hw Hx Ik Il Jj Jk Jn Jp Jr Ly Mb Mm Mt Mx Nj Ns Nx Of Oz Pc Pd Qa Qc Qd) Nk(Fr Ih Im Jt Lj Lx Mb
Mm Nc Nn No Nr Nt Nv Oh Oy Oz Pa Pc Pz Qa Qe) Mt(Fp Hw Hx Ik Il Jj Jn Jp Lh Mx Nj Ns Nx Oe Om Oz Pd Qb) Pf(Fp Hw Hx Ik Il Iu Jj Jn
Jp Lh Mb Mm Mw Mx Mz Nj Pc Qa) Nw(Fp Hw Ij Jk Jr Ms Mu Nd Ns Nx Oe Oy Pc Pd Pg Po Qa) Lh(Hr Hw Hx Ik Iu Jj Js Mb Mx Nj Oe Of
Oz Pc Pd Qa) In(Fr Ik Im Lj Lx Mm Nn No Nx Oh Om Pd Pz Qa Qe) Nx(Fp Fr Jj Jp Js Mb Mm Mw Mx No Oz Pc Pd Pe) Jp(Fp Hw Jk Js Ly
Mx Nj Oz Pc Pd Qa Qb) Mw(Fp Hw Hx Ik Js Ly Mb Oz Pc Pd Qb) Mm(Fp Hw Hx Ik Mb Pc Qb) Qb(Fp Im Jt Nv Pd Qa) Js(Fp Jt No Pd Pe)
Ik(Fr Jj No) Mx(Fp Pe) Qa(Pe Qe) Jj(Jt Pd) FrMb LyIm} Mt{Ik(Fp Hw Il Iu Jk Jp Js Li Lj Mm Ms Mx My Nc Ng Nj Nq Ns Oe Of On Oz Pc Pf
Qb) Pf(Fp Hw Hx Il Jk Js Ly Ma Mp Ms Nc Nd Nk Nl Nq Nw Nx Of Oz Pc Qb) Fp(Hw Hx Jj Jk Jn Mm My Nc Nd Nq Ns Nw Nx Oe Og Oz Pc
Qa Qc) Nj(Aa Hw Hx Im Jj Jp Js Jt Lh Li Lj Mm Nx Oh On Oz Pc Pd Qb) In(Ih Im Jt Lh Li Lj Ly Mm Ms Nd Ne Nt Og Oh Om On Oz Pc Pd)
Nx(Hw Hx Il Jj Jk Js Ms Nc Nd Nk Nl Oe Of Oz Pc Qb) Nw(Hx Js Ly Ms Mu Mw My Nd Ne Nq Nv Oz Pd Qb) Nc(Hw Hx Jj Js Li Mm Oz Pc
Pd Qb) Mb(Aa Hx Jj Js Lh Lj Mw Ns Qb) Pc(Hx Lj Ly Ms My Nd Nl Oe Qb) Li(Hx Il Jk Js Nd Qb) Nk(Lj Ms Nd Ne Oz) Hx(Jj Jp Lj Mm)
Nd(Aa Jp Mm) Qb(Im Nl Pe) Js(Lj Nl Pe) ImOz} Nw{Mb(Hx Ij Jn Li Lj Ms Mu Mv Mx Nb Ne Nf Ns Nv Nx Oh Oy Oz Pd Pg Po Qb) Nl(Hw
Il Jn Ly Ml Ms Mu Mw My Nd Nq Nv Nx Ny Oy Oz Pc Pd Pf Pg Qa) Nc(Fp Hw Ij Il Jn Jr Li Ml Ms Mu Mz Ns Nx Oe Oy Pc Pd Pg Po Qa)
Hx(Fp Im In Js Li Ly Ml Mm Mu Mw My Nd Ne Nq Ny Oz Pf) Nd(Fp Im Js Li Ml Mm Ms Mu Mw My Oz Pd) In(Ih Im Ly Nk Nt Nx Oz Pd
Pe Pf) My(Fp Ly Ne Nx Of Oz Pc Pd Pf) Pf(Il Js Ly Mp Mw Ne Nq Qb) Fp(Il Js Mw Mx Nv Ny Qb) Ne(Js Ly Mw Mx Nk Qb) Ik(Hr Ii Iu Jh Jn
Lj) Nj(Ij Iu Jn Li) Ly(Ms Oz) QbQe} Ik{Mm(Fp Hw Jp Li Lj Ly Ma Mb Mp Nc Ng Nj Nk Nl Nq Ns Nx Of Oh Oz Pe Pf Qb) Jj(Fp Fr Im Jl Jt
Lx Ly Mz Nc Nj Nk Nl Nm Nn No Nr Ns Nv Nx Pa Pd Pe Qa) Jp(Fp Hw Hx Jh Js Li Mb Mu Nf Nk Nl Nn Ns Nv Oe Of Oz Pf) On(Ij Il Mu Mv
Mw My Nc Nj Nk Nq Ns Oe Oy Qb) In(Fp Im Jl Lh Lj Lx Mw No Nv Oh Pf Qa Qe) Nk(Fp Im Li Lj No Oh Pe Pf Qa Qe) Li(Hr Il Jk Nc Nf Nj
Of Oy Qb) Lh(Il Jk Nc Ng Oe Of Qb) Pf(Ly Mz Nc Nj Nl Of Qb) Fr(Jk Nc) Il(Pe Qe) Qb(Lj Pe) NoNc QeOf} Pj{sC(An cB Ch cM Cp Ct dB
Dc dH eC Ef Im Jd Ks Ng Or Oy qA Ri Ua Uc Uu Vo Vs) vC(Ap Ar aX dH Ii Jp Kn Lv qT Ri Ue) pS(cB cM Gp iC kQ Mn oK Ri rV Ue)
uN(aC Ii Qy Ri rQ rR Uu) uW(Aw cB Cp Ef Iz Jh Ng) jE(qH rN rO rS sK sO) Js(aY Lh Ok On Qe) cB(uY uZ vA vB vH) IK(qH rO rS sO)
uG(Fa Kq Om Ut) cM(uM uX uY) rP(Ip jV kQ) vI(Ct Ef Ua) aC(uO vA) rW(hV sK) rV(jK qB) vB(cH Vo) UusM jFsO qlkQ} Nc{Nk(Ih Ir Jl Jr
Lj Lx Ly Ma Mg Mu Nb Nj Nl Nm Nn No Nr Nt Ny Oh Oy Oz Pc Pg Po Qa Qb) Pf(Fp Hw In Jp Js Lh Mb Mm Mz Nx On Pc Qb) Li(Hw Hx Js
Ly Mb Nx Pc Qa Qb) Nx(Fp Fr In Jj Jp Mm Pc) On(Hw Hx Jk Ly Nd Oz) Mb(Fr Jp Lh Mm Mw) In(Fp Jt Lh Nv Pe) Lh(Jj Js Qb) Jp(Hx Ly)
FpMm} Nj{On(Fp Hr Hw Hx Il Jj Jk Js Ly Mm Mp Mw My Nq Ns Oe Of Oy Oz Pc Pd Pf) Jp(Fp Im In Js Li Lj Mb Mm Mw Ni Nx Oh Pc Pd
Pe Qb) Nk(Fp Im Jl Lh Mm Mw Nl Nv Qa Qe) Li(Hx Jj Js Ly Mm Mw Nx Pc Pf Qb) Pf(Fr Im In Lh Ly Mw Mz Nx Oh) In(Jt Lh Nv Pe)
Mm(Fp Mb Nx) AdOf QbQe JjLh} Mb{On(Fp Hw Hx Ij Il Iq Jj Jk Js Lj Ml Mm Mp Ms Mu Mv Mw Ne Nf Ng Nk Nl Nq Ns Nv Nx Oe Oy Oz
Pd Pf) Mm(Fp Fr Jp Lh Li Lj Ly Mw Nx Oh Pe) Jp(Fp Hx Li Lj Nl Nx Pf) Ly(Fr Im Li Mw Pf) EtdE NxPf} Nl{Nk(Im Jl Jt Lh Lj Lx Mm Nn
No Nv Nx Oh Pd Qa Qe) Pf(In Jp Js Ly Mm Nx On Qb) In(Jt Lh Li Nv Pe) Qb(Li On Qe) Hx(Jp On) LyJp JjLh JkOn JsLi} Js{Ok(Ad aH al Ap
aY Bn bQ bX cK cW Dd dE Kf Kj Tz Uk) Et(Ad aY bM cK Kf Kj Kx Tz Uk Un) AdMz} Ad{Bo(Aj Bg bM Bn Cq Cu dE) Of(In Io Ly Nd Pg
Tj) Jv(vB vI) AjBn CtbM bLuW jVrP} In{Fp(Im Jp Lh Mm Mw Nx Pf) Ne(Li On) LyPf NdOn} Pf{Ly(Im Jp Mm Ne Nx) Nd(Jp Mm On)}
Et{Ij(Mk Mr) aY(cK dE) FwKf} On{Nd(Jj Of) Qb(Fp Ne) HxOf} Bo{Dl(dB dE) fR(aK aV)} Ne{Nk(Fp Li) QbQe} Ok{sC(jG qB) KkvB}
Dl{KeeM cPdE} Jp{AaNd FpHx} aW{fR(aK aV)} BbNrrP LyImJj IcqGoE KecMvI Constrained panels with 3 analytes, where 1.0E-8 >= 'model p-value' > 1.0E-9. Contains 3,323 panels of 37,261,550 total panels evaluated. :
Mt{Li(Hw Iq Ji Jj Jn Jr Ly Mj Mp Ms Mw Mx My Ne Ng Nk Nl Nq Ns Nw Nx Oe Of Oy Oz Pc Pg Po Qa Qc Qd) Nw(Hw Ij Il Iq Jj Jk Jn Lj
Me Ml Mp Mv Mx Ng Nk Nn Ns Nt Nx Ny Oe Of Og Om Oy Pc Pe Pg Po Qa) Js(Ad Hw Hx Ih Im Jj Jp Jr Jt Lh Ly Ml Mm Ms Nd Ne Nk Ns
Nt Og Oh Oz Pc Pd Qe) Jj(Hw Im Jt Lh Lj Ly Mf Mm Ms Nd Ne Nk Nl Nm Nt Og Oh Oz Pc Pd Pe Pf Qb) Qb(Hw Hx Ih Jp Jr Jt Lh Lv Mm Ms
Nd Ne Nm Ns Nt Og Oh On Oz Pd Qa) Hx(Im In Jt Lh Mr Ms Mw Nk Nl No Oe Og Oh On Oz Pb Pd Pe Qe) Lj(Hw Il Iq Jn Jr Ly Mm Ms Mx
Nc Nd Nl Nx Oe Og Oz Pd Qa Qc) Nd(Hw Im Jt Lh Ly Mr Mw Nc No Nr Ns Og Oh On Oz Pd Pe) Hw(Im Jp Jt Lh Ly Mm Ms Ne Nk Nl Og
Oh Oz Pc Pd Pe) Ms(Im Jn Jp Lh Ly Mf Mm Ne Nm Ns Og Oh Oz Pd) Ly(Im Jp Mm Nc Ne Nk Ns Oe Og Oz Pd Pe) Nl(Jn Jp Lh Mm Mx Nm
Ns Oz Pd Qa) My(Jp Lh Nk Nx Og Om On Pd Pf) Nc(Il Jn Jp Lh Mx Nm Ns On Qa) Ne(Jp Mm Mx Ns Nx Pc Pd Pf) Nk(Im Jr Mf Nt Og Pc Pd
Pe) In(Iv Jp Jr Mf Nm Pz Qa Qe) Jg(Ii Io Md Mm Ny Oh Pa Qa) Nq(Jp Lh Mm Nx On Pc Pd) Jk(Im Jp Jt Lh Og On Pd) Oe(Aa Im Jt Lh Nt Og
Oh) Of(Jt Lh Mm Nm Og On Pd) Oz(Jp Jt Lh Mm Ns Og) Aa(Fp Ik Me Mp Pc) Pe(Il Ji Jn Mx Qa) Pf(Iq Jn Ng Ns Qa) Pc(Im Mp Mw Ns)
Nx(Mp Ng Ns) Mm(Mp Og) Iq(Ji Pd) Om(Ji Mw) On(Oy Pg) MkOy llPd QaQe PjyK} Ik{Li(Hq Hw Hx Ij Iq Iu Js Lh Ly Mb Mw Mx My Mz
Nb Ng Nl No Nq Ns Nx Oe Oh On Oz Pc Pf Pg Po) Oh(Fp Hw Il Im Iu Js Lj Ly Mb Mw Nc Nf Nh Nj Nl No Ns Nx Oe Of Oz Pa Pc Pd Pe Pf
Qb) Mw(Fp Fr Hw Il Jk Lh Lj Ly Mb Nc Nf Ng Nj Nk Nl Ns Nx Oe Of Oz Pc Pd Pe Qb) Fr(Fp Hw Il In Lj Ly Mb Mu Mv My Ng Nj Nk Nl

Figure 14 Continued

Nq Ns Nx Oe Of Oy Oz Pc Qb) Lh(Fp Hr Hw Ii Iu Jo Js Lj Ly Mb Ms Mu Mx My Nf Nj Nk Nl Nq Ns Oy Oz Pf) Nc(Fp Hw Im In Jt Lj Lx Ly Ma Mz Nm Nn Ns Nv Nx Pa Pc Pd Pe Pz Qe) On(Fp Hr Hw Hx Ii Iu Jh Js Lj Ly Mp Ms Mx Nb Nf Nl Nn Nv Oz Pc Pf) No(Hw Il Jk Js Ly Ne Nf Nj Nl Nq Ns Nx Of Oz Pc Pd Pe Pf Qb) Qe(Hr Hw Iu Jk Js Ly My Nf Ng Nh Nj Nl Ns Nx Oe Oz Pc Qa Qc) Pe(Hr Hw Jk Js Ly Mx My Mz Nf Nh Nj Nl Ns Nx Of Oz Pc) Fp(Im Js Ly Mx Mz Nf Nh Nj Ns Nx Oz Pd Pf Qb) Nh(Im Js Jt Lj Lx Mx Mz Nn Ns Nx Pa Pc Pd) Nk(Ih Jl Lx Mz Ne Nn Nr Nv Nx Oz Pa Pd) In(Ih Jt Nj Nl Nn Nr Nx Om Pa Pd Pz Qd) Lj(Hw Il Js Mx Nf Nj Nx Om Oz Pc Pd Pf) Im(Hw Il Ly Nj Ns Nx Of Oz Pc Pf Qb) Pf(Hw Il Iu Jk Js Ma Ng Ns Nx) Qb(Jl Lx Nj Nn Nv Pa Qa) Of(Ad Nm Nn Nv Nx Pz Qa) Nx(Mz Nj Nl Ns Oz) Il(Lx Mm Nv Qa) Nv(Jk Ng Nq) Et(Cu dE) Lx(Nj Pg) Mz(Nj Nl) MyOm IqJg QaJs PjsC} Ji{Js(aH aK aR bU dB dE dI Hw Ih Im Iq Jd Je Jj Jn Jq Kf Kj Ko Ly Mp Mw My Nf Nr Ns Nx Oh Oz Pc Pd Ph Pj Qa Qe Qz Ra Ue Uf Uk) Li(Ii Ij Iq Jj Jk Jn Jq Jr Lx Ly Mj Ml Mu Mv Mw Mx My Nb Nf Ng Nn Ns Nv Ny Oe Of Oy Pc Pd Po Qa Qc Qd) Pe(Hr Hw Ii Il Iq Jj Jk Jn Jq Ly Ml Mp Ms Mu Mv Mw Mx My Nf Nk Nq Ns Nv Ny Of Oy Pg Qc) Pd(Hw Ii Il Iq Iu Jj Jk Jq Lj Ly Ml Mp Mu Mv Mw Mx My Nf Nq Ns Nv Ny Of Oy Pg) Mw(Fr Hw Ii Il Jj Jk Jq Ly Mp Mu My Nf Ng Nq Nw Oe Of Oy Pc Qb) Mp(aY Fp Fr Hw Jj Jq Ml Mm Mr Mx Nr Nx Oe Oh Oz Pc Qe) Pc(Fp Im Jj Jq Lj Ly Mu My Nf Nn Nq Ns Nv Nx Oy) Lj(Il Iq Jj Jn Ly Ms Nc Nf Nk Oe Oy Po Qc) My(Fr Hw Jh Jj Jq Ly Mx Nw Of Om Oz Qb) Pg(bM Fp Iv Jg Lx Mi Mr No Nr On Pa) Nq(Fr Hw Jj Jq Ly Nw Nx Of Oz Qb) Ms(Jj Jq Mu Mx Ns Nv Nx Ny Oe Oh) Mx(Jg Jq Ly Mu Mv Nf Ns Nt Nx) Im(Hw Ii Il Iq Jj Ly Nf Oe) Qe(Ii Il Jk Nv Of Qa Qc) Nx(Ii Il Jj Nf Oe Of Oz) Mu(Fp Hw Jj Jk Jq Mm) Ly(Mm Nf Ns Oe Qb) Oy(Fp Jq Mk Nr On) Nt(Il Jj Nk Oe) Hw(Jq Mm Oz Qb) Nr(Jj Nb Qb) Ns(Jq Ml Oz) Jg(Iu Jh Ml) dE(aR aY Na) Mm(Iq Qb) Nd(Iu Oe) Jj(Ml Oz) FrJk LzIl MrNb IvQb NyOm PjyK} Nw{Pf(Fp Hq Hw Ij Iq Jk Jn Jr Ma Ml Ms Mu Mv Mx Nb Nf Ng Nn Ns Nv Nx Ny Of Oy Oz Pc Pg Po Qa Qc Qd) Ly(Fp Hw Im Jj Js Li Lj Md Me Ml Mm Mu Mv Mw Mx Nf Nq Ns Nv Nx Ny Oe Of Oy Pc Pd Pg Qb) Ne(Fp Hw Ij Il Iu Jj Jk Jn Jr Li Ml Mp Ms Mu Mv Nq Ns Nv Nx Ny Oy Oz Pc Pd Pg Po Qa) Fp(Hw Ij Jn Jr Ml Mm Ms Mu Mv Mz Nb Nf Nk Nq Ns Nx Oe Oy Oz Pc Pd Pg Po Qa Qc) Hx(Ih Jj Jp Lj Mk Mp Mr Ms Mv Mx Nf Ns Nv Nx Oe Oy Pb Pd Pe Pg Po Qb) Js(Ad Ih Li Lj Mp Ms Mu Mv Mw My Nk Nn Nq Nr Ns Nt Nx Oy Oz Pd Pe) In(Iv Jr Li Lj Me Mf Mp Ms Mu Mw My Nn Nr Ns Nu Oy Pc Pz) Oz(Im Li Lj Ml Mm Mp Ms Mu Mv Mw Mx Nq Nt Nv Nx Ny Oy Qb) Jg(Hw Ii Ij Jh Jn Ml Mp Ms Mx Nb Nf Nn Ns Oc Pg Po Qb) Qb(Ih Im Li Lj Mw My Nd Nk Nq Nt Nx Pd Pe Qa) Nx(Il Jj Mp Ms Mu Mw Nf Nq Of Oy Pc Pg) Pd(Il Ml Mp Ms Mu Mv Mw Nq Nv Ny Oy Pg) Nd(Jj Lj Md Mv Nq Ns Ny Oe Pe) Mw(Hw Li Me Mu Nk Of Pc Pe) My(Hw Jh Li Me Mx Nk Pe) Nl(Ij Iu Jj Jr Ns Po) Pc(Ms Mu Nq Nv Ny Oy) Nq(Hw Li Me Of) Pg(Li Mi Mr Nr) Ny(Me Om Pe) Il(Li Pe) PoLi MmMp MrNb MuMx} Nh{In(Ih Ii Ij Jl Jq Ly Ma Mb Mg Mu Mz Nm Nr Nt Ny Of Oy Oz Pa Pc Pg Po Qd) Ly(Fp Fr Jj Jt Lh Lj Lx Ma Mb Mm Nk Nm Nn No Oh Pa Pc Pd Pe Qe) Fr(Fp Hw Hx Il Jj Jk Js Mm Mx Nj Nq Ns Of Oz Pc Pd Qa Qb) Mb(Im Jt Lj Lx Ma Mz Nm Nn No Nv Oh Om Oy Pa Pd Pe Pz Qe) Jt(Fp Hr Hw Hx Iu Jn Mx Nj Ns Nx Oe Of Oz Pc Pd Qa Qd) Jj(Fp Im Jp Mg Mm Mw Nm Nn No Nr Nv Oh Oy Pe Pz Qe) Js(Ad Dg Im Lj Lx Ma Mm Nm Nn Nv Oh Om Pa Pz Qa Qe) Oh(Fp Hw Hx Im Mm Mx Nj Nx Oz Pc Pd Pe Qb) No(Fp Hw Hx Jn Mx Nj Ns Oz Pc Pd Qa Qb) Mw(Il Jn Lj Mm Mx Nd Nj Nm Ns Of Pe Qa) Lj(Hw Jn Jp Mg Mm Mx Nx Oz Pc Pd Qb) Pe(Hw Hx Il Iu Jn Jr Mm Nj Nm Oz Pc) Nn(Hw Hx Mx Nj Ns On Oz Pc Pd Qb) Im(Hw Hx Nj Nx Oz Pc Pd Qa) Qb(Jl Lx Nm Nr Nx Oy Pa Pz) Lh(Fp Il Jk Jn My Nf Ns Nx) Qe(Hw Hx Jn Mx Oz Pc Qc) Nv(Hw Hx Mx On Oz Pc Qa) Fp(Hw Jn Nm Oz Pc Pd) Jp(Il Jn My Nd Ns Of) Mm(Iu Mx Nj Oz Pd) Nk(Jl Jr Mu Pg Po) On(Iu Jn Ms Nd Ng) Pc(Lx Ma Mz Nm) Pd(Hw Iu Jn Mx) Nm(Hw Of) Lx(Hx Mx) Nx(Hw Pa) Om(My Oz) MzOz IuLi} Jg{Li(Hr Hw Ij Iq Jh Jn Jr Js Ma Mj Ml Mu Mx Nb Nf Nn Nv Nx Ny Po Qb Qc Qd) Pe(Hw Iq Iu Jh Jj Jn Ml Mp Ms Mx Nb Nf Nk Nn Ns Nv Ny Oe Pc Pg Qa Qc) Js(Bg bM bX Ih Iq Jh Jj Jr Me Mf Ml Ms Mu Nf Nk Nt Oh Oy Pd Pj) Oh(Hw Ij Il Io Iq Iu Mp Ms Mu Mv Nf Nn Nv Ny Oy Qb) Pd(Hw Ij Il Iu Jh Ma Mp Ms Nf Nn Ns Nv Ny Oe Qb) Me(Ij Il Iu Jh Jj Mm Ms Nf Nk Nn Nv Ny Qb) Qb(Ih Im Jr Lv Mf Mm Nk Ns Pa) dE(aR aY bM Io Na Oe Of Pc) Mp(aY Jj Mm Mr Nr Nx Pa) Ij(Im Iv Lx Mk Mr Nr Pa) Il(Im Jr Nr Ns Pa Qa Qe) Pg(Iv Lx Mi Mr No Nr Pa) Nn(bM Io Iu Mm Nx Pf) Ms(Io Iu Ma Mf Nk Pf) Hw(Im Mm Mu Mv Ns Oy) Jh(Io Iq Iu Nx Pf) Mv(Iu Lj Nk Ns) Nb(Iv Lx Mk Pa) Nx(Ii Iq Iu Nv) Pj(Fw Io Na Of) Ma(Jj Mm Oe) Mf(Iu Nk Oc) Qe(Mw Qa Qc) Aj(Ly Nd) Mu(Mm Om) Jr(Nf Nk) Ny(Nr Om) Of(aH bM) Oy(Io Iv) bX(aR aY) HuPc IiLh ImIq JjOe aLtN} Nc{On(Fp Hr Il Jj Jn Js Mm Mp Ms Mu Mw Mx My Ng Ni Nq Ns Nx Oe Of Oy Pc Pd Qa) Lh(Fp Hr Hw Hx Iu Jk Li Ly Mm Mx Nd Nj Nx Oe Of Oz Pc Pd) Fp(Fr Jp Js Jt Ly Mb Mg Mw Mx Nm Oh Oz Pc Pd Pz Qb) Nx(Hw Im Js Jt Lj Ly Mb Mw Mz No Oz Pd Pe Pz Qb Qe) Mm(Fr Hw Hx In Jj Jp Li Ly Nd Nj Oz Pc Pd Pe Qb) Li(Il Iq Jj Jk Jn Jp Jr Mx Nd Oz Pd Pf Qc Qd) Fr(Hx In Jk Js Ly Nd Nj Oz Pc Pd Qb) Jt(Hw Hx Jj Js Ly Mb Oz Pc Pf Qb) Nk(Hu Ii Iv Jh Mv Mz Of Pa) Jp(Hw In Js Nd Oz Pc Pd Qb) Mb(Im Nv Oh Pd Pe Pz Qe) Mw(Hw In Ly Oz Pc Pd Pf) Js(Ad Dg Nv Pe Pj) In(Im Pd Pz Qe) Qb(Im Nv Pe Qa) Pf(Hx Jj Nj Nm) Ly(Im Pe Qe) Jj(Pd Pz) AdOf QaQe} Nj{Mm(Fr Hu Hx Im In Jj Jr Jt Lh Lj Ly Mw Mz Nn No Nr Nv Oh Om Oz Pa Pc Pd Pe Qe) Fr(Aa Fp Hx Im In Iu Jj Jk Js Jt Lh Lj Ly Mb Mw Nq Nx Of Oh Pc Pd Pe Qb) Lh(Fp Hr Hw Hx Im Iu Jp Js Li Lj Ly Mb Mw Mx Nx Oe Of Oz Pc Pd Pe Qb) Mw(Aa Fp Im In Jj Lj Ly Mb Nx Oh Oz Pc Pd Pe) On(Aa Ii Ij Is Iu Jp Li Lj Ms Mu Mx Ni Nx) Nk(Ad Jt Lj Lx Mu Nn No Nr Nt Nx Oh Pd) Pf(Aa Fp Jj Js Jt Nm No Pc Qb) Li(Hw Iu Jk Jn Mb Mx Oz Pd) Nx(Fp Im Jj Jt No Pd Pe Qe) Js(Ad Ap Dg Nv Pe Pj) Im(Fp In Jj Ly Qb) In(Ad Fp Qa Qe) Jj(Jt Nv Pd Qe) Jp(Aa Mz Of Oz) Et(Bo Cq Cu) Qb(Nv Pe Qa) Oh(Fp Pd) Ok(Cq Cu) Pe(Il Ly) AaQe EfvS HrJt} Nl{Nk(Ih Ii Ir Iv Jh Jj Jr Ma Mb Mg Mu Mv Mz Nb Nm Nr Nt Ny Of Om Oy Oz Pa Pc Pg Po Pz Qd) On(Fp Hr Hw Il Iu Jj Jn Js Ly Mp Ms Mu Mw Mx My Nd Nq Ns Nv Nx Oe Of Oy Oz Pc Pd Qa) Li(Hw Hx Il Jj Jk Jn Jp Jr Lh Ly Mb Mm Mw Mx Nx Oz Pc Pd Pf Qa Qc Qd) Lh(Fp Hw Hx Il Iu Js Ly Mb Mx Oe Of Oz Pc Pd Pf Qb) Pf(Fp Hw Hx Iu Jj Jn Jt Mb Mw Mx Mz Nm Oh Pc) Jp(Fp Hw In Js Mm Nd Nx Oz Pc Pd Pe Qb) Fr(Fp Hx In Jk Js Ly Mb Nx Pc Pd Qb) Mm(Fp Hx In Jj Ly Mb Nx Pc Pd Pe) Mw(Fp Hw In Ly Mb Nx Oz Pc Pd) In(Fp Im Nx Pd Qe) Nx(Fp Jj Pd Pe) Qb(Im Nv Pe) Ad(Js Of) Jj(Jt Pd) FpPd LyIm QaQe JsPe} Pj{Js(Ad bX Ch Dg Et Ih Jd Je Jn Jp Jr Kf Kl Ko Kq Mg Mw Mz Nv Oh Ou Pd Pf Ph Qa Tz Un Ut) yK(Ap Ar cB dH Gl Ii Jp Kc Kn kQ Lh Lx Mq Po qT Rg Ri Ue uU) kQ(qG rQ uI uW uX vP vQ vU zI tM) vT(Aj cB jE lK lN Ra Ri rR sC Vo) xA(aD cB cM Ms Mw Ra Ri Vo) Jd(aY bX Dk In Qx Vp yE) yH(aC cB dA Uu Vo Vs) Di(uO uR vH vP vU) jE(uN vP vV zH yE) Ue(Bo Na uG uN) Vo(uT vQ vU vW) cM(uV vO vW zI) lK(uY vP vV zH) Of(Ad Kl Ss) aC(sM uG uU) aU(rS rV yE) jF(qH vP vV) sC(Aw dA Qz) Bo(Je Og) Fw(Et Mw) Ng(vI yE) cB(vC yJ) uN(Hw Ph) TjKq PovC FarW IcaY RcbX QbQe JeRa SsuW UtPg UuuY gWyE} Ad{Of(aR bM Bn bQ bX cK Cu dE Ed Et Hr Hx Jn Ma Mb Mx Na Nk Oe Og Ok Pc Pd Qb Ue Vp) Aj(aK Ap aR aU bM bU cG cK Cq Cu cY Dc dE Dg Dl Js Tj) Bo(aH aK aM aR aU bQ bU bX cC cP Ct DB Dk Dl Js Tj) bM(aK aM aN aR aU aY Bn cG cN Cq cR Cu cY Dc dE Js) Js(bX Hv Io Jr Lh Mm Nd Nv On Pc Pd Qe Un) aM(aC aK aR aU aV Bn bU bX cK Ct cY Dc dE) Ct(aH aK aR aY Ba Bn bU bX cP Dc dE) aR(aK aU Bn bU bX cC cN cW cY dE) aK(aH cN dE dJ) Bn(Cq Cu Dc) dE(aJ aY cP) Cq(Aw Cp) Jv(vP zG) jV(vB zH) EtOe} Mb{Mm(Hx Im In Jj Jl Jt Mu Mz Ne Nk Nn No Nr Nv Of Og Om Oz Pa Pc Pd Pz Qe) Lh(Fp Hw Hx In Jj Jp Js Li Lj Ly Ml Mw My Ne Nf Nk Nx Oe Of Oh Pd Pf Qb) Li(Hw Hx In Iq Jj Js Ml Mw Ne Nf Nk Nx Oh On Oz Pc Pd Pf Pz Qb Qd) Jp(Iq Js Ml Mw My Na Nd Nc Nk Ns Of Oh Pd Pe Pz) Pf(Fp Fr Im Jt Ml Mw Mz Na Ne Nk Nv Oh Pz) Fr(Fp Lj Ml Mw Ne Nx Oh Pd) Mw(Fp Lj Ne Nx Oh Pd Pe) Nx(Aa Fp Oh Pd Pe) Ly(Nv Oh Pe Qe) Fp(Nk Oh) In(Nv Pe) On(Hr Nn) EtaH QbQe OhPd OkdE} On{Nd(Fp Hw Hx Ii Il Iu Jk Jp Js Li Lj Ly Mm Ms Mu Mv Mw My Ng Nk Nq Ns Oe Oy Oz Pc Pd Pe Qb) Hx(Fp In Jj Jk Li Lj Ly Mp Mu Mw My Ne Ng Nq Ns Oe Oy Oz Pf) Fp(Hw Il Jk Js Ly Mw Mx My Ne Nk Nv Oe Of Oy Oz Pf) Ly(Hw In Jj Ne Ns Oe Of Oz Pf) Ne(Hw Jj Jk Nk Of Oz Pf) Pf(In Jk Mp Nq Of Qb) Js(Bg Bn Dd Dg Uk) Qb(Lj Of Pe Qe) In(Lj Nt Pe) Of(Nx Oz)} Pf{Nx(Fp Hw Hx Il In Jj Jk Jp Js Mm Mp Nd Ne Nf Nk Of Oz Pc Qb) Ly(Fp Hw Jj Js

Figure 14 Continued

Lh Li Mw Mz Nf Nk Of Oz Pc) Ne(Fp Hw In Jp Js Lh Li Mm Mw Mz Pc Qb) Lh(Hw Hx In Jj Js Nd Of Qb) Mm(Fp Hw Hx In Ma Mp Of)
Nd(Aa Im Li Mw Nk Oh) Fp(Jp Js Mx Nk Qb) Nt(In Js) Hx(Jp Li) ImIn QbQe} Et{Js(aF aH al aK aR Ax bQ bX cE CP dB Dd dE Jd Je Jf Ou
Ph Qz) dE(aH al aR bM cl cK cP cQ Hx Mp Na Nd Oe Pb Pc) Fw(Kx Ou Qt Qz Ri Tz Ue Un) Pg(aY bM Je Kf Kx Wm) Tj(aY Io Mx Na)
Mp(aH aR bM Kx) Nd(aH al aY) Kf(In Mx Qb) cK(aF aH aO) Ue(Ks Na) aY(aI bZ) BoLy NnbM JdVp OeaH} Li{Ly(Hw Hx Im In Jj Jp Js
Mm Nd Ne Nf Ns Nx Oe Oz Pc) Nx(Hx Il In Jj Jk Nd Ne Nf Of Oz Pc Qb) Nd(Im In Jj Jp Lh Mm Mw Nk Pc Qb) Ne(Hw Hx Jj Jk Js Mx Oz Pc
Qa Qb) Hx(Im In Jj Jp Lh Mm Mw Oz Pc) In(Fp Im Lh Nt Pc Pd) Qb(Fp Pc Qe)} Fp{Mm(Hw Hx Jj Js Ly Mp Mx Nd Ne Nf Nk Nx Oz Pc Pd
Qb) In(Fr Jt Ly Mg Ne Nt Nv Oh Om Pd Pz) Jp(Js Ly Mx Nd Ne Nk Nx Oz Qb Qc) Nx(Jj Mw Mx Ne Nk Oz Pc Pd) Im(Ly Nk Oz Qb) Lh(Hx
Jj Js Qb) Mw(Ly Oz) NkPd QbQe} Ok{Js(aF aR bZ cE cP cQ dB dl Jd Kx Ra Ue Uf Un Ur Ut Tj) Tj(Ap bM li Md Mr Mx Na Of Pd Ue) dE(aR
cQ Hx Mp Na Oe Of Pc) bM(Mp Nn Pg) cM(rP rQ uY) CuNd QdrQ KkvQ PgaH qBrA jGrW} Jp{Nd(Hx Lj Ly Mm Mw Nr Nx Oh Pd Pe)
Ly(Hx Im Lj Ne Nx Oz Pd Pe) Hx(Lj Mm Ne Nx Pd Pe) Ne(Nk Nx) cZtR} Pe{In(Lh Ly Mm Nd Ne Nt Nx) Mm(Hx Ly Nd Qb) Nx(Il Jj Js Qb)
Ne(Nk Qb) NtJs NdNk QbQe} Aa{Ng(sO uG uM uP uR uT uZ vB vO vT zG tM) Nd(Fr Im Mw Qe) JhuP} Dl{Bo(aK aU bM Bn cP Cq Db)
cP(aK aR bU Cq) aK(aR dE) CpCq} Ne{Nk(Im Lh Mw Nv Nx Pd) In(Jt Lh Nv) Jj(Lh Nx) MmNx QbLh} Js{Lh(Kf Ko Ph Ra Uk) Dg(Jn Jr Nd)
Kf(Kq Mm Mz) MzKq} fR{aM(aK aQ aV cY) aW(aQ aU cY) gW(bB bU cM) BocY aVbC} Jj{Nx(Lh Ly Mm Nr Pd Qe) Lh(Hx Ly Nd)
ApvQ} Ly{Im(Hw In Oe Oz Pc) QbQe} dV{aV(Aj Dd) BccY DeaK} Ap{vQ(aC 1K) cZvV} Dg{BnBo aKaR cPdE} Mm{Nd(Fr Lj Nx)}
Qb{Qe(Nt Nx Pd)} Ng{aLwP bLuW} Ii{FwrR QlwF} DkjVvQ MgjGqH MwNxOz UfcZwP

Constrained panels with 3 analytes, where 1.0E-7 >= 'model p-value' > 1.0E-8. Contains 6,911 panels of 37,261,550 total panels evaluated. : Pj{Js(aM Ap Ax Ba bM Bo bU cN Co cP cQ cS Cu Cw dI Dl Ef Fa Fb Fr gL Ib Ic Ii Im Io Jf Jl Jt Jy Kc Kj Kn Kx Li Mj Mm Mt Mu Na Ne Ng Nh Nl Nn No Nw Og Oy Pc Pe Qd Ql Qt Qv Qz Ra Rc Rg Ss Tn Ua Ue Uf Uh Vs) vC(Aj Aw Bb bP Co Cp Ct Cw Dc Ef Fa Fr Gl HC Hq Hu Hw Ij Io Jg Jh Ji Kc Ke Kg Kl Ko KQ Ky Lh Lx Mp Mq Mt Mw Ng Nr Om On Oy Pb Pc Pd Pe Ph Qt Ra Rc Rg rQ rR rV Ua Ub Uc Un uO Ut Vs Vu wL) sC(Aa Ad Af Ar aS Bb bF bM Bo cF cH cR cT Cw Cx dE Gp Hu iA Ii Ij Il Iq Iz Jg Jh Jk jO Ki Kj Kk Md Mg Mn Mp Mq Mv Mw My Ny Of Ph Pi qB qD Qh QT qY RC Rg tR tS Tt Ue vA vH wL wP tL) Ue(aM aR aY bX Ch cN cP cQ Et Fn Fw Ih Ik In Jd Je Jf Jg Jp Jy Kc Kf Ks Mb Mw Nc Ne Nh Nj Nl Oe Of Og Ok Ou Pc Pd Pf Ph Qv Qz Rc Rg rP rW Un Us Uv Tj) Na(Ad Bn bX Ch cP cQ Et Fr Fw gL Jd Je Jf Ji Jl Jp Kc Kf Kl Ko Kq Lh Ly Mp Mt Mw Nn Nw Og Ok On Ou Pd Ra Rc Um Un Tj) Tj(Ad Ax Bo Ch Cw Et Fa Ii Io Jd Je Jf Jg Kc Kf Kl Ko Kx Lh Md Mw Ok On Ou Pc Pd Pf Qe Qt Qz Ra Rg Tz UN Ut) Fw(Ad Ap Ba Bo Ch cQ Cw Jd Je Jf Ji Kc Kf Kl Ko Kq Lh Ok On Ou Pf Qa Qe Qt Qu Qz Ra Rc Rg Ss Tz Ua Uf UN) Jg(Aj aY Bo bX Cu Dk Hb Hx In Je Jf Jt Jv Ks Ma Mp Mx Nt Oe Og Ou Pc Pg Qb Qc Qx Qz Ra Rg Us Uu Vp) Jd(aF aM bM Bo bQ bU bZ cQ Hx Io Jv Kf Ks Mp Mw Mx Nt Ny Oe Of Og Ou Pg Qz Ra tN tQ tR tS tT uW) Je(aM aY bX Ch Et Hw Io Jv Jy Kf Ks Mw Oe Of Og Ou Pc Pd Pf Pg Qt Qx Qz Rc Us Vp wE) Jf(Ap aY Bo Ch Cw Et Fn Io Kf Kl Mw Oe Og Ou Pc Pd Qt Qx Qz Ra Rc Rg sK Un wL) Bo(Ad An Bn Ch cQ Et Jl Jy Kf Kl Kq Ly Mp Mw Nc On Ou Pd Qx Qz Ri Ss Tz) Ch(Et Hr Hw In Io Jo Jv Jy Kc Ks Ma Mp Nn Oe Of Ou Pg Qv Qx Qz Ra Um) Kf(aY bX Et Hw In Mp Ms Mx Nk Nn Oe Of Og Ou Pc Pg Qb Qz Ra Um Vp) pS(Aw bP bX Ct Dc dH eF Hv Hw Kn lN Ms Mw Nr oN qH Ra Ub uZ wL) rW(Bc gW hA hW Ic Ik Io jR jY Kl Kq qA qD qO tR tX Vt wP) Qz(Ad Et Ib Jp Jy Kc Kl Ko Kq Mw Og Qt Rc Rg Ss Um Un) wL(aC cV dB dR gL Hq iB iP jD jE Lv Oz Pa Up Uu yJ yK) rP(Bc lC Io jD lK lN Nr Ok Om Ra rC rV Tz Ua uZ Vt) uN(Ed Fa Kn Lh Lu Md Mq Nf Ns Nx Om rA rX rY Ul Ut tF) Mw(Hx In Ks Mp Mx Nk Of Ou Pc Pg Qb Qx Ra Vp yK) Et(aY Hx In Io Ks Mp Mx Nt Oe Of Og Pc Qb Ra) Ou(Bn Io Mp Nn Of Og Ow Pd Pg Qb Qt Qx Ra Rc) yK(Aw aX Co Cp Di Fr Hq Hw Ke Ng Om On tV Ut) Uu(tN tO tQ tR tT tV vU wC wF wH wJ yL tL) jE(rV tR tS tV tX uU uW uZ wB wD wH wP xA) Ra(Kl Ko Kq Lz Og On Pc Pd Rc Un vH) Of(Ef Iz Kq On Qt Rc tN tQ Ua Un Vs) Vo(tN tO tU tV wB wE wF wG wJ wK yL) rV(gW Ic jF jG jQ lK Md uO vH vT xA) vB(Aa Aj cT dB dH Kr Mp Ny uW Vs vU) cM(sO tO tQ tU tV wB wC wE wH yH) Di(rR uV vO wC wD wE wG wH zI) In(Ad Kq On Pd Qe Qt Tz Un Ut) Pg(Kq Kx Lh On Pd Pf Qe Un xA) kQ(tN tR tT tU tX uO vH wB wC) tV(aQ cY dA gW jF Jj lK Up) Un(Hx Ks Mp Ms Mx Oe Qb) aC(tQ tT vT wC wH wJ yL) bX(Kc Kl Nn Qb Rg Um Vp) tR(Aw Ef iC Mr Ng Ua Wm) lK(rN sK tX wD wH wP yE) aY(Kc Ko Nn Qb Rc Um) tN(Cp Ct Ef Iz Ng Ua) uW(Ct eF oN Oy Ri Ua) Kq(Cu Ks Mx rN rR) qA(qX rA rQ rR wE) uZ(cH dE dH jK Ny) Aj(Kl Ss uY vH) Rc(Io Og Pc Rg) Ks(Ad On Rg Ss) Pd(Ha Nn Qb Um) rS(Ic jF jQ qP) vT(Aa bO dH jV) Ef(tQ tS yE) Mn(uV vW wC) Ms(uM uO wD) Up(uO wH yE) cB(vW wQ tM) cQ(dI Kc Pc) cR(uG yH xA) rQ(aU gW jM) vI(Jh lN Oy) Ad(Us Tk) Cu(On Ut) Mp(Kx wE) Mq(uG zI) Ng(tQ wK) Qb(On Qa) Kl(Oe vU) Rg(Io Mx) Og(Qv Vp) Um(bM Cw) dA(tT yL) vH(bP Ub) GpvW NnbM MewE NcNk UatQ IpxA SsvU JjwH JkyE TkVs aIsO cHuO iBtL iCtU qDrR jGqH jUjV} Et{aY(aF aH aK aO aR bG bL bM bQ bX cE Cu dB dF dG dH dI Ed Fw Hq Hr Hx Ic Ik In Jg Kr Ly Ma Mb Mj Mx Na Nf Nj Nk Nn Nq Oe Oh Pc Qb Ue Vp) aH(aF aK aQ aR Bo bX bZ cP cY Hq Hr Hw Hx Ik In Io Jg Ji Ly Ma Ml Mx Na Nf Nj Nk Nn Nq Ns Nx Ny Of Ok Pb Pc Pg Qb Qd Vp Tj) Cu(Ad cK Cp Io Jd Je Jf Jg Ji Kf Kl Kq Ks Kx Mb Mg Mt Nc Ne Nh Nl Nx Og Ok On Ou Pc Qt Qz Ri Tz Ue Un Ut) Tj(aF aI bM bQ cE Gp Hx Ii Jd Je Jf Jg Ji Kc Kf Kq Kx Md Mp Nk Nq Nx Oe Og Ok Ou Pc Pd Qz Ra Tz Ub Ue Un) Kf(aI bZ Cq cR dE Ed Ha Hq Hw Hx Io Je Jf Jn Ks Kx Mj Mp Na Nk Nn Nt Ny Oe Of Pc Qz Ri Rm Ub Ue Vp) cK(aI aL aR bC bG bQ bZ cE cI cR cZ dI dJ Fw Hq Hv Hx In Ly Mb Mp Mx Na Nk Nn Nx Ny Oe Pc Pg Qb) aI(aC aF aK aR aU bX cP cY Ed Fw Hx Ik In Kx Ly Mb Mp Nk Nn Nq Nx Oe Pc Pg Qb Vp) Mp(aF aO bC Bo bX Ch cI cP cR cZ dI Jd Je Jf Ks Ou Qz Ri Ub Ue Uk Un Vp) Ue(As Bg Bo Ed Fn In Jd Je Jf Kx Ld Mx Ns Oe Of Ou Pc Pg Qz Us Vp) Fw(Ch dE Hx Ik Io Jg Ji Lh Mb Mw Nd Nh Nx Og Oy Pc Pd Pe Pf) Pg(Ad aF aG aR bX cE cI CP dE Jd Jf Ks Ou Qz Tz Uk Un Ut) Je(Cq Hx In Jn Jr Mx Na Nk Ny Of Qb Qz Ra Rm Ub Vp) Kx(Cq Ed Hq Hx In Jf Ks Mj Mx Nf Nk Nn Ny Qb Rm Vp) dE(aF aG Bo cE dJ Io Jd Jg Ml Mx Nc Nj Nl Nn Nx Of) Jf(Ed Hx In Io Jn Mx Na Nk Nt Ny Of Qb Ub Vp) Mb(aF aG aO aR bG Bn bQ bX bZ cE cQ dB) Nd(aF aO aR bM bQ bX bZ cE cI cR cZ dI) In(Ad bM Bn Cp Jd Kj Qt Qz Tz Uk Un) Hx(Ad bM Bo CP Jd Ks Ou Qz Un) Qb(Ad bM bX cP Jd Kj Ou Qz Tz Un) Of(Ch Ed Iz Jd Kg Kj Kl Ri Ub Vp) Ks(Ed Io Ly Nk Og Oy Ub Un Vp) bZ(aR cI CP cR Ik Js Nf Pc) Oe(aF aO bM cE Ch Cp dB Kj) Bo(Ed Ji Ma Nc Nl Nx Og) Vp(Io Kc Na Nc Og Qz Un) aR(aF aO bQ bX cE Ly Nn) Ed(Io Mx Na Ou Qz Ra) Ik(aF aO Bg bM bQ cE) Jd(Bg cE Cq Dk Nk Ny) Ad(Aj Hr Io Ma Ny) Cp(Hr Mx Nq Ny) Ub(Nc Nf Ou Qz) Js(aC aO bU dI) Rm(Io Ji Nc Ou) Bg(Ib Jg Qt) Ch(Io Ma Nq) Cq(Ji Nc Nl) Qz(Kz Nf Nk) Nn(bX Uk) Ly(dX eP) Mx(Tz Un) Na(Ou Un) cE(Nx Pc) AjJg CtOg HaTz NedX HqIb IoVu OhbM} Ad{Js(AR aV Ax aY Bg Bn bQ bU cK dL Fp Hr Hw Ih Jd Jg Jn Jt Kc Kf Kq Kx Lx Ly Ne Nx Oe Oh Ou Pe Ph Qa Ra Tz Uh Uk Tj) aV(aF aH aI Aj aR aY Bg bH bM Bn Bo bQ bU bX cC cG cN cP Cq cR Ct Cu cW dA dB Dc dE dJ fR) cG(aH aI aK aM aR aU Bg Bn Bo bQ bU bX bZ cC cF cK cN cP Cq Ct Cu cY dB dE dH Dk Of) Aj(aH aJ aM aY bC bX cC cF cN cP dB Hr Hx Ik In Io Ly Mb Na Nd Nj Oe Pc Pg Qb) Tj(AR aY bM Ii In Io Ji Kc Kx Lh Ma Mb Md Mm Mx Na Nj Nk Nw Oe Pc Th) Of(aH aI aK bZ cF cR cW cZ Ic Jd Je Jv Kc Kf Kl Kx Ou Ph Qh Qz Ra Ub Uh) Cq(aC aF aH aJ aK aM aU aY bQ bU bX cC cF cK cN cP cW cY dB dE Dl Nj) cN(aC aF aH aM aQ aU aY Bo bQ bU bX bZ cC cF cK cP Ct Cu cY Dc dE) Nd(AR Bo Cu Hr Hw In Io Ji Jp Lh Mm Mw Na Nk Nw Oe Pc Pg Qb) cP(aF aH aM aR aU Bb Bg bM Bn bQ bU bX bZ cC cK cR Dc Dk In) aY(aK aQ aR aU Bg Bn Bo bU bX bZ cC cF cK cR Cu cW cY dB) In(bM Bn bX cK Io Ji Ly Ma Nc Ne Nh Nl Ok On Pc Pd Un) cY(aH aI Bg bH Bn Bo bQ bU bX cC cR Ct Cu cW dE dJ) Nj(AR Bo Ct Cu Dc Hr Hx Mx Na Oe Pc Pg Qb) aU(aH aI aW Bg Bn bU

Figure 14 Continued

Im Jj Lj Nv Pd Qe) Pe(Fr In Mw) Jj(Im Nv) Lj(Fr Mw) InNv QbQe} Kf{Fw(aY bX cR dE dI Jd Ko Kq Mm Mw Ou Qe Qz Ra Ue Un) Ue(Mm Of Pc Tj) dE(Jd Jv Ko Pc) Kq(Cu Tj) MmPg QbQe JdVp} Qb{Qe(Ih Im Jj Jp Lj Lv Mm Mw Nu Nv Oh Oz Pc Qc) Pe(Im Jp Nt Oh Pc Qa) Qa(Lv Nt Pd) Jp(Lj Nt) MmLj} In{Nt(Fr Im Jp Lj Mm Mw Nv Om Pd Qa Qe) Pe(Im Jp Jt Mg Mw Nv Oh Om Pc Pz) Lj(Mg Mm) ImPd} Bb{cP(aK aM aR bM Bn bU cC cK dE) aM(aK aU bU cK) tS(rW sC) aKbM cUtV tRrW rTrP sCvI} Mg{jG(qI rW sK tN tO tU tV tX uL wB wF wH wJ wL yK) Mp(aR bM vI) AauR NnbM} Mm{Oz(Im Lj Nt Pe) Ue(Bo Fw Tj) Jj(Nt Pd) Pe(Hw Mp) Pg(Kx Ut) JdVp LjPc aSrR} tV{Cw(cR cZ dB rW) Vo(An jV IK Pi) cR(Kc Kj KI) Kn(cM Ql) DdRh MshP IcIK} Bo{dB(Aa aK aM aQ aR aU aV bM cP) AabM cPdE} dX{Jn(aM cP cS Dc eM) Hv(cW eM Pb) Gn(aM dD) PbdD} Ic{oE(qI rQ rR rW) qP(fP gW pF) TzqQ aSrR tSoF} Aa{uP(Bg Cp Ef Iz) Ef(sK zl) bEtR b

Figure 14 Continued

Mz Nf Nk Nn No Nr Of Pa Po sC) Lh(aC aD aF aK aN bQ bZ cN CQ dl dU iA iB jV Jy kF lW oF pI qZ wF) Oz(Ex Hu Ih Ii Ij Ir Is Iv Jh Jo Jq Jr Lv Ma Mr Mu Mv Nu Om Pg Po Qd) Ra(Dk Ed Ex Hb Ii Ik Iz Kj Ly Mt Ng Nv Om Ph Qe Rc rQ sC Tr Tz Uc) Aw(aC aD aH aN aQ bC Bg bH cC cF cG cN cR Cv dl dL Fr Ly rW tV) sC(Ap aS bF bL cH cR Dg Et Fy Ik Jd Jh IL Ma Mv Or Tz Uk wF wL) Mz(cQ dl dU Hu Hx Ir Iv Jj Lv Mf Mu Nr Oh Oy Pa Pg Po qA Zq) Ii(Ed Fi iB Jj jV jY IL qA qB qC qD rB Rc Rm uR Vp vQ wG tL) On(aD aF aH aK aN bQ bZ cO cQ cR dH dI dU Ha Kx Qg Rc Uk Vu) cY(aD aH aJ Ao Ax cF cG Ch cN Co cR Cu Cv Dd De Dk Fr Gc Ly) Nn(Co Hu Hw In Iq Iv Jl Ko Lv Lx Me Mf Ms Nf Nr Nu Oy Qa) No(Ed Hu Hw In Iq Ir Iv Jj Jl Kq Lv Me Mf Mu Nq Oh Oy Ub) cC(aC aD aJ aK aN Ao aV Ax bA Bg cG Ch Co Cv dG Dk Fr Zq) rW(Al Dg Et Gl Hb Im Iz Jd Ji Kf Ko Kp Kq Om Tz Uk Un Vt) Ly(aQ cG cN cR dV Gc Gl Hb Hu Hw Iv Jr Lv Nu Ny Qt Rc) Ed(aF Ax cQ dl Im Kx Nv Nw Oh Ou Pf Ph Qe Qm Qz Tt) Gn(Ad Af aK Ao Ap aV Ax Ch Co Cs Cu Dg Dk Dl dQ gT) vQ(aC bE Dg Dl Fy Iz Jd Jg Ji Jo Kf Ms Og Om Un Vo) Gc(Af aK aV Et Fp Na Nh Nj Nl Nx Pe Qv Qz Ri Vo) fR(AN Ax bB bC Bg Ch cM Cu Dg Fp Ik Nj Pb Ph) Fc(cG Ch cQ dN Fb iC iO Jd jU IL oN Un Ut Zq) Fw(eC Hb Ik Iz Kj Nw Ou Pf Ph Qe St Tr Tz Uc) Jp(aF aK bQ bZ cQ dl iB Ko Ou Ph qY rB Rc Ug) dO(Af aG aJ aN aP cE cl cJ dF DG dl dL gT) Zq(aH Ap Bc bN cZ dN Fi Hx Nf Pk Qn Qv Vq) Js(Ch Co Cu Fy Hb Jl Kj Nr Ph Po Tr Tz Uc) Kq(eP Fn Hv pS Qb Qc Qh rR uG Uk Um vH Vt) Nw(Bg Ch Dk dV Fn Ha Je Jy Kx Qz Rc Ub Uk) aK(aH aJ aN bA bR cF cG cN dG dl Dq dX eP) tV(Al Ap cW Dg Dl Ik Jg Kj Ma Ms Ub Vo Ti) Dl(eM gL gT gW Kx Ou Ph Qx Qz Tz Ur) Fr(aC aD aF aH aQ aV bC cF Cq Ex qZ) Ik(bQ dU Ex gT Je qZ Tz Ub Vp Vt yH) Oh(Hu In Iq Ir Iv Jh Jl Me Ms Pa Qa) aQ(aD aH AJ cG Ch Cu De Dq dV) aV(Af Ao Bg Ch Co cR Dd De Dk dQ) IW(bH bl hF Ih Jn iY Mn Nc Nj Yl) iB(Ad dl Et Ji Kf Ok Pi Tz Uk Un) Po(Hw Hx In Jj Lv Nf Nk Qb qZ) Nh(aF aN Ch cQ cR Cx De dl Dk) Qe(cQ Cu Je Lv Of Qg Rc Ub Vp) Jd(bF bZ cE dH oF rQ uP uR Ti) jV(Ad Im Ir Ji JU Kf Tz Uk) Qa(Hu Il Iq Lv Mf Nf Qc Qd) Jl(Hu Hw Iq Iv Lv Mf Nf Nk) Om(aF cQ In Ny qZ uP vH wH) cG(aC aD aH bQ bR Cv dl dQ) kl(bH hF Ho Hp Mn Nj Vb Yl) Dq(cZ dD Et Fp Fy Mb Nx) Ti(Ch pS Uk uN wF yJ tL) Mt(aF cO cQ Kx Rc Ub Vp) Hb(cQ Na Nk Ou Pf Pg Ph) Ok(iA oF qA qB qD wJ yH) rQ(cR Fy Jg Li wF wG wL) Et(dU pl pS qA qD vH) Nj(cR Cv De dl Ex gT) Rc(cQ Je Ou Ph Qz Vt) Jj(Ir Iv Jo Mu Oy Pg) Nx(Ch cN cR dl dQ pl) Vp(Im Je Li Nv Tz Uc) Nr(Iq Iv Mf Oy Qb) Ng(Kx qB QZ Vt) Un(Fi iA qB qC rV) aC(cR uO vl vS wH) wF(bE dH Jh Jo Mq) Ap(gW qA qB tR) Ch(Fp Hr Id Vt) Dg(eM gW pS vH) Nk(cQ Ih Iz Ph) Tz(aF In Ou Qg) Ub(Im Nv Ou Ph) Jg(iA oF qZ uP) mM(Du Fd Vz Yl) IL(Eq Wc Yh Yf) Lv(Ir Iv Oy) Mf(dV gT Ir) Tr(Kx Ou Ph) Ji(dU iA qZ) Kp(dX Em rR) Nv(Cq Cu Il) Of(Iz Kj Uc) Vt(cQ dl Ph) Pg(Co Hx Kx) bE(vS vT wH) eM(Af Ao gV) Do(Jy Mb) Th(Dd nR) Fy(hF rR) Lx(Hu Iv) Nl(dl Dk) Hp(Mh Rt) Jh(wH wK) Ko(eX Fd) Lj(lq Iv) Pj(eQ jY) cH(qH rA) eP(aH Qz) mF(rX rY) tR(cW cZ) AdiA DiqY Film FpaF GlgW MbgT UcUr HuPa HxQd Ihln SirA RbeQ JePf Srdl QueX JnnJ KfPs KkdX RyhV RfOu NyqZ VowJ VwiC aDbA aJbR cRtX dFdQ dRdV wBlM kKpH Unconstrained panels with 3 analytes, where 0.0E0 >= 'AUC p-value' > 0. Contains 50,000 panels of 37,261,550 total panels evaluated. :
Pj{rP(AA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp dR eC ED EF ET EZ Fa Fb FN FP Fr Fw FY GL GP gW HA HB HC HF hG hL hO hP Hq HR Hu HV HW HX iA IB IC Id IH Ii IJ Ik Il Im In IO iP Iq Ir Is It Iu Iv IZ JD JE JF JG JH JI Jj JK JL JM Jn JO JP JQ JR Js JT JU Jv JY Kc Kd Ke Kf Kg Ki Kj Kk Kl Kn Ko Kp Kq KR KS Kx Ky Kz Ld Lh Li Lj lK lL lM lN lO Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pk Po pS pY Pz QA QB QC QD Qe QG QH qI Ql Qm Qn qO qP qQ QT QU QV QW QX QY QZ RA RB RC Rf Rg Rh Ri Rj Rm rN rO rQ rR rS rT rU rV rW rX rY rZ sC sK sM sO Sr Ss St TN TO tQ TR tS TT tU TV tX Tz Ua Ub Uc Ud Ue Uf UG Uh uI Uk UL UM UN UO UP UR Us UT UU UV uW uX uY uZ vA vB vC vH vI VO VP vQ VS VT VU VV vW wB wC wD wE wF wG wH wJ wK wL wP wQ yD yH yJ yK yL zG zH zI yE tM tL xA Wm Tj Th tF) uZ(AA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cC cD cE cF cG CH cI cJ cK cL cM cN CO CP CQ cR CS CT CU CV CW CX cY cZ dA DB DC DD DE dF DG dH DI dJ DK DL dM dN Dp dR eC ED EF ET EZ Fa Fb FN FP Fr Fw FY GL GP gW HA HB HC HF hG hL hO hP Hq HR Hu HV HW HX iA IB IC Id IH Ii IJ Ik Il Im In IO IP Iq Ir Is It Iu Iv IZ JD JE JF JG JH JI Jj JK JL JM Jn JO JP JQ JR Js JT JU JV JY Kc Kd Ke Kf Kg Ki Kj Kk Kl Kn Ko Kp KQ KR KS Kx Ky Kz Ld Lh Li Lj lK lL lM lN lO Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pk Po pS pY Pz QA QB QC QD Qe QG QH qI Ql Qm Qn qO qP qQ QT QU QV QW QX QY QZ RA RB RC Rf Rg Rh Ri Rj Rm rN rO rQ rR rS rT rU rV rW rX rY rZ sC sK sM sO Sr Ss St Tn TO tQ TR Tt tU TV tX Tz Ua Ub Uc Ud Ue Uf UG Uh uI Uk UL UM UN UO UP UR Us UT UU UV uW uX uY vA vB vC vH vI VO VP vQ VS VT VU VV vW wB wC wD wE wG wH wJ wK wL wP wQ yD yH yJ yK yL zG zH zI yE tM tL xA Wm Tj tF) zG(AA aC AD aE AF aG aH aI AJ aK AL aM AN AO AP aQ AR AS aU aV AW AX aY aZ BA BB BC bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp dR eC ED EF ET EZ Fa Fb FN FP Fr Fw FY GL GP gW HA HB HC HF hG hL hO hP Hq HR Hu HV HW HX iA IB IC Id IH Ii IJ Ik Il Im In IO IP Iq Ir Is It Iu Iv IZ JD JE JF JG JH JI Jj JK JL JM Jn JO JP JQ JR Js JT JU JV JY Kc Kd Ke Kf Kg Ki Kj Kk Kl Kn Ko Kp KQ KR KS Kx Ky Kz Ld Lh Li Lj lK lL lM lN lO Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pk Po pS pY Pz QA QB QC QD Qe QG QH qI Ql Qm Qn qO qP qQ QT QU QV QW QX QY QZ RA RB RC Rf Rg Rh Ri Rj Rm rN rO rQ rR rS rT rU rV rW rX rY rZ sC sK sM sO Sr Ss St Tn TO tQ TR TT tU TV tX Tz Ua Ub Uc Ud Ue Uf UG Uh uI Uk UL UM UN UO UP UR Us UT UU UV uW uX uY vA vB vC vH vI VO VP vQ VS VT VU VV vW wC wE wG wH wJ wL wP wQ yH yJ yK yL zH zI yE tM tL xA Wm Tj tF) vC(AA aC AD aE AF aG aH aI AJ aK AL aM AN aP aQ AR AS aU aV AW Ax aY aZ BA BB BC bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG DI dJ DK DL dM dN Dp dR eC ED EF ET EZ Fa Fb FN FP Fr Fw FY GL GP gW HA HB HC HF hG hL hO hP Hq HR Hu HV HW HX iA IB IC Id IH IJ Ik Il Im In IO IP Iq Ir Is It Iu Iv IZ JD JE JF JG JH JI Jj JK JL JM Jn JO jP JQ JR Js JT JU JV JY Kc Kd Ke Kf Kg Ki Kj Kk Kl Ko Kp KQ KR KS Kx Ky Kz Ld Lh Li Lj lK lL lM lN lO Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pk Po pS pY Pz QA QB QC QD Qe QG QH qI Ql Qm Qn qO qP qQ QT QU QV QW qX QY QZ RA RB RC Rf Rg Rh Rj Rm rN rO rQ rR rS rT rU rV rW rX rY rZ sC sK sM sO Sr Ss St TN TO tQ TR tS TT tU TV tX Tz Ua Ub Uc Ud Ue Uf UG Uh uI Uk UL UM UN UO UP UR Us UT UU UV uW uX uY vA vB vH vI VO VP vQ VS VT VU VV vW wB wC wD wE wF wG wH wJ wK wP wQ yD yH yJ yK yL zH zI yE tM tL xA Wm Tj Ti Th tF) vB(aA aC AD aE AF aG aH aI AJ aK AL aM AN AO AP aQ

Figure 14 Continued

AR AS aU aV AW AX aY aZ BA BB BC bF BG bH bI bJ bL bM BN BO bP bQ bR bS bU bV bW bX bZ cA cB cC cD cE cF cG Ch cI cJ cK
cL cM cN CO CP CQ cR CS CT CU CV CW CX cY cZ dA DB DC DD DE dF DG dH DI dJ DK DL dM dN Dp dR eC ED EF ET EZ Fa Fb
FN FP Fr Fw FY GL GP gW HA HB HC HF hG hL hO hP Hq HR Hu HV HW HX iA IB IC Id IH Ii IJ Ik Il Im In IO IP Iq Ir Is It Iu Iv IZ JD
JE JF JG JH JI JJ JK JL JM Jn JO JP JQ JR Js JT JU JV JY Kc Kd Ke Kf Kg Ki Kj Kk Kl Kn Ko Kp KQ KR KS Kx Ky Kz Ld Lh Li Lj lK lL
lM lN lO Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd
Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF
Pg Ph Pi Pk Po pS pY Pz QA QB QC QD Qe QG QH qI Ql Qm Qn qO qP qQ QT QU QV QW QX QY QZ RA RB RC Rf Rg Rh Ri Rj Rm rN
rO rQ rR rS rT rU rV rW rX rY rZ sC sK sM sO Sr Ss St TN TO tQ TR tS Tt tU TV Tz Ua Ub Uc Ud Ue Uf UG Uh ul Uk UL UM UN UO UP
UR Us UT UU UV uW uX uY vA vH vI VO VP vQ VS VT VU VV vW wC wG wH wK wL wP yH yJ yK yL zH zI yE tM tL xA Wm
Tj tF) vT(aA aC AD aE AF aG aH aI aJ aK AL aM AN AO AP aQ AR AS aU aV AW AX aY aZ BA BB BC bE bF BG bH bI bJ bL bM BN
BO bP bQ bR bS bU bV bW bX bZ cA cC cD cE cF cG CH cI cJ cK cL cM cN CO CP CQ cR CS CT CU CV CW CX cY cZ dA DB DC DD
DE dF DG dH DI dJ DK DL dM dN Dp dR eC ED EF ET EZ Fa Fb FN FP Fr Fw FY GL gP gW HA HB HC HF hG hL hO hP Hq HR Hu HV
HW HX iA IB IC Id IH Ii IJ Ik Il Im In IO IP Iq Ir Is It Iu Iv IZ JD Je JF JG JH JI Jj JK JL JM Jn JO JP JQ JR Js JT JU JV JY Kc Kd Ke Kf Kg
Ki Kj Kk Kl Kn Ko Kp KQ KR KS Kx Ky Kz Ld Lh Li Lj lL lM lO Lu Lv Lw Lx Ly Lz Ma Mb Mc Md Me Mf Mg Mh Mi Mj Mk Ml Mm Mn
Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF
Og OH Oi OK Om ON Or Ou Ow Oy Oz Pa Pb Pc Pd Pe PF Pg Ph Pi Pk Po pS pY Pz QA QB QC QD Qe QG QH qI Ql Qm Qn qO qP qQ QT
QU QV QW QX QY QZ rA RB RC Rf Rg Rh Rj Rm rN rO rQ rS rT rU rV rW rX rY rZ sK sM sO Sr Ss St TN TO tQ TR tS TT tU TV tX Tz
Ua Ub Uc Ud Ue Uf UG Uh ul Uk UL UM UN UO UP UR Us UT UU UV uW uX uY vA vH vI vO VP vQ VS Vt VU VV vW wB wC wD wE
wF wG wH wJ wK wL wP wQ yD yH yJ yK yL zH zI yE tM tL xA Wm Tj tF) pS(AA aC AD aE AF aG aH aI AJ aK AL aM AN AO AP aQ
AR AS aU aV AW AX aY aZ BA BB BC bF BG bH bI bJ bL bM BN BO bP bQ bR bS bU bV bW bX bZ cA cC cD cE cF cG CH cI cJ cK cL
cN CO CP CQ cR CS CT CU CV CW CX cY cZ dA DB DC DD DE dF DG dH DI dJ DK DL dM dN Dp dR eC ED EF ET EZ Fa Fb FN FP Fr
Fw FY GL gP gW HA HB HC HF hG hL hO hP Hq HR Hu Hv HW HX iA IB Ic Id IH Ii IJ Ik Il Im In IO IP Iq Ir Is It Iu Iv IZ JD JE JF JG JH
JI Jj JK JL JM Jn JO JP JQ JR Js JT JU JV JY Kc Kd Ke Kf Kg Ki Kj Kk Kl Kn Ko Kp Kq KR KS Kx Ky Kz Ld Lh Li Lj lK lL lM lN lO Lu
Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nc Nd Ne Nf Ng Nh Ni
Nj Nk Nl Nm Nn No Nq Nr Ns Nt Nu Nv NW Nx NY Oa OE OF Og OH Oi Ok Om ON Or Ou Ow Oy Oz Pa Pb Pc Pd Pe PF Pg Ph Pi Pk Po
pY Pz QA QB QC QD Qe QG QH qI Ql Qm Qn qO qP qQ QT QU QV QW QX QY QZ RA RB RC Rf Rg Rh Rj Rm rN rO rQ rR rS rT rU rW
rX rY rZ sC sK sM sO Sr Ss St TN TO tQ TR tS TT tU TV tX Tz Ua Ub Uc Ud Uf UG Uh ul Uk UL UM UN UO UP UR Us UT UU UV uW
uX uY vA vH vI VO VP vQ VS Vt VU VV vW wB wC wD wE wF vA wH wI VO VP vQ wK wP wQ yD yH yJ yK yL zH zI yE tM tL xA Wm Tj tF)
uO(AA aC AD aE AF aG aH aI AJ aK AL aM AN AO AP aQ AR AS aU aV AW AX aY aZ BA BB BC bF BG bH bI bJ bL bM BN BO bP bQ
bR bS bU bV bW bX bZ cA cB cC cD cE cF cG CH cI cJ cK cL cM cN CO CP CQ cR CS CT CU CV CW CX cY cZ dA DB DC DD DE dF
DG dH DI dJ DK DL dM dN Dp dR eC ED EF ET EZ Fa Fb FN FP Fr Fw FY GL GP gW HA HB HC HF hG hL hO hP Hq HR Hu HV HW
HX iA IB IC Id IH Ii IJ Ik Il Im In IO IP Iq Ir Is It Iu Iv IZ JD JE JF JG JH JI Jj JK JL JM Jn JO JP JQ JR Js JT JU JV JY Kc Kd Ke Kf Kg Ki
Kj Kk Kl Kn Ko Kp KQ KR KS Kx Ky Kz Ld Lh Li Lj lK lL lM lN lO Lu Lv Lw Lx Ly Lz Ma Mb Mc Md Me Mf Mg Mh Mi Mj Mk Ml Mm
Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE
OF Og OH Oi OK Om ON Or Ou Ow Oy Oz Pa Pb Pc Pd Pe PF Pg Ph Pi Pk Po pY Pz QA QB QC QD Qe QG QH qI Ql Qm Qn qO qP qQ QT
QU QV QW QX QY QZ RA RB RC Rf Rg Rh Ri Rj Rm rN rO rQ rR rS rT rU rV rW rX rY rZ sC sK sM sO Sr Ss St TN To tQ TR tS Tt TV
Tz Ua Ub Uc Ud Ue Uf UG Uh ul Uk UL UM UN Uo UP UR Us UT UU UV uW uX uY vA vH vI VO VP vQ VS Vt VU VV vW wD wG wH
wL wQ yH yJ yK yL zH zI yE tM tL xA Wm Tj tF) vH(AA aC AD aE AF aG aH aI AJ aK AL aM AN AO AP aQ AR AS aU aV AW AX aY
aZ BA BB BC bF BG bH bI bJ bL bM BN BO bP bQ bR bS bU bV bW bX bZ cA cC cD cE cF cG CH cI cJ cK cL cM cN CO CP CQ cR CS
CT CU CV CW CX cY cZ dA DB DC DD DE dF DG dH DI dJ DK DL dM dN Dp dR eC ED EF ET EZ Fa Fb FN FP Fr Fw FY GL GP gW
HA HB HC HF hG hL hO hP Hq HR Hu Hv HW HX iA IB IC Id IH Ii IJ Ik Il Im In IO IP Iq Ir Is It Iu Iv IZ JD JE JF JG JH JI Jj JK JL JM Jn
JO JP JQ JR Js JT JU JV JY Kc Kd Ke Kf Kg Ki Kj Kk Kl Kn Ko Kp KQ KR KS Kx Ky Kz Ld Lh Li Lj lK lL lM lN lO Lu Lv Lw Lx Ly Lz
Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm
Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pk Po pY Pz QA QB
QC QD Qe QG QH qI Ql Qm Qn qO qP qQ QT QU QV QW QX QY QZ RA RB RC Rf Rg Rh Ri Rj Rm rN rO rQ rR rS rT rU rV rW rX rY rZ
sC sK sM sO Sr Ss St TN To tQ TR TT TV Tz Ua Ub Uc Ud Ue Uf UG Uh ul Uk UL UM UN Uo UP UR Us UT UU UV uW uX uY vA vl VO
VP vQ VS Vt VU VV vW wB wC wE wG wH wL yH yJ yK yL zH zI yE tM tL xA Wm Tj tF) vQ(AA aC AD aE AF aG aH aI AJ aK AL aM
AN AO AP aQ AR AS aU aV AW AX aY aZ BA BB BC bF BG bH bI bJ bL bM BN BO bP bQ bR bS bU bV bW bX bZ cA cB cC cD cE cF
cG CH cI cJ cK cL cM cN CO CP CQ cR CS CT CU CV CW CX cY cZ dA DB DC DD DE dF DG dH DI dJ DK DL dM dN Dp dR eC ED EF
ET EZ Fa Fb FN FP Fr Fw FY GL GP gW HA HB HC HF hG hL hO hP Hq HR Hu HV HW HX iA IB IC Id IH Ii IJ Ik Il Im In IO IP Iq Ir Is It
Iu Iv IZ JD JE JF JG JH JI Jj JK JL JM Jn JO JP JQ JR Js JT JU JV JY Kc Kd Ke Kf Kg Ki Kj Kk Kl Kn Ko Kp KQ KR KS Kx Ky Kz Ld Lh Li
Lj lK lL lM lN lO Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na
Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb
Pc Pd Pe PF Pg Ph Pi Pk Po pY Pz QA QB QC QD Qe QG QH qI Ql Qm Qn qO qP qQ QT QU QV QW QX QY QZ RA RB RC Rf Rg Rh Ri
Rj Rm rN rO rQ rR rS rT rU rV rW rX rY rZ sC sK sM sO Sr Ss St TN To tQ TR Tt TV Tz Ua Ub Uc Ud Ue Uf UG Uh ul Uk UL UM UN Uo
UP UR Us UT UU UV uW uX uY vA vl vO VP VS Vt VU VV vW wC wE wG wH wL wQ yH yJ yK yL zH zI yE tM tL xA Wm Tj tF)
xA(AA aC Ad aE AF aG aH aI AJ aK AL aM AN AO AP aQ AR AS aU aV AW AX aY aZ BA BB BC bF BG bH bI bJ bL bM BN BO bP bQ
bR bS bU bV bW bX bZ cA cC cD cE cF cG CH cI cJ cK cL cN CO CP CQ cR CS CT CU CV CW CX cY cZ dA DB DC DD DE dF DG dH
DI dJ DK DL dN Dp dR eC ED EF ET EZ Fa Fb FN FP Fr Fw FY GL GP gW HA HB HC HF hG hL hO hP Hq HR Hu HV HW HX iA IB IC
Id IH Ii IJ Ik Il Im In IO IP Iq Ir Is It Iu Iv IZ JD JE JF JG JH JI Jj JK JL JM Jn JO JP JQ JR Js JT JU JV JY Kc Kd Ke Kf Kg Ki Kj Kk Kl Kn
Ko Kp KQ KR KS Kx Ky Kz Ld Lh Li Lj lK lL lM lN lO Lu Lv Lw Lx Ly Lz Ma Mb Mc Md Me Mf Mg Mh Mi Mj Mk Ml Mm Mn Mp Mq
Mr Mt Mu Mv Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om
ON Or Ou Ow Oy Oz Pa Pb Pc Pd Pe PF Pg Ph Pi Pk Po pY Pz QA QB QC QD Qe QG QH qI Ql Qm Qn qO qP qQ QT QU QV QW QX QY
QZ rA RB RC Rf Rg Rh Ri Rj Rm rN rO rQ rR rS rT rU rV rW rX rY rZ sC sK sM sO Sr Ss St TN To tQ TR TT TV tX Tz Ua Ub Uc Ud Ue Uf
UG Uh ul Uk UL UM UN Uo UP UR Us UT UU UV uW uX uY vA vl vO VP VS Vt VU VV vW wC wD wE wG wH wJ wL wQ yD yH yJ yK
yL zH zI yE tM tL Wm Tj Ti tF) uL(AA aC AD aE AF aG aH aI aJ aK AL aM AN AO AP aQ AR AS aU aV AW AX aY aZ BA BB BC bF

Figure 14 Continued aYmU} hV{Ry(aE bN cB cC cO Hf jF Ji Jl JY Ml Mr Mz Nc Nd Nf Ni Nk Nl Tz Uv We Tl) Uv(Fd Gb Ho Rz Sf Wd Zx Ye Xa) bB(Hp Ps We Ye) Nd(Rx Yi) Wd(Vb Wh) TvVb lpRt WeaL WhKc WfaE OrsC UxdM} Dv{aV(Af aG AJ aN aP aU Ba bJ BN bU Cp dA DD De dF dM fR Gl Gn) cY(Af aU BC bM BN De fR Gn) aK(Bc BN Cp dA dM fR Gn) Gn(aM bU dD) AfdD AnaM BcBo bBcP} Jp{cZ(tN tS tX vH vU wD wG wH wK wL yH yL zH tL) al(vH wB wC wD wE wH wK wL zA) uW(aL aQ cU dJ Ra) Rh(pS sC uN vB) aL(tS vH wG) sC(bM Or) vH(Ra Ub) TkdE qArT} iC{Nt(Em Eq Gc Gh Gn Lp Ry Sf Uy Vb Vj Vw Wb Wc We Wf Yi Zx) Vw(cZ dM hW Mw) Yj(cX Fn Lv) Zq(cI Fn Uv) Ko(Dr Op Ps) Yg(Bc Uv) Wh(Kc Rf) GbbB LyTk TvVb UrkO UsmS cEmE} jT{nL(Af Aw Ax Bn Co Cs Cw Cx Dg Di gP Tz) nC(Aw Ax Bn Co Cs Cw Cx Dg Di Tz) kO(Bg Dd Tz Ur) mI(An Ax Tz) nK(aY gP) hC(kC mY) kG(Cu Dg) AnnN WmkF FyUx RcWh UmkN cEmF} Ri{hR(Du Em Eq Fd Hl Ho Hp Ps Rv Rz Ux Vw We Zq Zw Zx Ye Tl Xa) jD(Eq Ry Ux Vj Vw) Mq(wH wK) Tl(hW jL) Vw(jF jR) qT(Dr Gc) jY(Sj Yd) GnjR cFjB} dE{Tk(aL Cw Dc Dd Dl Fy Ip Ji Jm Kf Kj Lh Nd Nm Oi Pi Pz Qd Ub Uh Un Vt) Ut(fA fB oT oV pI) Wn(Dc Lh) Uh(uW tM) CwuL ThnF MwpI QgtM} gW{fR(aK aM aW bB bR bU Ex Gn Ji Ko Vb) Ji(Dr Em Gn Vb) dR(Ps Vh Wd We) Gc(bB bM Ko) Qa(Sh Uy) Kc(Ru Wh) AnYg EmKo FnZq VzbN JyVc NxUy VbVh aDgV mEjY} rP{Kq(aI bB dD Nr qZ rR) Un(jG Or qA qB qC Ql) Im(aL Js Ub) Ra(Hb Kj Ko) Jd(Al Uk) Qg(Ih Tz) Or(Dl Kl) Vt(iA Pi) Pd(Nk Nn) qC(cC dB) DgjG bLvT dIrR} Dg{Mn(tN tO tQ tS tT tU tX) aL(tS uL vP vU vV wB wP) sC(aS Fw jG Or qB qC) qB(tO tS tX uP) pS(aS Pi Qg) cZ(vP vV) VpuW jGqH} aY{jO(Gb Gc Rz Sj Uw Ux Vh Yg Zq Zx Xa) kC(Du Fd Fi Hp Rt Uy Vi Wc Zq Xa) Th(kK nR) nD(jQ jR) qU(mS nL) SflN UymI aDgV} Kl{vH(bL cU Jo Jv Mr Mt Nr Pi) Pi(sC sK tS vU) aL(tS vU wB) bL(sC uM vU) cZ(tS vU vV) RapS KkuL OrsC cDfB cUuW tSuN qBuP kKpH} Jd{uP(aI Al jG Kp qB Uk uW zA) Wn(Al Cp Dc Dd Ip) zA(aI cO rU sC) aI(wD wK) bL(uW wB) uL(Kk Ql) JouW LdwL PhsC cOtN wJwK} Un{jG(qH qZ sC sM uG uN uW vA) qD(bE Oe Ql uG tM) Or(rR sC uG uN) Ql(uM uW uZ) qB(sC uG) EdgZ LueQ aLuR aUvP} pI{Nx(aJ aM cS dG dN eC Mk Ml mY nH nN Og oN oP) Lh(lW mS nJ) Mw(bX Kc) cF(Nw Qz) eC(Lz Ug) NuaR JibC QgUs} oE{Nf(Du Fd Hp Yg Yh Yi Yj Yk) Hp(Gn nD Qv Yj) Yg(An De Qv) Vz(bN Cs Dc) Qv(Yh Yi) Vj(Ar Rg) CsTl JnVb} Ef{vH(Ar aS bL hC Jv Uh) bL(uW vU wK wP) uL(jG Jv Kp Oi) As(wP tM) Nn(vS wP) Kp(vB vI) wK(qZ wJ) cUuI} mF{rB(Hw Oc Oh Qa) jE(Ct Hw Oe Ur) rX(Ih jD Nc Oe) jL(Bn Ug Uk) jY(cW Hw Qa) cE(iB jF) ToVz cWqX} eQ{Mz(bF bV cF Ld My Qn) Me(Gp Qy Uo Us) Lv(Kf Qy) Ky(eC Qw) On(aL bG) LydN MxaF RbbG LhOu} Vz{To(lW mP mS mY nI nJ nK nT) mT(aK bW nK) mY(Iq oF Uh) MfnU MrnR NknH HpkF aMlX} Ji{Fd(hA jG jH jI jK) gC(bC Bo cC) uP(cW qA Ql) oV(bU cC) GnrA ZxjY JsbM RvhW QlvB eCoT} Ry{hR(bP Hx Nf Nj Uv) Mr(hW jM jQ) iB(jD Wc) jQ(Hf Tl) jY(Or Wm) NihX TtlM YjjP bRjD cUjE} Th{bG(mT mZ nC nD nO nR nT oP oQ) nR(Ao bM Bn cS Gp Nf) NynF UskO cSnN} Fy{Qd(qZ rR vU) Mn(wH wJ) Wd(hW iB) hR(Gc Ux) qY(vH Tk) uL(Bo Kk) TjpK GbjD QgrR aIvV dAzA} lN{Nj(kO mY nD nH nJ nL oP oQ) Qv(Gb Gc Uw Vw Yg) FnYi NknD loYj aHmT} dB{Cw(sK sM uI uL uM uY vA vB vH vI) Qg(vA vT yL) Tk(jD qY) LhoD} jG{Jo(rS rT tO vU) Mt(tS vH wG) Ip(Hp Va) Vt(tQ tT) Oy(tS wK) TzkO IjsC OnvU} Ed{rR(Mq Nv Pi Sr zA) jB(cD Lj Qd) Im(rQ sC) gZ(bN Lv) ArsC NrrQ MqvS} jY{mE(aP aU aV bQ cU dM hB Uu) Em(bB Fn) Nj(nN oQ) RvPe UvVa nBhC} Yj{jP(bL cX Fn Io Iv Rx Yf) Fn(jD jH jI jO) ChhG bAjD cXjO} cZ{Ar(tQ tU uL uP wB wL) Uh(tN uR wB wE wH) Co(tS wG) AwtS} Ko{Em(gC nD rA St) gC(Jr Mw Mz) Hp(Rm St) GcqX WbjD TldR} gV{aD(aK aM aQ aU aV bO cP cW cY) aM(aN cP) aQcW} sC{Im(Vp Vu) Pz(aS Ur) bF(Or zA) DlqC TzoH IhQg IjqB JoaS PfzA} Lh{dR(gZ pH pK) oT(hF nH pH) Hx(pH pK) oD(Jn Vv) kCpK} jO{aL(Hp We Ye) ExRx GcIp GdoK YibP ZqaK RzbB VbVs mYhC} Iz{Jv(uL vH wK) bL(uW wK) uP(Kp uW) NjvS LpnK OruL} kR{Hp(Bo Gn Qv Tj) Vw(It Pz Qv Tj) Ph(Fi Gn)} Tz{Di(hR qH wB wL) Ps(kC kK) kO(jH qY) QgqH} Jo{qA(rT tO wJ xA) Ur(uT xA) qB(rT xA) gLuW} aI{Gl(wE wH wL) Co(wD wH) Uh(wE wH) ArwK ZqnK} dN{kF(Em Gd Rv Rz Ux Wb Zq Ye) NxjB} lW{Tl(Mv Mw Nq Qm) Lp(aS nY) Vi(Mw Qm) TjVw} Om{Mn(wH wK) uP(eT qB) AsuG FwvH LdwL QlwH} Zx{Ql(mE mY nC nR) QykC KpmT UmkK} Kq{Ld(tS vU wK yE) RaqZ aLwG uGvH} Pi{mZ(Fd Fi Uw We Tl Yf) tSjE} hR{Db(Fd Gc Ps) Qv(Gb Vw) DpGc WfaE} jD{kO(Ch Ct Ur) Wf(aR Fn) DdVb UwbZ} pK{Tj(Jq Mw Nx Qm Tn) MzcF IqOn} Wn{Dc(aN bH eC gP iB) MrjM} bL{tM(Ch Co Hc) ChwK KfiB KjvS} mS{To(Dr Sf Xa) DirA HxSf IqLt} oT{eC(Lz Mn Nt) MzcF NxOg UhbU} Nj{nN(rB rX rY) YihX UuvS} cW{qW(mY nC nK) qX(mH nO)} rA{Gn(Nl qU) DrbP GcNc mYhC} kK{pH(kP Rh Ut) bQiB dLgC} Gl{aL(wG zA) aUzA bEvS} Mq{wH(dD Ql) QgvU PhuN} Zq{Ch(bZ hG) AnhG QvjH} bG{UcfA TlnJ OpmZ mEjP} hW{HuRv ItVw SfUv WfaE} uP{qA(Dl Ms Nw) NwqB} vH{Ut(Kd Ld) ArbE CuUb} Cw{LywQ HfpS iHvB} Gc{qU(Ex Ip) QvqV} Im{uW(Ub Vp) QgrR} Kj{QdwK QgvS JvvB} Lp{nK(Hu Rz) mHoH} jP{DimE WfcP VhbB} kP{Vb(aH bZ) WhcE} Bo{DlgC aKfR} Dr{ExqU bPqT} Em{Kc(dR Qv)} Mz{pH(bC cF)} Hp{VjiO cUoN} Iq{RumY OnjB} Sh{QmnR UtkF} Wc{CxiB UvjE} Tk{DdLy PbaL} eC{NtfA QzoV} lM{GbbB YgQv} vS{UbNy KpbE} CoaUzA TjVwhG FdUajK FiPhiO GngPnU NnJhwK NrQgpS MbaVfR MtOrrR HlRfiB HbaLwL IpRzjH YibPhA QaQbfA JnrBkC JrLtlY TlOgnK VhmIoN VumHjQ bXnCjL cEmEjF mYhCqX qZoOoQ

Unconstrained panels with 2 analytes, where 1.0E-8 >= 'AUC p-value' > 0. Contains 1,067 panels of 197,786 total panels evaluated. : Et(AA aH aY bM cK dE dO Dq Ed Ef Fn Fp Fr Fw Ha Hq Hr Hu Hv Hw Hx Ih Ii Ij Ik Il Im In Io Ip Iq Ir Is It Iu Iv Jd Je Jf Jg Jh Ji Jj Jk Jl Jm Jn Jo Jp Jq Jr Js Jt Kc Kf Ks Kx Ld Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Ra Rm Ub uR Vp vQ Wn Tj) Ok(AA aH bM bQ cE Ch cK cQ Cu dE DO Dq dV dX eM eP eX Fp Fr gN Gw Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe qI qZ rP rQ rW uR vB vQ Tj) Jg(aR Bg bM bX dE Fp Fr Hq Hr Hu Hv Hw Hx Ih Ii Ij Ik Il Im In Io Ip Iq Ir Is It Iu Iv Jh Ji Jj Jk Jl Jm Jn Jo Jp Jq Jr Js Jt Lh Li Lj Lu Lv Lw Lx Ly Lz Ma Mb Mc Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe rP sC) Pj(dU eQ pI pS qH rN rO rP rQ rR rS rT rU rV rW sC sK sM sO tN tO tQ tR tS tT tU tV tX uG uI uL uM uN uO uP uR uT uU uV uW uX uY uZ vA vB vC vH vI vO vP vQ vS vT vU vV vW wB wC wD wE wF wG wH wJ wK wL wP wQ yD yH yJ yK yL zG zH zI yE tM tL xA Tk) Nw(dV Fp Fr Gt Hq Hr Hu Hw Hx Ih Ik Im In Io Ir Iu Iv Ji Jn Js Li Lu Lv Ly Ma Mb Mc Me Mf Mg Mi Mj Mk Ml Mp Mq Mr Ms Mt Mu Mv Mw Mx My Mz Nc Nd Ne Nh Ni Nj Nk Nl Nm Nn Nq Nr Ns Nt Nv Nx Ny Oe Og Oi On Oy Oz Pa Pb Pc Pd Pe Pf Qb Qd Qe) Ji(Aa Bo dE eM eX Fp Fr Hr Hu Hw Hx Ik Il Im In Iq It Iu Iv Jj Jk Jn Jq Js Li Lu Ly Mb Me Mf Ml Mm Mp Ms Mt Mu Mw Mx My Nc Nd Ne Nf Nh Nj Nk Nl Nm Nn Nq Nr Ns Nt Nx Ny Oe Og On Oy Oz Pc Pd Pe Pf Pg Po Qb Qc Qd Qe) Ik(Dq Fp Fr gT Im In Jj Jl Jp Lh Li Lj Lx Ma Mm Mt Mw Nc Ne Nf Nh Nj Nk Nl Nn No Nv Nx Oh On Oz Pa Pc Pe Pf Pz Qa Qd Qe) Ng(pS rQ sC sK tN tR tV uG uI uL uM uN uO uP uR uV uW uX uY uZ vA vB vC vH vI vQ vS wB wC wF wH wJ wK wP yK yL zA tL) Nh(Fp Fr Im In Jj Jp Js Jt Lh Li Lj Lx Mb Mm Mt Mw Mx Ne Nk Nm Nn No Nv Nx Oh On Oz Pc Pd Pe Pf Pz Qb Qe) Ad(aC Aj aK Ap aR aV Bg bM Bo bU bX cN cP Cq Ct Cu Dc Dd dE In Js Nd Nj Of pS qZ rP sC tV uM vC vH Tj) Mt(Aa Fp In Jj Jk Js Lh Li Lj Mb Ms Nc Nd Ne Nj Nk Nl Nq Nt Oe Oz Pc Pd Pe Pf) lL(Eq Fc Gh Hl Rv Rz Si Uy Va Vh Vi Vw Wb Wc Wd Wf Wh Yd Yg Yh Yi Yj Tl Xa Yf) Nj(Do Dq Fr gT Gw Im Jp Lh Li Mm Mw Nv Nx On Pf Qc) gT(aK aV cY dR Ly Mb Mf Mg Mk Oz Pb Pc) Nl(DO Fr

Figure 14 Continued

Jp Lh Li Nk Nv Nx On Pf) Nc(Fp Fr Jp Lh Li Nk Nv Nx On Pf) Mm(pS rQ rR rW sC tV vH vQ vT) Mb(Dq dV Fr Gt Jp Lh Li On) dU(Jt Ke Ld
Mw Qn Rg Un Ut) dX(Jn Kc Kf Kk Ko Kp Oz Pb) Ti(pS uN vQ vV wF yJ tL) bB(DO DQ eX Gt Gw) eP(Kc Kf Ko Kp Kq Pb Qz) Nd(Jp Lh Li
Nx On Pe) Yl(kl kK mM nA qX rA) aV(dO Dq DV eX fR) dQ(Bo Gn Nx Oz Pb Pc) Ap(sC tR uU vC yE) Fc(eD iC jO jU rA) Ic(qG rR rW vP
xA) Si(jD jT qT qX rA) Ko(Do Dq eM eX Gw) dV(aK cY Ly Mf Pb) kI(Ho Hp Vb Yf) Bb(rP rW sC) Dg(bM cP Js) Dq(Fy Kf Kq) Em(jV jY
Kc) Li(Hx Ly Oz) Vq(qG qH qZ) eX(Jy Kq Qu) fR(aK dO gW) gN(Oz Pb Pc) mM(Du Fd Vz) tV(Cw Dd Kn) vQ(Jt Kg Mg) Fp(Nx On) Gn(dO
Kc) Ke(rR rW) Uf(uT uW) Vw(iC iP) tR(Kg Kn) rP(Jt Un) AavO CpaM CwrW DlcP DoJy GwQu LyPf MguW liwF VznA JdVp RyhV VjiC
VowJ Unconstrained panels with 2 analytes, where 1.0E-7 >= 'AUC p-value' > 1.0E-8. Contains 751 panels of 197,786 total panels evaluated. : Et(Ad
aF al An aR Bc BG Bo bX bZ cE Ch Cp CQ Cu dB Dd dU eX Fa Fb Fy Gl Gp Hb Hc Hf Ib Ic Iz Ju Jv Jy Kd Ke Kg Ki Kj Kk Kl Kn Kp Kq Kr
Ky Kz Oa Or Ou Ph Pl Qh Ql Qn Qt Qx Qy Qz Rc Rf Rg Ri Rj rQ sC St Tn Tv Tz Ud Ue Uf Uk Um Un Uo Ur Us Uv Vs Vt Vu) Ji(Ad aF aH
aR bM bX Ch cK cP CQ Cu dl dO Dq dU eP Gw Hq Hv Ih Ii Ij Io Ip Ir Is Jh Jl Jm Jo Jp Jr Jt Lh Lj Lv Lw Lx Lz Ma Mc Md Mg Mh Mi Mj Mk
Mn Mq Mr Mv Mz Na Nb Ng Ni No Nu Nv Of Oh Oi Om Pa Pb Pz Qa Ra Rm rP Vp Tj) Ad(AF aH aJ Al aM AN Ao aQ Ar As aU AW Ax aY
Ba Bb Bc Bn bQ cB cC cF cG Ch cK Co Cp cQ Cs Cv CW Cx cY DB De Dg Di Dk DL dM Fr Hr Kx Na Nl Oe Ok Pc Pg Pj tR uN uW uZ vQ)
Ik(Aa Ap AR Dg dU Hr Hv Hw Ih Ii Ij Il Io Ir Iu Jh Jq Jr Js Jt Lv Me Mf Mh Mi Ml Mn Mu Mx My Mz Na Ng Nm Nq Nr Ns Nt Nu Ny Oe Om
Oy Pd Pg Po Qb Qc rW) Nh(Hr Hu Hv Hw Hx Ih Ii Ij Iu Jh Jl Jn Jo Jq Jr Lv Ly Ma Mf Mg Ml Mn Mq Ms Mu Mv Mz Na Nb Nc Nd Nf Nj Nl
Nr Ns Nt Ny Oe Om Oy Pa Pb Pg Po Qa Qc Qd) Nw(dQ eP gT Hv Ii Ij Il Ip Iq Is It Jh Jj Jk Jl Jm Jo Jp Jq Jr Jt Lh Lj Lw Lx Lz Md Mh Mm Mn
Na Nb Nf Ng No Nu Of Oh Om Pg Po Pz Qa Qc) Ok(aF aG aI aM Ao Ap aR bC BG Bn Bo bX bZ cO Cq Cs Dc Dd De dF Dl Dk dU Fw Kf Ks
Ld qG Ra Rm rR rS rV sC Vp) Dg(aC Aj aK aV Aw aY Bn Bo bU bX bZ Ch cK Cp CQ Dc Dd dE Di Nd Nj tV vQ) Mt(Hw Im Iq Iv Jp Jr Jt Ly
Me Mf Ml Mm Mp Ns Nx Of Og Om On Qb Qe) Ng(rP rV sM sO tS tT tU tX uU vO vP vT vU vV vW wD wL wQ yH zH tM) Jg(Aa aF aH Aj
aM aY Bn bZ cE cP cR Cu Dk Ic Md Pj tN Ub Uu Vp Tj) Fp(Fr Im In Jp Lh Li Mb Mm Mu Mw Ne Nj Nk Nl Nt Oz Pc Pd Pf) Ap(aC Aj Aw
aY bM Bo bU CP Cq Di Dk Nd Nj tV vP vU tM) On(Cu dE dQ dU Hr Hw Hx Jk Ly Me Ml Mp Ne Oe Of Oz Pc Tj) Nj(Aa dQ dU Gt Jl Jt Lx
Mu Mz Nk Nm Om Pc Pd Pe Qa) Pj(bM Bo Ch cQ eM iB Jd Je Jf Js Mw Na oT Un Vs) Dl(aC aK aU aV Aw bM Bo bU bX Cp cQ rP) Ne(Fr Jp
Lh Li Mw Nk Nv Nx Pe Pf) Jd(Bg bU dE Dk Ed Hq Mm Mz Qx Tj) Nc(Jj Jt Lx Mm Mw Nm Pd Pe Qe) Nl(Dq Im Jt Mm Mw Nm Pd Pe Qe)
Nd(Aa Fr Jt Mw Nv Oh Pf Qe) Kf(aM dE Ed Fw Js Nk Rm Tj) Pe(Hx In Js Ly Nf Nt Nx) Dq(aH aU Bo dD Mg Qu) Nt(In Jj Li Oz Pf) Kq(Cu
Fw Js rP Tj) Ti(rP tV vA vH) Mm(Pf qG vB wJ) Li(Jk Nf Nx Pc) dO(bM Bo gT Ko) dU(Lh Lx Mx Mz) Fc(gW jD kI) Mb(Nv Pf Qe) Ic(qI qP
uT) Jt(eM eP sC) Ke(pS sC vC) Lp(kI mM nA) Uf(pS sC vI) aQ(dV fR gT) tV(cW Ef Vo) IL(Ux Zq Zx) rP(Im Pd rR) Aa(bM uR) Ly(Fr Jp)
Hx(Jp Nv) Ii(qZ uR) Qb(Qa Qe) Kg(vC wJ) Yl(mP rZ) Nx(Oz pl) dV(dR Pc) gV(aD cW) EfvQ FydX GcgW GnKo LxOm MgvH MwKc IzuP JhvS JneX KlrW KnwF LhpI aMcK aVgN aYmP cPdQ cYfR Unconstrained panels with 2 analytes, where 1.0E-6 >= 'AUC p-value' > 1.0E-7. Contains 1,494 panels of 197,786 total panels evaluated. : Ad(Aa aD aE aG aI aL aO aP aS aX aZ bA bB bC bE bF bG bH bI bJ bL bN bO bP bR bS bV bW bZ cA cD cE cH cI cJ cL cM cO cR cS cT cU cV cX cZ dA dC dD dF dG dH dI dJ dK dN Ed EF Fp Fw GL Gp Hq Hw Hx Ic Ij Ik Il Io Ip It Iu Jd Jg Jk Jn Jp Jv Kc Kq Ly Ma Mb Me Mh Mj Mm Mp Mr Ms Mt Mw Mx Nc Ne Nf Ng Nh Nk Nn Nw Nx Ny Og On Oz Pb Pd Pf Qb qG qH qI Qz Ra rQ rV rW sK sM Ue uG uL Un uX vA vB vI vO Vp vW zG tM Wn) Ok(aC aD Af Aj aK AL AN aO aQ Ar AS aU aV Aw AX aY Ba BB Bc bF bH bL bR bS bU cA cB cC cF cG cH cI cJ cL cN Co CP cR CT cU CV CW Cx cY cZ DB DG dH dJ Dl dN Ed Ef Fn gC Gl GP gW Ha Hc Hf Ic Jd Je Jf Jy Kc Kj Kn Kr Kx Oa Or Pi Pk pS Qg Qh Qt Qx Qz Rc Rh Ri Rj rN rO rT rU Tn Tv Ub Ue Uk uL Um Un uZ vH Vu Wm) Et(aC aD Af aG Aj aK AL aN AO Ap Ar AS Aw Ax Ba Bb bC bF bH bI bL Bn bQ bS bU cA cC cD cI cM cN CO cP cR Cs Ct cU CV CW CX cZ dA Db Dc De dF DG dH DI dJ Dk Dl Dp dR eF eM Ez gC gL gP Gw Id iP Ko oE Ow Pj Pk qB Qg Qm Qu Qv Qw Rb Rh rW Sr Ss To Tr Tt Ua Uc Ug Uh Ul Up Ut Uu vH Vo Vv Wm) Ap(aD Af aK Al AN Ao aQ AR As aV Ax Ba Bb Bc Bg Bn bX bZ cA cC Ch cK cM CO cQ Cs Ct Cu Cv Cw Cx Dc Dd dE Dg Dl Fw Je Jg Ji Js Kx Nl Nn Oe Of Pj pS rR rW Tn uG uL uT uW vB Vp vQ vS wB yH yJ yK zG tL xA Tj) Ji(aA aC Af aG aI Aj aK Al aM AN Ao Ar As AW Ax aY Ba Bb BC BG bL Bn bQ bU bZ cA cH cI Co Cp cR Cs Ct Cv CW Cx cZ dB Dc Dd De Dg dH Di dJ Dk Dl Do dR Ed eF gL gP Ha Jd Ld Pj Qg Qx Qz Rc Ub Ue) Dg(aD AF aH Al AN AO aQ AR As aU aW Ax Ba Bb Bc BG cB cC cH cM cN CO Cs CT Cu Cv Cw Cx cY Db De Dk Dl Fr Fw Gl Ic Jd Je Mp Nl Oe Pc pS sC Un vH Tj) Fp(dQ Hr Hu Hw Hx Ii Il Jh Jj Jl Jn Js Jt Lv Lx Ly Ma Me Mf Mg Mh Mi Ml Mq Mv Mx My Mz Nb Nd Nf Ng Nm Nn No Nr Ns Nu Nv Ny Of Og Oh Om Oy Pa Pb Pe Pg Pz Qa Qb Qe) Jg(aA aD aG aI aK aL aO Ar aU aV Ax Ba Bb Bc bG bH bL Bo bQ bU cC cF CH cK CQ Ct Cv cZ dB Dc dG dH dI Dl Ed Fw Je Jv Kx pS Qw Qz Ra rW Tz Ue uL Un uP uW vQ) Ik(aA aF aM aY Bb Bn Bo Ct Cu Cw dE dI Dl Hq Hu Hx Ip Iq Is It Iv Jk Jm Jn Jo Lu Lw Ly Lz Mb Mc Md Mg Mj Mk Mp Mq Mr Ms Mv Nb Nd Ni Of Og Oi Pb rP rQ sC) Mt(aR Bb dE Dl Fr Hu Hx Ih Ii Ij Il Ip Ir It Iu Jl Jm Jn Jo Lv Lw Lx Lz Ma Mc Md Mg Mi Mk Mn Mq Mv Mw Mx My Mz Nb Ng Nm Nr Nu Oh Oy Pa Pb Pg Po) On(Cq Ed Fw Hq Hu Ic Ij Il Im In Iq Jj Jr Js Li Lj Ma Mf Mm Mu Mv Mw Mx My Ng Nk Nm Nn Nq Nr Ns Nt Nu Nx Oy Pd Pe Pf Pj Qb Qc Ra) Pj(aR aY Ba bC bX cN cP cR Cw Dl Fr gL hP Ic Jp Kc Kf Kl Kq Kr Ks Kx Lh Mp Ne Nj qA Qe qG qI Qu Qv QZ Ra Rc Ss Us zA Ti) Jd(aK An bZ Cq Cs Cv Dd dI Dl dX Il Iq It Jj Kc Kf Kn Kp Kx Lh Mg Mr Mv Mx My Nq Ns Pc Pg Ra rP Ud Ue Un uP) Li(Hr Hw Il In Iq Js Jt Lh Lv Me Mf Mm Mp Mu Mw Mx My Mz Nk Nn Nq Nr Ns Oe Of Oy Pa Pd Pe Pf Po Qb Qd Qe sC) Nh(Aa Gw Hq Il Io Ip Iq Ir Is It Iv Jk Jm Lu Lw Lz Mc Md Me Mh Mi Mj Mk Mp Mr My Ng Ni Nq Nu Of Og Oi) Nt(Fr Im Jp Js Lh Lj Lv Lx Mb Mu Mw Mx Nc Ne Nj Nk Nl Ns Nv Nx Oe Pa Pc Pd Qa Qe) Mm(Fr Hu Hx Kc Kf Lh Mb Nd Ne Nx Oz Pe qH qI rS rT rV tR tU uL uR wG wQ yH Tk) Un(aF Cu dE Ed eQ Fw Hr Hx Ic Js Kc Kf Ms Mx Na Nk Pg QB qD Ra Ue uW Vp Tj) Nl(eX Gw Hw In Jj Jl Lj Lv Lx Ma Mb Mg Mz Nn No Nr Oh Om Oy Oz Pc Pz Qa) Nc(Hw Im In Jl Lj Lv Ly Ma Mb Mg Mz Nd Nn No Oh Om Oy Oz Pc Pz Qa Qd) Nj(Bb Dl dO eX Iv Lj Lv Ma Mg Mq Mv Nn No Nr Oh Oy Oz Pa Po Pz Qd) Ng(gT qG qH qI rR rU rW tO tQ uT wE wG yD yJ zG zI yE xA) Lh(dE Ed Hx In Jj Js Lj Mc Ms Nf oD Oz Pc Pd Pf Qe Tj) Mg(Ct pS sC sK tR tV uL uM uO uZ vA vB vI wJ) Cp(aK aQ aR aU aV Bg bM bU cC cK cM dE eM) Ne(Im Jj Jt Lj Lx Ma Nm Nn No Oh Pc Pd Qe) Nx(dE dU Fr gT Jj Jp Jt Lj Mb Pc Pd Pf Qe) Kf(Cu Do Hq Jk Mx Pg Qb Qh Ra Ub Ue Vp) Dl(aQ aY Ba Ch cY dE Di Ic Js vQ Tj) Mb(Aa Do Gw Jl Lj Lx Mw Oh Pe Pz Qa) Nd(Do Im Ma Mz Nm Nn No Nr Om Pd Qa) Jp(dE Lj Nm Oz Pc Pd Pf qZ rP Ub Ue) Kg(Of sC tV vB vH wB wD wF wH wL yK) Fr(dE Hw Hx Jk Me Mf Oz Pc Pd Pe) Jt(aR dE qG qI qZ Ra rW uR vC vI) Kl(aM Of qG qH qI qZ rP tR vH vQ) Uf(Fw Hq Js Mp Ue vT vU wP xA Tj) Dq(aK cY cZ Gn Jy Kn Nw Qe Ut) Ti(rO rR sC tQ uR vI wC yK yE) Kc(bU Dr eM Fc Ru Uy Vp Vz Zx) Kq(Bg Cw Hq Mj Mw Ny Oe Pg Ra) Pe(Hr Hw Mf Mp Mu Mz Oz Pc Qb) kI(Du Ex Lt pK Ru Vh Vz We Tl) rP(cH dB Ic jV Ke Mz Om Pz Vt) Kn(tS wC wD wG wH wJ wL wQ) lL(Em Gb Gc Gn Lp Uw Yk Zw) Nw(aR Ch dE dX eM qZ Tj) Pf(Hx In Mf Mw Nk Oz Pc) dB(Bo tV uP uV vO vS tL) Ke(eM pK sO uL vH vQ) Ko(aM dE Em fR GC) Ef(aM tR uL uP vS) Yl(kN lX nK nR qU) Om(Mf vC vI vU wF) eP(aV bB Jn Oz Qe) eX(aK aQ aU cY Kd) Ba(Bn Bo Ct dE) Fc(hW jY mY qT) Ly(aR Im Nv Qe) Ic(qO vQ wB tM) dQ(aV cG dF fR) dU(Fa Ir No Up) Bb(aM bM cP) Gn(dX gT gW) Gw(aV Pk Ue) Nm(Mu tR vQ) Im(Oz Pc qZ) Si(gW hV iC) Vo(tR vQ wB)

Figure 14 Continued

Pd(Jj Lj qZ) dV(Co Mk Oz) nA(Vb Wc Yc) Aw(aK aM) Ue(cP wF) Qe(In Pc) Vw(jO rB) aU(fR gT) dO(Bn cY) oE(Yg Yi) AltV DoaV DvaK FyvU MlNv MwLj MzJs IiwG IzuL YjqX VzlW WcrB QwdX XalK KjvQ OyvI bMcR qZoQ

Unconstrained panels with 2 analytes, where 1.0E-5 >= 'AUC p-value' > 1.0E-6. Contains 3,288 panels of 197,786 total panels evaluated. : Jd(Aa aF Al aN Ap aQ AR As aU aV Aw Ax aY Bb Bc bM Bn bQ bX cA cC cF Ch cK cM Cp Ct Cw Cx cY DB Dc De dG dH Di Ez Fa Fb Fw Ha Hr Hu Hw Hx Ib Ic Ih Ii Ij Ik In Ip Ir Is Iu Iv Je Jf Jg Jh Jk Jn Jp Jq Jr Js Jt Ju Jv Kd Kg Kj Kk Kl Ko Kq Ky Lw Ly Lz Ma Mc Md Me Mf Mh Mi Mj Ml Mn Mq Mt Mu Mw Na Nb Nc Nd Ne Nf Ng Nh Nk Nl Nm Nn Nv Nw Nx Ny Og On Or Oy Oz Pa Pb Pd Ph Po Pz Qd Qe Qh Ql Qm Qn Qw Qy qZ Rb Rm rW Sr tN To Tv Tz Ua Ub Uf Ug Uh Uk Ul Up UR Us Ut Uu Uv vQ Vs Vu Vv Wn Wm) Ad(aA dQ dR eM Fa Fn Gn gP gW Ha Hb Hf Hu Hv IB Id Ih Ii Im Iq Ir Is Iv Je Jf Jh Jj Jl Jm Jo Jq Jr Jt Ju jV Jy Kf Kn Ko Kp Ks Ky Kz Ld Lh Li Lj Lu Lv Lw Lx Lz Mc Md Mf Mg Mi Mk Ml Mn Mq Mu Mv My Mz Nb Ni Nm No Nq Nr Ns Nt Nu Nv Oh Oi Om Or Ou Oy Pa Pe Ph Pi Pk Po Pz Qa Qc Qd Qe Qg Qh qQ Qv Qw Qx Rc Rg Rm rN rO rR rT rU sO Sr Ss Tn To tS Tz Ub Uc Uf Uh uI Um UO UR Us Uu UV uY Vo VS VT VU VV wC wF wJ yH yK zH zI yE tL xA Tk) Ap(aF aG aH aJ aM aO aU aW bA bB bE bF bG bH bI bJ bN bQ bR bS cB cD cE cF cG cH cN cR cS cT cW cY dA DB dD De dF dG dH dI dJ dL dM Ed EF Ez Fn Fr GL GP Hb Hr Hv Hw Ic In Io Jf Jp Ju Jv Kc Ke Kf Ki Kn Kp Kq Ks Ld Ly Ma Mp Mt Na Nc Ne Nh Nq Nw Nx Oh On Or Oz Pc Pg Ph Qb QG qH qI Qu Qv Qw Qz Ra Rh Rm rP Sr To Tr Tt Tv Tz Uc Uh Uk Um UN uP UR Us Uu UV uZ vH vI VO Vt vV vW wD wF wH wK wL yL zH zI) Jg(aC aE Af aJ Al AN Ao aP aQ AS AW aX aZ bA bB bC bE bF bI bJ bN bO bP bR bS bV bW cA cB cD cG cI cJ cL cM cN CO Cp CS cT cU cV CW CX cY dA Db dC DD De dF Dg Di dJ dK dL dM dN Dp dU Ef Ez Fn Gl GP Ha iA Ib Id Iz Jf Ju Jy Kc Kf Kg Ki Kl Kn Ko Kz Ld Oa Or Ou Ph Pi QG Qh qI Qm Qx Rb Rg Rh Ri Rm rQ rT Sr Ss Tn tO tR tX Ua Uc Uf uG Uh Uk Ul uM uN UR Us Uv uY uZ vB vC vI Vo Vs Vt Vu Vv tM Wm) Pj(aD aF aH aI aJ aM aP Ar bE BG bU bZ cE cF cM Co Cp cS cZ dA dE Dg dJ Dk Dl dR Ed EF Fa Fb Fn Gl gP Hf Hx Ib IH Ik Il In Io Iz Jj Jl Jo Ju Jv Jy Ke Kn Ko Kp kQ Lu Ma Mb Mg Mk Ms Mt Mx Nc Ng Nh Nk Nl Nn No Nt Nu Nv Nw Nx OF Og Oh Ok Or Ou Oy Oz Pb Pc Pd Pf Pg Qa QB Qc QD Qt Qx Qy Rg Ri rZ Sr Tn To Tr Tt Tz Ua Ub Uc Ud Ue Uf Ug Uh Um Uo Ur Uv Vp Vt Vu Wn Wm Tj) Ji(aD aE aJ aL aO aP aQ aS aU aV aX aZ bA bB bE bF bH bI bJ bN bO bP bR bS bV bW cB cC cD cE cF cG cJ cL cM cN cO cS cT cU cV cX cY dA Db dC dD dF dG dK dL dM dN dX Ef Fn Fw Fy gC Gl Gp gW Ib Ic Je Jv Kc Kf Kl Ko Kq Kx Oa Or Ou Ph Pl Pk Qh Qt Qu Qv Qw Qy qZ Rb Rf Rg Rh Ri Rj rW Ss St Tn To Tr Tt Tv Tz Ua Uc Ud Uf Ug Uh Uk Ul Um Un Uo Up Ur Us Ut Uu Uv Vo vQ Vs Vt Vu Wm) Ok(aE aJ aP aW aZ bA bE bI bJ bN bO bP bV bW cD cM cS cX dA dC dD dK dL dM Dp dR eF Ex Ez Fa Fb Fy gL Hb Ib Id Iz Ju Jv Kd Ke Kg Ki Kk Kl Ko Kp Kq Ky Kz oF Ou Ow Ph qA qB qH Ql Qm Qn Qu Qv Qw Qy Rb Rf Rg sK Sr Ss St To Tr Tt Tz Ua Uc Ud Uf UG Uh uI Ul uM UO UP Ur Us Ut Uu Uv uX uY vC vI Vo vP Vs Vt vU Vv wJ yH) Dg(Aa aE aG aI aJ aL aM aP aS aX aZ bA bB bC bE bF bH bI bJ bL bN bP bQ bR bS bV bW cA cD cE cF cG cI cJ cL cR cU cV cW cX cZ dA dB dC dD dF dG dH dI dJ dK dL dM dN Ed Ef Fn gL Gn GP Hr Ib In Jf Ju Jv Jy Kc Kf Ki Kq Kr Kx Ly Ma Mt Na Nc Ne Nh Nn Nw Nx Of Oh On Or Pg Qb Qz Ra Ri tR Ue Us Uu Uv uW uZ vB vC Vp) Un(Aa aO AR aY Bb Bg Bn Bo bU bX bZ Ch cP CQ cR Cw Cx dI Dl Ef eM Fa Fc Fn Ha Hf Hq Hv Hw Ik In Iz Je Jf Jl Jn Jr Jt Jy Kg Ki Kj Kl Kn Ko Kp Kq Ks Kx Kz Ld Lh Lw Mg Mh Mj Mm Mp Mr Mw Nc Nf Nj Nm Nn Nq Ns Nx Oa Or Ou Pc Pd Ph Pi Pk Po QA QC Qg Qh Ql Qx Qz Rc rQ rV rW Ub Uf Ug Uk Um vC Vu) Kq(aF aH aI Aj AL aM An AR As Aw Ax aY BC bG Bn Bo bQ bX cE Ch Co Cp CQ cR Cs Ct Cv cW Db Dd dE DI Dk Dl Do dX Ed Fa Fn Gw Hx Ic Ik In Io Iv Jn Jp Jv Jy Kc Kf Kg Kx Kz Ld Lv Ly Mg Mi Ml Mm Mp Mr Mx My Na Nb Nc Nj Nk Nl Nn Nq Nv Of Oy Pc Pd Ph qG qI Qx QZ rW Ub Ue uG Vp) Lh(aR bX eQ Fr Fw Hq Hr Hu Hv Hw Ih Ii Ij Il Im Io Iq Ir Iu Iv jB Jh Jk Jl Jm Jn Jo Jp Jq Jr Jt Kc kF kI Ko Ld Lu Lv Lw Lx Ly Lz Mc Mf Mg Mi Ml Mp Mq Mu Mv Mw Mx My Mz Na Nb Ng Nk Nm Nn No Nq Nr Ns Nu Nv Nx Ny Oe Of Og Oh Om On oT Oy Pa Pb Pe Pg pK Pz Qa Qb Qc Qd Qg qZ Ra Ub Ue Vp) On(Aa AF Aj AR Bb Bc Bg bM Bn Bo bZ cK Co Cp cQ Cv Cx Dc Dd De Di Dk Dl Fr Ha Hv Ih Ii Io Ip Ir Is It Iu Iv Jh Jl Jm Jn Jo Jp Jq Jt Kf kI Ld Lu Lv Lw Lx Lz Mc Mg Mh Mi Mj Mk Mn Mq Mr Ms Mz Na Nb Nf Ni No Nv Ny Og Oh Oi Om Pa Pb Pg Po Pz Qa Qc Qd Qx qZ Rm Ub Ue Uk Vp) Mm(aR Ch Ed Fn Im Je Jf Jj Jp Jr Jv Kj Kl Kn Ko Kx Lj Lx Me Mf Ml Mw Mz Nr Nt Nv Or Pc Ph Qa Qe Qz Ra Rf Rg Ri rN rO rP rU sK sO tN tQ tT tX Uf uM uN uO uP uT uV uW uY uZ vA vC vI vO VP vS VU vV vW wB wC wD wE wF wH wK yD yJ zH zI yE tM tL Wn Tj) Pe(aA Dq dU Hq Hu Hv Ih Ii Ij Il Im Io Iq Is It Iv Jh Jj Jk Jl Jm Jn Jp Jr Jt Lj Lu Lv Lw Lx Ma Mc Md Me Mg Mh Mi Mk Ml Mn Mq Mr Ms Mv Mw Mx My Na Nb Ni Nk Nm No Nq Nr Ns Nu Nv Ny Oe Of Og Oh Oi Om Oy Pa Pb Pd Pf Pg Po Pz Qd Qe) Nt(Hq Hr Hu Hv Hw Hx Ih Ii Ij Il Io Ip Iq Ir Is It Iu Jh Jk Jl Jm Jn Jq Jr Jt Lu Lw Ly Lz Ma Mc Md Me Mf Mg Mh Mi Mj Ml Mn Mp Mq Mr Ms Mv My Mz Na Nb Nd Nf Ng Ni Nm Nn No Nq Nr Ny Of Og Oh Oi Om Oy Pb Pg Po Pz Qb Qc Qd) Dl(aD AF aH Aj Al aM AN Ao AR As aW Ax BB bC bG bH Bn bZ cB cC cF cG cH cK cM cN Co Cq Ct Cu Cv Cw Cx DB Dc Dd De Dk Ed Ef Fr Fw Gl gT Hr Hv Hw In Jp Kc Kf Mp Nc Nd Nh Nl Nn Oe Of Pc Qb Ra Uf) Nj(aA AR Cp Cw Hr Hu Hv Hw Hx Ih Ii Ij Il In Io Ip Ir Is Iu Jh Jj Jm Jo Jq Jr Js kI Lw Ly Lz Mb Mc Md Mf Mh Mi Mj Mk Mr Ms Mx My Na Nb Nc Ne Nf Ng Ni Nl Nq Ns Nu Ny Of Og Oi Pb Pg Qb) Li(Fr Hq Hu Hv Ih Ii Ij Im Io Ip Ir Is It Iu Iv Jh Jj Jl Jm Jn Jo Jp Jq Jr Lj Lu Lw Lx Lz Ma Mc Md Mg Mh Mi Mj Mk Ml Mn Mq Mr Ms Mv Na Nb Ng Ni Nm No Nu Nv Ny Og Oh Oi Om Pb Pg Pz Qa Qc) Fr(Aa aF bM Bn Cp Hq Hr Hu Ih Im In Iq Iv Jj Jl Jn Jp Jr Js Jt Lj Lv Lx Ma Mc Ml Mq Mu Mv Mw Mx My Mz Na Nb Nf Ng Nk Nm Nq Nr Ns Nu Nv Ny Oe Of Oi Om Oy Pa Pf Pg Pz Qa Qb Qd Qe Tj) Et(aE aJ aM aP aQ aU aV aW aX aZ bA bB bE bJ bN bO bP bR bV bW cB cF cG cH cJ cL cS cT cY dC dD dK dL dM dN Do dX eP fP gW iA oF pS qA qD qG qH rP rR tR uO yH Tk) Jt(aF bM Bo bX cK cP cQ Cu Do Dq eQ Fw Hr Ic Iq Je Jj Jp Kf Lj Lx Mb Nv Oz Pc Pf pS qH Qw Qx Qz Rg rR rT rV Ub Ue uL UM Ur uV uY uZ vB vH Vp Vs Vu Wn Tj) Nl(Aa Ar Bb dE Hr Hu Hx Ih Ii Ij Il Io Ip Ir Iu Iv Jh Jm Jn Jq Jr Js Ly Mf Mi Mq Mu Mv Mx My Nb Nc Nd Ne Nf Ng Ni Nq Ns Nu Ny Of Oi Pa Pb Pg Po Qb Qc Qd) Kc(aH aM An aY bH bI bM bX bZ cC CH cK cP cQ cR cS dB dE dI Gc Gd Hq Hw Ik Js Kf Ld Lp Lz Mx Nx Oe Pd Pg Ps Qx Ra Rt Ry Sf Sh tV Tz Ue Uf Wf Yi Yl Tj) Mg(AR aY bM Bo Jp Lj Lx Nd Ne Pf Qe qO rP rQ sM sO tO tQ tX uG uI uP uR uU uX uY vC vO vS vT vV wB wC wD wE wF wG wH wK wL wP wQ yD yH yK zH tM tL) Cp(Aa aC aF aH aN Ao Ar Ax aY BA BB Bc bH bX bZ cA cF cG Co cP CQ cR Cs Cu Cv CW cY dB dD dH Dl Dk dL Gn Ik kI Nw Pd rP vS Tj) Ik(Af Aj Al An Ao AW Ax Ba Bc Bg bM bU bW bX bZ cA cG CH cN Co cP CQ cR Cs Cv cW Cx DB Dc Dd De Di Dk fR Fw Kf pH pK uR uV Tj) Jp(aR Bn Ed Hr Hw Ic Ih Im In Iq Jj Jk Jr Js Kf Lv Lx Me Mf Ml Mp Ms Mu Mv My Mz Nb Nf Nk Nq Nr Ns Nu Of Qb Qc Qe qI Qx Ra rW Vp Tj) Nc(Aa Ar dE Hu Ih Ii Ij Ip Ir Iu Iv Jh Jo Jq Jr Js lW Me Mf Ml Mp Mq Mr Mu Mv Mx My Nb Ne Ng Ni Nr Ns Nu Ny Oi Pa Pb Pg Po Qb Qc) Kf(aR Bn bQ bX bZ cR Cx dI dO dU eM eX Ha Hr Hw Hx iB Ic In It Je Jl Mj Mp Mw Na Nn Nw Of Pc Qa Qc Qw Qx Qz rW Ul vQ Vt Vv) Fp(aA Dq Hq Hv Ih Ij Io Ip Iq Ir Is It Iu Iv Jk Jm Jo Jq Jr Lj Lu Lw Lz Mc Md Mj Mk Mn Mp Mr Ms Na Ni Nq Oe Oi Po Qc Qd) dB(aQ Ba bM Ko Nw pS sC sK sM sO tN uG uL uM uO uR uT uU uZ vB vC vQ vU wB wD wF wG wH wL yH yK yL zH zI yE xA) Pf(dE Hr Hw Il Im Iq Iv Jj Jk Jr Js Lj Lv Lx Mp Ms My Mz Na Nb Nf Ng Nm Nr Nu Nv Oe Of Oh Om Oy Pd Qa Qb Qe) Mt(aA aM aO Ar bZ dI Hq Hr Hv Io Is Jq Lu Mh Mj Mr Mu Na Nf Ni Nn No Nv Ny Oi Pz Qa Qc Qd qZ Vp) Kg(dU Fw Js pS rR rW tN tO tQ tS tT tX uI uL uP uR uT uV vA vP vT vU wC wG wK wP wQ zG tM tL xA) Nw(AA aF aH aM Ba bM Bn Bo bX cK cP CQ Cu Cw DI Do Ed gN Gw Kn Ld pI Qx Ra Rc rR Vp) Ne(Aa Dq Hw Ih Ii Ij In Ir Iv Jl Jq Js Lv Ly Mb Mu Mz Nb Nr Ns Om Oy Oz Pa Pg Pz Qa Qb Qd) Qe(Aa dE Ed Hr Hu Hw Hx Im Jj Jn Js Lj Me Mf Ml Mu Mw Nf Nk Nu Nv Om Oz Pd Qa Qc Qd Tj)

Figure 14 Continued

Nx(Aa aM aR cK Dq eM Hr Hw Im Jr Js Lx Me Ml Mp Mw Mz Nf Nm No Nr Ns Nu Nv Oe Om Pz Qa) Ko(aH aR aY bC bG bM bU bX bZ Ch cP cQ cR dI Dr Ed Fw Gd Je Mw Ps Ru rW Ub Yd Tl Tj) Ba(aC aF aH Aj aK aM aQ AR aU aV Aw Ax Bb Bg bM bZ cP Cq Cu Cv Cx cY Js Nd Tj) bM(aK aM aN aQ aR aU aV aW aY bA bB bF Bg bU cG cP cY dF Dk Dq Gc kl Nm Pd) Mz(aM aR cK dl eM eQ fR Hr Lj Lx Ly Mb Mh Mq Mu Ns Om oT Oz Pd pl) Ke(Js qB qG ql qZ rN rO rT rV tR tV ul uM uO uP uT uW uY vB vl zG) Uf(Ed iB Je Kx Mj Na Nk Nn Of Pg Qz Ra Um oT Oz Pd pI) Ke(Js qB qG ql qZ rN rO rT rV tR tV ul uM uO uP uT uW uY vB vl zG) Uf(Ed iB Je Kx Mj Na Nk Nn Of Pg Qz Ra Um vH VP vQ vS wH wJ tM) Nv(dE Ed Hr Hw In Jj Jk Js Lj Lx Me Mf My Nf Oe Oz Pc Pd Qb Tj) Nd(AR Bb Cw Gw Ih Ii Ij Io Ir Jl Lj Lx My Oy Pa Pg Pz Qd) Kl(Aj dE eP Fw Ic Js Mw Pc Ra rR rT rV sC tV uP uR vC vU) aM(Aa aN aQ Bg bR bU cB cF cP cT dE Di DK Ic Kj Sr) Ly(Bo cP Cw dQ eP Jl Lj Lx Mb Mw Nn No Pa Po Qa) Ic(aY qX rA rO sC tV uV vV wH wQ yH yJ yK zI) Pd(aR dU In Lx Mb Mu Mw Nf Nm Nr Nu Oz Qa rW) lL(Fd Ho Hp Ps Rt Ru Ry Sf Sh Vb Vz We Yl Ye) rP(Al Cv Cw cZ Dc dI Hb Ii Ms Nr Ny Pc sC Tz) Ti(rU rV uM uY uZ vO vS wG wJ wK wL yD tM) kl(bH dL Eq Gn Gz Hl Rt Rv Ux Uy Vw Yd Zq) Pc(Aa aR dX eP Gt Lj Lx Mw Nm Nr Oh Qa) dE(aK aQ AR Bo cP Cu Mb Mw Nh Pb Uh) Fc(dN hX iB iO jH jV lK mM oE qU qX) Kn(qG tQ tT tU tX wB wE wK wP yD zA) dO(aG aH aK aQ aU cG cI dD dF Gl Jy) Bb(aK aR aU aV aY bU cC cK tV vC) Dq(aQ cG Fb Kd Ks Kx Oz Tn Tr Ua) Nm(aR cP dU Js Lj Lx Ml Ms Om Oz) Mb(dQ Ex fR gN Im Mu Na Nn No Om) Qa(Hw Hx In Iq Js Lv Ml Mu Oz) dU(Aa Im Jf Jo Nr Oa Ph Ql Tv) Ar(aK bU cC dQ Mh Nh rW sC) Lj(Hu Hx Im Mu Nf Nu Oz Qb) Om(Mu Nq rW uW vQ vS wH wK) Aa(aR aY Bo Jr Me Nr pI) Si(jK jO jR jV jY lM qU) nA(Fi Gn Lt Sh Uw Uy Tl) tV(aV Aw Ch Dc Iz Kj Ma) sC(cH Fy Ma Or Ph Pz Rh) Ii(iB rQ rW vQ wL Tj) Aw(aQ aU aV cY vI) Fy(eP qZ uL uW vQ) Gt(aV dD Gn Oz Pb) Mw(Fw Me Nu Oz pI) Ng(qQ rN rO rS rT) Yl(kC kF lW mY nB) Do(Bo cG Kx Qn) Lx(dQ Im Og Oz) Ue(iB Jf lW Ou) Vo(wF wH wQ zA) cP(aR Bn Gd gV) tR(cW Dk Iz Ub) rW(Hb Im Kp Vt) Gw(Bo Gn Ir) Jo(vI vQ vT) Ry(hX jD qU) Vw(kR qU Tj) dQ(aL Bg Cw) eP(Kk Kx Tn) fR(aW Bo cM) Ef(Ct wK) Th(nF nR) Ub(vQ vS) Hx(Jl Oh) Im(Mf qI) Yj(jP rA) Zq(Nf Vq) Jh(wH wK) Tl(lW qU) Kp(Em rR) Wn(Dc Ip) Uh(rQ rR) Oz(No Oh) aR(bU cC) dX(aV Vt) eM(Ao gV) eX(aH Gn) gT(bB Ml) gW(Ex Ho) jV(Ju Pi) BnbU CwvI DvcY GcjO NrJj MqwF NhaA HpiO IzvQ YhoE VznK KjvS VcjY VjjD aYlW bLiB cRtX

Unconstrained panels with 2 analytes, where 1.0E-4 >= 'AUC p-value' > 1.0E-5. Contains 6,047 panels of 197,786 total panels evaluated. : Kc(aA aC aD aE AF aG aI aJ aL AO AR As aV aW aX bA bB bC bE bF BG bJ bL BN bO bP bQ bR bS bV cA cD cE cF cG cI cJ cL cM cN cO Cq Cs CT CU cV CW Cx cZ dA Db DC Dd De dF dG dH Di dJ DK dN dR Du Ed EF Eq Ex Fa Fb Fd Fi Fn fP Fr Fw GP Gz Ha Hb Hc Hf Hl Ho Hr Hu Hv Hx iA Ii In Io iP Iq Ir It Iu Iv Iz Je Jf Jh Jk Jl Jn Jp Jq Jr Jt Jv Kd Ke Kg Ki Kj Kl Kn Ko Kp Kr Ks Kx Ky Kz Lj Lt Lu Lv Lw Ly Ma Mc Md Me Mg Mh Mi Mj Ml Mp Mq Mr Mt Mu Mv My Mz Na Nb Nc Nd Ne Nf Ng Nh Ni Nj Nk Nl Nm No Nr Ns Nu Nw Ny Oa Of Om On Ou Ow Oy Pb Pc Ph Pk Pz QB Qd Qg Ql Qm Qn Qt Qv Qy Qz Rb Rm rP Rv Rx Rz Si Sr Tn To tR Tt Tv Ub Ud Ug Uh Uk Ul Um Uo Up Us Ut Uv Uw Ux Uz Va Vb Vc VH Vi Vu Vw Wc Wg Wh Yd Yh Yk Zq Zw Wm Th Yf) Kq(Aa aC aD aE Af aG aK aN AO aQ aS aV aW aX aZ BA BB bE bF bH bI bL bM bN bP bR bS bU bW bZ cA cB cC cD cF cG cH cI cK cL cM cN cO cP cS cT cU cV CX cY cZ dA dB DC De dG dH dJ dK dL dM dN dO Dp dR Ef Ez Fb Fp Fr Fy Gl Gp Ha Hb Hc Hf Hr Hu Hv Hw IB Id Ih Ii Ij Il Im Ip Iq Ir Is It Iu Iz Je Jf Jg Jh Jj Jk Jl Jm Jo Jq Jr Jt Ju Kd Ke Ki Kj Kl Kn Ko Kp Kr Ks Ky Lh Li Lj Lu Lw Lx Lz Ma Mb Mc Md Me Mf Mh Mk Mn Mq Ms Mt Mu Mv Mz Nd Ne Nf Ng Nh Ni Nm No Nr Ns Nt Nu Nw Nx Oa oF Og Oh Oi Om On Or Ou Ow Oz Pa Pb Pe Pf Pi Pk Po pS Pz Qb Qc Qd Qg QH Ql Qm Qn Qt Qu Qv Rb Rc Rf Rh Ri Rj Rm rN rO rR Sr Tn To Tv Tz Ua Ud Uf Ug Uh Uk Ul Um Uo Up Ur Us Ut Uv vC vH Vo vQ Vs Vt Vu Vv tM) Un(aA aD aE Af aH aI Aj aK AL aM An Ao aQ As aU aV Aw AX aZ Ba bB BC bE bF bG bH bL bM bN bQ bR bS cA cB cC cD cE cF cG cH cJ cK cL cN CO Cp Cs CT CV cW cY dA DB Dc DD De dG dH Di DK dN Dp Dq dR eF Ex Ez Fb Fi fN Fp Fr Fy Gc GL Gn GP HB Hc Hu iA IB Id Ih Ii Ij Il Im Io Ip Iq Ir Is It Iu Iv Jh Jj Jk Jm Jo Jp Jq Ju Jv Kd Ke Kk Kr Ky Li Lj Lu Lv Lx Ly Lz Ma Mb Mc Md Me Mf Mi Mk Ml Mn Mq Mt Mu Mv My Mz Nb Nd Ne Ng Nh Ni Nl No Nr Nt Nu Nv Nw Ny Oe OF Og Oh Oi Om On Ow Oy Oz Pa Pb Pc Pf pY Pz Qd Qe Qm Qn Qt Qu Qv Qw Qy Rb Rf Rg Rh Ri Rj Rm rR rS Sr Ss St Tn To Tr Tt Tv Tz Ua Uc Ud Uh Ul Uo Up Ur Us Ut Uu Uv uX uZ vH vI Vo Vs Vt vU Vv wF Zw Wm Th) Pj(AA aC aE Af aG Aj aK AL AN AO aQ AS aU aV AW AX aZ bA BB Bc bF bH bI bJ bL BN bO bP bQ bR bS bV bW cA cB cC cD cG cH cI cJ cK cL cO Cq Cs CT CU CV cW CX cY DB DC DD De dF dG dH dK dL dM dN Dp Dq eC eP eT Ez fB fN FP Fw FY Gp gW Ha HB Hc hG hO Hq HR Hu Hv Hw Id Ii Ij Im iO IP Iq Ir Is It Iu Iv iZ Jh Jk Jm Jn jO Jq Jr JT jV Kd Kg Kl Kj Kk kR Ky Kz Ld Li Lj Lv Lw Lx Ly Lz Mc Md Me Mf Mh Mi Mj Ml Mm Mn Mq Mr Mu Mv My Mz Nb Nd Nf Ni Nm Nq Nr Ns NY Oa OE Oi oK Om Ow Pa Pe pF Ph Pi Pk Po pY Pz Qg Qh Ql Qm Qn qO qP qQ qV Qw qY rA Rb Rf Rh Rj Rm rX rY St Tv Uk Ul Up Ut Uu Vo Vv Th) Jt(aC aD Af aG aH aI Aj aK Al aM AN AO Ap aQ Ar As aU aV AW AX aY Ba BC BG bH Bn bQ bR bS bU bZ cA cC cE cF Ch cI cL cN Co Cp Cq cR Cs Ct Cv Cw Cx cY cZ DB Dc Dd De Dg DI Dk DI dR Ed EF Ez Fn gC gL gP Ha Hw Hx iA Ib Im In Ir Iu Iv Jf Jk Jl Jr Js Ju Jv Jy Kl Kn Ko Kp Kx Kz Ld Lv Me Ml Mm Mp Mu Mw Mx Mz Nf Nk Nn Nr Ns Nu Of Oh Om Or Ou Oy Pa Pd Ph Po Qa Qb Qd Qc Qg Qh Qt Qu Qv Qy Rb Rc Rf Rh Ri Rj Rm rN rQ rS rU sK sM sO Sr Ss St TN To TR TV Tz Ua Uc Ud Uf UG Uh uI Uk Ul uN UO UP Us Ut Uu Uv uW uX vA Vo VT vU Vv wF wG yH zH zI yE tM tL xA Tk) Ap(AA aE aI aL aP aS aX aZ bC bL bO bP bV bW cI cJ cL cU cV cX cZ dC dK dN Dp dR eM Ex Fa Fb Fp Fy Gn Ha Hc Hf Hq Hu Hx IB Id Ih Ii Ij Il Im Ip Iq Ir Is It Iu Iv Iz Jh Jj Jk Jl Jm Jn Jo Jq Jr Jy Kd Kg Kj Kk Kl Ko Kr Ky Kz Lh Lj Lu Lv Lw Lx Lz Mb Mc Md Me Mf Mg Mh Mi Mj Mk Ml Mm Mn Mq Mr Ms Mu Mv Mw Mx My Mz Nb Ng Ni Nk No Nr Ns Nt Nu Nv Ny Oa Og Oi Om Ou Ow Oy Pa Pb Pd Pe Pf Pi Pk Po Pz Qa Qc Qd Qe Qh Ql Qm Qn qP Qt Qx Qy qZ Rb Rc Rf Rg Ri Rj rN rO rQ rS rT rV sK sO Ss St tO tQ tS tT tU tX Ua Ub Ud Ue Uf Ug uI Ul uM UO Up Ut uX vA Vs vT Vu Vv wC wG wJ wQ yD Wn Wm) Kf(aD AF aG aH aI Aj AL An aO Ar AS aW aX aY Bb Bc Bg bH bM bU cC cE cF cJ cN CO CP CQ Cs Ct Cv DB Dc Dd De Di dJ Dk dM Dp Ef Ez Fa Fn Fp Fr Fy Gp Hb Hc Hv iA Ib Id Ii Ij Il Iq Ir Is Iu Jf Jh Jj Jm Jn Jo Jq Jr Ju JV Kd Ke Kg Kl Kl Kn Ko Ks Kx Ky Kz Ld Lh Li Lj Lu Lv Lw Ly Lz Ma Mc Md Mc Mf Mg Mh Mi Mk Ml Mn Mq Mr Ms Mt Mu Mv My Mz Nb Nc Ne Nf Ng Ni Nj Nl Nm No Nq Nr Ns Nt Nu Nv Nx Ny Oa Oe Og Oh Om Or Ou Oz Pa Pd Pi Po Ps Qd Qe Qg Qm Qn Qt Qu Qy Rb Rc Rf Rg Rh Ri Rj sC Sh Ss St Tn To TR TV Tz Ua Uc Ud Uf Ug Uh Uk Um Up Ur Ut Uu Vo Vs Vu Wm) Dg(aA bO cS Dp DQ dR DV eF eM eP Ez Fa Fb Fp Fy gC gN GT gW Ha Hb Hc Hf Hq Hv Hw Hx Id Ih Ii Il Im Io Ip Iq Is It Iu Iv Iz Jh Jj Jk Jm Jn Jo Jp Jq Jr Kd Ke Kg Kj Kk Kl Kn Ko Kp Ks Ky Kz Ld Lh Li Lv Lw Lx Mb Mc Md Me Mf Mg Mh Mi Mj Mk Ml Mm Mn Mq Mr Ms Mu Mv Mw Mx My Mz Nf Ng Ni Nk No Nq Nr Ns Nt Nv Ny Oa Og Ou Ow Oy Oz Pb Pd Pe Ph Pi Pk Po Pz Qa Qc Qe QG Qh qI Ql Qm Qn Qt Qu Qv Qw Qx Qy Rb Rc Rf Rg Rh Rj Rm rP rR rT rV rW sO Sr Ss St Tn To Tr tS Tt Tv Tz Ua Ub Uc Ud Uf UG Uh uI Uk UL UM uN Uo UP Ur UT uY Vo VS Vt Vu Vv yH tL Wm) Uf(Af aM AR aY Bg bM Bn Bo bX bZ cE Ch CQ Ct Cu Cw Cx dE dI Ef Fa Fn hB Hr Hu Hv Hw Hx iA Ib Ic Ij Ik Il In Io iP Iq Ir Is It Iv Jf Jh Jj Jk Jl Jn Jo Jp Jr JV Ke Kg Ki Kl Kn Ko KR Kz Ld Lh Lv Lw Lx Ly Lz Ma Mb Md Mg Mh Mi Mk Ml Mr Ms Mw Mx Mz Nb Nc Ne Nf Ng Nh Ni Nj Nl Nq Ns Nt Nw Ny OE oF Og OH On Ou Pc Pd Pf Ph Pi Po Qa QB Qc Qd Qg Qh Qm Qt Qw Qx Qy qZ Rc Rf Rg rP rQ rR rW sM sO Tn tO tR Tt tV tX Tz Ua Ub Ud UG Uh Uk UL Uo Up UR Us Ut Uu UV uY vA vB vC Vo Vs Vt Vu Vv wB wC wF yH yJ zG Tk Wn) Mm(Aa aH aN aQ Ar bM Bo bX bZ cK cN CP cQ Cu dE Dk Dl Dp Dq dU Ef Ez Fa Fb Fw Fy Gl Ha Hb Hc Hr Hw iA Ib Ic Id Ih In Iq Ir Iv Iz Jh Jl Js Ju Jy Kd Ke Kg Ki Kk Kp Kr Ky Kz Ld Lu Lv Ly Ma Mh Mj Mp Ms Mu Mv Mx Nb Nf Ng Nk Nm Nn Ns Nu Oa Oe Og Oh Oi Om Ou Ow Oy Pa Pb Pd Pg pI Pk Po qB Qd Qg Qh Qm Qn Qt Qu Qv Qw Qx Qy qZ Rb Rc Rh Rj

Figure 14 Continued

Figure 14 Continued

Bn bQ dE Dr Em fB Fd fR Gb hC hF Ib Mn oH Op Ps Ql Rx Ry Sf Sh Si Up Uw Uz Va Vc Vi Vj Wb Wc Wd Wf Wg Wh Zx Ye Tm Th) Ar(aF aU aV Bg bX cK cP cY Ed Gn Hb Hq Hr Hw Hx In Js Ly Ma Mj Mr Mw Nf Nk Nn Nr Ny Of Og Oi Ou Oy Oz Pc Pg pS Ue uN uZ vH Tj) Om(Hq Hr Hw Hx Ij Iv Js Lv Lw Ly Lz Mc Mi Ml Mq Mv Nr Ns Nu Of Oz Pb Pc Pg Po rQ sC tR uM uO uP vB vH wB wG yL tM Tj) dE(aJ aU aV Aw aY bA Bg cG Ch Co Cw cY dF dG Fp iB Im Ir Is Jh Jl Li Lx Ly Ng Nj No Nr Oi Oy Oz Pc Pe Pz Qd Ut Tk Wn) dB(aK aU aV cP Cu cY iB iH Mb rV tO tQ tR tS tU tX uI uN uW uX uY vA vH vP vT vV vW wC wE wJ wP wQ yD yJ zA zG tM) Nl(aA aN Bo Cw dQ dU GT Hq Hv Iq Is It Jk Jo Lu Lw Lz Mc Md Me Mh Mj Mk Ml Mn Mp Mr Ms Na Oe Og Ue) Ii(Ed jV lL Mb qB qC qD qI qV qY rA rB rR rV sC tR tU uI uV vC vH vP vT vU wB wC wE wH wK wP yH tL) Nc(Hq Hr Hv Hx Il Io Iq Is It Jk Jm Jn Lu Lw Lz Mc Md Mh Mi Mj Mk Mn Ms Na Nf Nq Oe Of Og Ue Uh) Ok(eT fP hP iB pI pY qD qQ sM sO tR tS tV uN uT uV uW vA vO vT vV vW wB wF wG wH yJ yK tM tL Wn) Mw(Aa Ed Hb Hw Im Iq Iv Je Jj Jl jV Kj Kp Kx Lv Lx Mf Ml Nq Oi Qg Ub Ue Ug Uh Vp Vt wF Tj) cP(Aa aC Af An Ao Aw aY Bg Bo bU cC cK cR Cu Cv Cw Cx De dI Dk Dr dX fR Gn GT Nh Nk Pc) Im(Ed Hw Hx In Iq Jh Jj Jr Js Lv Me Ml Ms Mu Nf Nk Nq Ns Nu Oy Pa Qb qG qH rQ rV sC Tj) Ue(aY cQ Cw dL Dq Ed Ex Fw gL Ih Je Kn kR Li Nh nY Ph Qd rW Sr Ur vU wH wL tM) dO(aC Af aI aJ aL aN aP bA bN cE cJ cK cZ dG dI Fp Gp Hv Jn Mb Nh Ql Qu Ut) Lx(Aa dX Hu Hx Ih Iq Iv Jh Jl Lv Me Mf Mk Mu Nf Nq Nr Ns Nu Oh Oi oT Pb) Nj(Ao Bo Ch Co Cv Dd De Dk Ex fR Hq Iq It Jk Jn Lu lW Me Ml Mn Mp Oe Qc) Ti(bX Ch qG qH qI qZ rN rQ rS rT rW tR tU uG uI uW vC vU wD wH wQ) Fy(Ed eM Je pS qG qI rQ rR rW tR tV uG uM vB vC Vp vS wF yL zG yE) sC(aS bF bL fP Gl Hb Ij Jo jY Kp lL Pc qC Ra Rf tR Ub Uh vQ Vt yL) Aa(aJ aU aV Aw Bg Bn cF Ch cY Fp Ir Iv Li Mf Ml Nt Oz Pe qH tV) Ly(aN aY Ch cQ Dq dX eM gN Ir Jh Jj Ma Nr Ny Oh Oz Pc Pg Qd) Jo(Nt Pe pS rR rS rW tR tV uR uW uY uZ vA vB vC vH wF wH wJ) cC(Af aK aN Ao aQ aU aV Ax bA Bn Bo cG cK cN Co Cu cY Zq) dQ(aH aI aN aQ bA bQ cR Cu cW cY cZ dD dG dX eM Ex Fw gC) Mb(Bn eX Ih Ij Io Ir Iv Lv Ma Mv Nr Oy Pa Pg Po Qc Qd) Yl(kG kO kP lY mF mI mT mU mZ nF nH nI nJ oE qV qW) aY(aK aQ aU aV Bg bU cK Ed Fc Fi kC mI Mp nD Rc Zq) Kn(Do dX Pc qH rN rS rW sK sM tN tO uW vH Vp vS) Uh(aF Ch Cu Dd dU Fw Js Kx Mr Pg Ra rW uW wH Tj) bU(aJ aK Ao aU aV Aw bA Bg Bo cG Co Cv cY dL fR) Iz(Dq Nk Of qI rW uV vB vH vO vS vU vV wK yK) Zq(An bZ Ch Fd Fi hG Hx iP mM Ny Or Qn qT Tj) Bg(aC aF Ax Bn Bo cK cO Cq Cs Dk fR gN gT) Cw(aC aK aU aV Bn Db Ed gW Je Nh Rb vB Tj) Gn(Ao bN Bo bX cB Ch Co Cu dN Do DV eP) Vo(Gc tU tX uP uT vS vU wC wD wG wL wP yL) dU(dN Ed Hb Ij Je Li lW Mk Qc Qd Qm Qw Ri) tV(Aj cR Kp Kr lK Ms Pz Qg Ql rQ Ub Uu Vt) Pc(cQ Dk Ih Iv Jh Jl Nn No Nu Po Qd qY) Bn(aK aQ aU aV Aw Bo cB cG Co Cu cY) Ch(Fp Hb Hl iB jV Ph qY tR Ur vQ Vt) Tj(Co Cu Dk Hb Ph pK Qd Rz Sr Ut Ux) Gw(aH aU cG cY Ij Jy Kd Ma Mk Rh Tr) Oz(Ih Ir Jh Jl Ma Nn Nr Nu Po Pz Qd) Pe(Ip Ir Iu Jq jV Lz Mj Ng Nn Qc qZ) dX(Bo cY dD Fa Hv Jr Kd Kx Ow Qz) tR(Al Aw Ct cZ jK Kp lK Ma Ms Pi) Gc(aC aU aV Bo hV iP Nh Qv Wm) Jl(Hw Iq Iv Jj Lv Me Mf Ml Qb) iB(bX Dc Dd dI Pi Si Ub Uk Wd) vQ(aE Ct Dk Jh Ms Og Pz Uc Vt) Do(aH cY dD Kr Ky Nh St Tn) Nr(Hw Iq Jh Js Lv Me Nu Pz) Oh(Hw Iq Lv Me Mf Ml Ms Mu) gW(Dr Em gC gT Ps Vi Vj Vw) wF(cW Hw Jh Kj Ms Pz rR Ub) Bo(aK aU Db Em EX Gt) Ed(bX Co Nn No Ph Qd Sr) lL(Du Op Sj Vc Vj Wg Tm) oE(Fd Gd Hp Vi Vz Yj Yk) Cu(aF aK aU aV Db eM) Dq(aC bE cB Fa Kr Uv) Mu(Ih Iv Jn No Po Qd) Hb(cQ eM eP Fw Ra Ss) Fc(jK jM jP oN rB) Ng(fN fY qO qZ Vt) aK(Ao Ax Co cR gN) iP(Hp kC nD Ry Ux) jV(Ih Ir Po Ra Va) uP(cW Dk Jh lK Ub) Gt(aH aQ cG cZ) Nt(aA Iv Mk Nu) Ms(tU uM vI wK) Vz(bN kF mY nB) Kj(Of qU rW vB) eX(cG dD Tn Vq) jO(Rz Uw Ux Vh) uW(Co Qh Ub Vv) vS(aC bE cH dH) Dv(aQ bB Bc) No(Hx Mf Ml) Hp(kR Rt Vj) Jh(vI zG tM) Jn(lW nJ qY) Ny(pS uR vB) Vt(qH uR wK) aH(cG gT qH) aU(Ao cZ dV) eP(cY Jr Qw) Gl(pS rW) Nu(Lv Po) Ma(Mf uT) Nh(bX cQ) Ub(Li Qd) Qz(pH pI) Jj(Nn Pz) Lp(dN nK) Vw(hG hV) aC(vI wH) aF(Fp gV) aV(Ao gC) cR(tN zA) dV(bB Bc) gN(aQ cY) lW(Ih Th) nA(Rt Sf) vC(Al Dc) CoJs DktM EmhV FidN FwSt MlQd TtqY SikR RbcQ Srdl WfjD TlrX RxqU LirQ RfbX OfyL OiuR UuwK VjjH VqhB VsrW PiqH aNgV bEwH cGcK cOvT cUrZ cWwG cZtT dRfR nFqZ kKpH kPpK Constrained panels with 3 analytes, where 9.1E-13 >= 'AUC p-value' > 0. Contains 50,000 panels of 37,261,550 total panels evaluated. :
Ti{pS(Af Ap Ar aS Aw aZ Bc bF bI bL bN bP cB CH cM CQ cR Cs Cv CW CX dE dL Dp ED Ha Hq Hv Ic Ii Ik In Ir jD jE jH Jk Jl Jn jP Jr Js jT jU Ke Kg Ki Kp KQ Ks Lj lN Lw Ly Ma Md Mk Mq Mr Na Ne Nf Nh Nr Ns Nu Oa On Or Pa Pb Pc Pe Pf Pg Ph Pi pY qA Qb qC qD Qg Ql Qn Qt Qz rB Ri Rj Rm rR rT rU rV rX rY sO tR Tt Ub Ue Uf uN uP uR uY uZ Vp VS wD wF wG wH zH yE tM tL Tj tF) uN(aI aL Ap aQ Ar aV AW Ba BB bE CH cI Ct cZ dA Dc Dd Di Dk dM eC Ef eT Ez Fp Hb Hf Hq Hu iA Ib Id Ij Ik Il Im Iq JG Jh JK Jp Jr jT Jv Ke Kf Kk Kl Kq Ks Kx Ky Lj lM Lv Mg Mj Ms Mv Nd Nh Ni Nm Nq Nu Og Oi Om Pd Pf qA qB qC Ql Qt Qw Rc rR rZ St Tt Ua Uc Ue Ug Uk Um Un uO uV vI Vs vT Vu Vv) vH(aE AO Aw Ax Ba Bc bF bJ bL Bo bP Cq Cs cU dB dE Di dJ Ed Ef fP Fw gL Ha Hr Hw Hx iA Ik It Iv iZ jG jH jI Jl Js jV jY Kg Kp Kq Ld Lj Lw Md Ml Ms Mv Ne Nh Nj Nk Nl Nn Nr Ns Nu Oa Or Oz Pi qA Qb qC Qd qH qU Qy Qz rB Rc Ri rR rV rX rY sC sO Tr tV Uf uM UR uT uY uZ vI vO Vp Vt Tj tF) vV(aJ AR aS aZ bF bI bL bM Bo bP cH Cs dE dJ ED Fp Fw Ha Hr Hw Il In Iv jE Jl Jn jT jY Kq Ld Lj lN Lw Md Mn Ne Nf Nh Nj Nn Nr Ns Nu Nv Nx Oa Oi Or Pa Pb Pc Pe Pi QA Qb qC QD Qg Ql Qn qX Qz rB Ri rR rU rV rX Sr Tr Ub uM uR uY uZ Vp vS Vt wC wD wF wH wL yE tM tL Tj tF) wF(Ad An AP aV Aw Bb bE Bg bJ cB cF Ch Cp Ct Cu cX Dc dE dH Dk Ef Fr Gp Hc hW Hx Ib Ii Il Iq Iz jE Jg Jh Ji jK Jo Jp jY Kk Lv Lx Mg Mh Mk Ms Mv Nd Ng Nh Nq Nw Of On Oy Pa Pb Pc Pf Po qD Qg Ql Qn QT qU Qy Rj Ua Ue Uf Uk Um Vo VS Vu wD tL) tV(aK AL Ar As aU aV Aw bA Bc bI bL bN cB Ch cJ cM cN cR cU Cw CX cY cZ dA Dd dE Ed fY gW Hu Hx Iq Ir jK JM jP jQ JU kQ Kx Mf Ms Nd Nn Ns Nx oH Pb Pc Pd pY qD qG qH qI Ql Qn Qt qU Rc rQ Tt tU Tz Uk uR vA vI vP Vs wB wC wK yJ zG tL) wG(Al As Ax BB bL bO bP cH cI cM Cs cZ Dd dE dJ dL Ef Ha Hu Hv Hw Hx Ik In Iv Jl Jm Js Kk Lj Lv Lw Md Mr Ms Mv Nf Ng Nh Nr Ns Nu Nv Oa Pa Pe Pi Pz Qb qC qT Qz rA rB Rc Ri rR rU rV rX rY Ue Ug Uk uM uY uZ Vp vS Vt wC wD wH wL zH tM tL Tj tF) vA(aI Ap Aw bM cB cF cH cM Cp Ct cV Dc dH Di dJ Dk Ef gP Hu iA Ib Ik Iq Iz Jd JG Jh Ji jK jO JU Ki Kj Kk Ko Kq Ks Mg Mq Mv Mw My Nb Ne Ng Nh Nu Oi Om Or Oy qA qC Qh Qt qU Rc Rg tR Uc Ue Uk Uu vI vQ Vs vT zG xA) tL(Ad aF aO Ap aV Bg bR cB cF Ch cI cM Cu cW cX dB dH Di dJ dL eD fN Hf hR Hu Ic Ij Iq iZ jH jK Jl JV jY Kc Kg Kk Kn Kp Lx Ma Ms Nj Nw Ny oH Om Oz Pf Pk Po Qd qH Ql qU rB Rj sC tN Tv Ub Uf Uk Um Vo Vs wK yE Th) vS(aI aO Ap aV Ax Bb bL Cq Cs cW Cx dB Di ED Fw Hr Hu Hw Hx Iq jK Js jV Kc Kg Kk Kn Kp Lw Ma Md Ms Ne Nf Nh Nw Ny Oa oH Om Or Pa Pb Pf Pi Pk Qb rB Rc Ri Rj rR rV rX sC tQ Uk Um vI Vo Vp Vs wD wH tM Tj) uZ(Ad aI Aj Ap aQ Ar aU aV AW Bb cM Co Cp cU cV dA dH Di dJ Ef Hf Ic Ij Im Iq Ir Iz Jd Jg Jh Jo Jp Jt Ke Kj Kn Ko Ks Mz Nb Ne Ng Nh Ny Of Og Oi Om Oy Pb Pc Pf Qt Rb Rc Rj tQ tU Tv Uc Um uO vI Vv wD) wH(Ad aO Ap aR aV Aw Ch Cp cW Cx dB Dc Di eC eD Hu hW Ii Ij Im Iq Jd jK Jo jV Kc Kg Kk Kn Ko Kp Kq Lx Ma Mg Ms Mt Mv Mw Ng Nq Ny Of oH Om Pb Pc Pf Pk Po qA qD Qt Rc tQ Tt Tv Uc Um Vo wD wK) wL(Ad aO Ap Ar aV Aw Ch Co Cp CX dB Dc Di eD Ef Hu hW Im Iq Jh jK Kc Ke Kg Kk Kn Ko Kp Kq Mq Ms Mt Mv Nb Ng Nq Nw Ny Of oH Om Pb Pc Pd Pf Pk Po Qd Qh Qn Qt Rc rP Tv Uk Um Vo wD yE) wD(Ad aO Ap aV Aw bL bM cF Co Cp cX dB Dc dE dH Di ED Hu Ii Ij Im Iq jK Jo jT jV Kc Kg Kk Kn Ko Kp Ma Ms Mv Ng Ny Of oH Om Pb Pc Pf Pj Po rB rV rX rY tQ Tv UM Vo Vs tM Tj) yJ(Ad aG aH aM As Aw BB bE bM Bo bZ cB Ch CX cZ dF dH Di Ef Hu iA Iq Ju Kj Kx lL Mn Mp Ne Nh Ny Or Oy Oz Pk qA Qd Qh Qm qU qY Rc Tt Uk uP uY Vs VT wP wQ zG zI) wC(aK aV Aw Bb Ch Co Cu cW Cx dB Dc dH Di dJ dL eD fN Hu Ii Ij Im Iq jK Jo jV Ke Kg Kk Kn Ko Kp Lv Ms Mv Ng Nw Ny Of oH Ok Om Pb Pc qC qU Rc sC tQ Tt Uf Uk Um Vo) tQ(Ax bL bP cH Cq cX Fw Ha Hr Hx Ik Iv Jl jM Js jY Lj Lw Md Mr Ne Nf Nh Nr Ns Nu Nv Oa Or Pe Pi Pj qD Ql qU Qz rA rB Rc Ri rR rU rV rX rY uM uY Vp Vt tM tF) vI(AD aI aJ aL bL bP cW

Uf) oP(Bc Bo Cp Cq Ct Cv Db Dc Di Dp Ed Fy Pk Qg Ra Rh Uo Us Uv) Hp(aL bB cU cW cZ Di Il In Iq Jm Kr Ms Qh Tz) Rx(Af Ar As cQ cV cX Fa jI jY Nc Nk Nl Ss Uv) Vj(aD As Db iC jD Je Jl Ks Mn Mr Pk Qd Rm Vt) Gn(aR aX bN Hx iC Ih Jl jR jU Ky Nu Qd Ri) sC(Et Ii Ik Jg Kl Mg Mq Ng Om Pi Pz Uf yL) Em(Af cZ dD hV Ip jY Kx Mr Ni) Sf(aJ Ju Jv JY Pd Pf Uo Vz) Rt(aL bB cU cV cW Dp Dr In Up) We(aG aL cW dD hV jI jQ qT) Vb(cO CV dA jI Ky Ni Uv) mU(Ba Bg Bo Ef Ez Iz Jd Ke) rP(Ad Jd Jg Kl Mg Ms Mz Om) Yk(aY iB jF Ni Nl qU rA) Ye(aL bB cU cW cZ Og) Uu(kC kE kI mM nA nB) Sj(hV Ip Jp Mv Ua) Yl(Jf jY Nd Pk Uv) pS(Ii Ke Kl Kq Uf) Du(cU In jQ Tt) Qw(nJ nO nT nU) Jy(kG mM oO oQ) mP(Bo Jd Kl Or) Dr(cJ Nl Pk) Ed(nA nD nK) Vz(aY Ju Nc) Sh(dJ Iv jF) Op(Ko Nx Tt) Vc(Fa hV jI) cQ(kF oO oQ) kO(Ih Jn Kj) Di(lY nU) Dp(Lt mF) Gd(Ni oK) Ra(mW mY) nD(cW Rb) tV(Ms Ub) qP(Ap Ue) oQ(Qg qZ) BakG ThGz FaFi IkrQ YjRi KeqG KlvC TkdB PkmS} Ok{rQ(aC aI aK aL aQ aR aS aU aV Ax bN bP cH cI cJ cM cQ cR CU cY cZ dA dE dI dJ Ed eZ Fw gW Hq Hw Hx iA Ih Il In Is Jd Jn Jr Js JV jY Kk kS Ld lK Mg Mk Mm Mr Mz Nb Ng Nn Nt Nv Ny Oe On Or Ou Pg QA QB QC QD Qg Ql qU rA Ri Rm rP rW rX sC Tn Ub Ul vB vC vH Vp vQ wF Tj tF) Js(Ad aF aH aI Ap aR aY bM Bn bQ bX bZ cE cK cP cQ cW dB Dd dE dI Dq Et Fp Hw Hx Ik Iq Jd Jj Jo Jr Kf Kj Kx Lj Ly Mb Me Ml Mp Ms Mt Nc Nd Ne Nf Nh Nj Nk Nl Oe Of Oh Oz Pc Pd Pe Pf Pj Ra rR rS Tz Ue Uf Uk uL Un UR vQ wB wJ Tj) vQ(aC aI aL aU aV bB bE bJ CH cI cJ cM cQ Ct cZ dA Dd dF dJ Ef Gp Hv Iv jE jF Jh Jj jK Jn jQ Jr JU JV Kd Ld lK lN Mg Mn Ms Mv Ng Nj No Nt Of Og Ow Oy Pe Pg qB Qc Qd Qg Ql Ra rW sC Ut wG wJ) rR(aG aH AS Ax bN cH cI Cq Cs Cu dE dJ Ed eZ Gp Hq Hr Hx iA iB Il In jE jF jM Jn Jr Jv jY Ld Lw Mz Nn On Or Pc Pg Pi QB qC qD Qg Qn rA rB Ri Rj rP rV Sr Ub Vp wF tL Tj) rP(aC aH aI Al BB cH cI cJ cM cY cZ dA Dd dF dI dJ Ed Hx iA Ik Iv jG jM jY Kk Ld lN Mk Mr Ng Nn Nt Nu oF Or Ou Pg Pi Pj qA qB qC QD Ql Rc Ri Tn Uk uR Ut Vp wJ) uR(aG aH aI aL aS bB cH cJ cR cW cZ dF dG dJ eZ Ha Hx iA Is Jn Jr lK Mn Mz Nb No Nq Nt oF Ou Ow Pe Pg Pi Qa Qb Qc Qd qG Ri rW uT vH vP wQ) vB(aC aH aI aL AS aV bB Bc Bo cH cI cJ cQ CW Cx cZ dA Db dG Di dJ Ed iA Ic jG jK jM Jr jV Kd Ld lN Nj Of Or Pi Pj qA qB qC Qg Ql) Mt(Fp Gw Hw Hx Ii Ij Ik Il In Iq Ir Jg Jj Jk Jn Jo Mb Mp Ms Mw Mx My Mz Nb Nc Nd Ng Nq Nv Oe Of Om Oz Pc Pd Pe Pf Pg Qa Qb Qc Qd) sC(aG Al aO aS BB bL cH cI cM Cu dE dG dJ Ed Fw iA Ik jD Jr jY Ki Ld Md Mr Mu Mv My Nt Nw OF Or Pi qA qC qD Ql Uk Ur Vu Tj) Pf(Et Hr Hw Hx Ii Ij Ik Il In Iq Ir Iu Jj Jk Jn Jo Ly Ma Mb Mp Ms Mx Nc Nd Ne Nf Ng Nh Nj Nk Nl Nq Oe Of Oh Oz Qa Qb Qc Qd) vH(aA aS aU Aw bL Bo cH cI CQ Cu Dd dE Hx Iv jG jI jM Jn Jr jY Kd Kk Kn lK Nj Nt Or Pg Pi qA qB Qm qY rA rW Tn Ub Vp) Ik(dU Hr Hw Hx Ii Ij Il In Is It Iu Jj Jk Jo Jt Mg Mp Mx My Nc Nf Ng Nh Nk Nl Nq Ns Oe Of Oy Oz Qa Qb Qd qG qZ rW yH) Et(Hr Hw Hx Ii Ij Il In Iq Ir Jo Ly Ma Mb Me Mp Ms Mx My Nb Nc Nd Ne Nf Ng Nj Nk Nq Ns Oe Of Oz Pc Pg Qb Qc Qd) rW(Al aR aS Bb bP Ch cI cQ Cw Dd dE dI Ed iA Ic Iv Jd jG jM jY Ld Lw Mk Mr Nu Or Pd Pi qA qB qC qD Qn Ri rV rX) Nk(Hr Hw Hx Ii Il In Iq Ir Iu Jj Jk Jn Jo Ly Mp Mx Mz Nc Ne Nh Nj Nl Ns Oc Of Oh Oz Pc Pd Qa Qb Qc Qd) wJ(aJ aL aQ aU aV cH cI cR cW CX cY dA dB dE dL gW Ha Hx Jd Jr Mn Pe qA qB Qg Ql Qn Ri) Nc(Hr Hw Hx Ii Il In Ir It Iu Jj Jk Jn Jo Ly Mb Mp Mx Mz Nd Ng Oe Of Oz Pc Qa Qb Qc Qd) rV(aG aH aI aK aQ aV bB cI cJ cQ Cw cY dA eZ Gp gW iB jE jF Jr lK Na Ng Qg Ql qX rA vP) Fp(Hr Hw Hx Ii Ij Il In Iq Jj Jk Jn Jo Ly Ml Mp Mx Mz Nf Nv Oe Of Oz Pc Qa Qb Qc Qd) Pd(Hr Hw Ii Il In Iq Iu Jj Jk Jn Jo Mb Me Mp Ms Mx Nd Nf Ng Nq Oe Of Qa Qb Qc Qd qZ) wB(Af aR As bL bP cH cR Cs cX dA Di dJ eF hG jY Ld Ng qA qB qD Qg Ql Qm Qn Ri Ub Vp) uL(As Aw Ax bB bN Bo CH Cs Cu CW cZ Ed jM Jn jQ Kd Kk Kx Ld Nj Or Pg Pi Qg qP) Jg(Ii Ij Il In Io Jk Jo Jt Ma Mu Mv Mw My Nb Ng Nq Ns Nv Ny Oe Of On Oy Oz Pg Qb) Pe(eX Hr Hw Hx Ii Ij Il In Iu Jk Jn Jo Mp Mx My Mz Nd Nf Ng Nq Nv Pg Qa Qb Qc Qd) Ne(Hr Hw Hx Ii Il In Iq Ir Iu Jj Jk Jn Jo Ly Mp Ms Mx Ng Oe Of Oz Qa Qb Qc Qd) Nl(dO eX Gw Hr Hw Hx Ii Il In Iu Jj Jn Jo Ly Mb Mp Mx Ng Oe Of Oz Qa Qb Qc Qd) Nh(Hr Hw Hx Ii Ij Il In Ir Iu Jj Jk Jn Jo Mb Mp Mx Ng Oe Of Oz Qa Qb Qc Qd) Gw(aD aE Af aJ aR Aw Bb bM Bn cM cO cY dM dR gP Hv Jj Ma Mf Mx Nu Tn) eP(aD aM Bb bV cK DC Di Dk Dl dM Ii Ij Ji Lh Mv Mw Mz Nq Om Qz) Nj(Cq Cu dU Hw Hx Ii In Is It Iu Jj Jn Jo Mb Mx Ng Oe Of pS Qb) Ly(Hw Ii In Jj Jo Mb Me Mp Ms Mx Nf Ng Ns Oe Of Oz Pc Qb) dU(aE aK aL aU aY cD dN dR lW lX Mk Ml Mq mT Nt Nu Uk Ut) Dq(aC aF As Co cU dG dH Ed Gz Jd Jh Kk Ml Mx No Oi Oy) Me(Hr Ii In Iq Ir Iu Jj Jo Ms Mw Mx My Nf Ng Qa Qb Qd) eX(aD Ar aV AX aZ bC Bg Ch cT Db Ic Li Lx Og Om Rm) vT(aL aR bL cH cR cU cX dD dE Ld Na Qg Qm Qn Ri uP Vp) pI(aC bC cR cZ eQ fB kC Kq Lv Mq Mw Nf nJ nU Nx Pa St) Mp(aH aY bM bQ dE Hw Hx In Jj Jo Nx Oe Of Oz Pc Qb) tL(Ad aG aH aI aV dA eZ Gp gW hP iB jE jF lK Ng rA) uY(aH aI aQ aS bU cM cR cU Cw cY dA eC eZ gW Ql Ri) uZ(Ad aG aH aI cM dA eZ Gp gW iB jE jF lK lN Ng rA) In(Ad Hw Hx Im Iq Jr Lj Mb Ms Nb Nd Nt Of Oz Pc) Qb(Hw Im Iq Jo Jr Lj Lv Mb Ng Of Oz Pc Qa Qc uP) tR(Af aL As aU cJ cW cZ Dd iB jK jM jY Pi qA sM) wC(aH aI cM dA Dd eZ hP iB jE jF jK lK lN Pk Ql) vP(bL cH dE dI dR iA Jh jR qB Qd Qg Qn rB Ri Vp) uM(Ad aG aH aI cJ eZ Gp gW iB jE jF lK rA Vp) Hx(bM Hw Jj Jo Mb Nd Nf Ng Oe Of Oh Oz yH) wF(aH aI eD eZ hP iA iB jE jF lK lN rA tF) uT(aC bE cH cO cX dE jY Qg Qn rB Ri Uf Vp) Of(Ad aH Hw Iq Mb Mx Nd Nx Oz Pc qB Qd) rN(Ax Cq Cv jG jM jY Or Pi qA qB qC qD) Oe(aH dE Hw Iq Jo Lj Mb Ms Nd Oz Pc) zA(aK aV Ct cY dA Dc Dd iB jE Kg yK) uX(aR cR cU dA Jn Jv Qg rA Sr Ub Vp) Qd(Jj Jo Jr Li Lj Mb Ms Nf Og uO) zG(Af aS cM cW jG Pi qA qB qD Ql) rO(aH aI eZ Gp iB jE jF jK lK lN) Pc(Hw Ii Iq Iu Jj Jo Ms Nf Ng) qB(qX qY rA rX rY uP wE yH yK) wD(aH aI eZ hP iB jE jF lK Ql) wH(aH aI bE cH cZ eZ iB jF lK) tM(aH aI aV eZ Gp gW iB jF lK) Mb(dE Hw Iq It Jo Ml Ng Oz) bM(aH dE Hq Nn Ny Oh Pg Tj) dO(cH Cv Di Dk Lj Nb Om Rg) qG(Al aV cM Dd hC Io jL Ql) uP(Aa aI cJ cW dL jG jK qA) vC(Al Bb cI Cw dB dE jM Kx) Li(Il Jk Jr Mj Mx Pg Po) eQ(aL Kn Kq Pk Qh St Uk) sO(Cq iA jY qA qD Ri Vp) rS(Cu Jn jQ Nn On Qg qP) uO(cH Jn jV Nt oF Tn Vp) Nd(Cu Hw Iu Jj Jo Ng) Lj(Il Jn Mx Oh Qa Qc) Nx(Ii Il Is Jj Jk Jo) tX(aL aU cW jG Pi yK) wE(aI cH cI dJ Pj Ql) qI(cM Mk Nn Or rB Vq) Qg(pS vA vW wP xA) Yl(nR qV qW rA rZ) Oz(Hw Iq Iu Jo Ms) dE(aR Bo cQ eM Na) dX(bX cK Db Fr Pb) Tj(cE jB oD pK) Ng(Mu Mx Mz uV) Ji(Ii Jq Nb Pg) Jr(Il Jn Nf Qa) Ql(pS sM tV xA) yH(Iv Ld Nn Nv) jG(qZ sK vU vV) uI(cM dG iA oF) uW(cM Dd gP Vp) Jo(Iq Mf Ms) aL(eM vI vU) tV(Al Dd jL) wG(aH iA oF) rA(qA qC qD) qZ(lK Nt Vq) pS(Al jV jY) Qa(Im Qe) Jj(Iq Ms) Nw(Nb Pg) eM(cZ Hq) eZ(rB vO) tN(cR iA) iP(kC nC) jF(yL zH) vI(aI bE) CsyK DdwP DiDo EdjB YfhV FinA NnqQ NsMx MuJk SiqX QcQe JduV LpmM RvqV NyOm VbiC VpzI VwkI dJtT eCoT iByL lKvO} Pj{rP(Aa aG AJ aQ Bc bJ bP cM Ct dH dR Gp Ha Hr Hv Hw hX IC Ii Im Io iZ jD Jh jO jU Kn kS Lh lK lN Lx Mj Mn Mr Mt Mw Nf Nh Nl No Nr Nx Ny Of Om On Oy Pd Pe Po qH Qy Ra rC Ri Rm rR rV Sr tR TV Tz Ua Ue Un Ut Uu Uv uZ Vs Vt Vu wE zG) vC(Aj Ar Aw Bb bP bX cB Co Cp Ct Cw Dc dE Ef Fa Fr Gl hA HC Hq Hu Hw iC Ij Io Jg Jh Ji Kc Ke Kg Kl Ko KQ Ky Lh Lx Mp Mq Mt Mw Ng Nr Om On Oy Pb Pc Pd Pe Ph Po QT Ra Rc Rg rQ rR rV tQ tT tV Ua Ub Uc Ue Un uO Ut uU Vs Vu wH) yK(aJ Ar Aw aX bO bP cH cI Co Cp Ct Cu Cw Di Ef Fa Fr hA HC Hq Hu hV HW iC Ij Io Jg Jh jR jV Ke Kg Kn Kp Kq Lv Mg Mw Ng Nr Om On Oy Pc Pd Ph qH QT Ra rQ rV tQ tR tT tX Ua Uc Un Ut Vs Vu wH yL yE) pI(aD aV bC bE bG bN bU bW bX cI cR cS cV cZ dB dH dJ dN dU eQ fP Gp hB hF Hx iA In Kc Kl kK Kp Li mI Mk Ml mM Mq Mw mY Mz nB Nd nJ Nk nT Ny Og oP Ph Qb Qc Qn Qv Qy Rg Rj St To Tr Ud Uf Uk Ul Ut Wm) sC(Ad Af Ar aS Aw Bb bF bM Bo cF cH cR cT Cw Cx dA dE Gp Hu iA Ii Ij Ik Il Iq Iz Jg Jh Jk jO Ki Kj Kk Md Mg Mn Mp Mq Mv Mw My Ny Of Ph Pi qB qD Qh QT qY Qz RC Rg tR Tt tX Ue vA vH vU tL) rW(Aa AP Ar Aw Bc Ch Cp Cw cX Fa Gl gP gW HA hW Ic iH Ii Ik Im Io iZ Jh Ji jR jY Kl Kq kS Lx Mw Om On Oy Pd Pe Po qA qD qO QT Rc rS tR tS Tt Tv tX Tz Uc Ue Uh Un Vs VT Vu vV wL) xA(Af aG Al aM aV bJ bN bO bP bX cG cO cR Cv dA eF Hb Hr Hw IC Il In Io Ip jD jE Jo JV Kd Kn lN Ma Mn Mp Nr Oe Og Pd Pg Ql Qn Ri rQ rR rV tN Ub Uo vB Vv wE wL zG) dU(aC aE aG aW bE bJ bN bS bV bW cA cB cF cU cY cZ dE dM dN dR eQ Ik Ip Iq Iv Jk Jr Ko Ld lW Lx Mk Mp Mq Mw Mx nA Ni Nj No Nr Nt oV Pd Ph Qn Qv Rg Tt Ut Vv tF) eQ(aH aU bB bC bE bG bV cI cR cZ dR Fa fB fP Gp iH Ip Iq Jn Ju kC kP Lj Ly Mk Ml Mq Mr mY Mz Nf Ni NK Nm Oa oT Pi Qw Ra Rg St Uk Un Uo Ur Vt Wm) pS(Aa Af

Nr Nw Of Og Ql Qm Ss To Un Us Uu Uv Vt) Vb(aI aP cZ Ef Hu Id Jh Jr kC Kl Kn Ko kP Kz Nc Nd Nf oE Om Pi Ql Qu Qz Tv Um Ut Vj Vv Wh) Ye(aP cC cF cH dN Hq Hx Jn kC Kl kP kR Ky Kz mM Mq Nc Nd nJ Pc Pi Ql Qm Qz Tv Ut Vj) Gn(aA cF cR cS cX dN Fn GP hF Hq Kc Lt Ma Mh nC oK oN Qm Rc Ss Ue Uo Us Vt Wf) jT(Aj Ba Bb bM Cv Di Ed Fn gP Jd Kz Or pF Ql Qm Qw Qz Rb Tr Tv Ue Um) Uy(aA aS bG cD cF cL dN eC fP Fr Gz Jr Lt mF Mh Of Pf To Us Uu) Lt(aN aP bJ bO bP cQ Dp Fa Je Kn Ky Me Pz Qg Tv Ub Ur Tj) Vj(bU cI dB dE Ef fP Jq Ju Jv Kc kK Mh oN Qh Qv Sf St) Zw(Dp Ex Hf Kc Ko kR mH mM Mz nF nT Ql Qm To Un Us) Tm(aS aY cD cF cT dN Ex Hq Jr Kc Mh Of Og To Uu) Sf(bI cD cF Ex Fa Fb Hq Ic Jn Ma Mc mT Tj) Ho(bI bU Hu In Jm Ma Nf Ql Qv Um Tj) Hf(eD gW iC jD jQ jR jU jY lK qU) Sh(bG bI Fb Jn Ko Me Of Tj) qX(Ap aY Bo cZ Dg Ed Kl Or) Ex(aP Dr Fd Ps Rx Vh Zx) Nf(Gb Gc Hp Rz Wb Zq Yf) Ru(cF cR cS dN Jr kS Ue) Ps(aS bI Fb Og Pc Ql) dN(Fd Gc rX Sj Vh Yf) Zq(cR kK Kz Qh Ua) Zx(Jn kC kK Kz Ql) Pc(Du Fd Hp Rz Vi) bG(Dr Du Em Fc Wc) Fa(Du Rx Si Va) Wb(Hq Hx Jm mM) Op(cI Fb Fn kK) Vh(cP Ko Qm Un) Tj(Dr Rx Ry) Fd(bI Mj Qm) Hp(bO cQ Jm) Vi(Fb Jn Jr) Vw(Mh nT Vo) aY(iB jY qV) cZ(jQ lK Sj) dC(hA qV rZ) fP(Rv Uw Wc) jD(Ed Jy Qw) qY(Fn Or Pk) lN(bQ iP Ky) Di(jY lM) Yf(cP Qm) Mb(Rz Xa) Hq(Rx Ry) Wf(aN Tv) Kf(jG jL) Ql(Hl Va) aD(hA qW) aP(Du lK) iB(iP Pi) AsjL EmbO EqcM FccD GblK GcQv GddB MhRx MwpI SiJn SjKz JhUw WcOf JrRv KceQ KoVa bElK cGhX cWeD dRhV} rW{Bb(aA aM AR aX bC bR cD cO cQ cR Cv Cw dK Fa fP Fy Gl gW hL Hr lC Ii Ik jD Ji JO jY Kc Kg Kp Kq Lh Md Mg Mm Mr Mt Nx Pd Pi Pk Qg Ra rC sK sM tO tX Tz Ue Uh Un uP Ut uU Uv vH vI vQ Vt yE tM) Ic(Ad Al Ap Ar aS Aw Ba cH Cp Cv Cw Dg Ef Fn HB Ik Jd JG Ji Jp Jt Ke Kg Kl Kq Lu Mg Mm Mq Mv Nd nY oE Oi Om Or Oz Pd Pz qB qC Qh rR Tz Uk Ur Uu Vp vT wJ) Mm(aH al aO aS bB Bc cH cI cJ cM dA dF dN eC Ed iA Ik Iv Iz JG jK Jp Js Kl Mn Mp Nn Nt Nu Or Pg Pi qB qC Qg Ql Ri rQ rR Tz uT uW vH vQ VT wJ wP) Ik(Ad Ap cD cH cP dB dI eD Ez fY Hb hR hV hW hX Im Jg Ji Jp jQ jR Jt jY Kc Ke Kg Kj Kl Ko Kp Kq lK Lu Ni Nj Nw Ny Om Pi qO qP Qw rS tN Uh Un Ur uW) Ad(aC aR aS Ax cR Cw Db Fa Fn Gl gW hG hV hX iA iH Io Jd Js jY Kp Kq Ld lM Me Mt Mw Na Or Pc qA qB qC Qd Rg Ri tS Tz Uh Un vH Vt) Kl(aC Ap AR aS bL cH Cw Ed Fn Ii Ke Kg Kp Ld Md Mt My Or Pa Pc Pi qC Ra tS Tz Un Ur vH vQ Tj) Cw(Al Cv dI ED Fy Ii Ji Ke Kq Kz Ly Mt Mz Nw oH Pd Pi Pz Ra tS Tz Ue Uh uI Uk Un vI tF) Ii(Ar aS Aw Ax Bo cI Cq ED Fw Hw iA jE jG jY Ld Or Pi qA QB qC qD Qg rX Ur) Pd(Ap Ax cH Cs Fw Gl Hb hX Jp jR jY Ke Ko Kp Kq Ld Nk Nn Or Pi qB qC qD Qg Ur) Ap(aS Ed eZ gW iA jG jM jY kS Mt Nx Pi qA qB qC Qu rX tS Tz uL vH vQ) Jt(aR aS cH Ed Gl hV iA Is jE Js jY Ld Na QA qB qC QD Qg Vp vQ) Kg(aS hV iH jG jQ jY Pc qB qC Qg qO sC tQ tS uI vH vP vQ vV zA) Jg(aA aU Iv jY Kx Pi qB qC rX tO tX Tz uU uW uZ vH wF yL tM) Un(Ar aS Ax Bo Cq Ed Fw jG jY Kp Ld Nd Nu Or Pi qA qB qC qD) Kq(AL bB bL cM Dc Fn Jm Kf Ld Mg Oe Ra Tr Tz Uk Vo) qB(Co Dg Hb Ij Im Jo Jp Kc Lx Mg Po Uf Uh Vo Vs) jY(Dg Ef Ij Ji Jo Kf Kj Mg Mq Pz Tt Uc Ue Vs Vt) qC(Ar Dc Dg Ef Hb Im Ji Kc Kf Mg Mt On Qt Vs) jG(Ao Co Dg Hb Ij Ji Ke Kf Mg On Uf Uh Vo) Tz(Ba Bo CP Di Gl Jp Ke Ko Kp Qg Ur) Kf(cH iA Nu Or Pi qD Qg Tr tS vH vQ) Ji(As Bo cH cI jF jR Js qD Qg Rh) Kp(Al Iz Jd Oy Tr tS tX Ue Vt yL) Uh(Al Ch Dc Dd Ef Kj Kx Or Pi Uk) Ed(Ar Im Jp Ke Lx On Pe Po Vu) Im(Jn Js Nn Qb Qd Qg Tr Vp) Ef(Pc tS uI uL vH vQ vS) Jp(Gl Or Rh rX vH wF yL) Ke(Ld Or Pz rX Uk vH Vt) Ld(Fy Lx No On Pe tS) vQ(Ch Dg Dl Iz Jd Kj) Ar(Tr Ue uZ vH Vt) Qg(Dg Ih Om Pe Rm) Uf(Pi uT uW vA wP) Mg(jR qA qD qO) Hb(hV hX qD vH) Iz(Jk Jv Pc tS) Al(hV jF vP) Cp(aL Pc uI) Dg(iA qA tS) Gl(aC Pz Uk) Om(As cH cI) Vt(cH Pi Ur) Vs(hV rX Th) Aa(hA uR) Aw(sM tS) Ue(aS Or) Tr(Kc Pi) Jd(cH zA) Ko(Pa Pc) Pe(Ax Cs) wF(dH Mq) BavH ChtS DlqD FwLx FyIv MtOr JouW KjPc RhwG VoyL} qU{Gh(Ap Ar aX bC bF Bo cG Ch Co CW Dg Di dJ Dk Dl Ez Fc Gc Gl Hu Id Ik Ip Iz Jd Jg Jj Jn Jp Jt Ju Jy Ke Kf Kg Kk Kl Kp Lh Li Mg Mh Mk Mn Nf Nj Nm No Nt Oi Ow Oy Pb Pc Pd Pf Qm qT Qu qW Rc Si Sr Tz Ua Un Up Uv Uw Ux Uy Vj Vv Vw Wb Wc Yg Zq Xa) Tl(aI aS aY bA cG cI Cs dM Ed Fa Fb Fw Hl iB Id jT Ml Mp Mt Ni Nq Nt Of Pe Pz Qu Qw Ri rX RY Ug Um Uo Vb Wh Yj) Ry(aD aM aY bO bX cC cM Cq cS cW dN Fn Jm Jn Kg Kp Ky Lt Mr Mt Nf Pb Pc Qe Qn Qy Rb Si Tz Ut Vz Wm) Zq(aQ aU aW aY Bg bL cS cT Cv cY dM Fb Fd Fn Gb iB Is Jk Jm jT Ke Kl Or Pz Qn Ul Ur Uu Ux Vq Zx) Vw(aD aG cB cE cM cS CW Cx dH Fd Gp HR Io Je jT jY Ki Ky Lj lN Lv Nk No Ns Oa Or Pa Rc Ri) Lp(aD aP bB bL bM bR bV bZ cE cM Dd dG dM Fc Fd Hp Id Ir Iv Jy Me Po qX Qy Uu Vq Wh Wm) Gc(aD aL aQ aW aY bB bM cM cW cY dD dN Fn Gp Ip It Je Ko Ms Or Pb Pc Qv qY) Yj(aD aI cB cM CX dM Fd Fn hR Ik Io Jm jT Ki Kk Nr Oa Oh Or qV Rg Rj Rv) Vj(aG aI aK aQ aZ bB bL cB cM cY Id Io It jD Je Kn Mz Nr Ns Pb Pc Qc Sr) Fc(aL cX Dp Fd Fn Ip Iq Jm Ki Lv Ns Ny Og Oh Or Oz Pc Pd Qc qW Rg Th) Yg(aI aW BA BB cM cT CW Fd Gb jT Ki Mk Or Pk Rc Uc Uh Ur Uu) Rt(AD cW Cx cZ dD Ef Id Jn Kg Kj Lv Mg Mw qY Ri Rj Rx Tz Us) Rx(aY bL bM cV Fn Jm Ju Jv Jy Kp Mb Mn Mr Oz Pf qT Vv Vz) Mk(Du Fd Gz Ho Op Rv Sj Ux Vb Vi Vq Wf Wh Zw Zx Xa) cW(kC kO lX mF mH mI mU mY nC nH nK nL Ux Wd Zx Xa) Si(aI aQ aU cM dL Fn Hr Jk Nr Ns Og Oz Pc Pd qX) Vb(aD Ao Ax cP Ho Kp Ky Lv Oa Oy Rf Rj Tn Tv Vs) Fd(aL Ap bP Id Kp Kq Lh Ma Mb Nt Pf Qm Qy Ut) Rv(Ao cP Ez Gn In Jd Mb Mn Pc Pf Qm Qu Ur Vv) Vi(bA cT Jd Jm Jt Kn Kq Mb Mg Mt Nt Ql Qm Ua) aY(Gz Ho mS nL Rz Va Vq Wc Wd We Yd Yh Xa) bB(Eq Gb Ho Lt Op Rz Va We Wf Yh Zw Yf) Vz(cX Ez Id Ik Ip Iq Lv Pd Tn Ur Yi) Ur(Eq Ho Lt mE mF mI nI nK nN Uy) Xa(cM cN Cx dN Fn Jm Kp Qn Rf) Ux(aI bA dH iB jE jT Or Ri Uu) aL(Du Fi Ho Hp Ps Rz Vc Zw Ye) Gb(aW Ez Jm Jt Kg Mg Qv) Ho(bL cT Pd Qc qX Ri) Yh(bM cQ cV Je Jy Nc) Wc(aI Cv Dc jT Of Wh) Ps(aW Je Ko Mm Oi Qm) Yf(bP cG lK Mn Qy) Sj(Ao cM Ma Oa Vs) Zw(cP Id Pb Rf Rj) Rz(dH Ed Fn Of Uu) Vh(Fn Ko Mg Of Pc) mF(Ct iP Kj Tv Tz) nD(aD As bO Cv Cx) hC(kF kO nC nH nL) Du(dJ Ez Ik Vv) Em(dN Fn Kp Pc) Hl(Pc Pd Ri Tn) Uy(Ad Ik Iq Lv) Va(hX Id Ko lK) kO(Ct Jd St Ut) Gd(Ip Pc Pd) Gn(aD Or qX) Yi(cQ cV Jy) Sh(Ji Kg Mt) Wh(Kp Mg Tn) Uw(dH jD Or) Eq(Kd Ri) Hp(cM Iq) Hf(mS nK) Wb(Id Or) Sf(Iq Qc) Wd(cP Qw) We(aD cM) Jy(kC oO) Pi(mY nK) mE(iP Kj) ApsC TzmH TrlW TvmW YdjT WfcT QwmZ JpvC YejY KlrP RfOp nRiP} hV{Ry(Ad aE An bN bR bS bX bZ cB cC Ch cO cU cW Dc Dd dE Ef Em Fc Hb Hf Ho Hp Hu Ib Iq Iv jE jF Jh Ji Jk Jl jU JY Ko Ky Lu Mh Mk Ml Mr Mz Nc Nd Nf Ni Nk Nl Nm Nt Nw Pk Ps Rg Tv Tz Uc Up Us Uv Vs Vu Wc Wd We Zq Ye Tl Tj) Yf(Ad Ap bN Ch Dc Ed Ef Fd Gb Gc Hu Id Ih Ii Iz Ji Jk Jl Jn Jt Kc Ke Kf Kg Kj Ko Kq Mg Mw Nm Nt Nx Oy Pe Pk Ps Qa Qt Qz Rf Si Sj St Tv Ua Uc Ue Wd Yg) Rx(Ad aE Al aZ Ch cJ cY Dc Dd dE Ef Ho Hp Is Jk Jn Kg Nd Nm Og Ps Qt Qz Rf Si Uc Ug Uv Vs Wd Ye) Vb(Ap Ch Cw Dc Dd Dg Dl Ef Gc Hp Is Iz Jk Jn Jt Kf Kg Ko Mg Mh Mm Og Pd Qa Qt Qz Tv Ua Uc Wd) Wh(cT Dc Dg Gc Iq Jn Kc Kg Kj Kn Mg Nt Pa Pd Qt Qz Rf Tv Uc Us Ux Vu Vw Wd Yg) Ru(cX Dd Dk Dl Ef Em Gc Ib Jn Jt Kg Kj Kn Lv Nm Nt Pd Rf Tv Vs Vw Wd Yi) Fc(aE Al bL bX cX dE Fn Hl Hp Iv Mw Ne Ns Og Pd Rg Uv Vz Yi Tm) Si(aF aL aY cF cM cT cX dK Fd Fn hR Io jD Ki Lx Ms No Ns Uh) nL(aD Af AS bI bO cK Cs Cv cY dR Gl gW Kf Kk Kp oH Qn Tv) Gh(Ad Ch Dd Ef Gc Hp Ji Jk Jn Kc Ke Mz Tv Un Up Us Vs We) We(AF aL aM aY aZ bB Bn cM cN cP Cx dE dK Fn Mb Ri) Gc(aF aL aM aZ Bc bZ dE dM Ed Fn Io Ip It Ns Ny Of) Wd(aF aM bA Bb cM cT dM Fn Jk Nd Nj qT qX Rg Uv) Vj(Ad aE aQ bA bS cY dB Dd dE Io Iq Kc Ns Pd Rf) nC(Af As cK Cv cY dR Gl gW hC Kf Kk Kp oH Qn) Em(aE aF aZ bB bL hW Io Ip Iv jY Nr Og Pd) Yg(aE aF cT dM Io Ip It Iv Jk Of qT qV Rg) Uv(Du Fd Gb Gd Ho Rz Sf Sh Yi Zq Zx Ye Tm) Ux(bZ cT dE dG dH dM Fn Jk Kl Of qW Vq) mM(Af bQ Cv Dp Ha hC Iz Jv Kf Kk Kp Vu) Hp(aF aL aM bB cP hR Jm Ns Of Qc) Ps(aF aL bB cP Ed Ip Ns Of Qc Rg) mH(Bb bO bR cE dE dR gW Tz Ug Um) Fd(aF Dc Mm Nm Nt Qz Tv Ua Vs) Vc(Cs Id Ik Iq Mt Pd Qu Ua Vv) Va(cM cP Fn Ip Ir Of Qc qW qX) Vh(aE bL bS Fn jD Lx Nr Ns Rg) cY(kC mI mS nD nH nJ nK nN oQ) Yi(Ch cQ Jy Nc Nd Nj Nk Nt) sC(Aa Ad Bb Ik Jt Or Pd Tz) Gb(bB Fn Kq Mh Ns Nt Ur) dR(kC kF kO mS nH nI nK) oQ(Af Cv gW hC Kf Kk Qn) Tm(cC Ch Ko Nt Rf Un) Uy(Ad Dl Iq Kc Mm Pd) Vw(aZ Hf Of qT qW qY) kO(Al Kk Kr Oa Ug Um) Sj(aF cT Fn jR Pd) Zq(aE Dd dE Fn Gn) Xa(bB cM cT dM Fn) Ye(aF aL bB cM cP) gW(kC lY mS nH nK) Vi(aF Ip Nr Rg) lX(cE cQ Qv Ug) mE(bG Cp Fa Um) mI(aD An Oa oH) mS(As Cv Pk Qn) nF(Cp cQ Ez Oa) hC(kC kF mY nJ) Zx(aL qT qW) oH(kC nH nK) Cs(nI nN) Gd(Ns Nt) Nd(Wc Tl) Ho(aF Ip) Yj(Ri Th)

Figure 14 Continued

Sh(Ji Mm) Rt(Ip Tv) Um(mF mP) Ug(kN mF) kF(Kk Kp) kG(Ar Iz) AnlY DikN EqMv GnNt NsUw YdaY SfcP JynJ KoOp OanN VtnD cKnK cQmU} qT{Zq(aD AJ Ar aS aU aV Ax cG cL cT dG dH Di dL Dp Em Fa Gn Gp Ha Hc Hv hW iB JD Jh jK Jn jQ Ko Lt Lv Mb Ml Nd Nf Nh Nj Nk Nl Nu Nx Oa Or Oy Pb Pz Qc Qt Qy Rb Rf Rv rX Ry Ss Tn Ub Uc Uk Uo Up Uu Vi Vv Vz Wh Yj Wm) Rv(aC Ad Af Ao Bb Bn cH Cw Cx Di Dk dL Ed Gc Hb Hu Ic Ii Iq Jd Jg Jj Jp Jt Ke Kg Kj Kn Ko Kq Li Lv Mh Mm Ni No Nw On Ow Qt Qu Rc Rj Ry Sj Ss St Uc Uh Un Us Uw Vj Vo Vq Wc We Yg Yj) Yj(aD aH aM As Ax bA cE Ch cJ cN cT dM Gh Hb hR Hw hX Id Ip Iz Jh jK Jt Kc Kj Ko Ks Lt Mg Mt Oa Pa Qm Rb Rg Ri Rj Rx Tz Un Up Us Yd Zw Wm Yf) Fc(Ad aH aM aP As Ax aY bR bX cD cN cQ cS dH dK Du Fp Ha Kg Ki Kj Lj Lt Mj Mx Na Nf Nu Or Oz Pa Pk Qh Qn Rb rC Ri Uk Up Uv Yk Tj) Rx(aH aJ An aW bL bM bO bR cB CH cM Cx De dG dH Du Gh Hq Hr Hu Jj Ki Mk Mx Na Nc Ne Nl Nn Pk Qn Qy Tv Vb Wc Tm) Si(Ax bL bN bX Cq Cs Di Dk dM Dp Du Gh Gn Gp Ha Iu Iv Lj Lt Lu Me Nl Or Qb Qc Rb Ri Rt Tv Up) Gh(aC Ad Bb Ch dL Gb Gc Hb Hu Ic Jt Jy Kc Ke Kf Kj Ko Mh Nx Pd Ri Ua Uh Vh Wc Yg) Du(An Co Cx Dg dJ Id Ii Iz Jg Jn Jp Kg Ko Mg Mt Nd Nj No Nt Oh Ow Rz Ua Ut Vv) Dr(aL bP cN Cp Di Ez Ib Id Ip Jg Jj Jt Mg Mk Ni Nj Oh Ow Qg Rj Uf Un Vj) Vj(aD aH bZ cE Ch cM cP cQ cT dG dH dL iC jD Jn Js Nl Nn Nr Nu Wm) Vb(Ad Ap Hb Id Ik Il Jh Jt Kj Ko Mt Mw Nw On Oy Rj Un) Wc(aF bP dG dL Fb Hb Jy Ko Mb Mg Nd Nj Oh Qm Ri Un) Fd(Ad Hb Ic Im Jn Jt Jy Kj No Nt Nw Qy Zx) cN(Gb Hp Ps Rt Sf Sh Va Vw Wd We Zx Ye) Yd(aY bP dJ Ic Mg Oh Or Ow qY rZ) Lt(dL Hb Ic Ji Jy Kj Lu Mb Ni No) Vz(Ez Hb Id Jt Kq Mg Oi Un Va) mF(aW bM Ct cW Fn Kj Tv Tz) Gn(Hw Id Jn Ri Tz Up Wm) Zw(Ad Ef Ii Kj Mt Un Us) Ry(bA dH Fp Hr Lj Oa Tz) Vh(bL bV dG eD Jm jO Vq) Zx(bA cT dH dM Qc Tn) Wh(Ch dM Ic Ip Mg rY) Ko(Gd Uw Ux Vw Yg Yi) mW(Af bM Cv Kf Kk Kp) Kg(Hl Ho Wf Yh Yi) Lp(aS Hb Kj Lu Nl) Ux(bA dG dH dM Un) Va(bL cI jL Jq jY) Vw(Ax cE dH eD hR) mZ(Ap Iz Qw Qz Vu) Yg(Jm jO jR rY) Wd(cL eD Iz Ub) Oa(Gd oP We Wf) Ur(mI nI nK nN) Vc(Af eD Oh Qn) Vi(dG Hb Jt Nw) nL(aU Kn Sr Tz) Em(Ax Ch Qn) Fi(Af Oh Qn) Gb(aJ Mx Nu) Hl(cQ Kj Pa) Ic(Sh Sj Xa) Tl(Kj Or Um) Jy(kC mT Uy) Ri(Ru Uy Xa) Pk(mS nC nH) cW(lX mH nO) dM(Op Sj Uw) oP(Cq Cs Or) Ap(eZ tM) Di(oQ Yf) Hb(Uw Yk) Sh(bL Mx) Wf(Kj Qm) Ps(Ip Jm) Rz(aJ aP) Rt(Qy Un) cQ(mE We) iP(mE nR) AlHp EqQm GcdH MmqB UbWn IdTm IvOp SfbL JtRu XaaP KcnD RmnH PimS aUnC} Ad{sC(aR AS aW Ax aZ Bb bF bL bM bN Bo cH cR Cs Cv Cw CX Db dJ Ed Fw hG Hw hX iA Ic iH Ik jF Jg Jk Jn Jq Js Jv jY Ld Lj Lv Ly Md Nd Nj Nk Nn Nq Nt Nv Ny Oa Oe Of Or Ou Ow Pc Pg Ph Pi QA QB qC QD Qg Ql Qn Qw qX Ri Rm To tS Ub Uf Ur vH Vp vQ vU wF tL Tj) vH(aC Ar aS bL bN cB cG cM Cv Di Ez hC Io It Jp JU Jv Ke Kn Ms Nj Nk Nr Nt oK Om Oz Pc Pg Qn Qw qY Ra Ri rY Tn Ub Ue Uf Uh Ul Uo vO yH) rP(aC aL aU bN cM Cw Di hG hX iA Ic iH Ik Io JU Jv Kn Ld lK Me Mn Nk Nr Nt Om Pc Pg qC Qn Ra Ri rR tU Tz Ue Un Uo vC Vt) vC(Ap aR cG dB dE hC Io lP Jo Jp Kc Kg Lv Nb Ni Om Ou Ow Pc pS Qn Qw Rg Tz Ub Ue Un vB vW) pS(aS bL cO cV Gl hX Ic Io iP Jq Jv Ni Nj Nq Nt oK Pg Qg Ql Qn Qw Ra Ub Ue Uf Uh Uo vQ) Of(aR bM dE Hx iB Ik In Io Js Na Nd Nj Nk Nl Oe Pc Pg Qb Vp Tj) vQ(aC bE cO dH hX Ic Io Jo JU Ke Kf Kg Me Ms Mw Ra Un Vo Vv) dQ(Aa aM aS Aw bA Bo cG cL Cp Dc Dd dF gT Lx Nx On Pa) zG(Af aR cO cX dH Ic Io Ip Jv Kn Ni Nk Nr Pc Pi Qn Ri) Js(Aj bX Ji Jr Kx Lh Mz Nh Nj Nv Nw On Pc uL) vW(aI aL aS cH cM cZ jG Nn Nq Nt Qb Qd Tn) cX(Iu Ji Jy Md Mt Ne Nh Nl Nw Pe Rg To) wC(aC bN cO Ic Ju Jv Kn Me Nd qZ Vo) vB(aC Ap Cw Db Di Ic Kp Ld Me Nk Pc) Yj(iC jH jI jK jO jP lK qV qW qX) qY(Du Hl qA qB qC qD Rz tS vU Zx) qG(hX Ic Io jY Kq lM qA qD uN uZ) uZ(cU Ii JU Me Mq Nd Un vU) In(bM bX Ik Jd Ji Jv Kx Nj) gT(aK cL cY Ly Mv Mw Nb Pc) hR(Fd Hl Lp Ux Uy Wf Yh Zw) iB(Gh Hp Lp Nn Op Ps Sh Zw) qZ(cH cO Cv Ke Mr Mt Qn Ri) rR(Ii Kq Or Qd Qg Qw Un Vt) uM(cR jU Me Nb Nd Ou Ow Vv) uW(cL cU hL iP oK Ri Uf Vp) vO(aS cR Nb Nq Ou Ow Qc Qd) vU(bL Kn Lv Nk Pi Rg Ue) tS(aL bL cU cZ Nn Pi) yH(aW cR Ed Fw Jv Ld) dV(Ly Mk Mm Mu Mv) wF(cO Ju Kn Lh Vo) jT(kG nF Op Uy Vj) rQ(aW cR Ed Ik Ld) uL(aC Cw Di Qg Uf) uN(bL iP Nd Nq Nt) Do(Ez Jy Rc Vv) Zw(jG jH jK lK) cZ(vP vV wB wL) jD(Em Gh Hl kO) wD(cO Jv Me Vo) tL(cU Ii Ju Vo) rV(Me Nd Un Vt) Bo(bM dE dO) Fc(eD iC jU) Nj(Nk vI vS) Zx(jO jY lN) Uy(jM jR lM) aL(uX wB Tk) aR(bU bX wL) eM(Ly Uh Um) Du(qW qX) Th(wL Tj) Mn(wQ zI) Nk(qI tX) Yd(eD jO) Lp(jO lK) Vj(hA iC) bM(Aj Ct) cR(wJ yE) gN(Mp Oz) gW(qO qP) mF(jE jY) hX(qO qP) tM(Ii Vo) rO(Un Vt) uV(Pg Ra) uT(Jv Uf) vP(cU fY) AaTk FwKx GnkR NnqQ NqwG MzWn NdvA YijK WdqX WehW WfjU KpvI KqrN LdwL VbiC VqdO PcqI PitX aIwB bLwK cWuP dGuX zIlK} iC{Vw(aD aI aJ aS aZ bA bB bC bI bJ bL bN bV bZ cD Cq cW cZ dG dH dJ Dl dM Dr Fa hW Ii Il Ip Ir Iu Jl Jn Js Jt Ju Kd Kg Kn Kq lN Md Mh Mk Mv Mw Nc Nd Ne Nl Nr Ns Oh Om Ow Pe Qg Ql Qm qY Rm Rx Ry Sr Ss Tv Ue Un Uv Vc Vj Vq Vu Yg Yi Yj Tm Wm) Vb(Ao Ap Ch Co Dg Dk Ef Gb Gc Hb Ho Id Ii Im Iz Jd Jg Jk Jn Jt Ke Kg Kj Kl Kn Kp Kq Mg Mm Mw Nm Nw Om Qt Si Tt Tv Ua Uc Uf Un Uw Ux Vh Wh) Fc(aE aI AL aZ bB Cu cX Dl Fn hA Hq hW Jo Jt Kd Kn Ko Lu Lv Mh Mm Mr Mv Mw Nb Ne Nl Ns Ps Rf Ry Ur Vo Yh Yi Yj Tm Th) Zq(aD aE aL aR aS aZ bA Bb Bc bI bJ bM bV bZ cG cI cU cW dK dM Em Fa Fn Fy Kd Kg Ko Kr lK Nf Qm Qt Qv Ry Ug Ur Uv Vc) Vj(Ar Bo cI cW cZ dB dD Dk Fa Gp Hq hR hX Id Io jG jQ Jr Ki Ky lN Lv Mf Mh Mk Ms Ns Pd Qm Qv Rj Ry Ul Ur) Si(aE aL Ar cM cX Dk dN Fn Fp hR Ip Jk Ko Lj Mh Ne Nf Nr Ns Nu Oh Oi Pc Pd Qb Qc Rg Rt Ry Ut Uv Yf) Yg(aH aL Ap aY bB Bc bP Cq Cs Dc dD dJ Fn Fy It Nb Nf Op Or Pz qV Rh Ry Sj Sr Uh Uv Uy Vq Wh) Yj(aD aE bB cM CX Dg dK Fa Fn Gb Gh Hb Id Kc Kj Kq Lv Mb Ps Qm Rf Rj Rx St Uf Ur Yi) Gc(aL Ar bB bZ cF Cv dD Fa Fn Gl Gz Hf Hu Jy Lh Li Mr Nf Ni Or Rf Ua Ur Tl Wm) Ux(bA cL cM dG dH Em iB Mv Ni Or Pe Qm Qt qV Rz Uv Vu Wh Wm) Uy(Ch Dg Dl Ef Gb Hb Iq Kc Kf Kg Kj Kn Kq Mg Mh Nm Rf Wd) kO(aC Ch cR cS Fn GL hC iP Kj Kn kS Qm Rj Ur Ut Vs) Gb(aI aY bB Bc Bo cM Cs Cv dD Ed Fa Fp hR Qv Ur Vq) Tl(aL aS bB cL Cs cU dA dM Fa Fy Ji Qm rC Ry Wh) mZ(Ao Ef Fn Fy HC Hf Kz Qu Rb Ue Ug Uh Uk Um) Wh(Ap Co Dg Kc Kg Kj Kn Ko Kp Kq Qy Rf Un) Ry(cQ Fn hR Jy Kc Nf Nw Qd Qm Ri Tt Un) Rx(Fn Gl Hu Li Nf Nv Nw On Pe Qd Qm Tt) Uv(Ho Ps Rz Uw Vh Yi Zw Zx) mW(bO Fn hC Ju Kf Kj Ou Uo) Vh(aL cF Fn hR Nf Pe qV) cM(Hp Ps Va We Ye Xa) mS(hC Hf Or Pk Us Vt) Em(Ch Fn Jg Li Mk) Tr(nC nF Rt Rv Wd) Yh(Cv dJ dK Ip Nj) Un(Fd Gh Tm Xa Yf) Uw(cF dD Fa qV Vq) Vc(cG Pd Rz Tn Ua) Ho(dK Ip Pe Ur) Tz(nJ nO nT nU) Hb(Dr Sh Yd Zx) Hf(mE nC nH nK) Wf(Kc Kg Ko Qm) Ko(Dr Op Ps) Rz(Mh Mz Pe) Ru(Jr Kc Qy) Rf(Eq Gn We) Or(kE mY nB) Vi(cP hR Ip) Vt(nF nT nU) mE(cE iP Kr) mF(Dp Fn Vs) Yi(dK Jy) Ps(bP Ur) Rv(Gl Jg) aY(mT Yd) bM(nO nT) nF(Fy pF) hC(mM nJ) kG(Ao Uk) BbsC ChnH YfJi FdIp GnIq MmHp ZxKq WdbP JtYe TmQm KgOp RtNw WncL OwnD cWmU nRiP} mM{Lp(aA aQ aS aY bB bI bN bP bS bZ cI cK cY dR Du Ed Fa Fd Ha Hf Hp Hq Ih Ik Il Im Iq Ir Is It Iv Jd Je Jl Jn Jr Js Jt Kg Kl Kn kP Kq Kr Ks Lh Li Lj lX Me Mj Mr Mv Mw Mx mY Nc Nj Nl No Nq Nr nU Nv Oa Oe Of oH Op Ou Ow Pd Pe Pf Pg Ps Qa Qd Qe Qh Qm Qn Qy Qz Rt Tv Tz Uf Ux Vi Vs Wb Zq Xa Wm) Fd(aE aR aY bO cO cQ dK dN Dr Ex Ez Fc Fn gL hC Hu Ik iZ Ji Jm Ju Jy kE kG kK Kn Ko Kp mF Mg Mn Mr mY nB nC Nf Ny Oe oN Pc Pd Pf Qb Qg Qm Qy Rt Sf Sh Sj Up Us Ut Uv Uy Vw Vz Tl) Du(aY bP cG cO cQ dG dK dN Dr Ex Fc Fn Gn hC Iq Ji Jm Jv Jy kC kE kG kK Kl Ko Kp kQ mF Mg Mr nB nC nW Ny Oe oN Pc Pd Pf Pg Qg Qv Rt Sh Um Up Us Uy Vv Tl) Vz(aK aS aV aY aZ bA bH bI bJ bN bP bS bW cB cK cT cW cY dJ dK dN Fn Ih Il Iv Jo kP Kr KS Li lW lX mF Mg Mr Mx Nd nI Oa Oe Og Qn Tr Uy Yf) Fc(aQ bN bP bS cK cM cQ cW dB dN Ex Fy hC Hp Im It Jd Jr Jt kG Ko kP kQ Ks Ld Lx Me Mj Mn Mr mS Mx Nj Nv Oe Pf Pg Qm Rz Up Wb Th) Zq(aK aQ cF cK cP cY dC dJ dN dR Eq Hb Hf Hx iA Iq Iv Je Kg kP Ks Lj Mh Nf Nr Nu nW Nx Oa Oe Or Pa Pd Pe Ph Qh Qt Qv St To Tv) jL(aD An Ao Ar As aZ Ba Di Dk Dp Ez Ha Hb Jy Ke Ki Kp Qt Qw Rf Ss Uf Ug Uk Um Ur Vs Vu Vv) jT(aJ An Ap Ar Ax BA Bn Dk Ef Fb Ha Iz Kj Kl Kp pF Qh Qv Rf Tv Ue Ur Vo) Hp(cK Gn Hr Hu Hx Ik iP Iq lW Mq Na nC Ni Oe Pz Qb Um) Tl(bS Fa Im Ir Li Lj Mx Nj No Nr Oa Og Pe Ph Pi Qn) Zx(Hf Jr Ko Kp Lj mW No Nt Pe Pi Qm Un Ut Vi Vs) Vw(bS dB Hf iP It Kn Mh Mx Ni Oe Og Pz Qv Uc) Sf(bS Ij Im Ir Li Mn Mx No Og Pi Qg Qm Th) Rt(bS Ih Im Ir Je mW Mx nC Ph Tv Ut) hX(aZ bZ cW Kc oK oN Or Ou Ph Rh) Ko(Gb Ps Sh Vj Wd Wh Yd) Uy(bS cK Im Iv kP Mx Og) lN(aG aY bZ cE dM iJ Nj) Wb(bS Ir Mx

Figure 14 Continued

Oh Pa Pf Pg) Lx(aA aD An aO aR aV bB bC bF Bg Bn Bo bQ bU Ch cM cO Cu Dd De Di Dk Ii In Mf Ml Mv Nd Ny Og Pa) bB(BA bI Bo bP bR bU cA cF cG cK cV Cw dB dG dI dL dM Ef fR Fw gN Nv Of) aV(Aa aD al bC Bo cG cH Cw dA dB dC dF dG Di dM dO dR fR gC gN gW Im Pg) Pb(aG aM Ap BA Bc bH bU cT dC DD Dg Gp Mb Mt Nc Ne Nj Nv Ny Oi) cG(aD Af Al An aR As Aw bF Bg bM bN Bo Cp Cq Cu Cv De Fp Gn Il Nk Pe) Nx(Aa al bH Bo cH cK cM dB dI dJ dO eM Fp gC gN Mg Mx Nf Ni NI) On(aA Af aG aP aR bF Bn Bo cR cY Dk Dr gL Il In Ms Nf Pa Tj) Nl(aA aR aX bF Bn cE cL cR DK dN Dr Fp Nc Nf Pa Pe) Oz(Aa aH Al aM Ap bJ cH cl Dg Im Ma Mf Mg Ne Nj Of Om) cP(Af aR bQ cL Cp Cs Cu De dF Di Dk dM fR Il Nd Nf) dF(Af aO aQ aR bF Bn Bo cM cY Di dN In Mf Nf Tj) Gn(Aa aS aY bE BO bQ cL Cp Ct cW Dc dL gC) cR(aL Bo Cp cW Mb Mf Mg Ml Mt My Ne Nh Og Pd) Nw(aD Af al An bC bF cD cM cU Dd Di Mk Mx) Bo(aR bO bQ bU cD Cq Ex Gt Mt Mv Na) Mv(cK Cs dG dI Fp FR gC gN Pe) aR(bA bQ Cw cZ dD gC Mk Ne Nv) Pa(Cs dB Ef Fp fR gC gN) Pe(aH cM dB Mt Na Ne Oh) cY(aD Di dO dR dV fR gW) aH(Af Aw Bn Di dM Nf) Nd(bR cI cJ Nh Pd) Dk(gC Mt Nh Oh) Fp(cJ Mt Na Nc) Ly(aM dV Gc gN) Ne(bF cL dN In) Mb(Aa Pd Pg) aM(bF cE Ef) aO(dG Ih Nv) bQ(cK Cs dI) dM(aQ dO gW) Bn(aL bE) Cp(bO dJ) Di(aQ Mk) Em(gC Oh) Mt(dK Nf) Il(Im Mx) aI(Aw Cq) cM(fR Pf) AaMf AfaL BgbO EfOe FwcA MkcH MndV NadI NidJ NjbM InOf OhaZ aWgC bFdL cLcZ cVcW} lK{oP(aF Aj aO Ar aS aY bE bG bO cF cG Ch cN cS cT cW dC dK dM Fy gL hC iH Jf Kc Kr Kz oE oK Or Ou Ph Rh To Tv Uo Vt) oQ(aC aF aL aO aQ aV aZ bA bB bO bR bV cD Ch Co cP dA dC dD Fa GL hC hG Jf nW nY oK oN Pi Rh St To Tz Uo Ut Vt) Xa(Af aY Bn cP cW Cx dJ dK Fc Fn In Ip Is Mr Ni Pd Pi Qn Rj Rx Ur Wb) Yj(aF aZ bL cT Cx Dd Io Iv Jn Kc Ns Og Pd Qz Rg Ry Tv Wd) vH(Ap Ar Dg Fy Ii Jp Ke Kg Kl Kp Kq Lx Mt Po Uf Uh Un) Kp(nC nH rS sK uL vA vB vP vV wG wL wP yK) kG(An Ao bE bZ cE dG dM dN eF Tv Tz Uk Um) mZ(aX bA Cu EF Fn Hb Hc Hf Iz Or Uh) Ap(nF qP tQ tT tU uL uP vC yL tM tL) aY(Fc mP mS mW nU oO Ru Ry Si Vh Zq) Bb(qP rP rQ rT uL uP wL yD tL) cP(Eq Ho Hp Sh Va Vw We Wf Ye) mW(dH Hc Ju Kj Oa Ou Qv Um Vs) dM(kE kK kN lX mH nO nR nT) nD(dA Hb hC Hf iP Ju Ke Pi) oO(aZ cH cS dC dK Qw To Uo) Fc(Aw bL Eq jF Qz To Wc) Fd(Id Ji Jt Ko Li Nt Tt) hC(mP mS mU nF nJ nT nU) Wd(aL bB bP dH iB Ni) Uf(uI uL vA vS vT wP) Vw(dD Gp Mn Nd Pi Qv) vP(Jo Kc Kg Nm Pc Vo) Tt(Rx Ry Vb Wh Yf) Tr(Ru Sf Sh Uw Wc) Ii(uR wD wH wL yL) Kf(nB nC nH nK nO) Ko(Ps Ru Wb Wh Yd) dH(Gc kN mI mU nF) Gl(uL uR vB yK) Nj(Ry Ux Wc Tl) Zq(Dd Mr Pi Qv) Jt(rO rP rV uZ) Kg(tQ uL vV yK) Uh(rQ uO uR wB) Un(uM uR uZ tL) Vo(wD wJ yK Wn) aP(mE mS mT nF) cW(kK kN mE mY) nT(bE dN oE Or) Eq(dJ Ji Uv) Gh(bP Ji Uv) Nt(Rv Yh Yi) Ni(Gd Hl Wc) Yd(Hb Kj Kq) Ru(Ib Pd Vs) Uu(kC kF mU) aL(Va We Zx) cE(lY mF nN) nC(Cv Kk Vs) nH(Cv iP Kk) Aa(qH rS) An(kC mF) Aw(nU Si) Cw(uL wP) Dg(uM wC) Nm(uU vV) Mr(Yg Tl) Ic(uL wJ) Wb(Iq Um) Ss(Em Rx) Wc(bP dJ) Jp(rT uR) Ke(tQ uP) Ry(Hu Pd) Wn(Ly Rb) mP(bE qZ) nF(Di pF) iP(kC nL) BakN CozA YfbP FnlW GbQv GcNd NuwG HlRf UaPs UbmF IdZw IpWe SibL WfPd QuRv KjkO KmB RxcQ OamT TkcH UwdD VtnU PcwD PinJ PknK mEiA} gW{Ho(aD aI Aj aK aL aW Bg bM cM Ct CV cW Dd Ed Fn gP Hl Hx Jh Jl Jn Ko Kr Kx Mk Nf Nh Nx Oe Of oK Ow Qa Qe Rf Ry Ur Vb Wf) fR(aD aL aM aQ aU aV aW bB bE Bg Bo bR bU cH cM cW cZ Db dD dH dJ Dk dO Ex Gc Gn Gp Jn Mb Na Nj Rx Uy Vb Wd Wh Yk) Si(aD aK aL An aW BB bO cR cS cV cW dL dR Ed Fn Gd In Iq Kr Ky Lx Mk Mq Nf Of Ou Pg Po Qd Rt Ur Va Vz) Fc(bL Bn bO cR cS cV dB dE dR Ex Fn Fw gP Il Iq Jl Kr Kx Lx Mn Nh Nx Ow Ph Po Ps Qa Qb Qc Qd Qe St Us) Ps(aD aW bB bM cM CV cY dR Fn Ip Is It Je Jy Kp Mk Mr Nc Nf Ni Ru Ur Uy Vb) Uy(bN cR Gc Ih Il Im Iq Jl Jt Kf Kg Kj Kn Ko Kr Nx Qa Qb Qd Qe St Vq Vs) Vj(aJ aQ aV aW aZ bO cD cR cY dB dE dR GP iH iO Kp Mb Mf Mk Nf Rf) oP(aZ Ch cS cU cW Fy Iq Jf Kc Li oN Ou Pb Ph Ql Rh Uo Us Vt) dR(Fd Hl Hp Ux Va Vc Vh Vi Vw Wb Wc Wd We Yg Ye Tl) Vb(Dg Gc Il Jn Jt Ko Lx Qa Qe St Tr Tv Us Vh) Vw(aD An aW bM cR cV Fn iH iO iP Nf Nh Ur) Nx(Hp Rt Ru Sh Va Vz Wb Wf Zw Zx Tl) Fn(Fd Ry Rz Vh Vi Wc Wf Yg Zq) cV(Fd Hp Op Sj Vh Wd Wh Yg Ye) oQ(bB Ch Fr Lh Ny On Rh Ut) Gn(bN Cp dB dV Iq kR Qe) Vz(bN Jl Ko Pe Qa Qb Qd) Jy(GC Op Ry Vc Yj Yk) Ru(cR Il Ko Kp Kr Qa St) An(kC kO mI nK nN Yg) Gc(bB bM Bo Ip Jr) Wb(iJ Ko Qa Qd Qe) Vi(aW Kp Mk Nc Nf) Yg(Bc bM Nf Vt) Qa(Rt Sf Sh Zw) mW(Io Nv Ny Oa) Ic(qO qP tT) Ji(eM Gh kO) Wf(Mn Nf Pg) dV(bB Bc Mk) nH(Kp Ny Ph) nK(Fp nN Oa) Ap(qG uZ) Bb(rP rQ) Du(Pe Qd) Fi(Ex oN) Hp(aL Ur) Zq(bV kQ) Wd(bB Nh) Ko(Gb Va) Ry(Mn Nf) Op(Cv iP) nC(Kp Ny) kC(Lx Mx) BgkN CozA GtMb HlQd TrRt IjmF YkPe YjJl SfiP ShSt QzeM QudO JpmZ JrnI UfuW VccG PdkO aDgV aYmP dMnR} rP{Bb(aC aH aI AL aM aQ aU Bc bE bN cD cR Cv cY cZ dI dJ eZ Hr iB Ic Ih Ii Ip jE jF Jj jQ Ki Kj Kn Kz Ly Mr Mt Mz Nd Nh Nx Om On Ow Pd Qh Qx qY qZ Ra Rb rR rT sC sO Tz Ue Un uP Uv vC vI Vo Vt) rR(aE Ap bL cH dB dE dI Ed Ic Jp Jt Ke Kg Kp Kq Lu Mz Ny Om Pc Pd Pi Pz qV Rf Uh wG) Jt(aC aU cH cM dJ Hx iA jG Jv Ld Mn Nj Nk Nr Nt Oe Or Pg qA QB Ra Tz vC) Kq(aC aI Al bB cM DD Ed Ld Mp Ms Nr Or Pd Pg Ql qZ Ra Tz Uk Uu Vt) Im(aC aL cH cZ dG Ed Hq iA jG Jn Js Nk Nn oN Qa Qb Qd qY Ub vC Vp) Jd(aC aE AL bN cH Cw dI Ic Jp Jv Kc Nd Nr Pa Pd Qu Tz Uk uP) Dl(aC bN cH cR dJ Ed Hr jG Jv Ld Nk Nr Or Pd Pi qA Qd Ra rX) Un(aU Ax cH cM Cq Ed Fw Hr iA jG Ld Mp Nd Or qA qB qC qD Ql) Vt(bL cH cM dE Hr iA jG Mk Mp Ny Or Pi qB QD Uk Vp) Om(Aa bB cH cI Ed Fw jG Lu Nn Or Ph Pi Qg Ql yL) Ic(aH aI Cv hB jG oF Oi Pd Pz Qh Tz Uk wJ) Ra(Aa Aw Ch Cp Cv Cw Hb Iz Kj Kl Ko Pi qB) Tz(Ap cH cI Cp Cw Di Ef Iz Jp Ko Qg) Ii(Ed Fw Ld Or Ou Pg Pi qB qC rX yL) Ji(bB cM dJ Jq Nk Nn Or Ow Pg Ql Rh) Ap(aL cM iA Nx Or Qu uT tL xA) Kl(bB bN cM cZ dB dE Md Nr Or) Pd(cH cI Nj Nk Nn Nu Or Pi) aC(Ar Ax Cs Fp Gl Nd vT Th) Dg(aL iA jG Or qB Qd) Uf(cE iA uT vT wP xA) Aa(Bc Cp Jh Nr uR) Or(Cp Jp Mt On Ue) qC(bL cC dB Ms Mz) Nr(jG Ke oN Qg) Al(cH Nk Ub) Ar(cZ Ed Ue) Th(Kj oE Pz) Fy(aI bB iA) Mz(Ed Fw Uk) Jp(aI cZ dJ) Pc(Cp Ef Iz) sC(Pz tS yL) Qg(Ih Rm) cH(Cv dI) jG(Il On) AfbN CpQu CwPi EdSr PoNn TrKc PzqB KgtS KjPg LiaL NycZ UhbB bLvT cIdB} Ap{vC(aG aJ aM AR aS bL cU dB dC dE dG eZ fN iA Ip jG Jh Jo Lv Ly Mg Mt Nb oE Or Ou Ow Oz Pd Pi qA qB qP Qu Tz Ub Uk uL vB vH) tM(aS bL Cu cX dE eZ fN Fw Ha Hr Hx iA Ij jM Jq Js Lj Lw Nn Or Pa Pe Pg Po qA QB Qm Qn Qu Ri Tn Tv Ub Um Vp Vu tL) sC(aO aS aZ bM cH dG Ed fN Fw iA iZ jG Md Mp Or Pi qA qB qC QD Qu rX tS Uk uT vH Vp wB zA Tj) uT(aJ bL cO cU cX Dl fN Ic iZ jM Jq Mt Ni Nn oK Pi qA qC qD Qg Qm Qn rC Uf uN uP uZ vA) uU(Af aS cH cM Cx fN iA Jq Js Ky Mn Nt Oe Pi Qd Qn Qu Ri Tn Tv Vu) wB(cO cR CX Ic Jq Jv Ni Nn oK Ql Qn qY Ra rC Tn tU) vB(aC aJ cH dG fN Fw jG Jv Kk Kp lN Ny Ph qA qB qC uG) uL(aC aL aU cH cZ jQ Kk qB qC Ql qO qP Ub uG) vH(aC aM aU bL cU Dd Mg Mt qP uG Uk Ut) eZ(rO rR rT rV uM uZ wC wD wH yL tL) xA(aM bL cG cO De Ic jM Mt qC Qn Rj) pS(aJ aS cF dI iZ qC Ql Qu Ra tQ Uf) uP(aI cW cZ dL eT Mn oF qA qB uW vT) vU(aL bL iA iZ Ly Mn Qu Ub uY uZ Vp) tS(aK aL aS aU cM cY Ha Mn Pc Ub) vI(aK aS aU cH cM cY jG Oe) uG(aR iA Nb Ou Ow Tn Tt) vP(cH cZ fN qB qC QD) yE(aS Mn Oe Qd Qm Vu) cR(tN uX vW wJ zA) rR(Ed fN Ic Pi Qg) qP(aO dG qO uI uX) cU(uI uX vT zA) wK(aI cM Mn qG) qY(qA qB qC qD) Wh(hA lM rC) Vo(wC wD tL) aS(sK sM uZ) eD(mP nF oQ) eM(Ke Qg Uh) wQ(aJ Ic iZ) Mn(tT wJ) Zq(Qz Vq) aL(tQ tU) zG(aC cM) qI(Oe Qu) tL(jE Jj) zA(dR Up) qQ(dG Pi) uW(iP oE) DuqW MquZ YhhR WfjP OfqB OutN PbgN aOyK bLvT cHwH dJtT fNrN mHjR wLiZ qOuX} Ic{xA(AL aQ aZ bE bL Ch cQ Cv cW cZ dB Dd Dg Dk EF hP Iz Jd jF Jh jM Jp Ke Kg Kx Ly Ms oF Og Oi pS qP qW qY rR sC uI vB) rR(AR aS aV Aw BA bL cH dB dE Ed iA jG Jv Ke Kg Kn Kq Ml Mq Nd nY oE Om Pd QA qP Tz Ub Uk Ur Ut wC yJ tL) wB(aE Ao aZ dB dE EF Hc iH Jd Jh Kl KQ Mq Mr Mv My Oi Om QY Ue Uf uL Ut vB Vo) wJ(aC aQ aU bE cL cR dB Dk Ha iH iZ Jd kS Mg Oi pS sC Tr Ub Vo yJ) qG(Al Ar aS Ba dB Dc Dd dE Fy Jd Jt nY oE Pd Qh tN Tz Uk uR vP yH) sC(Ar aS Bb jG Jt Lu Mq Nd nY oE Or Pd Pz Qh Tz Uk uT vT wQ tL) uT(aC Aj bE Ch dE Ef Jh Kg Kl Kq Mg Oi rC Uf Vo yJ yK) vP(dI hB iH Jh Mn Mq Mv Mx Oi Om pF Pz Qd Ue Uk uZ Vp) yH(aH aI AL bB cM Db eZ iB Mb Mn oE oF Pg qB uW) pS(Ar Aw Db Gl jG Jp Kg Kl Kn Kq Ks lN nY qQ vT) qP(aI cS fP hB hX jR Oi pF Pz Qd qO Ra rS St uL) zG(aE Aw bE Bn Ch cM Cp Ef hB Iz Jh Kj Kl Uu) qI(Al Ar Bb bL cM dE hB iA jG nY oE Pd Tz Ub) wQ(aG cJ hP iH Ke Kg Kl Kq oH qY rQ) rQ(aU kR Mg oE Pd Tz Uk uU) oE(qQ rO

Figure 14 Continued

Figure 14 Continued

Nk Rh Tr) Wh(Bg Ch Co Cp Ct Dk Qz Ss) oP(Cq Fy Mn Or Ow Pb Pf Wm) Fn(Hl Rt Rv Wd Wf Yh Yi) nT(aW Bb bM oH Qw Tr Vt) nK(cW
cZ Ed Hf Mk Pi Vs) Eq(aE aZ cI Mv Ns Ur) Mh(Gb kE kN nB nN Ru) Zx(Bg Ch Ct Dc Qt Qz) mW(Hx In It Kj Nc Ri) oO(bO Je Jy kQ Pb Qt)
aY(kP mT nF Si Vc) mF(Dp Hx Kj Ri rY) mY(Hf Mb Me Mk Rh) Nj(kO nF nN nU) aE(Rv Wf Yh Yi) cW(mI nI nL nN) mT(Dp Hx Kg Kj)
nC(Ch Qm Ut Vs) Ct(kO mH Vb) Me(mS nB nH) Mk(mS nD nN) Wd(Bc Cq Jk) Xa(Fy Qn Ur) oQ(hC Je Wm) Ch(nF nL) Gp(Vj Vw) Ms(nD
Va) Yh(dK Rf) Yi(bP Rf) Qz(Lp mZ) Qm(kO nH) Wn(Ue Vo) Ur(Hp Ye) Uw(Bc dD) Vb(Bg Of) Vs(nH Sj) Pi(Ps We) nU(Bb Tr) iP(mI nR)
kN(Hx Uu) ArEm BonF CumZ YfNs FdVv FyUx MbnD MflW HfmS ItVw YgKo YkcP WbUm SidH SfPd JnVa RvPf RmmH NyVh UtkO aGmE lYrY} dV{Mf(AA aK aM aN aR Bb bO bR cD cG cJ cP dK Ex Gt Lv Lx Ly Mk Ms Mt Mv Na Ne Nh Nl Nx On Pb) aV(aA aN aS BC Bg bJ bU cH cJ cL cX De Dg Dl EF Gn Mt Nd Nw Nx Oz Pb Pe Pf) Ly(aH aL aQ Bb Bg bM bO bX bZ cG cI cP Cw dB dE DG Gn Ma Md Mk Ni Nw Om On) Mb(Ao aY bV cC cG cZ Dg Di dJ Dk Fr gN Gt Il Lx Me Mh Mj Mn Nd Nw Oh Oy Pb) Mk(aA Af AN AO aP aQ aR Bb Bn bZ cA cO Cx Dk Em Fp Gp Mr Mv Mw Nf) Gn(aC aH aK aQ aU aW aY Co cS cY cZ dD dR eF Ij Il Mw Ni Pg) aK(aA Af aN aR As Ax Bc Bg BN Bo cE cH cL Ef Fp Nf Oz) cY(aA aM aU bB bC Bg bN bU cH De dI Dl Ef Pb Pc) Il(aH bU cG Cq Cw Gc gP Ih Mg Mj Mn Mp Nl Pb) Bc(aQ aU dR In Mv Mw Nc Nd Nf Pc) cP(Af Bn Dk Nf Nx Oz Pa Pb) Fp(aH aQ eF Ih Mz Nj Nl) Nw(bC bE cD dA dM Mg Nd) Gc(Ma Oy Oz Pa Pb Pf) aQ(bU cH dI Ma Md Oz) On(aO aP aU dH Nv) Pb(aL bX Mn Ne Oe) Mz(aR bB dN Em) Nj(Ar Cs Gt Nk) Cq(In Mv Na) Cx(dD Oz Pc) Ml(aW cL Oi) Nd(Gt Lx Me) Co(aN Bn) Dk(dD Nk) Dl(Cp Ni) Em(Lx Mp) Mg(aO In) Oz(cJ cO) Pc(bG Me) aR(Mj Oi) bB(dR Oy) BbdD LucG MnPe NfaH NkNl IhaO InOf NxNy aAdR aMeF} hX{Wh(aC Aw bP Cx Dc Dg Dl Gb Il Im Jd Jh Jn Jp Kc Kf Kg Kj Kq Lx Ow Pd Pf Po Qg Qt Qz Ri Rj Ry Rz Tr Tt Tv Un Us Va Vq Vw Zx) Vj(Ch cY Dc dL Fy Hp Hu Iz Jh Ji Jn Mh Ms Or Oy Pd Qh Qt Qv Qz Si Tv Tz Ua We Ye) Ru(bP Dl Em Gc Ib Il Iv Ji Jn Jt Kf Kg Ko Kr Lu Ni Oi Pd Ri Ry Si Ug Uk Wf Xa) mE(Af bX Cs cU Cv Cx dB dR Ez hC Kc Ke Kf Kk Kp Pk Qn Qu Rh Ua Ug Uk Vv) kN(Af Aj As Cv Di Ed Gl Ha hC Kf Kg Kk Kp Kx Ph Qw Ra Rb Ug Us Tj) nR(Af As Cv Cw cY Dg hC Jy Kf Kg Kk Kp kS Ph Pi Pk Ri) Si(aY bB Bo Cq dJ Ed Fd Hv Jm Lh Ms Nd Pi Qd Ql Yd) mF(An Ch Ct cW Ed Fy Jf On Ou To Ub Vs) Ry(cB Fy iB Mv Nc Ni Nl Oz Qt To) Nd(Em Fc Gc Gn Vh Vw Wf Zw) Gc(aM Db hW Is Mv Of) Fc(dJ Fw Hc Kz Vt) We(aM bB cV Di Pk) Of(Em Hp Va Vh Vw) Gb(Ko Mv Un Vq) cG(lW mZ nH oQ) mH(Or Ou Uk Us) Em(Ip Mv Uv) Ni(Gd Hl Yi) Wd(bB Pz Vq) Wf(Hf hW Uv) Xa(Hf Pk Ur) Um(kK mP mZ) Vh(bB hW Vq) nN(Nj Ou Ph) lX(aZ cW hC) oF(nC nH nL) Aa(sC uR) Yi(Nc Nj) Yj(bA bL) Wb(Ji Qm) Kx(kK nC) Ri(Rv Yd) Vb(Aw Tt) Vw(Cq rC) iB(Rx Zq) BbqP FbkK GhcB HphW IpRt ZxbB JiPs TldJ KjkO OrnU OulY UkmZ UskP UwVq VaaM PkmS nBhC} rC{Xa(aH aP Ax bA cH Ct Cv Dc dI Fc Fd Fy Ni Ou Qh Qu Ri Rt Rv Sr Tn Vb Vi Vu) Rv(Em Hu Jn Jr Jt Kn Ko Kq Nt Pd Pe Rf Ss St Un Vw Tl) mE(An Bg cE Cs Cu dE Dk Iz Kd Kp Oa Qu Tn Um Up Us Vp) Kp(Eq Fd Gh Ps Rt Ry Sh Sj Uw Vb Vh Wh Yd Yf) kO(Al AN Dd dN Kj Kn Ky nY Pk Ql Rm Ue Um) Si(Db dI Fy Hv Ip Jl Me Nj Qd Vp Yh Yi) Yj(aF bA bE Dl Em Iq Ji Jn Ki Pd Tz) Hl(Aw Gc Jn Kg Ko Lu Mh Nt Ps Ua) Wf(Hb Hv Ip Ji Jn Kg Ko Pe Qm Tz) Nj(Dr Du Fc Fi Gc Ps Vc Vw Wb) Yi(Gc Hb Jr Jt Kg Ko Nc Nt Pe) Yh(Hb Jr Jt Kg Ko Nc Ni Nt) Zw(Dl Gc Hb Iq Ko Nt Pd Tv) mI(aM An bM Cp Iz Tv Tz tF) Em(Aw Bc Ch Di Kd Mh Zq) Fd(Gb Gc Jn Jt Kf Pd Rc) nC(Cw Dl Ha Kx Pk Qw Rm) nL(An bM Dl Ha Ph Ql Tv) Rx(Nc Nd Ni Nk To) Vw(dI It Iu Nu Ri) nJ(bM cG iA Qw Tv) Fc(Ki Lj Me Oi) Wh(Aw Iz Rc Zx) cM(vS vT wH yE) Me(Hp Sj Vh) Ni(Ry We Yg) Ji(Ho Vi Yg) Wc(jE jG Mk) Ko(Gc Ps Yd) nH(cG iA Ue) Aa(uR vO) Aw(Gd Vb) Bb(sC yH) Du(Kr Vv) Eq(Mh Nf) Ub(mF Wd) Ip(Hp We) Tl(Qv Ri) Jy(Gh kG) Ps(Jt Mh) Um(mP mW) dI(Ry Yg) dJ(Fi Vc) jF(Uw Zq) rZ(Dr Gc) oQ(Ue Ug) AnkG AxnN CtnF DiSh NcUy HbYd IrVa WbbL SfUv WeRi aMkC bEvS cWoP} sC{Bb(aA aJ bF bL cD cH cR cU dK fP Fy hL Ii iZ Jo jR Kg Kp Ks Mg Mt My Nd oH oK Ph Pi Ra sK sM To Uk uP uU vH vI Vo vU wK wL yE tM) Jt(aS Ax aZ bL bM cH dE dJ Ed fN Fw Hw iA Is jG Jn Js Ld Mv Nt Or Pg Pi QA QB qC QD Qe Qg Ql Rm Ur Vp Vu Tj) cH(Al Ar Cv Dc Dg Dl Fp Ii Ij Im Jd Ji Jo Jp Kf Kl Mq Or Pd Pz Ra Rf Tz Ub Uc Uk Vs Vt yL) Dg(aS aZ Ed Fw Hr iA jG Ld Md Mp Or Pi qA qB qC QD Qg tS vH Vu wP) Or(Ar bF Bg Ef Ii Ij Iz Jo JP Ke Kf Kl Mg Mt Nm Sr Un wG) Aa(Ar bF Bg cG Ch Cp eT hA iJ Jh kS lM Mg Mv My qH rS uR) Fw(Ar Ii Im Ji Jo Ke Kg Kl Lx Mg Nm Pd) qC(Dl Ii Il Im Ji Ke Mg Nr Ra) Ed(Ar Fp Ii Im Jp Li Pe Ra) tS(Ef jG Kf Kl Kn Ko Kp Ld) Ij(bL iA jG Pg Pi qB Ub) Qg(Al Ih Im Mq Pd Tz) aS(Ii Ji Jo Nm Pz wG) Kl(Md Nd Pi vH Tj) Rh(Dc dI Fy Jp Ra) Im(Js Ub Vp Vu) Ur(Ji Pz Ug Uk) bF(Tz Uk yL zA) jG(Fy Kf Uh Un) Mg(Jk Mp qB) Ph(Jd Mq wP) Pi(Cw Li Lu) bL(Aj Kp Li) qD(Ii Un Vt) zA(Co lM Pf) Ar(bM Tr) Fy(bU qB) Jp(bM Uk) wL(dH Pz) oH(Kg Tz) MdKe NdJd UnqB aZdB hPyL} Ke{pK(aD aW bC cF cZ dN dR fA HB Hx Il In Iq Kg Kp Kx Ml Mq mT Nf oP Pa Pc Pd Qb Qc St Tn Uk Vv Tj tF) vH(aC aS aU Bb bL cM cU dD Fw Jv Ld lN Mq Nd Nr Pg Qu Ra rR Ub Uk Uu vO) rR(aS bN cH dJ Ed Fw Js Jv Mp Nd Nn Ny Or Ow Pi Qd Qg Qu Rh Vp) eM(Af Ao Bn cC Dg Dl Gp hF Iv Jt Mz Uc Ug Ur Us Wm) vC(aH Bb dB dE eZ Ip Jo Pd Qh Qm Qx Ra Tz Ub Uk) pH(bF cC cZ dN Hx kC kK Nk Ny oT Ou Oz Qb Qh) uP(Aa aI bB cW cZ jG jK Mn qA qB Uu uW) uL(aC aI bB bE cM cZ Kk qB qC Ql Qz) jH(kC kF mI mS nF nI nN Yj) pS(bN dJ Il Ow Ph Qu Ra Rh) uT(aC bN cO cX Ld Ma Ra Rh) qZ(cM Fw kQ Pi qD Qn Ra) iB(kC kE mY nC nD Ps) aC(uM uO vA wP yK) oD(hB kC mE Mw Us) Mn(tO wG wJ yK) Ra(qB vU wB zA) cZ(tS vP vV wL) gZ(dR Mw nC Ri) jG(Fd nD sK vU) jK(Fd tQ tT tU) jQ(kE mF mH mP) lN(mP nD oP vB) aI(tQ tU yK) fB(aF Qb Rj) nH(iP oT pI) sO(Jq qD Qu) aL(tQ tS) cM(rT sK) cR(tS wJ) dD(vT wP) mS(jB pI) nC(iP jU) zI(bL cH) qB(Me qY) jI(nD nR) jL(mZ Wh) jR(mF mH) DuqW ThtL NnqD SjhA JjtM RylM RhvB UspI ViqY VoyL aZjB bBuM bNxA cUuI nOjU mEjP nLiP hBoT} Ji{Js(aH aK aR aY bM Bo bU bX Ch cK cP dB dE Dg dI Jd Je Kf Kq Mb Mt Nc Nd Nh Nj Nl Nt Pf Ph Qz Ra Ue Uk) eM(aL aM Bb bC cC Ch Co cZ dE dN dR Gp Hx Jr Ju Ki Kl Mv Nd Pk To Tv Ue Us Wm) Nh(Hw Hx Il In Iu Jj Jn Jq Mb Ms Mt Mw Mx My Nj Nk Nq Ns Oe Oz Pf Qa Qb) pI(bC bU cC cD cF cR hF Ii In Jm kK Lv lW Mk Mq Nk Pa Qb St Vp) Nc(Hw Hx In Jj Jn Jq Mb Ms Mt Mx My Nk Ns Oz Pc Pf Qb) Nj(Fr Hw Hx In Jj Jp Mb Ms Mt Mw Mx Nk Oz Pf Qb) Mt(Hw Hx In Mb Ms Nd Nq Oe Oz Pc Qb) jH(Eq Fd Lp Ps Rv Si Va Vb Vi Yj Zw) jI(Eq Fd Gc Hl Ho Lp Si Va Zw) Mb(Hw Hx In Ms Nk Ns Qb) Nl(Hw Hx In Mx Nk Oz Qb) hA(Fd Gn Ho Rv Ry Zx Yf) Nd(In Iu Jj Li Nk Pf) jL(Ru Rz Sh Va Vb) In(Fp Ne Nt Pf) Qb(Ne Pf Qa Qe) iP(kC nC nH nL) jK(Fd Ps Wc Yf) uP(aS cW qA Ql) Mp(aR aY bM) bU(jB oT oV) cH(rR uR wG) dE(aR aY vC) qY(Gh Rt Va) qV(Wb Yj Zw) Fd(jG jP) Hx(Li Pf) Qg(uM vB) Pg(bM bX) aS(vH wG) bC(gC pH) cC(fB oV) jF(Yk Zx) qW(Lp Yj) jU(Rt Sh) oT(eC oP) pK(Mq Tj) ThtL NnbM HolN WerZ JquR RvhW QluL QnzA VqqG cMwK cRwJ} qW{Yj(aF aM An Bc bG bI bL bN bP bR bS bU bV cN cP cQ Cs cY dB Dc dE dJ Dp Du Ef Fn Gc Gz Hu Ii Ip Jn Jp Jy Ko Ks Ky Lp Lv Mf Mt Pa Pb Qt Rh Ri Rx Sj Tz Uk Ur Us Vh Vj Vt Wc Tl Yf) Du(bP Ch Co Cp Cw Dl Ef Ez Gc Hb Hu Iz Jd Jh Jt Kf Ko Mg On Ow Oy Pf Po Rz Un Uw) Rv(cP Hu Ko Lu Nt Og On Oy Pc Pd Qy Ri Vh Yg Zq) Si(bN bX CV Db Di Fy Ks Lp Nv Rm Sr Tn Wf) Zq(bR dI Gp Hl hW iB Nc Nl Oe Qv Ri Vp) Wc(Cs CV Db dJ Em Iv Nh Nl Vb Vj) Lp(aS bZ dG dL Lu Ms Nb Nl Nx Ri) Vh(aP bZ dG iB Jm Nc Oe Of Vq) aD(kF kP mF mT mU nD nF nJ nN) kO(bG cE cW Gp Kj Uc Uk Ur Us) Zw(Ii Kg Kj Mg Mt Un Us) Qy(Eq Fd Hl Sf Wb Yh Yi) cW(mF mH mS mY nC nK) Di(lY mP nT nU Wb) nC(aW bM Ch Ju Tv) iP(kC kF kG mS nK) Yi(Kg Kj Ko Mb) Ri(Em Gn Sf Vw) cT(Rz Uw Wd Xa) Fc(aR Oa qV) Nu(Gc Vj Vw) Hu(Ux Vb Vi) nH(aW Tv Vs) Fd(Nm On) Gh(Dd Ni) Hl(Hb Iz) aY(lX nF) mI(Ax Cs) kC(cS Vs) oP(Rh Us) EmOz GbUn GdNc MgeT NeUw NlWd UeRu IzUx YhKg JhVb WhOn WfKc JmPs KlmZ KrmF RzbR PhnL cZnK} Fc{mY(aH aI aS aW aY aZ bG bJ bQ bU bZ cD cE cM cN cQ cZ dB dD dE dF Fi Fn gL iH iP Je kG kK Kn Kp kR Kz Mq Ms Mv Nc Nd Ne Nf Nl Nn nR Ny oE oF Oz Pc Qh Ru We Tl Tj) hW(aA Af aX bV cJ dD Em Hx Lv Ml Ms Ne Nh No Ny Or Ql Uh Ut Zq) jR(aI aZ bA bL cX cY dE Fn Io Iv Kx Ne Ns Og Pd Rf Ri Ry Yi Tm) jU(aF AL aZ bL cP Fn Hl Iv Ki Lj Nr Ns Og Oh Ow Qu Qz Uv) jH(An dI Eq Gd Gz Hv Ih Ip It Iu Jh Jl Lj Qd Rx Wc)

Figure 14 Continued

Figure 14 Continued

Pg Qb) Hx(Fp Ih In Js Li Mt My Nd Ne Nl Ns Oe Oz Pe Pf) Nd(In Js Ml Ms Mt Mw My Pf) pI(cF cR dB hF Jr Mw nJ Ut) Nl(In Js Mt Mx My Nk Qb) Js(Kf Mt Ne Nt Pf) rR(cH Ed Or Vp) uP(cM Or qA qB) In(Mt Ne Pf) gN(aH Dg gC) Fd(jE jF) cM(vI vU) CwvB GtcD UbrQ WdrY cHuR cRwJ dEvC} IN{oP(An Ba bM Cs Cu cY dA De dR Ef Fw Hb Jm Kq Ni Nj Oa Pk Qz Ug Ut) mY(aD BG bO bQ cD cS Fb Ky Me Nj Pi Ra Rj Vs) nD(aD aG aW bQ bZ cZ dC Ed Jd Nj Nk Qw Rb Tv) Nj(kO mE mS mW nC nH nJ nK nL nU oQ Yi) Qv(Gb Gc Op Ps Rz Sf Uw Ux Vj Vw Wc Yg) Fn(Eq Hl Rv Wf Yi Yj Zw Yf) Yi(aE Ar bP DK Rf Uv) Yj(aZ CX Io Kr Ql Ry) Pi(Gb Si Vw Wc We Yd) Yh(aE DK Rf Uv) Sf(aY Hu jU Nf Pf) Zx(Ch Ef Iz Vs Wd) Wc(aL Db Dp Wh) bQ(kG nC nK nL) Rf(nC nK nL) Uh(mP mZ nU) Vj(cJ Fw Gp) cQ(nF oO oQ) mF(hC Hw In) mH(aG Dp Kj) kO(hC Kj St) Eq(cU Mv) Mr(Vi Vw) Wh(Co Tr) Ry(aD dH) Vo(wD wH) aY(Vc Vh) dM(nC Zq) nF(Bg Rc) nH(Ky Or) BakC DkFd FyUx GhUv MtvH IdnL IzmZ YgKo YdUn JnVa XaQn JyoQ KnwL KrUy PknC aHmT bGmU dHlX nBhC} Jt{eM(Aj Al aX bC Bo bU Ct Db dE eC fP In Io Iq Je Jk Ju Ki Ks Kz Ly Mv Mw Nd Ny Oe Qu Qz Tv Ul Ur Us Vo Vt Wm) vC(aR dB dE Hx Is Jk Js Kg Kp Nj Ow Qa Qb Qd Qg Qw Vp) uW(aR bL cH cR dE eF iA Mg oK oN Ri Ub Vp) fB(bU iZ Ki Ks Nh nJ Rj) gZ(fA Il kC kK Ks nU Ny) cH(uL uZ vB vH vP xA) jB(eC Ed Il Nf nU Ql) pK(Iq kC Mq Nf St Tj) Qd(qH rR uP uZ vI) Jv(rV uY uZ vB vI) cR(oW rQ uM uR wJ) pH(aX bC kC nJ St) pl(bG eC mS nJ Nx) Mn(uP uR wP zI) qI(Mk Oe Or Ri) Fd(jG jH jK) Nt(qH uN vH) Qa(uL uP uZ) Qg(pS rR uL) eC(oD oT oV) qB(rQ rT rY) oW(bC bW dN) Nj(pS vB) Qb(qH uL) Ps(kK nR) bU(oT oV) qA(rT uP) uZ(Is Vu) vI(aC Dp) FwyH NipS IqfA WhjM KpvB RujH WnPg OerT OrrR aLwB bGoV cUuY cZvV dJrQ mSoT} jL{mF(aY Bn cW Di Fn Gp hC Kf Kg Kj Qv Rb Tr Tv Uc Ug Uh Uk Um Vs) nC(bM bX Di Gl HC Id iH Kk Kn Kp Ks Ph Rm Sr St Tv Uk Um) nH(Di Gl Ha hC Kf Kk Kn Kp Ph St Tv Tj) mE(aH bG cQ Di Kg Kj Kr Ug Uh Uk Ur) mS(Bo cG Ed Kg Ko Kp Pi Pk Qw Tz) mT(Ba Ed Fb Jd Jy Kz Or Qm Qw Tv) nK(HC Hf Kf Kk Kp Pk) Vb(Ch cP Dc Pd Ua Xa) mH(hC Jy Qm Sr Tz Ut) Ug(kE kG kK nD nI) Ur(lY nB nI nN Wc) hC(kC kF kG mI nL) Wh(cP Jn Qt Ua) Uv(Rx Si Wd Xa) mY(Kf Kg Pk Ra) Yj(aD Rf Rj) Uk(kE kN nR) mP(Or Qw Ue) kP(cQ Jy Qw) An(mI nN) Bo(Si Va) Xa(aR cU) Vc(Fw Tz) aD(Vj Zq) bM(kE nD) cP(Uy Yk) nO(aY cW) nI(Ib Jv) nL(Kf Sr) AsmW EmIp FbkK HlRf SiJs JfmU WecU QvRx JnVa TlRi KgkC KrkO RyRm UmkE bXnD cQmI oQoN} Mg{rQ(aU hW Nk qA qB qC qD rX uW vT wG wL yL zH) uL(Bb Bg cM Cq jG Kk Kp Ne Nj Or Pi qA qB uW) wJ(aS cR cW Mp Ni Nj Nk Or qA qB qD wK) uO(Bb Bg cM Fw jG Mp Nd Nk Nt qB qC Ql) jG(qH qI sK tO tU vV wB wH wL yK) Gt(aI Aj aL aR aZ Bo cH dD Mb) Nj(uI uT vA vB vH vI vS vT wP) vA(Bg cM Cq Nk Or Qg Ql) vH(Ar Bg hW Kn Kp Kq Pi) Lp(kC kE mZ nC nK nR) uP(eT Kr Mp qA qB) uW(aA cM hW Kq Pi) vB(As Bg Kp Mp Nk) vI(cM Hr Mp Ne Ny) gN(bB In Oz Pc) wL(Kn rX rY Th) wP(aA Bo jM Pi) wH(Di Mp Ny) rX(Gc qC qD) Bg(uY vV) Zx(kC nT) Uy(mY nB) hA(Em Wh) wQ(qA qB) tN(cJ Ou) jK(Fd yK) rY(qC qD) vC(dE Jk) AsvT DiwB TjpK GlpS NnqQ MzfB YjjH UwnI UxqV aAuI cZvV tXqB wDjM kKpH} pI{Nx(aJ aM bE bV bW bX cF cP cR cS dB dG dH dN eC hF Hq kO Lh Mk Ml mT Mw mY Mz Nf nH Nk Nm nN Og oH oK oN oP Ow Pa Pb Ri Ud Ut) Lh(aF aR aZ bC bP bU bX cC cD eF Gp hB Iq Jf Jk Jl kK Lv Lz mF Mk mS Mw nJ Nk oD Oh Pc Pg pK Qb Qy Rg Wm) Mw(aM bC bP bX dE dL eC Hq Jh Jj Kc kK Lv Ly Me mF Ml mP Mq Mv Nk Nu oO) eC(hB Hu Io Ly Lz mS Na Oe Rb Uc Ug) Mz(bZ cI Jf Js Ml mU My nD) Nk(Ij Lx Mx No Nv Ut) Qz(cF Js Ml Ne Nh) Ut(Is Jk Kc nD) cF(Mx Rb Un Up) Ml(cD Ip nD) nJ(Ld Nv Qm) Nu(aR cM) Ij(Jk St) Ip(dN mT) bX(Io Iq) kK(Kq Mn) EdkO LvUm LxaZ QgUs KccD NvcR UhbU mPhF} Jp{uW(aC aH aL aQ aU bL bN cH cM cR cU cY cZ Dd dE dI dJ Ql Qx Ra Ub Vo Vp) vC(aH AL cW dB dE Jd oF Or qB Qx Ra Rh Tz Ub Ug Uk) vH(aC aI aL aU aW bL cM cU cZ jG Kl Ra Rh Tz Ub Uk) Nh(Hx In Jk Jn Js Mb Mx My Nj Nk Ns Nx Qa Qb) cZ(tN tO tS tX vU wG wH wK wL yH zH tL) Nj(Hx In Js Mb Mt Mw Nk Nx Qb) aC(uM uT vA vI vT wH wP) uY(aH aI aL cM cU jG) Nl(Hx Js Mb Mx Nk) Nc(Hx Mb Nd Nk) oT(Gp Rg To Ur) Vo(wJ yL zA) aI(sK wH yK) aL(tS vT wG) fA(Gp Rg Ur) tM(bL dE qB) pS(aJ iZ Rh) rT(qA qB Ub) Mb(Ly Mt) cW(sK uP) EdxA GpgZ MtNd ZwqV RyjQ RhvB RgoD OrsO VbjH aHuN bNuZ cMuU cRwJ cUvT dLuP} Kg{vC(Ar aS Bb cH dE Ip Jd Jf jG Kl Mq nY Pc Tz Ub uL Ur vB vP vV wJ yK zA) vH(aC Ar aS bL cU hC Jf Jv Kd Kl Ne Nk nY Pg Ra Ub Vu) wJ(aK aU cR cT Oe qA qD Ql Qn Vo) zA(aC dA Ef Jd jE kQ Ra rR Uu yK) aC(uL vA vB vP vV wP yD yK) vT(bL cH Nn oK Qm Tv uP wC) yK(aI cM cZ Di jG Ql) cH(rR uL uT vA vB) wB(bH Di Pg qG Ra) uP(Jd Js Mp qA qB) tO(aS jG Mn Ql) vP(aK aL aU cZ) vU(jG Kl Qd Vp) vV(aL aU cM cZ) Zw(jH jK qV) iO(wC wD wH) xA(bF bL Nn) pS(cF Ra tQ) rR(jR Pc Qg) uT(bF UR) cU(uI vA) mH(jE jF) tU(cZ jK) qV(Hl Rv) ThuX NnvW NtwG MpvB YjjH ZxkC QgvA OewQ OfqB aSuV bEtQ bLtM gLtS tFwL mEjE nCjU kGrY} hA{Vj(aZ Dc Dk Fa Id Il Jq Kc Kr Lv Mv Ne Ns Oy Qv Qz Ry Tz Tm Xa) Xa(aL aV aY bB Cq Cs cU Cx dK Fn Gd Hf Pk Qn Qv Sr Un) Wh(Ar Co Cu Dg Dk Gc Hu Ij Kn Qt Rc Tr Uw) Fa(Eq Gb Uw Ux Vh Vw Wd Tl) Gc(bB cI Ed Fd Of Pi Rh Tr) Si(aY bB cI Cs Hv Mv Nr) Tz(nC nH nJ nL nT nU) Tr(Dr Ry Sj We Tl) Yj(cX Il Io Jn Yi) Vb(Iz Of Oy Qz Ua) Cs(Uw Vh Wc Wd) Nt(Fd Hl Yh Yi) mZ(cE Hb Uk Um) nC(cE Rf Rm St) bB(Gb Vw Zx) mY(aD cS Or) nH(hC Rm St) nL(hC Rf Sr) Mh(Ru Uy) Mv(Uw Ux) Yd(Hb Ko) Vc(aY Qn) dD(Uw Vw) mH(aG Dp) EmUv EqdH FdMw GbcI UbWn UemE HuRy HfRv YibP WdKr JnVa JyoQ KjkO RxPe OrnK aDnD bQkG cEkN hCkC} jH{Yj(Bb Ch cT cX Dp Dr Ef Fn Hb Id Ip Iv Iz Kc Kj Kq Mt Pd Rg Rx Tz Us Vs Wd Zq Tl) Zq(aY bP cO cP cU Cv dI Ed Gp Hl Hx Ip Ks Ky Nj Pk Qv Rh Rm Rv Vo Vt) Ip(Fd Gb Gc Ho Op Ps Rz Si Uw Ux Vi Vj Vw Wc Wh Yg Zx Xa) Wc(bP Cv Nc Ni Nj Ow Si Wf Th) Vj(aW bL cP dD Gz Je Mr Pc) Or(mY nC nH nJ nK nL Vc) kO(Kr Ky Nj Ql Rm To Tz) Ko(Gd Lp Op Ps Wb Zw) Un(Fd Op Ps Yd Zw) cP(Ru Vi Vw Wf Yf) Tv(kG nC nH nL) Si(Ih In Js Qa) Ax(mI nN) Ef(Ps Zw) Tt(Rx Vb) Tr(Ru Uy) Ph(nC nL) mW(An Cp) hC(mU nJ) DinF DpmH EmNs FdUa GbaM GdNi GnVs NtYi NjnL IdZw HbYd HfnD IzVb QvnH RzdH RtUv UmkG kCoK} Kl{fB(aF aQ bU cD cM cR dJ Jh Jk Jr Ki kK Lh Lu Lv mP mS Mw Mz nD nJ Nm Nx pH Rj St To) vH(aC AR bL cH cU Fy Jo Jv Kn Mr Mt Mw Nd Nk Nr oK Pc Pi Ra uP) vU(aC AL bL cO cX cZ Fy Ip Ld Nn Or Ow Pi uN uY uZ) tS(aC aL cM cU cW cZ dJ Ip Pi uN) pH(bP bX eC kK kR Lv nD nU Ny) uP(aI Ki Ld Mn Pi qA qB uW) aC(uL uM vB vS vV wP yK) vC(aR dB dE Ip Jo Lv Pc) vP(aL cH cR cZ) Pi(sK tX wG) bL(uM uW tM) cO(uT wB zI) tN(cR Ou Ow) Jv(vB yE) aL(sK wB) cZ(vV yK) mH(jQ jR) qH(aH cH) pS(Ra tQ) uW(cU Jo) MdrT MzeM KkuL LdwK LhpK LpnK OwuG VoyL VwhW PcqI aRzG cRyK} rX{mF(bG cC cE cW Ih iJ Kj Nc Ni Oe Oh Pz Qn Uh Uk Ur Vo) Tl(Hx Iu Jl Mn Mr Ni Nj Nu Nv Qd Wb Wf Yh Yi Zw) mE(aN bP bQ cE dB Di hC iJ Qn Ri Uh Ur) oP(aM cG Cq cS cW hC oK oN Wm) Wd(In It Jo Ms Mw Mz Nq Nr) hC(kC kF nB nC nH nL oQ) bP(kO nC nH nK nL oQ) dC(mP mU mY nC nD nH) Ur(mI mW nI nK nL) bQ(kN mZ nD nI nR) mH(bO bX Oa Pi Ut) kO(aN aR bJ kR Ql) aP(mP nB nI nK) nU(cQ Fb Nj Um) Gc(Jk Jm Ms) cZ(mP nC nH) mT(bX Uk Um) oQ(Jy Nj Tz) Fb(kK kN) Yj(Oz Pa) Zx(Jm Ms) Wc(Mf Mk) Pi(mS mY) nR(cE iJ) mP(cQ dA) nD(bM Um) rQ(Jo Un) AjnC DrcP NtWb NjnN WfOz JykC aDoO bBnH nBhG nJkR} jR{Si(aE aL aW aZ bB cM Cq Fn Fy Io Iv Js Ki Lp Mn Nx Oe Pd Rf Rm Ry Ur Vu) mH(Ao Ax aY Ba Bg Cq Cu Dg Dp Je Kd Oa Qu Qy Qz Rj Ss Vu) Ry(cO Fn Hu Ip Jy Kc Ko Ky Mr Nf Pd Qy Tt Tz Wm) Ri(Gb Gn Rz Vw Yj Zq Yf) Rf(Ho Ru Uy Vj Wf Zq Zw) Uv(Ho Yg Yh Yi Zw Tl) aL(Gc Hp Wd We Zx Ye) Yj(aJ bV cU dM Th) Un(Fd Hl Yh Yi Zw) kO(Dd Jy Kr Ky Ul) Vj(aX aZ cY Nu) Yg(It Jk qV) Kp(nC nH nL) Vw(aW bA cY) aY(mW nD Yd) cM(Hp We Ye) hC(mS mY oQ) Fn(Em Zq) Ho(Ip Ur) Vb(Kc Tv) Ux(bZ dM) nC(Af Kk) kN(Ba Bg) AnnN BbqP YfKo GbVt IqRu ZqcY JfoP WeaW TlbB OanK UkmZ UwcU UyPd PhnH aDnD cWlX} jQ{mH(An Ax Ba Bg Bn Cp Cq Cs Cu Dg Dk Fw Iz Kf Kp Oa Pi Qy Qz Ri Rm Tn Uk Um Up Us Uu Vp Vu Tj) Ry(aQ Aw Ch cQ cY Hf Hu jE jF jU Kc Ko Ky Mr Nc Nd Nl Si Tt Ua Vs Wc Tl Wm Tj) aW(Gc Hp Ps Si Wd We Yg Ye Xa) Uv(Eq Hp We Wh Zw Zx Ye Xa) aL(Hp Si Va Wd We Zx Ye) bA(Rz Ux Vw Wc Wd Wh Xa) bB(Gc Hp Si Wd We Ye) oP(aZ Jf Kc oN Ph) aY(mP mS mW nD) cM(Hp Si Ye Xa) cT(Si Vh Wd) cW(nD oO oQ) Cv(nC nH) Nd(Rx Yi) Ue(tS Wn) Kp(nC nL) Ru(Iq Pd) Ri(Gn Vj) Vb(Kc Pd) cY(Gc Si) mZ(Hb Uk) kN(Ba Bg) BbuL

Figure 14 Continued

Figure 14 Continued

Na No Nt Ph Rb) cD(Fy Jd Ld Li Lj Lx Nv Oa Qn Uh) dE(Fa Im Ir Iv Lx No Nr Ph Po Ut) Lx(aF dL hF Og Ri) Mz(cF cL Ld mF Qw) Tj(Fp Ha Qw) Nx(aM Mh Og) Uh(bU bX fP) No(dJ kK) Ld(aS mP) Qn(aS bU) bX(Fy Ph) fP(Qw Ut) MxcF UcbG KoUs LjbU NvcL UndJ} Th{nR(aA Af aM An Ao aS aW aY bG bI bM Bn cP cS Ct Cu dE Gp hF Je Kp Kz Nf nW Ny oK Rb Ub Ur) nF(An aY cC dE fP Gp Ju Kp Nf Nn Ny Pk Qh Tn) nT(bG dR Gp Ny Sf) cS(kC nC nH nN) Kq(uI uX tM) aY(kK mF nU) bG(nC nO oP) fP(pS vH tL) An(gC oQ) Ny(kF kK) Vs(wK zG) bZ(mS nB) kO(Lt Us) GzkC NfgC TrvV SfkF JotL bXnC cEnJ} Lp{kK(aA aY bI cM cO dB Il Ko Ks Of Ph Pi Qz Rx Ut Vs Wm) kC(aA aS aZ bG bI bJ bV cE cM dB Gd Il iO Of oH To) nR(Mw mY Ph Pi Vw Wm) lY(bG cR cS Jr To Uo) Vv(nC nH nL nT) mS(bG cR To Uo) dR(mH nO nT) kE(aS bI Of) kF(cZ dN oH) Hu(nJ nU) aA(mH nD) bG(nJ nU) mY(cE Jj) mZ(Pi Ut) oH(mH mU) WmnD GdmE UonC VwnH} Ed{jB(bA cD cT hC Hu Iz Jj Jk kS Ld Lj Mk mU Mv Nm Oa Ou Pb Pc Ph Qd Qm Qn Rf Ua Un) gZ(aK bN dC fA Fp kO Lj Lv Mk Ml Nm Oa Un) rR(Fy Lh Mq Nv Pi Po Ra Sr Uh Ut zA) oD(Fp Ir Lj Mw Nb Oa To Tv Un) fB(cD iZ Lv Mz Qm) rQ(Ar Im Li Nr) tM(Kq Ue) oV(kO To) vS(Mq Sr) ImqG nDjI} Hp{iO(Dc Fi Ko Nf Oe Qc Rt Ur Vj Tj) kF(bO Gn Hu In Iq Ju Kn Kp Sf Um) kR(Bo Gn Hl Hr Hu In Qv Um Zw Tj) oE(cM Gn Hu nD Nf Og Qv Yj Tj) nR(aY bP bZ hB mF Nf Qm) Ko(Fd Ps Qv Rm St) bZ(kP nB nD Ur) Kn(mH mT nB) bO(kC nN) mU(cR Qv) nD(aP kK) IqmS ZwRf JmnB VqnN PcmY aYkC cUoN} Jd{uP(aI Al cW Jv Kn Kp Mn Ms Nn oF qB Tz Uk uW zA) Nd(rV uM uR uZ vA vH) tN(aX bL cJ cO cR Nb) zA(cO Fy Jo Kn Nr rO) uW(bL cU Jo oK Ph Un) Nn(uL uR wJ yD) wJ(iZ Kp wK) uL(Kk Nj Ql) Jo(rQ uV) Wn(Al Qe) bL(wB tM) cM(tO wK) oD(eC Mw) uR(cR vH) NkqI KfVp KnvH KpvB LdwL UkrU PitX cDgZ wDtM wHrR} jI{Yj(DC Fn Gn Id Iv Jn Nd Tv Tz Uk Up Yf) Bg(mW mY nD nF nR) kO(Dd Kj Kr Ql Tv) Fb(mS nD nF nR) Nt(Hl Yh Yi) Tr(Op Ux Wh) Tv(nC nH nL) Yd(Hb Ko Un) Ry(cE dH Ri) nD(aW bM cY) nJ(aY cW Or) An(oO oQ) Nj(Vw Wc) Si(bN Ms) oP(Oa Ub) DpmH FdUn FyZq MtYi TtWh WdRi KpoQ KynC QnVc UhoO cWmF} Tl{mY(aS bM cT Fp Lv mU Of Pa Pe Qm Yd) nJ(aS bA bG bN cL dN Ib Jv oN) kP(bA cE dM eF Hc Wd Wh Zx) nU(bG Of Oy Yd Zx) lY(cL Lj Mh Pf Qm) Pi(jM mZ nL nR) cL(mE mF mZ) jM(Cx Nd Pk) kF(dN Ha Lj) Fa(kN mW) aS(mS nI) dR(Ko nH) CsoE ZxmS LihG OgmZ PhkR bAnB dNmF} Mt{Fp(Hw Hx Il In Js Mb Mx Nc Nh Nj Nk Nx Oz Pc Qa Qb) In(Lj Mb Nc Ne Nh Nj Nl Nt Pe) Nk(Mb Nc Ne Nh Nj Nl) Js(Lj Nc Nd Nh Nj Nl) vH(Aw Bb Cu Kd Kk Pi) Pc(Nc Nh Nj Nl) Qb(Lj Nh Qe) Bb(uT vB) Hw(Nc Nj) Or(rQ rR) wG(oF Pi) FwrR GpfA MbLj NdLi cWwJ} Vq{qH(aI aS aV aX bB bQ cB cG cL cO cX cY dA dF dG dM eF hB Hr iA iO Jn Mu Oa Oi On Pg Pz Ql To Tv tF) qG(aI iA Ih Jh Ma Qb Qc Ql Rm Sr Tn Tt) qZ(aX cP dF Ih Rm Ul Uo) Zq(Dd dN Ny Qn Wm) qI(aD cU dK Jh Jk)} Zx{kC(aS bI bJ Kp Qd Ql Qm Qy To Un Ut Uu Vv Wc) kK(Ko Mw Qm Tz Um Ut Vs Vv Wd) Ql(mE mI mY nC nH nL nR) Kp(kF kN mH mT) lX(Dp To Un Us) kP(dH dM kR Wm) Qm(kE mY nR) Vv(kF mH nN) mS(Lt To) NtnR JrnU UvjM PcmY PimZ aInJ bJmE dRnF} cR{wJ(Dg Dk Fy Jh Kf Kn Ko Kq Nm Ny Uc) Ko(jB tT tX vP yD) mU(Fd Ps Vw Wb Xa) tN(Bb Cp Dg Iz Jh) Bb(rQ wL tL) Iz(tS vP yK) tX(Aw De Kq) Dg(uI uW) Sj(lX lY) Zq(kN kR) zA(Fr Jh) oV(Qm Uh) AwtS DcWn PzyE KfbZ KjvP KpwK KxfA RunB RioW NyuR UnqD VcgL VioE} Ue{wG(aG aI aJ aS cJ cW cZ eZ oF Ou Pi) tM(As Ax Fw hP Kk Ou Ow qC qD Ql) wL(aI Kp Ld Mn oE Or Pk qB) vU(Al Bb Bg Cv Kk Kp Ph Pi) Ld(tN tO tT tX uP) wH(Kk Kp Ny Ql) uP(Kk Or qB uW) yD(aU dJ) EqkG KptT OrvS cUuW tXqB} Un{aU(qD qO rN rO rR rV uW uZ vP vV) qD(bE Nn Oe Ql rQ uG vH tM) uW(cM dE iA Pi Ql Vp) qB(cB Ql uP uR yK) qA(bE cB uG uP) rV(Ar Kk Kp Ql) Iq(jB oV) Ql(uZ tM) Pi(uG wG) eM(Gc Mz) rQ(Fw Ub) JrtL KkvB VcgL VhlY aLuR cMwK dJfA jBkC} oE{Nf(Du Fd Rt Rx Si Vi Vw Zq) Yg(An Bc De It Of Pk Qv) Vi(aY Bn Cv De dN) Vj(Ar Ax Cs Dc Rg) Yi(aY cV Oe Qv) Si(Ar Ax Cs Rg) Zq(Ar Ax Bc Qv) Vb(Dc Im Jn Ko) Du(Kp Qn) Fd(Kp Qv) Yh(cV Qv) Wf(Dc Rg) Ph(Lt Uy) MzfR YjdB SrwK RgVw} Nk{Nc(Fp Fr Lh Li Mb Mw Nh Nj Nt Nv Nx On Pd Pe Pf Qa Qe) Nh(Fp Fr Im Lh Li Mw Nj Nn No Nv Nx Oh On Pd Pe Pf) Nl(Fp Fr Li Mw Nv Nx On Pe Pf) Nj(Fr Li Mw On Pe Pf Qa Qe) vH(Dg Iz) nDlO} Dg{pS(aS Hr Oe Or Pi Qg Ra Vu) uW(aU Dd iA oK Pi Vp) Mn(tQ tT uP wC) Js(Nd Nj Nl tM) aL(tS vH vP vV) eM(Id Jy Qg Um) vB(Hr Kk Or Qd) uP(dL qA qB) vH(bL Qd Ub) cZ(vP vV) tS(aU cM) MpuZ QgrR KkuL PivU aIwC aSuN wJqA} Fy{uL(aI aL Bo dJ Kd Kk Ld Qg Rh) Qd(qZ rO rQ rR uP vU) Mn(vT vU wH zG) Vp(qZ uW vS vU) cM(vU yD yK xA) Cw(pS qG vB) aI(uP vP vV) zA(dA Di Ri) vT(aL Ld Ql) Qg(pS rR) ArvH TjoD ShkF UrpS bUfA fPuW qBuP} Vw{nO(bG cM dB It Kn nD Ny St We) kR(An It Pz Qv Ud Tj) dB(mH nB nF nT) To(kK lY nD) We(kK lY nT) Kn(lX mH nF) nB(Ps Qh St) Tj(hG iA) It(mH nF) Ny(mU nT) aH(lY mT) oN(cU nR) AnhG NdjM HxmU PcmY dRnT gLnI tFnH} kP{Vb(aG aH bZ cE cM Mf pF To tF) Uy(aH aW bZ cE cM dF dM To) Wh(cE cM kR Nn To) cE(Hl Wd Zw Ye) Wm(Ps Uw Ux) To(Ru Uw Zw) aH(Sj Wd Zw) cM(Eq Fi Rz) We(bM Hq) bZ(Du Op) fR(aQ Ut) LygZ MfVh SfeF fBnD} kF{Du(aY cZ Jm Jv Kn Kp Kz Nf oN Pc Qm Qv) dN(Em Gd Ru Rv Rz Ux Wb Zq Ye Tm Xa) Sf(Ij Iv Lj Og Ph Pi Ut) Sh(Iv Jn Ko Pf Pi Tz Ut) Zq(hF To Wm) CuEx DrWm FdKp GnTo LdjB VbVv lYqZ} Lh{oD(aK dB Fw Jn Kx mE mI Mp mW mY Nn Oh oV oW Qe St Ud Uk Vu Vv Tj) cM(vU wH wK wL) jB(aZ Ky nO Qb) Js(Kf Nh Ph) fA(Hx Rg) gZ(aZ dR) oV(bU cC) NhIn QgrR LdvH UseM dNoW qAuP} Kq{Ld(rO tS vU wK yE tM) cM(qI tS uU vU yE tM) Ra(pS qZ vU wB) tS(aI aU cU cZ) tM(bL cX Pg Qi) aL(uG vU wG) uP(aI cZ dL) cO(uT wB) qZ(cB Jo) vH(bL uG) KkwH aIwK bEvS cUuI wGrN oKuW} Kn{wL(aH aI eZ Mn Pk qD) wJ(aS qA qC qD) wQ(cM cQ cX Qx) zA(cL cP dM Ra) Zq(kC nC nH) tS(Af dE Qn) vH(Jo Ub wP) Wb(lX mT) Uu(wC wH) aI(tU wB) nB(Dr Gd) DumH MnwG LtnJ cZvV tQpS qBwD} Ko{fB(Ir Jf Jr Kd Mz Ne Nl Nm Ns Nx Om Qz Rj Ul) Ps(Jl kK mF Nj) gZ(Mx Mz Qz Ri) Ru(nH nL St) oW(Hq Ri Us) nR(We Ye) EmnD FdNj GbkC LvoV MwoD ShkG RapS VbmP VhkR VjmF aLwB} eM{Ao(Fa Hf Je Ju Jy Kd Ki Kp Kx Nd Qg Qw Uh Um Ur Ut) Gc(Af BN Fa Ha Iv Oa Rg Rh Tv Uh) Mz(Uc Us Vp) gV(aD dI) DlQg UceC IvdE JraM JuOn NxUs UtkK} wK{Kj(bL Js Mn Nn Pg Qd) Mq(cM cZ Ld qB Ri) Iz(bL cM Jv qZ wJ) Aw(bL cZ oF qG) Jh(cM cZ Mn Nn) aI(Ar Bb Fr Om) Di(Al Ug) Om(cM Mn) bL(Ch Cp) BbcZ PzRi QtqG UuwJ PdcM} jM{Si(Gd In Nr Rm) Wd(aM Is Pk Uy) Tr(nD Sh Uy) Mr(Ry Ux) Nd(Uw Yj) Ni(Yi Yf) Hf(Ry Wf) Rf(nC nL) Uv(Em Eq) Vb(Dd Ye) cE(kN mZ) nJ(hC Nj) BgkN IpVc WbKc JoxA XaRi RuUw TkdB hCkC} lY{Hx(Du Eq Fd Ps Sj Wb Zq) Sf(cP dN Mh Mw nB) Lt(bH bJ Jr Ni) Du(Jm Nf Pc) nB(Rx Vb We) Ex(Mq Rj) To(Hl Vh) Jr(Rx Wf) qZ(mZ nI) FiTz WeJn YeaI UsVh UyaM} Jo{uW(aS cM gL hC iA nY Ra Vp) xA(Fw hP qA qB qD Ur) qA(rT tO uP wJ) vA(Cq iA Or qB) vT(bL Js Nt) qB(rS rT) pS(Ar Bb) rQ(wL tF) UruT} fA{fP(aE aR Ri Ua Ut) eC(Jf Nt Ph Rj) Nx(cL dN Og) Mw(aM Ju) Mz(Ju mU) Iv(dE nD) Ri(dJ To) bG(Qn Uc) bU(Lj Uh) cL(Fr Oi) QaQb JjRj KfcD RgnD UscM UtcC} vH{Ut(Bb Cw Dl Fb Kd Ld Ow Pi qC) Ub(Ar Cu Kf Kp Nr Ny) Ar(bE Iz Ms Nm) Aw(Ks Mr) Cw(dB dE) Iz(Jv Qw) Om(Fw Pi) bL(Cu Kp) DdUh MsUr SrOr} cZ{Ar(tQ tU uL uP vV wB wL) Uh(rQ tN uR wB wE wH) vV(Cw Gl Kc Kj) tS(Aw Co Cp) nJ(Lt Wf) wB(Cw Kf) wH(Mq Ut) BbwL CowG ZqbZ WemS PftO} Nh{In(Fp Fr Im Li Mw Mz Nv Nx Oh On Pe Pf Qe) Qb(Li On Pe Pf Qc) Js(Li Nv On Pe Pf) Li(Hw Hx Mx) MxPe QaQe JjNx} fB{Uc(cM Iq iZ mZ Oe Qg Rc) Qn(aF bU Nm Rj) Rc(dE kR Lv) Nm(Ld Qz) Ki(aZ Nx) aF(Ld Qm) cM(Us Uu) TjaZ MzdI HxnD UhbU UtdE} kC{aY(Du Fd Fi Rt Uy Vi Wb Wc Zq Xa) dN(Ps Uw Ux Vh) To(Gn Zq Xa) Vi(bS Mx) DuJm ExcM HlaS TzPs TtbG UuUx VhoN} Iz{uL(bN Hr Jv Kp Nj Or) uP(cW Kp Or uW) Nn(uV wP) Nj(vS tM) Jv(uV vB) bL(uW vU) cW(tS wL) MnwQ KpvB PcvU aLtS cUuW} mS{To(Dr Hl Rt Sf Uy Vh Zw Xa) Hx(Sf Vb Zw Ye) Vi(bS Hu Mx) Dr(Dp Us) Du(Jm Pc) Lt(Iq Jr) FinH MwSf VbnB UyaM} kR{Ph(Fi Gn Hl oW Yk Yf) Tj(Ps Si Ux Yh) Ch(Yj Yk Ye) cQ(Ry Vc Yi) Gn(Dc Dd) Rt(Is Jl) DrmY FiTz ZqQv QzYe PsOe} nB{Uy(aA aW aY bZ dR kK Vv) Gc(cB dB) St(Wb Zq) Vb(dR lX) bZ(Dr Lt) DuaP WmRt GddB HlbQ ShbJ JnPs RudR ViVv VjcB} wH{Mq(aH cM Cx dA dD qB Ql Qn Ri rR) rR(Cp Jh Mv Om Vs) aI(Co Gl Om Uh) Di(Nm Ug) Om(Mn Ql) GlbE} Qg{Tz(qH rR rS uM uO vU) rR(Id Ih Im On zA) Ms(uM wP) Ih(rV yH) pS(Nr Rm) MqvU ImqG KjvS dBvT dEtM} Cw{vB(dB Hf iH Ks Mr Mz Rb) dE(tU uL vS) vI(Ly Mp Mr) Ra(wB tM) dB(uI uL) pS(Hf Ks) TzyK bLtM} Pi{mZ(Fd Fi Hl Ho

Figure 14 Continued

Ps Uw We Yf) Sf(kE kK nL nR nT) TrvW SimU ShnR SrqH SstS LtkO UhrR VtuR} fR{aV(aM aW Bo Dl dN Mb Mp Nd Nj) aK(aN aW Bo
Dl) Mb(cM Mh Mz) cY(aW Bo Mz) MzNd aQaW} uP{qA(Dl Kj Ms Om Ug Vt) Om(dL eT qB Ql) Mq(dL qB) Tz(Cp Di) Jh(cW eT) BauW
Fral MsaS KpbP RgdB} gV{aD(aG aK aM aQ aU aV aY bO cP cW cY dR) aM(aN cP cW) aN(bU cM) cW(aQ cY)} mT{Sf(aH aZ cB cE cY
dB dR nJ) dR(Ru Sj We Ye) Wb(aH bG St) Vv(Vb Vi) UcUx YdKp} Bb{cU(rS rT tO uI uU uY uZ vI vT) fY(qP wL) LyvU RapS KpvB aLwL
aUrQ bLtM oKuW} Ph{mU(Sf Sh Si Zw) Ps(kG mP nT) Fi(iO nR) Zw(nF nT) Om(vB wB) MquN XanR RtnT bEwP dBzG} oW{Ri(bX cF fP
kK Ny To) dN(aF Ly Nm Nx) Nm(cS Kc) Ur(hB hF) DpUs TvhB UhbU UtcC} vS{Nj(Ch Ms Oy Uu) bE(Gl Kp qA qD) Jh(Hr Nn Ny) Kj(bL
Ha Nn) Ny(Ct Ub) ChRg MqQn} Zq{hG(An Ch Kp Nf Ny) bZ(An Bc Ch Di) Fd(Dd Kc) iO(Aj Bc) FiaY NfdR PcnI} Uh{dE(rQ rR uW tM)
cM(uW vI) AlpS DcWn NrwB StoV QhuW alwE aLuR bEvI dBuT tFrQ} bG{mW(Dr Rv Uw Uy) nJ(Lt Wc We Wf) mU(Eq Wb We) ExmF
UcoV XanO RvnH OpmZ} mY{Pc(Du Fd Hl Rz) Vi(gL Hu Ut) Iq(Ru Wb) Sf(bJ Lu) Uy(aM Wm) NiLt UwVv} Ut{Sh(mU nJ nN nT) mZ(Ps
Rt Wd) Yd(kK nT) dE(nH oV) PskK LtlX} aY{Uy(mE ml mW) Du(nR nT) ml(Eq Ex) mP(bH cF) FdnR UwmE} bL{tM(Ch Co Cp Hc Hu Ij
Mw) vU(Dk Kj) BauW DcWn} oV{Lv(Qn Qv Rg Ul Vp) Nx(dN Og) MkVv IpdN RgkK PdaK} oD{Mw(Dp Ki Ld Lx Tj) Tjlt FwLi NqTo
LxaZ IocC KiOn} Dv{Dl(Af Bn Bo Cp) Af(cG dD) BnaK GnbU aUcY aWdD} Kc{Dc(Yh Yi) Nj(Fd Rt) TjRy GnaS MrYk UbtS IpRu aLtU}
vI{bE(Ar Kp Li Ur) Aw(Mp Nj) DdKp NmaS MaMq MpOy} nR{Qm(Sh Vj Yd Ye) DuNf GdcP HaRt McSh SfOg} nI{gL(Ux Vi Wf Wh) EqcM FicE NiLt ShbJ XaaH} jB{dN(mP nD Nx) Ld(Nc Tv) On(Iq Ki) RicF NxOg} Ex{mI(aZ cM dM hG To) cM(nC nL) RjmU} Im{Vp(qZ rO uW) Vi(mF nO) UbuW OiqZ VuuZ} aL{Tk(dE Pb) wL(Dk Hb) wB(Dl Kj) BatS CptU} kK{gC(dL Ld Us) Ps(Qm Tz) DuJm GnTo RypF} Nc{Fp(Nx On) In(Nv On) FrMb QbQe LtnD} Nm{DiuT FwyH NtwG UbvT aSrR wJqA} To{lX(Gn Vj Xa) GnnU XamU RtnJ} Ra{tM(Cp Hc) GlwB TrrQ HbpS KjwC} Jr{mF(Lt Rx Wf) DrnC RxmU LtlX} Wn{Dc(aE aN kS) DdgP IppF KjPg} aI{Gl(wE wL zA) Co(wC wD) UbwB} Ch{hG(Yh Yj Yk Ye) EqiO} Du{NfmU JmnN RtnT aPnC cUoN} Ms{Ni(vT vV) aS(wE yK) hPvV} Kp{UbvT VcgL cMwQ dBtU dErR} Om{AsuG MawB QxvU LdwL QnzA} Vi{Mx(mW nH) bS(mW nH) IvnO} Vv{Uw(nC nL) NjvT WfnC UynH} dN{Vh(nF nT) nN(Rv Uw) HlmU} Dl{Bo(dB dE) cPdE dJtT} On{Nj(In Of) NlIn IqgZ} nD{TjcE GdMl OpUo mPqZ} nF{qZ(mZ nO) HaRt VbdR} nJ{GcaH MlWe HuSh LtcM} zA{Co(aU cU cY) DicO} Aw{tN(Nb Ou) cJtS} Nn{DktM PorR cCvT} Ub{Ny(pS yD) RhyD} Ye{Qz(mZ nH) mUoH} Kj{HruL QdqH JvvB} bE{GlyL GptS TzqO} nT{FddR HaRt SjaU} Ar{TrpS cGwB} Yf{NfmU JmnO} Lt{NilX cQnU} Vh{IvnO mIoN} Vs{qG(wC wD)} cU{DkuI FdoN} dB{TkeC oKvT} mW{EqdM ShbJ} kG{WmUw UoUy} AoNyvB GcQvtF GngPnU NrcWtX MjtTqA MqQlwD MzJsKf NecOuT NlInNv TzKkwL SfQmnL WhJnmZ KscMwB UseCgZ VcaRgL aAqZoO aHbFwE Constrained panels with 2 analytes, where 1.0E-8 >= 'AUC p-value' > 0. Contains 530 panels of 197,786 total panels evaluated. : Et(aH aY bM cK dE Dq Ed Fp Fw Hw Hx Ik In Iq Jd Je Jf Jg Jr Js Kf Ks Kx Li Lj Ly Mb Mf Ml Mp Mt Mu Mx My Nc Nd Ne Nf Nh Nj Nl Nq Ns Nx Of Ok Oz Pc Pd Pe Pf Qb Ra Rm Ub uR Vp vQ Tj) Ok(aH bM bQ cE cK cQ Cu dE Fp Hr Hw Hx Ii Ik In Iq Jj Jo Js Ly Mb Me Mp Ms Mt Mx Nc Nd Ne Nf Ng Nh Nj Nk Nl Oe Of Oz Pc Pd Pf Qb Qd rP rQ rW uR vB vQ Tj) Jg(aR Bg bM bX dE Fp Hw Hx Ik Il In Iq Jh Ji Jj Jk Js Lj Ly Mb Me Ms Mt Mu Mv Mw My Nc Nd Ne Nf Ng Nh Nj Nl Nq Ns Nx Oe Of Oy Oz Pc Pd Pe Pf Qb rP sC) Nw(dV Fp Hw Hx Ik In Js Li Ly Mb Mf Ml Mp Ms Mt Mu Mv Mw Mx My Nc Nd Ne Nh Nj Nl Nn Nq Ns Nt Nv Nx Ny Oe Oy Oz Pc Pd Pe Pf Qb) Ji(Bo dE eM Fp Hw Hx Ik In Iq Jj Jq Js Li Ly Mb Mp Ms Mt Mu Mw Mx My Nc Nd Ne Nf Nh Nj Nl Nq Ns Nx Oe Oy Oz Pc Pd Pe Pf Qb) Nh(Fp Fr Ik Im In Jj Jp Js Jt Lh Li Lj Lx Mb Mm Mt Mw Nk Nm Nn No Nv Nx Oh On Oz Pc Pd Pe Pf Pz Qb Qe) Ik(Dq Fp Fr gT Im In Jj Jl Jp Lh Li Lj Lx Mm Mt Mw Nc Nj Nk Nl Nn No Nv Nx Oh On Oz Pa Pc Pe Pf Qe) Ad(aC Aj aK aR aV bM Bo bU bX cN cP Cq Ct Cu Dc dE In Js Nd Nj Of rP sC tV Tj) Mt(Aa Fp In Jj Jk Js Li Lj Mb Ms Nc Nd Ne Nj Nk Nl Oz Pc Pd Pf) Nj(Do Dq Fr gT Gw Im Jp Lh Li Mm Mw Nv Nx On Pf Qe) Nc(Fp Fr Jp Lh Li Nk Nv Nx On Pf) Mm(pS rQ rR rW sC tV vH vQ vT) Nl(Fr Jp Lh Li Nk Nv Nx On Pf) Pj(dU eQ pI qH rP rV sC vC wL) Mb(Dq dV Fr gT Jp Lh Li On) dU(Jt Ke Ld Mw Qn Rg Un Ut) lL(Eq Fc Wc Yh Yi Yj Yf) Ti(pS uN vV wF yJ tL) Nd(Jp Lh Li Nx On Pe) Yl(kI mM nA qX rA) dV(aK aV cY Ly Mf) gT(aK cY dR Mf Mg) fR(aK aV dO gW) rW(Bb Cw Ic Ke) vQ(Jt Kg Mg Ng) Ap(sC tR vC) Dg(bM cP Js) Dq(hB Fy Kq) Fc(iC jU rA) Si(qT qX rA) Li(Hx Ly Oz) dQ(bB Gn Nx) dX(Kc Kk Kp) eX(Ko Kq Qu) mM(Du Fd Vz) kI(Ho Hp Vb) rP(Bb Jt Un) uW(Mg Ng Uf) Em(jV jY) Fp(Nx On) Vw(iC iP) dO(bB Gn) eP(Kq Qz) tV(Cw Dd) AavO BbsC CpaM DlcP DoJy LyPf IcrR IiwF VznA JdVp RyhV UfuT VjiC VqqZ VowJ Constrained panels with 2 analytes, where 1.0E-7 >= 'AUC p-value' > 1.0E-8. Contains 368 panels of 197,786 total panels evaluated. : Ad(aH aM aQ aU aY Bn cC cF cG cK cY Dk Hr Ji Kx Na Nl Oe Ok Pc Pg Pj) Dg(aC aK aV Aw aY Bn Bo bU bX bZ cK Cp Cq dE Ik Nd Nj tV vQ) Fp(Fr Im In Jp Lh Li Mb Mm Mu Mw Ne Nj Nk Nl Nt Oz Pc Pd Pf) Et(aF aI aR Bo bX bZ cE cQ Cu dB dU Ic pI Qz Ri rQ sC Ue) Ji(aF aH aR bM bX cK cP CQ Cu dI dU Lj Ra Rm rP Vp Tj) Ok(aF aG aI aR Bn Bo bX bZ Cq dI dU Fw Kf Ld Ra Rm sC Vp) Jg(aF aH Aj aM aY bZ cE cP cR Cu Dk Ic Pj Ub Uu Vp Tj) On(Cu dE dQ dU Hr Hw Hx Jk Ly Me Mp Ne Oe Of Oz Pc Tj) Nj(Aa Ap dU Jl Jt Lx Mu Mz Nh Nk Nm Om Pc Pd Pe Qa) Dl(aC aK aU aV Aw bM Bo bU bX Cp cQ rP) Pj(Bo Ch cQ eM iB Jd Je Jf Js Mw Na Un) Ik(Aa Ap AR dU Jt Mz Nr Ns Pd rW) Ne(Fr Jp Lh Li Mw Nk Nv Nx Pe Pf) Nw(Ij Il Iq Jk Lj Mm Nb Nf Pg Po) Nc(Jj Jt Lx Mm Mw Nm Pd Pe Qe) Nd(Aa Ap Fr Jt Mw Nv Oh Pf Qe) Nh(Hw Ly Ma Mg Mz Nr Om Oy Pa) Mt(Hw Jp Ly Mm Ns Nx Og Qb) Nl(Im Jt Mm Mw Nm Pd Pe Qe) Kf(aM dE Ed Fw Js Nk Rm Tj) Ap(aC aY bM Bo bU cP tV) Jd(bU dE Ed Hq Mm Qx Tj) Pc(Hx In Js Ly Nf Nt Nx) Dq(aH aU Bo dD Mg) Nt(In Jj Li Oz Pf) Kq(Cu Fw Js rP Tj) Li(Jk Nf Nx Pc) dU(Lh Lx Mx Mz) Ti(tV vA vH) Mb(Nv Pf Qe) Jt(eM eP sC) Lp(kI mM nA) dO(bM Bo gT) rP(Im Pd rR) Aa(bM uR) Ly(Fr Jp) Hx(Jp Nv) Ii(qZ uR) Qb(Qa Qe) Nx(Oz pI) Uf(pS sC) aQ(dV fR) cW(gV tV) EfvQ FckI GcgW MmPf MwKc IcqP IzuP KgvC KlrW LhpI YlrZ VotV aDgV aMcK aYmP cPdQ cYfR dRdV Constrained panels with 2 analytes, where 1.0E-6 >= 'AUC p-value' > 1.0E-7. Contains 639 panels of 197,786 total panels evaluated. : Ad(Ed Hq Hw Hx Ic Ik Io Jd Jk Jn Jv Kc Kq Ly Ma Mb Mp Mx Nc Nh Nk Nn Ny Qb Qz Ra rW Ue Un Vp) On(Cq Ed Fw Ic Il In Iq Jj Js Lj Mf Mm Mu Mv Mw My Ng Nn Nq Ns Nt Nx Oy Pd Pe Pf Pj Qb Ra) Un(aF Cu dE Dg Ed eQ Fw Hr Hx Ic Jd Jg Js Kc Kf Ms Mx Na Nk Ok Pg QB qD Ra Ue uW Vp Tj) Ap(aD aK aN aQ aR aV Bn bX bZ cC cK cO cQ dE Dl Je Js Kx Nl Nn Oe Of Pj rW Vp vQ Tj) Nl(Dg Hw In Jj Jl Lj Lv Lx Ma Mb Mg Mz Nn No Nr Nt Oh Om Oy Oz Pc Pz Qa) Nc(Hw Im In Jl Lj Lv Ly Ma Mb Mg Mz Nn No Nt Oh Om Oy Oz Pc Pz Qa Qd) Jg(aD aG aI aO bQ bU cK CQ dI Ed Fw Je Jv Kx Qw Qz Ra rW Ue uP vQ) Dg(aD aF aH aN aQ aR aU aW cC cO cY Ic Jd Je Mp Oe Pc pS sC vH Tj) Nt(Fr Im Jp Js Lh Lj Lx Mb Mw Ne Nj Nk Ns Nv Nx Oe Pa Pc Pd Qe) Ji(aI aK aM aN aY bQ bU bZ dB Ed Ha Jd Ld Qg Qx Qz Rc Ub Ue) Pj(aR aY bX cN cP cR dI Et gL Ic Kc Kf Kl Kq Ks Mp Qz Ra Rc) Nj(Bb Dl Iv Lj Lv Ma Mg Mv Nn No Nr Oh Oy Oz Pa Po Pz Qd) Lh(dE Ed Hx In Jd Jj Js Li Lj Mm Ms Nf Oz Pc Pd Pf Tj) Li(Hw Il In Iq Js Mm Nk Nq Ns Of Pd Pf Qb Qd sC) Ne(Im Jj Jt Lj Lx Ma Mm Nm Nn No Oh Pc Pd Qe) Jd(bZ dI Dl dX Kc Kf Mg Mx Ok Pg Ra rP Ue uP) Et(aG aK aO bQ cI cP dI eM iP oE qB rW vH) Mb(Aa Do Gw Jl Lj Lx Mm Mw Nx Oh Pe Pz Qa) Dl(aQ aY Ch cY dE Di Ic Ik Js Mt vQ Tj) Fp(Hw Hx Jj Js Jt Ly Mg Nm Nn Oh Pz Qb) Fr(dE Hw Hx Jk Me Mf Mm Nx Oz Pc Pd Pe) Nd(Do Im Ma Mm Mz Nm Nn No Nr Om Pd Qa) Cp(aK aQ aR aU aV Bg bM bU cC cK dE) Ik(aF aM aY Bb Bn dE dI Ly rP rQ sC)

Figure 14 Continued

Nx(dE dU Jj Jp Jt Lj Mm Pc Pd Pf Qe) Kf(Cu Hq Mm Mx Pg Qb Ra Ub Ue Vp) Ok(cP cW dB Ha Ic Qx Qz Tn Ub Ue) Jp(dE Lj Oz Pc Pd Pf rP Ub Ue) Uf(Fw Hq Js Mp Ue vT wP xA Tj) rP(cH dB Ic jV Mz Om Pz Vt) Mm(Hu Hx Kc Oz Pe yH Tk) Kq(Bg Hq Mj Mw Ny Pg Ra) Jt(aR dE qZ Ra rW uR) Kc(bU Fc Ru Vp Vz Zx) Pe(Hr Hw Mf Oz Pc Qb) Pf(Hx In Mw Nk Oz Pc) Dq(aK cY cZ Kn Qe) Kl(aM Of tR vH vQ) Nw(aR Ch dE qZ Tj) Ba(Bn Bo Ct dE) Bb(aM bM cP Mt) Ti(sC uR vI wC) Ly(aR Im Nv Qe) Kg(Of tV vB vH) dQ(aV cG dF fR) dU(Fa Ir No Up) vQ(Ke Kj Nm Vo) Ef(aM tR uL) Mg(Ct uO wJ) Mt(aR dE Hx) Ue(cP Gw wF) Im(Oz Pc qZ) Qe(eP In Pc) Pd(Jj Lj qZ) gT(aU Gn Ng) Aw(aK aM) Ke(pK vH) Ko(aM dE) Yl(nK qU) Om(Mf wF) Vw(jO rB) dB(Bo tV) dV(Co Mk) eP(aV bB) nA(We Ye) AaNh AltV BndO FcmY GngW NmMu MwLj IcwB IiwG IzuL YjqX VzlW SiiC WcrB XalK aUfR bMcR klpK Constrained panels with 2 analytes, where 1.0E-5 >= 'AUC p-value' > 1.0E-6. Contains 1,088 panels of 197,786 total panels evaluated. : Kq(aF aI aL aM aR aY bQ bX Cq cR cW dE Dg dI Dk Ed Fn Hx Ic In Iv Jd Jn Jy Kc Kf Kz Ld Mg Ml Mm Mp Mr Mx My Na Nb Nk Nn Nq Nv Of Pc Qx Qz rW Ub Ue uG Vp) Un(Ap aR aY Bo bX cP CQ cR dI Dl Fc Ha Hq Hw Ik In Je Ko Ld Mg Mj Mm Mp Mw Nm Nn Ou Pd qA qC Qg Qx Qz Rc rV rW Ub Uf Uk Um vC) Dl(aF aH aM AR bC Bn cC cF cG cK cN Cq dB Ed gT Hr Hw In Jp Kc Kf Mp Nc Nd Nh Nl Nn Oe Of Pc Qb Ra Uf) Ap(aF aH aM aU cF cY DB dI Hr Hw Ic Io Jd Kc Kf Ly Ma Mp Mt Nc Ne Nh Nq Nw Nx Pc Pg Qz Ra rP Tz Uh) Jd(Aa aF aR aY bM bQ bX dH Fw Ic In Jp Js Jt Kg Kl Ko Ly Mw Nk Nm Nn Pd Ph Qe rW Uf Ug Uh Uk uR vQ) Kf(Ad aR bQ bX bZ cR Dg dI dU Hr Hw Hx iB Ic In Je Jg Ji Jp Kc Mj Mp Mw Na Nn Nw Of Pc Qx Qz rW vQ) bM(aK aM aN aQ aR aU aV aY BA bB bF Bg bU cG cP cY dB dF Dk Dq Fr Gc Ik Jt kl Mg Nm Nw On Pd) Dg(aM cF dB dI Ed Gn Hr In Jf Jv Kc Kx Ly Mt Na Nc Ne Nh Nn Nw Nx Of Pg Qb Qz Ra tR Uc Vp) Mm(aR Ch Ed Im Je Jf Jj Jp Jr Kl Ko Kx Lj Lx Me Mf Ml Mw Mz Nr Nt Nv Pc Ph Qe Qz Ra Vp Tj) Jt(aF Bo bX cK cP cQ Cu eQ Fw Hr Ic Iq Je Jj Lj Lx Mb Oz Pc Pe Pf Qx Qz Ub Ue Um Ur Vp Tj) Lh(aR bX Fw Hr Hw Im Iq Iu Jk Kc kF kl Ko Ld Ly Mp My Ns Nx Oe Of Pe Qb Qg qZ Ra Ub Ue Vp) Jp(aR Bn Ed Hw Ic Im In Iq Jj Jr Li Lv Lx Me Mf Ml Nk Nr Nu Pe Qe Qx Ra Vp Tj) Kc(aM aY bX Ch cP cQ cR dB dE dI Hq Ik Jg Ji Js Pd Qx Ra tV Tz Ue Uf Wf Yi Tj) Ne(Aa In Ir Iv Jl Lv Ly Mb Mg Mu Mz Nb Nj Nr Om Oy Oz Pa Pg Pz Qa Qd) Cp(Aa aC aH aN aY Bb bH bX cA cF cG cP Cq cR cY dB Gn Nj Pd rP Tj) Nd(AR Ba Bb Cw Gw Ih Ii Ij Io Ir Jl Lj Lx Mg My Oy Pa Pg Pz Qd) On(Aa aF AR Bn Bo bZ cK cQ Ha kl Ld Ms Nf Nv Qx Rm Ub Ue Uk Vp) Nw(aF aH aM Bn Bo bX cK cP CQ Cu dB dI Ed Ld pI Qx Ra Rc Vp) Qe(Aa dE Ed Hu Hw Hx Im Jj Js Lj Mf Mw Nf Nk Oz Pd Qa Qc Tj) Pj(aF aM In Io Jy Ko Mx Nc Og Ok Ou Pc Pd Pf Qt Rg Ue Um Tj) Nv(dE Ed Hw In Jj Jk Js Lj Me Mf My Nf Oe Oz Pc Pd Qb Tj) Ba(aC aF aH aK aM aQ AR aU aV Bg bZ cP cY dB Js Tj) Fr(Aa aF Bn Im In Iq Iv Jj Jr Lj My Nk Nq Nr Ns Of Tj) Ly(Bo cP Cw Jl Lj Lx Mb Mw Mz Nj Nl Nn No Nt Pa Po Qa) dE(aK aM aQ AR Bo cP Cu Kl Mb Mw Nc Nh Nl Pb Pf Uh) Ko(aR aY bX bZ dI Ed Fw Je Ji Mw Ps Ru rW Ub Yd Tj) Nc(Aa Ar Hu Ir Iv Jh lW Mu Nb Nj Nr Nu Pa Pg Po) aM(Aa aQ Bg bR bU cB cF cP cT Dk Ic Kj Mz Nx Sr) rP(Al Cv Cw cZ Dc dI Et Hb Ii Mg Ms Nr Ny sC Tz) Nj(AR Cw Ih Ii Ir Jh Jj kI Mb My Nb Nu Pg) Uf(Ed iB Je Kx Mj Na Nn Of Pg Ra Um vH Vp vS) Ad(dQ Gn gW iB Je jV Ks Ou Qh Qx Rm Uh Vt) Pd(aR dU In Lx Mb Mw Mz Nf Nm Nr Oz Qa rW) Nl(Aa Ar Bb Ir Iv Jh Mu Nb Of Pa Pg Po) Kl(Aj eP Fw Ic Js Mw Pc Ra sC tV uP vU) Pe(Dq dU Il Im Iq Jj Jn Mw Mx Nk Nm Oh) Mz(aR cK dI eQ fR Mb Mu Nt Om Oz Pf) Ar(aK bU cC dQ Mg Mh Mt Nh rW sC) Bb(aK aR aU aV aY bU cC cK tV vC) Lj(Hu Hx Im Mg Mu Nf Nm Oz Pc Qb) Nx(aR cK Dq Hw Im Lx Mw No Nr Qa) Aa(aR aY Bo dU Jr Me Nr Pc pI) Ik(bX cP cQ cR Cx dB fR Fw Tj) Jg(cI dU iA Ld Qh Qx rQ Uk Vt) tV(aV Aw Ch Dc Ic Iz Ke Kj Ma) sC(cH dB Fy Ic Ma Or Ph Pz Rh) Nm(aR cP dU Lx Om Oz Pc Pf) Mb(Ex fR Im Mu Na Nn No Om) Qa(Hw Hx In Iq Js Lv Oz Pc) Ji(Fw Ic Je pI Qh qZ rW vQ) Pf(Hw Im Iq Jj Js Oh Qb) Mw(Fw Me Nu Oz Pc pI) dO(aG cG cI dD dF Gl) rW(Hb Im Kg Kp Om Vt) vQ(dB Fy Ii Iz Jo Om) Dq(aQ Fp Kd Oz Tn) Et(iA oF pS qA qD) Ok(oF qA qB wJ yH) aR(bU cC cP Mg Pc) Aw(aQ aU aV cY) Ti(vS wG wL tM) Fc(dN iO mM qX) Nt(Nn Og Oh Qb) Lx(dQ Im Oz Pc) Ue(iB Jf lW Ou) tR(cW Dk Iz Ke) Nr(dU Jj Pc) Mt(bZ dI Vp) Tl(lW nA qU) Oh(Hx Oz Pc) Vw(kR qU Tj) dQ(aL Bg Cw) fR(aW Bo cM) Bn(bU cP) Ef(Ct wK) Th(nF nR) Mg(Bo rQ) Ic(aY rA) Ii(iB Tj) Im(dU Mf) Yj(jP rA) Zq(Nf Vq) Jh(wH wK) Js(Ke Kg) Kp(Em rR) Om(Nq wH) Uh(rQ rR) eM(Ao gV) lW(aY Yl) jD(Ry Vj) jV(Ju Pi) kl(bH dL) DoQn FinA FwKg GcjO GwIr NoOz MlgT MqwF HogW HpiO UbvS HxJl TneP VznK JjLi JovT KeqB VcjY PhdU aQdB bLiB cRtX Constrained panels with 2 analytes, where 1.0E-4 >= 'AUC p-value' > 1.0E-5. Contains 1,686 panels of 197,786 total panels evaluated. : Pd(Aa aH aN Ap Ar aY Bb Bo cK cP cQ dE Dg Dl Ed Fw Gn gT Ha Hw Hx iA iB Ic Il Im Iq Ir Iv Je Js Jt jV Kf Kl Ko Kx Lv Ly Mm Nk Nn No Oh Pc qY Ra rB sC Uf Ur Vp Tj) rP(Aa aC aH aI aL aQ Ar aU aV Aw bE cC cI cM cR cW dA Dd dE Dg Dp Ed Ef Fy Gl Ih Ip Iz jM Kc Kj Kn Ko Li Nm Nw Oi oN Qh Ra Rc Ub Ue Uf Uh Uk vI vT) Jt(aC aH aK Ar aY Bn Cq cR dB Dc dI Ed Fn Ha Hw Hx iA Im In Ir Iv Jf Jr Jv Jy Kc Kx Lv Me Mm Mw Nf Nk Nn Nr Ns Of Oh Ou Pa Qe Qh Rm Uc Uh) aR(aC aK aM Ar aU aV Aw aY Bg Bn bR bX cB cG cK dB dQ Ed Ef Fc Fr Hq Ic Ih Je Jl Kc Kl Mb Mp Mw Nh Nk Nl Nn Nr Nt Nv Om Pe Pf Pz Qe Ue Uf) Mm(Aa aH aN aQ Ar bM Bo bX bZ cK CP cQ Cu dE Dk Dl dU Hw iA Ic In Iq Ir Iv Lv Ly Mp Nk Nn Nu Oh Ou Oy Pa pI qB qZ Rc Tz Ub Ue) Ue(aM Ap Ar aY Ba cQ Cw DL Ed Ex Fr Fw gL Ic Ih Ik Je Ke Kl Kn Ko kR Li Mt Mw Nc Ne Nh Nl Nw nY Ph Qd Qe rW Sr Ur vU wL tM) dE(aJ aU aV Aw aY bA Bb Bg bM cG Ch Co Cw cY dF dG Ef Fp iB Ic Im Jh Li Lx Ly Mg Mz Ne Ng Nj Nm No Nr Oi Oy Pc Pe Pz Qa Uf Ut) aM(aC Af aK Ao Ar aU aV aY bA bF Bn bX cG Ch cR cY dB dI dO dQ Ed eM eP FR Gn gT Hb Iz Jd Je Ke Kg Kp Nd Nh Nj Pc Uf Vt) Ar(aF aU aV Bb Bg bM bX cK cP cY Ed Ef Gn Hb Hq Hr Ic Jp Js Kc Kl Lh Ly Mw Ne Nk Nn Nw Nx Og Ou Oy Pc Pg uN vH Tj) Kc(aF Bn Cw Ed Fr Fw Hb Hl iA Je Jp Ke Kg Kj Kl Kn Ly Mg Mt Ng Nk Nm No Nw On Ou Pc qB Qt Qz tR Ub Uh Uk Zq) Bb(aC aD aQ Aw bC bH Bn Bo bX cF cG cN cQ cY dB dI dL Ed Ef gL Ic Ly Mg Mw Nc Ne Nh Nx Ou Oy Pc uP Tj) bM(Ao Aw Bn Bo cC Ch cK Co cQ cT Cv Cw dD dQ Ef Fp Gn Jp Js Lh Ly Mp Mt Mw Nj Nk Nn Nx Om Pg Uf Zq Tj) Mw(Aa Cp Dl Ed Hb Hw Ic Im Iq Iv Je Jj Jp jV Kx Lv Lx Mf Ml Mz Nm Nv Qg Ub Uf Uh Vp Vt wF Tj) Nd(Ao Ch Co CP cQ Dk Dq Hu Is Iv Jh Jj Jo Jq Lv Ly Mi Mj Mk Mr Mu Mv Nk Nu Ny Of Oz Pc Po) aY(aK aQ aU aV Ba Bg bU cK cP Ed Fc Fi Fr Jp kC Kf Kg kI Kl Lh Ly ml Mp Mt nD Nm Nw Rc Uf Zq) Aa(aJ aU aV Aw Ba Bg Bn cF Ch cP cY Fp Ir Iv Jp Lh Li Lx Mf Ml Nt Nv Oz Pe Pf Qa tV) Nm(Bo bX cK Cp cQ Iv Je Jj Jr Kf Kn Kq Kx Lv Mb Mf Mz Nf Nn Nr Pa Qa Qe Ra tV uR) Mg(aN bX cK cP dI Dl Hb hR Hw Ic Ir Iv Je Jf Ko Kx Mb Mz Nu Pc Qz Ra Uh Um Vt Tj) Kl(bX cP Cu dI fB Hq In Je Jp Kf Kx Mj Mp Mx Na Nk Nn No Nw Oe Pg Ph Qz Ub Vp Tj) Ba(aD bH bQ bU bX cC cF cK cN dI fR Hw Ic Ly Mp Nh Nj Nk Nl Nn Oe Of Pc Pg) Ko(aF Dl Fc Fd Fn Ic Ik Jp Js Kf Kq Kx Ne Nh Nl Pg Qx Qz Ra Sf Sh Tz Uf Vp) Lh(aF aH aN Bn Bo bQ bZ cK cN cP cQ Cu dB Ha iA iB Ic jV Qx Qz Rc Rm Um Ur) sC(aS bF bL fP Gl Hb Ij Im Jd jY Kf Kp lL On Pc Pf qC Ra Rf tR Ub Uh vQ yL) Cp(aD bC Bn Bo dQ Hq Hr In Jk Ly Mj Na Nh Nk Nl Nn Nx Of Pc Pg Qe rW uL) Tj(Co Cu Cw Dk Ef Hb Im Ke Kg Mt Mz Nx Om Ph pK Qa Qd Rz Sr Uh Ut Ux Zq) Uf(Bn bX bZ cE cQ Cu dI hB iA Ic jV Kf Ly Ma Mx oF Ou Ph qB rW tV Tz Uh) cP(Af Aw Bo bU cC cK cR Cu Cv Cw dB dI Fr Gn gT Kf Mt Mz Nh Nk Nx On Pc) Dl(eM Gn gW Je Ke Kx Ly Mb Na Ne Nk Nw Nx Pg Qx tR tV Tz Uh Vp) Mz(cQ De Iv Je Jh Jj Jr Lv Mf Nr Nu Of Og Pa Pc qA qD Qx Vp Zq) Kq(cN Hv Hw iB Ij Jr Mt No Po pS Qb Qc Qh rR Uh Uk Um vH vQ Vt) Bn(aK aQ aU aV Aw Bg Bo cB cC cG Co Cu Cw cY Ef Kg kl Mb Mt) Jp(aH bQ bX bZ cK cQ dB dX iB Kx Oh Ph qA qB qY Qz rB Rc Ug) Lj(dU Hw In Iq Iv Jh Jj Jl Js Lv Lx Nk Nn Nr Of Oh Om Oy Pz) Ly(aN Ch cQ Dq Ir Jh Jj Kf Ma Nr Nx Ny Oh Om Oz Pc Pg Qd) Ed(bX Co Cw Fr Fy Ic Ii Im Ke Kg Mt Nn No Ph Qa Qd Sr) Nw(aD aN Bg bQ bZ Dk Fn Fw Ha Ic Je jV Kx Qz rQ Ub Uk) On(aD aH aK aN bQ bX cO cR dB dH dI Kx Qg Qz Rc Uh Vu) bU(aJ aK Ao aU aV Aw bA Bg Bo cG Co Cv cY dL FR Kf) Mb(Ap dB Dg Ih Ii Ij Io Ir Ma Mv Nr Oy Pa

Figure 14 Continued

Pg Po Qd) cC(aK aN Ao aQ aU aV aY Ax bA Bo cG cK cN Co cY Fr Zq) Ef(aF aK aQ aU aV Bo Cq dI dQ Gn Nk Of Pc rW vH) Kf(aF aH cF dB Jn jV kI Kx Ms Ou Ps Sh tR tV Uh) Nv(aF cK Cu dU Il Im Iq Nk Nq Nr Ns Of Oh Ra Vp) Ic(cQ Cw Fr Ik Iz Kx Ng pS Qe qY Rc rQ Ss Uc) Pc(cQ Dk Ih Iv Jh Jl Kn Nn No Nu Om Po Qd qY) dO(aC Af aI aJ aL aN aP bA cE cJ cK dG dI Ql) iB(Ap bX Ch dB Dc Dd dI Kg Ok Pi Ub Uk Un Wd) tV(Ik Jg Jo Kp Kr IK Ms Pz Qg Ql rQ Ub Uu Vt) Im(Hw Hx In Iq Jj Js Lv Me Nf Nk Qb rQ rV) Qe(Cu Il Iq Je jV Lv Nr Of Oh Qg rB Ub Vp) Mt(aF aH Bo bQ bX cK cO cQ cR dB Kx Qg) Uh(aF Dg dU Fw Ik Js Nc Pg Ra rW Un uW) Oz(Ih Ir Jh Jl Ma Nn Nr Nu Om Po Pz Qd) Cw(aC aK aU aV Db gW Je Nh NI Rb vB) jV(Ch Ih Ii Ir Jd Ji Pe Pj Po Ra Va) Bo(aK aU Bg Db Fr Gc Gn Gt Nj Nl) Qa(Hu Il Jj Mf Nf Nk Nn Oh Qc Qd) Ke(Cu Fw Hq Nk Pg qC qD Ra Ub Vp) Om(Hw Hx Iv Lv Ml Mv Nu Pg uP vH) dQ(aI bA bQ Cu cW cZ Dg Ex Fw gC) vQ(aE Ch Ct Dk Jh Ms Og Pz Uc Vt) Fr(aK aU Aw cK dB Ex Il Oh wF) Gc(aC aU aV Et hV iP Nh Qv Vo) Gn(Ao Ap bN bX cB Ch Co Cu dN) Nj(Ao Ch Co Cv De Dk Ex fR lW) dU(Ij Jd Li lW Mk Nl Qd Qm Qw) Dg(eM eP gW Io Ou rW Tz Ur) Zq(bZ Fi hG Hx iP mM Qn qT) Kg(Hr Je Nk Pg Qb Qz Ra Vp) Oh(Hw Iq Lv Lx Mc Mf Ms Nx) tR(Al Aw Ch Ct cZ jK Kp Pi) Jl(Hw Iq Iv Jj Lv Mf Qb) wF(Hw Jh Jo Kj Pz rR Un) Ii(lL qB qC qD rB tL) Ik(bQ cK Ex Ra Ub Vt) Jd(bF cE Of Ou Qz rQ) dB(aK aU aV Cu cY iH) kI(bG bQ hF Mn Pj Th) Ch(Fp Ph qY Vt Ti) Nr(Hw Iq Js Lv Pz) Lx(Hu Hx Iv Mf oT) Hp(iP kR oE Rt Vj) Hb(cQ eM eP Fw Ra) Iz(Nk Of rW vH wK) Nx(bX cQ In Nn Pa) aC(Bg Dq vI vS wH) Ap(Hq Jy Ou Qx) Fy(Je rQ rR Vp) Vz(bN mY nB oE) Ji(iA lL qB uR) Un(Fi iA uZ Zw) aK(Ao Ax cR Cu) iP(kC nD Ry Ux) qZ(Et Jg nF Ng) jO(Rz Uw Ux Vh) rW(Gl Kj Kn Vs) uW(Co Pf Qh Vv) Bg(cK Cq fR) Dq(bE cB Uv) Ti(bX wD wH) Gw(Ij Ma Rh) No(Hx Mf Mu) Ny(pS uR vB) aF(Cu Fp gV) aU(Ao Cu dV) dX(dD Hv Ow) lW(Ih Jn Th) Ad(fR iA) Do(Kr St) Fw(Pj St) Mu(Ih Iv) Ne(Jh Po) Nh(bX cQ) Ub(Li Qd) Jj(Nn Pz) Kn(vH Vp) Of(Kj Nc) Ok(pI qD) Vt(Ng uR) aH(cG qH) aN(gV Nl) bE(vS wH) gW(gT Ps) oE(Fd Vi) uP(cW Dk) vC(Al Dc) AoaV BcdV CoJs EmhV FcoN FidN GlpS NuLv MaMf TtqY SikR RbeQ JgoF SrdI WfjD JnnJ TlrX RxqU LirQ LpnK RfbX OiuR UuwK VjjH VqeX VwhG PiqH cGcK cHvS cUrZ cYeP cZtT dRfR kKpH kPpK

Constrained panels with 2 analytes, where 1.0E-3 >= 'AUC p-value' > 1.0E-4. Contains 2,691 panels of 197,786 total panels evaluated. : aY(aC aD Aj An Ao Aw bA Bn bR bX cB cC cF cG Ch Co cR cT Cu Cv Cw cY dB dI Dk Ef Fp Fy Gc Gn gW Hb Hp Hq Hr Je Js jV Ke Kj kK Kp Mm Mz NC Nd NH Nj Nk NL Nn Nr nT Nx Pb Pc Qe Qg Qw Ra Sj Tr Tz Uc Uh Vt Wh Tj Ti) bX(Aa Af aK aN Ao aV Aw Bg Bn Bo Ch Co cR Cu Cv Cw Dk Ef Fp Fr Fy Hb Ic Ii Im Iz Je Ke Kg Kj Kn Kp Li Ly Mb Mw Mz Nc Nd Ng Nj Nl Nr Nv Om Pc Pd Ph Qe Qg Rc Sr Tr Tz Uc Ue Uh Zq) Ed(aF Ax Ba bM Bo Ch cN CP cQ dE dI dL Ex Fa Fp Gl Hb Ih Ik jB Je Kj Kn Kx Li Lx Ma Mg Mz Ng Nh Nj Nm Nr Nx Oh Ou Pc Pe Pf Qm Qz Ra Rf rR rW sC St Tr Tt Uc Uh) cP(aK aQ aU aV bC bR cB cG cY dO Ef eX Fc Fp Fy Gc Gl Hb Hq Hr Ic Jp Js Ke Kg Kj Kp Kx Mb Md Mf Mp Mw Nj Nl Nn Nv Om Pf Pg Pz Qe Ra Rc Tr Tz Ub Uc Uf Vp Vt Tj) dE(Aa aD Aj aN Ao aP aW Ax bB bF Bn bR bU cB cF cK cN cQ De Dk dL Fy GL Hb Ih Ii Iz jV Kc Kg Kn Kp lW Nd Nn Oh Om Ou Ph Qg Rc rR sC Sr Tr Tz Uc vS Vt Zq Ti) Pc(aN Aw bM Bn Bo bU cC Ch cK cN cR Cw dB De Dq fR Gc Gn Hb Hu iB Ii Ij Ir Iz Je Jj Jr Kg Kj Kx lL Lv Ma Mb Mf Mu Mv Ny Pg Ph Pz qZ rW Sr Ss Tr Uc Ue wF) Tj(aM aN Ao aR Ax Bg Ch Fa Fy Gl Ir Iz Je Kj Kn Kx Li lW Lx Ly Ma Ng Nm Nn Nr Oh Oi oQ Ou Oy Pa Pe Pf Po Pz Rf Ry Si Ss St Tn Tr Tt Uc Ue Uw Vq Vt Ti) Ue(aF aP Ax Bb bM Bo bV cK cN dI Fa Fc Fn Gl Hb Im jT jV Kg Kx lL Lx Mg Na Nn No Nv Of Oh Oz Pd Pf Qa qD Qz Ra Rc Rf Uh uW vQ vS Vt wG Zq Ti Th) jV(aH Al bL cG cH Cw dB Dd Dl Et Fp Gl Hb hC Ic Id Im Jh Jl Jt jU Kg Ma Mc Mg Mt Mv Nh Nj No Nr Ny Oh Ok Om On Pa Pf Pz Sf Tz Uk Un uO vQ) Aa(aC aD aK aQ aS bU cB cC cG cK cN De dG dI dL Hu Hw Ih Im Je Jh Jn Jt Lv Ly Mg Oh oK Om Oy Pa Pg pK Po Pz Rc sC uP Ut vQ) aR(aE aF Aj Ao aQ bA bC bH Bo cF Ch Co cT Cu Cw cY Db dG dI Dk dL Fp Fy Gc Hb Iz Jh Ke Kg Kj Kp Ou Ph Rc Tz Ub Uc Uh Vt Vz) Ar(aC aD aH Aj aN aQ Aw bC bH cF cG Ch cQ cR Cu dB dI eF Gl gW Iz Je Jy Kg Kj Kx Nm Pf Qe Qx Ra Rc Ss Tr Tt Tz Ub Uc Vp) Je(Ba Bb Ch Fr Hb Ic Ii Ik Im Ke Kj Kx Li lW Mt Ng No Oh Pf Ph Qa Qm Qt Qx Ra Rc Rf Tr Tt Tz Ub Uc Ug Uh Uk Vp Vt) aM(Aj An bC Bo cC Co cQ Cu Cv Cw Cx Db De Fp Fy Gl gV gW Jh kI Kn Kx lW Ly Nk Om Ph Qg Qm Rc Tr Tt Ub Uc Uh Uk Vp) Nm(aH Aw Ba cN Cw Di Dl Fn Hu Hw Ic Ih Iq Ir Jl Jt Kl Ly Mc Nk No Nu Oh Ou Ph Po Qx QZ rW sC Tz Uh Ur Vp Vt) Ra(Ba Bb Ch Co Cp Cv Cw Dk Ef Ex Fr Fy iB Ic Ii Iz jY Kj Kx Li Ly Mt Mw Nx Qd Qe rW Ss TR tV Uc uW Vt wF wH) sC(Al Ao Co Cp cR CW Dc dI Dl Fp Fw Iz Jh Ji Jp Kj Ko Kq Mw Oy Pi Po qD Rc sO Tr Uk Un Ur Vo wF wG wL) dB(aD aJ Aw bA Bg Bn bU cG cN Co Cw dF dG dL Fp Gn Ic Mm Nc Nd Ne Nh Nj Nl Nv Nx Pb Pd Qe Rc Uf Vj Vt) Ch(aC aK aQ aU aV Bo bU cC cK Fc fR Hr Hw Ic Id Js Kx Nh Nk Nl Nn Nx Of Oz Pg Qe Rf rW Tr uL Vz Yi) Kg(aF Bo bU cN cQ Cu dI Gn Hq Hw Ic In Jf Jj jT Kx Ly Mp Mt Mx Nn No Nw Ou Pd Ph qB qD Rc Um Ur Vt) Gc(Af aK aN aQ bB Bn cY Fp Fr Ic jT Jy Kd kR Ly Mb Mh Na Nd Ne Nj Nl Nx Oh Or Oz Pd Pe Pf Qz Ri) Mg(Bg Bn cN cQ cR Ex Fc fR Gn iB Ih In Jj Jr lL Ly Mf No Ou Oz Pa Ph qA qB Qd Qg Qx Rc rW Ur Vp) Cw(aQ bU cC cY HB Hr iB Id Js Kx Kz Mp Nc Ne Nk Nn Nx Ou Pg qB qD Qx qY Qz Tz Ub uL Um Vp) dI(aK aU Bg cG Cu dQ Fp Fr Fy gT Hb Ic Id Iz Jp Ke Kp Lh Ly Mm Nh Nj Nl Nt Nv Nx Om Pd Uh Vq) Mw(aN Ba Bn Bo Hx iA In Ir Jr Kz lL Ms No Nr Oh Ou Pa Ph Pz qB Qx QZ Rc Tr vH wH Ti) Nk(cN cQ Dk Fy Gl Hb Ic Jl Jy Kj Ko Lx Mb Mz Nr PH pI Po Pz Sr Ss Tn Tt Ua Uc Uh uR) Ub(Ba cN cQ Dk Ef Fr Ii Im Iz Kj Mt Nc Ng Nh No Nv Ou Pd Ph Qa Rf Sr Tn Tr Tt Uh wG tM) Ke(aF aH bQ bU bZ cN cQ cR Fn Hv Hx Ic In Jn Kx Mj Mp Mx Na Nn oF Ou Pd Ph Qb Qx Qz Rc) rW(Ao Aw Co Cv Dl Jh jY Kc Li Mt On Pe Po qC Qg Qm Qt Rc rX Tr Tt Tz Uc Ut Vo vS Vu yL) Nv(aH aN bM Bn Bo bQ bZ CQ cR dQ Fw Ha Ic Kx Ld pI pK Qg Qh Qt Qx QZ Rc Rm Vt) Ly(aQ aU Aw cG cK cN cR cY Ef Gl Hb Hu Ih Ij Iv Jr Jt Kx Lv Me Mu Mv Nu Oy Pz Rc) iB(aC Al cK Et Fr Ic Ih Im Jg Ji Jl Mt Mv Ng Nj Nr On Po Ry Tz Uw Ux Vh Vw Wc Zq) Vp(Ba Bb Co Cp Ef Fr Hb Id Ii Ik Iz Kj Li Nr Nx Om Qa Qd rR Sr Tr Uc Uh Ut Wn) wF(aL bE cM dH Fa hO Hu Ij Im Kc Lh Mv My Nf Ny Of Og Oi Oy Pd Po rQ Uh Vs Vt) Gn(aC Af aK aN aS aU aV bC cC cG Cs Dk Hp Ik Jr Mz Nd Nj Nx Or Ug Vt Vu Wm) Qe(aF aH Bb Bn Bo bZ cK cQ Cx Fw Ha KC kI Kx lL lW Ny Pz Rc Rm Tr Um Vt) Ef(aD bQ bU cK cN cR cY Dq fR gW Hq Hw In Jk Js Kx Mx Na Nn Nx Pg Qz Vt) Fc(bN cC cG cQ Et Ex Fb Fr Jg Kf Kp Mm Mt Mz Nh Oh Rj Ry Rz Uf Ut Vw Zq) Pz(cK cQ In Iq Ir Iv Lv Lx Me Mm Mu Mz Nf Nn No Nu Oh Pa Po tR vU wK yE) bM(Af bP Dc Fy gV gW Hq Hr Im Jh Kl Mb Mz Nd Nh Nl No Nr Oh Qb Rf Tr Vq) rP(Af Ba Bc Co Dk jY Kf Kp lL Or Pe Pi qC qY rQ rT Ug Uo Uu Vo vQ vV wG) Fr(aC aD aH aN aQ aV bC bH bZ cF cO Cq cY Fi Kx Ph Qx qZ uW vC vH wH) bU(aC aD Af aN aQ cK cN cR De dG Dk Hb Jp Kl Mz nC Nd Nh Nj Nl Nx Rc) Co(aC aF aN aV Bg Bo cK cO CQ cY Dq gT gW Hq Nc Ne Nn Pg tR vC) Ic(aH Bn fR Fw Im Js Kc Kn Mt Mz No Ou Ph qB Qt Qz rZ Tr Tz Uh Ur) Jj(Hu Ih Ii Ij Ir Iv Jo Jr Lv Lx Mb Mf Mu No Nu Oh Oy Oz Pa Po Qd) vQ(aC Ao bE Bg cC cH Cp Dc dH Hb Im Kc lK lM Ny Of Oi On Qu Un Uu) Ba(dQ gW Hq Hr Kc Kx Ma Mb Mm Na Nc Nx Ou Qx Qz tR Tz uW vH Vt) Dk(aC aK aQ aU aV bC Bn cC cY dQ Gl Hr Kx Nc Ne Nh Nl Oz Ph Vt) Uh(aH aI cE cQ eQ Jf Jp Kl Ko Mp Ng Nn Pd qB qD Qt Qz Rc Ss Tz) Bb(aH gW Iv Js Jy Kx Mb Mm Mp Nn Of Oz Pf Pg Ph Qx Qz Tz wK) Cu(aC aH aN aQ bH bZ cF cK cN CQ Cx cY eP fR Js Kn Mt Pg) Dq(Ad aI aJ aL An Bg dL dO dR Fw gW Iv Lv Mk Mp Nt Pd Pf St) cR(aC aU aV Bg Bn cK Cx gW Kl Mm Mz Nd Nh Nj Nx Pd rQ Uf Uk) Kj(cN Fw Hq Hr Id In Js Kx Nn No Pg Ph Qb Qz rB Um vH Th) Bn(bA bR cF cK dQ eF Gl Li Mm Nc Nd Ne Nh Nj Nl Nx Pd) Hb(aF Bo cN Ik Js Mt Mx Na Of Ou Pd Pf Pg Ph qD Rc Tz) Oz(Ex Ii Ij Io Is Iv Jo Jq Jr Lv Mb Mf Mr Mu Ny Pg Ss) aK(aH aJ aN bA bR cF cG cN De dG dX eP Fp Jp Lh Mm Nj) aU(aD aH aJ aN bA bR cF cG cN cQ eP Fp Jp Mm Pd qH tV) fR(aC AN Ap bF bR cB cJ Cv dD Dg Dl Kc Kd Ml Nd Pb) Nn(Fy Hw Hx Im Iq Iv Jl Ko Lv Lx Me Mf Ms Nf Nr Nu) Mz(aD aF aN Hu Hw In Ir Me No Oh Oy Pg Po qB qC) Tr(cN cQ Fw Js Kc Kx Mt Na Nh Of Ph Qz rQ tV Ur) Ii(cK Fw Jf jY lW Ou Ph qA Qx Qz Rc Rm Um Ur Vt)

Figure 14 Continued

Qd(Hu Hw Hx In Iq Js Lv Me Mf Nf Nu Om Pa Qb Qc) cC(aC aD aJ Aw bB bF Bg cT Cv dG Fp Nj Nl uW vS) Om(aF aN cK cQ Ih In Ir Jh IL My Nf Ny Pa qZ) Pd(aF cY hR IL Ph Qg Qx Qy Qz Rc Sf tV Vt Vz) aV(aD Af aJ bA Bg Bo bR cF cG cK cN Dd De tR) dU(cF dL Fp Fy Ha Iv Ko Ml Mn Nd Nw Oe pH Qz) Aw(aC aD aH aN bC cG cK cN Cv dL gW Mm vH) Nr(Gw Hx Im In Iv kI lW Mf Oh Oy Qb tR vH) dQ(aC Ap Ax Bc bE cK Cq Cs cV dL dM gT Gw) tV(Ao cM Cv Gl Iq jF jK jQ Kq Li Og Pf Ph) Cp(Gl Hv Hw Hx Js Kx Mp Mx Nq Ou Pf vH) Fi(Et Jg Kf Li Oh Ph Ry Rz Uf Ut Vw Wm) Nu(Hw Ih In Iv Jh Ma Mb Mu Ns Oy Pa Pg) cQ(Cv Fy Kl Mb Nj Nl Nt Rc Uc Ug Vq Vt) kI(aD aF aS bl cD Gp Ih Ir Nc Nx Oe oQ) Po(Hu Hw Hx In Iq Iv Lv Mf Nf qZ wH) Fw(eC Fy Iz Kn Ou Ph Sr Ss Tz Ua Uc) No(Hu Hw In Iq Iv Jl Lv Me Nq Oy Pa) Zq(Ap Bc bN cZ dN iO kQ oE Pk Qv rA) Oh(dV Hu Im In Ir Iv Jh Jl Kc Oy Pa) aC(AJ Ao cG Cv dF dG Lh Mm uO vT) aN(Bg cG Cv dF dG Fp Jh Jl Jn Nc Nh) cY(aD aH aJ Ao Ax Bo cF Dd De Fp Mm) qB(Ap Dg Jt Kn Kq Ng Nw Pe Sr Vo Ti) Ko(eQ In Na Nb Nc OF Ou Qb tR) Uf(aF aH al aO bQ cN Jy pl qA qY) Bo(Aj cG Hp Iz Nc Ne Nh Ss Ye) Mb(Cx Hv Is Jh Jo Jq Lw My Of) Mt(lW IY Ph Qx Qz Rc rQ Tt uR) Ik(Id Jf Kx Ou Ph Tz Ug yH Ti) Vz(Jg Kf kR nH Qz Ry Un Vs Vw) aQ(aD aH AJ Ao Bg De dG eP) cK(Ao BC Cv dF dG dL Im Ng) Qg(Ih Kn Ne Nh Nl Qa rR Tz) Jp(aF hX iA IL oF Ou qD yH) Kx(Ao Iz Kn Li Nc Ng Rc Uc) Lh(aD Cq hR Jy IL lW oF uR) On(eQ iA IL rB rQ uR wG wH) Vq(iO iP kR Mh Nf ql qY Ux) qA(Ap Dg Ji Jl Jt Mm Ng Ti) Cv(bA cF cG cN dG Nd qH) Ex(kF Kq ml Mx Nd Pk Rc) Fy(cN Hq Jf Js kR Pg qY) Im(aF II Iv Of qY rB Vt) Kl(aF aH bQ cE cN Ou pH) nC(bG cD cF cM dA fP hC) qD(Ji Jt Kc Kn Mq Nw Ti) Bg(aD aH bH cF cN Iz) Gw(Hw Iu Ml Mr Na Pg) Lv(gT Hu Ih Iv Jh Mu) Mf(Ij Ir Iv Jh Jt Pg) Mm(aF al Cx De eT oF) Hp(Du hV In kF Pk Ur) Uc(iA Js Of Qw Qz Ur) cG(bQ bR cF cO Cx hA) dO(aW bO Dg Di dL dV) eQ(Ji Kc Kf Ld Nt Ri) IW(bH hC Lp IY Nx Qa) tR(Aj Dc Dd jQ Oi Qu) iP(nH Ps Si Sj Vj Ti) rB(Ad Pe Ux Wd Yg Tl) qH(Af aL cH qG qP vT) Dl(gL Ou Ph Qz Ur) Ir(Hw Hx In Iq Mu) Iz(Jk Js Pg uW Vt) Rc(Kc Ou Qw Qz Vt) Ss(Kc Nx Of Ph Qz) Jl(aF Hu In Js Nf) Kn(Js Mx Pg Qx Vt) Ut(aF kO Mr Pg wH) cU(rQ rS uW uY vT) qZ(Is Jh IK Ny Pa) Gl(gW rR vB vC) Lx(Hw In Js Qb) Ih(Hw Iq Jh Rm) Kf(Rt Ru Sf vH) Rz(An Bc bZ Nf) Ry(jY kR Pk Yl) Nw(iA Jy IL qC) Un(jY uR Yk tL) IY(Lp mP nD rY) nJ(jD Qa qU Tl) hV(Ps Tz Wd Yg) qY(Ad Di Ok Pi) vS(Aj aL bL cW) Cx(Nc Nh Nl) De(Nc Nh Nl) Do(Ki Ou Ur) Ma(Iv Mu pS) Nd(Ax cN Lw) Hq(Sr Tn Tt) Jd(Fd oF Ti) Ji(hR qC yH) Vc(gL jD oN) Ux(iC Ip Uu) Oy(Me uW wH) aH(dF eP Fp) gT(Bc cl cL) mP(Mn mY nN) nL(cD cM hC) kC(Lp pH Qa) kO(Ad jD Up) kR(Kq Ps Tl) oE(Du Si Ti) pK(Ml Mx tF) Ao(cF Ne) Mv(wH tM) Ng(Qw Qz) Tz(Na Ph) Ij(Iq pl) Jg(eM pl) Sr(Mx Ur) Kp(Rx vB) Li(aF pS) Rf(Jf Zw) Nx(cN Qx) Vj(An bG) Vw(Ip Rj) Pa(Iv Jh) bC(bA pH) bR(aJ dG) cH(rA vW) eP(Ad aW) gW(Ap dV) gV(cM cX) mF(rX rY) mZ(bG bZ) iA(Dg Ok) wG(rC rR) AfeM AxNe DrqT EtIL MquR MuJr NcnK TnJs YgrA YjIK SidN SfjU QzVb JtOe TlmY KcPf LpqU RhpS QmaF OguV VhjD VorR VvuY PjjY aDcB bEvT bLrZ cOuT dHwH nDpH tSjQ hCkF

Figure 14 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.9E1 | 4.8E1 | 8.1E1 | 5.1E1 | 5.8E1 | 3.3E1 | 1.0E0 | 1.2E1 | 4.8E2 | 1.1E2 | 1864 | 8 | 312 | 8 | 0.35 |
| Ad | ug/mL | 3.9E-2 | 5.0E-2 | 7.4E-2 | 5.1E-2 | 8.9E-2 | 3.8E-2 | 2.7E-4 | 7.8E-4 | 5.4E-1 | 1.0E-1 | 534 | 10 | 204 | 10 | 0.49 |
| Af | ng/mL | 1.2E0 | 3.6E-1 | 1.6E0 | 4.9E-1 | 6.0E1 | 5.7E-1 | 1.7E-3 | 1.7E-3 | 5.3E2 | 1.9E0 | 534 | 10 | 204 | 10 | 0.29 |
| Aj | ug/mL | 1.5E0 | 9.9E-1 | 2.6E0 | 2.0E0 | 2.4E0 | 2.2E0 | 1.5E-3 | 1.3E-3 | 6.1E0 | 5.6E0 | 534 | 10 | 204 | 10 | 0.40 |
| Al | mg/mL | 8.8E-5 | 7.8E-5 | 2.5E-4 | 2.3E-4 | 4.1E-4 | 4.4E-4 | 2.3E-6 | 7.8E-6 | 2.2E-3 | 1.5E-3 | 534 | 10 | 204 | 10 | 0.48 |
| An | U/mL | 5.0E1 | 7.5E1 | 1.7E2 | 1.3E2 | 4.4E2 | 1.1E2 | 9.8E-4 | 2.7E1 | 5.5E3 | 3.4E2 | 534 | 10 | 204 | 10 | 0.65 |
| Ao | pg/mL | 8.8E1 | 8.7E1 | 4.6E2 | 1.4E2 | 3.2E3 | 2.0E2 | 1.5E0 | 4.1E0 | 3.9E4 | 6.9E2 | 534 | 10 | 204 | 10 | 0.44 |
| Ap | ng/mL | 3.3E1 | 4.1E1 | 4.8E1 | 5.7E1 | 5.1E1 | 6.2E1 | 8.4E-5 | 4.4E0 | 3.3E2 | 2.1E2 | 534 | 10 | 204 | 10 | 0.53 |
| Ar | ng/mL | 9.7E-1 | 2.1E0 | 1.1E1 | 8.4E0 | 1.8E2 | 1.5E1 | 3.4E-3 | 3.4E-3 | 4.1E3 | 5.0E1 | 534 | 10 | 204 | 10 | 0.61 |
| As | ng/mL | 8.7E-3 | 1.1E-2 | 1.3E-2 | 9.9E-3 | 1.8E-2 | 6.3E-3 | 1.7E-3 | 1.7E-3 | 1.3E-1 | 1.9E-2 | 534 | 10 | 204 | 10 | 0.52 |
| Aw | pg/mL | 1.6E1 | 1.7E1 | 1.7E1 | 1.9E1 | 6.2E0 | 5.2E0 | 2.9E-2 | 1.4E1 | 4.8E1 | 2.9E1 | 534 | 10 | 204 | 10 | 0.64 |
| Ax | ng/mL | 2.1E0 | 1.9E0 | 1.6E1 | 1.1E2 | 6.0E1 | 2.7E2 | 1.2E-2 | 1.0E-4 | 7.7E2 | 8.5E2 | 534 | 10 | 204 | 10 | 0.56 |
| Ba | ng/mL | 6.5E1 | 7.6E2 | 4.5E2 | 1.6E3 | 1.1E3 | 2.5E3 | 2.7E-1 | 4.1E0 | 8.1E3 | 8.1E3 | 534 | 10 | 204 | 10 | 0.67 |
| Bb | ng/mL | 3.1E0 | 3.7E0 | 6.6E0 | 5.1E0 | 1.4E1 | 5.6E0 | 4.1E-3 | 3.5E-1 | 2.5E2 | 1.9E1 | 534 | 10 | 204 | 10 | 0.48 |
| Bc | ng/mL | 3.9E1 | 9.8E1 | 1.1E2 | 2.0E2 | 2.0E2 | 3.0E2 | 1.1E-1 | 2.9E0 | 1.2E3 | 9.9E2 | 534 | 10 | 204 | 10 | 0.64 |
| Bg | ng/mL | 8.5E-2 | 6.7E-1 | 5.4E0 | 1.4E0 | 2.9E1 | 1.6E0 | 5.3E-4 | 2.2E-2 | 4.4E2 | 4.1E0 | 534 | 10 | 204 | 10 | 0.63 |
| Bn | ng/mL | 5.6E-2 | 5.6E-2 | 1.2E0 | 1.4E-1 | 2.0E0 | 1.6E-1 | 5.6E-2 | 5.6E-2 | 9.7E0 | 5.2E-1 | 534 | 10 | 204 | 10 | 0.36 |
| Bo | ng/mL | 1.2E1 | 1.9E1 | 1.4E1 | 2.2E1 | 1.8E1 | 9.2E0 | 1.6E-2 | 1.0E1 | 2.8E2 | 3.6E1 | 534 | 10 | 204 | 10 | 0.73 |
| Ch | uIU/mL | 1.0E0 | 1.3E0 | 1.6E1 | 1.4E1 | 9.4E1 | 3.3E1 | 3.4E-3 | 1.7E-1 | 1.8E3 | 1.1E2 | 534 | 10 | 204 | 10 | 0.55 |
| Co | pg/mL | 3.8E1 | 6.6E1 | 1.7E2 | 2.7E2 | 8.9E2 | 6.3E2 | 1.5E-1 | 8.8E0 | 1.7E4 | 2.1E3 | 534 | 10 | 204 | 10 | 0.57 |
| Cp | ng/mL | 2.2E1 | 2.2E1 | 2.9E1 | 3.4E1 | 3.1E1 | 2.3E1 | 6.0E-1 | 1.1E1 | 3.7E2 | 7.2E1 | 534 | 10 | 204 | 10 | 0.58 |
| Cq | ng/mL | 3.0E-2 | 4.2E-2 | 1.4E-1 | 4.9E-2 | 8.1E-1 | 4.2E-2 | 8.0E-4 | 8.0E-4 | 1.7E1 | 1.3E-1 | 534 | 10 | 204 | 10 | 0.55 |
| Cs | ng/mL | 6.1E1 | 1.8E2 | 3.1E2 | 1.2E3 | 1.1E3 | 2.1E3 | 2.7E-2 | 5.7E0 | 1.8E4 | 5.3E3 | 534 | 10 | 204 | 10 | 0.62 |
| Ct | ng/mL | 5.9E-1 | 5.8E0 | 3.8E1 | 1.6E1 | 1.1E2 | 2.5E1 | 1.1E-4 | 3.8E-2 | 6.2E2 | 7.2E1 | 534 | 10 | 204 | 10 | 0.55 |
| Cu | ng/mL | 2.5E-1 | 7.3E-1 | 5.1E-1 | 8.4E-1 | 1.4E0 | 8.5E-1 | 9.0E-5 | 1.7E-2 | 2.1E1 | 2.9E0 | 534 | 10 | 204 | 10 | 0.66 |
| Cv | ng/mL | 5.5E0 | 3.8E0 | 2.5E1 | 7.6E0 | 6.3E1 | 1.1E1 | 1.4E-4 | 1.0E-1 | 5.3E2 | 3.5E1 | 534 | 10 | 204 | 10 | 0.42 |
| Cw | mIU/mL | 3.0E-2 | 4.1E-2 | 3.9E-2 | 5.0E-2 | 3.3E-2 | 3.3E-2 | 1.5E-4 | 1.1E-2 | 2.4E-1 | 1.2E-1 | 534 | 10 | 204 | 10 | 0.62 |
| Cx | ng/mL | 3.2E-1 | 1.4E-2 | 6.1E1 | 1.1E-1 | 1.1E2 | 2.1E-1 | 9.3E-5 | 9.3E-5 | 3.9E2 | 6.2E-1 | 534 | 10 | 204 | 10 | 0.32 |
| Db | ug/mL | 7.4E0 | 7.8E0 | 9.1E0 | 1.0E1 | 1.0E1 | 5.6E0 | 4.5E-1 | 4.3E0 | 1.4E2 | 2.3E1 | 534 | 10 | 204 | 10 | 0.58 |
| Dc | nmol/L | 1.9E-2 | 2.3E-2 | 6.0E-2 | 4.1E-2 | 1.4E-1 | 5.7E-2 | 5.2E-6 | 1.6E-3 | 1.6E0 | 2.0E-1 | 534 | 10 | 204 | 10 | 0.51 |
| Dd | ug/mL | 7.0E-2 | 4.4E-2 | 1.7E-1 | 1.5E-1 | 2.6E-1 | 2.1E-1 | 8.3E-5 | 6.4E-3 | 1.9E0 | 6.9E-1 | 534 | 10 | 204 | 10 | 0.49 |
| De | ng/mL | 3.4E-3 | 3.4E-3 | 8.1E-2 | 1.2E-1 | 1.5E-1 | 3.5E-1 | 3.4E-3 | 3.4E-3 | 1.2E0 | 1.1E0 | 534 | 10 | 204 | 10 | 0.40 |
| Dg | ng/mL | 3.3E1 | 4.0E1 | 4.5E1 | 4.0E1 | 4.0E1 | 3.6E1 | 1.0E-1 | 1.9E0 | 1.9E2 | 1.2E2 | 534 | 10 | 204 | 10 | 0.47 |
| Di | pg/mL | 1.9E0 | 3.0E0 | 2.2E0 | 2.8E0 | 2.0E0 | 1.5E0 | 1.8E-1 | 1.8E-1 | 1.3E1 | 5.4E0 | 534 | 10 | 204 | 10 | 0.63 |
| Dk | uIU/mL | 1.7E-2 | 2.5E-2 | 7.9E-2 | 1.3E-1 | 4.7E-1 | 3.0E-1 | 1.1E-4 | 5.8E-3 | 8.9E0 | 9.8E-1 | 534 | 10 | 204 | 10 | 0.58 |
| Dl | ng/mL | 2.3E2 | 3.3E2 | 3.1E2 | 3.5E2 | 2.9E2 | 3.3E2 | 1.7E0 | 4.4E0 | 1.5E3 | 8.3E2 | 534 | 10 | 204 | 10 | 0.51 |
| Dp | ng/ml | 2.4E0 | 1.8E0 | 5.4E0 | 1.8E0 | 8.0E0 | 1.5E0 | 3.7E-3 | 4.9E-2 | 5.6E1 | 4.0E0 | 332 | 7 | 193 | 7 | 0.36 |
| Ef | ng/ml | 1.3E-1 | 5.6E-1 | 8.8E-1 | 1.8E0 | 1.9E0 | 3.6E0 | 5.7E-4 | 1.3E-3 | 1.0E1 | 9.9E0 | 398 | 7 | 200 | 7 | 0.49 |
| Wm | % | 4.9E-1 | 3.4E0 | 3.3E1 | 9.4E1 | 1.8E2 | 2.7E2 | 5.4E-2 | 8.5E-2 | 2.4E3 | 8.6E2 | 432 | 10 | 217 | 10 | 0.70 |
| Ed | pg/ml | 5.2E-1 | 5.2E-1 | 5.5E1 | 2.9E1 | 4.0E2 | 4.0E1 | 5.2E-1 | 5.2E-1 | 7.3E3 | 1.0E2 | 332 | 7 | 192 | 7 | 0.51 |
| Tj | pg/mL | 3.7E-1 | 3.7E-1 | 4.9E1 | 8.4E0 | 2.7E2 | 1.4E1 | 3.6E-1 | 3.7E-1 | 3.5E3 | 3.2E1 | 396 | 7 | 203 | 7 | 0.51 |
| Po | pg/ml | 6.9E-1 | 1.2E1 | 8.0E0 | 3.4E1 | 2.2E1 | 6.0E1 | 8.0E-3 | 2.6E-2 | 2.7E2 | 2.2E2 | 932 | 13 | 343 | 13 | 0.63 |
| Et | ng/ml | 1.4E3 | 2.7E3 | 1.7E3 | 2.5E3 | 1.2E3 | 1.6E3 | 7.5E1 | 4.0E2 | 5.0E3 | 5.0E3 | 931 | 13 | 343 | 13 | 0.64 |
| Fa | ng/ml | 4.4E1 | 5.9E1 | 1.2E2 | 8.5E1 | 5.1E2 | 7.0E1 | 3.4E-2 | 1.6E0 | 8.0E3 | 2.2E2 | 327 | 7 | 190 | 7 | 0.61 |
| Ez | ng/ml | 3.8E0 | 6.6E0 | 1.7E1 | 4.1E1 | 5.0E1 | 7.4E1 | 1.3E-2 | 1.3E-2 | 7.1E2 | 2.0E2 | 332 | 7 | 193 | 7 | 0.53 |
| Fb | ng/ml | 2.5E1 | 2.9E1 | 2.3E1 | 2.7E1 | 1.2E1 | 1.3E1 | 5.9E-1 | 4.6E0 | 5.7E1 | 4.0E1 | 328 | 7 | 190 | 7 | 0.62 |
| Ex | ng/ml | 7.6E-2 | 1.2E-1 | 2.2E-1 | 3.2E-1 | 6.5E-1 | 3.3E-1 | 3.5E-5 | 6.2E-2 | 8.9E0 | 9.2E-1 | 293 | 7 | 138 | 7 | 0.70 |
| Fn | ng/ml | 2.1E-1 | 1.8E0 | 5.5E0 | 2.8E0 | 2.4E1 | 3.0E0 | 1.1E-14 | 2.1E-1 | 4.2E2 | 8.7E0 | 332 | 7 | 193 | 7 | 0.58 |
| Fp | ng/ml | 1.3E1 | 4.5E1 | 2.5E1 | 4.9E1 | 2.8E1 | 4.2E1 | 6.0E-3 | 2.3E0 | 1.4E2 | 1.4E2 | 965 | 13 | 344 | 13 | 0.68 |
| Fr | ng/ml | 3.9E4 | 3.7E5 | 1.1E5 | 3.9E5 | 1.7E5 | 3.5E5 | 1.9E2 | 7.0E3 | 9.0E5 | 8.9E5 | 1079 | 15 | 348 | 15 | 0.75 |
| Fw | pg/ml | 1.1E0 | 1.1E0 | 5.6E1 | 1.3E1 | 4.4E2 | 1.8E1 | 1.1E-14 | 1.7E-14 | 6.9E3 | 4.2E1 | 398 | 7 | 201 | 7 | 0.53 |
| Gl | pg/ml | 7.2E3 | 1.1E4 | 1.1E4 | 1.4E4 | 9.3E3 | 1.1E4 | 9.1E1 | 1.0E3 | 3.4E4 | 3.0E4 | 388 | 7 | 199 | 7 | 0.60 |
| Gp | U/ml | 1.5E0 | 1.8E0 | 3.9E0 | 1.7E0 | 6.6E0 | 2.0E0 | 1.3E-3 | 1.5E-2 | 6.7E1 | 5.4E0 | 400 | 7 | 201 | 7 | 0.41 |
| Gz | ug/ml | 1.2E0 | 8.4E-1 | 7.8E0 | 5.4E0 | 3.4E1 | 7.9E0 | 2.9E-16 | 3.1E-1 | 4.8E2 | 2.1E1 | 224 | 7 | 126 | 7 | 0.48 |

Figure 15

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ha | ng/ml | 2.7E0 | 1.3E0 | 9.4E0 | 2.7E0 | 2.0E1 | 3.3E0 | 6.4E-3 | 1.7E-2 | 1.3E2 | 9.7E0 | 330 | 7 | 192 | 7 | 0.38 |
| Nm | pg/ml | 1.4E4 | 1.7E4 | 3.3E4 | 6.5E4 | 7.8E4 | 1.2E5 | 1.0E-9 | 1.0E-9 | 1.6E6 | 4.4E5 | 935 | 13 | 345 | 13 | 0.53 |
| Nn | pg/ml | 1.6E2 | 2.0E3 | 1.7E3 | 1.4E4 | 7.6E3 | 2.3E4 | 1.0E-9 | 1.0E-9 | 1.0E5 | 6.9E4 | 935 | 13 | 345 | 13 | 0.70 |
| No | pg/ml | 1.6E1 | 1.9E1 | 3.6E1 | 2.1E2 | 1.1E2 | 4.5E2 | 1.0E-9 | 1.6E0 | 2.5E3 | 1.4E3 | 935 | 13 | 345 | 13 | 0.58 |
| Nq | pg/ml | 2.0E0 | 5.4E0 | 1.8E1 | 6.5E1 | 7.2E1 | 1.0E2 | 1.0E-9 | 1.0E-9 | 1.2E3 | 3.0E2 | 935 | 13 | 345 | 13 | 0.63 |
| Nr | pg/ml | 9.9E-1 | 2.4E0 | 2.8E1 | 6.8E2 | 1.7E2 | 2.4E3 | 1.0E-9 | 1.0E-9 | 4.1E3 | 8.5E3 | 935 | 13 | 345 | 13 | 0.58 |
| Ns | pg/ml | 1.0E-9 | 1.0E-9 | 9.0E0 | 1.5E0 | 5.1E1 | 4.6E0 | 1.0E-9 | 1.0E-9 | 1.1E3 | 1.6E1 | 935 | 13 | 345 | 13 | 0.52 |
| Nt | pg/ml | 1.0E2 | 1.3E2 | 1.3E2 | 2.0E2 | 1.1E2 | 1.8E2 | 1.0E-9 | 6.6E1 | 1.5E3 | 6.8E2 | 935 | 13 | 345 | 13 | 0.65 |
| Nu | pg/ml | 2.0E1 | 1.2E2 | 5.4E1 | 1.3E2 | 8.9E1 | 1.5E2 | 1.0E-9 | 1.0E-9 | 8.9E2 | 5.8E2 | 935 | 13 | 345 | 13 | 0.76 |
| Lu | pg/ml | 1.0E4 | 5.7E3 | 1.8E4 | 1.1E4 | 6.1E4 | 1.6E4 | 3.5E2 | 1.0E3 | 1.3E6 | 6.1E4 | 938 | 13 | 345 | 13 | 0.35 |
| Lv | pg/ml | 1.0E-9 | 4.3E1 | 1.1E1 | 6.1E1 | 2.2E1 | 4.9E1 | 1.0E-9 | 1.0E-9 | 2.6E2 | 1.9E2 | 938 | 13 | 345 | 13 | 0.88 |
| Lw | pg/ml | 1.0E-9 | 1.0E-9 | 3.9E-1 | 3.0E0 | 4.0E0 | 7.2E0 | 1.0E-9 | 1.0E-9 | 8.0E1 | 2.1E1 | 938 | 13 | 345 | 13 | 0.60 |
| Lx | pg/ml | 1.0E-9 | 2.5E2 | 1.4E2 | 1.4E3 | 4.1E2 | 2.8E3 | 1.0E-9 | 1.0E-9 | 6.2E3 | 1.0E4 | 938 | 13 | 345 | 13 | 0.78 |
| Ly | pg/ml | 1.0E-9 | 1.1E1 | 1.0E1 | 1.0E1 | 2.0E1 | 1.0E1 | 1.0E-9 | 1.0E-9 | 1.6E2 | 2.6E1 | 938 | 13 | 345 | 13 | 0.60 |
| Lz | pg/ml | 1.0E-9 | 1.0E-9 | 3.8E0 | 1.6E1 | 3.0E1 | 5.8E1 | 1.0E-9 | 1.0E-9 | 6.0E2 | 2.1E2 | 938 | 13 | 345 | 13 | 0.50 |
| Ma | pg/ml | 2.8E2 | 2.1E3 | 1.3E3 | 5.0E3 | 3.5E3 | 9.7E3 | 1.0E-9 | 2.4E1 | 6.5E4 | 3.6E4 | 938 | 13 | 345 | 13 | 0.66 |
| Mb | pg/ml | 2.5E1 | 3.4E1 | 3.1E1 | 4.1E1 | 1.5E1 | 2.1E1 | 5.4E0 | 1.9E1 | 2.1E2 | 8.7E1 | 938 | 13 | 345 | 13 | 0.65 |
| Mc | pg/ml | 1.0E-9 | 1.0E-9 | 4.1E-2 | 1.0E-9 | 5.6E-1 | 0.0E0 | 1.0E-9 | 1.0E-9 | 1.3E1 | 1.0E-9 | 938 | 13 | 345 | 13 | 0.49 |
| Md | pg/ml | 1.0E-9 | 1.0E-9 | 3.9E-1 | 1.0E-9 | 3.4E0 | 0.0E0 | 1.0E-9 | 1.0E-9 | 6.8E1 | 1.0E-9 | 938 | 13 | 345 | 13 | 0.47 |
| Me | pg/ml | 3.3E1 | 2.5E1 | 3.2E1 | 2.5E1 | 2.0E1 | 1.9E1 | 1.0E-9 | 3.2E0 | 3.2E2 | 7.9E1 | 938 | 13 | 345 | 13 | 0.31 |
| Mf | pg/ml | 1.0E-9 | 1.0E-9 | 5.2E-1 | 2.6E-1 | 2.9E0 | 6.1E-1 | 1.0E-9 | 1.0E-9 | 5.6E1 | 2.2E0 | 938 | 13 | 345 | 13 | 0.57 |
| Mg | pg/ml | 1.6E0 | 3.6E0 | 7.4E0 | 1.9E1 | 1.3E1 | 4.0E1 | 1.0E-9 | 1.0E-9 | 9.4E1 | 1.5E2 | 938 | 13 | 345 | 13 | 0.58 |
| Mh | pg/ml | 1.0E-9 | 1.0E-9 | 1.3E0 | 3.8E0 | 9.4E0 | 1.1E1 | 1.0E-9 | 1.0E-9 | 1.6E2 | 3.8E1 | 938 | 13 | 345 | 13 | 0.56 |
| Mi | pg/ml | 1.0E-9 | 1.0E-9 | 4.8E-1 | 2.6E1 | 5.2E0 | 4.6E1 | 1.0E-9 | 1.0E-9 | 1.2E2 | 1.6E2 | 938 | 13 | 345 | 13 | 0.72 |
| Mj | pg/ml | 1.0E-9 | 1.0E-9 | 4.3E0 | 4.5E1 | 2.4E1 | 1.5E2 | 1.0E-9 | 1.0E-9 | 4.6E2 | 5.4E2 | 938 | 13 | 345 | 13 | 0.56 |
| Mk | pg/ml | 9.1E-1 | 9.3E0 | 1.4E1 | 4.4E2 | 8.4E1 | 1.5E3 | 1.0E-9 | 1.0E-9 | 1.7E3 | 5.6E3 | 938 | 13 | 345 | 13 | 0.62 |
| Ml | pg/ml | 1.0E-9 | 1.0E-9 | 4.9E0 | 2.5E0 | 7.2E1 | 5.0E0 | 1.0E-9 | 1.0E-9 | 2.1E3 | 1.6E1 | 938 | 13 | 345 | 13 | 0.57 |
| Mm | pg/ml | 5.9E2 | 4.8E2 | 1.0E3 | 2.0E3 | 1.2E3 | 2.5E3 | 1.0E-9 | 1.0E-9 | 1.1E4 | 6.9E3 | 938 | 13 | 345 | 13 | 0.55 |
| Mn | pg/ml | 5.5E0 | 9.3E0 | 1.0E1 | 1.4E1 | 2.2E1 | 1.7E1 | 1.0E-9 | 6.9E-1 | 3.5E2 | 6.6E1 | 938 | 13 | 345 | 13 | 0.63 |
| Mp | pg/ml | 1.0E-9 | 7.1E0 | 8.9E0 | 6.2E1 | 2.9E1 | 9.1E1 | 1.0E-9 | 1.0E-9 | 6.3E2 | 2.7E2 | 937 | 13 | 345 | 13 | 0.64 |
| Mq | pg/ml | 1.0E-9 | 1.0E-9 | 2.7E0 | 1.4E1 | 1.6E1 | 4.0E1 | 1.0E-9 | 1.0E-9 | 2.4E2 | 1.4E2 | 937 | 13 | 345 | 13 | 0.55 |
| Mr | pg/ml | 1.0E-9 | 1.0E-9 | 2.5E1 | 9.1E2 | 1.4E2 | 3.3E3 | 1.0E-9 | 1.0E-9 | 2.2E3 | 1.2E4 | 937 | 13 | 345 | 13 | 0.57 |
| Ms | pg/ml | 4.1E2 | 2.6E2 | 5.6E2 | 3.3E2 | 6.6E2 | 3.4E2 | 1.0E-9 | 1.0E-9 | 5.9E3 | 8.6E2 | 937 | 13 | 345 | 13 | 0.39 |
| Mt | pg/ml | 2.5E-1 | 9.0E0 | 6.8E0 | 2.1E1 | 4.1E1 | 2.8E1 | 1.0E-9 | 1.0E-9 | 8.7E2 | 7.8E1 | 937 | 13 | 345 | 13 | 0.76 |
| Mu | pg/ml | 1.0E-9 | 8.4E-1 | 1.2E0 | 9.2E0 | 1.0E1 | 1.5E1 | 1.0E-9 | 1.0E-9 | 2.3E2 | 4.8E1 | 937 | 13 | 345 | 13 | 0.72 |
| Mv | pg/ml | 1.0E-9 | 5.9E1 | 6.8E1 | 1.9E2 | 3.1E2 | 2.9E2 | 1.0E-9 | 1.0E-9 | 4.5E3 | 9.0E2 | 937 | 13 | 345 | 13 | 0.71 |
| Mw | pg/ml | 3.8E1 | 6.6E2 | 5.0E2 | 1.4E3 | 3.2E3 | 2.3E3 | 1.0E-9 | 1.0E-9 | 6.2E4 | 8.5E3 | 937 | 13 | 345 | 13 | 0.68 |
| Mx | pg/ml | 1.0E-9 | 1.0E-9 | 2.4E-1 | 3.6E-1 | 1.3E0 | 8.6E-1 | 1.0E-9 | 1.0E-9 | 3.2E1 | 3.0E0 | 937 | 13 | 345 | 13 | 0.62 |
| My | pg/ml | 1.0E-9 | 2.1E2 | 4.5E2 | 5.3E2 | 2.9E3 | 9.3E2 | 1.0E-9 | 1.0E-9 | 3.9E4 | 3.4E3 | 937 | 13 | 345 | 13 | 0.75 |
| Mz | pg/ml | 1.1E1 | 2.2E1 | 2.7E1 | 5.3E1 | 6.3E1 | 6.3E1 | 1.0E-9 | 5.1E0 | 1.2E3 | 2.0E2 | 937 | 13 | 345 | 13 | 0.68 |
| Na | pg/ml | 1.0E-9 | 1.0E-9 | 6.6E-1 | 8.8E-1 | 2.6E0 | 3.0E0 | 1.0E-9 | 1.0E-9 | 3.6E1 | 1.1E1 | 937 | 13 | 345 | 13 | 0.48 |
| Nb | pg/ml | 2.1E0 | 4.6E0 | 3.8E0 | 2.4E1 | 1.1E1 | 6.5E1 | 1.0E-9 | 1.0E-9 | 2.3E2 | 2.4E2 | 937 | 13 | 345 | 13 | 0.68 |
| Nc | pg/ml | 3.4E2 | 1.7E2 | 5.6E2 | 2.3E2 | 7.2E2 | 2.3E2 | 1.0E-9 | 1.0E-9 | 9.2E3 | 6.7E2 | 937 | 13 | 345 | 13 | 0.40 |
| Nd | pg/ml | 2.9E1 | 1.0E1 | 2.7E1 | 4.6E1 | 4.4E1 | 5.8E1 | 1.0E-9 | 1.0E-9 | 1.2E3 | 1.5E2 | 937 | 13 | 345 | 13 | 0.51 |
| Ne | pg/ml | 4.4E2 | 2.7E2 | 5.7E2 | 5.0E2 | 5.7E2 | 9.6E2 | 1.0E-9 | 1.3E1 | 7.0E3 | 3.6E3 | 937 | 13 | 345 | 13 | 0.37 |
| Nf | pg/ml | 1.0E-9 | 1.0E-9 | 2.6E0 | 7.9E0 | 9.4E0 | 2.3E1 | 1.0E-9 | 1.0E-9 | 1.6E2 | 8.2E1 | 937 | 13 | 345 | 13 | 0.51 |
| Ng | pg/ml | 1.9E1 | 4.4E0 | 1.3E2 | 1.1E2 | 2.5E2 | 1.5E2 | 1.0E-9 | 1.0E-9 | 2.3E3 | 4.7E2 | 937 | 13 | 345 | 13 | 0.47 |
| Nh | pg/ml | 6.9E1 | 3.2E1 | 9.0E1 | 8.0E1 | 8.2E1 | 1.3E2 | 1.0E-9 | 2.2E0 | 5.6E2 | 5.1E2 | 937 | 13 | 345 | 13 | 0.35 |
| Ni | pg/ml | 1.0E-9 | 4.4E1 | 7.2E1 | 1.3E2 | 1.2E2 | 1.5E2 | 1.0E-9 | 1.0E-9 | 7.1E2 | 3.9E2 | 937 | 13 | 345 | 13 | 0.63 |
| Nj | pg/ml | 7.5E0 | 4.8E0 | 1.1E1 | 5.9E0 | 1.2E1 | 5.5E0 | 1.0E-9 | 1.0E-9 | 1.1E2 | 2.0E1 | 937 | 13 | 345 | 13 | 0.38 |
| Nk | pg/ml | 1.7E1 | 2.0E1 | 3.3E1 | 1.9E1 | 3.9E1 | 1.1E1 | 1.0E-9 | 1.0E-9 | 2.0E2 | 3.7E1 | 937 | 13 | 345 | 13 | 0.48 |
| Nl | pg/ml | 4.5E1 | 2.2E1 | 6.1E1 | 4.3E1 | 6.8E1 | 5.0E1 | 1.0E-9 | 1.0E-9 | 1.1E3 | 1.8E2 | 937 | 13 | 345 | 13 | 0.41 |
| Tz | pg/ml | 5.1E3 | 6.2E3 | 2.0E4 | 5.8E3 | 1.3E5 | 4.7E3 | 1.0E-9 | 6.3E2 | 2.1E6 | 1.1E4 | 334 | 7 | 191 | 7 | 0.46 |
| Ua | pg/ml | 3.8E3 | 4.7E3 | 2.0E4 | 2.1E4 | 1.2E5 | 3.6E4 | 1.0E-9 | 2.0E3 | 2.1E6 | 9.9E4 | 334 | 7 | 191 | 7 | 0.57 |
| Ub | pg/ml | 5.6E2 | 2.4E2 | 8.3E2 | 3.4E2 | 1.0E3 | 2.3E2 | 1.0E-9 | 1.4E2 | 9.8E3 | 7.8E2 | 334 | 7 | 191 | 7 | 0.33 |
| Uc | pg/ml | 2.7E1 | 1.5E1 | 3.8E1 | 2.6E1 | 4.1E1 | 3.8E1 | 9.8E-2 | 4.5E0 | 4.4E2 | 1.1E2 | 334 | 7 | 191 | 7 | 0.27 |
| Uc | pg/ml | 8.9E2 | 5.0E2 | 1.7E3 | 1.2E3 | 2.6E3 | 1.9E3 | 1.0E-9 | 4.1E1 | 2.9E4 | 5.4E3 | 334 | 7 | 191 | 7 | 0.36 |

Figure 15 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ud | pg/ml | 1.0E-9 | 1.0E-9 | 1.3E0 | 1.0E-9 | 2.1E1 | 0.0E0 | 1.0E-9 | 1.0E-9 | 3.9E2 | 1.0E-9 | 334 | 7 | 191 | 7 | 0.50 |
| Hq | pg/ml | 1.1E0 | 2.4E0 | 9.6E1 | 2.6E1 | 1.6E3 | 8.2E1 | 1.0E-9 | 1.0E-9 | 3.4E4 | 3.0E2 | 933 | 13 | 344 | 13 | 0.61 |
| Hr | pg/ml | 1.1E2 | 8.2E1 | 7.5E2 | 9.6E2 | 1.6E3 | 2.9E3 | 1.0E-9 | 2.7E1 | 1.7E4 | 1.1E4 | 933 | 13 | 344 | 13 | 0.43 |
| Hu | pg/ml | 5.3E0 | 3.2E2 | 3.0E3 | 1.2E3 | 2.6E4 | 1.8E3 | 1.0E-9 | 1.0E-9 | 6.3E5 | 5.9E3 | 933 | 13 | 344 | 13 | 0.73 |
| Hv | pg/ml | 1.4E0 | 3.4E0 | 3.3E0 | 8.2E0 | 1.2E1 | 1.6E1 | 1.0E-9 | 9.7E-1 | 2.5E2 | 5.9E1 | 933 | 13 | 344 | 13 | 0.74 |
| Hw | pg/ml | 6.4E0 | 3.2E0 | 1.8E1 | 2.8E2 | 6.9E1 | 9.5E2 | 1.0E-9 | 1.0E-9 | 1.7E3 | 3.4E3 | 933 | 13 | 344 | 13 | 0.42 |
| Hx | pg/ml | 8.8E0 | 2.2E1 | 3.7E1 | 1.8E2 | 3.1E2 | 5.4E2 | 1.0E-9 | 2.9E0 | 9.3E3 | 2.0E3 | 933 | 13 | 344 | 13 | 0.71 |
| Ib | ng/ml | 4.9E-2 | 2.0E-2 | 1.7E0 | 9.2E-1 | 6.5E0 | 2.3E0 | 1.0E-9 | 1.0E-9 | 5.3E1 | 6.1E0 | 324 | 7 | 190 | 7 | 0.45 |
| Ic | U/ml | 2.2E2 | 2.2E2 | 1.0E3 | 2.6E2 | 6.6E3 | 1.6E2 | 1.5E0 | 2.4E1 | 9.3E4 | 5.4E2 | 324 | 7 | 190 | 7 | 0.60 |
| Id | U/ml | 6.9E-1 | 9.5E-1 | 1.4E0 | 1.1E0 | 2.4E0 | 1.0E0 | 1.0E-9 | 2.4E-1 | 2.3E1 | 3.2E0 | 324 | 7 | 190 | 7 | 0.51 |
| Tt | pg/ml | 1.6E2 | 1.8E2 | 1.7E2 | 1.7E2 | 5.1E1 | 4.2E1 | 4.3E1 | 1.2E2 | 3.6E2 | 2.3E2 | 308 | 7 | 184 | 7 | 0.50 |
| To | pg/ml | 1.6E0 | 2.7E0 | 1.9E0 | 2.6E0 | 2.3E0 | 8.6E-1 | 1.0E-9 | 1.8E0 | 2.3E1 | 4.1E0 | 321 | 7 | 188 | 7 | 0.71 |
| Tr | pg/ml | 3.0E0 | 3.1E0 | 5.9E0 | 3.9E0 | 1.8E1 | 3.6E0 | 1.0E-9 | 1.4E0 | 3.1E2 | 1.2E1 | 317 | 7 | 187 | 7 | 0.50 |
| Tn | pg/ml | 2.8E1 | 3.7E1 | 7.4E1 | 9.0E1 | 1.9E2 | 9.7E1 | 1.0E-9 | 1.3E1 | 1.8E3 | 2.3E2 | 321 | 7 | 188 | 7 | 0.61 |
| Tv | ng/ml | 1.2E1 | 6.2E0 | 2.3E1 | 1.2E1 | 1.4E1 | 1.4E1 | 1.0E-9 | 1.0E-9 | 7.9E2 | 3.1E1 | 321 | 7 | 188 | 7 | 0.43 |
| Ih | ng/ml | 7.2E1 | 1.9E2 | 2.4E2 | 3.2E2 | 4.8E2 | 3.9E2 | 1.0E-9 | 2.4E0 | 7.4E3 | 1.2E3 | 937 | 13 | 344 | 13 | 0.63 |
| Ii | ng/ml | 9.5E1 | 7.2E1 | 2.4E2 | 8.5E2 | 6.6E2 | 2.5E3 | 1.0E-9 | 7.5E-1 | 1.0E4 | 9.2E3 | 937 | 13 | 344 | 13 | 0.47 |
| Ij | ng/ml | 7.6E1 | 1.3E2 | 1.7E2 | 7.4E2 | 5.7E2 | 1.8E3 | 1.6E-1 | 9.5E0 | 6.4E3 | 6.4E3 | 924 | 13 | 342 | 13 | 0.63 |
| Ik | ng/ml | 1.3E1 | 1.9E2 | 7.9E2 | 3.8E2 | 8.0E3 | 5.0E2 | 5.9E-1 | 6.2E-1 | 1.2E5 | 1.5E3 | 932 | 13 | 342 | 13 | 0.66 |
| Il | ng/ml | 3.3E2 | 2.0E2 | 1.3E3 | 2.3E3 | 2.8E3 | 4.6E3 | 1.0E-9 | 1.0E-9 | 1.3E4 | 1.2E4 | 916 | 12 | 342 | 12 | 0.42 |
| Im | ng/ml | 2.1E2 | 7.0E2 | 4.0E2 | 8.7E2 | 7.6E2 | 1.1E3 | 1.3E1 | 2.2E1 | 1.5E4 | 4.0E3 | 931 | 13 | 343 | 13 | 0.68 |
| In | ng/ml | 3.3E0 | 5.4E-1 | 2.1E1 | 5.3E1 | 1.5E2 | 1.6E2 | 1.0E-9 | 1.0E-9 | 3.9E3 | 5.9E2 | 937 | 13 | 344 | 13 | 0.40 |
| Hb | ng/ml | 2.5E1 | 8.9E0 | 3.6E1 | 1.5E1 | 3.5E1 | 1.2E1 | 4.8E-1 | 1.5E0 | 2.1E2 | 3.2E1 | 333 | 7 | 191 | 7 | 0.30 |
| Hc | pg/ml | 6.6E2 | 1.7E3 | 3.4E3 | 3.5E3 | 1.2E4 | 4.1E3 | 1.0E-9 | 3.4E2 | 1.0E5 | 1.1E4 | 333 | 7 | 191 | 7 | 0.64 |
| Hf | ng/ml | 1.6E2 | 1.6E2 | 3.7E2 | 2.8E2 | 5.1E2 | 3.8E2 | 1.0E-9 | 1.0E-9 | 3.2E3 | 1.0E3 | 333 | 7 | 191 | 7 | 0.46 |
| Io | ng/ml | 8.3E3 | 8.0E3 | 2.5E4 | 5.0E4 | 1.4E5 | 1.5E5 | 1.0E-9 | 9.1E2 | 4.0E6 | 5.5E5 | 928 | 13 | 344 | 13 | 0.47 |
| Ip | ng/ml | 1.0E1 | 3.0E1 | 2.0E1 | 3.9E1 | 2.4E1 | 4.3E1 | 1.0E-9 | 1.1E-2 | 2.6E2 | 1.4E2 | 928 | 13 | 344 | 13 | 0.63 |
| Iq | ug/ml | 1.0E-1 | 2.5E-1 | 3.0E1 | 5.9E1 | 6.3E2 | 2.1E2 | 1.0E-9 | 1.0E-9 | 1.4E4 | 7.5E2 | 928 | 13 | 344 | 13 | 0.49 |
| Ir | ug/ml | 3.5E-1 | 1.3E0 | 3.4E0 | 1.1E1 | 2.4E1 | 3.1E1 | 1.0E-9 | 3.5E-2 | 5.1E2 | 1.1E2 | 927 | 13 | 344 | 13 | 0.69 |
| Is | ng/ml | 1.6E0 | 4.3E1 | 6.4E0 | 2.7E1 | 2.2E1 | 6.2E1 | 1.0E-9 | 4.3E-1 | 5.5E2 | 2.3E2 | 928 | 13 | 344 | 13 | 0.70 |
| It | ng/ml | 2.0E0 | 1.6E0 | 2.3E1 | 5.7E1 | 1.4E2 | 1.6E2 | 1.0E-9 | 1.0E-9 | 2.8E3 | 5.9E2 | 928 | 13 | 344 | 13 | 0.52 |
| Iu | ng/ml | 2.2E2 | 2.6E2 | 1.3E3 | 3.1E3 | 4.0E3 | 7.0E3 | 1.0E-9 | 1.0E-9 | 2.9E4 | 2.4E4 | 928 | 13 | 344 | 13 | 0.53 |
| Iv | ng/ml | 1.3E1 | 3.0E1 | 6.0E1 | 5.4E2 | 5.4E2 | 1.8E3 | 1.0E-9 | 4.1E-1 | 1.6E4 | 6.4E3 | 927 | 13 | 344 | 13 | 0.66 |
| Iz | ng/ml | 1.4E2 | 2.8E2 | 5.9E2 | 4.1E2 | 3.5E3 | 4.7E2 | 9.2E-1 | 8.8E-1 | 6.2E4 | 1.1E3 | 333 | 7 | 191 | 7 | 0.48 |
| Rc | pg/ml | 5.6E2 | 6.8E3 | 7.1E3 | 6.2E3 | 5.7E3 | 5.3E3 | 1.9E2 | 9.6E2 | 3.9E4 | 1.6E4 | 331 | 7 | 191 | 7 | 0.45 |
| Rb | pg/ml | 8.2E-1 | 1.1E0 | 2.6E0 | 1.7E0 | 4.2E0 | 1.9E0 | 1.0E-9 | 1.0E-9 | 4.3E1 | 5.4E0 | 331 | 7 | 191 | 7 | 0.54 |
| Pz | ng/ml | 3.8E3 | 1.0E4 | 8.1E3 | 6.6E3 | 3.7E4 | 4.8E3 | 1.3E1 | 4.0E1 | 1.0E6 | 1.4E4 | 929 | 13 | 342 | 13 | 0.58 |
| Qa | ng/ml | 3.5E2 | 1.1E4 | 6.3E3 | 1.2E4 | 7.4E3 | 8.8E3 | 1.2E1 | 9.4E2 | 5.2E4 | 3.1E4 | 929 | 13 | 342 | 13 | 0.72 |
| Qb | ng/ml | 9.7E1 | 2.1E2 | 2.1E2 | 3.5E2 | 4.8E2 | 4.2E2 | 7.9E-1 | 3.2E1 | 8.3E3 | 1.6E3 | 929 | 13 | 342 | 13 | 0.65 |
| Qc | ng/ml | 2.3E2 | 4.1E2 | 6.3E2 | 4.1E2 | 5.5E3 | 3.5E2 | 1.0E-9 | 3.2E1 | 1.7E5 | 1.2E3 | 929 | 13 | 342 | 13 | 0.55 |
| Qd | ng/ml | 9.2E3 | 2.3E4 | 2.1E4 | 4.8E4 | 7.7E4 | 6.2E4 | 1.5E2 | 1.9E3 | 2.0E6 | 2.2E5 | 929 | 13 | 342 | 13 | 0.68 |
| Qe | ng/ml | 9.2E2 | 2.3E3 | 1.8E3 | 3.8E3 | 3.8E3 | 3.7E3 | 1.0E-9 | 1.2E2 | 9.7E4 | 1.4E4 | 929 | 13 | 342 | 13 | 0.73 |
| Jd | ng/ml | 9.4E-1 | 3.1E0 | 5.8E0 | 4.5E0 | 3.8E1 | 6.2E0 | 1.0E-9 | 1.0E-9 | 6.5E2 | 1.8E1 | 332 | 7 | 193 | 7 | 0.63 |
| Je | ng/ml | 1.0E-9 | 1.5E0 | 2.0E0 | 1.5E0 | 7.0E0 | 1.3E0 | 1.0E-9 | 1.0E-9 | 8.8E1 | 2.9E0 | 332 | 7 | 193 | 7 | 0.62 |
| Jf | ng/ml | 1.0E-9 | 8.7E-1 | 1.1E0 | 1.5E0 | 2.2E0 | 2.0E0 | 1.0E-9 | 1.0E-9 | 1.2E1 | 5.6E0 | 332 | 7 | 193 | 7 | 0.65 |
| Jg | ng/ml | 4.9E2 | 1.3E3 | 8.2E2 | 2.0E3 | 1.0E3 | 1.9E3 | 1.0E-9 | 8.4E1 | 1.0E4 | 5.4E3 | 933 | 13 | 344 | 13 | 0.68 |
| Jh | ng/ml | 3.0E0 | 2.9E1 | 2.7E1 | 7.8E1 | 1.1E2 | 9.6E1 | 1.0E-9 | 1.0E-9 | 1.6E3 | 2.9E2 | 933 | 13 | 344 | 13 | 0.73 |
| Ji | ng/ml | 5.3E1 | 6.9E1 | 7.7E1 | 2.8E2 | 8.0E1 | 4.9E2 | 1.0E-9 | 2.3E1 | 6.9E2 | 1.8E3 | 933 | 13 | 344 | 13 | 0.69 |
| Sr | pg/mL | 3.8E2 | 6.7E2 | 8.5E2 | 1.3E3 | 1.3E3 | 1.5E3 | 1.0E-9 | 7.9E1 | 9.8E3 | 4.1E3 | 322 | 7 | 188 | 7 | 0.60 |
| Ss | pg/mL | 9.5E4 | 2.0E5 | 1.5E5 | 1.2E5 | 1.8E5 | 5.5E4 | 2.7E3 | 7.8E3 | 1.8E6 | 2.0E5 | 322 | 7 | 188 | 7 | 0.45 |
| St | pg/mL | 2.6E7 | 5.3E7 | 5.6E7 | 1.1E8 | 9.4E7 | 1.3E8 | 1.0E-9 | 4.4E6 | 1.2E9 | 3.0E8 | 326 | 7 | 189 | 7 | 0.55 |
| Ra | pg/ml | 1.0E-9 | 1.0E-9 | 6.1E-1 | 1.6E-1 | 1.2E0 | 2.7E-1 | 1.0E-9 | 1.0E-9 | 7.3E0 | 5.6E-1 | 331 | 7 | 191 | 7 | 0.47 |
| Qz | pg/ml | 1.0E1 | 3.9E1 | 6.3E1 | 5.9E1 | 1.0E2 | 6.5E1 | 1.0E-9 | 1.0E-9 | 7.1E2 | 1.5E2 | 331 | 7 | 191 | 7 | 0.51 |
| Qy | pg/ml | 4.4E-1 | 5.3E-1 | 1.6E1 | 1.1E2 | 7.6E1 | 2.7E2 | 1.0E-9 | 1.0E-9 | 6.5E2 | 7.3E2 | 331 | 7 | 191 | 7 | 0.57 |
| Qx | pg/ml | 1.0E-9 | 1.0E-9 | 5.4E0 | 1.2E0 | 4.5E1 | 2.6E0 | 1.0E-9 | 1.0E-9 | 5.8E2 | 7.1E0 | 331 | 7 | 191 | 7 | 0.63 |
| Qw | pg/ml | 1.0E-9 | 1.0E-9 | 2.9E0 | 4.5E-1 | 1.4E1 | 1.2E0 | 1.0E-9 | 1.0E-9 | 1.3E2 | 3.2E0 | 331 | 7 | 191 | 7 | 0.37 |
| Qv | pg/ml | 2.3E4 | 4.9E3 | 3.5E4 | 6.4E3 | 5.5E4 | 5.1E3 | 1.0E-9 | 1.5E3 | 7.4E5 | 1.5E4 | 331 | 7 | 191 | 7 | 0.15 |

Figure 15 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Qu | pg/ml | 7.8E0 | 5.3E1 | 8.2E1 | 1.4E2 | 1.7E2 | 2.6E2 | 1.0E-9 | 1.0E-9 | 9.8E2 | 7.3E2 | 331 | 7 | 191 | 7 | 0.57 |
| Qt | pg/ml | 1.0E1 | 5.7E0 | 4.9E1 | 5.6E1 | 1.2E2 | 8.7E1 | 1.0E-9 | 1.0E-9 | 1.0E3 | 2.2E2 | 331 | 7 | 191 | 7 | 0.52 |
| Qh | ng/ml | 1.7E1 | 3.5E1 | 4.0E1 | 3.3E1 | 7.7E1 | 2.6E1 | 1.0E-9 | 3.3E0 | 8.0E2 | 7.0E1 | 331 | 7 | 191 | 7 | 0.57 |
| Qg | ng/ml | 8.3E0 | 8.4E0 | 2.0E1 | 8.1E0 | 6.3E1 | 2.3E0 | 5.1E-2 | 4.9E0 | 1.0E3 | 1.2E1 | 331 | 7 | 191 | 7 | 0.48 |
| Jj | ng/ml | 6.0E2 | 1.4E2 | 1.7E3 | 2.3E2 | 1.2E4 | 2.7E2 | 2.3E0 | 8.7E0 | 3.4E5 | 1.0E3 | 933 | 13 | 344 | 13 | 0.19 |
| Jk | ng/ml | 3.1E0 | 2.3E1 | 2.1E1 | 4.6E1 | 4.7E1 | 6.4E1 | 1.0E-9 | 1.0E-1 | 3.9E2 | 1.8E2 | 933 | 13 | 344 | 13 | 0.63 |
| Jl | ng/ml | 4.4E-1 | 2.5E0 | 1.9E0 | 1.7E1 | 5.6E0 | 4.3E1 | 7.6E-4 | 7.2E-2 | 1.1E2 | 1.6E2 | 933 | 13 | 344 | 13 | 0.73 |
| Jm | ng/ml | 1.8E1 | 8.8E0 | 5.8E1 | 4.4E1 | 1.3E2 | 6.7E1 | 1.0E-9 | 4.0E-1 | 2.1E3 | 2.0E2 | 933 | 13 | 344 | 13 | 0.45 |
| Jn | pg/ml | 4.0E-1 | 1.1E0 | 2.5E0 | 2.4E0 | 2.2E1 | 3.5E0 | 1.0E-9 | 1.0E-9 | 6.2E2 | 9.5E0 | 932 | 13 | 344 | 13 | 0.62 |
| Jo | pg/ml | 3.6E3 | 1.9E3 | 4.7E3 | 6.2E3 | 3.8E3 | 1.0E4 | 2.0E1 | 2.4E1 | 2.4E4 | 3.8E4 | 933 | 13 | 344 | 13 | 0.41 |
| Jp | pg/ml | 7.0E4 | 1.0E5 | 7.4E4 | 1.0E5 | 3.8E4 | 2.9E4 | 5.8E2 | 6.8E4 | 3.8E5 | 1.7E5 | 933 | 13 | 344 | 13 | 0.77 |
| Jq | pg/ml | 9.4E1 | 7.5E1 | 1.5E2 | 3.8E2 | 2.1E2 | 1.0E3 | 1.0E0 | 1.3E1 | 4.0E3 | 3.7E3 | 933 | 13 | 344 | 13 | 0.47 |
| Jr | pg/ml | 5.2E0 | 1.2E1 | 3.3E1 | 3.1E1 | 3.6E2 | 5.2E1 | 1.0E-9 | 1.0E-9 | 1.1E4 | 1.9E2 | 933 | 13 | 344 | 13 | 0.67 |
| Js | pg/ml | 1.3E1 | 1.2E1 | 4.9E1 | 2.2E1 | 3.6E2 | 2.4E1 | 1.0E-9 | 2.7E0 | 1.0E4 | 9.4E1 | 933 | 13 | 344 | 13 | 0.52 |
| Jt | pg/ml | 2.6E3 | 2.3E3 | 3.2E3 | 4.9E3 | 2.4E3 | 8.6E3 | 2.2E1 | 1.5E2 | 2.2E4 | 3.3E4 | 933 | 13 | 344 | 13 | 0.46 |
| Ju | mIU/ml | 8.7E0 | 8.1E0 | 1.9E1 | 1.1E1 | 2.9E1 | 1.1E1 | 4.8E-2 | 1.0E0 | 2.3E2 | 3.5E1 | 332 | 7 | 193 | 7 | 0.48 |
| Jv | mIU/ml | 1.2E1 | 8.7E0 | 3.3E1 | 7.7E0 | 5.7E1 | 5.3E0 | 9.4E-3 | 1.8E-1 | 4.4E2 | 1.3E1 | 332 | 7 | 193 | 7 | 0.38 |
| Jy | ng/ml | 1.6E-3 | 1.6E-3 | 2.1E-3 | 1.9E-3 | 3.8E-3 | 1.1E-3 | 1.0E-9 | 8.6E-4 | 5.2E-2 | 4.0E-3 | 332 | 7 | 193 | 7 | 0.51 |
| Kc | pg/ml | 2.6E1 | 1.3E2 | 4.6E1 | 1.4E2 | 4.9E1 | 1.0E2 | 1.0E-9 | 1.0E-9 | 2.7E2 | 3.2E2 | 333 | 7 | 191 | 7 | 0.77 |
| Kd | pg/ml | 1.0E-9 | 5.7E2 | 2.1E2 | 9.0E2 | 6.4E2 | 9.8E2 | 1.0E-9 | 1.0E-9 | 5.0E3 | 2.3E3 | 333 | 7 | 191 | 7 | 0.77 |
| Ke | pg/ml | 1.3E4 | 1.4E4 | 1.5E4 | 1.6E4 | 1.1E4 | 1.5E4 | 3.4E2 | 3.5E3 | 7.0E4 | 4.9E4 | 333 | 7 | 191 | 7 | 0.49 |
| Kf | pg/mL | 7.2E0 | 9.4E0 | 7.4E0 | 7.8E0 | 6.0E0 | 7.1E0 | 1.0E-9 | 1.0E-9 | 4.4E1 | 1.8E1 | 333 | 7 | 191 | 7 | 0.53 |
| Kg | pg/mL | 1.1E3 | 7.6E2 | 1.9E3 | 6.3E3 | 2.4E3 | 1.3E4 | 7.3E1 | 2.1E2 | 2.2E4 | 3.6E4 | 333 | 7 | 191 | 7 | 0.46 |
| Ki | pg/ml | 5.9E1 | 6.4E1 | 7.0E1 | 7.4E1 | 5.3E1 | 1.9E1 | 1.0E-9 | 5.9E1 | 3.8E2 | 1.1E2 | 332 | 7 | 191 | 7 | 0.61 |
| Kj | pg/ml | 1.0E3 | 4.6E2 | 1.6E3 | 1.5E3 | 1.6E3 | 2.8E3 | 1.4E1 | 3.9E1 | 1.0E4 | 7.7E3 | 333 | 7 | 191 | 7 | 0.34 |
| Kk | pg/ml | 6.9E0 | 3.3E1 | 1.2E1 | 3.4E1 | 1.5E1 | 2.5E1 | 1.0E-9 | 7.8E0 | 1.6E2 | 6.1E1 | 333 | 7 | 191 | 7 | 0.80 |
| Kl | pg/ml | 2.0E4 | 1.7E4 | 2.8E4 | 2.4E4 | 2.5E4 | 2.3E4 | 1.6E2 | 6.2E2 | 1.6E5 | 5.0E4 | 333 | 7 | 191 | 7 | 0.41 |
| Kn | pg/ml | 3.0E1 | 6.2E1 | 6.3E1 | 1.2E2 | 1.0E2 | 1.5E2 | 1.0E-9 | 1.0E-9 | 7.3E2 | 4.1E2 | 333 | 7 | 191 | 7 | 0.60 |
| Ko | pg/ml | 3.5E2 | 7.0E2 | 5.0E2 | 6.7E2 | 5.1E2 | 4.4E2 | 1.0E-9 | 1.5E2 | 3.8E3 | 1.5E3 | 333 | 7 | 191 | 7 | 0.66 |
| Kp | pg/ml | 3.4E2 | 5.9E2 | 3.6E2 | 4.6E2 | 2.6E2 | 3.3E2 | 1.0E-9 | 6.4E1 | 1.7E3 | 7.9E2 | 333 | 7 | 191 | 7 | 0.60 |
| Kq | pg/ml | 3.3E2 | 6.1E2 | 4.7E2 | 1.2E3 | 7.6E2 | 1.9E3 | 1.6E0 | 7.0E1 | 9.8E3 | 5.5E3 | 325 | 7 | 185 | 7 | 0.61 |
| Kr | pg/ml | 4.5E-1 | 1.0E1 | 2.4E0 | 1.2E0 | 4.6E0 | 1.5E0 | 1.0E-9 | 1.0E-9 | 3.9E1 | 3.3E0 | 325 | 7 | 185 | 7 | 0.44 |
| Ks | pg/ml | 1.4E4 | 4.9E3 | 2.0E4 | 9.6E3 | 1.8E4 | 9.3E3 | 5.1E1 | 4.2E2 | 1.1E5 | 2.4E4 | 325 | 7 | 185 | 7 | 0.33 |
| Kx | ng/ml | 1.1E-4 | 8.9E-3 | 6.7E-3 | 7.8E-3 | 1.3E-2 | 6.4E-3 | 1.0E-9 | 1.0E-9 | 1.0E-1 | 1.5E-2 | 330 | 7 | 190 | 7 | 0.63 |
| Ky | ng/ml | 9.8E-2 | 3.8E-1 | 3.9E-1 | 3.6E-1 | 8.5E-1 | 2.1E-1 | 1.0E-9 | 8.8E-2 | 6.3E0 | 6.0E-1 | 330 | 7 | 190 | 7 | 0.72 |
| Kz | ng/ml | 1.0E-9 | 1.0E-9 | 3.4E-3 | 5.0E-3 | 5.6E-3 | 9.3E-3 | 1.0E-9 | 1.0E-9 | 3.6E-2 | 2.5E-2 | 330 | 7 | 190 | 7 | 0.53 |
| Ld | pg/ml | 1.0E-9 | 7.3E0 | 3.6E0 | 8.0E0 | 8.6E0 | 1.0E1 | 1.0E-9 | 1.0E-9 | 8.4E1 | 2.9E1 | 331 | 7 | 190 | 7 | 0.68 |
| Lh | pg/ml | 1.3E4 | 3.0E4 | 2.1E4 | 6.3E4 | 2.6E4 | 1.1E5 | 1.0E-9 | 2.0E3 | 2.6E5 | 4.1E5 | 932 | 13 | 345 | 13 | 0.68 |
| Li | pg/ml | 3.5E3 | 1.6E4 | 1.7E4 | 1.0E5 | 6.2E4 | 1.8E5 | 1.0E-9 | 3.6E1 | 1.3E6 | 5.9E5 | 932 | 13 | 345 | 13 | 0.67 |
| Lj | pg/ml | 2.8E3 | 1.1E4 | 2.3E4 | 5.0E4 | 6.4E4 | 1.9E5 | 1.0E-9 | 8.9E1 | 5.2E5 | 3.5E5 | 932 | 13 | 345 | 13 | 0.65 |
| Rm | ng/ml | 1.9E1 | 3.7E1 | 5.2E1 | 4.0E1 | 8.1E1 | 4.2E1 | 2.2E-1 | 2.3E-1 | 6.5E2 | 1.0E2 | 326 | 7 | 190 | 7 | 0.47 |
| Rh | ng/ml | 1.3E2 | 5.0E2 | 3.5E2 | 6.3E2 | 1.2E3 | 8.7E2 | 3.6E0 | 2.5E1 | 1.7E4 | 2.5E3 | 326 | 7 | 190 | 7 | 0.62 |
| Ri | ng/ml | 1.0E-9 | 1.0E-9 | 4.3E0 | 2.0E0 | 1.5E1 | 2.8E0 | 1.0E-9 | 1.0E-9 | 2.2E2 | 7.1E0 | 327 | 7 | 191 | 7 | 0.48 |
| Rg | ng/ml | 1.0E-9 | 3.0E-3 | 6.7E-2 | 6.6E-3 | 4.1E-1 | 8.4E-3 | 1.0E-9 | 1.0E-9 | 4.6E0 | 2.2E-2 | 326 | 7 | 190 | 7 | 0.66 |
| Rj | ng/ml | 1.0E-9 | 1.0E-9 | 1.3E0 | 1.0E-9 | 5.2E0 | 0.0E0 | 1.0E-9 | 1.0E-9 | 8.0E1 | 1.0E-9 | 327 | 7 | 191 | 7 | 0.36 |
| Rf | ng/ml | 3.9E-1 | 5.3E-1 | 9.7E-1 | 1.6E0 | 1.7E0 | 2.6E0 | 7.8E-3 | 7.0E-2 | 1.5E1 | 7.5E0 | 326 | 7 | 190 | 7 | 0.58 |
| Ql | pg/ml | 4.5E0 | 4.5E0 | 1.4E1 | 1.4E1 | 2.9E1 | 2.0E1 | 1.0E-9 | 1.0E-9 | 2.9E2 | 5.5E1 | 332 | 7 | 193 | 7 | 0.52 |
| Qm | pg/ml | 3.2E0 | 1.0E-9 | 2.0E1 | 1.3E1 | 3.7E1 | 1.8E1 | 1.0E-9 | 1.0E-9 | 3.6E2 | 4.4E1 | 332 | 7 | 193 | 7 | 0.46 |
| Qn | pg/ml | 6.1E-1 | 1.0E-9 | 8.0E0 | 2.6E-1 | 2.6E1 | 3.2E-1 | 1.0E-9 | 1.0E-9 | 2.4E2 | 6.1E-1 | 332 | 7 | 193 | 7 | 0.28 |
| Nv | pg/ml | 4.0E3 | 1.1E4 | 1.1E4 | 2.4E4 | 4.2E4 | 3.7E4 | 1.0E-9 | 1.6E2 | 1.1E6 | 1.3E5 | 939 | 13 | 345 | 13 | 0.72 |
| Nw | pg/ml | 8.9E3 | 1.7E4 | 1.3E4 | 4.2E4 | 1.6E4 | 6.2E4 | 8.6E1 | 3.6E3 | 2.1E5 | 2.1E5 | 939 | 13 | 345 | 13 | 0.72 |
| Nx | pg/ml | 2.2E2 | 2.2E2 | 4.1E2 | 5.5E2 | 6.4E2 | 8.7E2 | 1.0E-9 | 1.0E-9 | 7.4E3 | 2.8E3 | 939 | 13 | 345 | 13 | 0.51 |
| Ny | pg/ml | 6.2E0 | 2.3E1 | 5.2E1 | 7.2E1 | 8.3E2 | 1.7E2 | 1.0E-9 | 1.0E-9 | 2.5E4 | 6.2E2 | 939 | 13 | 345 | 13 | 0.65 |
| Oa | pg/ml | 1.8E2 | 3.5E2 | 4.6E2 | 5.6E2 | 7.3E2 | 8.1E2 | 1.0E-9 | 1.0E-9 | 4.8E3 | 2.4E3 | 332 | 7 | 193 | 7 | 0.55 |
| Oe | pg/ml | 7.1E1 | 1.0E-9 | 2.9E2 | 1.9E2 | 7.4E2 | 4.5E2 | 1.0E-9 | 1.0E-9 | 1.9E4 | 1.6E3 | 930 | 13 | 344 | 13 | 0.40 |
| Of | pg/ml | 1.8E2 | 9.1E1 | 5.9E3 | 6.4E3 | 2.8E4 | 2.0E4 | 1.0E-9 | 1.0E-9 | 6.2E5 | 7.4E4 | 938 | 13 | 345 | 13 | 0.46 |
| Og | pg/ml | 8.2E-2 | 1.0E-9 | 7.1E-1 | 1.5E-1 | 4.7E0 | 3.3E-1 | 1.0E-9 | 1.0E-9 | 8.3E1 | 1.2E0 | 938 | 13 | 345 | 13 | 0.34 |

Figure 15 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oh | pg/ml | 2.6E0 | 5.3E0 | 1.8E1 | 3.7E1 | 1.4E2 | 7.5E1 | 1.0E-9 | 1.0E-9 | 3.5E3 | 2.2E2 | 938 | 13 | 345 | 13 | 0.58 |
| Oi | pg/ml | 2.6E0 | 1.4E0 | 6.3E0 | 4.3E0 | 9.8E0 | 5.9E0 | 1.0E-9 | 1.0E-9 | 8.6E1 | 1.9E1 | 938 | 13 | 345 | 13 | 0.46 |
| Ok | pg/ml | 3.9E2 | 6.5E2 | 5.4E2 | 6.8E3 | 5.7E2 | 1.9E4 | 1.3E1 | 5.3E1 | 7.0E3 | 7.0E4 | 938 | 13 | 345 | 13 | 0.66 |
| Om | pg/ml | 3.9E2 | 6.9E2 | 8.2E2 | 3.3E3 | 2.1E3 | 5.4E3 | 1.0E-9 | 1.0E-9 | 3.6E4 | 1.7E4 | 938 | 13 | 345 | 13 | 0.59 |
| On | pg/ml | 1.8E2 | 5.3E2 | 2.8E2 | 2.3E3 | 3.9E2 | 4.6E3 | 1.0E-9 | 1.6E1 | 4.5E3 | 1.5E4 | 938 | 13 | 345 | 13 | 0.75 |
| Or | pg/ml | 1.4E1 | 1.8E1 | 3.5E1 | 1.5E2 | 6.6E1 | 2.8E2 | 1.0E-9 | 1.0E-9 | 5.0E2 | 7.6E2 | 334 | 7 | 191 | 7 | 0.57 |
| Ow | pg/ml | 3.3E1 | 1.1E2 | 1.2E2 | 4.2E2 | 3.3E2 | 5.4E2 | 1.0E-9 | 4.7E1 | 3.2E3 | 1.5E3 | 334 | 7 | 191 | 7 | 0.81 |
| Ou | pg/ml | 4.8E2 | 6.4E3 | 9.8E2 | 5.5E3 | 1.6E3 | 3.4E3 | 1.0E-9 | 3.1E2 | 9.8E3 | 9.6E3 | 334 | 7 | 191 | 7 | 0.88 |
| Ul | ng/ml | 1.0E-9 | 1.0E-9 | 1.6E0 | 6.7E-1 | 7.5E0 | 1.8E0 | 1.0E-9 | 1.0E-9 | 1.0E2 | 4.7E0 | 340 | 7 | 195 | 7 | 0.52 |
| Uo | ng/ml | 1.0E-9 | 1.0E-9 | 9.9E-2 | 1.2E-1 | 2.6E-1 | 2.2E-1 | 1.0E-9 | 1.0E-9 | 2.6E0 | 5.0E-1 | 340 | 7 | 195 | 7 | 0.52 |
| Uk | ng/ml | 1.0E-9 | 1.0E-9 | 7.2E-3 | 2.0E-4 | 2.4E-2 | 5.2E-4 | 1.0E-9 | 1.0E-9 | 3.2E-1 | 1.4E-3 | 340 | 7 | 195 | 7 | 0.35 |
| Um | ng/ml | 1.0E-9 | 1.0E-9 | 4.0E-1 | 2.2E-1 | 9.5E-1 | 5.8E-1 | 1.0E-9 | 1.0E-9 | 7.2E0 | 1.5E0 | 340 | 7 | 195 | 7 | 0.41 |
| Uf | ng/ml | 6.0E-2 | 9.6E-2 | 1.4E-1 | 8.0E-1 | 2.7E-1 | 1.9E0 | 1.0E-3 | 3.5E-3 | 2.5E0 | 5.1E0 | 340 | 7 | 195 | 7 | 0.54 |
| Uh | ng/ml | 2.0E0 | 2.2E0 | 3.2E0 | 3.8E0 | 3.4E0 | 3.5E0 | 1.3E-2 | 7.0E-1 | 1.8E1 | 1.1E1 | 340 | 7 | 195 | 7 | 0.59 |
| Un | ng/ml | 1.9E0 | 1.9E0 | 2.2E0 | 2.3E0 | 1.3E0 | 1.3E0 | 1.3E-1 | 7.4E-1 | 8.0E0 | 4.4E0 | 340 | 7 | 195 | 7 | 0.53 |
| Ug | ng/ml | 1.5E1 | 2.3E0 | 2.8E1 | 6.7E0 | 3.0E1 | 7.6E0 | 6.9E-1 | 1.0E0 | 2.1E2 | 2.2E1 | 340 | 7 | 195 | 7 | 0.20 |
| Ur | ng/ml | 1.6E-1 | 1.0E-9 | 7.6E-1 | 2.7E-2 | 5.2E-1 | 7.2E-2 | 1.0E-9 | 1.0E-9 | 9.3E1 | 1.9E-1 | 339 | 7 | 194 | 7 | 0.16 |
| Up | ng/ml | 1.0E-9 | 1.0E-9 | 5.0E-3 | 1.0E-9 | 2.2E-2 | 0.0E0 | 1.0E-9 | 1.0E-9 | 3.3E-1 | 1.0E-9 | 339 | 7 | 194 | 7 | 0.34 |
| Us | ng/ml | 3.5E-3 | 1.0E-9 | 1.9E-2 | 2.4E-4 | 4.4E-2 | 4.1E-4 | 1.0E-9 | 1.0E-9 | 4.0E-1 | 8.6E-4 | 339 | 7 | 194 | 7 | 0.24 |
| Uv | ng/ml | 2.7E-3 | 1.0E-3 | 1.1E-2 | 4.4E-3 | 3.8E-2 | 7.2E-3 | 1.0E-9 | 1.0E-9 | 4.3E-1 | 1.9E-2 | 339 | 7 | 194 | 7 | 0.40 |
| Ut | ng/ml | 6.3E-1 | 1.9E0 | 2.6E0 | 3.3E0 | 8.0E0 | 4.6E0 | 1.0E-9 | 1.0E-9 | 7.8E1 | 1.3E1 | 339 | 7 | 194 | 7 | 0.58 |
| Uu | ng/ml | 7.1E0 | 3.6E0 | 8.1E0 | 4.7E0 | 5.8E0 | 3.4E0 | 4.5E-1 | 8.1E-1 | 4.0E1 | 9.1E0 | 339 | 7 | 194 | 7 | 0.32 |
| Vp | ng/ml | 1.0E-9 | 1.0E-9 | 3.5E-1 | 1.0E-9 | 3.1E0 | 0.0E0 | 1.0E-9 | 1.0E-9 | 5.0E1 | 1.0E-9 | 340 | 7 | 195 | 7 | 0.43 |
| Vt | ng/ml | 6.7E0 | 5.4E0 | 9.4E0 | 9.3E0 | 9.8E0 | 8.2E0 | 4.3E-1 | 1.4E0 | 8.6E1 | 2.3E1 | 340 | 7 | 195 | 7 | 0.50 |
| Vu | ng/ml | 1.0E-9 | 1.3E0 | 2.3E0 | 3.1E0 | 6.4E0 | 4.8E0 | 1.0E-9 | 1.0E-9 | 7.1E1 | 1.3E1 | 334 | 7 | 195 | 7 | 0.60 |
| Vo | ng/ml | 2.5E1 | 2.2E1 | 2.4E1 | 1.8E1 | 5.2E0 | 9.4E0 | 2.4E0 | 1.9E0 | 4.8E1 | 2.6E1 | 340 | 7 | 195 | 7 | 0.26 |
| Vs | ng/ml | 1.0E-9 | 1.0E-9 | 6.1E0 | 2.6E0 | 2.2E1 | 4.0E0 | 1.0E-9 | 1.0E-9 | 2.3E2 | 9.4E0 | 325 | 7 | 190 | 7 | 0.49 |
| Vv | ng/ml | 3.0E0 | 3.0E0 | 5.9E0 | 1.4E1 | 9.5E0 | 2.9E1 | 1.0E-9 | 1.0E-9 | 8.4E1 | 8.0E1 | 339 | 7 | 195 | 7 | 0.51 |
| Oy | pg/ml | 4.9E-1 | 6.5E-1 | 5.7E0 | 2.3E1 | 2.8E1 | 7.5E1 | 1.0E-9 | 1.0E-9 | 4.0E2 | 2.7E2 | 937 | 13 | 344 | 13 | 0.57 |
| Oz | pg/ml | 1.2E-2 | 3.0E-2 | 3.2E-1 | 2.4E-1 | 1.3E0 | 3.0E-1 | 1.0E-9 | 1.0E-9 | 2.9E1 | 7.1E-1 | 937 | 13 | 344 | 13 | 0.52 |
| Pa | pg/ml | 3.9E-1 | 6.1E-1 | 1.4E0 | 2.6E1 | 4.9E0 | 8.1E1 | 1.0E-9 | 1.0E-9 | 8.6E1 | 2.9E2 | 937 | 13 | 344 | 13 | 0.63 |
| Pb | pg/ml | 1.0E-9 | 1.3E-1 | 7.4E-1 | 1.4E1 | 1.6E1 | 5.0E1 | 1.0E-9 | 1.0E-9 | 4.9E2 | 1.8E2 | 937 | 13 | 344 | 13 | 0.65 |
| Pc | pg/ml | 5.4E-2 | 4.2E-1 | 3.5E-1 | 1.7E0 | 8.4E-1 | 3.4E0 | 1.0E-9 | 1.0E-9 | 1.6E1 | 1.1E1 | 937 | 13 | 344 | 13 | 0.62 |
| Pd | pg/ml | 1.8E0 | 2.5E0 | 4.8E0 | 8.3E0 | 2.8E1 | 1.5E1 | 1.0E-9 | 1.0E-9 | 8.4E2 | 5.5E1 | 937 | 13 | 344 | 13 | 0.55 |
| Pe | pg/ml | 2.2E1 | 9.4E1 | 1.0E2 | 1.3E3 | 3.4E2 | 3.9E3 | 1.0E-9 | 3.3E0 | 4.7E3 | 1.4E4 | 937 | 13 | 344 | 13 | 0.69 |
| Pf | pg/ml | 1.6E0 | 6.3E0 | 1.0E1 | 2.8E1 | 5.7E1 | 6.2E1 | 1.0E-9 | 1.0E-9 | 1.5E3 | 2.3E2 | 937 | 13 | 344 | 13 | 0.68 |
| Pg | pg/ml | 3.5E0 | 6.4E0 | 4.1E1 | 1.9E2 | 3.3E2 | 5.2E2 | 1.0E-9 | 5.5E-1 | 7.7E3 | 1.9E3 | 937 | 13 | 344 | 13 | 0.67 |
| Ph | ng/ml | 1.8E-1 | 5.8E-1 | 3.5E-1 | 8.3E-1 | 5.5E-1 | 9.3E-1 | 1.0E-9 | 1.0E-9 | 4.4E0 | 2.3E0 | 334 | 7 | 191 | 7 | 0.56 |
| Pi | ng/ml | 2.0E-1 | 3.5E-1 | 2.9E-1 | 3.3E-1 | 4.2E-1 | 2.0E-1 | 1.0E-9 | 1.0E-9 | 4.8E0 | 6.4E-1 | 334 | 7 | 191 | 7 | 0.64 |
| Pj | pg/mL | 5.4E0 | 5.1E0 | 6.2E0 | 6.6E0 | 5.2E0 | 7.7E0 | 3.8E-2 | 6.6E-1 | 3.7E1 | 2.3E1 | 334 | 7 | 191 | 7 | 0.43 |
| Pk | ng/ml | 8.9E-3 | 9.0E-3 | 1.3E-2 | 1.1E-2 | 2.0E-2 | 8.5E-3 | 1.0E-9 | 1.0E-9 | 2.5E-1 | 2.5E-2 | 334 | 7 | 191 | 7 | 0.52 |
| aA | mg/dL | 8.1E-1 | 1.3E0 | 9.5E-1 | 2.0E0 | 4.9E-1 | 1.4E0 | 2.0E-1 | 6.2E-1 | 4.2E0 | 5.4E0 | 2722 | 25 | 517 | 25 | 0.82 |
| aC | mg/mL | 2.8E0 | 2.4E0 | 3.1E0 | 2.6E0 | 1.4E0 | 1.3E0 | 7.7E-1 | 1.1E0 | 8.9E0 | 5.5E0 | 551 | 12 | 213 | 12 | 0.39 |
| aD | ug/mL | 3.1E0 | 4.2E0 | 4.4E0 | 5.7E0 | 3.9E0 | 4.6E0 | 4.3E-1 | 9.9E-1 | 3.5E1 | 1.7E1 | 551 | 12 | 213 | 12 | 0.58 |
| aE | mg/mL | 5.6E-1 | 6.3E-1 | 5.7E-1 | 6.4E-1 | 1.5E-1 | 1.9E-1 | 1.8E-1 | 4.3E-1 | 1.1E0 | 1.2E0 | 551 | 12 | 213 | 12 | 0.61 |
| aF | ng/mL | 2.2E0 | 2.4E0 | 4.0E0 | 5.8E0 | 5.7E0 | 6.7E0 | 4.3E-3 | 4.3E-3 | 5.0E1 | 1.8E1 | 551 | 12 | 213 | 12 | 0.48 |
| aG | mg/mL | 1.4E-1 | 1.2E-1 | 1.6E-1 | 1.6E-1 | 8.7E-2 | 1.4E-1 | 1.7E-2 | 5.9E-2 | 5.4E-1 | 5.2E-1 | 551 | 12 | 213 | 12 | 0.43 |
| aH | ug/mL | 7.5E1 | 6.4E1 | 8.2E1 | 8.1E1 | 4.4E1 | 4.4E1 | 4.6E0 | 3.6E1 | 2.9E2 | 1.8E2 | 551 | 12 | 213 | 12 | 0.48 |
| aI | ug/mL | 1.9E2 | 1.5E2 | 1.9E2 | 1.7E2 | 6.0E1 | 5.1E1 | 2.8E1 | 1.0E2 | 3.7E2 | 2.7E2 | 551 | 12 | 213 | 12 | 0.39 |
| aJ | ug/mL | 2.5E0 | 5.0E0 | 3.1E0 | 6.5E0 | 2.2E0 | 3.8E0 | 7.3E-1 | 2.2E0 | 1.7E1 | 1.5E1 | 551 | 12 | 213 | 12 | 0.82 |
| aK | ng/mL | 1.5E0 | 1.6E0 | 2.4E0 | 2.4E0 | 2.6E0 | 2.2E0 | 2.9E-4 | 1.3E-1 | 1.8E1 | 6.5E0 | 551 | 12 | 213 | 12 | 0.52 |
| aL | mg/mL | 8.0E-1 | 6.9E-1 | 8.1E-1 | 7.3E-1 | 2.6E-1 | 2.5E-1 | 1.9E-1 | 4.0E-1 | 1.7E0 | 1.2E0 | 551 | 12 | 213 | 12 | 0.41 |
| aM | U/mL | 2.2E1 | 4.5E1 | 4.6E1 | 6.6E1 | 9.3E1 | 1.0E2 | 4.2E-2 | 4.2E-2 | 1.6E3 | 3.8E2 | 551 | 12 | 213 | 12 | 0.60 |
| aN | U/mL | 1.4E1 | 2.4E1 | 2.2E1 | 3.1E1 | 3.0E1 | 3.0E1 | 2.5E-3 | 3.9E0 | 3.8E2 | 9.2E1 | 551 | 12 | 213 | 12 | 0.63 |
| aO | pg/mL | 3.3E1 | 1.6E2 | 3.0E2 | 8.7E2 | 7.7E2 | 1.2E3 | 6.0E-2 | 6.0E-2 | 6.6E3 | 3.5E3 | 551 | 12 | 213 | 12 | 0.69 |
| aP | ng/mL | 1.7E0 | 3.3E0 | 2.1E0 | 3.5E0 | 1.8E0 | 1.7E0 | 4.5E-1 | 1.6E0 | 2.8E1 | 6.1E0 | 551 | 12 | 213 | 12 | 0.76 |
| aQ | ng/mL | 3.0E-1 | 3.6E-1 | 4.5E-1 | 3.6E-1 | 4.5E-1 | 3.1E-1 | 2.0E-4 | 5.2E-2 | 4.0E0 | 9.9E-1 | 551 | 12 | 213 | 12 | 0.44 |

Figure 15 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aR | ng/mL | 1.8E0 | 2.9E0 | 2.8E0 | 2.8E0 | 3.3E0 | 1.8E0 | 1.8E-1 | 3.2E-1 | 3.4E1 | 5.0E0 | 551 | 12 | 213 | 12 | 0.56 |
| aS | ng/mL | 2.7E-1 | 3.6E-1 | 6.3E-1 | 6.2E-1 | 1.7E0 | 7.4E-1 | 4.2E-3 | 8.0E-2 | 3.3E1 | 2.6E0 | 551 | 12 | 213 | 12 | 0.54 |
| aU | pg/mL | 7.5E1 | 8.5E1 | 1.2E2 | 1.5E2 | 1.5E2 | 1.5E2 | 7.4E-2 | 7.4E-2 | 1.3E3 | 5.1E2 | 551 | 12 | 213 | 12 | 0.56 |
| aV | ng/mL | 6.2E-1 | 5.9E-1 | 1.0E0 | 1.2E0 | 1.8E0 | 1.5E0 | 7.6E-4 | 1.0E-1 | 3.3E1 | 4.2E0 | 551 | 12 | 213 | 12 | 0.50 |
| aW | pg/mL | 1.8E1 | 2.5E1 | 1.9E1 | 5.8E1 | 1.8E1 | 1.2E2 | 7.2E-2 | 7.2E-2 | 2.4E2 | 4.5E2 | 551 | 12 | 213 | 12 | 0.65 |
| aX | ng/mL | 9.5E0 | 1.5E1 | 1.6E1 | 2.9E1 | 2.6E1 | 3.4E1 | 3.0E-1 | 3.3E0 | 3.1E2 | 1.1E2 | 551 | 12 | 213 | 12 | 0.63 |
| aY | pg/mL | 5.7E1 | 6.6E1 | 7.5E1 | 9.0E1 | 8.2E1 | 7.2E1 | 4.1E-1 | 2.7E1 | 1.2E3 | 2.7E2 | 551 | 12 | 213 | 12 | 0.58 |
| aZ | pg/mL | 2.2E2 | 3.3E2 | 5.4E2 | 6.8E2 | 1.1E3 | 7.5E2 | 1.7E0 | 7.2E1 | 1.2E4 | 2.1E3 | 551 | 12 | 213 | 12 | 0.63 |
| bA | ng/mL | 9.0E0 | 1.1E2 | 3.5E1 | 2.0E2 | 9.2E1 | 2.5E2 | 3.0E-2 | 4.7E0 | 9.7E2 | 8.1E2 | 551 | 12 | 213 | 12 | 0.86 |
| bB | ng/mL | 3.0E2 | 2.7E2 | 3.2E2 | 2.8E2 | 1.7E2 | 1.4E2 | 2.1E0 | 7.8E1 | 1.0E3 | 5.5E2 | 551 | 12 | 213 | 12 | 0.45 |
| bC | ng/mL | 3.4E2 | 4.2E2 | 6.0E2 | 1.2E3 | 7.9E2 | 1.4E3 | 9.8E0 | 1.8E2 | 4.7E3 | 4.0E3 | 551 | 12 | 213 | 12 | 0.64 |
| bE | mg/mL | 5.5E0 | 5.7E0 | 5.8E0 | 6.7E0 | 2.1E0 | 2.8E0 | 9.8E-1 | 3.2E0 | 1.3E1 | 1.0E1 | 551 | 12 | 213 | 12 | 0.57 |
| bF | pg/mL | 2.0E1 | 4.9E1 | 1.5E2 | 6.3E1 | 8.8E2 | 4.4E1 | 5.0E-2 | 8.1E0 | 1.1E4 | 1.5E2 | 551 | 12 | 213 | 12 | 0.72 |
| bG | ng/mL | 1.6E0 | 2.0E0 | 2.7E0 | 5.5E0 | 3.2E0 | 5.7E0 | 2.2E-2 | 2.4E-1 | 2.6E1 | 1.5E1 | 551 | 12 | 213 | 12 | 0.59 |
| bH | pg/mL | 5.7E-1 | 5.7E-1 | 4.7E0 | 6.5E0 | 1.4E1 | 8.1E0 | 5.7E-1 | 5.7E-1 | 2.8E2 | 2.3E1 | 551 | 12 | 213 | 12 | 0.57 |
| bI | ng/mL | 4.0E-3 | 4.0E-3 | 6.0E-2 | 4.7E-2 | 1.5E-1 | 1.1E-1 | 4.0E-3 | 4.0E-3 | 1.3E0 | 3.9E-1 | 551 | 12 | 213 | 12 | 0.50 |
| bJ | mg/mL | 2.3E0 | 2.4E0 | 2.6E0 | 3.2E0 | 2.0E0 | 2.4E0 | 2.5E-4 | 9.6E-1 | 1.3E1 | 8.9E0 | 551 | 12 | 213 | 12 | 0.55 |
| bL | pg/mL | 3.8E0 | 6.5E0 | 8.5E0 | 8.5E0 | 1.1E1 | 7.1E0 | 4.6E-2 | 4.6E-2 | 8.0E1 | 2.0E1 | 551 | 12 | 213 | 12 | 0.58 |
| bM | mg/mL | 1.7E0 | 2.1E0 | 2.1E0 | 2.1E0 | 1.4E0 | 9.3E-1 | 9.2E-3 | 5.5E-1 | 8.9E0 | 3.5E0 | 551 | 12 | 213 | 12 | 0.56 |
| bN | ng/mL | 4.2E1 | 2.6E1 | 1.3E2 | 3.1E1 | 2.7E2 | 2.4E1 | 1.4E-1 | 2.2E0 | 1.9E3 | 7.7E1 | 551 | 12 | 213 | 12 | 0.36 |
| bO | ng/mL | 4.0E-2 | 4.0E-2 | 1.0E1 | 1.8E1 | 2.3E1 | 5.5E1 | 4.0E-2 | 4.0E-2 | 2.0E2 | 1.9E2 | 551 | 12 | 213 | 12 | 0.42 |
| bP | mg/mL | 5.3E-1 | 7.3E-1 | 7.6E-1 | 8.8E-1 | 6.9E-1 | 7.1E-1 | 4.9E-2 | 9.2E-2 | 4.8E0 | 2.9E0 | 551 | 12 | 213 | 12 | 0.60 |
| bQ | pg/mL | 1.6E1 | 4.1E1 | 5.8E1 | 4.8E1 | 5.8E2 | 4.0E1 | 1.5E-1 | 6.7E0 | 1.3E4 | 1.4E2 | 551 | 12 | 213 | 12 | 0.69 |
| bR | ng/mL | 1.2E-2 | 1.2E-2 | 1.3E-1 | 7.5E-2 | 4.2E-1 | 1.5E-1 | 1.2E-2 | 1.2E-2 | 8.7E0 | 3.9E-1 | 551 | 12 | 213 | 12 | 0.41 |
| bS | pg/mL | 9.4E-1 | 9.4E-1 | 7.0E0 | 8.8E0 | 2.6E1 | 2.1E1 | 9.4E-1 | 9.4E-1 | 3.9E2 | 7.2E1 | 551 | 12 | 213 | 12 | 0.52 |
| bU | ng/mL | 1.2E-1 | 1.3E-2 | 1.9E-1 | 9.5E-2 | 3.5E-1 | 1.2E-1 | 1.3E-2 | 1.3E-2 | 6.6E0 | 3.4E-1 | 551 | 12 | 213 | 12 | 0.38 |
| bV | pg/mL | 4.7E2 | 8.6E2 | 5.9E2 | 8.9E2 | 8.9E2 | 4.8E2 | 1.5E2 | 3.5E2 | 1.7E4 | 2.2E3 | 551 | 12 | 213 | 12 | 0.79 |
| bW | pg/mL | 3.3E2 | 4.2E2 | 5.1E2 | 7.4E2 | 5.5E2 | 1.0E3 | 8.4E1 | 1.8E2 | 6.4E3 | 3.9E3 | 551 | 12 | 213 | 12 | 0.60 |
| bX | ng/mL | 2.5E-5 | 3.1E-3 | 2.7E-3 | 2.8E-3 | 3.4E-3 | 2.7E-3 | 2.5E-5 | 2.5E-5 | 2.0E-2 | 7.2E-3 | 551 | 12 | 213 | 12 | 0.52 |
| bZ | pg/mL | 2.5E2 | 6.2E2 | 8.5E2 | 2.0E3 | 3.7E3 | 2.5E3 | 1.5E-1 | 1.6E2 | 5.8E4 | 7.4E3 | 551 | 12 | 213 | 12 | 0.73 |
| cA | pg/mL | 6.0E-1 | 6.0E-1 | 2.7E0 | 2.3E0 | 1.6E1 | 5.9E0 | 6.0E-1 | 6.0E-1 | 3.7E2 | 2.1E1 | 551 | 12 | 213 | 12 | 0.48 |
| cB | ng/mL | 5.5E-2 | 4.1E-2 | 8.7E-2 | 6.8E-2 | 1.0E-1 | 7.2E-2 | 1.7E-3 | 1.7E-3 | 5.7E-1 | 2.6E-1 | 551 | 12 | 213 | 12 | 0.47 |
| cC | pg/mL | 4.6E1 | 3.7E1 | 4.7E1 | 3.8E1 | 3.9E1 | 2.4E1 | 1.0E0 | 1.0E0 | 4.5E2 | 6.7E1 | 551 | 12 | 213 | 12 | 0.44 |
| cD | pg/mL | 5.2E0 | 6.7E0 | 1.5E1 | 8.6E0 | 5.2E1 | 1.0E1 | 3.3E-1 | 3.3E-1 | 7.2E2 | 3.8E1 | 551 | 12 | 213 | 12 | 0.51 |
| cE | pg/mL | 3.9E1 | 6.4E1 | 1.5E2 | 9.1E1 | 4.3E2 | 8.7E1 | 1.2E-1 | 2.0E0 | 3.8E3 | 2.8E2 | 551 | 12 | 213 | 12 | 0.58 |
| cF | pg/mL | 1.3E1 | 5.3E-1 | 2.0E1 | 7.5E0 | 3.0E1 | 2.0E1 | 5.3E-1 | 5.3E-1 | 2.7E2 | 7.2E1 | 551 | 12 | 213 | 12 | 0.30 |
| cG | pg/mL | 4.6E1 | 8.4E1 | 1.1E2 | 1.1E2 | 4.7E1 | 9.6E1 | 6.4E0 | 1.5E1 | 1.0E4 | 3.8E2 | 551 | 12 | 213 | 12 | 0.66 |
| cH | uIU/mL | 2.8E0 | 2.3E0 | 6.0E0 | 7.7E0 | 1.1E1 | 1.0E1 | 8.6E-3 | 8.6E-3 | 1.6E2 | 3.4E1 | 551 | 12 | 213 | 12 | 0.51 |
| cI | ng/mL | 5.7E0 | 9.2E0 | 1.2E1 | 1.9E1 | 1.7E1 | 3.2E1 | 1.0E-3 | 1.1E0 | 1.2E2 | 1.2E2 | 551 | 12 | 213 | 12 | 0.59 |
| cJ | ug/mL | 6.2E1 | 6.1E1 | 1.1E2 | 7.4E1 | 1.4E2 | 4.7E1 | 4.0E0 | 1.5E1 | 9.6E2 | 1.7E2 | 551 | 12 | 213 | 12 | 0.50 |
| cK | ng/mL | 3.8E-3 | 3.8E-3 | 4.7E-2 | 5.3E-2 | 1.7E-1 | 9.1E-2 | 3.8E-3 | 3.8E-3 | 1.7E0 | 2.4E-1 | 551 | 12 | 213 | 12 | 0.55 |
| cL | pg/mL | 2.0E2 | 2.2E2 | 3.9E2 | 3.0E2 | 1.3E3 | 3.4E2 | 1.6E1 | 6.7E1 | 2.4E4 | 1.3E3 | 551 | 12 | 213 | 12 | 0.53 |
| cM | pg/mL | 2.7E2 | 2.5E2 | 2.9E2 | 2.7E2 | 1.9E2 | 7.7E1 | 8.7E0 | 1.5E2 | 1.6E3 | 4.3E2 | 551 | 12 | 213 | 12 | 0.48 |
| cN | pg/mL | 1.2E2 | 1.5E2 | 1.3E2 | 1.5E2 | 6.2E1 | 4.4E1 | 3.8E1 | 9.6E1 | 1.1E3 | 2.2E2 | 551 | 12 | 213 | 12 | 0.68 |
| cO | pg/mL | 2.2E2 | 3.1E2 | 3.0E2 | 4.4E2 | 8.3E2 | 3.9E2 | 5.4E1 | 9.6E1 | 1.9E4 | 1.5E3 | 551 | 12 | 213 | 12 | 0.65 |
| cP | ng/mL | 2.5E3 | 3.7E3 | 2.6E3 | 3.6E3 | 9.0E2 | 1.4E3 | 6.2E2 | 1.4E3 | 5.7E3 | 5.9E3 | 551 | 12 | 213 | 12 | 0.72 |
| cQ | ng/mL | 5.1E-2 | 1.3E-1 | 1.4E-1 | 1.8E-1 | 2.8E-1 | 1.7E-1 | 2.0E-3 | 2.0E-3 | 2.2E0 | 4.9E-1 | 551 | 12 | 213 | 12 | 0.65 |
| cR | ng/mL | 3.0E2 | 4.9E2 | 5.2E2 | 6.6E2 | 8.3E2 | 5.7E2 | 2.0E1 | 1.6E2 | 8.9E3 | 2.2E3 | 551 | 12 | 213 | 12 | 0.67 |
| cS | ng/mL | 2.6E2 | 5.7E2 | 4.4E2 | 8.8E2 | 1.0E3 | 8.2E2 | 4.1E1 | 1.4E2 | 2.2E4 | 2.6E3 | 551 | 12 | 213 | 12 | 0.75 |
| cT | ng/mL | 3.3E1 | 1.4E2 | 8.8E1 | 3.5E2 | 2.0E2 | 5.2E2 | 3.6E0 | 1.9E1 | 2.1E3 | 1.9E3 | 551 | 12 | 213 | 12 | 0.83 |
| cU | ng/mL | 5.4E1 | 1.2E2 | 7.7E1 | 1.4E2 | 9.6E1 | 9.2E1 | 5.4E0 | 3.0E1 | 1.6E3 | 3.3E2 | 551 | 12 | 213 | 12 | 0.75 |
| cV | ng/mL | 1.8E-1 | 1.6E-1 | 4.0E-1 | 2.2E-1 | 2.1E0 | 1.5E-1 | 3.4E-4 | 6.4E-2 | 4.7E1 | 4.5E-1 | 551 | 12 | 213 | 12 | 0.50 |
| cW | mIU/mL | 5.2E-2 | 9.0E-2 | 1.3E-1 | 9.8E-2 | 6.5E-1 | 5.7E-2 | 3.7E-4 | 2.7E-2 | 9.7E0 | 2.0E-1 | 551 | 12 | 213 | 12 | 0.68 |
| cX | ng/mL | 1.1E-1 | 2.9E-2 | 1.3E0 | 1.5E-1 | 4.3E0 | 3.1E-1 | 2.3E-4 | 2.3E-4 | 2.8E1 | 1.1E0 | 551 | 12 | 213 | 12 | 0.35 |
| cY | ng/mL | 8.6E0 | 9.0E0 | 1.2E1 | 1.2E1 | 1.3E1 | 1.1E1 | 1.5E-1 | 6.0E-1 | 8.3E1 | 3.6E1 | 551 | 12 | 213 | 12 | 0.50 |
| cZ | ug/mL | 1.4E1 | 1.6E1 | 1.6E1 | 1.6E1 | 7.1E0 | 6.4E0 | 2.3E0 | 8.0E0 | 5.7E1 | 3.0E1 | 551 | 12 | 213 | 12 | 0.54 |
| dA | pg/mL | 3.3E2 | 5.1E2 | 3.7E2 | 5.2E2 | 2.8E2 | 2.8E2 | 9.0E1 | 1.7E2 | 5.8E3 | 8.8E2 | 551 | 12 | 213 | 12 | 0.65 |

Figure 15 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| dB | ug/mL | 1.7E1 | 2.1E1 | 1.7E1 | 2.3E1 | 1.5E1 | 7.8E0 | 9.4E-1 | 1.4E1 | 2.5E2 | 4.1E1 | 551 | 12 | 213 | 12 | 0.69 |
| dC | nmol/L | 3.5E1 | 3.2E1 | 3.8E1 | 3.7E1 | 1.8E1 | 1.8E1 | 7.6E0 | 2.1E1 | 1.4E2 | 8.2E1 | 551 | 12 | 213 | 12 | 0.44 |
| dD | ug/mL | 3.6E1 | 2.9E1 | 3.7E1 | 3.3E1 | 1.1E1 | 1.1E1 | 1.3E1 | 1.5E1 | 7.6E1 | 5.6E1 | 551 | 12 | 213 | 12 | 0.38 |
| dE | ng/mL | 4.7E-1 | 7.3E-1 | 6.0E-1 | 9.5E-1 | 6.9E-1 | 8.5E-1 | 8.4E-3 | 3.0E-1 | 7.2E0 | 3.3E0 | 551 | 12 | 213 | 12 | 0.66 |
| dF | ng/mL | 2.3E2 | 3.2E2 | 2.8E2 | 4.2E2 | 1.9E2 | 2.6E2 | 5.6E1 | 1.7E2 | 1.3E3 | 9.7E2 | 551 | 12 | 213 | 12 | 0.71 |
| dG | ng/mL | 1.2E1 | 1.6E1 | 1.5E1 | 2.0E1 | 1.3E1 | 8.9E0 | 2.2E0 | 6.7E0 | 1.8E2 | 3.5E1 | 551 | 12 | 213 | 12 | 0.70 |
| dH | pg/mL | 7.9E0 | 1.0E1 | 1.3E1 | 1.1E1 | 3.6E1 | 6.4E0 | 4.0E-2 | 8.3E-1 | 6.7E2 | 2.2E1 | 551 | 12 | 213 | 12 | 0.58 |
| dI | pg/mL | 4.6E-1 | 4.6E-1 | 2.2E0 | 2.1E0 | 1.5E1 | 2.7E0 | 4.6E-1 | 4.6E-1 | 3.3E2 | 8.4E0 | 551 | 12 | 213 | 12 | 0.57 |
| dJ | ng/mL | 1.9E0 | 2.6E0 | 2.2E0 | 2.5E0 | 1.2E0 | 1.0E0 | 3.2E-2 | 8.4E-1 | 6.9E0 | 4.0E0 | 551 | 12 | 213 | 12 | 0.60 |
| dK | uIU/mL | 1.9E0 | 1.0E0 | 3.0E0 | 1.8E0 | 6.0E0 | 1.9E0 | 2.8E-4 | 3.8E-2 | 7.9E1 | 6.1E0 | 551 | 12 | 213 | 12 | 0.41 |
| dL | ng/mL | 8.8E2 | 1.2E3 | 1.0E3 | 1.1E3 | 5.2E2 | 2.8E2 | 2.6E2 | 6.3E2 | 3.8E3 | 1.4E3 | 551 | 12 | 213 | 12 | 0.59 |
| dM | ng/mL | 9.7E2 | 1.9E3 | 1.2E3 | 2.9E3 | 1.3E3 | 2.4E3 | 3.4E2 | 7.1E2 | 1.6E4 | 8.3E3 | 551 | 12 | 213 | 12 | 0.78 |
| dN | ug/mL | 9.3E1 | 1.4E2 | 9.9E1 | 1.4E2 | 3.7E1 | 3.8E1 | 1.6E1 | 6.9E1 | 2.8E2 | 2.0E2 | 551 | 12 | 213 | 12 | 0.77 |
| dR | pg/ml | 1.6E3 | 8.3E2 | 2.3E3 | 1.4E3 | 2.3E3 | 1.5E3 | 1.4E2 | 1.3E2 | 1.5E4 | 5.1E3 | 378 | 9 | 202 | 9 | 0.36 |
| eF | ng/ml | 4.1E0 | 7.2E0 | 5.0E0 | 6.9E0 | 4.3E0 | 2.6E0 | 1.2E0 | 2.8E0 | 4.6E1 | 1.1E1 | 393 | 9 | 203 | 9 | 0.75 |
| eC | pg/ml | 3.0E2 | 2.6E2 | 3.7E2 | 2.6E2 | 2.6E2 | 1.5E2 | 9.9E0 | 1.1E2 | 1.6E3 | 5.4E2 | 304 | 7 | 190 | 7 | 0.36 |
| fP | ng/ml | 2.6E2 | 2.6E2 | 2.9E2 | 3.1E2 | 1.9E2 | 2.0E2 | 1.8E0 | 1.2E2 | 1.6E3 | 7.5E2 | 358 | 9 | 193 | 9 | 0.52 |
| fR | ng/ml | 1.4E5 | 2.9E5 | 1.9E5 | 3.2E5 | 1.5E5 | 1.9E5 | 2.9E4 | 1.2E5 | 8.3E5 | 7.2E5 | 363 | 11 | 111 | 11 | 0.75 |
| gL | pg/ml | 6.4E4 | 1.1E5 | 7.1E4 | 1.1E5 | 3.2E4 | 3.2E4 | 1.1E4 | 6.5E4 | 3.2E5 | 1.6E5 | 378 | 9 | 202 | 9 | 0.84 |
| gP | U/ml | 2.7E2 | 2.6E2 | 2.8E2 | 2.7E2 | 1.1E2 | 5.1E1 | 1.2E1 | 2.1E2 | 1.1E3 | 3.7E2 | 389 | 9 | 203 | 9 | 0.51 |
| gW | pg/ml | 6.1E2 | 5.1E2 | 1.3E3 | 7.2E2 | 1.6E3 | 5.4E2 | 3.1E-1 | 2.4E2 | 9.5E3 | 1.7E3 | 329 | 7 | 192 | 7 | 0.49 |
| tF | pg/mL | 1.4E3 | 5.8E3 | 1.3E4 | 1.9E4 | 4.0E4 | 3.4E4 | 1.2E1 | 1.8E1 | 3.2E5 | 9.4E4 | 305 | 7 | 190 | 7 | 0.63 |
| iA | pg/ml | 1.4E2 | 1.6E2 | 2.7E2 | 4.7E2 | 5.5E2 | 7.6E2 | 5.8E0 | 5.6E1 | 7.1E3 | 2.2E3 | 306 | 7 | 190 | 7 | 0.61 |
| iH | ng/ml | 1.6E5 | 2.0E5 | 1.6E5 | 1.9E5 | 4.9E4 | 5.3E4 | 2.9E3 | 8.1E4 | 2.7E5 | 2.5E5 | 306 | 7 | 190 | 7 | 0.70 |
| iJ | ng/ml | 5.0E4 | 5.0E4 | 5.4E4 | 5.6E4 | 2.8E4 | 2.8E4 | 1.8E3 | 1.5E4 | 2.5E5 | 9.7E4 | 306 | 7 | 190 | 7 | 0.55 |
| hB | ng/ml | 4.3E-1 | 9.4E-1 | 5.5E-1 | 8.4E-1 | 4.5E-1 | 4.7E-1 | 1.0E-9 | 1.5E-1 | 3.4E0 | 1.6E0 | 306 | 7 | 190 | 7 | 0.72 |
| hC | pg/ml | 3.7E3 | 1.0E4 | 6.6E3 | 8.0E3 | 9.4E3 | 5.9E3 | 1.0E-9 | 1.7E3 | 1.1E5 | 1.7E4 | 306 | 7 | 190 | 7 | 0.64 |
| hF | ng/ml | 1.0E-9 | 1.0E-9 | 1.6E1 | 1.0E-9 | 2.3E2 | 0.0E0 | 1.0E-9 | 1.0E-9 | 4.0E3 | 1.0E-9 | 306 | 7 | 190 | 7 | 0.49 |
| hG | pg/ml | 6.8E3 | 8.7E3 | 7.4E3 | 9.7E3 | 3.2E3 | 4.5E3 | 2.8E1 | 5.3E3 | 2.0E4 | 1.7E4 | 306 | 7 | 190 | 7 | 0.66 |
| iO | ng/ml | 3.7E5 | 3.4E5 | 3.9E5 | 3.5E5 | 1.7E5 | 1.3E5 | 1.1E4 | 1.0E5 | 1.1E6 | 4.6E5 | 306 | 7 | 190 | 7 | 0.47 |
| iP | ng/ml | 4.5E4 | 7.0E4 | 5.4E4 | 6.9E4 | 4.8E4 | 3.1E4 | 1.0E-9 | 3.2E4 | 5.5E5 | 1.2E5 | 306 | 7 | 190 | 7 | 0.68 |
| iZ | ng/ml | 1.7E3 | 2.5E3 | 1.8E3 | 3.0E3 | 7.5E2 | 1.7E3 | 4.7E2 | 1.5E3 | 5.7E3 | 6.5E3 | 305 | 8 | 188 | 8 | 0.73 |
| kQ | pg/ml | 4.1E3 | 6.1E3 | 5.0E3 | 6.5E3 | 3.4E3 | 2.6E3 | 5.6E2 | 2.7E3 | 2.5E4 | 1.0E4 | 306 | 7 | 190 | 7 | 0.71 |
| kR | pg/ml | 2.1E1 | 2.1E1 | 3.0E1 | 3.1E1 | 6.1E1 | 2.6E1 | 1.0E-9 | 2.9E0 | 1.0E3 | 6.9E1 | 306 | 7 | 190 | 7 | 0.53 |
| kS | pg/ml | 8.1E2 | 6.9E2 | 9.6E2 | 1.1E3 | 9.6E2 | 8.3E2 | 7.9E1 | 5.1E2 | 1.4E4 | 2.8E3 | 306 | 7 | 190 | 7 | 0.54 |
| nW | pg/ml | 1.1E5 | 1.0E5 | 1.1E5 | 1.2E5 | 2.7E4 | 3.8E4 | 3.6E4 | 8.4E4 | 2.1E5 | 1.9E5 | 306 | 7 | 190 | 7 | 0.52 |
| nY | pg/ml | 2.0E3 | 3.6E3 | 2.3E3 | 3.6E3 | 1.5E3 | 1.5E3 | 5.1E2 | 1.3E3 | 1.3E4 | 5.7E3 | 306 | 7 | 190 | 7 | 0.75 |
| oE | pg/ml | 1.5E2 | 3.9E2 | 3.9E2 | 4.0E2 | 5.6E2 | 3.3E2 | 1.0E-9 | 2.7E1 | 4.7E3 | 1.1E3 | 306 | 7 | 190 | 7 | 0.61 |
| oF | pg/ml | 8.8E3 | 1.7E4 | 2.2E4 | 6.0E4 | 3.5E4 | 8.3E4 | 6.4E1 | 7.8E2 | 2.5E5 | 1.8E5 | 306 | 7 | 190 | 7 | 0.62 |
| oH | pg/ml | 4.3E1 | 5.6E1 | 9.3E1 | 8.3E1 | 1.4E2 | 5.0E0 | 1.0E-9 | 1.3E1 | 9.9E2 | 3.1E2 | 306 | 7 | 190 | 7 | 0.51 |
| oK | pg/ml | 8.5E2 | 1.5E3 | 1.9E3 | 9.1E3 | 2.8E3 | 1.9E4 | 5.2E1 | 5.5E2 | 2.5E4 | 5.3E4 | 306 | 7 | 190 | 7 | 0.65 |
| oN | pg/ml | 5.1E2 | 5.8E2 | 7.2E2 | 1.2E3 | 1.2E3 | 1.7E3 | 1.1E2 | 2.8E2 | 1.8E4 | 5.0E3 | 306 | 7 | 190 | 7 | 0.57 |
| pF | pg/ml | 4.9E-1 | 9.3E-1 | 9.9E-1 | 2.1E0 | 5.0E0 | 3.5E0 | 1.0E-9 | 2.0E-1 | 8.7E1 | 1.0E1 | 306 | 7 | 190 | 7 | 0.66 |

Analyte panel data:

Unconstrained panels with 3 analytes, where 1.0E-9 >= 'model p-value' > 0. Contains 247 panels of 7,710,078 total panels evaluated. : Lv{aA(Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jj(Fr Hu Hv Hw Hx Ih Ij Il Is Jg Jk Jl Jp Lh Li Lx Ma Mg Mi Mk Mp Mr Mt Mu Mv My Mz Nb Nn Nq Nr Nu Nv Og Ok On Oy Pa Pb Pc Pe Pg Po Qa Qe) Il(Fr Hv Hx Jl Jo Lu Lx Mi My Mz Nn Nx Of Og Ok On Pa Pb) Mi(Hq Jo Js Md Ms Of Og Om Pg) On(Jo Jt Nx Of Og) Fr(Jo Of Og) Og(Hu Ok) JqOk} Mi{Hq(Fp Hu Hv Iq Jj Jt Lu Ly Mb Mf Mg Ms Nj Oe Of Og Om Pb) Jj(Hu Ik Iq Ly Md Ms Nj Om Pb) Mb(Js Md Of Pg) Ly(Md Of) Hu(Of Og) JqOk NxOn} Ou{Ur(Io Jv Qn) QvaF} Jj{FrLy HuJl} Nx{On(Oe Og)}

Unconstrained panels with 3 analytes, where 1.0E-8 >= 'model p-value' > 1.0E-9. Contains 728 panels of 7,710,078 total panels evaluated. : Mi(Lv(Fp Fr Hu Hv Hw Hx Ih Ii Ij Ik Im In Io Ip Iq It Iu Iv Jg Jh Ji Jl Jm Jn Jp Jq Jr Jt Lh Li Lj Lu Lw Lx Ly Lz Ma Mb Mc Me Mf Mg Mh Mj Mk Ml Mm Mn Mp Mq Mr Mt Mu Mv Mx My Mz Na Nb Nc Ne Nf Ng Nh Ni Nk Nl Nm Nn Nr Ns Nt Nu Nw Nx Ny Oe Oh Oi Ok On Oy Oz Pa Pb Pc Pd Pe Pf Po Pz Qc Qd Qe) Hq(Fr Hr Hw Hx Ih Ii Ij Ik Im In Io Ir Is Iu Iv Jg Jh Ji Jk Jl Jn Jo Jp Jq Jr Js Lh Li Lj Lw Lx Lz Ma Mc Md Me Mh Mk Ml Mm Mn Mp Mq Mr Mt Mu Mv Mx My Mz Na Nb Nc Nd Ne Nf Ng Ni Nk Nl Nm Nn No Nq Ns Nt Nu Nw Nx Ny On Oy Oz

Figure 15 Continued

Pa Pc Pd Pe Pg Po Pz Qa Qb Qc Qd Qe) Jj(Fp Fr Hv Hw Hx Ih Ii Ij Im In Iv Jg Jk Jl Jn Jp Jq Jr Js Jt Lh Li Lu Lx Mb Mc Me Mf Mg Mh Mj Mk Ml Mp Mr Mt Mu Mv Mx My Mz Nb Nc Nd Ne Nf Ni Nk Nn Nt Nu Ny Oe Of Og Ok On Oy Pa Pc Pg Qc Qe) Ms(Fr Hu Iq Jg Jp Js Ly Md Mu Mv My Mz Ni Nk Nn Of Og Ok Om On Pc Pg) Md(Fp Hu Hv Ik Io Iq Jo Jr Jt Mf Ml Mu Ni Nj Nn Oe Of Og Om) Js(Fp Hu Hv Hx Iq Iv Jn Jp Lh Lx Ly Nb Nw Om On Pa Qa Qe) Of(Fp Fr Hv Ik Iq Jo Jr Jt Mf Mu Mv My Ni Nj Nn Og Om On) Iq(aA Fr Hu Hv Hx Jg Jo Jp My Og Ok Om On Pg) Og(Fp Ik Jg Ly Mb Mu Nn Ok Om On Pb Pg) Om(aA Fr Hu Hx Jg Jp Mu Nn On Pg) Jo(Hu Ik Lh Ly Mu My On Pb) Mb(Fr Hx Ml Ny On Pb) Jt(Hu Jp Ok On) Pg(Fp Hu Hv Ly) On(Ii Oe) NcNi} Lv{Il(Et Fp Hq Hr Hu Hw Ih Ii Ij Ik Im In Io Ip Iq Ir Is It Iu Iv Jg Jh Ji Jk Jm Jn Jp Jq Jr Js Jt Lh Li Lj Lw Ly Lz Ma Mb Mc Md Me Mf Mg Mh Mj Mk Ml Mm Mn Mp Mq Mr Ms Mt Mu Mv Mw Mx Na Nb Nc Nd Ne Nf Ng Nh Ni Nj Nk Nl Nm No Nq Nr Ns Nt Nu Nv Nw Ny Oe Oh Oi Om Oy Oz Pc Pd Pe Pf Pg Po Pz Qa Qb Qc Qd Qe) Jj(Et Fp Hq Hr Ii Ik Im In Io Ip Iq Ir It Iu Iv Jh Ji Jm Jn Jo Jq Jr Js Jt Lj Lu Lw Ly Lz Mb Mc Md Me Mf Mh Mj Ml Mm Mn Mq Ms Mw Mx Na Nc Nd Ne Nf Ng Nh Ni Nj Nk Nl Nm No Ns Nt Nw Nx Ny Oe Of Oh Oi Om Oz Pd Pf Pz Qb Qc Qd) Og(Hv Hw Hx Ij Is Jg Ji Jl Jq Lw Lx Md Mk Mr Mu Mv My Mz Nb Nn No Nr Nw Pa Pb Pc Pe) Fr(Ii Iq Js Jt Md Ms Ng Nx Oi Om) Jo(Hu Jl Lx My Ok) On(Il Md Ms Oe) MyOf} Ou{Ii(aF aW bN cS dK dN Hv Kc Kd Kg Kn Kq Ld Mg Nn On) Qv(aG aH aW aX bC bP cX cZ dK Jv Kc Mu Nn Uf Ur) Ur(Af aG aW Bn CX Hb Jq Ms Rg) aF(Ao Jt Of Uu) Kc(Aa Hb Us) aW(aX cF Io) Ao(Mg Mu) aE(Io Jv) FwbN MuOm HbKd OfbJ} Jj{Fr(Fp Hu Hv Ik Iq Mb Mp Ms Nc Nj Nu Of Og Om Pb) Hu(aA Lx Mp My Nn Nu Ok On Pa Qa Qe) On(Jt Ly Mb Nj Nx Oe Of Og Om) Ik(Jl Og) LyJl NjaA} On{Nx(Iq Jt Ly Mb Ms Nj Of Om) Og(aA Hu Iq Jt Mb Md Ms Of) Jt(Ii Md Ms Of Om) Of(Ii Jq Ms) HuIi OeaA} gL{cX(Qv Us) AfUr} Mu{MdHu OmbA}

Unconstrained panels with 3 analytes, where 1.0E-7 >= 'model p-value' > 1.0E-8. Contains 2,608 panels of 7,710,078 total panels evaluated. :
Mi{Iq(Et Fp Hr Hw Ih Ii Ij Ik Im In Io Ip Ir Is It Iu Iv Jh Ji Jk Jl Jm Jn Jq Jr Jt Lh Li Lj Lu Lw Lx Ly Lz Ma Mb Mc Me Mf Mg Mh Mj Mk Ml Mm Mn Mp Mq Mr Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Oh Oi Oy Oz Pa Pb Pc Pd Pe Pf Po Pz Qa Qb Qc Qd Qe) Og(aA Et Fr Hr Hv Hw Hx Ih Ii Ij Im In Io Ip Ir Is It Iu Iv Jh Ji Jk Jl Jm Jn Jo Jp Jq Jr Js Jt Lh Li Lj Lu Lw Lx Lz Ma Mc Me Mf Mg Mh Mj Mk Ml Mm Mn Mp Mq Mr Mt Mv Mw Mx My Mz Na Nb Nc Nd Ne Nf Ng Nh Ni Nj Nk Nl Nm No Nq Nr Ns Nt Nu Nv Nw Nx Ny Oy Oz Pa Pc Pd Pe Pf Po Pz Qa Qb Qc Qd Qe) Md(aA Et Fr Hr Hw Hx Ih Ii Ij Im In Ip Ir Is It Iu Iv Jg Jh Ji Jk Jl Jm Jn Jp Jq Js Lh Li Lj Lu Lw Lx Lz Ma Mc Me Mg Mh Mj Mk Mm Mn Mp Mq Mr Mt Mv Mw Mx My Mz Na Nb Nc Nd Ne Nf Ng Nh Nk Nl Nm No Nq Nr Ns Nt Nu Nv Nw Nx Ny Oh Oi Ok On Oy Oz Pa Pb Pc Pd Pe Pf Pg Po Pz Qa Qb Qc Qd Qe) Ms(aA Et Fp Hr Hv Hw Hx Ih Ii Ij Ik Im In Io Ip Ir Is It Iu Iv Jh Ji Jk Jl Jm Jn Jo Jq Jr Jt Lh Li Lj Lu Lw Lx Lz Ma Mb Mc Me Mf Mg Mh Mj Mk Ml Mm Mn Mp Mq Mr Mt Mw Mx Na Nb Nc Nd Ne Nf Ng Nh Nj Nl Nm No Nq Nr Ns Nt Nu Nv Nw Nx Ny Oe Oh Oi Oy Oz Pa Pb Pd Pe Pf Po Pz Qa Qb Qc Qd Qe) Of(aA Et Hr Hv Hx Ih Ii Ij Im In Io Ip Ir Is It Iu Iv Jg Jh Ji Jk Jl Jm Jn Jp Jq Js Lh Li Lj Lu Lw Lx Lz Ma Mc Me Mg Mh Mj Mk Ml Mm Mn Mp Mq Mr Mt Mv Mw Mx My Mz Na Nb Nc Nd Ne Nf Ng Nh Nk Nl Nm No Nq Nr Ns Nt Nu Nv Nw Nx Ny Oe Oh Oi Ok Oy Oz Pa Pb Pc Pd Pe Pf Pg Po Pz Qa Qb Qc Qd Qe) Om(Et Fp Hv Hw Ih Ii Ij Ik Im In Io Ip Ir Is It Iu Iv Jh Ji Jk Jl Jm Jn Jo Jq Jr Jt Lh Li Lj Lu Lw Lx Ly Ma Mb Mc Me Mf Mg Mj Mk Ml Mm Mn Mp Mq Mr Mt Mv Mw Mx My Mz Nb Nc Ne Nf Nh Ni Nj Nk Nl No Nq Nr Ns Nu Nv Nw Nx Ny Oi Ok Oy Oz Pa Pb Pc Pd Pe Pf Po Qa Qb Qc Qd Qe) Js(aA Fr Hr Hw Ih Ii Ij Ik Im In Ip Ir Is It Jg Jh Ji Jl Jm Jo Jq Jr Jt Li Lj Lu Lz Ma Me Mf Mg Mh Mj Mk Ml Mn Mp Mr Mt Mu Mv Mx My Mz Nc Nd Ne Nf Ni Nj Nk Nn No Nr Ns Nt Nu Oe Ok Oy Oz Pb Pc Pd Pe Pf Pg Po Qb Qd) Hu(aA Fp Fr Hv Hw Hx Ih Ii Iu Iv Jg Ji Jk Jl Jm Jn Jp Jq Jr Li Lu Lw Ly Mb Mc Mg Mj Mk Ml Mm Mp Mt Mu My Mz Na Nc Ne Ng Ni Nj Nk Nl Nm Nn Nr Ns Nx Ny Oe Oi Ok On Oy Oz Pb Pc Pd Po Qc) Jo(Fp Fr Hv Hw Hx Ih Ii Ij Im Ip Is Iv Jg Jh Ji Jj Jl Jp Li Lu Lx Mb Me Mf Mg Mk Ml Mr Mt Mv Mz Nb Nc Nd Ne Ni Nj Nk Nn Nr Nt Nu Nw Ny Ok Oy Pa Pc Pe Pg Qe) Pg(Fr Hr Hw Hx Ii Ik Io Ir Iv Jl Jn Jp Jq Jr Jt Lh Li Lj Lu Lx Mf Mg Ml Mn Mp Mt Mu Mv My Mz Nc Nd Nf Ni Nj Nk Nn Nu Nx Oe Pb Pc Pe Qa Qd Qe) Jj(aA Et Hr Io Ip Ir Is It Iu Jh Ji Jm Lj Lw Lz Ma Mm Mn Mq Mw Na Ng Nh Nl Nm No Nq Nr Ns Nv Nw Nx Oh Oi Oz Pd Pe Pf Po Pz Qa Qb Qd Wm) Ly(aA Fr Hv Hx Ii Iu Iv Jg Ji Jm Jp Jq Jt Lu Lx Mb Mj Ml Mu Mv My Mz Na Nc Ne Ng Ni Nk Nl Nn Nw Nx Oe Oi Ok On Pc Pd) Jt(aA Et Fp Fr Hv Hw Hx Ik Ip Is Iv Jg Jh Ji Jl Lh Li Lx Mb Mk Mr Mt Mu Mv My Mz Ni Nn Nr Nu Nw Pa Pb Pc Qd Qe) Mb(aA Hv Ii Jg Ji Jl Jp Jq Jr Lu Lw Lx Mc Mh Mj Mk Mt Mu My Mz Nb Ne Nf Ni Nn Nw Oe Oi Ok Oy Pa Pc Po) Ni(aA Fp Fr Hv Hw Hx Ik Iv Jg Jl Jp Lu Mu Nj Nk Nn Ok On Pb Pc) On(Hr Hv Hw Jq Jr Lu Mf Mj Mn Mp Nc Nj Nl Nv Ny) Hq(aA Et Ip It Jm Mj Mw Nh Nr Nv Oh Oi Ok Pf) Lv(Et Hr Ir Is Jk Mw Nd Nj No Nq Nv Qa Qb) Jq(aA Fp Fr Ik Jg Ji Jp Mu Nw) aA(Fp Mf Ml Nj Nn Oe Pb Pc) Fr(Fp Mp Nc Nj Nx Ny Oe) Pf(Hx Ml My Nf Ny Pb) Nn(Mp Nj Oe Ok Oy) Jp(Mm Mp Nm Ny Pz) Pd(Hx Ml Nf Ny Pb) Lz(Hx Ml Ny Pb) Mn(Hx Ml Ny Pb) Nj(Mu Ne Nk Ok) Nx(Jg Ji Nw Ok) Ii(Hv Mu Ou) Mp(Mu My) Nc(Ne Nk) PoFp LuOk QvOu} Ou{Ii(aA aD aE Af aG aJ Ap aQ aU AX bA BC bG bJ Bn bO bP bS bU bZ cA cD cF cI CO cP cR Cs CT cU cW CX De dM Ef Ez Fa Fb Fn Fp Fr GL Gp Hb Hc Hf Hu Hx Ih Im In Io Is Jh Jn Jp Jr Jv Ki Kk Ko Li Lv Lx Ma Mj Ml Mn Mp Mq Ms Mt Mu Mv My Mz Nb Ng Nj Nk Nl Nq Oa Of Og Oh Ok Om Pe Ph Pi Qa Qc Qd Qe Qn Qv Qy Qz Rf Rh Rm Tn Uf Uk Uo Up Ur Us Ut Uu Vv Wm) Qv(aA aD aE Af al aJ aL aN AO aQ aU aV aZ bB bE bF bG bH bJ bM BN bQ bS bV bW bX bZ cA cC cE cF cG cH cl cM cN cP cQ cS cV cW Cx dB dC dF dH Di dJ dM dN dR Ez Fw gL Hb Im Io Jj Jq Kd Kg Ki Kk Ko Kq Lv Md Mg Mj Ms Mx Nc Ne Nh Nl Oe Of Om Qn Qy Ug Uk Uo Up Us Uu Vo Vp Vv) Ur(Aa aE aF aH Ao Ar aX bC bN bU cl cP cS cW dK Dl dN Fw Hv Ij In Iq Iz Jt Kc Kd Ke Kg Kk Kl Kr Ky Lu Lv Lz Mj Mn Mp Mu Mx Ng Nm Nn No Nw Oe Of Og Om Po Qb Qg Qm Qx Rb Rf Rh Rm Tz Uf Ug Uh Uo Up Us Uu Vv Wm) aW(Aa AF aG aH Ao bJ BN cD Cq cR cS CX Hb Jj Jo Jq Jt Ju Jv Kf Lh Mj Mn Mp Mu Ni Nm Nn Oe Of Og Om Pg Qn Up Us Uu Vo) aF(Aa aE Af aG aS aX cP cS Dl Hb Ij Io Iz Jg Jj Jo Jq Jv Kl Kr Lu Mg Ng Nm Og Om Pg Pz Qn Vo) Kc(aE Af aG Ao Cq Dg dH Dk Fw Ha Hr Jj Jo Jq Kf Kr Ks Lh Mj Nl No Of Pg Tv Up Vs Tj) Of(aE aX bN cF cS cZ dK gL Hb Hc Io Jh Kd Kg Mg Mj Mu Nn Qy Uf) Ao(aE aX cS De Ef gL Kd Kg Kq Mv Nn Qy Uf) Us(aX bV cl cS cX dK dN Fw Io Jv Kd Kk) Kd(Aa Iz Jj Jo Jq Jt Kl Mj Pg Up) aX(aE Af cE cX Hb Io Jj Jq Mj Om) bN(Aj Iz Jj Jo Jt Jv Kl Ug Vo) dK(Af aG cP Jj Jq Jv Mp Om Pg) cX(aE cF cS Dp gL Jv Pg Up) Io(cF cS Dp Hr Jj Mj Up) Fw(Aa aE cA Mj Nl Up) Mu(cE Jo Jq Mp Uc) Nn(Jo Jq Mp Pg) Jv(bG Jj Mj Up) aE(bS Jj Jq Mj) gL(Af Iz Kl Uu) Mg(Jo Jq Jt) Up(cl dN Uu) cS(fP Jj Om) cF(Af Qn) MacE MjKk MpUf MyUu UcKq JqKg PgdN} Lv{Fr(Et Fp Hq Hr Hu Hv Hw Hx Ih Ij Ik Im In Io Ip Ir Is It Iu Iv Jg Jh Ji Jk Jl Jm Jn Jp Jq Jr Li Lj Lu Lw Lx Ly Ma Mb Mc Me Mf Mg Mh Mj Mk Ml Mm Mn Mp Mq Mr Mt Mu Mv Mw Mx My Mz Na Nb Nc Nd Ne Nf Nh Ni Nj Nk Nm Nn No Nq Nr Ns Nu Nv Nw Ny Oe Oh Oi Om Oy Oz Pa Pb Pc Pd Pe Pf Pg Po Pz Qa Qb Qc Qd Qe) Og(Et Fp Hq Hr Ih Ii Ik Im In Io Ip Iq Ir It Iu Iv Jh Jk Jm Jn Jo Jp Jr Js Jt Lh Li Lj Lu Lv Lz Ma Mb Mc Me Mf Mg Mh Mj Ml Mm Mn Mp Mq Ms Mt Mw Mx Na Nc Nd Ne Nf Ng Nh Ni Nj Nk Nl Nm Nq Ns Nt Nu Nv Nx Ny Oe Of Oh Oi Om Oy Oz Pd Pf Pg Po Pz Qa Qb Qc Qd Qe) On(Fp Hq Hr Hu Hv Hw Hx Im Io Iq Iu Jl Jm Jp Jq Jr Js Lj Lu Lx Ly Lz Ma Mb Me Mg Mm Mn Mp Mu Mv Mw My Mz Na Nb Nc Ne Nf Ng Nh Ni Nl Nm Ns Nt Nu Nv Ny Oi Om Oy Pb Pd Pg Po Pz Qa Qc) Jo(Hv Hw Hx Jg Ji Jp Lh Ma Mk Mr Mu Mv Mz Nv Nw Pa Pe Qa Qe) Ok(Hu Hv Hx Ii Iu Jl Jp Jt Lu Md Ms Mu Mv My Mz Nn Nx Of Om) Js(Hv Hw Hx Iv Jl Lx Mj Mk Mr Mz Nr Pa Pb Pe) Of(Hu Hx Jg Ji Jl Jp Lx Ma Mu Mv Mz Nw) Hu(Hv Ii Jq Jt Lu Ms Ng Nn Nx Om) Nx(Hx Ji Jl Lx Mu My Mz Nw) Md(Hx Jg Lx Mp Nd Nw Pc) My(Jl Lx Ms Mz Ng) Jl(Ii Jt Om) Ms(Mu Nw) Nd(Hq Oz) Ng(Jg Mv) Ji(Jq Lu) Om(Mu Mz) HxIi JpJt OePa} Jj{Fr(Et Hq Hr Hw Hx Ih Ii Ij Im In Io Ip Ir Is It Iu Iv Jg Jh Ji Jk Jl Jm Jn Jo Jp Jq Jr Js Jt Lh Li Lj

Figure 15 Continued

Lu Lw Lx Lz Ma Mc Md Me Mf Mg Mh Mj Mk Ml Mm Mn Mq Mr Mt Mu Mv Mw Mx My Mz Na Nb Nd Ne Nf Ng Nh Ni Nk Nl Nm Nn No Nq Nr Ns Nt Nv Nw Nx Ny Oe Oh Oi Ok On Oy Oz Pa Pc Pd Pe Pf Pg Po Pz Qa Qb Qc Qd Qe) Hu(Fp Hv Hw Hx Ih Ii Ij Ik Im Ip Ir Is Iv Jg Ji Jk Jn Jo Jp Jr Jt Lh Li Lj Lw Ly Ma Mf Mg Mj Mk Mm Mr Ms Mt Mu Mv Mx Mz Nb Nc Nj No Nr Nt Nv Nw Og Om Oy Pb Pc Pe Pg Po Qb Qd Wm) On(aA Fp Hr Hv Ih Ii Ik Iq Iv Jl Jp Jq Js Lh Li Lu Lx Ma Md Me Mf Mg Mm Mp Ms Mt Mu Mv My Mz Nc Nd Ni Nn Nu Nv Ny Pa Pb Pe Pg Qa Qd Qe) Ik(aA Hv Hw Hx Jp Lh Lx Mk Mp Mr Mu My Mz Nn Nr Nu Pa Pe Qe) Nu(aA Hv Hw Hx Jl Lh Lx Mu Mv My Pa Pb Pe) My(aA Fp Hv Jl Lh Lx Mb Mp Nj Pb Pe Qe) Mu(Af Hw Lx Ly Mb Mp Nj Ok Om Pa) aA(Fp Ly Mb Mf Mg Nn Og Pb Pe) Jl(Mb Mg Ms Nj Og Ok Om Pb) Ly(Jg Lh Mv Pe Qe) Og(Ij Lh Lx Nt Ok) Om(Jk Lh Pe Qe) Wm(Hv Jp Mg) Nn(Hv Ok Pe) Nj(Hx Lh Lx) AfMv LxMb} On{Nx(aA Fp Fr Hr Hu Hv Hw Hx Ii Ik In Io Ir Is Iv Ji Jl Jo Jp Jq Jr Js Lh Li Lu Lw Lx Lz Ma Md Mf Mg Ml Mp Mt Mu Mv My Mz Nb Nc Nd Nf Ng Ni Nk Nn Ns Nu Nw Ny Oy Pb Pe Pg Qa Qd Qe) Og(Fp Fr Hq Hr Hv Hw Hx Ii Ik Im Io Is Iv Jl Jo Jp Jq Jr Js Lj Lu Lx Ly Ma Mf Mg Ml Mt Mu Mv My Mz Na Nb Nc Nd Nf Ni Nj Nk Nn Nu Nv Ny Oe Om Oy Pb Pg Qa Qd Qe) Oe(Fr Hq Hr Hu Hv Iq Jl Jo Jt Lx Mb Md Ms Mu Mv My Mz Nn Of Om Qa) Of(aA Fr Hu Iq Jo Js Lu Ly Ma Mb Md Mm Mu Mv My Ni Nj Nn Om Qc) Jt(aA Fp Fr Hu Hw Iq Iv Jp Li Lx Ly Mb Mz Nj Ns Nu Ok Qa) Ii(aA Fr Hv Jl Lx Ly Mb Ms My Nj Om Pa) aA(Iq Ly Mb Ms Nj Om) Ms(Hr Hu Nn Om) Jo(Hu Mb Om) Md(Jq Mb)} aA{Og(aF Fp Hu Ik Ji Jq Lw Ly Mb Mg Nj Nn Nw Ok Pb) cX(aC aW bA bM cF cP cS cT dB dE dH dN) Ok(Iq Jq Jt Ly Mb Ms Nj Of Om) Qm(Fr Ji Lx Nw Pe) dH(bA bZ cU dN) Nw(Iq Ms Nj) Ji(Iq Nj) cP(aF dB) AfMg NgHu bAcV bJcT} bA{cX(aJ aS aW bE cE cF dB dE dN) bJ(aF aW bP cE dB) cP(AF aJ aS dB) Mu(Af cE Ii Jq) dN(aF cE cV dH) dE(aF cF cV) Mg(Jo Jt) aJ(dG dH) AfDe aWcF cScV} gL{cX(Ao Ef Hb Ii Iz Jo Kl Kr Ks Of Uu Vo Vv) Cx(aE aW bN cI dH Qv Us Uu) Af(Kc Qv) HbUr} Og{Ok(Fr Hu Hv Iq Jl Jt Mb Mu Mv Nn Pb) Fr(Hv Iq Ji Ly Mb Ms Of Om) Ji(Hu Hv Nn) MdOm} Fr{Of(Hv Ly Mb Ms Ok) Ly(Jo Ng) Ii(Hv Wm) MbNg JtOk} cT{Af(bC bJ cP Mu) aJ(cP cX dH) MgJo MuOm} Kc{My(Af Ao Hb Ii Jt Kj Of) HbUr} Kk{MgJo UscS} cP{AfMu aJdL} JpJtOk

Unconstrained panels with 3 analytes, where 1.0E-6 >= 'model p-value' > 1.0E-7. Contains 12,024 panels of 7,710,078 total panels evaluated. : Mi{Ik(aA Et Fp Fr Hr Hu Hv Hw Hx Ih Ii Ij Im In Io Ip Ir Is It Iu Iv Jg Jh Ji Jk Jl Jm Jn Jp Jr Lh Li Lj Lu Lw Lx Ly Lz Ma Mb Mc Me Mf Mg Mh Mj Mk Ml Mm Mn Mp Mq Mr Mt Mu Mv Mw Mx My Mz Na Nb Nc Nd Ne Nf Ng Nh Nj Nk Nl Nm Nn No Nq Nr Ns Nt Nu Nv Nw Nx Ny Oe Oh Oi Ok On Oy Oz Pa Pb Pc Pd Pe Pf Po Pz Qa Qb Qc Qd Qe) Lu(aA Et Fp Fr Hr Hv Hw Hx Ih Ii Ij Im In Io Ip Ir Is It Iu Iv Jg Jh Ji Jk Jl Jm Jn Jp Jq Jr Jt Lh Li Lj Lw Lx Lz Ma Mc Me Mf Mg Mh Mj Mk Ml Mm Mn Mp Mq Mr Mt Mu Mv Mw Mx My Mz Na Nb Nc Nd Ne Nf Ng Nh Nj Nk Nl Nm Nn No Nq Nr Ns Nt Nu Nv Nw Nx Ny Oe Oh Oi Oy Oz Pa Pb Pc Pd Pe Pf Po Pz Qa Qb Qc Qd Qe) My(aA Et Fp Fr Hr Hv Hw Hx Ih Ii Ij Im In Io Ip Ir Is It Iu Iv Jg Jh Ji Jk Jl Jm Jn Jp Jq Jr Lh Li Lj Lw Lx Lz Ma Mc Me Mf Mg Mh Mj Mk Ml Mm Mn Mq Mr Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Oh Oi Ok On Oy Oz Pa Pb Pc Pd Pe Po Pz Qa Qb Qc Qd Qe) Jg(aA Et Fp Fr Hr Hv Hw Hx Ih Ii Ij Im In Io Ip Ir Is It Iu Iv Jh Ji Jk Jl Jm Jn Jp Jr Lh Li Lj Lw Lx Lz Ma Mc Me Mf Mg Mh Mj Mk Ml Mm Mn Mp Mq Mr Mt Mu Mv Mw Mx Mz Na Nb Nc Nd Ne Nf Ng Nh Nj Nk Nl Nm Nn No Nq Nr Ns Nt Nu Nv Nw Ny Oe Oh Oi Ok On Oy Oz Pa Pb Pc Pd Pe Pf Pg Po Pz Qa Qb Qc Qd Qe) Pc(Et Fp Fr Hr Hv Hw Hx Ih Ii Ij Im In Io Ip Ir Is It Iu Iv Jh Ji Jk Jl Jm Jn Jp Jq Jr Lh Li Lj Lw Lx Lz Ma Mc Me Mf Mg Mh Mj Mk Ml Mm Mn Mp Mq Mr Mt Mu Mv Mw Mx Mz Na Nb Nc Nd Ne Nf Ng Nh Nj Nk Nl Nm Nn No Nq Nr Ns Nt Nu Nv Nw Nx Ny Oe Oh Oi Ok On Oy Oz Pa Pb Pd Pe Pf Po Pz Qa Qb Qc Qd Qe) Fp(Et Hr Hv Hw Hx Ih Ii Ij Im In Io Ip Ir Is It Iu Iv Jh Ji Jk Jl Jm Jn Jp Jr Lh Li Lj Lw Lx Ly Lz Ma Mb Mc Me Mf Mg Mh Mj Mk Ml Mm Mn Mp Mq Mr Mt Mu Mv Mw Mx Mz Na Nb Nc Nd Ne Nf Ng Nh Nj Nk Nl Nm Nn No Nq Nr Ns Nt Nu Nv Nw Nx Ny Oe Oh Oi Ok On Oy Oz Pa Pb Pd Pe Pf Pz Qa Qb Qc Qd Qe) Nc(aA Et Hr Hv Hw Hx Ih Ii Ij Im In Io Ip Ir Is It Iu Iv Jh Ji Jk Jl Jm Jn Jp Jq Jr Lh Li Lj Lw Lx Lz Ma Mb Mc Me Mf Mg Mh Mj Mk Ml Mm Mn Mp Mq Mr Mt Mu Mv Mw Mx Mz Na Nb Nd Ne Nf Ng Nh Nj Nl Nm Nn No Nq Nr Ns Nt Nu Nv Nw Nx Ny Oe Oh Oi Ok On Oy Oz Pa Pb Pd Pe Pf Po Pz Qa Qb Qc Qd Qe) Hv(aA Et Fr Hr Hw Hx Ih Ij Im In Io Ip Ir Is It Iu Iv Jh Ji Jk Jl Jm Jn Jp Jq Jr Lh Li Lj Lw Lx Lz Ma Mc Me Mf Mg Mh Mj Mk Ml Mm Mn Mp Mq Mr Mt Mu Mv Mw Mx Mz Na Nb Nd Ne Nf Ng Nh Nj Nk Nl Nm Nn No Nq Nr Ns Nt Nu Nv Nw Nx Ny Oe Oh Oi Ok Oy Oz Pa Pb Pd Pe Pf Po Pz Qa Qb Qc Qd Qe) Ok(aA Et Fr Hr Hw Hx Ih Ii Ij Im In Io Ip Ir Is It Iu Iv Jh Ji Jk Jl Jm Jn Jp Jr Lh Li Lj Lw Lx Lz Ma Mc Me Mf Mg Mh Mj Mk Ml Mm Mn Mp Mq Mr Mt Mu Mv Mw Mx Mz Na Nb Nd Ne Nf Ng Nh Nk Nl Nm No Nq Nr Ns Nt Nu Nv Nw Ny Oe Oh Oi On Oy Oz Pa Pb Pd Pe Pf Pg Po Pz Qa Qb Qc Qd Qe) Pb(Et Fr Hr Hw Hx Ih Ii Ij Il Im In Io Ip Ir Is It Iu Iv Jh Ji Jk Ji Jm Jn Jp Jq Jr Lh Li Lj Lw Lx Ly Ma Mc Me Mf Mg Mh Mj Mk Ml Mm Mp Mq Mr Mt Mu Mv Mw Mx Mz Na Nb Nd Ne Nf Ng Nh Nj Nk Nl Nm No Nq Nr Ns Nt Nu Nv Nw Nx Ny Oe Oh Oi On Oy Oz Pa Pe Po Pz Qa Qb Qc Qd Qe) aA(Et Fr Hr Hw Hx Ih Ii Ij Il Im In Io Ip Ir Is It Iu Iv Jh Ji Jk Jl Jm Jn Jo Jp Jr Lh Li Lj Lw Lx Lz Ma Mc Me Mg Mh Mj Mk Mm Mn Mp Mq Mr Mt Mu Mv Mw Mx Mz Na Nb Nd Ne Nf Ng Nh Nk Nl Nm No Nq Nr Ns Nt Nu Nv Nw Nx Ny Oh Oi On Oy Oz Pa Pd Pe Pf Pg Po Pz Qa Qb Qc Qd Qe) Nj(Et Hr Hw Hx Ih Ii Ij Im In Io Ip Ir Is It Iu Iv Jh Ji Jk Jl Jm Jn Jp Jq Jr Jt Lh Li Lj Lw Lx Ly Lz Ma Mc Me Mf Mg Mh Mj Mk Ml Mm Mn Mp Mq Mr Mt Mv Mw Mx Mz Na Nb Nd Nf Ng Nh Nl Nm No Nq Nr Ns Nt Nu Nv Nw Nx Ny Oe Oh Oi Oy Oz Pa Pd Pe Pf Po Pz Qa Qb Qc Qd Qe) Nn(Et Fr Hr Hw Hx Ih Ii Ij Im In Io Ip Ir Is It Iu Iv Jh Ji Jk Jl Jm Jn Jp Jq Jr Lh Li Lj Lw Lx Lz Ma Mc Me Mf Mg Mh Mj Mk Ml Mm Mn Mq Mr Mt Mu Mv Mw Mx Mz Na Nb Nd Ne Nf Ng Nh Nk Nl Nm No Nq Nr Ns Nt Nu Nv Nw Nx Ny Oh Oi On Oz Pa Pd Pe Pf Po Pz Qa Qb Qc Qd Qe) Mu(Et Fr Hr Hw Hx Ih Ij Im In Io Ip Ir Is It Iu Iv Jh Ji Jk Jl Jm Jn Jp Jr Lh Li Lj Lw Lx Lz Ma Mc Me Mf Mg Mh Mj Mk Ml Mm Mn Mq Mr Mt Mv Mw Mx Mz Na Nb Nd Ne Nf Ng Nh Nk Nl Nm No Nq Nr Ns Nt Nu Nv Nw Nx Ny Oe Oh Oi On Oy Oz Pa Pd Pe Pf Po Pz Qa Qb Qc Qd Qe) Jq(Et Hr Hw Hx Ih Ii Ij Im In Io Ip Ir Is It Iu Iv Jh Jk Jl Jm Jn Jo Jr Jt Lh Li Lj Lw Lx Lz Ma Mc Me Mf Mg Mh Mj Mk Ml Mm Mn Mp Mq Mr Mt Mv Mw Mx Mz Na Nb Nd Ne Nf Ng Nh Ni Nk Nl Nm No Nq Nr Ns Nt Nu Nv Nx Ny Oe Oh Oi Oy Oz Pa Pd Pe Pf Po Pz Qa Qb Qc Qd Qe) Fr(Et Hr Hw Hx Ih Ii Ij Im In Io Ip Ir Is It Iu Iv Jh Ji Jk Jl Jm Jn Jp Jr Lh Li Lj Lw Lx Lz Ma Mc Me Mf Mg Mh Mj Mk Ml Mm Mn Mq Mr Mt Mv Mw Mx Mz Na Nb Nd Ne Nf Ng Nh Nk Nl Nm No Nq Nr Ns Nt Nu Nv Nw Oh Oi On Oy Oz Pa Pd Pe Pf Po Pz Qa Qb Qc Qd Qe) Jp(Et Hr Hw Hx Ih Ii Ij Im In Io Ip Ir Is It Iu Iv Jh Ji Jk Jl Jm Jn Jr Lh Li Lj Lw Lx Lz Ma Mc Me Mf Mg Mh Mj Mk Ml Mn Mq Mr Mt Mv Mw Mx Mz Na Nb Nd Ne Nf Ng Nh Nk Nl No Nq Nr Ns Nt Nu Nv Nw Nx Oe Oh Oi On Oy Oz Pa Pd Pe Pf Po Qa Qb Qc Qd Qe) Ni(Et Hr Ih Ii Ij Im In Io Ip Ir Is It Iu Jh Ji Jk Jm Jn Jr Lh Li Lj Lw Lx Lz Ma Mc Me Mf Mg Mh Mj Mk Ml Mm Mn Mp Mq Mr Mt Mv Mw Mx Mz Na Nb Nd Ne Nf Ng Nh Nl Nm No Nq Nr Ns Nt Nu Nv Nw Nx Ny Oe Oh Oi Oy Oz Pa Pd Pe Pf Po Pz Qa Qb Qc Qd Qe) Iv(Hw Hx Ih Ii Ij Im In Io Ip Ir Is It Iu Jh Ji Jl Jm Jn Jr Lh Li Lw Lx Lz Ma Mb Mc Me Mf Mg Mh Mj Mk Ml Mm Mn Mp Mq Mr Mt Mv Mx Mz Na Nb Nd Ne Nf Ng Nh Nk Nl Nm Nq Nr Ns Nu Nw Nx Ny Oe Oh Oi On Oy Oz Pa Pd Pe Pf Po Pz Qc Qd Qe) Mz(Hw Hx Ih Ii Ij Im In Io Ip Ir Is Iu Jh Ji Jl Jm Jn Jr Lh Li Lw Lx Lz Ma Mc Me Mf Mg Mh Mj Mk Ml Mm Mn Mp Mq Mr Mt Mv Mw Mx Na Nb Nd Ne Nf Ng Nh Nk Nl Nm No Nq Nr Ns Nu Nw Nx Ny Oe Oh Oi On Oy Oz Pa Pd Pe Pf Po Pz Qc Qe) Hx(Hr Hw Ih Ii Ij Im In Io Ip Ir Iu Jh Ji Jk Jl Jm Jn Jr Lh Li Lj Lw Lx Ma Mc Me Mf Mg Mh Mj Mk Ml Mm Mp Mq Mr Mt Mv Mx Na Nb Nd Ne Nf Ng Nh Nk Nl Nm Nq Nr Ns Nu Nv Nw Nx Ny Oe Oh Oi On Oy Oz Pa Pe Po Pz Qa Qc Qd Qe) On(Et Ih Ij Il Im In Io Ip Ir Is It Iu Jh Ji Jk Jl Jm Jn Lh Li Lj Lw Lx Lz Ma Mc Me Mg Mh Mk Ml Mm Mq Mr Mt Mv Mw Mx Na Nb Nd Ne Nf Ng Nh Nk Nm No Nq Nr Ns Nt Nu Nw Oh Oi Oy Oz Pa Pd Pe Pf Pg Po Pz Qa Qb Qc Qd Qe) Hw(Hr Ih Ii Im In Io Ip Ir Is Iu Jh Ji Jl

Figure 15 Continued

Il Im In Io Ip Ir Is It Iu Jg Jh Ji Jk Jl Jm Jn Jo Jq Jr Js Lh Lj Lu Lw Lz Ma Mc Me Mf Mg Mh Mj Mk Ml Mm Mn Mp Mq Mr Mt Mu Mv Mw Mx My Na Nb Nc Nd Ne Nf Ng Nh Ni Nk Nl Nm Nn No Nq Nr Nt Nv Nw Ny Oh Oi Oy Oz Pa Pb Pc Pd Pe Pf Pg Po Pz Qb Qc Qd Qe) Oe(Et Fp Hw Hx Ih Ij Ik Il Im In Io Ir Is It Iu Iv Jg Jh Ji Jk Jm Jn Jp Jq Jr Js Lh Li Lj Lu Lw Ly Lz Ma Mc Me Mf Mg Mh Mj Mk Ml Mm Mn Mp Mq Mr Mt Mw Mx Na Nb Nc Nd Ne Nf Ng Nh Ni Nj Nk Nl Nm No Nq Nr Ns Nt Nu Nv Nw Ny Oh Oi Ok Oy Oz Pa Pb Pc Pd Pe Pf Pg Po Pz Qb Qc Qd Qe) Of(Et Fp Hq Hr Hv Hw Hx Ih Ij Ik Il Im In Io Ip Ir Is It Iu Iv Jg Jh Ji Jk Jl Jm Jn Jp Jr Lh Li Lj Lw Lx Lz Mc Me Mf Mg Mh Mj Mk Ml Mn Mp Mq Mr Mt Mw Mx Mz Na Nb Nc Nd Ne Nf Ng Nh Nk Nl Nm No Nq Nr Ns Nt Nu Nv Nw Ny Oh Oi Ok Oy Oz Pa Pb Pc Pd Pe Pf Pg Po Pz Qa Qb Qd Qe) Og(Et Ih Ij Il In Ip Ir It Iu Jg Jh Ji Jk Jm Jn Lh Li Lw Lz Mc Me Mh Mj Mk Mm Mn Mp Mq Mr Mw Mx Ne Ng Nh Nl Nm No Nq Nr Ns Nt Nw Oh Oi Ok Oz Pa Pc Pd Pe Pf Po Pz Qb Qc) Ms(Fp Fr Hq Hv Hw Hx Il Io Iq Iv Ji Jl Jo Jp Jq Js Lu Lx Ly Lz Ma Mb Md Mf Mg Ml Mm Mt Mu Mv My Mz Na Nc Nf Ng Ni Nj Nl Nm No Nq Nu Nv Nw Ny Oy Pb Pc Pz Qa Qe) Nx(Et Hq Ih Ij Il Im Ip It Iu Jg Jh Jk Jm Jn Lj Mc Me Mh Mj Mk Mm Mq Mr Mw Mx Na Ne Nh Nl Nm No Nq Nr Nt Nv Oh Oi Ok Oz Pa Pc Pd Pf Po Pz Qb Qc) Jo(Fp Fr Hv Ik Iq Iv Jl Jp Lh Lx Ly Ma Md Mf Mg Ml Mu Mv My Mz Ni Nj Nu Qa Qd Qe) Om(Fr Hr Hu Hv Hx Iq Jl Jp Jq Js Lu Lx Lz Mp Mu My Mz Nb Nu Nv Ny Oy) Iq(Fr Hr Hu Hv Hx Im Ir Jl Jp Lx Ma Md Mv My Mz Oy Qa Qe) Md(Fr Hr Hu Hv Io Js Lu Ly Ni Nj Nn Pb Pc) Jq(My Nb Ng Ok Oy) Nv(Fr Hu Jl Nn) Oy(Fr Hu Nn) Ng(Fr Hu) Hr(Ly Nj) NcNi QaJs} bA{bJ(aC aD aE Af aG aH al aJ aK aL aM aN aO aP aQ aR aS aU aV aX aY aZ bB bC bE bF bG bH bI bL bM bN bO bQ bR bS bU bV bW bX bZ cA cB cC cD cF cG cH cI cJ cK cL cM cN cO cP cQ cR cS cT cU cV cW CX cY cZ dA dC dD dE dF dG dH dI dJ dK dL dM dN) cP(aD aE aG aH aK aL aN aR aU aW aX aY bB bC bE bF bG bI bL bM BN bO bP bQ bR bU bV bW bX cB cC cE cF cG cJ cK cL cR cS cT cU cV CX cY cZ dA dE dF dH dJ dK dM dN) cX(aD aE aF aH aK aL aN aU aX aY bC bF bI bM bN bO bP bQ bR bU bV cC cG cK cN cQ cR cS cT cU cV cW cY cZ dA dH dJ dK dM fR) cF(aD aE AF aG aJ aL aN aS aU aY bE bF bM bN bO bP bQ bW cB cE cG cK cN cO cR cS cU cV cW Cx cY dA dB dH dJ dK dM dN) Af(aD aF aJ aS AW aX aY bC bE bM BO bP bU cE cS cU CV Cx cZ DB dE dH Dk dN Fr Jh Kg Mg Nq Qy) Cx(AD aE aF aH aJ Ao aS aW aX aY bC bE bF Bg bM Bn bO bP bU cE Cq cS Ct CV cZ dB Dc dE dM dN gL) dM(aD aE aF aG aH aJ aL aQ aS aW bE bF bL bN bO bP bQ bR bU cC cE cG cS cV dB dE dG dH dN) dB(aD aF aH aJ aS aU aW bE bF bN bO bP bU bW cB cC cE cG cR cS cU cV cZ dA dE dH dN) dE(aD aH aJ aL aN aS aW bE bF bL bM bN bO bP bQ bR bU cC cE cG cL cS cU dH dN) aJ(aE aF aH aP aS aW bE bF bL bN bO bQ bR bU cC cE cG cS cU cV dF dL dN) aW(aD aF aS aU bC bE bF bN bO bP bU cC cE cR cS cU cV cZ dH dN) aF(aD aE aO aS aU aY bE bO bP cE cR cS cU Cv cZ Jt Og) Mu(Ao Bb Bn De Iq Jk Jo Jt Mp Ny Of Oy Pg Po Uc Us) dN(aH aS bE bF bL bN bO bP bU cG dF dG dI) aS(aD aE bO bP cE cS cU cV dH) bE(aC aD aE bN bP cE cV dH) cS(bO bQ cE cG cL dH Ii Io) Ii(Kq Mg Mv My Nn Nq) cV(aX aY bO bP cR cU) Mg(Ao Jq Of Po) Us(aX Ez My Qy) cE(aD bO bP cU) dH(bP cO cU dA) Nn(Jq Pg) bO(aD bP) HbKc QyOm JqKg bQcO cGcU} Fr{Of(Et Fp Hu Hw Hx Ih Ij Ik Im Ip Iq Ir Is Iv Jg Ji Jl Jo Jp Jq Jr Js Jt Lh Li Lj Lw Lx Ma Md Me Mf Mg Mj Mk Mm Mp Mr Mt Mu Mv Mx My Mz Nb Nc Nd Ng Ni Nj Nk Nn No Nr Ns Nt Nu Nw Oe Oi Om Pa Pb Pc Pe Pg Qa Qb Qd Qe) Og(Fp Hu Hw Hx Ii Ij Ik Ip Ir Is Iv Jl Jo Jq Jr Jt Lh Li Lj Lw Lx Md Me Mf Mk Mp Mq Mr Mx Mz Nb Nc Nd Ng Nj Nk Nn No Nr Nt Nu Nw Ny Pa Pb Pc Pe Qe) Om(Fp Hu Hv Hw Hx Ih Iq Ir Is Iv Ji Jl Jo Jr Lj Lw Lx Ly Mb Md Mk Mp Mr Ms Mx My Mz Nc Ng Nj Nr Ns Nu Nw Oe Oi Ok Pa Pe Qa Qe) Mb(Hu Hv Hw Hx Ii Iq Ji Jl Jo Jt Lw Lx Ly Md Mk Mp Mr Ms Mz Nr Nx Oi Ok Pa Pe) Iq(Fp Hv Hw Hx Ir Is Ji Jo Lw Lx Md Mk Mp Mr Ms Mz Ng No Nr Ok Pa Pe Qa Qe) Ms(Fp Hu Hv Hw Hx Is Ji Jo Lw Lx Ly Md Mp Mz Ng Ni Nu Nw Oe Ok Pa Pc) Jt(Fp Hv Hw Ir Is Iv Ji Jp Lw Lx Ly Mr Mz Nr Nu Pa Pe Qa Qd Qe) Jo(Fp Hv Hw Iv Lx Mp Mr Nj Nr Ok Pa Pe) Oe(Hv Hw Lx Ly Mk Mr Nr Ok Pa Pe) Ng(Hu Hv Hx Ik Nc Nj) Ly(Hu Ii Md Ok) Nx(Ji Nw Ok) Md(Hv Mp) Jq(Ji Ok) Js(Hv Pa) AfcT Mzli} gL{cX(Ad Af Aj Al Ap As Bg Bn Bo Cp Cq Cs Cx Db Dc Dd De Dg Dk Dl Dp Ex Ez Fb Fw Gl Gp Gz Ib Jd Jt Kc Kd Kj Kn Kq Ky Ms Nm Oe Og Om Ow Ph Pi Pj Pk Pz Qw Ra Rh Rj Rm Ss St To Tr Tt Tv Tz Ub Uc Ug Uk Um Up Ur Uv Vs Tj) Cx(aC AD AF aG Aj Ao aP aQ Bg bL Bn Bo bP bQ bS bU bX cA cD cE cF cG cL cP cR cT dB dC dF DG dJ Dk Dl Ef fP Hb Ii Iz Jo Kl Ks Mm Of Og Om Ss Ur Vo Vs Vv) Af(aF aQ aU aW bN cA cI dB De dH fP Ii Jh Kg Kk Kq Ld Mg Mu Oe Ow Ph Qy Ra Rm Uf Uh Us Uu Vo) Ii(cS Hc Kc Ow Qv Ur Us Vv) Qv(aF Kc Ow Qn Vo) Vo(Bn dK Kc Kq) Ao(Kg Kq Mg) JqKc} Og{Ok(Fp Hw Hx Ih Ii Ij Ik Im Ir Is Iv Jg Jh Ji Jk Jo Jp Jq Jr Js Lh Li Lj Lu Lw Lx Ly Ma Md Me Mf Mg Mj Mk Ml Mp Mr Ms Mt My Mz Nb Nc Nd Ni Nj Nk Nq Nr Nt Nu Nw Nx Of Oi Om Oy Pa Pc Pe Pg Po Qa Qc Qd Qe) Ji(Fp Hw Hx Ij Ik Iq Iv Jg Jl Jp Jq Jt Lh Lu Lx Ly Mb Mj Mk Mr Ms Mu Mv My Nc Nj Nr Nu Nx Om Oy Pa Pb Pc Pe) Nw(Hu Hv Ik Js Mb Md Ms Mu Nn Nx Ny) Hu(Jl Lw Lx Mk Mr Nn Nr Pa Pe) Lx(Iq Lz Mb Mu Mv Nn) Mu(Af Mb Pa) Hv(Jg Nn) Jl(Mb Om) MdMp} cT{aJ(aE AF aG aH aP aW bE bF bJ bL bN bO bR bU bX cE cF cG cS cU cV Cx dB dE dG dL dM dN) Af(AW aX bE cF cN cS cU dB DE dM dN Nq Qy) dM(aF bJ bN cE cF cP cS CX dB dE dN) dN(aF bN cE cV cX dE dH) Cx(aW aX bC cP cS dB) dE(aF bJ cF cP cX) Mu(Ao Ii Jo Jq) cS(bJ cX Ii) aW(bJ cF) cP(Bn dB) cXfR} Ok{Jt(Hu Jg Jl Lx Mg Mt Mu Mv My Mz Nn Qa Qe) Nn(Iq Jo Jq Mb Ms Nx Oe Of) Jo(Hu Jl Mu Mv My) Jq(Hu Hv Ji Jl Mu) Of(Hu Jl Mu Mv My) Om(Jl Mu Mv) Ms(Hu My) MbMy} Kc{cP(Af Hb Ii Jo Jt Of Ow Qv Us Vo) My(Dg Dl Iz Jo Qv Us Uu Vo Vs) Qv(Af CX Jv Ow Vp) Af(aQ bN Ur) Hb(Jp Mz) Us(bV cX) CxUr LucX} Ur{Hb(Af cS CX Hv Jp Jr Kd Kg Kk Kq Mg My Or Ow Qd Tn Vu) Af(Jh Kq Mg Mu Mv My Ow) Ow(Jq Qn Qv) cS(cX Io Us) CxQv} aJ{cP(aF aW bN bO bU cF cU cX dB dG dH) dG(bC bN bQ bZ cS cU cX dN) dH(bF bN bQ bZ cO cU dN) dL(bN cS cX dN) bNcX} Qv{aX(cX Kd Kk Or Ow) Af(Jh Kg Kq Mg) cS(cX Io Jv Kk) Ow(Jv Kd Mj) Or(dK Mg)} Mu{cP(Ao Bn De Ii Jo Jq Om) Af(aW Il) AoJp KkOm} Us{My(bV dK Kk) CxKd MgJo StdK JpcS} Kk{cS(bN bX Hb Ii) MyIi} Ms{Ji(Hu My Nn) NnNw} Jo{Mg(Kd Qw Ue) LxHu} Md{LxLz MbNd MpHu} Wm{Jp(Ii Jt)} Kq{Vo(bN Jq)} aX{cP(Af Cx)} IiKdOw JiJlOm Unconstrained panels with 2 analytes, where 1.0E-7 >= 'model p-value' > 0. Contains 36 panels of 66,377 total panels evaluated. : Mi(aA Hq Hu Iq Jj Jo Js Jt Lv Ly Mb Md Ms Ni Nn Of Og Om On Pg) Lv(aA Fr Il Jj Og Ok On) On(Jj Nx Of Og) Ou(Ii Qv Ur) Jj(Fr Hu)

Unconstrained panels with 2 analytes, where 1.0E-6 >= 'model p-value' > 1.0E-7. Contains 185 panels of 66,377 total panels evaluated. : Mi(Et Fp Fr Hr Hv Hw Hx Ih Ii Ij Ik Im In Io Ip Ir Is It Iu Iv Jg Jh Ji Jk Jl Jm Jn Jp Jq Jr Lh Li Lj Lu Lw Lx Lz Ma Mc Me Mf Mg Mh Mj Mk Ml Mm Mn Mp Mq Mr Mt Mu Mv Mw Mx My Mz Na Nb Nc Nd Ne Nf Ng Nh Nj Nk Nl Nm No Nq Nr Ns Nt Nu Nv Nw Nx Ny Oc Oh Oi Ok Oy Oz Pa Pb Pc Pd Pe Pf Po Pz Qa Qb Qc Qd Qe) Jj(aA Ik Jl Lh Lx Mp Mt Mu Mv My Nu Ok Ou Pc Pg Qc Wm) bA(aA AF aJ aS aW bE bJ bO cF cP CX dB dE dM dN) Lv(Hu Hv Hx Ji Jl Jp Lw Lx Mr Mu Mv My Mz Nw Pa Pe) Ou(aE aF Ao aW aX cX Io Jq Jv Of Om Us) aA(aW cP cT cX dH Fp Ji Nw Og Ok On Pb) On(Ii Jt Mb Ms Oc) Fr(Mb Of Og Om) CxgL OgOk aJcT Unconstrained panels with 2 analytes, where 1.0E-5 >= 'model p-value' > 1.0E-6. Contains 425 panels of 66,377 total panels evaluated. : aA(aC aE aF aG aJ aN aO aP aQ aZ bC bE bF bG bJ bL bM bN bO bP bQ bR bU bV bZ cE cF cI cJ cR cS cU cV Cx cZ dB dD dE dG dJ dL dM dN Fr Hu Hv Hx Ik Iq Ir Iv Jg Jn Jp Jq Jr Jt Lh Li Lw Lx Ly Ma Mb Md Mf Mg Ml Mm Mp Mq Ms Mt Mu Mv My Mz Ng Ni Nj Nn Ns Nt Nu Oe Of Om Ou Pa Pc Pe Po Qa Qd Qe) Ou(Aa AD Af aG aH Aj bG bJ BN cD cE cF cI cP Cq cS cW Cx Dc Dg dH DK Dl dN Dp Ef Fw gL Ha Hb Hr Ij In Iq Iz Jk Jo Js Jt Kc Kd Kf Kj Kk Kl Kr Ks Lh Lu Lv Lz Mg Mj Mm Mn Mp Ms Mu Mx Ng Nl Nm Nn No Oe Og Pf Pg Po Pz Qb Qn Rm

Figure 15 Continued

To Uf Ug Uk Up Uu Vo Vp Vv Tj) bA(aC aD aE aG aH aI aK aL aM aN aO aP aQ aR aU aV aX aY aZ bB bC bF bG bH bI bL bM BN bP bQ bR bS bU bV bW bX bZ cA cB cC cD cE cG cH cI cJ cK cL cM cN cO cQ cR cS cT cU cV cW cY cZ dA dC dD dF dG dH dI dJ dK dL) Lv(Et Fp Hq Hw Ih Ii Ij Im Io Ip Iq Ir Is Iu Iv Jg Jh Jk Jn Jo Jq Jr Js Jt Lh Li Lj Lu Ly Ma Md Mf Mg Mj Mk Mm Mn Mp Mq Ms Mt Mw Mx Nb Nc Ne Ng Ni Nk Nn No Nq Nr Nu Nv Nx Oe Of Oi Om Pb Pc Pg Po Qa Qb Qd Qe) Jj(Fp Hv Hw Hx Ih Ij Im Ir Is Iv Jg Ji Jk Jo Jp Li Lw Ly Ma Mg Mk Mr Mz Nb Nj Nn Nr Nt Nv Nw Pa Pb Pc Po Qa Qd) On(Fp Fr Hr Hu Hv Iq Jo Lu Lx Ly Ma Md My Nc Nj Nv Om Oy) Fr(Fp Hv Iq Ji Jo Jt Lw Ly Md Ms Nc Ng Nj Oe Ok) Ok(Hu Hv Iq Jq Jt Lu Mb Nn Of) cT(Af bJ cP CX dE dM dN) Og(Ji Jl Lx Mu Nw) aJ(bN cF cP dG dL) Af(gL Mu Ur) Qv(Kc Ow) Ur(Cx Hb) MiII KccP Unconstrained panels with 2 analytes, where 1.0E-4 >= 'model p-value' > 1.0E-5. Contains 935 panels of 66,377 total panels evaluated. : Ou(aC aI aJ aK AL aM AN aO AP aQ AR AS aU aV Aw Ax aY aZ BA BB BC bE bF Bg bH bI bL bM BO bP bQ bR bS bU bV bW bX bZ cA cB cC cG CH cJ cK cL cM cN CO Cp cQ cR Cs CT CU CV Cw cY cZ dA DB dC DD DE dF dG Dl dJ dL dM dR Ed eF Et Ex Ez Fa Fb Fn FP FR Gl GP Hc Hf Hq Hu Hv Hw Hx Ib Ic Id Ih Ik Il Im Ip Ir Is It Iu Iv Jd Je Jf Jg Jh Ji Jl Jm Jn Jp Jr Ju Jy Ke Kg Ki Kn Ko Kp Kq Kx Ky Kz Ld Li Lj Lw Lx Ly Ma Mb Mc Md Me Mf Mh Mi Mk Ml Mq Mr Mt Mv Mw My Mz Na Nb Nc Nd Ne Nf Nh Ni Nj Nk Nq Nr Ns Nt Nu Nv Nw Nx Ny Oa Oh Oi Ok On Or Ow Oy Oz Pa Pb Pc Pd Pe Ph Pi Pj Pk Qa Qc Qd Qe Qg Qh Ql Qm Qt Qu Qw Qx Qy Qz Ra Rb Rc Rf Rg Rh Ri Rj Sr Ss St Tn Tr Tt Tv Tz Ua Ub Uc Ud Ue Uh Ul Um Un Uo Ut Uv Vs Vt Vu Wm) aA(aD Af aH aI aK aL aM aR aS aU aV aX aY bB bH bI Bn bS bW bX cA cB cC cD cG cH cK cL cM cN cO cQ cW cY dA dC dF dI dK Et Hq Hr Hw Ih Ii Ij Il Im In Io Ip Is It Iu Jh Jk Jl Jm Jo Js Lj Lu Lz Mc Me Mh Mj Mk Mn Mr Mw Mx Na Nb Nc Nd Ne Nf Nh Nk Nl Nm No Nq Nr Nv Nx Ny Oh Oi Oy Oz Pd Pf Pg Pz Qb Qc Us) Fr(Et Hq Hr Hu Hw Hx Ih Ii Ij Ik Im In Io Ip Ir Is It Iu Iv Jg Jh Jk Jl Jm Jn Jp Jq Jr Js Lh Li Lj Lu Lx Lz Ma Mc Me Mf Mg Mh Mj Mk Ml Mm Mn Mp Mq Mr Mt Mu Mv Mw Mx My Mz Na Nb Nd Ne Nf Nh Ni Nk Nl Nm Nn No Nq Nr Ns Nt Nu Nv Nw Nx Ny Oh Oi Oy Oz Pa Pb Pc Pd Pe Pf Pg Po Pz Qa Qb Qc Qd Qe) On(Et Hq Hw Hx Ih Ij Ik Il Im In Io Ip Ir Is It Iu Iv Jg Jh Ji Jk Jl Jm Jn Jp Jq Jr Js Lh Li Lj Lw Lz Mc Me Mf Mg Mh Mj Mk Ml Mm Mn Mp Mq Mr Mt Mu Mv Mw Mx Mz Na Nb Nd Ne Nf Ng Nh Ni Nk Nl Nm Nn No Nq Nr Ns Nt Nu Nw Ny Oh Oi Ok Oz Pa Pb Pc Pd Pe Pf Pg Po Pz Qa Qb Qc Qd Qe) Jj(Af aX bA Bn cF cP cS cT Cx Et gL Hq Ii Il Ip Iu Jh Jm Jn Jq Jr Jt Kc Kd Lj Lu Mb Me Mf Mj Ml Mm Mn Mq Mw Mx Nc Nf Ni Nk Nl Nm No Nq Og Oh Om Ow Oy Pf Pz Qb Qc Us) Ok(Fp Hw Hx Ii Ik Il Ir Is Iv Jg Jl Jo Jp Jr Js Lx Ly Ma Md Mf Mg Ml Mp Ms Mt Mu Mv My Mz Nc Ni Nj Nk Nq Nu Nw Nx Oe Om Pa Pb Pc Pe Pg Qa Qd Qe) aJ(aC aE AF aN aP aW aX aZ bC bF bG bJ bL bO bQ bR bU bV bX bZ cE cO cQ cR cS cU cV CX dB dD dE dH dK dM dN) Lv(bA Hr Ik In It Jm Lz Mb Mc Me Mh Ml Na Nd Nf Nh Nj Nl Nm Ns Nt Ny Oh Oy Oz Pd Pf Pz Qc Qv Ur Us) cT(aD aE aF aN aP aS aW aX aY bC bE bF BN bP bV bW bZ cE cF cN cR cS cU cV cW dA dB) Og(bA Fp Hu Hv Hw Hx Ik Is Iv Jg Jp Kc Lh Lw Mk Mr Mv My Nn Nr Pa Pb Pc Pe Qe Ur) bA(Ad Ao Bo Cq Ct Cv Db Dc De Dg fR Ii Io Jo Jq Jt Mg Mu Nn Oe Of Om Us) Lx(Hq Hu Hv Iq Ji Jo Jp Js Mb Md Ms Mu Mv My Ni Nn Oe Of Om) Ur(Bn cS cX dK gL Hv Ii Io Jq Jv Kc Kd Kk My Ow Qn Qv Us Wm) Ji(Hu Hv Iq Jl Jp Jq Lu Ly Mb Ms Mu Mv My Nn Of Om Pa Pb) Qv(Af aX cS CX dK gL Im Kd Kg Kk Mg Or Uf) dM(aC bG bN bV bZ cF cP cS cU CX dB dE dN) Kc(Aa Af Ao CX Hb Ii Jo Jq My Of Us Vo) Us(bV cS cX gL Jp Kd Kk My Ow St) cP(Af Bn bV bZ cS cU Cx dB fR Mu) gL(aF aW cX Ii Qn Uu Vo) Nw(Js Jt Md Ms Of) Mu(Ao Bn De Of) Mp(Hq Md Pd) Jl(Ms Of Om) Cx(cS fR) Ii(Kd Ow) WmMi LwHu MdOm MgUg NgJg KkcS bNdN cXfR Unconstrained panels with 2 analytes, where 1.0E-3 >= 'model p-value' > 1.0E-4. Contains 2,240 panels of 66,377 total panels evaluated. : Ur(AA AD aE aF aG aH AJ Al An Ao Ap aQ Ar As aV AW AX aY aZ BA Bb BC bE Bg bJ bN Bo bP bS bV bW bX bZ cA cE cF Ch cI Co CP Cq cR Cs CT CU CV CW DB Dc Dd DE Dg Di Dk Dl dM dN Dp dR Ed EF Et Ex Ez Fa Fb Fn Fp Fr Fw Gl Gp Ha Hc Hf Hq Hr Hu Hw Hx Ic Id Ih Ij Ik Il Im In Ip Iq Ir Is It Iu Iv Iz Jd Je Jf Jg Ji Jj Jk Jl Jm Jn Jo Jp Jr Js Jt Ju Jy Ke Kf Kg Ki Kj Kl Kn Ko Kp Kq Kr Ks Kx Ky Kz Ld Lh Li Lj Lu Lw Lx Ly Lz Ma Mb Mc Md Me Mf Mg Mh Mi Mj Ml Mm Mn Mp Mr Ms Mt Mu Mv Mw Mx Mz Na Nb Nc Nd Ne Ng Nh Ni Nj Nk Nl Nm Nn No Nq Nr Ns Nt Nu Nv Nw Nx Ny Oa Oe Of Oh Oi Ok Om Or Oy Pa Pb Pc Pd Pe Pf Pg Ph Pi Pj Pk Po Pz Qa Qb Qc Qd Qe Qg Qh Ql Qm Qu Qw Qx Qy Ra Rb Rc Rf Rg Rh Rj Rm Sr Ss St Tn To Tr Tt Tv Tz Ua Ub Uc Ue Uf Ug Uh Uk Ul Uo Up Ut Uu Uv Vo Vp Vs Vu Vv Tj) Qv(aA aD aE aF aG aH aJ An Ao AP aQ aU aV AW aZ BA bC bE bH bJ bM BN Bo bP bS bV bW bX bZ cA cF Ch cI cN cP cR CT cU cV cW cY cZ DB Dc DE Di dM dN dR EF Fn Fr Fw Gl Ha Hb Hc Hr Hu Hv Hx Ic Ih Ii In Io Ip Iq Is It Je Jf Ji Jj Jn Jo Jp Jq Jr Ju Jv Ki Kj Kn Ko Kp Kq Kx Ky Ld Li Lx Ly Lz Ma Mb Md Me Mf Mi Mj Ml Mm Mn Mp Ms Mv Mx My Mz Ne Ng Ni Nk Nl Nm Nn Nu Nx Oe Of Og Om Pb Pd Ph Pj Qa Qd Qe Qn Qu Qw Qx Qy Ra Rb Rg Rh Rj Sr St Tn To Ua Ub Ug Uh Uk Un Up Us Uu Vo Vp Vu Vv Wm) Kc(aA aC AD aE aF aG AJ Al An aQ aS aV aW AX aY bA Bb BN Bo bP bS bV bX cA cE cF cI Cp CQ cS cT Cv CW cY Dc Dd De Dg dH dI dJ DK Dl dM Dp dR EF Fw gL Ha Hc Hr Hu Hv Hx Id Il In Io Iq Iu Iz Jf Jk Jn Jp Js Jt Jv Kd Kf Kj Kk Kl Kr Ks Ky Kz Lh Lu Lv Ly Lz Md Mj Ml Mm Mp Mr Ms Mx Mz Ni Nk Nl Nm No Nx Ny Oe Oi Om Or Ow Oy Pg Ph Pj Po Pz Qn Rj To Tr Tv Ub Uc Ug Uk Up Uu Vp Vs Vv Tj) bA(Aa Aj Al An Ap Ar As Aw Ax Ba Bb Bc Bg Ch Co Cp Cs Cu Cw Dd Di Dk Dl Et Fr gL Hb Hq Hr Hu Hv Hw Hx Ij Il In Iq Ir iZ Jg Jh Jk Jm Jn Jp Jr Js Jv Kk Lu Ly Lz Ma Mb Md Me Mf Mi Mj Ml Mm Mn Mp Mr Ms Mv Mx My Mz Na Nb Ne Ng Ni Nk Nl Nm No Nq Nr Nt Nv Nw Nx Ny Oh Oy Oz Pa Pb Pc Pd Pe Pf Pg Po Pz Qb Qd Qe Qn Uf Ug Up Uu Vo) Ji(Et Fp Hq Hr Hw Hx Ih Ii Ij Ik Il Im In Io Ip Ir Is It Iu Iv Jg Jh Jk Jm Jn Jo Jr Js Jt Lh Li Lj Lw Lz Ma Mc Md Me Mf Mg Mh Mj Mk Ml Mm Mn Mp Mq Mr Mt Mw Mx Mz Na Nb Nc Nd Ne Nf Ng Nh Ni Nj Nk Nl Nm No Nq Nr Ns Nt Nu Nv Nw Nx Ny Oe Oh Oi Ok Oy Oz Pc Pd Pe Pf Pg Po Pz Qa Qb Qc Qd Qe) Jj(aE aF aJ An Ao aP AW aY Ba bC bE Bg bJ bM bN Bo bP bS bU bV bW bZ cA Ch cI Co Cp Cs Ct CU Cv CW cX cZ DB Dc DE Di DK dM dN Ex Fb Hb Hc Hr In Io Iq It Js Jv Kg Kk Ko Kq Ky Ld Lz Mc Md Mh Ms Na Nd Nc Ng Nh Ns Nx Ny Oe Of Oi Or Oz Pd Qn Qy Rj To Ua Ub Uf Ug Up Vo Vv) Lx(Et Fp Hr Hw Hx Ih Ii Ij Ik Il Im In Io Ip Ir Is It Iu Iv Jg Jh Jk Jl Jm Jn Jq Jr Jt Lh Li Lj Lu Lw Ly Lz Ma Mc Me Mf Mg Mh Mj Mk Ml Mm Mn Mp Mq Mr Mt Mw Mx Mz Na Nb Nc Nd Ne Nf Ng Nh Nj Nk Nl Nm No Nq Nr Ns Nt Nu Nv Nw Nx Ny Oh Oi Oy Oz Pa Pb Pc Pd Pe Pf Pg Po Pz Qa Qb Qc Qd Qe) Mu(Ad aE aG AJ Al aW aX aY Bb bF Bg bN Bo bP bV cE cF cI Co CQ cS CT cW CX dB Dc Dd dE Dg dI Dk Dl dM dN Fp gL Hu Hv Hw Hx Ip Iq Ir Is Iv Jl Jo Jp Kk Lh Li Lj Lw Ly Ma Mb Md Mj Mk Mm Mp Mr Ms Mt My Mz Nc Ng Ni Nj Nn No Nr Nu Nw Oe Oi Om Pa Pb Pc Pe Qa Qd Qe Us) cT(aC Ad aG aH aI Aj aK aL aM AO aQ aR aU aV Ax aZ BB bG bH bI bL bM BO bQ bR bS bU bX cA cB cC cD cG cH cI cJ cK cL cM cO CQ Ct Cv cY cZ Db DC dD De dF dG dH dI dJ dK dL FR gL Ii Io Jo Jq Jt Lv Mg My Nn Oe Of Og Om Pg Us Vo) dM(aD aE AF aG aH aI aK aL aM aN aO aP aQ aR aS aU aV aW aX aY aZ bB bC bE bF bH bI bJ bL bM Bn BO bP bQ bR bS bU bW bX cA cB cC cD cE cG cH cI cJ cK cL cM cN cO cQ cR cV cW cY cZ dA dC dD dF dG dH dI dJ dK dL fR gL Lv Og) gL(aC aD aE aG aJ aQ bJ bL bM BN bP bQ bR bS bU cA cE cF cI cL cP cQ cS cV dB dC dH eC fP Hb iA iH Io IZ Jo Jq Jt Jv Kd Kj Kk Kl kQ kR Lv Mj Mm Ms nY OE OF Og oK Om Or Ow pF Ss Ub Ug Up tF) Nw(Fp Hu Hv Hw Hx Ii Ik In Iq Ir Is Iv Jl Jo Jp Jq Jr Lh Li Lj Lu Lw Ly Ma Mb Me Mg Mj Mk Ml Mm Mp Mr Mt Mv Mw My Mz Nc Ng Ni Nj Nk Nm Nn Nr Ns Nu Nx Oe Oi Om Pa Pb Pc Pe Pz Qa Qc Qd Qe) Og(AF aJ aW aX Bn Bo bV cF cP cS CX Et Ii Ij Im Ip Ir Jh Jk Jq Jr Jt Kd Kk Li Ly Ma Mb Mg Mj Mm Mp Mt Mx Mz Nb Nc Nj No Nt Nu Nv Om Or Ow Oy Pg Po Qa Qb Qd To Uf Ug Us Wm) Ok(Et Hq Hr Ih Ij Im In Io Ip It Iu Jh Jk Jm Jn Lh Li Lj Lw Lz Mc Me Mh Mj Mk Mm Mn Mq Mr Mw Mx Na Nb Nd Ne Nf Ng Nh Nl

Figure 15 Continued

Nm No Nr Ns Nt Nv Ny Oh Oi Oy Oz Pd Pf Po Pz Qb Qc) Jl(Fp Hu Hv Hw Ii Ip Iq Is Iv Jg Jm Jo Jp Jq Js Jt Lh Li Lu Lw Ly Ma Mb Md Me Mg Mk Mm Mp Mr Mt Mv My Mz Ne Ng Ni Nj Nk Nm Nn Nr Ns Nu Nx Oe Oi Pa Pb Pc Pe Pz Qa Qd Qe) Us(Af aJ aQ aU aW aX bN Co cP Cx cY dK dR EF Ex Ez Fr Hc Hu Hv Hx lu Jh Jn Kg Ko Kq Ld Li Mg Mi Mp Mv Mw Mz Ng Nn Nq Of Or Pd Ph Qd Qe Qn Qy Tn To Uf Ug Ut Vo Vv) aJ(aD aG aH aI aK aL aM aO aQ aR aS aU aV aY bB bE bH bI bM Bn bP bS bW cA cB cC cD cG cH cI cJ cK cL cM cN cW cY cZ dA dC dF dI dJ Ii Lv Oe oK) Kk(Aa aE Af Ao aQ aU aV aX BN bP bX cF cP CX cY dK dR Hb Ii Io Jo Jq Jt Kd Kg Ks Lv Mg Mj My Nn Of Om Ow Qn To Uf Ug Up Vo) Jp(Af Fp Hb Hu Hv Hw Hx Ik Iq Is Iv Jt Lh Li Lu Lw Ly Ma Mb Me Mk Mp Mr Ms Mv My Ni Nj Ns Nr Nu Of Om Pa Pb Pc Pe Qn Vo Wm) Cx(aC aE aN aP aW AX Ba BC bN Bo bU bV bZ cF cN cQ Cs cU dB dE dF dN eF Fr Hr iZ Jo Kd Lu Lv Mi My Ow To Ug Up Vo) Af(aP AW AX Ba bC Bg bN Bo bV bZ cF cS cU dB De dF Dk dN FR Hu iZ Jh Kd Kg Kq Lu Lv Mi Mv My Nq Ow Uf Ug) Hu(Fp Hv Hw Hx Ir Is Iv Jo Lh Li Mj Mk Mm Mp Mr Ms My Mz Nb Ng Nn No Nr Nu Of Om Pa Pb Pc Pe Po Qa Qe Ug) Hv(Hw Ip Iq Is Jg Js Lh Lw Ma Mb Mg Mk Mm Mp Mr Ms Mt Mv My Mz Ni Nk Nn Nr Nu Om Pa Pb Pc Pe Qe) Ow(aA aE Ao aW aX bN cF cP cS cX dK Hb Io Jo Jq Jt Jv Kd Mj Mm Ms Of Qn Ug Up Uu Vo) Pa(Fp Hr Iq Is Jg Jo Js Lw Ma Mb Mg Mm Mp Ms Mt Mv My Mz Ni Nn Nu Oe Of Om Qa Qe) cP(aP aW AX Ba bC bG bN Bo cF cO cR cX dA Db DE dF dN Fr Jo Lv Mi Oe) My(aW Fp Hw Iv Jg Lh Lw Mb Mk Mp Mr Ms Nj Nn Nr Of Om Pb Pc Pe Ug Vo) cS(aW Ax bG BN cF dE Ii Io Iq iZ Jo Jt Kd Lu Lv Oe Of Or Ug Up Vo) Mv(Ao Fp Hw Iq Jo Lh Li Lw Ly Mk Mp Mr Ms Mz Ng Nr Nu Of Om Pb Pe) Ug(aQ aX BN cF cX dK Hc Io Kd Kg Kq Lv Mj Qy To Uf Up Vv Wm) Mp(Fp Hw Hx Ir Is Iv Jg Lh Mb Mr Mz Nd Nn Ns Oz Pf Pg Qe) Pe(Hr Iq Jg Jo Js Lw Mb Ms Mt Mz Ni Nn Nu Oe Of Om Pc Qa) Lw(Fp Hx Is Iv Jg Lh Lu Mb Mt Mz Nn Pb Pc Qa Qe) Kd(aX cX dK Hb Io Jo Jq Jt Mj Of Qn To Up Vo) iZ(aE aW aX aZ bG bO bZ cU cX dB dE dK eF oK) Vo(aQ aX Ba cX Kg Ko Kq Lv Ma Mg Or Sr Uf) Nn(Fp Hw Ir Iv Lh Mb Md Mr Ms Mz Of) Ii(Ba Ex Hc Kg Kn Ko Kq Or Tn Uf Vv) cF(aP aW bV bZ cU dA dE dN fR Lv Of) Lh(Iq Jo Jt Mb Ms Mz Ni Oe Of Om) aA(Aa Ax Bo Cv De eC fR oK pF Qn) Mz(Lu Mb Mk Mr Ms Om Pb Pc) Of(Ba Hc Is Jg Kg Ma Nv Uf) cU(aW BN Bo dB dE dN fR) Jo(aX Ba bZ Kg Kq Uf Wm) cX(aP dN Ex Or Rj To Up) Lv(Aa aW aX Bn bV dB) Jg(Fp Jt Mb Md Ms Om) Iq(Hx Ir Is Qa Qe) dN(aW bG bV dB dE) Mb(Aa Hx Mk Mr) Jq(aX Kg Kq Uf) Om(Hx Is Qa Qe) aP(aW bN dB dH) bZ(aW bN cE dE) Mk(Fp Mt Qa) Jt(Ba Ko Kq) Pc(Md Ms Ns) fR(aF aW bN) Wm(Fr In) No(Js Md) Lu(aF aX) Mr(Mt Qa) Is(Ms Pb) AaNd BnBo FrIi GzOu MgUe MtHw UcKq lobV OrdK bEoK eFnY Unconstrained panels with 2 analytes, where 1.0E-2 >= 'model p-value' > 1.0E-3. Contains 7,447 panels of 66,377 total panels evaluated. :
Ug(AA aC AD aE aF aG aH aI AJ aK AL aM AN AO AP AR AS aU aV aW Ax aY aZ Ba BB BC bE bF BG bH bI bJ bL bM BO bP bQ bR bS bU bV bW bX bZ cA cB cC cD cE cG CH cI cJ cK cL cM cN CO CP CQ cR Cs CT CU CV CW cY cZ dA DB DC DD DE dF DG dH DI dJ Dk DL dM dN Dp dR Ed EF Et Ex Ez Fa Fb Fn Fp Fr Fw Gl Gp Ha Hb Hf Hq Hr Hv Hw Hx Ib Ic Id Ih Ii Ij Ik Il Im In Ip Iq Ir Is It Iu Iv Iz Jd Je Jf Jg Jh Ji Jk Jl Jm Jn Jo Jp Jq Jr Js Jt Ju Jv Jy Ke Kf Ki Kj Kl Kn Ko Kp Kr Ks Kx Ky Kz Ld Lh Li Lj Lu Lw Lx Ly Lz Ma Mb Mc Md Me Mf Mh Mi Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv Nw Nx Ny Oa Oe Of Oh Oi Ok Om On Or Oy Oz Pa Pb Pc Pd Pe Pf Pg Ph Pi Pj Pk Po Pz Qa Qb Qc Qd Qe Qg Qh Ql Qm Qn Qt Qu Qw Qx Qz Ra Rb Rc Rf Rg Rh Ri Rj Rm Sr Ss St Tn Tr Tt Tv Tz Ua Ub Uc Ud Ue Uh Uk Ul Um Un Uo Ut Uu Uv Vo Vp Vs Vt Vu Tj) Kk(aA aC AD aF aG aH aI AJ aK AL aM AN aO AP AR AS AW Ax aY aZ Ba BB BC bE bF BG bH bI bJ bL bM BO bQ bR bS bU bV bW bZ cA cB cC cD cE cG CH cI cJ cK cL cM cN CO Cp CQ cR Cs CT CU CV CW cZ dA DB DC DD DE dF DG dH DI dJ Dk DL dM dN Dp Ed EF Et Ex Ez Fa Fb Fn FP Fw Gl GP Ha Hc Hf Hq Hr Hu Hv Hw Hx Ib Ic Id Ih Ii Ij Ik Il Im In Ip Iq Ir Is It Iu Iv Iz Jd Je Jf Jg Jh Ji Jk Jl Jm Jn Jp Jr Js Ju Jv Jy Ke Kf Ki Kj Kl Kn Ko Kp Kq Kr Kx Ky Kz Ld Lh Li Lj Lu Lw Lx Ly Lz Ma Mb Mc Md Me Mf Mh Mi Mk Ml Mm Mn Mp Mq Mr Ms Mt Mv Mw Mx Mz Na Nb Nc Nd Ne Nf Ng Nh Ni Nj Nk Nl Nm No Nq Nr Ns Nt Nu Nv Nw Nx Ny Oa Oe Oh Oi Ok Om On Or Oy Oz Pa Pb Pc Pe Pf Pg Pi Pj Pk Po Pz Qa Qb Qc Qg Qh Ql Qm Qt Qu Qw Qx Qz Ra Rb Rc Rf Rg Rh Ri Rj Rm Sr Ss Tr Tt Tv Tz Ua Ub Uc Ud Ue Uh Uk Ul Um Un Uo Up Uu Uv Vp Vs Vt Vu Wm Tj) gL(AA Ad aH aI Aj aK AL aM aN AO AP aR AS aU aV AX aY aZ bB BC bE bF bG bH bI BO bV bW bX bZ cB cC cD cG cH cJ cK cM cN cO Cq cR CU Cv cW cY DB Dc DD DE dF DG dl dJ DK DL dN Dp dR Ed eF Et Ez Fa Fb Fn Fp gP gW Ha hB HC HF hG Hq Hr Hu Hv Hw Hx Ib Ic Id Ih lJ Ik Il Im In iO IP Iq Ir Is It Iu Iv Jd Je Jf Jg Jh Ji Jk Jl Jm Jn Jp Jr Js Ju Jy Ke Kf Kg Ki Kn Ko Kp Kq KS Kx Ky Kz Ld Lh Li Lj Lu Lw Lx Lz Ma Mb Mc Md Me Mf Mg Mh Mi Mk Ml Mn Mp Mq Mr Mt Mv Mw Mx My Mz Na Nb Nc Nd Ne Nf Ng Nh Ni Nj Nk Nl Nm Nn No Nq Nr Ns Nt Nu Nv NW Nx Ny Oa OH Oi Ok ON Oy Oz Pa Pb Pc Pd Pe Pf Pg Ph Pi Pj Pk Po Pz Qa Qb Qc Qd Qe Qg Qh Ql Qm Qt Qu Qw Qx Qy Qz Ra Rb Rc Rf Rg Rh Ri Rj Rm Sr St Tn To Tr Tt Tv Tz Ua Uc Ud Ue Uf Uh Uk Ul Um Un Uo Ut Uv Vp Vs Vu Vv) Ow(Aa aC AD aF aG aH AJ Al AN AP aQ Ar AS aU aV Ax aZ bA Bb bC bF BG bJ bM Bn bO bP bR bS bU bV bX cA cD cE cI cK Co Cp CQ cR Cs CT cU CV cW cY DB DC DD DE Dg dH DI Dk DI dM dN Dp dR Ed EF Ex Ez Fb Fn Fp Fr Fw Gp Ha Hc Hf Hq Hr Hu Hv Hw Hx Ib Ij Ik Il Im In Iq Ir Is It Iu Iz Jd Je Jf Jg Jk Jl Jm Jn Jp Jr Js Ju Jy Ke Kf Kg Kj Kl Kn Ko Kp Kq Kr Ks Ky Ld Lh Li Lu Lv Lw Ly Lz Ma Mb Md Me Mf Mg Mi Mk Ml Mn Mp Mr Mu Mv Mx My Mz Na Nb Nd Ne Nf Ng Nh Ni Nk Nl Nm Nn No Nr Ns Nt Nv Nx Ny Oe Oh Oi Om Or Oy Oz Pa Pb Pc Pe Pf Pg Ph Pj Po Pz Qb Qg Qh Qm Qw Qx Qy Ra Rb Rc Rf Rg Rh Rj Rm Sr Ss St To Tr Tt Tv Tz Ub Uc Ud Ue Uf Uh Uk Um Uo Uv Vp Vs Vu Vv Wm Tj) Cx(Aa AD AF aG aH aI Aj aK AL aM An AO Ap aQ AR AS aU aV Aw aY aZ BB bE bF BG bH bI bJ bL bM Bn bO bP bQ bR bS bW bX cA cB cC cD cE cG CH cI cJ cK cL cM CO Cp CQ cR Ct Cu CV CW cX cY cZ dA Db DC DD Dc DG dH DI dJ DK DL Dp dR Ef Ex Ez Fn FP Fw Gl GP Ha Hb Hc Hq Hu Hv Hw Hx Ib Ii Il Im In Io Iq Ir Is Iu Iv Iz Je Jf Jg Ji Jl Jn Jp Jq Jr Js Jt Ju Jv Kg Ki Kj Kn Ko Kp Kq Kr Ks Kx Ky Ld Lh Li Lj Lx Ly Lz Ma Mb Md Me Mf Mg Ml Mm Mn Mp Ms Mt Mv Mx Mz Nc Ne Ni Nj Nk Nl Nm Nn Nu Nw Nx Oe Of Om On Or Oy Pb Pd Pe Pg Ph Qa Qb Qc Qd Qe Qg Qn Qu Qw Qx Qy Ra Rb Rg Rh Rj Sr Ss St Tn Ub Ue Uf Uh Uk Um Uu Vp Vu Vv Wm Tj) Kc(aH aI aK aL aM aN aO AP AR As aU Aw aZ Ba bB BC bE bF BG bH bI bJ bL bM bO bQ bR bU bW bZ cB cC cD cG CH cJ cK cL cM cN CO cR Cs Ct CU cV cZ dA DB dC dD dE dF dG Di dL dN Ed Et Ex Ez Fa Fb Fn FP FR Gl GP Gz Hf Hq Hw Ib Ic Ih Ij Ik Im Ip Ir Is It Iv Jd Je Jg Jh Ji Jl Jm Jr Ju Jy Ke Kg Ki Kn Ko Kp Kq Kx Ld Li Lj Lw Lx Ma Mb Mc Me Mf Mg Mh Mi Mk Mn Mq Mt Mu Mv Mw Na Nb Nc Nd Ne Nf Ng Nh Nj Nn Nq Nr Ns Nt Nu Nv Nw Oa Oh Ok On Oz Pa Pb Pc Pd Pe Pf Pi Pk Qa Qb Qc Qd Qe Qg Qh Ql Qm Qt Qu Qw Qx Qy Qz Ra Rb Rc Rf Rg Rh Ri Rm Sr Ss St Tn Tt Tz Ua Ud Ue Uf Uh Ul Um Un Uo Ut Uv Vt Vu Wm) cS(Aa aC AD aE aF Aj AL AN AO AP aQ Ar As Aw aY aZ Ba Bb BC bE bF Bg bH bJ BO bQ bR bU bV bX bZ cB cE Ch cI cN CO Cp CQ Cs Ct CU CV CW cX dA DB Dc DD De dF DG dH DI dJ Dk Dl dN Dp dR Fn FP FR Fw Ha

Aw Ax Ba Bb Bc Bg Bo Ch Co Cp Cq Cs Ct Cu Cv Cw Db Dc Dd De Dg Di Dk Dl dR eC eF FR gP gW Hb Hr Hx In Io Iq Jn Jq Js Jt Kg Lu Mb Md Mg Mi Mj Ml Mm Mp Ms Mx Mz Ne Ni Nk Nl Nm Nn Nq Nx NY OF Oi Om pF Pg Qn Up tF) aP(aC aD aE aF aG aH aI aK aL aM aN aO aQ aR aS aU aV aX aY aZ bB bC bE bF bG bH bI bJ bL bM Bn bO bP bQ bR bS bU bV bW bX bZ cA cB cC cD cE cG cH cI cJ cK cL cM cN cO cQ cR cV cW cY cZ dA dC dD dE dF dG dI dJ dK dL Ii Jt Oe oK Qn Ur) Pa(Et Hq Hw Hx Ih Ii Ij Ik Il Im In Io Ip Ir It Iu Iv Jh Jk Jm Jn Jq Jr Jt Li Lj Lu Ly Lz Mc Md Me Mf Mh Mj Mk Ml Mn Mq Mr Mw Mx Na Nb Nc Nd Ne Nf Ng Nh Nj Nk Nl Nm No Nq Nr Ns Nt Nv Nx Ny Oh Oi Oy Oz Pb Pc Pd Pf Pg Po Pz Qb Qc Qd) Is(Et Fp Hw Hx Ih Ii Ij Ik Il Im In Ip Ir It Iu Iv Jg Jh Jm Jn Jq Jr Js Jt Li Lj Lu Ly Ma Mb Md Me Mf Mg Mj Mk Ml Mm Mq Mr Mt Mx Mz Na Nb Nc Nd Ne Nf Ng Ni Nj Nk Nm Nn No Nq Nr Ns Nt Nu Nv Nx Ny Oe Oi Oy Pc Pg Po Pz Qa Qc Qd Qe) Mp(aX cF Et Ha Ih Ii Ij Ik Il Im Ip Iq Iu Jh Jk Jm Jn Jq Jr Js Jt Li Lj Lu Lw Ly Lz Ma Me Mf Mg Mj Mk Ml Mm Mn Mq Ms Mt Mw Mx Na Nb Nc Ne Nf Ng Ni Nj Nk Nl Nm No Nq Nr Nt Nu Nv Nx Oe Of Oi Om Oy Pb Pc Po Qa Qb Qd Uf Uk Up) aX(aW Ax BN Bo bZ cF Dp Fp Fr Hb Hr Hx Ii Il In Io Ip Iq Iu Iv Jf Jn Jr Jt Jv Kj Ky Lw Lx Ly Ma Mb Md Mf Mg Mi Mj Ml Mm Ms Mx Mz Ne Ng Ni Nj Nk Nl Nm Nn Nq Nu Nx nY Oe Of Oi oK Om Or Oy Pb Qn Rg Rj To Ub Uk Up Uu Vv) Lw(Et Hq Hw Ih Ii Ij Ik Il Im In Ip Iq Ir Iu Jh Jk Jm Jn Jq Jr Js Jt Li Lj Ly Ma Mc Md Me Mf Mg Mh Mj Mk Ml Mm Mn Mq Mr Ms Mw Mx Na Nb Nc Nd Ne Ng Ni Nj Nk Nl No Nq Nr Ns Nt Nu Nv Nx Oe Of Oi Om Oy Pg Po Qb Qd Wm) Nn(aW Bo Et Hb Hx Ih Ii Ij Ik Il Im Ip Iq Iu Jg Jh Jm Jn Jq Jr Jt Kj Ks Li Lj Lu Ly Lz Ma Mc Me Mf Mg Mh Mj Mk Ml Mm Mn Mq Mt Mx Nb Nc Nd Ng Ni Nj Nk Nl No Nr Ns Nt Nu Nv Oe Oi Om Or Pb Pc Pg Po Qa Qb Qd Qe) aA(Ad Aj Al An Ao Ap Ar As Aw Ba Bb Bc Bg Ch Co Cp Cq Cs Ct Cu Cw Db Dc Dd Dg Di Dk Dl dR eF fP gP gW HB hC hF hG iA iH iJ iO iP Iz Jv Kg KQ kR kS nW nY oE oF oH oN Or Qw Qy Rj To Ub Uf Up Uu Vp Wm tF) Hx(aW Bn Bo cF Et Fp Hb Hw Ii Ik Il Im Ip Ir Iv Jg Jh JI Jm Jq Jr Js Jt Li Lj Lu Ly Ma Md Me Mf Mg Mj Mk Mm Mr Ms Mt Mx Mz Nb Nc Nd Ne Ng Ni Nj Nk No Nr Ns Nt Nu Oe Of Oi Pb Pc Pg Po Qa Qd Qe Qn To Up Wm) Jg(Et Hw Ih Ii Ij Ik Il Im Ip Iq Ir Iu Iv Jh Jm Jn Jq Jr Js Li Lu Ly Lz Ma Me Mf Mg Mh Mj Mk Ml Mm Mq Mr Mt Mw Mx Mz Nb Nc Nd Nf Ni Nj Nk Nl Nm No Nr Ns Nt Nu Nw Nx Oe Oi Pb Pc Pg Po Qa Qb Qd Qe Uu) Ii(AW Bg BN Bo bP bV bZ cF Co Cp Cu Cw dB dF Dk dM dR EF Fa Fb Fp fR Gl Gp Je Jf Ke Kp Kx Ky Ld Mt Mz Nu Oa Pg Ph Qa Qe Qh Qn Qu Qx Qy Rf Rg Rh Rj Sr St To Ua Ub Uh Uk Un Up Vt Vu Wm) Ur(aC al aK aL aM aN aO aR aS aU bB bF bG bH bI bL bM bO bQ bR bU cB cC cD cG cH cJ cK cL cM cN cO cQ cY cZ dA dC dD dF dG dH dI dJ dL fP fR gP Gz Ib Jh Mk Mq Nf On Oz Qt Qz Ri Ud Um Un Vt) Of(Aw Bg Bn Bo bV bZ dR eF Et Ex Fp Hw Ij Ik Im Ir Iv Jf Jk Jt Kn Ko Kq Ky Ld Li Mg Mj Mk Mm Mr Mt Mz Nb No Nr Nt Nu Om Or Pb Pc Pg Ph Po Qa Qd Qe Qn Qw Qx Qy Rj Sr Tn To Ua Up Vv Wm) aW(aO Ax aZ Ba bC bE bF bG bJ BN Bo bQ bU bV bW cG cO cQ cR dA dB dE dF dG eC eF Fr HB hG iH iP Jq Jt Jv Kg Kq Lu Mb Mg Mi Mz Ni nY Oe oF oK Or pF Qn Qy Rj To Uf Uk Up Vv) Mr(Et Fp Hr Hw Ih Ik Il Im Ip Iq Ir Iv Jh Jk Jn Jq Jr Js Jt Li Lj Lu Ly Lz Ma Md Mf Mg Ml Mm Mn Mq Ms Na Nb Nc Ng Ni Nj Nk Nl No Nq Nt Nu Nv Oe Om Pb Pc Pg Po Qb Qd Qe) Qe(Et Fp Hw Ij Ik Il Im Ip It Iu Iv Jh Jm Jq Jr Js Jt Li Lu Ly Ma Mb Md Me Mf Mg Mj Mk Mm Mq Ms Mt Mx Mz Nb Nc Ne Ng Ni Nj Nk Nm No Nr Nt Nu Nx Oe Oi Om Pb Pc Pg Po Qa Qd Up) Jl(Et Hq Hr Ih Ij Ik Il Im In Io Ir It Iu Jh Jk Jn Jr Lj Lz Mc Mf Mh Mj Ml Mn Mq Mw Mx Na Nb Nc Nd Nf Nh Nl No Nq Nt Nv Ny Oh Oy Oz Pd Pf Pg Po Qb Qc) Mz(Bo Et Fp Hb Ij Ik Im Ip Iq Ir Iv Jh Jk Jq Jr Js Jt Li Ly Ma Md Me Mf Mg Mj Mm Mq Mx Nb Nc Nd Ng Ni Nj Nk No Nr Nt Nu Nv Oe Oy Pg Po Qa Qd Qn Wm) bV(Aa aC aF aN aO aQ Ax aZ bE bF bG bJ BN BO bR bU bZ cA cB cC cE cI cN cO cV cW dB dE dF dH dI dK FR Iq Ir Iv Jq Jt Lu Mg Mi Oe Om Qn Up) Nr(Et Fp Hr Ih Ik Il Im Ip Iq Ir Iv Jh Jq Jr Js Jt Li Lu Ly Lz Ma Mb Md Mf Mg Mm Mq Ms Mx Na Nc Ni Nj Nq Nt Nu Nv Oe Om Pb Pc Pg Po Qa Qb Qd) Qn(aE aF aQ aU aV bN Bo bP cI cY dB dD DE dK dR eF Ex FR Hr Im Io Iq Jn Jr Kg Ko Kq Ky Ld Mb Mg Oe Or Pb Ph Qy Rg Rj Sr To Ub Uf Uk Up) bZ(aC aD aE aF aG aH aN Ao aQ aZ bC bE bF bG bJ bL Bn BO bQ bR bU cA cC cG cI cL cQ cR cV cW dA dB dD De Dg dH dI dJ dK fR Jq Jt Lu Oe) Qa(Et Fp Ih Ij Ik Ip It Iu Iv Jh Jm Jq Jr Js Jt Li Lu Ly Ma Mb Md Me Mg Mj Mm Mq Ms Nb Nc Ne Ng Ni Nj Nk No Nu Oe Oi Pb Pc Pg Po Pz Qc) Nw(Et Hq Hr Ih Ij Il Im Io Ip It Iu Jh Jk Jm Jn Lz Mc Mf Mh Mn Mq Mx Na Nb Nd Ne Nf Nh Nl No Nq Nt Nv Ny Oh Oy Oz Pd Pf Pg Po Qb) Mg(Aa Ad Aj Ao Bn Bo Dl dM Dp Fp Ha Hb Ir Iv Iz Jf Jv Kj Ks Lu Mj Ms Mx Nb Nc No Nu Om Or Pb Pc Qd Qw Rg Rj To Ub Uc Uk Up Uu) Uf(aE Aj Ao BN cI De Dg dK Dl Ex Ha Hb Il In Io Iq Iz Jf Jt Kj Ks Ky Lu Mj Ms Oe Om Or Qw Rj To Ub Uc Ue Uk Up Uu Vv) Pc(Et Fp Ik Im Ip Iq Ir Iv Jq Jr Li Lj Lu Ly Ma Mb Mc Mj Mm Mq Mx Nc Ng Ni Nj No Nt Nu Nv Oe Oi Om Oy Pb Pg Po Qd) Bn(aC aE aF aN Aw Ax aZ Ba bC bN bQ bU cN cO Cs dA dB dE dF dG Dk FR Hr Jt Kg Kq Lu Mi Nq Oe Or Rg Rj To Up) dM(Ad Aj Al An Ao Ar As Aw Ax Ba Bb Bc Bg Ch Co Cp Cq Cs Ct Cu Cv Cw Db Dc De Dg Di Dk Dl Fr Lu Mb Mi nY Oe oK) Pb(Et Fp Il Im Ip Ir Iv Jq Jr Li Lu Ly Ma Mb Md Mj Mm Ms Mx Nb Nc Ni No Nt Nu Nv Om Pg Po Qb Qd To Wm) Or(aE aF Ao aQ aV bN Bo cI cY dB Ex Fw Hb Hr Io Iq Jq Jt Jv Kg Ks Ky Mj Ms Oe Om Rj To Uk Up Uu) dK(Dp fR HB Hc hG iH Jf Jv Kj Ko kQ Ks Ky Lu nY Oe oF oK pF Ph Qw Rg Rj To Ub Ue Uk Up Uu Vv) bN(aN aO Ax Ba bC bG Bo bQ cN cO cR cS dA dB dE dF dG eF Fr Jv Kg Lu Mi Oe Rj To Up) Fp(Et Ij Ip Iq Ir Iv Jh Jq Li Lu Ma Md Mj Mm Ms Nb Nc Ni Nk No Nu Nv Oi Om Pg Po Qd) To(aE aF Ao aQ aV cY dR Hb Io Jq Jt Jv Kg Ld Li Lu Mj Mm Ms Oe Om Rj Ub Uk Up Uu) Iv(Et Ij Im Ip Ir Jq Js Li Lu Ly Ma Mb Mj Mm Mq Ms Nb Nc Ni No Nu Oe Om Pg Po Qd) Qd(Ij Il Ip Iq Js Jt Li Lu Ly Ma Mb Mm Ms Nb Nc Ng Ni Nj No Nu Oe Om Po Qc Up) Bo(aC aF Ao Ax Ba bC bG bO bU DE Fr Hb Iq Jq Jt Jv Lu Md Mi Mm Nx Oe Om) fR(aC aH aN Ax bC bG bH bJ bL bO bR bU cC cE cH cV dA dB De dH dL Iq Jt) No(Ik Im Ip Iq Ir Jr Lu Ly Ma Mb Mc Ml Mm Ms Na Nc Ni Nj Nq Oe) Li(Et Ip Iq Ir Jh Jq Ly Ma Mb Mm Ms Ni Nv Om Up) Fr(aC Ad aE aF Aj Ao Ax bC Bg bO Cv De Dg Hb) Kq(aE Ao Bb Ha Hb Hr Iz KI Ks Oy Pg Up Uu Vs) Ma(Iq Ir Jr Jt Ly Mb Ms Nc Ng Nj Om Uu Wm) Mi(aE aF Aj Al Ao bS cA cI Dc Dl Uk Up) Om(Ba Et Ij Im Ir Ko Mb Mm Ms Nv Pg Up) Hb(aQ aV dD dR Et Jn Ko Ky Ph Uh Up) Qy(aE Ao aQ Jq Kj Oy Qw Ub Up Uu) Ba(Ad Aj Ao Ax Dg Dl Jq Oe Uu) Mm(Ir Jr Ko Ly Mb Me Ms Up Wm) Io(dR Ko Ky Rj Ub Up Vv) Jq(dR Kn Ko Ky Mb Ph Vv) Jt(Cu Cw Dk Et Ir Nv Sr) aF(Ax dF Oe oK Rj Ub Uk) Wm(Hr Iu Ji Ly Ok On) Ms(Et Ij Im Ir Nv Pg) Iq(Aa Ij Im Nv Pg Qb) Up(aE aQ bP Jn Rj St) Uu(aQ Bg Ef Hc Ko Ph) bE(aC eC hC hG nY oF) Ao(Hc Ko Nq Ph Vv) Mb(Et Ij Ir Nv Pg) Ni(Ir Nc Nk Nv Pg) oK(aE bJ bP cI nY) bC(Aj Ax Cs Cv) Aa(Ax Ne Nj) Md(Nd Nv Pg) Ly(Im Ir) Ko(Dl Ks) Oe(bP dR) bU(Ax dA) dF(bJ cE) DkMw NcNk NgNv lUr IpIr JvaE RjaQ bGcR bOnY bRdA

Figure 15 Continued

Constrained panels with 3 analytes, where 1.0E-9 >= 'model p-value' > 0. Contains 117 panels of 7,710,078 total panels evaluated. : Lv{Jj(aA Fr Hu Hv Hw Hx Ih Ij Jg Jk Jl Jp Lh Li Lx Ma Mg Mi Mk Mp Mr Mu Mv My Mz Nb Nn Nq Nr Og Ok On Oy Pa Pb Pe Qa Qe) aA(Ii Jo Js Mg Mm Ms Ng Nx Oe Of Og Oi Om Pb) Mi(Hq Jo Js Md Ms Of Og Om Pg) On(Jo Jt Nx Of Og) Fr(Jo Of Og) Og(Hu Ok) JqOk} Mi{Hq(Fp Hu Hv Iq Jj Jt Lu Ly Mb Mf Mg Ms Nj Oe Of Og Om Pb) Jj(Hu Ik Iq Ly Md Ms Nj Om Pb) Mb(Js Md Of Pg) Ly(Md Of) Hu(Of Og) JqOk NxOn} Ou{Ur(Io Jv Qn) QvaF} Jj{FrLy HuJl} Nx{On(Oe Og)}

Constrained panels with 3 analytes, where 1.0E-8 >= 'model p-value' > 1.0E-9. Contains 353 panels of 7,710,078 total panels evaluated. : Mi{Of(Fp Fr Hv Ik Iq Jj Jo Jr Jt Md Mf Ms Mu Mv My Ni Nj Nn Og Om On) Js(Fp Hu Hv Hx Iq Iv Jj Jn Jp Lh Lx Ly Ms Nb Nw Om On Pa Qa Qe) Md(Fp Hu Hv Ik Io Iq Jo Jr Jt Mf Ml Ms Mu Ni Nj Nn Oe Og Om) Jj(Fp Fr Hx Lh Mb Me Mh Ml Mu My Nc Nf Nn Nu Ny Oe Og Pg) Ms(Fr Hu Iq Jg Jp Ly Mu Mv My Mz Ni Nn Og Ok On Pc Pg) Iq(aA Fr Hu Hv Hx Jg Jo Jp Lv My Og Ok Om On Pg) Lv(Jq Jt Mh Mj Ml Mt Nf Nx Ny Oe Oy Pb Po) Og(Fp Ik Jg Ly Mb Mu Nn Ok Om On Pb Pg) Om(aA Fr Hu Hx Jg Jp Mu Nn On Pg) Jo(Hu Ik Lh Ly Mu My On Pb) Hq(Ik Io Jq Ml My Ni Nx) Mb(Fr Hx Ml Ny On Pb) Jt(Hu Jp Ok On) Pg(Fp Hu Hv Ly) On(Ii Oe) NcNi} Ou{Ii(aF aW bN cS dK dN Hv Kc Kd Kg Kn Kq Ld Mg Nn On) Qv(aG aH aW aX bC bP cX cZ dK Jv Kc Mu Nn Uf Ur) Ur(Af aG aW Bn CX Hb Jq Ms Rg) aF(Ao Jt Of Uu) Kc(Aa Hb Us) aW(aX cF Io) Ao(Mg Mu) aE(Io Jv) FwbN MuOm HbKd OfbJ} Lv{Og(Hv Hw Hx Ij Is Jg Ji Jl Jq Lw Lx Md Mk Mr Mu Mv My Mz Nb Nn No Nr Nw Pa Pb Pc Pe) Fr(Ii Iq Js Jt Md Ms Ng Nx Oi Om) Jo(Hu Jl Lx My Ok) On(Ii Md Ms Oe) MyOf} Jj{Fr(Fp Hu Hv Ik Iq Mb Mp Ms Nc Nj Nu Of Og Om Pb) Hu(aA Lx Mp My Nn Nu Ok On Pa Qa Qe) On(Jt Ly Mb Nj Nx Oe Of Og Om) Ik(Jl Og) LyJl NjaA} On{Nx(Iq Jt Ly Mb Ms Nj Of Om) Og(aA Hu Iq Jt Mb Md Ms Of) Jt(Ii Md Ms Of Om) Of(Ii Jq Ms) Huli OeaA} gL{cX(Qv Us) AfUr} Mu{MdHu OmbA}

Constrained panels with 3 analytes, where 1.0E-7 >= 'model p-value' > 1.0E-8. Contains 1,190 panels of 7,710,078 total panels evaluated. : Ou{Ii(aE aJ aU aX bA bC bJ BN bP bU cl cP cR Cs cW CX De dM Ef Ez Fa Fb Fn Fp Fr GL Hc Hu Hx Ih Im In Io Jh Jn Jr Jv Kk Ko Li Lv Ma Mi Mp Mq Mu Mv My Mz Ng Nj Nk Nq Ok Pi Qd Qv Qy Rf Tn Uf Uk Ur Ut Vv) aW(Aa AF aG aH Ao bJ BN cD Cq cR cS CX Hb Jj Jo Jq Jt Ju Jv Kf Lh Mj Mn Mp Mu Ni Nm Nn Oe Of Og Om Pg Qn Up Us Uu Vo) Ur(Aa aE aF aH Ao Ar aX bC bN bU cl cP cS cW dK dN Fw Iq Jt Kc Kd Lu Mj Mp Oe Of Og Om Qm Qx Up Uu Vv) Qv(aA aD aL bE bJ bM bN bW cl cS dM dN Ez Fw gL Hb Im Io Jj Kd Kg Lv Mg Mi Mj Nh Nl Of Om Qn Ug Uu) aF(Aa aE Af aG aS aX cP cS Dl Hb Ij Io Iz Jg Jj Jo Jq Jv Kl Kr Lu Mg Ng Nm Og Om Pg Pz Qn Vo) Kc(aE Af aG Ao Cq Dg dH Dk Fw Ha Hr Jj Jo Jq Kf Kr Ks Lh Mj Nl No Of Pg Tv Up Vs Tj) Of(aE aX bN cF cS cZ dK gL Hb Hc Io Jh Kd Kg Mg Mj Mu Nn Qy Uf) Ao(aE aX cS De Ef gL Kd Kg Kq Mv Nn Qy Uf) Us(aX bV cl cS cX dK dN Fw Io Jv Kd Kk) Kd(Aa Iz Jj Jo Jq Jt Kl Mj Pg Up) aX(aE Af cE cX Hb Io Jj Jq Mj Om) bN(Aj Iz Jj Jo Jt Jv Kl Ug Vo) dK(Af aG cP Jj Jq Jv Mp Om Pg) cX(aE cF cS Dp gL Jv Pg Up) Io(cF cS Dp Hr Jj Mj Up) Fw(aE cA Mj Nl Up) Mu(cE Jo Jq Mp Uc) Nn(Jo Jq Mp Pg) Jv(bG Jj Mj Up) aE(bS Jj Jq Mj) gL(Af Iz Kl Uu) Mg(Jo Jq Jt) Up(cl dN Uu) cS(fP Jj Om) cF(Af Qn) MacE MjKk MpUf MyUu UcKq JqKg PgdN} Mi{Js(aA Fr Hr Hw Ij Ik In Ir Is Ji Jl Li Lj Lu Lz Mf Mg Mj Mk Ml Mn Mr Mt Mu My Mz Nc Nd Nj Nn No Nr Ns Og Oy Oz Pb Pc Pd Pe Pf Pg Qd) Jt(aA Fp Fr Hv Hw Ik Is Iv Jg Ji Jl Lh Lx Ly Mk Mt Mu My Mz Ni Nn Nw Pb Pc Pg Qe) Jo(Fp Fr Hv Hw Ip Jg Jl Jp Mb Mk Ml Mv Ni Nj Nn Ny Og Ok Om Pc Pg Qe) Mb(aA Ii Jg Jp Lw Mc Mh Mt Mu My Nb Nf Nn Oe Ok Oy Pc Po) Ni(aA Fp Fr Hu Hv Hx Jp Ly Nj Nk Og Ok Om On Pb Pc Pg) aA(Hq Hu Jj Ly Md Mf Ms Nj Oe Of Og Pb) Pg(Ik Jr Mf Mu Nj Nn Oe Of Pb) Ly(Fr Jm Jp Ne Nn Oi Ok On) Hu(Ii Iu Jm Jq Mt Mv Mp Nm Nv Of Pz) Og(Hv Hx Iv Ji Nj Nw Pc) Pb(Lz Md Mn Of Pd Pf) Jq(Fp Jg Ji Nw On) Ny(Lz Mn On Pd Pf) Fr(Mp Nc Nj Oe) Ml(Lz Mn Pd Pf) Hx(Lz Mn Pd Pf) Nx(Jg Ji Nw Ok) Of(Jg Oe Ok Qe) Om(Mv My Mz Ok) Mp(Mu My On) Nc(Md Ne Nk) Nj(Ne Nk On) Nn(Oe Oy) Nf(Pd Pf) WmJj PoFp LuOk MyPf Hvli NvOn} Jj{Hu(Fp Hv Hw Hx Ih Ij Im Ir Is Iv Jg Ji Jp Jr Lh Li Lw Ly Mg Mj Mk Mm Mr Mt Mu Mv Mz Nb Nj Nr Nt Nv Nw Og Pb Pc Pe Pg Po Qb Qd Wm) On(aA Fp Hv Ii Ik Iq Jl Jq Lu Lx Ma Md Mf Mg Ms Mt Mu Mv My Nc Nu Pb Qa Qe) Ik(aA Hv Hw Hx Jp Lh Lx Mk Mp Mr Mu My Mz Nn Nr Nu Pa Pe Qe) Nu(aA Hv Hw Hx Jl Lh Lx Mu Mv My Pa Pb Pe) My(aA Fp Hv Jl Lh Lx Mb Mp Nj Pb Pe Qe) Mu(Af Hw Lx Ly Mb Mp Nj Ok Om Pa) aA(Fp Ly Mb Mf Mg Nn Og Pb Pe) Jl(Mb Mg Ms Nj Og Ok Om Pb) Ly(Jg Lh Mv Pe Qe) Og(Ij Lh Lx Nt Ok) Om(Jk Lh Pe Qe) Wm(Hv Jp Mg) Nn(Hv Ok Pe) Nj(Hx Lh Lx) Fr(Hw Mf) AfMv LxMb} On{Og(Fp Fr Hr Hv Ii Ik Jl Jo Ly Ma Mf Mg Mu Mv Nc Nj Nn Nu Nv Ny Oe Om Pb) Oe(Fr Hq Hr Hu Hv Iq Jl Jo Jt Lx Mb Md Ms Mu Mv My Mz Nn Of Om Qa) Jt(aA Fp Fr Hu Hw Iq Iv Jp Li Lx Ly Mb Mz Nj Ns Nu Ok Qa) Nx(aA Fp Fr Hu Hv Io Jo Lu Lx Md Mf Nc Ni Ns Oy Pb) Of(aA Fr Hu Iq Js Ly Ma Mb Md Mm Mv My Ni Nn Om) Ii(aA Fr Hv Jl Lx Ly Mb Ms My Nj Om Pa) Lv(Hr Hv Jq Js Mm Nm Nv Om Oy Pz) aA(Iq Ly Mb Ms Nj Om) Ms(Hr Hu Nn Om) Jo(Hu Mb Om) Md(Jq Mb)} Lv{Jo(Hv Hw Hx Jg Ji Jp Lh Ma Mk Mr Mu Mv Mz Nv Nw Og Pa Pe Qa Qe) Js(Hv Hw Hx Iv Jl Lx Mj Mk Mr Mz Nr Og Pa Pb Pe) Of(Hu Hx Jg Ji Jl Jp Lx Ma Mu Mv Mz Nw Og Ok) Hu(Hv Ii Jq Jt Lu Ms Ng Nn Nx Om) Nx(Hx Ji Jl Lx Mu My Mz Nw Ok) Ok(Hv Hx Jl Jt Lu Ms My Nn) Md(Hx Jg Lx Mp Nd Nw Pc) Og(Ik Iv Jp Lh Lu Mg) Fr(Hv Jq Ly Mb Oe) My(Jl Lx Ms Mz Ng) Jl(Ii Jt Om) Ms(Mu Nw) Nd(Hq Oz) Ng(Jg Mv) Ji(Jq Lu) Om(Mu Mz) HxIi JpJt OePa} aA{Og(aF Fp Hu Ik Ji Jq Lw Ly Mb Mg Nj Nn Nw Ok Pb) cX(aC aW bA bM cF cP cS cT dB dE dH dN) Ok(Iq Jq Jt Ly Mb Ms Nj Of Om) Om(Fr Ji Lx Nw Pe) dH(bA bZ cU dN) Nw(Iq Ms Nj) Ji(Iq Nj) cP(aF dB) AfMg NgHu bAcV bJcT} bA{cX(aJ aS aW bE cE cF dB dE dN) bJ(aF aW bP cE dB) cP(AF aJ aS dB) Nw(AF cE cV dH) dE(aF cF cV) Mg(Jo Jt) aJ(dG dH) AfDe aWcF cScV} gL{cX(Ao Ef Hb Ii Iz Jo Kl Kr Ks Of Uu Vo Vv) Cx(aE aW bN cl dH Qv Us Uu) Af(Kc Qv) HbUr} Og{Ok(Fr Hu Hv Iq Jl Jt Mb Mu Mv Nn Pb) Fr(Hv Iq Ji Ly Mb Ms Of Om) Ji(Hu Hv Nn) MdOm} Fr{Of(Hv Ly Mb Ms Ok) Ly(Jo Ng) Ii(Hv Wm) MbNg JtOk} cT{Af(bC bJ cP Mu) aJ(cP cX dH) MgJo MuOm} Kc{My(Af Ao Hb Ii Jt Kj Of) HbUr} Kk{MgJo UscS} cP{AfMu aJdL} JpJtOk Constrained panels with 3 analytes, where 1.0E-6 >= 'model p-value' > 1.0E-7. Contains 3,789 panels of 7,710,078 total panels evaluated. : Ou{Kc(AD aH Aj Al aW bN cE cF Co CP cS Cu Cw CX DC Dd De dF dG dK Dl Dp Ed Ef Fa Hq Id In Iq Ir Iz Jf Jk Jl Js Jt Ju Jv Ke Kj Kl Kx Li Lu Lx Lz Mg Mh Ml Mn Mp Mr Mx Ng Nm Nr Nv Nw Nx Ny Og Om On Oy Pb Pe Pf Po Pz Qb Qh Qn Rg Rm To Tr Uc Ug Uu Uu Vo Vp Vu) aE(Aa Af aG aH Al An bC bJ BN bU cE cl cM cS Cx dH dK dN Ha Hb Ij Iq Iz Jo Jp Js Jt Ju Kd Kf Kg Kk Kl Kq Lh Lv Lz Mg Mi Mm Mn Mp Mu Mx My Ng Nm Nn Nr Oe Og Om Pf Pg Po Qb Qm Qn Qy Rm Uf Ug Up Us Uu Vo Vv) Kd(Ad AF Aj Al aX cE cF Co Cq cS cX Dc Dg dH DK Dl Dp Ef Ha Hq Hr Ij Io Jk Js Jv Kf Kj Kr Ks Lh Mm Mn Mp Ms Mx Nb Nl Nm No Nr Nv Nx Ny Oe Om On Oy Pf Po Pz Qb Qn Rm Tr Tv Ug Uk Uu Vo Vs Vv Tj) cS(Ad Af aG aH Aj aO bG Nn bX cE cF cG cl cP cV dF Dg dH Dl Dp Ef Fw Ha Hb Hr Ij Iq Iz Jo Jq Jt Jv Kf Kj Kk Kl Ks Lh Mg Mj Mm Mn Mp Ng Nm Ne Oi Pg Po Qn Rm Ug Up Uu Vo Vv) Jv(Af aG Al Ao aX bJ Bn bU cF cP Cq Dc dF dH Dk Dp gL Ha Hb Hr Im Io Jl Jo Jq Kr Lh Lz Mg Mr Mu Mx Nd Nl Nn Oe Of Om Pa Pb Pf Pg Qh Qn Qy Rg Rm To Tr Tv Uk Vp Tj) bN(AD Af aG aH Ao aX Bn bP cE cl Cq cX Dg dK Dl Dp Ef Ha Hb Ij Io Jg Jq Kf Kj Kk Ks Lh Mg Mj Mm Ng Nm Nv Oe Oi Om Pf Pg Po Pz Qn Qu Rm Ss Tt Tv Up Us Uu Vv) aF(AD aH Aj Ap bA Bn cE cF cl Co Cq cR Cw CX Dg dM dN Dp Ef Fw gL Ha Ik Iq Iu Jk Kf Ks Lz Mj Mk Mm Mn Mp Nn No Oe Oi Pj Po Qm Ss Tt Uc Ug Uk Up Us Vv) aX(AD aG Aj Al Bn bP bX cG cl cP Cq Cx dF Dg dH dK Dl Dp Ef fP Ha Hr Iz Jl Jo Jt Kf Kj Kl Kr Lh Mg Mn Mp Ms Ng Nl Nm Oi Pg Po Qn Qu Rm Ss Up Uu Vo Vv) dK(aD aH Aj Ao Bn bX cE cF Cq CX dC Dg Dp Ef Fw gL

Pd) Hx(Fp Hr Hv Jq Mf Nd Ns Oz) Ii(Mz Nw Pd Pf Wm) Pb(Mf Nd Ns Oz) Hr(Hw Li Mb) On(Mm Nm Pz) Mz(Jq Nw) Nb(Pd Pf) Lh(Jq Nx) LxNx Mblj MpMv NcNl UsbA} bA{Mu(Ao Bb Bn De Iq Jk Jo Jt Mp Ny Of Oy Pg Po Uc Us) Cx(aD aF aS aW aX bC bJ bO cE cF cP cS cZ dB gL) Af(aF AW bC bE bJ cF cS dB Jh Kg Mg Nq Qy) aF(aJ aS bE bO cF cR cS cU Cv dB dM Jt Og) cP(aL aW bE bF bJ Bn bO cE cF cG cV cX dF) bO(aD aJ aW cE cF cS cV dM dN) dH(bE bJ bP cO cS cU dA dE dM) cE(aJ aS bP cF cS cU dB dM) Ii(cS Kq Mg Mv My Nn Nq) cF(aJ aS bP cV dB dM dN) aW(aJ aS bE cV dB dE) cV(aJ bE cR dB dM) dE(aS bJ bU cC dM) Mg(Ao Jq Of Po) Us(aX Ez My Qy) cS(bQ cG cX Io) dB(aS bE dM dN) cX(bJ cR dM) Nn(Jq Pg) bE(aC aD) bQ(cO dN) cG(cU dN) HbKc QyOm JqKg aJaP} On{Jo(Fp Hv Ik Iq Iv Jl Jp Lh Lx Ly Ma Md Mf Mg Ms Mt Mu Mv My Mz Ni Nj Nu Qa Qd Qe) Iq(Hr Hu Hv Hx Ii Im Ir Jl Jp Lx Ma Mb Md Ms Mv My Mz Om Oy Qa Qe) Om(Hr Hu Hx Jl Jp Lx Ma Mb Md Mm Mu Mv My Mz Ng Ni Oi Oy Qa) Ms(Hv Jq Lx Ly Mb Md Mm Mu Mv My Mz Ng Ni Nm Nv Ny Oy Pz) Md(Hr Hu Hv Ii Io Js Lu Ly Ni Nj Nn) Mb(Hr Hv Jl Jp Jq My Mz Nv Ny Oy) Jt(Hr Im Jg Jl Ma Mt Nc Oy Qd) Ii(Hw Hx Lh Li Mm Pb Pe Wm) Oe(Hx Jp Lu Mt Nv Ny) Jq(My Nb Ng Ok Oy) Hu(Ng Nv Oy) Nn(Nv Oy) Hr(Ly Nj) NqOf NcNi QaJs JlNv} gL{Af(aF aQ aU aW bN cA cI cX dB De dH Ii Jh Kg Kk Kq Mg Mu Oe Ow Ph Qy Rm Uf Us Uu Vo) Cx(aC aF aG Ao bS cA cE cF cT DG Dl Ef Hb Ii Iz Jo Kl Ks Mm Of Og Om Ss Ur Vo Vv) cX(Aj Bn Dg Dk Dl Ez Jt Kj Ms Nm Oe Og Om Ph Pi Pz Ra Rm Ss Up Ur Uv) Ii(cS Hc Kc Ow Qv Ur Us Vv) Qv(aF Kc Ow Qn Vo) Vo(Bn dK Kc Kq) Ao(Kg Kq Mg) JqKc} Og{Ji(Fp Hw Hx Ik Iq Iv Jg Jl Jq Jt Lu Lx Ly Mb Mk Mr Ms Mu Mv My Nc Nj Nr Nu Om Pa Pb Pc Pe) Ok(Hx Ik Iv Jq Lu Ly Mg Ms My Nc Nj Nu Nx Of Om Pc) Nw(Hu Hv Ik Js Mb Md Ms Mu Nn Nx Ny) Hu(Jl Lw Lx Mk Mr Nn Nr Pa Pe) Lx(Iq Lz Mb Mu Mv Nn) Mu(Af Mb Pa) Hv(Jg Nn) Jl(Mb Om) MdMp} cT{Af(aJ AW aX bE cF cN cS cU dB DE dM dN Nq Qy) aJ(aF aW bJ bN bO cE cF cV Cx dE dG) dM(aF bJ cE cF cP cS CX dB dE dN) dN(aF bN cE cV cX dE dH) Cx(aW aX bC cP cS dB) dE(aF bJ cF cP cX) Mu(Ao Ii Jo Jq) cS(bJ cX Ii) aW(bJ cF) cP(Bn dB) cXfR} Ok{Jt(Hu Jg Jl Lx Mg Mt Mu Mv My Mz Nn Qa Qe) Nn(Iq Jo Jq Mb Ms Nx Oe Of) Jo(Hu Jl Mu Mv My) Jq(Hu Hv Ji Jl Mu) Of(Hu Jl Mu Mv My) Om(Jl Mu Mv) Ms(Hu My) MbMy} Kc{cP(Af Hb Ii Jo Jt Of Ow Qv Us Vo) My(Dg Dl Iz Jo Qv Us Uu Vo Vs) Qv(Af CX Jv Ow Vp) Af(aQ bN Ur) Hb(Jp Mz) Us(bV cX) CxUr LucX} Ur{Hb(Af cS CX Hv Jp Jr Kd Kg Kk Kq Mg My Or Ow Qd Tn Vu) Af(Jh Kq Mg Mu Mv My Ow) Ow(Jq Qn Qv) cS(cX Io Us) CxQv} aJ{dG(bC bN bQ bZ cP cS cU cX dN) dH(bF bN bQ bZ cO cP cU dN) cP(bN bU cF cU cX dB) dL(bN cS cX dN) bNcX} Qv{aX(cX Kd Kk Or Ow) Af(Jh Kg Kq Mg) cS(cX Io Jv Kk) Ow(Jv Kd Mj) Or(dK Mg)} Mu{cP(Ao Bn De Ii Jo Jq Om) Af(aW Il) AoJp KkOm} Us{My(bV dK Kk) CxKd MgJo StdK JpcS} Kk{cS(bN bX Hb Ii) MyIi} Ms{Ji(Hu My Nn) NnNw} Jo{Mg(Kd Qw Ue) LxHu} Md{LxLz MbNd MpHu} Wm{Jp(Ii Jt)} Kq{Vo(bN Jq)} aX{cP(Af Cx)} IiKdOw JiJlOm Constrained panels with 3 analytes, where 1.0E-5 >= 'model p-value' > 1.0E-6. Contains 6,169 panels of 7,710,078 total panels evaluated. : Ou{Mg(AA AD aH Aj Ap Bb bC bF Bg bJ bV cE cF cG Co Cp Ct Cw De Dk Dl Dp Et Ez Fw Hq Hr Hu Ij Ik Il In Jk Ju Kd Ke Kf Kg Kl Kq Kr Lh Lu Lv Mj Mk Mn Ms Mw Nm Nn Nt Nx Ny On Oy Po Pz Qm Qu Qw Qy Rm Ss Tr Tt Ue Uf Uk Up Vs Vv Tj) Uf(Aa AD aH Aj Bn cF cG cI Co Cq Cw Dc De dH Dk Dl Dp Ha Hq Hr Ij Ik Il In Iq Jg Ji Jk Js Ke Kf Kj Kk Kl Kr Ks Lh Lu Lz Mj Mk Mm Mn Mr Ms Mw Ng Nm No Nt Ny Oy Pf Po Pz Qu Qw Rm Ss Tr Tt Uh Vs Vv) Mu(AD aH Aj Bg Bn cF cI cL Cp Cq Cw dH dI Dk Dl Dp Fw Hr Ik In Iq Jg Ji Jk Js Kd Ke Kf Kg Kk Lh Lz Mj Mk Mm Mr Ms Mw Nm No Nt Ny Og Oy Pf Pz Qu Qw Rm Ss Tr Tt Ue Uh Uk Ut Vs Vv) Qy(Aa AD aH Aj bF Bg cG Co Cp Ct De Dg dH Dl Dp Fw Hq Hr Hu Ij Ik Il In Jg Jk Ju Kj Kl Kr Ks Lh Mk Mn Ms Mw Ng Ny Oy Po Pz Qu Qw Ss Tr Tt Ub Uc Ue Uh Uk Up Vs Tj) Nn(AA AD aH Aj cG Co Cq Cw dH Dl Dp Fw Hq Hr Ij Ik In Iq Jk Js Ke Kf Kl Ks Lh Lu Lz Mj Mm Mn Ms Mw Nm Nt Og Oy Pf Pz Rm Ss Tr Tt Ue Uh Uk Up Vv Tj) dN(Ad aH aV bF BG bN bQ cF cG Co Cq Ct Dc DG Dk Ha In Jk Jl Js Kr Lh Lx Lz Mk Mr Mx Ni Nl No Nr Nv Nx On Oy Oz Pa Pb Pe Pf Qh Qw Rg To Tr Tv Uc Vp) Kk(AD aH Bg Bn cE Co cP DC Dd Dg Dl Ef Ha Hq Ij In Jk Jo Js Ju Kf Kl Kr Lh Lx Ly Lz Ml Mn Mp Ms Nb Ng Nr Nv Ny Og Oi On Oy Pf Po Pz Qh Qx Uk Vp) Kg(Aa Ad aH Aj bQ cG Co Cq De dH Dl Dp Et Fw Ha Hq Hr Ij Ik Il In Iq Jg Ke Kf Kj Kl Kr Ks Lh Mn Ng Nm Ny Oy Po Pz Qu Ss Tr Tv Uc Uh Uu Vv) bC(Aj bF Bg Bn cG Cq Dc dF DG dH Dk Dp Ef Ha Hq Hr In Iz Jk Jl Jo Kl Ks Lx Mp Mr Nv Oy Pa Pb Pf Rg Ss Tr Tt Uu Vo Vp Vs Tj) Kq(aG aH bQ cG Co Cq Dc dH Dk Ef Hq Hr Ij In Iz Jg Jk Jl Jo Kl Kr Ks Lh Mk Mn Mp Mr Mx Nm Nv Oy Po Tz Up Ut Vp Vs Tj) Og(aA aD aH bE bG bJ BN bU cE cF Cq cZ Dc dF Dp Fw gL Ha Hr Jl Kd Lh Lx Lz Md Mp Mr Nd Nl Pa Pf Rg To Tr Uk Vp Tj) bJ(Aa aC AD Aj bP bX Co cW Dc Dg dH Dk Dl Dp Hr Ij In Iu Jk Ju Kj Kl Ks Lh Mm Ms Mw Nr Ny Oi Oy Po Pz Rm Tv Ub) dM(aH Al bG cE cF cK Cq Dc dF DG dH Dk Ha Iz Jk Jl Jo Kl Kr Ks Lx Mn Mx No Nv On Pa Pf Qb Qh Rm Tr Tv Vp Vs Tj) cI(Al aQ cE cW DC dH Fw gL Hr Id In Ir Jo Ju Kr Ks Lh Lu Lx Mn Mp Mr Mx My Nx Pa Pf Qb Rg To Vp Tj) Lv(cE Cq dB Dc dF dH Dk Dp Ha Hr Jk Jl Js Ks Lh Lx Lz Mn Mx No Nv Ny Pa Pf Po Qb Qh Tr Tv Tz Vp Tj) Kd(aG aH bG bX Cp Cx dC Dd dG Fw Ik In Iu Jg Jl Jm Ju Ke Li Lx Ly Lz Mk Ng Ok Ph Qh Ss To Tt Vp) gL(Aa Ad Al Ba bN cE cG cS dC dF dH Hr Ij Iq Jg Kj Ks Lh Mm Mn Mp Ms Nv Ny On Pf Pz Tv Tz Ug) bG(AA aD aH bA BN bP bV cE cF cP cW Dp Fw Ij Iz Jt Ju Lu Lz Ms Ng Oe Pf Ub Uk Uu) bP(aV bU cE Cq dG dH Dk Ha Hr Il Jl Lx Mn Mr Mx Nd No Oz Pa Pb Pe Pf Qh Tr Vp Tj) aD(Ad aH bB Bn bU cE cZ dH Dp Fw Ha Hc Ij Iz Lz Mm Mp Ny Oe Po Pz Rg To Ub Vv) Bn(Aa aG aH cS Dp Ha Jo Jt Ju Kf Kl Kr Lh Lz Mm Mp Nl Nm Pg To Tt Uu Vv) My(Ad Aj Bg Ct Dg Dk Dl Ij Jg Kf Mm Ms Nm Nv On Oy Pz Qu Ss Tr Tt Ue Vs) aH(Aj aV bA Bo bU cP cR cT cW dB Dp Ex Hr In Iz Kj Ks Lz Ms Ug Uk Tj) cP(Ad Aj Al Cx Dg Dl Fw Ha Ij Kl Ks Lh Ng Nm Nv Pf Po Pz Rm Ug Vv) cW(Ad Al bB bE cE cZ Dg dH Ef Ha Iz Jo Kl Mm Mx Nv Pf Rg Tr Vo Tj) Mp(aN Cq Cx dH Dp Ex Ez Ha Hq Hv Hx Lz Mi Mn Mz Oe Po Tr Up Vp) Aa(aA aJ aV bN bS cD cE cF cR dB dF Ha Ko Li Mb Md Nd Pj Vp) Cx(Cq cS dH Ha Iz Jk Jo Jt Ju Ks Lh Lz Pf Po Qb Tt Uk Vo) Ms(bU cD cE cF cZ DC dF Ha Hv Lz Nl Pa Pf To Uo Vp) aJ(bU dG dK Dl Fw Ha Iz Jt Kr No Nv Ny Pz Qb Rm Vo Vv) bA(cG Cq cZ Dc dF Jl Kl Ny Pa Qb Qh Qu Tr Tt Tv Vp Vs) Ex(aG Ao cX dK Jq Jt Kf Lh Mj Mx Of Om Rm Up Vo Vv) Ez(cE Co De Dg Il In Iz Jo Kj Kl Ks Ng Ss Uc Vs) Hv(Af dH Dk Hr Jk Jl Ks Lh Mn No Nv Po Qn Vs Tj) Im(Dl Ef Ha Ij Iq Js Kr Ks Mx No Ny Qb Qm Rm Tv) cF(bN Dg Ij Iq Jk Jo Kf Kj Ks Lh Mn Nm Oi Po Qm) cS(aQ bB Dc dI dK Ik Jl Mw Nq Nv Pf Pz Ss Tt Uk) Mi(bS cE Cq dH Hq Il Jk Jo Ks Mn Mr Oy Pf Uk) Hx(cE Dg Dk Dl Ij Jg Jk Jl Jt Kl Lh Mn Nm Nv) Li(Dc Fw Ha Jl Lh Lz Mr No Pf Po Rg Tv Up Vp) bU(Ad bN bV bX cE dB Ij Ks Mn Nx Oi Oy Qm Uk) aA(aG cE dC dH Ef Iz Kl Ng No Nv Ny Oi Tv) Lz(Ad Aj cE dC Dg dK Iz Jo Kj Ng Uc Ue) To(aG cE Dg Dl Ij Jt Kf Kl Kr Nm Qn Vv) Ko(Dg Dl Ij Iz Jg Jk Ke Lh Mn Nm Pz Vv) Ef(Ad aU De eF Fr Hc Hu Ij Jo Oy Vs) Fw(Al aQ bF bQ cR Iz Kl Kr Lh Ra Vs) Mv(Bg Hq Ij Jk Jo Mk Mn Oy Pg Vs) Hu(cE Iz Jo Ke Kl Oy Po Vo Vs) aG(Dc eF Iz Ks Mn Pf Rg Vp Tj) bN(bX Dc Iq Iu Ju Ke Lu Ny Tr) Kl(aQ aV Ba bV cY eF Jp Ma) Nl(Ij Mn Nb Ne Oe Ub Uu) cE(bV bZ Co cT De eF Jp) Mx(Aj bX Kj Oe Qd Qn) Ug(dF dH Dk Jl Nd Qn) Cq(cT Mt Oe Ph Uk) bX(cD Dk Qb Qm Tz) Aj(cZ Jf Qb Rg) De(Hq Iz Jo Pg) Ma(dH Hq Jo Uu) Mt(dH Ha Mr Tj) Qd(No Pg Rm Up) Ki(Dk Lh Mn Tz) Ld(Dk Mr No Up) Uk(cD Iq Kc Ng) bV(dF Iq Ng Tt) cR(Ks Lh Tv Ub) Nq(Pg Po Up) Uc(aV Hc Ua) Jp(Jt Ke Uu) Rm(bF Ih Qe) Rg(bM cM Nc) Oi(bB bE cZ) Vo(aV Fb Sr) Co(Hq Oy) Ha(dC Oe) Ub(bS cD) Hr(cD Vv) Qb(Kj Qa) Jh(Om Oy) Uu(aQ cY) cO(bQ dH) cT(dF Tv) cZ(Iz Kj) DcdC DpIq PoFp LudF LyRb TtdK JfSs QuQg JnJs JoPb OePg OmeF VvbM aCbE bWdH} Jj{Og(bA Cx Et Ih Ii Im Ip Ir Iu Jh Jn Jo Jp Jq Jr Jt Kc Li Lw Ly Ma Mb Me Mf Mj Mm Mw Mx Nc Nj No Nq Om Oy Pc Qb Qd) Kc(Aa An Ao BN bX cF cS De Fb gL Ii Io Jf Jq Jv Kd Lu Lv Mj Ml My Of Or Ow Qn Up Us Uu Vo Vp Vv Wm) Us(aA aX BA bC bV Co Ct CX dK gL Hc Hu Iu Jh Kd Kg Kq Li Mg Mi Mp Mu Mv Ng Nn Ua Uf Ut Vv Wm) cS(AF bA BN cF cP cT CX dB dR Hb Hu Hv Io Jq Jt Kd Kk Lu Lv Mf Mg My Nn Or Ow

Figure 15 Continued

Qn Qv Up) Ly(Et Fp Hq Ii Il Ip Jh Jn Jo Jr Jt Lj Lw Mj Mk Mm Mn Mr Mw Nb Nc Nr Om Oy Pb Po Qb) Mg(aJ Ao bA Bb Bn bV cT Cx De
dM Hb Ih Ji Jr Kk Li Mb Mj Mx Nb No Nv Om Or Qn Qv Ue) Nc(Et Hw Ii Im Ip Jh Ji Jo Jt Lw Ma Mj Mk Mm Mr Nb Ni Nr Nw Om Oy Pb Pc
Po Qd) Af(aA Aw aX BA Bg cF Ch CP CT De Hc Kd Kg Kq Lv My Nn Nq Qy Ut) Mb(Et Ih Ii Im Ip Ir Iu Jo Jt Li Lw Ma Mj Mm Mn Mw Nb
No Om Oy Pb Pc Qb) Nj(Et Ih Ii Il Im Ip Ir Jh Jo Jt Lw Mj Mq Mw Nf Ni No Nq Om Pb Qb) Li(Hw Ih Im Ip Is Jh Ji Jp Lu Lw Ma Me Mf Mk
Mr Mz Nb Nr Nt Pc Qb) Pb(Et Im Jh Jo Jr Jt Lw Ma Md Mf Mj Mk Mm Mr Nb No Nr Po Qb) Cx(aA aX bA bC cF cP CT dB Ez Hu Hv Hx Kk
Lu Lv My Nn) bA(aF An aW aX bJ Bn cF cP cX Ii Io Jq Lv My No Ny Om) Ma(Fp Ih Ii Ir Ji Jp Jt Lu Lw Me Mz Nb Of Po Qb) cF(aA aF aJ
aW aX Bn bV cT cX dM Hv Lv My Nn Ow) Nr(Ih Im Ir Iv Ji Jp Jr Mf Na Nt Nv Nw Qb Qd) Om(Et gL Ih Im Ir Jh Jo Jp Jt Mn Mw No Po Qb)
aX(aC cP cT cX Hu Hv Jq Kd Kk Lv Or Ow Qv) Nn(aW Bn bV cP cT dM Hb Jg Jr Kd Kk Nv) Ih(Ii Jk Jo Lu Lw Mj Mk Mr Nb Oy Pc Po)
Jr(Hw Ii Ip Jo Jt Mk Mm Mr No Oy Pc) Po(Fp Ir Iv Jp Js Lw Md Mf Mz Qd) Nb(Fp Im Ir Jg Ji Jp Md Mf Mz Qd) Nw(Fp Iv Jk Js Mf Mk Mr Ms Mz Pe) Pc(Im Ir Ji Jp Mc Md Mf Ms Mx Ns) Bn(aA cP CT gL Hu Lv Mv My) Lw(Fp Iv Jp Lu Me Nq Oy Qb) gL(bN Hb Lv Ms Ow Qn Qv Uu) Mz(Fp Ii Jo Lu Me Ms Oy) Im(Ii Jk Jo Lu Mj Mk Mr) Ir(Hw Jk Mk Mr Oy Pa Pe) Qd(Ij Iq Jk Js Ms Pe Qc) Mf(Ii Jp Jt Mk Mr No) Is(Fp Jk Js Lu Mk Mr) Qb(Hw Ii Iq Mk Mr Oy) Ji(Fp Iv Jp Jq Oy Qa) cT(aF cX Io Jq Lv Mu) Md(Ii Nd No Nv Oy) Hb(Jp Kd Kg Ko Kq) Ow(bN dK Kd My Qv) Fp(Ii Iv Jo) No(Js Mc Na) Qa(Jk Jo Ms) Jp(Jo Me Ni) Jq(Kd Kg Kq) aA(aF cP cX) Ao(Hu Mv) Et(Lu Oy) Lv(bC bV) Mu(cX Kk) My(aW dB) Nv(Ms Of) Ok(Mk Mr) cP(bV dB) BaJt DeQy LuMm LzMj MpNd NaHw NiNk IvOy QvcX QnUr OrdK} Og{Jg(Fp Hu Hw Hx Ik Ip Iq Is Iv Jl Jt Lh Li Lj Lw Lx Ly Mb Md Mk Mp Mr Ms Mv My Mz Ng Nj No Nr Ns Nu Of Om Pa Pb Pe Qa Qd Qe) Mu(aJ Ao aW bA Bn bV cE Cx De Fp Hu Hv Hw Hx Iq Is Iv Jl Jp Jq Lh Lw Ly Mj Mk Mr Ms Mz Nj Nn No Nr Nu Of Om Pb Pc Pe Qe) Nn(bA Fp Hw Hx Ik Ip Ir Is Iv Jl Jp Jq Lh Lw Ly Mb Md Me Mk Mr Ms Mt Mv My Mz Nc Nj No Nr Nt Nu Pa Pb Pe Qa Qd Qe) Jl(Fp Hv Hw Hx Ik Iq Is Iv Jp Jq Jt Lw Lx Ly Ma Mg Mk Mr Ms Mt Mv My Mz Nj Nr Nu Nw Of Pa Pb Pc Qa Qe) Mv(Af Ao Fp Hu Hv Hw Hx Iq Is Iv Lh Li Lw Ly Mb Mk Mr Ms Mz Nb Ng Nj Nr Nu Nw Of Om Pa Pb Pc Pe) Hu(AF Fp Hv Hw Hx Ij Ip Ir Is Iv Jp Jq Lh Li Mb Mg Mj Mm Mp My Mz Nb No Nu Pb Pc Qa Qe) Lx(Hq Hv Ik Iv Jo Jp Js Md Mf Mg Mk Mr My Mz Ni Nj Nr Nu Nw Of Om Pa Pe Pg Po) Hv(Hw Ik Ip Iq Is Jp Lh Lw Mb Mg Mk Mm Mp Mr Mt My Nj Nr Nu Pa Pb Pc Pe) Pa(Fp Hr Ik Im Iq Is Iv Jp Jq Ma Mb Mg Mt My Mz Nj Nu Pb Qa Qe) Pb(Hw Hx Is Iv Jp Lh Lw Mr My Mz No Nr Nu Nw Pe Qa Qd Qe) Ik(Hw Hx Jp Lh Lw Mj Mk Mr My Mz No Nr Pc Pe) Kc(Af cX Hb Ii Mj My Of Ow To Up Ur Us Vp) Nw(Iq Is Iv Jt Ml Mp My Nc Nj Nu Om Pc) Mb(Hw Hx Jp Lh Lw Mk Mr My Nr Pc Pe) bA(Af aW cE Cx Ii Io Jq Mr Nx Pg) My(Fp Hw Iv Lh Mk Mr Nj Nr Pe) aA(aG Al aQ aW aX Bn cS dH Ow) Af(cT gL Jh Kq Lv Mg Nq) Pc(Fp Is Iv Md Ms Mz Pe) aF(aJ bV cS cT fR gL Lv) Mg(Hw Mk Mr Nr Pe Qv) Mp(Hq Nd Ns Oz Pd Pf) Fp(Hw Lw Mk Mr Nr) Jp(Hw Ly Mk Mr Pe) aJ(Cx dG dH Io Mx) Lv(aW Bn Cx Dc) Mt(Hw Mk Mr Nr) Hx(Iq Lw Nu Om) Is(Hw Iq Mk Mr) Ii(Ba gL Ow) Io(bV cS Ow) Lh(Iq Jo Lw) Ur(dK Jv Ow) No(Js Md) Kk(cS cX) Us(bV Ez) aX(aW Qv) gL(Qn Vo) WmOk LwIv MdNb OrdK} Mu{bA(aA AD aE aF aG Al aW aX aY Ba bF Bg bP bQ cF cG Co CP Cq cS Ct Cv Cw CX Dc Dd Dg Dk Dl Ha Hq Hr Hu Ij In Io Jg Jh Lh Lv Mb Md Mj Mk Ml Mm Mn Mq Mr Ms Mw Na Nb Nf Nq Nt Nv Nx On Qb Vo) cP(aA Ad aJ Al aX Bb bF Bg bV cE Co Cq Cx Dc Dk Hq Hr Hu In Jh Jk Jt Md Mq Mr Mw Na Nf Nq Of Oy Pg Po Qb) Af(aC aE aJ Ao aQ aS bN Bo bV cF cQ cW dB dD Hr Ii Iq Jo Jp Jq Kd Kk Lu Ly Mb Ms My Of Om Pc Qv Ug) Ao(aE aJ aW aX Ba bV cS CX De dM Fr gL Hr Hu Hx Il Iq Jn Kk Lv Lx Ly My Mz Nw Ok On Pc) De(aA aJ aW Cs cT cX Ii Il Iq Jo Jq Jt Kk Lu Lv Ly Mb Of Pc Qv) Jo(aE aJ aW aY Ba Bn bV cF CS cW CX dM dN gL Ji Kk Lx) Jq(aE aJ aW Bo bV cF cS CX dB Ex Ji Kd Kk Kn On) Om(aC aE aJ aS aW Bo bV cS CX Ji Jl Lw Lx Mz Or) cT(Bb Bn cE Hq Iq Jk Jt Of Oy Pg Uc Us) aA(aC aE aG aW Bn cF dH Dl Mx Ng Oe) Ii(aJ aW Bn bV cS Cx Ex gL Kn) Of(cF Hu Ji Jl Lw Lx Nw Pa) Ms(Ji Lw Lx Mz Nw Ok Pc) On(Js My Nb Ng Nv Ny Oy) Jt(aJ aW bV cS Ji Ko) Qv(cX gL Kd Kk Or) Bn(aW Il Iq Lv) Ok(Iq Mb Nx Oe) Us(bV Kk St) Lx(Js Oe) Md(Mp Nw) Hr(CX) Ji(Mb Nx) bV(Io Iq) ExHa LvcE MmcS UcKk HbUr NwNx OePa VogL OycX} Kc{cP(Aa aC Ad Al Ao aQ aX BN bV bX cS CX Dc dK Dl dR gL Ha In Iq Iu Jf Jk Jq Ks Lu Mj Mm My Oy Pf Qb Qn Rj Rm To Tv Ub Ug Up Ur Vp) Ur(Aa An Ao Ar bA Bn cS cX De Dg Dl Ii Ij Io Iq Jo Jq Jt Jv Kd Kl Lu Lv Ml Mm My Nx Of Ow Pj Qn Qv Rc To Us Uu Vo Wm) Af(aA aE aK aU aV bA cF cS cT cY dD dJ dR eF Ha Hb Hr Hu Ii Iq Jf Jn Jp Kd Kq Lu Lv Mj Mz Nl Of Ow Rj To Up Us Vp) My(Aa Ad aE Aj Ap Cp Cw CX De dH Ef Ha Ij Jg Jk Jq Ke Kf Kl Ks Mj Om Oy Pz Qn Ss Tr Uc Ug) Ii(bA bN cS cT CX Fb Fn Hc Hu Hv In Jn Jp Kd Kn Ml Mz Or Ow Qv Vv) Hb(aQ aV bN bV cS cT CX cY dR Ex gL Kd Ko Lv Or Ow Qv To Uh) Qv(An aX Bn bX cS Io Jq Kd Lv Mj Ml Ne Nl Of Or Qn Us Uu Vo) Of(aQ bA bN cF cS Ct cX gL Hc Jf Lu Lv Ni Or Ow Us Vv) Us(aA bA bN cS cT Cx gL Jp Kd Lv Mz Ow Qn St To) Vo(aQ aV BA bN cF cS cT cY Jf Jp Kd Ko Ma Sr) cX(AA Ao bA bN Dd Ha Iq Jo Mj Up) bA(Dc Ha Jq Kf Mj Nx Tv Up Vp) Ao(aQ bN cS gL Hc Kd Lv Ow) Jo(bN cS gL Kd Lv Mg Ml) Jq(aQ bN cS cT dR Hv Jn) Jt(bN cS gL Jp Ko) gL(Bn Iz Kj Uu) Aa(aA bN Ow) cT(Ha Tv) CxUp LuMl ToUu IqcS} aA{Af(aF aW bC bN bO bU cF Co cS cT cU dB De Dk dN Hu Io Iq Jh Kg Kq Lv My Nn Nq Oe Om Uf Ur Us) cX(Ax Cv Hb Hu Ii Io Iq Jq Jt Jv Kg Lu Lv Mg Ms My No Oe Of Om Qb Qv Rj Up Ur Us Vo) Jt(aF cS Et Hu Hx Ir Is Jl Jp Jq Jr Lj Ma Mt My Mz Nn Nu Nv Om Pa Pg Po Qa) Oe(Cx Hw Ir Jl Jn Jq Jr Lh Mf Mg Mk Mr My Mz Nb Nr Nt Nu Po Qa Qd Qe) Cx(aF bO bU cU Ii Iq Lv Mg Ms My Ni Of Om Qb Qv Us) Mg(aG aW Bn cP De Dl Hv Jo Jr Ml Ni Pc Qv Us) Ms(aX cF Hx Ik Jn Lh Mf Ml Mv Nb Nu Pa Qd Qe) Us(aF dK Ez Jp Kg Kq Ld Mi Mv My Nn Ow Uf) Ng(Jg Lh Ma Mb Mf Mt Mv My Nn Nt Nu Qd) Ni(Hv Hx Jn Lh Li Nc Nk Pa Pe Po Qe) Js(Hv Is Jn No Pa Po Qa Qd Qe) Lv(Aa aF aG Bn cF cP Wm) Mb(Hx Jg Lh Mm Pa Pc Po) Jq(aX cS Hu Ma Mf Ml Nn) aP(aJ bC bG bV bZ dE dM) Ii(cS Hv Ir Lh Ow Pg) Bn(bN cP dB My Ur) Mf(Fr Hx My Mz Pc) Io(aF bA cF Hx Pa) Of(cF cS Hx Nv Pa) Ma(Hv Hx Jr Mz) Md(Jg Mq Nd Nn) bO(cS cU dM dN) Ns(Jg Mq Nd) Pc(My Om Oy) bG(bJ bU cE) bQ(bZ cU dN) dG(bZ cU dM) Fr(Jr Ml) Nn(Hv Pe) Jg(Ml Nj) Qv(aX Kg) dE(aC bM) dL(aJ dN) AoMv NoNa LzLi MmNw MxPe HwHx IqPa JoLh QnUr aFoK aNbJ aQaU bZcV cEcU cSdM} Qv{aX(Af aQ bA bJ Bn bP cA cI cP cV Cx dK dR fP gL Hu Hx Im Jv Ko Lv Mf Mg My Mz Nn Qn Ug Up Ur Us Vo Wm) cX(aF aJ aU bC bE bJ bP cR cZ dB dK fR Hv Im Iq Jp Jv Kd Kg Kk Ld Lv Mg Mi My Nn Or Ow Uf Up Ur Us) Ow(Af aJ aQ aV bE bF bJ BN bP cE cF cS Cx dK Ez Ii Io Jq Kk Ko Lv Nn Qn Up Us Vp) Mg(aG Ao bP Cx De gL Hb Ii Jo Jq Jv Kd Kk Lv Of Om Qn Qw Uc Ug Ur Us Vo) gL(Ao Bn bP dK fP Io Jo Jq Jv Kd Kg Kk Lv Mj Mm Nn Of Ur Us Uu) Kg(Ao Cx De Ii Iq Jo Jq Jv Kd Kk Om Or Qn Uc Ur Us Vo) Af(bC De Ef Jp Kd Kk Lv Mv My Ng Nn Nq Uf Ur) Us(cS Ez Im Kd Kq Lv Mi Mt Mv My Nn Qy Uf) Cx(aF aU bC bP cS dK Ez Jp Kd Kk Nn Uf) Ur(Bn cS dK Io Jv Kd Lv Mi My Qn Wm) cS(aQ cV dI dR fP Iq Kd Ko Or Up) Kd(Ii Io Jv Mj Nn Qn Up) Im(Ha Io Jv Mj Mx Vp) Nn(bA cP Kk Mj Or) Lv(Bn Ez Jv Kk Mj) Uf(Jv Kk Or Vo) Ii(Ko Kq On) Mj(Ma Qd) Jp(Io Jv) Kk(My Qn) Kq(Ha Vo) BaVo WmdK EzUp KoQn} Ok{Jo(Fp Hv Hx Ik Iq Iv Jp Jq Lh Lu Lx Ly Ma Mb Mf Mg Mp Ms Mt Mz Nc Nj Nu Pb Pc Pe Pg Qa Qd Qe) Jt(Fp Hv Hw Hx Ik Iq Is Iv Jq Lh Lu Ly Ma Mb Mj Mk Mp Mr Nb Nc Nr Nu Nw Of Pa Pb Pc Pe Pg Qd) Of(Hv Iq Is Jg Jp Jq Lu Lx Ly Ma Mb Mg Mp Ms Mt Mz Nc Nj Pb Pg Qa Qe) Nx(Fp Hu Hv Iq Jl Jp Lu Lx Ly Mb Mg Mp Mt Mv My Nc Nj Nq Pc Pg Qa) Iq(Hu Hv Hx Ir Is Jl Jp Jq Lu Lx Ma Mb Mp Mv My Mz On Qa Qe) Om(Hu Hv Hx Is Jp Lu Lx Ma Mb Mg Mp Mt My Mz Nn Pe Qa Qe) Jq(Hx Is Jp Lu Lx Mb Mg Mp Mt Mv My Mz Nj Nw Oe Qa) Ms(Hv Hx Jl Jp Lx Ly Mg Mp Mt Mv Mz Nq Nu Pc Qa) Lu(Hu Hv Jl Jp Lx Mb My Mz Nn Nu Oe) Oe(Hu Hv Hw Hx Jl Mk Mv My Pa Pc) Mb(Hu Hv Hx Jl Jp Mp Mv Mz) Nn(Hu Hv Ly Md Nc Nj Nv) Fr(Hv Md Nc Nj) Ii(Hu Hv Jl Pg) Ly(Jp Mv) Md(Mp Pc) Ng(Hu Mv) Ni(Nc Nk) Nj(Jp My) Hv(Hu Js) JlJs} Us{cS(AF aQ bA bN bV cT CX dD dK dR Ez fP gL Hv Hx Ii Iq Jo Kd Lv Mm My Ng Of Or Ow Qy St Ug Vo) bV(aF aU aX cM dK Ef Ez gL Hv Hx Iu Jh Jp Jv Kd Kg Kk Kq Lv Mg Mi Mp Mv Nn Nq Ow Qd Qy Uf Ur)

Figure 15 Continued gL(aF Ao aW bA Bn dK Ez Hb Io Jo Jp Jq Jv Kk Lv Mj Mm My Of Ow Qn Qy Ug Ur Uu Vo) bA(aF aU bP Co CX Hv Iu Jh Jv Kd Kg Kq Ld
Li Lv Mg Mp Mv Nn Nq Ow Qd Uf) Kk(Af aX CX Ef Ez Fr Hu Iu Kg Kq Lv Mg Mi Mp Mv Nn Nq Ow Qy Uf) My(Af aW cT CX Hb Ii Jo Jv
Kd Ld Lv Ms Of St Ug Ur Vo) Jp(Af aX CX Hb Io Jv Lv Ow Qy) Ug(aX Ez Kd Kg Kq Mg Mv Nn Vv) cX(cT Cu Ez Hc Hx Kd Ur Ut) St(aX
Hb Mi Mv Nn Of Qy) Kq(Af cP Hb Ii Jo Jq Vo) Kd(aX Ii Jo Lv Ow) Ez(cP cT dR Lv) Ur(Cx Lv Ow Wm) Af(Jh Mg Ut) Qy(cP cT Qw) aX(cP
cT Qx) Cx(Cu Ut) Of(Hc Ng) Ow(cT Lv) BaVo MgUe HbKo JqUt OrdK} Ur{Hb(aJ aQ aX bE bJ Bn cP dK dR eF Et Ex Ez Fr Ih Im Is Ji Jn Kn
Ko Lh Li Mf Mv Mz Ne Ng Nn On Ph Qa Qc Qe Rg Sr Uf Un Wm) Af(Aw aX bA bC bE Bg bJ bN Ch cP cS CT cZ dB De dK EF Hc Hu Hv
Im Io Jv Kd Kg Kk Lv Mi Nn Nq Qy Uf Ut Wm) Ow(Aa Ao Ar aX bA Bn cP cS CX dK Ii Io Jt Jv Kd Kk Lu Mm Ms Nx Of Rb Rh Ue Ug Up
Wm) Cx(aE aW aX bA bN cF cS cT cW dB dK Hv Ii Io Jv Kd Kk Lu Ms My Wm) cX(aE aX bA bN cF cT cW dB dE dK Hv Ii Io Jv Kd Kk Lu
Ms My Wm) Jq(cS dK gL Hv Jr Kd Kg Kq Lv Mg My Uf) cS(aG Bn cP fP Ii Iq Jv Kd Kk Or Qn) Qn(bA dK gL Hv Kd Kk Lv My Wm) My(Ao
Bn Ii Jv Ms Of Vo) Kd(An Ii Io Jo Jt Mm Ms) Ii(Hu Hv Kn Tn Wm) gL(Ao Bn Jt Ms Uu) Bn(Io Jv Lv) Mg(Ao Jo Ue) Or(dK Ms) aX(bA cP)
CtOf WmUg ExJv IobA cPdK} Fr{Ii(bA cP cS cT Fp gL Hu Hw Hx Ir Is Iv Ji Kd Lx Mr Nj Nu Nw Ow Pa Pe Qa Qe) Js(Fp Hw Hx Ir Is Iv Jn Lx Mj Mr Mz No Nr Nu Nw On Pb Pe Qa Qe) Md(Fp Hu Hx Iv Ji Jo Jt Lw Lx Nc Ng Nj Nu Nw Oe Pb Pc) Jo(Hu Hx Ik Ip Ir Is Ji Lh Lw Mk Ns Nu Pb Qe Wm) Jt(aF Hu Hx Ih Ip Jl Lh Lj Mk Mm Mp Nj No Nw) My(Hu Hv Hx Jl Lx Ly Nb Nc Nj Nw On Pa Pc) Oe(Fp Hu Hx Iv Ji Jl Lw Nj Nu) Mp(Hq Ng Ns Oz Pd Pf Pg) Nc(Hu Ji Lw Ni Nk Ns On) Ni(Lx Ng Nj Nk Pa Pe) Hv(Hw Jk Ly Nj Oi Po) Nx(Fp Hx Iv Lw Lx Nu) Hr(Hw Mr On Pa Pe) Oi(Fp Hu Iv Ly Nu) Nj(Hu Ji Lw On) Hq(Hw Lx Pa Pe) Ny(Ir Nw On Qe) Af(cP dB Kk) Po(Fp Lx Pe) Ns(Lw Pc) Ly(Ji On) Ms(Ij Nn) Qe(Jm Pz) Oy(Mk Pa) WmOf NmJi HwHx JqOn NvNw} gL{Ii(aD aE aF aQ aW bA BN bP cF cP Cs cT cW Ex Fp Hv Hx Ih Ji Jn Kd Kg Kk Kn Ko Kq Ld Lj Lx Mf Mg Ml My Mz Nn On Qa Qe Qn Qy Rf Tn Vo Wm) Vo(aF aW aX bA bN Bo bV cB cF cS cT CW dB Gp Hb Jq Kd Kg Kk Lv Ma Mf Mg Ml Ms My Oe Om Ow Pb Qn Uf Vv) cX(aE aF aW bA bN cA cE cI Hr Hv Ij Io Jk Jq Lu Mb Mj Ml Mm Mp Mw Nd Nj) Af(bS bU cT cV Io Jo Jt Mm Mv Nd Nj Nn Nq Of Om) Cx(Io Iu Jk Jt Kj Kr Lv Mj Ml Mp Ms Oe Pz Rm Uk) Uu(aW Bn cS dK Kk Kq Lv Ma Ow Qn) Ao(Hc Jp Lv Mv Nn Ow Qn Qy Uf) Jo(aF cS Kg Lv Mf Mg Ow Qy) Bn(fP Hb Kk Lv Ow To) Jq(Kg Kk Kq Ow) Qn(bN dK Mj) Om(Kk Kq Qy) Ow(Iz Mm Of) Lv(Hb Of) aF(aE bA) UcKq HbKk cSfP} bA{Ii(AF aJ aS aX bJ bP cF cP cW Cx Hu Hv Hx Ih Kd Kg Lv Mi Ow Qa Qc Qy Uf) Nn(Af Ao cE cP Ha Hb Hr Jo Js Jt Ks Lv Ny Oe Of Om Po Vo) Mg(Ad Ba Bb Bn cE Cx Dc Dg Dl Hb Ij Nx Ny Om Oy Pg Vo) Jq(aF aX cF cP cS Io Kq Lv Mv My Nq Qy Uf) Af(Hu Io Jt Kq Lv Mv Mw My Oe Om Uf) Bn(aF aW bJ bM bO cF cS CV dB Jt) Cv(aX bC bJ bN bO cE cP cS cV cX) aF(Ad Io Jo Lu Nx Oe Of Vo) cS(De fP Iq Jo Jt Lv Of Om) Jt(aX cF CX Lv My) aX(Io Iq Mj Om Vo) dH(aP aY bW cN cR) Ao(cP Mv My Nq) Of(bJ cF Lv My) dA(bQ bR bU dI) Cx(Io Iq Om) De(bJ cP dB) cG(aY bC cO) Nq(Om Oy) Lv(cF Jo) Io(bP Ow) Qy(Hu Vs) Kq(Ha Uc) Vo(Kg Uf) cP(Ad Cq) cU(bF bQ) MacE MyJo JvcX LiPg bEoK} cT{cS(aD aF aW BN cF cG cL cP CV dB dE fP Io Iq Jo Jq Jt Of) cX(aD aE aN Ao aP aW aY bE bJ Bn bV cE cF cN cP cR cU Cv dB) bJ(aD aE aN Ao aY BN bP bV cE cF cP cU Cx dA dB dN) cP(aE aF Ao aS aW bF bP bV cE cF cU De dN Ii) cU(aD aF aW bF bN cE cF cG Cx dB dE dH) Cx(aD aE aF Ao aY cE cF dE dN Jt) Ii(aJ aX Kq Mg Mv My Nn Nq Qe) cF(aD aF aP aY bN bP dA dB dN) Af(Bo Jh Kg Kq Mg Mv My Uf) aW(aP bE Bn bW dA dB dE dN) Jq(aX Kg Kq Mg Nn Qy Uf) dB(aF bE BN bW dA dN) aP(aF cE cG cV dH) Mg(Ao Jt Of Vo) dE(aD bP cC cV) Bn(aJ bC dM) NnPg MyOf QyOm JtaF aDbE bFdN bUdA} On{Jq(Fp Hr Hu Hv Is Iv Ji Jl Jp Lx Ly Mf Mt Mv Mw Mz Nj Nu Nv Ny Pe Qa Qd) Js(Fp Hv Im Ir Is Iv Jl Jn Jp Lj Lx Ma Mg Mt My Mz Nc Ng Nu Pa Pe Qd Qe) Nv(Fp Hv Jp Lu Lx Ly Ma Mg Mv My Nc Nj Om Qa) Ni(Hv Jl Jp Lx My Nb Nf Ng Nj Nk Nm Qa) My(Hu Io Lu Ly Mv Ng Nj Nn Nq Oy) Lu(Hr Mz Nb Nf Ng Nu Ny Oy) Ly(Jp Ma Mz Nb Nf Ng Ny Oy) Ng(Mg Mm Mt Mv Nm Nn) Hv(Hr Hw Nb Nj Ny Oy) Iq(Mm Nm Oi Pz) Ny(Fp Hu Jl Nj) Om(Im Mg Mt Nb) Oy(Mv Nj Pb Pc) Nn(Mw Ns Oi) Ma(Hq Nc Nf) Hw(Hx Jl Qa) Ii(Fn Hb Uk) Wm(Jt Of) Mp(Hq Mn) Hr(Fp Hu) NmMb LzLi NbHu NjJp QaQc} Lv{Iq(Hw Ij Im Ir Jg Lh Li Mg Mj Mk Mr Nb No Nr Po Qe) Om(Ij Im Ir Li Mn Ms Mt Nu Nv Nx Pc Qd) Js(Ih Im It Jg Jt Ma Mg Nc Nf Of) Ms(Ij Mg Mt Mw Nq Nu Nv Po Qe) Nx(Et Ij Ik Ir Jq No Pc Po Qd) Ng(Ij Ik Jk Mg Mt Nq Nv) Jt(Et Im Ir Mg No Nv Qd) Ly(Jg Jo Mg Nu Of Pc) Jq(Ir Jg Lu Mg Mt Mv) Of(cS Ik Iv Nq Nu) Pb(Ml No Nu Ny Oz) Af(aX cP Jh My) Md(Nq Nv Ny Pg) Nc(Ne Ni Nk Nl) Is(Iu Jn Jr) Iv(Jn Jr Mx) Jo(cP cS Nt) No(Ml Na) Ma(Mm Nm) Io(Mr Pa) Iu(Ih Ir) Nv(Ii Oi) Oe(Ij Pc) aX(cP Lu) MjMx NdPf HqPg QeJm KkcS} Lx{Js(Hu Hv Is Ji Jl Jn Jp Lz Mb Mg Mt Mv My Mz Nw Pa Qa Qd Qe) Jo(Ik Jl Ma Mb Md Mv My Ni Nj Nn Nu Qe) Hu(Hq Iq Jt Md Ms Ng Ni Oe Of Om Po) Jt(Jg Ji Jl Jp My Pa Qa Qd Qe) Of(Jg Jl Jp Lz Ma Mv My Ni Nn) Md(Iq Mb Mp Mv My Nn Pf) Om(Ji Jl Jp Mv My Mz Qa) Ms(Ji Mv My Nn Nw Pc) Iq(Jp Mv My Qa Qe) Ji(Jq Lu Nx) Oe(Mv My Nn) Ni(Nc Nj) NnOy MbMy MpHq NwNx} Ji{Lu(Hu Hv Iq Jl Jq Mb Md Ms My Mz Nj Nu Nx Of Om) Jl(Hu Ii Iq Jo Jq Js Jt Mb Ms Nx Oe Of) Ms(Hv Hx Jp Jq Ly Mv Mz Nq Pa Pc) Hu(Hv Ii Iq Jo Jq Jt Md Nx Of Om) My(Iq Jo Jq Jt Mb Nx Of Om) Hv(Ii Iq Jq Js Jt Mb Of Om) Nn(Iq Mb Md Nx Of Om) Mv(Iq Jo Jq Jt Of Om) Jp(Jt Mb Of Om) Oe(Hw Mk Pa) Hx(Iq Om) Jq(Is Mb) Pc(Md Nx) JgJt JsPa} Kk{cS(Aa Af aG Ao aQ Bn cE cF cP CX DG dH Dl dR fP fR Il Io Iq Jo Jq Jt Jv Kd Kj Kl Kr Ks Ly Mj Mm Mp My Nm Of Om Or Ow Pf Pg Pz Qb Qn Rj Up Uu Vo) Af(Jh Kg Kq Mg My Nn Nq Ow Uf) Mg(Ao Ii Jq Jt Ks Of Om) My(Ao Jo Jt Ks Mj Of) Of(aQ cF Kg Nn) aX(bN cP Mj Vo) Jq(Kg Nn Uf) Jo(Kg Nn) Ow(Ii Up) Vo(aQ bN) DeUf HbaQ} cP{Af(aF aJ aP AW Ba bC Bg bN Bo bQ bV bZ cS cU Cw dB De dF Dk dM fR Kq Mv Nq Qy) Bn(aF aJ AW aX bC bN Bo bV bZ cS cU dB fR) Cx(aF aJ aW bC bN bV bZ cS cU dB dM fR) dM(bN bV bZ cF cS dB dE dN) fR(aF aW bN bU cC cF cX) aX(Jo Jq Mb Vo) dB(bV cS cU) MgJo MvIi aWcU} aJ{dH(aW aZ bC bG bO bV cF cS CX dE dF dM) dG(Af bF bG bV cF cO Cx dF dM) aW(bC bG bO cF cU CX dL) dL(aC Af bU cF cU Cx dK) bN(Af Bn cF cS Cx dN) cU(aF aP bO cF cX) cX(cF dE dM dN) Cx(aC cF) Mg(Jo Jt) cE(bF bZ) IiOw aFdE bOcF bUbX} Ii{Ow(bN cS Fb Hc Hu Hx Ih Jn Jp Kn Ko Kq My Mz Vv) Ex(bN Ez Hc Ld Mg My Qy) Kd(cS Jp Mg My Mz Nn Tn) cS(dR Hu Kn Ko Or Vv) Kq(Af Hv Jn Jp Vo) My(Gl Ko Kp) Kn(Jp Mg Mv) Ba(Hv Vo) AfMv HvKo ImVv HcJp} Nw{Md(Hu Hv Iq Jo Jt Lu Mb Mp Ms Mv My Nn Oe Of Om Pc) Ms(Hu Hv Jl Jp Js Mv My Pc) Nx(Hu Hv Jl Js Mp My Nj Nn) Js(Hv Jl Mb Pa Qa) Of(Hu Mp Mv My) My(Jt Nn) Hu(Jo Jt) LuNy JlOm} Jo{Mg(Af aW aX Ba bV bZ cF CS Cx dM dN Jv Kn Ko Kp Ph Rg Rh Ug Uk Up Vv Wm) Hu(Jl Lh Lw Pa Pc) Wm(Jp Mi) Kd(cS Nn) AfKq MbJl MdOm MyaW IocS} Md{Mp(Fp Hv Iq Jg Jl Jp Js Ly Mb Ms Mv My Of Om Pb Pc) Om(Mb Ms Nn Oe Of) Pc(Hu My)} Jt{Jp(cF Cx Hw Jl Kd Kg Lh Lw Mk Mr Pa Pe) Ko(Kq Mg Ow) Jg(Pa Pe) BaaF WmMi LwJl KdcS} Vo{Ba(AF aX Bn cX Hb Jq) Kq(aE Af Ao aX cS Hb) cS(aQ cX Kd) Ex(aQ bN) aX(Kd Or)} dM{dE(aC aF bN bU cF cS cX) cF(aC bN cS dB dN) bN(cS dB dN) bZ(cE dH) cS(cX dB) dBdN} Hu{Mp(Hq Oz Pd) Ms(Lw Nn Pc) Jl(Ng Of Om) My(Of Pc) LwOf NgJg OePa} Ug{Mg(Af cX Jq Mp Om) Af(Jh Kg Kq) cS(bN cX Io) Ow(bN Up) MjaX} Nn{Ms(Hv Hx Jg Jp Me My Mz No) JqKd OePa} Mi{Wm(Hr In Of Pg) Nb(Ns Oz) Hr(Lj Nx) PoQd IjPf} Af{Mv(aE Bo Hr) Ba(aW dB) QyQw JqKq bNcS} Hb{Jp(Bn cX Io Kg Up) Ex(aQ aU) UcKq} Jl{Of(Jg Lw My) Om(Lw Mv Ne) Js(No Pa)} Jq{Ex(aU Kg Qy) Mg(Kd Ue) UcKq KdOw} cS{Kd(cX Io Up) CxbN LuaF HcOf cXiZ} Js{Pa(Hr Jn Qa) Mp(Hq Pd)} Cx{aW(bC fR) MjKd aCfR} Wm{In(Jp Mg) JpOf} My{MsPc UcKq OfcF} Jg{MgNg MkOf MsHv} cX{fR(aW cF) MgUe} Om{MvMz QyQw} MbNdHq OraXdK aWcFcU

Constrained panels with 2 analytes, where 1.0E-7 >= 'model p-value' > 0. Contains 35 panels of 66,377 total panels evaluated. : Mi(aA Hq Hu Iq Jj Jo Js Jt Lv Ly Mb Md Ms Ni Nn Of Og Om On Pg) Lv(aA Fr Jj Og Ok On) On(Jj Nx Of Og) Ou(Ii Qv Ur) Jj(Fr Hu)

Figure 15 Continued

Constrained panels with 2 analytes, where 1.0E-6 >= 'model p-value' > 1.0E-7. Contains 88 panels of 66,377 total panels evaluated. : Jj(aA Ik Jl Lh Lx Mp Mt Mu Mv My Nu Ok Ou Pe Pg Qe Wm) bA(aA AF aJ aS aW bE bJ bO cF cP CX dB dE dM dN) Lv(Hu Hv Hx Ji Jl Jp Lw Lx Mr Mu Mv My Mz Nw Pa Pe) Ou(aE aF Ao aW aX cX Io Jq Jv Of Om Us) aA(aW cP cT cX dH Fp Ji Nw Og Ok On Pb) Fr(Mb Mi Of Og Om) On(Ii Jt Mb Ms Oe) CxgL MiMu OgOk aJcT Constrained panels with 2 analytes, where 1.0E-5 >= 'model p-value' > 1.0E-6. Contains 212 panels of 66,377 total panels evaluated. : Ou(Af aG bG BN cE cF cI cP Cq cS Cx Dg dK Dl Dp Ef Fw gL Ha Hb Hr Iz Jo Jt Kc Kd Kf Kk Kl Ks Lh Mj Mp Mu Ng Nm Nn Oe Og Pg Po Qn Uf Ug Uk Up Uu Vo) Jj(Fp Hv Hw Hx Ih Ij Im Ir Is Iv Jg Ji Jk Jo Jp Li Lw Ly Ma Mg Mk Mr Mz Nb Nj Nn Nr Nt Nv Nw Pa Pb Pc Po Qa Qd) aA(aF bN cF cU cV Cx dB dE dM dN Fr Hu Hv Iq Jg Jq Jr Lh Lw Lx Ly Ma Mb Mg Ml Mp Ms Mz Nj Nn Nu Of Om Pa Pe Po) Lv(Hw Is Jg Jo Js Lh Li Lu Ma Mg Mk Mm Mp Ms Nb Nn No Nr Of Pb Pc Qa Qe) Fr(Fp Hv Iq Ji Jo Jt Lw Ly Md Ms Nc Ng Nj Oe Ok On) On(Hr Hu Hv Iq Jo Lx Ma Md My Nc Nj Nv Om Oy) Ok(Hu Hv Iq Jq Jt Lu Mb Nn Of) cT(Af bJ cP CX dE dM dN) Og(Ji Jl Lx Mu Nw) aJ(bN cF cP dG dL) Af(gL Mu Ur) bA(Bn cE cV) Qv(Kc Ow) Ur(Cx Hb) KccP Constrained panels with 2 analytes, where 1.0E-4 >= 'model p-value' > 1.0E-5. Contains 263 panels of 66,377 total panels evaluated. : Jj(Af aX bA Bn cF cP cS cT Cx Et gL Ii Il Ip Iu Jh Jn Jr Jt Kc Kd Mb Mf Mj Mm Mw Mx Nc No Nq Og Om Ow Oy Qb Us) Og(bA Fp Hu Hv Hw Hx Ik Is Iv Jg Jp Kc Lh Lw Mk Mr Mv My Nn Nr Pa Pb Pc Pe Qe Ur) Lx(Hq Hu Hv Iq Ji Jo Jp Js Mb Md Ms Mu Mv My Ni Nn Oe Of Ok Om) Ur(Bn cS cX dK gL Hv Ii Io Jq Jv Kc Kd Kk Lv My Ow Qn Qv Us Wm) Ji(Hu Hv Iq Jl Jp Jq Lu Ly Mb Ms Mu Mv My Nn Of Om Pa Pb) Qv(Af aX cS CX dK gL Im Kd Kg Kk Lv Mg Or Uf) bA(Cv De Ii Io Jo Jq Jt Lv Mg Mu Nn Oe Of Om Us) Kc(Aa AF Ao CX Hb Ii Jo Jq My Of Us Vo) Us(aA bV cS cX gL Jp Kd Kk Lv My Ow St) Ok(Jl Jo Jp Mp Ms Mu Mv My Nc Nx Om) cP(Af Bn bV bZ cS cU Cx dB dM fR Mu) cT(aD aE aP aW bE Bn bP cF cS cU dB) dM(aJ bN bZ cF cS CX dB dE dN) aJ(Af aW cU CX dH dN) gL(aF aW cX Ii Qn Uu Vo) Nw(Js Jt Md Ms Of) Mu(Ao Bn De Of) Mp(Hq Md Pd) Jl(Ms Of Om) On(Mm Nm Pz) Cx(cS fR) Ii(Kd Ow) aA(Af Bn) LwHu MdOm MgUg NgJg KkcS bNdN cXfR Constrained panels with 2 analytes, where 1.0E-3 >= 'model p-value' > 1.0E-4. Contains 975 panels of 66,377 total panels evaluated. : Og(AF aJ aW aX Bn bV cF cP cS cT CX dM Et gL Ii Ij Im Ip Ir Jh Jk Jq Jr Jt Kd Kk Li Ly Ma Mb Mg Mj Mm Mp Mt Mx Mz Nb Nc Nj No Nt Nu Nv Om Or Ow Oy Pg Po Qa Qb Qd Qv To Uf Ug Us Wm) Us(Af aJ aQ aU aW aX bN Co cP cT Cx cY dK dR EF Ex Ez Fr Hc Hu Hv Hx Iu Jh Jn Kg Ko Kq Ld Li Mg Mi Mp Mu Mv Mw Mz Ng Nn Nq Of Or Pd Ph Qd Qe Qn Qv Qy Tn To Uf Ug Ut Vo Vv) Mu(aE AJ aW aX Bb Bg bV cE cF Co Cq cS cT CX Dc Dd Dk dM Fp gL Hu Hv Hw Hx Is Iv Jl Jo Jp Kk Lh Li Lw Mb Mk Mp Mr Ms Mz Ng Nr Nw Oi Om Pa Pb Pe Qe) Kk(aE Af Ao aQ aV aX bA BN bP bX cF cP CX cY dK dR gL Hb Ii Io Jj Jo Jq Jt Kd Kg Ks Lv Mg Mj My Nn Of Om Ow Qn To Uf Ug Up Vo) Af(aP AW AX Ba bC Bg bN Bo bV bZ cF cS cU dB De dF Dk dM dN FR Hu iZ Jh Jp Kd Kg Kq Lu Lv Mi Mv My Nq Ow Uf Ug) Hu(Fp Hv Hw Hx Ir Is Iv Jl Jo Jp Lh Li Mj Mk Mm Mp Mr Ms My Mz Nb Ng Nn No Nr Nw Of Pa Pb Pc Pe Po Qa Qe Ug) Kc(aA aE aQ bA BN cF cS cT De dK Dl gL Ha Hr Iq Iz Jf Jt Kd Kj Ks Lu Lv Mj Ml Mm Or Ow Qn To Ug Up Uu Vp) Jp(Fp Hb Hv Hw Hx Iq Jl Jt Lh Li Lu Lw Ly Mb Mk Mp Mr Ms Mv My Ni Nj Nn Nr Nu Nw Of Om Pa Pb Pe Qn Qv Vo) Cx(aC aP aW AX Ba BC bN Bo bV bZ cF cU dB dF dN Fr Hr iZ Jo Kd Lu Lv Mi My Ow To Ug Up Vo) gL(aC aE aG bA BN bS dB dH Hb Io Iz Jo Jq Jt Jv Kd Kj Kl Lv Mj Mm Ms Oe Of Om Ow Ss Ug Up) My(aW bA cT Fp Hv Hw Iv Jg Jl Lh Lw Mb Mk Mp Mr Ms Nj Nn Nr Nw Of Om Pa Pb Pc Pe Qv Ug Vo) Ow(aA aE Ao aW aX bN cF cP cS cX dK Hb Io Jo Jq Jt Jv Kd Mj Mm Ms Of Qn Ug Up Uu Vo) Pa(Fp Hr Hv Iq Is Jg Jo Js Lw Lx Ma Mb Mg Mm Mp Ms Mt Mv Mz Ni Nn Nu Oe Of Om Qa Qe) Jj(aJ aW bC Bo bV Ct cU cX dB dM Ex Fb Hb Jv Kg Ko Ky Ld Or Qn Qv Qy To Uf Up Vv) Hv(Ip Iq Jg Jl Lh Lw Ma Mb Mg Mk Mm Mp Mr Ms Mt Mv Mz Ni Nn Nr Nu Nw Pb Pc Pe) Mv(Ao Fp Hw Iq Jl Jo Lh Li Lw Ly Mk Mp Mr Ms Mz Ng Nr Nu Nw Of Om Pb Pc) cS(aW Ax bG BN cF dE Ii Io Iq iZ Jo Jt Kd Lu Lv Oe Of Or Ug Up Vo) Mp(Fp Hw Hx Ir Is Iv Jg Jl Lh Mb Mr Mz Nd Nn Ns Nw Oz Pf Pg Qe) Ug(aQ aX bA BN cF cX dK Io Kd Kg Lv Mj Qy To Uf Up Ur Vv Wm) Pe(Hr Iq Jg Ji Jo Js Lw Lx Mb Ms Mt Mz Ni Nn Nu Oe Of Om Pc Qa) Jl(Fp Ii Iq Is Iv Jo Js Jt Lw Mb Mt Mz Ng Ni Nw Pb Qa Qd Qe) Vo(aQ aX BA cT cX Kd Kg Ko Kq Lv Ma Mg Or Qv Sr Uf Ur) cP(aP aW AX bG bN Bo cF cR dE dN Jo Lv Mi Oe Ur) Lw(Fp Hx Is Iv Jg Lh Lu Mb Mt Mz Nn Pb Pc Qa Qe) cT(Ao Cv De Ii Io Jo Jq Jt Lv Mg Nn Oe Of Om Pg) Nw(Ii Iq Jo Lu Mb Ml Mm Mt Nc Nj Nn Nu Nx Om) Kd(aX cX dK Hb Io Jo Jq Jt Mj Of Qn To Up) iZ(aW aX aZ bA bG bZ cU cX dB dE dK eF oK) Ii(aJ Ba Ex Hc Kg Kn Ko Kq Or Tn Uf Vv) Of(Ba cF Hc Is Jg Kg Lh Ma Nn Nv Uf Ur) Qv(aA bA bC bJ Bn bP Io Jv Ko Mi Qn) Ur(aA aG An aW aX bA bN cU dB Lu Or) Nn(Fp Hw Ir Iv Lh Mb Md Mr Ms Mz) cF(aP aW bV bZ cU dA dE dN fR Lv) Mz(Lh Lu Mb Mk Mr Ms Om Pb Pc) bA(Hb Iq Jv Ny Pg Qn Uf Up Uu) Jo(aX Ba bZ Kg Kq Lh Uf Wm) cU(aW BN Bo dB dE dN fR) Lv(aJ aW aX Bn bV dB dM) Lh(Iq Jt Mb Ms Ni Oe Om) Jg(Fp Jt Mb Md Ms Om) Lx(Jt Mk Mr Nr Po) Iq(Hx Ir Is Qa Qe) aP(aW bN cX dB dH) Mk(Fp Mb Mt Qa) Jq(aX Kg Kq Uf) Om(Hx Is Qa Qe) aA(Ax Cv oK Qn) bZ(aW bN cE dE) cX(Or Rj To Up) dN(aW bG dB dE) Bn(aJ Bo dM) Mr(Mb Mt Qa) Jt(Ba Ko Kq) Pc(Md Ms Ns) fR(aF aW bN) No(Js Md) Lu(aF aX) Hw(Ji Mt) Is(Ms Pb) aJ(Oe oK) BodM WmIn MbHx MgUe UcKq IobV JiNx OrdK bEoK eFnY Constrained panels with 2 analytes, where 1.0E-2 >= 'model p-value' > 1.0E-3. Contains 1,518 panels of 66,377 total panels evaluated. : Jo(AF aJ aP AW bC Bg BN Bo bV cF Co Cp Ct cU Cw cX dB dM dN eF Et Ex fR Hc Hw Hx Ij Ik Ir Is Iv Jg Jt Kn Ko Li Ma Mg Mk Mm Mp Mr My Nb Nn Nr Nt Nu Nv Or Pg Ph Po Qa Qd Qe Qn Qy Rj Tn To Up Vv) Of(aJ Aw aX Bg Bn Bo bV bZ cP cU CX dN dR eF Et Ex Hw Hx Ij Ik Im Ir Iv Jk Jt Ko Kq Ky Li Lw Mg Mj Mk Mm Mp Mr Mt Mz Nb No Nr Nu Om Or Pc Pg Ph Po Qa Qd Qe Qn Qy Tn To Up Vv Wm) Mg(Ad Af AJ Ao aW Bn bV cP Cx Dl dM Dp Fp Ha Hb Hw Iz Jf Jv Kj Ks Lu Mj Mk Mr Ms Mx Nc No Nr Nu Om Or Pb Pc Pe Qn Qw Rg Rj To Ub Uc Uk Up Uu) Vo(aA AF aJ aU aV aW bC Bg BN Bo bV bZ cF cP CU Cw cY dB dK dR eF Ex Fb Fr Hc Hu Hx Im Jf Jg Jn Og Pb Ph Qd Qe Qn Qy Tn To Ua Uh Up Vv) Ii(aP Aw aX Xg BN Bo bP bV bZ cF Co CP CU Cw cX dB dF Dk dM dN dR EF Fa Fb fR Gf Ky Ld Pg Ph Qy Rj Sr St To Ua Uh Un Up Vu Wm) bN(aN aO aW AX Ba bC bG Bn Bo bQ bV cF cN cO cR cX dA dB dE dF dG eF Ex Fr Hu Hv Jp Jv Kd Kg Lu Lv Mi Mv My Oe Og Or Qn Rj To Uf Up) My(Ad aE AJ Al Ao aX Bn Bo bV cF cP cS cX dB Dc dM Hb Hx Iq Is Iz Jv Kd Kj Ks Ky Li Mz Nc No Nu Qa Qe Qn Qw Rj To Ub Uk Up Uu) Om(aJ aX Ba Bo bV cS Et Fp Hw Ij Im Ir Kg Ko Li Lw Ma Mb Mj Mk Mm Mp Mr Ms Mt Nb Nn No Nr Nu Nv Or Pb Pc Pg Po Qd To Uf Up) Bn(aC aP aW AX Ba bC bV bZ cF cN dB dF dN FR Hr Hu Hv Hx iZ Jp Jt Kd Kg Kq Lu Mi Mv Nq Oe Or Ow Rg Rj To Uf Up) aW(aO Ax Ba bC bG Bo bQ bV cO cR cX dA dB dE dF eC eF Fr Hu Hv Jp Kg Kq Lu Mi Mv Nn Oe oF oK Or pF Qn Qy Rj To Uf Up) Kk(aA Bg Cq Dc Dd Dk Ha Ij In Ir Iv Jd Je Js Jv Jy Md Mm Mr Ms Mw Mx Nb No Nv Nx Oe Oy Pg Qx Ra Tv Uu Vp Vs Wm Tj) IIb(aA aJ aQ aV aX Bo cP cS cT cX dD dK dR eF Et Ex Fr Hv Hx Jn Kg Ko Kq Ky Lv Mu Mv Mz Nn Og Or Ph To Uf Uh Up) Uf(aA aE Aj Ao cF cI cP cT Cx De Dl Ex Ha Il Io Iq Jf Jt Kj Ks Lu Lv Mj Mp Ms Or Qn Qw To Ub Uc Uk Up Uu) Up(aA aE Af aJ aQ aX bP bV cP cT cU dK Ex Hv Hx Io Jn Jp Kg Kq Li Lv Mi Mm Mp Mt Og Or Qd Qn Qy Rj St To) Qn(aE aJ aQ aU aV aX Bo bV cF cP cS cT dB

Ni Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe Us)
Il(aX Et Fp Hq Hr Hu Hv Hw Ih Ii Ij Ik Im In Io Ip Iq Ir Is It Iu Iv Jg Jh Ji Jk Jl Jm Jn Jo Jq Jr Js Jt Lh Li Lj Lw Lx Ly Lz Ma Mb Mc Md Me Mf Mg Mh Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Ow Oy Oz Pa Pb Pc Pd Pe Pf Pg Po Pz Qa Qb Qc Qd Qe) Hv(Aa aX bA bV Et Fp Hq Hr Hu Hw Ih Ii Ij Ik Im In Io Ip Iq Ir Is It Iu Iv Jg Jh Jk Jl Jm Jn Jo Jr Js Jt Lh Li Lj Lw Lx Ly Lz Ma Mb Mc Md Me Mf Mg Mh Mj Mk Ml Mm Mn Mp Mq Mr Ms Mt Mu Mv Mw Mx Mz Na Nb Nc Nd Ne Nf Ng Ni Nj Nk Nl Nn No Nq Nr Ns Nt Nu Nv Nw Nx Ny Oe Of Oh Oi Ok On Oy Oz Pa Pb Pc Pd Pe Pf Pg Po Pz Qa Qb Qc Qd Qe Us) Hu(Et Fp Hq Hr Hw Ih Ii Ij Ik Im In Io Ip Iq Ir Is It Iu Iv Jg Jh Jk Jl Jm Jn Jo Jq Jr Js Jt Lh Li Lw Lx Ly Lz Ma Mb Mc Md Me Mf Mg Mh Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe Us) Mv(Af bA Et Fp Hq Hr Hw Ih Ii Ij Ik In Io Ip Iq Is It Iu Iv Jh Jk Jl Jm Jn Jo Jq Jr Js Jt Lh Li Lj Lw Lx Ly Lz Ma Mb Mc Md Me Mf Mg Mh Mj Mk Ml Mn Mp Mq Mr Ms Mt Mu Mw Mx Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qc Qe) Mu(Af bA bV cT Fp Hq Hr Hw Ih Ii Ij Ik In Io Ip Iq Is It Iu Iv Jh Jk Jl Jm Jn Jo Jq Jr Js Jt Lh Li Lj Lw Lx Ly Lz Ma Mb Mc Md Me Mf Mg Mh Mj Mk Ml Mn Mp Mq Mr Ms Mt Mw Mx Mz Na Nb Nc Nd Ne Nf Ng Nh Nj Nl Nm Nn No Nq Nr Ns Nt Nv Nw Nj Nk Nl Nn No Nq Jr Js Jt Lh Li Lw Lx Ly Lz Ma Mb Mc Md Mf Mh Mj Mk Ml Mm Mn Mp Mq Ms Mt Mz Na Nb Nc Nd Ne Nf Ng Ni Nj Nk Nl Nm Nn No Nq Ns Nt Nu Nv Nw Nx Ny Oe Of Oh Oi Ok Om Oy Oz Pa Pb Pc Pd Pe Pf Pg Po Pz Qa Qb Qc Qe Us) Us(Af aJ AP aQ aV aX BA Bg BN Bo bP bV cF CS CT CU cW CX cY dD dJ DK dR Ex Ez Fp Hb Hc Ih Im Io Is Jf Ji Jn Jv Kc Kd Kg Kk Kn Ko Kq Ky Ld Li Lj Lx Ma Mf Mg Mj Mr Mt Mz Ng Nw Oe Of Om Ow Pe Ph Pi Qa Qd Qe Qn Qt Qu Rb Rf Rj Sr Tn To Ua Ub Ug Up Ur Ut Vo Vv Wm) Mt(Fp Hq Hr Hw Ih Ii Ij Ik Im In Io Iq Ir It Iu Iv Jh Jk Jl Jm Jn Jo Jq Jr Js Jt Li Lw Lx Ly Lz Ma Mb Mc Md Me Mf Mh Mj Mk Ml Mn Mp Mq Mr Ms Mw Mx Mz Na Nb Nd Ne Nf Ng Ni Nj Nk Nl Nm Nn No Nq Nr Ns Nt Nu Nv Nw Nx Ny Oe Of Oh Oi Om Oy Oz Pa Pb Pc Pd Pe Pf Pg Po Pz Qa Qc Qe) Jl(Et Fp Hq Hr Hw Ih Ii Im In Io Ip Iq Ir Is It Iu Iv Jh Ji Jk Jo Jq Jr Js Jt Li Lj Lx Ly Lz Mb Mc Md Me Mf Mh Mj Mk Ml Mm Mn Mp Mq Ms Mw Mz Na Nb Nd Ne Nf Ng Ni Nk Nl Nm Nn No Nq Nr Ns Nu Nv Nw Nx Ny Oe Of Oh Oi Ok Om Oy Oz Pa Pb Pc Pe Pf Pg Po Pz Qa Qc Qd Qe)
Nn(bA Hq Hr Hw Ih Ii Ij In Io Iq It Iu Iv Jh Jk Jo Jq Js Jt Lh Li Lw Lx Ly Lz Mb Mc Md Me Mf Mg Mh Mj Mk Ml Mn Mp Mq Mr Ms Mw Mx Mz Na Nb Nc Nd Ne Nf Ng Ni Nj Nk Nl Nm No Nq Nr Nt Nu Nv Nw Nx Ny Oe Of Oh Oi Om Oy Oz Pa Pc Pd Pe Pf Pg Po Pz Qb Qc Qe)
Jo(aJ aX Ba bV bZ Co cS Et Ez Fp Hq Hw Ih Ii Ij Ik Im Io Ip Ir Is It Iu Iv Jg Jh Ji Jk Jt Kc Kd Kg Kq Lh Li Lj Lw Lx Lz Ma Mg Mj Mk Mm Mn Mp Mq Mr Mw Mx Mz Nb Ne Nf Nm No Nq Nr Nt Nu Nv Nw Ny Oh Ok Om Oy Pa Pb Pc Pe Pf Pg Po Qa Qb Qd Qe Sr Ur) Nx(Fp Hq Hw Ih Ii Ij Ik Im Io Ip Iq Ir Is It Iv Jg Jh Ji Jn Jr Lh Li Lj Lw Lx Lz Ma Mc Md Mf Mh Mj Mk Ml Mn Mp Mq Mr Mw Mx Mz Nb Nd Nf Ni Nj Nk Nm No Nq Nr Ns Nt Nu Nv Nw Ny Of Oh Ok Om Oy Oz Pa Pb Pc Pe Pf Po Pz Qa Qb Qc Qd Qe Ur) Nu(Hq Hr Hw Ij Ik Im In Io Iq It Iu Jg Jh Jm Jn Jr Js Jt Li Lw Lx Lz Ma Mb Mc Md Me Mf Mh Mj Mk Ml Mp Mq Mr Ms Mw Mx Mz Na Nb Nd Nf Ng Ni Nj Nk Nl Nm No Nq Nr Ns Nt Nv Nw Ny Oe Of Oh Oi Oy Oz Pa Pb Pc Pd Pe Pf Po Pz Qa Qc) Jh(Af Hq Hr Hw Ih Ij Ik Im In Io Iq Iu Jk Li Lw Lx Lz Mb Mc Md Me Mf Mh Mj Mk Ml Mn Mp Mq Mr Mw Mx Mz Na Nb Nd Ne Nf Ng Ni Nj Nl Nm No Nq Nr Nt Nv Nw Ny Oe Of Oh Om Oy Oz Pa Pb Pc Pd Pe Pf Po Pz Qa Qe) Of(aJ aX Ba Bg bV cF cS Ct Cu Et Hc Hq Hw Ih Ij Ik Im Ip Ir Is It Iu Iv Jg Ji Jk Lh Li Lj Lx Lz Ma Mg Mj Mk Mn Mp Mw Mx Mz Nb Nc Ni No Nq Nr Nv Nw Ny Oe Oh Ok Om Oy Pa Pb Pe Pf Pg Po Pz Qa Qb Qd Qe St) Lx(Et Hq Hr Hw Ih Ii Ij Im In Io Ip It Iu Iv Jg Jk Jq Jr Lh Li Lw Lz Ma Mb Mc Md Mf Mh Mj Mk Ml Mn Mp Mq Mr Na Nb Nd Nf Ni Nj Nk Nl Nm No Nq Nr Nv Nw Ny Oe Oh Ok Oy Oz Pa Pb Pc Pe Pf Pg Po Pz Qc) Mp(aX Hq Hr Hw Ih Ii Ij Ik In Io Iq Iu Js Jt Li Lw Lz Mb Mc Md Me Mf Mh Mj Mk Mq Mr Ms Mx Mz Na Nb Nc Ng Ni Nj Nl Nm No Nq Nr Nt Nv Nw Ny Oe Oh Oi Om Pa Pb Pc Pd Pe Pf Pg Po Pz Qa Qc Qe Ur) Ur(Aa aD aE Af An Ar As aX bA Bb BN bV cF cP cS Ct cU cW CX DB De Dl Ex Hb Ii Iq Jf Jn Jq Js Jt Jv Lz Mj Ml Ms Mx Mz Na Nj Ny Oe Om Ow Qn Qw Rb Rc Rh Rj To Ub Ue Ug Up Vo Vu Wm) Nq(Af Fp Hq Hr Hw Ih Ii Ik In Io Iq It Js Li Lj Lw Lz Mb Mc Md Me Mf Mh Mj Mk Ml Mq Mr Ms Mx Mz Na Nc Nd Nf Ng Ni Nj Nk Nl Nm No Nr Ns Nt Nv Ny Oe Oi Om Oy Pa Pd Pe Pf Pg Qa Qe) Li(Hq Hr Hw Ii Ij Ik In Io It Iu Jk Js Jt Lw Lz Mc Md Me Mf Mh Mj Mk Ml Mq Mr Ms Mw Mx Na Nb Nc Nd Nf Ng Ni Nj Nk Nl Nm No Nr Ns Nt Nw Ny Oe Oh Oy Pa Pb Pc Pd Pf Pg Po Pz Qc) aX(aC aD aE Af aJ Ao aP aW aY bA BN Bo bP bS bV cA cE cF cl cL cQ cS cT cW CX dB DE dI dM Hr Ii In Io Jq Kc Kd Kk Ly Me Mj Ms Na Om Oy Pg Ug Up) Md(Hq Ij Im Io Iq Is Jk Jr Lw Lz Ma Mc Mh Mj Mk Mq Mr Mw Mx Mz Na Nb Ni Nj No Nr Ns Nv Nw Ny Oe Oh Ok Oy Oz Pa Pb Pd Pf Pg Pz Qa Qe) Nw(Hb Hq Hr Hw Ii Ij In It Iu Jn Jq Js Jt Lw Lz Mc Mf Mh Mj Mk Mm Mr Na Nb Nd Ni Nl Nm Nr Nt Nv Oe Oh Om Oy Oz Pc Pd Pe Po Pz) Om(bA bV dR Hq Hr Ii Ik Im In Ir Is It Iv Jg Jk Jt Kq Ma Mb Mc Me Mf Mg Mw Mx Mz Na Nd Ni Nl Nm Nv Oe Oh Ok Pd Pf Pg Qa Qe) Ni(Hq Hw Ih Ij Io Iq Ir Is It Jg Lw Ly Lz Mg Mj Mk Mr Ms Mw Mx Mz Nb Nc Nj Nk Nl No Nr Ns Nv Oe Ok Oy Pa Pe Pg Qa Qe) Ii(Aa aJ BA bV cS cT Ex Hc Ik Im In Ip Ir Is Jg Jk Kc Kd Ko Lh Ma Mg Mx Mz Na Nv Ok Ow Pa Pe Qa Qd Qe Sr St Tn Vu)
Nb(Hq Hr Hw In Io It Lw Lz Mb Mc Mh Mj Mk Mq Mr Na Nd Nf Nj Nl Nm Nr Nt Ny Oe Oh Oy Oz Pb Pc Pf Pg Po) bA(aE AF aU bC bJ bM BN bP bW cF cS Cv CX cZ dB Dc dE dK dN Io Jq Kc Mg Mj Mx Oe Ow Pg Qb) Mk(Hq Hr Hw In Io Lw Lz Mb Mc Mf Mh Mj Ml Mq Mw Na Nd Nf Nj Ny Oe Oh Ok Oy Oz Pb Pf Po Pz Qc) bV(Af bC BN bS cA cF cM Cx dA dB Dc dH Hw Io Iq Ir Is Jm Js Jt Mx Ne Nl Oe Oi Pg Pz Qb Up) Ns(Fp Hq Hw Ih In Io Iq It Ji Lj Mc Mr Mw Mz Nj Nk Nl No Nr Ny Oh Ok Pd Pf Pz Qa) Mz(Lm In Iq It Iu Jg Jm Jq Js Jt Ly Ma Ms Na Nc Ng Nk Nm Oe Oi Pb Pz Qa Qc) Mw(Hq Hw In Io Iq Iu Js Lw Mb Mc Mf Mh Ml Nd Ng Nj Nk Nm Nr Oe Oh Pe Pf) Js(Et Fp Ih Ik Ip Ir It Jg Ji Jn Lj Ma Mg Mh Mm Mx Nc Nt Nv Ok Pg Qe) Qa(Ik In Iq It Iu Jg Jm Jt Ly Ma Mf Mm Ms Nc Ne Ng Nk Nm Oi Pz Qc) Mb(Hw Ij Iq Lw Ly Me Mf Mg Mj Mq Mr Nd Nf Nr Oe Pa Pc Pe) In(cS Hq Hw Ih Ij It Lw Mg Mj Mr Mx Nf Nr Oy Pa Pe Po Qe) Pz(Hq Io Is It Jg Ma Mc Mg Mh Mq Nd Nj Nv Ny Oh Pf Qc Qe) Im(Aa Fp Hb Ik Iq Iu Jt Mm Mn Ms Nc Ne Ng Nk Nm Oi Vo) Oe(Aa Hw Ij Jg Kk Lh Lw Ml Mr Mx Nc No Nr Ok Pa Pc Pe) Na(Ij Io Jg Ji Lw Lz Mj Mr Mx Nr Oh Ok Pa Pe Pf Qe) Ow(Af cE Dk Hb Jq Kj Kk Mj Ms Pg Qn Rh Ue Up Uu Vo) Mc(Hq Ij Io Lw Mg Mh Mx Nd Nj Nr Ny Oh Pe Pf Qc) Jt(aJ Ik Is Iv Jg Kc Kd Ma Mg Mx Nt Nv Ok Pe Qe) Io(Aa cT Ex It Lw Lz Mh Mq Nd Nl Ny Oh Pf Qc) Jq(Aa aJ cS cT Ik Iv Jg Kc Kd Kq Mg Nv Ok) Pf(Hq Ij Lz Mg Mh Mq Mx Nj Ny Oh Qc) Nd(It Lz Mh Mq Mx Nr Ny Oh Pe Qc) Qe(It Iu Jg Jm Mm Ms Ne Nk Nm Qc) cS(Af Al bN cF cT fP Kc Kk Pg Ug) Mg(Hq It Jg Ma Me Nc Nk Oz Qc) Vo(aQ Ba bN Kc Kd Ko Kq Sr Uf) Af(aJ bC Bo cF cT dB Kc Kd) Nr(Hr Hw It Lw Lz Mh Mj Mq) Mx(Jm Lw Mh Ms Nm No Ny Oi) Nv(Iu Mm Ms Ne Nj Nk Nm Oi) Ok(Jm Mf Mr Nm Nt Oi Pa Pe) Ma(Iu Mm Ms Ng Nm Oi Pa) Ij(Hr It Lw Mh Nl Ny Oy) Hb(aQ Ex Kc Kd Kk Ko Sr) Jg(Iq Iu Ly Ms Nm Oi Pa) cT(aF Bn bP CX dN) Lw(Hr Jk Lz Mh Nf) Hq(Iu Mh Nj Nk Ny) Lz(Mr No Pa Pe) Mj(Aa Ex Hr Kk) Iq(Ih Ik Nc Pg) Is(Jn Jr Nm Oi) Qc(Iv Nc Ny Oh) cF(bP dM fR Kk) Et(Ms Ng Oi) Ue(Kq Qy Uf) Hr(Hw Pa Pe) Kd(Qn Ug Up) Ms(aJ Mm) Hw(Mr Pa) Kc(Aa cP) Ny(Ml Oh) Pe(It Nf) WmUg PoPa LyRb NcNk NjOh UcKq IvJr KkQn aJdH} Qv{Ow(AA aC AD aE AF aG aH al aJ aK AL aM AN AO AP aQ AR AS aU aV AW AX aY aZ BA BB BC bE bF BG bH bI bJ BL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp dR Ed EF Et Ex Ez Fa Fb Fn FP FR Fw Gl GP Gz Ha Hb Hc Hf Hq Hr Hu Hv Hw Hx Ib Ic Id Ih Ii Ij Ik Il Im In Io Ip Iq Ir Is It Iu Iv Iz Jd Je Jf Jg Jh Ji Jk Jl Jm Jn Jo Jp Jq Jr Js Jt Ju Jv Jy Kc Kd Ke

Mg Nn) MaUu} Ba{PzbP KIKo OmcF} Im{Ha(Ex Il) IIQn} Lu{LxOe MzaF} aC{BnfR bEoK} bN{ExIo cUdN} dB{HcUu cUiZ} dK{bEoK bGiZ}

Unconstrained panels with 2 analytes, where 1.0E-7 >= 'AUC p-value' > 0. Contains 391 panels of 66,377 total panels evaluated. : Lv(aA aX bV Et Fr gL Hq Hu Hv Hw Hx Ih Ii Ij Il Im Io Ip Iq Ir Is It Jg Jh Ji Jj Jk Jl Jm Jn Jo Jp Jr Js Lh Li Lu Lw Lx Ly Lz Ma Mc Md Mf Mg Mh Mi Mj Mk Ml Mn Mp Mq Mr Mt Mu Mv Mw Mx My Mz Na Nb Nd Nf Ni Nj Nk Nl Nm Nn No Nq Nr Ns Nt Nu Nv Nw Nx Ny Oe Of Og Oh Ok Om On Ou Oy Oz Pa Pb Pc Pd Pe Pf Pg Po Pz Qa Qc Qe Qv Ur Us) Ou(aD aE AF aG aH AJ Ao aW aX bG BN bP bU cI cS cW CX DC Dg dK Dl dM dN Ef Fw gL Ha Hb Hr Ii In Io Iq Iz Jj Jo Jq Jv Kc Kd Kj Kk Kl Mg Mj Ml Ms Mx Nb Ng Ny Oe Of Om Pg Qn Qv Ss To Tz Ug Uk Uo Up Ur Us Uu Vo Vv) bA(aD aE AF aG aH aJ aL aN aP aR aS aW aX aY bC bE bF bG bH bI bJ bM BN bO bP bR bU bW bX bZ cA cC cE cF cI cK cN cO cR cS cU cV CX cZ dB dC dE dH dK dM dN Io Jj Mu Nn Ow Us) Jj(aA Af aX bV cS Ct Cx Fp Fr gL Hq Hu Hv Hx Ih Ij Ik Im Ir Is Jk Jl Kc Kd Lh Ly Mi Mp Mt My Mz Nn Nv Ow Pa Pb Pe Pg Qa Qb Qd Qe Wm) cT(AF aJ aX bC bJ BN bW bZ cO cS cU CX dB dE dN) gL(aC Af cI CX dH Ii Iz Of Qn Qv Ug Ur Us Uu Vo) Qv(Af aX cS CX Im Jv Kc Kd My Ow Ur) Ur(Af bV cS cU Cx Hb Jq Lu My Ow Qn) aA(bU cS cU CX dN Mi Mp Og) aJ(Af bN cS cU CX dH Og) Us(bV cS Jp My Ow) Mi(Ly Mb Ms Nj) Ii(Ba Kq On Tn) Og(aF Hv Kc Nw) Of(Ba Jl On) Ow(Hb Jq Ms) Kc(Af cP) Kk(aX cS) Ug(Kd My) Vo(Ba Kq) FrLy JtOn Unconstrained panels with 2 analytes, where 1.0E-6 >= 'AUC p-value' > 1.0E-7. Contains 336 panels of 66,377 total panels evaluated. : Ou(AA Ad Al aN aV bA bB bJ bM Bo bS bV cA cD cE cF cG cJ cP Cq cV dB Dd dF dH Di Dk Ex Gl Hu Hv Hx Ij Il Jf Jk Jl Jm Jn Jp Js Jt Ko Kr Ks Ky Lh Lz Md Mp Mw Mz Nd Nl Nr Nx Oi Oy Po Qb Qg Qh Qm Qu Ra Rh Rj Rm Tt Tv Ub Uc Ue Vp) bA(aA aC al aK aM aO aQ aU aV aZ bB bL Bo bQ bS bV cB cD cG cH cJ cL cM cP cQ cT Cv cW cY dA Db dD dF dG dI dJ dL gL Ii Kc Lv Mg Mi Oe Ur) Jj(aJ Bn cF cT cU Hw Ip Iu Iv Jh Ji Jp Lj Lx Ma Mb Me Mf Mu Mv Mx Nj Nq Nt Nu Nw On Oy Pf Po Qv Us) gL(Ao aW bP bU cE cS cT dB dK dN fP Hb Io Jo Jq Kc Kj Kk Kl Ks Ms Oe Rm Ss) Qv(aA aJ bC bE bJ Bn cU dB dR Jp Kg Kk Ko Li Mi Mp Or Qn Qy Uf Us) Lv(cS Fp Hr Ik In Iu Iv Jq Lj Me Mm Ms Nc Ng Nh Oi Qb Qd) aA(Af bC bJ BN bR cT dB dE Hv Iq Li Ms Nn Oe Of Pb Us) cT(aD aE aN aP bG bV cF cN cR cV dK dM Mu) Ur(aX Bn Ch cW cX Hx Ms Og Ue Ug Us Vu) Ow(Af cS Ii Kj Kk Og Qn Rh Ug Uu) Og(Fr Ji Kk Lx Mi Mu Ok On) aJ(aC bR bU dB dG dK dL dN) cS(Af Cx dM Jo Jq Kc Ug) Mi(Hv Jo Lu Me Nd Nu) Fr(Hv Jo Mb Ms Of) Kd(Af Jo Jq Us Vo) Kk(aV Cx Qn Us) bV(Cx Io Oe Up) dM(aC bN cU dB) Kc(Hb Jt Lu) Ii(Ex Vu) Of(Qa Qe) fR(CX) AaMb AjMy CuVo LxOe MsMu JtNw OmOn UgaX Unconstrained panels with 2 analytes, where 1.0E-5 >= 'AUC p-value' > 1.0E-6. Contains 741 panels of 66,377 total panels evaluated. : Ou(aC al aK aL aM An aO AP aQ aR AS aU Aw aY aZ Ba BC bE bF Bg bH bI bL bO bQ bR bW bZ cB cC CH cK cL cM cN CO Cp cQ cR Cs CT CU Cv Cw cY cZ dA Db dD DE dG dI dJ dL Dp dR Ed eF Et Ez Fa Fb Fn FP Fr GP Hc Hf Hq Hw Ib Ic Id Ih Ii Ij Il In Ip Ir Is It Iu Iv Jd Je Jg Jh Ji Jr Ju Jy Ke Kf Ki Kn Kp Kq Kx Kz Ld Lj Lu Lw Lx Ly Ma Mb Mc Me Mf Mh Mi Mk Mm Mn Mq Mr Mv My Na Nc Ne Nf Nh Ni Nj Nk Nm Nn No Nq Ns Nt Nu Nv Nw Oa Og Oh On Or Ow Oz Pa Pb Pc Pd Pe Pf Pj Pk Pz Qa Qc Qd Qe Ql Qt Qw Qx Qy Qz Rb Rc Rf Rg Ri Sr St Tn Tr Ua Ud Uh Ul Um Ut Uv Vs Vu Wm Tj) Jj(aF aP Aw Ba Bg bN Bo bP bZ Ch Co cP cW cX dB dM Et Fb Hb Hc Ii Il In It Jg Jm Jn Jo Jr Js Jt Kg Kk Ko Ld Li Lu Lw Lz Md Mg Mj Mk Mm Mn Mr Ms Mw Nb Nc Ne Ni Nk No Nr Og Oh Ok Om Pc Pz Qc Qn Qy Uf Up Ur Vu) cT(aC aG aH al aL aM aO aQ aR aS aW aY aZ bB bE bF bH bI bL bM Bo bP bQ bR bS bU bX cA cB cC cD cE cH cI cM cP Cv cW cZ dC dD dF dG dH dI dJ dL FR Io Lv Mi Nn Oe Ow Ur Us) Qv(aF An aP aQ aU aZ bA bH bN bP bV bW bX bZ cF cI cY cZ dE dK Ef Hb Hc Hu Hv Hx Io Jf Jn Jq Jr Ky Ld Ma Mb Mf Mg Mj Mm Mv Mz Ne Ni Nl Nn Pb Qd Qu Rj To Ua Ug Up Vp) aA(Aa aC aF aJ aN aQ aX aZ bG bM bO bP cI cJ cQ cR cV dD dH dK Fp Hu Hw Ii Io Ip Iv Ji Jp Jr Lw Lx Ma Md Mf Mq Mz Ng Nj Nm Ns Nw Om On Ow Pe Po Qn Ur) Ur(Aa aE aQ Ar aZ Bb bN bZ cP Ct eF Fb Hc Hq Ii Io Iq Jf Jo Jp Jt Jv Kd Kk Ml Mv Mz Ni Nx Or Pb Pc Pj Qe Rh To Ub Vo Wm) aJ(aF aG al aN aO aQ aS aU aX aZ bC bF bG bJ bL Bn bQ bS bV bZ cD cE cF cI cJ cM cP cR cV dD dE Lv Oe Qn Us) gL(aE aF aG Aj Al aN BN Bo bQ bR bS cA cL cU dD dG Iq Iu Jk Jt Jv Mm Ng nY Og Om Tz Ub Ue Uv) bA(Ad An Ao As Aw Bg Cq Ct Dc De FR Hv Jq Kd Ma Mv My Ni Nq Qy) Ow(bV CX dK Ex Ha Il Iq Jo Jp Jv Ks Mj Mp Qw Rg Ub Ue Up Vo) Og(Bo bP bV cS dB Fp Hu Hx Is Iv Jg Jp Kd Nt Qd Qe) bV(Af bN cU dB dN Jm Li Ma Mi Mp Mt Mu Mx Rj) dM(Af aQ aU aX bC bU cF cR CX dK dN) Ug(BN cF CX Kc Mf Mg Us Vv) Af(aX bC bZ cU FR Jp Kk Lv) Of(Cu Hc Im Ir Is Jg My Nv Nw) On(Hw Il Io Iq Lu Mb Nd Oe Vo) Mi(Hu Jq Jt Mm My Oe Om Pb) Jo(Is Ji Kc Kq Mp Pe Qd Qe) Kd(aX cS Hb Ii Jt Lu Ms Qn) Lx(Hw Lu Mb Nd Nu Pf Pz) cS(aP bG In Lu Mb Uk Up) Fr(Jt Nj Nu Oe Om Pb) Kc(Aa cX Jq Ph Qn Us) dN(bG bN cP cU Cx dB) Kk(Bn cF cX Hb My) Vo(aQ Im My Qe Uf) Lv(Aa Jt Mb Ne) Ii(Hc Ko Sr St) aX(Jq Mb Qx Rg) Jp(Cx Hu Mb) cU(Bo Cx iZ) Nu(Mu Mv) Kq(Jt Uc) Us(cX Hc) LuaF MbMp MvHv HbKo JlOm Unconstrained panels with 2 analytes, where 1.0E-4 >= 'AUC p-value' > 1.0E-5. Contains 1,446 panels of 66,377 total panels evaluated. : Qv(AD aE aH al aK Al aM AO Ap Ar AS aV Aw aY Ba Bc bF Bg bI bM BO bQ bR bS bU cA cB cD cE Ch cJ cL cM cN CO CP CQ cR CT CV cW dA Db DC DD De dF Dg dH DI Dk Dl dM dN Dp Ed eF Et Ez Fa Fb Fn FR Gl Gp Ha Hf Hq Hr Hw Ib Ic Id Ih Ii Ij Il In Ip Iq Ir Is It Iu Iv Iz Jd Je Jh Ji Jk Jl Jm Jo Js Jt Ju Jy Ke Kf Ki Kj Kl Kn Kp Kq Ks Kx Kz Lh Lu Lx Ly Lz Mc Md Me Mh Mk Ml Mn Mr Ms Mt Mu Mx Na Nb Nc Nd Nf Ng Nj Nk Nm No Nr Ns Nt Nu Nv Nw Nx Ny Oa Oe Of Og Ok Om On Oy Oz Pa Pc Pd Pe Pf Pg Ph Pi Pj Po Qa Qb Qc Qe Qg Qh Ql Qm Qt Qw Qx Ra Rb Rc Rf Rg Rh Ri Sr St Tn Tr Tt Tv Tz Ub Uc Ue Uh Uk Ul Un Uo Uu Uv Vo Vs Vu Wm Tj) gL(AA AD aH al aJ aK aL aM aO aP aQ aR aS aU aV aX aZ bB bC bF bG bH bI bJ bL bM bO bV bW bX bZ cB cC cD cG cH cI cK cN cO CQ cR Cu CV cW cY cZ dA DC dE dF Dg dI dJ Dk DL dM Dp dR eC Ef Ez gP gW Ha hC Hr iA iH IJ In iP iZ Jp Kd Kf Kn kQ kS Ky Ld Mj Ml Mw Nd Nj Nm No Nr Nv nW Ny Oa oE Oh Oi oN Ow Oy pF Pg Ph Pj Pz Qm Qu Qw Rc Rg Rh Rj To Tr Tt Tv Uc Uk Up Vp Vs tF) aA(aD aE aG aH al aK aL aM aO aR aS aU aV aW aY bB bE bF bI bQ bS bV bW bX bZ cA cC cD cE cF cH cK cN cO cW cY cZ dA Db dC dF dM Et Fr Hq Hr Hx Ih Ik Il In Ir Is It Iu Jg Jh Jk Jm Jn Jo Js Jt Lh Lu Ly Lz Mb Mc Me Mg Mh Mj Mk Ml Mm Mn Mr Mt Mu Mv Mw Mx My Na Nb Nc Nd Ne Nf Nk Nl No Nq Nr Nt Nu Nx Ny Oh Oi Ok Oz Pa Pc Pd Pf Pg Pz Qa Qd Qe) bV(aM aN aO aP bF bG bJ Bn bO bP bQ bR bU bW bX cA cD cF cM cX Db dD dE dH dK dM Et Ez Hr Hu Hv Hw Hx Ii Im Ip Iq Ir Is It Iu Iv Jh Jk Jp Jq Js Jv Kd Lw Lz Mb Mc Md Mj Mq Mv Mw My Mz Ne Nh Ni Nl Nn No Nq Nr Ns Nv Ny Of Oi Om Oz Pz Qb Qd Qn Qy To Tv Tz Vo Vp) Ur(aD aJ An AO Ap aS aV aY bM bP cF cR cY DB De Dg dH Di dK Dl dM dN dR Ex Fn FR Ha Hv Id Ih Il Ip It Iv Je Jl Jn Jr Js Ke Ki Kj Kn Ko Kq Kr Ks Ky Kz Lx Mb Mj Mk Na Nc Nj No Nt Ny Oe Om Oy Ph Pi Po Qa Qc Qh Qm Qw Rb Rc Rj Sr Tn Ua Uc Uk Up Uu) Jj(aE An aY aZ BC bE bJ bM bS bU bW cI cN cO Cp cR Cs Cu Cv Cw cY cZ Db Dc DE Di DK dN dR EF Ex fR Hr Io Iq Jf Jq Jv Kj Kn Kq Ky Mc Mh Ml Mq Na Nd Nf Ng Nh Nl Nm Ns Nx Ny Oe Of Oi Oz Pd Ph Qu Qx Rb Rg Rj Sr St Tn To Ua Ug) bA(Aa Aj Al Ap Ar Ax Ba Bb Bc Ch Co Cp Cs Cu Cw Dd Dg Di Dk Dl gW Hb Hr Hu Hw Hx In Iq Jk Jn Jo Jr Js Jt Jv Kg Kq Lu Ly Mb Md Mf Mj Ml Mr Mx Mz Ne Nk Nl No Nv Ny Of Og Om Ow Pb Pg Qb Qn Rj To Uf Up Vo) Ow(Aa Ad aE Aj Ao aS aX Bn cE cF cU cW Dd De Dg dH Dk Dl dM Fw Hr Ij In Io Je Jf Jk Jl Kc Kd Kr Ky Lu Lv Ml Na No Ny Oe Of Om Oy Pc Pg Qx Rb To Tr Uc

Figure 15 Continued cF cI cN Cs Cv CW cZ dG dK Fb fR Hq Ih Ip Jk Jn Kn Kx Ld Lw Ma Mb Mn Mt Nh Nn Pa Pe Pf Pg Po Qb Qx Rg To Un) dM(aD aG aH aI aK aL aM aN aR aS aV aW aY bB bE bG bH bI bL bM BO bP bS cA cB cC cD cE cG cH cK cL cN cP cQ cV cW cZ Db dC dF dG dI dJ dL fR gW ti Io) Hu(Af aX cP cW Et Fp Il Im Ip Iq Ir Is Iv Jg Jh Ji Jo Jr Jt Lh Li Lj Lu Ly Mb Md Ml Mp Ms Mt Mu Mv Mx Ng Ni Nv Nw Oe Oi Ok On Pb Pc Pe Po Qb Qd Uu Vo) Vo(aA aK Ap aU aV aX Bg bH bZ CO Ct Cw Dl dR eF Ex Ez fR Hx It Jh Ji Jn Ke Kg Kl Kn Ma Mb Mg Mt Mv Mz Nn Nr Nv Nw Ok Pb Ph Qc Qy St Ua Vu) Lv(aD aE AL Ao Aw aZ bC bN bO bQ bR bS bU bZ cA cI cQ cR Cs cU Cv Cw Db Dc De dF dG Di dK dR Ex Hb Jf Jv Ky Qn Rj To Ue Uu Wm) Af(aC AN aZ Bc bF Bg bN bQ bU cN CO Cp cQ Cu CW dF dG dR Ex Hr Il iZ Jh Jo Ko Ky Ld Lu Mi Mu Mv Qu Qx Rg To Ue Ut) Mt(Hx Ii In Io Iu Jh Jl Jo Jr Js Jt Lw Lx Ly Mc Md Me Mi Ml Mr Mu Mv Mz Nb Nd Ng Ni Nm Ny Oe Of Oh Oi On Pa Pb Pc Pd Qe) aA(An aV Aw bH bL Bo cB cG cL cM cP Cq Cv dG dI dJ dL eC Ex fR Hb Ij Im Jl Jq Jv Ks Lj Nh Ni Nv Oy Qb Qc Rj Up Uu) aX(Bo Hb Hr Hx Il In Io iZ Je Jf Jn Jr Jt Jv Kj Ky Ml Mp Ms Mz Na Nc Nj Oe Of Om Oy Pb Rb Rj To Ub Ue Uk Up Uu) Cx(aC aE AN aQ Aw aZ Ba Bc bF Bg bM bN bQ bU cF cI cQ cR Cs Cu cW dG dR eF Ex Hb Ii Il Jo Kj Ky Ms To Ue) cU(aC aD aE Aj aN AO aQ bE bG BN bP bR bU bZ cA cE cI cN cQ Cv cW cX dA dF dG dK Ii In Jo Oe Om Qn Qx) Nu(Fp Hx Ij Il Jg Jh Jk Jl Jr Li Lw Mc Md Mj Mk Mp Mq Ms Mx Na Nb Nd Ne Ni Nm Nr Nw Om Pa Pb Pd Pe Po) Ii(Bg Co cP dR eF Fa Fb fR Gl Gp Hx Is Jf Ke Kg Lh Mu Mv Nv Nw Ok Pe Ph Po Qa Qe Rm To Ua Uh Ut Vv Wm) On(Hx Ik In It Iu Iv Jk Jm Lx Lz Md Mf Mh Mi Mn Mr Na Nb Ni Nj No Nq Ns Nt Nv Nx Oy Pb Pf Po Pz Qe Uu) Lx(Hx Il Iq Iu Jh Jm Js Jt Lw Mc Me Mh Mk Ml Mq Mr Ms Na Nj Nn No Nq Nr Nx Ny Of Oh Pa Pb Pe) Jo(Ap Ba BN Bo cO cP Cu Cw Ex Fp Hx Ij Im Ip Jg Jl Ko Lh Li Mu Mv Nn Po Qy Sr Tn Uf Wm) Mi(cP cW Il Ir Is It Iv Jl Js Lj Mf Mp Mz Na Nb Nc Ng Nr Nt Nv Nw Of Pa Pd Pe Qa Qd) Mu(cP cW cX Fp Ik Io Iq Jn Jr Jt Lu Mz Nc Nd Ng Nl Oe Of Oh Oi Pa Pb Pc Qe) Mv(cP cX Hx Il Iq Jr Jt Lj Lu Mb Me Ml Mz Nb Nd Ng Nj Oi Om Pb Pc Qe Ue) cX(Ba Bo bZ dE dF Dp Fn Hb Hc Hx Jf Ko Ky Ld Qw Rj Ub Ue Uk Up Uu) cF(aO aW bF bN bQ bZ cG cN cP cQ cR cW dA dB dE dF dG fR Hx Lu) eF(aE aF bN cI cW dB eC Hb hC iH iJ iO kQ kR kS oE oK pF Uu tF) fR(aE aF aG aH aN Ao aW bC bM Bn bR cE cI cP cV dK Of Qn) Lu(aE bJ BN Bo bP cI Cs dB Fp Is Jg Ji Lw Nn) Mb(Hx Ip Is Ji Lh Li Nn No Nv Ok Om Pg Qa Qb Qe) Of(bQ bZ Co dR Ip Jh Ji Jk Li Ma Mw Pg Qb Tn Vu) Hx(Bo Hb Iq Jg Jl Jt Ma Mf Ni Nj Nn Pb Qn Wm) Iq(Bo dB Ij Ir Jg Mp Nv Nw Pe Pg Qa Qd Qe) Jl(Hw Iv Js Jt Ly Me Mf Mm Nd Ng Ni Nj Nm) Qn(aQ aV bN Bo cY dB dD dK dR Ex Ko Ld To) bZ(Ao bJ Bo bR cE cI cN cP cR dA iZ Jq) Nw(Jq Js Ly Mm Ms Nm Nx Oe Om Pb Pz) dB(Ax Bn bQ dF dG iZ Jf kQ nY oK Wm) Hb(aQ cY dR Ex Im Ji Ma Mz Sr St) Qe(Jg Jm Js Ni Nk Nn Om Pb Pz Qc) cP(bE Bn bW cO cR JA cK Ma Nn Oe) Bo(Ax bC bG BN Jq Jt Jv Mz) Ms(Is Jh Ji Lh Mp Mw Mz Om Qa) Ue(aF aU Kg Li Mg Mp Nn Qd Uf) Ba(Ao Dg Dl Hw Io Jm Jq Om) Ly(Ji Lh Li Ma Mm Mz Qa) Jq(dR Ex Ji Ke Kg Ko To) Jt(Ap Ir Jg Ji Nv Qa Sr) Ni(Ir Is Nv Pe Pg Qa) Om(bQ Im Ir Is Qu Qy) Uu(aQ Bg Fb Hc Jg Ua) bN(aO Bn cN dF dG Ex) Io(dR Ko Ky Ph To) dK(dA iH iZ Jf Or) Nn(Me Ml Nd Ny) Nj(Jg Mp Mz Po) Il(Jk Kq Po Qy) bP(cC hG pF To) dF(aF bJ cI cR) Jg(Ik Ml Oe) Ko(Aa Dg Ks) bQ(aE cI cN) dE(bU iZ nY) Ex(Jv Mj) Qa(Jm Nk) Kq(Dl Kl) Lh(Hw Oe) Nx(aF Ok) Pb(Jh Mz) aO(aF bC) bE(hB oF) iZ(bF eC) nY(bG bO) AjCu AoMa BndG LwMe MdNv MlMp UcQd ToaQ HcOe RgaV cIoF cNcR Unconstrained panels with 2 analytes, where 1.0E-2 >= 'AUC p-value' > 1.0E-3. Contains 7,084 panels of 66,377 total panels evaluated. : Ug(Aa aC AD aG aH aI aJ AL aM aN AO aP AR AS Aw Ax aY BB bE bF BG bH bI bL bM bO bQ bR bS bU bZ cA cB cC cD cE cG CH cI cJ cK cL cM cN cO Cp CQ Cu CV Cw cZ dA DC Dd dF DG dH DI dJ Dk DL dM dN Dp Ed eF Et Fa Fb fP fR Fw gP Gz Ha Hf Hq Hr Hw Ib Ic Id Ij Ik Il In Ir Is It Iu Iz Jd Je Jg Jh Jk Jl Jm Jo Jq Js Jt Ju Jy Ke Kf Ki Kj Kl Ko Kx Kx Li Lu Lw Ly Lz Mb Mc Md Me Mh Mk Mm Mn Mq Ms Mt Mu Mw Na Nb Nc Nd Nf Nh Nj Nm No Nq Nr Ns Nt Nu Nv Nw Nx Ny Oa Of Oh Oi Ok Om Or Oz Pa Pc Pd Pe Pf Pg Pi Pj Pk Po Pz Qb Qc Qg Qh Ql Qm Qt Qw Qx Qz Ra Rb Rc Rg Rh Ri Rm Ss St Tr Tt Tv Tz Ub Uc Ud Ue Uk Ul Um Un Uo Ut Uu Uv Vo Vs Vt Tj) Kc(Ad aF aH AJ aK AL aM AN AP As aU Ax aY Ba BC bE bF Bg bJ bL bM BO bP bR bS bU bX cA cB cC cD cE cG Ch cI cJ cK cL cM Co Cp cQ cR Ct Cu CV Cw cZ dA DB DC dE dF dG DI dJ DK dL dM dN Dp Ed Ef Et Ez Fa Fb fP Fr Fw Gl gP Hc Hf Hq Hu Hw Hx Ib Id Ih Ij Ik Ip Ir Is Iu Iv Iz Jd Je Jg Jh Ji Jk Jl Jm Jn Jr Js Ju Jy Kd Ke Kg Ki Kl Ko Kp Kr Kx Lh Lw Ly Lz Ma Mc Md Me Mf Mg Mh Mk Mm Mn Mq Mr Mv Mx Na Nc Nd Ne Nf Ng Nh Nj Nk Nl Nm No Nq Nr Ns Nt Nu Nv Nw Oa Of Oh Oi Ok Om Oy Pc Pe Pf Pg Pk Po Pz Qb Qc Qd Qe Qg Qh Qt Rb Rf Rg Ri Rm Sr Ss St Tn Tr Tt Tv Tz Ub Uf Uh Ul Un Uo Uv Vp Vs Vt Vu Vv Tj) Kk(aC Ad aE aF aG aH aI Aj aL aM aN Ao AP aR AS AW Ax aY BA BB Bc bE bF BG bH bl bJ bL bM bQ bX cG cH cI cJ cK cM cN Co CP Cs Ct Cu cV Cw cZ DC Dd De dF DG dH dJ Dk dL dM Ed EF Et Fa Fb Fp Fw Gl gP Gz Ha Hc Hq Ib Ic Ih Ik Il In Ip Ir Is It Iu Iz Jd Je Jf Jg Jh Ji Jk Jl Jm Jr Js Ke Ki Kj Kl Kn Ko Kx Ld Lh Li Lj Lw Lx Lz Mb Mc Me Mf Mh Mk Mm Mn Mp Mq Mr Mt Mw Wa Nb Nc Nd Ne Nf Ng Nh Nj Nk Nl No Nq Nr Ns Nt Nu Nv Nw Oa Of Oh Ok Om On Or Oy Oz Pa Pd Pe Pf Pg Ph Pk Po Pz Qa Qc Qd Qe Qg Qh Qm Qt Qu Qz Rb Rf Rg Rh Rm Sr Ss St Tn Tr Tt Tu Uc Ud Ue Uh Ul Um Un Uo Ut Uv Vs Vt Vu Vv Wm) Us(Aa aC AD aF aG aH Aj Al aM aN AO Ap aW Ax aY aZ Bc bE bF bH bl bJ bM Bn BO bQ bR bS bW bX cA cD cE cG cI cL cM cN CO Cp cQ cs Cv cZ DB dC Dd De dF dG dI dJ Dk dL Dp Ed Ef Et Fa Fn fR Fw Ha Hf Hw Ik Im Jg Jh Jr Jt Ju Jy Ke Kf Kg Kl Kp Ks Kx Lh Li Lj Ly Lz Mb Md Me Mi Mj Ml Mm Mn Mp Mq Ms Mw Mx Nb Nc Nf Nh Ni Nj Nk Nn Nt Nu Ny Oa Oe Of Ok Or Oy Oz Pa Pb Pc Pd Pe Pf Ph Pk Pz Qc Qg Ql Qm Qu Qw Qz Rc Ri Rj Sr Ss St Tr Uf Ul Um Un Uo Up Uu Uv Vp Vv) Kd(AD aE aG aJ aK An Ao aP As aU aV AW aZ bC bG bL BN BO bP bQ bR bS bU bW bX bZ cA cC cD cG Ch cI cK cL cM cP cQ Ct Cv cW cY dA Db Dc dE dF dG DI Dk dL dM Ed Ef Fa Fb FR Fw Gl GP Gz Hc Hq Hu Hv Ib Ij Ik Ir Is It Iv Iz Jd Jf Jg Jh Ji Jm Jn Ju Jy Ki Kn Kq Kx Kz Ld Lh Lw Ly Lz Ma Mb Md Me Mi Mk Ml Mn Mp Mq Mr Mt Mv Mw Mx Na Nb Nf Ng Ni Nk Nv Nw Of Oi Ok On Or Oz Pb Pe Pg Pk Qa Qb Qh Qt Qu Rg Rm Ss St Tn Tr Tt Tz Uh Ul Um Un Uo Vp Vu Vv) Bo(aC AD aE aF Aj AN Ao aP aQ aZ Ba Bb Bc bF Bg bH bJ bL bM bO bQ bR bU bX cD cE cF CH cJ cM cN cO cP CQ cR Cs Ct Cu CV cW cY DB dD DE dF dG dH dI DK eF Fn Fp fR Hb Hc Hr Hu Hw Ih Ii Ij Il Im In Io Ir Is Iu Jf Ji Jk Jl Jn Jr Js Ki Ky Lh Li Lj Lw Lx Ly Lz Ma Mb Mc Md Me Mf Mi Mj Ml Mm Mn Mr Ms Mu Mv Mx Nc Ne Ng Ni Nj Nk Nl Nm Nn No Nq Nr Ns Nu Nw Nx Ny Oe Of Oh Om On Oy Pb Pc Pe Pf Pg Pz Qa Qb Qc Qd Qe Rb To Ub Up Uu Vo Wm) cS(aC aD aE aF aG aH aI Aj aK aL aM aN aQ AR aS aU aV aW aX aY aZ bB bC bE bF bH bI bJ bL bM bP bR bS bU bW bX cA cB cC cD cE cG cH cI cJ cK cL cM CO Cs Cu cV cW cY cZ dC dD dH DI dK DL dR eC Ed Ef Ex Ez Fa Fb Fp Fr Fw Gl GP Gz hB hC Hf Ib Iz Jd Jh Ji Jy Kg Kp KQ Lj Lx Mg Ml Mn Mq Nb Nd Nk Nq Nw nY oH On Pb Pc Pe pF Ph Pi Pk Qc Qd Qe Qh Ql Qm Qt Qu Qy Qz Rc Rf Rh Ri Sr Ss Tn Tt Tv Ua Ud Uf Uh Ul Um Un Uo Ut Uv Vt Vu Vv Wm Tj) Jp(Aa aC AD aE aF aH Aj aK AN AO AP aQ Ar As aV Aw aY aZ Ba Bb BC bE bF BG bH bJ bM bO bQ bR bS bU bW bX bZ cA cD cE Ch cI cJ cK cL cM cN CO CP cQ cR Cs Ct cU cV CW cY cZ dA Db dC Dd DE dF dH DI dJ DK Dl dM dN Dp dR Ed eF Et Ez Fa Fb Fn fR Ha Hc Hf Ib Ic Id Il Je Jq Ju Ke Kf Kg Ki Kj Kl Ko Kq Kr Ks Ky Kz Ld Ok Ph Pj Pk Qg Qh Qm Qw Qx Qy Ra Rb Rc Rg Rj St Tn Tr Tv Tz Uc Ue Uf Ul Um Un Ut Vp Vs Vt Tj) My(aD aF aG aH aI aL aM aN aO AP aS aV Aw aY aZ Bb BC bE bM BN bO bR bS bU bX bZ cA cB cD cE cG cL cN Co cP CQ cR Cs CU cW dC DD De dF dH DI Dk dM Dp dR eF Et Ex FR Fw Gz Hq Ib Ih Ij Ik Im Ip Ir Iv Jf Jk Jn Jv Kl Kp Kr Kx Ld Lh Lj Lu Lz Ma Mc Mg Mh Mj Mk Mm Mn Mq Mr Mw Mx Na Nb Nf Ni Nk Nl Nm No Nq Nr Ns Nt Nv Nx Ny Oh Ok Oy Oz Pd Pf Pg Pj Po Pz Qb Qc Qd Qm Qw Ra Rg Rh Rj Rm Ss Tt Tv Tz Uk Um Ut Uv Vp Vv Wm) aX(Aa An AO Ax bG BN bZ cF cP cU cX dA dB De dG Dp eF Et Ex Fn Fp fR Ha Hc Hq Hw IH Ij Ik Im Ip Ir Is It Iu Iv Jg Jh Ji Jk Jl Jm Js Ki Kl Kn Ko Kp Ks Kx Ld Lh Li Lj Lw Lx Lz Ma Mc Md Me Mf

Iv(Nx Pg) Qx(aV dD) Pc(Mx Qy) aZ(dA Uk) AdBg AwAx CsNx CuDl EtNc LwMk MdMw NhIj RcPh KlcY RjaV OrdD aNcO bJiH bLoF bRdA cZhC

Constrained panels with 3 analytes, where 1.0E-9 >= 'AUC p-value' > 0. Contains 13,529 panels of 7,710,078 total panels evaluated. :
Ou{Kc(Aa AD aE Af aG aH Aj Al Ao aW bN cE Co CP Cq cS Cu Cw CX DC Dd De dF DG dH DK Dl Dp Ed Ef Fa Fw Ha Hb Hq Hr Id Ii In Iq Ir Iz Jf Jj Jk Jl Jo Jq Js Jt Jv Ke Kf Kj Kl Kr Ks Kx Lh Li Lu Lx Lz Mg Mh Mj Ml Mn Mp Mr Mx Ng Nl Nm No Nr Nv Nw Nx Ny Of Og Om On Oy Pb Pe Pf Pg Po Pz Qb Qh Qn Qv Rg Rm To Tr Tv Uc Ug Uk Uo Up Ur Us Uu Vo Vp Vs Vu Tj) Kd(Aa Ad aE AF aG aH Aj Al Ao aX bG bX cE cF Co Cp Cq cS CX DC Dd DG dH DK Dl Dp Ef Fw Ha Hb Hq Hr Ii Ij Ik In Io Iu Iz Jg Jj Jk Jl Jm Jo Jq Js Jt Ju Jv Ke Kf Kj Kl Kr Ks Lh Li Lx Ly Lz Mg Mj Mk Mm Mn Mp Ms Mu Mx Nb Ng Nl Nm No Nr Nv Nx Ny Oe Of Og Ok Om On Oy Pf Pg Ph Po Pz Qb Qh Qn Qv Rm Ss To Tr Tt Tv Ug Uk Up Ur Us Uu Vo Vp Vs Vv Tj) aF(Aa AD aE Af aG aH Aj Ao Ap aS aW aX bA Bn cE cF cI Co cP Cq cR cS Cw CX Dg Dl dM dN Dp Ef Fw gL Ha Hb Ii Ij Ik Io Iq Iu Iz Jg Jj Jk Jo Jq Jt Jv Kf Kl Kr Ks Lu Lz Mg Mj Mk Mm Mn Mp Ng Nm Nn No Oe Of Og Oi Om Pg Pj Po Pz Qm Qn Qv Ss Tt Ue Ug Uk Up Ur Us Uu Vo Vv) cS(Ad aE Af aG aH Aj AO aQ aW bB bG BN bX cE cF cG cI cP cV CX Dc dF Dg dH dI dK Dl Dp Ef fP Fw gL Ha Hb Hr Ii Ij Ik Io Iq Iz Jj Jl Jo Jq Jt Jv Kf Kj Kk Kl Ks Lh Mg Mj Mm Mn Mp Mw Ng Nm Nq Nv Oe Of Oi Om Pg Po Pz Qn Qv Rm Ss Tt Ug Uk Up Ur Us Uu Vo Vv) Ii(aE aJ aU aW aX bA bC bJ BN bP bU cI cP cR Cs cW CX De dK dM dN Ef Ex Ez Fa Fb Fn Fp Fr GL Hc Hu Hv Hx Ih Im In Io Jh Jn Jr Jv Kg Kk Kn Ko Kq Ld Li Lv Ma Mg Mi Mp Mq Mu Mv My Mz Ng Nj Nk Nn Nq Ok On Pi Qd Qv Qy Rf Tn Uf Uk Ur Ut Vv) Kk(Aa AD aE Af aG aH Ao Bg BN cE cF cP Cq DC Dd Dg dH DK Dl Dp Ef Ha Hb Hq Hr Ij In Iz Jj Jk Jo Jq Js Jt Kf Kl Kr Ks Lh Lx Ly Lz Mj Ml Mn Ms Mu Ng No Nr Nv Nx Ny Oe Of Og Oi Om On Oy Pf Pg Po Pz Qh Qn Qx Tv Uf Uk Up Us Vp Vs Tj) aE(Aa Af aG aH Al An Ao aX bC bJ BN bS bU cE cI cM CX dH dK dN Fw Ha Hb Ij Io Iq Iz Jj Jo Jp Jq Js Jt Ju Jv Kf Kg Kl Kq Lh Lv Lz Mg Mi Mj Mm Mn Mp Mu Mx My Ng Nm Nn Nr Oe Of Og Om Pf Pg Po Qb Qm Qn Qy Rm Uf Ug Up Ur Us Uu Vo Vv) dN(Ad Af aH Ao aV bF BG bN bQ cE cG Co Cq Ct Dc dF DG dH Dk Dp Ha Hb Hq Hr In Jj Jk Jl Jo Js Kr Ks Lh Lx Lz Mj Mk Mn Mp Mr Mx Nl No Nr Nv Nx Of On Oy Oz Pa Pb Pe Pf Pg Po Qh Qv Qw Rg To Tr Tv Uc Up Ur Us Vp Vs Tj) bN(AD Af aG aH Aj Ao aW aX bG Bn bP bU cE cI Cq CX Dc Dg dK Dl Dp Ef Fw Ha Hb Ij Io Iq Iu Iz Jg Jj Jo Jq Jt Jv Kj Kl Ks Lh Mg Mj Mm Ng Nv Ny Oe Of Oi Om Pg Po Pz Qn Qu Qv Rm Ss Tr Tt Tv Ug Up Ur Us Uu Vo Vv) Mu(AD Af aG aH Aj Ao aW cE cG cI cL Co cX De Dg Dk Dl Ef Fw Ha Hb Hr Ij Ik Il In Iq Iz Jg Jj Jk Jo Jq Jt Kg Kj Kl Kr Ks Mg Mk Mp Ms Mw Ng Ny Of Om Pd Pg Po Qu Qv Qw Rm Ss Tt Uc Ue Ug Uk Up Us Ut Uu Vo Vv) dK(aD Af aG aH AJ Ao aX Bn bX cE cF cP Cq CX dC Dg Dp Ef Ex Fw gL Ha Hb Hq Hr In Io Iz Jj Jk Jo Jq Jt Jv Kj Kl Ks Lz Mg Mj Mn Mp Ng Ni Oe Of Og Om Pg Po Qn Qv Rb Tt Tv Ub Ug Uh Uk Up Ur Us Uu Vo) cI(Aa aD Af Al Ao aQ aX Bn cE cF cP Cq cW Cx DC dH Dp Fw gL Ha Hb Hr Id In Ir Jj Jo Jq Ju Kr Ks Lh Lu Lx Lz Mj Mn Mp Mr Mx My Nl No Nx Oe Of Pa Pf Pg Po Qb Qn Qv Rg Rm To Tv Uf Up Ur Us Vp Tj) gL(Aa AD Af aG Aj Al Ao aW Ba Bn cE cG Cq CX dC dF Dg dH Dl Ef Hb Hr Ij Iq Iz Jg Jj Jk Jo Jq Jt Jv Kj Kl Ks Lh Mg Mj Mp Ms Ng Ny Oe Of Oi Om On Pz Qn Qu Qv Rm Ss Tv Tz Ug Ur Us Uu Vo) aX(AD Af aG Aj Al Ao aW Bn bP cE cG cP Cq CX dF Dg dH Dl Dp Ef fP Ha Hb Hr Io Iz Jj Jl Jo Jq Jt Jv Kj Kl Kr Lh Mg Mj Mp Ms Ng Nl Of Oi Om Pg Po Qn Qu Qv Rm Ss Up Ur Us Uu Vo Vv) Mg(aA AD Af aG aH Aj Ao bC bJ bV cE cG Co Dg Dl Ef Ez Fw Hb Hu Ij Ik Il In Iz Jg Jj Jo Jq Jt Kg Kj Kl Kq Kr Ks Lv Ms Mw Ng Nn Of Om Pg Qu Qv Qy Rm Ss Tt Uc Ue Uf Ug Uu Vo Vv) aW(Aa Af aG aH Ao bJ Bn cD cF Cq cR CX Dk Dp Ha Hb Ib Io Jd Jj Jk Jo Jq Jt Ju Jv Kf Lh Mj Mn Mp Mx Ni Nm Nn No Oe Of Og Om Pf Pg Pz Qb Qn Qv Qy Uf Ug Up Ur Us Uu Vo Tj) Uf(AD Af aG aH Aj Ao cE cG Co Dc De Dg Dk Dl Ef Ha Hb Hr Ij Ik Il In Iq Iz Jg Jj Jk Jo Jq Jt Kj Kl Kr Ks Mk Mp Ms Mw Ng Ny Of Om Pg Qu Qv Rm Ss Tt Uc Uu Vo Vv) cX(aA aD aG Ao bG cD cE cF cP Cq cW Dc Dk dM Dp Ex Fw Ha Hb Hq Hr Hv Hx Ik Io Jj Jk Ju Jv Ks Lh Lz Mj Mn Mx Nr Oe Of Om Pf Pg Po Qb Qv Tr Tv Ug Uk Up Ur Us Uu Tj) Qy(AD Af aG aH Aj Ao cE cG Co De Dg Dl Ef Fw Hb Hr Ij Ik Il In Iz Jg Jj Jk Jo Jq Kj Kl Kr Ks Mk Ms Mw Ng Ny Of Om Pg Qu Qw Ss Tt Uc Ue Ug Uk Up Us Uu) Nn(AD Af aG aH Aj Ao cE cG Co Dg Dl Ef Fw Ha Hb Hr Ij Ik Il In Iq Iz Jj Jo Jq Jt Kj Kl Kr Ks Mp Ms Mw Ng Of Om Pg Po Qv Rm Ss Tt Uc Ug Uk Uu Vo Vv) Fw(aD Af aG aJ Al Ao aQ bF BG Bn bQ bS cA cD cE cF cK cP Cq cR dH Hb Iz Jq Kg Kl Kr Lh Li Mj Mp Ms Nc Nl Og Om Qv Rj Tz Up Ur Us Uu Vs) bJ(aC AD Af Aj Ao bP Co cW Dc Dg dH Dk Dl Ef Hb Hr Ij In Iz Jj Jo Jq Jt Jv Kj Kl Ks Lh Ms Mw Ng Nr Ny Of Oi Om Oy Pg Qv Rm Tv Ug Ur) dM(aH Al Ao bG cE cF cK Cq Dc dF DG dH Dk Ha Iz Jj Jk Jl Jo Kl Kr Ks Lx Mn Mx No Nv On Pa Pf Pg Qb Qh Qv Rm Tr Tv Up Us Vp Vs Tj) Io(Af Ao aV Bn bP bV cE cF cP Cx dH Dp Ex Hb Hq Hr Jj Jn Jo Jq Jv Ks Ky Mj Ml Nl Oe Of Og Om Pg Qn Qv To Tv Ug Uk Up Ur Us Tj) Jv(Af aG Al bG Bn bU cF cP Cq Dc dF dH Dk Dp Ha Hb Hr Jj Jl Jo Jq Kr Mj Mx Nd Nl Oc Of Om Pg Qn Qv Rm To Tv Uk Up Ur Us Vp) Kg(Ad Af aG aH Aj Ao cE cG Co Dg Dl Ef Ha Hb Ij Il In Iq Iz Jj Jo Jq Jt Kj Kl Kr Ks Ng Of Om Pg Qu Qv Ss Uc Ug Uu Vo Vv) Up(aD Af aG aH Aj Ao bC Bn bP Cx dC Dg Dl Ex Hb Hv Jj Jo Jt Kf Kj Kl Li Lv Mi Mt Ng Nm Oe Of Og Om Qd Qn Ug Ur Uu Vo) bG(AA aD Af aH Ao bA Bn bP bV cE cP cW Cx Dp Ex Hb Ij Iz Jq Jt Lu Lz Mj Ms Ng Oe Of Og Om Pf Pg Qn Ub Ug Uk Us Uu) Ex(Ad aG aH Al Dc Dk Hb Ir Iz Jq Js Jt Kf Kl Ks Lh Mj Mm Mx Ng Nm Nv Nw Ny Of Om Pz Qb Rm Tz Uu Vo Vp Vv) Lv(cE Cq dB Dc dF dH Dk Ha Hr Jk Jl Jq Js Ks Lh Lz Mj Mx No Nv Ny Of Om Pf Pg Po Qb Qh Qv Tr Tv Tz Us Vp) Cx(aD aG Ao cE cF cP Cq dH Dp Ha Hb Hr Iz Jj Jk Jo Jt Ks Lh Lz Mj Mp Om Pf Pg Po Qb Tt Uk Ur Us Uu Vo) bP(aV bU cE cF Cq dF dG dH Dk Ha Hr Il Jl Lx Lz Mn Mr Mx Nd No Oz Pa Pb Pe Pf Pg Qh Qv Rg Tr Us Vp Tj) aD(Ad Af aH bB Bn bU cE cF cZ dH Dp Ha Hb Hc Ij Iz Jq Lz Mm Ny Oe Of Pg Po Pz Qn Qv Rg To Ub Us Vv) aG(aA Bn cF Cq Dc Dp eF Ha Hr Iz Jj Jq Kq Ks Lz Mj Mn Oe Oz Pa Pf Pg Po Qv Rg To Ug Uk Ur Us Vp Tj) Om(Af Ao aU bA Bn bU bV cF Dp eF Hx Im Jh Jj Jp Ki Ko Kq Lz Mj Mz Of Pg Qn Qv Ra To Ug Ur) Uu(aQ bC Bn bU cF cP cY Dp Ef Hb Hc Hu Hx Jp Jq Ko Lz Ma Mj Mx My Nl Pg Qu Qv Rg To Ur Us) aH(Aj aV bA Bn Bo bU cP cR cT cW dB Dp Hr In Iz Jj Kj Kq Ks Lz Ms Oe Of Og Qv Ug Uk Ur) Qn(bU cD cE cF cP Cq dF dH Dp Ha Hv Jj Jo Lz Mj Mx Nl Of Pf Pg Qv To Tt Ug Ur Us Vo) Kq(Af Ao cE cG Dc Dk Ef Ha Ij In Iz Jg Jk Jo Jq Jt Kl Kr Ks Nd Of Pg Tz Uc Vo) Ur(Aa Af Ao Ar bC Bn bU cP cW Hb Iq Jq Jt Lu Mj Mp Ms Oe Of Og Qm Qv Qx Rg Vv) Ug(Bn bU cE cF cP Cq dF dH Dk Hb Jl Lz Mj Mp Mx My Nd Nk Nl Pg Qv Rg Us Vp) bU(aA Ad Af aJ bV cE dB Hb Ij Jj Jq Ks Mj Mn Ms Nx Oc Og Oi Oy Qm Uk Us) Bn(bC cF Dp Ha Hb Jj Jo Jt Kf Kl Kr Lh Mj Mm Mp Nl Nm Pg To Tt Vo Vv) Of(aA bC bE cF cZ EF Ez Hb Hc Im Jh Jq Md Mj Mp Mx My Ni Qv Uk Us) cE(AA bA bC bV bZ cF Co cT cW De eF Hu Hx Jp Lz Ma Mi Mp Ms Mv To) Kl(aA aQ aV BA bC bV cF cP cW cY eF Ez Hu Hx Jp Ko Ma My To) Hv(Af Ao dH Dk Hr Jj Jk Jl Jq Ks Lh Mj Mn Ms No Nv Po Us Vs) Pg(Af bA bC bW Co De Hb Jj Ld Li Mi Mp Ms Mt Mv Nq Oe Pd Qd) Vo(aJ aQ aV BA bC cF cP cW Fb Hu Hx Ko Ma Mj My Sr To) Ef(aA Ad Ao aU bC cF cW De eF Ez Fr Hc Hu Im Iz Jo My) aJ(Aa dG dH Dl Ha Hb Iz Jt Kr No Nv Ny Pz Qb Rm Vv) Mj(Af Aj Ao cD cF cP Hx Iz Jj Jo Ki Ld Li Ng Qv) Ms(cD Cq cZ DC dF Dp Ha Lz My Nl Pf To Uo Vp) Qv(aA aL bC bE bM bW cZ Ez Hb Im Jj Mi Nh Nl) cW(Ad Al bB bE cF cZ Dg dH Ha Iz Jo Mx Nv Tr) Hx(Ao Dg Dk Dl Hb Ij Jg Jk Jl Jq Jt Lh Us) Jj(Aa Af bC cF cP cZ Ez Hb Jq Lz Mi My Us) Ko(Aa Ao Dg Dl Hb Ij Iz Jg Jk Jt Lh Pz Vv) bA(Cq Dc dF Jl Ny Qb Qh Qu Tt Tv Us Vp) bC(Aj Ao cG Dc dF In Iz Jo Ks Ss Tt Us) cP(Ad Af Aj Al Ao Dl Hb Iz Ng Oe Rm Vv) aA(Aa dC dH Hb Iz Ng No Nv Ny Oi Tv) Af(cD cF De Dp Ha Hb Jh Lz Mv Pf) Im(Ao Dl Ha Hb Ij Iq Jq Mw Ny Rm) Aj(cF cZ Jf Lz Mx My Qb Rg) Ez(Ao Dg In Iz Kj Ng Ss Us) Mi(bQ Ha Il Jk Jo Ks Uk Us) To(Dg Dl Hb Ij Jt Kr Og Vv) Lz(Ad dC Iz Kj Ng Oe Uc) bV(dF fP Iq Ng Qu Tt Us) cF(Hb Iz Jq Ng Oe Us Vv) Ao(Ap cR De Ma Mv My) Li(Dc Ha Jl Mr Po Tv) My(Dl Iz Kj Ss Vv) Hu(Iz Jo Oy Po Vs) Rm(bF Ih

Jp Kc Ko Kq Li Ma Mf Mu Nn Qa Qd) Or(aF aU bC bJ dK Jp Kc Kg Mg Mi Mu Nn Qy Uf) Kg(aA aJ Ao De Ha Hb Jo Jq Om Uc Ue Ug)
Kc(An bX cP Hb Jq Ml Ne Nl Uu Vo Vp) Ko(An bV bX cI cU Hb Jq Jt Uu Vo Vp) Kq(Ao Ha Hb Jo Jq Jt Kl Uc Uu Vo Vp) dB(aA bC bJ bN
bP bX Ki Ld Mp Wm) aJ(An bX dH Mg Mu Og Qy Vo) aQ(bE bJ bV cI cU dN To Vo) Uf(aA De Ha Hb Jq Og Qw) aF(aA cF cU eF Hu Og
To) bJ(bP dR Jp Mz Og To Vo) Mg(aA Hb Jo Jq Qw Ug) Up(bV cU Ez Jp Qa Qe) Qd(Ha Hb Jq Jt Vo) bE(bN Jn Mf Mz Og) bV(cA cV cY dR)
Ba(Of Uu Vo) Ha(Li Mi Mp) Ua(Of Uu Vo) Jq(aU Ji Mv) bP(bX cU Hu) De(Mu Qy) Qa(Mx Qb) Qw(Mi Qy) cF(Hu Hv) dR(dM To) AoEf
WmdK MacE MfUg HbJi HcOf QeVo JpbX} Ii{My(aE Af aJ aP aX Ba BN Bo bV bZ cF Cp cS cT CU CW CX DB dE dM Ex Ez Fb Gp Kc Kd Ke Kg Kk Kn Ko Kp Kq Kx Ky Ld On Or Ow Ph Qy Ra Rh Rj Sr St Tn To Uf Ug Uh Up Ur Us Vo Vu Vv Wm) On(AA Af aJ aX BN bV cF cS cT cU Cx dB dE Dl dM Fb Fn Fr Hb Hu Hv Hw Hx Iq Jl Jt Kd Kg Lh Li Lx Ly Mb Md Mi Mm Ms Nj Of Og Om Ow Pa Pb Pe Tn Uf Uk Us Uu Vo Wm) Ba(Af aX BN bP cF cP cS CU CX dM dN Ex Fn Hb Hu Hv Hx Ih Jn Jr Jt Kd Kl Ky Mi Ml Mu Mv Mz Nn Oe Of Og Om Ow Qa Qe Rj Ss To Uk Us Uu Vo) Ex(aK aQ aU bC bJ bN cS Ct cX cY De dK dR Ef Ez Fn Hc Hu Hv Hx Im Io Jv Kc Kd Kg Kq Ld Mg Mi Mp Mu Mv Ng Ni Nn Ow Pd Qu Qy Ua Uf Ur) Tn(aA aE Af aJ bJ BN bP cI cS cT cU CX Fb Hu Hv Hx Ih Io Jn Jp Jv Kd Kk Kn Ko Mz Ni Nk Of Og Ow Qa Qe To Uk Up Ur Us Uu Vo) Hc(Af aX BN bP bV bZ cS cU CX dE dK Gl Hv Hx Ih Is It Ji Jn Jp Kc Kd Ko Ky Lh Ma Mz Nn Nw Oe Of Ow Pb Qa Qe To Ur Us Vo) Kq(aA aE Af An Ao bN cS cT cU CX Dd Fb Fn Hb Hv Il In Iq Jn Jo Jp Jr Jt Kd Kj Kn Ky Ml Og Ow To Uk Us Uu Vo) Ow(aA BN bV cP cS cT Cu CX Fa Fr Hx Ih Jn Jp Jr Kd Kk Kn Ko Ma Mg Mz Ng Og Ph Qa Qc Qe Ur Us Vv) cS(aA aJ bN cP cT dR Fb fP Hu Ih Jl Kc Kd Ki Kk Kn Ko Lh Nv Nw Or Ph Qe Rf St To Up Ur Us Vu Vv Wm) Fr(Af aJ An BN bV cF cP cT CX dB dM Fn Hu Hv Jv Kd Kk Kn Ko Ly Or Qn Rg Ur Us Vv Wm) cT(aX bZ Cx De dR Ef Hv Ih Ji Kc Kg Lh Li Mg Mi Mu Mv Nn Nq Qa Qd Qe Qy) Kk(aQ aU aV aX bN bZ cF Ch cU Cx cY Ef Gl Ih Jp Mg Mv Mz Og Qa Vu Wm) Kd(aX bZ cU Cx dR eF Gl Hx Ih Jl Jn Jp Lh Mz Og Qa Qe To Up Us Vu) Us(Bg bV Cu Hx Ih Is Jp Ko Lh Mg Mz Ng Nv Nw Qa Qe St Ut Vu) Qe(aJ aX BN bV bZ Cx Fn Hb Kg Or Qy Uk Up Ur Vo Vv) Ih(aX Bg bV bZ dR eF Fb Gl Kg Ko Ky Qy To Ua Uh Ur) Ur(Bg cP Ct cU CX eF Hx Jn Jp Og Qa Rm Vu Wm) Lh(Af aJ aX bN bP bV bZ cF cP cU Cx dE dM Fn) Kc(Af aQ bN cF cP CX Hx Jn Jp Ml Mz Og) Vu(aJ aQ BN cW Cx Fb Hv Jn Jr Kn Nk Rj) Kn(aX bZ Ch cU Gl Jp Lx Mv Mz Qa Uh) Ko(aQ bN bV bZ cU Cx dR Hx Jn Og Qa) Nv(Af Bn Cx Fb Fn Qn Rj To Vo Wm) Jp(cF dR Ef Fb Kg Or Qy Up Wm) aA(aX Bn cF Co CX dK dR) cP(aX bZ Hu Ji Ld Ma Mu Qd) Wm(Et Im Jg Mi Nw Ok) Mz(aX dR Kg Mi Ph Ua) Sr(bN CX Fn Ni Pb) aJ(aX BN Cx Ma Og) Cu(bV Rf To Vo Vp) Qa(aX Hb Kg Uk Up) Ji(Aa bV Ct dM eF) Fb(aQ cY Hx Og) Gl(Ng Ph Qx) Hu(Mi St Vv) bN(fR Jl St) dR(Hx Jn Ok) Co(bV dM) Cx(Fa Jl) Mg(Or Ug) To(aQ cY) Og(Cp Ez) Ph(aX cU) MaOr MubV HvSt HxaX HbNw RfbZ UgVv} Us{bV(aA aD aF An aQ aU aV aX bP bU cM Co cS CX De dK dR EF Ez Hc Hv Hx Iu Jh Jp Jv Kc Kd Kg Kk Kq Ld Li Ly Me Mg Mi Mp Mu Mv Mw My Mz Nn Nq Og Ow Qd Qe Qn Qw Qy St Uf Ug Ur Vo Wm) Ow(aA Af aQ aS aW aX bN bU cF cP cS cT CX dK dM eF Ex Fr Hc Hu Hv Hx Jn Jp Jv Kc Kd Kk Kn Ko Ld Mg Mm Mt My Mz Of Og Ph Qe Qn St To Ug Ur Vv) cT(AF aU aV aX bC bP bW Co cS CX De dR Ef Ez Fr Hv Io Iu Jh Jp Jv Kc Kd Kg Kq Ld Li Mg Mi Mp Mu Mv Mw My Nn Nq Pd Qd Qn Qy To Uf Ur Ut) aA(Af aQ aU aV aX BN bU cM cS cU CX cY dA dK dR Ez Hv Io Jp Kc Kd Kg Kq Ld Li Mg Mi Mp Mt Mu Mv My Mz Nn Nq Og Pi Qd Qn Qy Uf Ur Ut) Kk(Af aQ aU aX bN cF cS cU CX cY dK dR Ef Ez Fr Hv Iu Jh Jp Kd Kg Kq Li Mg Mi Mp Mu Mv Mw My Mz Nn Nq Og Pd Qd Qn Qu Qy Uf Ur Ut Wm) Jp(aE Af aJ aX bN bP Co cP cS CX Ez Hb Hu Hv Io Jh Jq Jv Kc Kd Kg Kq Ld Li Mg Mi Mp Mt Mu Mv My Nn Or Qn Qy St Uf Ug Ut Vo Wm) cX(aJ aP aV aX Ba bN Ch cP cS Cu cW cY dK dR eF Ez FR Hc Hu Hv Hx Jn Kc Kd Ko Kq Ld My Mz Ng Og On Pi Qe St To Ug Ur Ut) My(aE Af aW aX cS cU Cx dK dM Fw Hb Hv Hx Io Jo Jv Kc Kd Ki Ld Mm Ms Of Qn To Ug Ur Vo) Ug(aX bN cS Ct Cx Ez Hc Hv Ih Kc Kd Kg Kq Ld Mg Mt Mz Ng Pi Qd Qe Qt Tn Ut Vv Wm) Kd(Af aX cS cU Cx dK dR eF Fr Hb Hc Hx Io Jo Jt Mm Ms Mv Og Qn Rh Ur Ut Vo) cS(Af aQ bN Cx dD dI dR Ez fP Hv Hx Iq Jo Kc Mm Ng Of Or Qy St Up Ur Vo) Ur(aX cP Ct cU Cx eF Hc Hu Hv Hx Ih Jq Jv Mv Qe Tn Ua Ut Wm) Vo(Ba Bg Cu Ez Fr Hc Im Ko Kq Mt Ng On Qa Qd Qe Tn Ua Uf) Kc(Af bN cP cU Cx Hb Iq Jq Jv Ml Mz Og Qe Qn St To Wm) Cx(aJ aQ aX cY dR eF Fr Hc Hv Hx Jn Ko Ld Mz Qe) Kq(Af Ao Hb Il Iq Jo Jq Jt Jv Kj Of Og Om Qn Ue) aX(bN dM dR Ez Hc Hv Hx Jn On Qx Rb Rg St) Af(aJ Ez Fr Hc Hx Jh Ko Ld Ng Qd Ua Ut) Hb(Fr Hc Ji Kn Ko Mz Ng Nw On Qa Qe) Qn(aJ aP dR Hv Hx Ld Mz Ng On Qa Qe) Of(Ba Bg Ct Cu Fr Hc Ng On Qa Qe Tn) Jo(Ap Ez Fr Kg Ko Mg Mt Ng Qe Tn) Og(aF aJ Ez Hu Hv Ko Ld Qd Ua) Jq(Ez Im Ji Qa Qd Ut) Jv(Fr Jn Ko On Qe Tn) dK(aJ aQ cP Hc St Wm) Io(Fr Hc Ko Qe St) Hx(bN bP dR eF) Iq(Ez Hu Ua) Jt(Ko Ng Qd) Uu(Ba Bg Hc) Ue(Kg Mg) Hv(bN eF) Ld(cP Or) AoUt BaKl DlNg EzIl ToHc PhcU aQdN bPdD dMdR} Ow{Kk(Aa Af aQ aV aX Bn cE cF Cq cS CX dH Dk Ha Hb Hr In Io Iq Jo Jq Js Jt Jv Ks Md Mj Mr Ms Mx No Nv Nx Oe Og Oy Pg Po Pz Qn Qx To Tv Tz Ug Uk Up Ur Uu Vo Vp Vs Tj) Jq(aA aE aQ aV aW aX bJ bN cF cS cT CX dK Ex Fa Hu Hv Hx Io Ji Jn Jp Jr Kc Kd Kg Kn Ko Kq Ld Mg Mu My Mz Nn Og To Up Ur Vv) Ms(aA aE Af aJ aQ aV aX BN bV cF cS CX Ha Hv Hx Io Jf Jn Jp Jv Kd Ko My Mz Pg To Up Ur Vo Vp) Og(aA aE AF aJ Ao aW Bn bV cS CX dK Fw Ha Hb Io Jv Kc Kd Mj Mx Of Pg Qn Ug Uk Up Ur Uu Vp) cS(aA Af Ao cE cT CX fP Ha Hb Il Io Iq Jo Jv Kc Kj Mj Mm Mp Of Pg Qn Qw Ug Uk Up Ur Uu Vo) Ur(Aa Af Ao Ar aW aX BN cP cT CX dK Hb Io Jt Jv Lu Mm Nx Qn Rb Rh Ue Ug Up Wm) Hb(aA aE Af aQ aV BN cF cT CX Ex Hx Jn Jp Kc Kd Ko Ky My Mz Nw Ph To Up) aA(Aa Af aX Bn CX dH Ha Io Jt Jv Mj No Oe Pg Qb Qn Tz Up Uu Vo) Jp(Af Dg Ha Il Io Jo Jt Jv Kj Ks Mj Mp Pg Qn Tr Up Uu Vo Vp Vs) cT(Af aX Bn Cq Ha Io Jv Ks Mj Oe Pg Qb Qn Tt Tv Up Uu Vo Vp Vs) Uu(aX Ba BN bV cF CX eF Hc Hx Jn Ko Mj My Qn Up) Ex(Af Ha Ij Io Iq Jo Jv Mj Mm Of Pg Qb Tz Up Vo) Ug(Af aV BN cF cP CX Io Kd Mj My To Up Vp) bV(cA cE dH Ha Io Iq Jt Jv Kj Mj Mp Pg Up Vo) cX(aE aX bN cW dK Ha Iq Jo Jv Lu Mj Qw Uk Up) dK(Af bN cP Cx Jf Jv Mj Mp Pg Qn Qw Uk Up) Af(aE aX bN Hx Io Kc Kd Mj Ph Up) Jv(aE aS bN Hr Kc Mj Ph Qn To Up) Vo(bN Cx Gp Hx Jn Kd Ko Kq My Ph) Cx(aE Iq Kc Kd Mj Pg Qw Up) Jo(bN Kc Kd Kn Mg Ph Vv) Jt(bN Jn Kc Kd Kn Ko Ph) Qn(bN Hx Jn Kc Kd Mj Up) My(Aj Ao Iz Kj Of) Ha(Cs Hx Kd Lj) Io(aS cP Hr Ub) Iq(Bo cF Kc Uk) Rh(Aa Mj To Up) Hc(Ao Iz Of) Kc(Aa cP Lu) Mg(Om Ue) Mj(Ax Hx) Il(Mu Nn) Kq(Om Uc) cF(aW Fw) cP(Mm Of) AobN CsKr JnJs KdNx KjaX PgcU aEdD} Ur{Hb(Af aJ aQ aX bJ Bn cP cS CX dK dR eF Et Ex Ez Fr Hv Ih Im Is Ji Jn Jp Jr Kc Kd Kg Kk Kn Ko Kq Lh Li Mf Mg Mu Mv My Mz Ne Ng Nn On Or Ph Qa Qc Qd Qe Rg Sr Tn Uf Vu Wm) Af(aA Aw aX bC bE Bg bJ bN Ch cP cS CT cZ dB De dK EF Hc Hu Hv Im Io Jh Jr Jv Kc Kd Kg Kk Kq Kx Mg Mi Mu Mv My Nn Nq Qy Uf Ut Wm) Jq(aA aX cP cS cU dK dR Ex Hu Hv Im Ji Jn Jp Jr Kd Kg Kk Kn Kq Ld Li Mg Mi Mv My Og Or Qa Qd Qy Rj Tn To Uf Vu Vv Wm) cS(Aa aG Ao aZ BN bX cE cP cV CX dB fP Ij Io Iq Jo Jt Jv Kc Kd Kk Ks Mm Ms Of Og Or Qn Uu Vo Wm) My(aE Ao Bn cU CX dB Dg Dl Ef Io Iz Jo Jt Jv Kj Kk Kl Lu Mm Ms Nx Of Og Om Qn Ub Ug Up Uu Vo) aX(aA aE Ao BN cP cT CX Hv Hx Iq Jo Jv Kd Kk Lu Ms Og Or Qn Rg Ug Vo) Jv(aA aE BN bV bZ cF cT cU CX DB Ex Fr Jn Ju Og Or Tn Vu) Jt(Ba Bn Ct Hc Hv Hx Im Kc Kg Ko Kq Ma On Pb Qd Sr Tn Ua Vu) Qn(aA aE bN cF cT cU dB dK dR Hu Hv Io Kd Kk Lu Mv Og Rj Wm) Cx(aA aE aW bN cF cT cW dB dK Hv Io Kd Kk Lu Ms Wm) Og(aA aF aJ BN bP bV cV Hv Io Kc Kd Kk Or) cX(aA aE bN cF cT cW dB dE dK Hv Io Lu Ms Wm) Lu(aF An bN cV dK Hv Hx Kc Mg To Uf Wm) cU(aQ bN cP cW dB Io Kk Or To Ug Up) Bn(aA bN cP cT dK Hv Kk To Vo Wm) cP(dB dK Kc Mi Mu Nn Ub Uf) Ar(aE Ex Fp Kc Kd Vu) Ug(An bN Ct Mg Vv Wm) Uu(Ba Bg Ch Ct Hc Mv) bV(cF dR Io Mu Rj Up) Ms(aA Kd Or Rj To) Jo(Ct Kg Kq Mg Pb) Vo(Ba Ct Im Kq Pb) Nx(bN Hu Hv Kc) Wm(dB To Ub) Kq(Bb Dl Om) Ao(Bg Tn) Mv(Dc Om) Ue(Kg Mg) Io(aA Or) bN(Aa Ub) BaKl CtDl NiNj HxUp HcOf IqOr NyVu aGeF bZcE} Kc{Og(aA aE AF Ao aW bN bV cE cS CX Dc Dd dH dR Fw Ha Hb Hr Hu Io Jf Jo Jq Jt Jv Kd Kf Kr Ks Lu Lz Mj Ml Mr Mx My Nl No Nx Of Or Pe Pf Pg Qn Rg To Tr Tv Up Vo Vp)

Figure 15 Continued

My(Aa aC Ad Af Aj Ao Ap Bb Cp cX De Dg dH Dl Ef Ez Ha Hb Ij Il Iq Iz Jg Jk Jo Jq Jt Jv Ke Kf Kg Kj Kl Ks Lu Ms Nx Ny Of Om Oy Ph Pz Qn Tv Uc Ue Ug Uu Vo Vs) cP(Aa aC Ad Af Al Ao aQ aX Bn bV bX cS CX Dc dK Dl dR Ha Hb In Iq Iu Jk Jo Jq Jt Ks Lu Mj Mm Of Oy Pf Qb Qn Rj Rm To Tv Ub Ug Up Vo Vp) Hb(aA Af aK aQ aU aV BN bV cS cT CX cY dR eF Ex Fr Gl Hc Hr Hx Jf Jn Jp Ko Kq Ky Ma Ml Mn Mz On Or Rh Sr St To Ug Up) cS(Aa Af Ao aQ bN bX cE cF cT Cw CX De Dg dl Ha Il Io Jo Jq Jt Ke Kj Ks Lu Mj Mp Nm Of Qn Uc Ug Up Uu Vo) Af(aA aE aK aQ aU aV bN cF cT cY dD dJ dR eF Ha Hr Hu Iq Jf Jn Jp Kd Kq Lu Mj Mz Nl Rj To Up Vp) Jt(aA aQ aV Ba BN bV cF cT Cx cY Ex Fr Hc Hx Jf Jn Jp Kd Ko Kq Ma Ml Mz Nk On Sr) Lu(aE aQ BN bV CX dJ Ha Iq Jn Jp Kd Mj Ml Mz Qn To Uu Vp) Jq(aQ aV bN cT CX cY dR Ex Gl Hv Jf Jn Jp Kd Ml Mz Ug) Vo(aA aQ aV Ba bN bV cF cT cY eF Hc Jf Kq Mz Or) Jo(aQ aV aX BN bV cF Cx Ex Mg Ml Ni Nk) aQ(Aa Ao Cx Dg Dl Iq Jv Pj Qn Ug Uu) Aa(aA BN bV cT cX Jf Mz Or) bN(CX Dl Iq Jv Nx Qn Ug) cX(aA aV cF cW Iq Ph Up) Cx(aA aE aV cT cW Iq) Qn(aA aV cF cT Jf Or) Ug(Bn cF Iq Ml Ni Wm) Jf(Dl Iq Ks Nx) cT(Jv Ks Tv) Dl(aV Mz) Iq(bV Or) Ph(cF Kd) BnaV DeaX DgMa ExLi HaMl HcOf JnJs JvaE OrUu aGeF bZcE cFcW} aA{cX(aC aW Ax bC bM bN bU cF cS cT dB dE dH dN Hb Hu Io Iq Jt Jv Kg Lu Mg Ms Mu My No Oe Of Og Om Qb Qy Rj Up Vo) Og(AF aX Bn cS Cx Fp Fr Hu Hv Jg Ji Jr Kg Lw Lx Ma Mg Mi Mp Nn Nt Nu Nw Ok On Pb Pe Po Qy Uf) Af(aF bC bN bU Co cS cT cU dB De dN Ef Hu Io Jh Kg Kq Mg Mu Mv My Nn Nq Oe Om Qy Rj Uf Up) Iq(aX Bn cS Cx Fp Fr Hu Hv Hx Ir Is Ji Jn Jr Lx Ma Mi Mp My Mz Nn On Pa Pb Pe Po Qa Qd Qe) Cx(aC aF aW bC bN bO bU cF cS cT cU dB dN Hb Mg Ms Mu My Ni Oe Of Om Qb Rj Up Vo Vp) cS(Aa bN bO cV dB dG dH Hb Io Jo Jq Jt Jv Ks Lu Mm Ms Oe Of Om Qn Tz Up Uu Vo) aX(Aa Hb Io Iz Jo Jq Jt Kd Kj Kl Mb Mj Mp Ms Nd Of Om Qn Rj Ss Tz Up Uu Vo) Of(Bn cF Fr Hx Jg Ji Lh Lx Ma Mg Mi Mp Mz Nn Om On Pb Pe Qd Qe) dH(aJ bC bJ bN bZ cO cU dE dN Io Li Ma Mp Mu Mv My Nn Nq Pd) Ms(bC dN Fr Hu Hv Jg Jn Lw Lx Mi Mp Mu Nn Nw Ok Om On Pb) Jt(aF Bn Fp Fr Is Ji Kq Lh Lx Ma Mi Mm Mp On Pe Qa Qd Qe) Qn(aQ aU aV bN cF cY dA dK dR Io Kg Kq Mg My Mz Uf) Oe(Bn cF Fr Hv Ji Lw Lx Mi Mp Mz Nw Ok Om On Po) Om(cF Fr Ji Lx Ma Mi Mp Mz Nj Nn On) Vo(aQ aV BN cY Kg Kq Ma Mg) cU(aF aP aW bO bQ cE cV dB dG) Mi(Hu Js Ly Mb Mf Nj Pb) Aa(aF cF Ji Mb Mg Nd) Nj(Fr Lw Lx Mp On Pb) Io(BN cF dK Ex) cT(aF bJ BN dN) Ao(Mg Mu Mv Nn) Ly(Fr Lw Mp Nn) bN(Bn dB dN) Lw(Hu Mb) Mg(Dl Ng) Mp(Mb Ml) Jq(Kg Kq) aC(bJ dE) dB(Bn dN) DeMu MaNg HbKq JrPb bOdN} Kk{cS(Aa Af aG Ao aQ aV BN bX cA cE cF cK cP CX DG dH dJ Dl dR fP fR Hb Il Io Iq Jo Jq Jt Jv Kd Ke Kj Kl Kr Ks Lu Ly Mj Mm Mp My Nm Of Og Om Or Pf Pg Pz Qb Qn Rj Ug Up Uu Vo) aX(aC aE Af aG Ao aQ BN bP bS cA cE cF cT CX dC Dg dH Dl dR Hb Jo Jq Jt Kd Kj Kl Kr Ks Ky Lu Mj Ml Mm Mp Ms My Nm Of Og Om Qn Rj Ug Up Uu Vo) My(Aa Ad Af Aj Ao Bn Cq cX Dg dH dK Dl Ha Hb Io Iz Jo Jq Jt Jv Kl Kr Ks Mj Ms Mx Nx Ny Oe Of Og Oi Pz Qb Qn Tv Ug Up Uu Vo) Og(aF aQ aU aV BN CX dK dR Hu Hv Io Jv Kd Kg Ly Mg Mj Mu Mx Nn Nx Qn Uf Up) Af(aQ aU aV bC bN cF De dK dR Fr Jh Kg Kq Mg Mu Mv Nn Nq Qu Qy Uf Up) Hb(aQ aU aV bN cF CX cY dR Gp Kg Ma Mg Mu Mv Nn Qy Uf Uh) Qn(aQ aU aV bN cF cY dR Kd Kg Kz Mg Mj Mu Nn Qy To Uf) Cx(aE aQ aV bN cF cY dB dR Mj Ms Rj To Ug Up) Aa(aQ aU BN Kg Li Mg Mu Nn Qy Uf) cF(aQ aV BN cX Jv Oe Ug) Jq(Fr Kq Mu Mv Nn Qy Uf) Jt(aU Kg Kq Mg Mu Nn Uf) Ks(Kg Kq Mi Mu Mv Qy Uf) Vo(aQ aU aV Ba cY Ma) Jo(Kg Mg Mu Nn Uf) Oe(aQ BN Mj Up) aV(Bn cU cX Mj Up) bN(cX Nx Ug) cU(aQ Mj Up) Mu(Bb Om) Mv(Om Vs) cX(Lu Up) OfaQ cPdK} cT{cS(aD AF Ao aW bJ BN cF cL CV CX dB dE dM Dp fP Io Iq Jo Jq Jt Jv Kd Mm Mu Nx Oe Of Og Om Pg Qn Up Vo) cX(aD aE aJ aN aP aW aY bE bJ Bn bV cE cF cN cP cR cU Cv dB dE dM dN fR Io Jv Mi Mu Oe Rj To Uf Up Vp) Af(aJ AW aX bC bE bJ Bo cF cN cP cU dB DE dM dN Ef Fr Hu Io Jh Kg Kq Mg Mu Mv Mw My Nq Qy Uf) Mu(aD aG Ao Bn bP cE Cx De Ha Hb Il Io Iq Jo Jq Jt Ks Mp Oe Of Om Oy Uc Ue Vo) Cx(aD aE aF aJ Ao aW aX aY bC bJ cE cF cP cU dB dE dM dN Io Mg Oe) aF(aJ aP Bn bZ cF cR cU Cv dE dM dN fR Jt Lu Nx Oe Og) bJ(aD aE aJ aN aW BN bV cF cP cU Cv dB dE dM dN) Jq(aX De Hv Ji Kg Kq Mg Mi Mv Nn Nq Qd Qy Uf) dN(aW bF BN cE cF cP cV dB dE dH dM Io) Nn(aD aG Ao Hb In Io Jo Js Jt Of Om Vo) cU(aD aS aW bF BN cE cP Cv dB dE) aJ(BN bO cE cF cV dE dG dH Oe) aX(Io Kd Mb Mj Oe Of Om Qn Ug Vo) Qy(De Hb Jo Om Uc Ue Vo) Bn(bC Bo Cv dB Hv Io) Kq(Ha Hb Ks Om Uc Vo) Io(bP bV Jp Mi My) bN(aP cR Cv dB) cE(bW bZ cO Ma) Ao(Mg Mv Nq) Jo(Kg Mg Uf) cO(bF bQ dH) dB(aD cP dM) My(Oe Of) Jt(Mg Qd) Kd(Qn Tv) Kg(Hb Vo) Uf(Ks Vo) bZ(bF dH) dE(aD cV) CvbC NqOm OebP aPdH bEoK} Og{Hu(AF aJ Al aW Bn bP bV Cq CX dB Dc Fp Fr Hv Hx Is Jg Ji Jl Jp Lh Li Lw Lx Mi Mm Mp Mu Mz No Nu Nw Ok On Pb Pc Qa Qe Up) Hv(aF Cx Fr Ha Ip Is Jg Ji Jp Jq Lw Lx Ma Mb Mi Mm Mp Mt Mu Mv Mz Nn Nw Ok On Pb Up) aF(Af aJ aP Ba Bo bV cF cP cS Cx dB dE dM dR eF fR Jr Lu Mb Mv My Or To Ub Ug Up) aJ(Af aP aQ BN bS cS CX dG dH dK Io Mg Mj Mu Mx Nn Nx Oe Qn) Kd(Af Al aX bV cS CX dB dR Hb Io Jo Jq Jt Jv Nx Qn To Ug Up) Mb(bP cS Fr Hx Is Jg Ji Lw Lx Mi Mp Mu No Nw Ok Om On Po) Mu(aE Ao aY bV dM Fp Hx Lx Ly Ms Nj Nu Om Pb) Mi(Fp Hx Ik Iq Jo Ly Ms Ni Nj Om Pb) On(Fp Ik Jt Ly Nj Nu Oe Of Om Pb) Fr(Fp Ly Nj Nu Of Om Pb) Nw(Js Jt Nj Nu Nx Om Pb) Ug(aX bN Kg Mg Uf) bV(CX Io Nn Qy) Nu(Lx Mv My Nn) Ji(Jq Ly Nj Pb) Kq(Ao Jq Uc Vo) Cx(aE cS dB) Mp(Fp Ly Pb) Mv(Fp Ly Pb) Of(Ba Jg Nv) Af(Aw Bo) Io(Ko Ph) Jp(Ik Pb) Or(cS dK) bN(bP cS) cX(dB fR) dM(Mg Nn) BaVo BnBo LxMf JgOm} Jo{Mg(Af aJ aP aX Ba Bn Bo bV bZ cF cP cS CX dB dF dM Ex fR Kd Kn Ko Kp Or Ph Qw Rg Rh To Ue Ug Uk Up) Kd(Af aX Ba BN bV bZ cF cS cU CX eF Fr Hc Kg Kq Ma Mu Mv My Nn Pb Qy To Uf Up) cS(Af aJ Ba BN cF cP Ct CX dR fP Hc Hu Hv Hx Kn Ko Kq Mb Mf My Ph Up) Fr(Af bN CX Fp Hu Hv Ik Ir Is Ly Mb Ms Nj Pb Qe Wm) Kq(AF BN bV CX Hb Io Iq Jq Jv Om Pb Ph Qn Uu) Mi(bV cP Ex Fp Hu Hv Ik Jp Lh Ly Mb My Nj Pb Qe Wm) Nn(bV cP dM Ex Hu Is Kn Ko Nv Ph Qd Qe) Kg(Af cP cX dM Ex Jp Kn Ko Pb Ph Vv) Qd(Af bN Hb Jg Lx Mp Nw Ok On) Ex(aF aQ aU bN Ez Mu Qy Uf) My(aE AF aW Bn Cx) Mp(Ik Is Nv Ok Qe) Mu(bV cP cX Kn Ph) On(Ik Ma Mb Oe Om) Ba(aF cX Of Om) Co(Af aJ bV dM) Qe(aF aX bN Ji) Ph(aX Mv Qy Uf) cP(Mv Nq Qy Uf) aJ(bN Cx Ma) Ik(Jg Lx) aF(Hc Lh) bV(Nq Qy) CxJp LwHu JibN KnaX UfVv} Vo{Ba(aE AF aG Ao aQ aV aW aX BN bP bV cF cS CX dB dK Hb Jq Jv Kd Kg Mg Mj Ms Mu My Nn Oe Of Om Or Qn Uf Ug Uu) Kq(aE Af Ao aQ aW aX BN bV cF cP cS CX dB Dk Ha Hb Hr Jq Kd Md Mj Mr My Om Or Pg Qn To Uc Ug Up Vp) bN(aJ aQ Bg bV cS Cu Ex Fr Hc Im Jg Ko My On Qd Qc Uf Vu) aQ(aE aW bJ bV cS CX dM Ex Fb Hv Hx Kd Ko Pb Sr) My(aE AF aW Bn cS Cx dB dK Kd Mb Mj Ph Ug Up) Im(Af Bn CX Hb Jf Pb Qn Up) Kd(Af aX cF cS Cx eF Pb Qn Up) cP(aF Kg Mg Mu Nn Qd Qy Uf) cS(aJ CX Hc Or Ph Sr) bV(Cu cX cY dR Mu) Bn(aJ Hc Nv On) Cx(aJ Ez Ko Sr) cX(Cu cY fR Jg) Sr(Ni Pb Qn) Uf(Af Jq Mp) Cu(Up Vp) Mj(On Qe) Or(Ma Mg) AfFr MbMz NiJp HxPb HcaX QdJq QcUp aJcY dMdR} Kd{Jt(aX Ba bN bV bZ cF cS cU Cx eF Et Fr Hc Hx Im Jn Jp Kg Ko Kq Ma Mg My Mz Nn Nw On Sr To Uf Uh Up) cS(Ad Af Ao CX Dg Dl dR Hb Io Iq Jq Jv Kj Ks Lu Mj Mm Nm Of Ph Pz Qn Ug Up Uu) Ug(Af An aX BN cF CX dH dK Hb Io Mg Mj Mx My Ne Nl Nn Up Vp Vv) Af(aX cF dB De dK dR eF Hb Jh Jp Kg Kq Lu Mg Mu My Oe Rj To Up) Hb(aQ aX bV CX dB dR eF Jp Jr Ky My To Uh Up) Jq(aX cU cX dB dK dR Fr Gl Ji Jp Kq Mv Nn To Up) aX(Aa CX Dl Kj Lu Mj Mm Ph Qn Up) Lu(CX dK Mj To Up) eF(Dl Jv Kl Of Uu) Qn(dB Jp To Up) Cx(dB Ms Up) My(Dl Kj Of) Ms(Or To) Up(bV cU) Ph(bV cX) AaMu} Of{Ba(Af aX BN cF cS CX Hb Io Jq Jt Lu Mi Mu My Qn Rj To Up Uu) Hc(Af aQ aV aX Bn cF cS CX dB dR Ky Ma Mj Mu Mz Nn To Uf Up) My(aJ aX Bo bV cF cS cU Cx dB Jl Ky Ld Lw Mi Ms Nn Nw On Ug) On(cF Fr Iq Jq Js Jt Ly Ma Mb Md Mi Mm Ms Mv Ni Nx Oe) cF(aJ aP Bg bV cS Cu Fr Hx Im Jl Kq Qe) Jl(Hu Jg Ma Mb Mg Mp Ni Nn Ok Pb) Fr(Cx Hu Hv Hx Is Ly Mb Ms Ni) Qe(Hu Jg Mp Mu Mv Nn) Qa(Hu Jg Lx Nn Nw) Mi(cP Hu Ly Mb) Kq(Af Cx Hb) aQ(eF Ex To) Or(cS Mg) CuVp NuMv LuNw LxIm KgcP aJcS} cS{Ug(Af aQ BN bX cF CX dR fP Mf My Up Vv Wm) Af(Ba bN Bo dB dM Hu Hv Lu My Rg To Uk Up) Jq(aJ Ba Bo cF dR Hu Hv Ko Kq Mu My Up) Io(bV Dp dR Ko Ky Or To Ub Uk Up) cX(Hb Ld Lu Or Rb Rj Uk Up Uu) aJ(bN bR dG dH dL Jt Mm Oe) My(Ad Aj Ao Jt Kj Oe Uu) Cx(bN dB dM Lu Uk Up) Lu(aF BN fP Hv) Ko(Ao Hb

Figure 15 Continued

Jt Mm) Or(fP Iq Kj Uu) bN(dM In Rg) bX(Qn To Up) fP(In Uk Up) Ao(Hc Kq) Jt(Ba On) MjRg MpMu UcKq HbQx dBdM} Jt{On(aF Fp Fr Hu Hw Im Iq Iv Li Ly Mb Md Mi Ms Mt Nc Nj Ns Nu Oc Ok Om Qa Qd) Mi(Fp Fr Hu Hv Ik Is Jp Lh Lx Ly Mt My Mz Nw Ok Pb Qe) Kq(aE Af Ao BN bV CX De Hb Jp Jq Ko Ph) Ko(aF bN Cx Im Kg Ma Mg Mu Nn) Nw(Fr Hu Hv Im Mp My Nn Qd Qe) Fr(Fp Hv Ly Mb Qa Qd Qe) aJ(BN Cx Ma Mg My Nn) Ba(aF bP cX) Mu(bV cP Qe) Qd(bN bV Jg) AlQe NnbV LxIm MgdM MyaF QaOk} Af{aJ(aC aX bC bN bU cU dB dG dH dL Fr Mu Mv Oe) Jp(cF Hu Jh Kg Kq Mi Mu Mv Ni Nq Qy Uf Up) Kq(Ao Ha Hb Il Io Jq Kj Qw Rg Uc Ue Ug) aX(Bo Hr Hu Hv Hx Mb My Ph Rg Ug) fR(aC aF bC bN bU dB dN) My(Bo dB Hr Oe To Ug) Jh(bV dM Il Rg Ue Ug) Mu(bV cP Il Ue) Fr(aC Bo dB) Ug(aU Kg Mg) Ba(Aj dN) Mi(bV Il) Ue(Kg Mg) dK(Dk Hc) BocU NqbV LuaF ToLd HbNw bZdB} Ug{My(aE aF aX Bn bX cF cI CX dB dH dK Hb Io Mg Mj Ms Om Up Uu) Mg(Ao Bn cP CX De Hb Jq Jv Ml Mp Om Ue) bN(aX Bn cU CX Db Ex To Vv Wm) aX(aQ Bn cF cP cX Hc Vv Wm) cX(aQ aV cF cR Vv Wm) Cx(cF Jp Vv Wm) Vv(aW Bn Io) Wm(cF dB) Kq(Hb Uu) BaUu BnNg NncP MfMj HvcF IoJp aQcU} aJ{dH(aZ bC bF bG BN bO bQ bV bZ cF cO cU CX dE dF dN Mu Oe Qn) dG(bC bF bN bQ bV bZ cF cU CX dF dN eF) Cx(aC aW bN bU cF cU dB dL Iq Lu Oe) cX(bN cF cU dE dL dN Hb Lu) dL(aC bN bU cU dK dN) aX(aC Io Iq Jq) cU(aF aP aW) Bn(aC bN) Mu(Iq Jq) Qn(cF dK) DlMg bFcE bNdN} bV{Io(Ba BN cF dB Ex Fr Ko Ky Mi Mu My Oe Qn Rj To Up) Mu(CX De dI Il Iq Jq Mm Mp Oe Qw Up) Up(BN CX Hx Jp Mi Mj Qn Qy Rj) Qy(De Mj Mp Om Qw) Mi(cX Il Iq Jq) Oe(bN cA Cx Hv) Kq(Hb Jq Uc) Cx(bU dB) Mv(De Iq) Rj(cX Mj) Qn(cA dR) DgMg LuaF JqKg} Mi{Ms(Hu Jp Js Ly Mu Mv My Ni On Pc) Ly(Fr Jp Js Ne Ni Oi Ok On) Mb(Hq Hr Jp Js Md Nf Oe On) Oe(Hu Hv Jp My Qe) Iq(Hu Hv Hx My) Jq(cP Ex Hu Mz) Om(Hu Hx My Mz) Nj(Hq Js) AjMy AoEx MpJp NfHv} My{Aj(aX Bo cF Cx dB Mb Up) Uu(Bo cX dB Hu Ko Ky To) Ao(aX Bo bZ Kq Mu Oe) Kj(aX cX dB dK Kg Mu) Qn(cI dB dK Jp) Hb(Bo cX Ky) Jq(aX dB) Oe(cX dB) FrLy NnOm UbcX UcKq IoKy} Hb{Ko(aQ Bn CX DB dE dR Io Mb Up) cX(Ex Hc Hv Hx Ji Jp Kq Mz Nw On) Jp(aQ Cx dR Io Mb Or) Nw(aQ bX dB Mj Up) Kq(Ao Kj Rg Uc) Ex(aQ dR)} Jq{Ex(aU dR Ez Kg Kq Mg Mp Mu Mv Nn Pd Qy Uf) Kq(cX Dl Il Io Jn Jp Jr Kl Qw Uc Uu) aX(Bo Hv Ji Jn Mb Mz) Jp(Kg Qy Uf) Mu(cP Kn) Ji(Cx dB) MvcP} Ao{Ex(Ez Kg Mu Qy Uf) Hc(aX Kq Mu Nn Uf) Kq(Io Jv Oe Ue) cP(Kg Mu Mv Uf) aX(On Qe) BaMu FrMb} cX{Ue(Kg Kq Mg Mu Qy) fR(aC bN bU dN Rb) Ba(Kl Uu) Kq(Om Uc) LuHv MvUu NiTo HcOe QwdR JpUp UkaX dBdM} Fr{Ly(Hu Hv Md Ms Oe Oi Om On) Hv(Iq Js Mb Ms Oe) Mb(Ms Ng Om) Nu(Ms Oe) HuOe} Cx{fR(aC bU dB dH dN) Lu(aF dK Jp) aX(dM Hr Hv) dB(cP dM) UcKq JpUp aEcF bNdM} Mu{Ms(Hu Hv Lx Ly Mz) Om(Hc Hx Kn Lx On) Oe(Lx On) cP(Aj Ue) ExUc} Kq{Uc(aX Ex Iq Jp Qn) Uc(Ha Mj Pg) Om(In To Up)} On{Oe(Hr Hu Hv Jp Lu Mb Md Nv) MbMd MvOm HuIq} Jp{Io(Or Qn Ub Up) bN(Jv Qn) AaMb LuaF} aX{Hc(Uc Uu) aC(dM Qx) RgbN OrUu} Om{Mv(Kn Lx) BacF MbJl QyQw} dM{bN(dB dN) aCdE aQcU bUdB} Ex{Io(bN Mj) HaIm UcQy} Or{Kj(Kg Mg Nn) MaUu} eF{nY(bO bP) IocW} Ba{PzbP KlKo} Lu{aF(Mb Mz)} Mj{NnUe StdN} Mv{LxOe MsHv} Il{Im(Ha Qn)} aC{BnfR bEoK} dK{bEoK bGiZ} AaMbMz UeQyQw HcUudB

Constrained panels with 3 analytes, where 1.0E-8 >= 'AUC p-value' > 1.0E-9. Contains 4,903 panels of 7,710,078 total panels evaluated. : Jj{Og(Bn bP bV cX dB Hw Ip Iu Iv Jg Jo Jp Jr Lh Li Lx Ly Mb Me Mg Nj Nu Nw Ok Om Pa Po Qb Uf) Hb(aA aJ aU bA Bg bZ Ch Cp cY Dk dR Et Ex Ez Jn Jp Ke Kj Ky Lh Li Mp Nv Nw Ph Qc To Up) Jv(aE aJ BA bJ bN bV cF cT dB Hx Ih Jn Jp Kg Ld Ma Nn On Pb Sr St Tn To) Nn(aX Fp Jk Jp Jr Lx Mc Md Me Mg Ms Mu Mv Ns Nu Ok Up) Mb(bN Ii Ip Jg Ji Lw Ma Mk Mn Mr Mw Nb No Nr Nw Ok Pc) Pb(eF Et Jo Jr Jt Ko Ky Ld Li Mf Mj Mk Mm Mr Nb Nr) Bn(cI Co De dK dM Ez Jh Kg Ko Mp Nq Ph Tn To Uf) Mf(cF dE dK dM dN Hw Ip Jg Jh Jp Li Lx Po Ub) Mz(aF cF cX dB Ii Jl Lh Mk Mr Nb Nr Nw Pc Po) Nj(Ip Iv Jg Jh Ji Jp Lh Li Lx Ma Mg Nq Pe Po) Ly(Et Hw Ii Il Ip Jo Mj Nb Nc Nu Ok Om) Mg(aE Bb dE Ha Jk Mt Nc Nv Pa To Ug Vo) Qn(Ba bJ Bo bZ cR cU cY dB Jn Ky Uf Up) bN(bM cU dB dR Hc Jl Kg Kk Ko Mv To Ur) Up(aA aJ bA Ld Li Ma Mi Qv Qy St Uf) Fr(aA Ao cF dB Dc Mi Mp Nc Nu Om) Lx(Iv Jl Lh Mk Mr Nb Nr Oe Ok Pc) Mv(dB dM Iv Mp Mt Nt Nu Ok Om Pg) Ii(bA Bg Cu Ex Ih Kg Kn Kq Qb Vu) Kk(An aV cF dR Hv Io Jq Kd Lv Wm) Ma(bP cE cX Fp Ih Jp Nu Ok On) Mp(Fp Jp Kg Md Mu Nu Ok Oy) Mt(Jl Lh Mk Mr Nb Nr Ok Pc) Pa(Fp Hr Iv Ji Jk Jp Js Nw) aA(Ct dB Kc Kq Ml Om Qy Uf) Af(aE cP dK eF Ex Ph Vv) Jq(aJ Bg cU Cw Hc Ji To) Fb(aF aZ cF dE Oe Vo) Hv(dM eF Lw Or Qy Vp) Ir(Mk Mr Nb Nr Pc Po) Om(aX bA Co Jh Nw Vu) Us(aZ Ch cP De eF Ex) dB(bC bJ Hu Hx Ld Mi) Fp(Jp Lh On Pe Po) Jk(Hw Im Iv Li Nu) aF(dE Hu Or Ow Wm) aX(Ml Nd Rj Vo Vv) cF(aE aW cP dE Ld) Ao(Bg Kc Kg Qe) Ct(cU Jt Ky Rj) Mi(Ex Js Md Nu) Mu(Ih Ok Or Pg) Hx(bJ Iq Jg Ji) Hc(aE dE Of Uu) Kq(Ha Mj Pg Uu) Nv(Hw Mk Mr Nr) cX(cP dM Ko Vv) Cu(Dc Vo Vp) Me(Lj Mn Mw) Ml(cS Qy Uf) Ub(bJ Kg Lv) To(aQ bJ Ld) Ih(Jo Lw Mr) Qa(Dc Ji Ok) Qe(cZ dE Vo) Qv(bA Jp Or) cT(An cV Mj) dM(cY Kg Qy) dR(aE bP My) Ba(bM Kl) Bg(aE Uu) Cx(aW Vv) Nu(Iv Lu) Ms(Jg Mw) Ua(An Vo) Io(Kd Ky) Qb(Mr Oy) Kc(bX dK) On(Dc Nx) AaKo WmNa ExaU NobA LvLd MjTn MyOr NcIm NiNk HuUu IvLh QyQw JpLi KgbV KybJ OwaW UraZ UtPg VvcS aJbC bMbZ cPcZ} Ii{Hc(aJ aV bA Cs DB dR Jr Kg Kk Ld Lx Mg Mi Mu Qd Rj Sr Uf Uh Uu) Kn(CX dK Ex Hu Hv Hx Im Jh Mg Mi Mp Mu Nn Qv Qy Us) Kk(cX dR Fb Im Jn Kg Kq Lv Ma Mi Mu On Qv Qy Ur) cT(aF bJ Bn bW cF cX dK Ex Hu Hx Ld Mz Uf Ur Vu) aJ(bZ cF Co Ct dR Gl Ih Ji Jn Lx Mz Oe Ow Qv) cS(cF Cp Cx Fr Hx Ji Jp Lu Mu Mz Og Pe Rm Uk) Ko(Af aX bJ cW cX dE Hb Io Jr Ma Mg Rh Vv) Qv(aA bA Bg bZ Ct Hx It Ld Mg Mz Qy Sr) Ba(Aj Ao aY dB Fb Is Ji Jl Nw Qd Rf) Ow(aX bJ cF dK dM eF Fb Hv To Uk Up) Vu(aA Af aX dM Hu Ky Og Ok Rf To Uk) bV(cF dR Ma Mi Mv Mz Nv Qa Up Ur) cP(Bg Cw Kd Kq Lv Mi Mv Qa Tn Ua) Wm(aQ Cw Lh Mv Mz Qa Tn Us) Fb(bN dD Kd Lh Mg Qa St Ur) Ih(Bn Co Cx Ef Or Uf Uk Vv) Kd(bA bN cX Im Jr Sr Uh) Og(Aw bA Bg Bo Cu Kg Ua) Us(Ct Ez Ji Jl Jn Ma Ua) Ex(aA bA eF Ki Mf Nk) Fr(cU Hb Ir Kg Nj Uk) Mz(aP bZ cF Qy To Uf) Tn(aX Jr Ld Lx Ml Or) Kq(Bn Hu Ij Of Pg Rh) Af(Jg Mv Qe Sr Ut) Jn(aX Kg Ph To Ua) dR(dM Lv Qd To Ur) Cx(Cu fR Jp Ph) My(aW dN Gl Un) Hx(bA cF Kg Up) Hb(Im Ji Lh Nv) Sr(Bn cU On Vo) Or(Is Ji Lx Ur) eF(cX Hv Kc Pb) Jl(cX Hu Hv) Jp(Ct Ld Vv) Nv(cF dE Uk) Nw(cF Ct Qn) On(aW bC Uh) aA(aF Gl Kg) bA(bP Cp Nk) Bg(Ji Uu) Cu(dM Ky) Lv(bZ fR) Ma(aP dM) Mg(Qw Ue) Mi(Hv Mb) Im(Vo Vv) Qa(Bn Fn) Qe(cF dE) Qx(aQ aX) Lh(To Uk) Uh(bN Pb) FacX NnPa MrKc NgKy StbJ QhUp JrUr VvbZ aXbN} bA{Qy(Bb bF bQ Cp Dc Dl Dp Hq In Iq Jh Ke Ml Mr Mw Nv Po Qb Tv Uk Uv) Mg(aF Aj cF Co Cv dB Hq Hr Lu Mn Mr Ms Nr Qw Tr Tv Ur) Kc(aQ Dc Dd Dk Dp Hr Lz Mp Mr Ni Nl Nw Of Pe Po To Uc) Kg(Cq Dl In Jg Jk Kj Mj Nt Ny Oe Pg Qb Qn To Ug Up Vp) Uf(Cq Cw Cx Dc dH Il In Jg Lv Mj Mx Nt Og Qb Qn Ug Vp) Lv(Ad aG Al Ao cE Hb Jo Jt Jv Of Og Up) My(aE Al Cq Ct Jq Jv Mx Om Qb Up Uu Vo) Ow(aV bJ dE Dg Dp Jo Jt Kd Kl Ks Mp Qh) Nn(aA Al Dp Iz Jf Mm Ss To Tt Uk Uv) Nq(Ad Bg bQ Dc Dk Hq Hr Hu Nv Po Vs) Kq(Cq Dc Jg Jk Kl Nv Oy Po Qb Tv Uu) Cx(Dp Jt Kk Mr Og Rj Tv Up Uu Vo) Mv(Ad Bg cE Ct De Hq Nx Of Uu) Kd(Af Bn cF Cq Nx Ny Ph Qb To) Qn(aQ aV bP cY dR Jv Qv To) aX(Dp Jt Kl Ks Lu Ny Or Ss) cX(Jq Ks Og Om Pg Qw Tr Ug) Mu(aA Dp Mm Tn Tt Ug Uk) Ur(aF dK Jq Ny To Up Uu) cF(aW cE dM Jq Mp Om Qv) Io(Dp Hr Jq Nx Og Ug) Af(Jt Jv Om Rj Vp) Mi(Cu Js Jt Uk Vs) aW(aJ aS bE bO cV) bJ(De Hb Jv Nx Vo) cG(bC cS cU dN Ma) gL(bQ cV Kl Om Ss) Mp(Lw Lz Nd Pf) Hv(Cq Ny Pg Vp) Qd(Iq Ir Tv Up) Qv(aQ dR Mj Up) Li(Lz Pf Vp Vs) aF(eC Ks Tv Uu) Bn(Jv Of Ug) Hb(Ap aU Ji) Us(Og Ug Vo) aA(bM bO dH) cP(aL cV dE) cS(Ko Ks Or) Ma(Hq Mx) Oe(Al Cv) Ou(cZ Vs) Up(bP Ez) bO(cV dM) dH(aY dA) MfQb MxbP NiOf ToJv IqdB OmdR UgbN cEdM} Ow{Uu(aJ aQ aV Bg cP cY Ex Fr Gp Hu Jg Kc Kd Kq Ma Ng Ph To) Jo(aA aE Af Bn bV cP cT Cx Hc Hx Ko Kq Lv Ma My Og Pb) Kd(Aa cX dH Dl Jv Kj Ks Lu Mj Mm Oe Ph Up Ur) Jp(Aa aE Ao Bn cE Cq Dl Iq Ke Kl Oy Qb Uc) Kk(aE Bg bN Ct Dd dR Ib Ij Jk Mm My Nb Of) Cx(Ao aW aX bN cF Hr Io Jt Jv Of Uk) gL(aE Dg Jk Kc Mj Mp Ng Ny Oc Og Pz) Af(aW cF dB eF Hc Kq Mg My Of To) Qn(aE aJ aX Bo cF cP Hv Io To Uk)

Figure 15 Continued cS(bX dH Hr In Jt Kr Ks Lu Oe Vv) Ex(Al Ao aX Dc Jt Kj Lh Ms Tv) Hx(Il Io Iq Jk Jv Ks Pg Qw Up) Hb(aW aX Bo cP Gp Hv Io Mg Ug) cT(bP cE Dk Iq Jk Jt Ny Of Tz) Og(bN cE Cq Hr Md Oy To Vo) aA(Ao cE dK Ks Mp Ny Of Om) Ha(aS cU Fp Kc Kn Lv Ub) Jq(cP eF Hc Mv Qy Uf) Ug(aQ aX bU Kc Mg Nl) cX(aV cF cP Hr Io Jt) Lv(Io Ks Mp Oe Ub) Of(bN cF eF Kn Ur) Vo(aQ Bn cY Sr Up) Ao(aX cF eF Fr) Mj(Cs dM Jn To) Il(Kc Kg Mg Uf) Iq(aJ bN Ly To) Jv(Bn Bo Jn Oe) Kj(bJ cF Kg Ph) Mp(aX cU Nn) Ms(aF bJ cP) Io(aE Jn Ky) Kc(Dd Dg Up) Mu(Om Ue) My(Ef Vv) Jt(cP Sr) Ks(bV Jn) Up(aE Ub) Pg(aS Ax) dH(aJ dM) dK(Bn Lu) BaKl MgUc NgUs UeaV RhUv aEeF aXcW} Us{Ug(aU Ba CU dR Fr Hu Hx Jh Jn Kk Kn Ko Mi Nn St Uf) Af(aU aX bN Cu cY dK dR eF Hv Jn Mg Mw Mz Qe Qy Tn) Lv(aU cP Ef Iu Jh Mi Mp Mu Mv Mw Nn Qy St Uf) dK(bN cS cT Cx dR Jp Mz Ng Og Or Qe Ur) Qn(cY Fr Hc Hu Jn Kn Ko Nw Pi Sr Tn) aJ(aX bN cT Hx Iq Jv Ld Mz Qv Ur Vo) Hb(Cu dR Hx Jn Kk Ld Mg Sr St Tn) Jq(aU aX dR Hv Jn Ld Mg Mt Mz Qe) aQ(aE cT cU cX dM Hv Hx To Vo) bN(cT Cx dR eF Hc Ld Qv Ub Ur) Ex(aX bV cX Hu Io Kd My Qy) Og(aP Cp Fr Hc Hx Jh Qy Ur) Kc(Bn cF Hu Jn Ky Or Ur) Vo(cY Hx Ih Ma Mg Sr Ut) aA(aF Ef Hx Iu Jh Jn Of) aX(cP cW Jv Mz Ng Or Qe) Hc(Aj Ao cI Iz Jv Ld) Jp(Aa aH aU Iu Jt Nm) Kd(Hu Jh Kq Mi Nq St) cX(aU Ih Mg Mu Ph Qy) Cx(aE aV Hu Kq On) Jo(Cu Ld Ma On Qd) Ko(Aa cU Dl Nm Uu) cT(aD Bn cY Kk Qa) dR(aE cR cU cW dN) Ba(Aj Iz Ss To) Io(Jn Mz Tn Ur) Iq(Qa Qd Qy Ut) Jv(aV Cu Ma Qa) cP(bV Ez Hu Nn) Mm(Fr Qe Qv) Uu(Jg Ng Ua) cS(aF cA cK) Ez(Hr Hx) Mi(My Ue) To(Mt Tn) Qv(De Jh) Kk(Hu Kz) Kq(Rb Ur) eF(aE aG) AlQe WmHr MuUr MzOm UaKj HvcY TnbP StOf OrPi aUdM} Qv{Mj(Hc Hx Is Jn Ld Mi Mv Mz Nq Or Qe Qu Qy St To Vu) Io(aE aU bC dB dK Et Ex Hv Hx Is Ji Lx Mi Ph Un) bP(cT Ef Hc Jp Kg Kq Mf Mg Mi Mu Nn Og Qy To Up) Vp(Hu Hv Jp Li Mi Mp Mt Mu Mz Nn Qd Qy St) Up(aJ Kk Ko Kq Ld Li Mi Or Qd Qy St) Mg(Ao Bn cI De Iq Mp Og Om Uc) Hb(Ap dR Ef Jp Ke Ma Mv Mz Pj) cF(bN cI Hx Mi Mp Or Qd Ua) Ao(Ba Co Jh Ko Mu Ua Uf) Kq(bX cE Md Mr Oy Pg Po) Mi(bJ cP Iq Ne Og Uk) Jq(Hv Jn Jp Mz Pj Qa) bX(bJ eF Hx Kk Mz To) Bn(cT De Hc Kg Uf) Mp(dI Kg Ky Qw Uf) Mx(cU Mz Nn Qd St) Of(Kc Ng Qa Qd Qe) Vo(aU Ez Fb Kg Qa) cI(aJ aU bC Kg Qn) To(bC dK Li Ni) Iq(Kg Qy Ua Uf) Jv(cT dK Lx Ng) aQ(aE dM Im Rj) cE(bZ Mu Mv Qy) Qn(aF dK Ph) Or(dN My Og) Ug(Hc Hu Qy) bE(dD dR Kk) cP(dB Nn Uf) Dc(Qa St) aU(dB dM) bV(aV dI) AfOg AncU BaKl EzHc ExcZ NnUr MadH UbbC HuUu QbQe QdRj JoPb JpdR KkdK KnNx aFcT aJdG aWdB} gL{Hb(aQ aX bN Kg Mg Mu Nn Qw Qx Qy Uf Uh) Kl(eF Kg Ky Mf Mg Mu My Nn Qy Uf Ug Vv) Jt(cF Cs Ex Ky Ma Mf Mg Mz Nn Qy Uf) Kc(aE bS cA cF cP Jh Ml Nx Oi Up Ur) cS(dH Iq Jv Mj Ng Nm Oe Pz Up Vv) Jq(aQ aU bN dR Ex Jn Mb Mf Og) Kk(aE aG bP bX cF dC dR Ml Ph) Mm(aW bN Io Ko Ky Ms Ou To) Kd(dH dK Jv Mj Nm Ny Oe Ss) Aj(Mg Ml Mu Nn Qy Uf Vv) Dl(Fp Kg Ky Mb Mf Up Vv) Om(Bn bV cF dR Oe Og To) Mj(Bn bV Jv Ld Og Ub) Iq(cF Mb Ms To Ub Up) bN(Bn bP bU dB Io Ou) Ss(bP cT Ex Jf Up) Jo(aD aQ Ex Hc My) aC(bE bJ cE cV dC) cI(aD bQ bU Ug Up) dK(In Ng Oe Ub Up) Ef(Mg Mu My Uf) Ms(bV cF Hv Or) Jv(aW bX Ju Qw) Ao(aF Hr Vv) Bn(Al bU Nj) Jk(bV Ko Ky) Oe(aE aG aW) Og(Nd Ou To) bS(aW bP dB) Dg(Jp Ko) Lv(aD cF) Uc(Mu Qy) Hv(Io Ur) Or(Iz Uu) aE(bU dH) aX(Mp Ng) cA(aW dB) cE(Bo bU) cX(aF iZ) DpIo ExKf MfUu InLd KjdB KqKs QnaQ NvOu UgaG UrcP UpbV bQcT} Jo{Cx(aX Ba bZ Co Ez Kg Ko Lv Ma Mu Nv On Qe Sr) Mp(cP Ex Hu Ir Jp Lh Ly Mt My Mz Pe Qa Wm) My(aX Bo bZ cX dB dM Fp Ji Kq Nn Ph Up) Qe(Bn Hu Hv Jg Lx Ma Mu Nw Ok Om On) Mg(aA AW cU dN Jv On Ub Vv Wm) Kd(bJ dB dK Ex Jp Mz Ne Nk Rj Ur) aX(aJ Ba bN cP cT Hc Hv Ko Kq Mb) cS(aF dB dM Kg Nk Or Pb Vv Wm) Ma(aF bV Hv Kk Ko Ok Ur) Kg(aA aE Cs Hc Jn Mz Og) Kq(aE Ao cP Mj Of Pg Uc) Nn(aJ Hc Ik Ir Ok Ur) Mu(aJ Cs dM Fp Is Ko) Qy(cX Jp Kk Kn Ok Pb) Kc(aE cX Hc Nl Or Up) Hu(Is Ji Nw Ok Ur) Qa(Ji Lx Ok On Up) Uf(Jp Jv Kn Ko Pb) Fr(dB Hx Nu Og) Lv(Bn cF Jq Ly) Mv(bV cX Fp Kn) Hv(Ba Is Jg On) Ik(Ji Jp Lw Nw) Co(aE aF Om) Qd(Jl Om Qn) Ur(cP Im Wm) bN(bZ Cw Ko) Ex(bW Pd) Mi(Iq Ok) Mt(cP Up) Sr(cX Pb) On(Lx Md) Ou(Ez Lz) aF(aA cT) AfJh BadN BnaJ WmJp NqcT NiPe HccX JlPb KkaU KocU LicP bJbV} Og{Hv(Af Al Bn cS cX dB Dc Ik Iv Jl Lh Ly Mg My Nb Nj Nu Vp) Mu(aF aW cP cT Iv Ji Jp Mz Nw Of Ok Pc Qe) Hu(Ao bF cS dM Ir Iv Mv Nb Nn Pa Pe Ug) aA(Al aQ Hx Ik Jq Mf Nj Of Ou Pa) Nu(Hx Jg Ji Jp Jq Md Ok Pb Qd) Pb(Fp Hx Jg Jl Mt My Nt Ok) Mb(aX Jl Jp Lh Mz Nv Qe) Mv(aE bV Hx Lx Ms Nj Nw) aF(aX bZ Fr Hx Kd Mi Mz) aJ(aW cY Dl Jv Md Of Up) Ik(Fr Ji Lx Mp Nw Ok) Ou(aD BN Dc Mj Mx) Af(Cp cS dB Kk Kq) Fp(Jg Ji Jp My Nn) Mi(aE Iv Js Nw Pc) Ur(cI dK dM dR Ms) cX(aX cS To Ub Up) Lv(aW cF Ug Up) Md(Bo Kk Nw On) Mp(Hx Jp Nd Nj) Of(Ez Is Jl Kq) bP(Bn Io To Up) dM(aU cS Cx dR) Ly(Jg Jp Ok) My(aE aW dB) Nj(Jg Lx Ok) Ji(Lu Ms Om) Kk(To Vp Tj) bV(bN cV Up) Cx(aX cT) Nn(cT Me) Io(cS fR) Qy(aY Ug) Kd(dK Mj) Om(Is Jl) On(Hr Iq) BndB BobN EzVo FrMs LwMe ImQn KqaY NxOk} My{Kc(aS Bn cP Cw Cx Dc Dk In Io Mj Nt Oe Qm Ss) Kk(aE Dk Ib Jk Js Kj Ky Lv Nv Rj Ss Tz Ub Vs) Cx(Ao cS dB Il Jq Jt Kj Lv Ms Oe Om Uu) Of(aA Af Bn bZ dR eF Hx Is Qe Qn To Up) Aj(aA aJ cT Hu Kd Ky Ms Mu Nn Ra Rj) Lv(aE Al aW aX Bn cS cT Dl Iz Kj Ub) Vo(aQ aX cX cY Gp Jp Ra Rj Sr To) Uu(aA aW aX Hx Jp Kd Kp Qn Up) Hb(Af cS dB dK Ko Ld Oe To) Iz(aJ Ba cS dB Kd Ko Kq Mh) Ao(dB Fr Ky Mb Mi Mv Up) Af(aW In Jt Ky Ms Om) Qn(aJ cS Hr Kd Ra To) Ms(aA Bo cX Lw Mu) Jt(aE aW Bo dB Ko) cS(Dg fP In Ks Vv) dK(Jv Ks Qw Uk Up) Jq(Bo Kd Kq Ky) Kj(Bn Nn Qy Uf) Ou(Ad Dg Qu Tt) Mb(Aa Dl Mi) Oe(aJ Lx On) Om(Li Lw Up) Ur(aG aW Ij) cX(Ky Ue Uk) Ug(aW Kg) BnaA BoIq DlaJ PzKd JpJv KlKo UpbV} cT{Mu(aE aX bV Cq Ct Dg In Jg Jk Mj Na Ny Pg Po Qn Qw) Nn(Bn cE cP Ha Iq Ks Lv Ny Oe Pg Qn Ug) Cx(Hb Hr Jq Jv Of Om Rj To Ug Up Vp) cX(Ao Dp Hb Hr Kc Kd Mg Tv Ub Ug Uk) Bn(bP cF dM Kc Mp Mv Nq Oe To Ug) Io(aA aF aJ bN cF Mg Oe Qn To Ur) Mg(bP Dg In Ks Of Om Ug Vo) aX(Hb Iq Ni Rj Up Uu Vp) cF(aW bN cU dB dE dM Lv) Uf(Ao cE De Ha Hb Uc) aF(aY cN cP dB Jq Ug) dE(aA aW bP cC cP dM) Kd(Af Hb Jv Nx Ph) cE(bJ Mp Mv Nq Qy) Lv(Cv dB Dc Oe) Mi(aD Cq Om Pg) bN(aD cN fR Oe) cS(cP Hb Ms Uu) Ha(Im Kc Qy) bJ(aY bP Ct) dB(aA aH bW) Af(Oe To) Ao(Kq Qy) Cv(dN Fr) Mp(Il Pg) Hv(Mj Mx) Ks(Kg Qy) Ur(An To) aW(aJ bW) cU(cG dH) CtbC MvHb IqKc KqOf OedN VoaU aAcV bPeC} Vo{bN(Cx cY eF Fb fR Hx Jp Kd Kk Mv Mz Ph Qc Sr To Ua Ur) bV(aK aU aV bJ Fr Hx Kd Kg Lv Nn Pb Qy Uf Up Ur) Kk(aK Bn cF Cx dR Gp Kg Mg Mu Nn Qy Uf) Kd(aZ Bn bZ cP cU Jq Ma Nn Qy To Ug) Cx(Cu cY Fb Fr Jp Kc Lv Ph Qe Uf) Ko(Af aX aZ Bn cF cS Hb Mb Pb) Kc(aK aX Bg Ct cX Jn Jp Ma) Ur(aZ bZ cP cU Ma Or Tn) cX(aJ Bg Fr Hc Jp Qe Sr) Mj(aJ Cu Im Qa St Uf) cS(Af bX cF cP Lv Mf) Af(Cu Nv On Sr) Bn(Cu Fr Kn Ng) Im(cF cP Jq Oe) Qd(eF Hb Jf Pb) Up(Ez Qa St Uf) aQ(Fr Jp Rj To) Lv(aX Ez Jn) Hx(cF cY Ni) Mg(Jf Ug) Qb(Qa Qe) Qn(aJ On) Or(aU aX) Pb(eF Fb) cP(Mi Mt) BadR CuaE NndM HbOn JfKg JiJq JtKq KnaX UfcF bJcY} aA{Oe(Aa aF dK Fp Jn Jr Lh Nn Nt Nu Pb Qa) Of(Bg bN Co dR Fp Hv Ik Jn Jr Lw Nv Nw) Jt(bN Et Hv Kg Mg Mz Nn Nt Nw Om Po) Nj(Hv Jg Ji Ma Mz Ng Nn Nw Pc) Bn(aC cS dH Hb Kc Mu Om Uu) Iq(Af Lh Lw Mg Nu Nw Ok) Om(dR Jg Jr Lw Mm Nw Pe) Aa(aV bN Kd Kq Nn Ur) Ms(cF Ji Jq Lh Mz Nb) Ng(Hu Mb Mf Nn Nt Qd) dH(aF Kc Kg Mg Qy Uf) Pb(Hu Hv Mp Mz Nu) cS(cF Iz Kc Kl Mb) dB(aF bJ bU dM Lv) Nn(aC aG Dl Hb) Mg(aC Dg Hb Ks) Lx(Ly Mb Mf) Cx(cP Kg) Lv(aG Wm) Ly(Jg Ma) Mi(Md Ni) Hb(Et Kg) Jq(cX Kc) Js(Hv Qa) Kl(Kq Ma) Qn(Kk Mj) aC(bE Mu) aF(bG dE) AfbO AnUr AoKq CvcX FrMl LuaX LwMf MbOn MpHu HwHx IoKy aJdG aQaU bGbU bMbN bZcE} Ou{Jv(Ao Im Lh Lz Mg Mr Mu Nn Pa Pf Qh Qy Rg Tr Tj) cF(Ao bG bN Dl dN Jk Kc Kj Ks Mg Ms Po Qm) Aa(bJ BN bS dB Ex Ha Nd Vp) bC(Co Cq Dg Dk Ha Hr Il Jk Tr) cP(Dg Ef Ha Jt Ks Lh Mu Nn Po) Kq(Co Cq Hr Jl Mp Po Up Ut) Uf(Cq Mj Mr Po Qw Up) Ez(cE Il Ks Mp Uc) Im(Jt Kr Ks Pg Qm) bN(Ke Kf Lu Nm Pf) Nn(Cq Mj Ue Up) Mi(Cq Mp Mr Qw) Qy(Jt Mp Oy Po) Tj(aH cW Hv) Mg(Ny Qm Uk) Mu(Cq Mj Mr) Mv(Bg Jk Mk) Ju(Cx Kc Kk) Kg(Hr Ny Po) Li(Lh No Pf) Up(Ld Mp Nq) bJ(Jk Po Pz) Dk(Ki Ld) Ef(Ij Oy) Nm(aX To) Lv(Ao Dp) Lz(Bn Dg) Ub(cD Nl) Rg(bM cW) Pf(cS Uu) ExKr MjQd MmcW MnaX MpaD NidN UcHc HxNv ToKf JhOy JpUh PgcO} Lv{Ms(Is Ji Kd Lh Lw Lx No Nw Ok Om Po) cS(Ad aJ Ao cA Cx dB Hb Hx Io Jt Up) Jt(aX Ba Et Ir Js Lx Mm No Qd) aJ(BN cF Cx dG Dl Hb Lu Nx) Af(bN Hu Hv Kq Lu Mw Oe Up) bV(bP cV cX dI dR Jq Jv Qn) Js(Im Lh Lx Po Qa Qd) Mz(Aa Hb Lx Mm Pa) Of(aP Lw Mm Mr Pc)

Figure 15 Continued

Md(Jg Lh Om Pe) Hb(aX Ba cX Hv) Iq(Ir Li Mg Qe) Iu(Ih Ir Is Pe) Jq(cF Ir Ji Nx) Kd(Lu Mj Oe To) Ur(Ao dK Hv Kk) Bn(dB Lu Ug) Dc(Ex Hx Jp) Ng(Mm Nv Qe) Io(Ky Mr Pa) Om(Li Mn Pe) aX(Al cP Qn) cF(Cx dE Jp) Ao(Ba bZ) Nn(Lj Ok) Ly(Mg Nu) Nc(Ne Nl) Hx(dB Up) Jv(aE Jp) Nx(Et Mm) Oz(Mp Pb) BaKl DeMu NoNa MgUe UbUp HvJi IvJn QeOi JfKc UgbN} Jt{Qd(Af Ba Bo bS cF cP CX dM Lx Mp Mu Ok) Ur(bJ bN bV cP Ex Hu Jn Jp Kd Kk Mg Wm) Fr(CX Hx Ir Is Lj Mz Nj Nu) Kc(aE cX Hr Hu Lx Or To Up Vv) Kq(aF cE Mj Of Om Pg Qn To) aJ(Af aX cF cX Ji Jn Mi Mu) Kd(dB Ex Fb Kk Mu Ne Um) Ba(aE Bn Cx Hv Lj Om) Im(bV cS Cx Kk Lh Lw) Ko(aX cU cX Mp Qy Uf) On(bN CX dK Nx Oy) aF(Ex fR Hc Qe St) Mp(Jp Nv Qe) Mu(Is Nw Pe) Kk(aQ Cx Ma) Nn(cP Qe) Lx(Mt Qa) Mg(bV Ug) Mi(cP Ji) Jg(Hv Qa) CobV EzEx LwHu MtOk IsJp QeJi NwPa bNcS} Kk{Hb(Af Bn dK eF Et Hu Hv Jp Kd Ko Mz Ug Up) cX(Aa aQ bC cW dB dE dR Ly Mj Rj To) cF(aE dE Io Jq Mj Of Om Ph Rj Ur) Cx(aU cP dK Hr Io Ks Mu Vp) Jq(aU De dK Gl Kg Kz Mg Mi) Af(cY Hu Ly Mj Oe Rj To) aQ(Bn Dl Io Jv To Ug Uu) aV(Aa Mi Mu Nm To) Kd(Aa Oe Ph Ug) Ks(Im Mg Mp Nn) aX(cP dK Iz Ub) cY(cS cU Oe Of) dR(bN Ny Of Om) Bn(Fr Ug Up) Qn(dJ dK Up) Lu(aF bN) Ma(dH Mj) Io(bV Ug) Jv(bN Ur) Uu(Ch Mv) aU(Dl Of) cS(aK dI) AoFr WmUr NnUg MucP UcKq QyOm} Kc{cS(cA dH Dl dR fP Iq Iu Jf Kf Kr Mm Pg Pz Tr) Cx(cF Dd Ha Hr Jf Kj Ks To Up Ur) aQ(cX De Kf Kj Ks Nx Of To) Jq(aE Hu Hx Jr Or To Ur) Qn(aE dR Iq Jn Ml To Ur) cX(Dd Jf Mp Rj To Ug Ur) Aa(aE dR Iq Jp Ml) Dl(bV cF cW cY Ko) Ug(Ha Mj Nk Up Vp) Mz(Ha Js Ks Om) Hb(Hu Hv Rj Uh) Iq(aE Bn cF Ly) Uu(Ba cF Hc Jf) Dg(aV bN Jp) Lu(aW dR Of) Nx(aV cW Kd) Jv(cF Or) Ks(bN bV) Om(Kq Mv) cU(Ha Mp) AoeF DeaV ExKf ToLi OrdH UpbV aCaX bNcF} Of{Mv(Hv Hx Ir Is Jl Lx Ly Mz Nw Qa Qd Wm) Jl(Iq Ji Lx Ly Ms Mu Nk Nw Qa Qe) Mu(bV Hx Ir Is Ms Mz Qa) Hc(bP bV Kg Mb Mg Mi Qn) Hu(Ir Lw Mz Nn Nw On) eF(bN cF CX Kq Pb) Qa(Ji Lh Lw Mp Ok) Ba(dB dR Nn Or) Fr(Af Iv Nj Wm) Nn(cP Ir Nv) Mb(aX cS Nv) Ni(Hx Is Pg) Im(Hb Lh Wm) On(Af Cx Om) Ur(cU Tn Vu) aQ(Ko Kq Rj) cF(Mz Qd Tn) dR(bV cS Kq) Lx(Mt Qe) Mi(Ms Nj) Nw(Mt Qe) AfBg CxaJ MaOr MgcP MjSt IkJp IrJg KdaX bNcS} Af{Ug(bN cF cY De Jp Mu Nn Qy Uf Vv) dB(Ba bC bV cP cU dM dN Hc Mu Mv) aX(dM Hc Ld Lu Mz Rj To Uk Up) cS(Dk Hc Hx Jh Ld Mw Oe Ph) Mv(aE cP cW Il Kd Ue) Kq(aE Dl Iq Om To Uk) Mu(aC aE Bo cW Hr) Qy(Ex Il Kd Qw Rg) aJ(Aw cF De Jh Lu) Io(bV Ex Jp Ko) Bo(bC bZ Jh) Jp(dR Hb Oe) bN(bZ cU dN) fR(Co cU dH) Ba(Hv Uu) Jh(cP Hr) bV(Oe Up) dM(bC De) NnKd NqcP HbKo JiJq QwQu LdaV aFdF aPbU} Kd{Jq(aQ aV Hx Jn Jr Kg Mg Mi Mu Mz Qy Ug) cS(Aa bX cF dB dH Ha Iz Kr Mp Po To) Hb(aU aV dE dK Ko Ma Or) aX(Ao Dg dH Mp Pf Pz Uu) Qn(aQ cF dK dR Lu) cX(bV dB dR Io To) Cx(dK dR Hr Oe) Mj(bV cU eF Jp) Jp(Cq Nx Up) Ug(aQ Mu Qy) cF(Io Jv Ph) eF(Ao dH To) Aa(Qy Uf) Ur(Bn cU) Up(Ms Nm) aQ(Mm Ph) bV(Io Jv) BgUu HaUb MuOm NxdR} Ur{Ms(aJ An bN bV cP cU eF Hu Hv Wm) cP(An bW Im Mm Mp To) Jv(Bo dE Rj To Wm) Lu(bJ Fw Im Kg) Nx(bJ Kn Mf To) Ny(Jn Jr Kq Tn) cF(bP Hx Io Ug) cU(aG aV aW cE) Aa(Hu Hx Or) An(aE Ex Ub) Ao(eF Hc Vu) Dg(aX Ct Ma) Bn(Hu Io) Ue(Kq Qy) Hb(bE Un) Jq(aJ Mf) Om(dR Hx) Pj(Kg Nn) aX(aW Dl) eF(aE Uu) MgQn MlIo NiNk HuUg JnJs KlKq OrdK bZdH dMdR} Ug{Mj(aX cS Hv Hw Ih Jp Oa Vv Wm) Io(aQ bV cF Ex Jn Ko Ma Mz Wm) Cx(aQ aV Ez Ni Nk To Up) Mg(bN cE cF cS Iq Up) aQ(bJ BN Hb Mf Wm) aX(bX dR Nk Rj Up) cX(aU Hc Hv Ni To) Hb(Ji Ko On Qd) cF(aF BN Vv) Mf(aV cY Up) Bn(Hc Hu) Wm(Db dK) Jv(cS Jp) Vv(Qy Up) aV(bN cU) cP(Kg Mu) MtcE bNbV cUcY} Jq{aX(bN cW Cx dR Hu Hx Is Jp Jr Kn On Qx) cS(bN dB fP Hc Im Ji Kg Ld Mb Mi Qx To) Mi(aJ Fp Hx Jp Lh Nw Ok On) Ji(Aa aJ Ao Bo cF cI dE) Kq(Ao cP Ko Mf To) Kn(Mv Nn Qy Uf) Kg(cP Jf Jn) dR(Hv Jp To) Ex(Im Io) Nq(bV cP) Mv(aJ bV) BaHv MgUe MucX ToLd IoKo QycP} cX{Hb(aQ aV Ba bV cY dR eF Fr Qd Sr Tn) aX(Ex Hr Hv Ky Lu Rj To Ub) Lu(aF bV Jp Ko Ld Ph) Up(aE aJ cU Hv Hx) cS(dM iZ Je Kj Kr) fR(aN cF cU dH Uu) dM(aC aJ cF dN) bV(Kr Oe Qy) cF(Ky Om Rj) Ba(Aj Ao) Ex(bN Io) aJ(aW Oe) BgUu DpHv MuIl TocW IoKy JpJv RjdR OrdK cUiZ} Cx{cS(aC cQ fP Hb Hr Hv In Kj Ld) Ba(aC Aj Ao Kl Uu) aJ(bC Hb Io Mm Mx) aX(aC Hx Lu Rj Uk) fR(aW bN cF cU Iq) Jp(cF Dc Jv Uk) Lu(bP cF Hv) Mu(cP Il Ue) Hb(Kq Nw Sr) aC(bE dM Fr) cU(Bo dB iZ) Uu(Fr Ko) bC(cP dB) dM(bU cF) dR(Om Qw) UeQy KjKq UpaE bNbV bPeF dKiZ} bV{Io(Bo eF Hx Jp Kq Or Ub) Mi(Ao cA Oc Om Pg Qw) Mu(cA Jk Nq Nt Oy) Up(dR Hv Mp Nn Uf) Kq(Ao Dg Ke Qn) Ha(Im Mt Nn) Nq(De Iq Qw) Mv(Il Jk Qw) Qn(bN cK Qy) Oe(Bn cV dI) BndB NnIn HbKo QyJv OmdR UuaQ bGbU} Hb{Ko(aV bN bX cY eF Gp Kg Mj Mu Nn Qn Uu) Ex(aU Ez Mu Qy) Nw(cF dE Mx Vp) aX(Ph Qx Rg St) Jp(Bn dB Up) Kq(dB Mb Up) aQ(cS Hx To) cS(bX dR) BaUu BoMz InQa} Mi{Mb(Hx Mc Mh Ml Nb Ny Oy Pb Pc) Oe(Ir Is Lx Mz Nw Qa Qd) Nj(Md Ni On Oy) Hv(Hq Js Md) Ao(Ba Hc) Ly(Md Nn) Ms(Iq Mz) Js(Hu Jn) Om(Jp On) aJ(dH Iq) WmIn} cS{Ao(Ba Hu Jg Ld Nw Up) fP(dB dE Dp eF Hc Hx) Qn(aQ dR Jp Up) Uu(Ba Hc Ko) Io(aJ Ba) Jp(Dc Up) dM(cF dE) BnRg DgKo LuHx MjTo MsOr UcHc HvIn JvbX KjbN bOiZ} On{Om(Mb Md Mm Mt Ni Nx Oe Oy) Mb(Hr Hv Ms Nv) Md(Io Js Lu) Ms(Hu Mu) Iq(Mm Nx) Oe(Hq Mv) LyNx HrHv HuOy HwHx} aJ{cF(bN bO cU dL Iq Oe) Bn(cU dG dL Iq Mm) Oe(bN dK Iq) bU(bG bX dE) dH(aW dM Ma) MjQn MsaX bGdG bOcU dBdN} Kq{Uc(cF cP De Hc Jf Jv Mj Mp To Up) Om(cI Dc Ha Hu Mj) Qn(Ao Kj Uu) Ue(Up Vp) AoDl BaKl OrUu} Jp{Io(cF dR Ky Uk) Or(aX Mj Up) Wm(In Js) Lu(BN) Ly(Mp Mu) Ms(Mu Mv) AaNd LxOe MbMp JvaE} Fr{Mb(Iq Md Mz Oi) Ly(Ji Ng Ok) Nj(Hv Ng Oe) Ao(Hv Ko) Ms(Hu Om) Uu(dB Or) AaNd HvOm} aX{Rg(Bn Ha Mj Rj) Mb(Ao bN Hv) Hc(Iz Kj) Iq(Bo Or) AoNw LuaF MjQx InbN} Mu{Ms(Ng Ni Nu Nw Oi Om Pa) Ue(bN De) Om(Lh Mz) LyOi HxIq KjcP} Hu{Iq(Jl Lw Lx Mp) Ms(Jg Lw Nn) Ng(Jl Nn) Oe(Lx Pc) JlOm} bN{dM(cF cU dE) fR(aC bU dN) AaKo ExJv LudK UeQy dEdN} Ao{Ex(aU Mg Mv) Mg(cP Or) Hc(aU Kg) BaOe CuVp} Lu{aF(Bn cF cU Hx Jn Jr Oe) BndK} Ba{Uu(aE Bn bP Ko Qn) BnKl} Ex{Io(aQ Hr Ky) Jv(aQ Mj) KlaQ} dM{bU(cU dE) cF(dB dE) dBdN} Om{Mv(Mz Ph) MpJl dReF} cP{dB(cU dN) NnKj TodK} Lx{Oe(Hv Pf) QaJs} Ms{NuMv ToaQ IoKo} Bn{ImKj bUfR} Mg{In(Ue Wm)} Io{KoQn aEcF} bE{nY(bG eF)} cU{iZ(aQ dH)} DeUeQy MbNgJl HvJgOe HxQncF

Constrained panels with 3 analytes, where 1.0E-7 >= 'AUC p-value' > 1.0E-8. Contains 7,041 panels of 7,710,078 total panels evaluated. : Jj{Og(bA bC Ct dM Et Fb Ii Il Jn Jt Kg Kk Lw Ma Mf Mj Mk Mr Mw Mx Nb No Nq Nr Pc) Mg(aW Fp Hw Iv Jp Jr Lx Mb Mj Mk Mp Mr Mv Mx Nb Nr Nt Nu Nw Ok On Pc Ub Ur) Ji(Fp Hw Iv Jp Li Lu Ma Mk Mr Mu Mv Nb Nc Nn Nr Om Oy Pb) Nu(aA Fp Hw Ii Jp Lh Li Lx Mk Mr Mu Nb Nr On Pa Pe Po) Mf(aF aW bN eF Ii Jv Mk Mr Mu Nb No Nr Nw Om Pc To Ur) Hb(aP aV bC Bn bV cT CU De dK eF Kn Mn Ok Uh Un Vv) Nn(Hw Iv Jg Ko Li Ma Mi Mp Mr Nr Nt Nw To Ub Ur Vp) Nj(Et Hw Ii Jt Lw Mj Mk Mr Nb Ni No Nr Nw Ok Om Pc) Mv(aY Bb bP cI cU Hw Jv Lh Li Lw Lx On Pa Pe Ub) Mp(bN cF dB dE Hq Hw Jg Jk Jv Nt Nw Pa Uf Up) Jq(Aw bC bZ Ch dB DE Dk dR Ex Ko Sr Up Vu) Ma(Ao Iv Jk Lu Lw Me Nc Om Pa Pe Po To Vo) Ii(Aw Ch Cp Ef Fb Fp Kj Ko Ld Qh Qy Sr St) bN(bC bE bW cP dK dM dN eF Lu Nq Or Uf Ug) bP(Aw Ba Ch cP dE eF Kg Kq Nq Oe Pb Qv Vv) Fp(Hw Jg Lw Lx Mk Mr Nb Nr Nw Ok Pc) Jv(aA Bo bZ Co cU Cw Ky Mz Ph Qy Uf) aF(Bo bQ dR eF Fr Hv Ih Jl Jn Jr Kd) Mu(aA Iv Lh Lw Lx Mi Nt Om On Pa) To(cF cT cU dK Hv Io Kg Ms Uf Up) bC(Bn cI dM Hv Hx Lu Ms Oe Pb Up) Wm(aJ aQ bJ Bo bZ Ch Db dE Ky) Iv(Hw Jg Jl Mk Mr Nr Nw Pc Po) Jo(Ba Co Ct Im Kg Lx Mb Mt Mz) Ko(aE An aZ bJ cU dE Jt Oe Vo) Ly(Jn Jr Jt Lw Mk Mr Nr Pc) Md(Lx Nb Nq Nw Om Pd Po Ut) Hc(An Ao bF bV cU dB Om Vo) Qy(aJ An Ao aQ Hu Mj Mz Or) Kg(aJ cE Hv Hx Ml Ug Ur Vo) Kq(Bb De Dl Iq Kl Ub Vp Vs) aA(Aa aG bM cP Cv Iq Nw Ok) Bn(aE dR Ef Ex Kn Or Up) Ct(aW De dM Lu Ml Ug Uu) Mi(bM Fb Hq Nf Of Or Qw) Jp(Hw Jl Mk Nb Ni Pe Po) cP(aJ Bo bV dE dR Hx Mz) Nt(Hw Li Mk Nr Om Pa) Mj(Ex Kd Ld Lz Ph St) Uf(aJ aZ dM Iq Or Ur) aE(cT eF Fb Qn Up Us) An(Ex Ld Ph Sr St) Ba(Ad Cv Dc Dl Ny) Nc(Jh Lh Ni On Pa) Ok(Hx Jk Jl Lu Pb) bA(aW cE Iq Ny Vp) Ao(Hu Nq On Qd) Bg(Ad Of Om Vo) Fr(bM Hw Of Vo) Mb(Et Jt Li Mm) Ua(Iq Ms Ny Om) Io(aP eF Sr St) Qn(aV Ch De Vv) Nw(Hw Mk Nr Pe) Or(Af bJ Pb Us) Up(cT dK Hx Kk) Ex(aK cV Pb) Lw(aX Hx Me) Hv(bE cI cZ) Jk(Mk Mr Nr) Jr(Hw Ip Mm) Li(Ip Jh Lu)

Figure 15 Continued

Vv(Kc Lv Qv) aW(Af aX cU) cT(cZ Om Vp) dB(bW dN Fb) dR(aJ bJ Pb) Co(Ad Jt) Nq(Lj Ms) Iq(On Qb) Jg(Ih Mz) Js(Lx Po) Kk(Aa cY) Of(Kc Vu) bE(cW Ml) bZ(dH Om) dK(cX Vu) dM(Hu Us) CvaX EtOy HaQd NoPb LuMn HrHw TnVo QvaZ bMdE cWcZ} Ii{Qv(AP aU Aw cT Ef Et Ez Jn Jp Li Mf Mi Mv Nm Nn Nw Ok Pd Pe Pj Qu Vv) Kn(Af aU Aw dN dR Ef Fb Jn Kc Kd Kg Ky Ld Li Lv Ma Mq Og Qn Uf Ur) Fb(Co CU CX dR Ex Hc Is Ji Kc Lv Nw Ok Pb Pe Sr Us Vv) Mz(Bg bN Bo cP Ct Cx dE dM Ef Fr Gl Hu Kq Ld Or Qn Qu Vv) Wm(aA aV bN bZ dB dR eF Hc Hx Is Ji Kc Lv Mn Qe Ug Uh) cP(bA Cu Cx Im Is Jl Ke Kg Ko Nq Nw On Pe Qe Qy Sr Uh) Cx(aP aX bV bZ Hx Jg Ji Lv Lx Ma Mu Nw Pe Qa Uh) Vv(bA Ch cX Ex Hv Hx Kc Kk Kq Lv On Qa Tn Uh Ur) bN(aP bV bZ cT Cu dR eF Fa Ih Jp Nv Qa To Ur Us) Af(aJ cS cT Cu Fa Ih Ji Jl Kg Ma Mu Nw Qa Qd) Hu(aJ aX CU Ir Is Kk Lw Lx Nw Ow Qe Ur Us) Hc(aA aQ aU aZ Bo cF cT cW cY Li Mf Ml Og Pe) bV(Bg cA Jl Kc Kg Kq Mn Nq Nw Pe Qd Sr Vu) cS(Bg Bn Ct Hv Jn Jr Kg Ld Mb Mi Mv Qa Ug) Kk(bA dE dK Ex Hv Hx Kz Mp Ng Nn Qu Sr) aJ(BA bS cT Ex Hx Jp Mg Mi Mu Mv Pe) Us(aA aP cT Ex Fa Hv Kc Lx Mt Pe Sr) Lv(aP Bn cF dE dM Ky Ph Rj To Up) Jn(aP bZ cT Cu Ex Gl Or Qy Rj Uf) aA(Hv Ir Kc Kd Ko Ld Pg Qn Sr Ur) dR(aP Ba CU cW cX Hv Is My Qc) Kq(dK Dl Hx Kl Md Ok Qw Ur Vs) aX(cW dM Hv Jl Jp Mb Pe Rf Ur) Bn(aP Bg Cu Fa fR Jg Jl Nw) Ih(aP Bo cF Cp DB dE Vo) Og(AP bZ Cw Ld Ph Qy Sr) cX(fR Gl Ld Mu Ph Qc To Uh) eF(aQ Cs cW Hx Is Lj Lx Rf) St(cU dE dK Fn Jr Mj Up) Kd(cT dB Is Ji Or Rh Rj) Ko(Aa bA Hv Kg Lu Nn Uu) Ng(Or To Ug Uh Up Ur) Jl(Bo cF CW Db Pb) Ba(aW bZ dK Lu Lx) Cu(Fn Hb Mv Uk Uu) Hv(fR Gl Lh Rh Sr) Hx(Ld Or Ph Qy Uf) Tn(aW cR dK Iq Mf) Kg(Jf Nw Ow Uk Ur) bA(aS bE cW dB dN) cF(aP bZ dM Ji Lx) cT(bC bP Lx Qn To) cY(Qn Qx Rg Rj Up) Hb(Jp Ok Qd Sr) Qa(bZ Cp dE Qy) Kc(Fn On Or Ow) Ur(Mg Mv On Ua) Aw(Lh My Qe) Bg(Cs Rf Vo) Is(Rj To Up) Ji(bZ Qn Up) Ld(On Ow Qe) Vu(cU Fn Ni) aQ(Ky Rj Ua) Fr(bM Pe) Mg(Fa Uk) Sr(An Jr) Jp(bZ Uf) Nv(dM Uu) Ok(Fn Qn) cU(Qe Qx) CoRf CsMu HaPe NnOw MvcW MyVt NiQh ImUk QdVo JgUu QyQw LhaW} Us{Af(aP aQ aV Aw Ba Bg cF Cp Ef Hu Kg Kn Ma Mi Mu Mv Nv On Ph Pi Sr To Ug) Ug(aA aJ aW bC Co cR cT Ef Im Iu Li Mp Mu Mv Mw Nq Pd Qy To Ua) Qn(aQ aV aX bN CU eF Ez Lx Mg Mt Mv Mw Nv Ph St To Ua Ut) cP(bA Cx Hv Iu Kg Kq Li Mg Mi Mp Mt Mu Mv Nq Qd Qv Qy Uf Ut) Jq(aJ cT Cu Ef Fr Hx Jh Ke Kg Ko Mv Nn On Qy Ua Uf) bN(aP bP cU dN Ex Hu Jn Jv Kd Ko My Mz Ph To Ut Vo) dR(aJ Ba bJ bP cF eF Hc Hv Jv Ko Ld Mz Og To Wm) Ex(aA Aw bA Cx Ez Jh Kc Ld Mi Mu Mv Mw Ur) Jo(Ba bZ Hc Hv Im Jh Li Mv Mw Nn Qt Ua Ut) Og(aQ Aw aX Ba dM Im Kg Mu Mw Ng Qe Tn Ut) eF(aF bP bX Cs cW Hu Io Jn Jv Kk Mz Of To) Ez(aE aG aJ aV dK dM Jn My Mz Of Ur) Hx(aG aV cF cT cY dK Hc Iq Ko Kq Om) Vo(aP Ct Fb Jg Jn Kg Kn Ph Qt Qy St) cX(cF Ef Jh Li Mi Mv Mw Nn Qd Uf Vv) Cx(aP aU Cu Ih Kn Mg Ng Ph Sr Ut) Hv(aJ aV cF dK Fr Hr Iq Ko Ma St) Io(aJ Ba cF Cu cY Hu Ma On Qa Ut) Kq(aS Dl Ha Jf Mm Nm Qw To Uc Uk) Jv(aP aQ Ba Mz Ph Pi Sr St Ua) aX(aE aQ aV dK Iq Je Ko Ly Uk) Hb(aQ Ba Cp cY Ma Mt Ph Qd) Of(aU Ih Kc Ko Ma Ua Ut Wm) Ur(bJ Ef Jh Kg Mg Mi Qy Vv) Ng(Aj Ba Iq Iz Kd Kk Kl) To(Cu cY dK Fr Hu Kk Mz) aJ(aQ Bn cY Kc Mg Mj Mt) bP(aQ aV cR cU cY Hc Jn) Jt(Ba Fr Hc Mg On Qe) Kd(Ef Kc Mg Mu Mw Qy) bA(aG aH cE Kk Or St) My(aF bX Mu Mv Ut) Ue(aU Mv Qy Uf) Qe(cT Hu Qb Qg) Vv(aA dN Kc Qv) aF(aS cU Hc Lv) aV(aP cU dM Hc) dK(aP cY Dk Ko) Ao(Ba Jp Mg) Iq(Im Kg Tn) Jf(Mu Mv Pi) Om(Jh Qa Ut) aA(bW De Kk) aU(aE Rb Rg) Wm(aW cT) Hu(cU Mz) Il(Kg Mv) St(bC Ld) Ko(aQ Lu) aG(Hc Jp) dN(cY Qv) BaDl CucI CvKn LxMj MmOn MuaS TnaE RbQd LdaQ cScV} My{Of(cX Fp Hv Ip Ir Jg Jh Ji Jp Kg Lh Lx Mp Mt Mu Mv Mz Nu Nv Ok Or Pb Pc Pe Ph Qa Qd) Kc(aE bN cE Co Cq cW Hr Ml Mm Mp Ng Nm Nv Oi Ow Po Qw To Tr Up Ur Uv Vv) Kk(Al aQ aV bN cF Cp dB Dc Dp dR Hr Ij Jg Jl Lh Nm Om Oy Ph To Uk Vp Vv) Jo(bA cU Cw Db dE dN Fw Is Kg Ko Ky Ld Li Lw Lx Ok On Ou Qe Qn Rj To) Ms(aJ aX bV dB Fw gL Hv Jg Jp Kd Lx Nn Nu Nw On Or Qn To Up Vo) Ao(aA bA Bn bV cU Ex Gp Hr Hu Ji Jp Kd Kg Ma Mg Nw Qy To Uf) Jt(bA BN bV Cs cX dM Is Ji Kq Kx Ky Lw Mp Nn Ou Ow Ph Sr) Vo(aA aJ aU aV aZ Bo cT CW dR Hu Kg Ko Ky Ma Oe Qn) Og(aJ CX Hu Hx Iv Ji Jp Lw Lx Mp Nt Ok) Kj(Af Bo Ko Kq Ky Mb Mg Oe Qn Rj To Up) Cx(aE aJ Al aW aX cF Dc Hb Hr In Oy) Qn(aE aX Bo bP cT Io Ky Lv Oe Ow Ub) bA(Ad aW cF Cv Hb Hr Jk Mb Mj Ng Oy) cX(Ad aX bV dB Dp Jq Kd Lu Rj To Up) Af(aE aJ cF dM Hu Ra Rj Uk Up) Uu(aJ cT dK Gp Mb Oe Ph Ra Rj) cS(Al Dc Dl Io Jv Kl Ss Uk Up) Lv(aJ Bg cF Dg Ef Jg Kl Up) Kd(Ad Ha Jk Kl Ks Mm Nx Ph) Om(bV cT dB Jl Lx Mp Mu On) Aj(aE Ba BN cU Kg Uf) Hb(aW cT Hr In Mb Mz Up) Oe(aA aE aW aX dM Pc Ub) Jp(Ad Dc Dg Iq Kl Vs) Jq(aW cF cT Kg To Up) aA(Ad dB Dl Iz Ng Nj) cT(aF Bn Ct dB Dc) dK(Dp In To Ub Ue) Bo(Ad Dl Iz Jv) Ow(Dl Jv Ks Ue) Ou(Dk Ij Jg Ue) Iq(dB Hx Lx) Iz(Ky Pb To) Ad(Hu To) Lu(aF On) Mi(Js Mp) Jv(dB Ky) Kq(Kl Qv) aE(aX Up) aJ(dG dH) cI(Hr In) gL(Ks Vv) DcHu DlbV NnNj LwMb UbIo UeaF OydB aCaX aWcF} Ow{Kd(Ao aX cF cS dK Hr In Iu Iz Jk Kr Mp No Of Pg Po Pz To Tv Uk) Kk(aG Ao Bb cP cY Dc dK Il Iz Jd Je Jy Lh Mk Mn Pa Pb Qh Uc) Jp(Ad Bg Dc dH Dk Ij Jk Mm Mn Mx Ny Om Po Tz Vv) Mj(aE aJ aW aX BN cF cP Hv Io Jo Kc Mh Oh) Hx(Ao cE dH Dk Hr Ij In Jt Mp No Oe Om Qb Vp) Ex(Bn cE Cq Iu Kf Mp Mx Nn Ny Po Rm Vp Vs) Up(Aj Ao aW aX BN cP dM Fw gL Jn Jo Of) Kc(aS bN cF cT De Jf Kj Kr Ml Mp Ur Vo) aX(aE aW cE dK Ha Io Jo Jv Lv Og Uk Vo) bA(aG Ao cF Dl Ij Iz Js Lh Mm Ny Po) Jo(aQ Ba bJ dK dM Io Jv Kg Nn Qn) cT(Ao Dc dE Js Kl Mp Om Po Tr Vv) cS(Aj aQ bN cF dR Iz Nm Om Pf) dK(Ha Hb In Io Ks Ms To Ug Uu) gL(Aa aW cE Lv Nm Om Pf Pg Uk) Af(bJ cP Jh Kg Lu Mm Mu Vv) Jt(aE Ba Bn Kq Mg Mz Ok Qe) Vo(aJ aV cF eF Fb Nn Qn To) Ao(bV cP cX Jn Ma Mg Vv) Lv(aE Bn Jf Of Om Tz Vp) Mm(aA aE bN bV dM Jf Ph) Io(aQ aV bN cF dM Mz Uk) Og(aV bF bJ Hq Mr Pa) Ha(Aa Ax Hv Mt Ue) Kj(eF Mg Nn Qy Uf) aW(cX Jv Lu Qn Uu) cF(aE dM Jv Ub Vv) Ms(Fw Mu Nn Or) Hb(aF bJ eF Kg) Ks(Hv Kn Ko Mz) Ph(Dg Mp Of Pg) Aa(BN Iq) Cx(aV cP dB) To(cX Hr Mp) Iz(aA Ba bN) Uu(Bo Sr Ua) Vp(aS Ax Ub) bV(cV Dl dR) cE(aS bZ cU) Ue(Hc Qy) Ij(Fr Jn) Il(Ez Qy) Jv(cP dB) Kn(Js Tv) Ug(aE bJ) Pg(bZ Cs) aQ(Iq Vv) cX(dB Of) AxMx CqaA DgKo NnUc LyRb MpJn MuRh MvOm RgbN OecP UraG aPdH aSbJ cIcW} Og{Nu(Ik Im Ir Is Iv Lh Lw Mg Nb No Nv Pe Qa Qe) aA(aG aW dH dR Iq Mb Ml Ms Om Pc Qn Qv To Up) Mv(Ao aY bP Is Iv Ji Mb Mz Of Ok Om On Qe) Hv(aX bN Hw Iq Mk Mr Nr Pa Pc Pe Qn To) Hx(Fp Fr Ik Jg Ji Jp Ma Ni Nj Nn Nt Ok) Ou(bJ Cq cZ dF Ha Hr Md Nd Nl Pg Uk Vp) Pb(Ik Im Is Iv Lh Li Mb Nv Om Qa Qd Qe) Mu(Af cX Iq Is Kd Lh Mi On Pa Pe) Qd(Ao Dc Jg Lw Mb Mp Nn No Om Qc) bV(aQ bS cA cB cY gL Kg Kk Mg Uf) Fr(Dc Iq Ji Jt Md Nc Ng Nw On) aJ(cT dR Ha Hb Jq Jt Kg Kr Uf) Qv(bC bW dK Hu Io Jv Qn To) Of(Bg Cp Fb Ij Jk Lx Nt Pe) On(Jo Ma Mf Mi Ms Nv Nx Ny) dM(aQ bN cF cX dB dK Io Mb) Nw(Iq Iv Lx Mp Ms Nn Ny) Ug(aQ aU dR Io To Up Wm) gL(aG Al cS fP Kj Mr Mx) Mb(bN Cx dK Ip Li Nn) Jp(Is Li Lx Me Nj Nn) Kk(Cq Hb Jr Ms Ny Tv) aE(dR eF Kd Kg Qy Uf) aF(cW dN Jt Jv Qn Vo) Fp(Is Lw Mt No Om) bN(Cx dB dN Hu Kd) cS(Al fP Jo Jq Lu) Bo(bF Dc Nx Pg) Ik(Jg Lw Mz No) Om(Ba Nj Pe Qa) cX(cT dR Mi Or) Af(aX bA Jh) Lx(Lz Md Ni) Ly(Is Li No) Mp(Ir Iv Ms) Hu(Ip Jq Vp) Io(aP Ky To) Ji(Iq Jt Nc) Ko(Hb Mj Nx) bP(cT Mg Qy) dB(dK Mi Mz) Ao(Jh Lv) Bn(Aw bA) Nn(cP Ok) Mt(Iv Lw) Mx(Kd Ph) Jg(Iv Ms) Jo(Kq Pe) Jq(Kg Uf) Kc(bX dK) aW(aX Qy) CpDc WmUr HaIm LvbF MiOk HbKq JsPe KdVo NxPh aXcT} Jo{Hv(Bn cF Co Cw Cx Ip Ji Lx Mp Mt Mu Mv Nv Nw Ok Qa Qd) Qd(cF Ed Hu Ik Ip Lh Li Lw Mu Mv Nb No Pc Pe Po) Qe(cX dB Ik Jl Jp Lh Lw Mm Mv Nb Nt Pc Po Qc Up) Fr(aF aX Bn cS Lx Md Ns Ok Om On Pa Pe Ph Qn) Is(Fp Ik Jg Jp Li Lx Ma Mb Mv Ni Nw Pb Po) aF(Bg bQ bV bZ cF cP Ct dF fR Ih Jp Lv Tn) bN(aP bA bV Co fR Jp Lv Ma Mi Mv On Qa Uf) Bn(aP Ba bZ Co Hu Kg Ko Mu Nv On Tn) Kq(aW aY cE cI Fw Jt Nn No Tz Up Vp) Af(aJ aX bZ Lv Ma Mi Mu Mv Nv On) Hu(aX cU Cx Ip Jl Kc Li Lx On Qa) Nw(Lu Ly Ma Mp Mt Nn Om Pb Qa Wm) cX(aJ aX bA bZ Ko Ma Mi Nq Nv On) Kc(aY Ct eF Kd Kg Nn To Vp Vv) Cx(bV cP cT Cw Kk Mi Nn Ph) Ba(aE Io Mu Oe Pb Qv Uu) Lv(bC Bo cP CT cU Ko) Mi(aJ Hc Ip Ni Om On Ur) Ik(Hx Jl Lh Mz Nv Ok Po) Kg(De Hx Ml Ng Pc Rb To) cS(cA dE Io Lu Lz Mu Qy) Lx(Ji Mb Mg Mt Nn Ok) Mt(Ji Li Nn Ok On) Mu(cF cW Hx Ly Pb) Ko(aZ Io Mp Pb Qy) Wm(Im Ma Ok On) Kd(Io Kk Nl Vv) Uf(Hc Io Ur Vo) aJ(cF Mv Nq Oe) aX(dM Ex Hx Pb) Fp(Jg Mp On) Nn(Jp Pe Qa) Ur(bJ Qy Vv) Co(aA aW) Ma(Nv Qv) Mg(Cs Ed) Mp(Hx Mb) Qa(Jg Lh) Kk(aQ cU) On(Mf Ni)

Figure 15 Continued cS(bX dH Hr In Jt Kr Ks Lu Oe Vv) Ex(Al Ao aX Dc Jt Kj Lh Ms Tv) Hx(Il Io Iq Jk Jv Ks Pg Qw Up) Hb(aW aX Bo cP Gp Hv Io Mg Ug)
cT(bP cE Dk Iq Jk Jt Ny Of Tz) Og(b

Wm{In(Hx Mt Qd)} To{Uu(Fb Hc) aQdK} cU{Bo(BN) dEiZ} dN{aPdH bNcF bQcE} Aa{Nd(Mz Nw)} Fr{Md(Hv Nu)} Js{LxLz QaNw} Nx{HvOk aFcF} aE{Mull JvdR} bE{nY(dE oK)} BnRgaV LyMvOi Constrained panels with 3 analytes, where 1.0E-6 >= 'AUC p-value' > 1.0E-7. Contains 9,635 panels of 7,710,078 total panels evaluated. :
Ii{Hv(aJ Bg bV bZ cF Cu Cx Fb Is Jg Kd Kg Ky Ma Mv Nv Nw Pe Ph Qe To Uf Ug Ur) Bn(aX bV bZ Co Cp dR eF Fb Hu Hx Ji Jp Kn Lx Mu Mz Pe Qd Ua Ut) Cx(Bg dF dM dR eF Ez Gl Hu Im Is Jn Kg Ky Ld Mi Mv Qd Rj To Up) aJ(cP cX dG Kc Kg Kk Ko Kq Ld Mt Nn Nq Nw Qn Sr Uh Ur Us Vv Wm) Fb(Af aU aV aX bA bZ cT cW Et Gl Im Kg Lx Ma Mb Mf Ng Ph To) To(aA aU aV aX bJ bZ cP cU Kc Kk Kn Mg Ni Og Pb Ph Qv Sr) Kd(dK Ef Hu Kg Kk Ld Ma Mg Mu Mv Nn Qu Qy Ua Uf Ur Vo Vv) Us(aU aX bZ cU Ef Gl Im Jd Jh Kg Ld Mf Mv Mw Ok Qd Qy Vv) Af(aP Bg bZ Co Cp dR fR Hu Im Jp Ld Lx Mi Pe Ph Uh) Wm(aP bA cF cY Db dE Hr Jl Ky Ma Mp Mq Mu Nm Om Pe) Kq(bF cI De Dk Hc Jf Ko Lv Lx Mm Mw Om Oy Tn Uc Up) Hu(aP bN bV bZ cF Cs Hx Ko Lh Ok Pa Pe Qa Rm Sr) Qv(Ch Cp Cw De Dk Ex Gl Iu Jr Ke Kf Lx Mm Ph Uh) cP(aP Aw cT cU dB Ef fR Hx Ih Jg Jp Jr Kk Nv Uf) eF(aV cY Jj Jn Kk Kn Ld Lv Mf Og Ok Pe Ph Qd Sr) Vu(Ap aV aW cR dE dK Iq Ld Mf Ng Om Uh Vo Vv) bV(cB cV Ef Hx Jn Jr Kk Ld Mg Nn Og Qy Rj Ua) St(bP cR Hb In Jv Mg Ml Nl Of Og Uk Vo Vp) Ur(An aP Aw bJ dK Ef Im Kc Ld Li Mi Mp Nn) bN(Bg Gl Hx Jg Ji Kg Ky Lv Ma Nw Pe Qd Rj) cU(Bo Dk Ex Fa Jg Jl Jp Lv Mz Nv Nw Or Ua) Ko(An cT dB dK In Kn Ld Mu Mv Or Uk Vo) Vv(aA Aw aX Cp dN Gl Jj Jn Lx Nw Or) Co(aP Hb Hx Jn Jo Ky Og Uk Up Vo) Sr(cF cT Ez Gl Io Jv Kn Mb Mf Uk) Qy(aA aQ cS cX Jf Lh Ng Nw Ok Ph) dM(Bg Ct Cw cY Jg Jn Mg Mu Pe Qd) Mz(bC Cp dB Is Jg Mu Mv Qe Ut) Hc(aW cI Fp Kn Mb Mv Rf Ug Uk) Ir(Jg Jl Jp Lh Lx Mp Mu My Nn) Jj(Cw Jr Kk Ky Ma Md Nc Ph Uf) Vo(Ap Ct Ex Jg Lh Ma Ng Ok Uf) cT(aP Cp cW dB dN Kk Ky Oe Og) Bg(aP Hx Jn Lv Mi Pe Rj Up) Ph(aU bA Io Li Mu Mv Nn Qn) aX(Bo cF cX dR Jr Og Or Rj) Ef(aA cX Hx Jn Nw Og Ok) Ex(An Hb Jr Mj Mm Or Up) Fr(Fp Hx Is Nu Pa Qa Qe) Lx(dE dR Jl My Pa Pe Pf) Kg(Je Jo Kj Lv Or Qw Ue) Uf(aA Fn Hb Jo Kk Nw Og) Pg(Is Jg Ji Lh My Ok Qe) cF(Cu Jn Ma Mu Pe Qa Qd) cS(cA cX dI Mf Mn Pi Uh) Jl(bZ dB dE Ly Mb My) fR(bS Ct dR Jn Og Qn) Lv(Cp dB Ez Gl Uh) Ih(Aw cX dF dN Un) Jr(bZ Cu dR Kc Kk) Kn(bA De Qu Ug Up) Nw(dE Fn Lu Mi My) Uk(Is Ma Ng Ok Qd) Hx(bC Bo bZ Mu) Im(Fn Jf Qw Tn) cX(Cu Mi Nv Rj) Ba(aP Mg Ug) Fa(Nn Pb Qn) Is(Hb Jp My) Qd(dE Fn Jo) Kk(bJ dN Ky) Ld(cW Jn Qa) Lh(aA Ao Uu) Og(bP Dk Qu) Or(aU aV dK) Bo(bZ Ct) Cu(Lu Of) Gl(Cs Rf) Mv(De Qw) Ua(Pb Pe) Ji(dE Fn) Qx(aU aV) Ow(aW Mu) Uh(aA aQ) dN(On Tn) dR(bJ bZ) CwLu MaUg MgUp NgUu QcRf QeJp QhcR KyPb RgaQ OeaP aAbA} Jo{Hu(Af aJ BA bV bZ cP cX Hv Hx Ir Jg Jp Lh Mm Mu Mz No Nv Om Ow Pc Po Us) Us(aJ aP aU aX bN Co Cp Ef Hx Kn Mi Mp Mu Nq Ok Pb Ph Pi Qu Qy Sr St Uf) Is(Hw Hx Iq Jl Lh Lw Mg Mj Mk Mm Mr Nb Nj Nr Nt Nu Pa Pc Pe Wm) Qa(Hw Ik Ip Jl Jp Lw Mj Mk Mr Mu Mv My Nb No Nr Pa Pb Pc Pe Po) Qd(aW cP dB Et Hw Hx Ij Iv Jv Ma Mk Mm Mr Mt My Mz Nr Pa Pb Up) Qe(Af bC bV cF dE Et Hw Mb Mg Mj Mk Mr Mz Ni No Nr Nu Pa Pb Pe) Kq(aQ bF cF cU DK dN Ha Jy Lz Md Mr Mw Mx Nk Oy Qb To Vs) Bn(Aw aX Bo bV CP cT Cw fR Hc Jh Jp Ma Mi Mv Nn Ph Sr) Cx(BC Bg bN Bo cF Cp dM Ex fR Hc Hx Lh Lx Mv Mz Qy Uf) Fr(bC dM Hw Ip Iq Iv Ji Jv Lh Mi Mk Mp Mr Nr Up Vp) My(Ba cF cT Hv Hx Ip Ir Jl Nt Nw Pb Pc Po Qy Uf Wm) Af(Ba bV Cw Ji Jp Ko Nn Nq Nw Qy Sr Tn Uf Ut) Lx(bN Hw Jp Lh Ma Mf Mk Mr Mz Nr Oe Og Pa Pe) Nv(Fp Hw Ip Jl Ly Mb Md Mk Om Pa Pb Pc Pe Wm) Nn(Ba Bc bN Cw Fp Hv Hx Ih Ji Lh Mi Mx Mz) Pb(Co Ef Hc Jg Ji Kk Ma Mp Mv Mz Pe To Wm) cX(bV cT Cw eF Ex fR Jp Kn Lh Ph To Uf Vv) bN(Bg Bo cT Hc Kg Kk Lh Mz Ph Qy Sr Tn) Im(Hb Ip Jl Li Mp Nb No Pa Pe Po Qn) Jp(cF dR Ij Ir Ji Jj Li Mu Nu On Up) aF(aJ aX Cw eF Kg Kn Ko Mz Ow Uf Wm) cF(aA aX bA bV bZ Co Hx Kg Mt Ow) Mu(aE aY De Ip Ir Kc Mz Ok Wm) Mv(aE Ba cS dM Hx Nu Ok Vv Wm) Hv(Bg bV bZ cP Et Ij Ik Lh Mm) Ji(Fp Hb Jl Ma Mp Ms Nu Up Wm) Lv(bE Bg dB dM Ex Qy Uf Wm) Mt(Hx Ip Lh Lw Om Pe Po Vp) Ik(Et Ip Ir Li Mm No Om Pc) Kg(aW Jq Ly Of Pa Qn Up) Lh(aA aX Hx Mg Of Ok On) Uf(aA aE cS dM Ml Og Qw) Ma(cP dM Hx Ly Nu Or) Mp(Ij Jl Lj Nj Nu Pa) Kd(bA cP cT Mf Ph Rh) Bo(aX Ct cU Hx Mz) Mi(aE Hw Jl Mk Pc) Tn(aE Io Nk Up Vp) Kk(aV bJ cY dK Qn) Nw(Ir Mb Mg Pa Pe) On(dB Ms Mz Nj Qn) aJ(Ct Og Qn Qy Ur) Ni(bA bV Hx Ij) To(aU cY Ld Ow) Jj(Fp Nc Nj Nu) Ko(bJ dE dK Qn) Ex(aK cY Io) Mg(Ir Jl Ok) Nk(aX bA Co) Qy(aE Qw Vv) Up(Ap bV Li) Pe(Iq Js Ok) bJ(cT dR Kn) bZ(cP Hc Vv) cS(aW Jv Nq) Wm(Et Nm) Nt(Hx Og) Mb(Jg Jl) Mf(aX bA) Mz(aX Ok) CwIo EfKn EzOw FpPg NqdM LyJg HcdK SrQn KcUr PhcU bVdR cPgL} Og{Nn(aW dB Ik Ir Is Iv Ji Kd Lj Lx Ly Mu Mv My Mz Nj Nt On Ou Pb Pe Qa Qe) Jp(Af Al Bn Cv Dc Hw Ij Iv Jl Lh Lw Mk Mr Nb Ni No Nr Of Om Pa Pc Pe Up) Mb(Af aW bC cX Hu Ij Ir Jk Jq Jt Mm Mq Mt Nb Nf Pa Pc Pe Qa) My(Af Al Ao bV cS Dc dM Is Kd Li Mz Nj No Nw Of Pc Po Qe) Om(Hx Ij Im Ir Iv Jk Kk Lh Lj Lx Ly Ms Mz Nu Nv Ok Po Qe) Us(Af bN cT Cx EF Io Jn Li Mg Mv Mz Nq Ph Qn To Uf) Fp(Hw Ij Ip Jl Md Mj Mk Mr Mz Nb Nr Nu Pa Pc Pe) Fr(aE Af Al Ao Hw Iv Lw Lx Mk Mr Mz Nr Ok Pa Pe) Qd(Al Ha Iq Jl Ly Mk Mr Ms Nb Nj Nr Pc Po Up Vo) Ou(bE cE cF Jl Lh Lz Mp Mr Mu Pa Pf Rg Tr Tj) Ly(aA Et Hx Im Jl Lw Ma Mt Mz Nv Pe Qa Qe) Jg(Iq Is Ji Li Lj Lx Md Mi Mp Mz Ns Qa Qe) Kk(aA aE bX Dc Dk Ir Mr Nb Nd Or Pa Ra Vo) Af(bV cT dK dM dN fR Hc Ko Mv Nq Qu) No(Hx Im Iv Me Mt Nj Nt Nv Pb Qa Qe) Lw(Hx Im Is Iv Mu Mv Nt Pb Pe Qa Qe) Of(aP cS Et Hc Ik Ko Lh Mi Ok Ua Ur) Nu(Ip Jl Jr Li Ma Mp Mz Pa Pc Po) Mg(aE Ao cP cT Hu Hx Ok On Pb Ur) cS(Ao aW cA cP dI dR Jv Qn To Up) Hu(aX Ha Hw Ij Mj Mk Mr Nr Vo) Jj(cT dR Jv Ko Mm Nc Qn To Up) cF(bA bN bV CX dK Hv Io Ow) Mz(cX Iv Lx Me Mp Nj Nt Pb) Ji(Iv Jl Lx Mi Nr Pa Pc Pc) gL(aD aX bF cE dH Jt Mu Nx) Ao(aJ Aw Kd Kg Mi Qy Uf) Mv(Lh Li Nb Ng Pa Pc Pe) Hx(Hw Iq Is Iv Jq Mt Up) Qe(Al Dc Ik Iq Mp Ms Qc) Ug(aV bV dK Jv Mj Nk Nl) Pb(Ip Ir Jr Mm Nb Nc Nj) Mu(De Hw Jl Mk Mr Nr) Io(aY Ba cT dN Ub Up) Is(Ik Iq Js Jt Ms Nw) Jq(Aw aX Bo Cp Ok Qy) aW(aF bC bV dR Kd Ur) bA(Al CV Dc Mx Nx) Lx(Iq Iv Jl Js Pg) To(aQ bV dK Ld Lv) Jv(aA Bo dB Ko Ph) Ok(Iv Jl Lu Ms Nc) Mp(Im Ni Pc Qa) Mt(Nb Pa Pc Pe) Nj(Ip Jl Lh Po) In(Kg Kq Ld Qy) Ko(Jt Mx Qn Vo) Nw(Jl Ml Nc Pc) Bn(bN cT dM) Lv(Qn Uf Vp) Up(aE dK Ez) Vo(aJ Fb Im) aP(Al bS Mx) cP(Cx dK Mi) Nt(Nb Pc) Lu(bP dK) Md(Mi Pe) Hv(Hb Ks) Jh(Jr Li) Jt(Kq Pe) Kd(Or Uf) Qn(bV dB) On(Jl Nc) aX(bN Or) cX(aE Uf) dR(bV Cx) AjBa AwDc BoHr CpPg HaKq MeMm MjPh MsNv NkaJ UbbJ UeQy IkLh ImKs HbaA bWdB cYdM} My{bA(Ba bF Bg cE Dg Dl Dp Ij Iq Iz Kl Mm Mr Ms Nv Ny Pg Pz Qy Rj Ss Tv Tz Vp Vv) Ao(aJ aP aW Ba cF cT Cw cX Db dM dN dR Et Hx Jn Ko Kx Mz Nn Ra Rj Sr Uh) Of(aE bN cP dM Et Hb Hu Hw Ik Im Iv Ly Ma Mb Mj Mk No Nr Pa Pg Po Uf Vo) Ow(Ad aW Dg Dk Fw Ha Ij Il In Io Iq Jk Kl Mj Mm Oe Om Oy Qw Ss Uk Up) Kk(aW bP bX Ct dC Ef Il In Je Md Mm Mn Mr Nb No Po Qw Uc Tj) Iz(aF aQ aX bN bZ dK Fr Hx Im Jp Kx Ld Nn Ph Ra Rj) Jt(AP aX Ba cT Cw Ex Fp gL Jl Jp Ld Lx Ok To Up) Uu(aE aF Bg Bn bZ Ch Jg Kq Mj Ms Rh Sr Ua Uf) Iq(aJ aX Hv Is Jl Lw Mp Nn On Pa Pe Po Qa) Kj(aE aQ aW bV cI dR Hu Jp Ld Ma Mf Mj Pb) Ky(Ad Cx Ef Kl Ks Lv Mj Ms Oe Om Ss Up Vv) cT(Ad aE Al aW Cq Cv Dl Jv Mb Ms Mu Ny Oy) To(Io Jk Jv Kd Kl Ks Lv Mj Oe Om Ub Up) Hb(aA aE aX Bn dD dE Fw Io Mj Ph Ra Rj) Kd(Cx dB Dg dH dK Hr In Js Jv Oe Om) Ad(aE aJ Bn bV dB Fr gL Hr Ko Mb) Qn(aV aW bN Hx Ko Mb Mj Rj Uk Up) Aj(aW bC cP dM Fr Hr Lu Ma Mg) Cx(bN dM Dp Ks Lu Qw Ub Uk Up) dB(aW Bn cS Dl Ef Ha Hr In Kl) Af(bN Dp dR Fr Lu Mb Mi Mu) Bo(Bn Dc Dg Kl Mm Om Oy Pg) Ms(aW Bn cF cS dN Hu Pc Qw) Jq(aJ dE Ex Ko On Ra Rj Uf) Ou(Bg Ct Nv On Oy Pz Tr Vs) cX(aJ Al cS Hr In Jv Om Oy) Lv(DE dM Jv Ks Ue Vs) Mb(aX cS Ef Jp Kl Ng On) Oe(Bn cF Jl Jv Nu Ok Up) Vo(cF Hx Kp Mg Rh Uf Uh) Om(aX cF cS Ji Po Ra) Kl(aA aJ Ba bV dK) aW(Al aX cU Lu Oy) Dl(aF Bn gL Ko) Nj(Jp Lw Lx Mp) Kc(aG Iu Jf Pg) Ks(aA aE Jp Ko) aX(Dg Ef In Vv) cI(cW Dp Ha Rj) Nn(Ly Ng Nu) Ub(Ha Mj Up) Us(aU Mg Qy) aE(cF Jv Nx) aJ(Dg Mm Pz) Wm(Hr In) Fr(Hu Hv) Jp(Ha Ng) Js(Lx On) Ld(In Ur) aF(Nx Ur) DcEx DgKo LucS MiHq MvQv UcUf IoUp RjdK PbaA bVcA} Us{Hb(Ap aU aV Co Dk Ef Et Im Is Jh Ke Kf Kg Ky Lh Li Lx Pi Uf Ut) Ex(aQ bC cT dK dR Ef Hv Kf Ki Kk Kq Li Mp Mt Nn Nq Uf Ug Ut)

Figure 15 Continued

Jq(Ba Co Hc Ih Is Kn Li Lx Mi Mm Mp Mu Mw Nq Nw Pd Pi Sr St) Qn(aU cF Cp Cs dK fR Ih Jh Jl Mi Mu Nn Nq Qd Ql Qy Uf) aJ(aU Iu Kg Kq Li Mi Mm Mp Mu Mv Ng Nn Nq Of Qy Uf Vv) Jv(aU Bg Bo bZ cF cU Dk Ih Je Jf Kn Ky Lx Ng To Ut) Vo(Ap aU aV aX bZ cT dR eF Hu Jh Kf Mu Mv Mw Qu Vv) cP(AF aU cT De dR Ef Fr Hx Im Jh Kd Kk Mm To Ua) Hc(aQ aW cY Li Mi Mj Mp Mu Mv Mz Nn Qy Uf) Iq(Ba bW Cu Fr Jh Jn Mg Mt Mu Mv Qu Sr Uf) Af(aE aF Co De Ih Iu Li Mp Nn Nq St Uf) Io(aP aQ Bg Ch dR Ih Ky Lx Ng Sr To Ua) cF(aF aQ aV bN Cx cY Hu Ld Mz Rg Ua Wm) dM(bN cX cY Kg Kq Li Mg Mi Mz Nn Qd Ua) Ng(aG Ao bP cU Hv Hx Kj Mz Ss To) Hu(aV bP cY dR Jn Ko Of Rb St Uu) Ez(bP cI Cx dR Kd Ko Oy To Ub) Hx(aF aU Fr Kg Li Mi Mz Nn Qy) aQ(aP aW bJ bN eF Fw Jn Qx Tn) Ao(Ap Bg Ef Kg Ko Mv On Qd) Mg(aC aE bP In Jf Lu Rb To) bN(Bn cR Cu Fr Kq On Qe Rg) dK(CU eF Ih Jn Kq Mv Ug) Mj(aP cU Jn Kq On Qe Tn) Ua(aE Aj aV cU dR Om Ph) Qy(aS aX Il Je Jf Jn Qx) Kd(Kg Ko Mp Nn Qd Uf Vv) Mv(Cx Je Qw Rb To Uk) aU(bP Hv Je Ly Qx To) dR(aW Jn Qe Tn Ut Vv) Jf(Mi Nq Qa Uf Ut) Of(aP cT cU Ef Jn) Ur(Im Li Mp Nn Uf) aE(cY dD Hv Kq Ld) cX(Ax De Iu Kg Mp) Ub(bC cU Mt Tn) To(aV bP Cx Ph) St(aF Cx Dl Jt) Or(bU cT cU dN) aW(cT cU Lv Tn) cY(aP eF Jn Qx) Cu(bP Ha Jt) Mm(Ko Nv Tn) Ue(Jh Mp Mu) Kq(cl Ly Me) Ug(bW De Uc) aF(dF Mz Qe) eF(cl Ld Pi) Ba(aG Om) Fr(bP Ko) Ma(cE Uu) Il(Nn Uf) Je(Mi Mu) Kg(aS Kj) BnLd CxNq FwQc HaUt LyKk MzHv NiNj IhRm QdQw JlOm JtKn VvaX aGcT aSbJ aVdN bZcE} Vo{bN(Af Bo cF Ch cP cT cU Db dE Dg dM Hu Jj Mg Mi Mu Nn Or Qn Qy Ug Uh Up) dB(aU cS Cu CX Fb Fr Hx Jn Kk Ko Lv Ma Mg Mz On Qd Qv Uf Vv) Af(Ap bZ cT Cw cY eF Ez Fb Hx Jg Jh Jp Ke Mg Nw Pb Ua) cF(aF aQ bA bV Ez Fb Fr Hu Jp Mt Nn Ph Qe To Ua) cS(aF aU aV aZ cB Ct cV fP Hu Jp Mz Qn Rf Ug) Bn(aV aX cT eF Fb Hx Jp Ma Nw Qa Qd Tn Ua) Mj(bA Bg Co Ex Ih Jp Kk Kn Ma Mz Nn Ph Qd) Ko(aA bA bJ cW dE eF Jq Mg Ms Qy Uf Ug Up) aQ(aX cU Cw eF Hb Hu Kg Ma Mu Nn Or Qh Qy) Qv(aF Ap bA bC bW cU Jn Jp Mz Pj To Up) cX(aE aU cP Ct cU Cw Hv Jn Mz Pb Ph Ua) Cx(aE bZ cP cW dK dR Kg Mz Nn Qy To) Up(aA aJ bA Bg cY Jp Kk Mt Ph Qd Tn) Lv(aE Bo Cw dR Hu Jf Kg Nn To Vv) eF(aE bP Cs cW Hx Im Kg Kk Ph To) Cu(aX bJ Cq Ed Hb Io Jf Mx Of) Sr(aA aV aX cP Jf Jj Kc Kk Nk) Qn(bA cY fR Hc Jg Jp Ma Nw Qa) Ex(aX cY dR Kg Mi Mu Nn Uf) Hu(aA bV Jj Kc Kk Ni Ow Ur) bJ(aA aV cT cW dR Hx Jj Jp) bA(aV dK Jj Ma Ni Nk Vp) Mg(aE aJ Kd Qw Ue Ur) Pb(aU aV dR Mz To Ua) Ph(Hx Kg Mu Nn Qy Uf) bV(cA cV Kk Mn Mz Ua) dK(cP Hc Im Kd Kq Ow) Qc(aF aW Gp Oe Qg) aX(dR Ez Hx Jf Jp) cT(bC cY Fb Fr Ur) Cw(aA cP Jj Kd) Hr(Hc Kc Ng Vu) Tn(aE Ha Jq Vp) Hb(Ap Jg Kk Qa) Uf(Ao dM Jf Ms) aF(aA Bg dF Or) aJ(Kg Mu Nn Oe) Bo(Fr Mz Ow) Fb(bX Db dE) Ua(aZ Jk Mb) St(Io Nl Qb) Jj(bZ Mv Qy) Jq(Nv On Qa) Kc(aE Gp Nl) aV(dM Hc Hx) To(cY Kn) Qw(Qu Qy) Kd(Kk Rh) dR(aA Hc) CtUg EdQd EzaZ HaPe NiNj HxKg ImOf IoJg QaQg KqdH RjcY OeOn OwaW UrVv aEaU bZcP} Jt{Qc(aX BA Bn bV cF cX dB Et Hv Jg Jl Lh Lw Mm Nb No Nt Nu Pc Pe Po Qc) Jp(aJ Ba cS dR Hu Hx Im Ip Ir Ji Kk Ko Lx Mt Nn Nt Nu Nw On Pb Qv) Hv(Bo Cx Et fR Im Ji Jl Kk Kq Lx Ma Nv Ok Qa Qd Sr) cS(Af Bc Bn cP Cs dR Hu Jg Jn Kn Lj Mf Mz Pe Qd Sr) Im(bN Bo cT cX Hw Jf Jl Mk Mp Mr Nr Pa Pc Ph Po) Ba(aG Aj aW aX Ji Jn Kk Mg Mi Mu Mz Nn Nw Oe) Qa(Al bN Bo bV Hu Jl Lh Lw Mp Mu Nb No Om Pc) Fr(aF bA Bn bV dB Iv Ko Lx Md Ok Ow Pa Pe) Qd(aF aW aX eF Hx Jl Lh Mm Nb No Pc Ph Po) Hu(aA aJ bN bV cP Cx Hx Kk Ko Lx Mm Mz) Bo(aA Af BN Cx Ji Jn Lv Mg Nw Ow) Is(Et Jg Ji Li Lx Mp Mt Nn Nt Nu Ok) Lv(aF BN cF cP Cs Cw dB dM Ow) Jg(aJ cX Hx Lj Lx Mb Mt Nw Ok On) Jj(Ap Bg Cp Cu Cw Jr Ma Mf Nc Ua) Af(AP cT Jh Ji Mg Nv Nw Sr) Ko(aA dB Fp Kk Ms Pb Ph Up Vv) bN(aP aX Cw Ex fR Ji Kk Ph Sr) Nw(aX cF cX Lw Mm Nc Nj Ok) Ow(aJ aQ aV bJ dK dM To Up) aF(aJ aP cF Kn Lh Mz Sr Ur) Cx(AP bV Ji Ma Nv Pe) Mp(Ir Jl Lx Mt Mz Ok Pe) cX(aX bV cT fR Hc Kn Ph) Ex(aU Kg Mi Mu Nn Uf) Mg(cP fR Jf Or Ph Qx) Jl(Ji Mb Mu Nu Ok On) aA(dB Ir Jn Jr Lj Pa) aJ(bA cT Cu Et Lh Uf) Nn(dM Ir Ok Pe Ph) Hx(aX bV Ji Mt Mv) Kn(aX Kg Mu Qy Uf) cF(aP bA bV dM Ur) Lx(Ji Ma Mu Nv) Kk(aV cY dR Sr) Kq(aG aX dK Ky) cT(Bn Kg Qy Uf) Kd(Js Ph Rh) bV(cA Ji Mf) cP(Mt Qy Uf) Bn(aP Nv) Co(aE dM) Mu(Ir Lj) Mv(Nu Ok) Ur(Mf Vv) Pe(Nt Nv) Ph(aX Uf) bA(bP gL) ApaE EzSr LwMt MaOk MiHw QwgL QvOn JnaP KcdJ} Jj{Vv(aE aF aJ BN dB dK Io Jq Jv Kg Nn Or Qy Uf Ug Up Ur) Om(aJ Ch eF Et Fb Jg Jm Jp Kg Lx Mg Mn Nc Ok Po Pz Tn) Nc(Et Hw Ip Jg Lx Mj Mk Mm Mr Nb Nr Nw Ok Pc Po) Dc(bZ Co Ex Im Is Kq Li Ma Mi Nv Qd St Tn Vu) Ma(Cv Dg Hw Li Mk Mr Mu Nb Nr Of Pc Ub Uu) Mv(Ad aF aW bF Bg Cp dE Dk Mk Mr Nr Uc Vs) Lu(Aw Ba bP Co Cp cU Et Lw Mm Nm No Uf) Kq(aG aY bF dE Dk Jd Md Mr Ms Mw Of Ug) Qy(bP cF Jh Mf Ms To Ub Ug Uu Vs) aW(aJ Ba Bn cT Hu Mi Mu Nn Qe Wm) Jg(aA Hw Li Md Mk Nb Nu Of Pa) Mi(Cv Hx Mh Ml Ny Pg Uk Vp) Jq(aP bE Bo eF Fb Gl Kn Ky) Up(aZ bP cI cP dM Ex Io Or) Lw(Iv Jp Li Nq Oy Pb Qb) Mu(Hw Li Mg Mk Mr Nr Vp) Uf(Ao bP cF cI dB Ky Ub) Pc(Ji Jp Jr Md Mx Nt Nu) aF(Aw bJ cI Jv Ko Nq To) dR(aD cU dK Ex Fb Io Mf) Wm(bA cF cI dM eF Ug) Mp(aE bJ dI Ky Nd Oz) Hb(aZ bP Gl Lx Or Tr) Kk(aZ bJ Mf Mj Ml To) bC(aE Bo dE Ky Mf Ml) cP(bA cI dM Jp Ko To) Ao(Ch Ef Ex Tn Ua) Md(cO In Ny Oy Pb) Mr(Jp Jr Nt Nw Ok) Jv(Cs dE Pc Qh Rj) Ch(Ad aE bF Uu) Fb(dK Mb Ml Ms) Ub(Ct Hc Nk Ua) Li(Ha Me To Vp) Oe(bM dK dM dN) Ok(Iq Jp Mk Nu) Or(cY Io Qn To) Ex(cY Mx Vp) Nr(Jp Jr Na) Hc(Dk Ms Ug) Kg(cF dE Pg) Rj(bN cF cY) bJ(aE Cs Ug) An(Ef Ky) Aw(bM De) Mg(Ji No) Ml(bV In) Mx(Cs St) Nj(Mq Nf) Ua(Aa Of) Kn(Id Nx) Qn(aZ cI) Nw(Js Nu) Ut(bF Dk) Uu(Ef Ko) Vp(Qd St) cO(dH dI) dB(dK dM) eF(aG bX) BocZ CobF CvFr FwaQ MeMm MjSr MkJr NaHw IoPh IqcT JfbZ JlaE LjOy VuVs PbdN aCbE aJdL} cT{Mu(AJ bF Bg bQ cF Ij Jh Jv Kj Mk Mm Ms Mw Nb On To Tr Tv Up Uu Uv Vp Vs) Kc(cF Dd Dg dH Id Io Jk Ke Kl Kr Mp Mx No Of To Tr Uc Ur) Nn(aA AJ aW bN cF dB Hr Hv Kj Mj To Tr Tv Uk Up Uu) Jq(aJ bJ Bo bP cF dB dK dN gL Hx Io Jn Jr Kd Mz Qv To) Mg(aE cE Cq Ct Cv Dc De dN Il Iq Nm Oy Po Qn Uc) aF(Ad Ao Jv Ks Mm Of oK Om Ow Rc Rj To Uk Up Ur) Mi(Ao aW bN Dc Iq Lu Mr Nd Ny Qb Qw Tr Up Vp) Qy(aG Cq Ct Jk Jv Kj Ny Of Pg Tr Uk Up Vp Vs) Uf(aD aE Dg Il In Io Kj Mj Mp Ny Tr Ug Uu) Qn(aJ aQ aU aV cF dB dR Jv Kg Lv Rj Uk) Hb(Af Ap aQ aU bJ Bn dR Ji Ko Lv To) cP(aE aW bF Bn bP cE cF Cv dM Oe) Lv(aG Al Ao cE Jv Rj Up Vp) Io(aW aY dE dR Kd Kk Ug Up) Bn(Jv Kd Kq Lu Of Om Rj) Ow(aG bJ Dp Ij Iz Kj Pa) aJ(De Iq Mj Mx Ny Of Qb) Cv(aD aE aP Ct gL Oe) Nq(Cq Ct Dk Hr Jk Ny) Mp(cA Cq dI Hq Po Tr) Kd(Aa An Mx Ny Qb Rj) aX(Dp IZ Kj Kl Or) Cx(Ha Ks Qw Uu Vs) Mv(bF De Dk Hu Nv) Hv(dE In Tv Up Vp) To(aQ aV bP Jv Ld) Kg(Dg Jv Of Om Uu) Af(Kk Qw Ug Vp) Fr(Ad Ao bF Mj) Mx(bW cU Ma Qd) Ks(bW cX Im Mt) bJ(De Nx oK Om) bP(Jv Mb Rj Up) cS(Ki Kj Ss Vv) Cq(Hu Kq Pd) Li(Pe Pf Tv) Ug(aQ aV Wm) Uu(bW Ua Ur) aA(aW cE cF) bE(aE dB nY) dA(bN bU dB) gL(aG Dc dF) Ao(bC Ef) De(bC dN) Mj(Kq Qd) Qa(Dc Js) Jv(Im Kq) Nx(dK dN) Oe(cF dK) Of(bN Hu) Om(cF Ur) cE(cN dG) cV(aY Ct) cX(Qw Tr) EfOy MabF PgbW aDaS aWfR cLcN} Kk{Mu(Ao aQ Cq cW Dd Ha Il In Iq Jk Js Kj Lv Mj Mp No Nt Of Qw Up Uu Vs) Mj(aJ bV dB dE dN dR Ex Hv Im Io Jp Jv Kq Kz Mi Mz Nq Qy Uf Ug) cF(aF aU aW bA bV bX cP dB Hx Ky Kz Ly Mi Mp Nn Uf Uu) Bn(aU bA dB dE dK Dp Jp Kq Ky Ly Mp Nn Of Uf) Up(bN bV cY dE dK dN dR Io Jp Mi Nq Qy To Ug) Lv(Aa aE bV cY dH dR Io Jq Ju Ky Of Om To) Uf(Ao bA Cq De Dl Ha Il Iq Js Of Om Tv Uu) Qy(Ao Bb Dl Jk Ml Mp Ny Qw Ug Uk Uu Vs) Oe(aA bA bV Dk Iq Js Ms Nx Ny To Tv Tj) dR(aE cP cU dH Dl Jq Nm Nx Oi Ug Uk Uu) Af(aE bA cP DB dE eF Io Jv Ky Lu) Nn(Ao Cq cX In Iq Js Mp Nm Of Qw Uu) aV(bA bJ bX cI Dg dK Dl Kl Ly Mm) Tv(dE Hu Hv Kd Kg Kz Li Mg Qn) aU(aG Ao cX Dg Kl Ml Pz Ug Uu) Mi(cP dH Il Jk Js Of Uk Uu) Jq(cX cY dE Hu Jp Ly Mz To) cU(cE Dc dJ Dp Ha Pg Qb Vp) Fr(cE Cq dH Dk Nv Oy Vs) Mg(Ao cP cX Ny Of Om Ue) Kd(Cq dB Dl Jv Kr Ks To) Kg(Ao bA cX Dl Of Om Ug) aQ(aG bJ bN cI Dg Ly Pz) Aa(aE Jp Ky Ly Pj Vp) Kq(Bb Ha In Js No Pz) cY(aG Dl Mm Nx Om Uu) Ma(Ao Js Kl Of Uu) Im(Cq Ha Jv No Ny) cX(Dp eF Ju Jv Ky) Io(aA To Ub Ur) Qn(bA cF Of Tj) Nx(aF Hv Jp Mz) dK(bN Jv Ks Ug) Cx(Ao Dc Je) Mv(Ao dH Uk) Hu(Ks Ms Ny) Hb(aA Or Vp) Qv(Nb Ny Qx) Uu(Ef Qu Ua) aF(aX bA gL) bZ(bF dH Pg) Ha(Li Mp) Of(bN eF) Om(eF Ly) Ou(Co Mp) BaKl DegL NqVs MmbN MsHv NiNj ToUr QaQb JvRj KsbJ dHdN} Af{bN(Aw Bg bU cF cN cP dB dF dG Dk Hu Hv Kd Ko Ld Lu Mu Mv Mw Rg To) dB(aN Aw Ax Bc bU cF Cs Dk Ef Ez Hu Hx Jf Jh Mi Mw Nq Qy) Lu(aU Bo bP bV cF Fr Hu Jh Ji Kg Ko Mi Mv Nn Nq Nw Ph)

Figure 15 Continued

Jh(aE aW fR Hu Hv Iq Jf Ko Oe Of Om Oy Rb To) aX(AW Ba Bg bU cF Dk dN Fr iZ Mg Mi Mw Or) cF(aP Bo bV cU dN Fr Hu Hx Kq Mi
Mw Mz To) Ex(aQ aU Co Dc dR Hb Mi Mj Mv Nq Qu Uf) Kg(aE aJ cP cW dM Hr Jf Jq Kj Lv Rg Uk) Up(aJ cY dK Fr Hv Hx Qd To Ug Ut)
Mu(Hc Jf Kj Ko Kp Ly Ph Rh To) Io(dR eF fR Hc Ky Ph Sr Tn Ug) Fr(aW bC cU Hb Iq Mb Mm Uk) Kg(Bo dM Jp Kj Lv Rg To Uk) cP(aA aF
aJ bC Bo cS cU Jp) Nq(Bo cS dM Hr Jf Kp Ph) Hb(aJ aQ Hx Ke Lv Qd Sr) Hc(bA Bo bP Iz Kd To Uu) Aw(aP Ax Cs dE Ms Oe) Qy(aQ aS dD Ko To Uk) Uf(aE aJ cS cW Lv Rg) Ug(dR Hu Lv Ni Nk To) bZ(aF aW dH dM Hr Of) cU(aF aQ aW Ba Bg Dk) dK(eF iZ Jf Ph Rj Uk) De(Jp Lv Ow Ph Rg) Im(Fw Jf Ks Qw Rb) cS(Ax Iq iZ Kj Of) eF(aE aQ cI Hv Of) Nn(Je Jf Kj Uk) Mi(Bo Hr Iq Jq) Mv(In Iq Jq Ko) Kq(aW Kr Mp Rh) Ld(cY Hr Mj Vp) Ut(In Of Om Uk) dR(aA bJ Ph Rj) Ef(aE aJ Uk) Mw(aE aJ dD) Jp(Kr Mb Mm) bU(aZ bQ dE) dM(aQ Ba Bg) Dk(bC fR) Lv(Jf Nx) Hv(Hr Vp) To(aU aV) Kd(Bo Rh) Rj(aQ cY) Oe(aP Ng) aC(aP bJ) AxbC BaOm BgUu CoUk MaOf HxdN InQd QxaU KoKs RgcY aFbQ bJiZ dLfR} Of{Qe(Hv Hw Iq Jh Mg Mk Mr Ms Mz Nb No Nr Nu Pa Pe Po Qc) Ma(Cx Hu Ij Ir Is Iv Lx Mu Mv Nu Nw Pa Pe Qd Qx Wm) Jp(cF Cx Hc Hu Hv Hx Ij Is Iv Mb Mi Mu Or Pb Qv) Mt(Hu Hv Hw Hx Ji Mk Mp Mz Nr Ok Pa Pb Pg) Nv(Hv Hw Iv Lw Ly Md Mg Mk Mr Ni Nr Pa Pe) Hu(cF cS Hv Ip Iv Ji Lh Li Mu Mv Nu Qd) Im(dR eF Hv Ij Ly Mj Mk Mr Nb Nr Nu) cF(bN cP cU dM Hv Is Jg Ji Kc Lh Mv) eF(aA aE aV Bn Kg Ko Ky Mb Ph Qd) Fr(dB Hw Iq Ji Lw Mi Ok Om Up) Lv(bN Bo dB Ex Ez Js Kc Kd Up) Jh(Hw Hx Ir Iv Mz Pa Pg Po Qa) Kq(Iq Jq Md Mj Mm Rj Uc Up Uu) Is(Hv Jl Js Lh Lu Mp Nn Qv) Jg(Ip Iv Lx Ly Md Ms Ni Pb) Mu(Fp Hv Iv Lx Mb Pb Wm) aX(bN cX dR Kn Or Ow Ur) Ba(aF aG cP dN Kc Kd) Mz(Ik Jk Mb Mp Nn Wm) Ni(aJ Ij Ir Jk Lh Mi) aA(Iq Mf Nj Nu Qy Uf) dR(aJ aP cU dM On To) Bg(BN cX Up Uu) Qa(Iq Ly Mg Nu Qc) Kc(Ct CX Ex Jf) bV(bJ Ct Nq Qy Rj) Wm(dB Et Hx Mn) Mi(Hv Iq Mf Oe) Mp(Ik Mv Qd Qv) Hc(aE aF Or Ug) Qn(aJ Ow St Tn) Nw(Lx Md Pa Qd) cS(cX dB Ld To) Bn(aP On Tn) Cu(Jq Lu Mx) Cx(bZ Ez Ko) Nn(Ik Pe Qd) Mv(Iv Ji Qv) Hx(Ik Ji Up) Or(aU dK Ur) aQ(Kn Qx Qy) Co(Jq Lu) Ex(aU Io) Lx(Hv Iv) Mb(Fb Jk) Mg(aJ Ue) Ms(Ji Lh) Ko(cU Io) Ow(Mj To) Ug(Ct Vv) bA(bE bP) bN(bZ fR) cX(aJ fR) ApLu TnUp IqJk IrOm QdJl KdcU OkPg OndB aUdM bZcP} bA{Qy(Al aW Ba Co dE Fa Hc Ib Je Jl Jy Mm Nb Nd On Qx Tz Ub Tj) Kq(bF bQ De Dk Dp Hq Hr Iz Kj Lh Md Mu Nx Qt Tn Tz Ut Uv) Kd(Aa aF Al aQ bP Dl Ha Js Ks Mg Mm Nl Nm No Qh Vs) Kg(aF aH Aj bF bQ dH Dk Ef gL Hr Iz Nx Rc Ss Ub Uh) Mg(aA aJ Bg Dp Ef Fw Mm Nv Nx Qm Ss Tt Ub Uk) To(aD aV bN bP cF Cq dK Ha Jq Mx Ni Rj Uu Vp) gL(Cv Dc Ha Ij Jk Jq Kf Ks Mm Mu Nn Pg Uf) Uf(Ad Al aW cF Cu Dk Ji Kf No Nr Tz) Hb(bN cY dK Hx Ko Mz Ni Qn Rj) Up(aD aE aG aQ aV bN dK Om Ug) Lv(Dp Ha Ks Nx Rj Ub Ug Uu) bP(De Dp Iq Mr No Ny Pg Uu) Jv(aE cF Ex Ni Tv Ug Vp) Kc(aF Al bX dK Ir Lh) Uu(BN Hc Hu Mj Qn) aJ(Iq Mx No Ny Qb) Cv(aW cE cF cP) Mj(Ex Hx Rj Ug) Ni(Ao bF cE Mr) Hv(Ha Jk Ks Mr) Ow(Kj Nm Nv Uc) bJ(Iq Jk Oy Pg) dK(Dp In Js Or) Aa(aA aQ cV) Nn(Kf Or Vv) Nq(Bb Cw On) Mu(Ef Iz Or) Ld(Pg Tv Vp) Li(Dp Fw Qh) Rj(aV bN cF) Oe(aW cE Vp) Ug(cF dR Wm) Vs(De Jh Qd) aE(eC Mx Qn) cP(aA Bn Jq) Bo(Iq Md) Dg(cS Mv) Tj(Mi Mp) Hu(Ao Oy) Ks(BN) Ny(dB dR) bE(eC tF) dA(bQ dI) dN(Mr Pg) AxDc FwcF LubN MsMv MxdB IocE KlaU QnaD aAaW cXiZ} Lv{cP(aA aF aJ Al Ao bP bV cF Cv Dc dE Hv Hx Jq Mi Oe) Hb(aF BN Bo cF cY Et Ez Fr Ji Kn Mg On Ph Rj) Kc(aA aE Ao Dd De dH Ha Jk Kr Mp Nx To Uc Ur) Qn(aE aQ bN dB Hx Im Io Jn Ky Mz Rj To Up) Ao(aA aP Jg Jp Kd Kq Mi Nn Nq On Ow) Iq(Hw Ij Lh Mj Mk Mr No Nr Pa Pe Po) Uu(aA bN bV Fr Hu Hx Im Jg Jp Kq Sr) Ub(BN Hv Io Jf Jp Oe Om Rj To) Jq(aP Cs dB Ko Ky Rj Sr To Uf) bN(Bn CX dN Ex Hv Hx Oe Rj) Jv(cF cX dB Ex Hx Kd Ky To) Nx(aE aF aX Bn Bo cF CX) Up(aJ bP dB Ky Oe Om Rj Ug) Bn(dM dR Ex Hv Rj To) Mj(dR Js Ky Rj Ug) Hv(Al cW cX dE Ha) Jp(Cv Dd Dg Vp Vs) Kd(Dl Io Nm Om Rj) Ow(dB Dc Lu Po Qb) aE(bC cF Fr Mi Mv) Mm(Hw Mk Mr Nr) To(aQ aV cF Om) cX(dB dM Mi Oe) Bo(Dc Om Pg) Ex(aX Lh Mx) Ms(bC Ij Pc) Mu(aJ cF Cx) Nd(Hq Oz Pd) Hr(bP Cx dB) Il(Ez Uf Wm) Kj(cS Ez Kq) dE(bP cA dM) dR(aD dM Io) Dc(Jn Mz) No(Jr Ml) Ng(Ik Jk) In(cU Wm) Jf(dB dK) Ko(Dg Io) Pc(Ly Oi) Pg(bZ cU) aF(bV Ue) aW(bV cS) AlJn BaOm DeMv TjOu MlPb HxVp JsPa KscS OedM OraX UgaQ aGeF aJdL dHfR} cS{Mb(bN cA cP dI Ha Hx Iq Js Mi Mm Mu Mx Nx) Or(Aj Ao Cx Jv Kc Kd Kl Ks Mm Nm Oe Ug Uk) cF(bG Hv Hx Il Jp Jv Kj Ms Oe To Uk Uu) Bn(aC Bo dM fP Hu Hv Io Iq Mm Uu) Oe(bN cP cX dI dM dR Hu Hv Hx Mz) Up(cP dD Il Iq Ks Mj Mm Om Ub Uu) Io(aX bN Ha Hr Hu Hv Hx Il Jf) dB(bN cP dA Hu Hv Hx Iq iZ Kj) Hc(Ad Aj Dg Ef Kl Mj Ss Ue) Jv(Hv Hx Ky Mj Rj To Ub Uk) Ko(Ad Ij Kj Kl Mj Mp Pz Qn) Uu(bN dR eF Hu Jg Kq To Ua) Ao(Dk Kg Mn Nq Qy To Uf) Mm(Ba dR Hu Hv Jp Mu To) Hb(bN dD fP Kq Sr To Ug) In(cA cV Iq Ld Mg Mi) fP(bN Bo dM Jf Js Kr) gL(Al cQ cV Nq Ow Tz) Jq(cV Ki Mn Nq Uf) Mu(cX Lu Nq Qw) Hu(Dg Iq Kj Nm) Qy(De Mp Qw Uc) Ks(aQ Hv Hx Mf) Qn(aV cA Iq Mz) Uk(aQ cV Hv Ld) dE(bG bN cX iZ) dR(Ha Js Om Pg) Bo(aC bO cV) Cx(Ax Fr Ms) Mj(Kn Ph St) Kc(aG Iz Po) Ow(aW cP Po) Al(Hx Mz) Ba(Ad Dg) Lu(aW aX) Uc(Mg Ua) To(Iq Ki) Il(cX Mi) Kd(aQ cK) Kj(aQ bJ) Kq(Dg Mp) Rg(cA cE) aJ(Kr Om) bG(bU cE) bN(fR Hv) nY(bE bO) DpcI NmPh LyRb NeNh UbKi UeaF HrcX UgcV PbaA dAdH} aA{Kc(aG aQ bN cF Cq Ha Io Ks Mj Nx Ow Up Ur) Oe(cP Hw Jl Mf Mk Mr Nr Pc Qd Qe Rj Up) cF(aF dB dH dM Hb Jq Jv Kd Mu Nn Ow Uu) Mg(aG Aj De Iz Kj Lw Ly Nj Pb Ur) Kd(Cq Hb Io Jq Mx No Ph Qb Tv Uu) Om(Hu Jn Kq Md Ok Pa Qd Qe Qy Uf) Ma(cE cP Dl Hx Iz Mz Nw Ok On) Ms(aF bN Hx Ly Ml Qd Qe Rj Wm) Hb(aF bN dD Ex Hx Jn Mz Nw) Io(aW cP Hx Pa Rj To Ub Up) Jq(aF bR bU dB dD dR On Pb) Fp(Fr Ji Lw Mp Mx Nn On) Mb(Hv Hx Jg Ji Lh Mm Nn) Ni(Aa Hv Mp Nk Pa Pb Pe) Uu(dR Hc Hu Ko Mv Qu Uf) Iq(Aa Bo Kq Nj Qy Uf) dK(In Js Ne Qw To Up) Nn(bN Ji Kj Ok Pe) Mp(bU Ns Pd Pf Pg) Ly(Jr Mz Ok Pe) Ml(Aa dB Jg Ji) Kj(Kq Mu Qy Uf) Ks(aF Kq Mu Uf) aP(aJ bC dN gL) aW(bJ Bn dB Ow) dM(aC aF bO dH) Ao(Ef Qy Uf) Ex(Jv Kf Tv) Ha(Kg Kq Li) Mf(Hx Mz Ok) Ng(Mt Mv Nu) Hu(Mz Nw On) cP(aF cU dB) Aa(dR Ko) Dl(Kg Mv) Wm(Jp Oi) Mq(Md Ns) Js(Is Nw) Ow(aE bN) Ur(aG Kg) bZ(cV dG) cE(bF dN) cU(Cv Up) dH(bG bV) BnUf MxdB NjOk HvJi IzKq QyQw NxaF OraX PbPc bOnY cVdE dGdN} Cx{bN(aC aP bC Bo bU bZ cF cP dB dF Ex Fr Hv iZ Jp Jv Kd Ko Ky Ld Rg Rj To Ub Up) Hb(aV aX cY dB dD eF Et Ex Fr Hv Jn Ke Ky Ld On Ph To) Lu(aU aW Bo dR Hr Hu Ji Jn Ko Mg Mi Mu Mz Ph) dB(aP Ax Ba bU cF cQ Hr Hv Hx Iq Jp Up) Kd(aE aW cF Dd Ha Jq Ph Rj Tv Vp Tj) Jp(Ad aE Al cP Dd Dg Ha Ms Om Uu) Hv(Bo cP cW Fr Ha In Ms Up Vp) aE(dR Ez Fr Ju Jv Ld Mi Mv Rj) cF(aP aX Bo cN cQ cU dN Hu Ub) To(aV dK dR Io Ld Ms Ni) Uu(Bg eF Hc Hx Jg Sr Ua) Ba(aW dM Iq Iz Jq Om) Fr(Ad Bg bV dM dN Iq) Ko(Ao Io Iq Jq Kj Ms) aX(aW dN iZ Kj Ld Or) dR(dM Io Ky Mj Rj Up) Hx(Bo dN Hr Up Vp) aQ(cU Ex Fw Ld Up) dE(aC bC bU cN iZ) Ao(Hc Jh Ma Tn) Mu(aJ Iq Jq Om) cP(dM fR Mg Oe) Jq(Ez Mi Mv) dK(eF Rj Up) dN(aC Bo Hr) Hu(bP Iq) Qw(aU cY) Kc(Nl Vp) Kg(Kj Ue) Ld(aD In) Om(Ez Hc) aF(cU dF) bC(Bo cQ) bU(bZ dA) bV(cV Ni) DlKq ExMj MmOw HrdM IlUf SrKs KraJ OefR UpaV aCaP aWcF bJiZ bZcE} bV{Mu(aG Bn cF cP cV Dg Dl Ha Hb Kj Ks Lu Ms Pg) Kc(aG cA De dR Ha Kj Kr Mj Mp Nm Nx Ur Uu) bN(Bo bR bU cF dE Hu Hv Lu Mi Mv Mz Uu) Hb(aU bJ cA cY Ez Hv Ji Kg Mg Mz Qy) cX(bR bU dB dE dM Hr Hv Kg Ph) Lu(bJ Bn Hv Kd Mg Mi Nn Oe) Jv(bJ Bn Hx Im Kq Mj Rj To) Ow(aQ aV cF cY Iz Pf Ph Po) dR(Jq Kd Ks Rj To Uk Uu Vp) Iq(aF Db dE Hx Kg Mg Uf) Oe(aF bU Fr Hc Ko Mg Mn) cA(Hu Kd Mp Om Qy To Uf) Uu(Bg cF cY Hu Ko Ua) Nq(Ao cE Dg In Pg) Hv(cF dB Ha In Nx) Qy(cE dI Hu Kj Mm) Ks(aQ bJ Mt Uf Up) Qn(aK aU aV dI Mz) Mg(Io Mm Uc Ur) Mi(Bn Lw Tr Vp) Mv(Dg dI Pg Uk) Kd(dH Dl Nm Rj) Kq(De Dl Ha Mj) Om(Fr Hx Io Uf) bU(Bn dB dE dM) cV(cU Mx Rj Ur) Mp(dI Il Pg) Ug(aF bJ Ni) cF(Jp Jq Ms) Co(Hq Pg) Nn(Hr Mx) Ma(bS cE) Mj(Kg Ko) Mz(dB Mx) Ld(Ha In) Ur(aG bJ) Up(Hc Jq) Oy(Ef Jh) aF(aO Nx) bR(dE dM) BaKl BnHu ToaQ IodM KgKj RjcK UfcE aJaP bOnY} Jp{Ao(aX cF dR Fr Kc Kg Kq Ma Mi Mu Mv Ni Nn Nq Qv Uf Ur) Mb(Dg Dl Ji Jl Lh Md Mu Nn Nw Ok Om Pa Pb Pc Pe) Hb(aE aF aV aX cP Db Mg Mx Nk To Uf Ug Vp) Kd(Dc Dg Dl Ha Js Kl Kr Ks Ph Qb Vp Vs) Oe(Bn cF Hw Hx Jl Jv Lh Nr Ok Or Pa Pc) Kc(De Ha Io Kf Mj Mp Nm Tr Up Uu) cF(Bn cX Dc Dg dM Jv Lu Ms Om Ow) Hu(Dc Hv Lw Ly Md Mp Om Pb Uu) Ms(Ik Jv Ly Nn Nq Nu Pb Qn) Dg(Kg Ma Mu Nn Qy Uf Up) Jv(aQ bX dR Jq Mx Rj To) Om(dR Mp Ni Nn On Or Qa) Ow(Dp Jg Kf Lh Nm No Pz) Uu(aQ bN cX dR Hc Qv) dB(Bn

Figure 15 Continued

Figure 15 Continued

Pb Pe Po) Fr(Hx Ij Ji Lw Lx Mp Mz Ng Nn Nw Ok On Pc) Mu(aJ De Hw Jg Jl Lw Mk Mp Mr Ok Pe) On(Hr Hv Md Ng Nm Ny Oy) Hu(Hx Ji Lh Mm Mp Ok) Hv(Ma Mp Ni To) Mi(aJ Hq Pg) Mb(Jg Jl) Mp(Jl Ni) Io(Ex Ky) NqJi LxNi MdJg} Ao{Kq(aE Bn De Hr Hu Hx Jn Kg Kj Ko Ks Mg Mm Mu Mv Nf Nn On Qw Qy To Uc Vp) Fr(dB Hr Hu Mu Mv Qy Up) Mg(aJ Jf Lu Ue Uk) Mu(Hx Jf Mz Nw Ok) Hc(aQ De Ma Oe Qy) Ba(bN cU Io Qy) Mv(aJ Hx Ok) Kg(eF Hx Mz) cP(Ef Hu Mt) Tn(Mj Up) CoHr MaHv MzQy HxdR QaUp KobZ OeOn} Uu{Hc(aF aJ aQ Bn Bo bP dE dK Mv) Ba(aF aG aQ aW cl Mj Ny Rj) Ko(Bg Bn dR eF Lu Mj Or Ua) Kq(aE aQ bN dR Hu Jf Ks Rj) aJ(aQ cF Ch Hu Ma) Fr(aQ Bn To Up) cF(aE Hv To Ua) Bg(Bn dB To) Jg(bP Io Or) aQ(aE dM Hx) Or(Kg Nn) FbdB MvUp NiSr HxPb ImJf} Lu{aF(aJ aZ Bo bP bZ cl dE Ji Mg Rj To) bP(BN Hu Hv Jn Mb Mg) dK(Bo cF cP Ji Ko Mz Nw) On(Mz Nb Nu Nv Ny Oy) Bn(Bo cF Hu Hx Nw) aW(Mf Mg Mu Nn) Ok(Hv Mi Nn) Lw(Fp Mb) Mp(Md Pd) Mu(aE De) Ko(Io Mj) bN(dN Mb) BoHv MiHq ToLd OeaJ} Ex{Io(aJ Al bP Cq Jv Ki Md Mi Or Oy Pg Qb Tv Vp) Ez(Dg Ha Js Kj Li Mj Nm Oy) aQ(Ad Dl Ha Ij Kf Pz Rm) Mi(Cw Kj Mp Uc) Mj(Kf Ki Ld Qy) Jv(aF aU Mx Qy) bN(Kf Ub Up) Mp(Nn Uf) Uc(Kg Mg) Qy(Oy Ue) CwKg MuKf UpbX PjaF} Hu{Ng(Fr Hx Ma Mz Nw Pc Qa Qe) Nn(Hv Md Mz Oe Oi) Ni(Hv Hx Lw Lx Mi) Iu(Ir Jl Mi Qa Qe) Oe(cP Hx Jl Lh) On(Hr Nb Nx Ny) Pc(Md Oi Oy) Bn(aJ cP) Mb(Mp Mz) Mi(Md Oy) Nw(Nm Nx) FrOi LwHv HrPe NxOk cFcW cPdB} Hv{Js(Ir Jg Jl Lx Ma Mv Mz Nw Qa Qe) Mb(Ma Mu Mv Mz Nn Nw) On(Hw Md Nj Nv Ny Oy) Mi(Hx Ml Ni Ny Oy) Oe(cP Lh Ok) Bn(Bo dB) Fr(Jk Ng) In(cU Wm) Nx(Bo Nw) LxHw LyMa MvNg NiNk HrPa cFdM} aJ{dH(Ba Bo cP Mp Qy Uf) Bn(AW cF Io) Oe(cP Mg Mu Mv) cU(Js Mj Mp Mx) Dl(Ba Mu Nn) aF(bG bZ dE) dG(Fr Mu Mv) dK(Ha In Up) Io(Nx Ub) aW(bC dL) bO(bR dN) DgMa MiMp JvbN bUdA cPdL} Ue{Kq(bN cF Ij Js Mr Nv Ny Oy) Qy(aE aQ cF Ha Il Oy Rj) Mg(Js Ks Mj To Uk) Mi(dl Uk Up Vp) aF(aQ aV dR Hc) Mj(Kg Mv Nq) Mu(aE cF Vp) Kg(De Ha) Uf(bN Up) MacE aVbJ} cP{Mu(Ad Al Bn Hr Mm Mp Na) dB(aP Bn bU bZ dM Mi Nn) Bn(aF Mp Mv Nq) cU(Bo dE dM) dK(Jv Oe Uk) dN(bG cF dM) Nn(In Oe) Io(Ko To) aF(dE fR) AjMv MgIn MjLd bUfR} Mb{Jl(Ji Js Lw Mp Nw Ok) Mu(Hx Mz Ng Oi) Jg(Hx Mi Mz Oi) Po(Js Md Mi) Fr(Ji Lw Ok) Lx(Lz Mv Nn) Aa(Ko Mg) Mp(Hq Pf) Mv(Hx Ng) DlOn NnHx LwMz HrPa NwNx} Oe{Fr(Fp Hw Hx Jl Lx Md Mk Mr Nr Pe) Mi(Lh Lj Mv Ni Ny Pa) Lx(Hq Jg Jl Mt Mz) Jg(Hx Ly Pa Pe) Nw(Md Nn Pa) Ba(Dl Kl) Mu(Hx Pa) MvPa HxcF} Io{Ko(aE BN Hr Ks Ky Mj Uk Up) Ky(aE Bn eF Hx Jf Or To) Ba(cF Hr Iz Kl) Fr(cF De) Ub(aQ bN) To(cF Mz) aE(Hc Uh) eF(aG Ml) RbaQ KjKq cWdR} Bn{bN(aP Bo cN dG dN fR) dM(aQ Aw Bo cF dB) aC(aP bC bE bZ) To(aQ aV dR) Ba(Aj Dl) Kq(Kj Kl) cU(dB iZ) Mull RgaQ OrdK dHfR} cU{aW(Bo cF dB dE fR iZ) dB(aN bU cF cQ) dE(aC bN bU cF) aP(cE dH) aQ(Bo Fw) dN(cE dH) iZ(bO dK) aFdM bUfR} Mi{Js(Hx Ik Ml Pa Qd Qe) Nj(Fr Nk Pg Po) On(Mm Nm Ny Pz) Md(Ml Pb) WmHr HcKj NwNy} Kq{Kl(aQ cF Mj To Up) Kj(aE aY Ha Up) Uc(An Ha Vv) aE(Jv Mm) DgcF DlMj Hall Hclz} bN{Jv(Hx Ko Ky To Ub) aP(cF dH) aW(dN fR) cF(bP cl) AjBa DbdM MmKo OrdK bZdB cFfR} Fr{Nj(Md Ni On) Js(Fp Nu Qa) Pz(Qd Qe) aC(bE bJ) Wmln MdPb NcNg ljcF} Hx{Hw(Jg Jl Ma Mp Mv) Ni(Nj Nk) WmHr MuNj JvcF UpbP} On{Nj(Hr Nv Oy Pz) Ly(Ma Md Oy) Js(Fp Lx Qa) MmNy} Ko{Dg(dR Ma Mg Mu) Kj(Mu Qy) Kl(aQ dR) AaMj DlaQ} dK{Or(Jv To Up) bE(iH oF) bO(hB hG) StJv bGhG eFiZ} dM{bZ(cE cF dB) dH(cO dN) DbaC DgMg aFdE bFcE} aP{bU(bG dE) dH(bZ dB) aCdE aWcF bFcE} aQ{To(aE cl Jv) BaKl Hclz JvaE cleF} dN{cE(bZ fR) cF(bG dE) MjKn aCdE cQdB} Ly{Mv(Mz Ng) Jg(Md Oi) Nx(Ji Nw)} Kj{Jf(Mu Uf) Or(Mv Qy) CuVp HcUf} Ba{Kl(Bo dB Hr Rj) AjbJ} Wm{In(Hr Li Mp Qa) NnHr} Lx{Hr(Js Nx) Pf(Js Md) NwNx} fR{aC(aF bC cF) bU(bG De)} Mu{Il(cF De) MzNj UcHc} eF{ToaG aFiH aWiA dEiZ} bE{aW(oF oK) aCnY} bP{eC(aO kQ) UpdD} dB{HcJv bUoK bZcE} Mv{FpOi NuMd} AlDlQe NjNwNx IllmVp QaJsOk JvaEdD bFcEiZ Constrained panels with 2 analytes, where 1.0E-7 >= 'AUC p-value' > 0. Contains 259 panels of 66,377 total panels evaluated. : Lv(aA aX bV Fr gL Hu Hv Hw Hx Is Jg Ji Jj Jl Jo Jp Js Lh Li Lu Lw Lx Ma Mg Mi Mk Mp Mr Mu Mv My Mz Nb Nn No Nr Nw Of Og Ok On Pa Pb Pc Qa Qe Qv Ur Us) Ou(aE AF aG Ao aW aX bG BN cl cS CX Dg dK Dl Ef Fw gL Ha Hb Hr Ii Io Iz Jj Jo Jq Jv Kc Kd Kk Kl Mj Ng Oe Of Om Pg Qn Qv Ug Uk Up Ur Us Uu Vo) Jj(aA Af aX bA bV cS Ct Cx Fp Fr gL Hu Hv Hx Ih Ij Ik Im Ir Is Jk Jl Kc Kd Lh Ly Mi Mp Mt My Mz Nn Nv Ow Pa Pb Pe Pg Qa Qb Qd Qe Wm) bA(AF aJ aS aW bE bJ Bn bO cE cF cV CX dB dE dM dN Io Mu Nn Ow Us) gL(aC Af CX dH Ii Iz Of Qn Qv Ug Ur Us Uu Vo) Qv(Af aX cS CX Im Jv Kc Kd My Ow Ur) cT(Af aJ bJ Bn cS cU CX dB dE dN) Ur(Af cS cU Cx Hb Jq Lu My Ow Qn) aA(cU CX dN Mi Mp Og) aJ(Af bN cU CX dH Og) Us(bV cS Jp My Ow) li(Ba Kq On Tn) Og(aF Hv Kc Nw) Mi(Ly Mb Ms) Of(Ba Jl On) Ow(Hb Jq Ms) Kc(Af cP) Kk(aX cS) Ug(Kd My) Vo(Ba Kq) FrLy JtOn Constrained panels with 2 analytes, where 1.0E-6 >= 'AUC p-value' > 1.0E-7. Contains 165 panels of 66,377 total panels evaluated. : Jj(aJ Bn cF cT cU Hw Ip Iu Iv Jh Ji Jp Lx Ma Mb Mf Mu Mv Mx Nj Nq Nt Nu Nw On Oy Po Qv Us) aA(Af bA BN cT dB dE Hv Iq Ms Nn Of Pb Qv Us) gL(aW bA dB Hb Io Jo Jq Kc Kj Kk Kl Ms Oe Ss) Qv(bC bJ Bn Jp Kg Kk Ko Mi Or Qn Uf Us) Og(Fr Ji Kk Lx Mi Mu Ok On Ow Ur) Ou(cE cF cP Cq Jt Ks Lh Mp Po) cS(Af Cx dM Jo Jq Kc Lv Ow Ug) bA(cP Cv Ii Kc Lv Mg Oc Ur) Ow(Af Ii Kk Qn Ug Uu) cT(aD aE aP cF dM Mu) Fr(Hv Jo Mb Ms Of) Kd(Af Jo Jq Us Vo) Ur(aX Bn cX Ug Us) Kk(aV Cx Qn Us) bV(Cx Io Oe Up) Kc(Hb Jt Lu) aJ(dG dL dN) Lv(Mm Ms) Ii(Ex Vu) Of(Qa Qe) dM(bN dB) fR(CX) AjMy CuVo LxOe MiJo MsMu JtNw OmOn UgaX Constrained panels with 2 analytes, where 1.0E-5 >= 'AUC p-value' > 1.0E-6. Contains 248 panels of 66,377 total panels evaluated. : Jj(Bo cP cX dB dM Et Fb Hb Ii Il Jg Jn Jo Jr Jt Kg Kk Ko Ld Li Lw Mg Mj Mk Mm Mr Mw Nb Nc No Nr Og Ok Om Pc Qn Qy Uf Up) aA(aF cV dH Fp Hu Ji Jr Lw Lx Ma Mz Nj Nw Om On Ow Pe Po Qn Ur) Og(bV cS dB Fp gL Hu Hx Is Iv Jg Jp Kd Nt Ou Qd Qe) gL(aE aF aG Al BN bS Iq Jt Jv Mm Om) Af(aX bC bV bZ cU dM FR Jp Kk Lv) Kd(aX bA cS Hb Ii Jt Lu Ms Qn Ur) cT(aW bE bP cP Cv Io Lv Nn Oe Us) Ug(BN cF CX Kc Mg Us Vv) Ur(cP li Io Jv Kk Or Vo Wm) Jo(Is Kc Kq Mp Ow Pe Qd Qe) Of(Hc Im Ir Is Jg My Nv Nw) Ow(CX dK Jv Mj Up Vo) aJ(Bn cF cP Lv Oe Qn Us) dN(bG bN cP cU Cx dB dM) Mb(aX cS Jp Lx Mp On) Qv(bA bP dK Io Mg) Kc(Aa cX Jq Qn Us) Kk(Bn cF cX Hb My) Ou(Dp Kf Mu Nm Nn) Vo(aQ Im My Qe Uf) bV(bN dB Mi Mu Rj) cS(bG In Lu Uk Up) Fr(Jt Nj Oe Om) Ii(Hc Ko Sr St) Cx(cU dM Jp) Mi(Hu Jt Om) bA(De Jq My) Mv(Hv Nu) Kq(Jt Uc) On(Iq Oe) Us(cX Hc) cU(Bo iZ) dM(cF cX) LuaF HuJp HbKo JlOm JqaX Constrained panels with 2 analytes, where 1.0E-4 >= 'AUC p-value' > 1.0E-5. Contains 429 panels of 66,377 total panels evaluated. : Og(bA CX dM Et Ij Ik Im Ir Jh Jl Lh Li Mp Mv My Mz Nb No Nu Nv Om Pb Qa Qv Ug) Us(Af aP aQ aX bN cU cY dK dR eF Fr Hu Hv Hx Jn Ko Kq Ld Mz Qe Qn Tn) My(Af Ao Bo bV cS cT CX dB Hb Hv Jp Kc Kj Lw Lx Ms Nu Qn Uu) Jp(Dc Hb Hv Hx Jv Ly Mp Ms Mu Mv Ni Nj Nn Nu Of Om Pb Qn Up) Vo(aJ bA bN bV cS Cx cY Fb Fr Hc Jg Kc Kk Ko Lv Qd Qv Sr Tn) Of(aJ bA Bg bV cS eF Hu Hx Ij Kq Lh Mv Mz Ow Pc Qd Wm) Kk(aQ bN Cq cY dR Ii Io Jv Kd Lv Mj Oe Om To Ug Up) bV(Bn bR bU cF cX dE Hu Hv Ii Jq Jv Kd Mv Om Qn Qy) cS(BN Bo dB fP Hb Hu Hv Hx Ii Io iZ Jv Oe Qn To) Cx(aP aX bC Bo bZ cP dB dF Fr iZ Kc Kd Lu Lv) Ow(aE Ao aX Bn cF gL Io Jt Kc Kd Lu Oe To Uk) bA(Hb Iq Jo Jt Jv Kg Ny Om Pg Qn Rj To Uf Up) Lv(Bn Bo bP cF cP cX dB dE dM Kd Ub Ug Up) aA(aW cF dM Fr Jg Lh Ly Mb Mg Ml Nu Ok Pa) Jo(aJ aX bZ Co Ir Kg Lx Nv Nw Ok On Qa) Kc(aQ bN cT Dl Ii Iq Jf Ks Ml Or Uu) Af(aP Aw Ba Bo cF cP dB dN Kq Ug) Hv(aX Hu Jg Jl Lx Mb Ms Mu On Ur) Hu(Hx Jl Lw Lx Mz Nn Qa Qe) li(aJ aP aX bZ cT Cu Jl Kn) Mb(Jg Jl Lw Mu Mz Nw Po) Jt(aJ Ba Is Ko Pe Qd Qe) Om(dR eF Jg Mt Mu Nv Qa) cU(aP aW cF cP dB dE fR) Jj(bC dR Ex Jv Ky To) Kd(cX gL Nm Oe To Up) Kq(Ao Dg Hb Jq Kj Uu) Lu(aJ aX

Figure 15 Continued cX dK Nw) Ms(Jg Jl Mt Mv On) Iq(aJ Fr Is Jl Mi) aP(bN cF cX dB dH) Lx(Md Mu Mv Ni) dM(aJ Bn bZ dE) fR(aC bN bU dH) gL(Cv Mj Ml Up) Ba(Aj Kl Uu) Wm(Hr In Ug) Ly(Jg Mv Nn) On(Hr Mm Nm) Ur(An dB dK) cT(De Jq Qn) cX(Fr iZ To) eF(bP iZ nY) Fp(Fr Mv) Hx(Hw Mu) Io(Ex Ug) aJ(aW Jq) bE(nY oK) bZ(bN dB) cP(dB dE) dN(cF dE) NnNu MiNi UeQy HbNw JlPb KoUu QnaX OuUf UgaQ

Constrained panels with 2 analytes, where 1.0E-3 >= 'AUC p-value' > 1.0E-4. Contains 722 panels of 66,377 total panels evaluated. : My(Ad aE aJ Al aW aX cF Dc Fp Hu Hx Iq Is Iz Ji Jl Jo Kd Ks Ky Li Mb Mp Mz Nc Nj Nn Om On Pa Pb Pe Qa Qe To Ub Up) Jo(Af aP Ba BN Bo bV cP cT cU Cw Cx Ex Hu Hx Ij Ip Jg Jl Kk Ko Lh Li Mu Mv Nn Po Qy Tn Uf Wm) Jp(Al BN cF Cv cX dB Dg Fp Hw Iq Ji Jl Jt Lh Li Lu Lw Lx Mk Mr Nr Nw Or Pa Pe To Uu Vo) Hu(Af aX cP Fp Ir Is Iv Ji Lh Li Mp Ms Mu Ng Nw Ok On Pb Pc Pe Po Ug Uu Vo) Hv(Af Bo cF CX Ip Iq Ji Lh Lw Ma Mp Mt Mz Ni Nn Nu Nw Ok Pb Pc Qn) Kk(aA bP dK Jq Jt Kg Ks Md Mg Ms Mu Mx Nn Nx Of Qx Tv Uf Uu Vp Tj) Vo(aA aU aV aX Bg bZ cT Cw dR eF Ex Hx Jn Kg Ma Mg Pb Ph Qy Ua Us) Ii(Bg Co cP cU Cx dM dR eF Fa Fb fR Gl Kg Nw Ph To Ua Uh Vv Wm) Of(aP aX bZ cT dR fR Ip Jh Ji Jk Li Lx Ma Mi Mt Mu Pg Qb Tn Ur) Og(Af aX BN cF cT Ip Jk Lw Ma Mb Mt Nn Pa Pe Pg Po Qb To Us) Hb(aA aJ aQ aX bV cT cX cY dR eF Ex Fr Hx Ji Lv Ma Mz Sr St) cF(aW bN bQ bZ cN cP cS Cx dA dB dE dF dG fR Hx Kc Kd Lu Us) Bo(AX bC BN bV bZ cX dM dN Fr Hx Iq Jq Jt Jv Lu Qn) Nu(Fp Hx Jg Li Lw Mj Mk Mp Ms Nb Nr Nw Om Pa Pb Pe Po) Af(Bg bN bQ dF Dk Ex Hr iZ Jh Ko Ky Lu Mi Mu Mv To) Iq(cS cT Hx Ij Ir Jg Lx Mp Mv Nv Nw Pe Pg Qa Qd Qe) Us(aU aV cP Cx Ex Ez Mg Mu Mv Ng Nq Qd Qy To Ut) Om(aJ aX Ba cS cT Im Ir Is Mb Ms Mv Nw Qe Qy) Uu(aA aJ aQ aX bA Bg bV cS eF Fr Hc Jg Kd Ua) cX(Ba bZ cS cU dE dF Hx Ky Ld Mu Rj Ub Uk Up) Kc(aA aE Ao Bn De Ha Hr Kj Lv Mj To Up Ur) bN(aO Bn cN cU Cx dF dG eF Ex Lu Lv Ow Qn) cP(aA aP Bn bZ cR cS dM fR Mi Mu Nn Oe Ow) Mb(Hx Is Ji Lh Li Nn No Nv Ok Pg Qa Qe) Jt(AP aX bV cS cT Jg Jl Lx Nv Qa Sr) Kd(aA Al aQ dB dK Dl dR Io Jv Mj Mm Rj) Ms(aX cS Is Jh Ji Lh Lx Mp Mz Nw Qa) Hx(aX Jg Ma Mt Mv Ni Nj Nn Pb Qn Wm) cT(Aa Ao Jv Ks Mg Pg Rj To Uf Ug Up) dB(Ax Bn dF dG eF Fr iZ Jf oK Qn) Mu(cS Fp gL Mz Ng Oi Pa Pb Qe) Jq(aA Ba bZ dR Ex Ji Kg Ko To) On(Fr Lx Md Mi Nj Nv Nx Oy Pz) Lu(Bn bP bV dN Fp Is Ji Lw) Lv(dR Jf Jv Ky Qn Rj To Wm) Mt(Jl Lw Mr Nb Ng Pa Pb Pc) Ug(bA dK Kg Mj Qy To Uf Up) Lx(Js Mk Mr Nn Nr Pa Pe) Ko(Aa bV cS Dg Io Ks Qn) aW(aP bV dN fR Jj Ow Ur) aX(iZ Kj Oe Rj To Uk Up) Ni(Is Jl Pe Pg Qa Qe) Qn(aQ aV dK dR Ex To) cS(Ax dE Kj Ks Or Ub) Cx(aC Ba Bc Ky To) Io(aJ dR Ky Ph To) Qe(Jg Mv Nn Pb Qc) bA(Dp Ha iZ Ks Vp) Bn(aP cU dN fR) Fr(aC Md Mi Nc) Ly(Ji Ma Mm Mz) Oe(aP Hc Jg Lh) dE(aP bU iZ nY) dK(iH iZ Jf Or) Ba(Ao Dg Dl) Mv(Mz Ng Pb) Jl(Iv Js Ng) Kq(bV Dl Kl) Nw(Js Mm Nx) aA(Cv Rj Up) aF(aO eF fR) Ex(Jv Mj) Mg(bV Ue) Mz(Nj Pb) Jj(Or Vv) aJ(Jv Mx) bZ(cE iZ) cI(eF oF) AoMa MdNv MiJs MmOw ToaQ IncU NxOk UraG aEeF bCfR bEoF bOnY bVcV Constrained panels with 2 analytes, where 1.0E-2 >= 'AUC p-value' > 1.0E-3. Contains 1,019 panels of 66,377 total panels evaluated. : Hb(aE Ap aV Ba BN Bo cF cP dD dK Et Hu Hv Jn Ke Kg Ky Li Lx Mg Mu Mv Nn Og On Ph Qy Rj To Uf Uh Up) bN(aN aX Ba bC bG bQ cO cP cR cX dA dB dE Fr Hu Hv Hx Ii Jv Kd Ky Mv My Mz Oe Rg Rj To Ub Uk Up) Ms(Aw eF Et Ex Hx Im Ir Jk Ko Li Lw Ma Mm Mn Mx Nn No Nq Nv Ok Or Pa Pe Pg Po Qb Qd Qe To) Jo(aF Aw bC Bg cF Cp Ct cX dB dM dN eF Et fR Hc Ik Iv Kn Ma Nt Nu Pa Pg Ph Qn Rj To Up Vv) Ao(Bg Co Cw Ef Ex Hc Hu Hx Jh Ji Jp Kd Kg Kk Ko Lh Mi Mu Mv Mz Nq Nw On Qd Qe Qy Tn Uf) Om(aP Bo bZ Et fR Hx Ij Ip Jh Ji Jk Kg Kq Ky Lh Li Lx Ma Mp Mz Nn Of Pe Pg Po Qd Uf) Jt(aF Aw Bn bZ cF Co Cp Cs CU Cw dB Et Ex fR Hc Im Kg Kn Lh Ma Og Ok Ph Tn) cP(aW aX bG Bo bV Hr Hv In Jp Kd Kg Kk Lu Mb Mg My Mz Of Og Qn To Ub Uf Up Vo) Ex(aF Al aQ Dc Ha Iq Kf Ki Kj Kl Ks Mi Mm Mp Mx Of Pg Qb Tv Uf Up Uu Vp) Mv(aE aJ cF Ct De dM Is Iv Ji Jl Kj Lh Li Lw Mk Mp Mr Nn Nr Nw Ok Pa Pe) Kk(aE bA Bg bX Dc Dd Dk Ha In Ir Jd Je Js Mm Mr Mw Nb No Nv Oy Pg Vs Wm) Bn(aC Aw aX Ba bC bZ cF cN dF Fr Hr Hu Hv Hx Ii iZ Kd My Oe Rg To Vo) Og(aW dR Jq Jr Ly Mg Mj Mk Mm Mr Mx Nc Nj Nr Or Oy Pc Qn Uf Up Vo Wm) Nn(Fp Iq Ir Is Iv Kj Lh Md Mi Mt Mz Nc Nj Nr Nw Of Pa Pe Qa Qd Us) Mu(aE aJ aX cF Cx De dM Is Iv Ji Jl Kj Lh Lw Mi Mk Mr Nr Nw Ok Pe) Ma(Aj Dg Dl Fp Iq Iv Kj Kl Ks Mb Mz Nc Ng Nj Nu On Pb Qe Qw Uu) Mp(Fp Hx Ir Is Iv Jl Lh Mt Mz Ni Nw Of Pb Pc Pe Qa Qd Qe Us) Hv(dB dM dN dR Ha Ks Mg Mk Mm Mr Nr Pa Pe Rj To Uk Up Vp Wm) Ii(Aw Bo cF Cp Cw cX dB dF Dk Ef Ky Ld Or Pg Qy Rj Uf Un Up) Jq(aP Aw cF cU dB dE dN fR Gl Kn Ky Ok Ph Qy Rj Sr Tn Uf) Uu(aV Bo bZ cF Ch cT cY dR Hx Jf Jn Ky Mz Or Qu Sr Tn To) Of(Bo cF cU dB Et Ik Iv Kc Kd Ko Mn Nt Nu Ok Ph Po Us) cX(aN aO Ax bC bQ cF cN cQ dB dG eF Hr Hu Mi Oe Or Vo) Hx(Af Al Cx dB dN dR Fp Ha Iv Ks Li Lw Mk Mz Rj Up) Pb(Et Fp Im Ir Is Iv Jg Ji Jr Li Nb Nt Qa Qd Uk Wm) aW(Af Ba bC bQ bZ cO cR cS Cx dB dF eC eF Lu Lv Us) Hu(Aj bP cF Cx dB dM Hw Mj Mk Mm Mr Nb No Nr Pa) Jv(aE aQ bZ cF dB dR eF Jn Ko Ky Mb My Ph To) Up(aE Af aJ aQ bP cU Cx dK dR Io Jn Qn To Vo) Us(aF Co Ef Jh Kg Li Mi Mw Or Pd Ph St Uf Vv) Fr(aE aF cU De dM Iz Ji Kj Kl Ks Lw Ng Ok) Iq(Ba dE Ih Im Ji Jk Kq Lh Mz Ok Po Qb) Qe(Dc Dl Hw Jl Ks Lw Mk Mr Nr Pa Pc Pe) Rj(Af aJ aQ cF Cx dK dR Io Jp My Qn To) Oe(Af Ba bP bZ cF Cx dM dN dR fR Pa Pe) Vo(AF Bo cF cU dB dK Jf Qn To Uh Vv) Mb(bP dM cF Et Ij Mm Nb Nu Pa Pc Pe) Qa(Hw Jg Jl Js Lw Mk Mr Nr Pa Pc Pe) Ks(cU dK Hc Im Jn Jp Kq Mg Mz Ph Sr) My(dM Iv Lh Mk Mr No Nr Ok Qw Uk) Ni(Ih Jk Lh Lj Nc Nj Nk Pa Po Qb) Kj(Ba Ef Hc Jp Kg Ko Mg Mi Qy Uf) Qn(aE aU cF Io Jn Ky Mg Mz Qy Uk) Nu(Hw Ir Lu Mg Mm Mr Mz No Pc) Kq(Ad aE Aj Ha In Io Iz Nm Pz) dB(aN Ba bG bU cO dA Hr Mz oF) Af(Ax Hc Kg Mz Nq Ph Qy Uf) Lu(Et Ko Mm Mz Nt Ok Pe Qd) To(aA aF aV cF dK dR Ld Mj) Jg(Fp Is Iv Md Mz Pa Pe Qd) Jl(Fp Is Ji Lw Mz Nw Ok Qd) oK(aA aJ aP bA bP cI cT dN) Hr(bZ cI cU Cx dN Pa Pe) Io(eF fR Jf Or Sr St Ub) Jp(Ad Dl Ha Ke Kf Kl Ok) Ba(aC Ad aE Iz Ng Ss) Ly(Et Im Ir No Rb Wm) Mi(aE aJ Bo cF dM Md) Mt(Hw Mj Mk No Nr Pe) Uk(aF cF cU dK dR Lv) Pc(Fp Li Mx Nj Pe Qd) Ax(aA aX bC bV dN) Lx(Al Hq Ji Ok Po) Kc(dK Iz Kd Mm Vp) Ko(Ad Dl Kl Mj Nm) dE(aF bC bG bZ dF) Wm(Il Iu Mj Na) Ub(cF dK eF Jf) Uf(aA Il Lv Uc) Dp(cT cU dK) Ha(Im Ld Qd) Nc(Nk Nw On) Hc(Aj Iz Ue) Ji(Aa Nx Pa) Js(Is Pe Po) bG(cF fR iZ) bZ(bF dH Pg) cE(bF bQ dF) Ad(Bg On) Dl(On Qd) Lw(Mk Nb) Md(Nb Nw) Mg(aJ Uc) Mj(eF Ky) Mz(Fp Iv) Kg(aA cT) Or(aX bA) aE(Kd Qy) aF(Bo Ow) bE(aC hC) cF(cO Rg) dA(bR bU) nY(cS dM) DefR NgNv NjNw UaUc InLd JhLi VpcT aJeC aOaX aZiZ bPoF cZhC dKhB

Figure 15 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Po | pg/ml | 9.0E-1 | 2.8E1 | 8.7E0 | 5.3E1 | 2.3E1 | 7.7E1 | 8.0E-3 | 2.6E-2 | 2.7E2 | 2.2E2 | 969 | 7 | 353 | 7 | 0.73 |
| Et | ng/ml | 1.4E3 | 2.8E3 | 1.7E3 | 2.4E3 | 1.2E3 | 1.6E3 | 7.5E1 | 5.9E2 | 5.0E3 | 4.4E3 | 968 | 7 | 353 | 7 | 0.64 |
| Fp | ng/ml | 1.4E1 | 2.5E1 | 2.6E1 | 3.2E1 | 2.9E1 | 2.6E1 | 6.0E-3 | 2.3E0 | 1.4E2 | 6.7E1 | 1004 | 7 | 354 | 7 | 0.59 |
| Fr | ng/ml | 4.1E4 | 6.5E5 | 1.3E5 | 5.1E5 | 1.9E5 | 3.3E5 | 1.9E2 | 7.0E3 | 9.0E5 | 8.5E5 | 1121 | 8 | 359 | 8 | 0.81 |
| Nm | pg/ml | 1.4E4 | 5.7E3 | 3.4E4 | 3.0E4 | 8.2E4 | 3.5E4 | 1.0E-9 | 1.0E-9 | 1.6E6 | 7.9E4 | 972 | 7 | 355 | 7 | 0.49 |
| Nn | pg/ml | 1.7E2 | 2.0E3 | 1.9E3 | 1.8E4 | 8.0E3 | 2.7E4 | 1.0E-9 | 1.0E-9 | 1.0E5 | 6.9E4 | 972 | 7 | 355 | 7 | 0.70 |
| No | pg/ml | 1.6E1 | 6.1E1 | 4.0E1 | 2.8E2 | 1.2E2 | 5.3E2 | 1.0E-9 | 1.6E0 | 2.5E3 | 1.4E3 | 972 | 7 | 355 | 7 | 0.65 |
| Nq | pg/ml | 2.0E0 | 1.6E1 | 1.9E1 | 3.3E1 | 7.4E1 | 4.4E1 | 1.0E-9 | 1.0E-9 | 1.2E3 | 1.1E2 | 972 | 7 | 355 | 7 | 0.70 |
| Nr | pg/ml | 1.1E0 | 1.2E0 | 2.9E1 | 1.2E3 | 1.7E2 | 3.2E3 | 1.0E-9 | 1.0E-9 | 4.1E3 | 8.5E3 | 972 | 7 | 355 | 7 | 0.55 |
| Ns | pg/ml | 1.0E-9 | 1.0E-9 | 8.7E0 | 5.1E-1 | 5.1E1 | 1.4E0 | 1.0E-9 | 1.0E-9 | 1.1E3 | 3.6E0 | 972 | 7 | 355 | 7 | 0.51 |
| Nt | pg/ml | 1.0E2 | 1.2E2 | 1.4E2 | 1.9E2 | 1.2E2 | 2.2E2 | 1.0E-9 | 6.6E1 | 1.7E3 | 6.8E2 | 972 | 7 | 355 | 7 | 0.57 |
| Nu | pg/ml | 2.2E1 | 6.5E1 | 5.5E1 | 1.3E2 | 8.9E1 | 2.0E2 | 1.0E-9 | 1.0E-9 | 8.9E2 | 5.8E2 | 972 | 7 | 355 | 7 | 0.68 |
| Lu | pg/ml | 1.0E4 | 3.0E3 | 1.7E4 | 6.2E3 | 6.0E4 | 7.1E3 | 3.5E2 | 1.0E3 | 1.3E6 | 2.1E4 | 975 | 7 | 355 | 7 | 0.26 |
| Lv | pg/ml | 1.0E-9 | 6.3E1 | 1.2E1 | 6.8E1 | 2.4E1 | 3.0E1 | 1.0E-9 | 3.3E1 | 2.6E2 | 1.0E2 | 975 | 7 | 355 | 7 | 0.95 |
| Lw | pg/ml | 1.0E-9 | 1.0E-9 | 4.6E-1 | 2.5E0 | 4.2E0 | 6.3E0 | 1.0E-9 | 1.0E-9 | 8.0E1 | 1.7E1 | 975 | 7 | 355 | 7 | 0.63 |
| Lx | pg/ml | 1.0E-9 | 4.9E2 | 1.9E2 | 2.1E3 | 8.4E2 | 3.6E3 | 1.0E-9 | 1.0E-9 | 2.2E4 | 1.0E4 | 975 | 7 | 355 | 7 | 0.82 |
| Ly | pg/ml | 1.0E-9 | 4.2E0 | 1.0E1 | 7.1E0 | 2.0E1 | 8.8E0 | 1.0E-9 | 1.0E-9 | 1.6E2 | 2.4E1 | 975 | 7 | 355 | 7 | 0.57 |
| Lz | pg/ml | 1.0E-9 | 1.0E-9 | 3.9E0 | 3.1E1 | 2.9E1 | 7.8E1 | 1.0E-9 | 1.0E-9 | 6.0E2 | 2.1E2 | 975 | 7 | 355 | 7 | 0.61 |
| Ma | pg/ml | 3.0E2 | 3.6E3 | 1.4E3 | 3.4E3 | 3.6E3 | 3.3E3 | 1.0E-9 | 2.4E1 | 6.5E4 | 9.5E3 | 975 | 7 | 355 | 7 | 0.71 |
| Mb | pg/ml | 2.5E1 | 2.2E1 | 3.1E1 | 3.0E1 | 1.5E1 | 1.2E1 | 4.1E0 | 2.1E1 | 2.1E2 | 5.0E1 | 975 | 7 | 355 | 7 | 0.49 |
| Mc | pg/ml | 1.0E-9 | 1.0E-9 | 3.9E-2 | 1.0E-9 | 5.5E-1 | 0.0E0 | 1.0E-9 | 1.0E-9 | 1.3E1 | 1.0E-9 | 975 | 7 | 355 | 7 | 0.49 |
| Md | pg/ml | 1.0E-9 | 1.0E-9 | 4.1E-1 | 1.6E0 | 3.5E0 | 4.1E0 | 1.0E-9 | 1.0E-9 | 6.8E1 | 1.1E1 | 975 | 7 | 355 | 7 | 0.54 |
| Me | pg/ml | 3.3E1 | 2.6E1 | 3.2E1 | 2.9E1 | 1.9E1 | 2.5E1 | 1.0E-9 | 3.2E0 | 3.2E2 | 7.9E1 | 975 | 7 | 355 | 7 | 0.37 |
| Mf | pg/ml | 1.0E-9 | 1.0E-9 | 5.1E-1 | 1.0E-9 | 2.8E0 | 0.0E0 | 1.0E-9 | 1.0E-9 | 5.6E1 | 1.0E-9 | 975 | 7 | 355 | 7 | 0.43 |
| Mg | pg/ml | 1.6E0 | 1.8E0 | 7.5E0 | 3.0E0 | 1.3E1 | 3.6E0 | 1.0E-9 | 1.0E-9 | 9.4E1 | 9.0E0 | 975 | 7 | 355 | 7 | 0.44 |
| Mh | pg/ml | 1.0E-9 | 1.0E-9 | 1.3E0 | 5.4E0 | 9.3E0 | 1.4E1 | 1.0E-9 | 1.0E-9 | 1.6E2 | 3.8E1 | 975 | 7 | 355 | 7 | 0.51 |
| Mi | pg/ml | 1.0E-9 | 2.7E1 | 9.8E-1 | 4.1E1 | 1.2E1 | 5.9E1 | 1.0E-9 | 1.0E-9 | 3.2E2 | 1.6E2 | 975 | 7 | 355 | 7 | 0.78 |
| Mj | pg/ml | 1.0E-9 | 7.8E0 | 4.5E0 | 8.4E1 | 2.4E1 | 2.0E2 | 1.0E-9 | 1.0E-9 | 4.6E2 | 5.4E2 | 975 | 7 | 355 | 7 | 0.71 |
| Mk | pg/ml | 9.1E-1 | 5.3E0 | 1.4E1 | 8.0E2 | 8.3E1 | 2.1E3 | 1.0E-9 | 1.0E-9 | 1.7E3 | 5.6E3 | 975 | 7 | 355 | 7 | 0.58 |
| Ml | pg/ml | 1.0E-9 | 1.0E-9 | 5.5E0 | 3.9E-1 | 7.2E1 | 1.0E0 | 1.0E-9 | 1.0E-9 | 2.1E3 | 2.8E0 | 975 | 7 | 355 | 7 | 0.48 |
| Mm | pg/ml | 6.1E2 | 4.8E2 | 1.1E3 | 1.7E3 | 1.5E3 | 2.5E3 | 1.0E-9 | 1.0E-9 | 1.2E4 | 6.9E3 | 975 | 7 | 355 | 7 | 0.50 |
| Mn | pg/ml | 5.7E0 | 1.2E1 | 1.0E1 | 1.9E1 | 2.2E1 | 2.1E1 | 1.0E-9 | 1.1E0 | 3.5E2 | 6.6E1 | 975 | 7 | 355 | 7 | 0.72 |
| Mp | pg/ml | 1.0E-9 | 2.7E1 | 1.0E1 | 5.5E1 | 3.4E1 | 6.9E1 | 1.0E-9 | 1.0E-9 | 6.3E2 | 1.8E2 | 974 | 7 | 355 | 7 | 0.73 |
| Mq | pg/ml | 1.0E-9 | 1.0E-9 | 3.2E0 | 1.0E-9 | 1.8E1 | 0.0E0 | 1.0E-9 | 1.0E-9 | 2.4E2 | 1.0E-9 | 974 | 7 | 355 | 7 | 0.46 |
| Mr | pg/ml | 1.0E-9 | 1.0E-9 | 2.8E1 | 1.7E3 | 1.6E2 | 4.5E3 | 1.0E-9 | 1.0E-9 | 2.2E3 | 1.2E4 | 974 | 7 | 355 | 7 | 0.58 |
| Ms | pg/ml | 3.9E2 | 8.0E1 | 5.4E2 | 2.3E2 | 6.5E2 | 3.3E2 | 1.0E-9 | 1.0E-9 | 5.9E3 | 8.6E2 | 974 | 7 | 355 | 7 | 0.31 |
| Mt | pg/ml | 3.1E-1 | 9.0E0 | 1.1E1 | 2.5E1 | 1.1E2 | 3.7E1 | 1.0E-9 | 1.0E-9 | 3.2E3 | 1.0E2 | 974 | 7 | 355 | 7 | 0.79 |
| Mu | pg/ml | 1.0E-9 | 7.1E0 | 1.2E0 | 8.6E0 | 1.0E1 | 1.0E1 | 1.0E-9 | 1.0E-9 | 2.3E2 | 2.7E1 | 974 | 7 | 355 | 7 | 0.74 |
| Mv | pg/ml | 1.0E-9 | 5.9E1 | 7.0E1 | 1.5E2 | 3.1E2 | 2.3E2 | 1.0E-9 | 1.0E-9 | 4.5E3 | 6.2E2 | 974 | 7 | 355 | 7 | 0.75 |
| Mw | pg/ml | 4.0E1 | 6.6E2 | 5.0E2 | 1.9E3 | 3.1E3 | 3.1E3 | 1.0E-9 | 1.0E-9 | 6.2E4 | 8.5E3 | 974 | 7 | 355 | 7 | 0.75 |
| Mx | pg/ml | 1.0E-9 | 1.0E-9 | 2.8E-1 | 4.7E-1 | 1.5E0 | 1.1E0 | 1.0E-9 | 1.0E-9 | 3.2E1 | 3.0E0 | 974 | 7 | 355 | 7 | 0.63 |
| My | pg/ml | 1.0E-9 | 8.8E1 | 4.4E2 | 5.7E2 | 2.9E3 | 1.2E3 | 1.0E-9 | 1.0E-9 | 3.9E4 | 3.4E3 | 974 | 7 | 355 | 7 | 0.68 |
| Mz | pg/ml | 1.2E1 | 6.3E1 | 3.1E1 | 1.1E2 | 9.7E1 | 1.3E2 | 1.0E-9 | 8.0E0 | 1.9E3 | 3.6E2 | 974 | 7 | 355 | 7 | 0.82 |
| Na | pg/ml | 1.0E-9 | 1.0E-9 | 7.1E-1 | 1.5E0 | 2.9E0 | 4.0E0 | 1.0E-9 | 1.0E-9 | 4.2E1 | 1.1E1 | 974 | 7 | 355 | 7 | 0.48 |
| Nb | pg/ml | 2.1E0 | 4.6E0 | 4.0E0 | 3.7E1 | 1.2E1 | 8.9E1 | 1.0E-9 | 9.2E-2 | 2.3E2 | 2.4E2 | 974 | 7 | 355 | 7 | 0.63 |
| Nc | pg/ml | 3.3E2 | 1.5E2 | 5.5E2 | 1.7E2 | 7.2E2 | 2.3E2 | 1.0E-9 | 1.0E-9 | 9.2E3 | 6.7E2 | 974 | 7 | 355 | 7 | 0.35 |
| Nd | pg/ml | 2.9E1 | 4.1E1 | 2.9E1 | 6.9E1 | 8.0E1 | 6.2E1 | 1.0E-9 | 7.2E-1 | 2.1E3 | 1.5E2 | 974 | 7 | 355 | 7 | 0.69 |
| Ne | pg/ml | 4.3E2 | 2.7E2 | 5.6E2 | 7.0E2 | 5.7E2 | 1.3E3 | 1.0E-9 | 1.8E1 | 7.0E3 | 3.6E3 | 974 | 7 | 355 | 7 | 0.40 |
| Nf | pg/ml | 1.0E-9 | 1.0E-9 | 2.8E0 | 1.2E1 | 1.1E1 | 3.1E1 | 1.0E-9 | 1.0E-9 | 1.6E2 | 8.2E1 | 974 | 7 | 355 | 7 | 0.47 |
| Ng | pg/ml | 1.8E1 | 1.0E-9 | 1.2E2 | 3.8E1 | 2.5E2 | 8.6E1 | 1.0E-9 | 1.0E-9 | 2.3E3 | 2.3E2 | 974 | 7 | 355 | 7 | 0.34 |
| Nh | pg/ml | 6.7E1 | 3.5E1 | 8.9E1 | 1.1E2 | 8.1E1 | 1.8E2 | 1.0E-9 | 2.2E0 | 5.6E2 | 5.1E2 | 974 | 7 | 355 | 7 | 0.40 |
| Ni | pg/ml | 1.0E-9 | 2.3E1 | 7.4E1 | 7.2E1 | 1.2E2 | 1.2E2 | 1.0E-9 | 1.0E-9 | 1.1E3 | 3.4E2 | 974 | 7 | 355 | 7 | 0.53 |
| Nj | pg/ml | 7.4E0 | 5.8E0 | 1.1E1 | 5.0E0 | 1.2E1 | 3.8E0 | 1.0E-9 | 1.0E-9 | 1.1E2 | 9.5E0 | 974 | 7 | 355 | 7 | 0.36 |
| Nk | pg/ml | 1.7E1 | 2.3E1 | 3.2E1 | 1.6E1 | 3.9E1 | 1.3E1 | 1.0E-9 | 1.0E-9 | 2.0E2 | 2.7E1 | 974 | 7 | 355 | 7 | 0.42 |

Figure 16

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nl | pg/ml | 4.5E1 | 2.3E1 | 6.0E1 | 5.0E1 | 6.7E1 | 6.6E1 | 1.0E-9 | 1.0E-9 | 1.1E3 | 1.8E2 | 974 | 7 | 355 | 7 | 0.42 |
| Hq | pg/ml | 1.1E0 | 1.7E0 | 9.6E1 | 4.5E1 | 1.6E3 | 1.1E2 | 1.0E-9 | 1.0E-9 | 3.4E4 | 3.0E2 | 970 | 7 | 354 | 7 | 0.56 |
| Hr | pg/ml | 1.1E2 | 4.5E1 | 7.6E2 | 1.6E3 | 1.6E3 | 4.0E3 | 1.0E-9 | 2.1E1 | 1.7E4 | 1.1E4 | 970 | 7 | 354 | 7 | 0.36 |
| Hu | pg/ml | 7.1E0 | 8.5E1 | 2.9E3 | 8.2E2 | 2.5E4 | 1.1E3 | 1.0E-9 | 1.0E-9 | 6.3E5 | 2.5E3 | 970 | 7 | 354 | 7 | 0.69 |
| Hv | pg/ml | 1.5E0 | 2.3E0 | 4.2E0 | 1.0E1 | 3.1E1 | 2.1E1 | 1.0E-9 | 9.7E-1 | 8.9E2 | 5.9E1 | 970 | 7 | 354 | 7 | 0.67 |
| Hw | pg/ml | 6.3E0 | 2.1E0 | 2.7E1 | 5.0E2 | 3.1E1 | 1.3E3 | 1.0E-9 | 3.2E-1 | 9.4E3 | 3.4E3 | 970 | 7 | 354 | 7 | 0.36 |
| Hx | pg/ml | 9.2E0 | 3.9E1 | 3.8E1 | 3.2E2 | 3.1E1 | 7.3E2 | 1.0E-9 | 1.0E-9 | 9.3E3 | 2.0E3 | 970 | 7 | 354 | 7 | 0.79 |
| Ih | ng/ml | 7.4E1 | 2.9E2 | 2.6E2 | 4.0E2 | 5.8E2 | 4.3E2 | 1.0E-9 | 2.4E0 | 8.1E3 | 1.2E3 | 974 | 7 | 354 | 7 | 0.66 |
| Ii | ng/ml | 9.3E1 | 8.9E1 | 2.4E2 | 1.5E3 | 6.6E2 | 3.4E3 | 1.0E-9 | 7.5E-1 | 1.0E4 | 9.2E3 | 973 | 7 | 354 | 7 | 0.54 |
| In | ng/ml | 3.3E0 | 5.4E-1 | 2.5E1 | 9.4E1 | 2.0E2 | 2.2E2 | 1.0E-9 | 3.1E-2 | 4.5E3 | 5.9E2 | 974 | 7 | 354 | 7 | 0.41 |
| Io | ng/ml | 8.2E3 | 8.0E3 | 2.4E4 | 8.7E4 | 1.4E5 | 2.1E5 | 1.0E-9 | 1.3E3 | 4.0E6 | 5.5E5 | 965 | 7 | 354 | 7 | 0.55 |
| Ip | ng/ml | 1.0E1 | 3.0E1 | 2.0E1 | 4.0E1 | 2.5E1 | 4.6E1 | 1.0E-9 | 1.1E-2 | 2.6E2 | 1.4E2 | 965 | 7 | 354 | 7 | 0.65 |
| Iq | ug/ml | 1.0E-1 | 2.5E-1 | 2.9E1 | 1.1E2 | 6.2E2 | 2.8E2 | 1.0E-9 | 1.0E-9 | 1.4E4 | 7.5E2 | 965 | 7 | 354 | 7 | 0.53 |
| Ir | ug/ml | 3.7E-1 | 1.7E0 | 4.4E0 | 2.1E1 | 2.8E1 | 4.2E1 | 1.0E-9 | 3.5E-2 | 5.1E2 | 1.1E2 | 964 | 7 | 354 | 7 | 0.77 |
| Is | ng/ml | 1.7E0 | 1.3E1 | 7.1E0 | 5.5E1 | 2.3E1 | 8.7E1 | 1.0E-9 | 4.3E-1 | 5.5E2 | 2.3E2 | 965 | 7 | 354 | 7 | 0.76 |
| It | ng/ml | 2.0E0 | 2.0E0 | 2.3E1 | 8.7E1 | 1.3E2 | 2.2E2 | 1.0E-9 | 1.0E-9 | 2.8E3 | 5.9E2 | 965 | 7 | 354 | 7 | 0.55 |
| Iu | ng/ml | 2.1E2 | 1.0E3 | 1.4E3 | 4.5E3 | 4.1E3 | 8.8E3 | 1.0E-9 | 1.0E-9 | 2.9E4 | 2.4E4 | 965 | 7 | 354 | 7 | 0.59 |
| Iv | ng/ml | 1.4E1 | 1.8E1 | 6.8E1 | 9.6E2 | 5.5E2 | 2.4E3 | 1.0E-9 | 5.7E0 | 1.6E4 | 6.4E3 | 964 | 7 | 354 | 7 | 0.64 |
| Pz | ng/ml | 3.9E3 | 4.3E3 | 8.1E3 | 6.4E3 | 3.6E4 | 5.1E3 | 1.3E1 | 4.0E1 | 1.0E6 | 1.4E4 | 966 | 7 | 352 | 7 | 0.59 |
| Qa | ng/ml | 3.6E3 | 1.6E4 | 6.8E3 | 1.5E4 | 1.0E4 | 1.0E4 | 1.2E1 | 9.4E2 | 2.2E5 | 3.1E4 | 966 | 7 | 352 | 7 | 0.76 |
| Qb | ng/ml | 1.0E2 | 6.0E2 | 2.2E2 | 5.8E2 | 4.8E2 | 5.3E2 | 7.9E-1 | 3.2E1 | 8.3E3 | 1.6E3 | 966 | 7 | 352 | 7 | 0.75 |
| Qc | ng/ml | 2.3E2 | 5.0E2 | 6.2E2 | 7.2E2 | 5.4E3 | 8.3E2 | 1.0E-9 | 3.2E1 | 1.7E5 | 2.4E3 | 966 | 7 | 352 | 7 | 0.61 |
| Qd | ng/ml | 9.4E3 | 2.6E4 | 2.2E4 | 6.2E4 | 7.6E4 | 6.5E4 | 1.5E2 | 1.9E3 | 2.0E6 | 1.7E5 | 966 | 7 | 352 | 7 | 0.72 |
| Qe | ng/ml | 9.7E2 | 3.7E3 | 2.0E3 | 4.9E3 | 4.7E3 | 4.6E3 | 1.0E-9 | 1.2E2 | 9.7E4 | 1.4E4 | 966 | 7 | 352 | 7 | 0.76 |
| Jg | ng/ml | 5.1E2 | 1.4E3 | 8.4E2 | 2.1E3 | 1.0E3 | 2.0E3 | 1.0E-9 | 8.4E1 | 1.0E4 | 5.4E3 | 970 | 7 | 354 | 7 | 0.68 |
| Jh | ng/ml | 3.2E0 | 6.0E1 | 2.8E1 | 6.8E1 | 1.1E2 | 7.5E1 | 1.0E-9 | 1.0E-9 | 1.6E3 | 2.1E2 | 970 | 7 | 354 | 7 | 0.74 |
| Ji | ng/ml | 5.4E1 | 1.6E2 | 8.4E1 | 2.0E2 | 1.1E2 | 2.0E2 | 1.0E-9 | 2.3E1 | 1.8E3 | 5.9E2 | 970 | 7 | 354 | 7 | 0.70 |
| Jj | ng/ml | 5.7E2 | 9.8E1 | 1.6E3 | 2.4E2 | 1.2E4 | 3.5E2 | 1.5E0 | 8.7E0 | 3.4E5 | 1.0E3 | 970 | 7 | 354 | 7 | 0.20 |
| Jk | ng/ml | 3.3E0 | 4.2E1 | 2.2E1 | 7.1E1 | 4.6E1 | 7.8E1 | 1.0E-9 | 1.2E-1 | 3.9E2 | 1.8E2 | 970 | 7 | 354 | 7 | 0.70 |
| Jl | ng/ml | 4.5E-1 | 2.0E1 | 2.6E0 | 3.3E1 | 1.8E1 | 5.6E1 | 7.6E-4 | 2.5E-1 | 5.4E2 | 1.6E2 | 970 | 7 | 354 | 7 | 0.87 |
| Jm | ng/ml | 1.8E1 | 1.9E1 | 5.8E1 | 4.4E1 | 1.3E2 | 7.2E1 | 1.0E-9 | 4.0E-1 | 2.1E3 | 2.0E2 | 970 | 7 | 354 | 7 | 0.48 |
| Jn | pg/ml | 4.0E-1 | 1.2E0 | 3.9E0 | 2.5E0 | 3.8E1 | 3.1E0 | 1.0E-9 | 2.8E-2 | 7.3E2 | 7.2E0 | 969 | 7 | 354 | 7 | 0.67 |
| Jo | ng/ml | 3.5E3 | 1.6E3 | 4.8E3 | 6.8E3 | 4.9E3 | 1.4E4 | 2.0E1 | 2.4E1 | 1.0E5 | 3.8E4 | 970 | 7 | 354 | 7 | 0.32 |
| Jp | pg/ml | 7.2E4 | 1.1E5 | 7.5E4 | 1.3E5 | 3.8E4 | 5.2E4 | 5.8E2 | 6.8E4 | 3.8E5 | 2.2E5 | 970 | 7 | 354 | 7 | 0.81 |
| Jq | pg/ml | 9.5E1 | 1.2E2 | 1.7E2 | 6.9E2 | 3.7E2 | 1.5E3 | 1.0E0 | 1.3E1 | 8.7E3 | 4.1E3 | 970 | 7 | 354 | 7 | 0.51 |
| Jr | pg/ml | 5.5E0 | 2.6E1 | 4.6E1 | 6.3E1 | 4.6E2 | 7.9E1 | 1.0E-9 | 9.5E0 | 1.1E4 | 1.9E2 | 970 | 7 | 354 | 7 | 0.84 |
| Js | pg/ml | 1.3E1 | 1.6E1 | 5.5E1 | 2.9E1 | 3.8E2 | 3.2E1 | 1.0E-9 | 2.7E0 | 1.0E4 | 9.4E1 | 970 | 7 | 354 | 7 | 0.58 |
| Jt | pg/ml | 2.6E3 | 2.1E3 | 3.3E3 | 6.2E3 | 2.8E3 | 1.2E4 | 2.2E1 | 1.5E2 | 5.2E4 | 3.3E4 | 970 | 7 | 354 | 7 | 0.40 |
| Lh | pg/ml | 1.3E4 | 3.4E4 | 2.2E4 | 1.1E5 | 3.2E4 | 1.4E5 | 1.0E-9 | 2.0E3 | 4.8E5 | 4.1E5 | 969 | 7 | 355 | 7 | 0.78 |
| Li | pg/ml | 3.7E3 | 5.4E3 | 1.8E4 | 1.1E5 | 6.4E4 | 2.2E5 | 1.0E-9 | 3.6E1 | 1.3E6 | 5.9E5 | 969 | 7 | 355 | 7 | 0.57 |
| Lj | pg/ml | 2.9E3 | 8.3E3 | 2.5E4 | 5.9E4 | 7.0E4 | 1.3E5 | 1.0E-9 | 8.9E1 | 6.1E5 | 3.5E5 | 969 | 7 | 355 | 7 | 0.58 |
| Nv | pg/ml | 4.0E3 | 1.2E4 | 1.1E4 | 3.0E4 | 4.2E4 | 3.5E4 | 1.0E-9 | 1.6E2 | 1.1E6 | 8.4E4 | 976 | 7 | 355 | 7 | 0.75 |
| Nw | pg/ml | 9.2E3 | 1.9E4 | 1.4E4 | 5.8E4 | 1.8E4 | 7.1E4 | 8.6E1 | 4.5E3 | 2.1E5 | 1.7E5 | 976 | 7 | 355 | 7 | 0.73 |
| Nx | pg/ml | 2.2E2 | 4.6E1 | 4.2E2 | 4.7E2 | 6.6E2 | 7.2E2 | 1.0E-9 | 1.0E-9 | 7.4E3 | 1.9E3 | 976 | 7 | 355 | 7 | 0.47 |
| Ny | pg/ml | 6.7E0 | 2.3E1 | 5.5E1 | 1.6E2 | 8.2E2 | 2.5E2 | 1.0E-9 | 1.0E-9 | 2.5E4 | 6.2E2 | 976 | 7 | 355 | 7 | 0.68 |
| Oe | pg/ml | 7.0E1 | 1.0E-9 | 2.8E2 | 2.3E2 | 7.3E2 | 6.1E2 | 1.0E-9 | 1.0E-9 | 1.9E4 | 1.6E3 | 967 | 7 | 354 | 7 | 0.31 |
| Of | pg/ml | 1.7E2 | 8.1E1 | 5.8E3 | 1.1E4 | 2.7E4 | 2.8E4 | 1.0E-9 | 1.0E-9 | 6.2E5 | 7.4E4 | 975 | 7 | 355 | 7 | 0.44 |
| Og | pg/ml | 8.2E-2 | 1.0E-9 | 7.0E-1 | 4.7E-2 | 4.6E0 | 1.0E-1 | 1.0E-9 | 1.0E-9 | 8.3E1 | 2.7E-1 | 975 | 7 | 355 | 7 | 0.24 |
| Oh | pg/ml | 2.8E0 | 5.3E0 | 2.1E1 | 3.9E1 | 1.4E2 | 8.3E1 | 1.0E-9 | 1.0E-9 | 3.5E3 | 2.2E2 | 975 | 7 | 355 | 7 | 0.53 |
| Oi | pg/ml | 2.5E0 | 3.3E-1 | 6.2E0 | 1.9E0 | 9.7E0 | 2.7E0 | 1.0E-9 | 1.0E-9 | 8.6E1 | 6.4E0 | 975 | 7 | 355 | 7 | 0.38 |
| Ok | pg/ml | 3.9E2 | 6.5E2 | 6.5E2 | 1.9E3 | 2.3E3 | 3.5E3 | 1.3E1 | 5.3E1 | 7.0E4 | 9.8E3 | 975 | 7 | 355 | 7 | 0.61 |
| Om | pg/ml | 4.0E2 | 8.0E2 | 8.9E2 | 5.9E3 | 2.6E3 | 8.5E3 | 1.0E-9 | 7.0E1 | 5.1E4 | 2.0E4 | 975 | 7 | 355 | 7 | 0.63 |
| On | pg/ml | 1.9E2 | 7.5E2 | 3.2E2 | 2.9E3 | 5.2E2 | 5.4E3 | 1.0E-9 | 1.6E1 | 9.8E3 | 1.5E4 | 975 | 7 | 355 | 7 | 0.78 |
| Oy | pg/ml | 4.8E-1 | 2.4E-1 | 5.5E0 | 4.1E1 | 2.8E1 | 1.0E2 | 1.0E-9 | 1.0E-9 | 4.0E2 | 2.7E2 | 974 | 7 | 354 | 7 | 0.48 |
| Oz | pg/ml | 7.0E-3 | 1.0E-9 | 3.1E-1 | 2.3E-1 | 1.3E0 | 3.3E-1 | 1.0E-9 | 1.0E-9 | 2.9E1 | 7.0E-1 | 974 | 7 | 354 | 7 | 0.49 |
| Pa | pg/ml | 4.0E-1 | 3.5E0 | 1.5E0 | 5.0E1 | 5.9E0 | 1.1E2 | 1.0E-9 | 1.7E-1 | 1.0E2 | 2.9E2 | 974 | 7 | 354 | 7 | 0.82 |
| Pb | pg/ml | 1.0E-9 | 6.9E-2 | 7.5E-1 | 2.6E1 | 1.6E1 | 6.8E1 | 1.0E-9 | 1.0E-9 | 4.9E2 | 1.8E2 | 974 | 7 | 354 | 7 | 0.57 |

Figure 16 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Pc | pg/ml | 4.7E-2 | 4.2E-1 | 3.6E-1 | 2.8E0 | 8.6E-1 | 4.4E0 | 1.0E-9 | 1.0E-9 | 1.6E1 | 1.1E1 | 974 | 7 | 354 | 7 | 0.62 |
| Pd | pg/ml | 1.9E0 | 2.3E0 | 4.9E0 | 3.7E0 | 2.8E1 | 6.4E0 | 1.0E-9 | 1.0E-9 | 8.4E2 | 1.8E1 | 974 | 7 | 354 | 7 | 0.44 |
| Pe | pg/ml | 2.3E1 | 1.2E2 | 1.2E2 | 2.4E3 | 4.3E2 | 5.3E3 | 1.0E-9 | 3.3E0 | 6.7E3 | 1.4E4 | 974 | 7 | 354 | 7 | 0.75 |
| Pf | pg/ml | 1.7E0 | 1.3E1 | 1.1E1 | 4.1E1 | 5.8E1 | 8.4E1 | 1.0E-9 | 1.0E-9 | 1.5E3 | 2.3E2 | 974 | 7 | 354 | 7 | 0.70 |
| Pg | pg/ml | 3.6E0 | 4.9E1 | 4.2E1 | 3.5E2 | 3.3E2 | 6.9E2 | 1.0E-9 | 1.9E0 | 7.7E3 | 1.9E3 | 974 | 7 | 354 | 7 | 0.80 |
| aA | mg/dL | 8.3E-1 | 1.9E0 | 9.7E-1 | 2.6E0 | 5.2E-1 | 1.7E0 | 2.0E-1 | 1.1E0 | 4.2E0 | 5.4E0 | 2812 | 12 | 531 | 12 | 0.89 |

Analyte panel data:

Unconstrained panels with 3 analytes, where 1.0E-8 >= 'model p-value' > 0. Contains 150 panels of 260,130 total panels evaluated. : Lv{aA(Et Fp Hr Hv Hw Ih Ii In Ip Iq Ir Is It Iu Ig Jh Ji Jj Jn Jo Jq Jr Js Jt Lh Li Lu Md Me Mf Mg Mh Ml Mm Mq Mr Ms Mt Mx Mz Na Nd Ne Nf Ng Nh Ni Nk Nm Nn Ns Nt Nv Nx Ny Oe Of Og Oh Oi Ok Om Pa Pc Pd Pf Po Pz Qa Qe) Og(Fr Hx Iq Jj Jl Jo Lu Mf Mg Mi Mk Mr Mz Nn Nr Nw Nx On Pa Pb Pc) Nx(Fr Hx Iq Jj Jl Jp Lu Mi Mu Mz Nd Nn Oe On Pa Pc Pg) Jo(Hx Jl Lu Mi Mk Mr Nr Pa Pe Pg) Pa(Iu Jj Jt Li Mg Ng Oe Pd Pe) Jj(Jk Jl Lu Mq) Mg(Fr Lu Nn) Mi(Nt Pd) Jl(Jt Mm) NrOe LuNg PdPe} Mi{Pa(Pd Pe) HqOg PdPg} aA{Jt(Jl Pg) NjOg} Pa{NnPd JjPe}

Unconstrained panels with 3 analytes, where 1.0E-7 >= 'model p-value' > 1.0E-8. Contains 576 panels of 260,130 total panels evaluated. : Lv{Og(Et Fp Hq Hr Hu Hv Hw Ih Ii In Io Ip Ir Is It Iu Iv Jg Jh Ji Jk Jm Jn Jp Jq Jr Js Jt Lh Li Lj Lw Lx Ly Lz Ma Mb Mc Md Me Mh Mj Ml Mm Mn Mp Mq Ms Mt Mu Mv Mw Mx My Na Nb Nc Nd Ne Nf Ng Nh Ni Nj Nk Nl Nm No Nq Ns Nt Nu Nv Ny Oe Of Oh Oi Ok Om Oy Oz Pd Pe Pf Pg Po Pz Qa Qb Qc Qd Qe) Nx(Hr Hu Hv Ih Ii Io Ip Ir Is It Iu Iv Jg Jh Jk Jn Jo Jr Lh Li Lw Lx Ly Lz Ma Mb Me Mf Mg Mh Mj Mk Ml Mm Mn Mp Mq Mr Ms Mt Mv Mw My Nb Nc Ne Ng Nh Nk No Nq Nr Nu Nv Nw Oi Om Oy Pb Pd Pe Po Qa Qb Qd Qe) Jj(Fp Fr Hu Hv Hx Ih Ii In Io Iq Is Iu Ji Jo Jp Jr Lh Li Lx Lz Mb Mf Mg Mh Mi Mj Mk Ml Mr Ms Mu Mv Mw Mz Nb Nc Nd Ne Nh Nk Nm Nn Nq Nr Oe Oi Ok On Oy Pb Pc Pd Pe Pg Po) aA(Fr Hq Hu Hx Io Iv Jk Jl Jm Jp Lj Lw Lx Ly Lz Ma Mb Mc Mi Mj Mk Mn Mp Mu Mv Mw My Nb Nc Nj Nl No Nq Nr Nu Nw On Oy Oz Pb Pc Pg Qb Qc Qd) Pa(Et Fp Hq Ii Iq Jl Jm Jn Jq Js Lu Ly Mf Mh Mi Ml Mm Mq Mr Ms Mx Na Ne Nf Nh Nj Nm Nn Nq Nr Ns Nt Nv Ny Of Oh Oi Ok Oy Oz Pc Pf Po Pz) Jo(Fr Hw Ih Ii Io Iq Ir Is Iu Jk Jp Jr Lh Li Mb Mf Mj Mq Mu Mv Mz Nb Nd Nn No Nv Nw Oe On Pb Pc Po) Lu(Fr Hq Hx Iu Jl Jp Jr Js Ly Mb Mf Mh Mi Ml Mm Mq Mz Na Nd Ne Nf Nh Nn Nq Nt Nw Oe Of Oi Pc Pd) Jl(Et Ii Iu Ji Jq Js Li Mf Mg Mq Ms Mx Ng Nh Nm Nv Ny Oe Of Oh Oi Ok Pd Pz) Oe(Fr Hx Io Iq Mf Mg Mi Mk Mq Mr Mz Nd Ng Nn Nw On Pb Pc Pe) Mi(Hq Iu Js Jt Li Lx Mf Mg Mm Mq Ms Ng Nh Nm Nq Oh) Fr(Et Jt Li Mm Mq Ms Ng Nm Ok) Jt(Hx Ir Jp Mr Mz Nr On Pe) Mg(Jg Jp Lh Mv Nd Pc) Ng(Mk Mr Mw Nn Pb Pc) Mq(Hx Mz Nd Nw Om) Pd(Lh Lx On Po) Mm(Jp Mz On) Nn(Ms Oi) Mf(Hx Mz) Pc(Ms Oi) NtLx NcNl IsJs} aA{Og(Hx Ih Iq It Iu Jg Jj Jl Jn Jo Jr Js Jt Li Lw Ly Mg Mi Ml Mm Mq Ms Mt Mv Mx Mz Ne Nf Ng Nh Nq Oe Oh Oi Oz Pa Pb Pc Pd Pf Pg Qb) Jt(Hx Lw Mi Pa Pc Pe) Jl(Iq Mm Oe Oh Ok) Pa(Iq Js Pd Pe) Pc(Nf Oe Oi) Pg(Jo Js) NnOi MiIq MsOe} Pa{Pd(Fr Jj Jl Jo Lh Mu Mv Oe Og) Pe(Fr Jo Oe Og) Js(Hr Jl Mi) Jj(Nj Og) Jo(Oe Og) Jt(Jl Jp)} Mi{Pd(Nn Og Pc Pe Po) Hq(Jt Ms Oe) NqOg} Jl{Og(Jt Mm)} Pd{NnPe LhOe}

Unconstrained panels with 3 analytes, where 1.0E-6 >= 'model p-value' > 1.0E-7. Contains 2,289 panels of 260,130 total panels evaluated. : Lv{Fr(Fp Hq Hr Hu Hv Hw Hx Ih Ii In Io Ip Iq Ir Is It Iu Iv Jg Jh Ji Jk Jl Jm Jn Jp Jq Jr Js Lh Lj Lw Lx Ly Lz Ma Mb Mc Md Me Mf Mh Mi Mj Mk Ml Mn Mp Mr Mt Mu Mv Mw Mx My Mz Na Nb Nc Nd Ne Nf Nh Ni Nj Nk Nl Nn No Nq Nr Ns Nt Nu Nv Nw Ny Of Oh Oi Om On Oy Oz Pa Pb Pc Pd Pe Pf Pg Po Pz Qa Qb Qc Qd Qe) Mi(Et Fp Hr Hu Hv Hw Hx Ih Ii In Io Ip Iq Ir Is It Iv Jg Jh Ji Jk Jl Jm Jn Jp Jq Jr Lh Lj Lw Ly Lz Ma Mb Mc Md Me Mh Mj Mk Ml Mn Mp Mr Mt Mu Mv Mw Mx My Mz Na Nb Nc Nd Ne Nf Ni Nj Nk Nl Nn No Nr Ns Nu Nv Nw Ny Of Oi Ok Om On Oy Oz Pb Pc Pe Pf Pg Po Pz Qa Qb Qc Qd Qe) Oe(Et Fp Hq Hr Hu Hv Hw Ih Ii In Ip Ir Is It Iu Iv Jg Jh Ji Jk Jm Jn Jp Jq Jr Js Jt Lh Li Lj Lw Lx Ly Lz Ma Mb Mc Md Me Mh Mj Ml Mm Mn Mp Ms Mt Mu Mv Mw Mx My Na Nb Nc Ne Nf Nh Ni Nj Nk Nl Nm No Nq Ns Nt Nu Nv Ny Of Oh Oi Ok Om Oy Oz Pd Pf Pg Po Pz Qa Qb Qc Qd Qe) Jl(Fp Hq Hr Hu Hv Hw Hx Ih In Io Ip Iq Ir Is It Iv Jg Jh Jk Jm Jn Jp Jr Lh Lj Lw Lx Ly Lz Ma Mb Mc Md Me Mh Mj Mk Ml Mn Mp Mr Mt Mu Mv Mw My Mz Na Nb Nc Nd Ne Nf Ni Nj Nk Nl Nn No Nq Nr Ns Nt Nu Nw Om On Oy Oz Pb Pc Pe Pf Pg Po Qa Qb Qc Qd Qe) Lu(Et Fp Hr Hu Hv Hw Ih Ii In Io Ip Iq Ir Is It Iv Jg Jh Ji Jk Jm Jn Jq Js Jt Lh Li Lj Lw Lx Lz Ma Mc Md Me Mj Mk Mn Mp Mr Ms Mt Mu Mv Mw Mx My Nb Nc Ni Nj Nk Nl Nm No Nr Ns Nu Nv Ny Oh Ok Om On Oy Oz Pb Pe Pf Pg Po Pz Qa Qb Qc Qd Qe) Jo(Et Fp Hq Hr Hu Hv In Ip It Iv Jg Jh Ji Jm Jn Jq Js Jt Lj Lw Lx Ly Lz Ma Mc Md Me Mg Mh Ml Mm Mn Mp Ms Mt Mw Mx My Na Nc Ne Nf Ng Nh Ni Nj Nk Nl Nm Nq Ns Nt Nu Nv Ny Of Oh Oi Ok Om Oy Pa Qb Qc Qd Qe) Mf(Hr Hv Hw Ih Ii Io Iq Ir Is It Iu Iv Jk Jn Jp Jq Jr Jt Lh Li Lj Lw Lx Ly Lz Ma Mb Mg Mj Mk Ml Mm Mp Mq Mr Ms Mu Mv Nb Nc Nd Nf Ng Nh Nj Nk Nm Nn No Nq Nr Nw Of Oi Om On Pb Pc Pd Pe Pg Po Pz Qa Qb Qd) Mz(Et Fp Hv Hx Ii In Io Iq Iu Ji Jk Jm Jn Jp Jq Jr Js Li Ly Me Mg Mh Mj Mk Ml Mr Ms Mu Mv Mx Na Nb Nc Nd Ne Nf Ng Nh Ni Nm Nn Nr Nt Nw Of Oh Oi Ok On Oy Pa Pc Pd Pe Pf Pz Qa) Mq(Hr Hv Hw Ii Io Iq Ir Is Iu Jg Jk Jn Jp Jq Jr Jt Lh Li Lw Lx Ly Ma Mb Mg Mj Mk Ml Mm Mr Ms Mu Mv Mw My Nb Nc Nf Ng Nn No Nq Nr Of Oi Ok On Oy Pb Pc Pd Pe Pf Pg Po Qa Qb) Nd(Et Fp Hq Hx Ii Io Iq Iu Jm Jp Jq Jr Js Jt Li Ly Mh Mj Mk Ml Mm Mp Mr Ms Mv Na Nb Nc Ne Nf Ng Nh Nj Nk Nm Nn Nq Nr Ns Nt Nw Ny Of Oh Oi Ok On Oy Oz Pa Pb Pc Pd Pe Pf Pz) Pa(Hr Hu Hv Hw Hx Ih In Io Ip Ir Is It Iv Jg Jh Ji Jk Jp Jr Lh Lj Lw Lx Lz Ma Mb Mc Md Me Mj Mk Mn Mp Mt Mu Mv Mw My Nb Nc Ni Nk Nl No Nu Nw Om On Pb Pg Qa Qb Qc Qd Qe) Jj(Et Hq Hr Hw Ip Ir It Iv Jg Jh Jm Jn Jq Js Jt Lj Lw Ly Ma Mc Md Me Mm Mn Mp Mt Mx Na Nf Ng Ni Nj Nl No Ns Nt Nu Nv Nw Ny Of Oh Om Oz Pf Pz Qa Qb Qc Qd Qe) Hx(Et Fp Hq Ii Iq Iu Ji Jm Jn Jp Jq Jr Js Li Ly Me Mg Mh Mk Ml Mm Mr Ms Mx Na Nc Ne Nf Ng Nh Nm Nn Nr Nt Ny Of Oh Oi Ok Oy Pc Pd Pf Pz) Mg(Hr Hu Hv Ii Io Iq Ir Is Iu Jk Jr Lw Lx Ma Mb Mj Mk Ml Mn Mp Mr Mu Mv My Nb Nc No Nq Nr Nw Of Oi Om On Oy Pb Pc Pg Po) Mm(Hv Ih Io Iq Ir Is Jg Jh Jk Jr Lh Lx Ma Mj Mk Mr Mu Mv Mw Nb Nn No Nq Nr Nw Oi Pc Pd Pe Pg Po Qa Qb Qd Qe) Ng(Ii Io Iq Ir Is Iu Jg Jk Jp Jr Lh Li Ma Mb Mj Ml Mu Mv My Nb Nc Nq Nr Oi On Oy Pd Pe Pg Po) Nx(Et Fp Hq Hw In Ji Jm Jq Js Jt Lj Mc Md Mx Na Nf Ni Nj Nl Nm Ns Nt Ny Of Oh Ok Oz Pf Pz Qc) Nn(Hu Io Iq Iu Jh Jm Jp Jr Jt Li Mk Ml Mr Mv My Nc Nf Nh Nm Nq Nr Ns Of Oh Oy Pd Pe Pz) Jt(Ii Io Iq Is Jg Jr Lh Lx Ma Mb Mj Mk Mn Mu Mv My Nb No Nq Nw Om Pc Pg Po Qa) Ms(Ii Io Iq Jg Jp Jr Mb Mj Mk Mr Mu Mv Mw Nb No Nr Nw Oi On Oy Pb Pd Pe) Iu(Ih Io Iq Ir Is Jn Jp Jr Lh Mj Mk Mr Nb Nc Nr Nw On Pc Pd Pe Pg Qb) Jp(Et Iq Jg Li Mk Ml Mr Nc Nh Nm Nr Ny Of Oh Oi Ok Pc Pd Pe Pf Pz) Oi(Ii Io Iq Is Jk Jr Mj Mk Mr Mu Mv Nb Nc Nq Nr Nw On Pb Pd Pe) Mr(Hr Ii Jr Js Li Me Mh Ml Mx Na Nf Nh Nt Of Ok Pd) Pe(Fp Ii Js Li Me Mh Ml Mx Na Nf Nh Nm Nt Of Pf) Pd(Hw Io Iq Jr Li Mj Mk Nb Nr Nw Om Pb Pc

Figure 16 Continued

Pg) Nr(Ii Js Li Me Mh Ml Mx Na Nf Nh Nt Of) Pc(Hu Jh Li Mv My Nc Nf Nh Nq Ns Of Oy) Mk(Ii Jr Li Me Mh Mx Na Nf Nh Nt Of) On(Ji Li Nf Nm Nt Of Ok) Js(Hw Iv Jr Lh Mj Pb) Nw(Ji Jq Nh Nm Ok) Ml(Hw Is Jr Pb) Nh(Mu Mv Nc) Is(Jn Jq Mx) Nm(Lw Om) Nf(Lh Nb) Jr(Jn Jq) NtLh McHw MjMx MuOf NcNe} aA{Oe(Et Fp Fr Hq Hr Hu Hv Hw Hx Ih Ii In Io Ip Iq Ir Is It Iu Iv Jg Jh Ji Jj Jk Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Oh Oi Ok Om On Oy Oz Pa Pb Pd Pe Pf Pg Po Pz Qa Qb Qc Qd Qe) Jt(Et Fp Fr Hr Hu Hv Hw Ih Ii In Io Ip Iq Ir Is It Iu Iv Jg Jh Ji Jj Jk Jm Jn Jo Jp Jq Jr Js Lh Li Lj Lu Lx Ly Lz Ma Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nm Nn No Nq Nr Ns Nt Nu Nv Nw Nx Of Oh Oi Ok Om On Oy Pb Pd Po Qa Qb Qc Qd Qe) Og(Et Fp Fr Hq Hr Hu Hv Hw Ii In Io Ip Ir Is Iv Jh Ji Jk Jm Jp Jq Lh Lj Lu Lx Lz Ma Mb Mc Md Me Mf Mh Mj Mk Mn Mp Mr Mu Mw My Na Nb Nc Nd Ni Nk Nl Nm Nn No Nr Ns Nt Nu Nv Nw Nx Ny Of Ok Om On Oy Pe Po Pz Qa Qc Qd Qe) Jl(Et Hv Ih Ii Iu Ji Jj Jn Jo Jq Jr Js Li Ly Mf Mg Mi Mq Ms Mt Mx Na Ne Nf Ng Nh Nj Nm Nn Nt Nv Nx Ny Of Oi Pa Pc Pd Pf Pz) Pa(Hq Hv Ih Iu Ji Jj Jn Jo Jq Jr Li Lj Ly Lz Md Mg Mh Mm Mr Ms Mt Mx Na Ne Nf Ng Nh Nj Nn No Nt Nx Ny Of Oh Oi Ok Pc Pf) Iq(Fr Hx Ir Is Iu Jg Jj Jk Jn Jo Jr Lh Lw Ma Mf Mm Ms Mv Mz Nd Ne Ng Nh Nj Nn Nx Oh Oi Pc Pe Pg Qa Qb) Mi(Hq Ih Iu Ji Jj Jn Jo Jq Jr Js Ly Mg Mm Mr Ms Mt Mx Ne Nf Ng Nh Nj Nm Nt Nx Ny Of Oh Oi Ok Pc Pd) Ms(Fr Hx Iu Jg Jj Jn Jo Jr Js Lw Ly Mg Mm Mv Mw Mz Ne Ng Nh Ni Nj Nn Nx Oi Pc Pg) Pg(Ih Ii Iu Jj Jq Mg Mm Mx Na Ne Nf Ng Nh Nj Nt Nx Ny Of Oh Oi Ok Pd Pf) Nj(Fr Iu Jj Jo Jq Js Me Mf Mm Mq Mz Nd Ne Ng Nh Nn Nx Oh Oi Pc) Pc(Iu Jj Jo Js Ly Mg Mm Mt Mx My Ng Nh Nq Ns Nx Of Oh Pd) Jj(Hu Hx Jk Jm Jq Jr Lh Ly Mm Mv Ne Nh Oh Pe) Ly(Iu Jo Mm Na Ng Nh Nx Oi) Mm(Fr Jp Lh Lx Ma Mz Nh) Jo(Hu Hx Jk Lh Lw Nh Pe) Fr(Iu Ng Nh Nx Oh) Lw(Ji Nh Nm Nx Ok) Js(Hx In Jr Nn Pe) Pd(Nn Pe Po) Mz(Jq Oh) Ne(Nc Oi) Nh(Iu Oi) Jr(Jn Oh) NnMx NgJk IuQb} Pa[Pd(Hr Hu Hv Hw Hx Iq Is Iu Iv Jg Ji Jp Jr Js Jt Lj Lu Lw Lx Lz Ma Mf Mh Mk Mp Mr Ms Mt Mz Na Nc Nf Ng Ni Nj Nw Om On Pb Pc Pe Pg Po) Jj(Fp Hu Iq Jk Jl Jn Jo Jr Js Jt Lj Lu Ly Mf Mh Mi Ml Ms Mx Nh Oe Pc Pf Pg) Pe(Hq Hr Ii Iq Iu Jl Jm Jp Jr Js Jt Lu Ma Ms Mu Mv Mz Nf Ng Ni Nj Nw Nx Oi) Jo(Fr Hu Iq Jl Js Lh Lw Ly Mh Mi Mk Ml Ms Nf Nj Nn On Pc Pf Pg) Js(Fr Hq Is Ji Jp Jr Lh Mz Nn Nw Oe Og) Oe(Fr Hq Iq Jl Na Nf Ng On Pc) Og(Iq Jl Jt Na Ng Nj Pc Pf) Ng(Fr Jk Jl Lj Mi Mu) Jt(Fr Hq Mi Mz Nf On) Jl(Mm Nx Oh Pf) Mi(Hq Iq) MsPc} Mi{Pd(Fr Hq Hu Hv Hw Hx Ii In Iq Iu Iv Jg Jj Jk Jl Jp Jr Js Lh Li Lu Lx Ly Md Mj Mk Mr Ms Mu Mv Mz Nb Nc Ne Nj Nk Nq Nr Nt Oe On Oy Oz Pb Pf Qa Qb Qe) Hq(Iq Iu Ji Jj Jl Jo Jq Lu Mg Mq Nd Nf Ng Nj Nm No Nx Ok Pg) Jo(Hx Ii Lh Lu Ly Mk Mr Ms Nj Nr Og Pc Pe Pg) Jt(Is Jl Jp Lh Mk Mr Mz Nr On Pc) Js(Hx In Jl Jr Lh Ms Mz Qa Qb) Og(Hx Jl Mg Nd Nr Nt On Pb Pc) Jl(Mm Ms Ng Nq Nt Oh) Pc(Mg Ms Ng Nx Oe) Jj(Lu Ly Ms Nj) Nt(Jr Ng Nj) Oe(Nq Nr On) Mg(Fr Lu) Ng(Jk Pg) NqMu MmJp MsNe NxOm} Jl{Og(Hu Hx Ii Iq Is Iu Jj Jo Jp Js Li Lu Lw Ly Mg Mj Mk Mq Mr Ms Nb Ne Ng Nh Nj Nm Nn Nr Nw Nx Ny Oe Of Oh Oi Ok Om On Pb Pc Pd Pe Pz) Jt(Ii Is Jp Lh Lw Mj Mk Mm Mr Ms Nr Oe Om On Pc Pe Pg) Mm(Ii Iq Iu Jj Jp Ms Ne Ng Nh Nx Oe Oi) Oe(Ii Jj Lu Mk Mr Ms Nr Nx On Pc) Jj(Ms Nx Oh Pg) Pc(Ms Ng) Pd(Lh Pe) JoPg} On{Oe(Fr Jj Jo Jt Ms Nf Nx Og Ok Pd) Og(Jj Jo Jt Ms Nf Ng Ok Pd) Ok(Ms Ng Nx) JoPg JpJt NxOm} Pd{Pe(Fr Lh Mu Mv Oe Pc Pg) Lh(Jj Jo Jt Og) JjPg} Og{Hx(Jj Pc) IsJs JjPg JoLh} Fr{Mk(Ng Oe) NrOe MgPg} Jo{Pg(Jj Mr) JsLh} NrMuOe MgJjPg NgJkPc JpJtPe

Unconstrained panels with 3 analytes, where 1.0E-5 >= 'model p-value' > 1.0E-6. Contains 11,958 panels of 260,130 total panels evaluated. :
aA{Lu(Et Fp Fr Hq Hr Hu Hv Hw Hx Ih Ii In Io Ip Iq Ir Is It Iu Iv Jg Jh Ji Jj Jk Jl Jm Jn Jo Jp Jq Jr Js Lh Li Lj Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Pz Qa Qb Qc Qd Qe) Ml(Et Fp Fr Hq Hr Hu Hv Hw Hx Ih Ii In Io Ip Iq Ir Is It Iu Iv Jg Jh Ji Jj Jk Jl Jm Jn Jo Jp Jq Jr Js Lh Li Lj Lw Lx Ly Lz Ma Mb Mc Md Me Mf Mg Mh Mi Mj Mk Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Pz Qa Qb Qc Qd Qe) Nb(Et Fp Fr Hq Hr Hu Hv Hw Hx Ih Ii In Io Ip Iq Ir Is It Iu Iv Jg Jh Ji Jj Jk Jl Jm Jn Jo Jp Jq Jr Js Lh Li Lj Lw Lx Ly Lz Ma Mb Mc Md Me Mf Mg Mh Mi Mj Mk Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Pz Qa Qb Qc Qd Qe) It(Et Fp Fr Hq Hr Hu Hv Hw Hx Ih Ii In Io Ip Iq Ir Is Iu Iv Jg Jh Ji Jj Jk Jl Jm Jn Jo Jp Jq Jr Js Lh Li Lj Lw Lx Ly Lz Ma Mb Mc Md Me Mf Mg Mh Mi Mj Mk Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Pz Qa Qb Qc Qd Qe) Pz(Et Fp Fr Hq Hr Hu Hv Hw Hx Ih Ii In Io Ip Iq Ir Is Iu Iv Jg Jh Ji Jj Jk Jm Jn Jo Jp Jq Jr Js Jt Lh Li Lj Lw Lx Ly Lz Ma Mb Mc Md Me Mf Mg Mh Mi Mj Mk Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Qa Qb Qc Qd Qe) Nc(Et Fp Fr Hq Hr Hu Hv Hw Hx Ih Ii In Io Ip Iq Ir Is Iu Iv Jg Jh Ji Jj Jk Jl Jm Jn Jo Jp Jq Jr Js Lh Li Lj Lw Lx Ly Lz Ma Mb Mc Md Me Mf Mg Mh Mi Mj Mk Mm Mn Mp Mq Mr Ms Mt Mu Mv Mw Mx My Mz Na Nd Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Qa Qb Qc Qd Qe) Mq(Et Fp Fr Hq Hr Hu Hv Hw Hx Ih Ii In Io Ip Iq Ir Is Iu Iv Jg Jh Ji Jj Jk Jm Jn Jo Jp Jq Jr Js Lh Li Lj Lw Lx Ly Lz Ma Mb Mc Md Me Mf Mg Mh Mi Mj Mk Mm Mn Mp Mr Ms Mt Mu Mv Mw Mx My Mz Na Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Qa Qb Qc Qd Qe) Hu(Et Fp Fr Hq Hr Hv Hw Hx Ih Ii In Io Ip Iq Ir Is Iu Iv Jg Jh Ji Jk Jl Jm Jn Jp Jq Jr Js Lh Li Lj Lw Lx Ly Lz Ma Mb Mc Md Me Mf Mg Mh Mi Mj Mk Mm Mn Mp Mr Ms Mt Mu Mv Mw Mx My Mz Na Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Qa Qb Qc Qd Qe) Qb(Et Fp Fr Hq Hr Hv Hw Hx Ih Ii In Io Ip Ir Is Iv Jg Jh Ji Jj Jk Jl Jm Jn Jo Jp Jq Jr Js Lh Li Lj Lw Lx Ly Lz Ma Mb Mc Md Me Mf Mg Mh Mi Mj Mk Mm Mn Mp Mr Ms Mt Mu Mv Mw Mx My Mz Na Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Qa Qc Qd Qe) Li(Et Fp Fr Hq Hr Hv Hw Hx Ih Ii In Io Ip Iq Ir Is Iu Iv Jg Jh Ji Jj Jk Jm Jn Jo Jp Jq Jr Js Lh Lj Lw Lx Ly Lz Ma Mb Mc Md Me Mf Mg Mh Mi Mj Mk Mm Mn Mp Mr Ms Mt Mu Mv Mw Mx My Mz Na Nd Ne Nf Ng Nh Ni Nj Nk Nl Nm Nn No Nq Nr Ns Nt Nu Nv Nw Nx Ny Of Oh Oi Ok Om On Oy Oz Pb Pc Pd Pe Pf Pg Po Qa Qc Qd Qe) Ns(Et Fp Fr Hq Hr Hv Hw Hx Ih Ii In Io Iq Ir Is Iu Iv Jg Jh Ji Jj Jk Jl Jm Jn Jo Jp Jq Jr Js Lh Lj Lw Lx Ly Lz Ma Mb Mc Md Me Mf Mg Mh Mi Mj Mk Mm Mn Mp Mr Ms Mt Mu Mv Mw Mx My Mz Na Nd Ne Nf Ng Nh Ni Nj Nk Nl Nm Nn No Nq Nr Nt Nu Nv Nw Nx Ny Of Oh Oi Ok Om On Oy Oz Pa Pb Pc Pd Pe Pf Pg Po Qa Qc Qe) Mf(Et Fp Fr Hq Hr Hv Hw Hx Ih Ii In Io Ip Ir Is Iu Iv Jg Jh Ji Jj Jk Jm Jn Jo Jp Jq Jr Js Lh Lj Lw Lx Ly Lz Ma Mb Mc Md Me Mg Mh Mi Mj Mk Mm Mn Mp Mr Ms Mt Mu Mv Mw Mx My Mz Na Nd Ne Nf Ng Nh Ni Nj Nk Nl Nm Nn No Nq Nr Nt Nu Nv Nw Nx Ny Of Oh Oi Ok Om On Oy Oz Pa Pb Pc Pd Pe Pf Pg Po Qa Qc Qd Qe) Mv(Et Fp Fr Hq Hr Hv Hw Hx Ih Ii In Io Ip Ir Is Iu Iv Jg Jh Ji Jk Jl Jm Jn Jo Jp Jq Jr Js Lh Lj Lw Lx Ly Lz Ma Mb Mc Md Me Mg Mh Mi Mj Mk Mm Mn Mp Mr Mt Mu Mw Mx My Mz Na Nd Ne Nf Ng Nh Ni Nj Nk Nl Nm Nn No Nq Nr Nt Nu Nv Nw Nx Ny Of Oh Oi Ok Om On Oy Oz Pa Pb Pc Pd Pe Pf Pg Po Qa Qc Qd Qe) Ny(Et Fp Fr Hq Hr Hv Hw Hx Ih Ii In Io Ip Iq Ir Is Iu Iv Jg Jh Ji Jj Jk Jm Jn Jo Jp Jq Jr Js Jt Lh Lj Lw Lx Ly Lz Ma Mb Mc Md Me Mg Mh Mj Mk Mm Mn Mp Mr Ms Mt Mu Mw Mx My Mz Na Nd Ne Nf Ng Nh Ni Nj Nk Nl Nm Nn No Nq Nr Nt Nu Nv Nw Nx Of Oh Oi Ok Om On Oy Oz Pb Pc Pd Pe Pf Po Qa Qc Qd Qe) Mt(Et Fp Fr Hq Hr Hv Hw Hx Ih Ii In Io Ip Iq Ir Is

Mu Mw My Ni Nl Nm No Nq Nr Nt Nu Nv Nw Om On Oy Oz Pb Po Qc Qd Qe) Jl(Fp Hq Hr Hw In Io Ip Ir Is Iv Jg Jh Jm Jp Lh Lj Lx Lz Ma Mb Mc Md Me Mh Mj Mk Mn Mp Mr Mu Mw My Nd Ni Nl No Nq Nr Nu Nw Om On Oy Oz Pb Po Qa Qc Qd Qe) Nm(Hq Hv Hw Ii In Ip Ir Is Iv Jg Ji Jm Jp Lh Lj Lx Ma Mb Mc Md Me Mh Mj Mk Mn Mp Mr Mu Mw My Nd Ni Nl Nq Nr Nt Nu Nw Om On Oy Oz Pa Pb Po Qa Qd Qe) Pa(Et Fp Hr Hw Ii In Io Ip Ir Is Iv Jg Jh Jm Jp Lh Lx Ma Mb Mc Me Mj Mk Mn Mp Mu Mw My Nd Ni Nl Nq Nr Nu Nv Nw Om On Oy Oz Pb Po Qa Qc Qd Qe) Pb(Et Fp Hq Hr Hv Hw Ii In Io Ir Is Iv Jg Jh Ji Jp Lh Lj Lx Ma Mb Mc Md Me Mh Mj Mk Mn Mr Mu Mw My Nd Ni Nl Nq Nt Nu Nw On Oy Po Qa Qe) Ji(Hq Hv Ii In Ip Ir Is Iv Jg Jm Jp Lh Lx Ma Mb Md Me Mj Mk Mn Mr Mu Mw My Nd Ni Nl Nq Nr Nt Nu Nw Om On Oy Oz Po Qa Qc Qd Qe) Lx(Et Fp Hq Hv Hw Ii In Io Ir Jg Jp Lh Lj Lz Ma Mb Mc Md Me Mh Mj Mk Mn Mp Mr Mu My Nd Ni Nl No Nq Nr Nt Nv On Oy Oz Qe) Jg(Et Fp Hq Hr Hv Hw Ii In Io Ir Iv Jh Jp Lh Lj Ma Mb Mc Md Me Mh Mj Mn Mr Mu My Nd Ni Nl No Nq Nr Nt Nv Oy Oz Qa Qe) Hv(Et Fp Hq Hw Ii In Ir Iv Jp Lh Lj Ma Mb Md Me Mh Mj Mk Mn Mr Mu My Nd Ni Nl Nq Nr Nt Nu Om On Oy Oz Po Qa Qe) Me(Et Hq Hw Ii In Ir Is Iv Jp Lh Lj Ma Mb Md Mj Mk Mn Mu Mw My Nd Ni Nl Nq Nr Nt Nu Om On Oy Oz Po Qa Qe) Nt(Ii In Ip Ir Is Iv Jp Lh Ma Mb Md Mj Mk Mn Mp Mr Mu Mw My Nd Ni Nr Nu Om On Oy Oz Po Qa Qe) Ir(Et Fp Ii In Is Iv Jp Lh Lj Ma Mb Md Mh Mj Mk Mn Mr Mu My Nd Ni Nl Nr Om On Oz Po Qa) Md(Ii In Is Iv Jp Lh Lj Ma Mb Mj Mn Mp Mu Mw My Nd Ni Nl Nu Nw Om On Oz Po Qa Qe) Nd(Et Hq Hw Ii In Iv Jp Lh Lj Ma Mb Mh Mj Mk Mn Mr Mu My Ni Nl Nq Nu On Oz Qa) Ma(Et Fp Hq Ii In Io Jp Lh Lj Mb Mh Mj Mk Mr Mu Ni Nl No Nq Nr Nv On Oz) Jp(Et Fp Hq Ii In Io Lh Lj Mb Mh Mj Mk Mr Mu Ni Nl Nq Nr Nv On Oz) Ii(In Is Iv Jm Lh Mb Mj Mk Mn Mu Mw My Ni Nr On Oz Po Qa Qe) Lh(Et Fp Hq Hr Hw Lj Mb Mh Mr Mu Ni Nl Nq Nr Nv Oz) Nl(In Iv Jt Mb Mj Mk Mp Mr Nr On Oy Oz Po) Ni(Et In Iv Mb Mj Mk Mn Mr Mu Nr On Oz) Et(Ip Is Iv Mj Mn Nw On Po Qa Qe) Mb(Jt Lj Mh Mj Mn Mu My On Oz Qa) Mj(Fp Hq Hr Lj Mh Mr Nq Oz) Mk(Hq Hr Io Iv Lj Lz Mh) On(Hr Lj Mh Mr No Oz) Oz(Jt Mn Mu My) Po(Lj Mh Mr) Nq(Mp Mu Mw) Nr(Hr Lj Mh) Mr(Hr Qa) Hq(Jt Mp) McJt MuIn MwMy] Lv(Lz(Et Fp Hq Hr Hu Hv Hw Hx Ih Ii In Io Ip Iq Ir Is It Iu Iv Jg Jh Ji Jk Jm Jn Jp Jq Jr Js Jt Lh Li Lj Lw Lx Ly Ma Mb Mc Md Me Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Ny Of Oh Oi Ok Om On Oy Oz Pb Pc Pd Pe Pf Pg Po Pz Qa Qb Qc Qd Qe) Lw(Et Fp Hq Hr Hu Hv Hw Hx Ih Ii In Io Ip Iq Ir Is It Iu Iv Jg Jh Ji Jk Jm Jn Jp Jq Jr Js Jt Lh Li Lj Lx Ly Ma Mb Mc Md Me Mh Mj Mk Ml Mm Mn Mp Mr Ms Mt Mu Mv Mw Mx My Mz Na Nb Nc Nd Ne Nf Ng Nh Ni Nj Nk Nl Nn No Nq Nr Ns Nt Nu Nv Nw Ny Of Oh Oi Ok Om On Oy Oz Pb Pc Pd Pe Pf Pg Po Pz Qa Qb Qc Qd Qe) Qb(Et Fp Hq Hr Hu Hv Hw Hx Ih Ii In Io Ip Iq Ir Is It Iv Jg Jh Ji Jk Jm Jn Jp Jq Jr Js Jt Lh Li Lj Lx Ly Ma Mb Mc Md Me Mg Mh Mj Mk Ml Mn Mp Mr Ms Mt Mu Mv Mw Mx My Mz Na Nb Nc Nd Ne Nf Ng Nh Ni Nj Nk Nl Nm Nn No Nq Nr Ns Nt Nu Nv Nw Ny Of Oh Oi Ok Om On Oy Oz Pb Pc Pd Pe Pf Pg Po Pz Qa Qc Qd Qe) Ly(Et Fp Hq Hr Hu Hv Hw Ih Ii In Io Ip Iq Ir Is It Iu Iv Jg Jh Ji Jk Jm Jn Jp Jq Jr Js Jt Lh Li Lj Lx Ma Mb Mc Md Me Mg Mh Mj Mk Ml Mm Mn Mp Mr Ms Mt Mu Mv Mw Mx My Na Nb Nc Ne Nf Ng Nh Ni Nj Nk Nl Nm Nn No Nq Nr Ns Nt Nu Nv Nw Ny Of Oh Oi Ok Om On Oy Oz Pb Pc Pd Pe Pf Pg Po Pz Qa Qc Qd Qe) Hv(Et Fp Hq Hr Hu Hw Hx Ih Ii In Io Ip Iq Ir Is It Iu Iv Jg Jh Ji Jk Jm Jn Jp Jq Jr Js Jt Lh Li Lj Lx Ma Mb Mc Md Me Mh Mj Mk Ml Mn Mp Mr Ms Mt Mu Mv Mw Mx My Na Nb Nc Nd Ne Nf Ng Nh Ni Nj Nk Nl Nm Nn No Nq Nr Ns Nt Nu Nv Nw Ny Of Oh Oi Ok Om On Oy Oz Pb Pc Pd Pe Pf Pg Po Pz Qa Qc Qd Qe) No(Et Fp Hq Hr Hu Hw Hx Ih Ii In Io Ip Iq Ir Is It Iu Iv Jg Jh Ji Jk Jm Jn Jp Jq Jr Js Lh Li Lj Lx Ma Mb Mc Md Me Mh Mj Mk Ml Mn Mp Mr Mt Mu Mv Mw Mx My Mz Na Nb Nc Nd Ne Nf Ng Nh Ni Nj Nk Nl Nm Nn Nq Nr Ns Nt Nu Nv Nw Ny Of Oh Oi Ok Om On Oy Oz Pb Pc Pd Pe Pf Pg Po Pz Qa Qc Qd Qe) Mb(Et Fp Hq Hr Hu Hw Hx Ih Ii In Io Ip Iq Ir Is It Iu Iv Jg Jh Ji Jk Jm Jn Jp Jq Jr Js Lh Li Lj Lx Ma Mc Md Me Mh Mj Mk Ml Mm Mn Mp Mr Mt Mu Mv Mw Mx My Mz Na Nb Nc Nd Ne Nf Nh Ni Nj Nk Nl Nm Nn Nq Nr Ns Nt Nu Nv Nw Ny Of Oh Oi Ok Om On Oy Oz Pb Pc Pd Pe Pf Pg Po Pz Qa Qc Qd Qe) Po(Et Fp Hq Hr Hu Hw Hx Ih Ii In Io Ip Iq Ir Is It Iu Iv Jg Jh Ji Jk Jm Jn Jp Jq Jr Js Lh Li Lj Lx Ma Mc Md Me Mh Mj Mk Ml Mn Mp Mr Ms Mt Mu Mv Mw Mx My Mz Na Nb Nc Nd Ne Nf Nh Ni Nj Nk Nl Nm Nn Nq Nr Ns Nt Nu Nv Nw Ny Of Oh Oi Ok Om On Oy Oz Pb Pc Pe Pf Pg Pz Qa Qc Qd Qe) Ir(Et Fp Hq Hr Hu Hw Hx Ih Ii In Io Ip Iq Is It Iv Jg Jh Ji Jk Jm Jn Jp Jq Jr Js Lh Li Lj Lx Ma Mc Md Me Mh Mj Mk Ml Mn Mp Mr Ms Mt Mu Mv Mw Mx My Mz Na Nb Nc Nd Ne Nf Nh Ni Nj Nk Nl Nm Nn Nq Nr Ns Nt Nu Nv Nw Ny Of Oh Oi Ok Om On Oy Oz Pb Pc Pd Pe Pf Pg Pz Qa Qc Qd Qe) Jk(Et Fp Hq Hr Hu Hw Hx Ih Ii In Io Ip Iq Is It Iu Iv Jg Jh Ji Jm Jn Jp Jq Jr Js Jt Lh Li Lj Lx Ma Mc Md Me Mh Mj Mk Ml Mn Mp Mr Ms Mt Mu Mv Mw Mx My Na Nb Nc Nd Ne Nf Nh Ni Nj Nk Nl Nm Nn Nq Nr Ns Nt Nu Nv Nw Ny Of Oh Oi Ok Om On Oy Oz Pb Pc Pd Pe Pf Pg Pz Qa Qc Qd Qe) Pg(Et Fp Hq Hr Hu Hw Hx Ih Ii In Io Ip Iq Is It Iv Jg Jh Ji Jm Jn Jp Jq Jr Js Lh Li Lj Lx Ma Mc Md Me Mh Mj Mk Ml Mn Mp Mr Ms Mt Mu Mv Mw Mx My Mz Na Nb Nc Nd Ne Nf Nh Ni Nj Nk Nl Nm Nn Nq Nr Ns Nt Nu Nv Nw Ny Of Oh Oi Ok Om On Oy Oz Pb Pc Pe Pf Pz Qa Qc Qd Qe) Nq(Et Fp Hq Hr Hu Hw Hx Ih Ii In Io Ip Iq Is It Iu Iv Jg Jh Ji Jm Jn Jp Jq Jr Js Lh Li Lj Lx Ma Mc Md Me Mh Mj Mk Ml Mn Mp Mr Ms Mt Mu Mv Mw Mx My Mz Na Nb Nc Ne Nf Nh Ni Nj Nk Nl Nm Nn Nr Ns Nt Nu Nv Nw Ny Of Oh Oi Ok Om On Oy Oz Pb Pc Pd Pe Pf Pz Qa Qc Qd Qe) Pb(Et Fp Hq Hr Hu Hw Hx Ih Ii In Io Ip Iq Is It Iu Iv Jg Jh Ji Jm Jn Jp Jq Jr Jt Lh Li Lj Lx Ma Mc Md Me Mh Mj Mk Mm Mn Mp Mr Mt Mu Mv Mw Mx My Mz Na Nb Nc Ne Nf Nh Ni Nj Nk Nl Nm Nn Nr Ns Nt Nu Nv Nw Ny Of Oh Ok Om On Oy Oz Pc Pe Pf Pz Qa Qc Qd Qe) Mu(Et Fp Hq Hr Hu Hw Hx Ih Ii In Io Ip Iq Is It Iu Iv Jg Jh Ji Jm Jn Jp Jq Jr Js Lh Li Lj Lx Ma Mc Md Me Mh Mj Mk Ml Mn Mp Mr Mt Mv Mw Mx My Na Nb Nc Nd Ne Nf Ni Nj Nk Nl Nm Nn Nr Ns Nt Nu Nv Nw Ny Oh Ok Om On Oy Oz Pc Pd Pe Pf Pz Qa Qc Qd Qe) Lh(Et Fp Hq Hr Hu Hw Hx Ih Ii In Io Ip Is It Iv Jg Jh Ji Jm Jn Jp Jq Jr Li Lj Lx Ma Mc Md Me Mh Mj Mk Ml Mn Mp Mr Ms Mt Mv Mw Mx My Mz Na Nb Nc Nd Ne Nh Ni Nj Nk Nl Nm Nn Nr Ns Nu Nv Nw Ny Of Oh Oi Ok Om On Oy Oz Pc Pe Pf Pz Qa Qc Qd Qe) Mv(Et Fp Hq Hr Hu Hw Hx Ih Ii In Io Ip Iq Is It Iu Iv Jg Jh Ji Jm Jn Jp Jq Jr Js Li Lj Lx Ma Mc Md Me Mh Mj Mk Ml Mn Mp Mr Mt Mw Mx My Na Nb Nc Ne Nf Ni Nj Nk Nl Nm Nr Ns Nt Nu Nv Nw Ny Of Oh Ok Om On Oy Oz Pd Pe Pf Pz Qa Qc Qd Qe) My(Et Fp Hq Hr Hu Hx Ih Ii Io Ip Iq Is It Iu Iv Jg Jh Ji Jm Jn Jp Jq Jr Js Li Lj Lx Ma Mc Me Mf Mh Mj Mk Ml Mm Mn Mp Mr Ms Mw Mx Mz Na Nb Nc Nd Ne Nf Nh Ni Nj Nk Nm Nr Ns Nt Nu Nw Ny Of Oh Oi Ok Om On Oy Oz Pd Pe Pf Pz Qa Qc Qd) Nb(Et Fp Hq Hr Hu Hw Hx Ih Ii In Io Ip Iq Is It Iv Jg Jh Ji Jm Jn Jp Jq Jr Js Li Lj Lx Ma Mc Md Me Mh Mj Mk Ml Mn Mp Mr Mt Mw Mx Na Nc Ne Nh Ni Nj Nk Nl Nm Nn Nr Ns Nt Nu Nv Nw Ny Of Oh Ok Om On Oy Oz Pc Pe Pf Pz Qa Qc Qd Qe) Nh(Et Fp Hr Hu Hw Hx Ii In Io Ip Iq Is It Iu Iv Jg Jh Ji Jm Jn Jq Jr Js Jt Li Lj Lx Ma Mc Md Me Mg Mh Mj Ml Mm Mn Mp Mq Ms Mt Mw Mx Na Ne Nf Ng Ni Nj Nk Nl Nm Ns Nt Nu Nv Ny Of Oh Oi Ok Om On Oy Oz Pd Pz Qa Qc Qd Qe) Io(Et Fp Hq Hr Hu Hw Hx Ih Ii In Ip Iq Is It Iv Jg Jh Ji Jm Jn Jp Jq Jr Js Li Lj Lx Ma Mc Md Me Mh Mj Mk Ml Mn Mp Mr Mt Mw Mx Na Nc Ne Nf Ni Nj Nk Nl Nm Nr Ns Nt Nu Nv Nw Ny Of Oh Ok Om On Oy Oz Pc Pe Pf Pz Qa Qc Qd Qe) Is(Et Fp Hq Hr Hu Hw Hx Ih Ii In Ip Iq It Iv Jg Jh Ji Jm Jp Jr Li Lj Lx Ma Mc Md Me Mh Mj Mk Mn Mp Mr Ms Mt Mw Mz Na Nc Nd Ne Nf Ni Nj Nk Nl Nm Nn Nr Ns Nt Nu Nv Nw Ny Of Oh Ok Om On Oy Oz Pc Pd Pe Pf Pz Qa Qc Qd Qe) Mj(Et Fp Hq Hr Hu Hw Hx Ih Ii In Ip Iq It Iv Jg Jh Ji Jm Jn Jp Jq Jr Li Lj Lx Ma Mc Md Me Mh Mk Ml Mn Mp Mr Mt Mw Na Nc Ne Nf Ni Nj Nk Nl Nm Nn Nr Ns Nt Nu Nv Nw Ny Of Oh Ok Om On Oy Oz Pc Pe Pf Pz Qa Qc Qd Qe) Ml(Et Fp Hq Hr Hu Ih Ii In Ip Iq It Iu Iv Jg Jh Ji Jm Jn Jq Js Jt Li Lj Lx Ma Mc Md Me Mh Mk Mm Mn Mp Ms Mt Mw Mx Na Nc Ne Nf Ni Nj Nk Nl Nm Ns Nt Nu Nv Nw Ny Of Oh Oi Ok Om On Oy Oz Pc Pd Pf Pz Qa Qc Qd Qe) Nc(Et Fp Hq Hr Hu Hw Ih Ii In Ip Iq It Iv Jg Jh Ji Jm Jn Jq Jr Js Jt Li Lj Lx Ma Mc Md Me Mh Mk Mm Mn Mp Mr Ms Mt Mw Mx Na Nf Ni Nj Nk Nm Nr Ns Nt Nu Nv Nw Ny Of Oh Ok Om On Oy Oz Pd Pe Pf Pz Qa Qc Qd Qe) Of(Et Fp Hq Hr Hu Hw Ih Ii In Ip Iq It Iu Iv Jg Jh Ji Jm Jn Jq Jr Js Jt Li Lj Lx Ma Mc Md Me Mh Mm Mn Mp Ms Mt Mw Mx Na Ne

Figure 16 Continued

Nf Ng Ni Nj Nk Nl Nm Ns Nt Nu Nv Nw Ny Oh Oi Ok Om Oy Oz Pd Pf Pz Qa Qc Qd Qe) Iq(Et Fp Hq Hr Hu Hw Ih Ii In Ip It Iv Jg Jh Ji Jm Jn Jq Jr Js Li Lj Lx Ma Mc Md Me Mh Mk Mn Mp Mr Mt Mw Mx Na Ne Nf Ni Nj Nk Nl Nm Nr Ns Nt Nu Nv Nw Ny Oh Ok Om On Oy Oz Pc Pe Pf Pz Qa Qc Qd Qe) Li(Et Fp Hq Hr Hu Hw Ih Ii In Ip It Iu Iv Jg Jh Ji Jm Jn Jq Jr Js Jt Lj Lx Ma Mc Md Me Mg Mh Mm Mn Mp Ms Mt Mw Mx Na Ne Nf Ni Nj Nk Nl Nm Ns Nt Nu Nv Nw Ny Oh Oi Ok Om Oy Oz Pf Pz Qa Qc Qd Qe) Nw(Et Fp Hq Hr Hu Hw Hx Ih Ii In Ip It Iv Jg Jh Jm Jn Jp Jr Js Lj Lx Ma Mc Md Me Mh Mk Mn Mp Mr Mt Mw Mx Na Ne Nf Ng Ni Nj Nk Nl Nn Nr Ns Nt Nu Nv Ny Oh Om On Oy Oz Pc Pe Pf Pz Qa Qc Qd Qe) Nm(Et Fp Hq Hr Hu Hw Ih Ii In Ip It Iu Iv Jg Jh Ji Jn Jq Jr Js Jt Lj Lx Ma Mc Md Me Mg Mh Mk Mm Mn Mp Mq Mr Ms Mt Mw Na Ne Nf Ng Nk Nr Ns Nu Nv Oh Oi Ok Oy Oz Pc Pd Pf Pz Qa Qc Qd Qe) Ne(Fp Hr Hu Ih Ii Ip It Iu Iv Jg Jh Jn Jp Jq Jr Js Jt Lj Lx Ma Me Mf Mg Mh Mk Mm Mn Mp Mq Mr Ms Mt Mw Mx Na Nf Ng Ni Nj Nk Nl Nn Nr Ns Nu Oh Oi Om On Oy Oz Pc Pd Pe Pf Pz Qa Qd Qe) Ii(Et Fp Hq Hr Hu Hw Ih In Ip It Iu Iv Jg Jh Ji Jm Jn Jp Jq Jr Js Lj Lx Ma Mc Me Mh Mm Mn Mp Mt Mw Mx Na Nf Ni Nj Nk Nl Nn Ns Nt Nu Ny Oh Ok Om On Oy Oz Pc Pd Pf Pz Qa Qc Qd Qe) Jn(Et Fp Hq Hu Hw In Ip It Iv Jg Ji Jm Jp Jq Js Jt Lj Lx Ma Mc Me Mg Mh Mk Mm Mn Mp Mr Ms Mw Mx Na Nd Nf Ng Ni Nk Nn Nr Ns Nt Nu Ny Oh Oi Ok Om On Oy Oz Pc Pd Pe Pf Pz Qa Qd) On(Et Fp Hq Hr Hu Hw Hx Ih In Ip It Iv Jg Jh Jm Jp Jq Jr Js Lj Lx Ma Mc Md Me Mh Mk Mn Mp Mr Mt Mw Mx Na Ni Nj Nk Nl Nn Nr Ns Nu Nv Ny Oh Om Oy Oz Pc Pe Pf Pz Qa Qc Qd Qe) Iu(Et Fp Hq Hr Hu Hw In Ip It Iv Jg Jh Ji Jm Jq Js Jt Lj Lx Ma Mc Md Me Mh Mm Mn Mp Ms Mt Mw Mx Na Nf Ni Nj Nk Nl Ns Nt Nu Nv Ny Oh Oi Ok Om Oy Oz Pf Pz Qa Qc Qd Qe) Jr(Et Fp Hq Hr Hu Hw Ih In Ip It Iv Jg Jh Ji Jm Jp Lj Lx Ma Mc Md Me Mh Mn Mp Mt Mw Mx Na Nf Ni Nj Nk Nl Nr Ns Nt Nu Nv Ny Oh Ok Om Oy Oz Pc Pe Pf Pz Qa Qc Qd Qe) Ms(Et Fp Hq Hr Hu Hw Ih In Ip It Iv Jh Ji Jm Jq Js Jt Lj Lx Ma Mc Md Me Mg Mh Mm Mn Mp Mt Mx Na Nf Ng Ni Nj Nk Nl Ns Nt Nu Nv Ny Oh Ok Om Oz Pf Pz Qa Qc Qd Qe) Oi(Et Fp Hq Hr Hu Hw Ih In Ip It Iv Jg Jh Ji Jm Jq Js Jt Lj Lx Ma Mc Md Me Mh Mn Mp Mt Mw Mx Na Nf Ni Nj Nk Nl Ns Nt Nu Nv Ny Oh Ok Om Oy Oz Pf Pz Qa Qc Qd Qe) Pc(Et Fp Hq Hr Hw Ih In Ip It Iv Jg Ji Jm Jq Js Lj Lx Ma Mc Md Me Mh Mk Mn Mp Mr Mt Mw Mx Na Ni Nj Nk Nl Nn Nr Nt Nu Nv Ny Oh Ok Om Oz Pe Pf Pz Qa Qc Qd Qe) Ng(Et Fp Hq Hr Hu Hw Ih In Ip It Iv Jh Ji Jm Jq Js Jt Lj Lx Mc Md Me Mg Mh Mm Mn Mp Mt Mx Na Nf Ni Nj Nk Nl Ns Nt Nu Nv Ny Oh Ok Om Oz Pf Pz Qa Qc Qd Qe) Pd(Et Fp Hq Hr Hu Ih In Ip It Iv Jg Jh Ji Jm Jq Js Jt Lj Ma Mc Md Me Mg Mh Mn Mp Mt Mw Mx Na Nf Ni Nj Nk Nl Ns Nt Nu Nv Ny Oh Ok Oy Oz Pf Pz Qa Qc Qd Qe) Mk(Et Fp Hq Hr Hu Hw Ih In Ip It Iv Jg Jh Ji Jm Jq Js Lj Lx Ma Mc Md Mn Mp Mr Mt Mw Ni Nj Nk Nl Nr Ns Nu Nv Ny Oh Ok Om Oy Oz Pc Pf Pz Qa Qc Qd Qe) Jt(Et Fp Hq Hr Hu Hw Ih In Ip It Iv Jh Ji Jm Jq Js Lj Mc Md Me Mg Mh Mm Mp Mt Mw Mx Na Nf Ni Nj Nk Nl Ns Nt Nu Nv Ny Oh Ok Oy Oz Pf Pz Qc Qd Qc) Nr(Et Fp Hq Hr Hu Hw Ih In Ip It Iv Jg Jh Ji Jm Jq Lj Lx Ma Mc Md Mn Mp Mr Mt Mw Ni Nj Nk Nl Ns Nu Nv Ny Oh Ok Om Oy Oz Pe Pf Pz Qa Qc Qd Qe) Jp(Fp Hq Hr Hu Hw Ih In Ip It Iv Jh Ji Jm Jq Js Lj Lx Ma Mc Md Me Mh Mn Mp Mt Mw Mx Na Nf Ni Nj Nk Nl Ns Nt Nu Nv Om Oy Oz Qa Qc Qd Qe) Pe(Et Hq Hr Hu Hw Hx Ih In Ip It Iv Jg Jh Ji Jm Jq Lj Lx Ma Mc Md Mn Mp Mr Mt Mw Ni Nj Nk Nl Ns Nu Nv Ny Oh Ok Om Oy Oz Pz Qa Qc Qd Qe) Nn(Et Fp Hq Hr Hw Ih In Ip It Iv Jg Ji Jq Js Lj Lx Ma Mc Md Me Mh Mn Mp Mt Mw Mx Na Ni Nj Nk Nl Nt Nu Nv Ny Ok Om Oz Pf Qa Qc Qd Qe) Mm(Et Fp Hq Hr Hu Hw In Ip It Iv Ji Jm Jq Js Lj Mc Md Me Mg Mh Mn Mp Mt Mx Na Nf Ni Nj Nk Nl Ns Nt Nu Nv Ny Oh Ok Om Oy Oz Pf Pz Qc) Mr(Et Fp Hq Hu Hw Ih In Ip It Iv Jg Jh Ji Jm Jq Lj Lx Ma Mc Md Mn Mp Mt Mw Ni Nj Nk Nl Ns Nu Nv Ny Oh Om Oy Oz Pf Pz Qa Qc Qd Qe) Mg(Et Fp Hq Hw Ih In Ip It Iv Jh Ji Jm Jq Js Lj Mc Md Me Mh Mt Mx Na Nf Ni Nj Nk Nl Ns Nt Nu Nv Ny Oh Ok Oz Pf Pz Qa Qc Qd Qe) Lx(Et Fp Hq Hr Hu Hx Ih Ip Iv Jg Ji Jm Jq Js Lj Ma Me Mh Mn Mp Mw Mz Na Nd Nf Nj Nk Ns Ny Oh Ok Om Oy Oz Pf Pz Qa Qd) Mq(Et Fp Hq Hu Ih In Ip It Iv Jh Ji Jm Js Lj Mc Md Me Mh Mn Mp Mt Mx Na Ni Nj Nk Nl Ns Nt Nu Nv Ny Oh Oz Pz Qc Qd Qe) Me(Fp Hr Hu Ih In Ip It Iv Jg Jh Jm Jq Js Lj Ma Mc Md Mf Mn Mp Mw Na Nd Nf Nk Nu Oh Om Oy Oz Pf Pz Qa Qd Qe) Mf(Et Fp Hq Hu In Ip Jg Jh Ji Jm Js Mc Md Mh Mn Mt Mw Mx Na Ni Nl Ns Nt Nu Nv Ny Oh Ok Oy Oz Pf Qc Qc) Hx(Hr Hu Hw Ih In Ip It Iv Jg Jh Lj Ma Mc Md Mn Mp Mt Mw Ni Nj Nk Nl Ns Nu Nv Om Oz Qa Qc Qd Qe) Jg(Et Fp Hu Ih Iv Jh Ji Jm Jq Js Lj Ma Mh Mw Mz Na Nd Nf Nj Nk Ns Nt Ny Oh Ok Oy Pf Pz Qa Qd) Mz(Hq Hr Hu Hw Ih Ip It Iv Jh Lj Ma Mc Md Mn Mp Mt Mw Nj Nk Nl Ns Nu Nv Om Oz Qc Qd Qe) Nd(Hr Hu Hw Ih In Ip It Iv Jh Ji Lj Ma Mc Md Mn Mt Mw Mx Ni Nl Nu Nv Om Qa Qc Qd Qe) Js(Hr Hu Ih In It Jh Jq Lj Ma Md Mh Mn Mp Mt Mw Mx Nf Nk Nu Oh Om Oy Oz Pz Qa Qd Qe) Nk(Fp Hr Hu Iv Jh Jm Jq Lj Ma Mh Mn Mp Mw Na Nf Ni Nl Oh Om Oy Oz Pf Pz Qa Qd) Oh(Fp Hr Hu Ih It Iv Jh Lj Ma Mh Mn Mp Mt Mw Na Nu Nv Om Oy Oz Qa Qc Qd Qe) Jq(Hr Hu Hw Ih It Iv Jh Ji Lj Ma Mh Mn Mp Mt Mw Mx Nf Om Oy Oz Qa Qd Qe) Oy(Fp Hr Hu Ih It Iv Jh Jm Lj Ma Mh Mn Mp Mw Na Nf Ns Om Pf Pz Qa Qd) Fp(Hr Hu Hw Ih It Iv Jh Lj Ma Mn Mp Mt Mw Nf Nu Om Qa Qd Qe) Na(Hr Hu Hw Ih It Iv Lj Ma Mn Mp Mw Nf Nu Om Oz Pz Qa Qd) Ma(Et Hq Hr Hu Iv Jm Lj Mh Mw Nf Ns Ny Ok Oz Pf Pz) Pz(Hu Ih Iv Jh Lj Mh Mn Mp Mt Mw Om Qa Qd Qe) Pf(Hq Hu Ih Jh Lj Mn Mp Mt Mw Oz Qa Qd Qe) Mw(Et Hu Iv Jh Jm Lj Mh Nf Ns Ny Ok) Qa(Hu Hw Jm Mh Mx Nf Ny Ok Om) Om(In Ji Mx Nf Ni Nt Ny Ok) Mh(Hu Ih It Iv Lj Nu Qd) Mp(Et Hq Jm Nf Ok) Lj(Hu Mx Nf Ok Oz) Qd(Hu Nf Ny Ok) Mx(It Iv) Nf(Hr Hu) Hw(In Ni) Ok(Mn Qe) NtNu IhJm} Mi{Jo(Et Fr Hr Hu Hv Hw Ih In Io Ip Iq Ir Is It Iu Iv Jg Jh Ji Jj Jk Jl Jm Jn Jp Jq Jr Js Jt Li Lj Lw Lx Lz Ma Mb Mc Md Me Mf Mg Mh Mj Ml Mm Mn Mq Mt Mu Mv Mw Mx My Mz Na Nb Nc Nd Ne Nf Ng Nh Nk Nm Nn No Nq Ns Nt Nu Nv Nw Nx Ny Oe Of Oh Oi Ok Om On Oy Oz Pb Pd Po Qa Qb Qc Qd Qe) Ms(Fp Fr Hr Hu Hv Hx Ih Ii Io Ip Iq Ir Is It Iu Iv Jg Jh Jk Jm Jn Jp Jr Jt Lh Li Lu Lw Lx Ly Ma Mc Md Mf Mg Mh Mj Mk Ml Mm Mn Mp Mq Mr Mt Mu Mv Mw Mx My Mz Na Nb Nc Nd Nf Ng Nh Ni Nj Nk Nl Nm Nn Nq Nr Ns Nt Nw Nx Ny Oe Of Og Oh Oi Om On Oy Oz Pa Pb Pe Pf Pg Qa Qb Qd Qe) Hq(Et Fp Fr Hr Hu Hv Hw Hx Ih Ii In Io Ip Ir Is It Iv Jg Jh Jk Jm Jn Jp Jr Js Lh Li Lj Lw Lx Ly Lz Ma Mb Mc Md Me Mf Mh Mj Mk Ml Mm Mn Mp Mr Mt Mu Mv Mw Mx My Mz Na Nb Nc Ne Nh Ni Nk Nl Nn Nq Nr Ns Nt Nu Nv Nw Ny Of Oh Oi Om On Oy Oz Pb Pc Pe Pf Po Pz Qa Qb Qc Qd Qe) Og(Fr Hr Hu Hv Hw Ih Ii In Io Ip Iq Ir Is It Iu Iv Jg Jj Jk Jm Jn Jp Jq Jr Js Jt Lh Li Lu Lw Lx Ly Ma Me Mf Mh Mj Mk Ml Mm Mp Mq Mr Mt Mu Mv Mw Mx Mz Nb Nc Ne Ng Nh Ni Nj Nk Nm Nn No Ns Nu Nw Nx Ny Oe Of Oh Oi Om Oy Oz Pa Pe Pf Pg Pz Qa Qb Qd Qe) Jj(Et Fr Hr Hu Hv Hx Ih Ii In Ip Iq Ir Is It Iu Iv Jg Ji Jk Jl Jn Jp Jq Jr Js Jt Lh Li Lx Mc Mf Mg Mh Mj Mk Ml Mm Mq Mr Mt Mu Mv Mx My Mz Nb Nc Ne Nf Nh Nk Nm Nn Nq Nr Nt Nu Nx Ny Oe Oh Oi Ok On Oy Pb Pc Pe Pg Po Qb Qe) Jt(Et Fr Hr Hu Hv Hw Hx Ii Io Ip Iq Ir It Iu Iv Jg Jh Ji Jk Jm Jn Jr Js Li Lu Lw Lx Ly Ma Mc Mf Mg Mh Mj Ml Mm Mn Mq Mt Mu Mv Mw My Nb Nc Ne Ng Nj Nn No Nq Nt Nu Nv Nw Nx Oe Oh Oi Om Oy Pd Pe Pg Po Qa Qb Qd Qe) Pd(Et Fp Hr Ih Io Ip Ir Is It Jh Ji Jm Jn Jq Lj Lw Lz Ma Mb Mc Me Mf Mg Mh Ml Mm Mn Mp Mq Mt Mw Mx My Na Nd Nf Ng Nh Ni Nl Nm No Ns Nu Nv Nw Nx Ny Of Oh Oi Ok Om Pz Qc Qd) Nt(Fr Hu Hv Iq Ir Is Iu Iv Jg Jk Jn Jp Js Lh Lu Lw Lx Ly Mb Md Mg Mj Mk Ml Mr Mt Mu Mv My Mz Nb Nc Nf Nk Nn Nq Nu Nw Nx Ny Oe On Pa Pc Pe Pg Qa Qb Qd Qe) Pc(Hu Hx Ii Iq Iu Jh Ji Jl Jm Jn Jp Jq Jr Js Li Lu Lx Ly Mc Mf Mh Ml Mm Mq Mt Mv Mx My Mz Na Nc Ne Nf Nh Nj Nm Nn Nq Nr Ns Ny Of Oh Oi Ok Oy Pa Pf Pz) Mg(Hu Hx Ii Iq Iu Jg Jk Jl Jn Jp Js Lh Lw Lx Ly Ma Mf Mk Ml Mm Mr Mu Mv Mx Nb Nd Ne Ng Nh Nj Nn Nr Nx Oe Oh Oi Om On Oy Pa Pb Pe Pg Po) Jl(Et Hu Ii Iq Iu Jm Jn Jq Jr Li Lu Lx Ly Md Mf Mh Mk Ml Mq Mr Mt Mx Na Nc Ne Nf Nh Nj Nm Nn Nr Nv Nx Ny Oe Of Oi Ok Pa Pe Pg Pz) Iq(Fr Hx Ii Ir Is Iv Jk Jp Jr Js Lh Lu Mf Mj Mk Ml Mm Mr Mv Mz Nb Nc Ne Ng Nh Nj Nm Nr Nw Nx Oe Oi On Oy Pe Qb) Js(Fr Hw Ii Ir Is Iu Iv Jn Jp Lu Lx Ly Mj Mk Mm Mr Nb Nc Ng Nj Nm Nn No Nq Nr Nw Oe Om On Pb Pe Pg Po Qd Qe) Ng(Fr Hu Hx Ii Jg Jp Jr Lh Lu Lx Ly Mj Mk Mr Mu Mv Mw My Mz Nb Nd Ne Nj Nn Nq Nr Of Oy Pb Pe) Oe(Fr Hu Hx Ii Iu Jg Jp Jr Lh Lu Ly Mf Mj Mk Ml Mm Mr Mu Mz Nb Nc Nd Ne Nj Nm Nn Nx Oy Pa Pe) Nx(Fr Hx Ii Is Iu Jg Jk Jp Jr Lh Lu Ly Mf Mk Ml Mr Mz Nb Nj Nn Nq Nr Nw Om Oy Pa Pe Pg) Pa(Iu Jm Jn Lu Lx Mf Mh Ml Mm Mr Mx Na Ne Nf

Figure 16 Continued

Nh Nj Nq Nr Ny Oh Oi Oy Pf) Lu(Iu Jm Jp Jr Mf Mh Ml Mm Mt Mz Ne Nf Nh Nj Nq Nr Of Oh Oi) Iu(Fr Hu Hx Is Jp Jr Lh Ly Mk Mr Nc Nh
Nj Nq Nr On Pe Qb) Nj(Fr Jp Mf Mk Mm Mr Ne Nh Nm Nn Oh Oi On) Jp(Et Jn Ly Nh Nm Nn Nq Ny Oh Oi Ok Pz) Nq(Fr Jk Jr Lx Mv Nf Nn
Pg) Mm(Fr Lh Mk Mz Nn Nw On) Mk(Mx Na Nh Of Oi) Mx(Is Iv Mj Nr) Jr(Jn Lx Ml Oh) On(Ji Nf Nm Ok) Oi(Ly Mr Nn) Ml(Hx Nn) Mz(Jn
Oh) Nc(Ne Nh) FrOh NmLw NrNa NfLh IsJn} Jl{Jj(Et Fp Fr Hq Hr Hu Hv Hw Hx Ih Ii In Io Ip Iq Ir Is It Iu Iv Jg Jh Ji Jk Jm Jn Jo Jp Jq Jr Js Jt
Lh Li Lj Lu Lw Lx Ly Lz Ma Mb Mc Md Me Mf Mg Mh Mj Mk Ml Mn Mp Mq Mr Mt Mu Mv Mw Mx My Mz Na Nb Nc Nd Ne Nf Ng Nh Ni
Nj Nk Nl Nm Nn No Nq Nr Ns Nt Nu Nv Nw Ny Of Oi Ok Om On Oy Oz Pb Pc Pd Pe Po Pz Qa Qb Qc Qd Qe) Oe(Et Fp Fr Hq Hr Hu Hv Hw
Hx Ih In Io Ip Iq Ir Is It Iu Iv Jg Jh Ji Jk Jm Jn Jo Jp Jq Jr Js Lh Li Lj Lw Lx Ly Lz Ma Mb Mc Md Me Mf Mg Mh Mj Ml Mn Mp Mq Mt Mu
Mv Mw Mx My Mz Na Nb Nc Nd Ne Nf Ng Nh Ni Nj Nk Nl Nm Nn No Nq Ns Nt Nu Nv Nw Ny Of Oh Oi Ok Om Oy Oz Pb Pd Pe Pf Pg Po
Pz Qa Qb Qc Qd Qe) Mm(Et Fp Fr Hq Hr Hu Hv Hw Hx Ih In Io Ip Ir Is It Iv Jg Jh Ji Jk Jm Jn Jo Jq Jr Js Lh Li Lj Lu Lw Lx Ly Lz Ma Mb Mc
Md Me Mf Mg Mh Mj Mk Ml Mn Mp Mq Mr Mt Mu Mv Mw Mx My Mz Na Nb Nc Nd Nf Ni Nj Nk Nl Nm Nn No Nq Nr Ns Nt Nu Nv Nw
Ny Of Oh Ok Om On Oy Oz Pb Pc Pd Pe Pf Pg Po Pz Qa Qb Qc Qd Qe) Jt(Et Fp Fr Hq Hr Hu Hv Hw Hx Ih In Io Ip Iq Ir It Iu Iv Jg Jh Ji Jk Jm
Jn Jo Jq Jr Js Li Lj Lu Lx Ly Lz Ma Mb Mc Md Me Mf Mg Mh Ml Mn Mp Mq Mt Mu Mv Mw Mx My Mz Na Nb Nc Nd Ne Nf Ng Nh Ni Nj
Nk Nl Nm Nn No Nq Ns Nt Nu Nv Nw Nx Ny Of Oh Oi Ok Oy Oz Pb Pd Pf Po Pz Qa Qb Qc Qd Qe) Nx(Fr Hu Hx Ii Ip Iq Is Iu Iv Jg Ji Jk Jn
Jo Jp Jq Jr Js Lh Li Lu Lw Lx Ly Lz Mf Mg Mj Mk Ml Mn Mq Mr Ms Mt Mu Mv Mx Mz Nb Nc Ne Ng Nh Nj Nk Nm Nn No Nq Nr Ns Nu
Nw Ny Of Oh Oi Om On Oy Pb Pc Pd Pe Pg Po Pz) Og(Et Fp Fr Hq Hr Hv Hw Ih In Io Ip Ir It Iv Jg Jh Ji Jk Jm Jn Jq Jr Lh Lj Lx Lz Ma Mb Mc
Md Me Mf Mh Ml Mn Mp Mt Mu Mv Mw Mx My Mz Na Nc Nd Nf Ni Nk Nl No Nq Ns Nt Nu Nv Oy Oz Pf Pg Po Qa Qb Qc Qd Qe) Ms(Fp
Fr Hu Hx Ii Iq Is Iu Jg Jm Jo Jp Jq Jr Js Li Lu Lw Ly Mf Mg Mh Mj Mk Mq Mr Mt Mv Mx Mz Nb Nc Nd Ne Ng Nh Ni Nj Nk Nl Nm Nn Nq
Nr Ns Nw Ny Of Oh Oi Ok Om On Oy Pa Pb Pd Pe Pg Pz) Pa(Fp Hq Ih Ii Iq Iu Jn Li Lu Mg Mh Ml Mq Mr Mx Na Ne Nf Nh Ni Nj Nm Nn Nr
Ns Nt Nv Ny Of Oi Ok Oy Po Pz) Oh(Fr Ii Iu Jo Jp Jr Lu Lw Mg Mk Mq Mr Mz Ne Ng Nh Nj Nn Of Oi On Pc Pe Pg) Jo(Hu Hx Ii Lh Lu Lw
Ly Mj Mk Mr Mt Mx Nb Nh Nj Nr Om On Pc Pe Po) Ng(Fr Hu Ii Jg Jk Lh Lu Mk Mr Mx Nb Nh Nj Nn Nr On Oy Pb Pe Pg) Oi(Hu Ii Iq Jp Lu
Ly Mk Mq Mr Mx Ne Nh Nj Nn Nr On Pc Pe Pg) Lu(Ii Iq Iu Js Mg Mq Ne Nh Nj Nn Nq Nr Ny Of Pd) Ii(Mg Mq Ne Nh On Pc Pg Pz) Mg(Fr
Lh Mx Nh Pc Pg) Pd(Lx Mk Mr On Pg Po) Nh(Iq Iu Jp Nj) Js(Is Jr Lh Pe) Ok(Jp Mr On Pe) Iu(Hu Nj Pg) Ne(Nc Nj) Pz(Pc Pg) Pc(My Ns)
NnJp NtLh Mxls OfPg} Pa{Og(Fp Fr Hq Hr Hu Hv Hw Hx Ih Ii In Ip Ir Is It Iu Iv Jg Jh Ji Jk Jm Jn Jp Jq Jr Lh Li Lj Lu Lw Lx Ly Lz Ma Mb
Mc Md Mc Mf Mg Mh Mj Mk Ml Mm Mn Mp Mq Mr Ms Mt Mu Mv Mw Mx My Mz Nb Nc Nd Ne Nf Nh Ni Nk Nl Nm Nn No Nq Nr Ns Nt
Nu Nv Nw Nx Ny Oe Of Oh Oi Ok Om On Oy Oz Pb Pg Po Pz Qa Qb Qc Qd Qe) Jo(Et Fp Hq Hr Hv Hw Hx Ih Ii In Io Ip Ir Is It Iu Iv Jg Jh Ji
Jk Jm Jn Jp Jq Jr Jt Li Lj Lu Lx Lz Ma Mb Mc Md Me Mf Mg Mj Mm Mn Mp Mq Mr Mt Mu Mv Mw Mx My Mz Na Nb Nc Nd Ne Ng Nh Ni
Nk Nl Nm No Nq Nr Ns Nt Nu Nv Nw Nx Ny Of Oh Oi Ok Om Oy Oz Pb Po Pz Qa Qb Qc Qd Qe) Jj(Et Fr Hq Hr Hv Hw Hx Ih Ii In Io Ip Ir Is
It Iu Iv Jg Jh Ji Jm Jp Jq Lh Li Lw Lx Lz Ma Mb Mc Md Me Mg Mj Mk Mm Mn Mp Mq Mr Mt Mu Mv Mw My Mz Na Nb Nc Nd Ne Nf Ng
Ni Nk Nl Nm Nn No Nq Nr Ns Nt Nu Nv Nw Nx Ny Of Oh Oi Ok Om On Oy Oz Pb Po Pz Qa Qb Qc Qd Qe) Pe(Et Fp Hu Hv Hw Hx Ih In Io
Ip Ir Is It Iv Jg Jh Ji Jk Jn Jq Lh Li Lj Lw Lx Ly Lz Mb Mc Md Me Mf Mg Mh Mj Mk Ml Mm Mn Mq Mr Mt Mw Mx My Na Nb Nc Nd
Ne Nh Nk Nl Nm Nn No Nq Nr Ns Nt Nu Nv Ny Of Oh Ok Om On Oy Oz Pb Pc Pf Pg Po Pz Qa Qb Qc Qd Qe) Oe(Fp Hu Hx Ii Ir Is Iu Iv Jg
Jh Ji Jm Jn Jp Jr Jt Lh Lu Lw Lx Ly Lz Ma Mf Mg Mh Mk Ml Mm Mq Mr Ms Mt Mu Mv Mz Nb Nc Nd Ne Ni Nj Nl Nn Nq Nr Ns Nt Nw Nx
Oh Om Oy Oz Pf Pg Qa Qb Qd Qe) Pd(Et Fp Hq Ih Ii In Io Ip Ir It Jh Jk Jm Jn Jq Li Ly Mb Mc Md Me Mg Mj Ml Mm Mn Mq Mw Mx My Nb
Nd Ne Nh Nk Nl Nm No Nq Nr Ns Nt Nu Nv Nx Ny Of Oh Oi Ok Oy Oz Pf Pz Qa Qb Qc Qd Qe) Js(Et Hu Hv Hw Hx Iq Ir Iu Iv Jg Jh Jm Jn Jq
Jt Lu Lx Lz Ma Mg Mh Mj Mk Mp Mq Mr Ms Mt Mu Mv Na Nc Nf Ng Ni Nj No Nq Nr Ns Nv Of Om On Oy Oz Pb Pc Pf Pg Qa Qb Qc Qd
Qe) Jt(Et Hw Iq Is Iu Iv Jg Jh Ji Jm Jr Lh Lu Lw Lx Ma Mh Mk Ml Mr Ms Mt Mu Mv Ni Nj Nn Nr Nw Om Oy Oz Pc Pf Qa Qd) Ng(Hr Hu Hv
Iq Jg Jh Jp Jr Lh Lu Lz Ma Mf Mh Mj Ms Mt Mv Mx Mz Na Nf Nj Nn On Pc Pf Pg) Hq(Fr Hu Hv Hx Ih Iq Jn Jr Lj Lu Lz Mf Mh Mj Ml Ms
Mu Mx Nb Nd Nj Nn Pc Pf Pg Qd) Nf(Fr Hv Hx Iq Iu Jn Lh Lj Lu Lz Mf Mh Ml Ms Mx Nn Nw On Pc Pf) Iq(Fp Fr Ir Is Jp Jr Lu Mf Mg Ms
Mv Nj Nn Nx Oi Oy Pc Pf) Hr(Iu Mg Mm Ms Nj Nx Oi Pf) Ms(Iu Jg Mz Na On Pf) Nj(Iu Lu Nr Pf) Mg(Jg Lu Pc) Nx(Om On Pc) Mh(Na Nt)
Mm(Jp Mz) Iu(Oy Pf) Oi(Nn Pc) MlNa JpPf} On{Oe(Et Fp Hq Hr Hu Hv Hw Hx Ih Ii In Io Ip Iq Ir Is It Iu Iv Jg Jh Ji Jk Jm Jn Jp Jq Jr Js Lh Li
Lj Lu Lw Lx Ly Lz Ma Mb Mc Md Me Mf Mg Mh Mj Mk Ml Mm Mn Mp Mq Mr Mt Mu Mv Mw Mx My Mz Na Nb Nc Nd Ne Ng Nh Ni Nj
Nk Nl Nm Nn No Nq Nr Ns Nt Nu Nv Nw Ny Of Oh Oi Om Oy Oz Pb Pc Pe Pf Pg Po Pz Qa Qb Qc Qd Qe) Og(Fr Hq Hr Hu Hv Hx Iq Is Iu Iv
Jg Jh Jk Jp Jq Jr Js Lh Lj Lu Lw Lx Mf Mg Mh Mj Mm Mq Mt Mu Mv Mx My Mz Na Nb Nc Ne Nh Nj Nk Nn Nq Nt Nw Nx Of Oh Oi Oy Pc
Pe Pf Pg Qa Qb Qd) Jt(Fr Is Iv Lh Lx Mj Mk Mm Mq Mr Ms Mz Nf Nj Nr Nx Pe Pg Qa) Ms(Fr Jo Mz Nf Pc Pd) Ok(My Nf Of Oy) Nx(Fr Nf
Pg) Pd(Lh Pe Pg) FrMg JjPg JoLh} Pg{Jj(Et Fp Fr Hq Hu Hv Hx Ih Ii In Ip Iq Ir Is Iu Iv Jh Ji Jk Jn Jp Jq Jr Js Jt Lh Li Lu Lx Ly Lz Mc Md Mf
Mh Mj Mk Ml Mm Mq Mr Ms Mt Mu Mv Mx My Mz Na Nb Nc Nd Ne Nf Ng Nh Ni Nj Nk Nl Nm Nn No Nq Nr Ns Nt Nu Nv Nw Nx Ny Oe
Of Oh Oi Ok Oy Oz Pc Pe Pf Pz Qb) Jo(Fr Hq Hw Ii Ip Iq Is Iu Iv Jm Jp Jq Jr Js Jt Lh Lu Lw Ma Mf Mg Mj Mk Mq Ms Mu Mv Mz Nb Ne Ng
Nn No Nr Ns Nw Nx Oe Og Oi Pc Pd Pe) Ng(Fr Jg Lu Pc) Jt(Jp Mz) Pc(Ms Og) Pd(Lh Lx) NrOe IsJs NxOm} Og{Pc(Fr Hu Ii Ir Is Iv Jj Jk Jo
Jp Jq Jr Lh Lu Lx Ly Mf Mg Mj Mq Ms Mv My Mz Nb Ng Nj Ns Nw Oe Oh Pe Pa Qa Qb Qd) Fr(Hx Is Iv Jj Jo Jr Jt Lw Ly Mg Mj Mk Mr Ms
Mz Nb Nc Ng Nj Nr Nw Oe Pb Pe) Nr(Hx Is Jj Jo Jp Jr Ms Mv Mz Oe Qb) Mk(Hx Is Jj Jo Jp Jr Ms Mv Mz Nw Oe) Pb(Hx Is Jj Jr Ms Mu Mv
Mz Nn Nw Oe) Pe(Jj Jo Jp Jr Jt Mv Mz Pd) Mr(Jj Jo Jp Jr Mv Mz Oe) Is(Ir Jn Jr Jt Ml Mx) Lh(Jj Js Jt Mg Nt) Hx(Jo Oe) Jj(Ii Jk) Nw(Js Mt)
MqOm MsNb NgJg} Fr{Oe(Hx Ii Is Jj Jo Jr Jt Ly Mg Mj Mr Ms Mz Nb Ng Nj No Nx Pc Pd Pe Qb) Ng(Hu Hx Ii Iu Jk Jr Lh Lu Ly Mm Mr Ms
Nb Nc Nj Nr Oy Pb Pc Pe) Mg(Hx Ii Jr Lh Lx Ly Mk Mr Ms Nb Nc Nj Nr Om Oy Pb Pc Pe Po) Jt(Hx Ir Is Iv Jp Jr Lh Mj Mk Mr Mz Nr Pe)
Ms(Mk Mr Nb Nr Pc) Jo(Lh Mk Mr Nr Pe) Nx(Hx Jr Om) Oi(Nn Pc) IsJs JjPe JrLi LhPd} Lh{Jo(Hq Jp Lu Lw Ly Mg Mj Mk Mm Mr Ms Ne
Ng Nj Nq Nr Nt Nx Oe Oh Pc Pe) Pd(Iq Iu Jr Lu Lw Ly Mf Mg Mp Mq Ms Nc Nf Ng Nj Nn Nx Oi Pc) Jj(Jk Js Jt Lu Mf Mg Mk Mm
Mq Mr Ms Nf Nn Nt Nx Oe Ok Pc) Jt(Is Jp Lw Mk Mr Mz Nr Nt) Pc(Mg Ms Nf Ng Oe Oi) Ng(Jk Js Mq Nx) Oe(Js Mg Mk Nr) Js(Jr Mz)
NtNx} Pe{Pd(Hr Hu Hx Ih Iq Is Iu Iv Jg Ji Jj Jk Jn Jo Jp Jq Jr Js Jt Lj Lu Lw Lx Lz Ma Mf Mh Mj Ml Mp Ms Mt Mx Mz Na Nb Nc Nf Nj Nv
Nw Om Pf Po Qa Qb Qd) Jo(Jk Jp Js Ml Mv Mz Nj Nn Oe Pc) Jj(Jt Lu Oe Pc) Jt(Is Mz) Pc(Ms Oe) NgJk} Oe{Nr(Hx Is Jg Jj Jo Jp Jr Lx Mv Mz
Nn Nw Pc Qa Qb) Mk(Hx Is Jg Jj Jo Jp Jr Lx Mv Mz Nn Nw Qa Qb) Mr(Jj Jo Jp Jr Lx Mv Mz Nn Nw Qb) Pc(Hx Jr Ms Mz) Is(Jn Js) Jj(Hx Jk)
PoPd} Pc{Ms(Hu Hx Is Jo Jp Jr Lx Mj Mv My Mz Nw Qa Qb) Ng(Hu Hx Jr Lu Mv My Mz) Mz(Jt Oi) JrOi NxOm} Ng{Jk(Jg Mk Mr Nr Oy
Pb) Mv(Mk Mr Pb) Mu(Mk Pb) LuJg} Jj{Qb(Lu Mk Mr) Jr(Jk Mk Mr) LuMz IsJs} Jt{Mz(Mj Mk Mr Nr) Jp(Mk Mr Nr)} Mz{LuJs MkMs}
Jr{NnOi IsJs}

Unconstrained panels with 2 analytes, where 1.0E-6 >= 'model p-value' > 0. Contains 55 panels of 6,786 total panels evaluated. : Lv(aA Fr Hx Iq
Iu Jj Jl Jo Jp Lu Mf Mg Mi Mk Mq Mr Mz Nd Ng Nn Nr Nw Nx Oe Og Oi Pa Pc Pd Pe) aA(Fr Iq Iu Jj Jl Jo Jt Ly Mi Mm Ms Nh Nj Nx Oe Og
Oh Oi Pa Pc Pg) Pa(Jj Pd) MiPd JlOg

Figure 16 Continued

Unconstrained panels with 2 analytes, where 1.0E-5 >= 'model p-value' > 1.0E-6. Contains 223 panels of 6,786 total panels evaluated. : aA(Et Fp Hq Hr Hu Hv Hw Hx Ih Ii In Io Ip Ir Is It Iv Jg Jh Ji Jk Jm Jn Jp Jq Jr Js Lh Li Lj Lu Lw Lx Lz Ma Mb Mc Md Me Mf Mg Mh Mj Mk Ml Mn Mp Mq Mr Mt Mu Mv Mw Mx My Mz Na Nb Nc Nd Ne Nf Ng Nj Nk Nl Nm Nn No Nq Nr Ns Nt Nu Nv Nw Ny Of Ok Om On Oy Oz Pb Pd Pe Pf Po Pz Qa Qb Qc Qd Qe) Lv(Et Fp Hq Hr Hu Hv Hw Ih Ii In Io Ip Ir Is It Iv Jg Jh Ji Jk Jm Jn Jq Jr Js Jt Lh Li Lj Lw Lx Ly Lz Ma Mb Mc Md Me Mh Mj Ml Mm Mn Mp Ms Mt Mu Mv Mw Mx My Na Nb Nc Ne Nf Nh Ni Nj Nk Nl Nm No Nq Ns Nt Nu Nv Ny Of Oh Ok Om On Oy Oz Pb Pf Pg Po Pz Qa Qb Qc Qd Qe) Mi(Hq Iq Iu Jj Jl Jo Js Jt Lu Mg Mk Ms Nj Nt Oe Og Pa Pc) Jl(Jj Jt Lu Mm Ms Nx Oe Oh Oi Pa) Pa(Iq Jo Js Jt Oe Og Pe) Oe(Fr On) Og(On Pc) Pd(Lh Pe) Pg(Jj Jo)

Unconstrained panels with 2 analytes, where 1.0E-4 >= 'model p-value' > 1.0E-5. Contains 266 panels of 6,786 total panels evaluated. : Mi(Et Fp Fr Hr Hu Hv Hw Hx Ih Ii In Io Ip Ir Is It Iv Jg Jh Ji Jk Jm Jn Jp Jq Jr Lh Li Lj Lw Lx Ly Lz Ma Mb Mc Md Me Mf Mh Mj Ml Mm Mn Mp Mq Mr Mt Mu Mv Mw Mx My Mz Na Nb Nc Nd Ne Nf Ng Nh Ni Nk Nl Nm Nn No Nq Nr Ns Nu Nv Nw Nx Ny Of Oh Oi Ok Om On Oy Oz Pb Pe Pf Pg Po Pz Qa Qb Qc Qd Qe) Jl(Et Fp Fr Hq Hr Hu Hv Hw Hx Ih Ii Ip Iq Ir Is Iu Iv Jg Jk Jm Jn Jo Jp Jq Jr Js Lh Li Lw Lx Ly Lz Ma Mb Mc Mf Mg Mh Mj Mk Ml Mq Mr Mt Mu Mv Mx My Mz Na Nb Nc Nd Ne Nf Ng Nh Ni Nj Nk Nl Nm Nn No Nq Nr Ns Nv Nw Ny Of Ok Om On Oy Oz Pb Pc Pd Pe Pg Po Pz Qb) Pa(Fp Fr Hq Iu Jm Jp Jr Lu Mf Mg Mh Mk Ml Mm Mq Ms Mu Mz Ne Nf Ng Ni Nj Nn Nr Nx Of Oh Oi On Oy Pc Pf) Fr(Jj Jo Jr Jt Mg Mk Mr Ms Mz Ng Nj Nr Nx Og Oi Pe) Jj(Hx Jk Jr Lh Mk Mr Nr On Pe) Og(Hx Is Mk Mr Mz Nr Nw Pb Pe) Oe(Hx Mk Mr Nr Pc Pe) Lh(Jo Jt Mg Nt) On(Jo Jt Ms Nf) Pc(Ms Ng Oi) LuMz IsJs JoPe Unconstrained panels with 2 analytes, where 1.0E-3 >= 'model p-value' > 1.0E-4. Contains 441 panels of 6,786 total panels evaluated. : Fr(Et Fp Hq Hr Hu Hv Hw Hx Ih Ii In Io Ip Iq Ir Is It Iu Iv Jg Jh Ji Jk Jm Jn Jp Jq Js Lh Li Lj Lu Lw Lx Ly Lz Ma Mb Mc Md Me Mf Mh Mj Ml Mm Mn Mp Mq Mt Mu Mv Mw Mx My Na Nb Nc Nd Ne Nf Nh Ni Nk Nl Nm No Nq Ns Nt Nu Nv Nw Ny Of Oh Ok Om On Oy Oz Pb Pc Pd Pf Pg Po Pz Qa Qb Qc Qd Qe) Pa(Et Hr Hu Hv Hw Hx Ih Ii In Io Ip Ir Is It Iv Jg Jh Ji Jk Jn Jq Lh Li Lj Lw Lx Ly Lz Ma Mb Mc Md Me Mj Mn Mp Mr Mt Mv Mw Mx My Na Nb Nc Nd Nh Nk Nl Nm No Nq Ns Nt Nu Nv Nw Ny Ok Om Oz Pb Pg Po Pz Qa Qb Qc Qd Qe) Jj(Hu Ih Ii Ir Is Iu Iv Jg Jp Lu Lx Ma Mj Mt Mu Mv Mz Nb Nn Nu Nv Nw Oe Og Om Oy Pc Po Qa Qb Qd Qe) On(Hx Iq Is Iu Jp Jr Lh Lu Lx Mg Mm Mq Mu Mv Mz Nc Ng Nj Nm Nn Nx Of Oi Ok Pd Pe Pg Qa Qb) Og(Ii Ir Iv Jg Ji Jk Jp Jr Lh Lw Lx Mj Mu Mv Nb Nn No Om Pg Po Qa Qb Qe) Pc(Is Iu Jp Jr Jt Lu Lx Mg Ms Mu Mv Mz Na Nf Ng Nn Nw Oi Pc Pf Pg Qb) Oe(Ii Ir Is Jg Jp Jr Lh Lx Mj Mu Mv Mz Nb Nn Nw Pg Po Qa Qb Qe) Jl(In Io It Jh Ji Lj Md Me Mn Mp Mw Nt Nu Pf Qa Qc Qd Qe) Mz(Jo Jp Jt Lh Mj Mk Mm Mr Ms Mv Nj Nn Nr Nx Oi Pc Pg) Pg(Iu Jp Jr Jt Lu Mg Mk Mr Ms Ng Nr Nx Of Oi Pd) Lh(Iu Jp Jr Js Lu Mk Mm Ms Nf Ng Nj Nx Oi Pc) Nw(Jo Js Jt Lu Mk Ml Mm Mr Ms Nj Nr Nx Oi) Lu(Hx Ir Is Ji Jp Jr Lw Mk Mr Nr Qb) Mk(Is Jo Jp Jr Jt Ms Mv Ng Qa Qb) Mr(Jo Jp Jr Jt Ms Mv Ng Nn Qb) Is(Iu Jn Jo Jr Jt Ml Ms Mx Nx) Jp(Hx Jr Jt Lw Mj Mm Nr Pc) Jo(Hx Mj Nb Nr Pc Po) Ng(Jg Jk Mv Nb Pb) Pc(Ir Jr Mg My Ns) Ms(Hx Jg Nb Nr) Nr(Jr Mv) PoPd NnOi LxHq MgJg JrJs Unconstrained panels with 2 analytes, where 1.0E-2 >= 'model p-value' > 1.0E-3. Contains 1,646 panels of 6,786 total panels evaluated. : Nr(Et Fp Hq Hr Hu Hv Hw Hx Ih Ii In Io Ip Iq Ir Is It Iu Iv Jg Jh Ji Jk Jm Jn Jq Js Jt Lh Li Lj Lw Lx Ly Lz Ma Mb Mc Md Me Mf Mg Mh Mj Mk Ml Mm Mn Mp Mq Mr Mt Mu Mw Mx My Na Nb Nc Nd Ne Nf Ng Nh Ni Nj Nk Nl Nm Nn No Nq Ns Nt Nu Nv Nx Ny Of Oh Oi Ok Om On Oy Oz Pb Pc Pd Pe Pf Po Pz Qa Qb Qc Qd Qe) Mr(Et Fp Hq Hr Hu Hv Hw Hx Ih Ii In Io Ip Iq Ir Is It Iu Iv Jg Jh Ji Jk Jm Jn Jq Js Lh Li Lj Lw Lx Ly Lz Ma Mb Mc Md Me Mf Mg Mh Mj Mk Ml Mm Mn Mp Mq Mt Mu Mw Mx My Na Nb Nc Nd Ne Nf Nh Ni Nj Nk Nl Nm No Nq Ns Nt Nu Nv Nx Ny Of Oh Oi Ok Om On Oy Oz Pb Pc Pd Pe Pf Po Pz Qa Qc Qd Qe) Nw(Et Fp Hq Hr Hu Hv Hw Hx Ih Ii In Io Ip Iq Ir Is It Iu Iv Jg Jh Ji Jk Jm Jn Jp Jq Jr Lh Li Lj Lw Lx Ly Lz Ma Mb Mc Md Me Mf Mg Mh Mj Mk Ml Mm Mp Mq Mt Mu Mv Mw Mx My Mz Na Nb Nc Nd Ne Nf Ng Nh Ni Nk Nl Nm Nn No Nq Ns Nt Nu Nv Ny Of Oh Ok Om On Oy Oz Pb Pc Pd Pf Pg Po Pz Qa Qb Qc Qd Qe) Mk(Et Fp Hq Hr Hu Hv Hw Hx Ih Ii In Io Ip Iq Ir It Iu Iv Jg Jh Ji Jk Jm Jn Jq Js Li Lj Lw Lx Ly Lz Ma Mb Mc Md Me Mf Mg Mh Mj Ml Mm Mn Mp Mq Mt Mu Mw Mx My Na Nb Nc Nd Ne Nf Nh Ni Nj Nk Nl Nm Nn No Nq Ns Nt Nu Nv Nx Ny Of Oh Oi Ok Om On Oy Oz Pb Pc Pd Pe Pf Po Pz Qc Qd Qe) Jp(Et Fp Hq Hr Hu Hv Hw Ih Ii In Io Ip Iq Ir Is It Iu Iv Jg Jh Ji Jk Jm Jn Jo Jq Js Li Lj Lx Ly Lz Ma Mb Mc Md Me Mf Mg Mh Ml Mn Mp Mq Ms Mt Mu Mv Mw Mx My Na Nb Nc Nd Ne Nf Ng Nh Ni Nj Nk Nl Nm No Nq Ns Nt Nu Nv Nx Ny Of Oh Oi Ok Om On Oy Oz Pb Pd Pf Po Pz Qa Qb Qc Qd Qe) Jr(Et Fp Hr Hu Hv Hw Hx Ih Ii In Io Ip Iq Ir It Iu Iv Jg Jh Ji Jk Jm Jn Jo Jq Jt Li Lj Lw Lx Ly Lz Ma Mc Me Mf Mg Mh Mj Ml Mm Mn Mp Mq Ms Mt Mu Mv Mw Mx My Mz Na Nb Nc Nd Ne Nf Ng Nh Ni Nj Nk Nm Nn No Nq Ns Nu Nv Nx Ny Of Oh Oi Ok Om Oy Oz Pb Pd Pf Po Pz Qa Qb Qd Qe) Pg(Et Fp Hq Hr Hu Hv Hw Hx Ih Ii In Io Ip Iq Ir Is It Iv Jg Jh Ji Jk Jm Jn Jq Js Lh Li Lj Lw Lx Ly Lz Ma Mb Mc Md Me Mf Mh Mj Ml Mm Mn Mp Mq Mt Mu Mv Mw Mx My Na Nb Nc Nd Ne Nf Nh Ni Nj Nk Nl Nm Nn No Nq Ns Nt Nu Nv Ny Oh Ok Om Oy Oz Pb Pc Pf Po Pz Qa Qb Qc Qd Qe) Mz(Et Fp Hq Hr Hu Hv Hw Hx Ih Ii In Io Ip Iq Ir Is It Iu Iv Jg Jh Ji Jk Jm Jn Jq Js Li Lj Lw Lx Ly Lz Ma Mb Mc Md Me Mf Mg Mh Ml Mn Mp Mq Mt Mu Mw Mx My Na Nb Nc Nd Ne Nf Ng Nh Ni Nj Nk Nl Nm Nn No Nq Ns Nt Nu Nv Ny Of Oh Ok Om Oy Oz Pb Pd Pf Po Pz Qa Qb Qc Qd Qe) Lh(Et Fp Hq Hr Hu Hv Hw Hx Ih Ii In Io Ip Iq Ir Is It Iv Jg Jh Ji Jk Jm Jn Jq Li Lj Lw Lx Ly Lz Ma Mb Mc Md Me Mf Mh Mj Ml Mn Mp Mq Mt Mu Mv Mw Mx My Na Nb Nc Nd Ne Nh Ni Nk Nl Nm Nn No Nq Ns Nu Nv Ny Of Oh Ok Om Oy Oz Pb Pe Pf Po Pz Qa Qb Qc Qd Qe) Pe(Et Fp Hq Hr Hu Hv Hw Hx Ih Ii In Io Ip Iq Ir It Iv Jg Jh Ji Jk Jm Jn Jq Js Li Lj Lw Ly Lz Ma Mb Mc Md Me Mf Mh Mj Ml Mm Mn Mp Mq Mt Mw Mx My Nb Nc Nd Ne Nh Ni Nj Nk Nl Nm No Nq Ns Nt Nu Nv Nx Ny Of Oh Ok Om Oy Oz Pb Po Pz Qa Qc Qd Qe) Hx(Et Hq Hr Hu Hv Hw Ii Ip Iq Ir Is Iu Iv Jg Jh Ji Jk Jm Jn Jq Js Jt Li Lw Lx Ly Lz Ma Mc Md Mf Mg Mj Ml Mm Mn Mp Mq Mt Mu Mv Mw Mx My Na Nb Nc Nd Ne Nf Ng Nh Ni Nj Nk Nl Nm No Nq Ns Nu Nv Ny Of Oh Oi Om Oy Pc Pd Po Pz Qa Qb Qd Qe) Is(Hr Hu Hv Hw Ih Ii Io Ip Iq Ir It Iv Jg Jh Ji Jk Jm Jq Li Lw Lx Ly Lz Ma Mc Mf Mg Mh Mj Mm Mn Mp Mq Mt Mu Mv Mw My Na Nb Nc Nd Ne Nf Ng Nh Ni Nj Nk Nm Nn No Nq Ns Nu Ny Of Oh Oi Om Oy Pb Pc Pd Pf Po Pz Qa Qb Qd Qe) On(Et Fp Hq Hr Hu Hv Hw Ih Ii In Io Ip Ir It Iv Jg Jh Ji Jk Jm Jn Jq Js Li Lj Lw Ly Lz Ma Mb Mc Md Me Mf Mh Mj Ml Mn Mp Mt Mw Mx My Na Nb Nd Ne Nh Ni Nk Nl No Nq Ns Nt Nu Nv Ny Oh Om Oy Oz Pb Pc Pf Po Pz Qc Qd Qe) Jj(Et Fp Hq Hr Hv Hw In Io Ip Iq It Jh Ji Jm Jn Jo Jq Js Jt Li Lj Lw Ly Lz Mb Mc Md Me Mf Mg Mh Ml Mm Mn Mp Mq Ms Mw Mx My Na Nc Nd Ne Nf Ng Nh Ni Nj Nk Nl Nm No Nq Ns Nt Nx Ny Of Oh Oi Ok Oz Pb Pd Pf Pz Qc) Pc(Hu Hv Hw Ih Ii Ip Iq Iu Iv Jh Ji Jk Jn Jq Jt Li Lj Lu Lw Lx Ly Lz Ma Mc Mf Mj Ml Mm Mn Mp Mq Mt Mu Mv Mw Mx Nb Nc Nd Nf Nh Nj Nk No Nq Nu Nv Nx Of Om Oy Pb Po Qa Qb Qd Qe) Lu(Et Hu Hv Hw Ih Ii Io Ip Iu Iv Jg Jk Jn Jo Jq Jt Li Lx Lz Ma Mf Mj Mn Mp Mt Mu Mv Mw Mx My Nb Nc Nd Ng Nj Nn No Nq Nu Nv Oe Og Oi Ok Om Oy Po Qa Qd Qe) Og(Et Fp Hr Hu Hv Hw Ih Io Ip It Iu Jh Jn Jo Jq Jt Li Lj Ly Lz Ma Mf Mh Mn Mp Ms Mt Mw Mx My Nc Nd Nf Nj Nk Nq Nt Nu Nv Oe Ok Oy Qc Qd) Mj(Hu Hv Iq Ir Iu Iv Jg Jh Ji Jk Jn Js Jt Lj Lw Lx Ma Mf Mg Ml Mn Mp Mq Ms Mt Mu Mv Mx Nb Nc Nd Ng Nj Nn Nq Nv Oi Om Pd Po Qa Qb Qe) Mv(Hv Ii Ir Iu Iv Ji Jo Jt Li Lw Lx Mf Mg Mm Mq Ms Nb Nc Nd Nj Nn No Nu Nx Of Oi Om Po Qa Qb Qd Qe) Nn(Hv Ip Ir Iv Ji Jn Jo Lw Lx Ma Mf Mg Ms Mt Mu Nb Nc Ng Nj No Ns Nu Om Po Qa Qb Qd Qe) Oe(Et Hu Hv Ih Ip Iu Iv Ji Jk Jn Lw Ma Mn Mp Mt Mw Mx My Nc No Nq Nu Nv Ok Om Oy Pb Qd) Po(Iq Ir Iu Iv Js Jt Lw Lx Mf Mg Ml Mq Ms Mu Nc Nf Ng Nj Nx Oi Qa Qb Qd Qe) Nb(Ir Iu Js Jt Lw Lx Ma Mg

Figure 16 Continued

Ml Mq Mt Mu My Nc Nf Nj Nx Of Oi Qa Qb Qd Qe) Mu(Hv Ii Ir Iv Jo Jt Lw Lx Mf Mg Ms Nc Ng Nj No Nx Oi Om Qa Qb Qd) Jo(Hw Ii Ir Iv Jg Ji Jk Jt Lw Lx Ma Mt No Nv Om Qa Qb Qd Qe) Lx(Ii Iu Jt Lw Mg Mm Ms Nd Ne Ng Nq Nt Nx Oi Om Pd Qb) Ms(Ii Ir Ji Lw Mt No Nv Om Oy Qa Qb Qd Qe) Ir(Ii Iq Iu Jg Jt Lw Mf Mm Ng Nx Oi) Qb(Ii Iq Iu Jg Jt Lw Ma No Oi Om) Oi(Ii Jg Jk Om Oy Qa Qd Qe) Jt(Jg Ji No Nv Om Qa Qd) Lw(Iv Jg Jk No Qa Qe) Hw(Hv Js Mf Ml Mq Pd) Mg(Jk Ma Om Oy Pb) Ng(Ii Ma Nv Om Oy) Qa(Ii Iu Jg Mf) No(Js Mc Ml) Iv(Jn Js Ml) Om(Mf Mm Nx) Iu(Qd Qe) Ji(Mm Nx) MlPb NdNj QdJg

Unconstrained panels with 2 analytes, where 5.0E-2 >= 'model p-value' > 1.0E-2. Contains 1,484 panels of 6,786 total panels evaluated. : Qa(Et Fp Hq Hr Hu Hv Hw Ih In Io Ip Iq Ir It Iv Jh Ji Jk Jm Jn Jq Js Li Lj Lx Ly Lz Ma Mb Mc Md Me Mg Mh Ml Mm Mn Mp Mq Mt Mw Mx My Na Nc Nd Ne Nf Ng Nh Ni Nj Nk Nl Nm No Nq Ns Nt Nu Nv Nx Ny Of Oh Ok Om Oy Oz Pb Pd Pf Pz Qb Qc Qd Qe) Lw(Et Fp Hq Hr Hu Hv Hw Ih Ii In Io Ip Iq It Iu Jh Ji Jm Jn Jq Js Jt Li Lj Ly Lz Ma Mb Mc Md Me Mf Mg Mh Ml Mm Mn Mp Mq Mt Mw Mx My Na Nc Nd Ne Nf Ng Nh Ni Nj Nk Nl Nm Nq Ns Nt Nu Nv Nx Ny Of Oh Oi Ok Om Oy Oz Pb Pd Pf Pz Qc Qd) Ir(Et Fp Hq Hr Hu Hv Hw Ih In Io Ip It Iv Jh Ji Jk Jm Jn Jq Js Li Lj Lx Ly Lz Ma Mb Mc Md Me Mg Mh Ml Mn Mp Mq Mt Mw Mx My Na Nc Nd Ne Nf Nh Ni Nj Nk Nl Nm No Nq Ns Nt Nu Nv Ny Of Oh Ok Om Oy Oz Pb Pd Pf Pz Qb Qc Qd Qe) Qb(Et Fp Hq Hr Hu Hv Hw Ih In Io Ip It Iv Jh Ji Jk Jm Jn Jq Js Li Lj Ly Lz Mb Mc Md Me Mf Mg Mh Ml Mm Mn Mp Mq Mt Mw Mx My Na Nc Nd Ne Nf Ng Nh Nj Nk Nl Nm Nq Ns Nt Nu Nv Nx Ny Of Oh Ok Oy Oz Pb Pd Pf Pz Qc Qd Qe) Mu(Et Fp Hq Hr Hu Hw Ih In Io Ip Iq It Iu Jg Jh Ji Jk Jm Jn Jq Js Li Lj Ly Lz Ma Mb Mc Md Me Mh Ml Mm Mn Mp Mq Mt Mv Mw Mx My Na Nd Ne Nf Nh Ni Nk Nl Nm Nq Ns Nt Nu Nv Ny Of Oh Ok Oy Oz Pb Pd Pf Pz Qc Qe) Om(Hq Hr Hu Hv Hw Ih Ii In Io Ip Iq It Iu Iv Jg Jh Ji Jk Jm Jn Jq Js Li Lj Ly Lz Ma Mc Md Me Ml Mn Mp Mq Mt Mw Mx My Na Nb Nc Nd Ne Nf Nh Ni Nj Nk Nl Nm No Nq Ns Nu Nv Ny Of Oh Oy Oz Pb Pd Pf Po Pz Qd Qe) Lx(Et Fp Hr Hu Hv Hw Ih In Io Ip Iq It Iv Jg Jh Ji Jk Jm Jn Jq Js Li Lj Ly Lz Ma Mb Mc Md Me Mf Mh Ml Mn Mp Mq Mt Mw Mx My Na Nc Nf Nh Ni Nj Nk Nl Nm No Ns Nu Nv Ny Of Oh Ok Oy Oz Pb Pf Pz Qc Qd Qe) Po(Et Fp Hq Hr Hu Hv Hw Ih Ii In Io Ip It Jg Jh Ji Jk Jm Jn Jq Li Lj Ly Lz Ma Mb Mc Md Me Mf Mg Mh Ml Mm Mq Ms Na Nd Ne Nf Ng Nh Ni Nj Nk Nl Nm No Nq Ns Nt Nu Nv Ny Of Oh Ok Oy Oz Pb Pf Pz Qc) Nn(Et Fp Hq Hr Hu Hw Ih Ii In Io Iq It Iu Jg Jh Jk Jm Jq Js Jt Li Lj Ly Lz Mb Mc Md Me Mh Ml Mm Mn Mp Mq Mw Mx My Na Nd Ne Nf Nh Ni Nk Nl Nm Nq Nt Nv Nx Ny Of Oh Ok Oy Oz Pb Pc Pd Pf Pz Qc) Nb(Et Fp Hq Hr Hu Hv Hw Ih Ii In Io Ip Iq It Iv Jg Jh Ji Jk Jm Jn Jq Li Lj Ly Lz Mb Mc Md Me Mf Mh Mm Mn Mp Mw Mx Na Nd Ne Nh Ni Nk Nl Nm No Nq Ns Nt Nu Nv Ny Oh Ok Oy Oz Pb Pd Pf Pz Qc) Mv(Et Fp Hq Hr Hu Hw Ih In Io Ip Iq It Jg Jh Jk Jm Jn Jq Js Lj Ly Lz Ma Mb Mc Md Me Mh Ml Mn Mp Mt Mw Mx My Na Ne Nf Nh Ni Nk Nl Nm Nq Ns Nt Nv Ny Oh Ok Oy Oz Pb Pd Pf Pz Qc) Oe(Fp Hq Hr Hw In Io Iq It Jh Jm Jo Jq Js Jt Li Lj Ly Lz Ma Mf Mg Mh Ml Mm Mq Ms Na Nd Ne Nf Ng Nh Ni Nj Nk Nl Nm Ns Nt Nx Ny Of Oh Oi Oz Pd Pf Pz Qc) Qd(Hu Hv Hw Ii Ip Iq Iv Jh Ji Jk Jm Jn Jq Js Li Ly Lz Ma Mf Mg Mj Ml Mm Mn Mp Mq Mt My Nc Nd Ne Nf Ng Nh Nj Nk Nm No Nq Nu Nv Nx Of Oh Oy Pb Pd Pz Qe) Jg(Hr Hu Hv Hw Ih Ii Ip Iq Iu Iv Jh Ji Jk Jm Jn Jq Li Lj Ly Lz Ma Mf Ml Mm Mn Mp Mq Mt Mw Mx My Nc Nd Nf Nh Nj Nk No Nq Ns Nu Nx Of Oy Pb Pc Pd Pz Qe) Mj(Et Fp Hq Hr Hw Ih Ii In Io Ip It Jm Jq Li Ly Lz Mb Mc Md Me Mh Mm Mw My Na Ne Nf Nh Ni Nk Nl Nm No Ns Nt Nu Nx Ny Of Oh Ok Oy Oz Pb Pf Pz Qc) Qe(Hu Hv Hw Ii Ip Iq Iv Jh Ji Jk Jm Jn Jq Jt Li Ly Lz Ma Mf Mg Ml Mm Mn Mp Mq Mt My Nc Nd Ne Nf Ng Nh Nj Nk Nm No Nq Ns Nu Nv Nx Of Oh Oy Pb Pz) Ii(Et Hu Hv Hw Ih Ip Iq Iu Iv Jh Ji Jk Jn Jq Jt Li Ly Lz Ma Mf Mg Ml Mm Mn Mp Mq Mt Mw Mx My Na Nc Nd Nf Nh Nj Nk No Nq Ns Nu Nv Nx Of) Lu(Fp Hq Hr In Iq It Jh Jm Js Lj Ly Mb Mc Md Me Mg Mh Ml Mm Mq Ms Na Ne Nf Nh Ni Nk Nl Nm Ns Nt Nx Ny Of Oh Oz Pb Pd Pf Pz Qc) Iv(Hu Hv Ip Iu Jh Ji Jk Jq Jt Li Lz Ma Mf Mg Mm Mn Mp Mq Ms Mt Mw Mx My Nc Nd Ne Ng Nh Nj No Nq Nu Nv Nx Of Oi Oy Pb Pd) No(Hu Hv Hw Ip Iq Iu Jh Ji Jk Jn Jq Li Ly Ma Mf Mg Mm Mn Mp Mq Mt Mw Mx My Na Nc Nd Ng Nh Nj Nk Nq Nv Nx Oi Oy Pb) Ji(Hu Hv Ip Iq Iu Jk Jq Li Ly Lz Ma Mf Mg Ml Mn Mp Mq Mt My Nc Nd Ne Ng Nh Nj Nk Nm Nq Nu Of Oh Oi Oy Pz) Og(Hq In Iq Jm Js Mb Mc Md Me Mg Ml Mm Mq Na Ne Ng Nh Ni Nl Nm Ns Nx Ny Of Oh Oi Oz Pd Pf Pz) Mt(Hu Hv Hw Ip Iu Jk Jq Jt Li Lz Ma Mf Mg Mm Mn Mp Mq Nc Nd Ne Ng Nh Nj Nx Oh Oi Oy Pb) Jo(Et Fp Hu Hv Ih Io Iq Jh Jn Jq Li Mn Mp Mw Mx My Nc Nd Nf Nj Nq Nt Nu Ok Oy Pb Qc) Pc(Et Fp Hq Hr In Io It Jm Js Mb Md Me Mh Na Ne Ni Nl Nm Nt Ny Oh Ok Oz Pd Pf Pz Qc) Hv(Hu Ip Iu Jh Jk Jn Li Ma Mf Mg Mn Mp Mq Ms Nc Nd Ng Nj Nq Nv Nx Oi Oy Pb) Ma(Hw Iq Iu Jk Jn Jq Jt Li Ly Lz Mf Mm Ms Nc Nd Nj Nk Nu Nx Of Oi Oy) Jk(Hu Ip Iq Iu Jn Jq Jt Li Lz Mf Mm Mn Ms Nc Nd Nj Nu Nx Of) Hx(Fp Ih In Io It Lj Mb Me Mh Nl Nt Nv Ok Oz Pb Pf Qc) Ms(Et Hu Iu Jn Mn Mp Mw Mx My Nc Nd Nq Nu Ok Pb) Is(Et Fp Hq In Lj Mb Md Me Nl Nt Nv Ok Oz Qc) Nc(Mf Mn Mp My Nd Ne Nh Nl Nq Nv Oi Oy Pb) Oi(Hu Ip Iu Jn Mn Mp Mx My Nj Nq Nu Nv) Nv(Iu Lz Mf Mg Mm Mq Nj Nx Of) Mp(Hq Jt Mg Ng Nj Pd) Hu(Iu Li Mf Mg Nd Ng) Jr(Hq Mb Md Nl Nt Qc) My(Mg Ng Nj Oy Pb) Jt(Et Jn Mf Mn Ok) Nj(Mf Mn Nq Oy) Hw(Jn Me Na Nm) Jq(Mf Ml Mq) Pb(Hq Js Ny) Mn(Mg Ng) EtMm NsOy NuNd MqOk IuJn LiPd Constrained panels with 3 analytes, where 1.0E-8 >= 'model p-value' > 0. Contains 107 panels of 260,130 total panels evaluated. : Lv{aA(Iu Ji Jj Jo Jq Js Jt Li Me Mf Mg Mm Mq Ms Mx Na Nf Ng Nh Nm Nt Nx Oe Of Og Ok Pd) Og(Fr Hx Iq Jj Jl Jo Lu Mf Mg Mi Mk Mr Mz Nn Nr Nw Nx On Pa Pb Pc) Nx(Fr Hx Iq Jj Jl Jp Lu Mi Mu Mz Nd Nn Oe On Pa Pc Pg) Jo(Hx Jl Lu Mi Mk Mr Nr Pa Pe Pg) Pa(Iu Jj Jt Li Mg Ng Oe Pd Pe) Jj(Jk Jl Lu Mq) Mg(Fr Lu Nn) Mi(Nt Pd) Jl(Jt Mm) NrOe LuNg PdPe} Mi{Pa(Pd Pe) HqOg PdPg} aA{Jt(Jl Pg) NjOg} Pa{NnPd JjPe}

Constrained panels with 3 analytes, where 1.0E-7 >= 'model p-value' > 1.0E-8. Contains 258 panels of 260,130 total panels evaluated. : Lv{Jo(Fr Hw Ih Ii Io Iq Ir Jk Jp Jr Lh Li Mb Mf Mj Mq Mu Mz Nb Nd Nn No Nx Oe On Pb Pc Po) Oe(Fr Hx Io Iq Jj Jl Lu Mf Mg Mi Mk Mq Mr Mz Nd Ng Nn Nw On Pb Pc Pe) Jl(Et Ii Iu Jq Js Li Lu Mf Mg Mq Ms Ng Nm Of Oh Oi Ok Pz) Mi(Hq Iu Jj Js Jt Li Lu Lx Mf Mg Mm Mq Ms Ng Nh Nm Nq) Pa(Fp Hq Ii Iq Js Lu Mf Mh Mm Mq Ms Na Nf Nt Oy Pf Po) Nx(Io Is Jk Jr Lh Mf Mk Mq Mr Mv Mw Nb Nr Nw Pe Po) Lu(Hq Jp Js Ly Mf Mq Mz Ne Nf Nt Pd) Jj(Hx Mf Mk Mr Nd Nn Nr Pc Pe Pg) Fr(Et Jt Li Mm Mq Ms Ng Nm Ok) Jt(Hx Ir Jp Mr Mz Nr On Pe) Ng(Mk Mr Mw Nn Og Pb Pc) Mg(Jg Jp Lh Mv Nd Pc) Mq(Hx Mz Nd Nw Og Om) Pd(Lh Lx On Po) Mm(Jp Mz On) Og(Jr Nb Pe) Nn(Ms Oi) Mf(Hx Mz) Pc(Ms Oi) NtLx NcNl IsJs} aA{Jt(Hx Lw Mi Og Pa Pc Pe) Jl(Iq Mm Oe Og Oh Ok) Og(Iq Js Lw Pc) Pa(Iq Js Pd Pe) Pc(Nf Oe Oi) Pg(Jo Js) NnOi Milq MsOe} Pa{Pd(Fr Jj Jl Jo Lh Mu Mv Oe Og) Pe(Fr Jo Oe Og) Js(Hr Jl Mi) Jj(Nj Og) Jo(Oe Og) Jt(Jl Jp)} Mi{Pd(Nn Og Pc Pe Po) Hq(Jt Ms Oe) NqOg} Jl{Og(Jt Mm)} Pd{NnPe LhOe}

Constrained panels with 3 analytes, where 1.0E-6 >= 'model p-value' > 1.0E-7. Contains 640 panels of 260,130 total panels evaluated. : Lv{Jt(Ii Io Iq Is Jg Jr Lh Lx Ma Mb Mj Mk Mn Mu Mv My Nb Nd Nn No Nq Nw Om Pc Pg Po Qa) Mg(Hx Jk Jr Lw Lx Mb Mf Mk Mr Mu Mw My Mz Nb Nq Nr Nw Om On Oy Pb Pe Pg Po) Ms(Hx Io Jg Jp Jr Mb Mj Mk Mr Mu Mv Mw Mz Nb Nd No Nr Nw On Oy Pb Pe) Mm(Hx Ih Is Jh Jr Lh Lx Ma Mu Mv Mw Nn No Nw Pc Pe Pg Qb) Ng(Hx Io Iq Jg Jk Jp Lh Mj Mv Nb Nd Nq Nr Oy Pe Pg) Iu(Hx Ih Iq Ir Is Jr Lh Mj Mk Mr Mz Nb Nr Nw On Pe) Pd(Hw Hx Li Mk Mr Nb Nn Nr Om Pb Pc Pg) Mq(Jg Jp Jr Lw Mu Mv Nn Oi On Pc Pe) Pe(Fp Js Li Mf Mx Na Nf Nt Pf) Mz(Jq Js Ml Nm Nn Oh Ok Pc) Oi(Hx Io Jp Mk Mr Nr) Jr(Jn Jq Js Mf Ml) On(Li Nf Nm Of Ok) Nt(Lh Mk Mr Nr) Nh(Fr Mu Mv Nc) Hw(Js Me Mf Ml) Is(Jn Jq Ml Mx) Jp(Et Li Ok Pz) Nw(Ji Jq Nm Ok) Pc(Jh My Nq Ns) Na(Mk Mr Nr) Nf(Lh Mr Nb) Js(Iv Lh Pb) Nm(Lw Om)

Figure 16 Continued

Ne(Mi Nc) Of(Fr Mu) NnNs MjMx MlPb HxLi} Pa{Jo(aA Fr Hu Iq Jl Js Lh Lw Ly Mh Mi Mk Ml Ms Nf Nj Nn On Pc Pf Pg) Pe(Hq Hr Iq Iu Jl Jm Jp Jr Js Jt Lu Ma Ms Mu Mv Mz Nf Ng Ni Nw Pd) Pd(Hr Hw Iq Jg Jp Js Jt Lu Lw Lx Ma Mk Mr On Pb Pc Pg) Js(Fr Hq Is Ji Jj Jp Jr Lh Mz Nn Nw Oe Og) aA(Hq Iu Jj Mm Ms Nf Ng Nj Nx Oe Oh Pf) Oe(Fr Hq Iq Jj Jl Na Nf Ng On Pc) Jj(Hu Iq Jl Jn Jt Jx Lu Ly Ml) Og(Iq Jl Jt Na Ng Nj Pc Pf) Ng(Fr Jk Jl Lj Mi Mu) Jt(Fr Hq Mi Mz Nf On) Jl(Mm Nx Oh Pf) Mi(Hq Iq) MsPc} Mi{Pd(aA Fr Hq Hu Hw Hx Jk Jl Jp Jr Js Lh Li Lu Ly Mk Mr Mu Mv Nc Nj Pb) Hq(aA Iq Iu Ji Jj Jl Jo Jq Lu Mg Nd Nf Nj Nm Nx Ok Pg) Jo(aA Hx Ii Lh Lu Ly Mk Mr Ms Nj Nr Og Pc Pe Pg) Js(aA Hx In Jl Jr Lh Ms Mz Qa Qb) Jt(Is Jl Jp Lh Mk Mr Mz Nr On Pc) Og(Hx Mg Nd Nr Nt On Pb Pc) Ng(aA Jk Jl Nt Pc Pg) Ms(aA Jj Jl Ne Pc) Nt(aA Jl Jr Nj) Oe(Nq Nr On Pc) Mg(Fr Lu Pc) Jj(Lu Ly Nj) Jl(Mm Nq Oh) Nx(aA On Pc) aA(Iu Jq) NqMu MmJp} Jl{Jt(Is Jp Lh Lw Mj Mk Mm Mr Ms Nr Oe Om On Pc Pe Pg) aA(Iu Jj Jo Jq Js Ms Mx Ne Nh Nn Nx Ny Oi Pd Pz) Og(Iq Jj Mk Nj Nn Nr Ny Oh On Pb Pc) Oe(Jj Lu Mk Mm Mr Ms Nr Nx On Pc) Mm(Jj Jp Ms Nx Oi) Jj(Ms Nx Oh Pg) Pc(Ms Ng) Pd(Lh Pe) JoPg} aA{Pg(Ii Iq Iu Jj Mg Mm Nf Ng Nt Nx Oh Ok Pd Pf) Nj(Iu Jj Jo Mm Nd Nh) Ly(Iu Jj Jo Ng Nx) Lw(Ji Nm Nx Ok) Js(Hx In Jr Pe) Pc(Jo Ms Ng Nx) Jt(Fr Lh Mz) Pd(Nn Pe Po) Jo(Hx Lh) NnMx NcNe NgJk NhIq JnJr} On{Oe(Fr Jj Jo Jt Ms Nf Nx Og Ok Pd) Og(Jj Jo Jt Ms Nf Ng Ok Pd) Ok(Ms Ng Nx) JoPg JpJt NxOm} Pd{Pe(Fr Lh Mu Mv Oe Pc Pg) Lh(Jj Jo Jt Og) JjPg} Og{Hx(Jj Pc) IsJs JjPg JoLh} Fr{Mk(Ng Oe) NrOe MgPg} Jo{Pg(Jj Mr) JsLh} NrMuOe MgJjPg NgJkPc JpJtPe

Constrained panels with 3 analytes, where 1.0E-5 >= 'model p-value' > 1.0E-6. Contains 1,072 panels of 260,130 total panels evaluated. :
Pa{Hq(Fr Hu Hv Hx Ih Iq Jl Jn Jo Jr Lj Lu Lz Mf Mh Mj Ml Ms Mu Mx Nb Nd Nj Nn Og Pc Pf Pg Qd) Ng(Hr Hu Jg Jh Jo Jp Js Lh Lu Lz Ma Mf Mh Mj Ms Mv Mx Mz Na Nf Nj Nn On Pc Pg) Oe(Hx Is Jg Jp Jr Lx Mg Mi Mk Mr Mu Mv Mz Nd Ne Nj Nl Nn Nr Nt Nw Pf Qa Qb) Nf(Fr Hv Hx Iq Jj Jl Jn Js Lh Lj Lu Lz Mh Mi Ml Ms Mx Nn Nw Og On Pc Pf) Jl(Fp Ii Iq Iu Li Mg Ms Mx Na Nm Nn Nr Nt Nv Ny Of Oi Ok Oy Pz) Jt(Iq Is Jg Jh Ji Jr Lh Lw Lx Mh Mk Mr Mu Nj Nn Nr Pc Pf Qa Qd) Js(Ir Jg Jq Lu Lx Ma Mh Mu Mv Na Nj Om On Oy Pc Pf Qa Qb) Og(Fr Iu Jg Jp Jr Lx Mi Mv Mz Nl Nt On Pb Qb) Mi(Iu Lx Mg Ms Mx Nj Nq Nt Nx Pf) Fr(Iq Iu Mg Mm Ms Nj Nx Oi Pf) Ms(Iq Iu Jg Mz Na On Pf) Jo(Jg Jp Lu Mr Mv) Nj(Iu Lu Nr Pf) Iq(Lu Mf Oy Pf) Mg(Jg Lu Pc) Nx(Om On Pc) Mh(Na Nt) Mm(Jp Mz) Iu(Oy Pf) Oi(Nn Pc) MlNa JpPf} Mi{Ng(Fr Hu Hx Ii Jg Jp Jr Js Lh Lu Lx Ly Mg Mj Mk Mr Mu Mv Mw My Nb Nd Nc Nj Nn Nq Nr Of Og Oy Pb Pc) Js(Fr Hw Ir Is Iv Jn Jp Lu Lx Ly Mj Mk Mr Nb Nj Nn Nq Nr Nt Nw Oe Pb Pe Pg Qd Qe) Nx(Fr Hx Ii Jg Jl Jp Lh Ly Mk Mr Mz Nb Nj Nq Nr Om Oy Pe) Nt(Iq Jj Jo Lh Mg Mk Mr Ms Mz Nc Nn Nq Oe Pc Pe Qa Qb) Nq(Fr Jj Jk Jo Jr Jt Lu Lx Mv Nf Nn Pc Pg) Mg(Iq Jg Jk Jl Lh Lx Ly Ma Ms Mv Nd Pg) Jl(Iq Iu Jj Jo Lx Mx Nj Ny Ok) Jt(Fr Hx Iv Jg Jr Mj Nb Og Pe) Oe(Hx Ii Jg Ly Mk Mr Nb Nd Ne) Og(Jj Jr Mk Mr Ms Nb Ne Nj) Jo(Hu Hw Jk Mj Nb On Oy) Ms(Jp Mk Mr Nr On Oy) Nj(Fr Iu Lu Mm Nh Pc) Iq(Hx Jp Lu Mk Mr Nr) Jj(Jk Lx Mk Pc Pg) Mx(Is Iv Mj Nr) On(Ji Nf Nm Ok) Lx(aA Jr Pc) Mm(Fr Lh Mz) Jn(Is Jr Mz) Jp(Nh Oh Ok) Ml(Hx Jr) Oi(Nn Pc) NmLw NrNa LuIu NcNe NfLh} Jl{Ng(Fr Hu Jg Jk Lh Lu Mk Mr Mx Nb Nh Nj Nn Nr On Oy Pb Pe Pg) Jo(Hu Hx Lh Lu Lw Ly Mj Mk Mr Mt Mx Nb Nh Nj Nr On Pc Pe) Lu(Iu Jj Jt Mg Ms Nh Nj Nq Nx Of Oh Oi) Ms(Iu Mk Mr Nb Nr Nx Ny Oh On Oy) Jt(Hu Hx Jj Mz Nb Nj Nw Oh Qd) Nx(Iq Iu Jp Lw Ly Om Pc Pg) Mg(Fr Lh Mx Nh Pc Pg) Jj(Hu Jk Mx Nh Nj Ok) Pd(Lx Mk Mr On Pg Po) Oi(Iq Nj Nn Pc Pg) Nh(Iq Iu Jp Nj) Js(Is Jr Lh Pe) Ok(Jp Mr On Pe) Iu(Hu Nj Oh) Pg(Ii Of Pz) Ne(Nc Nj) Jp(Nn Oh) Pc(My Ns) NtLh MqOe MxIs PzPe OfOh} Og{Pc(Fr Hu Is Jj Jk Jo Jr Lh Lu Mg Mj Ms Mv My Mz Nb Ng Ns Om Pe Pg Qb) Fr(Hx Is Jj Jo Jr Jt Mg Mk Mr Ms Mz Nb Nc Ng Nj Nr On Pb Pe) Nr(Hx Is Jj Jo Jp Jr Ms Mv Mz Oe Qb) Mk(Hx Is Jj Jo Jp Jr Ms Mv Mz Nw Oe) Pb(Hx Is Jj Jr Ms Mu Mv Mz Nn Nw Oe) Pe(Jj Jo Jp Jr Jt Mv Mz Pd) Mr(Jj Jo Jp Jr Mv Mz Oe) On(Hr Iq Mm Mq Mv Nj Nx) Is(Ir Jn Jr Jt Ml Mx) Lh(Jj Js Jt Mg Nt) Hx(Jo Oe) Jj(Ii Jk) Nw(Js Mt) MqOm MsNb NgJg JoPg} Fr{Ng(Hu Hx Ii Iu Jk Lh Lu Ly Mr Ms Nb Nj Nr Oe Oy Pb Pc Pe Pg) Mg(Hx Ii Lh Ly Mk Mr Ms Nb Nj Nr Oe Om On Pb Pc Pe) Jt(Hx Ir Is Iv Jp Jr Lh Mj Mk Mr Mz Nr On Pe) Oe(Hx Jj Jr Mr Mz Nb Pc Pe) Ms(Mk Mr Nb Nr On Pc) Jo(Lh Mk Mr Nr Pe Pg) Nx(Hx Jr Om On) Oi(Nn Pc) IsJs JjPe JrLi LhPd} Lh{Jo(Hq Jp Lu Lw Ly Mg Mj Mk Mm Mr Ms Ne Ng Nj Nq Nr Nt Nx Oe Oh On Pc Pe Pg) Jj(Js Jt Lu Mg Mk Mm Mq Nf Nt Nx Oe Ok Pc) Pd(Iq Iu Jr Lw Ms Mz Ng Nn Oi Pg) Jt(Is Jp Lw Mk Mr Mz Nr Nt On) Pc(Mg Ms Nf Ng Oe Oi) Ng(Jk Js Mq Nx) Oe(Js Mg Mk Nr) Js(Jr Mz) NtNx LvLi} Oe{Nr(Hx Is Jg Jj Jo Jp Jr Lx Mv Mz Nn Nw On Pc Pg Qa Qb) Mk(Hx Is Jg Jj Jo Jp Jr Lx Mv Mz Nn Nw On Qa Qb) Mr(Jj Jo Jp Jr Lx Mv Mz Nn Nw Qb) Pc(Hx Jr Ms Mz Pe) Jj(Hx Jk Pe Pg) Is(Jn Js) Jo(Pe Pg) On(Mz Ng) PoPd} Pe{Pd(Iq Jg Jj Jo Jp Jr Js Jt Lj Lu Lw Lx Lz Ma Mf Ml Mp Mx Mz Nj Nw On Pf Po) Jo(Jk Jp Js Ml Mv Mz Nj Nn Pc Pg) Jt(Is Jj Mz On) Jj(Lu Pc) MsPc NgJk} Pc{Ms(Hu Hx Is Jo Jp Jr Lx Mj Mv My Mz Nw On Pg Qa Qb) Ng(Hu Hx Jr Lu Mv My Mz Pg) Mz(Jt Oi) JoPg JrOi NxOm} Jt{On(Is Iv Lx Mj Mk Mm Mq Mr Ms Mz Nf Nj Nr Nx Pg Qa) Mz(Mj Mk Mr Nr Pg) Jp(Mk Mr Nr Pg) LvJk JjPg} Lv{Hw(Hv Jn Jr Na Nm) Iv(Jn Jr Ml Mx) Lx(Hq Ne Ng) Js(In Ir Om) No(Li Nm) Pg(Hq Of) MeOm MwMy NfPd IrJq IsJr} Pg{Jo(Is Jp Lw Mj Mk Mz Nr) Ng(Jg Jj Lu) Nx(Jj Om On) Pd(Lx On) MqJj IsJs} Ng{Jk(Jg Mk Mr Nr Oy Pb) Mv(Mk Mr Pb) Mu(Mk Pb) LuJg} On{Ms(Jo Mz Nf Pd) Ok(My Nf Of Oy) NfNx} Jj{Qb(Lu Mk Mr) Jr(Jk Mk Mr) LuMz IsJs} aA{NnMt NqMu NdHq HxNx} Mz{LuJs MkMs} Jr{NnOi IsJs}

Constrained panels with 3 analytes, where 1.0E-4 >= 'model p-value' > 1.0E-5. Contains 1,992 panels of 260,130 total panels evaluated. :
Og{Mj(Hu Ih Jg Jj Jk Jp Js Lh Lu Lz Mf Mk Ml Mu Mv Mx Mz Nb Nj Nn Nw Om Pb Pg Qb) Nw(Ii Is Jg Jj Jn Jo Jr Jt Lu Ml Mm Mr Ms Mv Mx Mz Nb Nj Nr Nx Oh Oi Pd Pe) Lh(Hq Is Iu Jg Jp Jr Lw Mk Mm Mv Mz Nb Nd Ne Ng Nj Nn Nq Nr Nx Oe Pb) Jj(Ir Is Iv Jg Jp Jr Mt Mu Mv Mz Nb Nn No Nu Nv Om Oy Po Qa Qb Qe) Ii(Fr Ir Is Jg Jo Jp Jr Ms Mu Mv Mz Ng Nj Nn Oe Om Pe Qa Qb) Jr(Hx Jg Jk Jn Jp Js Lu Lw Mu Mv Nb Nj Nn Om Pg) Jg(Hx Iv Jo Lu Mg Mk Mr Ms Mz No Nr Oe Pb) Jp(Hx Jt Lu Lw Ly Mm Mv Nb Nj Om Pb Pg Qb) Mz(Jk Jt Lu Ms Mu Mv Nb Nj Oe Oy Pg) Is(Hx Iq Iu Jo Lu Mr Mv Nb Nx Oe Pe) Pb(Hu Jk Jo Lx Ml Nj Om Pe Pg Qa Qb) Nn(Hx Mk Mr Nb Nj Nr Oi Om Pe Pg) Nb(Jo Jt Mu Mv Ng Nj Oe Qb) Om(Jo Jt Lu Mg Ms Ng Nr Nx) Pg(Hq Iu Jt Mg Ng Nr Nx Pd) Mr(Hx Jt Ms Mu Nj Qa Qb) Mk(Jq Mu Ng Nj Qa Qb) Mv(Hx Iv Jo Lw Ng Nj) Nr(Jt Mu Nj Qa) Pe(Hx Nj Oe Qb) Mu(Hu Ms Nj) Jo(Jk Nv Po) No(Js Pc) Lu(Lw Qb) Ng(Jk Oy) Hw(Mf Mq) Hx(Lw Nj) PoPd LxHq MsOy IvJs OiPc} Oe{Pc(Ii Ir Is Iv Jj Jk Jn Jp Lu Lx Mg Mj Mk Mr Mt Mu Mv My Nb Nc Ng No Ns Nw Pb Pg Po Qa Qb Qd Qe) Jj(Ii Ir Is Iv Jg Jp Jr Lx Mj Mt Mu Mv Mz Nb Nn Nv Nw Om Oy Po Qa Qb Qd Qe) Nw(Hx Ii Jg Jn Js Jt Lh Lu Mj Ml Mm Ms Mt Mv Nb Nx Pe Pg Qb) Pg(Hq Ii Is Jp Jr Lu Mg Mj Mk Mq Mr Mz Ng Nn Nx Pd) Hx(Iq Jg Jo Jp Lu Mf Mj Ml Mr Ms Mu Mv Nn Pe) Is(Iu Jg Jo Jp Jr Jt Lu Ml Mr Ms Nb Nn Nx) Pe(Jg Jp Jr Jt Lx Mk Mv Mz Na Nf Nn Nr Qb) Lh(Iu Jp Jt Lu Mj Mm Mr Ne Ng Nn Nt Nx) Mz(Ii Jg Jk Jt Lu Mj Ms Mv Nb Nn Oy) Nb(Jo Jp Jr Lx Mq Ms Mv Ng Nn Qb) Jg(Ii Jr Lu Mg Mj Mr Ms Ng No Qb) Mj(Jp Js Lu Mk Ml Mu Mx Nn) Nr(Ir Jk Ma Ms Mt Qd Qe) Mk(Ir Ms Mt Mu Ng Qd Qe) Mr(Ma Ms Mt Mu Qa Qe) Jr(Jn Jp Js Lu Mv Nn) Ii(Jp Lx Mv Nn Qb) Lu(Ir Jp Qb Qe) Ng(Mv Oy Pb) Hw(Mf Ml Mq) Qb(Jp Mv Nn) Lx(Hq Mi) Js(Iv No) MlPb} Jo{Nr(Hu Hx Ir Is Jg Jk Jp Jq Jr Lx Ma Mj Ms Mt Mu Mv Mz Nj Nn Nv Nw Om On Pc Pe Po Qa Qb Qd) Mr(Hu Hx Ir Is Jk Jp Jq Jr Lx Ma Mj Mt Mu Mv Mz Nj Nn Nv Nw Om On Pc Pe Po Qa Qb Qd) Mk(Hu Hx Ir Is Jk Jp Jq Jr Lx Ma Mj Mt Mu Mv Mz Nj Nn Nv Nw Om On Pe Po Qa Qb Qd) Pe(Fp Hu Hx Ii Is Jj Jr Lu Lw Lx Ma Mh Mj Ms Mu Nb Nf Nv On Pf Qa Qb Qd) On(Fr Hu Hx Ji Jk Jp Jr Lu Mj Mm Mq Mv Mz Nf Nj Nm Nn Ok Qa Qb Qd) Pc(Fr Hx Ir Is Iv Jr Ma Mj My Mz Ng Ns Nw Oi Qa Qd) Fr(Hw Hx Ii Is Iv Jr Lu Ly Mj Nb Nj Qb) Lh(Hw Is Iv Jk Jr Ml Mv Mz Nb Nd Nf Nn) Mj(Hx Is Jk Jp Mu Mv Mz Nn Nw) Hx(Jp Lu Lw Mv Nj Nn) Is(Jn Jr Js Lu Ml) Lu(Mz Nw Om) Nb(Jp Ms Mv) PoPd LxHq MzIi HwJl} Jj{Jk(Ih Ir Is Iv Jp Jt Mg Mj Mk Mr Mt Mz Ng Nr

Figure 16 Continued

Nw On Pc Pe Qa Qb Qd) Jr(Fr Hu Hx Ii Is Iu Jn Js Lh Lu Nb Nj Nn Nr On Oy Pc Pe Po) Lu(Hx Ih Ir Is Jg Jp Mj Mt Mv Nw Om On Pc Qa Qd Qe) Mz(Hu Ii Ly Mj Mk Mr Ms Mv Nj Nr On Oy Pc Pe) Nj(Fr Hx Lh Mj Mk Mr Nb Nn Nr On Pc Pe Po) Mv(Hx Ii Is Ly Mj Mk Mr Nb Nr On Pc Pe) Qb(Hu Ii Lh Ly Mj Nb Nn Nr On Pc Pe Po) Pc(Ih Ir Is Mg Mj My Ns Oi Qa Qd) Pe(Fp Js Mf Mk Ml Mx Na Nf Pf) Fr(Hx Jt Lh Ly Mk Mr Ms Nr) On(Mm Mq Ms Nf Nx Ok Pd) Nn(Ir Mj Mr Nb Nr Oi) Jp(Ii Ly Mk Mr Nb Nr) Mj(Hu Ih Mf Mu Mx) Ms(Hx Is Nb Nr Oy) Mt(Ii Mk Mr Nb Nr) Is(Ir Jn Ml Mx) Qa(Ii Mk Mr Nr) Ml(Hx In) Na(Hw Nr) PoPd LxHq Lylr MfHw MmNw MrMu} Ng{Lh(Fp Hv In Ir Jg Jn Jp Jr Jt Lu Me Mf Mk Ml Mm Mr Mu Mv Mx Na Nf Nm Nn Ny Oy Pb Pg Qa) Jg(Hu Hx Ii Jr Ly Mj Mk Mq Mr Ms Mv Nb Nj Nn Nr Oy Pb Pc Pe Po) Pg(Ii Iu Jk Jp Js Jt Mk Mr Mu Mv Nb Nn Nr Nw Nx On Oy Pb Pe) On(Ji Jk Jp Lu Mk Mm Mq Mr Mu Mv Nf Nn Nx Oy Pb Pc Pe) Mk(Hu Is Jp Jr Lx Ma Mt Mz Nn Nv Nw Om Pa Qa Qb) Jk(Hx Ii Jp Jr Lx Ma Mj Mp Mv Mz Nb Nw Om Po) Pc(Is Jp Lx Mj Ms Mu Nb Pe Qa Qb Qd) Lu(Hx Is Jp Mv Mz Nw Om Pe) Pb(Is Jp Jr Ma Mt Mz Nn Pa) Mr(Jp Jr Ma Mu Mz Nn Pa) Oy(Jp Mu Mv Mz Nn Pa) Nb(Jp Ma Mu Mv Nn) Pe(Jp Ma Mu Mv Nn) Li(Jp Mv Nn) NnHx NrMv IsJs} Fr{Nx(Ii Is Lh Lw Ly Mk Mr Mz Nb Nj Nr Pc Pe Pg Qb) Iq(Hx Ir Is Jr Lh Mj Mk Mr Mz Nr On Pe Qb) Pd(Hw Hx Lx Ly Mj Mk Mr Nr Om On Pb Pg Po) Jt(Hw Ih Jn Lw Ly Nb No Pc Pg Qa Qb Qd) Iu(Hx Ir Is Jr Lh Ly Mk Mr Nr Pe Qb) Mm(Hx Ir Is Jp Jr Lh Mz Nw Pe Qb) Ms(Hx Is Jr Ly Mj Mz Oi Oy Pe Qb) Nj(Hx Jl Jr Mk Mr Mz Nr Oi Pe) Of(Hx Jl Ly Mk Mr Nr Pa Pe Pg) Nq(Hx Jl Lh Lu Lx Pc Pg) My(Hx Mk Nb Pa Pb Pc) Oi(Hx Jr Mk Mr Nr Pe) Nf(Hx Lh Mk Mr Pe) Is(Jn Ml Mx Oh Pz) Pa(Mh Nt Oh Oy Pz) Qb(Nn Ny Oh Pz) Nt(Lh Lx Pe) Mz(Nn Oh Ok) Js(Jr Lh Pe) Pc(Jh Mv Ns) Nc(Ne Nh) Pz(Hx Jp) Jl(Nn Ny) LxMi MfHw liPg IrNy JrOh PePf} Jt{Pe(Ir Jg Jk Jn Jr Lh Lx Ma Mk Mr Mt Mu Mv Nn Nr Nv Nw Om Pc Pg Qa Qb Qd Qe) Mz(Hu Ii Ir Is Jg Jk Jp Lu Lw Ma Ms Mu Mv Nb Nj Nn Oy Qd) Lh(Hq Ir Iu Iv Jr Js Mf Mg Mj Mm Ms Ne Nn Nq Nx Pc Qd) Is(Ii Jn Jp Jr Js Lu Lw Mj Mk Ml Mr Nb Nr Nw Pc Pg) Jp(Hx Ii Ir Jr Lw Mj Nb Nw Om Pc Po Qa Qd) Mr(Jg Jr Lx Ma Mt Mv Nv Nw Pg Qa Qb Qd) On(Ir Jg Jk Jr Lu Ma Mt Mv Nw Oh Qb Qe) Nr(Jg Jr Lx Ma Mv Nv Nw Pg Qa Qb Qd) Mk(Ir Jg Jr Lx Ma Mv Nw Pg Qa Qb Qd) Pg(Ir Jr Lw Mg Mj Pa Pd Qd) Pc(Ir Ns Qd) Mj(Jg Nw) LuNw LxHq QbPa} Pa{Mg(Hr Lh Lj Lz Ma Mh Mu Mv Mx Mz Na Nn On Pg) Nx(Is Jg Ji Jp Jq Lh Lw Mu Mz Nj Nn Nw Pg) Ms(Jp Jr Lw Lx Mk Mv Ni Nl Nn Nt Oy Qb) Na(Hr Hx Ii Jr My Nb Ny Of Oy Pb) Nj(Hr Jp Mm Ne Ni Nn Nt Oi Oy Pc) Mx(Is Jp Jq Jr Mz Nw) Nt(Hr Lh Lx Mz Pg) Mh(Lx Nd Ne Nl Nq) Lu(Iu Nq Oy Pf) Pc(My Ns Of Oy) Mm(Lh Nw On) Mz(Nn Oh Pf) Jp(Li Nn Pz) Nq(Hr Mu) Hq(Lh Mv) Ii(On Pg) Is(Jn Oh) NrLj LwMq MwMy NcNe JgOi JnNw JrLi OfOn} On{Nx(Hx In Iq Is Jp Jq Jr Lh Lu Lx Mg Mm Mq Ms Mu Mv Mz Nj Nn Nv Nw Of Oi Pc Pe Pe Qa Qb) Pd(Hx Jp Jr Lu Lx Mj Mq Mv Mz Nd Nf Nj Nn Po Qa Qb) Ms(Jp Jr Mg Mk Mm Mq Mr Mu Mv Nn Nr Pg Pz Qb) Mg(Jl Jp Lu Ma Mm Mu Mv Nj Ok Pc Pg) Mm(Iq Jp Jr Mz Nj Of Oi) Oi(Lu Mq Nn Ok Pc) Nf(Jl Jr Lu Nn) Ok(Jp Mw Mz Nq) Jr(Iq Js Lu) Jl(Iq Mx) LuJp MqOf IiPg} Pc{Mg(Hu Hx Ir Is Jg Jk Jp Jq Jr Lu Lx Ma Mt Mu Mv Mz Nj Nw Om Pe Pg Qa Qb Qd) Oi(Hu Hx Ir Is Jk Jp Lu Lx Mj Mt Mu Mv My Nb Nw Pe Pg Qa Qb Qd) Mz(Js Lu Mm My Nf Nj Ns Nx Oh Pd) My(Hx Jp Jr Lh Lu Pg Qb) Ns(Hx Jp Jr Lu Pg Qb) Nx(Jq Lh Nw Pe Pg) Jl(Nf Nq Of Pz) Nf(Nw Pe) LxPd} Ms{Mk(Hx Is Jg Jp Jr Lh Lx Mp Mt Mu Mv Nn Nw Pg Qa Qb) Nr(Hx Is Jp Jr Lh Lx Mu Mv Mz Nn Nw Pg Qb) Nn(Hx Mr Mx Mz Nb Oi Pe Pg) Mr(Jp Jr Mu Mv Mz Nw Qb) Nw(Lu Mm Nb Oy Pe Pg) Mz(Mv Nb Oy Pe) Lh(Js Mm Nt Nx) Is(Jn Jr Js) Mv(Nb Pe) Jg(Hx Mg) Jp(Nb Pe) PoPd JrOy} Jl{Js(Iv Jp Lx Mj Mr No Nr Nw Om Pb Pg) Pd(Hw Li Mj Nr Nw Om Pb) Mx(Iv Mj Mr Nr Pe) Ok(Lh Mj Mk Nr Nw) Iq(Jp Mr Ne Pe) Jp(Nm Ny Pz) Pe(Fp Nt Pf) Pg(Nn Nv Ny) Jn(Is Jr) Jq(Nw Om) NnNq NrNa NtLx LwMg MkOf MlOm MqNj MtNw NcNl NfLh HvHw} Nn{Oi(Hu Hv Hx Ii Ir Is Iv Jg Jk Jn Jp Lh Lu Lx Mf Mj Mk Mr Mv My Mz Nb Nc Nj Nr Nw Pe Pg Qa Qb Qd Qe) Pd(Lx Mr Nr) Nf(Lh Pe) LxMi MgPg} Js{Jr(Iv Lu Lx Mj Mk Mr Mz Nj Nr Pb Pe Pg) Lh(In Is Iu Mg Mq Nx Oi Qa Qb) Is(Iq Jp Lu Lx Mz Nj Pe) Mz(Mj Pe Pg) Nw(Lu Mq Nx) Mi(Mt Mv)} Nx{Lh(Hq Is Iu Jp Jr Mg Mm Ne Nq Nw Om Pg) Pg(Is Iu Jp Jr Mg Mz Nw Pd) Nw(Jn Lu Mm Nj Pe) Mz(Mk Mr Pe) LuIs LxHq MiNd OmPe} Pd{Pg(Li Lu Lw Mj Mk Mr Nr Nw Om Pb) Lx(Hq Hx Jp Jr Mv Mz Nw Po) Nw(Hw Li Mk Mr Nr) Mz(Lu Mk Mr) PoMp MkPc} Mg{Pg(Iu Jg Jp Lh Lu Lw Mu Mv Nw Om) Lh(Iq Jg Jp Mm Mv) Lu(Mz Nw Om) Mv(Mk Pb Pe) Jg(Hx Om Pe)} Mm{Jp(Hx Is Lh Lw Mk Mr Mz Nr Nw Pe Pg) Mz(Lh Lx Mk) Lh(Iu Oi) LuNw} Mi{Nd(Mh Mt My Nf Of Pb) Nf(Ii Nb Ne Pe) Lx(Mt Mz Nj) MzJq HvHw NwOk} Lu{Mz(Ml Nf Nj Oi) Nw(Ml Mt Nj Oi) Is(Mx Oi) Jp(Lw Nj) LxHq} Nf{Nw(Lh Mk Mr Pe) NtLh PePf} Hq{Nd(Mk Mr Pb Pe) LxMq} Nt{Lh(Iq Iu)} Mk{MvOf MzOi} NqLxMu IsJnJr Constrained panels with 3 analytes, where 1.0E-3 >= 'model p-value' > 1.0E-4. Contains 3,210 panels of 260,130 total panels evaluated. :
Jo{Lw(Hu Hw Ii Ir Is Iv Jg Jk Jp Jr Lu Lx Mj Mu Mv Mz Nb Nn No Nv Pc Po Qa Qb Qd Qe) Hw(Hv Is Jg Jk Jn Jp Jr Js Lx Ma Mf Ml Mp Mq Mu Mv Mz Nb Nn Nw Og Om On Pc Pd) Ii(Ir Is Iv Jg Jk Jp Jr Lx Ma Mj Ms Mu Mv Nj No Ns Nv Nw Oe Oi Po Qa Qb Qd Qe) Mj(Hu Ih Ir Jg Ji Jr Jt Lu Lx Ma Mf Mn Mx Nb Nj Nv Oe Og Om Oy Po Qa Qb) Nn(Ip Ir Is Iu Iv Jk Jp Jr Jt Lx Ma Mv Mz Nb Nj No Nu Om Po Qa Qb Qd) Pc(Ih Iu Jh Jk Jp Jq Jt Lx Ly Mu Mv Nb Nc Nj No Nq Nv Om Po Qb Qe) Nb(Hu Ir Is Jk Jr Lx Ma Mu Mz Ng Nj Nw Om Po Qa Qb Qd Qe) Lu(Et Ir Iv Jg Ji Lx Ma Mn Mu No Nv Ok Po Qa Qb Qd Qe) Jk(Ip Ir Is Iv Ji Jp Jr Jt Lx Mz Ng No Nw Oe Om Po Qd) Mv(Ir Is Iv Jp Jr Jt Lx Ly Mz Nj Nw Oe Om Po Qb) Po(Hu Ir Is Jp Jr Ma Mu Mz Nj Oe Qa Qb Qd) Om(Ir Iv Jp Jr Ma Ms Mu Nj Oe Qa Qb Qd Qe) Og(Ip Ir Iv Ji Jt Ma Oy Qa Qb Qd Qe) Oe(Ir Iv Jg Ji Ma Nv Qa Qb Qd Qe) Ms(Hx Is Jg Ji No Nv Nw Oy) Mu(Hx Ir Iv Jr Jt Nj Qb Qd) Hu(Ir Is Jr Mz Nw Qa Qb Qe) Nj(Is Jp Jr Ma Mz Nv Nw) No(Hx Jg Js Mc Ml Qb) Lx(Jp Jr Nd Ne Nq Qd) Ir(Iq Is Jg Jp Ly Oy) Iv(Jg Jn Jp Jr Js Ml) Ly(Jp Ma Mz) Is(Hx Mx Nv) Qb(Jg Jp Jt) Oy(Mz Ng Qd) Jg(Jr Qd) Jt(Nv Nw) Pb(Ml Ny) MfJj IuNw JpJr OhOn} Jt{Mj(Hu Hx Ir Ji Jk Jr Lw Lx Ma Mf Mk Mn Mr Mt Mu Mv Nn No Nr Nv Om Pc Pe Qa Qb Qe) Hx(Ir Is Jg Ji Jr Lw Lx Ma Mk Ml Mr Mt Mu Mv Mz Nn No Nr Om Pc Pe Qd) Nr(Et Hu Ir Ji Jk Jn Jq Lw Mn Mp Mt Mu Mw My Nn No Nq Om Po Qe) Mk(Et Ji Jk Jn Jq Lw Mn Mp Mt Mu Mw My Nn No Nq Nv Om Po Qe) Mr(Et Hu Ir Ji Jk Jn Jq Lw Mn Mp Mu Mw My Nn No Nq Om Po Qe) Nw(Iv Jk Lx Ma Ml Mm Ms Mt Mv Mz Nc Nj Pc Pg Qa Qb Qd Qe) Jr(Hu Ii Ir Jg Jk Lw Lx Ma Mu Mv Mz Nb Nj Nn Om Pc Qd) Qa(Ii Jg Lw Ma Mu Mv Mz Nb Nn No Oe Og Om Pc Pg Po) Lw(Ir Jg Jk Lx Mv Nb Nv Om Pc Pe Qb Qd Qe) Ir(Ii Jg Jk Lx Ma Mn Mu Mv Nb Nn Om Po) Pc(Iv Jn Lx Ma Mv My No Ok Om Pg Qb Qe) Jp(Hw Iu Iv Jg Jk Lx Mv Nn No Nu Qb) Pe(Et Iu Ji Jq Lu Mp Mw Nf Nq Pf) Qd(Ii Jg Nb Nn Oe Og Om Po) Is(Hu Jg Ms Mv Mx Nn Po) Og(Jg Ji Jk Ma No Nv Qe) Om(Iv Lu Lx Ms No Oe Qb) Nb(Lx Ma Mv Qb Qe) No(Jg Js Nn Pg) Lh(Lx Nd Nf Nj) Jj(Mf Mq Nv) Lx(Ii Nn) Jg(Ms Qb) Pg(Hq Iv) LuJi MaIi NvOe} Ms{Mj(Hu Hx Ih Is Jg Ji Jk Jp Jr Js Lh Lw Lx Mf Mk Ml Mt Mu Mv Mx Mz Nn Nw Om Oy Pg Qb) Oy(Hx Ir Is Ji Jp Lh Lw Lx Mg Mp Mt Mu Mv Ng Nn Oe Om Pe Qa Qb Qd Qe) Nn(Ii Ir Is Jg Ji Jp Lh Lw Lx Mu Mv Nj No Om Pb Pd Qb Qd) Mu(Hu Hx Ii Is Jp Jr Lw Mf Mg Mz Nb Ng No Oe Oi Pe Qb) Ii(Jg Ji Jj Jp Jr Lw Lx Mp Mv Mz Ng Nw Oe Oi Om Qb) Is(Ir Iu Jg Jp Lw Ml Mr Mv Mx Nb No Nw Oi Pb Pe) Jg(Jj Jr Lu Mr Mz Nb No Nr Nw Oi Pe Pg Po Qb) Mv(Hx Jl Jp Jr Lw Mg Ng No Nw Oi Po Qb) Jp(Hx Ir Jr Lh Lw Ly No Nw Pg Po Qb) Mr(Hx Ji Lh Lx Ma Mp Mt Om Pg Qa) Nb(Hx Jr Lh Lx Ma Mp Mt Pg Qb) No(Jj Jr Lw Mz Oe Og Om Qb) Lh(Hq Iu Lu Lw Ne Ng Nw Oi) Nr(Ji Ma Mp Mt Om Pe Qa) Jr(Hx Jk Jn Js Lw Mw Pe) Nw(Hx Jj Jk Jn Js Nx Oi) Mk(Ji Ma My Ng Om Pe) Mz(Lw Mm Nx Oi Pg) Ji(Jj Lu Nx Oe Og) Om(Jj Lu Mg Nx Oe) Og(Lw Mp Mt Nv) Pe(Fp Lx Nf Qb) Hx(Lu Lw Oi) Oe(Mt Nv Qb) Lx(Hq Ne) Hw(Mf Mq) Pg(Iu Pd) LwQb MlPb MtJj IvJs} Ng{Lu(Et Ii Ir Ji Jk Lx Ma Mk Mn Mr Mt Mu Nb Nn No Nr Nv Oy Pb Po Qa Qb Qd Qe) Oy(Hu Hx Ir Is Jj Jr Lw Lx Ma Mf Mj Mp Mt Nd Nq Nv Nw Om Pe Qa Qb Qd Qe) Lx(Hx Ii Is Jh Jp Jr Ma Mj Mr Mu Mv Mz Nb Nd Ne Nn Nr Om Pb Pe) Pb(Hu Hx Ir Jj Mj Mp Mw My Nd Nq Nv Nw Om Pe Po Qa Qb Qd Qe) Nn(Hu Ir Is Iu Jk Jp Jr Mj Mu Mv Mx My Nj Nr Nw Om Po Qb) Nr(Hu Hx Is Jp Lh Ma Mt Mu Na Nv Nw

Figure 16 Continued

Om On Pe Qa Qb) Ii(Hx Is Jr Lh Ma Mp Mu My Mz Nq Nw Om On Pe Po Qb) Mj(Hu Hx Is Jp Lh Ma Mf Mk Mt Mu Mv Mx Nw Pg) Hx(Iq Jp Ma Mk Mp Mr Mu Mv Nb Nw Om On Po) Po(Hu Is Jp Ma Mh Mu Mv Mz Og Pd) Mr(Hu Is Mt Nv Nw Om Pe Qa Qb Qd) Nb(Hu Is Jr Lh Mt Mz Nf Nw On Qb) Mu(Is Jk Jp Jr Mf Mz Nw Og Qb) Mk(Ir Jh My Nd Pe Qd Qe) Mv(Iu Jp Lw Ly Mz Nj Nw) Jk(Is Iu Jh Ji Lw No Oe) On(Hu Jr Ma Mz Nj Nm) Pe(Hu Jr Lh Mz Nw Qb) Is(Jn Jr Mx) Jp(Hu Ly) Nv(Oe Og) MfHw NjLh JqOm} Mg{Mv(Hx Ii Is Iu Jg Jp Jr Lu Lw Lx Ly Mj Mp Mr Mz Nb Nn Nr Nw Oe Om Oy Po) Nn(Hx Ii Is Jg Jp Jr Lx Ma Mj Mk Mr Mx Nb Nj Nr Om On Pb Pe Po) Mu(Hx Ii Is Jp Lu Lw Lx Mj Mk Mr Mz Nb Nr Nw Om Oy Pb Pe Po) Jg(Ir Is Jj Jp Jr Lu Lw Lx Mj Mk Mp Mr Mz Nr Nw On Pb Po Qb) Jk(Hx Is Ji Jp Jr Lw Lx Mk Mr Mz Nb Nr Nw Oe Om On Pb Pe Po) Lx(Hx Is Jp Jr Lw Ma Mk Mz Nj Nw Og Om Pb Pe) Pb(Is Jj Jp Jr Ma Mt Mz Nw Oe Om Pe Qa Qb) Po(Hx Is Jp Lj Lu Ma Mh Mz Oe Og Om) Mk(Hx Is Jp Jq Lh Ma Mt Nv Nw Om Pg) Pe(Hx Is Jp Lu Lw Ma Mt Mz Nw Om) Ma(Hx Ii Lu Mr Nb Nr Om Oy) Jp(Hx Ii Lw Ly Mr Nb Om Oy) Nw(Hx Ii Jn Js Lw Mt Oy) Om(Hx Jq Jr Mr Nx Oe) On(Hu Ji Jr Mq Mz Oh) Oy(Is Jr Mz Oe Og) Lu(Hx Is Ji Mn) Lw(Hx Is Mz) Nb(Is Jr Mz) Nv(Oe Og) MrMt MzIi HxIq JsPg} Nx{Jp(Hx Ii Ir Is Iv Ji Jr Lw Lx Ly Mj Mk Mr Mu Mz Nb Nj Nn Nr Nw Om Pc Pe Po Qb) Is(Iq Ir Iu Jr Lw Mk Mr Mu Mv Mx Mz Nb Nn Nr Nw Om Pc Pe) Om(Hx Ii Jg Jr Lu Lw Mk Mr Mz Nb Nn Nr Nw Oe Oy Po Qb) Pe(Hx Iq Jg Ji Jq Lh Lx Ma Mt Mu Mv Nb Nn Nv Pg Qa) Nw(Hw Hx Ii Jg Jr Lw Mj Mk Mr Mt Mx Nb Nr Oh Oy) Mz(Hu Ii Jg Jk Jr Lh Lw Mu Mv Nb Nj Nn Nr Oy) Ji(Hx Jk Jr Lu Mk Mr Mu Mv Nn Nr Oe Og Pc Pg) Pc(Hx Ir Iv Jr Lx Ma Mj Mv Po Qa Qb Qd) Nb(Jq Jr Lh Lx Mv Oe Pg Qa Qb) Hx(Jg Jr Lw Lx Ma Mu Mv Nj Nn) Nr(Jq Lx Ma Mt Mu Mv Pg Qa) Mk(Jq Lx Ma Mt Mu Mv Qa) Mr(Jq Lx Ma Mt Mu Mv Qa) Jr(Hu Ii Jg Jk Lw Mu Nj) Lh(Jg Lu Lw Lx Nd Nf Nj) Pg(Ii Jq Lw) Mu(Ir Qb) NnIr LwMv NaPa IiJq NvOe} Oi{Jp(Hx Ii Ir Is Jg Jk Jr Lh Lu Ly Mk Mr Mu Mv Nb Nj Nr Nw On Oy Pe Pg Po Qb) Mk(Hu Hx Ir Is Jg Jk Jr Lh Lu Lx Ma Mj Mt Mu Mv Nw Pe Pg Qa Qb Qd) Mr(Hu Hx Is Jg Jk Jr Lh Lx Ma Mj Mt Mu Mv Mz Nj Nw Pe Pg Qa Qb Qd) Nr(Hu Hx Is Jg Jk Jr Lh Lx Ma Mt Mu Mv Mz Nw Pe Pg Qa Qb Qd) Lu(Hx Ii Ir Jg Ji Jr Lh Lx Ma Mu Mv Om Pg Qa Qb Qd Qe) Jr(Hx Ii Is Jg Jk Lh Mu Mv Nb Nw On Oy Pg) Mz(Hu Ii Jg Jk Ly Mu Mv Nj On Oy Pg) Is(Iq Jg Jn Mu Mv Nw On Oy Pe Pg) Ii(Jg Jj Lx Ma Mt Mu Mv Qa Qb) On(Hx Lh Lx Mu Mv Nj Pg Qa Qb) Jg(Hx Ir Mj Pe Qa Qb Qd) Mu(Hx Ir Mj Nb Pe Qb) Nw(Mq Mv Nc Nj Pe Pg) Mv(Hx Mj Nb Pe) Lx(Nb Pa Pe) Qb(Nb Pa Pe) Hx(Iq Nj) Pg(Hq Pd) IuLh QaPa} Oe{Lu(Et Hv Ih Ii Ip Iv Ji Jj Jk Jn Lw Lx Ma Mn Mp Mt Mw Nn No Nu Nv Ok Om Oy Po Qa Qd) No(Ii Jj Jk Jp Lw Lx Mc Mj Ml Mt Mu Mv Nn Og Om Oy Qa Qb Qd Qe) Jj(Hu Ih Ip Iu Ji Jn Ma Mn Mp Mw My Nc Nj Nq Nt Nu) Mj(Hu Ih Jk Lx Mf Mt Mv Nb Nv Qb Qe) Ir(Ii Iq Is Iu Jg Jp Mu Mv Nn Og Oy) Lx(Mm Mu Nd Ne Nn Nq Nt Og Pd) Ii(Jr Ma Mt Mu Pe Qa Qd Qe) Iv(Jn Jr Lw Ml Nd Nn Og Oy) Nn(Jp Mv Nj Qa Qd Qe) Hw(Hv Jn Jr Js Me Pd) Lw(Jk Jp Mt Mv Qb) Qa(Jg Jn Js Mf Og) Qe(Jg Mu Mv Nb Og) Qd(Jg Mf Og Oy) Mu(Jr Nb Qb) Jp(Ly Mm Po) Ml(Jr Nb) My(Oy Pb) Is(Mv Mx) Qb(Og Po) Ji(Jk Mm) Lh(Hq Nf) Ny(Hx Pb) MqOk IuJk JrOy NvOg} Pd{Lx(Hu Hw Ii Ir Is Iv Jg Jj Jk Jq Li Lw Ma Mj Mk Mr Mt Mu Nb Nd Ne Nj No Nq Nr Nv Og Om Oy Pb Pf Qa Qb Qd Qe) Mr(Hx Ir Is Jp Jq Jr Ma Mj Mp Mt Mu Mv Nv Om On Po Qa Qb Qd) Nr(Hx Ir Is Jq Jr Ma Mj Mp Mt Mu Mv Mz Om On Po Qa Qb) Mk(Hx Ir Is Jq Jr Ma Mj Mp Mt Mu Mv Om On Po Qa Qb Qd) Po(Is Jp Jq Jr Js Lw Ma Mq Mz Nj Om Pb Pg) Hw(Is Jj Jp Jq Jr Mp Mv Mz Nn Og Pg Qb) Nw(Fr Hx Ii Jr Lu Mj Mp Mq Mv Nn Pb Pc) Li(Fr Hx Jp Jr Mp Mz Nn Om) Pg(Iu Jp Jq Jr Mp Mz) Mj(Hx Mp Mv Nn) Hx(Lw Mp Om) Mz(Nn Pb) FrNb NoJs JrPb} Pc{Nf(Hw Hx Ii Ir Is Jq Jr Lu Lx Mj Mk Mr Nb Nr Om Pg Po Qb Qd) Nq(Hx Is Jk Jp Jr Lh Lu Lx Mj Mv Nw On Pg Qa Qb Qd) Jh(Hx Is Jp Jq Jr Lh Lu Mv Nw Om Pg Qa Qb) Mv(Jp Jr Lh Lx Mu My Nw Pg Qa Qb) Nj(Hx Jp Jr Lh Lu Ma Mc Ml Nd Nw) Lu(Ir Jr Lw Lx Ma Qa Qb Qd) Of(Lh Mk Mr Nb Nr Pb Pe) Pe(Hr Iq Iu My Ns Pf) Mq(Jq Ma Mc Om Qa) Oy(Lh Mk Mr Nr On) Mm(Jp Lx Ma Qd) Iq(Hx Ir Is) Iu(Ir Qa Qd) NsLh LyJp McHu MlJq NcNe IiPg JrJs} Og{Jj(Hu Hv Ih Ip Iu Ji Jn Lu Lw Lx Ma Mw Nc Nj Nq Nt Qd) Lu(Et Ip Ir Ji Jn Lx Ma Mn Mt Nj No Qa Qd Qe) Lw(Hu Hv Ir Iv Jg Jk Mj Mu No Qa Qb Qe) Nj(Hv Ma Mp My Nd No Nq Po Qd) Oy(Hq Hu Ir Mq My Nc Nn Of Qd) Hw(Hv Jn Js Me Ml Na Nm) No(Jk Mc Ml Nn Qb Qe) Lx(Mm Nd Ne Nq Nt Om) Iv(Ii Ir Jn Ml Mx Nn) Jq(Jn Js Mf Ml Mq) Ir(Iq Iu Jg Nn) Qb(Jg Mu Nn Po) Ji(Jk Mm Mq) Nc(Ii Ne) Jk(Ip Iu) NnMx MfMu MpHq MqOk} Pe{Iq(Fp Hx Ir Is Jp Jr Lh Ma Mf Mr Mv Mz On Pg Qa Qb) Js(Hr Hx Ir Iv Jq Lu Mj Mq Nn Nw Pb Pf Pg Qa Qb Qd) Iu(Ir Is Jr Lu Lx Mv Nn Nw On Pf Pg Qa Qb) Nt(Hr Jg Mt Mz Nw On Pg Qa) Nf(Hx Jr Lu Mk Mr Mv Mz Qb) Jq(Hv Jn Mf Ml Mq Mx Na Nm) Mx(Is Jr Mj Mz Qa) Na(Is Jr Mh Mu Nr) Mm(Lx Ma Mz Nn) Nj(Jp Nd Nn Nw) Ok(Lh Nw On) Pf(Jp Lx Nn) Mq(Lw Mu) Ii(On Pg) Of(Jg Ma) NqMu LuQb MfQa NcNe JnJr} Jr{Jn(Hw Iv Lh Lu Lw Mj Mv Mz Nb Nj Nn No Nr Nw Pg) Ml(Hw Hx Is Lh Mj Mv Mz Nb Nn No Nw Om Pb) Iq(Hx Is Jp Lh Mj Mk Mr Mv Nb Nr Pg) Js(Hw Hx Jp Mq Mv Nb Nn No Ns Nw Po) Lu(Is Jp Mk Nj Nr) Mf(Hw Lh Lw Mj Nj) Iu(Hx Is Mv Nj Pg) Mz(Hw Is Iv Oh) Nf(Lh Mk Mr) Li(Lh Mv On) Oh(Lh Nw On) Nr(Na Pg) Lx(Ne Nt) Mq(Hw Lw) Mx(Is Mj) Nj(Nd Nn) Jp(Is Mm) MtNw NcNe HvHw IiPg} Mz{Js(Hw Hx Ii Iv Jk Lx Mr Mu Mv Nb Nn No Nr Nw Om Pb Po) Ml(Hw Hx Is Iv Mj Mv Nb Nn No Nw Om Pb Po) Mm(Is Mj Mr Mv Nj Nn Nr Pg Qb) Iq(Hx Ir Lh Mj Mk Mr Mv On) Nj(Iu Jp Lh Mf Mj Nn On) Jn(Hw Is Iv Nb Nn Nw) Mx(Is Iv Mj Nn) Hw(Hv Mf Mq Nm) Oh(Is Mv Pg) Mt(Nn Nw) Nf(Lh Mr) Pb(Hx Ny) Pg(Ii Iu) NmLw NrNa NtLx LyJp NcNe IrIs} Iu{Mr(Ir Is Jk Lh Lx Ma Mt Mv Nj Nw Pg Qa Qb Qd Qe) Nr(Ir Is Lh Lx Mt Mv Nj Pg Qa Qb Qd Qe) Mk(Ir Is Lh Lx Mt Mv Nj Pg Qa Qb Qd Qe) On(Ir Is Lh Lx Mv Nj Pg Qa Qb Qd) Ir(Is Jp Lu Mv Nn Nw Pg) Lh(Lu Mv Nf Nj Nw Qb) Mj(Mv Nj Nw Pg Qb) Is(Jn Lu Mx Nj Pg) Nw(Mv Nj Qa Qb) Lu(Pg Qa) Hx(Mv Nj) NnJj} Jj{Lu(Hu Ii Ip Iv Ji Jn Lw Lx Ma Mn Mu My Nn No Nu Nv) Nj(Ii Lx Ma My Nd Nq Nw Oy Qc) Oy(Ih Ir Ma Mt My Nc Qa Qd) Hw(Hv Jn Js Mc Ml Mq Nm) Ly(Jg Ma Nd Nn No Nq) Ml(Iv Nn No Om Pb) Mj(Ii Jp Mt Nw) Iv(Jn Js Mx Nn) Lx(Mm Nd Ne) Mq(Nw Ok Om) Nc(My Ne Nq) Ii(Ir Ma Mu) No(Js Mc) Pb(My Ny) NqHu NuMa MfOm InJp} Pg{Js(Hq Hw Hx Ir Iv Jq Lx Mj No Nw Pb) Ii(Hx Is Lh Mj Mk Mq Mr Nn Nr Nw) Nq(Jg Lu Lx Mu Nn Nw) Iq(Ir Is Mj Mr Nr On) Nw(Ml Mt My Nf Ny) Of(Jp Mk Nb On) Fr(Hq Oy Pf) Nn(Mv My Ns) Is(Mm Mx Oh) Pa(Lj Lz Mh) Nt(Lx Mr) Mq(Jq Lw) Hq(Nd Pb) NrNa MfHw MjMx MrNf MyJg NcNe PzJp} Lh{Hq(Hv Jn Lu Mf Ml Mq Mx Na Nd Nm) Iq(Hx Ir Is Jp Mj Mv Ne On Qb) Nj(Jp Lu Mf Mq Nd Nh Nn Nw) Nq(Mf Mq Mu Mx Na Nm Nn) Nf(Hx Jp Lw Mk Mr Ne Nr) Na(Is Lw Mk Nr) Of(Mk Mv Nb Pb) Ok(Mr Nr On) Lw(Mf Nm) Mq(Jq Lx) Ne(Lu Nc) Is(Mx Oh) IiOn} Nw{Nf(Hw Hx Ii Lx Mj Nn Nr Oy) Ok(Js Mk Ml Mr Mt Nr On Pa) Nj(Jp Mk Mm Mr Nd Nh Nr) Jn(Hw Ir Iv Lu Mj Nc Qa) Js(Hx Ji Mj Nc Nm) Ml(Hx Mq Nm Nn) Mt(Ji Mq Nm Nn) Nc(Ne Nh Nl) Iq(Ir Is Qb) Nt(Lx Pa) Lw(Mq Nm) Mx(Iv Mj) MfHw IsJq} Jp{Nj(Hx Lx Mj Mk Mr Nb Nd Nn Nr On Po) Mm(Ir Lx Mj Nb Po Qa Qb) Hw(Hv Jn Js Mf Ml Mq Nm) Is(Iq Ir Jn Ml Mx Oh) Js(Iv Lx Mj No Pb Po) Iq(Hx Ir On Qb) Nn(Fr Mv) Lx(Nq Nt) Pz(Ir Qb) Pb(Ml My) MjMx NcNe IvJn} On{Ok(Hr Jh Jq Lx Ma Mj Mr Mv Nb Nj Nr Ns) Iq(Hx Ir Is Mq Mv Qa Qb) Nj(Lu Mq Nd Nh Nn Pz) Of(Ji Lu Ma Mk Nm) Ii(Hx Mk Mr Nr) Ji(Jq My Nb) Nm(Hr Jq) Nc(Ne Nh) Qa(Jn Js) NqMu NtLx MqHr MxIs NdHq} Lx{Nt(Hu Hx Ir Is Iv Jg Lu Lw Ma Mj Mt Mu Mv Nj Nn Nu Qa Qb Qd Qe) Lu(Mk Mr Nr) Mm(Mk Mr Nr) Js(Hx Qa Qb) Nn(Nj Nq) Ne(Nc Nj) Hq(Fr Nd) NqMv HrPa} Mk{Of(Hx Jg Jk Jq Ma Mu Nn Om) Nf(Hx Jq Mv Nn Qb) Iq(Hx Ir Is Qa Qb) Jq(Hr Mf Mq Na) Nn(My Nj Oy) Lu(Qa Qb) NqMu MaMm NcNe NdNj QaJs} Mr{Nf(Hx Jq Mu Mv Nn Om Qb) Iq(Hx Ir Is Qa Qb) Jq(Hr Mf Mq Na) Nj(Nd Nn) Of(Jg Mv) NqMu LuQb MaMm MxIs NcNe HrHx QaJs} Is{Iq(Hx Jn Lu Mj Ml Mm Nd Nh Nr) Lu(Ir Jn Ml) Mv(Ir Mm Mx) Nr(Mx Na) FrNy NnMl MfHw MjMx NaPa NcNe NdNj} Nn{Nj(Hx Lu Mj Nd Nr) Hx(Mv My Nf Ns) Mj(Mf Mx) Nb(Nf Of) FrMv NoJs NrNf MyPb NcNe HrPa IqIr} Nr{Iq(Hx Ir Qa Qb) Jq(Js Mf Mq Na) Na(Mu Qa) Nd(Hq Nj) LuQb MaMm NcNe NfHx QaJs} Lu{Lw(Hx Ir Mv Qb) Nj(Hx Mn Nd No) Iq(Ir Qb) Jg(My Nq) NoJs MlOm MmJi NfHx} Js{Qa(Iv Mj Nb No Pb) Qb(Hw Iv Mj No Pb) Fr(Hw Pb) MjJq HxOm} Pa{Nt(Jq Mt Mv Mx Qa) Hr(Jq Nd Ne) Mx(Na Qa) Hv(Hw Qa) NqLz} Fr{Pb(Hq Ml Ny Of) Hw(Ml Mq Nm) NmLw MyOy NbOf NfIi} Mj{Mx(Jq Mv Qa Qb) Hx(Iq

Figure 16 Continued

Nf) MfMv NcNe NdNj IqQb} Hx{Lw(Iq Nf) MlOm MyJg NcNe NdNj Iqlr} Hw{Mf(Jq Mv Qa Qb) Mq(Jq Mv)} Mv{MyPb NbOf NcNe}
Mu{My(Hu Mf)} Ndlqlr Constrained panels with 2 analytes, where 1.0E-6 >= 'model p-value' > 0. Contains 34 panels of 6,786 total panels evaluated. : Lv(aA Fr Hx Jj Jl
Jo Jp Lu Mf Mg Mi Mk Mq Mr Mz Nd Ng Nn Nr Nx Oe Og Oi Pa Pc) aA(Iq Jl Jt Oe Og) Pa(Jj Pd) MiPd JlOg Constrained panels with 2 analytes, where 1.0E-5 >= 'model p-value' > 1.0E-6. Contains 38 panels of 6,786 total panels evaluated. : Mi(Hq Iq Jj
Jl Jo Jt Lu Mg Ms Nt Oe Og Pc) Jl(Jj Jt Lu Mm Ms Nx Oe Oh Oi Pa) Pa(Iq Jo Js Jt Oe Og Pe) Oe(Fr On) Og(On Pc) Pd(Lh Pe) Pg(Jj Jo)

Constrained panels with 2 analytes, where 1.0E-4 >= 'model p-value' > 1.0E-5. Contains 68 panels of 6,786 total panels evaluated. : Fr(Jj Jo Jr Jt
Mg Mk Mr Ms Mz Ng Nj Nr Nx Og Oi Pa Pe) Jj(Hx Jk Jr Lh Mk Mr Nr On Pe) Og(Hx Is Mk Mr Mz Nr Nw Pb Pe) Pa(Hq Iu Lu Ms Nf Ng Nj
Oy Pf) Oe(Hx Mk Mr Nr Pc Pe) Jo(Jl Lh On Pe) Lh(Jt Mg Nt) On(Jt Ms Nf) Pc(Ms Ng Oi) Jl(Iu Ng) NqMi LuMz IsJs Constrained panels with 2 analytes, where 1.0E-3 >= 'model p-value' > 1.0E-4. Contains 229 panels of 6,786 total panels evaluated. : Jj(Hu Ih Ii
Ir Is Iu Iv Jg Jp Lu Lx Ma Mj Mt Mu Mv Mz Nb Nn Nu Nv Nw Oe Og Om Oy Pc Po Qa Qb Qd Qe) Og(Ii Ir Iv Jg Ji Jk Jp Jr Lh Lw Lx Mj Mu
Mv Nb Nn No Om Pg Po Qa Qb Qe) Oe(Ii Ir Is Jg Jp Jr Lh Lx Mj Mu Mv Mz Nb Nn Nw Pg Po Qa Qb Qe) Mz(Jo Jt Lh Mj Mk Mm Mr Ms Mv
Nn Nr Nx Oi On Pc Pe Pg) Lu(Hx Ir Is Ji Jp Jr Lh Lw Mk Mr Nr Nw On Pe Pg Qb) Jp(Hx Jr Jt Lh Lw Mj Mk Mm Mr Nr On Pc Pe Pg) Mk(Is
Jo Jr Jt Lh Ms Mv Ng Nw Pg Qa Qb) Nw(Jo Js Jt Ml Mm Mr Ms Nj Nr Nx Oi) Pg(Iu Jr Jt Mg Mr Ms Ng Nr Nx Oi Pd) Lh(Iu Jr Js Mm Ms Nf
Ng Nj Nx Oi) Pe(Iu Jr Jt Ms Mv Nf Ng Nn Pc Pf) Is(Iu Jn Jo Jr Jt Ml Ms Mx Nx) On(Jr Mg Mm Mq Ng Nx Of Oi Pd) Mr(Jo Jr Jt Ms Mv Ng
Nn Qb) Jo(Hx Mj Nb Nr Pc Po) Ng(Jg Jk Mv Nb Pb) Pc(Ir Jr Mg My Ns) Ms(Hx Jg Nb Nr) Nr(Jr Mv) PoPd NnOi LxHq MgJg JrJs Constrained panels with 2 analytes, where 1.0E-2 >= 'model p-value' > 1.0E-3. Contains 236 panels of 6,786 total panels evaluated. : Jo(Hw Ii Ir
Iv Jg Ji Jk Jr Jt Lw Lx Ma Mt Mu Mv Nn No Nv Om Qa Qb Qd Qe) Lu(Et Iv Jg Jn Lx Ma Mj Mn Mt Mu Mv Nb Nn No Oe Og Om Pc Po Qa
Qd Qe) Ms(Ii Ir Ji Jp Lw Lx Mj Mt Mu Mv Nn No Nv Om Oy Pb Qd Qe) Oe(Hu Hv Iv Ji Jk Jn Lw Ma Mn Mp Mt No Nu Nv Om Oy Qd)
Oi(Hx Ii Ir Is Jg Jk Lx Mk Mu Mv Nb Om Oy Qa Qb Qd Qe) Lx(Jt Mg Mk Mm Mr Nb Nd Ne Ng Nq Nr Nt Pc Pd) Pc(Hx Is Jh Lw Ma Mv Nc
Nj Nq Nw Qa Qb Qd) Nn(Ir Iv Jr Lw Mg Mj Nc Ng Nj Nr Qb Qd) Og(Hu Hv Ip Jn Ma Mt Nj Nv Oy Qd) Mg(Hx Jk Ma Mu Mv Om Oy Pb Po)
Ng(Hx Ii Ma Mu Nr Nv Om Oy Po) Jt(Ir Jg Ji No Nr Nv Om Qa Qd) Nr(Hx Is Lh Mu Qa Qb) Mj(Mf Mu Mv Mx Nj Qb) Hw(Hv Js Mf Ml Mq
Pd) Ir(Iq Is Iu Lw Mu) No(Jj Js Mc Ml) Mr(Is Lh Mu Qa) Iu(Qa Qb Qd Qe) Jr(Hx Jn Mv Nw) Lw(Mu Mv Qb) Nj(Jj Jp Nd) Iv(Jn Js Ml) Nb(Mv
Qb) Ji(Mm Nx) Jj(Jn My) Jp(Is Nw) Om(Mf Nx) NmLh MlPb MuQb QdJg Constrained panels with 2 analytes, where 5.0E-2 >= 'model p-value' > 1.0E-2. Contains 69 panels of 6,786 total panels evaluated. : Jo(Et Hu Hv
Ip Iu Jn Jq Mn Mp My Nu Oy) Ms(Hu Jk Jn Ma Mn Mp Mw My Nd Nq Pb) Oi(Hu Ip Iv Ma Mt Nu Nv) Jt(Et Jk Ma Mf Ok) Mq(Ji Jq Ok Om)
Ng(Hu Mp Mt My) Hw(Jn Mc Na Nm) Pb(Hq Js My Ny) Mg(Ii Nv) Mm(Et Jg) Mp(Hq Pd) Nc(Nd Ne) Nj(Lx Nq) MaHv MfJq MlOm MxIv
MyOy IuJk LiPd NvNx Unconstrained panels with 3 analytes, where 1.0E-8 >= 'AUC p-value' > 0. Contains 15,796 panels of 260,130 total panels evaluated. :
Lv{Po(aA Et Fp Fr Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb
Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No
Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Et(aA Fp Fr Hq Hr Hu Hv Hw
Hx Ih Ii In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml
Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of
Og Oh Oi Ok Om On Oy Oz Pa Pb Pc Pd Pe Pf Pg Pz Qa Qb Qc Qd Qe) Fp(aA Fr Hq Hr Hu Hv Hw Hx Ih Ii In Io Ip Iq Ir Is It Iu Iv Jg Jh Ji Jj
Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx
My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe
Pf Pg Pz Qa Qb Qc Qd Qe) Fr(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Lu Lw Lx Ly
Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl
Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Nm(aA Hq Hr Hu
Hv Hw Hx Ih Ii In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj
Mk Ml Mm Mn Mp Mq Mr Ms Mt Mu Mv Mw Mx My Mz Na Nb Nc Nd Ne Nf Ng Nh Ni Nj Nk Nl Nn No Nq Nr Ns Nt Nu Nv Nw Nx Ny Oe
Of Og Oh Oi Ok Om On Oy Oz Pa Pb Pc Pd Pe Pf Pg Pz Qa Qb Qc Qd Qe) Nn(aA Hq Hr Hu Hv Hw Hx Ih Ii In Io Ip Iq Ir Is It Iu Iv Jg Jh Ji Jj
Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx
My Mz Na Nb Nc Nd Ne Nf Ng Nh Ni Nj Nk Nl No Nq Nr Ns Nt Nu Nv Nw Nx Ny Oe Of Og Oh Oi Ok Om On Oy Oz Pa Pb Pc Pd Pe Pf Pg
Pz Qa Qb Qc Qd Qe) No(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Lu Lw Lx Ly Lz
Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nq
Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Nq(aA Hq Hr Hu Hv Hw Hx Ih Ii In
Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp
Mq Mr Ms Mt Mu Mv Mw Mx My Mz Na Nb Nc Nd Ne Nf Ng Nh Ni Nj Nk Nl Nr Ns Nt Nu Nv Nw Nx Ny Oe Of Og Oh Oi Ok Om On Oy
Oz Pa Pb Pc Pd Pe Pf Pg Pz Qa Qb Qc Qd Qe) Nr(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh
Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf
Ng Nh Ni Nj Nk Nl Ns Nt Nu Nv Nw Nx Ny Oe Of Og Oh Oi Ok Om On Oy Oz Pa Pb Pc Pd Pe Pf Pg Pz Qa Qb Qc Qd Qe) Ns(aA Hq Hr Hu
Hv Hw Hx Ih Ii In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj
Mk Ml Mm Mn Mp Mq Mr Ms Mt Mu Mv Mw Mx My Mz Na Nb Nc Nd Ne Nf Ng Nh Ni Nj Nk Nl Nt Nu Nv Nw Nx Ny Oe Of Og Oh Oi Ok
Om On Oy Oz Pa Pb Pc Pd Pe Pf Pg Pz Qa Qb Qc Qd Qe) Nt(aA Hq Hr Hu Hv Hw Hx Ih Ii In Io Ip Iq Ir Is It Iu Iv Jg Jh Ji Jj Jk Jl Jm Jn Jo Jp
Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb
Nc Nd Ne Nf Ng Nh Ni Nj Nk Nl Nu Nv Nw Nx Ny Oe Of Og Oh Oi Ok Om On Oy Oz Pa Pb Pc Pd Pe Pf Pg Pz Qa Qb Qc Qd Qe) Nu(aA Hq
Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh
Mi Mj Mk Ml Mm Mn Mp Mq Mr Ms Mt Mu Mv Mw Mx My Mz Na Nb Nc Nd Ne Nf Ng Nh Ni Nj Nk Nl Nv Nw Nx Ny Oe Of Og Oh Oi Ok
Om On Oy Oz Pa Pb Pc Pd Pe Pf Pg Pz Qa Qb Qc Qd Qe) Lu(aA Hq Hr Hu Hv Hw Hx Ih Ii In Io Ip Iq Ir Is It Iu Iv Jg Jh Ji Jj Jk Jl Jm Jn Jo Jp
Jq Jr Js Jt Lh Li Lj Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc

Jg Jh Ji Jj Jk Jl Jm Jn Jo Jp Jq Jr Js Jt Lh Li Lj Ne Nf Ng Nh Ni Nj Nk Nl Nv Nw Nx Ny Oe Of Og Oh Oi Ok Om On Oy Oz Pa Pb Pc Pd Pe Pf Pg Pz Qa Qb Qc Qd Qe) Ne(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Nf Ng Nh Ni Nj Nk Nl Nv Nw Nx Ny Oe Of Og Oh Oi Ok Om On Oy Oz Pa Pb Pc Pd Pe Pf Pg Pz Qa Qb Qc Qd Qe) Nf(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Ng Nh Ni Nj Nk Nl Nv Nw Nx Ny Oe Of Og Oh Oi Ok Om On Oy Oz Pa Pb Pc Pd Pe Pf Pg Pz Qa Qb Qc Qd Qe) Ng(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Nh Ni Nj Nk Nl Nv Nw Nx Ny Oe Of Og Oh Oi Ok Om On Oy Oz Pa Pb Pc Pd Pe Pf Pg Pz Qa Qb Qc Qd Qe) Nh(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Ni Nj Nk Nl Nv Nw Nx Ny Oe Of Og Oh Oi Ok Om On Oy Oz Pa Pb Pc Pd Pe Pf Pg Pz Qa Qb Qc Qd Qe) Ni(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Nj Nk Nl Nv Nw Nx Ny Oe Of Og Oh Oi Ok Om On Oy Oz Pa Pb Pc Pd Pe Pf Pg Pz Qa Qb Qc Qd Qe) Nj(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Nk Nl Nv Nw Nx Ny Oe Of Og Oh Oi Ok Om On Oy Oz Pa Pb Pc Pd Pe Pf Pg Pz Qa Qb Qc Qd Qe) Nk(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Nl Nv Nw Nx Ny Oe Of Og Oh Oi Ok Om On Oy Oz Pa Pb Pc Pd Pe Pf Pg Pz Qa Qb Qc Qd Qe) Nl(aA Hq Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Hq(aA Hr Hu Hv Hw Hx Ih Ii In Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Hr(aA Hu Hv Hw Hx Ih Ii In Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Hu(aA Hv Hw Hx Ih Ii In Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Hv(aA Hw Hx Ih Ii In Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Hw(aA Hx Ih Ii In Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Hx(aA Ih Ii In Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Ih(aA Ii In Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Ii(aA In Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) In(aA Io Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Io(aA Ip Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Ip(aA Iq Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Iq(aA Ir Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Ir(aA Is It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Is(aA It Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) It(aA Iu Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Iu(aA Iv Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Iv(aA Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Pz Qa Qb Qc Qd Qe) Pz(aA Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Qa Qb Qc Qd Qe) Qa(aA Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Qb Qc Qd Qe) Qb(aA Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Qc Qd Qe) Qc(aA Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Qd Qe) Qd(aA Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg Qe) Qe(aA Jg Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jg(aA Jh Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jh(aA Ji Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Ji(aA Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jj(aA Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jk(aA Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jl(aA Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jm(aA Jn Jo Jp Jq Jr Js Jt Lh Li Lj Nv Nw Nx Ny Oe Of Og Oh Oi Ok Om On Oy Oz Pa Pb Pc Pd Pe Pf Pg) Jn(aA Jo Jp Jq Jr Js Jt Lh Li Lj Nv Nw Nx Ny Oe Of Og Oh Oi Ok Om On Oy Oz Pa Pb Pc Pd Pe Pf Pg) Jo(aA Jp Jq Jr Js Jt Lh Li Lj Nv Nw Nx Ny Oe Of Og Oh Oi Ok Om On Oy Oz Pa Pb Pc Pd Pe Pf Pg) Jp(aA Jq Jr Js Jt Lh Li Lj Nv Nw Nx Ny Oe Of Og Oh Oi Ok Om On Oy Oz Pa Pb Pc Pd Pe Pf Pg) Jq(aA Jr Js Jt Lh Li Lj Nv Nw Nx Ny Oe Of Og Oh Oi Ok Om On Oy Oz Pa Pb Pc Pd Pe Pf Pg) Jr(aA Js Jt Lh Li Lj Nv Nw Nx Ny Oe Of Og Oh Oi Ok Om On Oy Oz Pa Pb Pc Pd Pe Pf Pg) Js(aA Jt Lh Li Lj Nv Nw Nx Ny Oe Of Og Oh Oi Ok Om On Oy Oz Pa Pb Pc Pd Pe Pf Pg) Jt(aA Lh Li Lj Nv Nw Nx Ny Oe Of Og Oh Oi Ok Om On Oy Oz Pa Pb Pc Pd Pe Pf Pg) Lh(aA Li Lj Nv Nw Nx Ny Oe Of Og Oh Oi Ok Om On Oy Oz Pa Pb Pc Pd Pe Pf Pg) Li(aA Lj Nv Nw Nx Ny Oe Of Og Oh Oi Ok Om On Oy Oz Pa Pb Pc Pd Pe Pf Pg) Lj(aA Nv Nw Nx Ny Oe Of Og Oh Oi Ok Om On Oy Oz Pa Pb Pc Pd Pe Pf Pg) Nv(aA Nw Nx Ny Oe Of Og Oh Oi Ok Om On Oy Oz Pa Pb Pc Pd Pe Pf Pg) Nw(aA Nx Ny Oe Of Og Oh Oi Ok Om On Oy Oz Pa Pb Pc Pd Pe Pf Pg) Nx(aA Ny Oe Of Og Oh Oi Ok Om On Oy Oz Pa Pb Pc Pd Pe Pf Pg) Ny(aA Oe Of Og Oh Oi Ok Om On Oy Oz Pa Pb Pc Pd Pe Pf Pg) Oe(aA Of Og Oh Oi Ok Om On Oy Oz Pa Pb Pc Pd Pe Pf Pg) Of(aA Og Oh Oi Ok Om On Oy Oz Pa Pb Pc Pd Pe Pf Pg) Og(aA Oh Oi Ok Om On Oy Oz Pa Pb Pc Pd Pe Pf Pg) Oh(aA Oi Ok Om On Oy Oz Pa Pb Pc Pd Pe Pf Pg) Oi(aA Ok Om On Oy Oz Pa Pb Pc Pd Pe Pf Pg) Ok(aA Om On Oy Oz Pa Pb Pc Pd Pe Pf Pg) Om(aA On Oy Oz Pa Pb Pc Pd Pe Pf Pg) On(aA Oy Oz Pa Pb Pc Pd Pe Pf Pg) Oy(aA Oz Pa Pb Pc Pd Pe Pf Pg) Oz(aA Pa Pb Pc Pd Pe Pf Pg) Pa(aA Pb Pc Pd Pe Pf Pg) Pb(aA Pc Pd Pe Pf Pg) Pc(aA Pd Pe Pf Pg) Pd(aA Pe Pf Pg) Pe(aA Pf Pg) Pf(aA Pg) PgaA} Jl{Mm(aA Et Fp Fr Hq Hr Hu Hv Hw Hx Ih Ii In Io Ip Iq Ir Is It Iu Iv Jg Jh Ji Jj Jk Jm Jn Jo Jp Jq Jr Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ms(aA Et Fp Fr Hq Hr Hu Hv Hw Hx Ih Ii In Io Ip Iq Ir Is It Iu Iv Jg Jh Ji Jj Jk Jm Jn Jo Jp Jq Jr Js Jt Lh Li Lj Lu Lw Lx Ly Lz Ma Mb Mc Md Me Mf Mg Mh Mi Mj Mk Ml Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Iu(aA Et Fp Fr Hq Hr Hu Hv Hw Hx Ih Ii In Io Ip Iq Ir Is It Iv Jg Jh Ji Jj Jk Jm Jn Jo Jp Jq Jr Js Jt Lh Li Lj Lu Lw Lx Ly Lz Ma Mb Mc Md Me Mf Mg Mh Mi Mj Mk Ml Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Pz(aA Et Fp Fr Hq Hr Hu Hv Hw Hx Ih Ii In Io Ip Iq Ir Is It Iv Jg Jh Ji Jj Jk Jm Jn Jo Jp Jq Jr Js Jt Lh Li Lj Lu Lw Lx Ly Lz Ma Mb Mc Md Me Mf Mg Mh Mi Mj Mk Ml

Hv Hw Ih Ii In Io Ip Ir It Iu Iv Jg Jh Ji Jj Jk Jm Jn Jq Js Lh Li Lj Lu Lw Lx Ly Lz Ma Mb Mc Md Me Mf Mg Mh Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe Of Oh Oi Ok Om Oy Oz Pb Pc Pd Pe Pf Pg Po Qa Qb Qc Qd Qe) Pg(Et Fp Hq Hr Hu Hv Hw Ih Ii In Io Ip Iq Ir It Iu Iv Jg Jh Ji Jj Jk Jm Jn Jo Jq Js Lh Li Lj Lu Lw Lx Ly Lz Ma Mb Mc Me Mf Mg Mh Mj Mk Ml Mm Mn Mp Mq Mr Ms Mt Mu Mv Mw Mx My Na Nb Nc Nd Ne Nf Ng Ni Nj Nk Nl Nm Nn No Nq Nr Ns Nt Nu Nv Nx Ny Oe Of Oh Oi Ok Om Oy Oz Pb Pc Pd Pe Pf Po Pz Qa Qb Qc Qd) Pe(Et Fp Hq Hr Hu Hv Hw Io Ip Ir Iu Iv Jg Jh Ji Jj Jk Jm Jn Jo Js Lh Lj Lu Lw Lx Ly Lz Ma Mb Mc Md Mf Mh Mj Mk Mn Mp Mq Mr Ms Mt Mu Mv Mw Mx My Na Nc Nf Ng Nj Nm Nn Nq Nr Ns Nu Nv Ny Oe Ok Om Pc Pd Po Qa Qb Qe) Om(Hv Hw Ih In Io Ip Iq Ir It Iu Iv Jj Jk Jn Jo Jq Js Jt Lh Li Lu Lw Lx Ma Mb Mc Me Mf Mg Mh Mj Ml Mm Mp Mq Ms Mt Mu Mv Mx Nc Ng Nj Nk Nl Nm Nn No Ns Nu Ny Oe Of Oh Oi Oy Oz Pc Pf Po Pz) Lh(Hq Hv Ii Iq Ir Iu Jh Ji Jj Jn Jo Jq Js Jt Lu Lx Ma Mg Mh Mj Mk Mm Mn Mr Ms Mt Mu Mv Mw Na Nb Nc Ne Nf Ng Nj Nk Nl Nm Nn No Nq Nr Nt Nu Nx Oe Of Oh Pd Pf Po Pz Qa Qb Qc Qd Qe) Po(Fp Hu Hv Ih Ip Ir Iu Iv Jh Ji Jj Jn Jo Js Jt Li Lu Lx Ma Mb Me Mf Mh Mk Mm Mq Mr Ms Mt Mu Mv My Na Nc Nd Nf Ng Nj Nk Nm Nu Nv Ny Oe Oh Pd Pf Pz Qa Qb Qd Qe) Ir(Hr Hu Hv Hw Ii Iq It Iu Jg Ji Jj Jm Jo Jq Js Li Lu Lw Ly Lz Mf Mg Mj Mk Ml Mm Mp Mq Mr Ms Mu Mv Mx Nb Nc Nf Ng Nj Nk Nn No Nr Nt Nu Nx Oe Of Oh Oi Oy) Iv(Hu Hv Hw Ip Iu Jg Jh Ji Jj Jk Jo Li Lu Lw Lx Lz Ma Mf Mg Mj Mk Mm Mn Mp Mq Mr Ms Mt Mu Mw My Nc Nd Ng Nj Nn No Nq Nv Oe Oi Qa Qb Qd) Mu(Hr Hv Ih Ip It Iu Jj Jn Lu Ly Lz Me Mh Mj Mk Mm Mq Mr Ms Mx Nb Nj Nl No Nr Nt Nu Nv Oh Ok Oy Pb Pc Qa Qb Qd Qe) Jj(Hu Hv Ih Ii Ip Iu Ji Jk Lx Mj Mk Mn Mr Mt Mx My Nb Nn No Nr Nv Oy Pc Qa Qb Qd Qe) No(Hu Jh Lu Lx Ma Mb Ms Mt Mv Na Ng Nj Nv Oe Pc Qa Qb Qd Qe) Lx(Hq Hu Jn Lu Mj Mk Mm Mr Nb Nm Nn Nr Nt Nu Oh Pb Pf) Mv(Hv Ip Lu Lz Mj Mk Ms Mx Nb Ng Nr Nu Pb Qb Qd) Nn(Hu Ip Lu Me Mt Mx Nj Nr Oy Qa Qb Qd Qe) Mj(Jh Lj Ma Ms Mt Na Nj Nv Oe Pc Qa Qb) Qb(Hu Jg Lu Mk Mr Nb Nc Nj Nr Nu Oy) Mt(Lu Lz Mh Mk Mp Mr Nb Nl Nr Pb) Ji(Hu Hv Jk Lu Ly Mm Ms Nc Nj) Nv(Hu Jo Lu Mk Mm Mr Nj Nr Oy) Qd(Hu Jg Lu Mk Mm Nc Nj Pc) Ms(Jg Mk Mr Nb Nr Pb) Qa(Hu Lu Mk Mr Nb Nr) Qe(Lu Mk Mm Mr Nj Nr) Oe(Ii Mk Nb Nr Pb) Jg(Jn Mg Ng Nj) Lu(Hv Jk Mp) Pe(Hu Jk Jq) LwJn NbNg Njli} Oe{aA(Et Fp Fr Hq Hr Hu Hv Hw Hx Ih Ii In Io Ip Iq Ir Is It Iu Iv Jg Jh Ji Jj Jk Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Pg Po Pz Qa Qb Qc Qd Qe) Hx(Et Fp Fr Hq Hr Hu Hv Hw Ih Ii In Io Ip Iq Ir Is It Iu Iv Jg Jh Ji Jj Jk Jm Jn Jo Jp Jq Jr Js Jt Lh Li Lj Lu Lw Lx Ly Lz Ma Mb Mc Md Me Mf Mg Mh Mi Mj Mk Mm Mn Mq Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Oh Oi Ok Om On Oy Oz Pa Pb Pc Pd Pe Pf Po Pz Qa Qb Qc Qd Qe) On(Fp Fr Hq Hr Hu Hv Hw Ih Ii In Io Ip Iq Ir Is It Iu Iv Jg Jh Ji Jj Jm Jn Jo Jp Jq Jr Js Jt Lh Li Lj Lu Lw Lx Ly Lz Ma Mb Mc Md Me Mf Mg Mh Mi Mj Mk Mm Mn Mq Ms Mt Mu Mv Mw Mx My Mz Na Nb Nc Nd Ne Nf Ng Ni Nj Nk Nl Nm Nn No Nq Nr Ns Nt Nu Nv Nw Nx Ny Of Oh Ok Om Oy Oz Pa Pb Pc Pd Pe Pf Pz Qa Qb Qc Qd Qe) Pg(Et Fp Fr Hq Hr Hu Hv Hw Ih Ii In Io Ip Iq Ir Is It Iu Iv Jg Jh Ji Jj Jm Jn Jo Jp Jq Jr Js Jt Li Lu Lw Ly Lz Ma Mb Mc Md Me Mf Mg Mi Mj Mk Ml Mm Mn Mp Mq Mr Ms Mu Mv Mw Mx My Mz Na Nb Nc Nd Ne Nf Ng Ni Nj Nk Nl Nm Nn No Nr Ns Nt Nu Nv Nw Nx Ny Of Oh Oi Ok Om Oy Oz Pa Pb Pc Pd Pe Pf Po Pz Qc) Pa(Et Fp Fr Hq Hr Hu Hv Hw Ih Ii In Io Ip Iq Ir Is It Iu Iv Jg Ji Jj Jm Jo Jp Jq Jr Js Jt Lh Li Lj Lu Lw Lx Ly Lz, Ma Mb Mc Md Mf Mi Mj Mk Ml Mm Mn Mp Mq Mr Ms Mt Mu Mv Mw Mx My Mz Na Nb Nc Nf Ng Ni Nj Nm Nn No Nr Ns Nu Nv Nw Nx Ny Of Oh Oi Ok Om Oy Oz Pb Pc Pd Pe Pf Pz Qa Qb Qc Qe) Jr(Fr Hq Hr Hu Hv Ii In Io Ip Ir It Iu Jg Jh Ji Jj Jk Jm Jn Jp Jq Js Lh Li Lj Lu Lw Lx Ly Mc Md Me Mf Mi Mj Mk Ml Mn Mp Mq Mr Ms Mt Mu Mv Mw My Mz Nb Nc Nj Nk Nl Nm Nn No Nq Nr Ns Nt Nu Nw Nx Ny Of Ok Oy Pb Pc Pd Pe Pf Po Pz) Mz(Fr Hr Hu Hv Ii Ip Ir Is Iu Iv Jg Jj Jk Jn Jp Jq Js Lh Li Lu Lw Ly Lz Mf Mi Mj Mk Ml Mm Mp Mq Mr Ms Mu Mv My Nb Nc Nj Nk Nn No Nr Nu Nw Nx Of Oh Om Oy Pb Pc Pe Po) Mi(Fp Hu Hv Ih Ip Ir Is It Iv Jj Jo Jp Jq Jt Lh Lu Ly Mb Mf Mg Mj Mk Mm Mn Ms Mv My Na Nb Nc Nf Ng Nj Nk Nm Nr Nu Nv Nx Oh Ok Oy Pb Pc Qa Qb Qd Qe) Pe(Fr Hq Hr Hu Hv Hw Iq Ir Is Jh Ji Jj Jo Jp Jq Js Jt Lh Lu Lx Ma Mf Mh Mn Mq Ms Mt Mv Mx Na Nf Nj Nq Nu Nv Nw Ny Oh Pc Pd Pf Qa Qb Qe) Is(Hu Ii Iq Ir Iu Jg Jj Jo Jp Jq Js Jt Lu Ly Mf Mj Mk Mm Mq Mr Ms Mx Nb Nc Nj Nm Nn No Nr Ns Nu Nw Ny Of Oh Oy Pb Pc Pe Po Pz) Fr(Hv Ii Ip Ir Iu Jj Jn Jo Jp Li Lu Ly Mf Mg Mj Mk Ml Mm Mq Mr Ms Nb Ng Nh Nj Nk Nl Nm Nr Nu Nx Of Oh Oi Ok Pc Pd Pf Pz Qb) Jp(Hr Hu Hv Hw Ii In Ip Ir Iu Iv Jk Lh Li Lu Lw Lx Ly Mj Mk Mr Ms Mv Nb No Nr Nu Nw Oy Pb Pc Po Qa Qb Qe) Po(Fp Hr Hu Ih Iq Ir Iu Iv Jj Jn Jo Js Jt Li Lu Ly Mb Mm Ms Mt Mv My Nf Nj Nk Nm Nx Oh Pc Pd Pz Qa) Lh(Hq Ii Iu Jj Jo Js Jt Lu Lx Mg Mj Mk Mm Mr Ms Nb Nf Ng Nm Nn No Nq Nr Nw Of Oh Pc Pd Pz) Ir(Ii Iq Iu Jg Jj Jo Li Lu Lw Mf Mj Mk Mm Mp Mr Ms Nb Nc Nn No Nr Nu Nw Oy Pb Pc) Jj(Ih Ii Iu Iv Jk Lx Mj Mk Mr Mt My Nb No Nr Nv Nw Oy Pc Qa Qb Qd Qe) Nw(Hu Ii Jk Jo Js Jt Lu Ly Md Mf Mj Mm Ms Nj Nk Nm Nx Oh) Nr(Hw Jh Jo Lx Ms Mt Mu Mv Nn Nv Qa Qb Qe) Mj(Jh Jo Lj Lw Lx Ms Mt Mu Mv Nf Nl Nq Qa) Pc(Hu Jn Lu Lx Ms Mt Nv Qa Qb Qd Qe) Mk(Hr Lx Mt Mu Mv Nv Qa Qb Qe) Lu(Jg Lw Lx Mu Mn Om Qa Qb) Mr(Lx Mt Nv Qa Qb Qe) Ms(Jg Ji Mu No Om) Nb(Jo Lx Mt Mv Qa) Lx(Hq Mm Oh) Ii(Jo Nv Qa) Jg(Ly Mg Ng) No(Hu Qa) NnHu NuMv LyMu} Jj{Pa(aA Et Fp Fr Hq Hr Hu Hv Hw Hx Ih Ii In Io Ip Iq Ir Is It Iu Iv Jg Jh Ji Jk Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Oh Oi Ok Om On Oy Oz Pb Pc Pd Pe Pf Pg Po Pz Qa Qb Qc Qd Qe) Pg(aA Et Fp Fr Hq Hr Hu Hv Hw Hx Ih Ii In Io Ip Iq Ir Is It Iu Iv Jg Jh Ji Jk Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nv Nw Nx Ny Of Oh Oi Ok Om On Oy Oz Pb Pc Pd Pe Pf Po Pz Qa Qb Qc Qd Qe) Hx(aA Et Fp Fr Hq Hr Hu Hv Hw Ih Ii In Io Ip Iq Ir Is It Iu Iv Jg Jh Ji Jk Jm Jn Jo Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mv Mw Mx My Mz Na Nb Nc Nd Ne Nf Ng Nh Ni Nj Nk Nl Nm Nn No Nq Nr Ns Nt Nv Nw Nx Ny Of Oh Oi Ok Om On Oy Oz Pb Pc Pd Pe Pf Po Pz Qa Qb Qc Qd Qe) Mz(aA Et Fp Fr Hq Hr Hu Hv Hw Ih Ii In Io Ip Ir Is It Iu Iv Jh Ji Jk Jm Jn Jo Jq Jr Js Jt Lh Li Lj Lu Lw Lx Ly Ma Mb Mc Md Me Mf Mg Mh Mj Mk Ml Mm Mn Mp Mq Mr Ms Mt Mv Mw Mx My Na Nb Nc Nd Ne Nf Ng Nh Ni Nj Nk Nm Nn No Nq Nr Ns Nv Nx Ny Of Oh Oi Ok Om On Oy Oz Pb Pc Pd Pe Pf Po Qa Qb Qd Qe) Qb(aA Fp Fr Hq Hr Hu Hv Hw Ih Ii In Io Ip Iq Ir Is It Iu Iv Jg Jh Jk Jm Jn Jo Jq Jr Js Jt Lh Li Lj Lu Lw Lx Ly Lz Ma Mb Mc Me Mf Mg Mh Mj Mk Ml Mm Mn Mp Mq Mr Ms Mt Mv Mw My Na Nb Nc Nf Ng Ni Nj Nk Nm Nn No Nq Nr Ns Nt Nv Nw Nx Ny Of Oh Oi Om On Oy Pb Pc Pe Po Qa Qd Qe) Qa(aA Et Fp Hq Hr Hu Hv Hw Ih Ii In Io Ip Ir Is It Iu Iv Jh Ji Jk Jn Jo Jq Jr Js Li Lj Lu Lw Lx Ly Lz Mb Mc Me Mf Mg Mh Mj Mk Ml Mm Mn Mp Mq Mr Ms Mt Mw My Na Nb Nd Ne Nf Ng Nh Ni Nj Nk Nm Nn No Nq Nr Ns Nt Nw Nx Ny Oh Oi Ok On Oy Oz Pb Pc Pd Pe Pf Po Pz Qd Qe) Pe(aA Et Fp Hq Hu Ii In Io Ip Iq Ir Is Iu Iv Jg Jh Ji Jk Jn Jo Jq Js Jt Li Lj Lu Lw Lx Ly Lz Mc Md Me Mf Mg Mk Ml Mm Mn Mp Mq Mr Ms Mx My Nb Nd Ne Nf Nk Nl Nm Nn No Nr Ns Nt Nx Ny Oh Oi Ok On Oy Pb Pc Pf Pz Qd Qe) Qe(aA Et Hu Hv Hw Ii In Ir Is Jk Jn Jo Jr Js Jt Lh Lj Lu Lw Lx Ly Lz Ma Mb Mc Me Mg Mh Nj Nk Nm Ns Nx Ny Oh Oi Ok Om On Oy Pb Pd Pf Po Pz Qd) Jk(aA Fr Ih Ii In Ip Iq Ir Is Iv Ji Jn Jo Jp Jr Jt Lh Lu Lw Ly Ma Mf Mg Mi Mk Mm Mn Mq Mr Ms Mt Mv My Nb Nc Ng Nj No Nr Nv Nw Nx Ny Oh On Pc Po Pz Qc Qd) Ir(aA Hu Hv Ih In Jh Jm Jn Jo Jq Jr Js Jt Lu Ly Mf Mg Mh Ml Mm Mp Mq Ms Mw Mx My Na Nd Ne Ng Nh Nj Nk Nm Nx Oh Oi Ok Pd Qd) Qd(Hu Hv Hw Ii In Ip Jn Jo Jr Js Lj Lu Lx Ly Mf Mg Ml Mm Mq Ms Mw My Ne Ng Nj Nk Nm Nx Ny Oh Oi On Oy Pb Pc) Is(Hu Hv In Ip Iq Jo Jq Jt Lj Lu Lx Ly Mf Mg Mj Mm Mq Ms My Na Nd Ne Ng Nj Nk Nm

Pf Pg Po Pz Qa Qb Qc Qd) Pf(Fr Iu Jg Jh Jp Jr Js Lh Lw Lx Ma Ms Mt Mv Mz Nc Ni Nj Nn Nw Nx On Pc Pg Qa) Iu(Fp Fr Hu Ir Jr Lu Ly Mb Ms Mv Mz Nc Nf Nj Nx Ny Pe) Fr(Js Mm Ms Ng Nj Nm Nn Nv Nx Ny Of Oh Pz) Js(Hr Jg Ji Jp Jr Ma Mv Mz Nw Pc Pg Qa) Mm(Jg Jp Lh Ma Ms Mv Mz Nj Nw On Pc) Ms(Jg Jp Lu Mv Nj Nx Of Oh Oy) Jp(Hq Li Lu Ng Nj Nx Oh Pe) Mv(Hq Ng Of Oh Pd Pe Pz) Nj(Ii Nx Of Oh Oi Pc) Lu(Lw Ng Nn Of Pc) Nf(Hr Hw Ii Jr Nx) Mz(Ii Nn Oh) Nc(Hq Oh Pe) Jr(Nx Oh Pe) Ng(Hr Hu) Pz(Jg Ma) Pc(Hq Pe) NnNx NaHr IiPg}
Fr{Ms(Et Fp Hu Hv Hw Hx Ii In Ir Is Iu Iv Ji Jk Jn Jp Jq Jr Js Lh Li Lu Lw Ly Lz Mf Mg Mj Mk Ml Mm Mq Mr Mv Mw Mx My Mz Na Nb Nf Ng Nj Nk Nm Nn No Nq Nr Ns Nu Nw Of Oh Oi Ok Om On Oy Pb Pc Pd Pe Pf Pg Po Pz Qa Qb Qc Qd Qe) Mm(Hx Ir Is Jn Jr Lh Lx Ly Mg Mx Mz Ne Ng Nh Nk Oi Pe Pg Qa Qb Qd Qe) Ng(Hu Hx Ii Jk Jr Lu Ly Mk Mr Nb Nk Nm Of Oh Ok Oy Pb Pe Pg) Jr(Jg Jn Jq Js Li Ly Mg Nj Nm Nn Nx Of Oh Oi Ok Pd Pz) Oh(Hx Is Jn Ly Mg Mz Nh Nk Oi Pg Qa Qb) Pz(Hx Is Mz Ne Nh Pg Qa Qb Qd) Of(Hx Ly Mz Ne Nh Oi Pg Qa Qb) Ok(Hx Jn Ly Mg Mz Nw Oi Pe) Pg(Ii Iu Mg Nm Nn Nv Pf) Oi(Hu Lu Ly Mg Nj Nk) Nn(Hx Mz Qa Qb) Mg(Hu Ly Nj Nk) Mz(Nm Nx) Pd(Lx Ly) NhNj PePf} Nx{Pg(Hq Hv Hx Iq Is It Iu Iv Jm Jp Jr Js Lw Ma Mf Mg Ml Mm Mq Ms Mu Mv My Mz Na Nc Nf Ng Ni Nj Nm Nn Ns Of Oh Oi Om On Oy Pd Pf Pz) Mz(Is Jk Jp Jr Lw Mm Ms Nj Nn Oi On Po) On(Jp Jr Md Mq Nf Ok Om) Iu(Ir Is Pe Qd) Nn(Hu Jr) Iq(Is Pe) Jp(Is Qb) PoLj LwJr LxHq MsNw NgLh} Ms{Jr(Jg Ji Jk Jp Js Lw Ma Mu Mv Mw Mz Nn On Pc) Lh(Hq Iu Jp Mm Mz Na Nf Ng Nm Nq Nw Of Pz) Mu(Hx Jn Jp Mj Mk Mr Mz Nb Nr Oi Pe Pg) Mv(Hx Jp Mz Nb Nr Pe Pg) Lu(Mz Nn Nw Pg Po) Jg(Hx Mg Mz Ng Oi) Mz(Jp Nn Oi) Jp(Mg Ng) NnHu MmOn JiOi} Mm{Mz(Ir Jg Jh Jk Jr Js Lh Lw Lx Ma Mn Mp Mt Mu Mv Mw Nd Ng Nn Nq Nv Oi On Pc Pg Po Qa Qb Qe) On(Ii Iq Jr Lu Mg Nc Nf Ng Nj Ny Oi) Lh(Iq Iu Lw Mg Ng Nn Oi Pc Pg Qa) Lx(Lw Nn Oh Pc) Pg(Ma Mv Ng) Pc(Jr Mt)} Jr{Js(Iq Is Iu Jg Jp Lh Lw Lx Mj Mp Mv Mz Ng Nj Nn Nw On Pc Pe Pg Po Qa) Pc(Lu Mf Mq Nf Ng Oh Pd) Iq(Jk Jn Ml Pg) Nn(Li Lu Oh) Lw(Lu Nj Nm) Mv(Ng Oi) LxPd MgJg NgOn} Lu{Pg(Ii Iq Iu Lw Mg Nf Ng Nn Of Oi Pc Pd) Mz(Iq It Iu Js Lw Ng Oi Pc) Iu(Hx Ir Is Pe Qa Qb Qd) Ng(Jp Lh Ma Mv Nn Po) Iq(Pe Qb) On(Nf Of) PoPd NnMg IsOi} Ng{Mv(Hu Lx Ly Mk Nb Nr Oy Pb Pe) Lh(Iq Iu Js Li Lj Ly Ns) Hu(Jg Lw Nn Pc) Jp(Jk Pg)} Mv{Pg(Ii Of Pf) Pd(Lx On) LyOi MzOh} Lh{Iu(Mg Mz Nf) MgPc MzOh IiPg IqPd} On{Nm(Lw Nb) Li(Hr Na) MbOk NfOh} Po{Pd(Hu Nc Nj) Li(Js Nf)} Lx{Hq(Js Lj Nm Ny Oh)} Mz{MuOh NjOi Hulu IiJk} Hu{NnOh Irlu} Pe{NfHw HrJs} LwMjLj IqOiPg Unconstrained panels with 3 analytes, where 1.0E-7 >= 'AUC p-value' > 1.0E-8. Contains 3,697 panels of 260,130 total panels evaluated. :
Jj{Is(aA Et Fp Hq Hr Hw Ih Ii Io It Iu Iv Jh Ji Jm Lh Li Lw Lz Ma Mb Mc Md Me Mh Mk Mn Mp Mr Mw Nb Nc Nf Nh Ni Nl Nn No Nq Nr Ns Nt Nw Ny Of Om Oy Oz Pb Pc Pf Po Pz Qd) Lh(Hr Ih Ii Io Ip Iq Ir It Iu Iv Jh Ji Jm Jn Jr Lj Lx Mb Mc Md Mg Mi Mj Mk Ml Mp Mr Mt Mw Mx Nb Nc Nd Nf Ng No Nq Nr Ns Nv Nw Ny Om On Oy Oz Pb Pc Pe Pf Po Qd) Ir(Et Fp Fr Hq Hr Hw Ii Io Ip Iq It Iu Iv Ji Li Lj Lw Lx Lz Mb Mc Md Me Mj Mk Mn Mt Nb Nf Ni Nl Nn No Nq Nr Ns Nv Nw Ny Of On Oy Oz Pb Pc Pf Po Pz) Qd(aA Et Fp Hq Hr Ih Io Iq It Jh Jm Jq Jt Li Lw Lz Mb Mc Md Me Mh Mk Mn Mp Mr Mt Mx Na Nb Nd Nf Nh Ni Nn No Nq Nr Ns Nw Of Ok Om Pd Pf Po Pz) Qe(Fp Hq Hr Ih Io Ip Iq It Iu Iv Jh Ji Jm Jq Li Lw Lz Md Mh Mk Mn Mr Mt Nc Nf Ni Nl Nn No Nq Nr Nt Nw Of Oz Pc) Jr(Fr Hq Hv Ih Ii Io Ip Iv Jh Jt Lw Lx Ma Me Mh Mi Mj Mk Mn Mp Mv Mx Ng Nk Nm Ns Nx Oh On Oy Pb Pc Pd Pe Po) Jk(Hq Hu Hv Hw Iu Jq Js Lx Mb Mc Me Mj Ml Mp Mx Na Nf Ni Nk Nm Nn Ns Nt Of Oi Ok Om Oy Pb Pd Pf) aA(Hv Ih Ip Iv Ji Jo Jq Js Li Mf Mh Mn Mq Mx Na Nb Nd Nf Nl Nm Nq Ns Ok Pd Po) My(Hu Hv Hw Ii Ip Iv Jn Lx Mg Mi Mn Mp Mq Mt Mw Nd Ng Nn Nv Oi On Po) Lx(Hu Ii Mf Mj Mk Mq Mr Ms Nb Nh Nk Nr Nx Oh Oi On Oy Pb Pc Po) Qb(Et Ji Jp Md Mh Mu Mx Nd Ne Nh Nl Nu Ok Oz Pd Pf Pz Qc) Hu(Fr Hv Ii In Ip Lw Ly Mi Mj Mp Mx Ne Nn Nq Oe Pc) Qa(Fr Iq Jg Jm Jp Ma Md Mu Mv Mx Nc Nl Nu Nv Of Qc) Mj(Ii Ip Mg Mq Mt Nd Ns Nx Oi On Pc Pd Pe Po) Nh(Hv Ip Jg Jp Mt Mw Nc Nn No Nw Pc Pe Po) Mz(Iq Jg Jp Lz Mi Mu Nl Nt Nu Nw Pz Qc) Mt(Hv Ii Mf Mm Ne Nj Nk Oi On Pe Po) Ms(Hv Ii Mn Mp Mu Mw Nd Nv On Po) Ne(Ip Iv Jn Mw No Nv Nw Pc Po) Og(Jg Jn Jt Lu Mv Mw Nt Nu) Oe(Hv Io Ip Jg Mn Nu Om) Pe(Ih Jm Mh Mw Na Ni Oz) On(Ii Jm Nm Nr Ny Ok) Lu(Ii Mp Mw Nd Nv) Nj(Mn Mw Nd Nq Nv) Ly(Ma Mn Mp Mv) Hx(Jp Mu Nu) In(Mq Mw Nv) Po(Mh Pd) Nd(Ih Jn) Nv(Mm Oi) FrMg MwNk IhOi} Og{Iv(Et Fp Hq Hr Ih Ii In Io Iq Jt Lh Lj Ly Mb Mc Md Me Mh Mv Na Nb Ne Nf Nh Ni Nk Nl Nm Nr Ns Nt Nu Nx Ny Of Oh Ok Oy Oz Pd Pf Pz Qc Qe) Ir(Et Fp Hq Ih In Io Ip Jk Jn Jt Lj Ma Mb Mc Md Me Mh My Na Ni Nl Nm Ns Nv Ny Ok Oz Pc Pd Pf Pz Qc Qd) Ji(Hr Hw Ii Ip Jn Jo Jq Li Lz Mf Mg Mj Mk Mq Mr Mu Mv Mx My Nb Nk Nm Nn No Nr Nu Oe Oh Om Oy Pz Qb Qd) Om(Et Fp Hq Hr Hu Ii Jg Jm Lz Mk Mn Mr Mw My Na Nb Nd Ne Nf Nh Ni Nq Nr Nt Nv Nx Ok Pb Qa Qb Qc Qd) Po(Et Hq In Io Iq It Jg Jk Jq Lw Lz Mc Mg Mj Ml Mn Mp Mw Mx Nb Ni Nr Ns Nt Nx Of Oi Ok Oy Oz Qc) No(Hv Ih In Ip Jk Jn Jo Jq Js Jt Mh Mj Mn Mp Mw My Nc Nd Nk Nu Nx Pd Pe) Qd(Hr Hv Hw Ip Iu Jk Jq Li Lw Ly Lz Mf Mp Mr Ms Nb Nf Nr Nu Oe Oy Pe Pz) Mv(Hw Ii It Jn Lw Ly Mg Mh Mm Mp Mr Mu Nj Nk Nn Oe Oy Pc Qa Qe) Lx(Hv Hw Ip Jk Jq Lw Ly Lz Mb Mh Mu Mx Nc Nd Ne Nf Of Oy Pd) Mj(Hv Lw Md Mf Mh Mk Mn Mp Mq Mr Mw Nf Ng Nl Nn Nq Pb Qe) Mt(Hu Hv Io Ip It Jm Jn Lw Me Mf Mm Mu Mx Nt Nu Ok Oy Oz) Pe(Ih Ii Iq Li Me Ml Mm Nd Ni Nk Oh Oy Oz Pb Pf Pz Qc) Lh(Hu Hw Ip Jg Jk Jm Li Lw Mf Nd Ny Oi Ok Oy Pb Pc) Qb(Hv Ii Ip Jm Jn Jq Li Lw Ly Lz Mm Nf Pb Pc) Mu(Et Hw Ii Lw Mg Mn Nc Nd Nk Nm Ns Nx Oe) Nn(Hv It Jk Jn Mk Mr My Nc Ng Nl Nu Nv) Mk(Hw Jh Jk Jn Jo Ma Mp Mw Na Nj Nu) Qa(Hv Ii Jg Lw Lz Mm Nc Nj Nu Oy Pb) Qe(Hu Iu Jg Jo Jq Lw Nb Nc Oh Pg Pz) Mr(Jh Jk Jn Jo Ma Mp Mw Nj Oe On) Lu(Et Jg Jn Jq Lw Ma Mn Mx Pc) Nr(Jh Jk Jn Jo Ma Mp Mw Nj) Nj(Hv Jk Lz Nb Nd Pb Pc) Hu(Et Hv Lw Lz Mn Mp Pb) Nv(Hv Hw Jq Lw Lz Nc Nu) Pc(Jn Ms Mx My Nb Oe) Jg(Hv Jq Mx Nc Oe) Ma(Hv Nb Nu Oy) Jk(Ip Nb Of) Jp(Iq Jo Pz) Oy(Jn Jq Ms) Lw(Ih Me) Nh(On Pg) Ii(Jo Ms) Jh(Hv Nb) Jt(Mz Pg) NuOe MpHq NaPb NeOn IpJq} Oe{Fr(Et Hq Hw Ih In Io Is It Iv Jh Jk Js Jt Lh Lw Lx Ma Mb Mc Md Mi Mp Mv Mw Mx My Nc Nd Ne Nf Nn No Nq Nv Nw Ny Om Oy Oz Pb Po Qa Qd Qe) Mz(Et Fp Hq Hw In Io Iq It Jh Ji Jm Jo Lj Lx Ma Mb Mc Md Me Mg Mu Mv Nd Ng Ni Nl Nm Nq Ns Nt Ny Oi Ok Oz Pd Pf Pz Qa Qb Qc Qd Qe) Nw(Hv Iu Iv Jq Lw Lx Mg Mi Mk Mn Mp Mq Mr Mt Mv Mw Mx Nb Nc No Nr Nu Nv Of Ok Oy Pd Pf Po Pz Qa Qb Qd Qe) Po(Et Hv Ip Jg Jh Ji Lh Lx Ma Mf Mh Mk Mn Mq Mr Na Nc Nq Nr Nu Nv Ny Of On Pa Pf Qd) Jr(Et Fp Ih Iq Is Jo Lz Ma Mb Mg Mm Mx Na Nd Nf Ng Ni Nv Oh Oi Om Oz Qa Qb Qc Qd Qe) Pe(Et In Ip Iu Iv Jg Jk Jm Lw Ly Mb Mc Md Me Mi Mk Mr Mu Mw My Ng Nm Nr Ns Oi Pb Qd) Jp(Ih It Jg Jn Lz Mf Mg Mp Mq Mt Mu Mx My Nc Nd Nf Nh Nj Nk Nn Nq Nx Of Qd) Is(Hq Hv Hw Io It Iv Jk Jm Li Lw Lz Mg Mp Mu Mv Mw Nk Ok Pf) Ir(Hr Hu Hv It Iv Ji Jk Jm Jt Ly Lz Ml Mq Mu Nt Nx Ok) Mi(Ii Jh Ji Jk Js Md Mh Mq Mr Mw Nd Ny Pd Pz) Lh(Hv Iq Iv Jg Mf Ne Nj Nk Nu Nx Oy Pb Pf Pg) Mj(Hq Ma Mf Mh Mm Mr Mp Mw Na Ng Nv Qb Qe) Mv(Hv Ii Ip Lu Ly Mh Mr Ms Mx Nn Oy Pc) Lx(Hu Ii Ly Nm No Nu Nx Oy Pd Pf Pg) Mk(Hw Jh Jo Ma Mn Mp Ms Mw Nn Qd) Nb(Jh Lw Ma Ms Mu Ng Nn Qb Qe) Ii(Hr Jg Jh Ma Mn Ms Mt Qb Qe) Pg(Jk Lj Mh Mt Nh Nq Qa Qb Qd) No(Ly Mn Mt Nm Ns Nv Nx Qb) Mr(Hr Jo Mp Ms Mu Mw On Qd) Jg(Hv Iv Mx Nu Qa Qb Qd Qe) Pa(Jh Jk Jn Me Nd Nh Nk Qd) Lu(Ji Jk Mn Mp Mt Qd Qe) Pc(Ih Jk Jo Mu Mw Nj) Nr(Ma Mn Mp Qd) Mu(Ip It Iv Pb) On(Jk Lj Mp Oi) Oy(Ms Mt Nv Qa) Nn(Iv Ly Qd) Mm(Ji Nv Qe) LwHu NdIv IuQe} Jl{Lu(Fp Fr Hq Hr Hu Hv Hw Hx Ih Io Ip Is Iv Jh Ji Lj Lx Lz Mc Md Me Mj Mk Mn Mp Mt Mu Mw Nb Nc Nd Nh No Nu Nw Om On Oz Pb Pe Pg Po Qa Qc Qe) Ny(Hq Hv Hw In Io Ir It Iv Jg Jh Ji Jn Lj Ly Lz Mc Me Mj Mn Mp Mt Mu Mw Mx My Nc Ne Nf Nh Ni Nl Nq Ns Nu Oy Oz Pb Pe Pf Qa Qb Qc Qe) Mg(Et Fr Hr Hv Hw Ii In Io Ip Is It Iv Jg Jh Ji Jk Jq Lz Mc Md Me Mj Mp Mt Mu Mv Mw Mz Nf No Nq Nr Ns Nt Nu Nv Nw Oz Po Qa Qc Qe) Oi(Fr Ih Ii In Io Ip Ir Is It Jg Jh Ji Jk Lh Lw Lx Lz Mc Md Me Mj Mn Mv Mw My Nd Nf Ni Nn No Ns Nt Nw Om On Oy Pb Pe Po Qa Qc Qe) Nj(Hr Hu Hv Hw Hx Is Jk Jm Jn Lh Lj Lx Ly Me Mj Mk Ml Mr Mx My Mz Nb Nc Ne Nf Nh Nl Nn Nq Ns Nw On Oz Pb Pe) Ng(Fr Hr Hw Ih In Io Ip Ir Is It Iv Lw Lz Md Me Mp Mt

Figure 16 Continued

Mu Mv Mx My Nf Ni No Ns Nt Nv Nw Om Oz Qa Qc) Iq(Fr Hq In Io Ip Ir Jg Jh Ji Lw Ly Mn Mt Mu Mw My Nl Nq Nu Qa Qb Qc Qd Qe)
Nv(Fp Hq Hv Hx Ih Iv Jm Jn Jq Js Lh Mb Ml Mq Mx Na Nc Nf Nk Nn Om On Pc Pd) Js(Hw Hx Iv Jm Jp Lh Li Mb Mf Mj Mq Mr Mz Nc Nk
No Nr Pb) Ii(Fr Hr Ip Jg Jm Lz Mh Mv Nd Ne Nh Nl Oz Qb Qc Qd) Pd(aA Hw Jp Lh Li Mb Mf Mj Nb Nc Nk Pc Pg Po) Jr(Fp Hq Ih Ly Mf Mq
Mx Na Nf Nr Oy Pf) Li(Hq Hu Mf Ml Mn Mq Mz Na Nc Nf Pc) Ly(Et Hw It Nc Ne Nf Nt Pf) Jq(Hq Is Jm Mb Na Nc Nk Ns) Ok(Mh Mt Mx
Nd Nl Qb Qd Qe) Hq(Hu Mf Mq Na Pa) Mb(Fp Mf Mq) Pa(Na Nf Pe) Mf(Hu Jm) Oy(Hu Pg) aA{It Na) MqJm NcNe LhNx} aA{Ng(Fp Hq Hr
Hv Hw Ii In Io Ir Is It Iv Ji Jn Js Li Lj Lz Ma Mb Mc Me Mg Mh Mi Mj Ml Mm Mr Mt Mw Mx Nb Nc Nd Nk No Nr Ns Nt Nv Nw Om Oz Pd
Qa Qc Qd Qe) Iu(Hv Ih Ii Iq Iv Jh Ji Jn Jo Jq Js Li Lj Lu Lw Md Mf Mg Mh Mj Mn Mp Mq Mw Mx Nb Nd Nk Nl Nm Nn Nq Nr Ns Nt Nv Oi
On Oz Pc Pd) Iq(Hu Hv Ih In Ip Iv Jm Jo Jt Lh Lw Lx Mg Mj Ml Mm Mp Mq Mt Mw Mx My Nb Nf Nj Nl Nn Ns Nu On Oz Pb Pc Pd Po Qd
Qe) Jt(Et Hq Ih Ii Io Iv Jq Js Li Lj Ly Mc Md Mf Mg Mj Ml Mq Mx Nb Nf Nh Ni Nj Nk Nl Ns Ok Om Oz Pd Pz) Pc(Fp Hu Hx In Ip Jg Jh Jk Jn
Js Lj Lu Mb Md Mh Mq Mv Mx My Nn No Nt Nw Of Ok Pg Pz Qb) Jo(Fp Hv Ih Ii Iv Jg Jn Li Md Me Mf Ml Mq Mu Mv Mx My Na Ne Nf Nk
Nl Ns Nw Om Pd) Oi(Hv Ip Ir Is Iv Jp Js Li Lw Lx Ma Mf Mi Mq Mx Nc Nf Ns Oz Qa Qe) Mz(It Jn Li Lj Ly Mf Mg Mq Mx Nf Nj Nk Nm Nt
Nv Nx Ok Pf) Lw(Hu Ji Jq Js Lu Mf Mq Mx Nf Nk Ns Nt Of Oh Pd) Nn(Ji Jq Js Mf Mq Nf Nq Ns Nx Of Oh Pa Pd) Jr(Hv Ii It Lj Ly Me Mf
Mq Mx Nf Nt Nx Oh) Mi(Hx Jq Lj Lu Md Mq Mx Nf Nk No Nq) Na(Jq Ly Mf Mp Mq Ns Nu On Pe Pg Po) Jq(Ir Jk Jn Lh Lx Ly Pb Pe Qa)
Pa(Hq Ii It Ly Nf Nx Ny Oy Pz) Mm(Fr Ip Lh Ma Ms Mt Qa Qb) Pg(Ih It Ly Nf Nr Oy Qd) Fr(Mg Of Oh Ok Pd) Ms(Li Mj Ny Oh Ok) Ip(Js Mf
Mx Pd) Ly(It Jg Jp) Lx(Nx Of) Mp(Js Pd) Oh(On Qa) PoNf MaOk MfMu NdNj InJs QbNx} Jo{Hx(Ii Io Is Li Lx Mf Mh Mj Mk Mq Mw My Nf
Ng Ni Nj Nm Ns Ok Pb Pe Qe) Is(Fp Hr Hw Iq It Jp Jq Jt Ly Md Me Ne Nk Nl Nt Nu Ny Oz Pz Qb Qc) Mz(Hv Io Iv Jh Ji Jn Jp Js Jt Ma Mf Ml
Mt Mw My Nd Nq Nx Of Oi) Ir(It Iv Jp Jq Jt Lj Mb Me Mh Mm Ms My Na Ng Nk Nu Nx Ny Qa Qb) Pe(Hq Ih In Iu Jg Jp Jt Lj Lz Mc Mf Ml
Na Nc Ng Nk Nx Of Pb) Jr(Hw Ii Ip Jk Js Mj Mn Mp Mv Nn Nr Nv Nw Qe) On(Fr In Jm Ma Mi Mp Mv Na Nd Ne Ng Nw Pd Pz) Po(Fr Hu Io
Jn Ma Mi Ms Nf Ng Nj Nm Nw) Qa(Hr Hw Ji Jk Li Lu Mn Mp Nf Nn Nu Om) Qb(Ip Iv Ji Jt Li Mn Mv Nf Nn Pb) Nv(Hr Iu Nf No Nu Nw Om
Oy Pb Qd) Fr(Ii Ip Jn Lh Mj Mx Nd Pb) Mw(Ip Mk Mr Nb No Nr Nw Pc) Lx(Hq Jh Jt Li Mn Mp Nu) Qe(Hr Io Iu Jt Mu Nd Nu) Jk(Hw Iv Ji Li
No Om Oy) Mt(Hr Ip Iu Li Nf Om) Lh(Ih Jn Ma Na Nl Nn) Mi(Hv Ii Lu Nd Nk) Mj(Jh Ma Mn Nq) Mn(Ii Ip Qd) Pa(Jq My Nt) Ms(Jg Ji) Nd(Ip
Iv) Ii(Jh Ma) Qd(Ji Nf) LwIh MxJg NeNw} Jt{Mi(Fp Fr Hr Hw It Iv Ji Jq Js Li Lj Lu Lw Lz Ma Mb Mc Md Mk Mm Mr Mx Na Nf Nl Nm Nn
No Ns Nu Ny Of Oh Om Pc Pf Pz) Lh(Et Hu Ih In Io Iq Jm Jq Lj Lu Mb Mc Me Mv Mw Mx My Na Nl Ns Nx Ok Oz Pb Pf Qe) Nw(Hv Hw Ih
In Ip Iu Iv Jn Lw Mm Mn Mp Mq Mw Nj Nn No Nq Oi Om Oy Pb) Jr(Ii Io Ip Ji Jk Jp Mj Mk Mr Mu Mv Mz Nb Nd No Nr Nv Oy Qe) Po(Fp Fr
Hr Ji Js Ma Mb Mg Mp Ms Mx My No Ns Ny Pb Pf) Hx(Io Jg Mf Ml Mm Mq Ms Ne Nf Ni No Oi Ok Pe Qa Qe) Ir(Et Hv It Jm Js Mq Mv Nf
Nu Oi Ok Om Oy Pf) Fr(Ii Ip Jk Mg Mj Mn Mt Nb Nd Ng Nr Oi) Jp(Lx Mk Mr Mz Nb Nr Pc Qb) Pe(Hr Jm Mh Mv Nf Nn Nq Oz) Qe(Hw Ii
Mp Mr Mz Nr Om) Jk(Ji Lw Mj Mk Mr Nb Nr) Mt(Mk Mr Nb Nr Pc) Qd(Ip Mu Nf Nu Ok) Mz(Ml Mn Mp Nf) Is(Ne Nh Qa) On(Mv Ne Nh)
Qa(Lw Oy) Qb(Lu Oy) Om(Lx Nv) Pg(Md Pf) MsJi} Pa{Iu(Hv Hw Hx Ii Is Iv Jp Lh Li Lj Lx Ma Me Mf Mg Mm Mq Mt Mx Na Nb Ni Ns Of
Oh Oi Oy Pg Qa) Pf(Et Hw Hx Ii Ir Is Iv Ji Jm Lu Ly Mb Mf Mh Mq Mu Mw Na Nk Nq Ns Oi Qe) Ms(Mq Hx Jm Jr Lj Lw Ly Mu Mw Mz Nn
Ny Oi On Pc Pe Pz) Nx(Hq Is Iv Ji Ly Mm Mu Mv Nc Of Oh On Oy) Lu(Fr Ii It Jr Mm Mz Nj Nr Oh Oi Oy) Jp(Ii Ly Mx Nf Nm Nn Nt Ny Pz)
Mm(Et Ji Jr Lw Mt Nc Ni Nn) Nj(Jq Jr Mf Nm Nn Oy Pe Pz) Fr(Ii Mg Ok Oy Pd Pe) Js(Et Lw Lx Nc Nf Nn) Ii(Ly Ma Mi Na Pe) Iq(Jh Mr Ni
Nk Qe) Oh(Ma Nf Nn Nw Pc) Jr(Hr Li Ng Of) Pe(Hq Hr Lw Nn) Oy(Mi Mv Pc) Nm(Mv Mz) Ma(Ng Nn) Nf(Mb Pc) LxNg MiOf HqHr}
Fr{Ms(Hq Hr Ih Io Ip Iq It Jg Jh Lj Lx Ma Mb Mc Md Me Mn Mp Mt Mu Nc Nd Ne Nh Nl Nt Nv Nx Ny Oz) Mm(Hv Ih Ii In Mf Mj Ml Mn
Mp Mq Mt Mv My Nd Nf Nq Oh On Pd Po) Oh(Hv In Ir Lx Mf Mi Ne Nq Of Pd Qd Qe) Ng(Et Jp Li Lj Nj Nr Nu Oi Pf Pz) Jr(Et Hq Iq Iu
Lu Mf Ml Mq Nf Nk Pf) Of(In Ir Jk Nd Nk Pe Qd Qe) Ly(Jp Li Mf Mz Nk Nm Pz) Iu(Hx Ir Mz Ne Nh Qa Qb) Oi(Hx Li Mz Nm Nu Pf Pg)
Mg(Hx Jp Lu Mi Nm Nu) Ne(Iq Nc Nj Nm Nn) Ok(Jp Lh Nk On Pg) Nx(Hx On Pe Pg) Pd(Nk Nr On Po) Nn(Is Nh Pe) Mz(Lu Nj Nv) Nh(Iq
Nc) Pz(Jr Qe) NkLi} Mi{Nm(Hv Hw Iv Jk Jp Lw Lx Mc Md Mq Mw Mx Nb Nr Pf) Lu(Et Ir Is Jk Mf Mj Mw Na Nf Nj Nl Ok On Qb Qe)
Ly(Et Hr Ji Lh Ma Mf Mw Nb Ne Of On Pd Pf Qd) Nx(Hq Iv Jk Mf Mk Mr Nf Ng Nr Nu Pb Pc Qd Qe) Jr(Fp Hv Hx Mc Md Mj Mt Nk Oi Ok
Pe Pz) Mm(Hu In Ma Mf Mq Mw Na Pz Qd) Nj(Fp Hq Jq Li My Na Nt Oh Pc) Ng(Ip Jp Mt Mz Nk Pg) Pz(Hu Is Lh Ly My Oh Qb) Li(Ip Ir Is Nb
Oy Pb) Mg(Jp Lj My Nk) Hx(Hu Na Ny Pd) Mz(Lj Mb Pd) Of(Ir Lh Lx) Oh(Jq Nw Om) Ok(Hu My Pg) Iq(Qd Qe) NnLh MyJq NcNe HuPc
QePf OyPg} Mz{Mm(Hv Hw Hx Ih Is Ji Jm Jn Jp Li Lu Mb Mc Md Mf Mg Mh Mj Mk Ml Mq Mr Mx My Na Nb Ne Nj Nm No Nr Ns Pd Pe
Pf Qc Qd) Ms(Is Ji Jk Lw Ma Mk Mr Mw Nb Nc Nj Nr Nw On Oy Pc Pe Po) Nx(Hv Hx Iq It Jg Js Ly Ml Mp Mu Nc Nk Of Oh Pc Qb) Lu(Ii Jn
Jq Ml Nf Of Pd Pg) Oh(Jg Jp Jr Nn Pc Pg) Mv(Nn Of Ok Pz) Iq(Hu Jk Jr Lh) Js(Is Lh Lx) Jg(Of Ok) Jr(Iu Oi) Lh(Of Ok) Pd(Lx On) NnMu
NgJk NjJp HuOi IiPg} Pg{Nx(Et Fp Hr In Ip Ir Jg Jh Ji Jn Lu Lx Lz Mb Mc Me Mh Mn Mp Mt Mw Nd Ne Nk Nl No Nq Nt Nu Nv Ny Ok Oz
Pb Po Qa Qb Qc Qd) Lu(Hu Jp Jr Js Mf Mm Mq Mu My Na Oh Oy) Ng(Hu Iq Iu Jg Jr Lh Mv Oh Pf) Mm(Jg Jm Jp Jr Ni Oi On Pd) Ii(Hu Jg Jr
Ma Mu Pd) Oi(Jr Ms Mv Nc Nj) Mg(Iq Jg Jp Mv) Pd(Jr Lh Lx On) Ms(Jg Jp Jr) Ma(Of Pf) Mv(Oh Pz) Js(Is Lh) IqLh IuJr} Jr{Js(Hw Hx Iv Mk
Mq Mr Nb Nc No Nr Ns Nx Oi Pb) Ng(Jg Jk Jp Lu Lx Mp Mu Nn Po) Pc(Fp Ih Jk Jn Li Mx Na Nj Nx) Ms(Jn Ml Mn Mp Nd Oi Om Po) Oh(Jg
Lh Lw Lx Ma Mv On) Nn(Hu Ly Mm Nj Pd) Iq(Hx Lh Ne Oi Qd) Lw(Hu Li Nf Pd) Iu(Hu Ir Lu My) Oi(Jp Lu Mu Nj) Mm(Lh Ma Mv) Nx(Jp
Mp Qb) Pd(Mp On Po) Mg(Jp Mv) Nj(Jn Mf) PoNf NaOn JqNw} Ms{Jp(IIw Hx Ir Is Ji Jk Jn Lu Ns Nw On Pe Qa Qb) Mu(Ii Ir Is Ji Lw Ly Mg
Mw Nw On Oy Pb Qa) Mv(Is Mg Mj Mk Mr Ng Nw Oi Po Qb) Lu(Hx Is Jg Lw Mp On) Jg(Jn Ly My Nm Pe) Lh(Js Mg Oh Pc Pd) Nw(Ma Mm
Ng Pd) Lw(Hu Mj My) Is(Iu Nx Oi) On(Nf Of Pd) Nn(Jn My) Pc(Hu Mj) PoNx} Ng{Mv(Hx Ii Is Jk Lh Mf Mj Mm Mr Nk Nu Oi On Pd Po)
Lh(Hr Hx Jp Mf Mx Nf Pd Pz) Lu(Is Mt Pc Qa Qb) Jp(Hu Hx Ly Oy Pe) Pc(Hx Mj My) Jg(Hx Ly)} Mm{On(Hx Ir Iv Jn Li Ly Ma Mb Ni Of
Oh Pc Qa) Lh(Hx Is Jq Lx Ma Mf Mv Nf Qb) Lx(Iu Mp Nx Om) Mt(Lw Nn) MaHx IqPe NvPc} Lu{Oi(Hx Jp Nn Nw Pc Qa Qb) Nn(Hx Nf Nh
Pd) Lw(Hx Mj Pe) Iu(Lh Lx Qe) On(Nx Pz) PoNf MpPd IqIs QbJp} Nx{Nw(Hw Js Lw Mj Mx Oh On Pc) Jp(Hx Jk Ne Nh Qa) On(Hx Is Of Pz)
Is(Nn Oi) PoOm IuLh} On{Nf(Ii Iu Li Nj Nm) Oh(Na Of) NmIu MqLi NjPd} Mg{Jg(Hu Hx Ly Nj) Hu(Nn Pc) LyMv IqLh JkJp} Lh{Iu(Oh Pd
Pz Qa) Iq(Nh Qb) NfOf QaJs} Lx{Hq(Li No Pf) Oh(Mf Mq) NjPd QaJs} Po{Li(Mf Mq Na) Pd(Ly Mv) NfOh} Oi{Mv(Hx Nu) Hu(Lw Nn)
LyJp HxIq} Nj{Jp(Nd Ne Nh) MpPd IrIu} Pe{Hw(Hr Mx Na) MvPd JsNw} MkHwIn PzQaJg

Unconstrained panels with 3 analytes, where 1.0E-6 >= 'AUC p-value' > 1.0E-7. Contains 6,105 panels of 260,130 total panels evaluated. :
aA{Jr(Fp Fr Hq Hr Hw Io Ip Ir Is Iv Jg Jh Ji Jm Jp Lw Lz Ma Mb Mc Md Mg Mi Mk Ml Mm Mn Mp Mr Mt Mu Mv Mz Nb Nc Nd Nj Nk Nl
Nn No Nq Nr Ns Nu Nv Nw Of On Oy Oz Pb Pc Po Qc Qd Qe) Oi(Fp Hq Hr Hu Hw Ih Ii In Io It Jg Jh Ji Jm Lh Lj Lu Lz Mb Mc Md Mg Mh
Ml Mm Mn Mp Mr Mt Mu Mw My Nb Nd Ni Nk Nl Nm No Nq Nr Nt Nv Nw Nx Ny Oh Om On Pa Pd Pe Pf Qb Qc Qd) Na(Fp Fr Hq Hv Hw
Hx Ih Ii In Io Ip Ir Is It Iv Jh Jk Jn Jp Js Lj Lz Mb Mc Md Me Mg Mh Mj Mk Ml Mm Mr Mt Mu Mx Nb Nc Nf Nj Nk No Nr Nt Nv Nw Of Om
Oy Oz Pb Pd Qc) Mz(Fp Hq Hr Hv Hw In Io Ip Ir Is Iv Jh Ji Jm Jp Lu Lz Ma Mb Mc Md Me Mk Ml Mn Mp Mr Mt Mu Mw Nb Nc Nl Nn No
Nq Nr Ns Nu Nw Ny Om On Oy Oz Po Pz Qa Qb Qc Qd Qe) Pc(Et Hq Hr Hv Hw Ih Ii Io Ir Is Iv Jj Jl Jm Jp Lh Lw Lz Mc Me Mi Mj Mk Ml
Mn Mp Mr Mt Mu Mw Nb Nc Nd Nl Nm Nr Ns Nu Nv Ny Om On Pa Pb Pe Pf Po Qa Qc Qd Qe) Jj(Et Fp Fr Hq Hr Hw Ii Io Iq Iu Jh Jn Jp Lj

Figure 16 Continued

Lu Lw Lz Ma Mc Md Mi Mk Ml Mm Mp Mr Mt Mu Mv Mw Nc Ni Nn No Nr Nt Nv Nw Nx Ny Of Oh Om On Oy Pf Pz) Mi(Hq Hr Hv Hw Io Ip Ir Is Iu Iv Jh Jk Jn Js Lh Lw Lz Mb Mc Me Mk Mn Mp Mt Mu Mv Mw My Nb Nn Ns Nu Nv Nw Ny Of Om On Pa Pe Pf Pg Po Qb Qc) Lw(Fp Hq Hr Hv Hw Hx Ih Ii Io Ip Ir Is Iv Jh Jk Jn Lj Lz Mb Mc Md Mk Ml Mp Mt Mu My Nb Nl Nn No Nq Nv Nw Ny Ok Om On Pb Pf Pg Po Pz) Jq(Fr Hv Ih In Iq Iv Jh Ji Jm Jo Jp Js Me Mf Mg Mh Mj Ml Mn Mp Mq Mt Mw Mx Nb Nc Nd Ne Nf Nj Nk Nl Ns Nt Nv Nw On Oz Pd Po Qd Qe) Iq(Et Fp Hq Hr Hw Ii Io It Jh Ji Jp Js Li Lj Lu Lz Ma Mb Mc Md Me Mh Mk Mn Mr Nm No Nq Nr Nt Nv Nw Ny Of Oh Ok Om Oy Pf Pz) Nn(Fp Hq Hr Hv Ii In Io Ir Jh Jn Lj Lu Lx Lz Mb Mc Md Mk Mt Mx Nl Nm No Nt Nv Ny Ok On Pf Pz Qa Qb) Iu(Et Fp Fr Hq Hr Hw Io Jp Lz Ma Mb Mc Mk Ml Mm Mr Mt Mv Nc Nh No Nw Nx Ny Of Oh Ok Om Oy Pf Po Pz) Jo(Hq Hr Hw Io It Jh Ji Js Jt Lj Ly Lz Mc Mh Mj Mk Mr Mt Mw Nb Nc Ni Nj Nm No Nr Nt Nu Oy Pb Qc) Mf(Ih Ii In Iv Jl Jn Js Ly Lz Ma Md Mm Mp Mq Mr Mx Nf Nj Nk Ns Of On Pd Pg Qa) Ng(Et Hu Jh Jm Lh Lu Mk Mn My Ni Nl Nm Nq Nu Nx Ny Of Oh Oy Pb Pe Pf Pz Qb) Pg(Fp Hr Hu Hw Io Ji Jk Jn Jp Lj Lu Mb Md Me Mk Mq Mx My Nk Nq Ns Nt Ok On) Jl(Et Fp Ih Io Jg Ji Jk Jn Lu Mb Mp Mq Mx Nf Nk Nq Nt Nw On Oy Pa Po Qd) Jt(Hr Hu Hw It Lu Lz Mb Mh Mk Mm Mr My Nc No Nr Nu Ny Of Oh Oy Pb Pf Qc) Pd(Hx In Is Iv Jn Jp Li Lx Ly Mq Mu Nc Nj Nk Ns Nw Om On Oz Pb Po Qa) Mm(Hx Ir Is Jg Mc Mh Mn Mv Mw Nd Nf Nw Oz Pb Pc Qe) Of(Hx Ip Is Lh Ma Mn Mw Nd Nf On Oz Pb Pe Qa Qb Qe) Nf(Fr Hx Jn Jp Js Ly Mg Mp Mq Nk Ns Om On Pe) Ly(Hx Ih Js Lx Ma Me Mg Mq Mv Mx Nd Nt) Ii(Hx In Ip Is Jk Lx On Pb Pe Qa Qb) Oh(Hv Hx Is Jp Lh Ma Mt Nw Pb Pe Qe) Mg(Hx Ip Jg Jp Mc Mp Mu Mv Pb Po) Js(Hv Hx Is Jn Jp Mq Nk Ns On Pa) Ip(Hv Ih Ir Jn Lj Md Me Mq Nk) Qa(It Jn Li Mq Nm Nx Pf Pz) Po(Hv Lj Md Mx No Nt Nx) Lx(Hq Nm Nt Ny Ok Pf Pz) Nj(Fr Hx It Me Ne Qb) Nx(Fr Hx Is Ms Om Pe) Mx(In Mj Mp Mu On) Pa(Li Lu Mb Nm Pe) Mq(Ih In Nk Ns) Fr(Et Li Nk) Mp(Hq Nq Nt) Ms(My Nh Pz) On(Ji No Nt) Hx(Ih It) In(Jn Me) Qb(Ny Pz) Pb(Nk Pf) MbNd MvOk NcNl JpLi PePf} Og{Ji(Et Fp Hq Ih In Io Iq It Iu Jg Jm Js Lj Lw Ma Mb Mc Md Me Mh Ml Mn Mp Mt Na Nd Ne Nf Ng Nh Ni Nl Nq Ns Nt Nv Nx Ny Of Oi Ok Oz Pd Pf Qa Qc Qe) Qd(Et Hq Ih Ii Io Iq It Jm Jn Js Lj Ma Mc Md Mg Mh Ml Mn Mq Mx My Na Ne Ng Ni Nk Nl Nm Ns Nt Nx Ny Of Oh Oi Ok Oz Pb Pf Qb) No(Et Fp Hq Hw Ii Iq Iu Jg Lj Ly Mc Md Me Mf Mk Ml Mq Mr Mx Nb Ni Nl Nm Nn Nq Nr Ns Nt Ny Of Oi Ok Oy Pf Po Pz Qc) Nn(Hr Hw Ih Ii Io Iu Jg Jh Jq Li Lw Ly Lz Ma Mb Mm Mn Mp Ms Mu Mw Nb Nk Nm Nt Nx Oe Oh Oi Ok Pb Pd Po) Qb(Et Hr Io Ir Iu Jk Lj Mb Md Me Mf Mg Mh Ml Mq Ms Mx My Nm Ns Nt Nv Nx Ny Oe Of Oh Oi Ok Oz Pf Pz Qe) Jk(Et Hu Hv Hw Ii Iu Jg Jn Jo Jq Li Lw Lz Ma Mg Mj Mm Mn Ms Mt Mu Mv Nc Nu Nv Oe Ok Oy Pb Pz Qa Qe) Nu(Et Hu Hv Ih Iu Jg Jh Jn Lu Lz Md Mf Mj Mn Mp Mq Mr Ms Mw Mx My Nb Nq Nr Ns Oi Pb Qe) Lx(Ii It Iu Jg Jm Li Md Me Mf Mg Ml Mp Mq Mv Ng Nj Nk Nl Nx Ny Oe Ok Pc Pz Qc Qe) Mt(Et Hq Hr Hw Ii In Ir Jg Jq Li Lj Ly Mb Ml Mq Mv Nc Nf Ng Nk Nm Ny Oh Pc Pf Qc) Ip(Hu Hv Iu Jg Jh Jn Lu Lz Ma Mg Mj Mk Mn Mp Ms Mw Mx My Nb Nc Nd Nj Nq Nv Oe Qa) Mj(Et Hq Hu Ih Jg Jm Jo Lu Mc Me My Nb Nd Ni Nr Ns Nt Nx Ny Of Oh Ok Pd Pz) Qe(Hv Hw Iq Ir It Jm Jn Li Ly Lz Mf Mg Ms Mx Nf Ng Nk Nm Nx Oe Om Oy Pb Pc) Hv(Et Iu Jn Jo Li Lw Lz Mf Mk Mn Mp Mr Ms Mw My Nb Nc Nq Nr Oe Ok Oy) Mu(Fp In Io Jg Jh Jo Jq Js Lj Ma Mb Mc Md Mp Na Nf Ng Ni Nq Pz Qc) Lh(Et Fp Hr Ih In Io It Lj Ly Lz Mb Mc Mc Ml Mp Mq Mx My Ns Nv Oz) Nv(Hr Ii Iu Jg Jn Li Ly Mf Mp Ms Mv Mx Nf Nk Nm Of Oh Pb Pc Pz) Mn(Hw Ir Iu Jg Jn Jq Li Lw Lz Mk Mr Mv Mx Nb Nc Nf Nj Nr Oy) Lu(Hw Ih Ii Iu Jh Jt Li Mk Mr Mw Nc Nd Nq Nr Nt Ok Oy) Qa(Hr Hw Ir Iu Jm Jn Jq Li Ly Mf Mp Nf Nk Of Oh Pc Pz) Jg(Hw Ih Iu Lz Me Mf Mm Mp Mq Mr Nd Nk Nr Of Oh Oi Pz) Jj(Hr Hw Io Jh Jm Jq Li Lw Lz Ma Mp Nf Nq Ok Pb) Pb(Hr Hw Ir Iv Jh Jn Jo Ma Mf Mw Nc Nf Ng Po) Mk(Et Hr Hu Ih Lw Md Mh Mx Nf Ng Nq Pc Qc) Hu(Ih Ii Jh Jn Ma Mr Mw Mx Nb Nd Nr Ok) Jh(Hw Iu Jn Jq Li Lw Lz Mh Mx Nc Om) Po(Hr Hw Ii Jm Lj Ne Nh Nl Nq Pc) Mp(Jn Lz Mq Mw Mx Nb Nc Nj Oy Pd) Mv(Et Hr Ih Jq Md Ml Nc Nf Nl Oi) Pe(In It Jq Jt Mg Nb Nl Nt Of Oi) Ma(Hw Ii Jn Li Lw Lz Mx Nc Nf) Nr(Et Hw Ih Md Na Ng Nq Qc) Mr(Et Hr Hw Ih Na Ng Nq Qc) Jn(Li Me Mf Mw Nb Nc Nd Nq) Oy(Et Ih Md Mw Ng Nj Oe Qc) Ii(Hw Iq Jt Na Ng Pc) Lw(Iu Mw Mx Nb Nj) Lz(Et Mw My Nc Pc) Nb(Et Ih Jo Na) Nj(Iu Jt Mx Ok) Ir(Nd Ne Nh Nq) Om(Lj Ly Md Pd) Mw(Jq Me Mh) Jt(Jo Jp Jr) Nw(Jr Mx Oh) Pc(Iv Mg Ng) Nc(Et Ok) Iu(Ms Oc) Jq(Ih Nd) MdPg MlIv MqOk NlPa HwJo} Jl{Li(Et Fp Fr Hr Hv Hw Hx Ih In Io Is It Iv Jg Jh Ji Jk Jn Lh Lj Lw Lx Lz Mc Md Me Mj Mk Mp Mr Mt Mu Mx My Nb Nn No Nq Nr Ns Nt Nu Nw Om On Oy Oz Pg Po Qa Qc) Ly(Fr Hq Hr Hu Hv Hx Ih In Ip Is Iv Jg Jh Ji Jn Lj Lx Mb Mc Md Me Ml Mn Mp Mt Mu Mv Mw Mx My Mz Nb Nk No Nq Ns Nu Nw Om On Oz Pa Pc Po Qa Qc Qe) Nv(Et Fr Hr Hw In Io Ip Ir Is It Jh Ji Jk Lj Lw Lx Lz Mc Md Me Mj Mk Mn Mp Mr Mt Mu Mv Mw My Ni No Nq Nr Ns Nt Nu Nw Oy Oz Pb Pe Po Qa Qb Qc Qe) Jq(Fp Fr Hr Hw Hx Ih Io Ir It Iv Jh Ji Jk Lh Lj Lx Lz Mc Md Mj Mk Mn Mp Mr Mu Mw My Nb Ni No Nq Nr Nt Nu On Oy Oz Pb Pc Pe Pf Pg Po Qb Qc Qe) Nj(Fr In Io Ip Ir Iv Jg Jh Ji Lw Lz Ma Mb Mc Md Mh Mn Mp Mt Mu Mv Mw Nd Ni No Nu Om Pg Po Qa Qb Qc Qd Qe) Jr(Et Hr Hu Hv Hx It Jh Ji Jm Lj Mb Mc Me Ml Mp Mt My Mz Nc Nq Ns Nt Oz Pc Po Qc Qe) Pd(Et Fp Hq Hv Hx Ii Iv Jm Jn Js Lw Mh Ml Mp Mq Mz Na Nf Nn No Nq Ns Nu Nw Om Oy Pf) Jm(Et Fp Hq Hu Hv Hx Ih In Jh Jn Jp Lu Mb Mi Ml My Mz Na Nb Nf Nq Ns Nt Pc) Js(Et Fp Hu Hv In Io Jn Lz Mk Ml My Nb Nf Nq Ns Nu Nw Om On Pc Pg Po Qa) Mf(Et Fp Hr Hv Ih Jn Jp Mi Ml Mq Mx My Mz Na Nb Nc Nf Nk Nq Ns Oy Pa) Mq(Et Fp Hr Hu Hv Hx Ih Jn Jp Ml Mx My Mz Na Nb Nc Nf Nk Nq Pa) Hq(Et Fp Hv Hx Jp Lj Mb Ml Mx Mz Nc Nf Nk Nr Ns Nt Pc Pg) Hu(Et Fp Hw Ih Jn Jp Mi Ml My Mz Na Nc Nf Nq Ns Nt Po) Nc(Et Fp Ih Jn Ml Mx Mz Na Nh Nl Nr Nt Oy Pf) Mb(Et Ih Jn Jp Mi Ml Mz Na Nf Nr Oy Pa Pf) Ng(Jg Ma Mh Mn Ne Nh Nl Nq Pf Qb Qd) Mg(Ir Ma Mh Mn My Ni Nl Pf Qb Qd) Nf(Hx Jp Lh Mk Mr Nb Nr On Pc Pe) Lu(Ir Lh Ma Mh Ne Ni Nl Qb Qd) Na(Jp Mk Mr Nk Nr Nu On Pe) Jp(Ih Jg Jn Mp Mx Nk Pf) Ny(Fr Ip Ma Mh Mv Nd Qd) Oy(Jk Jn Mr Mx Nk Nr Pb) Pa(Ih Jk Mp Mx Nr Nt Po) Oi(Mh Nh Nl Pf Qb Qd) Nr(Mz Nb Nk Pg) Nt(Lx Mi Mr Pe) Iq(Ma Mh Mv Nd) Nk(Fp Ih Pf) Mi(Nq Po) Mx(Pe Pf) Ok(Ne Nh) EtMz FpPg MkOf MrHr NiIi PcPf} Oe{Ir(Et Fp Hq Hw Ih In Io Ip Jn Jq Js Lh Lj Mb Mc Md Me Mg Mn Mv Nd Ng Ni Nj Nk Nl Nm Ns Ny Of Oh Oi Om Oz Pd Pf Pz Qc Qd) Is(Et Fp Hr Ih In Ip Jh Ji Jn Lh Lj Ma Mb Mc Md Me Ml Mn Mt My Na Nd Nf Ng Ni Nl Nq Nt Oi Om Oz Pd Qa Qb Qc Qd Qe) Jp(Et Fp Hq Io Jh Ji Jj Jm Jq Js Lj Ma Mb Mc Md Me Mh Ml Mm Mn Mw Na Ne Ng Nl Nm Ns Nt Nv Ny Oh Oi Ok Om Oz Pd) Nw(Et Fp Hq Hr Hw Ih In Ip Iq It Jg Ji Jm Jn Li Lj Lz Ma Mc Me Mu My Na Ng Nh Nl Nn Ns Nt Ny Om Oz Pb Pc Qc) Mj(Et Hu Hv Ih Ip Iq Iu Iv Jg Ji Jk Lu Lz Mc Me Mq Mr Nd Nj Nn No Nu Oh Pb Pc Pe Po Pz Qc) Po(Hq In Io It Jk Lw Lz Mc Md Me Mg Mi Ml Mw Nb Nd Ng Ni Nt Oi Ok Oy Oz Pe Qb Qc Qe) No(Hv Ih Ip Iq Jh Jk Jn Jo Lu Ma Mf Mh Mv Mw My Na Nd Nj Nq Nu Pc Pd Pe Qd Qe) Nu(Hu Hv Ii Iv Jh Lu Ma Mf Mn Mq Mt Mu Mw My Nb Nn Nq Nr Nv Qa Qb Qd) Mi(Et Hq Io Iq Iu Lw Lz Ma Mc Ml Mp Mu Ne Nh Ni Nt Of Oi Pf Qc) Nn(Ii Ip It Jj Lx Mr Ms Mt My Nj Nl Oy Pb Pc Pe Qa Qb Qe) Fr(Fp Hr Hu Iq Jg Ji Jq Lj Lz Me Mh Mn Mt Mu Na Ns Nt) Nb(Hr Hu Hw Jg Ji Jk Jn Li Lu Mn Mp Mw Na Nd Nf Nq Qd) Iv(Ii Iu Ji Jk Jo Lu Lw Mf Mn Mv My Nq Nv Om Pc Qb Qd) Lh(Hu Ip It Jk Jq Lw Lz Ml Mq Mu Mv Nc Nt Ny Oi Ok) Pe(Ih Ii It Jn Lj Lz Ml Mp Nc Nd Nx Of Om Oz Pz Qc) Lw(Ih Jj Jn Lx Mn Mt Mv My Nv Qa Qb Qd Qe) Lu(Hv Ii Ip Iu Jj Jn Ma Mk Nd Nr Nv Oy) Lx(Iu Jg Jn Mf Mh Mu Mv Nc Nd Pb Pz) Pc(Ii Iu Ji Jq Ma Mn Mp Mx Nc Ng Nq) Jg(Ih Ip Iu Jn Mm Nc Nd Nj Nk Nr) Jj(Jn Jt Li Mu Mv Mw Mx Nq Nt Pb) Mz(Ih Jt Mh Mx Na Ne Nf Nh Nv) Mr(Hu Hw Jh Ji Jk Ma Mn Nq) Mu(Hu Hv Ii Jn My Nt Oy Qe) Pb(Mn Mt Mv Nv Qa Qb Qd Qe) Ii(Et Ji Jk Jn Nj Nq Qd) Oy(Jo Ma Mn Mw Qb Qd Qe) Nr(Hr Ji Jk Jn Mw Nq) Mk(Hu Ji Jk Jn Nq) Mv(Hw It Ng Nk Qb) Mm(Mt Om Qa Qd) Hu(Mn Nd Qa Qb) Jr(Jt Mh Ne Nh) On(Et Ml Ne Nh) Ly(Ji Om Qb) Iu(Jh Mn Qd) Mh(Mt Pa) Nc(Qb Qd) Qe(Jo Pg) Ji(Hv Jk) NtPa MpHq IpQd JoNv NxOm} Jj{My(Fp Hq Hr Io It Iu Jh Ji Jp Jq Js Jt Li Lj Lu Lw Lz Ma Mc Me Mf Mh Mk Ml Mm Mr Na Nb Nc Nf Ni Nm No Nq Nr Ns Nt Nu Nw Nx Ny Of Oh Ok Pd Pf Pz) Mt(Hr Hw Ih Ip Is It Iu Iv Jm Jn Jo Js Li Lw Lx Lz Me Mg Mh Mk Ml Mn Mp Mq Mr Mw Nb Nc Nd Nf Ng Nm Nn No Nq Nr Ns Nw Nx Oh Om Oy Pb Pc) Jr(Et Fp Hr Hw Iq It Iu Jg Ji Jo Jp Jq Li Lj Lz Mb Mc Md Mg Mm

Ly Mj Mk Mr Mw Mx My Nb Ni Nj Nn No Nr Nx Oi Oy Pb Pc Po Qd Qe) Jg(Hv Ii Is Mf Mj Ml Mm Mq Mx Ne Nj Nk Nn No Nw Of Oh Om Oy Pb Po Pz) Mv(Hv Ii Ir Ji Lw Ly Mf Mw Mx Nn No Nu On Oy Pb Pc Qa Qd) Mu(Hv In Ip It Lu Lz Mq My Ng Nm Nn No Nu Pc Po Qd) Ji(Hu Hv Hx Iu Jk Lu Mf Mg Mm Mp Mw Nd Ng Nm Nx Of) Lh(Hx Iq Lx Mj Mk Mr Mt Nb Ne Nj Nr Nx Oi On Pe Pf) On(Hr Hv Hx Li Lj Mf Mq Na Ng Nm Nt Nx Oi Ok Pz) Pg(Hu Hx Iu Jm Js Mf Mg Mm Nc Nj Of Oh Pd Pf) Hx(Iq Iu Lw Nj Nn Nx Oi Pc) Nw(Fp Hu Mg My Nd Nf Of Ok) Po(Jn My Nj Pd) Nn(Ir Ng Nx Qd) Lu(Lx Pc Qb) Iu(Ir Pe Qd) Lx(Hq Pd) Oi(Ir Om) LwJn MwOf MyPc IsJm} Pg{Lu(Hq Hr Hv Jg Jh Ma Mc Me Ml Mw Mx Nc Nd Ne Ni Nk Nm Nq Ns Nt Ny On Oz Pf Pz) Ng(Fp Hx Jh Jk Jm Jq Js Li Lj Lx Ly Mf Mk Mr Mu Nb Nm Nr Ny Of On Oy Pc Pe Pz) Nx(Hu Hw Ih Io Jk Lh Li Lj Ly Md Mj Mk Mr Mx Nr Nw Qe) Ii(Hx Ir Jh Ji Jm Jn Jp Js Lx Mf Mq Mt Mw Nc Ni Nj) Pd(Iq Iu Jp Mj Mk Mr Mv Nc Nj Nm Nr Of Oh Pb Po Pz) Mm(Jh Ji Js Lx Mf Mg Mq Mt Mu Mw Nc Nf Nj Nk Nw) Jp(Iq Js Li Nj Nm Ny Of Oh Oi Ok) Of(Iq Jg Jm Lh Mf Mu Ni) Pf(Jm Lh Lx Mg Mu Ni Oi) Iu(Lh Mg Mv Ni Nj Oi) Oh(Ma Mg Mu Oi) Iq(Hx Mf Mu) Nm(Ma Mv) Mg(Mu Nj) LxJs MaPz MfNj MxHq JqNw NyOi} Mm{On(Et Fp Hq Hr Hu Hv Hw Ih Ip Is It Iu Jk Jm Jq Js Lh Lw Lx Mc Mf Mj Mk Mq Mr Mt Mu My Na Nb Nk Nm Nn No Nr Ns Nt Nx Om Oy Pb Pd Pe Pf Po Pz Qb Qc Qe) Lh(Hr Hv Ii Ip Ir It Iv Jg Jh Jk Jp Ly Mn Mq Mr Mt Mu Mw Na Nc Nd Nj Nk Ns Nw Nx Of Oh Pe Po Pz Qe) Lx(Hq Hx Iq Jg Jp Mu Of Pf Po) Ir(Iq Iu Jg Jp Lw Ma Nn Pc) Qa(Jg Ji Jm Jp Ma Nn Nw Pc) Mv(Hx Is Mg Nn Oi Qb) Qe(Jg Jp Nn Nw Pc) Nn(Hx Jn Nv) Is(Iq Lu Nx) Jg(Mg Mt Ng) PoMt QbJp QdPc NwNx} Ng{Lh(Hu Hv Hw Ih Ip Ir It Iv Jm Jn Jq Mb Mc Md Mq Na Nc Nj Nk Ny Of Oh Pf) Jp(Ii Ir Is Lx Mk Mr Mv My Nb Nr Nx On Pb Pc Po) Mv(Hv Ip Iu Jn Lw Ml Mp Mq Mw Na Nt Oh) Lu(Hx Ir Jg Lw Mp Mu Mw Nw Pe) Lx(Hu Iq Nj Pc Pd) Hx(Iq Iu Mu Nn On) Hu(Mu On Pb Pe) Jk(Ip Jg Pc) Nx(Is Nn Po) Jh(Ip Pc) On(Ok Pd) Pe(Hr Jg) NnMy LyMu MaOy Irlu} Lu{Nn(Hv In Jn Ly Mf Mp Mu Nd Nj Nk Nq Ns Pe Po Qa Qb) Lw(Ir Is Oi Qa Qb Qd) Pc(Hx Is Mx Pe Qa Qb) Is(Ii Jp Of Oh) On(Iu Mq Oh Pd) Iq(Hx Ir Qa) Oi(Jg Lx Mv) Jp(Ne Nh) LxHq NdNj IuJk QbOh} Iu{Ir(Jk Jm Js Mf Mg Mj Mq My Na Oi On Pd) Lh(Hu Hx Jn Ly Mt Na Nj Nm Nn Oi Ok Qe) Hu(Hx Is Pe Qa Qe) Hx(Nf Nj Nx Oi) Pe(Fp Li Nj) QeNx} On{Nm(Hq Hr Ii Io It Jm Js Mb Mf Mx Na Nn Nx) Na(Hq Ny Pd Pf) Li(In Io It Nl) Pd(Iq Jp Nc) Mv(Of Oi) Nf(Mg Of) Js(In Ok) Nx(Mu Nj) Oh(Mq Mw) HwOk} Nx{Is(It Lw Mf Nj Nw Of Oh Po Pz) Nn(Hx Ir Jn Pc Qa Qb Qd) Nw(Hx Jk Jn Lh Mt) Jp(Ii Ir Ly) LwPe HxOi IqIr OmPc} Mv{Mg(Hu Hx Jp Lx Mj Mp Nb Nk Nu Oi) Oi(Jp Mj Nb Nj Nk Nr Pd Pe Po) Qb(Oh Pz) Pe(Hw Pf) HxOf} Lx{Hq(Hw Mb Mf Mq Mx Na Nf Nj) Oh(Jh Lw Ns Of) Pd(Hx Iq Jp Nc) NtNj MfJs MqLj} Lh{Iq(Hx Na Ne Nf Qa) Nn(Li Ly Mg Pz) Na(Of Oh) Pd(Jp Nj) NqJq LwMg NfOh PzPc QaOf} Jp{Oi(Hu Hx Jk Nj) Mg(Hx Ly Nj) Nc(Ne Nh Nl) PoPd Nhlq InJs} Pe{Hw(Io It Mc Ny Pb) Hr(Mb Pc) Iq(Oi Pf) NfJs} Nn{Oh(Mf Mr Nf Nr) MjLi NhNj HuPd} Oi{Ly(Jg Mu) Hx(Nf Nj) Iq(Ir Is) HuPc} Po{Pd(Hx Iq) MbJs HqLi} Mg{Hu(Lw Mu) MjPc NkJg} Hx{MaOf JgOh} NmLwNw MpHuPd IsQaJs Unconstrained panels with 3 analytes, where 1.0E-5 >= 'AUC p-value' > 1.0E-6. Contains 11,452 panels of 260,130 total panels evaluated. :
aA{Ns(Fp Fr Hq Hr Hv Hw Hx Ih Ii In Io Ip Ir Is It Iv Jh Ji Jk Jl Jm Jn Jp Li Lj Ly Lz Mb Mc Md Me Mg Mh Mk Ml Mm Mp Mr Mt Mu Mv Mx Nb Nc Nd Nj Nk Nl No Nq Nr Nt Nu Nv Nw Of Oh Om On Oy Pa Pb Po Qa Qb Qc Qd) Nf(Et Fp Hq Hr Hv Hw Ih Ii In Io Ip Ir Is It Iv Jh Ji Jk Jm Lh Li Lj Lx Lz Ma Mb Mc Md Me Mh Mj Mk Ml Mr Mt Mu Mv Mx Nb Nc Nd Ni Nj Nl Nm No Nq Nr Nt Nu Nv Nw Nx Ny Oh Ok Oy Oz Pb Pd Pf Pz Qa Qb Qc Qd Qe) Ly(Hq Hr Hv Hw Ii In Io Ip Ir Is Iv Jh Jk Jm Jn Lh Li Lj Lz Mb Mc Md Mh Mj Mk Ml Mm Mn Mp Mr Mt Mu Mw My Nb Nc Ne Ni Nj Nk Nl Nm No Nq Nr Nu Nv Nw Ny Of Oh Om On Oy Oz Pb Pe Po Qa Qb Qc Qd Qe) Jp(Et Fp Fr Hq Hr Hv Hw Hx Ih Ii In Io Ip Ir Is Iv Jh Ji Jk Jl Jn Lj Lu Lw Lz Ma Mb Mc Md Me Mf Mh Mi Ml Mm Mq Mr Mu Mx Nc Nd Nj Nk Nl Nm No Nq Nt Nv Nw Nx Ny Of Ok On Oz Pa Pb Pe Pz Qa Qc) Me(Fp Fr Hq Hr Hv Hw Hx Ih Ii Io Ir Is It Iu Iv Jh Ji Jj Jl Jm Jn Js Li Lj Lu Lw Lz Mb Mc Md Mk Mp Mq Mr Mt Mv Nb Nc Nd Nk Nl No Nr Nt Nv Nw Nx Ny Of Oh Oi On Oy Oz Pa Pb Pd Qa) Mq(Fp Fr Hq Hr Hv Hw Hx Ii Io Ir Is It Iv Jh Jk Jm Jn Li Lj Lx Lz Mb Mc Md Mg Mk Ml Mm Mn Mp Mr Mt Mu Mv Pa Pb Qc Qd) Nk(Fp Hq Hr Hv Hw Hx Ih Ii In Io Ir Is It Iv Jg Jh Ji Jm Ln Lh Lj Lx Lz Ma Mb Mc Md Mg Mk Ml Mm Mn Mp Mr Mt Mu Mv Mx Nd Ni No Nq Nr Nt Nv Nw Of Om On Oy Oz Pa Pe Qa Qc Qd Qe) Js(Et Fp Fr Hq Hr Hw Ii Io Ir It Iv Jg Jh Ji Jk Lh Li Lj Lx Ma Mb Mc Md Mg Mh Mk Ml Mm Mn Mr Mt Mu Mv Mx Nb Nc Nd Nj Nl No Nq Nr Nt Nu Nv Nw Of Oh Om Oy Oz Pb Pd Pf Qb Qe) Pd(Et Fp Hq Hr Hv Hw Ih Ii Io Ir It Jg Jh Ji Jk Jm Lh Lj Lz Ma Mb Mc Md Mg Mh Mk Ml Mm Mn Mr Mt Mv Mw Mx Nb Nd Ni Nl No Nq Nr Nt Nu Nv Ny Of Oh Oy Pf Qb Qc Qd Qe) Mf(Fp Fr Hq Hr Hv Hw Hx Io Ir Is It Jg Jh Ji Jk Jm Li Lj Lx Mb Mc Mg Mh Mk Ml Mn Mt Mv My Nb Nc Nd Nl Nm No Nq Nr Nt Nu Nv Nw Ny Oh Om Oy Oz Pa Pb Pf Qc Qd Qe) Ip(Et Fp Fr Hq Hr Hw In Io Is It Iv Jh Ji Jl Jm Li Lz Mb Mc Mk Ml Mn Mp Mr Mt Mu Nb Nc Nd Nj Nm No Nq Nr Nt Nu Nv Nw Nx Ny Oh Om On Oy Oz Pb Pf Pg Po Qc Qd) Ih(Fp Fr Hq Hr Hv Hw Ii In Ir Is Iv Jh Ji Jk Lj Lx Lz Mc Md Mg Mh Mi Mk Ml Mp Mr Mv Nb Nc Nd Nj Nl Nm Nn No Nq Nr Nt Nv Nw Of Om On Oy Oz Pa Pb Po Qa Qe) Jl(Fr Hq Hr Hu Hv Hw Hx In Ir Is Iv Jh Jm Jr Lh Lj Lw Lx Lz Ma Mc Md Mi Mj Mk Ml Mm Mr Mt Mu Mv Mw My Mz Nb Nc Nd Nl No Nr Nu Om Oz Pb Pe Pg Qa Qb Qc Qe) Mx(Et Fp Fr Hq Hr Hv Hw Hx Ii Io Is It Iv Ji Jk Jn Li Lj Lx Lz Mb Mc Md Mg Mh Mk Mm Mr Mv Nb Nc Nd Nj Nl No Nr Nt Nu Nv Nw Of Oh Om Oy Oz Pa Pb Pf) Jn(Fp Fr Hq Hr Hv Hw Hx Ii Io Is It Iv Jh Jk Li Lj Lx Lz Mc Md Mg Mh Mk Ml Mm Mp Mr Nb Nc Nd Nj Nl No Nq Nr Nt Nv Of On Oy Oz Pa Pb Po) Fr(Fp Hq Hr Hv Hx Ii In Io Iq Ir It Iv Jg Jh Ji Lj Lu Lw Lz Mb Md Mi Ml Mr Mv Mw My Mz Nb Nm Nn No Nq Nt Nv Ny Oy Pa Pc Pf Pg Pz Qb) Pg(Et Hq Hv Hx In Ir Is Iv Jg Jh Jm Jr Lh Lx Lz Ma Mc Mj Ml Mn Mp Mt Mu Mv Mw Mz Nb Nd Nl No Nr Nu Om Oz Pa Pb Pe Qa Qb Qc Qe) Mm(Fp Hq Hr Hv Hw Ii Io It Iv Jh Ji Jk Jm Jo Jq Lj Lz Mc Md Mg Mk Ml Mp Mr Mu Nc Ni Nl No Nq Nr Nt Nv Ok Om Oy Pf Po Pz Qc Qd) On(Fp Hq Hr Hv Hw In Io Ir Is Iv Jh Li Lj Lz Mb Mc Md Mg Mh Mk Ml Mp Mt Mu My Nc Nj Nm Nq Nr Nt Nv Nw Ny Ok Om Oy Pa Pb Pf Pz) Of(Hq Hv Hw Ii In Ir Iv Jg Jh Jk Jm Jo Jq Lj Lz Mc Md Mg Mh Mk Mp Mt Mu Mv Nb Nc Ni Nj No Nq Nr Nt Nv Nw Oi Om Po Qc Qd) Md(Fp Hr Hv Hx Ii In Io Ir Is It Iv Jh Jq Lj Lz Mc Mg Mk Ml Mp Mr Mu Mv Nc Nj Nl No Nq Nr Nt Nw Oh Om Oy Oz Pa Pb) Jq(Et Fp Hq Hr Hu Hw Ii Io It Jg Li Lj Lu Lz Ma Mb Mc Mk Mr Mu Mv My Nb Nc Nl Nn No Nq Nr Nt Nv Ny Oy Pa Pb Pf Pz Qc Qd) It(Hu Hv In Ir Is Iu Iv Jj Jk Jm Lh Li Lu Lw Lx Mg Mh Mn Mw My Nb Nd Nm Nq Nt Oz Pb Pc Pe Qb Qd Qe) Na(Et Hr Hu Jg Ji Jm Lh Li Lx Ma Mn Mv Mw My Nd Ni Nl Nm Nn Nq Nx Ny Oh Ok Pa Pf Pz Qa Qb Qd Qe) Ii(Hq Hv Ir Iv Jh Jm Lh Lj Ma Mc Mh Mi Ml Mn Mp Mw My Nb Nd Nl No Nq Nt Nv Nw Nx Om Oz Po Qd Qe) Pb(Fp Hq Hr In Io Iv Ji Li Lj Mb Mi Ml Mp Mr Mt Mz Nb Nc Nj Nm Nn No Nq Nt Nu Nv Nx Ny Ok Oy Pz) Nj(Is Jg Jk Lx Ma Mg Mh Ml Mn Mp Mr Mt Mu Mv Mw Nb Nc Nh Nl Nq Nt Nw Oh Oz Pe Po Qa Qe) Nt(Hq Hv Hw In Ir Is Iv Jg Jk Lj Mc Mg Mh Mi Mk Mr Mu Mv Nc Nr Nu Nw Om Oy Oz Qa) Mg(Hv Ir Is Iv Jk Jo Lj Lx Lz Ma Mh Ml Mn Mw Nc Nd Nq Nw Om Oz Pa Qa Qb Qc Qe) Mp(Fp Hr Hv Hw In Ir Is Iv Ji Li Lj Lz Mb Mc Mr Mt Mu Nl No Nr Nv Oh Om Oy) Nc(Hv In Iq Is Jk Lj Lw Lx Lz Mi Ml Mr Mu Nb Nd Ne Nh Nq Nu Oh Oz Pe Pu Qa) Hv(Hq Hr Hw In Io Ir Is Iv Li Lj Lz Mb Mc Mj Nd Nl No Nq Nx Oz Pa Qa) Lw(In Jg Jm Lh Lx Mj Mn Mw Mz Nd Ni Nr Nu Oy Oz Pa Pe Qa Qc Qd Qe) Oh(Ir Iv Jg Jh Jk Jm Jo Mh Mn Mu Mv Mw Nd Ni Nl Nq Nv Om Oz Po Qd) In(Hr Hw Ir Is Iv Jr Lj Lz Mc Ml Ml Mt Mu No Nq Nu Nw Oy) Pa(Hr Hw Io Is Jh Jk Jm Lj Ma Mj Mk Mn Mu My Nb Nr Nv Qd) Jr(Et Hu Jk Lh Li Lu Lx Mh Mw My Ne Ni Nm Ny Ok Pf Pz Qa) Is(Fp Io Iv Li Lj Lz Mb Mu Nm Nn No Nq Nv Ny Oy Pf) Oz(Li Lj Mb Ml Mr Nm Nn Nq Nx Ny Oy Pc Pf Pz) Mz(Et Hu Jg Jk Lh Lx Mh Mi Mj Mv My Nd Ni) Qa(Hw Io Lj Lu Mb Mi Ml Nq Nv Ny Ok Oy Qd)

Jh Js Li Lz Mf Mh Ml Mm Mn Mp Mq Mt Na Nc Nd Ne Nf Nh Nk Nl Nq Nu Nv Oh Ok Pd) Nw(Hv Ir Is Iu Jk Jn Js Lx Md Mf Mj Mk Mp Mq
Mr Mw Mx Nb Ni Nj Nk Nm Nq Nr Ns Oi Oy Pb Pc Pe Pf Pz Qa) Mv(Hr In Ip It Jk Jn Lh Li Lu Lx Lz Mc Md Mh Ml Mm Mp Mq My Na Nf
Nj Nk Nm Nt Of Oh Pd Qe) Lh(Hu Hv Ii Is It Jn Lu Lw Ly Mf Ml Mq Mw Nc Nd Nn No Nt Nu Ny Ok Oy Pb Po) Is(Hv Iq It Lw Ma Mf Mg
Mm Mq Mw Mx Ng Ni Nm Of Oh Pc Pd) Lx(Jo Lw Mj Mk Mm Mr Nb Nn No Nr Nu Oi Oy Pb Pc Pe Po) Po(Fp Hu Hv Js Li Lj Ma Mf Mt Mw
Nc Nf Oh Oi) Nn(Hv Mf Mq Mt Nj Nk Nm Nr Ns Oi Pz) Mt(Lw Mj Mr Nb No Pc Pe) Pe(Hr Jn Lu Ma Pc Pf) Mp(Hq Lw Mj Mr Pc) Lu(Mn Nd
Om Qa) Jo(Mj Nv Om Qe) Ma(Hw Ii Mj) Pc(Ir Jn Qb) Fr(Jm Ni) Lw(Ir Jk) Om(Ng Nx) MmNv IuQe QdOi} Fr{Ly(Fp Hq Hr Hv Hw Ih In Io Ip
Iq Ir Is It Iv Jh Jk Jq Js Lh Lj Lw Lx Lz Ma Mb Mc Md Me Mh Mj Mk Mn Mp Mr Mt Mu Mv Mw Mx Nb Nc Nl No Nr Ns Nu Nv Nw Ny Om
On Oz Pb Pc Pe Po Qa Qb Qd Qe) Mg(Et Fp Hq Hw In Iq Ir Is It Iu Iv Jh Jq Lw Lz Mc Md Me Mj Mk Mp Mq Mr Mt Mu Mv Mw Mx My Na
Nc Nd Ne Nf Nh Nn No Nq Nr Nt Nv Nw Ny Of Om Oz Pd Qa Qb Qd Qe) Jo(Et Fp Hq Hr It Iv Jg Jh Ji Jq Js Jt Li Lj Lu Lw Lz Ma Mc Md Me
Mh Ml Mq Mu Mv Mw My Na Nc Nf Ni Nl Nm Nn No Nq Nt Nu Nw Nx Of Ok Om Pc Pd Pf Pz) Of(Et Fp Hq Hr Hw Io Ip It Iv Jg Jh Jp Jq Js
Jt Li Lj Lu Lw Lx Lz Ma Mc Md Me Mh Mi Mp Mr Mt Mv My Na Nm Nn No Nq Nr Ns Nt Nu Nv Nw Nx Ok Om Pc) Oi(Fp Hq Hr Hw Iq Ir
Is It Iv Jg Jh Jm Jq Lh Lw Lx Lz Ma Mc Md Me Mh Mi Mn Mp Mt Mu Mv Mw My Nc Nd Nh No Ns Nv Nw Ny Om Oz Pb Po Qa Qd) Ng(Hq
Hw In Ip Iq Is It Iv Jh Lw Lz Mb Mc Md Me Mn Mp Mt Mu Mv Mx My Na Nc Ne Nf Nh Nn No Nt Nv Nw Ny Om Oz Qa Qb) Jt(Hq Hr Hu It
Jg Jh Ji Jq Js Li Lu Lz Ma Mb Mc Md Me Mh Mu Mw My Na Nc Nf Ni Nl Nm Nn Nq Nx Oh Ok Pb Pd Pf Pz) Nm(Hv Ii In Ip Ir Jh Jp Js Lh
Lw Lx Mf Mj Ml Mq Mv Mx My Na Nd Nf Nj Nq Oh On Pd Pe Po Qd Qe) Ok(Fp Hw Ii Ir Iv Jg Jh Ji Jq Lw Lx Mc Ml Mp Mu My Nf Nj Ns
Nt Nu Om Pb Pc Pd Qa Qd) Nj(Et Hq Hv Iu Jg Jn Jp Li Lu Mi Ml Mq Mx Nd Nl Nn Nv Nx Pd Pe Pf Qa Qb) Nk(Et Hq Hx Iu Jn Jp Js Lu Mi Ml
Mq Mv My Mz Na Nf Nh Nq Ns Nt Pa Pf Pg) Oh(Hq Hr Io It Iu Ji Jk Lj Lu Lz Ma Mb Mu Ni Nl No Nu Nw Nx Pf) Mm(Hq Hr Iu Ji Lu Ma Mb
Nl Nx Pf Pz) Pz(Hv Ih In Iv Mf Mx Nd Nf Pd Pe) Nx(Hv In Ir Jn Jp Mi Nb Om Pc Qa) Lu(Hv Hx Jn Jp Mf Mx Nf Pd Qb) Pd(Ii Jp Lh Li Mi Mp
Mz Nu) Nn(Hv Ih In Jn Lx Mx Nd) Nh(Hq Jp Mb Nl Ny Oy Pf) Iu(Hv Ih In Jk Jn Mx Pe) Pa(Jg Mb Mf Mz Nc Nf Nt) Hx(Et Js Li Mb Ny Oy)
Ne(Hq Jp Nl Ny Oy) Pf(Hv In Mx Qb Qd) Pg(Jg Jk Jp Nf Po) Mz(Hq Js Li) Iq(Ir Qa Qd) Mx(Ii Li) In(Js Li) Qb(Ii Ny) Jq(Is Pe) NcNl}
Pa{Nj(Et Hq Hr Hu Hv Hw In Io Ip Ir Is Iv Jh Ji Jk Jn Js Lh Lj Lx Ly Lz Mb Mc Md Mj Mk Ml Mn Mp Mt Mw Mx My Na Nc Nd Ng Nk No
Nq Ns Nu Nv Nw Ok Om Oz Pb Pd Pg Po Qa Qb Qc Qe) Nx(Et Hr Hu Hw Ih In Io Ip Ir Jg Jk Jm Jn Lh Li Lj Lw Lx Lz Mc Md Mg Mj Ml Mn
Mp Mq Mt Mw Mx My Nd Ne Ng Ni Nl No Ns Nt Nw Ny Ok Om Oz Pb Pe Pg Po Qa Qb Qc Qd Qe) Oh(Et Hr Hu Hw Ih In Io Ip Ir It Jm Jn Jq
Li Lj Lx Lz Mc Md Mf Mg Mj Mk Ml Mm Mn Mq Mr Mw Mx My Na Nb Nd Ni Nm No Nq Ns Nt Nv Oi Ok Om On Oz Pb Po Pz Qb Qc Qe)
Lu(Et Hr Hu Hv Hw Ih In Ip Ir Is Iv Ji Jk Jn Li Lj Lz Ma Mb Mc Md Mf Mg Mj Mk Ml Mq Mt Mu Mw Mx My Nb Ne Nf Ni Nq Ns Nt Nu Nv
Ny Ok Om On Oz Pg Qa Qb) Of(Et Hu Hv Ih Ii Ir Is Iv Ji Jm Lh Lj Lw Lx Lz Mb Mc Mg Mj Ml Mm Mq Mr Mt Mu My Nb Ne Ng Ni Nm Nn
Ns Nw Oi Om On Oy Pc Pf Pz Qa) Mm(Fp Hr Hu Hw In Io It Jk Jn Jq Lz Mc Md Mj Mk Ml Mp Mr Mx My Nb Nd Ne Nf Nk Nl Nm No Nr Nt
Ny Om Oy Oz Pb Po Pz Qb Qc Qd) Oy(Hu Hv Hw Hx Ih Ir Is It Jm Jn Lw Lx Ma Mf Mg Mq Mu Mx Mz Nb Ng Nm Ns Oi On Pb Pg Pz)
Ng(Hw It Iu Jm Jt Lh Lz Mb Mf Mi Mk Ml Mq Mr Mu Mw Mx Mz Nc Nr Nu Oz Pb Pe Pg) Pz(Hx Ii Ir Is Iv Ji Jm Lw Lx Mb Mt Ni On Pf Pg
Qa) Ny(Ii Is Iv Jg Ji Lw Ma Mf Mu Nc Nn Nw Oi Pc Pg) Pd(Hr Hw Iu Jt Lh Lw Ma Mk Mr Mz Nc Nn On Pb) Nm(Et Ii Jg Ji Lh Ly Mb Mu Nc
Nn Nw Pc Pg) Nf(Hx Lw Lz Ma Mf Mi Mj Mz Na Ni No Oi Qd) Ii(Hu Hv Ir Is Li Lw Mb Mf Nb Nn Nw Pc) Nc(Ih Jm Jp Ly Mf Mg Mv Ni Nr
Nt Pc) Hq(Et Hw Ip Iv Lh Mf Mx Mz Oi) Js(Ir Iv Jn Jt Lh Mn Mt Na Qc) Pe(Hw Hx Lx Me Mu Na Nh Nw Om) Mi(Hu Jp Lj Mb Mg Nt Nv
Ok) Ly(Jm Mf Mg Mv Mz Nn Pc) Jp(Hr Hu Mb Mf Mp Ni Po) Pf(Fp Hu Me Mr Nh Nr Nu) Mz(Fp Li Mf Nt Nv Oi) Nn(Hr Is Ji On Pg) Mv(Li
Mf Nv Ok Po) Iu(Mh Nh Nr Nu) Jq(Is Ji Om On) Oi(Hu Hx Mb Pc) NtHr MbMf MgPc NaNb} Mz{Oh(Et Hq Hu Hw Hx Ih Ii Io Iq It Iu Iv Jh Ji
Jm Jn Jo Jq Jt Li Lj Lz Mb Mc Md Mf Mg Mh Mj Mk Ml Mn Mq Mr Mw Mx My Na Nd Ne Nf Ni Nk Nl Nm No Nq Nr Ns Nt Nu Nv Ny Of
Ok Om Oy Oz Pb Pd Pe Pf Qc Qd Qc) Lu(Fp Hq Hr Hu Hv Hw Hx In Io Ip Ir Iv Jh Ji Jk Li Lj Lx Lz Ma Mb Mc Md Me Mh Mj Mk Mn Mp Mr
Mw My Nb Nc Ne Nh Nl Nm Nn No Nq Nr Ns Nt Nu Nv Nw Ny Om Oy Oz Pb Pe Pf Po Qa Qc Qd Qe) Nj(Et Hq Hu Hv Hw Hx Ih Iq Jg Jk Jm
Jn Lh Li Lj Lw Lx Ly Mc Md Me Mj Mk Ml Mp Mx Na Nc Nd Nf Nh Ni Nl Nq Nr Ns Nt Nu Ny Ok Om On Oz Pb Pd Pe Pf Pg Po Pz Qc)
Iu(Hv Hw Ih Ii Is Iv Jg Jp Lx Ly Mb Me Mf Mj Mk Mp Mq Mr Mu My Nb Nc Nk Nn No Nr Ns Nw Ok On Pb Pe Po Qa Qd) Of(Hu Hx Iq Ir Is
Iv Jp Jq Js Lw Lx Ly Ma Mb Mf Mj Ml Mp Mq Mr Mu My Nc Ni Nk Nn Nr Nw Oi Pb Po) Mi(Et Fp Hq Hv Hw Hx Ih Ip Jn Mc Md Mf Mj Mp
Mq Mt Mx My Nb Nc Nl Nt Pb Pc Pe Pg Po Qc Qe) Jt(Et Fp Hq Ih In Iq Jm Jn Lj Mb Mc Md Me Mg Mh Mq Ne Ng Nh Ni Nm Ns Ny Oz Pd
Pf Pz Qa) Nx(Et Fp Hr Ih Ii In Io Jh Lj Lz Ma Me Mh Mn Mx My Nb Nq Nv Oy Qc Qe) Iq(Hv Ir Is Jg Jp Lx Ly Mf Mg Mj Ml Mu Mv Nk Nm
On Pe Pg Po Qb) Ng(Hx Ii Iv Jq Lw Ly Mp Mr Mu Nb Nc Nk Nm Nn Nr Nw Pb Pg Po) Nm(Hu Ir Is Jk Jp Lh Lw Ma Mb Mj Mp Mu Nc Nn
On Pc Po) Oi(Hx Ir Iv Jg Jk Jq Js Mf Mq Mu Nk Nu Ny On Pc Pg Pz) Pd(Hu Hw Jp Li Mj Mk Mr Nb Nc Nr Nw Pb Pc Pe Pg) Js(Hu Hx Jp Mj
Nc Nr On Pb Pg Po) Pz(Jk Jp Lh Lw Ma Nn Pc Pg) Jq(Hx Is Jo Jp Mu Mv Nc Pg) Ok(Lw Mu Nc Nn On Pg Po) Mg(Hu Jk Mu Nc Pc Pg) Jp(Hu
Li Mq Nk Nn Ny) Ii(Mj Nb On Pe Po) Ly(Jg Mm Mu Mv) Nc(Hu Jk Mf Nh) Jo(Jm Ne Nh Ny) Lh(Na Nf Nv Pf) Nn(Jk On) Nt(Lx On) Mm(Et
Me) Mv(Nv Pf) Hu(It Pc) Ny(Mu Pg) MbMf NiNk NvPg PePf} Jo{Mi(Et Hq Hr It Iv Jh Ji Jn Jq Js Jt Li Lj Lw Lz Mb Mc Md Ml Mp Mq Mt
Mv Mw Mx Na Nc Nf Ni Nl Nn No Nt Nu Nw Ny Of Ok Om Oz Pd Pz Qc) Po(Fp Hr Ii It Iu Jm Jq Li Lw Ly Lz Mc Md Me Mj Mk Ml Mm Mp
Mr Na Nb Nc Ni Nn No Nr Nt Oh Oi Ok Om Oy Oz Pc Qc) Nv(Hv Ih In Io It Ji Jk Jn Jp Lj Md Me Mf Mg Mh Ml Mm Mn Mq Mt Mu Mv Mx
My Na Nc Nd Ng Nk Nl Ns Nt Nx Pf Qa) Qe(Fp Hq Hw Ih In Jn Js Ma Mc Md Me Mg Mm My Nc Ng Ni Nk Nl Nm Ns Nx Ny Oz Pd Pz Qa
Qb Qc Qd) Nw(Hu Hv Hw Ii Io Ip Lu Lx Ly Ma Md Mf Mh Mj Mm Mp Mq Mv Ng Nk Ns Nx Oh Om Oz Pb Pd) On(Et Hr Hu Ii Iu Jg Jq Li Lj
Lu Lw Ly Lz Mb Mc Md Me Mg Mu Nc Ni Nn Nt Of Om Oy Pc) Lx(Hw In Io It Ji Jn Jp Lh Ly Ma Mf Ml Mm Mq Mv Mx My Nc Nk Ns Nt
Of Oh Oi) Qa(Et Hv Io Jh Jm Ma Mf Mh Ml Mq Mt Mw My Nc Nd Nq Nt Of Oi Ok Pf Qd) Mv(Hv Hw Ip Iu Iv Jk Lw Ly Mk Mn Mr Mt Mx
Nb Nd Ne Nh Nr Nu Oy Pc) Mn(Hr Hv Hw Iu Iv Jg Ji Li Lu Lz Mp Mt Mx Nf Nu Pb) Qd(Et Hv Jh Lu Lz Mf Mh Mw Na Nc Nd Nq Nt Of Pf
Qb) Pe(Hv Hw It Mb Me Mg Mj Mq My Ne Nh Ni Nl Ns Qc) Mp(Hq Hw Ih Ii Io Ip Jn Mj Mk Mr Mw Nr) Jg(Hv Hw Ii In Jn Lh Ly Mg Mj Nd
Ng Nh) Ji(Hv Hw Ii In Ip Ly Mj Mt My Nb Nh Nq) Jh(Hv Ip Iu Li Lw Mr Nb Nf No Oy Qb) Jp(Ii In Jt Lu Ly Mj Mk Mr Nb Nr Pc) Nq(Hv Iu
Iv Lw Mk Mr No Nr Qb) Pc(In It Lu Ma Mx Nd Ne Nh Nj) Ih(Ii Ip Mk Mr Nb No Nr Oy) Jk(Hv Lu Ly Lz Ma Mt Mu Nc) Nn(Ii Io Jn Lu Mj
Mw) Ma(Hv Iv Jt Mr No Oy) Mt(Hv Hw Iv Lz Mu Qb) Nd(Ii Mj No Ok Oy) Qb(Et Hv Io Mu My) Ly(Hx Mu No Om) Mw(Iu Iv Nf Pb) Lw(Jn
Lu Mx) Mj(Jm Jn Pz) Is(Ir Jn Js) Lh(Js Mu Ni) Nm(Nb Oy) Hw(Ip Nj) Hx(Mm Oh) Ok(Ne Nh) MuIp MyOm HuIr IiPz} Pg{Ii(Et Fp Hq Hv Hw
Ih Io Iq Iv Jk Li Ly Mc Md Me Mh Mj Ml Mm Mn Mp Mx My Na Nb Nd Ne Ng Nh Nk Nl Nm Nn No Ns Nt Nv Nw Ny Of Oh Ok Om On Oy
Oz Pb Pc Pe Po Qa Qb Qc Qd Qe) Lu(Et Fp Hw Hx Ih In Io Ip Is It Iv Ji Jk Jm Jn Jq Li Lj Ly Lz Mb Mh Mj Mk Mn Mp Mr Mt Mv Nb Nj Nl
No Nr Nu Nv Nw Ok Om Pb Pe Po Qa Qb Qc) Mm(Et Fp Hq Hr Hu Hv Hx Ih Iq Ir Is Iv Jk Jn Jq Lw Mc Mh Ml Mn My Na Nb Nd Ne Nm Nn
No Ns Nt Ok Oz Pc Pe Po Qa Qb Qc Qd Qe) Ng(Et Hv Ih In It Ji Jn Lw Mc Md Me Mp Mq Mx My Na Ne Ni Nl Nn No Nq Nt Nu Nv Nw Oi
Ok Pb Po Qc) Of(Fp Hx Ir Jh Ji Jn Js Li Lx Mg Mh Mn Mq Mt Mw Na Nc Nd Ne Nf Nj Nk Nn Ns Nt Nw Ny Oi On Pc Qa) Iq(Fp Hv Jg Jm Jn
Jq Js Ly Ma Ml Mq Mv Na Nc Ne Nf Nj Nm No Nw Oh Om On Oy Pf) Iu(Hx Ih Ir Is Jg Ji Jm Jn Jp Js Ma Mf Mq Mt Mu Na Nc Ne Nf Ns Nw
Qa Qd) Oh(Hv Hx Jg Ji Jm Jn Js Lh Lx Mf Mq Mt Na Nc Nf Ni Nj Nn Nw On Pc) Pf(Hv Hx Ir Jg Jh Ji Jp Js Mf Mq Mt Na Nc Ne Nf Nj Ns Nw

Figure 16 Continued

On Qa) Mg(Fp Hq Hu Jm Js Lh Li Lj Lw Ma Mf Na Nm Nn Ny Oi On Pd Pz) Oi(Fp Hx Iv Jm Jn Js Ma Mb Mf Mi Mq Na Nf Nk Nm Oy Pd Pz) Pd(Hq Hv Hw Hx Jm Li Ly Mf Mp Nb Nw Ny Oy Pc Pe) Nj(Jg Jm Js Lh Mq Mu Mv Ne Ni Nm Nn Oy Pc) Mi(Hq Hu Hw Ih Lx Mf Mq Na Nf Nk Nt) Jp(Hq Jq Ly Mf Mq Na Nc Nf Nn Nv Pz) Nm(Jg Jm Js Lh Mf Mu Nc Nf Ni Nw) Lh(Jq Li Nf Nn Ok Pz) Mv(Li Nv Ny Oy) Nc(Js Li Mf Oy) Pz(Jg Jm Mu Ni) Jm(Li Ly Ny) Nn(Jg Nw) Mu(Li Ny) Nx(Nh Pe)} Mi{Nj(Et Hr Hw Ih Ii In Io Ir Is It Iu Iv Lh Lj Lw Lx Lz Ma Mb Mc Me Mh Mj Mk Ml Mn Mr Mv Mw Nb Nn No Nr Ns Nu Nv Nw Ny Of Om On Oy Pb Pe Pf Po Pz Qa Qd Qe) Hx(Et Hr Hv Io Ip Iv Jh Jk Jn Jp Lw Mc Md Me Mj Mk Ml Mt Mv Mw My Nb Nc Ng Nl Nu Om Oz Pe Qc) Ly(Hw Ih Io It Jg Jn Lj Lw Lz Mc Md Me Mh Mk Mp Mr Mu My Ni Nn No Nr Ns Nv Ny Om Pb Qc) Nm(Hq Ih Iq Iu Ji Jn Jq Js Li Mn Mv Ne Nl Nn Nv Nw Ny Of Oi Om Pz Qa) Ng(Hv Is Ji Lh Ma Md Mf Mg Mj Mq Mw My Nb Nc Nr Ns Nu Oi Ok Oy Pe Qe) Hu(Et Fp Hq Ii Ip Iq Ir Ji Jp Lx Mb Mf Ml Mv Na Nc Nf Nt Nv Pb Qe) Nx(Fp Hr Hw Jh Jp Js Lz Ml Mu Mv Ne Nn No Ns Ny Of Oi Om Pd Pz) Mm(Fp Hq Ii Io Ji Jk Js Li Lz Nb Nd Ne Ni Nk Nn Nw Oi Pd Qc) Lu(Hq Io Jh Jn Js Lw Lz Mb Mc Me Mr Mx My Nc No Nw Pc) Jq(Hq Ii Jp Lh Ma Me Mf Mj Na Nc Nf Nh Nl On Oy Pd Po) Pd(Ii In Ip Iq Ir Is Iv Jk Jt Mx My Oh Pb Pc Po Qa) Li(Hr Io It Iv Jp Lw Mb Mk Mr Nc Nn No Om Pc Qb) Mg(Hv Ir Ma Mj Mt Na Nc Nf Nu Oi Ok Qc Qe) Nk(Iq Ji Js Mf Mv My Na Nf Ny Pb) Ok(Hv Jp Lx Mn Mt Nf Nw Pb Qe) Jt(Et Iq Iu Jg Mu Nt Qc) Pf(Ip Lx Mj My Pe Qb Qd) Jk(Fp Iu Js Nc Ny Po) Oh(Iu Jg Jp Nc Nh Ni) Oi(Iq Jp Lx Nb Nf Nu) Ip(Iu Ji Mf Na Ny) Pz(Iv Jh Mn Mv Pb) No(Is Mk Oy Pe) My(Iq Js Lj Nf) Ny(Lx Mt Pc Qd) Of(Mn Mv Nv Qb) Mb(Hv Mj Pe) Ii(Ir Qb Qe) Iq(Lh Lx Nt) Js(Ir Nc Qd) Lj(Hv Is Nc) Nr(Na Nf) Iu(Ih Lx) MeNf MjPc Hwls} Jt{Hx(Hq Hu Ii In Iq It Iu Jm Jn Lj Lu Lz Mb Md Me Mg Mk Mr My Na Nh Nk Nl Nr Nu Nx Ny Of Oh Oy Oz) Po(Hw In Io Ip It Iu Lu Md Mj Mk Mm Mr Mu Nb Nh Nk Nr Nu Oh Ok Oy Qc) Ir(Hu Ih Jh Jn Jq Lu Ly Md Mg Mh Mt Mw My Na Nc Ne Nj Nk Nv Qa Qc Qe) Ji(Hv Hw Ii Ip Iv Mf Mk Mp Mr Mx My Nb Nd Ne Nh Nn No Nr Oy Pc) Om(Hv Ih Ii Io Iv Jn Lu Lw Ly Mk Mn Mr Mt Mx Ne Nh Nn No Pc) No(Hv Hw Ip Iv Lw Ma Mk Mr Mx My Nb Nn Nr Oy Pc) Qe(Hr Hv Io Ip Iu Iv Jm Mm Mn Mv Nf Nt Ok) Mn(Hv Hw Ii Ip Iu Lz Mj Mx Nb Qb) Pe(Et Jq Mj Na Nd Nm Ny Ok Pd Pz) Nw(Iq Jm Ma Mh Mu Mv Nc Ny Qc) Nn(Hv Ih Iu Iv Lx Nd Ns Nv) Qa(Hw Ip Li Mu Mv Nf Nu Pb) Qb(Et Io Ip Lz Mu Mv Nf Ok) Mp(Iv Mj Mk Mr Nb Nr Pc) Jp(Hr In Lu Mx Nd Nf Pb) Qd(Et Iv Lx Lz Mf Nt) Jk(Ip Iv Li Nu Ok Oy) Nv(Hr Ip Iv Li Lu Nf) Lw(Hu Ih Mx My) Lx(Iu Lu Ne Nu) Mj(Mu Mv Mw Nq) Pc(Hu Jq Mw Mx) Ma(Mk Mr Nr) Jg(Ih Ng Oi) Lh(Mg Mh Nt) Mt(Hw Oy) Mv(Ii Nb) Mw(Nb Nr) MuIi} Mm{Lh(Et Fp Hq Hu Hw Ih In Io Ji Jm Jn Li Lj Lu Lz Mb Mc Md Me Mh Mj Mk Ml Mp Mx My Nb Ne Nh Ni Nl Nm No Nq Nr Nv Ny Ok Om Oy Oz Pb Pf Qc Qd) Lx(Fp Hu Hw Ip Ir Is Jh Ji Jn Js Li Lj Lu Ma Mb Md Mf Mj Mk Mq Mr Mt Mv Nj No Nr Nw Ny Oi Pb Pd Pe Pz Qa Qc) On(In Io Jg Jh Ji Lj Lz Md Me Mh Ml Mn Mp Mv Mw Mx Nd Nl Nq Nv Ok Oz Qd) Nw(Hx Ir Is Jk Lu Ma Mf Mg Mv Nd Ne Ng Nh Nj Oi Pd Qb Qd) Ma(Hv Is Jk Jp Mt Pe Po Qb Qd Qc) Mv(Ir Jn Jp Mp Pc Pe Po Qa Qd Qe) Hx(Jg Jp Lw Mt Mu Nf Ng Oi Pc) Is(Jg Jp Mg Nc Ng Nj Oi Pc) Qa(Lu Lw Mp Mu Nx Oi Pe Po) Qe(Iq Iu Ji Jm Lw Mu Oi Po) Ir(Jm Js Mf Na Nx Oi Po) Nv(Jg Lw Mf Ng Oi Pe Po) Qb(Jg Ji Lu Nx Pc) Mt(Iu Jp Li Mu) Po(Jh Jn Nx) Nn(Ih Jh Qd) Pe(Jp Nx Pc) Qd(Iq Jg) Jn(Lw Mu) MwPc NdNj NgJp} Ng{Lh(Et Is Jg Jh Lx Lz Me Mh Mk Mn Mr Mt Mw My Nl Nm Nn No Nq Nu Nw Ok Om Oy Oz Pb Pc Pe Qc Qe) Jp(Hv Ih In Ip Iu Iv Jg Jh Jn Lw Mf Mp Mq Mw Mx Ne Nf Nh Nj Nn No Nw Of Qa Qb Qe) Lx(Hq Jg Jn Js Lu Mf Mk Ml Mr Mt My Na Nb Nf Nk Nr Ns Oh On Oz Pb Pe) Mv(Hq In It Jh Js Li Lj Lz Mc Md Mg Mt Mu My Nj Nm Nn No Nw Of Pc Pz) Hx(Hu Lw Ma Mf Mj Mk Mp Mq Mr Mt Na Nc Nf Nj Nr Nw Nx Oh Oi Oy Pe Po) Pc(Ir Is Jn Mt Mu Mw Po Qd) Pe(Ma Mt Mx My Na Nf Nj Nq) Po(Fp Hu Lj Ly My Pd) On(Iv Lu My Nf Nj Nm) Ma(Ii Mk Mr Nb Pb) Mt(Mk Mr Nb Oy Pb) Hu(Mk Mr Nb Nq Oy) Is(Iq Iu Js Oh) Jg(Ii Nj Nk Oh) Lu(Jh Qd Qe) Mw(Mk Mr Pb) Jk(Et Ly Nw) Mu(My Nj) Oy(Jh Nq) NnLy LwMy IrNx} Nx{Is(Hq Hu Hv Hw Hx Ih Ii Iv Jg Ji Jk Jm Li Lj Lu Lx Ly Mb Mc Mg Mj Mk Mp Mq Mr Mt Mu Mv Na Nc Ne Nk Nm No Nr Ns Nt Nu Ny Pb Pc Pd Pe Qa Qb) Jp(Hv In Jn Lw Lx Mf Mg Mj Mp Mq Mt Mw Mx Nb Nd Nj Nk Nn Ns Oi Pc Pe Po Qd Qe) Qb(Hx Iq Iu Jg Lu Lw Mp Mv Nc Nj Nw On Po) Lx(Iu Js Mf Ml Mq Mt Mu Oh Om On Pc Pd) Nw(Hu Iu Ly Mk Ne Nh Nj Nk Oi Ok Pe Qa) On(Hr Ir Iu Ji Lh Mv Nc Nv Pd Pe Qa) Po(Hx Ir Mp Nf Nj Oi Pd Pf Qa Qd) Hx(Iq Jg Lw Mu Nf Nj Om) Lw(Ir Jn Om Qa Qd) Nn(Lu My Nj) Pe(Mp Mu Pf) Ir(It Oi) MpPd MtMu MvOi IqQd IuQa JqPc} Iu{Ir(Fp Hq Hv Hw Hx Ih Ii In Io Iq It Iv Jg Ji Jn Jp Jq Lh Li Lj Lw Lx Ly Lz Ma Mb Mc Md Me Mh Mk Ml Mp Mr Mv Mx Nb Nc Nf Ni Nk Nl Nm Nn No Nq Nr Ns Nw Ny Of Oh Ok Oy Oz Pb Pc Pe Pf Po Pz Qa Qc Qd) Hx(Is Jg Jh Jn Jp Js Lx Ma Mf Mg Mq Mt Mu Mv Na Nb Ne Ni Nq Pd Pe Qa Qb Qd) Lh(Hq Jk Li Lx Ne Nk Nq Nt Of On Pe Qb Qd) Lu(Mp Mt Nn Nv Nw) Pe(Iq Lx Mt Nc Qa) Nj(Is Nd Qd Qe) On(Mq Na Pd Qe) Is(Mg Mv Oi) Lx(Hq Oh) Hu(Qb Qd) MvQb QaNw QeOh JkJn} Lu{Nn(Fp Hq Hw Ip Ir Is Jk Jp Jq Lx Mc Mh Mj Ml Mq Mr Mv Mw Mx My Nb Ne No Nr Nv Ny Of Oh Om On Pb Pf Pz Qd) Lw(Hu Hv Jk Jn Jp Lx Mg Mp Mw Mx My Nb Nd Ne Nh Nk On Pd Po Qe) Qb(It Jm Js Mf Mg Mq Na Nc Nf Nj Of On Pd Po Pz) Pc(Hv Ir Jk Jp Mg Mj Mp Nd Ne Nf Nh Po Qd) Oi(Ir Ji Lh Ma Mn Mt Mu Om On Pe Qe) Is(It Jq Mf Mg Nf Pd Pz) Jp(Hx Iq Lx Ly Mg Nd Qa) Po(Js Mg Ml My) Qa(Of Oh Pz) Mg(Jg Mu) Ok(Nw On) LxPd MpHq NfHx OfPe} Hx{Iq(Hu Ir Is Jg Jk Jp Mf Mg Ml Mq Mt Mu Mv Na Nf Nh Nj Pd Qb Qd) Oi(Hq Hu Hw Jg Js Lw Lx Ly Ma Mb Mf Mq Mt Mu Na Nb Nc Of Oh Pd) Nf(Jg Jp Lh Lw Mv Nn Oh On Pc Po) Pd(Jg Jp Li Lw Mp Mv Nn Nw On Pc) Nj(Jg Jp Lw Mf Mg Mu Mv Nn Pc) Oh(Jp Ma Mu Mv Nn Nw Pc) Jp(Jq Js Mq Of Ok) Of(Lw Mu Nn) Mg(Mu Nn) Mv(Ii Pz) Jg(Ii Nm) Js(Is Lh) Ok(Nw On) LwHu MaPz HrPc} Jp{Mg(Hu In Ir Is Jg Lh Lw Lx Mp Mt Mu Mv Nc Nh Nk Nn On Pc Pe Po Qa Qb) Nj(Ir Jk Lh Mf Mq My Nl Nn Nq Pc Po Qa Qb) Oi(Ir Is Jn Lh My Nc Nh Nk Qa) Ly(Mf Mu Mv Nd Ne Nh Pd Qb) Pd(Hw Mj Mk Mr Nr Pe) Oh(Ir Is Qa Qb Qe) Pe(Js Mx Nf Nt) Nm(Lw On Qa) Iq(Ir Nc Qb) Is(Jq Js Ok) Mv(Ne Nh) In(Ml Mq) Pz(Qa Qb) NhPc IrOk QaJs QbNy} On{Pd(Hr Hv Iv Ly Mb Mf Mt Nf Of Oh Oi Ok Pc) Nm(Et In Ip Iq Md Me Mh Mq My Nj Of Om) Nf(Hu Iq Ly Mb Nc Nt Ny Ok Pz) Nj(Mq Nd Nt Of Ok Pz) Li(Lx Me Mu Mv Nn Om) Oh(Lh Lx Mu Mv Nn Pz) Iq(Mq Of Ok Pe Qb) Of(Hu Ly Nn Pz) Ok(Hr Ly Ma Oi) Mb(Mq Na Nt) Mg(Jg Mq Mv) Js(Nn Pc Pf) NnMq HrPf HuOi HwLj IiPe} Lx{Oh(Et Hw Io Js Lh Li Mb Mc Md Mh Mj Mk Mp Mr Mt Mu Mw Nm Nn No Nw Ny Ok Om Pb Pc) Pd(Hu Hv Iv Jn Js Ly Ma Mb Mc Mf Ml Mq Mt Na Nk Nl Nn Ns Nu Oi Pc Qa) Hq(Hr Ii Io Iq It Ji Ly Lz Pb Pc) Oi(Hu Ly Mv Pc) Nm(Mf Mq) Mg(Jg Pc) Js(Is Mq) Lj(Hw Lw) PoLi FpMf NtLy MvOf PePf} Mv{Oi(Hv Ii Ip Is Iv Jn Lw Mf Mk Ml Mp Mq Mr Mx Nm Nn Nt Nw Of Oh Oy Pb Pc) Mg(Ip Jn Lh Lw Ml Nj Nn Nr Nt Oh Oy Pb Pc Pd Pe Po) Of(Ii Ir Is Mj Mk Nd Po Qa Qb Qe) Pd(Hw Lh Mj Mp Mr Nb Nr Pb) Oh(Is Mp Nn Po Qa) Pz(Is Lh Qa Qd) Pe(Jk Js Li) PoLi NcNe} Po{Pd(Fp Iv Jn Js Mb Mg Na Nf Nk Oh Oi Pc Pz) Js(Fp Hr Jn Nf Nj Ny Oh Pc) Li(Hw Md Mu Nn No Ny) Oh(Jn Mf Mq Na Nm Nq) Nj(Mg Nd Nf Oi) Mb(Mf Nf) Hu(Iq Oi) FpNf MgJg} Lh{Iq(Hu Ir Is Jk Nm Oi Pz Qd) Nj(Lw Mg Nd Nn Oi Pc) Pz(Is Lw Oi Qa Qb) Oh(Nm Nn Of Oi Pc) Pc(Nk Nm Nn Pd) Nf(Oi Pd Pf) Of(Mh Mt Qe) Nn(Jq Ok) Js(In Pd) NmOi MgJg NaPd HqJq NwOk} Pe{Iq(Fp Hr Hu Mf Mj Mw Oh Pd Pz Qb) Hr(Io Mf Mx Na Nf) Pd(Lw Nn Pc) Ma(Of Pf) Js(Hq Qa) NnHw} Oh{Nn(Ir Jn Js Mc Mq Mw) Mu(Jn Mf Mp Mq Mt) Is(Iq Oi) Jg(Mg Qa) LwMj IrPc QbNw} Mg{Jg(Ii Ip Jn Mj Oy) Mu(Ly Nj) Pc(Mt My) NnNj IqIs} Oi{Nj(Is Jg Mu Nn) Is(Hu Jq Nc) Ly(Ma Nw) MuHu IqQd} Of{Ir(Iq Jg Nn Pc) My(Lw Nn) Pc(Hu Mw) IqIs QaJg} Mj{Hw(Lw Lz Pb) Js(Nw Qa) Lj(Mu Nn) MfPc MpLi} Js{Is(Hr Na Nf) Qa(Mr Nr Pb) InNw} Nn{Hu(Nm Ny) NcNh NdNj} Nj{Lw(Jk My) NwOk} Iq{Mfls IrJk QbNw} Pz{Jg(Ir Qe) MuQa} Hw{In(Mr Nr)} LyNwOk MbMpPd IiIrJk Unconstrained panels with 2 analytes, where 1.0E-6 >= 'AUC p-value' > 0. Contains 246 panels of 6,786 total panels evaluated. : Lv(aA Et Fp Fr Hq Hr Hu Hv Hw Hx Ih Ii In Io Ip Iq Ir Is It Iu Iv Jg Ji Jj Jk Jl Jm Jn Jo Jp Jq Jr Js Jt Lh Li Lj Lu Lw Lx Ly Lz Ma Mb Mc Md Me Mf Mg

Figure 16 Continued

Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu
Nv Nw Nx Ny Oe Of Og Oh Oi Ok Om On Oy Oz Pa Pb Pc Pd Pe Pf Pg Po Pz Qa Qb Qc Qd Qe) Jl(Ii Iq Iu Jj Jo Jq Jt Li Lu Ly Mg Mm Ms Ng
Nj Nm Nn Nv Nx Ny Oe Of Og Oh Oi Ok Pz) Og(aA Fr Hx Ir Is Iv Ji Jp Jr Lh Mi Mj Mu Mz No Nw Om On Pa Pe Pg Po) aA(Fr Iq Iu Jj Jo Jr Jt
Lw Mi Ms Mz Na Ng Nn Oe Oi Pc) Jj(Hx Ir Is Jk Jr Lh My Mz Pa Pe Pg Qa Qb Qd Qe) Oe(Fr Hx Ir Is Jp Jr Mi Mz Nw Om Pa Pe Pg Po) Jt(Ir Is
Lh Mi Nw On Pa Pg Po) Jo(Hx Ir Is Lh Mz Pa Pe Pg) Mi(Jr Mm Ms Nm Nx Oh) Fr(Mm Ms Oh) Pa(Iq Iu Pf) Mz(Mm Nx) HwPe JrPc LiOn
NxPg

Unconstrained panels with 2 analytes, where 1.0E-5 >= 'AUC p-value' > 1.0E-6. Contains 130 panels of 6,786 total panels evaluated. : aA(Hv Ih
Ii In Ip Jl Jn Jp Jq Js Ly Lz Md Me Mf Mm Mp Mq Mr Mu Mx Nf Nk Ns Nt Of On Pd Pg) Jl(Et Fp Hq Hu Hw Ih Jm Jn Jp Jr Js Mb Mf Ml Mq
Mx My Mz Na Nc Nf Nk Oy Pa Pd) Og(Hv Jg Jh Jn Lx Mk Mt Mw Nb Nn Nu Nv Pb Qa Qb Qd Qe) Jr(Fr Iq Jq Js Lw Ms Mv Nn Oi) Fr(Jo Jt
Ly Mg Ng Of Oi) Mi(Hx Jo Lu Ly Nj) Ms(Jg Mu Mz On Pa) Jj(Hu Ih Mt Mw Nv) Oe(Lh Mj No Nu) Pa(Mm Nj Nx Oh) Lu(Mz Nn Pg) Ng(Lh
Mv Pg) Jo(On Po Qe) Lx(Oh Pd) Mm(Lh On) Mz(Jt Oh) PoLi NmOn HxJt IiPg Irlu Unconstrained panels with 2 analytes, where 1.0E-4 >= 'AUC p-value' > 1.0E-5. Contains 302 panels of 6,786 total panels evaluated. : Jl(Fr Hr
Hv Hx In Io Ip Ir Is It Iv Jg Jh Ji Jk Lh Lj Lw Lx Lz Ma Mc Md Me Mh Mi Mj Mk Ml Mm Mn Mr Mt Mw Mx My Nb Nc Nd Ne Nh Ni Nl No Nq Nr
Ns Nt Nu Nw Om On Oz Pb Pc Pe Pf Pg Po Qa Qb Qc Qd Qe) aA(Et Fp Hq Hr Hw Hx Io Ir Is It Iv Jg Jh Ji Jk Jm Jn Js Lh Li Lj Lu Lx Ma Mb Mc
Mg Mh Mk Ml Mn Mt Mv Mw My Nb Nc Nd Nj Nl Nm No Nq Nr Nu Nv Nw Nx Ny Oh Om Oy Oz Pa Pb Pc Pf Po Qa Qc Qd Qe) Jr(Ih It Iu
Jg Jn Jo Jp Jt Lh Lu Lx Mf Mg Mp Mq Mu Mz Na Nf Ng Nj Nx Oh On Pa Pd Pg Po) Jj(Fr Hv Ii In Iv Jh Jm Jn Jp Lu Lx Ly Mi Mj Mn Mv Mx
Nd Nq Og On Po) Og(Et Ih Ii Ip Jk Lu Lw Lz Ma Mn Mp Mr Mv Mx Nr Ok Oy Pc) Pa(Fr Hq Ii Jp Lu Mv Mz Nc Nf Ng Nm Ny Of Oy Pz)
Mz(Hu Iq Iu Jp Jq Mi Nc Ng Nj Nm Of Oh Oi Pd Pf) Pg(Iq Iu Jp Mg Mi Mm Ms Nm Of Oh Oi Pd Pf) Ms(Hx Is Ji Jp Lh Mv Nn Nw Po) Oe(Iv Jg Ji
Lx Mn Mt Nb Qd Qe) Fr(Lu Nj Nk Nm Nn Nx Ok Pz) Mi(Hu Ip Jq Lj Mg Ng Nk Pd) Lx(Hq Jo Lj Mm Ng Nm Nx) Jp(Lu Ly Mg Ng Nj Nx Oi)
Hx(Iq Iu Ng Oi) Jo(Nv Nw Qa Qd) On(Hw Js Pd Pf) Oh(Mu Nn Po) Mm(Ir Nv) Mv(Mg Oi) PoPd LuQb HrPe IsNx Unconstrained panels with 2 analytes, where 1.0E-3 >= 'AUC p-value' > 1.0E-4. Contains 514 panels of 6,786 total panels evaluated. : Jr(Et Fp
Hq Hu Hv Hw Hx Ii In Ip Ir Iv Jh Jk Jm Li Lj Ly Lz Ma Mb Mc Md Me Mh Mj Mk Ml Mm Mn Mr Mt Mw Mx My Nb Nc Nd Ne Ni Nk Nl
Nm No Nq Nr Ns Nt Nu Nw Ny Of Ok Oy Oz Pb Pe Pf Pz Qa Qb Qc Qe) Mz(Et Fp Fr Hq Hv Hx Ih Ir Is It Iv Jg Jh Ji Jk Jm Jn Js Lh Lj Lw Lx
Ly Ma Mb Mc Mf Mg Mj Ml Mn Mp Mq Mt Mu Mv Mx My Na Nd Ne Nf Ni Nk Nn Nq Ns Ny Ok On Oz Pc Pd Pe Pf Pg Po Qa Qb) Pa(Hr Hu
Hv Hw Hx Ih Ir Is It Iv Jg Jh Ji Jm Jn Js Lh Li Lj Lw Lx Ly Lz Ma Mb Mf Mg Mh Mi Mn Mq Mt Mu Mx My Na Nb Ne Ni Nk Nn Nq Nr Ns
Nt Oi On Pc Pe Pg Po Qa) Jj(Fp Hq Hr Hw Io Ip It Iu Jg Ji Js Jt Li Lj Lw Lz Ma Me Mf Mk Mp Mr Mu Nb Nc Ne Nf Nh Nj Nk Nn No Nr Nt
Nw Oe Ok Om Oy Pb Pc Pf) Jp(Fr Hu Hx Iq Ir Is Jk Jn Jo Js Jt Lh Mf Mi Mm Mq Mv My Nc Ne Nh Nk Ns Ny Oh Pd Pe Qa Qb) Oe(Hv Ih Ii Ip
Iu Jh Jk Jn Lu Lw Ma Mk Mp Mr Mu Mv Mw My Nd Nn Nq Nr Nv Ok Om Pc Pf Qa Qb) Hx(Fr Hw Ii Jg Lh Lu Lw Lx Mf Mg Mm Mu Mv Nf
Nj Nn Nx Of Oh Pc Pd Pg) Og(Fp Hu It Iu Jq Js Jt Li Lj Me Mh My Nc Nd Nl Nq Nt Ny Of Pf Qc) Lx(Fp Jm Jt Lu Mc Mf Mh Mi Ml Mq Ms
Nl Ny Of Oi Pc Pf) Pg(Fr Jm Js Lh Mf Mq Mu Mv Na Nc Nf Ni Nj Ny Oy Pz) Mi(Fp Iq Ir Js Mb My Nc Nf Nr Oi Ok Pc Pz Qa Qe) Jo(Hw Ii Ip
Jg Ji Jk Lw Mj Mn Mt Mv Nb No Pc Qb) On(Fp Hr Iu Lu Mb Mg Na Nf Ng Nt Nx Of) Fr(Et Hq Hv Iu Jg Li Nh Nu Pd Pf Qb) Mm(Is Mt Mu
Mv Nn Nw Pe Po Qa Qb Qe) Lh(Iq Iu Na Nf Nm Oh Oi Pc Pd Pf Pz) Jt(Ji Nn No Nv Om Pe Qa Qb Qd Qe) Lu(Is Lw Mp Ng Nw Pc Pe Po Qa)
Nx(Ir Mt Mu Nn Nw Pe Po Qa Qb) Is(Iq Iu Js Mg Ng Of Oh Oi) aA(Hu Mj Ne Ni Ok Pz Qb) Po(Fp Js Mb Ng Nj Pc) Ms(Ir Lw No Pc Pe) Iu(Pe
Qa Qb Qd Qe) Nn(Hu Ng Nm Pd) Mt(Hq Js Mf Pd) Ir(Iq Of Oh Oi) Ng(Jg Mp Nw) Nm(Mu Om) Mj(Hr Pc) Mv(Of Oh) Nw(Ok Pd) MgJg
MpPd NdNj HuPc IqQb QaOi PePf Unconstrained panels with 2 analytes, where 1.0E-2 >= 'AUC p-value' > 1.0E-3. Contains 1,243 panels of 6,786 total panels evaluated. : Hx(Et
Fp Hq Hr Hu Hv Ih In Io Ip Ir Is It Iv Jh Ji Jk Jm Jn Jq Js Li Lj Ly Lz Ma Mb Mc Md Me Mh Mj Mk Ml Mn Mp Mq Mr Mt Mw Mx My Na Nb
Nc Nd Ne Nh Ni Nk Nl Nm No Nq Nr Ns Nt Nu Nv Nw Ny Ok On Oy Oz Pb Pe Pf Po Pz Qa Qb Qc Qd Qe) Ir(Fp Fr Hq Hu Hv Hw Ih In It Iv
Jg Jh Ji Jk Jm Jn Js Lh Li Lj Lu Lw Lx Ma Mb Mc Md Me Mf Mg Mh Mj Ml Mn Mp Mq Mt Mu Mv Mw Na Nc Nd Nf Ng Ni Nj Nk Nl Nm
Nn No Nq Ns Nv Nw Ny Ok On Oz Pb Pc Pd Pe Pf Pg Po Pz Qa Qb Qc Qe) Pg(Et Fp Hq Hr Hu Hv Hw Ih In Io Ip Is It Iv Jg Jh Ji Jk Jn Jq Li Lj
Lw Lx Ly Lz Ma Mb Mc Md Me Mh Mj Mk Ml Mn Mp Mr Mt Mw Mx My Nb Nd Ne Nh Nk Nl Nn No Nq Nr Ns Nt Nu Nv Nw Ok Om On
Oz Pb Pc Pe Pe Po Qa Qb Qc Qd Qe) Jp(Et Fp Hq Hr Hv Hw Ih Ii In Io Ip It Iu Iv Jg Jh Ji Jm Jq Li Lj Lw Lx Lz Ma Mb Mc Md Me Mh Mj Mk Ml
Mn Mp Mr Mt Mu Mw Mx Na Nb Nd Nf Ni Nl Nm Nn No Nq Nr Nt Nu Nv Nw Of Ok Om On Oy Oz Pb Pc Pf Po Pz Qc Qd Qe) Fr(Fp Hw Ih
Ii In Io Ip Iq Is It Iv Jh Jn Jq Js Lh Lj Lw Lx Lz Mb Mc Md Me Mf Mh Mi Mj Mk Ml Mn Mp Mq Mr Mt Mu Mv Mw Mx My Na Nb Nc Nd Ne
Nf Nl No Nq Nr Ns Nt Nv Nw Ny Om On Oy Oz Pb Pc Pe Po Qa Qd Qe) Qa(Hu Hv Hw Ih Iq Is It Iv Jg Jh Ji Jk Jm Jn Js Lh Li Lw Lx Ly Ma
Mf Mg Mj Mk Ml Mn Mp Mq Mr Ms Mt Mu Mv Mw My Nc Nd Ne Ng Ni Nj Nk Nm Nn No Nq Nr Ns Nv Nw Ny Of Oh On Pb Pc Pd Pe Po
Pz) Lh(Et Hq Hr Hu Hv Hw Ii Ip Is It Jh Jq Js Li Lu Lw Lx Mb Mc Md Me Mf Mg Mh Mi Mj Mk Ml Mn Mq Mr Mt Mu Mv Mw Nb Nc Nj
Nk Nl Nn Nq Nr Ns Nv Nw Nx Ny Of Ok On Oy Oz Pb Pe Po Qb Qe) Lx(Et Hu Hv Hw Ih In Io Ip Iq It Iu Jg Jh Jn Lw Ly Lz Ma Mb Md Me
Mj Mk Mn Mp Mr Mt Mu Mv Mw Mx My Na Nb Nc Nf Ni Nk Nn Nr Ns Nt Nu Nv Nw Ok On Oy Oz Pb Pe Po Pz Qc Qe) On(Hq Hu Hv Ih Ii
In Io Ip Iq Is It Iv Jh Jm Jn Lj Lw Ly Mc Mf Mh Mi Mk Mn Mq Mr Mt Mv Mw Mx Nb Nc Nj Nk Nl Nq Nr Ns Nu Nv Ny Oh Oi Ok Oy Oz Pb
Pc Pz Qb Qc) Mt(Hu In Io Is Jh Jm Jt Lu Lw Lz Mc Md Mg Mh Mj Mk Ml Mn Mp Mq Mr Ms Mu Mv Mw My Nb Nd Ng Nl Nm Nn Nq Nr Ns
Nt Ny Of Oh Oi Pb Pc Pe Po Qb Qe) Is(Hq Hu Hv Ih It Iv Jg Jh Jk Jm Jq Lw Ly Ma Mf Mi Mq Mu Mv Mx My Na Nc Nd Nf Ni Nj Nk Nm Nn
Nq Ns Nw Ny Ok Pc Pd Pf Po Pz Qb) Qe(Hv Iq It Jg Jh Jm Js Lu Lw Ma Mf Mg Ml Me Mf Mh Mi Mj Ml Mn Mp Mq Ms Mu Mv Mz Na Nc Nd Ne Ng Ni Nj
Nn Nq Ns Nw Nx Of Oh Oi Pa Pc Pd Po Pz) Mv(Hv Ip Jh Jm Jn Jt Lu Ly Me Mf Mh Mi Mj Ml Mn Mp Mq Mw Mx Nb Nc Nd Nh Nj Nk Nm
Nn Nr Nu Nx Pd Pe Po Pz Qb Qd) Ms(Hu Hv Ii Ip Iu Iv Jj Jk Jn Li Lu Lz Ma Mj Mk Mn Mp Mr Mw My Nb Nd Nf Nq Nr Nu Nv Oe Og Om
Oy Pb Qb Qd) Mi(Et Hv It Iu Iv Ji Lw Mc Md Mf Mh Mj Mk Mn Mp Mq Mr Mw Na Nb Nd Ni Nt Nu Ny Of Oy Pb Pe Pf Qb Qd) Pa(Et Fp In
Io Ip Jk Jq Mc Md Me Mj Mk Ml Mp Mr Mw Nd Nh Nl No Nu Nv Nw Ok Om Oz Pb Pd Qb Qc Qd) Qb(Hu Hv Jg Jh Ji Jm Jn Ly Ma Mf Mg
Mn Mq Mu My Nc Ne Ng Ni Nj Nm Nq Nw Ny Of Oh Oi Pc Pz) Mz(Hr Hw Ii In Io Ip Li Lz Md Me Mh Mk Mr Mw Nb Nh Nl No Nr Nt Nu
Nv Nw Om Oy Pb Qc Qd) Jj(Et Iq Jo Jq Mb Mc Md Mg Mh Ml Mm Mq Na Ng Ni Nl Nm Ns Nu Nx Ny Of Oh Oi Oz Pd Pz Qc) Pe(Hq Ii Io Iq
Jg Jh Js Li Lj Ma Mb Mf Mh Mq Mx Na Nf Ng Nj Nm Nq Nu Ny Of Oh Pc Pd) Lu(Hu Hv Iv Jg Ji Jk Jn Ma Mf Mg Mm Mn Mu Mx My Nd Ne
Nh Nj Nk Nq Nv Oi Om Qd) Jo(Hv Io Iu Iv Jh Jt Li Ma Mk Mp Mr Mu Mw My Nd Nf Nn Nq Nr Nu Ok Om Oy Pb) Mu(Ip It Jn Jt Ly Mb Me
Mf Mg Mj Mk Nc Ng Nj Nk Nr Oi Pb Pc Pd) Oe(Et Fp Hu Io It Js Jt Li Lj Lz Mx Nc Nj Nl Nt Ny Og Oy Pb Qc) Nw(Iq Iu Jk Jq Js Ly Mf Mg
Nc Ne Nf Nh Nj Nk Nm Of Oh Oi Pz) Po(Hr Iq Iu Jh Jn Ly Ma Mf Mg Na Nf Nk Nl Nm Of Oi Pf Pz) Ng(Ii Ip Iu Iv Jh Ji Jn Li Lw Ma Mj Mn

Figure 16 Continued

My Nb Nq Nv Og Pc) Og(Hq Hr Hw Io Ly Md Mf Ml Mm Mq Nf Nj Nk Oh Pz) Oi(Hu Hv Ip Iv Jg Ji Ma Mn Mw Nn Nu Nv Qd) Ma(Hv Jk Ly Mg Mm Nc Nd Nj Nk Of Qd) Mp(Jh Js Mb Me Mf Mg Mm Na Nj Nm Nx) Nv(Iu Jr Js Mf Mg Mq Nd Nj Ns Nx Of) Jk(Iq Iu Jt Mg Mm Nc Nj Nl Of) Qd(Iq Jr Mm Nc Nj Nx Of Pc) Jg(Ly Mm Nc Nj Nx Of Oh Pz) Nn(Jn Ly Mb Me Nf Nj) Mj(Jh Lj Lw Na Nf Nl) Mn(Iu Jt Mg Mm Nj Of) Mw(Hq Js Mf Mm Mq Oh) Ji(Iu Jr Mg Mm Nx Oh) Lw(Hu Jn My Nj) Jh(In Mf Mq Nd) Jr(Hr Io Nh Om) Jt(Hv Iv Mx Ok) Jn(Iu Mm Pc) Mk(Hr Hw) Nd(Iv Nc) Nj(Nq Pc) Nx(Hv Om) Pd(Om Pf) NrHw NhaA IhIu

Unconstrained panels with 2 analytes, where 5.0E-2 >= 'AUC p-value' > 1.0E-2. Contains 1,460 panels of 6,786 total panels evaluated. : Nv(Et Fp Hq Hr Hu Hv Hw Ih Ii In Io Ip Iq Is It Iv Jg Jh Ji Jk Jm Jn Jq Li Lj Lw Ly Lz Ma Mb Mc Md Me Mh Mi Mj Mk Ml Mn Mp Mr Mt Mu Mv Mw Mx My Na Nc Ne Nf Nh Ni Nk Nl Nm Nn No Nq Nr Nt Nu Nw Ny Oh Ok Om Oy Oz Pb Pc Pd Pe Pf Po Pz Qb Qc Qd Qe) Ma(Et Fp Fr Hq Hr Hu Hw Ih Ii In Io Ip It Iu Iv Jg Jh Ji Jn Jq Js Jt Lh Li Lj Lw Lz Mb Mc Me Mf Mh Mi Mj Mk Ml Mn Mp Mq Mr Mt Mu Mv Mw Mx My Na Nb Ne Nf Nh Nl Nm Nn No Nq Nr Ns Nt Nu Nw Nx Oh Ok Om On Oy Pb Pc Pd Pf Pz Qc) Mn(Hq Hu Hv Hw Ih In Io Ip Iq Is Iv Jg Jh Ji Jk Jn Jq Js Li Lw Ly Mb Mc Md Mf Mh Mj Mk Ml Mp Mq Mr Mu Mw Mx My Nb Nc Nd Ne Nh Ni Nk Nm Nn No Nq Nr Ns Nw Nx Ny Oh Om Oy Pb Pc Pd Pe Pf Po Pz Qc Qd) Qd(Et Hu Hv Hw Ih Ip Ir Is It Iv Jg Jh Ji Jk Jm Jn Js Lh Li Lj Lw Lx Ly Mc Mf Mg Mj Mk Ml Mp Mq Mt Mu Mw My Na Nd Ne Ng Ni Nk Nm Nn No Nq Ns Nw Ny Oh Ok Om On Pb Pd Pe Pf Po Pz Qa Qb Qe) Lu(Et Fp Hq Hr Hw Ih Ii In Io Ip Iq It Iu Jh Jm Jo Jq Js Jt Li Lj Ly Lz Mb Mc Md Me Mh Mj Mk Ml Mq Mr Mw Na Nb Nc Nf Ni Nl Nm No Nr Ns Nt Nu Nx Ny Of Oh Oy Oz Pb Pd Pf Pz Qc) Qb(Et Fp Hq Hr Hw Ih Ii In Io Ip It Iv Jk Jq Js Li Lj Lw Lx Lz Mb Mc Md Me Mh Mj Mk Ml Mp Mr Mw Mx Na Nb Nd Nf Nh Nk Nl Nn No Nr Ns Nt Nu Ok Om Oy Oz Pb Pd Pe Pf Po Qa Qc Qe) Nw(Et Fp Hq Hu Hv Hw Ih Ii Ip It Iv Jg Jh Ji Jm Li Lj Lw Lz Mb Mc Md Me Mh Mi Mj Mk Mp Mq Mr Mt Mu Mv Mx My Na Nb Nd Ni Nl Nn No Nr Ns Nt Nu Ny Om On Oy Oz Pb Pf) Mp(Hq Hu Hv Ih Ip Is Iu Jg Jk Jn Jt Lh Lw Ly Mc Md Mh Mj Mk Ml Mq Mr Mu My Nb Nc Ni Nl Nq Nr Ns Of Oh Oi On Oz Pb Pc Pe Pf Po Qc) Mw(Fp Hu Hv Hw Ih In Ip Is It Jh Ji Jm Jn Jt Lw Ly Lz Mb Mc Md Mg Mh Mj Mk Ml Mp Mr Mu Mx My Na Nd Ne Ng Ni Nj Nl Nm Nn No Nq Nr Ns Nx Ny Of Oy Oz Pb Pd Pe Pf Po Qc) Qe(Et Fp Hq Hr Hu Hw Ih Ii In Io Ip Is Iv Ji Jk Jn Jq Li Lj Ly Lz Mb Mc Md Me Mh Mj Mk Mr Mx My Nb Nf Nh Nk Nl Nm No Nr Nt Nu Ny Ok Om Oy Oz Pb Pe Pf Qa Qc) Jh(Hq Hu Hv Hw Ih Ii Ip It Ji Jk Jm Jn Jt Lw Ly Lz Mb Mc Md Mg Mh Mi Mk Mm Mr Ms Mu Mx My Na Nb Nc Ne Nl Nm Nn Nq Nr Ns Nx Ny Of Oh Oi Oy Pb Pd Pf Qc) Po(Et Hq Hu Hv Ih In Io Ip It Iv Jg Ji Jk Lw Mc Md Me Mh Mi Mj Mk Ml Mp Mq Mr Mu My Nb Nc Nd Ne Ni Nr Ns Nt Nu Ny Ok On Oy Oz Pb Pe Qc) Mv(Et Fp Hq Hr Hw Ih Ii In Io Iq It Iu Iv Ji Jk Jq Js Li Lj Lw Lz Mb Mc Md Mk Mr Mu My Na Ne Nf Ni Nl Nt No Nq Ns Nt Ny Om Oy Oz Pb Pf) Mp(Hq Hu Hv Ih Ip Is Iu Jg Jk Jn Jt Lh Lw Ly Mc Md Mh Mj Mk Ml Mq Mr Mu My Nb Nc Ni Nl Nq Nr Ns Of Oh Oi On Oz Pb Pc Pe Pf) Mt(Et Fp Hr Hv Hw Ih Ii Ip Iq It Iu Iv Jg Ji Jk Jn Jq Li Lj Ly Mb Me Mi Mx Na Nc Nf Ni Nj Nk No Nu Ok Om Oy Oz Pf Pz Qc) Is(Et Fp Hr Hw Ii In Io Ip Ir Ji Jn Jr Li Lj Lx Lz Mb Mc Md Me Mh Mj Mk Ml Mr Nb Ne Nh Nl No Nr Nt Nu Om Oy Oz Pb Pe Qc) Jk(Et Fr Hu Hv Ip Iv Jg Ji Jm Jn Lh Lw Lx Mf Mi Mq Mu Nd Ne Ng Ni Nm Nn Nq Ns Nt Nu Nx Oh Oi Ok On Oy Pc Pe Pz Qc) Pe(Et Fp Hu Hv In Ip It Iv Ji Jm Lw Ly Lz Mc Md Me Mj Mk Ml Mr Mu My Nc Nd Nn No Nr Ns Nt Oi On Oy Oz Pb Pz Qc) Mu(Hq Hv Ih Ii In Iq Iu Iv Jm Js Lw Lz Mc Md Mh Mi Ml Mq Mr Mx Na Nb Nd Ni Nl Nq Nt Nu Ny Of On Pf Pz) Ji(Fr Hu Hv Iq Iv Jn Jq Js Lh Lx Ly Mf Mj Mq Mx Mv Nc Nd Ne Nf Nh Nj Nk Nm Nq Ns Ny Of Ok On Pc Pz) Mj(Hq Hu Hv Ip Iq It Jg Jn Jt Lz Mb Mf Mh Mq Mr Md Ni Nj Nn Nq Nu Nx Of Oh Oi Ok On Pb Pd Pf) Qa(Et Fp Hq Hr Ii In Io Ip Jq Lj Lz Mb Mc Md Me Mh Mx Na Nb Nf Nh Nl Nt Nu Ok Om Oy Oz Pf Qc) Hu(Et Fr Hv Ih Ip Iv Jn Jo Jt Ly Lz Mf Mg Ml Mq Mx My Nc Nd Ng Nj No Nq Nu Nx Ny Of Pb Pf) Nn(Hv Ih In Ip Iq Iv Jm Js Md Mf Mg Mi Mk Mq Nb Nc Nd Nh Ni Nk Nl Nr Ns Nu Of On Pc Pz) Ng(Et Hq Hv Hw Ih Io Lj Lz Me Mk Mr Mx Nc Nf Nj Nl No Nr Nu Oe Ok Om Oy Pb Qc) Nd(Et Hv Ih Ip Iu Jg Jn Jq Js Lh Lx Mb Md Mf My Ni Nk No Nq Ns Ny Ok On Qc) Oi(Et Ih Ii Io Iu Jn Li Lj Lw Ly Mr Ms My Nb Nc Nj No Nq Nr Nt Og Ok Om Pc) Nq(Hq Hv Ih In Ip Iv Jm Jn Js Jt Lw Ly Me Mf Mq Mx My Nc Ns Nu Qc) Ir(Et Hr Ii Io Ip Jq Ly Lz Mk Mr Mx My Nb Ne Nh Nr Nt Nu Om Oy) Ms(Et Hr Hw Ih Io It Jo Jq Js Jt Mf Mh Mx Nc Ni Nj Nk Nt Ok) Jo(Et Fp Hq Hr Ih In Jm Jn Js Lz Mx Nc Nj Nm Nt Oe Og Pz) Jg(Hv Ih Ip Iq Iu Iv Jn Jt Lh Mf Mx Ne Nk Nm Nu On Oy) Mi(Hq Hr Hw Ih Ii In Io Jm Lz Ml Mx Ne Nh Nl Ns Qc) My(Hq Hv Ip Iu Jt Lh Md Mf Mg Nc Nj Nk No Nu Of On) Oe(Hq Ly Mb Mf Mg Mh Mm Na Nf Nk Of Oh Oz Pd Pz) Pc(Hv Ih Iv Jq Jt Mg Mm Mx Nb Nc No Nx Of Om Pd) Og(In Iq Jm Mb Mc Mg Na Ne Ni Nm Ns Nx Oz Pd) Nj(Et Hv Ip Iv Jn Lx Lz Mf Mg Mx Nb No Om) Lh(Ih Io Iv Jm Jn Lj Lz Ne Ni No Nt Nu) Lw(Ih Jt Me Mg Mm Nb Nm Nx Of Oh Pd) Hv(Iq Iu Ly Mf Mg Mm Na Nc Ni Of Oh) On(Et Jq Lz Md Me Ml Ni No Om Qc) Lx(Hr Ii Iv Jq Li Ne Nh No Om) Nc(Et Ip Iv Jn Ne Nh Ni Nk Nl) Nu(Iq Jt Mf Na Ni Nm No Nx) Of(Ih Ip Iv Jn Li Mk No Om) Jt(Hw Ii Mk Mr Nb Nr Oy) Nx(Et Ip Iv Jn Lz Mx Ny) Mm(Et Ih Iv No Ok Om) Mf(Ip Iv Jn Ny Pf) Mg(Et Ip Iv Jn Om) Fr(Hr Jm Ni Qc) No(Ip Iq Js Pd) Nb(Hr Hw Na Nf) Iq(Iu Jn Mx) Pd(Ip Li Lz) Pf(Mq Ns Pz) Nm(Iu Jn) Mr(Hr Hw) NrHr MqNy NiNk HxOm IuIv JnOh Constrained panels with 3 analytes, where 1.0E-8 >= 'AUC p-value' > 0. Contains 2,641 panels of 260,130 total panels evaluated. : Lv{Jt(aA Fr Hx Ii Io Iq Ir Is Jg Jk Jl Jp Jr Lh Lx Ma Mb Mi Mj Mk Mn Mr Mu Mv My Mz Nb Nd Nn No Nq Nr Nw Om On Pa Pc Pe Pg Po Qa) Jo(aA Fr Hw Hx Ih Ii Io Iq Ir Jk Jl Jp Jr Lh Li Lu Mb Mf Mi Mj Mk Mq Mr Mu Mz Nb Nd Nn No Nr Nx Oe Og On Pa Pb Pc Pe Pg Po) Mg(aA Fr Hx Jg Jk Jl Jp Jr Lh Lu Lw Lx Mb Mf Mi Mk Mr Mu Mv Mw My Mz Nb Nd Nn Nq Nr Nw Oe Og Om On Oy Pa Pb Pc Pe Pg Po) Nx(aA Fr Hx Io Iq Is Jj Jk Jl Jp Jr Lh Lu Mf Mi Mk Mq Mr Mu Mv Mw Mz Nb Nd Nn Nr Nw Oe Og On Pa Pc Pe Pg Po) Ng(aA Fr Hx Io Iq Jg Jk Jl Jp Lh Lu Lx Mi Mj Mk Mr Mv Mw Nb Nd Nn Nq Nr Oe Og Oy Pa Pb Pc Pe Pg) Ms(aA Fr Hx Io Jg Jl Jp Jr Mb Mi Mj Mk Mr Mu Mv Mw Mz Nb Nd Nn No Nr Nw On Oy Pa Pb Pc Pe) Mm(aA Fr Hx Ih Is Jh Jl Jp Jr Lh Lx Ma Mi Mu Mv Mw Mz Nn No Nw On Pa Pc Pe Pg Qb) Mq(aA Fr Hx Jg Jj Jl Jp Jr Lu Lw Mi Mu Mv Mz Nd Nn Nw Oe Og Oi Om On Pa Pc Pe) Oe(aA Fr Hx Io Iq Jj Jl Lu Mf Mi Mk Mr Mz Nd Nn Nr Nw On Pa Pb Pc Pe) Og(aA Fr Hx Iq Jj Jl Jr Lu Mf Mi Mk Mr Mz Nb Nn Nr Nw On Pa Pb Pc Pe) Pd(aA Hw Hx Lh Li Lu Lx Mi Mk Mr Nb Nf Nn Nr Om On Pa Pb Pc Pe Pg Po) Iu(aA Hx Ih Iq Ir Is Jl Jr Lh Mi Mj Mk Mr Mz Nb Nr Nw On Pa Pe) Pa(Fp Hq Ii Iq Jj Js Li Lu Mf Mh Na Nf Nt Oy Pe Pf Po) Jj(aA Hx Jk Jl Lu Mf Mi Mk Mr Nd Nn Nr Pc Pe Pg) Js(aA Hw In Ir Is Iv Jl Jr Lh Lu Mi Mz Om Pb Pe) aA(Ji Jq Li Me Mf Mx Na Nf Nh Nm Nt Of Ok) Jl(Et Ii Jq Li Lu Mf Nm Of Oh Oi Ok Pz) Mi(Hq Li Lu Lx Mf Ne Nh Nm Nq Nt) Mz(Jq Lu Mf Ml Nm Nn Oh Ok Pc) Hw(Hv Jn Jr Me Mf Ml Na Nm) Oi(Hx Io Jp Mk Mr Nn Nr Pc) Pc(Fp Li Mf Mx Na Nf Nt Pf) Lu(Hq Jp Ly Mf Ne Nf Nt) Fr(Et Li Nh Nm Of Ok) Jr(Is Iv Jn Jq Mf Ml) Nm(Lw No Nw Om On) Nt(Lh Lx Mk Mr Nr) Li(Hx Jp Lh No On) Nf(Lh Mr Nb On) Is(Jn Jq Ml Mx) Pc(Jh My Nq Ns) Na(Mk Mr Nr) Nc(Ne Nh Nl) Iv(Jn Ml Mx) Jp(Et Ok Pz) Nw(Ji Jq Ok) Of(Mu On Pg) Lx(Hq Ne) Nh(Mu Mv) NnNs McOm MfHx MjMx MlPb MwMy HqPg IrJq OkOn} Og{Jj(Fr Hu Hv Hx Ih Ii Ip Ir Is Iu Iv Ji Jk Jl Jp Jr Lh Lx Mi Mj Mk Mr Mt Mu Mz Nb Nn No Nr Nv Nw Om On Oy Pa Pc Pe Pg Po Qa Qb Qd Qe) Jr(Fr Hx Ii Is Jg Jk Jn Jp Js Lh Lu Lw Mi Mk Mr Mu Mv Nb Nj Nn Nr Om Pa Pb Pc Pe Pg) Pa(Fr Hq Iq Iu Jg Jl Jo Jp Js Jt Lx Mi Mv Mz Na Nf Ng Nj Nt On Pb Pc Pd Pe Pf Qb) Is(Fr Hx Ii Iq Ir Iu Jn Jo Js Jt Lh Lu Mk Ml Mr Mv Mx Nb Nr Nw Nx Oe Pb Pc Pe) Lh(Hq Iu Jo Jp Js Jt Mg Mj Mk Mm Mv Mz Nb Ne Ng Nj Nn Nq Nr Nt Nx Oe Pd) Nw(Ii Jn Jo Js Jt Lu Mj Mk Ml Mm Mr Ms Mt Mv Nb Nj Nr Nx Oi Pb Pd Pe) Mz(Fr Ii Jg Jk Lu Mj Mk Mr Ms Mu Mv Nb Nj Nr Oe Oy Pb Pc Pe Pg) Mi(Hq Hx Jo Jt Mg Mk Mr Ms Nb Nd Ng Nj Nq Nr Nt On Pb Pc Pd) Jp(Hx Ii Lu Lw Ly Mj Mk Mm Mr Mv Nb Nj Nr Om Pb Pe Pg Qb) Fr(Hx Ii Jo Jt Mg Mk Mr Ms Nb Nc Ng Nj Nr On Pb Pc Pe) On(Hr Iq Jl Jo Jt Mm Mq Ms Mv Nf Ng Nj Nx Oe Ok Pd) Hx(Jg Jo Lw Mk Mr Mv Nj Nn Nr Oe Pb Pc Pe) Qb(Jg Lu Mj Mk Mr Mu

Figure 16 Continued

Nb Nn No Nr Pe Po) Jl(aA Iq Jt Mk Mm Nj Nn Nr Ny Oh Pb Pc) Pg(Hq Iu Jo Mg Mj Ng Nn Nr Nx Pb Pc Pd) Om(Jo Jt Lu Lx Mg Mj Mq Ms Ng Nn Pc) Ir(Ii Iq Iu Jg Jo Lu Lw Nn Oe Oy) Ms(Jg Ji Mk Mr Mu Nb No Nr Pb) Nj(aA Ii Mj Mu Nn No Pe Po Qd) Oe(Ii Iv Mk Nb No Nr Pb Pe) Lu(Ji Lx Mt No Qa Qd Qe) Mv(Mj Mk Nb Ng Nr Pb Pe) Mu(Mj Mk Mr Nb Nr Pb) Pc(aA Hu Jk Mj No Pe) Nn(Iv Mx Nr Oy Pe) Lx(Hq Mm Nt Pb) Jo(Iv Nv Pc Po) aA(Iq Js Jt Lw) Ng(Jg Nb Po) Qa(Mk Mr Nr) Iv(Jg Lw) Ji(Jk Mm) Pd(Pe Po) NoQe MgJg} Jt{Pe(aA Fr Ir Is Iu Ji Jj Jk Jl Jp Jr Lh Lu Lw Lx Ma Mi Mk Mp Mr Mt Mw Mz Nr Nv Nw Oe Om On Pa Pc Pf Pg Qa Qb Qd Qe) On(Fr Ir Is Iv Jk Jl Jp Jr Lh Lu Lx Ma Mi Mj Mk Mm Mq Mr Ms Mt Mz Nf Nj Nr Nw Nx Oe Oh Pa Pg Qa Qb Qe) Pa(aA Fr Hq Iq Is Jg Jh Ji Jj Jl Jp Jr Lh Lw Lx Mh Mi Mk Mr Mu Mz Nf Nj Nn Nr Pc Pf Pg Qa Qb Qd) Lh(aA Fr Ir Is Iu Iv Jj Jl Jp Jr Lw Lx Mf Mi Mj Mk Mm Mr Ms Mz Ne Nf Ng Nn Nr Oe Pc Pd Qd) Is(Fr Hu Hx Ii Jg Jl Jp Lu Lw Mi Mj Mk Mr Ms Mv Mx Mz Nb Nn Nr Nw Oe Pc Pg Po) Jl(aA Hu Hx Jj Jp Lu Lw Mi Mj Mk Mm Mr Ms Mz Nb Nj Nr Nw Oe Oh Om Pc Pg Qd) Mz(aA Fr Hx Ii Ir Jg Jk Lu Lw Mi Mj Mk Mr Mu Mv Nb Nn Nr Nw Oy Pc Pg) Pg(aA Fr Hq Ir Iv Jj Jp Jr Lw Mg Mj Mk Mr Ng No Nr Nw Pc Pd Qa Qd) Ir(Fr Hx Ii Jg Ji Jp Jr Lw Mj Mk Mn Mr Mu Nb Nn Nr Pc Po) Qd(Fr Hx Ii Jg Lw Mj Mk Mr Nb Nn No Nr Nw Om Oy Pc Po) Hx(aA Fr Ji Jp Jr Lw Lx Ma Mi Mt Mu Mv Nn Om Pc) Qa(Fr Ii Jg Mj Mk Mr Nb No Nr Nw Pc Po) Qb(Fr Ii Lw Mj Mk Mr Nb No Nr Nw Pc Po) Lx(Hq Ii Mj Mk Mr Nb No Nr Nw Pc Po) Qe(Jg Lw Mj Mk Nb Nn No Nw Pc Po) Nw(Jk Mj Mk Mr Ms Nr Oe Pc) Mi(aA Hq Jp Jr Mj Nb Nr) Nv(Lw Mj Mk Mr No Nr Pc) Fr(aA Ih Jn Jr Ly) Jk(Jj Om Pc Po) Jr(Lw Nn Om Pc) Mj(Jp Lw Mt) Po(Jp Mt) aA(Lw Pc) NoMt IiJp} Oe{Jj(Fr Hx Ih Ii Ir Is Iu Iv Jk Jl Jr Lh Lx Mj Mk Mr Mt My Mz Nb No Nr Nv Nw On Oy Pa Pc Pe Pg Po Qa Qb Qd Qe) Pa(aA Fr Hq Hx Iq Is Jg Jl Jo Jp Jr Js Lx Mi Mk Mr Mu Mv Mz Na Nf Ng Nj Nn Nr Nw On Pc Pd Pe Pf Qa Qb) Pc(aA Fr Hx Ir Is Jl Jn Jp Jr Lh Lu Lx Mi Ms Mt Mz Pc Pg Po Qa Qb Qd Qe) Nr(Fr Hx Ir Is Jl Jo Jp Jr Lh Lx Mi Ms Mt Mu Mv Mz Nn On Pg Qa Qb Qe) Mk(Fr Hx Ir Is Jl Jp Jr Lh Lx Mi Mt Mu Mv Mz On Pg Qa Qb Qe) Lu(Hx Ir Is Jg Jl Jp Jr Lh Lw Lx Mz Nn Nw Om Pg Po Qa Qb) Hx(Fr Iq Jg Jo Jp Mf Mi Mj Ml Mr Ms Mu Mv Nn Nw Pe) Pg(Hq Ii Is Jo Jp Jr Mg Mj Mq Mr Mz Ng Nn Nw Nx Pd) Jp(Ii Ir Is Jr Lh Lw Ly Mj Mr Nb No Pe Po Qb) Mz(Fr Ii Jg Jk Mj Mr Ms Mv Nb Nn On Oy Pe) Jr(Fr Ii Jg Jn Js Ml Mr Mu Mv Nb Nn Oy Pe) Lh(Hq Iu Jo Js Mg Mj Mm Mr Nf Ng Nn Nw Pd) Is(Ir Iu Jg Jo Js Mr Ms Mx Nb Nn Nx) On(Fr Jl Jo Mi Ms Nf Ng Nx Ok Pd) Pe(Fr Jo Lx Mv Na Nf Nw Pd Qb) Ms(aA Jg Ji Jl Mu No Nw Om) Mr(Fr Jl Lx Mt Qa Qb Qe) Ir(Ii Iq Iu Jg Jo Nn Oy) Mj(Jo Lx Mt Mu Mv Nw) Nb(Fr Jo Lx Mi Mv) Jl(aA Mm Mq Nx) Nw(Ii Js Mm Nx) Po(Jo Pd) Fr(Mg Ng) Lx(Hq Mm) Ii(Jo Qa) Jg(Mg Ng) NoQa LyMi} Jo{Pe(Fp Fr Ii Is Jj Jk Jl Jr Js Lh Lu Lw Lx Ma Mh Mi Mk Mr Ms Mv Mz Nb Nf Nj Nr Nv On Pa Pc Pg Qa Qb Qd) Lh(aA Hw Is Iv Jk Jl Jr Lu Lw Ly Mi Mj Mk Ml Mm Mr Ms Mz Nb Ne Nf Ng Nr Nx Oh On Pa Pc Pd Pg) Pa(aA Fr Hq Hu Iq Jg Jl Jp Js Lu Lw Ly Mh Mi Mk Ml Mr Ms Mv Nf Ng Nj Nn On Pc Pf Pg) Jl(aA Hu Hw Hx Lu Lw Ly Mi Mj Mk Mr Mt Mx Nb Nh Nj Nr On Pc Pg) Mz(Hw Ii Jk Lu Lw Mj Mk Mr Mv Nb Nn Nr On Oy Pc Pg Po) Ir(Ii Jg Jk Lw Mj Mk Mr Mu Mv Nb Nn Nr Om Oy Pc Po) Is(Ii Jk Lu Lw Mj Mk Mr Ms Nb Nj Nn Nr Nv Pc Pg Po) Qb(Fr Ii Jg Lu Lw Mj Mk Mr Nb No Nr Om On Pc Po) Qd(Ii Jg Lw Lx Mk Mr Nb Nn No Nr Om On Oy Pc Po) Qa(Ii Jg Lw Lx Mj Mk Mr Nb No Nr On Oy Pc Po) Jk(Ii Ip Lw Lx Mi Mj Mk Mr Nb Nr Nw On Pc Po) On(Hx Jr Mk Mm Mq Mr Nf Nm Nr Oh Ok Pg) Pg(aA Fr Jj Jp Lw Mi Mj Mk Mr Nr Pc) Lx(Ii Jr Mj Mk Mr Mt Nb No Nr Qc) Hx(aA Fr Jp Lw Mi Ms Mu Mv Nn Pc) Nv(Ii Lw Mj Mk Mr Nr Pc) Qe(Ii Lw Nb No Om Pc) Mi(aA Hu Ly Ms Nj) Mt(Ii Mk Mr No Nr) Jr(Fr Jg Lw Pc Po) Pc(aA Ih Mj) Lw(Hu Mj) PoPd FrLy MsNw} Jl{Pa(Fp Ii Iq Iu Jj Js Li Mg Mm Ms Ng Nm Nn Nv Nx Ny Of Oh Oi Ok Oy Pd Pf Pz) Ng(Hu Jk Lh Lu Mi Mk Mr Nb Nj Nn Nr On Oy Pb Pc Pe Pg) Ms(aA Iu Jj Lu Mi Mk Mm Mr Nb Nr Nx Ny Oh On Oy Pc) Jj(aA Hu Jk Lu Mi Mm Mx Nh Nj Nx Oh Ok Pg) Nx(aA Iq Iu Jp Lu Lw Ly Mi Mm Om Pc Pg) Ok(aA Jp Lh Mi Mj Mk Mr Nr Nw On Pe) aA(Iq Iu Jq Js Mm Nn Ny Oh Oi Pz) Mi(Iq Iu Js Mg Mm Nj Ny Oh Pd) Pg(Ii Mg Nn Nv Ny Of Oi Pz) Lu(Iu Mg Nj Nq Of Oh Oi) Iq(Jp Mr Ne Nh Oi On Pe) Pd(Lx Mk Mr Nr On Pb Pe) Jp(Mm Nm Nn Ny Oh Pz) Mg(Lh Lw Mx On Pc) Iu(Hu Nh Nj Oh) Js(Is Jr Lx Pc) Of(Fr Oh Pc) Oi(Mm Nj Pc) Pz(Pc Pe) Jq(Nw Om) FrNn MqNj JnJr PePf} Jj{Jk(Ih Ir Is Iv Jp Jr Mg Mi Mk Mr Mt Mz Ng Nr Nw On Pc Pe Qa Qb Qd) Lu(Hx Ir Is Jr Lh Lx Mj Mt Mz Pa Pe Qa Qb Qd Qe) Mz(Hu Ii Ly Mj Mk Mr Ms Mv Nj Nr On Oy Pc Pe) Qb(Hu Ii Lh Ly Mj Mk Mr Nb Nn Nr On Pc Pe Po) Pa(aA Hu Iq Jn Js Ly Ml Nf Nj Pd Pe) Pc(Fp Js Mf Mk Ml Mx Nf Pc Pf) Ms(Fr Hx Is Ji Mi Mt Nw Om) Pg(aA Mg Mi Mq Ng Nx Pd) Ly(aA Fr Ir Ml Nd Nq) Qa(Ii Mk Mr Nr Oy Pc) Hx(Fr Jr Ml Nv Nj) Lh(Mm Mq Nx Ok Pd) Jr(Hu Jn Js Nj) On(Mm Nf Nx) Nj(aA My) Qd(Oy Pc) LxMm MlIn NcNe} Pa{Js(Fr Hr Jg Ji Jp Jr Ma Mi Mv Mz Nw Pc Pf Qa) Iq(aA Fr Hq Lu Mf Mi Ms Nf Oy Pd Pe Pf) Fr(Iu Mm Ms Ng Nj Nx Of Oh Pf Pz) Nj(aA Iu Jp Mi Mm Nx Oi Pc Pf) Ms(aA Iu Jg Jp Mi Mv Oy Pf) Mm(aA Jp Lh Mz Nw On) Ng(aA Hr Hu Jp Lu Mv) Iu(aA Lu Mi Pe Pf) Jp(Li Nx Pe Pf) Mi(Nx Pe Pf) Mv(Hq Pd Pe) Mz(Nn Oh Pf) aA(Oh Pf) NnNx NaHr HqPc IiPg JrPe} Ms{Fr(Hx Is Jr Ly Mg Mj Mk Mr Mz Nb Ng Nr Oi On Oy Pc Pe Qb) Mi(aA Hq Jp Js Mg Mk Mr Ne Nr On Oy Pc) Mu(Hx Jp Jr Mj Mk Mr Mz Nb Nr Oi Pe) Jr(Jg Jk Jp Js Lw Mv Mw Nn On Pc) Mv(Hx Jp Mz Nb Nr Pe) Lh(Hq Iu Jp Mm Ng Nw) Jg(Hx Mg Mz Ng Oi) Mz(Nn Nx Oi) Nw(Lu Nx) MmOn PcaA} Ng{Fr(Hu Hx Ii Jk Lu Ly Mi Mk Mr Nb Oy Pb Pc Pg) Mv(Lu Lx Ly Mi Mk Nb Nr Oy Pb Pe) Lu(Jp Lh Ma Mi Mz Nr Nw Pa Po) Hu(Jg Lw Mi Nn Pc) aA(Jk Ly Pc Pg) Mi(Jr Ly Nj) Lh(Js Mm Nx) Jp(Jk Pg) Jr(On Pc) MmOn NxPg} Nx{Mz(Fr Is Jk Jp Jr Lw Mi Nj Nn On Pg) Pg(aA Is Iu Jp Jr Lw Mg Om On Pd) Mi(aA Hx Ii Ly Nb On Oy Pe) On(Jp Jr Mq Nf Ok Om) Is(Iq Iu Jp) Lw(aA Jr) FrJr LxHq IqPc QbJp PcaA} Fr{Mm(Hx Ir Is Jr Lh Mi Mz Pe Qb) Jr(Js Li Nj Oh Oi) Pg(Ii Mg Of Pf) Ly(Mg Of Pd) Mz(Nn Oh Ok) Pz(Hx Is Qb) Nj(Mg Oi) Qb(Nn Oh) LxPd HxOf IsOh PePf} Jr{Js(aA Is Jp Lh Lx Mi Mj Mv Mz Nj Nn Nw On Pc Pe Pg Po) Mi(Jn Pd) Pc(Lu Nf) LxPd MgJg MmOn MvOi IqPg JnaA} Mm{Mz(Lh Lx Mi Mv Nn On Pc Pg Qb) Lh(Iu Mg Mi Oi) On(Iq Mg Nj Oi) Lx(Lw Nn Pc) PgaA} Lu{Iu(Ir Is Pe Pg Qa) Mz(Js Oi Pc) Pg(Mg Oi Pd) Mi(Mg Pd) On(Nf Of) IqQb IsOi} aA{Pg(Ii Iq Iu Js Mg Oh Pd Pf) Iu(Ly Nj) Pc(Nf Oi) NmLw NqMu MiPd NhIq} Mi{Js(Hx In Ly Mz Pg Qa) Mg(Ly Pg) Nj(Nh Pd) NmOn MzJq HxIq PdPg} Lh{MgPc Nflu IiPg IqPd} Mv{Pd(Lx On) MzOh} Nj{PoPd MzOi} HrJsPe Constrained panels with 3 analytes, where 1.0E-7 >= 'AUC p-value' > 1.0E-8. Contains 631 panels of 260,130 total panels evaluated. :

Og{Lw(Hu Lh Lu Mj Mu Mv Qa Qb Qe) Ii(Iv Jo Ms Mu Mv Om Pe Qa Qb) Nj(Hv Mk Mr Mv Nb Nd Nr Pb) Lu(Et Jg Jj Jn Ma Mn Pc) Pb(Hu Lh Mj Om Pe Qa Qb) Jj(Jg Jn Mv Mw Nt Nu) Pc(Lh Ms Mv My Nb Qb) Jo(Ji Mk Mr Nr Qe) Nn(Mj Mk Mr) No(Jk Js Jt) Lx(Nd Ne Pd) Oe(Jg Mr Qd) Mj(Mf Mk) Mv(Iv Mr) Jt(Mz Pg) Lh(Jg Nd) Om(Nr Nx) Oy(Ms Qd) PoMg MpHq MqJi IpJk} Oe{Ii(Jg Lx Ma Mi Ms Mt Mv Qb Qe) Lu(Ji Jk Mn Mp Mt Qd Qe) Nb(Ms Mu Ng Nn Nw Qb Qe) Mk(Jo Ms Nn Nw Pe Qd) Mr(Jo Mi Ms Mu Mv Nw) Jg(Jj Pe Qa Qb Qd Qe) Jj(Hu Ip Mn Nu Om) Nn(Iv Jp Mv Qd) Nr(Ma Nw Pe Qd) Mj(Mf Nv Qb Qe) No(Lx Mt Qb) Mv(Is Nw Pc) Nd(Iv Mi Pa) Mu(Ir Pc) Lh(Ne Nx) Nw(Mt Qb) LwHu LxPd MiJs MmJi MsOy IsJr JkPc} Jr{Js(Hw Hx Iv Mk Mq Mr Nb No Nr Ns Pb) Jt(Ii Jk Jp Mj Mk Mr Mu Mv Mz Nb Nr) Jj(Fr Ii Lh Mk On Oy Pc Pe Po) Jo(Hw Ii Jk Mj Mv Nn Nr) Ng(Jg Jk Lx Mu Nn) Nj(Jn Mf Nn Pc) Oi(Jp Lu Mu Pg) Pd(Mp On Pg Po) Iq(Fr Hx Lh) Oh(Lh Mz On) Ms(Jn Pa) Iu(Fr Pg) Nx(Jp Pc) MaMm MgMv IiPg LiPa} Ms{Mv(Is Mg Mj Mk Mr Ng Nw Oi Po Qb) Mz(Lw Mk Mr Nb Nr On Oy Pa Pc Pe) Jp(Hx Ir Is Nw On Pe Pg Qb) Mu(Ii Ir Is Lw Mg On Oy) Pa(Lw Nn On Pc Pe) Jg(Jo Lu Pe Pg) Jj(Ii Mp On) Lh(Js Pc Pd) Lw(Hu Mj) Is(Iu Oi) Ji(Jo Jt) On(Nf Pd) Pc(Hu Mj) LuHx MmNw} Jt{Jp(Lx Mk Mr Mz Nb Nr Pc Qb) Jk(Ji Lw Mj Mk Mr Nb Nr) Mi(Fr Iv Mk Mr Pc) Mt(Mk Mr Nb Nr Pc) Qe(Ii Jo Mr Nr Om) Pe(Hx Mv Nf Nn Nq) Fr(Mj Nb Nr) Hx(Jg Ml No) Ir(Mv Om Oy) Nw(Iv Mm Nj) Po(Ji Ma) Lx(Jo Om) LwQa MuQd MvOn QbJo LhNx} Ng{Mv(Hx Ii Jk Lh Mj Mr On Pg Po) Jp(Hu Hx Lh Ly Mi Oy Pe) Lu(Is Mt Pc Qa Qb) Lh(Mf Mx Nf Pd Pg) Fr(Jl Nj Nr) Jg(Hx Ly Pg) Pc(Hx Mj My) Mi(aA Pg) MaPa MxJl MzJk IuPg} Jo{Jk(Hw Iv Ji No Om Qa) Hx(Is Mj Mk Nj Pe) Fr(Ii

Lh Mj On) Qa(Hw Lu Nn Om) Po(Hu Ma Nj) Mi(Ii Lu On) Nn(Lh Qb) Lx(Hq Mn) Ma(Ii Mj) Mv(On Qb) Jp(Ir Pe) MjMn MlPe HwIs}
Nx{Nw(Hw Js Lw Mj Mx Oh On Pc) On(Fr Hx Is Lu Of Pa) Mi(Hq Mk Mr Nr Pc) Pa(aA Is Ji Mu) Fr(Hx Pe Pg) Mz(Jg Mu Pc) PoOm NnIs
HxJp IuLh JiPg} Pa{Oy(Fr Iu Lu Nj Pc) Nf(aA Jl Js Pc) Pe(Fr Hq Hr Jl) Nn(Jp Js Nj) Fr(Mg Pd) Lu(Nj Pf) Na(Ii Jl) Hq(aA Jl) Jp(Mx Pz) LxJs}
Jj{Mj(Hu Ii Jk Mt Pc) Ir(Ii Nn Oy Pc) Lh(Mg Mk Nf Pc) Nq(Hu Nj) Lu(Ii Nv) Ly(Ma Mv) PoPd MtIi NaPe NdNj IsPc OkOn} Pd{Jl(aA Hw Lh
Li Mj Pg Po) On(Fr Mz Nj Pg) Lx(Mz Nj Pg) Fr(Nr Po) Lu(Mp Mz) Mi(Hx Ly) Lh(Iu Pg) NnaA MvPe} Mz{Mm(Is Jp Mj Mk Mr Nj Nr Pe)
Js(Is Lh Lx) Lu(Ml Nf) Nj(Fr Jp) Oh(Pc Pg) HuOi IiPg IqLh} Jl{Js(Iv Jp Lh Mj Mr No Nr Pb) Ne(Nc Nj) Nh(Lu Nj) FrMg NnOi} Oi{Lu(Hx Jp
Nn Nw Pc Qa Qb) Hx(Fr Iq Mv) Hu(Lw Nn) LyJp} Mg{Pg(Jg Jp Mv) Fr(Hx Mi) LyMv HuPc HxJg IqLh JkJp} Mi{Nj(Hq Lu Nt Pc) NmLw
NcNe JqaA} Fr{Iu(Hx Ir Qb) Nc(Ne Nh) OfPe} Js{Qa(Lh Lx) InaA IsPg NwPe} Lu{PoNf LwHx Iqls IuLh} Mm{LwMt MaHx JpPg OfOn}
aA{LwJi NdNj NfPg} NdNjJp IqQbLh Constrained panels with 3 analytes, where 1.0E-6 >= 'AUC p-value' > 1.0E-7. Contains 765 panels of 260,130 total panels evaluated. : Jo{Mi(Hw Mj Mk Mr Nb Nr Oy Pc) Fr(Hw Is Mk Mr Nb Nj Nr) Jp(Hw Jk Jr Lh On Po Qb) Lu(Hx Ir Lx Nv Po Qe) Og(Hw Jk Jt Mj Nb Pb) Mv(Ii Is Lh Mj Po) Nj(aA Lh Mz Nd On) Jr(Mk Mr Mu Nb Om) Oe(Iv Nv Oy Qe) On(Hw Ji Mj Ms) Ly(aA Ir Mz) Ma(Nb Nr Qb) Hx(Mr No Nr) Jk(Jt Nn Qd) Lh(Hq Nq Nt) Pe(Mu Nn Pf) Hu(Is Mz) Hw(Po Qb) Ih(Jg Mj) Jt(Mt Nv) MuQd MxIs NbNw IqIr} Ms{Jp(Ii Lw Ly Mj Mk Mr Nb Nn No Nr Oy Pc Po) Mv(Ii Ir Ji Lw Nn No On Oy Pc) Jg(Ii Is Jj Mj Nn No Nw Po) Jr(Ii Mk Mr Nb No Nr Oy Pe) Lh(Mj Mk Mr Nb Ne Nr Nx Oi) Mz(Ii Mj Mm No Pg) Nn(Hx Ir Mu Qd) Ji(Jk Lu Mm Nx) On(Mq Nx Ok Pz) Hx(Lw Oi Pc) Jj(Nb No Oy) Pa(Lx Mk Ni) Mu(Ng No) Iu(Pg Qd) Om(Jt Oi) Pd(Pg Po) NtMi LwJn LxHq MyPc NvOg} Ng{Jp(Ii Lx Mk Mr Mv Nb Nr On Pb Pc Po) Pg(Jk Js Mk Mr Mu Nb Nr On Oy Pc Pe) Lh(Fr Hv Ir Jn Jr Mq Na Nj Ny) Lu(Hx Ir Jg Mp Mu Mw Nw Pe) Mz(Lx Mk Mv On Oy Pc Pe) Pc(Fr Jk Lx Oe Og Pa) Jr(Mk Mr Oy Pb Pe) Hu(Lx On Pb Pe) Hx(Iq Mu Nn On) Og(Ii Mk Mu Oy) Mv(Iu Lw Oe) Jg(Jk Jl Pe) Pa(Na Nf) FrIu NnMy LxNj MaOy NhJl OkOn} Oe{Lu(Hv Ii Ip Iv Jj Jn Ma Mj No Nu Nv Oy) Nn(Ii Jj Lx Mj Mr Nj Pe Qa Qb Qe) Jj(Jn Jp Mu Mv Mw Nq Nt) No(Jk Mj Mv Pc Qd Qe) Mj(Hu Ih Jg Jk Pc) Lw(Iv Mt Mv Qb) Ii(Mu Pc Pe Qd) Nt(Lh Mi Pa) Lx(Mu Nd Og) Qb(Mv Og Po) Nw(Jg Jn Pc) Nr(Jg Jk) Mi(Hq Ne) Is(Jn Ml) Qe(Mu Og) Pc(Iv Nc) PoMg MaMr MmJp MpHq MvIr MzJt NdHu QdOy JiJk NxOm} Jt{Jp(Fr Hw Iu Iv Jk Lw No Nu Nw Og Qa Qd) Fr(Hw Iv Lw Mk Mr No Pc) Lx(Hw Ir Iv Jr Lw) Mj(Hx Ji Ma No Om) Nn(Mn Po Qa Qb) Ii(Jk Ma Mt No) Ir(Iq Jk Ma Nq) Is(Jn Jr Js Ml) Mz(Hu Nj Qd) Nw(Lu Ml Mt) Om(Nr Qa Qb) No(Jk Mp) Mu(Pe Qe) Mv(Po Qd) Lh(Hq Nq) Pc(Ih Jn) EtJk LwMt MaNb NdIv QdJr JjNv OgPe} Jr{Iq(Jp Mv Nd On Pe Po) Jn(Is Lw Mv Mz Nn Pg) Oi(Hx Jg Nn Nw On Pc) Iu(Hx Jj Jk Mv Nj) Nx(Hx Jg Lx Mu Nw) Jj(Mr Nb Nn Nr) Pd(Lh Li Nw Om) Nf(Lh On Pe) Lu(Jp Js) Lw(Mf Mq) Mu(My Ns) Mx(Is Pa) Nw(Og Oh) NtLx MgPc MlMv MmMt NaPa NdNj} Pd{Pg(Fr Iu Jp Mj Mk Mr Nr Pa Pb Po) Fr(Hw Hx Mj Mk Mr Nb Pb Pe) Mi(Hu Jp Mv Nc Pa) Lx(Hx Jj Jp Pa) Po(aA Jp Mz) On(Jj Jp Lu) Mp(Hu Og) Jl(Nw Om) Pa(Jp Pc) MzLh JjPe} Nx{Mz(Hu Mk Mr Mv Nr Om Pa Pe) Nw(Hx Is Jn Lh Mm Mt Pg) Nn(Hx Ir Pe Qa Qb Qd) Fr(Ii Is Ly Qb) Jp(Ii Ir Ly) On(Mm Mu Nj) Lh(Mm Pg) Pc(Om Pa) NrPg LwIs MiNj HxaA JiOg} Og{Mj(Hu Ih Jg Jk Lu Nb) Nn(Ii Nb No Oi Pb) Jj(Lw Ma Nq Pb) No(Jg Mc Ml) Jk(Iu Lw Pb) Mg(Lx Pc) Jg(Mr Nr) Nw(Mx Oh) LuIp LwHv MlIv MpNj MqOk NlPa} Fr{Mg(Ii Lh Nb On Pb Pc Pe) Oi(Mk Mr Nr Pa Pc Pe) Hx(Iq Nf Nj) Mm(Jp Nw) Iq(Mz Qb) Jl(Nj Ny) LyIu HqPa JsPe OyPg} Jj{Nj(Lh Lx Mi Mj On Pe Po) Mt(Mk Mr Nb Nr Oy) Ih(Lu Mj Oy Pc) Jp(In Lu Ly) My(Lu Nc) NoLy NtLh MqOn MxIs} Pa{Js(aA Hq Lu Mu Qb) Nj(Ne Ni Nr) Jl(Mx Nr Nt) Pe(aA Mz Nf) Mg(Jg Mv) MxNf NaOy HqHx IiOn IsOh} Oi{Mv(Jp Lu Mj Mz Nb Nr On Pe) Jp(Hx Jk Nj Pg) Lu(Jg Lx) Iq(Ir Is) LyMz NjHx HuPc IuLh} Mg{Mv(Hx Jp Lx Mi Mj Mp Mz Nb) Mi(Lh Pc) Mz(Jg Lu) Jp(Hx Ly) Pg(Iu Mu) LwHu} Jl{Nt(Lx Mi Pe) Nf(Lh On Pc) Js(Nw Om Pg) Mx(aA Pe) NqMi NrNa MkOf NcNl} Mm{Jp(Ir Lh Lx Qa Qb) Lx(Hx Mu) Is(Iq Mv) Jg(Qa Qe) MaIr MiNj QdPc} Lu{Nq(Mi Nn Pg) Nj(Mz Nd Nn) Lw(Ir Qb) Pc(Qa Qb) LxHq IqIr} Mz{Nj(Iu Mf Nn Pc) LyJp HxIq IsOh IuPg JsPe} aA{Mi(Hq Iu Js) Nn(Mt Mx) Ok(Lw Pg) NtPg HxJs} Iu{Nj(Hx Lh) Hu(Qa Qe) IrOn} Js{Mi(Jn Lx Nj Qb) LxPg} Pg{Ii(Hx Mq) MxHq JpOf} Nm{LwNw HrOn} Lx{NtNj MqHq} Ne{NcJp IqLh} HrPcPe HxIqLh Constrained panels with 3 analytes, where 1.0E-5 >= 'AUC p-value' > 1.0E-6. Contains 993 panels of 260,130 total panels evaluated. : Ng{Pa(Lh Lz Mf Mi Mk Mr Ms Mu Mx Mz Nj Oy Pb Pe Pg) Lh(Jg Me Mi Mk Mr Nm Nn Oy Pb Pc Pe) Hx(Ma Mi Mj Mk Mp Mr Nr Nw Oy Po) Lx(Lu Mk Mr Mt My Nb Nr Pb Pe) Mi(Mg Mj Mw My Nb Nr Oy Pe) Ma(Ii Mk Mr Nb Pb Pe) Mz(Ii Mr Mu Nb Pb Po) Hu(Mk Mr Nb Nq Oy Po) Mt(Mk Mr Nb Oy Pb) Lu(Jh On Qd Qe) Mv(Nj Nn Nw Pc) Pg(Ii Nn Nw Pb) Oe(Mk Oy Pb) On(Nf Nj Nm) Pc(Is Mu Qd) Ii(Jg Jr) Oy(Jj Nq) PoPd NnJp MmNv MsOm MwPb NbJr NjJg IsJs JkNw} Jt{No(Iv Ji Lw Ma Mk Mr Nb Nn Nr Oe Om Oy Pc) Ji(Ii Iv Mk Mr My Nb Nn Nr Og Pc) Om(Iv Jn Lu Lw Mk Mr Nn Oe Pc) Mj(Mn Mp Mu Mv Mw Nq Pe Po) Ma(Jo Jr Mk Mr Nr Nw) Mv(Ii Nb Nw Qa Qb Qe) Po(Mk Mr Mu Nb Nr) Mp(Iv Mk Mr Nb Nr) Ir(Hu Jh Mt My Nv) Mn(Hw Ii Nb Qb) Jg(Ih Jr Mi Ms) Mu(Ii Qa Qb) Hx(Mk Mr Nr) Iv(Jk Nn Nv) Pe(Et Jq Pd) Lx(Nn Qd) Mz(Ms Qa) Lh(Mg Nt) Pc(Jq Mx) FrJj NrMw LwHu MfQd NbOg NcNw JkOk JoOe PaPd} Jo{Mv(Hw Iv Lw Lx Ly Mk Mr Nb Nr Nw Og Pc) Hw(Ip Jg Ji Lx Mn Mp Mt Nw Oe Qe) Po(Ii Lw Mj Mk Mr Nb Nn Nr Pc) Jp(Ii Lx Ly Mj Mk Mr Nb Nr Pc) Og(Ip Jg Ok Oy Pc Qa Qb Qd) Ma(Hv Iv Lx Mr No Oy Pc) Lu(Fr Lw Mn Nw On Qd) Oe(Jg Ji Om Qa Qb Qd) Mj(Jg Ji Nn Nw Pe) Is(Ir Jn Jr Js) Hu(Ir Nw On) Ii(Jg Ji Nw) Fr(Iv Pc) Ly(Jg No) Mi(Hq Nt) Mn(Iu Nu) Ms(Nv Om) NnOn LxNe MuQb NjPc IhOy JhLi JsLh} Ms{Nw(Hx Is Jk Jn Js Mj Mk Mr Nb Nr Oi Oy Pc Pe Pg) Lx(Lw Mj Mk Mr Nb Nn Nr Oy Pb Pc Pe) Pg(Mj Mk Mr Nb Nn Nr On Pc) Ji(Ii Mj Mk Mr Nn Nr Oy) Lw(Ir Is Jk Lh Mt Og) Nn(Lh Nj Nr Oi On) Hx(Jr Mj Mk Mr Nr) Jg(Mk Mr Nb Nr Qb) Mt(Mj Mr Nb Og) Pa(Hq Na Nf Qb) Mp(Hq Mr Oe) Lh(Lu Nt Oy) Pc(Is Pe Qb) Oe(Mw Pb) Om(Lu Nx) NrJj MjJr MxIs QbOn QdOi} Nx{Jp(Lw Lx Mi Mj Nb Nj Nn Pc Pe Po) Is(Lu Mk Mr Mu Mv Nr Pc Pe) Jr(Hu Ip Ji Jk Lh Ma Nj Om) Lw(Hx Ir Om Pa Qa Qb Qd) On(Lh Lx Mv Nv Pe Qa Qb) Po(Hx Ir Nj Qa Qb) Fr(Mi Nb Nj Om Pc) Pa(Jg Lh Nw Om Pg) Hx(Jg Mu Nj Om) Lx(Mu Om Pc) Mz(Ii Nb Oy) Nw(Mk Nj Pe) Qb(Jg Mv) Pe(Mu Pg) NnNj MiOm JiOe JqPc} Pd{Pa(Hr Hw Lh Lw Ma Mk Mr Nn On Pb) Mz(Hw Li Mk Mr Nr Pb Pc Pe Pg) Lx(Hu Iv Ma Mt Nn Pc Qa) Mv(Hw Mj Mp Mr Nb Nr Pb) Pe(Iq Jp Lw Nn Pc Pg) Mi(Fr Jk Pb Pc Po) Hx(Li Lw Mp Nw On) Jr(Hw Mk Mr Nr Pb) Pg(Hw Li Mp Nw Oi) Fr(Lh Li) Jp(Hw Mr) Oe(Li Mp) PoJs NfOn} Mg{Mv(Lh Lw Nn Nr Oe On Oy Pb Pc Pe Po) Jp(Jg Lh Lw Lx Mu Nn On Pc Pe Po) Jg(Jj Lh Lu Lx Mj On Po) Pc(Lu Lx Mt Mz Oc Pa) Pg(Js Lh Lw Nn On) Fr(Mk Mr Nr Om) Lu(Is Mu Pa Po) Nn(Hx Jr Nj) Mi(Ma Pa) Mu(Hx Mz) Og(Nv Oy) MqOn MzJk NhJl HxIq OeOm} Nj{Jj(Fr Ii Ma Mk Mr Nb Nn Nr Nw Og Oy Pc) Nn(Hx Jp Lh Nd Oi) On(Mq Mz Nd Ok Pz) Iu(Is Mi Qd Qe) Jp(Hx Lh Pc Po) Og(Lu Ma My Nq) Lh(Mz Nd Pc) Pa(Hq Hr Js) Fr(Mi Pe) Lx(Jr Mi) LuJr MjMz MmNw NdOe NhaA HxPc} Oe{No(Ii Jg Js Lw Mc Mu Nn Oy) Lu(Et Mw Ok) Lx(Mi Ne Nt) Mf(Ji Qa Qd) Mj(Mk Ml Nb) Jg(Mi Mk Mr) Ml(Iv Nw) Mq(Nb Ok) Jj(Ji Mp) Jk(Iu Lw) Og(Nv Qa) Oy(Iv Jn) MaHv MuQb MvQe NbPc NcNd NlPa HxNy} Oi{Lu(Ir Ji Lh Ma Mt Mu Om On Qe) Mv(Ii Is Mk Mr Nn Nw Pc) Jr(Jk Lh Mk Mr Nb Nr Oy) Mz(Jg Jk Mu On Pc Pg) Jp(Ir Is Lh) Pc(Lx Og Pa) Hx(Jg Mu) NnaA IiJj OkOn} Jj{Lu(Ip Iv Jn Ma Mi Mv Nn Nu Nw On) Mv(Ii Is Mj On Pe) Fr(Lh Pe) Lx(Hq Ne) Ly(Jg Nn) Mj(Mf Mx) Nc(Nq Og) Is(Jn Js) NrNa MaIi JsLh} Iq{Jr(Jg Mj Mk Mr Nb Nr) Mz(Ir Mj Mv On Pe) Ir(Fr Hx Jp Lh) Qb(Jp Nw On Pe) On(Mq Pe Pg) Mi(aA Nt) Hx(Is Jp) Pe(Fp Mf) IsLh} Mm{Lx(Ji Mj Mk Mr Mv Nr Pe) Ma(Mt Pc Qb Qd Qe) Mv(Ir Qa Qd Qe) Jp(Hx Is Jr Pe) Qd(Jg Nn) LuNw LwNv MtHx IsPg} Iu{Ir(Jp Mk Mr Mv Nn Nr Nw Pc Pe Pg) Pe(Fr Jr Lx Qa) Qb(Hu Lh Mv) Lh(Nt On) MvHx IsPg QaNw JkJn} Js{Mz(Hx Mj Nr Pb Pg Po) Qa(Jp Mj Mr Nr Pb Pe) Mi(Ir Lu Qd) Pa(Ir Lh Na) Is(Jp Lx) MjNw InLh IvOg} Mi{Hq(Jl Jq Lu Nm Pg) Nt(aA Jr

Figure 16 Continued

Qe) Nv(Hw Mk Mr Ms) Mv(Mr Nn Nr) Nb(Is Ji Lx) Ma(Hv Qb) Mp(Nj Nu) Ji(Mm Nn) Jk(Ir Iv) PoQe NqMi IsJr} Pd{Mp(Hw Ii Ir Iv Jk Li Lw Lz Mj Nb Nn No Nw Om Pf Po Qa) Nw(Hw Ii Li Mj Mk Mq Mr Nn Nr Pb Pe) Nr(Ir Is Ma Mt Mu Nn On Qa Qb) Mr(Ir Is Ma Mt Nn On Qa Qb) Li(Ir Is Lu Mi Mt Om Qa Qb) Mk(Ir Is Ma Mt On Qa Qb) Pb(Ir Is Ma Mt Nn Qa Qb) Hw(Hx Is Mt Mu Om Qa) Lx(Ne Nq Nv Pe Qd) On(Mj Nd Pe Qb) Po(Jq Om) Nn(Ir Ms) Pa(aA Js) Pe(aA Lu) MjMu NbOm JqPg} Jt{Jg(Hv Ii Iv Mj Mr No Nr Ns Om Po) Ma(Iv Ji Jk Lw Om Qa Qb Qe) Et(Hv Ii Mj Mk Mr Nb Nr) Jq(Jk Mk Mn Mr Nr Oy) Nn(Mk Mr Mv Nr Ok) Jn(Jk Mj Mv Nb Nv) Mn(Hu Mt My) Og(Jk Ok Qa) No(Js Mc) Mf(Jj Oe) Mj(Ih Ii) Mt(Jk Nd) Iv(My Pc) Ji(Mu Mv) NqMi LwHv MqJj MsNv NdLh HuQe IiOk} Js{Mi(Fr Hw Iv Mk Mr Mv Nb Nq Nr Nt Nw Pb) Lx(Hw Iv Jn Mj Mv Qd Qe) Hx(Iv No Om Pe Qa Qb) Is(Iq Lh Lu Nj Pa Pe) Ir(Mj Pb Pe Pg Po) Qa(Jg Lw Mu Nn Om) Jp(Hw Iv No Pb) Jj(Hw Iv No) Jq(Og Pa Pg) Mj(Ms Og) Mq(Lh Pe) Nw(Lu Nc) FrLh MzOm HqPg HwOg QbPe} Ms{Om(Ii Mj Mk Mr Nn No Nr Oy Qb) Mj(Hu Ih Mf Ml Mx Oy Qa) Pb(Hu Ir Iv Lw Nc Qd Qe) Oy(Ir Lw Pe Qd Qe) Lw(Ii Qe) Is(Jr Ml) NsMw NuNd MfHw MkMy Mpli MqOk MuHu NlPa IhIu} Nf{Lh(Fr Mk Mr Ne Nn Nr Nt Nw) Pa(Hv Jn Lj Ml Nw Pf) Pc(Ir Is Lx Qb Qd) Mi(Nb Nd On Pe) Fr(Ii Mk Mr) Nb(Lx Mv Pg) Qb(Mk Mr Pe) Hx(Ii Ml) Nw(Pe Pg) NnOn LxOy MkMv IiPg} Mz{Ml(Hw Hx Is Iv Mj Nb Nn No Om Pb Po) Hw(Hv Jn Jr Mf Mq Na Nm) Jn(Is Iv Nb Nn No Nw) Mx(Is Iv Nn) Mt(Nn Nw) Pb(Hx Ny) Pc(My Ns) LxNe IrIs IvJr} Iu{Qd(Ii Jg Mr Mu Nb Nn Nr Po) Qb(Mj Mk Mr Nb No Nr Po) Fr(Mk Mr Nr) Mv(Lh On Po) Nj(No Nw On) Is(Mk Mr Nr) Qe(Mr Nb Nr) Nn(Jj Pe) Lx(Jn Mj) Nw(Lh Pe)} Lx{Nt(Fr Ir Is Iv Lu Mt Mv Nb Nu Nw On Qb Qd Qe) Nj(Jg Mu Mv Ne Nn) Lu(Mk Mr Nr) Nq(Fr Jr) Mi(Jj Pa) Ne(Jr Nc) MfMj MlHx NdJj HrPa} Iq{Is(Fr Jn Ml Mr Nd Pc) Qa(Mj Mk Mr Nb Nr) Mi(Hq Mk Mr Nr) Nd(Ir Qb Qd Qe) Fr(Lh Mj On) Hx(Mk Mr Nr) Ir(Lw Nn Pc) Lh(Mj On) JpOn} Nj{Lu(Lh Mn Nq Nw On Po) Nn(Mj Mk Nb On Pe) Nd(Ii Ni Qa Qd) Nh(Lh Mu Nw On) Ma(Mf Pc) Mq(Lh Mp) MjHx QcJj NwPc} Jj{Ml(Iv Nn No Om Pb) Nn(Mr Nb Nr) Mq(Jq Ok Om) Mu(Ii Mj Mr) Hw(Hv Jn Nm) Iv(Jn Mx) Pc(My Ns) NoMc NqMi NyPb} Pa{Hq(Ih Jr Lj Mh Mu) Nt(Lh Mt Nw Qa) Na(Hx Is My Of) Mx(Is Nw Qa) Hv(Hw Qa) NqHr NrLj LwMq JmPe} Jr{Ml(Hw Hx Is Mj Nb No Nw Pb) Pc(Jh Mv Nq) Hx(Ny Pb) NmHw NqMi MqOk MtNw MyOy LiOn NyPb} Nc{Ne(Hx Is Jg Ji Lh Lw Ni Oe Og On Pc Pg Po) Nl(Iv Ji) NhJi} Hw{Og(Hv In Mf Ml Mq Nm) Nm(Jp Mu Mv Oe) Jp(Mf Mq Na) MeOe MfPg} Lw{Nm(Ir Is Jq Lh) Mf(Ir Lh Qa) Lu(Mv Pc) Mq(Hx Pg) MmJp NaLh JkOf} Mx{Is(Fr Jp Lu Mi Mv Pg) Mj(Mi Mv Nw Og Pg) Iv(Oe Pg) QaPe} Mm{Jp(Mj Mk Mr Nb Nr) Et(Jk Oe) Ji(Lu Pc) MaMu Mtlv IrOm} Pc{My(Hx Jp Lu Oe) Ns(Jp Lu Oe) Qa(Ml Mq) LuMa MrOe} Na{Nr(Lh Mu Pg Qa) Lh(Is Mk Nq) Pe(Is Mh)} Jg{Lu(My Nq Ns) My(Hx Pg) Pe(Nt Of) NqHx MqQa} Nt{Pe(Mi Nw On Pg Qa) MiQb MrPg} Hq{Mp(Hu Mv) Pb(Jp Pg) FrPg MfLh MiOk} Of{Nb(Fr Hx Pg) Mk(Hx Pg) FrPb Mali} On{Ii(Mk Mr Nr) MiJi MqHr LhOk} Nq{Mi(Fr Mv) Lh(Mf Mu)} Lu{Nw(Jn Ml) MkQa} Mf{MjMv HrOg QaOm} Nm{MtNw JqPg} Nn{Hx(My Ns)} Ml{FrIs OePb} Jn{IsJp JqOg} MdOePb MvMyNb NdNiNk LjOgOy Constrained panels with 2 analytes, where 1.0E-6 >= 'AUC p-value' > 0. Contains 117 panels of 6,786 total panels evaluated. : Lv(aA Fr Hx Jj Jl Jo Jp Lu Mf Mg Mi Mk Mq Mr Mz Nd Ng Nn Nr Nx Oe Og Oi Pa Pc) Og(aA Fr Hx Ir Is Iv Ji Jl Jp Jr Lh Mi Mj Mu Mz No Nw Om On Pa Pe Pg Po) Jj(Hx Ir Is Jk Jl Jr Lh My Mx Pa Pe Pg Qa Qb Qd Qe) Oe(aA Fr Hx Ir Is Jl Jp Jr Mi Mz Nw On Pa Pe Pg Po) Jl(Iu Jo Jt Lu Mm Ms Ng Nx Oh Oi) Jt(aA Ir Is Lh Mi Nw On Pa Pg) Jo(Hx Ir Is Lh Mz Pa Pe Pg) Pa(Iq Iu Pf) Ms(Fr Mi) Mz(Mm Nx) IqaA JrPc NxPg Constrained panels with 2 analytes, where 1.0E-5 >= 'AUC p-value' > 1.0E-6. Contains 55 panels of 6,786 total panels evaluated. : Og(Hv Jg Jn Lx Mk Mt Nb Nn Nv Pb Qa Qb Qd Qe) Fr(Jo Jr Jt Mg Ng Oi) Ms(Jg Mu Mz On Pa) Lu(Mi Mz Nn Pg) Jj(Hu Ih Mt Nv) Jo(Mi On Po Qe) Oe(Lh Mj No Nu) Ng(Lh Mv Pg) Jr(Js Mv Nn) Mm(Lh On) Jl(aA Pa) LxPd MzJt NjPa Irlu Constrained panels with 2 analytes, where 1.0E-4 >= 'AUC p-value' > 1.0E-5. Contains 85 panels of 6,786 total panels evaluated. : Jj(Fr Ii Iv Jn Jp Lu Lx Mi Mj Mv Og On Po) Og(Ii Ip Jk Lu Lw Ma Mr Mv Nr Oy Pc) Ms(Hx Is Ji Jp Lh Mv Nn Nw Pg Po) Oe(Iv Jg Ji Lx Mn Mt Nb Qd Qe) Jr(Jn Jo Jp Lh Lu On Pg) Pa(Fr Hq Lu Nf Ng Oy) Jo(Lx Nv Nw Qa Qd) Pg(Iu Jp Mg Oi Pd) Lx(Hq Mm Ng) Mi(Jl Mg Pd) Oi(Hx Mv Mz) Fr(Nj Nx) Lu(Jp Qb) Pd(On Po) MgMv NgHx NjJp IsNx Constrained panels with 2 analytes, where 1.0E-3 >= 'AUC p-value' > 1.0E-4. Contains 135 panels of 6,786 total panels evaluated. : Oe(Hv Ii Jj Jk Jn Lu Lw Ma Mk Mp Mr Mu Mv Nn Nr Nv Om Pc Qa Qb) Jj(Iu Jg Ma Mk Mr Mu Nb Nj Nn No Nr Nw Om Oy Pc) Jo(Hw Ii Ip Jg Ji Jk Lw Mj Mn Mt Mv Nb No Pc Qb) Lu(Hx Is Lw Lx Nw On Pc Pe Po Qa) Mz(Fr Lh Mj Mv Nn On Pc Pe Pg) Jt(Ji Jp Lx No Nv Om Pe Qa Qd) Iu(Is Lh Pe Qa Qb Qd Qe) Ms(Ir Lw Lx No Pc Pe) Jr(Hx Mk Mr Nr Nw Pe) Ng(Jg Mp Nn On Po) Jp(Hx Is Lh Mm Pe) Oi(Ir Is Lh Lx Qa) On(Mg Nf Nx Of) Lh(Nf Nm Pd) Pc(Hx Lx Mi) Mg(Hx Jg) Iq(Ir Mi) Js(Is Pa) Nw(Mm Nx) Pe(Pa Pf) MpPd NdNj HuOg Constrained panels with 2 analytes, where 1.0E-2 >= 'AUC p-value' > 1.0E-3. Contains 157 panels of 6,786 total panels evaluated. : Ms(Hu Ii Jk Jn Ma Mj Mk Mn Mp Mr Mt Mw My Nb Nd Nq Nr Nv Om Oy Pb Qb Qd Qe) Jo(Hv Iu Iv Jt Ma Mk Mp Mr Mu My Nn Nr Nu Om Oy) Oi(Hu Ip Iv Jg Ma Mn Nu Nv Nw On Qb Qd Qe) Lu(Ir Iv Jg Ji Jn Lh Ma Mn Mt Mu Mv Om Qd Qe) Nr(Fr Hx Jp Lh Lx Mu Mv Mz Pg Qa) Ng(Ii Ma Mt Mu My Nb Nv Pc Pe) Pc(Ir Is Jp Nj Pe Qa Qb Qd) Mk(Fr Jp Lh Lx Mz Pg Qa) Mr(Fr Jp Lh Lx Mz Pg Qa) Mg(Jk Lh Ma Mu Nv Po) Nj(Lh Nn Nq Nw Og) Jp(Lw Mj Nw On) Nx(Ji Lh Nv Om) Pe(Fr Mv Nf Pd) Mu(Ir Mj Qb) Nt(Lx Mi) Mm(Jg Ji) Mv(Mj Nb) Ir(Lw Nn) Jk(Iu Jt) Js(Lh Nw) Oe(Hu Oy) NuJj LxNb MaHv MqOn MxIs NcNd JtOk PaPd Constrained panels with 2 analytes, where 5.0E-2 >= 'AUC p-value' > 1.0E-2. Contains 76 panels of 6,786 total panels evaluated. : Nn(Iv Mg Mj Nc Nr Pe Qb Qd) Mr(Is Jt Lu Mu Mv Ng Nw Qb) Mk(Is Jt Lu Mv Ng Nw Qb) Nr(Is Jt Lu Ng Nw Qb) Ng(Hu Jk Om Oy Pb) Oi(Ii Jk Nb Om Pc) Lu(Et Mj Nb No) Is(Ir Jn Jr Ml) Pc(Ma Mg Nc Nw) Lw(Mu Mv Qb) Lx(Nd Ne Nj) Mj(Mf Nj Qb) Jo(Et Hu Jn) Hq(Mi Mp) Jg(Jt Qd) EtMm NoJs NtLh MaJt MgOm MqJi NbQb NcNe LiPd

Figure 16 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ad | ug/mL | 4.1E-2 | 6.4E-2 | 7.5E-2 | 6.5E-2 | 9.0E-2 | 4.8E-2 | 2.7E-4 | 1.1E-2 | 5.4E-1 | 1.5E-1 | 454 | 7 | 168 | 7 | 0.55 |
| Af | ng/mL | 1.1E0 | 3.6E-1 | 1.5E1 | 3.2E-1 | 6.0E1 | 1.5E-1 | 1.7E-3 | 1.7E-3 | 5.3E2 | 4.6E-1 | 454 | 7 | 168 | 7 | 0.28 |
| Aj | ug/mL | 1.6E0 | 4.8E-1 | 2.6E0 | 1.9E0 | 2.4E0 | 2.1E0 | 1.5E-3 | 4.0E-3 | 6.1E0 | 4.8E0 | 454 | 7 | 168 | 7 | 0.38 |
| Al | mg/mL | 8.7E-5 | 9.7E-5 | 2.5E-4 | 3.1E-4 | 4.0E-4 | 5.2E-4 | 2.3E-6 | 3.7E-5 | 1.9E-3 | 1.5E-3 | 454 | 7 | 168 | 7 | 0.58 |
| An | U/mL | 5.1E1 | 7.2E1 | 1.8E2 | 1.4E2 | 4.4E2 | 1.1E2 | 9.8E-4 | 2.7E1 | 5.5E3 | 3.4E2 | 454 | 7 | 168 | 7 | 0.65 |
| Ao | pg/mL | 8.9E1 | 5.0E1 | 5.1E2 | 7.6E1 | 3.4E3 | 7.9E1 | 2.8E0 | 6.1E0 | 3.9E4 | 2.4E2 | 454 | 7 | 168 | 7 | 0.35 |
| Ap | ng/mL | 3.3E1 | 5.9E1 | 4.5E1 | 5.1E1 | 4.4E1 | 3.1E1 | 8.4E-5 | 5.7E0 | 2.9E2 | 9.7E1 | 454 | 7 | 168 | 7 | 0.60 |
| Ar | ng/mL | 9.7E-1 | 1.9E0 | 1.2E1 | 1.1E1 | 1.9E2 | 1.8E1 | 3.4E-3 | 3.6E-1 | 4.1E3 | 5.0E1 | 454 | 7 | 168 | 7 | 0.66 |
| As | ng/mL | 9.0E-3 | 1.5E-2 | 1.3E-2 | 1.2E-2 | 1.9E-2 | 7.3E-3 | 1.7E-3 | 1.7E-3 | 1.3E-1 | 1.9E-2 | 454 | 7 | 168 | 7 | 0.57 |
| Aw | pg/mL | 1.6E1 | 1.7E1 | 1.6E1 | 1.7E1 | 6.1E0 | 3.1E0 | 2.9E-2 | 1.4E1 | 4.8E1 | 2.3E1 | 454 | 7 | 168 | 7 | 0.56 |
| Ax | ng/mL | 2.4E0 | 1.5E1 | 1.7E1 | 1.6E2 | 6.5E1 | 3.1E2 | 1.2E-2 | 5.8E-1 | 7.7E2 | 8.5E2 | 454 | 7 | 168 | 7 | 0.70 |
| Ba | ng/mL | 7.0E1 | 5.8E2 | 4.4E2 | 9.0E2 | 1.2E3 | 1.0E3 | 3.7E-1 | 5.5E0 | 8.1E3 | 3.0E3 | 454 | 7 | 168 | 7 | 0.68 |
| Bb | ng/mL | 3.1E0 | 4.3E0 | 6.5E0 | 4.8E0 | 1.4E1 | 2.6E0 | 4.1E-3 | 5.5E-1 | 2.5E2 | 8.2E0 | 454 | 7 | 168 | 7 | 0.57 |
| Bc | ng/mL | 3.9E1 | 1.2E2 | 1.1E2 | 2.6E2 | 2.0E2 | 3.4E2 | 1.1E-1 | 3.7E1 | 1.2E3 | 9.9E2 | 454 | 7 | 168 | 7 | 0.78 |
| Bg | ng/mL | 9.1E-2 | 5.4E-1 | 5.9E0 | 7.9E-1 | 3.5E1 | 1.1E0 | 5.3E-4 | 2.2E-2 | 4.4E2 | 3.3E0 | 454 | 7 | 168 | 7 | 0.59 |
| Bn | ng/mL | 5.6E-2 | 5.6E-2 | 1.2E0 | 1.1E-1 | 2.0E0 | 1.0E-1 | 5.6E-2 | 5.6E-2 | 9.7E0 | 3.2E-1 | 454 | 7 | 168 | 7 | 0.36 |
| Bo | ng/mL | 1.2E1 | 2.0E1 | 1.5E1 | 2.3E1 | 1.9E1 | 9.5E0 | 1.6E-2 | 1.1E1 | 2.8E2 | 3.6E1 | 454 | 7 | 168 | 7 | 0.76 |
| Ch | uIU/mL | 1.2E0 | 7.8E-1 | 2.1E1 | 1.1E0 | 1.1E2 | 1.0E0 | 3.4E-3 | 1.7E-1 | 1.8E3 | 3.2E0 | 454 | 7 | 168 | 7 | 0.38 |
| Co | pg/mL | 4.0E1 | 5.0E1 | 1.7E2 | 5.6E1 | 9.5E2 | 5.7E1 | 1.5E-1 | 1.1E1 | 1.7E4 | 1.7E2 | 454 | 7 | 168 | 7 | 0.45 |
| Cp | ng/mL | 2.2E1 | 2.1E1 | 2.9E1 | 2.6E1 | 3.2E1 | 1.4E1 | 6.0E-1 | 1.8E1 | 3.7E2 | 5.6E1 | 454 | 7 | 168 | 7 | 0.53 |
| Cq | ng/mL | 3.0E-2 | 5.3E-2 | 1.6E-1 | 5.7E-2 | 8.8E-1 | 4.6E-2 | 8.0E-4 | 7.8E-3 | 1.7E1 | 1.3E-1 | 454 | 7 | 168 | 7 | 0.59 |
| Cs | ng/mL | 7.3E1 | 2.7E2 | 3.4E2 | 1.7E3 | 1.1E3 | 2.4E3 | 2.7E-2 | 3.0E1 | 1.8E4 | 5.3E3 | 454 | 7 | 168 | 7 | 0.74 |
| Ct | ng/mL | 6.0E-1 | 3.8E-1 | 4.0E1 | 1.8E1 | 1.1E2 | 3.1E1 | 1.1E-4 | 3.8E-2 | 6.2E2 | 7.2E1 | 454 | 7 | 168 | 7 | 0.48 |
| Cu | ng/mL | 2.5E-1 | 6.4E-1 | 5.0E-1 | 8.2E-1 | 1.4E0 | 9.6E-1 | 9.6E-3 | 8.1E-2 | 2.1E1 | 2.9E0 | 454 | 7 | 168 | 7 | 0.66 |
| Cv | ng/mL | 5.1E0 | 1.1E1 | 2.1E1 | 2.5E1 | 5.2E1 | 3.8E1 | 1.4E-4 | 2.3E0 | 5.3E2 | 1.1E2 | 454 | 7 | 168 | 7 | 0.62 |
| Cw | mIU/mL | 3.0E-2 | 4.3E-2 | 3.8E-2 | 5.9E-2 | 3.1E-2 | 3.9E-2 | 1.5E-4 | 1.6E-2 | 2.4E-1 | 1.3E-1 | 454 | 7 | 168 | 7 | 0.68 |
| Cx | ng/mL | 2.2E-1 | 7.4E-3 | 5.6E-1 | 6.8E-2 | 1.0E2 | 1.3E-1 | 9.3E-5 | 9.3E-5 | 3.9E2 | 3.6E-1 | 454 | 7 | 168 | 7 | 0.33 |
| Db | ug/mL | 7.3E0 | 6.6E0 | 8.8E0 | 9.4E0 | 9.4E0 | 6.3E0 | 4.5E-1 | 4.3E0 | 1.4E2 | 2.3E1 | 454 | 7 | 168 | 7 | 0.54 |
| Dc | nmol/L | 1.9E-2 | 3.4E-2 | 6.2E-2 | 5.0E-2 | 1.5E-1 | 6.7E-2 | 5.2E-6 | 1.6E-3 | 1.6E0 | 2.0E-1 | 454 | 7 | 168 | 7 | 0.54 |
| Dd | ug/mL | 6.9E-2 | 1.8E-1 | 1.7E-1 | 2.0E-1 | 2.6E-1 | 2.3E-1 | 1.9E-4 | 1.5E-2 | 1.9E0 | 6.9E-1 | 454 | 7 | 168 | 7 | 0.60 |
| De | ng/mL | 3.4E-3 | 3.4E-3 | 8.0E-2 | 3.4E-3 | 1.4E-1 | 0.0E0 | 3.4E-3 | 3.4E-3 | 9.2E-1 | 3.4E-3 | 454 | 7 | 168 | 7 | 0.33 |
| Dg | ng/mL | 3.5E1 | 4.6E1 | 4.6E1 | 4.4E1 | 4.0E1 | 3.0E1 | 1.0E-1 | 4.4E0 | 1.9E2 | 8.4E1 | 454 | 7 | 168 | 7 | 0.52 |
| Di | pg/mL | 1.9E0 | 2.9E0 | 2.2E0 | 1.9E0 | 2.1E0 | 1.6E0 | 1.8E-1 | 1.8E-1 | 1.3E1 | 3.5E0 | 454 | 7 | 168 | 7 | 0.48 |
| Dk | uIU/mL | 1.7E-2 | 1.8E-1 | 8.5E-2 | 1.6E-1 | 5.1E-1 | 3.6E-1 | 1.1E-4 | 5.8E-3 | 8.9E0 | 9.8E-1 | 454 | 7 | 168 | 7 | 0.51 |
| Dl | ng/mL | 2.4E2 | 5.6E2 | 3.3E2 | 4.7E2 | 3.0E2 | 3.2E2 | 1.7E0 | 2.5E1 | 1.5E3 | 8.3E2 | 454 | 7 | 168 | 7 | 0.63 |
| Wm | % | 4.7E-1 | 6.4E0 | 3.9E1 | 1.3E2 | 1.9E2 | 3.2E2 | 5.4E-2 | 8.5E-2 | 2.4E3 | 8.6E2 | 358 | 7 | 178 | 7 | 0.76 |
| Po | pg/ml | 8.0E-1 | 9.0E0 | 8.3E0 | 4.6E1 | 2.2E1 | 7.5E1 | 8.0E-3 | 2.6E-2 | 2.7E2 | 2.2E2 | 799 | 8 | 262 | 8 | 0.62 |
| Et | ng/ml | 1.5E3 | 2.7E3 | 1.7E3 | 2.8E3 | 1.2E3 | 1.7E3 | 7.7E1 | 4.0E2 | 5.0E3 | 5.0E3 | 798 | 8 | 262 | 8 | 0.69 |
| Fp | ng/ml | 1.4E1 | 6.2E1 | 2.6E1 | 6.2E1 | 2.9E1 | 4.6E1 | 6.0E-3 | 3.3E0 | 1.4E2 | 1.4E2 | 828 | 8 | 264 | 8 | 0.76 |
| Fr | ng/ml | 4.1E4 | 2.9E5 | 1.2E5 | 4.0E5 | 1.8E5 | 3.5E5 | 1.9E2 | 2.6E4 | 9.0E5 | 8.9E5 | 916 | 11 | 265 | 11 | 0.78 |
| Nm | pg/ml | 1.7E4 | 3.8E4 | 3.4E4 | 8.6E4 | 8.2E4 | 1.5E5 | 1.0E-9 | 1.0E-9 | 1.6E6 | 4.4E5 | 802 | 8 | 264 | 8 | 0.63 |
| Nn | pg/ml | 1.7E2 | 4.8E3 | 1.9E3 | 1.6E4 | 8.2E3 | 2.5E4 | 1.0E-9 | 2.6E1 | 1.0E5 | 6.9E4 | 802 | 8 | 264 | 8 | 0.76 |
| No | pg/ml | 1.7E1 | 4.0E1 | 3.7E1 | 3.2E2 | 1.1E2 | 5.6E2 | 1.0E-9 | 4.0E0 | 2.5E3 | 1.4E3 | 802 | 8 | 264 | 8 | 0.62 |
| Nq | pg/ml | 2.3E0 | 1.1E1 | 2.0E1 | 5.6E1 | 7.7E1 | 9.0E1 | 1.0E-9 | 1.0E-9 | 1.2E3 | 2.6E2 | 802 | 8 | 264 | 8 | 0.61 |
| Nr | pg/ml | 1.3E0 | 1.2E0 | 3.0E1 | 1.1E3 | 1.9E2 | 3.0E3 | 1.0E-9 | 1.0E-9 | 4.1E3 | 8.5E3 | 802 | 8 | 264 | 8 | 0.53 |
| Ns | pg/ml | 1.0E-9 | 1.0E-9 | 9.6E0 | 2.1E0 | 5.5E1 | 5.8E0 | 1.0E-9 | 1.0E-9 | 1.1E3 | 1.6E1 | 802 | 8 | 264 | 8 | 0.51 |
| Nt | pg/ml | 1.1E2 | 1.4E2 | 1.4E2 | 2.3E2 | 1.1E2 | 2.0E2 | 1.0E-9 | 1.1E2 | 1.5E3 | 6.8E2 | 802 | 8 | 264 | 8 | 0.70 |
| Nu | pg/ml | 2.4E1 | 1.3E2 | 5.6E1 | 1.8E2 | 8.9E1 | 1.7E2 | 1.0E-9 | 2.8E1 | 8.9E2 | 5.8E2 | 802 | 8 | 264 | 8 | 0.84 |
| Lu | pg/ml | 1.0E4 | 6.8E3 | 1.8E4 | 1.4E4 | 6.5E4 | 2.0E4 | 3.5E2 | 1.6E3 | 1.3E6 | 6.1E4 | 805 | 8 | 264 | 8 | 0.42 |
| Lv | pg/ml | 1.0E-9 | 4.1E1 | 1.1E1 | 6.7E1 | 2.3E1 | 6.1E1 | 1.0E-9 | 1.0E-9 | 2.6E2 | 1.9E2 | 805 | 8 | 264 | 8 | 0.86 |
| Lw | pg/ml | 1.0E-9 | 1.0E-9 | 3.2E-1 | 4.8E0 | 3.7E0 | 8.9E0 | 1.0E-9 | 1.0E-9 | 8.0E1 | 2.1E1 | 805 | 8 | 264 | 8 | 0.68 |
| Lx | pg/ml | 1.0E-9 | 5.0E2 | 1.5E2 | 2.1E3 | 4.3E2 | 3.5E3 | 1.0E-9 | 1.0E-9 | 6.2E3 | 1.0E4 | 805 | 8 | 264 | 8 | 0.79 |
| Ly | pg/ml | 1.0E-9 | 9.4E0 | 1.0E1 | 1.1E1 | 2.0E1 | 1.1E1 | 1.0E-9 | 1.0E-9 | 1.6E2 | 2.6E1 | 805 | 8 | 264 | 8 | 0.60 |
| Lz | pg/ml | 1.0E-9 | 1.0E-9 | 3.8E0 | 2.6E1 | 3.1E1 | 7.4E1 | 1.0E-9 | 1.0E-9 | 6.0E2 | 2.1E2 | 805 | 8 | 264 | 8 | 0.53 |

Figure 17

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ma | pg/ml | 3.0E2 | 1.8E3 | 1.3E3 | 2.7E3 | 3.8E3 | 3.3E3 | 1.0E-9 | 4.0E1 | 6.5E4 | 9.5E3 | 805 | 8 | 264 | 8 | 0.65 |
| Mb | pg/ml | 2.5E1 | 3.1E1 | 3.1E1 | 4.2E1 | 1.5E1 | 2.6E1 | 5.4E0 | 1.9E1 | 2.1E2 | 8.7E1 | 805 | 8 | 264 | 8 | 0.61 |
| Mc | pg/ml | 1.0E-9 | 1.0E-9 | 4.3E-2 | 1.0E-9 | 6.0E-1 | 0.0E0 | 1.0E-9 | 1.0E-9 | 1.3E1 | 1.0E-9 | 805 | 8 | 264 | 8 | 0.49 |
| Md | pg/ml | 1.0E-9 | 1.0E-9 | 3.7E-1 | 1.0E-9 | 2.8E0 | 0.0E0 | 1.0E-9 | 1.0E-9 | 6.5E1 | 1.0E-9 | 805 | 8 | 264 | 8 | 0.46 |
| Me | pg/ml | 3.3E1 | 2.3E1 | 3.2E1 | 2.7E1 | 2.0E1 | 2.3E1 | 1.0E-9 | 3.2E0 | 3.2E2 | 7.9E1 | 805 | 8 | 264 | 8 | 0.32 |
| Mf | pg/ml | 1.0E-9 | 1.0E-9 | 5.5E-1 | 3.4E-1 | 3.0E0 | 7.5E-1 | 1.0E-9 | 1.0E-9 | 5.6E1 | 2.2E0 | 805 | 8 | 264 | 8 | 0.60 |
| Mg | pg/ml | 1.8E0 | 7.7E0 | 7.6E0 | 1.2E1 | 1.2E1 | 1.4E1 | 1.0E-9 | 1.0E-9 | 9.2E1 | 4.0E1 | 805 | 8 | 264 | 8 | 0.62 |
| Mh | pg/ml | 1.0E-9 | 4.2E-2 | 1.3E0 | 6.1E0 | 9.8E0 | 1.3E1 | 1.0E-9 | 1.0E-9 | 1.6E2 | 3.8E1 | 805 | 8 | 264 | 8 | 0.63 |
| Mi | pg/ml | 1.0E-9 | 1.4E1 | 4.8E-1 | 3.7E1 | 5.4E0 | 5.6E1 | 1.0E-9 | 1.0E-9 | 1.2E2 | 1.6E2 | 805 | 8 | 264 | 8 | 0.74 |
| Mj | pg/ml | 1.0E-9 | 1.0E-9 | 4.3E0 | 6.8E0 | 2.4E1 | 1.9E2 | 1.0E-9 | 1.0E-9 | 4.6E2 | 5.4E2 | 805 | 8 | 264 | 8 | 0.53 |
| Mk | pg/ml | 9.1E-1 | 4.6E0 | 1.5E1 | 7.0E2 | 9.1E1 | 2.0E3 | 1.0E-9 | 1.0E-9 | 1.7E3 | 5.6E3 | 805 | 8 | 264 | 8 | 0.57 |
| Ml | pg/ml | 1.0E-9 | 1.0E-9 | 5.2E0 | 3.7E0 | 7.7E1 | 6.2E0 | 1.0E-9 | 1.0E-9 | 2.1E3 | 1.6E1 | 805 | 8 | 264 | 8 | 0.61 |
| Mm | pg/ml | 6.4E2 | 1.6E3 | 1.1E3 | 2.5E3 | 1.3E3 | 2.6E3 | 1.0E-9 | 8.0E1 | 1.1E4 | 6.9E3 | 805 | 8 | 264 | 8 | 0.65 |
| Mn | pg/ml | 5.7E0 | 7.2E0 | 1.1E1 | 1.8E1 | 2.4E1 | 2.2E1 | 1.0E-9 | 6.9E-1 | 3.5E2 | 6.6E1 | 805 | 8 | 264 | 8 | 0.62 |
| Mp | pg/ml | 1.0E-9 | 2.1E1 | 9.3E0 | 6.3E1 | 3.0E1 | 7.9E1 | 1.0E-9 | 1.0E-9 | 6.3E2 | 1.8E2 | 804 | 8 | 264 | 8 | 0.63 |
| Mq | pg/ml | 1.0E-9 | 1.0E-9 | 2.7E0 | 1.8E1 | 1.7E1 | 5.1E1 | 1.0E-9 | 1.0E-9 | 2.4E2 | 1.4E2 | 804 | 8 | 264 | 8 | 0.53 |
| Mr | pg/ml | 1.0E-9 | 5.8E-1 | 2.8E1 | 1.5E3 | 1.5E2 | 4.2E3 | 1.0E-9 | 1.0E-9 | 2.2E3 | 1.2E4 | 804 | 8 | 264 | 8 | 0.58 |
| Ms | pg/ml | 4.1E2 | 4.7E2 | 5.5E2 | 4.4E2 | 6.5E2 | 3.7E2 | 1.0E-9 | 1.0E-9 | 5.9E3 | 8.6E2 | 804 | 8 | 264 | 8 | 0.48 |
| Mt | pg/ml | 4.8E-1 | 1.5E1 | 7.2E0 | 2.2E1 | 4.4E1 | 2.7E1 | 1.0E-9 | 1.0E-9 | 8.7E2 | 7.8E1 | 804 | 8 | 264 | 8 | 0.76 |
| Mu | pg/ml | 1.0E-9 | 4.0E0 | 1.4E0 | 6.6E0 | 1.1E1 | 9.3E0 | 1.0E-9 | 1.0E-9 | 2.3E2 | 2.7E1 | 804 | 8 | 264 | 8 | 0.76 |
| Mv | pg/ml | 1.0E-9 | 3.5E1 | 7.6E1 | 1.2E2 | 3.3E2 | 1.6E2 | 1.0E-9 | 1.0E-9 | 4.5E3 | 4.4E2 | 804 | 8 | 264 | 8 | 0.70 |
| Mw | pg/ml | 4.0E1 | 4.9E2 | 5.5E2 | 1.7E3 | 3.5E3 | 2.9E3 | 1.0E-9 | 1.0E-9 | 6.2E4 | 8.5E3 | 804 | 8 | 264 | 8 | 0.68 |
| Mx | pg/ml | 1.0E-9 | 1.0E-1 | 2.6E-1 | 5.7E-1 | 1.4E0 | 1.1E0 | 1.0E-9 | 1.0E-9 | 3.2E1 | 3.0E0 | 804 | 8 | 264 | 8 | 0.67 |
| My | pg/ml | 1.0E-9 | 3.7E2 | 5.1E2 | 7.6E2 | 3.1E3 | 1.2E3 | 1.0E-9 | 1.0E-9 | 3.9E4 | 3.4E3 | 804 | 8 | 264 | 8 | 0.75 |
| Mz | pg/ml | 1.2E1 | 3.0E1 | 2.8E1 | 6.4E1 | 6.5E1 | 7.7E1 | 1.0E-9 | 5.1E0 | 1.2E3 | 2.0E2 | 804 | 8 | 264 | 8 | 0.65 |
| Na | pg/ml | 1.0E-9 | 1.0E-9 | 6.3E-1 | 1.3E0 | 2.7E0 | 3.8E0 | 1.0E-9 | 1.0E-9 | 3.6E1 | 1.1E1 | 804 | 8 | 264 | 8 | 0.48 |
| Nb | pg/ml | 2.1E0 | 5.8E0 | 4.0E0 | 3.6E1 | 1.2E1 | 8.3E1 | 1.0E-9 | 1.0E-9 | 2.3E2 | 2.4E2 | 804 | 8 | 264 | 8 | 0.70 |
| Nc | pg/ml | 3.4E2 | 1.8E2 | 5.6E2 | 2.0E2 | 7.4E2 | 1.8E2 | 1.0E-9 | 1.0E-9 | 9.2E3 | 5.2E2 | 804 | 8 | 264 | 8 | 0.37 |
| Nd | pg/ml | 2.8E1 | 2.0E1 | 2.7E1 | 4.9E1 | 4.7E1 | 5.8E1 | 1.0E-9 | 1.0E-9 | 1.2E3 | 1.4E2 | 804 | 8 | 264 | 8 | 0.52 |
| Ne | pg/ml | 4.5E2 | 1.7E2 | 5.8E2 | 2.4E2 | 5.9E2 | 2.6E2 | 1.0E-9 | 1.3E1 | 7.0E3 | 7.6E2 | 804 | 8 | 264 | 8 | 0.31 |
| Nf | pg/ml | 1.0E-9 | 1.0E-9 | 2.5E0 | 1.2E1 | 9.5E0 | 2.9E1 | 1.0E-9 | 1.0E-9 | 1.6E2 | 8.2E1 | 804 | 8 | 264 | 8 | 0.53 |
| Ng | pg/ml | 2.8E1 | 6.2E1 | 1.3E2 | 1.4E2 | 2.5E2 | 1.8E2 | 1.0E-9 | 1.0E-9 | 2.3E3 | 4.7E2 | 804 | 8 | 264 | 8 | 0.49 |
| Nh | pg/ml | 6.8E1 | 3.1E1 | 9.1E1 | 3.5E1 | 8.5E1 | 2.2E1 | 1.0E-9 | 2.2E0 | 5.6E2 | 6.9E1 | 804 | 8 | 264 | 8 | 0.27 |
| Ni | pg/ml | 1.0E-9 | 6.4E1 | 7.4E1 | 1.1E2 | 1.2E2 | 1.4E2 | 1.0E-9 | 1.0E-9 | 7.1E2 | 3.9E2 | 804 | 8 | 264 | 8 | 0.63 |
| Nj | pg/ml | 7.3E0 | 6.9E0 | 1.1E1 | 7.4E0 | 1.2E1 | 6.4E0 | 1.0E-9 | 6.8E-1 | 1.1E2 | 2.0E1 | 804 | 8 | 264 | 8 | 0.45 |
| Nk | pg/ml | 1.7E1 | 1.9E1 | 3.3E1 | 2.0E1 | 4.0E1 | 7.4E0 | 1.0E-9 | 5.7E0 | 2.0E2 | 2.8E1 | 804 | 8 | 264 | 8 | 0.52 |
| Nl | pg/ml | 4.6E1 | 1.9E1 | 6.1E1 | 2.8E1 | 6.9E1 | 2.5E1 | 1.0E-9 | 1.0E-9 | 1.1E3 | 7.0E1 | 804 | 8 | 264 | 8 | 0.34 |
| Hq | pg/ml | 1.1E0 | 2.4E0 | 1.1E2 | 3.9E1 | 1.7E3 | 1.0E2 | 1.0E-9 | 4.8E-1 | 3.4E4 | 3.0E2 | 800 | 8 | 263 | 8 | 0.65 |
| Hr | pg/ml | 1.1E2 | 1.2E2 | 7.4E2 | 1.4E3 | 1.6E3 | 3.8E3 | 1.0E-9 | 2.7E1 | 1.7E4 | 1.1E4 | 800 | 8 | 263 | 8 | 0.46 |
| Hu | pg/ml | 7.3E0 | 2.0E2 | 3.1E3 | 6.1E2 | 2.7E4 | 1.0E3 | 1.0E-9 | 1.0E-9 | 6.3E5 | 3.0E3 | 800 | 8 | 263 | 8 | 0.69 |
| Hv | pg/ml | 1.5E0 | 3.8E0 | 3.3E0 | 1.0E1 | 1.2E1 | 2.0E1 | 1.0E-9 | 1.3E0 | 2.5E2 | 5.9E1 | 800 | 8 | 263 | 8 | 0.80 |
| Hw | pg/ml | 6.3E0 | 3.2E0 | 1.9E1 | 4.4E2 | 7.4E1 | 1.2E3 | 1.0E-9 | 1.0E-9 | 1.7E3 | 3.4E3 | 800 | 8 | 263 | 8 | 0.39 |
| Hx | pg/ml | 9.2E0 | 1.9E1 | 4.0E1 | 2.7E2 | 3.4E2 | 6.9E2 | 1.0E-9 | 2.9E0 | 9.3E3 | 2.0E3 | 800 | 8 | 263 | 8 | 0.69 |
| Ih | ng/ml | 7.7E1 | 1.4E2 | 2.4E2 | 3.5E2 | 4.9E2 | 4.9E2 | 1.0E-9 | 2.4E1 | 7.4E3 | 1.2E3 | 804 | 8 | 263 | 8 | 0.60 |
| Ii | ng/ml | 9.8E1 | 7.3E1 | 2.5E2 | 1.2E3 | 6.8E2 | 3.2E3 | 1.0E-9 | 7.4E0 | 1.0E4 | 9.2E3 | 804 | 8 | 263 | 8 | 0.45 |
| Ij | ng/ml | 8.1E1 | 1.1E2 | 1.8E2 | 8.9E2 | 5.5E2 | 2.2E3 | 1.6E-1 | 2.8E1 | 6.4E3 | 6.4E3 | 794 | 8 | 261 | 8 | 0.57 |
| Ik | ng/ml | 1.3E1 | 1.4E2 | 9.0E2 | 3.3E2 | 8.7E3 | 4.8E2 | 5.9E-1 | 4.5E0 | 1.2E5 | 1.5E3 | 800 | 8 | 261 | 8 | 0.67 |
| Il | ng/ml | 3.7E2 | 1.8E2 | 1.3E3 | 1.8E3 | 2.8E3 | 4.5E3 | 1.0E-9 | 1.0E-9 | 3.3E4 | 1.2E4 | 787 | 7 | 261 | 7 | 0.34 |
| Im | ng/ml | 2.3E2 | 7.0E2 | 4.1E2 | 7.4E2 | 6.1E2 | 5.7E2 | 1.3E1 | 4.2E1 | 6.8E3 | 1.7E3 | 800 | 8 | 262 | 8 | 0.69 |
| In | ng/ml | 3.3E0 | 4.7E-1 | 2.2E1 | 1.0E1 | 1.5E2 | 2.4E1 | 1.0E-9 | 1.0E-9 | 3.9E3 | 6.8E1 | 804 | 8 | 263 | 8 | 0.33 |
| Io | ng/ml | 9.2E3 | 6.7E3 | 2.7E4 | 7.7E4 | 1.6E5 | 1.9E5 | 1.0E-9 | 9.1E2 | 4.0E6 | 5.5E5 | 796 | 8 | 263 | 8 | 0.49 |
| Ip | ng/ml | 1.2E1 | 3.0E1 | 2.0E1 | 4.6E1 | 2.4E1 | 5.2E1 | 1.0E-9 | 4.1E-1 | 2.6E2 | 1.4E2 | 796 | 8 | 263 | 8 | 0.64 |
| Iq | ug/ml | 1.1E-1 | 2.8E-1 | 1.8E1 | 9.5E1 | 4.8E2 | 2.7E2 | 1.0E-9 | 1.0E-9 | 1.4E4 | 7.5E2 | 796 | 8 | 263 | 8 | 0.47 |
| Ir | ug/ml | 3.7E-1 | 1.1E0 | 2.6E0 | 1.6E1 | 1.5E1 | 4.0E1 | 1.0E-9 | 1.3E-1 | 2.4E2 | 1.1E2 | 795 | 8 | 263 | 8 | 0.68 |
| Is | ng/ml | 1.6E0 | 8.4E0 | 6.0E0 | 3.9E1 | 1.3E1 | 7.8E1 | 1.0E-9 | 6.2E-1 | 1.5E2 | 2.3E2 | 796 | 8 | 263 | 8 | 0.72 |
| It | ng/ml | 2.0E0 | 9.5E-1 | 2.0E1 | 8.9E1 | 1.3E2 | 2.1E2 | 1.0E-9 | 1.0E-9 | 2.8E3 | 5.9E2 | 796 | 8 | 263 | 8 | 0.47 |
| Iu | ng/ml | 2.3E2 | 2.0E2 | 1.3E3 | 3.2E3 | 3.8E3 | 8.5E3 | 1.0E-9 | 1.0E-9 | 2.9E4 | 2.4E4 | 796 | 8 | 263 | 8 | 0.45 |

Figure 17 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Iv | ng/ml | 1.4E1 | 5.1E1 | 4.5E1 | 8.5E2 | 1.6E2 | 2.3E3 | 1.0E-9 | 4.1E-1 | 3.8E3 | 6.4E3 | 795 | 8 | 263 | 8 | 0.67 |
| Pz | ng/ml | 4.7E3 | 1.0E4 | 8.8E3 | 7.3E3 | 4.0E3 | 5.1E3 | 1.3E1 | 3.1E2 | 1.0E6 | 1.4E4 | 796 | 8 | 261 | 8 | 0.59 |
| Qa | ng/ml | 3.6E3 | 1.3E4 | 6.5E3 | 1.1E4 | 7.6E3 | 6.5E3 | 1.2E1 | 1.8E3 | 5.2E4 | 1.8E4 | 796 | 8 | 261 | 8 | 0.71 |
| Qb | ng/ml | 1.0E2 | 2.2E2 | 2.2E2 | 3.0E2 | 4.8E2 | 2.5E2 | 7.9E-1 | 5.2E1 | 8.3E3 | 6.0E2 | 796 | 8 | 261 | 8 | 0.66 |
| Qc | ng/ml | 2.6E2 | 3.5E2 | 6.8E2 | 3.7E2 | 5.9E3 | 2.7E2 | 1.0E-9 | 3.9E1 | 1.7E5 | 8.6E2 | 796 | 8 | 261 | 8 | 0.53 |
| Qd | ng/ml | 1.0E4 | 1.8E4 | 2.2E4 | 3.5E4 | 8.3E4 | 3.9E4 | 2.4E2 | 4.8E3 | 2.0E6 | 1.2E5 | 796 | 8 | 261 | 8 | 0.66 |
| Qe | ng/ml | 1.1E3 | 2.3E3 | 1.9E3 | 4.2E3 | 4.1E3 | 4.5E3 | 7.6E0 | 7.8E2 | 9.7E4 | 1.4E4 | 796 | 8 | 261 | 8 | 0.73 |
| Jg | ng/ml | 5.4E2 | 1.8E3 | 8.6E2 | 2.5E3 | 1.0E3 | 2.2E3 | 1.0E-9 | 1.0E2 | 1.0E4 | 5.4E3 | 800 | 8 | 263 | 8 | 0.73 |
| Jh | ng/ml | 3.3E0 | 4.5E1 | 2.9E1 | 7.7E1 | 1.2E2 | 8.3E1 | 1.0E-9 | 1.0E-9 | 1.6E3 | 2.1E2 | 800 | 8 | 263 | 8 | 0.76 |
| Ji | ng/ml | 5.4E1 | 1.1E2 | 7.6E1 | 3.7E2 | 1.6E2 | 6.2E2 | 1.0E-9 | 4.6E1 | 5.4E2 | 1.8E3 | 800 | 8 | 263 | 8 | 0.73 |
| Jj | ng/ml | 6.6E2 | 1.3E2 | 1.8E3 | 1.5E2 | 1.3E4 | 1.1E2 | 4.8E0 | 1.7E1 | 3.4E5 | 2.7E2 | 800 | 8 | 263 | 8 | 0.12 |
| Jk | ng/ml | 3.4E0 | 1.9E1 | 2.3E1 | 3.8E1 | 4.9E1 | 5.9E1 | 1.0E-9 | 1.0E-1 | 3.9E2 | 1.7E2 | 800 | 8 | 263 | 8 | 0.61 |
| Jl | ng/ml | 4.7E-1 | 1.9E0 | 2.1E0 | 2.4E1 | 6.0E0 | 5.4E1 | 7.6E-4 | 7.2E-2 | 1.1E2 | 1.6E2 | 800 | 8 | 263 | 8 | 0.69 |
| Jm | ng/ml | 1.9E1 | 1.4E1 | 6.0E1 | 3.9E1 | 1.3E2 | 5.8E1 | 1.0E-9 | 9.6E-1 | 2.1E3 | 1.5E2 | 800 | 8 | 263 | 8 | 0.45 |
| Jn | pg/ml | 4.0E-1 | 7.0E-1 | 2.0E0 | 3.3E0 | 1.0E1 | 4.2E0 | 1.0E-9 | 1.0E-9 | 2.4E2 | 9.5E0 | 799 | 8 | 263 | 8 | 0.57 |
| Jo | pg/ml | 3.8E3 | 1.9E3 | 4.9E3 | 7.4E3 | 3.8E3 | 1.2E4 | 4.2E1 | 7.2E2 | 2.4E4 | 3.8E4 | 800 | 8 | 263 | 8 | 0.42 |
| Jp | pg/ml | 7.3E4 | 1.2E5 | 7.6E4 | 1.1E5 | 3.7E4 | 3.2E4 | 2.1E3 | 7.0E4 | 3.8E5 | 1.7E5 | 800 | 8 | 263 | 8 | 0.81 |
| Jq | pg/ml | 9.3E1 | 6.6E1 | 1.5E2 | 5.5E2 | 2.1E2 | 1.3E3 | 1.4E0 | 2.7E1 | 4.0E3 | 3.7E3 | 800 | 8 | 263 | 8 | 0.49 |
| Jr | pg/ml | 5.4E0 | 6.1E0 | 2.4E1 | 4.0E1 | 1.3E2 | 6.7E1 | 1.0E-9 | 1.0E-9 | 2.4E3 | 1.9E2 | 800 | 8 | 263 | 8 | 0.59 |
| Js | pg/ml | 1.3E1 | 1.4E1 | 4.2E1 | 2.6E1 | 1.7E2 | 3.0E1 | 1.0E-9 | 3.5E0 | 3.0E3 | 9.4E1 | 800 | 8 | 263 | 8 | 0.54 |
| Jt | pg/ml | 2.8E3 | 3.3E3 | 3.3E3 | 6.7E3 | 2.2E3 | 1.1E4 | 7.7E1 | 4.2E2 | 1.8E4 | 3.3E4 | 800 | 8 | 263 | 8 | 0.54 |
| Lh | pg/ml | 1.4E4 | 2.2E4 | 2.2E4 | 7.7E4 | 2.7E4 | 1.4E5 | 1.0E-9 | 5.6E3 | 2.6E5 | 4.1E5 | 799 | 8 | 264 | 8 | 0.65 |
| Li | pg/ml | 3.6E3 | 3.3E4 | 1.6E4 | 1.2E5 | 4.8E4 | 2.0E5 | 1.0E-9 | 1.5E3 | 9.2E5 | 5.9E5 | 799 | 8 | 264 | 8 | 0.78 |
| Lj | pg/ml | 3.0E3 | 1.7E4 | 2.3E4 | 7.6E4 | 6.4E4 | 1.2E5 | 1.0E-9 | 1.1E3 | 5.2E5 | 3.5E5 | 799 | 8 | 264 | 8 | 0.76 |
| Nv | pg/ml | 4.1E3 | 1.5E4 | 1.2E4 | 3.4E4 | 4.6E4 | 4.5E4 | 1.0E-9 | 1.8E3 | 1.1E6 | 1.3E5 | 805 | 8 | 264 | 8 | 0.74 |
| Nw | pg/ml | 9.4E3 | 2.5E4 | 1.3E4 | 6.0E4 | 1.6E4 | 7.5E4 | 8.6E1 | 3.6E3 | 2.1E5 | 2.1E5 | 805 | 8 | 264 | 8 | 0.78 |
| Nx | pg/ml | 2.2E2 | 3.6E2 | 4.2E2 | 8.7E2 | 6.6E2 | 9.9E2 | 1.0E-9 | 1.0E-9 | 7.4E3 | 2.8E3 | 805 | 8 | 264 | 8 | 0.67 |
| Ny | pg/ml | 7.1E0 | 3.2E1 | 5.9E1 | 1.1E2 | 8.9E2 | 2.1E2 | 1.0E-9 | 1.0E-9 | 2.5E4 | 6.2E2 | 805 | 8 | 264 | 8 | 0.72 |
| Oe | pg/ml | 8.8E1 | 9.6E1 | 3.0E2 | 3.1E2 | 7.9E2 | 5.5E2 | 1.0E-9 | 1.0E-9 | 1.9E4 | 1.6E3 | 797 | 8 | 263 | 8 | 0.51 |
| Of | pg/ml | 2.1E2 | 8.4E1 | 6.5E3 | 1.0E4 | 2.9E4 | 2.6E4 | 1.0E-9 | 1.0E-9 | 6.2E5 | 7.4E4 | 805 | 8 | 264 | 8 | 0.43 |
| Og | pg/ml | 8.5E-2 | 8.2E-2 | 7.9E-1 | 2.3E-1 | 5.0E0 | 4.1E-1 | 1.0E-9 | 1.0E-9 | 8.3E1 | 1.2E0 | 805 | 8 | 264 | 8 | 0.43 |
| Oh | pg/ml | 2.7E0 | 1.3E1 | 2.0E1 | 5.9E1 | 1.5E2 | 9.1E1 | 1.0E-9 | 9.7E-1 | 3.5E3 | 2.2E2 | 805 | 8 | 264 | 8 | 0.73 |
| Oi | pg/ml | 2.9E0 | 2.5E0 | 6.6E0 | 5.5E0 | 9.9E0 | 7.1E0 | 1.0E-9 | 1.0E-9 | 8.6E1 | 1.9E1 | 805 | 8 | 264 | 8 | 0.47 |
| Ok | pg/ml | 4.2E2 | 9.9E2 | 5.6E2 | 1.1E4 | 5.2E2 | 2.4E4 | 1.3E1 | 1.5E2 | 5.2E3 | 7.0E4 | 805 | 8 | 264 | 8 | 0.78 |
| Om | pg/ml | 3.9E2 | 1.3E3 | 8.5E2 | 4.6E3 | 2.2E3 | 6.6E3 | 1.0E-9 | 1.0E-9 | 3.6E4 | 1.7E4 | 805 | 8 | 264 | 8 | 0.65 |
| On | pg/ml | 1.9E2 | 7.3E2 | 3.0E2 | 3.6E3 | 4.0E2 | 5.7E3 | 1.0E-9 | 9.9E1 | 4.5E3 | 1.5E4 | 805 | 8 | 264 | 8 | 0.79 |
| Oy | pg/ml | 5.1E-1 | 6.2E-1 | 6.0E0 | 3.4E1 | 3.0E1 | 9.5E1 | 1.0E-9 | 2.4E-1 | 4.0E2 | 2.7E2 | 804 | 8 | 263 | 8 | 0.59 |
| Oz | pg/ml | 1.2E-2 | 1.2E-1 | 3.2E-1 | 2.2E-1 | 1.4E0 | 2.6E-1 | 1.0E-9 | 1.0E-9 | 2.9E1 | 7.1E-1 | 804 | 8 | 263 | 8 | 0.54 |
| Pa | pg/ml | 4.0E-1 | 5.6E-1 | 1.5E0 | 3.8E0 | 5.2E0 | 1.0E2 | 1.0E-9 | 9.6E-2 | 8.6E1 | 2.9E2 | 804 | 8 | 263 | 8 | 0.64 |
| Pb | pg/ml | 1.0E-9 | 1.7E-1 | 8.5E-1 | 2.3E1 | 1.7E1 | 6.4E1 | 1.0E-9 | 1.0E-9 | 4.9E2 | 1.8E2 | 804 | 8 | 263 | 8 | 0.73 |
| Pc | pg/ml | 6.4E-2 | 5.2E-1 | 3.6E-1 | 2.5E0 | 8.9E-1 | 4.1E0 | 1.0E-9 | 1.0E-9 | 1.6E1 | 1.1E1 | 804 | 8 | 263 | 8 | 0.71 |
| Pd | pg/ml | 2.0E0 | 3.2E0 | 5.0E0 | 6.2E0 | 3.0E1 | 6.7E0 | 1.0E-9 | 6.7E-1 | 8.4E2 | 1.8E1 | 804 | 8 | 263 | 8 | 0.64 |
| Pe | pg/ml | 2.3E1 | 6.1E1 | 1.1E2 | 1.9E3 | 3.6E2 | 5.0E3 | 1.0E-9 | 1.5E1 | 4.7E3 | 1.4E4 | 804 | 8 | 263 | 8 | 0.69 |
| Pf | pg/ml | 1.8E0 | 1.5E1 | 1.0E1 | 4.0E1 | 5.8E1 | 7.8E1 | 1.0E-9 | 5.2E-1 | 1.5E3 | 2.3E2 | 804 | 8 | 263 | 8 | 0.71 |
| Pg | pg/ml | 3.8E0 | 6.3E0 | 4.6E1 | 2.4E2 | 3.6E2 | 6.6E2 | 1.0E-9 | 5.5E-1 | 7.7E3 | 1.9E3 | 804 | 8 | 263 | 8 | 0.62 |
| aA | mg/dL | 8.1E-1 | 1.4E0 | 9.4E-1 | 1.9E0 | 4.7E-1 | 1.3E0 | 2.0E-1 | 6.2E-1 | 8.2E0 | 5.4E0 | 2235 | 16 | 391 | 16 | 0.81 |
| aC | mg/mL | 2.7E0 | 2.4E0 | 3.0E0 | 2.6E0 | 1.3E0 | 1.5E0 | 7.7E-1 | 1.3E0 | 8.2E0 | 6.3E0 | 465 | 8 | 174 | 8 | 0.39 |
| aD | ug/mL | 3.1E0 | 5.6E0 | 4.4E0 | 7.1E0 | 3.4E0 | 5.0E0 | 7.5E-1 | 2.2E0 | 3.1E1 | 1.7E1 | 465 | 8 | 174 | 8 | 0.70 |
| aE | mg/mL | 5.5E-1 | 6.8E-1 | 5.7E-1 | 6.9E-1 | 1.5E-1 | 2.0E-1 | 1.8E-1 | 4.5E-1 | 1.1E0 | 1.2E0 | 465 | 8 | 174 | 8 | 0.71 |
| aF | ng/mL | 2.3E0 | 8.9E-1 | 4.1E0 | 3.9E0 | 5.8E0 | 5.4E0 | 4.3E-3 | 4.3E-3 | 5.0E1 | 1.5E1 | 465 | 8 | 174 | 8 | 0.38 |
| aG | mg/mL | 1.3E-1 | 1.2E-1 | 1.5E-1 | 1.9E-1 | 8.1E-2 | 1.6E-1 | 4.3E-2 | 7.3E-2 | 5.0E-1 | 5.2E-1 | 465 | 8 | 174 | 8 | 0.49 |
| aH | ug/mL | 7.5E1 | 7.6E1 | 8.0E1 | 9.1E1 | 4.2E1 | 5.1E1 | 9.6E0 | 3.6E1 | 2.9E2 | 1.8E2 | 465 | 8 | 174 | 8 | 0.55 |
| aI | ug/mL | 1.8E2 | 2.1E2 | 1.8E2 | 1.9E2 | 6.0E1 | 4.7E1 | 4.7E1 | 1.4E2 | 3.7E2 | 2.7E2 | 465 | 8 | 174 | 8 | 0.55 |
| aJ | ug/mL | 2.5E0 | 6.2E0 | 3.2E0 | 7.2E0 | 2.2E0 | 3.9E0 | 7.3E-1 | 3.3E0 | 1.7E1 | 1.5E1 | 465 | 8 | 174 | 8 | 0.88 |
| aK | ng/mL | 1.5E0 | 1.6E0 | 1.9E0 | 2.6E0 | 1.4E0 | 2.9E-4 | 2.1E-1 | 1.8E1 | 4.7E0 | | 465 | 8 | 174 | 8 | 0.51 |
| aL | mg/mL | 7.9E-1 | 8.7E-1 | 8.0E-1 | 7.9E-1 | 2.5E-1 | 2.8E-1 | 2.2E-1 | 4.0E-1 | 1.7E0 | 1.2E0 | 465 | 8 | 174 | 8 | 0.52 |
| aM | U/mL | 2.2E1 | 4.5E1 | 4.5E1 | 8.5E1 | 9.2E1 | 1.3E2 | 4.2E-2 | 1.5E1 | 1.6E3 | 4.0E2 | 465 | 8 | 174 | 8 | 0.68 |

Figure 17 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aN | U/mL | 1.5E1 | 3.0E1 | 2.3E1 | 4.0E1 | 3.2E1 | 3.3E1 | 2.5E-3 | 3.9E0 | 3.8E2 | 9.2E1 | 465 | 8 | 174 | 8 | 0.69 |
| aO | pg/mL | 3.5E1 | 9.8E1 | 3.3E2 | 6.7E2 | 8.2E2 | 1.2E3 | 6.0E-2 | 6.0E-2 | 6.6E3 | 3.5E3 | 465 | 8 | 174 | 8 | 0.60 |
| aP | ng/mL | 1.7E0 | 3.2E0 | 2.0E0 | 3.6E0 | 1.3E0 | 1.8E0 | 5.4E-1 | 1.6E0 | 1.1E1 | 6.1E0 | 465 | 8 | 174 | 8 | 0.80 |
| aQ | ng/mL | 2.9E-1 | 2.8E-1 | 4.4E-1 | 2.7E-1 | 4.6E-1 | 1.6E-1 | 2.0E-4 | 6.1E-2 | 4.0E0 | 4.5E-1 | 465 | 8 | 174 | 8 | 0.41 |
| aR | ng/mL | 1.8E0 | 3.5E0 | 2.8E0 | 3.4E0 | 3.4E0 | 1.4E0 | 1.8E-1 | 7.7E-1 | 3.4E1 | 5.0E0 | 465 | 8 | 174 | 8 | 0.70 |
| aS | ng/mL | 2.8E-1 | 3.6E-1 | 6.9E-1 | 5.6E-1 | 1.8E0 | 5.6E-1 | 4.2E-3 | 9.1E-2 | 3.3E1 | 1.6E0 | 465 | 8 | 174 | 8 | 0.54 |
| aU | pg/mL | 7.4E1 | 1.0E2 | 1.2E2 | 1.2E2 | 1.5E2 | 7.6E1 | 7.4E-2 | 1.3E1 | 1.3E3 | 2.6E2 | 465 | 8 | 174 | 8 | 0.60 |
| aV | ng/mL | 6.0E-1 | 5.9E-1 | 1.0E0 | 1.0E0 | 1.9E0 | 1.3E0 | 7.6E-4 | 1.0E-1 | 3.3E1 | 4.2E0 | 465 | 8 | 174 | 8 | 0.51 |
| aW | pg/mL | 1.9E1 | 3.0E1 | 2.0E1 | 7.8E1 | 1.9E1 | 1.5E2 | 7.2E-2 | 7.2E-2 | 2.4E2 | 4.5E2 | 465 | 8 | 174 | 8 | 0.72 |
| aX | ng/mL | 9.6E0 | 9.2E0 | 1.4E1 | 1.4E1 | 1.5E1 | 1.2E1 | 3.0E-1 | 3.6E0 | 1.4E2 | 3.5E1 | 465 | 8 | 174 | 8 | 0.53 |
| aY | pg/mL | 6.0E1 | 6.2E1 | 7.7E1 | 1.0E2 | 8.4E1 | 8.3E1 | 4.1E-1 | 4.4E1 | 1.2E3 | 2.7E2 | 465 | 8 | 174 | 8 | 0.60 |
| aZ | pg/mL | 2.3E2 | 4.5E2 | 5.3E2 | 7.6E2 | 1.0E3 | 8.3E2 | 1.7E0 | 1.2E2 | 1.2E4 | 2.1E3 | 465 | 8 | 174 | 8 | 0.65 |
| bA | ng/mL | 9.5E0 | 9.1E1 | 3.4E1 | 1.6E2 | 8.4E1 | 2.0E2 | 3.0E-2 | 2.2E1 | 9.4E2 | 6.2E2 | 465 | 8 | 174 | 8 | 0.88 |
| bB | ng/mL | 2.9E2 | 3.8E2 | 3.1E2 | 3.8E2 | 1.7E2 | 1.5E2 | 8.6E0 | 1.6E2 | 1.0E3 | 6.1E2 | 465 | 8 | 174 | 8 | 0.65 |
| bC | ng/mL | 3.5E2 | 4.2E2 | 5.9E2 | 1.0E3 | 7.6E2 | 1.3E3 | 2.7E1 | 1.8E2 | 4.7E3 | 4.0E3 | 465 | 8 | 174 | 8 | 0.64 |
| bE | mg/mL | 5.4E0 | 6.3E0 | 5.7E0 | 6.5E0 | 2.0E0 | 2.6E0 | 1.4E0 | 3.2E0 | 1.3E1 | 9.6E0 | 465 | 8 | 174 | 8 | 0.58 |
| bF | pg/mL | 2.2E1 | 4.0E1 | 1.9E2 | 3.7E1 | 1.0E3 | 1.5E1 | 5.0E-2 | 8.1E0 | 1.1E4 | 5.3E1 | 465 | 8 | 174 | 8 | 0.63 |
| bG | ng/mL | 1.7E0 | 1.9E0 | 2.9E0 | 4.7E0 | 3.6E0 | 5.0E0 | 2.2E-2 | 2.4E-1 | 3.0E1 | 1.3E1 | 465 | 8 | 174 | 8 | 0.56 |
| bH | pg/mL | 5.7E-1 | 5.7E-1 | 4.9E0 | 6.2E0 | 1.5E1 | 8.9E0 | 5.7E-1 | 5.7E-1 | 2.8E2 | 2.3E1 | 465 | 8 | 174 | 8 | 0.54 |
| bI | ng/mL | 4.0E-3 | 4.0E-3 | 6.5E-2 | 3.9E-2 | 1.6E-1 | 1.0E-1 | 4.0E-3 | 4.0E-3 | 1.3E0 | 2.9E-1 | 465 | 8 | 174 | 8 | 0.47 |
| bJ | mg/mL | 2.1E0 | 2.6E0 | 2.4E0 | 3.0E0 | 1.9E0 | 1.9E0 | 2.5E-4 | 1.2E0 | 1.3E1 | 7.1E0 | 465 | 8 | 174 | 8 | 0.61 |
| bL | pg/mL | 3.8E0 | 7.5E0 | 8.4E0 | 9.1E0 | 1.0E1 | 6.8E0 | 4.6E-2 | 4.6E-2 | 4.9E1 | 2.0E1 | 465 | 8 | 174 | 8 | 0.60 |
| bM | ng/mL | 1.8E0 | 2.1E0 | 2.1E0 | 2.2E0 | 1.4E0 | 1.0E0 | 9.2E-3 | 6.4E-1 | 8.9E0 | 3.5E0 | 465 | 8 | 174 | 8 | 0.55 |
| bN | ng/mL | 4.6E1 | 2.2E1 | 1.3E2 | 2.7E1 | 2.5E2 | 2.2E1 | 1.4E-1 | 2.2E0 | 1.9E3 | 6.7E1 | 465 | 8 | 174 | 8 | 0.32 |
| bO | ng/mL | 4.0E-2 | 4.0E-2 | 9.5E0 | 2.7E1 | 2.3E1 | 6.7E1 | 4.0E-2 | 4.0E-2 | 2.0E2 | 1.9E2 | 465 | 8 | 174 | 8 | 0.48 |
| bP | mg/mL | 5.2E-1 | 8.2E-1 | 7.3E-1 | 9.8E-1 | 6.7E-1 | 8.5E-1 | 8.2E-2 | 9.2E-2 | 4.8E0 | 2.9E0 | 465 | 8 | 174 | 8 | 0.61 |
| bQ | pg/mL | 1.6E1 | 1.8E1 | 6.1E1 | 3.5E1 | 6.3E2 | 3.2E1 | 1.5E-1 | 6.7E0 | 1.3E4 | 9.3E1 | 465 | 8 | 174 | 8 | 0.59 |
| bR | ng/mL | 1.2E-2 | 1.2E-2 | 1.3E-1 | 1.2E-1 | 4.5E-1 | 1.7E-1 | 1.2E-2 | 1.2E-2 | 8.7E0 | 3.9E-1 | 465 | 8 | 174 | 8 | 0.51 |
| bS | pg/mL | 9.4E-1 | 9.4E-1 | 7.2E0 | 9.9E0 | 2.8E1 | 2.5E1 | 9.4E-1 | 9.4E-1 | 3.9E2 | 7.2E1 | 465 | 8 | 174 | 8 | 0.50 |
| bU | ng/mL | 1.1E-1 | 6.8E-2 | 1.9E-1 | 1.1E-1 | 3.7E-1 | 1.3E-1 | 1.3E-2 | 1.3E-2 | 6.6E0 | 3.4E-1 | 465 | 8 | 174 | 8 | 0.43 |
| bV | pg/mL | 4.6E2 | 9.6E2 | 5.7E2 | 9.8E2 | 8.0E2 | 5.6E2 | 1.5E2 | 3.5E2 | 1.7E4 | 2.2E3 | 465 | 8 | 174 | 8 | 0.81 |
| bW | pg/mL | 3.4E2 | 4.4E2 | 5.0E2 | 4.1E2 | 5.6E2 | 1.7E2 | 8.4E1 | 1.8E2 | 6.4E3 | 6.8E2 | 465 | 8 | 174 | 8 | 0.55 |
| bX | ng/mL | 2.5E-5 | 3.2E-3 | 2.7E-3 | 2.9E-3 | 3.4E-3 | 2.7E-3 | 2.5E-5 | 2.5E-5 | 2.0E-2 | 7.2E-3 | 465 | 8 | 174 | 8 | 0.53 |
| bZ | pg/mL | 2.4E2 | 3.4E2 | 9.4E2 | 9.9E2 | 4.3E3 | 1.5E3 | 1.5E-1 | 1.6E2 | 5.8E4 | 4.6E3 | 465 | 8 | 174 | 8 | 0.65 |
| cA | pg/mL | 6.0E-1 | 6.0E-1 | 2.8E0 | 3.1E0 | 1.8E1 | 7.2E0 | 6.0E-1 | 6.0E-1 | 3.7E2 | 2.1E1 | 465 | 8 | 174 | 8 | 0.51 |
| cB | ng/mL | 5.1E-2 | 4.1E-2 | 8.2E-2 | 8.1E-2 | 1.0E-1 | 8.3E-2 | 1.7E-3 | 1.1E-2 | 5.7E-1 | 2.6E-1 | 465 | 8 | 174 | 8 | 0.54 |
| cC | pg/mL | 4.6E1 | 4.6E1 | 4.8E1 | 4.2E1 | 4.0E1 | 2.2E1 | 1.0E0 | 1.0E0 | 4.5E2 | 6.4E1 | 465 | 8 | 174 | 8 | 0.48 |
| cD | pg/mL | 5.2E0 | 8.4E0 | 1.3E1 | 6.9E0 | 3.6E1 | 5.0E0 | 3.3E-1 | 3.3E-1 | 4.8E2 | 1.2E1 | 465 | 8 | 174 | 8 | 0.54 |
| cE | pg/mL | 3.9E1 | 4.0E1 | 1.5E2 | 4.3E1 | 4.5E2 | 3.3E1 | 1.2E-1 | 2.0E0 | 3.8E3 | 9.9E1 | 465 | 8 | 174 | 8 | 0.45 |
| cF | pg/mL | 1.2E1 | 5.3E-1 | 2.0E1 | 1.2E1 | 3.1E1 | 2.5E1 | 5.3E-1 | 5.3E-1 | 2.7E2 | 7.2E1 | 465 | 8 | 174 | 8 | 0.39 |
| cG | pg/mL | 4.7E1 | 6.4E1 | 1.1E2 | 7.2E1 | 5.1E2 | 4.2E1 | 6.4E0 | 1.5E1 | 1.0E4 | 1.4E2 | 465 | 8 | 174 | 8 | 0.59 |
| cH | uIU/mL | 2.8E0 | 1.8E0 | 6.2E0 | 6.9E0 | 1.2E1 | 1.2E1 | 8.6E-3 | 8.6E-3 | 1.6E2 | 3.4E1 | 465 | 8 | 174 | 8 | 0.41 |
| cI | ng/mL | 5.5E0 | 9.9E0 | 1.2E1 | 2.1E1 | 1.7E1 | 3.8E1 | 1.0E-3 | 9.7E-1 | 1.2E2 | 1.2E2 | 465 | 8 | 174 | 8 | 0.58 |
| cJ | ug/mL | 5.6E1 | 7.6E1 | 1.1E2 | 8.9E1 | 1.4E2 | 5.2E1 | 4.0E0 | 3.8E1 | 9.6E2 | 1.7E2 | 465 | 8 | 174 | 8 | 0.60 |
| cK | ng/mL | 3.8E-3 | 3.8E-3 | 4.9E-2 | 2.3E-2 | 1.7E-1 | 5.3E-2 | 3.8E-3 | 3.8E-3 | 1.7E0 | 1.6E-1 | 465 | 8 | 174 | 8 | 0.49 |
| cL | pg/mL | 2.0E2 | 1.6E2 | 4.0E2 | 1.7E2 | 1.3E3 | 6.8E1 | 1.6E1 | 8.4E1 | 2.4E4 | 2.9E2 | 465 | 8 | 174 | 8 | 0.40 |
| cM | pg/mL | 2.7E2 | 2.4E2 | 3.0E2 | 2.5E2 | 1.9E2 | 6.9E1 | 8.7E0 | 1.5E2 | 1.6E3 | 3.7E2 | 465 | 8 | 174 | 8 | 0.44 |
| cN | pg/mL | 1.2E2 | 1.7E2 | 1.3E2 | 1.6E2 | 6.5E1 | 4.3E1 | 3.8E1 | 1.0E2 | 1.1E3 | 2.2E2 | 465 | 8 | 174 | 8 | 0.75 |
| cO | pg/mL | 2.2E2 | 2.5E2 | 3.1E2 | 3.3E2 | 9.1E2 | 2.4E2 | 5.4E1 | 1.3E2 | 1.9E4 | 8.8E2 | 465 | 8 | 174 | 8 | 0.59 |
| cP | ng/mL | 2.5E3 | 3.7E3 | 2.6E3 | 3.7E3 | 9.5E2 | 1.1E3 | 6.2E2 | 2.1E3 | 7.3E3 | 5.1E3 | 465 | 8 | 174 | 8 | 0.78 |
| cQ | ng/mL | 5.3E-2 | 1.6E-1 | 1.4E-1 | 1.6E-1 | 2.8E-1 | 1.4E-1 | 2.0E-3 | 2.0E-3 | 2.2E0 | 3.9E-1 | 465 | 8 | 174 | 8 | 0.66 |
| cR | ng/mL | 2.9E2 | 4.9E2 | 4.8E2 | 1.4E3 | 6.9E2 | 2.6E3 | 2.0E1 | 1.6E2 | 7.7E3 | 7.7E3 | 465 | 8 | 174 | 8 | 0.68 |
| cS | ng/mL | 2.6E2 | 5.2E2 | 4.3E2 | 6.0E2 | 1.1E3 | 3.9E2 | 4.7E1 | 2.3E2 | 2.2E4 | 1.2E3 | 465 | 8 | 174 | 8 | 0.73 |
| cT | ng/mL | 3.5E1 | 1.2E2 | 8.9E1 | 2.3E2 | 2.0E2 | 2.3E2 | 3.7E0 | 5.7E1 | 2.1E3 | 6.5E2 | 465 | 8 | 174 | 8 | 0.84 |
| cU | ng/mL | 5.4E1 | 6.9E1 | 7.7E1 | 1.1E2 | 1.0E2 | 1.0E2 | 5.4E0 | 3.0E1 | 1.6E3 | 3.3E2 | 465 | 8 | 174 | 8 | 0.65 |
| cV | ng/mL | 1.8E-1 | 1.4E-1 | 4.4E-1 | 1.8E-1 | 2.3E0 | 1.5E-1 | 3.4E-4 | 6.4E-2 | 4.7E1 | 5.1E-1 | 465 | 8 | 174 | 8 | 0.39 |
| cW | mIU/mL | 5.1E-2 | 9.7E-2 | 1.4E-1 | 1.1E-1 | 7.0E-1 | 5.8E-2 | 3.7E-4 | 2.7E-2 | 9.7E0 | 2.0E-1 | 465 | 8 | 174 | 8 | 0.73 |

Figure 17 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cX | ng/mL | 1.2E-1 | 2.8E-2 | 1.5E0 | 1.6E-1 | 4.6E0 | 3.7E-1 | 2.3E-4 | 2.3E-4 | 2.8E1 | 1.1E0 | 465 | 8 | 174 | 8 | 0.33 |
| cY | ng/mL | 8.5E0 | 9.0E0 | 1.2E1 | 1.2E1 | 1.3E1 | 8.8E0 | 1.5E-1 | 6.6E-1 | 8.3E1 | 2.8E1 | 465 | 8 | 174 | 8 | 0.53 |
| cZ | ug/mL | 1.4E1 | 1.6E1 | 1.5E1 | 1.6E1 | 6.4E0 | 5.1E0 | 2.7E0 | 8.0E0 | 3.9E1 | 2.2E1 | 465 | 8 | 174 | 8 | 0.56 |
| dA | pg/mL | 3.3E2 | 5.1E2 | 3.6E2 | 5.4E2 | 3.0E2 | 2.6E2 | 9.0E1 | 1.7E2 | 5.8E3 | 8.8E2 | 465 | 8 | 174 | 8 | 0.73 |
| dB | ug/mL | 1.7E1 | 1.9E1 | 1.8E1 | 2.2E1 | 1.6E1 | 9.4E0 | 9.4E-1 | 1.3E1 | 2.5E2 | 4.1E1 | 465 | 8 | 174 | 8 | 0.61 |
| dC | nmol/L | 3.5E1 | 3.5E1 | 3.9E1 | 4.1E1 | 1.8E1 | 2.1E1 | 7.6E0 | 2.2E1 | 1.4E2 | 8.2E1 | 465 | 8 | 174 | 8 | 0.51 |
| dD | ug/mL | 3.5E1 | 2.8E1 | 3.6E1 | 3.1E1 | 1.1E1 | 1.0E1 | 1.3E1 | 1.5E1 | 7.6E1 | 4.8E1 | 465 | 8 | 174 | 8 | 0.38 |
| dE | ng/mL | 4.6E-1 | 4.3E-1 | 5.8E-1 | 9.0E-1 | 6.9E-1 | 1.0E0 | 8.4E-3 | 3.5E-1 | 7.2E0 | 3.3E0 | 465 | 8 | 174 | 8 | 0.61 |
| dF | ng/mL | 2.3E2 | 3.1E2 | 2.9E2 | 3.8E2 | 2.0E2 | 2.3E2 | 5.6E1 | 1.7E2 | 1.3E3 | 8.9E2 | 465 | 8 | 174 | 8 | 0.66 |
| dG | ng/mL | 1.2E1 | 1.7E1 | 1.5E1 | 2.0E1 | 1.3E1 | 9.1E0 | 2.2E0 | 1.1E1 | 1.8E2 | 3.5E1 | 465 | 8 | 174 | 8 | 0.73 |
| dH | pg/mL | 7.5E0 | 8.3E0 | 1.3E1 | 1.0E1 | 3.7E1 | 5.9E0 | 4.0E-2 | 3.0E0 | 6.7E2 | 2.2E1 | 465 | 8 | 174 | 8 | 0.57 |
| dI | pg/mL | 4.6E-1 | 4.6E-1 | 2.3E0 | 2.6E0 | 1.6E1 | 3.2E0 | 4.6E-1 | 4.6E-1 | 3.3E2 | 8.4E0 | 465 | 8 | 174 | 8 | 0.61 |
| dJ | ng/mL | 1.9E0 | 2.6E0 | 2.1E0 | 2.5E0 | 1.2E0 | 9.5E-1 | 3.2E-2 | 1.1E0 | 6.9E0 | 3.8E0 | 465 | 8 | 174 | 8 | 0.61 |
| dK | uIU/mL | 1.9E0 | 1.4E0 | 3.1E0 | 2.1E0 | 6.4E0 | 2.2E0 | 2.8E-4 | 3.8E-2 | 7.9E1 | 6.1E0 | 465 | 8 | 174 | 8 | 0.43 |
| dL | ng/mL | 8.9E2 | 1.3E3 | 1.0E3 | 1.1E3 | 5.3E2 | 2.4E2 | 2.6E2 | 7.7E2 | 3.8E3 | 1.4E3 | 465 | 8 | 174 | 8 | 0.65 |
| dM | pg/mL | 9.7E2 | 2.5E3 | 1.3E3 | 3.2E3 | 1.4E3 | 2.4E3 | 3.4E2 | 1.1E3 | 1.6E4 | 8.3E3 | 465 | 8 | 174 | 8 | 0.88 |
| dN | ug/mL | 9.3E1 | 1.3E2 | 9.8E1 | 1.4E2 | 3.5E1 | 4.5E1 | 1.6E1 | 6.9E1 | 2.4E2 | 2.0E2 | 465 | 8 | 174 | 8 | 0.75 |
| fR | ng/ml | 1.4E5 | 2.2E5 | 1.8E5 | 2.7E5 | 1.4E5 | 1.5E5 | 2.9E4 | 1.4E5 | 8.3E5 | 4.8E5 | 302 | 7 | 87 | 7 | 0.72 |

Analyte panel data:

Unconstrained panels with 3 analytes, where 1.0E-8 >= 'model p-value' > 0. Contains 181 panels of 597,622 total panels evaluated. : Mi{Hq(Fp Hu Hv Hw Ik Io Iq Jj Jo Lj Lv Ly Mb Mf Mj Ml Mp Ms My Nd Ne Nh Ni Nj Nk Nl Nq Nu Nx Oe Of Og Ok Om Oy Oz Pb Pc) Pd(Fp Hu Hv Hw Ii Ik In Iq Jj Li Lj Lv Lx Ly Mb Mf Ml Nd Ne Nf Nh Nj Nl Nu Of Ok Om Oz Pb Pc Pe Pg) Jj(Fp Hx Ij Ik In Js Lv Ly Md Mf Mh Ml Mt Mv Mw My Mz Ne Nf Nh Nl Nu Ny Of Om Pb Pg) Pg(Fp Hv Iq Lj Lv Ly Mb Mf Mj Ml Nd Ne Nh Nl Nu Of Ok Om Pb) Md(Fp Iq Mb Mj Ne Om) In(Fp Iq Mb Ne Nu Om) Of(Fp Iq Ne Om) On(Ii Om) NqaA LvIl} aA{Lv(Fp Ii Ij Iq Jj Lw Mj Mk Ng Nk Nq Nr Nu Of Ok Om Pb) Om(Lw Ok On) NuJj} Jj{Nu(Fr Hq Lv Nn Ok On Oy Pb) Om(Fr Nn Ok On) On(Of Qc) LwHu} On{Om(Ii Iq Jk Jo Md Nx Of) Of(Ii Iq)}

Unconstrained panels with 3 analytes, where 1.0E-7 >= 'model p-value' > 1.0E-8. Contains 1,000 panels of 597,622 total panels evaluated. : Mi{Pg(Et Fr Hq Hr Hu Hw Hx Ih Ii Ij Ik Im In Io Ip Ir Is It Iu Iv Jg Jh Ji Jk Jl Jm Jn Jo Jp Jq Jr Js Jt Lh Li Lu Lw Lx Lz Ma Mc Md Me Mg Mh Mk Mm Mn Mp Mq Mr Ms Mt Mu Mv Mw Mx My Mz Na Nb Nc Nf Ng Ni Nj Nk Nm Nn No Nq Nr Ns Nt Nv Nw Nx Ny Oe Og Oh Oi On Oy Oz Pa Pc Pe Pf Po Pz Qa Qb Qc Qd Qe) Pd(Et Fr Hq Hr Hu Hv Hw Hx Ih Ij Im In Ip Ir Is It Iu Iv Jg Jh Ji Jk Jl Jm Jn Jo Jp Jq Jr Js Jt Lh Lu Lw Lz Ma Mc Md Me Mg Mh Mj Mk Mm Mn Mp Mq Mr Ms Mt Mu Mv Mw Mx My Mz Na Nb Nc Ng Ni Nk Nm Nn No Nq Nr Ns Nt Nv Nw Nx Ny Oe Og Oh Oi On Oy Pa Pf Po Pz Qa Qb Qc Qd Qe) Hq(Et Fr Hr Hx Ih Ii Ij Im In Ip Ir Is It Iu Iv Jg Jh Ji Jk Jl Jm Jn Jp Jq Jr Js Jt Lh Li Lu Lw Lx Lz Ma Mc Md Me Mg Mh Mk Mm Mn Mq Mr Mt Mu Mv Mw Mx Mz Na Nb Nc Nf Ng Nm Nn No Nr Ns Nt Nv Nw Ny Oh Oi On Pa Pe Pf Po Pz Qa Qb Qc Qd Qe) Jj(Fr Hr Hu Hv Hw Ih Ii Im Iq Ir Is Iv Jg Jk Jl Jp Jr Lh Li Lj Lw Lx Mb Mg Mj Mk Mm Mp Mr Ms Mu Na Nb Nc Nd Ni Nj Nk Nn Nt Nv Nx Oe Og Oh Ok On Oy Oz Pa Pc Pe Pf Po Qa Qc Qe) Of(Hu Hv Im Io Lj Lv Ly Mb Md Mf Mj Ml Mn Mu Nd Nh Ni Nl Nn Nu Ok On Pb) In(Hu Hv Ik Jo Li Lj Lv Ly Mf Mj Ml Mn Nd Nh Ni Nk Nl Nn Ok Pb Pf) Md(Hv Hw Io Iu Jo Js Lj Lv Ly Mf Ml Mn Nd Nh Ni Nl Nq Nu Ok Pb) Js(Fp Iq Jn Jo Lj Lv Mb Mf Mn Na Nk Nu Nw Ok Om Pf) Jk(Fp Iq Lj Lv Mb Mu Ne Nh Nl Nu Om) Om(Jg Li Lj Lw Mt Mu Nk Nn Ok Pb) Jo(Hx Ml Mt Mv My Ny Ok Pb) Mn(Hx Ij Ml Mt Nf Ny Pb) Nk(Fp Ne Nl Nu) Mb(Ml Mt Pb) Il(Fp Ne Nq) Ok(Iq Jq Mj) Oy(Lj Ne On) Po(Fp Lj) LvaA NcNi IqOn} On{Jj(Et Fp Fr Hq Hr Hu Hv Hw Hx Ih Ii Ij Ik Im In Io Iq Ir Iu Iv Jg Jh Ji Jk Jl Jm Jn Jo Jp Jq Jr Js Jt Lh Li Lj Lu Lv Lw Lx Ly Lz Ma Mb Mc Md Mf Mg Mj Mk Ml Mm Mn Mp Mq Mr Ms Mt Mu Mv Mw My Mz Na Nb Nc Nd Ne Nf Nh Ni Nj Nk Nl Nm Nn No Nq Nv Nw Nx Ny Oe Og Oh Ok Oy Oz Pa Pb Pc Pd Pe Pf Pg Po Pz Qa Qb Qd Qe) Om(Et Fp Hq Hr Hu Hv Hw Hx Ih Ij Il In Io Ip Ir Is It Iu Iv Jg Jh Ji Jl Jm Jn Jp Jq Jr Js Jt Lh Li Lj Lv Lw Lx Mb Mc Mf Mg Mh Mj Mk Ml Mm Mn Mp Ms Mu Mv Mw Mx My Mz Na Nb Nc Ne Nf Ng Nh Ni Nj Nk Nl Nm Nn Nq Nr Ns Nu Nv Ny Oe Og Oh Oi Ok Oy Pd Pg Po Pz Qb Qc) Ii(aA Fp Hu Hv Hw Iq Iv Jl Lj Lv Lw Lx Ly Mb Md Mf Mk Ml Mp Mr Nd Ne Nk Nq Nr Nu Nx Ok Pa Pb Pe Qc) Of(Fp Ij In Jk Jo Jq Js Jt Lv Lw Ly Mb Md Mf Mj Mp Ms My Nd Ne Nh Ni Nk Nu Nv Nx Og Ok Po Pz Qb Qc) Jo(Fp Iq Lv Mb Mf Nu Oe) aA(Iq Lv Nq) Mj(Md Pg) Il(Lv Nq) NuIn} Jj{Nu(Fp Hu Hv Hw Hx Ii Ij Ip Is Iv Jg Ji Jk Jl Jo Jp Jt Lh Li Lw Lx Ma Mg Mj Mk Mn Mp Mr Mu Mv My Na Nb Nd Nf Nk Nr Nv Nw Og Oh Om Pa Pc Pe Po) Ok(Fp Fr Hu Hv Hw Ik Iq Jq Li Lv Lw Ly Mb Md Mf Ml Mq Mu Nc Nd Ne Nh Nk Nl Nn Of Oh Oy Pb Pc Qc) Nn(Fp Hu Hv Hw Ik Iv Lw Lx Ly Md Mr Nd Ne Nh Nk Of Oy Pb) Fr(Fp Hv Hw Lv Lw Ly Nd Ne Nh Nq Pb) Lv(Hw Il Jg Jl Lw Lx Mk Mr Mu Oy) Lw(aA Fp Hq Hv Ik Mu Nh Oy Pb) Lx(Fp Js Md Mj Mz Ne Nh Ni Om) Om(Jg Jk Li Mu Nv Nw Oh) WmNa FpaA MpOy LiPb} aA{Lv(Et Fr Hq Hr Hu Hv Hw Hx Ih Ik Il Im In Io Ip Ir Is It Iu Iv Jg Jh Ji Jk Jl Jm Jn Jo Jp Jq Jr Js Jt Lh Li Lj Lu Lx Ly Lz Ma Mb Mc Md Me Mf Mg Mh Ml Mm Mn Mp Mq Mr Ms Mt Mu Mv Mw Mx My Mz Na Nb Nc Nd Ne Nf Nh Ni Nj Nl Nm Nn No Ns Nt Nv Nw Nx Ny Oe Og Oh Oi Oy Oz Pa Pc Pd Pe Pf Pg Po Pz Qa Qb Qc Qd Qe) Lw(Fp Iq Mf Ml Nd Of Pc) Ok(Iq Jq Jt Nd Of Pc) Om(Ji Nw) BccX FpNr aDbO aFcP} Ok{Nn(Ii Jq Of Om) Om(Mu Oh) NuIi LvJq} Lv{Il(Iv Lw Mk Mr Pa Pb)} bA{cE(aM bO dM)}

Unconstrained panels with 3 analytes, where 1.0E-6 >= 'model p-value' > 1.0E-7. Contains 2,931 panels of 597,622 total panels evaluated. : Jj{Lx(aA Et Fr Hq Hr Hu Hv Hw Hx Ih Ii Ij Ik Il Im In Io Ip Iq Ir Is It Iu Iv Jg Jh Ji Jk Jl Jm Jn Jo Jp Jq Jr Jt Lh Li Lj Lu Lv Lw Ly Lz Ma Mb Mc Me Mf Mg Mh Mk Ml Mm Mn Mp Mq Mr Ms Mt Mu Mv Mw Mx My Na Nb Nc Nd Nf Ng Nj Nk Nl Nm No Nq Nr Ns Nt Nv Nw Nx Ny Oe Of Og Oh Oi Ok Oy Oz Pa Pb Pc Pd Pe Pf Pg Po Pz Qa Qb Qc Qd Qe) Fr(aA Et Hq Hr Hu Hx Ih Ii Ij Ik Im In Io Ip Iq Ir Is It Iu Iv Jg Jh Ji Jk Jl Jm Jn Jo Jp Jq Jr Js Jt Lh Li Lj Lu Lz Ma Mb Mc Md Me Mf Mg Mh Mj Mk Ml Mm Mn Mp Mq Mr Ms Mt Mu Mv Mw Mx My Mz Na Nb Nc Nf Ng Ni Nj Nk Nl Nm Nn No Nr Ns Nt Nv Nw Nx Ny Oe Of Og Oh Oi Oy Oz Pa Pc Pd Pe Pf Pg Po Pz Qa Qb Qc Qd Qe) Nn(aA Et Hq Hr Hx

Pc(Il Jt Md Nf Oy) Nn(Jt Mj Ne Oe) Fp(Jt Mj Nk) Lv(Il Mj) Nc(Ni Nk) Ii(Hv Oh) Pb(Il Mj) NeNk JpJt} bA{cE(aD Af aJ aN aP aS aW aY bC bJ cN cP cS cX dA dN) bO(aD aJ aM aW dM) aJ(aO cP cV) AfBc aDbJ} Il{Lv(Fp Hv Hw Ij Jl Lj Lx Mj Nb Nn No Nr Nu Nw Of Om Pc Pe) Lx(Iq Mj Om Pc Pd)} Om{Fr(Fp Ji Lv Lw Nu) Nn(Ji Lv Lx) Mu(Ji Lv Lw) Lx(In Pd) Li(Lv Lw) MdNw} aJ{Af(bN dG) cT(cE cP) CxdG} Lx{In(Iq Nu) NcNk} Nw{Nk(Nc Ne) MdMj} cEcTdM

Unconstrained panels with 3 analytes, where 1.0E-5 >= 'model p-value' > 1.0E-6. Contains 13,009 panels of 597,622 total panels evaluated. : Jj{Wm(Et Fp Fr Hr Hu Hv Hw Hx Ih Ii Ij Ik Im In Ip Ir Is It Iu Jg Jh Ji Jk Jl Jm Jo Jp Jq Js Lh Li Lj Lv Lw Lx Ly Lz Ma Mb Mc Md Me Mf Mg Mh Mj Mk Ml Mm Mn Mp Mq Mr Ms Mt Mu Mv Mw Mx My Mz Nb Nc Nd Ne Nf Ng Nh Ni Nj Nk Nl Nm Nn No Nq Nr Ns Nt Nu Nv Nw Oe Of Og Oh Oi Ok Om On Oz Pa Pb Pc Pd Pe Pf Pg Po Pz Qa Qb Qc Qd Qe) Lh(aA Et Hq Hr Hv Hw Hx Ih Ii Ij Ik Im In Io Ip Iq Ir Is It Iu Iv Jg Jh Ji Jk Jl Jm Jn Jo Jp Jq Jr Js Jt Lj Lu Ly Lz Ma Mb Mc Md Me Mf Mg Mh Mj Mk Ml Mm Mn Mp Mq Mr Ms Mt Mv Mw Mx My Mz Na Nb Nc Nd Ne Nf Ng Ni Nj Nk Nl Nm No Nq Nr Ns Nt Nv Nw Nx Ny Oe Of Og Oi Oz Pa Pc Pd Pe Pf Pg Po Pz Qa Qb Qc Qd Qe) Jt(aA Et Hq Hr Hv Hw Hx Ih Ii Ij Ik Im In Ip Iq Ir Is It Iv Jg Jh Ji Jk Jl Jm Jo Jp Jq Jr Js Li Lj Ly Lz Ma Mb Mc Md Me Mf Mg Mh Mj Mk Ml Mm Mn Mp Mq Mr Ms Mt Mv Mw Mx My Mz Na Nb Nc Nd Ne Nf Ng Nh Ni Nj Nk Nl Nm No Nq Nr Ns Nt Nv Nw Nx Oe Of Og Oh Oi Oy Oz Pa Pc Pd Pe Pf Pg Po Pz Qa Qb Qc Qd Qe) Nr(aA Et Hq Hr Hv Hw Hx Ih Ii Ij Im In Ip Iq Ir Is It Iu Iv Jh Jk Jl Jm Jn Jo Jp Jq Jr Js Lj Lu Ly Lz Ma Mb Mc Md Me Mf Mg Mh Mj Mk Ml Mm Mn Mp Mq Mr Ms Mt Mv Mw Mx My Mz Na Nb Nc Nd Ne Nf Ng Nh Ni Nj Nk Nl Nm No Nq Ns Nt Nx Ny Oe Of Og Oh Oi Om Oz Pa Pc Pd Pe Pf Pg Po Pz Qa Qb Qc Qd Qe) Pe(aA Et Hq Hr Hv Hw Hx Ih Ii Ij Il Im In Io Ip Iq Ir Is It Iu Iv Jh Jk Jl Jm Jn Jo Jp Jq Jr Js Lj Lu Ly Lz Ma Mb Mc Md Me Mf Mg Mh Mj Mk Ml Mm Mn Mp Mq Mr Ms Mt Mv Mw Mx Mz Na Nb Nc Nd Ne Nf Ng Ni Nj Nk Nl Nm No Nq Ns Nt Nw Nx Ny Oe Of Og Oi Oz Pa Pc Pd Pf Pg Po Pz Qa Qb Qc Qd Qe) Nb(aA Et Hq Hr Hw Hx Ih Ii Ij Im In Io Ip Iq Ir Is It Iu Iv Jg Jh Ji Jk Jl Jm Jn Jo Jp Jq Jr Js Lj Lu Ly Lz Ma Mb Mc Me Mg Mh Mj Mk Ml Mm Mn Mp Mq Mr Ms Mt Mv Mw Mx My Mz Na Nc Nd Nf Ng Ni Nj Nk Nl Nm No Nq Ns Nt Nv Nw Nx Ny Oe Of Og Oi Oz Pa Pc Pd Pf Pg Po Pz Qa Qb Qc Qd Qe) Pa(aA Et Hq Hr Hv Hw Hx Ih Ii Ij Il Im In Io Ip Iq Ir Is It Iu Iv Jh Jk Jl Jm Jn Jo Jp Jq Jr Js Lj Lu Ly Lz Ma Mb Mc Md Me Mf Mh Mj Mk Ml Mm Mn Mp Mq Mr Ms Mt Mv Mw Mx Mz Na Nc Nd Ne Nf Ng Ni Nj Nk Nl Nm No Nq Ns Nt Nw Nx Ny Oe Of Og Oi Oz Pc Pd Pf Pg Po Pz Qa Qb Qc Qd Qe) Po(Et Hq Hr Hv Hw Hx Ih Ii Ij Im In Io Ip Iq Ir Is It Iu Iv Jg Jh Ji Jk Jl Jm Jn Jo Jp Jq Jr Lj Lu Ly Lz Ma Mb Mc Me Mf Mg Mh Mj Mk Mm Mn Mp Mq Mr Ms Mt Mv Mw Mx My Mz Na Nc Nd Nf Ng Ni Nj Nk Nl Nm No Nq Ns Nt Nv Nw Nx Ny Oe Of Og Oi Oy Oz Pd Pf Pg Pz Qa Qb Qc Qd Qe) Nv(Et Fp Hq Hr Hu Hx Ih Ii Ij Ik Im In Io Ip Iq Ir Is It Iu Jg Jh Ji Jk Jm Jn Jo Jp Jq Jr Js Lj Lu Ly Lz Ma Mb Mc Me Mf Mg Mh Mj Ml Mm Mn Mp Mq Ms Mt Mu Mv Mw Mx My Mz Na Nc Nd Nf Ng Ni Nj Nk Nl Nm No Nq Ns Nt Nw Nx Ny Oe Of Og Oh Oi Oz Pc Pd Pf Pg Pz Qa Qb Qd Qe) Iv(aA Et Hq Hr Hv Hw Hx Ih Ii Ij Im In Io Ip Iq Ir Is It Iu Jh Jk Jl Jm Jn Jo Jp Jq Jr Js Lj Lu Ly Lz Ma Mb Mc Md Me Mh Mj Mk Ml Mm Mn Mp Mq Mr Ms Mt Mw Mx Mz Na Nc Nd Ne Nf Ng Ni Nj Nk Nl Nm No Nq Ns Nt Nx Ny Oe Of Og Oi Oz Pc Pd Pf Pg Pz Qa Qb Qc Qd Qe) Ji(Et Fp Hr Hu Hx Ih Ii Ij Ik Im In Io Ip Iq Ir Is It Iu Jg Jh Jk Jm Jn Jo Jp Jq Jr Js Lj Lu Lz Ma Mb Mc Md Me Mf Mg Mh Mj Ml Mm Mn Mp Mq Ms Mt Mv Mw Mx My Mz Na Nc Nd Nf Ng Ni Nj Nk Nl Nm No Nq Ns Nt Nw Nx Ny Oe Of Og Oi Oz Pd Pf Pg Pz Qa Qb Qc Qd Qe) Jl(aA Et Hq Hr Hv Hw Hx Ih Ii Ij Im In Io Ip Iq Ir Is It Iu Jh Jk Jm Jn Jo Jp Jq Jr Js Lj Lu Ly Lz Ma Mb Mc Md Me Mh Mj Mk Ml Mm Mn Mp Mq Mr Ms Mt Mv Mw Mx Mz Na Nc Nd Ne Nf Ng Ni Nj Nl Nm No Nq Ns Nt Nx Ny Oe Of Og Oi Oz Pc Pd Pf Pg Pz Qa Qb Qc Qd Qe) Mk(aA Et Hq Hr Hw Hx Ih Ii Ij Im In Io Ip Iq Ir Is It Iu Jh Jk Jm Jn Jo Jp Jq Jr Js Lj Lu Ly Lz Ma Mb Mc Md Me Mh Mj Ml Mm Mn Mp Mq Mr Ms Mt Mw Mx Mz Na Nc Nd Ne Nf Ng Ni Nj Nk Nl Nm No Nq Ns Nt Nx Ny Oe Of Og Oi Oz Pc Pd Pf Pg Pz Qa Qb Qc Qd Qe) Hv(aA Et Fp Hq Hr Hx Ih Ii Ij Im In Io Ip Iq Ir Is It Iu Jh Jk Jm Jn Jo Jp Jq Jr Js Lj Lu Ly Lz Ma Mb Mc Md Me Mf Mg Mh Mj Ml Mn Mq Ms Mt Mv Mw Mx My Mz Na Nc Nd Ne Nf Ng Nh Ni Nj Nl Nm No Nq Ns Nt Nx Ny Oe Of Og Oi Oz Pd Pf Pg Pz Qa Qb Qc Qd Qe) Mr(aA Et Hq Hr Hw Hx Ih Ii Ij Im In Io Ip Iq Ir Is It Iu Jh Jk Jm Jn Jo Jp Jq Jr Js Lj Lu Ly Lz Ma Mb Mc Md Me Mh Mj Ml Mm Mn Mp Mq Ms Mt Mw Mx Mz Na Nc Nd Ne Nf Ng Ni Nj Nk Nl Nm No Nq Ns Nt Nx Ny Oe Of Og Oi Oz Pc Pd Pf Pg Pz Qa Qb Qc Qd Qe) Fp(Et Hq Hr Hu Hx Ih Ij Ik Il Im In Ip Iq Ir Is It Iu Jh Jk Jm Jp Jq Jr Js Lj Lu Ly Lz Ma Mb Mc Md Me Mf Mg Mh Mj Ml Mm Mn Mq Mt Mv Mw Mx Mz Na Nc Nd Ne Ng Nh Ni Nj Nk Nl Nm No Nq Ns Nt Nx Oe Of Og Oh Oi Om Oz Pd Pf Pg Pz Qa Qb Qc Qd Qe) Pc(Et Hq Hr Hw Hx Ih Ii Ij Il Im In Io Ip Iq Ir Is It Iu Jh Jk Jm Jn Jo Jp Jq Jr Js Lu Lz Ma Mb Me Mf Mg Mh Mj Ml Mm Mn Mp Mq Ms Mt Mv Mw Mx Mz Na Nc Nd Nf Ng Ni Nj Nl Nm No Nq Ns Nx Ny Oe Of Og Oi Om Oy Oz Pb Pd Pf Pg Pz Qa Qb Qc Qd Qe) Oh(aA Et Hq Hr Hx Ih Ij Im In Io Ip Iq Ir Is It Iu Jh Jk Jm Jn Jp Jq Jr Lj Lu Lz Ma Mb Mc Me Mf Mg Mh Mj Ml Mm Mn Mp Mq Ms Mt Mv Mw Mx Mz Na Nc Nd Ne Ng Nh Nj Nl Nm No Nq Ns Nt Nx Ny Oe Of Og Oi Oz Pd Pf Pg Pz Qa Qb Qc Qd Qe) Oy(Et Hq Hr Hu Hx Ih Ii Ij Im In Io Ip Iq Ir It Iu Jh Jk Jm Jn Jo Jp Jq Jr Js Lj Lu Ly Lz Ma Mb Mc Md Me Mf Mg Mh Mj Ml Mn Mq Ms Mt Mv Mw Mx My Na Nd Nf Ng Ni Nj Nl Nm No Nq Ns Nx Ny Oe Of Og Oi Oz Pb Pd Pf Pg Pz Qa Qb Qc Qd) Hw(aA Et Hq Hr Hx Ih Ii Ij Im In Io Ip Iq Ir Is It Iu Jh Jk Jm Jn Jo Jp Jq Jr Js Lj Lu Ly Lz Ma Mb Mc Md Me Mh Mj Ml Mn Mp Mq Ms Mw Mx Mz Nc Nd Ne Nf Ng Nj Nk Nl Nm No Nq Ns Nx Ny Oe Of Og Oi Oz Pf Pg Pz Qa Qb Qc Qd Qe) Li(Et Hr Ih Il Im In Io Ip Ir Is It Iu Jh Jk Jm Jn Jo Jp Jq Jr Lj Lu Lz Ma Mb Mc Md Me Mf Mg Mh Mj Ml Mm Mn Mq Ms Mt Mv Mw Mx Mz Na Nc Ne Ng Nh Ni Nj Nl Nm No Nq Ns Nt Nx Ny Oe Of Og Oi Oz Pd Pf Pg Pz Qa Qb Qd Qe) Mp(aA Et Hq Hr Hx Ih Ii Ij Im Ip Iq Ir Is It Iu Jh Jk Jm Jo Jp Jq Js Lj Lz Ma Mb Mc Md Mf Mg Mh Mj Ml Mm Mn Mq Mt Mv Mw Mx Mz Nc Nd Ne Nf Ng Ni Nj Nk Nl Nm No Nq Nt Nw Nx Oe Of Og Om Oz Pd Pf Pg Qa Qb Qc Qd Qe) aA(Et Hq Hr Hx Ih Ii Ij Il Im In Io Ip Ir Is It Iu Jh Jk Jm Jn Jo Jp Jr Js Lu Lz Ma Mc Md Me Mh Mj Mn Ms Mt Mu Mv Mw Mx My Mz Na Nc Ne Nf Ng Nh Nj Nl Nm No Nq Ns Ny Oe Of Og Oi Oz Pd Pf Pg Pz Qa Qb Qc Qd Qe) Nt(Hq Hr Hu Hx Ih Ii Ij Ik Im Ip Iq Ir Is It Iu Jg Jh Jk Jo Jp Jq Js Lj Ly Ma Mb Mc Md Mf Mg Mh Mj Ml Mm Mn Mq Ms Mt Mv Mw Mx My Mz Na Nc Nd Ne Nf Nh Ni Nj Nk Nl No Nq Ns Nw Nx Of Og Pd Pf Pg Qa Qb Qc Qe) Nw(Et Hq Hr Hx Ih Ii Ij Il Im Io Ip Iq Ir Is It Iu Jg Jh Jk Jm Jn Jo Jp Jq Jr Lu Lz Ma Mb Mc Me Mg Mh Mj Mm Mn Mq Ms Mt Mv Mw Mx Na Nf Ng Ni Nj Nk Nm No Nq Ns Nx Oe Of Og Oi Oz Pd Pf Pg Pz Qa Qb Qd Qe) Pb(Et Hq Hr Ii Ij Im In Io Ip Iq It Iu Jh Jm Jn Jq Jr Js Lu Ly Lz Ma Mb Mc Md Me Mf Mh Mj Ml Mn Mq Ms Mw Mx Mz Na Nc Nd Nf Ng Ni Nj Nk Nl Nm Nq Ns Nx Ny Oe Of Og Oi Om Oz Pd Pf Pg Pz Qa Qb Qc Qd) Ik(Et Hq Hr Hu Hx Ih Ii Ij Im Ip Ir It Iu Jh Jk Jm Jo Jp Jq Lj Ly Lz Ma Md Mf Mg Mh Ml Mm Mn Mq Mt Mv Mw Mx My Mz Nc Nd Ne Nf Nh Ni Nj Nk Nl Nm No Nq Nx Oe Of Og Om Pd Pf Pg Pz Qa Qb Qd Qe) Mu(Et Hr Ih Ij Im In Io Ip Iq Ir It Jh Jk Jm Jn Jp Jq Jr Js Lu Lz Ma Mb Mc Me Mg Mh Ml Mn Mq Ms Mt Mv Mw Mx My Mz Na Nc Ng Ni Nj Nm No Nq Ns Nx Ny Oe Of Og Oi Oz Pf Pg Pz Qa Qb Qc Qd Qe) Jg(Et Hr Hx Ih Ii Ij Il Im In Io Ip Ir It Iu Jk Jm Jn Jo Jp Jq Jr Js Lu Lz Ma Mb Mc Me Mg Mh Ml Mm Mn Mq Ms Mt Mv Mw Mx Mz Na Nf Ng Nj Nm No Nq Nx Ny Oe Og Oi Oz Pd Pf Pg Pz Qa Qb Qc Qd Qe) Hq(Et Hu Hx Ih Ii Ij Im Ip Iq Ir Is It Iu Jh Jk Jo Jp Jq Js Lj Ly Ma Mc Md Mf Mg Mj Ml Mm Mn Mq Mt Mv Mx My Mz Nc Nd Ne Nf Nh Ni Nj Nk Nl Nm No Nx Oe Og Om Pd Pf Pg Pz Qa Qb Qc Qd Qe) Hu(Et Hr Hx Ih Ii Ij Im Io Ip Iq Ir It Iu Jh Jk Jm Jo Jp Jq Lj Ly Lz Ma Mb Md Mf Mg Mh Ml Mm Mn Mq Mt Mv Mx My Mz Nc Nd Ne Nf Nh Ni Nk Nl Nm No Nx Of Og Om Pd Pf Pg Pz Qa Qb Qd Qe) Is(Et Hx Ih Ii Ij Im Ip Iq Ir Iu Jh Jk Jo Jp Jq Jr Js Lj Ly Ma Mb Md Mf Mg Mj Ml Mm Mn Mq Mt Mv My Mz Na Nc Nd Ne Nf Ng Nh Ni Nj Nk Nl Nm No Nq Nx Og Pd Pf Pg Pz Qa Qc Qe) Nh(Et Hr Hx Ih Ii Ij Im Ip Ir It Iu Jh Jk Jo Jp Jq Js Lj Ly Ma Md Mf Mg Mh Mj Mm Mn Mq Mt Mv Mw Mx My Mz Nc Nd

Figure 17 Continued

Ne Ni Nj Nm No Nq Nx Oe Of Og Om Pd Pf Pg Qa Qb Qc Qe) Jo(Hx Ih Li Ij Im Ip Iq Ir Jh Jk Jp Jq Jr Lj Ly Ma Mb Mc Md Mf Mg Ml Mm Mn Mq Mt Mv Mw Mx My Mz Na Nc Nd Ne Nf Ni Nj Nk Nl No Nq Nx Of Og Om Pd Pf Pg Qa Qb Qd Qe) Ii(Et Hx Ih Ij Im Ip Ir Jh Jk Jm Jp Jq Lj Ly Ma Mb Md Mf Mg Ml Mm Mn Mq Mt Mv Mx My Mz Na Nc Nd Ne Ni Nj Nk Nl Nm No Nq Nx Og Om Pd Pf Pg Pz Qa Qb Qd Qe) My(Et Hx Ih Ij Im Ip Iq Ir It Iu Jh Jk Jp Jq Lj Ly Ma Mb Md Mf Mg Mj Ml Mm Mn Mq Ms Mt Mv Mx Mz Nc Nd Ne Nf Nj Nk Nl No Nx Of Om Pd Pf Pg Qa Qb Qe) Nf(Et Hx Ih Im Ip Ir Jh Jk Jp Jq Lj Ly Ma Mb Md Mf Mg Mm Mq Mt Mv Mx Mz Nc Nd Ne Ni Nj Nk Nl No Nx Om Pd Pf Qa Qb Qd Qe) Mv(Hx Ih Ij Im Ip Ir It Iu Jk Jp Jq Js Lj Ly Md Mf Mg Mj Mm Mn Mq Mt Mx Mz Nc Nd Ne Ni Nk Nl No Nx Of Pd Pg Qc Qe) Jk(Hx Ij Ip Iq Ir It Iu Jp Jq Lj Ly Mb Md Mf Mg Mj Ml Mm Mq Mt Mx Mz Nc Nd Ne Ni Nk Nl No Of Og Pd Qc Qe) Hx(Ij In Ip Iq Ir It Jh Jp Jq Js Lj Ly Md Mf Mg Mj Ml Mm Mq Mt Nc Nd Ne Ni Nk Nl No Ny Pd Pf Qc Qe) Om(Et Ih Ij Im Ip Ir Jh Jm Jp Jq Lj Ma Mg Mj Mn Mt Mw Mx Mz Ne Nk Nl No Nx Ny Pd Pf Pg Qa Qb Qd) Lv(Et Hr In Io Iq Jn Jr Js Lu Lz Mb Mc Me Mf Mh Ml Mq Ms Na Ng Ni Ns Ny Of Oi Oz Qb Qc Qd) Ij(Ih Im Ir Jp Lj Ly Md Mf Mg Mm Mq Mt Mz Nc Ne Ni Nk Nl No Pd Pf Qa Qe) Lw(Et Il In Io Jn Jq Jr Js Lz Mq Ms Na Nm Ns Nx Ny Og Oi Pz) Qe(Iq Iu Jq Js Ly Md Mg Mj Mm Nc Nd Ne Ni Nk Nl No Pd Pg Qc) Mj(Ih Im Jp Jq Jr Js Ly Lz Mg Mm Mt Nc Ne Nl Nx Pd Qd) Mg(Ih Ir It Jp Lj Ly Mt Mz Nc Nd Ne Nk Nl No Pg) Nc(Et Ip Jp Jq Ma Mm Mn Mq Mz Ni No Nx Pd Pg) Ly(Im Ir Jp Jq Lj Ma Mm Mt Mz No Pd Pf Qa) No(Jn Mc Md Mf Ml Mm Mt Na Pd) Nk(Ir Jp Lj Mt Pd Pf Pg) Nl(Jp Jq Mm Ni Pd) Lj(Jq Mm Mq Nq Pg) Jp(Mf Nd Ni Pd) Md(Ny Pd Pg) Nc(Mm Ni Pd) Il(Fr Nn) Ir(Iq Mm) NdPd} On{Nf(aA Et Fr Hq Hr Hu Hv Hw Hx Ih Ij Ik Il Im In Io Ip Ir Is It Iu Iv Jg Jh Ji Jk Jl Jm Jn Jp Jq Jr Js Lh Li Lj Lu Lw Lx Ly Lz Ma Mc Me Mf Mg Mh Mk Ml Mm Mn Mp Mq Mr Ms Mt Mu Mv Mw Mx My Mz Na Nb Nc Nd Ne Ng Nh Ni Nj Nk Nl Nm Nn No Nq Nr Ns Nt Nv Nw Nx Ny Oe Og Oh Oi Ok Oy Oz Pa Pc Pd Pe Pf Pg Po Pz Qa Qb Qc Qd Qe) In(aA Et Fr Hq Hr Hu Hw Hx Ih Ij Ik Il Im Io Ip Ir Is It Iu Iv Jg Jh Ji Jk Jl Jm Jn Jp Jq Jr Js Jt Lh Li Lj Lu Lw Lx Ly Lz Ma Mc Me Mf Mg Mh Mk Ml Mm Mn Mp Mq Mr Ms Mt Mu Mv Mw Mx My Mz Na Nb Nc Ng Ni Nj Nk Nl Nm Nn No Nq Nr Ns Nt Nw Nx Ny Oe Oh Oi Ok Oy Oz Pa Pb Pc Pd Pe Pf Pg Po Pz Qa Qb Qc Qd Qe) Lv(Et Fp Fr Hq Hr Hu Hv Hw Hx Ih Ij Ik Im Io Ip Iq Ir Is It Iu Iv Jg Jh Jl Jm Jn Jp Jq Jr Js Jt Li Lj Lw Lx Ly Lz Ma Mb Mc Me Mf Mg Mi Mj Mk Ml Mm Mn Mp Mq Mr Ms Mt Mu Mv Mw Mx My Mz Na Nb Nc Nd Ne Ng Nh Ni Nj Nk Nl Nm Nn Nq Nr Ns Nt Nu Nw Ny Oc Oh Oi Ok Oz Pa Pb Pc Pd Pe Pf Po Pz Qa Qb Qc Qd Qe) Mb(Et Fp Fr Hq Hr Hu Hv Hw Hx Ih Ij Ik Im Io Ip Ir Is It Iu Iv Jg Jh Ji Jl Jm Jn Jp Jq Js Jt Li Lj Lu Lw Lx Ly Lz Ma Mc Me Mf Mg Mh Mk Ml Mm Mn Mp Mq Mr Ms Mt Mu Mv Mw Mx My Mz Na Nb Nc Nd Ne Ng Nh Ni Nj Nl Nm Nn No Nq Nr Ns Nt Nw Nx Ny Oe Oh Oi Ok Oz Pa Pb Pc Pd Pe Pf Po Pz Qa Qb Qc Qd Qe) Og(Et Fr Hu Hv Hx Ih Ij Ik Il Im Io Ip Ir Is It Iu Iv Jg Jh Ji Jk Jl Jm Jn Jp Jq Jr Js Jt Li Lj Lu Lw Lx Ly Lz Ma Mc Me Mf Mg Mh Mj Mk Ml Mm Mn Mp Mq Mr Ms Mt Mu Mv Mw Mx My Mz Na Nb Nc Ng Nh Ni Nj Nk Nl Nm Nn No Nq Nr Ns Nt Nw Nx Ny Oe Oh Oi Ok Oz Pa Pb Pc Pd Pe Pf Po Pz Qa Qb Qc Qd Qe) Pg(aA Et Fr Hq Hr Hu Hv Hx Ih Ij Ik Im Io Ip Ir Is It Iu Iv Jg Jh Ji Jl Jm Jn Jp Jr Js Lh Li Lj Lu Lw Lx Ly Lz Ma Mc Me Mf Mg Mh Mk Ml Mm Mn Mp Mq Mr Ms Mt Mu Mv Mw Mx My Mz Na Nb Nc Nd Ng Nh Ni Nj Nk Nl Nm Nn No Nq Nr Ns Nt Nv Nw Ny Oh Oi Ok Oy Oz Pa Pc Pd Pe Pf Po Pz Qa Qb Qc Qd Qe) Jk(Et Fr Hq Hu Hv Hx Ih Ij Ik Il Im Io Ip Ir Is It Iu Iv Jg Jh Ji Jl Jm Jn Jp Jr Js Jt Lh Li Lj Lu Lw Lx Ly Lz Ma Mc Md Me Mf Mg Mh Mk Ml Mm Mn Mp Mq Mr Ms Mt Mv Mw Mx My Mz Na Nb Nc Nd Ng Ni Nj Nk Nl Nm No Nq Nr Ns Nt Nv Nw Ny Oe Oh Oi Ok Oy Oz Pa Pc Pd Pe Pf Po Pz Qa Qb Qc Qd Qe) aA(Et Fr Hq Hr Hu Hv Hw Hx Ih Ik Im Io Ip Ir Is It Iu Iv Jg Jh Ji Jl Jm Jn Jo Jp Jq Jr Js Lh Li Lu Lx Lz Ma Mc Md Me Mg Mh Mi Mj Mk Mm Mn Mq Mr Ms Mt Mu Mv Mw Mx My Mz Na Nb Nc Ne Ng Nh Ni Nj Nk Nl Nm Nn No Nr Ns Nt Nv Nw Nx Ny Oh Oi Ok Oy Pa Pd Pe Pf Po Pz Qa Qb Qc Qd Qe) Nu(Et Fp Fr Hq Hu Hv Hw Hx Ih Ik Im Io Ip Ir Is It Iu Iv Jg Jh Ji Jl Jm Jn Jp Jq Jr Li Lj Lu Lw Lx Ly Lz Ma Mc Me Mf Mg Mh Mk Ml Mm Mn Mp Mq Mr Mt Mu Mv Mw Mx My Mz Nb Nc Nd Ne Ng Nh Ni Nj Nl Nm Nn No Nq Nr Ns Nw Ny Oh Oi Ok Oz Pa Pb Pc Pd Pe Pf Po Pz Qa Qb Qc Qd Qe) Md(Et Fr Hq Hu Hv Hx Ih Ik Im Ip Ir Is It Iv Jg Jh Ji Jl Jm Jn Jp Jr Lh Li Lj Lu Lw Lx Ly Lz Ma Mc Me Mf Mg Mh Mk Mm Mn Mp Mq Mr Ms Mt Mu Mv Mw Mx My Mz Na Nb Nc Nd Ng Nh Nj Nk Nl Nm Nn No Nq Nr Ns Nt Nv Nw Ny Oh Oi Ok Oy Oz Pa Pb Pd Pe Pf Po Pz Qa Qb Qc Qd Qe) Oy(Et Fr Hq Hr Hu Hv Hx Ih Ij Ik Il Im Io Ip Ir Is It Iu Iv Jg Jh Ji Jl Jm Jn Jp Jr Li Lj Lu Lw Lx Ly Lz Ma Mc Me Mf Mg Mh Mk Ml Mm Mn Mp Mq Mr Ms Mt Mu Mv Mw Mx My Mz Na Nb Nc Ng Nh Nj Nl Nm No Nq Nr Ns Nt Nw Ny Oe Oh Oi Ok Oz Pa Pd Pe Pf Po Pz Qa Qb Qd Qe) Mi(Et Fr Hr Hu Hv Hw Hx Ih Ij Ik Il Im Io Ip Ir Is It Iu Iv Jg Jh Ji Jl Jm Jn Jp Lh Li Lj Lu Lw Lx Ly Lz Ma Mc Me Mf Mg Mh Mk Ml Mm Mq Mr Ms Mt Mu Mv Mw Mx My Mz Na Nb Nc Ng Nh Nj Nl Nm Nn No Nq Nr Ns Nt Nw Ny Oh Oi Ok Oz Pa Pb Pc Pe Pf Pz Qa Qb Qc Qd Qe) Ne(Fp Fr Hq Hr Hu Hv Hw Hx Ih Ij Ik Im Io Ir Is It Iu Iv Jh Jm Jn Jp Jq Jr Js Jt Lh Li Lj Lw Lx Ly Lz Ma Mc Me Mf Mj Mk Ml Mm Mn Mp Mq Mr Ms Mu Mv Mw My Mz Na Nb Nc Nd Ng Nh Nj Nl Nm Nn Nq Nr Ns Nt Nw Nx Ny Oe Oh Oi Ok Oz Pa Pb Pc Pd Pe Pf Po Pz Qb Qc Qd) Fp(Fr Hq Hr Hu Hv Hw Hx Ih Ij Ik Io Ip Ir Is It Iu Iv Jh Jm Jn Jp Jq Jr Js Lj Lw Ly Lz Mc Me Mf Mk Ml Mm Mn Mp Mq Mr Ms Mu Mv Mw Mx My Mz Na Nb Nc Nd Ng Nh Ni Nj Nl Nm Nn No Nq Nr Ns Nt Nw Nx Ny Oe Oh Oi Ok Oz Pa Pb Pc Pd Pe Pf Po Pz Qa Qb Qc Qd Qe) Oe(Fr Hu Hv Hw Hx Ih Ij Ik Il Im Io Ir Is It Iu Iv Jg Jh Ji Jl Jp Jq Jr Js Jt Li Lu Lw Lx Ly Lz Ma Me Mf Ml Mm Mn Mp Mq Mr Ms Mt Mu Mv Mw Mx My Mz Na Nb Nc Nd Ng Nh Ni Nj Nk Nl Nm Nq Nr Ns Nt Nw Ny Oh Oi Ok Oz Pa Pb Pc Pd Pe Pf Po Qa Qb Qc Qe) Il(Et Fr Hw Hx Ih Ij Ik Im Io Ip Ir Is It Iv Jg Ji Jl Jm Jn Jp Jq Jr Js Jt Lh Li Lu Lw Lx Ly Lz Ma Mc Me Mg Mh Mk Mm Mn Mp Mr Ms Mt Mu Mv Mx Mz Na Nc Ng Nh Ni Nj Nk Nl Nm Nn No Nr Ns Nt Nw Oh Oi Ok Pa Pe Pf Po Pz Qa Qb Qc Qd Qe) Jt(Fr Hq Hr Hu Hv Hw Ij Im Ip Ir Is It Iu Iv Jg Jh Jl Jm Jo Jp Jq Js Lh Li Lw Lx Ly Lz Mf Mg Mh Mj Mk Ml Mm Mp Mr Ms Mt Mu Mv Mw Mx My Mz Na Nb Nc Nd Ng Nh Ni Nk Nl Nn No Nq Nr Ns Nv Nw Nx Ny Oh Oi Oz Pa Pb Pc Pd Pe Po Qb Qc) Iq(Et Hu Hw Hx Ih Ij Ik Io Ip Ir Is It Iu Iv Jg Ji Jl Jm Jn Jq Jr Js Lu Lw Lx Ly Lz Ma Mc Mc Mg Mh Mk Ml Mm Mn Mp Mq Mr Mt Mu Mv Mx Mz Nd Ng Nh Nj Nl Nm No Nq Nr Ns Nt Nw Ny Oi Oz Pa Pb Pc Pd Pe Pf Po Pz Qa Qb Qc Qd Qc) Nv(Fr Hq Hu Hv Hw Hx Ij Ik Im Io Ir Iu Iv Jh Jl Jp Jq Jr Js Lh Li Lj Lu Lw Lx Ly Lz Mf Mj Ml Mm Mn Mp Mq Ms Mt Mu Mv Mw Mx My Mz Na Nb Nc Nd Ng Nh Ni Nj Nk Nl Nn Nq Ns Nw Nx Ny Oh Ok Oz Pa Pb Pc Pd Pe Pf Qa Qc Qe) Hw(Fr Hq Hr Hu Hv Hx Ij Im Iu Jh Jm Jp Jq Jr Js Lh Li Lj Lw Lx Ly Mf Mj Ml Mm Mn Mp Mq Ms Mt Mu Mv Mw My Mz Na Nb Nc Nd Ng Nh Ni Nk Nl Nm Nn Nq Nr Ns Nx Ny Oh Oi Ok Oz Pb Pc Po Pz Qc) Lh(Fr Hq Hr Hu Hv Ij Ik Iv Jh Ji Jo Jp Jq Jr Js Li Lj Lw Lx Ly Mf Mj Ml Mm Mn Mq Ms Mt Mu Mv Mw Mx My Mz Na Nb Nc Nd Nh Ni Nj Nk Nl Nn Ns Nw Nx Ny Oh Ok Oz Pa Pb Pc Pf Qc Qe) Ms(Fr Hq Hr Hu Hv Ij Io Iu Jp Jq Jr Js Li Lj Lw Lx Ly Mf Mj Ml Mm Mp Mq Mt Mu My Mz Na Nb Nc Nd Ng Nh Ni Nk Nl Nm Nn Nq Nr Nw Nx Ny Oh Ok Oz Pb Pc Pd Po Pz Qc) Hr(Hu Hv Ij Jg Jh Jo Jq Jr Js Li Lj Lw Lx Ly Mf Mj Ml Mm Mn Mp Mq Mr Mu Mv Mw My Na Nb Nc Nd Ng Nh Ni Nj Nk Nl Nn Nq Nr Ns Nx Ny Oh Oi Ok Oz Pa Pb Pc Pe Qc) Nx(Fr Hq Hu Hv Ij Io Iu Jh Jo Jp Jq Jr Li Lj Lw Lx Ly Mf Mj Ml Mm Mn Mp Mq Mt Mu Mv Mw My Na Nb Nc Nd Ng Nh Ni Nj Nk Nl Nm Nn Nq Ns Nw Ny Oh Ok Oz Pb Pc) Jo(Et Hx Ih Ij Im Io Ip Ir Is It Iu Jg Ji Jl Jm Jn Lu Lz Mc Me Mh Mk Mp Mr Mt Mx Ng Nm No Nr Nt Nw Oi Pa Pe Po Pz Qa Qb Qd Qe Wm) Mj(Fr Hq Hu Hv Jh Jp Jr Li Lw Lx Ly Mf Ml Mm Mn Mq Mt Mu Mv Mx Mz Na Nb Nc Nd Ng Nh Ni Nj Nk Nl Nn Ns Nw Ny Oh Ok Oz Pb Pc Pf) Nd(Fr Hq Hu Hv Ij Iu Jh Jp Jq Jr Li Lj Lw Lx Mf Ml Mm Mn Mu Mv Mw My Mz Na Nb Nc Ng Nh Ni Nk Nm Nn Nr Ny Oh Oi Ok Pb Po Qc) Nb(Hq Hu Hv Ij Iu Jp Jq Jr Js Li Lj Lx Ly Mf Ml Mn Mp Mq Mu Na Nc Ng Nh Ni Nk Nl Nn Nq Oh Ok Oz Pb Pc Pd Po Qc) Nh(Hq Hu Hv Ij Iu Jh Jp Jq Jr Js Lj Lw Mf Ml Mm Mq Mw My Na Nc Ng Ni Nj Nk Nl Nn Nr Nt Ny Ok Oz Pb Pc Pd Qc) Lj(Hq Hv Ij Io Iu Jq Jr Lw Ly Lz Mf Ml Mn Mp Mu Mz Na Nc Ng Ni Nk Nl Nm Nn No Nq Nr Ny Oz Pb Pc Pd Po Qc) Ni(Hq Hu Hv Jh Jp Jq Li Lw Lx Ly Mf Ml Mm Mq Mu Mv Mw My Na Ng Nj Nk Nl Nn Ny Oh Ok Oz Pb Pc Qc) Nk(Hq Hu Hv Ij

Figure 17 Continued

Jh Jm Jp Jq Li Lw Lx Ly Mf Ml Mv Mw My Na Ng Nj Nm Nn Ny Oh Ok Oz Pb Qc) My(Hq Hv Ij Io Iu Jq Jr Js Ly Mf Ml Mn Mp Mu Mz Na Nc Nn No Oz Pa Pb Pc Pd Qc) Mf(Hq Hu Hv Ij Iu Jh Jp Jq Jr Js Lw Mw Na Nc Ng Nn Ny Pb Pd Qc) Nc(Hq Hv Ij Iu Jq Jr Js Ml Mw Na Ng Nl Nn Nr Ny Pb Pc Pd Qc) Mw(Hq Hv Ij Io Iu Jr Js Ly Ml Mn Mu Na Nn Pb Pc Pd Qc) Ng(Fr Hq Ij Jq Js Lw Ly Mp Nl Nn Nq Ny Ok Pb Pc Po Qc) Qc(Hq Hu Hv Jp Li Lx Ml Mp Nn Nr Oh Ok Qa Qe) Ij(Fr Hu Hv Jp Li Lx Ml Mp Nn Nw Oh Ok) Js(Hu Hv Jh Jn Jp Li Lx Ml Nn Oh Ok) Jq(Hq Hv Jh Ji Lx Ml Mv Nn Ny Oh) Hq(Hv Ly Ml Mv Nl Ok Oz Pb) Ny(Hv Ly Ml Na Nl Nn Pb Pc) Nn(Hu Mn Mp Mv Nq Po) Na(Hv Jh Ly Mv Nl) Ok(Iu Ml Mp Pb Pd) Jr(Hv Li Ml Oh) Po(Li Lw Lx) Wm(Ii Of) Nr(Mp Nl) Mv(Iu Pc) Hu(Nm Pb) Jh(Io Pc) Pd(Lx Oz) MpPb} Mi{Ij(aA Et Fr Hr Hu Hv Hw Hx Ih Ii Ik Il Im Io Ip Ir Is It Iu Iv Jg Jh Ji Jk Jl Jm Jn Jo Jp Jq Jr Js Jt Lh Lu Lw Lx Ly Lz Ma Mc Me Mg Mh Mj Mk Ml Mm Mq Mr Ms Mt Mu Mv Mw Mx My Mz Na Nb Nc Ne Nf Ng Nh Nj Nl Nm Nn No Nq Nr Nt Nv Nx Ny Oe Og Oh Oi Oy Pa Pb Pc Pe Po Pz Qa Qb Qc Qd Qe) Po(Et Fr Hr Hu Hw Hx Ih Ii Ik Il Im Io Ip Ir Is It Iu Iv Jg Jh Ji Jk Jl Jm Jn Jp Jq Jr Jt Lh Lu Lx Ly Lz Ma Mc Me Mg Mh Mk Ml Mm Mn Mp Mq Mr Ms Mt Mu Mv Mw Mx My Mz Na Nb Nc Nd Nf Ng Nj Nk Nm No Nr Ns Nt Nv Nx Ny Oe Og Oh Oi Oy Oz Pa Pb Pc Pe Pf Pz Qa Qb Qc Qd Qe) Nu(Et Fp Fr Hr Hu Hv Hw Ih Ik Im Io Ip Ir Is It Iu Iv Jg Jh Ji Jl Jn Jp Jq Jr Jt Lh Li Lj Lu Lv Lw Lx Ly Lz Ma Mc Me Mf Mg Mh Mk Mm Mn Mp Mq Mr Ms Mu Mv Mw Mx My Mz Nb Nc Nd Ne Nf Ng Nh Nj Nl Nm Nn No Nq Ns Nv Nw Nx Oe Og Oh Oi Oz Pa Pc Pe Pf Pz Qa Qb Qc Qd Qe) Hx(aA Et Fr Hr Hu Hv Hw Ih Ii Ik Il Im Io Ip Ir Is It Iu Iv Jg Jh Ji Jk Jl Jm Jn Jp Jq Jr Jt Lh Li Lu Lw Lx Ly Ma Mc Me Mg Mh Mj Mk Mm Mq Mr Ms Mt Mu Mv Mw Mx My Mz Nb Nc Ne Nf Ng Nh Nj Nl Nm Nn No Nq Nr Nt Nv Nx Ny Oe Og Oh Oi Ok Pa Pb Pc Pe Pz Qa Qb Qc Qd Qe) Lv(Fp Fr Hr Hu Hv Hw Ih Ii Ik Im Io Ip It Iu Iv Jg Jh Ji Jl Jm Jn Jp Jq Jr Jt Lh Li Lu Lw Lx Ly Lz Ma Mb Mc Me Mf Mg Mh Mk Mm Mn Mp Mq Mr Ms Mu Mv Mw Mx My Mz Na Nb Nc Nd Ne Nf Ng Nh Nj Nl Nm Nn Nq Nr Ns Nt Nv Nw Nx Oe Og Oh Oi Oz Pa Pc Pe Pf Pz Qa Qb Qc Qd) Ny(aA Et Fr Hr Hu Hv Hw Ih Ii Ik Im Io Ip Ir Is It Iu Iv Jg Jh Ji Jk Jl Jm Jn Jp Jq Jr Js Jt Lh Li Lu Lw Lx Ly Ma Mc Me Mg Mh Mj Mk Mm Mq Mr Ms Mt Mu Mv Mw Mx My Mz Nb Nc Ne Nf Ng Nh Nj Nl Nm Nn No Nq Nr Nt Nv Nx Oe Og Oh Oi Pa Pb Pc Pe Pz Qa Qb Qc Qd Qe) Iq(Et Fr Hr Hu Hv Hw Ih Ii Ik Im Io Ip Ir Is It Iu Iv Jh Jl Jm Jn Jo Jq Jr Jt Lh Lu Lw Lx Ly Lz Ma Mb Mc Me Mf Mg Mj Mk Mm Mn Mp Mq Mr Ms Mu Mw Mx Mz Na Nb Nc Nd Ne Ng Nh Nj Nk Nl Nm Nn No Nq Nr Ns Nt Nv Nx Oe Og Oh Oi Oz Pa Pc Pe Pf Pz Qa Qb Qc Qd Qe) Pb(aA Et Fr Hr Hu Hv Hw Ih Ii Ik Im Io Ip Ir Is It Iu Iv Jg Jh Ji Jl Jm Jn Jp Jq Jr Jt Lh Li Lu Lw Lx Ly Ma Mc Me Mg Mh Mj Mk Mm Mq Mr Ms Mt Mu Mv Mw Mx My Mz Nb Nc Ne Nf Ng Nh Nj Nl Nm Nn No Nq Nr Nt Nv Nw Nx Oe Og Oh Oi Oy Pa Pc Pe Pz Qa Qb Qc Qd Qe) Ml(aA Et Fr Hr Hu Hv Hw Ih Ii Ik Im Io Ir Is It Iu Iv Jg Jh Ji Jl Jm Jp Jq Jr Jt Lh Li Lu Lw Lx Ly Ma Mc Me Mg Mh Mj Mk Mm Mq Mr Ms Mu Mv Mw Mx My Mz Nb Nc Ne Nf Ng Nh Nj Nl Nm Nn No Nq Nr Ns Nt Nv Nw Nx Oe Og Oh Oi Ok Pa Pc Pe Pz Qa Qb Qc Qd Qe) Nk(aA Fr Hr Hu Hw Ih Ii Ik Il Im Io Ip Ir Is It Iu Iv Jg Jh Ji Jl Jm Jo Jp Jq Jr Jt Lh Li Lx Ly Lz Ma Mc Me Mf Mg Mk Mm Mn Mp Mq Mr Ms Mu Mw Mx Mz Na Nb Ng Nj Nm Nn No Nq Nr Ns Nt Nv Nw Nx Oe Og Oh Oi Oy Oz Pa Pc Pe Pf Pz Qa Qb Qc Qd Qe Wm) Mt(aA Et Fr Hu Ih Ii Ik Il Im Io Ip Ir Is It Iu Iv Jg Jh Ji Jl Jm Jn Jp Jq Jr Jt Lh Lu Lw Lx Ly Lz Ma Mc Me Mg Mh Mk Mm Mp Mq Mr Ms Mv Mw Mx My Mz Nb Nc Nf Ng Nj Nm No Nq Nr Ns Nt Nv Nx Oe Og Oh Oi Oz Pa Pc Pe Pz Qa Qb Qc Qd Qe) Fp(Fr Hr Hu Hv Hw Ih Ik Im Io Ip It Iu Jg Jh Ji Jl Jm Jn Jp Jq Jr Jt Li Lj Lu Lw Lx Ly Lz Ma Mb Mc Me Mf Mg Mk Mm Mn Mp Mq Mr Ms Mu Mx Na Nb Nc Nd Ne Ng Nh Nj Nl Nm Nn Nq Ns Nt Nv Nw Nx Oe Oh Oi Oz Pa Pc Pe Pf Pz Qa Qb Qc Qd) Ni(Et Fr Hr Hu Hw Ih Ik Il Im Io Ip Ir Is It Iu Iv Jg Jh Ji Jl Jm Jn Jo Jp Jq Jr Jt Lh Lu Lx Ly Lz Ma Mc Me Mf Mg Mj Mk Mm Mn Mp Mq Mr Ms Mu Mx Na Nd Ng Nj Nm No Nq Nr Ns Nt Nv Nw Nx Oe Og Oh Oi Oz Pa Pe Pf Pz Qa Qb Qc Qd Qe) Lj(Et Fr Hu Hv Ih Ik Im Io Ir It Iu Iv Jg Jh Ji Jl Jm Jn Jp Jq Jr Jt Li Lw Ly Lz Ma Mb Mc Mf Mg Mk Mm Mn Mp Mq Mr Ms Mu Mv Mw Mx My Na Nc Nd Ne Ng Nh Nj Nl Nm Nn No Nq Ns Nt Nv Nw Nx Oe Og Oh Oi Ok Oz Pc Pf Pz Qa Qb Qd) Lw(Fr Hr Hu Hv Hw Ii Ik Il Im Ir Is Iv Jg Jh Ji Jl Jm Jo Jp Jq Jr Js Jt Li Lu Lx Ly Lz Ma Mc Me Mf Mj Mk Mn Mp Mq Mr Ms Mu Mw My Mz Na Nb Nc Nd Ne Nf Ng Nj Nl Nm Nn Nq Nr Ns Nw Oe Og Oh Ok Oy Oz Pa Pc Pf Qb Qc) Il(Et Fr Hu Hw Ih Ii Ik Im In Io Ir Is It Iu Iv Jg Jh Ji Jl Jm Jo Jp Jq Jr Js Jt Lh Li Lx Ma Md Mh Mk Mm Mp Mr Ms Mu My Mz Na Nb Nc Nf Ng Nj Nn Nr Ns Nt Nv Nw Nx Oe Of Og Oh Ok Oy Oz Pa Pe Pf Pg Qa Qb Qd Qe) Oy(aA Fr Hu Hv Hw Ih Ii Ik Im Ip Ir Is It Iu Iv Jg Jh Ji Jl Jm Jo Jp Jq Jr Jt Li Lx Ly Lz Ma Mg Mh Mj Mm Mn Mp Ms Mu Mv Mw My Mz Na Nd Nf Ng Nj No Nr Nv Nw Nx Oe Og Oh Oz Pa Pe Pf Qa Qc Qd Qe Wm) Ok(aA Et Fr Hu Hv Ih Ik Im Io Ip Ir Is It Iv Jg Jh Ji Jl Jm Jn Jp Li Lu Lz Ma Mc Me Mg Mh Mk Mm Mn Mq Mr Ms Mu Mv Mw Mx My Nc Ng Nj Nl Nm No Nq Nr Ns Nw Oh Oi Oz Pa Pf Pz Qa Qb Qd Qe) Nh(aA Fr Hr Hu Hv Hw Ii It Iu Jg Ji Jm Jp Jq Lh Li Lx Lz Mb Mf Mg Mh Mj Mk Mn Mp Ms Mu Mv Mw My Mz Na Nb Nc Nd Ne Nf Ng Nj Nl Nn Nr Ns Nt Nw Oe Og Oz Pa Pc Pe Pf Qc) aA(Hr Hu Hv Hw Ii Ih In Io Iu Jg Ji Jk Jo Js Li Lu Lx Ly Mb Md Mf Mh Mj Mk Mm Mp Mq Ms Mv Mw Mx My Mz Na Nb Nc Ne Nf Ng Nj Nl Nn Nr Ns Nw Nx Oe Og Oh Oi Oz Pa Pe Qc) My(Fr Hr Hu Hv Hw Ii Ik Im Io Ir Iu Iv Jg Jh Ji Jp Jt Li Lx Ly Ma Mf Mj Mk Mp Mq Ms Mu Mv Mz Nc Nd Ne Ng Nl Nn Nq Nr Ns Nw Oe Og Oh Oz Pa Pc Pe Qe) Jk(Et Ih Io Ip It Iu Iv Jh Ji Jl Jm Jn Jq Jt Lh Lu Lz Mc Me Mg Mh Mk Mm Mp Mq Mr Ms Mw Mx Mz Nb Nf Ng Nm No Nr Ns Nt Nx Oe Og Oi Pa Pe Pz Qb Qc Qd) Ii(Fr Hu Hv Hw Im Ir Is Iv Jg Jl Jm Jo Jp Js Li Lx Ma Mf Mg Mh Mj Mm Mn Mp Mr Ms Mu Mv Mz Na Nc Nd Ne Nf Ng Nl Nq Nr Ns Nw Og Oz Pa Pc Pe Qe) Mv(Fr Hr Hu Hv Hw Im Io Ir Iu Iv Jg Ji Jp Js Li Lx Ly Lz Ma Mf Mj Mk Mp Mq Ms Mu Mz Nc Nd Ne Ng Nl Nn Nr Ns Nw Og Oh Oz Pa Pc Pe Qe) Pc(Fr Hr Hu Hv Hw Ik Jg Ji Jm Jp Lh Li Lx Ly Lz Mb Mf Mh Mj Mn Mp Ms Mu Mw Mz Na Nb Nc Nd Ne Nf Ng Nl Nn Nr Ns Nw Og Pa Pe Pf Qc) Mb(Fr Hr Hu Hv Hw It Jg Ji Jo Jp Lh Li Lx Lz Ma Mc Mg Mj Mk Mm Mq Ms Mu Mz Na Nc Ne Ng Nj Nl Nn Nq Nr Nw Oe Og Oh Pa Pe Qc) Mh(Fr Hr Hu Hv Hw Im Ir Iv Jg Ji Jp Js Li Lx Ly Lz Ma Mf Mj Mk Mp Ms Mu Mz Nc Nd Ne Ng Nl Nn Nq Nr Ns Nw Oe Og Oh Oz Pe Qe) Om(Hr Ih Io Ir It Iu Jn Jr Lu Ly Lz Ma Mc Me Mg Mn Mp Ms Mx Na Nc Nd Ng Nj Nl Nm No Nq Ns Nt Nx Oe Og Oi Pf Pz Qa Qb Qc Qd) Js(Et Hu Ih Ik Io Ip It Iu Jh Jl Jm Jq Jr Jt Lh Lu Ma Mc Me Mg Mj Mm Mr Ms Mw Mx Nf Ng Nj Nm Nq Nr Nt Oe Oi Pa Pz Qc) Ne(Fr Hr Hu Hw Jg Ji Jm Jo Jp Jq Lh Li Lz Mf Mj Mu Mw Mz Na Nb Nc Nd Nf Ng Nl Nn Nr Ns Nt Nw Oe Og Oz Pa Pe Pf) Nf(Fr Hu Hv Hw Im Ir Iv Jg Ji Jm Jo Jp Li Lx Ly Lz Ma Mf Mj Mk Mp Ms Mu Mz Na Nc Ng Nl Nn Nq Nr Ns Nw Oh Qe) Li(Hr Hu Hw Jm Jo Jt Lh Lx Ly Lz Mf Mg Mj Mn Mp Ms Mw Mz Na Nb Nc Nd Ng Nl Nn Nq Nr Nt Oe Og Pa Pe Pf Qc) Mj(Fr Hv Hw Ik Ip Ir Is Iv Jg Jl Jm Jp Jt Lh Lx Ly Mf Mk Mp Mr Mu Nb Nd Nn No Nr Oh Oz Pa Pe Qe) Jo(Fr Hv Hw Ik Jg Ji Jl Jp Lx Ly Mf Mg Mk Mm Mr Ms Mu Nb Nc Nd Nl Nn Nw Og Oh Wm) Nn(Hr Hu Hw Ji Jm Lh Ly Mg Mp Ms Mu Mw Mz Nb Nc Nd Ng Nl Nq Nr Nw Oe Og Qc) Mz(Hr Hv Hw Ir Jg Ji Jp Lx Lz Ma Mf Mn Mu Na Nd Ng Nl Ns Oz Pe Pf Qe) Nw(Hw Jn Jq Jr Jt Lh Ly Mf Mp Ms Mw Nb Nc Nd Nl Nm Nq Nr Oe Og Qc) Nr(Fr Hu Hv Hw Ik Jg Jl Jp Lx Ly Mk Mu Na Nc Nd Nl Pe) Mw(Fr Hr Hv Hw Jg Jp Lx Lz Mf Mp Mu Na Nd Ng Ns Oz) Mf(Hr Hu Hw Jg Ji Jp Lh Mg Ms Mu Nb Ng Og Pe) Jg(Hu Hw Jm Ly Mp Ms Nc Nd Ng Nl Nq Og Qc) Nd(Fr Hw Ji Jl Jm Jp Lx Mm Mu Nb Og) Wm(Hq Hr In Md Mk Mp Mr Na Pd Pg) Hw(Hv Iu Jp Lx Na Nb Nc Nl Og Oh) Nl(Fr Hr Na Nb Nc Ng Og Pe) Ji(Jq Ly Mp Nc Nv Og Qc) Nq(Fr Hr Jp Lx Mu Pe) Na(Hu Iv Mg Mk Nc Og) Nb(Hv Ma Mn Ns Oz Pf) Mp(Fr Jp Lx Mu Oh) Og(Hv Ik Ly Mu Nc) Ng(Fr Jp Mu Nc) Jm(Hu Ik Ly Mu) Pe(Iv Mg Mr Nc) Hr(Mg Mr Nc) Ly(Fr Jp) Qc(Jp Qe) NoJr MnHu MrPa MsMu} aA{Fp(Fr Hq Hr Hu Hv Hw Hx Ih Ii Ij Ik Il Im In Io Ip Ir It Iu Iv Jg Jk Jl Jm Jn Jo Jp Jq Jr Js Jt Li Lj Lu Lx Ly Lz Ma Mb Mc Md Me Mf Mg Mh Mj Mk Ml Mm Mn Mp Mq Mr Ms Mu Mw My Mz Nb Nc Nd Ne Ng Nh Ni Nj Nl Nm Nn No Nq Ns Nt Nu Nv Nw Nx Ny Oe Of Og Oh Oi Oy Oz Pa Pd Pf Pg Po Pz Qa Qb Qc Qd) Nw(Hq Hr Hu Hv Hw Hx Ih Ii Ij Ik Il Im In Io Ir Is Iu Jh Ji Jk Jl Jm Jn Jo Jq Jr Js Jt Lh Li Lj Lu Lx Ly Lz Mb Mc Md Me Mf Mh Mk Ml Mm Mn Mp Mq Mr Ms Mt Mv Mw My Mz Nb Nc Nd Ne Ng Nh Ni Nj Nl Nm Nn No Nr Ns Nv Nx Ny Oe Og

Figure 17 Continued

Oh Oi Ok Oy Oz Pa Pb Pd Pe Pf Pg Pz Qa Qc Qd) cX(aC Ad Af aH aI AJ aK AL An Ao AP aQ AR AS aU aV Aw aX aY Ba BB bE bF BG bH bI bL bM Bn Bo bP bQ bR bS bU bV bW bX bZ cA cB cC cD cF cG CH cI cJ cK cM CO Cp CQ CS Ct Cu Cv Cw Cx cY cZ DB Dc DD De dF DG dH Di dJ DK DL Fr) aG(aC aD aE Af aH aI aJ aK aL aM aN aO aP aQ aR aS aU aV aW aX aY aZ bB BC bE bF bG bH bI bL bM BN bP bQ bR bS bU bV bW bX bZ cA cB cC cD cE cF cG cH cI cJ cK cL cM cN cO cQ cR cS cU cV cW Cx cY cZ dA dB dC dD dE dF dG dH dI dJ dK dL dN) bA(aC aE Af aH aI aJ aK aL aM aN aP aQ aR aS aU aV aX aY aZ bB bC bE bF bG bH bI bL bM bN bP bQ bR bS bU bV bW bX bZ cA cB cC cD cF cG cH cI cJ cK cL cM cN cO cQ cR cS cT cU cW Cx cY cZ dA dB dC dD dE dF dG dH dI dJ dK dL dM dN) aD(aC aE Af aH aI aJ aK aL aM aN aO aP aQ aR aS aU aV aX aY bB Bc bE bF bG bH bI bL bM Bn bP bQ bR bS bU bV bW bX bZ cA cB cC cD cE cF cG cH cI cJ cK cL cM cN cO cQ cR cS cU cV cW Cx cY cZ dA dB dC dD dE dF dG dH dI dJ dK dL) dN(aC aE Af aH aI aJ aK aL aM aN aP aQ aR aS aU aV aW aX aY aZ bB bC bE bF bG bH bI bJ bM bP bQ bR bS bU bV bW bX bZ cA cB cC cD cE cF cG cH cI cJ cK cL cM cN cO cQ cR cS cT cU cW Cx cY cZ dA dB dC dD dE dF dG dI dJ dK dL dM) aO(aC aE Af aH aI aJ aK aL aM aN aP aQ aR aS aU aV aX aY aZ bB bC bE bF bG bH bI bL bM BN bP bQ bR bS bU bW bX cA cB cC cD cE cF cG cH cI cJ cK cL cM cN cO cQ cR cT cU cV cW Cx cY cZ dA dB dC dD dE dF dG dH dI dJ dK dL) bO(aC aE aH aI aJ aK aL aN aP aQ AR aS aU aV AX aY aZ bB BC bE bF bG bH bI bL bM Bn bP bQ bR bS bU bW bX bZ cA cB cC cD cE cF cG cH cI cJ cK cL cM cN cO cQ cR Cs cU cV Cx cY cZ dA dB dD DE dF dG dH dI dJ dK dL) bN(aC aE aH aI aJ aK aL aN aP aQ aR aS aU aV aX aY aZ bB bC bE bF bG bH bI bL bM Bn bP bQ bR bS bU bV bW bX bZ cA cB cC cD cE cF cG cH cI cJ cK cM cN cO cQ cT cU cV cW cY cZ dA dB dC dD DE dF dG dH dI dJ dK dL) Ok(Fr Hq Hu Hv Hx Ih Ik Im Io Ip Ir Is It Iv Jg Jh Ji Jl Jm Jn Jp Lh Li Lu Lx Lz Ma Mc Md Me Mg Mh Mk Mm Mn Mq Mr Ms Mt Mu Mv Mw My Mz Nb Nc Nf Nh Nm No Nr Ns Nt Nv Nx Ny Oh Oi Oy Pa Pe Pf Pg Po Pz Qa Qb Qd Qe) bJ(aC Af aH aI aJ aK aL aP aQ aR aS aU aV aX aY bB bC bE bF bG bH bI bL bM bP bQ bR bS bU bV bW bX bZ cA cB cC cD cE cF cG cH cI cJ cK cL cM cN cO cQ cR cS cU cV cW Cx cY cZ dA dB dC dD dE dF dG dH dI dJ dK dL) dM(aC aE Af aH aI aJ aK aL aM aN aP aR aS aU aV aW aX aY aZ bB bC bE bF bG bH bI bL bM Bn bP bQ bR bS bU bV bW bX bZ cA cB cC cD cF cG cH cI cJ cK cM cN cO cQ cR cS cU cW Cx cY cZ dA dB dD dE dF dG dI dJ dK dL) aF(aC aE Af aH aI aJ aK aL aN aP aQ AR aS aU aV AX aY aZ bB bE bF bG bH bI bL bM Bn bP bQ bR bS bU bW bX bZ cA cB cC cD cE cF cG cH cI cJ cK cM cO cQ cV Cx cY cZ dB dD De dF dG dH dJ dK dL) aW(aC aE aH aI aJ aK aL aN aP aQ aR aS aU aV aX aY aZ bB Bc bE bF bH bI bL bM Bn bP bQ bR bS bU bW bX bZ cA cC cD cF cG cH cI cJ cK cM cN cO cQ cS cU cW cY cZ dB dC dD DE dF dG dI dJ dK dL) cP(aC Af aH aI aJ aK aL aM aN aP aQ aR aS aU aV aX aY aZ Bc bE bF bG bH bL bM Bn bP bQ bR bS bU bW bX bZ cA cC cD cF cG CH cI cJ cK cM cO cQ cS Cx cY cZ dA dB dC dD DE dF dG dJ dK dL) Lw(Et Fr Hq Hx Ih Im Ip Ir Is It Iu Iv Jg Jh Ji Jl Jm Jn Jo Jp Jq Jr Lh Lu Lz Ma Mc Me Mg Mj Mk Mm Mn Mq Mr Mt Mu Mv Mx My Nb Nc Nf Nm Nn No Nr Nt Nv Oy Pa Pd Pe Pf Pg Po Pz Qa Qb Qd Qe) Nu(Fr Hq Hu Hv Hw Ih Ii Ij Il In Io Ip Iq It Iu Jg Jk Jo Jp Jq Js Jt Li Lj Lu Lx Mb Md Mf Mj Mk Ml Mm Mp Mq Ms Mx Mz Nc Nd Ne Ng Nh Ni Nk Nl Nm Nn Nq Ns Nt Nx Oe Of Og Oi Pa) Ji(Hq Hu Hv Hw Ih Ii Ij Ik Il In Io Iu Jk Jo Jq Jr Js Jt Li Lj Lx Ly Mb Md Mf Mj Mm Mp Ms Mw Mx Mz Na Nc Ne Nf Ng Nh Ni Nj Nk Nl Nn Nq Nr Ns Nx Ny Oe Of Og Oh Oi Oz Pa Pd Qc) cT(aE Af aH aI aJ aL aM aN aP aQ aR aS aU aX aY aZ bB bC bF bG bH bI bM bP bQ bS bU bV bX cB cD cF cG cH cI cJ cK cL cM cN cO cQ cR cS cU cV cW cZ dA dB dC dE dF dH dI dJ dK) Pc(Fr Hu Hv Hw Il Iq Ir Is Iv Jg Jn Jr Lh Li Lj Ly Mb Md Mf Mh Ml Mm Mp Mq Ms Mu My Mz Nd Ne Ng Nh Ni Nj Nk Nl Nn No Nq Ns Nt Nv Nx Of Og Oh Oi Oy Oz Pb Pe Po Qd Qe) aE(aC Af aJ aK aL aM aN aQ aR aS aX aY aZ BC bE bF bG bH bI Bn bP bR bU bV bW bX cB cC cD cE cG cH cK cL cM cN cQ cR cS cU cV Cx cY cZ dA dB dC dD dE dH dI) cL(aC aH aI aJ aM aN aP aQ aR aS aV aX aY aZ bB bC bG bH bI bP bU bV bW bX bZ cA cB cC cE cF cH cI cK cM cN cO cQ cR cS cU cV cW cZ dB dC dE dF dH dI dJ) Lx(Hq Hr Hu Hw Ii Ij In Iu Jk Jo Js Jt Lh Lj Ly Lz Mb Md Mf Mh Mj Mk Ml Mm Mp Mt Mx Na Ng Ni Nj Nk Nl Nn Nq Nr Nx Oe Of Og Oi Oy Oz Pb Pe Pf Pg Po) Om(Et Fr Hu Hv Hx Im Ip Iq Ir Is Iv Jn Jp Jr Lh Lu Ma Mb Mf Mg Mh Ml Mn Mp Mq Mr Mu My Mz Ne Ng Nm No Nq Ns Nt Of Og Oi Pa Pe Pf Po Qa Qb Qd Qe) cW(aC Af aH aI aJ aL aM aN aQ aS aU aX aZ bB bC bF bG bH bI bL bP bU bV bW bX cB cC cD cE cG cH cI cJ cN cR cS cU cV cZ dA dB dC dE dH dI dJ dL) aM(aC aH aJ aN aQ aS aX aZ bB bC bG bH bI bU bV bW bX cB cC cD cE cF cG cH cI cJ cM cN cQ cR cS cU cV dA dB dC dD dE dH dI dL) cE(aC Af aJ aN aQ aR aS AX aY aZ bC bF bG bH bI bP bQ bV bX bZ cA cC cI cM cN cO cR cS cU cV Cx dA dB dC dD dE dF dH dI) Pb(Fr Hu Hv Iq Ir Jg Jn Jp Jq Jr Li Lj Lu Ly Md Mf Ml Mm Mp Mq Mz Nd Ng Nh Ni Nk Nm Nn No Nq Ns Nt Nx Of Og Oh Oi Pe) cV(aC Af aJ aN aQ aZ bC bG bI Bn bP bV bW bX cB cC cD cG cI cM cN cQ cS cU Cx dA dB dC dD dE dH dI) dC(aC Af aH aJ aN aQ aS aX aZ bC bG bI bP bV bW bX cB cI cM cN cQ cR cS cU Cx dA dB dD dE dH dI) dH(aJ aN aP aQ aR aS aX aY aZ bC bG bH bI bP bV bZ cA cB cI cN cO cQ cR cS cU dB dE dI) bC(aC Af aJ aQ aS bF bG bI Bn bP bV bW cB cC cD cG cI cN cR cS Cx dB dE dI) cR(aC Af aJ aN aQ aZ bB bF bG bI bP bV cB cC cG cI cN cS dA dE dI) Iq(Fr Hv Ir Jg Li Lj Mf Ml Mm Mp Mq Ni Nk Nn Nv Nx Oh Pa Pe Po) cS(aH aI aN aQ aS aZ bG bI bW bX cB cG cI cJ cN dA dE dG dI dL) Jq(Hw Lj Ly Mb Mf Ml Nd Ne Ni Nk Nq Nx Oe Of Og Oz) dA(aQ aV aZ bF bI bQ bR bU bV bW cD cG cM cO dE dI) Af(aN AR Ax aZ bH bW cN Cs cU Cv De Dk Dl) bV(aN aQ aS aZ bB bI bW bX cD cG cJ cM cN dE) Nk(Hv Li Lj Ml Mm Nd Ne Nj Nl No Nx Of) aQ(aH aJ aN aU aX bB cB cI cN cU dE dI) Of(Fr Jg Li Lj Mf Ml Ni Nn Nv Nx Oh) Ng(Fr Jg Li Mf Mg Mm Nn Nx) Cx(aN Ar Ax Bc Cs De) Nd(Jg Li Lj Mm Ni Nx) aZ(aJ aS bI bP cB cG) Ml(Jg Mm Mq Ni Nx) cG(Ax cN cU dE dI) De(Ar Ax Bc Dk) Ni(Li Lj Mm Nx) Jg(Hu Lj Mv Nq) aJ(bW bX dG dL) bI(aN cU dE dI) Nr(Li Lj Nx) dE(aC bP cB) Bc(Ao Bn) Il(Lj Pa) Js(Jn Nx) cI(cM cN) dD(aI bB) ArBn NnIi NqLi NxOi aCcB bUdI bWcN} Ok{Lv(Et Fp Fr Hq Hr Hu Hv Hw Hx Ih Ii Ij Ik Im In Io Ip Ir Is It Iu Iv Jg Jh Ji Jk Jl Jm Jn Jp Jr Js Jt Lh Li Lj Lu Lw Lx Ly Lz Ma Mb Mc Md Me Mf Mg Mh Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Oh Oi Oy Oz Pa Pb Pc Pd Pe Pf Pg Po Pz Qa Qb Qc Qd Qe) Ne(Et Fp Fr Hq Hr Hu Hv Hw Hx Ih Ii Ij Ik Il Im In Io Ip Ir Is It Iu Iv Jg Jh Ji Jk Jl Jm Jn Jp Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nd Nf Ng Nh Ni Nj Nl Nm No Nq Nr Ns Nt Nu Nv Nw Nx Ny Oe Oh Oi Oy Oz Pa Pb Pc Pd Pe Pf Pg Po Pz Qa Qb Qc Qd Qe) Og(Et Fp Fr Hq Hr Hu Hv Hw Hx Ih Ii Ij Ik Il Im In Io Ip Ir Is It Iu Iv Jg Jh Ji Jk Jl Jm Jn Jo Jp Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nf Ng Nh Ni Nj Nk Nl Nm No Nq Nr Ns Nt Nv Nw Nx Ny Oe Oh Oi Oy Oz Pa Pd Pe Pf Pg Po Pz Qa Qb Qc Qd Qe) Jo(Et Fr Hq Hr Hu Hv Hw Hx Ih Ii Ij Ik Il Im In Io Ip Ir Is It Iu Iv Jg Jh Ji Jk Jl Jm Jn Jp Jr Js Jt Lh Li Lj Lu Lw Lx Ly Lz Ma Mc Md Me Mf Mg Mh Mj Mk Mm Mn Mp Mq Mr Ms Mt Mu Mv Mw Mx My Mz Na Nb Nc Nd Nf Ng Nh Ni Nj Nk Nl Nm No Nq Nr Ns Nt Nv Nw Nx Ny Oe Oh Oi Oz Pa Pd Pe Pf Pg Po Pz Qa Qb Qd Qe Wm) Nu(Et Fp Fr Hq Hr Hu Hv Hw Hx Ih Ij Ik Il Im Io Ip Ir Is It Iu Iv Jg Jh Ji Jk Jl Jm Jn Jp Jr Js Lh Li Lj Lu Lw Lx Ly Lz Ma Mc Md Me Mf Mg Mh Mk Ml Mm Mn Mp Mq Mr Ms Mt Mu Mv Mw Mx My Mz Nb Nc Nd Nf Ng Nh Ni Nj Nl Nm Nn No Nq Nr Ns Nv Nw Nx Ny Oe Oh Oi Oy Oz Pa Pb Pc Pd Pe Pf Pg Po Pz Qa Qb Qd Qe) Iq(Et Hr Hu Hw Hx Ih Ii Ij Ik Im In Io Ip Ir Is It Iu Iv Jg Jh Ji Jk Jl Jm Jn Jr Js Lh Lu Lx Ly Lz Ma Mc Md Me Mf Mg Mh Mk Mm Mn Mp Mq Mr Ms Mt Mv Mw Mx My Mz Nb Nc Nd Nf Ng Nh Ni Nj Nl Nm No Nq Nr Ns Nt Nv Nw Nx Ny Oe Oi Oy Oz Pa Pd Pe Pf Pg Po Pz Qa Qb Qd Qe) Fp(Et Fr Hq Hr Hu Hv Hw Hx Ih Ii Ij Ik Il In Io Ip It Iu Jg Ji Jk Jm Jn Jp Jr Js Lh Lj Lu Lw Ly Lz Mb Mc Md Me Mf Mk Ml Mm Mn Mp Mq Mr Ms Mu Mv Mx My Mz Na Nc Nd Nf Ng Nh Ni Nj Nl Nm Nn Nq Nr Nt Nv Nx Ny Oe Oh Oi Oy Oz Pa Pb Pc Pd Pf Pg Po Pz Qa Qb Qc Qd Qe) Nn(Et Fr Hq Hr Hu Hv Hw Ij Il Im In Io Iu Iv Jh Ji Jk Jm Jn Jp Jr Js Lh Li Lj

Figure 17 Continued

Lu Lw Lx Ly Lz Mb Mc Md Mf Mk Ml Mn Mp Mq Ms Mt Mu Mv Mw Mx My Mz Na Nb Nc Nd Nf Ng Nh Ni Nj Nk Nl Nm Nq Nr Ns Nt Nv Nx Ny Oh Oi Oy Oz Pa Pb Pc Pd Pf Pg Po Pz Qb Qc Qd Qe) Jq(Et Hq Hr Hu Hw Hx Ih Ii Ij Ik Im In Io Ip Ir It Iu Iv Jg Jh Jk Jl Jm Jn Jr Js Lh Lu Ly Lz Ma Mc Md Me Mg Mh Mj Mk Mm Mn Mp Mq Mr Ms Mw Mx My Mz Nb Nf Ng Nj Nl Nm No Nq Nr Ns Nt Nv Nx Ny Oe Oi Oy Oz Pa Pd Pe Pf Pg Po Pz Qa Qb Qc Qd Qe) Jt(Et Fr Hq Hr Hu Hv Hw Hx Ii Ij Ik Il Im In Ir Is Iu Iv Jg Jh Ji Jl Jr Js Lh Li Lj Lw Lx Ly Ma Mb Md Me Mf Mg Mj Mk Ml Mm Mp Mq Mr Ms Mt Mu Mv Mx My Mz Na Nb Nc Nd Nf Nh Ni Nk Nl Nr Ns Nv Nw Nx Oe Of Oh Oy Oz Pa Pb Pd Pe Pf Qa Qc Qe) Mb(Fr Hq Hr Hu Hv Hw Hx Ii Ij Ik Il In It Iu Jg Jh Jk Jl Jp Jr Js Lh Li Lj Lu Lw Lx Ly Lz Mc Md Me Mf Mj Mk Ml Mm Mn Mp Mq Mr Ms Mt Mu Mv My Mz Na Nc Nd Nf Ng Nh Ni Nj Nk Nl Nm Nr Ns Nt Nv Nw Nx Oe Oh Oy Oz Pa Pb Pc Pd Po Qc Qd) Of(Et Hq Hu Hw Hx Ih Ii Ij Ik Il Im In Io Ip Ir Is It Iu Iv Jh Ji Jk Jm Jn Jr Js Lh Lu Lw Lz Ma Mc Me Mg Mh Mk Mm Mn Mp Mr Ms Mt Mw Mx Mz Na Nb Nf Ng Nj Nl Nm No Nq Nr Ns Nt Nv Nw Nx Ny Oe Oi Oz Pa Pd Pe Pf Pg Po Pz Qa Qb Qd Qe) Pb(Fr Hq Hr Hu Hv Hw Hx Ii Ij In Iu Iv Jh Jk Jm Jp Jr Js Lh Li Lj Lu Lw Lx Ly Lz Md Mf Ml Mm Mn Mp Mq Ms Mt Mu Mv My Mz Na Nb Nc Nd Nf Ng Nh Ni Nj Nk Nl Nm Nq Nr Nt Nv Nx Ny Oe Oh Oy Pc Pd Pg Po Pz Qc Qd) Hw(Fr Hq Hr Hu Hv Hx Ii Ij Il Im In Is Iu Iv Jk Jl Jp Js Lh Li Lj Lu Lw Lx Ly Md Mf Ml Mm Mp Mq Ms Mt Mu Mv My Mz Na Nc Nd Nf Ng Nh Ni Nj Nk Nl Nm Nt Nw Nx Oe Oh Oy Oz Pa Pc Pd Pf Qa Qc) Mj(Fr Hq Hr Hu Hv Hx Ii Il Im In Is Iu Iv Jh Jl Jp Li Lj Lu Lw Lx Ly Md Mf Ml Mp Mq Ms Mt Mu Mv Mx My Mz Na Nc Nd Nf Ng Nh Ni Nk Nl Nr Nw Nx Oe Oh Oy Oz Pa Pc Pd Pe Pf Po Qa Qc Qe) Qc(Et Fr Hq Hr Hu Hv Hx Ii Il Im In Is Iu Iv Jl Jp Lh Li Lj Lu Lw Lx Ly Md Mf Ml Mm Mq Ms Mt Mu Mv My Mz Na Nc Nd Nf Ng Nh Ni Nk Nl Nm Nw Nx Oe Oh Oy Oz Pa Pc Pd Pf Pg Qa Qe) Nd(Fr Hq Hr Hu Hv Hx Ii Ij Il Im In It Iu Jl Jp Js Lh Li Lj Lw Lx Md Mf Ml Mm Mp Mq Ms Mt Mu Mv Mx My Mz Na Nc Nf Ng Nh Ni Nj Nk Nl Nm Nt Nw Nx Oe Oh Om Oy Oz Pa Pc Pd) Nh(Fr Hr Hu Hv Ii Ij Il In It Iu Jk Jp Jr Js Lh Li Lj Lw Lx Md Mf Ml Mm Mq Ms Mu My Na Nc Nf Ng Ni Nj Nk Nl Nm Nr Nt Nv Nx Oe Oh Oz Pc Pd Po) Ml(Fr Hr Hv Ii Ij Il In Iu Jk Jp Jr Js Lh Lj Lu Lw Lx Ly Md Mf Mm Mq Ms Mu My Na Nc Nf Ng Ni Nk Nl Nm Nr Nt Nx Oe Oh Oz Pc Pd Po) Pc(Et Fr Hq Hr Hu Hv Ii Ij In Iu Jh Jk Jr Js Lh Lj Lw Ly Mf Mn Mq Ms Mv Mw My Na Nb Nc Ng Ni Nk Nl Nm Ns Nv Nx Ny Oe Oz Pd Pg) Nk(Fr Hr Hu Hv Ii Il In Iu Jl Jp Li Lj Lu Lw Lx Ly Md Mf Mp Mq Ms Mt Mu Mv Mx Mz Na Nf Ng Ni Nj Nl Nx Oe Oh Oy Oz Pa Pd Pf) Om(Ij Ik Io Ip Ir It Iv Lu Ly Lz Mc Me Mg Mh Mk Mn Mr Ms Mw Nb Ng Nm No Nq Nr Ns Oi Oz Pe Pg) Ni(Fr Hr Hu Hv Ii Il Iu Jp Li Lj Lw Lx Ly Md Mf Mq Ms Mu Na Nf Ng Nj Nl Nx Oe Oh Oz Pd) Nc(Fr Hr Hv Ii Ij In Iu Jk Jp Js Lh Lw Md Mf Mq Ms Mu Na Nf Ng Nj Nl Nt Nx Oe Pd) Ii(Fr Hq Hr Hu Il Ir Jl Jp Li Lj Lu Lw Lx Ma Md Mf Mk Mm Mq Mt Mu Mz Na Nl Nw Oz) Mu(Hr Hu Hv Ij In Jk Js Lh Lj Lw Md Mp Mq Ms Na Nf Ng Nq Nt Nv Nx Oe Pd) Hv(Fr Hr Ij Il In Iu Jk Jr Js Lw Ly Md Mf Mp Mq Ms Na Nf Nx Oe Oz Pd) Il(Et Iu Iv Lj Lw Ly Md Mf Mk Mq Mr Ms Na Ng Nl Oe Oz Pa Pd) Hv(Fr Hr Ij In Jk Lh Ly Md Mf Mp Mq Na Nf Ng Nq Nv Nx Oe Pd) In(Hr Hu Iv Li Lj Lw Lx Ly Md Mf Mk Mq Mr Nl Nx Oh Pd) Pd(Li Lj Lx Ly Mf Mp Mv Na Nf Nl Oe Oh Oy Oz) Na(Hr Hu Lj Lw Ly Md Mq Ng Nl Nx Oh) Mf(Hr Iu Jp Lj Md Mq Ms Ng Nt Nx) Lj(Ij Iu Jr Js Ly Nf Nr Oe Po) Md(Iu Jp Js Lw Ly Nf Oe Oz) Mq(Js Li Ly Nf Nl Oe Oz) Hr(Js Lw Ly Mk Oe Oy Oz) Nx(Li Lx Ly Nf Oe Oh Oy) Oh(Ij Js Ms Nf Oe) Jp(Js Ly Ng Oe) Li(Ij Js Ng Po) Lw(Nf Oe Oz) Lx(Js Lh Po) MvNg NlIu HuOe} bA{cE(aC aE aF aG aH aI aK aL aO aQ aR aU aV AX aZ bB Bc bE bF bG bH bI bL bM BN bP bQ bR bS bU bV bW bX bZ cA cB cC cD cF cG CH cI cJ cK cL cM cO cQ cR cT cU cV cW Cx cY cZ dB dC dD DE dF dG dH dI dJ dK dL) aD(aE AF aI aJ aL aM aN aO aS aW aY bB bC bE bF bN bV bX cB cG cL cN cP cR cS cT cV CX cZ dA dB dE dM dN) aJ(aE AF aG aH aI aM aP aS aW bB bC bF bJ bN bX cG cJ cL cR cT cX dC De dF dG dH dL dM) cP(aE AF aH aI aL aM aO aS aU aW bB bE bF bJ bO cB cG Ch cL cN cR cV DE dM) bO(aE AF aG aH aN aP aS aY bB bF bJ bV cJ cL cR cS cT cV cW dE dN) dM(aE AF aG aH aL aM aO aQ aS bB bF bJ bN cG cJ cL cV cX dE dF) aM(aE AF aG aI aL aS aW bB bE bF bJ bN cG cJ cL cT cV dE) aW(Af aP aS bB bE bF bJ cL cR cT cV CX dA DE) Af(aF aH aL aS bB bC bF bJ Ch cL cN cR cV) bF(aE aP aY bJ cN cS cW cX dA dN) aF(aP bE bJ cR cT dE dN) cG(aP aY cN cS cW dA dN) cV(aE bV cR cS cT dE dN) bJ(aE aG aN bB cL De) cX(Ao Bc Ch DE) aS(aE aG bB cL) dN(aO bB dF dH) cL(aY cN dA) bB(cN cW) ChCx bUdA cNdH} Lx{In(Fp Fr Hu Hv Hw Hx Ik Il Im Iv Jo Jp Js Lj Lv Lw Ly Lz Mb Md Mf Mj Ml Mm Mp Mq Mt Mu My Na Nc Nd Ne Nh Ni Nj Nk Nl Nn Nq Nw Of Og Oh Oy Oz Pb Pc Pd Pf Po Qe) Om(Fp Fr Hq Hr Hv Im Iq Is Jg Jh Ji Jk Jo Jp Js Li Lj Lv Lw Md Mf Mh Mm Mu Mv My Mz Ni Nk Nu Nv Nw Of Oh Oy Pg Po Qa Qe) Il(Fp Hv Hw Iv Li Lw Lz Mf Mk Ml Mp Nd Ne Ni Nj Nk Nn Nu Of Pa Pb Pf) Pd(Fp Hr Hw Iq Jo Lv Lw Mb Mf Mj Mm Na Nd Ne Nh Ni Nk Nn Nu Of Pb Pc) Nk(Fp Hq Ii Ij Js Lv Mb Md Ne Nf Nh Nl Nu Ny Of Pg Po) Lv(Hq Iq Jo Js Md Mj Ni Nu Of Pg Po) Iq(Fr Hq Js Lw Md Ni Nn Of Pg Po) Of(Fr Jg Lw Lz Mj Mu Ni Nn Nu) Jo(Hq Js Md Mh Ml Nu Ny Po) Js(Fp Jn Lz Nn Nu Nw Oh) Ni(Lw Md Nc Ne Nu Po) Po(Fp Mj Nn Nu) Nu(Ii Na Nr) Lz(Jk Md Pg) Mj(Hq Md Pg) Jk(Fr Jg) Pc(Md Oy) Nnli} Lv{Il(Et Fr Hq Hr Hu Hx Ih Ii Ik Im In Io Ip Iq Ir Is It Iu Jg Jh Ji Jk Jm Jn Jo Jp Jq Jr Js Jt Lh Li Lu Ly Lz Ma Mb Mc Md Me Mf Mg Mh Ml Mm Mn Mp Mq Ms Mt Mu Mv Mw Mx My Mz Na Nc Nd Ne Nf Ng Nh Ni Nj Nk Nl Nm Nq Ns Nt Nv Nx Ny Oe Og Oh Oi Oy Oz Pd Pf Pg Po Pz Qa Qb Qc Qd Qe) Nu(Fp Fr Hv Hw Ii Iq Iu Iv Jg Ji Jl Jo Jp Js Li Lj Lw Ly Md Mj Mk Mr Mu Mv My Na Nb Ne Ng Ni Nj Nk Nn Nr Nt Nw Of Og Oi Om Pa Pb Pc Pe Qc) Om(Hw Iv Jg Ji Lj Lw Mk Mr Mv Nr Nw Oh Pa Pe) Lw(Fp Fr Hv Li Lj Ne Ni Nk Nw Of Og) Nw(In Js Lj Md Ny Of Og Qc) Li(Iq Mj Nk Of Qc) Fr(Fp Iq Of Qc) Of(Jg Mu Nn) No(Js Nk) MdPc NcNk} Om{Fr(Hu Hv Hw Hx Ih Ip Iq Ir Is Iv Jl Jp Jq Jt Li Lj Mb Md Mk Mm Mp Mr Mv Mx Mz Nc Ne Ng Nh Nk Nl Nn No Nr Nw Of Oh Pa Pb Pc Pe Qc) Ji(Fp Hv Hw Hx Il Iq Is Iv Jg Jh Jl Jp Jq Li Lj Lw Mj Mk Mm Mr Mv My Ne Nh Ni Nk Nr Nu Nv Nw Og Oh Oy Pa Pb Pc Pe) Nn(Fp Hv Hw Is Iv Jl Jq Li Lj Lw Mk Mr Mz Nk Nr Nu Nw Of Og Pa Pe) Nw(Hv Hw In Jl Js Li Lj Lw Ml Mm Mt Mu My Nk Nu Ny Of Og Oh Qc) Lw(Fp Hv Is Jg Jl Jp Mv Nu Nv Oh Pc) Mu(Is Iv Li Lj Mr Nu) Nu(Jg Jp Md) Nk(Li No) MdOg HxLi IIPa JgOh} aJ{bN(aD aE aF aM aN aQ aW aZ bC bM Bn bO bX cE Ch cL cM cP cR cS cT cV CX De dG dH dK dL dM dN) cP(aE AF aW aZ bB bC bM Bn bO bV bW bX cE cJ cL cM cR cV CX De dG dH dL dM) cT(aD aE AF aG aM aO aW bB bF bJ bO bX cG cL cV cX dC dG dH dM) dG(aW Ax aZ bC Bn bO bV cM cR cS cX dA De dM dN) bO(aD aE AF aW bB bF bJ cN cS cV De dH dL) aW(Af bC bX Cx De dH dL) dL(aD Af Cx De dN) bW(Af bC Bn Cx) dH(aZ bC Cx dN) Af(Bc Cv) De(Ax Cs) BcCx aQdM} Nw{Md(Fp Fr Hv Hw In Iq Jo Js Jt Lz Mb Ml Mu Mz Na Nc Nd Ne Nh Ni Nk Nn Nu Oe Of Og Pb Pc Qc) Nu(Ii In Js Mj Ms My Mz Nk Nx Ny Of Og Qc) Js(Hv Iq Jn Lj Nc Ne Nh Of Og Oh) In(Hv Iq Mj Ne Nh Nk Of) Of(Fr Li Lw Nk Nn Ny) Nn(Ii Ms My) Mj(Lj My Ny) Il(Mk Pa Pc) Nk(Nh Nl) Ny(Iq Og) Pc(Ms My)} Nu{Fr(Ii Iq Ji Lw Mb Md Mj Na Nd Ng Nk Nq Nr Of Og Po) Ji(Ii Jq Mj Na Nk Nn Of Og Pb Pc Qc) Nk(Hv Jp Li Lw Mp Nn No Pb) In(Hw Iv Mr Nb Pa Pb Pc) Il(Iv Mk Pa Pb Pc) Md(Jg Mp Nd Pc) Of(Jg Lw Nn) Na(Is Lw) NoJs NrLi} Nk{No(Fp Mb Nc Ne Nh Nl) Fr(Fp Nc Ne Nt Of) Lw(Fp Hv Li Ne Nh) Nn(Nc Ne Nl Of) Ji(Nc Ne Nh) Li(Nc Of)} Il{Pa(Fp Ji Lw Mb Nn Nx Pb Pc) Pc(Fp Ji Lw No) Iv(Fp Lw Pb) Pb(Ji Lw) FpMk} Fr{Of(Fp Hv Ji Lw Ly Nh Oh) Lw(Fp Iq Mb Nd) Iq(Hv Ji) FpNr MkOy} dM{cX(Ax Bo Cs Dl fR) aQ(Af Bn Cx De) cT(aD Af bB) AfbN CsDe bVcV} Ji{Nn(Ii Iq Of Og) Og(Ne Pb Pc) Pc(Md Ms) MuOf IqJl} cT{Af(aW BC bJ) cE(aP cN cP dN)} Bc{cX(aE Ao aW cR) aW(Af Cx)} Lw{Of(Li Mu Nn)} Md{Pc(Fp Jq) MuIlu} De{CsaW aQdA} AfBaaW Unconstrained panels with 2 analytes, where 1.0E-7 >= 'model p-value' > 0. Contains 13 panels of 14,881 total panels evaluated. : Mi(Hq In Jj Pd Pg) Jj(Nn Nu Ok On) On(Ii Of Om) LvaA

Figure 17 Continued

Unconstrained panels with 2 analytes, where 1.0E-6 >= 'model p-value' > 1.0E-7. Contains 30 panels of 14,881 total panels evaluated. : Jj(aA Fr Jg Li Lv Lw Lx Mu Nw Oh Oy) aA(aD aF aW cP cX Lw Ok) Mi(Jk Js Md Of Ok Om) Ok(Iq Jq Of Om) On(Iq Jo)

Unconstrained panels with 2 analytes, where 1.0E-5 >= 'model p-value' > 1.0E-6. Contains 251 panels of 14,881 total panels evaluated. : aA(aC aE Af aG aH aJ aM aN aO aQ aR aS aX aY aZ bA bB bC bF bG bH bI bJ bN bO bP bV bW bX cB cC cD cE cG cH cI cJ cL cM cN cQ cR cS cT cU cV cW dA dB dC dD dE dH dI dM dN Fp Fr Ji Jq Lx Mi Nu Nw Om On Pb Pc) Ok(Fp Fr Hr Hv Hw Ii Il In Iu Jo Jp Js Jt Li Lj Lv Lw Lx Ly Mb Md Mf Mj Ml Mq Ms Mu Na Nc Nd Ne Nf Ng Nh Ni Nk Nl Nn Nu Nx Oe Og Oh On Oz Pb Pc Pd Qc) On(Fp Hq Hr Hv Hw Il In Jk Jt Lh Lj Lv Mb Md Mf Mi Mj Ml Ms Mw My Na Nb Nc Nd Ne Nf Ng Nh Ni Nk Nl Nu Nv Nx Ny Oe Og Oy Oz Pb Pg) Jj(Fp Hq Hu Hv Hw Hx Ii Ij Ik Is Iv Ji Jk Jl Jo Jp Jt Lh Lj Mg Mk Mp Mr Mt Mv My Nb Nf Nh Nr Nt Nv Pa Pb Pc Pd Pe Pf Po Qe Wm) Mi(Fp Hx Ii Ij Il Iq Jg Ji Jp Li Lj Lv Lw Mb Mh Mj Ml Mt Mu Mv Mw My Mz Nd Ne Nf Nh Ni Nk Nn Nu Nw Ny Oy Pb Pc Po) aJ(bA bN cP cT) Om(Fr Ji Lx) bA(aD cE dM) Lv(Il Nu) LxIn MdNw Unconstrained panels with 2 analytes, where 1.0E-4 >= 'model p-value' > 1.0E-5. Contains 502 panels of 14,881 total panels evaluated. : Mi(Et Fr Hr Hu Hv Hw Ih Ik Im Io Ip Ir Is It Iu Iv Jh Jl Jm Jn Jo Jq Jr Jt Lh Lu Lx Ly Lz Ma Mc Me Mf Mg Mk Mm Mn Mp Mq Mr Ms Mx Na Nb Nc Ng Nj Nl Nm No Nq Nr Ns Nt Nv Nx Oe Og Oh Oi Oz Pa Pe Pf Pz Qa Qb Qc Qd Qe) On(Et Fr Hu Hx Ih Ij Ik Im Io Ip Ir Is It Iu Iv Jg Jh Ji Jl Jm Jn Jp Jq Jr Js Li Lu Lw Lx Ly Lz Ma Mc Me Mg Mh Mk Mm Mn Mp Mq Mr Mt Mu Mv Mx Mz Nj Nm Nn No Nq Nr Ns Nt Nw Oh Oi Pa Pc Pd Pe Pf Po Pz Qa Qb Qc Qd Qe) Ok(Et Hq Hu Hx Ih Ij Ik Im Io Ip Ir Is It Iv Jg Jh Ji Jk Jl Jm Jn Jr Lh Lu Lz Ma Mc Me Mg Mh Mk Mm Mn Mp Mr Mt Mv Mw Mx My Mz Nb Nj Nm No Nq Nr Ns Nt Nv Nw Ny Oi Oy Pa Pe Pf Pg Po Pz Qa Qb Qd Qe) Jj(Et Hr Ih Im In Io Ip Iq Ir It Iu Jh Jm Jn Jq Jr Js Lu Ly Lz Ma Mb Mc Md Me Mf Mh Mj Ml Mm Mn Mq Mw Mx Mz Na Nc Nd Ne Ng Ni Nj Nk Nl Nm No Nq Ns Nx Ny Oe Of Og Oi Om Oz Pg Pz Qa Qb Qc Qd) aA(aI aK aL aP aU aV Ax Bc bE bL bM Bn bQ bR bS bU bZ cA cF cK cO Cx cY cZ De dF dG dJ dK dL Hv Hw Iq Jg Li Lj Ly Mb Mf Ml Mm Mp Mq Mz Nd Ng Ni Nk Nn Nx Oe Of Og Oh Oi Pa Pe Po) bA(aE AF aG aH aL aM aN aP aS aU aW aY bB bE bF bJ bN bO bV cG cJ cL cN cP cR cS cT cV cW CX dA DE dN) Lx(Fp Fr Hq Hw Il Iq Ji Jk Jo Js Lv Lw Mb Md Nh Ni Nk Nn Nu Of Og Pc Pd Pg Po) aJ(aD aE AF aQ aW aZ bC bO bW bX cE cL cR cV CX De dG dH dL dM dN) Lv(Fp Fr Hw Iv Ji Jl Li Lj Lw Mk Mr Mu Nn Nr Nw Om Pa Pb Pc Pe) Ji(Fp Fr Hv Hw Iq Jl Li Lw Mk Mr Mu Ne Nh Nn Nu Of Og Pb Pc) Nw(In Js Lj Lw Ml Ms Mt My Ne Nk Nu Of Og Om Qc) Lw(Fp Fr Hv Jp Li Mu Nu Om Pb Pc) Nu(Fr Jg Jp Nk Nn Pb Pc) Fr(Fp Iq Ng Nh Of) Om(Li Md Mu Nn) dM(aQ bN cT Cx) Af(aW cT) BccX CsDe CxaW NnOf MdPc NkLi IlPa aDcT Unconstrained panels with 2 analytes, where 1.0E-3 >= 'model p-value' > 1.0E-4. Contains 1,081 panels of 14,881 total panels evaluated. : aA(Ad Aj Al An Ao Ap Ar As Aw Ba Bb Bg Bo Ch Co Cp Cq Cs Ct Cu Cv Cw Db Dc Dd Dg Di Dk Dl Et Hq Hr Hu Hx Ih Ii Ij Ik Il Im In Io Ip Ir Is It Iu Iv Jh Jk Jl Jm Jn Jo Jp Jr Js Jt Lh Lu Lz Ma Mc Md Me Mg Mh Mj Mk Mn Mr Ms Mt Mv Mw Mx My Na Nb Nc Ne Nf Nh Nj Nl Nm No Nq Nr Ns Nt Nv Ny Oy Oz Pd Pf Pg Pz Qa Qb Qc Qd Qe) Nw(Et Fp Fr Hq Hr Hu Hv Hw Hx Ih Ii Ij Ik Il Im Io Ip Iq Ir Is It Iu Iv Jg Jh Ji Jk Jl Jm Jn Jo Jp Jq Jr Jt Lh Li Lu Lx Ly Lz Ma Mb Mc Me Mf Mg Mh Mj Mk Mm Mn Mp Mq Mr Mu Mv Mw Mx Mz Na Nb Nc Nd Nf Ng Nh Ni Nj Nl Nm Nn No Nq Nr Ns Nt Nv Nx Ny Oe Oh Oi Oy Oz Pa Pb Pc Pd Pe Pf Pg Po Pz Qa Qb Qc Qd Qe) Ji(Et Hq Hr Hu Hx Ih Ii Ij Ik Il Im In Io Ip Ir Is It Iu Iv Jg Jh Jk Jm Jn Jo Jp Jq Jr Js Jt Lh Lj Lu Ly Lz Ma Mb Mc Md Me Mf Mg Mh Mj Ml Mm Mn Mp Mq Ms Mt Mv Mw Mx My Mz Na Nb Nc Nd Nf Ng Ni Nj Nk Nl Nm No Nq Nr Ns Nt Nv Nx Ny Oe Oh Oi Oy Oz Pa Pd Pe Pf Pg Po Pz Qa Qb Qc Qd Qe) Lx(Et Hr Hu Hv Hx Ih Ii Ij Ik Im Io Ip Ir Is It Iu Iv Jg Jh Jl Jm Jn Jp Jq Jr Jt Lh Li Lj Lu Ly Lz Ma Mc Me Mf Mg Mh Mj Mk Ml Mm Mn Mp Mq Mr Ms Mt Mu Mv Mw Mx My Mz Na Nb Nc Nd Ne Nf Ng Nj Nl Nm No Nq Nr Ns Nt Nv Nx Ny Oe Oh Oi Oy Oz Pa Pb Pe Pf Pz Qa Qb Qc Qd Qe) Nu(Et Fp Hq Hu Hv Hw Hx Ii Ij Il Im In Ip Iq Ir Is It Iu Iv Jh Jl Jm Jo Jq Js Jt Lh Li Lj Ly Ma Mb Md Mh Mj Mk Ml Mm Mn Mp Mq Mr Ms Mt Mu Mv Mx My Mz Na Nb Nc Nd Ne Nf Ng Nh Ni Nj No Nr Ns Nv Of Og Oh Oi Om Oy Pa Pe Pf Po Qa Qc Qe) Lw(Et Hq Hu Hw Hx Ii Ij Ik Il Im In Ip Iq Ir Is Iv Jg Jh Jl Jm Jo Jq Jr Jt Lh Lj Lu Ly Ma Mb Md Me Mf Mh Mj Mk Ml Mr Ms Mt Mv Mx My Mz Nb Nc Nd Ne Ng Nh Ni Nj Nk Nl Nn No Nr Ns Nt Nv Of Og Oh Oy Oz Pa Pe Pf Po Qa Qc Qe Wm) Fr(dM Et Hu Hv Hw Hx Ii Ik Ip Ir Is Iu Iv Jk Jl Jm Jo Jp Jq Jt Lh Li Lj Ly Mb Md Mf Mh Mj Mk Ml Mm Mp Mq Mr Ms Mu Mv Mx My Mz Nb Nc Nd Ne Ni Nj Nk Nl Nn No Nq Nr Ns Nt Oe Og Oh Oi Pa Pb Pc Pe Po Qc Qe) Lv(Et Hq Hr Hu Hv Hx Il Ij Ik Im Ip Iq Ir Is It Iu Jg Jh Jo Jp Jq Js Jt Lh Ly Lz Md Me Mh Mj Ml Mm Mp Mq Mt Mv Mx My Mz Nb Nc Nd Ne Nf Ng Nh Ni Nj Nk Nl Nm No Nt Nv Of Og Oh Oy Pd Pf Po Qa Qb Qc Qe) aJ(aC aG aH aI aK aL aM aN AO aP aR aS aU aV AX aY bB Bc bE bF bG bH bI bJ bL bM Bn bP bQ bR bS bU bV bZ cA cB cC cD cF cG CH cI cJ cK cM cN cO cQ cS cU cW cY cZ dA dB dC dD dE dF dI dJ dK) dM(aC aD aE AF aG aH aK aM aN aO aP AR aU aW Ax aY aZ Ba bB BC bF bG bI bJ bL Bn BO bU bV bW bX cE cF cH cI cJ cK cL cM cP cQ cR CS cV CW cX cY dA DB dD DE dG dH dI dK dN) bA(aC aI aK AO aQ aR aV AX aZ BC bG bH bI bL bM Bn bP bQ bR bS bU bW bX bZ cA cB cC cD cF CH cI cK cM cO cQ Cs cU cY cZ dB dC dD dF dG dH dI dJ dK dL) Nn(Fp Hu Hv Hw Ii Ip Iq Is Iv Jl Jm Jp Jq Li Lj Ly Mb Md Mj Mk Mr Ms Nb Nc Nd Ne Ng Nh Ni Nk Nl No Nr Og Pa Pb Pc Pe) Li(Hv Hw Ip Iq Is Iv Jg Jl Jp Jq Mk Mp Mr Mu Nb Ng Nh Ni Nr Of Og Pa Pb Pc Pe) Mu(Fp Hv Hw Is Iv Jl Lj Mk Mr Ng Nk Nr Of Pa Pb Pe) Om(Hw Is Iv Jg Jl Jp Lh Mk Mr Mv Nr Nv Oh Pa Pc Po) Fp(Hw Is Iv Jg Jl Jp Mk Mr Nk Nr Pa Pb Pc Pe) cP(Af aP aW Ax Bc Bn bV Ch cR Cs cT Cx De) Jp(Hw Iv Jl Mk Mr Nh Nr Pa Pb Pe Wm) cT(aE aM aP aW bJ bV cE Cx dA dE dN) No(Jr Js Mc Md Na Nk Pb Pc) Jg(Hu Hv Lj Md Mv My Ng Of) Il(Iv Jj Mk Mr Pb Pc Pe) In(Hw Iv Mr Nb Pa Pe Wm) Af(aP Ax Ba Bc Bo Cs) Nk(Hv Jl Nc Ne Nh Pc) aW(aP Ax Bc Bn bV De) Mm(Is Jl Mr Pa Pe) Jq(Jl Mk Mr Pe) Pb(Hv Is Iv Jl) Pc(Lj Ms My Ns) aP(aF bN bO cE) Ax(CX De) Cs(bO CX) Wm(Mi Ok On) Ni(Jl Pa Pe) Iq(Is Pa Pe) Nb(Md Of) bV(cE cV) BcCx MsJj NvOf bNdN cXfR Unconstrained panels with 2 analytes, where 1.0E-2 >= 'model p-value' > 1.0E-3. Contains 2,523 panels of 14,881 total panels evaluated. : Pe(Et Hq Hr Hu Hv Hw Hx Ih Ii Ij Ik Im Io Ip Ir Is It Iu Iv Jg Jh Jk Jl Jm Jn Jo Jr Js Jt Lh Lj Lu Ly Lz Ma Mb Mc Md Me Mf Mg Mh Mj Mk Ml Mn Mp Mq Mr Ms Mt Mv Mw Mx My Mz Na Nb Nc Nd Ne Nf Ng Nh Nj Nl Nm No Nq Nr Ns Nt Nv Nx Ny Oe Of Og Oh Oi Oy Oz Pa Pb Pc Pd Pf Pg Po Pz Qa Qb Qc Qd Qe) Pa(Et Hq Hr Hu Hv Hw Hx Ih Ii Ij Ik Im Io Ip Ir Is It Iu Iv Jg Jh Jk Jl Jm Jo Jq Jr Js Jt Lh Lj Ly Lz Ma Mb Mc Md Me Mf Mg Mh Mj Mk Ml Mn Mp Mq Mr Ms Mt Mv Mw Mx My Mz Na Nb Nc Nd Ne Nf Ng Nh Nj Nk Nl Nm No Nq Nr Ns Nt Nv Nx Ny Oe Of Og Oh Oi Oy Oz Pb Pc Pd Pf Pg Po Qa Qb Qc Qd Qe) JI(Et Hq Hr Hu Hv Hw Hx Ih Ii Ik Il Im In Ip Iq Ir Is It Iu Iv Jg Jh Jk Jm Jn Jo Jr Js Jt Lh Lj Ly Lz Ma Mb Mc Md Me Mf Mg Mh Mj Mk Ml Mn Mp Mq Mr Ms Mt Mv Mw Mx My Mz Na Nb Nc Nd Ne Nf Ng Nh Nj Nl Nm No Nq Nr Ns Nt Nv Nx Oe Of Og Oh Oi Oy Oz Pc Pd Pf Pg Po Pz Qa Qb Qc Qd Qe) Mu(Et Hq Hr Hu Hx Ih Ii Ij Ik Im In Io Ip Iq Ir It Iu Jg Jh Jk Jm Jn Jo Jp Jq Jr Js Jt Lh Lu Ly Lz Ma Mb Mc Md Me Mf Mg Mh Mj Ml Mm Mn Mp Mq Ms Mt Mv Mw Mx My Mz Na Nb Nc Nd Ne Nf Nh Ni Nj Nl Nm Nn No Nq Ns Nt Nv Nx Ny Oe Og Oh Oi Oy Oz Pc Pd Pf Pg Po Pz Qa Qb Qc Qd Qe) Is(Et Hq Hu Hv Hw Hx Ih Ii Ij Ik Il Im In Ip Ir It Iu Iv Jg Jh Jm Jn Jo Jp Jq Jr Js Jt Lh Lj Ly Ma Mb Mc Md Me Mf Mg Mh Mj Mk Ml Mn Mp Mq Mr Ms Mt Mv Mx My Mz Na

Figure 17 Continued

Nb Nc Nd Ne Ng Nh Ni Nj Nk Nl Nm No Nr Ns Nt Nv Nx Oe Of Og Oh Oi Oy Oz Pc Pd Pf Po Qa Qc Qd Qe) Mr(Et Hq Hr Hu Hv Hw Hx Ih Ii Ik Im Io Ip Iq Ir It Iu Iv Jg Jh Jm Jo Jr Js Lh Lj Ly Lz Ma Mb Md Mf Mg Mh Mj Ml Mn Mp Mq Ms Mt Mv Mx My Mz Na Nb Nc Nd Ne Ng Nh Ni Nj Nk Nl Nm No Nq Nr Ns Nt Nv Nx Oe Of Og Oh Oi Oy Oz Pb Pc Pd Pf Pg Po Qa Qb Qc Qd Qe) aP(aC aD aE aG aH aI aK aL aM aN AO aQ aR aS aU aV AX aY aZ bB BC bE bF bG bH bI bJ bL bM Bn bP bQ bR bS bU bV bW bX bZ cA cB cC cD cF cG CH cI cJ cK cL cM cN cO cQ cR CS cU cV cW CX cY cZ dA dB dC dD DE dF dG dH dI dJ dK dL dN) Mk(Et Hq Hr Hu Hv Hw Hx Ih Ii Ik Im In Ip Iq Ir It Iu Iv Jg Jh Jo Jr Js Lh Lj Ly Lz Ma Mb Mc Md Mf Mg Mh Ml Mm Mn Mp Mq Ms Mt Mv Mx My Mz Na Nb Nc Nd Ne Ng Nh Ni Nj Nk Nl Nm No Nr Ns Nt Nv Nx Oe Of Og Oh Oi Oy Oz Pb Pc Pd Pf Pg Po Qa Qb Qc Qd Qe) Li(Et Fp Hq Hr Hu Hx Ih Ii Ij Ik Il Im In Io Ir It Iu Jh Jk Jm Jn Jo Jr Js Jt Lh Lj Lu Ly Lz Ma Mb Mc Md Me Mf Mg Mh Mj Ml Mm Mn Mq Ms Mt Mv Mw Mx My Mz Na Nc Nd Ne Nf Nj Nl Nm No Nq Ns Nt Nv Nx Ny Oe Oh Oi Oy Oz Pd Pf Pg Po Pz Qa Qb Qc Qd Qe) cT(aC aF aG aH aI aK aL aN AO aQ aR aS aU aV AX aY aZ bB BC bE bF bG bH bI bL bM BN BO bP bQ bR bS bU bW bX bZ cA cB cC cD cF cG CH cI cJ cK cL cM cN cO cQ cR CS cU cV cW cX cY cZ dB dC dD De dF dG dH dI dJ dK dL) Nr(Et Hq Hr Hu Hv Hw Hx Ih Ii Ik Il Im In Ip Iq Ir It Iu Iv Jg Jh Jo Jq Jr Js Lh Lj Ly Lz Ma Mb Mc Md Mf Mg Ml Mm Mp Mq Ms Mt Mv Mx My Mz Na Nc Nd Ne Ng Nh Ni Nj Nk Nl Nm No Nt Nv Nx Oe Of Og Oh Oy Oz Pb Pc Pd Pf Po Qa Qb Qd Qe Wm) Jp(Et Hq Hr Hu Hv Hx Ii Ij Ik Il Im Ip Iq Ir Iu Jg Jh Jm Jo Jq Js Jt Lh Lj Ly Lz Mb Md Me Mf Mh Mj Ml Mm Mp Mq Ms Mt Mv Mx My Mz Nb Nc Nd Ne Nf Ng Ni Nj Nk Nl Nm No Ns Nt Nv Of Og Oh Oi Oy Pc Pd Pf Po Qa Qc Qe) Af(aC AD aE aF aI aM AN Ap aQ AR AS Aw aY aZ BB bC BG bH bJ bN bO bQ bV bW bX bZ cB cE Ch cI cJ cL cN cO Cp CQ cR cS CU CV CW cX dA dB DD DE dF dG dH dI dJ Dk Dl dN FR) Nn(Et Hq Hr Hx Ih Ij Ik Il Im In Io Ir It Iu Jg Jh Jk Jn Jo Jr Js Jt Lh Lu Lz Ma Mc Me Mf Mg Mh Ml Mm Mn Mp Mq Mt Mv Mw Mx My Mz Na Nf Nj Nm Nq Ns Nt Nv Nx Ny Oe Oh Oi Oy Oz Pd Pf Pg Po Pz Qa Qb Qc Qd Qe Wm) Hv(Et Fp Hq Hu Hw Hx Ii Ij Ik Il Im In Ip Iq Ir It Iv Jh Jm Jq Js Jt Lh Lj Ly Ma Mb Md Mf Mj Ml Mm Mn Mp Mq Mt Mv Mx My Mz Na Nb Nc Nd Ne Nf Ng Nh Ni Nj Nl Nm No Nt Nv Of Og Oh Om Oy Pc Pd Pf Po Qc Qe) Hw(Et Hq Hr Hu Hx Ik Il Im Ip Iq Ir It Iu Iv Jg Jh Jo Jq Jt Lh Lj Ly Ma Mb Md Mf Ml Mm Mp Mq Ms Mt Mv Mx My Mz Na Nb Nc Nd Ne Ng Nh Ni Nk Nl Nm No Nt Nv Nx Oe Of Og Oh Oy Oz Pb Pc Pf Po Qa Qb Qe) cP(AD aE aF aI aJ aM aN Ao aQ AR aU aY aZ Ba bB bC bE bF BG bI bJ bN BO bP bX bZ cB cE cH cI cJ cL cM cN Co cS CU CV CW cX cZ dA DB DD dE dG dI dJ dK Dl dN FR) Fp(Et Hq Hu Hx Ii Ij Ik Il Im In Ip Iq Ir It Iu Jh Jm Jo Jq Js Jt Lh Lj Ma Md Mj Mm Mn Mp Mq Mt Mv Mx My Mz Na Nb Nc Nd Ne Nf Ng Nh Ni Nj Nl Nm No Nt Nv Of Og Oh Oi Om Oy Pd Pf Po Qc Qe) Iv(Et Hq Hu Hx Ik Im Ip Iq Ir It Iu Jg Jh Jo Jq Jr Js Lh Lj Ly Ma Mb Md Me Mf Ml Mm Mp Mq Mt Mv Mx My Mz Na Nb Nc Nd Ne Ng Nh Ni Nj Nk Nl Nm No Nt Nv Of Og Oh Oy Oz Pc Pd Pf Po Qa Qb Qe) Jg(Et Fr Hq Hx Ii Il Im In Ip Iq Ir Jh Jk Jm Jo Jq Jt Lh Ly Lz Mb Mf Mh Mj Ml Mm Mp Mq Ms Mt Mw Mx Mz Nb Nc Nd Ne Nf Nh Ni Nk Nl No Nq Ns Nt Og Oh Oi Pb Pc Pd Pf Po Qa Qc Qd Qe) Lh(Et Hu Hx Ii Ik Il Im In Ip Iq Ir It Iu Jh Jo Jq Js Lj Ly Mb Md Mf Mj Ml Mm Mp Mq Ms Mt Mv Mx My Mz Na Nc Nd Ne Ng Nh Ni Nk Nl No Nv Of Og Oh Oy Pb Pc Pf Pa Qc Qe) Pc(Et Hq Hu Hx Ik Im Ip Iq Ir Jh Jq Jt Ly Ma Mb Mc Mf Mh Mj Mm Mp Mq Mt Mv Mx Mz Nb Nc Nd Ne Ng Nh Ni Nj Nk Nl Nt Nv Of Og Oh Oi Om Oy Pb Pd Pf Po Qa Qd Qe) aW(aD aE aM aN Ao aQ aR aZ Ba bB bC bE bG bJ bN BO bQ bZ cE cF CH cL cN cO cQ cR CS CU CV CW cX dA dB dD dE dF dG dI dJ Dl dN FR) dM(Ad aI Aj AL An Ao Ap AS aV Aw aX Bb bE Bg bH bM bP bQ bR bS bZ cA cB cC cD cG Ch cN CO Cp Cq Ct CU Cv cZ DC Dd dF Dg Di dJ Dk DL fR) Cx(aC aD aE aF aI aM AN Ao aQ AR aY aZ Ba bB bC bH bJ bN BO bV bX cE Ch cI cJ cL cN cQ cR cS CU Cv CW cX dA dB DE dG Dl dN FR) Pb(Et Hu Hx Ii Im In Ip Iq Jt Lj Ly Ma Md Mj Mm Mp Mq Mt Mv Mx My Mz Nb Nc Ne Ng Nh Ni Nk Nl Nm Nt Nv Of Og Oh Om Oz Pf Po Qa Qb Qd Qe Wm) Fr(aJ bA Ch cX De Hq Hr Ih Ij Il Im In Io It Jh Jn Jr Js Lu Lz Ma Mc Me Mg Mn Mt Mw Na Nf Nm Nv Nx Ny Oy Oz Pd Pf Pg Pz Qa Qb Qd Wm) No(Et Hu Hx Ik Il Ip Iq Ir Jn Jq Lj Ly Mb Mf Mj Ml Mm Mp Ms Mt Mv Mw Mx My Mz Nb Nc Nd Ne Nh Ni Nt Nv Of Og Oh Om Oy Pf Po Qa Qe Wm) Nb(Et Hu Il Im Iq Ir Jq Js Lj Mb Mf Ml Mm Mp Ms Mt Mv Mw Mx My Mz Nc Nd Ne Ng Nh Ni Nk Nl Ny Og Oh Om Pf Qa Qe) bV(aD aE aF aG aK aM aN aQ aR AX aZ bB Bc bJ BN BO cG Ch cL cN CS cW cX dA dB DE dN) cX(Ad Aj Al An Ao Ap Ar As Aw Ba Bb Bg Bn Bo Ch Co Cp Cq Ct Cu Cv Cw Db Dc Dd De Dg Di Dk Dl dN) Oh(Et Hu Hx Ii Ip Iq Jh Jm Jq Js Jt Mb Mj Mm Mp Mt Mv My Mz Nc Ne Ng Nh Ni Nk Nl Nv Of Og Po) Om(Et Hx Ii Ij Im Ip Ir Jh Jq Jt Lj Ma Mj Mm Mp Mt Mx My Mz Ne Nh Nk Nl Nt Pf Qa Qb Qd Qe Wm) Lw(Hr Ih Io It Iu Jk Jn Js Lz Mc Mg Mm Mn Mp Mq Mw Na Nf Nm Nq Nx Ny Oe Oi Pd Pg Pz Qb Qd) Lv(Ih In Io Jk Jm Jn Jr Lu Ma Mb Mc Mf Mg Mn Ms Mw Na Nq Ns Nx Ny Oe Oi Oz Pg Pz Qd Wm) aJ(Ad Aj Al An Ap Ar As Aw Ba Bb Bg Bo Co Cp Cq Cs Ct Cu Cv Cw Db Dc Dd Dg Di Dk Dl fR) Nu(Hr Ih Ik Io Jk Jn Jr Lu Lz Mc Me Mf Mg Mw Nl Nm Nq Nt Nx Ny Oe Oz Pd Pg Pz Qb Qd) bA(Ad Aj Al An Ap Ar As Aw Ba Bb Bg Bo Co Cp Cq Ct Cu Cv Cw Db Dc Dd Dg Di Dk Dl fR) Ax(aD aE aF aH aI aM Ao aQ bB BC bF bJ BN BO cE cG Ch Co cR cV dA dN) Nh(Et Hx Ii Ij Ip Iq Jt Lj Mj Mm Mp Mq Mv My Mz Ne Nf Ni Nj Nv Of Og Pf Po Qe) Po(Et Il In Ip Iq Jq Js Lj Mb Md Mf Mm Mt Nc Nd Ne Ng Ni Nk Nl Of Og Qe) Lj(Et Hu Hx Ii Il Ip Iq Jt Ly Mj Mm Mp Mv My Ne Ni Nk Nv Of Og Oy) De(aE aF aM aN Ar aZ Ba BC bN BO cN cR Cw dA dG Dk dN fR) Mj(Et Hu Il Im Iq Jq Mm Mp Ms Mt Mv Mw Mx Ne Ni Nk Nv Of Og Wm) dN(aD aE aF aN aQ aZ bB Bc bO bW cE cL cN cQ cR cW dA dB dE) Cs(aD aE aF aM Ao aZ bB BC bJ BN Bo Ch cR cV dA) Nk(Hx Ir Jt Mm Mp Mt Mv Mx My Nl Nt Nv Pf Qa Qe Wm) Wm(Hr Ii Iu Ji Jo Jq Lx Mm Na Nw Of Og Oi Oy) Jt(Il Iq Jq Mb Mm Mp Mt Mv Ne Ng Ni Nv Of Og) bN(aD aE aM aN Bc Bn Bo cN cR cS Cw dA dG fR) Bc(aD aE Ao bB Bn BO Ch cl cR fR) Jq(Hx Ir Mm Mv Mx Ne Nl Og Pf Qe) Bn(aE aM Ar bC Bo cN cR dA fR) Mm(Hu Hx Ir Mv Ne Nv Pf Qe) Mp(Hq Ir Md Nd Ns Oz Pd Qe) Bo(aM Ao bB bO cE Ch dA) Nv(Ip Iq Md Ne Ng Ni Og) Of(Et Ir Mt Mv My Pf Qe) dA(aD aE aQ aV bU cL) Hx(In Iq Md Ni) fR(aA aD aF cV) Mv(Ne Ng Og) Iq(Ir Pf Qe) Ao(Ba Cw) Ch(Ba Cw) My(Mb Ne) Ni(Nc Pf) Qe(Og Qc) aE(aM cN) EtNe aDaZ cEdF cLcN

*Constrained panels with 3 analytes, where 1.0E-8 >= 'model p-value' > 0. Contains 157 panels of 597,622 total panels evaluated.* : Mi{Jj(Fp Hq Hx Ij Ik In Js Lv Ly Md Mf Mh Ml Mt Mv Mw My Mz Ne Nf Nh Nl Nu Ny Of Om Pb Pd Pg) Pd(Fp Hu Hv Hw Ii Ik Iq Lj Lv Ly Mb Mf Ml Nd Ne Nh Nj Nl Nu Of Ok Om Oz Pb Pc) Hq(Fp Hu Hv Iq Lv Ly Mb Mf Ml Mp Nd Ne Nj Nl Nu Of Om Oz Pb Pc) Pg(Fp Hv Iq Lj Lv Ly Mb Mf Mj Ml Nd Ne Nh Nl Nu Of Ok Om Pb) Md(Fp Iq Mb Mj Ne Om) In(Fp Iq Mb Ne Nu Om) Of(Fp Iq Ne Om) On(Ii Om) NqaA LvIl} aA{Lv(Fp Ii Ij Iq Jj Lw Mj Mk Ng Nk Nq Nr Nu Of Om Pb) Om(Lw Ok On) NuJj} Jj{Nu(Fr Hq Lv Nn Ok On Oy Pb) Om(Fr Nn Ok On) On(Of Qc) LwHu} On{Om(Ii Iq Jk Jo Md Nx Of) Of(Ii Iq)}

*Constrained panels with 3 analytes, where 1.0E-7 >= 'model p-value' > 1.0E-8. Contains 321 panels of 597,622 total panels evaluated.* : Mi{Of(In Jo Lj Lv Ly Mb Md Mf Mj Ml Mn Nd Nh Ni Nl Nu Ok On) Js(Fp Iq Jn Jo Lj Lv Mb Mf Mn Na Nk Nu Nw Ok Om Pf) Md(Hv Jo Lj Lv Ly Mf Ml Mn Nd Nh Ni Nl Nu Ok) In(Hv Jo Lj Lv Ly Mf Ml Mn Nd Nh Ni Nl Ok) Jj(Ii Jk Lj Mb Mj Nb Nc Nd Ni Nn Ok Pc Po) Jk(Fp Iq Lj Lv Mb Mu Ne Nh Nl Nu Om) Om(Jg Li Lj Lw Mt Mu Nk Nn Ok Pb) Jo(Hx Ml Mt Mv Mv Ny Ok Pb Pg) Mn(Hx Ij Ml Mt Nf Ny Pb Pg) Nk(Fp Ne Nl Nu) Pg(Hu Nq On Pc) Mb(Ml Mt Pb) Il(Fp Ne Nq) Ok(Iq Jq Mj) Oy(Lj Ne On) Po(Fp Lj) NcNi IqOn} Jj{Nu(Hu Hv Hw Ii Iv Jg Ji Jl Lw Lx Mk Mp Mr Mu Na Nb Nf Nw Og Pa Pc Pe) On(Fp Hw Ii Iq Lv Md Mf Mj Nd Ne Nh Nn Nv Pb Pg) Lv(Fr Hw Jg Jl Lw Lx Mk Mr Mu Nn Ok Oy) Lw(aA Fp Fr Hq Hv Ik Mu Nh Oy Pb) Lx(Fp Js Md Mj Mz Ne Nh Ni Nn Om) Fr(Fp Hv Ly Nd Ne Nh Nq Pb) Nn(Fp Hv Hw Ly Nk Ok Pb) Om(Jg Jk Li Mu Nv Nw Oh) Ok(Fp Iq Jq Ne Pb) WmNa FpaA MpOy LiPb} On{Om(Ij Il Jt Mj Mp Ms My Nb Ng Ni Nk Nn Nv

My(Io Iu Pc) Ng(Fr Iq Mp) Jr(Fp Hv Lj) Nv(Hv Ms Nh) Nm(Jk Lj) Ly(Hq In) Mv(Iu Pc) Na(Fp Ne) NuPz LvJm MlNb MrIn MsHq MwIo NeNl NfIu NhPg HuPb JhPc} Jj{Om(Et Fp Ih Ii Ij Im Ip Ir Jh Jm Jo Jp Jq Lj Ma Mg Mj Mn Mp Mt Mw Mx My Mz Ne Nf Nh Nk Nl No Nr Nx Ny Pc Pd Pf Pg Qa Qb Qd) Ly(Hv Ir Jk Jp Jq Lj Ma Mj Mm Mt Mv Mz No Pf Qa) Nf(Hu Ik Lj Mf Mg Mt Mv My Nc Ne Nl Pc Qe) Nh(Hq Hu Hv Hx Ii Ij Is Jo Jp Jt Mn My Nr) Hu(Fp Hx Ii Ji Jo Lj Mm My Ne Nt Qe) Ik(Hx Ii Jp Jt Lh Lj My Nk No) Pc(Hq Hx Mf Mj Mp Nc Nl No Ns) Ne(Et Ii Ij Jq Mm Mp My) Pb(Hq In Md Mj Mz Pf Wm) Nr(Mf Mg Mv My Na Nk) Ij(Fp Lj Md Mf Nc Nl) Mg(Hv Ii Is Lj Mp) Hx(In Md Ml Nd Ny) Fp(Hq Hv Is Nk) Mm(Is Jk Mj Nl) Mp(Hq Mv Nl Nt) My(Hv Ii Nc Nl) Wm(Jp Mn Og) No(Mc Md Na) Nk(Hq Jk Jp) Po(In Nc) Nt(Hq Hv) Md(Ny Pg) Mj(Ih Js) Ii(Mf Mv) NcNi NlJq HvJs IqIr QcQe} bA{cP(aE AF aH al aL aO aS aU aW bB bE bF bI bO cB cG Ch cL cN cR cV DE) bF(aD aE Af aJ aM aP aW aY bJ bO cN cS cW cX dA dM dN) Af(aD aJ aL aM aS aW bB bC bJ bO cL cN cR cV dM) aM(aE aF aS aW bB bE bJ bN cG cJ cL cV dE dM) bO(aE aF aG aS bB bJ cL cR cT cV cW dN) aW(aD aJ aS bE bJ cR cV CX DE) aF(aD aJ aP bE bJ cR cT dE dM dN) cG(aJ aP aY cN cS cW dA dM dN) cV(aD aE bV cR cS cT dE dM dN) bB(aD aJ aS bJ cN cW dM dN) cX(aD aJ Ao Bc Ch DE) cE(Ax Bc Bn Ch Cx De) aD(aS bN Cx dE dM) bJ(aE aG aN cL De) aJ(bN De dG dH) cL(aS aY cN dA) dN(aO dF dH) aG(aS dM) ChCx aEaS aQdM bUdA cNdH} Lx{Om(Fp Fr Hq Im Iq Jg Ji Jp Js Li Lv Lw Md Mm Mu Mv Ni Nk Nu Nw Of Oh Pg Po) Nk(Fp Hq Ii Ij Il In Js Lv Mb Md Nc Nf Nh Nl Nu Ny Of Pd Pg Po) Il(Fp Hw Iv Lw Lz Mf Mk Ml Nd Nn Nu Of Pa Pb Pf) Of(Fr In Iq Jg Lv Lw Lz Mj Mu Ni Nn Nu Pd) Lv(Hq In Iq Jo Js Md Mj Ni Pd Pg Po) Iq(Fr Hq Js Lw Md Ni Nn Pd Pg Po) Js(Fp Jn Jo Lz Nn Nu Nw Oh Ok) Ni(In Lw Md Nc Ne Nu Pd Po) Mj(Hq In Md Ok Pd Pg Po) Jo(Hq Md Mh Ml Nu Ny Po) Pd(Hw Lw Nd Nh Nu Pb) Nu(Ii Na Nr Po) Lz(In Jk Md Pg) In(Nd Ne Nh) Po(Fp Nn) Jk(Fr Jg) Pc(Md Oy) NnIi JtOk} Om{Fr(Hv Hw Hx Iq Is Iv Li Lj Mk Mm Mr Mx Mz Ng Nh Nk Nn No Nr Nw Of Oh Pa Pe) Nn(Fp Hv Hw Is Iv Jl Jq Li Lj Lw Mk Mr Mz Nk Nr Nu Nw Of Og Pa Pe) Nw(Hv In Js Li Lj Lv Lw Ml Mm Mt Mu My Nk Nu Ny Of Og Oh) Ji(Hv Hw Jl Jp Li Lj Lv Lw Mk Mr Mv My Nk Nu Oh Pc) Lv(Hw Iv Jg Lj Lw Mk Mr Mv Nr Nu Oh Pa Pc Pe) Lw(Fp Hv Is Jg Jl Jp Mv Nu Nv Oh Pc) Mu(Is Iv Li Lj Mr Nu) Nu(Jg Jp Md) Nk(Li No) MdOg HxLi IlPa JgOh} aJ{bN(aD aW bC Bn bO Ch cM cP cR cT CX De dG dH dK) cT(aD aE AF aO aW bB bF bO cG cL cV cX dG dH) dG(aW Ax aZ bC Bn bO bV cP cS cX dA De dM dN) cP(aE AF aW bC Bn bO cR Cx De dH dL) bO(aD aE AF aW bX Cx dH dL dM) aW(Af bC bX CX De dH dL) cX(Ax Bc Cs Cv De dH dL) dL(aD Af Cx De dN) bW(Af bC Bn Cx) dH(aZ bC Cx dN) Af(Bc Cv) De(Ax Cs) BcCx aQdM} Ok{Jt(Fr Hw Is Iv Jg Jl Li Lj Lw Mk Mr Nb Nr Pa Pb Pe Qc) Nn(Et Fp Ij Jk Mb Md Ms Nd Nf Nk Nm Nv Nx Qc) Pc(Hr Ii In Jh Jk Lh Ms My Nm Nv Nx Ny Oe) Mj(Hv Li Lj Ml Mu Mx Nc Ne Nh Oh) Qc(Fp Hr Lj Lv Mb Nm) Mb(Js Md Nj Nk) Jo(Mf Mk Mr Wm) Nm(Lv Ne Pb) Nk(Hv Nh Nl) Js(Fp Lj Oh) Fr(Jk Nx) Ii(Ma Mm) Il(Mk Pa) Oe(Md Mq) Pb(In Pd) NtLv NeNi NhOg HvHw} Nu{Nw(Ii In Js Md Mj Ms My Mz Nk Nx Ny Of Og Qc) Fr(Ii Iq Lv Mb Md Mj Na Ng Nk Nr Of Og) Nk(Hv Ji Jp Li Lv Lw Mp Nn No Pb) In(Hw Iv Mr Nb Pa Pb Pe) Ji(Ii Mj Of Og Pb) Lv(Na Of Og Pb) Md(Jg Mp Nd Pc) Il(Iv Mk Pa Pc) Of(Jg Lw Nn) Na(Is Lw) NoJs NrLi} Nw{Js(Hv Iq Jn Lj Lv Nc Ne Nh Of Og Oh) Of(Fr In Li Lv Lw Md Nk Nn Ny) Md(Iq Lv Ne Nk Nn Og Pc) In(Hv Iq Lv Mj Ne Nh Nk) Lv(Lj Ny Og Qc) Nn(Ii Ms My) Mj(Lj My Ny) Nk(Nh Nl) Il(Mk Pa) Ny(Iq Og) Pc(Ms My)} Nk{No(Fp Lv Mb Nc Ne Nh Nl) Lw(Fp Hv Li Lv Ne Nh) Fr(Fp Nc Ne Nl Of) Nn(Nc Ne Nl Of) Nc(Ji Li Lv) Ji(Ne Nh) Li(Lv Of)} Lv{Lw(Fp Hv Li Lj Ne Of Og) Of(Fr Jg Li Mu Nn) Fr(Fp Iq Qc) Li(Iq Mj Qc) NoJs MdPc} Fr{Of(Fp Hv Ji Lw Ly Nh Oh) Lw(Fp Iq Mb Nd) Iq(Hv Ji) FpNr MkOy} dM{aQ(Af Bn Cx De) cX(Ax Bo Cs Dl) cT(aD Af bB) AfbN CsDe bVcV} Il{Pa(Fp Ji Lw Mb Nn Nx Pb Pc) Iv(Fp Lw Pb) FpMk NoPc} Ji{Nn(Ii Iq Of Og) Og(Ne Pb Pc) Pc(Md Ms) MuOf IqJl} cT{Af(aW BC bJ) cE(aP cN cP dN)} Bc{cX(aE Ao aW cR) aW(Af Cx)} Lw{Of(Li Mu Nn)} Md{Pc(Fp Jq) MuHu} De{CsaW aQdA} AfBaaW

Constrained panels with 3 analytes, where 1.0E-4 >= 'model p-value' > 1.0E-5. Contains 3,155 panels of 597,622 total panels evaluated. : Lv{Of(Hu Hv Hw Ii Ij Is Iv Ji Jl Jp Jt Lh Lj Ly Mj Mk Mm Mr Mv My Nb Ne Nh Nk No Nr Nv Oh Om Oy Pa Pb Pc Pe Pf Po) Om(Fp Hu Hv Hx Ij Im Ir Is Jl Jp Jt Lh Md Mj Mm My Mz Nb Nh Nk No Nv Pb Pf Po Qe) Iq(Hv Hw Hx Ir Is Iv Jg Jl Jp Jt Lh Lj Mj Mk Mr My Nb Nn No Nr Nw Pa Pc Pe Po) Nk(Fp Hu Hv Hw Hx Is Iv Jl Jp Lj Mk Mm Mp Mu Nb Ne Nh Nl Nn Nr Oh Pb Pe Po) Og(Fp Hv Hw Is Iv Jg Ji Jl Jq Jt Li Lj Lx Mk Mr Nb No Nr Oh Pa Pb Pc Pe) Js(Hv Hw Hx Is Iv Jl Jn Jt Li Lj Mj Mk Mr Nb Nr Oh Pa Pb Pe Po) Mj(Fp Hv Hw Iv Jl Jt Lh Lj Mk Mr Nb No Nr Nw Oh Pa Pe) Fp(Hw Iv Jg Jl Jp Mk Mr Mu Nn Nr Pa Pb Pc Pe Qc) Mm(Hu Hv Hw Is Iv Jl Lj Mk Mr No Nr Pa Pe) Jg(Hu Jh Lj Ly Md Mv My Ne Ng Nh Qc) Fr(Jm Jo Lj Ly Md Ne Ng Nh Nr Pb) Jq(Hw Iv Ji Jl Lj Mk Mr Nr Pa Pe) Ni(Iv Jl Mk Mr Nc Nr Pa Pe) In(Hw Hx Iv Mr Nb Pa Pb Pe) Qc(Ji Jp Lj Mu My Nn Oh Qe) Nn(Ii Ji Jm Lj Ng Nr) Md(Mp Nb Nd No Po) Jo(Jt Mk Mr Pa Pe) Lj(Hu Mu Nr Pb Pc) My(Ne Nw Pb Pc) Na(Iv Mr No Nr) Jp(Ly Ng Nh Pb) Pc(Mv Nh Ns) No(Jr Mc) Mu(Ng Pb) Hv(Ji Pb) Nw(Ii Ne) PoLi LwNh NdOz JiJl} Nw{Iq(Fr Hv Hw Is Iv Jl Jp Li Lj Lw Mk Ml Mm Mr Ms Mt My Mz Ne Nk Nn Nr Nx Og Oh Pa Pc) Og(Li Lj Lw Mj Ml Ms Mt My Mz Nc Nd Ne Nh Nk Nn Nx Of Oh Pb Pc Qc) Qc(Fp Fr Hv Ii Jp Li Lj Lw Lx Mb Mf Mm Ms Ne Nh Nn Oh Qa Qc) Mj(Fp Hv Hw Il Iv Jl Li Lx Mk Mr Mt Ne Nh Nn Nr Oh Pa Pe) Ne(Fr Jn Lw Ml Ms Mt Mw My Mz Nc Nr Nv Nx Ny Of Om) Nx(Fp Fr Hq Hv Hx Li Mu Nc Nh Nl Nn Oh Om Pc) Ms(Fr Hq Hv Hx Js Lw Mu Mz Nc Nh Oh Om Pd) Hw(Hq Hr Hv Hx Ii Ij Il Jl Jo Jt Lj Oh Pg) Nk(Fp Hv Li Lj Mb Mv My Nn No Ny Oh Pc) Js(Fp Is Iv Mb Mr My Nf No Nr Pa Pe) Of(Jp Lj Lx Ml Mq Mt Mu My Mz Nh Oh) Nn(Ij Jk Jo Lj Mu Mv Mw Nd Ng Nv) Fr(Ii Jk Mb Mv Mw My Nc Nd Nv) Mz(Fp Hv Lj Nc Nf Nh Nl Nv Om) Pc(Jh Lw Mu Mv Mw Nf Ns Nv Oy) Ii(Hv Jl Lw Lx Mk Mr Nr Oh) Mk(Ij Jo Jt Ni Oy Pg) Mr(Ij Il Jo Jt Ni Pg) Nr(Il Jt Na Nh Nu) Lw(Jt Mb Nd Nh Nu) Nv(Hx Mu Nc Nh Nl) Ij(Iv Jl Lx Pa) Nu(Ml Mt Na) Ni(Jl Nc Pa) Iv(Il Jt Pg) Wm(In Jo) Mw(Nc Nh) Om(Im Jp) NoJr LxLh MbMl NdLj NhPz HxPb IlPe JlJt PaPg} Lw{Of(Fp Hu Hv Hw Ik Ir Is Iv Jg Ji Jl Jp Lh Lj Mk Mr Mt Mv My Nb Ne Nh Ni Nk No Nr Nv Oh Oy Pa Pb Pc Pe Pf Qe Wm) Ni(Fp Hu Hv Hw Is Iv Ji Jl Jp Lh Li Lj Mk Mr Mu Mx Nb Nc Ne Nh Nk Nl Nn No Nr Nu Oh Om Pa Pb Pe) Nk(Fr Hu Hw Is Iv Jl Jp Lj Lx Mb Mh Mp Mr Mu Mx Nc Nl Nn No Nr Oh Om Pa Pb Pc Pe Pf) Iq(Hv Hw Hx Ir Is Iv Jg Ji Jl Jp Lh Li Lj Mk Mr Nb Nn No Nr Nv Oh Pa Pb Pe Qe) Om(Hw Hx Im Ir Iv Lh Lj Md Mk Mr Mt Mx My Mz Nb Nh No Nr Pa Pb Pe Qa Qe) Mb(Hv Is Iv Jl Jp Lx Mk Mr Mu Nj Nn No Nu Pa Pc) In(Hv Hw Hx Is Iv Mk Mr Nb Nu Pa Pb Pe Wm) Og(Fp Hu Hv Is Iv Jg Jl Mr Nb No Nu Pb Pc) Nd(Is Jg Ji Jl Jp Li Lx Mu Nn No Pc) Hw(Hr Hv Hx Is Iv Jl Jo Lx Mr) Md(Jg Lx Mp Nb Nn No Nu Pc) Nh(Fr Ji Jp Nn Pb Pc) Fp(Jp Lx Mu Pb Pc) Nu(Ii Jp Ns Pb Pc) Ne(Fr Jg Ji Nj Pb) Hv(Ii Ji Js Pb Pc) Il(Is Mj Mk Mr Pe) Jo(Lx Mk Mr Pa Pe) Na(Iv Lx Nr Pe) Js(Is No Oh) Hr(Mr Pa) NnIi LxHq QcQe JgLj JpPb LiPc} Om{Nu(Hv Hw Hx Ip Ir Is Iv Jh Jl Jq Jt Lh Li Mk Mm Mr Mv My Mz Na Nb Nk Nr Nv Of Og Oh Pa Pc Pe Po Qe) Jg(Fp Hu Hv Hw Hx Ir Is Iv Jh Jl Li Lj Md Mk Mm Mr Mv Mw Mx My Mz Ng Nk No Nr Ns Of Pa Pe Qe) Oh(Fp Hw Hx Is Iv Jh Jl Jp Jq Jt Lh Mk Mr Mu Mv My Nb Ni Nk Nr Nv Pa Pc Pe) Mu(Et Fp Hv Hw Hx Ir Jl Jp Jq Jt Lh Mj Mk Mm Mz Nb Nk No Nr Pa Pe Qe) Li(Hv Hw Is Iv Jl Jq Mk Mp Mr My Nb Ni Nj Pa Pb Pc) Jp(Fp Hw Is Iv Jl Md Mk Mr Mx Ni Nk Nr Pa Pb Pe) Md(aA Fp Jo Lj Mb Mj Ml Nb Ne Ni No Of Pc) Mm(Hv Hw Is Iv Jl Lh Mk Mr Nb Nr Pa Pe) Nv(Hw Is Iv Jl Lj Mk Mr Nk Nr Of Pa Pe) Mv(Hw Is Iv Jl Mk Mr Mz Nr Pa Pe) Jq(Hw Iv Jl Mk Mr Nr Pa Pc Pe) Fp(Is Jl Mk Mr Nr Pa Pc Pe) Pc(Lj Mx My Mz Ns Pe) Nk(Hv Is Jl Mp Pe) Nn(Ip Mh Ng) No(Jr Js Mc) Jl(Is Mz Ni) Wm(Fr Mi) aA(Jk Nd) IlIv PzJj} Lx{Jo(Fp Fr Hx Jk Li Mf Mj Mm Mt Mu Mv My Mz Nc Nd Ne Nh Nn Of Og Pb Pc Pg Wm) Nk(Hv Hx Iq Jk Lh Li Lj Mh Ml Mt Mv Mw My Nb Nn No Oe Og Oy Pb Pc) Lz(Hq Hx Ij Lh Lj Mb Mh Ml Mt Mv Mw My Mz Nc Ne Nf Nh Ny Pb) Pf(Hq Hx Ii Ij Jk Js Lh Md Ml Mv My Mz Nf Ny Of Pb Pg) Nn(Hw Ij Jk Mb Md Mj My Nd Ng Ni Nr Og Oy Pg) Of(Fp Hq Hw Jp Js Li

Figure 17 Continued

Md Mm My Nh Oh Pc Pg Po) Mj(Fp Fr Hv Ji Li Lj Mb Mf Mu Na Oh Oy) Js(Fr Hv Ji Jp Li Lj Mb Mf Ml Na Nh No) Nr(Fp Fr Li Lj Mt Ne Nh Oh) Nu(Hq Iq Jk Md Ng Nt Og Pg) Hw(Fr Hq Hr Md Nh Og Pg) Mb(Fr Ji Lh Mh Mm Nj) Na(Iq Lh Mh Ne Nh Ny) Ii(Hv Ir Ma Mm Mz Oh) Jg(Ij Md Mv Mw My Ng) Po(Hv Mu Nc Nh Og) Fr(Ij Md Nd Ng) Nd(Jp Mm Og) Ng(Jp Mf Mu) Nl(Ne Nh Ni) Iq(Ji Jp Li) Jk(Mu Mv My) Pc(My Og Pg) WmIn MdIu MkOy MrPe NhNi HqLi QcQe JiOg LhOz} Nk{Fp(Hv Hw Is Iv Jg Ji Jl Jp Lh Li Mk Mp Mr Mu Nb Nc Nn Nr Nu Pa Pb Pc Pe Po) Nu(Hq Hw Hx Is Iv Jg Jl Jq Lj Mk Mq Mr Mu Mv Nb Nc Nr Nv Og Pa Pc Pe Po) Nc(aA Hv Hw Hx Is Iv Jg Jl Jp Lh Mk Mp Mr Mu Nb Nr Pa Pb Pc Pe Po) Hv(Fr Ji Jp Li Lj Mb Mm Mp Mu Ne Nh Nl Nn No Oh Pb) Nn(Hw Iq Iv Ji Jl Lj Mb Mr Nh No Nr Pa Pb Pe) Fr(Hw Iq Iv Lj Mb Mp Nd Nh Nj No Nr Pb) Nh(aA Jg Jl Jp Li Mp Mu Pb Pc Pe Po) Ji(Iv Jl Li Lj Mb Mu Nl Nr Of Oh Pc) No(Iq Jp Li Md Mu Nd Nj Of Og Pb) Ne(Jg Jl Jp Li Mp Mu Nb Pc Po) Nl(Jg Jl Jp Li Mp Mu Pc Po) Jg(aA Lj Md Mv Ng Of) Li(Iq Jl Mp Mu Ng Pb) aA(Mb Mq Pe Po) Po(In Md) Mb(Jl Mp) Mu(Lj Of) Jj(Mf Ni) MpPb IlPe LjPc NvOf} bA{Bn(aD aF aJ aM Ao aS aW aY bB BC bF bJ bO Ch cN cP cR cV dA dM) Cx(aE aF aH aJ aL aM aN Ao bB Bc bF bJ bO cG cL cP cR cV De dM) De(aA aD aF aM aS aY BC bF BO cN Cs cT cV dA dM dN) Ch(aA aD aF aJ aM aW BC bJ bO cV dA dM dN) Bc(aD aE aJ Ao aW bB bF bO cG Co cV dM) dA(bI bJ bN bQ bR bZ cA cO dB dH dI) Ao(aF aJ aM aS bC bJ bO cP cV Cw) cG(aN Ax bC bJ bP bV cR cX dG) cX(aL aN aS aY bE cL Co cR) cN(aE aF aO bN bQ cV dF) bB(aP aY cR cS cT dE) aH(cW dB dE dN) aY(aF bJ cV dH) bE(aG aO cL cW) cL(aN dE dN) cP(Bg Co Cs) aF(aE aS) al(cS dN) aO(aP cS) cV(aN bJ) dH(aP dG) CsbO aGcR aLcW aQaU aScT bZdN cBdB} Ji{Of(Hv Hw Iv Jg Jl Jp Li Mk Mr Mv My Ne Nh Ny) Iq(Hq Hv Hw Is Iv Jp Jq Li Lj Mj Mk Mr Nr Og Pa Pb Pc Pe) Og(Fp Fr Hv Hw Iv Jl Li Mk Mr Mu Nh Nr Oh Pa Pe) Nn(Fp Jq Lj Mb Md Mp Ms Mv My Nc Nd Ne Nh Qc) Mb(Fr Hw Iv Jl Jp Mk Mr Nj Nr Pa Pc Pe Qc) Mj(Fp Hv Hw Is Iv Jl Li Mk Mr Nr Oh Pa Pe) Pc(Fp Jh Lj Mv My Nc Ne Nf Nh Ns Oy) Ni(Iv Jl Mk Mr Nc Ne Nl Nr Pa Pe) In(Hw Hx Iv Mr Nb Pa Pb Pe Wm) Qc(Fp Fr Hv Jp Li Lj Mu Oh Qe) Fr(Jq Md Nc Nd Ne Nh) Hv(Hw Ii Jq Js Pb) Fp(Jq Mk Mr Pa) Il(Iv Mk Mr) Oh(Ii Jq Js) Mu(Jq Lj) Jo(Mk Mr) Jp(Ly Nd) Pb(Ne Nh) MdJg MiMs} Nu{Of(Hw Is Iv Jl Jp Jq Lh Li Mk Mr Mu Mv My Nb Nr Nv Pa Pc Pe) Og(Hv Hw Is Iv Jg Jl Jq Li Mk Mr Mu Mv Nb Nn Nr Pa Pb Pc Pe) Na(Hv Hw Iv Jl Jp Lh Mj Mk Mr Mu Mv My No Nr Pa Pc Pe) Nr(Fp Ir Is Jg Jl Jp Lh Lj Mu Mv Ni Nn Pa Pb Pe) Ii(In Is Jg Jl Jp Lh Li Nn Nv Pa Pe) Nn(In Jm Jo Jq Js Md Mj Ms Ng) Ni(Is Iv Jl Jp Mk Mr Pa Pe) Jg(Hu In Jk Ms Mv My Ng Oi) Jq(Hw Jl Mk Mr Pa Pb Pc) In(Hx Is Jl Lh Mk Pc) Mp(Hq Oz Pd Pf Pg) Pc(Ms My Ns Oi Oy) Md(Jp Nb No Nv) Ng(Jl Jp Mu Mv) Il(Is Mj Mr Pe) Jo(Mk Mr Pa Pe) Js(Is Jn Jp Nb) Nd(Hq Oz Pd) NoJr MkOy MuOi JpPb} Fr{Iq(Fp Hw Ir Is Iv Jl Li Lj Mj Mk Mr Nh No Nr Of Pa Pe) Ng(Fp Hv Hw Iv Lj Ly Mb Mk Mr Nd Ne Nh Nl Pa Pb Pe) Of(Hw Is Iv Li Lj Mk Mr Nd Ne Nl Nn Nr Pa Pb Pe Wm) Hv(Hw Ii Jk Js Mb Md Mj Nd Nq Nr Po) Mb(aA Hw Iv Md Mk Mr Nr Pa Pe) Md(Fp Ly Mp Ne Nh No Pb Pc) Hw(Iiq Hr In Jk Jo Nd Nr Oe) Lj(Ly Nd Ne Nh Nr Pb Qc) Pc(Ms Mv My Ne Nl Ns Og) Jk(aA Iv Mk Mr Pa Pe) Nr(Iv Ne Nh Nl Oh) Hu(Ly Ne Nh Nl Pb) Ii(Mr Nn Oh Wm) Il(Iv Mk Mr Pa) Fp(Mj Po Qc) aA(Nd Nq Oe) Wm(In Jo) Mv(Jg Nn) Ni(Nc Nl) Iv(In Nd) dM(Af De) NoJs MrJo NeJq} aA{Ax(aD aG AO aW bJ bN cP Cq cV dM) Nd(Hv Mp Mq Mz Ng Nn Of Og Oh Pa Po) Jg(Il Jk Ly Mf Mw My Ni Ns Oe Og Oi) Nn(Hu Jk Lj Mu Mv Nq Nr Oe Oi) Ar(aD aG aM AO cE cV dM) Bc(aF aO bJ bN cE Ch dC dM) Ng(Hu Ik Lh Mb Mu Ni Nv) Cs(aD aF aO cE cV dH) De(aD aE aG bJ cV dM) Il(Iv Lh Mk Mr Pe Po) No(Jr Js Lz Md Na) Nr(Nt Nv Oh Pc Pf) Mq(Lj Md Mf Nj Ns) Ao(bC bJ Cw dN) Ch(bJ bN cV dN) Mm(Lj Nq Of Oi) Oh(Ii Js Nm Oi) Mf(Mp Og Oi) Ni(Nj Nl Po) Nv(Md Nq Oe) Of(Mu My Pe) Hw(Hv Lj) Js(Lj Pe) BnaN PoIn NqLh MvPe LiOi} cT{cE(aD Af aM aN aW Ax aY BC bJ bP bV cS cU CX dA dB dE dG) cP(aE Af aW bB bF Bn bO bV cB cG Ch cL cN cR dA DE) Af(aD aM aN aP aY Bo cL cN cR Cw Dk dN) dM(aE aF aG aM bF BN bO cL Cx DE) aW(aD aM aP bJ Bn cR CX dA DE) aD(bB bJ bN bO bV CX dA dE) aM(aE bB bJ BN bO cL Cx dE) aP(aE aF aG aO bB bF bO cG cL) aJ(Ao Bc Bn Ch Cx De) cL(aY cN Cx dA dN) cX(Ao Bc Ch De) dN(bB bF cV) Bc(Ao Cx) aE(bJ cN) ChCx aFdE bBcN bVcV} aJ{Bc(aD aE Ao aW BN bO bW Ch cP De dG dL) aF(Af Ax aZ bC bM Bn bX Ch cR Cx De dL dM) cE(Af aZ bC bF bG Bn bQ bV cR CX dM) Bn(aO aW aZ bO bX CV dH dL dM) De(aG Ar bO bW bX CV dH Dk dM) Cx(aE aG aO aP Ax bX Cv dM) dH(aE Af Ax bV bX CV dM) bO(Ao Ax Ch cM Cs cX) cX(aE aZ bW bX dM) Af(aP Ax bX cV) Ch(aW cP dG dL) aQ(aU bB cR dL) Ao(Ax Ba bN) aD(aZ bC bM) cV(bV cR dN) aE(aM dL) bB(cM dD) bU(bX dA) AxfR CsdG aldD bXdM cLdA} dM{Af(Ad aE Ar Ax Ba Bb Bc Bg Bo cP Cq Cs Cv Cw Dk Dl) cE(aP aQ Ax Ba bF Bo bQ bV cZ cR Cw Cx dD dE dF dN) bN(aD aM Ax Bn Bo cP cR Cw Cx Db DE dN) aQ(Ax bB Bc bJ Bo bV cR Cw dA Db dE dN) De(Ar Ax Ba Bc Bg Bo cP Cq Cw Dk) Cx(aE aW Ax Bc Bo cP Cs Cw Dl) bB(bV cM cP dB dD dE) cP(Ax Bn bV cR Cs) Ax(Bn bO cV) Cs(Bn bO cV) cX(Ba Bc dE) Ao(Ba Cw) Bo(Bn bO) aXbV} Nn{Of(Fp Hv Hw Iq Is Iv Jg Jl Lh Li Ly Mk Mr Nh Ni Nr Pa Pb Pe Wm) Ii(Fp Hv Hw Is Iv Jl Jt Lh Mk Mr Nb Nr Pa Pe) Iq(Hv Hw Is Iv Jl Mk Mr Nr Pa Pe) Ni(Hw Iv Jl Mk Mr Nc Nr Pa Pe) Wm) Og(Fp Hw Iv Mr Pa Pb Pc) Fp(Jm Md Nr) No(Jr Js Md) Mr(Il Jo Ng) Nr(Lj Nh) Mk(Il Oy) Ng(Hw Nh) MdPc MvJg HrHw IIIv JnJs} Il{Pa(Hv Ik Iq Ir Is Jg Li Lj Mf Ml Mu Mv Na Nd Nh Nl Nv Oh Qa Qb Qe) Iv(Hv Is Jg Li Lj Mb Mf Mu Nh Nl Nv Nx Oh Pc Pe Po Qb Qe) Mk(Hv Ir Is Jg Li Lj Mp Mu No Nx Oh Pb Pc Pe Qa Qe) Pc(Hv Hw Is Lh Lj Mj Mr Nb Nr Pe) Mr(Fp Hv Jg Nx Pb Qe) Pb(Hw Jl No Nr Pe) FpMj LzPe MdNb} Of{Jg(Fp Hu Hv Hw Is Iv Jh Jl Lh Li Lj Md Mj Mk Mp Mr Mu Mv My Ng Nh No Nr Ns Oh Pa Pb Pe) Mu(Et Fp Hw Is Iv Jl Jt Lh Li Lj Mk Mm Mr Nb Nr Pa Pb Pe) Li(Hw Iq Is Iv Jl Mk Mp Mr My Nb Ni Pa Pb Pc) Wm(Jp Ok) NoJr NbPc} cP{Bc(aE Af Ao aW bB bO Ch cR CX De) cR(Af aP aW Ax BN Ch Cs Cx De) Ch(Ba Bn Bo Cw CX) De(aW Ax BO Cw cX) Af(aW Ax BO Cw) Cx(aW Ax bC bO) Bn(aW BO) Ax(bO cX) Cs(bO cX) AoCw aFfR aPaW bVcV} aW{Af(aP Ax bC bN Bo cR Cs Cu Cv Cw Dk fR) Cx(aP Ax bC bN bO bV cR Cs Cu fR) De(aP Ax Ba Bc bN Dk) aP(BN bO cE) cX(Ax Cs Cu fR) AxbO bVcV} In{Fp(Hw Hx Iv Mk Mr Nb Pa Pb Pe) Wm(Jp No Nv Og Ok On Pb) Iv(Hv Li Mm Mu Nh Oh) Hw(Li Mm Mu Nh Oh) Mm(Nb Pa Pe) Mu(Mr Pa Pe) Li(Mr Pb)} Md{Pc(Hu Hv Jg Jp Li Mb Mq Mu Mx My Nb Nh Ni No Nv) Jg(Fp Hv Lj Mp Nh Ni Pb) Fp(Mp Nb Nd No) No(Iq Mb Ni) Nd(Jj Mb Nh) MpPb} Bc{cX(aD aN aQ bJ bN bV bW cE Ch cQ DE) Af(aD aE aQ bJ bN Bo cQ cR Cs fR) Cx(aD aE Ao bJ bN bW cE Ch cR De)} Js{No(Fp Hv Iq Jp Li Mb Mf Ml Mu Ne Nh Og Oh Ok On) Jn(Jj Pe Po) On(Iv Mv) FpIs} Iq{Li(Hw Hx Is Iv Jl Mk Mr Nb Nr Pa Pc Pe) No(Jr Mc) Jg(Lj Mv) Mmls JlJp LjPc} Cs{De(aF bC bN BO cN cR CX dN) bO(Af CX) AfbJ aMbN cRcX} Pc{Fp(Ms My Nr Ns Og) My(Hu Jg Jq Mu) Jq(Lj Ms Ns) NsMq MvJg NiLj} Wm{Mi(Ii Mb Nt Po) Jp(Ii Ij Jo Pg) Ok(Ii Nt Og) On(Hr Ij Jt)} Af{bN(aM aP Bo cN fR) Ax(bJ bO cR) Ba(aD Bo Ch) BoCv aPbW} Mi{Na(Hv Is Mj) Pc(Hw Mk) NqPa MsOh MuHu QaQc LhPf} Fp{Nr(Jl Mk Mr Pa) NoJr MpPd OgPa} Ni{Li(Iv Jl Mk Mr Pa Pb) JlJp} Jg{Lj(Ng Nr Og Pb) Pb(My Ng) MkOy} cX{Ax(aE bO cR De) Ba(Ao Ch) cEfR} bN{aM(Ar Ax Bo) aP(aD Cx De)} De{AxBo bVcV} No{MbJr OgPb} Jj{LyIh QcQd} On{NmMy MjJm} aQ{dA(Bn cL)} MkMuOy bVcEdN Constrained panels with 3 analytes, where 1.0E-3 >= 'model p-value' > 1.0E-4. Contains 5,338 panels of 597,622 total panels evaluated. :
Om{My(Et Fp Hv Hw Hx Im Ip Ir Is Iv Jl Jp Jq Jt Lh Lj Mj Mk Mm Mp Mr Mx Mz Nb Nh Nk No Nr Pa Pb Pe Pf Qa Qe) Jq(Et Fp Hv Hx Ii Ir Is Jg Jp Jt Lh Lj Lv Ma Mj Mm Mp Mt Mv Mx Mz Nb Ne Nh Nk No Nt Pb Pf Po Qa Qe Wm) Nk(Fp Hw Hx Im Ir Iv Jt Lh Lj Mj Mk Mm Mr Mt Mv Mx Mz Nb Nc Ne Nh Nl Nr Nt Pa Pc Pf Po Qa Qb Qe) Hv(Et Fp Hw Im Ip Iv Jh Jl Jp Jt Lj Ma Mk Mp Mr Mv Mz Nb Ni No Nr Oh Pa Pb Pc Pe Pf Po Qe) Hx(Et Fp In Ir Iv Jh Jl Jp Jt Lj Ma Mj Mk Mm Mp Mr Mt Mv Mx Mz Nh Ni No Nr Pb Pc Pf Qe) Pb(Et Fp Hw Im In Ir Is Iv Jg Jl Jt Lj Mj Mm Mt Mv Mx Mz Ne No Nt Og Oh Pf Qa Qe) Pc(Et Im Ir Is Jg Jl Jp Ma Mm Mp Ms Mt Mv Ne Nh No Nt Nv Pf Po Qa Qd Qe)

MbNj NcJn} aW{Bn(aM Ax Ba BC Bo cR Cs fR) aM(Ax Ba Bc Bo Cs Cw fR) Ch(aP Ba BC Bg Cw) Bc(Ax Bo cR fR) Cs(bC bJ cV) Ax(aJ cR) bC(Bo fR) CubB aPdH cEdF cRdN cVfR} Md{Nb(Fr Jp Li Mb Mf Mu Nh Pb) Po(Jp Lw Mb Mu Nu Pb) Lv(Hx Mw Nv Ny Oy Pg) No(Mj Mu Na Pb) Nv(Lw Mb Mk Pb) Nu(Hx Mq Ny) Mu(Et Hx Pg) FrNl LwMb} Jo{Nv(Iv Lv Lw Mk Mr Nu Pa Pe) Mr(Et Li Mu Mv Oh) Li(Lh Mk Nb Pe) Et(Mk Pa Pe) Fr(Iv Jt Pe) L

Mm(Lu Md Me Ms Mw Ni Nj Of) Jh(Iq Jm Lz Md Mn Ni Nj Qc) Pz(Md Me Ni Oe Of Qc) Md(Jm Mw Ng Ny) Ni(Jm Mn Ng Nj) Lz(Js Mw Ng) Nj(Il Ma Nq) Iq(Et Ng) Jm(Oc Qc) lJr JnJs} bA{Af(aA aC AD aE aF aG aH aI aJ aK AL aM AN AO AP aQ AR AS aU aV AW AX aY aZ Ba BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN FR) cE(aA aC AD aE aF aG aH aI AJ aK AL aM AN AO AP aQ AR AS aU aV AW AX aY aZ Ba BB BC bE bF BG bH bI bJ bL bM BN BO bP bQ bR bS bU bV bW bX bZ cA cB cC cD cF cG CH cI cJ cK cL cM cN CO CP CQ cR CS CT CU CV CW CX cY cZ dA DB DC DD DE dF DG dH DI dJ DK DL dM dN FR) Cx(aA aC AD aE aF aG aH aI AJ aK AL aM AN AO aP aQ AR AS aU aV AW AX aY aZ Ba BB BC bE bF BG bH bI bJ bL bM BN BO bP bQ bR bS bU bV bW bX bZ cA cB cC cD cF cG CH cI cJ cK cL cM cN CO CP Cq cR CS CT CU CV CW cY cZ dA DB DC DD DE dF DG dH DI dJ DK DL dM dN FR) De(aA aC AD aE aF aG aH aI AJ aK AL aM AN AO AP aQ AR AS aU aV AW AX aY aZ Ba BB BC bE bF BG bI bJ bL bM BN BO bP bQ bR bS bU bV bW bX bZ cA cB cC cD cF cG CH cI cJ cK cL cM cN CO CP CQ cR CS CT CU CV CW cX cY cZ dA DB DC DD dE dF DG dH DI dJ DK DL dM dN FR) cX(aA aC AD aE aF aG aH aI AJ aK AL aM AN AO AP aQ AR AS aU aV AW AX aY aZ Ba BB BC bE bF BG bH bI bJ bL bM BN BO bP bQ bR bS bU bV bW bX bZ cA cB cC cD cF cG CH cI cJ cK cL cM cN CO CP Cq cR CS CT CU CV CW cY cZ dA DB DC DD dE dF DG dH DI dJ DK DL dM dN FR) Bn(aA aC AD aE aF aG aH aI AJ aK AL aM AN AO AP aQ AR AS aU aV AW AX aY aZ Ba BB BC bE bF BG bH bI bJ bL bM bN BO bP bQ bR bS bU bV bW bX bZ cA cB cC cD cF cG CH cI cJ cK cL cM cN CO CP Cq cR CS CT CU CV CW cY cZ dA DB DC DD dE dF DG dH DI dJ DK dL dM dN FR) Ch(aA AD aE aF aG aH aI AJ aK AL aM AN AO aP aQ Ar AS aU aV AW Ax aY aZ BB BC bE bF bG bI bJ bM bN BO bP bQ bR bS bU bV bW bX bZ cA cB cC cF cG cH cI cJ cK cL cM cN CO CP Cq cR CS CT CU CV CW cY cZ DB DC DD dE dF DG dH DI dJ DK dL dM dN fR) aF(aA aC aD aE aG aH aI AJ aK aL aM aN AO aP aQ aR aS aU aV aW AX aY aZ BB BC bE bF BG bH bI bJ bL bM bN BO bP bQ bR bS bU bV bW bX bZ cA cB cC cD cF cG cH cI cJ cK cL cM cN CO CP Cq cR cS CT cU CV CW cY cZ d

Hv Hw Hx Ih Ii Ij Ik Il Im In Io Ip Iq Ir Is It Iu Iv Jg Jh Ji Jk Jl Jm Jn Jo Jp Jq Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Oy Oz Pa Pb Pc Pd Pe Pf Pg Po Pz Qa Qb Qc Qd Qe Wm) Nw(Fr Hq Hr Hv Hw Hx Ih Ii Ik Il Im In Io Ir It Iv Jg Jh Jk Jl Jn Jo Jq Jr Js Lu Lw Mb Md Mg Mj Mk Mp Mr Mu Mv Mx Mz Na Nb Nc Ne Nh Ni Nj Nm No Nr Nu Oe Of Oh Oy Pa Pc Pe Po Pz Qa Qc Qd) Jg(Hq Hv Hw Hx Ih Ij Ik Il Im In Ir Is It Iv Jh Jk Jl Js Lw Lx Ly Mb Mc Md Me Mf Mk Mr Mt Mu Mw Mx My Nb Nc Ne Nh Ni Nj Nk Nr Ns Nu Nv Ny Oe Of Og Oh Ok Oy Oz Pa Pb Pc Po Qa Qc Qe) Mu(Et Fp Fr Hv Hx Ih Im Ip Ir Is Ji Jp Lh Li Lj Lx Mb Mh Mt Mx Mz Nh Nu Nv Oh Ok Pf Qa Qd Qe) Im(Fr Ip Is Ji Jp Li Lw Lx Mp No Nu Nv Oh Ok Pc Po Wm) Fr(Hv Ly Mb Mf Ne Nh Ni Nl Nu Oh Ok Pb Qa Qe) Nv(Il In Jh Js Lw Md Ne Nh Ni Nk Nu Og Oh Qc) Ok(In Jh Jl Jo Mj Mv Ni Qa) Nu(Jp Li Mm Mv Og) Mv(Jp Li Lx Oh) Nk(Jl Li Oh Qa) Ni(Jp Li Oh) Lw(Mt My) NoIl MbJp MpMt MyLi JhOh} Nu{Fr(Fp Hv Hw Ii Ij In Iq Jk Jo Jp Js Jt Mb Md Mf Mj Ml Mp Ms Na Nd Ne Ni Nk Nm Nq Nt Oe Of Og Pb Pc Pd Po Qc) Na(Hv Hw Hx Il In Is Iv Jg Jl Jp Li Lw Lx Mk Mm Mp Mr Mu Mv Mx Nk Nn No Nr Nw Og Ok Pa Pc Pe) Jp(li Il In Iq Jo Js Jt Mb Md Mf Mj Mu Nd Ne Ng Ni Nk Nm Nr Nt Oe Of Og Oi Pb Po Pz Qc) Nk(Fp Hq Hv Il Jg Li Lj Lw Lx Mp Mu Mv Mx Nc Ng Nn Of Og Pa Pb) Il(Fp Ij Is Iv Li Lj Lw Lx Mj Mk Mr Ng Nw Ok Pa Pb Pc Pe Po) In(Hw Hx Is Iv Jl Li Lx Mk Mr Mu Nb Nn Nw Ok Pa Pb Pe Wm) Of(Et Im Jg Jh Li Lx Ma Mm Mu Mv Nn Nv Nw Oh Ok) Jo(Et Hq Jg Li Lw Lx Ma Mm Mp Mu Nn Nv Nw Ok) Og(Hu Jg Jh Li Lw Lx Mu Mv No Nw Ok Pb) Nn(li Iq Jk Js Jt Mj Nd Ng Nm Nr Oi) Ii(Jg Li Lw Lx Mu Mv Nv Nw Ok) Ok(Jq Js Jt Mj Nt Qc) Mu(Fp Lj Ml Ms Oi) Lx(Mj Nt Oe Qc) Li(Js Jt Ni Qc) Nw(Js Jt Mj)} Of{Nn(Fp Fr Hq Hr Hu Hv Hw Hx Ih Ii Ij Ik Im In Io Iq Ir Is It Iu Iv Jg Jh Ji Jk Jl Jn Jp Jq Jr Js Jt Lh Li Lj Lu Lw Lx Ly Lz Mb Mc Md Me Mf Mg Mh Mj Mk Ml Mm Mn Mp Mq Mr Ms Mt Mu Mv Mw Mx My Mz Na Nb Nc Nd Ne Nf Nh Ni Nj Nk Nl Nm No Nq Nr Ns Nt Nv Nw Nx Ny Oe Oh Ok Oy Oz Pa Pb Pc Pd Pe Pf Pg Po Pz Qa Qb Qc Qd Qe Wm) Nw(Fr Hq Hu Hv Ik In Jg Js Lu Lx Ly Mb Md Mf Mj Mu Mv Mz Ne Nh Ni Nk Oe Oh Ok Oy Qc) Ok(Hv Im In Jg Jh Jo Jt Lu Mf Mg Mj Mt Mu Mv Na Ne Nf Nh Ni Qa Qc) Jg(Hv Il Lx Mb Mf Ne Nh Ni Nk Nv Oh Pb Qe) Mu(Fp Jp Li Lj Mb Nv Oh Pf Qe) Nv(Mb Md Ne Nh Ni Nk Oh Qc) Im(Lw Lx Mp Oh Pc Wm) Fr(Hv Ly Mb Mf Ne) Ni(Jp Li Lx Oh) Nk(Li Oh Qa Qe) Mb(Jp Lw Lx) Mv(Fp Oh) My(Li Lw) WmNa LxJh MgOh NhJp QcQe} Bc{cX(aC AD aE aF aG aH al Aj aK AL aM AN AO AP aQ AR AS aU aV AW AX aY aZ Ba BB bC bE bF BG bH bI bJ bL bM BN BO bP bQ bR bS bU bV bW bX bZ cA cB cC cD cE cF cG CH cI cJ cK cL cM cN CO CP CQ cR CS Ct cU CV CW Cx cY cZ dA DB Dc DD DE dF DG dH DI dJ DK DL dN FR) Af(aD aE aF aH al AI aN aP aQ aR aU AW aY aZ bB bE bJ bN BO bP bV bW cE cG Ch cI cJ cL cN cR CS Cw cZ dB DE dJ dK dN fR) Cx(aD aE aF aH al Aj aN Ao aW aY bB Bg bJ bN Bo bP bW cE cG Ch cI cN Co cP Cs dB De dN fR) Bo(aF Bn cE Ch De) De(aF cN) AobO aFcR aQaU} Ok{Jo(Et Fr Hq Hr Hu Hv Hw Hx Ih Ii Ij Ik Il Im In Io Ip Iq Ir Is Iv Jg Jh Jk Jl Jm Jn Jp Jr Js Jt Lh Lu Lw Lx Ly Lz Mb Mc Md Me Mf Mh Mj Mk Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nv Nw Nx Ny Oe Oh Oi Oy Oz Pa Pb Pc Pd Pe Pg Po Pz Qa Qb Qc Qd Qe Wm) Hw(Hv Ii Il In Ip Jr Js Lh Mj Mr Mt Mu Mv Na Ne Nf Nh Nm Nx Oe Po) Ii(Hq Hv In Js Mj Mu Nn Oh Pg) Jt(Im Jg Mu Mv Nn Qc) Hv(Il In Jr Js Mj) Nd(In Mj Mu Ni) Og(Mb Ne Pb) Nk(Nc Ne) WmIn MfMj IlPb} Hv{Il(Ij Is Iv Jl Lw Lx Mk Mr Nk Nn Nw Pa Pb Pc Pe) Fr(Hw Ii In Iq Js Ly Mb Md Mj Mp Nd Nk Oe Pb) Nk(Jp Li Lx Mm Mu Mv Mx Nc Nh Nn Og) Ii(Jg Li Mm Nn Nv Nw) In(Jg Lx Mm Nw Wm) Lx(Jo Jr Mj) Nn(Hw Nd) Mb(Lw Mm) Jg(Jk Oe) Nw(Js Mj) WmNa Mulq} Af{Ba(aD aE aF aG Aj Ao aW Bo cN cP dN) fR(aF al aW bB bN bU bW cE cG) bN(aP aW Bo cN cR Cw Fr) cP(aW BO cR Cv Cw) aP(al bB bW cE cG) Bo(bJ Cs Cv) Dl(aE cN) CvcN aEcR bObV bWdG} Lx{Jo(Ih Ik Il Ly Mb Mf Mj Nd Ne Nf Nh Nk Po Wm) In(Hu Ik Ly Mb Mf Ml My Nd Ne Nh Wm) Il(Ik Ly Mb Mf Oz Pb) Mj(Hu Hw Ii Mf Mu) Hw(Hu Jh Mb Ne) Nk(Nc Ne Nh) Nn(Il Nd) MbOg MuJk} cX{fR(aE aF al aN Ao bB bF bJ bN bW cE cG Ch cJ cL cM cP De) cP(Ba Bo Ch Cv Cw De Dl) aP(Ao Bn Ch De) Ao(Ba Cu) Cs(bJ bO) Dl(aE cN) bN(Bo Cw) CvaE DebV} Nk{Ne(Fr Jg Jp Li Lw Mp Nw) Nc(Jp Li Lw Mp Nw) Nl(Fr Jp Mu Mv Nn) Mb(Fr Jp Mp) Mu(Fp Lj Ml) Nd(Jg Nn) Jp(Mf Nh) FpMv} Mb{Fr(li Iq Jo Ly Nd Ng Ny Og Pb Pc Qc) Lw(Il In Jo Jp My Og Qc) Il(Iv Pa) MdMp JgJo NwOg} Nw{Js(Hw Ii Jo Mf Ml Nd) Ii(Mz Nn Oh Wm) Jo(In Md Mz Wm) Hw(Md Mz Ne) NnNd NeOg} Il{Pb(Fp Is Iv Lj Lw Mu Pa Pe) Fp(Iv Mk Mr Pa Pc) Lw(Ly Mf Nd Oz) MfPa} Wm{In(Fp Jn Jp Lj My Na Pb) Ii(Jg Jp Nn Nv) Jo(Jp Li) NaHr} Mu{Fp(li Jk Jo Js Md Mj Nd Ni Og Qc) Lj(Hw Iq Nd)} cP{bO(Bn bV Cx De) Ch(Ba Cw Cx) Bn(Bo dA) De(aW Cw) CxaW} bN{aP(bB cE dN) fR(Bn Ch De) AoCw BnBo CxaW cNcR} Lw{Nd(Mt My Nn) Hu(li Ml) Nnli NeOg IkJo} Cx{fR(aF cE cG) aP(cE cG) AoBa DlaE} Fr{Ly(Hw Ii Jo Pb) AobO MpPb} bO{bV(Ao cE cM De) AoBa} Nn{Ii(Ly Pb) NdNj} aF{cR(aP Ax fR)} aQ{aU(aP Cs) dAdN} Ao{Ba(bJ Ch)} MlJgJo NdNiJp Unconstrained panels with 3 analytes, where 1.0E-7 >= 'AUC p-value' > 1.0E-8. Contains 7,221 panels of 597,622 total panels evaluated. :
bA{aS(aC aG aK Ao aP aR aV aX aZ Bc BG bH bL bM Bo bQ bR bS bU bV bX cA cC cD cH cI cK cM CO cP Cq cU Cv cW cY cZ dA dB DC dD dG dI dJ dL) dC(aA aC aN aP aQ aR aW aZ Bc BG bH bI bL bM Bo bQ bR bS bU bV bX bZ cA cC cD cH cI cM cO cP Cq cS Ct cU Cv cW Db Dc dD dG DI DL) aW(aA aE aK aN aP aV aX aY aZ Bc bE bG bH bI bL bM bP bQ bR bU bV bZ cA cC cD cH cI cK cM cO cS cT cU cW cY cZ dA dB dD dI dJ dK dL) Ao(aK aN aO AP aR aU aV aY aZ Ba bF bG bL Bo bP bQ bU bW bZ cD cI cJ cM CO Cq CU Cv Cw cY dB Dc dF Dg dH dI DI fR) aG(aA aC aD aE aH aK aN aO aP aQ aR aV aZ BC bI bL bM bP bQ bU bX bZ cD cH cI cJ cK cM cN cO cS cU cV cZ dB dF dG dI Dl dN) cB(aC Aj aK aN aP aV aX aZ BG bH bL Bo bR bS bV bX cA cC cD cH cI cK cM CO Cq cS cU cY dA Db dD dG dI dJ dL) dE(aA aC aK aQ aR aV aX aZ bG bH bI bM bR bS bV bW bX cA cC cD cH cI cK cM cO Cq cU cW cY dA dB dD dG dI dJ dL) aN(aC aK aR aU aV aZ Bc BG bH bL bM bR bS bV bW cA cC cD cF cI cM cO Cq cS cU cY cZ dA dD dG dI dJ dK dL) aI(aA aC Aj An aR bE Bg bH bL bM bR bS bW cA cC cF cH cI CO Cp cQ Cs Ct Cv cY cZ Db Dc Dd dG DI Fr) bC(aA aC aK aP aQ aR aV aX aZ BG bH bL bR bS bU cA cC cD cH cK cM cO cR cS cU cW cY dD dG dI dJ dK dL) dF(aA aK aP aQ aR aV Ax aY aZ Bc bE bG bI bP bQ bR bU bV bX cD cI cK cM cO cU cW cY cZ dB dG dH dI dJ dL) aE(aC aK aP aR aX aY aZ bG bH bI bL bM bR bS bV bW cA cC cD cF cI cO cP cS cW DB dD dG DI dK dL) cT(aP aQ aY aZ Bc bG bH bL bM bR bS bV bW bX bZ cA cC cD cH cI cK cM cO cR cS cU cY cZ dA dG dI dJ dK) aU(aA aC aP aR aV aX Bc bE bG bH bL bQ bR bS bW cA cC cF cI cK cO Cq cU Cv cZ dA dD dG dI dJ dK) aY(aQ aX aZ Bc bE bH bI bL bM bQ bS bU bW bX bZ cA cD cH cI cM cO cS cW cY cZ dD dG dI dJ dK dL) cR(aA aK aP aQ aV aX aZ bG bH bM bS bU bV bW bZ cC cD cI cK cM cO cU cY cZ dD dG dI dJ dK dL) dH(aC aQ aR aX aZ bG bH bL bM bQ bR bU bV bW bX bZ cC cD cH cM cO Cq Ct cU cW Dc dD dI dK dL) bN(aC aP aR aX aZ BG bH bL bM Bo bR bS bW bX cA cD cH cI cM CO cU Dc dD dG dI dL) cJ(aC aP aR aV aX aZ Bc bG bH bL bR bS bV bW bX bZ cA cC cD cM cO cU cW Db dD dG dL) cN(aA aC aD aK aP aR aZ Bg bH bL bM bR bS bV cA cC cH cM cO CQ cU cW dB dD Dl) dB(aA aK aQ aZ bI bL bM bQ bU bV bW bX bZ cC cD cI cK cM cU cW cY cZ dI dJ dK dL) cP(aA aC aP aQ aR aZ bM bQ bU bW cC cD cH cI cM cO cS cU cW Db dD dG Di dK) bE(aC Aj aL aQ aZ Bc bI bL bM bO bP bQ bU bV bW bX bZ cD cF cI cM Cs dK dL) aM(aC aK aR aX BG bH Bo bR bS bX cA cC cF cH cM CO CQ cU Db Dg) cG(Ad Al An Ar Aw Ax Ba Bb Bg cF Co Cp cQ Cs Cu Cw Dc Dd Dg Di Dk FR) dJ(aK aZ bI bL bM bR bU bV bW bX bZ cD cH cI cM cO cS cW cY dI dK dL) aD(aA aX Bb Bc BG bH bR bS bV bX cA cF Cp CQ Cv Cw Dc Dl) aL(Ad Al An Ap Ar As Aw Ba Bb Bg Co Cu Cw Dc Dd Dg Di Dk Dl Fr) bF(Ad Aj Al An Aw Ax Ba Bb Bg cF Co Cp cQ Ct Cu Cv Dc Dd Dg Di) bJ(Ad Al An Ap As Aw Ax Bb Cs Cu Cv Cw dA Db Dd Dg Di Dk Fr) cS(aA aK aQ aV bI bL bU bW bX cA cD cH cK cM cO cU

Nl Nm Nr Ny Pa Pb Pe Qe Wm) Jg(Fp Hq Ik Iq Ir Is Lj Lw Ly Md Ml Mu Mx Nb Nc Nl Oe Og Oy Pc Pe) Mu(Hv Hx Ik Ir Is Ji Lx Mf Ml Mx Nh Pb Qa Qd) Oh(Fr Hv Jk Jp Js Lw Mb Mf My Nh) Im(Fr Hv Ip Is Ji Jp No Pe Po) Nn(Et Ip Jo Ma Ng Og Oi) Fr(Ik My Nh Nl Pb Qe) Lx(Mg Mt Mv Ne Nh Qa) Li(Hv Hv Ly Mb Ne Nh) Ni(Hx Is Ji Qe) Jp(Ik Mf Nk Wm) Wm(Hr Jh) Mb(Mp Om) MgQe MvLj} Om{Nw(Hu Ij Ip Iq Is Iu Jm Jp Jt Lh Lx Ly Lz Mc Me Ml Mn Mq Nd Nf Nl Ns Nt Ny Oi Ok Oz Pb Pd Pg Qb Wm) Jg(Fr Hr Hu Ii Ji Jn Jp Lh Li Lj Lu Lz Mj Ml Mp Mq Mv Na Nd Nf Nl Nm No Nx Pd Pg Pz Qb Wm) Nv(Fr Hv Ii It Iu Jl Jo Jp Li Lx Mb Mm Mp Mt Mv Mx Na Nc Nj Nx Ok Pc Qa) Mu(Jt Ma Mf Mm My Nc Ni Nt Nx Ny Og Pb Pe Po Qb) Ok(Hr Iu Jr Js Lh Mt Na Nc Nf Nh Nx Og Oh) Fr(Fp Ih Ik Ir Lj Mt Nc Pc Qb Qd) Im(Et Hv Jl Lh Mm Nb Nk Pe Pf) Lx(Jh Jl Mb Mt Nh Ni Qa) Mv(Et Fp Ip Jt Lj Mz Qe) Oh(In Jp Js Lw Mm Mp Mt) Jp(Jh Mt Nh Nk Wm) Ni(Ir Is Pf Qe) Li(Hv Jh Mt Nh) Mm(Hv Mb Qe) Mp(Jh Qa) WmNa LwQa NdIl QcQe} Af{Bc(aG Aj aK aL aM AO Ar AS aV AX bC bF Bg bH bI bL bM Bn bR bS bU bX bZ cA cB cC cD cH cK cM Co CP CQ Ct cU CV cW Cx cY dA Db Dc Dd dG dH dL Fr) aP(aD aF aH AN aQ aW bJ Bo bU Ch cJ cP cX dH dL dN) fR(aD aE aH An bJ Ch cI cJ cL cM cP Cv cX dH) cP(Ap BB bE bJ Ch Cq cX dA dJ Dl Fr) Bo(aM AN Ar Ax bC bV dA Dl Fr) bV(An bJ bN bW cE Ch cR Db) Ba(aN bN Ch cI) aW(bC bJ cR) bN(Cv dG Dl) Fr(aI bJ) aF(cR Dl) CsbJ CvaE CwcN bCbW cEdG} Hv{Nk(Fp Im Jg Jl Lj Lw Ma Mp Ne Nl Nv Nw Oh Ok Pb Pf Qa Qe) Jg(Hw Ij Il Iq Jo Mb Ml Na Nd Ni Og Qc) Fr(Ij Jo Jr Mf Ml Na Pc Pd Qc) Mu(Fp In Md Mj Ms Na Og) Lx(Hw Na Ni Nx Og Qc) Ok(Jq Na Nx Oe Og Qc) Js(Jp Li Mm Nn Oh) Lw(In Mj Mx Og) Il(Mj Mp No Nr) Nw(Hw Jr Mz Og) In(Is Jl Po) Mm(Iq Nd) Ii(Et Jp) WmHr NnIq MjJi NiJp HwLi} cX{fR(aC aD aH An aR aW Ax bC Bg Bn bO bU cD cN Co cQ cR Cs Cv cW dH DL dN) Bo(aM aN aP Ax bC bV Cs Cv dA De) Cs(aI aM aP bC bE bN cZ dB dE) Ba(aD aE Ch cL cN Co De) Ao(Ap bV Cv Cw dA Dl) cP(Ax Bn Cu Dd Di Fr) aP(An Bg cE Co Cv) Ch(bC Bg bV dG) De(bC dG) Dl(bC bN) Fr(aI bN) AxaI BcdC CvcN CwaE DbbV} Lx{Jo(Ij In Ir Jp Jr Li Me Mn Mx Na Nm Nt Nw Oe Pf Pg Qb Qd) In(Fp Ih Iv Lj Mj Mn Na Nc Ni Nl) Mb(Fr Hr Jp Js Lh Mj Na Qc) Mj(Ly My Nd Ne Nh Ni) Mu(Hw Ii Iq Na Nd Oe) Mf(Hr Ii Lh Md Na) Ne(Il Ni Nl Og) Na(Hw Ly Ni) Il(Fp Mp Nl) Hw(Ii Nh) Oh(Ii Js) PoPc MvJk NdOg NkNl HuLh} Ok{Hw(Et Hq Hr Hx Ik Im Io Lu Lw Lz Mb Md Mn Mq Nj Nk Nn Nt Nw Oy) Jo(Fp It Iu Li Lj Ma Mg Ml Og Pf) Jt(Fr In Iv Jl Mk Nb Nh Nr Pa) Nd(Ii Js Mv Na Nk Nn Og) Ii(Jr Lu Mn Na Oy) Mu(Ij Iq Jq Ml) Js(Io Mf Pb Pc) Nh(In Nk Og) FrMb MfIn NeNi JqOg} Cx{Bc(Ad aG Ap aQ aU aZ Bb bE bF bM bO bU bV cJ cL cR cS Ct cW cZ Dc Dg dJ dK) cP(Ax bB bE Bo cL cR Cv Cw dA De Dl) aE(aM bC cR Cv fR) bN(aP bV cN cR fR) aF(aM aP cR) aP(bB bW) bV(cE De) cN(cL Dl) fR(bB Ch) aWbC cEdG} Fr{Mb(Hu Ik Jk Jp Js Lj Lw Md Mj Ms Mv Mw Nq Oi Pz) Ly(In Jk Lj Md Mf Mj Ml Na Nd Ni Nk Oe Og Pc) Pb(Ii Jo Mf Mj Ml Nd Ne Ni Nk Og) Nk(Fp Mf Nc Nd Nh Nj) Mf(Ii Iq Jo Pc) Wm(Ii Jo) MpPc NdNi NeIq IiOh} Mu{Fp(Hu Ik In Iq Jm Mb Ms My Na Ne Ng Nj Nq Oe Oi Pb Pd Po Pz Qa Qb) Lj(Ii Jk Js Ly Mj Nq Nr Qc) Nk(Nc Ne Nh) Jp(Iq Ly Nd) Pb(Ml Nd Og) MdMl IlIv IqPe} Nk{Nc(Fp Jg Ji Lj Mv My No Nv Pb) Nh(Fp Jg Li Nn Nv Nw Pb) Ne(Ji Nn No Nv) Nl(Jg Li Lw Mp) Jp(Ly Nd Nj Pb) Fp(Il My) Mb(Li Lw) WmNa NnIi MlJg MvLj NdNv} De{Bc(aE aW bN bP bV cI cP dN) bN(aP aW Bo bV cN Cw) Bo(Ax cP Cs dA) cN(Ba Cw Dl) cP(cR dA fR) cE(aP fR) AoBa aFfR bVcR} In{Wm(Hr Hx Li Mg Nn Nv Nw Oh Qe) Fp(Hw Iv Mr Nb Pa Pb) Lw(Ly Mf Ml Nd) Mf(Hx Pa Pe) NdNw IsJo} Nn{Ii(Hu Hw Is Iv Ji Lh Mk Mr Nb Nd No Nr Pa Pe) Nd(Jo My Ni Pb) Ly(Jo Ng) MbNg JoPb} Nw{Nh(Hw Jo Mj Og) Js(Lj Lu Md Ne) Jo(Mf Nv Ny) Mj(Mf Nc) Mz(Jt Nd) Il(Oz Pb) MbJp MdNd NeNi OgPb} Lw{Ml(Mk Mw My Nb) Nd(Im Jh Nq) Hu(Jo Mb Og) My(Ii Ne) MbHq NeHw IiOh} aP{bN(aN aW Bn cL cR) cE(aQ Bn cR dN) bW(bC Bn dN) BnaF aDbO aQbB} Il{Pb(Ji Jl Jp Li Mk Mp Mr Po Qe) Mf(Iv Pe) NoNd IvLj PaPc} Ni{Jp(Fp Ly Ne Nh Nl Pb) Fp(Jg Jl Mp Mv) Nd(Jg Li)} bO{bV(aD aG aQ bB Ch cJ cL cW) cP(Ax Bo Cs Cw)} Bc{Bo(aI bB cG cV) aE(aM cR) ChaF aWcR bBbN} Wm{Na(Hx Iu Jp Lj) Jp(Js Mj Mr) IiLi JoNv} Jg{Ii(Hq Ml Oh) Jo(Fp Ik Ly) MfNd OgPb} bN{aM(bV dN) cR(Bo bV) AoBa BncN bBfR} cP{Cw(aI Bn cE) Bo(Ch Di) BnaW cLdA} Mb{Mp(Hq Jp Pd Pf) NoOg NgJp} Ba{AoBn ChdN aEaM} Bn{BodA aFfR} Jo{Li(Ly Pb)} Og{FpMv NeJi} aQ{aU(Ax bV)} AoCwbJ NoIiOh aFaMfR

Unconstrained panels with 3 analytes, where 1.0E-6 >= 'AUC p-value' > 1.0E-7. Contains 11,758 panels of 597,622 total panels evaluated. : bA{Bg(aE aG Aj aK An Ao aP aQ As aU aW Ax aY aZ bE bG bI Bo bQ bU bW bZ cI cJ cK cL cM Co cP Cq cR cS CT cU Cv Cw cY cZ dA DB Dc Dd dE dF dH dJ Dk) Co(aD aE Aj aN aP aQ aU aW Ax aY aZ bC bE bG bI bM Bo bQ bU bW cH cJ cK cM cN cP Cq cR CS CT cU Cv CW cY dA dB DC Dd dE dF dH dI dJ Dl) Cq(Ad aE aG Aj aK Al An aQ aW Ax aY aZ Ba bC bE bG bI bM bQ bU bW bZ cI cJ cK cM CP cR CS CT CU Cv cY cZ dA DB Dc Dd dF Dg Di dJ) Bo(aD aE aK AN aU aV AW aY Ba Bb bC bE bG bI bM bQ bU bW bZ cD cI cJ cK cN CP cR CS cT CU Cv cY cZ dA Db Dc dE dF Dg dJ) Ao(aC AD Aj Al An aQ As Aw AX BB bC bH bI bM bR bS bV bX cA cC cG cH CP cQ cS CT cW dA dC DD dG DK dL dN fR) cI(aA aC aG aQ aR aV aX aZ Bb bG bH bI bL bM bR bS bV bW bX bZ cA cC cD cH cK cO Cp cS cU Cv cY dA Db Dc dD dG DI dK dL) aP(aA aC aK aQ aR aV aX aY aZ bE bG bH bI bL bM bQ bS bU bV cA cC cD cH cK cM cO cS cU cW cY dA dB dD dE dG dI dJ dK dL) bW(aA aC aG aQ aR aV aW aX aZ Bc bG bH bI bL bM bQ bR bS bU bV bX bZ cA cC cD cK cM cO Ct cU cW cY dD dF dG dI dK dL) dK(aA aG aK aQ aV aX aZ Bc bG bH bL bM bQ bR bS bU bV bX bZ cA cC cD cH cJ cK cM cO cS cU cW cY dC dD dF dG dI dL) Bc(aK aM Ap aQ aR aZ Ba bC bI bM bN bQ bU bZ cA cB cD cN CP cR cS Cu cY dA DB dE DG dH dJ Dk Dl Fr) dL(aA aG aK aQ aR aV aZ bH bI bL bM bQ bR bS bU bV bX bZ cA cC cD cK cM cO cP cS cT cU cW cY cZ dA dD dG dI) aR(aK aQ aV aW aY aZ bE bI bL bM bQ bS bU bZ cA cB cD cK cM cO cR cS cT cU cW cY cZ dA dB dD dG dI dJ) bG(aA aG aK aQ aV aY aZ bE bH bI bM bP bU bV bX bZ cA cC cD cK cM cN cP cS cU cY cZ dA dB dD dI dJ) Ct(AD aE aJ aM aN aS aU aV aW aY bC bE bI bN bQ bU cB cJ cM cN Cp cR cZ Db Dc Dd dE dF Di dJ) aX(aG aK aN aQ aV aZ bE bI bL bM bQ bU bV bZ cA cD cK cM cN cP cS cT cU cY cZ dA dB dC dF dI dJ) bL(aA aC aK aQ aV aZ bH bI bM bQ bR bU bV bX bZ cA cD cK cM cO cP cR cU cW cY dA dD dF dG dI) Ba(aD aE aH aI aM aN aO aS aU aW bC bE bI bN bP bQ bU cB cJ cP cR Cv Db DC dE dF dH dN) bM(aA aC aK aQ aV aZ bH bI bQ bR bS bU bV bX bZ cA cC cD cK cM cO cS cU cW cZ dD dF dG dI) cA(aG aK aQ aZ bE bI bQ bR bU bV bX bZ cC cD cK cM cP cR cU cW cY cZ dB dD dF dH dI dJ) dD(aG aK aQ aV aZ bE bI bQ bR bU bV bX bZ cC cD cK cM cS cT cU cW cY dA dB dF dI dJ) aC(aA aK aQ aW aY aZ bI bQ bU bV bX bZ cK cM cR cS cT cU cW cY cZ dA dB dF dI dJ) bH(aG aK aQ aZ bE bI bQ bU bV bX bZ cD cK cM cP cS cU cW cY cZ dA dB dF dI dJ) bR(aA aG aK aQ aV aY aZ bE bI bQ bV bX bZ cD cK cM cP cR cS cU cW cY cZ dB dI) bS(aG aK aQ aW bE bI bQ bU bV bX bZ cD cK cM cP cS cU cW cY cZ dB dF dH dI dJ) cQ(aE aG aN aS aU aW aY bC bE bN cB cJ cP cR cT cX cY cZ dA dB dC dE dF dH dJ) Aj(aD aE aH aM aO aS aU aY bI bN bP bQ cJ cR Cv cZ dA Db DC Dd dE dF dH) Cp(aE aG aM aN aU aW aY bC bE bI bN cB cJ cL cN cP cR cS Cv dB dC dF dH dJ) cF(aK aO aS aW aY bC bI bN bP cB cJ cN cP cR cS cT cY cZ dB dC dE dF dH dJ) Bb(aE aH aI aM aN aO aS aU aW aY bC bN bP cB cJ cL cR Db dC dF dH dM dN) Ax(aD aJ aO aS aU bC bE bN bQ bU bZ cB cJ cL cN cR cZ DC dH dM dN) Cs(aD aH aJ aM aO aS aU bC bF bN bP cB cL cR cT cV cZ Db dC dF dJ dN) aA(aK aQ aV aY aZ bE bQ bZ cC cD cH cJ cM cO cT cU cW cY dA dG dI dJ) Ad(aD aH aI aN aO aS aU bC bI bN bO bP cB cJ cR CV Dd dH dM dN) Dc(aE aM aN aU aW aY bC bI bP bQ cB cJ cN cP cR Cv dA Db Dd dE dN) cC(aG aK aQ aV aY aZ bE bQ bU bV bZ cD cK cM cS cU cW cY cZ dF dI) cK(aK aV aY aZ bE bU bV bX cD cH cM cN cO cU cW cY cZ dG dI dJ) As(aD aI aJ aM aN aS aW bC bF bO bP cG cJ cL cN cP cV dC dH) Db(aG aN aS aU aW aY bC bI bN bO bQ bV cN cR cS cT cV dF dH) cO(aK aQ aZ bE bI bQ bU bV bX bZ cD cM cU cW cY cZ dB dG dI) dG(aK aQ aW aZ bE bI bQ bU bV bX bZ cD cM cW cY cZ dB dJ) Dd(aD aE aM aN aS aU bC bN bO cB cJ

Figure 17 Continued

Pc(Hw Qe) PoLy NoJs} cP{De(aM Ax Ba bB bE bJ BN Cv Dd dJ Dl) Ch(Ap bB Bg bJ Bn bO cR dA Dl fR) Bn(Ba bB bE bJ cR Cv dJ fR)
Cw(aL Ao bB Bg cG) dA(Bo bU cE cR dN) bO(cR dE dN fR) aQaU bBdE bEcL cRdB} Wm{In(Hq Hu Ih Iq Ir Is Iu Ji Mh Mj Mn Mt Mx Mz
Ng Og Oy Pa Pf Qa Qb Qc Qd) Jp(Et Ij Ik Iu Jt Nt Oy Pg Po) Na(Fp Hq Oy Pg) Hr(Hq Hx Iu) Jo(Ji Nn Pe) Mmli} bN{Bo(aM bB bC cE Ch Di)
cR(aE Ax Bn De dG dN) Cw(aH bB cE Ch) dG(Bn cE cL De) dN(dA De Dl fR) fR(aM aW cE) AoAp BabB DebC aEaM cLcN} Jp{Mf(Jg Jm Jo Js Lw Md Mp Ng Pb Pc Qc) Ni(Hu Lj Ml Nc Nj) Ii(Hu Ik Oh Pb) Nh(Ne Pb) Iq(Mv My) LwLy IkJo OgPb} Bo{De(aM aN Ar aZ bC bJ cN Cv) Bn(bC bJ cN cR CV) Ch(bC bJ dA) cE(bG dA) cV(bC cR) AoBa CsbO} Fp{Ni(Hq Lw Mk Mr No Nr Oy) Mv(In Jm Jo Js Md Qc) My(Lw Mm Og) In(Jl Mk Pe) Jg(Og Qc) NnIi} Nn{Ii(Hx Ij Ik Jg Jl Me Ml My Nh Nl Nt Pc Po) Pb(Iq Ng Nh Og) LwIq NgHu HwHx JoPc} Ba{Ao(aE aF aM aN cB cE cL cV dA dN) cN(Bn cE Ch) De(aD dN) ChaG cEdN} Jg{Ml(In Md Mf Oe Qc) Ne(Iq Jo Ni Og) Ly(Ii Iq Og) Iq(Hq Md) Jo(Mf Oz)} Lw{My(Iq Jk Ly Oe) Hu(Iq Ly Mf Ne) Jo(Mf Oh) NeNi NhOg InIt} In{Nb(Iq Lj Ml Nc Nh) Mf(Is Pb) Ml(Hx Pe) PoLy NhPe HuPc} Li{Ni(Iq Ly Nc Ne Nh Nl Pb) My(Ii Iq) Jo(Hu Mf) OgPb} aF{cR(Ar Cs Cu) fR(bB Ch) AxaM} Og{No(Ne Nh) Pb(Mv Nh) NeJq} Oh{Ii(Hu Ji Mp Nb) NgHu} Ao{Cw(cV dA) BndA CsbO} De{cN(Ax Cs Cu Cv)} Bn{bW(dG fR) cEfR} Iq{NoIm MvLj QcQe} aQ{dA(aD aG) AraU} Nh{MyNg NiPb} MfMpJm NcNiLj HwHxJh JiJoOy Unconstrained panels with 3 analytes, where 6.3E-6 >= 'AUC p-value' > 1.0E-6. Contains 15,037 panels of 597,622 total panels evaluated. : aA{Hv(Hq Hr Hx Ih Ij Im Io Ip Ir Is It Iu Iv Jg Jk Jm Jn Jo Jr Jt Li Ly Lz Ma Mc Me Mf Mh Mm Mq Mv Mw Mz Nh Nj Nm No Nt Nw Ny Ok Oy Oz Pa Pg Po Pz Qc Qd) Nk(Et Fr Hr Hx Ih Ik Io Ip Ir Is Iu Jk Jl Jm Jn Js Lh Lz Ma Mc Md Me Mj Mm Mq Mr Ms Mt Mu Mv Mw Mx My Nb Nf Ni Nm Nn Nq Ns Ny Oh Pd Pf Pg Qb Qc) Lj(Et Hq Hr Hu Hx Ik Ip Ir Is Iv Jg Jh Jl Jn Jq Jr Lh Li Lu Ma Mc Me Mg Mh Mm Mn Mr Ms Mt Mu Mv My Nb Nf Nh No Oh Oy Pd Pe Pf Pg Pz Qa Qb Qd Qe) Nx(Et Fr Hq Hr Hx Ih Ir It Iu Jg Jh Jl Jn Li Ma Mb Mc Me Mm Mn Mp Mq Mr Mt Mu Mv Mx Mz Nb Nc Nf No Nt Nv Oh Oy Pd Pe Pf Po Pz Qa Qb Qd Qe) De(aD aH aI An aQ Ar aS aU aV Aw Ax aY bB bC bF bM bP bR cC cG cH cI cL cM cO CS Ct Cu Cv Cw cZ dA dB Dd dH Di dJ dK FR) Ml(Hq Hr Hu Ih Ii Im Io Ir Iv Jh Jm Jn Jo Jr Js Lz Mc Me Mh Mn Mr Mt Mw Mx Nh No Ns Oe Of Oi Oy Pd Pf Pg Pz Qa Qc Qd Qe) dN(aC aE aI aN aO aR aS aU aV aW aY bC bF bG bL bM bP bR bU bV bZ cB cD cG cJ cM cN cO cS cW cY DB dD dG dI dJ dK dL) Lw(Et Fr Hx Ih Im Ir Is Iu Iv Jh Jl Jm Jn Jp Li Lx Lz Mc Mi Mr Mv Mx My Mz Nf Nt Oh Ok Oy Pd Pe Pf Pg Po Pz Qa Qb Qd) Nr(Hr Hu Hx Ih Ii Ij Il Io Ip It Iu Jg Jk Jl Lh Ly Lz Ma Mb Mc Md Mk Mp Nb Nd Ni Nm Nn Nv Nw Pd Pg Qa Qb Qc Qd) Nd(Hq Hr Hu Hw Il Im In Ir It Jh Jq Md Me Mg Mh Mj Mk Mn Ms Mt Mv Mx Nb Ne Nf Nh Nj Nl Ns Nt Oe Oy Pd Pz Qd) Ch(aH aI An aS aU aV AW AX aY bB bG bM Bo bP bR cA cB cI cL cM Ct cU Cw cZ dA dB dG dH dJ DK fR) Mi(Fr Hq Hx Ik Im Io Iu Iv Jh Jl Jm Jn Jp Jr Js Lh Li Lz Ma Mc Mv Mw Mx My Mz Nc Nf Ny Pa Pe Pf Po Pz Qd) Bn(Ad aG Aj aK Al Ao Ap Ar As aX Ba bE bS bV bW bX bZ cA cH Cq Ct Cv CW cY dD Dg Di DK dL FR) Lx(Et Hq Hx Ih Im Ir Is Iu Iv Jm Jp Jr Lz Mc Mn Mr Mt Mv My Mz Nc Nf Nl Nn No Ny Oy Pe Pf Pz Qa Qb Qd) Og(Et Hq Hw Hx Ih Ii In Ip Ir It Jl Jm Js Lh Lu Ma Md Mh Mm Mr Ms Mt Mu Nf Nj Ns Nv Oe Oy Pd Pf Qd Qe) cP(aC aD aG aP aR aX aY Bc bE bH bL bM bQ bR bS bV bX bZ cA cC cD cF cH cO cQ cW Db dC dD dF dG dK dL) aO(aH aK aL An Ap Ar aS aV AX bC bH Bo bX cA cD cF cJ cK cQ Cs Cv Cw cY cZ dD Di dJ Dl FR) aJ(aL aP aQ aS aU aV aW Bc bF bG bI bL bP bR cC cD cH cI cM cN cO cS cZ DB dC dF dJ dK) aM(aG aH aP aQ aS aV aY BC bE bF bG bM bQ bR bV cD cM cN cU cW cZ Db dC dF dG dJ dK dL) bJ(Ad Aj aK aL aP aS aV AX bH bL bM Bo bS bX bZ cA cF cH CO Cp Cq Cs cY cZ dF dJ dL) aZ(aG aI aL aP aV aW aY Bc bF bG bL bQ bR bW cC cD cI cM cS cU cW cZ dB dE dF dI dJ dL) Mk(Hq Hu Ik Is Iv Ji Jr Mb Md Mh Mr My Mz Nc Nh Ni Nj Ns Nt Nw Ok On Oz Pa Pe Po Qe) aF(AD aG Aj aK Ap Ar As AW Ba Bg bH Co Cs Ct Cu Cv Cw Dc dD Dg Di Dk Dl Fr) cE(aD aH aQ aS aU aW Ax aY bM bP bQ bV bZ cH cI cJ cL cM cO cW dC dF dG dH dJ dK) cT(aK Ao aQ aR aX Bc bE bG bL bR bS bV bW bX bZ cA cD cI cO cY dA dD dF dG dK dL) aN(aC aH aP aQ aV aX bB bF bG bL bM bP bV bW cB cG cI cM cO cW Db dG dI dJ dK) cN(aC aI aQ BC bF bG bI bR bU bW cB cC cD cG cH cI cS cU dA DB dG dI) dE(aD aG aH aI aS aU aV aW bB bC bF bG bI bL bM bP bR cD cH cI cM cR dC dI) dM(aD aR aU aV aX bE bH bM bS bV bX bZ cA cF cJ cK cO cW cY cZ dA dD dJ dL) Na(Hu Ii Il Io Ji Jr Li Md Mf Mp Ms Mw Mz Ni Nl Ns Nt Nw Ny Oe Oz Pa Po) Pa(Hu Ii In Io Jk Jp Jr Js Mb Mh Mj Mp Mw Ne Nh Ni Nn Ns Nw Oi On Oz) cV(Aj aK aL Ao aR aV aW Ax bE bX cA cF cJ cK Cp Cq cY cZ Db dD dL fR) aC(aI aL bB Bc bE bF bG bI bP bU cG cL cS cZ dA DB dH dI dJ) cR(aD aH aI aP aS aY bB bC bF bG bM bU cB cG cI cS cU dB dC dI) cU(aG aH aI aS aW bB bI bP bR bU cB cH cI cL cM cS cW dB dF) Bc(Ad aG aH aI Ao bA bB Bo bP bU bW cB cL Cp cS Dg dH Dl) bO(aI aL Ax aY bH bL Bo bQ bS bZ cA cH cK cO cZ dF dG dJ) Ng(Fr Ih Ii Io It Jh Jk Jm Jo Jq Jt Me Mm Mw Nf Ny Oi) Jp(Hq In Jm Jo Jr Md Mh Mj Mp Mx Ni Nl Nn Ns Oz Pz Qc) Oe(Is Iv Jg Jq Jr Mh Mm Mq Mr Mu My Mz Ni Nm Oi Pe Qe) aE(aH aP aR aS aU aY bF bI bL bW cC cG cW dA DB dJ) dH(aI aL aP aQ aS aU aY bE bI bM bP cC cL cO cS dB dC) Oi(Il Jl Jr Ma Mf Mm Mz Nh Nl Nt Nv Of Qa Qb Qe) On(Hr Hu In Iu Jr Lh Mh Mx Nf Nh Ni Nm Ns Nv Ny) bA(Ad Ao aR aX Bg bS bV bX cA cF Co Cp Cq Db dD) bN(Al An Ap Ar Aw Ba Bb Ct Cu Cv Dc Dg Dk Dl Fr) Ii(Is Iv Jg Mq Nm No Ns Nt Nw Ok Om Oy Po Qc) dI(aG aH aQ bB bC bF bI bP cG cL cM cS cW dC) Il(Fr Ij Jl Mh Mj Mz Nb Nh Nl No Ns Nt Pe) Po(Hu In Jk Jo Js Ly Mp Ms Ni Nl Ny Oz) Ji(In Io Jk Jo Mw Ne Nj Nl Nm Nq Pd Qc) Nw(Hu In Io Jq Jr Mb Nf Nh Ni Nm Ns Pd) Om(Hq Hu Ih Ik Io It Jk Jm Mr Nj Nq Oz) cL(aD aH aQ aV bG bI bU cC cK cS dB dC) Mp(Hu In Jg Jk Jo Li Mb Mh Ne Nh Ns) Ok(Im Iu Jk Jr Mx Ne Nf Nj Nl Nq Pd) Fr(Hu Jk Jo Mb Mh Ms Ne Ny Oz) Mf(In Ip Jl Lh Mq Mu Nm No Of) bG(aG aH bB bC bF bU cG cS dC) cB(aQ bC bI bW cC cH cS DB) Nn(Hu Ij Jr Jt Ly Mw Nj Nl) Mz(Ij In Jm Ms Mw Nl Nq Oz) bU(aI aU aV bB bI cS dB dJ) Li(Hu Io Mj Ms Ni Oz Qc) Ij(Ir Is Nt Nv Oh Qe) Jk(Is Nv Oh Pe Pf Qe) Ly(Jr Mq Mu Nm No) Ni(Hw Jr Nc Nh Nl) In(Mh Nl Ns Nt Pe) Jg(Ms Nj Nl Ny Oz) Jt(Ip Ir Jn Jr Qd) bC(bI bP bW cG Db) Cx(aR Bb bH cF) Nq(Mv No Nv Pe) Of(Ik My Ne Nj) Oz(Ip Jq Mh Nt) cG(aP bI cC cS) cS(aI bW dB) Nm(Jo Nl) Ms(No Nt) Hw(Mh Mr) Pe(Js Ny) aQ(cK cY) bB(bR dB) cC(aH bR) cX(cJ dD) CsDb MmNj MvPc HuJh aUcY dAdC} Nu{Ni(Hu Hw Ih Ij Ik Im Io Ip Iq Ir Iu Iv Ji Jk Jm Jn Jq Jr Js Lh Lu Lz Mc Me Mf Mg Mh Mj Mk Ml Mq Mr Ms Mt Mw My Nb Nd Nf Nj Nl Nm Nq Nr Ns Nt Nx Ny Oe Oz Pa Pd Pe Pg Pz Qa Qb Qc Qd Qe) Lw(Et Hq Hr Ih Ik Im Io It Iv Jh Jk Jl Jm Jn Li Lx Ly Lz Ma Mc Me Mf Mg Mh Mk Mm Mn Mp Mq Mr Mt Mv Mw Mz Nb Nf Ng Nh Nj Nl Nm Nq Nr Nv Nw Ny Oh Ok Oz Pa Pe Pf Pg Qa Qb Qd Qe) Li(Fp Hr Hu Hw Hx Im Ir Is Iu Iv Jg Jh Ji Jl Jr Lj Lu Lx Ly Ma Mc Me Mg Mh Mk Mm Mn Mp Mq Mr Ms Mt Mw Mx Mz Nb Nf No Nq Ns Nv Nw Oh Ok Oy Oz Pa Pc Pe Pf Pg Qa Qb Qd Qe) Hq(Et Hr Hu Hx Ih Ik Im Ip Is Jh Ji Jl Jn Jq Lj Ly Lz Ma Mc Me Mf Mg Ml Mn Mp Mq Ms Mt Mw My Mz Nb Nc Nf Nh Nl No Ns Nt Nv Oe Oh Om Oz Pd Pf Pg Pz Qa Qc Qd Qe) It(Hu Hw Ih Ik Il Im Is Iu Iv Jg Jh Jl Ly Ma Mb Mc Md Mf Mk Ml Mm Mn Mp Mr Ms Mv Mx Mz Nb Nc Nd Nh Nj Nl Nq Nr Ns Nv Oe Om Oy Oz Pa Pc Pd Pe Pf Po Pz Qc Qe) Nw(Fp Hr Hx Ih Ik Io Iu Jg Jh Jl Jm Jn Jr Lh Lj Lu Lx Ly Lz Ma Mc Me Mf Mg Mh Mk Ml Mm Mn Mp Mr Mw Mx Nb Nh Nj Nl No Ns Ny Oh Ok Oy Pa Pe Pf Pg Qb Qd) Hv(Et Hr Hu Hx Ih Ik Im Ip Ir Is Iu Jh Ji Jl Jm Jr Lz Mb Mf Mh Ml Mn Mq Mt Mx My Mz Nc Nd Nj Nl Nm No Ns Nt Nv Oe Oh Om Oy Oz Pf Po Pz Qc Qe) Oi(Et Fp Ih Ir Is Iu Jl Jm Jo Js Lj Lx Ly Md Mf Mg Ml Mn Mp Ms Mt Mw Mz Nb Nd Ne Ng Nh Nj Nl Nm No Nq Oe Of Om Oz Pc Pd Pe Pf Pg Po Qb Qc) Mm(Hx Ih Ik Im Iq Jh Jk Jm Jr Lu Lx Ly Ma Mc Me Mf Mh Mn Mp Mt Mu Mv Mx Mz Nb Nh Nj Nl Nn Nq Ns Nv Nx Ny Oe Oh Ok On Oy Pc Pd Pe Pf Qe) Ng(Fp Ih Ik Io Ip Iq Is Iu Ji Jk Jl Jm Jn Jr Js Lj Lu Lx Lz Mc Me Mf Mg Mh Ml Ms Nb Nf Nl Nm No Nr Ns Oe Of Om Oz Pc Pd Pg Qb Qc Qd) In(Et Ik Il Im Io Ip Iq Ir Ji Jk Jm Jn Jq Jr Js Lz Mb Mc Me Mf Mg Mh Mn Mt Mw Nd Nh Nl Nm Nq Ns Nt Nx

Figure 17 Continued

Nv Oh) Mm(Hu My Nh) Ni(Lj Nc Oh) li(Mt Nv Oh) Nh(My Ne) MvLj QcQe} Jj{Mq(lo Jn Jq Js Mc Me Ms Na Nm Ns Ny Oi Oz Qc) Jq(Jn Me Ns Ny Oi) Oz(Ms Na)} Bo{Ch(Ax Ba BG CV) Ax(aF al aL cE) aF(bC cR Cv) Cs(al bJ) aM(aE cV) bCbW cEcU} Nv{Jo(Hw Iv Ly Mk Ml Nb Nh Nr) li(Hq Ly Ml Ne Nh Oh Qc) Iq(My Qc) LyOg MlQc} cE{cN(bQ cR Cw dF) dG(aZ bJ bW cR) dA(aQ cS dN) aF(dF fR) ChfR} Lj{Mv(Jk Js Ly Ni Nq Ny Og Qc) Hu(Mm Ni Og) NhNi} cR{cN(Ax cL cS cV cW) aF(Ba dG Dk) cV(Cs dN) aDdA} li{Oh(Is Lh Mv My Pe Po) Mt(Nb No) NqIs HqJi} Ni{Ne(Hx Ji Mp No) MpNh NcHx IsJo QcQe} Ch{Bg(aE aF cN dN) Ba(aD aE) CwcN} Iq{Mp(Hu My) Mv(Nb Qe) NoMy MdNb HuOh} dA{aQ(aW bU cL cS) aDaZ aEaM cHdN} Nh{Og(Ji Jq Mq) HwHx} Jo{Ik(Mp Po) NaIs HqJi} aF{fR(bC cC Di) CuaM} Cs{bO(aD bB) aMbJ} No{LyOg NeNl} Md{MlNy MyPc} Ng{MyNc QcQc} Hu{LyMm OyPc} aE{aM(Cu Cw)} BacLcN HwHxIm QcQeJi aQbJdN bCbWfR

Unconstrained panels with 2 analytes. where 1.0E-7 >= 'AUC p-value' > 0. Contains 213 panels of 14,881 total panels evaluated. : Jj(aA Fp Fr Hq Hr Hu Hv Hw Hx Ih Ii Ij Ik Im Ip Ir Is It Iu Iv Jg Jh Ji Jk Jl Jm Jo Jp Jt Lh Li Lj Lv Lw Lx Ly Lz Mb Mf Mg Mh Mi Mj Mk Ml Mm Mp Mr Mt Mu Mv Mx My Mz Nb Nc Ne Nf Ng Nh Nk Nl Nn No Nr Nt Nu Nv Nw Nx Oh Ok Om On Oy Pa Pb Pc Pd Pe Pf Pg Po Qa Qb Qd Qe Wm) bA(aD aE AF aG aH aI aJ aL aM aN aO aS aU aW aY bB bC bF bJ BN bO bP cB cE cG Ch cJ cL cN cP cR cV CX dB dC DE dH dM dN) aJ(AF aG aO aQ aZ bJ BN bO bU bW cE Ch cL cM cP cR cT cV CX De dG dH dL dM) dM(AF aM aQ aZ bJ bL BN cE CH cM cP cR cT cV CX De dH) aA(Af bN Cx Fp Iq Lv Nu Pb Pc) Lv(Il In Mi Nq Nu Og Qc) On(Ii Jt Nd Of Om) Mi(Hv Mb Nd Nu) Om(Jg Nn Nw) cT(Af bB dN) BccX NnOf JoOk Unconstrained panels with 2 analytes, where 1.0E-6 >= 'AUC p-value' > 1.0E-7. Contains 172 panels of 14,881 total panels evaluated. : bA(aA aK Ao aP aQ aR aV aZ bE bG bI bL bM bQ bR bU bV bW bX bZ cA cC cD cI cK cM cS cT cU cW cY cZ dA dF dI dJ dK dL) Jj(Et Il Io Iq Jn Jr Js Lu Ma Mc Md Me Mn Ms Mw Na Nd Ni Nj Nm Nq Ns Ny Oe Of Og Oi Pz Qc) dM(aC aE aG aI aL aV aX BC bF bI bO bP bU bW bX cB cD cG cL cN cO cU cW dB dC dE) aJ(aC aD aE aH aI aM aN aW bB bC bF bL bV cB cD cG cN cS cU cW dB dE dI dK dN) Lv(Hq Hu Hv Jp Lu Ma Mb Mk Mp Mu Mx My Nb Nj Nk Ny Of On) aA(aF aO Bn cV cX Hw Of Om) Nu(Fr Jp Na Nk Og On) cT(aM bC cE CX) Mi(Fp Lj Ly Ne) Af(Bc fR) Fr(Hv Mb) Nv(Of Om) BcCx FpMu LxJo HvOn HwOk NwOf Unconstrained panels with 2 analytes, where 1.0E-5 >= 'AUC p-value' > 1.0E-6. Contains 234 panels of 14,881 total panels evaluated. : aJ(aA aK aL aP aR aS aU aV AX aY Bc bE bG bH bI bM bP bQ bR bS bX bZ cA cC cF cH cI cJ cK cO cQ cY cZ dA Db dC dD dF dJ) dM(aA aD aH aK aN aP aS aU aW aY bE bG bH bM Bo bQ bR bS bV bZ cA cC cF cI cJ cK Co cS cY cZ Db dD dF dG dI dJ dK dL dN) bA(aC Ad Aj An aX Ba Bb Bc Bg bH Bo bS cF cH CO Cp CQ Ct Cv Db Dc DD dG) Lv(Fr Ih Ik Io Jg Jk Jl Lx Md Mf Mg Mt Ne Nh Nr Nw Ok Oy Pd Pg Pz Qb) aA(aE aM aN aZ bJ bO cE cP cT De dN Hv Lj Lw Lx Mi Ml Ng Nk Nr Nx) Nu(Hq Hv Il In It Jg Li Lw Lx Mm Mp Mu Ng Ni Nn Nw Of Ok Pb) cT(aD aH aN bF Bn bV cB cL cN cP cS De) On(Hw Io Iq Jo Ml Mn) Mu(Hv Lj Ml Nd Pb) Of(Jg Jp Li Oh Ok) Af(aP Bo bV cP) Fr(Ly Mf Nd Pb) Jj(In Jq Mq Oz) Ok(Ii Js Nd Om) Lx(Hw Mj Ni) Mi(Ii Mf Nl) Om(Jp Li Oh) Nd(Jg Nn) Hv(Jg Nk) cX(Cs fR) CxcP WmIn FpMv LwMb MfJp JsNw aPcE bObV Unconstrained panels with 2 analytes, where 1.0E-4 >= 'AUC p-value' > 1.0E-5. Contains 397 panels of 14,881 total panels evaluated. : Nu(Et Fp Hu Hx Ik Im Ip Ir Is Iu Jh Ji Jl Jm Jo Js Lj Ly Ma Mb Md Mf Mh Ml Mn Mq Ms Mt Mv Mx My Mz Nc Nd Ne Nh Nj Nm No Nt Nv Oe Oh Oi Om Oy Pc Pd Pf Po Pz Qa Qc Qe) aA(aC aD aH aU Bc bG bI bP bR bU cB cC cG Ch cL cN cR cS cU dB dE dH dI Hu Ii Ij In Jp Jt Li Mf Mk Mp Ms Na Nd Ns Nw Oe Og Oi On Pa Po) Lv(Et Hx Ii Ij Ip Is Iu Iv Jh Jm Js Li Lj Lw Ly Lz Mc Mh Mj Ml Mm Mn Mq Mr Mv Na Nc Nd Ni Nl Nm No Nv Oe Oh Oi Om Oz Pb Pe Qa) cT(aE aF aI aK aL AO aP aQ aR aU aW aY Bc bJ bN Bo bU bX cG Ch cI cJ cM cR cU cW cY cZ dB dC dE dG dH dJ dL) aJ(Ad Aj An Ao Ap Ar Aw Bg Bo Co Cp Cq Cs Ct Cv Dc Dg Di Dk Dl FR) dM(Aj An AO aR Aw bB Cp CQ Cs Ct Cu Cv dA Dc Di Dl fR) bA(Al Ap Ar As Aw Ax Cs Cu Cw Dg Di Dk Dl FR) Hv(Il In Jl Jp Lw Lx Mm Mp Mv Mx Ni Og Ok Pb) On(Fp Ij Il Iu Jq Mb Mj Ne Ng Nh Ni Nm Oc Pb) aP(aD aF aH bB BN bW cG cL cP CX De dH) Lx(Ii In Ly Mb Mf Mu Na Nd Ne Of Pb) Jp(Iq Ly Mb Ml Nd Nh Ni Nk Pb Wm) bV(aM bJ BN cE Ch cL cR Cx De) Fr(Af Fp Ii Ml Ne Of Om Pc) Mi(Ik Iq Jo Me Mp Nh Ni Nq) Nw(Hw Ii In Jt Mf Nd Nc Qc) Ok(In Jt Mf Mj Nm Oe Og) Af(aW Ba bC cN Cs Dl) Om(Im Is Ml Mu Nd Qa) Bc(aF aW Bo Ch De) Cx(aE Bo cN Cs fR) Nk(Li Nc Ne Nh) Jg(Iq Mb Ml Ne) Of(Im Qa Qe Wm) cP(Bn Cw dA De) Nn(Ii Iq Pb) Nd(Lw Nv Oh) Li(Jo Ni Pb) Ba(Ao cX) Bo(cX De) Wm(Hr Na) Mb(Mp Mu) In(Is It) FpNi MuIq MvLj IsJo bNdN Unconstrained panels with 2 analytes, where 1.0E-3 >= 'AUC p-value' > 1.0E-4. Contains 864 panels of 14,881 total panels evaluated. : aA(aG aI aK aL aP aQ aR aS aV aW aX aY bB bC bE bF bL bM Bo bQ bS bV bW bX bZ cA cD cF cH cI cJ cK cM cO Cs cW cY cZ dA Db dC dD dF dG dJ dK dL Fr Hq Hr Hx Ih Ik Il Io Ip Ir Is It Iu Iv Jg Jh Ji Jk Jl Jm Jn Jo Jr Js Lh Ly Lz Ma Mc Md Me Mh Mj Mm Mq Mr Mt Mu Mv Mw Mx My Mz Nb Nc Ne Nf Nh Ni Nj Nl Nm Nn No Nq Nt Ny Oh Ok Oy Oz Pd Pe Pf Pg Qc Qe) Jp(Fp Hq Hu Ik In Io Iv Js Li Lj Lu Lw Lx Lz Mc Md Mh Mi Mk Mp Mr Ms Mt Mu Mv Mw My Mz Na Nb Nc Ne Ng Nj Nl Nm No Nq Nr Ns Nw Ny Oe Og Oi Ok On Oy Oz Pa Pc Pe Pz Qc) Hv(Et Fp Hq Hu Ik Im Ip Iq Ir Is It Jh Ji Js Li Lj Ma Md Mf Mq Ms Mt My Mz Na Nb Ne Nh Nj Nm Nn No Nq Nv Nw Nx Ny Oe Of Oh Oy Pa Pc Pd Pe Pf Pg Po Qa Qb Qd Qe Wm) bV(aC aD aE aF aH aI aL aN aP aQ aW aX aY bB BC bE bF bG Bo bP bR bS bU bW bZ cA cC cD cG cH cJ cM cN cP cU cV cW cX cZ dA DB dC dE dH dJ dK dN) cT(aC aG Aj AI An aS aV AX aZ bE BG bH bI bL bM bO bP bQ bR bS bW bZ cA cC cD cF cK CO Cp CQ Cs Ct CV Cw dA DD dF dI dK FR) Nu(Hr Hw Ih Ii Ij Io Iq Iv Jk Jn Jq Jr Jt Lh Lu Lz Mc Me Mg Mj Mk Mr Mw Nb Nf Nl Nq Nr Ns Nx Ny Oz Pa Pe Pg Qb Qd) On(Hr Ik In Ip Iv Jk Js Lj Lu Lx Ly Md Mf Mg Mp Mq Na Nc Nf Nk Nl Nq Nr Ny Og Oy Oz Pc Pd Pg Pz Qb) aP(aC aE aG aI aM aN AO aQ aU aW aZ bC bF bJ bO bU cB cD Ch cI cJ cM cN cR cS cW dC dE dK dL dN) Lv(Fp Hr Hw Im Iq Ir It Ji Jn Jq Jr Jt Lh Me Ms Mw Mz Nf Nn Ns Nt Nx Pa Pc Pf Po Qd Qe) Af(aE aF aM aN AR aZ Bb Bg bJ bN CQ cR cS CU Cv CW dA dF dG dN) Ok(Hr Io Ip Iq Jq Jr Lh Lx Ly Mb Ml Mn Mu Na Ne Nf Ng Nh Ni Nk Nx Oz Pb Qc) Li(Hu Ii Iq Js Ly Mb Md Mf Mj Mu My Na Nc Nd Ne Ng Nh Nl Nm Og Qc) Nw(Fp Iq Jo Jq Ly Mb Md Mi Mj Mu Mz Nc Nf Nh Ni Nk Nm Pb Pc Po Pz) cP(aM aN aW bB Bc bE bN BO Ch cL cN cR DB dE dG dI dJ dN fR) Lx(Ik Il Io Jh Jr Lh Lz Md Mi Mn Mp Nf Nh Oe Og Oz Pc Pf Pz Qc) Fr(cX De dM Ik Iq Jo Js Lj Md Me Mu Nh Ni Nj Nk Nl Nq Oe Og) Pb(Et Fp Il Im Is Jg Jh Ji Lj Mt Mv My Ne Nh Nt Nv Oh Qa Qe) Mu(Hq Il Jk Ly Me Mf Mh Ms Mw Ne Nh Nl Nq Nx Of Og Pc) Bc(aD aE aH aI Ao aY bB BN bP cE cI cN Co dN) Fp(Hq Hu Il Im Jg Jl Mm Mp Mx My Nh Nk Nn Og Qc) Mi(Hu Il In Iv Jk Lu Ms Nc Nx Of Om Pc Qe) dM(Ad Al Ap Ar As Ax Ba Bb Bg Cw Dd Dg Dk) Nn(Jo Ly Mb Ml Ne Ng Nh Ni Nk Nl Nm Pc) Cx(aF aN Ar aW bC bN cQ cS cW dG dN) Lw(Hu Ik Il In Jo Me Ml My Ne Nh Ni) Bo(aM Ax bC BN Ch Cs cV dA) Nh(Jg Lj Mp My Ne Ni Nv Og) cX(An Ao Ar Ax Cu Cv Cw Dl) Nk(Lj Mt Nl Nv Oh Qe Wm) Ji(Jo Mb Nd Ne Ni Of Og) aJ(Al As Ba Bb Cu Cw Dd) Ml(Jl Mp Mv Mw Nv Ny) Il(Iv Nb No Pa Pc Pe) Jg(Jo Lj Ly Mf Ni Oz) Om(Et Ir Mb Pf Qc Wm) bN(cN cR cS Cw dG fR) In(Hx Iv Lj Mx Po) Nv(Ii Iq Jo Ne Og)

Figure 17 Continued dA(aD Ao aQ dK dN) fR(aF Bn cE Ch De) Wm(Hx Iu Jo Mr) Is(Hw Ii Ni Of) cN(Bn cL cR De) Ax(al aL cR) Mb(Mm No Po) Iq(Ir Oh Qe)
Lj(Hu My Ni) Of(Ir My Pf) dG(Bn cE De) Ao(Cu Cw) Mm(Ly Ne) Mp(Mf Nd) Pc(Hu Mx) aE(aM cR) CsDe NtOg NbIi NiOh QcQe cEdF

Unconstrained panels with 2 analytes, where 1.0E-2 >= 'AUC p-value' > 1.0E-3. Contains 2,290 panels of 14,881 total panels evaluated. : Fr(aD
aE aF al Ao aP bB Bc bJ BN Bo bV cE Ch cP Cx Hq Hr Hu Hw Hx Ih Ij Il Im In Io Ir Is It Iu Iv Jg Jh Ji Jk Jl Jn Jp Jr Lh Li Lw Lx Lz Ma Mc
Mg Mh Mi Mj Mk Mn Mp Mq Mr Ms Mt Mv Mw Mx My Na Nb Nc Nf Ng Nm Nn No Nr Ns Nt Nv Nw Nx Ny Oh Oi Ok On Oy Pa Pd Pe Pf
Pg Po Pz Qa Qb Qc Qd Qe Wm) Bc(aC Ad aG Aj aK AL aM AN aO AP aQ AR AS aU aV Aw AX aZ Bb bC bE bF BG bH bI bJ bL bM bO bQ
bR bS bU bW bX bZ cA cB cC cD cF cG cH cJ cK cL cM cO Cp cQ cR CS Ct cU CV CW cY cZ dA DB DC DD dE dF DG dH DI dJ DK DL
fR) Li(Et Fp Hq Hr Hw Hx Ih Ij Ik Il Im In Io Ip Ir Is It Iu Iv Jg Jh Ji Jk Jl Jm Jn Jq Jr Jt Lh Lj Lu Lw Lx Lz Ma Mc Me Mg Mh Mi Mk Ml Mm
Mn Mp Mq Mr Ms Mt Mv Mw Mx Mz Nb Nf Nj Nn No Nq Nr Ns Nt Nv Nw Nx Ny Oe Oh Oi Ok On Oy Oz Pa Pc Pd Pe Pf Pg Po Pz Qa Qb
Qd Qe Wm) cP(aC AD aE aF aG aH al Aj aK AL An AO Ap aQ AR AS aU aV Aw AX aY aZ Ba Bb bC bF BG bH bI bJ bL bM bP bQ bR bS
bU bW bX bZ cA cB cC cD cE cF cG cH cl cJ cK cM CO Cp CQ CS Ct CU CV cW cX cY cZ DC DD dF Dg dH Di DK DL) Nn(Hq Hr Hu Hw
Hx Ih Ij Ik Im In Io Ir Iu Iv Jg Jh Ji Jk Jm Jn Jp Jr Js Lj Lu Lw Lx Lz Mc Md Me Mf Mg Mh Mi Mj Mk Mn Mp Mq Mr Ms Mt Mu Mv Mw Mx
My Mz Na Nb Nc Nf Nj No Nq Nr Ns Nt Nv Nw Nx Ny Oe Og Oh Oi Ok On Oy Oz Pa Pd Pe Pf Pg Pz Qa Qb Qc Qd Qe Wm) Lj(Et Fp Hq Hx
Ih Ik Il Im Io Iq Ir Is It Iu Iv Jh Ji Jk Jl Jm Jn Jq Jr Js Lw Lx Ly Ma Mb Mc Md Mf Mh Mk Ml Mm Mp Mq Mt Mw Mx Mz Na Nb Nc Nd Ne Nf
Ng Nj Nl Nm No Nq Nr Ns Nt Nv Nw Nx Ny Oe Of Og Oh Oi Ok Om Oz Pa Pc Pd Pe Pf Po Pz Qa Qb Qc Qe Wm) Fp(Et Hw Hx Ih Ii Ij Ik In
Io Ip Ir Is It Iv Jh Ji Jk Jn Jq Jr Js Jt Lh Lu Lw Lx Ly Lz Ma Mb Mc Md Me Mf Mg Mj Mk Ml Mq Mr Mt Mw Mz Na Nb Nc Nd Ne Nf Nj Nl
Nm No Nq Nr Ns Nt Nv Nx Ny Oe Of Oh Ok Oy Oz Pa Pc Pd Pe Pf Pg Po Pz Qa Qb Qd Qe Wm) Nw(Et Hq Hr Hu Hx Ih Ij Ik Il Im Io Ip Ir Is
It Iu Iv Jg Jh Ji Jk Jl Jm Jn Jr Lh Lu Lw Lx Lz Ma Mc Me Mg Mh Mk Ml Mn Mp Mq Mr Mv Mx Na Nb Ng Nj Nl No Nr Ns Nt Nv Nx Ny Oe
Og Oh Oi Ok On Oy Oz Pa Pd Pe Pg Qa Qb Qd Qe Wm) Wm(Hq Hw Ih Ii Ij Ik Iv Jg Jh Ji Jk Jm Jr Js Lu Lv Lw Lx Ly Lz Mb Mc Md Me Mf
Mh Mi Mj Ml Mn Mp Mq Ms Mu Mv My Mz Nb Nc Ne Ng Nh Ni Nj Nl No Nq Nr Ns Nu Nv Ny Oc Oh Oi On Oy Pa Pb Pc Pd Pe Pf Pg
Po Pz Qd Qe) Ok(Et Hq Hu Hx Ih Ij Ik Il Im Ir Is It Iu Iv Jg Jh Ji Jk Jl Jm Jn Lu Lw Lz Mc Md Me Mg Mh Mi Mk Mm Mp Mq Mr Mt Mv Mw
Mx My Mz Nb Nc Nj Nl No Nr Ns Nt Nv Ny Oh Oi On Oy Pa Pc Pd Pe Pf Pg Po Pz Qa Qb Qd Qe) aP(Aj aK aL An Ap aR aS aV AX aY bE
BG bH bI bL bM Bo bP bQ bR bS bX bZ cA cC cF cH cK CO Cp CQ Cs Ct cU CV Cw cY cZ dA DB Dc dD dF DG DI dJ) Bo(aD aE aF Al
AN Ao aQ AR aU AW aX aZ Ba bB bF bG bH bJ bO bX bZ cB cE cH cI cL cN CO Cp cQ cR cS CU Cv CW Dd dE dG dH DI Dk Dl dN fR)
bV(Ad aG Aj aK Al An AO Ap aR AS aU aV Aw aZ Bg bH bI bL bM bQ bX cB cF cI cK CO Cp CQ CS Ct Cv Cw cY Dc DD dF DG DI DL
fR) dN(aE aF al aM aN aQ aR aW Ax aY aZ Ba bB bC bE bF bG bH bJ Bn bO bW bX cB cE cG CH cJ cL cN cQ cR CS cU cV cW cX dB dD
DE dF dG dI dJ Dl fR) Pb(Hq Hu Hx Ih Ik In Ip Iq Ir Jk Jl Lh Lw Ly Ma Mb Md Me Mf Mg Mh Mk Mm Mn Mp Mw Mx Mz Nb Nc Ng Ni Nk
Nl Nm No Nq Of Og Oi Om Oz Pe Pf Pg Po Qb Qd) Mt(Hq Hu Hx Ik Im In Iu Iv Jg Jh Ji Jm Jn Js Lw Ly Mb Mc Md Mf Ml Mr Mu Mv My Nb
Nd Ne Ng Nh Ni Ns Nv Ny Of Oh Oi Om On Pa Pc Pe Pf Po Pz Qa Qe) Jp(Et Hr Hw Hx Ih Ii Ij Il Im Ip Ir Is It Iu Jg Jh Ji Jk Jl Jm Jn Jo Jq Jr Jt
Lh Ma Me Mg Mj Mm Mn Mq Mx Nf Nt Nv Nx Oh Pd Pf Pg Po Qa Qb Qd Qe) Mu(Hx Ih In Is Iu Iv Jh Ji Jm Jn Jo Jr Js Lw Mc Md Mg Mi Mr
Mv Mx My Mz Na Nb Nc Ng Ni Nk Ns Nt Nv Ny Oe Oh Oi On Oy Pa Pe Pf Po Pz Qa Qd Qe) Hv(Hr Hw Hx Ih Ii Ij Io Iu Iv Jk Jm Jn Jo Jq Jr Jt
Lh Lu Ly Lz Mb Mc Me Mg Mh Mj Mk Ml Mn Mr Mw Nc Nd Nf Ng Nl Nr Ns Nt Oi Om Oz Pz Qc) Af(aC AD aH al Al An Ap aQ AS aU Aw
Ax aY bB bE bF bG bH bP bQ bU bX bZ cB cE cF cJ cL cO Cp cV cX cZ dB DD dE Dg dH dJ dK) Nh(Et Hq Hu Hx Im Ip Iq Ir Is It Jh Ji Jl Jq
Lh Ma Mb Md Mf Mm Mn Mq Mv Mx Mz Nc Ng Nj Nm No Nt Nx Of Oh Oi Om Pc Pf Po Qa Qb Qd Qe) On(Et Hq Hu Hx Ih Ir Is Jg Jh Ji Jm
Jr Lh Lw Lz Mc Mh Mi Mk Mr Ms Mv Mw Mx My Mz Nb Nj No Ns Nt Nv Oh Oi Pa Pe Pf Po Qa Qc Qd Qe) cN(aE aM aN aQ aR aS aU aW
Ax aZ Ba bB bC bG bJ bW bX cE CH cM cQ CS CU CV CW cX dA dB dD dE dF dG dH Di dJ dK Dl) aA(Ad Aj Al An Ao Ap Ar As Aw Ax
Ba Bg bH Co Cp CQ Ct Cu Cv Cw Dc Dd Dg Di Dk Dl Et fR Im Jq Lu Mb Mg Mn Nv Pz Qa Qb Qd) My(Hx Il In Iq Is Iu Jh Ji Jm Ly Md Me
Mf Ml Mm Mp Ms Mv Mw Nc Nd Ne Ng Ni Nk Nl Nm No Nt Nx Oe Og Oh Oi Pa Pe Pf Qe) Lx(Hr Hu Hx Ih Ij Im Iq Iu Jk Jn Js Jt Lw Mc Mg
Mh Ml Mq Mr Mx Nc Nj Nk Nl No Nq Nv Nx Ny Oi Om Oy Pe Pg Qa Qe) Cx(aC aD aH al aM An Ao Ap aQ aR aS aY aZ Ba Bb bJ bP bQ
bX Ch cl cJ cL Cq cR CU CV Cw cX dA dD dF Dl) Mv(Hq Hx Ik Il Iq Iv Ji Jk Jm Ly Mb Me Mf Mh Ms Nb Nc Nd Ne Ni Nl Nq Nt Nx Of Og
Oh Om Pe Pf Qe) Mi(Hr Hw Ij Ir Is It Iu Jh Ji Js Lz Ma Md Mg Mj Mk Mn Mr Mw Na Nf Ns Nt Nv Oe Og Oh Pd Pg Po) De(aE aF aM AN Ap
AR aW Ax aZ Ba bC Bg bJ bN Cq cR cS CU CV CW cX dA dF) Ji(Hq Hu Ii Ik Il In Iq Jq Js Lu Ly Md Mf Ml Mq Mx Na Nf Nk Nl Nx Oe Om
Oz Qc) bN(aD aE aM aN Ao AR aW Ax aY aZ Ba bB bJ Bn Ch Cs Cu cW cX dA dE dF DL) Nv(Hq Ik In Jk Js Ly Mb Md Mf Ms Na Nc Ng
Ni Nj Nl Nm Ny Oe Oy Oz Pc Pz Qc) cS(aD al aM aQ aR aW aY bE bG bJ Bn bO cE CH cL cR cV dA dB dE dG dH fR) Cs(aD aF aH al aM
aN Ao aQ bB bC bE bJ Bn bO Ch cV Cw cZ dA DB dE dJ) dG(aD aE aF aH al aN aQ aW Ax aZ bB bF bJ bW cG Ch cL cR cW cX dB dH dK)
Ne(Et Hu Hx Ip Is Jh Jq Ma Mp Mq Mx Mz Ni Nj No Og Oh Om Pf Po Qa Qe) Of(Et Hx Ip Jh Jk Lh Lw Ma Mg Mn Mw Mx Mz No Nt Ny
Om Pd Pg Po Qb Qd) Jg(Hq Hx Ik In Jk Js Md Me Ms Nc Nj Nk Nl Nm Nt Oc Og Oy Pc Qe Qe) Ni(Hx Ip Ir Jl Lh Mp Mx Nb Nc Nl Nt Om Pa
Pc Pe Pf Pg Po Qa Qe) Nd(Et Hx Im Ip Ir Is Jh Jl Ma Mm Mw Mz Nb No Pf Po Qa Qb Qe) dA(aE aG aM aN aR aW Ax aZ Bn bU cE Ch cL
cM cQ cR cW cX dD) fR(aD aE aG aH al Ao aW bB bC bF bJ bU bW cG cl cL cV dH dK) Oh(Hu Ik Jh Jm Jo Js Ly Mb Mf Ml Na Nc Ng Nl
Og Oi Oy Qc) Qe(Hu In Jm Js Lw Ly Mb Md Mf Ml Mp Nc Ng Nl Og Pc) Om(Hx Il Ip Iq Jk Ly Ma Mf Mm Mp Mz Nc Nt Og Pd Qb) aE(aW
aZ Ba bC bG bJ Bn bQ CU Cv Cw dF dl Dl) cT(Ad Ap Ar As Aw Ba Bb cH Cu Db Dc Dg Di Dk Dl) Ml(Et Hu Ij Im Ir Is Jh Mm Nq Pc Pe Pf
Qa Qb) In(Hw Jl Lh Lz Mh Mj Mk Mr Nb Nr Pa Pc Pe) aD(aZ Ba bG bJ bO bQ cQ cR CU Cw dE dF) cX(Al Ap As Ch Co Cq cR cW Db Dd
dE Di Dk) Ax(aF aM bB bC bE bJ Bn bO bP Ch cZ dJ) Nk(Et Hx Ik Im Ir Jh Nt Pe Pf Qa Qb Qd) Il(Ij It Jh Jl Lz Mj Mk Mp Mr Mw Nf Nr)
Iq(Et Hx Im Ip Mp Mx No Nt Pd Pf Qa Qd) Lw(Hq Jh Lu Ly Mf Nb Nc Nl Og Oz) Pc(Hx Ik Is Ly Mb Me Mf Mp Nb Pe) aF(aM aO Ba Bn cR
Cu Cw dE dF Dk) Bn(aM aN Ar aW aZ Ba bC cW) Mf(Et Hx Is Jl Mw No Nt Pf) Jh(Iv Js Mc Md Mr Nb Pe Pz) Og(Hu Hx Ir Nb No Pf Qa Qd)
Ly(Et Ma Mp No Pf Po Qa) Mb(Et Ip Is Mx Mz Nt Pf) cW(aV aW bG bO cC cR dl) Ba(aG Aj aW Bb cE Ch) Hu(Hx Is Mm Mz Pf Qa) Jo(Lh
Lv Nb Nt Pf Po) Mp(Ik Lu Me Nc Nl) Is(Jr Js Mj Na Oz) aN(bE cH cR dB dE) Ao(Ap BG Dl) Cw(aH cE Ch cV) Po(Ii Ik Me Nl) Ng(Im Lv Pf
Qa) Jl(Hr Ik Iv Me) aM(Ar aW aZ dE) Mm(Ik Me Nl) Mx(Iu Nl Oz) Na(Nb Nt Pe) Qc(Ir Qa Qd) aW(aR cR Cu) Ch(bC Bg) Nb(Iu Oe) Hw(Lh
Pe) Ii(Lh Pe) bB(dD dE) EtNl MdNy MwJs Hrlv QaJm aQaU Constrained panels with 3 analytes, where 1.0E-8 >= 'AUC p-value' > 0. Contains 3,059 panels of 597,622 total panels evaluated. : Jj{Om(aA Et
Fp Fr Hv Hw Hx Ih Ii Ij Im Ip Ir Is Iv Jg Jh Ji Jk Jl Jm Jo Jp Jt Lh Li Lj Lv Lw Lx Ma Md Mg Mi Mj Mk Mm Mn Mp Mr Mt Mu Mv Mw Mx
My Mz Nb Ne Nf Nh Nl Nn No Nr Nt Nv Nw Nx Ny Oh Ok On Pa Pc Pd Pe Pf Pg Po Pz Qa Qb Qd Qe) Pb(aA Fp Fr Hq Hu Hv Hw Hx Ih Ik In
Ir Is Iv Jg Ji Jk Jl Jo Jp Jt Lh Li Lj Lv Lw Md Mg Mi Mj Mk Mm Mp Mr Mt Mu Mv My Mz Nb Ne Nh Nn No Nr Nt Nu Nv Nw Oh Ok On Pa
Pe Pf Po Qe Wm) Lv(aA Fp Fr Hq Hu Hv Hw Hx Ii Ik Is Iv Jg Ji Jk Jl Jo Jt Lh Li Lw Lx Ly Mi Mk Mm Mp Mr Mu My Nb Nc Ne Nf Nh Nk
Nn Nr Nu Nv Nw Oh Ok On Oy Pa Pc Pe Po) Mi(aA Fp Hq Hx Ii Ij Ik Il In Jk Js Lj Ly Mb Md Mf Mj Ml Mt Mv Mw My Mz Nb Nc Nd Ne Nf

Db DE dN) Bc(aD Bo cP cR CX De) De(aF Bo bV cP Cq Cs) cX(Ax Ba Bo Cs dE Dl) Cx(aE Bo cP Cs Dl) aF(Bo cR dE) cP(Bn Ch cR) aD(Db dE) AoBa BnBo bOdD} Lv{Mj(Hv Il Is Jl Lx Mk Mx Nb Nr Nw Ok) Nk(Hu Hv Jp Mu Nc Ne Nh Nl) Il(Ij Iv Lx Mk Mr Pa Pe) Og(Hv Mk Nb Ne Nr Nw Ok) In(Hw Hx Iv Lx Mr Pb) Qc(Jp Lj My Nv Oh Qe) Jo(Fr Lx Ok Wm) Fr(Ly Md) My(Iq Ne) FpMu NnIi LxNi Mvlq} Bc{cX(aD aE aN Ao aQ aW bJ bN bV bW cE Ch cP cQ cR DE) Cx(aD aE Ao aW bJ bN bW cE Ch cP Cs De) Af(aD aE aQ aW bJ bN Bo cR Cs fR) Bo(Bn cE Ch De) AobO DecN aFcR aQaU} Hv{Fr(Hw Ii Iq Js Mb Md Mj Nd Nk) Nk(Jp Li Lx Mm Mu Nc Nh Nn) Il(Ij Iv Mk Mr Pa Pc Pe) Ii(Jg Nn Nv Nw Ok) Mj(Lx Nw Ok) In(Jg Nw Wm) Hw(Nn Ok) WmNa LwMb JgJk JsNw} Af{bN(aP aW Bo cN cR Cw FR) Ba(aD aE aW Bo cN cP) cP(aW BO cR Cw) fR(aF aW bW cE) Bo(bJ Cs Cv) aE(cR Dl) aP(bW cE) CvcN bObV bWdG} Nk{Ne(Fr Jg Jp Li Lw Lx Mp Nw Ok) Nc(Jp Li Lw Lx Mp Nw Ok) Nl(Fr Jp Mu Mv Nn) Mb(Fr Jp Mp) Fp(Mu Mv) Nh(Jp Lx) MuLj} cX{fR(aE aF aI aN Ao bN bW cE Ch cL) Ao(aP Ba Cu) De(aP bV cP) Cs(bJ bO) bN(Bo Cw) ChcP DlaE} Jo{Ok(Mb Mf Mk Mr Ne Nn Oy Pb Pc Qc Wm) Lx(Mf Mj Nd Ne Nh Po Wm) Wm(Jp Nw) LwIk} Il{Fp(Iv Mk Mr Pa) Pb(Iv Lx Pa Pe) Mb(Iv Pa) Mf(Lx Pa)} cP{bO(Bn bV Cx De) Ch(Ba Cw Cx) Bn(Bo dA) De(aW Cw) CxaW} Nn{Ii(Lw Lx Nw Ok Pb Wm) Nd(Lw Lx Nw) JtOk} Wm{In(Jp Lx My Ok Pb) Ii(Jp Nv) NaHr} bN{fR(Bn Ch De) AoCw BnBo CxaW aPcE cNcR} Cx{fR(aF cE cG) AoBa DlaE aPcE} Lx{In(Nd Ne Nh) Mj(Mf Mu) MuJk} Og{Ne(Nw Ok) FpMu LwMb OkPb} Ao{Ba(bJ bO Ch) FrbO} Mb{FrNg LwJp MdMp} Ok{Jt(Jg Qc) IiOh} aQ{aU(aP Cs) dAdN} Nd{LwMy NiJp} aF{cR(aP Ax)} bO{bV(cE De)} IiNwOh Constrained panels with 3 analytes, where 1.0E-7 >= 'AUC p-value' > 1.0E-8. Contains 887 panels of 597,622 total panels evaluated. : aA{Nk(Mi Nd Nh Nj Nw Po) On(Jk Lj Ly Mf Ms Og) aO(aW Bc bV bZ cP) Mf(Iq Mp Nw Ok) Ml(Iq Jq Mq Ni) Ng(Hu Mg Nn Nv) bO(aM bJ dC De) cX(aG aW Ax cW) Bc(aE bJ cE) Ch(cP cV dN) Cx(Ar Ax Cs) Nr(Ji Nt Oh) Mj(Mi Nw Ok) Js(Ji Lx Nx) bA(aD aG aW) dH(cN dA dN) Bn(bC cP) Nn(Ii Jk) Nq(Li Nw) Ni(Lj Nd) Jq(Nu Pb) DecP LwNa LxJk LyJg MbMi MhOm MmPc MuOf IiOh aDaZ aEaM aGbJ} cT{bB(aN Ax Bo bP dA dG dL dN) Ch(aD aP Bc Bn Bo bV cP) aW(Bn cE cP cR De dN) Bc(aD aJ bA Bn Co) cL(aN aP bV cS dE) bC(aE bF Bn cG) cE(Ax bJ Cs De) dH(aP cN dG dN) bN(aD cN cR) cG(bV cN dG) cP(aL bO dE) cX(aE aY cR) Ao(aM Bn) aF(aP dN) aH(Ax dE) bF(aP cS) BnaY BocB DecR aDbV aJfR aMdA bOdN} Nk{Nc(Fp Fr Jg Ji Lj Mu Mv My No Nv Pb) Nu(Hx Ji Jl Nv Nw Ok Om Pc Pe Po) Nh(Fp Fr Jg Li Mu Nn Nv Nw Ok Pb) Hv(Fp Lj Lw Mp Ne Nl Nw Oh Ok Pb) Jp(Ly Nd Nj Of Om Pb) Ne(Ji Mu Nn No Nv) Nl(Jg Li Lw Lx Mp) Fr(Fp Nd Nj Pb) Om(Im Jj) WmNa FpMy NnIi LwMb MvLj} Mi{Fp(Iq Ml Mw Nb Ni Ny On Pb) Mf(Js Md Mv My Mz Nf Po) Ne(Hq Ij Jk Nc Ng Oy) Lj(Hr Ij Il Nf Ni Pg) Nl(Ii Jk Na Ni Pd) Nd(Fr Hx Il Jp) Ml(Mh Pd Pg) Mb(Jg Nj) Ni(Ii Nj) Hq(Ly Pb) Jo(Li Oh) WmIi LvMy MhJj MpLi NhIn HuJk HvPd IqJs QcQe JpOm JqOk OgPc} Om{Jg(Hu Jp Lh Li Lj Mj Mp Mv No) Nu(Is Jh Lw Lx Na Oh Ok) Mv(Et Fp Ji Lj Mz Qe) Mm(Hv Mu Nv Oh Qe) Im(Hv Jl Lh Nb Pe) Ni(Is Lx Pf Qe) Nw(Jp Lx Ml Ny) Lv(Hu Of Qe) Oh(Jp Lw Ok) Fr(Fp Lj) Mp(Jh Qa) Mu(Jt Pe) Nv(Jl Pc) LwQa NhJp HvLi QcQe} Lv{Og(Fp Hw Hx Ii Ij Iv Lj Lx Mr No Pa Pb Pc Pe) Of(Hv Lx Ok Oy Pf) On(Jk Md Oy Pg Po) In(Nb Pa Pe Wm) Js(Hv Li Nw Oh) Fr(Iq Ng Pb) Md(Lx Mw Ny) Jo(Jt Nv Pe) Mj(Iv No) Iq(Jp Nn) Qc(Li Ok) NrNa LyJp MmHv MuLj NcNi HwHx} Of{Jg(Fp Ir Is Lj Lw Ly Md Mu Mx Pe) Nv(Hw Jl Lw Mk Nr Pc Wm) Mu(Hv Is Ji Lx Nh Pb) Oh(Fr Hv Jp Lw My Nh) Fr(Nh Nl Ok Pb) Nw(Lw Ml Ny Wm) Nu(Hx Lw My) Wm(Hr Jp) Ni(Hx Is) LxNh MvLj IkJp OkPc} On{Ne(Hr Lh Md Na Nv Oe Pg) Jt(Hu Lw Mv My Nn Nw) Fp(Nv Nx Og Qc) Nd(Hu Jo Nr Po) Hw(Nf Nh Oy Pg) Iq(Hr Il Md Ng) Lh(Il Mf Ok) Oe(Hr Iu Nv) Mb(Js Mj) Nh(In Og) Jo(Nf Og) NuNx MpNg HvNv IlPc} Nu{Nr(Fr Hq Mu Mv My Pb) Na(Iq Lh Mj My Nb Wm) In(Hv Jg Lh Lw Pc Po) Lw(Jp Mb Ni Pb) Ng(Fr Hq Mu Mv) Og(Hv Ji Jq Nn) Nn(Jm Md) Lx(Js Ni) Ii(Is Ji) Jo(Lh Pe) Nw(Nx Qc) MjJi} De{bN(aP aW Bc Bo bV cN Cw) Bo(Ax cP Cs cX dA) dM(Ba Bg Cu Dk Dl) Bc(aE aW bV cP) Ba(Ao cN cX) cP(cR Cx dA) fR(aF cE) CwcN bCcX} Af{Bo(aN Ax bC dA Fr) aP(aF aW cP dL) bV(bJ bN cE Ch) Cv(aE bN fR) cP(bB Bc Ch) aW(bC cR) bJ(Cs Fr) AxdM BaCh BccQ CwcN aFcR bCbW bNdG} cX{fR(aD aW Ax bO cQ cR Cs cW) Ao(Ap Cv Cw dA Dl) Ba(aD aE Ch cL Co) Bo(aM aN bC dA) Cs(aP bC bN) Ax(aI cP) BgCh} aJ{Bc(aD Ao aW bA bO cP dM) Ax(aF cG Ch) aW(bX Ch dL) Ao(aZ Ba) bB(cM dD) bX(Bn dM) cV(bV dN) dA(bU cL) CsfR aEcP aIdD} bA{dA(bJ bQ bR cA Ch cO dI) Bc(aD aG aW bO cJ cV) Ao(Ap aS Cw) Ax(bF cG dF) Bo(aH cB) aS(aG cP) aEcP aWbE} Hv{In(Is Jl Lw Po) Js(Jp Li Nn Oh) Iq(Jg Mm Nn) Og(Jg Lw Mu) Mj(Il Ji) Hw(Jg Nw) WmHr MzNw NiJp JqOk} Cx{bN(aP bV cN cR fR) cR(aE aF Bc cP) Ax(cP dM) aE(aM bC) aP(aF bW) cE(bV dG) CwdM aWbC bBcP cLcN} Jj{Ji(Iv Jl Mk Mr Nr Pa Pc Pe) Lw(Iv Jg Mk Mr Pe) Po(In Ml) Mm(Is Mj) NsPc} Ii{Nn(Hw Is Iv Ji Lh Mk Mr Nb No Nr Pa Pe) Oh(Fr Jg Lw Lx) WmFr} Lx{Mb(Fr Js Lh Mj) Ne(Ni Nl) In(Mj Ni) Jo(Li Pg) FpIl MvJk NdOg NhHw JsOh} Ok{Jt(Fr Iv Jl Mk Nb Nr Pa) Nd(Nn Og) Jo(Fp Ml) MuJq NeNi NhOg} dM{Ax(aF aQ bN cE) bV(aQ cP) cE(Cu dD) BaaD BcaE BnCq BobO CsbN bBcP} Fp{In(Hw Iv Mr Nb Pa Pb) Ni(Jl Jp Mp) Mu(Ng Pb)} aP{Bn(aF bN bW cE) cE(aQ cR dN) aDbO aQbB aWbN bCbW} Jp{Ni(Ly Ne Nh Nl Pb) Wm(Js Mr Na) MbMp MuIq} cP{Bo(bO Ch Di) Cw(aI cE) bO(Ax Cs) BnaW cLdA} Il{Iv(Lj Mf Mu) Pb(Jl Mk Mr) MfPe PaPc} Nw{Mj(Mf Ne Nh) Js(Lj Nc) Og(Nh Pb) WmIn} Fr{Ly(Jk Lj Md) Mb(Lw Md) WmJo OgPb} bN{aM(bV dN) bB(Bc fR) BncN BocR} bV{bO(aD aQ Ch cW) aQaU} Bc{Bo(aI bB) aEaM aWcR} Wm{In(Nn Nv) NaIu JoNv} Mb{Mp(Hq Pd Pf) NnNg} Og{Pb(Jg Mu) LwHu NeJi} Ba{ChdN aEaM} Bn{BodA aFfR} Mu{NrLj IqPe} AoCwbJ AxaQaU NnLyNg aFaMfR Constrained panels with 3 analytes, where 1.0E-6 >= 'AUC p-value' > 1.0E-7. Contains 1,325 panels of 597,622 total panels evaluated. : Of{Jg(Hu Hw Iv Jh Ji Jl Jp Lh Li Mj Mp Mr Mv Mw My No Nr Ns Pa Wm) Lv(Et Hw Ij Is Iv Jl Jt Mj Mk Mr Nb Nr Pa Pb Pe Wm) Oh(Hu Jh Ji Jl Lx Mk Nb Nr Pa Pb Pc Wm) Nv(Iq Is Iv Lj Mr My No Om Pa Pb Pe) Nu(Hq Ip Is Ji Jl Om Pc Po) Lw(Hu Ik Mt Ne Nh Qe) Lx(Hw In Jo Jp Mj My) Pb(Im Jp Li Mt My Ok) Wm(Mu My Nk No Ok) Mi(Iq Lj Ml Ne) Nk(Im Ir Is Pf) Qe(Jl Mp Mv Nh) Jp(Hv Mv My Nw) Im(Mk Mr Nr) Fr(Fp Lj) Mp(Nh Qa) Mt(Pc Pe) Mu(Et My) Jq(aA Ok) MmHv MvJi NiPf QaPc LiNw} Om{Nv(Hw Is Iv Lj Mj Mk Mr No Nr Pa Pe) Nk(Fr Is Lv Mu Nw Pf Qe Wm) Im(Hw Iv Mj Mk Mr Nr Pa Pb) Nu(Ip Ir Ji Md My Mz Qe) Jp(Hv Ir Lw Lx Mp My Pb) Li(Fr Hx Lw Mp Nj Nw Pb) Lv(Hv Hx Ir Jl Pf) Mm(Ir My Nh Nw Qa) Mv(Hv Hx Ir Is Po) Oh(Et Hv Lx My Nb) Mu(Hw Mi Nb Wm) Lw(Jl Nh Qe) Ni(Hx Ne Qa) Jg(Fp Jq Pf) Wm(Mi Nj) Fr(Hx Mi) No(Mt Qa) Lx(Il In) Mp(My Nh) Jq(aA Jj) Nw(Nx Og) EtQa MbMd IlPa JlPb} Nk{Lv(Hw Hx Iv Jl Li Lj Lx Mk Mx Nb Nr Pb Pe Qe) Nh(Hx Ji Lj Lw Mp Mv My Oh Pa Po Qe) Nu(Hw Is Iv Jq Mk Mq Mr Nb No Nr) Nc(Hq Hx Nn Oh Pf Po Qe) Ne(aA Jq Mm Mv My Pb Po) Nl(Mm My Nv Nw Ok Pb Po) Jp(Fp Iq Lj Mu Ni Wm) aA(Jg Li Ok On Pe) Mb(Jg Lx Mu On) Fp(Jg Nn On) Iq(Jg Li Nn) Pb(Li Mu Nn) Hv(Ji Wm) Lj(Fr Hu) MsOn QcQe} On{Mj(Il Jk Lj Mf Nf Oy Pg) Hw(Jk Md Mp Ms Nb Ng Po) Fp(Md Na Nf Pg Po) Nh(Hr Jk Jt Ni Pg) Nx(Iq Jt Lv Ly Mb) Oe(Hq Lh Lj Mq Ny) Ne(aA Jk Mi Nr) Nf(Iu Lh Ni Pb) Jq(Jk Md Ng Ok) Nu(Mb Ms Po) Lv(Jm Nr Nv) Mp(aA Ij Qc) Js(Hv Jn Md) Oy(Lh Pb Qc) Nb(Jo Ml) Ni(Jo Nc) Ij(Md Wm) In(Nd Og) Jk(Mu Pg) Jt(Jp Li) MbaA MfHr NgQc IlIu} Mi{Lj(Hx Jk Lx Md Mt Mv Mw Ny Og Oy Pa Pb Pe) Ni(aA Iq Lx Nc Nh Pc) Ne(Ji Md Nw Pe Po) Nl(Hq Hr Nc Nh Pg) Iq(Ii Jg Jp Li Pd) Pc(Fp Il Li Nw Pg) aA(Hu Ii Md Oy Pg) Nd(In Jo Li Mw) Fp(Lw My Nt) Nn(Jo Mb Mp) Mf(Mh Ng Oy) Ml(Hx Ij Il) Nh(Il Na Pd) Ok(Ii In Nm) Mb(Mu Nr) Nj(Hq Pd) Nw(Ii Oe) NqIl NuJm HwLi} cT{cP(aF aH aP aY bF cB cG cN dA) Ao(AP bC bJ bO cR Fr) Bc(aE aF aW bF cG cL) aP(aG aI aO aW bN cB) bJ(aN Bn bV cL cN De) Ch(aM aW cE cS) De(aE Ar aY Dk) dE(aF aN aW bV) bF(Bo cW dG) bO(aM bV Cx) cE(aY bP dB) cL(aY Bo dA) cR(aG Bn cV) Cs(aM bB) aF(cN dG) aH(cW dN) aW(aD bV) BndA aAaG aLcW aNbN cGcS} aA{Lx(Hr Hu In Mx Ni Pg) aW(Bc bJ Bn bO cP Cx) Nw(Il Jk Js Lj Ms) Bc(aD bO dC dM) Nd(Hv Mq Ng Og) Jg(Mf Ng Og Oi) Il(Mk Mr Po) Ji(Ly Mf Mj) Pc(Md Ns Oy) aE(cL De dH)

Figure 17 Continued

Ax(aF bN) Nn(Lj Oi) Ni(Nj Nx) Ok(Et Ly) aG(Cx dM) cV(bV Cs) dA(bU cE) AobJ ArbO BnaD FrOe NrPf MqLj JqOg bCcL} Lv{Og(Is Jg Ji Lh Li Lw Oh) Mj(Lh Li Lj Mr Oh Pe) Qc(Fp Fr Ir Jg Nn Nw) Md(Nb Nv Nw Oy Pg) Fr(Fp Lj Ne Nr) Iq(Hv Jg Jl Oh) Pb(Hv Jp Mu My) Lx(Hq Pg Po) Lj(Hu Js Mm) Ok(Jq Nm Nt) Nn(Jm Nr) Na(Iv Wm) Ng(Jp My) In(Nw Po) LwHv MkJo MmHu NeNj NhJp NiJl liNw} bN{Cx(aM aN bC Bo cP Cs Cw dG dN) Af(aM aN Ar Ax bC Cs dN) Bo(aM bB BC cE Ch Di) bV(aN bB Bn cE Ch cN dN) De(bC cP cR dG dN Fr) cR(Ax Bc Bn dG dN) Cw(aH bB cE Ch) dG(Bn cE cL) Bc(aW dN) aM(aE fR) aP(aD Ch) AoAp AxcX BabB aWfR cLcN dAdN} Nu{Nr(Ir Jg Li Ma Nv Nw Oh Oy Qe) Og(Is Jl Mk Nb Pa Pc Pe) Lx(Hq Iq Jk Md Pd Pg) In(Ii Ij Mj Nf Nv) Md(Jg Lw Mp Nw) Jo(Jt Mk Mr Pa) Mp(Pd Pf Pg) Ng(Ma Nv Oy) Ni(Is Jl No) Ii(Jl Lh Na) Jg(Jk Ms Oi) Qe(Jm Qc) Js(Is Jn) Nw(Ms Mz) LwPc NaJt JiPb} cP{Ch(Ap Bc Bg Bn bO cR) Af(Ax bC bV cN Cs) Cx(aF bC bV cN Cs) aP(bB Bn bO cE De) bA(Ao Bc Bg bI Co) bB(Bn Cw DE) bO(Bc cR dN fR) dA(Bo bU cE cR) Bc(aW Bn) Cw(Ao Bg) De(Ax Ba) BncR CscX aQaU} Bo{Bc(aE aH Ao aW Bb bF Bg bO cB) De(aM aN Ar cN Cv Cx Fr) Ch(bC bJ bV CX dA) Af(aW bB bO Dk) Bn(bC cN CV) cE(aJ cX dA) Cx(aN bC) bO(bV Cs) AoBa aMdM cQcX cRcV} Hv{In(Hw Hx Iv Mk Mr Nb Nn Nv Pa Pb Pc Pe) Ni(Jl Lj Lw Mm Mp Nc Nn Pb Pc) Hw(Jp Mm Mu Oh) Og(Ji Jq Pb) Md(Jg Mp) Iq(Mv Nw) FrNq NnJk LxIi MmPb NeNh} Af{cR(Ar Ax aZ cN Cq cV fR) Cv(aN aP aW bJ bV) Fr(aE aF bO Ch) Ax(aP bJ cN) Cs(aW Ba bO) aQ(aU bV dA) fR(aN bC bO) ArBa BgCh CqdN CuaW CwaD aEaM aFbQ aPbO} Fr{Mb(Hw Iv Ji Mk Mr Nr Nw Pa Pe) Nd(Lj Lw Lx Nw) De(cN cX dM) Fp(Mj Qc) Ii(Ir Nn) Iq(Lj Nh) Pb(Lj Md) cX(Ao Ch) WmIn LyHu NePc NiNl} dM{Ch(Bg bV Dk Dl) Cw(aD aQ cE De) Bn(Ar Ba Cs) bB(bV dD dE) cE(Ba bZ Cs) Ao(Bc Cu) De(Ar Ax) bO(aP Cs) CxaW aHdD aJfR bUdA bVcV} Cx{fR(aD aN aW bW cL) Ao(Ap Cv Dl) aP(aE aW De) bV(bJ bO Ch) cN(cE Ch De) Cs(bJ bO) aW(cR Cu) bW(bC dG) BaaD CvaF aQaU} Lx{Jo(Hq Hx Md Mz Nn Og Pb) Mb(Lz Mh Mm) Hw(Il Md Pg) Na(Mj Ne) Ii(Pf Wm) In(Iq Lz) Jt(Jg Ok) NnIq MdNi MfJs NdIl NhNl} cX{De(aN Bg cN Cu Cw dA) Ax(aP bC bJ cR) Ch(cN cQ Cw dA) Cs(aW cQ cR) Cu(aE aW cE) Ao(Bg cR) fR(aG cV) BacE CvbV} Ok{Jt(Hw Is Jp Lw Mr Pc Pe) Mj(Ml Mu Ne Nh Pb) Jq(Jo Mf Ne Nn) Nm(Ne Qc) Ii(Mm Wm) In(Pb Pc) NnMb JsLj} Nw{Iq(In Js Mz Ne Nn Nx) Js(Mb Nf Nh Og) Hw(Jl Jo Jt) In(Mj Ne Nh) Qc(Ii Lj Qe) Jt(Iv Jl) MbMj NcNi} Mu{Fp(Iv Lw Mk Mr Nr Pa Pe) Iq(Hx Is Nb Pa Qe) Lw(Mb Nd) Il(Mk Pa) Lj(Ni Pb) MzNd HwHx IiOh OgPc} Il{Pa(Ik Lj Nh Nl Nx Qe) Iv(Mv Nh Nx Qe) Mk(Ik Nx Qe) Mr(Ik Lj Nx) Hw(Pb Pc) FpMj NrPb} Ao{Ba(aE aM Bc cE dA dN) aJ(CV Cw dL) bA(bC bI dN) Bc(De fR) Cw(cV dA) bO(aP Cs)} Bc{Ch(aW bV cN dN) De(aD aP aZ bJ) Bn(aW cN) cE(bV cN) aJdL aQbB bAcR bWdN} Ni{Fp(Lw Mk Mr No Nr) Nc(Jp Li Lj) Ne(Jg Lw) Jp(Lj Nj) LiPb} bV{aM(aE bJ bO cE De) Ch(bJ De) bO(cS dN) BncN DebJ bFcE cRcV} Nn{Ii(Fp Hx Jl Nh Po) Nd(Ji Jp Mz Ng) Pb(Ng Og) LwIq} In{Nb(Iq Lj Ne Nh) Fp(Jl Mk Pe) Wm(Ji Og) LwIt MfPb NhPe} Og{Jg(Fp Ly Ne) Pb(Li Mv Nh) FpMy NoNh LwNd NeJq} aJ{fR(Ax bO dA) Ch(Ba bX) aD(bC bM) AxdL CscV CwaO} aP{cE(aF aW aZ bO) De(aF bW) aQ(aI cL) ChaF dHdN} Wm{Jp(Ij Jt Oy Pg) Hq(Hr Na) MmIi JiJo} Lw{Nd(Jg Mv Mx) Mb(Jl Md) Iq(Hu My)} bA{dA(Bg Co Cq dB) CoCs cScV} Ba{cE(cN dN) ChcN DeaD} Iq{NoIm MdJg MvLj QcQe} Oh{Ii(Hu Ji Nb) NgHu} Bn{bW(dG fR) cEfR} Jp{Nh(Ne Pb) MbMd} Cs{DecN aFcR} AxDecN ChaFfR MbMpOz MdMlJg MyNdLi aDaQdA

Constrained panels with 3 analytes, where 1.0E-5 >= 'AUC p-value' > 1.0E-6. Contains 1,775 panels of 597,622 total panels evaluated. : Of{Jp(Hu Hw Is Iv Ji Jl Lw Ly Mk Mp No Nr Pc Pe Po) Li(Fr Hw Iq Is Iv Ji Jl Lw Lx Mk Mp Mr Nb Pa Pc) My(aA Fp Hv Hx Ir Is Ji Lj Mp Nh Pf Qe) Nu(Hw Iv Jq Lh Mk Mr Nb Nr Oy Pa Pe) Lv(Ii Ji Lh Lj Lw Ly Mm Mz No Pc Po) Nh(Et Ir Ji Mi Mm Mv Mz Nk Om Pf Po) Oh(Et Fp Hw Is Iv Jq Jt Lh Mr Pe Po) Mt(Hw Iv Jl Mk Nr Pa) Mv(Hv Is Ly Mz Nk Pb) Wm(Fr Lw Lx Mm Pb) Ni(Lh Lw Mi Om Po) Nk(Fr Hx Jk Mu Pe) Qa(Jl Mk Mr Nr Pb) Lx(Il Md Pf Pg) Qe(No Pb Pc Po) Mm(Ik Ir Lj) Hv(Et Lw Ma) Mi(Nd Nl) Mu(Lh Pe) Nv(Jt Lh) Pb(Et Is) aA(Mf Ml) FpNb FrNd MpIr NeJi IiIm JgPf NwOg} Om{Jp(Fp Hw Hx Is Iv Ji Jl Jq Mk Mm Mr Mx Nb No Nr Pa Pc Pe Po) Li(Hw Is Iv Ji Jl Jq Lx Mk Mr Nb Pa Pc) Oh(Is Iv Ji Jl Jq Mz Pb Pc Pe Po) Ni(Hv Im Jk Jl Lw Mp Mt Nc Po) Mm(Fp Hu Hx Jg Lj Mt Mv Pf) Nk(Ir Jk Mb Nc Ne Nh Nl Pe) Wm(Fr Ii Lv Lx Mv No Ok) Nu(Hv Hx Jl Jq Pc Po) Qa(Jl My Nb Pb Pc Pe) Et(Hv Ir My Pb) Fr(Ji Mx Mz No) Mi(Ii Il In Ji) Mp(Ir Mb Nd Qe) Mu(Iv Lw No Nr) Lv(Jt Md Mz) Mv(Lh Mx Pb) My(Im Ji Pf) Hv(Jh Lw Ma) aA(Hu Jk Nq) Mt(Nb Pb) Ne(Jl Og) Im(Ii Jq) Qe(Mx Pc) Jg(Mz Pe) FpOg MdMl MnNh IpJh} Mi{Iq(Ij Il Jk Lx Md Mv Mw Mz Nf Nk Og Ok On Pg Po) Ni(Ij Il In Md Mv Mw Nf Ny Oy) Nh(Hr Ii Jk Md Ng Oy Pg Po) Ml(Hq Lj Mt Mv Nd Ny Pb) Nl(Md Ng Nn Oy Pe Po) On(Ij Jo Jq Mn Nq Pg) Mj(Il Jp Lx Nw Ok) Lj(Mh My Nb Nr) Mt(aA Mf Ne) Hq(aA Mf Oz) Hu(Nk Pd Pg) Jk(Fp Mu Nd) Nn(Hw Ij) Mp(Mu Nf) Ii(Mm Pc) Jo(Fr Lx) Js(aA Oh) Ok(Lh Pd) WmMb IlQe JiJq LiOe OyPc} Nk{Nc(Hw Is Iv Jl Lh Mk Mr Nb Nd Nf Nr Pa Pc Pe) Nl(Hx Ji Jl Jq Lj Mz Nd No Oh Pc Pf Qe) Ne(Fp Hx Jl Lj Mn Mz Nd Oh Pc Pf Qe) Lv(Fp Ir Is Mj Mm Mp Mz Nn Oh Po) Pb(Fp Jg Lj Mt My Nt Nv Oh Qa Qe) Nh(Is Jl Jq Mz No Pf) Fp(Jl Mm Mp Nv) Mb(Hv Nn Nw Po) Lj(Jg Mp Nn On) Iq(Fr Nw Qe) In(Lx Nw) Li(Mu Ng) aA(Mm Mq) NtOg LwIk NfOn} bN{aM(Ar aW Bc Bn CS dA De dG) Bn(aN aW BC cP Cw dN) Bo(aN Ax cN cP Cs dA dN) Ch(BC cN cP cT dG Fr) cR(aD aN Ao aW cP Cs) dA(aD Af cN cP cT Cx) De(aE aN aZ Ba cS) bB(Ax Cs Cu dG Fr) bV(aD aQ aX Bc cS) Ao(aP Bc cT fR) cE(cN dF dN) Bc(aE cT) aP(bO cP) dG(aW dH) dN(cP Cs) fR(aF aN) AxCx CwaD bJcT cNcS} Ni{Jp(Hw Iq Iv Jl Lw Mk Mp Mr No Nr Pa Pc Pe) Nc(Fp Fr Hx Jg Ji Lw Lx Ok Pb) Ne(Hx Ji Lj Mp Nn No Nv Pb Po) Nl(aA Hx Jg Lw Lx Nn On) Nu(Iv Mk Mr Nr Pa Pe) Lv(Iv Mk Mr Nr Pa Pe) Nh(Hx Lj Lw Lx Mp) Hv(Is No Oh Pa Pe) Lj(Mp Mv On Pb) Fp(Is Pa Pe) Pb(Hx Nn Oh) Po(aA Lx) QcOn LiaA} On{Oe(Fp Hu Iq Lv My Nb Nn) Hw(Hu Lj Mv Mw My Nx) Il(Hq Hr Md Nf Pd Pg) Jt(Fr Jk Mf Mw Oh Wm) Mj(Jh Md Nc Nl) Jk(Fp Iq Nm Pb) Lh(Lx Nd Nh Og) Lj(Nd Nm Nx Og) Ij(Mw Nn Nv) Js(Mw Oh Pg) Oy(aA Nv Pc) Mb(Lz Mc) Mf(Jq Nx) My(Iu Jq) Nh(Nr Nv) Og(Iq Nf) WmNa PoLx FpHr LyHq MdIn MsQc NeNx PbPg} bV{cE(aA aD aP aQ Bn Bo cN cP De dN) aQ(aM bB bJ Bn cL dA De dN) Bc(aW bJ Bn BO cG cT) cV(Af aM BO cT dN) cP(bB Bn Ch cT De) aF(Bo Ch DE) aM(aW aX bB Bn) bJ(aD aN Bn Bo) bO(aN aW aX Cs) Cx(aW Cv) aX(dM dN) cL(cN dA) cT(aG cW) AfaZ DecN aJfR aPcG bUdA bWdN cXdE} aA{Ax(aO bJ bO cE cV De) Ar(aF aO Bn De) Nw(Ii In Mp Nr) Bc(aG Ao cP) Cs(aF aO De) Fr(Jk Mb Ng) Nq(Ji Nv Ok) Lx(Hq Mt Pe) Mm(Lj Ng Oi) Js(Jn Oh Pe) aD(aF De dM) dA(bR cG cL) Nn(Hu Nr) Mf(Mq Oi) Il(Lh Pe) Jg(Lj Oe) Jq(Lj Nd) Nv(Nr Oe) aE(cW dD) BnaG PoIn MuNg MvPc IiOk aOdN aWcV} cT{bF(aE aR Ax aY bJ dA Fr) bO(aP aW Bn cN cS cW De) bJ(aE aG aW Ch Cs dE) cP(aE aS Bg Co Cp) Ch(aF Ax cR Fr) cV(aN cN dE dN) dA(aW bU De dH) Bo(Ao Co Cp) cW(bE cG cJ) Bc(aG aM) Co(Cw Fr) aE(aP cN) aF(cS fR) bC(Ax Cs) bP(cL dE) dB(aH cB) dN(AO) FrcG} Nw{Ne(Fr Lv Md Mz Nc Nx Qc) Mj(Fp Lj Md Nc Nl Wm) Qc(Fp Hv Jp Mb Mf Nh) Nu(Lw Ml My Ny) Nd(Jp Lw Mm Og) Js(Fp Jn My Nc) Jt(Lw Mk Mr Nr) Lv(Iq Lj Ny) Jo(Mk Mr Nn) Og(Lj Md Nc) Wm(Lh Mr) Mb(Lw Mp) Hv(Nv Nx) Iq(Jp Md) MsMu MzNf NhNx} Fr{Nd(Hu Hw Is Iv Ji Mr Mx No Nr Pa Pe) Ch(bJ Bo cP Cx dM) Cx(aD Ao cE De) Ne(Hu Lj Md Ng) Af(aD bC cR) De(aF bJ dA) dM(aF cE cV) Ao(bJ dA) Fp(Iq Md) Lv(Jm Nh) Ii(Mr Mz) Pc(Nl Og) cX(aD Co) WmNa LyNg HuPb HvJk HwHx IqIr QcLj} cP{Ch(aP aW Bb bC Cu dB De) Bo(aI bB bF cB cE Co) Cw(aH bF cB cL Co) dA(aW bF bR cA dH) Bc(aI bB cE cL) Bn(aF bC cN) aE(Af cR Cx) aP(aF aW cR) bO(aW cS dG) Ba(Ao cE) Cs(bA dM) aQ(aV cY) AfaF AxdM CubB DecN} Hv{Js(Is Ji Jn Lj Lw Lx Nh Po Qe) Mp(Hq Iq Nd Pd Pf Pg) Lw(Hw Ii Iq Pb Pc) Hw(Et Ip Is Ji) In(Fp Ij Jt Lh) Iq(Et Jp Li Nv) Og(Fp Ip Nb Nn) Ji(Ii Lv Qc) Wm(Hq Mj) Nn(Ng Nr) Jg(Ms Ns) MuNg NdJp QcQe} Wm{Jo(Et Jq Mm Mp Mq Mu My Na Nm No Pb) Ii(Im Is Ji Jq Lv Lw Mq Mu My) Hr(Jp Lv Lw Mu My No Pb) Mj(Lv Lx No Ok) Na(Lw My Ok) In(Lw No Po) Mr(Lv Ok) Jp(Md Nr) NtOk MyIu JnJs} Nu{Md(Mq Nb No Nv Ny Pc Po) Nr(Is Lj Og Pa Pe Pf) Pc(Jq No Oi Oy) Mp(Hq Nd Oz) Ng(Jl

Figure 17 Continued

Lx Mg) Ii(Jt Pa Pe) Js(Jr Nb No) Og(Hw Iv Mr) Nn(Jq Ms) Jg(Hu My) PoLx NsLw MbOk MkOy InJt IsJm JqPb} Af{bJ(aM aN aQ Ar aZ cR Dl) bC(aE Ar Ax cR Cs Cv) aZ(aD aE aM aN) Cw(aN aW Ch) bO(Ar Ax cQ) Ba(aM cR) Dk(aE dK) aD(Bg Cu) cN(aN cL) AoCv AxaW CscR aFdG aQcU bUdA cEdF cVfR} Ao{Cw(aP Bc bO Ch Cx De dM) Ba(aP aW bB bC cR Cs) Cu(bJ bO Cx dA De) Ap(bJ bO dA dM) aJ(aF Ax bC dH) cX(bC bJ Bo Dk) Bc(aP aW cR) Dl(bJ dM) AxbO BgCh aPbW} Iq{Nn(Hw Is Iv Ji Jl Mj Mk Mr Nb No Nr Pa Pe) Mu(Hw Ir Iv Jl Lh Mk Mr No Nr Po) Jg(Jp Pb Qe) No(Jp My) Md(Nb Nv) Il(Lx Pa) Li(Lv Pb) LwJp MpNd MvNb MyLj} Bo{Bc(aD aG Ap Ax Co cR Cs) Ax(aI Bn bO cE Ch) Bn(aM aN bB bO) Ch(Ba Bg cV) Cx(aM bB cE) De(Ba bO Dk) cX(aI bB bO) Cs(aI bJ) aM(aE cV) bC(bW cE) aFcR aPcE bBdM} Lv{Jg(Fp Ly Md Ne Nh) Mj(Fp Hw Jt Pa) Ng(Mu Mv Nn Nv) Lw(Li Ne Nh) Og(Jl Jq Jt) Fp(Jp Nn) Md(Hx Mp) Mr(Jo Na) Qc(Ji Mu) PoLi NnJi NoJr NrOh MpPd NhPc JnJs JoPa LjPb} Mb{Lw(Hw Is Iv Lx Mk Mr Nb Nj No Nr Pa Pc Pe) Mm(Hw Mr Nr Pa Pc Pe Po) Jg(Jl Md Mp) Ji(Jp Pc Qc) Ok(Jq Js Qc) PoJs MpPc NjLi JlJp} Cx{Ax(aD aF aW bC bJ bO cR fR) Ba(Aj bB cE Ch Co De) Cs(aW bC De) aZ(aM aN bB) Ch(Bg Cw) cQ(aF bO) cR(bC cV) ArDe CwaD aEcN aNbJ aQdA cEdF} Il{Iv(Ir Jp Ne Nl Qa Qb) Pc(Lj Ly Mk Mr Nr Ok) Mk(Lj Mf Mv Qa) Mr(Mf Mu Mv Qe) Lj(Ij Mj Pe) Pa(Ml Nd Qa) Lx(Ml Pd) Pb(Mj No)} De{aE(aM Ba Cw Dl fR) aW(aP Ba bC Cu fR) aF(Ba bQ cR dG) Ax(aP dA fR) Bc(Ar cR fR) cX(bJ Cs Cv) CsdN aDfR aPbO aQaU bWdG cNcR} In{Oh(Hw Iv Mr Pa Pb Pe) Nh(Hx Is Iv Pa Po) Lj(Hw Hx Iv Mk) It(Ij Mu Pc) Hw(Ik Mf) Iv(Li Pb) Pc(Ik Pb) FpHx LwIs NbLi} Lx{Jo(Fp Js Ml Nc Ny Pc) Js(Lj Lz Nh Ok) Mj(Fp Md Oy) Nn(Hw Po) Na(Lh Nh) Nd(Jp Lw) Ii(Ir Mm) LzNe HqHw QcQe} Og{Pb(Hx Ji Mx My Ne Nt Oh Qe) Pc(Jg Jp Li Nn) Fp(Ji Lw No) Nh(Jg Ji Jq) Lj(Hu Mv) NnNd NoLy MuLi IkJp} Bn{cN(aQ Ax aZ cR Cs) aD(Ba Bc fR) aP(aQ aW Bc) aF(cR dG) dA(aQ cX) dM(Ax Cw) aEaM aWfR cEdG} Ii{Oh(Is Jl Jt Lh Mv My Nv Pa Pe Po) Nn(Ir Jt Li Ne) Ir(Jg Mu) MaOk} dM{Ba(aF aM bB Ch) Cw(aF aG Ch cV) Cs(aF bB cV) aE(dD Dl) bB(cM dB) aDdD} Bc{Ch(aP bJ cI) aD(bO cR fR) aW(aM bO) cE(aP dN) cN(bW cL) AjbJ aEbO aHfR} Jo{Nv(Hw Iv Lw Mk Mr Nr Pa Pe) Li(Hw Lh Mk Mr Nb Pe)} Jp{Nd(Lw Mp Mx Oh) Nh(Lw Nr Pc) Ly(Nn Pc) Ng(Hu Ik) Qc(Fp Qe) HwHx} Ok{Fp(Js Mj Qc) Nm(Nn Pb Pc) Mj(Lj Nc) Qc(Hr Lj) JqPb JsOh JtLi LhPc} dA{aQ(aE aW bU cE cL cS) cE(cN cS dN) aD(aZ cR) aEaM bAbI dHdN} cX{Ax(aE aW bO cQ) Cu(aI Ch Co) Ba(aM Bg) Cs(Co cW) ChbJ aPdE} Nh{Pb(Jg Lw Mm Ne) Nn(Ng Nr) FpNj MuNg MyNe HwHx} aP{aE(aQ bO dH) aW(Ch dH) aDdL aFdN aGaQ bOdH cRcV} Md{Nn(Fp Mc Pb) Jg(Fp Ly Ne) MpNe MyPc NdJj} cR{cV(aE CS dN) cE(cN dG) aFdG aJfR} Ch{Bg(aE cI dN) aF(Ba dG) CwcN cEfR} Mu{Fp(Is Mm) NnJk HwIs JnJs LjPc} aJ{Ax(aW bC cV) CoCs CwaD} cN{cE(bQ Cw dF) cL(aQ Ba)} Nr{Nn(Ne Nl) MyLi HuOh} Lw{Nd(Jl Nb) NePb QcQe} Jg{LyMs NePb HwHx JtLj} aM{Cs(bJ bO) aE(Cu Cw)} Qc{Qe(Fp Ji Pb)} Mm{MyNd HuLj} Ng{FpMv NnNe} Li{NdNj HwHx} aD{AdBa CsbO} bC{fR(aF bW)} NoMlJr HuOyPc aZcEdG

Constrained panels with 3 analytes, where 1.0E-4 >= 'AUC p-value' > 1.0E-5. Contains 2,504 panels of 597,622 total panels evaluated. : Iq{Jg(Hu Hw Ir Is Iv Jh Jl Lh Lj Lw Mj Mk Mp Mr Mv Mw Mx My No Nr Ns Og Oh Pa Pe) Jp(Hw Hx Ir Is Iv Ji Jl Jq Lh Lj Lx Mj Mk Mr Nb Nr Oh Pa Pc Pe Po) Fr(Hw Iv Ji Jl Li Lx Mi Mj Mk Mr No Nr Nw Of Ok Om Pa Pe) Im(Hw Iv Mj Mk Mp Mr Nb Nr Pa Pb Pc Pe Po) Mi(Hq Hw Hx Ji Lw Mh Mt Nb Ny Oy Pb Pc) Li(Iv Jl Lw Lx Mk Mp Mr Nb Nr Nw Pa) Nv(Hw Iv Lw Mj Mk Mr No Nr Pa Pc Pe) Lv(Hx Ir Jt Lj Lx Mk Mr Nb Nr Pf) Nw(Hw Iv Jl Ml Mm Mr Ny Og Oh Pa) Hv(Ir Ji Jq Nb No Oh Pf Qe) No(Hq Jr Mv Oh Qa Qe) Nk(Hx Ir Mp Pe Pf Qa) Nn(Ir Jq Lh Lj Ok) Mv(Lw Mz Oh Pa Pe) Qe(Lw Mp Of Pb) Ok(Jq Of Og Om) Pb(Hx Ir Qa) Lw(Oh Qa) Mm(Hu My) Mu(Jt Mj) On(Fp Lj) LxNi MyPa NbOf InPe IsOm} Om{Lv(Hw Is Iv Lj Lw Lx Mj Mk Mr Nb No Nr Pa Pb Pc Pe) Fr(Hw Is Iv Lw Lx Mk Mm Mr Nr Of Pa Pe) Nk(Et Hv Hx Lj Lx Mi Mt Mv Mz Nt Qb) Nu(Hw Iv Jt Lh Mk Mr Nb Nr Pa Pe) My(Fp Ip Ir Jl Lj Mz Nh Of Qe Wm) Qa(Hw Ii Iv Jq Jt Mj Mk Mr Nr Pa) Pb(Ir Is Jh Mm Mp Mz Ne Og Pf Qe) Hx(Et Jh Ma Mp Mt Nh Oh Pf Wm) Jl(Hw Is Mk Mr Mu Nr Pa Pc Qe) Of(aA Fp Hv Ir Lj Mt Mx Ne Pf) Oh(Fp Hw Jt Lh Mk Mr Nr Pa) Hv(Ip Ji Mp Pf Po Qe Wm) Wm(In Ji Jo Jq Mz) Mu(Jq Mj Mk Mr Pa) Ni(Jt Lh Lj Mn Nl) Et(Mp Mt Pc Po) Lw(Ir Is Mv Mx) Md(aA Fp Ne) Mi(Jo Nf Pg) Mm(Lh Lx Mz) Mt(Pa Pc Pe) Mv(Jt Nb Pe) Nh(Lj Ma Ne) Jh(Mz No Qb) Jp(Jt Lh Mj) Po(Is Qe) Lj(Nw Og) Pc(Ir Is) NoQe MfaA MzPf NgNv IlIv InIt} Of{My(Et Hw Im Ip Jl Lh Mm Mv Mx Ne Nk No Nr Nt Nw Pe Po) Is(Fr Hw Iv Jl Lw Mk Mr Nh Nr Pa Pc Pe Pf Po) Mu(Hw Iv Jl Jt Lw Mj Mk Mr No Nr Pa Pc) Fr(Hw Iv Ji Lw Lx Mk Mr Nr Pa Pe) Pb(Hv Hx Ir Ji Mm Mp Nh Nt Oz Pf) Pf(Et Hw Jl Lw Ly Mk Mm Nr Pc) Nk(Et Ji Mt Mz Nt Pd Qb Qd) Qe(Hw Iv Jq Mk Mr Nr Pa Pe) Lj(Et Hu Jh Lw Mp Nh Nw) Ni(Im Jk Jt Pe Pg Qa) Mt(Mj Mp Mr No Oy) Nh(Hx Lh Ma Mn No) Jp(Jt Lh Mj Mr Pa) Wm(Ji Jq Me Nm) Et(Fp Mv Oy Pc) Lx(Hq Lw Lz Po) Hu(Mm Mx Mz Qa) Mi(In Jo Mj) Ir(Lw Oy Pc) Nu(Ii Jt) Ly(Im Mm) Mv(Lh Pc) Mx(Jh Pc) Hv(Ji Jl) Hx(Mm Mp) Qa(Ii Jq) Jg(Ms Nq) FpJl LvJq MzIk NdaA JiOy} Nk{Fp(Hw Hx Iv Ji Lw Lx Mj Mk Mr Nb Nl Nr Nw Oh Ok Pa Pc Pe Po) Jp(Hw Is Iv Jl Lw Mk Mp Mr Mx Nb Nr Oh Pa Pc Pe) Ne(Hw Ij Is Iv Lh Mj Mk Mr Nb Nf Nr Pa Pe) Nh(Hw Iv Lh Mj Mk Mr Nb Nd Nf Nr Pc Pe) Nl(Hw Ir Is Iv Lh Mk Mr Nb Nf Nr Pa Pe) Lj(Hx Is Ji Jl Jq Lw Lx Nb Nv Nw Pc Po) Pb(Hx Ir Mv Mx Mz Ni Og Pe Pf Wm) Mb(aA Et Ji Jl Mm Nv Oh Ok) Lx(Il Js Lh Li Oe Og Wm) Wm(Fr Lv Mu Nw Ok) Li(Ji Jl Lw Mp Nw) Nc(Ii Ij Jt Mj) Ni(Fr Jg Mi On) Hu(Lw Mm Mp On) Nn(Jm Og Ok) No(aA Hv Lv) Md(Nv Nw) Mi(Mp Oe) LvLw MpIk NdHx NgNv IlPe JgOg JqaA NwPc} Ni{Ne(Et Is Iv Jl Jq Lh Mm Mn Mu Mv My Mz Nb Oh Pa Pc Pe Pf Qe) Lj(Hw Hx Ij Iv Jl Lw Mk Mm Mr Nb Nl Nn No Nr Nv Pa Pc Po) Nc(Is Iv Jl Lh Mp Mu Nb Nf Nn No Nv Oh Pc Pf Po Qe) Li(Hw Is Iv Jl Lw Mi Mk Mp Mr Nr Pa Pc Pe) Pb(Im Ir Is Jl Lw Mm Mp Mx Nl Pf Po Qa Qe) Nh(Is Jl Lh Mn Nf Nn No Oh Pc Pf Po) Mi(Jk Js Lw Mr Mz Nn Og Ok On Po) Nl(Et Ji Mm Mp Mv Nb No Oh Po Qe) Hv(Hw Iv Jq Lh Mk Mr Nr) On(Hu Lh Md Ms My) Fr(Mk Nr Pa Pe) Jp(Is Lh Mx Oh) Lw(Hu Lx Mx) Fp(Iv Jt) In(Hx Po) Pe(Il Mu) aA(Jg Ji) MpNd} In{Pb(Hu Hw Hx Ik Is Jp Li Lj Mr Mt Mx Nb Nh Nn Nr Nv Pa Qa Qe) Mr(Ik Is Jp Li Lj Mf Mt My Nh Nn On Qa Qe) Iv(Hu Ik Is Jp Mf Mt My Ne Nn Nv Qa Qe) Hw(Hu Is Jp Li Mt My Nh Nn Nv Qa Qe) Pa(Hu Ik Is Jp Li Mt Nn Qa Qe) Pe(Hu Is Jp Li Mt Nn Nv Pc) Mk(Is Li Mx Nh Oh Qa Qe) Nb(Fr Ji Mx Nn Oh Qa) Hx(Is Jp Li Nt Nv Oh) Fp(Is Nn Nr Po) Mi(aA Jo Mn) Mj(Ik On) Hu(Is It) Qe(Jl Nr) Lh(Ne Nh) MpIt MuIs NfHv JlLj} dA{Bo(aF Ao aQ Ax bF bU cG cL Co Cq Cs dH) bN(aQ aW Bn bU cE cL cR Cs De fR) dN(aF bF bR bU bW cA cG cL De dI) cT(aE aF bR cG Ch cO dB dE dI) Cs(Ao aQ Bn bU cE Co Cq) cP(aF Bg bQ cG CO Cq) bV(bF bR bZ cA dH dI) Ao(Ad Ax Cv Dl fR) Af(aF cE cL De) Bn(aE aW Ax Bc) Cx(aF bU cE cL) cX(Bg Co Cq dE) De(aQ aW Bc) cN(bU cL dH) aA(bF bQ) aQ(aU bB) cE(Bc dF) cR(aF aW) dM(aV cK) CwaD bBdD} Mi{Jo(Hw Hx Ij Js Lw Md Mk Ml Mt Mv Mw Mz Nc Nf Ny Pb Pg Po) Ok(Ij Js Mn Mz Nf Og Pg Po Qc) Js(Ji Jp Li Nd Nw Qe) Li(Ij Mj Ng Og Qc) Nw(Lh Mz Og Po Qc) On(Jk Mj Nf Oe Oy) Nd(Mm Mt Pd Po) Ii(Ma Mn Pd Pf) Nr(Fp Ne Nh) Mf(Hx Og Pb) Ji(Mj Ms Nf) Jm(Fp Ly Pb) Fr(Mj Ne) Nn(Ng Oe) Mp(Jg Lw) Na(Iv Nc) Hq(Hu Pc) WmNt NqPg MbMg MlMy MvPc NcHw NgJp NhPe QaQc QeJk PdaA} Il{Iv(Hx Is Ji Li Lw Lx Nn No Nv Nw Oh Pc Pe Po) Mk(Im Ir Is Jp Li Lx Nh Nl Nv Pa Pe Qb Qd) On(Hu Jh Jk Mq Ms Mw My Nb Nn Nv Nx Ny Pa) Mr(Ir Is Jp Li Nh Nl Nv Pe Qa Qb) Pa(Ir Is Ji Li Mv Na Nv Oh Qb) Pe(Jp Ml Mu Mv My Nw Nx Pc Qe) Pc(Is Lx Nb No Nt) Mj(Lx Mu Nx Qe) Nw(Hw Nr) LxPf JgaA} Nw{Mj(Hw Iv Jl Li Lx Mk Mr No Nr Ny) Ne(Jn Lw Ml Ms Mw My Nr Nv Ny) Js(Is Iv Lx Mr Nr Oh Pa Pe Wm) Ii(Fr Hw Jl Lw Lx Mk Mr Nr) Og(Li Lw Ml Mt My Mz Ny Qc) Nh(Ms Mz Nr Nv Pz) Qc(Li Lw Lx Oh Qa) Fp(Mz Nn Nx) Lj(Hw Mz Nd) Wm(Hr Jr) Mb(Ml Nj) NnIj NrNc NuMt MdaA MmHv MzNv HwOh} De{Ax(aF aW bC bN bO cR CX) Ar(aF bC bN cN cP cR cX) aZ(aD aF aM aN bV cR) Cs(aF bC bN bO cR) Dk(aA aF Bc bN cP) aW(aA aM Bo bV cR) Ch(Ba Bg Cw Fr) aE(bC cP Cu Fr) aN(bJ cN cR Cw) bV(aX cS CV) fR(aG bC bO cV) Ao(Ap Bg) Cx(Cv Cw) aF(cP Cu) cV(aP cR) BaaM BobB FrbO aAaG aQcU cEdF} Lx{Js(Fp Jn Jp Li Lv Ml Nn No On Pf) Jo(Fr Jk Lw Mh Mm Mu Mv My) Mj(Fr Ji Li Lj Ok Pg) Po(Hv

Figure 17 Continued

Mu Nh Og Wm) Lz(Lh Md Mz Nf Nh) Pf(Hx Md Mz Nf Pg) Wm(Hr Nt Pg) Nn(Ij Mb Md) Hw(Fr Lw Og) Mb(Ji Nj) Na(Lw Mh) Ii(Ma Mz)
Ij(Fr On) Pd(Lv Nh) NrNu Mdlu MmNd MuNg MyJk JtOn OgPc} Bc{Ch(Ax aZ bO CS Cw fR) aD(aP Ax aZ bB bN bV cI) cP(aE aF Ao bN
bV cI cR) Bn(aZ bO cR Cs fR) Cs(bB bJ bN bO) aQ(bJ bV Co cS) fR(aG aW bN cE) Ax(aW bB bN) aE(Ao aP cN) aF(aZ cS dN) bV(Ao aX
cV) aP(aG bW) aZ(aN cE) bO(cS cT) cV(cR cT) AjBa aMbJ bWdG cEcS cGcN} Og{Fp(Hw Is Iv Jl Jq Jt Mk Mr Nb Nn Nr Pa Pb Pc Pe)
Hv(Hw Iv Jl Lh Mk Mr Nr Oh Pa Pc Pe) On(Hq Hr Hw Iu Jk Md Mj Nv Pg) Pb(Ir Is Lj Lw Mz Nb No) Nh(Hx Lh Lj Mv My Nn) No(Hu Ik Jr
Js) Pc(Hx Nv Qe) NnOk LwIk MfaA MuJi JgLj} Bo{Ax(aM bB bC bF bJ cG cV Di) aM(aF aW bB bJ bV cE Ch) cV(cB cP CS cT dN fR)
Ao(bJ bO cP Fr) Ch(aF bB bO dN) cE(Ba bQ cR dF) Cs(bB bC Co) aF(cB cP cU) bV(al bB cG) cT(aH aY cG) aQ(aU cU) aW(BN) bO(bN Cx)
cP(Bg Cp) aEbC aNbJ aPcG} Nn{Jo(Hw Iv Lh Mj Mk Nb Nr Pa Pe) Hw(Is Iv Jl Mk Mr Pa Pe) Ok(Et Ij Mj Ne Oe Qc) Jm(Fp Hv Ly Pb Pc) Nr(Fp Lj Nc Wm) Nh(Ji Lw Md Ne) aA(Mu Mv Nq Oe) Mb(Ji Lw Md) Fp(Jp Ng) Ne(Ji Jq) WmOi LvLj MdHv MpOn MsPb IiIp QcQe} bO{aP(aF aW Bn bW Ch cL Cs Cx) aD(Ax aZ Cw dF FR) Af(Ba cR Cw dD dG) Cs(bC BN cR cT) Cx(aE Ar aW FR) cT(aG aY Ch cR) dM(Ar Ax Ba Fr) Ao(Ar Bg fR) bN(dG fR) cE(dF dG) dN(cQ dD) BnfR FrcX aEaM aZbV cNcP} Wm{Mj(Fr Hx Ji Mu My Nv On) Hr(Fr Ji Jq Mp Mq Ok On) Ii(Hx Mn Mv Nm No Oh Pa) Mr(Fr Ji My No Pb) On(Js Lh Nt Oe Pd) Jo(Ma Mg Mv Oy) Na(Ji Mp Mq) Iu(No Ok Pb) Oy(Jh My Pb) Pg(Lv Mu) NoNt NrMy HqPb JtOk} Jg{Jt(Hw Is Iv Lw Mk Mr Nr Pa Pe) Ne(Hu Jh Lw Ms Mw My Ns) Hv(Hu Jh Mv Mw My Nr) Lv(Hu Jm Lj Mv My) Ly(Jh Mm Mw My) Pb(Lj Md Ms Mx) Mb(Mr Nr Pa) aA(Jk Nq Ns) Nu(Mv Ng) Nh(Md Ms) MxNd QcQe JnJs} bN{cN(aE aN Ax cP Cs cX dN) aD(aZ Ba cS dG dN fR) Ch(aN Ba Bg cS dN) Ao(Cu dG Dl Fr) Bn(Ar aZ Cs) bC(Ax Cs fR) cS(aN aQ bB) Ba(Aj cE) aM(aN Ax) aW(Cw dN) aZ(bV cR) aQaU bBdF bVcV cPdG dHdN} Fr{Hw(Is Iv Jo Mk Mr Pa Pe) Ch(aF bB bC Bn dN) Ng(Fp Hv Nh Nl Pb) Nr(Fp Hv Ne Nl) Ne(Ji Jq Lw) Nh(Hu Lj Md) Po(Fp Hv) Nl(Hu Md) Jo(Iv Pe) AodM CoCx FpLw MmNd IjOn QcQe JnJs aIcP cRcV} bV{aW(aQ bJ cE Ch cP cX) Bn(aX aZ cS CV) aD(aQ aX aZ cS cV) bB(aX cN cW dD dE) bJ(Ao aZ cS cW) dH(aA cN dG) Ao(Cv Dl) Cx(aZ cV) aM(aZ cS) dE(aX cV) dN(cG cS) ChCv aIdD aNcX} cP{Ax(aA aI bB bJ Bn Ch cR cT) Cs(aI bB bJ Bn cR cT) bB(cN cR dB dD dN) aF(Ch cR dE fR) Ao(Ap cT Dl) Ba(Aj Bg Co) aE(aP Cw) cE(bZ dG) ChaZ CuaI aKaQ aWcR bIcT cLdG cVfR} Js{Nb(Fp Hv Jp Li Lj Lv Oh) Is(Fp Jp Li Lj Mb Nh Oh) Lv(Jl Jt Lh No Po) Oh(Iv Nh No Pa Pe) On(Hu Iv Li My) Jn(Jp Mp Mv) No(aA Fp) Li(Iv Nr) PoJp LjNv} On{Mj(Mv Mw Mx My Nb Ng) Jq(Fp Jh Mw Nb Nv Oh) Hr(Jk Md Ms Nv) Hu(Ij Pb Qc) Nx(Nd Nh Nq) Ms(Nv Po) My(Io Nm) Ij(Li Oh) NrNc MbNj MdPc MvIu JtNv} cT{cV(aE Ao aP aW aY Ch CS dB) Ao(aD aF Ar Ax Cs) Ax(aD aF bJ cG) aY(aF bJ cG) Co(bJ Cs) aE(aS cW) aG(cN cS) cG(aR dL) ChDk CsaF bPcR} Hv{Mm(Mk Mr Mu Nr Pa Pc Pe) Na(Hw Iv Mk Mr No Nr Pa) Hw(Hr Jl Lh Pc Pe) Ji(Jq Lw Pb) Nr(Li Oh) Ng(Mg Mv) Pb(Hq Jq) MdNv MpOz IiLh} Lv{Mm(Hw Is Iv Mk Mr No Nr Pa Pe) Lj(Jq Lw Nr Pc) Fp(Jl Lw Pb) No(Md Na) Mp(Hq Oz) Ji(Jl Jq) Jm(Is Nv) MaNg MdPc HqPb} Jp{Nd(Is Ji Jl Lh Mm Nb Pa Pe Po) Hw(Jl Mb Mr Pa Pe) Mb(Mk Mr Pa) Ji(Ly Qc) Pb(Fp Lw) NrNa MdPc MkOy MuNg NeJq} Cx{cR(aN Ar aZ bJ Cs fR) Ba(aM Bg cL) cE(bQ Cu Cw) Ch(bJ Cu) bB(aQ dD) fR(aM cV) AoBb AxaE CvbJ aDaZ aFcN aIdD cGdF} Ao{dM(Ad Bb Bg Dk) Ap(aE Ch cR) Cu(aF Bn cR) Cw(aA aM Cs) aP(aF Cv Dl) Ax(Ba bJ) fR(aF cV) BbaJ CsbJ DlaZ} Oh{Ii(Et Hw Hx Ij Iv Mk Mr Nr Pc) Hw(Hx Lw Pa Pe) Nr(My Ne Nh) NmaA MzNd NeNh NgIk JqOk} cE{dF(aD aW cX dN) Ba(Aj Ch cS) aZ(cN dN fR) aA(Ar Cs) cS(bG cN) dG(aE aW) AfbQ AxaP BgCh CudN bCfR} Mp{Mb(Hw Hx Iv Jq Nb) Ne(Hq Oz Pd Pf Pg) Fp(Hq Md Pd Pf) Nd(Hx Pb) NsNu MdNh HwHx OkaA} Bn{bC(aE aW bW Cs fR) Ba(Aj aW Ch) cV(aP cR fR) Cs(aM bJ) aN(aZ fR) CwaD aEcR aMaZ} Nu{Nr(Fp Jl Jt Lh No Po) Nd(Hq Md Pd) Pc(Ms My Ns) No(Jr Mc) Ng(Jt Lh) MdHx JlJq} Af{dD(aI bB bE bJ cZ) Dk(aW cN cR Cv) Ax(aD aE) aF(cN cQ) CubJ aEcN aMdB bBbQ} Pb{Ng(Li Mt Mu Mv Nv) Nh(Ji Jq Lj) Fp(Jl Mm) Ne(Ji My) Ok(Jt Pd) MdNv MkOy MmLj} Ch{Bg(aI aW bB cS) Cw(bJ cV dN) aW(Ba bC fR) bC(aE Ba) bJ(Cs dG) aFbQ aQaU} Ax{aQ(aH aI bB) dM(aA bB cV) aF(aI fR) aM(aE bJ) cR(aW cV) aAaD aPcG cWcX} Nv{Ii(Hw Mk Mr Nr Pa Pe) Hw(Lj Lw Mk Nr) Md(aA Ml) NgNh QcLj} Mu{Ms(Nb No Pc) Na(Iv Mr) Ji(Jq Lj) Pc(Md Mv) MbJl NeNh NgLi QcQe} aA{Mq(Md Nj Ns) No(Md Na) Jq(Ly Mf) aD(bC Cs) ArcV NqLh MbJi} bB{Ba(aD aE aF) Cs(aM aP aQ) aP(aD dD) aQ(cU fR) CuaF cNdD} Hx{Hw(Jl Lj Lw Mk Nr Pf) Nd(Lw Mm) NeNh} Ok{Pc(Ii Jq Nf) Md(Mb Oe) Mj(Li Mx) FpJq MqOe} cR{aF(cN dE dN) aE(aZ cW) cV(dG fR) aDaZ aNcN} Ba{Aj(aD bJ cV) dM(aE cV) aMaW cNdH} Mb{Mm(Jl Md Mk My) PoMd LwLh JiJl} Nh{Nr(Li Lj) Ne(Jq Lj) MdNb MvNg QcQe} aQ{aU(cN cS dG dN fR) CsbJ aDcU} Fp{Jo(Mk Mr) NoJr NrMy MdNb QcJi} Nd{Lw(Is Li) Mm(Is Nb) MvMz MyLj} Qc{Qe(Jl Nb Pc) Ji(Li Lj)} aM{aE(aZ bJ Cs) cV(Cs fR)} Hu{Ng(Qa Qe) NrLj MdPc} Ii{Ir(Jl Lw) LzPe MmIs} cX{cN(cL dE) CoCw bWdG} aF{aP(aE Cs) dEdG} fR{aDaJ aWbC cVdN} Nr{Lj(Mv My)} Mk{JiJo LiOy} aI{dD(aP dN)} ArcVdM CsaNbJ LwNeNj MdMxPc MrIsJo bCbWdG Constrained panels with 3 analytes, where 1.0E-3 >= 'AUC p-value' > 1.0E-4. Contains 2,848 panels of 597,622 total panels evaluated. :
Ni{Mr(Fr Jg Ji Lw Mt Mu Mv Nc Ne Nh Nl Nn Nv Nw Oh Pb Wm) Hw(Fr In Jg Lw Mp Mu Mv Nc Ne Nh Nl Nn Nv Of Oh Pb Pf) Nr(Jg Ji Lw Mt Mu Mv Nc Ne Nh Nl Nn Nv Nw Oh Pb) Mk(Jg Ji Lw Mi Mt Mu Nc Ne Nh Nl Nn Nv Nw Oh Pb) Pa(Jg Ji Mt Mu Mv Nc Nh Nk Nl Nn Nv Nw Of Oh Pb) Iv(Fr Jg Ji Lw Mp Mt Mu Mv Nh Nl Nn Oh Pb) Pe(Iq Jg Ji Lw Nc Nk Nl Nn Nw Oh Om Pb) Jl(Fr Jg Ji Lw Mi Mu Nk Nn Nw Of Oh) Nl(Ii Ij Jq Jt Mj Mn My Mz Nf Pc) No(Hx Jg Ms Nn Oh Om Pb Pc Qe) Nc(Et Ii Ij Jq Jt Mj Mm Mv My) Md(Jg Mp Nb Nn Nv Om Pc Po) Oh(Hx Lh Lw Mj Mu Nb Pc Po) Mi(Hx Mh Ml Mt My Nb Pb) Mp(Hx Ir Mt Nb Of Pc Qe) Lw(Is Ji Mu Nb Nk Nn) Ne(Ii Ij Jt Mj Nf) Nk(Et Lh Mz Om Pc) Lj(Jq Jt Lh Oy) Of(Ij Oy Pd Qb) Pb(In Jt Lh Mj) Hx(Mm Og Pf) Is(Mu Nn Og) On(Mv Mw Nb) Pc(Ir Mx Pf) Lx(Nn Pd) Mj(Jg Nv) Nh(Ij Jt) aA(Jq Mm) PoJs MsJg NbPf QaQc QbOm} Om{Mm(Hw Ij Ip Is Iv Jl Jt Mi Mj Mk Mr Mx Nb Nk No Nr Pa Pc Pe Po) Mi(Hq Hx Ij Jk Js Lw Md Ml Mv Mw Ny Of Oy Pb Pc Pd Po) Qe(Fp Hw Hx Iv Jq Jt Mj Mk Mr Nb Nr Pa Pe) Et(Hw Iv Jl Mj Mk Mr Mx Nb No Nr Pa Pe) Nk(Fp Ip Ji Mp Mx Of Pd Pg Po Qd) Pb(Fp Hv Hx Lj Mx My Nt Of Qd Wm) Mt(Hw Iv Jq Jt Mj Mk Mr Nr Nw) Mv(Hw Iv Jl Mk Mr No Nr Pa Pc) My(aA Hv Hx Is Mx Nb No Nw) Lj(Hv Iq Ji Lw Md Mp No Po) Pc(Hv Ma Mx Nh Nt Pe Pf Qd) Is(Hw Lh Mk Mr Nr Pa Pe) Of(Ik Ip Lx Md Nl Oy Qd) Jl(Fp Hv Ji Ma Mx Pe) Lv(Fp Ij Ji Lh Po) Mz(Hv Hx Lw Mp Mx) Nb(In Ma Md Mp Pf) Wm(Hr Iu Nm Oy) Pf(Hw Iv Jq Mr) Mx(Hx Jh Mn) Ne(Jq Ma Mn) Ng(Fr Hu Nh) In(Iv Pe Po) Iq(Ir Qa Qd) Fp(Hv Mp) Lw(Hx Pe) Lx(Ji Js) Md(Jo Jp) NoHv MaIv MpIp NfJh NhJq HxIr} Iq{Oh(Et Hw Hx Is Iv Jl Jq Mj Mk Mm Mr Nb Nr Pa Pc Pe Po) Hv(Hw Iv Jl Jt Lh Lj Mj Mk Mr Nr Pa Pc Pe Po) Qe(Hw Iv Jl Jq Jt Mj Mk Mr Nb Nr Pa Pc Pe Po) Is(Fr Hw Iv Jl Li Lv Mk Nb No Nr Nw Pa Po) No(Hx Ir Js Lj Lv Mm Mp Mt Na Nk Pb) Qa(Hw Iv Jl Mj Mk Mr Nr Pa Pc Pe Qc) Lv(Hw Ij Iv Lh Mj Pa Pc Pe Po) Ir(Jl Jq Lw Mk Mm Mp Nb Nr Pc) Mv(Et Hw Iv Jt Mj Mk Mr Nr) My(Hw Iv Mi Mj Mk Mr Nr) Hq(Ji Jq Mm Mt Mx Mz Nk) Lw(Fr Hx Lj Mt Nw Pb) Lx(Js Md Na Nk Of Po) Ji(Jl Jq Li Lj Og Pb) Mp(Et Hx Lj Md Pd) In(Hw Hx Lh Pa Pb) Li(Hw Hx Jq Pc Pe) Nw(Lj Mk Nr Pc Wm) Mt(Iv Mk Mr Pa) Nb(Et Mm Nk Pb) Jt(Jg Jp Nv Pb) Nk(Im Jk Qb) Mm(Hx Lj) Il(Mk Mr) Jl(Mj Pb) Nv(Lj Ng) MiMl HxPf JgJq} Of{Et(Hu Hw Is Iv Jl Lh Mj Mk Mp Mr Nb No Nr Pa Pe Po) Ma(Hw Ii Ij Iv Jl Ly Mk Mr Ne Nk Nr Pa Pc Wm) Mv(Hw Iv Jl Jt Lw Mj Mk Mm Mp Mr No Nr Pa Pe) Nh(Hw Iv Jh Jl Jq Jt Nb Nf Nr Oy Pa Pc Pe) Fp(Is Jt Lh Lw Lx Mk Mr Pa Pc Pe Po) Ji(Hw Iv Jl Lw Mk Mr Nr Pa Pc Pe) My(Ii Ik Iv Jt Mb Mj Mk Mr Pa) Nk(Hu Ih Ik Lh Lw Lx Mp Nx Pg) Pb(Hu Jl Jt Lh Lw Nb No Po Qd) Mp(Hu Ip Mz Nd Nt Oy Wm) Nb(In Jp Lj Md Ne Og Wm) Mi(Hq Il Jk Md Pd Pg) Mm(Ip Is Lh Lx Mu Oy) Jq(Ir Lj Mt Mu Pf) Pc(Hv Lx Nt Pe Qd) No(Hu Hx Ik Jr) Pf(Iv Jt Mr Pa) Hu(Hx Ip Is) Oy(Lw Mx Mz) Po(In Lj) Mt(Jt Nw) Hv(Jt Mk) WmOg NtHx LxJs LyIr MnNe MqNw

Figure 17 Continued

MzHq IsLh JILj} dA{aQ(Ao bF Bg bJ bQ bR bW cA cD cF cG Ch cO Cq cR dB dE dH dI) Cs(aF aW bF Bg bJ bQ bZ cA cG Ch cL cO cR dH dI) Cx(aV bF Bg Bn cA cG CO De dH dI fR) Ax(bF Bg bN bU cA cE cG Ch cL Co Cq) Bn(AF aK aN Ar aV aZ Cw Fr) cE(aK aV aZ bZ cR Cw cY dG Fr) cL(aK aU aV aW aZ Bc cY dG Fr) cT(aV Bg bJ bQ cA cF Co Cq) De(aF aK aN Ar aV Ba Cw) bU(aK aP aU aV aW Bc cY) dN(aE aV Bg bQ cK cO dB) Bo(aM aW bQ cA cO dI) Ao(aF Ar Bb bO Dk) bN(bF bR cG Cw dI) cN(bF cA cD cG cO) Af(aV bF cG Co) aW(cC cF Ch cK) Bc(Bg Co) Ch(Cw Fr) aE(aK dD) aF(dE fR) dG(bW dH) AjBa BgFr aNcR aPcO aVcP bBcW cSdI} Nk{Nn(Hw Is Iv Ji Jl Lw Lx Mk Mr No Nr Nw Pa Pe) Oh(Jg Jl Lw Mk Mv Nb Nw Og Pa Pc) Lx(Ii Ij Md Nf Oy Pc Pd Pg Po) Mt(Hw Iv Mj Mk Mr Ng Nr Pa Pe) Lj(Hw Iv Lh Mk Mr Nr Pa Pe) Nv(Hw Iv Mj Mk Mr Nr Pa Pe) Pb(Is Jl Lh Lw Mm Mp Nb Po) Wm(Jg Ji Jq Mp No Og On) Mb(Hx Is Mz Nb No Pc Qb) Qa(Hw Iv Mk Mr Nr Pa) Og(Hu Ik Mi No Nw Pd) Fp(Is Jt Lh Li No) Mu(Is Ji Ng Pc) Hu(Is Mx Mz Ng) Fr(Iv Mr Nr) No(Jp Li Nw) Mi(Ii Js Ok) Nl(Ij Jt Mj) Hx(In Mm Mx) Qe(Lw Mk Mr) Jg(Ir Md Ms) Ng(Ik Nt) Jt(Ne Nh) On(Mw My) Pc(Mx Nj) MvIr NbIn NwNy} Mi{Ok(Hr Hx Il Jk Lx Md Mt Mv Mw Nx Ny Oy Pa Pb Pe) Nw(Hx Ij Jk Ml Ms Mv Mw My Nb Nf Ny Pb) Js(Lx Lz Mn Mp Na Nn No Ns On Oy Pf) Li(Ii Jk Lh Mv Mw Mz Nf Nr Oy Po) Nr(Jp Lx Ly Na Nn On Oy Wm) Nn(Jk Mj Ms Mv Mw Og) Mn(Ij Il Md Mv Nf Pg) Jo(Hu Jk Jl Mh Mm My) Na(Ij Is Mj Mw Nf) Mp(Ij Mv Mw Ny) Hw(Hr Mv Og Pd) Po(On Pc Wm) Mj(Is Jk Md) Oy(Iv Nc Nq) Ns(Ij Nf) Lz(Mw Nf) Mf(Mg Ml) Nd(Mh My) Ng(Fr Jg) Nh(Jm Mt) Il(Jr Pd) Og(Ji On) NqPa LvLx MsOh MwPc HuJm} Og{Nh(Hw Ii Ij Is Iv Jl Jt Mk Mr Nb Nf Nr Oh Pa Pc Pe) Li(Hw Is Iv Jg Ji Jl Jq Mk Mr Nb Nn Nr Pa) Pb(Iv Jl Jq Jt Lh Mk Mr Nr Pa Pc Pe Wm) Mu(Hw Is Iv Jl Mk Mr Nb Nr Pa Pe) Ne(Hx Ip Mz Nb Nf Nn Oy Pc) Ji(Fr Jl Lx Mk Mr Nn Nr Oh) Jg(Hu Jh Md Mv My Ns Oh) No(Md Na Nv Oy Pc Qe) Jq(Hx Lj Ly Nl Nt) Pc(Is Lj Lw Nb Nt) Wm(Hr Iu Lv Na) Nb(Lj Lw Md) Fp(Ii Ij) Hu(Mz Pa) Nv(Iv Nr) Nw(Mj Oh) NnLx LwQe MbJl MmIk MvPe NdHx IsJs} In{Mu(Hw Hx Iv Lh Mr Nb Pa Pb Pe Po) Nr(Ik Jg Lw Lz Md Na Nn Nv Qa) Iv(Fr Hw Jg Ji Jl Lw Mp Mr Mv) Mk(Ir Lw Mt Ne Nn Nt Nv Pe) Hx(Fr Ji Jl Lw Mt Ne Nn Qa) Hw(Fr Ir Mb Mx Ne Nt Pe) It(Ii Jg Nf Nh Nn Nv Po) Pb(Fr Ir Ji Lh Lw Ne Nt) Mr(Hu Ir Lw Ne Nv Pe) Is(Ik Jg Jl Nn Nv Po) Fp(Ij Jt Lh Nf Nv) Po(Fr Ji Nn) Nv(Lj On Pa) Pe(Fr Ji Lz) Nb(Lw Md) Nh(Jt Nf) Ij(Lj Mx) Jl(Oh Qa) Pa(Ne Pc) NnLh MjOh} Js{Oh(Hw Hx Ji Jl Jn Jp Lh Lw Mj Mk Mr Ne Nr Pb Po) No(Hv Jp Li Mb Mf Ml Ne Nh Nn Nw Ok On Wm) Lv(Hw Hx Is Iv Mj Mk Mr Nf Nr Pa Pb Pe) Nn(Hx Is Iv Jn Mj Nb Nr On Pa Pb Pe) Nv(Hx Is Iv Jn Mb Nr Pa Pb Pe Wm) Fp(Hx Iv Mj Pb Po) Jn(Jl Li Lj Nh Pc) Nb(Mt Nh Qa Qe) Iv(Hv Lj Qa Qe) Li(Hx Mj Pa Pb) Lx(Ji Na Wm) Is(Mt Ne Pe) Jp(Hx Mj Pb) Lj(Hx Nt Po) On(Mv Ng) WmJr NrHv MpNd MsNw QaPe QePb} Nw{Wm(Hq Hw Hx Ij Ir Iv Md Mz Nr Nv Nx Oy Pg Pz) Mj(Il Is My Nn Oh Pa Pe Pf) Ij(Hw Iv Jl Lx Mk Mr Pa Pe) Nv(Fp Fr Hq Hx Mu Nc Nl Nn) Nx(Hq Hx Li Nc Nl Oh Pc) Nf(Hw Mk Mr Pa Pc) Nn(Lj Md Ng Qc) Il(Jl Mk Mr Pa) Pg(Iv Mk Mq Mr) Ms(Hv Nc Qc) Mw(Hv Nh Nl) Pc(Lw Md Oy) Mq(Hq Hx) Mz(Nc Nl) NrNa LvMy LwNh LxLh MkOy MpPd MtNe NcJn HxPz} Ao{bO(Ad aM Bb bC cS dF DG Dk Dl) bC(aA Ap bN Bo Cu Cw Dl fR) cR(aF Ar Ax Bg Bo Cs Dk Fr) Ax(aA aP Bc bN Cv Cw) Bb(aM aP bJ bN cP) Cu(aE aM bB cP dN) Bo(aM Cv Dk Dl) Cw(aI aW bB fR) bJ(aQ bG dF dG) Dk(BN Cx) Dl(aE cN cS) Fr(aF bV cP) Ap(aM aW) Ar(aA Bc) Cs(aP Bc) Cv(Bn De) BgaM aAdN aPcP cVdF} Nn{Nr(Hw Ir Iv Li Lx Mh Mr Mx Pa Pe) Ng(Hw Is Iv Jl Lh Lx Mk Mr Pa Pe) Il(Lx Mj Mk Mr Pa Pe) Fp(Ji Jq Ok Pa Pe) Lx(Jk Mj Oy Pg) Mb(Jl Mk Mr Pa) Md(Jp Li Ok Pc) Hr(Hw Mr Pa Wm) Oe(Hw Mk Mr Pa) Ji(Jq Mp Qc) Jm(Ir Lj Ns) On(Jk Lh Oy) Fr(Jk Nq) No(Pb Pc) Mv(Jp My) Jo(Jt Mr) Ok(Nf Nx) Pg(Pe Wm) MkOy MuJp NhLj} Wm{Oy(Lx Mp Mt Mv Mw Nb No Nq Nv Pa Pc) Hq(Fr Ii Lv Mu Mv My Nv) On(Hw Jk Ms Nf Nr Nx Po) Pg(Fr Mp Mt Mw No Nv Pb) Mj(Jg Jq Mq Mv Pb) Mr(Mp Mq Mz Nv Pa) Ij(Fr Mv No Nv Ok) Nr(Im Lx Nu Pb) Nt(Ji Jq Nm Nu) Md(Fr Mt Nv) Ii(Ma Pb) Iu(Im Jq) FrMk NmOk LyMe NaJq NcNl} Fp{Mm(Hw Is Iv Jl Lh Mj Mk Mr Nb No Nr Pa Pc Pe) Lv(Hw Iv Mk Mr Nr Pa Pc Pe) Jp(Hw Jl Lw Mk Mr Nr Pa Pe) Na(Hw Is Iv Mk Mr Nr Pa) Pb(Hw Is Iv Jq Lw No Nr) Jg(Hu Ms Mv My Ng) Mj(Is Ji Lh) Md(No Nv) Pc(Is Lw) NrMv MpOz NgNv NjLi HrHw JlJq JtOk} Il{Mk(Fr Jg Ji Lw Mb Ml Mp Ne No Oh Ok Pf Po) Mj(Ir Is Jp Li Lw Nh Nv Pc Pe) Ij(Hw Ir Li Lw Ne Nl Nr Qe) Mr(Fr Jg Ji Lw Mb Mp Oh) Pa(Fr Jg Lw Lx Ok) Pe(Is Jg Lw Lz) Iv(Fr Jg Jq) Qe(Hw Jl Nr) Lx(Lw Lz) Nb(Md Nq) Pc(Lh Lz) NrNa NsJl MuIs} Ng{Hu(Et Hx Ir Is Jl Lh Mm Mp Mt My Po) Li(Hw Iv Jl Mk Mr Nb Pc) My(Et Ik Jl Lh Mg Nt) Jp(Lh Lx Mg Mv Nt Po) Nh(Jh Lh Ma Oy) Ik(Et Hx Lw Mm) Jg(Lv Lx Ly Md) Fr(Lj Nd On) Mt(Iv Nb Oy) Mu(Is Lh Pe) Mg(Lj Ne) NtPb LxMf LyMv MaNe MdNv NbIm} bO{aD(Ar Ba Bo bZ cR cS dD dG dN) Fr(aE bB BN bV Ch Co) Ax(aP bB BC bN bV) Bo(aE aM bB cE cR dN) dG(aE Bn bW cL De dH) Ar(aM BN cR De) cN(Bn cR cS De) fR(aF aW Bc Ch) aM(cQ cS Cx) Cs(aF aW) De(aW dN) AfCu AjBa BccR ChcS CwdM} Hw{Oh(Is Iv Jl Jt Lh Mk Mr Nb Po) Is(Jl Lw Mk Mr Nb Nr Pa) Hv(Iv Mk Mr Nb Nr Pa) Hx(Iv Mj Mm Mr No) Lj(Jl Lh Lw Nb Po) Nv(Iv Mr No Pa Pe) Hr(Li Mu Mv My) Jo(Et Lw Mp) Na(Li Nh) Oe(Fr Jg) NuJq MbJi MmIi NhPb LhOn} bB{Cu(aD aE aQ Bn Ch cW dD De) cW(Ba cN cR Cs cU dF) dD(aE Bc Bn DE dG) aF(Ax Bo Cs Cw Fr) aQ(Bo cN Cw dF dN) Ba(Aj aM aW cN) dE(aM cN cS dG) aD(aZ bV fR) cR(cN dG Fr) Ax(aM aP) CsbV CwaE FraZ} Ax{bJ(aD aN aQ Bc bV Ch De) bN(aD aE Bn cE Ch cP) Ch(aP bC Cw dN) aM(aW Bn bV cV) cE(Ba bV cN cR) aA(aG cG Cq) bC(Bn bW cP) cR(Bc bZ cG) cV(cT dN fR) De(aE bV) aP(aF dH) BnbV BoaH aEcT aWcP} Pc{Md(Fr Hv Jg Li Lx Mb Nb Ok) Ns(Fr Hv Lv Mu Mx) Oy(Fr Hv Lx Mx Ok) Ne(Ji Jp Jq Mm) Lv(Jq Mv My) Lw(Li Nd Nh) Mu(Jh My Oi) Ok(Hr Nx Oe) Ms(Hu My) FrMv LxPg LyMm NhJi IiIr} Ch{bJ(aM aN aQ aZ Ba Bg bN cS dF) aZ(aF bN dG dN Fr) Dk(aE bN Cx dK) aW(Bo Cu Cw Fr) bC(Bg bW Cw) cR(aE Bc bN) Ba(aM aP) Bn(Bg dN) ArbN CuaE CwaM aQcU cEdF cVfR} Nr{Nh(Fr Lx Na Nl Pb Pe Pf) Lj(Fr Hv Ik Jg Mt Ne Nv) Lx(Jl Mk Mr Ne Pe) Oh(Fr Jp Mt Mv Nl) Lv(Jq No) Na(Li Mt) Ji(Mb Mj) Jo(Et Lw) FrNc MmIi NePe HvPf JgOe LiPb} cE{cN(aQ bG Bo bZ cX dD dN) bQ(aD aE Bc bN cS) Cs(bV cR dN fR) Ba(aE aW aZ) Cw(aZ cR dN) Fr(aZ bC) bN(bZ cS) dF(Bc Bn) dN(Bo dD) CubC DebZ aMbF aQcU cRcS} Jg{Pb(Hu Jh Mv Mw My Ns) Nh(Hu Jh Mw My Ns) Jo(Lh Mk Mr Pe) Oe(Mk Mr Pa Pe) Ii(Hx Lx Mm) aA(Hu Mv My) Md(Li Lj) Qc(Qa Qd) Jt(Mj No) LvJh LwLj NeJq} Mp{Pd(Hu Jp Lj Ly My Nh Pb) Md(Jp Lj Ly My Nl Pb) Nd(Lw Mu Mv My Nh) Nh(Hq Oz Pf Pg) Mb(My Nj Ns) Hq(Lj Ly) Jo(Mr Pa) NsHv MyPg OzPb} cR{cX(aE aW bN cN cW dE) Bn(aN Ar aW aZ Cs) aF(aD aE aZ cW) aQ(aE Af aP) bN(aM bC cV) Bc(aP aZ) De(bC bJ) aD(cN Fr) aN(aZ bJ) CwcV aWdN dGdH} Cs{aW(aM bC bJ BN cP De) bV(aM bJ Bn cV) Bc(aD Co cP) bC(aF bW cP) cV(aP dN fR) Co(aA aP) bJ(aD aF) BoaM aAdH bNcP cGfR} Jo{Et(Iv Mk Mr Nb Oy Pa Pe) Lw(Iv Lh Mk Mr Pe) Mr(Fr Ji Mu Oh) Jt(Fr Nv Oh) Mu(Pa Pe) LxMt MkOh MmPe IkPa} Jq{Lv(Iv Jl Mk Pb Pe) Ne(Lj Mm Mu Oh Pb) Nu(Mk Mr Pa) Mb(aA Jl Mm) Md(Hv Jp) Pb(Lj Oh) FrJi LyMm MuNh MvOn QcQe} De{Dk(aP aW cN CX) bJ(aF aQ aZ Ba Cu) Ar(Af aM aW) aF(cN cU dE) Cw(aM aW) aE(aZ cN) cV(dF dG) FraW} aD{bN(Ar bC Bo cN Fr) fR(aF aW aZ bC cV) aZ(aW Bn dN) Cw(Ad aI) bJ(Cu dF) AraA BaaE BnFr bVdN dGdL} Md{Nb(Fr Jp Li Lw Mu Pb) Jp(Hx Ii Nv Pg Po) Mb(Et No Nv) Lv(Nd Po) Lx(Fr Lw) MqNh MuHx LjNv} Nd{My(Is Jl Lh Mx Mz No) Lw(Ji Lh Lj No) Lv(Hq Oz Pd) Mm(Jl Lh Po) Mb(Hq Pd) NuOz} cN{aN(bJ Bn cX dE) Ba(bF cG Co) aE(Bn cP cX) cL(Bo Cw dN) aF(Bn dE) bW(bC cW) CwcG aIdD} Ji{Mj(Iv Jl Li Mk Mr Nb Pa Pe) Mb(Iv Mk Mr Nj Pa Pe) Lw(Ne Nh) FrNh QcOh} Lx{Lz(Hx Ij Lj Mh Ml Pg) Pf(Ij Lh Ml Pb) Mj(Hq Oh) PoNe FrJk NaNy LhOz PbPd} cV{fR(aE aF aW Bc bN cS cT) aE(Bo Cw Fr) bV(aW bW cP) AjCw BndG bNcS} On{Nx(Jk Oe Ok Oy Pg) Hr(Mv Mw My) Mj(Jm Ms) PoLw MmJt MsHq MwIo NbaA} Bn{aM(aW Ba fR) aQ(bJ cU dN) aZ(aE aF bC) Ar(BC) aFcU aNbJ aWbV} Mm{Ii(Fr Iv Lh Nb Pa Pe Po) Jl(Hv Lv Pb) NoLy HvIv} Nh{Pb(Mk Mr Pa Pe) Nl(Iv Mr Pa) No(Jr Na) FrLw NaIv} Ba{Bo(bF Bg Co Cp) Co(aF Bc) cP(Ad bF) AjbC cLdN} Qc{Qe(Mk Mr Pa Pe) Ir(Fr Lw) Qa(Nb Po)} dN{Bo(aF bF cB) aF(cQ dE) dH(dG fR) DgDl} Fr{Oe(Mk Mr Pa) NqLi MjMx MwNb} No{Mb(Jr Mc) aA(Jr Lz) LvMc NaNe} aG{Cw(bV fR) cT(aS bE) AraA BcaZ} aQ{aU(aE aM) cU(aW dE) bNdJ cLfR} cX{bN(aW cQ) CoDk CqCu aNdE bVcW}

Figure 17 Continued dG{dH(aE aW dE) aldD aNbJ bVbW} Jm{Hu(Oh Qa Qe) MyQe IsPb} Bc{aZ(aM cL) AjfR CoCw} Ii{Lh(Ir Ma Mz) HvJt} aF{CuaI aZfR cPdI cSdE} dD{al(cP Cw) aEaM aNbE} Ar{aA(aM dM) bFcT} Bo{BgDk aEcP aWbC} DI{Dg(bV cS) aEaZ} Mb{Nj(Hv Ok) PoMI} Na{Iv(Li Lj Lw)} bJ{AjCw bNdL bPcT} Mj{MxLi OhOk} Mu{MwNb HxNy} Lj{HuJh JtOk} bN{bEcW cLdF} bV{aKaU aWaX} CxaMdB LvHxNy MkNvOy HqLiPb bFbPcT Constrained panels with 2 analytes, where 1.0E-7 >= 'AUC p-value' > 0. Contains 142 panels of 14,881 total panels evaluated. : Jj(aA Fp Fr Hq Hu Hv Hw Hx Ii Ij Ik Ir Is Iv Jg Ji Jk Jl Jo Jp Jt Lh Li Lj Lv Lw Lx Ly Mg Mi Mj Mk Mm Mp Mr Mt Mu Mv My Mz Nb Nc Ne Nf Nh Nl Nn No Nr Nt Nu Nv Nw Oh Ok Om On Oy Pa Pb Pc Pd Pe Pf Pg Po Qa Qe Wm) bA(aD aE AF aG aJ aM aS aW bB bF bJ Bn bO cE Ch cL cP cV Cx DE dM dN) aJ(AF BN bO Ch cP cT CX De dG dH dL dM) aA(Af bN Cx Fp Iq Lv Nu Pb Pc) dM(Af aQ BN cP cT Cx De) Om(Jg Nn Nw On) Mi(Lv Mb Nu) On(Ii Jt Of) cT(Af bB dN) BccX NnOf NuLv JoOk Constrained panels with 2 analytes, where 1.0E-6 >= 'AUC p-value' > 1.0E-7. Contains 43 panels of 14,881 total panels evaluated. : Lv(Hu Hv Jp Mk Mu My Nb Of On) aA(aF aO bA Bn cX Of Om) Nu(Fr Jp Nk Og On) cT(aM bA cE Cx) Bc(Af Cx dM) Mi(Fp Lj Ne) Fr(Hv Mb) Nv(Of Om) aE(aJ dM) bA(Ao bE) AffR FpMu NwOf aJaW Constrained panels with 2 analytes, where 1.0E-5 >= 'AUC p-value' > 1.0E-6. Contains 78 panels of 14,881 total panels evaluated. : aA(bJ bO cP De dM Lj Lw Lx Mi Ml Ng Nk Nx) Nu(Jg Li Lw Lx Mu Nn Nw Ok Pb) Lv(Fr Jg Jl Lx Ne Nh Nr Nw Ok) cT(aD Bn bV cL cN cP De) Of(Jg Jp Li Oh Ok) Af(aP Bo bV cP) Om(Jp Li Oh Ok) Fr(Ly Nd Pb) Mu(Hv Lj Pb) On(Hw Iq Jo) aJ(Ax Bc bX) dM(Bo bV dN) Lx(Hw Ni) Hv(Jg Nk) cX(Cs fR) BcbA CxcP WmIn MiIi JsNw aPcE Constrained panels with 2 analytes, where 1.0E-4 >= 'AUC p-value' > 1.0E-5. Contains 130 panels of 14,881 total panels evaluated. : Lv(Hx Is Iv Li Lj Lw Mj Mm Mr No Om Pb Pe) cT(aE Ao aP aW aY Bc bJ Ch dE) On(aA Fp Il Mb Ne Ng Nh Oe) Jp(Hv Iq Ly Nh Ni Nk Pb) aP(aD aF BN cP Cx De) bV(aM BN cE Ch Cx De) Af(aW Ba bC cN Cs Fr) Of(Fr Im Lx Qa Qe Wm) Om(Fr Im Is Mu Nu Qa) Bc(aA aW Bo Ch De) Hv(Jl Lw Mm Ni Pb) Nw(aA Ii In Ne Qc) Cx(aE Bo Cs fR) Nu(Is Ji Jl Pc) Mi(Iq Jo Nh Ni) Nk(Li Nc Ne Nh) Fr(Fp Ne Pc) Nn(Ii Iq Pb) Li(aA Ni Pb) cP(Bn dA De) Ao(aJ Ba) Wm(Hr Na) Jg(Iq Ne) Ok(Nm Og) aA(aD Nd) dM(bB Cs) BoDe LxIn MbMp MvLj aJfR bNdN Constrained panels with 2 analytes, where 1.0E-3 >= 'AUC p-value' > 1.0E-4. Contains 226 panels of 14,881 total panels evaluated. : Pb(Et Fp Is Jg Ji Lj Mv My Ne Nh Nt Oh Qe) Nk(Fp Fr Lj Mt Nl Nn Nv Nw Oh Qe Wm) Jp(Fp Iv Lw Mk Mr Mu Nb Nr Pa Pc Pe) Lv(Fp Hw Ji Jq Jt Mz Nn Pa Pc Po) On(Hr In Jk Md Mp Nf Nr Og Oy Pg) bN(Af Bc Bo cN cP cR cS Cx dG fR) Nh(Fr Jg Lj Lw Lx My Ne Nn Nw) bV(aD aQ aW aX Bc Bo cP cV dN) Nu(Hw Iv Jq Mk Mr Nr Pa Pe) Mi(Il In Jk Nc Nw Of Om Pc) aA(aG aW Cs Jg Ji Mm Ni Ok) cP(aW bB Bc Ch cN cR dB dN) Fp(Jg Jl Mm Mp My Nn Og) Iq(Fr Ir Li Nv Nw Ok Qe) Bo(aM Ax Bn Ch Cs dA) Hv(Ip Ji Nn Pa Pc Pe) Of(Ir Is Ji Mu My Pf) Af(aE Ar cR Cv Cw) Ne(Ji Lw Mm Nn Ok) Om(Et Ir Pf Qe Wm) aP(aE Ao aW bO Ch) Bc(aD aE Ao Bn) De(cN Cs FR) Ni(Is Lj Lw Oh) Il(Iv Lx Pa Pe) cT(aG Ax Cs dA) Cx(aN aW bC) In(Hx Iv Po) Og(Ji Mu Nt) cN(Bn cL cR) fR(aF Bn Ch) Ao(Cu Cw) Ax(cX dM) Wm(Iu Jo) Fr(Lj Nl) Md(Lx Nw) cE(dF dG) dA(aD aQ) CwdM NnNg LwHu MpNd MxPc MzNw QcQe JgLj JqOk aEaM Constrained panels with 2 analytes, where 1.0E-2 >= 'AUC p-value' > 1.0E-3. Contains 328 panels of 14,881 total panels evaluated. : Fp(Hw Is Iv Ji Jq Lh Lw Lx Mj Mk Mr Nb No Nr Ok Pa Pc Pe) Om(Hv Hx Ip Ji Lj Lx Ma Mm Mp Mt Mv Mz Ne Nh Nt Qb) Pb(In Ir Jl Lh Lw Md Mk Mm Mx Mz Nb Nk No Og Pe Wm) De(aE aM aN Ar aW Ax Ba bC bN cR Cw dA dN) Nn(Hw Iv Ji Lj Lw Mk Mr Nr Nw Og Ok Pa Pe) Mi(Hw Ij Js Li Md Mw Nf Og Ok On Pd Pg Po) Of(Et Jh Jk Lh Lw Ma Mt Mv Nt Pd Pg Po Qd) Nk(Hx Im Ir Jg Lx Mu My Nt Pe Pf Qa Qb) Cs(aF aM bB BC bJ BN bO bV cP) Ax(aA AF aP bB bC bJ bN bO cP) Fr(Ao bB Ch Hw Iv Ji Lw Mr Ng Nr) Nh(Ji Jl Jq Lh Mm Mv No Oh Pc Po) Ni(Hx Jl Lh Mp Nc Ne Nl Pa Pe Po) Lj(Iq Jl Jq Lw Mk Mp Nb Nv Nw Pc) Bn(aE aM aN Ar aW aZ bC bN dA) Ch(Ba bC Bg cN cS Cw dA dN) Og(Hu Hx Jg Mv Nb No Nw Oh) cR(aD aF aN aW Bc CX dA) Mu(Is Iv Lw Mr Ng Pa Pe) Iq(Hx Im Ji Lx No Pf Qa) Bo(aF Ao aW bB bO cE) Hv(Hw Iv Lh Mk Mr Nr) Li(Ji Lw Mk Nr Nw Pc) aD(aZ Ba bN Cw dG fR) dA(aE aW bN bU cE cL) Wm(Ji Lv Nr Ok On) Ne(Et Hx Jq My Mz) In(Hw Mr Nb Pa Pe) Jp(Hw Is Jl Oh) Nv(Md Ng On Pc) bN(aE aM aN aW) fR(Ao BC cV) Ba(Aj bB cE) Lw(Lx Nb Nw) Il(Mj Mk Mr) On(Lh Ms Nb) cN(aE bB cE) dE(aF aN cX) Ao(Ap Dl) Bc(aP bO) Lx(Js Pg) Md(Jg Ny) Hu(Mm Mz) Is(Js Pc) aA(Ar Jq) aW(aM dN) bV(aZ cS) dG(aE cL) CwcE MlNw MsJg HxPc aQaU bBdD bOdN

Figure 17 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.6E1 | 7.1E1 | 7.7E1 | 6.6E1 | 5.2E1 | 4.4E1 | 2.0E0 | 1.2E1 | 4.4E2 | 1.5E2 | 1475 | 23 | 252 | 23 | 0.44 |
| Ad | ug/mL | 3.4E-2 | 4.9E-2 | 6.8E-2 | 7.4E-2 | 8.7E-2 | 8.1E-2 | 6.8E-4 | 6.9E-3 | 5.4E-1 | 3.2E-1 | 421 | 17 | 165 | 17 | 0.57 |
| Af | ng/mL | 1.1E0 | 5.6E-1 | 1.6E1 | 4.7E1 | 6.2E1 | 1.3E2 | 1.7E-3 | 1.7E-3 | 5.3E2 | 4.8E2 | 421 | 17 | 165 | 17 | 0.48 |
| Aj | ug/mL | 1.8E0 | 3.6E-1 | 2.7E0 | 1.5E0 | 2.5E0 | 1.9E0 | 1.5E-3 | 5.5E-3 | 6.1E0 | 5.8E0 | 421 | 17 | 165 | 17 | 0.33 |
| Al | mg/mL | 8.7E-5 | 8.2E-5 | 2.5E-4 | 2.6E-4 | 4.1E-4 | 4.7E-4 | 2.5E-6 | 2.3E-6 | 2.2E-3 | 1.5E-3 | 421 | 17 | 165 | 17 | 0.49 |
| An | U/mL | 4.9E1 | 4.4E1 | 1.6E2 | 2.8E2 | 4.5E2 | 3.4E2 | 9.8E-4 | 9.0E-1 | 5.5E3 | 9.1E2 | 421 | 17 | 165 | 17 | 0.57 |
| Ao | pg/mL | 8.6E1 | 8.1E1 | 5.4E2 | 9.4E1 | 3.6E3 | 8.3E1 | 1.5E0 | 5.4E0 | 3.9E4 | 3.5E2 | 421 | 17 | 165 | 17 | 0.44 |
| Ap | ng/mL | 2.9E1 | 4.3E1 | 4.5E1 | 4.3E1 | 5.0E1 | 3.3E1 | 8.4E-5 | 3.2E0 | 3.3E2 | 1.3E2 | 421 | 17 | 165 | 17 | 0.54 |
| Ar | ng/mL | 8.5E-1 | 1.5E0 | 1.3E1 | 4.9E0 | 2.0E2 | 1.1E1 | 3.4E-3 | 1.5E-1 | 4.1E3 | 4.7E1 | 421 | 17 | 165 | 17 | 0.57 |
| As | ng/mL | 8.7E-3 | 1.0E-2 | 1.3E-2 | 1.2E-2 | 1.7E-2 | 1.4E-2 | 1.7E-3 | 1.7E-3 | 1.3E-1 | 6.1E-2 | 421 | 17 | 165 | 17 | 0.52 |
| Aw | pg/mL | 1.6E1 | 1.7E1 | 1.6E1 | 1.7E1 | 6.0E0 | 5.1E0 | 2.9E-2 | 1.1E1 | 4.8E1 | 2.7E1 | 421 | 17 | 165 | 17 | 0.57 |
| Ax | ng/mL | 2.0E0 | 6.1E0 | 1.3E1 | 1.1E1 | 5.3E1 | 1.7E1 | 1.9E-2 | 9.6E-2 | 7.7E2 | 6.0E1 | 421 | 17 | 165 | 17 | 0.59 |
| Ba | ng/mL | 5.7E1 | 1.3E2 | 4.1E2 | 6.7E2 | 1.1E3 | 1.4E3 | 2.7E-1 | 4.1E0 | 8.1E3 | 5.2E3 | 421 | 17 | 165 | 17 | 0.58 |
| Bb | ng/mL | 2.9E0 | 3.8E0 | 6.3E0 | 4.3E0 | 1.5E1 | 4.0E0 | 4.1E-3 | 4.1E-3 | 2.5E2 | 1.2E1 | 421 | 17 | 165 | 17 | 0.48 |
| Bc | ng/mL | 3.4E1 | 6.9E1 | 9.9E1 | 1.2E2 | 1.9E2 | 2.1E2 | 1.1E-1 | 7.0E0 | 1.2E3 | 8.9E2 | 421 | 17 | 165 | 17 | 0.63 |
| Bg | ng/mL | 7.4E-2 | 1.6E-1 | 4.5E0 | 7.3E-1 | 2.1E1 | 1.4E0 | 5.3E-4 | 5.3E-4 | 2.5E2 | 5.3E0 | 421 | 17 | 165 | 17 | 0.53 |
| Bn | ng/mL | 5.6E-2 | 5.6E-2 | 1.2E0 | 1.4E0 | 2.0E0 | 2.1E0 | 5.6E-2 | 5.6E-2 | 9.7E0 | 6.5E0 | 421 | 17 | 165 | 17 | 0.50 |
| Bo | ng/mL | 1.2E1 | 2.2E1 | 1.4E1 | 1.9E1 | 1.9E1 | 1.1E1 | 1.6E-2 | 1.6E-2 | 2.8E2 | 3.9E1 | 421 | 17 | 165 | 17 | 0.67 |
| Ch | uIU/mL | 1.1E0 | 9.5E-1 | 1.9E1 | 1.9E0 | 1.1E2 | 3.5E0 | 3.4E-3 | 3.4E-3 | 1.8E3 | 1.4E1 | 421 | 17 | 165 | 17 | 0.39 |
| Co | pg/mL | 3.6E1 | 3.3E1 | 1.8E2 | 4.7E1 | 9.9E2 | 4.9E1 | 1.5E-1 | 6.2E0 | 1.7E4 | 2.1E2 | 421 | 17 | 165 | 17 | 0.47 |
| Cp | ng/mL | 2.2E1 | 2.3E1 | 2.8E1 | 2.8E1 | 3.2E1 | 2.0E1 | 6.0E-1 | 2.5E0 | 3.7E2 | 8.1E1 | 421 | 17 | 165 | 17 | 0.54 |
| Cq | ng/mL | 2.8E-2 | 4.5E-2 | 1.4E-1 | 7.9E-2 | 8.8E-1 | 1.1E-1 | 8.0E-4 | 8.0E-4 | 1.7E1 | 4.0E-1 | 421 | 17 | 165 | 17 | 0.55 |
| Cs | ng/mL | 5.3E1 | 2.1E2 | 2.7E2 | 2.6E2 | 8.0E2 | 3.1E2 | 2.7E-2 | 4.4E0 | 1.1E4 | 1.2E3 | 421 | 17 | 165 | 17 | 0.58 |
| Ct | ng/mL | 8.6E-1 | 1.8E-1 | 3.5E1 | 6.8E0 | 1.0E2 | 1.6E1 | 1.1E-4 | 2.5E-2 | 6.2E2 | 4.9E1 | 421 | 17 | 165 | 17 | 0.40 |
| Cu | ng/mL | 2.3E-1 | 2.8E-1 | 4.1E-1 | 3.7E-1 | 7.8E-1 | 3.0E-1 | 9.0E-5 | 4.6E-2 | 9.2E0 | 1.1E0 | 421 | 17 | 165 | 17 | 0.56 |
| Cv | ng/mL | 4.7E0 | 8.7E0 | 2.2E1 | 3.2E1 | 6.0E1 | 5.1E1 | 1.4E-4 | 2.4E-2 | 5.3E2 | 1.7E2 | 421 | 17 | 165 | 17 | 0.59 |
| Cw | mIU/mL | 3.0E-2 | 3.6E-2 | 3.9E-2 | 3.4E-2 | 3.3E-2 | 1.8E-2 | 8.9E-4 | 3.5E-3 | 2.4E-1 | 6.4E-2 | 421 | 17 | 165 | 17 | 0.50 |
| Cx | ng/mL | 2.6E-1 | 4.6E-1 | 5.8E1 | 9.0E1 | 1.1E2 | 1.5E2 | 9.3E-5 | 9.3E-5 | 3.9E2 | 3.9E2 | 421 | 17 | 165 | 17 | 0.56 |
| Db | ug/mL | 7.5E0 | 7.3E0 | 9.1E0 | 9.5E0 | 8.7E0 | 8.9E0 | 4.5E-1 | 9.7E-1 | 1.0E2 | 3.1E1 | 421 | 17 | 165 | 17 | 0.49 |
| Dc | nmol/L | 1.8E-2 | 2.4E-2 | 5.5E-2 | 7.1E-2 | 1.3E-1 | 1.5E-1 | 5.2E-6 | 1.6E-3 | 1.6E0 | 6.3E-1 | 421 | 17 | 165 | 17 | 0.58 |
| Dd | ug/mL | 7.1E-2 | 1.4E-1 | 1.8E-1 | 1.6E-1 | 2.6E-1 | 1.7E-1 | 8.3E-5 | 3.2E-3 | 1.9E0 | 6.0E-1 | 421 | 17 | 165 | 17 | 0.56 |
| De | ng/mL | 3.4E-3 | 3.4E-3 | 7.6E-2 | 5.2E-2 | 1.4E-1 | 8.1E-2 | 3.4E-3 | 3.4E-3 | 9.2E-1 | 2.4E-1 | 421 | 17 | 165 | 17 | 0.48 |
| Dg | ng/mL | 2.8E1 | 4.6E1 | 4.1E1 | 5.5E1 | 3.9E1 | 4.3E1 | 1.0E-1 | 2.2E0 | 1.9E2 | 1.9E2 | 421 | 17 | 165 | 17 | 0.61 |
| Di | pg/mL | 1.9E0 | 1.5E0 | 2.2E0 | 2.1E0 | 2.0E0 | 2.3E0 | 1.8E-1 | 1.8E-1 | 1.3E1 | 9.2E0 | 421 | 17 | 165 | 17 | 0.47 |
| Dk | uIU/mL | 1.6E-2 | 1.5E-2 | 9.0E-2 | 3.8E-2 | 5.3E-1 | 5.6E-2 | 1.1E-4 | 1.1E-4 | 8.9E0 | 2.1E-1 | 421 | 17 | 165 | 17 | 0.47 |
| Dl | ng/mL | 2.1E2 | 2.7E2 | 3.0E2 | 3.3E2 | 2.8E2 | 3.1E2 | 1.7E0 | 1.7E1 | 1.5E3 | 1.3E3 | 421 | 17 | 165 | 17 | 0.53 |
| Dp | ng/ml | 2.4E0 | 2.7E0 | 5.2E0 | 5.9E0 | 7.5E0 | 7.7E0 | 3.7E-3 | 3.7E-3 | 4.6E1 | 2.6E1 | 249 | 16 | 162 | 16 | 0.49 |
| Ef | ng/ml | 1.3E-1 | 9.4E-2 | 8.3E-1 | 6.8E-1 | 1.8E0 | 1.5E0 | 5.7E-4 | 4.1E-3 | 1.0E1 | 5.2E0 | 304 | 17 | 164 | 17 | 0.48 |
| Wm | % | 5.9E-1 | 1.6E0 | 2.0E1 | 4.5E1 | 1.5E2 | 1.8E2 | 5.4E-2 | 8.5E-2 | 2.4E3 | 7.7E2 | 341 | 18 | 184 | 18 | 0.55 |
| Ed | pg/ml | 5.2E-1 | 2.4E1 | 5.7E1 | 4.6E1 | 4.6E2 | 4.8E1 | 5.2E-1 | 5.2E-1 | 7.3E3 | 1.3E2 | 249 | 16 | 161 | 16 | 0.65 |
| Tj | pg/mL | 3.7E-1 | 3.7E-1 | 5.9E1 | 6.3E0 | 3.1E2 | 1.5E1 | 3.6E-1 | 3.7E-1 | 3.5E3 | 5.6E1 | 304 | 16 | 167 | 16 | 0.45 |
| Po | pg/ml | 4.8E-1 | 8.9E-1 | 8.6E0 | 5.4E0 | 2.5E1 | 7.3E0 | 8.0E-3 | 2.6E-2 | 2.7E2 | 2.1E1 | 690 | 28 | 279 | 28 | 0.52 |
| Em | ng/ml | 2.9E-3 | 2.9E-3 | 5.5E-2 | 8.4E-2 | 1.1E-1 | 1.9E-1 | 1.9E-16 | 2.9E-3 | 6.0E-1 | 5.0E-1 | 190 | 7 | 87 | 7 | 0.50 |
| Et | ng/ml | 1.3E3 | 2.1E3 | 1.5E3 | 2.1E3 | 1.1E3 | 1.2E3 | 7.5E1 | 1.4E2 | 5.0E3 | 4.1E3 | 689 | 28 | 279 | 28 | 0.63 |
| Fa | ng/ml | 3.9E1 | 8.8E1 | 1.2E2 | 8.2E1 | 5.6E2 | 6.1E1 | 3.4E-2 | 1.6E0 | 8.0E3 | 2.2E2 | 243 | 17 | 159 | 17 | 0.64 |
| Ez | ng/ml | 3.8E0 | 3.4E0 | 1.8E1 | 1.4E1 | 5.5E1 | 2.3E1 | 1.3E-2 | 1.3E-2 | 7.1E2 | 8.9E1 | 249 | 16 | 162 | 16 | 0.51 |
| Fb | ng/ml | 2.5E1 | 2.6E1 | 2.2E1 | 2.3E1 | 1.2E1 | 1.3E1 | 6.6E-1 | 8.1E-1 | 5.7E1 | 4.3E1 | 244 | 17 | 159 | 17 | 0.52 |
| Ex | ng/ml | 7.4E-2 | 9.5E-2 | 2.4E-1 | 1.5E-1 | 7.2E-1 | 1.5E-1 | 3.5E-5 | 1.7E-4 | 8.9E0 | 5.0E-1 | 224 | 13 | 113 | 13 | 0.57 |
| Fn | ng/ml | 2.1E-1 | 2.1E-1 | 6.1E0 | 2.4E0 | 2.7E1 | 4.0E0 | 1.1E-14 | 1.1E-14 | 4.2E2 | 1.6E1 | 249 | 16 | 162 | 16 | 0.46 |
| Fp | ng/ml | 1.2E1 | 1.9E1 | 2.3E1 | 2.8E1 | 2.8E1 | 3.0E1 | 6.0E-3 | 1.3E-1 | 1.4E2 | 1.3E2 | 720 | 28 | 280 | 28 | 0.53 |
| Fr | ng/ml | 3.2E4 | 5.2E4 | 1.1E5 | 1.7E5 | 1.7E5 | 2.4E5 | 1.9E2 | 3.2E2 | 9.0E5 | 7.4E5 | 823 | 28 | 284 | 28 | 0.60 |
| Fw | pg/ml | 1.1E0 | 2.5E0 | 6.2E1 | 1.3E1 | 5.0E2 | 1.8E1 | 1.1E-14 | 1.2E-1 | 6.9E3 | 5.3E1 | 304 | 17 | 165 | 17 | 0.55 |
| Fy | ng/ml | 3.5E1 | 2.3E1 | 5.5E1 | 3.9E1 | 5.6E1 | 5.6E1 | 1.2E-1 | 1.5E0 | 3.3E2 | 2.3E2 | 246 | 15 | 161 | 15 | 0.41 |
| Gl | pg/ml | 7.4E3 | 5.7E3 | 1.1E4 | 1.0E4 | 9.4E3 | 9.0E3 | 9.1E1 | 2.5E2 | 3.4E4 | 2.8E4 | 295 | 17 | 164 | 17 | 0.49 |

Figure 18

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Gp | U/ml | 1.7E0 | 9.8E-1 | 4.1E0 | 2.8E0 | 6.6E0 | 5.1E0 | 1.3E-3 | 1.5E-2 | 6.7E1 | 2.0E1 | 306 | 17 | 165 | 17 | 0.41 |
| Gz | ug/ml | 1.4E0 | 9.2E-1 | 9.2E0 | 5.6E0 | 3.9E1 | 6.6E0 | 2.9E-16 | 4.6E-1 | 4.8E2 | 1.9E1 | 165 | 13 | 106 | 13 | 0.53 |
| Ha | ng/ml | 2.6E0 | 2.5E0 | 9.9E0 | 5.3E0 | 2.1E1 | 8.2E0 | 1.7E-2 | 1.7E-2 | 1.3E2 | 3.3E1 | 247 | 16 | 161 | 16 | 0.46 |
| Nm | pg/ml | 1.4E4 | 1.4E4 | 3.0E4 | 2.7E4 | 8.2E4 | 3.2E4 | 1.0E-9 | 1.0E-9 | 1.6E6 | 1.2E5 | 693 | 28 | 281 | 28 | 0.52 |
| Nn | pg/ml | 1.5E2 | 1.5E2 | 1.9E3 | 6.5E2 | 8.6E3 | 1.0E3 | 1.0E-9 | 1.0E-9 | 1.0E5 | 4.0E3 | 693 | 28 | 281 | 28 | 0.53 |
| No | pg/ml | 1.4E1 | 1.3E1 | 3.5E1 | 2.7E1 | 1.2E2 | 3.5E1 | 1.0E-9 | 1.0E-9 | 2.5E3 | 1.4E2 | 693 | 28 | 281 | 28 | 0.49 |
| Nq | pg/ml | 1.9E0 | 2.6E0 | 1.7E1 | 9.6E0 | 7.0E1 | 1.6E1 | 1.0E-9 | 1.0E-9 | 1.2E3 | 7.3E1 | 693 | 28 | 281 | 28 | 0.53 |
| Nr | pg/ml | 6.5E-1 | 1.3E0 | 3.1E1 | 1.0E1 | 2.0E2 | 2.7E1 | 1.0E-9 | 1.0E-9 | 4.1E3 | 1.4E2 | 693 | 28 | 281 | 28 | 0.51 |
| Ns | pg/ml | 1.0E-9 | 1.0E-9 | 9.7E0 | 8.8E0 | 5.6E1 | 4.5E1 | 1.0E-9 | 1.0E-9 | 1.1E3 | 2.4E2 | 693 | 28 | 281 | 28 | 0.50 |
| Nt | pg/ml | 1.0E2 | 1.0E2 | 1.3E2 | 1.3E2 | 1.1E2 | 7.1E1 | 1.0E-9 | 2.3E1 | 1.5E3 | 3.5E2 | 693 | 28 | 281 | 28 | 0.54 |
| Nu | pg/ml | 1.9E1 | 2.0E1 | 5.4E1 | 6.2E1 | 9.4E1 | 7.8E1 | 1.0E-9 | 1.0E-9 | 8.9E2 | 2.6E2 | 693 | 28 | 281 | 28 | 0.52 |
| Lu | pg/ml | 1.0E4 | 8.5E3 | 1.6E4 | 1.0E4 | 4.6E4 | 1.1E4 | 3.5E2 | 2.1E3 | 7.5E5 | 5.5E4 | 695 | 28 | 281 | 28 | 0.42 |
| Lv | pg/ml | 1.0E-9 | 1.0E-9 | 1.1E1 | 3.3E1 | 2.1E1 | 6.3E1 | 1.0E-9 | 1.0E-9 | 2.4E2 | 2.6E2 | 695 | 28 | 281 | 28 | 0.56 |
| Lw | pg/ml | 1.0E-9 | 1.0E-9 | 3.7E-1 | 3.7E-1 | 4.0E0 | 1.9E0 | 1.0E-9 | 1.0E-9 | 8.0E1 | 9.9E0 | 695 | 28 | 281 | 28 | 0.53 |
| Lx | pg/ml | 1.0E-9 | 2.8E1 | 1.3E2 | 1.8E2 | 4.2E2 | 3.1E2 | 1.0E-9 | 1.0E-9 | 6.2E3 | 1.4E3 | 695 | 28 | 281 | 28 | 0.59 |
| Ly | pg/ml | 1.0E-9 | 9.9E0 | 1.0E1 | 1.5E1 | 2.0E1 | 1.7E1 | 1.0E-9 | 1.0E-9 | 1.6E2 | 7.0E1 | 695 | 28 | 281 | 28 | 0.63 |
| Lz | pg/ml | 1.0E-9 | 1.0E-9 | 4.9E0 | 1.0E-9 | 3.4E1 | 0.0E0 | 1.0E-9 | 1.0E-9 | 6.0E2 | 1.0E-9 | 695 | 28 | 281 | 28 | 0.46 |
| Ma | pg/ml | 2.7E2 | 3.2E2 | 1.4E3 | 1.8E3 | 3.8E3 | 3.7E3 | 1.0E-9 | 1.0E-9 | 6.5E4 | 1.7E4 | 695 | 28 | 281 | 28 | 0.52 |
| Mb | pg/ml | 2.5E1 | 2.6E1 | 3.1E1 | 3.1E1 | 1.6E1 | 1.5E1 | 5.4E0 | 1.4E1 | 2.1E2 | 5.5E1 | 695 | 28 | 281 | 28 | 0.47 |
| Mc | pg/ml | 1.0E-9 | 1.0E-9 | 3.6E-2 | 8.9E-2 | 5.3E-1 | 4.7E-1 | 1.0E-9 | 1.0E-9 | 1.3E1 | 2.5E0 | 695 | 28 | 281 | 28 | 0.51 |
| Md | pg/ml | 1.0E-9 | 1.0E-9 | 5.0E-1 | 1.7E-2 | 4.0E0 | 9.2E-2 | 1.0E-9 | 1.0E-9 | 6.8E1 | 4.9E-1 | 695 | 28 | 281 | 28 | 0.48 |
| Me | pg/ml | 3.2E1 | 2.9E1 | 3.1E1 | 3.0E1 | 2.0E1 | 1.2E1 | 1.0E-9 | 2.4E-1 | 3.2E2 | 5.6E1 | 695 | 28 | 281 | 28 | 0.47 |
| Mf | pg/ml | 1.0E-9 | 1.0E-9 | 5.0E-1 | 1.0E-1 | 2.9E0 | 4.2E-1 | 1.0E-9 | 1.0E-9 | 5.6E1 | 2.2E0 | 695 | 28 | 281 | 28 | 0.46 |
| Mg | pg/ml | 1.7E0 | 8.3E-1 | 7.3E0 | 5.7E0 | 1.2E1 | 7.4E0 | 1.0E-9 | 1.0E-9 | 9.2E1 | 2.6E1 | 695 | 28 | 281 | 28 | 0.51 |
| Mh | pg/ml | 1.0E-9 | 1.0E-9 | 1.5E0 | 3.7E-1 | 1.1E1 | 1.5E0 | 1.0E-9 | 1.0E-9 | 1.6E2 | 7.8E0 | 695 | 28 | 281 | 28 | 0.49 |
| Mi | pg/ml | 1.0E-9 | 1.0E-9 | 4.9E-1 | 1.1E0 | 5.8E0 | 5.9E0 | 1.0E-9 | 1.0E-9 | 1.2E2 | 3.1E1 | 695 | 28 | 281 | 28 | 0.51 |
| Mj | pg/ml | 1.0E-9 | 1.0E-9 | 4.8E0 | 2.2E0 | 2.7E1 | 5.8E0 | 1.0E-9 | 1.0E-9 | 4.6E2 | 2.2E1 | 695 | 28 | 281 | 28 | 0.51 |
| Mk | pg/ml | 9.1E-1 | 1.0E-9 | 1.5E1 | 4.3E0 | 9.7E1 | 8.8E0 | 1.0E-9 | 1.0E-9 | 1.7E3 | 4.0E1 | 695 | 28 | 281 | 28 | 0.44 |
| Ml | pg/ml | 1.0E-9 | 1.0E-9 | 5.8E0 | 3.3E-1 | 8.2E1 | 1.5E0 | 1.0E-9 | 1.0E-9 | 2.1E3 | 8.0E0 | 695 | 28 | 281 | 28 | 0.44 |
| Mm | pg/ml | 5.4E2 | 7.3E2 | 9.2E2 | 1.4E3 | 1.1E3 | 2.1E3 | 1.0E-9 | 8.8E-2 | 7.3E3 | 9.9E3 | 695 | 28 | 281 | 28 | 0.55 |
| Mn | pg/ml | 5.3E0 | 5.8E0 | 1.0E1 | 9.8E0 | 2.4E1 | 1.1E1 | 1.0E-9 | 1.0E-9 | 3.5E2 | 5.2E1 | 695 | 28 | 281 | 28 | 0.56 |
| Mp | pg/ml | 1.0E-9 | 1.0E-9 | 8.4E0 | 1.8E1 | 2.9E1 | 3.6E1 | 1.0E-9 | 1.0E-9 | 6.3E2 | 1.5E2 | 694 | 28 | 281 | 28 | 0.55 |
| Mq | pg/ml | 1.0E-9 | 1.0E-9 | 2.8E0 | 3.4E0 | 1.6E1 | 1.3E1 | 1.0E-9 | 1.0E-9 | 2.1E2 | 6.2E1 | 694 | 28 | 281 | 28 | 0.52 |
| Mr | pg/ml | 1.0E-9 | 1.0E-9 | 1.6E1 | 1.2E1 | 7.9E1 | 5.5E1 | 1.0E-9 | 1.0E-9 | 1.4E3 | 2.9E2 | 694 | 28 | 281 | 28 | 0.48 |
| Ms | pg/ml | 4.1E2 | 2.9E2 | 5.6E2 | 4.0E2 | 6.4E2 | 3.8E2 | 1.0E-9 | 1.0E-9 | 5.6E3 | 1.5E3 | 694 | 28 | 281 | 28 | 0.44 |
| Mt | pg/ml | 1.0E-9 | 7.9E-1 | 6.8E0 | 4.3E0 | 4.6E1 | 1.3E1 | 1.0E-9 | 1.0E-9 | 8.7E2 | 7.0E1 | 694 | 28 | 281 | 28 | 0.60 |
| Mu | pg/ml | 1.0E-9 | 1.0E-9 | 1.3E0 | 6.2E-1 | 1.2E1 | 1.6E0 | 1.0E-9 | 1.0E-9 | 2.3E2 | 6.2E0 | 694 | 28 | 281 | 28 | 0.54 |
| Mv | pg/ml | 1.0E-9 | 1.0E-9 | 6.8E1 | 5.1E1 | 3.3E2 | 1.2E2 | 1.0E-9 | 1.0E-9 | 4.5E3 | 5.3E2 | 694 | 28 | 281 | 28 | 0.53 |
| Mw | pg/ml | 3.2E1 | 3.4E1 | 4.3E2 | 2.0E2 | 2.9E3 | 3.5E2 | 1.0E-9 | 1.0E-9 | 6.2E4 | 1.4E3 | 694 | 28 | 281 | 28 | 0.51 |
| Mx | pg/ml | 1.0E-9 | 1.0E-9 | 2.3E-1 | 2.8E-1 | 1.4E0 | 7.7E-1 | 1.0E-9 | 1.0E-9 | 3.2E1 | 3.4E0 | 694 | 28 | 281 | 28 | 0.53 |
| My | pg/ml | 1.0E-9 | 1.0E-9 | 4.3E2 | 1.5E2 | 2.9E3 | 3.5E2 | 1.0E-9 | 1.0E-9 | 3.9E4 | 1.7E3 | 694 | 28 | 281 | 28 | 0.53 |
| Mz | pg/ml | 1.0E1 | 1.3E1 | 2.4E1 | 3.7E1 | 6.8E1 | 6.4E1 | 1.0E-9 | 1.0E-9 | 1.2E3 | 2.7E2 | 694 | 28 | 281 | 28 | 0.56 |
| Na | pg/ml | 1.0E-9 | 1.0E-9 | 7.7E-1 | 5.7E-1 | 2.9E0 | 1.7E0 | 1.0E-9 | 1.0E-9 | 3.6E1 | 7.2E0 | 694 | 28 | 281 | 28 | 0.50 |
| Nb | pg/ml | 1.9E0 | 3.0E0 | 4.0E0 | 3.1E0 | 1.3E1 | 2.6E0 | 1.0E-9 | 1.0E-9 | 2.3E2 | 1.0E1 | 694 | 28 | 281 | 28 | 0.56 |
| Nc | pg/ml | 3.8E2 | 1.2E2 | 6.2E2 | 3.6E2 | 7.7E2 | 5.4E2 | 1.0E-9 | 1.0E-9 | 9.2E3 | 2.1E3 | 694 | 28 | 281 | 28 | 0.39 |
| Nd | pg/ml | 2.9E1 | 6.4E0 | 2.7E1 | 1.4E1 | 5.0E1 | 1.6E1 | 1.0E-9 | 1.0E-9 | 1.2E3 | 5.2E1 | 694 | 28 | 281 | 28 | 0.33 |
| Ne | pg/ml | 4.7E2 | 2.0E2 | 6.0E2 | 3.2E2 | 5.9E2 | 3.7E2 | 1.0E-9 | 1.0E-9 | 7.0E3 | 1.5E3 | 694 | 28 | 281 | 28 | 0.34 |
| Nf | pg/ml | 1.0E-9 | 1.0E-9 | 3.2E0 | 5.5E-1 | 1.0E1 | 1.6E0 | 1.0E-9 | 1.0E-9 | 1.6E2 | 6.9E0 | 694 | 28 | 281 | 28 | 0.44 |
| Ng | pg/ml | 2.1E1 | 2.5E0 | 1.3E2 | 9.8E1 | 2.6E2 | 1.8E2 | 1.0E-9 | 1.0E-9 | 2.3E3 | 6.4E2 | 694 | 28 | 281 | 28 | 0.44 |
| Nh | pg/ml | 7.1E1 | 3.9E1 | 9.4E1 | 5.8E1 | 8.6E1 | 5.7E1 | 1.0E-9 | 3.1E0 | 5.6E2 | 2.2E2 | 694 | 28 | 281 | 28 | 0.36 |
| Ni | pg/ml | 1.0E-9 | 1.7E1 | 7.6E1 | 1.0E2 | 1.2E2 | 1.5E2 | 1.0E-9 | 1.0E-9 | 7.1E2 | 4.8E2 | 694 | 28 | 281 | 28 | 0.54 |
| Nj | pg/ml | 8.2E0 | 2.8E0 | 1.2E1 | 6.8E0 | 1.2E1 | 7.8E0 | 1.0E-9 | 1.0E-9 | 8.3E1 | 2.8E1 | 694 | 28 | 281 | 28 | 0.36 |
| Nk | pg/ml | 1.9E1 | 1.4E1 | 3.4E1 | 2.3E1 | 4.0E1 | 2.5E1 | 1.0E-9 | 1.0E-9 | 2.0E2 | 8.7E1 | 694 | 28 | 281 | 28 | 0.45 |
| Nl | pg/ml | 4.9E1 | 2.1E1 | 6.5E1 | 3.7E1 | 7.2E1 | 4.4E1 | 1.0E-9 | 1.0E-9 | 1.1E3 | 1.4E2 | 694 | 28 | 281 | 28 | 0.35 |
| Tz | pg/ml | 5.2E3 | 4.9E3 | 1.3E4 | 1.9E4 | 6.4E4 | 4.2E4 | 1.0E-9 | 7.5E2 | 1.0E6 | 1.7E5 | 251 | 16 | 160 | 16 | 0.49 |
| Ua | pg/ml | 3.8E3 | 2.8E3 | 2.3E4 | 6.3E3 | 1.4E5 | 7.6E3 | 1.0E-9 | 2.7E2 | 2.1E6 | 2.4E4 | 251 | 16 | 160 | 16 | 0.43 |
| Ub | pg/ml | 5.7E2 | 2.9E2 | 8.6E2 | 3.8E2 | 1.0E3 | 3.7E2 | 1.0E-9 | 1.5E1 | 9.8E3 | 1.4E3 | 251 | 16 | 160 | 16 | 0.32 |

Figure 18 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ue | pg/ml | 3.0E1 | 2.0E1 | 3.7E1 | 2.3E1 | 3.2E1 | 1.7E1 | 9.8E-2 | 2.9E0 | 3.5E2 | 7.4E1 | 251 | 16 | 160 | 16 | 0.34 |
| Uc | pg/ml | 8.6E2 | 8.6E2 | 1.6E3 | 2.0E3 | 2.7E3 | 2.8E3 | 1.0E-9 | 2.1E1 | 2.9E4 | 9.4E3 | 251 | 16 | 160 | 16 | 0.52 |
| Ud | pg/ml | 1.0E-9 | 1.0E-9 | 1.7E0 | 1.0E-9 | 2.5E1 | 0.0E0 | 1.0E-9 | 1.0E-9 | 3.9E2 | 1.0E-9 | 251 | 16 | 160 | 16 | 0.49 |
| Hq | pg/ml | 1.1E0 | 1.3E0 | 1.3E2 | 1.6E1 | 1.8E3 | 6.5E1 | 1.0E-9 | 1.0E-9 | 3.4E4 | 3.4E2 | 691 | 28 | 280 | 28 | 0.51 |
| Hr | pg/ml | 1.3E2 | 1.0E2 | 8.2E2 | 7.7E2 | 1.6E3 | 1.2E3 | 1.0E-9 | 2.3E1 | 1.4E4 | 4.6E3 | 691 | 28 | 280 | 28 | 0.49 |
| Hu | pg/ml | 7.1E0 | 3.1E0 | 3.0E3 | 3.8E2 | 2.9E4 | 1.3E3 | 1.0E-9 | 1.0E-9 | 6.3E5 | 5.8E3 | 691 | 28 | 280 | 28 | 0.47 |
| Hv | pg/ml | 1.4E0 | 2.5E0 | 3.3E0 | 2.3E0 | 1.2E1 | 1.6E0 | 1.0E-9 | 1.0E-9 | 2.5E2 | 6.9E0 | 691 | 28 | 280 | 28 | 0.60 |
| Hw | pg/ml | 7.1E0 | 5.0E0 | 2.0E1 | 7.4E0 | 8.0E1 | 7.3E0 | 1.0E-9 | 1.0E-9 | 1.7E3 | 2.3E1 | 691 | 28 | 280 | 28 | 0.40 |
| Hx | pg/ml | 8.8E0 | 1.4E1 | 4.4E1 | 2.8E1 | 3.6E2 | 4.3E1 | 1.0E-9 | 1.0E-9 | 9.3E3 | 2.2E2 | 691 | 28 | 280 | 28 | 0.55 |
| Ib | ng/ml | 6.2E-2 | 8.4E-3 | 1.4E0 | 6.8E-2 | 5.0E0 | 1.7E-1 | 1.0E-9 | 1.0E-9 | 3.6E1 | 6.8E-1 | 241 | 16 | 159 | 16 | 0.27 |
| Ic | U/ml | 2.2E2 | 2.2E2 | 7.3E2 | 5.5E3 | 6.1E3 | 1.7E4 | 2.4E0 | 2.2E1 | 9.3E4 | 6.5E4 | 241 | 16 | 159 | 16 | 0.55 |
| Id | U/ml | 6.4E-1 | 9.1E-1 | 1.2E0 | 2.2E0 | 2.0E0 | 3.1E0 | 1.0E-9 | 2.7E-1 | 2.3E1 | 1.2E1 | 241 | 16 | 159 | 16 | 0.60 |
| Tt | pg/ml | 1.6E2 | 1.5E2 | 1.7E2 | 1.6E2 | 5.1E1 | 4.0E1 | 4.3E1 | 1.1E2 | 3.6E2 | 2.3E2 | 231 | 14 | 153 | 14 | 0.42 |
| To | pg/ml | 1.6E0 | 1.9E0 | 1.9E0 | 2.3E0 | 2.4E0 | 1.9E0 | 1.0E-9 | 1.0E-9 | 2.3E1 | 6.0E0 | 242 | 14 | 157 | 14 | 0.61 |
| Tr | pg/ml | 2.8E0 | 2.7E0 | 5.8E0 | 5.7E0 | 2.0E1 | 8.4E0 | 1.0E-9 | 3.3E-1 | 3.1E2 | 3.2E1 | 238 | 14 | 156 | 14 | 0.50 |
| Tn | pg/ml | 2.6E1 | 3.3E1 | 8.0E1 | 6.8E1 | 2.2E2 | 8.4E1 | 2.4E0 | 8.8E0 | 1.8E3 | 3.0E2 | 242 | 14 | 157 | 14 | 0.59 |
| Tv | ng/ml | 1.2E1 | 3.7E0 | 1.9E1 | 4.2E1 | 3.7E1 | 8.8E1 | 1.0E-9 | 1.0E-9 | 4.9E2 | 3.2E2 | 242 | 14 | 157 | 14 | 0.43 |
| Ih | ng/ml | 6.9E1 | 4.4E1 | 2.1E2 | 1.6E2 | 3.7E2 | 2.5E2 | 1.0E-9 | 1.0E-9 | 2.6E3 | 9.0E2 | 694 | 28 | 280 | 28 | 0.46 |
| Ii | ng/ml | 9.0E1 | 6.3E1 | 2.6E2 | 1.5E2 | 7.4E2 | 2.1E2 | 7.3E-1 | 9.1E0 | 1.0E4 | 8.1E2 | 694 | 28 | 280 | 28 | 0.46 |
| Ij | ng/ml | 7.3E1 | 7.7E1 | 1.8E2 | 8.7E1 | 6.4E2 | 6.6E1 | 2.1E0 | 1.0E-9 | 6.4E3 | 3.0E2 | 686 | 28 | 279 | 28 | 0.48 |
| Ik | ng/ml | 1.4E1 | 4.9E1 | 9.8E2 | 2.3E2 | 9.3E3 | 3.9E2 | 5.9E-1 | 2.1E0 | 1.2E5 | 1.5E3 | 690 | 28 | 279 | 28 | 0.54 |
| Il | ng/ml | 3.3E2 | 3.3E2 | 1.2E3 | 6.4E2 | 2.7E3 | 8.1E2 | 1.0E-9 | 1.0E-9 | 1.2E4 | 3.2E3 | 680 | 28 | 279 | 28 | 0.48 |
| Im | ng/ml | 1.9E2 | 2.1E2 | 3.4E2 | 3.5E2 | 5.0E2 | 3.2E2 | 1.3E1 | 2.5E1 | 6.0E3 | 1.1E3 | 689 | 28 | 279 | 28 | 0.53 |
| In | ng/ml | 3.9E0 | 1.6E0 | 2.5E1 | 6.1E0 | 1.7E2 | 1.6E1 | 1.0E-9 | 1.0E-9 | 3.9E3 | 8.4E1 | 694 | 28 | 280 | 28 | 0.37 |
| Hb | ng/ml | 2.4E1 | 2.0E1 | 3.2E1 | 3.1E1 | 2.9E1 | 3.4E1 | 4.8E-1 | 2.1E0 | 1.5E2 | 1.2E2 | 248 | 17 | 160 | 17 | 0.45 |
| Hc | pg/ml | 6.7E2 | 4.6E2 | 3.7E3 | 9.8E2 | 1.3E4 | 1.6E3 | 1.0E-9 | 2.2E2 | 1.0E5 | 6.8E3 | 248 | 17 | 160 | 17 | 0.44 |
| Hf | ng/ml | 1.5E2 | 1.3E2 | 3.8E2 | 2.7E2 | 5.3E2 | 3.2E2 | 1.0E-9 | 1.0E-9 | 2.5E3 | 8.5E2 | 248 | 17 | 160 | 17 | 0.48 |
| Io | ng/ml | 7.5E3 | 8.8E3 | 2.4E4 | 1.5E4 | 1.6E5 | 2.2E4 | 1.0E-9 | 9.0E2 | 4.0E6 | 1.1E5 | 687 | 27 | 280 | 27 | 0.52 |
| Ip | ng/ml | 8.7E0 | 1.3E1 | 1.9E1 | 3.0E1 | 2.4E1 | 4.1E1 | 1.0E-9 | 1.6E-2 | 2.6E2 | 1.6E2 | 687 | 27 | 280 | 27 | 0.55 |
| Iq | ug/ml | 9.5E-2 | 8.1E-2 | 4.0E1 | 1.8E-1 | 7.3E2 | 2.8E-1 | 1.0E-9 | 1.0E-9 | 1.4E4 | 1.4E0 | 687 | 27 | 280 | 27 | 0.45 |
| Ir | ug/ml | 3.3E-1 | 4.8E-1 | 3.8E0 | 1.5E0 | 2.8E1 | 3.1E0 | 1.0E-9 | 1.0E-9 | 5.1E2 | 1.6E1 | 686 | 27 | 280 | 27 | 0.59 |
| Is | ng/ml | 1.4E0 | 3.7E0 | 5.7E0 | 9.9E0 | 2.3E1 | 2.1E1 | 1.0E-9 | 2.7E-1 | 5.5E2 | 1.1E2 | 687 | 27 | 280 | 27 | 0.67 |
| It | ng/ml | 2.0E0 | 1.7E0 | 2.6E1 | 4.7E0 | 1.5E2 | 9.1E0 | 1.0E-9 | 1.0E-9 | 2.8E3 | 4.7E1 | 687 | 27 | 280 | 27 | 0.53 |
| Iu | ng/ml | 2.1E2 | 1.9E2 | 1.4E3 | 1.7E3 | 4.3E3 | 4.7E3 | 1.0E-9 | 1.0E-9 | 2.9E4 | 2.4E4 | 687 | 27 | 280 | 27 | 0.53 |
| Iv | ng/ml | 1.2E1 | 2.4E1 | 6.1E1 | 3.7E1 | 6.1E2 | 3.4E1 | 1.0E-9 | 1.0E-9 | 1.6E4 | 1.0E2 | 686 | 27 | 280 | 27 | 0.59 |
| Iz | ng/ml | 1.4E2 | 7.5E1 | 6.8E2 | 2.8E2 | 4.0E3 | 4.2E2 | 1.5E0 | 1.3E1 | 6.2E4 | 1.5E3 | 248 | 17 | 160 | 17 | 0.41 |
| Rc | pg/ml | 5.5E3 | 6.1E3 | 7.3E3 | 7.8E3 | 6.0E3 | 5.4E3 | 1.9E2 | 3.0E2 | 3.9E4 | 1.6E4 | 248 | 16 | 160 | 16 | 0.54 |
| Rb | pg/ml | 7.9E-1 | 8.6E-1 | 2.6E0 | 2.1E0 | 4.4E0 | 2.8E0 | 1.0E-9 | 1.0E-9 | 4.3E1 | 9.1E0 | 248 | 16 | 160 | 16 | 0.52 |
| Pz | ng/ml | 3.3E3 | 7.8E3 | 6.8E3 | 4.2E3 | 1.8E4 | 1.9E5 | 1.3E1 | 9.5E1 | 2.8E5 | 1.0E6 | 687 | 28 | 278 | 28 | 0.57 |
| Qa | ng/ml | 3.1E3 | 6.0E3 | 5.8E3 | 7.8E3 | 7.1E3 | 6.7E3 | 1.5E2 | 2.9E2 | 5.2E4 | 2.5E4 | 687 | 28 | 278 | 28 | 0.61 |
| Qb | ng/ml | 9.1E1 | 1.2E2 | 2.1E2 | 1.8E2 | 5.2E2 | 1.9E2 | 7.9E-1 | 2.4E0 | 8.3E3 | 7.2E2 | 687 | 28 | 278 | 28 | 0.53 |
| Qc | ng/ml | 2.1E2 | 1.9E2 | 4.4E2 | 2.7E2 | 7.6E2 | 2.7E2 | 1.0E-9 | 2.0E0 | 1.1E4 | 1.2E3 | 687 | 28 | 278 | 28 | 0.45 |
| Qd | ng/ml | 8.7E3 | 9.1E3 | 1.9E4 | 2.5E4 | 8.2E4 | 4.0E4 | 1.5E2 | 1.1E3 | 2.0E6 | 1.9E5 | 687 | 28 | 278 | 28 | 0.56 |
| Qe | ng/ml | 8.0E2 | 1.5E3 | 1.7E3 | 2.2E3 | 4.2E3 | 2.4E3 | 1.0E-9 | 5.5E1 | 9.7E4 | 9.3E3 | 687 | 28 | 278 | 28 | 0.60 |
| Jd | ng/ml | 9.2E-1 | 8.0E-1 | 6.7E0 | 1.7E0 | 4.4E1 | 2.3E0 | 1.0E-9 | 1.0E-9 | 6.5E2 | 8.0E0 | 249 | 16 | 162 | 16 | 0.48 |
| Je | ng/ml | 1.0E-9 | 2.2E-1 | 2.3E0 | 8.4E-1 | 8.0E0 | 1.2E0 | 8.8E1 | 3.6E0 | 1.9E4 | 3.6E1 | 249 | 16 | 162 | 16 | 0.49 |
| Jf | ng/ml | 1.0E-9 | 1.6E-1 | 1.1E0 | 9.2E-1 | 2.3E0 | 1.3E0 | 1.0E-9 | 1.0E-9 | 1.2E1 | 3.9E0 | 249 | 16 | 162 | 16 | 0.56 |
| Jg | ng/ml | 4.4E2 | 7.3E2 | 7.3E2 | 9.2E2 | 9.6E2 | 7.3E2 | 1.0E-9 | 2.1E1 | 1.0E4 | 2.5E3 | 691 | 28 | 280 | 28 | 0.60 |
| Jh | ng/ml | 2.9E0 | 3.2E0 | 2.4E1 | 1.3E1 | 1.1E2 | 1.9E1 | 1.0E-9 | 1.0E-9 | 1.6E3 | 6.8E1 | 691 | 28 | 280 | 28 | 0.54 |
| Ji | ng/ml | 5.0E1 | 7.6E1 | 7.0E1 | 1.1E2 | 6.9E1 | 9.7E1 | 1.0E-9 | 8.5E0 | 5.3E2 | 3.8E2 | 691 | 28 | 280 | 28 | 0.65 |
| Sr | pg/mL | 3.4E2 | 3.8E2 | 8.1E2 | 1.2E3 | 1.3E3 | 1.8E3 | 1.0E-9 | 1.0E-9 | 9.8E3 | 5.5E3 | 239 | 16 | 157 | 16 | 0.52 |
| Ss | pg/mL | 9.2E4 | 9.2E4 | 1.5E5 | 1.2E5 | 1.9E5 | 1.0E5 | 2.7E3 | 9.6E3 | 1.8E6 | 3.5E5 | 239 | 16 | 157 | 16 | 0.50 |
| St | pg/mL | 2.2E7 | 3.8E7 | 4.9E7 | 5.0E7 | 9.0E7 | 4.7E7 | 1.0E6 | 1.6E6 | 1.2E9 | 1.3E8 | 244 | 15 | 158 | 15 | 0.54 |
| Ra | pg/ml | 1.0E-9 | 1.0E-9 | 6.4E-1 | 3.2E-1 | 1.3E0 | 7.5E-1 | 1.0E-9 | 1.0E-9 | 7.3E0 | 3.0E0 | 248 | 16 | 160 | 16 | 0.49 |
| Qz | pg/ml | 1.1E1 | 1.0E-9 | 6.1E1 | 4.0E1 | 1.0E2 | 8.5E1 | 1.0E-9 | 1.0E-9 | 7.1E2 | 3.2E2 | 248 | 16 | 160 | 16 | 0.38 |
| Qy | pg/ml | 4.3E-1 | 5.8E-1 | 1.0E1 | 1.5E0 | 5.7E1 | 2.9E0 | 1.0E-9 | 1.0E-9 | 6.5E2 | 1.2E1 | 248 | 16 | 160 | 16 | 0.54 |
| Qx | pg/ml | 1.0E-9 | 1.0E-9 | 6.8E0 | 5.0E-2 | 5.2E1 | 2.0E-1 | 1.0E-9 | 1.0E-9 | 5.8E2 | 7.9E-1 | 248 | 16 | 160 | 16 | 0.46 |

Figure 18 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Qw | pg/ml | 1.0E-9 | 1.0E-9 | 2.5E0 | 1.1E-2 | 1.1E1 | 3.1E-2 | 1.0E-9 | 1.0E-9 | 1.2E2 | 9.0E-2 | 248 | 16 | 160 | 16 | 0.30 |
| Qv | pg/ml | 2.4E4 | 9.5E3 | 3.4E4 | 7.3E4 | 5.7E4 | 2.3E5 | 1.0E-9 | 1.6E3 | 7.4E5 | 9.4E5 | 248 | 16 | 160 | 16 | 0.33 |
| Qu | pg/ml | 7.7E0 | 1.9E0 | 8.8E1 | 2.7E1 | 1.7E2 | 5.5E1 | 1.0E-9 | 1.0E-9 | 9.8E2 | 2.1E2 | 248 | 16 | 160 | 16 | 0.43 |
| Qt | pg/ml | 1.0E1 | 6.3E0 | 5.3E1 | 3.7E1 | 1.3E2 | 8.2E1 | 1.0E-9 | 1.0E-9 | 1.0E3 | 3.3E2 | 248 | 16 | 160 | 16 | 0.49 |
| Qh | ng/ml | 1.7E1 | 2.3E1 | 3.6E1 | 4.2E1 | 6.1E1 | 5.1E1 | 1.0E-9 | 7.8E-1 | 6.4E2 | 2.0E2 | 248 | 16 | 160 | 16 | 0.56 |
| Qg | ng/ml | 8.5E0 | 8.3E0 | 2.1E1 | 1.5E1 | 7.1E1 | 2.2E1 | 5.1E-2 | 6.9E-1 | 1.0E3 | 7.4E1 | 248 | 16 | 160 | 16 | 0.46 |
| Jj | ng/ml | 6.7E2 | 4.1E2 | 1.9E3 | 1.0E3 | 1.4E4 | 1.5E3 | 2.3E0 | 1.3E1 | 3.4E5 | 6.7E3 | 691 | 28 | 280 | 28 | 0.43 |
| Jk | ng/ml | 3.0E0 | 3.0E0 | 2.2E1 | 2.0E1 | 4.7E1 | 3.2E1 | 1.0E-9 | 1.2E-1 | 3.9E2 | 1.2E2 | 691 | 28 | 280 | 28 | 0.50 |
| Jl | ng/ml | 3.9E-1 | 5.1E-1 | 1.7E0 | 4.4E0 | 4.2E0 | 7.5E0 | 7.6E-4 | 2.3E-3 | 3.2E1 | 2.0E1 | 691 | 28 | 280 | 28 | 0.60 |
| Jm | ng/ml | 1.7E1 | 1.5E1 | 5.2E1 | 4.5E1 | 1.1E2 | 6.8E1 | 1.0E-9 | 3.8E-1 | 1.4E3 | 3.2E2 | 691 | 28 | 280 | 28 | 0.50 |
| Jn | pg/ml | 3.8E-1 | 4.4E-1 | 2.4E0 | 8.5E-1 | 2.4E1 | 9.0E-1 | 1.0E-9 | 4.7E-2 | 6.2E2 | 3.2E0 | 691 | 28 | 280 | 28 | 0.59 |
| Jo | pg/ml | 3.6E3 | 3.6E3 | 4.9E3 | 4.2E3 | 3.9E3 | 3.3E3 | 2.0E1 | 2.7E2 | 2.4E4 | 1.3E4 | 691 | 28 | 280 | 28 | 0.46 |
| Jp | pg/ml | 6.8E4 | 7.5E4 | 7.1E4 | 8.0E4 | 3.6E4 | 3.0E4 | 5.8E2 | 8.9E3 | 3.0E5 | 1.4E5 | 691 | 28 | 280 | 28 | 0.61 |
| Jq | pg/ml | 9.5E1 | 1.4E2 | 1.5E2 | 1.9E2 | 2.2E2 | 1.9E2 | 1.0E0 | 2.6E1 | 4.0E3 | 7.5E2 | 691 | 28 | 280 | 28 | 0.58 |
| Jr | pg/ml | 5.1E0 | 6.2E0 | 3.5E1 | 1.0E1 | 4.1E2 | 1.2E1 | 1.0E-9 | 1.0E-9 | 1.1E4 | 4.8E1 | 691 | 28 | 280 | 28 | 0.56 |
| Js | pg/ml | 1.3E1 | 1.3E1 | 5.2E1 | 2.1E1 | 4.0E2 | 2.6E1 | 1.0E-9 | 4.5E-1 | 1.0E4 | 1.1E2 | 691 | 28 | 280 | 28 | 0.49 |
| Jt | pg/ml | 2.5E3 | 2.5E3 | 3.1E3 | 2.9E3 | 2.3E3 | 2.0E3 | 2.2E1 | 3.5E2 | 2.2E4 | 7.8E3 | 691 | 28 | 280 | 28 | 0.49 |
| Ju | mIU/ml | 8.5E0 | 6.7E0 | 2.0E1 | 1.4E1 | 3.2E1 | 2.5E1 | 6.5E-2 | 1.7E-1 | 2.3E2 | 1.0E2 | 249 | 16 | 162 | 16 | 0.43 |
| Jv | mIU/ml | 1.1E1 | 1.3E1 | 3.5E1 | 2.7E1 | 6.3E1 | 4.6E1 | 1.0E-2 | 9.4E-3 | 4.4E2 | 1.8E2 | 249 | 16 | 162 | 16 | 0.45 |
| Jy | ng/ml | 1.6E-3 | 1.6E-3 | 2.2E-3 | 1.7E-3 | 4.3E-3 | 9.2E-4 | 1.0E-9 | 4.5E-4 | 5.2E-2 | 3.5E-3 | 249 | 16 | 162 | 16 | 0.49 |
| Kc | pg/ml | 2.3E1 | 4.6E1 | 4.1E1 | 7.0E1 | 4.3E1 | 5.7E1 | 1.0E-9 | 6.1E0 | 1.9E2 | 1.6E2 | 249 | 17 | 160 | 17 | 0.64 |
| Kd | pg/ml | 1.0E-9 | 1.0E-9 | 1.6E2 | 2.0E2 | 5.4E2 | 5.3E2 | 1.0E-9 | 1.0E-9 | 4.8E3 | 1.8E3 | 249 | 17 | 160 | 17 | 0.53 |
| Ke | pg/ml | 1.2E4 | 1.2E4 | 1.4E4 | 1.5E4 | 1.1E4 | 1.3E4 | 3.4E2 | 1.3E3 | 7.0E4 | 4.4E4 | 249 | 17 | 160 | 17 | 0.49 |
| Kf | pg/mL | 6.4E0 | 8.7E0 | 6.8E0 | 9.5E0 | 5.6E0 | 5.4E0 | 1.0E-9 | 1.0E-9 | 2.6E1 | 1.6E1 | 249 | 17 | 160 | 17 | 0.65 |
| Kg | pg/mL | 1.1E3 | 5.1E2 | 1.9E3 | 1.3E3 | 2.6E3 | 1.4E3 | 7.3E1 | 2.1E2 | 2.2E4 | 4.6E3 | 249 | 17 | 160 | 17 | 0.38 |
| Ki | pg/ml | 6.1E1 | 5.6E1 | 7.0E1 | 5.6E1 | 5.2E1 | 2.3E1 | 1.0E-9 | 1.8E1 | 3.8E2 | 1.0E2 | 248 | 17 | 160 | 17 | 0.43 |
| Kj | pg/ml | 1.0E3 | 6.3E2 | 1.6E3 | 1.1E3 | 1.6E3 | 1.4E3 | 1.4E1 | 9.4E1 | 1.0E4 | 6.1E3 | 249 | 17 | 160 | 17 | 0.36 |
| Kk | pg/ml | 6.9E0 | 8.2E0 | 1.1E1 | 1.6E1 | 1.5E1 | 1.7E1 | 1.0E-9 | 1.0E-9 | 1.6E2 | 4.8E1 | 249 | 17 | 160 | 17 | 0.53 |
| Kl | pg/ml | 2.0E4 | 1.7E4 | 2.7E4 | 2.9E4 | 2.5E4 | 2.4E4 | 1.6E2 | 8.3E2 | 1.6E5 | 6.9E4 | 249 | 17 | 160 | 17 | 0.53 |
| Kn | pg/ml | 2.9E1 | 2.9E1 | 5.8E1 | 8.4E1 | 9.0E1 | 1.2E2 | 1.0E-9 | 1.0E-9 | 7.3E2 | 3.8E2 | 249 | 17 | 160 | 17 | 0.52 |
| Ko | pg/ml | 3.2E2 | 4.4E2 | 4.3E2 | 5.5E2 | 4.4E2 | 4.9E2 | 1.0E-9 | 1.0E-9 | 2.2E3 | 1.5E3 | 249 | 17 | 160 | 17 | 0.57 |
| Kp | pg/ml | 3.0E2 | 4.0E2 | 3.4E2 | 4.5E2 | 2.6E2 | 2.7E2 | 1.0E-9 | 1.0E-9 | 1.7E3 | 1.1E3 | 249 | 17 | 160 | 17 | 0.62 |
| Kq | pg/ml | 3.0E2 | 3.4E2 | 4.8E2 | 5.8E2 | 8.7E2 | 6.1E2 | 1.6E0 | 8.8E1 | 9.8E3 | 2.1E3 | 240 | 17 | 154 | 17 | 0.57 |
| Kr | pg/ml | 3.8E-1 | 2.9E-1 | 2.2E0 | 1.2E0 | 4.2E0 | 2.2E0 | 1.0E-9 | 1.0E-9 | 3.5E1 | 8.0E0 | 240 | 17 | 154 | 17 | 0.47 |
| Ks | pg/ml | 1.4E4 | 8.0E3 | 2.0E4 | 1.3E4 | 1.8E4 | 1.4E4 | 5.1E1 | 4.1E2 | 1.1E5 | 5.0E4 | 240 | 17 | 154 | 17 | 0.37 |
| Kx | ng/ml | 1.0E-9 | 4.2E-3 | 6.6E-3 | 7.4E-3 | 1.4E-2 | 1.0E-2 | 1.0E-9 | 1.0E-9 | 1.0E-1 | 4.1E-2 | 247 | 17 | 160 | 17 | 0.57 |
| Ky | ng/ml | 8.5E-2 | 1.5E-1 | 3.5E-1 | 8.3E-1 | 7.8E-1 | 1.6E0 | 1.0E-9 | 1.0E-9 | 5.4E0 | 6.4E0 | 247 | 17 | 160 | 17 | 0.67 |
| Kz | ng/ml | 1.0E-9 | 1.0E-9 | 3.7E-3 | 2.7E-3 | 5.9E-3 | 3.9E-3 | 1.0E-9 | 1.0E-9 | 3.6E-2 | 1.4E-2 | 247 | 17 | 160 | 17 | 0.50 |
| Ld | ng/ml | 1.0E-9 | 3.6E0 | 3.6E0 | 4.3E0 | 9.2E0 | 5.1E0 | 1.0E-9 | 1.0E-9 | 8.4E1 | 1.9E1 | 246 | 17 | 159 | 17 | 0.63 |
| Lh | pg/ml | 1.2E4 | 1.7E4 | 2.0E4 | 2.4E4 | 2.5E4 | 2.4E4 | 1.0E-9 | 4.0E2 | 2.6E5 | 1.0E5 | 691 | 27 | 281 | 27 | 0.58 |
| Li | pg/ml | 2.8E3 | 4.0E3 | 1.5E4 | 1.0E4 | 5.9E4 | 1.6E4 | 1.0E-9 | 1.2E2 | 1.3E6 | 6.8E4 | 691 | 27 | 281 | 27 | 0.52 |
| Lj | pg/ml | 2.3E3 | 3.9E3 | 2.1E4 | 1.4E4 | 6.5E4 | 2.5E4 | 1.0E-9 | 3.4E1 | 4.7E5 | 9.4E4 | 691 | 27 | 281 | 27 | 0.52 |
| Rm | ng/ml | 1.9E1 | 2.4E1 | 4.9E1 | 6.1E1 | 7.4E1 | 8.0E1 | 2.2E-1 | 4.0E-1 | 4.0E2 | 2.5E2 | 245 | 16 | 159 | 16 | 0.53 |
| Rh | ng/ml | 1.3E2 | 7.9E1 | 3.6E2 | 2.1E2 | 1.2E3 | 2.5E2 | 3.6E0 | 1.8E1 | 1.7E4 | 8.5E2 | 245 | 16 | 159 | 16 | 0.42 |
| Ri | ng/ml | 1.0E-9 | 4.1E-2 | 4.4E0 | 6.4E0 | 1.6E1 | 1.3E1 | 1.0E-9 | 1.0E-9 | 2.2E2 | 4.1E1 | 246 | 16 | 160 | 16 | 0.54 |
| Rg | ng/ml | 1.0E-9 | 1.0E-9 | 7.1E-2 | 3.3E-3 | 4.2E-1 | 7.1E-3 | 1.0E-9 | 1.0E-9 | 4.6E0 | 2.8E-2 | 245 | 16 | 159 | 16 | 0.57 |
| Rj | ng/ml | 1.0E-9 | 1.0E-9 | 1.6E0 | 4.4E-2 | 6.0E0 | 1.8E-1 | 1.0E-9 | 1.0E-9 | 8.0E1 | 7.0E-1 | 246 | 16 | 160 | 16 | 0.38 |
| Rf | ng/ml | 3.7E-1 | 3.2E-1 | 9.8E-1 | 6.4E-1 | 1.9E0 | 6.9E-1 | 7.8E-3 | 3.9E-2 | 1.5E1 | 2.1E0 | 245 | 16 | 159 | 16 | 0.48 |
| Ql | pg/ml | 4.5E0 | 4.3E-1 | 1.4E1 | 6.0E0 | 3.1E1 | 7.8E0 | 1.0E-9 | 1.0E-9 | 2.9E2 | 2.4E1 | 249 | 16 | 162 | 16 | 0.42 |
| Qm | pg/ml | 3.9E0 | 1.0E-9 | 2.0E1 | 1.9E1 | 3.9E1 | 3.3E1 | 1.0E-9 | 1.0E-9 | 3.6E2 | 1.1E2 | 249 | 16 | 162 | 16 | 0.47 |
| Qn | pg/ml | 6.1E-1 | 1.2E0 | 6.9E0 | 1.4E1 | 2.2E1 | 2.5E1 | 1.0E-9 | 1.0E-9 | 2.2E2 | 7.5E1 | 249 | 16 | 162 | 16 | 0.57 |
| Nv | pg/ml | 3.8E3 | 5.0E3 | 1.1E4 | 1.5E4 | 4.8E4 | 3.1E4 | 1.0E-9 | 9.8E1 | 1.1E6 | 1.6E5 | 696 | 28 | 281 | 28 | 0.57 |
| Nw | pg/ml | 8.1E3 | 1.3E4 | 1.2E4 | 1.5E4 | 1.7E4 | 1.1E4 | 8.6E1 | 7.5E2 | 2.1E5 | 5.0E4 | 696 | 28 | 281 | 28 | 0.64 |
| Nx | pg/ml | 2.0E2 | 3.7E2 | 3.8E2 | 6.8E2 | 6.6E2 | 6.3E2 | 1.0E-9 | 1.0E-9 | 7.4E3 | 2.1E3 | 696 | 28 | 281 | 28 | 0.69 |
| Ny | pg/ml | 5.5E0 | 9.6E0 | 6.2E1 | 6.2E1 | 9.6E1 | 2.3E2 | 1.0E-9 | 1.0E-9 | 2.5E4 | 1.2E3 | 696 | 28 | 281 | 28 | 0.56 |
| Oa | pg/ml | 1.6E2 | 5.7E2 | 4.0E2 | 6.9E2 | 6.9E2 | 7.7E2 | 1.0E-9 | 1.0E-9 | 4.8E3 | 2.9E3 | 249 | 16 | 162 | 16 | 0.65 |
| Wn | ng/ml | 1.3E1 | 1.1E1 | 5.8E1 | 4.0E1 | 2.1E2 | 4.6E1 | 8.9E-1 | 9.8E-1 | 1.8E3 | 1.0E2 | 86 | 7 | 63 | 7 | 0.49 |

Figure 18 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Tk | ng/ml | 1.3E2 | 7.1E1 | 3.1E2 | 1.5E2 | 5.6E2 | 1.9E2 | 3.0E0 | 5.8E0 | 4.2E3 | 5.6E2 | 92 | 7 | 66 | 7 | 0.37 |
| Oe | pg/ml | 4.9E1 | 1.1E2 | 2.9E2 | 3.0E2 | 8.1E2 | 4.4E2 | 1.0E-9 | 1.0E-9 | 1.9E4 | 1.6E3 | 688 | 28 | 281 | 28 | 0.51 |
| Of | pg/ml | 1.8E2 | 1.1E2 | 6.4E3 | 8.6E3 | 3.1E4 | 2.5E4 | 1.0E-9 | 1.0E-9 | 6.2E5 | 1.2E5 | 695 | 28 | 281 | 28 | 0.47 |
| Og | pg/ml | 8.4E-2 | 1.0E-1 | 5.3E-1 | 2.9E-1 | 1.7E0 | 7.5E-1 | 1.0E-9 | 1.0E-9 | 2.0E1 | 4.0E0 | 695 | 28 | 281 | 28 | 0.48 |
| Oh | pg/ml | 2.4E0 | 4.5E0 | 2.3E1 | 8.0E0 | 1.6E2 | 1.2E1 | 1.0E-9 | 1.0E-9 | 3.5E3 | 5.6E1 | 695 | 28 | 281 | 28 | 0.56 |
| Oi | pg/ml | 2.3E0 | 3.1E0 | 6.1E0 | 5.5E0 | 9.9E0 | 7.7E0 | 1.0E-9 | 1.0E-9 | 8.6E1 | 3.6E1 | 695 | 28 | 281 | 28 | 0.52 |
| Ok | pg/ml | 3.5E2 | 6.1E2 | 5.0E2 | 8.1E2 | 5.2E2 | 9.7E2 | 1.3E1 | 4.2E1 | 5.2E3 | 5.2E3 | 695 | 28 | 281 | 28 | 0.63 |
| Om | pg/ml | 3.8E2 | 5.7E2 | 8.5E2 | 6.9E2 | 2.3E3 | 6.3E2 | 1.0E-9 | 1.0E-9 | 3.6E4 | 2.5E3 | 695 | 28 | 281 | 28 | 0.55 |
| On | pg/ml | 1.6E2 | 2.6E2 | 2.7E2 | 4.0E2 | 4.1E2 | 4.1E2 | 1.0E-9 | 1.2E1 | 4.5E3 | 1.7E3 | 695 | 28 | 281 | 28 | 0.62 |
| Or | pg/ml | 1.2E1 | 2.7E1 | 3.1E1 | 6.4E1 | 6.0E1 | 8.7E1 | 1.0E-9 | 1.0E-9 | 5.0E2 | 3.4E2 | 249 | 17 | 160 | 17 | 0.66 |
| Ow | pg/ml | 3.3E1 | 9.7E1 | 1.2E2 | 7.2E2 | 3.5E2 | 1.9E3 | 1.0E-9 | 1.0E-9 | 3.2E3 | 8.1E3 | 249 | 17 | 160 | 17 | 0.72 |
| Ou | pg/ml | 4.6E2 | 8.4E2 | 8.6E2 | 1.7E3 | 1.3E3 | 1.8E3 | 1.0E-9 | 1.0E-9 | 9.8E3 | 6.6E3 | 249 | 17 | 160 | 17 | 0.66 |
| Ul | ng/ml | 1.0E-9 | 1.0E-9 | 1.2E0 | 1.3E0 | 4.6E0 | 3.5E0 | 1.0E-9 | 1.0E-9 | 3.4E1 | 1.0E1 | 257 | 16 | 164 | 16 | 0.52 |
| Uo | ng/ml | 1.0E-9 | 1.0E-9 | 9.2E-2 | 9.1E-2 | 2.1E-1 | 1.7E-1 | 1.0E-9 | 1.0E-9 | 1.3E0 | 5.8E-1 | 257 | 16 | 164 | 16 | 0.54 |
| Uk | ng/ml | 1.0E-9 | 1.0E-9 | 7.8E-3 | 4.7E-3 | 2.7E-2 | 1.8E-2 | 1.0E-9 | 1.0E-9 | 3.2E-1 | 7.1E-2 | 257 | 16 | 164 | 16 | 0.41 |
| Um | ng/ml | 1.0E-9 | 1.0E-9 | 3.7E-1 | 6.7E-1 | 8.5E-1 | 1.1E0 | 1.0E-9 | 1.0E-9 | 6.8E0 | 2.7E0 | 257 | 16 | 164 | 16 | 0.53 |
| Uf | ng/ml | 5.1E-2 | 8.6E-2 | 1.2E-1 | 6.2E-1 | 1.9E-1 | 2.1E0 | 1.0E-3 | 3.5E-3 | 1.7E0 | 8.6E0 | 257 | 16 | 164 | 16 | 0.56 |
| Uh | ng/ml | 1.8E0 | 2.0E0 | 2.9E0 | 4.5E0 | 3.2E0 | 5.4E0 | 3.2E-2 | 1.3E-2 | 1.7E1 | 2.1E1 | 257 | 16 | 164 | 16 | 0.57 |
| Un | ng/ml | 1.8E0 | 2.3E0 | 2.1E0 | 2.0E0 | 1.3E0 | 1.1E0 | 2.0E-1 | 1.3E-1 | 8.0E0 | 3.9E0 | 257 | 16 | 164 | 16 | 0.52 |
| Ug | ng/ml | 1.4E1 | 6.2E0 | 2.7E1 | 1.9E1 | 2.8E1 | 2.8E1 | 6.9E-1 | 1.8E0 | 1.8E2 | 1.1E2 | 257 | 16 | 164 | 16 | 0.34 |
| Ur | ng/ml | 1.5E-1 | 6.5E-2 | 7.7E-1 | 5.8E-1 | 5.9E0 | 1.2E0 | 1.0E-9 | 1.0E-9 | 9.3E1 | 4.7E0 | 256 | 16 | 163 | 16 | 0.41 |
| Up | ng/ml | 1.0E-9 | 1.0E-9 | 5.4E-3 | 2.6E-3 | 2.5E-2 | 8.6E-3 | 1.0E-9 | 1.0E-9 | 3.3E-1 | 3.5E-2 | 256 | 16 | 163 | 16 | 0.48 |
| Us | ng/ml | 3.2E-3 | 1.0E-9 | 1.8E-2 | 7.9E-3 | 4.4E-2 | 1.7E-2 | 1.0E-9 | 1.0E-9 | 4.0E-1 | 6.3E-2 | 256 | 16 | 163 | 16 | 0.37 |
| Uv | ng/ml | 3.0E-3 | 1.5E-3 | 1.3E-2 | 5.3E-3 | 4.2E-2 | 8.9E-3 | 1.0E-9 | 1.0E-9 | 4.3E-1 | 3.3E-2 | 256 | 16 | 163 | 16 | 0.42 |
| Ut | ng/ml | 6.6E-1 | 3.1E-1 | 2.9E0 | 1.3E0 | 9.1E0 | 1.9E0 | 1.0E-9 | 1.0E-9 | 7.8E1 | 5.0E0 | 256 | 16 | 163 | 16 | 0.42 |
| Uu | ng/ml | 7.0E0 | 7.6E0 | 7.7E0 | 8.3E0 | 5.0E0 | 5.3E0 | 4.5E-1 | 1.3E0 | 2.6E1 | 2.1E1 | 256 | 16 | 163 | 16 | 0.54 |
| Vp | ng/ml | 1.0E-9 | 1.0E-9 | 4.0E-1 | 7.3E-2 | 3.6E0 | 1.7E-1 | 1.0E-9 | 1.0E-9 | 5.0E1 | 6.0E-1 | 257 | 16 | 164 | 16 | 0.52 |
| Vt | ng/ml | 6.0E0 | 8.4E0 | 8.4E0 | 9.3E0 | 9.1E0 | 6.7E0 | 4.3E-1 | 1.7E0 | 8.6E1 | 2.2E1 | 257 | 16 | 164 | 16 | 0.57 |
| Vu | ng/ml | 1.0E-9 | 5.3E-1 | 2.3E0 | 1.7E0 | 5.6E0 | 2.6E0 | 1.0E-9 | 1.0E-9 | 5.1E1 | 9.3E0 | 253 | 15 | 164 | 15 | 0.55 |
| Vq | ng/ml | 1.6E2 | 4.5E2 | 4.1E3 | 7.6E2 | 4.8E4 | 8.3E2 | 2.0E-1 | 1.7E1 | 6.8E5 | 2.3E3 | 203 | 11 | 135 | 11 | 0.61 |
| Vo | ng/ml | 2.6E1 | 2.5E1 | 2.4E1 | 2.3E1 | 5.4E0 | 5.1E0 | 2.4E0 | 8.0E0 | 4.8E1 | 3.0E1 | 257 | 16 | 164 | 16 | 0.41 |
| Vs | ng/ml | 1.0E-9 | 1.0E-9 | 6.7E0 | 9.5E0 | 2.4E1 | 2.3E1 | 1.0E-9 | 1.0E-9 | 2.3E2 | 9.4E1 | 253 | 16 | 161 | 16 | 0.53 |
| Vv | ng/ml | 2.9E0 | 3.0E0 | 6.1E0 | 4.2E0 | 1.0E1 | 6.5E0 | 1.0E-9 | 1.0E-9 | 8.4E1 | 2.6E1 | 256 | 16 | 164 | 16 | 0.47 |
| Oy | pg/ml | 5.3E-1 | 4.9E-1 | 6.6E0 | 2.2E0 | 3.2E1 | 4.0E0 | 1.0E-9 | 1.0E-9 | 4.0E2 | 1.5E1 | 694 | 28 | 280 | 28 | 0.50 |
| Oz | pg/ml | 1.3E-2 | 5.4E-2 | 3.4E-1 | 2.4E-1 | 1.5E0 | 3.9E-1 | 1.0E-9 | 1.0E-9 | 2.9E1 | 1.7E0 | 694 | 28 | 280 | 28 | 0.51 |
| Pa | pg/ml | 3.8E-1 | 4.1E-1 | 1.5E0 | 8.1E-1 | 5.5E0 | 1.0E0 | 1.0E-9 | 1.0E-9 | 8.6E1 | 4.4E0 | 694 | 28 | 280 | 28 | 0.55 |
| Pb | pg/ml | 1.0E-9 | 1.0E-9 | 9.3E-1 | 1.1E0 | 1.9E1 | 5.3E0 | 1.0E-9 | 1.0E-9 | 4.9E2 | 2.8E1 | 694 | 28 | 280 | 28 | 0.51 |
| Pc | pg/ml | 4.7E-2 | 2.7E-1 | 3.7E-1 | 3.8E-1 | 9.4E-1 | 4.7E-1 | 1.0E-9 | 1.0E-9 | 1.6E1 | 1.8E0 | 694 | 28 | 280 | 28 | 0.57 |
| Pd | pg/ml | 1.7E0 | 2.5E0 | 5.1E0 | 3.4E0 | 3.3E1 | 3.4E0 | 1.0E-9 | 1.0E-9 | 8.4E2 | 1.4E1 | 694 | 28 | 280 | 28 | 0.57 |
| Pe | pg/ml | 2.0E1 | 3.4E1 | 1.0E2 | 5.5E1 | 3.5E2 | 6.2E1 | 1.0E-9 | 1.0E-9 | 4.7E3 | 2.5E2 | 694 | 28 | 280 | 28 | 0.56 |
| Pf | pg/ml | 1.4E0 | 2.3E0 | 1.1E1 | 7.5E0 | 6.4E1 | 1.5E1 | 1.0E-9 | 1.0E-9 | 1.5E3 | 7.7E1 | 694 | 28 | 280 | 28 | 0.57 |
| Pg | pg/ml | 3.0E0 | 4.8E0 | 4.7E1 | 2.9E1 | 3.8E2 | 5.2E1 | 1.0E-9 | 1.0E-9 | 7.7E3 | 1.9E2 | 694 | 28 | 280 | 28 | 0.58 |
| Ph | ng/ml | 1.7E-1 | 1.7E-1 | 3.2E-1 | 3.6E-1 | 4.5E-1 | 5.5E-1 | 1.0E-9 | 1.0E-9 | 2.9E0 | 2.3E0 | 249 | 17 | 160 | 17 | 0.49 |
| Pi | ng/ml | 2.0E-1 | 2.2E-1 | 2.8E-1 | 2.9E-1 | 3.6E-1 | 2.6E-1 | 1.0E-9 | 1.0E-9 | 3.2E0 | 8.6E-1 | 249 | 17 | 160 | 17 | 0.53 |
| Pj | ng/mL | 4.8E0 | 5.1E0 | 5.9E0 | 5.5E0 | 4.5E0 | 3.7E0 | 3.8E-2 | 8.8E-1 | 3.1E1 | 1.3E1 | 249 | 17 | 160 | 17 | 0.48 |
| Pk | ng/ml | 8.9E-3 | 7.6E-3 | 1.4E-2 | 1.0E-2 | 2.2E-2 | 1.2E-2 | 1.0E-9 | 1.0E-9 | 2.5E-1 | 4.3E-2 | 249 | 17 | 160 | 17 | 0.42 |
| aA | mg/dL | 8.0E-1 | 9.0E-1 | 9.2E-1 | 1.0E0 | 4.7E-1 | 5.5E-1 | 2.0E-1 | 4.0E-1 | 4.2E0 | 3.2E0 | 2240 | 35 | 436 | 35 | 0.57 |
| aC | mg/mL | 2.9E0 | 1.9E0 | 3.2E0 | 2.4E0 | 1.4E0 | 1.3E0 | 8.5E-1 | 1.0E0 | 8.9E0 | 5.6E0 | 437 | 17 | 174 | 17 | 0.31 |
| aD | ug/mL | 3.1E0 | 4.1E0 | 4.4E0 | 5.3E0 | 3.9E0 | 4.2E0 | 4.3E-1 | 1.1E0 | 3.5E1 | 1.7E1 | 437 | 17 | 174 | 17 | 0.54 |
| aE | mg/mL | 5.6E-1 | 5.5E-1 | 5.8E-1 | 5.5E-1 | 1.5E-1 | 1.6E-1 | 2.1E-1 | 2.5E-1 | 1.1E0 | 8.6E-1 | 437 | 17 | 174 | 17 | 0.44 |
| aF | ng/mL | 2.1E0 | 2.0E0 | 4.1E0 | 5.1E0 | 6.1E0 | 7.8E0 | 4.3E-3 | 4.3E-3 | 5.0E1 | 2.9E1 | 437 | 17 | 174 | 17 | 0.49 |
| aG | mg/mL | 1.4E-1 | 1.3E-1 | 1.6E-1 | 1.5E-1 | 9.1E-2 | 8.2E-2 | 1.7E-2 | 5.6E-2 | 5.4E-1 | 3.8E-1 | 437 | 17 | 174 | 17 | 0.45 |
| aH | ug/mL | 7.5E1 | 7.6E1 | 8.3E1 | 8.5E1 | 4.4E1 | 4.1E1 | 4.6E0 | 2.3E1 | 2.9E2 | 1.4E2 | 437 | 17 | 174 | 17 | 0.54 |
| aI | ug/mL | 1.9E2 | 1.7E2 | 1.9E2 | 1.7E2 | 6.0E1 | 6.7E1 | 2.8E1 | 7.7E1 | 3.7E2 | 2.8E2 | 437 | 17 | 174 | 17 | 0.43 |
| aJ | ug/mL | 2.4E0 | 3.7E0 | 2.9E0 | 4.2E0 | 2.1E0 | 2.8E0 | 7.6E-1 | 9.5E-1 | 1.7E1 | 1.1E1 | 437 | 17 | 174 | 17 | 0.65 |
| aK | ng/mL | 1.6E0 | 8.3E-1 | 2.5E0 | 1.8E0 | 2.7E0 | 1.9E0 | 2.9E-4 | 9.1E-2 | 1.8E1 | 5.6E0 | 437 | 17 | 174 | 17 | 0.42 |
| aL | mg/mL | 8.1E-1 | 8.3E-1 | 8.2E-1 | 8.5E-1 | 2.5E-1 | 3.2E-1 | 1.9E-1 | 2.9E-1 | 1.7E0 | 1.6E0 | 437 | 17 | 174 | 17 | 0.52 |

Figure 18 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aM | U/mL | 2.2E1 | 2.1E1 | 4.5E1 | 4.5E1 | 9.6E1 | 4.3E1 | 4.2E-2 | 4.2E-2 | 1.6E3 | 1.3E2 | 437 | 17 | 174 | 17 | 0.55 |
| aN | U/mL | 1.3E1 | 2.1E1 | 2.0E1 | 3.1E1 | 2.8E1 | 2.6E1 | 2.5E-3 | 2.5E-3 | 3.8E2 | 9.5E1 | 437 | 17 | 174 | 17 | 0.66 |
| aO | pg/mL | 3.1E1 | 3.2E1 | 3.2E2 | 2.1E2 | 8.3E2 | 4.0E2 | 6.0E-2 | 6.0E-2 | 6.6E3 | 1.3E3 | 437 | 17 | 174 | 17 | 0.52 |
| aP | ng/mL | 1.6E0 | 1.8E0 | 2.0E0 | 2.2E0 | 1.8E0 | 1.4E0 | 4.5E-1 | 7.0E-1 | 2.8E1 | 6.6E0 | 437 | 17 | 174 | 17 | 0.55 |
| aQ | ng/mL | 3.0E-1 | 2.8E-1 | 4.7E-1 | 3.0E-1 | 4.8E-1 | 2.5E-1 | 2.0E-4 | 6.7E-2 | 4.0E0 | 9.2E-1 | 437 | 17 | 174 | 17 | 0.39 |
| aR | ng/mL | 1.7E0 | 2.4E0 | 2.7E0 | 2.4E0 | 3.3E0 | 1.7E0 | 1.8E-1 | 3.6E-1 | 3.4E1 | 7.9E0 | 437 | 17 | 174 | 17 | 0.54 |
| aS | ng/mL | 2.6E-1 | 2.9E-1 | 6.5E-1 | 4.5E-1 | 1.9E0 | 4.0E-1 | 4.2E-3 | 7.2E-2 | 3.3E1 | 1.3E0 | 437 | 17 | 174 | 17 | 0.53 |
| aU | pg/mL | 7.8E1 | 5.3E1 | 1.3E2 | 9.4E1 | 1.5E2 | 8.7E1 | 7.4E-2 | 6.5E0 | 1.3E3 | 3.3E2 | 437 | 17 | 174 | 17 | 0.44 |
| aV | ng/mL | 6.3E-1 | 3.6E-1 | 1.1E0 | 8.3E-1 | 2.0E0 | 1.4E0 | 7.6E-4 | 3.3E-2 | 3.3E1 | 6.0E0 | 437 | 17 | 174 | 17 | 0.37 |
| aW | pg/mL | 1.9E1 | 1.9E1 | 2.0E1 | 1.8E1 | 2.0E1 | 9.1E0 | 7.2E-2 | 7.2E-2 | 2.4E2 | 3.1E1 | 437 | 17 | 174 | 17 | 0.50 |
| aX | ng/mL | 9.4E0 | 7.1E0 | 1.5E1 | 2.3E1 | 1.9E1 | 5.0E1 | 3.0E-1 | 1.4E0 | 2.2E2 | 2.1E2 | 437 | 17 | 174 | 17 | 0.47 |
| aY | pg/mL | 5.4E1 | 7.8E1 | 7.7E1 | 9.6E1 | 8.7E1 | 6.9E1 | 4.1E-1 | 1.7E1 | 1.2E3 | 2.4E2 | 437 | 17 | 174 | 17 | 0.62 |
| aZ | pg/mL | 2.2E2 | 1.7E2 | 5.0E2 | 5.0E2 | 9.8E2 | 1.0E3 | 1.7E0 | 1.7E0 | 1.2E4 | 4.3E3 | 437 | 17 | 174 | 17 | 0.48 |
| bA | ng/mL | 8.0E0 | 2.7E1 | 3.0E1 | 8.7E1 | 7.8E1 | 1.3E2 | 3.0E-2 | 1.4E0 | 9.4E2 | 4.6E2 | 437 | 17 | 174 | 17 | 0.69 |
| bB | ng/mL | 3.1E2 | 2.2E2 | 3.4E2 | 2.8E2 | 1.7E2 | 1.9E2 | 2.1E0 | 1.2E1 | 1.0E3 | 6.2E2 | 437 | 17 | 174 | 17 | 0.40 |
| bC | ng/mL | 3.3E2 | 4.7E2 | 5.6E2 | 1.2E3 | 7.4E2 | 1.4E3 | 9.8E0 | 1.5E2 | 4.7E3 | 4.7E3 | 437 | 17 | 174 | 17 | 0.66 |
| bE | mg/mL | 5.5E0 | 5.9E0 | 5.8E0 | 6.2E0 | 2.0E0 | 3.1E0 | 9.8E-1 | 1.9E0 | 1.3E1 | 1.3E1 | 437 | 17 | 174 | 17 | 0.50 |
| bF | pg/mL | 1.9E1 | 2.3E1 | 1.6E2 | 2.4E2 | 9.8E2 | 4.7E2 | 5.0E-2 | 8.5E0 | 1.1E4 | 1.7E3 | 437 | 17 | 174 | 17 | 0.62 |
| bG | ng/mL | 1.6E0 | 2.8E0 | 2.7E0 | 3.2E0 | 3.3E0 | 3.3E0 | 2.2E-1 | 1.6E-1 | 2.6E1 | 1.1E1 | 437 | 17 | 174 | 17 | 0.54 |
| bH | pg/mL | 5.7E-1 | 5.7E-1 | 4.9E0 | 2.6E0 | 1.6E1 | 3.4E0 | 5.7E-1 | 5.7E-1 | 2.8E2 | 1.1E1 | 437 | 17 | 174 | 17 | 0.46 |
| bI | ng/mL | 4.0E-3 | 4.0E-3 | 6.5E-2 | 4.7E-2 | 1.6E-1 | 1.0E-1 | 4.0E-3 | 4.0E-3 | 1.3E0 | 3.1E-1 | 437 | 17 | 174 | 17 | 0.50 |
| bJ | mg/mL | 2.4E0 | 1.6E0 | 2.7E0 | 2.4E0 | 2.1E0 | 2.3E0 | 2.5E-4 | 2.1E-2 | 1.3E1 | 9.0E0 | 437 | 17 | 174 | 17 | 0.43 |
| bL | pg/mL | 4.0E0 | 4.7E0 | 8.3E0 | 8.1E0 | 1.1E1 | 9.2E0 | 4.6E-2 | 4.6E-2 | 8.0E1 | 3.2E1 | 437 | 17 | 174 | 17 | 0.50 |
| bM | mg/mL | 1.7E0 | 2.4E0 | 2.0E0 | 2.6E0 | 1.4E0 | 1.9E0 | 9.2E-3 | 7.1E-1 | 8.8E0 | 8.4E0 | 437 | 17 | 174 | 17 | 0.61 |
| bN | ng/mL | 4.3E1 | 3.9E1 | 1.4E2 | 8.4E1 | 2.9E2 | 1.4E2 | 1.4E-1 | 1.8E0 | 1.9E3 | 5.7E2 | 437 | 17 | 174 | 17 | 0.48 |
| bO | ng/mL | 4.0E-2 | 4.0E-2 | 1.0E1 | 8.5E0 | 2.3E1 | 1.4E1 | 4.0E-2 | 4.0E-2 | 1.9E2 | 3.8E1 | 437 | 17 | 174 | 17 | 0.51 |
| bP | mg/mL | 5.3E-1 | 6.8E-1 | 7.6E-1 | 8.2E-1 | 6.8E-1 | 7.4E-1 | 4.9E-2 | 9.7E-2 | 4.8E0 | 3.1E0 | 437 | 17 | 174 | 17 | 0.52 |
| bQ | pg/mL | 1.5E1 | 1.4E1 | 6.4E1 | 3.5E1 | 6.5E2 | 4.4E1 | 1.5E-1 | 4.4E0 | 1.3E4 | 1.8E2 | 437 | 17 | 174 | 17 | 0.52 |
| bR | ng/mL | 1.2E-2 | 1.2E-2 | 1.4E-1 | 6.4E-2 | 4.6E-1 | 1.0E-1 | 1.2E-2 | 1.2E-2 | 8.7E0 | 3.2E-1 | 437 | 17 | 174 | 17 | 0.41 |
| bS | pg/mL | 9.4E-1 | 9.4E-1 | 7.2E0 | 3.3E0 | 2.9E1 | 9.9E0 | 9.4E-1 | 9.4E-1 | 3.9E2 | 4.2E1 | 437 | 17 | 174 | 17 | 0.46 |
| bU | ng/mL | 1.5E-1 | 6.8E-2 | 2.0E-1 | 1.4E-1 | 3.8E-1 | 1.6E-1 | 1.3E-2 | 1.3E-2 | 6.6E0 | 4.9E-1 | 437 | 17 | 174 | 17 | 0.44 |
| bV | pg/mL | 4.7E2 | 4.9E2 | 5.5E2 | 6.2E2 | 5.8E2 | 3.9E2 | 1.6E2 | 2.6E2 | 1.2E4 | 1.6E3 | 437 | 17 | 174 | 17 | 0.52 |
| bW | pg/mL | 3.2E2 | 3.7E2 | 4.9E2 | 1.7E3 | 4.8E2 | 4.7E3 | 8.4E1 | 1.3E2 | 4.8E3 | 2.0E4 | 437 | 17 | 174 | 17 | 0.55 |
| bX | ng/mL | 1.5E-3 | 2.5E-5 | 2.8E-3 | 1.6E-3 | 3.5E-3 | 3.2E-3 | 2.5E-5 | 2.5E-5 | 2.0E-2 | 1.2E-2 | 437 | 17 | 174 | 17 | 0.38 |
| bZ | | 2.3E2 | 2.8E2 | 9.1E2 | 7.0E2 | 4.1E3 | 7.6E2 | 1.5E-1 | 7.4E1 | 5.8E4 | 1.9E3 | 437 | 17 | 174 | 17 | 0.57 |
| cA | pg/mL | 6.0E-1 | 6.0E-1 | 2.8E0 | 1.2E0 | 1.8E1 | 2.5E0 | 6.0E-1 | 6.0E-1 | 3.7E2 | 1.1E1 | 437 | 17 | 174 | 17 | 0.46 |
| cB | ng/mL | 6.0E-2 | 3.6E-2 | 9.3E-2 | 5.1E-2 | 1.0E-1 | 5.0E-2 | 1.7E-3 | 1.7E-3 | 5.7E-1 | 1.6E-1 | 437 | 17 | 174 | 17 | 0.39 |
| cC | pg/mL | 4.6E1 | 3.8E1 | 4.8E1 | 4.1E1 | 4.0E1 | 2.4E1 | 1.0E0 | 1.0E0 | 4.5E2 | 9.6E1 | 437 | 17 | 174 | 17 | 0.44 |
| cD | pg/mL | 5.4E0 | 3.8E0 | 1.5E1 | 8.5E0 | 5.7E1 | 1.3E1 | 3.3E-1 | 3.3E-1 | 7.2E2 | 4.1E1 | 437 | 17 | 174 | 17 | 0.41 |
| cE | pg/mL | 3.2E1 | 6.7E1 | 1.5E2 | 5.1E2 | 4.6E2 | 1.0E3 | 1.2E-1 | 1.2E-1 | 3.8E3 | 3.8E3 | 437 | 17 | 174 | 17 | 0.63 |
| cF | pg/mL | 1.3E1 | 9.4E0 | 2.1E1 | 1.3E1 | 3.2E1 | 1.3E1 | 5.3E-1 | 5.3E-1 | 2.7E2 | 4.1E1 | 437 | 17 | 174 | 17 | 0.46 |
| cG | pg/mL | 4.3E1 | 6.0E1 | 1.1E2 | 1.3E2 | 5.2E2 | 1.5E2 | 7.8E0 | 1.0E1 | 1.0E4 | 5.6E2 | 437 | 17 | 174 | 17 | 0.65 |
| cH | uIU/mL | 3.1E0 | 2.9E0 | 6.5E0 | 3.0E0 | 1.2E1 | 2.7E0 | 8.6E-3 | 8.6E-3 | 1.6E2 | 1.0E1 | 437 | 17 | 174 | 17 | 0.40 |
| cI | ng/mL | 5.7E0 | 4.4E0 | 1.1E1 | 1.7E1 | 1.5E1 | 2.6E1 | 1.0E-3 | 3.2E-2 | 1.0E2 | 1.0E2 | 437 | 17 | 174 | 17 | 0.50 |
| cJ | ug/mL | 7.0E1 | 4.0E1 | 1.2E2 | 6.9E1 | 1.5E2 | 8.7E1 | 4.0E0 | 1.2E1 | 9.6E2 | 3.3E2 | 437 | 17 | 174 | 17 | 0.37 |
| cK | ng/mL | 3.8E-3 | 3.8E-3 | 5.5E-2 | 7.8E-3 | 1.9E-1 | 1.7E-2 | 3.8E-3 | 3.8E-3 | 1.7E0 | 7.3E-2 | 437 | 17 | 174 | 17 | 0.45 |
| cL | pg/mL | 1.9E2 | 2.2E2 | 3.6E2 | 5.4E2 | 1.3E3 | 6.7E2 | 1.6E1 | 6.5E1 | 2.4E4 | 2.6E3 | 437 | 17 | 174 | 17 | 0.64 |
| cM | pg/mL | 2.8E2 | 2.2E2 | 3.1E2 | 2.3E2 | 2.0E2 | 1.3E2 | 8.7E0 | 4.7E1 | 1.6E3 | 4.8E2 | 437 | 17 | 174 | 17 | 0.39 |
| cN | pg/mL | 1.2E2 | 1.3E2 | 1.3E2 | 1.6E2 | 6.4E1 | 7.3E1 | 3.8E1 | 6.8E1 | 1.1E3 | 3.5E2 | 437 | 17 | 174 | 17 | 0.64 |
| cO | pg/mL | 2.2E2 | 2.3E2 | 3.1E2 | 2.8E2 | 9.3E2 | 2.2E2 | 5.4E1 | 1.0E2 | 1.9E4 | 1.1E3 | 437 | 17 | 174 | 17 | 0.52 |
| cP | ng/mL | 2.5E3 | 2.8E3 | 2.6E3 | 2.8E3 | 9.2E2 | 9.6E2 | 6.2E2 | 1.4E3 | 5.7E3 | 4.8E3 | 437 | 17 | 174 | 17 | 0.55 |
| cQ | ng/mL | 4.3E-2 | 5.9E-2 | 1.3E-1 | 2.6E-1 | 2.4E-1 | 4.8E-1 | 2.0E-3 | 2.0E-3 | 2.2E0 | 1.9E0 | 437 | 17 | 174 | 17 | 0.56 |
| cR | ng/mL | 2.8E2 | 3.7E2 | 4.9E2 | 6.5E2 | 8.0E2 | 1.1E3 | 2.0E1 | 3.6E1 | 8.9E3 | 4.8E3 | 437 | 17 | 174 | 17 | 0.56 |
| cS | ng/mL | 2.6E2 | 2.4E2 | 3.8E2 | 4.0E2 | 3.8E2 | 3.2E2 | 4.1E1 | 9.1E1 | 2.7E3 | 1.2E3 | 437 | 17 | 174 | 17 | 0.52 |
| cT | ng/mL | 2.9E1 | 8.2E1 | 8.3E1 | 2.2E2 | 1.8E2 | 4.0E2 | 3.6E0 | 5.1E0 | 2.1E3 | 1.3E3 | 437 | 17 | 174 | 17 | 0.64 |
| cU | ng/mL | 5.4E1 | 7.8E1 | 7.5E1 | 7.2E1 | 9.9E1 | 4.6E1 | 6.2E0 | 5.4E0 | 1.6E3 | 1.5E2 | 437 | 17 | 174 | 17 | 0.54 |
| cV | ng/mL | 1.7E-1 | 2.8E-1 | 3.8E-1 | 1.0E0 | 2.3E0 | 2.4E0 | 3.4E-4 | 3.0E-2 | 4.7E1 | 9.7E0 | 437 | 17 | 174 | 17 | 0.63 |

Figure 18 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cW | mIU/mL | 5.3E-2 | 4.2E-2 | 1.5E-1 | 6.4E-2 | 7.2E-1 | 5.5E-2 | 3.7E-4 | 1.9E-2 | 9.7E0 | 2.1E-1 | 437 | 17 | 174 | 17 | 0.46 |
| cX | ng/mL | 9.9E-2 | 3.6E-1 | 1.3E0 | 4.9E0 | 4.2E0 | 9.9E0 | 2.3E-4 | 2.3E-4 | 2.8E1 | 2.8E1 | 437 | 17 | 174 | 17 | 0.57 |
| cY | ng/mL | 8.9E0 | 7.9E0 | 1.3E1 | 1.1E1 | 1.3E1 | 1.1E1 | 1.5E-1 | 6.1E-1 | 8.3E1 | 3.7E1 | 437 | 17 | 174 | 17 | 0.45 |
| cZ | ug/mL | 1.5E1 | 1.5E1 | 1.6E1 | 1.7E1 | 7.1E0 | 9.2E0 | 2.3E0 | 5.6E0 | 5.7E1 | 4.0E1 | 437 | 17 | 174 | 17 | 0.54 |
| dA | pg/mL | 3.3E2 | 3.2E2 | 3.8E2 | 3.6E2 | 3.1E2 | 2.1E2 | 9.0E1 | 1.6E2 | 5.8E3 | 9.3E2 | 437 | 17 | 174 | 17 | 0.46 |
| dB | ug/mL | 1.7E1 | 2.1E1 | 1.7E1 | 1.9E1 | 1.6E1 | 9.9E0 | 9.4E-1 | 2.5E0 | 2.5E2 | 3.2E1 | 437 | 17 | 174 | 17 | 0.63 |
| dC | nmol/L | 3.5E1 | 3.6E1 | 3.9E1 | 3.9E1 | 1.8E1 | 1.5E1 | 7.9E0 | 1.3E1 | 1.4E2 | 7.5E1 | 437 | 17 | 174 | 17 | 0.52 |
| dD | ug/mL | 3.7E1 | 3.0E1 | 3.8E1 | 3.5E1 | 1.1E1 | 1.3E1 | 1.3E1 | 1.6E1 | 7.6E1 | 6.2E1 | 437 | 17 | 174 | 17 | 0.42 |
| dE | ng/mL | 4.7E-1 | 3.8E-1 | 6.1E-1 | 3.3E-1 | 7.3E-1 | 2.8E-1 | 8.4E-3 | 8.4E-3 | 7.2E0 | 7.4E-1 | 437 | 17 | 174 | 17 | 0.39 |
| dF | ng/mL | 2.2E2 | 2.7E2 | 2.6E2 | 3.7E2 | 1.8E2 | 2.9E2 | 7.5E1 | 6.1E1 | 1.3E3 | 1.2E3 | 437 | 17 | 174 | 17 | 0.63 |
| dG | ng/mL | 1.1E1 | 1.6E1 | 1.4E1 | 2.1E1 | 1.2E1 | 1.8E1 | 2.5E0 | 4.2E0 | 1.8E2 | 7.6E1 | 437 | 17 | 174 | 17 | 0.65 |
| dH | pg/mL | 7.5E0 | 9.0E0 | 1.3E1 | 1.7E1 | 4.0E1 | 1.9E1 | 4.0E-2 | 2.2E0 | 6.7E2 | 7.9E1 | 437 | 17 | 174 | 17 | 0.63 |
| dI | pg/mL | 4.6E-1 | 4.6E-1 | 2.3E0 | 1.8E0 | 1.6E1 | 2.1E0 | 4.6E-1 | 4.6E-1 | 3.3E2 | 6.2E0 | 437 | 17 | 174 | 17 | 0.58 |
| dJ | ng/mL | 1.9E0 | 2.3E0 | 2.2E0 | 2.4E0 | 1.2E0 | 1.2E0 | 3.2E-2 | 3.2E-2 | 6.9E0 | 4.4E0 | 437 | 17 | 174 | 17 | 0.56 |
| dK | uIU/mL | 1.9E0 | 2.4E0 | 3.1E0 | 3.0E0 | 6.0E0 | 3.4E0 | 2.8E-4 | 4.3E-1 | 7.9E1 | 1.5E1 | 437 | 17 | 174 | 17 | 0.54 |
| dL | ng/mL | 8.7E2 | 1.2E3 | 1.0E3 | 1.3E3 | 4.9E2 | 8.1E2 | 3.4E2 | 3.3E2 | 3.4E3 | 3.8E3 | 437 | 17 | 174 | 17 | 0.62 |
| dM | pg/mL | 9.6E2 | 9.5E2 | 1.1E3 | 1.4E3 | 8.8E2 | 8.8E2 | 3.5E2 | 3.4E2 | 1.2E4 | 3.6E3 | 437 | 17 | 174 | 17 | 0.57 |
| dN | ug/mL | 9.3E1 | 1.2E2 | 9.9E1 | 1.2E2 | 3.6E1 | 5.0E1 | 2.5E1 | 1.6E1 | 2.8E2 | 2.0E2 | 437 | 17 | 174 | 17 | 0.62 |
| dR | pg/ml | 1.6E3 | 1.3E3 | 2.4E3 | 2.4E3 | 2.4E3 | 2.7E3 | 1.4E2 | 1.8E2 | 1.5E4 | 8.9E3 | 287 | 17 | 167 | 17 | 0.46 |
| dX | ng/ml | 8.1E-2 | 8.2E-2 | 1.2E-1 | 2.1E-1 | 1.9E-1 | 2.8E-1 | 2.6E-3 | 2.6E-3 | 1.2E0 | 7.6E-1 | 121 | 7 | 43 | 7 | 0.53 |
| eF | ng/mL | 4.0E0 | 4.5E0 | 4.9E0 | 5.8E0 | 4.2E0 | 2.8E0 | 1.2E0 | 2.6E0 | 4.6E1 | 1.2E1 | 302 | 17 | 168 | 17 | 0.65 |
| eC | pg/mL | 3.1E2 | 2.2E2 | 3.6E2 | 4.4E2 | 2.2E2 | 4.2E2 | 9.9E0 | 1.3E2 | 1.4E3 | 1.6E3 | 231 | 15 | 159 | 15 | 0.45 |
| eD | pg/ml | 2.3E2 | 2.0E2 | 5.8E2 | 1.9E2 | 1.2E3 | 7.8E1 | 5.2E-1 | 3.1E1 | 8.3E3 | 3.0E2 | 197 | 16 | 131 | 16 | 0.41 |
| eM | ng/ml | 3.2E0 | 8.0E0 | 4.9E0 | 7.7E0 | 5.5E0 | 5.6E0 | 3.3E-1 | 1.6E0 | 3.9E1 | 1.7E1 | 155 | 7 | 67 | 7 | 0.69 |
| eP | ng/ml | 3.7E-3 | 1.7E-1 | 6.4E-1 | 4.5E-1 | 1.6E0 | 8.0E-1 | 3.7E-3 | 3.7E-3 | 1.2E1 | 2.2E0 | 121 | 7 | 43 | 7 | 0.58 |
| fP | ng/ml | 2.4E2 | 3.1E2 | 2.8E2 | 3.4E2 | 1.7E2 | 1.5E2 | 1.8E0 | 1.1E2 | 1.0E3 | 5.9E2 | 276 | 17 | 162 | 17 | 0.63 |
| fR | pg/ml | 1.2E5 | 2.1E5 | 1.7E5 | 3.0E5 | 1.4E5 | 2.1E5 | 3.1E4 | 1.0E5 | 7.7E5 | 6.3E5 | 295 | 10 | 90 | 10 | 0.71 |
| gL | pg/ml | 6.3E4 | 7.1E4 | 7.0E4 | 7.9E4 | 3.1E4 | 3.3E4 | 1.4E4 | 4.3E4 | 2.0E5 | 1.7E5 | 287 | 17 | 167 | 17 | 0.60 |
| gP | U/ml | 2.8E2 | 2.5E2 | 2.9E2 | 2.4E2 | 1.1E2 | 8.0E1 | 1.2E1 | 7.1E1 | 1.1E3 | 3.9E2 | 298 | 17 | 168 | 17 | 0.38 |
| gW | ng/ml | 6.8E2 | 6.8E2 | 1.3E3 | 9.6E2 | 1.7E3 | 1.3E3 | 3.1E-1 | 3.5E1 | 9.5E3 | 5.4E3 | 252 | 16 | 157 | 16 | 0.46 |
| tF | pg/mL | 1.4E3 | 1.9E3 | 1.5E4 | 5.5E3 | 4.5E4 | 7.6E3 | 1.2E1 | 1.8E1 | 3.2E5 | 2.3E4 | 231 | 15 | 159 | 15 | 0.52 |
| hA | ng/ml | 2.0E0 | 2.5E0 | 9.2E0 | 1.1E1 | 3.7E1 | 1.9E1 | 1.7E-2 | 1.7E-2 | 3.5E2 | 6.1E1 | 197 | 16 | 131 | 16 | 0.57 |
| nM | pg/ml | 1.0E-9 | 1.0E-9 | 7.9E1 | 1.0E-9 | 9.0E2 | 0.0E0 | 1.0E-9 | 1.0E-9 | 1.0E4 | 1.0E-9 | 131 | 13 | 103 | 13 | 0.49 |
| nN | pg/ml | 1.2E3 | 1.8E3 | 5.1E3 | 2.1E3 | 2.5E4 | 1.8E3 | 1.1E2 | 1.1E2 | 2.7E5 | 6.2E3 | 131 | 13 | 103 | 13 | 0.55 |
| nO | pg/ml | 2.7E1 | 3.3E1 | 4.3E1 | 6.7E1 | 4.2E1 | 8.3E1 | 3.5E0 | 9.6E0 | 2.4E2 | 3.1E2 | 131 | 13 | 103 | 13 | 0.59 |
| nR | pg/ml | 1.3E1 | 1.9E1 | 3.8E1 | 9.6E1 | 8.7E1 | 1.1E2 | 1.0E-9 | 2.2E0 | 8.2E2 | 3.1E2 | 131 | 13 | 103 | 13 | 0.66 |
| nT | pg/ml | 8.5E1 | 4.3E1 | 2.2E2 | 1.1E2 | 8.0E2 | 1.3E2 | 1.0E-9 | 2.0E1 | 6.6E3 | 4.9E2 | 131 | 13 | 103 | 13 | 0.48 |
| nU | pg/ml | 2.9E1 | 1.2E2 | 2.6E2 | 1.5E2 | 1.5E3 | 1.9E2 | 1.0E-9 | 1.0E-9 | 1.3E4 | 7.5E2 | 131 | 13 | 103 | 13 | 0.71 |
| lW | pg/ml | 1.0E-9 | 1.0E-9 | 1.3E1 | 1.9E1 | 4.7E1 | 4.7E1 | 1.0E-9 | 1.0E-9 | 3.9E2 | 1.6E2 | 131 | 13 | 103 | 13 | 0.51 |
| lX | pg/ml | 1.0E3 | 8.6E2 | 1.1E3 | 9.1E2 | 5.6E2 | 5.1E2 | 1.2E2 | 3.3E2 | 2.6E3 | 1.8E3 | 131 | 13 | 103 | 13 | 0.41 |
| lY | pg/ml | 2.0E1 | 1.8E1 | 2.3E1 | 1.9E1 | 2.1E1 | 9.5E0 | 1.0E-9 | 4.2E0 | 1.4E2 | 3.9E1 | 131 | 13 | 103 | 13 | 0.45 |
| mE | pg/ml | 1.0E-9 | 1.0E-9 | 2.9E0 | 3.4E0 | 8.3E0 | 7.7E0 | 1.0E-9 | 1.0E-9 | 5.8E1 | 2.8E1 | 131 | 13 | 103 | 13 | 0.51 |
| mF | pg/ml | 1.0E-9 | 8.7E-1 | 4.0E0 | 2.8E0 | 2.3E1 | 3.4E0 | 1.0E-9 | 1.0E-9 | 2.5E2 | 9.6E0 | 131 | 13 | 103 | 13 | 0.63 |
| mH | pg/ml | 3.6E0 | 2.7E0 | 5.1E0 | 4.6E0 | 6.7E0 | 5.0E0 | 2.3E-1 | 7.6E-1 | 5.3E1 | 1.8E1 | 131 | 13 | 103 | 13 | 0.46 |
| mI | pg/ml | 1.0E-9 | 1.0E-9 | 1.2E1 | 1.2E1 | 2.7E1 | 2.1E1 | 1.0E-9 | 1.0E-9 | 1.8E2 | 6.1E1 | 131 | 13 | 103 | 13 | 0.47 |
| mM | pg/ml | 2.2E1 | 3.2E1 | 6.5E1 | 9.3E1 | 1.5E2 | 1.3E2 | 1.0E-9 | 1.0E-9 | 1.1E3 | 4.0E2 | 131 | 13 | 103 | 13 | 0.58 |
| mP | pg/ml | 1.4E1 | 1.9E1 | 1.8E1 | 2.6E1 | 2.3E1 | 1.7E1 | 1.0E-9 | 1.3E1 | 1.9E2 | 7.7E1 | 130 | 13 | 102 | 13 | 0.73 |
| mS | pg/ml | 1.8E3 | 2.0E3 | 2.0E3 | 2.0E3 | 1.6E3 | 1.2E3 | 1.0E-9 | 6.6E2 | 1.3E4 | 5.1E3 | 131 | 13 | 103 | 13 | 0.51 |
| mT | pg/ml | 4.8E1 | 3.5E1 | 1.2E2 | 1.6E2 | 2.1E2 | 2.4E2 | 9.7E0 | 1.2E1 | 1.4E3 | 8.0E2 | 130 | 13 | 102 | 13 | 0.48 |
| mU | pg/ml | 2.2E0 | 3.2E0 | 5.5E0 | 5.2E0 | 2.1E1 | 5.6E0 | 1.0E-9 | 1.7E0 | 2.2E2 | 2.2E1 | 130 | 13 | 102 | 13 | 0.66 |
| mW | pg/ml | 2.3E3 | 2.6E3 | 2.6E3 | 3.0E3 | 1.4E3 | 2.3E3 | 3.1E2 | 5.7E2 | 1.0E4 | 9.8E3 | 130 | 13 | 102 | 13 | 0.55 |
| mY | pg/ml | 5.6E2 | 8.9E2 | 8.6E2 | 1.0E3 | 1.3E3 | 7.7E2 | 1.0E-9 | 1.5E2 | 1.1E4 | 2.6E3 | 131 | 13 | 103 | 13 | 0.65 |
| mZ | pg/ml | 2.2E2 | 2.7E2 | 3.8E2 | 4.3E2 | 4.4E2 | 4.8E2 | 1.0E-9 | 1.6E1 | 3.1E3 | 1.5E3 | 130 | 13 | 102 | 13 | 0.49 |
| nA | pg/ml | 2.0E0 | 3.3E0 | 1.1E1 | 1.3E1 | 4.4E1 | 2.2E1 | 1.0E-9 | 1.0E-9 | 4.4E2 | 6.5E1 | 130 | 13 | 102 | 13 | 0.61 |
| nB | pg/ml | 3.0E2 | 4.2E2 | 3.1E2 | 4.2E2 | 1.5E2 | 1.7E2 | 3.0E1 | 1.5E2 | 8.2E2 | 7.8E2 | 131 | 13 | 103 | 13 | 0.69 |
| nC | pg/ml | 1.0E-9 | 1.5E2 | 3.7E3 | 4.9E4 | 3.2E4 | 1.2E5 | 1.0E-9 | 1.0E-9 | 3.7E5 | 3.8E5 | 131 | 13 | 103 | 13 | 0.65 |
| nD | pg/ml | 8.5E0 | 2.0E1 | 3.5E1 | 3.9E1 | 2.0E2 | 7.3E1 | 1.0E-9 | 1.0E-9 | 1.7E3 | 2.6E2 | 130 | 13 | 102 | 13 | 0.64 |

Figure 18 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nF | pg/ml | 1.0E-9 | 1.0E-9 | 5.0E0 | 8.2E0 | 2.6E1 | 1.4E1 | 1.0E-9 | 1.0E-9 | 2.4E2 | 4.7E1 | 131 | 13 | 103 | 13 | 0.63 |
| nH | pg/ml | 3.8E-1 | 5.4E0 | 8.9E1 | 1.0E3 | 8.8E2 | 2.8E3 | 1.0E-9 | 1.0E-9 | 1.0E4 | 1.0E4 | 130 | 13 | 102 | 13 | 0.62 |
| nI | pg/ml | 4.6E1 | 4.6E1 | 1.6E2 | 1.5E2 | 8.4E2 | 3.3E2 | 1.0E-9 | 1.0E-9 | 9.2E3 | 1.2E3 | 131 | 13 | 103 | 13 | 0.54 |
| nJ | pg/ml | 1.7E-1 | 1.1E0 | 4.1E1 | 1.2E1 | 4.5E2 | 3.6E1 | 1.0E-9 | 1.0E-9 | 5.2E3 | 1.3E2 | 131 | 13 | 103 | 13 | 0.62 |
| nK | pg/ml | 1.0E-9 | 2.3E1 | 5.8E1 | 4.3E1 | 3.4E2 | 6.5E1 | 1.0E-9 | 1.0E-9 | 3.2E3 | 2.2E2 | 130 | 13 | 102 | 13 | 0.64 |
| nL | pg/ml | 1.0E-9 | 5.2E0 | 3.9E2 | 1.5E3 | 3.9E3 | 3.8E3 | 1.0E-9 | 1.0E-9 | 4.5E4 | 1.4E4 | 131 | 13 | 103 | 13 | 0.66 |
| wJ | pg/ml | 1.5E5 | 9.6E4 | 1.7E5 | 1.2E5 | 1.0E5 | 5.5E4 | 1.1E4 | 8.4E4 | 5.8E5 | 2.4E5 | 113 | 7 | 91 | 7 | 0.31 |
| wK | pg/ml | 3.5E4 | 6.2E4 | 4.8E4 | 5.5E4 | 5.4E4 | 2.9E4 | 3.7E3 | 1.6E4 | 5.0E5 | 1.0E5 | 113 | 7 | 91 | 7 | 0.62 |
| wL | pg/ml | 3.9E0 | 1.3E0 | 4.1E1 | 7.7E0 | 1.1E2 | 1.1E1 | 1.0E-9 | 1.0E-9 | 8.4E2 | 2.9E1 | 113 | 7 | 91 | 7 | 0.43 |
| wP | pg/ml | 2.6E4 | 2.6E4 | 4.2E4 | 8.5E4 | 4.6E4 | 1.1E5 | 1.1E3 | 2.0E4 | 3.0E5 | 3.0E5 | 113 | 7 | 91 | 7 | 0.61 |
| wQ | pg/ml | 3.7E1 | 4.3E1 | 6.1E1 | 8.0E1 | 8.1E1 | 7.6E1 | 1.0E-9 | 1.7E1 | 5.1E2 | 2.4E2 | 113 | 7 | 91 | 7 | 0.64 |
| hR | pg/ml | 2.6E4 | 2.3E4 | 2.7E4 | 2.5E4 | 1.1E4 | 9.9E3 | 1.1E1 | 1.3E4 | 5.8E4 | 4.5E4 | 189 | 15 | 129 | 15 | 0.43 |
| hV | pg/ml | 4.4E2 | 4.9E2 | 4.7E2 | 4.2E2 | 2.4E2 | 2.0E2 | 6.8E1 | 9.6E1 | 1.5E3 | 7.1E2 | 189 | 15 | 129 | 15 | 0.45 |
| hW | pg/ml | 1.5E3 | 1.9E3 | 2.0E3 | 2.0E3 | 1.6E3 | 9.2E2 | 2.2E2 | 7.1E2 | 1.0E4 | 3.5E3 | 189 | 15 | 129 | 15 | 0.58 |
| hX | pg/ml | 9.0E2 | 1.1E3 | 1.0E3 | 1.1E3 | 7.8E2 | 5.3E2 | 1.3E2 | 2.1E2 | 8.6E3 | 2.2E3 | 189 | 15 | 129 | 15 | 0.57 |
| iA | pg/ml | 1.4E2 | 1.9E2 | 2.8E2 | 3.1E2 | 6.2E2 | 3.0E2 | 5.8E0 | 4.1E1 | 7.1E3 | 9.5E2 | 231 | 15 | 159 | 15 | 0.61 |
| iB | ng/ml | 4.8E0 | 5.5E0 | 6.0E0 | 8.3E0 | 4.9E0 | 7.1E0 | 3.3E-2 | 1.6E0 | 3.8E1 | 2.4E1 | 197 | 16 | 131 | 16 | 0.60 |
| iC | U/ml | 2.1E-1 | 4.9E-1 | 9.0E-1 | 1.1E0 | 4.6E0 | 2.6E0 | 1.0E-9 | 1.0E-9 | 5.5E1 | 1.1E1 | 197 | 16 | 131 | 16 | 0.68 |
| tQ | pg/ml | 1.1E3 | 1.7E3 | 1.2E3 | 1.6E3 | 5.5E2 | 4.0E2 | 2.8E2 | 1.0E3 | 2.5E3 | 2.0E3 | 108 | 7 | 88 | 7 | 0.73 |
| tT | pg/ml | 1.7E1 | 3.0E1 | 2.0E1 | 3.8E1 | 1.5E1 | 2.8E1 | 5.4E0 | 1.3E1 | 1.2E2 | 9.3E1 | 109 | 7 | 89 | 7 | 0.76 |
| tS | pg/ml | 1.1E0 | 7.7E-1 | 1.3E0 | 3.2E0 | 1.3E0 | 4.6E0 | 1.0E-9 | 1.0E-9 | 8.5E0 | 1.0E1 | 109 | 7 | 89 | 7 | 0.47 |
| tX | pg/ml | 9.9E-1 | 2.1E0 | 1.2E0 | 3.7E0 | 9.8E-1 | 3.9E0 | 2.5E-2 | 7.6E-2 | 7.0E0 | 1.0E1 | 109 | 7 | 89 | 7 | 0.66 |
| tO | pg/ml | 4.4E0 | 3.8E0 | 5.1E0 | 7.0E0 | 3.3E0 | 7.1E0 | 1.0E-9 | 8.6E-1 | 1.8E1 | 1.9E1 | 109 | 7 | 89 | 7 | 0.49 |
| tR | pg/ml | 2.1E-1 | 2.5E-1 | 2.9E-1 | 7.9E-1 | 2.9E-1 | 1.1E0 | 1.0E-9 | 3.1E-2 | 1.6E0 | 2.5E0 | 108 | 7 | 88 | 7 | 0.56 |
| tU | pg/ml | 9.1E0 | 1.3E1 | 1.1E1 | 1.3E1 | 6.9E0 | 8.5E0 | 2.2E-1 | 1.5E0 | 4.4E1 | 2.5E1 | 111 | 7 | 90 | 7 | 0.59 |
| tN | pg/ml | 1.8E1 | 4.8E1 | 2.3E1 | 6.2E1 | 1.9E1 | 5.9E1 | 1.0E-9 | 6.0E0 | 1.5E2 | 1.6E2 | 109 | 7 | 88 | 7 | 0.63 |
| tV | ng/ml | 4.7E2 | 9.5E2 | 6.4E2 | 1.2E3 | 5.0E2 | 8.6E2 | 5.3E1 | 4.8E2 | 2.9E3 | 3.1E3 | 113 | 7 | 91 | 7 | 0.78 |
| iH | ng/ml | 1.6E5 | 2.0E5 | 1.5E5 | 1.8E5 | 4.7E4 | 6.7E4 | 5.1E4 | 2.9E3 | 2.7E5 | 2.5E5 | 231 | 15 | 159 | 15 | 0.67 |
| iJ | ng/ml | 5.4E4 | 4.3E4 | 5.5E4 | 4.7E4 | 2.9E4 | 3.4E4 | 5.5E3 | 1.8E3 | 2.5E5 | 1.5E5 | 231 | 15 | 159 | 15 | 0.35 |
| hB | ng/ml | 4.1E-1 | 6.2E-1 | 5.0E-1 | 8.0E-1 | 3.3E-1 | 6.8E-1 | 1.0E-9 | 1.2E-1 | 2.3E0 | 2.4E0 | 231 | 15 | 159 | 15 | 0.64 |
| hC | pg/ml | 3.9E3 | 5.2E3 | 6.8E3 | 8.9E3 | 1.0E4 | 1.1E4 | 1.0E-9 | 1.0E-9 | 1.1E5 | 4.3E4 | 231 | 15 | 159 | 15 | 0.55 |
| hF | ng/ml | 1.0E-9 | 1.0E-9 | 2.1E1 | 1.0E-9 | 2.7E2 | 0.0E0 | 1.0E-9 | 1.0E-9 | 4.0E3 | 1.0E-9 | 231 | 15 | 159 | 15 | 0.49 |
| hG | pg/ml | 6.9E3 | 6.9E3 | 7.4E3 | 7.3E3 | 3.2E3 | 2.4E3 | 2.8E1 | 3.7E3 | 1.9E4 | 1.2E4 | 231 | 15 | 159 | 15 | 0.51 |
| iO | ng/ml | 3.8E5 | 3.2E5 | 4.0E5 | 3.3E5 | 1.8E5 | 1.5E5 | 1.1E4 | 6.4E4 | 1.1E6 | 6.7E5 | 231 | 15 | 159 | 15 | 0.40 |
| iP | ng/ml | 5.0E4 | 4.2E4 | 5.5E4 | 4.7E4 | 5.2E4 | 2.5E4 | 1.0E-9 | 3.4E3 | 5.5E5 | 9.7E4 | 231 | 15 | 159 | 15 | 0.48 |
| iZ | ng/ml | 1.6E3 | 1.8E3 | 1.8E3 | 2.0E3 | 7.8E2 | 7.6E2 | 4.7E2 | 1.1E3 | 5.7E3 | 4.1E3 | 230 | 15 | 158 | 15 | 0.59 |
| yD | ng/ml | 1.5E-2 | 1.3E-2 | 1.5E-2 | 1.7E-2 | 6.7E-3 | 7.9E-3 | 1.0E-9 | 6.3E-3 | 4.3E-2 | 2.9E-2 | 113 | 7 | 91 | 7 | 0.54 |
| wB | pg/ml | 7.4E3 | 1.2E4 | 9.4E3 | 1.7E4 | 7.2E3 | 1.3E4 | 1.7E3 | 5.1E3 | 4.1E4 | 4.2E4 | 113 | 7 | 91 | 7 | 0.71 |
| rC | pg/ml | 1.6E3 | 1.5E3 | 2.2E3 | 2.0E3 | 2.2E3 | 1.7E3 | 1.0E-9 | 1.9E2 | 1.5E4 | 7.3E3 | 189 | 16 | 128 | 16 | 0.48 |
| rB | pg/ml | 2.4E1 | 3.5E1 | 4.3E1 | 5.7E1 | 8.9E1 | 6.5E1 | 1.0E-9 | 1.0E-9 | 9.5E2 | 2.5E2 | 189 | 16 | 128 | 16 | 0.60 |
| jD | ng/ml | 3.1E1 | 2.4E1 | 4.8E1 | 3.4E1 | 6.1E1 | 3.3E1 | 1.0E-9 | 1.0E-9 | 5.1E2 | 1.0E2 | 196 | 16 | 131 | 16 | 0.45 |
| jE | ng/ml | 1.0E-9 | 1.0E-9 | 7.1E0 | 6.5E0 | 1.7E1 | 1.3E1 | 1.0E-9 | 1.0E-9 | 1.2E2 | 3.6E1 | 196 | 16 | 131 | 16 | 0.51 |
| jF | ng/ml | 4.2E1 | 3.4E1 | 5.7E1 | 3.8E1 | 6.3E1 | 4.2E1 | 1.0E-9 | 1.0E-9 | 3.5E2 | 1.5E2 | 196 | 16 | 131 | 16 | 0.43 |
| jG | ng/ml | 4.6E3 | 3.7E3 | 4.7E3 | 4.1E3 | 2.0E3 | 2.4E3 | 7.6E2 | 6.7E2 | 1.1E4 | 7.8E3 | 197 | 16 | 131 | 16 | 0.42 |
| jH | ng/ml | 7.6E1 | 6.5E1 | 8.5E1 | 7.4E1 | 4.8E1 | 3.1E1 | 1.3E1 | 4.2E1 | 3.3E2 | 1.3E2 | 197 | 16 | 131 | 16 | 0.44 |
| jI | ng/ml | 6.8E1 | 7.5E1 | 7.3E1 | 8.4E1 | 3.3E1 | 3.5E1 | 1.9E1 | 5.0E1 | 2.5E2 | 1.8E2 | 197 | 16 | 131 | 16 | 0.61 |
| wC | ng/ml | 1.5E0 | 1.5E0 | 1.9E0 | 1.7E0 | 1.7E0 | 1.3E0 | 2.5E-1 | 6.1E-1 | 1.5E1 | 4.3E0 | 113 | 7 | 91 | 7 | 0.48 |
| wD | ng/ml | 1.7E1 | 4.8E1 | 4.8E1 | 6.0E1 | 2.0E2 | 5.4E1 | 2.1E0 | 9.1E0 | 2.1E3 | 1.5E2 | 113 | 7 | 91 | 7 | 0.73 |
| wE | ng/ml | 4.8E1 | 5.0E1 | 4.9E1 | 4.5E1 | 2.3E1 | 1.6E1 | 3.2E0 | 2.0E1 | 1.4E2 | 6.3E1 | 113 | 7 | 91 | 7 | 0.47 |
| wG | ng/ml | 6.4E-2 | 2.3E-2 | 1.0E-1 | 6.0E-2 | 1.3E-1 | 7.4E-2 | 1.0E-9 | 1.0E-9 | 7.1E-1 | 1.8E-1 | 113 | 7 | 91 | 7 | 0.44 |
| wH | ng/ml | 1.8E-2 | 9.5E-2 | 1.5E-1 | 5.4E-1 | 5.2E-1 | 7.4E-1 | 1.0E-9 | 1.0E-9 | 4.2E0 | 1.9E0 | 113 | 7 | 91 | 7 | 0.63 |
| wF | ng/ml | 1.4E-1 | 4.3E-1 | 1.5E0 | 1.4E0 | 7.1E0 | 1.8E0 | 1.0E-9 | 1.0E-9 | 5.7E1 | 4.7E0 | 113 | 7 | 91 | 7 | 0.65 |
| rA | pg/ml | 2.6E1 | 3.8E1 | 3.1E1 | 4.0E1 | 2.5E1 | 2.4E1 | 1.0E-9 | 5.8E0 | 2.0E2 | 9.3E1 | 197 | 17 | 131 | 17 | 0.61 |
| qZ | pg/ml | 4.1E1 | 2.7E1 | 3.7E2 | 1.0E3 | 1.8E3 | 3.1E3 | 1.0E-9 | 5.2E-4 | 1.0E4 | 1.0E4 | 155 | 10 | 118 | 10 | 0.49 |
| qY | pg/ml | 2.6E1 | 2.3E1 | 5.1E1 | 3.3E1 | 6.6E1 | 2.7E1 | 8.7E-1 | 5.1E0 | 5.3E2 | 9.8E1 | 197 | 17 | 131 | 17 | 0.48 |
| qX | pg/ml | 5.9E1 | 8.7E1 | 6.5E1 | 9.5E1 | 4.2E1 | 6.7E1 | 1.0E-9 | 2.9E0 | 2.1E2 | 2.1E2 | 197 | 17 | 131 | 17 | 0.61 |
| qW | pg/ml | 9.2E0 | 1.0E1 | 1.4E1 | 1.1E1 | 1.6E1 | 7.7E0 | 1.0E-9 | 1.0E-9 | 1.2E2 | 2.8E1 | 197 | 17 | 131 | 17 | 0.49 |

Figure 18 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| qV | pg/ml | 2.2E3 | 2.2E3 | 2.9E3 | 2.7E3 | 2.1E3 | 1.5E3 | 1.0E2 | 1.7E2 | 1.1E4 | 5.2E3 | 197 | 17 | 131 | 17 | 0.51 |
| qU | pg/ml | 6.1E1 | 1.0E2 | 1.6E2 | 1.3E2 | 2.8E2 | 1.5E2 | 1.0E-9 | 1.0E-9 | 2.1E3 | 5.1E2 | 197 | 17 | 131 | 17 | 0.52 |
| qT | pg/ml | 4.0E1 | 8.7E1 | 6.8E1 | 1.1E2 | 9.8E1 | 1.0E2 | 1.0E-9 | 1.2E1 | 9.0E2 | 4.4E2 | 197 | 17 | 131 | 17 | 0.67 |
| jK | ng/ml | 1.6E3 | 1.7E3 | 1.7E3 | 1.7E3 | 6.5E2 | 5.0E2 | 2.8E2 | 8.7E2 | 4.3E3 | 2.4E3 | 197 | 16 | 131 | 16 | 0.52 |
| jL | ng/ml | 1.9E2 | 2.3E2 | 2.8E2 | 3.4E2 | 2.5E2 | 3.8E2 | 3.6E1 | 9.8E1 | 2.1E3 | 1.7E3 | 197 | 16 | 131 | 16 | 0.57 |
| jM | ng/ml | 7.4E4 | 6.7E4 | 7.8E4 | 7.5E4 | 3.9E4 | 4.2E4 | 3.9E2 | 1.1E4 | 1.9E5 | 1.6E5 | 197 | 16 | 131 | 16 | 0.48 |
| jO | pg/ml | 2.1E5 | 2.2E5 | 2.6E5 | 2.7E5 | 1.5E5 | 1.8E5 | 5.2E4 | 1.2E5 | 1.1E6 | 8.1E5 | 197 | 16 | 131 | 16 | 0.50 |
| jP | pg/ml | 2.2E5 | 2.4E5 | 2.6E5 | 2.5E5 | 1.6E5 | 1.1E5 | 3.6E4 | 7.8E4 | 9.2E5 | 5.0E5 | 197 | 16 | 131 | 16 | 0.53 |
| jQ | pg/ml | 2.7E3 | 2.7E3 | 3.8E3 | 3.0E3 | 3.5E3 | 2.0E3 | 1.0E-9 | 2.9E2 | 1.8E4 | 7.1E3 | 197 | 16 | 131 | 16 | 0.49 |
| jR | pg/ml | 7.7E3 | 7.0E3 | 1.2E4 | 9.7E3 | 1.3E4 | 9.5E3 | 1.0E-9 | 2.9E2 | 9.0E4 | 3.4E4 | 197 | 16 | 131 | 16 | 0.47 |
| jT | pg/ml | 1.8E5 | 1.7E5 | 1.8E5 | 1.7E5 | 6.6E4 | 6.0E4 | 6.8E4 | 8.8E4 | 4.5E5 | 3.1E5 | 197 | 16 | 131 | 16 | 0.44 |
| jU | mIU/ml | 4.6E0 | 2.6E0 | 1.1E1 | 7.3E0 | 1.7E1 | 1.1E1 | 6.2E-2 | 6.3E-2 | 1.1E2 | 4.3E1 | 197 | 16 | 131 | 16 | 0.40 |
| jV | mIU/ml | 1.5E0 | 1.7E0 | 3.8E0 | 3.4E0 | 6.4E0 | 4.9E0 | 1.7E-3 | 1.1E-3 | 3.5E1 | 1.8E1 | 197 | 16 | 131 | 16 | 0.46 |
| jY | ng/ml | 5.9E-4 | 2.7E-3 | 5.8E-3 | 9.8E-3 | 2.7E-2 | 2.3E-2 | 1.0E-9 | 1.0E-9 | 3.0E-1 | 9.4E-2 | 197 | 16 | 131 | 16 | 0.59 |
| kC | pg/ml | 9.7E1 | 1.0E2 | 1.8E2 | 3.1E2 | 3.8E2 | 7.3E2 | 2.1E1 | 3.6E1 | 3.5E3 | 2.7E3 | 131 | 13 | 103 | 13 | 0.48 |
| kE | pg/ml | 1.3E5 | 1.2E5 | 1.3E5 | 1.2E5 | 3.8E4 | 4.1E4 | 1.2E4 | 3.8E4 | 2.3E5 | 1.9E5 | 131 | 13 | 103 | 13 | 0.44 |
| kF | pg/mL | 6.0E1 | 6.5E1 | 6.8E1 | 7.0E1 | 4.8E1 | 2.5E1 | 2.6E1 | 4.0E1 | 5.1E2 | 1.3E2 | 131 | 13 | 103 | 13 | 0.57 |
| kG | pg/mL | 9.2E3 | 8.4E3 | 1.2E4 | 1.3E4 | 1.4E4 | 1.4E4 | 7.5E2 | 3.2E3 | 1.2E5 | 5.8E4 | 131 | 13 | 103 | 13 | 0.51 |
| kI | pg/ml | 1.8E2 | 2.0E2 | 2.2E2 | 2.6E2 | 1.3E2 | 1.4E2 | 4.4E1 | 8.8E1 | 8.7E2 | 5.5E2 | 131 | 13 | 103 | 13 | 0.58 |
| kK | pg/ml | 1.0E2 | 1.2E2 | 1.6E2 | 2.3E2 | 1.9E2 | 2.6E2 | 6.4E0 | 5.1E1 | 1.6E3 | 9.1E2 | 131 | 13 | 103 | 13 | 0.59 |
| kN | pg/ml | 9.5E2 | 8.8E2 | 2.0E3 | 1.1E3 | 5.2E3 | 9.4E2 | 7.6E1 | 9.5E1 | 5.5E4 | 3.8E3 | 131 | 13 | 103 | 13 | 0.47 |
| kO | pg/ml | 7.2E3 | 6.9E3 | 8.6E3 | 1.9E4 | 1.1E4 | 3.9E4 | 3.4E3 | 3.3E3 | 1.3E5 | 1.5E5 | 131 | 13 | 103 | 13 | 0.49 |
| kP | pg/ml | 6.3E3 | 5.4E3 | 7.5E3 | 6.4E3 | 6.2E3 | 3.5E3 | 8.6E2 | 1.5E3 | 4.8E4 | 1.3E4 | 131 | 13 | 103 | 13 | 0.48 |
| kQ | pg/ml | 4.1E3 | 4.3E3 | 4.9E3 | 4.4E3 | 3.0E3 | 1.4E3 | 5.6E2 | 2.5E3 | 2.5E4 | 7.0E3 | 231 | 15 | 159 | 15 | 0.50 |
| kR | pg/ml | 2.1E1 | 2.0E1 | 3.1E1 | 2.8E1 | 6.9E1 | 2.1E1 | 1.0E-9 | 5.6E0 | 1.0E3 | 7.7E1 | 231 | 15 | 159 | 15 | 0.50 |
| kS | pg/ml | 8.0E2 | 1.0E3 | 9.7E2 | 1.0E3 | 1.0E3 | 4.5E2 | 8.2E1 | 2.5E2 | 1.4E4 | 1.7E3 | 231 | 15 | 159 | 15 | 0.61 |
| rZ | ng/ml | 1.0E-9 | 5.7E-3 | 5.4E-3 | 2.6E-2 | 1.5E-2 | 7.4E-2 | 1.0E-9 | 1.0E-9 | 1.1E-1 | 3.0E-1 | 190 | 16 | 126 | 16 | 0.65 |
| rY | ng/ml | 5.7E-2 | 5.1E-2 | 3.6E-1 | 1.2E0 | 2.3E0 | 4.4E0 | 1.0E-9 | 1.0E-9 | 2.3E1 | 1.8E1 | 190 | 16 | 126 | 16 | 0.55 |
| rX | ng/ml | 1.0E-9 | 1.0E-9 | 6.9E-2 | 1.7E-1 | 4.2E-1 | 6.0E-1 | 1.0E-9 | 1.0E-9 | 3.7E0 | 2.4E0 | 190 | 16 | 126 | 16 | 0.54 |
| lK | pg/ml | 9.9E1 | 4.0E1 | 1.9E2 | 9.8E1 | 3.1E2 | 1.4E2 | 1.0E-9 | 1.0E-9 | 3.3E3 | 5.0E2 | 196 | 16 | 131 | 16 | 0.36 |
| lL | pg/ml | 1.6E3 | 1.1E3 | 2.6E3 | 1.7E3 | 3.7E3 | 1.8E3 | 1.5E1 | 3.8E2 | 4.2E4 | 7.7E3 | 197 | 16 | 131 | 16 | 0.40 |
| lM | pg/ml | 1.1E3 | 1.2E3 | 3.5E3 | 5.0E3 | 7.5E3 | 7.7E3 | 1.2E2 | 2.8E2 | 5.1E4 | 2.7E4 | 197 | 16 | 131 | 16 | 0.58 |
| lN | pg/ml | 1.0E-9 | 1.0E-9 | 4.2E0 | 3.8E0 | 1.5E1 | 6.0E0 | 1.0E-9 | 1.0E-9 | 1.5E2 | 2.0E1 | 197 | 16 | 131 | 16 | 0.53 |
| lO | pg/ml | 1.0E-9 | 1.0E-9 | 1.6E0 | 1.0E-9 | 1.1E1 | 0.0E0 | 1.0E-9 | 1.0E-9 | 1.3E2 | 1.0E-9 | 196 | 16 | 131 | 16 | 0.48 |
| nW | pg/ml | 1.1E5 | 1.1E5 | 1.1E5 | 1.2E5 | 2.5E4 | 3.5E4 | 5.8E4 | 6.7E4 | 1.8E5 | 1.7E5 | 231 | 15 | 159 | 15 | 0.52 |
| nY | pg/ml | 2.1E3 | 2.0E3 | 2.4E3 | 2.4E3 | 1.6E3 | 1.4E3 | 5.1E2 | 7.6E2 | 1.3E4 | 5.0E3 | 231 | 15 | 159 | 15 | 0.50 |
| oO | pg/ml | 7.8E4 | 1.2E5 | 1.1E5 | 1.5E5 | 9.7E4 | 8.2E4 | 1.5E4 | 5.1E4 | 6.2E5 | 2.8E5 | 123 | 12 | 97 | 12 | 0.69 |
| oP | pg/ml | 1.2E5 | 2.0E5 | 1.4E5 | 2.2E5 | 9.1E4 | 1.2E5 | 2.4E4 | 7.8E4 | 4.5E5 | 4.8E5 | 123 | 12 | 97 | 12 | 0.72 |
| oQ | pg/ml | 2.8E3 | 4.4E3 | 3.5E3 | 5.4E3 | 2.8E3 | 3.2E3 | 9.3E2 | 1.9E3 | 2.1E4 | 1.2E4 | 123 | 12 | 97 | 12 | 0.72 |
| oE | pg/ml | 1.3E2 | 1.4E2 | 3.6E2 | 5.4E2 | 5.4E2 | 8.4E2 | 1.0E-9 | 2.7E1 | 4.7E3 | 2.8E3 | 231 | 15 | 159 | 15 | 0.52 |
| oF | pg/ml | 7.7E3 | 1.3E4 | 2.0E4 | 2.6E4 | 3.6E4 | 3.2E4 | 6.4E1 | 4.6E2 | 2.5E5 | 1.1E5 | 231 | 15 | 159 | 15 | 0.55 |
| oH | pg/ml | 4.4E1 | 2.7E1 | 9.3E1 | 6.7E1 | 1.4E2 | 8.0E1 | 4.2E0 | 4.3E-1 | 9.9E2 | 2.6E2 | 231 | 15 | 159 | 15 | 0.40 |
| oK | pg/ml | 7.6E2 | 1.3E3 | 1.8E3 | 1.5E3 | 2.5E3 | 1.6E3 | 5.2E1 | 1.8E2 | 1.8E4 | 6.8E3 | 231 | 15 | 159 | 15 | 0.54 |
| oN | pg/ml | 5.0E2 | 5.8E2 | 7.5E2 | 6.9E2 | 1.4E3 | 4.3E2 | 1.5E2 | 2.2E2 | 1.8E4 | 1.9E3 | 231 | 15 | 159 | 15 | 0.57 |
| pF | pg/ml | 4.5E-1 | 3.8E-1 | 1.0E0 | 1.3E0 | 5.7E0 | 2.1E0 | 1.0E-9 | 1.0E-9 | 8.7E1 | 7.8E0 | 231 | 15 | 159 | 15 | 0.54 |

Analyte panel data:

Unconstrained panels with 3 analytes, where 1.0E-10 >= 'model p-value' > 0. Contains 1 panels of 17,333,483 total panels evaluated. : ChTvkE Unconstrained panels with 3 analytes, where 1.0E-9 >= 'model p-value' > 1.0E-10. Contains 4 panels of 17,333,483 total panels evaluated. : oP{nK(Ef Iz) ChmF} liLdmP Unconstrained panels with 3 analytes, where 1.0E-8 >= 'model p-value' > 1.0E-9. Contains 7 panels of 17,333,483 total panels evaluated. : Ib{kE(dF Tv) oP(mF Ow) oQoH} AjnAoP BaNgPz Unconstrained panels with 3 analytes, where 1.0E-7 >= 'model p-value' > 1.0E-8. Contains 23 panels of 17,333,483 total panels evaluated. : oP{mF(Kj Ld oK Ut) mS(Cp Ef) ApnK ChaN MxIb} Qw{cX(gP Ib Mf Ub) Ub(bC Pz) IbbA} Ng{Pz(bA Dg Kf)} Ib{JinU nRoH kIlM} LdaYmF

Figure 18 Continued

Unconstrained panels with 3 analytes, where 1.0E-6 >= 'model p-value' > 1.0E-7. Contains 283 panels of 17,333,483 total panels evaluated. :
Qw{cX(aJ aX bC bE bW cH cN cZ dG dK Ed eF Hw Ij Jn Ju Kg Kr Ky Lw Md Me Mi Nf Ng Ow Pk Pz Qc Qy Rj Uf Ur) Ub(aJ aY bA Bc bW cH cJ cL cN cT cV DG eF gP Ib Ji Jj Jl Jn Mp Nx Or Ow Pk Qa Qx Rj Uc) Ib(aJ aX Ba bC cL cN cT cV eF gP Ji Jn Kf Kq Nj oH Pz Tn) gP(aJ aY bA Bc cH cJ Ed Jn Ml Ng Or Rj) Ng(BA bC Dg eF Jg Kf Pz Uc) Is(Js Kr Mf) mF(oP oQ) PzUk QaQc RjbW bGoP dGkE} oP{mF(Aj Al AX bG Di dL Ef Gl Hb Hf Id iJ iO Iz Kk Ko KR Ph) Ib(cF cS Ed Et Ji kE kI Kk Ld nA nC Nj nK nL oH Oi) Ch(aX Ed kE Kk mP mS nA nC nF nK nL Ow) Cp(nA nC nD nK nL Oa Pa) nA(bG Ef Iz oH) nK(Ad Ao Bb Bg) Di(nC Ng nL) Aw(nC nL) Ef(iO Kk) Iz(Kk mS) NgiO} Ib{nR(In Ji kE Kn Ld IK Ow) kE(cE dM Fy hB Ji Ma) oH(Ad Dg Kf Kl Kp Uu) Tv(kI mF nC nL) Ow(nJ nU oO oQ) nC(Fy Ji) ExNx KkmU LhmP} Ng{Pz(Ad aJ BC cT dF dG eF Kq) Kf(gP Kk Mf Pk) Nx(Ex Gz) DgqX OwbC} Is{Hw(Ij Iq Ly Nd Ne) Ml(Ij Iq Nd) li(fR nC) Iq(Ij Lv) InPz} Ch{Ow(kE mP nF nJ nR nU) Tv(kI mF mP) LdmP Ohkl} Em{Kg(Nx Ok Ou) JoOu LdbP} Pz{Ct(bA cT) Of(bA cT) InJn} Ii{Nx(Ex fR Gz)} Jn{Lv(Ij Iq) LyHw} Ld{aY(nA nL) InnU} nF{oH(dG oQ) aSbA} cN{JjdX aVeP} AwnRIK CtOwnU Unconstrained panels with 3 analytes, where 1.0E-5 >= 'model p-value' > 1.0E-6. Contains 3,276 panels of 17,333,483 total panels evaluated. :
Qw{cX(AA AD aE AF aG aH al Aj aK AL aM AN AO AP aQ AR AS aU aV aW Ax aY aZ BA BB Bc bF BG bH bl bJ bL bM BN BO bP bQ bR bS bU bV bX bZ cA cB cC cD cE cF cG Ch cl cJ cK cL cM CO CP CQ cR CS CT CU CV CW Cx cY dA DB DC DD DE dF Dg dH DJ dJ Dk DL dM dN Dp Ef Et Ex Ez Fa Fb Fn Fp Fr Fw GL Gp Ha Hb HC Hf Hq Hr Hu Hv Hx Ic Id Ih Ii iJ Ik Il Im In IO Ip Iq Ir Is It Iu Iv Iz Jd Je Jf Jg Jh Ji Jj Jk Jl Jm Jo Jp Jq Jr Js Jt Jv Jy Kc Kd Ke Kf Ki Kj Kk Kl Kn Ko Kp Kq Ks Kx Kz Ld Lh Li Lj Lu Lv Lx Ly Lz Ma Mb Mc Mg Mh Mj Mk Ml Mm Mn Mp Mq Mr Ms Mt Mu Mv Mw Mx My Mz Na Nb Nc Nd Ne Nh Ni Nj Nk Nl Nm Nn No Nq Nr Ns Nt Nu Nv Nw Nx NY Oa Oe Of Og OH Oi Ok Om On Or Ou Oy Oz Pa Pb Pc Pd Pe PF Pg Ph Pi Pj Po Qa Qb Qd Qe Qg Qh Ql Qm Qn Qt Qu Qv Qx Qz Ra Rb Rc Rf Rg Rh Ri Rm Sr Ss St Tz Ua Uc Ud Ue Ug Uh Uk Ul Um Un Uo Up Us Ut Uu Uv Vo Vp Vs Vt Vu Vv Wm Tj) Ub(aA aC AD aE aF aG aH al Aj aK AL aM AN AO AP aQ AR AS aU aV AW AX aZ Ba BB bE bF BG bH bl bJ bL bM BN BO bP bQ bR bS bU bV bX bZ cA cB cC cD cE cF cG Ch cl cK cM CO CP CQ cR CS Ct CU Cv CW Cx cY cZ dA DB DC DD DE dF dH Dl dJ DK DL dM dN Dp dR Ed Ef Et Ez Fa Fb Fn FP Fr Fw Fy GL Gp Ha Hb Hc Hf Hq Hr Hu Hv Hw Hx Ic Id Ih Ii IJ Ik Il Im In Is Iu Iz Jd Je Jf Jg Jh Jk Jm Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Ny Oa Oe Of Og OH Oi Ok Om On Ou Oy Oz Pa Pb Pc Pd Pe PF Pg Ph Pi Pj Po Qb Qc Qd Qe Qg Qh Ql Qm Qn Qt Qu Qv Qy Qz Ra Rb Rc Rf Rg Rh Ri Rm Sr Ss Tv Tz Ua Ud Ue Uf Ug Uh Uk Ul Um Un Uo Up Ur Us Ut Uu Uv Vo Vp Vs Vt Vv Wm Tj) Ib(aC AD aE aF aG aH al aK aL aM aN aO AP aQ aR aS aU aV aW Ax aY aZ bB Bc bE bF bG bH bl bJ bL bM bN BO bP bQ bR bS bU bV bW bX bZ cA cB cC cD cE cF cG cH cl cJ cK cM cO cP CQ cR CS CU CW cY cZ dA DB DC dD dE dF dG dH dl dJ dK dL dM dN Ed Ef Et Fn Fr gL Gp Hf Hw Ic Id Is Iu Jg Jj Jl Jp Jq Kc Ki Kk Kl Kn Kp Kr Ks Kx Ky Lh Li Lj Lv Lx Mf Mi Ml Mm Mp Mq Mt Mx My Nc Ne Nf Nh Nk NL Nm No Nq NR Nw Nx Oa Og On oP Or Ou Ow pF Pi Pk Qa Qd Qe Qh Qn Qt Qv Qx Ra Rj Rm Sr Ss To Tr Tt Tv Uc Ue Uf Uh Uu Vs Vv) gP(Af Aj aM Ao AX bC BO bV bW cF Ch cl cL cM cN Co Cs CT cV Dc dD dE dF DG dH dM Dp eF Fr Fy gL Hc Hq Hu Hv Hw Ic Ii Ij Il In Is Ji Jj Jl Jo Jp Jq Kc Kf Kg Kj Kk Kp Kq Kr Ks Ky Ld Lj Lv Lw Lx Mb Mc Me Mf Mg Mi Mm Mp Mt Mx Mz Nc Ne Nf Nj Nk Nl Nm Nq Nw Nx Oa Of Og oH Ou Ow Oy Oz Pb Pc pF Pk Pz Qa Qd Qe Qh Qn Qx Ra Tv Ue Uf Ug Uh Uk Ur Us Vs Vv Wm Tj) bA(AJ AO aS aY bC Bg bW CH cN Co Cp Ct De Dk Ed Hb Hc Hq Hu Hw Ii Ij Is Iu Jd Je Jn Jo Kc Kg Kk Kr Ks Mf Mg Ml My Nc Ne Nf Nj Nk Nl Nt Of Ow Oz Pb Pg Pk Pz Qc Qu Qx Rj Ut Vv) bC(AJ Ao Ax aY CH cl cT cV Ed Hw Ik In Is Ji Jj Jn Jo Kg Kj Ld Lj Mf Mg Mf Nj Nk Nl Nm Nt Oa Of Og Or Ow Oz Pk Pz Qa Rj Sr Tv Ue Ug Wm) Ed(aE aJ aY Bc bW cH cJ cL cM cN cT CV Dg eF Fw Hw Ij Is Ji Jj Jl Jn Kr Mf Ml Nc Ne Nf Ng Nl oH oP Ow Pk Pz Qc Qx Rj Tn Tv Uc Uf Tj) Rj(aE AJ aX aY bV CH cl cJ cL cN cT cV dG eF Hw Id Ij Is Ji Jj Jl Jn Jq Lw Mf Mi Mp Nf Ng Nj Nk Oa oH Ow Pf Pk Pz Qn Qx Ri Uf) Ng(Ad aJ Ap aY Bc bF bW cG cH cJ cL cN cT cV Dc dF dG Ef Et Fr gL Is Ji Jl Jn Jp Jq Kl Kq Mp Mt Nq Nx On oP Ow Qa Qt Ss Uu Vs) Jn(AJ Ao aY bW CH cL cN Hb Hw Ii Ij In Is Jj Jo Js Kg Kk Kr Ks Mf Mi Ml Nc Ne Nf Nj Nk Nl Nm Nt Ow Pk Pz Qc Qx Ue) Pz(AJ aY bW CH cN cT cV dG eF Hw Ii Ij In Is Jj Jl Kj Mf Mp Nc Ne Nf Nj Nk Nl Nm Og Or Ow Ue Uf Ug) Is(aO bW cH Fy Ha Hb Hq Hw Ic Ii Ij Iq Jf Jj Kk Ks Lu Lz Me Mj Ml Nf Nw Pk Qc Qx Tv Un Tj) aJ(Aj aP cH Co cT cV Hw Jd Je Js Kr Md MF Nf Nk Nl Nt oH Ow Pg Pk Qc Ql Qx Rg Sr Tv) Mf(Ax aY bW cH cJ cL cN cT cV Ji Jl Jq Mp Nc Ne Nj Nk Nl Oa Or Ou Ow Qa Qd Tv) oP(aF Aj aM Bb Ch Cp cS Ef Ii iJ In Iz kE kl Kj Kk mP Ms nA nC nL Nm nU Oy) Ji(Ao cH Hb Hw Ii Jo Js Ke Kg Kk Kr Nf Nm Pj Pk Qc Ql Qx Un) cT(AO bW CH Co Ct Hc Hq Hu Hw Ij Nf Nk Nl Of Pk Vv) cN(cH cM cV Hw Ic Jj Kr Md Nf Nk Nl Og Ow Pk Ql Qx Ur) Nf(aY bW cH cJ cL cV dG Mp Nk Oa) Ow(Aj bW cH cV eF Fy Jj nJ nU Qx) Jj(Bc cH Iu kE Nk Nl Qx Ur) eF(Aj Ao Ch Co Mg Nk Of Ue) qT(kI kP mM nB nN nR nT nU) cH(aY cl cQ cV Jl Nk Or) oH(aY bW Ij Ne Nk Nl pF) mF(aY cE dG hB Nx oN) Aj(Ad Ba Dg Kf Uu) Vs(Ao Ch Hu Of) Pk(cV Nk Or Qa) Dg(Jo Kg Nm) Uc(Ch Of Ue) Hw(bW Iu Ur) Kf(Jo Kg Mg) Kr(Jl Mp Qa) Oa(Ha Pe Rg) cV(aY Ch Nk) Ml(aY Iu) Qc(Qd Qe) Js(Mp Qa) Ld(fR Gz) cE(kE nF) dG(kl nT) qX(cJ Cv) FyJl NkbW InnR nOlK kEoQ} oP{mF(aC AD aE AF aG aH al aJ aK aL aM AN AO AP aQ AR AS aU aV aW aY aZ BA BB BC bE bF Bg bH bl bJ bL bM BN BO bP bQ bR bS bU bV bW bX bZ cA cB cC cD cE cF cG cH cl cJ cK cL cM cN CO CP CQ cR CS CT CU CV CW CX cY cZ dA DB DC DD DE dF DG dH dl dJ DK Dl dM dN dR eC eF Fa Fb fP Fw gL GP hB HC hF hG iA Ic iH iP iZ Jd Je Kc Kd Ke Kf Kg Ki Kl Kn Kp KQ KS Kx Ky Kz Nq nW nY oE oF oH oN Or Ou Ow pF Pi Pj Pk Qy Ua Ub tF) Ib(aD aG aJ AN Ao aP aR aS aY Aw AX aY aZ BA BB Bc bF Bg bH cK cL Co CP cQ Cs CT Cu cV cX dA DC Dd De dF Dg Dl dJ Dl Ef Ez fP Fw Fy Gl Hc Hu Hx Id Im In IZ Jd Je Jl Jn Jp Jq Js Kc Kf Ki Kj Kl Kn Ko Kp Kq Ks Kx Ky Kz Lh Lj Lv Ma Mj Mk Mm Mn MP Mr mS Mv Mw Mz Na Nb nD nF Ng Nl Nk Nm Nn No Ns Nw Ny Oa OE Of Oh OK Om On Or Oy Oz Pd Pj Pz Qa Qb Qd Qe Qh Qv Qz Ra Rb Rf Rg Rm Sr To Tr Tv Tz Uc Uf Uh Uk Un Uv Vo Vt Vu) Ch(aM aV aY Bb bF bG bl bL bN cC cF cJ Co Cq cR cS cX Db Dc dD dl dJ DL Et Fw Hv iJ In Jn kC Kf kI Kn kO kR Ld mE mH Ms nB ND Ng nH nI NJ Nm Ns NU Og OH Or Pa Wm) nA(Ad Af Al aN Ao AP Ar As Aw aX Ba Bb Bg Bn Bo cJ Co Cq cS Ct Cv Cw Dc De Dg Di Dk Dl Fb gL Hc iJ Kj Kk Ld Or Ow) Ef(aS Aw aX cF cH Dc Di Dl Ez Hv iJ In kC kO Ld Me Ml nB nC nD nF nH nI nJ Nk nL Nu Ow Pa Qz Wm) Ng(aF aN aR aS aV Aw aX aZ Bo bU bX cD cF cH cM Cp cS Cv cX dA Dl iJ iZ Kk Ld oH oK Ow) nK(Af Aj Al Ar As Aw aY Ba bF Bn Bo bQ Co Ct Cw De Di Dk dL eF fP gL Hb Hc Jv Kj oE oN) Cp(aN AX Ed iJ kC kO Mx nF nH nJ Qa Wm) Aw(Ed Fw Hv Kf mS nJ nU Oa Oh Or Pa Ub) mS(Ad Ao As Ba Bg Ct Cw De Di Dk Kj) nL(Ao As Bg Ct Cw De hG Iz Kj nH) aX(Ad Ao Bb Bg Cw Ii Iz Mv Of) Di(Aj aY Ed In mP nI nJ Ub) Iz(iO Kc kl nD nJ Qz) Fb(Ed mP nD Oa Wm) In(aG aN aR Kk Ks) Kk(Bb Hb Ii Of) nF(Ct Hc Kj Og) Bg(nC nD nJ) Ct(nC Ow) Dk(iJ nD) Hc(nD nJ) Ld(mP Of) AdnJ AjPo CwnC DlJg NtbG MgOw IiOa aPiZ aYiO} Ib{Ow(Ad bA BC cB cT cX Dg eF Jn kC KF kO mE mF mP mS mT mW nA nB nC nD nF nH nI Nj nK nL nT Pz Tn) Tv(aX bA bC bE cT cZ Dc eF iJ kC KF kP ml mP mS mT mU mY nA nB nD nF nH nI nJ nK nL nN nO nT) oH(Ap Ba BC cJ Cu Cw cX Dc eF fR Ic Id Jg Jn kF mP Nj Nl Nm Pz Rj Tn Uc Uf) Kn(kE kF kG kK IW IX IY ml mP mT mU mY nA nB nC nD nF nL nN nU) cX(Ad aX BC bE cZ Dc Dg eF Ic Jn Kc kE Kf Kp Kq Nm Pz Qz Rj) kE(BA bQ bZ cL dG Et Is Kk Ko On oQ Or Tn Tr Tz) Pz(bA BC cN

Figure 18 Continued cT eF iH In Jn Kf Mp Nj Og To Ub) nR(Ba dI Et Kc Kk Ko Kp Ma Mw Nk nL Nw Oi Pk To) Ma(kG kI lY mP mT mU mW mY nC nF nH nL nT) bA(BC Ic Jn Kf kI nA nF Nj nL Nm Pk Rj) Kf(bC cT cV gP Hw Ik Mg Ng Nt Of Pk) bC(Ax cT cV Dc Jn Nj Og Rj Ub) nL(Ba cI dM Et Fy Kk Ko Ld Vs) kI(Ba bZ cE dF dH Fy Ld Or) Nj(Ba cT eF Jn Ni Pk Tn) nU(Ba Et Kk Ld Nw Oh) Dg(Jt Ng NT) nC(Ba dM Et Kk) Bc(cT gP Ub) Ng(Ad Ba Ef) Jn(cT eF Pk) Ko(kK lY mP) Et(nT oO) Nt(eF Tn) Or(mT nJ) Pk(cT Tn) cJ(qU qX) gP(eF Kq) oQ(dI Qv) GzNx IcIs QcrC KckK KklW LdfR VsnH cEnA dMnT mFhB mPoN} Ng{Kf(Ad Af Ao aV BA BC CH cL cM cV cX Dg eD EF Et Fp Fr Fw gW Hb Hc Hq Hu Hv Hw Ih Ii Ij Ik In Jj jM Jn Jo Jp Jr Js Ke Kg Ki Kj Kr Ks Ky Ld Lu Lv Ly Lz Mb Md Me Mk Ml Mp My Nd Nf nJ Nm Nt Nu Ou Ow Oz Pb Pg Ph Po Qc qT qU qX rA Rj Ub) Ba(Ad aS BC Et Gl gP Hq Hu Hv Hw Ic Iu Jg Ji Jj Jn Jp Kc Kk Ly Mf My nA Nc Nd Ne Nf NJ Nk Nl Om Ou Ow Pa Pc Pg Pk Qa Qc Rj Ub Um) Pz(AP bB bF Bg Bo bR bW bX cE cG cH cJ cL cN Cu cV Cw cX Dc dH DL dN Ef fP gL hB Hc hF Ic Kc Kk Kl Kn Kp Ky Ou Ow Qz Rj Ub Uf Uk) Dg(Ao bA bC gP Hb hC Hv Jj Jn Jo Jt Kk Kr Ly Mf Nc Ne NF Nj Nk Nl Nm Ow Pk qT rA Rj Ub) bC(Ad bA cT cV cX Dc Et Jg Ji Jn Ly Mt Ne Nj Nl Ou Rj Ub) Ad(bA cL cN eF gP Jj Jn Ly Ne Nf Ow Pk Rj Ub) Ow(bA Bc dG eF Ex Gz Jg Jn Jp Kq nJ nU oQ) bA(aS Bc Et Jg Jn Ly Ne Nj Nl Nm) Rj(Bc eF gP Jg Jn Uc) eF(Bc Et Nj Ub Uc) qX(Ap Bc cJ Kc Uu) Jn(cL Ou Pk Uu) Ly(cL cV cX) Bc(Nj Ub) Et(cT Kk) Uc(gL gP) NfcL IcIs KkOn KnnU KqgP UueD} Ch{Ow(kC kF kG kI kK kN kO kP lW lX lY mE mF mH mI mM mS mT mU mW mY mZ nA nB nC nD nH nI nK nL nM nN nO nT oO oQ) Tv(kC kK kO kP lW mE mH mI mS mT mU mZ nA nB nC nD nF nH nI nJ nK nL nR nT nU) kE(cE cL dF dG Fy Is nR Ok ON oQ Or Ou Qa Rc Tr Uc Vs) nF(bF cE cL dF Dg Et Kf nR ON) mF(aJ bF cE cL hB Kn ON oQ) nR(aN Kk Ld lK nJ Ns Qv Qy) kI(aY cE cL Is Ld oN) mP(Et Ip Is Kn Oh) Ld(kF lW mU nL) cE(nA nC nJ nL) Kk(lW mU nL) nJ(Is Oh oN) Pz(bA cT) mT(Is Or) ExNx KnmU aCbC} Is{Iq(Hu Ih Ii Ik Il In It Ji Jj Jl Jn Jo Jr Js Ly Lz Md Mf Mk Ms Nd Ne Nf Nx Om Oy Pz Qc) Hw(Hr Ic Ih In Ji Jl Jn Lu Lv Lz Mk Ml Ms Nc Nh Nj Nl Nx Ok Om Pc Pz Qc) Ij(Ih In It Ji Jn Jo Lu Lv Ly Lz Mk Ms Mt Nd Ne Nf Nx Ok On Pz Qc) In(Ly Ml Ms nC ND Ne nH nL) Ml(Aj Il Lv Ly Ne) nD(Fb Gp Ha It) Nd(Ik It) Ic(Jj oH) nK(dJ Kk) LvQc MsIh} Ld{fR(aN aQ bP bR cH Dp Ez Ha Ii Ik Mb Nf Or Ow Ql Qn Qz Ri Rj Tv Ub Uk Ur Us Ut Uu Vv) nA(bA bW cE cL dM Ii In Ky lW Mp oN pF To) Ii(mU nJ nR oQ) Jj(Em kE kI mF) mF(cO Id pF) kI(aY Ij pF) Em(bJ dL) In(mP nR) nK(aY pF) NfmP} In{Rm(kE kI kN lW mE mI mZ nA nD nF nJ nK nU) Pz(bA Ji Jl Lv Nd Ne Nh Nl Nx Tv Ub) Jn(Jl Lv Ly Nd Ne) Tv(kE mS nJ) Jl(Ly Nd Ne) Em(Ou Ow) Kf(nJ nU) cJ(nD nJ) DinR MpnD KnnU lYrZ} Jn{Hw(Ij Ip Iq Jl Lv Nd Ne Nh Nj Nl Nx Pz) Nd(Ij Ik Iq Lv Lz Mf Ml Mp Nt Qc) Lv(Jr Js Ly Lz Po Qc) Ij(Ji Ly Ne Nx) Iq(Jl Ml Ne) LyNf} Mw{cE(mF nA nF nJ nK nL) dG(kE mS nA nJ nK nN) hB(mF mS nK nL) UhnF dMnL lYrZ} Ow{Em(Jo Kc Kg Ly) nJ(Ct Iq Mc Of) nF(cH cJ Ct) Jo(bC Kf) AjbC CtnB McnA MgoQ PzJj OrfR} Nx{Ex(Aj Hw Jo Kj Ks Mg Of Og Ub Uk) Em(Ii Kj) Hw(Jl Ly) GzMg LvIj aNfR} qX{cJ(Aj Ct cX Hc Oz qU Vv Wm) Vv(Dg Kf Kp) Hc(cX Kc) AjDg CtPz KcOz} bA{aS(kO mF nC nH nJ nL) Hu(Ly Nj Nl Pz) Pz(Aj Ii Mg)} Em{Ly(aN cV Kg Lv Mp) Ou(Ii Kc Kj Mg Po) JoOk} Lv{Nd(Mb Mf Ml) Ij(Mt Ne Pz) Hw(Ly Ne) MlIq} Hw{Jl(Ip Ly Nd Ne Nl Pz) LyJi} nR{lK(aF aO Cp cY dA Dk Ke)} Mp{nD(It Nb Nn nT) NbnF nHnL} dX{cN(aQ aV bB bJ) HuKf cLcO} qT{cJ(Hc Qu Vv) aW(kN mF) DgVv} fR{Qz(cV cX) EtOr aCbE} lY{rZ(Ii Mf Mj Nn)} nF{oH(aJ hB) CpcE NbJl} nJ{dL(nT oH) MeOr IqcL} Pz{EflM IltN KfKj} Wm{cJ(jM qU)} Nt{Ub(Bc eF)} Iq{Ji(Ml Ms)} Kf{AjgP VvjQ} eM{MgcL NfaN} FpOamZ StJjkE aOmSlM cZmTqV Unconstrained panels with 2 analytes, where 1.0E-5 >= 'model p-value' > 0. Contains 7 panels of 114,449 total panels evaluated. : Qw(cX gP Ib Ub) oP(Ch Ib) NgKf Unconstrained panels with 2 analytes, where 1.0E-4 >= 'model p-value' > 1.0E-5. Contains 101 panels of 114,449 total panels evaluated. : Qw(AJ AX aY bA BC bW CH cJ cL cN cT cV DG Ed eF Hw Ij Is Ji Jj Jl Jn Jq Kf Kk Kr Ky Lw Mf Mi Ml Mp Nc Ne Nf Ng Nj Nk Nl Og oH oP Or Ou Ow pF Pk Pz Qa Qd Qx Rj Ue Uf) Ib(bA bC cT cX eF Kf Nj nR oH Tn) Ng(Ad BA bC DG eF Kq) Is(Hw Ij In Iq Ml) Jn(Hw Ij Lv Ly Nd) oP(Bb Cp Ef Iz) Lv(Ij Iq Ly) ChnR MpnD HubA HwJl LdfR cJqX nHnL Unconstrained panels with 2 analytes, where 1.0E-3 >= 'model p-value' > 1.0E-4. Contains 834 panels of 114,449 total panels evaluated. : Qw(AA aC AD aE AF aG aH aI aK AL aM AN AO AP aQ AR AS aU aV AW aZ Ba BB bE bF BG bH bI bJ bL bM BN BO bP bQ bR bS bU bV bX bZ cA cB cC cD cE cF cG cI cK cM CO CP CQ cR CS Ct CU Cv CW Cx cY cZ dA DB DC DD DE dF dH DI dJ DK DL dM dN Dp dR eD Ef Et Ex Ez Fa Fb Fn FP FR Fw Fy GL Gp Gz Ha HB HC Hf Hq Hr Hu Hv Hx iA Ic Id Ih Ii iJ Ik Il Im In IO Ip Iq Ir It Iu Iv Iz Jd Je Jf Jg Jh Jk Jm Jo Jp Jr Js Jt JU Jv Jy Kc Kd Ke Kg KI Kj Kl Kn Ko Kp Kq Ks Kx Kz Ld Lh Li Lj Lu Lv Lx Ly Lz Ma Mb Mc Md Me Mg Mh Mj Mk Mm Mn mP Mq Mr Ms Mt Mu Mv Mw Mx My Mz Na Nb nC Nd Nh Ni nJ nL Nm Nn No Nq Nr Ns Nt NU Nv Nw Nx Ny Oa OE Of Oh Oi Ok Om On oQ Oy Oz Pa Pb Pc Pd Pe Pf Pg Ph Pi Pj Po Qb Qc Qe Qg Qh Ql Qm Qn QT Qu Qv qX Qy Qz Ra Rb Rc Rf Rg Rh Ri Rm Sr Ss St Tn To Tr Tt Tv Tz Ua Uc Ud Ug Uh Uk Ul Um Un Uo Up Ur Us Ut Uu Uv Vo Vp Vq Vs Vt Vu Vv Wm Tj) Ib(Ad aJ Ap AX aY Ba Bc bE bF bR bW bX cB cE cH cJ cL cM cN CV Cw cZ dB Dc dF DG dM Et Fn gL gP Ic Id iH Is Jg Ji Jn Jp Jq Kc kE kF kI Kk Kl Kp Kq Ky Ml mP mT mU mY NC nD Ne Nf nJ NL Nm nU Og On oO oQ Ou Ow Pk Pz qU qX Qz Rj To Tv Ub Uf Uh Uu) oP(Ad aF Aj Al aM aN AO Ap AS Aw aX aY Ba bF Bg Bo bQ cH Co Ct Cw cX De Di dJ Dk dL Ed Fb fP Hc hG iH iJ iO iZ Je Kj mF Mp nF nL oE oK) Ng(aJ Ap Bc bF Bg Bo bW cE cG cH cL cN cT Cu cV cX Dc dF dH Dl Ef Ex fP fR gL hB Hc Ic iJ Kc Kl Ko Kp Ky Lv Nx Ou Ow Pk Qz Rj Uc Uf Uu) qX(aG aI AJ aM aQ aR aY bA bB bC bF bS bX cB cC cE cG CH Co Ct cV cX dB dF dL GP hB Hc Ic iH iJ Kc Kn Kp Ky oE oH Ph Pk Rj Vv) Lv(Et Hv Hw In Ip Is It Ji Jj Jl Jo Jr Js Lu Lz Md Me Mf Mk Ml Mm Mt Nc Nd Ne Nf Nh Nj Nl Nx Ok Om Pc Po Pz Qb Qc) Jn(Aj Ih Ii Il In Iq Is It Jj Lu Lz Ml Ms Ne Nf Nh Nj Nl Nx Om Pc Pz Qc Rj) Nd(Et Fr Hw Ij In Is Ji Jl Jp Ly Mb Me Mf Ml Mm Mp Mt Nw Nx Ok On Pz) Is(Aj Ic Ih Ii Il It Jj Jo Lu Ly Lz Mk Ms nD Ne Nf Om Qb Qc Tv) Ji(Hw Ii Ij In Iq Jo Ly Lz Ml Ms nD Ne Nf Om Qc) Nx(Ex fR Hw Ij In Iq Jj Jo Ly Lz Ms Ne Nf Pz) bA(Aj Ch Ct Hq Hw Jj Jk Nj Of Oy Pz Qu) Ch(bC Kf kI mP mU nJ nU oQ Pz) Jj(BC cT dX Kc Kf Ky Ow Rj) Aj(bC Dg Et Kf Ne Nj Ow Pz) Ly(cX Em Et Hw Ij Jl Ne Nf) Rj(bC bW cH cX gP Ij oH Ub) fR(aC An cT Nj oH Or Ow Qz) nF(cE cJ dG hB Jl Mp Ok On) tX(Il Ip Mk Nu Pz Qc tQ tS) In(Jl nC nD Ne nH nL Pz) nA(cE cL dG dN Ld Or Ow) tT(Et Hx Ip Jp Jr Ml Pz) Hw(Mt Ne Nh Nl Ok On) Mp(kC nC nI nK nN) Ub(BC eF Pk Pz) Ij(Mt Ne Nw Ok On) Kf(Jo Kg Kj Mg Of) nJ(dL dN Or Ow To) Ld(Em kI mF nL) Ne(Lz Ml Pz) Jl(Il Iq nD) mF(dN hB Tv) tN(Il Mk Pz) rZ(nM nT nU) Hu(aJ cT) aC(bC bE) cX(bC Qz) mP(Kk Mz) nD(It Ok) qT(cJ Ic) EmKc MkwB OrmT aNeM dLoH dNkE Constrained panels with 3 analytes, where 1.0E-10 >= 'model p-value' > 0. Contains 1 panels of 17,333,483 total panels evaluated. : ChTvkE Constrained panels with 3 analytes, where 1.0E-9 >= 'model p-value' > 1.0E-10. Contains 4 panels of 17,333,483 total panels evaluated. : oP{nK(Ef Iz) ChmF} IiLdmP Constrained panels with 3 analytes, where 1.0E-8 >= 'model p-value' > 1.0E-9. Contains 7 panels of 17,333,483 total panels evaluated. : Ib{kE(dF Tv) oP(mF Ow) oQoH} AjnAoP BaNgPz

Figure 18 Continued

Constrained panels with 3 analytes, where 1.0E-7 >= 'model p-value' > 1.0E-8. Contains 23 panels of 17,333,483 total panels evaluated. :
oP{mF(Kj Ld oK Ut) mS(Cp Ef) ApnK ChaN MxIb} Qw{cX(gP Ib Mf Ub) Ub(bC Pz) IbbA} Ng{Pz(bA Dg Kf)} Ib{JinU nRoH kIlM} LdaYmF Constrained panels with 3 analytes, where 1.0E-6 >= 'model p-value' > 1.0E-7. Contains 259 panels of 17,333,483 total panels evaluated. :
Qw{cX(aJ aX bC bE bW cH cN cZ Ed eF Hw Ij Jn Kr Md Me Mi Nf Ng Ow Pk Pz Qc Qy Rj Uf) Ub(aJ aY bA Bc bW cH cL cN Dg eF gP Ib Ji Jj Jl Jn Mp Nx Or Ow Pk Qa Qx Rj Uc) Ib(aJ aX Ba bC cL cN cT cV eF gP Ji Jn Kf Kq Nj oH Pz Tn) gP(aJ aY bA Bc cH cJ Ed Jn Ml Ng Or Rj) Ng(BA bC Dg eF Jg Kf Pz Uc) Is(Js Kr Mf) mF(oP oQ) PzUk QaQc RjbW bGoP dGkE} oP{Ib(cF cS Ed Et Ji kE kl Kk Ld nA nC Nj nK nL oH Oi) mF(Aj Al AX bG Di dL Ef Hb Id iO Kk Ko kR) Ch(aX Ed kE Kk mP mS nA nC nF nK nL Ow) Cp(nA nC nD nK nL Oa Pa) nA(bG Ef Iz oH) nK(Ad Ao Bb Bg) Di(nC Ng nL) Aw(nC nL) Ef(iO Kk) Iz(Kk mS) NgiO} Ib{nR(In Ji kE Kn Ld lK Ow) kE(cE dM Fy hB Ji Ma) oH(Ad Dg Kf Kl Kp Uu) Tv(kl mF nC nL) Ow(nJ nU oO oQ) nC(Fy Ji) ExNx KkmU LhmP} Ng{Pz(Ad aJ BC cT dF dG eF Kq) Kf(gP Kk Mf Pk) DgqX OwbC} Is{Hw(Ij Iq Ly Nd Ne) Ml(Ij Iq Nd) Iq(Ij Lv) IinC InPz} Ch{Ow(kE mP nF nJ nR nU) Tv(kl mF mP) LdmP OhkI} Pz{Ct(bA cT) Of(bA cT) InJn} Em{Kg(Nx Ok Ou) JoOu} Jn{Lv(Ij Iq) LyHw} Ld{aY(nA nL) InnU} nF{oH(dG oQ) aSbA} cN{JjdX aVeP} AwnRlK CtOwnU Constrained panels with 3 analytes, where 1.0E-5 >= 'model p-value' > 1.0E-6. Contains 1,740 panels of 17,333,483 total panels evaluated. : Qw{Ib(Ad Ax aY Bc cH cJ Cq Cw Dc Dg Ed Ef Et gL Ic Id Is Iu Jg Jl Jp Jq Kc Ki Kk Kl Kn Kp Ky Mf Mi Mp Mt Nc Ne Nf Nk NL Nq nR Nx On oP Ou Ow pF Pk Qa Qd Qt Rj Rm To Tv Uc Uf Uu Vs Vv) bA(Aj AO aS aY bC Bg CH Co Cp Ct Dk Ed Hb Hc Hq Hu Hw Ii Ij Jd Je Jn Kk MF Mg My Nf Nk Nl Of Ow Pb Pk Pz Qc Qu Qx Rj Ut Vv) Ng(Ad aJ Ap aY Bc bF bW cG cH cJ cL cN cT cV Dc dF dG Ef Et Fr gL Is Ji Jl Jn Jp Jq Kl Kq Mp Mt Nq Nx On oP Ow Qa Qt Rj Ss Uu Vs) Pz(AJ aY bC bW CH cN cT cV dG Ed eF Hw Ii Ij In Is Jj Jl Jn Kj Mf Mp Nc Ne Nf Nj Nk Nl Nm Og Or Ow Rj Ue Uf Ug) Jn(AJ aY bC bW CH cL cN Ed Hb Hw Ii Ij In Is Jj Jo Js Kg Kr Ks Mf Ml Nc Ne Nf Nj Nk Nl Nm Ow Pk Qc Qx Rj) Is(aO bC bW cH Ed Fy gP Ha Hb Hq Hw Ic Ii Ij Iq Jf Jj Kk Ks Lu Lz Me Ml Nf Ow Pk Qc Qx Rj Tv Ub Un Tj) bC(AJ aY CH cI cV Ed gP Hw Ji Jj Jo Kg Kj Mf Mg Nf Nk Nl Nm Oa Of Og Or Ow Pk Rj Tv Ue Ug Wm) gP(Aj bW Ch cN cT cV dG dM eF Hu Hv Hw Ij Ji Jj Jl Ky Lw Mf Nc Ne Nf Nk Of oH Pb pF Qa Qd Tv Uf) Rj(aJ aX cH cJ cL cN cT dG Ed eF Hw Id Ij Ji Jj Jl Jq Lw Mf Nk Oa oH Ow Pf Pk Qn Qx Ri Uf) Mf(aJ Ax aY bW cH cJ cL cN cT cV Ed Ji Jl Jq Mp Nc Ne Nj Nk Nl Oa Or Ou Ow Qa Qd Tv) oP(aF Aj aM Bb Ch Cp cS Ed Ef Ii iJ In Iz kE kI Kj Kk mP Ms nA nC nL Nm nU Oy) Ed(aJ aY Bc bW cH cL cN cV eF Fw Hw Ji Jj Nf oH Ow Pk Qc Qx Tv Tj) Ji(Ao cH Hb Hw Ii Jo Js Ke Kg Kk Kr Nf Nm Pj Pk Qc Ql Qx Un) cT(AO bW CH Co Ct Hc Hq Hu Hw Ij Nf Nk Nl Of Pk Vv) aJ(aP Hw Jd Je Kr mF Nf Nk Nl oH Ow Pk Qc Ql) Nf(aY bW cH cJ cL cN cV dG Mp Nk Oa) Ow(Aj bW cH cN cV eF Jj nJ nU Qx) oH(aY bW cX Ij Nc Nk Nl pF Ub) Jj(Bc cH Iu kE Nk Nl Qx Ur) eF(Aj Ao Ch Co Mg Nk Of Ue) cH(aY cI cQ cV Jl Nk Or) mF(aY cE dG hB Nx oN) Aj(Ad Ba Dg Kf Uu) Ub(iJ Iu Kn pF Tv) Pk(cN cV Nk Or Qa) Vs(Ao Ch Hu Of) cX(hC iJ iO pF) Dg(Jo Kg Nm) Uc(Ch Of Ue) Hw(bW Iu Ur) Kf(Jo Kg Mg) Kr(Jl Mp Qa) Oa(Ha Pe Rg) cN(cM Nl Ql) cV(aY Ch Nk) Ml(aY Iu) Qc(Qd Qe) Js(Mp Qa) cE(kE nF) dG(kI nT) qX(cJ Cv) qT(kI nU) FyJl NkbW InnR nOlK kEoQ} oP{Ib(AN aV Ax bI cP cQ dA Dc Dd Dg dI Dl Ez Fw Fy Hc Hx In Jn Jp Jq Js Kc Kf Ki Kn Ko Kp Ks Lh Ma Mk Mm mP Mz Nk Nm Nw Oa Oe Oh Om Or Qv Rf Rm Sr To Tr Tz Uh Uk Un Uv Vo Vt Vu) Ef(aS Aw aX cF cH Dc Di Dl Ez Hv iJ In kC kO Ld Me Ml nB nC nD nF nH Ni nJ Nk nL Nu Ow Pa Qz Wm) nK(Af Aj Al Ar As Aw aY Ba bF Bn Bo bQ Co Ct Cw De Di Dk dL eF fP gL Hb Hc Jv Kj oE oN) Ch(aM aY bG bI bN cR Fw iJ In Jn kC Kf kI Kn kO Ld mE nD nH NJ Og Oh Or Pa Wm) nA(Ad aN Ao AP As Aw aX Ba Bb Bg cJ Co Ct Cw De Di Dk Fb gL Hc Kj Kk Or Ow) Ng(aF aN Aw aX bU bX cD cF cH Cp cS Dl iJ Kk Ld Ow) Cp(aN AX Ed iJ kC kO Mx nF nH nJ Qa Wm) Aw(Ed Fw Hv Kf mS nJ nU Oa Oh Or Pa Ub) mS(Ad Ao As Ba Bg Ct Cw De Di Dk Kj) nL(Ao As Bg Ct Cw De hG Iz Kj nH) aX(Ad Ao Bb Bg Cw Ii Iz Mv Of) Di(Aj aY Ed In mP nI nJ Ub) mF(aN Cw Jd Je Nq Qy Ua Ub) Iz(iO Kc kI nD nJ Qz) Fb(Ed mP nD Oa Wm) In(aG aN aR Kk Ks) Kk(Bb Hb Ii Of) nF(Ct Hc Kj Og) Bg(nC nD nJ) Ct(nC Ow) Dk(iJ nD) Hc(nD nJ) Ld(mP Of) AdnJ AjPo CwnC DlJg NtbG MgOw IiOa aPiZ aYiO} Ib{oH(Ap Ba BC cJ Cu Cw cX Dc eF fR Ic Id Jg Jn kF mP Nj Nl Nm Pz Rj Tn Tv Uc Uf) cX(Ad aX BC bE cZ Dc Dg eF Ic Jn Kc kE Kf Kp Kq Nm Ow Pz Qz Rj) bA(BC Ic Jn kE Kf kI nA nF Nj nL Nm Ow Pk Pz Rj Tv) Pz(BC cN cT eF iH In Jn Kf Mp Nj Og Ow To Ub) kE(Ba bQ bZ cL dG Et Is Kk Ko On oQ Or Tn Tr Tz) Ow(Ad BC cB cT Dg eF Jn KF nB nF Nj Tn) Tv(aX bC bE cT cZ Dc eF iJ Kf mP Nj nK) nR(Ba dI Kc Kk Kp Mw Nk nL Nw Oi Pk To) Kf(bC cT cV gP Hw Ik Mg Ng Nt Of Pk) bC(Ax cT cV Dc Jn Nj Og Rj Ub) kI(Ba bZ cE dF dH Fy Ld Ma Or) nL(Ba cI dM Fy Ji Kk Ld Vs) Nj(Ba cT eF Jn Ni Pk Tn) nU(Kk Kn Ld Nw Oh) Dg(Jt Ng NT) Bc(cT gP Ub) Ng(Ad Ba Ef) Jn(cT eF Pk) Nt(eF Tn) Ji(mT nF) Kk(lW nC) Kn(mI mU) Or(mT nJ) Pk(cT Tn) cJ(qU qX) gP(eF Kq) oQ(dI Qv) BanC IcIs QcrC KckK VsnH cEnA dMnT mFhB mPoN} Ng{Pz(AP bB bF Bg Bo bR bW bX cE cG cH cJ cL cN Cu cV Cw cX Dc dH DL dN Ef fP gL hB Hc hF Ic Kc Kk Kl Kn Kp Ky Ou Ow Qz Rj Ub Uf Uk) Dg(Ao bA bC gP Hb hC Jj Jn Jo Jt Kk Kr Ly Mf Nc Ne NF Nj Nk Nl Nm Ow Pk qT rA Rj Ub) Ba(Ad bC gP Ic Jn Kc Kf Kk Ly Mf nA Nc Ne Nf NJ Nk Nl Om Ou Ow Pk Rj Ub Um) Kf(bA BC cH cV cX eF Hw Jj Jn Ks Ml nJ Nt Ou Ow qX rA Rj Ub) bC(Ad bA cT cV cX Dc Et Jg Ji Jn Ly Mt Ne Nj Nl Ou Rj Ub) Ad(bA cL cN eF gP Jj Jn Ly Ne Nf Ow Pk Rj Ub) Ow(bA Bc dG eF Jg Jn Jp Kq nJ nU oQ) bA(aS Bc Et Jg Jn Ly Ne Nj Nl Nm) Rj(Bc eF gP Jg Jn Uc) eF(Bc Et Nj Ub Uc) qX(Ap Bc cJ Kc Uu) Jn(cL Ou Pk Uu) Ly(cL cV cX) Bc(Nj Ub) Et(cT Kk) Uc(gL gP) NfcL IcIs KkOn KnnU KqgP UueD} Is{Ij(Ih In It Ji Jn Lu Lv Ly Lz Mk Ms Mt Nd Ne Nf Nx On Pz Qc) Iq(Ii Ik Il In It Jl Jn Jo Ly Lz Md Mf Mk Ms Nd Ne Nf Om Qc) Hw(Ic Ih In Ji Jl Jn Lu Lv Ml Ms Nh Nj Nl Nx Ok Om Pz Qc) In(Ly Ml Ms nC ND Ne nH nL) Ch(kE kI mP mT nJ) Ml(Aj Il Lv Ly Ne) nD(Fb Gp Ha It) Nd(Ik It) Ic(Jj oH) nK(dJ Kk) LvQc MsIh} Ch{kE(cE cL dF dG Fy nR Ok ON oQ Or Ou Qa Rc Tr Uc Vs) nF(bF cE cL dF Dg Et Kf nR ON) mF(aJ bF cE cL hB Kn ON oQ) nR(aN Kk Ld lK nJ Ns Qv Qy) Ld(kF kI lW mU nL) cE(kI nA nC nJ nL) Tv(mH nA nK nL) mP(Et Ip Kn Oh) Kk(lW mU nL) kI(aY cL oN) Pz(bA cT) nJ(Oh oN) KnmU OrmT aCbC} In{Pz(bA Ji Jl Lv Nd Nc Nh Nl Nx Tv Ub) Rm(kE kI kN mE mI mZ nA nJ nK) Jn(Jl Lv Ly Nd Ne) Tv(kE mS nJ) Jl(Ly Nd Ne) Ld(mP nA nR) Kf(nJ nU) cJ(nD nJ) DinR MpnD KnnU lYrZ} Jn{Hw(Ij Ip Iq Jl Lv Nd Nc Nh Nj Nl Nx Pz) Nd(Ij Ik Iq Lv Lz Mf Ml Mp Nt Qc) Lv(Jr Js Ly Lz Po Qc) Ij(Ji Ly Ne Nx) Iq(Jl Ml Ne) LyNf} Ld{nA(bA bW cE cL dM Ii Ky lW Mp oN pF To) fR(aQ Ii Ik Mb Ow Ut) Ii(mU nJ nR oQ) mF(cO Id Jj pF) kI(aY Ij Jj pF) nK(aY pF) NfmP JjkE} Mw{cE(mF nA nF nJ nK nL) dG(kE mS nA nJ nK nN) hB(mF mS nK nL) UhnF dMnL lYrZ} Ow{nJ(Ct Iq Mc Of) Em(Jo Kg Ly) nF(cH cJ Ct) Jo(bC Kf) AjbC CtnB McnA MgoQ PzJj} qX{cJ(Aj Ct cX Hc Oz qU Vv Wm) Vv(Dg Kf Kp) Hc(cX Kc) AjDg CtPz KcOz} bA{aS(kO mF nC nH nJ nL) Hu(Ly Nj Nl Pz) Pz(Aj Ii Mg)} Lv{Ij(Mt Ne Nx Pz) Nd(Mb Mf Ml) Ly(Em Hw) MlIq NcHw} Hw{Jl(Ip Ly Nd Ne Nl Nx Pz) Ly(Ji Nx)} Em{Ou(Ii Kj Mg) Ly(Kg Mp) JoOk KjNx} nR{lK(aF aO Cp cY dA Dk Kc)} Mp{nD(It Nb Nn nT) NbnF nHnL} qT{cJ(Hc Qu Vv) aW(kN mF) DgVv} Ex{Nx(Ks Og Ub Uk)} Kf{AjgP HudX PzKj VvjQ} lY{rZ(Ii Mf Mj Nn)} nF{oH(aJ hB) CpcE NbJl} nJ{dL(nT oH) MeOr IqcL} cN{dX(aQ bB bJ)} Wm{cJ(jM qU)} Nt{Ub(Bc eF)} Iq{Ji(Ml Ms)} Pz{EflM IltN} FpOamZ MgcLeM StJjkE aCbEfR aOmSlM cZmTqV

Figure 18 Continued

Constrained panels with 2 analytes, where 1.0E-5 >= 'model p-value' > 0. Contains 7 panels of 114,449 total panels evaluated. : Qw(cX gP Ib Ub) oP(Ch Ib) NgKf Constrained panels with 2 analytes, where 1.0E-4 >= 'model p-value' > 1.0E-5. Contains 81 panels of 114,449 total panels evaluated. : Qw(aJ aY bA bC bW cH cL cN cT cV dG Ed eF Hw Ij Is Ji Jj Jl Jn Mf Mi Mp Nc Ne Nf Ng Nj Nk Nl oH oP Or Ow pF Pk Pz Qa Rj Uf) Ib(bA bC cT cX eF Kf Nj nR oH Tn) Ng(Ad BA bC DG eF Kq) Is(Hw Ij In Iq Ml) Jn(Hw Ij Lv Ly Nd) oP(Bb Cp Ef Iz) Lv(Ij Iq Ly) ChnR MpnD HubA HwJl cJqX nHnL Constrained panels with 2 analytes, where 1.0E-3 >= 'model p-value' > 1.0E-4. Contains 425 panels of 114,449 total panels evaluated. : Ib(Ad Ap AX Ba Bc bE cB cH cJ cL cN CV Cw Dc Dg Et gL gP Ic Id iH Is Jg Ji Jn Jp Kc kE kI Kl Kp Kq Ky Ml NC Nf NL Nm nU Og On oQ Ou Ow Pk Pz qU qX Qz Rj To Tv Ub Uf Uh Uu) Ng(aJ Ap Bc bF Bg Bo bW cE cG cH cL cN cT Cu cV cX Dc dF dH Dl Ef Ex fP fR gL hB Hc Ic iJ Kc Kl Ko Kp Ky Nx Ou Ow Pk Qz Rj Uc Uf Uu) oP(Ad Aj aN Ao AS Aw aY Ba bF Bg Bo bQ Co Ct Cw De Di Dk Ed Fb Hc hG iH Je Kj mF nF nL) Jn(Aj Ih Ii Il In Iq Is It Jj Lu Lz Ml Ms Ne Nf Nh Nj Nl Nx Om Pc Pz Qc Rj) Nd(Et Fr Hw Ij In Is Ji Jl Lv Ly Mb Me Mf Ml Mm Mp Mt Nw Nx Ok On Pz) Is(Aj Ic Ih Ii Il It Jj Jo Lu Lv Ly Lz Mk Ms nD Ne Nf Om Qb Qc Tv) qX(Aj bX cE CH Ct cX dL hB Hc Ic iH iJ Kc Kp oE Pk Qw Rj Vv) Ji(Hw Ii Ij In Iq Jo Ly Lz Ml Ms nD Ne Nf Om Qc) Nx(Ex Hw Ij In Iq Jj Jo Lv Ly Lz Ms Ne Nf Pz) bA(Aj Ch Ct Hq Hw Jj Jk Nj Of Oy Pz Qu) Qw(eD jU kI mP nC nJ nL nU oQ qT Tv) Lv(Hw Lz Mf Ml Ne Nf Nh Nl Pz Qc) Ch(bC Kf kI mP mU nJ nU oQ Pz) Jj(BC cT dX Kc Kf Ky Ow Rj) Aj(bC Dg Et Kf Ne Nj Ow Pz) Ly(cX Em Et Hw Ij Jl Ne Nf) Rj(bC bW cH cX gP Ij oH Ub) nF(cE cJ dG hB Jl Mp Ok On) tX(Il Ip Mk Nu Pz Qc tQ tS) In(Jl nC nD Ne nH nL Pz) nA(cE cL dG dN Ld Or Ow) tT(Et Hx Ip Jp Jr Ml Pz) Hw(Mt Ne Nh Nl Ok On) Ub(BC eF Pk Pz) Ij(Mt Ne Nw Ok On) Kf(Jo Kg Kj Mg Of) nJ(dL dN Or Ow To) mF(dN hB Ld Tv) Ne(Lz Ml Pz) Jl(Il Iq nD) aC(bC bE fR) tN(Il Mk Pz) rZ(nM nT nU) Mp(nK nN) Hu(aJ cT) Ld(kI nL) cX(bC Qz) fR(An oH) mP(Kk Mz) nD(It Ok) qT(cJ Ic) MkwB OrmT dLoH dNkE Unconstrained panels with 3 analytes, where 1.0E-10 >= 'AUC p-value' > 0. Contains 8,393 panels of 17,333,483 total panels evaluated. :
oP(Ch(aA aC AD aE AF aF aG aH aI aJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG cH cI cJ cK cL cM cN CO CP CQ cR CS CT CU CV CW CX cY cZ dA DB DC DD DE dF DG dH DI dJ DK DL dM dN Dp dR eC Ed EF Et Ez Fa Fb Fn FP Fr Fw Fy GL GP Ha HB HC HF hG Hq Hr Hu Hv Hw Hx iA Ic Id IH Ii IJ Ik Il Im In iO iP IZ Jd Je Jf Jg Jh Ji Jj Jk Jl Jm Jn Jo Jp Jq Jr Js Jt Ju Jv Jy KC Kd KE KF KG KI Kj KK Kl KN KO KP KQ KR KS Kx Ky Kz Ld Lh Li Lj Lu Lv LW LX LY Lz Ma Mb Mc Md ME MF Mg MH MI Mj Mk Ml MM Mn MP Mq Mr MS MT MU Mv MW Mx MY MZ NA NB NC ND Ne NF Ng NH NI NJ NK NL NM NN NO Nq NR Ns NT NU Nv NW Nx NY Oa OE OF Og OH Oi OK Om ON oO oQ Or Ou Ow Oy Oz Pa Pb Pc Pd Pe PF Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss Tn To Tr Tt Tv Tz Ua Ub Uc Ud Ue Uf Ug Uh Uk Ul Um Un Uo Up Ur Us Ut Uu Uv Vo Vp Vs Vt Vu Vv Wm Tj tF) Ib(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG cH cI cJ cK cL cM cN CO CP CQ cR CS CT CU CV CW CX cY cZ dA DB DC DD DE dF DG dH DI dJ DK DL dM dN Dp dR eC Ed EF Et Ez Fa Fb Fn FP Fr Fw Fy GL GP Ha HB HC HF hG Hq Hr Hu Hv Hw Hx iA Ic Id IH Ii IJ Ik Il Im In iO iP IZ Jd Je Jf Jg Jh Ji Jj Jk Jl Jm Jn Jo Jp Jq Jr Js Jt Ju Jv Jy KC Kd KE KF KG KI Kj KK Kl KN KO KP KQ KR KS Kx Ky Kz Ld Lh Li Lj Lu Lv LW LX LY Lz Ma Mb Mc Md ME MF Mg MH MI Mj Mk Ml MM Mn MP Mq Mr MS MT MU Mv Mw Mx MY MZ NA NB NC ND Ne NF Ng NH NI NJ NK NL NM NN NO Nq NR Ns NT NU Nv NW Nx NY Oa OE OF Og OH Oi OK Om ON oO oQ Or Ou Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss Tn To Tr Tt Tv Tz Ua Ub Uc Ud Ue Uf Ug Uh Uk Ul Um Un Uo Up Ur Us Ut Uu Uv Vo Vp Vs Vt Vu Vv Wm Tj tF) Aw(aA aC AD aE AF aG aH aI AJ aK AI aM AN AO Ap AR AS aU aV aW AX aY aZ BA BB bC bE bF BG bl bJ bL bM BN BO bO bP bQ bS bU bV bW bX bZ cA cB cC cD cE cF cG cH cJ cK cL cM cN CO CP cQ cR CS CT CU CV CW CX cY dB DC DD DE dF DG dH Di dJ DK DL dM dN Dp dR eC Ed Ef Et Ez Fa Fb Fn FP Fr Fw Fy GL Gp Ha HB HC HF Hq Hr Hu Hv Hw Hx iA Ic Id IH Ii IJ Ik Il Im In iO iP IZ Jd Je Jf Jg Jh Ji Jj Jk Jl Jm Jn Jo Jp Jq Jr Js Jt Ju Jv Jy KC Kd KE KF KG KI Kj KK Kl KN KO KP KQ KR KS Kx Ky Kz Ld Lh Li Lj Lu Lv LW LX LY Lz Ma Mb Mc Md ME MF Mg MH MI Mj Mk Ml MM Mn MP Mq Mr MS MT MU Mv Mw Mx MY MZ NA NB NC ND Ne NF Ng NH NI NJ NK NL NM NN NO Nq Nr Ns NT NU Nv NW Nx NY Oa OE OF Og OH Oi OK Om ON oQ Or Ou Ow Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss Tn To Tr Tt Tv Tz Ua Ub Uc Ud Ue Uf Ug Uh Uk Ul Um Un Uo Up Ur Us Ut Uu Uv Vo Vp Vs Vt Vu Vv Wm Tj tF) Ef(AD AF aH aI aJ aK AL aM AN AO AP aQ AR AS aU aV aW AX aY aZ BA BB BC bE bF BG bH bI bJ bM BN Bo bP bQ bR bS bU bV bW bX cA cB cC cD cE cF cG cH cl cJ cK cL cM CO CP Cq cR CS CT CU CV CW CX cY cZ dA DB Dc DD DE dF Dg dH Dl dJ DK DL dM eC Ed eF Et Ez Fa Fn FP Fr Fw Fy GL GP Ha hB HC HF hG Hq Hu Hv Hw Hx iA Ic IH Ii iJ Ik Im In iO iP IZ Jd Je Jf Jg Ji Jj Jk Jl Jn Jp Jq Jr Js Jt Ju Jv Jy KC KE KF kG KI Kj KK Kl KN KO Kp KQ KR KS Kx Ky Kz Ld Lh Li Lj Lu Lv LW LX LY Lz Ma Mb Md ME MF MH Mi Mj Mk Ml MM Mn MP Mq MS MT MU Mv MW Mx MY MZ NA NB NC ND Ne NF Ng NH NI NJ Nk NL NM NN NO NR NT NU Nv NW Nx NY Oa OE OF Og OH Oi OK Om ON oO oQ Or Ow Oy Oz Pa Pb Pc Pd Pe PF Pg Ph Pi Pj Pk Po Pz Qa Qb Qc Qd Qe Qh Ql Qm Qt Qu Qv Qw Qx Qy Qz Ra Rb Rj Rm Sr Ss Tn To Tr Tv Tz Uc Ud Uf Ug Uh Uk Ul Um Un Uo Up Ur Us Ut Uu Vo Vp Vt Vu Wm tF) Qw(aA aC AD aE AF aG aH aI AJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG cH cI cJ cK cL cM cN CO CP CQ cR CS CT CU CV CW CX cY cZ dA DB DC DD DE dF DG dH DI dJ DK DL dM dN dR eC Ed eF Ez Fa Fb FP Fr Fw GL GP Ha HB HC HF hG Hu Hv Hw Hx iA Id IH Ii IJ Ik Il Im In iO iP IZ Jd Je Jf Jg Jh Ji Jj Jk Jl Jm Jn Jo Js Jt Ju Jv Jy KC Kd kE KF KG KI Kj KK Kl KN KO Kp KQ KR KS Kx Ky Kz Ld Lj Lv LW LX LY Lz Ma Mb Mc Md ME mF mH Mj Mk Ml mM Mn MP Mq Mr MS MT mU Mv Mw Mx MY mZ NA NB NC ND Ne NF Ng nH NI NJ nK nL Nm NN NO Nr Ns NT NU Nv NW nY OE OF Og OH Oi oK Om oN oO oQ Or Ou Ow Oy Oz Pa Pc Pe PF Pg Ph Pi Pj Pk Po Pz Qc Qe Qg Qh Ql Qm Qn Qt Qv Qx Qz Rb Rg Ri Rj Rm Ss Tn To Tt Tv Tz Ua Ub Uc Uf Ug Uk Ul Um Un Ur Us Ut Uv Vp Vs Vv Wm tF) Di(aA AD aE Af aG aH aI aJ AL aM AN Ao Ap AR AS Ax aY BA Bb bC bF Bg bL bM Bn Bo bP bQ bU bW bX cA cC cD cE cF cG cH cJ cL cM cN Co Cp Cq cR CS CT CV Cw CX cZ dA dB Dc DD DE dF DG dH dl dJ dK dL dM dN Dp eC Ed eF Ez Fa Fb Fp Fr Fw Gl GP Ha HB Hc hF Hq Hr Hu Hv Hw Hx iA Id IH Ii IJ Ik Il Im In iO IZ Jd Je Jg Jh Ji Jj Jk Jl Jm Jn Jo Jp Jq Jr Js Jt Ju Jy KC Kd kE kF KG kI Kj KK Kl kN KO Kp KQ KR Ks Ky Ld Lh Li Lj Lu Lv LW Lx Ly Lz Ma Mc Md Me MF Mg Mi Mj Mk Ml MM MP Mq Mr MS Mt MU Mv Mw Mx MY Mz NA NB NC nD Ne NF Ng NH nI NJ NK NL Nm NN NO Nq nR Ns Nt NU Nv NW Nx NY Oa OE Of Og Oh Oi OK Om ON oQ Or Ou Ow Oy Oz Pa Pb Pc Pd Pe PF Pg Ph Pi Pj Pk Po Pz Qa Qb Qc Qd Qe Qh Ql Qt Qv Qx Qy Qz Ra Rb Rg Rh Sr To Tz Ua Ub Ue Uf Ug Uh Uk Ul Um Uo Ut Uv Vo Vs Vt Vu Wm Tj tF) mF(aC AD aE AF aG aH aI aJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG cH cI cJ cK cL cM cN CO CP CQ cR CS CT CU CV CW CX

Figure 18 Continued cY cZ dA DB DC DD DE dF DG dH dI dJ DK DL dM dN Dp dR eC Ed eF Ez Fa Fb Fn fP Fw Fy GL GP Ha HB HC HF hG iA Ic Id iH iJ iO iP IZ Jd Je Jf Ju Jv Jy Kc Kd Ke Kf Kg Ki Kj Kk Kl Kn Ko Kp KQ KR KS Kx Ky Kz Ld nW nY Oa oE oF oH oK oN Or Ou Ow pF Ph Pi Pj Pk Qg Qh Ql Qm Qn Qt Qu Qv Qx Qy Qz Ra Rb Rc Rf Rg Rh Ri Rj Rm Sr Ss Tn To Tr Tt Tv Tz Ua Ub Uc Ud Ue Uf Ug Uh Uk Ul Um Un Uo Up Ur Us Ut Uu Uv Vo Vp Vs Vt Vu Vv Wm Tj tF) Ng(aC AD aE AF aG aH aI AJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG cH cI cJ cK cL cM cN CO CP CQ cR CS CT CU CV CW CX cY cZ dA DB DC DD DE dF DG dH dI dJ DK DL dM dN dR eC Ed eF Ez Fa Fn fP Fw Fy GL GP Ha HB HC HF hG iA Ic Id iH iJ iO iP IZ Jd Je Jf Ju Jv Kc Kd Ke Kf Kg Ki Kj Kk Kl Kn Ko Kp KQ KR KS Kx Ky Kz Ld nW nY Oa oE oF oH oK oN Or Ou Ow pF Ph Pi Pj Pk Qg Qh Ql Qm Qn Qt Qu Qv Qx Qy Qz Ra Rb Rf Rg Rh Ri Rj Sr Ss Tn To Tr Tt Tv Tz Ua Uc Ud Ue Uf Uh Uk Ul Um Un Uo Ur Us Ut Uu Uv Vo Vp Vs Vt Vu Vv Tj tF) In(aC AD aE AF aG aH aI AJ aK AL aM AN AO AP aQ AR AS aU aV aW AX aY aZ Ba BB BC bE bF BG bH bI bJ bL bM BN BO bP bQ bR bS bV bW bX bZ cA cB cC cD cE cF cG cH cI cJ cK cM cN CO CP CQ cR CS CT CU CV CW cX cY cZ dA dB DC DD DE dF DG dH dI dJ DK DL dM dN dR eC Ed eF Fa Fb fP Fw GL GP HB HC HF hG Ic Id iH iJ iO iP Is IZ Jd Je Jf Kc Kd Ke Kf Kg Ki Kj Kk Kl Kn Kp KQ KR KS Kx Ky Kz Ld nW nY Oa oE oF oH oK oN Or Ou Ow pF Ph Pi Pj Pk Qh Qu Qv Qx Qy Qz Ra Rg Rm Ss Tn To Tr Tt Tv Tz Ug Ul Ur Vp Vt tF) nA(aC AD aE AF aG aH aI AJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG cH cI cJ cK cL cM cN CO CP CQ cR CS CT CU CV CW CX cY cZ dA DB DC DD DE dF DG dH dI dJ DK DL dM dN dR eC eF Fa Fb fP Fw GL GP HB HC HF hG iA Ic Id iH iJ iO iP IZ Je Kc Kd Ke Kf Kg Ki Kj Kk Kl Kn Ko Kp KQ KR KS Kx Ky Kz Ld nW nY oE oF oH oK oN Or Ou Ow pF Ph Pi Pj Pk Qu Qy Rg To Ut Uu Vp tF) Kj(aE aF aG aK AI aM AN Ao aP aR aS aW AX aY BG bI bL BN bQ bU bV bX cA cD cF cH cK cM cO Cp Cq cS Ct Cv cZ dA Dc Dd De Dg dI dJ Dk Dl Dp eC Ed Et fP Fr Fw Fy gP Hf hG Hr Hu Hv Hx IH iJ iO IZ Jd Je Jh Jj Jn Js KC kE Kf Kg KI Kk Kl KO Kp KQ Kr Ks Kx Ky Ld Lj Lu lW Ly Ma Mb Mc ME Mg Mj Ml mM Mn mP Mr mS Mt Mv MW Mx MY mZ NB nC nD Ne NF nH NI NJ NK NL Nm nO Nq Ns NT NU Nw Nx Oa Oe Of Og Oh Oi Om On Or Ow Oy Oz Pa Pc Pd Pe Pi Pk Po Pz Qa Qb Qt Qu Qv Qz Rb Sr Ss To Tr Tv Tz Ub Uc Um Ur Vp Vs Vu Wm Tj) nK(aC AD aE Af aG aH aI AJ aK AL aM AN AO AP aQ AR AS aU aV aW AX aY aZ BA BB BC bE bF BG bI bJ bL bM BN Bo bP bQ bR bS bU bV bW bX bZ cA cB cC cD cE cF cG cH cI cJ cK cL cM cN CO CP CQ cR CS CT CU CV CW CX cY cZ dA DB DC DD DE dF DG dI dJ DK DL dM dN dR eC Ed eF Ez Fa Fb fP Fw GL GP HB HC hF hG iA Ic iH iJ iO iP iZ Jd Je Jv Kc Kd Ke Kg Ki Kk Kl Kn Ko Kp KQ KR KS Kx Ky Kz Ld nW nY Oa oE oF oH oK oN Or Ou Ow pF Ph Pj Pk Qy Rb Ss Uk Ut tF) Cp(aE aG AJ aM AN Ar As AX aY bA BB bG bW cF CS CT cV Cw cX DB dF dH dK dL dN Ed Fw HC Hu Hv Hx IH Ii iJ Il iO IZ Je Jh Jj Jl Jn Js kC kE KF kI Kk KO Kp Kq Ks Ld Li Lj Lv Lx Mb mE Mg Mj Ml mM Mn mP Mq MS mU Mv mY Mz Na nB nC nD Ne NF nH nI nJ nL Nm No Nr Nt NU Nv nW Oa Oe OF Oh Oi On Or Ow Oy Oz Pa Pb Pd Pe Pf Qa Qb Qe Qg Qh Qt Qz To Tz Uc Ug Uh Uk Ul Um Uo Ut Vu Wm) Iz(aF aN Ao aP aR As AX BA bE bG bI bN bU cF cH cS cU Cv dA dE Dg dJ Dl Et Ez Fb Fw Hu Hv Ic iH Ii iJ iO iZ Jg Jn KC kE Kf KI Kk KN KO Kq Kr Kz Ld Lv Mb ME Mh Ml Mm mP mS Mw mY mZ nB nC ND Ne nF nH Ni nJ Nk nL Nm Ns Nt Nu Nv Nw Nx Ny Oe Of OH Oi oK On Or Ow Oy Pa Pd Pe Po Pz Qv Qx Qz Rb To Uk Vt Wm) nJ(aC Ad AF aG Aj Al aM AN Ao AP Ar AS aX aY aZ Ba Bb Bc bF Bg bI Bn Bo bQ bX bZ cB cD cF cI Co Cq CS Ct Cu Cv Cw dA dC DE Dg dJ Dk DL eC eF Fb fP GL HB Hc hG iA iH iJ iO Je Kd Kk Kp kQ kR kS oE oF oH oK Or Ow Qu Ut tF) aN(Ad aF Aj Al aM An AO AS aX aY aZ Bb Bg bH Bn Bo bQ bX cA cC cD cF cH cM Co Ct Cw DE Dk dL Gl Hb hG Hu Ii iJ iO Jh Jk Jv kI Kk kN kO Ly ME mP mS MT Mv nB nC Nf nH nI nL Nq NU nW nY Of oH Po Qz Ua Ut Uv) nL(Ad AF aH Aj Al aM AO AP AS aX aZ Ba Bb bF BG bI bL Bn Bo bQ bV bZ cF cH Co Cq cS Ct Cu Cv Cw DE dJ Dk dL Fb fP GL HB Hc hG iH iO Jd Je Jv Ke Ki Kl Ld nF nY oK pF Ph Qu Qy Ua Ut Vs tF) Cw(aA aF aM As AX aY bG bI bN cH cS Ct Dg Dl Et Fw Hv iJ iO KC kE Kf kI Kk Kn KO Ld ME mP mS Mt Mv Mw mY Mz nB nC ND nF nH NI Nk Nt NU NW Oe Og Oh Oi Ok On Pa Qz To Uh Wm) Ld(Ad Aj Al Ao Ap AS aY Bb bF Bg Bn bQ cH Co Ct De dJ Ed Hb Hc hG Hq Hu Ii IJ iO Jd Je Jf Jg Jh Jj Jk Jv kI Mg Mk mP Mr MS Mt Mv My nC nD Nf Nm Nq Nt Of Om Oy Pb Po Qx Qy Tt Ua Uk Ut) Kk(Ad aG Aj Ao aY Bb bF Bg bQ Co Ct De fP Hb Hc hG Hq Hu Ii Ij Jd Je Jg Jh Jk Jv Lj mE Mg mM mP Mt Mv Mw My nD NF nI Nq Nt Nv Oa Of Om Oy Po Ql Qx Qy Tt Uk Ut Vs Vu) iO(Ad aG Aj Ao AP aY Ba Bb bF Bg bL Bo bQ cD cF Co cS Ct DE dJ fP Fr Hc Hu Ii Jd Je Jg Jh Jk Jy kG kN Mg mM mP Mt Mv Mw My nB nC nF nI Nm Nq Oa Of Oy Qt Qx Qy Ss) aX(Ad aF Ao AS Bb bF Bg Bo bQ Co Ct De Ez Hb Hc Hu Ii iZ Jd Je Jg Jh Jk Jy Kc Mg mP Mt Mv Mw My nB nC Ne nI Nq Nt Oa Of Om Oy Po Qx Qy Qz Tt Ua Ub Uk Us Ut Uv) nC(Ad AF Aj Al AO AP AS aZ Ba Bb bF Bg Bn Bo bQ cF cH Co Cq cS Ct Cu Cv dB DE Dk Fb fP Gl Hb Hc hG iH Jd Je Ke nY oK Ou pF Ph Qu Ut tF) Bb(aF AS bG Bn cF cH cS Ct Dl Hu Hv iH iJ kC kE kI kO kR mE mP mS Mv Mw nB nD nF nH NI Nk Nt NU OH oK Po Qz Rb Vs Wm) Ct(Aj Ao As bG bI cF cS cX Hu Hv iH iJ iZ KC kE kO kR mE mM mP mS Mw nB nD nF nH Ni Nm NT Nu Oh Or Ow Pa Qz Wm) Qz(Ad Aj Al Ao AP As aY Ba Bg Bo bQ cF cH Co cS Dk fP Fr gL gP Hb Hc hG Hu Ii Je Jh Kl Ko Ms Mt Mv Mw Nm Pj Qy) Of(aE aF aL aM aR aS aZ bA bE bG bL cD cF cG cH cS cU Cv cX dA DL fP Fw hG iH iJ iZ Kc Ko Kq kR oE oF Ow Ph To) mS(Ad AF Ao AP Ar As Ax Ba Bg Bn Bo bQ Co Cq Cu Cv De Dk Fa Fb Gl Hb Hc Jd Jc Jy Ke Kl Kp Ow Ph Qu Ut) iJ(Ad aG Ao Ap As aY Ba bF Bg Bo bQ cD Co De Fb fP Hc Hu Ii Jd Je Jg Jh kF kG mM Mt Mv Mw Nq NT Qu Ss Vs) Bg(Aj bG cF cH cS Hv iH Il iZ Jn kC kI kO kR ME Ml mP nB nD nF nH NI Nm Nt NU Pa Wm) Ii(aF aJ aR aS Ax Bo cH CS Cv cX Dc dE DL Fw iZ Ki Oa Or Rm To Vp Vt Vu) Ao(bG cF cS Dl Hv iH iZ kC kI kO Mb mE mP nB nD nF nH Ni Nk Nt NU Oe Or) Hc(aF bG cF cS cU Hv iH kC kO Ly ME mP nB nD nF nH Ni Nu oK Po Rb Wm) nF(Ad Al An Ar As cF cH cJ Co cS De Dl Fb Ji Kc nW Ny oE oH oK Ph Ra) Aj(AS aV Bo bQ cF dA De Dk Hu iZ kE kI mP Mv Mw nD Ne Ow Po Qv) mP(Ad Af AP As Ba Bn bS cD cH Cv De Dk Dl Fb Jd Kc Kl Kr Ph) Nt(aF AS Ax aZ bG bQ cS dL Fb Fw Gl iH Kc Ki Kp Kq Kz To) nD(Ad Al Ap As Ba Bo Co Cq Cs Cv De Dk Dl Fb Jd Je Kc Qu) As(aF aM aS Ax cS cX dD Hv iZ mY nB nI nU oF) Mw(aJ Ax bG bW cH cL cM cN dG iZ oK Ub Ug Uh) cF(dL Ed Hu Hv iZ Lj Mv nI Nq Oa Ub Ue Uk Vu) aS(bA bG cT Jo kO Mg Ms nH Nm Nu Pa Ug Wm) Fb(Ax Ed iH kC kO Lj nH nI Oa Oe Pa Wm) nB(Ad aP Bo bQ Co dI dJ fP hG Je oH Ow) cS(Co dN Ed Jh Mv nI Oa Tn Tt Uv Vu) cH(Ad Ap Hu iH Jg Jh kC kO Nm Oy) nI(AF bG Bn Co Dk Hb hG Kc oK) Wm(bQ bX cD cJ cM Kc Nj oH Qu) Mv(An bB bG bI dJ iH iZ kR Or) Dk(Ax kC kO nH nW oE Pa) aF(Ed Jg Jh Mg Nm Oa Pa) bQ(Jj kO Ml nH Ni Nu oF) Mt(An bG iZ Or To Ug) De(cX Hv iZ Jj Pa) Nm(Ax aZ Cv Dg Dl) aY(Bn Ni Nu Po Vs) bG(Ba Hu Jh Jk Nq) kC(Ad cJ Kc oH Qu) Ow(Jo Mg Ou Qv) cX(Bn Jk Tt Vs) kI(Ap Co Gl Ou) Ad(kO nH nU) Dl(Ap Jg Jh) Po(Ax Ed Or) aP(aJ iZ Ne) iH(Kc Nq oH) hG(aJ Hv Uk) Bn(Hv Oa) Nu(Co dA) Ni(aM Hb) Jh(Kc Or) Qu(kO nH) dL(kE oH) iZ(Hu mM) ApnU AxQc EdcU EtHb MgdJ MpVs UaOr QtdD KeNw OabV UkmE UrOy VvcV} Ib{nR(aD AN aV BA bE cH cT cZ dA Dc Dg dI dM Et Ez gL hA In iO Ip Is Ji Jn jP Kc kE Kf kI Kk Kn Ko Kp Kq Ld lK Ma Mb Mg Mk Ml Mm Mw Mx nA Nb nC Ni NJ NK nL Nm Ns nT Nv Nw Oa Oc OH Oi Om On Or Ow Pd Pk Pz QV Qw Qz Rg Tv Un Uv) kE(aO aY BA bF bQ bZ cE cG cI cL cN Cu cX Dc dF DG dH dM Et Fy Gl hB Hf iB Id Ik Im Is Ji Jn Jp jY Kf Kk Kl Kn Ko Kq Ld Lh lM Lx Ma Mk Mn Mz No Nv Nw OH Ok ON oQ Or Ow Oz Qa Qd Qe qV Qw Rm Sr St Tn To Tv Tz Uc Uf Uh Un Vs) kI(aD aY BA bF bQ bZ cE cL cN cX Dc dF Dg dH dM Fy hB iB Id Im Is jD Ji Jn Kk Kl Ko Ld Lh Lx Ma No Nv Nw Oa OH ON Or Ou Ow Qa Qe qT Qw Rm Tn Tv Vu) Ji(kC kF kG kK kN kO kP lW lX lY mE mF mH mI mM mP mS mT mU mW mY mZ nA nB nC nD nF nH nI nJ nK nL nM nN nO nT nU oO oQ Qw) nL(aD BA bF bQ bZ cE cI cL cX Dc Dg dI dM Fy Id Ik Ip Is jD Jn Kk Kn Ko Ld Ma Mk Nw OH On oO Or Ow

Unconstrained panels with 3 analytes, where 1.0E-8 >= 'AUC p-value' > 1.0E-9. Contains 6,464 panels of 17,333,483 total panels evaluated. :
oP{Iz(aA aC AD Af aG aH AL aM aO Ap aQ Ar aS aU Bg bH bJ bM BO bP bQ bR bS bX bZ cA cB cG cl cK cL CO cP CQ cR Ct CW CX cZ
DB DC DD dF dG dH dl Dk eF Fa Fn Fp Fr Gl gP Ha hB hC hF Hq Hr iA Id lm iP Jd Je Ji Jj Jo Js Jt Ju Jv Ke kF kG kK kS Kx Li Lj Lu Lw lX
Lz Mc Md Mg mH Ml Mr Ms mT Mv Mx My Na Nf Nh Nl nM Nn NO Nq NR nW nY Ok oQ Ou Pg Pj Pk Qa Qb Qe Qg Qh Qm Qu Qy Rf Rg
Ri Rj Rm Tn Tr Tv Uc Ud Ue Uf Ug Uh Ur Vv Tj tF) Cp(aC aD aH al aO Ap aZ Ba Bc bE bl bJ bM Bn Bo bQ bS bV bX cB cD cE cH cl cK
cM cO cP Cu cW cY cZ dA Dc dD De Dg dl Dk Dl Dp eC eF Fn Fy gL Gp Ha HB HF Hq Hr Hw Id Ik Im Jd Jf Ji Jm Jo Jp Jt Ju Jv Kd Ke Kg
kK Kl kP kQ kS Kz Lh lW lY Lz Mc Me Mf mH Mi Mk Mm Mr MT Mu MW mZ Nc Nd Nh Ni Nl nM Nn nO Nq Nw Ny oE oH OK oN oO Pc
Po Pz Qd Ql Qm Qv Ra Rb Rf Ri Rj Sr Ss Tr Ua Ud Uf Uu Vv Tj tF) Cw(aC Ad Af Al AO aQ aR aU aV bA BB bE bF Bg bL bQ bS bU bV cC
cD cE cG Co cT cU cX dB dC dD De dJ dR Fn fP gL gP hC hG Hx Ic Ik II Je Jh Ji Jj Jk Jp Js Jt Jv kF kG kN kS Lh Lj lW lX LY Mb Mg MH
Ml mM Mn Mp Mr mU mW Mx Nf nM Nq Ns nT oE Of oK oO oQ Or Pe Ph Qe Rj Sr Tr Ub Uk Us Vp Vt Vu) Bg(aG aJ Al An Ao aR aS Ax
aY BB bl bL BN bQ bU bV bX cB cE cL cR CT cU Cv cX dA dC dD dE dG dL FP Fw hG Hu Hx iA Kc kE kG Ki Ko Lj Lu Lv Mb Mc Md Mf
Mh Mk mM Mn MT Mu Mz Nb Nc Nd Ne Nf Nj Ns NW oE OF Og Oh Oi oQ Or Ow Oz Pc Pe Pf Pj Qb Qx Rb To Tt Ub Ul Um) Of(aC aD Af
aJ Al An Ao Ap aQ Ar As aV bC bJ bM Bn bO bP bR bV bW bX bZ cC cI cK cL cN CO cP CQ cR Cs CT Cu cV cW Cx cY cZ DB Dd De dF
dG dl DK dM dN dR eC Ed Ez Fn GL GP hB Hc HF Jf Ke Kf Ki Kl Kn kQ KS Kx Ky Kz nY oH oN Or Pi Qm Ri Ss Uu Vo tF) aN(aC aE Af
aH al aJ aP aW bB Bc bJ bR bS bW cE cG cK cQ cS Cx cZ dA DC Dd dF dG dH dK dR eC eF fP gP hB HC HF Hv iA Ij lm iP Jd Jj Jm Jn kE
Ki Ko kP kQ kR Kz Ld Lh Lj lX Mg ml mM Mr Mu mZ Na nD Nr nT Oa oF Og Oi oN oO oQ Or Oz Pi Pj Tt Ue Uk Up Us Uu Vs Wm) Ct(Ad
aF aJ AL An Ap aS bA bE bH bL Bo bQ bV cM cU CV dA Db Dc dD DE dL dM Ez Fr Fy Gp HB hG Il iP Jg Jn Jt Kg Ki Kl kN Ko KQ Lu Lv
Ly Mb Mc Mp Mr mY Nd Ne nN nU Oc Om oO Ou Oy pF Pj Po Qm Qv Rb Rj Ss Ug Uk Ul Um Ut Uu Vu) Ao(aG AJ AL aM aP As aV aZ Bb
Bn Bo bS bU bV cA cC cD cH cZ Dc DE dL hG Hu Ii Il Jn Kc kE Ki kQ kR Lv Ly Me Ml mM MT Mv mW Nc Ne nN Ns Nw oE oF Og Oh Oi
oK Om Ow Oz Po Qx Rb tF) Ii(aC AD aH aO aP aV aY Ba Bc bG bJ bL bV bW bX cB cD cW cY dA Db De dG Dp eC Ed Ez Fn Gl GP Hb Hc
hG Ic iH Jd Ju Jv Kd Kf Kn kR Ky oF oK Ou Ow Pi Qh Ql Qt Rb Ri Ss Tn Tr Uf Uh Tj) Bb(aA Al aM An aO Ba Bc bl bJ bL bN bQ cA cD cQ
Dc dE dJ dL fP Fw GL hG Ik II iP iZ Jf Jh Jn Jv Ki Ks lW Mt MZ Nc Nj Nm nO Nq nT Nw Nx Oe Og Oi Ok Om Or Oy Pd Ph Rj To Ua)
As(aG al AL Ap aR Ba bG bJ bL bN bQ cA cB cF Co CV dC dE DG dJ Dl eF Fn fP Hc hG iO Jj Kc kE Kl Kq kR lW mE Mg mT Mv Mw Ne
Nm nT OE Og Oh oQ Or pF Rj To Ua Wm) iJ(AF aX bl cE cH cl cM cQ cS dC Dg dJ eF Fn Gl gP hG Hq iA iH iZ Jv Jy Kc kE Kl Ko kQ MP
Mu nC NF Ni nR nU Om Oy Pc Qm Qt Qx Qy Qz Tt Ua Uk Ut) Kj(aJ aU bB Bo bR cJ cL Co cR cU dC dG dH Ez Fp Ha hB Hc Ic Jk Jl Jq Jt
kN Lv Lw Lx Mf mH Ms nR nY oH Pb Pg Qc Qd Ql Rc Rf Ri Tn Tt Ud Uh Uo Up Uu tF) Mv(aC Ad aE aG al Al Ar aS aV Ax aZ bA bE bL
bN Bo bQ bU bX cG cR Cs cU Cv cZ Db Dc De dl Dk Dl Ed Fb fP Fw gP Hb Hc hF Ko kQ nW nY oE oF Ow Ub Wm) nJ(aE al aK aQ aR aU
bA bC bE bG bM bP bU cE cL cM cO cP cR cT cU cW Cx cY dD dG dK dM dN dR Gp iZ Jv Kg Ki Kl Kn Kr Ky Ld Ou Pi Pk Qy To Ua Us)
Qz(aE Af aV bC bG bU cA cB cD cE cM cQ Cs Cu cZ dA dB dD Dg dJ dK dL Fb Gl hB Jk Jt Ki Kp Kq kS Mc Mg mM Mu My oE oH oK oN
Oz Pk) nF(Aa aC Aj aK aM aP aQ aS aU AX aZ bF Bn bQ bU bX cD cQ cX dR Et Fa fP Fw Gp In Jd Jf Ki kS Ld mF Ml Mp Nj Nx On Ow
Uk) nC(aG aV Ax bB bH bL cA cB cC cI cO cQ cY cZ Db dF Dg dN Fa gP hB HF In Kc Kg Ko kQ kR KS Kx oE oH oN Pj Qt Tt Vs) nL(aE
An aQ aR aV Ax bB bH bJ bR bU cA cG cJ cM cO Cs cT cU cZ dD dl Dl eF gP hC iA iP Ju Kc Kd kR kS Kx nW oF Pi Ql Uk) Hc(Aj aP aS Bn
bQ bV cA cD cM Cv dD dJ Dl Fb hG iZ Jf Jn Kc kE Ko Kr Kx Mb Mh Mp Mt Mw mZ nl Nk Nm Oe Oi Pa pF To Vs) Ld(aM Bo cM Cq cR Fb
Gl iH II Jy kC kE KG Ks Lj Lv Ly Mb Ml mM mT mZ Nb Ni Nv Nx Ny Oa oK Ph Pj Qc Ra Tn Ue Ug Uv) iO(aA aC aM aX aZ bG bN bZ cA
cC cJ cL cO dA dC dl Dk eC Fa Fb Hb iH iZ kO Kp kR lY mT Nf nH nT Nu oH oK On Ua Ut Vu) Kk(aM aO Ap aS aX Ba Bn Bo bV bW bZ
Cq cR dC dJ Dk iH Il iZ kC KE KG kQ Ks Mc Mr mS Mu NB Ni Nm Nu Ny Qm) Hu(aE al aJ aK aP aS Ax aZ bl bN bQ bU bX cU Cv cX dA
Db dC dJ dK DL Fb fP Fw kQ kS Kx nW oK Or Qx To Ug) aX(Aj aM Ap aY aZ bC Cq Fa fP Fw Hq kE kG kl Kq kS Lj Md mM Mr mS mZ
Nf nH NN Nv oE oK oN Ql Qm Rb Tn Vt) mP(An aO aR bF bl bN CO Cq Cs cU Cx Db dC dE dL Fa Gp Hb iH iZ Kf Kg Ki Kn Kp Kx Or Ou
Pi Pk Ss Ut tF) De(aM aY bA bG cS dA dC dJ Ed Il Kc Ki kO Kq Ms Mw mY Ne nH Nj Nk Nm Nu Oh Or Ow Oy Oz Po Rb Ss To Ub) Nt(aC
aE aG al aJ Al aO Ap Ar Bc bL Bo bX cF cM Cv Db dC dD dE dJ Dk Dl dN Fa Hb mF nW Oa oF oK Rb) Mw(Af al Al aM Ar aS bA bF bl Bo
cG cJ cO Cq cR cS Cv dH dl dL dM dN eC Ed iH Ki Kr Kx Ky Or pF Uk) Aj(aL aP aY Ba bE bF Ed fP Fr Gl hG Hq Hr Jh Jk KC Ke Lv Mk
mM Mt Nf Nl Ns Oe oK Om Pb Uk) cF(Ax aY bF eC Hb hG Hq Jd Je Jk Jv kO Ly Mk mS Mt nB Nf nH Nm NU Oh Om Or Qx Qy Ua Ug)
mS(aM aS Bc bF cD Cx Dd dL Ez fP gL gP iZ Jf Kc Kd Kn Ko Ks Ky oH oN Pk To Uu) nl(Ad Al aO Ap Ar aS aY Ba bF cB cH Cv dA dJ DL
fP Gl gP iH Je Ki Kl kS nY) In(Aa Jn mF nD nK Qg Qm Rb Rf Ri Rj Sr Ua Ub Uc Ud Ue Uk Un Uo Uu Vo Vs) Jh(aG An aR aS Ax bl bU bX
cB cM Cv dA dD Ef fP iZ Ki Kn kQ Kr Kx Ky Ow) hG(Ad aM aS bQ cH dL kC KO Ly Mg Nm nU oK Ph To Ub Ug Us Uv Wm) iH(Ad aO
aY bF bQ cD cJ Co Dk Je Jg kF kl mM My Nm nT Oy Qu Wm) Di(aF bE bG bJ bR cB cl cU cY Dl dR gL mT oH Qm Rm Tv Uu Vv) bQ(cL
cV hC Il iZ Mb mE Mp nU Nw oE oK Or Oy Pa Po Ug) cS(aH Bo cZ eC Gl Hq Je kO Mg nB Nf nH Nm Nq nU Pb Wm) Bn(Ax Jj Jl Jv Lj Mg
Mk Mp Ms Mt Nm Nq nU Or Oy Vu) aS(Ad An Ax aY bJ Hb Jj Jt kN Lj mM My oK Or Vu) nD(An Ar Ax Bc bS Db Dc Dd Dg Kg Kn Og Ow
Ph Qy) Ad(bG Hv Jn kl mE mY Ne Ni Nk Nu nW Pa To) aP(Ax dG dL Dp Il kC kO nH nU oQ Or Uk Wm) iZ(AF aG Ba bG bV fP mE Mg nT
Nu oH Po) Bo(Ax aY Jj mE Ms Ni Nm NU Og Pa Wm) Jk(aF aG aM bl cH dJ Ed fP Hb Oa oK To) Co(aF aR bG cH dJ kO nH Ni oK Po Wm)
Gl(bA cX Dl Hv Jj Nm Nu Oa oE Pa Ub) nA(Ju Jv Oa Qx Sr Ug Uh Ul Vs Tj) Wm(aY dD dJ fP iA Kl Ng nK qT) Nm(aJ Ba bF bX cX dK
fP Kc oF) Mt(aG aM aR Ed Kc Rb Rj Uk Vs) Ni(aE Ba bF bL bW Fa oE Ub Uk) Oa(cB Cs dA dJ Fa mE Ph Po Ut) aF(cX dL Jj Lj mM nU Oy
Uv Vu) nH(aC Ba bl bX Cq Cv dA iA Je) Jg(Ax aZ bG Cv Dg Kc Ko oF) Or(aY bF bX Je Mc mE mT Tt) mF(Ml Mu Mx Nb Nn Nq Nu Og)
nB(aE aO aY cB Dk kQ kS Ut) kO(Ap Ba cJ cM dJ fP Jd Je) cH(Dk Ed Fr Hb Jt Jv mM) Fb(Jn Mg Oh Pb To Vu) Nu(bG cD cY Dk Kc oK)
My(aG aR bV dA Kc Rb) Oy(aG aM aZ bG Cv Fw) dL(dJ Hv Kr nO nT oK) mE(Fa gP Je Kc Kf Ow) nK(Id Jf Jy Oi Vp Tj) kC(aY bF cD Cq Jd
Je) Ax(Ap dJ Kl Mp Qu) Dl(Dk Hb Jt Mg Qt) Ef(aA Ri Ub Vs Tj) Ed(aO kl Qm Rb Tt) Po(aJ cX Ki Ra) Tt(dD Ky Nj To) Vs(cL Dc Ub Uk)
aR(Hq Lj Nf Om) nU(Je Kc oH Ut) kI(dE Jd Je Ki) Aw(aQ Bc bR) Mg(bX dA Kn) Ua(bG cT Tz) Hv(aO bF bG) aM(Nq nT oK) dJ(bJ Nf Om)
Af(cX Ne) Ap(aZ Nk) Il(bV cD) Hb(Kc Nw) Kg(Mb Me) Kl(Lj Pa) AlNc BaoK DkUg LyOw MhKc MpVv QtaY JvkR KqUt OglK aOcV bGmM kEoE} Qw{Ub(aD aE AF aG aH aI Aj aK AL An Ao AP aQ AR aU aV AW AX aZ Bb bE bF bG bH bI bJ bL bM bN Bo bP bQ bR bS bU bV bW bZ cA cC cD cF cK CO CP CQ CS Ct CU Cv CW Cx cY dB dC Dd Di dJ dK Dl Ez Fa FP Fr Fw Gl gW Ha Hb Hc Hf Hq Hu Ih Ii Ij Ik Il In Jd Je Jf Jo Jp Js Ju Jv Kc Kg Ki Kj Kk Kl Ko Kp Ld Lh Li Lj Lu Lv Lw Lz Ma Mb Mc Md Me Mk Mm Mn Mp Mq Mr Ms Mt Mw Mx Mz Na Nb Nc Nh Nn No Ns Nt Nu Nv Nw Oa Of oH Oi Ok Om On Oy Pb Pc Pd Pg Pj Qb Qc Qg Qh Ql Qv Qz Ra Rb Rc Rg Rh Sr Ss Tn To Tv Tz Ua Ue Uf Ug Uk Up Us Uu Vo Vs Vt Tj) gP(Aa Af aM Ax bB bV cE cM Ct dH dK dL Dp Ez FR gL Gp hB Hu Hv Ic Id Ij Il iO Is Ji Jl Jo Jq Kf Kg Kq Kr Ks Lw Lx Mg Mt Nc Nf Nk Nm No Oa oE Og On Oy Oz Pb Pc pF Pk Qd Qh Qx Ra To Ue Ug Uh Tj) nU(aM aR As Ba Bb bF bL cE cF cL Cq Dg dN eF Et Ez Fw Gp hB Hu iB Ii IO Iv Jj Jl Jp jT Jv Kl Ko Lh lO mF Mj Mk Mp Mv Mw mZ Nl nR Nv Nx Oh Om Oz Pd Pf Pg Qc Qv Ra Rb To Tz Uc Uh Um Ur Vo Vt Vu) Ib(aJ An aQ aV aZ Ba bB bF Bo bQ bR cE cG Cw dB dF Dg Ed eF Et Hf Im Iu Jg Jn Jp

Figure 18 Continued

Figure 18 Continued cJ(nH nL) dX(Hv Ou) nK(dG pF) EmLy ExNx NjfR Kfml KnmU OrnL OweM aYnH mSpF} mF{oQ(bE dE Di dL Gp Iz Jd Kc Kk Kl Kp Kr
Ou Ph Pi Qu Ss Ur Ut) hB(Bg cI Fb Iz Ke Kj Nf Ng nT Of Ou Rj To) Kc(bA dG dH jl jK jL jR jU qX rA) oO(dL Fb Fw Hc Iz Ki Ph Pj Qz)
cl(cG cH hC iO Jj lM oF Uh) Di(bF cE nR oN) Mw(dF pF rZ Uh) dL(Fn Fy Mh Mt) aY(jD nT Uk) Dg(Ng Nm) Tv(aR Tt) Kk(cL pF) Or(mT
Pk) aJ(nT oH) cG(Dk qU) cX(jV lK) dF(jV lK) dM(jD Ng) dN(cH oH) MfrZ TorA IpQg IqcL lrPk QzbA OaaR OfdG cEjP dllM} nF{cJ(aN Bc
cT dM Et Hx Id Kn Ko Ml nA oN Pd) Ow(bA cE cG DG Jd Kd My nU oF Oy) Uh(bA cL Mc Nf Nk nU qV rA Rg Rj Tv) Kc(jD jl jM jR Mp
Ou qX) Kn(Aj aY cG cL Ii Ng Or) Nx(Jh Md MP My nU) oN(Aw Hu Mv nA Ng Uk) Kk(lW MP nU To) bA(Ct Fb Ng Nj Ra) oH(aY dH nR
Uf) cE(Aw nA Qz) dM(cH lK qW) Cp(dF lM) Dg(Ad Jt) Fb(Kl nR) To(Ji rA) MwUf HubF HwKf aSdF bXjG} dX{Jj(aU Ax bC bR eF Gl Gp
Gz Hw Iq Iz Kc Kj Kl Kq Ml Nb Nj Nx Pk) cL(aF al aQ bA bM Bo cH Ct cZ dD li Nd Nf Ow) cT(aK aM aQ aV aZ bB cU dA) bA(Aj Al cl cU
dE Oe) Kj(lk Io Kf Mn Nw) cN(cE Gp Ji Ok) Aj(Et Kp Ou) Bo(Al aV dE) Ng(Dc Dg Ko) li(Et Nv Ok) Qd(Hu Ih Nr) Nb(bB Kc) Ik(Iz Kq)
Ow(cE Jp) aV(Kr Ky) DgKl MzKp HcOy IsJs JiKg JocV KdNw aCbE aNbL cEcP} Ng{Kf(Ao Bc cM eD eF jD Jn jP jU oH Om Pk Pz qU qX
rA Rj) Dg(Kk mP nC nL nU Pz qX rA Rj) nU(cA Dc Kc Kl Ko Kp To) Ow(Ex fR Gz Jg nB Ph) Pz(Ad Bc cX eF Ou) mT(Ad Ap cE Cu dF)
nA(aJ dG Ef Kl) Uu(gP lL qX) Ba(mM nl) Kp(qX rA) Vq(lM Nx) nK(cE dM) kE(aJ Ef) kl(aY hB) BcRj EmOu QvoQ JneF KknL KnnB KqgP
aNeM lYrZ} Mw{oQ(aN Ar aS Aw cF cl cJ cM Dc dJ Dk dN gP Kc Kk Kn) dG(kC kK kP IX mE mZ nB nH nl nR) mS(aJ bC Dg dL dM dN
Uh) Uh(kE ml mP nD nK) mP(cE hB Kk oN) mT(Bc cE dF Vt) nA(bA cL dF dL) nK(bZ cN Dg dH) nL(Dg eF Id To) nU(cE Kf Kq) kI(dH hB
Uf) Kk(lW mU) nR(iJ Kc) kE(aY dL) DgnC UfmZ cJnD dMnT mEhB} Em{Ly(aC aH aJ An Bn cX Hu Io Ji Jl Jq Kg Qb) Ou(aJ Ct dB Iv Jk Kk
Mk Nf Nr Pd Ph) Kg(aQ bB Dc Ji Jp Me Qa) Nx(aJ aN aV Kk Ks Ow) Or(aJ bC cT Mh Nj Ok) aV(Hv Ji Jl Lv Mp) Mg(bA cT Is Qd) Jo(Et Ji
Lh Qa) Kj(cT Kq Ok Qe) Nb(bJ Hu Oy) li(Is Nw On) Jj(aQ Ow) NmOk LuOw IsKs KkNw KyaQ bCbJ} nA{Is(aY bX dL Kz Pk Rb Vv) jV(bA
cG cL Or pF To) dL(Ip nT Nx rA Tv) dN(cX dD Kn Or qV) oN(Ao Jh Jv Mc Ut) To(Cv Nx Or rA) It(cE cL cX Ou) dG(Kk Mv Of oH) Nw(cI
Dk Ur) aY(Hc Ii nT) cE(Af Di Mc) cJ(jU Pa Rj) cL(Dk Iq Jv) Cp(Lx Oh) Or(Me Ur) dF(Iq Ur) CtOw MchB KjOh KkpF aJnT dJlK} eM{aN(Ap
bM bX cD cE cF Ct Fp gP Kc Kg Ki Kp Mp Nb Nq Nx Ou Oy Qd) cL(aQ Ax aY bL bQ bZ Ct cU dA dC Kj Nd) Bo(aQ Bc bW Cv Hv Nx)
Mg(Dc Jq Kf Kp Nx) aV(cT cV dF Nw Or) Nb(bB cV Nj) Is(cH Jj Jm) bJ(bC cN) cV(Hf Kc) AjHb JjNx JqKj JsNw aDcE} mT{Or(aS Di dL Ir
kl nL nU qW Qz) qV(aM aS aY bE bH Ct) Kk(Io Ir lK Oa pF) Is(aZ cH Cp Di) Qz(cE Dc oN Ou) aJ(eD jQ IO qU) IN(Cs dl hG iA) Ct(iB jT
qW) cX(lK Vt) dL(jQ oH) hB(eD Mv) qW(aL cl) jY(aF Us) CpQa NtdG NecV KdlK KjOh aMjU} nK{Is(Aw bG Cp cX dI Dk Fn Ha Or Tt Ug
Uk tF) Tv(bC Bn Ef lj Jv Mv Qc) cl(dG Et Mp To Uc Vt) dG(Di Dk Ii Je nT) Dk(nR Oh Or) Gp(Ip Iv St) dN(bA cX Kk) Mv(bZ To) Or(bX Me)
dL(Kn Nj) IobA lpdF IrQg ItdM OhcJ} lK{nR(aD Af aW aZ bE bJ bL bZ cC cH Co Cw dC dl dN fP Hf Ic Kn nY Ou Vu) nO(Ad cl Ct dJ Gp
Hb Pk Qu Tr) mH(Ax cR Ct dL Lf Kc Qm) dM(kG IY mE mM) mP(bX De Kc Nv) IX(aY hB) QunD KckC nMrZ} Ow{nU(Aj Bg De dL Iq Mg
Nf Oz Qv Qy) oQ(Af Ef Hb Ii Jk nB Ou Vs) Mc(kE kl kO mY mZ nC nN) Ct(kE ml mS mW nN nO) eP(Hf Jp Oe) fR(gP Kc Mg) mS(Hb Io It)
dL(nO nT) nB(hB Mh) ItnD nLoO} fR{Nx(aC Co Ed Ef Fp Hu Iz Kg Ki Kj Kk Nf Nl Oi To Tv Ue Uf Uk Up) Qz(cE Ik Kn Lh Mz Nw) aN(bR
cE Ly Og) Is(cD Og Oy) Or(bR Nf Pz) EtiH MeQn NiNj IpUr} Kc{jU(kK kN lY mH mU mW mZ nL nM nT nU) nD(eD gW Is jD rA) nB(jF
jQ lO qW) nU(aY dL dN) qX(Aj Qc Vv) jM(kl kO nH) IN(lW mP mW) OueP OznC PbrA eDkF mlnl mPjR} mS{Is(aN aO dA Gp Kn oH Vv)
dL(cl Dk Ip Kn Nb Nl Pk) Ip(Ao bG cH Gp Qg) dG(li Jd nT Of) Dk(dM hB) Mx(Bg cl) Iq(aY ld) It(dl Kn) aS(qX rA) MvcJ NbOr Jlcl KkbC
iHjV} tT{Qc(lo Jl Jq Lj Ml Mn Mq Mx Nx Pz Qa Qe) Pz(Ik It Jm Js Ml Mt Mz Nl Oi) Ji(Hu Hx Il Jp Js Ml) Mk(Et Iu Lh Mm Mt) Iu(Jp Nu)
MaMm} Kk{nU(Ao As aY dL dN Ed Iu Ju Nb Nq) mP(Dk dL iC Ir Iu Nb Ur) dN(kE kN lW nC nL) Dk(lW oQ) It(kF nR) jU(ml nL) jV(mY nl)
TokE aYnC dLnO nBrA} kl{jV(bA Gp hB Jv pF Qz) Or(Jv Ly Ou Pg) aY(Af Di qV qY) dL(jM jP nT qV) dN(Di eD lO oH) jU(bA cl hB pF)
dG(iC Mc) AwlM DkhA EfjY JjUr cZqV} kE{Jj(Fw Qz Rj Vp Vt Vu) dL(bA cl Di Kn Ml Rj) aY(Di oF Rj To) Tv(Kj nB) dG(jP Of) DicE
DkhA McOr aSbA} eP{Is(Mg Of Og Oy) bL(bA cG dF Nw) Hu(Hf Kz Nd) Dc(Kj Og) Jj(aU Om) aN(Ly Og) aQ(bA cL) MgcT QcQd aVdF
bJcN} nL{oO(Bo Ha Ju Kj) Tv(Ju Kj Ph) Kn(Ju JV) Or(jV Mc Me) Jj(cZ Qz) cl(cH Hq) cX(jU Me) CvOz HaOa HcaY JvoQ} nU{Ef(Dc Kl
oH) Kn(Ao Iz jU) Dg(Ad Jt) dM(Dk nT) oH(bW Of) EtHb FbOh GpNb NtbX MeOr MvaN IidG IpKj QxNx aSbA} mP{Di(cJ dG oN) dN(cH
nT oH) Gp(Ip Iq) cJ(aN Rj) nT(dG Vt) IO(aS bX) oH(Iv Ur) CpTv DelM IpKj IsaF cllL cZqW} nD{Is(aF bX Cp Ih Pk Qu) Gp(Ir Iu St) Qu(cE
oQ) Vp(Of Pb) nT(aJ dG) DicJ ToVt IpQg ItoH JdoN UhjV aLqW} qX{cJ(Aj Ex Hc Oz Wm) Aj(Jg Kp qU) Vv(Bc cH qU) Oz(cH Kp oE)
Ct(Pz qU) nR(aF Aw) DgJk aSnB} oQ{Di(dl Hc Jv Mx To) Dk(cV Hu Kq Oi Or) li(Dc Rm) AwMx IzdI SsiO JvnC KeNw VsbA aNaS}
nR{Bn(jl jU lN) Aw(jU Kp) Di(dN Vp) Dk(jl lN) BolN CpjT EtHb IuKj aFjU} lY{rZ(Ih Jl Jn Li Lz Mc Mp Mt Mu Mv Nd Nf) AwlM MprY}
nB{Tv(As Jk Kj) Kn(Ed Jh rA) Oh(Dk Fb) liRm aLqV aScT dLoH} nC{Di(dG Id pF) Tv(JV Kj) Is(li Jm) MecX QuoN cHdN cJjM} Nx{Ex(Ap
Co Ik Iz Jt Ks Oy Ql) Gz(Co Ct Kj)} Vv{Kf(eD iC jE jM jO jQ jR) DgjR bCrC} dL{oH(kO IX mE ml nN nT) Kn(nl nO nT)} Qc{tX(Jp Nw
Qa) Mk(tV wB) Wn(aA cH) IhwB} aS{bA(kC kP lW IX mE mW nM nN)} Fb{Oh(kF ml mM mY nH nO)} Mz{ll(tN tX) Js(tV wB) QatN}
nT{dN(aM cH) EtHb KnjU aJiC} nl{Di(cE pF) DgNm TorA cHcl} tQ{Et(lj Jk) MkHv MtNb PztN} rA{To(mU mZ) aJkN cJkC} jV{KnkO
OrmE cXnH dFmM} gP{MgKf JjRj TkcM} nN{DidG McOr SsaJ} kK{jl(dA dI) KnjU} Mk{NbwB HvtX} ll{l dH dI DK dM dN dR Ed eF Ez Fr Fy GP hB hC hF iA Jj Jk KF kG kN Ko KP kQ kS Kx Ky Kz Lh Lj Lv lX LY Mc Md Me Mg MH mI Mk mM Mn Mp Ms mT MU My Na Nb Nc Nd nM NN No Ns Nv nW Ny Oa oE oF ON oO oQ Oz Pc PF Qg Rg Ss Tn Tr Tt Ug Uh Uk Ul Um Uu Uv Vp Vt tF) Cw(aE aG aH aL An Ap aW Ba BC bH bJ bM BO bP bR bW bX bZ cB cI cJ cK cL cM cN cO cP Cq Cs Cu cW Cx cY cZ dA Db Dd dE dF dH dI dK dM eC Ed eF Fp Fr Gl Hb Hc hF Hq Hr Hw Id Ih iP Jl Jm Jq Jr Kd Ke Ki kK Kl kP kQ Ks Kx Kz Li Lu Lv Lw Lx Lz Ma Mc Md Mf Ml Mj Mk Mm Mq mT Mu mZ Na Nb Nh Nl NN nO NR Nx nY Oa oN Ou Pb Pc PF Pg Pi Pj Pz Qa Qb Qc Qd Qg Qt Qu Qx Qy Ra Ss Tn Ua Uc Ue Ug Ul Um Uo Ut Uv Vo Vs Tj tF) aN(aA aL Ap aQ AR aU aV Ax bA bC bE bM bN bP bU bV bZ cB cL cN cO cP Cs cT cV cW cX cY Dg dI dM dN Dp Ed Et Fn Fp Fr Fw Fy Ha Hr Hx Ih Ik Il Je Jl Jo Jp Jr Js Jt Jy Kd KF Kg Kl Kp Kr Kx Li Lu LW Lz Ma Mb MH Mi Mm Mn Mp Mq Ms mW Mx mY Mz Nc Nd Ne Nh Nl nM NO nR Ns Nv Ny Oe Oh Ok Ou Pa Pb PF Pg Ph Qa Qe Qg Ql Qm Qt Qu Qx Qy Rg Rj Tv Uh Ul Ur Vu Tj tF) iO(aD aE AF aI aK Al An aO aU aV Ax bA bB bE bH bJ Bn bO bR bS bV bX cB cE cG cH cI cN CQ cR cT cV cW Cx dB Dc DD DG dH dK dM Fn Gl gP hB hC hF Hq Hv iA Ic iJ Jt kC KE Kg kI KK Kl Ko KQ kS lW Mc Md Mh Mk Mn Mr MS mW Mx mY ND Ni nM nO nR nW nY oE oF Oh oO oQ Or Ow Oz Ph Po Ql Qu Qz Rb Ub Uu Vs Wm Tj) Ii(Af aI AL An Ap Ar aW bB bC bE bF bH bM bN bO bP bR bS bU bZ cC cE cJ cK cL cM cN CO cP cQ cT cU cV Cx cZ dB Dd dH dI dJ DK dN dR eF Fy gL hC HF Id iP Je Jy Kg Kl kQ Kr kS Kz mF nC nW nY oE oH oN pF Ph Pj Pk Qg Qm Qv Qy Rc Rf Rg Rj Tt Tz Ua Uk Um Uo Ur Ut Uu Uv Vs Wm tF) Mv(aD Af aH aJ aK aL aO aU aW aY Ba BC bF bH bJ bM bO bP bS bW bZ cA cC cE cI cJ cK cN CO cP cQ cT Cu cV cW Cx cY dB dD dE dF DG dH dL dM dN dR eC eF Fn GL Gp Ha hB hC iA iP Je Kd Ke Kf Ki Kl Kn Kp Kq KS Kx Ky Kz oH oN Ou pF Ph Pi Pk Qm Qx Rb Rj Ug Ul Us Uv Vp tF) nF(aD Af aI aJ aO aR aV aW bA Bc bI bJ bL bM bP bR bS bW bZ cL cM cR cT CU dA DD Dg dI dJ dK eC eF gL gP HB hC hF Hw iA iP Is Jl Jq Ke Kf Kg Kl Ko Kq KR Kx Lh Lv Lz Md Mf Mg Mk Mm Mr Mx My Mz Na Nd Ng Ni Nk Nn Nq Ns Nt Nu Nv nY Oe oF Oi oN Or Oy Pk Qy tF) De(aE aF aG aJ Al An AP Ar aS aV aZ bI bJ cB cG cH cL cT CV cY dB Dc dE dG dH dL Fw Hb HC hG Hu iH Ij Jn Ju Jv kE kI kN Ko Kp kR Lj Lu Ma Mb Mc mE Mj Mk Mp Mt My Nc Nd Ns nT OE oF Og oK Om On oQ Pc Pd Qg Ql Qv Ri Tt Tv Tz Ua Ug Uk Ul Ut Uu Vp) Mw(aC Ad aE aG aH aO Ap aR aV aW aZ Ba BC bE bL bM BN bO bP bS bU bX bZ cA cB cD cF cK cQ Cs cT CU cV cW Cx cY cZ DB DC dD dE Dp dR eF Fa fP gP Hb hC hF hG iA iP Je Jf Kd Ko kQ kR kS Kz nD nI nK nY oE oH Ou Pj Pk Qy Rb Ul Wm tF) Qz(aC aD aH aI aJ aK aL An Ax Bc bE bH bJ bL bM bP bR bS bW bX bZ cC cI cJ cK cL cN cO cP CV cW Cx cY Db dG dH dM dN eC Ed hF iA Ic iP iZ Jd Jj Jp Kd Kf Kn Kr Kx Ky Mx nA nJ nK Nr nT nW oF Og Om Or Ow Oy Pf Pi Po Qg Qu Qx Ss To Ub Ut Uu Vs) aX(aA aD aE Af aG aJ Al Ar bM bN bP bR bS bZ cA cB cD cF cS cU CV cZ dE Dg dH dJ DK Dl eC Ed eF gP hF hG iH Jt kC kK Kl kQ kR Ks Ld Ly mE Mf Mk Mn Mp MU Nc ND Nj nO nR nT nU nW NY Og Oi On oQ Pa Pb Pc Pg Qt Ra Rc Rj Ug Vv) Hc(aG aM aO aR aZ bA bI bL bN Bo bS bX cB cQ Cu dA dB DC Dg dK Ed GL gP Hb Hu Ih Ik Il Im Jh Jj Jm kN kR Kz Lu Lv Mc Md Mk mM Mn Ms Na Nc Ne Nf nN Nr Ns nT Oa Og Oh Om oO Oy Pc Ph Pj Qc Qg Qm Tt Ug Uk Ul Us Ut Uv Vp Vv) bQ(aC Ad aF aI aJ Al An Ap aR aS aV bA bB bG BN bS bV cA cB cD cG cH cN cT Cv cX cY dE dF dG dH dI dJ DL Ed eF fP gL hF Jo kE Lu Lv Ly Mg Mk mM Ms Mt mY Nc Ne nO Nq Ns nT nW Oe Og oH Ok oN oQ Ow Oz Rj Ss Uk Um Vp) Jh(aE aH aI aK AL aM aO aP aV aW aZ bA bB Bc bE bH bN Bo bP bR bS bV cA cC cD cJ cK cU Cx cY dB Dc Dd dE dF dI dJ Fw Gl Gp HB hF hG Iz Kf Kg Ko Kp Kq Ks Kz mF nK oE oF oH Ph Pi Pj Pk Qv Qx Rg Ub Ug Uk Ul Um) Aj(Af aK Al Ap Ax aZ bO bP bX bZ cA cD cE cK Co Cq cS Cv cX cY cZ Dc dF Dl Fb Hb Hv iJ Je Jn Jv kG Ki Kn kO Kz Lj Me Ml Mn Mp mT Mu My mZ Nb Nc Nd Ni Nj Nn nU Oy Oz Pa pF Pg Qm Qx Ss Ua Us Uv Wm tF) nC(aC aD aE aJ aK An aQ AR aU aW bA BC bE bJ bR bS bU bW bX cG cJ cK cM cP cR Cs cT cU cV cW CX DD dH dI dK Dl dM dR eC eF Ez Ha hC iA iP Ju Kk Kn Kp Kq Kz nW oF Or Pi Pk Uk Vu Wm) Ld(aF aG Ar aV aZ Ba bG bW bZ cB cG cL Cv dC DK Ez fP gL gP Ha Ik Jm Jo Jt Kc Kl KO Kx Kz Li lW Mj Mn mU Ne nH Nk Nn Ns nY oE Og oH Oi Or Pa Pf Pi Ql Qm Qu Rb Rg Rh Ss Ub Vp Vs Vv) aS(aC aF aI Al aM cF cG cH Co cS cV dD dE dJ dL Fb gL Ik Je Jg Jk Jn kC kE Kg Ki Ko kQ KR Kx mE mH Mk MP Mr Mt mY nB Ni Nj Nn Nq nT nU Oe Og OH Om Po Qc Ra Ss To Tz Ut Uu Vp) Nt(AD aH An aP aU aV BA bB bE bF bH bI bJ bN bO bU bW cA cB cC cI cJ cO CQ cR Cs cU cZ Dc Dg dI dK dM eC Ed fP gL Gp hC Hf Kd Kf Kg Kl kQ Kr Ks Ky oE oH Oi oN Or Qt Rg Ri) Hu(aC Af aH AL An aO Ap aQ Ar aU aV bB bF bJ bV bW cB cC cI cM cQ cR cY cZ Dc dE Dg dR eC Fn Gl Gp Hb hG iP Je Ki Kn Ko Kq Kr Ks mF nL oE oF oH Ph Pi Pj Ql Qm Rb Ub Un Ur Us Uv) nL(aC aD aI aJ aK aL Ar aU aW bA BC bE bN bO bP bS bW bX cI cK cL cN cP cR cV cW Cx Dc Dd dH dK dM eC Ed Fw hF Ic Ij Jf Jy Kf Kk Kn Kq Kr Kz Oa Og Or Qt Qx To Uu Uv Vv Wm) Cp(Ad Af aK aL aP aQ aR aU aV bC bH bO bU cJ cQ cU Cv dC dR Ez Fb Fp Gl Ic Ij iP Jy kG Kx Lu lX Nb nN nT nY pF Pg Ph Pi Pj Pk Qu Rc Rg Rh Tn Tt Un Up Ur Vo Vt) Kk(aD AF Al aZ bH bN cS Cu dB dE dK dL Ih iJ Im kK Kl kN Kp Kq Kx Lw LY Ma Me Mh Mk Mn mY MZ nH Ns Nx oE Og ON Or Pb Pg Ph Qc Qn Qu Rc Rm Tn Ub Ug) hG(aF Al Ap Ax aY bF bL cD cJ Co cS cX dE dK Fb Fw Jg Jk Jn Ju kE Kl kN KR Lj lW Md Mf Mt MY Nd Nf Nn Og Oh Oi Om Or Pa Qm Qx Ra Rj Ss Ur Ut Vp Vs Vt) Iz(aE An bC bF bL bW cE cN Cs cV dL dM dN Dp dR eC gL Hb Hf Hw Ih Ij Jk Jl Jm Jq Jr Kd Lx lY Ma Mf Mj Mk Mp Mq mU oN Pb pF Qd Ql Qn Rc Rh Sr Tt Tz Ua Un Up) cF(Ad aO Ap Ba bL Bo cH cM Cq Dk dN Fb Fw Gl gP Id iH Ij Il Jg Jj Jn Ju kC Kd kE KG kN Ko kR Ky Md mP Mr Ms Mu Nd Ne Nj Nv nW oE Oi oK Oy Po Rb Ut Uv Wm) mS(aC aD aE aH aI aL An aO aV aY aZ bE bG bL bP cB cI cJ cO cQ cS cZ Db DC dI dJ eC Fw Hf iH Kf Ki kQ kS Kx Kz Oa oF Ou Pj Qt Qx Uv tF) Nm(AD aE aG aK aM aO aP Ar aV bB BC bI bN bV bW cA cC cD cI cM cY dA DB Dc Dd dE dG dH dJ eC hB hC Kg Ki Ko mF nY oE oH oK Uk) nB(aD aF aG AL An Ax bG bL bN bP bR bS bX cA cC cD cE cH CQ Cs cU cV dA DC Dd dE Dg dH dR Fa Fb hB iH iJ Jd Kc Ke oE oK oN Qy) iZ(aA Ad aM Ap Ar aY bF bI Bn cH Co Cq dC dE Dk dM Ed Fr gL gP iH Jd Je Jg Jk Jv kC kE kG kO Md Ms My Nf nH nO Nq nU oK Om Oy Tt Ue Vs) iJ(aU aV aZ bE BN bO bV bX cA cG Cv dE dI dK dL Hv Jf Jt Ke kI kN lX Ly Md Mr Nd Nj nO Oa oH ON oQ Po Qc Ql Ue Uf Us Uv) Wm(aC Af aG aM An aO Ap aR aZ bI Bn bR bV bZ cP CQ Cs cU dA dC dI Fa Gl gP Jf Jy Ki Kn lK Mt Nq nT nY Of Ow Pk Qy Uk Ut) nH(Af aG Al aM An aO Ap aR aW aZ bJ bL Bn Bo bV bZ cA cM cQ Cu dC dD dE dI DL eF gL gP In Kl kQ kR nY oE oK oN Ph tF) mP(aD aH aW bG bW bZ cE cJ cM dA dB Dc DD dI dM eF Fn fP gP hB Hf Ke Ko KQ kR KS Kz oE oF oK oN Ow pF To Vs) kO(aC Af Al aO aV aW aZ bI bJ bL Bn Bo bV bX bZ cI CQ Cv cY dA dE dI Dl eF GL gP iA iH Kl kQ nY oE oK Ph Ut tF) cS(Ad aL Ba bC bE bF cC cD Cv dB Dk Ez gP Hv Ij Jd Jy kC kE Kg kN Kx mM Mu Nd Ne Nu Oh Oz Pa Qt Qx Qy Rc Ua Ub Ut) Mt(aD aE aF aJ Ap aY aZ bA bL bN bU cB cP Cv cX dA DC dG dJ dL Fw iA Je Jv Ki Kn Ko Kr nW Ql Qt Ri Tt Uh Um) Co(aG aM aO Ax aZ bI BN bU bV cM Cv dA dC DL Fw Jj Kc kE Ki kN Mb Ml mY Nj Nk nO nT nU Og Pa Pd Qx Ss) iH(aA Al AP Ba bI Bn Bo bX cM cU dC dI fP gL Hq Jd Jk kE kG kN Mk Mr Nf Nn oE Og oK Om Pc Ph Ss Uk Us Uu) Fb(Ad Al aM aY Ba cX Fw Jg Jv Kl Ko Kp Lv Md Mk mM Mr mU mY Ne nU Nx oE Oi Oz Po Qa Ra Rb Ub Ue Ug Uv) Of(aO aW bF cE cJ dH Fa Fy Ic Id Jd Je Jv Kd Kg Kr Oa Ou Pk Qg Qu Qv Ra Rh Rj Tz Ub Ul Un Us Ut Vu) aF(Ad Ap Ax bG cV dA dH dJ Dk Hb Il Jo Jt Ju kC kE Mk Ms Mu My Nd Ni Oh Om Oz Pb Pj Ss Ub Ue Uk) nI(aG aK aM An aV Ax bI bN bV bZ cD cM Cq Cu CX dB dE dI Fa gL Kn kQ kR Kz oN Or Ou Ow Pj Pk) Gl(Al An aU Ax aY bB bG cH cL cR cV Hx kC kR Mg Mp Ms Nc nD Nj Nk Ny Og OH oK Or Ow Oy Uk) Bn(aZ bG cV dL Ed Id Il Jd Je Jn kC Kg Ki Ly My Ne Nf Nn nW Oh Oi oK Pa Qx Qy Ub Ue Ug Uv) Vs(aJ aM bA bB bG cH cR Cs CV dD dF dG dH Fw Hb iA Jq Ko Kq kR Lj Ms nJ nK Oa Oy Qa To) nA(Dp Ed Ez Fy Ha Jy Qg Qh Ql Qn Qt Qv Rb Rc Rf Rj Rm Tn Tr Tt Tv Tz Ua Uf Um Uo Up Uv Vv) Ad(aJ aM aO aR bI Cv dB DC Dg dL iA Il Jj kE Kq kR Lj Ly Ml oF Oh Oi Oy Pd Po) Ni(aJ Ap aZ bN bP cD Cq cX dC dE dK dL eC Fw Je Kl Kr Ky mF Oa Or Ph Pj Qm Ue Ut) cH(aE aP Ba bI cB cI cZ dA dL Il Jc Ke Mg Mu My Nd

Ar aU aX Ba Bg bH bI bQ bR bU bZ cA cJ cK cL Cq cR cS Cv CW Db dD dJ eC fP Fw Gp hC hF iH iJ Kd Kf Kj Kl Kp Kr kS nY oN Ph Qx
Rg rX rY Sr Tt Tv Tz Ug Uh Ul Un Vo Vu tF) kN(aC aD aG aM Ar As bI bN bO bP cD cL cM Cp cQ cS cU cV cX dB dM dR Ez Kg Kn nY
oH oK pF Rb Tt Uh Vu) nU(aY bA bL bR cC cD cE cG cH cI cN cO Dg dI dJ dM dR gL gW hB Hc Kl Kp kQ Kr Oa oE oH Qy Ua Ub Wm)
nA(aQ aY bB bJ cD CX cY dB dD dG dJ dL dR fP iA iZ Kk Ko Us tF) kK(aE aJ aS aZ Bc cJ cT dA dE dL dM Ef Kc Kj Kn Kr Uh Uk Us)
Bg(kG kO lW lX lY mE mH mP mS mT mU mW nD nK nL nM nN) mF(aF aY bJ bX cN cR dL Ez iA Kk Kl Ko Ua Vs) cJ(Co Jd kE kO lY mP
nB nC Ng nH nK Ua Ut) mT(Bc bJ cH Ct dB Dg Dk Kk Kn Ko Kr Or Qu) kI(aJ aS Bn cZ Dc DE dI Ez Hc Kc Kr Qu) lX(aS cH cN cX Ef Kc
Kk Ko kQ rZ To Vp) nF(bA Bn Dg dI Gp hV Kn Ko Ny Ra Uh) kG(aR bF cC cH dF dM dR hB iZ Kr To) Us(kE kO lW mH mI mU mW mY
nH nK) Qu(kC kE kF mW mY nD nK nL nO) aS(kE kP lY mH mI mM nD nK nR) mS(aJ Bn dB dL Ez iH Kk pF Ua) dR(kC kP lW mH mM
mU nM) mI(As Cp dJ Kc Kn Qz To) nO(aY Bn cX Kn To Vv) nR(aJ bZ Hc Iz Ph Vs) mE(aP dH Ef Kc Ko Rj) mM(aJ aP cH dJ Rj Uh) mW(bJ
bS De Ef iP To) nB(aY dB Ef Hc oH Tz) nD(aQ bB bJ bS cW gW) nL(aM aY Bn cX dG Ef) kP(bJ De iP iZ Kc To) nM(cH cX dB iP Kc)
lW(cH dB dJ iP Qz) nN(cH cX Kc Rj) nI(Ax cI dL Kr) nK(aJ Ef Ko) kC(bX dB iH) kE(aY cH Tz) Ng(Ap Kp) To(lY mZ) Vv(bC kF) mH(De
dL) mP(Ct Kr) mU(iP iZ) WmoO UanC IccX KclY dFmZ nHiP} Ng{Kf(aV bC cH cQ Dk Fp Gl Hb hC Hu Hw iC Ih Ii jE jF jH Jj jK JO jV jY
Ke Kg Ks lK lM lN Ly MF mS NF Nt pF Ph Pj Qc qV qW qY Tv Ub) Dg(Ao cQ eD hA hC Hw jD jF jI jL Jn jO jP jQ jR jU jV kI lK lL lN lO
mM mS mY nD Nf nI Nj nT Om qU qV qY rY) nU(Ad aJ aN Ap bA bZ cE Cq Cu Cv cX dF dG dL gL hB Qv Uc Ul Un Uu) Ad(bC cQ eF fR
gL gP Jn Jo Kk Ly Ne Nf Nj Ow Pk Rj Ub) Ba(bC eF Gl gP hC kI kP Ly mF mZ nB nD nH Om rA Rj Um) Pz(aN aY Bo bR cG cQ cT cV Dc
dG fR gL Ky Or Pk tN wD) Ow(Bc cK cX dI eF fP Jn mE Mf nA nD NF Nm Nx) Bc(eF fP Jn Kc My Ne Nf Nj Nl Pk qX Ub) Rj(bA bC cE Et
Fr gP Jg Jn Nx On Uf) eF(bF Dc Dd Et Is Kc Nj Qz Ub) nL(bF cG cL Cv dM Ef Fy gL Tv) Uu(eD iC jI jM Jn jP jV lK) dX(aN cL Ef Gl Hb Im
Kl Kr) Vq(iB jK jO jT lK qU qV) bA(bC Ly Nc Ne Nf Nj Nl) nA(cE Dc dF dL hB Kn) kI(bZ Cq dH Kl oN Tv) Jn(Bo Kc Ks Ky Ou) mT(cG Dc
Kk Kn Ko) nC(dM dN Fy Kk Kp) Et(Kk Ks Pk tT) Kc(bC Ou qX rA) kE(aY dM hB oN) Ex(aV qX rA) Nd(aJ dG fR) Kn(kF mI mP) bC(Dc Nj
rC) dG(nK nT) dM(nF nT) qX(cJ Kl) BooQ DcLy EfmZ MeOu MttQ NlfR UcHw TvmF IuwB QycX KkOn KogP NxmP OkPk aNeP bFnF
cImS nKhB} nF{cJ(aJ Ba cE cX DG dH Di Ez Gp Hu Ic Ik In Jd jI Jp Kf Kk lN mS Mw nC Nk Oa Oh On oQ Or Pz qW qX rA To Um) bA(As
aY bX cH Cp De Dg Dl Hc iH Ii Mv Mw Nb Nf Ni Of oH Qu Rj To Tt) Kn(aJ cV dF hB Iz jL Kg Ky Lw mP mU nL nU nW oF oN pF Uh)
Uh(aS cH cI cX dI jU Kk Ko Mv nA Nt Og oH Or Ow qX) On(Cp Ct Fb Hw In Jd Jm My Nk Nt Om Oy Pe) Ow(aJ aY bX cA dF dL Dp Jh Ly
Mk Qv Ra Rg) oN(aS Bg cF Ct De Ef Ii Jd Je Jk kl Kk Of) cE(aS Bg Ct De Dk Ii In Mv Ni Of Qv Uk) Kk(aY cG DG dL dM dN Ij jL Ky mU)
Kc(dM hA iC jF jG jK jY qU rA To) rZ(Iq Jg Mf Mm Mw Nd Ne Nj Nq Oi) In(cL dM Is Kd nR Nx Ok oQ) dF(Bn cH De Ii Mv Mw oH Qz)
Qz(aW cL Ed Or Ou To) Nx(Hu Jn Lz Ml Nm Oy) cH(AN Is Kf oH Or) Cp(bF dM hB Ji nR) Mw(bB cG cL Dg) Tv(iO kI Kj Ph) nR(Aa aF Dl
qW) hB(Di Fb Ii mF) oH(bW cN mP Qe) Is(Kj Ml Qg) Or(aF Me mZ) cL(kI nL Uk) oQ(aN Jn Og) Ji(Kj Nt) Nv(Hw Nn) bX(jT rA) dM(iH Og)
lM(aF aO) AarY BaEf DkcG DlcX MvbF IiKf JjKo NwaY bBcI} mF{oO(Al aN Ao aR As dE Di Dk Gl GP Hf Jd Je Jf Kc Kd Kf Kl Kn Kq Kx
Ky Kz Ou Pi Ql Qt Qv Tz Uc Ur Vs) oQ(Af AL AS Aw Bg bI Bo cI Ct Cw Ef Fw gP Hb IIc Hf Ic In iO Kd Kf Kg Kn Ko KQ Ks Kx Kz Nb Qt)
hB(Af aN Aw Ef Jd jU Jv Kk Kl Ko Kr Mv Nm Nt Ow Ql Qm Qt Qz Rb Ss Tv Ur Us Ut) Kc(cX dF dN eD gW hA iC jG jH jM jP jQ jT lK Or
qU qW) dG(aR cI dI Dk Ha Ii In jO Kk Kn Nl Nm oH Tv tF) aY(aS jF jM jQ Kn Ko lL Ow qW Rj) cI(aI aJ aM bA cE Dg In lK Nw) Tv(aJ As
Jj JU Kj Qc Qz) Mw(bZ cG Dg dH dN oN) Or(bX iB In jU Mv Ne) dL(bF Kk Mr nT oH tF) lM(As Aw De Ef Vv) Qz(bF cE dN pF) aR(aJ dH
jD jK) cG(lK lO Mv nT) Rj(bA cL dM) cE(lK Mv Pk) rZ(Ii It nT) Di(Kd Uf) Dk(dF nR) To(Cv Kk) Kn(Ju jV) Qm(bF oN) aJ(Kk lK) dM(Ql
qU) dN(cL Mt) FbOh FnjU McOw MedF IibZ IrQg IsVv JjKf UkbF UfnT cJlN dAhA} In{oQ(aC Ad aF aG Al aO AS aU bI bN bP bV bX cK
cQ cZ dC dE Dg Dk Dl Ed Fa Fy Gl gP Hb Hc Ic Jf Jn Jv kE Kn Kq Kr nC Pi rZ Ug Ul Vp Wm) nR(aO As aY bI cF dA DE dL Fw Ic iO Iz Kg
Kn Ks Kz Ow rZ) nU(Aa aJ Al aN aY bA Bc cI Cu cX Dg Di dL dM Fy hB Is Ko St) oO(aJ bE Cq dG Di Dl dN Kk Ko Og oH Ur Vo Vt)
Fy(kC kN kP mE mH nB nI nL) Is(eM kC kO Ly mU nA nO Pz) mS(Al cJ dG hB Kf Vu) kE(aR hB Kd Kn Ko St) nA(cX Dc Kf Kk St) Jn(Ly
Nd Ne Nl) mP(aR cI Dc St) Nb(dX eM eP) Kd(kP nI nL) mE(Dc St Uc) rZ(kG nC nT) Pz(Kf Tv) Kk(Kf mU) Kn(kO nB) Ko(nC nL) aY(nD nL)
cJ(kC kO) dG(nN nT) fR(Or Ow) kI(cI hB) kN(St Vu) EmaN GzNx UcnD IltN OanI cNdX} dX{Jj(aC Aj As Bc bN cP cT cY dN Ef Ex Hu Hv
Iv Jn Ke Ky Lu Mw Na Nd Og Qd Qe) cL(aC aM bE bJ bL bU cA cB cC cK cR dB dC dL eM Hc Hu Kd Kg Kj Ly Nr) bA(aH aU bJ cB cH cO
dA dI Ex Gp Mx Nd Of Og Oy) cN(aH aL aQ dA dD Et Hf Kp Kz Nx Pj Pz) Aj(bC Bo dF Fr Hb Iz Kl Ko Kq Lv Ok) Is(bJ cI Ii Jm Jo Nd Nr
Og Oy) aN(aQ aX Ba cE Jp Ly Mu Nb Nf) bL(bB bJ Bo dF Ko Nw Ow) dE(aV bB cE cT cV Gp Kg) Bo(aQ bJ bR cE cI) Ou(Js Kc Og Pd Po)
Ik(Hc Kc Kg Kp) Ky(cE Hu Mh Pe) Kg(aG bB Nw) Kj(Et Nx On) Ks(Dc Mn Nw) cE(As Jo Nf) cT(Al cD dD) Mi(Ke Ow) Mz(Kc Kk) Nb(cV
Nd) Hu(Hc Nw) bB(As Hc) ExNr MeOw MpKc IiNx QaaV JpKk KrOy aCaX} nA{dN(bA cE cH cL dF Ip Is jO Kc Mp Mw Nw Nx Ow qW
Tv) dG(dJ Ef Fb Hu jV Kc kE lK mT Mu Nm Ow Ss To) aY(Ct Cv De Ip Ki Lv nO oH Or Pj Vp) To(aN aR Bc cL dL Kn Mv oN Vt) Is(aR aS
aZ bA Cp Ct Cv Ua Vu) Kc(cV dE jD jM lN Mp Or) It(bA dF dM Gp Or Tv) cE(bC jU Mv Nn Qt Rj) Mw(aJ bF Kq Uf Uh) Or(aS Dk Mf mT
Qc) Ur(cX dM hB Ow Uh) cJ(jM jV lN Mc Ow) dL(dI kE Nj Of qX) oN(As dE mT Mv Qu) Kk(aM Ed Ju mI) dF(Af lK Mc Mv) bA(Af bX
Mv) dM(Af Ef Mc) lK(cG cL Us) Dg(Dk Nm) Lx(bX dE) Tv(Ju Ph) Nx(Ao Ed) Oa(Ha Ii) Ow(bX Qm) Uh(jU jV) bZ(Di Mv) cX(Iq Vt) EtPj
FbOh MpcI UalM HbNw IrQg IvcL QzjV JuKn bWoH hBjU} fR{Nx(Ap aQ bL bR cA cH cN cO Ct cV Cw dC dE gW Gz Hc Hf Hw Ih It Jd Jk
Kf Kl Kn Ko Kp kQ Kr Ks Kx Mp Mv Na Nn Nt Pd Qt Qx Rf Rg Tn Tz Ua Uc Ud Ul Um Ur Uu Vv) Qz(aC aP Cv Dc dD Dg Et Fa Jj Jp Kk
Mb Mn Nj Nv Oa Or Ow To Tv Ur) Or(aN aQ bL cH Dg gP Ji Jp Kc Kn Nl Nt Tv) Ow(bC bX Fp iH Ii Ks Ly Mi Mr Nl Og Pd Tv) Is(aN cH Iq
Jm Kj Nd Nf Tv) aN(bC eM Ii Iq kQ Mw Ne) iH(gP Mv Mw Nf Nj Pz Qu) Me(Kj Kp Oa Rj) Et(hB Nm oH) Nj(bL Mw) Nl(aQ Ur) Ii(Lh Ok)
aC(An gP) UroH} mS{Is(aF Ao aR aY Bg cI cJ cK cL cM cR Cs Ct Di dM Ef Hb Hc iZ Kd Kk Kp Kr Us) cI(Ao cH dG Et Hv jU kI Mp nL To
Uf) aY(Dk Ir It Iu jV Mw Nl Nt Ow Qz) dG(Di Ef Fb Je kE Mv Nb Nj Ow Qu) dL(aV cH Di dJ Kc Kk Nd Nt Oz Qv) Ip(bA cL Co dI dM dN
Ed Jv To) cJ(aN gW jG jP lK qX) Ow(Iq Iu Iv Mc pF) To(aN Kc Mw Nb) bA(aS Io Iv St) cL(Io Iu Iv Nb) dM(Iq Iu Iv lK) dN(cH Di Mv nT)
oN(As Jd Je Jh) Tv(Iu Mv Qc) aJ(jV nT rA) Dk(Dg nR) Mw(Kd Uf) hB(Of Qu) qX(aW bX) AoNj CplM DeMx EtHb FbOh McOr NbcH IiOa
IooH JeoQ QzjV KclN hGrA} eM{aN(aH aJ aR aU bP cA cK Cp cV Db dK dM Hb Hq Hv Hw Ii Ji Jl Jo Kk Ks Mg Mh Ml Nw Pd Pk Qb Qe)
cL(aK AS bJ Bn bV cA cD cF cH cK cM cR CV dI gL Lj Nf Of Or) Is(bJ Bo Ct Hu Jo Kc Kg Li Nd Nj Oe Og Oy Pd) Bo(aC bL cH cT cV dA
DC gP Ji Or) Mg(Ad bJ cB cG cT Cv Et Hc Ko Nj Ok) Or(bB Dg Et Io Ou Pd) cT(aK bL bV cH Ct cU) Ou(Hu Ii Kj Of Po) cE(As bL dC Fp)
aV(bB cX Ky) cV(bL Ks Nd) Dc(Kg Ks) Jj(bL Nj) Ow(Me Oe) cX(Ly Nb) AsbB EtNm NdcN HuKc IiNw HbdA JiJo aCbE aQbA} Em{Ou(aD
aF Al Bg bP bX cA Co Cp Cq cU dK Ex Fp Fw Gp Hc Hr Il It Iu Ke Ky Lu Mt Na Nb Nd Ne Nk Nn No Nw Nx Og) Ly(aF aI aK As aV aZ Dc
dH dM dN Et Ex Gp Hb Nb Nj Nx Oh Ok Pa Qa) Nx(bJ Bo Co Hu Hw Jt Kn Mk Ml Nb Of) aV(aJ bB cL dF Ex Kc Kg Kq Ok On Qa) Or(Ax
dG Et Jj Kg Me Nw Og Qd) Jo(aQ bB cE Cu Hb Kq Oh On) Kg(bA dF Kq Mz Ow Qe) aQ(aJ cT Ex Kc Mg) Ii(Lh Qa Qd) Kj(bA Mp Ow)
Hu(aJ Kc) Nw(bL Ow) LuLv MgKq NbNj IhQa QdbJ KccN KsOw bLcT} mT{Qz(aJ aN aY cG dG dH dL dM hB Kk oF oH pF) Or(aM bX cH
dG Iq Kc lN mE Mv nC Oa Ub Vp) lN(Ap Ax cJ Ct Dc iJ iP Kf Kk Ko nW) aJ(hA iB iC jD jI jK jL jO qV qW) qV(aE aI As bO cI cJ cQ Dk
dN) dL(jE jM jY Kk Mw qW) lK(dM Ef hB Kn pF) Di(cE oN oQ pF) Oa(Cs Fb Ii Nj) qW(aK bL dN pF) Mw(aP bF pF) Kk(Iu Iv Nb) aM(cX jT

Figure 18 Continued

Tv) dG(Ii jP Of) Ax(Nt Vp) Cp(Ir jY) Ef(Nv Oh) Ip(bG nW) Is(Aj Kc) Kj(Ir Tv) cX(mZ Ne) hB(Bg lM) AoOk CtOh DgJt WmiH NtKf TorA
JhoN KceD kQoQ} Mw{oQ(AF aY bA bG bJ Bn bO cH Dg dM iJ iO Kf Kj Kq pF Pk) dG(kF kG kN kO lW lY mH mI mU mW mY nM) nB(cE cG cJ dF Dg dM Kn oN Ow Tv Uf) nU(aJ bA cG cJ Dg dL dM oN Uf) nL(cG cJ Cv dF dL oN pF rZ Uh) dM(kE kI mW nH nI nN nO) Uf(kE nD nI nN nT) nC(aY cN dH oN rZ) cE(kE kI nD nH) nR(aF Aw dN iO) nI(bF Dg oN) nK(cG dN Or) hB(kP nN nO) kI(cN pF rZ) Uh(kK mU) aJ(mP nN) HutQ cHkF dLmP nDoN} kE{dL(aY bF cG cL cR Cv dD dI Ip Jj jO jP Mh Mr Mt Nd Nl oQ Or Qg Sr To Ug) dG(aX Bg Cv Ef Fb Ha jD Kk Mc nU Qg Qu Rj Tt Vu Vv) aY(Aj cH Gp jI Kj Kk oE QV Qz Uh Vp) aJ(cD Gp iC jD Jj jP nT qV) cG(Ao Bg Cp Di Ef Uk) Jj(Sr To Tv Uk Uu) oQ(Ao Cp Je Ss) Di(hB oN pF) Is(Gp Qg Vv) Or(Aw Cp Me) Oh(Cp Fb) AwoN DgNm TtTv TorA IpQg KcjU KjhB QmdF aShA cInW dDdN} nK{Is(aJ Ao aS aW cE cH cL Co cR Dc dF Di dN gL iZ Kj Ph Qz To Tv Ua Us Vu) Tv(aJ Co dG eF Hb Iu JU Kj Ph) To(cX Kk Oh Or Pa pF Sr) Or(aS dN Ip Kc Mc Mv) cI(dF dL Jl nW Oh Tr) dG(Nj Nm Of Ss) Ip(cL Qg Um) Jh(bF cE oN) Ow(Hb Mc oO) Uk(aY cJ dN) dF(Iq It Ur) Dk(cE cG) Ef(lM oN) Gp(Ir Iu) Mv(bF oN) Oh(dN Fb) dL(Kk oH) pF(Hv Rj) DcIt DgNm WmcJ FnjU IkSt HcaY IvcL OfcE UrbA} nU{Ow(aJ Ao aY aZ bC Bn bX Jd Jj Kk Ly Me My NT Om oO Or Qm To) Kk(aM bC Bg bW Ct Hc mP Nf Oz pF Ph) Nt(Dg dL Ko Kp Kq oH Uh) Kc(cX Fw It mI Oe Or To) Kn(dN It Ju mI Of To) aN(bX Nb Nf Pk To) oH(Bg Ii Iq Oz Qz) Ef(Ba Jn Nw On) Dk(bA Dg Nw) Qz(Ic Mc) dL(Ns nT) AdEt AscX BgOn CpOh DcVs DeMx DgIi DidG NmKf MecV MvTo TvPh IsKj OrbX PknL aJnT cHdN dJIK} kI{dN(Aj aN AX cH cL Cv cX Dc gW hA Is jD jG jH jI Jj Jn jR jT jY lL Mr Mv Oh qU qX qY Uk) aY(eD Hc iB jG lM Ly nO Qm Rj) Mc(Ax bZ dM Kd oN Qz St) jV(cI dH Kc Kd Rj Sr) lM(aO As Cp Ct Ke Qm) Kc(eD gW iC lK) Or(Bb Ju Me Qm) dL(eD jO tF) rA(Gp To Tz) Jj(cI cZ) Jv(hB Tv) Oh(Fb Gl) jU(cG Kd) DidG LycX UalK IiOa IsVv IvQg RjjD} nL{Di(cE dG dH dN hB Ij Kd oN oO oQ pF To) Mc(cE cJ dM Kn pF Qz Uh) oO(Ef Iz Je Ph Pj Qu Ss) Qm(aY bA cL dM Ji) cI(Cv Hu iO jU Oz) Tv(Cp dL Ij Tt) Kc(dN eD lN rA) Vv(bA Is jM rA) Dk(dG nR On) To(aY Kk Mv) Qu(bF cJ oN) Oz(aS cH Kk) dN(cH Kn Mv) Ct(Oh Ow) Fy(Jv Kj) aY(Mp Uk) BooQ DgNm MeId HbOw JvKk OfcE OraS aOlM rCjY} lK{nR(aN Ba bI bP bX cB cJ Cq cS dE dG Gp Id iO kQ Ks Mu Nn oK Ow Qy Uk) mH(aJ Ar aY Co cU dG dH dN hB Hc Iz Kd Kn Oa pF Qy Qz Ue Vv) nO(aK Bn Cp cX Di Dk dM Fn Hc Kc Kd Kk Kn Kr Qm Qy Tz Vu) mP(aR cI cJ Ct) dM(lX nI nN) nD(cJ Kc Nx) Vv(Dg Kf) AaoO KcnB aKmW lXpF} eP{Is(Aj bJ dC Hu Jo Kj Ma Nr Po) aN(Aj bA bU Jn Jo Nb Ni Qd) Ow(Gp Hb Hq Kp Me Nf Ni) Jj(aQ bL dE Jn Kd Ml) Bo(aQ aV bL dA) cL(aF bL Jo Nf) cV(aV Ii Jo Ks) bB(aV cN Hc) cT(bL cH cU) Nb(cE Nj) Kj(Nx On) Ou(bL Pd) cN(aC Nd) AxNr DcKs MgbA HuKf IiNx HcOy JoOk JpKk JsNw KcaQ KyaV} Ow{nB(aY cI De dL Fn Kd Mt Mv My Nl Or pF Tv Uk) Ct(kO kP lY Mi mM mZ nH oO oQ) Mc(kK lY mE mH mI mP nD nH nT) oQ(Ao De Di Jh Jv Mt Pf Po) Hb(kG kK mY mZ nT) oO(nC Ou Qm) ExNx MvnO TvOa QzlW JjmM QmnR cJnD dLkN nTmP} Kk{dN(kO kP lY mE mI mM mP mU mZ nD nH nI nN nR) mP(bC cI Io Iv IL lN nT St To) mU(Bb gP Hb Ii jV Mc Nb Nt) nI(aY dL Hb It pF) lW(Gl Hb Nb Ur) jV(kO nC nD nH) nB(Ed Is qX) Tk(cJ Pc) dL(nN nT) AjKf ExNx HbnR IzoQ dGmM} Kc{lN(kK lY mI nB nC nI nN nR) qX(Co Hc kC kO nD nH Pb) jU(kG lW lX nC nN nO) nB(eD Is jV Or) nC(aY dN mI rA) Vv(jQ lL lM) mP(iC jQ jV) nD(cJ jL lO) kC(Is lO rA) kO(gW Is jV) dL(mI nO) HcrA QchW PblL aNmI nRjP nHjV} tT{Qc(Et Fp Is Mb Mk Ms Ni Nm Nn No Oh Qd tV) Pz(Hx Jr Mm Mx Nt Oe Oz Pg tO wL) Ji(Ik Ir Iv Mf Mn Mz Nu Qd) Mk(Hx Jp Mf Mq Mz Nb) tO(Hv Ip It Iu Mf) Et(Ik Ml Pf) Il(Iu Lh) MlNi MzJs} nR{Di(dL Ii Ir Iu Iv Nf Of St To Us) dL(Dk hA jY oH rA) Aw(jI jP lM Ur) Bn(eD hA jY qW) aF(gW jM lO Of) Dk(Bc dG iO) Kj(cZ jG qX) jV(aJ aM bG) Cp(dN jH) Qz(Ao Mc) KeNw aSbA bGjU cZqV dAqW} qX{Aj(Ap BC Et Ex gP Kf Kl Nm Pz) Vv(Ap cX Dl Ic Jg Jp Kl) Ct(Bc cH cJ Gz Ml Oz) cJ(cX Gz Jk Mf nD) Hc(Ml Oz qW) Ph(cX Oz qU) dL(mH nT) DgIz EfPz ExUr UcJk KfOz aJkN} oQ{Dk(aY bA cL Di Jn nI OH Ou Tz Um) Di(aY Ii Je nC nT) Aw(Je Or To Tz) Cp(Oe Oh Tv Tz) oH(Bb dN Qm) Is(Jk Po) Iz(Bo Ns) Kj(Oe Uc) dI(dE mM) BbEt DcVs FndA FyIi SsaS QuaX} Nx{Ex(aN Ao Bg Cw dG Ed Ef Hc Ic Jh Jj Jk Ky Mf Mu My Nl Or Pd Rh Tv Ua Ue Ur Us Ut) Gz(Hw Jo Jt Kg Nm Ub Uk) mP(Is Jh lN Mg Nb) MgVq QunH} nC{Kn(dN Ju JV Mc) dN(cL Cv Di oH) Mc(dM Or Tv) aY(Hc Qm Uk) oO(Di Jv Kj) Tv(JU) Jj(cI cZ) Or(jV Me) dG(Dk nT) hB(Di Qu) HaOa TorA IiNv HcOz JiQm aOlM cHcI cXjU dJdL} rZ{lY(Fr Hu Hv Ij Ik Ir Iu Jg Jh Jj Lj Lx Mb Md Mg Mk Mr Nb Nc Nm No Nr Nt Nu Nv Oh Om Pd Pe Pf Qb Qc Qe) mZ(Hw Mf Mp) nTmP} nT{dG(aN aV aX Bo cY De dJ Ii nH Rj) dL(An aY dA dI dM ND Nj Nl Qz) mP(aJ aY Bc bL cA cE cG Or To Vp) QzdN aJrA aSbA aYiJ} Vv{Kf(hA iB jD jF jG jT lM lN lO qU qV qW qY rA) cJ(jO jQ jR lL qU qY rA) Dg(iB jO jU jV rA) lL(Ap Kp) TorA IsnD} nD{Is(aW Ef It Tt Vu) cJ(eD jD To Uk Us) Cp(Oh oN) Dk(cE dF) Gp(Io It) Qu(aJ Dg) bA(aS It) DidG EflM MvVp TorA TvIh IiVt IpaW QzjV} Qc{Wn(bQ Ed eF Qa Ql) tX(Hv Jl Jr Lh Mk) tQ(Mt Mz Nw) wB(Hu Ip Qa) Vt(hW rC) aJ(rB rC) hX(iJ Kp) MztR QaTk JrtV} mP{Is(Aw cD Di) dL(jO Kn rA) Cp(Lx Oh) Jn(Di Dk) BccI FbOh GpIu MeOr TorA IpUm UhjU aLqW aOlM bXjQ cJgW dGjO dNqV eDiH} Pz{tQ(Il Jp Mt tX) tN(Jj Nu Oi Pd) wB(Hu Il Mk) Ct(bA cT) Ua(bA lM) tX(Jm Nl) IkwJ JptR QlTk} cJ{Wm(cD jD jO jP rA) jM(Gz iJ kC Vq) aN(kO nH) kC(jP jU) QunH OzrA} kK{aJ(jK jL jR jV qV) jI(aY dJ Pk) qW(dM dN) lM(Aw Cp) FbOh TorA dLoH} Mk{tV(Js Nb Nr Pd Pe tQ) wB(Hv Hx Iu Mq) Mm(wD wQ) tQ(Hx Lh)} nB{Tv(aS Bn Dk Mv Tt Vs) aS(cX Or) DgNm NbcX TorA IpbG KndL VpdI} nI{Or(bX jV Me) Di(aY oN) Dk(cE cG) dL(dI Nj) FbOh aOlM cIiO cXjV dNoH} Is{Iq(Hw Ij Lv Ly Ml Ms) Ml(Nd Tv) Hw(Ly Ne) ExTv} dL{oH(kF kG kP mW mZ nH) mH(jE jP) KnnN dInO} Kf{Jk(eD jD jK) gP(Aj Jo Of) DkJo MgcM} Mz{tN(Ir Jn Oh tS) tX(Im Qa) JswH} mM{dG(dI dJ Dk) dN(cH Kn) TorA UhjV} tQ{Et(Ma Mf Ml) MaMm MtIl NbJl JiJs} iH{Gz(qU rA rC rY) Ex(rA rC)} To{rA(kO kP mI nH) aNkN} Tv{ExNj IuJj KjmZ iOkG jVkC} Jn{Hw(Ly Nd Ne) NtUb MlNd} Vq{eF(Ct Mg Nt Of) OfeD} cH{dN(lY nO) RjgP aCbE cIkO} oO{Aa(jL lN) iO(aN Ss) aSbA} Il{tN(Ji tS) IutX JlwQ} Oh{Fb(kG nN) Kj(mZ nN)} gP{Bc(Rj Ub) IcWn IdRj} Cp{kO(lM oN) nHlM} nO{AarC EtHb aYjP} jV{FnkC KnkF OrmI} kN{aSbA dIjI dNoH} Mm{MawH PfwP} Qu{nH(bF oN)} bE{AjaC WncM} lY{rY(Hx Mf)} mZ{IiOa OrPb} BcUbPk DgJtjO DidGmW ExNheD GzIcoH JptStX RjaObA aJmHjY

Unconstrained panels with 2 analytes, where 1.0E-8 >= 'AUC p-value' > 0. Contains 10 panels of 114,449 total panels evaluated. : oP(Aw Ch Cp Cw Di Ef Ib Iz Kj Qw)

Unconstrained panels with 2 analytes, where 1.0E-7 >= 'AUC p-value' > 1.0E-8. Contains 10 panels of 114,449 total panels evaluated. : oP(aN Ao As Bb Bg Ct iO) UbQw IbnR LdfR Unconstrained panels with 2 analytes, where 1.0E-6 >= 'AUC p-value' > 1.0E-7. Contains 15 panels of 114,449 total panels evaluated. : oP(Aj aS aX bQ Hc hG iJ Ld) Qw(gP nU) Ld(Em nA) CqIb OrnJ cLeM Unconstrained panels with 2 analytes, where 1.0E-5 >= 'AUC p-value' > 1.0E-6. Contains 78 panels of 114,449 total panels evaluated. : oP(Ad aF Ap aY aZ Ba bF bG Bn Bo cD cF cH Co cS De dJ dL Fb fP Gl iH iZ Kk mF nF Qz) Ib(Kf Lh Mk Ml Mt oH On Ow Pz Qw Rj) Qw(aJ bA bC cN cV Ed eF Jj Nx Ow) Ng(Ad Bc Dg Kf Nx Ow) nJ(cJ dL dN Ld oN) Nx(Ex fR In nF) Ld(mP nL nU) Ch(nR nU) Is(Hw Iq) Ow(nF nU) EmOu QctT OnnF aCbE aNeM cLdX

Figure 18 Continued

Unconstrained panels with 2 analytes, where 1.0E-4 >= 'AUC p-value' > 1.0E-5. Contains 339 panels of 114,449 total panels evaluated. : oP(aC aD aE Af aG aI aJ Al aM An aO aP AR aU aV aW Ax bA bE bI bJ bL bN bR bS bV bX bZ cA cB cE cG cJ cK cM cN cO CQ cT Cv cW cX cY cZ dA dB dC dD dE dF Dg dI DK Dl dN dR eC Ed eF Fa gL gP HB hF iA In Jd Jc Kc Ki Kl kQ KR kS mP nL nW nY oE oH oK oN Ow Ph Pj Qu Uk Ut Wm tF) Qw(Aj aN Ax aY Bc cH cJ cL Cv DG fR Hw In Is Kf Kg kI Kj Ks Ky Lu Mf nC Ne Ng Nh Nj Nk nL Nq nR Og oH oQ Or Ou Pk qT qX Rj Ue Ug) Ib(An bA bB BC Bo cH cJ cL cT cV cX dB Dc Et Fa gL gP iH Im Is Iu Ji Jn Jq kE Kx Ky mY Mz Nj NL Nw Nx Oa Ou Pi Rg Tn Vs Vv) Ng(aJ aN BA bC Bo cE cG Cu cV Dc dF dG EF Ex fP gL Kc Kp Kq Ky Ld Ou) Nx(Em Hw Ih Js Ly Lz Ml mP Nd Nl nU Of Po) nF(bA cJ Ji nR Nv Nw Ny Ok oN oQ Uh) nJ(aJ aY cE dG dM Kc Kd Kk Ow To) Ch(eF kE mF mP mT nC nL oQ) Ld(eM eP kI lW mF nC nK oQ) Is(Ij Il In Ly Ml Nd Tv) qX(Aj cH cJ Ct Kc Ph Vv) Ow(Aj Ct fR In Mc Mf) dX(bA Bo cT Jj Kk) fR(aC aN iH Nj Or) mF(aY dG dM hB oQ) nA(aY dG dL oN Or) tT(Ji Mb Mk Ml Pz) Ly(cV Ji Jn) Nd(Jl Jn Ml) Ne(Hw In Jl) dL(kE mS nT) In(Jn oQ) Kk(mP nU) eM(Bo cV) gP(Jj Rj) tQ(Et Mt) qT(kN IX) kE(aY dG) AoKf BcUb DinR DkoQ MktV MztN UabA HwJi OrnK VpnD aCbC aJnT dNkI mThB Unconstrained panels with 2 analytes. where 1.0E-3 >= 'AUC p-value' > 1.0E-4. Contains 1,313 panels of 114,449 total panels evaluated. : Ib(AD AF aH AL aM aN aP aQ Ar As aU aV AW Ax aZ Ba Bb bE bF bG bJ bM bN bO bP bQ bR bS bX cA cC cE cF cG cI cK cN cO cR CS CW Cx Db dC Dd dE dF DG dH dl dK dL dM dN ED eF Ex Ez Fb Fn Fr Gl Ha HB Hf Hu Hv Hw Hx iA iB Id Ih Ii Ik In Ip It Jd Jg Jh Jj Jk Jl Jm Jp jT Kc Kl Kl Ko KP Kq Kr Ld IL Lx Lz Ma Mb Me Mf Mj Mn MP Mq mS mT Mx My NA NC Nd Ne Nf Ng Nh nJ Nk Nm Nr Ns NT nU Nv Oe Og Oh Ok oQ Or Oy Oz Pa Pk Qa Qb Qd Qn Qt qU QX Qz Rb rC Rm rY Sr St To Tr Tv Tz Ub Uc Ue Ug Uh Ur Us Vu Tj) Qw(Aa aC aQ aV Ba bF bN Bo bV cC cE cG Ch cl cM cO Cq cR Cs CT cW CX cZ dB Dc dF dH dI dK dM dN eD Et Fa Fr Fy gL Gp HB Hf Hu Hv Id iH Ii iJ Ik Il iO Iu Jg Ji Jn Jo Jp Js jU Kc kE Kp Kq Kr Ld Lj Lx Me mF Mg Ml mP Mq mS mT Mw Mx MY Mz nA Nc ND Nf nJ Nl Nm Nr Nt Nu Nw Oa Of On Oy Oz PF Pi Pj Pz Qa Qc Qd Qe Qh Ql Qt rA Tn To Uc Uh Uk Us Ut Uu Uv Vs) oP(aH aK aL aQ bB BC bH bM bO bP bU bW cC cI cL cP cR Cs CU cV Cx Db Dc Dd dG dH dM Ez Fn Fw Gp Ha hC Hf Hu Ic iP Jf Jn Ju Jv Jy Kd Ke Kf Kg Kn Ko Kp Kq Ks Kx Ky Kz IK Mw NB nC Ng nH nJ nK Nt Nu Oa oF Og Oi Or Ou pF Pi Pk Qg Ql Qm QT Qv Qx Qy Ra Rb Rc Rg Rj Ss To Tt Ua Ue Ug Ul Uv Vs Vv Tj) Ng(aC aF aI aM An aO AP AR aV Ax aY bB bF Bg bM bQ bR bX bZ cB cH cJ cL cM cN Co cR cT Cv Cw cX DD dH dl DL dM dN Ez Fa fR Gp hB Hc iH iJ iO Is Ji Ke Kl Kn Ko Kr Nd Ne Oa On Or Ph Pk Qy Qz Rj Tn To Ub Uc Ue Uf Uh Uu Vq Vs Vv) Nx(Aj Ao Bg Bo Ch Gz Hq Hu Hv Hx ti Il Io Iq Is Iu Jo Jq Jt kO Lh Lu Lw Ma Mc Md Mf Mh Mi Mj Mk Mn Ms My Nc Ne Nf NH NJ Nm Nn No Nr Ns Nu Nv Ny Oe Og Oh Om Ow Oy Oz Pa Pc Pd Pe Pg Qb Qc Qd Qx Us Ut) Is(Aj Ct dX eM eP fR Ih Ii It Ji Jk Jl Jm Jn Jo Jr Js Kj Ks Lu Lv Lz Md Mf Mg Mj Mk mP Ms nB Ne NF Nh nK NI Nn Oy Pe Po Qb Qc Ub) qT(cJ He Ic kC kF kI kK kO kP IW IY mF mH ml mM mP mS mT mU mW mY mZ nA nB nC nD nF nH nI nJ nK nL nM nN nO nR nT nU oO oQ To Vv) Nd(bA Et Fr Hu Hv Hw Ik In Ji Jo Jp Lx Ly Lz Mb Me Mf MK Mp Mt Ne Nf Nh Nq Nt Nv Nw Ok On Pz Qa Qc Qd Qe) Ow(Bg cD Ch eP Ex Fy Gz Iq Jj Jo Js Kc Ks Ky Ly Mg Mi Ml nA nB Nf Nh nK Nq Of Og oO oQ Oy Pz Qv Ub Us) Ne(Aj bA CH Et FR Hu Ii Il Iq It Ji Jn Lu Lv Ly Lz Me Mf Mk Ml Nw Of Ok On Pc Qc) mP(aJ aN aR cI cJ Cv dL hA iB Ip jI Jn IK IM IX mH nC nF Nj nT Ok On oO oQ qW To) bA(aC bC CH Ct Dk EM eP gP Hu li Jk Js Ly Mg nA Nf nJ nK Of Pk Po Ut Uv) nF(aY Ba bF cE cG cL dF Dg dM Et Fr hA hB Hx Jl Kk Kn Ld Lh Ma Mn Or Pg rZ) nJ(aR Ba Bc bF bX bZ cG Ch cL Cv Dc dF Dg dH cF hB hG Kf Ko Kp rZ Uh Vp Vt) In(Ef Iv Ji Jr Kf Ly Mt nB Nc Nh Nj Nl Nw Oa Or Ou Pi Pk Qa Qx Rj rZ) Ch(aC Bo fR Jj KF kl kP Ky mS mU mY nA nD Nj Nl Or qX rC Tn) cJ(eD hA jD jF jM jO jP jR jU jV kC kO IL IO mS nA nH nU qU rA) Ly(Aj Bo cH Em Et Fr Hw Jg Jl Jp Jq Lh Mz Nw Ny Ok On Qa) Ub(bC cL Cv cX eF gP Hw Ji Jj Jn Kc Ld Nj Nt Pk Qz Rj) Aj(Ad bC eF Jn Kc Kf Ky Mt Nc Nj Nl Nm nU Ou Pz rA) qX(aI aM aN aV BC cC Co cX eC Hc Kj Kk Kp Ks Pk) Ld(Jj kE kF kN mH mS mT mU mY mZ nB nD nH nO nR) tT(Et Hv Hx Iu Jn Jp Jr Lh Mf Mm Mt Mz Ni Pf tV) eM(Af An aQ aV bB bJ Bn cE cT cX Ji Jj Or Ou) mF(aJ aR bZ cG cI dH dL dN Kc Kk oO Or Tv) nL(aY cI dH dJ dN Gp Hb Kc Kk oO oQ rC To) Ji(Ao Ii Ij Iq It Jo Ml Nf Om Qm tQ Ue) nA(aJ aR bZ cE cG cL dM dN hB Kc To Vt) Kf(Hu Hw Ii Jo Jt Kk Mg Nm Nt Of Ue) aY(kC kI kO IL mS nC nH nK nO nT nU) Jj(BC Em eP Kk Ky oH Rj Um Us) dX(aN bB bJ cB cE cG cN Ko Ky Ou) nU(aJ Dc dL dM Ef Kc Or Qz To Um) oQ(aN Aw DI Hu IK Mc Mw Nb Og) Hw(Et Jn Mt Nc Nh Nj Nl Nw Om) fR(aQ bR cD dB gP Mw Nf Nl Qz) mS(aJ bC bZ cI dG dN Kd Qz To) nK(bZ dG dL dM dN oN pF To Tv) tQ(Hv Jl Jp Mk Mm Mz Nb tN tV) Jn(lq Ks Ms Nh NI Tv Ue Us) gP(aJ bB Bc Ed hB Id Ug Uk) mT(aJ Ax cE dG dL Kk oN Or) tV(Hu Il Js Nt Pe Pg Qc wQ) Kc(Ao bC eD jD Kk nC rA) Ou(Hq Jk Me Mf Mg Nh Of) Tv(Dd Id Iu Nj Oa Qh) kE(aJ aR cG dN oN Or) bC(bF cT cX Nj Rj) li(dG Oa On Or) Iq(Jl Nw On Qa) Qc(Qa tX wB Wn) Pk(aJ iH IK Oa) dL(kI nN nO oH) nC(dH dJ dN To) Bc(Ed Nj Ue) Et(Ao Jo Ue) Jl(Nh Nj Nl) Kk(mU nB Tk) Of(dG hB On) Or(kI mZ nT) aC(aL aX cZ) aJ(Nj nN nO) eP(aN aQ Bo) nR(Aw Dk lK) tX(Jp Mz tS) rZ(kC IY mZ) Ct(cT rA) Dg(Jt Nm) Em(Nb Nw) Mk(wB wD) Hu(cL Nl) QueF iJ) Rj(Nt oH) dG(nO nT) dN(mY nT) nB(Kn Nb) tN(Il tS) IK(mU oO) AaoO CvEd McKs MmwQ MzqZ NfaN UeeF JocV NwOm Oakl OknD cHeD cLcM Constrained panels with 3 analytes, where 1.0E-10 >= 'AUC p-value' > 0. Contains 3,417 panels of 17,333,483 total panels evaluated. : oP[Di(Ad AJ Al aM aN Ao aR As aY Bb bF bL bW cJ cL Co cR Ct dG dL Ed Ef Fb Fw Hc Hq Hv Id li IJ In IZ Jd Je Jg Jh Jj Jk Jn Jy kC kE kI Lj Md mF Mg MP Mr MS Mt Mv Mw My nA nB nC nD Nf Ng nH nl nJ nK nL Nm Nq Nt NU Oa oE Of Oh Oi Om Or Oy Pa Pb Qa Qx Qy Qz Rb Ub Ue Uf Ug Uk Ut Uv Wm) Ib(AN aV Ax bI cF cP cQ cS dA Dc Dd Dg dI Dl Ed Et Ez Fw Fy Hc Hx In iO Ji Jn Jp Jq Js Kc kE Kf Kl Kk Kn Ko Kp Ks Ld Lh Ma Mk Mm mP Mx Mz nA nC Nj NK nL Nm Nw Oa Oe OH Oi Om Or Qv Qw Rf Rm Sr To Tr Tz Ub Uk Un Uv Vo Vt Vu) Cp(Aj AN AX aY Bb bG Cs cX dL Ed Ef Fw HC Hu Hv iH iJ Il IZ JI Jn Js kC kE Kk kO Ld Lj Mn mP mS nA nB nC nD nF Ng nH nl nJ nK nL NU Oa Oe Of Oh On Or Pa Pe Pf Qa Qb Qh Qw To Tz Vu Wm) aX(Ad Ao AS Aw Bb bF Bg Bo bQ Ch Co Ct Cw De Ef Ez Hb Hc Hu li In IZ Jd Je Jg Jh Jk Jy Kc Kj mF Mg mP Mt Mv Mw My nA Ne Ng nl Nq Nt Oa Of Om Oy Po Qw Qx Qy Qz Tt Ua Ub Uk Us Ut Uv) Kk(Ad Ao Aw aY Bb bF Bg bQ Co Ct Cw De Ef fP Hb Hc hG Hq Hu li Ij In Iz Jd Je Jg Jh Jk Jv Kj Lj mF Mg mM mP Mt Mv Mw My nA Nf Ng nl Nq Nt Nv Oa Of Om Oy Po Ql Qw Qx Qy Tt Uk Ut Vs) Ld(Aj Al Ao As aY Bb bF Bn bQ CH Co Ct De dJ Ed Ef Hb Hc hG Hq Hu li IJ Iz Jd Je Jf Jh Jj Jk Jv kI Kj mF Mk mP Mr Ms Mt Mv My Nf Ng nK Nm Nq Nt Of Om Oy Pb Po Qx Qy Tt Ua Uk Ut) aN(Ad aF Aj Al AO AS Aw aY aZ Bb Bg Bn Bo bQ CH Co Ct Cw De Dk dL Gl Hb Hu li In iO Iz Jh Jk Jv kI Kj kN Me mF mP MT Mv nA nC Nf Ng nH nl nL Nq Nu nY Of Po Qz Ua Ut Uv) Aw(Aj aM aY bF cH dL Ed Ef Fw Hc Hf Hv Id iJ In iO iZ Jn kC kE Kf kl kO MP MS Mx nA nB nC nD nF Ng nH nJ nK nL Nm NU Oa Og Oh Or Ow Pa Qa Qz To Ub Ug Uk Uo Wm) nK(Ad Af Aj Al Ao AP Ar As aY Ba Bb bF Bg bI Bn Bo bQ Ch Co Cq cS Ct cV Cw cX De Dk dL Ed eF Ez Fa fP Fw gL Hb Hc Jd Je Jv Ke Kg Kj Kq oE oN Or Qy Ss Uk Ut) Ef(aS bl bV cF cH cS Cv Dc Dl Ez Hv iH iJ In iO KC kl kO Kq ME mF Mh Ml mP mS nA nB nC nD nF nH Ni nJ Nk nL Nu Nw Oa Of Oi Ow Pa Qw Qz Rb Vu Wm) Kj(aS aY bI Dc Ed Fw Hu Hv iJ In Je kC kE Kf kl KO mE mF mP mS Mt nA nC nD nF nH NJ nL Nt NU Oa Oe Oh Oi Ow Pa Pd Qa Qw Qz Uc Ur Vp Vu Wm) Qw(aF Aj aM aY Bb bG bN Ch cR cS dJ Ed Fb Hb li iJ Il In Iz kE kl kO Lw mF Mk mP Mr Ms nA nC nD Ne nF Ng nH NJ nL Nm nU Og Or Ow Oy To) nL(Ad aF aM AO Ap AS Ba Bb bF Bg Bo bQ cF Ch Co cS Ct Cw DE Dk dL Fb fP Gl Hb Hc hG Lz Jd Je Jv Ke nF Ph Qu Qy Ua Ut Vs) iO(Ad Ao AP aY Ba bF Bg Bo bQ Co cS Ct fP Fr Hc Hu Iz Jd Je Jg Jh Jy kG mF Mg mM mP Mt Mv Mw My Ng nl Nm Nq Oa Qt Qx Qy

Ng Of To) Ow(Ct dE Ef Hb Mv Ng) Ng(Kf Kn oH) Ef(Kf Kn) Ii(Dc Kf) Kc(dE Oz) DgNm KndE dLoH} eM{aN(Aj bL bO bR bU cN Hr Jj Jn Jp Kj Mu Na Og Or) Mg(cE cL Hb) BobJ} mP{cJ(eD jQ jR IO) Kc(eD IO rA) Kk(jU jV IK) bX(eD IN) dL(nT oH) IqoH KnjU aMnT clqW} tT{Qc(Hx Ih Ip Ji Jp Lh Mm Mz Nw tO) Pz(Jp Mk Na Nu wJ) Mk(Hv Ji)} Ow{oQ(Aw Bb Cp Cw Iz Mc Mg Ng) Ct(mE nB) fR(Nf Nt) McnB NgPz bLeP dLnN} nD{Qu(cJ dG hB Ok oN Vp) jU(iH Kc Kk Kn) cJ(jM jV qU) jV(Kc Kn) aOlM} kE{Ng(Ba cG DG Kl) dL(Gp Kk nT) dN(qV qW) oQ(Iz Kj) DidG lrQg StJj} lK{nO(aY Bg Cu dA Dc Ef Or) mH(cX Fn Or Tv) lX(aJ cJ dL) aJkK} lY{rZ(Ii Mf Mj Nn Nq Po) dN(qV qW) CplM aYqV} Kc{nB(gW jR jU qX rA) jV(kC kF) mlnL jUkC} fR{aC(bE cZ) aN(Nf Ng) EtkQ MeOr NxgP} nK{Tv(As dL dN Iz) BaNg DkdF TorA} nL{Fn(jU jV) FbOh JvoO aYjM cXjV} Mz{Qc(tN tX wB) Js(tN tX)} Kk{mU(Dk It) NgKf nIjU jVkF} tQ{Mk(Et Mm Nb) EtHu IlJl} Pz{Ik(tN tX) Il(tN tX)} Ex{Nx(Nm Ub Uk)} Ng{Vq(eD eF) KfgP} Vv{qX(cJ Dg) KfjU} nT{dG(Di Hu) dJdL} oQ{Dk(aN Dc) DiEd} To{rA(kN mE)} Kn{kC(jU jV)} aS{bA(kO nH)} eP{aVcN bCbJ} nO{CplM dLoH} DeTvnB WmcJjM FpOamZ TkbEcM OfVqlM UhmMjU cXnCjV dAjIkN Constrained panels with 3 analytes, where 1.0E-9 >= 'AUC p-value' > 1.0E-10. Contains 1,314 panels of 17,333,483 total panels evaluated. : oP{aN(Ba bF Cq Fa Fb Hq Jg Ju Kc kG Md Mw My nF Nm Nt oE oK Om Oy Qc Tn Vv) cS(aY bW dL Hb iZ Jk Ju Jv Lj Mt My Om Po Ue Uk) Aj(aF aO Bb bI cB Cw mS nH Nq Nt Oa Oi Ut Vs) Kk(As Ed Fa Gl Jf Jo Ju Lh Md Ms Nn Ua Ue Uv) aX(aO Ba Bn cH Gl Ij Jv kN Nm Ph Qc Qu Ue Vs) Wm(Ad aF Ao Ba bF cH De Dk In Jd Je Nd) iJ(aO aP aS Dk Fr Jk Mg My nI Nm Nn Uu) aY(aF As cH kO Mp Mw nC nH nL Nm Nt) Ld(aO cF Fa Hw Ju Lh Md nB Pg Tj) Oa(Af aP As De Dk Ha hG Kl Mt Tt) iO(bI dL Ed Lj Mu Nn Om Ue Uk) Fb(aJ Cs Ct iZ Jh Nu Of Uk) As(Hu kC kO nH Nu Pa Tz) Ed(aS Dl Kc mS Ni nR Vs) nF(aF Je Jn Nw Og Qu Uh) hG(iZ Kc mP Ne nH Nu Ue) Jk(Dc Fw Or Ow Tz Vp) aS(Ap cX Hv Il Ub Uk) mS(Al bS Jv Kq Qy Vs) nB(Ap Ar Ba bF bI De) Bb(Et Kc Ml Ow Pa) Cp(Mp Mx Nj Vp Vs) Mw(bB cE Kc rZ Uf) aF(iH Jv kO nH Or) cH(Hc kE Nt Qt Ss) nC(aM dL Jv Qy Ua) kC(Ba Bo bQ Co De) Ax(Ad Jt Mt Vs) Dk(aI aJ dL nU) Nu(aV Ba bF dJ) Hv(Ba bQ Co Ut) nH(bF dJ fP Jd) nL(Ha oN Tt Vu) Ii(Kc Tv Uc) Or(Ou Vs Vv) Ow(Cw Hb Kg) Vp(Ct Hu Of) mP(Je Kd oH) kI(Ct Hc Kg) Dl(Ad Jv) Gl(Nw Ra) In(Ko Og) Jd(nA nJ) Uk(bV cD) Ut(nD nI) aP(Ly Mv) dL(aV Nm) nK(Og Qu) oH(Cw nI) AoPa BnTz ComE DenU DiTn PoFw FanJ NnQz NtJe MfmF MgKc NiQy HugP IlbI SsiZ JlVs JvbG OfdD OidC bFkO} Qw{Ib(cH cJ cL cN cV Dc gL Mt Nj nU Ou Ow Pz Rj Tn Ub) gP(Aj bW Ch cJ cV dM Ed Hw Ky Mf Ne Of Or Uf) nU(Bc cH cJ dE dF dI dM In Ip Kn lY Nb Oi) oQ(Ao Bo Ch Cx Di Ke kI Ph Pj To Ur) mF(cJ cL dN Kl Mt nR Or Qa Qe To) Ub(aJ Dg Is Iu Jl Or Pk Qa Qx) Is(cH Kr Mf mS nJ nK Tv) nL(cN cO hB Jn Kd Kk Ng) kI(cE cI dH fP Mc oN Ur) bA(Ct Ii kG mH mP Ut) nJ(bF bL cL Kc Kp Pz) Ng(BC Jg Kf Uc) nC(aJ dN hB Jn) nD(cE cJ dL lK) kE(cE dF Jn oE) aY(lL mS nA) mP(dL Kk oN) nF(dF dM Ow) Ed(cX Pz) Or(mZ nK) eF(Ch Mg) nA(dL dM) AoKf CpnR MfNx HbJi KkmU OwnB bCcX bLmS cEnH cJqT dGmM nOjQ lYlM jIkK} Ch{mF(aR aY cL dF dG Ip Jg Ko Kp Lx Nv Oe Oi Or Qe Tn To Uc Uh) nU(cE cX dF Dg gL Ip Ji Kc kI Kk Kq nR Oi Qa Qv Uh) kE(aN bZ dL Ef jI Kg Ld Mp Oz Qn Uh Vv) nJ(aY Bc cI dF Ip Kn Nj Nv Nw Oi Pz) nL(aY bF cI Id Jg Jn Lx Mt nR Or Qe) mP(dG Jn Kl Kp Ny oH Pz Qa St Uc) kI(bF Kl Lv Ok qX St Tn Tz Ut Vu) nC(Ar bF dM Ip Is Ld Mr nR Nx) nR(Ed Id Jn Ko Kq Qz Ub) nF(bA cL dM Ji Kl Rc Uh) nA(aJ bA Kl Lh Ny Or) mS(aN cJ dG dL Ji) mT(bF Jp Pa qV Vp) oQ(aV Kn Qv) mU(Is Nj) DcmH KglW KnnI nDoN} Ld{nL(cL Ct dN LW mP nA nR oO Pk Uf) kI(cE dG dM hB It Mc Mp Ng nR Oz To) mF(aJ bQ cH cL dF dH Kd mP oN) nA(Cv iO Ji Kq lM Mn Nf Ng Ow) mP(dK eD Fa jQ jR nC nN Uf) nK(aJ cE cN cV dF dG hB) oQ(As De Hc Hu Ib Jv Ng) nC(cO dJ dM dN Oz) fR(Cp Hu Li Md) nJ(dG dM Mp nR) mM(cE dG Uh) mS(aY dL To) nI(cH cO pF) nR(Ao Of) nU(Ef Uv) qT(mT nB) NfmU HueP IdkE IikF JjmZ OrlW aYnD} nJ{oN(Ad Aw De Di Ib Jd mT Ng nT Of) cJ(dE dL Ii It nT Of Us) Is(Bn dJ Ef Gp Kk Kr) Ii(Dg dL Kf Or St) Ow(aY cI Mv nT Qm) In(bF Dc Kk pF) It(bA cL dM Ou) dL(aV dJ Oz To) Dg(Ad Jt Nm) Kc(mI Mp To) Or(As Pk Us) nT(aJ bZ dH) Cp(Lx Oh) Di(aY pF) Ef(dM Kf) Qu(cE Kl) Kk(bC Jv) qT(bS Rj) AfdM BcNg NnhB MvcE IbKf IzNx OzdG aSdF} Ib{kE(aJ aP cJ cT cV Ip jD Jl Jq Js Mp Ou Rc Tr) nL(Ar aY cJ cR Fn gL Jq Kc Kl Mr Nj Nv tF) nC(aD aY cX dI Kc Nj Oz) nR(Bc Id Ii Lh Tz Um) kI(cG cI cJ Jq Oz) nU(Ns Nv Qv Vu) Kf(eD jD oH) Cq(Mk mP) nT(Dg dH) MkMt MycX IcoH IpnD PzOu QcrY KckF LhmT OwfR aDmY cImU cJqU mFoQ nFoN} nF{Kn(bA cE dG dL Hw oE To) cJ(kI nL Nw oH qV Ra Uh) oH(dN Id Jj oN oO) cE(Di Fb Kc Kk) Mw(dG ON) Ii(Dg On Uh) Ow(Jj Mv Um) To(Nw Uh) In(Fy Kf) bA(Et Kk) FbdF NqOn JjKf KcOr UhlO aScT dMqV} nA{aY(Di Ng Ow To Uk) Dk(bA dG Lx Ou) lK(cJ dM hB pF) Mw(cJ dM Id) Ng(bA Bc oN) Or(bX Jv Mc) jV(dF hB Tv) In(bZ Kn) Is(Ha Kc) Qu(cJ dG) Ow(Ly oO) McdG ToKc IqOu ItKk IzNx KndL RjoN aSbA cEmT} mF{hB(Dk Gl In Mc Pk Tt Vs) dL(dI Kn Nj Pk) oQ(aN aR Dk oH) Di(aY dG lM) cI(Bc iJ nW) dN(Kk Kn Tv) lK(cR dM Kd) aY(Kk Qz) nT(dH dM) oO(Kj Pk) MwbF ToaR TviO KnmI cGjM} mS{Is(aS cH Cp dJ Fb Kj Ph Tt) Mw(cE cJ oN) qT(aS cI Us) jU(cJ dB iH) jV(cJ cR pF) Dk(cE oQ) aY(Nb Nj) DipF IiSt IncI IpPk IqcL ItKk} mT{Ng(aJ Bc dG dM hB Kf Kl) Mw(cG Kf Ko oN) qV(Hc Or Us) Dg(lN Nm) Qz(cT cX) Kc(jI lK) CtlK IrcH KnlN OhOr aOlM dGjO} nU{Kk(Ii Ij In Mv Nt qT) In(bX cJ Or Ow) Ow(It nB Of) qT(cJ Kn Qz) Ng(Ba Bc) aN(Kc Qz) oH(dN It) AdKf} nL{Mw(cN dH dN hB) Tv(jU JV Mc) Ng(Ba cI Kn) Di(aY Id) Kk(aY Hb) DkoO FpOa MchB HcOz JjcI aSbA} oQ{Ow(Dk Gl Ij Pg Qm) Di(dN Fb Mw Ss) Dk(aX bG) Mw(aV rZ) In(dA Dd) BoIi FbOe GloH IzQv} Em{Ou(cO Cw Hu Jm Jt Kd Mf Mh) Ly(aQ dG dL) Kg(Mh Oh Qd) NbIn QdJo KjOh} kI{Mc(aY Oa pF Tv) dN(Ng Or Tv) aY(iC In) dA(lK lM) jU(dI Gp) MwdG TvJu cRjV dLjI} nK{Is(dM Hb iP Kn Kz Ml Um) Mw(aJ bF) Tv(It To) DgNg MvdN OrcZ aSbA} qT{nT(Ef gP Kc) Dg(Ng Vv) Qu(kN nC) nR(aF bI) kK(dJ Kk) DkmW HccJ aSnB bAkN} kE{dG(Gp Ii Jj Ss) dL(cH cX oH Tv) Mw(aJ cG) Jj(Uc Ur) AwhB OrnB cHdN} dX{Mg(bA cT) Jj(bA cL) Kg(Dg Et) cI(cN cT) HuOu HvIi JpKy OrbB} nR{lK(Ap cE dL nN) Aw(In jV) Di(bC Mf) InbX KjrA dLjV} nD{Is(Ph Ua) cJ(jP jU) CtOw FbOh IndG KcjM cZqW dLoH iHjV} Ng{Pz(BA Kk wB) Ba(Kk nC) Kn(mU nC) IseP RjeF} mP{cJ(iC Kk Mw) Kn(jV lK) DkNw IpQg KcgW NxlK aNnT} nB{Mw(hB Ko) Tv(Ii Ut) Ow(Hb Qm) NbOr IsdI aSrA} nC{Mw(dN Uf) In(cJ Or) DiaY FnjV MchB aSbA} eM{aN(bJ cB Is Nk) Mg(Ji Ow) BoKd} tT{Qc(Iu Jn Jr Mt) MltO IlPz} Ow{oO(Hb Iz Mg) fR(It Me)} qX{Vv(Kf Kp) AjDg TomE KcOz} rZ{lY(It Jk Jm) mZ(In Mw)} lK{mH(cI Hb Ua) UanO dGlX} oH{dN(kC kO nH) IvfR dLlY} In{DdoO FymZ KfmE} cJ{WmqU nHjM jVkC} Ex{Nx(Kg Og)} Ha{Is(kC kO)} Pz{EflM NutX} Kk{mZjU jVkC} Vv{lL(Dg Kf)} fR{MbOr aCbC} nT{QtdG aVdL} tQ{MkMt JlJs} FbOhkP HuQctV KcOzrA aJjVkN Constrained panels with 3 analytes, where 1.0E-8 >= 'AUC p-value' > 1.0E-9. Contains 2,056 panels of 17,333,483 total panels evaluated. : oP{aX(Ap Cq Fa Hq kE kG kI Kq Lj Md mM Mr Nf Nn Nv oE oK oN Qm Rb Tn) iJ(bI cI Gl Hq Jv Jy Kl Mu Nf Om Oy Qt Qx Qy Ua Uk Ut) Aj(aY bF fP Fr hG Hq Jh Jk KC Mk Mt NF Om Uk) aN(bW Ij Jd Ki Lh Lj Mg Mr Mu Oa Oi Pi Tt Ue Uk) Ed(aO cH Ii Jk Mt Mv Mw Of Qm Rb Tt) Kk(aM aO Ap Dk Ke Kg Ks Mr Nb Nm Qm) Ld(Cq Fb Jy Kg Nb Nv Ny Oa Ph Tn Ug) Or(aP AS bF Bn bQ Cw De Je Mc Tt) nF(bF bQ In Jd Jf mF Mp Nj On Ow Uk) Oa(cB Cs dA dJ Fa Gl Jk Ph Po Ut) hG(cH dL kO Nm Ph To Ub Ug Uv Wm) Bo(Ax Jj Ms Nm NU Og Pa Wm) Fb(Hc Hu Mg Mv Oh Pb Qz To Vu) Je(cF iH kC kI kO mE nH nI nU) aP(Ax dG dL Dp Il kC nU oQ Wm) Nu(Ad cF De Dk Gl Kc mF oK) Kc(Ao Hb Hc Jg Mt My nU) cF(Ax Hb nB Oh Qx Qy Ug) cH(Dk Fr Jk Jt Jv mM nI) Wm(As aY Co fP Mv Ng) cS(cZ Gl nB Nf Nq Pb) Dk(Dl iH iO nB Ug) In(Jn mF nC nD nK) aF(cX iZ Jj nU Oy) mS(aS bF dL Jf oN) nH(Ba bI Co Cq De) nJ(Jv Qy To Ua Us) kO(Ap Ba Co De Jd) Ad(Hv iH kI Pa) Bb(cD Mz Nw Oy) Bn(Ax Jl Mp Ms) Dl(Gl Hb Jt Mg) Tt(dD nC Nj To) mF(Mu Mx Nn Nq) Fa(iO mE Ni) Hu(Ao bQ To) Jh(cM Kn Ow) Qz(Mc My Oz) Ut(mP nB nU) aO(cV Hv nB) dL(dJ nO nT) nC(oN Qt Vs) nD(bS Og Qy) iH(aY cJ Qu) kC(bF Cq Jd) Af(cX iZ)

Figure 18 Continued

As(cV kI) Ax(dJ Qu) Gl(oE Pa) Ni(oE Ub) Ua(cT Tz) Ow(Ao De) bQ(cL Ug) iO(dl On) ApNk BaNm B

Figure 18 Continued

Ij Kd oN oO oQ pF To) Mw(cG cJ Cv dF dL oN pF Uh) Mc(cE cJ dM Kn pF Qz Uh) cI(Cv Hu iO jU mS Oz) Qm(aY bA cL dM Ji) oO(Iz Je Pj Qu Ss) Tv(Cp dL Ij Tt) In(aY Fy Kd Ko) Vv(bA Is jM rA) Dk(dG nR On) Qu(bF cJ oN) Mv(dN To) Kk(Jv Oz) aY(To Uk) BooQ CtOh FyKj MeId KcdN OfcE OraS OzcH aOlM rCjY} mS{dG(cI Di Ef Fb Je Mv Nb Ow Qu) Is(Ao cI Ct Ef Hb Kk Us) cI(Ao Et jU Mp To Uf) dL(aV cH Di Kk Nt Oz) aY(Dk jV Mw Nt Ow) cJ(aN gW In jG qX) To(aN Kc Mw Nb) Tv(Iu Mv Qc) Ip(Co Ed Jv) aJ(jV nT rA) Dk(Dg nR) Mc(Or Ow) hB(Of Qu) qX(aW bX) qT(dB Ez) oN(As Jh) AoNj DeMx EtHb FbOh MvdN MwKd NbcH IiOa JeoQ QzjV OwpF hGrA} mT{Or(aM bX cH lN mE Mv nC Oa qT Ub) qW(aJ aK bL dL dN pF) lK(dM Ef hB Kn pF) Qz(aN aY cG pF) Kk(dL lN Nb qT) Oa(Cs Fb Ii Nj) Di(cE oN pF) Mw(bF dL pF) aM(cX jT Tv) qV(aJ cI Dk) qT(Ct Dk Kn) Ef(Nv Oh) Nt(Ax Kf) Is(Aj Kc) Kj(Ir Tv) cX(mZ Ne) lN(cJ Kf) AoOk CpjY CtOh WmiH IpbG JhoN} nK{Tv(aJ Co dG Hb Is Iu JU Kj Ph) Is(cL Kj Qz To Us Vu) Or(aS dN Kc Mv Mw To) cI(dF dL Jl nW Oh Tr) dG(Nj Nm Of Ss) To(cX Kk pF) Jh(bF cE oN) Ow(Hb Mc oO) Uk(aY cJ dN) Mv(bF oN) Mw(cG dN) cE(Dk Of) dL(Kk oH) DcIt EfoN FnjU HcaY IpQg OhdN UrdF} kI{dN(Aj aN aX cL Cv cX Dc Is Jj Mv) Mc(Ax bZ dM Kd oN Qz) Mw(cE cN dM pF rZ) aY(Hc Ly nO Qm Rj) lM(aO As Cp Ct Ke) jV(cI dH Kc Rj) Or(Ju Me Qm) In(cI hB) Jj(cI cZ) Jv(hB Tv) Kc(eD lK) rA(Gp Tz) DidG GlOh LycX IsVv RjjD} kE{aY(cH dL Gp jI Kk qV Uh Vp) dG(aX Ef Fb Ha Rj Vu) dL(bF dD Jj Mh Or To) aJ(eD Gp Jj nT qV) Di(cG hB oN pF) oQ(Ao Cp Je Ss) Jj(To Tv Uu) In(Ko St) Is(Gp Qg) AwoN MeOr MwcE TtTv KjhB QmdF UkcG aShA cInW} Ow{nB(aY cI De dL Fn Kd Mv Mw My Nl Or pF Tv Uk) oQ(Ao Ct De Di Jh Jv Mt Pf Po) fR(bC Ii In Mr Nl Pd) Em(Kg Kj Ks) oO(nC Ou Qm) nD(cJ Mc) CtMi HqeP TvOa HbmY QmnR OeeM} nR{lK(Ba bI cJ Mu Nn Qy) qT(aS bZ Hc Iz Ph) Di(Ii Nf Of) Dk(Bc dL iO) jV(aJ aM bG) Mw(dN iO) In(dA Kn) Qz(Ao Mc) Kc(jP lN) aF(gW lO) cZ(Kj qV) AwjP CpdN HbKk KeNw bGjU dAqW dLjY} eM{aN(cV Hb Hq Jl Kk Ks Mg Pd Pk Qb Qe) Mg(Ad bJ cB Cv Et Hc Nj) Is(Ct Hu Kg Oe Og Oy Pd) cV(bL Ks Nd) Dc(Kg Ks) Or(Io Pd) EtNm NbcX NdcN HuKc OfcL aCbE} nC{aY(Hc Kc Mw Qm Uk) Di(dN hB oO oQ) Mc(dM Kn Or Tv) Mw(cN dH oN) Jj(cI cZ) Jv(Kn oO) Kc(dN mI) HaOa MeOr TvJu IiNv InKo HcOz JiQm QuhB KjoO aOlM cHcI cLdN cXjU dGnT dJdL} qX{Aj(Ap BC Et gP Kf Kl Nm Pz) Vv(Ap cX Dl Ic Jg Jp Kl) Ct(Bc cH cJ Ml Oz) Hc(Kc Ml Oz qW) Jk(cJ Uc) Kc(Co Pb) Ph(cX qU) DgIz EfPz KfOz KknB cJcX} mP{nT(aJ aY cA Kk rZ To) In(aR cI Dc) Kc(iC jQ jV) Kk(cI dN To) Nx(Jh lN Nb) cJ(gW lK qT) dL(jO Kn Mw) Di(Is Jn) lK(cI Ct) CpLx DkJn MeOr UhjU aLqW dGjO eDiH} oQ{Dk(Di Jn OH Tz) Cp(Oe Oh Tv Tz) Aw(Je Or Tz) Di(aY Ii Je) In(aF aG dE) Iz(Bo Kk Ns) Is(Jk Po) dI(dE mM) oH(Bb Qm) DcVs FndA FyIi SsaS QuaX KjOe} Em{Ou(cA Cp Cq Fw Gp Hr It Iu Na No) Kg(aV bA dF Kq Mz Or Qe) Ly(aF Et Gp Nb) Jo(Cu Hb Kq) Qa(Ih Ii) Kj(bA Mp) LuLv HuaJ KnNx KqaV} dX{Aj(Bo Hb Iz Kl Ko Kq) cN(aL aQ Et In Kp Pj) Kg(aG bB dE Nw) Ky(cE Hu Mh Pe) bA(cB Ex Gp) Jj(cT Mw) BocI ExNr GpdE MnKs KrOy OgOu} nD{Is(aW Ef It Tt Vu Vv) cJ(eD jD lK To Uk Us) Cp(Oh oN) Dk(cE dF) Mw(cE oN) In(aY Uc) Qu(aJ Dg) jV(Kk Qz) EflM TvIh IiVt ItbA KclK dLnT} fR{Or(aQ bL gP In Nl Nt Tv) Nx(aQ bL bR Jk kQ Mp) iH(gP Mv Mw Qu) aN(bC Ii kQ) Nj(bL Mw) aC(An gP) oH(Et Ur) NlaQ QzaP} qT{kK(dA dE dL dM Kj Kn Kr Uk Us) cJ(Co Jd Ua Ut) nT(rX rY Tz) kN(bI dM Vu) lX(rZ Vp) mI(aS Cp) IccX UhmM VvbC nBoH} tT{Qc(Et Ms Nm Nn No Oh Qd) Mk(Hx Jp Mf Mq Mz Nb) Et(Ik Ml Pf) Pz(Hx Jr wL) Il(Iu Lh) Ji(Ik Nu) MzJs IptO} lK{mH(aJ aY Co dG dH dN Hc Iz Kd Oa pF Qy Qz Ue Vv) nO(Bn cX Kr Qy Tz Vu) lX(dM pF) aKmW} nB{Mw(cG dF Dg Kn oN Tv) Tv(Bn Dk Mv Tt Vs) Kc(Is jV lN) Kk(Ed Is) aS(cX Or) DgNm NbcX IpbG KndL VpdI} In{Jn(Ly Nd Ne Nl) Is(Ly nO Pz) Pz(Kf Tv) Kk(Kf mU) cJ(kC kO) mE(St Uc) oO(Di Og) IltN OanI dGnT} nT{dG(aV aX Bo cY De dJ Ii nH Rj) dL(An aY dA dI dM Nj Nl Qz) MwUf aYiJ} Pz{tQ(Il Jp Mt tX) tN(Jj Nu Pd) wB(Hu Il Mk) Ct(bA cT) Ua(bA lM) IkwJ JmtX JptR} Kk{mU(Bb gP Hb Ii jV Mc Nb Nt) nI(aY dL Hb pF) lW(Gl Hb Nb) AjKf dGmM} Qc{tQ(Mt Mz Nw) wB(Hu Ip Qa) Jr(tV tX) MktX MztR QaTk QlWn aJrC} Nx{Ex(aN Ed Ic Jj Ky Mf Or Rh Ue Ur Ut) MgVq QunH} Is{Iq(Hw Ij Lv Ly Ml Ms) Ml(Nd Tv) Hw(Ly Ne) AjeP KckC} Kf{Jk(eD jD jK) gP(Aj Jo Of) DkJo MgcM VvrA} nI{Mw(bF Dg oN) Or(bX Me) DioN DkcE cIiO cXjV} tQ{Et(Ma Mf Ml) MaMm MkLh MtIl MwHu NbJl JiJs} Mk{tV(Js Nb Pd Pe) Mm(wD wQ) IuwB} Vv{rA(cJ Dg To) lL(Ap Kc Kp) DgjO} kK{jI(aY dJ Pk) lM(Aw Cp) aJqV dMqW} Jn{Hw(Ly Nd Ne) NtUb MlNd aNeP} cJ{aN(kO nH) jM(iJ kC) QunH jUkC} lY{rZ(Hu Mr Nb Nt Pd) MfrY} mM{dG(dI dJ) dN(cH Kn) UhjV} Mz{tN(Ir Oh) QatX JswH} Tv{IuJj KjmZ iOkG jVkC} Kc{dL(mI nO) HcrA aNmI} nH{Qu(bF oN) CplM MwcE} Bc{Ub(gP Pk) RjgP} Il{tN(Ji tS) JlwQ} cH{MwkF RjgP aCbE} Mm{MawH PfwP} Oh{FbnN KjmZ} Vq{eF(Ct Mg)} dI{dLnO jIkN} iO{oO(aN Ss)} AjaCbE BodAeP CpkOoN DgJtjO FnjVkC MwaJnN RjaObA OrPbmZ

Constrained panels with 2 analytes, where 1.0E-8 >= 'AUC p-value' > 0. Contains 10 panels of 114,449 total panels evaluated. : oP(Aw Ch Cp Cw Di Ef Ib Iz Kj Qw)

Constrained panels with 2 analytes, where 1.0E-7 >= 'AUC p-value' > 1.0E-8. Contains 8 panels of 114,449 total panels evaluated. : oP(aN Ao As Bb Bg Ct) UbQw IbnR Constrained panels with 2 analytes, where 1.0E-6 >= 'AUC p-value' > 1.0E-7. Contains 9 panels of 114,449 total panels evaluated. : oP(Aj aS bQ Hc hG) Qw(gP nU) LdnA OrnJ Constrained panels with 2 analytes, where 1.0E-5 >= 'AUC p-value' > 1.0E-6. Contains 54 panels of 114,449 total panels evaluated. : oP(Ad aY Ba bF Bo Co De Fb Gl iH mF nF) Qw(aJ bA bC cN cV Ed eF Ib Jj Ow) Ib(Kf Ml oH On Ow Pz Rj) Ng(Ad Bc Dg Kf Nx Ow) nJ(cJ dL dN Ld oN) Ld(mP nL nU) Nx(Ex In nF) Ch(nR nU) Is(Hw Iq) Ow(nF nU) OnnF aCbE Constrained panels with 2 analytes, where 1.0E-4 >= 'AUC p-value' > 1.0E-5. Contains 183 panels of 114,449 total panels evaluated. : Ib(bA BC cH cJ cL cT cV cX Dc Et gL gP iH Is Iu Ji Jn kE Ky Nj NL Ou Tn Vs) Ng(aJ BA bC Bo cE cG Cu cV Dc dF dG EF Ex fP gL Kc Kp Kq Ky Ou Qw) Qw(aY cH cL dG Hw Is kI Mf nC Ne Nj Nk nL nR oH oQ Or Pk qT qX Rj) nF(bA cJ Ji nR Nv Nw Ny Ok oN oQ Uh) oP(Dk Ed In Jd Je mP nL Qu Uk Ut Wm) nJ(aJ aY cE dG dM Kc Kk Ow To) Ch(eF kE mF mP mT nC nL oQ) Nx(Hw Ly Lz Ml mP Nd Nl Po) Is(Ij Il In Ly Ml Nd Tv) qX(Aj cH cJ Ct Kc Vv) Ld(kI mF nC nK oQ) nA(aY dG dL oN Or) tT(Ji Mk Ml Pz) Ly(cV Ji Jn) Nd(Jl Jn Ml) Ne(Hw In Jl) Ow(Aj In Mf) dL(kE mS nT) mF(dG hB oQ) Jj(dX gP) Kk(mP nU) aC(bC fR) tQ(Et Mt) AoKf BcUb DkoQ MktV MztN UabA HwJi InJn RjgP OrnK aYkE dNkI lXqT Constrained panels with 2 analytes, where 1.0E-3 >= 'AUC p-value' > 1.0E-4. Contains 548 panels of 114,449 total panels evaluated. : Ng(Ap aY bB bF Bg bX cH cJ cL cN cT cX dH DL Ez fR hB Hc iJ iO Kl Kn Ko On Or Pk Qz Rj Tn Ub Uc Uf Uh Uu Vq Vs) Ib(Ad Ax Ba bE cN Cw Dg eF Id Jg Jp Kc kI Kl Kp Kq NC Nf Nm nU Og oQ Pk qU qX Qz To Tv Ub Uh) Is(Aj Ct Ih Ii It Jm Jn Jo Jr Js Kj Ks Lu Lv Lz Md Mk mP Ms nB Ne NF nK Nx Pe Po Qb Qc Ub) bA(aC bC Ch Ct Dk gP Hu Ii Jk Ly Mg nA Nd Ne Nf nJ nK Of Pk Ut) Aj(Ad bC eF Jn Kc Kf Ky Ly Mt Nc Ne Nj Nl Nm Nx Ou Pz rA) nF(Ba bF cE cG cL dF Dg dM Et Fr hA hB Jl Kn Ma Mn Or rZ) Ch(aC Bo fR Kf kI Ky mS mU nA nD Ne NJ Nl Ow qX Tn) Ub(bC cL Cv cX eF gP Hw Ji Jj Jn Ld Nj Nt Ow Pk Qz Rj) Qw(cT cX eD Ji Jn jU mF mP nA Nc nD Nf nJ Nl pF Pz Qa) Nd(Et Fr Hw In Ji Ly Lz Mb Me Mf Mp Mt Nw Ok On Pz) Ow(Jj Jo Ks Ky Ly Mg Ml nA nB Nf Of Og oO oQ Pz) Ji(Ao Ii Ij In Iq Jo Ml Ne Nf Om

Figure 18 Continued

Qm tQ Ue) Jn(Hw Iq Ks mP Ms Ne Nh Nl oP Tv Ue Us) mF(aR bZ cG cI dH dL dN Kc Kk oO Or Tv) nA(aJ bZ cE cG cJ cL dM dN hB Kc To Vt) Kf(Hu Hw Ii In Jo Jt Kk Mg Nm Nt Of) oP(Jf Jv IK nB nC nH Og Oi Qy Ua Vs) Ly(cH Em Et Hw In Jl Ne Nw Ok On) nJ(aR cG cL dF Dg dH hB Ko Uh Vt) Ne(cH Et Iq It Lv Lz Ml Nx Ok) Jj(BC eM Kk Ky Ld oH Rj Us) mP(aN cI cJ jl IK nC Ok On qW) Hw(Et Mt Nc Nh Nj Nl Nw On) In(Mt Nc Nh Nj Nl Nw Ou Qa) Nx(Ii Iq Jo Md Ms Nf Qc Ut) nU(cJ dL dM Ef Kc Or Qz To) mT(aJ Ax cE dL Kk Ld oN Or) nL(cI dH dJ Kk oO oQ rC To) tQ(Hv Jl Jp Mk Mm Mz Nb tN) tT(Et Hx Jp Jr Mf Mt Mz tV) fR(aQ bR dB gP Mw Nf Nl) oQ(aN Aw Di Mc Mw Nb Og) Tv(Dd Iu Nj nK Oa Qh) tV(Hu Il Pe Pg Qc wQ) Kc(bC eD Kk nC rA) Ou(Hq Jk Mf Mg Of) cJ(jM kC mS qT rA) gP(aJ bB Bc Ed hB) Ii(dG Oa On Or) Iq(Jl Nw On Qa) bC(cT cX Nj Rj) nB(Kk Kn Nb qT) nC(aY dJ dN To) nK(dG dL dM To) qX(cX Hc Kp Pk) kE(aJ cG dN Or) Et(Ao Jo Ue) Qc(Qa tX wB) Jl(Nh Nj Nl) Of(dG hB On) nR(Dk Ld lK) mS(cl dG To) qT(Hc Ic Vv) Bc(Ed Ue) Ct(cT rA) Dg(Jt Nm) Mk(wB wD) Qu(eF iJ) Rj(Nt oH) aC(aX cZ) dL(nO oH) CvEd MeKs MmwQ UeeF HucL IltN KkmU KydX NwOm OknD OrkI aYIL cHeD lYrZ tStX

Figure 18 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.0E1 | 5.6E1 | 8.2E1 | 5.6E1 | 5.8E1 | 3.2E1 | 1.0E0 | 1.6E1 | 4.8E2 | 1.1E2 | 1777 | 11 | 298 | 11 | 0.38 |
| Ad | ug/mL | 3.8E-2 | 6.2E-2 | 9.1E-2 | 7.3E-2 | 3.8E-1 | 6.1E-2 | 2.7E-4 | 9.4E-3 | 8.5E0 | 1.9E-1 | 511 | 7 | 198 | 7 | 0.58 |
| Af | ng/mL | 1.2E0 | 3.6E-1 | 1.8E1 | 2.2E0 | 6.6E1 | 5.1E0 | 1.7E-3 | 1.7E-3 | 5.3E2 | 1.4E1 | 511 | 7 | 198 | 7 | 0.32 |
| Aj | ug/mL | 1.5E0 | 7.6E-1 | 2.6E0 | 1.3E0 | 2.5E0 | 1.4E0 | 1.5E-3 | 3.2E-2 | 6.1E0 | 3.5E0 | 511 | 7 | 198 | 7 | 0.39 |
| Al | mg/mL | 8.8E-5 | 8.5E-5 | 2.4E-4 | 1.3E-4 | 4.0E-4 | 1.4E-4 | 2.3E-6 | 2.2E-5 | 2.2E-3 | 4.4E-4 | 511 | 7 | 198 | 7 | 0.50 |
| An | U/mL | 5.0E1 | 2.9E2 | 1.9E2 | 3.7E2 | 5.6E2 | 4.5E2 | 9.8E-4 | 7.4E0 | 7.8E3 | 1.3E3 | 511 | 7 | 198 | 7 | 0.69 |
| Ao | pg/mL | 9.0E1 | 8.9E1 | 4.7E2 | 1.4E2 | 3.2E3 | 2.1E2 | 1.5E0 | 7.8E0 | 3.9E4 | 6.0E2 | 511 | 7 | 198 | 7 | 0.42 |
| Ap | ng/mL | 3.2E1 | 4.7E1 | 4.7E1 | 4.8E1 | 4.9E1 | 2.9E1 | 8.4E-5 | 6.8E0 | 3.3E2 | 9.7E1 | 511 | 7 | 198 | 7 | 0.59 |
| Ar | ng/mL | 9.8E-1 | 5.9E0 | 1.1E1 | 6.4E0 | 1.8E2 | 4.9E0 | 3.4E-3 | 1.7E-1 | 4.1E3 | 1.5E1 | 511 | 7 | 198 | 7 | 0.76 |
| As | ng/mL | 8.7E-3 | 1.0E-2 | 1.5E-2 | 9.4E-3 | 5.7E-2 | 5.7E-3 | 1.7E-3 | 1.7E-3 | 1.2E0 | 1.5E-2 | 511 | 7 | 198 | 7 | 0.51 |
| Aw | pg/mL | 1.6E1 | 1.8E1 | 1.6E1 | 2.0E1 | 6.3E0 | 7.5E0 | 2.9E-2 | 1.1E1 | 5.1E1 | 3.0E1 | 511 | 7 | 198 | 7 | 0.64 |
| Ax | ng/mL | 2.1E0 | 8.1E0 | 1.5E1 | 3.9E1 | 6.0E1 | 7.2E1 | 1.2E-2 | 3.9E-1 | 7.7E2 | 2.0E2 | 511 | 7 | 198 | 7 | 0.67 |
| Ba | ng/mL | 6.2E1 | 5.8E2 | 4.4E2 | 2.4E3 | 1.1E3 | 3.2E3 | 2.7E-1 | 1.1E1 | 8.1E3 | 8.1E3 | 511 | 7 | 198 | 7 | 0.70 |
| Bb | ng/mL | 3.2E0 | 6.3E0 | 6.6E0 | 6.9E0 | 1.4E1 | 6.5E0 | 4.1E-3 | 4.1E-3 | 2.5E2 | 1.9E1 | 511 | 7 | 198 | 7 | 0.58 |
| Bc | ng/mL | 3.8E1 | 8.9E1 | 1.1E2 | 1.5E2 | 1.9E2 | 1.3E2 | 1.1E-1 | 9.6E0 | 1.2E3 | 3.6E2 | 511 | 7 | 198 | 7 | 0.70 |
| Bg | ng/mL | 8.1E-2 | 6.2E-1 | 5.3E0 | 1.7E0 | 2.9E1 | 2.2E0 | 5.3E-4 | 3.1E-2 | 4.4E2 | 5.3E0 | 511 | 7 | 198 | 7 | 0.62 |
| Bn | ng/mL | 5.6E-2 | 5.6E-2 | 1.4E0 | 4.6E-1 | 3.2E0 | 1.0E0 | 5.6E-2 | 5.6E-2 | 5.8E1 | 2.8E0 | 511 | 7 | 198 | 7 | 0.38 |
| Bo | ng/mL | 1.2E1 | 2.7E1 | 1.4E1 | 2.9E1 | 1.8E1 | 1.8E1 | 1.6E-2 | 1.6E-2 | 2.8E2 | 5.3E1 | 511 | 7 | 198 | 7 | 0.78 |
| Ch | uIU/mL | 9.8E-1 | 9.2E-1 | 1.7E1 | 1.5E0 | 9.6E1 | 1.7E0 | 3.4E-3 | 1.2E-1 | 1.8E3 | 5.2E0 | 511 | 7 | 198 | 7 | 0.44 |
| Co | pg/mL | 3.7E1 | 5.5E1 | 1.7E2 | 8.1E1 | 9.1E2 | 7.9E1 | 1.5E-1 | 8.1E0 | 1.7E4 | 2.1E2 | 511 | 7 | 198 | 7 | 0.56 |
| Cp | ng/mL | 2.2E1 | 3.3E1 | 3.0E1 | 4.7E1 | 6.3E1 | 3.2E1 | 6.0E-1 | 8.6E0 | 1.3E3 | 8.4E1 | 511 | 7 | 198 | 7 | 0.69 |
| Cq | ng/mL | 3.0E-2 | 3.9E-2 | 2.3E-1 | 4.3E-2 | 2.3E0 | 3.3E-2 | 8.0E-4 | 8.0E-4 | 4.9E1 | 1.0E-1 | 511 | 7 | 198 | 7 | 0.54 |
| Cs | ng/mL | 6.6E1 | 2.7E2 | 3.2E2 | 1.1E3 | 1.1E3 | 1.9E3 | 2.7E-2 | 5.8E0 | 1.8E4 | 5.3E3 | 511 | 7 | 198 | 7 | 0.65 |
| Ct | ng/mL | 6.0E-1 | 3.5E-1 | 3.7E1 | 2.0E1 | 1.1E2 | 2.8E1 | 1.1E-4 | 6.8E-2 | 6.2E2 | 7.2E1 | 511 | 7 | 198 | 7 | 0.55 |
| Cu | ng/mL | 2.4E-1 | 6.8E-1 | 5.3E-1 | 8.3E-1 | 3.0E0 | 7.6E-1 | 9.0E-5 | 9.8E-2 | 6.6E1 | 2.4E0 | 511 | 7 | 198 | 7 | 0.72 |
| Cv | ng/mL | 5.6E0 | 6.5E0 | 2.6E1 | 7.5E1 | 6.5E1 | 1.7E2 | 1.4E-4 | 5.7E-2 | 5.3E2 | 4.7E2 | 511 | 7 | 198 | 7 | 0.50 |
| Cw | mIU/mL | 3.0E-2 | 4.3E-2 | 5.1E-2 | 4.0E-2 | 3.0E-1 | 1.8E-2 | 1.5E-4 | 3.5E-3 | 6.8E0 | 5.7E-2 | 511 | 7 | 198 | 7 | 0.58 |
| Cx | ng/mL | 4.6E-1 | 1.3E-2 | 6.3E1 | 4.1E1 | 1.1E2 | 1.1E2 | 9.3E-5 | 9.3E-5 | 3.9E2 | 2.8E2 | 511 | 7 | 198 | 7 | 0.38 |
| Db | ug/mL | 7.4E0 | 8.6E0 | 9.2E0 | 1.1E1 | 1.0E1 | 9.0E0 | 4.5E-1 | 1.3E0 | 1.4E2 | 2.9E1 | 511 | 7 | 198 | 7 | 0.57 |
| Dc | nmol/L | 1.9E-2 | 3.2E-2 | 8.4E-2 | 3.6E-1 | 6.3E-1 | 8.2E-1 | 5.2E-6 | 6.3E-3 | 1.4E1 | 2.2E0 | 511 | 7 | 198 | 7 | 0.61 |
| Dd | ug/mL | 7.5E-2 | 2.0E-2 | 1.8E-1 | 8.1E-2 | 2.9E-1 | 1.1E-1 | 8.3E-5 | 3.2E-3 | 3.6E0 | 2.5E-1 | 511 | 7 | 198 | 7 | 0.38 |
| De | ng/mL | 3.4E-3 | 3.4E-3 | 8.0E-2 | 6.5E-2 | 1.4E-1 | 8.1E-2 | 3.4E-3 | 3.4E-3 | 9.2E-1 | 2.0E-1 | 511 | 7 | 198 | 7 | 0.52 |
| Dg | ng/mL | 3.2E1 | 5.9E1 | 4.5E1 | 4.7E1 | 4.1E1 | 2.7E1 | 1.0E-1 | 1.1E1 | 1.9E2 | 7.6E1 | 511 | 7 | 198 | 7 | 0.58 |
| Di | pg/mL | 1.8E0 | 2.2E0 | 2.2E0 | 2.3E0 | 2.1E0 | 1.6E0 | 1.8E-1 | 1.8E-1 | 1.3E1 | 4.4E0 | 511 | 7 | 198 | 7 | 0.55 |
| Dk | uIU/mL | 1.6E-2 | 1.8E-2 | 8.3E-2 | 1.2E-1 | 4.8E-1 | 2.3E-1 | 1.1E-4 | 1.1E-4 | 8.9E0 | 6.3E-1 | 511 | 7 | 198 | 7 | 0.59 |
| Dl | ng/mL | 2.4E2 | 2.3E2 | 3.2E2 | 3.0E2 | 3.0E2 | 2.5E2 | 1.7E0 | 5.9E1 | 1.6E3 | 7.8E2 | 511 | 7 | 198 | 7 | 0.52 |
| Dp | ng/ml | 2.4E0 | 1.8E0 | 6.0E0 | 6.3E0 | 1.4E1 | 9.4E1 | 3.7E-3 | 1.9E-1 | 2.0E2 | 2.6E1 | 315 | 7 | 189 | 7 | 0.48 |
| Ef | ng/ml | 1.3E-1 | 5.6E-1 | 8.9E-1 | 1.1E0 | 1.9E0 | 1.4E0 | 5.7E-4 | 2.1E-2 | 1.0E1 | 3.9E0 | 379 | 7 | 195 | 7 | 0.62 |
| Wm | % | 7.0E-1 | 1.3E0 | 3.4E1 | 1.5E2 | 1.8E2 | 4.2E2 | 5.4E-2 | 8.5E-2 | 2.4E3 | 1.3E3 | 416 | 9 | 214 | 9 | 0.57 |
| Ed | pg/ml | 5.2E-1 | 1.1E1 | 5.6E1 | 4.7E1 | 4.1E2 | 6.9E1 | 5.2E-1 | 5.2E-1 | 7.3E3 | 1.6E2 | 315 | 7 | 188 | 7 | 0.61 |
| Tj | pg/mL | 3.7E-1 | 3.7E-1 | 5.1E1 | 8.7E0 | 2.8E2 | 1.7E1 | 3.6E-1 | 3.7E-1 | 3.5E3 | 4.4E1 | 378 | 7 | 198 | 7 | 0.46 |
| Po | pg/ml | 6.9E-1 | 3.3E0 | 8.6E0 | 1.0E1 | 2.4E1 | 1.3E1 | 8.0E-3 | 2.6E-2 | 2.7E2 | 3.1E1 | 899 | 13 | 335 | 13 | 0.58 |
| Et | ng/ml | 1.4E3 | 2.0E3 | 1.7E3 | 2.2E3 | 1.2E3 | 1.5E3 | 7.5E1 | 5.0E2 | 5.0E3 | 5.0E3 | 898 | 13 | 335 | 13 | 0.60 |
| Fa | ng/ml | 4.4E1 | 8.9E1 | 1.3E2 | 1.2E2 | 5.2E2 | 8.2E1 | 3.4E-2 | 3.4E0 | 8.0E3 | 2.3E2 | 311 | 7 | 186 | 7 | 0.69 |
| Ez | ng/ml | 4.1E0 | 7.4E0 | 1.7E1 | 2.7E1 | 5.0E1 | 3.3E1 | 1.3E-2 | 3.8E-1 | 7.1E2 | 8.9E1 | 315 | 7 | 189 | 7 | 0.64 |
| Fb | ng/ml | 2.5E1 | 3.5E1 | 2.3E1 | 3.2E1 | 1.1E1 | 1.3E1 | 5.9E-1 | 4.0E0 | 5.7E1 | 4.3E1 | 312 | 7 | 186 | 7 | 0.74 |
| Fn | ng/ml | 2.1E-1 | 2.1E-1 | 5.8E0 | 1.8E0 | 2.5E1 | 2.3E0 | 1.1E-14 | 1.1E-14 | 4.2E2 | 5.3E0 | 315 | 7 | 189 | 7 | 0.43 |
| Fp | ng/ml | 1.4E1 | 2.4E1 | 2.5E1 | 3.8E1 | 2.9E1 | 4.6E1 | 6.0E-3 | 1.3E-1 | 1.4E2 | 1.4E2 | 931 | 13 | 336 | 13 | 0.54 |
| Fr | ng/ml | 3.7E4 | 1.1E5 | 1.2E5 | 2.9E5 | 1.8E5 | 3.0E5 | 1.9E2 | 4.5E3 | 9.0E5 | 7.4E5 | 1043 | 13 | 340 | 13 | 0.69 |
| Fw | pg/ml | 1.2E0 | 9.8E0 | 5.8E1 | 1.5E1 | 4.5E2 | 1.7E1 | 1.1E-14 | 1.2E-1 | 6.9E3 | 3.9E1 | 380 | 7 | 196 | 7 | 0.60 |
| Gl | pg/ml | 7.2E3 | 8.6E3 | 1.1E4 | 1.2E4 | 9.2E3 | 1.2E4 | 9.1E1 | 4.9E2 | 3.4E4 | 3.1E4 | 370 | 7 | 194 | 7 | 0.51 |
| Gp | U/ml | 1.6E0 | 4.7E-1 | 4.0E0 | 8.9E-1 | 6.7E0 | 1.2E0 | 1.3E-3 | 1.5E-2 | 6.7E1 | 3.2E0 | 382 | 7 | 196 | 7 | 0.30 |
| Ha | ng/ml | 2.7E0 | 3.0E0 | 9.6E0 | 3.5E0 | 2.1E1 | 3.1E0 | 6.4E-3 | 1.7E-2 | 1.3E2 | 9.0E0 | 313 | 7 | 188 | 7 | 0.47 |
| Nm | pg/ml | 1.4E4 | 2.0E4 | 3.3E4 | 2.6E4 | 8.2E4 | 3.1E4 | 1.0E-9 | 1.0E-9 | 1.6E6 | 1.0E5 | 902 | 13 | 337 | 13 | 0.48 |

Figure 19

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nn | pg/ml | 1.6E2 | 4.9E2 | 1.9E3 | 1.7E3 | 8.2E3 | 2.4E3 | 1.0E-9 | 1.0E-9 | 1.0E5 | 7.7E3 | 902 | 13 | 337 | 13 | 0.57 |
| No | pg/ml | 1.6E1 | 1.5E1 | 3.8E1 | 9.8E1 | 1.1E2 | 2.1E2 | 1.0E-9 | 6.4E-1 | 2.5E3 | 7.7E2 | 902 | 13 | 337 | 13 | 0.53 |
| Nq | pg/ml | 2.0E0 | 5.8E0 | 2.0E1 | 1.9E1 | 7.6E1 | 3.2E1 | 1.0E-9 | 1.0E-9 | 1.2E3 | 9.9E1 | 902 | 13 | 337 | 13 | 0.56 |
| Nr | pg/ml | 1.2E0 | 1.0E-9 | 2.9E1 | 1.6E1 | 1.8E2 | 2.8E1 | 1.0E-9 | 1.0E-9 | 4.1E3 | 8.7E1 | 902 | 13 | 337 | 13 | 0.49 |
| Ns | pg/ml | 1.0E-9 | 1.0E-9 | 9.2E0 | 5.5E-1 | 5.2E1 | 1.3E0 | 1.0E-9 | 1.0E-9 | 1.1E3 | 3.6E0 | 902 | 13 | 337 | 13 | 0.52 |
| Nt | pg/ml | 1.0E2 | 1.5E2 | 1.4E2 | 1.6E2 | 1.2E2 | 9.1E1 | 1.0E-9 | 5.4E1 | 1.7E3 | 3.7E2 | 902 | 13 | 337 | 13 | 0.62 |
| Nu | pg/ml | 2.0E1 | 5.4E1 | 5.5E1 | 9.0E1 | 9.0E1 | 9.3E1 | 1.0E-9 | 1.0E-9 | 8.9E2 | 2.9E2 | 902 | 13 | 337 | 13 | 0.63 |
| Lu | pg/ml | 1.0E4 | 6.8E3 | 1.8E4 | 9.8E3 | 6.2E4 | 8.8E3 | 3.5E2 | 2.9E3 | 1.3E6 | 3.1E4 | 905 | 13 | 337 | 13 | 0.38 |
| Lv | pg/ml | 1.0E-9 | 2.2E1 | 1.1E1 | 4.3E1 | 2.2E1 | 5.5E1 | 1.0E-9 | 1.0E-9 | 2.6E2 | 1.6E2 | 905 | 13 | 337 | 13 | 0.66 |
| Lw | pg/ml | 1.0E-9 | 1.0E-9 | 3.7E-1 | 1.3E0 | 3.8E0 | 4.6E0 | 1.0E-9 | 1.0E-9 | 8.0E1 | 1.7E1 | 905 | 13 | 337 | 13 | 0.53 |
| Lx | pg/ml | 1.0E-9 | 2.2E2 | 1.7E2 | 4.4E2 | 8.6E2 | 6.7E2 | 1.0E-9 | 1.0E-9 | 2.2E4 | 2.3E3 | 905 | 13 | 337 | 13 | 0.69 |
| Ly | pg/ml | 1.0E-9 | 2.7E0 | 1.0E1 | 9.2E0 | 2.0E1 | 1.2E1 | 1.0E-9 | 1.0E-9 | 1.6E2 | 4.0E1 | 905 | 13 | 337 | 13 | 0.59 |
| Lz | pg/ml | 1.0E-9 | 1.0E-9 | 4.0E0 | 1.0E-9 | 3.0E1 | 0.0E0 | 1.0E-9 | 1.0E-9 | 6.0E2 | 1.0E-9 | 905 | 13 | 337 | 13 | 0.46 |
| Ma | pg/ml | 2.9E2 | 5.3E2 | 1.4E3 | 1.3E3 | 3.6E3 | 1.8E3 | 1.0E-9 | 2.0E1 | 6.5E4 | 6.8E3 | 905 | 13 | 337 | 13 | 0.58 |
| Mb | pg/ml | 2.5E1 | 4.3E1 | 3.1E1 | 4.0E1 | 1.5E1 | 1.7E1 | 4.1E0 | 1.9E1 | 2.1E2 | 7.3E1 | 905 | 13 | 337 | 13 | 0.64 |
| Mc | pg/ml | 1.0E-9 | 1.0E-9 | 3.8E-2 | 1.9E-1 | 5.7E-1 | 6.9E-1 | 1.0E-9 | 1.0E-9 | 1.3E1 | 2.5E0 | 905 | 13 | 337 | 13 | 0.53 |
| Md | pg/ml | 1.0E-9 | 1.0E-9 | 4.4E-1 | 4.6E-1 | 3.6E0 | 1.6E0 | 1.0E-9 | 1.0E-9 | 6.8E1 | 5.9E0 | 905 | 13 | 337 | 13 | 0.50 |
| Me | pg/ml | 3.3E1 | 3.0E1 | 3.2E1 | 2.9E1 | 2.0E1 | 1.1E1 | 1.0E-9 | 9.4E0 | 3.2E2 | 4.4E1 | 905 | 13 | 337 | 13 | 0.44 |
| Mf | pg/ml | 1.0E-9 | 1.0E-9 | 5.4E-1 | 1.7E-1 | 2.9E0 | 6.0E-1 | 1.0E-9 | 1.0E-9 | 5.6E1 | 2.2E0 | 905 | 13 | 337 | 13 | 0.46 |
| Mg | pg/ml | 1.6E0 | 3.5E0 | 7.4E0 | 6.4E0 | 1.2E1 | 1.1E1 | 1.0E-9 | 1.0E-9 | 9.2E1 | 4.0E1 | 905 | 13 | 337 | 13 | 0.50 |
| Mh | pg/ml | 1.0E-9 | 1.0E-9 | 1.3E0 | 2.0E0 | 9.6E0 | 4.1E0 | 1.0E-9 | 1.0E-9 | 1.6E2 | 1.1E1 | 905 | 13 | 337 | 13 | 0.53 |
| Mi | pg/ml | 1.0E-9 | 1.0E-9 | 9.0E-1 | 2.4E0 | 1.2E1 | 8.6E0 | 1.0E-9 | 1.0E-9 | 3.2E2 | 3.1E1 | 905 | 13 | 337 | 13 | 0.53 |
| Mj | pg/ml | 1.0E-9 | 1.0E-9 | 4.5E0 | 1.0E1 | 2.5E1 | 3.0E1 | 1.0E-9 | 1.0E-9 | 4.6E2 | 1.1E2 | 905 | 13 | 337 | 13 | 0.56 |
| Mk | pg/ml | 1.0E0 | 1.0E-9 | 1.3E1 | 5.6E0 | 8.5E1 | 1.0E1 | 1.0E-9 | 1.0E-9 | 1.7E3 | 3.6E1 | 905 | 13 | 337 | 13 | 0.47 |
| Ml | pg/ml | 1.0E-9 | 1.0E-9 | 5.6E0 | 2.0E0 | 7.5E1 | 4.8E0 | 1.0E-9 | 1.0E-9 | 2.1E3 | 1.4E1 | 905 | 13 | 337 | 13 | 0.49 |
| Mm | pg/ml | 6.1E2 | 5.3E2 | 1.1E3 | 8.5E2 | 1.5E3 | 7.8E2 | 1.0E-9 | 4.4E1 | 1.2E4 | 2.2E3 | 905 | 13 | 337 | 13 | 0.50 |
| Mn | pg/ml | 5.6E0 | 8.4E0 | 1.0E1 | 9.9E0 | 2.3E1 | 1.1E1 | 1.0E-9 | 1.0E-9 | 3.5E2 | 4.2E1 | 905 | 13 | 337 | 13 | 0.56 |
| Mp | pg/ml | 1.0E-9 | 6.4E0 | 1.0E1 | 1.1E1 | 3.4E1 | 1.3E1 | 1.0E-9 | 1.0E-9 | 6.3E2 | 4.0E1 | 904 | 13 | 337 | 13 | 0.61 |
| Mq | pg/ml | 1.0E-9 | 1.0E-9 | 2.9E0 | 9.4E0 | 1.7E1 | 2.5E1 | 1.0E-9 | 1.0E-9 | 2.4E2 | 8.6E1 | 904 | 13 | 337 | 13 | 0.54 |
| Mr | pg/ml | 1.0E-9 | 3.5E0 | 2.8E1 | 5.2E0 | 1.6E2 | 6.4E0 | 1.0E-9 | 1.0E-9 | 2.2E3 | 1.7E1 | 904 | 13 | 337 | 13 | 0.60 |
| Ms | pg/ml | 4.1E2 | 5.0E2 | 5.6E2 | 4.4E2 | 6.5E2 | 3.3E2 | 1.0E-9 | 1.0E-9 | 5.9E3 | 1.1E3 | 904 | 13 | 337 | 13 | 0.49 |
| Mt | pg/ml | 2.5E-1 | 2.6E0 | 1.1E1 | 9.6E0 | 1.2E2 | 2.0E1 | 1.0E-9 | 1.0E-9 | 3.2E3 | 7.3E1 | 904 | 13 | 337 | 13 | 0.64 |
| Mu | pg/ml | 1.0E-9 | 1.0E-9 | 1.3E0 | 3.3E0 | 1.0E1 | 6.0E0 | 1.0E-9 | 1.0E-9 | 2.3E2 | 2.1E1 | 904 | 13 | 337 | 13 | 0.63 |
| Mv | pg/ml | 1.0E-9 | 1.0E-9 | 7.0E1 | 6.0E1 | 3.2E2 | 1.1E2 | 1.0E-9 | 1.0E-9 | 4.5E3 | 3.1E2 | 904 | 13 | 337 | 13 | 0.58 |
| Mw | pg/ml | 3.8E1 | 6.4E1 | 5.2E2 | 3.5E2 | 3.3E3 | 4.2E2 | 1.0E-9 | 1.0E-9 | 6.2E4 | 1.2E3 | 904 | 13 | 337 | 13 | 0.65 |
| Mx | pg/ml | 1.0E-9 | 1.0E-9 | 2.8E-1 | 1.7E-1 | 1.5E0 | 3.7E-1 | 1.0E-9 | 1.0E-9 | 3.2E1 | 1.2E0 | 904 | 13 | 337 | 13 | 0.54 |
| My | pg/ml | 1.0E-9 | 7.5E0 | 4.7E2 | 1.8E2 | 3.0E3 | 2.5E2 | 1.0E-9 | 1.0E-9 | 3.9E4 | 7.7E2 | 904 | 13 | 337 | 13 | 0.63 |
| Mz | pg/ml | 1.1E1 | 2.6E1 | 3.0E1 | 4.6E1 | 9.9E1 | 6.4E1 | 1.0E-9 | 1.0E-9 | 1.9E3 | 2.1E2 | 904 | 13 | 337 | 13 | 0.67 |
| Na | pg/ml | 1.0E-9 | 1.0E-9 | 7.3E-1 | 1.8E0 | 3.0E0 | 4.7E0 | 1.0E-9 | 1.0E-9 | 4.2E1 | 1.6E1 | 904 | 13 | 337 | 13 | 0.52 |
| Nb | pg/ml | 2.0E0 | 4.1E0 | 3.9E0 | 5.5E0 | 1.2E1 | 3.9E0 | 1.0E-9 | 1.0E-9 | 2.3E2 | 1.3E1 | 904 | 13 | 337 | 13 | 0.72 |
| Nc | pg/ml | 3.4E2 | 3.0E2 | 5.6E2 | 4.9E2 | 7.3E2 | 5.0E2 | 1.0E-9 | 1.0E-9 | 9.2E3 | 1.6E3 | 904 | 13 | 337 | 13 | 0.53 |
| Nd | pg/ml | 2.9E1 | 4.8E0 | 2.9E1 | 2.2E1 | 8.3E1 | 2.8E1 | 1.0E-9 | 1.0E-9 | 2.1E3 | 9.4E1 | 904 | 13 | 337 | 13 | 0.40 |
| Ne | pg/ml | 4.4E2 | 3.1E2 | 5.8E2 | 4.1E2 | 5.7E2 | 3.5E2 | 1.0E-9 | 5.5E1 | 7.0E3 | 1.2E3 | 904 | 13 | 337 | 13 | 0.42 |
| Nf | pg/ml | 1.0E-9 | 1.0E-9 | 3.0E0 | 2.1E-1 | 1.1E1 | 7.6E-1 | 1.0E-9 | 1.0E-9 | 1.6E2 | 2.7E0 | 904 | 13 | 337 | 13 | 0.41 |
| Ng | pg/ml | 1.9E1 | 1.4E-1 | 1.3E2 | 9.0E1 | 2.5E2 | 1.6E2 | 1.0E-9 | 1.0E-9 | 2.3E3 | 4.7E2 | 904 | 13 | 337 | 13 | 0.41 |
| Nh | pg/ml | 6.9E1 | 5.3E1 | 9.0E1 | 6.4E1 | 8.2E1 | 4.7E1 | 1.0E-9 | 8.6E0 | 5.6E2 | 1.5E2 | 904 | 13 | 337 | 13 | 0.43 |
| Ni | pg/ml | 1.0E-9 | 1.5E2 | 7.3E1 | 2.1E2 | 1.2E2 | 1.7E2 | 1.0E-9 | 1.0E-9 | 1.1E3 | 4.8E2 | 904 | 13 | 337 | 13 | 0.75 |
| Nj | pg/ml | 7.3E0 | 5.4E0 | 1.1E1 | 1.1E1 | 1.2E1 | 9.1E0 | 1.0E-9 | 1.2E0 | 1.1E2 | 2.8E1 | 904 | 13 | 337 | 13 | 0.52 |
| Nk | pg/ml | 1.7E1 | 3.6E1 | 3.3E1 | 3.8E1 | 4.0E1 | 2.6E1 | 1.0E-9 | 1.2E1 | 2.0E2 | 8.7E1 | 904 | 13 | 337 | 13 | 0.63 |
| Nl | pg/ml | 4.6E1 | 4.1E1 | 6.1E1 | 5.7E1 | 6.8E1 | 4.9E1 | 1.0E-9 | 9.3E-1 | 1.1E3 | 1.4E2 | 904 | 13 | 337 | 13 | 0.50 |
| Tz | pg/ml | 5.3E3 | 8.5E3 | 1.4E4 | 6.6E3 | 6.2E4 | 4.0E3 | 1.0E-9 | 1.8E3 | 1.0E6 | 1.0E4 | 317 | 7 | 187 | 7 | 0.52 |
| Ua | pg/ml | 3.9E3 | 4.7E3 | 2.0E4 | 2.7E4 | 1.2E5 | 4.9E4 | 1.0E-9 | 8.8E2 | 2.1E6 | 1.4E5 | 317 | 7 | 187 | 7 | 0.58 |
| Ub | pg/ml | 5.6E2 | 2.3E2 | 8.4E2 | 2.5E2 | 1.0E3 | 1.8E2 | 1.0E-9 | 3.9E1 | 9.8E3 | 5.8E2 | 317 | 7 | 187 | 7 | 0.25 |
| Ue | pg/ml | 2.8E1 | 1.6E1 | 3.9E1 | 1.9E1 | 4.2E1 | 6.5E0 | 9.8E-2 | 1.0E1 | 4.4E2 | 3.0E1 | 317 | 7 | 187 | 7 | 0.27 |
| Uc | pg/ml | 9.2E2 | 1.0E3 | 1.9E3 | 9.5E2 | 4.1E3 | 6.5E2 | 1.0E-9 | 1.2E2 | 5.7E4 | 2.0E3 | 317 | 7 | 187 | 7 | 0.45 |
| Ud | pg/ml | 1.0E-9 | 1.0E-9 | 1.5E0 | 1.0E-9 | 2.2E1 | 0.0E0 | 1.0E-9 | 1.0E-9 | 3.9E2 | 1.0E-9 | 317 | 7 | 187 | 7 | 0.49 |
| Hq | pg/ml | 1.1E0 | 1.5E0 | 1.0E2 | 3.4E0 | 1.6E3 | 6.3E0 | 1.0E-9 | 1.0E-9 | 3.4E4 | 2.4E1 | 900 | 13 | 336 | 13 | 0.57 |

Figure 19 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Hr | pg/ml | 1.2E2 | 8.9E1 | 7.9E2 | 5.3E2 | 1.6E3 | 1.3E3 | 1.0E-9 | 2.5E1 | 1.7E4 | 4.6E3 | 900 | 13 | 336 | 13 | 0.48 |
| Hu | pg/ml | 5.6E0 | 1.2E1 | 3.0E3 | 6.4E2 | 2.6E4 | 2.0E3 | 1.0E-9 | 1.0E-9 | 6.3E5 | 7.2E3 | 900 | 13 | 336 | 13 | 0.50 |
| Hv | pg/ml | 1.4E0 | 2.0E0 | 4.1E0 | 2.4E0 | 3.2E1 | 2.5E0 | 1.0E-9 | 1.0E-9 | 8.9E2 | 9.4E0 | 900 | 13 | 336 | 13 | 0.58 |
| Hw | pg/ml | 6.5E0 | 5.1E0 | 2.9E1 | 9.8E0 | 3.2E2 | 1.8E1 | 1.0E-9 | 1.0E-9 | 9.4E3 | 6.8E1 | 900 | 13 | 336 | 13 | 0.38 |
| Hx | pg/ml | 8.8E0 | 2.5E1 | 3.9E1 | 4.1E1 | 3.2E2 | 5.6E1 | 1.0E-9 | 1.0E-9 | 9.3E3 | 2.1E2 | 900 | 13 | 336 | 13 | 0.67 |
| Ib | ng/ml | 4.9E-2 | 1.8E-2 | 1.4E0 | 8.8E-2 | 5.6E0 | 1.3E-1 | 1.0E-9 | 1.0E-9 | 5.6E1 | 3.1E-1 | 307 | 7 | 186 | 7 | 0.40 |
| Ic | U/ml | 2.2E2 | 2.2E2 | 9.5E2 | 3.1E3 | 6.7E3 | 7.7E3 | 1.5E0 | 4.2E1 | 9.3E4 | 2.1E4 | 307 | 7 | 186 | 7 | 0.60 |
| Id | U/ml | 6.9E-1 | 1.2E0 | 2.9E0 | 2.5E0 | 2.5E1 | 3.2E0 | 1.0E-9 | 2.7E-1 | 4.3E2 | 9.4E0 | 307 | 7 | 186 | 7 | 0.64 |
| Ih | ng/ml | 7.2E1 | 2.1E2 | 2.4E2 | 5.7E2 | 4.3E2 | 9.6E2 | 1.0E-9 | 1.0E-9 | 3.6E3 | 3.5E3 | 904 | 13 | 336 | 13 | 0.59 |
| Ii | ng/ml | 9.4E1 | 3.7E1 | 2.5E2 | 1.7E2 | 6.8E2 | 2.7E2 | 1.0E-9 | 2.5E0 | 1.0E4 | 7.9E2 | 903 | 13 | 336 | 13 | 0.40 |
| Ij | ng/ml | 7.7E1 | 9.9E1 | 2.0E2 | 1.1E2 | 9.9E2 | 8.4E1 | 1.0E-9 | 6.2E0 | 2.4E4 | 2.9E2 | 891 | 13 | 334 | 13 | 0.51 |
| Ik | ng/ml | 1.3E1 | 5.7E1 | 8.1E2 | 2.2E2 | 8.2E3 | 4.0E2 | 5.9E-1 | 2.8E0 | 1.2E5 | 1.5E3 | 898 | 13 | 334 | 13 | 0.57 |
| Il | ng/ml | 3.4E2 | 1.8E2 | 1.3E3 | 3.5E2 | 2.8E3 | 6.4E2 | 1.0E-9 | 1.0E-9 | 1.3E4 | 2.4E3 | 881 | 13 | 334 | 13 | 0.31 |
| Im | ng/ml | 2.1E2 | 5.7E2 | 3.9E2 | 9.4E2 | 6.0E2 | 1.8E3 | 1.3E1 | 3.2E1 | 6.2E3 | 6.8E3 | 897 | 13 | 335 | 13 | 0.58 |
| In | ng/ml | 3.7E0 | 8.9E-1 | 2.7E1 | 2.9E0 | 2.1E2 | 3.6E0 | 1.0E-9 | 1.0E-9 | 4.5E3 | 9.4E0 | 904 | 13 | 336 | 13 | 0.32 |
| Hb | ng/ml | 2.5E1 | 2.3E1 | 3.6E1 | 4.1E1 | 3.5E1 | 4.3E1 | 4.8E-1 | 4.1E0 | 2.1E2 | 1.2E2 | 316 | 7 | 187 | 7 | 0.52 |
| Hc | pg/ml | 6.4E2 | 8.3E2 | 3.4E3 | 5.0E3 | 1.2E4 | 6.0E3 | 1.0E-9 | 2.6E2 | 1.0E5 | 1.5E4 | 316 | 7 | 187 | 7 | 0.62 |
| Hf | ng/ml | 1.6E2 | 1.4E2 | 3.6E2 | 3.6E2 | 4.9E2 | 4.1E2 | 1.0E-9 | 6.8E1 | 2.5E3 | 1.0E3 | 316 | 7 | 187 | 7 | 0.57 |
| Io | ng/ml | 8.1E3 | 5.1E3 | 2.4E4 | 9.7E3 | 1.5E5 | 1.1E4 | 1.0E-9 | 9.0E2 | 4.0E6 | 3.3E4 | 896 | 13 | 336 | 13 | 0.43 |
| Ip | pg/ml | 9.7E0 | 5.2E0 | 1.9E1 | 2.9E1 | 2.4E1 | 4.0E1 | 1.0E-9 | 8.1E-2 | 2.6E2 | 1.4E2 | 896 | 13 | 336 | 13 | 0.54 |
| Iq | ug/ml | 1.0E-1 | 1.3E-1 | 3.2E1 | 2.3E-1 | 6.4E2 | 3.5E-1 | 1.0E-9 | 1.0E-9 | 1.4E4 | 1.3E0 | 896 | 13 | 336 | 13 | 0.44 |
| Ir | ug/ml | 3.5E-1 | 1.6E0 | 3.9E0 | 4.9E0 | 2.8E1 | 9.2E0 | 1.0E-9 | 7.7E-2 | 5.1E2 | 3.4E1 | 895 | 13 | 336 | 13 | 0.70 |
| Is | ng/ml | 1.5E0 | 9.0E0 | 6.6E0 | 1.2E1 | 2.3E1 | 1.2E1 | 1.0E-9 | 2.7E-1 | 5.5E2 | 3.5E1 | 896 | 13 | 336 | 13 | 0.73 |
| It | ng/ml | 2.0E0 | 2.9E0 | 2.4E1 | 1.8E1 | 1.4E2 | 3.3E1 | 1.0E-9 | 1.0E-9 | 2.8E3 | 1.2E2 | 896 | 13 | 336 | 13 | 0.53 |
| Iu | ng/ml | 2.2E2 | 1.7E2 | 1.4E3 | 4.2E2 | 4.2E3 | 6.3E2 | 1.0E-9 | 1.0E-9 | 2.9E4 | 2.3E3 | 896 | 13 | 336 | 13 | 0.46 |
| Iv | ng/ml | 1.3E1 | 5.0E1 | 6.1E1 | 1.2E2 | 5.5E2 | 2.3E2 | 1.0E-9 | 1.9E0 | 1.6E4 | 8.7E2 | 895 | 13 | 336 | 13 | 0.73 |
| Iz | ng/ml | 1.4E2 | 4.3E2 | 6.0E2 | 5.0E2 | 3.6E3 | 5.6E2 | 9.2E-1 | 2.1E1 | 6.2E4 | 1.5E3 | 316 | 7 | 187 | 7 | 0.55 |
| Rc | pg/ml | 5.9E3 | 5.3E3 | 7.3E3 | 9.8E3 | 5.8E3 | 9.2E3 | 1.9E2 | 2.8E3 | 3.9E4 | 2.9E4 | 314 | 7 | 187 | 7 | 0.58 |
| Rb | pg/ml | 8.7E-1 | 1.5E0 | 2.8E0 | 2.5E0 | 5.3E0 | 2.1E0 | 1.0E-9 | 8.6E-1 | 5.6E1 | 5.6E0 | 314 | 7 | 187 | 7 | 0.64 |
| Pz | ng/ml | 3.9E3 | 1.0E4 | 8.3E3 | 6.4E3 | 3.8E4 | 4.6E3 | 1.3E1 | 9.5E1 | 1.0E6 | 1.2E4 | 896 | 13 | 334 | 13 | 0.56 |
| Qa | ng/ml | 3.5E3 | 9.9E3 | 6.5E3 | 1.1E4 | 1.0E4 | 9.3E3 | 1.2E1 | 2.9E2 | 2.2E5 | 2.9E4 | 896 | 13 | 334 | 13 | 0.63 |
| Qb | ng/ml | 9.7E1 | 2.1E2 | 2.1E2 | 2.7E2 | 4.9E2 | 3.3E2 | 7.9E-1 | 8.7E0 | 8.3E3 | 1.2E3 | 896 | 13 | 334 | 13 | 0.58 |
| Qc | ng/ml | 2.3E2 | 4.8E2 | 6.3E2 | 4.3E2 | 5.6E3 | 3.7E2 | 1.0E-9 | 8.6E0 | 1.7E5 | 1.2E3 | 896 | 13 | 334 | 13 | 0.54 |
| Qd | ng/ml | 9.2E3 | 4.4E4 | 1.9E4 | 6.8E4 | 7.3E4 | 7.8E4 | 1.5E2 | 1.7E3 | 2.0E6 | 2.3E5 | 896 | 13 | 334 | 13 | 0.69 |
| Qe | ng/ml | 9.2E2 | 2.6E3 | 1.9E3 | 3.6E3 | 4.7E3 | 3.9E3 | 1.0E-9 | 1.2E2 | 9.7E4 | 1.3E4 | 896 | 13 | 334 | 13 | 0.65 |
| Jd | ng/ml | 9.5E-1 | 3.0E0 | 5.9E0 | 3.3E0 | 3.9E1 | 3.1E0 | 1.0E-9 | 1.0E-9 | 6.5E2 | 8.5E0 | 315 | 7 | 189 | 7 | 0.63 |
| Je | ng/ml | 1.0E-9 | 2.8E0 | 2.1E0 | 2.3E0 | 7.2E0 | 2.3E0 | 1.0E-9 | 1.0E-9 | 8.8E1 | 6.4E0 | 315 | 7 | 189 | 7 | 0.66 |
| Jf | ng/ml | 1.0E-9 | 2.7E-1 | 1.1E0 | 8.5E-1 | 2.2E0 | 1.2E0 | 1.0E-9 | 1.0E-9 | 1.2E1 | 3.0E0 | 315 | 7 | 189 | 7 | 0.58 |
| Jg | ng/ml | 5.0E2 | 1.3E3 | 8.3E2 | 1.2E3 | 1.0E3 | 1.0E3 | 1.0E-9 | 4.5E1 | 1.0E4 | 3.5E3 | 900 | 13 | 336 | 13 | 0.64 |
| Jh | ng/ml | 3.0E0 | 1.2E1 | 2.9E1 | 3.9E1 | 1.2E2 | 6.2E1 | 1.0E-9 | 1.0E-9 | 1.6E3 | 2.1E2 | 900 | 13 | 336 | 13 | 0.66 |
| Ji | ng/ml | 5.3E1 | 9.0E1 | 7.9E1 | 1.6E2 | 9.0E1 | 1.4E2 | 1.0E-9 | 2.7E1 | 1.3E3 | 4.6E2 | 900 | 13 | 336 | 13 | 0.72 |
| Sr | pg/mL | 3.9E2 | 2.1E3 | 9.5E2 | 2.6E3 | 1.7E3 | 2.1E3 | 1.0E-9 | 1.0E-9 | 2.1E4 | 5.4E3 | 305 | 7 | 184 | 7 | 0.68 |
| Ss | pg/mL | 9.4E4 | 2.0E5 | 1.5E5 | 1.4E5 | 1.8E5 | 8.4E4 | 2.7E3 | 2.6E4 | 1.8E6 | 2.0E5 | 305 | 7 | 184 | 7 | 0.55 |
| St | pg/mL | 2.7E7 | 7.5E7 | 5.5E7 | 3.4E8 | 9.2E7 | 5.9E8 | 1.0E-9 | 1.6E6 | 1.2E9 | 1.7E9 | 309 | 7 | 185 | 7 | 0.65 |
| Ra | pg/ml | 1.0E-9 | 5.2E-1 | 8.1E-1 | 6.5E-1 | 3.8E0 | 1.1E0 | 1.0E-9 | 1.0E-9 | 6.4E1 | 3.0E0 | 314 | 7 | 187 | 7 | 0.59 |
| Qz | pg/ml | 1.0E1 | 1.0E-9 | 6.2E1 | 5.3E1 | 1.0E2 | 1.2E2 | 1.0E-9 | 1.0E-9 | 7.1E2 | 3.2E2 | 314 | 7 | 187 | 7 | 0.37 |
| Qy | pg/ml | 4.4E-1 | 8.8E-1 | 1.3E1 | 6.9E0 | 7.1E1 | 1.2E1 | 1.0E-9 | 2.5E-1 | 6.5E2 | 3.1E1 | 314 | 7 | 187 | 7 | 0.68 |
| Qx | pg/ml | 1.0E-9 | 1.0E-9 | 5.9E0 | 1.6E0 | 4.6E1 | 3.9E0 | 1.0E-9 | 1.0E-9 | 5.8E2 | 1.0E1 | 314 | 7 | 187 | 7 | 0.57 |
| Qw | pg/ml | 1.0E-9 | 1.0E-9 | 3.1E0 | 1.0E-9 | 1.5E1 | 0.0E0 | 1.0E-9 | 1.0E-9 | 1.3E2 | 1.0E-9 | 314 | 7 | 187 | 7 | 0.28 |
| Qv | pg/ml | 2.3E4 | 6.6E3 | 3.6E4 | 8.2E3 | 7.3E4 | 5.7E3 | 1.0E-9 | 2.1E3 | 9.4E5 | 2.0E4 | 314 | 7 | 187 | 7 | 0.19 |
| Qu | pg/ml | 6.8E0 | 4.4E1 | 8.4E1 | 8.1E1 | 1.7E2 | 9.9E1 | 1.0E-9 | 1.0E-9 | 9.8E2 | 2.2E2 | 314 | 7 | 187 | 7 | 0.56 |
| Qt | pg/ml | 1.0E1 | 2.1E1 | 5.0E1 | 4.1E1 | 1.2E2 | 4.9E1 | 1.0E-9 | 1.0E-9 | 1.0E3 | 1.4E2 | 314 | 7 | 187 | 7 | 0.62 |
| Qh | ng/ml | 1.7E1 | 3.3E1 | 3.8E1 | 4.8E1 | 6.4E1 | 4.2E1 | 1.0E-9 | 7.8E-1 | 6.4E2 | 1.1E2 | 314 | 7 | 187 | 7 | 0.60 |
| Qg | ng/ml | 8.2E0 | 1.2E1 | 1.9E1 | 1.8E1 | 6.3E1 | 2.2E1 | 5.1E-2 | 7.7E-1 | 1.0E3 | 6.3E1 | 314 | 7 | 187 | 7 | 0.53 |
| Jj | ng/ml | 6.1E2 | 2.0E2 | 1.6E3 | 3.8E2 | 1.2E4 | 5.0E2 | 1.5E0 | 3.3E1 | 3.4E5 | 1.8E3 | 900 | 13 | 336 | 13 | 0.26 |
| Jk | ng/ml | 3.0E0 | 7.9E0 | 2.1E1 | 2.4E1 | 4.7E1 | 3.1E1 | 1.0E-9 | 2.0E-1 | 3.9E2 | 1.0E2 | 900 | 13 | 336 | 13 | 0.56 |
| Jl | ng/ml | 4.1E-1 | 1.3E0 | 2.6E0 | 4.3E0 | 1.9E1 | 7.1E0 | 7.6E-4 | 3.9E-2 | 5.4E2 | 2.0E1 | 900 | 13 | 336 | 13 | 0.68 |

Figure 19 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jm | ng/ml | 1.8E1 | 2.1E1 | 5.8E1 | 4.6E1 | 1.3E2 | 6.1E1 | 1.0E-9 | 4.1E-1 | 2.1E3 | 1.5E2 | 900 | 13 | 336 | 13 | 0.48 |
| Jn | pg/ml | 4.0E-1 | 1.0E0 | 3.7E0 | 2.0E0 | 3.8E1 | 2.3E0 | 1.0E-9 | 2.5E-2 | 7.3E2 | 8.3E0 | 899 | 13 | 336 | 13 | 0.65 |
| Jo | pg/ml | 3.6E3 | 1.8E3 | 4.9E3 | 3.2E3 | 5.0E3 | 2.9E3 | 2.0E1 | 2.6E2 | 1.0E5 | 9.2E3 | 900 | 13 | 336 | 13 | 0.36 |
| Jp | pg/ml | 7.0E4 | 1.1E5 | 7.3E4 | 1.0E5 | 3.8E4 | 3.4E4 | 5.8E2 | 2.3E4 | 3.8E5 | 1.5E5 | 900 | 13 | 336 | 13 | 0.76 |
| Jq | pg/ml | 9.6E1 | 1.4E2 | 1.6E2 | 3.7E2 | 3.6E2 | 8.9E2 | 1.0E0 | 1.5E1 | 8.7E3 | 3.3E3 | 900 | 13 | 336 | 13 | 0.52 |
| Jr | pg/ml | 5.3E0 | 1.7E1 | 4.4E1 | 2.3E1 | 4.7E2 | 2.7E1 | 1.0E-9 | 1.0E-9 | 1.1E4 | 1.0E2 | 900 | 13 | 336 | 13 | 0.70 |
| Js | pg/ml | 1.3E1 | 1.4E1 | 5.3E1 | 2.0E1 | 3.8E2 | 1.6E1 | 1.0E-9 | 3.5E0 | 1.0E4 | 5.6E1 | 900 | 13 | 336 | 13 | 0.53 |
| Jt | pg/ml | 2.6E3 | 2.6E3 | 3.2E3 | 3.1E3 | 2.8E3 | 2.1E3 | 2.2E1 | 8.5E2 | 5.2E4 | 7.5E3 | 900 | 13 | 336 | 13 | 0.50 |
| Ju | mIU/ml | 9.0E0 | 1.3E1 | 1.9E1 | 1.1E1 | 3.0E1 | 8.8E0 | 4.8E-2 | 2.7E-1 | 2.3E2 | 2.4E1 | 315 | 7 | 189 | 7 | 0.47 |
| Jv | mIU/ml | 1.2E1 | 8.9E0 | 3.4E1 | 1.2E1 | 5.9E1 | 1.2E1 | 1.0E-2 | 9.4E-3 | 4.4E2 | 2.9E1 | 315 | 7 | 189 | 7 | 0.41 |
| Jy | ng/ml | 1.6E-3 | 2.9E-3 | 2.2E-3 | 8.0E-3 | 3.9E-3 | 1.5E-2 | 1.0E-9 | 8.6E-4 | 5.2E-2 | 4.1E-2 | 315 | 7 | 189 | 7 | 0.73 |
| Kc | pg/ml | 2.6E1 | 1.4E2 | 4.5E1 | 1.2E2 | 4.8E1 | 6.0E1 | 1.0E-9 | 2.2E1 | 2.7E2 | 1.7E2 | 316 | 7 | 187 | 7 | 0.84 |
| Kd | pg/ml | 1.0E-9 | 1.0E-9 | 3.0E2 | 9.5E2 | 2.2E3 | 1.9E3 | 1.0E-9 | 1.0E-9 | 3.8E4 | 5.2E3 | 316 | 7 | 187 | 7 | 0.57 |
| Ke | pg/ml | 1.3E4 | 1.3E4 | 1.6E4 | 2.6E4 | 2.1E4 | 3.8E4 | 3.4E2 | 2.2E3 | 3.2E5 | 1.1E5 | 316 | 7 | 187 | 7 | 0.51 |
| Kf | pg/mL | 7.3E0 | 1.7E1 | 7.6E0 | 1.4E1 | 7.1E0 | 7.4E0 | 1.0E-9 | 1.0E-9 | 7.8E1 | 2.2E1 | 316 | 7 | 187 | 7 | 0.76 |
| Kg | pg/mL | 1.1E3 | 5.2E2 | 1.9E3 | 1.1E3 | 2.8E3 | 1.5E3 | 7.3E1 | 2.9E2 | 2.7E4 | 4.4E3 | 316 | 7 | 187 | 7 | 0.34 |
| Ki | pg/ml | 5.9E1 | 8.8E1 | 7.0E1 | 8.7E1 | 5.4E1 | 2.6E1 | 1.0E-9 | 4.2E1 | 3.8E2 | 1.2E2 | 315 | 7 | 187 | 7 | 0.69 |
| Kj | pg/ml | 9.7E2 | 3.2E2 | 1.6E3 | 6.9E2 | 1.8E3 | 6.5E2 | 1.4E1 | 2.1E2 | 1.5E4 | 1.8E3 | 316 | 7 | 187 | 7 | 0.29 |
| Kk | pg/ml | 7.0E0 | 5.5E1 | 1.2E1 | 4.0E1 | 1.6E1 | 2.6E1 | 1.0E-9 | 1.0E-9 | 1.6E2 | 6.4E1 | 316 | 7 | 187 | 7 | 0.78 |
| Kl | pg/ml | 2.0E4 | 3.3E4 | 2.8E4 | 3.5E4 | 2.5E4 | 2.5E4 | 1.6E2 | 3.2E3 | 1.6E5 | 6.8E4 | 316 | 7 | 187 | 7 | 0.60 |
| Kn | pg/ml | 3.0E1 | 6.2E1 | 7.7E1 | 1.5E2 | 2.9E2 | 2.0E2 | 1.0E-9 | 1.0E-9 | 4.9E3 | 4.7E2 | 316 | 7 | 187 | 7 | 0.58 |
| Ko | pg/ml | 3.6E2 | 7.5E2 | 5.2E2 | 6.8E2 | 5.5E2 | 5.1E2 | 1.0E-9 | 4.1E3 | 4.1E3 | 1.4E3 | 316 | 7 | 187 | 7 | 0.62 |
| Kp | pg/ml | 3.4E2 | 7.9E2 | 4.0E2 | 7.4E2 | 7.8E2 | 3.1E2 | 1.0E-9 | 2.8E2 | 1.3E4 | 1.1E3 | 316 | 7 | 187 | 7 | 0.83 |
| Kq | pg/ml | 3.2E2 | 8.7E2 | 1.0E3 | 2.5E3 | 9.1E3 | 4.1E3 | 1.6E0 | 2.9E2 | 1.6E5 | 1.2E4 | 308 | 7 | 181 | 7 | 0.77 |
| Kr | pg/ml | 5.0E-1 | 1.0E-9 | 3.6E0 | 5.6E-1 | 2.4E1 | 1.2E0 | 1.0E-9 | 1.0E-9 | 4.2E2 | 3.3E0 | 308 | 7 | 181 | 7 | 0.37 |
| Ks | pg/ml | 1.4E4 | 1.2E4 | 2.0E4 | 1.5E4 | 1.8E4 | 1.4E4 | 5.1E1 | 3.6E3 | 1.1E5 | 4.3E4 | 308 | 7 | 181 | 7 | 0.45 |
| Ky | ng/ml | 9.5E-2 | 9.4E-1 | 3.8E-1 | 1.1E0 | 8.2E-1 | 1.0E0 | 1.0E-9 | 1.0E-9 | 6.4E0 | 2.7E0 | 315 | 7 | 187 | 7 | 0.76 |
| Kz | ng/ml | 1.0E-9 | 1.0E-9 | 3.6E-3 | 6.7E-4 | 5.7E-3 | 1.8E-3 | 1.0E-9 | 1.0E-9 | 3.6E-2 | 4.7E-3 | 315 | 7 | 187 | 7 | 0.38 |
| Ld | pg/ml | 1.0E-9 | 3.6E0 | 3.7E0 | 4.5E0 | 8.8E0 | 4.4E0 | 1.0E-9 | 1.0E-9 | 8.4E1 | 1.2E1 | 314 | 7 | 186 | 7 | 0.68 |
| Lh | pg/ml | 1.3E4 | 2.3E4 | 2.2E4 | 2.8E4 | 3.2E4 | 2.6E4 | 1.0E-9 | 4.0E2 | 4.8E5 | 7.3E4 | 900 | 12 | 337 | 12 | 0.57 |
| Li | pg/ml | 3.3E3 | 9.7E3 | 1.7E4 | 2.3E4 | 6.2E4 | 3.3E4 | 1.0E-9 | 1.2E2 | 1.3E6 | 1.1E5 | 900 | 12 | 337 | 12 | 0.61 |
| Lj | pg/ml | 2.8E3 | 8.3E3 | 2.3E4 | 7.4E4 | 6.6E4 | 1.8E5 | 1.0E-9 | 1.9E2 | 5.2E5 | 6.1E5 | 900 | 12 | 337 | 12 | 0.58 |
| Rm | ng/ml | 2.0E1 | 5.2E1 | 5.3E1 | 5.1E1 | 8.2E1 | 3.6E1 | 2.2E-1 | 1.4E0 | 6.5E2 | 1.0E2 | 309 | 7 | 186 | 7 | 0.62 |
| Rh | ng/ml | 1.3E2 | 3.9E2 | 3.6E2 | 6.4E2 | 1.2E3 | 8.6E2 | 3.6E0 | 8.1E1 | 1.7E4 | 2.5E3 | 309 | 7 | 186 | 7 | 0.68 |
| Ri | ng/ml | 1.0E-9 | 1.0E-9 | 4.2E0 | 6.8E0 | 1.5E1 | 1.3E1 | 1.0E-9 | 1.0E-9 | 2.2E2 | 3.6E1 | 310 | 7 | 187 | 7 | 0.53 |
| Rg | ng/ml | 1.0E-9 | 3.0E-3 | 6.0E-2 | 3.1E-3 | 3.8E-1 | 4.5E-3 | 1.0E-9 | 1.0E-9 | 4.6E0 | 1.3E-2 | 309 | 7 | 186 | 7 | 0.65 |
| Rj | ng/ml | 1.0E-9 | 1.0E-9 | 2.2E0 | 1.0E-9 | 1.6E1 | 0.0E0 | 1.0E-9 | 1.0E-9 | 2.7E2 | 1.0E-9 | 310 | 7 | 187 | 7 | 0.36 |
| Rf | ng/ml | 4.2E-1 | 2.6E0 | 1.0E0 | 4.5E0 | 1.8E0 | 4.8E0 | 7.8E-3 | 3.9E-2 | 1.5E1 | 1.4E1 | 309 | 7 | 186 | 7 | 0.80 |
| Ql | pg/ml | 5.5E0 | 7.3E0 | 1.5E1 | 1.1E1 | 2.9E1 | 1.1E1 | 1.0E-9 | 1.0E-9 | 2.9E2 | 2.6E1 | 315 | 7 | 189 | 7 | 0.53 |
| Qm | pg/ml | 4.4E0 | 2.3E1 | 2.1E1 | 3.1E1 | 3.8E1 | 4.3E1 | 1.0E-9 | 1.0E-9 | 3.6E2 | 1.2E2 | 315 | 7 | 189 | 7 | 0.56 |
| Qn | pg/ml | 6.1E-1 | 6.0E-1 | 8.4E0 | 1.9E0 | 2.6E1 | 4.2E0 | 1.0E-9 | 1.0E-9 | 2.4E2 | 1.1E1 | 315 | 7 | 189 | 7 | 0.38 |
| Nv | pg/ml | 4.0E3 | 5.1E3 | 1.1E4 | 1.8E4 | 4.3E4 | 2.5E4 | 1.0E-9 | 4.7E2 | 1.1E6 | 7.7E4 | 906 | 13 | 337 | 13 | 0.64 |
| Nw | pg/ml | 8.9E3 | 1.6E4 | 1.3E4 | 3.5E4 | 1.7E4 | 5.7E4 | 8.6E1 | 3.9E3 | 2.1E5 | 2.2E5 | 906 | 13 | 337 | 13 | 0.70 |
| Nx | pg/ml | 2.2E2 | 1.1E3 | 4.1E2 | 8.2E2 | 6.5E2 | 6.3E2 | 1.0E-9 | 3.6E1 | 7.4E3 | 2.2E3 | 906 | 13 | 337 | 13 | 0.75 |
| Ny | pg/ml | 6.4E0 | 1.8E2 | 5.7E1 | 6.6E1 | 8.5E2 | 1.4E2 | 1.0E-9 | 1.0E-9 | 2.5E4 | 4.9E2 | 906 | 13 | 337 | 13 | 0.53 |
| Oa | pg/ml | 1.8E2 | 5.5E2 | 4.6E2 | 7.0E2 | 7.3E2 | 8.1E2 | 1.0E-9 | 2.6E1 | 4.8E3 | 2.4E3 | 315 | 7 | 189 | 7 | 0.63 |
| Oe | pg/ml | 6.8E1 | 7.8E1 | 2.9E2 | 1.9E2 | 7.5E2 | 2.5E2 | 1.0E-9 | 1.0E-9 | 1.9E4 | 7.7E2 | 897 | 13 | 336 | 13 | 0.49 |
| Of | pg/ml | 1.7E2 | 9.7E1 | 6.1E3 | 1.2E3 | 2.8E4 | 1.9E3 | 1.0E-9 | 1.0E-9 | 6.2E5 | 6.0E3 | 905 | 13 | 337 | 13 | 0.45 |
| Og | pg/ml | 8.2E-2 | 7.6E-2 | 4.8E-1 | 1.2E-1 | 1.6E0 | 1.6E-1 | 1.0E-9 | 1.0E-9 | 2.0E1 | 5.3E-1 | 905 | 13 | 337 | 13 | 0.44 |
| Oh | pg/ml | 2.7E0 | 4.8E0 | 2.0E1 | 2.9E1 | 1.5E2 | 5.9E1 | 1.0E-9 | 1.0E-9 | 3.5E3 | 1.9E2 | 905 | 13 | 337 | 13 | 0.60 |
| Oi | pg/ml | 2.6E0 | 3.3E-1 | 6.3E0 | 6.3E0 | 9.8E0 | 9.2E0 | 1.0E-9 | 1.0E-9 | 8.6E1 | 2.8E1 | 905 | 13 | 337 | 13 | 0.47 |
| Ok | pg/ml | 3.9E2 | 8.3E2 | 5.6E2 | 1.3E3 | 6.0E2 | 1.5E3 | 1.3E1 | 6.4E1 | 7.8E3 | 5.2E3 | 905 | 13 | 337 | 13 | 0.67 |
| Om | pg/ml | 4.0E2 | 5.9E2 | 8.9E2 | 1.1E3 | 2.7E3 | 1.5E3 | 1.0E-9 | 1.0E2 | 5.1E4 | 5.8E3 | 905 | 13 | 337 | 13 | 0.63 |
| On | pg/ml | 1.8E2 | 5.1E2 | 3.0E2 | 5.7E2 | 4.9E2 | 4.9E2 | 1.0E-9 | 4.2E1 | 4.5E3 | 1.5E3 | 905 | 13 | 337 | 13 | 0.69 |
| Or | pg/ml | 1.4E1 | 1.5E1 | 3.8E1 | 2.8E1 | 7.3E1 | 3.9E1 | 1.0E-9 | 1.0E-9 | 5.1E2 | 1.1E2 | 317 | 7 | 187 | 7 | 0.53 |
| Ow | pg/ml | 3.6E1 | 1.5E1 | 1.5E2 | 7.1E1 | 5.6E2 | 1.5E2 | 1.0E-9 | 1.0E-9 | 8.1E3 | 4.0E2 | 317 | 7 | 187 | 7 | 0.37 |
| Ou | pg/ml | 4.9E2 | 9.7E2 | 1.0E3 | 2.8E3 | 1.6E3 | 3.3E3 | 1.0E-9 | 1.0E-9 | 9.8E3 | 7.5E3 | 317 | 7 | 187 | 7 | 0.70 |

Figure 19 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ul | ng/ml | 1.0E-9 | 1.0E-9 | 1.8E0 | 1.0E-9 | 8.3E0 | 0.0E0 | 1.0E-9 | 1.0E-9 | 1.0E2 | 1.0E-9 | 323 | 7 | 191 | 7 | 0.45 |
| Uo | ng/ml | 1.0E-9 | 1.0E-9 | 9.2E-2 | 8.3E-2 | 2.2E-1 | 2.2E-1 | 1.0E-9 | 1.0E-9 | 1.5E0 | 5.8E-1 | 323 | 7 | 191 | 7 | 0.44 |
| Uk | ng/ml | 1.0E-9 | 1.0E-9 | 7.6E-3 | 3.6E-4 | 2.5E-2 | 6.2E-4 | 1.0E-9 | 1.0E-9 | 3.2E-1 | 1.4E-3 | 323 | 7 | 191 | 7 | 0.39 |
| Um | ng/ml | 1.0E-9 | 1.0E-9 | 3.9E-1 | 4.0E-2 | 8.7E-1 | 1.0E-1 | 1.0E-9 | 1.0E-9 | 6.8E0 | 2.8E-1 | 323 | 7 | 191 | 7 | 0.37 |
| Uf | ng/ml | 6.0E-2 | 1.5E-1 | 1.7E-1 | 1.5E-1 | 6.0E-1 | 1.2E-1 | 1.0E-3 | 8.6E-3 | 8.6E0 | 3.7E-1 | 323 | 7 | 191 | 7 | 0.64 |
| Uh | ng/ml | 2.0E0 | 2.0E0 | 3.3E0 | 3.5E0 | 3.6E0 | 5.1E0 | 1.3E-2 | 6.3E-2 | 2.1E1 | 1.5E1 | 323 | 7 | 191 | 7 | 0.48 |
| Un | ng/ml | 1.9E0 | 3.0E0 | 2.2E0 | 3.4E0 | 1.8E0 | 2.1E0 | 1.3E-1 | 8.5E-1 | 2.5E1 | 7.4E0 | 323 | 7 | 191 | 7 | 0.71 |
| Ug | ng/ml | 1.5E1 | 2.4E0 | 2.9E1 | 9.5E0 | 3.1E1 | 1.1E1 | 6.9E-1 | 1.3E0 | 2.1E2 | 2.7E1 | 323 | 7 | 191 | 7 | 0.24 |
| Ur | ng/ml | 1.5E-1 | 1.0E-9 | 8.0E-1 | 3.0E-1 | 5.3E0 | 6.8E-1 | 1.0E-9 | 1.0E-9 | 9.3E1 | 1.8E0 | 322 | 7 | 190 | 7 | 0.30 |
| Up | ng/ml | 1.0E-9 | 1.0E-9 | 1.2E-2 | 6.5E-3 | 1.3E-1 | 1.3E-2 | 1.0E-9 | 1.0E-9 | 2.4E0 | 3.5E-2 | 322 | 7 | 190 | 7 | 0.51 |
| Us | ng/ml | 3.6E-3 | 1.0E-9 | 2.4E-2 | 1.1E-3 | 1.0E-1 | 1.8E-3 | 1.0E-9 | 1.0E-9 | 1.7E0 | 4.8E-3 | 322 | 7 | 190 | 7 | 0.30 |
| Uv | ng/ml | 2.9E-3 | 2.0E-3 | 1.3E-2 | 4.4E-3 | 4.4E-3 | 4.9E-3 | 1.0E-9 | 1.0E-9 | 4.3E-1 | 1.3E-2 | 322 | 7 | 190 | 7 | 0.49 |
| Ut | ng/ml | 6.5E-1 | 2.3E0 | 2.8E0 | 5.5E0 | 8.9E0 | 1.1E1 | 1.0E-9 | 6.8E-2 | 7.8E1 | 3.0E1 | 322 | 7 | 190 | 7 | 0.60 |
| Uu | ng/ml | 7.1E0 | 7.2E0 | 8.2E0 | 7.0E0 | 5.8E0 | 4.7E0 | 4.5E-1 | 2.3E0 | 4.0E1 | 1.5E1 | 322 | 7 | 190 | 7 | 0.45 |
| Vp | ng/ml | 1.0E-9 | 1.0E-9 | 4.8E-1 | 5.1E-2 | 4.2E0 | 1.3E-1 | 1.0E-9 | 1.0E-9 | 5.0E1 | 3.6E-1 | 323 | 7 | 191 | 7 | 0.50 |
| Vt | ng/ml | 6.7E0 | 9.8E0 | 9.6E0 | 1.2E1 | 1.2E1 | 1.3E1 | 4.3E-1 | 1.7E0 | 1.6E2 | 3.8E1 | 323 | 7 | 191 | 7 | 0.54 |
| Vo | ng/ml | 2.5E1 | 2.5E1 | 2.4E1 | 2.3E1 | 5.3E0 | 3.1E0 | 2.4E0 | 1.7E1 | 4.8E1 | 2.6E1 | 323 | 7 | 191 | 7 | 0.37 |
| Vv | ng/ml | 2.9E0 | 3.4E0 | 5.9E0 | 1.5E1 | 9.4E0 | 2.9E1 | 1.0E-9 | 1.0E-9 | 8.4E1 | 8.0E1 | 321 | 7 | 190 | 7 | 0.54 |
| Oy | pg/ml | 4.9E-1 | 4.7E-1 | 5.7E0 | 5.5E-1 | 2.9E1 | 5.6E-1 | 1.0E-9 | 1.0E-9 | 4.0E2 | 2.1E0 | 904 | 13 | 336 | 13 | 0.45 |
| Oz | pg/ml | 3.1E-3 | 1.4E-1 | 3.1E-1 | 1.8E-1 | 1.3E0 | 1.9E-1 | 1.0E-9 | 1.0E-9 | 2.9E1 | 6.2E-1 | 904 | 13 | 336 | 13 | 0.55 |
| Pa | pg/ml | 3.9E-1 | 3.5E-1 | 1.6E0 | 1.2E0 | 6.1E0 | 2.0E0 | 1.0E-9 | 1.0E-9 | 1.0E2 | 6.5E0 | 904 | 13 | 336 | 13 | 0.47 |
| Pb | pg/ml | 1.0E-9 | 1.0E-9 | 8.0E-1 | 6.0E-2 | 1.6E1 | 1.0E-1 | 1.0E-9 | 1.0E-9 | 4.9E2 | 3.2E-1 | 904 | 13 | 336 | 13 | 0.44 |
| Pc | pg/ml | 4.4E-2 | 1.4E-1 | 3.6E-1 | 2.1E-1 | 8.8E-1 | 2.6E-1 | 1.0E-9 | 1.0E-9 | 1.6E1 | 8.5E-1 | 904 | 13 | 336 | 13 | 0.47 |
| Pd | pg/ml | 1.9E0 | 2.1E0 | 5.1E0 | 3.3E0 | 2.9E1 | 5.2E0 | 1.0E-9 | 1.0E-9 | 8.4E2 | 2.0E1 | 904 | 13 | 336 | 13 | 0.48 |
| Pe | pg/ml | 2.2E1 | 5.1E1 | 1.2E2 | 1.2E2 | 4.4E2 | 1.5E2 | 1.0E-9 | 1.0E-9 | 6.7E3 | 4.4E2 | 904 | 13 | 336 | 13 | 0.55 |
| Pf | pg/ml | 1.6E0 | 6.6E0 | 1.1E1 | 8.6E0 | 6.0E1 | 9.6E0 | 1.0E-9 | 1.0E-9 | 1.5E3 | 2.9E1 | 904 | 13 | 336 | 13 | 0.58 |
| Pg | pg/ml | 3.4E0 | 4.0E0 | 4.3E1 | 9.9E1 | 3.4E2 | 3.3E2 | 1.0E-9 | 1.0E-9 | 7.7E3 | 1.2E3 | 904 | 13 | 336 | 13 | 0.49 |
| Ph | ng/ml | 1.8E-1 | 8.8E-1 | 3.6E-1 | 1.0E0 | 6.1E-1 | 8.4E-1 | 1.0E-9 | 1.9E-2 | 5.4E0 | 2.3E0 | 317 | 7 | 187 | 7 | 0.75 |
| Pi | ng/ml | 2.0E-1 | 3.1E-1 | 5.4E-1 | 3.1E-1 | 4.6E0 | 2.2E-1 | 1.0E-9 | 1.1E-2 | 8.2E1 | 5.3E-1 | 317 | 7 | 187 | 7 | 0.59 |
| Pj | ng/mL | 5.6E0 | 5.8E0 | 6.3E0 | 7.1E0 | 4.5E0 | 5.3E0 | 3.8E-2 | 1.3E0 | 3.1E1 | 1.7E1 | 317 | 7 | 187 | 7 | 0.55 |
| Pk | ng/ml | 8.8E-3 | 1.3E-2 | 1.8E-2 | 1.5E-2 | 8.7E-2 | 1.1E-2 | 1.0E-9 | 1.0E-9 | 1.5E0 | 2.8E-2 | 317 | 7 | 187 | 7 | 0.61 |
| aA | mg/dL | 8.0E-1 | 1.3E0 | 9.4E-1 | 1.4E0 | 4.9E-1 | 8.1E-1 | 2.0E-1 | 5.0E-1 | 4.2E0 | 3.4E0 | 2667 | 17 | 507 | 17 | 0.71 |
| aC | mg/mL | 2.8E0 | 2.4E0 | 3.1E0 | 2.9E0 | 1.4E0 | 1.3E0 | 7.7E-1 | 1.7E0 | 8.9E0 | 5.6E0 | 535 | 7 | 207 | 7 | 0.47 |
| aD | ug/mL | 3.2E0 | 3.7E0 | 4.5E0 | 5.3E0 | 3.8E0 | 3.8E0 | 4.3E-1 | 1.3E0 | 3.5E1 | 1.1E1 | 535 | 7 | 207 | 7 | 0.58 |
| aE | mg/mL | 5.6E-1 | 6.3E-1 | 5.7E-1 | 6.6E-1 | 1.5E-1 | 1.7E-1 | 1.8E-1 | 4.8E-1 | 1.1E0 | 1.0E0 | 535 | 7 | 207 | 7 | 0.65 |
| aF | ng/mL | 2.2E0 | 1.1E0 | 4.0E0 | 2.8E0 | 5.7E0 | 4.4E0 | 4.3E-1 | 3.5E-1 | 5.0E1 | 1.3E1 | 535 | 7 | 207 | 7 | 0.34 |
| aG | mg/mL | 1.4E-1 | 1.3E-1 | 1.6E-1 | 1.5E-1 | 8.7E-2 | 8.6E-2 | 1.7E-2 | 8.0E-2 | 5.4E-1 | 3.3E-1 | 535 | 7 | 207 | 7 | 0.49 |
| aH | ug/mL | 7.5E1 | 6.3E1 | 8.2E1 | 8.0E1 | 4.4E1 | 4.3E1 | 4.6E0 | 3.6E1 | 2.9E2 | 1.5E2 | 535 | 7 | 207 | 7 | 0.48 |
| aI | ug/mL | 1.9E2 | 1.6E2 | 1.9E2 | 1.7E2 | 6.0E1 | 5.0E1 | 2.8E1 | 1.1E2 | 3.7E2 | 2.6E2 | 535 | 7 | 207 | 7 | 0.40 |
| aJ | ug/mL | 2.5E0 | 4.6E0 | 3.1E0 | 5.8E0 | 2.2E0 | 3.6E0 | 7.3E-1 | 1.9E0 | 1.7E1 | 1.1E1 | 535 | 7 | 207 | 7 | 0.75 |
| aK | ng/mL | 1.6E0 | 1.6E0 | 2.4E0 | 1.8E0 | 2.6E0 | 1.5E0 | 2.9E-4 | 2.1E-1 | 1.8E1 | 5.0E0 | 535 | 7 | 207 | 7 | 0.48 |
| aL | mg/mL | 8.0E-1 | 8.3E-1 | 8.1E-1 | 7.7E-1 | 2.6E-1 | 1.9E-1 | 1.9E-1 | 4.0E-1 | 1.7E0 | 9.9E-1 | 535 | 7 | 207 | 7 | 0.48 |
| aM | U/mL | 2.2E1 | 1.9E1 | 4.9E1 | 2.4E1 | 1.1E2 | 1.5E1 | 4.2E-2 | 5.8E0 | 1.6E3 | 5.2E1 | 535 | 7 | 207 | 7 | 0.46 |
| aN | U/mL | 1.4E1 | 1.7E1 | 2.2E1 | 1.8E1 | 3.1E1 | 1.2E1 | 2.5E-3 | 3.9E0 | 3.8E2 | 3.7E1 | 535 | 7 | 207 | 7 | 0.52 |
| aO | pg/mL | 3.1E1 | 1.8E2 | 3.0E2 | 4.4E2 | 7.8E2 | 8.6E2 | 6.0E-2 | 1.2E1 | 6.6E3 | 2.4E3 | 535 | 7 | 207 | 7 | 0.68 |
| aP | ng/mL | 1.7E0 | 2.4E0 | 2.1E0 | 3.0E0 | 1.8E0 | 1.6E0 | 4.5E-1 | 1.3E0 | 2.8E1 | 5.3E0 | 535 | 7 | 207 | 7 | 0.71 |
| aQ | ng/mL | 3.0E-1 | 2.3E-1 | 4.5E-1 | 3.3E-1 | 4.5E-1 | 2.7E-1 | 2.0E-4 | 6.1E-2 | 4.0E0 | 7.8E-1 | 535 | 7 | 207 | 7 | 0.43 |
| aR | ng/mL | 1.7E0 | 2.6E0 | 2.8E0 | 3.1E0 | 3.3E0 | 1.7E0 | 1.8E-1 | 3.6E-1 | 3.4E1 | 5.4E0 | 535 | 7 | 207 | 7 | 0.65 |
| aS | ng/mL | 2.6E-1 | 1.2E0 | 6.3E-1 | 2.0E0 | 1.7E0 | 3.0E0 | 4.2E-3 | 8.5E-2 | 3.3E1 | 8.7E0 | 535 | 7 | 207 | 7 | 0.70 |
| aU | pg/mL | 7.5E1 | 1.0E2 | 1.3E2 | 1.0E2 | 1.5E2 | 6.1E1 | 7.4E-2 | 1.3E1 | 1.3E3 | 1.9E2 | 535 | 7 | 207 | 7 | 0.52 |
| aV | ng/mL | 6.2E-1 | 3.6E-1 | 1.1E0 | 6.6E-1 | 1.8E0 | 5.3E-1 | 7.6E-4 | 1.8E-1 | 3.3E1 | 1.5E0 | 535 | 7 | 207 | 7 | 0.44 |
| aW | pg/mL | 1.9E1 | 2.0E1 | 2.0E1 | 4.9E1 | 1.8E1 | 7.9E1 | 7.2E-2 | 7.2E-2 | 2.4E2 | 2.3E2 | 535 | 7 | 207 | 7 | 0.61 |
| aX | ng/mL | 9.5E0 | 1.2E1 | 1.5E1 | 3.9E1 | 1.8E1 | 7.7E1 | 3.0E-1 | 2.5E0 | 2.2E2 | 2.1E2 | 535 | 7 | 207 | 7 | 0.55 |
| aY | ng/mL | 5.7E1 | 1.1E2 | 7.5E1 | 1.6E2 | 8.1E1 | 1.2E2 | 4.1E-1 | 4.7E1 | 1.2E3 | 3.9E2 | 535 | 7 | 207 | 7 | 0.76 |
| aZ | pg/mL | 2.2E2 | 2.2E2 | 5.0E2 | 7.7E2 | 9.5E2 | 8.4E2 | 1.7E0 | 4.6E1 | 1.2E4 | 2.1E3 | 535 | 7 | 207 | 7 | 0.61 |
| bA | ng/mL | 8.8E0 | 9.0E1 | 3.5E1 | 2.0E2 | 9.7E1 | 2.2E2 | 3.0E-2 | 1.4E1 | 9.4E2 | 5.7E2 | 535 | 7 | 207 | 7 | 0.89 |
| bB | ng/mL | 3.0E2 | 1.9E2 | 3.2E2 | 3.2E2 | 1.7E2 | 2.2E2 | 2.1E0 | 1.1E2 | 1.0E3 | 6.2E2 | 535 | 7 | 207 | 7 | 0.46 |

Figure 19 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| bC | ng/mL | 3.5E2 | 3.6E2 | 6.1E2 | 7.5E2 | 8.1E2 | 9.8E2 | 9.8E0 | 1.4E2 | 4.7E3 | 2.9E3 | 535 | 7 | 207 | 7 | 0.56 |
| bE | mg/mL | 5.5E0 | 6.7E0 | 5.8E0 | 7.6E0 | 2.1E0 | 3.3E0 | 9.8E-1 | 3.7E0 | 1.3E1 | 1.3E1 | 535 | 7 | 207 | 7 | 0.66 |
| bF | pg/mL | 2.1E1 | 2.3E1 | 1.6E2 | 2.9E2 | 8.9E2 | 7.0E2 | 5.0E-2 | 9.4E0 | 1.1E4 | 1.9E3 | 535 | 7 | 207 | 7 | 0.55 |
| bG | ng/mL | 1.6E0 | 1.9E0 | 2.7E0 | 2.2E0 | 3.2E0 | 1.8E0 | 2.2E-2 | 4.0E-1 | 2.6E1 | 4.8E0 | 535 | 7 | 207 | 7 | 0.51 |
| bH | pg/mL | 5.7E-1 | 6.8E0 | 4.8E0 | 5.6E0 | 1.4E1 | 5.8E0 | 5.7E-1 | 5.7E-1 | 2.8E2 | 1.7E1 | 535 | 7 | 207 | 7 | 0.60 |
| bI | ng/mL | 4.0E-3 | 1.4E-1 | 6.2E-2 | 2.0E-1 | 1.6E-1 | 2.8E-1 | 4.0E-3 | 4.0E-3 | 1.3E0 | 7.7E-1 | 535 | 7 | 207 | 7 | 0.70 |
| bJ | mg/mL | 2.3E0 | 2.6E0 | 2.7E0 | 2.8E0 | 2.1E0 | 9.7E-1 | 2.5E-4 | 1.3E0 | 1.3E1 | 4.0E0 | 535 | 7 | 207 | 7 | 0.59 |
| bL | pg/mL | 3.7E0 | 5.8E0 | 8.1E0 | 9.4E0 | 1.0E1 | 1.1E1 | 4.6E-2 | 4.6E-2 | 8.0E1 | 3.2E1 | 535 | 7 | 207 | 7 | 0.59 |
| bM | mg/mL | 1.7E0 | 2.0E0 | 2.1E0 | 2.1E0 | 1.5E0 | 8.6E-1 | 9.2E-3 | 1.2E0 | 8.9E0 | 3.7E0 | 535 | 7 | 207 | 7 | 0.56 |
| bN | ng/mL | 4.5E1 | 2.7E1 | 1.3E2 | 3.1E1 | 2.8E2 | 2.2E1 | 1.4E-1 | 2.9E0 | 1.9E3 | 6.2E1 | 535 | 7 | 207 | 7 | 0.37 |
| bO | ng/mL | 4.0E-2 | 4.0E-2 | 1.1E1 | 3.0E0 | 2.5E1 | 6.2E0 | 4.0E-2 | 4.0E-2 | 2.0E2 | 1.7E1 | 535 | 7 | 207 | 7 | 0.43 |
| bP | mg/mL | 5.4E-1 | 1.0E0 | 7.7E-1 | 1.0E0 | 6.8E-1 | 9.5E-1 | 4.9E-2 | 9.7E-2 | 4.8E0 | 2.9E0 | 535 | 7 | 207 | 7 | 0.57 |
| bQ | pg/mL | 1.6E1 | 1.5E1 | 5.8E1 | 3.7E1 | 5.9E2 | 3.3E1 | 1.5E-1 | 4.4E0 | 1.3E4 | 8.8E1 | 535 | 7 | 207 | 7 | 0.59 |
| bR | ng/mL | 1.2E-2 | 1.2E-2 | 1.3E-1 | 4.2E-2 | 4.2E-1 | 8.0E-2 | 1.2E-2 | 1.2E-2 | 8.7E0 | 2.2E-1 | 535 | 7 | 207 | 7 | 0.38 |
| bS | pg/mL | 9.4E-1 | 9.4E-1 | 6.8E0 | 9.4E-1 | 2.6E1 | 0.0E0 | 9.4E-1 | 9.4E-1 | 3.9E2 | 9.4E-1 | 535 | 7 | 207 | 7 | 0.43 |
| bU | ng/mL | 1.2E-1 | 1.2E-1 | 1.9E-1 | 1.2E-1 | 3.5E-1 | 1.2E-1 | 1.3E-2 | 1.3E-2 | 6.6E0 | 3.4E-1 | 535 | 7 | 207 | 7 | 0.44 |
| bV | pg/mL | 4.7E2 | 1.0E3 | 5.6E2 | 9.3E2 | 5.6E2 | 4.2E2 | 1.5E2 | 3.7E2 | 1.2E4 | 1.6E3 | 535 | 7 | 207 | 7 | 0.77 |
| bW | pg/mL | 3.3E2 | 3.7E2 | 6.1E2 | 4.2E2 | 1.7E3 | 2.2E2 | 8.4E1 | 1.8E2 | 2.5E4 | 8.4E2 | 535 | 7 | 207 | 7 | 0.54 |
| bX | ng/mL | 1.4E-3 | 2.5E-5 | 2.8E-3 | 4.5E-4 | 3.4E-3 | 1.1E-3 | 2.5E-5 | 2.5E-5 | 2.0E-2 | 3.0E-3 | 535 | 7 | 207 | 7 | 0.29 |
| bZ | pg/mL | 2.4E2 | 2.8E2 | 8.3E2 | 9.5E2 | 3.7E3 | 1.2E3 | 1.5E-1 | 2.6E2 | 5.8E4 | 3.4E3 | 535 | 7 | 207 | 7 | 0.69 |
| cA | pg/mL | 6.0E-1 | 6.0E-1 | 2.6E0 | 6.0E-1 | 1.6E1 | 0.0E0 | 6.0E-1 | 6.0E-1 | 3.7E2 | 6.0E-1 | 535 | 7 | 207 | 7 | 0.44 |
| cB | ng/mL | 5.7E-2 | 5.3E-2 | 8.8E-2 | 5.4E-2 | 1.0E-1 | 4.1E-2 | 1.7E-3 | 1.7E-3 | 5.7E-1 | 1.2E-1 | 535 | 7 | 207 | 7 | 0.44 |
| cC | pg/mL | 4.6E1 | 3.4E1 | 4.7E1 | 3.9E1 | 3.9E1 | 1.6E1 | 1.0E0 | 2.1E1 | 4.5E2 | 5.8E1 | 535 | 7 | 207 | 7 | 0.44 |
| cD | pg/mL | 5.3E0 | 3.1E0 | 1.5E1 | 8.8E0 | 5.2E1 | 1.4E1 | 3.3E-1 | 3.3E-1 | 7.2E2 | 3.9E1 | 535 | 7 | 207 | 7 | 0.42 |
| cE | pg/mL | 3.8E1 | 9.1E1 | 1.6E2 | 1.5E2 | 4.6E2 | 1.7E2 | 1.2E-1 | 6.4E0 | 3.8E3 | 4.5E2 | 535 | 7 | 207 | 7 | 0.58 |
| cF | pg/mL | 1.2E1 | 5.3E-1 | 2.0E1 | 5.9E0 | 3.0E1 | 7.1E0 | 5.3E-1 | 5.3E-1 | 2.7E2 | 1.7E1 | 535 | 7 | 207 | 7 | 0.35 |
| cG | pg/mL | 4.6E1 | 6.5E1 | 1.0E2 | 1.0E2 | 4.8E2 | 1.1E2 | 6.4E0 | 2.0E1 | 1.0E4 | 3.3E2 | 535 | 7 | 207 | 7 | 0.61 |
| cH | uIU/mL | 2.8E0 | 1.6E0 | 6.0E0 | 4.0E0 | 1.2E1 | 5.7E0 | 8.6E-3 | 8.6E-3 | 1.6E2 | 1.6E1 | 535 | 7 | 207 | 7 | 0.39 |
| cI | ng/mL | 5.7E0 | 1.0E1 | 1.2E1 | 4.4E1 | 1.6E1 | 6.9E1 | 1.0E-3 | 7.9E-1 | 1.2E2 | 1.9E2 | 535 | 7 | 207 | 7 | 0.64 |
| cJ | ug/mL | 6.2E1 | 7.6E1 | 1.1E2 | 7.9E1 | 1.4E2 | 4.7E1 | 4.0E0 | 1.8E1 | 9.6E2 | 1.6E2 | 535 | 7 | 207 | 7 | 0.52 |
| cK | ng/mL | 3.8E-3 | 3.8E-3 | 4.8E-2 | 1.4E-2 | 1.7E-1 | 2.6E-2 | 3.8E-3 | 3.8E-3 | 1.7E0 | 7.3E-2 | 535 | 7 | 207 | 7 | 0.49 |
| cL | pg/mL | 2.0E2 | 2.2E2 | 3.8E2 | 2.9E2 | 1.2E3 | 2.6E2 | 1.6E1 | 1.2E2 | 2.4E4 | 8.7E2 | 535 | 7 | 207 | 7 | 0.55 |
| cM | pg/mL | 2.7E2 | 2.1E2 | 2.9E2 | 2.5E2 | 1.9E2 | 1.3E2 | 8.7E0 | 1.2E2 | 1.6E3 | 4.9E2 | 535 | 7 | 207 | 7 | 0.42 |
| cN | pg/mL | 1.2E2 | 1.7E2 | 1.3E2 | 1.7E2 | 6.2E1 | 6.2E1 | 3.8E1 | 1.0E2 | 1.1E3 | 2.8E2 | 535 | 7 | 207 | 7 | 0.73 |
| cO | pg/mL | 2.2E2 | 2.4E2 | 3.0E2 | 2.7E2 | 8.5E2 | 8.3E1 | 5.4E1 | 1.7E2 | 1.9E4 | 3.9E2 | 535 | 7 | 207 | 7 | 0.61 |
| cP | ng/mL | 2.5E3 | 3.8E3 | 2.6E3 | 3.8E3 | 9.0E2 | 1.0E3 | 6.2E2 | 2.3E3 | 5.7E3 | 5.1E3 | 535 | 7 | 207 | 7 | 0.82 |
| cQ | ng/mL | 4.9E-2 | 1.9E-1 | 1.4E-1 | 3.3E-1 | 2.8E-1 | 3.1E-1 | 2.0E-3 | 6.7E-2 | 2.2E0 | 9.3E-1 | 535 | 7 | 207 | 7 | 0.80 |
| cR | ng/mL | 2.9E2 | 6.9E2 | 5.0E2 | 6.8E2 | 7.8E2 | 2.4E2 | 2.0E1 | 3.4E2 | 8.9E3 | 1.0E3 | 535 | 7 | 207 | 7 | 0.77 |
| cS | ng/mL | 2.6E2 | 6.1E2 | 3.8E2 | 5.6E2 | 3.8E2 | 2.2E2 | 4.1E1 | 2.4E2 | 2.7E3 | 8.7E2 | 535 | 7 | 207 | 7 | 0.77 |
| cT | ng/mL | 3.3E1 | 1.5E2 | 8.7E1 | 4.0E2 | 1.9E2 | 4.3E2 | 3.6E0 | 1.8E1 | 2.1E3 | 1.2E3 | 535 | 7 | 207 | 7 | 0.81 |
| cU | ng/mL | 5.4E1 | 8.0E1 | 7.5E1 | 8.9E1 | 9.4E1 | 4.5E1 | 5.4E0 | 5.2E1 | 1.6E3 | 1.8E2 | 535 | 7 | 207 | 7 | 0.67 |
| cV | ng/mL | 1.8E-1 | 1.1E-1 | 3.9E-1 | 1.8E-1 | 2.1E0 | 1.2E-1 | 3.4E-4 | 7.6E-2 | 4.7E1 | 3.8E-1 | 535 | 7 | 207 | 7 | 0.44 |
| cW | mIU/mL | 5.2E-2 | 6.5E-2 | 1.3E-1 | 9.2E-2 | 6.5E-1 | 6.4E-2 | 3.7E-4 | 4.0E-2 | 9.7E0 | 2.0E-1 | 535 | 7 | 207 | 7 | 0.63 |
| cX | ng/mL | 1.1E-1 | 3.2E-2 | 1.3E0 | 5.4E-1 | 4.2E0 | 9.0E-1 | 2.3E-4 | 1.4E-2 | 2.8E1 | 2.5E0 | 535 | 7 | 207 | 7 | 0.49 |
| cY | ng/mL | 8.6E0 | 1.0E1 | 1.3E1 | 1.1E1 | 1.3E1 | 9.1E0 | 1.5E-1 | 6.6E-1 | 8.3E1 | 2.3E1 | 535 | 7 | 207 | 7 | 0.48 |
| cZ | ug/mL | 1.5E1 | 1.5E1 | 1.6E1 | 1.9E1 | 7.2E0 | 1.0E1 | 2.3E0 | 8.0E0 | 5.7E1 | 4.0E1 | 535 | 7 | 207 | 7 | 0.58 |
| dA | pg/mL | 3.3E2 | 5.4E2 | 3.7E2 | 5.3E2 | 2.9E2 | 1.5E2 | 9.0E1 | 3.2E2 | 5.8E3 | 7.7E2 | 535 | 7 | 207 | 7 | 0.80 |
| dB | ug/mL | 1.7E1 | 1.9E1 | 1.7E1 | 1.8E1 | 1.5E1 | 8.4E0 | 9.4E-1 | 2.8E0 | 2.5E2 | 2.9E1 | 535 | 7 | 207 | 7 | 0.60 |
| dC | nmol/L | 3.5E1 | 4.0E1 | 3.9E1 | 4.2E1 | 1.8E1 | 1.8E1 | 7.6E0 | 2.2E1 | 1.4E2 | 7.5E1 | 535 | 7 | 207 | 7 | 0.57 |
| dD | ug/mL | 3.6E1 | 3.3E1 | 3.7E1 | 3.4E1 | 1.1E1 | 1.4E1 | 1.3E1 | 1.5E1 | 7.6E1 | 6.2E1 | 535 | 7 | 207 | 7 | 0.40 |
| dE | ng/mL | 4.7E-1 | 4.2E-1 | 5.9E-1 | 6.4E-1 | 6.9E-1 | 8.1E-1 | 8.4E-3 | 8.4E-3 | 7.2E0 | 2.4E0 | 535 | 7 | 207 | 7 | 0.49 |
| dF | ng/mL | 2.3E2 | 3.5E2 | 2.8E2 | 3.7E2 | 2.0E2 | 2.2E2 | 5.6E1 | 1.3E2 | 1.3E3 | 7.8E2 | 535 | 7 | 207 | 7 | 0.65 |
| dG | ng/mL | 1.1E1 | 1.4E1 | 1.5E1 | 1.9E1 | 1.3E1 | 8.7E0 | 2.2E0 | 9.2E0 | 1.8E2 | 3.2E1 | 535 | 7 | 207 | 7 | 0.70 |
| dH | pg/mL | 7.7E0 | 8.0E0 | 1.3E1 | 1.0E1 | 3.6E1 | 7.7E0 | 4.0E-2 | 2.2E0 | 6.7E2 | 2.3E1 | 535 | 7 | 207 | 7 | 0.54 |
| dI | pg/mL | 4.6E-1 | 2.1E0 | 2.8E0 | 2.8E0 | 1.5E1 | 2.9E0 | 4.6E-1 | 4.6E-1 | 3.3E2 | 7.5E0 | 535 | 7 | 207 | 7 | 0.68 |
| dJ | ng/mL | 1.9E0 | 2.1E0 | 2.1E0 | 2.2E0 | 1.2E0 | 1.0E0 | 3.2E-2 | 7.9E-1 | 6.9E0 | 3.4E0 | 535 | 7 | 207 | 7 | 0.53 |
| dK | uIU/mL | 1.9E0 | 1.4E0 | 3.1E0 | 1.5E0 | 6.1E0 | 1.1E0 | 2.8E-4 | 4.2E-2 | 7.9E1 | 3.1E0 | 535 | 7 | 207 | 7 | 0.39 |

Figure 19 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| dL | ng/mL | 8.8E2 | 1.2E3 | 1.0E3 | 1.1E3 | 5.7E2 | 1.9E2 | 2.6E2 | 7.5E2 | 4.8E3 | 1.3E3 | 535 | 7 | 207 | 7 | 0.64 |
| dM | pg/mL | 9.7E2 | 2.5E2 | 1.3E3 | 2.5E2 | 1.3E3 | 1.8E3 | 3.4E2 | 7.3E2 | 1.6E4 | 5.9E3 | 535 | 7 | 207 | 7 | 0.75 |
| dN | ug/mL | 9.3E1 | 1.4E2 | 1.0E2 | 1.3E2 | 4.0E1 | 4.6E1 | 1.6E1 | 6.9E1 | 3.3E2 | 1.9E2 | 535 | 7 | 207 | 7 | 0.72 |
| dR | pg/ml | 1.6E3 | 1.6E3 | 2.3E3 | 2.7E3 | 2.3E3 | 2.9E3 | 1.4E2 | 4.8E2 | 1.5E4 | 8.7E3 | 365 | 7 | 197 | 7 | 0.52 |
| eF | ng/ml | 4.1E0 | 6.9E0 | 5.0E0 | 7.2E0 | 4.0E0 | 2.4E0 | 1.2E0 | 4.1E0 | 4.6E1 | 1.2E1 | 380 | 7 | 198 | 7 | 0.81 |
| fP | ng/ml | 2.6E2 | 3.3E2 | 2.9E2 | 3.6E2 | 1.7E2 | 9.4E1 | 1.8E0 | 2.4E2 | 1.0E3 | 4.8E2 | 346 | 7 | 189 | 7 | 0.68 |
| gL | pg/ml | 6.5E4 | 1.1E5 | 7.0E4 | 1.1E5 | 2.9E4 | 5.2E4 | 1.4E4 | 5.2E4 | 2.0E5 | 1.7E5 | 365 | 7 | 197 | 7 | 0.74 |
| gP | U/ml | 2.7E2 | 2.6E2 | 2.8E2 | 2.8E2 | 1.1E2 | 7.2E1 | 1.2E1 | 2.0E2 | 1.1E3 | 3.8E2 | 376 | 7 | 198 | 7 | 0.51 |
| gW | ng/ml | 6.1E2 | 8.2E2 | 1.2E3 | 1.3E3 | 1.6E3 | 1.8E3 | 3.1E-1 | 3.1E2 | 9.5E3 | 5.4E3 | 318 | 7 | 187 | 7 | 0.57 |

Analyte panel data:

Unconstrained panels with 3 analytes, where 1.0E-8 >= 'model p-value' > 0. Contains 1 panels of 6,910,825 total panels evaluated. : AfNiSt Unconstrained panels with 3 analytes, where 1.0E-7 >= 'model p-value' > 1.0E-8. Contains 28 panels of 6,910,825 total panels evaluated. :
Ni{St(Bn Ii Il Io Qn) bA(cV Jo Mb Oy) Af(aA Mu Nw) Qw(bV Rf) BnMu MbbV NxaA} Mu{Bn(cP Iq) AfIl CsHa} Nb{cQ(Oy Us)} Qd{liNx IqOk} AfQwKq NkNxaA UpUsbA Unconstrained panels with 3 analytes, where 1.0E-6 >= 'model p-value' > 1.0E-7. Contains 480 panels of 6,910,825 total panels evaluated. :
Ni{bA(Af As aY bE bJ BN bQ Cq Ct Cw Dd Fp Gl Ha Hr Hv Hw Hx Ib Ii Ij Il In Io Iq Jn Jr Js Jt Kc Kr Lh Ly Mc Me Mn Mq Mr Na Nd Nf Nm Of Pb Pd Pe Pg Po Qa Qw Rf Rj Sr St Uc Ue Us Uv Vp) bV(Ad aM As bJ BN cC Cq cV Cw Dd dG dL Gp Hr Hv Hw Ij Il In Io Jo Js Jt Kc Ue Ug Uh Us) In(aY cI cP CS Kc Nx Ou Ph Rh Ub) aA(As BN cV Cx Iv Kc Mr Qw Us) aY(Kc Ly Mb Mu Nf Nw Rf Vv) Ih(Af BN Qw Ue Us) Kc(bN cP cQ cR Mc Ub) Jo(Cs cT Kf Nx Rf) Mc(Bo cT gL Ky) Rf(bN gW Qv Us) Bn(Kq Lx Nw) Mb(cQ cT gL) Qw(dA Qd Ub) Af(Kq Lx) Mu(aF Dk) Nx(Ii Jj) bN(Nc Ub) cT(cV Oy) dA(Ly Nf) UcKq IqQd OwOu} Mu{Bn(Ao Ar aW aY bA bN cI cQ cT Dd Ii Il Io Iv Kc Kk Kp Ly Mc Mr Nb Nq Ou Oy Ph Qv Qw Rb Vv) Af(bN bR bW cP Iq Iv Jk Mb Mp Nd Nk Oy Qv Qw Uk Um Us Uv) Qw(aF Ao aY Ii Il Kk) Uc(bA Kf Kp Kq) Oy(cP Kk Kp Nx) AoVv AxHa NbIb JkcP UvbA aFcQ} Kq{Uc(Af Ao aY BA Bn cI cP cQ cT eF GI Hb Hc Ii Il Io Iq Jq Kp My Nb Ny Pg Qv Rb Sr Uh Vv) Bn(aW aY bA cI cP cQ Ii Il Iq Qv Qw Rb Uh) Af(Io Kr Rj Us Vp Vv) Us(bA Nb) IiQw UvbA} Nb{Us(aY bA bV cT dA eF In Io Kp Lv Mi Nc Ne Ri) cQ(Af Bn Ib Jo Kj Mb Nf Of Qw Uc) Jo(aY bA cT eF Kf Kp Qw) Oy(bA cP eF Kc Kp Qy) Qw(aY bV Ub) bA(Nd Uc Uv) aY(As In)} aA{Nx(Af Ii Il In Iq Jj Jo Js Mx Nf Nm Nr Ny Oy Pf) Af(Io Iq Kc Ly Qw Rf Rh Us Vv) Nk(Iv Lv Mb Qd) Qw(aF cQ Cx) Io(BN) IqQd UpUs} bA{Io(Af In Ly Oy Pg Qw Rf Ub) Qw(Af cQ dA Oy Sr Ub Us) Rf(Af Ha Ii Mn Ny Sr Us) Jy(Bn Uc Uv) Us(Ly Qd Rb) AfRb LyPg IqSt KkOy aYcV} Qd{Iq(Aa Il In Iv Jj Lv Nk Nr Nx) Nx(Il In Jo Js) Nk(Il Im Lz)} Kk{Oy(Ba eF Jh Qy) InaY QwcQ QvbE JocF} Qw{Rf(aY cQ) AoJh IocT UsbV} Nx{Nk(Ii Jo) FrOy Inlv JoOk} Nw{cQ(Af Bn Cx) BncP} AfQvgL BnJycP UpUscT Unconstrained panels with 3 analytes, where 1.0E-5 >= 'model p-value' > 1.0E-6. Contains 6,261 panels of 6,910,825 total panels evaluated. :
Ni{bA(aA aC AD aE aF aG aH al AJ aK AL aM AN AO AP aQ AR aS aU aV AW aX aY aZ Ba BB BC bF BG bH bI bL bM BO bP bR bS bU bV bW bX bZ cA cB cC cD cE cF cG CH cl cJ cK cL cM cN CO CP cQ cR CS cT CU Cv cW CX cY cZ dA dB DC dD DE dF DG dH DI dJ DK DL dM dN dR Ef Et Fa Fn Fr Fw gL Gp gW Hq Hu Ic Id Ih Ik Im Ip Ir Is It Iu Iv Jd Je Jg Jh Ji Jj Jk Jl Jm Jp Jq Ju Jv Jy Kd Ke Kg Kj Kk Kn Ko Kp Kq Ky Kz Li Lj Lu Lv Lw Lx Lz Ma Md Mf Mg Mh Mi Mj Mk Ml Mm Mp Ms Mt Mu Mv Mw Mx My Mz Nb Nc Ne Ng Nh Nj Nk Nl Nn No Nq Nr Ns Nt Nu Nv Nw Nx Ny Oa Oe Og Oh Oi Ok Om On Or Ow Oz Pa Pc Pf Pi Pk Pz Qb Qc Qd Qe Ql Qm Qn Qt Qu Qv Qx Qy Qz Ra Rb Rg Rh Ss Tz Ub Ud Uf Ug Uh Uk Ul Um Un Up Ur Ut Uu Uv Vo Vp Vt Vv Wm Tj) St(aA aC aD aE aF aH aK aM AN aO aP Ar aU aV AW aX aY aZ Ba BB Bc bE bI bJ Bo bQ bR bS bV bW bX cC cE cG Ch cl cN CP CQ cR CT Cu Cw cZ dA dB DC Dd DE dF dG dH DI dJ DL dN dR Et Fn Fp Fr Fw Gp gW Ha Hq Hr Hu Hv Hw Ib Ic Id Ih Ii Ij Ik Il Im In Io Ip Iq Ir Is It Iu Jg Jh Ji Jj Jk Jl Jm Jn Jo Jp Jr Js Jt Kd Ke Kg Kj Kn Ko Kp Kq Kr Kz Lu Lv Lw Lx Ly Lz Ma Mb Mc Md Me Mf Mg Mh Mi Mj Mk Ml Mm Mn Mp Mq Ms Mt Mu Mv Mw Mx My Mz Na Nb Nc Nd Ne Nf Ng Nh Nj Nk Nl Nm Nn No Nq Nr Ns Nt Nu Nv Nw Ny Oe Of Og Oh Oi Ok Om On Or Oy Oz Pa Pb Pc Pd Pe Pf Pg Pi Pk Po Qb Qc Qd Qe Ql Qn Qv Qx Ra Rb Rf Rh Rj Sr Ub Uc Ud Ue Ug Uk Ul Um Up Uv Vp Vv Tj) Kc(aC aE Af al AJ aM aN AO aP AR aS aW AX aY aZ Ba Bb bE bl bJ bL Bn bO bP bR bS bW bX bZ cA cC cF CH cl cJ cN cO CS CT CU cV cW Cx dA dB Dd dE dG dH dI dK dM dN Dp Ed eF Ez Fa Fb fP Fr gL Gp gW Hc Hv Hw Ic Ih Ii Il Im Io Is Iv Jd Jf Jj Jl Jm Jn Jo Jp Jv Jy Kd Kg Kj Kk Kq Kr Ky Li Lj Lu Lv Lx Ly Ma Mb Mi Mk Mp Mr Mu Mw My Nb Nc Nf Ng Nk No Ns Nt Nw Nx Oa Oe Oh Om On Ou Ow Oy Pa Pb Pc Pg Ph Pi Po Qa Qb Qd Qe Ql Qn Qt Qv Qw Qy Ra Rb Rf Rh Rj Rm Sr Tz Ua Ue Ug Un Ur Us Ut Uu Vv Tj) aY(Ad Af AJ aM AN Ar AS aX Ba Bc bE bJ BN Bo bQ bR bS bV bW bX cC Ch cl cN CP CQ cR CT Cu cV Cw cx cZ dA Dc Dd DE dG dl DL Fp Fw gL Gp Hr Hv Hw Hx Ib Ih Ii Ij Il Im Io Iq Ir Iv Jj Jn Jo Jr Js Jt Jy Kj Kk Kn Kr Ky Kz Ld Lh Lv Lx Mc Md Me Mj Ml Mq Mr Ms Mx Mz Na Nb Nc Nd Ne Nj Nk Nl Nm No Nq Nr Nx Of Og Oh Om Ow Oy Oz Pb Pd Pe Pg Pi Qa Qd Qv Qw Qy Rb Rh Rj Sr Ub Uc Ug Uk Ul Um Ur Us Uv Tj) bV(aE AF Aj aK AN aS aU aW aZ Ba BB BC bE Bo bQ bS bW bX cG cl cP cQ cR CT Cu Cx cZ dA dB Dc DE dF DI dJ Dl Fn Fp Fw gL Ha Hx Ib Id Ih Ii Im Iq Ir Is It Iv Ji Jn Jq Jr Kd Ke Kg Kj Kk Kn Ko Kp Kq Kz Li Lw Md Mf Ml Mn Mq Ms Mu Mw Mx Mz Nb Nc Ng Nj Nk Nr Ns Nt Nw Nx Ny Og Ok Om Or Ow Oz Pc Pd Pe Pf Pg Pi Pk Po Qa Ql Qv Qx Ra Rb Rf Rj Sr Ub Uc Ud Ue Ug Uk Ul Un Up Ur Uv Vp Vt Tj) In(aE AF aJ Al aN aO aP Ar AS AW AX aZ Ba Bc bE bl bJ BN Bo bP bR bS bX cA cC cF Ch cN Cp cQ cR cT CU cV cW Cx dA DC dE dI dK dM dN eF Fn gL Gp gW Hc Hf Ic Ih Ir Is Iv Ji Kf Kk Kp Kq Ky Kz Oa Ok Or Pi Qd Qt Qv Qw Qy Ra Rb Rf Rg Rj Rm Sr Uc Ug Um Un Ur Us Ut Vv) cT(Af Aj As bE bJ BN bQ cl CQ Ct Cw dA Dd Ha Hr Hv Hw Hx Ib Ih Ii Ij Il Io Iq Jn Jr Js Jt Kj Kk Kr Kz Lh Ly Mc Mn Mq Mr Ms Na Nc Nd Nf Nk

Or Ow Oz Pa Pb Pc Pd Pe Pf Pg Pi Pj Pk Po Pz Qa Qb Qc Qd Qe Qg Qh Ql Qm Qn Qt Qu Qx Qy Qz Ra Rc Rf Rg Rh Ri Rj Rm Sr Ss St Tz Ua Ub Uc Ud Ue Uf Ug Uh Uk Ul Um Un Uo Up Ur Us Ut Uu Uv Vo Vp Vt Wm Tj) Af(aE aF Ao Ar As aV aW bF BG bJ bQ bS bU bV bX bZ cA cC cD cE cF cG Ch cI cK cL CO CQ cR CT cU dA dF dG dH dI gL Gp Ha Hq Hr Ib Ii In Io Jj Jl Jo Kc Kj Kk Kp Kr Ly Lz Ma Mc Md Mi Mk Mm Mn Mr Mt Nb Nq Ns Nw Nx Of Ok Or Ow Oz Pa Pb Pd Pe Pf Pg Po Rb Rf Rg Rh Uc Uf Ul Ur Vp Tj) Qw(Al aO aW Bb bF Bg bV cE cG Ch cl Co cQ Cs dA De Dk Ha Hc Hq Hr Hu Ib Io Iq Iu Jd Je Jk Jo Kc Kj Kp Md Mw My Nd Nq Nv Of Om Ou Oy Pd Pg Qd Qv Rf Ub Uc Uh Us Ut Uv) Ao(aF Ar bN cI cP cR Cx Gp li Il In Iq Jk Kc Kk Lw Ly Mb Nd Nf Or Oy Pc Pd Qn Rj Uc Ul Um Us) aY(aF bJ bN bW cG cP dH Ha Hq Ii Il In Io Iq Jk Jo Mn Mp Nd Nk Or Oy Pa Pd Uc Ul Us Uv) Oy(aF Ar aS aW Ax Ba bN bR cI cQ Cs cT Cx dK Gp Hc Hu Iv Kc Kf Ld Ok Ou Ph Qd) Uc(aF Ap Ar aW Ax Ba bV cl cP cQ Cs cT Cu Dg eF Fb Kc Kk Kl Kn Ou Ph) Ib(Ar aW bN cl cP cQ cT Cx Il Iq Jq Kc Kk Kp Mc Mn Ph Qn Qv Rh Us Vv) Us(aF aW bV Ch cI cP cQ cT Dk Hf Kc Kf Kk Kp Ou Ph) Jk(aF Ar aS aW bF bN cI cQ cT Cx dA Kc Kk Kp Ph) Dk(cl cP Il Iq Iv Kc Kk Kp Mb Nb Nd Nk Qv) Kk(aF CQ Dd Ha Hq Je Nf Nv Of Ut Vp) cP(Ch Cq De Ha Hq Iu Mw Nd Nv Of Om Ut) lq(aF bF Bg cE Ch Cq Qd) Ut(Ax cI cQ Cs Kc Kp Ou) Ha(Ar aW cI Kc Kp Ph) cQ(cI Kc Mb Nd Of Vp) Ch(aF bN cI Il Nd) Kp(Cq li Jo Kj) aF(Kc Mb Mc Qv) Nd(aW cl cT) Cs(Pe Vp) De(aW cl) Hq(cl Kc) li(Kc Nx) BgQn CqVv} Kq{Uc(aC Ad aF Aj Al aM AN Ar AS AW Ax Bb BC bE BG bH bl bJ bM bN Bo bR bS bV bX cC cF cG Ch cN Cp Cq cR CS Ct CU CV Cw Cx cZ dA Dc Dd DE dH Di DK dM dN Dp Ed Ef Et Ez Fb Fn Fp Fr Fw gL GP Ha Hf Hq Hr Hu Hv Hw Hx Ic Ih Ij Ik Im In Ip Ir Is It Iu Iv Iz Jd Jc Jf Jg Jh Ji Jj Jl Jm Jn Jo Jp Jr Js Jt Ju Jv Jy Kc Kd Ke Kf Kg Ki Kj Kk Kl Kn Ko Kr Ks Ky Kz Ld Lh Li Lj Lu Lv Lw Ly Lz Ma Mb Mc Md Me Mf Mg Mh Mi Mj Mk Ml Mm Mn Mp Mq Mr Ms Mt Mv Mw Mx Mz Na Nc Nd Ne Nf Ng Nh Nj Nk Nl Nm Nn Nq Nr Ns Nt Nu Nv Nw Nx Oa Oe Of Og Oh Oi Ok Om On Or Ou Ow Oy Oz Pa Pc Pd Pe Pf Ph Pj Pk Po Pz Qa Qb Qc Qd Qe Qg Qh Ql Qm Qn Qt Qu Qw Qx Qy Qz Ra Rc Rf Rg Rh Ri Rj Ss St Tz Ua Ub Ue Uf Ug Uk Ul Um Un Uo Up Ur Us Uv Vo Vp Vt Wm Tj) Bn(Ad aE AF Al Ao Ap aK aR aS Ba Bb bI bN bW cG Ch Co cT Cw dA Dd Dg dK eF Fn Fp Fw GL gW Ha Hb Hf Hq Hv Ij In Io Iu Iz Jf Jn Jo Jq Ju Jv Kc Ke Kg Kj Kk Kp Kr Kz Ld Lh Ly Ma Mc Me Mm Mn Nb Nj Nk Nm No Nq Nr Ns Nu Nx Ny Ou Oy Pa Pc Pd Pg Ph Po Qx Ra Rg Ri Rj Sr Ub Ue Uf Ug Um Ur Us Uv Vo Vv) Us(aF Ao aS aW aY Ba Bb bI bV cI cP cQ cT dA eF Gl li Il In Io Iq Ke Kk Kp Ny Oy Pg Qn Qv Qw Ra Rb Ri Sr Ub Uh Up) Qw(aF Ao aY Bb cI cQ dA Gl Hq Il Io Iq Iu Jo Ke Kk Kp Lh Oy Sr Ub Uh) Af(Cq gL Ha Ib li Ij Il In Jo Kc Kj Nf Oy Qv Sr Ud Ue Ul) Oy(cl cP Hc Io Kk Kp Mn Nb Sr Uh) Jo(cl cP cQ Io Iq Kp Nb Sr Vv) cI(Ad De Ha Ib li In Kj) Ib(cP Nb Uh) li(bN Rf Ul) Kj(cP Nb Uh) Ao(Nf Vv) In(lo Iq) HaKk NfUh} Nb{Us(aC AF aJ Ao aS aW aX Ba BC bE bI BN bR bX cC CH cI cJ cN cP cR Cu cZ dM dR Ez Fb Fp Fr gL Gp Ha Hc Hf Hq Hw Hx Ih Ii Il Iq Ir Jf Jj Jl Jn Jo Jp Ju Jv Kc Kf Ki Kk Kn Kr Ky Kz Ld Lx Ly Mb Mc Me Mr Mt Mw My Nd Nf Ng Nj Nk Nl Nw Nx Oa Oh Oi Om Ou Ow Oy Pb Pf Pg Ph Qd Qe Qt Qv Qw Qy Rb Rf Rg Rh Rj Sr St Ua Ub Ue Ug Uk Um Un Up Ur Ut Vv Wm) In(AF Ao As aW Bg bJ BN bQ bS bV bX Ch cl cN Co cP CQ cS cT cZ Dd De DK gL Ha Ib Jd Kc Kj Kz Ou Ph Qw Rh Ub Uc) cQ(Ad As bE bJ bN Cp Cq Ct Cw Dd De Ha Hr li Ij Il Iq Jt Kc Kg Kr Kz Ly Mr Na Nd Om Pb Qx Rj Uc Uk Ul Um Ur Uv Vp) Jo(Ap Ar aX Ba BC bE BN bV bX cN cP cR cS Ct Cu dA Dg dN Ez gL Gp Kc Ph Rb Rf Sr Vv) Oy(Aw aX aY Ba bJ Bo bV cN cT cW dA Ef gL Gp Hc Jv Kf Kk Qv Qw Rb Rf Sr Ur) Qw(aF Ao Ch Co dA Ib Io Kc Kg Kj Kk Kp Mi Nd Qd Rf Rg Sr Uc Ue) Ib(aY Ba bV cP cT dA eF Io Kc Kp Mv Mw Nc Ne Qy) Kj(aX aY Ba bV bX cP cR cT dA eF gL Kc Kp Nd Rf) Nd(As aY Ba bV cN cP cT dA eF gL Uc Ug) Uc(bV cT eF Kc Kf Kp Lv Rf) aY(bE bJ Gp Ha Il Io Kc Kr) Ha(bV cN dA Kc Ne Ub) bV(Io Jt Kr Ly Rj) Io(Bn gL) AfKc IqQd} Qd{Iq(Et Fp Fr Hq Hr Hu Hv Hw Hx Ih li Ij Ik Im Io Ip Ir Is It Iu Jg Jh Ji Jk Jl Jm Jn Jo Jp Jq Jr Js Jt Lu Lw Lx Ly Lz Ma Mb Mc Md Me Mf Mg Mh Mi Mj Mk Ml Mm Mn Mp Mq Mr Ms Mt Mv Mw Mx My Mz Na Nc Nd Ne Nf Ng Nh Nj Nl Nm Nn No Nq Ns Nt Nu Nv Ny Oe Of Og Oh Oi Om On Oy Oz Pa Pb Pc Pd Pe Pf Pg Po Pz Qa Qb Qc Qe Qw) Qw(Af Al aY Ba bI Bn cP cQ dA Dd Ha li Il Io Iu Ke Kk Kp Kr Nj Nk Qy Rb Ub Uh Us Vp) Il(Fr Hq Hv Hw In Io Is Iu Iv Jj Lj Lv Ly Nm Ok) Nk(Hw Ik In Jj Jo Js Lv Mc Nm Nx Oy) In(cP Ik Im Iv Js Lz Ok) Us(Ba cP cQ cT Kp Rb) Nx(Jj Jt Nm Nr Oy) cP(Cq Ha li Io Nf) cT(Ha Io Ly Uc) Lz(Iu Jj) BaUc LvJs licQ JoOk} Kk{Qw(Af aX aY Ba bE bI bV cP cS CT dA EF Ez Fb Fr gL Gp Hc Hw In Io Iv Jd Jn Jo Jy Kr Ky Lv Mc Mi Mp Mw My Nj Nk Oy Pg Ph Qt Qv Qy Rf Rh Ri Sr Ua Ub Tj) cQ(Af As Ba bE BN De Fp Gp Hw Ib li Il In Jd Jo Kg Kj Kr Nf Nw Of Oy Pg Ql Rf Rj Sr St Ub Ue Us) Ub(aM bE bJ bN cP Cq cZ Ha Ib fl In Iq Nf Nk Oy Pb Us Tj) Oy(aY cN cP cT Cu Ef Fr gL Hc Io Jy Kp Mi Mv Mw My Rb) eF(Af Bn De Ib Il In Kg Kj Kr Mn Sr Uc Ue Us) cP(As bE dI Fp Gp Hw In Io Jo Kr Rf Sr) aY(As bE Fp Jo Kj Mn Rf Us) Jo(Ba bE cT Mw Ph Vv) Us(Ba bE Nk Oh Ph) Rf(aY cQ cT) Ok(Lv Nk) BaKn RbcT OwOu PheF} Us{Kp(Af aY bV cP cQ dA eF Io Jy Lv Nw Oy Qv Rf Ri St Un Up) bV(bX dA Kc Kf Ly Rb Up) Rb(Ba cT Lv Rf) Kf(cP cQ dA) Rf(Ba cT eF) Lv(aW cl) St(cT Up) cP(Jy Un) BaUp NwcT aVdA} cQ{Kc(Af aY Ba bN cI cP Gp Hw Ip Jy Mr Nj Nk Nw Oh Oy Qv Rf St Ub) St(Af Ba Bn cI Cx Nk Nl) Nw(aF aS cl Ii Mb Qn) Rf(Af Ba bN cT Qv) Kp(Kj Kr) BnJy} Oy{Kp(Ba cP dA Io Jh Jy Kr Qy) Ba(Jy Kc Kf Kn Rf St) cT(Io Kc Ly Qy Rb Rf) Fr(Iv Ly Mb Mm Nk) Jh(aY cP Hc Kc Vv) Hc(Kc Kf) cP(Kc Kf) QyQv} cT{Rf(Af aY Ha li Io Mn Nr Ny Sr Uc) Uc(Jy Lw No Nw St) aY(Af bE bJ cV Io) St(lq Mn) Kc(Nj Sr) BnJy UbIo IbgW QvbE} Bn{Jy(aY Il Kc Kp Qv) Nw(aY li Il Kr Uh) cP(Jq St) LwKp QvbE RfgL} Nk{St(Af aY li Il Mc Ny Qv) Nm(Ji Nw) Ub(Kc Rf) Ills Iqlr IvJj} Rf{gL(Af Ao li Sr) Qv(aX bE Io) aY(bE bN Kc) Ba(Kj Uc) licF} Af{gL(Kc Kp Ou Rb St) Jy(cP Il Kc) Nw(aY cP) QvbE} Kc{Nj(aY cP Qv St) cP(Io Jy) SrJn aVdA} Nw{cP(aF aY li Nd) aY(Mn Nd) BaUc} Qv{bE(aY cI Cx dA Ou Rh)} Lv{Lj(Il Js) CsKr UcKf Iqlr} St{li(Io Nj Qy) Balq lllo} dA{aV(Rj Ur) CqKp} Ly{bV(bN Io)} Il{IvLj JyaY} NjKfKj UcKpeF Unconstrained panels with 3 analytes, where 8.9E-5 >= 'model p-value' > 1.0E-5. Contains 43,230 panels of 6,910,825 total panels evaluated. :
Ni{Ug(aC AD aE AF aG aH al AJ aK AL aM AN AO AP aQ AR AS aU aV AW AX aZ Ba BB BC bE bF BG bH bI bJ bL bM BN BO bP bQ bR bS bU bW bX bZ cA cB cC cD cE cF cG CH cl cJ cK cL cM cN CO CP Cq cR cS Ct CU CV CW CX cY cZ DB DC DD DE dF DG dH DI dJ DK DL dM dN Dp dR Ed EF Et Ez Fa Fb Fn FP Fr Fw GL GP gW Ha Hb Hc Hf Hq Hr Hu Hv Hw Hx Ib Ic Id Ii Ij Ik Im Io Ip Iq Ir Is It Iu Iv Iz Jd Je Jf Jg Jh Ji Jj Jk Jl Jm Jo Jp Jq Jr Js Jt Ju Jv Jy Kd Ke Kf Kg Ki Kj Kk Kl Kn Ko Kp Kr Ks Kz Ld Lh Li Lj Lu Lv Lw Lx Ly Lz Ma Mb

Figure 19 Continued cC Ch Cq cV Cw Cx cZ Dd dE dI dL Fw Gp Ha Kg Kj Kz Rh Rj Uk Um Ur Tj) Mr(aO aP bI bO bR bS bZ cA cF cH Cp CU Dc dG dK dN Ir Iv Ji Jl Jy Kd Kn Lj Mw No Nv Qa Qe Qh Un Vv) Dc(Ad aM As bJ Cq Cw Dd Hr Hw Ib Ii Ij Iq Ir Jr Js Jt Kj Kr Me Na Nm Of Pb Rj Uc Uk Ul Vp) aP(aF aM As aX bJ cC Ch cV Cw Cx dL Hr Hw Ib Ii Iq Jt Kr Kz Me Mq Ms Na Nm Of Pb Pg Rj) Cx(aE aO aX aZ bJ bO Ch Cv cX dE dI dK Fr Gp Ji Jj Li Lj Mi Mw Nc Nl No On Rj Ur) aX(aE bJ bL bS cC cV dD dK Hw Ip Jj Jm Jy Ms Mw Nb Ne Nl No Nt Rh Rj Um Vv) Ur(As Ch dI Fn gW Hw Iv Jv Jy Kr Mp Ms Mw Nb Ne Nl No Pg Ra Rh Rj Ua Vv) bA(Dp Ed Ez Fb fP gP Hb Hc Hf Iz Jf Ki Kl Ks Ld Pj Qg Qh Rc Ri Rm Ua Uo) Kj(Aw bI Cp Cu Ef Ez Fr Hc Ir Jk Li Mw My Nb On Qa Qe Qy Un Ut Vv) Mw(Ad aM Ao As aZ Bb bJ cC Ch cV Gp Ib Iv Jj Kr Kz Rj Uc Uk) Nb(aF aM aN As bJ bQ Ch Cq Ct cV cZ Dd De dI gW Ha Ib Qx Uc) Nl(aC aE aM aN As aZ bJ bS bZ cC Ch Cq cU cV Dd dE dI Gp) Ji(As Hw Ii Ij Iq Iu Iv Jj Jq Js Mf Mm Ng Nr Ny Of Pb Pd) Kr(cH dN Fr Gp Jj Li Lj Lw Mi Mp Oa On Qa Qe Rb Un) cC(bI bR bS cF CH cU Fr Jj Jl Kz Mi Ne No Nt Qe) Cu(aM As bJ Cq cV Dd Ib Ii Ij Iq Js Jt Of Pb Uc) Vv(Ao CH Co gW Ib Jj Lw Mk Ms Of Pb Un Tj) Fr(Ad aF Ao As aZ Bb bJ Ch cV Iv Jj Of Uc) Gp(aZ bI Ch dK gW Jv Lj Mi Ms Ne Pg Rb) Rj(bI cH Ir Jq Lj Lw Mi Ne Rh Ri Uk Un) On(Ao As Ch cV Ii Iv Jj Mm Ng Nm Of Uc) Ib(Bo Cp Hc Jh Jk Mv Nq Ny Qh Qy Ua) bJ(bR bS CH Jj Lj Mi Ms Mt Ne No) As(bI cH Cp Jj Jq Li Lw Mi Ne No) cH(aM Hr Iq Me Na Nm Of Pb Uk) Hw(Bc bI dK Ez Ok Qy Rb Ua) cV(dG dN Jj Li Mi Mp Ne No) Bo(Bg Co Hq Iu My Of) Uk(aZ Ir Mi Qe Ua Un) aE(bI bS Jj Mi Ms Nc) aM(Jj Lw Mi Mt Ne No) Ch(Bg Ip My Pg Qy) Un(Ii Me Nm Uc Ul) bS(aZ dE dI Na Pg) Cq(Lw Mt No Ny) Ok(Nm Of Pb Pd) aF(aO bZ Jy No) dI(bR cA cF Ms) Ao(Jy Pg Qy) Dd(Jq Lw No) Ne(aC aZ dE) Ir(Iu Iv Jj) Qh(Js Ul Um) Cp(Of Uc) Lw(Ad Ul) Ii(Rm Ut) Iv(Jj Me) bI(Hr Ms) gW(Jy Rh) AwOf FpOa NmdN NoaZ MiUm UcQa KnUl NyVp} bA{Kc(aA aC AD aE aF aG aH aI AJ aK AL aM AN AO AP aQ AR AS aU aV AW AX aZ Ba BB BC bE bF BG bH bI bJ bL bM BN BO bP bQ bR bS bU bV bW bX bZ cA cB cC cD cE cF cG CH cI cJ cK cL cM cN CO CP Cq cR CS CT CU CV CW CX cY cZ dA DB DC DD DE dF DG dH DI dJ DK DL dM dN Dp Ed EF Et Ez Fa Fb Fn Fr Fw gL GP gW Hb Hc Hf Hq Hr Hu Hv Hx Ib Ic Id Ih Ii Ij Ik Il Im Ip Ir Is It Iu Iv Iz Je Jf Jg Jh Ji Jj Jk Jl Jm Jn Jp Jq Jr Js Jt Ju Jv Jy Kd Ke Kf Kg Ki Kj Kk Kl Kn Ko Kp Kq Ks Ky Kz Ld Lh Li Lj Lu Lv Lw Lx Ly Ma Mb Mc Md Me Mf Mg Mh Mi Mj Mk Ml Mm Mp Mq Mr Ms Mt Mu Mv Mw Mx My Mz Na Nb Nc Nd Ne Nf Ng Nh Nm Nn No Nq Nr Ns Nt Nu Nv Nw Nx Oa Oe Of Og Oh Oi Ok Om On Or Ou Ow Oz Pa Pc Pd Pe Pf Pg Ph Pi Pj Pk Po Pz Qa Qb Qc Qd Qe Qg Qh Qm Qn Qt Qu Qv Qx Qy Qz Ra Rb Rc Rf Rg Rh Ri Rj Rm Ss St Tz Ua Ud Ue Uf Ug Uk Ul Um Un Uo Up Ur Ut Uu Uv Vo Vp Vt Vv Wm Tj) Jo(aA aC AD aE AF aG aH aI AJ aK AL aM AN aO AP aQ AR AS aU aV AW AX aZ Ba BB BC bF BG bH bI bL bM BN BO bP bQ bR bS bU bV bW bX bZ cA cB cC cD cE cF cG CH cI cJ cK cL cM cN CO Cp Cq cR CS CT CU Cv cW CX cY cZ dA DB DC DD DE dF DG dH DI dJ DK DL dM dN Dp dR Ed EF Et Ez Fa Fb Fn FP Fr Fw GL GP gW Ha Hb Hc Hf Hq Hr Hu Hv Hw Hx Ib Ic Id Ih Ii Ij Ik Il Im In Ip Ir Is It Iu Iz Jd Je Jf Jg Jh Ji Jj Jk Jl Jm Jn Jp Jq Jr Js Jt Ju Jv Kd Ke Kg Ki Kj Kl Ko Kp Kq Kr Ks Ky Kz Ld Lh Li Lj Lu Lv Lw Lx Lz Ma Mb Mc Md Me Mf Mg Mh Mi Mj Mk Ml Mm Mn Mp Mq Mr Ms Mt Mv Mw Mx My Mz Na Nc Ne Nf Ng Nh Nj Nl Nm Nn No Nq Nr Ns Nt Nu Nv Nw Ny Oa Oe Of Og Oh Oi Ok Om On Or Ou Ow Oy Oz Pa Pb Pc Pd Pe Pf Pg Pi Pj Pk Po Pz Qa Qb Qc Qd Qe Qg Qh Ql Qm Qn Qt Qu Qv Qx Qz Rc Rg Ri Rj Rm Ss St Tz Ua Ub Uc Ud Ue Uf Ug Uh Uk Ul Um Un Uo Up Ur Ut Uu Uv Vo Vp Vt Wm Tj) Uc(aA aC AD aE aF aG aH aI AJ aK AL aM AN AO AP aQ AR AS aU aV Aw AX aZ Ba BB BC bF BG bH bI bJ bL bM BN BO bP bQ bR bS bU bV bW bX bZ cA cB cC cD cE cF cG CH cI cJ cK cL cM cN CO CP Cq cR CS CT cU CV CW CX cY cZ dA DB DC DD DE dF DG dH DI dJ DK DL dM dN Dp dR Ed Ef Et Ez Fa Fb Fn Fp Fr Fw GL Gp gW Ha Hb Hc Hf Hq Hr Hu Hv Hw Hx Ib Ic Id Ih Ii Ij Ik Il Im Ip Iq Ir Is It Iu Iv Iz Jd Je Jf Jg Jh Ji Jj Jk Jl Jm Jn Jp Jr Js Jt Ju Jv Ke Kg Ki Kj Kl Ko Kr Ks Ky Kz Ld Lh Li Lj Lu Lx Lz Ma Mb Mc Md Me Mf Mg Mh Mi Mj Mk Ml Mm Mn Mp Mq Ms Mt Mv Mw Mx My Mz Na Nc Nd Ne Nf Ng Nh Nj Nl Nm Nn Nq Nr Ns Nt Nu Nv Ny Oa Oe Of Og Oh Oi Ok Om On Or Ou Ow Oy Oz Pa Pb Pc Pd Pe Pf Pg Ph Pi Pj Po Pz Qa Qb Qc Qe Qg Qh Ql Qm Qn Qt Qu Qv Qx Qz Ra Rc Rg Rh Ri Rj Rm Sr Ss Tz Ua Ub Ud Ue Uf Ug Uh Uk Ul Um Un Uo Up Ur Us Ut Uu Uv Vo Vp Vt Vv Wm Tj) Uv(aA aC AD aE aF aG aH aI AJ aK AL aM AN AO AP aQ AR AS aU aV Aw AX aZ Ba BB BC bF BG bH bI bJ bL bM BN BO bP bQ bR bS bU bV bW bX bZ cA cB cC cE cF cG CH cI cJ cK cL cM cN CO CP Cq CS CT CU CV CW CX cY cZ DB dC DD DE dF DG dH DI dJ DK DL dM dN Dp dR EF Et Ez Fa Fb Fn FP Fr Fw GL Gp gW Ha Hb Hc Hf Hq Hr Hu Hv Hw Hx Ib Ic Id Ih Ii Ij Ik Il Im Ir Is It Iu Iz Jd Je Jf Jg Jh Ji Jj Jk Jl Jm Jn Jp Jr Js Jt Ju Jv Ke Kf Kg Ki Kj Kl Kn Ko Kp Kr Ks Ky Kz Ld Lh Li Lj Lu Lv Lx Lz Ma Mb Mc Md Me Mf Mg Mh Mi Mj Mk Ml Mm Mn Mp Mq Ms Mt Mv Mw Mx My Mz Na Nc Nd Ne Nf Ng Nh Nj Nl Nm Nn Nq Nr Ns Nt Nu Nv Oa Oe Of Og Oh Oi Ok Om On Or Ou Ow Oy Oz Pa Pb Pc Pd Pe Pf Ph Pi Pj Pk Po Pz Qa Qb Qc Qd Qe Qg Qh Ql Qm Qn Qt Qu Qx Qy Qz Ra Rc Rg Rh Ri Rj Rm Sr Ss Tz Ua Ub Ud Ue Uf Ug Uh Uk Ul Um Uo Up Ur Ut Uu Vo Vp Vt Vv Wm Tj) bE(aA aC AD aF aG aH aI AJ aK AL aM AN AO AP aQ AR AS aU aV Aw AX aZ Ba BB BC bF Bg bH bI bJ bL bM BN BO bP bQ bR bU bV bZ cB cC cD cF cG cH cJ cK cL cM cN CO Cp Cq cR CS CT CU Cv CW cX cY cZ dA DB DC dD DE dF dG DI dJ DK DL dM dN Dp dR Ed EF Et Ez Fa Fb Fn FP Fr Fw gL GP Ha Hb Hc Hf Hq Hr Hu Hv Hx Ib Ic Id Ih Ii Ij Ik Im Ip Ir Is It Iu Iv Iz Jd Je Jf Jg Jh Ji Jj Jk Jl Jm Jn Jp Jq Jr Js Jt Ju Jv Jy Kd Ke Kf Kg Ki Kj Kl Kn Ko Kp Kq Kr Ks Ky Kz Ld Lh Li Lj Lu Lv Lw Lx Lz Ma Mb Md Me Mf Mg Mh Mi Mj Mk Ml Mm Mp Mq Mr Ms Mt Mu Mv Mw Mx My Mz Na Nc Ne Nf Ng Nh Nj Nl Nm Nn No Nq Nr Ns Nt Nu Nv Nw Nx Ny Oa Oe Of Og Oh Oi Ok Om On Or Ou Ow Oz Pa Pb Pc Pd Pe Ph Pi Pj Pk Po Pz Qa Qb Qc Qd Qe Qg Qh Ql Qm Qn Qt Qu Qx Qy Qz Ra Rc Rg Ri Rj Rm Ss St Tz Ua Ub Ud Ue Uf Ug Uh Uk Ul Um Un Uo Up Ur Ut Uu Vo Vp Vt Vv Wm Tj) Oy(aA aC AD aE AF aG aH aI AJ aK AL aM AN AO AP aQ AR AS aU aV AW AX aZ Ba BB BC bF BG bH bI bL bM BN BO bP bQ bR bS bU bV bW bZ cA cB cC cD cE cF cG CH cI cJ cK cL cM cN CO Cp Cq cR CS CT CU Cv CW CX cY cZ DB DC DD DE dF DG dH DI dJ DK DL dM dN Dp dR Et Ez Fa Fn FP Fr Fw gL GP gW Ha Hb Hq Hr Hu Hv Hw Hx Ib Id Ih Ii Ij Ik Il Im In Ip Iq Ir Is It Iu Iz Jd Je Jf Jg Ji Jj Jk Jl Jm Jn Jp Jq Jr Js Jt Ju Jv Kd Ke Kg Ki Kj Kl Kn Ko Kr Ks Ky Kz Lh Li Lj Lu Lv Lw Lx Lz Ma Mb Mc Md Me Mf Mg Mh Mi Mj Mk Ml Mm Mp Mq Mr Ms Mt Mv Mw Mx My Mz Na Nc Ne Nf Ng Nh Nj Nl Nm Nn No Nq Nr Ns Nt Nu Nv Nw Ny Oa Oe Of Og Oh Oi Ok Om On Or Ou Ow Oz Pa Pb Pc Pd Pe Pf Pg Ph Pi Pj Pk Po Pz Qa Qb Qc Qd Qe Qg Qh Ql Qm Qt Qu Qx Rc Rg Ri Rm Ss Tz Ua Ud Ue Uf Ug Uk Ul Um Un Uo Up Ur Uu Vo Vp Vt Vv Wm Tj) Rf(aA aC aD aE aF aG aH aI AJ aK aL aM AN aO AP aQ AR AS aU aV AW AX aZ Ba bB BC bF BG bH bI bJ bL bM bN BO bP bQ bR bS bU bV bW bX bZ cA cB cC cD cE cF cG CH cJ cK cL cM cN CO CP cR CS CT CU CV cW CX cY cZ dA DB DC dD dE dF DG dH DI dJ DK DL dM dN Dp dR Ed EF Et Ez Fa Fb Fn Fr Fw gL GP gW Hb Hc Hf Hq Hr Hu Hv Hx Ic Id Ij Ik Im Ip Ir Is It Iu Iv Iz Je Jf Jg Jh Ji Jj Jl Jm Jn Jp Jq Jr Ju Jy Kd Kf Kg Ki Kk Kl Kn Ko Kp Kq Ks Ky Kz Ld Li Lj Lu Lv Lw Lx Ma Mb Md Me Mf Mg Mh Mi Mk Ml Mm Mp Mq Mr Ms Mt Mu Mv Mw Mx My Mz Na Nb Nc Ne Nf Ng Nh Nl Nm Nn No Nq Ns Nt Nu Nw Nx Oa Oe Of Og Oh Oi Ok Om On Or Ou Ow Oz Pa Pc Pd Pe Ph Pj Pk Pz Qa Qc Qd Qe Qg Ql Qm Qn Qt Qu Qv Qx Qy Qz Ra Rb Rc Rg Rh Ri Ss St Tz Ua Ub Ud Ue Ug Uk Ul Um Un Uo Up Ur Ut Uu Vo Vt Vv Wm Tj) In(aA aC AD aE aF aG aH aI AJ aK AL aM AN AO AP aQ AR AS aU aV Aw AX aZ Ba BB BC bF Bg bH bI bL bM BN BO bP bQ bS bU bV bW bZ cA cB cC cD cE cG CH cI cJ cK cL cM cN CO Cp Cq Cs CT CU Cv CW CX cY cZ dA DB DC dD DE dF DG dH DI dJ DK DL dM dN Dp dR Ed EF Et Ez Fa FP Fr gL GP gW Hb Hc Hf Hq Hr Hu Hv Hw Hx Ic Id Ih Ii Ij Ik Im Ip Ir Is It Iu Iz Je Jf Jg Jh Ji Jj Jk Jl Jm Jn Jp Jq Jr Js Jt Kd Ke Kf Kg Ki Kj Kl Kn Ko Kp Kq Ks Ky Kz Ld Lh Li Lj Lu Lv Lw Lx Lz Ma Mb Md Me Mf Mg Mh Mi Mj Mk Ml Mm Mp Mq Mr Ms Mt Mu Mv Mw Mx My Mz Na Nc Ne Nf Ng Nh Nj Nl Nm Nn No Nq Nr Ns Nt Nu Nv Nw Oa Oe Of Og Oh Oi Ok Om On Or Ow Oz Pa Pb Pc Pd Pe Pf Pj Pk Po Pz Qa Qb Qc Qd Qe Qg Ql Qm Qu Qx Rc Rg Ri Rm Ss St Tz Ua

Mb(cS gW Ju Lz Mk Ng Nj) cE(Bb Cx Fb Ju Tz Ug Uk) No(dF Fw Jt Ke Po Vp) Rh(Cw gW Kg Lh Ng Of) bQ(Ar Bo cS dN Ug Uk) Cx(bG cF Cw cZ Ju) Nx(Hr Jt Lh Of Po) Dc(Ad As Cw Vp) Ju(aE bN dF Of) Bo(Ao Bg Co) Jt(cH Ih Jn) Kf(Kg Lh Mr) Un(Ke Lh Mj) bN(bG cN Jj) dG(aJ cN dN) Ar(Bb Cw) Me(Jd Tj) Js(Jn Jr) Of(eF Vv) Vp(Kd Lw) cS(cG dH) dF(cN Jj) gW(Jd Lh) AocA BbaF CwbR PoLx MjUu NjUg IcaE IhRm KgVv} aA{Kc(aC AD aE aF aG aH aI AJ aK AL aM AN AO AP aQ AR AS aU aV AW AX aZ Ba BB BC bE bF BG bH bI bJ bL bM BO bP bQ bR bS bU bV bW bX bZ cA cB cC cD cE cF cG CH cI cJ cK cL cM cN CO Cp Cq cR CS CT CU CV CW cX cY cZ dA DB DC DD DE dF DG DI dJ DK DL dM dN Dp dR Ed EF Et Ez Fa Fb Fn fP Fr Fw GL GP gW Hb Hc Hf Hq Hr Hu Hv Hx Ib Ic Id Ih Ii Ij Ik Il Im In Ip Ir Is It Iu Iv Iz Jd Je Jf Jg Jh Ji Jj Jk Jl Jm Jn Jo Jp Jq Jr Js Jt Ju Jv Jy Kd Ke Kf Kg Ki Kj Kk Kl Kn Ko Kp Kq Kr Ks Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Nl Nm Nn No Nq Nr Ns Nt Nu Nv Nw Nx Ny Oa Oe Of Og Oh Oi Ok Om On Or Ou Oz Pa Pb Pc Pd Pe Pf Ph Pi Pj Pk Po Pz Qa Qb Qc Qd Qe Qg Qh Ql Qm Qn Qt Qu Qv Qx Qy Qz Ra Rb Rc Rf Rg Rh Ri Rj Rm Sr Ss St Tz Ua Ub Uc Ud Ue Uf Ug Uh Uk Ul Um Un Uo Up Ur Ut Uu Uv Vo Vp Vt Wm Tj) In(aC AD aE aF aG aH aI AJ aK AL aM AN AO AP aQ AR AS aU aV Aw AX aZ Ba BB BC bE bF BG bH bI bJ bL bM bN BO bP bQ bR bS bU bV bW bX bZ cA cB cC cD cE cF cG CH cJ cK cL cM cN CO Cp Cq cR CS CT CU CV CW cX cY cZ dA DB DC DD DE dF DG dH DI dJ DK DL dM dN Dp dR Ed EF Et Ez Fa Fb Fn FP Fr Fw GL GP gW Ha Hb Hc Hf Hq Hr Hu Hv Hw Hx Ib Ic Id Ih Ij Ik Il Im Io Ip Iq Is Iu Iz Jd Je Jf Jg Ji Jj Jl Jm Jn Jp Jq Jr Js Ju Jv Jy Kd Ke Kf Kg Ki Kj Kl Kn Ko Kp Kq Kr Ks Ky Kz Ld Lj Lw Lx Lz Ma Mb Mc Me Mf Mh Mi Mj Mm Mn Mp Mq Mr Mt Mu Mv Mw Mx My Mz Na Nb Nc Nd Ne Nf Ng Nh Nj Nl Nm Nn Nq Nr Ns Nt Nu Nv Nw Ny Oa Oe Of Og Oi Om On Or Ow Oy Oz Pa Pb Pc Pd Pe Pf Pg Ph Pi Pj Pk Po Qa Qe Qg Qh Ql Qm Qn Qt Qv Qx Qy Qz Ra Rb Rf Rg Ri Rj Rm Sr Ss St Tz Ua Ub Uc Ud Ue Uf Ug Uh Uk Ul Um Un Ur Ut Uu Uv Vo Vp Tj) Us(aC AD aE aF aG aH aI AJ aK AL aM AN AO AP aQ aR AS aU aV Aw AX aZ Ba BB BC bE bF BG bH bI bL bM bN BO bP bQ bS bU bW bX bZ cA cB cC cE cF cG CH cJ cK cL cN CO Cp Cq Cs Ct CU CV CW cX cY cZ dA DB DC DD DE dF DG DI dJ DK DL dM dN Dp dR Ed Ef Et Ez Fa Fb Fn FP Fr Fw GL GP gW Ha Hb Hc Hq Hr Hu Hv Hw Hx Ib Id Ih Ii Ij Ik Il Im Ir Is It Iu Iz Jd Je Jf Jg Jh Ji Jj Jk Jl Jm Jo Jp Jq Jr Js Jt Ju Jv Jy Kd Ke Kg Ki Kj Kl Ko Kr Ks Ky Kz Ld Lh Li Lj Lu Lw Lx Lz Ma Mb Md Me Mf Mg Mh Mi Mj Mk Ml Mm Mn Mp Mq Ms Mt Mu Mv Mw Mx My Mz Na Nc Nd Ne Nf Ng Nh Nj Nl Nm Nn No Nq Nr Ns Nt Nu Nv Nw Ny Oa Oe Of Og Oh Oi Ok Om On Or Ow Oz Pa Pb Pc Pd Pe Pf Pi Pj Pk Po Pz Qa Qb Qc Qd Qe Qg Qh Ql Qm Qn Qt Qu Qx Qy Qz Ra Rc Rg Rj Rm Sr Ss Tz Ua Ub Uc Ud Ue Uf Ug Uh Uk Ul Um Un Uo Ur Ut Uu Uv Vo Vp Vt Wm Tj) Ly(aC AD aE aF aG aH aI AJ aK AL aM AN AO AP aQ AR aS aU aV AW AX Ba BB BC bE bF BG bH bI bJ bL bM BO bP bQ bR bS bU bV bX bZ cA cB cD cE cF cG CH cJ cK cL cM cN CO Cp Cq cR CS CT CU CV CW cX cY cZ dA DB DC DD DE dF DG dH DI dJ DK DL dM dN dR eF Et Fb Fn Fp Fr Gl GP gW Ha Hq Hu Hv Hw Ib Ic Ih Ii Ij Ik Il Im Io Ip Iq Ir Is It Iu Iv Jg Jh Ji Jj Jl Jn Jo Jp Jr Js Jv Jy Ki Kj Kk Kp Kq Kr Ky Ld Lj Lw Lx Lz Ma Mb Mc Md Me Mf Mh Mi Mk Mm Mn Mp Mq Mr Ms Mt Mu Mv Mw Mx My Mz Na Nc Nd Ne Nf Ng Nh Nj Nl Nm Nn No Nq Nr Ns Nt Nw Ny Of Og Oi Ok Om On Ou Oz Pa Pb Pc Pd Pe Pf Pg Ph Pi Pk Po Qd Qe Qn Qt Qv Rh Rj Sr Ss St Tz Uc Uf Uu Vv) Qw(Ad AJ AL An Ap aQ AR aV Aw Ax Bb BC BG bL bM Bo bP bS bU cA cB cD cF CH cJ cK cL CO Cp Cq Cs Ct Cu Cv CW cY DB Dc dD dE Dg Di dJ Dk Dl dN Dp Ed Ef Et Ez Fa Fb Fn fP Fr Fw gL Hb Hq Hr Hu Hv Hx Id Ih Ij Ik Im Ir Is It Iu Iz Jd Je Jf Jg Jh Ji Jj Jk Jl Jm Jp Jq Jr Js Jt Ju Jy Kd Ke Kf Kg Kj Kl Kn Ko Kr Ks Li Lj Lu Lv Lw Lx Lz Ma Md Me Mf Mg Mh Mj Ml Mm Mn Mp Mq Ms Mt Mv Mx My Mz Na Nc Nd Ne Ng Nh Nl Nm Nn No Nq Nr Ns Nt Nv Nw Ny Oa Oe Oh Oi Ok Om On Or Ow Oz Pa Pb Pd Pe Pf Pj Pk Po Pz Qa Qb Qc Qe Qg Qh Ql Qm Qu Qx Qz Rc Rm Ss St Tz Ua Uc Ud Ue Uf Ug Uk Ul Um Un Uo Ur Ut Uv Vo Vp Vt Wm Tj) Kk(aC AD aE aF aH aI Aj aK aL aM AN AO aP aR AS aU AW aX aY aZ Ba BB bE bF BG bH bI bJ bM bO bP bQ bR bS bU bV bW bX cA cC cE cF cG Ch cI cJ cL cM cN CO CP CQ cR cS CT Cu cV CW CX cZ dA dB DC dD dE dF dG dH dI DK dL dN dR eF Fn Fp Fw GL Gp gW Hq Hr Hv Hw Hx Ic Id Ih Ii Ij Ir Is It Iv Jd Je Jg Jh Ji Jk Jn Jo Jq Jr Js Jt Kd Ke Kg Kn Ko Kp Kq Kr Kz Ld Lh Mb Mc Md Me Mk Ml Mq Mr Ms Mt Mw Mx My Mz Na Nb Nd Ng Nk Nm Nq Nr Nv Nx Ny Of Og Om Or Pa Pb Pc Pd Pc Pf Pg Pi Pk Po Qa Qb Qh Ql Qn Qv Qx Qz Ra Rb Rf Rh Rj Rm Sr Tz Ub Ud Ue Ug Uk Ul Um Up Ur Ut Uu Uv Vp Vt Vv Tj) Mb(aC aE aF aG aI Aj aM AN Ao aP Ar AS aU aW AX aY aZ Ba Bb Bc bE bH bI bJ bM bN bO bQ bR bS bU bV bW bX bZ cA cC cD cE cF cG CH cI cL cM cN cO cP cR cS cT cV Cw CX dA dC Dd De dF dG dH dI dK dL dM dN dR eF Et Fb Fp Fr Gl gW Hf Hq Hr Hu Hv Hw Hx Ic Ih Ii Ij Ik Il Im Io Ip Iq Ir Is It Iu Iv Jg Jh Ji Jj Jk Jl Jm Jn Jo Jp Jq Jr Js Jt Jv Jy Kp Ld Lj Lu Lv Lw Lx Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Nl Nm Nn No Nq Nr Ns Nt Nu Nv Nw Ny Oe Of Og Oh Oi Om On Ou Oy Oz Pa Pb Pc Pd Pe Pg Po Pz Qa Qb Qc Qd Qe Qv Ra Rf Rj Ub Vv) Bn(aP Ar aW aY bN bQ bR bS bW bX cA cB cI cP cQ cT cV Dc dG dH Dp Ed Et Ez Fa Fb Fn FP Ha Hb Hc Hf Hq Hr Hu Hv Hw Hx Ib Id Ih Ii Ij Ik Il Im Ip Ir Is It Iu Iz Jd Je Jf Jg Jh Ji Jj Jk Jl Jm Jo Jp Jr Js Jt Ju Jv Kd Ke Kf Kg Ki Kj Kl Ko Kr Ks Ky Kz Lh Li Lj Lu Lx Lz Ma Md Me Mf Mg Mh Mi Mj Mk Ml Mm Mn Mp Mq Ms Mt Mv Mw Mx My Mz Na Nc Nf Ng Nh Nj Nl Nm Nn No Nr Ns Nt Nu Nv Ny Oa Oc Of Og Oh Oi Ok Om On Or Ow Oy Oz Pa Pb Pc Pd Pe Pf Pg Pi Pj Pk Po Pz Qa Qb Qc Qd Qe Qg Qh Ql Qm Qn Qt Qu Qx Qz Rc Rg Ri Rj Rm Sr Ss Tz Ua Ub Uc Ud Ue Uf Ug Uh Uk Ul Um Un Uo Up Ur Ut Uu Uv Vo Vp Vt) Io(aC Ad aG aI AJ aK AL AN AO AP aQ aR AS aV Aw Ax aZ Ba Bb BC bF BG bH bI bL bM BO bP bS bU bV bW bZ cA cB cD cF CH cJ cK cL cM cN CO Cp Cq Cs Ct CU Cv CW cX cY dA DB Dc dD dE Dg Di dJ DK Dl dM dN Dp dR Ed EF Ez Fa Fb Fn fP Fw GL GP Ha Hb Hc Hf Hw Ib Id Il Ir Is Iv Iz Jd Je Jf Ji Jj Jn Jp Ju Jv Jy Kd Ke Kf Kg Ki Kj Kl Kn Ko Kp Kq Kr Ks Ky Kz Ld Lv Mc Mw Nc Nf Nw Oa Ok Or Ou Ow Oy Pf Ph Pi Pj Pk Qd Qg Qh Ql Qm Qt Qu Qx Qy Qz Ra Rc Rg Ri Rj Rm Sr Ss St Tz Ua Ub Uc Ud Uc Uf Ug Uh Uk Ul Um Un Uo Up Ur Ut Uu Uv Vo Vp Vt Tj) Cx(aP Ar aW aY bE bN bR bS bW bX cD cF cI cP cQ cR cT cV Dd dG dH Ed Fb Fn Fp gP Ha Hc Hf Hr Hu Hv Hw Hx Ib Ic Id Ih Ii Ij Ik Il Ip Ir It Iu Iv Iz Jd Jf Jg Jj Jk Jm Jn Jo Jr Js Jt Ju Jv Jy Kg Ki Kj Ko Kp Kr Ky Kz Ld Lh Lu Lv Lw Lx Lz Ma Md Me Mf Mh Mi Mj Mk Ml Mm Mn Mr Ms Mu Mv Mw Mx My Mz Na Nb Nc Nd Ne Nf Ng Nh Nj Nl Nm Nn No Nq Nr Ns Nw Nx Ny Oe Of Og Oh Oi Om Or Ou Ow Oy Oz Pb Pc Pd Pe Pf Pg Ph Pi Pk Po Qa Qb Qd Ql Qt Qu Qv Qy Qz Ra Rf Rg Rh Rj Sr St Tz Ua Ub Uc Ud Ue Uf Ug Uk Ul Um Uo Up Ur Uu Uv Vp Vv) Iq(aC AD aE aF aG aH aI AJ aK aL aM AN AO aP aQ AR AS aU aV aW AX aY aZ Ba BB BC bE bF bG bH bI bJ bL bM bN BO bP bQ bR bS bU bV bW bX bZ cA cB cD cE cF cG CH cJ cK cL cM cN cO CP Cq cR CS CT CU CV CW cX cY cZ dA DB DC DD DE dF dG dH dI dJ dK dL dM dN dR eF Fn Fp Fr gL Gp gW Hc Hf Hw Ib Ic Ih Il Is Ji Jj Jl Jn Jp Jr Jy Kf Kp Kq Ky Kz Ld Lj Lx Mc Mi Mj Mr Mw Na Nc Ne Nf Nl No Ns Nw On Ou Oy Pf Ph Qe Qv Qy Rb Rh Rj St Ub Ur Vv) Iv(Ad aM An As bE bJ bN cI CP CQ Cu cV Cw Dc Dd De dG dL Et Fp Fr Fw Ha Hq Hr Hu Hw Hx Ib Ih Ii Ij Ik Im Ip Ir Is It Iu Jg Jh Ji Jj Jk Jl Jm Jn Jo Jp Jq Jr Jt Kj Kr Kz Lu Lv Lw Lx Lz Ma Mc Md Me Mf Mg Mh Mi Mj Mk Ml Mm Mn Mp Mq Ms Mt Mu Mv Mw My Mz Na Nb Nd Ne Ng Nh Nj Nl Nm Nn No Nq Nr Ns Nt Nu Nv Nw Ny Oe Of Og Oh Oi Ok Om On Oz Pa Pb Pc Pd Pe Pg Po Pz Qa Qb Qc Qd Qe Rj Uc Ul Um Uv Vp Vv) Oy(Ar aU aW Ax aY Ba bE bJ bN Bo bR bW bX cC cI cP cQ cR Cs cT Cu dA EF Et Fb Fp Hc Hq Hr Hv Hw Hx Ic Ih Ij Ik Il Im Ip Ir Is Iu Jg Jh Ji Jj Jk Jl Jm Jn Jp Jq Jr Js Kf Kq Ld Lj Lu Lw Lx Lz Ma Mc Me Mg Mh Mi Mj Mk Mm Mn Mp Mq Mr Ms Mt Mv Mw Mx My Mz Na Nb Nc Nd Ne Nf Ng Nh Nj Nl Nm No Nq Ns Nt Nu Nv Nw Ny Oi Om On Ou Oz Pb Pc Pd Pf Pg Ph Po Qa Qc Qe Qv Qy Rb Rf Sr Ub Vv) Af(aM An Ar AW aY Ba bE bI bN Bo bQ bR bS bW bX cA cB cF cI cP cQ cR cT cV dG dH dL Dp Ed EF Et Fa FP gL GP Hb Hq Hu Ik Im Is It Iu Iz Jd Je Jg Jh Ji Jk Jl Jp Jq Ju Kd Ke Kf Kg Kl Kn Ko Ks Lh Li Lj Lu Lw Mf Mh Mi Mk Mm Mp Mq Mt Mv My Nh Nj Nn No Nt Nu Nv

Figure 19 Continued

Oa Ok Ow Pa Pi Pj Pk Po Pz Qb Qc Qe Qg Qh Qm Qn Qu Ri Rm Ss Ua Uf Uh Un Uu Vo Vt Wm Tj) Rf(Ad aF Aj Al Ao aP As aW aX Ba Bb bE bI bJ bN bR cC Ch cI cP Cq cR cT Cw dA Dd De dF dG dH dR eF Fn Fp Fw GL Gp gW Hc Hf Hu Hw Ib Ic Id Ih Ij Il Iu Jd Jf Jk Jl Jo Jq Js Jt Jv Ke Kj Kn Kr Kz Ld Mc Md Me Mf Mj Mm Mn Na Nd Ne Nf Ng Nk Nm Nn Nq Nr Nv Nx Oe Of Og Or Ou Pc Pd Pf Pg Qn Qv Qy Qz Ra Rb Rg Rh Rj Tz Ub Uc Ue Ug Uh Uk Ul Um Ur Ut Uu Uv Vp Vv) cQ(aM aP bE bJ bN bS bX cI cP cV dG Fb Fn Ha Hr Hv Hw Hx Ib Ic Id Ih Ii Ij Il Ip Ir It Jm Jn Jo Jr Js Jt Kg Kj Kr Kz Ld Lh Lj Lv Mc Md Me Mj Ml Mn Mq Mr Ms Mu Mv Mw Mx Mz Na Nb Ne Nf Ng Nj Nk Nl Nm Nq Nr Ns Nw Nx Ny Oe Of Og Oh Om Or Oz Pb Pc Pd Pe Pg Pi Pk Po Qa Qd Ql Qn Qv Qx Qz Ra Rb Rh Rj Sr St Tz Ub Uc Ud Ue Ug Uk Ul Um Up Ur Uv Vp Vv) Lv(As bE bJ bN cI cV Dd De dF Et Fp Fr Hq Hr Hu Hw Hx Ih Ii Ik Im Ip Ir Is It Iu Jg Jh Ji Jj Jk Jl Jm Jn Jp Jq Jr Jt Kz Lh Li Lj Lu Lw Lx Lz Ma Mc Md Mf Mg Mh Mi Mj Mk Ml Mm Mn Mq Ms Mt Mu Mv Mw My Mz Na Nb Nc Nd Ne Ng Nh Nj Nl Nm Nn No Nq Nr Ns Nt Nu Nv Nw Ny Oe Og Oh Oi Ok Om On Oz Pa Pc Pe Pg Po Pz Qa Qb Qc Qd Qe Qn Uc Vv) cI(aM aP bE bJ bN bQ bR bS bX cA cB cH cP cR cT cV dG dH Fb FP Gp Ha Hf Hr Hu Hv Hw Ib Ic Ih Ii Ij Il Ip Ir Iu Jd Jj Jn Jo Js Jt Jv Jy Kj Kn Kr Ky Kz Ld Mc Me Mi Mj Ml Mn Mq Mr Ms Mu Mv Mx Na Nb Nd Ne Nf Ng Nj Nk Nl Nm Nn Nq Nr Ns Nw Nx Ny Oe Of Og Oh Ow Oz Pb Pc Pd Pf Pg Qn Qv Qy Rb Rh Rj Sr St Tz Ub Uc Ul Um Ur Uv Vv) cP(aF aM aN aP As aW Ba bE bJ bN bQ bR bS bW bX Ch Cq cR cT cZ Dd De dG dH dI dL Fp Ha Hr Hv Hw Hx Ib Ic Ih Ii Ij Il Ip Ir It Jn Jo Jr Js Jt Kj Kr Kz Lh Mc Md Me Mj Mk Ml Mn Mq Mr Ms Mu Mv Mw Mx Mz Na Nb Nd Ne Nf Ng Nk Nm Nq Nr Nw Nx Ny Oe Of Og Om Oz Pb Pc Pd Pe Pf Pg Po Qa Qd Qv Rh Rj Sr St Uc Ul Um Uv Vv) Qd(bN Cq Et Fr Ha Hq Hr Hu Hx Ib Ih Ii Ij Ik Im Ip Ir Is It Iu Jg Jh Ji Jj Jk Jl Jm Jn Jo Jp Jq Jr Kz Lu Lw Lx Ma Mc Md Me Mf Mg Mh Mi Mj Mk Ml Mm Mn Mp Mq Ms Mt Mu Mv Mw My Mz Na Nb Nd Ne Nf Ng Nh Nj Nl Nn No Nq Ns Nt Nu Nv Nw Oe Of Og Oh Oi Ok Om On Oz Pa Pb Pc Pd Pe Pg Po Pz Qb Qc Qe Qn Rj Uc) Vv(aE aG Aj Ao aP Ar As aU aW aY Bb bE bJ bN bR bX cC Ch Cq cR cT dA dC De dH dI dR Fb Fn Fp Gl gW Ha Hf Hu Hw Ib Ic Ih Ii Ik Il Iz Jj Jn Jo Jv Ki Kj Kp Ky Kz Ld Mc Mn Ms Nb Nd Ne Nf Ng Nk Nn Nq Nx Ny Oe Of Og Oi Ou Pf Pg Ph Qn Qt Qv Rb Rh Rj Sr Ss St Tz Ub Uc Ug Uh Ur Uu Uv) Mc(Ad aE aF aG aH Aj aM aN aP Ar As aU aW aX aY Ba bE bH bI bJ bN bQ bR bW bX cC cG Ch cJ cO Cq cR cT Cu cV Cw dA Db dC Dd De dF dG dH dI dL Fb Gp gW Ha Hv Hw Ib Ic Il Ir Is Ji Jj Jn Js Kj Kr Kz Ld Lz Mr Mw Mx Nc Ne Nf Nl Ns Nw Ok Ou Pf Qn Qv Qz Rb Rj Tz Ub Ur Uv) Qv(aC Ad aE aF aM As aU aW aX aY aZ bE bH bI bJ bN bQ bW cC Cq cR Cu cV Cw cZ dA Dd De dF dG dI dL dR Fb Fw Gp gW Ha Hf Hr Hv Ib Ic Id Ii Ij Il Jo Js Jt Jv Ke Kj Kr Kz Ld Me Mj Mn Mr Mx Na Nd Nf Nk Nx Ny Of Og Or Pb Pc Pg Pi Pk Qn Rb Rh Rj Sr Tz Ub Uc Ul Um Uv Vp) Nd(aC aD aE aF aG aH Aj aK aL aM aN AO aP Ar AS aU aW AX aY aZ Ba BB bE bH bI bJ bM bN BO bQ bR bS bU bV bW bX cA cC cD cE cF CH cL cM cN cR cS cT cU cV cX cZ dA dC Dd DE dF dG dH dI dK dL dM dN dR eF gL gP gW Hf Ic Kz Rb Rh) Il(aM Ar aW AX aY bE bJ bN bR cR cT Cu cV dA De dH Fp Fr Hq Hv Hw Ic Ih Ip Ir Is Ji Jj Jl Jn Jp Jr Js Jy Kp Kq Ld Lh Li Lx Lz Me Mj Mm Mr Mt Mw Mx My Nc Ne Nf Nj Nl Ns Nt Nv Nw Of Oi Ok On Ou Pb Pc Pf Ph Qe Rb Rh Rj St Ub) Jn(As bJ bN Cq cV Dd De Fp Ha Hq Hv Hw Ib Ih Ii Ij Ir Is It Iu Ji Jj Jo Jr Js Jt Kj Kp Kr Lz Md Mm Mp Mr Mt Mv Mx Mz Nc Ne Nf Ng Nj Nl Nm Nn Nq Nr Ns Nw Ny Of Oi Ok Oz Pa Pb Pc Pd Pe Pf Pg Po Pj Sr Tz Uc) Nk(Ad aE aF Aj aM An Ao Ar As aU aW aX aY aZ Ba Bb bE bJ bN bQ bW bX cC Ch Cp Cq cR CT Cu cV Cw dA Db Dc Dd DE dF dG dH dI DL Gp gW Ha Hx Ib Ic It Kj Kr Kz Ld Lh Li Qn Rj Sr St Tz Ub Uc Ue) Nw(aF Ao aY bN cG Dd De dH Fp Hq Hu Hv Hw Ih Ii Ij Ir Is Iu Jj Jo Jq Jr Js Jt Ke La Md Mm Mn Mp Mr Mv My Mx Mz Nc Ne Nf Ng Nj Nl Nn Nq Nr Ns Ny Of Oi On Oz Pa Pb Pc Pd Pe Pf Pg Po Qb Qn Sr Uc) Nb(Ad aF Aj aM An As Aw aX aY bE bJ bN bQ cC Cp cR Ct Cu cV Cw cZ Dc dF dG dH DL Fw Gp Id Kd Ke Kg Kn Ko Kq Kr Kz Ok Or Pi Pk Qn Qx Ra Rj Tz Ud Ue Ug Uk Ul Um Up Ur Ut Uv Vp Tj) aY(aM aP bE cV dG dL Fp Ha Hr Hv Hw Ib Ic Ii Ij Ir Jo Js Jt Kj Kr Kz Ld Me Mj Mn Mp Mr Ms Mu Mx Na Ne Nf Ng Nm Nq Nx Ny Of Og Ow Oz Pb Pc Pd Pg Rb Rh Rj Sr St Uc Uk Ul Ur Uv) Nf(Ao Ar aW AX aY aZ Ba bE bJ bN bR bW bX cC cR cT dA dC dH dI Fp Fr Hw Ic Ih Ip Ir Is Ji Jj Jq Jr Kf Kn Kp Kq Ld Lj Lw Lx Mq Mr Mw Nc Ne Nj Nl Ns On Ou Pf Ph Rb Ub) Ic(aE aM As bJ bN cC cV Cw Dd De dG dH Fw Gl Gp Ha Hv Hw Ib Ii Jo Jt Jv Ke Ki Kj Kr Kz Ld Me Mj Mn Na Ng Nm Nq Ny Ow Pg Ql Qn Rb Rh Rj Sr Tz Ub Uc Ue Uk Ul Um Ur Uv) Rb(cAd aE Aj aM As aU aZ bE bJ bN bW cC Cq cV Db Dd DE dG Gp gW Ha Hr Hw Ib Id Ii Jo Kj Kr Mj Mn Mx Na Nm Of Og Or Pc Qn Rh Rj Sr Tz Ub Uc Ue Ug Uk Ul Um Ur Uu) Ji(Fp Hq Hv Hw Ih Ii Ij Ir Is Iu Jj Jo Jq Jr Jt Lz Ma Md Me Mm Mn Mp Mr Mt Mv Mx Mz Nc Ne Nj Nl Nm Nn Nq Nr Ns Ny Of Oz Pa Pb Pc Pd Pe Pf Pg Po) Ld(aM As aW bE bJ bN Cq cR cV Dd De dG Fn Fw Gp gW Ha Hr Hv Hw Ib Ii Ij Jo Jt Kj Kr Kz Me Mj Mn Na Nm Ny Of Or Pb Qn Rh Rj Sr Uc Ug Uk Ul Um Uv) Nx(Ad aE aF Aj aM Ao As aU Bb bE bJ bN bQ cC cG Cp Cq Ct Cu cV Cw Dd De dF dG dH DL Fw Gl Gp Ha Ib Ke Kg Kj Kr Lh Li Lj Qn Rj Sr Tz Uc Uv) Kp(Ad aM As bJ bN Cp Cq Cu Cw Dd De dG Fw Ha Hr Hv Hw Id Ii Ij Ir Jo Jr Js Jt Kg Kj Kr Me Mj Mr Na Nm Of Or Pb Pi Pk Rj Uc Ud Ul Um Uv Vp) bN(aP bR bS bX cA cT cV dH Fp Hf Hv Ib Ih Ir Iu Jv Kq Ky Me Mi Mr Ms Mu Na Ne Ng Nl Nq Ns Ny Oe Og Oh Oi Ou Pc Pg Ph Rj Sr Ub) Ir(Fp Ha Hq Hv Hw Ih Ii Ij Is Iu Jj Jo Jr Jt Lz Mm Mr Mt Mx Mz Nc Ne Nj Nl Nm Nr Ns Ny Of Ok Pa Pb Pd Pe Pf Po Qa Qb Uc) Ar(aP bQ bS cV Fp Ha Hr Hu Ib Ih Ii Ij Jo Js Jt Jv Ke Kj Kz Me Mj Mn Mr Mv Na Ng Nm Nn Nq Nr Ny Pc Pf Pg Po Rj Sr Uc) Nc(Fp Fr Hq Hw Ih Ij Is Jj Jl Jp Jr Js Lx Lz Me Mm Mr Mw Mx Ne Ng Nh Nm Nq Ns Nt Nv Of Og Ok On Oz Pb Pc Pf Qe) bJ(aP bR bW bX cT dH Hw Ib Ih Ii Jo Kj Mi Mn Ms Mv Na Ng Nq Nr Ny Oe Og Ou Pc Pd Pg Ph Rj Sr Ss Tz Ub Uc Uu) Ok(Fp Hr Hw Ii Ij Is It Jj Jq Jr Jt Lz Md Me Ml Mm Mt Mz Ne Nl Nm Nr Ns Ny Of Om Pb Pd Pe Pf Po Qa) Pf(Fp Fr Hq Hw Ih Ik Ip Is Jg Jj Jl Jp Jr Js Lj Lx Lz Mm Mr Mw Mx Ne Nj Nl Ns Nv On Oz Pd Qe) cT(aM bE bQ bX cV dG Ha Hw Ib Ii Jo Kj Kr Me Mj Mn Na Nq Ny Of Pg Rj Sr Uc Uv) Kq(Ad As Cq Cw Dd De dG Ha Ib Ii Ij Jo Jt Ke Kj Kr Kz Me Nm Pd Po Qn Rj Uv Vp) Ou(aM As bE Cq cV Cw Dd De dG Ha Ib Ii Jo Kj Kr Kz Me Mj Ow Pg Rj Uc Ul Uv) aW(cA cV dH Fp Hw Ib Ii Jo Kj Kr Me Mj Mx Na Ne Ng Nq Ny Oe Og Pg Sr Uc) Mr(bE cC Cs De Fp Fr Hw Ih Is Jj Jq Jr Js Lj Lx Lz Mi Mw Na No Ns On) Ny(aE aM Ax Ba bE bR bW bX cC cR cV dA dI Fr Gp Is Mw On Rh St) Kj(Ax Ba cR dA dH eF Hc Hf Ip Kf Mu Ne Oh Pg Ph Qy Ra Rh Sr) Is(Hv Hw Ii Ij Iu Jj Jo Js Lz Mm Mt Mx Ne Nl Nm Nr Of Pd) Ph(As Cq Cw Dd De Ha Ib Ii Jo Jt Kr Me Na Nm Rj Uc Uv) Sr(aE bE bR bX cR eF Fb gW Ha Ii Jp Og Rj Uc Ur) Js(Fp Fr Ih Jj Jp Jq Jr Lj Mw Na No Ns On Qa Qe) bR(aM Ba bE cV Ii Jo Me Mn Na Nq Pc Pg Qn Rj) cR(aP bS cV dH Hw Ii Jo Na Ng Nq Oz Pc Pg Ub) Rh(Aj aU bE De Fb gW Ii Jo Jv Na Pg Tz Ub) Kf(Cq Cw Dd De Ha Ib Ii Jo Jt Kr Mj Uv) Nq(aE aM aU aX bE cC cV dA dI gL Mw) Hw(bE Fr Jj Jp Jr Lz Mw Ne Nl Ns On) Rj(Ax bV dA dH gW Hf Ms Ne Pg Ri Ub) Fr(Jj Lz Mm Mt Mv Mx Nm Ns Of) Mu(aF Ao cG Cq Dd De dH Dk Ib) Pg(As Ba bE cC De Fb Gp Hq St) Ax(Fp Ha Ib Ii Jo Jt Kr Uc) Mw(Jj Lz Mm Ng Nl Nm Ns Of) Ub(cV Ha Ib Kz Me Ur Uv) Ii(bX Cu Dc Fb Jy Kn St) Jj(Jr Lz Mm Mx Ne Nl Ns) Ib(Ba dA eF Fb Hc Qy) St(Al Dd De Ha Ke Qn) Jr(Hv Lz Mx Ne Nl Ns) Cs(Fp Ha Kr Li Mj) cV(aX Ba bI cN Og) Lz(Ih Lj Lx Ns) Uc(Ba Cu eF Kn) bE(dH Ne Oe Og) De(Jy Ne Og) Ha(Fb Fp Lj) Nm(Jg Jp On) Mn(dI eF Ky) Mx(Fp Ih Ns) Na(dH eF Hf) Jo(Cu dA Kn) Uv(aZ Ba dA) Mm(Et On) Ms(dG Kz) Jy(aF Qn) Oz(Pb Pc) bX(aM dI) BaUu CvQn DdKn MedA MgNg NeNl TzdH KzOg cNdG) Kk{cQ(aC AD aE aF aG aH al AJ aK AL aM AN AO aP aQ AR aS aU aV AW AX aY aZ BB BC bF BG bH bI bJ bL bM BO bP bQ bR bS bU bV bW bX bZ cA cB cC cD cE cF cG CH cI cJ cK cL cM cN CO CP Cq cR CS CT CU CV CW CX cY cZ dA DB DC DD dE dF DG dH DI dJ DK DL dM dN Dp Ed EF Et Ez Fa Fb Fn Fr Fw GL gW Ha Hb Hc Hf Hq Hr Hu Hv Hx Ic Id Ih Ij Ik Im Io Ip Iq Ir Is It Iu Iv Iz Je Jf Jg Jh Ji Jj Jk Jl Jm Jn Jp Jq Jr Js Jt Ju Jv Jy Kc Kd Ke Kf Ki Kl Kn Ko Kp Kq Ks Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mv Mw Mx My Mz Na Nb Nc Nd Ne Ng Nh Nj Nk Nl Nm Nn No Nq Nr Ns Nt Nu Nv Nx Ny Oa Oe Og Oh Oi Ok Om On Or Ou Ow Oz Pa Pb Pc Pd Pe Pf Ph Pi Pj Pk Po Pz Qa Qb Qc Qd Qe Qg Qh Qm Qn Qt Qu Qv Qx Qy Qz Ra Rb Rc Rg Rh Ri

Figure 19 Continued

Rm Ss Tz Ua Uc Ud Uf Ug Uh Uk Ul Um Un Uo Up Ur Ut Uu Uv Vo Vp Vt Vv Wm Tj) Qw(aC AD aE aF aG aH al AJ aK AL aM AN AO AP aQ AR AS aU aV AW Ax aZ BB BC bF BG bH bI bL bM BN BO bP bQ bR bS bU bW bX bZ cA cB cC cD cE cF cG CH cI cJ cK cL cM cN CO Cp Cq cR Cs CU CV CW CX cY cZ DB DC DD DE dF DG dH DI dJ DK DL dM dN Dp dR Ed Et Fa Fn FP Fw Gl gP gW Ha Hb Hf Hq Hr Hu Hv Hx Ib Ic Id Ih Ii Ij Ik Il Im Ip Iq Ir Is It Iu Iz Je Jf Jg Jh Ji Jj Jk Jl Jm Jp Jq Jr Js Jt Ju Jv Kc Kd Ke Kf Kg Ki Kj Kl Kn Ko Kp Ks Kz Ld Lh Li Lj Lu Lv Lx Ly Lz Ma Mb Md Me Mf Mg Mh Mj Mk Ml Mm Mn Mq Mr Ms Mt Mv Mx Mz Na Nc Nd Ne Nf Ng Nh Nl Nm Nn No Nq Nr Ns Nt Nu Nv Nw Nx Ny Oa Oe Of Og Oh Oi Ok Om On Or Ou Ow Oz Pa Pb Pc Pd Pe Pf Pi Pj Pk Po Pz Qa Qb Qc Qe Qg Qh Ql Qm Qn Qu Qx Qz Ra Rb Rc Rg Rj Rm Ss St Tz Uc Ud Ue Uf Ug Uh Uk Ul Um Un Uo Up Ur Us Ut Uu Uv Vo Vp Vt Vv Wm) cP(aC AD aE AF aH aI aJ aK aL aM AN Ao Ar aS aU aW aX aY aZ Ba BB Bg bH bI bJ bM BN bP bQ bR bV bX cA cC cE cF Ch cI cK cM cN Co Cp Cq cR cS CT Cu CV Cw CX cZ dA DB Dc Dd DE dG dH dK DL dM dN eF Fa Fb Fn Fr Fw gL gW Ha Hc Hf Hq Hr Hu Hv Hx Ib Ic Id Ih Ii Ij Ik Il Im Ip Iq Ir It Iu Iv Iz Jd Je Jf Jh Jj Jn Jr Js Jt Ju Jv Jy Kc Kd Ke Kg Ki Kj Kn Ko Kp Kq Ks Ky Kz Ld Lh Li Lu Lv Lx Ly Lz Mb Mc Md Me Mf Mg Mi Mj Mk Ml Mn Mp Mq Mr Ms Mu Mw Mx My Mz Na Nb Nc Nd Ne Nf Ng Nj Nk Nl Nm Nn No Nr Nw Nx Ny Oa Oe Of Og Oh Oi Ok Om Or Ow Oz Pb Pc Pd Pe Pf Pg Ph Pi Pj Pk Po Qa Qb Qd Ql Qn Qt Qv Qx Qy Qz Ra Rb Rg Rh Rj St Tz Uc Ud Ue Ug Uk Ul Um Up Ur Us Uv Vp Vv Tj) Us(aC Ad aE Af AJ Al aM aN AO aP Ar AS Aw AX Bb Bc bE Bg bl bJ BN BO bX cF Ch cI cN Co Cp Cq cR CS Ct Cu Cx cZ dA Dc Dd De Dg dI Dk dM dN Ed Ef Ez Fb Fn Fp Fr Fw gL Gp gW Ha Hc Hf Hr Hv Hw Hx Ib Ic Ih Ii Il Im In Io Ip Iq Ir Is It Iv Iz Jd Jf Jg Ji Jj Jk Jl Jn Jo Jp Jq Ju Jv Jy Kc Kd Ke Kf Kg Kj Kl Ko Kp Kr Ks Ky Kz Ld Lh Lj Lu Lw Lx Ly Lz Ma Mb Mc Md Mf Mg Mi Mk Mn Mp Mr Mt Mv Mw Mx My Mz Nc Nd Ne Nf Ng Nj Nk Nl No Ns Nt Nu Nv Nw Nx Ny Oa Of Og Oh Om On Or Ou Ow Oy Oz Pa Pb Pc Pf Pg Ph Pi Pj Qa Qd Qe Qh Ql Qn Qt Qu Qv Qy Qz Ra Rb Rh Ri Rj Sr Ss St Tz Ua Ue Uf Ug Uh Uk Um Un Ur Ut Uv Vv Wm Tj) Jo(aC Ad aE Af AJ aL aM aN aO AP Ar AS AW AX aZ BC Bg bl bJ bM BN BO bV bX bZ cA cC cF CH cI cN CO Cp Cq cR CS Ct CU CW Cx cZ dA Dc Dd dE DG dI Dl dM dN Dp EF Et Ez Fb Fn Fp Fr gL Gp Ha Hc Hf Hw Ib Ic Ih Ik Il Im In Io Ip Iq Ir Is Iv Iz Jd Je Jg Jh Ji Jl Jm Jn Jp Jt Ju Jv Jy Kc Kd Kf Kl Kn Kp Kq Kr Ks Ky Li Lv Lw Lx Ly Lz Ma Mb Mc Mg Mi Ml Mm Mn Mp Mr Mt Mu Mv Mx My Nb Nc Nd Ne Nf Ng Nj Nk Nl Nn Nt Nu Nw Nx Oa Og Oh Ok Om On Ou Oy Pb Pd Pg Pi Pj Po Qa Qd Qe Ql Qm Qn Qt Qu Qv Qx Qy Qz Ra Rb Rf Rg Rh Rj Rm Sr Ss St Tz Ua Ub Uc Ue Uf Uk Ul Um Un Ut Uv Vo Vp Wm Tj) Oy(aC aE Af AJ Al aN AP Ar AS AW AX aZ Bb BC bE Bg bl bJ BN Bo bV bX bZ cB cC cI CO Cp Cq cR cS Ct CW Cx cZ dA Db Dc Dd dE DG dI Dk dM dN Ed Ez Fb Fn Fp Fw Gp Hf Hr Hu Hw Ic Id Ih Ik Il Im In Ip Iq Ir Is Iu Iv Iz Jd Jf Jg Ji Jj Jk Jl Jn Jp Jq Ju Jv Kc Kd Kf Ki Kj Kl Kn Ko Kr Ky Lh Lu Lv Lw Lx Ly Lz Mb Mc Me Mf Mg Mh Mj Ml Mn Mp Mr Mt Mx Mz Na Nc Nd Ne Nf Nh Nj Nk Nl Nn No Nq Nr Nt Nu Nv Nw Nx Ny Oa Oe Og Oh Ok Om On Or Ou Ow Oy Oz Pa Pc Pd Pe Pg Ph Pi Pk Po Qa Qd Ql Qm Qn Qt Qu Qv Qz Ra Rf Rg Rh Ri Rj Sr Ss St Ua Ue Uf Ug Uk Un Ur Ut Uv Vv Wm Tj) In(aC aD aE AF aG aH aI aJ aK aL aM aN AO aP aQ AR AS aU aV aw aW aX aY aZ Ba BB BC bE bF BG bH bI bL bM BN bO bP bQ bR bS bU bV bW bX bZ cA cB cC cD cE cF cG CH cJ cK cL cM cN CO Cq cR CU cV cW cX cY cZ dA dB dC DD DE dF dG dH dI dJ DK dL dM dN Dp Fb Fn Fr Fw gL GP gW Ha Hc Hx Ib Ic Ih Ij Il Io Ip Iq Iv Jd Je Jn Js Ju Jv Jy Kc Kf Kj Kp Kq Kr Ld Lv Ly Mc Mi Mj Mk Ml Mn Mr Ms Mt Mu Mw My Mz Nb Nc Nd Ne Nf Nj Nk Nl Nq Nv Nx Ny Of Og Oh Ou Pb Pg Ph Pi Po Pz Qd Qt Qv Qx Qy Rb Rf Rh Rj Sr Tz Uc Ue Ul Um Un Ur Vp Vv Tj) Ub(aC aD aE aF aG aH al aJ aK aL an AO aP aQ aR aS aU aV aW aX aY aZ bB bC bF BG bH bI bL bM bO bP bQ bR bS bU bV bW bX bZ cA cB cC cD cE cF cG CH cI cJ cK cL cM cN CO cR cS CT cU cV cW cX cY dA dB DD DE dF dG dH dI dJ DK dL dM dN dR eF fP Fw gL gP gW Hv Hw Hx Ij Ir Iv Jd Je Js Ld Mj Mk Ml Mn Mr Ms Mt Mw My Nb Nd Nq Nv Ny Of Og Po Qh Qx Tz Uc Ul Um Ur Vp) aY(aC Ad aE Af AJ aM aN aS aX Ba Bb bl bJ BN Bo bV cA cC Ch cJ Cq cS CT cV Cx cZ Db Dd DE dH dL eF Fb Fn Fr gL Gp gW Ha Hf Hr Hw Ib Ic Ih Ii Ij Il Im Io Ip Iq Iu Jd Jj Jt Ju Jv Jy Kc Kg Ko Kr Ks Ky Kz Ly Mb Mc Me Mk Ml Mq Mr Mu Mw Na Nb Nc Ne Nf Ng Nj Nk Nl Nn Nw Ny Of Og Or Ow Pb Pd Pf Pg Ql Qv Qy Rb Rj Sr St Uc Ue Ug Uk Ul Um Ur Uv Vv Tj) eF(Ad aE aF Aj aM Ao AS aW Ba Bb bE bJ bN bQ cC cE cG Ch cI Co Cp Cq Ct Cu cV Cw cZ dC Dd dF dG dI DI Ef Et Fn Fp Fw gL Gp gW Ha Hr Hv Hw Id Ii Ij Io Iq Ir Iu Jd Jh Jn Jr Js Jt Ju Jv Ke Kn Ko Kz Lh Mb Mc Me Mj Mk Ml Mr Na Nd Nf Ng Nj Nm Nr Ny Of Ok Om Or Ow Pb Pd Pe Pf Pg Pi Pk Po Ql Qn Qv Qx Rb Rf Rj Ud Ug Uh Uk Ul Um Up Ur Uv Vp Vv Tj) bE(aE Af Aj Ao Ar AS aV aW Ba Bb bI BN bO bS bV cA cE Ch cI cM cS cT cW dA Dd De Fn Fp Gp Hr Hw Ib Ii Il Im Io Iq Iu Jd Jj Jn Ju Jv Jy Kg Kj Kp Kq Kr Ky Lu Lv Ly Mc Mi Mm Mn Mr Mu Mw Nb Nc Ne Nf Nj Nk Ny Oe Og Pf Pg Ph Ql Rb Rf Rj Sr Ue Ug Uh Uk Ur Vv) cT(aC aE Af Aj As Bb bJ BN Cq cS Ct cV Cw cZ Dd De dI Fa Fn Fw Gp Ha Hr Hv Hw Ib Ii Il Iq Jd Js Jt Ju Jv Kc Kg Kj Ko Kr Ld Lh Ly Mc Mj Mn Mr Mu Nf Ng Nj Ny Of Pb Pd Pe Pf Pg Po Ql Qn Qv Qx Qy Rb Rf Rj Sr Uc Ud Ue Ug Uk Ul Um Ur Uv Vp Vv Tj) gL(aE aF Aj Al Ao AS aW Ba Bb bI BN cA cE Ch cI cS CX dA dC Dd De dF dH Fp Gl Gp gW Ha Hw Ib Ic Ii Il Io Iq Iu Iz Jd Jq Ju Jv Kg Kj Ko Kr Ly Mc Mn Mr Nb Nf Ng Nj Nk Nr Ny Oe Of Og Pf Pg Ql Qn Qv Rb Rf Tz Uc Ue Ug Uh Ur Uu Uv) Il(aC Af As aX Ba bI bJ BN bV cN cR cS Cu dA Db dI dN Fb Fn Fp Fr Gp Hw Ic Io Ip Ir Iv Jd Jn Jq Ju Jv Kc Kf Kj Kp Kq Kr Lu Lv Lw Ly Mc Mi Mn Mp Mu Mw My Nb Nc Ne Nk Nl No Nw Nx Oh Ph Qd Qt Qv Qy Rb Rf Sr St Ue Ug Un) Mn(aC aE Af aJ aM aN aO Ar aS aX Ba bI bJ BN bS bV bX bZ cN cO Cq cR cS cU cZ dA dI dM dN Fb Fr Gp gW Ha Ib Ic Ih Iq Jj Jp Jy Kq Ky Ld Mc Mi Mu Mw Nb Nf Nk Nw Og Oh On Pb Ph Qd Qv Qy Rf St Ur Tj) Ba(aC aE aJ aL Ao aW aX Bg bJ bN bV cC cE Ch cI cM cN Co Cq cR cS Ct cV cZ dA Dd dI dN gW Ha Hw Ij Iq Jd Je Js Kc Kj Mj Mk Mr Ms Mw My Nb Nd Nf Nk Of Og Pb Po Pz Qx Tz Uc Ul Um Vp Tj) bN(aC Af AJ As aX Bb bI Bn bV cN cR cS cZ dA Dd dI dM dN Fb Fn Fp Fr Gp Hw Ic Io Jd Jv Jy Kc Kg Kj Kq Kr Ky Lu Lv Ly Lz Mc Mi Mu Mw Nb Nc Nj Nk Nw Ny Pf Pg Qv Rb Rf Rj Sr Ue Ug) bV(Af aM As bJ Bn Cq cZ Dd De Fn Fw Gp Ha Hw Ib Ii Io Iq Jd Jt Ju Jv Kg Kj Ko Ly Mc Mj Mu Nf Nk Ny Of Pf Pg Po Ql Qv Rb Rj Sr Uc Ue Ug Uk Uv Tj) dA(aE Aj As aV aX Bn Cq cS Dd De Fn Fp Ha Hr Hw Ib Io Iq Jj Ju Jv Kc Kg Kj Kr Mr Nf Nj Nk Ny Of Or Ow Pb Pd Pf Pg Qv Rf Rj Ue Uk Ul Ur Uv Tj) Io(aC aE aF aJ aM Ao aS aW aX bI bJ Bn bO bX cA Ch cI cN Cq cS cZ dC dI dM dN Gp gW Ha Ib Ic Im Iq Lv Mr Nf Nk Of Og Pb Qv Rf Um Ur Tj) Rf(aC Af Ao aS aX Bb bI bJ Bn cN Cq cS cZ Dd De Fp Ha Ib Ii Iq Js Kj Kr Mc Mj Mk Mr Mz Nd Nf Nk Ny Og Pb Pg Po Qv Qx Sr Uc Vp Tj) aX(aE Af Aj AS aW Bb bI cI cS Fn Fp Gp Hw Im Ip Jd Jj Ju Jv Jy Kj Ko Kr Mc Mr Mu Nb Nf Nj Nk Nw Pf Pg Rb Rj Sr St Ue Ug) Qv(aC aE aJ aL aM aZ bI bJ cI cN Cq cS cZ DD dI gW Ha Ib Ij Iq Js Kc Mj Mk Ml Mr Nf Nk Of Pb Qx Uc Ul Um Vp Tj) Gp(aC aE AF aJ Ao aS aW bB bF Bg bH bI bP cE Ch cI cN Co cS cZ Dd dI dM dN gW Ib Ij Jd Mk Nf Nk Of Qx Uc Tj) Mu(aC aE aO aW Bb bF Bg bH bQ cE cG Ch cI Co cS cZ De gW Ij Iq Jd Md Mk Mr Mt Mw My Nb Nd Nq Ny Pb Po Qx Tz Tj) bI(aE Af As Bn Dd De Fn Fp Hr Hw Ib Jd Ju Jv Kc Kg Kj Ko Kr Mb Mc Nf Nw Ny Of Ow Pg Rj Sr St Ue Ug Uk Um Tj) Ue(aC aM aN aS aW bJ bS bX cN Cq cR cS cZ Dd dH dI dM dN gW Ha Iq Mr Nd Nf Nk Pb Vp Tj) Nf(As cN cS Fn Fr Hw Ju Jv Jy Kj Kp Kq Kr Lu Lv Mc Mi Mw Nb Nc Ne Nj Nl Ny Rb Sr) Kj(aC aM aN aS bJ bX cI cN cR cS cZ dI dM dN Ef Ic Kp Kq Nk Ph Qy Sr Ua Tj) Ib(As Bo Cp Ef Fr Hc Jh Ju Jv Jy Kp Kq Lv Mi Mv Mw My Nb Nq Ny Ph Rb Sr) Ha(aJ cN Fr Ju Jv Jy Kf Kp Lv Lx Mc Mi Mw Nb Nw Qd Sr St Ug) cS(Af As Bn De Fp Hw Ii Ju Jv Kg Ko Kr Nj Ny Pf Pg Sr Ug) Dd(Af Dc dI Fr Hw Im Jy Kp Kq Kr Lv Lw Ly Nb Nw Ph St) Uc(Bo Cp Cu Fr Jy Kf Kp Lv Mi Mw Nb Nw Ph Qd Qy Sr) Jv(aC aE aM aN aS bJ Cq cR cZ dC dI Iq Mr Nd Pb Tj) Kq(Af Cq De Ij Iq Js Mj Mr Of Pb Po Ul Vp Tj) cN(Af As Bn De Fp Hw Ii Jd Kr Nj Nk Pf Pg Sr) Ju(aC aE aM aN aS bJ cI cZ dC dI gW Pb Tj) Tj(As Jy Kp Mi Mw Nb Nc Rb Ug) aJ(Af Fp Hw Jd Ko Kr Ny Pg Sr) dI(Af AS Hw Iq Kr Nj Ny Pg) Fp(aC aE aS aW bO cI cW) Jy(aF Cq Ij Mr Of Po Vp) Mi(bJ Cq Of Pb Ul Um) Nk(As Kc Mc Nc St Ug) Kr(aS bO dM dN gW Og) aC(Hw Jj Nj Pg Sr Ug) Af(aE Cv

Figure 19 Continued cX Kc Lv) Bn(Jq Lv Lw Nw St) Of(Mw My Nb Qy Rb) Sr(aE aS bO dM) Kp(Cq Iq Mr Pb) Ch(Bo Mw Qy) Po(Cu Fr Lx) Nj(aE cC dE) St(Al
Iq Vp) Nw(aF Ao Vp) aS(As Hw Ny) Lv(Iq Js) Mc(Mk Ml) dN(As De) AoBo NbJe HwaE IiJq NyVp} In{aY(aC AD aE AF aG aH aI AJ aK AL aM AN AO AP aQ AR AS aU aV AW AX aZ Ba BB BC bF BG bH bI bL bM Bn BO bP bQ bR bS bU bW bZ cA cB cC cD cE cF cG CH cJ cK cL cM cN CO Cp Cq cR CS Ct CU CV CW CX cY cZ dA DB DC DD DE dF DG dH DI dJ DK DL dM dN Dp dR Ed EF Et Ez Fa Fb Fn FP Fr Fw GL GP gW Ha Hb Hc Hf Hq Hr Hu Hv Hw Hx Ib Ic Id Ii Ij Ik Il Im Iq Is It Iu Iz Jd Je Jf Jg Jh Ji Jj Jk Jl Jm Jo Jp Jq Jr Js Jt Ju Jv Jy Kd Ke Kf Kg Ki Kj Kl Kn Ko Kq Kr Ks Ky Kz Ld Lh Li Lj Lu Lv Lw Lx Lz Ma Mb Mc Md Me Mf Mg Mh Mi Mj Mk Ml Mm Mn Mp Mq Mr Ms Mt Mv Mw Mx My Mz Na Nc Ne Nf Ng Nh Nj Nl Nm Nn No Nq Nr Ns Nt Nu Nv Ny Oa Oe Of Og Oh Oi Ok Om On Or Ou Ow Oy Oz Pa Pb Pc Pd Pe Pf Pg Pi Pj Pk Po Pz Qa Qb Qc Qd Qe Qg Qh Ql Qm Qn Qt Qu Qv Qx Qy Qz Ra Rc Rg Ri Rj Rm Sr Ss St Tz Ua Uc Ud Ue Uf Ug Uh Uk Ul Um Un Uo Up Ur Us Ut Uu Uv Vo Vp Vt Wm Tj) Iv(aC AD aE AF aG aH aI AJ aK AL aM AN AO AP aQ AR AS aU aV Aw AX aZ Ba BB BC bE bF BG bH bI bJ bL bM Bn BO bP bQ bR bS bU bV bW bZ cA cB cC cD cE cF cG CH cJ cK cL cM cN CO Cp Cq cR CS Ct CU CV CW CX cY cZ dA DB DC DD DE dF DG dH DI dJ DK DL dM dN Dp eF Et Ez Fb Fn Fp Fr Fw gL Gp gW Hc Hq Hr Hu Hv Hw Hx Ic Ih Ii Ij Ik Io Ip Iq Ir It Iu Je Jg Jh Jj Jk Jl Jm Jn Jo Jp Jq Jr Js Jt Jv Jy Kf Ki Kp Kq Kr Ks Kz Lj Lu Lw Lx Ly Lz Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Nj Nl Nm Nn No Nq Nr Ns Nt Nu Nv Nw Ny Oe Of Og Oh Oi Om On Or Ou Oy Oz Pa Pb Pc Pd Pe Pf Pg Ph Pi Po Pz Qa Qb Qc Qe Qn Qt Qv Qw Qy Qz Ra Rb Rf Rh Rj Sr St Tz Ue Ug Um Un Ur Vv) cP(aC AD aE AF aG AJ Al aM AN AO AP aQ Ar AS aV AW aX aZ Ba BC bE BG bH bI bJ bL bM BN bO bP bQ bR bS bX bZ cA cB cC cD cF CH cJ cK cM cN CO Cp CQ Cs Ct CU CV CW CX cZ dA DB Dc Dd DE dF DG dI dK Dl dM dN EF Et Ez Fb Fn Fp Fr Gp Hr Hw Ih Ik Il Im It Iu Jg Jh Ji Jj Jk Jl Jm Jo Jp Jq Jr Js Jt Jy Kf Kp Kq Ks Ky Kz Ld Lh Li Lj Lu Lv Lw Lx Ly Lz Ma Mb Mc Md Mf Mg Mh Mi Mj Mk Mm Mn Mp Mr Mt Mu Mx My Mz Na Nc Nd Ne Nf Nh Nj Nk Nl Nm Nn No Ns Nt Nu Nv Oa Oe Of Og Oh Oi Ok Om On Oy Oz Pa Pb Pc Pd Pe Pg Ph Pi Pj Po Qa Qb Qe Qt Qv Qw Rb Rj Rm Sr St Ue Uk Um Un Us Ut Vv) Nx(aE AF AJ Al Ao Ar AS AW Ax aZ Ba Bb bE bG bH bI bJ BN bP bR bS bV bX cA cF Ch cN Cp cQ cR CS cT CU cV Cx cZ dA Dd Dg dI dK Dl dM dN eF Et Fb Fn Fp Fr GL Gp Ha Hb Hc Hq Hr Hu Hv Hw Hx Ib Ih Ij Ik Im Ip Iq It Iu Jd Jg Jh Ji Jk Jl Jm Jn Jp Jq Jr Js Jt Ju Jv Jy Kc Ke Kg Ki Kj Kp Kq Kr Lh Lj Lu Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Nh Nj Nl Nn No Nq Nr Ns Nt Nu Nv Nw Ny Oe Of Og Oh Oi Om On Or Ou Oz Pa Pb Pc Pd Pe Pf Pg Ph Pi Po Pz Qb Qc Qe Qg Qt Qv Qw Qy Ra Rb Rf Rh Rj Sr Tz Ub Uc Ue Uh Uk Ur Uv Vp Vv Wm) Nb(aC AD aE aG aH aI AJ aK AL aM AN aO AP aQ AR aS aU aV Aw AX aZ Ba BB BC bE bF bG bH bI bL bM BO bP bR bU bW bZ cA cB cC cD cE cF cG cH cJ cK cL cM cO Cp cR Cs Ct CU CV CW CX cY dA DB DC dD dE dF DG dH DI dJ DL dM dN Dp dR Ed EF Ez Fa Fb Fn fP Fw Gl GP gW Hb Hc Hf Ic Id Iz Je Jf Ju Jv Jy Kd Ke Kf Kg Ki Kl Kn Ko Kp Kq Kr Ks Ky Ld Oa Or Ow Pi Pj Pk Qg Qh Ql Qn Qt Qu Qv Qx Qy Qz Ra Rb Rf Rg Ri Rj Rm Sr Ss St Tz Ud Ue Uf Ug Uh Uk Ul Um Un Uo Up Ur Ut Uu Uv Vo Vp Vv Tj) cT(aE Af aJ aP aW Bb bE bN bP bR bV bX cF CH cI cN cQ cR cS cU cV cW dA Dd dK dM dN Dp dR Ed EF Ez Fa Fb Fn Fw GL Gp gW Ha Hb Hc Hf Hw Ib Ic Id Ih Il Ip Iq Ir Iu Iz Jd Je Jf Jm Jn Jo Ju Jv Jy Kc Kd Kc Kf Kg Ki Kj Ko Kp Kq Kr Ks Ky Kz Ld Mb Mc Mn Mr Mu Nd Nf Nk Nt Nu Nw Oa Oh Or Ou Ow Oy Pg Ph Pi Pj Pk Qd Qg Qh Ql Qm Qn Qt Qu Qv Qx Qy Qz Ra Rb Rc Rg Ri Rj Rm Ss St Tz Ua Uc Ud Ue Uf Ug Uh Uk Ul Um Un Uo Up Ur Ut Uu Uv Vo Vp Vt Vv Wm Tj) cI(aJ aP aX Ba Bc bE bJ bR bV bX cB cF cH cN Cp cQ cR cS Cu Dc dM dN Dp Ed Ez Fa Fn fP Fr Fw Gl Gp Ha Hb Hf Ib Ic Id Ih Ik Io Ip Iq Ir Is Iu Iz Jd Je Jf Jl Jm Jn Ju Jv Kc Kd Ke Kf Kg Ki Kj Kl Kn Ko Kp Kr Ks Ky Kz Ld Lv Ly Mb Mi Mu Mw Nd Ne Nk Nt Nw Oa Oh Om On Or Ou Ow Pi Pj Pk Qd Qg Qh Ql Qm Qn Qu Qv Qw Qx Qy Qz Ra Rb Rc Rg Rh Ri Rj Rm Sr Ss St Tz Ua Uc Ud Ue Uf Ug Uh Uk Ul Um Un Uo Up Ur Us Ut Uu Uv Vo Vp Vt Wm Tj) Kp(aC Ad aE Af aJ Ar As aW Ax aZ Ba Bb Bc bE bI bJ BN bV bX cE Ch CQ cR cS Cw Cx dA Dd dM eF Fb Fn Fr Fw gL Gp gW Ha Hr Ib Ih Ii Ij Il Ip Iq Jm Jn Jo Js Jt Ju Jv Jy Kc Kg Kj Kq Kr Ks Ly Mb Mc Mj Mn Mr Mu Mw My Na Nd Nf Nj Nk Nm Nw Oa Of Oh Or Ou Oy Pb Ph Pi Qd Qt Qv Qy Rb Rf Rh Rj Sr Ub Uc Ue Ug Uk Ul Um Ur Us Uv Vp Vv) gL(aE AF Ao Ar aS aW Ax Bc BN bV cF Ch cQ CS Cx dA dC dH dM Dp Fb Fn Fp Gl Gp Hb Hc Hf Ib Ic Il Io Ip Iq Jd Jf Jn Jv Jy Kc Ke Kf Ki Kj Kq Kr Ks Ky Kz Ld Lj Ly Mb Mc Mn Mr Nd Nk Nq Oa Oh Or Ou Ow Pc Ph Pi Qg Qm Qn Qt Qv Qw Qx Qy Ra Rb Rf Rg Rh Ri Rj Sr St Tz Ub Uc Ue Uh Uk Ul Um Un Us Uu Uv Vo Vv Wm) Ph(Af Aj Al aM Ao aS aW Ba Bb Bc bI bJ BN bV cN cQ cR cS dA Dd dM dN eF Fb Fp Fr Gp Ha Hc Hw Ij Il Ip Iq Iu Jn Jo Ju Jv Jy Kc Ki Kj Kq Kr Lu Ly Lz Mc Mn Mr Mu Mw My Nc Ne Nf Nl Nr Oh Or Ou Oy Pg Qg Qt Qv Qw Qy Ra Rb Rf Rh Rj Sr Ub Ue Uk Un Us Vv) Ub(aE Ar aS aW Ax Ba Bc bI bJ bN bS bV cQ cR cS Ct CU dA dK dM dN Dp eF Ez Fb Fr Gp Hc Hf Ih Il Io Ip Iq Ir Is Jm Jn Jy Kc Kq Kr Ks Kz Ld Lv Ly Mb Mc Mw My Nf Nj Nl Nw Oh Om On Qd Qt Qv Qw Qy Rb Rf Rh Rj St Un Ur Us Vv Wm) Rf(Af Al Ao aS aW Ax Ba Bc bI BN bV cN cS Ct dA Dd dK dM dN eF Fb Fn Gp Ha Hc Hf Ii Il Iq Iu Jn Jo Ju Jv Jy Kc Kj Kr Kz Lu Ly Lz Mc Mf Mj Mn My Nd Ne Nf Nj Nk Nl Ns Ny Or Ou Qt Qv Qw Qy Qz Ra Rb Rh Rj Sr Ue Vp Vv) Kq(Ad aF Ao As aW Ba Bb bJ bN bV cQ cS Cw Dd De Fb Ha Ib Ii Ij Il Iu Jd Ji Jo Jq Jt Jv Kc Ke Kj Kr Kz Lh Ly Mc Me Mj Mn Mr My Nd Nf Nj Nk Ny Of Om Or Ou Oy Pd Pg Po Qn Qv Qw Qy Rb Rh Rj Sr Ue Uh Uv Vp Vv) Qd(cQ Fp Fr Hw Hx Ih Io Ir Is Iu Ji Jj Jl Jn Jo Jr Jt Jv Lu Lv Ly Ma Mb Mc Me Mf Mj Mk Ml Mm Mn Mq Mr Mu Mw Mx My Na Nc Ne Nf Ng Nh Nj Nm Nq Nr Ns Nu Nw Ny Oi On Or Oy Pa Pe Pf Pz Qc Qv Qw Rb Rh Sr Us) cQ(aE aJ Ar aW Ax Ba Bc bV bX CS Cu Dc dM dN eF Ez Fb Fr Hc Ih Ip Ir Is Jm Jn Jy Kf Kn Ks Ky Ld Lj Lv Lx Ly Mb Mr Mu Mw Nd Nt Nw Oa On Ou Pi Qa Qb Qe Qt Qv Qw Qy Rb Rh Rj Rm Sr St Un Ur Us Vt Vv) Kc(Af Ar aS aW Ax Ba Bc bI bJ BN bV cR cS Ct Cu dA Dd dM dN eF Ez Fb Fr Gp Hc Ih Il Io Iq Jn Ju Jv Jy Kr Ks Lv Mc Mr Mt Mu Mw My Nk Nl Nw Oh Ou Pi Qt Qv Qw Qy Rb Rh Rj Sr Un Us Vv) Ou(aS aW Ba Bc bE bI bJ bN bV bX cR cS Ct cZ dA dM dN Dp eF Fb Fr Hc Il Ip Iq Jn Ju Jv Jy Kr Kz Ly Lz Mc Mf Mj Mk Ml Mn Mu Mw My Nf Nj Nk Nw Or Qv Qw Qy Rg Rh Tz Ue Us Vv) bV(aW Bc bJ bN bR bX cV Dp eF Fb Fw Gp Hc Hf Ih Il Ip Iq Ir Iu Jd Jn Jv Jy Ki Kj Kr Ks Kz Ld Mb Mc Mn Mr Mu Nd Nk Nq Pi Ql Qt Qv Qw Qy Qz Ra Rb Rh Rj Sr Uh Uk Uv Vv) Io(aE aJ aP Ar aS aW Ax Ba bI bX Cp CS Cu Dc dM dN EF Ez Fa Fb Gp Hc Hf Ic Id Is Jy Kf Kl Ky Oa Qt Qv Qw Qy Rb Rh Rj Rm Sr St Ue Uf Ur) aW(Ba bE bI bX cR cS Cu dA dN eF Ez Fb Gp Hc Ip Ir Is Jn Jy Kf Kr Lv Ly Mu Mw Nk Nt Nw Oh Om Qt Qv Qw Qy Rb Rh Sr Un Us Vv) Qw(Ax Ba Bc cN cS Cu dA dM eF Ez Fb Fr Ih Il Ip Ir Is Jm Jn Jy Kf Ks Mr Mu Mw My Nw Oh Om Qt Qv Qy Rh Sr Un Vv) Jn(Af Ba bN bX cS dM Dp eF Fb Fn Fw Ha Hc Is Jv Kr Kz Lv Nk Ok Or Ql Qn Qv Qy Qz Rb Rh Rj Tz Ue Us Vv) Qv(aC aX Ba Bc bE bI bJ cN cR cS Cu cZ dA dM dN Dp eF Ez Fb Hc Ih Ip Jv Ks Mw Nj Qt Qy Rh Un Vv) Is(Fr Hw Ii Ij Ik Il Ir Iu Ji Jj Jr Js Jv Lv Ly Lz Mb Mm Mr Mu Mw Nc Nj Nm Nr Nw Ny Ok Oy Pf) Us(Ar Ba Bc cN Cp cS Cu dA dM eF Ez Fb Fr Hc Ih Ir Jm Jp Jy Kf Lv Mr Mw My On Qt Sr Un Vv) Vv(Bc bE Ch cN cS dA dM dN Fb Ib Il Ip Jo Kf Mk Mw Nf Nk Of Oy Rh Sr Ue Un Ur) Ba(Af Ch Fb Ib Il Iq Jv Kj Ly Mc Nd Rb Rh Rj Sr St Uc Ue Uu Uv Vo) Rb(aJ Ax Bc bE bH bI cN cR cS Cu dA dM Fb Ih Ir Lv Mw Qt Rh Un) Fb(Ax Bc bH bN cS dA dM Ih Il Iq Ir Mb Mc Mw My Rh Sr Ue) Sr(Ax Bc cS Cu dM Fr Ha Iq Jp Kj Mw Nf Nw On Rj Ue Un) Nk(Cs dA dM Ih Ir Ji Lv Nw Ok On Qa Qe St Ue Un) Rh(aJ Bc bI CS Cu dA dM eF Il Mw My Qt Un) Ok(Ih Im Ir Jo Jr Lv Ly Mb Mm Nf Nm Of Oy Wm) Mu(aF Bb bF Bg bN Ch Co Cq De Dk dM Hf Ib) Il(cS Cu Hc Ir Ji Jy Kf Ks Lj Lv Qt Un) eF(aE aS Ax bN Ip Kr Ks Mb Oh Pi Rj Ue) Kf(dA Dd Ha Iq Jo Kg Kj Kr Oy Uc Ue) cS(bN Hc Ip Kj Kr Kz Ly Nd Pi Qt Qy) Cu(bN Ha Iq Jo Kj Kr Ly Nd Oy Uc) Mw(Hb Hc Ir Jv Ki Kr Kz Lv Or) Qt(bN bX dM Hf Ki Kz Ly Mc Nf) dM(Ar bN Kr Ly Mb Mr Nd Pi) St(Al Iq Lz Nj Nl Or Vp) Un(Af Ao Iq Jv Ny Or Uh) Ir(Iu Ji Jv Lv Ly Oy) Ji(Lv Ly Mm Nm Oy) Ax(Jv Kr Ly Qy) Jy(Af BN Iq) Nw(Af Bn Nm Uh) Oy(Fr Hc

Figure 19 Continued

On Qy) dA(aV bX Nd Ur) Ch(Hc Qy) Cs(Fp Lz) Lv(Ih Lj) My(Ki Kz) Iq(Dc Rm) Jv(Bc Ip) Kj(Hc Qy) bN(cN dN) AfOm NmOn Mbbl NdcN
UeKs KrOh aSbJ} Mu{Ib(aC AD aE aF aG aH aI AJ aK AL aM AN AO AP aQ aR AS aU aV Aw AX aY aZ Ba BB BC bE bF BG bH bI bJ bL
bM BO bP bQ bR bS bU bV bW bX bZ cA cB cC cD cE cF cG CH cJ cK cL cM cN CO Cp Cq cR CS Ct CU CV CW cX cY cZ dA DB DC DD
DE dF DG dH DI dJ DK DL dM dN Dp dR Ed EF Et Ez Fa Fb Fn Fp Fr Fw GL Gp gW Ha Hb Hc Hf Hq Hr Hu Hv Hw Hx Ic Id Ih Ii Ij Ik Im
Io Ip Ir Is It Iu Iv Iz Jd Je Jf Jg Jh Ji Jj Jk Jl Jm Jn Jo Jp Jr Js Jt Ju Jv Jy Kd Ke Kf Kg Ki Kj Kl Kn Ko Kq Kr Ks Ky Kz Ld Lh Li Lj Lu Lv Lw
Lx Ly Lz Ma Mb Md Me Mf Mg Mh Mi Mj Mk Ml Mm Mp Mq Mr Ms Mt Mv Mw Mx My Mz Na Nc Nd Ne Nf Ng Nh Nj Nk Nl Nm Nn No
Nq Nr Ns Nt Nu Nv Nw Nx Ny Oa Oe Of Og Oh Oi Ok Om On Or Ou Ow Oy Oz Pa Pb Pc Pd Pe Pf Pg Pi Pj Pk Po Pz Qa Qb Qc Qd Qe Qg Qh
Ql Qm Qt Qu Qx Qy Qz Ra Rb Rc Rf Rg Ri Rj Rm Sr Ss St Tz Ua Ub Uc Ud Ue Uf Ug Uh Uk Ul Um Un Uo Up Ur Ut Uu Uv Vo Vp Vt Wm
Tj) Ao(aC AD aE aH Aj aK Al aM AN Ap AS aU aV AW AX aY aZ Ba BB BC bE bF BG bH bI bJ bM BO bQ bR bS bU bV bW bX cA cC cD
cE cF cG Ch cK cL Co Cp CQ CS CT Cu CV CW cX cZ dA DB DC Dd De dF DG dH Di DK DL dM dR EF Et Ez Fa Fb Fn Fp Fr Fw GL gW
Ha Hb Hc Hf Hq Hr Hu Hv Hw Hx Ic Id Ih Ij Ik Im Io Ip Ir Is It Iu Iv Jd Je Jf Jg Jh Ji Jj Jl Jm Jn Jo Jp Jq Jr Js Jt Kd Ke Kg Ki Kj Kn Ko Kp Kq
Kr Kz Ld Lh Li Lj Lu Lv Lx Lz Ma Mc Md Me Mf Mg Mh Mi Mj Mk Ml Mm Mn Mp Mq Mr Ms Mt Mv Mw Mx My Mz Na Nb Nc Ne Ng Nh
Nj Nk Nl Nm Nn No Nq Nr Ns Nt Nu Nv Nw Nx Ny Oe Of Og Oh Oi Ok Om On Ou Ow Oz Pa Pb Pe Pf Pg Ph Pi Pk Po Qa Qb Qd Qh Ql Qt
Qv Qx Qy Qz Ra Rb Rc Rf Rg Rh Sr St Tz Ub Ud Ue Uf Ug Uk Un Uo Up Ur Ut Uv Vp Vt Wm Tj) Qw(aC Ad aE aH AJ An Ap AR AS aU aV
Aw AX aZ Ba bB Bc bE bH bI bJ bN BO bP bQ bS bX bZ cA cB cF cH cK cL cN CP Cq cR cS CT CU CV Cw CX cZ Dc Dd dE dF Dg dH DI
dK dM dN dR Ed EF Et Ez Fa Fb Fn Fp Fr GL Gp gW Hb Hf Hv Hw Hx Ic Id Ih Ij Ik Im Ip Ir Is It Iv Iz Jf Jg Jh Ji Jj Jl Jm Jn Jp Jq Jr Js Jt Ju Jv
Jy Ke Kf Kg Ki Kn Kq Kr Ky Kz Ld Lh Li Lj Lu Lv Lw Lx Ly Lz Ma Mb Mc Me Mf Mg Mh Mi Mk Ml Mm Mn Mp Mr Ms Mt Mv Mx Mz
Na Nb Nc Ne Nf Ng Nh Nj Nk Nl Nm Nn No Nr Ns Nt Nu Nw Nx Ny Oa Oe Og Oh Oi Ok On Or Ow Oz Pa Pb Pc Pe Pf Ph Pi Po Pz Qa Qb
Qc Qe Qg Ql Qm Qn Qt Qu Qx Qy Qz Ra Rb Rc Rg Rh Ri Rj Sr St Tz Ua Ud Ue Uf Ug Uk Ul Um Un Uo Up Ur Uu Vo Vp Vt Vv Wm Tj)
Af(aC AD aG aH aI AJ aK AL aM AN aO AP aQ aR aS aU Aw AX aY aZ Ba BB BC bE bH bI bL bM BO bP cB cH cJ cM cN Cp CS Cu CV
CW CX cY cZ DB DC DD DE Dg Di dJ DK DL dM dN Dp dR Ed EF Et Ez Fa Fb Fn FP Fr Fw Gl gP gW Hb Hc Hf Hu Hv Hw Hx Ic Id Ih Ij
Ik Im Ip Ir Is It Iu Iz Jd Je Jf Jg Jh Ji Jm Jn Jp Jq Jr Js Jt Ju Jv Jy Kd Kc Kf Kg Ki Kl Kn Ko Kq Ks Ky Kz Ld Lh Li Lj Lu Lv Lw Lx Me Mf Mg
Mh Mj Ml Mq Ms Mv Mw Mx My Mz Na Nc Ne Nf Ng Nh Nj Nl Nm Nn No Nr Nt Nu Nv Ny Oa Oe Og Oh Oi Om On Ou Pc Ph Pi Pj Pk Pz
Qa Qb Qc Qd Qe Qg Qh Ql Qm Qn Qt Qu Qx Qy Qz Ra Rc Ri Rj Rm Sr Ss St Tz Ua Ub Ud Ue Ug Uh Un Uo Up Ut Uu Vo Vt Vv Wm)
Oy(aC AD aE aG aH aI AJ aK AL aM AN aO AP aQ aR As aU aV Aw aX aZ BB BC bE bF BG bH bI bJ bL bM BO bP bQ bS bU bV bW bX
bZ cA cB cC cD cE cF cG CH cJ cK cL cM cN CO Cp Cq cR cS Ct CU CV CW cX cY cZ dA DB DC DD DE dF DG dH DI dJ Dk DL dM dN
dR EF Fa Fb fP Fr Fw GL gP gW Hb Hf Ic Id Ir Is Iz Jg Ji Jn Jp Kd Ke Kg Ki Kj Kl Kn Ko Kq Kr Ks Ky Kz Li Lj Lv Mv Mw My Nk Nv Nw
On Or Ow Pi Pj Pk Vv) Uc(aC AD aE aG aH aI AJ aK AL aM AN aO aP aQ aR AS aU aV Aw aX aZ BB BC bE bF BG bH bI bJ bL bM bN
BO bP bQ bR bS bU bW bX bZ cA cB cC cD cE cF cG CH cJ cK cL cM cN CO Cp Cq cR cS Ct cU CV CW CX cY cZ dA DB DC DD DE dF
dG dH DI dJ DK DL dM dN dR Ef Fa fP Fw GL GP gW Hb Hf Ic Id Iz Kd Ke Kg Ki Kj Ko Kr Ks Ky Kz Ld Or Ow Pi Pj Pk) Jk(aC aD aE aG
aH aI aJ aK AL aM AN aO aP aQ aR As aU aV AX aZ Ba BB BC bE BG bH bI bJ bL bM BO bP bQ bR bS bU bV bW bX bZ cA cB cC cD cE
cF cG CH cJ cK cL cM cN CO Cp Cq cR CS Ct CU CV cW cX cY cZ dB DC DD DE dF dG dH DI dJ DK dL dM dN dR EF Fb fP GL Gp gW
Hc Hf Ic Kf Kq Ks Kz Ld Or Ou Pi) Us(Ad aE AJ Al aM An aO AP Ar AS aV Aw AX Ba BB BC bF Bg bH bI bJ bN BO bP bQ bR bS bW bX
cA cC cD cE cF cG cH cK cM cN Co Cp Cq cR CS Ct CU CV Cw CX dA DB DC Dd DE Dg dH Di dK DL dM dN dR EF Fa Fb Fw GL GP
gW Hb Hc Ic Id Iz Kd Ke Kg Ki Kj Kl Kn Ko Kq Kr Ks Ky Kz Ld Nb Or Ow Pi Pj Pk) Ut(Ad aE aF Aj Al Ar AS aV AW aY aZ Ba Bb Bc bF
BG bI bJ bM bN BO bR bS bU bV bW bX cA cD cE cF cG CH cK cL cM Co Cq cR cS CT CU cV cW Cx dC DD De Dg dH Di DK dM dN dR
EF Fa Fb fP Fw GL Gp gW Hc Hf Ic Id Iz Kd Kf Ki Kj Kn Kq Kr Ks Ky Kz Ld Or Ow Ph Pi Pj) Dk(aE aF Ar aS aW Ax Ba bF Bg bJ bN Bo
bR bS bU bV bW bX cA cE cF cG Ch cK cL Co CQ cR Cs CT Cx dH eF Fn Fp Gp Ha Hc Hq Hr Ii Io Jj Jn Jo Kf Kq Ky Ld Lw Ly Lz Mc Md
Mk Mm Mn Mp Ns Nw Nx Of Or Ou Oz Pa Pc Pd Pg Ph Qx Ra Rb Rf Rg Rh Rj Sr St Uk Ul Um Ur Uv Vp Vv Tj) aF(aE Aj Al Ar aS aW Ax
Bb bF Bg bV cI Co cP Cq cR Cs cT dA De dI dM gL Gp Ha Hf Hq Hr Hu Hw Ii Il Io Iu Iv Jd Jh Jj Jo Jv Kj Kp Ld Lj Lv Ly Mn Mr Ms Mw My
Nb Nd Nf Nk Nq Nv Nw Nx Ny Oe Of Og Om Ou Pg Ph Qt Qy Rb Rf Rh Rj Ub Ue Ug Uk Ur Uu Uv Vp) aY(aE As aV Ba bE bF BG bQ bR
bS bU bX bZ cA cC cD cE cF Ch cI cK cL CO CQ cR CT cU Dc dF dG dI dL Gp Hr Jl Kc Kr Lw Lx Ly Lz Ma Mb Mc Md Mk Mm Mr Mt Nm
Ns Nv Ny Of Om Ow Oz Pb Pe Pf Pg Po Qv Rf Rg Uf Uk Um Ur Vp Tj) Ch(aE aM Ar aS aW Ba bE bJ Bo bR bX cC cG CQ cR cT cV Cx Dc
Dd De dF dG dH dL Gp Ha Hc Hq Hx Ii Ij Jl Jo Jq Js Kc Ly Mb Mc Md Mj Ml Mn Mr Mt Mw Mz Nf Nk No Nu Nv Ny Of Or Pa Pb Pc Pd Pg
Po Qn Rh Rj Ul Um Vp Vv) Nd(Ad aE AJ Al aO Ar AS aV AX aZ Ba Bb Bc bF Bg bH bI bJ bN bO bQ bR bS bV bX cA cE cG cH cM cN Co
Cq cR CS CU Cv Cw CX dA dC Dd DE dH Di dK dM dN eF Hf Kc Kj Kp Ou Ph) Ha(Ad aE Aj Al AS Ba Bb Bc bF Bg bI bN bR bS bV bW
bX cE cH cQ cR cS cT CU CX dA dC Dd De Di dK dM dR EF Fa Fb GL Gp gW Hc Hf Ic Iz Ke Kf Ki Kj Kn Kq Kr Ks Ld Or Ou Pi) Kc(Ad Al
aS Bb bF Bg bI bN bQ bV cE cI Co cP Cq cT Cw Dd De Hf Hr Il Io Iq Iu Jd Je Jo Kj Md Mk Mn Mr Mw My Nf Nj Nk Nq Nv Ny Of Om Ow
Pb Pd Pg Po Qv Qx Ub Ug Uh Uk Ur Vp Tj) cQ(aE aJ Ar aS aW Ax bE bF Bg bN bQ bV bX cE Co cP Cq cT Cx De Gp Hq Hr Hw Ii Il Io Iq Iu
Jo Kj Lj Ly Mc Md Mk Mn Mr Nf Nk Nq Nv Om Pb Pd Pg Po Qv Rf Ue Uk Um Ur Uv Tj) cI(Al aX Bb bF Bg bQ bV cE cH Co cP Cq Fa gL
Hf Hr Hu Ii Iq Iu Jd Je Jh Jo Kj Ly Mb Mc Mk Mr Mw My Nf Nq Nv Ny Of Om Pb Pd Pg Po Qv Qx Qy Ub Ue Uk Vp Tj) Cq(Ar aS aW Ax bN
bV Cs cT Cx dA Fp Ii Il Io Iv Kf Kj Ld Lj Ly Mb Mc Mn Nb Nu Nx Ou Pc Ph Qn Qv Rb Rf Rh Rj Ub Ue) cP(Al Bb bF Bg bQ bV cE Co Hr
Hu Iq Jd Je Jh Jo Kg Kj Lj Mk Mr My Nf Nq Ny Pb Pg Po Qt Ub Ue Uv Vp Tj) cT(Bb bF Bg bQ cE Co Cw De Hq Iq Iu Jd Jo Kj Mn Mr Mw
Nf Nv Of Om Pg Po Ue Uv Vp) De(Ar aS Ba bF bN bV Hq Ii Il Iq Kp Ly Mb Mc Md Nb Nf Nk Ou Pg Ph Qv Ur Vp) bF(bN Cx Gp Ii Il Io Kj
Ly Mb Mc Mn Mw Nf Ny Pc Qn Qv Rh Rj Ue Ur Vv) Hq(Ar aS aW Ax Ba bI bN bR bS bV cR Cs Cx dA eF Gp Ic Kp Ld Ou Ph) Of(Ar aS aW
Ba bI bN bR bS bV cR Cx dA Dd eF Gp Ic Kp Ld Ou Ph) bV(bN cG Gl Ii Il Io Iq Jo Ly Mb Mn Nf Ny Om Pd Rj Vp) Kp(Dd Il Iq Md Mn Mr
Mw Nf Nv Ny Om Pb Pd Po Vp) Mw(bJ bN bR bS bW cA cE cG cL cR dH Or) Bg(Ba Cx Ii Il Ly Mb Nf Pc Qv Rj Vv) Co(bN Cx Ii Il Iq Ly
Mb Mc Nf Qn Vv) Kj(Ba Kf Md Nb Nf Nx Pg Ph Rf Vp) Om(Ar aS aW Ba bN bS cR eF Ou Ph) Jo(Ar Ax Ba Cs Cu Kf Nx Ou Ph) Ou(bQ Mn
Mr Nv Pg Po Vp Tj) bN(Al Hu Iu Nf Nv Pg Ue Vp) Ii(Bb bQ cE gL Hf Kf Ph) Vp(aW Ax Cx dA Iz Ph) Il(Al Bb Fa Hf Qd) Nf(aE cG cR dH)
Nk(Bb Iv Nx Qd) Iq(aJ Bb bQ gL) Qv(aX bE bQ cE) Nv(Ar aS aW Ax) Mb(Bb bQ cE) Pg(bS Ic Ld) Cs(Mr Po) Cx(gL Nq) cR(Iu Ue) JjNx
aVdA} Nb{Us(AD aE aG aH aI Aj aK AL aM AN aO AP aQ AR As aU aV Aw Ax aZ BB bF BG bH bJ bL bM BO bP bQ bS bU bW bZ cA
cB cD cE cF cG cK cL cM CO Cp Cq CS Ct cU CV CW CX cY DB DC DD DE dF DG dH DI dJ DK DL dN Dp Ed Ef Et Fa Fn fP Fw Gl gP
gW Hb Hr Hu Hv Ib Ic Id Ij Ik Im Ip Is It Iu Iv Iz Jd Je Jg Jh Ji Jk Jm Jq Jr Js Jt Jy Kd Ke Kg Kj Kl Ko Ks Lh Li Lj Lu Lw Lz Ma Md Mf Mg
Mh Mj Mk Ml Mm Mn Mp Mq Ms Mv Mx Mz Na Nh Nm Nn No Nq Nr Ns Nt Nu Nv Ny Oe Of Og Ok On Or Oz Pa Pc Pd Pe Pi Pj Pk Po Pz
Qa Qb Qc Qg Qh Ql Qm Qn Qu Qx Qz Ra Rc Rm Ss Tz Uc Ud Uf Uh Ul Uo Uu Uv Vo Vp Vt Tj) Kj(aC AD aE AF aG aH aI aJ aK aL aM aN
AO AP aQ AR aS aU aV AW aZ bB BC bE bF BG bH bI bJ bL bM BN bO bP bQ bR bS bU bW bZ cA cB cC cD cE cF cG CH cI cJ cK cL cM

Figure 19 Continued

Li Lv Mw Ok On) Ir(Fr Iq Iu Lh Li Lj Lv Ly) Lv(cV Fr Lh Li Mw Rb) Lj(Ji Jn Mb Ok On) dA(aV Ph Ur) Ji(Lh Li) Culi DccQ NmOn NocP SrbE LiOk} cQ{cl(aJ Ba bE bX cH cP Cx Gp Lv Oh) Ba(aE Af aY bE bX Ib Mb) Bn(cP Jq Kd Lv Sr) Kf(Kg Kj Kr Uc) Af(Fb Ph Ur) Kj(Dc Sr Un) Oh(Hw Kr Mb) Fb(Mc Ue) Lv(aE Ly) Ib(Mw Ny) bE(aY cP) bV(Ly Rj) bX(Cx Mb) BoCh CsKr NfNy UeUn UcSr cPcR} cP{No(Af Bn cI cR Ii Iq Nd) cl(aX bE cR dI Gp Lv) cR(Af aY bE bN Ub) Cu(Ii Kj Uc) Lv(Af Bn Nf) Kf(Kg Kj Uc) bV(cV Ly Rj) Ba(Aj Ch) Bo(Ao Ch) Dc(Bn Dd) Ib(Mw Ny) LxNd IiJq} dA{aV(Ha Ib Id Kj Kr Kz Ly Mb Nd Nf Ql Qz Rb Rh Uc Ue Ug Ul Um Uv Vv) Ur(Af As Bn bR cF Lz Mn) Kf(Ha Kg Kr Uc) CsKr CuHa GpLy} Lv{cl(cV gW Ly Nf Ow Rb Tz Uc) Iq(Ih Is Iv Jn Lj Mw Ok) Js(Ih Ir Is Iv) aW(Bn cV Nf Uc) Uc(Ba Sr) Rb(Bn Ue) Jj(Iv Mw) bV(cV Ly) NmJp NrLj IiOn} Ba{Rb(Af Bn Ch Ib Kj Nd Ub Uc Uv) Uc(Cu Dc Jq Kf Lw Lx No) aY(bE bX Iq Ly Nd) Ib(Jh Ny Ub) Ch(Bo Rj) Nd(Jj Lx) Kj(Kf Un) LybV} Kf{Uc(aY bI Cp eF Fb Fr Kg Kj Nj Qt Ub) Kj(Ha Kr Lz Nl Rg) Kg(Af Iq Sr Uh) Kr(Af aY Mc)} bV{Ly(aY Db Gp Kr Mb Nd Ne Og Sr) Rb(bN cC Gp Kr Mb Rj Sr Uc) Ld(Kr Rj) RaRj} Ib{Mw(Af aW bM bN bW cl dK Vv) Jh(Af Bn cA Vv) MvNy} Iq{Ir(Fr Ii Ij Iu Jj Nc Nr Ok) Is(Jj Ok) Iv(Jj Ok)} aY{bE(aS dD Ur) Rb(Gp Uk) CsKr NfNy SrKj} cI{Cu(Ha Ii Kr) Gp(bE Rb) eF(Nd Ub) EfKj} Kr{Cs(bE cN eF Fp) AxFp} Af{Ny(Nf Vp) PoLx RbaJ} Ub{FbMc GpRb MbeF} Ii{On(Iv Mm) CubN} Jj{Iv(Js Mr) MmOn} Bn{PoLx RbaJ} CxPoLx DcUceF IrIuJs Unconstrained panels with 2 analytes, where 1.0E-5 >= 'model p-value' > 0. Contains 24 panels of 60,152 total panels evaluated. : Ni(aA aY bA bV Kc St) aA(Lv Nk Nx Qw Us) bA(bE Io Qw Us) Nx(Ii Jj Jo) Bn(Kq Mu) NbUs UcKq IqQd QwKk Unconstrained panels with 2 analytes, where 1.0E-4 >= 'model p-value' > 1.0E-5. Contains 238 panels of 60,152 total panels evaluated. : Ni(aE Af AJ aP Ar aS aW AX aZ Ba bE bJ BN bS bX cC cl cN cP cQ cR CS cT Cx dA dI dM eF gL Gp Is Iv Ji Jp Ky Nx Ph Qd Qv Qw Rf Rj Ub Uc Ug Uk Ur Us) bA(Af Aj aW aY Bb bJ Bn bX Ch cl cP CQ cR Ct cV Cw Cx Dd Gl Ha Hw Ib II In Iq Jo Kc Kk Kr Ly Mb Mc Mn Nd Nf Nk Nw Ny Oy Pg Qv Rb Rf Rj Sr St Ub Uc Ue Ur Uv) aA(Af cl cP cV Cx Hv Hw Ic Il In Io Iq Ir Is Iv Ji Jj Jn Jr Js Kc Kj Kk Ly Lz Mb Mc Mm Mr Mw Mx Nc Ne Nf Nl Nm Ns Nw Of Ok Oy Pb Pc Pf Qd Qv Rf Rj Vv) In(aY bV cl cP cT Fb gL Is Iv Kc Kk Kp Kq Nx Ou Ph Qd Rf Ub) Kk(aX aY bE bN cP cQ cT eF gL Il Jo Nf Oy Us) Qw(aY bV cT gL Kp Kq Mu Nb Qd Rf) Kc(aY cP cQ cT gL Jy Nb Qv) Kq(Af Jo Kj Oy Us) Mu(AF Ao Ib) Kp(Jo Kj Oy Us) Rf(cQ cT Qv Us) Nx(Il Nk Nm Oy) Nb(Ib Kj) Nk(Iv Qd) Qv(bE gL) Jo(Kf Ok) FrOy IlQd NwcQ UsbV aYcT Unconstrained panels with 2 analytes, where 1.0E-3 >= 'model p-value' > 1.0E-4. Contains 1,531 panels of 60,152 total panels evaluated. : bA(aA aC AD aE aF aG aH aI aJ aK AL aM AN AO AP aQ AR AS aU aV Aw AX aZ Ba bB BC bF BG bH bI bL bM bN BO bP bQ bR bS bU bV bW bZ cA cB cC cD cE cF cG cH cI cK cL cM cN CO Cp CS cT CU Cv cW cX cY cZ dA DB DC dD DE dF DG dH DI dJ DK DL dM dN Dp dR Ed EF Et Ez Fa Fb Fn FP Fr Fw gL GP gW Hb Hc Hf Hq Hr Hu Hv Hx Ic Id Ih Ii Ij Ik Im Ip Ir Is It Iu Iv Iz Jd Je Jf Jg Jh Ji Jj Jk Jl Jm Jn Jp Jq Jr Js Jt Ju Jv Jy Kd Ke Kf Kg Ki Kj Kl Kn Ko Kp Kq Ks Ky Kz Ld Lh Li Lj Lu Lv Lw Lx Lz Ma Md Me Mf Mg Mh Mi Mj Mk Ml Mm Mp Mq Mr Ms Mt Mu Mv Mw Mx My Mz Na Nb Nc Ne Ng Nh Nj Nl Nm Nn No Nq Nr Ns Nt Nu Nv Nx Oa Oe Of Og Oh Oi Ok Om On Or Ou Ow Oz Pa Pb Pc Pd Pe Pf Ph Pi Pj Pk Po Pz Qa Qb Qc Qd Qe Qg Qh Ql Qm Qn Qt Qu Qx Qy Qz Ra Rc Rg Rh Ri Rm Ss Tz Ua Ud Uf Ug Uh Uk Ul Um Un Uo Up Ut Uu Vo Vp Vt Vv Wm Tj) aA(aE aF aG Aj aL aM AN AP Ar AS aU aW AX aY aZ Ba bE bH bI bJ BN Bo bQ bR bS bW bX cA cB cC cD cF cG CH cK cN CQ cR cS cT Cw cX cZ dA Db dC Dd De dG dH dI dK dL dM Dp Ed eF Et Ez Fa Fb Fn FP Fr Gl GP Ha Hb Hc Hf Hq Hr Hu Hx Ib Id Ih Ii Ij Ik Im Ip It Iu Iz Jd Je Jf Jg Jh Jk Jl Jm Jo Jp Jq Jt Ju Jv Jy Kd Ke Kf Kg Ki Kl Kn Ko Kp Kq Kr Ks Ky Kz Ld Lh Li Lj Lu Lw Lx Ma Md Me Mf Mg Mh Mi Mj Mk Ml Mn Mp Mq Ms Mt Mu Mv My Mz Na Nb Nd Ng Nh Nj Nn No Nq Nr Nt Nu Nv Ny Oa Oe Og Oh Oi Om On Or Ou Ow Oz Pa Pd Pe Pg Ph Pi Pj Pk Po Pz Qa Qb Qc Qe Qg Qh Ql Qm Qn Qt Qu Qx Qy Qz Ra Rb Rc Rg Rh Ri Rm Sr Ss St Tz Ua Uc Ud Uf Uh Ul Um Un Uo Up Ut Uu Uv Vo Vp Vt Vv Tj) Ni(aC AD aF aG aH aI aK AL aM AN AO Ap aQ aR As aU aV Aw BB BC bF BG bH bI bL bM BO bP bQ bR bU bW bZ cA cB cD cE cF cG CH cJ cK cL cM CO Cp Cq Ct cU CV cW cX cY cZ DB DC DD DE dF DG dH Di dJ DK DL dN Dp dR Ed Ef Ez Fa Fb Fn fP Fr Fw Gl gP gW Ha Hb Hc Hf Ib Ic Id Ih In Ir Iz Jd Je Jf Jj Jl Jn Jr Ju Jv Jy Kd Ke Kf Kg Ki Kj Kk Kl Kn Ko Kp Kq Kr Ks Lz Lv Mr Mw Nf Nw Oa Ok On Or Ou Ow Pi Pj Pk Qe Qg Qh Ql Qm Qn Qt Qu Qx Qy Qz Ra Rb Rc Rg Rh Ri Rm Sr Ss Tz Ua Uc Ud Uf Uh Ul Um Un Uo Up Ut Uu Uv Vo Vp Vt Vv Tj) Kk(aC aD aE AF aG aH aI aJ aK aL aM aN AO aP aQ aR aS aU aV aW aZ bB bC bF BG bH bI bJ Bn bO bP bQ bR bS bU bV bW bX bZ cA cB cC cD cE cF cG CH cI cJ cK cL cM cN CO Cq cR cS Ct cU cV cW cX cY cZ dA dB dC DD DE dF dG dH dI dJ DK dL dM dN fP GP gW Ha Hw Hx Ib Ij Io Iq Iv Jd Je Js Kc Kj Ks Ld Mj Mk Ml Mn Mr Ms Mt Mw My Nb Nd Nk Nq Nv Ny Of Og Pb Po Pz Qv Qx Qz Rf Tz Uc Ug Ul Um Ur Vp Tj) In(aE aJ aP Ar aS AW Ax Ba Bc bE bI bN bX cF cN Cp cQ cR CS CU dA Dc dM dN Dp EF Ez Fa Gp Hc Hf Ic Id Ih Ir Iz Je Ji Jn Jv Jy Kf Ki Kj Kl Kr Ks Ky Kz Ld Lv Nk Nw Oa Ok On Or Pi Qg Qt Qv Qw Qy Qz Rb Rg Rh Rj Rm Sr St Ua Ue Uf Ug Uk Um Un Ur Us Ut Vv) gL(Af aW cl cP cQ cT Cx Fb Hf Hw Ib Ic Ii Il Io Iq Iv Jn Jo Jv Jy Ki Kj Kp Kq Ky Kz Ld Lv Ly Mb Mc Mu Nb Nd Nf Nk Nw Nx Ny Ou Oy Pg Ph Qd Qn Qz Ra Rb Rf Rh Rj Sr St Tz Ub Uc Ue Ug Uk Um Ur Us Uu Vv). Kc(aE Af AJ aS aW aX Ba bI BN bV Ch cl cR cS dA Dd dM eF Fb Fr Gp Il Im Io Iq Iv Jj Jn Jo Jp Kg Kj Kq Kr Lu Lv Mi Mr Mu Mw My Nj Nk Nl Nw Nx Og Ow Oy Ph Qd Qt Qw Qy Rb Rf Rj St Ub Ug Ur Us) cT(aE Af AJ Ao Ar aW Bb bE bJ Bn bX Ch cl cN cP CQ cR cS Ct cV Cx dA Dd dM Hw Ib Il Io Iq Jo Kj Ly Mc Nd Nf Nk Nw Ny Oy Qd Qv Rb Rj St Ub Uc Ue Ug Ur Us) Qd(cP cQ Fp Fr Ha Hw Ii Ij Ik Im Io Iu Iv Jj Jo Js Jt Lv Ly Lz Mr Mx Nc Nf Ng Nm Nr Nx Ny Ok Oy Pf Pz Qc Qv Rj Uc Us) Nx(cP cQ Fr Hw Im Io Iq Iu Iv Js Jt Kj Lv Nb Mm Ms Nc Nf Ng Nj Nr Nw Ny Of Og Ok Pf Qv Qw Ug Us) Qv(aJ aW aX aY Ba bV cl cQ cR dA dM Fb Im Io Jy Kp Kq Lv Nb Nk Nw Ph Qw Qy Rb St Ub) Kp(Af Aj bE bJ Bn cP Cq Dd Ha Ib Ii Il Io Iq Jt Kg Kr Nf Nm Of Rj Uc Ue Ug Uk Ur) Nw(AF Ao aS aX aY Bn bV cl cP Ii Il Iv Jj Jo Js Lv Mm Mr Mt Nf Nk Nm Oy Qw Us) Rf(aS aY Ba bN bV cl cP dA eF Ii Il Io Jo Kj Kr Lu Mc Nb Rb Rj Sr Ub Ue Ug Ur) Kq(Ad bN cI Cq Dd De Ha Ib Ii Il Io Iq Jt Kg Kr Mr Nf Of Pd Po Ue Ug Ur) cP(AF aJ aX aY bE Bn bV cl cQ cR cS dA dI dM Jy Lv Mu No St Ub Us) Nk(bV Fr Ih Ir Is Ji Ij Jl Jn Jp Jr Lv Mb Ne No Ok On Qe St Ub) Qw(aJ Ba cl cN cQ dA dM eF Fr Jn Jp Jy Lw Mi Ph Qt Sr St Ub Ur) Nb(Af Aj aX aY bE BN bV Ch cl CQ cZ Ha Uc Ug Ur) Us(Ba Cu dA eF Fr Jn Jp Jy Kf Lv Lx On Rb Sr St Un Up) Mu(aY Bb bF Bg bQ bV cE Ch cl Co CQ De Dk Kj Oy) Lv(cl cQ Fr II Io Iq Iv Jj Jo Jp Lj Mw Oy) St(Al aX aY Ba Bn cl cQ Il Io Iq Nj Nl Ub) Jo(aY Ba Cu Is Iv Ji Kn On Ph Sr Vv) cQ(aJ Ba bE bX cl dM Fb Mb Oh Ur) Ik(Fr Ir Is Iv Ji Jy Lj On Sr) Ba(aY Ch Ib Io Kj Oy Ue) Jj(Fr Ir Is Iv Ji On) Oy(Is Iv Ji Kf Ok On) bV(Io Kr Ld Ly Rb Rj) Nm(Ji Ok On) Io(aJ Ph Ur) Kf(Kg Kj Uc) Fr(Iv Mb) Ub(eF Rb) Iq(Ir Is) Jy(Bn cI) Ok(Nf Of) Ur(aY dA) BoCh Gpcl Mwlb IiOn SrKj aYbE Unconstrained panels with 2 analytes, where 1.0E-2 >= 'model p-value' > 1.0E-3. Contains 5,431 panels of 60,152 total panels evaluated. : Qv(aC AD aE AF aG aH aI Aj aK AL aM AN AO AP aQ AR AS aU aV Aw Ax aZ BB BC bF BG bH bI bJ bL bM BN BO bP bQ bR bS bU bW bX bZ cA cB cC cD cE cF cG CH cJ cK cL cM cN CO CP Cq CS Ct CU CV CW CX cY cZ DB DC DD DE dF DG dH DI dJ DK DL dN Dp dR Ed EF Et Ez Fa Fn Fp Fr Fw Gl Gp gW Ha Hb Hc Hf Hq Hr Hu Hv Hw Hx Ib Ic Id Ii Ij Ik Il Ip Iq Ir Is It Iu Iv Iz Jd Je Jf Jg Jh Ji Jj Jk Jl Jm Jn Jo Jp Jq Jr Js Jt Ju Jv Kd Ke Kf Kg Ki Kj Kl Kn Ko Kr Ks Ky Kz Ld Lh Li Lj Lu Lw Lx Ly Lz Ma Mb Mc Md Me Mf Mg Mh Mi Mj Mk

Oz Pa Pb Pc Pd Pe Pg Po Pz Qa Qb Qc Qe Rj Sr Tz Ub Uc Ue Uk Um Ur Wm) Kq(aE AJ aM Ao AS aW aX aY Ba Bb bE bH bJ bQ bV Ch Cp cR cS Ct Cu cV Cw Cx cZ dA Dc dG DL dM Fb Fn Fp Fw Gl Gp gW Hr Hv Hw Hx Id Ij Im Ir It Iu Iv Jd Ji Jj Jk Jn Jq Jr Js Jv Kd Ke Ki Kk Kn Ko Kz Ld Lh Ly Mb Mc Md Me Mf Mj Mk Ml Mn Mq Mw Mx Mz Na Nd Ng Nk Nm Nr Ny Og Ok Om Or Ow Pb Pe Pg Pi Pk Qa Ql Qn Qx Qz Ra Rb Rj Sr Tz Ub Ud Uk Ul Um Up Ut Uv Vo Vp Vt Vv Tj) Qd(Af Aj Ao aS aW aX aY Ba bE bl bN bS bV cA Ch Cq cR dA dM dR Ed eF Et Fa Fn fP Fw GP gW Hf Hq Hr Hu Hv Hx Ib Ih Ip Ir Is It Jg Jh Ji Jk Jl Jm Jn Jp Jq Jr Kj Kk Kr Kz Lu Lw Lx Ma Mb Mc Md Me Mf Mg Mh Mi Mj Mk Ml Mm Mn Mp Mq Ms Mt Mu Mv Mw My Mz Na Nd Ne Nh Nj Nl Nn No Nq Ns Nt Nu Nv Oe Of Og Oh Oi Om On Oz Pa Pb Pc Pd Pe Pg Po Qa Qb Qe Rb Sr Ub Ue Ug Uh Uk Ur Tj) Iv(Aa aJ aS aX aY Ba bE bV dA dM Et Fp Hq Hr Hu Hv Hw Hx Ih Ii Ij Ik Im Io Ip Iq Ir Is It Iu Jg Jh Ji Jk Jl Jm Jn Jp Jq Jr Js Jt Lj Lu Lw Lx Ly Lz Ma Mb Mc Md Me Mf Mg Mh Mi Mk Ml Mm Mn Mp Mq Mr Ms Mt Mu Mv Mw Mx My Mz Na Nc Nd Ne Nf Ng Nh Nj Nl Nm Nn No Nq Nr Ns Nt Nu Nv Ny Oe Of Og Oi Ok Om On Oz Pa Pb Pc Pd Pe Pf Pg Po Pz Qa Qb Qc Qe Ub Ue Ug Ur Us) bV(aA aM aW aY Ba bE bl bN bR bS bX cA cV dH dM Fb Fn Fp Ha Hc Hf Hr Hw Ib Ic Ih Ii Il Im Ip Iq Ir Is Iu Jj Jn Jo Jt Jv Jy Kg Ki Kj Kz Lu Lz Mb Mc Me Mf Mi Mm Mn Mr Ms My Na Nd Ne Nf Ng Nj Nl Nm No Oe Of Og Oh Oi Ou Oy Oz Pc Pf Pg Ph Pi Ql Qn Qy Qz Ra Rg Rh Sr Tz Ub Uc Ue Uf Ug Uh Uk Ul Um Ur Uv Vv Wm) Kk(Aj Al An Ar As Ba Bb Bc Bo Cu Cv Cx Db dR Fb Fn Fp Fr Fw Hc Hf Hq Hr Hv Ic Ih Ii Im Ir It Iu Jg Jj Jk Jn Jp Jr Jt Ju Jv Jy Kg Ki Kr Ky Kz Lh Lu Lw Ly Lz Mb Mc Md Me Mf Mh Mi Mq Mu Mx Mz Na Nc Ne Ng Nj Nl Nr Ns Oe Oh Oi Ou Oz Pa Pe Pg Ph Pi Pj Qh Qn Qt Qy Ra Rb Rg Rh Rj Rm Sr Ub Ue Uk Un Ut Uu Wm) Ur(Af aJ aP Ar aS aW AX Ba Bc bE bl bJ BN bX Ch cN cR cS Cu Cx Dc dl dM dN eF Ez Fb Fr Gp gW Hc Hf Ic Ih Il Im Ip Iq Ir Is Jl Jn Jo Jp Jv Jy Kf Ki Kj Kr Kz Ld Lu Lw Lx Ly Mb Mc Mi Mn Mp Mr Mu Mw Mx My Ne Nf Nj Nk No Oh On Ou Oy Ph Qt Qy Qz Ra Rb Rg Rh Rj Sr Ua Ub Ue Ug Uk Un Us Ut Vv Wm) Ji(Et Fp Fr Hq Hr Hu Hv Hw Ih Ii Ij Ik Im Io Iq Ir Is It Iu Jh Jl Jm Jn Jp Jq Jr Js Jt Lh Li Lj Lu Ly Lz Ma Mb Mc Md Me Mf Mg Mk Ml Mm Mn Mp Mr Ms Mt Mu Mv Mw Mx My Mz Nc Ne Nf Ng Nj Nl Nn Nq Nr Ns Ny Oe Of Og Oi Ok Om On Oz Pa Pb Pc Pd Pe Pf Pg Po Pz Qb Qc Qe Ug Us) Ug(Af aJ Ar aS aW AX aY Ba Bc bE bl BN bX Cp cR cS Ct Cu Cv dA Dc dM dN EF Ez Fb Fr Gp Hc Hf Ih Il Im Io Ip Iq Ir Is Jg Jh Jn Jp Jq Jy Kf Ki Kl Kz Ld Lw Ly Mc Mi Mr Mu Mw My Ne Nf Nj Nk Nl No Nt Oh Om On Ou Ph Pi Qt Qy Qz Rb Rc Rh Rj Sr Ub Un Us Ut Vv Wm) Ni(Et Fp Hq Hr Hv Hw Hx Ii Ij Ik Il Im Io Ip Iq It Iu Jg Jh Jk Jo Jq Js Jt Li Lj Lu Lw Lx Ly Lz Ma Mb Mc Md Me Mf Mi Mj Ml Mm Mp Mq Ms Mt Mu Mv Mx My Mz Na Nc Ne Ng Nh Nj Nk Nl Nm Nn No Nr Ns Nt Nu Nv Ny Oe Of Og Oh Oi Om Oy Oz Pb Pc Pd Pe Pf Po Qa Qb Qc) Us(aJ aP Ar aS AW AX aY Bc bE Bg bl Bo bX cN Cp cR CS Dc dG Dk dM dN Ef Ez Fa Fb Gp Hc Hf Ih Il Im Io Iq Ir Is Jg Jj Jl Jq Kd Ke Kn Kz Ld Lw Ly Mc Mi Mp Mr Mt Mu Mw My Mz Nf Nk No Nt Nv Ny Oh Ok Om Ou Pg Ph Qa Qe Qh Qt Qy Ri Rj Ua Ub Ut Vv Wm) aY(aE Af aJ aM An Ar aS aW aX bl bJ bN Bo bR bS bX cA cF Ch cR cS cZ dM eF Fb fP Fr Gp Ha Hc Hf Hr Ib Ic Ih Il Im Io Ip Iq Ir Is Jj Jn Jy Ki Kj Kr Kz Ld Ly Mb Mc Mk Mn Mr Ms Nd Ne Nf Nk No Or Ow Oy Pg Ph Qy Qz Ra Rb Rg Rh Rj Ub Ue Uk Ul Um Vv Wm) Ba(aE Af AJ An Ao Ar aW AX Bb bE Bg BN bX cF cN Co Cq cR CS Ct Cu cV cZ dA Dd dl dM dN Fb Ha Hq Hr Hu Hw Ii Il Iq Jd Jj Jn Jv Jy Kg Ki Ky Ld Ly Mb Mc Mk Mn Mu Nd Nf Ng Nk No Ny Oa Of Ou Pg Ph Qt Qz Rb Rj Ub Uc Uk Uu Uv) Nk(aJ Ar aW aX cN dA dM eF Et Fp Hq Hv Hw Ik Il Im Io Ip Iq Iu Jg Jh Jk Jo Jq Jy Li Lj Lu Lw Lx Ly Lz Mc Mi Mj Mp Mq Mr Ms Mt Mu Mv Mw Mx My Mz Na Nc Nd Nf Ng Nh Nj Nl Nm Nt Nu Nv Of Og Om Ou Oy Oz Pb Pc Ph Po Qa Qb Rj Ue) Fr(Af Aj Ch dM Fp Hq Hu Hw Ib Ih Ii Ij Im Io Iq Ir Is Iu Jk Jn Jo Jp Jr Js Kj Kr Ly Lz Ma Mc Mg Mk Mm Mr Ms Mt Mv Mw My Nc Nd Ne Nf Ng Nj Nm Nn Nq Nr Ns Ny Oe Of Og Oi Ok Pb Pc Pd Pf Po Rb Rj Sr Ub Uc Ue) Mu(Ad aE AJ Al aM An aO aP AR AS aW AX bE bH bl bJ bN bR bS bX cA cF cG cH cN cR CS Ct Cw Cx cZ dA Dd dE dl dM dN eF Fb Gp gW Hf Ic Il Is Jj Jo Kg Ki Ks Ky Kz Ld Ou Ph) aA(Aa aC AD aH al aJ aK Al AO aQ aR aV Aw BB BC bF BG bL bM bO bP bU bZ cE cJ cL cM CO Cp Cs Ct CU Cv cW cY dB Dc dD dE dF Dg Di dJ Dk Dl dN dR Ef Fw gW Wm Tj) Jy(aE AF AJ Ao Ar aS aW aX bE bF bN bQ bS bX cA Ch Cq cR cS dM eF Gp gW Ha Ib Ii Im Io Iq Jj Jo Kj Kz Ld Ly Mb Mc Mk Mn Mr Nd Nf Of Oy Ph Rb Rh Rj Ub Uc Ue Uk Um Vp Tj) Is(Fp Hq Hv Hw Ih Ii Ij Im Io Ir It Iu Jm Jn Jp Jr Js Jt Lu Ly Lz Mb Mc Mf Mg Mk Mm Mn Mr Ms Mw Mx Nc Ne Nf Ng Nj Nl Nm Nr Ns Ny Oe Of Og Oi Ok On Oz Pa Pb Pd Pf Qb Ub) Ub(aJ aP Ar aS aW aX Bc bE bl bJ bN Bo bX cR cS dA dM dN Ez Fb Gp Hc Il Im Io Ip Iq Jj Jn Jo Jp Ki Ld Ly Mb Mc Mr Mw Ne Nf Nl No Oh Ou Ph Qy Qz Rh Rj Um Un) aJ(Af Aj aM An Ar aS aW bE bl BN bR bS bX cF Ch cR cV Cx dA dG dH dK dL Gp Ib Il Ip Iq Jn Jo Kr Kz Ld Ly Mb Mc Mi Nd Ne Nf Ny Oe Oy Ph Rb Rh Rj Ue Vv) Jj(aW aX bE cR dA dM Et Fb Fp Ih Ik Il Im Jg Jh Jk Jl Jn Jp Jr Ld Lj Lx Ly Lz Mb Mm Mr Mt Mv Mw My Mz Nc Nf Nt Nu Nv Ok Om Ph Qa Qb Qe Qy Rb Rh Vv) Jo(Ad AP Ar AW AX Bc bE Bg bX Cp cR cS dA Dc Dg dM dN EF Ez Fb Gp Hc Ir Jg Jl Jn Jp Kd Kl Ld Mw Nv Om Ou Qt Qy Rb Rh Uf Un Ut) Ok(Hq Hr Hv Hw Ih Ii Ij Il Im Io Iq Ir Iu Jn Jp Jr Js Jt Lh Lj Ly Lz Mb Mc Md Me Mf Ml Mm Mr Mw Mx Nc Ng Nj Nr Ny Og Om On Oz Pb Pd Pe Pf) Io(aE aO aP Ar aS aW AX Bc bE Bg bl bX cN cR CS Cu dA Dc dM dN EF Ez Fb Gp Hc Ic Ir Jp Kf Kl Ld On Ou Qy Qz Rb Rj Un Ut Vv) Jp(Ha Hw Ib Ii Il Im Iq Ir Jn Jr Jt Ke Kg Kj Kr Kz Ld Ly Lz Mb Mm Nc Nf Ng Nm Nr Ns Ny Of Oy Pf Rb Rj Sr Uc Ue Uh Uk) Il(Ar aS aX bE bX cR Cu dA Dc dM eF Fb Ih Im Jl Jn Kf Ld Lh Li Lx Mw Nv Ou Ph Qa Qe Qy Rb Rh Un Vv) Oy(Ar Aw Bo Cp Cu dA EF Fb Hc Im Ir Jg Jk Jl Jn Jr Lj Lx Mv Mw My Nv Om Ou Pg Qe Qy Sr Ut Vv) Rb(Af aP aS aW aX bE BN cR cS dA Db dM eF Gp Im Jn Kj Ly Mb No Og Ou Ph Qt Rh Rj Sr Ub Ut Vv) Rj(aS aV aW bN bR bS bX cA cB cF cK Fb Gp Ha Ib Iq Jn Ld Ly Mb Nd Ph Rg Rj Ue Uk Ul Um) Ph(Af Aj Ao aS aX bE BN Ch dM eF Ib Iq Jv Kg Ki Kj Kr Ld Ly Ng Nj Rj Uc Ue Uk) On(Hq Hw Ij Iq Ir Iu Jr Jt Kj Ly Mb Mm Mr Ms Nc Nf Ng Nr Ns Ny Oe Of Og Pf Uc) dM(aE Ar aS bl bN bS bX cR cS dl Fb Gp Im Iq Jn Ld Ly Mb Nd Qz Rj Ue) Ly(aE Af aP aS aW aX bE bl BN cN cR cS Cu dl dN eF Gp Ir Qt) Ue(aX bE Bo cR eF Fb Gp Hc Jn Kf Ld Lw Mw Om Ou Qy Sr Un) Ir(Hw Ii Ij Iu Js Lz Mb Mr Mw Nc Ne Nf Ng Nj Nl Nm Nr Ny) eF(aS Ib Im Kg Kj Kr Ld Mb Nd Nf Og Rh Rj Sr Uc Uk) Kj(Ar Cp Cu Dc Ef Ez Fb Hc Jn Oh Om Qy Ua Un) bE(Ar aS aW bl Gp Im Iq Jn Ld Mb Ou Rh Rj Uk) Sr(Bn Ha Hr Ii Kr Mb Nf Rj Uc Uk Um) Kf(Cq Dd Ha Hr Ib Ii Iq Kr Nm Rj) aX(aW Im Jn Ld Mb Mc Mr No Ou Rj) Cu(Aj Ha Ii Iq Kg Kr Nd Nf Uc) Fb(Aj aS aW Gp Mb Mc Og Rj) Ib(Bo Cp Hc Jh Mv Ny Om Qy) Mb(aS aW bl Jl Jn Mw Nj) Rj(aS cR Dc Jn Jq Ld Un) Iq(cR Dc Gp Ih Jn) Ld(aP aW cR cS Gp) No(aS aW bl Mr) Kr(Cs Jn Oh Un) bX(aW bl cR dl) Dc(Bn Dd Nf) Mi(Gp Uk Um) Ou(aS cR Ow) bN(cN cS dN) Aj(Ef Hc) Bo(Ao Co) Ch(Hc Qy) Lx(Ha Mr) Mc(aS Qt) Hw(Jn Mw) Ny(Cq Vp) BnJq CpUc CsFp GpaW NfKd NgJg IiUn QycR

Constrained panels with 3 analytes, where 1.0E-8 >= 'model p-value' > 0. Contains 1 panels of 6,910,825 total panels evaluated. : AfNiSt Constrained panels with 3 analytes, where 1.0E-7 >= 'model p-value' > 1.0E-8. Contains 28 panels of 6,910,825 total panels evaluated. :
Ni{St(Bn Ii Il Io Qn) bA(cV Jo Mb Oy) Af(aA Mu Nw) Qw(bV Rf) BnMu MbbV NxaA} Mu{Bn(cP Iq) AfIl CsHa} Nb{cQ(Oy Us)} Qd{IiNx IqOk} AfQwKq NkNxaA UpUsbA Constrained panels with 3 analytes, where 1.0E-6 >= 'model p-value' > 1.0E-7. Contains 475 panels of 6,910,825 total panels evaluated. :
Ni{bA(Af As aY bE bJ BN bQ Cq Ct Cw Dd Fp Gl Ha Hr Hv Hw Hx Ib Ii Ij Il In Io Iq Jn Jr Js Jt Kc Kr Lh Ly Mc Me Mn Mq Mr Na Nd Nf Nm Of Pb Pd Pe Pg Po Qa Qw Rf Rj Sr St Uc Ue Us Uv Vp) bV(Ad aM As bJ BN cC Cq cV Cw Dd dG dL Gp Hr Hv Hw Ij Il In Io Jo Js Jt Kc Kr Lh Ly Mc Me Mj Mr Na Nd Nf Nm Of Oy Pb Um Us) St(Ad Aj Al Ao aY cI cQ Cx gW In Jo Jt Kc Ke Kr Mb Mc Mn Nm Ny Pg Qv Uc Ue

Figure 19 Continued

Ug Uh Us) In(aY cI cP CS Kc Nx Ou Ph Rh Ub) aA(As BN cV Cx lv Kc Mr Qw Us) aY(Kc Ly Mb Mu Nf Nw Rf Vv) Ih(Af BN Qw Ue Us) Kc(bN cP cQ cR Mc Ub) Jo(Cs cT Kf Nx Rf) Mc(Bo cT gL Ky) Rf(bN gW Qv Qv Us) Bn(Kq Lx Nw) Mb(cQ cT gL) Qw(dA Qd Ub) Af(Kq Lx) Mu(aF Dk) Nx(Ii Jj) bN(Nc Ub) cT(cV Oy) dA(Ly Nf) UcKq lqQd OwOu} Mu{Bn(Ao Ar aW aY bA bN cI cQ cT Dd Ii II Io Iv Kc Kk Kp Ly Mc Mr Nb Nq Ou Oy Ph Qv Qw Rb Vv) Af(bN bR bW cP Iq Iv Jk Mb Mp Nd Nk Oy Qv Qw Uk Um Us Uv) Qw(aF Ao aY Ii II Kk) Uc(bA Kf Kp Kq) Oy(cP Kk Kp Nx) AoVv AxHa NbIb JkcP UvbA aFcQ} Kq{Uc(Af Ao aY BA Bn cI cP cQ cT eF GI Hb Hc Ii II Io Iq Jq Kp My Nb Ny Pg Qv Rb Sr Uh Vv) Bn(aW aY bA cI cP cQ Ii II Iq Qv Qw Rb Uh) Af(Io Kr Rj Us Vp) Us(bA Nb) IiQw UvbA} Nb{Us(aY bA bV cT dA eF In Io Kp Lv Mi Nc Ne Ri) cQ(Af Bn Ib Jo Kj Mb Nf Of Qw Uc) Jo(aY bA cT eF Kf Kp Qw) Oy(bA cP eF Kc Kp Qy) Qw(aY bV Ub) bA(Nd Uc Uv) aY(As In)} aA{Nx(Af Ii Il In Iq Jj Jo Js Mx Nf Nm Nr Ny Oy Pf) Af(Io Iq Kc Ly Qw Rf Rh Us Vv) Nk(Iv Lv Mb Qd) Qw(aF cQ Cx) Io(BN) IqQd UpUs} bA{Io(Af In Ly Oy Pg Qw Rf Ub) Qw(Af cQ dA Oy Sr Ub Us) Rf(Af Ha Ii Mn Ny Sr Us) Jy(Bn Uc Uv) Us(Ly Qd Rb) AfRb LyPg IqSt KkOy aYcV} Qd{Iq(Il In Iv Lv Nk Nr Nx) Nx(Il In Jo Js) Nk(Il Lz)} Kk{Oy(Ba eF Jh Qy) InaY QwcQ QvbE JoeF} Qw{Rf(aY cQ) AoJh IocT UsbV} Nx{Nk(Ii Jo) FrOy InIv JoOk} Nw{cQ(Af Bn Cx) BncP} AfQvgL BnJycP UpUscT

Constrained panels with 3 analytes, where 1.0E-5 >= 'model p-value' > 1.0E-6. Contains 3,406 panels of 6,910,825 total panels evaluated. : Ni{bV(Af Aj An bE bW Cp cQ Ct Cu Dc De Dl Fn Fw Ha Hx Ib Id Ii Iq Ir Iv Ji Jn Jr Kd Ke Kg Kj Kn Ko Kp Kq Kz Md Ml Mq Mx Mz Nb Nr Ny Om Or Ow Pd Pe Pi Pk Po Qa Ql Qv Qx Ra Rb Rf Rj Sr St Ub Uc Ud Ue Ug Uk Ul Up Ur Uv Vp Vt Tj) cT(Af Aj As aY bE bJ BN bQ cI CQ Ct Cw Dd Ha Hr Hw Ib Ih Ii Ij Il In Io Iq Js Jt Kc Kj Kr Kz Lh Ly Me Mr Ms Na Nc Nd Nf Nk Nm Of Om Pb Pg Qw Qx Rb Rf Rj Ub Uc Ue Ug Us Uv Vp) aA(Ad aM An bE bJ cC cI Cp Cq Cu Cw Dd De dG dL Fw Gp gW Ha Ib Ic Id In Jn Js Kj Kr Kz Lv Or Pi Pk Qd Qn Ra Rb Rf Rj Ub Uc Ud Ue Ug Uk Ul Um Up Uv Vp) Rf(Af Aj Ao Ba Bn cC Ch cI cP cQ Cx dA dR Hw Ii Ij Il In Io Iu Kc Kg Kj Kr Ly Mb Mc Me Mn Mr Na Nc Nd Nf Nk Nm Oe Oy Pg Rj Sr Ub Uc Ue Ug Vp) bA(Ad aL aM Bb cE cI Cp cQ Cx De dF dG Fw gW Id Iv Jd Ke Kg Kj Kk Kq Ky Kz Mj Ms Mx Nb Nc Nk Ny Om Pi Qx Ra Rb Ub Ud Ug Uk Ul Um Up Tj) Cs(Af aM As bE bJ BN Cq Dd Fp Hr Hw Ii Ij Il Io Iq Iv Jn Js Kj Kr Mb Mc Me Mj Ml Mr Na Nd Nf Nm Nr Of Oy Pb Pe Qw Ue Ug Ul Um Us) Ih(Ad Aj aM An As aX aY bE bJ cC cI CP CQ cR Cu Cw Cx Dc Dd De DL gL Ha Ib In Kc Kj Kr Lv Nx Qv Rj Uc Ug Uk Ul Um Ur Uv Vp) dA(Af aM aV aW BN bX cI cP cQ cS Dd Gp Hr Il In Iq Jo Kc Kj Kz Mb Mc Me Mr Nc Nd Nw Nx Oy Qv Rj St Ub Ue Ug Um Ur Us Vv) Ub(Af aY Ba bE bJ Bn Bo cI cN cP cQ cR cV gL Gp Il Io Jo Kz Ly Mb Mc Me Nf Oh Oy Pb Qv Rh Rj St Ue Ug Uk Ul Um Ur Us) Kk(aC aY bE bJ bN cN CQ cR Dd gL gW Ha Hx Ib Ij Il In Iq Jo Js Mj Ml Mr Nb Nd Nf Of Oy Pb Qw Qx Ul Um Us Vp Tj) aY(aM Ba bE bJ BN Bo cQ cR gL Gp Il Io Jo Jy Kr Kz Ld Mc Me Mr Ms Nc Nd Nk Nx Ow Oy Qw Rj Ue Uk Ul Um Ur Us) cQ(aE Af aJ As Ba bE bJ BN bX cI cN cS cV Cx dM gL Il Jo Ky Ly Mc Mr Mu Na Nc Nf Nk Nw Oh Qd Rj Ue Ug Vv) Us(Ax Ba cN cP Cu Dc eF Ir Is Jn Jp Kf Kp Kq Ky Lv Lx Mc Nc Nk Nw Nx On Qd Qh Qv Ri Sr Un Up Vv) Jo(aJ Ar aS Ax Ba bX cI cN CP cR cS Cu Dc dM dN eF gL Is Ji Kn Kp Kq Ok Ph Qd Qv Sr Vv) bN(aJ bE cI cN cP cR cS Dc dM gL Il In Ky Lv Lx Mb Mc Mu Nj Nk Nl Nw Nx Oh Ou Qd Qv St Ue) Mc(aJ aS aW Ax aZ Ba bE cI cN cP cR cS dE dM Fb Kf Ou Ph Qt Qv Qw Ue Ug Uk Uo Ur) cP(Af As bE Bn cI cV dI gL Hr Il Io Kj Mb Mr Na Nc Nd Nf Nk Nw Of Oy Qd St Ue) In(aE aJ Ar aW Ax bX cN cU dM Ic Ir Is Iv Ji Kf Kp Ky Ok Qd Qv Qw Ue Vv) Af(aJ Ar Ax bX cN Cv Fr gL Il Is Jn Jp Jy Kc Lv Nb Nc No Nx On Qd Qv) Bn(aJ Ar Ax bX cN Dc Il Jn Jp Jq Jy Kf Kp Lv Lw Nc Nk No Nx Qd Qv) Ue(Ba bE bI bX Ch cN eF gL Io Jn Kf Kp Kq Ky Lv Nc Nx Ou Qd Rh Un) cI(aJ aX Ba bE cH cN cR eF gL Gp Lv Ly Mb Mu Nc Nj Nk Nl Nw Qv Vv) St(aF aK aU aW aX cC cR dR Hw Ij Iu Jl Kj Mm Mr Nd Nr Qw Sr Uk) Qw(aJ cN Im Is Jn Kf Kp Kq Ky Lv Lx Mt Mu Nc Nk Nw Qh Qv Sr) Qv(aC aX bE bJ cR cV gL Il Io Kc Ky Kz Mb Mr Nc Nd Nf Oy) gL(aF Ao aW Bb Cx Hw Il Io Kc Ms Nc Nd Nj Nk Ou Pg Sr) Mb(aJ Ar aS Ax Ba bI bX cN cR cS Cu dM eF Kq Rb) Nx(As bE Il Iv Kj Lv Mr Nf Ng Nm Of Oy Qd Ug) Mr(Ar Ax Fr Is Jp Kq Lx Nw Ok On Qd) Oy(aJ Aw Ba Bo Cp Fr Kf Kp Kq On Qd) Il(Ax bE cN cR Cx Dc Is Kq Lj Qd) Mu(Ao Bb bF bQ cE Ch Cq De Ib) Nc(Aj aM As bE bJ Cx Dd Gp Ug) aJ(cV Cx dG dL Hw Io Ly Nd Nf) Nk(aM aW bE bJ cN Gp Kc Ur) Kp(As Ib Ij Kj Kr Nf Pb Rj) Kq(Ha Ib Ii Kj Lh Nf Of Ug) Ug(Jn Ky Oh Ou Ph Qd Vv) Io(Ar Ax Ba cN Kc Ph) Kf(Ad Ib Kg Kj Nm Uc) Qd(Aj Js Nf Rj Uc) Kc(bI Hw Jn Ky Oh) Ax(Fp Kr Nf) Nd(Ar Ba cN) Is(Ij Iq Js) Ao(Bo Nw) Ch(Ba Bo) Nm(Ji Jp) Lv(cV Uc) cN(Cx Ly) CuNf UaKj IqIr KrOh NwaF bXcC} bA{Rf(Ad Al Ao aY Bb bE Bn cI CQ Cw Dd De Fp Gl Hw Ib Ih Il Iq Jd Jk Jo Js Jt Jv Ke Kj Kr Lh Ly Lz Mc Mj Nd Nj Nk Nr Nv Oy Pb Pf Pg Pi Po Qb Qh Qw Rj Rm Uc Uf Uh Uv Vp) Qw(aF Ao aY bE Bn Cq cV Fp GL Ha Hw Ii Il In Iq Jo Jv Jy Ki Kj Kk Kr Lh Lw Mj Mn Mu Nd Nj Nk Nr Ny Pb Pg Qd Rb Ri Uc Uh Uv) Us(aA Af aW aY bE bX cD cP cQ cS Cu dA Dc eF In Io Iq Iv Jq Jv Jy Kc Kd Kf Kk Kn Kp Lv Lw Lx Mr Mu No Nw Nx Oy Pg Ra St Ub Un) Oy(aY bE bJ bX cP cQ cV dA Ed eF Hc Iv Jh Jy Kc Kf Kp Kq Ld Ly Mn Mu Nd Nk Nx Qv Qy Ra Rb Rh St Ut) Kk(Af bE Cq Dd Fa Fp Fw Ha Hv Hw Ib Ii Il Io Iq Jd Jo Kj Ko Kr Mn Mr Nf Ny Pb Pg Rj Sr Uc Uv Tj) Uv(aW aY bE cD cQ cR dA Dc Ed Io Ip Iq Iv Jq Kd Lw Ly Mr Nk No Nw Nx Ny Pg Qv Rb St Un) cV(aA Af Aj aW aX bE bX Ch cN cP cQ cR cS dN In Io Iv Jo Lv Mn Nb Nk Pg Rb Sr Ub) Uc(aW aY bE cQ Cu eF Io Jq Kc Kd Kf Kn Kp Lv Lw Ly Mr Nk No Nw Nx Qd Qy Rb St) Mu(AF Ao bQ cE Cq De Dk Ha Hq Ib Iq Jk Jo Mn Nd Nv Ny Of Om Po Ut Vp) Io(aA aE aY bE bN bX cE cP cQ Fp Ha Hw Ih Il Iq Jo Kc Mn Nd Nf Pf Qd Rb) In(Af aW aY bJ bR bX cF cP cQ Dd Il Iq Iv Jv Ly Mn Nb Nd Nk Rb Rh Sr) Kc(Af aY cQ Fp Gl Ha Hw Iq Jd Jo Kr Lz Mn Nj Nk Nl Ny Pb Ql Sr Ub Uh) cQ(Af bE bJ cI Cx Hw Ib Il Jo Ly Mb Nd Nf Nw Pg Rj St Ul) Rb(As bE Bn Cq Ha Ib Il Jo Kj Lh Mb Mr Nd Nf Of Pb Sr) cP(Af Aj aL As bE Bn Ch cI Cq Ct Cw De Ib Jo Nd Of Pg) Af(aW aY bE bG bJ bX Ha Ju Jv Jy Ly Nw Qv St Ur) Nb(bE Bn bQ Cq Cw cZ De Ha Ib Ii Kg Kj Lh Mr Of) Ly(aA Ao aY bE Ha Hw Jo Mn Pb Pf Sr Ub Uh) Jy(bQ cG Cq Ha Hq Il Jk Jo Mn Nd Pd Vp) Nw(Gl Ha Ii Iq Ke Mn Nd Ny Pg Po Uh) bE(aW aY cI Gl Mn Nd Nk Pg Qv Rh Sr) St(Al Dd Ha Lh Mj Mn Nj Nk Ny Vp) Jo(aY bJ Iv Kf Kn Nk Nx Ph Ra Rh) Sr(bJ Fb gL Hf Jn Kz Me Nk Qy) aY(bJ Bn bQ cG dG Iq Mn Nd) Ha(Kf Kq Ld No Pg Qd) Iq(Kq Pg Qd Qv Ub) Nd(aA bJ dA Hw) Mc(Fb Lz Nk) Mn(Ky Pg Qd) bX(Bn Cq Dd) Nk(Ub Ue) Qy(Ib Kj) Kq(Cq Lh) BnJq CsKr DcDd PoQd IldA PgbJ} Mu{Af(aA aE aF Ao Ar As aV aW bF BG bJ bQ bS bU bX bZ cA cC cD cE cF cG Ch cI cK cL CO CQ cR CT cU dA dF dG dH dI gL Gp Ha Hq Hr Ib Ii In Io Jj Jo Kc Kj Kk Kp Kr Ly Lz Ma Mc Md Mk Mm Mn Mr Nb Nq Ns Nw Of Or Ow Oz Pa Pb Pd Pe Pf Pg Po Rb Rf Rg Rh Uc Uf Ul Ur Vp Tj) Qw(aA Al aO aW Bb bF Bg bV cE cG Ch cI Co cQ Cs dA De Dk Ha Hc Hq Hr Hu Ib Io Iq Iu Jd Je Jk Jo Kc Kj Kp Md Mw My Nd Nq Nv Of Om Ou Oy Pd Pg Qd Qv Rf Ub Uc Uh Us Ut Uv) Ao(aF Ar bN cI cP cR Cx Gp Ii Il In Iq Jk Kc Kk Lw Ly Mb Nd Nf Or Pc Pd Qn Rj Ul Um Us) aY(aF bJ bN bW cG cP dH Ha Hq Ii Il In Io Iq Jk Jo Mn Mp Nd Nk Or Oy Pa Pd Uc Ul Us Uv) Uc(aF Ap Ar aW Ax Ba bV cI cP cQ Cs cT Cu Dg eF Fb Hc Kc Kk Kl Kn Ou Ph) Ib(Ar aW bN cI cP cQ cT Cx Il Iq Kc Kk Kp Mc Mn Ph Qn Qv Rh Us Vv) Oy(aA Ar aW bN cI cQ Cs cT Cx Hc Hu Iv Kc Kf Ld Ok Ou Ph Qd) Us(aF aW bV Ch cI cP cQ cT Dk Hf Kc Kf Kk Kp Ou Ph) Jk(aF Ar aS aW bN cI cQ cT Cx dA Kc Kk Kp Ph) Dk(cI cP Il Iq Iv Kc Kk Kp Mb Nb Nd Nk Qv) Kk(aF CQ Dd Ha Hq Je Nf Nv Of Ut Vp) cP(Ch Cq De Ha Hq Iu Mw Nd Nv Of Om Ut) Ut(Ax cI cQ Cs Kc Kp Ou) Ch(aF bN cI Il Iq Nd) Ha(Ar aW cI Kc Kp Ph) cQ(cI Kc Mb Nd Of Vp) Iq(aF bF Bg cE Cq) Kp(Cq Ii Jo Kj) aF(Kc Mb Mc Qv) Nd(aW cI cT) Cs(Pe Vp) De(aW cI) Hq(cI Kc) BgQn CqVv IiKc} aA{Us(aY cM cQ cR Cx eF Hf Ic Io Iq Iv Jn Kf Kk Kp Kq Lv Ly Mr Nb Nk Nx Ou Oy Pg Ph Rb Rf Rh Ri Vv) Bn(Ic Iq Iv Jq Jy Kc Kk Kp Kq Lv Lw Ly Mc Mr Nb Nk Nw Nx Ou Qv Qw Ra Rb Rf Rh St) Af(aP Hf Il In Iv Jy Kk Kq Lv Mb Mc Mr Nb Nd Nk Nq Nw Qv Rb St Ur) Qd(Fp Hv Hw Il In Js Jt Lz Mr Mx Nc Nm Nr Ny Oy Pf Qa) Kk(bN Dd De Ha Ib Il In Io Iq Kj Mj Mn Nf Oy Qw Uc) Qw(aW aY dA dH

Figure 19 Continued

Ha Io Kp Nb Pg Qv Rf Rh Ri Ub) In(aW aY cI cP cQ Ir Iv Lv Ly Ok Ou Rh Vv) Io(aF bJ cV Cx Ic Kc Qn Qv Rb Rf Rh Vv) Kc(bN cQ Cx Ha Hw Iq Nj Nk Ow Oy Pg) Ly(As aY aZ cI cQ Cx Nk Oy Rf Ub) Iv(Hv Il Iq Js Mr Mx Nc Nf Oy Pf) Ok(Hv Iq Jo Js Mb Mr Mx Nf Oy) Lv(Iq Js Me Mr Mx Nf Oy Pf) Nb(Cq Dd De Ha Ib Kj Uc) Rf(aY cQ Ha Ii Iq Ny Sr) Mb(cQ Nj Nx Pf Rb) Nk(Cx Hw Ir Jn Mc) Iq(cC cI cQ Cx Ir) Nx(Hw Mr Nc Of) Cx(Mc Rb) Uc(Kf Kq) Js(Ir Ji) Kp(Ib Oy) Nw(Mt Nm) FrOy NdcQ IlLj cPcV} Nb{cQ(Ad As bE bJ bN Cp Cq Ct Cw Dd De Ha Hr Ii Ij Il In Iq Jt Kc Kg Kr Kz Ly Mr Na Nd Om Pb Qx Rj Ue Uk Ul Um Ur Uv Vp) Jo(Ap Ar aX Ba BC BN bV bX cN cP cR cS Cu dA Dg dN Ez gL Gp Kc Kq Ph Rb Rf Sr Us Vv) Oy(Aw aX aY Ba bJ Bo bV cN cT cW dA Ef gL Gp Hc Jv Kf Kk Kq Qv Qw Rb Rf Sr Ur Us) Us(aX Ba bC bE bI bX Ch cN cP dM Ez Jn Jv Kc Kf Kk Mc Nd Nx Qw Rb Rf Ub Up) Qw(Af Ao Ch Co dA Ib In Io Kc Kg Kj Kk Kp Mi Nd Qd Rf Rg Sr Uc Ue) In(Af aW BN cI cP cS De gL Ha Ib Jd Kc Kj Ph Rh Ub Uc) Ib(aY Ba bV cP cT dA eF Io Kc Kp Kq Mv Mw Nc Ne Qy) Kj(aX aY Ba bV bX cP cR cT dA eF gL Kc Kp Kq Nd Rf) Nd(As aY Ba bV cN cP cT dA eF gL Ue Ug) Uc(bV cT cF Kc Kf Kp Lv Rf) aY(bE bJ Gp Ha Il Io Kc Kr) Ha(bV cN dA Kc Ne Ub) bV(Io Jt Kr Ly Rj) Bn(Io Kq) AfKc IogL} Qw{Qd(Af Al aY Ba bI Bn cP cQ dA Dd Ha Ii Il Io Iq Iu Ke Kp Kr Nj Nk Qy Rb Ub Uh Us Vp) Rf(Al Ao Ba bI Bn cI cP cT dA Dd Ii Il Io Iq Iu Jv Kk Kp Mi Ne Nj Nk Nl Qt Qy Ub Us) Kq(aF Ao aY Bb cI cQ dA Gl Hq Il Io Iq Iu Jo Ke Kk Kp Lh Oy Sr Ub Uh Us) Kk(Af aY Ba bI bV cP cT dA eF gL Hw Jy Lv Mi Mw My Nj Qt Qy Ri Ub) Kp(Af aY cQ dA In Io Jo Jy Lw Oy Qv Ri Sr Ub) aY(Ba bV cT dA eF gL In Jy Lw No Nw St Ub) dA(aK aU aV bV cT eF Fb gL Qv Ur) cT(Af cQ In Jo Ri Ub Us) bV(Io Nk Qv Rb Rj) Ub(eF Jy Nk Nx) gL(Af aW Cx Ri) Ba(Jo Oy Us) Ao(Mw Nq) Ib(Jh Mw) Jo(Kf Nx) AfJy ChJh IiNw IoaJ QvbE KccQ cIeF} In{aY(bE bJ bN bV bX cI cP cQ cT Ih Io Ip Ir Iv Jn Kc Kp Ly Nd Nk Nw Nx Ph Rb Rf Rh Ub Vv) cP(Ax bV cI cR cS cT gL Ip Ir Iv Jn Kc Kk Mw Nw Nx Ou Qd Rf Rh Ub) Iv(aW bN bX cI cQ cT Il Im Is Ji Kc Lv Mw Nk Ok Qd Ub Us) Nx(cI Ii Il Io Ir Is Jj Jo Lv Mb Ng Nk Nm Ok Oy Qa Us) cI(EF Fb gL Hc Jy Kk Kq Ph Qt Rf Ub Vv) Io(bV cT Kp Kq Ou Ph Rf Un Vv) cT(bJ Kk Ly Rf Rh Sr Ub Us) Ub(Ki Kk Mr Nk Ou) Qd(Il Js Lz Nk Ok) Kk(bJ cQ cS eF) Kq(Af Bn Iq Us) cQ(Kc Oh Rf) Nj(Kc Ph) Nk(Is Ph) Iq(Ir Is) Sr(Il Jn) Ou(Ow Rb) Us(bV Rf) CsKr LybV} Kk{cQ(Af As Ba bE BN De Fp Gp Hw Ib Ii Il Jd Jo Kg Kj Kr Nf Nw Of Oy Pg Ql Rf Rj Sr St Ub Ue Us) Oy(aY cN cP cT Cu Ef Fr gL Hc Io Jy Kp Kq Mi Mv Mw My Rb Ub) Ub(aM bE bJ bN cP Cq Ha Ib Il Iq Nf Nk Pb Us Tj) eF(Af Bn De Ib Il Kg Kj Kr Mn Sr Uc Ue Us) cP(As bE dI Fp Gp Hw Io Jo Kr Rf Sr) Us(aY Ba bV cT Kq Lv Rf Up) Jo(aY Ba bE cT Mw Ph Vv) aY(As bE Fp Kj Mn Rf) Bn(Jy Kq) Fp(bV cT) Ha(Cu Kq) Ib(Ba Qy) gL(Af Sr) GpdA LvMn IlJy IocT QvaX JubN KrbV} Kq{Us(aF Ao aS aW aY Ba Bb bI bV cI cP cQ cT dA eF Gl Ii Il Io Iq Ke Kp Ny Oy Pg Qn Qv Ra Rb Ri Sr Ub Uh Up) Bn(Ad aF Al Ao aS Ba bI bN cT dA Dd Dg Gl Io Iu Jo Ke Kp Kr Ld Ly Mn Oy Pd Pg Ra Sr Ur) Af(Cq gL Ha Ib Ii Ij Il Jo Kc Kj Nf Oy Qv Sr Ud Ue Ul) Uc(aW Bb Kc Lh Mn Ou Qy Ra Vp) Jo(cI cP cQ Io Iq Kp Sr Vv) Oy(cI cP Hc Io Kp Mn Sr Uh) cI(Ad De Ha Ib Ii Kj) Ii(bN Rf Ul) Uh(Ib Kj Nf) Ao(Nf Vv) cP(Ib Kj)} Jo{Kf(Af aY Ba cP cQ cT dA Dp Hc Io Ip Iq Iv Mc Nj Pg Sr Uh Vv) Nx(aY Ba bN cP cT dA Fr Ii Il Iv Jj Kp Lv Mb Nc Oy Ph Vv) Kp(bJ dA Io Ip Iv Mg Rf Sr Vv) Cu(aY cI cP cQ Io) Iv(cT Kc Nk Ok Ph) Rf(aY cQ cT) Ok(Lv Nk Qd) BaKn NkQd RbcT OwOu PheF} Us{Kp(Af aY bV cP cQ dA eF Io Jy Lv Nw Oy Qd Qv Rf Ri St Un Up) bV(bX dA Kc Kf Ly Nx Rb Up) Rb(Ba cT Lv Qd Rf) Qd(Ba cP cQ cT) Lv(aW cI Nx) Kf(cP cQ dA) Rf(Ba cT eF) Up(Ba Nx St) cP(Jy Un) cT(Nw St) aVdA} Oy{Kp(Ba cP dA Io Jh Jy Kr Qy) Ba(Jy Kc Kf Kn Rf St) cT(Io Kc Ly Qy Rb Rf) Fr(Iv Ly Mb Mm Nk) Jh(aY cP Hc Kc Vv) Nx(Jj Mv Nk Nm Qd) Kc(cP cQ Hc) Kf(cP Hc) NkQd QyQv} cQ{Kc(Af aY Ba bN cI cP Gp Hw Ip Jy Mr Nj Nk Nw Qv Rf St Ub) St(Af Ba Bn cI Cx Nk Nl) Nw(aF aS cI Ii Mb Qn) Rf(Af Ba bN cT Qv) Kp(Kj Kr) BnJy IiQd} Qd{Il(Fr Hq Hv Hw Io Is Iu Iv Lv Ly Nm Ok) Nk(Hw Jj Js Lv Mc Nm Nx) cP(Cq Ha Ii Io Nf) Nx(Jj Jt Nm Nr) cT(Ha Io Ly Uc) Lz(Iu Jj) BaUc LvJs} cT{Rf(Af aY Ha Ii Io Mn Nr Ny Sr Uc) Uc(Jy Lw No Nw St) aY(Af bE bJ cV Io) St(Iq Mn) Kc(Nj Sr) BnJy UbIo QvbE} Nx{Ii(Fr Ih Ir Is Iv Jj Jp Jr Lj Lv Mw Nj Nw) Jj(Lv Mm Nk Nm Ny) Nk(Iv Lv Nm) Qv(Af bE) IlLj} Bn{Jy(aY Il Kc Kp Qv) Nw(aY Ii Il Kr Uh) cP(Jq St) LwKp QvbE RfgL} Nk{St(Af aY Ii Il Mc Ny Qv) Nm(Ji Nw) Ub(Kc Rf) IlIs IqIr IvJj} Rf{gL(Af Ao Ii Sr) Qv(aX bE Io) aY(bE bN Kc) Ba(Kj Uc) IieF} Af{gL(Kc Kp Ou Rb) Jy(cP Il Kc) Nw(aY cP) QvbE} Kc{Nj(aY cP Qv St) cP(Io Jy) SrJn aVdA} Nw{cP(aF aY Ii Nd) aY(Mn Nd) BaUc} Qv{bE(aY cI Cx dA Ou Rh)} Lv{Lj(Il Js) CsKr UcKf IqIr} St{Ii(Io Nj Qy) BaIq IlIo} dA{aV(Rj Ur) CqKp} Ly{bV(bN Io)} NjKfKj UcKpeF IlJyaY

Constrained panels with 3 analytes, where 1.0E-4 >= 'model p-value' > 1.0E-5. Contains 13,032 panels of 6,910,825 total panels evaluated. :
Ni{Kp(Ad Af Aj aM An bE bJ bN cC Cp Cq Cs Ct Cu cV Cw Dd Fn Fw Gp Ha Hr Hv Hw Hx Id Ii Il Io Iq Ir Iv Jn Jr Js Jt Kg Kn Kq Kz Lh Ly Mb Md Me Mj Ml Mr Na Nd Nm Nr Of Om Or Pd Pe Pi Pk Qa Qx Ra Rb Uc Ud Uk Ul Um Up Uv Vp Tj) Kq(Ad Aj aM As bJ bN Cp Cq Cs Ct Cu cV Cw Dd De Fn Fw Hr Hv Hw Hx Ih Ij Io Iq Ir Iv Jn Jr Js Jt Ke Kf Kg Kr Kz Ly Md Me Mj Ml Mq Na Nb Nd Nm Nr Ny Om Pb Pd Pe Pi Po Qx Ra Rb Rj Uk Ul Um Ur Ut Uv Vp Tj) Ax(Ad Aj aM An As bE bJ bN Cp Cq Ct Cu cV Cw Cx Dd dL Ha Hr Hv Hw Hx Ib Ii Ij Iq Ir It Iv Jn Jr Js Jt Kg Kj Kz Lh Md Me Mj Ml Mq Mx Mz Na Nd Nm Nr Of Om Oy Pb Pd Pe Qa Qw Qx Rb Rj Sr Uc Ul Um Vp) Lv(Ad aE aM As aW bE bJ cC Cp Cq Cu Cw Cx Dd Fn Fr Fw Gp gW Ha Ib Id Il Im In Iq Ir Iv Jj Jn Jo Jp Js Kg Kj Kr Kz Lj Me Mr Mw Nf Nw Of On Or Oy Pb Pi Pk Qd Qx Ra Rb Rj Ud Uk Ul Um Up Uv Vp) Cs(Ad Aj An cC Cp Ct Cu cV Cw cZ Dc De dL Fn Fw Gp Ha Hv Hx Ib Id Ir It Jr Jt Kd Kg Kn Kz Lh Li Ly Md Mq Mx Mz Nb Ny Ok Om Or Pd Pi Pk Po Qa Qx Ra Rb Rj Sr Uc Ud Uk Up Uv Vp Tj) Sr(Ad aJ aM Ar As Ba Bn Cq cT Cw Dd Fr Ha Hr Hv Hw Ib Id Ii Ij Il Iq Ir Iv Jn Jp Jr Js Jt Kg Kj Kr Kz Lx Mb Me Mj Mr Mw Na Nf Nm Nw Of Oy Pb Qd Qx Rb Rj Uc Ud Ul Um Up Uv Vp) Kf(aM As bJ Cp Cq Cu Cw Dd Ha Hr Hv Hw Id Ii Ij Il Iq Ir Iv Jn Jr Js Jt Kr Kz Mb Me Mj Ml Mr Na Nf Of Om Or Pb Pd Pe Pi Pk Qx Ra Rb Rj Ud Ug Uk Ul Um Up Uv Vp) Kk(Af Aj Ao As Bb Bg Bn Ch Co Ct Cu De Dk Fw Gp Hv Hw Ic Io Ir Iv Jd Je Jn Kj Ks Ky Ld Mc Md Mk Mn Ms Mt Mw Mx My Mz Nj Nk Nq Nv Ny Og Pi Po Pz Qh Rh Tz Uc Ur) Kj(Ar aS Aw Ba bI bX Cp cQ cS Cu Dc EF Ez Fr Hc Im Ir Is Jk Jn Jp Ky Li Lx Mu Mw My Nb Nc Nj Nk Nn Nw Oh On Ou Ph Qa Qd Qe Qy Ub Un Ut Vv) Ou(Af aM As bE bJ Bn cC Cq cR Cx Fn Gp Hr Hw Ib Ii Il Io Jo Kg Kr Kz Ly Mb Me Mq Mr Na Nd Nf Nm Of Oy Pb Qw Qx Rb Rj Uc Uk Ul Um Us Tj) Ph(Af Aj AN As bE bJ BN cV Cx Gp gW Hw Ib Ii Il Iv Kg Kr Kz Ly Mb Me Mr Na Nd Nf Ng Nm Of Oy Pg Pi Pk Qw Rj Uk Ul Um Us) Qd(Ba Bb cC Cq cR Cx Fn Fw Gp gW Ha Hv Hw Ib Ij Iu Iv Jj Jn Jr Jt Kr Kz Lz Me Ml Mx Ng Nm Nr Of Pb Pd Pe Qn Uk Ul Um Ur Tj) Nw(Bb Ch Cq Cx Dd Dk gW Ha Ib Ih Ii Ij Il In Iv Jd Jj Jo Js Ke Kr Md Mt Nf Nk Nm Nr Of Oy Pb Pd Qx Uc Uh Ul Um Ut Vp Tj) Is(Aj aM As BN Cq cV Cx Dd Ha Hv Hw Ib Ii Iu Iv Jj Jn Jp Jr Jt Kr Kz Me Ml Mx Nf Nm Nr Of Oy Pb Pd Rj Uc Ul Um) Dc(Ad Af Aj aM As Cq Cu Cw Dd Hr Hv Hw Ib Ii Ij Io Iq Ir Jn Jr Js Jt Mr Na Nd Nf Nm Of Oy Pb Qw Uc Ul Vp) Ib(aJ aP Ar Ba Bo CP Cu dA Dk eF Fr Hc Im Jh Jk Jn Jp Lx Mv Mw Nb Nc Nj Nk Nq Nx Ny Qh Qy Ua Ub Vv) Ih(Fr Fw Gp gW Id Il Iq Iv Ji Jj Jo Jp Js Kg Kn Kz Mr Mw Nf Ok On Or Oy Pi Pk Ql Qn Qx Ra Rb Rm Ud Up) Qw(Af aP Ba bN cI cP cQ cR Cu Cx dM eF Hw Il Ji Jj Jp Jr Jy Lw Mb Mw Mz Nb Nj No Nx Qa Qt Rh Un) Jn(Aj aM As bE bJ bN cC Cq cV Cx Dd dM gW Ha In Jj Jo Kg Kr Kz Mr Nf Qx Rh Rj Uc Uk Ul Um Vp) Af(aP Ba bE bN Cp Cu Cx dM eF Fa Gp Im Ir Ji Jj Ky Lw Mw Nj Nk Nl Nv Oh Om Qa Un Ur Ut Vv) Us(aJ aP Ar aS bI Bo bX Cp cQ cR dM Ez Fr Hx Il Im Jr Jy Kn Lw Mw My Oh Qa Qe Qy Ua Ut Wm) Oy(aP Ar aS cH Cu Dk EF Ez Hc Ir Iv Jg Ji Jk Jp Jy Lj Mu Mw Nv Ok Qh Qy Rh Ua Un Ut Vv) Bn(aP Ba Cp Cu Cv dM eF Fa Fr Im Ji Jj Kd Ke Kn Ky Mw Nb Ne Nj Nl Oh On Qa Un Ur Ut Vv) Aj(aP Ar Ba Bg cS EF Ez Fr Hc Jg Jk Jp Kl Mu Mw My Nl Nx Oh On Qe Qy Rh Ua Vv) Jo(Ad aP Bg bN Ct Ef Ez Fr Gp Hc Ir Iv Jp Kd Ky Mw Nv Oa On Qe Qt Qy Rh Ua Un Ut) Nx(aE cC Cq cV Cx Gp gW Ha Hw Ic Kg Kr Ky Kz Og Qx Rb Rj Uc Uk Ul Um Ur Vp Tj) Ba(Ao aW Bb cV gW Hr Hw Ii Il Jd Jt Jv Kr Ky Mr Ms Nf Ng Of Rg Uc Uk Uu Uv) Mr(aJ aP aS cS Cu dN eF Ir Iv Ji Jl Jy Kd Kn Lj

Figure 19 Continued

Mw No Nv Qa Qe Qh Un Vv) Jp(Ao As Bb bN Ch cV Cx gW Ha Il In Iv Jj Jr Ke Kr Ly Mb Nf Ng Nk Uc Uk) Io(aP aS bN bX cR cS dM eF Ez
Fb Gp Ic Kl Ky Oa Qy Rb Rh Rj Ua Ur Vv) Nf(aP Ar bX cN cR dM eF Fr Ir Iv Ji Jy Kd Kn Mw Ok On Qh Qt Un Vv) Ky(aW aZ bE cC cI cP
cR cT dA Gp Il Im Ly Mb Nc Nd Qz Rb Rj Uk Ur) eF(aE As aW bN cC cV gW Ii Il Kg Kr Ly Na Nd Nm Of Rj Ub Uc Ul) Kr(aJ Ar cN cP cQ
cS dA dM Fr Gp Jj Ly Mw Nc Oa Qa Qe Un) Vv(aJ Ao aW bE Bg Ch Co gW Ha Ii Il Mk Ms Nd Nj Of Pb Tj) Il(aJ bX cS Cu Fr Ir Iv Ji Jy Li
On Qh Rh Un Ur) gW(Ar aS bN cP cQ cT Gp Jy Mu Nb Nj Qv Rh Ug Ur) Kz(aJ aP cC cP cQ cR cS Im Mp Mu Mw Nj Nk Oh) On(Ao As Hw
Ii Ij In Iv Jj Mb Mm Ng Nm Of Uc) bE(aS aW cH cW Cx dD Ly Nb Ne Nj Nl Qh Rh) bN(aP Ar aX bX Jy Ly Mi Nb Ne No Qe Rj Ur) As(Ar aS bI Cp Jq Lw Lx Mi Mu Nb Qv Un) Uc(aJ CP Cu Fr Lx Mw Nb Nc Qa Ua Un) Hw(aP Ar aS cR cS dM Ez Ok Qy Rb Ua Ut) Nd(aP aS Bo cR cS dM dN Jy Qh Qy Ut) Ji(Ii Ij Iv Jj Js Jt Lh Mx Of Pb Pd) Ul(cQ cT dA dM Kn Lw Lx Nc Nk Qh Un) Rj(aJ aS cI cP cR dM Im Nc Nj Nk) cV(aP Ar aS cR cS Fr Mi Mw Nb Oh) Cu(Cq Dd Ii Ij Iq Js Jt Of Pb) Lx(aF Cq Cx De Ha In Qx Vp Tj) Fr(Ch Cx In Iv Jj Mb Nm Of) Rh(aJ aX bX cN cP dA Im Ly) Uk(cP cQ cT dA Nc Nj Nk Oh) Um(cQ cT Mi Nc Nj Nk Oh Qh) cR(aW bX cN dM Ld Nj Ue Ug) Gp(aS aW cQ Cx dM Nj Oh) Nb(Ch Cq Ct cZ De Ha Qx) Bo(Bg Co Hq Iu My Of) In(Jl Lj Mw Nv Qa Qe) Un(Ii Jt Mb Me Na Nm) Ch(Ar Mw My Qy Ua) Lw(Ad aM Cq Cw Dd) Jj(Cx Ir Iv Jl Mw) Ur(cQ Cx Mb Nc Pg) aW(aX Mu Nl Oh Ow) bJ(aS cH Mi Ne Nj) dI(aS bR bX cA cF) Ao(Jg Jy Pg Qy) Fn(bX cP cQ Ld) Ii(Ar Rm Ua Ut) Of(Aw Cp Ok Ua) aF(aO bZ Jy No) cC(aS bI cN Rb) cH(aM Iq Nm Pb) Cq(Mt Ny Qa) Dd(Ir Jq No) Qh(Ij Iq Js) Ok(Nm Pb Pd) aJ(aM Qn Ug) Ar(Cx Ha) Ly(dM Qt) Mb(Fb Ra) Mu(Bg Co) Qv(cN cZ) Jy(cI cQ) Kg(cP cT) Oh(Ha Tj) BbJg FpOa MeQt MwIv NcRb NjUg IrIu NyVp UvdA aEbS aSaX bXdE} bA{Nb(Ad aE AF aH Aj aL Ao As Bb bN cE cG Ch Co Cp Ct Dd dF Fp Hq Hr Ij Il Iq Iu Jd Jk Jt Ke Kz Mb Me Mj Mk Mn Mq Mw Na Nf Ng Nm Nq Nr Ny Om Pb Pd Pe Po Qb Qx Ue Ut Vp Tj) Mu(Ad aE Aj AL As aY Bb bF Bg cG Ch cI Co Cp Ct Cw cZ Dd dF Fa Gl Hr Hu Ii Iu Jd Je Jh Kg Kj Lh Mb Mk Mr Mw My Nf Nq Nr On Pb Pd Pg Qb Qt Qx Tz Ue Uk Tj) Jy(aF Ao As bF Bg bN cE Ch Co Cp Ct Cw Dd De dF dG dH Gl Hr Ib Ii Iq Kj Kr Lh Ma Mb Md Mk Mm Mq Mr Nm Nq Nr Ny Of Om Or Pa Pb Pe Pf Pg Po Tz Ue Uk Ul Um Tj) Rb(Ad aE aF Aj aL bN bQ Ch cI Ct Cw Cx Dd De dF dG Fp Gl Gp Hr Hv Hw Ii Jt Ke Kg Kr Mj Mk Mn Mq Na Ne Nr Pd Pe Pg Po Rf Rj Ub Ue Uk Ul Vp Tj) aY(aF aL aM bN bS bW bX Cq dF dH dL Fp Gl Ha Hq Hw Ib Ii Il Kj Kr Mb Mp Mr Nf Nk Nw Ny Of Or Ow Pg Rg Rj Sr St Uf Ul Um Ur) St(aF Ao Bn cI cP Cq Cw De dF Fp Fw Gl Hr Ii Il Iu Jk Js Ju Jv Ke Kg Kr Lz Mr Nl Nr Or Pb Pd Pe Pg Pi Po Qh Sr Uf Uh) Ha(aA aE Ar aW bX cI cP cQ cR Cs dA DC Gl Ip Iq Iv Jq Kd Kp Lw Lx Mc Mr Nk Nx Ny Ph Qv Qz Ra Rh Rj Ub Un) Nw(aF Al Ao aW Bb bF Bn bQ cE cG cI cP Cx cZ Dd dF Fw Hq Hw Il Jk Jq Jt Kr Mc Nf Nk Nr Nv Pd Pf Sr Ub Vp) Sr(aA aE aF Aj As BN bQ bX cA cE cI cP cQ cR cS Ct Fr Jp Jt Ki Kp Ld Nf Nx Of Qd Qz Rj Ub Ur) Kr(aA Af aW Ax bV Ch cQ cS Ct Dc Hf Iq Iv Jq Jv Kd Kf Ki Kn Kp Ld Lw Ly Mc Me No Oh Ou Ph Qd Ub) Qv(aC aL As aX bJ Bn bQ Cq Cw cZ Dd De Fp Hr Hv Ib Ii Jt Jv Kg Lh Me Mj Mr Nf Of Pb Rj Ul Vp) Kp(Ad As Bn Cq Cw Dd Hv Hw Ib Ii Ij Iq Jo Js Jt Kg Kj Lh Mj Mr Na Nf Nm Of Pb Pi Rj Ul Vp) Nk(Af Ao aW bJ Bn cE cI cQ dA Gl gW Hw Ib Ii Il Jd Kj Mb Mn Nd Nf Ny Pg Qd Rj Ug Uu) Kq(Ad Af As Cp Cw Dd De Hr Ib Ii Ij Jo Jt Ke Kg Kj Mj Mr Nf Of Om Pb Pd Pi Po Vp) Iv(Cq Cw Dd Fw Hr Hv Hw Ii Ij Il Js Jt Lh Mr Na Nf Nm Of Pb Pd Pe Po Qa Uc Vp) Qd(Cq Cw Fa Fp Fw Gp Hq Hr Hv Hx Ii Il Ir Iu Jk Jt Ke Kz Lh Mj Nf Qh Rj Tz Tj) Kk(As bJ BN cV Cw De dF Gp Hr Js Jt Ju Jv Ke Kg Lh Mj Pe Pf Po Rm Ue Vp) aA(aM aP bQ Cx dG dH Hw Ib Il Jt Kj Kz Mb Mj Mn Na Nf Nq Ny Pg Rj Uc Ul Uv) dA(bQ bR bS cA dG dH Ib Jo Lz Mb Mk Mn Mr Of Or Ow Pb Pd Pe Pf Po Uk Ul Um) Ub(bJ BN cI Cq Ct De dF Fw Ib Il Ki Mb Mc Me Mj Nr Ny Of Rf Rj) Iq(Af bJ cP cQ cR cV Dc Fw gL Kf Mc No Rj Uc Ud Un Vp) Kc(Cq Dd Fa Fw Ii Il Iu Kj Li Mj Ow Pe Pg Qh Rg Uv Tj) Nx(Af Ao Bn Cq Cw Hr Hw Ii Jt Kj Lh Mn Nv Ny Of Pb Po) cP(bQ Hr Hw Ii Il Jd Kg Kj Mb Mk Mr Nf Pb Uc Ue Vp) cQ(aF aL BN bQ bX Gl Kj Mn Of Pb Ue Uk Um Ur Vp) cV(eF gL gW Hw Ib Il Jj Jv Kj Ly Mc Nd Ny Og Rj Uv) Qy(aE Aj Ao Ch Co Ct Dc Jk Mk Nd Nr Of Qt Ue Uu) gL(Af Cx Gl Hw Ii Il Ly Mc Mn Nd Nr Ny Pg Uu) Fp(Ar aW cE Ch cI cR Cs Ib Ld Nd Ph Rj Ur) Ra(As Cq Cw Hr Kg Kj Mj Mr Nd Pb Vp Tj) Rf(As dR gW Iu Me Mr Mz Ne Nf Nm Pd Tz) Uh(bJ Ct Kz Mb Me Mj Nf Pb Qz Rj Ul Vp) bX(bJ cI Cw Ii Il Mb Mc Mn Nf Pb Uc Vp) Ih(Cq Fb Fw Ii Jo Js Mn Nr Ny Rm Uc) Rh(Aj Cw gW Ib Ii Il Kg Kj Lh Ny Pb) Ly(Bn Dd Gl Ib Ii Il Kj Mk Nd Ny) Ld(Cq Dd Hr Il Jo Mn Pb Po Vp Tj) bJ(aW Ch cI Hw Il Jv Kj Mn Nr Ny) Rj(aF Ch Gl Hw Jv Lw Mj Pg Ri) cR(aF bQ Cw Hw Ii Il Kj Nf Pg) No(Dd dF Fw Ii Ke Mn Po Vp) Ib(aW bN Ed Jh Lw Mj Mn Mw) Nd(Af eF Gl Il Nj Ny Um) Uc(bR Cv Dc Ke Lx Nt Ou) Jq(Ad Cw Dd Ii Jt Pd Vp) Ju(aE BN cI Cx dF Mb) Kd(Cq Cw Dd Jo Mr Pb Vp) Pg(aW Bn Hq Kj Mb Nf Oy) Jv(aE bN Cx dF Mb Mj) Kf(Cq Ii Kg Lh Mr) aW(Bn cZ Hw Ow Vp) cN(bN cG dF dG dH) Bo(Ao Bg Ch Co) Dc(Ad Bn Cw Vp) Mc(cE Il Mk Mn) Qz(Ao As Nr Pf) Un(Dd Ke Lh Mj) Af(Il Mn Oy) Gl(Gp Hw Il) Nf(Lv Mn Ny) Nj(Mb Ue Ug) Ph(Cq Ii Mn) cS(bQ cG dH) Ar(Mr Nr) Cu(Ii Jo) Ed(Ct Kj) Lw(Ul Vp) Mj(Ue Uu) Js(Jn Jr) Kn(Oy Pb) Ny(Cq Vp) dG(aJ dN) eF(Of Uv) PoLx FbNr NqOy NgcI HwbG IpJo KzPf UgbQ} Kk{aA(aM As bE bJ Cq Ct Cu Cw dG Fp Fw Gp gW Hr Hv Hw Hx Ic Ii Ij Ir Iv Jd Je Jk Jn Jo Jr Js Jt Kr Kz Lh Ly Mb Mc Md Me Ml Mr Mt Mw Mx Mz Nb Nd Nk Ny Of Og Or Pb Pg Pi Po Qh Qn Qx Rf Rh Rj Sr Tz Ul Um Ur Ut Uv Vp Tj) eF(Ad aE Aj aM Ao As aY bE bN cG Ch Co Cq Ct Cw Dd dG Dl Et Fn Gp gW Ha Hr Hw Ii Ij Io Iq Iu Jd Jt Ke Ko Mb Mj Mr Nf Nj Nm Nr Of Om Or Pb Pd Pf Pg Po Qv Qx Rf Rj Ug Uk Um Uv Tj) Rf(Af Ao Bb bE bI BN Ch Cq cT Dd De Fp Gp Ha Ib Ii Ij Il In Io Iq Jo Js Jt Kj Kr Mc Mj Mk Mn Mr Mz Nd Nf Nk Ny Og Oy Pb Pg Pi Po Qv Qx Sr Ub Uc Ug Vp Tj) Mn(Af aX Ba bE bI BN cP cS dI Fb Fr gL Gp Ha Ic Ih Il In Iq Jj Jp Jy Kq Ky Ld Mc Mi Mu Mw Nb Nf Nk Nw Og Oh On Oy Pb Ph Qd Qv Qy St Ub Ur Tj) Ba(aE Ao aY bE Bg Ch Co Cq Ct Dd gW Ha Hw Hx Ij Il In Iq Jd Je Js Kj Mj Mk Ml Mr Ms Mw My Nb Nd Nf Nk Of Og Pb Po Pz Qx Tz Uc Ul Um Vp Tj) Ub(Ao Bg Ch Co Ct Dd Dk Fw gW Hv Hw Hx Ij Ir Iv Jd Je Jn Jo Js Ld Mj Mk Ml Mr Ms Mt Mw My Nb Nd Nq Nv Ny Of Og Po Qh Qx Tz Uc Ul Um Ur Vp) cT(Af Aj As bE BN Dd Fn Fw Ha Hr Hv Hw Ib Ii Il Iq Jd Js Jt Jv Kg Kj Ko Kr Nf Ny Pb Pe Pg Po Ql Rj Sr Uc Ue Ug Uk Ul Um Uv Vp Tj) Mu(aY Bb bF Bg bN bQ cE cG Ch Co De gW Ij Il In Iq Jd Js Md Mk Mr Mt Mw My Nb Nd Nq Ny Pb Po Qx Tz Ul Um Ur Tj) Io(Ao aS aY BN bV Ch CQ cS dA gL Gp Ha Ib Ic Il Im In Iq Jd Lv Mr Nf Nk Of Og Pb Qv Qx Ul Um Ur Tj) Qv(aC Af BN Cq cZ Dd gL gW Ha Hx Ib Ij Il Iq Jd Js Mj Mk Ml Mr Nf Nk Of Oy Pb Qx Uc Ul Um Vp Tj) bI(aE Af As bN Dd De Fn Fp Hw Ib Il Jd Jo Kc Kj Kr Mc Nf Ny Oy Pg Rj Sr St Ue Ug Uk Um Us Tj) Oy(As Aw aX bE Bg Bo bV cS dA Fn Gp Hu In Ip Ju Jv Kf Mp Nc Nk Nl Nq Nx Ph Qt Sr Ue Us) Gp(Af Ao aX aY bE Bg bV Ch Co Dd gW Ib Ij Il Jd Jo Mk Mr My Nf Nk Of Qx Uc Um Tj) Ha(aJ Ar As bV cN dA Fr Jn Ju Jv Jy Kf Kp Lv Lx Mc Mi Mw Nb Nw Ph Qd Sr St Ue Ug) Il(As aX bE bV cN cS Cu dA dI Fr gL In Jv Kq Lv Mc Mi Mw Nc No Nw Qd Rb Sr St) Ib(As aY Bo bV CP dA Ef Fr Hc In Jh Jv Jy Kp Kq Lv Mi Mv Mw My Nb Ph Rb) Jo(aC bN bV cS Cu dA dN Fr gL Hc Ih Ip Iv Kf Kp Kq Lv Mg My Nx Ou Qt Qy Sr) Kq(Af aM bN Cq Dd De Ij In Iq Js Mj Ml Mr Nf Ny Of Pb Po Ul Ut Vp Tj) bN(aX aY bE bV cN cP cS dA dN gL gW Jv Jy Kr Mc Mi Nb Nj Rb Sr Us) Tj(AS aW aY cP cQ dA Ju Jv Jy Kj Kp Mi Mw Nb Nc Ou Rb Ue Ug) In(Bn Cu Dd Fb gL Iq Jv Jy Kp Mi Mw My Nf Nk Ou Ph Rb Rh Ue Us) Uc(Bo bV Cp Cu Fr Jy Kf Kp Lv Mi Mw Nb Nw Ph Qd Qt Qy Sr Un) bV(bE bJ Bn De Hw Ii Iq Jd Kj Ko Ly Nf Ny Pf Pg Ql Rj Sr) Dd(bE dA Dc dI Fr Hw Im Jy Kp Lv Lw Ly Nb Nw Ph St Ue) Us(Af bE cP cS Cu dA Fr gL gW Iv Jy Mi Mw Ph Qd Qy Ri) Ue(Ao aY bE cP Cq gL Iq Js Mj Mr Nd Nf Nk Pb Ul Vp) gL(Ao Bb Bn cP cQ gW Hw Ii Iq Jd Jv Kj Nj Ny Pg) Kj(bE cP cS dA Ef Fb Ic Lv Nk Ph Qy Sr Ua) Nf(As cN cP Fr Ju Jv Jy Kr Lv Mw Nb Rb) dA(aE Aj As aV Bn Cq Fp Hw Pg Rj Ur Uv) Jv(aE aY bE Cq Iq Mr Nd Pb Ul Um Vp) Jy(aF Ao cP Cq Ij Je Mr Of Po Um Vp) aY(Bn De gW Ju Ko Kr Nw Pg Sr St) bE(Af aS cW Ju Nj Pg Rb Sr Ug Ur) cN(Af Bn De Hw Ii Jd Nj Pg Sr) cS(Fp Hw Kg Ko Kr Nj Pf Pg Sr) St(Af Al Bn cP Ii Iq Nk Vp) Of(As Kp Mi Mw My Nb Qy Rb) aJ(Fp Ii Jd Ko Ny Pf Pg Sr) aX(aE Fp Hw Jd Mc Pg Sr) cP(cZ Fn gW Jd Nw Pg Rj) Lv(Af Bn De Iq Js Mj) Nk(As Fn Kc Mc Nc Ug) Mi(bJ Cq Pb Ul Um)

Figure 19 Continued

Ch(As Bo Mw Qy) Cu(Cq Mr Po Vp) Mc(Mk Ml Mr Qx) Iq(aS dI Kp Qd) Nw(aF Ao Bn Vp) Af(Cv cX Kc) Kp(Cq Mr Pb) Ny(aS dI Vp)
aE(cQ Fp Sr) Ao(As Bo) Bn(Jq Lw) Po(Fr Lx) Nb(Cq Je) Nj(dI Kc) Ju(gW Pb) aC(Jj Ug) dN(De Ko) FpaS MwIj IiJq QycR KrOg UmcQ PgdI} aA{Kp(Ad aM As bJ Cp Cq Cu cV Cw Dd De dG Fw Ha Hr Hv Hw Hx Id Ii Ij Il In Iq Ir Jn Jo Jr Js Jt Kg Kj Kr Lh Me Mj Ml Mr Mx Na Nf Nm Of Or Pb Pd Pe Pi Pk Rj Uc Ud Ul Um Up Uv Vp) Nb(Ad Aj aM An As bE bJ bN Cp Ct Cu cV Cw cZ Dc dF dG dL Fn Fw Gp Id Jd Kd Ke Kg Kn Ko Kq Kr Kz Or Pi Pk Ql Qn Qx Ra Rh Rj Tz Ud Ue Ug Uk Ul Um Up Ur Ut Uv Vp Tj) cQ(AF aM Ba bE bJ BN bQ bS bX cI cV Cx dG Fb Hw Ib Il Kj Kz Mc Me Mu Na Nf Nk Nw Oy Qv Qz Rj St Uc Ul Um Ur Uv) aY(aM aP bE bN bW cV Cx dG dL Ha Ib Ic Il Jo Kj Kz Mb Mn Mp Mu Nd Nf Nw Of Ow Oy Pb Pd Pg Rh Sr St Uc Uk Ul Uv Vv) Kq(Ad As bN Cq Cw Dd De dG Fw Ha Ib Ii Ij Il Iq Js Jt Ke Kj Kr Me Mj Nf Nm Om Or Oy Pd Po Qn Rj Uv Vp) Nx(Ad Aj aM As bE bJ bN cC Cq cV Cw Cx Dd De dF dG Gl Gp Ha Ib Ke Kg Kj Kr Qn Sr Tz Uc Ue Uk Ul Uv) Ou(aM As bE bJ bN Cq cV Cw Dd De dG Fw Ha Ib Ii Jo Kg Kj Kr Kz Mb Me Mj Nf Nm Or Ow Oy Pb Uc Ul Uv) cP(Af aM aP bE BN cI cR Cx dG dL Ha Ib Ic Jo Jy Kj Kz Mb Mj Nd Nf Nw Oy Pg Rf Rh Rj Sr St Um Uv) Ic(bN cI Dd De dG dH Ib Ii Il Iq Jo Kj Kr Kz Mb Mc Mn Na Nd Nk Ny Oy Pg Rb Rj Sr Tz Uc Uv Vv) Iv(Ad aM An As bJ bN Cp Cq Cu cV Cw Dc Dd De dF dG dL Fw Ha Ib Kj Kr Kz Rj Uc Ul Um Uv Vp) Rf(Ao Ba bN cI Cx De Fp Gl gW Ib Il Ke Kj Kr Mc Mn Nd Nq Nr Oy Pg Qn Qv Rb Rj Tz Uc Vp) Ar(Af aP bQ bS cV Fp Ha Ib Ii Il Jo Jt Jv Ke Kj Kr Na Nf Nq Nr Ny Oy Pg Sr Tz Uc) Rb(aE As aZ bE bN cC cI Dd Gp gW Ha Hw Ib Il Jo Kj Kr Na Nd Og Oy Rh Rj Ub Uc) Jn(Cq Dd De Fw Ha Hw Ib In Iq Js Kj Kr Mr Mx Nc Ok Oy Pf Ql Rj Sr Tz Uc) Nw(aF Ao dH Gl Ha In Iq Js Ke Lz Md Mm Mr Mx Mz Nc Nf Ny Pd Pf Qn Sr Uc) cT(Af aM bE bJ BN bQ bX cV Cx dG Ha Hw Ib Jo Kr Mn Oy Uc Ul Um Uv) Ld(As bJ bN Dd De gW Ha Hr Ib Ii Il Iq Jo Kj Kr Nf Or Oy Rh Rj Uc) Cx(aP aW bE bR bS cI cV dG dH Ib Jy Kj Kz Mr Mu Nd Oy Qv Rh Rj) Ph(As Cq Cw Dd De Ha Ib Ii Il Iq Jo Jt Kj Kr Mj Nm Oy Uc Uv) Af(aM aW Ba bE bN bQ bR bS bW bX cA cB cI cV dG dH eF) Ok(Hw Ij Ir Jr Jt Me Ml Mm Mt Mz Nm Nr Of Om Pb Pd Pe) Qv(As aX bE bN cI Dd gW Ha Iq Kj Mb Na Nd Oy Pg Rj) Nk(As aW bE bN cC cI De gW Kj Kz Qn Rj St Ub Vv) Ha(aW Ax Cs dA Fb Fp Ir Kf Lj Oh Qd Sr St Ub) Rh(aU bE Fb gW Ii Il Iq Kj Na Nd Ny Pg Tz Ub) bR(aM Ba bE bJ BN cI Ii Mb Mc Na Nf Pc Qn) Sr(bE bJ bN bX cI cR Fb Ii Jp Og Qd Uc Ur) Vv(Aj Ao cI Gl Ib Iq Jo Mc Ng Ny Oy Pg Tz) Bn(aP aW bQ bS bW bX cA cB cV Dc dG dH) St(aF Al Ao Dd Ii Il Iq Ke Ny Pg Qn Vp) Kf(Cq Cw Dd Ii Iq Jt Kj Kr Mj Nm Oy) bJ(aP bS bW bX dH Iq Kj Nq Ss Tz Ub) Is(Hw Il In Iq Js Mr Mx Nm Ny Pf) Ji(In Iq Mm Mr Mx Nf Nm Ny Oy Pf) Ub(cR cV Ib Io Iq Me Oy Ur Uv) Ir(Hv Il Mr Mx Nc Nf Oy Pf Uc) aW(bE cA cV dG dH Ib Kr Mx Oy) bN(aP bS bX cA dH Iq Jv Mc Nq) Uc(Ax Ba Cu eF Kn Lv Qd) cI(bE cV Gp Mb Mc Nd Rj) Mu(aF Cq Dd De dH Dk) Qd(Cq Fw Io Nf Qn Rj) Lj(Iq Js Lz Mr Nf Pf) cR(aP bS cV dH Pc Pg) Ba(bX cV Ib Uu Uv) Cs(Fp Kr Li Mj Mr) Lv(cV Dd dF Or Qn) Ii(Cu Dc Fb Jy Kn) Nq(aX bE cC dI) Ly(gW Jj Ne Uu) Oy(Fb Hc Mb Qy) bX(aM bE dG dI) Ax(Fp Jt Kr) Fr(Mm Mt Nm) Jy(aF Il Qn) dH(bE dI Na) Fb(Mc Pg) Mn(eF Ky) Mr(De Lx) Kn(Dd Jo) Rj(gW Io) Uv(aZ dA) dG(cN Ms) CvQn GpNy NmOn LzMc MbeF MjIq NdHf IbQy IhJs HcKj JvaE KrOh KzOg UmdA UrgW bEbS} In{cQ(aE aJ Ar aS aW Ax Ba Bc bV bX cI CS cT Cu Dc dM dN eF Fb Fr Ih Ip Ir Is Ji Jl Jm Jn Kf Kn Kp Kq Lj Lv Lx Ly Mb Mr Mu Mw Nd Nt Nw Nx On Ou Pe Ph Pi Qa Qb Qd Qe Qt Qv Rb Rm Sr St Ub Un Vv) aW(Ar Ba bE bI bV bX cP cR cS cT Cu dA dN eF Fb gL Gp Hc Io Ip Ir Is Jn Jy Kc Kp Kq Lv Ly Mu Mw Nd Nk Nt Nw Nx Oh Om Ph Qd Qt Qv Qw Qy Rb Rf Rh Ub Us Vv) Qw(Ax Ba bI bV cN cS Cu dA dM eF Ez Fb Fr Hc Ih Io Ip Ir Is Iv Jm Jn Jy Kf Kq Mr Mu Mw My Nw Nx Oh Om Ou Ph Qd Qt Qv Qy Rf Rh Sr Ub Un Vv) Qv(aC aX Ba Bc bE bI bJ bV cN cR cS cZ dA dM dN Dp eF Ez Fb gL Ih Io Ip Iv Jn Jv Jy Kc Kp Ks Mw Nj Nx Ou Ph Qd Qt Qy Rf Rh Ub Un Vv) Io(aE aJ aP Ar aS Ax Ba bI bX cI Cp CS Cu Dc dM dN EF Ez Fb Hc Hf Ic Is Ji Jy Kc Kf Kl Oa Qd Qt Qy Rb Rh Rj Rm St Ub Ue) Us(Ar Ax Ba cN Cp cS Cu dA dM eF Ez Fb Fr Hc Ih Ir Is Jl Jm Jn Jp Jy Kf Kn Kp Lv Mr Mw My Nw Oh On Ph Qd Qt Qy Rm Sr St Un Vv) Ou(aS Ba Bc bE bN bV bX cR cS cZ dM dN eF Fb gL Ip Ju Jv Kc Kp Kz Ly Lz Mu My Nf Nj Nx Or Ph Rf Rg Rh Ue Vv) Rb(aJ Ax Ba Bc bE bH bI bV cI cN cR CS cT Cu dA dM Ih Ir Is Iv Jn Lv Mb Mw Oa Ph Qd Qt Rf Rh Rm Ub Un) Kp(bJ Bn Ch cP Cq cS dA Dd eF gW Ib Il Iv Jv Jy Kj Kq Kr Mu Mw My Nf Nw Oy Qd Qt Rf Rj Sr Ub Vv) Rh(aJ Ax Ba Bc bI bV cN Cs Cu dA dM eF Ez Fb Il Ir Iv Jn Jp Jy Mp Mw My Nx Ph Qd Qt Ub Ue Un) cI(bE bJ bR bX cF cH cN cR cS Cu dN Ez Ih Ip Ir Is Iu Jn Lv Ly Mu Nd Nk Nt Nw Oh Om) Sr(Ax Ba Bc bV cS Cu dM Fr gL Ha Iq Jp Kj Kq Mw Nf Nw Nx On Ph Qd Rj Ue Un Vv) Nk(Ba bV Cs cT dA dM Ih Ir Ji Jn Jr Kc Lv Nw Ok On Qa Qe Rf St Ue Un) Il(Ba cS cT Cu dA Dp gL Hc Ir Is Jy Kc Kf Kq Ks Lj Lv Ph Qt Rf Un Vv) Ph(Bc bN cP cS Dd dM eF Fb Fp Iq Iv Jn Jo Ju Jv Kj Kr Pg Qt Qy Ub) Kc(Ba bI bJ bV cS cT dA eF Fb Jn Jv Jy Mr Mu Mw My Qt Rf Ub Vv) Vv(Bc bE bV cN cS dA dM dN Fb gL Ib Jo Kf Nf Of Oy Rf Ub Un) Kq(aF Ao Bb bJ bN cP Dd Ha Ii Ke Kj Kr Mn Nf Or Oy Ue Uh) Rf(Ba Bc bI bN cS dM eF Hc Iq Iv My Nb Nj Qy Ub Vp) cP(Bc bE bN Cu dA eF Fb Jm Jy Mr Mu No Oh Qt St Un) Ly(Ax Ba bI cN cS Cu dA dM gL Ir Is Ji Ok Qd Qt) Ub(Ba Bc bJ bN cS eF Ez Fb Ip Jn Jy Nj Nx) Kf(dA Dd Ha Iq Iv Kg Kj Kr Nj Or Oy Uc Ue) Ok(Ih Ir Is Jn Jo Jr Lv Mb Mm Nf Nm Of Oy) bV(bJ bN cV Ip Iq Iv Jn Kr Mc Mu Nd Nx Rj) cS(Bc bN cT Ip Iv Jn Kr Lv Mb Nd Nx Pi) gL(aE Af Ax aY bN Cx Ip Iv Jn Mb Nd Nx) Mu(aF Bb bF Bg bN Ch Co Cq De Dk dM) Ba(Af Ch Iq Jv Kj Mc Nd Ue Uu Uv) Cu(Af bN Ha Iq Jo Kr Mn Nd Oy Uc) Lv(Ih Ir Is Ji Jn Lj Mw Nw Qd) St(Al Bn Iq Lz My Nj Nl Or Vp) Jv(Ax Bc Ip Ir Is Iv Jn Qd Un) Un(Af Ao Iq Mc Nj Ny Or Uh) eF(aE aS Ax bN Jn Mb Oh Ue) Iv(bJ Fb Jj Kz Oy Qy Ur) Qd(aY Is Mx Nm Or Pf Qc) Qt(bN bX Hf Ki Kz Mc Nf) Nx(Af Ao cT Ih Kr Nr Of) dM(Ar bN Jn Mb Mr Nd Pi) Oy(Hc Ir Is Ji On Qy) dA(aV bR bX cF Nd Ur) Af(cT Jn Jy Nw Om) Iq(aY cT Dc Jy Rm) Nm(Is Ji Nw On) Hc(Ch Ih Kj Ue) aY(bS Nt Rg Uk) bX(Bc cT Ip Jn) Fb(Bc Mc Ue) Ir(Iu Lz Nr) Qy(Ax Ch Kj) Kr(Ax Jp Oh) bN(cN dN Jy) Bn(Jy Nw) Cs(Fp Lz) Nd(cN cT) MbbI MccT MmJi MwKz NbTz UeKs IsJj NwUh aSbJ} Mu{aY(aE As aV Ba bE bF BG bQ bR bS bU bX bZ cA cC cD cE cF Ch cI cK cL cN CO CQ cR CT CU dA De dF dG dI dL Gp Hr Jl Kc Kj Kr Lw Lx Ly Lz Ma Mb Mc Md Mk Mm Mr Mt Nm Nq Nr Ns Nv Ny Of Om Ow Oz Pb Pe Pf Pg Po Qv Rf Rg Uf Uk Um Ur Vp Tj) cQ(aE aJ Ao Ar aS aW Ax bE bF Bg bN bQ bV bX cE Ch Co cP Cq cT Cx De Dk Gp Ha Hq Hr Hw Ii Il Io Iq Iu Jo Kj Lj Ly Mc Md Mk Mn Mr Nf Nk Nq Nv Om Pb Pd Pg Po Qv Rf Ue Uk Um Ur Uv Tj) Dk(aF Ar aS aW Ba bF bJ bN Bo bR bS bV bW bX cA cE cF cG Ch cK cL cR Cs cT dH Gp Hq Ii Io Jk Jn Jo Kf Ly Lz Mc Mn Mp Nw Nx Or Pd Rb Rf Rh Sr St Uk Ul Um Ur Uv Vp Vv) cI(aF Al aX Bb bF Bg bQ bV cE cH Co cP Cq Fa gL Gp Hf Hr Hu Ii Iq Iu Jd Je Jh Jo Kc Kg Kj Ly Mb Mc Mk Mr Mw My Nf Nq Nv Ny Of Om Pb Pd Pg Po Qv Qx Qy Ub Ue Uk Vp Tj) aF(Al aW bV cP Cq cR Cs cT dA De gL Gp Hf Hq Hu Ib Io Iu Iv Jd Jo Jv Kj Kp Ld Lv Ly Mn Mw Nb Nd Nf Ny Oe Ou Pg Ph Qt Qy Rb Rf Rh Rj Sr Ub Ue Ug Uk Ur Uu Uv Vp) Kc(Al Bb bF Bg bN bQ bV cE Ch Co cP Cq Dd De Il Iq Iu Jd Je Jo Kj Md Mn Mr Mw My Nd Nf Nj Nk Nl Nq Nv Ny Of Om Pb Pd Pg Po Qv Qx Ub Ug Uh Uk Vp Tj) Ch(Ba bJ Cq cT cV Cx Dd Gp Hc Ii Ij Jl Jq Js Ly Mb Mc Md Mj Mn Mr Mw Mz Nf Nk No Nu Ny Or Pa Pb Pc Pg Po Qn Qv Qy Rh Rj Ul Um Vp Vv) cP(Al Bb bF Bg bQ bV cE Co Hr Hu Iq Jd Je Jh Jo Kg Kj Lj Mk Mr My Nb Nf Nq Ny Oa Pb Pg Po Qt Ub Ue Uv Vp Tj) cT(Bb bF Bg bQ cE Co Cq Cw De Ha Hq Iq Iu Jd Je Jh Jo Kj Mn Mr Mw Nf Nv Of Om Pg Po Qw Ue Ut Uv Vp) Cq(Ar aS aW bN bV cR Cx dA Fp Ii Il Io Iv Lj Ly Mb Mc Nb Nu Nx Ou Pc Ph Qn Qv Rf Rh Ub) bF(Ao bN cR Cx De Gp Ii Il Io Jt Kj Ly Mb Mc Mn Mw Nf Nq Ny Pc Qn Qv Rg Rh Rj Ue Ur Vv) Ao(aM As bJ cG Dd De gL Ha Hr Jl Kj Kr Kz Mc Me Nk Pa Qv Rf Rh Uk Ur Ut Uv Vp) De(Ar aS Ba bN bV Ii Il Iq Kp Ly Mb Mc Md Nb Nf Nk Nu Ou Pg Ph Qv Ur Vp) bV(bN cG Gl Ii Il Io Iq Jo Ly Mb Mn Nd Nf Nk Nv Ny Om Pd Pg Po Rj Vp) Qw(aR As Ax bN bQ Cx gW Iv Iz Jv Kg Nf Nu Ny Oa Pa Pc Qn Qy Ri Ue) Oy(Fp Fr Ir Is Jg Ji Jn Jp Li Lj Lv Mv Mw My Nk Nv Nw On Qy Rf Vv) Kp(bQ Dd Hq Il Iq Jt Md Mn Mr Mw Nd Nf Nv Ny Of Om Pb Pd Po Vp) Ou(bQ cE Ha Hq Ii Jk Jo Mn Mr Nd Nv Of Om Pb Pd Pg Po Vp Tj) Mw(bJ bN bR bS bW cA cD cE cG cK cL cR Ct dH Or) Bg(Ba Cx Ii Il Io Ly Mb Mc Nf Pc Qv Rj Vv) Co(Ar bN Cx Ii Il Iq Ly Mb Mc Nf Pc

Figure 19 Continued

Qn Vv) bN(Al Bb Hq Hu Iu Jd Nf Nv Pg Ue Vp) Ph(Hq Ii Jo Kj Mr Nd Of Om Ut Vp) Ar(Bb Hq Jo Nd Nv Om Po Us Ut) Kj(Ba Kf Md Nf Nx Pg Rf Vp) aS(Ha Hq Jo Nd Nv Of Om Us) cR(Al Hq Iu Jo Nf Om Pg Ue) Ii(aW Bb bQ cE gL Hf Kf) Cs(Hq Jk Jo Mr Nd Po) Cx(gL Ha Hq Nd Nq Of) cE(Ly Mb Nf Qn Qv Rj) Ld(Ha Hq Jk Of Pg) aW(Jo Nv Of Ut Vp) dA(aV Ha Nd Us Vp) Ba(Jk Jo Nd Om) Bb(Il Iq Mb Nk) Ax(Jo Nv Vp) Nf(aE cG dH) Il(Al Fa Hf) Iq(aJ bQ gL) bS(Iu Om Pg) Qv(aX bQ) Jk(Hc Kf) Us(bl eF) CuJo GpNv MbbQ NdHf UccS IcPg IudH IzVp JdbR} Kq{Af(Ad aM Ao As aW Bb bE bJ bN cl CP cQ CT Cu Cv Cw Cx cZ Dd De eF Fn Fp Fw Gl Gp Hr Hv Hw Hx Id Iq Ir Iv Jn Jr Js Jt Ke Kg Kz Lh Ly Mb Md Me Mj Ml Mn Mr Mz Na Nb Nd Nj Nk Nm Nr Ny Of Om Or Pb Pd Pe Pg Pi Po Qa Qx Ra Rb Uf Ug Uh Uk Um Up Ur Ut Uv Tj) cl(As Bb bE bN Cp CQ Cw cZ Dd Fa Fp gL Gp Hr Hw Ij Il Io Iq Js Jt Kc Ke Kg Ko Kr Kz Lh Ly Mb Me Mj Mq Mr Na Nd Nf Nm Ny Of Om Or Ow Pb Pd Pe Pi Po Qa Qv Qx Rj Sr Ue Ug Uk Ul Ut Uv Vp Tj) Ii(Ad Ao As aW aY Bb bJ bW cP CQ cR cV Dd De DK Fb GL Ha Ib Ij Il Io Iq Jd Jg Jn Jo Jt Kc Kj Kp Kr Kz Mb Mn Mr Nd Nf Ny Of Om Oy Pb Pg Po Pz Qv Rh Rj Sr St Ub Ue Uh Uk Um Uu Vp) Ha(Ad aE Ao aS aW Ax aY Bb bN cP cQ cR Cs cT Cx dA Dg GL Il Im Io Iq Kc Ke Kp Kr Mc Mm Mn Nb Nm Ny Ph Qv Qw Ra Rb Rf Rg Rj Sr Ub Ue Ug Uh Us Vv) Qw(Ad Aj aO aS aW bF Bg bH Nh bN bV Ch Co cP cT Cw Cx De Dg Dk Et Hb Hr Ib Jd Jv Kc Kg Kj Kr Md Mm Mn Nm Nu Ny Of Ok Om Pd Pg Qn Qv Rb Ri Ue Ut) Il(Ad Ao aY Bb bN Ch cQ dA De Dk GL Ib Io Iq Jd Jt Kc Ke Kj Kp Mc Mn Nd Nf Nv Ny Oy Pg Po Qt Qv Sr Tz Ub Ue Uh Vp) Ao(Ad aM As bJ bN Cq Dd gL Ib Ia Jo Js Jt Kc Kj Kr Kz Ly Me Mr Na Nm Or Oy Pd Po Rj Ue Ul Uv Vp) cQ(Ad As bJ bN Cq Dd Hr Ib Io Jt Kg Kj Kr Mb Me Mr Nb Nf Nm Of Oy Pb Pd Po Rj Ue Uk Ul Um Uv Vp) Iq(Ad aE As Bb bN De gL Ib Io Jt Kc Kg Kj Kr Lh Mb Mn Nf Nm Of Oy Pd Po Qv Rj Ue Ug Uh Uk Ul) Kc(Ad Bb bN Cw Dd De Et Io Jo Jt Ke Kg Kj Kr Lh Mn Nj Nk Nm Ok Oy Pd Po Sr Ue Uh Vp) Ib(aS aW aY Ba Bb bN cT Cx dA Gl Hc Io Jq Ke Kp Kr Mn Ny Pg Qn Qv Qy Ra Sr Ub Vv) Nf(aF aY Bb bF cP cT Dg Dk Gl Io Jt Ke Kp Kr Mm Mn Nm Ny Oy Pd Qv Sr Ub Ue Us) Oy(aS aW aY Ba Bb bN cT Cx dA dK GL Ke Kr My Nm Ny Qn Qv Ra Rb Rj Ub Vv) Uh(aM As Cq Dd De Hr Hw Ij Jo Js Jt Kz Mj Mr Of Pb Po Qx Rj Ug Ul Um Vp) Kj(aS aW aY Ba bN cT Cx dK GL Hc Io Jq Kp Mn Ny Pg Qn Qv Ra Rb Sr) Jo(aS aW aY Ba bN cT Cx dA Dp Gl Iv Ke Mc Mn Ny Ph Qn Qv Rb Rh Us) Io(Ad aE bN Cw Dd De Hr Jt Kg Mn Nm Of Om Pd Po Qv Ub Ue Ug) Mn(Ad bN Cw De gL Jt Kg Kz Mb Me Nm Pd Ue Ug Ur Us Uv) aY(As bE bJ bN Cq De dL Kr Nm Or Pd Po Rj Uk Ul Uv Vp) De(aS aW Ba cP cT GL Kr Nb Pg Qv Rb Sr Ue) bN(Ad Bb bV dA gL Jt Jv Kc Mc Ny Ub Ue Us) Qv(Ad As Cq Cw cZ Dd Jt Lh Mr Of Po Vp) Us(Al Hf Hq Jd Jq Kz Lh Ly Nm Nu Pd) cP(Ad Cp Cq Cw Jt Kg Lh Of Om Ue) Sr(Cq gL Hr Mr Of Om Pd Po Vp) Kp(Ad Cq Dd Ij Jt Kr Lh Po Vp) Gl(As Cq Dd gL Gp Jt Mr Vp) Bb(Dd Jt Kr Po Rj Ue) Ny(Dd Jt Pd Ue Ug Um) Vp(aF cT Ke Pd Ub Ue) cT(Cq Cw Lh Of Uv) Po(dA Mc Ub Ue) Ke(aE Cq Of Um) aF(Cq Kr Rj Ul) dA(Cq Pd Uv) Ad(aW Nk) Ue(Dd Nk) Jt(aW Pg) Kr(bV Ch) Rj(bF bV) Of(Nb Vv) McMr JqgL UtVv} Nb{aY(Ad Af Aj aM aX Ba BN CP CQ cR Ct Cu cV Cw cZ Dd De dG dL Fn gL Hr Hv Hw Ii Ij Iq Ir Iv Jn Jr Js Jt Kg Kz Ly Mb Me Mj Mk Ml Mn Mq Mr Mx Na Nf Nm Nr Nw Of Om Or Ow Pb Pd Pe Po Rf Rj St Uc Ue Ug Uk Ul Um Ur Uv Vp Tj) cQ(aE aF Aj aM bQ bX Ch cl Cu cV Cx cZ Dc Fb Fn Fw gL Gp Hv Hw Hx Id Io Ir It Iu Iv Jd Jk Jn Jr Js Kd Ke Kn Kp Lh Md Me Mj Ml Mq Mw Mx Mz Nm Nr Nw Ny Or Ow Pd Pe Pi Pk Po Qa Ql Qv Qz Ra Rb Rf St Ud Ug Up Ut Tj) bV(Ad aM As bE bJ BN Cp Cq cV Cw cZ Dd De Fw Gp Hr Hv Hw Ii Ij Il Iq Ir Js Kg Kz Lh Mb Me Mj Mr Na Nf Nm Of Pb Po Qa Ql Ue Ug Uk Ul Up Ur Uv Vp) gL(Ad AF Aj Ao As Bb BN bQ Ch cl Cw Cx Dd De dH Gl Ha Hw Ib Ii Il Iq Jt Jv Kc Ly Mb Mc Mn Mr Nf Nq Nr Ny Of Pg Po Qw Sr Ub Uc Ue Uu) Kc(Ad Aj Ao As BN Ch Co cP Cq Cw dA Dd De Fp Fw Gp Ii Il Io Iq Iu Jt Kg Kr Lh Mj Mn Mr Nd Nj Nk Of Ow Pb Pe Po Qv Ub Ug Vp Tj) Uc(aJ aX Ba bE cN CP Cu dA Ez Fb Fr Gp Ih Io Ir Jj Jn Jv Kn Ky Lw Mi Mw Nc Nd Ne Nl Nw Nx Ph Qd Qv Rb Sr St Ub Ug Un Ur) Ha(aJ AX Ch cl cP CS cT Cu Ih Io Jn Jy Kf Kj Kp Ky Lx Mi Nc Nl Nw Nx Oa Ph Qd Qv Qw Rb Rf Sr St Ue Ug Un) Qw(aJ As aX bF Bg BN bQ cl cN cZ De dI Hc Hq Hr Hu Ii Il Iu Jd Jn Jv Ki Kr Ky Kz My Nc Ng Of Qt Qv) Ib(aJ aS aX bE Bo cl cN Cp cW Ef Ez Fr Gp Hc Jh Jp Jv Kr Mi My Nk Nl Nx Qv Rb Rf Ub Ue Ug Ur Vv) Io(aE Af aJ Ao As aX bE Bg bN bQ bX Ch cl cN Co Cq cS cT cZ dA De Dk Fb Jd Kj Rf St Ub Ug Ur) Nd(AJ Ar aS aX bE bN cl cS Dd dN Fn Gp Ju Jv Jy Kp Kr Ky Qv Rb Rf Rj St Ub Ur) Kj(bE bl Bn Dg Ef Ez Fb Hc Ic Il Kf Kl Ly Mi Mr Nf Nx Ph Qy Rb Rh Sr Ua) Ue(Ao aX bE Ch Cq cR cT Dd dH eF Fw Il Iq Js Nf Nk Oy Rf Vp Tj) dA(As BN Cq Ct De Gp Il Iq Mr Of Pb Pd Po Uk Ul Um Uv) Ch(As Ba bJ Bo cP Dd Fn Gp Il Iq Kr Ly Nf Qy Rj Ug Ur) Of(aX Ba cN cP cT eF Gp Jv Kp Qv Rb Rf Sr Ub Ur Vv) Af(cP cT Cv eF Gp Kp Lv Nw Qv Rb Rf St Ug Ur) Bn(cN cP cT eF Jy Kp Lv Nw Qv Rb Rf St Ug Ur) Oy(aJ Ar aS bN cl Cu Fb Fn Kr Ou Ph Ub Ug Vv) Cq(cN cP cT Kf Kp Mi Nc Ne Qv Rb Rf Ub) Ub(bE bJ cZ Dd Fw Il Iq Js Nf Ur Vp) Rf(Aj De Ii Il Iq Jt Mn Ny Ug) St(Al Dd Ii Il Iq Mn Ny Vp) cT(bE Ct Cw De Iq Kg Nf Uv) cl(aX bE Gp Iq Ly Nf Tj) Kp(Dd Ii Ij Il Iq Jt) Ur(Ao Co De Jd Jo Sr) cP(As Co cZ De Hr Kg) Qv(aX bE cZ Mr Nf) Ao(Bo Gp Kr Nw) eF(Aj De Kg) Jo(Fb Rh) aX(bN Ly) CoGp IqaJ SrJt NwaF} cT{Us(aE Af aJ aP Ar aW aY bE bP bX Ch cl cP cQ cS Ct Cu dA Dc dM dN eF Fr Id Ih Il Io Iq Is Iv Jj Jl Jn Jp Jq Jy Kc Kd Ke Kf Kp Lv Lw Lx Ly Mr Mz Nf No Nt Nx On Oy Qv Qy Ra Ri Sr Ub Un) Rf(Aj Ao Bb bE BN Ch cl cP Cq De dR Fp GL gW Hw Ib Ih Il Iq Iu Jt Jv Kc Ke Kg Kj Kr Ly Mc Me Mf Nd Nf Nk Nm Of Pf Pg Qv Rb Rj Ub Uh Vo Vp) Jo(Ar aY Bc bE bJ bX cP cQ cS Cu cV dA dN eF gL Hf Ih Io Ip Iq Ir Jn Jy Kc Kd Kn Kp Ld Ly Mc Nd Nk Nt Nw Oh Ph Qd Qv Qy Ra Sr St Un Vv) Qw(aF aJ Ao aW bE Bn Ch cl cL Cq cV gL Hf Ib Il Iq Jy Kc Kg Ki Kj Kr Lh Lw Ly Nd Nf Nw Oy Pg Qd Qv Rb Rj Sr St Tz Uc Uh) Oy(aY bE bJ Bo bX cP cQ cV dA eF Fb gL Hc Hf Iv Jh Jy Kf Kp Kz Ld Mw Nd Nk Nq Nw Nx Ny Pg Qd Qn Qv Ra Sr St Tz Ub) Io(aE Af aJ aW bE Bn bP bV bX Ch cl cP cQ cS Ct dA Fb gL Ib Ih Il Iq Iv Jn Kc Kp Ly Nf Nw Pg Qz Rb St Ue Ug Ur) aY(aF As BN bX cG cP Cq Cx dF Ha Hw Ib Il Iq Kc Kj Kr Ly Mb Mn Nd Nf Nk Nw Of Ow Pg Rb St Uc Ur Uv) St(AF Al Ao bJ Bn cl CQ Dd Ha Ii Il Iq Jq Jv Kj Ly Nd Nf Nj Nk Nr Ny Or Pg Po Tz Ub Uh Vp) Kc(aE Af bN cl Fp Fw Gl Ha Hw Ib Ii Il Iq Iu Jy Kg Kj Kr Lz Mn Nf Nk Nl Ny Ow Qv Rg Ub Uc Uh) Uc(aJ aW bJ Bo cl cP dA Dc dN eF Id Ih Jq Kd Ke Kf Kn Kp Lv Lx Ly Mr Nk On Qv Rb Sr Un) Af(aJ Ar aW bE bJ bX cl cN cP cQ cR dA gL Jy Ly Nw Qd Qv Rb Rj Ub Ug Uk Ur) Jy(aF bQ Ch cl Cq Ct Ha Hq Ib Il Iq Jk Kj Mn Nd Nf Of Pd Pg Po Ue Uv Vp) Nw(aF Ao bF Bn cl cQ Gl Ha Hq Ii Il Iq Ke Mn Nd Ny Pd Pg Po Tz Ub Uh Vp) cQ(aE bE bJ BN bX cl cP cV Cx Hw Ib Il Ly Mb Nf Of Qd Rj Ue Um Ur) cP(Aj Ao As bE Bg Bn Ch cl Co Cq Ct Cw Dc dI Ib Iq Kj Nd Nf Of) Rb(Aj As Bn cl Cq Ct Ha Hr Ib Il Kg Kj Mb Nf Of Sr Ub Ue Uv) Qd(Cq Ib Ii Il Iq Iu Jt Kr Kz Mn Nd Nf Nk Ny Po Rj Sr) Ly(aO bV Ch cl Ha Hq Hr Hw Ib Il Jj Pg Sr Ub Ue Uv) Ub(bE bJ Bn cl gW Ib Il Il Iq Ki Kj Nk Of Rj) Qv(aL bJ Bn cl Cq Ct cZ Ha Ib Iq Nf Of Uv) bE(aD aE Aj aW Ch cl Ib Il) bJ(Aj Ao aW Ch cl Ct Ue) dA(bX Ha Ib Il Nd Um Uv) Qy(Aj Ch Ct Ib Kj Of) Ib(Jh Kp Mw Ny) cV(AJ Ch dN) gL(cl Cx Hw Sr) Bo(Ao Ch Co) Ha(Kf No Un) Mc(Fb Lz Nk) Nf(Rj Uk Un) Bn(bX Jq) Nk(Ue Ug) Sr(Jp Kj) Kp(Cq Rj) CsKr CtTz DcDd Nolq MnKy NdJj RaKj bXcl} Us{Kf(Af AJ Ao aS aY Ba Bb bl bN Ch cl cR dM eF Fb gL Il Io Iq Iv Jj Jn Jv Jy Kg Ki Kj Lv Mi Mr Nj Nk Nw Nx Oy Qd Qv Rb Rf Ri Sr Ub Ue Ug Uh Un Up) Rf(Af aS aY bE bl bN bV bX cN cP cQ dA dM Fb Fr gL Hc Il Im Io Iq Jn Jo Jp Jy Kc Ld Lv Ly Mc Me Mi My Nx Ou Qv Qy Ri Rj Ub Up Wm) Nw(AF aS aW aY Ba bl Bn bV cl cP cQ Cx dA eF Ez Hc Ii Il Io Iq Kc Ke Mi My Nu Nx Qn Qw Qy Rb Ri Sr Ub Uh Up) Nx(Af aJ aY Ba bN cP dA dM eF Fr gL Ih Ii Il Im Io Is Jj Jo Jy Kc Kp Lx Mi Ph Qd Qv Qy Ri Sr St Ub Ue Ug) Up(aJ aS aY bl cN CP cQ dA dM eF Ez Fr gL Hc Ih Im Is Jl Jn Jp Kc Lv Mw My On Ph Qd Qv Qy Rb Sr Un Wm) St(Af Al aS aY Ba bl Bn bV cl cP cQ dA eF Ez Hc Il Io Iq Iv Jy Kc Lz Mi My Nj Nk Nl Nu Or Qy Rb Ri Vp) Lv(aS aY Ba bl bN bV cP cQ dA eF Ez gL Ih Il Im Jn Jp Kc Ly My Nf Ph Qv Qw Qy Ra Ri Sr Ub Vv Wm) bV(Ba Bc bG bJ cM cP cQ De eF gL Hf Ih Ip Is Jn Jp Jy Ld Me Mr Nf Nk Ny Pg Qd Qy Ra Sr Un) Ba(AJ Ar aY bX Ch cP cQ Ct Cu Dc eF Io Iq Iv Jj Jl Jo Jy Kc Ld Lw Lx Ly On Oy Ub Un) dA(aK Ar aU aY cP cQ Cu eF Fb Fr gL Hc Hf Jj Jp Jy Kc Lx On Ou Ph Qd Qv Rb Sr Un) Qd(Af aS aY bl Bn eF Ez gL Il Io Iq Kc Kz Ly Me Mi My Nf Ph Qv Ra Sr Ub Wm) eF(aS aW

Fp{Cs(bV cT dM Kr Mu Oz Ph Ug Ur) Ax(cT Fb Kr Ub Ur) bV(Ly Mb Rb Rj) KfOy} Ao{Nw(Bn Ha Ip Iv Ly Nd Nu Qn) gL(Ly Mr Rb Un)
Mu(Iq Rh) CuNf StQy JycT KfOy} Rb{Mb(bI cN cR cT Jy Ky Ly Ub) Ub(bN cR Gp Jj Nk) bV(bN Gp) LvIl HwcT} Lv{Il(aW cR gW Ky Lj)
aW(bN cR Ip) cI(cR Ip) UcKf bNcS} Bn{Jy(Ar cT Il Ou Ph) Mu(Il Iq Iv) PoLx HaQd NwUh} Oy{Qy(Mb Ou Rh) Iv(Ba gL) Kf(Bb Uh) HwcT
QnNw} Mu{Iq(aF aS cE cT Cx) CsHa DdIl} Nk{Ub(bN cR cU Jn Mb) StNy} Pg{cT(Ly Qd St) bV(Ic Ip) UcKf} Ha{BbKf PoLx QdRi QnNw}
Ly{Mb(cN Jy) HwcT bNbV} Jy{Il(Ld Rh) IqaS} bV{Rj(cD Ri) GpRa} Ba{MrIb aWcD} Nj{StNy KrPh} NIStNy UcHwKf IbQ

Ki Kq Ld Nw St) Qy(Ba Ik Iz Jg Kj Nq Qu) Kr(Ax Ki Kj Ld Me Mv Oh) Mj(Ql Qt Qu Rg Uf Ul) St(aF dF Jk Jq Ke Nq) Lh(Ed Oh Qd Ul Um Ut) aL(cM cP De dH Jk Rh) Af(Hc Ik Ke Ow Qn) Mu(bQ Hq Jg Pd Ut) Kj(dR eF Ip Ne Uk) Nw(aF bF dF Jt Nq) cI(aI cM cY Ip Ow) Ba(bS cM cX cY) Cv(aF bQ dF Qn) Jj(aU cL cP Uf) Co(bS cX dC) Nq(aA eF Ne) Qd(Dk Ij Jt) aH(aI Ip Og) Ap(cM cX) Mr(Po Uv) Ne(Ue Vv) Ic(Ou Ow) Jt(Jn Kq) aE(Ju Ow) aU(Ar cP) bQ(Ms Og) cY(cP dH) dC(De Ip) eF(dG Mv) DgcX NodF IkRh QwgL KeKq KkKo KyUf LddR}
Nb{Dd(aC Ad Aj aN aP aQ AR AS Bb Bc bE bF Bg bJ bM Bn bU bZ cC cF cH cT Cu Db dF dG Dk Dl dN Dp dR Ed Et Fa Fr Fw gP Hc Hf Hr Hv Hw Hx Ih Ij Il Iq Ir Je Jh Ji Jj Jk Jl Jm Jn Jr Js Ju Jv Kf Kl Ko Kp Kq Ks Ky Li Lx Lz Ma Md Me Mf Mh Mj Mk Ml Mm Mq Mw Mz Ng Nl Nm Nt Nv Og Oi Pa Pc Pe Pg Pi Pk Po Pz Ql Qn Rc Rg Ri Ss Tz Ua Ud Ul Um) cR(aA aH Al aM aO Ap aR aS aX bC Bg bI bM bO bZ cE cF cG cM Cp Cu cV dH dI DK Dl dR eF Fa fP Fw Hc Hf Hr Hv Hx Id Ih Ik Ir Iv Je Jg Jh Ji Jm Jn Jr Ju Kc Ke Ki Ko Kp Kz Ld Li Lj Lu Lv Lz Ma Me Mi Ml Mn Mw Mx My Nc Ne Ng Nj Nk Nn Nq Nr Nu Nv Oa Om Or Pb Pc Pd Pe Pf Pi Pk Pz Qa Qe Qh Ql Qn Qu Qx Rf Rm Ss Tz Ud Ug Uh Uk Up Uu Vo Tj) Uc(aG aH Aj aK aL aM An aQ aS aU aV Ax aZ bH bJ Bo bQ cC cE cI Cs cV CW cY DB Dc dD dE dH Di dL Dp Ed Et Fa Fp Fw Hq Hr Hv Hx Ij Ik Im Is Jd Ji Jj Jr Js Jt Jy Kr Ks Li Lj Lw Lx Lz Mf Mh Mj Mm Mn Mq Ms Mv My Mz Nh Nj Nk Nm Nn Nq Nr Nu Or Pa Pc Pd Pe Pf Pg Ph Pi Pz Qb Qc Qe Qg Ql Qn Qz Tz Ua Ud Ue Uf Ug Uh Up Ur Uu Vo Wm) De(Ad Af aJ aO Ar aS aU aW Ba BC Bg bJ bO bV bZ cF Ch cM cS CU cX cZ dG dK Ez Fb Fw gL GP Hw Ij Ik Iu Jj Jm Ju Jy Kf Kg Ki Kk Kq Kz Lx Mc Me Mf Mi Mj Mm Mn Ms Nj Nl Nm Nr Of Og Ou Pb Pg Pz Qa Qb Qh Qx Qy Ra Rh Ri Sr Ug Uh Un Ut Uv Vp Tj) eF(aA aH AN aQ aR aV aX aZ Ba bC bH bL BO bP bR bV bX cC cG cK cV Dc dI dL dM Dp Ef Ez Fa fP Gl GP gW Hx Id Is It Iv Jf Ji Jj Jm Kc Kd Ki Ld Lh Lw Lx Mh Mi Ml Mv Mx Mz Nc Nm Nq Ns Oi On Qb Qd Qe Qh Qn Ra Rb Rh Ri Tz Ua Ud Uf Vo Vt Tj) Kj(aC aG aH aI aK aL aM aN aO aP aS aU aV Ba BB Bc BG bM bO bQ bR bU bV bW bZ cC cD cE cF cG cH cK cL cM cN cO cU cY dB dD dE dF DG dJ dK dM Fb Fp gP Hc Hf Hq Hx Je Jn Kl Kr Lv Md Mj Ml Mn Mp Mt Mx Ne Nq Nx Ny Pz Qh Tz Ub Um) dI(aA Ad Al An aO Ar aS aW Ax Ba Bc bF Bg bI bN bO bP bQ bS cE cM Cs cT cV Cw Cx Dc dH dK dM Fw Hf Hv Ir Jd Jf Jh Jq Jr Js Jt Jv Kc Kk Kj Md Mi Mj Ml Mm Mw My Nc Nh Nj Nl Nv Oa Oh Or Pb Pi Pk Pz Qb Qt Qx Qy Rf Ud Up Ut Uv Vv) Ha(aD aG An aS aU aW aZ bB bP bU cB cl cL Cp Cq Cv cW DC dD dE Di dL Ed Ef Fp Fw Ic Ik Is It Jg Jm Jq Js Ke Li Lj Lw Mf Mg Mh Mq Mr Mv Mz Na No Nq Nt Nu Nv Oi On Oz Pa Pg Pj Qa Qh Qu Qz Rm Tz Ua Ud Uv Vo Vp Vt) Rb(aC aG Al aQ aR As aV Ba bL bQ cD cE cF cH cK cL CO cS cW cY DK Dl dM Et Fa gP Hx Id Jd Jr Ju Jv Kc Ke Kg Kn Lu Lz Mc Mk Ml Mm Mt Mw Mx Mz Nj Nm Nr Nu Nv Ny Pg Pi Pk Po Qa Qh Ql Qn Qv Qy Rf Rm Ud Ur Uv Vt) In(aD aJ aM An AP aQ aR As aU AX bB bH bL bM Bo bV cD cH cJ cO Ct Cu Cv Cw cX cY DB DC Dg Di dJ DL dM Fa fP Gl Gp Id Jf Jv Jy Kd Kg Ki Kl Kn Kq Kr Ow Qm Qt Qx Ra Rc Rg Rh Ri Rm Ua Ud Uf Ur Vt Vv) dA(aD aK aM aN aP aX aZ Ba Bb bJ bQ bW cC cE cG CH cK cL Cp CT Cu Cw dD dL dN dR Et Ez Fa Fr gP Hb Hw Ih Is It Iz Jg Ji Jl Jm Jq Kg Lx Lz Ma Mk Mm Mu Na Nq Nt On Ou Oz Pa Pe Pj Qd Qt Qu Ss St Uf Vo) Ao(Ad Af aJ Al AP As Ba Bc bE bI bR bS bX cA cF cS Ef Et fP Fw gW Hr Hu Hv Hw Ij Iu Jf Jj Jk Jl Jm Jp Js Ju Lz Ma Mj Mr Mw Mx Ng Nh Nj Nm Of Og Oh Or Pb Pg Qa Qc Qd Qx Rm Sr Ss St Tz Uk Ul Um Vp Vv) Cq(aC Ad aJ aO Ar Bb Bc bl bJ bO bR bX bZ cA cN cO cS cU Cx cZ dK dM Dp fP Fr gL Gp Hf lb lc lj lu Jd Jo Jy Ki Kk Kl Kq Lu Lx Mc Me Mm Mn Ms My Ng Nl Oh Om Qd Qg Qn Qx Qy Rg Rh Sr St Uh Ul Ut Uu Vv Tj) cP(Ad aH Aj aK aL aQ aU aV bM bO bS bZ cA cC cI Cp Cu CV cX cY Dg dJ dK dL Fa Fn Fw Hq Ik Ir It Jd Je Jg Jm Jr Ju Ky Lu Lx Me Ml Mq Ms Mw Nk Nr Nx Ny Og Pi Pk Pz Qc Rf Rh Sr Ub Ud Uk Ul Um Up Uu Uv) Ue(aC Af aL aO As aU aX bF bO bQ bU bV cA cC cD cF cG cH cl cJ cK cN cS cT cU CX dB dE dK dL Fw Gp Hf Hu Ih lj lu Jk Js Jt Kc Ky Me Mj Mr Mx Ng Nx Ow Pb Pf Pi Po Qh Qv Rh Rj Tz Ul) Jo(aD aE aK Al An aP aR aU aW Bb bE bF Bg Bo bP bQ bW cC cE cG cl cL Cp Cv Cw cY cZ dB DC dF dN Ed Ef Fa Fn Gl Hb Id Iz Jy Kd Ke Ki Ko Or Pk Qg Qh Qm Rc Rm Ua Ud Uh Uo Uu Vt) Rj(Ad aF Al aO aS aV Ba Bb bF Bg bJ bM bN bO bU bX bZ cA cF Ch cK cM cN cS cZ dB dH Dk dR Hf Hu li Jd Je Js Jt Kc Ky Lu Ly Mc Mj Mm Mr My Nc Nj Nx Oe Pb Pg Po Qn Qy Rf Rm Uk) Bn(Aj aO aP bC Bg bl bN bO bS bU bV bZ cD cF cJ Co cU Cv Cx Dc dK dR fP gW Hr Hw Ij Jd Jj Jq Js Jt Ju Jv Kd Kf Kp Kz Lu Lw Lx Mb Mj Mk My Nc Ne Nx Ny Oe Ph Qx Sr Uk Um Un) Ly(Ad aF aG aH al aJ aK Al aM aP aQ Ar aS aU aW Bb bE bG bH bP bU cC cD cE cG cH cl cK cL cO cW cY DB dE DG dJ Dk DL dM dN Gp Jd Jv Kc Ke Ky Qv Uk) II(aC Af aM aN aO AR Bb bC Bg bN bU bV cJ cM cS cT Cu Cv Cw cZ Db DG dL dM dR Ef Fa gL Hc Hf Jd Ki Kk Kn Ld Oa Ow Qg Qv Ri Ss Tz Uf Uh Ul Ur Uv Vo Vp) Ib(aD aK aL An aQ aU aV aW aZ bG bW cC cl cM Cp Cv CW cX cY dB DC dD Dk dL Et Fb Id Ip Ir Iv Jp Jq Ke Mt Mz No Ns Nv Ny Om Or Oz Ph Pj Pk Qm Qz Un) Nf(aC aO AR aS Bb Bc bE bF Bg bL bM bU bV bW bX bZ cF cK cM Co cS cT Cw CX dG dK Dl dM dN Dp dR Jf Ju Jy Kc Kg Ki Ko Kr Ky Ld Rf Rg Ri Uh Ul Tj) Jt(Af al aO aP aS aX Bb BC bF Bg bI bJ bV bX cA cE CH cJ cK cN Co cS cU cW dH DK dM gL gW Jd Kl Kp Kq Qv Rf Sr St Ul) Af(Aj aM aP aX Bg bJ bN bO bS b

UcIs} Nx{Jj(Hr Li Lj Mj) Us(Kr Ms Nk Rj) Oy(Bo Qd) bNdN} cT{Ly(Jj Mb Oy Pf Us) Pg(Iv No) HaUb IbbX RbKg} Il{Jy(Iv Ph) bE(Mb Mr) GpQd LvaD} HwIs} gL{Iq(cI Rh) AoKy MbRa MrOy RhNy RiUs} bV{Fp(bN Nk) Ly(Ne Pf) bNbX} Lv{CuaW OyaS aEbN cIgW} Rb{Ub(cS Ki) MbaJ KycI} Mu{Ao(cR Ly) IqbN} Kf{CqUh QyOy KrPg} Us{Up(aS Ih) RiUn} Bn{LxKr JyRg} Cu{Uh(aW Uc)} Nk{StgW JjOk} Qd{GpRa HacR} DcUbIq NjOfPh IbQnNw JhOuOy

Unconstrained panels with 2 analytes, where 1.0E-7 >= 'AUC p-value' > 0. Contains 158 panels of 60,152 total panels evaluated. : Ni(aE Af AJ aM aN aO aP Ar AS Ax aY aZ BA Bb bJ BN bO bR bS bV bW bX bZ cA cC cF CH cN cO cP cQ cR CS cT cU cV Cx dA Dc dD dI dK dM dN eF gL Gp Kc Kk Kp Kq Ou Ph Qv Qw Rf Rh Rj St Ub Ue Uk Ur Us Vv) bA(Af Aj Ao aY Ba Bb bJ BN bR bX cD Ch CQ Ct cV Cw dA Dd Fp Gl Hw Ib In Io Iq Jo Ly Mc Mn Nb Nd Ng Nk Nr Ny Oy Pf Pg Qv Qw Rb Rj Sr Uc Us) Nb(aY cP CQ cR dA Dd De dI eF Ha Ib Kj Qw Rb Rj Uc Us) Sr(aA bV Kk Kp) Kc(cQ Nj Qv) Io(cT Kp) Kq(Ao Uc) Nx(Jj Jo) aA(Af Nk) cP(In Lv) dA(aV Qw) FpKk IiSt RfaY Unconstrained panels with 2 analytes, where 1.0E-6 >= 'AUC p-value' > 1.0E-7. Contains 222 panels of 60,152 total panels evaluated. : Ni(aA aC AD aF aG aH aI aK AL An Ao Ap aQ aR aU aV aW bB BC bE bF BG bH bI bL bM bP bQ bU cB cD cE cG cI cJ cK cL cM Co Cp Cq Ct Cu Cv CW cX cY cZ dB dC Dd DE dF DG dH Di dJ DL dR Fn fP gP gW Hf Jv Ki Kj Kr Ky Kz Ld Nx Oa Qt Qy Ra Rb Sr Uc Ug Ul Um Ut) bA(Ad aE aF aG aH AL aM Ap Ar As aU bB bE Bg bQ bS bW cA cE cF cI cL Co cP cR cS CX cY dC De dF DG dH DI dJ DK Dl dN gW Ha Hu Ih Ii Il Iv Jd Jj Jt Jv Kc Kr Lh Mb Ms Ne Nf Nj Nn Nq Of Pb Qu Ra Tz Ub Uh Uu) Nb(Ad Af Al aN Ao bC bI bJ BN bR bS cA Ch cM gW Jv Kc Ke Or Ub Ue Vp) Kp(cQ dA In Mc Oy Qv Qw) Qv(bE cQ dA In Lv) Af(cT gL Kc Kq) aA(cQ Oy Qw) Mc(Bo cT) In(aS cT) Kk(cQ eF) Kq(Il Mn) Rf(gW Qw) Nx(Ii Us) dA(Iv Us) IoKc JoOk KfPg Unconstrained panels with 2 analytes, where 1.0E-5 >= 'AUC p-value' > 1.0E-6. Contains 474 panels of 60,152 total panels evaluated. : bA(aA aD aI aK AN aO aP aQ aR aS aV AW AX aZ BC bF bG bH bI bL bM BO bU bV bZ cB cC cG cH cJ cK cM cN cO Cp Cs cT CU Cv cW cZ Dc dL dM dR EF Et Fr Fw Gp Hf Hq Hr Hv Hx Ic Ij Ik Ip Ir It Iu Je Jg Jh Ji Jk Jl Jm Jn Jp Jq Jr Js Ju Jy Kg Ki Kj Kp Ky Kz Ld Li Lu Lv Lw Lx Lz Ma Md Me Mf Mg Mi Mj Ml Mm Mp Mr Mu Mv Mx Nh Nl Nm No Ns Nt Nu Nv Nx Oe Og Oi Ok Om On Ou Pc Pd Pe Po Pz Qa Qb Qc Qd Qh Ql Qm Qn Qt Qx Qy Rc Rf Rg Rh Ss St Ud Ue Uf Ug Uk Ul Um Vo Vp Vv Tj) Nb(aC aM aO AP AR aS aV aX Ba Bb bF Bg bL bM bO bU bV bW bX bZ cD cF cH cK cN Co cS cT cU Cw cX dD dF DG dH DK DL dN dR Fa Fw Gp Hf Id Jd Je Jf Ju Jy Kf Kn Ko Kp Kr Ky Ou Pi Pk Qh Ql Qn Qv Qx Qy Rf Ri Rm Sr Ss Tz Ud Uf Uh Uk Ul Um Uv Vo Vt Vv Tj) Ni(Aw aX Bo Db Dk Dp Ed Ef Ez Fa Fb Fw Gl Ha Hb Hc Ib Id Is Iv Iz Jd Je Jf Ji Jp Jr Ju Jy Kd Ke Kf Kg Kl Ko Ks Mw Or Ow Pi Pj Pk Qg Qh Ql Qm Qn Qu Qx Qz Rg Ri Rm Ss Tz Ud Uf Uh Un Uo Up Uu Uv Vo Vp Vt Tj) aA(Bn bR cP Cx Hw In Ip Iv Jj Jn Lv Mc Ne Nl Nr Ns Nx Pb Pf Pg Qv) Kc(aY bN cR eF Fp Ha Ii Il In Iq Jo Kr Ky Nk Oy Qw Rb Rj Ub Us) cQ(aJ bX cP cS cT dM In Iv Jy Kq Mu Nw Nx Qw St Ub Un Ur Us) Qw(aY bV cR cT eF Kk Kq Ky Qv Ub) Kp(cR Fp Ib Jo Kj Pf Pg Pz Us) cP(bE cR dA dI Io Jy Mu Nw Rf) In(cS Fa Iv Kf Ky Nx Ou Ph) Qv(aY bV cR cT cZ dI eF Nx) Kq(Gl Ii Io Iq Jq Uh Us) dA(eF Ic Ky Ly Mb Nx Rj) Kk(dI gW Ii Io Jo Oy) Nk(Is Iv Jp Ub) Rf(bI Bn dR Nm) cT(bX Hw Jo Ly) eF(aE cI Ub Us) bV(cD Io Ly) Af(dM Nw) Lv(aW aY) Mc(Kf Ky) Ii(Cu On) Qd(Ha Il) Nx(Nm Oy) AoNw UbcR IqaJ SrJp StaY JjOk KfUh Unconstrained panels with 2 analytes, where 1.0E-4 >= 'AUC p-value' > 1.0E-5. Contains 757 panels of 60,152 total panels evaluated. : aA(Aa aY bN cD cR Et Fr Hq Hr Hu Hv Hx Ih Ii Ij Ik Il Im Io Iq Ir Is It Iu Jd Jh Ji Jk Jl Jm Jo Jp Jq Jr Js Jt Lu Lw Ly Lz Ma Mb Md Me Mf Mg Mh Mi Mj Mk Ml Mm Mn Mp Mq Mr Ms Mt Mu Mv Mw Mx My Mz Na Nb Nc Nf Ng Nh Nj Nm Nn No Nq Nt Nu Nv Nw Ny Oe Of Og Oh Oi Ok Om On Pa Pc Pd Pe Po Pz Qa Qb Qn Rb Rh Ri Us) Nb(aD aF aG aH aI AJ aK aQ As aU AW aZ bB Bc bE bG bH bP bQ cC cE cG cI cJ cL cO Cp Cs Ct Cu CV cW Cx cY cZ DB DC dE Di dJ dM Dp Ed Ef Ez Fn fP GL gP Hb Hc Ic Iz Kd Kg Ki Kl Ks Kz Ld Nf Oa Ow Qg Qm Qt Qu Rc Rg Rh St Ua Ug Un Uo Up Ur Ut Uu) bA(aC aJ bP DB dD dE Dp Ed Ez Fa Fb Fn fP gL gP Hb Hc Id Im Is Iz Jf Kd Ke Kf Kk Kl Kn Ko Kq Ks Lj Mh Mk Mq Mt Mw My Mz Na Nc Nw Oa Oh Or Ow Oz Pa Ph Pi Pj Pk Qe Qg Qz Ri Rm Ua Un Uo Up Ur Ut Vt Wm) Kc(Aj Ao aS bI bJ Bn bO bS bX cA Ch cP cS cT cU Cx dA Dd dI dK dR Fw Gp gW Hf Hr Hw Ib Ic Ip Iu Iv Jn Jv Jy Kg Ki Kj Lv Mc Mf Mr Ne Nf Nl Nm Nx Ny Og Ow Pb Pg Ql Qn Qy Ra Uc Ue Ug Uk Um Tj) Qv(aC Af aJ aX Ba Bc bI bJ Bn cN cP cS dM Ez Fb Fr gL Io Iq Iv Jn Jy Kf Ki Kk Kq Ky Kz Ld Ly Mi Mw Ne Nk Ph Qd Qy Ra Rb Rf Rh Ub Un) cQ(aE An aP aY Bc bN Bo bV cN cR Cu dA Dc dN eF Fb gL Ih Io Ip Ir Jj Jn Kf Ky Ld Lv Ly Mb Mr Nk Nt Oh Ph Qd Qz Rf Rj Sr Ue Ug) Kp(Aj Ao As aY Bb bJ BN Ch cP Cq dI eF gW Ha Ic Il Ip Jj Jv Kr Ky Lu Lv Ly Nf Ng Nk Nn Of Rb Rj Ub Uc Ue Ug Uh Uk Um) cP(Af Aj aM bX bZ Ch cS Cu Cv Dc dN Gp Iv Jj Jo Kk Kq Lw Lx Ly Mb Mr Mt Nk No Nx Oy Qw St Ub Us) dA(bR bU bX cF cR cS cT fP Ha Hf Il Io Ip Iq Jn Kf Kq Nd Nf Nk Oe Og Ou Oy Rb Ub Uk Um Ur) Qw(aJ Ar Bo cN cS dM Fb Fr gL Iv Jh Jj Jn Jp Jy Kf Lv Lx Mt Mw Nx Ph Qd Qt) Ni(Fr Hx Ic Ih Il Ir Jj Jl Jn Kn Lj Lv Lx Mh Nk Nw Oh On Pb Qd Qe Rc Ua) Kq(Ad aY BN Cx Dg gW Iz Jo Jt Ke Kj Nm Ny Oy Pg Qm Qn Tz Ub Uu Vo) cT(Ao aY Bb bJ cD dI dN Fp Ib Iq Iv Jv Nk Oy Pg Ra Rb Rj Sr Ub Us) eF(Aj aS aW bV Ch cW Il Io Jo Kj Mb Qd Rf Uc Ue Ug Ur) In(aY Bc bN bV cR Cs cU cW Fb Is Jp Qx Rh Ub) Kk(aY bI bN cR Cx Dd Gp Hu Il Ip Ko Ky Mn Ub) Nx(Af aY bN Ha Il Iv Kj Ng Nk Pf Qd Ub Ue) Io(aJ Ar aY Ba Cu dM gL Kf Ph Rf Ub Ur) Us(Ar Ba bV dM Fr Jn Kf Ph Qd Rf St) Rf(Af aS fP Ly Nk Ra Rb Rj) bV(Af bN Fp Hw Mc Mr Ra Rb) cR(aY Iv Ld Ly Mb Rb Rj Ue) Is(Hw Ii Il Iu Jj Nr Oy) aY(gL Gp Ly Mb Nw Rb) Af(aJ Jy Mu St Ur) Lv(aE aS bI bN cI) Sr(dM Nj Nw Pg Qd) Ba(cD Ib Mr Of) Mc(dM Fb Jp Ph) Nk(Ir Ji Jj Ue) Il(Cu Fr Iv Jy) Jo(Kf Ou Ph Rh) Rb(Mb Ub Ug) Jj(Ir Iv Jn) Hw(aS Jp) Kf(Bb Oy) AoCu ChKy GpbI MmJi IqgL JpOy JyOu Unconstrained panels with 2 analytes, where 1.0E-3 >= 'AUC p-value' > 1.0E-4. Contains 2,326 panels of 60,152 total panels evaluated. : Kc(aA aC AD aE aF aG aH aI aJ aK AL aM AN aO AP aQ AR As aU aV AW AX aZ Ba BB BC bE bF BG bH bL bM Bo bP bQ bR bU bV bW bZ cB cC cD cE cF cG cH cI cJ cK cL cM cN CO Cp Cq Cs Ct Cu CV CW cX cY cZ DB DC dD DE dF DG dH Di dJ Dk DL dM dN Dp Ed Ef Et Ez Fa Fb Fn fP Fr GL gP Hb Hc Hq Hu Hv Hx Id Ih Ij Ik Im Ir Is It Iz Jd Je Jf Jg Jh Ji Jj Jk Jl Jm Jq Jr Js Jt Ju Kd Ke Kf Kk Kl Kn Ko Kp Kq Ks Kz Ld Lh Li Lj Lu Lw Lx Ly Lz Ma Mb Md Me Mg Mh Mi Mj Mk Ml Mm Mn Mp Mq Ms Mt Mu Mv Mw Mx My Mz Na Nc Nd Ng Nh Nn No Nq Nr Ns Nt Nu Nv Nw Oa Oe Of Oh Oi Ok Om On Or Ou Oz Pa Pc Pd Pe Pf Ph Pi Pj Pk Po Pz Qa Qb Qc Qd Qe Qg Qh Qm Qt Qu Qx Qz Rc Rf Rg Rh Ri Rm Sr Ss St Tz Ua Ud Uf Uh Ul Un Uo Up Ur Ut Uu Uv Vo Vp Vt Vv Wm) Kp(aA Ad aE Af aG aK Al aM aO Ap aQ AR aU aV aW BC bE bF BG bI bL bM BO bR bS bW bX cA cC cD cE cF cH cK cL cM cN CO Cp cS CT CU CV CW CX cY Db dC DD DE Dg dH Di dJ DK Dl dN Dp dR Ef Et Fb Fn fP Fw Gl Gp Hf Hr Hu Hv Hw Hx Id Ii Ij Ik Iq Ir Iu Iv Iz Jd Jg Jl Jm Jn Jr Js Jt Ju Jy Kg Ki Kk Kl Ko Ks Kz Ld Lh Li Lx Lz Ma Mb Me Mf Mi Mj Mk Ml Mm Mn Mp Mr Ms Mu Mv Mw Mx Na Nc Nd Ne Nj Nl Nm Nq Nu Nv Nx Ny Oa Oe Og Oi Oz Pb Pe Pi Pj Pk Qa Qb Qc Qg Qh Ql Qm Qt Qx Qy Ra Rf Rh Ri Rm Ss St Tz Ud Uf Ul Up Uu Uv Vo Vp Vv Tj) Qv(aE Aj aK aL aM An aO AP Ar AS aU Ax aZ bB Bg bH bL bN bX bZ cB Ch cI Cp CU cV Cx Db Dc Dd dE Dg DK dN Dp dR Ef Et Fa Fn Fp Gp gW Ha Hb Hc Hf Hw Ib Ic Id Ih Il Im Ip Ir Is It Je Jf Jg Jh Ji Jj Jk Jl Jm Jo Jp Jq Ju Jv Kj Kl Ko Kr Ks Li Lj Lx Ma Mb Mc Me Mk Mm Mn Mp Mr Mt Mu My Na Nd Nf Ng Nj Nl Ns Nt Nu Nw Oa Oe Oh Ok Om On Ou Oy Oz Pe Pg Pi Pj Po Qa Qe Qg Qt Qz Rc Rg Ri Rj Rm Sr St Ua Ue Uf Ug Uk Ul Um Ur

Figure 19 Continued

Us Ut Vt) dA(aA Af al aK aL aO aQ Ar aU aZ Ba Bc bI bN BO bS bV cA cB cK cM Cu cW cY DD dK dM Dp Et Ez Fa Fb Fn Gp Hq Hr Hu Hx Ib Id Ih Ij Ir It Iu Jd Jf Jo Jq Jr Js Ju Jv Jy Ke Ki Kj Kk Kz Ld Lv Lw Lz Ma Mc Me Mi Mk Mt Mx Mz Nc Ne Nh Nj Nq Nt Nw Of Oi Om Pb Ph Pi Pj Pk Qg Qh Ql Qn Qt Qx Qy Rf Rg Rh Ri Rm Sr St Tz Uc Ud Ue Ul Un Uo Up Ut Uu Uv Vo Vt Vv Tj) cT(aA aD aE aG aH Aj aK AL aM Ap AR As aU aW bB bE Bg BN bO bR bS cA cF Ch cl cM cN Co cP Cq cR cS Ct cU CV Cw CX cY cZ dC Dd Dg dJ dK DL dM dR eF Fb Fr Gl Gp gW Ha Hf fi Ik Il Iu Jj Jn Jy Kg Ki Kj Kr Ky Ld Lu Mb Mf Mm Ms Mu Nd Ne Nf Ng Nj Nn Nr Nt Nx Ny Oe Of Og Oi Pf Qd Ql Qu Qy Rf Rh Tz Ue Ug Uh Uk Ul Um Uu Uv Vv) cP(aE aI aJ aK AL An AO aP Ar As aU AW aY Bc Bg bI bJ bM BN bO bR bS bU bV cA cB cC cD cF cG cI cM cN Co Cp Cq Ct cU cV Cw Cx cZ DD De dF DG dJ DK dM eF Fb fP Fr gL Hr Hw Ib Ih Ik Il Ip Iq Ir Is Ji Jn Jq Jv Kg Ki Kj Kr Ky Ld Lu Ma Mc Ms Nd Ne Nf Ng Nj Nt Ny Oe Of Og Oh Om Pg Qd Rb Rh Rj Ue Ug Uk Um Un Ur) cQ(aD AF Aj aM aO AR aS AW Ax aZ Ba bE bI bJ Bn bP bR bS bZ cA cB cD cF CH cI Cp cU CV Cx dB dC dF dG dI dK dL Fa Fr Gp Hf Ic Id Il Im Iq Is It Ji Jl Jo Jp Jq Kd Ki Kj Kr Lj Lw Lx Mp Mt Mw Mx Nc Nd Ne Nf No Ns Nu Nv Oa Oe Ok Om On Ou Oy Oz Pe Pi Pj Qa Qb Qe Qy Ra Rb Rg Rh Rm Uk Ul Um Ut Vt Wm) aA(aE aF aG Aj Al Ao Ar AS aU Bb bI bJ bO bQ bS bU bW bX cA cB cF cG Ch cI cJ cK cM Cq cS cU cV Cw cX dC Dd De dG dH DI dK dN dR FP Gl Gp gW Ha Hf Ib Ic Iz Jg Jv Ke Ki Kj Kr Ky Ld Lh Li Lj Lx Nd Ow Oz Qc Qd Qe Ql Qm Rj Ss Tz Ub Uc Ue Uh Um Uu) Nx(Aj Ao Ar Bn Ch Cq cR cS Dd dI eF Fr Gp Hq Hu Hw Ib Ij Io Iq Ir Is Iu Jh Jm Jn Jp Jr Js Jt Jy Kg Kr Lu Lv Ly Lz Mb Mc Mf Mg Mm Ms Mw My Nc Ne Nf Nj Nl Nr Ns Ny Oe Of Og Pa Pb Pc Pd Pe Pg Pz Ql Qn Rf Rj Sr Tz Uc Ug Uh Uk Um Uv Wm Tj) Kk(Al As Bb bE bJ Bn bX Ch cM cS cZ De dN Fb Gl Ha Hf Ib Ic Ij In Iu Jj Jt Ju Jv Jy Kg Kj Kr Ks Kz Lh Lu Lv Ly Mb Mc Me Mf Mp Ms Nd Ne Nf Ng Nj Nk Nm Oi Ow Pf Pg Pz Qb Qc Qh Qn Rb Rh Rj Rm Tz Uc Ue Uh Um Us Uu Tj) eF(Af aG Ao Ar Ax aY Ba BC BG bH bI bN Bo bP bS bW cC cL cN Co cR cS Ct cV dC Dg dK dM Fn Ib Ih In Iu Iv Jj Jn Jy Ki Kq Kr Kz Ld Lj Ly Mn Mu Mx Nd Ne Nf Nj Nk Ns Nw Of Ou Oy Ph Ra Rb Rg Rh Rj Ss Uk Um Un) Jp(Et Hq Hu Hv Ii Ij Il Io Ip Iq Ir Is Iu Jh Jj Jk Jm Jn Jo Jr Js Jt Lv Ly Lz Ma Mb Me Mk Mm Mp Mr Mt Mv Mw Mx My Mz Nc Ne Nf Ng Nh Nj Nl Nm Nr Ns Ny Oe Of Og Oi Pa Pb Pf Po Pz Qc Rb Us) Jj(aY bl cR cS Fb Fr Ic Ih Il Im Jg Ji Jk Jl Jm Jr Kq Li Lv Lx Lz Ma Mb Mm Mq Mt Mu Mv Mw Mx My Nf Nh Nt Nu Nv Nw Oh Om On Ph Po Qa Qc Qd Qe Rb Rf Ub Us) Rf(Aj Al Ao bJ bN bX Ch Cq cR dN GP Ha Hf Ib Ic Ii Il In Iq Iu Iv Jo Jt Jv Kj Kr Ld Lu Lv Mn Nd Ne Nf Nj Nr Ny Oy Pb Pd Qy Sr Ss Ub Uc Ue Ug Uk Vp) Kq(aE aF Aj Al Bb bI cG Ch cI cR cS Dd De DK Et Ha Ib Ij In Iu Jg Jk Ki Kr Lh Ly Mb Mc Mm Nd Nf Nj Nk Nq Nv Oi Pd Pz Rh Rj Sr Ss Ue Uv) Qw(Af aO aP aS Ax Ba Bc bE bI bZ Cu dG dI dN Ez Fa Gp Hx Il In Io Ir Is Jo Jr Ki Kj Lu Mb Mp My Nt Nw On Ou Qe Qy Rh Sr Ue Ug Un Ur) aY(aJ aO Ba bN Bo bV bX cH cS Cu Cv dl Fr Hf Ih Il Ip Iq Ir Is Iv Jn Jo Jy Ky Ld Mr Ms Mu Nd Nf Nk No Nv Og Oh Rh Rj Ub Ue Um Ur Us) cR(aJ Ar aW bN bS bV bX cl cN dM dN Fn Hf Hw Il Io Iq Jn Jo Jv Jy Kf Ki Kj Ky Kz Lu Lv Mc Mu Nd Nf Ns Nw Ou Qy Rh Sr St Ug Ur Us) Ni(Hq Im In Jg Jh Jo Jq Li Lz Me Mj Ml Mn Mp Mr Mt Mu Mv Mx My Mz Na Ne Nf Ng Nn No Ns Nt Nu Nv Of Ok Om Oy Pg Pz Qa Qb Wm) In(aE aF Ar Ax aZ bI Bo Cu dK dM gW Ic Id Il Ir Ji Jn Jr Ki Ks Mr Mw Mz Nk Nw Oa Ok On Pi Pj Qd Qg Rg Rm Sr Ue Un Ur Us) Iv(Aa aJ aP Ar aS Ba bV bX cl cN dM gL Gp Io Is Iu Ji Jo Lu Lv Mw Nc Nf Nj Nm Nr Oi Ok Oy Pf Rb St Ub Ue Ug Ur Us) Us(aJ aP aS Bc Bo cS Cu Ez Fa Fb gL Hx Ih Im Ir Is Jg Jl Jy Li Lv Mr Mw Nt Nw Oh Ok On Qe Qy Rb Sr Ua Ub Uf Un) bV(Bb bJ bX dI Gp Ha Hf Ib Ic Ii Il Ip Iq Jd Jo Jy Kr Ld Lv Mb Mn Nd Nk Nr Ny Oy Pf Pg Rj Ub Uc Uh Um) Io(aP aS Ax Bc bX cN CS Dc Dg Ef Ez Fb Fr Gp Hc Is Ji Jy Kl Nw Ou Qy Qz Rb Rh Sr St Uf Ug Un) Ub(Ar Bc bN Bo bX cS Cu dM dN Fb Fr gL Gp Il Iq Jn Jy Ki Ld Lv Ly Mb Mr Ph Rh Un Ur) Is(Ih Ij Iq It Jm Jo Jr Js Jt Lv Lz Mb Mc Mm Nc Ne Nf Ng Nj Nl Nm Ny Of Og Oi Pd Pf) Il(aJ bE Dc dI gL Ir Ji Jr Kf Ld Lh Lv Mu Mw Nw On Qy Ue) Iq(aP Ba Bo Cu Dc Ir Jl Jy On St Ug) Rb(aJ Bo cN cS Gp Ir Kj Ly Ph Qd Ue) Kf(Bn Dd dI Ha Ib Nj Nn Pf Rj Uc Ue) Fr(Ao Ii Ij Iu Ly Nr Oy Pf Ra Uc) Mb(aJ bI bX cN cS dI Fb Jy Ok Qy) Qd(dR Fp Gp gW Nm Nr Oy Pf Uc) On(Ao Hw Jt Mm Nm Nr Ny Oy Pf) aJ(BN bR Ly Mc Mr Nd Oy Pg) Ir(Hw Ii Iu Ly Nr Ny Oy Pf) cS(Ba bN Ld Ly Mc Mu Nd) dI(aS Jn Ld Nu Ou St Ur) Cu(cI Gl Mc Pg Uc Uh) Lx(aF Bn Ha Hq Pa Ri) Hw(Bc Hx Jr Mw Ok Ph) Ba(cM dN Iz Kj Nr) Bo(bX Ch Oy Pg Ri) Ue(Fb Jn Jy Rh Un) St(Ao gW Nj Pg Qn) Ph(Fb Fp Ly Oy Pg) Mc(Jr Ou Un Ur) Jy(Bn Cx Ld Rh) Ug(Ip Jn Ly Rh) Mu(aF Ao bN) Kj(bI Im Qy) Kr(Cs Oh Ou) Ok(Ng Nm Pf) Oy(Jg Jl Qy) cN(bN Ly Rh) Fp(Cs Ur) Un(Pg Uh) bI(cV Rh) dN(aS bN) AoOm FbJn GpLy MwIb NfJr OwOu UrgW UvbA

Unconstrained panels with 2 analytes, where 1.0E-2 >= 'AUC p-value' > 1.0E-3. Contains 6,879 panels of 60,152 total panels evaluated. : Rf(aA aC AD aE aF aG aH aI aJ aK aL aM aN aO AP aQ AR As aU aV AW AX Ba BB BC bE bF BG bH bL bM BO bP bQ bR bS bU bV bW bZ cA cB cC cD cE cF cG cH cI cJ cK cL cM cN CO Cp Cq CS Ct CU CV CW CX cY cZ DB DC Dd DE dF DG dH DI dJ DK DL dM Dp Ed Ef Et Ez Fa Fb Fn Fp Fr Fw GL Hb Hc Hq Hr Hu Hv Hw Hx Id Ih Ij Ik Im Ip Ir Is It Iz Jd Je Jf Jg Jh Ji Jk Jl Jm Jn Jq Jr Js Ju Jy Kd Ke Kf Kg Ki Kk Kl Kn Ko Kq Ks Ky Kz Lh Li Lj Lw Lx Lz Ma Mb Mc Md Me Mf Mg Mh Mi Mj Mk Ml Mm Mp Mq Mr Ms Mt Mu Mv Mw Mx My Mz Na Nc Ng Nh Nl Nn No Nq Ns Nt Nu Nv Nw Oa Oe Of Og Oh Oi Ok Om On Or Ou Ow Oz Pa Pc Pe Pf Pg Ph Pi Pj Pk Po Pz Qa Qb Qc Qd Qe Qg Qh Ql Qm Qn Qt Qu Qx Qz Rc Rg Rh Ri Rm St Tz Ua Ud Uf Uh Ul Um Un Uo Up Ur Ut Uu Uv Vo Vt Vv Wm Tj) cR(aD aE AF aG aH Aj aK Al aM AN AO aP aR AS aU aV Aw Ax aZ Ba bB Bc bE Bg bH bI bJ bL Bo bP bR bU bW bZ cA cB cC cF Ch cJ cK cL cM CO Cp Cq CS CU cV CW CX dC DD dG dH DI dK dL Dp dR Ed Et Ez Fa Fb FP Fr Fw gL Gp Ha Hb Hc Hq Hr Hu Hv Hx Ib Ic Id Ih Ii Ij Ik Im Ip Ir Is It Iu Iz Jd Je Jf Jg Jh Ji Jk Jl Jm Jp Jq Jr Js Jt Ju Kd Ke Kg Kl Kn Ko Kr Ks Lh Li Lj Lw Lx Lz Ma Md Me Mf Mg Mh Mi Mj Mk Ml Mm Mn Mp Mq Mr Ms Mt Mv Mw Mx My Mz Na Nc Ne Ng Nh Nj Nk Nl Nm Nn No Nq Nr Nt Nu Nv Ny Oa Oe Of Og Oh Oi Ok Om On Or Ow Oy Oz Pa Pb Pc Pd Pe Pf Pg Ph Pi Pj Pk Po Pz Qa Qb Qc Qd Qe Qg Qh Ql Qm Qn Qt Qu Qv Vo Vp Vt Vv Wm Tj) eF(aC AD aF aH aI aJ aK AL aM AN aO AP aQ aR As aU aV Aw aX aZ BB BE bF bJ bL bM Bn bO bQ bR bU bX bZ cA cB cD cE cF cG cH cJ cK cM cO Cp Cq Cs CU Cv Cw CX cY cZ DB Dc DD DE dF dH DI dJ Dk DL dN Dp dR Ed Ef Et Ez Fb FP Fr Fw GL GP gW Ha Hb Hc Hf Hq Hr Hu Hv Hw Hx Ic Id Ii Ij Ik Im Ip Iq Ir Is It Iz Jd Je Jf Jg Jh Ji Jk Jl Jm Jp Jq Jr Js Jt Ju Jv Kd Ke Kf Kg Kl Kn Ko Ks Ky Lh Li Lu Lv Lw Lx Lz Ma Mc Md Me Mf Mg Mh Mi Mj Mk Ml Mm Mp Mq Mr Ms Mt Mv Mw My Mz Na Nc Ng Nh Nl Nm Nn No Nq Nr Nt Nu Nv Ny Oa Oe Og Oh Oi Ok Om On Or Ow Oz Pa Pb Pc Pd Pe Pf Pg Ph Pi Pj Pk Po Pz Qa Qb Qc Qe Qg Qh Ql Qm Qn Qt Qu Qx Qy Qz Rc Ri Rm St Tz Ua Ud Uf Uh Ul Uo Up Ut Uu Uv Vo Vp Vt Vv Wm Tj) Nx(Aa AD aE aF aG aH aJ aK AL aM AN aO AP aR AS aU aV AW Ax aZ Ba BB BC bE bF bJ bL bM Bn bO bQ bR bU bX bZ cA cC cD cE cF cG cH cI cJ cK cL cM cN Co Cp Cs Ct CU CV CW CX cY cZ DB dC dD DE dF DG dH dJ DK DL dM dN dR Ed Et Fb Fn FP Fw GL gW Hb Hr Hv Hx Ic Id Ih Ik Im Ip It Iz Jd Jf Jg Ji Jk Jl Jq Ju Jv Kd Ke Kf Ki Kk Kn Ko Kq Ks Ky Kz Ld Lh Li Lj Lw Lx Ma Md Me Mh Mi Mj Mk Ml Mn Mp Mq Mr Mt Mu Mv Mx Mz Na Nb Nd Nh Nn No Nq Nt Nu Nv Nw Oa Oh Oi Ok Om On Or Ou Ow Oz Ph Pj Pk Po Qa Qb Qc Qe Qg Qh Qm Qt Qx Qy Qz Ra Rb

Iu Ly Lz Mc Mm Nc Ne Nf Nj Nl Nm Nr Of Pd Pf) Oy(Bc Bg Cp dG Ef Ez Hc Jh Jk Li Mv Mw My Nv Om Qa Qe Rg Ua) Gp(aE Aj bP cl Jv Ki Kz Me Mw My Ns Nu Ou Qy Qz Ra Rg Rj) Bc(Aj An dN fP lb li Kg Kr Lu Ly Mc Nd Ng Og Rj Uc Uk) Ou(Aj aU bE dN Fp Hw Kg Lu Mf Mk Ng Nj Of Qy Ra Ri Rj) Ly(aE An aO Ax aZ bE bN bZ Cx Db dN Jg Jh Mw Qe Rh) Mw(Ch Ii Ki Kr Kz Mg Mr Nf Ng Nm Nr Nu Ny Oz Rj) dN(Ax Bn cH Cs Cx Hc Ic Ip Nd Nf Oh Rg Rj Vv) Hw(Ax Cs Fa Ih Jg Jh Mz Nu Nv Qa Qe Rg) Qy(aE Aj Ch cW Ib Ki Kr Ms Og Rg Rh Rj) Mc(An Ax Cp Cs dG Fa Hx Jh Mz Nb Qe) bE(bN dD Mr Nd Qx Ra Rg Rh Rj Uk Um) Lu(aE aW Ax bN cI Ic Rh Rj) bZ(aF Ao bN cI Ii Iu Mn Uc) Aj(Ez Hc Jg Kl Oh Rh Vv) dG(bN bW dK Nd Rh Uc) Mt(Ch Ib Kz Rj Uk) Nf(Fa Hx Jh My Mz) Ih(Dd Ha Ib Iu Ra) Ii(Dc Kd Nv Om Ut) Nb(Hu Lz Md Mi) Rj(Hx Jh Ki My) bN(An aO Cp fP) cl(al aO dF fP) Bn(Fa Mr Ut) Ch(Ez Jh Qt) Qe(Iu Kr Pf) Rh(Kg Kr Mp) Ao(Cp Hc) Ax(Fp Kr) Mm(Et Nv) Uc(Ef Om) Ib(Jh My) Qa(Ij Js) Ra(Og Oh) CpDd FaPg NmJg MiaR MpKi NgRg HrHx HcaE QtgW KgOh NvNy

Constrained panels with 3 analytes, where 1.0E-9 >= 'AUC p-value' > 0. Contains 7,159 panels of 6,910,825 total panels evaluated. : Ni{bV(Ad Af Aj aM An As bE bJ BN bW cC Cp CQ Ct Cu cV Cw Dc Dd De dG DL Fn Fw Gp Ha Hr Hv Hw Hx Ib Id Ii Ij Il In Io Iq Ir Iv Ji Jn Jo Jr Js Jt Kc Kd Ke Kg Kj Kn Ko Kp Kq Kr Kz Lh Ly Mb Mc Md Me Mj Ml Mq Mr Mx Mz Na Nb Nd Nf Nm Nr Ny Of Om Or Ow Oy Pb Pd Pe Pi Pk Po Qa Ql Qv Qw Qx Ra Rb Rf Rj Sr St Ub Uc Ud Ue Ug Uk Ul Um Up Us Uv Vp Vt Tj) bA(Ad Af aL aM As aY Bb bE bJ BN bQ cE cl Cp CQ Ct cV Cw Cx Dd De dF dG Fp Fw Gl gW Ha Hr Hv Hw Hx Ib Id Ii Ij Il In Io Iq Iv Jd Jn Jo Jr Js Jt Kc Ke Kg Kj Kk Kq Kr Ky Kz Lh Ly Mb Mc Me Mj Mn Mq Mr Ms Mx Na Nb Nc Nd Nf Nk Nm Ny Of Om Oy Pb Pd Pe Pg Pi Po Qa Qw Qx Ra Rb Rf Rj Sr St Ub Uc Ud Ue Ug Uk Ul Um Up Us Uv Vp Tj) Cs(Ad Af Aj aM An As bE bJ BN cC Cp Cq Ct Cu cV Cw cZ Dd dL Fn Fp Gp Ha Hr Hv Hw Hx Ib Id Ii Ij Il In Io Iq Ir It Iv Jn Jo Jr Js Jt Kg Kj Kr Lh Li Ly Mb Mc Me Mj Ml Mq Mr Mx Na Nb Nd Nf Nm Nr Of Ok Om Oy Pb Pd Pe Pi Pk Qa Qw Qx Ra Rb Rj Sr Uc Ud Ue Ug Uk Ul Um Up Us Uv Vp Tj) Ax(Ad Af aM An As bE bJ BN Cp Cq Ct Cu cV Cw Cx Dd Fp Ha Hr Hv Hw Hx Ib Id Ii Ij Il In Io Iq Ir It Iv Jn Jo Jr Js Jt Kg Kj Kr Kz Lh Mb Mc Me Mj Ml Mr Mz Na Nd Nf Nm Nr Of Om Oy Pb Pe Pi Pk Qa Qw Qx Ra Rb Rj Sr Uc Ud Ul Um Up Us Uv Vp) Kk(Af Ao As aY Bb bE Bg bJ BN Co CQ cR Ct Cu Dd De Dk Fw Gp gW Ha Hv Hw Hx Ib Ic Ij Il In Io Iq Ir Iv Jd Je Jn Jo Js Kj Ks Ky Ld Mc Md Mj Ml Mn Mr Ms Mw Mx My Mz Nb Nd Nf Nv Ny Of Oy Pb Pi Po Pz Qh Qw Qx Rh Tz Uc Ul Um Us Vp Tj) cT(Af Aj As aY bE bJ BN bQ cI CQ Ct cV Cw Dd gW Ha Hr Hw Ib Ih Ii Ij Il In Io Iq Jo Js Jt Kc Kg Kj Kr Ky Kz Lh Ly Mb Mc Me Mr Ms Na Nc Nd Nf Nk Nm Of Om Oy Pb Pg Qw Qx Rb Rf Rj Sr Ub Uc Ue Ug Uk Ul Um Us Uv Vp) Sr(Ad aJ aM An Ar As Ba Bn Cp Cq Cw Dd Fr gL Ha Hr Hv Hw Ib Id Ii Ij Il Iq Ir Jn Jo Jp Jr Js Jt Kj Lx Mb Me Mj Ml Mr Nf Nm Nw Oa Of Om Or Oy Pb Pd Pi Pk Qd Qe Qw Qx Rf Rj St Uc Ud Ul Um Up Us Uv Vp) Af(aA aJ aP Ar Ba bE bN bX cN cP cQ Cu Cv Cx dA Dc dM eF Fa Fr gL Gp Ih Il Ir Is Ji Jj Jn Jp Jy Kc Kp Kq Ky Lv Lw Lx Mu Mw Nb Nc Nj Nk Nl No Nv Nw Nx Oh Om On Ou Ph Qa Qd Qv Qw Rf St Ub Ur Ut Vv) Bn(aA aJ aP Ar aY Ba bX cN cP cQ Cu Cv dA Dc dM eF Fa Fr Ih Il Is Ji Jj Jn Jp Jq Jy Kd Ke Kf Kn Kp Kq Ky Lv Lw Lx Mu Mw Nb Nc Ne Nj Nk Nl No Nw Nx Oh On Ou Ph Qa Qd Qv Rf St Ub Un Ur Ut Vv) bN(aA aJ aP Ar aX aY bE bX cI cN cP cQ cR cS dA Dc dM eF gL gW Ih Il In Io Is Jn Jo Jp Jy Kc Kp Kq Ky Lv Lx Ly Mb Mc Mi Mu Nb Nc Ne Nj Nk Nl No Nw Nx Oh Ou Ph Qd Qe Qv Qw Rf Rj St Ub Ue Ur) Us(aA aJ aP Ar aS aY Ba Bo bX cN cP cQ cR Cu dA Dc dM eF Ez Fr Hx Ih Il Im Ir Is Jn Jp Jr Kf Kn Kp Kq Lv Lx Mc Mw My Nc Nk Nw Nx Oh On Ou Ph Qa Qd Qe Qh Qv Qy Rf Ri St Ua Ub Up Ut Vv Wm) Ih(Ad Aj aM An As aX aY bE bJ cC cI CP CQ cR Cu Cw Cx Dc Dd De DL Fw Gp gW Ha Ib Id Kc Kg Kj Kn Kq Kr Kz Or Pi Pk Ql Qn Qv Qw Qx Ra Rb Rj Rm Uc Ud Ue Ug Uk Ul Um Up Uv Vp) Qw(aA aJ aP aY Ba cI cN cP cQ cR Cu Cx dA Dc dM eF Hw Il Im In Is Ji Jj Jn Jp Jr Jy Kf Kp Kq Ky Lv Lw Lx Mb Mc Mt Mu Mw Mz Nb Nc Nj Nk No Nw Nx Ou Ph Qa Qd Qh Qt Qv Rf Rh St Ub) St(Ad aF Aj aK Al Ao aU aW aY cC cl cP cQ cR Cx dA dR gW Hw Ii Ij Il In Io Iu Jl Jo Jt Kc Ke Kj Kr Mb Mc Mm Mn Mr Nd Nm Nr Ny Pg Qn Qv Ub Uc Ue Ug Uh Uk) Kp(Ad Aj As bJ cC Cq cV Cw Dd De Fw Gp Ha Hr Hv Hw Ib Ij Il In Io Iq Jo Js Jt Kg Kj Kr Ly Mb Me Mj Mr Nd Nf Of Oy Pb Pi Qx Rj Uc Ud Ue Uk Ul Um Uv Vp Tj) cQ(aE aJ As aY Ba bE bJ bX cl cN cS cV Cx dA dM Fn gL Gp gW Il Jo Jy Kc Kj Kr Ky Kz Ly Mb Mc Mr Mu Na Nc Nf Nk Nw Oh Qd Rf Rj Ub Ue Ug Uk Ul Um Ur Vv) aA(Ad aM An As bJ cC cI Cp Cq Cu cV Cw Cx Dd De dG dL Fw Gp gW Ha Ib Ic Id Iv Kc Kj Kz Lv Nx Or Pi Pk Qn Ra Rf Rj Ub Uc Ud Ue Ug Uk Ul Um Up Uv Vp) Rf(Aj Ao aY Ba cC Ch cI cP Cx dA dR gW Hw Ii Ij Il In Io Iu Jo Kc Kj Kr Ly Mb Mc Me Mn Mr Na Nc Nd Nf Nk Nm Of Oy Pb Qv Rj Ub Uc Ue Ug Vp) Ou(aM As bE bJ cC Cq cR Cx Fn Gp Hr Hw Ib Il In Io Jo Kg Kj Kr Ly Mb Mc Me Mq Mr Na Nd Nf Nm Of Ow Oy Pb Qx Rj Uc Ue Ug Uk Ul Um Tj) dA(aM aV aW bX cl cP cS Dd Gp Hr Ib Il In Iq Jo Kc Kj Kr Ky Kz Ly Mb Mc Me Mr Nc Nd Nf Nw Nx Oy Qv Rh Rj Ub Ue Ug Uk Ul Um Ur Uv Vv) Kf(Ad aM As bJ Cp Cq Cw Dd Ha Hr Ib Id Ii Ij Il In Iq Jo Js Jt Kj Kr Mb Mc Me Mr Nf Nm Of Om Oy Pb Pd Qx Rj Uc Ud Ue Ul Um Uv Vp) aY(aM Ba bE bJ Bo cR gL Gp Il In Io Jo Jy Kc Kr Kz Ld Ly Mb Mc Me Mr Ms Mu Nc Nd Nf Nk Nw Nx Ow Oy Rj Ub Uc Uk Ul Um Ur Vv) cP(As bE cI cV dI Fn gL gW Hr Ib Il In Io Jo Kc Kg Kj Kr Ky Kz Mb Mc Mr Na Nd Nf Nk Nw Of Oy Rj Ub Uc Ue Uk) Ub(Ba bE bJ Bo cI cN cR cV eF gL Gp Ib Il In Io Jo Kc Kj Kz Ly Mb Mc Me Mr Nf Oh Oy Pb Qv Rh Rj Ue Ug Uk Ul Um Ur) Nx(aE Aj As bE cC Cq cV Cx Gp gW Ha Ib Ic Ii In Jj Jo Kj Kr Ky Kz Nm Oy Qx Rb Rj Uc Ue Ug Uk Ul Um Ur Vp Tj) Ph(An As bJ cV Cx Gp Hv Hw Ib Ii Il In Io Iv Jo Kj Kr Ly Mb Mc Me Mr Na Nd Nf Ng Oy Pg Pi Pk Rj Ud Uk Ul Um) Kq(Ad As bJ Cp cV Dd De Ha Ib Ii Ij Il Io Iq Jo Jt Kj Lh Ly Mb Me Mn Nd Nf Om Oy Pd Rj Uc Ue Um) Ba(Aj Ao aW Bb Ch cl cV Hr Hw Ib Il Io Jo Kj Ky Mb Mc Ms Nd Nf Ng Of Oy Qd Rg Uc Ue Uk Uu Uv) Jn(Aj aM As bE bJ cC Cq cV Cx Dd dM gW Ha Ib Kc Kg Kj Kr Kz Qx Rh Rj Uc Ue Uk Ul Um Vp) Jo(Ad aJ aP Ar aS bX cI cN cR cS Ct Cu Dc dM dN eF gL Gp Hc Kn Oa Ok Qt Qv Rh Ut Vv) Io(aJ aP Ar aS bX cN cR cS Dc dM eF Ez gL Gp Kc Kl Oa Qv Qy Rb Rh Rj Ua Ue Ur Vv) eF(aE Aj As aW cC cI cV gW Ib Ii Il Kg Kj Ly Mb Mr Nd Nf Nm Of Oy Rj Uc Ue Ul) Nc(Aj aM As bE bJ cI Cx Dd gL Gp Ib Kj Kr Ky Qv Rb Rj Uc Ue Ug Uk Ul Um Ur) Qv(aC As aX bE bJ cI cN cR cV cZ gL gW Il In Kc Ky Kz Mb Mc Mr Nd Nf Oy) cR(aW bX cI cN cV dM Hw Il Kc Ky Kz Ld Mb Mc Nd Nf Nj Qd Rj Ue Ug) aJ(aM cI cV Cx dG Hw Il In Ly Mb Mc Mr Nd Nf Oy Qn Rh Rj Uc Vv) Ar(Aj As Ch cV Cx gW Ha Hw Ib Ii In Kj Kr Mb Mr Nd Nf Oy) Mc(aS aW aZ Bo cN cS dE dM Fb gL Kc Ky Qt Ue Ug Uk Uo Ur) Nk(aM aW bE bJ cI cN gL Gp Ib Kc Kj Kz Rj Uk Ul Um Ur) Vv(Aj aW bE Ch cI Co gW Ib Il In Ms Nd Nf Nj Of Oy Ug) Lv(Ad aE aM As aW bJ cC cI cV Cx Dd gW Rj Uc Ue Um) Nb(As bE Ch Cq Ct cV cZ Dc gW Ha Ib Kj Qx Uc Vp Tj) Mb(aS bl bX cI cN cS Cu dM Fb gL Ky Ra Rb Un Ur) Il(bE bX cN cS Cu Cx Dc gL Is Jy Ky Qh Rh Un Ur) In(aE aW bX cl cN cS cU dM Ic Iv Kc Ky Rh Ue) Nw(aF Ao Bb cI Cx Dd Dk gW Ha Ib Ke Uc Uh Ut) Lx(aF As Cq Cx De Ha Ib Kj Qx Uc Ul Vp Tj) Oy(aP aS Bo cH Cu Dc Dk Ef Hc On Qh Qy Rh) Oh(Aj aW cV Gp Ha Kc Kj Kr Ug Uk Um Tj) gL(aF Ao aW Bb cl Cx Hw Kc Ms Nd Pg Ue) Kn(Cq Hw Ib Ij Js Mr Nf Pb Uc Ul Vp) Gp(aS aW cI Cx dM gW Kr Ky Nj Qd) Kj(aS bX cS Hc Mw Nj Nn On Qe Qy) Nd(aP Bo cN cS Dc dM dN Qh Ut) Nf(aP bX cN Cu Dc dM Kd Qh Qt) Ue(bE bl bX Ch cN Ky Qd Rh Un) Cx(bE cN Fr Is Jj Jp Qd Ur) Ly(bE cI cN dM Kr Ky Qt Rh) Uc(Fr Ir Is Ok On Qd Qh) Rh(Aj aX bE bX cN gW Im) cH(aM bE bJ cI Iq Nm Pb) cV(aP aS cS Fr Is Jp Mw) Nj(bJ cI Kz Rj Ug Um) Qd(Bb gW Ha Qn Rj Um) Aj(aP cS Fr Jg Nl) Ao(Jg Jp Mu On Pg) Ch(Bo Fr Jp Mw My) Hw(aP aS cS dM Kc) aF(aO bZ Jy Mu No) Ib(aP Hc Qa Qh) Is(As Dd Rj Um) cC(bX cN Kz Rb) gW(Jp Mu Ug Ur) Mr(aP cS dN) Ii(Cu Dc Ut) Ky(Kc Rb Ur) Rj(aS cl dM) dI(aS bX cA) As(Jp On) Dd(Dc Ir) Mu(cE Dk) Qh(Iq Um) bE(cW dD) bJ(aS Ne) BbJp CqQa FnLd FpOa HaLj MeQt NlcI QeKr JgUu Kcbl KgOk KzcS UrPg aEbS bXdE} Nb{cQ(Ad aE AF Aj aM As aY bE bJ BN bQ bX Ch cI Cp Cq Ct Cu cV Cw Cx cZ Dc Dd De Fb Fn Fw gL Gp gW Ha Hr Hv Hw Hx Ib Id Ii Ij Il In Io Iq Ir It Iu Iv Jd Jk Jn Jo Jr Js Jt Kc Kd Ke Kg Kj Kn Kp Kq Kr Kz Lh Ly Mb Md Me Mj Ml Mq Mr Mw

Figure 19 Continued

Mx Mz Na Nd Nf Nm Nr Nw Ny Of Om Or Ow Oy Pb Pd Pe Pi Pk Po Qa Ql Qv Qw Qx Qz Ra Rb Rf Rj St Uc Ud Ue Ug Uk Ul Um Up Ur Us Ut Uv Vp Tj) aY(Ad Af aM As Ba bJ BN CP Cq cR Ct Cu cV Cw Dd De dG dL Fn Fw gL Gp Ha Hr Hv Hw Hx Ib Id Ii Ij Il In Io Iq Ir Iv Jn Jo Jr Js Jt Kc Kg Kj Kr Kz Ly Mb Me Mj Ml Mn Mq Mr Mx Na Nd Nf Nm Nr Nw Ny Of Om Or Ow Oy Pb Pd Pe Pi Pk Po Qa Qv Qw Qx Ra Rb Rf Rj St Uc Ud Ue Uk Ul Um Up Us Uv Vp Tj) bA(Ad AF aH Aj aL Ao As Bb BN bQ cE cG Ch Co Cp Cq Ct cV Cw cZ Dd De dF Fa Fp Ha Hq Hr Ib Ii Ij Il In Iq Iu Jd Jk Jo Jt Kg Kj Lh Mb Me Mj Mn Mq Mr Mw Nd Nf Ng Nm Nq Nr Ny Of Om Oy Pb Pd Pe Po Qb Uc Ue Us Uv Vp) Ha(aA aJ Ar AX bE bN bV Ch cN cP cR CS cT Cu dA dI eF gL Ih Il Im In Io Ir Jn Jv Jy Kc Kf Kj Kk Kp Kq Ky Lv Lx Mc Mi Nc Ne Nk Nl Nw Nx Ny Oa Oh Pe Ph Qd Qv Qw Rb Rf Rj Sr St Ub Ue Ug Un Ur) Qw(aA Af aJ Ao As aX bF Bg BN bQ bV Ch cI cN Co cZ dA De dI gL Hc Hq Hr Hu Ib Ii Il In Io Iu Jd Jn Jo Jv Kc Kg Ki Kj Kk Kp Kr Ky Kz Mi My Nc Nd Ng Of Oy Qd Qt Qv Rf Rg Sr Ub Uc Ue Us) Io(aE Af aJ Ao As aX bE Bg BN bQ bV bX Ch cI cN Co Cq cS cT cZ dA De Dk Ez gL Gp Hf Ib Ic Jd Je Kc Kg Kj Kp Oa Ph Qt Qv Qx Qz Rb Rj St Ub Uc Ue Ur Us Ut Vp Tj) dA(As aV Bg BN bR bS bU cA Co cP Cq cR Dd De dG dH Hq Hr Ib Ii Il Iq Jk Jo Jt Kj Ly Mb Mn Mr Nd Nf Nk Ny Of Om Or Oy Pb Pd Po Rg Rj Uc Uk Ul Us Uv Vp Tj) eF(Ad aE Af Aj Ao As Bg Bn bQ Ch cI Co Cp Cq Ct Cw Dc Hq Hr Ib Ij Il Iu Jd Jh Jk Jo Jt Kg Kj Mb Mn Mr Mw Nd Nf Of Om Oy Pb Pd Po Qt Uc Ue Us Ut Uv Vp) Ib(aA aJ aS aX Ba bE bV cN cP cT Ef Ez Fr gL Gp Hc In Jh Jv Kc Kk Kp Kq Kr Mi Mu Mv Mw My Nc Ne Nk Nl Nx Qv Qy Rb Rf Ub Ue Ug Ur Vv) Uc(aA aJ aX Ba bE bV cN CP cT Cu Ez Fb Fr gL Gp In Jn Jv Kc Kf Kk Kp Kq Ky Lv Mi Mw Nc Nd Ne Nl Nw Nx Qd Qv Rb Rf Sr St Ub Un) Oy(aJ Ar aS Aw aX Ba bJ bN Bo bV cI cN cP cT Cu cW Ef Fb Fn gL Gp Hc Jv Kc Kf Kk Kp Kq Kr Ou Ph Qv Qy Rb Rf Sr Ub Ue Ug Ur Us Vv) Nd(AJ Ar AS aX Ba bE bN bV cI cN cP cS cT Dd dN Fn gL Gp Ju Jv Jy Kc Kj Kp Kq Kr Ky Qv Rb Rf Rj St Ub Ue Ug Ur Us) Rb(Af Ao aX Bg BN bV Ch Cq cR Dd De Gp Ij Il Iq Je Jo Jt Kj Kr Ky Mb Mr My Nf Of Pb Qx Ue Uk Ul Um Us Vp Tj) Us(aA aX Ba bC bE bI bV bX Ch cN cP cT dM Ez In Jn Jo Jv Kc Kf Kk Kp Kq Lv Mc Mi Nc Ne Nx Rf Ri Ub Up) Bn(aA aJ aX Ch cN cT dI gL Il In Iq Jo Jy Kc Kj Kq Kr Ky Lv Ly Mu Ng Nw Qv Rf Rj St Ub Ue Ug Ur) cP(Ao As bE Bg Ch Co Cq Ct Cw cZ De dI Hc Hr Hu In Iq Jo Jt Kg Kj Mr My Nf Ng Of Qt Rg Rj Vp Tj) Dd(aA Af Ao bV Ch Co cR De gL Hq Hu Iu Jd Kc Kg Kk Lv Ly My Nc Nx Oa Qt Qv Qy Rf Rj St Ub Ue) Jo(Ap Ar aX Ba BC bN bV bX cN cR cS cT Cu Dg Ez Fb gL Gp Kc Kf Kp Kq Ph Rf Rh Sr Ur Vv) Af(aA aJ bE Ch cN cR Cv CX gL In Jj Kc Kq Ky Lv Ly Mu Nk Nw Qv Rf Rj St Ug Ur) Ao(cR cT Fb Fr gL Gp Ii Il Iq Jt Kc Kr Ky Ly Mb Me Nf Nw Nx Rf Rj Ue Ur Uv Tj) Cq(aA aX Ba bN Ch cT dI Il Jn Jv Kc Kp Ky Lv Ly Mi Nc Ne Nx Ou Ph Qv Rf Ub Ue) Ub(As bJ bN cR Fw Ij Il In Iq Js Ly Mb Mc Mj Nf Nk Of Pb Rj Tz Ul Um Vp Tj) cR(Ad bN bQ Ch Co Cw De Hw Ii Iq Iu Jd Jt Jv Kg Kj Mr Nf Ny Qv Rj Ue Uv) De(aA aX bE cN cT dI Il In Kc Kp Kr Ky Lv Ly Mb Nk Nx Qv Rf Ur) Il(As aX bE Ch cN Co dI Je Jv Kc Kg Kj Qt Qy Rf Rg Ue Uk) Kc(Ad bN Fp Ii In Iq Jt Kj Kr Mn Nj Nk Of Ow Pb Qv Tj) cT(As Bb Co Cw Hw Iq Jt Kj Nr Ny Of Pg Sr Uv Vp) Ii(aX bN cN cS Cu Dc dI gL Gp Jd Ky Rf Sr St) dI(aF bJ cA cF Ch Co Hq Jk Mn Mr Nk Pd Uk) Iq(aJ aX bE Ch cN gL Gp Qv Qx Rf Ue Tj) Kj(aX bE bI bX gL Ic In Kp Ly Mr Nf Qy) bN(aA aX bE Ch cN cS cZ In Nf Ng Ny Of) Ch(Gp Js Kr Ly Nf Nx Ul Vp) bV(Fp Ly Mc Mn Ny Pg Rj Sr) Ue(bE dH Lv Nf Nk Vp Tj) In(aW cI cS Jd Ph Rf Tz) Of(aX Ba Gp Jv Kp Qv Rj) gL(Ad Mn Nq Nr Ny Pg Sr) Ly(As aX Bg Co cZ Tj) Ba(Bg Co Jd Jt Qt) Lv(Ad aF bJ Cw Uv) Ny(aJ Gp Qx Rf Ur) Nf(aX cZ Jv Qv) Jt(Dg Dl Kf Tj) gW(Gp Kz Rf Ur) St(Hq Ke Pd) Rj(aX Nk Tj) Pg(Fb Ky Ph) Mb(cN cZ) Mc(aX Fb) Sr(aJ Ur) Qv(bE cZ) Kr(Ou Ph) Nx(Ad Tz) DkMu FpUr GpJd MiUm NeVp IubE JkcN OwOu} bA{Rb(Ad aE Af Aj aL As bE BN bQ Ch cI Cq Ct cV Cw Cx Dd De dF dG Fp Gl Gp Ha Hr Hv Hw Ib Ii Il In Io Jo Jt Ke Kg Kj Kr Lh Mb Mj Mk Mn Mr Na Nd Ne Nf Nr Of Oy Pb Pd Pe Pg Po Qw Rf Rj Sr Ub Uc Ue Uk Ul Us Vp Tj) Sr(aA aE Aj As aY bE bJ BN bQ bX cA cE cI cP cQ cR cS Ct cV Fb Fr gL Hf In Jn Jp Kc Ki Kk Kp Kz Ld Ly Mc Nf Nk Nw Nx Of Qd Qw Qy Qz Rf Rj St Ub Ur) Qw(AF Ao aY bE Bn CQ cV dA Fp Gl Ha Hw Ii Il In Io Iq Jo Jv Jy Ki Kj Kk Kr Lh Lw Mj Mn Mu Nd Nj Nk Nr Ny Oy Pb Pg Qd Rf Ri Ub Uc Uh Us) cQ(AF aL bE bJ BN bQ bX cI cV Cx Gl Ha Hw Ib Il In Io Iq Jo Kc Kj Kr Ly Mb Mn Nd Nf Nk Nw Of Oy Pb Pg Rf Rj St Uc Ue Uk Ul Um Us Uv) Rf(Af Ao aY Bb Bn Cq dR Fp Gl gW Ha Hw Ib Ih Ii Il Io Iq Jd Jo Js Jt Ke Ly Mc Mn Nj Nk Nr Nv Ny Oy Pf Pg Tz Uh Us) cV(Af Aj aW aY bE bX Ch cN cP cR cS dN eF gW Hw Ib Il In Io Iq Iv Jo Jv Lv Ly Mc Mn Nd Nk Ny Og Oy Pg Rj Ub) Oy(Af aY bE bJ bX cP dA Ed eF Hc Io Iv Jh Jy Kc Kp Kq Ld Ly Mn Mu Nd Nk Nq Nx Pg Qv Qy Ra Rh St Us Ut) aY(Af aM bE bJ bN bS bW bX Cq Fp Ha Hw Ib Il In Io Iq Jo Ly Mb Mn Nd Nf Nk Of Ow Pg Rj Uc Uf Us Uv) Af(aW bE bG bJ bX cP gL Ha Il In Io Iq Ju Jv Jy Kc Kk Kq Kr Ly Mn Mu Nd Nk Nw Nx Qv St Ur Us) Nk(Ao bJ Bn cE dA Gl gW Ha Hw Ib Ii Il In Jd Jo Kj Mb Mc Mn Nd Nf Ny Pg Rj Ub Uc Ue Uu) Io(aA aE bE bN bX cE cP Fp Ha Hw Ih Il In Iq Jo Kc Kk Ly Mn Nd Nf Pf Pg Qd Ub Uc Us Uv) Ly(aA Ao bE Bn Dd Gl Ha Hw Ib Ii Il In Jo Kj Kr Mk Mn Nd Ny Pb Pf Pg Ub Uc Uh Us) Ha(bX cI dA Gl Iv Jy Kc Kd Kq Lw Lx Mc Mr Mu No Ny Pg Qd Qv Ra Rj Ub Un) dA(bQ bR bS cA dG dH Ib Il Jo Lz Mb Mn Mr Nd Of Pb Pd Pf Um Us Uv) Jy(aF Ao bF Bn bQ cE cG Cq dF Gl Hq Ib Ii Iq Jk Lh Mn Nq Nr Ny) Pg(aA aW bE bJ Bn cP cR Iq Kc Kj Kk Mb Mn Mu Nf Nw Rj St Us) Fp(Ar aW cE Ch cI cR Cs Ib Kc Kk Ld Nd Ph Qd Qv Rj St Ur) Qv(aL bE bJ Bn bQ Cq cZ De Ib Iq Jv Lh Me Mj Nf Pb Rj) Kc(Dd Gl Hw Ii Iq Jd Jo Kr Mn Nj Ny Ow Ql Uc Uh Us) Nw(Ao Bb Bn Gl Hw Ii Iq Jq Kc Mc Mn Nr Nv Ny Pf Uh) bX(bJ Bn cI Cq Cw Dd Ii Il In Mb Mc Mn Nf Pb Uc Us) Mu(aF Ao Bn cE cG Dd dF Gl Ii Iq Jk Mn Nr Ny Uc) Iv(Cq Cw Ij Il In Jo Js Jt Kr Lh Me Nf Of Qa Us) bJ(Ch cI Hw Il In Iq Jo Mn Nd Nr Ny Ub Uh) In(aW bR cP Dd Il Iq Jv Mn Nd Rh Us) Us(bE cD eF Jv Lv Mr Nx Ra Ub Up) St(Ao Bn Gl Ii Lh Mn Nr Ny Uh) Rj(Ch Gl Hw Iq Jv Mj Ri Ub Uh) Mc(Fb Il Iq Kr Lz Mk Mn Ub) Nd(bE eF Gl Hw Il Nj Ny Ra) Ib(bN Ed Lw Mj Mn Qy Rh Ub) Nx(Ao Hw Ii Jo Lh Mn Ny Uc) cR(Cw Hw Ii Il Iq Kj Nf) Uc(bE eF Kq Lv Mr Qy) Jo(cP Ih Ip Kp Ld Ra) Ub(Cq Iq Ki Nr Ny) Mn(bE Ky Nf No) Hw(aW bG cP Kk) Ii(Jq Kq No Qd) Ra(As Cq Kj Pb) Qy(Ao Ch Nr Uu) Ny(aA Ih Kk Rh) Bn(Dc Jq Kq) Gl(bE gL Gp) Iq(Kq No Qd) Uh(Ct Nf Pb) cP(bE Ch Cq) Nr(Ar Ih) Nj(Mb Ue) Jv(aE bN) Kk(Jd Pf) Kr(Ch Hf) Lh(Kp Kq) Rh(Aj gW) Of(Ed eF) Uv(cD eF) DcDd PoLx JubN dGdN} Kq{Af(Ad aM Ao As Bb bH bJ bN cC Cp CQ Cu Dc Dd Fn Fw GL Ha Hr Hv Ib Ii Ij Il In Io Iq Ir Jo Js Jt Kc Ke Kj Kr Kz Lh Mb Md Mn Mr Mz Nd Nf Nj Nm Nr Ny Of Om Oy Pb Pd Pe Pg Po Qv Qw Ra Rb Rj Sr Uc Ud Ue Uf Ug Uh Uk Ul Um Up Ur Us Ut Vp) Ao(Ad An As Ba bJ BN CP Cq cR Cu Cw Cx Dc Dd Fw Ha Hr Hv Hw Ib Id Ii Ij Il In Iq Ir Jn Jo Jr Js Jt Ke Kr Lh Ly Mb Md Me Mj Ml Mr Mz Na Nf Nm Om Or Oy Pb Pd Pe Pi Pk Qa Qw Qy Ra Rf Rj St Uc Ud Ue Ul Um Up Us Uv Vp Vv) Ii(Ad aY bJ BN cQ Dd dK Gl Ha Ib Ij Il Io Iq Jg Jn Jt Ly Mb Mj Mn Nj Nk Ny Or Oy Pd Qv Qw Rj Sr Uc Ue Uh Um Uu) Uc(aA aW aY Ba Bb Bn cI cP cQ cT eF Gl Hb Hc Il Io Iq Jq Kc Kp Lh Mn Mu My Ny Ou Pg Qv Qy Ra Rb Sr Uh) Il(aY Bb BN cQ dA Dk Gl Ha In Io Iq Jd Jq Jt Ke Kr Mc Mn Nv Ny Oy Pg Qv Qw Rh Sr Tz Ub Uh Us) Io(Ad aE aY BN cG cP cQ Dd gW Ha Ib Iq Iu Jo Jq Kj Ly Mn Nf Om Oy Pd Qv Qw Rb Ub Ue Us) Us(Bb cP cQ dA Gl Iq Jd Jq Kc Lh Ly Mn Ny Pg Qn Qv Ra Rb Ri Sr Uh Up) Qw(aF aY Bn cP cQ Cx dA Dg Gl Hb Iq Lh Mn Nu Ny Oy Qn Qv Sr Ub Uh) Mn(aY BN cP cQ Cx Dd Ha Mb Mc Me Nf Oy Qv Ub Ue) Iq(BN Cx Ib In Jo Kr Nm Oy Qv Ub Ue) Bn(aY cI cP cQ Gl Kr Qv Ra Sr Uh) Oy(bN cP cQ Gl Ny Qn Qv Ra Uh) Sr(aY bV cI cP Kc Kj Ue Ur) cQ(Ad bN gW Ha Jq Mb Tz Um) bN(aY Gl gW Jt Nr Ny) Qv(Ad Dd Ha Jo Kc) Qn(Ib Jo Nf Vp) cP(In Jo Jt) Dd(Gl Uh) Mb(Ny Ra) Ib(Cx Jq) GlcR UbPg UeNy IvJo JqKr UmUh} Qw{dA(aA aL aQ aS aU aV aY bI bN bO bV cP cQ cS cT Cu cY eF Fb Fr Gp Hf Hr Il Io Iv Jn Kc Kf Ki Kk Kp Ky Kz Ly Mw Nj Nk Nt Nx Om Ou Ph Qd Qt Qv Rb Rf Rj St Ub Ur) cQ(aA aJ aP aY bV cN cS cT dM dN eF Fb gL Ih Io Ir Iv Jy Kc Kf Kk Kn Kp Ky Lx Mt Mu Mw Nt Nw Nx Ph Qd Qv Rf Sr St Ub Un) Ub(aA aY Bc bJ bN bV cP cR cT eF Ez Fr In Io Iv Jn Jy Kc Ki Kk Kp Mr Nj Nk Nt Nx Qd Qt Qv Rb Rf Rh Sr Ut) aY(aA bV cT Dc dI Dk eF gL Gp In Io Jh Jn Jy Kc Kf Kk Kp Lw Lx Mu No Nv Nw Nx Ny On Qd Qv Rb Rf Sr St) Qv(aA aC Ba bE bI bV cN cR cT cZ dI dM eF gL In Io Iv Jy Kp Lv Mi Mu Mw Nj Nt Nx Qd Qy Rf) Io(aA aJ aS Ba bV cP cT dM eF Ez Fr gL Iv Jn Jp Kf Kp

Figure 19 Continued

Mw Nx Qd Rf Sr) Rf(Af Al Ao bI Bn cP Dd eF Ha Ii Il Iu Iv Mf Nj Nk Nl Qy Sr) eF(aE Aj aS aW bP bV cI Il Jo Kk Kp Nx Qd Sr) Af(aA cT gL
Jy Kk Kp Mt Mu Nw Nx Qd St Ut) Qd(Ao cP Ha Ii Il Nj Pg Qc Ri Sr Uh) In(bV cS cT Iv Jn Kf Kp Ou Ph) cT(Jo Lh Oy Pg Ri Sr Uh Us) aA(aF
Bn Cx Ha Pg Rh Ri) Ao(Cu gL Jh Kf Nw On) bV(bJ bN Iv Pg Rb Sr) Ii(Fr Lx Mt Nw Nx) Jo(cS Iv Kp Nx Qt) Jy(Bn cP Il Ou Qn) Kp(gW Oy
Ri Sr) Lv(aS bI Il) Nj(Kc Lx Ph) Ri(Kf Kk Ph) Mu(Il Iv) Sr(aJ Jp) Nw(Qn Uh) bN(aJ Kc) dl(aS cP) CsFp FbMc QyRh Kyc]} cQ{Qv(aA aY bV
cR dM Fb Fr gL Ln Is Jy Kc Kp Lv Mu Mw Nw Nx Oh Ph Qd Qy Rf St Ub) Io(aE aJ bV cS cT Cu Dc Fb Fr Ih Iv Jn Jp Kk Kp Nt Nw Nx Oh Ph
Qd St Un) Af(aA aJ cT Dc Fb gL Is Ji Jy Kc Kk Mu Nv Nw Nx Om On Qd Rf St Un Ur) Rf(aF aS aY BN cI cP cT Cx dR eF gW In Ip Kc Ly
Nd Ne Nk Rb Rj) Nw(aF aY BN cP Cx Gl Ii Il Iq Jd Kc Ke Mb Mn Nu Ny Qn Sr Us) Kc(aY BN Fp Gp Hw In Ip Jy Mr Mu Nj Nk Oy Ra St Ub Us) In(aS cS cT Fb Ip Iv Kf Kp Mb Mr Nx Ou Ph Un) Kk(bE BN Fp Gp Il Jd Kr Oy Ql Rj Sr Um Us) Us(aA Cu dA Dc dM eF Ih Is Kp Nx Qd Sr Un) St(aF aS aY Bn cP Cx gW Ii Il Iq Nj Qn) aA(BN Cx Il Iq Ly Mb Nd Nk Oy Rj) Mu(aF aY BN cP cT Cx Il Iq Mb) Ub(bX cR cS eF Jy Nk Rb) Qd(Cx Ii Il Iu Ly Sr Uc) Kp(bN Cq Ib Jo Kj Oy Ue) Jy(aF Bn cP Cx Il Mb) bN(aJ bX cS dN Ky Nx) Ip(aJ bV Jo Ug Ur) Bn(Kn No Sr Un) Lv(aE cP cS Il) Ly(aE bV Ir Mb) Kf(Jo Oy Uc Um) Nx(Ii Il Mb Oy) Sr(Jp Oy Uc) Bo(Ch Oy) Dc(Il Iq) Mb(bX Rb) Un(Il Ue) cP(bE No) cT(bX Hw) FbMc NddA IqaJ IvJo} Af{aA(aP Ar aW Ba bE bN bQ bR bW bX cA cB cI cP cT dG eF Hf Il In Io Iq Iv Kc Lv Ly Mb Mc Mr Nd Nk Nq Nx Qv Rb Rf Rh St Ur Us Vv) Kc(aY Bc bN cT Cu eF Fr gL Gp Iv Jn Jy Kp Lv Mr Mu Mw Nj Nk Nl Nx Om Qt Qv Qy St Un Ur Ut Tj) Qv(aJ Ba bE bV cT eF Ez Fr gL Is Ji Jp Jy Lv Mu Nw Nx Om On Qd Rf Un Ur) Kp(bJ Cq gL Gp Ha Ib Io Jo Jy Kj Kr Mu Nf Oy Pb Rf Rj Uk Um Ur Us) Nw(Ao aY cP dA eF Ha Ii Io Iq Jy Kr Ly Nk Pg Rb Rj Us Vp) Nx(bV cT gL Gp In Io Jj Jo Jy Kj Mb Rf St Ub Ug Ur Us) cT(aJ bE cN dA In Io Jy Kk Mu No Qd Rb Rf St) gL(Ar aW bN cI cP Il Io Iv Kk Ou Qd Rb Rf) Mu(Ar bN cP Il Iq Iv Kk Mb Rb Rh) Rf(aS aY Ba cP eF Fr Nk Rb Us) St(aY bV cP Iq Jy Nj Nk) Kk(bI cN eF Io Mn Us) Qd(eF Ha Il Io Us) Jy(Ax bV cP Il Ur) Kf(Ha Ib Jo Kr Oy) Ur(dA eF Iv Lv) Lx(cP Ha Po) Io(aJ Fr Jp) Sr(Hr Jp Us) In(Jn Qt) Rb(aJ Ky) cP(Cv No) FrUs} Qv{dA(aC aV aX bE bJ BN bR bS bU bX cA cF cG cK cL cP Cq cR dH Ha Hq Ib Il Io Iq Kc Lz Mk Nd Ne Nk Nx Of Oy Oz Pb Pd Qy Rg Uk Ul Us) In(Bc bI bJ bV cR cS dM Dp Fb Ip Iv Jn Kc Kp Ks Mw Nj Nx Ou Ph Qd Rh Ub Un) bE(aY Bc BN cI cT Cx Io Iq Iv Jn Kc Kk Kp Nj Nk Nx Ou Ra Rb Rf Rh) Kc(aY bI BN cZ eF Io Jv Jy Lv Ne Nj Nk Nl Qy Ub) Kp(As Cq Cw cZ Dd Ha Ib Ij Io Jv Kr Nf Oy Rj Uc Us) Io(aA Ba bV cZ Ez Fr Jp Lv Nx Ph Qd Rf Un) Nx(aY Bn cZ Dd Ha Ii Jo Nd Oy Ub Us) Lv(Bn cI cR gW Il Ly Nj Nk Rb Us) Qy(Ao aY cR Ib Kj Nd Oy Us) Bn(aA eF gL Jy Mu Nw Rf) aA(bN Cx gW Iq Oy Pg) eF(aE cI Kk Rf Ub Us) aY(Mu Nw Rb Rf St) Qd(Fp Ha Ii Sr) Nk(cN dI Ub) Iq(Dc gL Rf) Ub(cR Rb) Sr(gL Jp) Oy(Kf Kk) bV(Ly Rb) cZ(Iv Ou) FbMc FpPh MuaF JvcR RfbI aLcT bNcN cPdI gLgW} Io{Kp(As aY bJ BN cP Cq cT Cw dA Dd Gp Ha Hr Ib Ii Il In Iq Jo Kj Kr Ly Me Mr Nf Oy Pg Rb Rj Ub Uc Ue Ug Uk Um Us Uv) cP(aJ Ar bE cR cS Cu dA Dc dI Fr Iv Jn Jy Kc Kk Lv Ly Ma Mu No Nw Nx On Rf St) cT(aE aY Bn bX cI dA Ib In Iq Iv Jn Jo Kc Ly Nf Oy Pg Rb Rf Ub) Kc(aS aY bN eF Gp Il Iv Jn Nj Nk Oy Ub) Kk(aY BN eF Gp Ic Il Nf Nk Oy Ub) Nx(aS aY BN bV dA Gp Ub Us) Kf(Bn Ha Ii Il In Jo Me Oy) aY(Cu Fr Ih Jn Nw Rb Rf St) aA(aF BN Cx Qn Rb Rh) Ba(Ao Il Iq Iv Oy Uc) Iv(aJ dA gL St Ur) bV(bN Ly Nk Ra Rb) In(aS cS Ou Ph) Sr(Bn Ha Jp Oy) Cu(cI Il Jo) Ub(eF Ez Nk) dA(aV cS Jn) Iq(aJ gL) Qd(aS Gp) Qt(Ly Rb) eF(aE cI) AoOn BnNw CsFp DcIl IcRf JnUs JpUh PgPh aJbN} In{cP(aA aW Ax aY Bc bN bV cI cR cS cT Cu dA eF Fb Ip Ir Iv Jm Jn Jy Kc Kk Kp Mr Mu Mw Nw Nx Oh Ou Ph Qt Rf Rh Ub Un) Iv(aW aY bJ bN bV cS cT Fb Kc Kp Nx Ok Ph Rb Rf Rh Ub Ur Us) cS(bN cT Il Iq Kp Ly Mb Nd Nx Ou Ph Pi Rb Ub Us) Iq(aE aS Bc bN bV Cs cT Cu Kf Ph Qt Rm Un) Ph(aY bN Dd eF Fp Il Jo Nj Sr Ub Us) Ou(aS Bc bN cR eF Fb Ip Nj Ow Ub) cT(aY bJ Il Ly Nd Nk Rb Sr Ub Us) Kf(BN Dd Ha Ii Il Oy Uc Us) Kp(bJ Bn Dd Oy Rj Sr Us) Us(bV Jn Ks Mr Nx Rb) Il(cR eF Ks St Un) Sr(Ax bV Jp Nx Qd) Ub(Bc Mr Nk Nx) Cs(Fp Ha Kr) Ip(aW bV cI) Fb(Kk Rh) Kc(Mr Nj) aW(cR Cu) aY(Rf Vv) bI(Mb Rh) eF(aE Kk) AxKr UrgW aSbJ} eF{Kk(Ad aE Aj Ao As aY BN cG Ch Co Cq Cw Dd De dG Dl Et gW Ha Hw Ib Ii Il Iu Jd Jo Jt Ke Kg Kj Ko Kr Mb Mn Nj Nm Of Oy Pd Pf Pg Rj Sr Uc Ue Us) Kc(aE Ao BN cI Dd Ii Il Iu Jo Kr Mn Nj Nk Oy Sr Ub Uc Us) Uc(aA Dc Ih Jn Kf Kp Nw Nx On Ph Qd Rf Sr St Ub Un) Ub(aE cI cV Ib Il Ld Mb Ne Nk Oy Rb Rf Rh) Us(Ar aY bV cI dA Kp Ld Nx Qd Rf) Jo(Ax cT Kf Kn Kp Nx Ou Ph Rh) Rf(Aj aY Bn cI Ma Nm Rj) Oy(aY cI Kf Kp Ph Sr) Qd(Bn Ii Il Jq Mn) cI(Ib Kj Mb Rj Ue) Mb(aA Aj aY) Kp(aE As Ib) Ao(Nw Ph) Il(dA St) BnJy CsKr LvaE MnaA MyIb NkUe IiSt RhaY} Sr{bV(Fr Hc Hf Jn Jp Kc Kk Kp Kz Ld Ly Me Mu Nk Nw Nx Qd Qy Rb Rf Rj St) Kc(aS aY bX cP cS cT Cu dM Fr gL Iv Jn Jp Mt Mw Nw Nx Qd Ut) Rf(Ba Bc bI cP cT Fb Fr Ic Jp Kp Ly Mw My Nx Rb) aA(Ar aY bJ bN cI cP cR Fr Ic Jn Jp Kk Nx Og Qd) Kk(aE aJ aX aY bE bI bN cN cP cS cT Fr gL) Kp(aJ cT dM gL Hr Mu Nf Nw Rj St Ur) Jp(aE Ao Jj Jo Ld Ly Mc Nx Rb Rj) cT(Jn Ld Ly Nw Nx Rb Un) Nw(Ao aY cI cP dM) gL(aE aW cI Ou) Jn(dM Jo Ug) Kf(Jo Oy Us) Nx(aJ Ur) Us(Iq Ri) FrUr IldI RbaJ QdcP} dA{aV(bN bR bS bX Ha Hr Ib Il Iq Jo Jy Kc Kj Kr Ly Mb Mu Nd Nf Nk Nw Nx Oy Rf Rh Rj St Uc Ue Ul Um Us Uv Vv) Us(bO cP cS cT fP Hf Iv Jn Kp Ly Mr Nf Nk Nx Rb Rj) Nk(cP cS Ic Kp Ly Mb Rj Ub Ue) Nx(bN Ha Il Jo Mb Nd Oy Uv) Iv(bN Il Jo Mb Nf Oy) Kp(bN Ha Il Oy Uv) cS(Ly Mb Nd Rb) cT(bX Ib Nd Oy) Il(Cu Jy St) cP(Mb Mu Qd) Kc(bN Nj) Kf(Ha Oy) CuUc FpKk LyMb IiSt} Rf{aY(bJ BN cP cR Gp gW Ha Ii Il Iq Kr Ly Mc Mn Nd Nk Oy Pg Ra Rb Rj Uc Us) cP(Bn dI dR gW Ha Iq Jo Kr Mc Nm Ny Oy Pg Rj Us) Ii(Cu Fr gW Jn Ly Mi Nd Nk Nx Oh Rb) bI(BN Iq Mc Nk Ny Oy Rb Rj) Rb(Bn Kr Nm Ub Us) Ny(aS Ba bN cT) gW(Al Ne Nj Nk) Ly(Bn Kr Nm) Ao(Kp Mu) Ha(Iu Mi) Nr(Ba cT) Ub(Nk Ra) Qy(Oy Uc) BnIu NdNj IpJo IqaS RjbN PgcT} cP{Jy(aF Ao Bn Ch Ii Il Iq Jk Mb Mc Oy) Lv(cI cR Jo Nf Of Oy Us) Nw(Ao Bn Ii Iq Ke Ny Pg) dI(bX Kc Kk Kp Nk Nx) Oy(bE Dk Jh Nx Ny) Bn(Dc Jq No St) Jo(cR Iv Mr Nx) Ii(Jq Qd St) No(Iq Mc) St(Iq Pg) Kk(Fp Jd) Nx(Hw Us) FbMc NjKc NkUb UpUs PgaA} Us{Ri(aA Ba cT Fr Jn Kf Kk Kp Nw Nx On Ph Qd St) Up(aA Ba bV cT Jp Kf Kp Nx On St) Nx(aY bN Ii Il Jo Lv Ub) Rb(aY bV cT Iv Kp Ub) Lv(aY Il Kp) Mc(Ba Fb Un) Fp(Ax Cs) Mr(Ba cT) Kf(Bb Uh) Pg(aA bV) CuaY IqaA RabV KcbN KpOy bXcT} Kc{bN(aY cR cS gW Il Jo Jy Nj Nk Oy Ub) Fp(Ax aY bV Cs cT Iv Jn) Nj(aY Iv Jo Ky Og Oy Ub) Ii(Cu Iv Jn Mr Mu) Jo(cR Ip Iv Mr) Oy(cR Iv Jh Qy) Gp(gW Ra) Ha(cR Mr) Nk(Ub Ue) Iq(cR Mu) Jy(Bn Il) FbMc MrKr} aA{Bn(bR Iq Iv Ly Mc Mr Nk Ra Rb) Cx(bR Iq Ly Mr Nk Oy Rb) Nk(Hw Iv Jn Lv Mc Nx) Iq(bJ bN cC cI Rh Ub) Nx(Ii Jj Nr Oy Pf) bN(bR Iv Mc Nq) Fp(Ax Cs Ph) Mc(Fb Ic) Rh(gW Ny) Pg(cR Ic) LyaY IvPf} Kp{Oy(As aY Ba bJ Cx Hc Hu Jh Jy Kr Lv Mu Mw My Ny Qy Rj Ub Uc) Jo(bJ cR Ip Iv Rh) Fp(Ax bV Cs) Kr(Hf Mc Rb) Ao(gL St) Lv(Mn Uc) Ii(Nw St) BnJy FbMc NkUe LhgL RiRj bNcR} Ii{St(aY cR cS Iq Iv Jn Nj Nk Nx Qy Rb) Nw(Ao aY BN cR Dd dK Ha Nx Rb Rh) Nx(Cu Dc Fr Ir Is Jj Jo Nk Qd) Qd(bN cR Rb) Mu(Ou Ph) CucI IvgL} aY{St(BN cR Dd Ha Il Iq Nj Rb) Nw(BN Cx Il Iq Ke Qn Uh) Gp(Ly Nx Rb) Lv(bN cR Ly) Kk(bN Fp gW) Bn(Jy Kd) Ha(Lx Mt) Mu(bN Iq) Jo(Kn Nx) MbRb IlJy} Jo{Nx(BN cT Cu Gp Il Jj Nc Nk Ok Oy Rh) Iv(Ba cR cT Ok Rb) cT(bJ Ly Mc Rb) Kf(Iq Mc Pg) Ph(Mc Nj) CuIq NkOk IpKk OucR bNcS} Kk{Fp(aJ aS AX bI bV CS cT Oa) bI(Hw Jd Mc Pg) dI(Il Mn Nj) gW(bN Gp Lv) Fb(Bb Mc) Oy(Ip Qy) BnJy GpNy HwIc JdcT} Mc{Fb(aS bV cT Ou Ph Ub Ue Ur) cT(Jy Kr Mk Mu Nk) aS(Mu Nw Qd) Ha(Kf Qd) BcUb IpbV KfKr} Fp{Cs(bV cT dM Kr Mu Oz Ph Ug Ur) Ax(cT Fb Kr Ub Ur) RjbV} Rb{Ub(bN cR Gp Jj Mb Nk) Mb(bI cT Jy Ly) bV(bN Gp) AogL LvIl HwcT} Ao{Nw(Bn Ly Nd Qn) Mu(Iq Rh) gL(Ly Un) CuNf StQy JycT KfOy} Bn{Jy(Ar cT Il Ou Ph) Mu(Il Iq Iv) PoLx HaQd NwUh} Nx{Jj(Mm Nk Nm Ny Oy Qd) LvUc NkUb IldI} Lv{Il(aW cR Lj) cR(aW cI) UcKf bNcS} Iq{Mu(aF aS cE cT) JyaS aJbN} Oy{Iv(Ba gL) Qy(Mb Ou) KfUh QnNw} Nk{Ub(bN cR Jn Mb) StNy} cT{Pg(Ly Qd St) LyHw IbQy} bV{GpRa LybN IpPg RiRj} Jy{Il(Ld Rh) LyMb} Ha{CsMu QnNw} Nj{StNy KrPh} NlStNy

Figure 19 Continued

Constrained panels with 3 analytes, where 1.0E-8 >= 'AUC p-value' > 1.0E-9. Contains 3,175 panels of 6,910,825 total panels evaluated. :
Nb{Ao(Ad Ap As Ba bE bJ Fw Hr Hv Hw Ij Js Mj Mr Nm Pb Qx St Uk Ul Um Vp) Ch(aM aX bE bJ cT dA Ii Ij Jt Kc Mb Mj Ml Mr Pb Qv Qx
Qy Rj Um Tj) Ub(Af aM cP cV cZ Gp Hv Hx Ii Kr Me Mr Mx Ny Pi Po Qv Qx Rh) Ue(Af As aX bV cT Fw Gp Ij Js Mj Mr Mx Pb Pi Po Qh
Rh Tz Ul) Bn(Aj bN bV Cv Dc Dd Jj Jq Jv Kp Nc Ne Nx Ph Sr Un) bN(Af bV cT dI gL Hr Il Iu Jj Jv Ky Mb Mi Mk Qv) cT(Ad Af bQ Ct Dd Ii
Il Iu Kg Lh Mb Mn Nf Ng) Dd(aS Bg Hc Hr Jc Jv Kf Kp Ky Mk Ng Rg) Rf(Hq Ij Iu Jk Jt Nf Nm Of Pd Rb Rj Vp) dA(bJ bQ cG cK Cp Ct Kg
Lz Mk Na Pa Pe) Jd(aA aX cP Il Jt Kr Ly Nx Qv Rb Rj) Kc(As Co Cw Fw Gp Iu Lh Mj Mr Po Vp) De(Ar Ba bV gL Gp Jj Kk Kq Mc Ug)
cP(Ad Aj Cp Fa Hq Je Mq Mw Ny Uv) Cq(aJ cN Kk Kq Nl Qd Sr St Vv) Rb(As bQ Co Dk Kg Mk Mw Ny Po) Qv(aC As aX gW Il Mk Mr Pb
Vp) Jt(Bc Bg bV cN Co gL Kp Sr St) Af(aX bV Gp Il Iq Kr Ne Nx) Ii(aJ As Ba bE Bg bV Je Un) Rj(Bb Bg cZ Dk Je Mr My Pb) Ha(cI Is Lj Lw
Mz No Pg) Ly(aJ Bb bE cI Dk Gp Uk) Kj(Ba bV Dg Fb Hc Kl Nx) Uc(Is Jj Lw Ph Ug Ur) Ij(Kk Kp Ky Sr Uk Ur) Il(bV cZ gL Hf Oa Ur) Tj(bA
cI Jv Nx Ou) Mn(aX cR Gp Kk Ur) Nf(bE bV Kg Kr Ky) Iq(cI Kr St Uk Ur) Iu(aX Ba bJ cZ Ul) Vp(cN Jv Jy Ky Mc) eF(cG cV Fa Lh Nm)
gL(aF Gl Mc Of Uu) As(bX cN cZ Ky) Po(dI Jv Kk Kp) Mb(aX bE Bg Jv) Ib(cI Cp cW Jp) aA(bJ Fw Ko Tz) bA(bE Ke Qx Ul) cR(cV Hr Kz
Ng) Ba(Cp Je Ny) Kr(bV cS Nx) aY(bE Ug Ur) dI(bQ bS Pb) Bb(Fb Nx) Cw(cS Kp) Mi(bJ Ul) St(Ad Ny) Jy(aF bF) Of(Kk Vv) aX(Co Nq)
BgNx CsFp CtIo GpJe MuaF NcTz NebQ NiKz HqbJ InRh QdSr JjgW JkKq JodN KgOu KobV NyUm} Ni{Kq(aM Ax Cq Cs Cw Fw Jd Jh Js Ke Kf Kr Md Mj Mr Nm Ny Of Or Pb Sr Ug Uk Ul Ut Uv Vp) Kp(aM An Cp Cs Ct Cu Hx Id Ii Ir Iv Jr Kz Lh Ml Na Nm Om Pe Pk Ra Rb) Kf(An Cu Fw Hv Hw Ir Iv Jn Jr Mj Ml Mz Na Or Pi Pk Ug Uk Up) Kj(bI Cu Dc Ef Ez Fr Im Ir Is Jp Ky Li Lv Qa Ut Vv) Lv(Cp Cq Cu Cw Gp Ib Nx Or Uk Ul Uv) Cs(Dc De Fw Kn Kz Md Mz Ny Ow Po) Qh(bJ Cq cV Ha Ic Ij Js Mj Pb Ul) Aj(Ax Ez Is Jp Kk Kl On Ph) Ib(aJ Fr Is Jp Mt My Nj Qy) Sr(Cu Iv Kr Mw Na Pe Qa Ra) Vv(Ao Bg Ha Ii Mk Mr Pb Tj) Ax(dL Fw Kn Md Mq Mx Pd) Kk(Ch cN Mt Nj Nk Nq Og) Ky(cI Io Jo Rj Ug Uk Us) Ba(gW Ii Jd Jt Jv Mr) Uc(Cu Dc Ji Jp Mw Qa) Is(aM Cq Ha In Nr Ul) Qd(cC Cq Fw Nr Uk Tj) Kz(aJ aP Mw Oh Ou Ph) Nw(Ch Cq Jd Um Vp Tj) Nx(Ih Il Iv Kg Nf Ng) bE(aA aS cI Mc Ne Nj) As(aS bI Dc Lw Mu) Oy(Ez Ji Ua Un Ut) Ph(aN gW Nm Of Ug) Cu(Cq Dd Ij Iq) Hw(Fb Qy Rb Ut) Kr(aA cS eF Jj) Us(Cp Jy Lw Un) Af(Cp Im Un) Dc(Ad Iq Nm) Mi(bJ cV Um) Nj(gL gW Uk) Ii(Ji On Ou) Qa(Dd Ha Vp) Qy(Ch Jo Nd) cI(cN Mc Mu) Ao(Bo Jy) Bn(Cp Im) Fn(bX cH) Mt(Cq Ul) In(Ji Ok) Jn(aA Ug) Jo(Ez Kd) aJ(dL Ug) aS(cC Nd) aW(Nl Ow) dI(cF Ld) BbJg FbMs MubF NaeF IhgL IjKd IlIr ImRj IvJj RbOu QwUn JvaE KgRf UldM UrbV} cQ{Us(aJ bV bX cS cT Fb Fr Iv Jn Jy Kf Ld Lx Mr Mt Mu No Nt Oh Rb St Ub) Qw(CU Cx Dc Fr Jj Jn Ld Lv Lw Mp Mz No Oh Om On Qt Qy Rj Um Ur) Io(aP Ar Ax bX cP dM Ir Is Jg Mb Mw Ok On Qa Qb Qe Qz Rf Ub Ur) Mb(aJ bE bV cS cT dA dM eF Fb Ip Iv Jn Kp Nk No Nt Un) Ub(bJ cT dM Gp In Ip Kk Kp Lv Mr Mu Nw Nx St Um) Kq(aE cI Cx Dd Ib Jo Jt Kj Kr Lh Nf Rj Ue Uv) Kp(aE Aj As aY bE bJ Bn cV Kg Kr Of Rj Um) aA(bS bX cV Ib Kc Mc Nf Rf Uc Ul Um Uv) Ly(aJ aP aY cP cS cT In Iv Jj Mu Rb) Qd(bN bS cT Gp Ha Hw In Nf Nk Rb Rj) Af(An dM Fr Jn Lx No Oh Ph Qv Qz) Sr(Ha Ib Ii Il Jo Nf Rj Um Un Uv) Nk(aJ aP bV cS dA Mu Qv St Uc) Kk(De Ib Ii In Jo Nf Of Pg Ue) Qv(aJ Bc Bn cT Ih Rb Rj Ur) Cu(bN cI Ii Il Jo Oy Uc) Mu(aE aS Ii Mn Um Uv) Jy(aE bN bV Rj Ue Um) Nx(aE aY Bn Ch Kr Um) cT(bE bJ cV Jo Mc Oy) Ip(aE Aj cI Jj Ld) Iv(aE bN Il Oy Ue) Kf(Bn Ib Kg Nm Of) Rf(Aj bE dM Gp Wm) Un(bN Kj Oy Rj Uc) dA(bR bX cA cF Um) In(aE Bc Mw Pi) Nw(aS Nd Pg Uh) cP(bX dI Kc Lx) Bn(Dc Jq Kd) Fb(Ch Hw Jj) No(aY Cx Il) Lv(aS aW cI) bN(cN dM Ir) bV(bX Rb Rj) St(Ne Um) Jo(Oh Ph) Kr(Ih Oh) Ur(bA gW) BoaY DcUc PoLx MtIl UeLd KccI VpbA} Io{Kp(Ad aE Aj aM aS bV cI Cp Fw gL Hv Hw Ij Ir Js Kg Mf Mj Ml Nm Of Og Or Pb Pd Pi Pk Qx Rf St Ud Ul Up Ur Vp) Qv(aJ Ar aY Bc cR cS Cu EF Fb gL In Is Iv Jn Kk Kl On Qy) Kq(aS aW cI Cw dA De Hf Ij Jd Kc Kr Lh Mb Of Pg Po Rj Um Uv) Ub(aA Ar aY Ba Bc bV bX cP cR cS dA Fr Gp Iv Jp Rb Rf) cP(Ba cT Dg Gp Ih Ir Is Jg Jp Mb Nk Oh Qd Rh Rj Ut) Rb(aJ aS Ba dA Gp Jn Jp Kc Kk Mb Ph Rf Ur) Qw(Ar Bg cS Is Jg Kc Nw Ph Qt St Ur) Ly(aJ aS aY Ba Cu dA dM Gp Kf) Kc(aA bX dA Ic In Jy Mr Nx Og) Kk(aS cS cT dA Ha In Jn Lv Um) cT(aW Ch cS Ct Ih Il Qd Us) Jn(Af aS BN bV bX Ha) aY(Ba gL Gp Iv Jg Lv On) Ba(Af bN cI cS Ib) In(Bc bV Cs Fb Rh) dA(aS Cu Ic Jp Mb) Il(Ef Jy Sr St) Kf(Af Ib Nf Uc) Nx(aE aJ cI Ue) bN(Cu Fr gL Qd) Iv(aP aS dM) Ph(eF Hw Jo) aA(bJ Ic Rj) Af(Cu On) Ao(Jg Nw) Bn(aJ St) Ii(Sr St) bV(bX Ic) cI(gL Kl) CuOy DcIq FraS HaQd NfSr RfVp NwaF} bA{Rf(Ad Al Cw Dd De Iu Jk Jv Kr Lh Me Nd Nm Po Qb Qh Rj Rm Uf Vp) aY(aL Bn dG dH Gl Ii Kc Kj Kr Mp Mr Mu Nw Ny St Ul Um) Iv(Ad As bQ Dd Fw Hr Hv Hw Hx Ii Jn Mj Mr Pb Pe Po) Nw(aF bF cE Cx Dd dF Ha Il Jt Nd Nk) Mu(bQ Hq Ib Jo Mb Nd Pd Ut Uu) Ub(BN Ct Fw Il Kr Me Of) Jy(bN Cp Cw dH Jo Nd Om Uc) cP(Aj aL As Ct Ib Iq Of Us) Ha(cR dC Kk Kp Ld Nx St) Qy(Aj Ct Kj Nd Nq Of Qu) Kr(Ax Ct Jv Ki Ld Me Oh) Qd(Cq Il Jt Lh Nk Us) St(aF Cq dF Jk Ke Nj) Kq(Cq Ib Jo Jt Ke Us) Nx(Cq Cw Jt Nv Of) dA(Pe Po Rg Uf Ul) Mn(aA Ih Kk Ld) Nk(aW bE cI Kc) Ib(aW Jh Kk Mw) Ii(Cu Ih Kk Rh) Qv(aC Hv Of Um) Uh(Kz Mb Me Ul) gL(Nr Ny Pg Qw) Ra(Cw Mj Mr) Ju(aE Bn Mb) Kc(Cq Il Pb) Us(Iq Kp Un) aF(Rb Rj Sr) bJ(aW Jv Kj) cV(aX Jj Kj) Gl(Hw Il) Uc(Kf Kp) Jo(Ph Rh) Uv(bE Mr) aA(Hw Nq) bQ(cR cS) BbPh CwDc FbIh NodF LvNf LwRj MbJv MccE MqRb NgcI NjLd HqPg IncF KkKo KnOy LhOh RhbE bNcN cSdH} Qw{dA(aJ aK aO aW Ba cH Ez gL Hc Jp Jy Lv Lw Mi Mu Nw Sr Ut Vv) Ub(aJ bX cN Cu dM Fb gL Il Ip Is Jj Jp Kf Lv Mw Un) eF(Af aJ Ao bN Ch CS Iv Jn Kc Of Ph Rb Rh Ue Us) bV(bI Hf Il Ip Jo Jy Kr Ly Nk Qy Rh Rj Us) cT(Ao Cq cV Ib Kc Kg Ki Kj Kr Ly Rb Rf Rj) Kq(Ad bF bN cI Iu Jo Ke Kj Kr Pd Pg Ri) aY(aJ Ba Bo Hc Hf Jq Nt Om Qy) Qd(Bn In Iu Jo Ke Lu Mn Rb) Qv(aJ aX cS Ez Kf Qt Sr Un) Rf(aS cN Iq Jv Kp Ne Or Qt) Jo(Fr Jn Kf Mw Ou Ph Rh) Jy(aF Cx Ii Kp Nu Ph Rh) Sr(Fr gL Il Iv Jn Nw) Af(Fr Jn Nv On Un) Lv(aW cI cP cR cS) In(Fb Ir Nx Qt Rh) Ao(Fr Mu Mw Ut) Nj(aJ Kf Kk Mt) Rb(cN dM Ky Qt) Nx(Il Kj Lh Oy) bI(Jj Kj Kk Rh) cR(cP Kz Qy Rj) Mu(aF Cx Ii) Kc(Iv Mr Nk) Ri(gL Jp Qt) Gp(cS dM) Il(Fr gL) Ky(bN Hc) Rh(cN Mp) AxFp IiJn QyOu aAdH bNcN dIdM} Kq{Ao(aM cC De Fn gL Hx Iv Ji Jq Kc Kd Kj Kp Mx Nd Nw Ny Of Po Rb Ut Vt) Ii(As cP cR Cw Di Dk Jd Js Kj Kr Me Mx Nd Nf Pb Pg Rh St Ub Uk) Af(aW cI cP Ct eF Fp Hx Is Iv Jn Kd Kn Ly Ml Nk Pk Uv) Mn(Ad Ba cT dA Ib In Iq Jo Jt Kr Ky Ly Pd Rj Uv) Iq(Ad aE Ha Kc Kj Lh Mb Nd Of Pd Po Rj Ug Uk) Qv(Cw cZ gW Jq Jt Nd Nf Nm Pd Po Sr) Bn(aF aS aW bN dA Dd Iu Oy Rb) Il(Ad Ch Et Hf Ib Mb Nd Qt Uv) Us(aF aY bN eF Hf In Jo Nu) Ha(cI dA Gl Ny Ra Ub Uh) Oy(aY Cx dA Ke Kp Kr Sr) Uh(Ad Ib Nf Rj Ue Vp) bN(Ad Jo Ke Nm Vo) cP(Ad Ib Pg Tz) Gl(cS Mb Ue) Ny(Pd Ub Um) Cx(Jo Jt) Sr(aE Rg) Jq(aA Jt) Ke(aE cS) aY(bW cR) BbaW CsFp MbRb IugW JoRh RjaF UvdA} eF{Us(aA aS aW cP cT Iv Jn Kf Mr Nt Ph Rh Sr Ub Un) Kk(aM Ct Gp Hr Ij Nf Om Or Pb Po Uk Um Uv Tj) aE(bS Il Jo Jv Ld Ly Mb Nd Nk Oy Rb) Uc(Ax Bo bV cI cT dA Ir Ld Mu Ny) Kc(Aj Ch Co Cq Ib In Kg Kj Nl Uh) Jo(bV cI cP Cs Iv Ks Qd Rg Sr) Oy(bV cP cT dA Mb Nx Qd Qv Rf) Ub(Af BN cP cR Kj Rj Um) Rf(aW Ii Kr Mn Nk Pd Sr) In(aS aW cI Kp Qv) Qd(bN Ch Ha Iu Qn) Sr(Bn bV Ii Il) Kp(Cq Ij Mn Ue) cI(Gp Lv Nd St) Mb(dA Nx Rb) Qv(bN Ib Nd) aY(Ld Rj Ue) Af(Jy St) Rh(Aj Ue) Nw(Bn Uh) bV(Mn Rj) cP(Ib Kj) AoSt IiNx IlLd} dA{Il(bR bX cS cT Fb Ip Ir Jn Kc Kf Ly Qd Rb Rj Sr Ub Un Us) Qv(As bQ bW CO dG gL In Jo Mr Or Pf Um Uv Tj) cP(bX Jo Kc Kp Ly Nd Ne Nf Nw Nx Oy Rf Rj St Um) Us(Ar bI bX Cu Fr Gp Hc Kc Kz Me Nt Ou Ph Ub) Iq(aJ Dc gL Ih Ir Nw Nx Qd) Iv(bJ cR Ha Hr Ly Pb Um) Nk(cT Jn Kc Nc Nd Nx) Kp(cR Ib Jo Mn Nd Um) aV(aM cV In Kz Qd) bR(cT Ly Nf Nx Ub) Mb(bI Nf Rb Ub) cR(Ly Rb Rj Ub) cS(bN Ha Hf Rj) cT(Hw Jo Mn Of) Kf(Dd Jo Uc) Nx(Af cA Ii) Jn(Ha Nd) Nw(Ii Sr) Oy(Kc Kk) CsKr LybN UbUm RjbU} Qv{Kp(Ad Af bJ BN De Fp Hv Hw Iq Jn Js Jt Kg Kj Mr Nk Of Pb Ul) Iq(aJ bV cN cR cT Cu Ez Fr Ir Is Jn Jy Qy Ua Ub) Af(Bc cN Im Mw Ph Qy Rb St Ut) Nx(aC As bN Hw Il Kj Mn Sr Uc) cZ(Bc bV Jn Kk Oh Ph St Un) Lv(Ha Nd Nf Qy Rj Ub Uc) bV(bE Bn Hf Nk Qy Rj) cT(aY bJ cV Hw Kc Oy) In(aW Ih Jv Qt Qy) aY(Jy Ld Ly Nk) Ba(Kc Oy) Ez(Jo Ub) Mi(bJ Rh) Mu(Ao Dk) Qy(Ch Hu) aA(Dd Ha) aC(dI Rh) cN(Bn Nj) CxgL FrSr LyUb IlJy IvUs JocS KccP KeUn KkgW} cP{Oy(cR Jq Kc Kk Kp Lw Lx Mt Mw No Nq Nv Nw Pg) Jy(As cR De dI Ha Hq Hw Ib Kj Nf Pd Ub

Figure 19 Continued

Uc) dI(cI Jn Kz Lv Ly Nf Nw Qd Ub Us) Mu(aF Al aY Ch cI Cp Dk Rj Uc) Qd(cR Fp Ha Il In Ly Nk Us) Lv(aE Bn Ch Cq Ly Rj Uc) Rf(bN cR Ly Nd Nk Rb Ub) Nw(Ad aY Cx Il Mn Nd Uh) Jo(Cu Dc Jn Kp Mt Rh) Dc(Ad aM Cq) No(Ii In Pg) Nx(Kr Of Sr) bE(cR dD In) Lx(Nk Po) Hw(cT Kk) St(aY In) Kc(bN cR) dN(aM bN) BnCv UbRb SrJp KkPg aAcR} Af{Kp(bE bN Cv Fw Il Iq Kg Mb Of Qt Uc Ue Ug Ul Tj) Kc(aS Ba bI bV Cv Ez Fb Kk Kr Lu Nw Ph) Nw(aA aF Al aS bV Il In Nd Nj) Nx(aJ cN Il Lv Oy Qd Ue) cT(Ar bJ gL Ld Rj Ub Us) Jy(aA Ar Jn Kk Ou Us) Mu(aA cR Ly Nk Um) Qd(Gp Hr Ly Nf Rb) Lx(Lz Pe Pf Rg) Rf(aJ bN Jn Ly) Ur(cR dI Om St) Kf(Rj Uk Us) gL(Jn Ly Mb) Sr(Ha Rj) St(Il Us) bV(Gp Kr) BaKj JjPh OnUs aAbS} In{Iq(aJ Ax aY Dc Id Is Oa Sr) Nx(aA Ao aY cT Ii Jj Jo Nm) Kp(aY Cq Ib Mw Nf Qt Ub) bN(aY bV cR Qd Rf Ub Un) Rb(aY cR Ir Mb Ph Ub) cS(Ip Jn Kc Kk Nk Vv) Il(Bc bI Dp Rm Sr) Us(Fa Ih Ir Jm Lx) Nk(Kc Kf Ph Ue) Iv(aA cI gL) Kf(Ao Jt Nj) Bc(Nd Ph) Ly(aY bV) Ub(Kc Rh) Ue(cR Mr) bX(cT Ou) CucI NdbV IpaY SrJn QtaS RfbI aWcT} Sr{Qd(Ar aY bN cT gL Jn Jo Kk Kp Nx Rb Rf) Jp(Ar bE cT Iq Kj Nk Ub Ur Us) Kp(Ba bJ Gp Lx Mw Nx Ug Ul) Kc(aJ bI bO Fb On Qt Ur) cT(aE aJ Fr Kz Nk St) Nx(aY dM gL Mb Ug) bV(Bc bX Ic Oh On) Ur(Iv Jn Kf Rf) gL(Ar Ax aY Il) Fr(cI dM Us) Nw(aA aE Us) Jn(aJ Rf) Kk(Og Oh) LxaA MtRf IvJo StdM UpUs OyaY} Rf{cT(Ao Bb Gl Hw Ih Ii Mc Mn Uh) aY(aS bS bX Ip Jo Mc Ub Uk) Bn(aS bN Iq Jo Nm Qy Ra) Ii(Ba bN gL Hc Iu Mw Ra) Ha(bN Im Ly Nx Rb Ub) gW(aA Ba bI Jy Mf) Iq(aA Ba Im) Ra(Gp Nd Nk) Kp(Ny Oy Uc) Nm(bI Rj) Mn(Lv Mi) Ny(aA Qy) AoOm LybI MbRb NkJo OyaS bNcR} Kc{bN(bI dN Jv Kg Kr Nl Rb) Jy(Ao Iq Jo Nj Uc Us) Fp(cR cS Fr Nx Ph) Ub(bJ Il Iq Mr Rb) Us(cR Mr Nx Rb Up) Nk(aY Iv Jo Oy) cT(Hw Nj Oy Uh) Ii(cR Nw St) Iq(aA Gp Jn) Iv(Il Kr Uc) Fb(Bb Uh) Lv(Il Nj) Mr(Nj Oy) cR(Iu Kr) AogL JocS OyaY} Nx{Ii(aJ bE bN gL Gp Jp Jr Lj Lv Nj) Ub(bN Gp Ha Il Jo Oy Pg) Mb(aY bN Ha Jo Kr) Nk(Iv Nm Oy Ue) Qd(Il Jo Nm Pf) Qy(Oy Us) Jj(Lv Us) Jo(Kp Vv) aA(Nm Ny) cT(Hw Oy) AogL BnJy FbMc IlbE KpLh} Rb{Mb(aA bE bV dM Iv Jn Jo Kr Nj) Us(aA cN dM Jn Kf Lv Ph Qd Un) Ub(aY bJ bV cT Il Lv Rh) Il(aA dI Qd) Jo(bV cS Ph) Bn(aJ Qd) Nw(Ao aY) aA(bN gW) cT(Ib Of) GpQd UeIv KrbV aYcR} cT{Hw(aY bJ bX cR cS Nk Qd) Oy(bJ bX Iv Jh Qy Ra) Jo(aY Iq Nk Ra) St(Lh Ny Uh) Nw(Iq Mc Pg) Ha(Jy Lx) Ub(Ly Nk) ArFp LvUc IqQd RaUs RiRj PgcS bNdN bXdI} Ii{Nw(Cq Dk Ib Jd Um Vp Tj) St(Dd Fr Lz Mi Nl Ou) Qd(Gp Qy Ra Rh) Jn(Dc Jy Kk) Cu(bN Ki) Lv(Kk On) Rh(aA Un) DcIq LxUl MuKp NkOn JyOh aAbR} Jo{Iv(Ar bJ bV Cu gL Hc Kf Kk Ph Rh) Kf(Ao Nj Uh) Rh(Bc bI Qy) Ok(Lv Mb Mm) Fp(Ax Cs) Ly(bV cS) Ph(bJ cR) BaIq BnKp MrbV HccS IpOu} Us{Up(Fr gL Hc Ir Is Kk Nw Ph Un) Ri(Cu Ih Ir Jp Qe) aY(Hf Is St) Cu(Il Uh) Lv(cI Ph) Mr(aA bV) BcMc LybV NkUb IqSt JvKf QnNw aAcM} Kp{Oy(aA Ad Cq Cw Ef Ib Ij Nf Nq Ud Ul) Fp(Ar Ph Ur) Mc(bN Ha Lz) Uc(bX Jy) Lh(Fr Mw) gW(bN Gp) AoNw CxJy LyKr MndI IbbJ} Nk{Ub(aA aY bV cS Gp Ih Kk Lx Ly Mc Ph Rj Ue) aA(bN Ir Ly Mb) Ao(gL Nw St) Mc(Jp Ph) Ue(cR Iv) St(aY Qn) LybV} Il{Lv(aE aY bN cS Qy Rh Ub) Qd(Bn cR Iu) Jy(cR Mb Ub) Ao(Cu Mu) Mc(Cu Fb) Iv(bE St) Nw(Bn Ke) DcIq MtaY MuHf KfdI RhbE} Fp{Cs(aJ Ba bE Fb gL Jy Lv Mb Qd Qt Qy Ub) Kk(aA aE Ar Fr Ou Ph) Ax(bV Ph Ug) PhbV} aY{St(Al Ao Mn Or) bN(aA gL On) Lx(Nd Po) Ly(Mb Nw) Mu(Bn Mb) Kk(Ko Oy) CxaA MtOy NdNw IqgL} Iq{gL(dC Mb Mc Ub) St(aS Nj Ub) Bn(Jy Nw) Mu(cI cR) BoCh IcaA JnKr KkdI NwaS} aA{Bn(bX dH Jy Rh) Cx(Ib Nd Rj) Iv(Dd Oy) FbPg GpNy NqdI JnPf bNbX} Mc{Fb(Ba Ch Jn Qt St) Kr(Ou Ph) aS(gL St) NjPh UbUn QdbI} Ao{Nw(cR Ke Qy Rj Uh) Kf(Ha Ib) CuKr MuVv IvgL StcR} Kk{Jd(cN gL) Pg(cS dI) MnKy MpOy UbgW NydI} Ly{Gp(bV Qd Ub) Lv(aE cI) bV(Kr Pg)} Oy{Kf(Et Nj Ra) BacS BoHc MbgL JhRh} Jy{Bn(aF aS bV) Pg(Ou Ph) UbRh} cR{Ub(bN Jj Ki) MuaF bNcN} Ha{WmLx MuPh QdbN NwUh} Nj{St(Bn Kr) IbPh} Mu{BnMr JkPh} Rh{UbbX gLgW} Rj{QdRi RabV} CsLvKr MnJndI NdQnNw HwOwOu IvPggL StNyaS

Constrained panels with 3 analytes, where 1.0E-7 >= 'AUC p-value' > 1.0E-8. Contains 4,676 panels of 6,910,825 total panels evaluated. :
Nb{Ue(Bg Ch Dk gL Hv Hx Ic Jd Je Ki Mk Ml Mn Ms Mt Mw My Nv Ny Of Og Qx Um) Kr(aA aX Bb bF Bg Cq Cs dA Dk dM Hf Je Ld Ly Me Mr Ms Mw My Nk Oh St Vp) bV(Ad As bJ Cq Cw Gp Ij Iq Js Mb Nk Nm Of Po Qa Ql Uv Vp Tj) cT(aH aL Bg Cp cV cZ gW Jd Je Jv Mr Mw Nm Om Pb Po Qt Qx Tz) Ub(aX bE cI Ct Hw Ir Jd Jj Jn Kc Ki Kz Ml Mn Mz Rf) Rb(aJ bE cI Ct cZ Hq Hr Hw Ii Jj Jk Mn Ms Tz Ug) Jv(aM bE bJ Gp Ij Iq Mj Mr Mw Nk Ny Pb Qx Ul Um) aA(Ad As Cp Ct Cw dF dG Ke Kj Ql Qn Rj Ut Uv Vp) Ao(bN Fn Jn Kg Kq Kz Ml Ph Pi Qy Ra Ud Up) Co(bJ bN Gp Ii Js Mb Nx Qv Rg Rj Ul Vp) Ch(As Ba cZ Fb Fw Hr Hv Hw Me Pi Uk) Gp(Bb Bg Bn dA dI Dk Hq Iu Jt Mw Tz) Iq(Je Kg Kk Kp Ky Oa Qt Qy Rg Rj Sr) Kp(Af As bN Il Ko Mr Nf Ni Pb Vp) cP(Af aX Bn bQ Iu Jh Kc Mk Om Po) Ba(bQ Hc Hu Iz Lh Mw My Qu Qy) Kg(aX Kc Ly Ms Og Rh Ul Vp Tj) Ky(Js Jt Mj Mn Mr Pb Po Qx Ut) Rj(bE dM Hq Ki Mk Mn Mw Qx Tz) Uk(bE cZ Jd Je Mn Mw My Nk Tz) bN(AJ As gW Hq Jd Kk Mc Ur) Rf(Io Kj Ly Mc Pg Po Sr Ut) cN(bJ Cp Hq Mn Of Om Pd Uv) Tj(dI dM Kk Mc Ng Qd Qv) St(aF De gW Ij Il Pg Ut) Nw(aF Cq dA Dd Ke Ut Vp) gL(Bb bQ Cw dH Hw In Nf) As(aX Mb Mk Mn Nx Ur) Jd(bJ Kk Mb Nc Ne Ur) Sr(Ad cS Il Js Kj Of) Qv(bJ bQ Kz Mw Po Qx) dA(bX cF Fn Kc Kz Um) Ar(Af Bn Fp Ii Ny) Kj(Ez Kq Mi Ph Ua) Nx(bQ Ct Dk Qx Vp) Ul(dI Hq Hu Ny Qy) aJ(Ad Iu Jt Nf Nq) Aj(aY Kc Ly Nf) Bn(aW Mi Mn Qz) Ii(Bc cZ eF Ph) aX(Ad Cw Hr Uv) bA(aE Kz Mk Na) cI(cR De Nf Ow) Ly(Ct Jc Tz) Uc(Ih Ir Kn) Kf(Ad Cq Ni) Kk(Je Js Nf) Kq(Of Po Ut) Ur(cZ Of Uh) Af(Nc Qz) Cu(Cq Jt) Dd(Dc dM) Fp(Ax Ph) Ij(Ou Qy) Io(Fb Ug) Iu(Qx Um) Jy(Dk Hq) Kc(Pe Ug) aY(cZ Mk) gW(Lv Rh) AdMy BgNm BoIb CtNe CvQn CwOg DeQz DieF MbdM MucE NcVp TzJn HubJ IlKz JeJt OebQ OucZ UmdI} cQ{Us(aP Ar Ax aY Ba Bc bE Bo cH cN Cp dN Hf Ip Ir Jj Kd Kn Lv Lw Mp Mw Om On Ph Qe Qy Rf Um) Qw(Af Ar aS aW Ax Ba bE bP bX cI Cp Gp Hc Im Ip Is Jl Jp Kd Mb My Ou Qa Qb Rb Ua) Mb(An aY Bc bI cP Cu Dc dN Fr gL Jl Jq Mw Oh Om On Qd Sr Ub) Io(aS aY Bc dA Dg Et Ez Im Ji Jy Ld Lx Ly Mt Mu Nv Rb Rj Ut) In(aA Ax aY bV bX Cs Cu dM Ir Jm Jn Kn Nd Qe Qt Rb Rm Sr) Kp(Af Ct gW Ha Hv Hw Ij Il Iq Lh Ly Me Nf Nm Uc Ug Ul Uv) bN(aE An aY bE bV CP cR cT dA Dc Fb gL Lv Om Ub) Ub(Ar bE Bo Fb Il Ki Ld Ly Oh Ph Rf Ul Ur) Ue(Bo bX cR Cu eF Fb Jn Kf Mr Nt Nx Qd Rb) Jo(Ax Bc Dc eF Fb Ih Ir Jn Kn Mr Nt Nw Un) Bn(aJ Fb gL Is Ji Ke Lv Mt Qd Rb Ur Ut) Mu(Ao Ar aW bX cI gW Jk Kj Kk Nd Nf Nq) Il(bE cS dA Fr Ih Ir Jq Kf Lx Nt Om Rb) Rj(aJ cP cS cT dM Ir Iv Kf Ld Nw Nx Ur) Kq(bJ De Fw Iq Jd Kg Nm Of Pd Po Uk) Un(As Ch Cx Gp Ha Ib Ii Mc Nf Pg Um) Af(Cp Cu Fa Ih Jp Ld Lv Mw Qe Rb) Sr(Cq Dd Iq Jt Kj Kr Nm Of Rf Ul) St(aA cI cT Dd dM eF Fb Kk Nl Rb) Nx(Aj bE cP Cx Gp Hw Jj Kj Qd Uk) Iv(Aj aS aY bE cS Jj Nf Um Ur) Kf(Ad Cq Ha Ii Jt Kj Kr Nf Ul) Oy(Bc dA Dc eF Fb Ir Jn Jy Ph) Qv(Ar Ba cI Cx Ez gW Im Iq) aA(aF bJ bQ cI dG Hw Kj Me) Rb(aJ aP aY Gp Jj Ug Ur) Qd(cA Cq Fw Hf Mc Pg Qn) Kk(aE As Hw Kg Kj Rf Tj) cT(aE Ib Iq Nd Nf Nw Of) dA(bS bU cP Uk Ul Ur Uv) aJ(bS cV Cx dG Nd Rf) dM(bX cV Gp Ly Nd Nk) Uc(Fr Ih Ir Is On) Iq(aP Ir Jn No On) Kj(eF Fb Ip Qy Rf) Nk(aE cP Ih Jn) Ii(Dc Ji Oh On) Um(Bc cS Ir Ph) bX(aY Cx gL Ip) Jy(Ar aS Ch) Kr(bV Jn Kn) Rf(Ba Im Ur) cI(eF Gp Nw) cR(aY cP Ld) cS(cV Im Ip) Aj(Cu Fb) Bo(Ao Bg) Ly(Ih Lv) Nd(bV On) Nf(bV Ir) Kc(Ba gL) Ug(eF Mr) Ur(aY eF) CuNm CxFb HwPh IrIu NwaW NyOh OubE} Io{Ub(aJ aP bN Dg dM gL In Is Jg Jn Jy Ma Nw Oh Ok On Ou Ph Qd Qv St Uf Ur) dA(Ba bN bV bX eF Et Fb fP Fr Hf Ir Jg Nf Nk Nw Oh Ok Ou Ph Qd Rj Ur) Qv(Ap aX bX Dg dI Et Ic Im Ir Jg Jy Mw Nk Nw Oh Ok Rb Ua Ur Ut) Kc(aE Ba bI bV Fb Fr gL Hr Im Kk Lv Mw My Nl Qt St Ur) Kq(aM Cp Hr In Jt Ke Kg Me Nd Nm Pb Uk Ul Ur Ut Vp) Kp(aJ bE Cu Fb Id Im Iv Jn Jr Jt Na Nw Pe Qd Ra) Ba(aE aW Hw In Jn Jo Kk Mc Mn Nf Qd Rf Us Uu) Qw(aP bX cN Cu Ef Gp Hc Ih Jy My Nt On Qy Ss) Jn(aE aJ cI cS Dd gL Ib Ph Rj Ue Ug Ur) bN(Ar cR cS dM eF Jg Jp Kf Nw On Rb Rf) Kk(Ao De Fr gL Ib Iq Nd Og Pb Ul Tj) aY(aJ cP Dc eF Hf In Ip Is Jp Qd Ur) Cu(aE aW Bn Ii In Iq Kj Nf Rb Uc) Kf(Ad Cq Cw Iq Nm Of Pd Rj Um Us) Ph(Af cP Gp Hf Il Iv Ly Nk Nx Oy) eF(aS Ax Cs Ih Mb Rf St Ue Ur Us) bV(bJ cP cT Gp Jy Lv Nf Qy Rj) Rb(cS Fr gL Iv Ly Mw Qd St) gL(aW Bn cP Mb Nx Ou Ra) Ly(aP cN cR cS Rf Ur) Il(Ad Dg Ez Rf Un Ut) Us(aA Ar Ez Fr Qd Rf) Sr(Ib Iq Me Qd Rj) St(Af cT Iq Nk Qn) Nx(aW In Kj Ug Ur)

Figure 19 Continued cl(Dg Fr Gp Jg Lv) cP(Ax Bc Ez Ji Un) Ar(aS Ic Iv Oy) aE(Fr Jg Kl Lv) aJ(aS cT dK Rh) Bn(Fr Jy Ur) Iv(bX Gp Rf) Nw(aS cT Uh) dM(Gp Mb
Rj) Ax(Fp In) Fb(Mc Ni) Ue(cT Nk) Oy(Bg Qy) EzJo FrUc NiIc IhbX IncU QdRj JyOu bEcT} Kq{Ni(Aj Cu Dc Hr Hv Hx Id Ir Iv Jn Jr Kg Kp Kz Ml Mz Pe Pi Pk Po Qa Qx Ud Up) Iq(Aj As bJ cC cP Cq cR Dd De Dg Fn Gl Gp Ij Ji Jt Kg Nf Om Uh Um Uv) Qv(aC bJ bN cI Cq De Ib Ij Ji Kg Kj Kr Lh Of Om Pe Ut Uv Vp) Ii(Aj aM Bb bW cI cV De Hr Jo Kp Kz Mr Of Om Pz Rf Us Vp) Mn(aA bJ Cw De dI Ij Kc Ke Kj Kz Ld Lh Nd Nm Rf Um Vt) Ny(Ad AS bJ cT Dd Ib Jo Kj Nf Om Rf Rh Ut Vp) cP(bN Ch Co Cq Ha Jd Ke Kj Kr Lh Nf Nm Of Rj) Ao(aE Ct dG dL Is Kg Kn Lw Nr Ql Qx Rg Uk) Gl(Ad De Gp Ib Jo Kj Kr Nf Om Pd Rj Uv) Sr(Ad aW bN Ha Ib Jo Mb Nf Om Pd Qz Rf) Il(bE cE cI Cq De Kc Kj Kk Nf Ue Vp) Uh(bN Cq Fw Hr Jo Kc Mb Na Pd Ul Uv) Oy(cI dK Hc Kc Kk My Nf Rb Rj Ub Us) aY(bJ Dd De dG Ha Ij Jo Jt Nf Pg Uv) Bn(aA Ad bI Jo Ke Kp Ld Ly Pd Pg) bN(cI dA Ib Iu Kc Kr Pg Rj Tz Ub) Af(aA cT Cx De Gp It Kg Kk Qx) Qw(aS Bb Et Kp Rb Ue Us Ut) Nr(Ba bJ Mb Rg Rj) Rb(Ad Jo Kj Kr Nm) Ke(aW cT Kc Ue Um) Us(bI cI Kz Nf Ub) Ra(As De Ib Kj) Dd(bA Cx Dg) Ue(Ha Nk Pg) Jq(aW cR Dl) Dg(Ha Nf) Tz(gW Ub) Kr(Cs Uu) cI(De Ij) BbcT CoQn CxUb NfUu NjKc UcVp JkdA JoKp UvgW} Qv{Kp(aC Cp Cu Fw Gp gW Hr Hx Id Ii Il Ir Jr Lh Ly Me Mj Ml Mx Na Nm Pi Pk Qa Qx Ud Ue Uk Uv Vp Tj) Af(Ar aY Bg cR cS Cv cZ Dc Ef Et Fb Ir Jl Jn Kk Ld Lx Mi Nv Ok) bA(aM As aX Cw Dd Hx Id Ij Jn Jr Js Kg Mr Pi Pk Ud Ul Uv Vp) Bn(aJ cR cZ dM Fr Kf Kk Om Qd Qy Rb St Un) Ub(aY Bc bJ cS cT cZ dM Fb Jy Ki Qy Rf Rh) Iq(aC Ba cZ Ih Im Mw Nw Nx Ph Qd St) Rf(aX cN cP Ha Kc Nj Nk Qy Ra Sr Us) cT(cI Cq Ib Jo Jv Ly Nf Ny Rj Us) aY(aC Ba bJ cZ Hf Ic Kz Me Rj) Lv(aW bJ Dd Fb Fn Me Or Vp) Qy(aX cZ De Jo Jv Ki Ph Rh) Oy(Cu Ef Ez Fr Hc Iv Jy Ph) Kk(bN Dd De Ha Ic Nd Nk) Nw(cZ dA Ii Ke Ny Sr Uh) Nx(aX Ch Cx Ib Nf Ny Of) In(aC aX bE cN Ez Jy) Us(Ez Fr Jy Kf Qd Rb) aA(As bE cI Mb Nd Rj) bV(bJ bN Kc Kr Me Nf) cZ(cI cP Ih Ir Nk Qd) Iv(aC bJ Il Jo Nf) Nk(aC bJ dM Qd) Rb(aJ Mb Nc Qd) Qw(cI Ph St Up) eF(aW Mb Rj St) gL(aF cI Jv Kc) Sr(aJ Ba Ha) Jy(aF cP Nd) dA(Ct Gp Ur) Ez(Jv Ng) Mu(bF Kc) Ii(Cu Un) Jo(Fr Jn) Kf(Dd Ha) AxFp BaIb FbKc NfQd NjdI KybN aWbE aXbJ} dA{Us(aI aS aU aW aY Ba Bc bV cF dJ Ez Is Kd Kf Kn Ld Lx Mw Oh Qd Qt Un Up Ut) Il(cB cP Fr Hf Kk Lv Mb Mr Mu Nk Nt Nw Om Ph Qt Ur Ut) Nx(bS bU cF Ch cK Cq Ib Lz Mn Of Pb Pd Sr Uc Uk Um) bN(bR bX cF cR cT Fb fP Kf Kk Mb Nd Nk Rb Rf Rj Ub) Iq(bV bX cA cF cP cR cT Fr Gp Jn Mb Mu Nk St Ub) Kp(As bJ Bn bS cA Cq dG In Kr Lz Pb Rj Uc Ul) Iv(As Ba Bn Cq Kc Me Mr Of Pd Rj Ue Ul Tj) Rb(bR cF Db Gp Jj Kc Ne Nk Oy Rj Uk) Ly(bS bU cA cF Gp Jn Nd Ne Oy Qd) Jn(Af Ib Ii Jo Mb Oy Sr Tz Uc) cS(bS bW cP In Oy Uk Ul Um Uv) Ub(bJ bS cA cF cP Ha Oy Ul) Nd(Cu eF Jp Lx Nf Nw Rf) Ha(cT Cu Kc Lx Qd Rf) aV(aW Ba bE Kk Qz Ur) Nk(bV Nf Ou Ph Rf) Kf(Bn Cq Ib In Uv) Oy(Cu Ir Ou Qt Rf) cP(aM Gp No Rh) cT(cA Lz Mb Um) eF(Ib Kc Mn Uv) Ic(bS Kj Uv) Ii(Fr On Qd) Jo(Kc Ou Ph) Rj(aS bR Mb) bA(Mk Or Uk) Bn(Jy Rf) Mn(Cu Ky) Qw(In Jj) cR(Nf Ue) AfSt AoNw CsFp FrUc GpRa MbbX IbPh QdSr OwOu aWcB bIbR} Ni{Lv(bE Fn Fw Ha Iv Jp Kr Kz Lj Pi Pk Ra Rb Ud Up Vp) Kp(bE dL Fn Jn Kd Kf Kn Md Mq Mz Nr Or Pd Qa Up) Kf(Dc Hx Kd Kg Kn Lh Md Ny Pe Qa Ra Vt Tj) Kr(aJ Ba cN dM Fr Is Jp Mw Nw Oa Qa Qd) Aj(Dc Hc Mu Mw My Qd Qe Qt Qy Ut) Dc(Cq Cw Hr Ij Js Jt Mr Of Pb) Ib(aS Bo Cu Mu Mz Ny On Qd Ut) Ji(Ij Il Iv Jj Jo Lh Mr Pb Pd) Lw(Ad aM Cq Cw Dd Or Uc Ul) Cu(Jt Mj Mr Of Pb Ul Vp) Mu(aW Bg bQ Ch Co De Kj) Is(Hw Ii Jj Kz Oy Qx Vp) Iv(Fr Jo Jp Mw Nf On Oy) Uc(Bo Ef Jg Jy No Qe) Qd(Il Kj Kz Nx Ul Ur) Qh(aM Mr Of Qx Vp Tj) Un(As Ii Jo Kj Me Nf) Jp(Ha Jj Nk Oy Uk) Kd(Cq Cs Js Mr Vp) Jo(Bg Cp Ef Ua) Jy(gW Nd Nf Oy) Kk(aC gL Mk Ur) Ky(aZ cC Nd Qz) Kz(Im Lx Mp Sr) On(Il Jj Ng Ny) As(Cp Jq Mi) Bo(Bg Co Iu) Hw(Ez Nx Ua) Kj(My Nw Ua) Oy(Aw Cp Fr) Ao(Nq Qy) Ir(Iq Jj) Rb(aA Sr) Kg(Ph Sr) Nw(Qx Ul) Nx(Of Og) Vp(Mt Ny) bE(Nl Ph) bI(cC Us) AdQa BgNq CsOr DdNo FrIl HaPe NgQt IhUr InaA StaX QyOf JjJn JrUl OugL} cP{Jy(Ad Al aY bF Bg bN Co Cq gW Iu Jd Je Jk Jo Kc Kp Md Nd Of Pg Rf Rj Ue Uv Vp) Jo(aM aO Ar bZ cS Dg Fr Ip Kc Kf Kk Kn Lx Ly Mb Nk Nt Nw Oh Ph Qw) Us(bE cR Cu Dc Jq Kc Kd Kz Lw Lx Mr Mt Mu No Nt Nw Rb Rh Ri St Un) Nw(aF Al bA bN Ch Cq cR De gW Ha Nf Pd Qw Rj Uc) Mu(Bg Cq dI gW Ha Hq Ib Iu Nd Nf Of Om) Lv(aY bE bN gW Ib Il Iq Nd Rh Ub Ue) Qd(Cq Gp gW Ib Iq Iu Me Nf Rb Rj Uc) Qw(aJ bV Dc Kk Ky Lw Mt No Nx St Un) Oy(aA Bo Cu Dc Fr Iv Kf Om Sr Un Ut) Nx(bE Ch Cq Ib Kj Mb Ms Nf Ub Ue) No(aY cR dI Il Ly Mb Nd Nk) bA(cI Cw De Mb Nd Nf Pb Uc) St(Al gW Ha Il Nk Ub) Ly(bE Jj Mb Ne Ub) Sr(aJ Fr gL Kp Un) Rj(dI Kc Kk Kp Lw) aA(BN Cx Nd Rh) Lx(Cq Ha Iq Nd) cR(cI Kj Ld Ub) dI(Af cT Il Iq) Dc(Dd Nf Uc) Lw(Af Iq Nm) Nk(bE Kc Ue) Pg(gL Hq Kc) Bn(Kd Mt) Fp(Ax Cs) Kr(Kk Kp) Rh(bE Ub) eF(Aj Ue) ChbE CqMt GpKc MbRb MwIb HwJn IqaJ RfcZ} Qw{Il(bE cN cR cS cT Cu Dc dI dN Iv Mt Nw Om Qy St Un) Ub(Ba bI Bo Ef Jh Kd Kn Mt Mu Nw Om On Ou Qy St) aY(aS bJ Fb Jo Ke Kz Mw Nj Uk Un Ur Ut Vv) Jy(Ao aS Ba bN cT eF Jn Kc Kk Mb Nx) cT(bE Bn Ch cI Iq Lw Mu Nf Qd Uc) Jo(Ar aS Ba bI cR Cu Kn Nt Sr) In(eF Fr Ih Mr Mw My Rf Un) Qt(Af Jj Kc Ki Kj Kz Mc Ng) Ba(cS Ib Iv Kc Kj Of Us) Kc(bI Fb Gp Jn Lv Nx) Us(dM Fr Nt Ph Qd Rf) aJ(bI dH Fp Rb Rh Ri) cR(bN Hc Hf Ld Ou Rb) eF(Ax Im Ky Nw Oy Rj) Cu(cI Iu Nj Uh) Ha(Kf Lx Mt Sr) Mu(bN Iq Kp Nu) Mw(Af Ki Kj Kz) Iv(Jj Ue Ug Ur) Jn(Iq Js Kr Nj) Rh(dM Fb Kg Ky) Bn(Fr Nw Un) Ki(bV cS Mp) Nx(Ao Jj Kr) bN(bE cS Ph) gL(cI Cx gW) Af(Ez Jp) Fb(Mb Ph) Fr(Oy Ri) Rb(Kf Ly) Qd(aF aS) Kk(Hw Qy) Rf(Lu Vp) CsKr CxcN GpcI LwKp LxPe McJp NjSt NkdM SrKj KeNw KfOy KzbV UmcS UhUn} Af{Kp(aM As Ba cV Cw Cx Dd Hr Hv Hw Id Ij Ir Jn Js Jt Me Mj Ml Mr Na Nm Nw Pi Pk Qx Ra St Ud Up Uv) Nx(Aj aY bE bN Ha Hr Ii Kg Kr Ms Nd Og Qt Uk) Jy(aV aY Ba cK Hc Iq Jp Ld Ly Ph Rb Ul) Mu(aE bJ bR Gp Ii Jk Nd Nw Oy Rf Uv) Ur(aY Bc cN cT Cu Fr Jn Kf Kk Rb Un) Rf(Bc bI Hc Im Jp Om Ou Qt Rj Ub) Fr(Il In Jo Ly Mb Rb Rj St Ub) cT(aW aY cI cR Kr Nk Nw Ug Uk) Kc(aE aJ Jp Lw On Qd Rb) gL(aM An aS bS Jj Jo Nd) Cu(cI dM Jo Kj Ug) Rb(Jp Lv Qt St Ub) Qd(bN Iq Iu Kr Rj) Nw(bI Lz Mn Qy Ub) Us(Ba Ez Jn Lx Ut) Kk(cX Gp Lv Ug) On(aY Ii Uc Ug) Ba(Aj Jo Ug) St(aS cN Iv) Kf(Dd Kj Um) Om(dM Il Kj) Un(In Jj Ld) aA(aM dH) aJ(Gp Rh) bV(Iv Qy) eF(aE Ph) BcUg IbNv JhOy UtdM} bA{Jy(Ch Ct Dd dG Fw Il Jl Jt Ma Mb Of Pa Pb Pg Po Tz Ue Uv) Mu(Ad Al Bg Ch Ct Cw Dk Iu Jd Ke Lh Nf Nv Of Om Tz Us) Iv(Jr Kg Mq Na Nm Pd Qx Um Uv Vp) Kk(bJ BN Il Jo Jv Ke Kr Oy Rj) aA(bQ cV Cx dG Ha Ib Il Nd Rj Us) Qd(Cw Iu Jk Mn Nf Po Qh Rj Tz) Rf(As Mj Ne Nf Pb Pd Pi Ub Uc) St(Al De Il Iq Jv Nk Qh Uf) Qy(aE Bg Co De Jk Ue) Nw(Al bQ cG Jk Pd Po) Ub(cI De dF Kc Mb) Kp(Ib Jt Kj Kr Rj) gL(Hw Iq Mc Mn Uu) Cq(Ih Ld Ny Ph) Dc(Ad Ha Iq Uc) Ra(Hr Kg Vp Tj) Uv(cR Ed Nx Rb) Jq(Cw Dd Ha) Js(Ih Jr Kd) Ld(Il Lh Pb) Ug(bQ Nj Nk) Bn(aW Nx) Cu(Jo Uc) Qz(Nr Pf) Ju(cI dF) Kc(Fw Nl) Kg(cF Rh) Kr(Iq Ph) Lh(eF Rh) Uh(Mj Vp) aY(bQ dL) cN(dG dH) CtEd CxJv DdNo NtUc MnPh NfNy IiKd JoKf KzPf NxPb OwaW VpbX aFcR} eF{Mb(aS aW bV Ch Il In Jo Jy Kp Ly Mu Nj Nk Ra) Rf(aS bN gW Il Jo Nd Ne Nr Po Ue Ug) Qd(Aj Ao cI Cx Ib Kr Nd Pg Rj Ue) Jo(Ar aS Fp Jn Ld Lj Mr Rb Ub) Oy(Ar Ax Bo Iv Jn Ld Ou Rg Rh) Kk(bE Fn Iq Mj Mr Nr Qx Ug) Aj(Iv Jn Kp Nk Nx Ph Rj) Uc(Ar Cp Fr gL Is Kn Lx) Kj(aS aY Kp Nx Ph Sr Un) Us(Ax Ih In Jj Nk Rb Rj) Ib(aY bV cT Nx Ph Sr) Il(cI Lv Mt No Rh) Kc(aS Gp Iq Of Rh) aE(Im Mu Nx St Wm) Mn(Ld Nw Nx St) Ub(In Kr Mc Of) Kp(Ad Cw De Of) aY(cV Nd Uk Ul) cI(Hr Jy Mu Nw) Bn(St Un Ur) In(Ax bN Rh) Ao(Jp Nx) Ue(aW Nx) Rh(aS Ug) Ph(Ch Ii) bV(Mc Pg) AxKr CsFp HaSr MucE NwaF OfcT aScV} Us{Rb(aJ aP Ar Ba bI Bo Cp cS Cu Fr Gp Im Ir Jj Jp Jy Ky Mp Mw Nt Qt Sr St) aY(cR cT Ih Jn Kc Kd Kk Kn Kp Lx Ly Mt Nw Qd) Ly(aA cT dM Fr Ir Iv Jn Lv Ph Qd Rf Un) In(Cs dM Fb Fr Kn Nt Nw Oh Ok Qd St Un) Up(aJ aP aS Bc bI Bo Ez Ih Jn Qd Rf) Ri(aJ Bc Ez gL Is Kc Mt Qh Rf Un) Lv(aS aW bI bN dM Jn Kc Kk Ra) Iq(aJ Ba cT Im Is Jn Qd Rf) Kp(gW Iv Jo Jv Jy Nx Ub) Qd(BN Il Pg Ra Sr) Iv(aA Ba cT Kc Ub) Nx(Ba cT Jy Rf Ue) Mr(aS Im Qy) Ub(cR Jn Rf) cT(dN Nt Oy) Ii(Nw St) Hf(aA bV) Jy(Il Ph) Kf(Ao Nj) bX(bV Rf) CxaA McSr JnJo KkgW} Kc{Oy(aA aS Ba bI Cu Gp Hc Hu Jn Jy Lv Mp Mu Nx Ub) Mr(Cq Gp Il Iu Kg Nd Nk Rm Uc Tj) Nj(Ba bI Cs gL Jn Mp Mu Nx Qd Rf) Gp(aY bI bN Il Iv Jo Jy Rb) Ii(Dc Jq Jy Kd Lw No Nx Oh) Bn(aA Lv Lw Mu Rf St Tj) Ha(bV Iv Jy Lx Ny Pe St) Jo(aY bJ cT Jn Nx Ph Qy) bN(aA Lu Lv Lz Mi Mu Rf) Fp(Cu Lj Mw Oa Qd) Il(cR Cu Nx Qd St) In(aY bI cT Fb Jn) Iv(Cq Iu Ub Ug Tj) Jn(Hw Ny Pg) Kr(Cs Hw Ky) Ao(Cu Mu) Lv(Mn Uc) Mc(Nk Qt) Ub(aY Jy) Iq(Rf

Figure 19 Continued

St) Rb(aY Og) Sr(Lx Om) Uh(Cu Mw) bI(Nk Pg) cR(Kg Qy) DdMu MnKy JdbV RaRf JyaF OwcT} aY{St(bJ bR Gp Nl Ny Oy Pg Ub Uc Uf)
Jo(Cu Gp Iv Jn Kf Kk Oh Rh Vv) Ly(bN Bo cR cT Ir Mu Qd Rb) Kk(Bn De Gp In Kr Mn Pg Tj) Oy(Cu Ef gL Jh Kf Lv Lx Nx) Rb(Bo cT gL
Mu Qd Rh Ue) cR(bN Jy Ld Mu Nw Qy Ub) Nx(bN Il Kr Ks Nd Uk) Kp(bN Gp Kj Kr Sr) Nw(Ha Jq Mn Or Uc) Lv(bJ Mp Nd Nf) Lx(Mn Mp
Nk Tj) Mt(bJ Or Ul) Ub(Gp In Rh) Sr(Fr Is On) cT(bE bX cV) Bn(Ny Ut) Fp(Cs Ph) No(bN Iq) Il(Mu Qd) In(Jn Rh) Kr(Kn Oh) Rf(Hc Nm)
aA(Pg Rh) CuUc DcIq GpLd MnOn NfKd IiQd IpKj JybN bEdD} Nx{bN(aA cN cS dN Il Kr Ky Lu Lv Mu Nd Oy Sr Ue) Jo(aA Ba cI Iv Kk Lv Ou Ph Qy) Ii(bV Ih Iv Kd Kp Mw Rh Ub) Oy(Ba Bo Fr Iv Kr Nm Qd Rf) Ao(Gp Jy Lv Nw Qd Rf St) Mb(bI Dd In Jy Nj Ub Uc) Kr(Bn Cs Il Kj Oh Rf) Ub(bJ cR Hw Nd Uc) aA(Cx Hw Il Nc Of) Gp(Mn Uc Ue Uh) Lv(Bn Ha Nm Tz) Rf(Bn Nm Ny Uc) Nk(Il Ng Qd) In(Is Ou Qd) Mn(dI Ky) Il(Jy Lj) Iv(Nm Pf) CsFp CxKg FrPf IqaJ IrIu SraE PgcT} Kp{Oy(bE Bn cT gL Hv Jr Js Kk Mv Sr Vp) bN(cS Ii Jj Ju Jv Ly Nk Rb Ub) Sr(aE Ar cV Fr Im Ly Me) Gp(Gl Ly Mn Rb Rj Uc) Bn(Lv Lw Mu Rb Rf) Nk(dI Kr Mc Rj Uc) In(gW Il Kj Kr Ou) Jo(Cu Lv Mg Qy Rf) Ha(cR Lv Mr St) Ub(bJ cR Il Ly) Lh(Jp Nw On St) Mc(Il Js Mr) Mn(cR Ky Rf) Uc(Lw Mu St) Jy(Ao Ij Il) Kr(Ax Hw Oh) gL(Gl Ii Pg) Fp(aJ Lj) Rj(gW Uh) CqLv NoIi MbRb MuJk HwbJ IbQy StKc JvcR RfgW NwPg} cT{Rf(Bn Cq dR Fp gW Ha In Iq Oy Pf) Sr(Ar bX cS Hf No Oh Qy Ur) Mc(bN bQ cI Ha In Lz Mn) Rb(Cq Ct Kg Kj Kr Nr Oy) St(Ao Gl gW Hw Jq Mn Nr) Jo(bX cV dN Ip Nd Nt Qy) Nw(Ao Gl Hw Ii Ny Uh) Oy(cV Jy Ly Nk Ny Ub) Pg(cR Iv Kk No) Ly(Aj Ch Jj) Mu(Gl Ii Mn) Hw(aA aW Kk) Jy(Cq Jk Mn) bX(Ch Dd Ib) Ha(Lw Ub) Nk(dI Ue) Iq(bE No) Ra(Gp Ib) FpLj LvNf MrUc NddN InRh QdNy} Sr{Jp(Aj Ch cI gL Ib Il Lv Nd Oh Oy Qd St) Nw(aF aW gL Iq Jo Mn Nk Ny Rb Rf Ub Ur) gL(bV Cs dM Fp Jn Lj Ph Rb Rf Ur) Fr(Ch Il Jo Oy Ph) Qd(Ba Gp Ly Nk Ur) dM(Cu Oh On Rf Ut) Ur(aA bV Cu Un) Iv(Ha Ii Oy) bV(Ar Ba Jy) cR(Ii Il Oy) Mu(Ax Cs) Rb(Bn Mb) Kk(Ar Fb) Rf(aA Ub) aJ(Ly Ou) BaaE CqKf LvIl NkSt UeIq IncS QzJn OyPc} Jo{Iv(aO AP aS bX cS Dg Gp Kn Nk Qy Ub Vv) Rh(cS Cu Fb Fr Jn Ly Mw Rb Ub Un) Rb(Gp Ir Jn Mw Ou Qt Ub) cR(bN Hc Jn Kf Ly Mb Nt) Kk(bI bN cS Cu Gp) Ph(bN Ip Iq Jy Nk) Ou(Cu Jy Ow Qy) cS(Ba Jn Lv Mb) Ly(Gp Ok Qt) Ip(Ar bV Kf) Iq(Ad Dc gL) Kf(bJ Nk) Kn(bI Bn) Ok(In Is) BcMb CucI NeRf} Rf{Nm(cR Cu Gp Ha Iq Iv Nk) Ii(aW Fa Fb Im Me Ou Ub) Ny(gL Hc Im Jn Nd Ne) Rb(Aj Ao Nd Nj Oy) Ba(Ao dR Mn Oy) Ly(aS Jy Mb Nj) Nk(aS Il Rj Ue) Ra(aX bV Lv Oy) Bn(aA Kg Ub) Uc(Cu Ef Kl) gW(Gp Kk Lv) Ao(Fr Jn) Nj(In Ub) Hc(Nr Oy) Iu(Kr Rj) Jy(aF Il) CsFp WmHa MeKr MnQy UbcR IqUg RiRj bIbJ} aA{Iv(bJ Cq De dF dG Ha Il Iq Js Nc) Oy(Fr Ir Ji Jn Lv Mu Ok Rb) Bn(bQ bS bW cA Lv Lw) Pf(Ir Is Ji Lv Mb Qd) bR(aF bJ De Mb Pc Qn) Cx(aP dG dH Jy Mc) Rb(As Dd Nd Rh Ub) Ly(As gW Uu) cR(dH Pc Ub) Lv(In Iq) Il(Qd Rh) Jn(Hw In) dH(bN dI) gW(Nk Rj) DeMr NqbJ MbNj IqSt JiNy} In{Iv(bX Is Ji Kf Mw Nk Qy) Il(bJ Cu Jy Kk Qt Vv) Bc(aE cS Mb Rh) Rb(bV Kk Ou Rh) Kf(bJ Rj Ue Uh) Ph(Fb Jn Kr Pg) bN(bR Cs dM Ir) Nk(bV cU Is) Iq(Al Ba Cq) Ou(Nf Rg Ue) aS(cR Mc Nw) cS(aW Ir Kr) Mr(cF dM) cR(cI Rj) CsNj CuUc DdKn FaNf FbVv NrIr NddM UbJn UeKs IsOy aQgW} Rb{Mb(aJ aS Ba Fb gL Mk Qd Qt Ug) bV(bW Ha Ib Il Ne Oy Rj Uc) Ub(Bn Bo Na Og Qd Uk Ur) Gp(cI dM Kk Ue) Lv(aW Bn cI) Il(bE gL Ir) Kk(gW Ky Oy) bN(aJ cN Ky) Qd(Ha Uc) cR(Ly Ue) BnJy HwIr QtKj KrOu KycI} Nw{Ii(Ba Bg bW Ic Ou Qx Qy Uh Ul) Qn(Cq Ib Iq Js Nk Pb) Bn(Ha Ke Kr Ny Pg) Uh(bI cR Fb Il Pa) Ao(Ba bN Iq Ne) Ub(Iq Nk Pg) Ha(Cx Ke) Mc(bI Fb) aF(cR Ny) IlcR PgaS} Kk{Oy(bI cS Cu Gp Hc Jh Jy My Ub) Gp(Bn Fp Il Ly Mn) Fp(Jp Oh Qd) Ii(Dc Fr St) Jd(aJ aX bV) Il(Jy Mc) Qy(cR Ib) cS(Hw Pf) gW(Ju Jy) BnLv DddI UbbN IcJj NybI} Nk{Ub(Bo bZ dM gL Lv Oh Qd Qy St Ug Ur) Is(Hw Il Jj Mc Nm Oy) Ue(Jn Kf Kz Ld Qy) Jj(Ir Iv Jn Ok) Jp(Jr Oy) bV(bN Mc) CuIi StgW} Il{Lv(cV cX dM Hf Tz) Qd(Ha Hq Is Iv Ub) dI(Ar Iv Jn Ld Nt) Mc(gL Kf Un) Jy(Mi Ph Ue) bE(Mb Mr St) Ub(cR Iv) CuKr MuIb IvgL StcR} Ly{bV(bW Lv Mb Nd Ne Og) Ub(bN cR Jj Mb Rh) Ao(Cu Fr Mu) Mb(bE bI dM) bN(aJ cN cR) Qd(Bn cR) CuIi FrOy GpdM LvaW QtKj aSdI} Mc{Fb(aE gL Jp Kj Og Oy Rj Uk) bV(bN Jy Kr) Ub(Fr Jp) Kf(Dd Js) BoLz HaIr QdbN JpKr OwOu PhbI aWgL} Ii{Cu(aW cV Ih Jn Kj) St(Bn Ne Or Ra Vp) Ou(Dc Jy No) Is(Lv On) Jn(bE cR) ArMu DcDd FrbN QdRj UnVv} Iq{Mu(aE aJ bV Ch) Ub(cR Dc Jy) Qd(Ba cR Gp) aJ(Jn Lv Mb) gL(aE bN cI) Kr(Kf Oh) BaJy CucI NrIr LvaS} bN{cR(Iv Ld Lv Mu Rj Ue Ug) Mu(Ao Bn cS Iv) Jj(bI cS) Oy(aJ Kf) bV(bX Rj) MbbE} Jy{Bn(Ld My Rg Ur) Ph(Ao Ha Oy) Mb(Hf Me) AogL AxFp BaIb OuOy PgbV} Qd{Gp(Bn Mn Ra) Ha(cR Ub Uh) Iu(Bn cR) AogL HcOy RjPg QncR} Lv{aW(aS Bn Nf) Uc(Cu Jn) Ph(Bn Kr) bI(Mb Rh) NfcI RjaS} Fp{bV(Ld Lj Oa Rg) Ax(dM Oz) Cs(Bo Nd) OaUr OuaJ} Nj{St(Ao gW Nd Oy) Ph(Cq Of Rj) NdbV UecR OwOu} Mu{Bn(Ar Dd) Ha(Ax Ou) Mb(aF bI) AocR DkIv JkOu} Oy{Hc(dI Kf) Qy(Iv Kf) BaRh EfcI HwIs JhOu RabV} Ao{St(Ba Fr) gL(Jn Ph) MbOm KfRj OncR} Cu{Uc(Ba Ld Uh) cI(Hw Pg) RaKj} Gp{Ub(cR cS Ki) Ra(cS dM) NybV} Ib{Ba(bX Iv) MyKd QyOu} cR{Ub(Ld Rj) UeIv QyKj} gL{Ny(Iv Rh) CxaW OuPg} Kr{Cs(bX dI) BnLx} AlStgW BaMnKy UbUnPg KfRiRj OwOubX

Constrained panels with 3 analytes, where 1.0E-6 >= 'AUC p-value' > 1.0E-7. Contains 7,629 panels of 6,910,825 total panels evaluated. : cQ{Kq(Aj As bQ Cp Cq Ct Cu cV Cw dG Hr Hv Hw Ij In Ir Ji Jr Js Ke Kz Ly Md Me Mj Nd Om Or Pb Pe Qa Ql Qn Ug Ul Up Ur Ut Vp) Sr(Ad Af aM As bJ Cp Ct Cw Fr Hv Hw Hx Id Ij Ir Jn Js Kg Kz Me Mj Mr Nr Oh On Pb Pe Pi Pk Qa Ud Ue Up Vp) Kp(Ad aM cI CP Cw Cx Dd De Fn Fw Gp Hr Hx Id Ii Ir Js Jt Mj Ml Mr Mx Na Nr Pb Pi Pk Qa Ql Qx Ud Uk Ur) Io(Ba Bg cF Cs cU Dk Dl dN eF Gp Hc Ip Jl Kl Li Lj Lv Ma Mr Mx Nk Oa Om Ou Pe Qy Ug Um Wm) Af(Aw Bc Bo bV bX cS Dk dN Id Ir Iv Jl Kf Ly Mt Nt Oa Ok Pe Qa Ub Uf Um Us Ut) Us(aS aW cU dG Dk Ez gL Hc Id Im Ji Jl Jp Jq Kz Ly Ny Ou Qa Qb Qh Up Wm) Ue(Bc bE cT Dc dN Fr Id Ih Ip Ir Lv Ly Mu Mw Nw Oh Om Ph Rf Um) Qd(Ch cP Fa Fn Hq Hr Hv Hx Iq Ir Jj Jo Kj Kr Kz Mn Nd Oy Tj) Jy(As bF bJ bX cF cI cR dH Gp gW Hq Nk Pg Rf Uk Ul Ur Uv Vp) bN(Ar cF cU Fr Ih Is Ji Jj Jl Jn Kf Ld Mw No Oh On Ph Rb Rj) Mu(aA Ax bF Bg bV cE Ch Dk Fb Gp Ha Iu Md Oy Uc Uk Ul Ur) Un(Ad aE Aj Cq Dd Hw Ij Iq Jt Kr Ly Me Nm Pb Uk Ul Uv Vp) Kj(Bc bX cS cT Cu Dc Fr Ih Ir Jn Mw Oh Om On Ph Rb Ua) Bn(Bo bX cT dM Id Iv Ld Ly Mr Nk Nt Ny Om On Ub Um) In(aJ Ar aW cI eF Fr Ih Is Lj Lx Nt Nw Oh Qa Qb St) Kf(aM As bJ Ct Cw Dd Hv Ij Iq Js Mb Me Mr Na Pb Uv) Il(bV cT eF Ip Is Ji Jl Jn Ld Mw Nd Oh On Ph Rf) Nk(aS aY cN cU Cx eF Lx Ly Nc No Oh Ph Rj Ug) Jn(aE Aj bE Gp Hw Jj Kg Ly Rj Uc Ug Uk Um) Ld(aJ aP aY bV cS dM Fb Gp gW Jo Mb Mw Uk) Lv(bX cR Cx Iq Mb Nd Nf Oy Rb Rj Um Ur) cI(aJ bX cH cT Dc Fb Fr gL Iv Mb Nx Oh) Ly(aS bE Cu Cx Dc dN Fr gL Gp Mw No) Jo(Ar bX cU Fr Is Jm Ok Ou Pj Rb Rf) Kr(aJ aP Ax Cs Cu Ir Iv Nw Ph Qe Rf) Oy(Fr Is Jh Mw Nt Oh Om On Qy Rf Ua) Rj(aS bX Dc Ip Jj Kn Lw Mz No Ph) bE(aA aS aY Bc Ip Mr Oh Ph St Ur) Ch(Cp Fr Ip Mw Nt Oh Om On Qy) Mb(aS aW Im Is Ji Mr Qy Qz Rf) bV(bS cA cV Fb Hw Iq Mc Qy St) dA(aE bJ cB Gp Ha Hr Lz Mk Rg) Aj(Fr Jg Mw Nt Oh Ph Qt Rb) Cu(bJ Cq cV Hw Iq Nf Of Um) Cx(An cT Cv gL Iv Rb Ub Ur) Uk(aY bX Dc Ih Ip Iv Rb Rf) Gp(aW aY cP Ih Iv Qz Ra) Nd(aP Bo Fr Ih Jj Lx No) Mn(Fr Is Ky Lx Oh On) Ib(Bc Bo Dc Ir Mw Ny) Iq(Fr Ih Im Is Oh Ub) St(Al Jv Or Qy Ur Vp) Nw(aA Ba Et Kk Nm Wm) Nx(aS Kg Ny Tz Ug Ur) Hw(Bc dM Ir Is Mw) Ii(Fr Is Ke No Om) Um(aY cT Dc Is Oh) cP(aJ cT dM Ip Ne) Ba(aE bX Kk Ub) Bo(Co Iu My Uc) Ir(Ha Kg Ug Ul) Ip(aW gL Qz) Qw(Ez Ji Jq) Jj(bX Ph Rf) aA(Fb Kz Na) aP(bS cV Uv) cR(Ou Qy Rb) Ha(Ih Lx) No(aS bX) Nf(Kn Ny) Ub(Fr Qz) Uc(eF Om) Oh(Kg Ug) Ul(cT Kn) Ur(dN Fb) Ph(bJ Ng) aF(aJ gL) aW(gL Qv) BcaE CsFp CvQn DcDd WmcS McMw IvUg NyOn UvaJ aYcF bXdI cVeF} Kq{Mn(Aj aM An As bV cI Cp Cq Cu cV Dc Fw gL Gp Hr Hv Hw Id Ir Iv Jj Jn Jr Js Kg Kk Md Mj Mz Na Ng Nw Ny Of Om Or Pb Pi Pk Po Qa Rg St Ud Uk Ul Up Ur Ut Vp) Ny(aE Ba Cp Cq cV Cw De Fw gL Gp Hr Ij Io Iq Ji Js Kc Kr Lh Md Me Mr Nd Nm Or Pb Po Qv Rj Uh Uk Ul Ur Uv) Gl(As Ba bJ bV Cp Cq Dc dE Fw gL Hr Ij Js Jt Kc Ke Md Mj Mr Mz Na Nd Nm Of Or Pb Po Ra Uk Ul Um Ut Vp) Iq(aM aY Ba bE Cp Ct cV Dl Fw gL Hr Hw Im Js Ke Mc Md Mr Mz Na Or Pb Pe Ql Rb Sr Ul Ut Vp) Qv(aL aM As bQ Cp Cu dL Hv Hw Hx Ir Jd Js Kz Ly Mb Md Me Mj Ml Mr Or Pb Pi Qa Rj Ue Ul Um) Uh(As bJ Cp Fn Id Ij In Ir Js Jt Ke Kj Kr Lh Ly Md Mj Mr Mz Nm Of Om Or Pb Po Ud Uk Up

Figure 19 Continued

Ut) bN(aE Aj Al aW Cq cR cS Dd Ha Ij In Jv Kj Lh Ly Mc Nf Rb Ue) Qw(Aj aW Co cT Cw Dk Ha Hq Ib In Jv Kc Kg Kk Md Mm Nm Om) Kr(aY Ch cS Dd De gW Hf Ib Iu Kc Ly Nf Oh Om Ou Pg Ph Tz) cP(bJ bQ Cw Dd De gW Ij Iu Kg Mb Nd Pd Ue Ul Um Uv Vp) Ha(Ad aE aS aW cR Cs Cx Dk Kc Ke Kk Kp Rb Rj Us) aY(As Ch cV Gp Ji Kj Lh Ly Mb Me Or Rj Ul Um) Dd(Ch cI In Kc Ke Kk Mc Nm Pg Rb Rj Sr Ue) Ni(Ct Fn Hw Kd Kn Na Nb Nr Ra Rb Ur Tj) Io(Aj As bQ Cq Ct Gp Hw Im Kz Mr Qx Ug) Sr(aJ cS Hr Kz Ly Nm Rj Ug Uk Ut Uv Vp) Ii(aW bE Cq Dl In Kc Kg Po Qx Ug Ul) Ke(bV cI gW Ib Ly Mb Nf Rb Rj Ur Uv) Af(bE Cv cZ Hw Jr Me Mj Na Or Qa) Ub(bJ cR Ib Jt Ki Lh Ly Rh Rj) Jo(aS aW cI cT dA Dp Kc Kk Ph) Pg(Ad aE aW bV cR Kc Kj Nm Oz) bA(De dG Js Mj Nm Of Pb Po Uv) Lh(Cx Ly Nb Om Pd Qn Rb Ul) dA(bR bW cG dG dH Ib Pd Um) Ao(It Ko Kz Qn Un Ur Tj) Bb(aE cI Fb Kc Oy Ue Ur) Nf(Ad aF Dk Jt Nm Ra Ue) Tz(Ad bJ Cx Mb Nm Qn Ue) Il(aA aW Fa Kp Kz Po) Jq(aE Aj bV Kj Ng St) Us(aS aW cT Hq Kk Nm) Oy(aS aW Ba cT Ul Vp) gW(Jt Kz Or Rh Rj Ug) Bn(Al Dg Kk Ur) Nb(Cp Jd Om Vp) Rb(Cx Jt Ue Uv) Kc(Ad Et Jt Ko) Rj(cI Dk Ut Uu) Qn(aA Ch Cq Kj) Dg(Ib Ij Vp) Ra(Cq Om Vp) aF(Ib In Jt) Ad(Nk Rh) Cx(Kj Nk) Nm(Rf Rh) Mb(Iu Ly) Mc(aS Fb) Ue(In Nv) Ij(aW Kp) Uu(Pd Po) DeaW NrUm NuIb UcVv IucR JnJs JtKp OwcI} dA{Nx(Ao As Bg bJ Bn bQ bW bX cG cL CO Ct dG dH Gp Hq Hr Hw Kr Mk Mm Mp Mr Ns Ny Or Oz Pa Pf Po Rg Rj Tz Ul Tj) Us(aO aQ Ax Bg cH cN Cs cY Dc Dg Ef Fb gL Ih In Jg Jj Jy Ke Kk Kl Lv Lw Mi My Mz Nw Ok Om On Qy Sr St Uf Ur Vv) Ly(aE AS bJ Bn bQ bW bX Ch cK cL Db dH Ha Hq Hr Ir Jj Jo Kp Lz Mk Nw Of Pb Pf Qt Uk Ul Um) Io(aE aJ aQ Ar Ax cB cF Cs Dg Ez Gp Hc Ih Is Kl Mt Nt On Qa Qe St Um Un Vv) Ub(As bU cC cK cL Cq dH Gp Hq Ib Lz Nd Ns Of Oz Pb Pf Rg Uk Uv Tj) Rb(aE As Bn bS bU bW cA Cq Ha Hr Ib Jo Lz Mk Na Nd Of Rh Ul Um Ur) Oy(aQ aS Ba Bo bV bX Fb Fr gL Hc Hf Lx Mt Nf Nt Oz Ph Rj Sr St Un) Il(aO bN cF Dc Et gL Gp In Is Jg Ji Jq Ld Mt Mw Nd No Oh Ou Rh) Ha(aA Ax bV eF Fa Fb fP Fr Hf Kk Mw Nw Oh Ou Ph Qt Rj Sr St) Kp(bQ Ch Ct Dd Dc Gp Js Kj Lh Mb Mr Of Or Pd Pe Po Ue Uk Tj) bN(cB Fr Gp Hf In Iq Ir Jn Ld Lv Mu Nf Nw Ph St Um Ur) cT(Aj bJ Bn cF Ch Cq Ct Kr Nf Ng Ny Pb Pd Rj Uk Ul Uv) Rj(bS bV bW cA cF dH Iq Kf Ld Lz Nd Qd Uk Ul Um) Nk(bI bX cF Gp Hf Ih Kz Lx Nw Oh Qd St Ur Vv) Nd(aQ aS Bc bI Bo bV bX cF Fr Hf Nj Oh On) bR(aQ aS aU cS Hf Mu Oh Ou Ph Qd Ue) Iq(aE cS Cu Fb Is Iv Oh Ph Un Ur) Nb(aE Aj bE Mq Nm Nr Ow Pf Ur) Af(cP Iv Ji On Ph Qd Qt Un) Mb(Fr Hf Jo Lz Mu Nj Nw Qd) eF(bS bW Hr Jo Of Uk Ul Um) Ib(Ba bV cS Cu Hc Iv Kk) Ou(bU cA Cq cR Lz Of Tj) Jn(Cq Kr Mn Ny Ul Uv) Jo(cS Cu Ic Ip Kk Kn) Um(aA bV gL Kf Mi Ue) Bn(Kk Kn Nw Un Ur) Iv(aE Ch Gp Ii Uv) bS(cF cR Cu fP Nf) cS(cA cK Kr Lz Rg) Qv(aW cI Ow Rf) Kc(Gp Kr Nl Tj) Kf(De Jt Me Of) Ph(Hw Kr Pb Pg) Nf(bU cA Uk) Qd(cR Iu Uc) Kk(Dd Gp Tj) Ii(Ir Ji) St(Nj Ny) Ky(Lz Or) Rf(Ra Vp) Nw(aF Ny) Uv(bV Cu) cI(aV cB) fP(bW dH) AxKr ChIp DdSr PoLx FrMn LvaE UebU HfUk LdcR OwbA UlcP bIcF} Nb{bV(aM Cp Ct cV cZ dG Fa Fw Hr Hv Hw Hx Jn Jr Ke Kg Lh Me Mj Mr Mx Nr Om Or Pb Pd Pe Pi Pk Qx Ug Uk Ul Um Ut Vt) Kg(aA Ar Ba Bg Ch Dk Gp Ij Je Js Lv Mj Mn Mw My Nk Nv Nx Pb Qx Tz Um) Kp(Ad bJ Cp Ct Fw Hr Ii Jk Js Lh Mb Me Mj Mx Ny Om Pe Pi Qx Um Uv Tj) cN(bQ bS cG Co dH Gp Hr Mm Mq Mr Nk Ny Ow Pb Po Tz Ul Um Tj) Kr(aJ Co Hq Ki Ky Mc Mk Nq Nv Ny Pb Po Qx Sr Tz Tj) aA(aM An Cu cV cZ Dc Gp Or Pi Qx Rh Ue Ul Um Tj) Ch(Bo Fn gL Iv Jn Kz Na Ra St Ud Ug Up Ur Uv) Ba(Bb Bn Ct Cw Dk Hq Jg Jh Jk Mv Rg Uu Uv) Gp(Aj bF bQ cI Cw cZ dM Ki Mk Mr My Qd Qt) Ue(Co Ct Cu Hw Iv Jj Jn Ks Kz Nq Pz St) As(Bg Co gL Jd Lv Mi Mw My Nk Rf Rj) Sr(Ar Cw Fb Jn Mj Nf Nm Pd Qa Uv Vp) Jv(aE Ct cZ Fw gL Hr Hx Js Ml Og Ut) Ph(Dd Hw Il Js Jt Mj Mr Ny Pb Pi Vp) Aj(Cq cT gL Mr Qv Qx Rb Rf Rh Tj) cI(aX BN Cq cZ gL Mq Of Qv Rj) Kk(Ct cZ Mj Mr Pb Pi Qx Um Vp) Kz(cP cS Ic Jd Mk Mn Og Rb Rj) bJ(Bg Hc Je My Ng Oa Qt Qy Rg) Rf(aX bE bN cZ Jd Mn Mr Nr) aJ(Cw Fp Mb Mn Rj Tz Uv Vp) cT(bE Fa Hq Hr Jk Pd Uk Tj) Bg(bN Js Uk Ul Um Ur Uv) Co(Ar bE Mc Ug Uk Um Ur) Nc(Ct cZ Ki Pi Qx Ut Tj) Nw(Bb bF bN De Dk gW Tz) Ao(Ar Bo Iv Na Qz Ug) Ub(Cu gL Hr It Iv St) Fn(Bb Jd Je Ki Ld) Ij(Dc Je Oa Qt Un) St(Dk Jk Nf Tz Vp) Qv(aL Ct cV Hr Ut) Ou(bE Fw Ii Pb Po) Um(Hq Hu Jd Je Qt) Ne(cV cZ Ut Tj) Qy(Hx Jd Js Ml) Jy(Mr Nv Ut Tj) Kf(Cw Ii Kj Nm) Ky(bQ cZ Jd Mw) aX(aY Ct cV Uk) bE(Hr Mc Ny Uv) dI(bR bX Ct Mk) Fb(bN Hw Ii) Mi(Ct Uv Tj) Qz(Ii Mc Pg) Qt(Js Mj Ul) Rj(Jj Ms Nq) Nx(cZ Ks Ut) Bo(Hq Iu) Dd(Jq Kd) Lv(Or Tz) Mb(gL Je) Mr(dM dN) My(Ul Uv) Rb(Lh Ut) Qd(bS Fw) Js(Oa Rg) Kj(Ef Rh) Un(Iq Ke) Ug(Nk Of) cP(gW Mv) CqNy CwdN CxcX LuaF LygL MkeF MnLd NgQx NiQh IcJt JdJj UrbQ bHbX} Io{Kk(aA Bg bV Co Cq Ct Dk Fb Fw Hr Hw Hx Ij Im Jd Je Js Ks Ld Mi Mj Mk Ml Mr Ms Mt Mw My Nq Nv Ny Of Po Qx Rh Tz Uc Vp) Ub(Ad aO Ap aS Ax Bg Cu Dc Dl Et Fb fP Hc Ih Ip Ir Ki Kl Ld Lv Ly Mm Mr Mw Om Pj Qt Qy Rj Um Un Ut Vv) Qw(aO Ax bI bN Cs Dc Fb In Kl Ky Lx Ma Mu Mz Om Ou Qa Qe Rc Rh Ua Ug Un Ut) aS(bR cS Cu dM gL Gp Ih Is Jg Jp Jy Lv No Oh On Qv Qy Rj St) Rb(Ax cI eF Ez Ih Im In Ir Is Jg Kl Lv Ma Nw Og Rh Ug Un) aY(Ar bN Bo bX Ef Ez Hc Jy Mu Nf Nk No Nt Ph Qy Rj Ut Vv) cS(Ar Bc dM Gp Hc Hf Ih Il Im Jg Jo Jp Nf Rf Ur) Qv(Ax Ih It Ji Ld Lx Ly Om Ou Pj Qz Rh Rj St) Sr(Af Cq Dd Fr Jo Ly Nm Of Or Uc Ul Us Uv) Gp(aE aJ Ar gL Jn Ld Mx My Ou Qz Ra Rf) Iv(bE cI cN eF Ez Qy Qz Rc Rj Ug Um Us) Kf(aM Dd Hr Jt Kr Mb Nk Pb Ue Uk Ul Uv) bN(aP cN cP Dc dG Ir Is Ly Oh Ph Qa Qe) In(aE Ar dM eF Ic Is Ji Oa Qt Rm Un) Us(Bc Cu Ir Jg Jp Nt Nw On Ph Qy St) Ba(bX Ch dM Hf Kg Kj Of Og Ou Uk) Qd(Ar bS cA Fw gL Hf Kc Qn Uc) St(aF Ao bI Ha Jn Jo Nj Nu Oy) Ph(Bn bX Hr Ib Jj Jy Lv Nf Nj) Af(Dc Ez Jg Ji Jy Lv Mu Ur) Cu(Aj Hw Nd Nm Rj Ue Ug Um) Il(Ar bE Bg bX Cp Fb Kl Qy) Rf(aA bV Hf Im Iq Kc Nx Rj) Oy(Dc EF Ez Hc Kl Nx On) cP(cI Cs Fb Ic Kl Mw Ou Ur) cR(Hc Hf Nf Ou Qy Rj Ue Ur) Ar(dM Im Jo Ly Nf Nk) Jn(aW bE Fb Kg Kj Uk) Jp(aE bV bX Ib Kc Ue) Ug(cT eF Ip Kc Kl Oh) gL(aE cT Cx Hf Ly Nf) Ez(aE Nf Og Rj Ue) Jg(aW Ch dM Uc Uu) Rh(bI bX eF Fb Ue) aJ(Ic Kc Mb Nd Rj) On(Bn cI Uc Uh) Ur(bX cT Jy Lv) eF(aW Ch Im Ns) Bc(Hw Mb Mc) Fr(Ch Ib Ue) Mu(aF Bn Ou) Jo(Ap Ax Ou) Ly(Ax bX) Ih(bV Jy) Hc(aE bV) Qt(Hf Me) aW(Kl Lv) cI(aO Ef) cT(bP Fb) dM(Nk Nt) CsQy DcDd DgaE MbbI ImOu KcNw KgNx KrOh aAcV} cP{Us(bV Cp Dk Fr gL Gp Ir Is Ji Jl Jn Ke Kf Kk Kn Kp Mz Nk Ny Om On Ph Qw Qy Rj Sr Ub Um Ut) Jy(Aj Bb bQ cE cI Cp Cw Dk Hc Hf Hu Jh Jv Ki Kz Mw My Om Pb Po Qy Rg Uk Ut Tj) Mu(Ad As bF bQ cE Co Cw De Hf Hu Jh Jo Mw Nq Nv Pb Pd Qb Rg Tz Ub Ut Uv) Jo(aA Ad Ax Bc bE cT Et Gp Ih Ir Is Ji Jq Kd Ma No Om Rb Sr Un) Nx(Aj As bN Co Ct Ha Hr Ii Il Iq Kg Mn Nd Ny Pg Qd Rj Uk) Mt(Ad As Dd Ha Ib Ii Il Kg Kj Kr Nd Nf Nm Of Pd Rj Uc) No(bN Ch Cq Cx De Ha Ib Iu Kc Nf Pc Qn Rj Ub Uc) Oy(aJ aM Ar cS Ef gL Gp Ir Jn Ly Ma Mb Nk Qy Rh) Ib(aA cR Dc Jh Kc Kk Kp Lw Lx Nq Nw Ny Om) Qd(Af cZ Hf Hq Hr Hx Ih Jj Kr Pg Po Tz Tj) Rj(aA bE cR Dc eF Jq Kd Ne Nk Qv Qw Ub Un) bA(Bn bQ Ha Hr Ii Il Kg Kj Mk Mr St Ue) Af(aJ cN cR cT Fr Ji Lv Qv Qw Rb Ur) Cu(Aj aM Ch cI Cq cV Ii Iq Jt Kr Pg) Jq(Ad aM Cq Ha Il Jt Nf Nm Pd Qw Uc) Nw(cI Co cZ Dk Hq Iu Jk Kj Of Po Ub) Lv(aJ cV De Ha Kg Kj Kr Me Tz Uk) Kp(Aj bE bN Cq cR Kg Kj St Ub Ue) aA(aM aP bE cI cV dG Gp Mb Nf) Ub(aM bE Gp Iq Kc Ki Kk Ne) Ch(aJ aM Bo Gp Lx Nq Om) Qw(bE Bn Fb Kd Kf Rh Sr) Lx(Co Iu Kr Nf Pf Uc) Ly(aJ aY bV Gp Nk Rb) St(cR cZ Dd Iu Ne Nj) bE(cI Il Og Rb Rf Uk) Dc(As Cw Ii Ij Nm) Lw(Ha Kj Nd Qn Uc) Nf(Is Iv Kk Mr Ny) Nk(aJ Ih Mb Mc Nc) Hw(Fb gL Is Mw) Kk(bN Gp gW Tj) Rf(Aj cI cN Kj) cR(aY bN Qv Ue) eF(cI Of Uc Uk) Cq(Nv Ny Pg) Jj(aM bN Nd) Kr(Jn Kd Oh) dI(Ou Ph Ur) Bn(Ke Un) Gp(cI Rb) Ha(Pg Un) Uc(Kd On) Kc(aY gW) AjaM CvQn MbNj MrcZ IngL KgRh KybN bVbX} Qw{Af(aO cN Cu Dc Gp Hc Jh Ji Jj Lv Nj Nk No Ny Om Ph Rb Ur) Jo(aJ aO aP Ax Bc cN dM Ez gL Gp Jp My Oh Ok Qe Un Vv) Rb(aP bI cS gL Gp Ir Iv Jn Jp Lv Mb Mw Ph Ug Un) Kc(aS bV Ez Fr Lw Mi Mu Mw My Nl Nw Qy Ri Sr Ua) Us(aJ Ar Bo Fb Ih Im Ir Is Iv Jn Jy Lv Mt St Un) Il(Fb Gp Ir Ji Jn Kf Lw Lx Mw No Nt Ny Qt Ut) Nk(aJ cN cS Ir Jn Kf Ky Mb Ph Qd Sr Ue Ug) aS(aJ bE Dc dN gL Iv Kd Ky Lw No Nw St Un) Qt(Aj bI cN dI dM Jy Kg Ky Nx Qy Ue Ug) Ub(aW Bg cI Cp Dc Ji Lw Mi Mp My No) Qy(bN dM Jj Kf Ki Kj Ky Ph Qd Sr) Rf(aA aW aX Ba bV cI gL Lz Mi Mu) cR(aW bI Dc Fb Gp Im My Nj Ug Ur) Kf(Dd Hr Iq Iu Jj Kr Lu Nd Nl) Ba(aE aW cI cN dI Ki Ky Oy) Lv(Bn Cx Iv Kk My Rh Sr Ur) Nj(cN Ih Ir Jr Ky Mb Qa Qh) In(aJ Ax bI Cu dM Ip Jm Sr) Qd(Al cI Dd Hc Iq Kp Nl Or) Qv(Ih Im Lw No Nw Ou Ri) On(Bn Ii Kj Lh Oy Sr Uh) cS(cN Hc Im Jj Kr Kz Ri) cT(aJ aW Hf Nd Nw St Tz) Ao(Dk Ji Nq Ny Om) Is(Ii Qn Ri Tz Uc)

Figure 19 Continued

Constrained panels with 2 analytes, where 1.0E-7 >= 'AUC p-value' > 0. Contains 89 panels of 60,152 total panels evaluated. : Ni(Af aJ aY BA BN bV cN cP cQ cR cT dA gL Gp Kc Kk Ph Qv Qw Rf Rj St Ub Ue Uk Ur Us) bA(Af aY bJ bX cQ cV Gl Hw Ib In Io Iq Jo Ly Mc Mn Nd Nk Ny Oy Pg Qw Rb Rj Sr Uc Us) Nb(aY cP CQ cR dA Dd De Ha Ib Kj Qw Rb Rj Uc Us) Kc(cQ Nj Qv) Io(cT Kp) Kq(Ao Uc) Nx(Jj Jo) aA(Af Nk) cP(In Lv) dA(aV Qw) liSt RfaY Constrained panels with 2 analytes, where 1.0E-6 >= 'AUC p-value' > 1.0E-7. Contains 54 panels of 60,152 total panels evaluated. : Nb(Af Ao BN Ch Kc Ub Ue Vp) bA(bE cI cP Ha Il Kc Kr Nf Ub) Ni(aA bE cl Ky Nx Ug) Qv(bE cQ dA In Kp Lv) Kp(cQ dA In Oy Qw) Af(cT gL Kq) aA(cQ Oy Qw) Kk(cQ eF) Kq(Il Mn) Nx(cI Us) cT(In Mc) dA(Iv Us) IoKc QwRf JoOk Constrained panels with 2 analytes, where 1.0E-5 >= 'AUC p-value' > 1.0E-6. Contains 136 panels of 60,152 total panels evaluated. : cQ(aJ bX cP cS cT dM In Iv Jy Kq Mu Nw Nx Qw St Ub Ur Us) Nb(aX bV Co Gp Jd Je Kr Qv Qx Rf Tz Um Tj) Kc(aY bN eF Il In Jo Kr Nk Oy Qw Ub Us) Qw(aY bV cR cT eF Kk Kq Ky Qv Ub) cP(aA bE cR dA dl Io Jy Mu Nw Rf) Qv(aA aY bV cR cT cZ eF Nx) In(aA cS Iv Kf Nx Ou Ph) Ni(Is Iv Ji Jp Jr Mw) aA(Bn Cx Iv Lv Nx) Nk(Is Iv Jp Ub) Kp(Ib Jo Kj Us) Kq(Ii Io Iq Us) Rf(bA bl Bn Nm) cT(bX Hw Jo Ly) dA(Ly Mb Nx Rj) Kk(Io Jo Oy) eF(cI Ub Us) Ii(Cu On) Qd(Ha Il) Nw(Af Ao) Nx(Nm Oy) bV(Io Ly) LvaW UbcR IqaJ SrJp StaY JjOk KjbA Constrained panels with 2 analytes, where 1.0E-4 >= 'AUC p-value' > 1.0E-5. Contains 311 panels of 60,152 total panels evaluated. : Kp(Aj As aY bJ BN cP Cq Ha Il Kr Ly Nf Nk Of Rj Ub Uc Ue Ug Uk Um) cQ(aY bN dN Fb gL Io Ip Jj Jn Ld Lv Ly Mb Mr Nk Oh Ph Qd Rf Rj Ue Ug) Qw(aJ Ar cN cP cS dM Fb Fr gL Iv Jj Jn Jp Jy Kf Lv Mw Nx Ph Qd Qt) Qv(aJ aX Ba cP dM Fb gL Io Jn Jy Kk Kq Ly Nk Ph Qd Qy Rb Rf Ub) dA(bR bX cF cT Ha Il Io Iq Jn Kc Nd Nk Oy Rb Uk Um Ur) Ni(Fr Ih Il Ir Jj Jl Jn Lj Lv Lx Nk Nw On Qd Qe) cP(cS Gp Jo Kc Kk Kq Ly Mb Nk No Nx Oy St Ub Us) Io(aJ Ar aY Ba Cu dM eF gL Kf Ph Rf Ub Ur) Kq(Ad aY BN gW Jo Jt Ke Kj Nm Ny Oy Ub) Us(aA Ar Ba bV cT dM Fr Jn Kf Ph Qd Rf St) Nb(Aj As bE cI Ct cZ gL Kg Kz St Ug Ur) Nx(Af aY bN Ha Il Iv Kj Ng Nk Qd Ub Ue) eF(aS aW Il Jo Kj Mb Rf Uc Ue Ug Ur) Kc(aS bl cT Gp Iv Jn Jy Lv Nl Ug) aY(cR cT gL Gp In Kk Ly Mb Nw Rb) Is(Hw Ii Il In Iu Jj Nr Oy) Rb(aA bV cR cT Mb Rf Ub Ug) Kk(bA bN Dd Gp Il Mn Ub) cT(bJ Ib Iq Nk Oy Rj Ub) In(Bc bV Fb Jp Rh Ub) Rf(Af aS Ly Nk Ra Rj) cR(Iv Ld Ly Rj Ue) Af(Jy Mu St Ur) Nk(Ir Jj Ue) Ii(Cu Fr Iv Jy) Jo(Kf Ou Ph Rh) aA(Aa bN Ly Mb) Lv(aE aS cI) Jj(Ir Iv Jn) Ba(Ib Of) Mc(bV Fb) Sr(Nw Qd) Oy(Jp Kf) bA(Nw Ur) MmJi IqgL Constrained panels with 2 analytes, where 1.0E-3 >= 'AUC p-value' > 1.0E-4. Contains 677 panels of 60,152 total panels evaluated. : Kp(Ad aE Af aM bE Cu Cw Dd De Fw Gp Hr Hv Hw Id Ii Ij Iq Ir Jn Jr Js Jt Kg Kz Mb Me Mj Ml Mr Mu Na Nd Nm Pb Pi Pk Ra Rf St Ud Ul Up Uv Vp Tj) Us(aJ aP aS aY Bc Bo cR cS Cu Ez Fb gL Ih Im Ir Is Iv Jj Jl Jp Jy Kk Lv Mr Mw Nt Nw Oh On Qy Rb Sr Ub Un) Il(aY bE bV cP cR cT Dc gL In Ir Ji Jp Jr Kf Ld Lv Mu Mw Nw On Qw Qy Rb Rf Sr St Ub Un) Io(aP aS Ax Bc bX cN cR CS Dc Ef Ez Fb Gp Hc Is Jp Jy Kl Ou Qw Qy Qz Rb St Ug Un) Kk(As Bb bE Bn Ch De Fb Ha Ib Ic Ij In Jj Kc Kj Ks Lv Ms Nd Nf Nk Pz Qh Tz Uc Um Tj) Jo(Ar Ax aY Ba Bc bV bX cR cS Cu dA Ir Is Iv Ji Jn Jp Kn Ni Nw On Qw Rb Rf Sr Un) Kq(aE Aj Bb Ch cl Dd De Ha Ib Ij In Kc Kr Lh Ly Mb Mc Nd Nf Pd Rj Sr Ue Uv) Jj(cR Fb Fr Im Ji Jl Jp Jr Lv Mb Mu Mw Nt Nv Nw On Ph Qd Qe Rb Rf Ub) Nk(aJ Ar aY bV Fr Ih In Jl Jn Jr Lv Mb Ne Nv Nw Ok On Ph Qd Qe Ug) dA(Ar Ba bN bS cA cB cK Fb Gp Ib Kj Ld Lv Lz Nw Ph Rf Rg St Ue Ul) Nx(Aj Ao Ch Gp Hw Ib Kg Kr Lv Mb Nf Nr Of Og Rf Rj Sr Uc Ug Uk) Ub(aY Bc Bo bX cS dM Fb Fr gL Gp Iq Jy Ki Ld Lv Ly Ph Rf Ur) In(Ar bI Cu dM eF Ir Ji Jn Jr Mr Mw Ni Nw Ok On Qd Qw Rf Un) Iq(aP aY Ba bV cP cQ cR Cu Dc Ir Is Ji Jl Jp Jy On Rf St) Qw(aP aS Ba bE bl Cu Ez Gp Is Nw On Ou Qy Rh Sr Ug Un Ur) Oy(Ar Bo eF Fr Ir Iv Jg Ji Jl Nb Ni Nw On Ph Qd Qy Rf Sr) aY(aJ Ba bN Bo bV bX Iv Jy Ld Mu Nd No Rj Ue Um Ur) cQ(Af Ar Ba bE cF cl Cx Fr Gp Im Is Mw No Rb Um Wm) cP(aJ Bn bV cl cT Fb gL Ld Qd Rh Rj Ue Ug Ur) cR(aW bN bX cN Jn Jy Kj Lv Nf Ou Qy St Ug Ur) Rf(bN cT Ha Ii Kc Kj Kr Lu Nd Sr Uc Ue Ug) Iv(aS Ba bX cI Gp Ji Lv Nc Nf Ue Ug Ur) aA(bS bX cI cT cV dG dH Ic Kc Kj Qd Rj) Mb(bI bV bX dM Fb gL Is Jp Jy Ok Qy) cT(bE Ch cI cS Kj Nd Nf Ny Qd Ue Ug) Rb(aJ dM Gp Jp Kj Lv Ly Ph Qd Ue) Nw(aF Bn Ha li Kc Mm Nr Ny Qv Uh) bV(bX Hf Hf Ip Jy Kc Kr Ld Nd Rj) Af(Ar Cp Cu Fr Ld Ph Un Ut) Ni(Im Jg Mr Mu Nf Nv Ok Qa) Ue(dM Fb Jn Jy Kf Lv Rh Un) bN(aJ cN cS dN eF gL Ky Mu) Ly(aJ dM Fr Gp Ir Jp Ph) Kc(Ba cI Fb gL Mu St Ur) On(Ao Hw Jt Mm Nm Nr Ny) Is(Ij Js Nc Nf Nm Ny) Sr(Fr gL Ha Ii Jn Kj) Kf(Bn Dd Ha Ib Rj Uc) eF(Ib Jy Ld Nd Rh Rj) Qd(Gp Nm Nr Pf Uc) Lv(cS dM Jp Ur) Hw(gL Ir Mw Ok) Qv(cI Ih Im St) Kj(Ba bI Im Qy) Lx(Ha Hq Pa) Mc(gL Ou Un) Nd(aJ cS dM) Ir(Ii Iu Nr) Kr(Cs Oh Ou) Ao(Mu Om) Cu(cI Uc) Nm(Jp Ok) Nf(Ar Jr) Ji(Ii Nr) dM(Gp Rj) gL(cI Cx) BnJy BoCh CsFp FrUc MuaF MwIb NbQz NcJp NjSt JnUg LdcS OwOu UvbA aSdN Constrained panels with 2 analytes, where 1.0E-2 >= 'AUC p-value' > 1.0E-3. Contains 830 panels of 60,152 total panels evaluated. : Kk(aA Af Aj Ao Bg Co Cq CT Dk Fw gL Hr Hv Hw Hx Iq Ir Iv Jd Je Js Md Mj Mk Ml Mr Mt Mw My Mz Nq Nv Ny Of Og Pb Po Qx Rf Ug Ul Vp) Jo(Ad aJ aO AP aS bI cI cN Cs Dc Dg dM dN Et Ez Fb Fr gL Gp Hc Jg Jl Jy Kl Ld Lv Lx Ly Mw Nt Nv Qa Qd Qe Qt Qy Rj St Uf Ut Vv) Kq(aM As aW bJ Cp Cq Ct Cu cV Cw Fw Gp Hr Hv Ir Jd Js Kg Kz Md Me Mj Na Of Om Pb Pe Pi Po Ug Uk Ul Um Ur Ut Vp) Kj(Ar Bc Bg Bo bV bX cS Cu Dc Ef Ez Fb Fr Hc Ir Iv Jg Jn Jp Jy Kf Ly Mu Mw My Nw Oh Om On Ph Qt Ua Un Ut) Oy(Ba Bc Bg cN Cp Cu Ef Ez Fb Hc Jh Jk Jn Jy Li Lv Lx Mv Mw My Nv Ok Om Qa Qe Ua Un) bE(aA Ar aS aY bN dA dD Io Iq Iv Jn Ld Ly Mb Mr Nx Ou Ph Rb Rf Rh Rj Ub Ue Uk Ur Us) Qd(aY bI bN Cq cR dA Fw gL Hf Hw Io Iq Iu Js Jt Kr Kz Lv Lz Mr Qc Rj Ub Ue Uk Tj) Kf(Ad Af As bN Cq Cw Gp Hr Ii Iq Js Jt Kr Kz Mb Me Nf Nm Of Pb Uk Ul Um Uv Vp) Nw(aS bI bN Ch cI cT Dd Ib Iq Iv Js Kp Kr Lv Md Mr Mt Nf Nm Rb Rj Ub Uc Ue Ut) Us(Ax bI bX cN Cp Dc dG dN Ef Hc Hf Ji Kz Ld Lx Mp Mt Mu My Mz Nk Om Ou Qt Up) Il(Ar Ba bX cS dN Fb Gp Ih Im Jl Jn Li Lj Lx Mr Nk Nt Nv Ok Om Ph Qe Rh Rj) In(aJ aW Ba bX cI Cp dA Fr gL Hc Ih Im Jj Jl Jy Lj Lx Nt Nv Qa Qe Qt Rb Vv) Rj(aJ Ar aS Ba bI Fb Fr Gp Io Iv Jj Jn Jp Jy Ld Lv Ph Qw Sr Ub Un Ur) Sr(Ad Af Bn Cq Dd Gp Ib Ij Iq Js Jt Ly Mb Me Nm On Uc Ue Ug Uk) aS(aJ aY bX cN dA dM Fb Iq Jj Jn Ly Mb Mc Nd Nk No Ph Rb St) Ba(aA aE Af Aj aW cI cN cR Ii Jj Kp Mb Mc Rb Rf Ub Ue Ug) Jy(aJ Ao bF bN Ch cI Gp Ib Jj Ly Mc Nf Rf Uc Uk Um Ur) Kr(aJ Ar Ax aY cN cS Cu Fb Fr Ir Iv Jn Jp Ok Ph Qe Rb) Lv(AF aJ Bn bX cV cX Fr Hf Lj Mw Qn Qy Qz Uc) Ue(bI Bo Cu Fr Gp Hc Jp Ld Ly Mw Om On Ou Ph Qy) cI(aJ bV dA dM Fr Gp Io Jj Kp Lu Mu Nx Qw Rf Ur) Ug(aY Bc bV Cu Ez Fb Fr Ih Nj Ou Ph Qy Un Vv) Aj(Cu Ez Fb Fr Hc Iv Jg Jn Kl Ph Qy Rh Vv) Nk(aP Ax cN dM Fp Im Lx Mu Mw Nc Nf Qa St) Iq(Ar Ax cN cS Fr Gp Iv Jn Nv Ok Ph Qe Un) Rb(Af aP Bn Db gL Im Jn Og Ou Qt Qw Rh Ur) Nf(aJ aP Cu Fr Ji Jl Lx Mw Ok On Un) Mu(Bn bV cE Ch Dd Hf Ib Ki Of Qw) Rf(aA aJ aW bV dM gL Mc Og Ou Ur) Un(BN Dd Ha Ii Ly Me Og Uc Uk) Cu(bN Ha Hr Ib Jj Jt Nd Nm Uk) Ld(aJ aP Bn dM Fr Gp Io Jj Rh) Ph(bN Ch cP Ib Jv Kg Ng Nj Uk) Af(Aw Ez Hc Ji Jp Om On Qt) Fb(aY Ch dM Gp Og Ou Uk Ur) Mb(Fr Jl Jn Mw Ni Nj On Ra) St(Bn bV cT Dd eF Ha Qw Ub) Qy(aE bV Ch Ib Jj Og Ub) Nx(aE aJ bV dM gL Ks Ur) bX(aW bI dI Gp Jj Jn Rh) Uc(cT Ef Is Jp Om On) Ii(Ar Bc Dc Kd Nv Ut) Ok(Hr Ij Jt Kg Mm Of) aY(aM bI cF dM Im Uk) Fr(bN Ch Ib Iv Nm) Gp(Ar cN cS Qz Ra) Ly(bN gL Jj Mw Rh) Qw(aX Dc Im Ji Ua) Jn(dM Ha Hw Kg Uk) aJ(bI cT Kz Rh Ub) aW(dA gL Iv Jj Qv) bV(bI bS cA cV Kz) Nd(aP cN dN gL) Ib(Bo Jh Jp My) Io(bI dN Ic Ut) Kp(aX gL Pd Ur) Ar(bN

Figure 19 Continued dM Ha) Ch(Ez Mw Qt) Ub(Jp Mc Ou) Im(cR cS eF) Jj(dA Rh Vv) On(Bn Ng Of) aA(aM aP Vv) Bo(Ao Hr) Nm(Jg Ji) Nc(Ir Jl) Hw(Jl Nv) Qa(Ij Js) Ou(cP Nj) Ur(Bn cT) AnMc AxFp EtMm NrLx MwNg IuQe JpUh UkcS aPbN aXcP cFdI cTgL

Figure 19 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.5E1 | 7.3E1 | 7.6E1 | 7.1E1 | 5.2E1 | 4.6E1 | 2.0E0 | 1.2E1 | 4.0E2 | 1.5E2 | 1392 | 18 | 230 | 18 | 0.48 |
| Ad | ug/mL | 3.4E-2 | 5.0E-2 | 6.5E-2 | 9.6E-2 | 8.4E-2 | 1.0E-1 | 6.8E-4 | 6.9E-3 | 5.4E-1 | 3.5E-1 | 357 | 17 | 135 | 17 | 0.62 |
| Af | ng/mL | 1.0E0 | 9.8E-1 | 1.4E1 | 4.7E1 | 6.0E1 | 1.3E2 | 1.7E-3 | 1.7E-3 | 5.3E2 | 4.8E2 | 357 | 17 | 135 | 17 | 0.54 |
| Aj | ug/mL | 1.8E0 | 2.6E-1 | 2.7E0 | 1.8E0 | 2.5E0 | 2.4E0 | 1.5E-3 | 5.5E-3 | 6.1E0 | 5.8E0 | 357 | 17 | 135 | 17 | 0.35 |
| Al | mg/mL | 8.7E-5 | 8.2E-5 | 2.5E-4 | 3.0E-4 | 4.1E-4 | 4.8E-4 | 2.5E-6 | 2.3E-6 | 1.9E-3 | 1.5E-3 | 357 | 17 | 135 | 17 | 0.51 |
| An | U/mL | 4.9E1 | 6.9E1 | 1.6E2 | 2.8E2 | 4.6E2 | 3.3E2 | 9.8E-4 | 9.0E-1 | 5.5E3 | 9.1E2 | 357 | 17 | 135 | 17 | 0.60 |
| Ao | pg/mL | 8.5E1 | 8.2E1 | 6.0E2 | 1.3E2 | 3.9E3 | 1.5E2 | 2.8E0 | 5.4E0 | 3.9E4 | 6.5E2 | 357 | 17 | 135 | 17 | 0.51 |
| Ap | ng/mL | 3.1E1 | 4.1E1 | 4.2E1 | 4.5E1 | 4.3E1 | 3.2E1 | 8.4E-5 | 3.2E0 | 2.9E2 | 1.3E2 | 357 | 17 | 135 | 17 | 0.56 |
| Ar | ng/mL | 8.5E-1 | 1.1E0 | 1.5E1 | 4.4E0 | 2.2E2 | 1.1E1 | 3.4E-3 | 1.5E-1 | 4.1E3 | 4.7E1 | 357 | 17 | 135 | 17 | 0.54 |
| As | ng/mL | 9.5E-3 | 1.2E-2 | 1.3E-2 | 1.3E-2 | 1.8E-2 | 1.4E-2 | 1.7E-3 | 1.7E-3 | 1.3E-1 | 6.1E-2 | 357 | 17 | 135 | 17 | 0.54 |
| Aw | pg/mL | 1.6E1 | 2.0E1 | 1.6E1 | 1.8E1 | 5.9E0 | 4.8E0 | 2.9E-2 | 1.1E1 | 4.8E1 | 2.5E1 | 357 | 17 | 135 | 17 | 0.63 |
| Ax | ng/mL | 2.2E0 | 6.1E0 | 1.4E1 | 1.1E1 | 5.8E1 | 1.7E1 | 1.3E-2 | 9.6E-2 | 7.7E2 | 6.0E1 | 357 | 17 | 135 | 17 | 0.58 |
| Ba | ng/mL | 6.2E1 | 1.7E2 | 4.2E2 | 8.8E2 | 1.2E3 | 2.0E3 | 3.7E-1 | 4.1E0 | 8.1E3 | 8.1E3 | 357 | 17 | 135 | 17 | 0.62 |
| Bb | ng/mL | 2.8E0 | 3.8E0 | 6.1E0 | 4.4E0 | 1.5E1 | 3.8E0 | 4.1E-3 | 5.2E-1 | 2.5E2 | 1.2E1 | 357 | 17 | 135 | 17 | 0.51 |
| Bc | ng/mL | 3.4E1 | 6.9E1 | 1.0E2 | 1.3E2 | 1.9E2 | 2.1E2 | 1.1E-1 | 7.0E0 | 1.2E3 | 8.9E2 | 357 | 17 | 135 | 17 | 0.64 |
| Bg | ng/mL | 7.7E-2 | 2.8E-1 | 4.0E0 | 2.4E1 | 1.9E1 | 9.6E1 | 5.3E-4 | 5.3E-1 | 2.5E2 | 4.0E2 | 357 | 17 | 135 | 17 | 0.58 |
| Bn | ng/mL | 5.6E-2 | 5.6E-2 | 1.1E0 | 1.5E0 | 1.9E0 | 2.1E0 | 5.6E-2 | 5.6E-2 | 9.7E0 | 6.5E0 | 357 | 17 | 135 | 17 | 0.54 |
| Bo | ng/mL | 1.2E1 | 2.2E1 | 1.4E1 | 2.0E1 | 2.0E1 | 1.1E1 | 1.6E-2 | 1.6E-2 | 2.8E2 | 3.9E1 | 357 | 17 | 135 | 17 | 0.69 |
| Ch | uIU/mL | 1.2E0 | 9.6E-1 | 2.1E1 | 7.2E1 | 1.1E2 | 2.9E2 | 3.4E-3 | 3.4E-3 | 1.8E3 | 1.2E3 | 357 | 17 | 135 | 17 | 0.42 |
| Co | pg/mL | 3.8E1 | 4.6E1 | 1.8E2 | 7.4E1 | 1.1E3 | 1.1E2 | 1.5E-1 | 6.2E0 | 1.7E4 | 5.0E2 | 357 | 17 | 135 | 17 | 0.52 |
| Cp | ng/mL | 2.2E1 | 2.9E1 | 2.8E1 | 3.1E1 | 3.3E1 | 1.8E1 | 6.0E-1 | 2.5E0 | 3.7E2 | 7.0E1 | 357 | 17 | 135 | 17 | 0.60 |
| Cq | ng/mL | 2.8E-2 | 5.0E-2 | 1.5E-1 | 8.7E-2 | 9.5E-1 | 1.1E-1 | 8.0E-4 | 8.0E-4 | 1.7E1 | 4.0E-1 | 357 | 17 | 135 | 17 | 0.59 |
| Cs | ng/mL | 6.6E1 | 2.1E2 | 3.0E2 | 2.5E2 | 8.6E2 | 3.0E2 | 2.7E-2 | 4.4E0 | 1.1E4 | 1.2E3 | 357 | 17 | 135 | 17 | 0.58 |
| Ct | ng/mL | 8.9E-1 | 1.8E-1 | 4.0E1 | 5.3E0 | 1.1E2 | 1.2E1 | 1.1E-4 | 2.5E-2 | 6.2E2 | 4.9E1 | 357 | 17 | 135 | 17 | 0.39 |
| Cu | ng/mL | 2.4E-1 | 3.1E-1 | 4.0E-1 | 4.3E-1 | 7.0E-1 | 4.1E-1 | 9.6E-3 | 4.6E-2 | 9.2E0 | 1.7E0 | 357 | 17 | 135 | 17 | 0.58 |
| Cv | ng/mL | 4.1E0 | 8.7E0 | 1.8E1 | 3.2E1 | 4.9E1 | 5.1E1 | 1.4E-4 | 2.4E-1 | 5.3E2 | 1.7E2 | 357 | 17 | 135 | 17 | 0.59 |
| Cw | mIU/mL | 3.0E-2 | 3.7E-2 | 3.8E-2 | 3.8E-2 | 3.2E-2 | 1.8E-2 | 8.9E-4 | 9.0E-3 | 2.4E-1 | 6.4E-2 | 357 | 17 | 135 | 17 | 0.56 |
| Cx | ng/mL | 1.5E-1 | 6.2E-1 | 5.1E1 | 9.0E1 | 9.9E1 | 1.5E2 | 9.3E-5 | 9.3E-5 | 3.9E2 | 3.9E2 | 357 | 17 | 135 | 17 | 0.51 |
| Db | ug/mL | 7.2E0 | 7.3E0 | 8.6E0 | 8.8E0 | 7.3E0 | 7.2E0 | 4.5E-1 | 9.7E-1 | 5.9E1 | 3.1E1 | 357 | 17 | 135 | 17 | 0.61 |
| Dc | nmol/L | 1.9E-2 | 2.4E-2 | 5.7E-2 | 7.9E-2 | 1.4E-1 | 1.5E-1 | 5.2E-6 | 1.6E-3 | 1.6E0 | 6.3E-1 | 357 | 17 | 135 | 17 | 0.60 |
| Dd | ug/mL | 6.9E-2 | 1.4E-1 | 1.8E-1 | 1.7E-1 | 2.7E-1 | 1.7E-1 | 1.9E-4 | 7.7E-3 | 1.9E0 | 6.0E-1 | 357 | 17 | 135 | 17 | 0.51 |
| De | ng/mL | 3.4E-3 | 3.4E-3 | 7.8E-2 | 7.1E-2 | 1.4E-1 | 1.0E-1 | 3.4E-3 | 3.4E-3 | 9.2E-1 | 3.2E-1 | 357 | 17 | 135 | 17 | 0.63 |
| Dg | ng/mL | 2.9E1 | 4.7E1 | 4.2E1 | 5.8E1 | 3.8E1 | 4.2E1 | 1.0E-1 | 2.2E0 | 1.9E2 | 1.9E2 | 357 | 17 | 135 | 17 | 0.52 |
| Di | pg/mL | 2.0E0 | 1.6E0 | 2.2E0 | 2.4E0 | 2.0E0 | 2.3E0 | 1.8E-1 | 1.8E-1 | 1.3E1 | 9.2E0 | 357 | 17 | 135 | 17 | 0.53 |
| Dk | uIU/mL | 1.7E-2 | 1.8E-2 | 9.6E-2 | 6.3E-2 | 5.7E-1 | 9.2E-2 | 1.1E-4 | 1.1E-4 | 8.9E0 | 3.3E-1 | 357 | 17 | 135 | 17 | 0.52 |
| Dl | ng/mL | 2.3E2 | 2.8E2 | 3.1E2 | 3.3E2 | 2.8E2 | 3.1E2 | 1.7E0 | 1.7E1 | 1.5E3 | 1.3E3 | 357 | 17 | 135 | 15 | 0.48 |
| Dp | ng/ml | 2.3E0 | 3.0E0 | 5.1E0 | 4.6E0 | 7.9E0 | 5.6E0 | 3.7E-3 | 3.7E-3 | 4.6E1 | 1.8E1 | 217 | 15 | 134 | 16 | 0.48 |
| Ef | ng/ml | 1.5E-1 | 1.3E-1 | 8.1E-1 | 1.1E0 | 1.6E0 | 2.6E0 | 5.7E-4 | 4.1E-3 | 9.5E0 | 9.4E0 | 261 | 16 | 151 | 17 | 0.58 |
| Wm | % | 4.9E-1 | 2.4E0 | 2.3E1 | 4.8E1 | 1.6E2 | 1.9E2 | 5.4E-2 | 8.5E-2 | 2.4E3 | 7.7E2 | 283 | 17 | 134 | 15 | 0.62 |
| Ed | pg/ml | 5.2E-1 | 2.9E1 | 6.3E1 | 4.2E1 | 5.0E2 | 4.2E1 | 5.2E-1 | 5.2E-1 | 7.3E3 | 1.1E2 | 217 | 15 | 136 | 15 | 0.46 |
| Tj | pg/mL | 3.7E-1 | 3.7E-1 | 6.8E1 | 6.7E0 | 3.3E2 | 1.5E1 | 3.6E-1 | 3.7E-1 | 3.5E3 | 5.6E1 | 258 | 15 | 207 | 25 | 0.55 |
| Po | pg/ml | 6.7E-1 | 2.6E0 | 9.1E0 | 6.0E0 | 2.5E1 | 7.4E0 | 8.0E-3 | 2.6E-2 | 2.7E2 | 2.1E1 | 580 | 25 | 71 | 7 | 0.54 |
| Em | ng/ml | 9.2E-3 | 1.4E-2 | 6.7E-2 | 9.5E-2 | 1.2E-1 | 1.8E-1 | 1.9E-16 | 2.9E-3 | 6.0E-1 | 5.0E-1 | 149 | 7 | 207 | 25 | 0.65 |
| Et | ng/ml | 1.3E3 | 2.2E3 | 1.6E3 | 2.2E3 | 1.1E3 | 1.3E3 | 7.7E1 | 1.4E2 | 5.0E3 | 4.1E3 | 579 | 25 | 133 | 16 | 0.67 |
| Fa | ng/ml | 4.0E1 | 8.9E1 | 1.3E2 | 8.8E1 | 6.0E2 | 5.9E1 | 3.4E-2 | 1.6E0 | 8.0E3 | 2.2E2 | 212 | 16 | 135 | 15 | 0.49 |
| Ez | ng/ml | 5.0E0 | 4.1E0 | 2.0E1 | 1.1E1 | 5.9E1 | 1.3E1 | 1.3E-2 | 1.3E-2 | 7.1E2 | 3.4E1 | 217 | 15 | 133 | 16 | 0.50 |
| Fb | ng/ml | 2.5E1 | 2.7E1 | 2.3E1 | 2.3E1 | 1.1E1 | 1.1E1 | 6.6E-1 | 8.1E-1 | 5.7E1 | 3.5E1 | 213 | 16 | 89 | 13 | 0.54 |
| Ex | ng/ml | 7.8E-2 | 9.5E-2 | 2.5E-1 | 1.4E-1 | 7.6E-1 | 1.4E-1 | 3.5E-5 | 1.7E-4 | 8.9E0 | 5.0E-1 | 190 | 13 | 135 | 15 | 0.43 |
| Fn | ng/ml | 2.1E-1 | 2.1E-1 | 6.3E0 | 2.2E0 | 2.9E1 | 4.1E0 | 1.1E-14 | 1.1E-14 | 4.2E2 | 1.6E1 | 217 | 15 | 209 | 25 | 0.59 |
| Fp | ng/ml | 1.2E1 | 2.2E1 | 2.4E1 | 3.1E1 | 2.8E1 | 2.9E1 | 6.0E-3 | 2.8E-1 | 1.4E2 | 1.3E2 | 606 | 25 | 210 | 25 | 0.62 |
| Fr | ng/ml | 3.3E4 | 5.6E4 | 1.1E5 | 2.0E5 | 1.7E5 | 2.7E5 | 1.9E2 | 3.2E2 | 9.0E5 | 8.3E5 | 686 | 25 | 135 | 16 | 0.59 |
| Fw | pg/ml | 8.5E-1 | 2.7E0 | 7.0E1 | 1.2E1 | 5.4E2 | 1.8E1 | 1.1E-14 | 1.2E-1 | 6.9E3 | 5.3E1 | 259 | 16 | 134 | 14 | 0.47 |
| Fy | ng/ml | 3.5E1 | 2.2E1 | 5.5E1 | 5.6E1 | 5.7E1 | 7.7E1 | 1.2E-1 | 1.5E0 | 3.3E2 | 2.3E2 | 216 | 14 | 135 | 16 | 0.51 |
| Gl | pg/ml | 7.8E3 | 7.9E3 | 1.1E4 | 1.1E4 | 9.4E3 | 8.8E3 | 9.1E1 | 2.5E2 | 3.3E4 | 2.8E4 | 252 | 16 | 135 | 16 | 0.51 |

Figure 20

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Gp | U/ml | 1.5E0 | 9.1E-1 | 4.0E0 | 2.9E0 | 6.8E0 | 5.3E0 | 1.3E-3 | 1.5E-2 | 6.7E1 | 2.0E1 | 261 | 16 | 135 | 16 | 0.43 |
| Gz | ug/ml | 1.4E0 | 8.1E-1 | 9.7E0 | 3.8E0 | 4.2E1 | 6.0E0 | 2.9E-16 | 3.8E-3 | 4.8E2 | 1.9E1 | 143 | 13 | 86 | 13 | 0.45 |
| Ha | ng/ml | 2.7E0 | 2.4E0 | 9.9E0 | 5.7E0 | 2.1E1 | 8.3E0 | 1.7E-2 | 1.7E-2 | 1.3E2 | 3.3E1 | 215 | 15 | 134 | 15 | 0.50 |
| Nm | pg/ml | 1.6E4 | 1.4E4 | 3.2E4 | 2.9E4 | 8.8E4 | 3.3E4 | 1.0E-9 | 1.0E-9 | 1.6E6 | 1.2E5 | 583 | 25 | 209 | 25 | 0.52 |
| Nn | pg/ml | 1.5E2 | 4.7E2 | 2.2E3 | 8.3E2 | 9.4E3 | 1.2E3 | 1.0E-9 | 1.0E-9 | 1.0E5 | 4.7E3 | 583 | 25 | 209 | 25 | 0.58 |
| No | pg/ml | 1.5E1 | 2.1E1 | 3.7E1 | 3.0E1 | 1.3E2 | 3.7E1 | 1.0E-9 | 1.0E-9 | 2.5E3 | 1.4E2 | 583 | 25 | 209 | 25 | 0.52 |
| Nq | pg/ml | 2.0E0 | 4.0E0 | 1.9E1 | 2.0E1 | 7.6E1 | 5.0E1 | 1.0E-9 | 1.0E-9 | 1.2E3 | 2.4E2 | 583 | 25 | 209 | 25 | 0.56 |
| Nr | pg/ml | 8.8E-1 | 1.5E0 | 3.3E1 | 1.4E1 | 2.1E2 | 3.1E1 | 1.0E-9 | 1.0E-9 | 4.1E3 | 1.4E2 | 583 | 25 | 209 | 25 | 0.54 |
| Ns | pg/ml | 1.0E-9 | 1.0E-9 | 1.1E1 | 9.9E0 | 6.1E1 | 4.8E1 | 1.0E-9 | 1.0E-9 | 1.1E3 | 2.4E2 | 583 | 25 | 209 | 25 | 0.51 |
| Nt | pg/ml | 1.0E2 | 1.0E2 | 1.4E2 | 1.3E2 | 1.1E2 | 7.7E1 | 1.0E-9 | 2.3E1 | 1.5E3 | 3.5E2 | 583 | 25 | 209 | 25 | 0.53 |
| Nu | pg/ml | 2.3E1 | 2.0E1 | 5.7E1 | 5.8E1 | 9.5E1 | 7.5E1 | 1.0E-9 | 1.0E-9 | 8.9E2 | 2.6E2 | 583 | 25 | 209 | 25 | 0.50 |
| Lu | pg/ml | 1.0E4 | 9.8E3 | 1.7E4 | 1.0E4 | 4.7E4 | 1.1E4 | 3.5E2 | 1.0E3 | 7.5E5 | 5.5E4 | 585 | 25 | 209 | 25 | 0.43 |
| Lv | pg/ml | 1.0E-9 | 1.0E-9 | 1.1E1 | 3.8E1 | 2.1E1 | 6.9E1 | 1.0E-9 | 1.0E-9 | 2.4E2 | 2.6E2 | 585 | 25 | 209 | 25 | 0.59 |
| Lw | pg/ml | 1.0E-9 | 1.0E-9 | 4.0E-1 | 4.1E-1 | 4.3E0 | 2.0E0 | 1.0E-9 | 1.0E-9 | 8.0E1 | 9.9E0 | 585 | 25 | 209 | 25 | 0.53 |
| Lx | pg/ml | 1.0E-9 | 6.0E1 | 1.5E2 | 2.1E2 | 4.5E2 | 3.3E2 | 1.0E-9 | 1.0E-9 | 6.2E3 | 1.4E3 | 585 | 25 | 209 | 25 | 0.63 |
| Ly | pg/ml | 1.0E-9 | 1.5E1 | 1.0E1 | 1.5E1 | 2.0E1 | 1.8E1 | 1.0E-9 | 1.0E-9 | 1.6E2 | 7.0E1 | 585 | 25 | 209 | 25 | 0.62 |
| Lz | pg/ml | 1.0E-9 | 1.0E-9 | 4.9E0 | 1.0E-9 | 3.6E1 | 0.0E0 | 1.0E-9 | 1.0E-9 | 6.0E2 | 1.0E-9 | 585 | 25 | 209 | 25 | 0.46 |
| Ma | pg/ml | 3.1E2 | 3.3E2 | 1.3E3 | 4.0E3 | 3.8E3 | 1.1E4 | 1.0E-9 | 1.0E-9 | 6.5E4 | 5.2E4 | 585 | 25 | 209 | 25 | 0.55 |
| Mb | pg/ml | 2.5E1 | 2.8E1 | 3.1E1 | 3.2E1 | 1.6E1 | 1.5E1 | 5.4E0 | 1.4E1 | 2.1E2 | 5.8E1 | 585 | 25 | 209 | 25 | 0.48 |
| Mc | pg/ml | 1.0E-9 | 1.0E-9 | 4.2E-2 | 1.0E-9 | 5.8E-1 | 0.0E0 | 1.0E-9 | 1.0E-9 | 1.3E1 | 1.0E-9 | 585 | 25 | 209 | 25 | 0.49 |
| Md | pg/ml | 1.0E-9 | 1.0E-9 | 4.8E-1 | 2.0E-2 | 3.3E0 | 9.8E-2 | 1.0E-9 | 1.0E-9 | 6.5E1 | 4.9E-1 | 585 | 25 | 209 | 25 | 0.47 |
| Me | pg/ml | 3.2E1 | 2.9E1 | 3.1E1 | 2.8E1 | 2.0E1 | 1.3E1 | 1.0E-9 | 2.4E-1 | 3.2E2 | 5.6E1 | 585 | 25 | 209 | 25 | 0.43 |
| Mf | pg/ml | 1.0E-9 | 1.0E-9 | 5.2E-1 | 3.2E-1 | 3.1E0 | 1.1E0 | 1.0E-9 | 1.0E-9 | 5.6E1 | 5.0E0 | 585 | 25 | 209 | 25 | 0.49 |
| Mg | pg/ml | 2.0E0 | 1.1E0 | 7.7E0 | 6.6E0 | 1.3E1 | 7.9E0 | 1.0E-9 | 1.0E-9 | 9.2E1 | 2.6E1 | 585 | 25 | 209 | 25 | 0.51 |
| Mh | pg/ml | 1.0E-9 | 1.0E-9 | 1.5E0 | 4.1E-1 | 1.1E1 | 1.6E0 | 1.0E-9 | 1.0E-9 | 1.6E2 | 7.8E0 | 585 | 25 | 209 | 25 | 0.51 |
| Mi | pg/ml | 1.0E-9 | 1.0E-9 | 5.9E-1 | 1.1E0 | 6.3E0 | 5.4E0 | 1.0E-9 | 1.0E-9 | 1.2E2 | 2.7E1 | 585 | 25 | 209 | 25 | 0.51 |
| Mj | pg/ml | 1.0E-9 | 1.0E-9 | 4.8E0 | 3.8E0 | 2.7E1 | 7.7E0 | 1.0E-9 | 1.0E-9 | 4.6E2 | 2.4E1 | 585 | 25 | 209 | 25 | 0.54 |
| Mk | pg/ml | 5.3E-1 | 2.0E0 | 1.8E1 | 5.8E0 | 1.1E2 | 9.6E0 | 1.0E-9 | 1.0E-9 | 1.7E3 | 4.0E1 | 585 | 25 | 209 | 25 | 0.50 |
| Ml | pg/ml | 1.0E-9 | 1.0E-9 | 6.3E0 | 3.7E-1 | 9.0E1 | 1.6E0 | 1.0E-9 | 1.0E-9 | 2.1E3 | 8.0E0 | 585 | 25 | 209 | 25 | 0.45 |
| Mm | pg/ml | 5.9E2 | 8.2E2 | 9.8E2 | 1.6E3 | 1.1E3 | 2.2E3 | 1.0E-9 | 8.8E-2 | 7.3E3 | 9.9E3 | 585 | 25 | 209 | 25 | 0.57 |
| Mn | pg/ml | 5.4E0 | 6.0E0 | 1.1E1 | 1.1E1 | 2.6E1 | 1.2E1 | 1.0E-9 | 1.0E-9 | 3.5E2 | 5.2E1 | 585 | 25 | 209 | 25 | 0.57 |
| Mp | pg/ml | 1.0E-9 | 1.0E-9 | 9.2E0 | 1.9E1 | 3.2E1 | 3.8E1 | 1.0E-9 | 1.0E-9 | 6.3E2 | 1.5E2 | 584 | 25 | 209 | 25 | 0.52 |
| Mq | pg/ml | 1.0E-9 | 1.0E-9 | 2.9E0 | 3.8E0 | 1.7E1 | 1.3E1 | 1.0E-9 | 1.0E-9 | 2.1E2 | 6.2E1 | 584 | 25 | 209 | 25 | 0.53 |
| Mr | pg/ml | 1.0E-9 | 1.0E-9 | 1.9E1 | 1.3E1 | 8.5E1 | 5.8E1 | 1.0E-9 | 1.0E-9 | 1.4E3 | 2.9E2 | 584 | 25 | 209 | 25 | 0.48 |
| Ms | pg/ml | 4.1E2 | 1.7E2 | 5.6E2 | 3.5E2 | 6.5E2 | 3.6E2 | 1.0E-9 | 1.0E-9 | 5.6E3 | 1.5E3 | 584 | 25 | 209 | 25 | 0.40 |
| Mt | pg/ml | 2.2E-1 | 1.2E0 | 7.4E0 | 5.3E0 | 5.0E1 | 1.4E1 | 1.0E-9 | 1.0E-9 | 8.7E2 | 7.0E1 | 584 | 25 | 209 | 25 | 0.64 |
| Mu | pg/ml | 1.0E-9 | 1.0E-9 | 1.6E0 | 1.2E0 | 1.3E1 | 3.7E0 | 1.0E-9 | 1.0E-9 | 2.3E2 | 1.8E1 | 584 | 25 | 209 | 25 | 0.55 |
| Mv | pg/ml | 1.0E-9 | 1.0E-9 | 7.6E1 | 8.5E1 | 3.6E2 | 2.0E2 | 1.0E-9 | 1.0E-9 | 4.5E3 | 6.5E2 | 584 | 25 | 209 | 25 | 0.55 |
| Mw | pg/ml | 3.4E1 | 5.9E1 | 4.8E2 | 3.0E2 | 3.1E3 | 6.1E2 | 1.0E-9 | 1.0E-9 | 6.2E4 | 2.7E3 | 584 | 25 | 209 | 25 | 0.53 |
| Mx | pg/ml | 1.0E-9 | 1.0E-9 | 2.5E-1 | 3.1E-1 | 1.5E0 | 8.1E-1 | 1.0E-9 | 1.0E-9 | 3.2E1 | 3.4E0 | 584 | 25 | 209 | 25 | 0.54 |
| My | pg/ml | 1.0E-9 | 1.0E-9 | 4.7E2 | 1.9E2 | 3.1E3 | 4.2E2 | 1.0E-9 | 1.0E-9 | 3.9E4 | 1.7E3 | 584 | 25 | 209 | 25 | 0.57 |
| Mz | pg/ml | 1.0E1 | 1.2E1 | 2.5E1 | 4.4E1 | 7.2E1 | 6.9E1 | 1.0E-9 | 1.0E-9 | 1.2E3 | 2.7E2 | 584 | 25 | 209 | 25 | 0.57 |
| Na | pg/ml | 1.0E-9 | 1.0E-9 | 7.4E-1 | 3.7E-1 | 3.0E0 | 1.4E0 | 1.0E-9 | 1.0E-9 | 3.6E1 | 7.2E0 | 584 | 25 | 209 | 25 | 0.47 |
| Nb | pg/ml | 1.9E0 | 2.6E0 | 4.2E0 | 3.3E0 | 1.4E1 | 2.6E0 | 1.0E-9 | 1.0E-9 | 2.3E2 | 1.0E1 | 584 | 25 | 209 | 25 | 0.58 |
| Nc | pg/ml | 4.0E2 | 1.1E2 | 6.3E2 | 2.8E2 | 7.9E2 | 4.8E2 | 1.0E-9 | 1.0E-9 | 9.2E3 | 2.1E3 | 584 | 25 | 209 | 25 | 0.33 |
| Nd | pg/ml | 2.9E1 | 6.8E0 | 2.7E1 | 1.5E1 | 5.4E1 | 1.7E1 | 1.0E-9 | 1.0E-9 | 1.2E3 | 5.2E1 | 584 | 25 | 209 | 25 | 0.36 |
| Ne | pg/ml | 4.7E2 | 2.6E2 | 6.1E2 | 3.0E2 | 6.0E2 | 3.3E2 | 1.0E-9 | 1.0E-9 | 7.0E3 | 1.5E3 | 584 | 25 | 209 | 25 | 0.33 |
| Nf | pg/ml | 1.0E-9 | 1.0E-9 | 3.0E0 | 5.1E-1 | 1.1E1 | 1.7E0 | 1.0E-9 | 1.0E-9 | 1.6E2 | 6.9E0 | 584 | 25 | 209 | 25 | 0.44 |
| Ng | pg/ml | 3.6E1 | 6.3E0 | 1.4E2 | 9.1E1 | 2.6E2 | 1.8E2 | 1.0E-9 | 1.0E-9 | 2.3E3 | 6.4E2 | 584 | 25 | 209 | 25 | 0.43 |
| Nh | pg/ml | 7.1E1 | 3.2E1 | 9.5E1 | 5.5E1 | 8.8E1 | 5.8E1 | 1.0E-9 | 3.1E0 | 5.6E2 | 2.2E2 | 584 | 25 | 209 | 25 | 0.34 |
| Ni | pg/ml | 1.0E-9 | 1.0E-9 | 7.8E1 | 8.4E1 | 1.2E2 | 1.3E2 | 1.0E-9 | 1.0E-9 | 7.1E2 | 3.7E2 | 584 | 25 | 209 | 25 | 0.51 |
| Nj | pg/ml | 7.9E0 | 2.4E0 | 1.1E1 | 5.5E0 | 1.2E1 | 6.6E0 | 1.0E-9 | 1.0E-9 | 8.3E1 | 2.0E1 | 584 | 25 | 209 | 25 | 0.33 |
| Nk | pg/ml | 2.0E1 | 1.2E1 | 3.5E1 | 1.7E1 | 4.0E1 | 1.9E1 | 1.0E-9 | 1.0E-9 | 2.0E2 | 6.9E1 | 584 | 25 | 209 | 25 | 0.40 |
| Nl | pg/ml | 4.9E1 | 1.6E1 | 6.6E1 | 3.3E1 | 7.4E1 | 4.1E1 | 1.0E-9 | 1.0E-9 | 1.1E3 | 1.4E2 | 584 | 25 | 209 | 25 | 0.33 |
| Tz | pg/ml | 5.3E3 | 5.4E3 | 1.4E4 | 2.0E4 | 6.9E4 | 4.4E4 | 1.0E-9 | 7.5E2 | 1.0E6 | 1.7E5 | 219 | 15 | 133 | 15 | 0.51 |
| Ua | pg/ml | 3.9E3 | 3.7E3 | 1.6E4 | 9.4E3 | 2.9E4 | 1.5E4 | 1.0E-9 | 2.7E2 | 1.9E5 | 5.8E4 | 219 | 15 | 133 | 15 | 0.46 |
| Ub | pg/ml | 5.7E2 | 3.9E2 | 8.5E2 | 4.0E2 | 1.1E3 | 3.7E2 | 1.0E-9 | 1.5E1 | 9.8E3 | 1.4E3 | 219 | 15 | 133 | 15 | 0.35 |

Figure 20 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ue | pg/ml | 2.9E1 | 2.1E1 | 3.6E1 | 2.4E1 | 3.2E1 | 1.7E1 | 9.8E-2 | 2.9E0 | 3.5E2 | 7.4E1 | 219 | 15 | 133 | 15 | 0.34 |
| Uc | pg/ml | 9.2E2 | 1.4E3 | 1.7E3 | 2.5E3 | 2.9E3 | 3.1E3 | 1.0E-9 | 2.1E1 | 2.9E4 | 9.4E3 | 219 | 15 | 133 | 15 | 0.56 |
| Ud | pg/ml | 1.0E-9 | 1.0E-9 | 1.9E0 | 1.0E-9 | 2.6E1 | 0.0E0 | 1.0E-9 | 1.0E-9 | 3.9E2 | 1.0E-9 | 219 | 15 | 133 | 15 | 0.49 |
| Hq | pg/ml | 1.1E0 | 1.8E0 | 1.5E2 | 2.1E1 | 2.0E3 | 6.9E1 | 1.0E-9 | 1.0E-9 | 3.4E4 | 3.4E2 | 581 | 25 | 208 | 25 | 0.54 |
| Hr | pg/ml | 1.3E2 | 7.3E1 | 8.0E2 | 6.4E2 | 1.6E3 | 1.0E3 | 1.0E-9 | 2.3E1 | 1.4E4 | 3.7E3 | 581 | 25 | 208 | 25 | 0.46 |
| Hu | pg/ml | 1.1E1 | 1.5E1 | 3.2E3 | 6.2E2 | 3.1E4 | 1.4E3 | 1.0E-9 | 1.0E-9 | 6.3E5 | 5.8E3 | 581 | 25 | 208 | 25 | 0.53 |
| Hv | pg/ml | 1.5E0 | 2.4E0 | 3.4E0 | 2.3E0 | 1.2E1 | 1.7E0 | 1.0E-9 | 1.0E-9 | 2.5E2 | 6.9E0 | 581 | 25 | 208 | 25 | 0.60 |
| Hw | pg/ml | 7.0E0 | 5.0E0 | 2.2E1 | 8.1E0 | 8.6E1 | 7.4E0 | 1.0E-9 | 1.0E-9 | 1.7E3 | 2.3E1 | 581 | 25 | 208 | 25 | 0.43 |
| Hx | pg/ml | 9.6E0 | 1.4E1 | 4.7E1 | 2.9E1 | 4.0E2 | 4.5E1 | 1.0E-9 | 1.0E-9 | 9.3E3 | 2.2E2 | 581 | 25 | 208 | 25 | 0.56 |
| Ib | ng/ml | 6.7E-2 | 1.5E-2 | 2.3E0 | 8.6E-2 | 7.8E0 | 1.8E-1 | 1.0E-9 | 1.0E-9 | 5.3E1 | 6.8E-1 | 210 | 15 | 132 | 15 | 0.33 |
| Ic | U/ml | 2.2E2 | 2.2E2 | 8.1E2 | 4.5E3 | 6.5E3 | 1.7E4 | 2.4E0 | 2.2E1 | 9.3E4 | 6.5E4 | 210 | 15 | 132 | 15 | 0.50 |
| Id | U/ml | 6.5E-1 | 9.5E-1 | 1.2E0 | 2.3E0 | 2.0E0 | 3.2E0 | 1.0E-9 | 2.7E-1 | 2.3E1 | 1.2E1 | 210 | 15 | 132 | 15 | 0.61 |
| Tt | pg/ml | 1.7E2 | 1.6E2 | 1.7E2 | 1.7E2 | 5.1E1 | 5.1E1 | 4.3E1 | 1.1E2 | 3.6E2 | 2.6E2 | 202 | 14 | 127 | 14 | 0.48 |
| To | pg/ml | 1.6E0 | 1.8E0 | 1.9E0 | 2.3E0 | 2.0E0 | 2.0E0 | 1.0E-9 | 1.0E-9 | 1.0E1 | 6.0E0 | 211 | 14 | 130 | 14 | 0.59 |
| Tr | pg/ml | 3.0E0 | 3.0E0 | 6.2E0 | 9.6E0 | 2.2E1 | 1.5E1 | 1.0E-9 | 3.3E-1 | 3.1E2 | 5.4E1 | 207 | 14 | 129 | 14 | 0.54 |
| Tn | pg/ml | 2.9E1 | 4.2E1 | 7.5E1 | 2.0E2 | 2.0E2 | 5.1E2 | 2.4E0 | 1.3E1 | 1.8E3 | 2.0E3 | 211 | 14 | 130 | 14 | 0.62 |
| Tv | ng/ml | 1.2E1 | 8.0E0 | 2.0E1 | 4.5E1 | 3.9E1 | 8.8E1 | 1.0E-9 | 1.0E-9 | 4.9E2 | 3.2E2 | 211 | 14 | 130 | 14 | 0.48 |
| Ih | ng/ml | 7.5E1 | 4.5E1 | 2.1E2 | 1.8E2 | 3.6E2 | 2.5E2 | 1.0E-9 | 1.0E-9 | 2.6E3 | 9.0E2 | 584 | 25 | 208 | 25 | 0.50 |
| Ii | ng/ml | 9.8E1 | 9.1E1 | 2.7E2 | 1.5E2 | 7.6E2 | 2.0E2 | 7.3E-1 | 9.1E0 | 1.0E4 | 8.1E2 | 584 | 25 | 208 | 25 | 0.48 |
| Ij | ng/ml | 7.6E1 | 8.7E1 | 1.9E2 | 1.0E2 | 6.3E2 | 7.1E1 | 2.1E0 | 1.0E-9 | 6.4E3 | 3.0E2 | 579 | 25 | 207 | 25 | 0.52 |
| Ik | ng/ml | 1.4E1 | 4.2E1 | 1.1E3 | 2.7E2 | 1.0E4 | 4.4E2 | 5.9E-1 | 2.1E0 | 1.2E5 | 1.5E3 | 581 | 25 | 207 | 25 | 0.55 |
| Il | ng/ml | 3.4E2 | 5.3E2 | 1.3E3 | 1.1E3 | 2.7E3 | 2.4E3 | 1.0E-9 | 1.0E-9 | 1.2E4 | 1.2E4 | 574 | 25 | 207 | 25 | 0.49 |
| Im | ng/ml | 2.0E2 | 2.4E2 | 3.5E2 | 3.8E2 | 5.2E2 | 3.1E2 | 1.3E1 | 2.5E1 | 6.0E3 | 1.1E3 | 581 | 25 | 207 | 25 | 0.58 |
| In | ng/ml | 3.9E0 | 1.6E0 | 2.5E1 | 6.4E0 | 1.8E2 | 1.7E1 | 1.0E-9 | 1.0E-9 | 3.9E3 | 8.4E1 | 584 | 25 | 208 | 25 | 0.37 |
| Hb | ng/ml | 2.4E1 | 2.0E1 | 3.2E1 | 2.7E1 | 2.9E1 | 2.5E1 | 4.8E-1 | 2.1E0 | 1.4E2 | 9.0E1 | 217 | 16 | 134 | 16 | 0.45 |
| Hc | pg/ml | 7.6E2 | 5.3E2 | 4.0E3 | 3.7E3 | 1.4E4 | 1.2E4 | 1.0E-9 | 2.2E2 | 1.0E5 | 5.0E4 | 217 | 16 | 134 | 16 | 0.43 |
| Hf | ng/ml | 1.5E2 | 1.1E2 | 4.1E2 | 2.4E2 | 5.8E2 | 2.9E2 | 1.0E-9 | 1.0E-9 | 3.2E3 | 8.2E2 | 217 | 16 | 134 | 16 | 0.46 |
| Io | ng/ml | 8.4E3 | 1.2E4 | 2.7E4 | 1.7E4 | 1.8E5 | 2.3E4 | 1.0E-9 | 1.3E3 | 4.0E6 | 1.1E5 | 578 | 23 | 208 | 23 | 0.56 |
| Ip | ng/ml | 1.0E1 | 2.5E1 | 1.9E1 | 3.0E1 | 2.4E1 | 3.7E1 | 1.0E-9 | 1.1E-2 | 2.6E2 | 1.6E2 | 578 | 23 | 208 | 23 | 0.57 |
| Iq | ug/ml | 9.8E-2 | 1.1E-1 | 2.4E1 | 2.4E-1 | 5.7E2 | 3.6E-1 | 1.0E-9 | 1.0E-9 | 1.4E4 | 1.4E0 | 578 | 23 | 208 | 23 | 0.50 |
| Ir | ug/ml | 3.4E-1 | 6.0E-1 | 2.7E0 | 1.5E0 | 1.7E1 | 3.2E0 | 1.0E-9 | 1.0E-9 | 2.4E2 | 1.6E1 | 577 | 23 | 208 | 23 | 0.62 |
| Is | ng/ml | 1.5E0 | 4.1E0 | 5.4E0 | 1.1E1 | 1.1E1 | 2.3E1 | 1.0E-9 | 2.7E-1 | 8.8E1 | 1.1E2 | 578 | 23 | 208 | 23 | 0.68 |
| It | ng/ml | 1.9E0 | 1.7E0 | 2.2E1 | 5.3E0 | 1.5E2 | 9.7E0 | 1.0E-9 | 1.0E-9 | 2.8E3 | 4.7E1 | 578 | 23 | 208 | 23 | 0.57 |
| Iu | ng/ml | 2.2E2 | 2.0E2 | 1.3E3 | 2.0E3 | 4.0E3 | 5.1E3 | 1.0E-9 | 1.0E-9 | 2.9E4 | 2.4E4 | 578 | 23 | 208 | 23 | 0.56 |
| Iv | ng/ml | 1.4E1 | 1.8E1 | 4.1E1 | 3.1E1 | 1.0E2 | 3.1E1 | 1.0E-9 | 1.0E-9 | 1.6E3 | 9.1E1 | 577 | 23 | 208 | 23 | 0.54 |
| Iz | ng/ml | 1.5E2 | 9.6E1 | 7.3E2 | 3.1E2 | 4.3E3 | 4.5E2 | 1.5E0 | 1.3E1 | 6.2E4 | 1.7E3 | 217 | 16 | 134 | 16 | 0.44 |
| Rc | pg/ml | 5.7E3 | 6.3E3 | 7.2E3 | 8.0E3 | 5.4E3 | 5.3E3 | 1.9E2 | 3.0E2 | 2.3E4 | 1.6E4 | 216 | 15 | 133 | 15 | 0.56 |
| Rb | pg/ml | 7.6E-1 | 8.1E-1 | 2.7E0 | 2.4E0 | 4.5E0 | 3.3E0 | 1.0E-9 | 1.0E-9 | 4.3E1 | 9.4E0 | 216 | 15 | 133 | 15 | 0.53 |
| Pz | ng/ml | 3.7E3 | 1.0E4 | 7.4E3 | 4.7E4 | 1.9E4 | 2.0E5 | 1.3E1 | 2.7E2 | 2.8E5 | 1.0E6 | 577 | 25 | 206 | 25 | 0.60 |
| Qa | ng/ml | 3.2E3 | 7.0E3 | 6.1E3 | 8.6E3 | 7.4E3 | 6.6E3 | 1.5E2 | 3.6E2 | 5.2E4 | 2.5E4 | 577 | 25 | 206 | 25 | 0.67 |
| Qb | ng/ml | 9.9E1 | 1.5E2 | 2.2E2 | 2.1E2 | 5.2E2 | 1.9E2 | 7.9E-1 | 2.4E0 | 8.3E3 | 7.2E2 | 577 | 25 | 206 | 25 | 0.58 |
| Qc | ng/ml | 2.5E2 | 2.1E2 | 4.7E2 | 3.2E2 | 8.0E2 | 3.3E2 | 1.0E-9 | 2.0E0 | 1.1E4 | 1.2E3 | 577 | 25 | 206 | 25 | 0.47 |
| Qd | ng/ml | 1.0E4 | 1.1E4 | 2.3E4 | 2.1E4 | 9.4E4 | 2.3E4 | 2.4E2 | 1.1E3 | 2.0E6 | 8.7E4 | 577 | 25 | 206 | 25 | 0.57 |
| Qe | ng/ml | 8.8E2 | 1.8E3 | 1.9E3 | 2.4E3 | 4.6E3 | 2.4E3 | 7.6E0 | 5.5E1 | 9.7E4 | 9.3E3 | 577 | 25 | 206 | 25 | 0.64 |
| Jd | ng/ml | 9.6E-1 | 1.1E0 | 7.2E0 | 2.2E0 | 4.7E1 | 2.7E0 | 1.0E-9 | 1.0E-9 | 6.5E2 | 8.3E0 | 217 | 15 | 135 | 15 | 0.53 |
| Je | ng/ml | 1.0E-9 | 4.3E-1 | 2.5E0 | 9.8E-1 | 8.5E0 | 1.4E0 | 1.0E-9 | 1.0E-9 | 8.8E1 | 4.1E0 | 217 | 15 | 135 | 15 | 0.50 |
| Jf | ng/ml | 1.0E-9 | 1.0E-9 | 1.2E0 | 1.3E0 | 2.4E0 | 2.4E0 | 1.0E-9 | 1.0E-9 | 1.2E1 | 8.7E0 | 217 | 15 | 135 | 15 | 0.56 |
| Jg | ng/ml | 4.7E2 | 1.3E3 | 7.6E2 | 1.1E3 | 9.6E2 | 8.3E2 | 1.0E-9 | 2.1E1 | 1.0E4 | 3.0E3 | 581 | 25 | 208 | 25 | 0.64 |
| Jh | ng/ml | 3.1E0 | 3.9E0 | 2.6E1 | 1.6E1 | 1.1E2 | 2.3E1 | 1.0E-9 | 1.0E-9 | 1.6E3 | 9.1E1 | 581 | 25 | 208 | 25 | 0.55 |
| Ji | ng/ml | 5.0E1 | 8.5E1 | 7.1E1 | 1.2E2 | 7.0E1 | 9.7E1 | 1.0E-9 | 8.5E0 | 5.3E2 | 3.8E2 | 581 | 25 | 208 | 25 | 0.68 |
| Sr | pg/mL | 3.5E2 | 4.3E2 | 8.5E2 | 1.2E3 | 1.3E3 | 1.8E3 | 1.0E-9 | 1.0E-9 | 9.8E3 | 5.5E3 | 207 | 15 | 130 | 15 | 0.54 |
| Ss | pg/mL | 1.2E5 | 1.2E5 | 1.6E5 | 1.4E5 | 2.0E5 | 1.1E5 | 2.7E3 | 9.6E3 | 1.8E6 | 3.5E5 | 207 | 15 | 130 | 15 | 0.50 |
| St | pg/mL | 2.5E7 | 3.9E7 | 5.5E7 | 5.6E7 | 9.9E7 | 4.7E7 | 1.0E-9 | 2.1E6 | 1.2E9 | 1.3E8 | 212 | 14 | 131 | 14 | 0.58 |
| Ra | pg/ml | 1.0E-9 | 1.0E-9 | 6.4E-1 | 1.5E-1 | 1.3E0 | 2.5E-1 | 1.0E-9 | 1.0E-9 | 7.3E0 | 5.6E-1 | 216 | 15 | 133 | 15 | 0.46 |
| Qz | pg/ml | 1.0E1 | 1.0E-9 | 6.0E1 | 2.1E1 | 1.0E2 | 4.0E1 | 1.0E-9 | 1.0E-9 | 7.1E2 | 1.2E2 | 216 | 15 | 133 | 15 | 0.35 |
| Qy | pg/ml | 4.6E-1 | 5.4E-1 | 1.5E1 | 1.4E0 | 7.2E1 | 2.2E0 | 1.0E-9 | 1.0E-9 | 6.5E2 | 8.5E0 | 216 | 15 | 133 | 15 | 0.52 |
| Qx | pg/ml | 1.0E-9 | 1.0E-9 | 7.6E0 | 5.3E-2 | 5.5E1 | 2.0E-1 | 1.0E-9 | 1.0E-9 | 5.8E2 | 7.9E-1 | 216 | 15 | 133 | 15 | 0.46 |

Figure 20 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Qw | pg/ml | 4.5E-2 | 1.0E-9 | 2.2E0 | 1.5E0 | 8.8E0 | 5.8E0 | 1.0E-9 | 1.0E-9 | 8.6E1 | 2.3E1 | 216 | 15 | 133 | 15 | 0.33 |
| Qv | pg/ml | 2.2E4 | 8.6E3 | 3.5E4 | 7.7E4 | 6.4E4 | 2.4E5 | 1.0E-9 | 1.6E3 | 7.4E5 | 9.4E5 | 216 | 15 | 133 | 15 | 0.33 |
| Qu | pg/ml | 1.2E1 | 3.8E0 | 8.9E1 | 6.1E1 | 1.7E2 | 1.7E2 | 1.0E-9 | 1.0E-9 | 9.8E2 | 6.7E2 | 216 | 15 | 133 | 15 | 0.44 |
| Qt | pg/ml | 1.2E1 | 9.7E0 | 5.7E1 | 4.6E1 | 1.4E2 | 8.9E1 | 1.0E-9 | 1.0E-9 | 1.0E3 | 3.3E2 | 216 | 15 | 133 | 15 | 0.50 |
| Qh | ng/ml | 1.7E1 | 3.0E1 | 3.7E1 | 5.3E1 | 6.3E1 | 5.7E1 | 1.0E-9 | 5.4E0 | 6.4E2 | 2.0E2 | 216 | 15 | 133 | 15 | 0.63 |
| Qg | ng/ml | 7.9E0 | 4.6E0 | 2.0E1 | 1.2E1 | 7.5E1 | 1.8E1 | 5.1E-2 | 6.9E-1 | 1.0E3 | 7.4E1 | 216 | 15 | 133 | 15 | 0.43 |
| Jj | ng/ml | 7.5E2 | 7.9E2 | 2.2E3 | 1.1E3 | 1.5E4 | 1.5E3 | 1.7E1 | 1.3E1 | 3.4E5 | 6.7E3 | 581 | 25 | 208 | 25 | 0.43 |
| Jk | ng/ml | 3.3E0 | 4.2E0 | 2.4E1 | 2.3E1 | 4.9E1 | 3.4E1 | 1.0E-9 | 1.2E-1 | 3.9E2 | 1.2E2 | 581 | 25 | 208 | 25 | 0.54 |
| Jl | ng/ml | 4.4E-1 | 5.5E-1 | 1.8E0 | 6.6E0 | 4.3E0 | 9.5E0 | 7.6E-4 | 2.3E-3 | 3.2E1 | 2.6E1 | 581 | 25 | 208 | 25 | 0.63 |
| Jm | ng/ml | 1.9E1 | 1.6E1 | 5.2E1 | 5.0E1 | 9.7E1 | 7.0E1 | 1.0E-9 | 3.8E-1 | 1.0E3 | 3.2E2 | 581 | 25 | 208 | 25 | 0.52 |
| Jn | pg/ml | 4.0E-1 | 5.5E-1 | 1.7E0 | 9.7E-1 | 5.8E0 | 9.1E-1 | 1.0E-9 | 4.8E-2 | 6.2E1 | 3.2E0 | 581 | 25 | 208 | 25 | 0.61 |
| Jo | pg/ml | 4.0E3 | 4.7E3 | 5.1E3 | 4.6E3 | 3.9E3 | 3.4E3 | 4.2E1 | 2.7E2 | 2.4E4 | 1.3E4 | 581 | 25 | 208 | 25 | 0.47 |
| Jp | pg/ml | 7.0E4 | 7.8E4 | 7.3E4 | 8.6E4 | 3.4E4 | 3.5E4 | 2.1E3 | 8.9E3 | 2.1E5 | 1.9E5 | 581 | 25 | 208 | 25 | 0.61 |
| Jq | pg/ml | 9.5E1 | 1.4E2 | 1.5E2 | 2.0E2 | 2.2E2 | 2.0E2 | 2.6E0 | 2.6E1 | 4.0E3 | 7.5E2 | 581 | 25 | 208 | 25 | 0.59 |
| Jr | pg/ml | 5.2E0 | 7.7E0 | 2.2E1 | 1.2E1 | 1.0E2 | 1.4E1 | 1.0E-9 | 1.0E-9 | 1.9E3 | 4.8E1 | 581 | 25 | 208 | 25 | 0.58 |
| Js | pg/ml | 1.3E1 | 1.3E1 | 4.2E1 | 2.0E1 | 1.5E2 | 2.7E1 | 1.0E-9 | 4.5E-1 | 2.0E3 | 1.1E2 | 581 | 25 | 208 | 25 | 0.47 |
| Jt | pg/ml | 2.7E3 | 2.7E3 | 3.2E3 | 3.0E3 | 2.2E3 | 2.0E3 | 1.5E2 | 3.5E2 | 1.3E4 | 7.8E3 | 581 | 25 | 208 | 25 | 0.49 |
| Ju | mIU/ml | 9.0E0 | 1.3E1 | 2.1E1 | 1.7E1 | 3.3E1 | 2.5E1 | 6.5E-2 | 1.7E-1 | 2.3E2 | 1.0E2 | 217 | 15 | 135 | 15 | 0.51 |
| Jv | mIU/ml | 1.2E1 | 1.8E1 | 3.7E1 | 3.3E1 | 6.6E1 | 4.6E1 | 1.0E-2 | 1.4E-1 | 4.4E2 | 1.8E2 | 217 | 15 | 135 | 15 | 0.52 |
| Jy | ng/ml | 1.6E-3 | 1.6E-3 | 2.3E-3 | 2.9E-3 | 4.6E-3 | 5.5E-3 | 1.7E-4 | 4.5E-4 | 5.2E-2 | 2.3E-2 | 217 | 15 | 135 | 15 | 0.47 |
| Kc | pg/ml | 2.3E1 | 3.6E1 | 4.0E1 | 6.4E1 | 4.3E1 | 5.7E1 | 1.0E-9 | 6.1E0 | 1.9E2 | 1.6E2 | 218 | 16 | 134 | 16 | 0.60 |
| Kd | pg/ml | 1.0E-9 | 1.0E-9 | 2.0E2 | 2.1E2 | 6.0E2 | 5.5E2 | 1.0E-9 | 1.0E-9 | 4.8E3 | 1.8E3 | 218 | 16 | 134 | 16 | 0.53 |
| Ke | pg/ml | 1.3E4 | 1.3E4 | 1.4E4 | 1.7E4 | 1.1E4 | 1.2E4 | 3.4E2 | 1.3E3 | 7.0E4 | 4.4E4 | 218 | 16 | 134 | 16 | 0.55 |
| Kf | pg/mL | 6.7E0 | 8.8E0 | 7.3E0 | 9.9E0 | 5.9E0 | 4.9E0 | 1.0E-9 | 1.0E-9 | 2.7E1 | 1.6E1 | 218 | 16 | 134 | 16 | 0.65 |
| Kg | pg/mL | 1.2E3 | 6.9E2 | 2.0E3 | 1.6E3 | 2.4E3 | 1.5E3 | 7.3E1 | 2.1E2 | 1.7E4 | 4.6E3 | 218 | 16 | 134 | 16 | 0.44 |
| Ki | pg/ml | 5.9E1 | 5.3E1 | 7.0E1 | 5.2E1 | 5.5E1 | 2.4E1 | 1.0E-9 | 1.3E1 | 3.8E2 | 1.0E2 | 217 | 16 | 134 | 16 | 0.41 |
| Kj | pg/ml | 1.1E3 | 6.9E2 | 1.7E3 | 1.4E3 | 1.7E3 | 1.6E3 | 1.4E1 | 9.4E1 | 1.0E4 | 6.1E3 | 218 | 16 | 134 | 16 | 0.42 |
| Kk | pg/ml | 6.8E0 | 9.2E0 | 1.1E1 | 1.5E1 | 1.6E1 | 1.7E1 | 1.0E-9 | 1.0E-9 | 1.6E2 | 4.8E1 | 218 | 16 | 134 | 16 | 0.52 |
| Kl | pg/ml | 2.1E4 | 2.1E4 | 2.9E4 | 3.0E4 | 2.6E4 | 2.4E4 | 1.6E2 | 8.3E2 | 1.6E5 | 6.9E4 | 218 | 16 | 134 | 16 | 0.53 |
| Kn | pg/ml | 3.0E1 | 5.7E1 | 6.2E1 | 9.7E1 | 9.5E1 | 1.2E2 | 1.0E-9 | 1.0E-9 | 7.3E2 | 3.8E2 | 218 | 16 | 134 | 16 | 0.59 |
| Ko | pg/ml | 3.4E2 | 5.1E2 | 4.6E2 | 5.8E2 | 4.5E2 | 4.8E2 | 1.0E-9 | 1.0E-9 | 2.2E3 | 1.5E3 | 218 | 16 | 134 | 16 | 0.57 |
| Kp | pg/ml | 3.4E2 | 4.3E2 | 3.5E2 | 4.5E2 | 2.7E2 | 2.4E2 | 1.0E-9 | 1.0E-9 | 1.7E3 | 8.6E2 | 218 | 16 | 134 | 16 | 0.62 |
| Kq | pg/ml | 3.2E2 | 3.8E2 | 5.1E2 | 6.9E2 | 9.1E2 | 9.1E2 | 1.6E0 | 8.8E1 | 9.8E3 | 3.6E3 | 209 | 16 | 128 | 16 | 0.56 |
| Kr | pg/ml | 5.6E-1 | 6.4E-1 | 2.7E0 | 1.4E0 | 5.2E0 | 2.2E0 | 1.0E-9 | 1.0E-9 | 3.9E1 | 8.0E0 | 209 | 16 | 128 | 16 | 0.45 |
| Ks | pg/ml | 1.4E4 | 9.0E3 | 2.1E4 | 1.6E4 | 1.9E4 | 1.7E4 | 5.1E1 | 4.1E2 | 1.1E5 | 5.0E4 | 209 | 16 | 128 | 16 | 0.43 |
| Kx | ng/ml | 1.0E-9 | 1.7E-3 | 7.1E-3 | 6.3E-3 | 1.4E-2 | 1.1E-2 | 1.0E-9 | 1.0E-9 | 1.0E-1 | 4.1E-2 | 214 | 16 | 133 | 16 | 0.51 |
| Ky | ng/ml | 1.0E-1 | 1.8E-1 | 3.8E-1 | 7.9E-1 | 8.3E-1 | 1.6E0 | 1.0E-9 | 6.9E-2 | 5.4E0 | 6.4E0 | 214 | 16 | 133 | 16 | 0.67 |
| Kz | ng/ml | 1.0E-9 | 1.0E-9 | 3.4E-3 | 2.8E-3 | 5.7E-3 | 4.0E-3 | 1.0E-9 | 1.0E-9 | 3.6E-2 | 1.4E-2 | 214 | 16 | 133 | 16 | 0.52 |
| Ld | pg/ml | 1.0E-9 | 2.8E0 | 3.7E0 | 4.3E0 | 9.6E0 | 5.3E0 | 1.0E-9 | 1.0E-9 | 8.4E1 | 1.9E1 | 216 | 16 | 133 | 16 | 0.60 |
| Lh | pg/ml | 1.3E4 | 2.2E4 | 2.1E4 | 3.1E4 | 2.7E4 | 2.8E4 | 1.0E-9 | 5.3E2 | 2.6E5 | 1.1E5 | 580 | 25 | 209 | 25 | 0.64 |
| Li | pg/ml | 3.1E3 | 4.9E3 | 1.5E4 | 1.1E4 | 3.9E4 | 1.6E4 | 1.0E-9 | 3.7E1 | 3.6E5 | 6.8E4 | 580 | 25 | 209 | 25 | 0.54 |
| Lj | pg/ml | 2.4E3 | 5.3E3 | 2.1E4 | 1.6E4 | 6.5E4 | 2.5E4 | 1.0E-9 | 3.4E1 | 4.7E5 | 9.4E4 | 580 | 25 | 209 | 25 | 0.56 |
| Rm | ng/ml | 1.9E1 | 2.8E1 | 5.1E1 | 6.8E1 | 7.7E1 | 8.1E1 | 2.2E-1 | 4.0E-1 | 4.0E2 | 2.5E2 | 213 | 15 | 132 | 15 | 0.56 |
| Rh | ng/ml | 1.3E2 | 6.0E1 | 2.8E2 | 2.0E2 | 5.0E2 | 2.4E2 | 4.7E0 | 1.8E1 | 3.8E3 | 6.9E2 | 213 | 15 | 132 | 15 | 0.42 |
| Ri | ng/ml | 1.0E-9 | 1.0E-9 | 4.3E0 | 4.1E0 | 1.7E1 | 1.1E1 | 1.0E-9 | 1.0E-9 | 2.2E2 | 4.1E1 | 214 | 15 | 133 | 15 | 0.48 |
| Rg | ng/ml | 1.0E-9 | 1.0E-9 | 6.8E-2 | 6.6E-3 | 3.9E-1 | 1.4E-2 | 1.0E-9 | 1.0E-9 | 3.3E0 | 4.8E-2 | 213 | 15 | 132 | 15 | 0.59 |
| Rj | ng/ml | 1.0E-9 | 1.0E-9 | 1.6E0 | 4.7E-2 | 6.3E0 | 1.8E-1 | 1.0E-9 | 1.0E-9 | 8.0E1 | 7.0E-1 | 214 | 15 | 133 | 15 | 0.39 |
| Rf | ng/ml | 3.7E-1 | 2.4E-1 | 1.0E0 | 4.5E-1 | 1.9E0 | 5.1E-1 | 7.8E-3 | 2.2E-2 | 1.5E1 | 2.1E0 | 213 | 15 | 132 | 15 | 0.41 |
| Ql | pg/ml | 5.5E0 | 4.3E-1 | 1.5E1 | 6.4E0 | 3.2E1 | 7.9E0 | 1.0E-9 | 1.0E-9 | 2.9E2 | 2.4E1 | 217 | 15 | 135 | 15 | 0.44 |
| Qm | pg/ml | 4.4E0 | 1.0E-9 | 2.0E1 | 2.1E1 | 4.0E1 | 3.4E1 | 1.0E-9 | 1.0E-9 | 3.6E2 | 1.1E2 | 217 | 15 | 135 | 15 | 0.48 |
| Qn | pg/ml | 6.1E-1 | 1.6E0 | 5.8E0 | 1.5E1 | 1.9E1 | 2.6E1 | 1.0E-9 | 1.0E-9 | 2.2E2 | 7.5E1 | 217 | 15 | 135 | 15 | 0.64 |
| Nv | pg/ml | 4.0E3 | 6.2E3 | 1.2E4 | 1.8E4 | 5.2E4 | 3.3E4 | 1.0E-9 | 9.8E1 | 1.1E6 | 1.6E5 | 585 | 25 | 209 | 25 | 0.60 |
| Nw | pg/ml | 8.5E3 | 1.6E4 | 1.3E4 | 1.6E4 | 1.8E4 | 1.1E4 | 8.6E1 | 7.5E2 | 2.1E5 | 5.0E4 | 585 | 25 | 209 | 25 | 0.66 |
| Nx | pg/ml | 2.2E2 | 3.5E2 | 4.1E2 | 6.8E2 | 6.9E2 | 6.7E2 | 1.0E-9 | 1.0E-9 | 7.4E3 | 2.1E3 | 585 | 25 | 209 | 25 | 0.66 |
| Ny | pg/ml | 5.7E0 | 1.0E1 | 7.2E1 | 7.1E1 | 1.0E3 | 2.4E2 | 1.0E-9 | 1.0E-9 | 2.5E4 | 1.2E3 | 585 | 25 | 209 | 25 | 0.61 |
| Oa | pg/ml | 1.6E2 | 5.4E2 | 4.1E2 | 7.2E2 | 7.0E2 | 7.8E2 | 1.0E-9 | 1.0E-9 | 4.8E3 | 2.9E3 | 217 | 15 | 135 | 15 | 0.68 |
| Oe | pg/ml | 9.1E1 | 7.1E0 | 3.1E2 | 3.0E2 | 8.7E2 | 4.6E2 | 1.0E-9 | 1.0E-9 | 1.9E4 | 1.6E3 | 580 | 25 | 209 | 25 | 0.47 |

Figure 20 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Of | pg/ml | 2.3E2 | 1.2E2 | 7.1E3 | 9.8E3 | 3.3E4 | 2.6E4 | 1.0E-9 | 1.0E-9 | 6.2E5 | 1.2E5 | 585 | 25 | 209 | 25 | 0.45 |
| Og | pg/ml | 9.2E-2 | 9.3E-2 | 9.9E-1 | 2.8E-1 | 5.8E0 | 8.0E-1 | 1.0E-9 | 1.0E-9 | 8.3E1 | 4.0E0 | 585 | 25 | 209 | 25 | 0.42 |
| Oh | pg/ml | 2.4E0 | 5.3E0 | 2.5E1 | 8.9E0 | 1.7E2 | 1.2E1 | 1.0E-9 | 1.0E-9 | 3.5E3 | 5.6E1 | 585 | 25 | 209 | 25 | 0.61 |
| Oi | pg/ml | 2.8E0 | 2.5E0 | 6.5E0 | 5.0E0 | 1.0E1 | 7.5E0 | 1.0E-9 | 1.0E-9 | 8.6E1 | 3.6E1 | 585 | 25 | 209 | 25 | 0.48 |
| Ok | pg/ml | 3.9E2 | 6.0E2 | 5.2E2 | 7.4E2 | 5.0E2 | 5.3E2 | 1.3E1 | 4.2E1 | 5.2E3 | 2.0E3 | 585 | 25 | 209 | 25 | 0.64 |
| Om | pg/ml | 3.8E2 | 5.5E2 | 9.0E2 | 7.2E2 | 2.5E3 | 6.6E2 | 1.0E-9 | 1.0E-9 | 3.6E4 | 2.5E3 | 585 | 25 | 209 | 25 | 0.55 |
| On | pg/ml | 1.8E2 | 3.1E2 | 2.9E2 | 4.6E2 | 4.3E2 | 4.6E2 | 8.4E-1 | 1.2E1 | 4.5E3 | 1.7E3 | 585 | 25 | 209 | 25 | 0.63 |
| Or | pg/ml | 1.4E1 | 5.8E1 | 3.4E1 | 8.3E1 | 6.3E1 | 9.5E1 | 1.0E-9 | 1.0E-9 | 5.0E2 | 3.4E2 | 218 | 16 | 134 | 16 | 0.72 |
| Ow | pg/ml | 3.3E1 | 1.0E2 | 1.1E2 | 7.7E2 | 3.1E2 | 2.0E3 | 1.0E-9 | 2.5E1 | 2.7E3 | 8.1E3 | 218 | 16 | 134 | 16 | 0.80 |
| Ou | pg/ml | 4.7E2 | 1.3E3 | 8.8E2 | 2.3E3 | 1.3E3 | 2.8E3 | 1.0E-9 | 1.4E2 | 9.8E3 | 1.1E4 | 218 | 16 | 134 | 16 | 0.72 |
| Ul | ng/ml | 1.0E-9 | 1.0E-9 | 1.4E0 | 1.4E0 | 4.7E0 | 3.6E0 | 1.0E-9 | 1.0E-9 | 3.4E1 | 1.0E1 | 224 | 15 | 137 | 15 | 0.51 |
| Uo | ng/ml | 1.0E-9 | 1.0E-9 | 1.1E-1 | 5.8E-2 | 2.7E-1 | 1.1E-1 | 1.0E-9 | 1.0E-9 | 2.6E0 | 3.2E-1 | 224 | 15 | 137 | 15 | 0.50 |
| Uk | ng/ml | 1.0E-9 | 1.0E-9 | 8.7E-3 | 4.8E-3 | 2.9E-2 | 1.8E-2 | 1.0E-9 | 1.0E-9 | 3.2E-1 | 7.1E-2 | 224 | 15 | 137 | 15 | 0.37 |
| Um | ng/ml | 1.0E-9 | 1.0E-9 | 4.2E-1 | 7.0E-1 | 1.0E0 | 1.1E0 | 1.0E-9 | 1.0E-9 | 7.2E0 | 2.7E0 | 224 | 15 | 137 | 15 | 0.52 |
| Uf | ng/ml | 5.3E-2 | 1.0E-1 | 1.5E-1 | 6.7E-1 | 2.7E-1 | 2.2E0 | 1.0E-3 | 3.5E-3 | 2.1E0 | 8.6E0 | 224 | 15 | 137 | 15 | 0.60 |
| Uh | ng/ml | 1.9E0 | 3.1E0 | 2.9E0 | 5.0E0 | 3.1E0 | 5.4E0 | 3.2E-2 | 1.3E-2 | 1.7E1 | 2.1E1 | 224 | 15 | 137 | 15 | 0.62 |
| Un | ng/ml | 1.9E0 | 2.3E0 | 2.1E0 | 2.2E0 | 1.3E0 | 1.3E0 | 2.0E-1 | 1.3E-1 | 8.0E0 | 4.7E0 | 224 | 15 | 137 | 15 | 0.53 |
| Ug | ng/ml | 1.4E1 | 6.8E0 | 2.8E1 | 2.1E1 | 2.9E1 | 2.9E1 | 6.9E-1 | 2.2E0 | 1.8E2 | 1.1E2 | 224 | 15 | 137 | 15 | 0.36 |
| Ur | ng/ml | 1.5E-1 | 9.6E-2 | 8.5E-1 | 5.1E-1 | 6.3E0 | 1.2E0 | 1.0E-9 | 1.0E-9 | 9.3E1 | 4.7E0 | 223 | 15 | 136 | 15 | 0.41 |
| Up | ng/ml | 1.0E-9 | 1.0E-9 | 6.0E-3 | 9.0E-4 | 2.6E-2 | 1.5E-3 | 1.0E-9 | 1.0E-9 | 3.3E-1 | 4.9E-3 | 223 | 15 | 136 | 15 | 0.50 |
| Us | ng/ml | 4.3E-3 | 1.0E-9 | 1.9E-2 | 1.2E-2 | 4.6E-2 | 2.1E-2 | 1.0E-9 | 1.0E-9 | 4.0E-1 | 6.3E-2 | 223 | 15 | 136 | 15 | 0.43 |
| Uv | ng/ml | 3.2E-2 | 1.8E-3 | 1.3E-2 | 8.1E-3 | 3.9E-2 | 1.4E-2 | 1.0E-9 | 1.0E-9 | 4.3E-1 | 4.4E-2 | 223 | 15 | 136 | 15 | 0.43 |
| Ut | ng/ml | 7.6E-1 | 6.1E-1 | 3.2E0 | 2.9E0 | 9.7E0 | 6.2E0 | 1.0E-9 | 1.0E-9 | 7.8E1 | 2.4E1 | 223 | 15 | 136 | 15 | 0.44 |
| Uu | ng/ml | 7.2E0 | 8.6E0 | 7.8E0 | 9.0E0 | 4.8E0 | 5.3E0 | 5.7E-1 | 1.3E0 | 2.6E1 | 2.1E1 | 223 | 15 | 136 | 15 | 0.57 |
| Vp | ng/ml | 1.0E-9 | 1.0E-9 | 4.6E-1 | 8.2E-2 | 3.8E0 | 1.7E-1 | 1.0E-9 | 1.0E-9 | 5.0E1 | 6.0E-1 | 224 | 15 | 137 | 15 | 0.55 |
| Vt | ng/ml | 6.1E0 | 8.6E0 | 8.3E0 | 1.1E1 | 9.3E0 | 6.7E0 | 4.3E-1 | 1.9E0 | 8.6E1 | 2.2E1 | 224 | 15 | 137 | 15 | 0.64 |
| Vu | ng/ml | 1.0E-9 | 5.6E-1 | 2.9E0 | 1.9E0 | 7.5E0 | 3.1E0 | 1.0E-9 | 1.0E-9 | 7.1E1 | 1.1E1 | 219 | 14 | 137 | 14 | 0.55 |
| Vq | ng/ml | 1.5E2 | 5.6E2 | 6.3E2 | 8.4E2 | 1.4E3 | 7.8E2 | 2.0E-1 | 1.7E1 | 1.1E4 | 2.3E3 | 175 | 11 | 115 | 11 | 0.67 |
| Vo | ng/ml | 2.6E1 | 2.5E1 | 2.5E1 | 2.4E1 | 5.1E0 | 5.6E0 | 2.5E0 | 8.0E0 | 4.8E1 | 3.1E1 | 224 | 15 | 137 | 15 | 0.45 |
| Vs | ng/ml | 2.6E-1 | 1.0E-9 | 7.3E0 | 1.0E1 | 2.6E1 | 2.4E1 | 1.0E-9 | 1.0E-9 | 2.3E2 | 9.4E1 | 218 | 15 | 135 | 15 | 0.54 |
| Vv | ng/ml | 3.3E0 | 3.5E0 | 6.3E0 | 4.7E0 | 1.0E1 | 6.8E0 | 1.0E-9 | 1.4E-1 | 8.4E1 | 2.6E1 | 223 | 15 | 137 | 15 | 0.47 |
| Oy | pg/ml | 5.5E-1 | 5.0E-1 | 7.3E0 | 2.4E0 | 3.5E1 | 4.2E0 | 1.0E-9 | 1.0E-9 | 4.0E2 | 1.5E1 | 584 | 25 | 208 | 25 | 0.52 |
| Oz | pg/ml | 1.3E-2 | 5.8E-2 | 3.5E-1 | 2.6E-1 | 1.6E0 | 4.1E-1 | 1.0E-9 | 1.0E-9 | 2.9E1 | 1.7E0 | 584 | 25 | 208 | 25 | 0.52 |
| Pa | pg/ml | 3.9E-1 | 5.0E-1 | 1.5E0 | 1.0E0 | 5.8E0 | 1.1E0 | 1.0E-9 | 1.0E-9 | 8.6E1 | 4.4E0 | 584 | 25 | 208 | 25 | 0.61 |
| Pb | pg/ml | 1.0E-9 | 1.0E-9 | 1.1E0 | 1.2E0 | 2.0E1 | 5.6E0 | 1.0E-9 | 1.0E-9 | 4.9E2 | 2.8E1 | 584 | 25 | 208 | 25 | 0.51 |
| Pc | pg/ml | 4.9E-2 | 2.7E-1 | 3.8E-1 | 4.1E-1 | 1.0E0 | 4.9E-1 | 1.0E-9 | 1.0E-9 | 1.6E1 | 1.8E0 | 584 | 25 | 208 | 25 | 0.57 |
| Pd | pg/ml | 1.8E0 | 2.8E0 | 5.5E0 | 3.6E0 | 3.6E1 | 3.5E0 | 1.0E-9 | 1.0E-9 | 8.4E2 | 1.4E1 | 584 | 25 | 208 | 25 | 0.57 |
| Pe | pg/ml | 2.1E1 | 4.4E1 | 1.1E2 | 6.1E1 | 3.7E2 | 6.0E1 | 1.0E-9 | 1.0E-9 | 4.7E3 | 2.5E2 | 584 | 25 | 208 | 25 | 0.62 |
| Pf | pg/ml | 1.5E0 | 2.7E0 | 1.1E1 | 1.0E1 | 6.6E1 | 1.8E1 | 1.0E-9 | 1.0E-9 | 1.5E3 | 7.7E1 | 584 | 25 | 208 | 25 | 0.61 |
| Pg | pg/ml | 3.3E0 | 1.0E1 | 5.4E1 | 3.7E1 | 4.2E2 | 5.7E1 | 1.0E-9 | 1.0E-9 | 7.7E3 | 1.9E2 | 584 | 25 | 208 | 25 | 0.66 |
| Ph | ng/ml | 1.6E-1 | 2.2E-1 | 3.3E-1 | 3.8E-1 | 4.9E-1 | 5.5E-1 | 1.0E-9 | 1.0E-9 | 3.1E0 | 2.3E0 | 218 | 16 | 134 | 16 | 0.51 |
| Pi | ng/ml | 1.9E-1 | 2.5E-1 | 2.8E-1 | 3.2E-1 | 3.7E-1 | 2.6E-1 | 1.0E-9 | 1.0E-9 | 3.2E0 | 8.6E-1 | 218 | 16 | 134 | 16 | 0.59 |
| Pj | ng/mL | 5.2E0 | 5.4E0 | 6.1E0 | 5.8E0 | 4.7E0 | 3.6E0 | 3.8E-2 | 8.8E-1 | 3.1E1 | 1.3E1 | 218 | 16 | 134 | 16 | 0.51 |
| Pk | ng/ml | 8.9E-3 | 6.5E-3 | 1.4E-2 | 1.0E-2 | 2.2E-2 | 1.3E-2 | 1.0E-9 | 1.0E-9 | 2.5E-1 | 4.3E-2 | 218 | 16 | 134 | 16 | 0.42 |
| aA | mg/dL | 8.0E-1 | 9.0E-1 | 9.1E-1 | 1.1E0 | 4.4E-1 | 7.7E-1 | 2.0E-1 | 4.0E-1 | 4.2E0 | 4.1E0 | 1815 | 29 | 323 | 29 | 0.56 |
| aC | mg/mL | 2.8E0 | 1.8E0 | 3.1E0 | 2.2E0 | 1.3E0 | 1.1E0 | 8.5E-1 | 1.1E0 | 8.2E0 | 4.8E0 | 363 | 17 | 141 | 17 | 0.29 |
| aD | ug/mL | 3.1E0 | 5.8E0 | 4.3E0 | 5.5E0 | 3.5E0 | 4.2E0 | 8.5E-1 | 9.9E-1 | 3.1E1 | 1.7E1 | 363 | 17 | 141 | 17 | 0.56 |
| aE | mg/mL | 5.7E-1 | 5.7E-1 | 5.8E-1 | 5.7E-1 | 1.5E-1 | 1.7E-1 | 2.1E-1 | 2.5E-1 | 1.1E0 | 8.6E-1 | 363 | 17 | 141 | 17 | 0.47 |
| aF | ng/mL | 2.1E0 | 2.4E0 | 4.1E0 | 5.9E0 | 6.1E0 | 7.8E0 | 4.3E-3 | 4.3E-3 | 5.0E1 | 2.9E1 | 363 | 17 | 141 | 17 | 0.55 |
| aG | mg/mL | 1.4E-1 | 1.1E-1 | 1.6E-1 | 1.4E-1 | 8.4E-2 | 8.4E-2 | 5.0E-2 | 5.6E-2 | 5.0E-1 | 3.8E-1 | 363 | 17 | 141 | 17 | 0.39 |
| aH | ug/mL | 7.5E1 | 7.6E1 | 8.1E1 | 7.7E1 | 4.2E1 | 4.2E1 | 9.6E0 | 2.3E1 | 2.9E2 | 1.4E2 | 363 | 17 | 141 | 17 | 0.48 |
| aI | ug/mL | 1.9E2 | 1.5E2 | 1.9E2 | 1.7E2 | 6.0E1 | 7.3E1 | 4.7E1 | 7.5E1 | 3.7E2 | 2.8E2 | 363 | 17 | 141 | 17 | 0.41 |
| aJ | ug/mL | 2.4E0 | 3.7E0 | 3.0E0 | 4.3E0 | 2.2E0 | 2.9E0 | 9.0E-1 | 9.5E-1 | 1.7E1 | 1.1E1 | 363 | 17 | 141 | 17 | 0.66 |
| aK | ng/mL | 1.6E0 | 1.0E0 | 2.5E0 | 2.4E0 | 2.7E0 | 2.9E0 | 2.9E-4 | 9.1E-2 | 1.8E1 | 1.1E1 | 363 | 17 | 141 | 17 | 0.46 |
| aL | mg/mL | 7.9E-1 | 8.3E-1 | 8.0E-1 | 8.2E-1 | 2.4E-1 | 3.3E-1 | 2.2E-1 | 2.9E-1 | 1.7E0 | 1.6E0 | 363 | 17 | 141 | 17 | 0.49 |
| aM | U/mL | 2.2E1 | 2.4E1 | 4.4E1 | 4.8E1 | 1.0E2 | 4.4E1 | 4.2E-2 | 4.2E-2 | 1.6E3 | 1.3E2 | 363 | 17 | 141 | 17 | 0.57 |
| aN | U/mL | 1.4E1 | 2.1E1 | 2.1E1 | 3.1E1 | 3.0E1 | 2.6E1 | 2.5E-3 | 2.5E-3 | 3.8E2 | 9.5E1 | 363 | 17 | 141 | 17 | 0.65 |

Figure 20 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aO | pg/mL | 3.5E1 | 3.3E1 | 3.4E2 | 3.3E2 | 8.8E2 | 5.9E2 | 6.0E-2 | 6.0E-2 | 6.6E3 | 2.1E3 | 363 | 17 | 141 | 17 | 0.52 |
| aP | ng/mL | 1.6E0 | 1.8E0 | 2.0E0 | 2.3E0 | 1.2E0 | 1.5E0 | 5.4E-1 | 7.0E-1 | 7.0E0 | 6.6E0 | 363 | 17 | 141 | 17 | 0.58 |
| aQ | ng/mL | 3.0E-1 | 2.8E-1 | 4.6E-1 | 4.0E-1 | 4.9E-1 | 4.5E-1 | 2.0E-4 | 6.7E-2 | 4.0E0 | 1.8E0 | 363 | 17 | 141 | 17 | 0.44 |
| aR | ng/mL | 1.8E0 | 1.9E0 | 2.9E0 | 2.3E0 | 3.5E0 | 1.8E0 | 1.8E-1 | 3.2E-1 | 3.4E1 | 7.9E0 | 363 | 17 | 141 | 17 | 0.48 |
| aS | ng/mL | 2.7E-1 | 2.9E-1 | 7.2E-1 | 4.8E-1 | 2.0E0 | 4.7E-1 | 4.2E-3 | 7.2E-2 | 3.3E1 | 1.7E0 | 363 | 17 | 141 | 17 | 0.52 |
| aU | pg/mL | 7.8E1 | 5.3E1 | 1.3E2 | 1.3E2 | 1.5E2 | 1.6E2 | 7.4E-2 | 6.5E0 | 1.3E3 | 6.0E2 | 363 | 17 | 141 | 17 | 0.46 |
| aV | ng/mL | 6.3E-1 | 3.7E-1 | 1.1E0 | 1.1E0 | 2.1E0 | 1.6E0 | 7.6E-4 | 3.3E-2 | 3.3E1 | 6.0E0 | 363 | 17 | 141 | 17 | 0.42 |
| aW | pg/mL | 1.9E1 | 1.8E1 | 2.0E1 | 1.8E1 | 2.1E1 | 8.0E0 | 7.2E-2 | 7.2E-2 | 2.4E2 | 3.1E1 | 363 | 17 | 141 | 17 | 0.49 |
| aX | ng/mL | 9.5E0 | 1.6E1 | 1.4E1 | 2.4E1 | 1.4E1 | 3.5E1 | 3.0E-1 | 1.4E0 | 8.0E1 | 1.4E2 | 363 | 17 | 141 | 17 | 0.56 |
| aY | pg/mL | 6.0E1 | 6.6E1 | 8.0E1 | 9.4E1 | 9.2E1 | 6.9E1 | 4.1E-1 | 1.7E1 | 1.2E3 | 2.4E2 | 363 | 17 | 141 | 17 | 0.59 |
| aZ | pg/mL | 2.2E2 | 1.7E2 | 5.2E2 | 4.7E2 | 1.0E3 | 1.0E3 | 1.7E0 | 1.7E0 | 1.2E4 | 4.3E3 | 363 | 17 | 141 | 17 | 0.45 |
| bA | ng/mL | 8.5E0 | 2.7E1 | 3.0E1 | 1.1E2 | 7.7E1 | 2.0E2 | 3.0E-2 | 1.4E0 | 9.4E2 | 8.1E2 | 363 | 17 | 141 | 17 | 0.68 |
| bB | ng/mL | 3.0E2 | 1.9E2 | 3.2E2 | 2.5E2 | 1.6E2 | 1.7E2 | 1.6E1 | 1.2E1 | 1.0E3 | 6.2E2 | 363 | 17 | 141 | 17 | 0.36 |
| bC | ng/mL | 3.3E2 | 4.7E2 | 5.7E2 | 1.1E3 | 7.3E2 | 1.3E3 | 2.7E1 | 1.5E2 | 4.7E3 | 4.7E3 | 363 | 17 | 141 | 17 | 0.66 |
| bE | mg/mL | 5.4E0 | 4.9E0 | 5.7E0 | 5.8E0 | 1.9E0 | 2.8E0 | 1.4E0 | 1.9E0 | 1.3E1 | 1.1E1 | 363 | 17 | 141 | 17 | 0.46 |
| bF | pg/mL | 2.0E1 | 3.3E1 | 1.8E2 | 6.0E2 | 1.1E3 | 1.5E3 | 5.0E-2 | 8.5E0 | 1.1E4 | 6.3E3 | 363 | 17 | 141 | 17 | 0.66 |
| bG | ng/mL | 1.6E0 | 2.2E0 | 2.8E0 | 4.6E0 | 3.4E0 | 7.2E0 | 2.2E-2 | 1.6E-1 | 2.6E1 | 3.0E1 | 363 | 17 | 141 | 17 | 0.54 |
| bH | pg/mL | 5.7E-1 | 5.7E-1 | 5.2E0 | 2.7E0 | 1.7E1 | 3.6E0 | 5.7E-1 | 5.7E-1 | 2.8E2 | 1.1E1 | 363 | 17 | 141 | 17 | 0.46 |
| bI | ng/mL | 4.0E-3 | 4.0E-3 | 7.0E-2 | 2.2E-2 | 1.7E-1 | 7.4E-2 | 4.0E-3 | 4.0E-3 | 1.3E0 | 3.1E-1 | 363 | 17 | 141 | 17 | 0.43 |
| bJ | mg/mL | 2.2E0 | 1.1E0 | 2.5E0 | 2.1E0 | 1.9E0 | 2.3E0 | 2.5E-4 | 2.1E-2 | 1.3E1 | 9.0E0 | 363 | 17 | 141 | 17 | 0.41 |
| bL | pg/mL | 4.1E0 | 5.8E0 | 8.4E0 | 8.4E0 | 1.0E1 | 8.1E0 | 4.6E-2 | 4.6E-2 | 4.9E1 | 2.5E1 | 363 | 17 | 141 | 17 | 0.53 |
| bM | mg/mL | 1.7E0 | 2.4E0 | 2.1E0 | 2.7E0 | 1.4E0 | 1.9E0 | 9.2E-3 | 7.1E-1 | 7.9E0 | 8.4E0 | 363 | 17 | 141 | 17 | 0.61 |
| bN | ng/mL | 4.7E1 | 3.9E1 | 1.3E2 | 8.3E1 | 2.7E2 | 1.4E2 | 1.4E-1 | 1.8E0 | 1.9E3 | 5.7E2 | 363 | 17 | 141 | 17 | 0.44 |
| bO | ng/mL | 4.0E-2 | 4.0E-2 | 9.2E0 | 8.3E0 | 2.1E1 | 1.4E1 | 4.0E-2 | 4.0E-2 | 1.9E2 | 3.8E1 | 363 | 17 | 141 | 17 | 0.51 |
| bP | mg/mL | 5.1E-1 | 6.8E-1 | 7.3E-1 | 8.2E-1 | 6.6E-1 | 7.3E-1 | 8.2E-2 | 2.3E-1 | 4.8E0 | 3.1E0 | 363 | 17 | 141 | 17 | 0.55 |
| bQ | pg/mL | 1.5E1 | 2.0E1 | 7.0E1 | 4.5E1 | 7.1E2 | 5.2E1 | 1.5E-1 | 6.4E0 | 1.3E4 | 1.8E2 | 363 | 17 | 141 | 17 | 0.59 |
| bR | ng/mL | 1.2E-2 | 1.2E-2 | 1.4E-1 | 7.6E-2 | 5.0E-1 | 1.1E-1 | 1.2E-2 | 1.2E-2 | 8.7E0 | 3.2E-1 | 363 | 17 | 141 | 17 | 0.45 |
| bS | pg/mL | 9.4E-1 | 9.4E-1 | 7.8E0 | 3.3E0 | 3.1E1 | 9.9E0 | 9.4E-1 | 9.4E-1 | 3.9E2 | 4.2E1 | 363 | 17 | 141 | 17 | 0.46 |
| bU | ng/mL | 1.3E-1 | 6.8E-2 | 2.1E-1 | 1.5E-1 | 4.1E-1 | 1.7E-1 | 1.3E-2 | 1.3E-2 | 6.6E0 | 4.9E-1 | 363 | 17 | 141 | 17 | 0.46 |
| bV | pg/mL | 4.7E2 | 5.7E2 | 5.3E2 | 1.6E3 | 2.4E2 | 3.9E3 | 1.7E2 | 2.6E2 | 1.6E3 | 1.7E4 | 363 | 17 | 141 | 17 | 0.58 |
| bW | pg/mL | 3.4E2 | 4.0E2 | 4.9E2 | 1.7E3 | 5.0E2 | 4.7E3 | 8.4E1 | 1.3E2 | 4.8E3 | 2.0E4 | 363 | 17 | 141 | 17 | 0.56 |
| bX | ng/mL | 1.5E-3 | 2.5E-5 | 2.8E-3 | 1.6E-3 | 3.4E-3 | 3.2E-3 | 2.5E-5 | 2.5E-5 | 2.0E-2 | 1.2E-2 | 363 | 17 | 141 | 17 | 0.38 |
| bZ | pg/mL | 2.4E2 | 3.4E2 | 9.1E2 | 3.7E3 | 4.3E3 | 1.0E4 | 1.5E-1 | 7.4E1 | 5.8E4 | 4.3E4 | 363 | 17 | 141 | 17 | 0.61 |
| cA | pg/mL | 6.0E-1 | 6.0E-1 | 3.0E0 | 1.9E0 | 2.0E1 | 3.7E0 | 6.0E-1 | 6.0E-1 | 3.7E2 | 1.3E1 | 363 | 17 | 141 | 17 | 0.50 |
| cB | ng/mL | 5.4E-2 | 3.6E-2 | 8.6E-2 | 8.2E-2 | 1.0E-1 | 1.3E-1 | 1.7E-3 | 1.7E-3 | 5.7E-1 | 5.5E-1 | 363 | 17 | 141 | 17 | 0.45 |
| cC | pg/mL | 4.6E1 | 4.8E1 | 4.9E1 | 4.6E1 | 4.2E1 | 2.6E1 | 1.0E0 | 1.0E0 | 4.5E2 | 9.6E1 | 363 | 17 | 141 | 17 | 0.50 |
| cD | pg/mL | 5.2E0 | 3.8E0 | 1.3E1 | 8.6E0 | 3.9E1 | 1.2E1 | 3.3E-1 | 3.3E-1 | 4.8E2 | 4.1E1 | 363 | 17 | 141 | 17 | 0.43 |
| cE | pg/mL | 3.2E1 | 7.4E1 | 1.5E2 | 5.9E2 | 4.8E2 | 1.0E3 | 1.2E-1 | 1.2E-1 | 3.8E3 | 3.8E3 | 363 | 17 | 141 | 17 | 0.68 |
| cF | pg/mL | 1.2E1 | 9.4E0 | 2.1E1 | 1.2E1 | 3.4E1 | 1.3E1 | 5.3E-1 | 5.3E-1 | 2.7E2 | 4.1E1 | 363 | 17 | 141 | 17 | 0.45 |
| cG | pg/mL | 4.3E1 | 8.6E1 | 1.1E2 | 1.5E2 | 5.7E2 | 1.5E2 | 7.8E0 | 1.0E1 | 1.0E4 | 5.6E2 | 363 | 17 | 141 | 17 | 0.69 |
| cH | uIU/mL | 3.1E0 | 1.9E0 | 6.7E0 | 5.7E0 | 1.3E1 | 1.2E1 | 8.6E-3 | 8.6E-3 | 1.6E2 | 5.3E1 | 363 | 17 | 141 | 17 | 0.40 |
| cI | ng/mL | 5.6E0 | 7.4E0 | 1.1E1 | 1.6E1 | 1.5E1 | 2.5E1 | 1.0E-3 | 3.2E-2 | 9.4E1 | 1.0E2 | 363 | 17 | 141 | 17 | 0.52 |
| cJ | ug/mL | 6.5E1 | 3.1E1 | 1.2E2 | 6.9E1 | 1.5E2 | 8.7E1 | 4.0E0 | 1.2E1 | 9.6E2 | 3.3E2 | 363 | 17 | 141 | 17 | 0.39 |
| cK | ng/mL | 3.8E-3 | 3.8E-3 | 5.9E-2 | 3.9E-2 | 2.0E-1 | 8.9E-2 | 3.8E-3 | 3.8E-3 | 1.7E0 | 3.0E-1 | 363 | 17 | 141 | 17 | 0.50 |
| cL | pg/mL | 1.9E2 | 2.4E2 | 4.0E2 | 5.2E2 | 1.5E3 | 6.7E2 | 1.6E1 | 6.5E1 | 2.4E4 | 2.6E3 | 363 | 17 | 141 | 17 | 0.66 |
| cM | pg/mL | 2.8E2 | 2.5E2 | 3.1E2 | 2.5E2 | 2.1E2 | 1.3E2 | 8.7E1 | 4.7E1 | 1.6E3 | 4.8E2 | 363 | 17 | 141 | 17 | 0.41 |
| cN | pg/mL | 1.2E2 | 1.2E2 | 1.3E2 | 1.5E2 | 7.0E1 | 6.7E1 | 3.8E1 | 6.8E1 | 1.1E3 | 3.5E2 | 363 | 17 | 141 | 17 | 0.61 |
| cO | pg/mL | 2.2E2 | 2.1E2 | 3.3E2 | 2.9E2 | 1.0E3 | 2.3E2 | 5.4E1 | 1.0E2 | 1.9E4 | 1.1E3 | 363 | 17 | 141 | 17 | 0.51 |
| cP | ng/mL | 2.6E3 | 2.2E3 | 2.6E3 | 2.7E3 | 9.4E2 | 9.7E2 | 6.2E2 | 1.4E3 | 5.7E3 | 4.8E3 | 363 | 17 | 141 | 17 | 0.48 |
| cQ | ng/mL | 4.9E-2 | 5.3E-2 | 1.2E-1 | 1.9E-1 | 2.3E-1 | 4.5E-1 | 2.0E-3 | 2.0E-3 | 2.2E0 | 1.9E0 | 363 | 17 | 141 | 17 | 0.49 |
| cR | ng/mL | 2.8E2 | 3.1E2 | 4.3E2 | 1.0E3 | 6.0E2 | 2.0E3 | 2.0E1 | 3.6E1 | 7.7E3 | 7.7E3 | 363 | 17 | 141 | 17 | 0.56 |
| cS | ng/mL | 2.6E2 | 3.4E2 | 3.7E2 | 1.7E3 | 3.7E2 | 5.3E3 | 4.7E1 | 9.1E1 | 2.7E3 | 2.2E4 | 363 | 17 | 141 | 17 | 0.57 |
| cT | ng/mL | 3.1E1 | 7.9E1 | 8.6E1 | 2.6E2 | 1.9E2 | 5.2E2 | 4.6E0 | 5.1E0 | 2.1E3 | 1.9E3 | 363 | 17 | 141 | 17 | 0.65 |
| cU | ng/mL | 5.3E1 | 8.4E1 | 7.7E1 | 9.6E1 | 1.1E2 | 7.7E1 | 6.2E0 | 5.4E0 | 1.6E3 | 2.9E2 | 363 | 17 | 141 | 17 | 0.58 |
| cV | ng/mL | 1.7E-1 | 2.9E-1 | 4.2E-1 | 1.5E0 | 2.5E0 | 2.6E0 | 3.4E-4 | 3.0E-2 | 4.7E1 | 9.7E0 | 363 | 17 | 141 | 17 | 0.69 |
| cW | mIU/mL | 5.3E-2 | 4.5E-2 | 1.6E-1 | 6.8E-2 | 7.9E-1 | 5.6E-2 | 3.7E-4 | 1.9E-2 | 9.7E0 | 2.1E-1 | 363 | 17 | 141 | 17 | 0.48 |
| cX | ng/mL | 1.0E-1 | 3.6E-1 | 1.4E0 | 4.9E0 | 4.5E0 | 9.9E0 | 2.3E-4 | 2.3E-4 | 2.8E1 | 2.8E1 | 363 | 17 | 141 | 17 | 0.56 |

Figure 20 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cY | ng/mL | 8.8E0 | 7.9E0 | 1.3E1 | 1.3E1 | 1.4E1 | 1.4E1 | 1.5E-1 | 6.1E-1 | 8.3E1 | 5.2E1 | 363 | 17 | 141 | 17 | 0.47 |
| cZ | ug/mL | 1.4E1 | 1.4E1 | 1.5E1 | 1.5E1 | 6.1E0 | 7.4E0 | 2.7E0 | 5.6E0 | 3.9E1 | 3.4E1 | 363 | 17 | 141 | 17 | 0.49 |
| dA | pg/mL | 3.3E2 | 3.2E2 | 3.7E2 | 3.7E2 | 3.3E2 | 2.4E2 | 9.0E1 | 1.6E2 | 5.8E3 | 9.3E2 | 363 | 17 | 141 | 17 | 0.44 |
| dB | ug/mL | 1.7E1 | 2.2E1 | 1.8E1 | 2.0E1 | 1.8E1 | 9.0E0 | 9.4E-1 | 2.5E0 | 8.3E1 | 3.2E1 | 363 | 17 | 141 | 17 | 0.67 |
| dC | nmol/L | 3.5E1 | 3.5E1 | 4.0E1 | 3.8E1 | 1.9E1 | 1.5E1 | 9.1E0 | 1.3E1 | 1.4E2 | 7.5E1 | 363 | 17 | 141 | 17 | 0.49 |
| dD | ug/mL | 3.6E1 | 3.0E1 | 3.7E1 | 3.4E1 | 1.1E1 | 1.3E1 | 1.3E1 | 1.6E1 | 7.6E1 | 5.6E1 | 363 | 17 | 141 | 17 | 0.42 |
| dE | ng/mL | 4.7E-1 | 3.8E-1 | 6.1E-1 | 4.4E-1 | 7.4E-1 | 4.4E-1 | 8.4E-3 | 8.4E-3 | 7.2E0 | 1.8E0 | 363 | 17 | 141 | 17 | 0.45 |
| dF | ng/mL | 2.2E2 | 3.1E2 | 2.7E2 | 4.3E2 | 1.8E2 | 3.0E2 | 7.5E1 | 6.1E1 | 1.3E3 | 1.2E3 | 363 | 17 | 141 | 17 | 0.69 |
| dG | ng/mL | 1.1E1 | 1.6E1 | 1.4E1 | 2.1E1 | 1.3E1 | 1.8E1 | 3.1E0 | 4.2E0 | 1.8E2 | 7.6E1 | 363 | 17 | 141 | 17 | 0.65 |
| dH | pg/mL | 7.5E0 | 1.1E1 | 1.3E1 | 1.8E1 | 4.1E1 | 1.9E1 | 4.0E-2 | 2.2E0 | 6.7E2 | 7.9E1 | 363 | 17 | 141 | 17 | 0.66 |
| dI | pg/mL | 4.6E-1 | 4.6E-1 | 2.5E0 | 3.6E0 | 1.8E1 | 9.7E0 | 4.6E-1 | 4.6E-1 | 3.3E2 | 4.1E1 | 363 | 17 | 141 | 17 | 0.53 |
| dJ | ng/mL | 1.9E0 | 2.6E0 | 2.2E0 | 2.6E0 | 1.2E0 | 1.3E0 | 3.2E-2 | 3.2E-2 | 6.9E0 | 4.4E0 | 363 | 17 | 141 | 17 | 0.61 |
| dK | uIU/mL | 1.9E0 | 2.4E0 | 3.2E0 | 3.0E0 | 6.5E0 | 3.4E0 | 2.8E-4 | 4.3E-1 | 7.9E1 | 1.5E1 | 363 | 17 | 141 | 17 | 0.54 |
| dL | pg/mL | 8.8E2 | 1.0E3 | 1.0E3 | 1.3E3 | 4.9E2 | 8.3E2 | 3.4E2 | 3.3E2 | 3.4E3 | 3.8E3 | 363 | 17 | 141 | 17 | 0.56 |
| dM | pg/mL | 9.7E2 | 1.1E3 | 1.2E3 | 1.5E3 | 9.3E2 | 1.1E3 | 3.9E2 | 3.4E2 | 1.2E4 | 4.3E3 | 363 | 17 | 141 | 17 | 0.60 |
| dN | ug/mL | 9.4E1 | 1.1E2 | 9.9E1 | 1.1E2 | 3.4E1 | 4.8E1 | 2.5E1 | 1.6E1 | 2.4E2 | 2.0E2 | 363 | 17 | 141 | 17 | 0.60 |
| dR | pg/ml | 1.6E3 | 1.3E3 | 2.4E3 | 2.4E3 | 2.5E3 | 2.8E3 | 1.4E2 | 1.8E2 | 1.5E4 | 8.9E3 | 245 | 15 | 138 | 15 | 0.46 |
| eF | ng/ml | 4.1E0 | 4.4E0 | 4.6E0 | 5.3E0 | 2.2E0 | 2.5E0 | 1.4E0 | 2.6E0 | 1.8E1 | 1.2E1 | 257 | 15 | 138 | 15 | 0.61 |
| eC | pg/ml | 3.1E2 | 2.7E2 | 3.7E2 | 4.5E2 | 2.2E2 | 4.3E2 | 4.5E1 | 1.3E2 | 1.4E3 | 1.6E3 | 203 | 14 | 135 | 14 | 0.47 |
| eD | pg/ml | 2.1E2 | 1.7E2 | 5.9E2 | 1.9E2 | 1.2E3 | 8.6E1 | 5.2E-1 | 3.1E1 | 7.0E3 | 3.0E2 | 173 | 13 | 111 | 13 | 0.41 |
| fP | ng/ml | 2.5E2 | 3.1E2 | 2.9E2 | 4.1E2 | 1.7E2 | 3.7E2 | 1.8E0 | 1.1E2 | 1.0E3 | 1.6E3 | 240 | 15 | 137 | 15 | 0.61 |
| fR | ng/ml | 1.2E5 | 2.3E5 | 1.7E5 | 3.2E5 | 1.4E5 | 2.3E5 | 3.1E4 | 1.0E5 | 7.2E5 | 7.2E5 | 236 | 11 | 68 | 11 | 0.74 |
| gL | pg/ml | 6.3E4 | 7.1E4 | 6.9E4 | 7.2E4 | 2.8E4 | 2.6E4 | 1.1E4 | 3.1E4 | 1.8E5 | 1.4E5 | 245 | 15 | 138 | 15 | 0.55 |
| gP | U/ml | 2.8E2 | 2.7E2 | 2.8E2 | 2.4E2 | 1.1E2 | 8.4E1 | 1.2E1 | 7.1E1 | 1.1E3 | 3.9E2 | 253 | 15 | 138 | 15 | 0.40 |
| gW | ng/ml | 5.7E2 | 5.4E2 | 1.2E3 | 9.5E2 | 1.7E3 | 1.3E3 | 3.1E-1 | 3.5E1 | 9.5E3 | 5.1E3 | 213 | 14 | 129 | 14 | 0.46 |
| tF | pg/mL | 1.5E3 | 2.1E3 | 1.6E4 | 5.9E3 | 4.7E4 | 7.8E3 | 1.2E1 | 1.8E1 | 3.2E5 | 2.3E4 | 203 | 14 | 135 | 14 | 0.54 |
| hA | ng/ml | 2.2E0 | 2.6E0 | 1.0E1 | 1.4E1 | 3.9E1 | 2.1E1 | 1.7E-2 | 1.7E-2 | 3.5E2 | 6.1E1 | 173 | 13 | 111 | 13 | 0.61 |
| nM | pg/ml | 1.0E-9 | 1.0E-9 | 9.1E1 | 1.0E-9 | 9.6E2 | 0.0E0 | 1.0E-9 | 1.0E-9 | 1.0E4 | 1.0E-9 | 113 | 11 | 88 | 11 | 0.49 |
| nN | pg/ml | 1.4E3 | 1.8E3 | 5.8E3 | 2.2E3 | 2.7E4 | 1.8E3 | 1.1E2 | 4.1E2 | 2.7E5 | 6.2E3 | 113 | 11 | 88 | 11 | 0.53 |
| nO | pg/ml | 2.6E1 | 2.4E1 | 4.1E1 | 6.1E1 | 4.3E1 | 8.7E1 | 3.5E0 | 9.7E0 | 2.4E2 | 3.1E2 | 113 | 11 | 88 | 11 | 0.57 |
| nR | pg/ml | 1.5E1 | 8.6E1 | 4.3E1 | 1.6E2 | 9.3E1 | 2.1E2 | 1.0E-9 | 2.2E0 | 8.2E2 | 7.1E2 | 113 | 11 | 88 | 11 | 0.69 |
| nT | pg/ml | 7.3E1 | 5.3E1 | 2.2E2 | 8.9E1 | 8.5E2 | 7.4E1 | 1.0E-9 | 2.3E1 | 6.6E3 | 2.3E2 | 113 | 11 | 88 | 11 | 0.50 |
| nU | pg/ml | 3.9E1 | 1.2E2 | 3.0E2 | 1.4E2 | 1.6E3 | 1.3E2 | 1.0E-9 | 1.0E-9 | 1.3E4 | 4.4E2 | 113 | 11 | 88 | 11 | 0.71 |
| lW | pg/ml | 1.0E-9 | 1.0E-9 | 1.5E1 | 2.2E1 | 5.1E1 | 5.1E1 | 1.0E-9 | 1.0E-9 | 3.9E2 | 1.6E2 | 113 | 11 | 88 | 11 | 0.50 |
| lX | pg/ml | 9.4E2 | 8.9E2 | 9.9E2 | 9.2E2 | 5.3E2 | 5.5E2 | 1.2E2 | 3.3E2 | 2.5E3 | 1.8E3 | 113 | 11 | 88 | 11 | 0.46 |
| lY | pg/ml | 1.9E1 | 1.8E1 | 2.3E1 | 2.0E1 | 2.2E1 | 1.0E1 | 1.0E-9 | 4.2E0 | 1.4E2 | 3.9E1 | 113 | 11 | 88 | 11 | 0.51 |
| mE | pg/ml | 1.0E-9 | 1.0E-9 | 2.9E0 | 3.9E0 | 8.8E0 | 8.4E0 | 1.0E-9 | 1.0E-9 | 5.8E1 | 2.8E1 | 113 | 11 | 88 | 11 | 0.52 |
| mF | pg/ml | 1.0E-9 | 8.7E-1 | 4.3E0 | 3.9E0 | 2.5E1 | 4.7E0 | 1.0E-9 | 1.0E-9 | 2.5E2 | 1.3E1 | 113 | 11 | 88 | 11 | 0.69 |
| mH | pg/ml | 3.2E0 | 2.0E0 | 4.8E0 | 4.7E0 | 6.6E0 | 5.5E0 | 2.3E-1 | 7.6E-1 | 5.3E1 | 1.8E1 | 113 | 11 | 88 | 11 | 0.45 |
| mI | pg/ml | 1.0E-9 | 1.0E-9 | 1.3E1 | 1.2E1 | 2.9E1 | 2.2E1 | 1.0E-9 | 1.0E-9 | 1.8E2 | 6.1E1 | 113 | 11 | 88 | 11 | 0.46 |
| mM | pg/ml | 2.8E1 | 3.8E1 | 8.0E1 | 1.1E2 | 1.6E2 | 1.4E2 | 1.0E-9 | 1.0E-9 | 1.0E3 | 4.4E2 | 113 | 11 | 88 | 11 | 0.58 |
| mP | pg/ml | 1.4E1 | 1.8E1 | 2.0E1 | 2.5E1 | 2.6E1 | 1.9E1 | 1.0E-9 | 1.3E0 | 1.9E2 | 7.7E1 | 112 | 11 | 87 | 11 | 0.70 |
| mS | pg/ml | 1.8E3 | 2.0E3 | 2.0E3 | 2.0E3 | 1.7E3 | 1.2E3 | 1.0E-9 | 9.9E2 | 1.3E4 | 5.1E3 | 113 | 11 | 88 | 11 | 0.52 |
| mT | pg/ml | 5.4E1 | 4.9E1 | 1.2E2 | 1.2E2 | 1.9E2 | 1.5E2 | 1.0E1 | 1.2E1 | 1.4E3 | 5.0E2 | 112 | 11 | 87 | 11 | 0.48 |
| mU | pg/ml | 2.3E0 | 3.2E0 | 6.3E0 | 5.3E0 | 2.2E1 | 6.0E0 | 1.0E-9 | 1.7E0 | 2.2E2 | 2.2E1 | 112 | 11 | 87 | 11 | 0.63 |
| mW | pg/ml | 2.5E3 | 2.3E3 | 2.8E3 | 2.9E3 | 1.6E3 | 2.5E3 | 4.3E2 | 3.7E2 | 1.0E4 | 9.8E3 | 112 | 11 | 87 | 11 | 0.46 |
| mY | pg/ml | 6.2E2 | 8.9E2 | 9.1E2 | 9.8E2 | 1.4E3 | 6.0E2 | 1.0E-9 | 2.4E2 | 1.1E4 | 2.5E3 | 113 | 11 | 88 | 11 | 0.67 |
| mZ | pg/ml | 2.4E2 | 2.7E2 | 4.0E2 | 4.9E2 | 4.6E2 | 5.5E2 | 2.1E0 | 1.6E1 | 3.1E3 | 1.5E3 | 112 | 11 | 87 | 11 | 0.46 |
| nA | pg/ml | 1.6E0 | 2.5E0 | 1.2E1 | 1.0E1 | 4.7E1 | 1.9E1 | 1.0E-9 | 1.0E-9 | 4.4E2 | 6.5E1 | 112 | 11 | 87 | 11 | 0.55 |
| nB | pg/ml | 3.1E2 | 3.6E2 | 3.3E2 | 3.8E2 | 1.5E2 | 1.9E2 | 3.0E1 | 1.5E2 | 8.2E2 | 7.8E2 | 113 | 11 | 88 | 11 | 0.57 |
| nC | pg/ml | 1.0E-9 | 1.5E2 | 4.3E3 | 5.6E4 | 3.4E4 | 1.3E5 | 1.0E-9 | 1.0E-9 | 3.7E5 | 3.8E5 | 113 | 11 | 88 | 11 | 0.67 |
| nD | pg/ml | 7.9E0 | 1.1E1 | 3.8E1 | 3.5E1 | 2.2E2 | 7.5E1 | 1.0E-9 | 1.0E-9 | 1.7E3 | 2.6E2 | 112 | 11 | 87 | 11 | 0.65 |
| nF | pg/ml | 1.0E-9 | 1.0E-9 | 5.0E0 | 4.5E0 | 2.8E1 | 9.0E0 | 1.0E-9 | 1.0E-9 | 2.4E2 | 2.7E1 | 113 | 11 | 88 | 11 | 0.58 |
| nH | pg/ml | 3.8E-1 | 5.4E0 | 1.0E2 | 1.2E3 | 9.5E2 | 3.0E3 | 1.0E-9 | 1.0E-9 | 1.0E4 | 1.0E4 | 112 | 11 | 87 | 11 | 0.64 |
| nI | pg/ml | 2.8E0 | 4.6E1 | 1.7E2 | 6.8E1 | 9.0E2 | 9.9E1 | 1.0E-9 | 1.0E-9 | 9.2E3 | 3.5E2 | 113 | 11 | 88 | 11 | 0.54 |
| nJ | pg/ml | 1.7E-1 | 6.3E-1 | 4.8E1 | 1.3E1 | 4.8E2 | 4.0E1 | 1.0E-9 | 1.0E-9 | 5.2E3 | 1.3E2 | 113 | 11 | 88 | 11 | 0.60 |
| nK | pg/ml | 1.0E-9 | 1.0E-9 | 6.2E1 | 2.8E1 | 3.7E2 | 4.0E1 | 1.0E-9 | 1.0E-9 | 3.2E3 | 1.0E2 | 112 | 11 | 87 | 11 | 0.58 |

Figure 20 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nL | pg/ml | 1.0E-9 | 5.2E0 | 4.5E2 | 1.6E3 | 4.2E3 | 4.2E3 | 1.0E-9 | 1.0E-9 | 4.5E4 | 1.4E4 | 113 | 11 | 88 | 11 | 0.65 |
| hR | pg/ml | 2.6E4 | 2.2E4 | 2.7E4 | 2.6E4 | 1.1E4 | 1.1E4 | 1.1E1 | 1.3E4 | 5.8E4 | 4.5E4 | 165 | 12 | 109 | 12 | 0.44 |
| hV | pg/ml | 4.3E2 | 4.7E2 | 4.5E2 | 4.1E2 | 2.4E2 | 2.1E2 | 6.8E1 | 9.6E1 | 1.5E3 | 7.1E2 | 165 | 12 | 109 | 12 | 0.45 |
| hW | pg/ml | 1.6E3 | 2.4E3 | 2.1E3 | 2.3E3 | 1.7E3 | 8.4E2 | 2.2E2 | 1.1E3 | 1.0E4 | 3.5E3 | 165 | 12 | 109 | 12 | 0.65 |
| hX | pg/ml | 9.0E2 | 1.3E3 | 1.0E3 | 1.4E3 | 8.2E2 | 7.2E2 | 1.3E2 | 2.1E2 | 8.6E3 | 2.9E3 | 165 | 12 | 109 | 12 | 0.68 |
| iA | pg/ml | 1.5E2 | 2.3E2 | 3.0E2 | 3.4E2 | 6.6E2 | 3.0E2 | 1.1E1 | 4.1E1 | 7.1E3 | 9.5E2 | 203 | 14 | 135 | 14 | 0.64 |
| iB | ng/ml | 5.0E0 | 5.9E0 | 6.3E0 | 9.5E0 | 5.0E0 | 7.8E0 | 3.3E-2 | 1.6E0 | 3.8E1 | 2.4E1 | 173 | 13 | 111 | 13 | 0.61 |
| iC | U/ml | 2.3E-1 | 5.8E-1 | 1.0E0 | 1.3E0 | 4.9E0 | 2.8E0 | 1.0E-9 | 1.0E-1 | 5.5E1 | 1.1E1 | 173 | 13 | 111 | 13 | 0.71 |
| iH | ng/ml | 1.6E5 | 1.9E5 | 1.5E5 | 1.8E5 | 4.7E4 | 6.6E4 | 5.1E4 | 2.9E3 | 2.7E5 | 2.5E5 | 203 | 14 | 135 | 14 | 0.69 |
| iJ | ng/ml | 5.3E4 | 4.3E4 | 5.5E4 | 4.7E4 | 3.0E4 | 3.5E4 | 7.7E3 | 1.8E3 | 2.5E5 | 1.5E5 | 203 | 14 | 135 | 14 | 0.37 |
| hB | ng/ml | 4.3E-1 | 6.5E-1 | 5.4E-1 | 1.1E0 | 4.1E-1 | 9.5E-1 | 1.2E-1 | 1.2E-1 | 3.0E0 | 3.4E0 | 203 | 14 | 135 | 14 | 0.72 |
| hC | pg/ml | 4.1E3 | 7.6E3 | 7.1E3 | 9.4E3 | 1.0E4 | 1.1E4 | 1.0E-9 | 1.0E-9 | 1.1E5 | 4.3E4 | 203 | 14 | 135 | 14 | 0.55 |
| hF | ng/ml | 1.0E-9 | 1.0E-9 | 2.4E1 | 1.0E-9 | 2.9E2 | 0.0E0 | 1.0E-9 | 1.0E-9 | 4.0E3 | 1.0E-9 | 203 | 14 | 135 | 14 | 0.49 |
| hG | pg/ml | 7.0E3 | 7.0E3 | 7.7E3 | 7.3E3 | 3.3E3 | 2.5E3 | 1.7E3 | 3.7E3 | 2.0E4 | 1.2E4 | 203 | 14 | 135 | 14 | 0.49 |
| iO | ng/ml | 3.8E5 | 3.2E5 | 4.0E5 | 3.3E5 | 1.8E5 | 1.6E5 | 8.3E4 | 6.4E4 | 1.1E6 | 6.7E5 | 203 | 14 | 135 | 14 | 0.37 |
| iP | ng/ml | 5.1E4 | 3.5E4 | 5.7E4 | 4.6E4 | 5.5E4 | 2.6E4 | 2.4E3 | 3.4E3 | 5.5E5 | 9.7E4 | 203 | 14 | 135 | 14 | 0.44 |
| iZ | ng/ml | 1.6E3 | 1.8E3 | 1.8E3 | 2.0E3 | 7.6E2 | 7.8E2 | 4.7E2 | 1.1E3 | 5.7E3 | 4.1E3 | 201 | 14 | 133 | 14 | 0.59 |
| rC | pg/ml | 1.5E3 | 1.2E3 | 2.2E3 | 2.0E3 | 2.3E3 | 1.8E3 | 1.0E-9 | 1.9E2 | 1.5E4 | 7.3E3 | 163 | 13 | 105 | 13 | 0.49 |
| rB | pg/ml | 2.4E1 | 3.2E1 | 4.7E1 | 5.4E1 | 9.5E1 | 6.7E1 | 1.0E-9 | 1.0E-9 | 9.5E2 | 2.5E2 | 163 | 13 | 105 | 13 | 0.57 |
| jD | ng/ml | 3.6E1 | 2.2E1 | 5.2E1 | 3.0E1 | 6.3E1 | 3.0E1 | 1.0E-9 | 1.0E-9 | 5.1E2 | 1.0E2 | 172 | 13 | 111 | 13 | 0.39 |
| jE | ng/ml | 1.0E-9 | 1.0E-9 | 6.2E0 | 3.8E0 | 1.6E1 | 1.0E1 | 1.0E-9 | 1.0E-9 | 1.2E2 | 3.4E1 | 172 | 13 | 111 | 13 | 0.47 |
| jF | ng/ml | 3.1E1 | 2.3E1 | 5.0E1 | 2.4E1 | 6.1E1 | 2.3E1 | 1.0E-9 | 1.0E-9 | 3.5E2 | 5.7E1 | 172 | 13 | 111 | 13 | 0.40 |
| jG | ng/ml | 4.4E3 | 3.9E3 | 4.5E3 | 3.8E3 | 1.9E3 | 2.3E3 | 7.6E2 | 6.7E2 | 9.6E3 | 7.8E3 | 173 | 13 | 111 | 13 | 0.40 |
| jH | ng/ml | 7.7E1 | 5.5E1 | 8.6E1 | 6.2E1 | 4.8E1 | 2.9E1 | 1.3E1 | 1.5E1 | 3.3E2 | 1.3E2 | 173 | 13 | 111 | 13 | 0.33 |
| jI | ng/ml | 7.3E1 | 8.9E1 | 7.7E1 | 9.3E1 | 3.3E1 | 3.9E1 | 2.8E1 | 5.4E1 | 2.5E2 | 1.8E2 | 173 | 13 | 111 | 13 | 0.65 |
| rA | pg/ml | 2.5E1 | 3.0E1 | 3.0E1 | 3.6E1 | 2.3E1 | 2.2E1 | 1.0E-9 | 5.8E0 | 1.2E2 | 7.2E1 | 171 | 14 | 108 | 14 | 0.59 |
| qZ | pg/ml | 4.3E1 | 2.7E1 | 4.3E2 | 1.5E3 | 1.9E3 | 3.8E3 | 1.0E-9 | 5.2E-4 | 1.0E4 | 1.0E4 | 132 | 7 | 96 | 7 | 0.53 |
| qY | pg/ml | 2.3E1 | 1.9E1 | 5.3E1 | 3.3E1 | 7.1E1 | 3.1E1 | 8.7E-1 | 5.1E0 | 5.3E2 | 9.8E1 | 171 | 14 | 108 | 14 | 0.47 |
| qX | pg/ml | 5.3E1 | 7.0E1 | 6.3E1 | 9.0E1 | 4.2E1 | 7.0E1 | 1.0E-9 | 2.9E0 | 2.1E2 | 2.1E2 | 171 | 14 | 108 | 14 | 0.58 |
| qW | pg/ml | 8.6E0 | 8.0E0 | 1.2E1 | 1.0E1 | 1.2E1 | 8.3E0 | 1.0E-9 | 1.0E-9 | 7.1E1 | 2.8E1 | 171 | 14 | 108 | 14 | 0.48 |
| qV | pg/ml | 2.1E3 | 2.5E3 | 2.8E3 | 2.6E3 | 2.1E3 | 1.5E3 | 1.0E2 | 1.7E2 | 1.1E4 | 4.9E3 | 171 | 14 | 108 | 14 | 0.51 |
| qU | pg/ml | 5.6E1 | 1.2E2 | 1.6E2 | 1.6E2 | 2.8E2 | 1.6E2 | 1.0E-9 | 1.0E-9 | 2.1E3 | 5.1E2 | 171 | 14 | 108 | 14 | 0.57 |
| qT | pg/ml | 4.1E1 | 7.3E1 | 6.9E1 | 1.0E2 | 1.0E2 | 1.1E2 | 1.0E-9 | 1.2E1 | 9.0E2 | 4.4E2 | 171 | 14 | 108 | 14 | 0.65 |
| jK | ng/ml | 1.6E3 | 1.5E3 | 1.7E3 | 1.6E3 | 6.6E2 | 5.4E2 | 2.8E2 | 8.7E2 | 4.3E3 | 2.4E3 | 173 | 13 | 111 | 13 | 0.46 |
| jL | ng/ml | 2.0E2 | 2.0E2 | 3.0E2 | 3.6E2 | 2.6E2 | 4.3E2 | 3.6E1 | 9.8E1 | 2.1E3 | 1.7E3 | 173 | 13 | 111 | 13 | 0.51 |
| jM | ng/ml | 7.0E4 | 6.7E4 | 7.3E4 | 7.1E4 | 3.7E4 | 3.5E4 | 3.9E2 | 1.1E4 | 1.7E5 | 1.4E5 | 173 | 13 | 111 | 13 | 0.49 |
| jO | pg/ml | 2.2E5 | 2.5E5 | 2.7E5 | 2.5E5 | 1.5E5 | 1.3E5 | 5.2E4 | 1.2E5 | 8.0E5 | 5.6E5 | 173 | 13 | 111 | 13 | 0.48 |
| jP | pg/ml | 2.4E5 | 2.6E5 | 2.7E5 | 2.8E5 | 1.6E5 | 1.3E5 | 5.8E4 | 7.8E4 | 9.2E5 | 5.8E5 | 173 | 13 | 111 | 13 | 0.57 |
| jQ | pg/ml | 2.5E3 | 2.4E3 | 3.4E3 | 2.6E3 | 3.4E3 | 1.8E3 | 1.0E-9 | 2.9E2 | 1.8E4 | 6.1E3 | 173 | 13 | 111 | 13 | 0.47 |
| jR | pg/ml | 5.9E3 | 3.7E3 | 1.0E4 | 8.9E3 | 1.2E4 | 1.0E4 | 1.0E-9 | 2.9E2 | 9.0E4 | 3.4E4 | 173 | 13 | 111 | 13 | 0.46 |
| jT | pg/ml | 1.7E5 | 1.6E5 | 1.8E5 | 1.6E5 | 6.8E4 | 5.1E4 | 6.8E4 | 8.8E4 | 4.5E5 | 2.5E5 | 173 | 13 | 111 | 13 | 0.42 |
| jU | mIU/ml | 4.6E0 | 3.0E0 | 1.0E1 | 8.6E0 | 1.7E1 | 1.2E1 | 6.2E-2 | 6.3E-2 | 1.1E2 | 4.3E1 | 173 | 13 | 111 | 13 | 0.47 |
| jV | mIU/ml | 1.5E0 | 1.2E0 | 3.4E0 | 3.3E0 | 5.8E0 | 5.0E0 | 1.7E-3 | 4.1E-2 | 3.3E1 | 1.8E1 | 173 | 13 | 111 | 13 | 0.49 |
| jY | ng/ml | 7.4E-4 | 2.7E-3 | 6.5E-3 | 1.2E-2 | 2.9E-2 | 2.6E-2 | 1.0E-9 | 1.0E-9 | 3.0E-1 | 9.4E-2 | 173 | 13 | 111 | 13 | 0.66 |
| kC | pg/ml | 9.6E1 | 8.2E1 | 1.9E2 | 3.3E2 | 4.1E2 | 8.0E2 | 2.1E1 | 3.6E1 | 3.5E3 | 2.7E3 | 113 | 11 | 88 | 11 | 0.43 |
| kE | pg/ml | 1.4E5 | 1.4E5 | 1.4E5 | 1.3E5 | 3.9E4 | 4.2E4 | 1.2E4 | 3.8E4 | 2.3E5 | 1.9E5 | 113 | 11 | 88 | 11 | 0.48 |
| kF | pg/mL | 6.3E1 | 7.5E1 | 7.2E1 | 7.4E1 | 5.2E1 | 2.5E1 | 2.6E1 | 4.0E1 | 5.1E2 | 1.3E2 | 113 | 11 | 88 | 11 | 0.60 |
| kG | pg/mL | 9.2E3 | 1.2E4 | 1.4E4 | 1.4E4 | 1.7E4 | 1.5E4 | 7.5E2 | 3.2E3 | 1.2E5 | 5.8E4 | 113 | 11 | 88 | 11 | 0.56 |
| kI | pg/ml | 2.0E2 | 2.0E2 | 2.2E2 | 2.5E2 | 1.3E2 | 1.5E2 | 4.4E1 | 7.2E1 | 8.7E2 | 5.5E2 | 113 | 11 | 88 | 11 | 0.55 |
| kK | pg/ml | 1.0E2 | 1.2E2 | 1.8E2 | 2.1E2 | 2.3E2 | 2.6E2 | 2.1E1 | 5.2E1 | 1.6E3 | 9.1E2 | 113 | 11 | 88 | 11 | 0.56 |
| kN | pg/ml | 1.0E3 | 8.8E2 | 2.1E3 | 1.9E3 | 5.6E3 | 2.5E3 | 7.6E1 | 4.4E2 | 5.5E4 | 8.7E3 | 113 | 11 | 88 | 11 | 0.52 |
| kO | pg/ml | 7.1E3 | 6.9E3 | 8.7E3 | 2.1E4 | 1.2E4 | 4.2E4 | 3.4E3 | 4.4E3 | 1.3E5 | 1.5E5 | 113 | 11 | 88 | 11 | 0.49 |
| kP | pg/ml | 6.4E3 | 5.4E3 | 7.5E3 | 6.7E3 | 6.3E3 | 3.6E3 | 8.6E2 | 1.5E3 | 4.8E4 | 1.3E4 | 113 | 11 | 88 | 11 | 0.51 |
| kQ | pg/ml | 4.3E3 | 4.0E3 | 5.0E3 | 4.4E3 | 2.9E3 | 1.4E3 | 5.6E2 | 2.5E3 | 2.5E4 | 7.0E3 | 203 | 14 | 135 | 14 | 0.47 |
| kR | pg/ml | 2.3E1 | 2.0E1 | 3.3E1 | 2.8E1 | 7.3E1 | 2.2E1 | 1.0E-9 | 5.6E0 | 1.0E3 | 7.7E1 | 203 | 14 | 135 | 14 | 0.47 |
| kS | pg/ml | 8.0E2 | 1.1E3 | 9.6E2 | 1.2E3 | 1.1E3 | 8.3E2 | 8.2E1 | 2.5E2 | 1.4E4 | 3.6E3 | 203 | 14 | 135 | 14 | 0.63 |
| rZ | ng/ml | 6.0E-4 | 2.2E-3 | 6.3E-3 | 6.0E-3 | 1.6E-2 | 7.6E-3 | 1.0E-9 | 1.0E-9 | 1.1E-1 | 2.2E-2 | 165 | 13 | 104 | 13 | 0.57 |

Figure 20 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| rY | ng/ml | 6.1E-2 | 5.4E-2 | 4.1E-1 | 1.1E-1 | 2.4E0 | 1.3E-1 | 1.0E-9 | 1.0E-9 | 2.3E1 | 5.0E-1 | 165 | 13 | 104 | 13 | 0.53 |
| rX | ng/ml | 1.0E-9 | 1.0E-9 | 7.9E-2 | 2.8E-2 | 4.5E-1 | 7.9E-2 | 1.0E-9 | 1.0E-9 | 3.7E0 | 2.9E-1 | 165 | 13 | 104 | 13 | 0.52 |
| lK | pg/ml | 8.1E1 | 8.4E1 | 1.8E2 | 1.2E2 | 3.2E2 | 1.4E2 | 1.0E-9 | 1.0E-9 | 3.3E3 | 5.0E2 | 172 | 13 | 111 | 13 | 0.44 |
| lL | pg/ml | 1.6E3 | 1.1E3 | 2.7E3 | 2.1E3 | 4.0E3 | 2.3E3 | 1.5E1 | 3.8E2 | 4.2E4 | 7.7E3 | 173 | 13 | 111 | 13 | 0.44 |
| lM | pg/ml | 1.1E3 | 1.2E3 | 4.1E3 | 4.8E3 | 8.6E3 | 7.9E3 | 3.9E1 | 9.5E0 | 5.1E4 | 2.7E4 | 173 | 13 | 111 | 13 | 0.56 |
| lN | pg/ml | 1.0E-9 | 1.0E-9 | 4.5E0 | 3.0E0 | 1.6E1 | 5.4E0 | 1.0E-9 | 1.0E-9 | 1.5E2 | 2.0E1 | 173 | 13 | 111 | 13 | 0.52 |
| lO | pg/ml | 1.0E-9 | 1.0E-9 | 1.8E0 | 1.0E-9 | 1.2E1 | 0.0E0 | 1.0E-9 | 1.0E-9 | 1.3E2 | 1.0E-9 | 172 | 13 | 111 | 13 | 0.48 |
| nW | pg/ml | 1.1E5 | 1.1E5 | 1.1E5 | 1.2E5 | 2.5E4 | 3.4E4 | 5.8E4 | 6.7E4 | 1.8E5 | 1.7E5 | 203 | 14 | 135 | 14 | 0.52 |
| nY | pg/ml | 2.1E3 | 2.1E3 | 2.4E3 | 2.5E3 | 1.6E3 | 1.4E3 | 5.1E2 | 7.6E2 | 1.3E4 | 5.0E3 | 203 | 14 | 135 | 14 | 0.52 |
| oO | pg/ml | 8.6E4 | 1.1E5 | 1.2E5 | 1.3E5 | 1.0E5 | 8.0E4 | 2.6E4 | 5.1E4 | 6.2E5 | 2.8E5 | 105 | 10 | 82 | 10 | 0.58 |
| oP | pg/ml | 1.4E5 | 2.1E5 | 1.5E5 | 2.1E5 | 9.3E4 | 9.3E4 | 4.2E4 | 1.1E5 | 4.5E5 | 4.2E5 | 105 | 10 | 82 | 10 | 0.71 |
| oQ | pg/ml | 3.0E3 | 4.4E3 | 3.9E3 | 5.3E3 | 3.0E3 | 3.2E3 | 1.1E3 | 1.9E3 | 2.1E4 | 1.2E4 | 105 | 10 | 82 | 10 | 0.68 |
| oE | pg/ml | 1.5E2 | 1.1E2 | 3.8E2 | 5.6E2 | 5.5E2 | 8.8E2 | 1.0E-9 | 2.8E0 | 4.7E3 | 2.8E3 | 203 | 14 | 135 | 14 | 0.49 |
| oF | pg/ml | 8.5E3 | 1.3E4 | 2.2E4 | 2.7E4 | 3.6E4 | 3.3E4 | 6.4E1 | 4.6E2 | 2.5E5 | 1.1E5 | 203 | 14 | 135 | 14 | 0.53 |
| oH | pg/ml | 4.1E1 | 2.4E1 | 9.4E1 | 8.0E1 | 1.4E2 | 8.9E1 | 4.2E0 | 4.3E-1 | 9.9E2 | 2.6E2 | 203 | 14 | 135 | 14 | 0.43 |
| oK | pg/ml | 7.6E2 | 1.3E3 | 1.9E3 | 1.6E3 | 2.6E3 | 1.6E3 | 5.2E1 | 1.8E2 | 1.8E4 | 6.8E3 | 203 | 14 | 135 | 14 | 0.55 |
| oN | pg/ml | 5.1E2 | 6.0E2 | 7.9E2 | 7.1E2 | 1.5E3 | 4.4E2 | 1.5E2 | 2.2E2 | 1.8E4 | 1.9E3 | 203 | 14 | 135 | 14 | 0.57 |
| pF | pg/ml | 4.8E-1 | 6.6E-1 | 1.1E0 | 1.5E0 | 6.1E0 | 2.1E0 | 1.0E-9 | 1.0E-9 | 8.7E1 | 7.8E0 | 203 | 14 | 135 | 14 | 0.61 |

Analyte panel data:

Unconstrained panels with 3 analytes, where 1.0E-8 >= 'model p-value' > 0. Contains 7 panels of 16,766,520 total panels evaluated. : Ib{Is(kE nK) FykE OwnR mFoP} FbIsnD QzOwnR Unconstrained panels with 3 analytes, where 1.0E-7 >= 'model p-value' > 1.0E-8. Contains 40 panels of 16,766,520 total panels evaluated. : Ng{Ow(Ad Bg cV Ef Jg Jp Kr My Pz Uu) Pz(Ba cV)} Ib{Is(kI mT nC nL) Kn(mW nR) QznR} Or{IK(kI nO) oP(Aw mF) NenC} Qz{mF(bF dF) OunL aNnR} JI{Hw(Ne NI) InPz} nC{oP(aM Aw) MwhB} Ow{ChnR KrOz} MwnLhB IsRfnK KymFoP LdkIpF Unconstrained panels with 3 analytes, where 1.0E-6 >= 'model p-value' > 1.0E-7. Contains 373 panels of 16,766,520 total panels evaluated. : Ow{Ng(Af Al Ap Aw aX Ba BC bF Bo bV bZ Ch cR cS Cv CX Dc Dd Dg eF Et Fa fP Fr gP Hb Hc Hf Hv Ij Ik II In Iq Is Iv JI Jn Js Kf Ki Kk Kl Kn Kp Kq Ks Kx Ky Lw Mb Mf Mk Ml Mm Mp Mt Mu Nc Ne Nf Nh Nj Nk NI Nm Nq Nt Nu Nx Og On Or Ou Oy Oz Pa Pb Pc Pk Qn Tn) Oz(aX Bo bV Ch cR cS cV Hb Hf Hw Ij Iv Js Kk Ks Mp Nf Nt Nu Om QI) Ib(Ad aX cR cV Ef kN Kr mZ nJ Nu oP Pz) Pz(Ch Ct cV Ii Ik In Jj Mg Nt Oi Ue) cV(Co Ct GI Js Kr Mp Nt Pk Po) Kr(Ct Nf Oa Pb Qx Rm Ue) Co(Bg fP Is Tn) Ik(bV cS Is) Pb(Nt Ql Ue) Ch(fP gP) oP(mF nl) Ajlu PoLx NUn NenR IsJs QwgP OrnJ UknU nKpF} Ib{Is(kF IW IX ml mU mW mZ nA nB nD nH nI nJ nN nT) nR(Dc Ji kE Kf Kk Ld Lh Mz Nw oH Pd) Lh(kG IY mM mP nC nI nL) Fy(kI mF mW nC nH nI oP) Mz(kI IX mW nl oP) nC(Ba Ji On oP Tv) mW(Ba Dc Ji Rm) Kf(iB jD IM) kl(cE oN Tn) Nj(hB oH) Or(mT nJ) nL(cE On) kE(dF Tn) BtoO TvmF KknU KnkN} JI{Hw(Ip Iq Is It Ji Jn Ly Mt Nc Nd Nh Nj Nk Pz Qc) In(It Jn Ly Nc Nd Ne Nj NI) Mw(kI mP mZ nF nL) Ii(Ji Ly Nd Nj Pz) Nd(Iq Oi Po) AdNg PoJi} mF{oP(Aj aM Ax bG Ch Di dL Hb Id Kj Kk Ko Ld Ph) Qz(Or Ou pF) Ld(aY nR pF) MwhB NeOr Kcml} Ng{Pz(Ad bA bF cT dF Dg hB Ou) My(Ad Ba cV Dg) Ba(Et Jp) AdMu ExNx JgcV KflM UujH} Qz{Ou(kI mZ nA nC nF nH nJ) nR(bN Ch Cp Fw Kn) Or(nC nJ) MakI} Or{Ne(nH nJ) Pz(nC nL) oP(Di kI) MenJ NInC} nC{oP(aF Ao Cp Ct Di) HbJi} In{Rm(kE kI mZ nJ) PgnF} nR{IK(aF aO Aw) LdkI} nK{ApoP IsKk LdpF} Ms{Ji(Iq It)} Ii{Nx(Ex Gz)} Qw{cXgP kIoN} aC{fR(bC bE)} AjMIIs CtPzbA PoEmOu MwhBkI IpKynJ LdnApF Unconstrained panels with 3 analytes, where 1.0E-5 >= 'model p-value' > 1.0E-6. Contains 4,225 panels of 16,766,520 total panels evaluated. : Ow{Ng(aA aC aD aE aF aG aH al AJ aK aL aM AN AO aP aQ AR AS aU aV aW Ax aY aZ bA BB bE bG bH bI bJ bL bM BN bO bP bQ bR bS bU bW bX cA cB cC cD cE cF cG cH cI cJ cK cL cM cN CO CP CQ Cs CT CU CW cY cZ dA DB dC dD DE dF dG dH DI dJ DK DL dM dN Dp dR Ed Ex Ez Fb Fn Fp Fw Fy GL Gp Gz Ha hB hF Hq Hr Hu Hv Hx Ib Ih Ii iJ Im IO Ip Ir It Iu Iz Jd Je Jf Jh Ji Jj Jk Jm Jo Jq Jr Jt Ju Jv Jy Kc Kd Ke Kg Kj Ko kS Kz Ld Lh Li Lj Lu Lv Lx Ly Lz Ma Mc Md Me Mg Mh Mi Mj Mn Mq Mr Ms Mv Mw Mx Mz Na Nb Nd Ni Nn No NR Ns nU Nv Nw Ny Oa Oe Of Oh Oi Ok Om Pd Pe Pf Pg Ph Pi Pj Po Qa Qb Qc Qd Qe Qg Qh QI Qm Qt Qu Qw Qx Qy Qz Ra Rb Rc Rf Rg Rj Rm Sr Ss Tr Tt Tv Ua Ub Uc Ud Ue Uf Uh Uk Um Uo Up Ur Ut Uv Vo Vp Vq Vs Vt Vv Wm Tj) Oz(aA aC AD Af aH Aj Al aM AN AO Ap AR As aV AW Ax aY aZ BA BB BC bE bF Bg bH bI bJ Bn bR bS bW bX bZ cB cC cD cE cH cl cJ cL cM CO CP CQ Cs Ct Cu Cv Cw CX cZ DB Dc DD DE DG DI DK DL dN Ef Et Fa Fb Fn FP Fr Fw GI GP Gz hB Hc Hq Hr Hu Hv Hx Ib Ih Ii Ik Il Im In IO Ip Iq Ir Is It Iu Iz Jg Jh Ji Jj Jk JI Jm Jn Jo Jp Jq Jr Jt Kc Kd Ke Kf Kg Ki Kj Kl Kn Ko Kp Kq kS Kx Ky Kz Ld Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nh Ni Nj Nk NI Nm Nn No Nq Nr Ns Nv Nw Nx Ny Oe Of Og Oh Oi Ok On Or Ou Oy Pa Pb Pc Pd Pe Pf Pg Ph Pi Pj Pk Po Pz Qb Qc Qn Qw QX Qz Rf Rj Tv Ub Ue Ut Tj) Ib{Al Aw BC bF Bg bI bN Bo bV bZ cJ cS Ct Cv Cw cX DB Dc Dd Dg dK Et Fn Fr gP Gz Hb Hc Hf Hq Hw Id ik In Ip Is Iu Iv Jg Jh JI Jn Jp Js kC kE KF kG KI KK kO KP Kq Ks Ky Lv IW IX IY Ma mE mF mH ml Mk Ml mM MP MS mT mU Mv mW MY NA nB NC nD Ne NF nH nl Nj NK NL NM nN nO NT nU Oe Of Og Oi oO oQ Ou Pb Pc Pi Pk Po Qh Ql Qn Qw Qx Qz Ra Rf Rj Sr Tn Tt Tv Ub Uc Ue Uk Uo Ut Uu Vq Vv Tj) Kr(Aj Ao AX Ba Bb bl Bo bV CH Co Cp cR CS Cv Cw cX Dc Dd DE dL Dp Ed Et Ez Ha Hb Hq Hu Hv Hw Id Ii Ij Ik In Is Iu Iz Jd Je Jh Jj Jk Jl Jn Jo Jp Ju Kc Kf Kg Kk Ky Lj Lu Lv Lw Lx Md Me Mf Mg Mk Ml Mm Mp Ms Mu Mw My Nc Ne Nj Nk Nl Nt Nu Of Og Oi Om Or Ou Oy Pc Pd Pg Ph Pk Po Pz Qa Qd Qe Qh Ql Qm Qn Qt Qu Qw Qy Qz Ra Rb Rf Rg Rh Rj St Tt Tv Ua Ub Uc Uf Ug Uh Uk Um Up Ur Ut Uu Uv Vp Vt Vv Wm Tj) cV(aD aF aH Aj aL aM AO aS AW aX aZ Ba Bb bC Bg bH bI bV bX cA cD CH cM cO Cp cR cS Cu Cv Cw cZ DE Dc Ef Fn Gz Hb Hf Hq Hu Hw Ii Ij Ik In Iz Jh Jj Jk Jo Jt Kc Kg Kk Ks Ky Lv Ly Lz Ma Md Me Mf Mg Mi Mk Ml Mn Ms Mu Mv Mw My Nb Nc Nd Ne Nf Nj Nk Nl Nm Nn Nq Ns Nu Nv Of Og Oi Om Or Oy Pb Pc Pd Pe Pg Ph Qb Qc Ql Qm Qw Qx Qz Ra Rf Ua Ue Ut Vq Vv Tj) Nt(Ad Af

Figure 20 Continued

AJ aM aX aZ bC Bg bl Bo bV bW bZ cD CH Co cR cS Ct Cv cX dE Dg dL Et Fa fP Fw Hb Hv Hw Ij Ik In Io Iq Ir Is Iu Iv Ji Jj Jl Jo Jp Kf Kn Kq Ky Lw Lx Mb Md Mf Mg Mk Ml Mm Mp Ms Mt My Mz Nc Ne Nf Nk Nl Nq nR nU Oa Of Og Ok Or Ou Oy Pc Ph Pk Qa Qe Qh Qn Qx Ra Rf Rj Ub Ue Uh Vt Wm) Ct(Ad Aj aX BC bF Bg Bo bV bZ cE Ch cR cS Cv cX Dc Ef Et Fa fP Fr gP Gz Hb Hf Hv Hw Ij Ik In Iq Ir Is It Iu Iv Jj Jl Jn Jp Js Kf Ki Kk Kn Kq Kx Ky Lu Lv Ma Mb Md Mf Mk Ml Mm Mp Ms Mv My Nc Ne Nf Nh Nj Nk Nl Nm nR NU Og Oi On Or Ou Pb Pc Ph Pk Qc Qh Ql Qx Rf Rj Tn Ue Vq) Pb(aC Aj Ao aX Bc Bg Bo bV Ch Co Cp cR cS Cv Dk Fn Gl Gz Hb Hf Hw Ii Ij Ik In Ir It Iv Iz Jj Jo Jp Js Jt Kc Kg Ki Kk Ko Kq Ks Ky Lv Ma Mf Mg Mn Mp Ms Mw Na Ne Nf Nk Nl Nm Nu Oe Of Og Oi Om Or Oy Ph Pk Po Pz Qc Qw Qz Rf Rj Ub Ut) Ik(AD Aj aX BC bl Bo bW CH cJ cM Co cR Cv cX Et Fa Gz Hb Hf Hv Hw Ii Ij In Io Ip Iq Ir It Iu Iv Jj Jl Jn Jo Jp Js Kf Ki Kk Kn Ks Ky Lz Md Mf Mg Mk Ml Mp Ms My Nc Ne Nf Nk Nl Nu Of Og Or Oy Pc Ph Pk Po Qa) Pz(aC Aj As Bg Bo bV Co Cp cR cS Dk Ef Hb Hw Ij Ir Is It Iv Iz Jk Jn Jo Kg Kj Kk Ks Ky Lv Mk Mp Ms Mv Mw Ne Nf Nl Nm Nu Of Og Om Or Oy Pc Pd Ph Po Ql Qw Qx Ub Ug Uk Ut) Ky(Aj Ao Bc bV Ch Co Cp cR cS Cv cX Dk Gl Hb Hu Hw Ii Ij In Is Iv Jj Jn Jo Kk Ks Lv Mf Mg Mk Ml Mn Mp Ms Mw Nf nJ Nk Nl Nu Of Og Oi Or Oy Pc Ph Pk Po Ql Qx Rf Ue) Ch(Ad aX bC bF Bg Bo bV cR cS cX dR EF Et gL hB Hf Hw iH Io IP Iq Ir Is It Iu Iv Jj Jl Jn Jp Kf Ki Kk kS Ml Mp My Na Nc Ne Nf Nj Nk Nl Nu Og Ou Pc Pk) Co(Ad aX Bc bF Bo bV bZ cR cS Cv Dc dR eF Et gL gP hB Hc In IO Ip Iq Ir It Iu Iv Jl Jn Jp Kf Kq kS Ml My Nc Nk Nl Nu Og Pc Pf) Of(Aj Bc bF Bg bV cR cS EF Et fP gP HB IJ In Is Iv Jj Jl Jn Jp Ki Kk Kq Mf Ml Mp My Nc Ne Nk Nl nR Og On Or Pc Pk Rf Tn) Aj(Ad aX BC Bg bV cR cS Cv Dg Et Hb Ij Io Ip Iq Ir Is It Iv Jn Jp Kf Ki Kk Mk Ml Mp My Ne Nf Nk Nu Oy Pc Pk) Mp(bC Bo bV bW bZ cR cS cX Fa Hw Ij Iq Is Jj Jl Jn Jp Mm My Nf Nk Pc Qh Ql Qn Rj Ub Ue Uf Uk Vt) Jj(aX bI bV cR cS Cv Dk Hb Hf Io Ip Iq Ir Is It Iu Iv Jn Ki Kk Nc Nf Nk Nl Nu Pc Pk Po Qx) Jo(Ad bF Bg bV bZ cR cS Cv Dc Dd Et fP Io Ip Iq Ir Is It Ju Iv Jl Jn Jp Kf Kk Mm My Nk Pc) cR(bI Gl gP Hb Hw Ii Ij In Iz Js Kg Md Mf Mg Nf nJ Nu Oy Pc Ph Pk Po Ql Ue) Hw(bV cS Io Iq Is It Iu Iv Jl Jn Kk Ml My Nk Nl Oa Pc Qa Qx Rm) Ij(bI bV cS cX Dc In Is It Iv Jn Jp Kk Ml Nf Nk Nl Nu Pc Rj Ue) Mg(Ad bC Bg bV cS Cv Et Iq Is Iu Iv Jn Jp Kf Mm My Nk nR) nJ(aM aY dE eD Ii In Iq It nF nR Oi PF Qz Rf Uk) Oy(Bg Io Ip Iq Ir Is It Iu Iv Jn Jp Kk My Nk Og) Po(Bo bV bZ cS Fa Is Iv Jl Jn Jp Kq Nk Og Or) Pc(Bo bV cS Hb Ii Kk Nf Nu Ph Pk Ql Rf Ue) Ue(Ad Cv Jn Nf Nu Pk Qn Qx Ra Vq Tj) Ql(cX Is Jl Jn Ml Nk Oa Qn Qx Ra Ub) Is(Cp Jk Ks Mk Ml nK Ph Pk Vv) Jn(Hb Ii In Kk Mf Nf Pk Rf Ut) Iv(bI Lv Mk Ml Ms Nf Ph Pk) Qw(dR eF fP gL Nk pF Qx Ub) bV(cX Hb Js Lv Nf Nu Ph Pk) Jp(Bg Cp Dk Ef Hb Iz) cS(cX Hb Js Nf Nn Pk) Uk(mE mF nF Qx Ut) fP(Hc Hu Nn Nq Qu) nI(cI Fn Mh Mt Or) Ml(Iq Ir It Iu) Pf(kI Mk mM nA) Pk(cX Iu Qx Ub) pF(kC nA nD nF) Ad(Ef Iz Jt) Nf(Bo Js Kk) Qz(kN mF nU) hB(Bg Mv Nn) Et(Hb Jt) Gz(Oi Ph) Mk(It Og) In(Em nU) Iu(Kg Ph) Jk(Bg Jl) Js(bI cX) Kk(cX Og) Or(mE mF) fR(It Oi) gP(cH Qu) nR(nF Qm) CpMy NuQx MhmF HqTn IinU HbOk QaQb RfQn aMoP bIbW cJnF} Ib{nR(BA Bc bX cQ cT dF Dg dI dM Et Fw Fy Id Ih Im In Ip Is Jl Jn Jp Jq Kc KI Ko Kp Kq lK Ma Mk Mm Mw Mx Nb nC Nj NK nL Nn Ns Nt Nv Oa Oe Of Oh Oi Ok Om On Or Pa Pz Qa Qb Qe Qh Qv Qw Rm Sr Tn Tv Tz Uf Uh Ul Un Up Uv Vo Vt Vu) Kn(kC kE kF kG kI kK kO kP lW lX lY mE mF mH mI mM mP mS mT mU mY mZ nA nB nC nD nF nH nI nJ nK nL nM nN nO nT nU oP) Mz(kC kE kF kG kK kN kO kP lW lY mE mF mH mI mM mP mS mT mU mY mZ nA nB nC nD nF nH nJ nK nL nM nN nO nT nU oO oQ) Fy(kC kF kG kK kN kO kP lW lX lY mE mH mI mM mP mS mT mU mY mZ nA nB nD nF nI nJ nK nL nM nN nO nT nU oO oQ) Lh(kC kE kF kI kK kN kO kP lW lX mE mF mH mI mS mT mU mW mY mZ nA nB nD nF nH nJ nK nM nN nO nT nU oP) Kf(eD hA hX iC jE jF jG jH jI jK jL jM jO jP jQ jR jT jU jV jY kN lL lN lO mW oH qU) Or(kE kF kG kI kK kN kP lY mE mF mM mS mW mY nA nB nC nD nH nI nL nN nO nT nU oP) Nj(Bg eC eF fP gP hC hG iA iH iJ iO iP Jp kQ kR kS nW nY oE oF oK Ou pF Tn tF) Is(Ic kC kG kK kN kO kP lY mE mF mH mM mP mS mY nF nM nO nU) mW(cE dF Et Jp Jq Kk Ko Ma Nv Nw Oh Ok On Qa Qh Sr St Uf Uh) Ji(kE kP mH mI mM mP mS mY nA nD nF nH nI nJ nL nO nU oP) nC(bF cE Dc dF Et hB Jp Kk Ma Nv Ok Rm Tn Uh Uu) kE(bZ cE Dc hB Jp Ma Ok On Ou Qa Qh Rm Tr Tv) oP(cQ Dc Ed Et Fw Jn Jp Jq Ks Ma nK Rm Uv Vu) Ma(kI lY mP mT mY nA nF nH nI nL nT) Dc(kG kI kN kO mF mP nJ nL nO nT) Tn(Kk Md mP nA Ng nL Ou Pz) On(kG kI lY mF mM mP nI nJ) kI(bF bZ dF Jp Ou Pf Rm) Ad(cV cX Ng Nt oH Ou) Rm(kO mF nL nO nT) bF(nA nF nH nK nL) Et(mM nO nT oQ) dF(lW mM nA nT) oH(Dg fR hB Uu) Kk(kN lW nI) Ou(cV cX nA) cE(mF nA nK) Pz(cV Jl) Nv(mM mP) Nx(Ex nU) Oh(nN nT) nL(hB Tv) DdcV QanT QwgP JpKi OkmM nAoN} Jl{Hw(Et Fp Fr Hq Hr Hu Hv Hx Ih Ii Ij Ik Il Im In Io Ir Iu Iv Jg Jh Jj Jk Jm Jo Jp Jq Jr Js Jt Lh Li Lj Lu Lv Lw Lx Lz Ma Mb Mc Md Me Mf Mg Mh Mi Mj Mk Ml Mm Mn Mp Mq Mr Ms Mu Mv Mw Mx My Mz Na Nb Nf Ng Ni Nm Nn No Nq Nr Ns Nt Nu Nv Nw Nx Ny Oe Of Og Oh Oi Ok Om On Oy Oz Pa Pb Pc Pd Pe Pf Pg Po Qa Qb Qd Qc) Nd(Hv Hx Ih Ij Ik Il Ip Ir Is It Iv Jj Jk Jn Jo Jr Js Jt Lv Ly Lz Md Mk Ml Ms Mt Na Nb NF Nn Nt Nu Of Og Om Oy Pa Pe Pz Qc) Iq(Ii Ij Il In Is It Jh Ji Jj Jk Jn Lv Ly Lz Md Mk Ml Ms Mt Mu Mw My Nb Nc Ne Nf Ng Nh Nj Nk Nl Nn Nq Of Oi Om Oy Pa Po Pz) Mw(kC kE kF kG kK kN kO kP lW lX lY mE mF mH mI mM mS mT mU mW mY nA nB nC nD nH nI nJ nK nM nN nO nR nT nU oO oP oQ) In(Ii Ip Is Ji Jr Js kO Lv Lz Mc Md Mk Ml mM Ms Mt mZ nC nD NF NH Nk nL NN Nx Of Om oQ Oy Pa Pc Pe Po Qa Qc) Ii(Et Ip Is It Jg Jn Jr Js Lh Lv Lx Lz Mk Ml Ms Mt NC Ne nF Nh Nk Nl Nw Nx Ok Om On Pa Pc Pe Po Qc) Po(Il Is It Jn Js Lh Lv Lx Ly Lz Ms Mt Nc Ne Nh Nj Nk Nl Nw Nx Oi Om Pa Pc Pz Qc) Nj(Hv Ih Ij Il It Jn Jo Jr Js Lz Md Mk Ml Ms NF Nn Nt Oi Om Oy Pe Pz Qc) Ne(Hv Ih Ij Il It Jn Jr Js Lv Lz Md Mk Ml Ms Oi Pe Qc) Ly(Ij Il It Jk Jo Js Lz Md Mk Ms Nf Nt Oi Oy Pe Qc) Ij(Is It Ji Jn Js Lv Lz Mt Nc Nh Nk Nl Om Pc Pz) Js(It Ji Jn Lv Md Mk Mt Nc Nf Nh Nk Nl Oy) Lz(Jn Md Mk Ms Nc Nf Nk Nl Oi Om Qc) It(Md Mk Ml Ms nC nD nH Nn Om Pe Pz) Ms(Is Iv Ji Jn Mt Nc Nl Pz Qc) Nl(Hv Ih Il Jn Jr Mk Pe Qc) Ng(Ba Bc bF cS cV Dd Dg) Nc(Hv Il Jn Jr Mk Pe) nF(Jk Na Nb Nt Oi) Mk(Is Iv Jn Qc) Qc(Jn Lv Md) Nt(mZ nN) Is(Aj Ml) Pz(Ct Oi) Jn(Jr Pe) LvJr NkPe JiOm nHnL} Ng{Ad(AJ Aw aX BA bB BC bF Bg Bo bZ cE cL cS cT cV cX dF dG dH Ef Et Fr Hv Hw Is Jg Ji Jj Jn Jo Jp Jt Ky Lu Lv Lw Lx Mi Ml Mp Mt Mv Nc Ne Nj Nk Nm Nq Ns Nt Og Om On Ou Oz Pa Ph Qc Rf Rj) Jp(Af Aj Al An Ao Ap Ar As Aw AX bA Bb BC bF Bg bI Bn Bo bV cE Ch cL Co Cp Cq cR CS CT Cu CV Cw CX Db Dc Dd De dF Dg dH Dk Dl Kf Ki Kk Ky Ou) Kf(Bc Bg cV eD Ef gP hA hC Hw iB iC iJ iO jD jE jF jG jH jI jK jL jM jO jP jQ jR jT jU jV jY Kk kQ Kr Ky lK lL lN lO Mp My oH Ou Pz qT qU qX qY rA) Ba(BC bF Bg cS cV Dc Dd Hv Hw Is Jg Ji Jj Jn Jq Js Ly Mt Mv Nc Ne Nf Nj Nk Nl Og Ok Om On Ou Oz Pa Pb Qa Qc Qd Qe) Jg(aC Af aM Aw aX bA BB BC bF Bg bM bV bZ cE cG Ch cL cM cR cS cT cX Dc Dd dF DG dH Ou Rj) Pz(aF aJ Ap Aw aX bB BC Bg Bo bQ bV bZ cE cG cL cR cS Cw cX Dd dG dH fP hF iO Kq Ky Or Tn Uk) Ou(BC bF cS cV cX Dd Dg Ef Et Jv Jj Jn kI Kn Kr Ky Mf Mm My Nc Ne Nl Nu Oz Pk Rj Uu) Et(Aw aX bA BC bF Bg bV cL cS cT cV Dd Ef Hb Kk Kr Or) cV(aJ BC bF DG Fr Jn Lw Mt Mu Nc Ne On Qa Uu) My(Ap bA BC bF Bo bZ cE Cw cX dF Ky Or) bF(aX BC Is kI mF Mt NC nF nH nL) Dg(Bg Ef hC Is Jn Jt Kr Mu Mv Nc qX) Uu(iC jD jF Jn qX) kI(bZ hB oN Tn) Uc(jE Rj) Qw(eF gP) Nx(Gz Vq) On(BC) nR(Ld Qz) oP(bU Or) MtbC IsbB cEnC} oP{mF(aC AD aE AF aG aH aI aJ aK AL AN AO AP aQ AR AS aU aV AW aX aY aZ BA BB BC bE bF Bg bH bI bJ bL bM BN BO bP bQ bR bS bU bV bW bX bZ cA cB cC cD cE cF cG cH cI cJ cK cL cM cN CO CP CQ cR CS CT CU CV CW CX cY cZ dA DB DC DD DE dF DG dH dI dJ DK Dl dM dN Ef Fa Fb Fw Gl Gp Hc Hf Ic Iz Je Kc Kd Ke Kf Kg Ki Kl Kn Kp Kq Kr Ks Kx Kz Ou Pi Pj Pk Qy Ra Ub) nC(aD Aj AN aO AP Ar AS aY aZ Ba Bb Bc BG bI bM Bn Bo bP bQ cB cF cG CH cJ Co cQ cS CV Cw cX Db Dc DE Dg dJ dK DL Hb Iz Je Kd Or Ph Qy Ra) Or(aF Cp Cw nA) Aw(Fw nL Pa) Fw(In Nt) nL(aM cV) ApnA InPg aYnH} Qz{nR(aC Ad AF aH AJ aM An AO AP AR AS aV AW aX aZ bA BB BC bE bF BG bH bI bJ bL Bn bO bP bQ bR bS bU bV bW bZ cA cB cC cD cE cF cG cH cI cJ cK cL cM cN CO CQ cR cS CT Cu CV CW CX cZ DB DC DD DE dF Dg dH Dl Dk DL dM dN Ef Fb Gp Hb Hc Hu Ic Iz Kc Kd Ke Kf Kg Ki Kj Kk Kl Ko Kp Kq Kr Ks Kx Ky Kz Ld Mf Mu Mw Nn Or Ou Ph Pi Pj Ra) Ou(kC kE kG kK

Figure 20 Continued kN kO kP lW lY mE mH mM mS mU mW mY nB nD nI nK nN nO nT nU) mF(aY cE Fy hB Is Kq Ma Ok oN Tv) kI(bF bZ Kq oN pF Tn Tr Uc) nL(bF Is Ma Or pF Uc) nC(cE dF Is Tv Uc) nH(cE Is Or) Ma(mZ nF) dF(kG mM) UcnJ OrnU bFkG cEnI cXgP mWqT} Or{nJ(aF aL aM As BC bP bX Ch Cv cZ Dg Dl Et Fw In Iq Kc kE Kf kI Kk Kn Ky Mb Nb NC nF Nj Nl nT Pk Pz To Uh Uk Vt) kI(cE In Je jH jM Jp jQ jT jU jV Kn lN nC Nf Pf qU Rf) nC(aM aS cJ Di Kn Me Mh Mv Mw mZ Nb Nc Oh Uk) mF(Dg Kn Ld Me Nb Nl Pz) Pz(kE nA nH nI nK) nL(Kn Ne Nl Oh) Nb(mE nH nU) kE(Kn Oh Pf) Em(aV Mh) Me(nI nU) nF(bX cJ) nH(Nl Oh) EtfR MwmT QwgP KnnA} In{Rm(kC kF kG kK kN kO kP lW lX lY mE mF mH mI mM mP mS mU mW mY nA nB nC nD nF nH nI nK nL nM nN nO nR nT nU) Pz(cV Is Jn Lv Mt Ne Nl Ou Qa) Pg(kG mM nD nN oO oQ) Tv(mF nC nF nH nJ) Is(fR nC nD nH nL) nR(bP Di Ld) Jn(Lv Ne) Nv(mM nF) Pa(mF nN) FwoQ MsJi MzmZ KdmF PikI} Qw{gP(aJ Bc bV bW CH cJ cR Ct cV dM Ed Ij Ji Jn Ky Lw Ml Nc Ne Nj Nk Nl Of Ou pF Qa Qh Qn Ra Rj Ub Uf Uk) pF(cP cV cX hC kE kI Nc Nj Nk NL oH Pz Rj Ub) cX(eF hB hC iJ iO oH) mF(bF cE dF hB oN Pf) oH(Gz hB Nc Nj Nk) oN(kE nA nF) iA(kE Nj) UbeF} Is{Aj(Hw Jj Js Lu Lz Ms My Og Ou Pz) nC(Ch Ih Ii Kj Nk Tt Vv) nD(Cp Ha Ih Ph Pk Ur) nJ(Ha Kr Ky Ph Pk) Ch(Jj Lu nR Og) Fb(kC kO nA nH) Ms(Hw Iq Ji Pz) nK(cX dJ Ra Vv) Ct(Jj Lu nL) Lv(Hw Ij Iq) kI(Ha Kz Rf) Jj(Ap Dk) NeHw IhnH VvnL} nR{Ch(Cq cZ kE Kf Kk Ld lK Nb nC nF Nj nL Oh Pd) Ld(Ao Ii nA nC nK nL Nt Of Tt) lK(bZ cE Cp De Di Dk Ef Iz Kj) nL(Bc Ct cZ De Di Dk) nC(Bc cZ De Di) Cp(jI lN qT) Mw(dG Kc Kf) nF(Ad Kc) qT(aO Bn) DenH NbKk} Lv{Jn(Hw Ij Iq Jr Js Ly Ms Nc Nd Ne Nj Nk Nl Om Po Pz Qc) Ij(It Mt Nc Ne Nk Nl Pz) Mt(Hw Ms Qc) Ne(Hw Ml Pz) Iq(Ji Ml Qa) Nc(Hw Pz) MsJi QaQc} Ji{Ms(Hw Ii Ij Io Ip Ir Iu Iv Jn Jo Js Jt Lu Ly Lz Md Ml Mt Nc Nd Ne Nk Nl Om Pa Po Pz Qc) Nt(jF lN) IqOm UknF} bF{nL(Ao Hu Jh My Of Ra) nC(Ao Hu Jh My Ra) nH(Ao Hu Jh My Ra) nF(Ao Cp Jh Ra) kI(Hu Jh My) Mw(mF nI) fR(aN bR) LdmF} nC{cE(aM Aw Ct Di Mw Of) Tv(aM Ii Oi) Ii(Nv Rm) Ld(aY pF) DipF MwdF TnJk PzcX UkcG} Ou{Em(Jj Jo Kc Mg Oy) Ct(kI nF) Nt(Et Oz) NenA PzJj OfnL cJnF} fR{aC(aN bA cE cT) aN(bR cE Nf) Ld(kQ Li) aD(cE cT)} hB{Ch(kE mF Pz) Mv(Nj oH Pz) oH(Co nF) EfnJ MwnK PzOf} Nx{Ex(Ct Hw Jj Jo Mg Og Uk) EmIi UknF} Aj{qX(Dg Et Kf Pz) Ad(bC cS) rA(Kf Pz)} kI{oN(Ch Jh Mw) pF(Di Kk Mw) JePf VujH} Ct{Pz(cT cV qX) cE(nH nL) MzqX bCcT} nF{On(Jd Jh) ChoN KccV OkUk dGoH} Mw{cE(mF nI) OnmP nAoN nLpF} Uk{cG(mF nL) PzjH nKpF} Mz{mP(mZ nN) RfqX} nL{pF(Di Ld) MpdF} Em{MlaC KgOk} Hw{Jn(Ne Nl)} Tv{iO(kG mF)} cV{PzJj aCbE} nJ{BgoN KyLd} ChkEoN DicEnI IvNynK KcOzqX KknApF RgmFoO Unconstrained panels with 2 analytes, where 1.0E-6 >= 'model p-value' > 0. Contains 1 panels of 109,774 total panels evaluated. : NgOw Unconstrained panels with 2 analytes, where 1.0E-5 >= 'model p-value' > 1.0E-6. Contains 15 panels of 109,774 total panels evaluated. : Ow(Aj Ch Ct cV Ib Ik Kr Ky Nt Oz Pb) Jl(Hw Ii In) AdNg Unconstrained panels with 2 analytes, where 1.0E-4 >= 'model p-value' > 1.0E-5. Contains 187 panels of 109,774 total panels evaluated. : Ow(aC Ao aX Ba Bb BC Bg bI Bo bV cH Co Cp Cq cR cS Cv Cw cX Dk Ef Et Fw Gl gP Gz Hb Hf Hq Hu Hv Hw Ii Ij In Io Ip Iq Ir Is It Iu Iv Iz Jh Jj Jk Jl Jn Jo Jp Js Jt Kc Kg Ki Kj Kk Ko Ks Kx Lj Lv Lz Ma Mb Md Mf Mg Mi Mk Ml Mn Mp Ms Mu Mv Mw My Nc Ne Nf NJ Nk Nl Nm Nn Ns Nu Of Og Oi Om Or Oy Pc Pd Pe Pg Ph Pk Po Pz Qc Ql Qm Qn Qw Qx Qy Qz Ra Rf Rj Tv Ub Ue Uk Ut Vv Tj) Jl(Ij Il Iq It Jn Jr Js Lv Ly Lz Md Mk Ms Nc Nd Ne NF Nj Nl Nn Oi Om Oy Pe Po Pz Qc) Lv(Ij Iq Jn Ly Mt Nc Nd Ne Nj Nk Nl Pz) Ng(Ba bF cV Dg Kf Ou) Or(kI mF nC nJ nL) Ib(nR Ou Tn) Aj(Ad Is) Ms(Is Ji) Qw(gP pF) ChnR JiOm JjOu aCfR Unconstrained panels with 2 analytes, where 1.0E-3 >= 'model p-value' > 1.0E-4. Contains 940 panels of 109,774 total panels evaluated. : Ow(aA AD aE AF aG aH aI aJ aK AL aM AN aO AP aQ AR AS aU aV AW Ax aY aZ bA bB bE bF bG bH bJ bL bM BN bO bP bQ bR bS bU bW bX bZ cA cB cC cD cE cF cG cI cJ cK cL cM cN cO cP cQ Cs cT CU cW Cx cY cZ dA DB DC DD DE dF DG dH DI dJ dK DL dM dN Dp dR eC Ed eF Em Ex Ez Fa Fb Fn FP FR Fy gL Gp Ha hB Hc Hr HX Ic Id IH iJ Il Im iO iP Jd Je Jf Jg Ji Jm Jq Jr Ju Jv Jy Kd Ke Kf Kl Kn Kp Kq kS Kz Ld Lh Li Lu Lw Lx Ly Mc Me mF Mh Mj Mm Mq Mr mS Mt Mx Mz Na NB nC ND nF Nh Nl No Nq NR nU Nv Nw Nx Ny Oa OE OH OK ON Ou Pa Pf Pi Pj Qa Qb Qd Qe Qg Qh Qt Qu Qv Rb Rc Rg Rh Ri Rm Sr Ss St Tn To Tr Tt Tz Ua Uc Ud Uf Ug Uh Ul Um Un Uo Up Ur Us Uu Uv Vo Vp Vq Vs Vt Vu Wm) Jl(Aj Ct cV Et Hq Hr Hu Hv Hx Ib Ih Ik Im Io Ip Ir Is Iu Iv Jg Jh Ji Jj Jk Jm Jo Jp Jq Jt kC kI kN kO Lh Li Lj Lu LW Lx lY Ma Mb Mc Me MF Mg Mh MI Mj Ml MM Mn MP Mq Mr mS MT MU Mv Mw Mx MY MZ NA NB nC nD Ng NH NI nJ NK nL Nm nN No Nq Nr NT NU Nv Nw Nx Ny Oe Of Og Oh Ok On oO oP oQ Oz Pa Pb Pc Pd Pf Pg Qa Qb Qd Qe) Lv(aA Et Fp Fr Hq Hr Hu Hv Hw Hx Ih Ii Ik Il Im In Io Ip Is It Iu Iv Jg Jh Ji Jj Jk Jm Jo Jp Jq Jr Js Jt Lh Li Lj Lu Lw Lx Lz Ma Mb Mc Md Me Mf Mg Mh Mi Mj Mk Ml Mm Mn Mp Mq Mr Ms Mu Mv Mw Mx My Mz Na Nb Nf Ng Nh Ni Nm Nn No Nq Nr Ns Nt Nu Nv Nw Nx Ny Oe Of Og Oh Oi Ok Om On Ou Oy Oz Pa Pb Pc Pd Pe Pf Pg Po Qa Qb Qc Qd Qe) Ou(Aj bV Ch Co cR cS Ct cV cX Dk Em Hw Ii Ij Ik Is Iv Iz Jk Jn Jo kI Kr Ky Mf Mg Mk nA Nf NJ Nl Nm Nt Nu Of Og Oy Oz Pb Pc Ph Pk Pz Ql Qw Rj Ue) Ng(aJ Ap Aw aX bA bB BC Bg Bo bV bZ cE cG cL cS cT Cu Cw Dc Dd dF dG dH Ef fR hB iO Kq Ky Mt Or Rj Tn Uu) Ji(cV fR Hw Ib Ii Ij In Iq Is It jD jF Jn Jo Js Jt Lu Ly Lz Md Ml Mt Nc Nd Ne Nf Nj Nk Nl Of Po Pz Qc Rf) Or(Em fR kC kE kF kO kP Ky lW lY mE mH mI mP mS mT mU mW mY mZ nA nB nD nF nH nI nK nR nU oP Vq) nR(Aa Ad aJ aM aN Ao aS Ax aY BC bX cH cI cX cZ DE dG Dk dL dM dN Kc Kj Kk Kn Kp Ld Ra) Is(Ch Ct cV cX fR Hw Ib Ii Ij In Iq Jo Ky Lu Ml nC ND Ne Nf Nj nK nL Og Om Ph) cV(aC bA bC bF bI bW cE hB Ib Jj Jn Kc Ky Lw Nc Ne Nj Og Pk Pz Qw Qz Rj) Jn(Hw Ib Ij In Ky Lu Ly Lz Ms Mt Nc Nd Ne Nf Nh Nj Nk Nl Om Pz) aC(aJ aX bA BC bE bF bV bW bZ cE cG cR cS dF dH dM Em Ex) hB(Aj Bg Ch Co cX Hc Hu Ib Ik Mv Nj Nl Of oH Oz Pz Qw) Mt(Hw Ii Ij In Ly Lz Md Ms Nc Nd Ne Nj Nk Om Pz) Ib(Ad cX Dc Et Jp Kf Ky Lh nC Nj oP Pz Qh) fR(aD AN bA bF bR cE cT Dc Ld Nf Oi) Ne(Et Hw Ij In Lh Lz Ma Ml Mm Pa Pz) mF(bF cE dF Kf Kk Ld Mp Nv oP Qz Tv) nC(aY bF cE dF Dg Mp pF Qz Tv Uh Uk) Nj(Et Fr gP Hw Ij Jp Nw Pa Pz Qa) Aj(Ba bC bF bZ Dg Et Jp Pz qX) Qw(eF fP hC iA iJ iO oH Ub) Ky(cX Ik Jj Jp Nf nJ Nt qX) nF(cE dF Ma Mp Nv On Pg Uh) Ct(BA bF cE dF Jp) Jj(aX bA bV cS cT Dd) qX(bF bG cJ cX Kf Mz) Qa(Hw Ij In Om Qc) nL(cE dF nH pF Tv) oP(aM aN aY Cp Ed) nJ(cE dF pF Uk) Et(Nc Nd Nl) Mp(nD nH nN) Ms(Lh Nw On) Pz(bA Nl Uk) bF(aX bV cS) Mz(jH mP) kI(bZ pF) ChJp ExNx ManD MdOn NdPa NlHw QzcX OajH UkVq bAcS cEnI nApF Constrained panels with 3 analytes, where 1.0E-8 >= 'model p-value' > 0. Contains 7 panels of 16,766,520 total panels evaluated. : Ib{Is(kE nK) FykE OwnR mFoP} FbIsnD QzOwnR Constrained panels with 3 analytes, where 1.0E-7 >= 'model p-value' > 1.0E-8. Contains 40 panels of 16,766,520 total panels evaluated. : Ng{Ow(Ad Bg cV Ef Jg Jp Kr My Pz Uu) Pz(Ba cV)} Ib{Is(kI mT nC nL) Kn(mW nR) QznR} Or{lK(kI nO) oP(Aw mF) NenC} Qz{mF(bF dF) OunL aNnR} Jl{Hw(Ne Nl) InPz} nC{oP(aM Aw) MwhB} Ow{ChnR KrOz} MwnLhB IsRfnK KymFoP LdkIpF Constrained panels with 3 analytes, where 1.0E-6 >= 'model p-value' > 1.0E-7. Contains 279 panels of 16,766,520 total panels evaluated. : Ow{Ng(aX BC bF Bo bV cR cS Cv cX Dg Et fP Iv Jl Jn Kf Kk Kq Ky Nc Nk Nl Pb Qn Tn) Oz(aX Bo bV Ch cR cS cV Hb Hw Ij Iv Js Kk Mp Nf Nt Nu Om Ql) Ib(Ad aX cR cV Ef kN Kr mZ nJ Nu oP Pz) Pz(Ch Ct cV Ii Ik In Jj Mg Nt Oi Ue) cV(Co Ct Gl Js Kr Mp Nt Pk Po) Kr(Ct Nf

Figure 20 Continued

Figure 20 Continued mF{TviO RgoO UkcG} Ct{bCcT cEnH} Hw{Jn(Ne Nl)} nJ{BgoN KyLd} nK{IvNy UkpF} ChkEoN DicEnl EmKgOk TviOkG KcOzqX KknApF aCbEcV

Constrained panels with 2 analytes. where 1.0E-6 >= 'model p-value' > 0. Contains 1 panels of 109,774 total panels evaluated. : NgOw Constrained panels with 2 analytes, where 1.0E-5 >= 'model p-value' > 1.0E-6. Contains 15 panels of 109,774 total panels evaluated. : Ow(Aj Ch Ct cV Ib Ik Kr Ky Nt Oz Pb) Jl(Hw Ii In) AdNg Constrained panels with 2 analytes, where 1.0E-4 >= 'model p-value' > 1.0E-5. Contains 102 panels of 109,774 total panels evaluated. : Ow(aX bI bV Co cR cS cX Gz Hb Hw Ii Ij In Jj Jo Mf Mg Mk Mp Nf nJ Of Oy Pc Ph Pk Po Pz Ql Qw Qx Rf Rj Ub Ue Uk Ut Tj) Jl(Ij Il Iq It Jn Jr Js Lv Ly Lz Md Mk Ms Nc Nd Ne NF Nj Nl Nn Oi Om Oy Pe Po Pz Qc) Lv(Ij Iq Jn Ly Mt Nc Nd Ne Nj Nk Nl Pz) Ng(Ba bF cV Dg Kf Ou) Or(kI mF nC nJ nL) Ib(nR Ou Tn) Aj(Ad Is) Ms(Is Ji) Qw(gP pF) ChnR JiOm JjOu aCfR Constrained panels with 2 analytes, where 1.0E-3 >= 'model p-value' > 1.0E-4. Contains 410 panels of 109,774 total panels evaluated. : Ou(Aj bV Ch Co cR cS Ct cV cX Hw Ii Ij Ik Iz Jn Jo kI Kr Ky Mf Mg nA Nf nJ Nt Nu Of Og Oz Pb Ph Pk Pz Ql Qw Rj Ue) Ng(aJ Ap Aw aX bA bB BC Bg Bo bV bZ cE cG cL cS cT Cu Cw Dc Dd dF dG dH Ef fR hB iO Kq Ky Mt Or Rj Tn Uu) Ji(cV fR Hw Ib Ii Ij In Iq Jn Jo Js Jt Lu Lv Ly Lz Md Ml Nc Nd Ne Nf Nj Nk Nl Po Qc Rf) Is(Ch Ct cV cX Hw Ib Ii Ij In Iq Jo Ky Lu Lv Ml nC ND Ne Nf Nj nK nL Og Om Ph) cV(aC bC bF bI bW cE hB Ib Jj Kc Ky Lw Nc Ne Nj Og Pk Pz Qw Qz Rj) Jn(Hw Ib Ij In Ky Lu Ly Lz Ms Mt Nc Nd Ne Nf Nh Nj Nk Nl Om Pz) hB(Aj Bg Ch Co cX Hc Hu Ib Ik Mv Nj Nl Of oH Ow Oz Pz Qw) aC(aJ aX bA BC bE bF bV bW bZ cE cG cR cS dF dH dM) Mt(Hw Ii Ij In Jl Lz Md Ms Nc Nd Ne Nj Nk Om Pz) Ib(Ad cX Dc Et Jl Jp Kf Ky Lh nC Nj oP Pz Qh) nR(cH cZ dM Kc Kj Kk Kn Kp Ld Ow Ra) mF(bF cE dF Kf Kk Ld Nv oP Ow Qz Tv) nC(aY bF cE dF Dg Ow pF Qz Tv Uh Uk) Aj(Ba bC bF bZ Dg Et Jl Jp Pz qX) Nj(Et Fr gP Hw Ij Jp Nw Pa Pz Qa) Ne(Et Hw Ij In Lz Ml Mm Pa Pz) Jl(Ct Hv Hx Jk Ml Nb Nk Of Pa) Ky(cX Ik Jj Jp Nf nJ Nt Or qX) nF(cE dF Ma Mp Nv On Ow Pg Uh) fR(aD AN bR cT Dc Nf Oi) Ct(BA bF cE dF Jp) Jj(aX bA bV cS cT Dd) Or(kE mE mT nH nU oP) qX(bF bG cJ cX Kf Mz) Qa(Hw Ij In Om Qc) nL(cE dF nH pF Tv) oP(aM aN aY Cp Ed) Ow(hX nD nI nU) nJ(cE dF pF Uk) Et(Nc Nd Nl) Lv(Hw Nh Om) Ms(Lh Nw On) Pz(bA Nl Uk) bF(aX bV cS) Mp(nD nN) Mz(jH mP) Qw(oH Ub) kI(bZ pF) ChJp ExNx ManD MdOn NdPa NlHw QzcX OajH UkVq bAcS cEnI nApF Unconstrained panels with 3 analytes, where 1.0E-10 >= 'AUC p-value' > 0. Contains 7,153 panels of 16,766,520 total panels evaluated. : Or{kI(aC AD aE AF aG aH aI Aj aK AL aM aN AO Ap aQ AR AS aU aV AW AX aY aZ Ba Bb BC bE bF BG bH bI bJ bL bM BN BO bP bQ bR bS bU bV bW bX bZ cA cB cC cD cE cG CH cI cJ cK cM cN CO CP CQ cR cS Ct CU CV CW CX cY cZ dA DC DD dE dF DG dH DI dJ DK DL dM dN Dp dR eC eD EF Et Ez Fa Fb Fn fP Fr Fw gL GP HA HB HC HF hG Hq Hr Hv Hw Hx iA IB IC Id IH Ii IJ Il Im In IO IP Iq Ir Is It Iu Iv IZ jD JE JF JG jH jI JK JL JM Jn JO JP JQ JR Js JT JU JV JY KC Kd KE KF KG Ki Kj KK Kl Kn KO KP kQ KR KS Kx Ky Kz Ld Lh Li Lj lL lM lN lO Lu Lv LW LX LY Lz Ma Mb Mc Md ME MF MH MI Mj Mk Ml MM Mn MP Mq Mr MS Mt MU Mv MW Mx mY MZ NA NB NC ND Ne NF Ng NH NJ nK NL NM NN NO Nq NR Ns NT NU Nv nW nY Oa OE OF Og OH Oi OK Om ON oP oQ Ou Ow Oy Oz Pa Pb Pc Pd PF Pg Ph Pi Pj Po Pz Qa Qb Qc Qd Qe Qh Ql Qm Qn qT QU qV QW QX qY Qz RA Rf Rg Rh Ri Rj Rm St Tn To Tr Tv Tz Ub Uc Ud Uf Ug Uk Ul Un Up Ur Us Ut Uu Uv Vo Vp Vs Vt Vu Wm Tj tF) nJ(Ad aF aM aN AO Ap aR AS aV AW aY aZ Bb Bc bJ bL bM Bn bO bP bR bS bW bX cA cC cD cF CH cI cJ cK cM Co Cp CQ Ct Cu Cv dA Db Dc Dd DE Dg DI Dk Dl Ef Et Ez Fa Fb Fw Gl Ha Hb Hc Hf Hr Hu Hv Hw Ib Ih Ii In Io Ip Iq Ir Is It Iu Iz Je Jf Jg Jh Ji Jk jM Jn Jp Jr Js Jt Kc Kd kE Kf kG Kj KK Kn Ko Kp kS Ky Kz Ld Lh Lu Lz Mb Md ME MF MH Mj MM Mp Mq Mr Ms mT Mu Mv Mw Mx MZ nA Nb NC ND Ne NF Ng NH NI Nj nK NL Nm nN No Nq Ns NT nU Nw Nx Of OH Oi Ok Om On oP Ow Oy Oz Pa Pb Pe Ph Pi Pj Pk Po Pz Qb Qc Qm Qn Qt Qu Qv Qw Qz Ra Rf Rg St To Tt Ua Ub Uc Uh Uk Ul Un Up Us Vs Vt Vu Vv Tj) nC(aF aI aJ aK aL aM AP Ar aS aV aY aZ BA Bc bE bJ bO bP bR bX cE cF cG CH cJ cL Cp cQ Cv cY cZ dA Dc Dd De DG DI dJ Dl dM Et Ez Fn Hb Hc Hu Ib Ic Ip Iq Ir Is Iu Je Jf Jg Jh Ji Jn Jp Jt Kc Kd kE Kf Kk Kl Kn Ko Kp Kz Ld Lh Mb ME mF MH MP mS MT Mv Mw Mx mY mZ nA Nb Nc Ne Nf Nh Nj Nl nU Oa Oe Oh Oi Ok On oO oP oQ Ow Oz Pa Pb Pc Pk Pz Qa Qd Qe Ql Qm Qv Qw Qz RA Rj St Tt Tv Ue Uf Uh Uk Uu Vt Vu) oP(aF aM aN AO AP As Aw aX aZ Bb bL Bn Bo bP Ch Co Cp Ct Cw De Di Ez Fb Fw Hu Ib Ii Iz Jd Je Jh Jk KE kG Kj Kl Md ME mF Mk mM Mp Mr Mv Mw My nA Ne Nf Ng nH nI nK nL Nq Nt Oe Of Om Ow Pb Po Pz Qw Qz Ra Tt Uk Vs) mF(Ap aS bE bP bX Ch cI cJ Cv cZ Dg dI Et IB iC In Iq Jg jT jU jV Kc Kd kE Kf Kk Kn Ko Kz Ld lK lL Me Mh Mv Mw Nb Nc Ne Nf Nh Nl Oh Ok oO oQ Ow Pa Pk Pz Qw Qz Uh) nL(aF aM aS aY Bc bX cJ Cv cZ Dc Dg Et Fa Ha Hb Hc Hv Ib Is Je Jg Jp Kn Kz Me Mp mS Mw Nb Nc Ne Nf Nl nR nU Oh Ow Oz Pa Pb Pc pF Pz Qw Qz Ra Rf St Uf Uk) kE(Bc Cv DG Di Dl Et Fr Fw hB Hc Ib In Jg Jp Kn Ld ME Ne Nf nH nK nU Oa Oh Ok Ow Pa Pf Pz qW Qz Rj Uk Uu Vt) Ib(kC kF kG kK kN kO kP lW lX lY mE mH mI mM mP mS mT mU mW mY mZ nA nB nD nF nH nI nK nM nN nO nR nT nU) nH(aF aL aS bP bX cJ Dg DI Dl Et Fn Ip Jg Kc Kn Ld Me Mv Mw Nb Nc Ne Nf Nh Nl Oh Ow pF Pz Qw Qz Uk) Ow(Em kC kF kK kP lW lX lY mE mI mM mP mS mW mY mZ nA nB nF nI nK nN nO nR nT nU oQ) Qz(kG kK kN kO kP lW lX lY mE mH mI mM mT mW mY mZ nB nD nF nI nK nN nO nR nT nU) nU(aM As bE bP Ch Dl Fw Kc Kn Ld Me Mw Nb Ne Ng Nt Ph Pz Qw Ra Uk Vs Vt) Me(Em fR kC kF kN lY mE mH mI mP mS mT mY mZ nA nD nF nI nK nR nT) mE(aL bE bP cZ dN Mb mT Mx Nb Ne Nl Oa Oe Oh Pz Qv qX rA St Uk) nK(aL bE cJ cZ Et Ip Is Iv Md Mz Nb Oh Pa pF Pz Ra Rf To) mT(aF Ch Cp cQ Di Dl Fb Ir Ld lK Mp Mw Ne Nl QW) nA(bX cJ Dg Et In It Jp Kc Kn Nb Nf oH oN pF Pz) Pz(kC kG kN kO lW lX mM mP mS mY nD nF nI) Ne(kN lY mU mW mY mZ nI nN nO nR nT) Em(aQ aV Ld Ly Mh Nb Nx Ok Ou) nI(bX Cv Dg Jg Kc Kk Nb) mZ(Kn Md Pb RA Vu) nF(bX cJ Et Kc Kn Uh) Nb(mI mS mW mY nB) nR(Ch Di Mw Qw) Et(fR mM nD) mS(Ip Iq Uk) mH(Ld lK) DgmM KnnD NxfR cJkC nTqT} Ib{oP(aH AI AN AP AR aV Aw aY Ba bB BG bH bI bN BO bS bW bZ cA Ch Co cP CQ Ct cU cV dB Dc Dd dF dG DI Ed Et Ez Fw Fy Hw Hx Ii Ik Il Im In Je Jf Ji Jl Jn Jo Jp Jq Jr Js Ju KC Kd Kf KI Kk KN KO Kp Kq Kr Ks Kx Ky Kz Lh Lv Ly Ma Mf Mm Mn MS mW Mx mY Mz NA NC nD Ng nH NI nJ NK nL NR Nu Nv Nw Ny Oa Oh Ok Om On oO oQ Ow Oy Oz Pb Pf Pg Pi Pk Qa Qd Qe Qh Qv Qy Qz Ra Rg Rm Sr Tn To Tr Tv Tz Uh Uk Ul Um Uo Uv Vo Vs Vu) nR(aD aL AN aS aU aV BA bE bH bJ bO bX cK cQ cT cZ dA DB Dc Dd De Dg dI dJ Dl dM Et Ez Fy gL hA iB Ih Ii Im In Ip Is Iu jE jG Ji Jn Jo JP Jq Ju Kc kE Kf Kg kI Kk Kn Ko Kp Kq Ks Ld Lh lK lM Mb Me mF Mk Mm Mw Mx mY MZ nA Nb nC Nd Ne Nf NH Ni NJ nK NL Ns NT Nv Nw Nx Ny Oe Of OH Oi On Ow Pa Pd Pg Pk Pz Qb qT QV QW qX Qz rA Rg Rm St Tv Tz Uh Uk Un Up Us Uv Vu) mW(BA bF bQ bZ cE cL Cq Dc dF Dg dM Ef Et Ez Fy Gl hB Ik Im Is Jg Ji Jn Jp Jq Kf Kk Kl Kn Ko Kp Kq Ky Ld Lh Lx Ma Mn Mt Mz No Nv Nw Ny OH Ok Om On oQ Ow Oz Pg Qa Qb Qd Qe Qh qT qX Rc Rm Sr St Tn Tv Tz Uf Uh Un Vo) nC(Al aP Ba bF bQ bZ cE Cq Dc dF Et Fy hB Ih Im Ip Is Jg Ji Jm Jn Jp Jq Kf Kk Kn Lh Ma Mn Mt Nv Nx Oh Ok ON Ow Pg Qe Qh Rm St Tn Tv Uh Uu Vu) Dc(kC kE kF kG kI kK kN kO kP lW lX lY mE mF mH mI mM mP mS mT mU mY mZ nA nB nD nF nH nI nJ nK nL nM nN nO nT nU oO oQ) Lh(kC kE kF kG kI kK kN kO kP lW lX lY mE mF mH mI mM mP mS mT mU mY mZ nA nB nD nF nH nI nJ nK nL nM nN nO nT nU oO oQ) Ow(Ef fR Js kC kE kF kG kI kK kN kO kP Kr lW lX lY mE mF mH mI mM mP mS mT mU mZ nB nD nF nH nJ nL nM nN nO nT nU oO Pz) Fy(kC kF kG kI kK kN kO

Figure 20 Continued kP lW lX lY mE mF mH ml mM mP mS mT mU mY mZ nA nB nD nF nH nl nJ nK nL nM nN nO nT nU oO oQ) Ji(kC kE kF kG kl kK kN kO
kP lW lX lY mE mF mH ml mM mP mS mT mU mY mZ nA nB nD nF nH nl nJ nK nL nM nN nO nT nU oO) On(kC kE kF kG kl kK kN kO
kP lW lX lY mE mF mH ml mM mP mS mT mU mY mZ nA nB nD nH nl nJ nK nL nM nN nO nT nU oO oQ) Tv(kC kE kF kG kK kN kO kP
lW lX lY mE mF mH ml mM mP mS mT mU mY mZ nA nB nD nF nH nl nJ nK nL nM nN nO nT nU) Rm(kC kE kF kG kl kK kN kO kP lW
lX lY mE mF mH ml mM mP mS mU mY nA nB nD nF nH nl nJ nK nL nM nN nO nT nU oO) Is(kC kF kG kl kK kN kO kP lW lX lY mE mF
mH ml mM mP mS mT mU mY mZ nA nB nD nF nH nl nJ nL nM nN nO nT nU) kE(Ba bF bQ bZ cE dF hB lm Jp Jq Kq Ma Mn Mz Nv OH
Ok oN Ou Pf Pg Qa Qd Qe Qh St Tn Tr Uc Vu) Kk(kC kF kG kK kN kO kP lW mE mF mH ml mM mP mS mU mY mZ nB nH nl nJ nL nN nO
nT nU) oH(fR kC kF kK kN kO kP lW lX mE mH ml mP mS mT mU mY nA nB nD nF nH nl nL nM nO nU) Mz(kC kG kl kO kP lW lX mE
mH mM mP mS mT mZ nA nB nD nl nJ nK nN nT nU oO oQ) Jq(kC kG kl kK kN kO kP lW lX lY mF mH mM mP mS mT nB nD nF nH nJ
nK nL nM oO) Nv(kG kl kN kO kP lY mF mH mM mP mS mT mY nB nF nH nl nK nL nO nT nU oO oQ) Ba(kG kl kN kP lW mF mM mP mS
mT mY mZ nB nD nl nJ nL nN nO nT nU) Oh(kK kN kO kP lW mF mM mS mU mY nA nH nl nJ nL nN nO nT nU oO oQ) Kn(kC kG kN lW
lY mF mH ml mM mS mY mZ nB nD nH nl nL nO nT nU) bF(kG kl kK kN kP lX lY mF mH mM mP mT nA nB nH nl nJ nK nL nT) kl(bQ
bZ cE dF hB iB iC jl Jk Jl Kq Ma oN Ou PF Qh Tn) nT(bZ Cq dF Et Ez lm Jn Kf Kq Ma Pg Qh St Uc Vu) nL(bQ bZ cE dF Ef hB iB lm Jm Ma
Mn Nx oN Pg Tn) mF(bQ cE cl dF Et lm lp Kf Ko Pg St Tn) Ma(lY mP mT mY nA nH nl nJ nK nN nU) Kf(eD hX iB jD jE jL jM kN lM nJ)
nA(bZ cE dF Lx oN Ou Tn Tr Uc Vp) Et(ml mM nJ nO nU oO oQ) nK(bQ bZ cE dF oN Pg Tn) Im(kC kN kO mT nH nO) nU(dF lp Nw Nx Qz
Uh) nJ(cE dF Jn Kq oN Pg) Nw(mM nB oO oQ) Nx(Ex Gz mY nH) Pg(mM mZ nN oQ) Nj(hB kS) Tn(mP mZ) Kq(oO oQ) dF(nN nO) CqmT
LhmM cEnH cTk

Figure 20 Continued lX mW mY mZ nD nK nN nO nT nU oQ) hB(kC kE kP mP mS mY nD nI nK nN nU) oN(mP nD nI nK) cE(nI nK) pF(mS nK) OnmP bFnI} Qw{oN(kC kE kK kO lY mE mM mS mY mZ nD nI nK nU) gP(aJ Jj pF Ub Uk) iA(kE kF mH mZ nT) pF(kE mY nD nK) cEnI fRoH hBkE} nK{dF(Ip Iq Ir It Nb Nl St) pF(Di Kk Mv Sr Ss Uk) Ny(Iq It Iv) Ip(cV Ou) Uk(cE Ok) EfoN MvhB NlOu TvHb IkSt IrKy JlcI} nI{Kk(aY bC bP Hb jD Kd mI Nb pF qX rA) Kc(eD mI rA) cE(Di Ne) rA(dF Uh) DgNm TvbP KrOh UkjT} mM{Uh(eD iC jO lK lN qT qX rA) Et(bW cL dG Hb) Kk(Ky PF) oH(aJ dG) GpqX KnKy UkhA} nD{Ip(Gp Ky Uh Ur) Vp(Jf Ra Uk) Ny(It Iv) cJ(jM Uk) oN(Ch Jd) FbSt MpiH QuhB JlmZ KfIN} Nx{Ex(Ct fR Ii Jo Mg Of Og Uk) fR(Kr Ql qX Rh Ue Ut) GzIi RanU} kE{hB(Aw Bg Ch Di Ef) Ch(bZ Ma oN) Ok(Je Uk) aM(bF cE) nW(Mh Tv) DiPf UkcG} Uk{mE(Oh qT qX rA) cJ(kC kO) nO(jH lN) mZ(cG Ou) PzjH mHjD} nU{Ii(Dc Kf Kk Kn) Nt(Kk Kq Uh) Nb(aC Kk) DgNm EtHb KyqT} Et{Hb(mI mP mS nO nT oO) AjqX fRkQ} mY{Ne(Ou Tr) oN(Ch Ef) DePg DgNm DipF FbOh} lN{Kf(kC lX nO) Uh(kK lW mW) KcmI KynO} mZ{Mz(mP Nl) Oa(bF Ou) TnJk IiRm OhhG} qT{Ky(lW mE) KfOz RjmE OanT aWlW bZkN} Kc{Oz(qX rA) eD(kF mP) jI(kK mI)} mS{Nb(Ou Tn Tr) ChoN IpOu dLoH} fR{aC(bC bE) aN(cE Nf) IvoH} nO{jE(aY bG bZ Ch) KylK} mP{Ch(hB oN) Pf(Di Kn)} Fb{Oh(mI nN) StkO} qX{AjPz MzRf KfOz} mW{NedF aJqV} kO{UhjD iHpF} TomErA TviOkG IiRmoQ KkkCpF OaPkjH Unconstrained panels with 3 analytes, where 1.0E-9 >= 'AUC p-value' > 1.0E-10. Contains 3,760 panels of 16,766,520 total panels evaluated. : Ow{nJ(aC aE Af aN Ap bC bG bL bM bP bQ bS bW cA cD cH cN cV Cw dD Dg eF Fp Fr Fw gL HF Hx Ic Ik Jf jH Jl Kf Ki Ko Kr Ly Md Mf mI Mk Mn Mq Mt Mw Na Nb nD Nh nN nW Nx OE oF Oh Pb Pc Qa Qv Ra Rb Rg Ss St Tr Uh Vt Wm) nU(Aj Bb bF bM Bo bP bS bW bZ cA cD cK cV Dc Dd Ef Fa Fb Fy Gl Hu Ih Im Jn Jo Jq Jr Jv Ki kK Kl Kp kQ Lj lO Lw lX Ly Ma Mf MM mU MY mZ NC Nd nH Nl nO Nr Oh Ou Oy Pa Pc Pd Ph Qg Qv Qw Rh Tn Ua Ub Um Ut Uv) Ng(Ap Aw Ba BC bI Bo bV bX Ch cR cS Cw Dc Dd Dg Fa hB Hf Il In Is Iu Iv Iz Jl Js Kc Ki Kj Kk Kl kN Kp Lz Me Ml Mu Mv Na Ne Nf Nh Nj Nk Nm Nq Nt Nu Oe Og On Or Oz Pb Pc Pk Po Qh Ql Tn) Kr(Ad bI bZ cV Dd hB In Is Iu Iv Je Jp Kf Ko Lx Ml Mp Oa Of Ok Qa Ql Qw Qx Qy Ra Rf Rm St Ub Ue Uk Ut Uu Vt) nR(Af Aj aN Ao Aw Bb Bg bP Cp De dK Fy Ii Ij Iq Ir Iz Je Jh jI Jo Jq Ju Lj mF Mv mZ Oi oQ Pf Qy Rf Up Vp Wm) Rf(Ad Bo CV Et Ib Is Iu Jn kK Lx My NF nT Oa Of Oi Oy Pb Pc Qh Ql Qx Ue Uu) Mp(aJ cE cG Ct cV dF Et Fa hB Ib Is It Jp Kf Lw Mk Nf Of oP Qh Ql Qx Qz Rj) nF(bZ cE cG cR Cv fP Hw Ii Je Jy Ky Lx Ms Mt Nr Oa oE oH oK Ou Qv Ue Vp) nC(cE cI Ct Ip Is iZ Kd Nc Ne Nf Nh Nl Nr Oh Qm Qv Ue) nA(dR eF gL hF iA Ib iO Is kR nW nY oE oF oH Qz tF) Oz(aX bC Bo gP Ib It Iv jD Kk Ks Po qX rA) Em(bJ cD Ik Iu Jp Kd Ld Nb Nk Nm Oe Ok) Js(bF cD cE cS dF Mz Nf Og Or Pb Pi Pz) Nt(cV fP fR hB Is Jn Ky Lx Ou Pc Pk) Ct(Ad cV fR gP Iv Ky My Nc Nl Uu) Ib(Ad aX cV Jp Ml MY nK oQ Tn) Hb(kC kF kK lY mT mZ nD nL nM nO) Qz(gP kC kF kK kO kP lW mS mT mY) Uk(kG kP mS mY mZ nB nI nN Vq) mF(aM Is iZ Kn Ko Nf Nm Ok Ra) Or(fR kG kN kO mH mU nD nM) Ra(kN lY mE mI mM mW oQ) Of(Bg Ef fP hB My Ou Pz) Pb(Bo Gz Hf It Ki Oi Ue) lN(mH mP mS mW mZ nK nM) Pf(kE kO mI nD nM oO) fR(bR bV cA cQ Me Og) nB(bZ eC hB Is iZ Ma) Gz(bI Ii Ir Nf Pc) Oi(kC nD nH nL nN) aM(lY mE mM nL nO) fP(Ch Co Jk Mg Mv) It(Hw Iu Ml Pc) Pz(Iq Mg Nf nI) aY(mM mY nL nO) bX(kC kO nH nT) Po(Bo bZ Is) Ne(cV mW nT) Ue(nN nO nT) Iv(Hw Ky Mk) Je(lW nN oQ) Ql(cV Jn Pc) Oa(mI nI nO) mE(Io St Wm) nD(cS eD In) iZ(mT mY nK) kI(eC iJ oN) Ml(Is Iu) Vp(mP mS) gP(Bg cH) hB(Ch Nu) pF(mZ Qw) AjIs BoPc WmkO ExNx NmL MgcV MtnH NhnT IuKy JpmM RjkK cJkC dCoP eCnK eDnM} Or{nJ(aA Af aG aH aI aK An aQ aU AX BA bB bC bF Bg bH bI Bo bU cE cG cP CS CW Cx dJ dK dL Fr Hq Hx Ij Ik Im iO Iv Jv kC kF Kg Ki Kl kP Kq Kr Ks Kx Lw LX LY Ma Mc Mg Mi Mn mP mS Mt MY Na nM Nn Nv Ny Oa OE Og Ou Pd Pf Pg Qe Qx Qy rA Rb Rj Sr Ss Tn Tr Uo Ur Vp Wm) nC(Ad Aj Al AO aR Ax bC bF bI bL bM Bn cA cK cS Ct dE dF dL dN Fa Fb Fr Fw Fy Ha hB Hv Id Ih Ik Im In Jd Jj Jm Jr jU Jv Lv LY Md mI Mj Mk Mq Nd Ng nI nK Nm No NR Ns nT Nv Nw Nx PF Ph Pj Qh QX Qy Rb Rm Uc Un) kE(Ad aF aJ Ax bE bZ cG CH Cp Dc dF dN Ez Gp Ip Is jI Jn Kc KF Kk Kl Ko Md Mp MT Mu MW mZ nA Nc Nh nI nL Nr Nu Nw oE OF Oi On Qa Qd Qw Ra Rb St Tt Uc Uh Ul Vp Vu) kI(aA aJ An aP bA bB cF cL Cs cT DB De Ed Fp Fy Gl Hu Ik Jd Ji Jj kN Kq Mg mT My Nl Nk Nw Nx Ny oO Pe Pk Qg Qt Qv Qy Rb Rc Sr Ss Tt Ua Ue Um Uo Vv) nL(Al bO cE cG cL Cp dE dI dM Fp hB Hu Hw Ik In iO Jh Ji Jn Kf Ko Ld Lv Mb Md mE mF mY Nh Nj Nr Oi Ok Pf Pk Qa Qd Qe Qm Qx Rb Tv Uc Uu Vt) mF(aL BA BC bF cE Dd Di Dl dM dN Fr hB Ip Is jF Ji Jp Jv Lh Ly Mb Mp mS mT mY mZ Nj nT nU Oe Og Ql Uk Um Vt) nH(aM bE Cv Is Kf Kk Kz Mh Mp mS Oi Ok Oz Pa Pb Pk Qm Ra St Tv Uf Uh Uu Vt) oP(Ar cH dA Dk Dl Hf Ij In Jf Kg Lj Mt nF Nv Oa Oy Qt Qu Qx Qy Ua) nK(aI aM bX cI dE Dg Jg Kf Ld Mx Nc Ne Nl nR Nt Ok Qx St Uk Ul) nA(aM bG bS bZ Fw gP iO Ip Jg Ld mT Nc Ne Ni oE Pf Qz Uh) Pz(kF kK kP lY mH mI mT mU mW mZ nB nM nN nO nR nT) nU(aF aL Ct Di Ii In Mb mT Mv Nf Of qT Qu Qv Tt) Ne(kC kP lW lX mH mM mP mS nB nD nF nM) Me(kG kK kO kP lW lX mM nB nM nN nO) mZ(Ld lK Nb Nc nI Oa Oh Pa qX Ub Uk) mE(aV Dg Et Is Nc Pf Pk) Qz(kC kF mP mS mU nM) Et(kC kO lY mI mS) Nb(kF lY mH mT nD) Oh(kG kK mM nI nN) Kn(kG mP mT nB) Uk(lY mY nF nT) aF(kF mI nI nR) Ld(mP nI nR) mH(lL Nf Qw) mT(cH Fw qV) nD(cJ Dl In) Em(bB cH) Ra(lY mS) Uh(kP mM) nF(Dg Ji) nI(Ok Pa) IsmY KcmI VtlY bPmS nOjE} Ib{oP(aK Ao aQ As aX Bb bF bP bU bV cC cD cF cI cJ cK cM cO Cp Cv Cw cX dK dL Fa Gp Ha Hb Hf Hr Hu Ih Jd kE Kg Li Mj Mk Ml Mr mZ NB NF Nj Nm Nn Ns nT Oe Og Ou Qm Qn Uc Un Vp Vv Tj) nR(Al Ap Bb bF cH cI Co cP Cq Di Ef Fw Id iO Jg Jh Js Kj kQ lN Mt mW Nk Oz Sr Ul Um Vt) Im(kI kK kP mE mH mI mM mP mS mY nD nF nI nJ nM nU) mW(aJ Bb cG cN cT dG Ip Jd Jk Ks mY oN Pz Ua Uc Vu) Ba(kC kF kK kO lX mE mH mI nA nF nH nK nM) nC(Ao aY bA cL Ko Ld Lx Mf Mz Nw Pz Qa Uf) Oh(kC kF kI lY mE mH mI nB nD nF nK nM) nJ(Cq hB iB Jm Jp Ks Mn Nv Nx Ok Uh Vu) Cq(kN kO mH mM mP mZ nI nK nL nO) Et(kC kP lY mH mP mS mU mZ nB nN) Nv(kC kF kK lW lX mI mU mZ nM nN) Kn(kF kI kO kP lX mP mT mU nK) nT(cE Jq Mt Nw oH Qa Qd Qe Tn) Mz(kK lY mF mU nF nH nL nO) nU(Ik Jn Kc Ld Nb Ns Rg Vu) Jq(mE mI mU mY mZ nA nO) mF(bZ Jn Lx Nw Qh Uh Vu) mT(bQ cE dF Kk Kq Nw Rm) Kf(jF jH jP kC mZ nB) Pg(kG kI lW mP mY nF) Ma(kP lW mE mZ nO) St(mH mZ nB nH nK) Kk(kE lX nD nK nM) bF(lW mI mU nF nM) nL(Ko Pz Ut Uu Vu) kI(Jp Mn oH Ut Vu) Kq(mY nA nB nO) dF(kK lW mS mY) kE(aO Jl Nw Ua) kN(cL Jn Ld Mt) Tn(mH nH nI) mZ(oH qX Rm) Tv(oO oQ) Ji(jD oQ) Nx(fR kF) Ok(nB oO) nF(Nw On) nH(oN Qe) oH(nK nN) PzeD QwgP JnlW OmnB bQnA mPoN mYiH} nC{cE(aG aH aI aL aM aZ Bn cB cI cX cZ Dc dE Ip Jn kE lX Mv nA Nf nJ Oh Om Oz Pa RA Vs) Tv(Af bB Bn bW cL cQ dE Hc iJ Ju Kl Kq Lw mH Mm Nf Nw oE oN Pb pF Rf To Uf Uu) Qz(aC Al bL cL Dc Dg Dk iA Ir Jg Jl Jp Kf Kl Kn Oh Pi Qa) Uk(Ao Ap cL dF hA Jp Kk Lh Ne nR Nx oN Oz Pz Qa Qh Uc Vo) Is(Aj aM aY Di dJ dM Ef Ih In Kk Ky Kz mZ Pk Qm Ur Vs) Oh(aC bF Bn cI cJ dE Di dJ Gp Kn Ld Ph) oP(Dp Jy Qn Qu Ri Rj Ua Uf Uh Uo Up Vv) aY(Bc Dc Dg Ir Ko Mh Nw Pa Qw Uu Vt) dF(aS bI Bn Ir Mh Mv Nb Nc Nf Of rA) cG(aI aS Dk Ip Ir kE Kk Mh Ne nT) nR(aF aM Ao bX cZ Dk Dl Ef Kp Qm) hB(bS Je Jh Jk Ld Mu Ne Nj Oz Qu) oO(Bc cV Dc Hc Je Kn Ky Tn Uc) oQ(aN Ar Ba Bc bZ cV dE Je Ky) Qe(bS cI Cp dJ Fb Kr Ld Qw) Ok(aL Ct cX De Dk Je Oa Qx) oN(Cp Ct Di Ef Jd Je My Ra) Uh(aM cI Hb Ir Oz pF rA) Kn(aM dN Hb Ky Md Ng) Nl(cV Gp Ky Qh Uf) Qw(eF hG iZ Jp On) Oz(Dg Kc Kd Kk Ko) Nj(cV oF Ou pF) Hb(Dc Ip Kf Nw) Pz(aN cL cV jD) bF(Bc Lj Of Vt) Ba(Ct Ir Qm) Fy(Et Kj Ky) Ng(Al Kf Kl) Kk(aM Oi Pb) dJ(Dc Qa Qh) pF(Bc Hc Kf) Ct(Ip Lh) Dg(cI Ue) Mh(aM Bc) In(Kd Ld) Ir(Qg Ur) St(Ik Ur) Nv(Mp Nt) Nx(Jd Oa) Uf(Mw Oi) cX(Et Kc) dM(Je jH) DcIi DePg GpNe MtdL NbTn NcOu UccI HcPc IpdG ItNy JiaM QhdI PacJ} oP{Aw(aI aY bB bZ Et Fa Fp Fy Gp Il Jd Jg Jv Kc Kl Kx Lv Ml nI nL Nm Nn No Om Oz Pc Pe Qd Ql Qm Rb Tv Ub Uf Uh Vp Vu) Ng(Aa aC aD aH Aj aK Al aO aR aU bE bH bW cI cJ Cs CT cW Dd dI dL dM Ed Gp Ke Kg Qu Qv Qy Ra Rf Rg Sr Tn Ua Uc) nH(Ad aG An aQ aU aW bH bJ bN bS bX cH cO cP cR cS Cu Cv cW DB dC DD dE Dk Fa Fw Hb Iz Ou Qy Qz) nL(Ad aF aG Aj An aR aX Bc bE bJ bN Bo cA cC cE

Jv Kl Ra Tr Vp) Ip(dH dM dN Gp Kc Kd Kf Qg Tr Uh Ur) Qe(aM aN aW cJ Ct dA dE dM Qy Tt) pF(cF CH Dc Dg In iO Lh Pd Uu) Pz(Aj cI cJ dJ Fn Ko Ld Qy Uh) Qw(Ba bZ Ji Ko Ma Mn Nv Tn) Ld(Ba bZ iA Ji Ma nU On Sr) Oz(cJ cL Cv dG Fn Ou Sr Vt) Mh(Ba bB iO Kf nW Ou Qh) Uc(dI dJ Fn Kc Ne Ng Nj) oO(Bg Fw Jv Kk Tr Vp Vt) Dg(aN dJ Hb Nt Qm Ra) Tn(De Kc Mv Nc Of Ua) Uu(Ct Hu Kd Nb Of oP) Kk(bC cJ Hb Ir Mn) On(Ao cI Ef Je Qm) Uh(Fn jD mM nF Oi) cX(Ap dJ Me Nx qT) oN(Co Mv nA nJ Qx) Al(Hw Ii In Vt) St(dJ Fb Kj Nt) Kf(aM Ii Nt Ue) oP(Qg Ug Un Ut) Ba(Mw Nj Ue) Mn(De Hb Qm) Ir(bA cJ Ha) Qa(Ct Fb Kc) Jp(cI De Ra) Nv(In Nb nF) Pf(aN Dl) aM(Et Fn Mr) dJ(Cv Pa qT) Mw(Fr Pg) Ne(bQ cV) Nj(bA Kl) Kc(cV jD) Ny(Iq Iv) Oa(Ii Ji) Ou(Nb Of) bZ(Di kI) cI(iO Uf) cJ(aN Mt) ChMa CpQh FnNw InPe JfNx JnUp KdRg KoOi QmPg aWqT} oP{Ib(aC Ad Af aG Aj aM aU aW bA bC bM bQ bR bX cG cL cN cR Cs Cu cY Db dC DE dJ dN Ef Fn Fr Gl Hq Hv Ij Jg Jh Jj Jm Jv Jy kG Lj lW lX Mb Md Mg Mh Mi mM MP Mq Mt Mv Mw My Nl nO Nq Nt Nx Of Pa Pc Pd Po Pz Ql Qu Qx Rf Rh Ss Ua Ug Up Ut Wm) nL(aE Af aH aI aK Al aQ aU aV aZ bA bB bC bF bL Bn bR bU bW bX cB cD cI cJ cK cM cN cO cP cR CS cT cU cW Cx cY cZ DB dD De dF dG DK Dl dM dN Fb Gl Gp Hc Ic Kd Kg Ki Kj Kk Kn Kp Kq Kr Ld Pi Pj Pk Qx Qy Uc) nH(aE Af aH aJ aK Al aO aS aV aX aZ bA bM bO bQ bR bU bV bW cA cB cC cD cE cF cI cK cL cM cN Cs cT Cx dF DG dH Dl dK dL dM Fb Kf Ki Kj Kk Ky Ld Vp) Aw(Bg bL bN cE Cu cV Dc dF Ef Fr Hb Hf Ii Im Ji Jj Jq Jt kO Kp Ld Lh Mh Mm Mn mS Nc nF Nh Nl nR Qc Qn Qt Rm Tt Tz Ua Ug Ul Up Ur Us Vt Vv) nI(aD An Ap aV Ax aZ Ba bB bI Bn Bo bV cA cB CH cK cL Co CS Cw Cx dE Dg dJ Dk Gp Hc Hf Kg Kp Ks Kz Ph Pi Pj Pk Ra) Ng(aL bQ Fn Fy Hf Id Jd Jf Ju Jv Kd Ks Qh Qm Qw Qx Rc Rj Rm Tr Ub Ue Uf Ul Up Ut Vp Vu) Cp(aN aY bF Cs In Jl Jn Jp Kk Kn Kq Ma No nR Oh Rm Tn Uk Vu) nA(Aj Ax Bc Bg Bo bZ Ch Co Cq Cx Db Dc Di Hb Kg Pi Pj Qy) In(aF aR cD Cv Iz Kf Kk Kl Kp mF Oa Ph Qy Tv Ul Wm) Ra(aM bG cA Fb Gl Kr Ld Me nD nF Nt Oz Po Uk Vs) Fw(As cF Cw Fb Hu Jk Mb mP Ms nD nJ Nm Tt Ug) aN(aC aF Ar Bn Ct Cw dE Ii kI Nu Pb Pc Qz Uk) nK(Aj aM aX bI bJ bN Bo bS cQ Cu Hb Ou Vp) Cw(aX bB bG Im Jn Kq mE mY nD Ni Nw) Di(As Bb bF Hv Jp Ma nD Ou Qa Qz Uo) Uk(aM aX bV cA Fb Kk Kn Ky nD Nu) nJ(aM Ao Ap aY Bo bS cA dE Ky) Nu(aM Ao Ap aX Bb cQ Dc) bG(Aj Ct Hu Jh mM Mw Qz) Kj(bZ Il Jl Oa Pa Tr) Kk(Ao Bb Ct nF Nt Qy) aP(Ax dG Il kC mS Wm) Ch(Bg Ed kN mW Mz) nD(Ao Ar bS Cv Vp) kI(aM bZ Dc Ky Tn) Ct(kC Kr nF Uo) Nt(Dc Ky mF Ou) Ni(Ao Bb Ed Qy) As(Dc dD mY) Ii(Dg Sr Vt) Vs(aY Pg Qa) mF(Mb Mw Pa) mM(Kn Ky Uh) Ed(Bc cH) Fb(kO Qa) Qz(Ao cV) Oa(aX bV) AjVu ApnU ArmS AxNm BbaX BnJl EfbZ MsnF QwKx KrOh aMkE} nR{Ib(Bc bP cE cJ cR Cv Cw dF eD Fr Hw Hx IC iH Io It Iz Jd jH Jm jT Ki kP lL lO lW lY Ma Mn mT Na nD nI Nm Nr Oa Om Ph Pj Po Qc Qe qU Ra Rb Ri Rj Tn To) nL(Af aG aH aJ As aW aY aZ Bg bI bJ bL bM Bn Bo bP bS bV bZ cC cG cJ CU Cv DC DD dG dH dN Fb Gl Gp Hc iO Ke Kf Ko Kr Kz Qy Tv) Ch(Aj aM aU Ba bJ cB cK cQ Dd De Dg dI eD Ih In iZ jE JG Jl Jm Jp jV KP Ks lL lM lO Mb Mt nF nU Oa On Pe Qa Rb Rj To) Ld(Aj aN aS Aw Bb dE Hc Hu iO Jj lL Mf Mj mM Mp Nb Oz Pb Ph Po Pz Qw RA Uk Us Ut Vs) Qz(dR Hq Ii In Is iZ jL kG kI lK Lv Mz Na nK Nm nN Nt Ny oN Rj Uc Um Vs) Qw(aN Bc bG bJ bS cA DK DL Hb iJ Jk Ki Kj Kk Kn Kx Mf oN Ra) Mw(aN aW Ax bB bC cE cF Cp Cu Dc dF Di Fr iJ iZ Jl Kj Ky Nv Pg) Di(aJ aM As dL dN Ii Is Kp lL lW mY Nb Nf Pf qW Rj St Vs) kI(Af Ao aR As Ax Bc bW De Dk dL dN Fw Gl Gp Ko Kr Qm Qy) lK(AJ aP aX aY bV cF cJ cO cQ CW Dd dJ DL Qy Uk) lN(Ad Al An Cw dI Fb Ke Kq Kr Pi Pj Qn Qu Qy Up Us) aM(cQ De eD hA jD jE Kk Kn Nb Ne nJ Nl Qv qX rA) bP(hA iB jK jQ jR jT jY lO mF mY nA Nt Of Uk) Cp(hA iB Ir jH jK jM jT lM qV qY St Vu Wm) qT(aJ aN aS bN bS cH Cx Dc dL Fw Hc Hf Ph) Kk(Ao bC De Dk eD Hb Ii In Io Is Iu nI) Fw(eD Jk jP jR jV nA Nb Po) In(Al aR bX Fy Kc Ks Pe Tv) aF(aN hA jL lM nA nF nH qY) Kj(It jG jI Ko mZ Nb Pz) Bc(Dk kE mF nA Ng nJ) Ne(Aj bA cH dE Ef Tv) Kc(kC mM nI Of Wm) Uk(aS Aw jH mZ qV) Nt(Ax Dg iO Kz) Ra(mZ Pz Qm Vs) Kf(Aw mF Tt Vs) aO(jO jP jR qU) jI(Af dA dI Ke) Bn(jK jO lM) De(jE nK Vp) Dk(iC nA qW) Ef(jU lL nJ) dL(aV lL lM) Aa(mT mZ) Aw(lL Tv) Kn(mM nH) Ph(qX rA) aN(bX Vs) nF(Db Uh) nJ(Cv Dl) qW(aI aQ) AfnK AsrA CtnH WmiH IpbG aRmF bEqV cHkE} mF{Tv(Af aK Ap bG Bn cE cH Cv dE dM dN Et Fr Hb lJ Jj Jp Kk Kp Ky Lw Me mI mP Mu mY Nh nK Nu Nx oF oQ Pa Rh Ub Uf Uk Up) Qz(Al aN aQ bE cC cT dG dH Dk dM Et gL Gp iA Ik Im Jg Ji Ks Kx Mf Ms mW nT Nw nY Oa oQ Po Qe Rc St Uk Vp) Ld(aA aM bA bZ cI cU Cv cX Dg dH dM Et Fn Fy Gp Hw Jj Jl Kl Kn Ma Mh Nh Nn Pa Pb Po qX Rc To Ug Tj) oQ(aM An aQ As BG bR cA Ch cJ cL CO Cq cT cV Dc dF Ef Fn Gl Hf Ib Iz Kl Kz Pi Ra Ss To Uk) hB(Aw bN cI dA Dc Ez Ib Kc Ke Kk Ky Kz mM Ne Nf Nm Nn nT Oh Ph Pi Qv Qy Tt Ua Ul Ut) Kf(aY bZ Ct dE dF dG Hb It jG Jj jU Ky lN Mt Nf Ng Nl nT oO Oz pF Ql Qw rA Ue) Kk(aN bP bW bZ cL dE dF dL dM Hb Ij In Ky Lw mY Nf Nl Oa Oh Oi Oz Qw Uk) dF(De Di Dk jF jG kK lK lL lM lO Mv Nb Nf Nh Nj Nt Qm qU qX qY) Uk(bZ Cv Dg Fy Ip jH mI Mt Mx Nl Nw oN Pa pF Pg Pz Qa Qe Uh) Kn(aM bZ cE dG dL hA Ii In Is jM lN Nt nU Ok pF) Ib(bA Cq Jm jU Ma Mn Mt Nr oH Ok Pz Qe Rg) Kc(aY bA bF bZ cE cV iB iC jE jI Ky Pa rA) cI(aM bB Bc Et Fr hC iC iJ Jp No Nv Ug Uh) bF(bP Hu Ip Ir jE nF Of Oh Oy Ra Tt) Kd(dE Is Lx Ma Mt nT Ny Pz Ra Vp) cG(aL hA jO kE lM lO Mw Nb nT Qw) Ip(bW dL dM Ko Ky Qg Ub) Qw(bQ fP iZ Jp Ky Ma Qe) Oh(Cp Di Hb Ke Kj Kp Ql) cE(aM kE lK Mp Oa Of Rj) Is(Fn Gp Ha Kp Rj Tt) Mh(nW Ou Uf Uh Vt) Mt(aJ aM bP dG Vt) Nv(Ct Hb JD Je) Ch(iZ PF Tn) Fy(aM bW dG Pf) Nl(nW Ou Tr Ug) Ok(Hb Pk Qm Rj) aY(Dg Di Hc Pa) jD(aJ dM Ko Uu) Nt(Ko Pg Uf) Mw(Fr oN Uf) Ne(bZ Qh Tr) Nx(Jd Rb Wm) Uh(jF lK Pf) oO(dE Kp Ky) Fn(Nw Pf) Ng(bQ bZ) Ii(Rm St) Hb(Nw On) Pz(cX Ky) Rg(Jj Ug) dG(jU Jv) CvRj EfOn WmcJ NmbZ NbUg InPe IrcL ItNy QhaR KojM aJjU cXiC dMlK} kI{pF(Aj Bg Cs cX dE Dg Fa Fw Hf Hu Hv Iz Jn Kl Ko Kp Kq Lx Ly Ma Ml mS mY Mz nB Ne nF nH Nk Nm Nr Nv nW Of Oi Ok Ou Oz Pe Pi Pk Qe Qy Sr Tn Tr Tv Uc Vu) Is(AF aG aJ aL aO Ap aU aW Ba Bg bM bP bV bW cC cI cJ cN Cq cS Cv cZ dD Dg Dk Dl Fn Fw Ju Jv Kf Kq Qu Rg Sr Ss St Tn Tv Tz Ue Uu Uv Vu) bZ(aM As Bc dE dG Hu Ii Ip Iu Jk kK Ky Lj Mv Nf nL Nm Oz Pa Pb Qm qT St Tv Vu) Pf(Aj aN aX bA bN bQ bU cE cJ Cp cR Dc De dK Kd Kr Kx Ky Oa Pi Qw Rg Ri To) oN(aH aM Ax Bg Jk Jn Jo kO Kq Lx Md mI nA Nc Nj Pc Qg Qu Qx Rm Tv Ue Vs) bF(Ao Aw Bb Ch Cw Di dL Fw It Ne nI nL Nu Of Oh Qm qT Ra Rh Rm St Wm) hB(Ad Ao Fr gP Jk Ky nF Nj Nm nO Nq Qa Qu Tv Ua Up Vs) aY(Ch Fr hA Hc iB In jD jM Kk Oa Ou Pa Rj Uk Vp) Tn(Ch dE Gl Hb Hc Iu JH Lj Nb Nl Uk) Ou(cI cZ De iC Iq jE Kd Ly Me Ng Nt Vu) Ib(Cu Et hA jH Jn Kk Nw Ok Tr Tv) Oh(cF fP gL hF Kr kS nW oE Uk) Ma(aH aR Cs dL dN Hb Ko) Qz(Dc dR fP hC iA On Qh) cE(aM In Nf nI nL Oa Rj) Tr(cI Ir jD Qm Qw) Oa(eF gL hG iA Lv) Qw(eC gP iZ oF) jH(aJ Rg Rm Sr) Mw(dF Pg Qh) Tv(iA kS oK) In(Nv Pe Vu) Ld(eC iJ Jp) jD(Ch Kk Qh) Dc(eC Ii) Qa(cS iP) bQ(Ir jI) cV(Ip Nj) dF(Bn Qm) eD(cG Kl) nW(cI Mh) ChfP EfNg EtHb NloF JeOk UklN PaeC} nL{cE(aE aM Ao aQ aR As aU aV aY aZ bI Bo bS bV cA cB cD cI cY dA Dc De eD Hu Ip Is Jh kE Lj mW mY nF Nj Nm nO nT Og Om Oz Po Qm Ra Rb Tt Tv) bF(aS Ax bW Ch dE Dg Hb Ir Ld Nf nJ Nt Om Oy Oz Pb Vt) dF(bX cQ Ct dE Di eD Ip Kc Kk Me Ng Nj Pb Pz Qm Qw Uk) hB(Ao aP De Ii kG Kn Ne Nf nH Nq Oi Qm Qy Ra Tt) Ib(Et gL Hc Jg Jn Jp Kq Nw Ok PF Qd Qh St) Is(aY cL Cw dM Id Ko Kp Rj Ua Ug Uh Up Vp Vt) Ou(aS Hu Jh Kd Lv Mh Ng Nh Oa Oh Pb Pz Ra Vv) Uk(bZ cU Dd Et Jp Kf Ma Mn Oz Pg Pz Rm Uc Uf) Tv(dR eF hC iZ Jl Nf Oi oK Pz Qz Tr) oN(Co Cp De Ef Jd Ld Mv My Qm Ra) pF(Dc In Jd Kf Oa Oh Oz Pa Qe Qm) Kn(bZ cV Ii In jD Jl Jp mI Oi) Tn(Ii In Mw Nb Nf Nl Oi oO) Ld(Bg cV eF gL hC In tF) Qz(Bg Dc iJ Jl Jn Nv) aY(Dg In Kz Mp Pa Rj) bZ(aO Di Ef Mv Mw Oh) Nv(In Mp Oi Qy Ra) Tr(Mh Nj oO oQ) Hb(Nw Oh Ok Uh) Qw(Bg gL iP Jp) Pz(cV cX Ky) Je(Nx Ok Pf) Kk(mI Oi Pf) Oz(cJ Ko Kp) jD(Ny Sr Uh) Ch(Jp oQ) Dc(In Rf) Mh(iO oE) Nj(nW oF) Nl(hC Uc) Ii(Al Uc) Oh(iJ Kr) Ok(Jd Qy) On(Qx Vu) oO(BG) CtPg DiPf FyIn MweF TorA HcPc ItNy QeoH RajH QhdJ KccV KflN KoOi NxOa nTiA} Ib{mW(cJ Cw Fr Hx iC Jh Jm Js Kd Ke Ml Nx Oa Pa Ql Qz Ra To Uk Ul Um Ut Uv Vt) nU(bQ Cq iB iC iH Jp Jq Kf Ks Mx Nj Ok Pf Pg Uk Un Vp) kN(aD bA cE Dd dF dM Et Ip Ko Ma Mz Nw Nx Pg) Cq(kC kG kK kP mI mS mY nA nD nF nH nM) Ma(kC kF kG kK kO mI mM mS nB nD nF nM) Et(kE kF kG kK kO lW mY nA nD nF nH) Kf(iC jG jI jO jQ jU lL lN mI nI nO) Kn(kE kK mE nA nF nI nM nN oO) Im(kG lW lY mU nB nK nN oO) Pg(kC mI mT

Unconstrained panels with 3 analytes, where 1.0E-7 >= 'AUC p-value' > 1.0E-8. Contains 16,074 panels of 16,766,520 total panels evaluated. :
Ow{Rf(aA aE al aJ aK aM An Ap aQ aR aU aV aW Ax aY bB BC bE bG bH bJ bM BN bO bP bQ bR bS bU bV bW bX cA cB cC cF cG cl cJ
cL cM cN Cq Cs cT CU cW cY cZ dA DB dC DE dF dG dH Dl dK DL dM dN Dp ED FP FR Fw Fy Gl Gp Gz Ha Hq Hr Hu Hv Hw Hx Ic Id
Ih Ii Il Im Io Iq Ir It Iv JD Je Jf Jh Jj Jk Jm Jo Js Jt Ju Jv KC Kd Ke Kk Kl KO kQ Ks Kz Ld Lh Li Lu LW lX Ly Mc ME Mf Mg MH ml Mj
MM mP Mq Mr Ms mT mU Mx Na Nb nC Nd Ne Ni Nj nK NM Nn Nt Nu Nv Ny Oh Om On oQ Pa Pd Pe Pf Ph Pj Po Qb Qc Qe Qg Qn Qw Rc
Rg Ri Ss St To Tz Ua Uf Uh Ul Um Uo Up Ur Ut Vo Vp Vs Vt Vu Vv Tj) Mp(aA aD aE aG Aj aK AL AN AP aQ AR As aU aV aW Ax aZ bA
BB Bc BG bH bJ bM BN bP bQ bR bS bU bW bX cA cB cC cF cJ cK cM cN CO CP CQ Cs cT CU cY dA Db DE Dg Dl dJ dK Dl dM dN Dp
Ed Ef Ez Fb FP Fr GP Ha Hb Hc Hr Hv Hx Ic Ih Ik Il Im Iz Jd Je Jg Jh Jm Jq Jr Jt Ju Jv Jy Kd Ke Kg Kj Kk Kl Kx Ld Lh Li Lj Lu Lv Ma Mc
Me Mg Mh Mj mM Mn Mq Mr Ms Mu Mv Mx mY Na Nb nC Nd Ni Nj nL Nm Nn No Nr Nu Nv Nw Nx Ny Oe Oh Oi Om Pa Pf Ph Pi Pj Qb
Qc Qd Qe Qg Qm Qt Qu Qv Qw Rc Rg Rh Ri Rm Sr Ss Tn To Tr Tv Tz Ua Ud Ug Ul Um Uo Up Ur Us Ut Vo Vp Vq Vv Wm Tj) Kr(aA aC
aD aE Af aG al Aj aK aL AN AP aQ AR AS aU Aw aX aY aZ bA BB Bc bE bJ bM BN bO bP bQ bR bS bW cA cC cE cF cG Ch cJ cK cL cM
cN cO CP CQ Cs cT CU Cv cW Cx cY cZ dA Db dD De dG DI dJ Dk Dl dM Dp Ed EF Fp Fr Fw Fy GL Gp Gz Hb Hc HF Hq Hr Hv Hw Hx
iA Ic Ih Ii Ij iP Iz jD Jg Jh Jj Jk Jm Jo Jq Jr Jt Ju Jv Jy Kc Kd Ke Kg Kk Kl KQ Ks Kx Kz Lh Li Lj Lv Ma Mc Mf Mh ml Mj Mn Mq Mr Ms Mv
Mw Mx My Na Nb Nd Ne Ni Nj Nl Nn No Nr Nt Nu Nv Nw Nx Ny Oe Oh ON Or Pa Pd PF Ph Pi Pk Qb Qc Qd Qe Rc Rh Ri Sr Ss Tt Tv Ug
Un Up Ur Us Uv Vo Vs tF) Ct(aA aF aG al Al aM Aw aX Ba bB BC bl bQ bV bX cC cD cG cJ cL cM cP cR Cs cU Cv cX dB Dc DD dF dH dl
dR eC Em Et Fa Fn Fr Fw GL Gp gW hB Hq Hr Hx Ib Ih Ij Ik Il Io Ip Iq Ir Jg Jj Jl Jm Jo Jr Kc Ke Kf Kj Kk Kl Ko Kp kQ Ks Li lW Lx LY Lz
Mb Md Me Mf Mg Mi Mj Mk Ml mP Ms Mt Mu Mv mW Mz Na Nb Nd Nf nH Nj nL Nm Nq Ns Nu Nx Oe Og Oh Ok ON Oy Pa Pb Pd Pe Pf
Pg Pj Pk Po Qa Qb Qc Qe Qh Qw Qx Qz Ra Ub Uk Ut Vq) Oz(aA aC AD Aj aL aM AO Ap Ar aW Ax aZ Ba Bb bE bl bN bV cB cC cD CH cJ
CO cQ cR Cs Cv Cw dA Db DD De dl DK Dl dN eD Ef Fa Fb Fn Fw Gz Hc Hq Hr Hu Hv Hx iC Ih Ik Io iP Ir Is Iz jE jF Jh Jj Jk Jn Jp Jr jY Kc
Ke Kg Ki Kj Ko Kp Kq Kx Ky Kz Li lN Lz Ma Md Mg Mj Mk Ml Mm Ms Mu Mv Mw My Na Nd Ne Nh Nj NK Nl Nm Nn No Nv Nw Ny Oe
Of Oh On Or Ou Oy Pa Pb Pc Pd Pe Pg Pz Qm qT QW qY Qz Ub Us Vv) Ql(aA Af Al aM Ao As aX Ba BC Bg bl Bo bV cD cJ Cp cQ cR cS
Cv CX Db Dc Dd Di Ef Ez Fn FP Fr Fw Gl Ha Hc Hq Hr Hu Hv Ic Ii Ij Il Ip Iq It Iu Iv Jd Je Jf Jg Ji Jk Jm Jo Jq Js Jt Ju Jv Kf Ki Kn Kp Kq Ks
Kx Kz Lh Li Lj Ly Lz Mb Md Me Mf Mg Mi Mk Mt Ne nF Nk Nm Nn Ns Nt Nu Nv Nw Nx Of Oi Ok On Oy Pa Pd Pg Pi Pk Po Qa Qb Qc Qd
Qe Qn Qt Qw Qy Qz Rg Sr Tn Ua Uc Ud Ug Uh Up Ut Uu Vp Vq Vs Vv Wm Tj) nJ(AD aF aG aH al Aj AL aP aR AS AW AX bA bB Bc bE
bN bO bR bU bV cB cC cF Ch Cq Cs Cu cX dA dB dC Dd dH dl Dp dR Ef Ez Fb Ha hC Hq Hu Hv Hw iB Ij Im Iu Iz jE Jg Jh Ji Jj Jk Jo Jq Jr
Kg kl Kj Kl kO kP Kq Ks Lj lM Lw Lz Mb Mc mH Mi Mj Ml Mm mS Mu Mx My mZ nB nH nI Nk nL nM No Nq Ns Om Pg Ph Pk Qb Qd Qn
QT QX Qy Rc Rh Sr Tt Tz Ua Uf Um Un Uu Vo Vs Vu Vv Tj) Iv(aA AD AF Aj Al aM Ao aV aW Ax aZ Ba BC bF BG bH bl bN bR bS bU
bX cC cF cl cJ cK cO cP cR Cs cT cV Cx dA Dc Dd dF dl Et Ex Fa Fn Fw GP Ha Hb Hf Hr Hu Ih Ii Ik In Iq Is It Iu Je Ji Jl Jo Jp Js Kc Kd Kf
Ki Kn Kp Kq Kz Lj Lv Ly Lz Md Me Mg Mi mM Mr MS Mt Mz Nc Nd Ne Nf Nh NK Nl Ns Nu Nx Ny Oe Ok On Or Pd Pe Pg Pi Po Qa Qx Ra
Rb Rj Rm Sr Uc Uk Vq Vv Tj) Ng(aC aD aE aG aH al AJ aK aL aP aR aS aV aZ bA bE bH bL bM bO bP bR bS bU bW cA cH cK cN cO cQ
cT cY cZ dA dB dC dD dG dJ dL dM dN Ed Ex Ez gW Ha Hb hC hG Hu iA Ib Ic iH iJ Ik iZ Jd Je jH Ju Jv Kd kR kS Kx Lu Lv lY mE mF ml
mM Mw Mx nC nF nI NO nW NY Oa oE oF oH oN pF Qg Qm Qn Qv Qy Rc Rg Rh Ri Rm Sr Tr Tz Ua Ub Ud Uf Uo Up Ur Us Ut Uv Vo Vp
Vs Vt Wm Tj tF) Pb(Ad Aj aM aN Ap aV AW aX Ba Bb BC BG bl bV bX cD cJ cP cR CS CV Cw Dc DD Di Dl Et Fb Fn fR Fw Gl Hb Hc Hr
Hu Hv Hx Ih Ij Ik In Io Ip Iq Ir Iu jE Jf jH Jj Jk Jn Jp Jr Ke Kf Kg Kj Kn Kp Kq Li Lu Lw Ly Lz Ma Mb Md Mf Mg Mi Mj Mk Ml Mn Ms Mt Mv
Mz Nd Ne Nh Ni Nj Nl nN Nr Ns nT Nu Nx Oe Of Om Or Ou Oy Pa Pc Pd Pe Ph Pi Pj Pk Po Qb Qc Qm Qx Qz Qh Ut Vq Vv) nU(aC aD aH al
aK aP aQ Ar aU aZ bE bG bH bl bL bO bQ bU bV cB cG cH cJ cL cO Cq cU Cv cW cY cZ dA DB dC dD dF dG Dl dK DL eF Et fP Fr Fw gL
hF hG iC iJ Il Jf jH Ji Jj Jk Jl Jp jQ jR jV kC kE KG KN kR Kz Li lL Lu Lv Lx Mb mE mF Mr mS Mu mW Mz nA nB NI Nj NK No Ns Nw Nx
oF oH Ok ON Pe pF Po Qa Qh Qn Qt qU qW qY Rg Rm Ss St Tr Tt Tz Uh) Js(aA aC AD Af aG aH al aJ aK AL aN AO aP aQ aR aS aU bA bB
bC bE bJ bL bM bO bQ bU cB cI cK cM cN Co cT cW Cx cY cZ dB dC DD dE DG dl dJ dK dL dM dN dR eF Et Fa gL gW HF iA li Il Im In
Ip It Iu Jh Ji Jp Jq Kf Ki Kp Kq Lj Lu Lv Ly Lz Mb Md Mg Mj Mk Ml Mt nC Ne Nh Nj Nk Nl Ns Nt Nu Oa OE Oi Ok ON Oy Pd Pg Pk Po Qa
Qd Qx Qz Ub Ue tF) Nt(aF al Al aM Ao aW aY aZ Ba bB bC bF bG bH bl bN bX cD cE cG cJ cR Cu Dc Dd dF Dg dH dR eF Fa Fn Fr GL gP
Gz Hb Hc Hf Hr Hu Hv Hw Hx iA Ii Ik Il Im iO Ir It Jg Jh Jj Jk Jo Jy Kc Ki Kk Kl Kn Ko KQ KS Kz Lw Ly Lz Md Me Mf Mk Mm Mr Ms
nC Ne Nh Nk Nm nN Ns Nw Oe Of Oi On Oy Pa Pd Pg Ph Po Qd Qe Qh Qy Qz Ra Rb Rm Sr Tn Uc Uk Up Vt Vv Tj) lt(Ad AF aG al Aj Ao
aV aW bF BG BN Bo bR bX bZ cC cG cK cO cP CV CX dA Dc Dd dF Dg dH dN Et Fa Fp Fr Fw gL Ha Hf Hr Hu Hx Ii Il Ir Is Je Ji Jl Jo Jq Kc
Kf kK Kn KO Kp Kq Ks Kz Li Lu lY Lz Md Me Mg Mi Mj mM MS Mz NC Ne Nh nl Nk NL nM nR Ns Nu Nx Ny Oe Of Oi oK On Pa Pd Pe
Pf Pg Pi Po Qb Qx Qz Ra Rj Rm Ub Uc Ue Uu Tj) Ky(aA Ad Af Aj Al Ao aW aX aZ Ba bC bl BO bV bX bZ cC cD cJ cP cR cS CV CX Dc dH
Et Fa Fn Fw Gz Hb Hf Hu Hx In Io Ip Iq Ir Is Iz Jj Jk Jn Jo Jp Jt Kc Kf Kk KQ Ks Kx Lj Lu Lw Lx Ly Lz Mb Mc Md mE Mf Mg Mi Mk Ml
Ms Mt Mu Mv My Mz Na Nd Nh Nj Nk Nm Ns Ny Oe Of Og Om oP oQ Or Ou Oy Pa Pd Pe Pf Pg Pk Qw Ra Rj Ub Ut Uu Vv) li(Ad aF aM
Aw aX Bc bF Bg bl Bo bV bX bZ cE cG cX Db Dc dF Dg dH Et Ex fP fR Fw gP Hc Hf Ib Il Im In Io Ip Ir Is Iu Jg Jl Jm Kc Kf Kn kO Kp Kq
Lh Lu Lx lY Lz Mb mE Mi MM Mr MY MZ nC Ne Nf Nh Nk Nl Nm Ns Nu Nv Nx Oe Og Oi On Or Ou Oy Pd Pe Pf Pg Pi Qa Qe Qx Qz Rj
Ue Vq) Pz(aA Af Aj Ap As Ba Bb bF bl bJ Bn bV bX bZ cC cE Ch cP CQ Cs cX Db Dd Dl Em Fa Fn Fw Ha Hb Hf Hr Hu Hx Ih Ij Ik Jf Jh Jp
Ki Kk Kp KQ Kx Li lW Lx Ly Lz Md Me MF Mi Mj Mk Mq Ms Mx My Na Ne nF Nh Nj Nk nN nR Ns Ny Om Ou Pe pF Pg Ph Qb Qc Qm Qx
Rj Tv Ug Ut Vv) cV(Aj aL aM AO aS aV aX Ba Bb BC Bg bP bW cA cC cD cH CO Cp cQ cR Cu Cw De Di Dk Ef Em Ex Ez Gz Hb Hq Hu
Hx Ij Ik In Iz Jh Jj Jq Kc Ki Kq Ld Lz Ma Mb Md Me Mf Mi Mj Mk Ml Mv Mw My mZ nC Nd Nh Nk nL Nn Ns Og oQ Or Oy Pd Pe Pg Qu
Qx Ra Rj Ua Ub Up Vq) Nf(aA Ad aF Al aW aX bC bF Bg bl bV bZ cC cE cJ cR Cv Cx Et Fa Fn fP Hf Ib In Io Ip Iq Ir Iu Jk Jl Jn Jp Jt Ki kN
kO Kp KQ Ks lW Lx LY Lz Mb mE Mf Mg ml Ml mY nD Ne Nh nl Nj Nk NL Nm nN nO Nx Oe Of Og oP oQ Ou Oy Pd Pk Po Qa Qc Qh Qw
Qx Rj Ub) Ib(Al aW Bc Bg Bo bV bZ cC cE Ch cJ Cq cR cS Cw CX dB Dc Dd Dg eF Et Fa Fn fP Fr Fw Ha Hc Hf Hw Ik In Ip Iu Jg Ji Jl Jn Jv
Kf Ki Kj Kk Kl Kp KQ Lh Ma Mb Mk Mt Mu Mv Na Nc Ne nl NK Nl Nq Oe Og Oi Pi Po Qn Qz Ra Rb Rg Rm Sr Tr Uc Ue Uk Uo Vv Tj)
Pc(aA Aj Ba Bb Bc bl bV cD cM Cp cR CS Cv Db fR Fw Gl gP Hb Hw Ih Ij In Io Ip Is Iu jD Jk Jn Jo Jp Jt Kk Kp Ks Ly Lz Ma Md mE Mf Mg
Mk Mn Nc Nk nL Nm Ns Nu Nv Oe Of Og Oi Ou Oy Pa Pd Pe Pg Ph Qb Qc Qw Qx Qz Rj Tv Ub Ut Vq Vv) nC(aK Al Ao Ar Ax Ba bL bQ bZ
cJ cL cQ cR cU Cv Dc dF DG dH dM dN Fr Hv Hw Jd Jg Jh Jj Jl Jp Jy Kc Kf Kl Kp Lh Lx Ly Ma Md mE Mf ml Mk Mw Nb nF Nm nN No
Nv Nw Nx Of Og On Ou Oy Pa Pe Pg Pk Qd Qh Qx Rg Rm Tn To Un Up Vu Vv) Oi(Ad aM aQ BC bl Bo bX cD cE cR Dg dM Fa fP hB Hf
Hq Hw In Io Ip Iq Ir Is Iu Jp Jt kE Kf kG kl Kp Kq Ks lW Lx LY Me Mk Ms mT My mZ Na nB Nh Nk nM nO nT Nu Of Og oQ Or Ou Oy Pd
Pe Pg Po Qc Qd Qx Qz Ra Rj Ub Uk) Ue(aA aM aX bC Bg bl Bo bV bX cD cP cR Cs Cv dE Dg dH Et Ex Fn fP Gz Ha Hv Hw Hx Ij In Ip Jf Jn
Jp Kz Li Lz Mb Mk Ml mM Mv MY nB Nc nD Nm Ns Nu Of Oh oP Ou Oy Pd Pe Pk Qb Qw Qz Ra Rg Rj Ub Uc Uk Uu Vq Vt Vv) mF(aC aJ
Al aN AR Bb bC bF bl bQ cE cG cJ cQ cS cX dF DG dH eC eD Fr gL hA Hc Hx iB iJ Io Jd jE jH Jt JV JY Ki kK Kz Lj lK Ma mH Mw mY Nb

Lh Lx Mf Ml Mt Mv Na Ne Nf nH Nj Nk Nl Nm Ns Nt nU On Oy Oz Ph Pk Qa Qc qX Rf Rg Ub Um Vo) Pz(aC Aw bC bF Bg bQ bV bZ cC cG Ch cL cM cQ cR cS cT cU Dd Dg iB iO oH Rj Tn) Kf(aV Bc eC eF hB hF Hw iO iZ Jn Jp kR kS Ky mM mP mU MY nH nY oK Om oN rB) Dg(eD hC iB iC jD jE jF jH jI jL Jn jQ jR jT jU kN lN nH nl Om rA Rj) Uc(eD hR iB jF jL jO jP jR jU jV lM lN lO nD qU rY) nU(aN Ba bF cE gL hB Kc Ko Ou Tn To Uk Ut) Et(Bo Dc Dd Ef Hb hC Ki Ky Ph Pj Pk Rj) My(aC aN Ax cL cV cX Dc DD Ou Uu Vq) Jp(An Ax Ba Bc bI Cv Dc Dd Kk Ky Rj Vq) Uu(Bc cM hR hX jl Jn jO jU jY lN nH) Ou(gP Jn Mb Nc Ne Nh Nt Nu Rj) Ba(Jn Kk Ly mM Nc Nl Og Rj) oN(kC mP mS mT mY mZ nD) hB(Ex mY Nd nl Nl Nu) Nj(Bc bZ eF iJ iO) nA(dF gL hG oH pF) Dc(bC {R Ky Nc) Tn(Me nK Qz Rj) bF(bC mY Nc nl) Bc(Jg Mt On) Kk(mP mU nl) Ko(jF lN qX) cE(kE mY nl) cV(Ns Pa Qz) dF(kE Nc Nd) Dd(Jg Ky) Ef(kE mZ) Jl(Ne Nl) Rj(eF Jg) Nx(Em mP) Vq(Ky Uk) BoJn KnjH NvmZ bZmS cGqU nDiH} Qw{gP(aC Af aM aP aS Ax Bg bM Bo bQ bZ cF cJ Co cP cR Dg dH dl dK dL Dp Fa fR Hb Hc Hf Hu Hv hX iA Ij Ik Je Jf Ji Jo Jq Jv Kg Kn Kq KS Lj Mf Mg Mk Mm Mp Mq Mr Ms Mt Mv Mx My Mz Na Nf Nh No Nq Nt Nu Nw Oa On Oy Oz Pb Pc Pi Qd Qg Qt Qu Qx Qy Rc Rg Ue Ug Vs Tj) hB(Bg bl Cp Ed Ex Hu li Jt kC kG kK Kr lY Mg mH mS Mv nK Nt Nu Pz Tt) iA(cP kC kK kN kP lW lX lY mM mP mT mU mY Nc nD Nk nM nN nU Ub) Ub(dR fP gL gW iH iJ iO kQ kS oH oK Ou tF) pF(cF cP dN kO mH Nj Nk nO nU oH Pz Rj Uk) Pf(kN mE mS mW mY mZ nA) eF(kO Mg mP mY nH Nj Nk) dF(kG kK nA nH nl) Ou(Mf mY mZ Nl) iH(kO mP nA nH) kE(cE hC nW) Nk(iO oH) bF(nH nK) fR(Jp Li) iJ(cP Nc) oN(lX mU) ExNx RanU JlmY UkVq bCoH cEkK nDoE iZkG} nA{oN(aA Ad aO Aw bN cQ Ed Fr Fw Jk Jt kG Kk Kr lY Mu Ne nH Nm Nn Nq Of Oh Pa Qd Qx Rg Ri Sr Tt Tv Ub Uf Uo Tj) Ou(bC De Di gP li Jd Kc Me mM Nj Pf Pz Rg Up Ur Vp Vs Vv Wm) hB(Di Hu Iz Jh kE Kr Nm Nn Nt Of Oh Pa Vp Vt) pF(aN Cp Kn Ma nT nW Oh Pa Qt Qy Ss Tv Vp) Tn(aJ aM bS Ef Fw Jy Kd kE Ky Nb Ua Vt) bF(Ao Cp dE Di Hc Jh Ld Nt Qy Qz Wm) Ma(aJ bW Ct Cv Kc Qu Uk Ur Vt) bZ(aF Ch ln It Nq nT Of Qu Qz) cE(Aw Cp Ct Dk gP ln It Nb Nl) Ld(aY Bg iJ In iO nY oH Pf) Pf(iH Je Kk Ri Rj) ln(cJ Nv Pe Qa) Qz(Dk iH Jl oE) Uk(aY cG jH oH) Tv(aM Ih iO) Ip(aC Ny Uh) Oh(cQ gP oH) Vp(aY cJ Ra) dF(Dk Iq Qu) Ch(gL hG) Et(cI Pj) Mw(hC Nv) Je(Nv Nx) St(Fb li) Ok(cI Dk) cJ(Ky Tr) dM(gP kS) DePg DgNm NjnW NlcV HbLh ItcG RaqT JlKk bXjH} Ld{fR(aA Ad Ar bG bN bS bU bW cD cE Ch cM cO cV cZ dA Db DC Dd dI Ed Em gP Hc lH ln Je Ji Kd Kq Kx Lh Lv Lz Ml Mm Mz Na Nq Oe On Oz Pb Pd Pe Po Qh Qt Qx Rb Uc Uh Uk Ur Vs Wm) Em(aH aO Ar Bg bJ cA cG cV cW cZ Dc dl lu Iv Ji Kc Ko Kr Ky Lj Lv Lw Lx Ly Mn Mt Ni Nj Nk Nn Nv Ny Oh Oz Pa) mP(aM aY bG bQ cB cS Cx eC Ef Fr Fw gL Hc jl kN Kx nH Ni Nm nN Nr Nv Og Oi Ok Qd Ra Rg Uc Uo Ut Vp) ln(kE kG kK kO lW lX lY ml mS mU nD nK) Pf(kN lW mE mH mU mW mZ nl nM) nl(dF hB Ky nU Nv Oh Ou Pz) pF(kG kN lX ml mZ) nU(As Ic Lz Sr) nK(hB Ma oN Qh) Gz(iB jH) Ou(mH nD) bF(kG nD) mM(hB Uh) kE(aY Jl) ExlM limU ljmW PkjH cEnH mZqT} Qz{mW(aM bB bL bW Dk hB hC Id Ji Kf Lw Ma Mp nU Nx Oz PF Qa Qh rA) nU(aM aN aX Fy Jn Kq Ky Ma On Oz Pg qT Rg) Uc(kC kF kN kP lY mS mT mU mY nO oO) nH(bG bQ Dc Dk iA Kn Ok On Pg Pz Qa) nl(Ba bZ cG cV Gp hB Lv oH Pg Qa qT) kG(cE cG cV Dc Dk Jl Kf On Pf qT Tr) mM(hB Kn Kq Ma Nv Nx Pf Tr Uh) qT(kK kN lX mE mP mT mU nB nK) mZ(bF cE Fy iA Jl Jn Pg Qh) nO(bZ Ch kS nY oK pF) kE(Fy Kq Lv oF On Pg) oE(lX mE ml mP nB nD) oN(kF kK kN kP mE nN) Ma(kK kP lY mS nT) bF(kC lY mE nK nN) mY(cV Jl Kq pF Tn) Nx(fR lY ml mP) Tn(kK lW mH) Ou(Nt oO Ut) nD(Jl pF Tr) Kq(kO nB) Vp(mU nN) cV(mH Pz) nT(Jl Qa) lW(iH nY) hB(kO lY) kK(cE Cu) pF(mH nK) DcmP LvmE TrfR OzkN PfnB cXgP dFml} nH{cE(An Ao aY bI cA dA Ip Ir Lj Mh mY Nj Nt Oa oQ Ra Uk Vu) Tv(aM aY li Jp Kc Ky Ne nY Uh Uk Vt) Uk(Dc Et Ir Jn Jp Nh Ou Pz Rm) bF(aS Bc Ch Ct Jd Lj Po Qx Vt) cI(bB cG iO Jp Ok Qe Uh Vt) Kn(aY Ed In jD Md nU Oh) pF(Bc cQ ln mS Nd Uh Vt) Nl(aY cG Gp hB Tr Uh) Oh(aW aY Bn bX cJ cQ) Ct(dF lp Nv oN Pg) Kc(cX Ou Qa rA Rm) hB(Cp cQ Di Mv Nj) Ip(bB Jl Ny Uh) Nx(aY cX Je Vu) Ou(Kd Mh mZ oO) oN(As Ef Mv Ra) Uh(Mh mM rA) bZ(De mZ oO) Fb(Qa Qe) Mw(Fr Qh) Tn(Ch Jk) li(Dg Fy) Hb(Lh Nw) Kd(ln Pg) dF(Bn bX) mZ(Jl Mz) oQ(bG cV) MtbC lvNy PzjD QeVs JdOn KflN KyqT VtoO Pfdl dNoH} Em{Ou(Aa Ad aH al aJ aK aM An aO As bE Bg bH bl BO bW cB cC cD Co CS cT Cv cW Cx cY cZ dC Dd Ef Et Ex fR Hb Hc Hf Hv Hx Iq Jh Ji Ke Ki Kn Ko Kp Kq Kr Lh Lj Lw Lx Md Mp Mr Mt Mx My Nb Nc Nh Nn Ns Nv Oi Om Oz Pc Pe Pf Pj Pk Qb Qc Qd Qe) Nx(aC AJ aQ Bn Bo cN Ct Iz Ke Ky Lu Mg Og) aC(aJ aN aV bS cL dA dB dG dI dJ Hv Ni Ok) Ly(aH aI bB cE cL Ky Ma Qd) aV(cG dE Ex Gz Jl Ml Mp On) Nw(dA Ii Kf Kk Lu) Qd(aQ Ii Kj Li) Ok(Aa Kj Lu Om) Nb(bB bJ) aN(al Lu) AsbB liLh KgOn KjKq aDcV dAfR} nl{Kk(aJ aL bF cL cN dE dJ dN iC Id ln lt Iv JF jK Jl jM jQ Ky lW mP Nf Nj Nt Oi qU qW Ra St Tv Uf) cE(aM aR aS Bn cl Dk Kc kE lM mM Mp Qm Uk) cl(cG dF Et iC iO Nw Oh Ok Pf Pz) bF(Aw Cp De lM mZ Nt qT rA) Uk(cG Cv hA jD jH Oh rA) Kc(cX jD jM lN qT Tv) Kn(aM hA jD jM lN nU) dF(jE jK jO Ne Nj Nl) Mw(Dg Pg Qh Uf) ln(Fy Kd Kf Nv) Di(hB oN Pf) Tv(aJ li Vt) Hb(Et Ji Uh) Kf(Nm Oi rA) Ky(jY qT rA) Nv(Dk Je Nt) Ne(Ou Tr) li(Rm St) Ko(qT rA) Nx(Ao Bb) Oh(bX Cp) cG(Dk Nb) DePg NlOu UhjD Pfdl} ln{Pe(kC kG kN kO lW lY mH ml mM mS mU mW mY mZ nM nO) Nv(kC kE kP lY mE ml mP mT mU mY nO nT nU oO) nU(Al cl dM Fy Kc Pi Qh Vt Vu) nD(cE Ip Kn Pa pF Pg Vu) Fy(kP mH ml mS nB oO) Pi(kE mP mZ nB nK Vq) oQ(cQ Dd Ed Hx Kf Oa) Iv(kP mT mW nM nT) oO(aN bP Hx Jl Tz) Pg(mP mT nO nT) kE(Pf Qa Ra Tn) Jl(Nc Ne Nh) Jn(Nc Ne Nl) Kf(ml mM mY) Pa(kC mE mZ) Dc(mP mZ) Pz(hW Ou) Qa(kF mU) St(kG mE) Kn(kG kK) CqmP UeVq QhmZ KcmI KdmY OanN lYrZ nKpF} fR{Nx(Aa Fa Fb Fw GP Hb Hc Ic Ju Jv Kc Kf Kl Kn Ko Kq Ks Ky Kz Mi Ou Ph Pi Pj Qn Qu Rg Sr Tt Ub Ul Um Uo Vo Vu) aC(aP aR aX bA Bc bl bP cA cC cE cF cJ cK cQ cS CT Cv cW DB Dd dJ dN) aN(bF cQ dB Dc Et Jn Jp kQ Lh Na) Mw(bB Cv Dc iH Ji Jp Nf) bR(aD An bC Dc Nd Nf Nt) Et(iH Jt Nf oH Oi) Dc(Nf Og) aD(bF cE) kQ(Kn Nw) oH(It Ur) AadA CvOg NfNj IpRj IqJi KcOu aMcT aObF bCbW cDcE} mZ{Jl(De Hu Ii kO Lj Lv Mh mP Mu Mv Mz Ne Nf Oe Oy Qa Qe) Oh(BG bZ cV cF gL hF iH KR kS nY oE oF Uk) Mz(aA Io Ir Iu kF Lz mI Nb nD Ne oO Pf Qa) Uk(bF cE hA Jn Ok oN Qe Qh Tn) Ou(Ch De kO Mb Pa Ra Wm) Mw(dF Fr Nv Qh Tn) Oa(dF Kq Ma oH On) Tn(Cw De Jh Qy) Ra(bF bZ dF Ma) Vu(bF cE cV Ok) Pa(aY iA oE) Pg(Ct De Je) Ch(bZ Ma) Ii(Dc Qh) Nv(Je Jh) AnaY DgNm PoQh NfNy HubF TvPf IrcV KkpF KyqT aNoN aXbZ} Uk{nU(aM bO Et Fw Ip Kc kE Kp Ky Nb Ne Nl Oh Ok Pg Pz Ra Vp) Pz(hA jK jP jQ jT jV jY lK lL qY rA) mY(aM hA jT Nx Oh Ok Ou pF) nK(cJ hB Ir oN Pf Pg St Tv) kE(cE hA oN Pg Qa Qe Tn) Ok(kC kO mE mM mS mW) mE(cE jR jU Pg Qa) mH(hA jE jF jH lN) qT(kG mM mP nN nT) Et(jD kO mI) hA(kG kP mW) nD(cE Ip Ou) kK(Kn Oh qX) Nx(Gz Vq) mM(Kn Pg) IpmP KcjD KkVq OhnO cEkC mTjH} nD{Vp(aK Ar aW Bo bR bX Co Hq Hv Ii Ji Jk Jn Js Kn Ko Lw Nb NN Qy Up Us Vu) oN(As Bg De Je Mv Nq Ra) Mw(bF cE Fr Nv pF Pg) Ip(Af bA cG cJ cV Ny) Ou(Nb Ne Nj Nl Nt) iH(Ch Cx Ky Mx Vt) It(Dc Kq Nv Uh) Nb(oE oF Uh) Je(Et Nw Ok) Ny(Io Ir Iu) Gp(Io Ir) Nl(bB nW) Iv(Nv Uh) Oh(cJ Fb) ChbZ DgNm DipF NtcE MacJ MvhB NjoE PzjD JdOn QudF KnKy UheD bXlN dLoH} nK{pF(Aw Ch Ef Ez Hu iO Mu Nb Oh Qu Qv To Tt Tz Vt) Tv(aM As bG Ii Lw Oi Ou Rf) bF(dE dL Ip Ir Ra St Vt) bZ(dE Ip Iq It Of qT To) dF(Bn Dk Mp Ne Ur) hB(Bg Ch Nt Of) As(Lx oN Qa) Nb(Jl Ou Tn) Ip(bG Ky Tr) cE(Cp Ir Oa) Mw(Nv Pg) Nj(cV Ou) St(bA Ny) Pf(Di Qx) DePg GpIr MhOu NlUc IuNy PzcV KrOh KyqT OkcI} nU{Nt(Bb bF bX dF Kl Ql Sr Un) Ii(DG Qh Sr St Uh Vt Vu) Kk(aM Ed Ik Iu Nj Ra To Vs) Nb(Aj cT cX dF Ky Qv Um) Kn(aM Hb It Mw Pf) Kc(aN cV eD mI) Nx(Ao Qx Qy Wm) aN(cE Nl To) oH(dL dN Ef) Ch(hB pF) Mw(bF Kq) Ra(Nj Nl) Kf(lN Vs) qT(aY Bg) AscX CpNv DkOk EfhB EtKr NeOu QeVs KeNw UhmM dFrA} Jl{Nl(Hu Hw Hx Ii Il Jk Md Me Mf Mj Mp My Nf Nn Nq Om Oy Pc Pg) Ne(Hw Ii Il Iq Jk Jr Ly Lz Mj Mk Nf Nn Om Pc Po) Nh(Iq Jr Ly Lz Mj Mk Nf Nn Om Po) Nc(Js Ly Of Po) Nd(Ij Js Ly) Nb(mS mY) Nj(Ct Js) LyOf MwkG IpkO IqIt VsoQ PanT cImS} mM{Uh(aM cE dF Dg iA iB iO jH jK jL jM jP Kx Oz Pa Pf Pg Pz Rj Uu) Kn(aY cV Ii Ou pF Uf) Kk(cL dG Ij lW Ou) Et(dM hB Uf Ug) Ra(Nx Ok ON) Ch(ON Pg) Oh(bB bX Kr) Ok(aV bW Uf) hB(Di kE Ns) qT(aW bF cE) On(Ef Jd) FrMw MmdF HbJi KceD KflN bWoH} mP{Kk(aM bC cA gP Ip Ir It Iu Ky Mz Nb Nl Ra) Ch(gL hG iZ oH Pf Tn) Vp(bF bS cA Ko nN) Mw(bF Kq Mz pF)

Figure 20 Continued

Nx(Ed Iz IN Ra) Fb(Oh Pf St) oN(Di Ef Vs) Mz(Nl nN) Ne(Ou Tn) Ip(bG Um) Nv(Mp Vs) cA(cE nT) eD(bX cl) IN(Kf Uh) DePg DgNm NloE
TvaM liRm IvNy KcPf KyqT} mY{bF(aM Ao Bc Cp My Nf Of Vp) Ch(hG iH oH Ou pF Tn) Mw(cE dF Fr Nv oN Ou) hB(Bg Cp De Mv Of)
Nl(nW oE Ou Tr) Ou(Kc Mp Nb) cE(aN Aw Nf) oN(Ad De Ra) Ed(Kk Kn) Ii(Rm St) Ip(bG Ub) Je(Nw Nx) Oh(Cp Kr) aY(Kk Vp) bZ(Ef Of) dF(Bn lM) FbQa HbJi PzcV KflN} Kf{hX(aM Cw Dk Ij jE Jt Nt Nu St Up Ut Vt Vv) Oz(iC jF jI jM jV jY lK lO qU qV qW qY) lN(kF kO kP lW mH mI nB nT) jD(Jj Jk Js Nt Og Pb Vv) Aj(eD jE jM qT) Rf(eD jO) Of(gP Ou) lM(Ch Jj) NtOu IimI HbjH JkqX PbjM eDmT} kE{hB(Aj Ao Ax Fw Hu Iz Mv Nt Ra Ss) Ok(Jd Oa Qt Qx Ra Ue) Mw(dF Fr oN pF) aM(bZ dF Kk oN) Ch(bF iZ pF) Pf(Fb Qx Ra) cE(aN Di Rj) cG(cQ Cw kG) Ct(Ou Pg) Vp(aY Ko) DioN FbQa GpSt MpdF NeTr TnLj aYoF bFdL} qT{nT(aE aM aY bF bZ cV Fw Kn Ko Rj Rm Uh) Ky(kF kO mH mT nB nM nN) kK(bA Gp Kn Ra) Aj(gP Pz) Oz(Dg Vt) dB(kC kO) mE(Kk Ko) kN(Bg cV) MzRf RakP KcmW aWmH aYlW bFkG} Mw{Nv(kF kO lX lY mI mS nB nM nN nO nT) Pg(kF kP lW lX lY mI mS mU nN nT) hB(kG lW lX mI mU nM) Fr(kO mE mT mW nO) oN(kN kO nB) bFnB bGoQ cEmS} Nx{Ex(aN Bg Ch Cp cV Cw Ed Ez Hu Iz Jk Kj Ks Mu Nf Nm Oi Pd Rh Ut Uv) Gz(bI Co Mg Of Ub) Vq(Hw Ii) kO(Jd Qx) AaBo} mS{Nb(cE dF Ky oF) Ip(aM bF cE cV) oN(Ef Je Mv Of) aM(bF Kk Tv) Ch(iH pF) Nl(nW Tr) bZ(Ef Nt) MabP NeTr IqOu IrKy OfhB OhbX UhlN} qX{Oz(Aj Bc cJ Dg Kn Ky oE Ou) Aj(gW Kc Kl Ko kQ Lh) Mz(cC cJ Ky) Pz(Ct Ph) ChJp WmcJ KcPb KoPh KymE RfNw} hB{Nj(cF gP Hu Jk Mv Nn Nt Nu Pz) Pz(Bg Cp Ct Mg) Of(Nl Nt Nu) Ch(kC mH) Qu(kO Vq) gP(bI Hu) NtVq iOkG} Ou{Nt(Aa Mb Mm My Nc Nl oQ Pz Rj Vq) Ne(kC kP mW nB nT) Nj(Hq Of) Nl(kO nB) AaUt AdDk NbmE nOlN} jD{Kc(bS Ed Ic iJ Kr Rj) Nt(Fa Ji Ko) Kr(Dg Ko Pz) bG(Nj nO) AjEt WmcJ NuJi NliJ KknO UhOz} jH{Pk(Fa jI Kn Lj) Pz(Aj Ct Ub) cJ(Mb Oa Wm) Kc(Pb Wm) Kr(Ko Oa) Vv(Et Mz) aJ(kK mW) JiRf UhPb} kO{Nl(bB dF oE) oH(dL dN Kd) Ip(bB Uh) Ny(Iv Nf) oN(Ef Je) ChbF DgNm EtHb FbOh KceD KkKy} Ch{oN(kG kP lW mI mW nB nM nO nT) mW(bZ cE Qe Tn) bFkN gLnN kFoH} Dg{Nm(kC kF kK kP lX lY mH mT mU mW nN nO nT) Jt(jO kG) AjrA} Kk{lW(aM Ii Ip Iu Mp) mU(gP Ii It Oi) kG(bC Pf) pF(kF mI) JeoQ mErA iCkK} Oh{Fb(kC kF kG kN lY mW nO) Kr(lW mE mW) nN(aF cQ oE) CpkK bXkG} nO{jE(aM bF cV dF) lN(Bg bX Ji Nl) lK(aY Bg) MphA bPdF dLoH} kC{oN(Ef Jh Mv) pF(Di Kc oH) EtcI NbdF NloE IhRm IpKy IqNy KccV} kK{dF(lK Ne rA) jI(cZ dJ Pk) Uh(jR rA) BniC EtHb NecV aJjL aNcE} Ii{oQ(Dc Kn Ks Vp Vu) St(kP mI nN) Rm(mW nB) FwoO KnlY} Aj{Pz(eD jE jF qV qW) gP(rA rC) ItJi JgrA aCbE} Pg{De(kF kN lY mU mW nM) Ct(nN nT) NtnN} Et{Hb(kF kG kN lY mE mU nM) PjoQ} Jp{Vv(hA jE jR jY lL lN rA)} eD{Pz(Rf Ue) Kc(lW mI) NliJ RfOa} oH{dL(kN lX mI nN) Jj(It Iu)} Ne{Tr(mE mH) dF(mE nN) kGoN} hX{Vt(Nl Oz) iO(bO gP) WmKc} rA{To(kP lX) RjmE UhmH OzcJ} lN{Ji(kG nT) IdlW KcmT UhlY} Nj{Jj(gP iO) OfiJ VqkS} Nt{JnKy RmiO NvnN} Mz{qZ(Jn Of) NljF} Ik{Vq(aX It Ub)} mW{HbNw KjoQ QmUh} Ct{Pz(cV iC)} Fb{Qa(mI nT)} Ji{NuhR RflK} Ny{IqkN ItnN} aC{bE(cV Ex)} aM{cQoQ mTjU} aN{cE(kG lW)} AwMaoQ MvnTiA NliJjY UcKjoO IrbGrZ KcOzjF aLjIkP

Unconstrained panels with 2 analytes, where 1.0E-8 >= 'AUC p-value' > 0. Contains 4 panels of 109,774 total panels evaluated. : Or(kI nJ) Ow(Ng nU)

Unconstrained panels with 2 analytes, where 1.0E-7 >= 'AUC p-value' > 1.0E-8. Contains 8 panels of 109,774 total panels evaluated. : Ow(Kr Mp nJ Rf) Or(kE nC) AjIs IboP Unconstrained panels with 2 analytes, where 1.0E-6 >= 'AUC p-value' > 1.0E-7. Contains 52 panels of 109,774 total panels evaluated. : Ow(Bo cD cS Ct cV fR gP Gz Hw Ib Ii In Iq Is It Iv Js Ky Nc Nf Nl Nt Of Og Oi Oz Pb Pc Pk Po Pz Ql Ue) Or(mF mY nL oP) nC(cE cG dF) Ou(Em nL) nF(Nv Nx) AdNg NlJl QznR QwgP VpnD aCfR bFnL nJoN Unconstrained panels with 2 analytes, where 1.0E-5 >= 'AUC p-value' > 1.0E-6. Contains 194 panels of 109,774 total panels evaluated. : Ow(aA Ad Af Aj Al Ao aW aX aY Ba Bb BC bF bG bI bN bV bX bZ cC cJ cO CP cQ cR Cs Cv CX Db Dc Dd Dg Dl Em Et Fa Fn fP Fw Gl Ha Hb Hf Hq Hr Hu Hx Ij Ik Io Ip Ir Iu Jh Jj Jk Jl Jn Jo Jp Jt Kc Kd Ke Kf Ki Kk Kn Kp KQ Ks Li Lx Ly Lz Mb Md Me MF Mg Mi Mk Ml Mn Ms Mt Mv Mz Na nC Nd Ne nF Nh nI Nj Nk Nm NN nR Ns Nu Nx Ny Oc Om oP Or Ou Oy Pa Pd Pe Pg Ph Pi Qb Qc Qh Qw Qx Qz Ra Rj Ub Uk Ut Vv) Or(mE mS mT mZ nH nI nK nU) oP(aM aN Aw Ct Cw mF Ra) Jl(mZ Nd Ne Nh Nj) Ld(Em fR mF mP nR) Ng(Ba cV hB Ou) mF(cG hB Kf Tv) kI(bF bZ hB oN) Ib(mW nR Ou) nC(aY Dg Tv) nF(Lh On Pg) Kk(mP nI) aC(bE Em) cE(nJ nL) nR(Ch Di) ExNx MzmZ QwhB bFnJ dFnL nAoN Unconstrained panels with 2 analytes, where 1.0E-4 >= 'AUC p-value' > 1.0E-5. Contains 434 panels of 109,774 total panels evaluated. : Ow(aC aD aE aF aG aH aI aJ aK aL aM AN aO AP aQ AR AS aU aV Aw Ax aZ bA bB bE Bg bH bJ bL bM Bn bO bP bQ bR bS bU bW cA cB cE cF cG CH cI cK cL cM cN Co Cq cT CU CW cY cZ dA dB dC dD DE dF dG dH DI dJ DK dL dM dN Dp dR Ed EF Ex Ez Fb Fp Fr Fy gL Gp hB HC hF Hv Ic IH Il Im iO iP Iz Jd Je Jf Jg Ji Jm Jq Jr Ju Jv Jy Kg Kj kK Kl kN KO kS Kx Kz Ld Lh Lj Lu Lv LW lY Ma Mc mE MH mI Mj MM mP Mq Mr Mu Mw Mx MY Nb nD nH Ni nL NO Nq Nr Nv Nw nY Oa oF Oh Ok ON oQ Pf Pj Qa Qd Qe Qg Qm Qn Qt Qu Qv Qy Rb Rc Rg Rh Rm Sr Ss St Tn To Tv Tz Ua Uc Ud Uf Ug Uh Ul Um Un Uo Up Ur Us Uu Uv Vo Vp Vs Vt Vu Wm Tj tF) nC(Ba bF bZ cJ Cv dG dJ dM Fr hB Is Kc Kf Kk Kn Ky Nv oN oP Ou pF Qh Rm Tn Uc Uf Uh Uu) Or(Ct Em In Jk kF kP lY Me Mf mH mI mM mP mU nA nB nD nF Ng nN nT Of) oP(Ao AP As aX Bb bG bS cA Ch Cp cQ Di Ed Fw Kk Uk) Ng(bB Bc bF Bo cE Cu Cw Dc dF Dg Kf Tn Uu) mF(aY bF bZ cE dF Kd Kk Ko Nv Pa Qz Uh Uk) nL(aY bZ cG Fr hB Is Kn Nv oN pF Qh Tv) Ou(Ct kI Mf NJ Nl Nt Nu Of Qw) Is(Ct fR Hw Ib In Iq Ks Ms Ph) nJ(aY bZ cG cJ Dc dF Kk Ky Vp) nR(aF aM Aw bP Dk Fw Kk qT) nF(bF dF Fr Ji Nw Ny Ok Uh) Ib(Cq cV Ji Ky Lh Nj Tn) In(Jn Mt Nc Ne Pg Qa) hB(gP nA Nj Nt Nu Of) Ji(Iq Ms Ne Om) cE(kE nH nI nK) fR(aN bR Cv Nf) pF(kI nK Qw) Aj(Ad qX) Lv(Nc Ne) Qa(Iq Qc) Jl(Ly Nc) Nx(Em mP) bC(aC bF) cG(kE kI) nU(Kk Uk) jH(Oa Pk) FaOg MsMt MzqX NeHw TnnA QzmW KcjD KfhX NwOm UhmM bFnI bZnK dFnH hAmZ mYoN Unconstrained panels with 2 analytes, where 1.0E-3 >= 'AUC p-value' > 1.0E-4. Contains 1,292 panels of 109,774 total panels evaluated. : oP(aC aD aE aF aG aH aI AJ aK An aO aQ AR aS aU aV aW Ax aY aZ BA bB Bc bE bF Bg bH bI bJ bL BN BO bP bQ bR bU bV bW bX bZ cB cC cD cE cF cG cH cJ cK cL cM cN CO Cq cR CS cT Cu CV cW cX cY cZ dA DB DC dD DE dF DG dH dI dJ dK DL dM Fb Gl Hb Je Jf Kc Kf Ki Kj Kn Ko Kq Kr Kx Ky Ld nL Oa Ph Pi Qw Qy Qz Vu) Ou(Aa Aj aL aN aO Bc Bg bI Bo cC cD Ch Co Cp Cu cX Dd Dk dN Fw Gl gP Gz Hb Hq Hw Ii Ik Io Ip Iq It Iu Iv Jh Jj Jk Jn Jo Js Kc kE Ki Kn Kr Ks Ky Lv Ly Mb Md Me mF Mg Mk Ml Mp Mu Mw mY mZ nA Nb Nc Nd Ne NF NH Nk Nn Og Or Oy Oz Pb Pc Pk Po Qc Ql Qn Qv qX Qz Rf Rj St Ua Ub Ue Us Ut Vv) nC(Ad aJ Al aM AP Ax bA Bc bQ cL Cq CU cV Dc Dd dH dL dN Fa Fy Gp Hc iA Ib Ip Jg Jn Kd Kl Ko Kp Kq Ld Lh nR Nw Ny Oa Ok On oQ Pa Pe Pf Pg Qw Qz Rc Rg St To Uk Un Vp Vt) Is(Al aN CH cM Co cQ Fy Ii Ij Il It Ji Jl Jn Jo Js Kg Kj kO Lu Ly Lz Md Mk Ml mP Mr Mt Nc ND Ne NF nH nI Nj NK Nl Og Om Oy Pa Po Qc Tv Ub Ug Up Ur Us) mF(aJ aM An BA cI cJ Cv Dc DG dH dM dN Fa Fr Fy hR hV hW jF Kc Kn Kp Ky Lx Ma nR Nw Ny Oa

Figure 20 Continued

ON oQ Pe PF Pg Qh qT Qw rC Rg Rj Rm St Uc Uf Ug Vs Vt) Or(Aj aN bI Bo cV fR Hq Ib Ic Ii Js kC kG kK kN kO Ks Ky lW lX Ly Mh Mj
Mv mW Nf NI nM nO nR Og Oi oO oQ Pk Pz Qc Ql Qn Qw Qz Tv Ua Ub Us) Nj(AJ aX bA bC bZ cV dM Et FR gP Hw iA iJ In iO Ji Jn Jp Lh
Lu Lx Lz Ma Ml Mt Mz Nc Nf Ng Nv Nw Nx Of Og Ok On Pa Qa Qe Qw Ub) Ji(Aj Ct fR Hw Ih Ii In Io Ip Ir It Iu Iv jD Jo Js Jt Lu Ly Lz Md
Mg Ml Mt Na Nc Nd Nf Nh Nk Nl No Nu Oe Of Og Oi Pc Qa Ql Ub Ue) Ow(Aa eC eD gW hG hX iA iC Id iJ iZ jD jH jY kC kE kF kG kI kP
kR lX mS mT mU mZ nA nB nK nM nT nW oE oK pF qU Ri Tr Tt Vq) Ng(aI aJ Ap Aw bA bC Bg bQ bZ cG cL Co cT Dd dG dH eF Fa fP fR
gL iH iJ iO Jg Kc Kn Kp Kq kS Ky Lh Mt Nl Pg Qh Qz Vq) cV(Aj aV bM Ch Ct Ez Fy Ii Jj Jo Js Jt kI Ks Ly Mg mY nA Nc Ne Nf nJ NL Nu
Of Og Oi Pa Pk Pz Qw Qz Rg Ub Ue Vv) Ne(Et Fr hB Ii It Jg Jn Jp Js Lh Lu Lx Ly Lz Ma Md Ml Ms Mt Mz Na Nq Nv Nw Of Og Oi Ok On
Pa Pc Qa Qc Qe) fR(aD An aQ aY bC bF bI bL bU bX cA cD cE cJ cQ cX dB Dc dD Et Hv iH Ii In Mp Mw Nc Nd NI Nw Og Oi Pz Qw) Ib(Ad
Bo Dc Dd Ef Et Fa gP hB Ip Jn Jp Jq Kf kN Lx Ml Mt My Mz Nk nU Nx oH On Pi Pz Qh Rg Rj Rm Uc Vv) nL(Cu Dc Dg Fy Hc iA Jg Jl Jn Kf
Kk Kl Ko Ky Ld Lh Ma nR Ny Oa On Pf Pg Rm St Tn Tr Uc Uf Uh Uk Uu) hB(aP Bg bl bQ Ch Cp Dk Hc Hu Ii iJ Jk kE Mg Mp Mu Mv Mw
Nd Nf nH nJ Nl Nm Nn Og pF Pk Pz Qu) aC(AA Ad aJ aL Aw aX BA Bo bX bZ CT Dc Dd dF dG dH dJ dM Ex Fr My Qz) nJ(Al Ba CU Cv
DG dM dN Fw Kc Kf Kn Ko Ld Nx pF Qh qT Rm Tn Tv Uh Uk Vt) Nc(dF Et Hw Jj Jn Js Lh Lu Ly Lz Ma Ms Nd Ni Nk Nw Of Og Oi Ok Pa
Pc Qa) Nl(bA Et Hw In Jn Js Ky Lh Lu Lv Lz Ma Ml Ms Mt Nf Nq Nw Of Og Pa Pc Qa) nR(aJ aN AS Bc Bn bX Cp cQ Dc dL iO Kc Mw mY
mZ nF Nt Pa Pd Pe Qw Uk) Pg(Ii kE kI kO lW Ly Md mP mY nD nH nl nK nN nT nU Of Og Oi Om) nU(Aj An Ax cE cJ dE dF dM Fw Kc Kn
Ky Nx Qw Qz Ra Uh Vt) Et(Aj Ct Hb Hw Jo Jt Kk Ks Ly Ms Mt Nd nF Nk Og Om Ue) kI(aY cE Cu Dc dF Fr iA Nv Oa Pa Pf Qh St Tn Tr Tv Uc) nF(aY BA cE cG Jg Jl Jq Kk Kn Ma Mn Mz Oh oN) Qa(Aj Hw Ih Js Li Ly Lz Md Nd Nf Oe Om Pe Po) nH(aY bF bZ cG cJ Kd Kf Kk Kn Nv Nx Oa oN Tv) Ky(Dd gP Ik Jj Ml Mw Nt Nu qT Qw qX Ue Ut) dF(aO bC Ct Dk kE lW Mp mY mZ nD nK Nt) Qw(aN eF iA iH iJ In iO Jp Nk oH Ub) Kf(Hw jD jH Jt Nt Og Om qT qX rA Ue) Ct(BA cE cG Jl Jp Lx My On qX) mY(aY bF bZ cE cG Kk Nv Nx Uk Vp) Aj(bZ Dc Iu Jn Jp Mt Pz qT rA) Ly(Fr Jn Lh Ma Mt Nw Ny Pa) Jl(Iq Js Nf Nk Of Og Pc Po) Nv(kE kO mP mZ nA nD nI nN) cE(aD aO bC kC kO mM mZ Og) cG(bC bI kG mM nA nI nK Nt) Mz(eD jD jF jH qT qZ rA) In(Af Nh Nx Oa Pa Qe Vq) Nw(Iq Lz Md Ms Nd Nk Po) Jn(Hw Ms Nd Nh Us Ut) Og(bB cL Oa Qn Vq Vt) bF(Bc kC kE kO nA nK) gP(hX Id Jj Qz Rj Uk) mZ(aY bZ Ma Pa Qh Tn) iC(bS cA jD jH Nb Pk) qX(aI cJ cQ dA Kc Ph) Em(aN aV dA Nb Ok) Lh(Hw mP Ms Nd Om) Nx(Gz Js kO mM Qx) Vq(Hw Ik Ub Ue Uk) nA(bZ Ny pF qT Vp) jH(cJ Ra Uk Vt Vv) oN(kC kE kO mM nK) Nh(Hw Lv Of Pa) aY(kE kO mM nI) bC(bA cT cX Dc) qT(mE nK nN nT) Fr(kG mP nD) Mt(Hw Ii Jt) Nd(On Pa Qe) Ny(kO nD nK) Om(Fa Jg Ok) hX(Kc Rg Vt) jD(Fa Uh Uk) Jj(bI Dd) Jp(Ch Co) Jt(Dg Ok) Kk(lW mU) Of(Jg On) bZ(kE mS) mP(nT Vp) AfdB BcUb BoaM MyaN UeUh TvnK PzUk QcQe QzkN KcrA PfmT PkjI cJkO cQoQ dGmW iHiJ

Constrained panels with 3 analytes, where 1.0E-10 >= 'AUC p-value' > 0. Contains 3,594 panels of 16,766,520 total panels evaluated. : nC{Or(aL aM aS aY Bc bX Ch cJ Cv cZ Dg Dl dJ dM Fn Ib Ir Is Kc kI Kn Kz Ld Me Mh Mv Mw mZ Nb Nc Ne nJ Nl Oh oO Pk Pz Qe Qm Qv Qw Qz RA Tv Uh Uk) Qz(aY Ba bF bZ cE cG Cq CU cV dF Fy hB Ip Is jH Ji Jn Kq Ky Lh Lv Ma nR Nv Nx Ok ON Ou Oz PF Pz Qh Tn Tr Tv Uc) Ib(Al aP Ba bF cE Cq Et Fy hB Ih Im Ip Is Jg Ji Jm Jn Jq Lh Mn Mt nR Nv Nx Ok ON oP Pg Qe Qh St Tn Tv Uh Uu Vu) Uk(Al aY bF cE cG cJ Cv Dc Dd Dg Et hB Ir Is jH Ji Jn jT Kf Kn Ko Ks Mn Nh Oh Ok Ou Ow pF Pg Qe Rm Tv Uf) oP(aD aF aM aN Ao Ap Ar As Aw Bc bI Ch Co Cp Ct dE Di Ed Hb Iz Jd Je Jv Ph Qw Qy Ra Vt) cE(aN aU aV Aw aY bI Ch Cp Ct De Di Ir kI Lj Mh Mp Mw Ne Ng Nl Nt Oa Of Qm Qw) Tv(aM aY BC Cv dJ Ii In iO Ky mF Ne nI Oi Ok Oz Pf Pz Uh Vt) Is(aZ Ch Cp Ct cX De Fn Ha Ii Kc Kj Kn Kr Ph Qw Rf Tt Ug Vv) Nl(aY Ba cG cL dF Dg hB Kl Kq nW oF Ou Tn Tr Uc Uh Vt) bF(aM Ao Aw Ch Di Hc Hu Jh Ld Mw My Ne Ng Oa Qw Ra) hB(Aw Bg Ch Cp De Di Ef Hc Hu Iz Jd Mv Mw Ng Of Qw) dF(Ch Ct De Di kK Me Mp Mw Ne Ng Nj Qm Qw) nR(aS Bc Ch Ct De Di Kc Kk Kn Ld Qw) Ip(Af aM aY bW cL dJ Ky Ou Uf Ug) Ow(aM aY Ld Mh Mt Oi oO Oz Pc pF) Ng(Ad Ba Dg Ef Fy oN Tn Uf Uu) aY(Di Hc Kc Kk Kn Ld Nj Pz) oN(aS Ch De Jh Mw Ne Qu Qw) pF(Di Kc Kk Kn Ld Mw Qw Vt) Ct(Kn Nv Nx Oh On Pg Tn) Dg(cX Ii Jt Mh Mw Nm Oi) Ok(cI Fn Hb Jd Qm Qw Ra) Mh(Kq Ky Uc Uh Vt) Ne(Fy Ou Qh Tn Tr) Hb(Et Ji Lh Nv On) Oi(Kf Kl Kn St Uu) cG(Dc Hc Mw Nj Pa) Qw(iA Jl Ou Pf) Ky(Ir Nj Oh Pz) Ld(mP Ou qX To) Nx(Je Qx Qy Ra) On(De Dk Jd Qy) Ii(Kn Nv Rm) In(Fy Pi Rm) Kc(eD mI Qh) Oh(aW Fb Kr) Oz(Hc Kf Kp) oQ(BG cQ) Ch(gL Tn) Et(cI Fn) Mt(aM Vt) Mw(Nv Qh) Ue(Kn Ko) St(Gp Ha) oO(Ou Rg) FnVt FydL TnJk IrcL PzcX QeVs JeNv JiQm KnnU OadJ PfcI dMeD} nR{Ib(BA bX cQ cT Dc Dg dI dM Et Ez Ih Im In Ip Ji Jn Jp Jq Kc kE Kf kI Kk Kn Ko Kp Kq Ld lK Mk Mm Mw Mx mY Nb NJ nK nL Ns Nt Nv Nw Oe Of OH Oi oP Or Ow Pa Pd Pk Pz Qb Qv Qw Qz Rm St Tv Tz Uh Uk Un Up Uv Vu) Ch(bE Cq cZ dM Et Im iO Ip Is It Iu jP kE Kf kI Kk Kn Ld lK lN Mw mY nA Nb Ne nH NJ NL Ns Nt Oh oP Or Ow Pa Pd Pg Pz Qz Rm St Tv Up Vu) Ld(aM AO As Bn bP Cp Ct De Ii In Iz Jk kE kI Kj lN mF mP Mv Mw nA Ne Nf Ng nH nI nJ nK nL Nt Of Ow Qz Tt Ub Up Uv) lK(Ad aK aM aO Ap AS aU aV Aw aZ Ba Bb bF Bg bM Bn bP bQ bZ cE Co Cp Ct cY dA De Di Dk Ef Fb Gl Iz Ke Kj Kl Ph Ra) Ow(aM Ct Hb In Jk kI Ks lN Ma Mg Mp Mw nA nB Ne nF Ng nJ Nn Nt Nu Oa Of Qm Qw Qz Ra Tt Ue Uk Vs Vt) Qz(aM aN Ao bN cF Cp cT cV cX De Fw Hu Je Jk Kj Kn lN MF mM MU Mw Ng nH nL Nn Nq Qy Ra) lN(aF aS Aw Bn bP bX Cp cQ dA De Ef Kc Kf Kn Ph Ra Uh Uk) nL(Ad aM Bc Ct cZ De Di Dk Ef Hb Kc Kj Kk Kn Or) qW(aL aM aN aO aU Aw Bn bP bQ cB cE cY cZ De) qT(aF aO As Aw bI Bn Cp Ct Di Dk Ef Iz Kj Kr) Mw(aJ aM dG Fw iO Kc Kf Kk Kn Or Uh) aF(eD jF jK jP jQ jR lL lO Of qX rA) jI(aO As Aw Bn Cp De Dk Ef Hc) Ne(aN cV Fw Or Qw Ra Tz) In(aS bP Dc Di Fw Kn Ra) Kk(Nb nF Ng nH Nt Of Tt) Kj(Is Iu jU Oh rA St) Nt(Bc Fw Kf Ko Kp) Ng(iO Kc Kf Kn) Qw(aM De mF Or) qV(aL Aw bP cZ) Bn(iC jP jY) Cp(jU Oh rA) Di(bC Ub Up) Kc(eD mF nF) Aw(jP Up) De(iC nH) Fw(Ii jE) Or(kI Me) eD(bI Uk) nF(Fb Kn) DknK NcaN TtKp KeNw} oP{Ib(aH AN aP Ba bB bG bZ cP cQ cV Dc Dd Ed Ez Fw Fy Hw Hx Im In Ji Jl Jn Jq Jr Js Ju kC Kf Kl Kk Kn KO Kp Ks Ky Lv Ma Mf Mm mS mW Mz nA nD Ng nH nI nJ NK nL Nu Ny Oa Oh Om Or Ow Qa Qh Qv Ra Rm Sr To Tz Uh Uk Uv Vo Vu) Or(aF AO AP As Aw Bb Bn Bo bP Ch Co Cp Ct Cw De Di Ez Fb Fw Hu Ii Iz Jd Je Jh Jk KE kG kI Kj ME mF Mk mM Mp Mv Mw My nA Ne Nf Ng nH nI nJ nK nL Nq Nt Of Om Pb Po Qw Qz Ra Tt Uk Vs) Aw(aM bF bG Ed Fw Hv In Jl Jn Jp Kf Kk Kn Kq Ky Ma Ms Mu Mz nA nD nH nJ nK NU Nv Oa Og Oh Ok On Ou Ow Pa Pf Pg Qa Qh Qz Ra Sr Tn To Tr Uc Uk Uo Wm) mF(Aj aM Ax bG Ch Di dL Ed Hb Id Je Kj Kk Ko Ky Ld Qt Qw Qy Ra Ub) nH(aM Ao AP AR As aY Ba Bb bI Co Cp cQ Ct cV Cw De Je Ph Ra) Cp(Ed kO mS Mz nA nD nF nJ nL Nv Oa On Pa Pe Pf Pg Qa Qh Wm) Ow(aD Ap Bb Ct Cw Hb Ii In nF Ng nI Nt Nu Oa Qv Ra) Fw(Ct Ii In kI Kj nA Ni nK Nt Nu Po Qw Qz Uk) nL(aD aM Ao AP Bg bZ Ct cV dE Di Hb Je Ra) Ng(aN bB bG bU Je Kf Kk Qz Rb To Uk Uu) Cw(Et Kf Kk Kn Ko nJ nK Og Ok) Di(aY cV Ed Ms nI nJ Pf Ra Uk) Ii(AX Dc Kf Kk Oa Ra Vp Vu) In(aN aP aX bP bS cA Ed Kr Ra) nK(AP Ar As aY cV Je Ra) Ed(aF Dl Fb Kk Nu Po) nA(Ao Ap bS Fb Je Ra) bG(Jk Nt Nu Of Qw) Fb(nD Oa Pa Wm) aP(aJ nB Ne Qz) Ap(kI mS Qz) Kj(Pf Qa Vu) aN(aM As nI) Nm(Dg Dl) cQ(kO nJ) nI(aF Kk) AnaM AsPg ChMa NtKq NuaY JenD KeNw UkmE} mF{Qz(aC aF An aY BA bF bQ bZ cE cG cI Cq CU cV Dc dF Fy Gl hB Is Jl Jn Jq Kf Kk Kn Kq Ky Lh Lv Lx Ma Mt Mz Nv Nx oE Ok ON Or Ou Ow PF Pg Qa Qh Tn Tr Tv Uc Uh) Or(Ap bX Ch cI cJ Cv cZ Dg Et iB iC Jg jT Kc Kd kE Kf kI Kk Kn Ko Kz Ld lK Me Mh Mv Nb Nc Ne Nf Nh Nl Oh Ok oQ Ow Pa Pk Pz Qw Uh) Ld(aY bF bQ bW cE cG cL cO dF Fr hB hC Is Ji Kf Ky Mn Mt Oh ON Ou Ow PF Pz Qa Qe Qh Tv Uf Uh) hB(aN Bg Ch Di Ef Hc Jd Jk Kj Kr Mu Mv Mw Ng Nl Nq Nt Of Ow Qt Qu Qw Tv Uk Vs) Ow(cI cR Fn Hb jD Mh Mr Mt Nl Nr Og Oi oQ PF Ql Qm Tv Uk) Tv(aM As bC bW dK dL Ib In iO lK Ne Nf Nw Ok Pf Pz Vt) Qw(aY bF cE dF hG

Figure 20 Continued iA Jl Ok ON oQ PF) Kk(aM aY bC bF cE cG cl dN jD Kd Mh PF) Kf(aN bF Hw li ln jD jM Mh ml Nt Oi Uk) Uk(Al bF cE cG Dd jD jT Kd Oh Ok) cE(aN cl Di Ib jP Mw Ne Ng Nt) bF(aM Ch Di dL Ib Mw Ne Ng) cl(Ib iO Ky Nw Ok Pf Uf) dF(eD jD jE jP Mw Ne Nl) Kc(eD Is jD IN ml Oh) oQ(aN cQ dE Je Ky Ou) Kn(iC jD lK ml Pf) Is(Ch Kj Kz Vv) Kd(Dc ln jE Rg) Ky(Mh Oh Pa qT) Mw(bZ Nv pF) aY(jE jF Pz) Ch(gL oN) Di(PF) Mt(dL Rg) Ne(Fy Ou) Nj(cG Ug) Ib(bQ lp) Nv(nF Nt) Uh(jD jE) DgNm UeKo InPa HbLh IpUg KrOh RgoO RjjD NxOa Pfd Ur Vs) Qz(bL Dc Dg Dk Ir Jg Jl Jp Kf Kl Kn Qa) aY(Bc Dg Ib Ir Ko Mh Nw Pa Qw Uu Vt) hB(Je Jh Jk Ld Mu Ne Nj Oz Qu) Tv(Bn bW dE iJ Lw Nf pF Uf) oN(Cp Ct Di Ef Jd Je My Ra) Ib(Ao bA cL Lx Mf Pz Uf) Ok(aL Ct cX De Dk Je Qx) Nl(cV Gp Ky Ow Qh Uf) Ir(Ba cG dF Qg Uh Ur) Qe(cI Cp dJ Fb Kr Qw) Oz(Dg Kc Kd Kk Ko Uh) aM(Ji Kk Kn Mh nR Uh) pF(Bc Hc Kf Nj Or Uh) Hb(Dc Kf Kn Nw Uh) dF(aS Bn Mh Nb Nf) oQ(aN Ar cV dE Je) Ng(Al Kf Kl Kn) Pz(aN cL cV jD) cG(Ip Kk Mh Ne) cI(Dg Oh Uc Uh) dJ(Dc Oh Qa Qh) Ct(Ba Ip Lh) bF(Lj Of Vt) In(Kd Ld) Je(dM oO) St(Ik Ur) Qw(Jp On) Kk(Oi Pb) Kn(Ky Md) Nv(Mp Nt) Uf(Mw Oi) cX(Et Kc) nR(cZ Ef) BaQm BcMh DcIi DgUe FyKj GpNe MtdL NbTn NcOu NjcV HcPc ItNy JdNx QhdI OhdE OrqX PacJ dMjH} Ow{Ng(BC Bo bV cR cS Dg hB Iv Jl Kk kN Nk Pb Qh Tn) nR(Aj aN Ao Bg Cp De dK Ii Ij Iz Jh Jo Lj Mv Qy Wm) Kr(bI cV hB Is Je Ml Oa Of Qa Qx Qy Ra Rm Ub Ue) Mp(aJ cV dF Fa hB Ib Jp oP Qh Ql Rj) Rf(CV Ib Is Jn Nf Of Oy Pb Pc Qx) nF(bZ cE cG cR Hw Ii Ky Ms Mt Ue Vp) Oz(aX bC Bo Ib Iv jD Kk qX) nU(Aj Jo Nl Oy Pc Qw Ub Um) Ct(Ad cV gP Iv Ky My Uu) Nt(cV fP hB Jn Ky Lx Pc) Pb(Bo Gz Hf It Js Oi Ue) Ib(Ad aX cV Jp My Tn) Of(Bg fP hB My Pz) Em(Iu Kd Nm Oe) Gz(bI Ii Nf Pc) Js(cS Nf Og Pi) fP(Ch Co Mg Mv) Po(Bo bZ Is) Ql(cV Jn Pc) mF(iZ Nm Ok) nJ(jH Mw Vt) Mg(cV Pz) Iv(Ky Mk) Je(nN oQ) Oi(nD nH) gP(Bg cH) mY(aY iZ) nB(bZ Ma) hB(Ch Nu) BoPc ExNx NenT NfPz InnD IsnA RamI QwpF UkVq VpmP bVfR cJkC eCnK} mF{Or(Ba bF cE dM dN hB Ip Jp Ly Mb mT mZ Og Uk) Qz(cJ cL Dg Mh Mn Mr Og Oz Qd Rm) Uk(cJ Dc hA Is Kn Ko Ld Nx Pe Pf) bF(Ax Hc mM Mv Nl Nt Qm Vt) Ld(jF Jp Og Ok Oz Pk St) cI(cG dF Dg In Kf nW On) Kk(iC Is mI Nb nR Uf) hB(bS Dk Hu Ii Je Nj) Kc(cX dF jM pF Qh) bZ(Ch Di Nt oQ Qw) cE(Ch Ip jE NL) Mh(Dg iO Kq Uc) Is(Ct Ug Um Ur) Kf(cX eD Mw Nm) Lx(As Ib Qw) Ne(aY oN Uc) Nl(cG Uf Uh) Tv(iC Il Kz) Pa(jF Kd Ko) nT(dG iA Uf) Hb(Ji Kn) Ir(Ky Qg) Nv(In Qw) Pf(oH Pk) dF(Me Mp) AjPz BaNg CtOh DcIi DiKd FnOk NmKo NtQa NuoP StJj KnKy UhnF aYiB dMjH} nR{Ch(aJ aN cI Fw Jn Kc Ko Ky Mz oH Ra Uc Uk) Ib(Bb cH Cq Ef Fw Id Nk Sr Ul Vt) Kk(bP Iz mM nA Ne nJ Nl Nu Ub) Ld(bM Ed Ef Hb Ks nF Nm Or Rh) Qz(aA jH My Ne Nj Oz Ub Uk) Qw(aJ dG dM Kp lN nL Pz) Mw(bW cH dM Fa Ko Ra) Nt(aF aM Dl Kc Kn) Kj(cZ Ip Ir Kf nF) aN(aS In kI Me mZ) Ra(Me nL qV qW) lK(Ao Hb Hc Nq) De(Fw mY Pg) Di(bW Of oP) In(aF Bo Kf) Uk(Fw Ne nL) qW(bE Cp Ef) Ad(Pz qT) Or(aF nK) aM(kE qV) nH(aS Kc) nL(cI dE) jI(Ct Iz) AwKp AxNb DgNg FwlM NecT TtKo IiKf KnQm aJlL} oP{Cp(bG cV Fw Hv Jr kC Ky Lx nK NU Ou) Or(cH Dk Dl In Jf Oa Oy Qt Qu Qx Qy) Aw(aI aY bB bZ Et nL Nm Ub Vp Vu) Di(Fw Ii In Jl Jn Mz Nm Oa Pa Ub) Ib(bF kE nF Nm Nn Ou Un Vp) Cw(In Mz Nu Nv On Pa Pg) nH(Fa Hb Iz Qy Qz) Ii(aM Cv Kn Qw) aP(mP nJ Oa Uk) Fb(kC nF nI) Qz(aX Ed Ms) Kj(Dc Ma Mz) Kk(Hb Kg mM) Ap(Dl nD) As(nJ Vp) Wm(cJ cQ) Fw(Nk Oz) Nm(aZ Cv) Ra(aX Nu) Kr(mP Oa) aM(Jr Nt) bG(Iz nA) nK(Ao Ed) BgEf ChbZ CtaX DdIn GlMz MwbB NgTn JcnI JlVs OunA aFnL aNaY} nL{cE(Hb Ii Ir Ne nJ Nt Oa Of Oi Or Qw) Ou(De Ip Kc Kn Mw Nf Oz Qm) bF(Di Lj Md Mw Nb Po Qw Ut) Tv(aM Bg bZ Is Ma Or Pf) Qz(aY Ch Dk Jy Nx Ok Pf) Uk(Cv Dc Kn Oh oN Qa Qh) hB(Iz Jd Jk Mu My Nn) pF(Hc Nd Ne Nl oH Pz) Or(dM Ld Lv Qm) oN(aS Bg Ct Je) Ib(Pz Ut Uu) Is(Aj bX In) Kn(aY Ma Pf) bZ(Ng Of oQ) dF(De lM Nb) Tn(Jk Qw) Ra(Jp Nx) Nv(Ct nF) Oi(Rm Uc) On(Dk Jd) cI(iO Jp) AlIn ChMa FyNe GpSt NloE IiQh HcaY IvNy JfNx KcmI KyOh UhiJ} kI{bF(Hu In Is jD lO Mw Nt Oa Qy Uk Vt) hB(bS Dc Hu Iz Jd Je My Nn Pa Rj Wm) pF(Ef iJ Jh Mu Mv Nf Nw Qt Rj) Ou(Ct Ip It Mh Mw Nj Oa Pf) oN(Bb Hu Je Mh Mu Nl Nt Ra) aY(Bg Dc jE lN Ma Oh Tn) bZ(bS Jh My Oi Qw Qy) Is(bX Je Kc Ql Qw) Pf(Ar cQ Di oH Rj) cE(aN Qw Qz Uk) jH(bL cS dF Ra) Tn(jD Kd Ld) In(Dc Ld St) Oa(Ch gP iP) Ma(Qm Qw) Tr(Ld Mh) Oh(Bg Ky) Ok(Pj Uk) AlUk NfTv NjoF NlnW IbUt QagP JeNv QwJp OrnI aMjD nTiA} nJ{Ky(aM Cv Dc Et Kk Nj Nt Oh qT qX Rm Vp) Ou(aS Ip Kk Mw nT Qw Us) Ib(hB iB Jm Mn Nv Nx) In(Al bF cJ Dc Kk Ld) Is(aM aZ bX Rb Rf Uo) bZ(Iq Ld nT Of Qu Up) oN(Ad Je Jh kG nT Up) Uk(aY cE Et Ip Nw) bF(Dc Ng Nt Up Vt) Qz(Cu Dk Pf Tr) Nx(Qx Qy Ra Rb) cE(bP Cp mM Qw) hB(Ii Mv Of Qw) Oh(aM Cp Kr) Pf(Kk Ld Qw) Ng(Ba Dg) Kc(eD jD) Uh(Hb Nt) Oz(Fw Vp) dF(Iq Nb) DkOk EtdE NjnW IiKn PzcV RaqT KfOi OrbC VtaY dNoH nTpF} nF{cJ(Et Ik Ky Nx Ou qT rA Uh Um) Uk(cG Cv Nw ON Or Ou) Uh(aY Mw Nt nU Ou Pa pF) Nv(Cp Je Md Ng Nt Qz) oH(cG dL Ji Kd pF Qe) On(Ib Je Md My Nt) bF(Ib Kc Mw Ng Qw) cE(Cp Kk Mw Qw) Cp(dF Is) Ib(Nw Pg) Qz(hB oE) Jl(Ip Nj) Kk(lW Pf) Nx(Uo Tj) qT(Gp Ny) oN(Qu Ra) FbdF LvKc MpiH MzNe NlOu IiKf IsUr JeNw JiOr KnPf bBcI} Or{kE(aJ bZ Dc dF Gp Is jI Jn kF Kl nI Nw oE Qa Qd St Uc Vp Vu) nA(bG bS bZ gP Jg Ld Nc Ni oE Pf Uh) nH(aM Cv Is Kf Mh Pb Pk Ra St Tv Uh) nU(aF aL In Mb mT Mv Nf Qv) nK(aM bX Jg Ld Nc Nl Qx) mZ(lK nI Oa Ub) mE(Is Pf Pk) nD(cJ In Nb) nI(Ld Ok) NbmT IsmY aFkF nOjE} nA{Is(Aj bS Cp Cv Kn Qg Ua) oN(aM My Ss Uk Vt) pF(Bc Ef Et Mv Qz) Ng(bZ Kq Tn) bF(Mw Qw Ra) Tn(bC Ld) Ok(Jd Uk) Ou(In Uk) bZ(dE Mv) cE(Nt Qz) ChhB EtaY MacJ NjoE NldF IpKy VtoH PfcQ bAkS} nH{Is(Aj Ih In Ph Tt) Qz(Al cU Fy Lv Vp) Uk(Kn Ko Nx Oh Qa) Ne(bF Fy Tn) oN(aS Ib Jd) In(Fy Pi) Kn(Ii Pf) Nx(Bb Co) cE(Aw Qw) oQ(bZ cQ) MpdF TvPz JeNv KrOh OfbF} Ib{mW(aJ Bb cG cN dG Jd Jk mY Pz Ua Uc) nU(Kc Ld Nb Ns Rg) mP(oN Pg) kE(aO Ua) kN(cL Ld) CqnI PzeD QanT JijD StnK QwgP dFlW mYiH} Qw{gP(Bc cH cX hB Ky Ml Nc Ne Ng Nj Nk Of Ou Qa Ra) kE(bF oE oF Ou) nU(Ky oH) GzoH NghB NjiA PfmP bFnI nDiH kGoN} Is{nD(aC Cq Kn Pk Uk Vv) mS(cA Kr Rf) kC(bX cH Kr) Aj(Hw My) mP(Kz Ld) EmLy FbmY TtkE InnO KjmZ UkmE cHlX} nI{Kk(cE cG cI Oh) bF(aM Ch Di Ld) Mw(dF Nv) Hb(Kn Lh) cE(aN De) BaNg NeTn TvPz QzaY KnPf LdmP} nD{Et(cI Uk) In(cJ Pi) Ip(aY bB) jD(Kc Uh) oN(Ef Qu) pF(Kk Ld) GpSt HaVp MwdF} nU{In(Dc Kf Kn) Nt(Kf Kn) Ng(Kf Qz) Ld(mP Qx) MwcE IiRm QzKk KndE NxUk} mM{Et(cE Uk) Kn(dG hB) Nv(As In) qT(dF Gp) NeoN QzOn QvhB KkbW UhbL} Em{Ou(cA Gp Gz Iu Jk Kx Na) LvaD NbaC KlOk KnNx KqaV} mZ{Uk(cU dF Ma Pg Qa) Jh(bF On) MwMz NgbZ QzcV OaoN} nK{Mw(bF bZ) Tr(cI Nl) pF(Fr Na) EfbZ GpSt JhbF LdcV} Aj{qX(Ad Dg gP Kf Mz Uu) Kf(lM rA) PzrA} kE{hB(aN Kj Qz) ChOu TvoE IrKy aYjI cInW dFeD} fR{aN(aC bR Oi) Ld(Cs Mq) IlqW NxkQ aCaV} kO{Jd(ON) FyIn MwhB IpKy ItNy QzNx QuoN} Ng{My(Ad Bc) EtKk UcjE PzcV KojH} mP{Mw(Jl Nv Pg) IpcA IqNy JpLd} Kf{jD(Nm Rf Uk) InkG mTlN} mS{DipF MwoN NbKq NlOu IpKy} Ex{Nx(Hw Jj Oy Ub)} Qz{mW(cG Jq) bZkG jIkK} nN{In(Nv Qa) Oh(Cp Kj)} mY{cE(Cp Uk) MvoN} qT{nT(dF Ra) TomE} kC{NbOu NldF JdoN} Pz{OfhB UkhX} Jp{Vv(jH qX)} nO{jE(Bg Ou)} lN{KckK UhnB} DgNmkG NbKklW NjiJjD IiKnmI KomErA LdbWmW PkaMjH

Constrained panels with 3 analytes, where 1.0E-8 >= 'AUC p-value' > 1.0E-9. Contains 2,577 panels of 16,766,520 total panels evaluated. : Ow{Mp(aX bC bF bI bV bZ cR cS dL Ij Jj Jl Jn mF mP Nk Qn Ub Ue Uf Uk Vt) cV(aW bI Ch Gl Hw Ii Jk Jo NF Of Oi Om Oz Ph Pk Po Qm Qw Qz Ue Vv) Pz(aX cR cS hB Jj Jk Jo Ks Ky Nm Nu Or Oy Pb Pc Pd Po Qw Qz Ub) Ct(bF Bg bZ cE cS Is Jn Jp mF nF Nk Nt oQ Or Oz Pc Ql Rj Ue) Pb(gP Hw Ib Ii In Iv jD Jo Kk Ks Ky nC Nf Nm Nu Og Qw Rj Tv) Oz(cS Hb Hw Ij In jH Nf nJ Nu Og Oi Om Pk Qx Rj Tv Ue Ut) Kr(Ao bV Co cR dE dL Hu Ik Jd Jn mF Mg Mk Oy Tj) Po(bF cR cS Em Fa fP hB Jp My oP Or Pc Qa Qh) Ql(Ib Is Jl Ky Ml Nc nR Oa Qx Ra Rj Ub) Nt(bV cS Et Jl mF Ml Nf Qa Qx Rj Ub) Rf(bI cX gP Ji Ky Lj Mk Qy Ra Ub Uk) Oi(aX bV Jn mP mS mY nA nI nK oP Vq) hB(aO Bg Co gP Hc Js Mg Mv Nq oN Qc) oP(aN Cp Di kC Mg mM nA nK Nm Qx) Ib(bI Is Jh Pk Qh Qx Ub Uu Vq) Js(bI bV cR cX Jl Jn nJ Qh Qy) mF(Ii In Ky Ly mI nN Pc Qv Ug) nI(aY bF cE Ii jD Ky Nl Nm Pf) Nf(Bo cS Em Ky nR Nu Pc Ue) nF(dF Kc Mz Nm Tr Tv Uh Um) Em(aC Cw Gp Hw Jt Kx) Ii(cR Fa Jn Jp oQ Pc) Is(Ha Hw Jo kC Ks Up) nR(Ax dE Ef Mh nK rA) Ad(Aj Jo Jt Mg Ue) Gz(Ik Li Nx Og Ub) Jp(Co Gl Jo Mg Of) Ky(gP nC Nu Qx Ue) cS(Jo Mg mY Nm Ue) fP(Bg Hc Jo Nq Qu) nU(Ch Cw Hw Kj Nn) nD(aY cQ Ok pF Vp) My(Aj Cp Jk Mg) Ng(Cv cX iO Vq) gP(bV hX kI Qu) mM(cL Nw Nx Uf) mY(cR Je Nm Qm) nA(aY bF Jy Tr) oQ(Bb bG cQ Nu) pF(kC kO nH Of) Iv(Jn Of Oy) Qa(nN Qb Qc) Pc(aX Pk Ue) nC(Fn Mr Ok) Iu(Aj mE) Qx(Rj Ue) Jk(Bg Jl) bI(Ij Pk) bZ(kI Of) nN(cQ iC) nJ(cU dJ) ChkN CvfR GlcX NucR MhnH NemI UbQw HwJn InnT JlVv JoKf UgmE VpnB VtjD VqPd eDmP jIkK} nC{cE(AO Fn Hb Hu Ii Iz Jd Jh mF Mg Nb nF Po Qy Vt) aY(cQ Cv

Figure 20 Continued

Figure 20 Continued eD(cJ Kn) CpPf lpbS ltNy IvKk KeNw dLoH} jH{Oz(cJ Kf Uh Vt) Pb(cJ Kf Vt) Vv(Kf Ko) Pk(Ra Vt)} kC{oN(Je Mw Qu) ChbF FbSt ltNy JdOn KdoH} qT{Oz(cJ Uh) nT(bG Qh) kK(dF Kk) KcmI} oQ{Mw(Bg bZ) li(Fw Fy) ApEt EdNi KeNw} Ch{mW(Qa Uf) bZmY gLmU nTiA iHkF} Uk{Oh(nN nT) DdmE KnmI eDmH} mY{BgoN liKf HbLh JeNv dLoH} kO{CpoN lnNv lqNy UheD oHpF} mS{lp(aY bG) MwbF NbaY} rA{AjEt JiRf KymE UhOz} Em{Ok(Jo Ly) KdLd} Kf{hX(aO Oz) VvlM} mW{NeUh KkbW LdUf} jI{kK(aY dI Kn)} kG{bF(iO Ne) KnPf} Wm{cJ(jM qU)} In{StnN PimT} DePgnT NhnOIN QvVthX OhaMnN dLIYoH Constrained panels with 3 analytes, where 1.0E-7 >= 'AUC p-value' > 1.0E-8. Contains 4,168 panels of 16,766,520 total panels evaluated. :
Ow{lb(Bc Bg Bo bV cJ cR cS Cw cX Dc Dd Fn Hc Hf Jl Jn Kf Ki Kk Mv Nk Nl Og Qn Qz) Pb(Aj aX bI bV cR cS Ct cV Fn Hb Ij Ik jH Jj Mg Of Om Ph Pk Qc Qx Qz Ub Ut Vq) cV(Aj aL aO Co Cp Dk Hb Hq Ij Ik In Iz Jj Kc Ky Mf Mk Mv Nn Oy Qx Ra Rj Ua) Pc(bI bV cR cS Hb Hw Ij jD Jo Kk nL Nu Of Og Oi Ph Qw Qx Rj Tv Ut) Pz(Aj bI bV Ch cX Hb Ij Ik Kk Mk Ms Oz Ph Qm Qx Rj Tv Ug Ut) cR(Aj Ct Gl gP Hw In Ky Mf Mg mS Nf Nt Oz Pk Ql Rj Ub Ue) Jp(Bg Ch Cp Dk Ef Hb Hu Jk Jt Ma Mu nA Nn Om Oy Ut Vv) Ct(aX BC bV Cv cX hB Ik Jl Kk Nu Og Qh Qx Vq) Of(bF cS Et iJ iO Jl Jn Jy Ky Nk Og Or Rj Tn Tr) My(Ch Dk Hu Hw li Iz Jh Jo Mk Mw Om Oy Qy) aX(Aj cD cX dE Ik In Jj Jo Kr Ky Mg Po Rj) cS(Aj bI Hw Ik In Ky Nu Oy Pk Ql Qx Rj Vv) Bg(Ch Co Hq Hu Mg nB nL Nn Nq Qw Ua Vv) oP(As aY Je Jh Kj Ms nD Nf Oy Qy Ub Ue) Po(bV cX Jl Jn Kq Nk nU Oa Og On Ub) gP(AJ Il Ne Nl Qx Qy Rg Rj Ua Uk) nR(Ad Co Jj Kj Nb nl Nl Nm Qv Ub Ug) Ue(bV Cv Hw Ij Jn mY Nu Pk Ra Vq) Ky(bV cX Hb Kk mE Mf Pk Ra Ub Ut) nF(bA In Is jD Jj Kq Ld mF Ng Ql) hB(bI cO Cp Gl Jk Jo Nj Nl Qu Ut) Hw(bI bV Jl Ml nJ Qh Qx Rj Ub) Kr(Aj Ch jD Jj Jo Lj Pk Qd Qe) Bo(Cp Cw Hu Mf Ml Nl Qx Vv) Rj(Cv Mk Nf Nu Oy Pk Qn Ub) Rf(Id jD Jj Jo Mg Nn Qn Tj) mM(bQ bW cE dF Kn Nv oQ Tn) Gz(iH Jn Oz Ph Qu Tv Ur) Qx(In Nu Og Pk Qw Ub Uk) bF(Gl Hq Jo kl mF Mg nD) bl(bC bW Iv Jj Mf Oi Ql) nN(Ij Jd Jh mP Oh Oy Qe) Em(aM aQ cA Hr Mh Na) Nt(Ik Jj Mf Mm Qh Ra) Nf(bV fP Jn mY oQ Qw) Oz(bV Ch Fn nK Qw Qz) nl(Cv In iZ jF Kk Qm) Mp(bW cJ fP mY Vq) Nl(Jk Mf Mk Og Vq) li(cX Et Jl mY Vq) Is(Co Ij It Jk Tv) jD(aM kl nO Oa Uk) Nu(bV Ml Or Pk) Qw(Jl Nc Pk Ra) Jn(In Jt Mg Qc) Ql(bV cX Nk Qn) Og(Hu mP mY Nk) oQ(Ap Hb Ke Oi) Et(Hb Jo Jt) Ub(Bc Cv Ra) It(Jl nC nL) cD(bC bW Ij) cJ(Gl nA nC) fP(aO Hq Hu) fR(cO Il kQ) Ad(Ef Iz) Co(Pf Tn) Mg(bV Kf) Ng(jH Qn) Qh(Tv Vv) Js(Lj Qa) Ut(Pk Uk) mF(cE Rg) nB(bG Il) AjUu CvnC NmbV LvVv MakI MlHb NiNk HuHc InkF RaOi QueF JjnU JobZ LdmP OajH OknA VthX PkaD aYmS nOjE} nC{aM(Ba cJ cL cT cX dF Dg hB Ko Ky Lh Mn Nj Nl Nv Ok On Qz Rm Uk) oN(AO Aw Ax Hb Hc Hu Iz Jk Lj Mh Mp Nb Nl Nt Of Qm Qy Tt Ut) aY(Ba bF dl Fn jH jM Kp Ky Mt Mz Nb Ng Nv Pf Pg Qe qX rA Rg) Ib(cG cR Cw Ez Fn Gl Iz Kq Ks Ky Nr Ny Qc Rc Un Vo) Ra(dF Et In Ip Is Jg Ky Lh nR Oh On Pf Pz Qh Tn Uu) Oi(Ba cE Dc dM Ez hB Kc Kp Nv Qh Qz Rm Sr Tn Uc Un) dJ(bZ cJ Et Jg Jp Kn Lh Nv Nw Ok oQ Ou Rg Rm Uu Vt) Mh(cJ Cv Dc dE dM iJ Kk Kl Kn Qz Rg Uf Uk Uu) Qw(Bg dM iH Jg Jq Kl Kn Mt Qa Qd Qh Tr Uc Uf) cl(Bc Cv Dc iJ Jg Ji Kq Lh Mn Nw Pg Qh Uu Vt) Qz(bA bG cJ cR cT Cv Et Ms Nc Nh St Uk Vp) bF(aO cX cZ De dL Jd Je mP Mv Nf Nl Om Oy) hB(aN aV cQ Ct cX li Ij nA Nb Nt Qm Qy Ua) Kf(aN Ct cX Hw Ik In Ir Jj Ky Mw Nm Qm) pF(aN aV Ax Et Kp Nd Oa OH Pa Pz Vu) Tn(Hu Ii In Iz Je Mw Nj Nt Qu Tt Vu) Ng(Ao bZ Dc gL Hc Iz Kk Ko Nv Ou) cJ(dH Hc In Ky lX Mr Pf rA Uu Wm) li(Cv dF Kk Kl Ko Pg Qh Uc Vt) cE(Co cQ Hq Ij In Je My Nm Qx) cG(aN Cv dA jM Kn Nb Oa Ue Vu) Ky(Cv Di Iu Kd Nb nU Pa rA) On(Ch Cp cQ Iz Mw nF Oa Tt) Uk(Kd Ma ml Nl Pa Pb rA Vt) Uh(Is ml Ne Nt Qm qX Rg Vu) Ip(bG cV Dg Pk Qh Ql Wm) Pf(aV Cp cQ De Je Kk Ld) Ct(Fy Jp Ou Pz Qd Uc) Fn(Bc Cv Ji Kq Qh Rg) Mw(bZ eF Ko Ou St Uc) Nl(cX dD Kk Rc Tv Ug) Kn(dL Jl Mn Mp nF Qm) Rf(Ji Jn Nw Oa qT rA) dM(lt Ma Nf Og Oz Ql) Cp(Mn Nv Ok Qa Uf) Nt(Fr Kl Pg Qh Rm) Ne(cL cU Hc Ko Rc) cX(Cv Jp jV Nc Uu) Dg(dE Ik Kr Mp) Mt(BC dE Rg) Nj(cL Kq Oa Tr) Hb(Ba Ko nR Pg) St(Ij Ms Pk Ug) Kc(bA jQ Mf Ou) Ld(cV hC Qd Qx) Nv(As It Jd Qy) Ok(aV Ch Di Qy) Nb(Fy Hc Kk) To(Dc Jn rA) Tv(Is jH Rg) Qe(As aV dI) Qm(Et Jq Ko) Oa(Ha Ou Pe) Uu(dI Jh Qy) Vt(dF Mr Og) Oz(Bc Kl Ue) Ba(Hu Jh) Di(Mn Uf) In(Dc Qh) Ir(Pk Rb) Qa(dl Kr) Je(Jp Pg) Oh(Fw Kj) Ou(De Pb) Ug(Pz Rm) aV(dF oQ) bA(Pb rA) bZ(aO Of) dG(Mf oH) nF(Ny Pg) AoNx AsLx CvUe MpcL UaIs UcJj JnoP KddE KkPc aljH aScV cQoO nTiA} mF{Uk(aY cL dH dl Et Ir Jn Kc Kx Lx Mh Mr Nh Nj Nv qV Rg Rm St Uf) cl(aI bF bZ cL Cv dG dL Kn Ko Kq Lx nR oF Oh Pg Pz Rj Uc Vt) Kk(Af bQ Dg Id li jF lW Lx Mp nF Nj nU Pa Pz Rj) bF(Ao aS Ct Hq In jD Ko Md Mh nA Nj Oa Pa Up) Qw(Dg gL Is Ji Jq Ko Mn Oh Ou Pg Qa Tn Uf) Qz(aM cX Fa Fn lp jF Jp Kd No Pa Pz Rg) aY(An Cv Ib jT Kn Ko Nj nT Nv Nw Nx Rj) Mh(Ba bZ cE Cv dF dL hB Ko oF Rg) Kd(cQ Ip It Ky Lh nF oH Oz Uo Up) Rj(bA Dg dM Jn Kp Nw Or Pa Pf Pz) aN(bZ cG dF Dg Ko nR Oh PF St) Nt(cG Fr Pf Pz Qh St Tn Tv Uh) Kf(Aj cL Is jE Js Nu Og Ug Up) hB(aM aX In Iz Mp Oi Pa Qm Ss) Ko(aM cL iC In ml Nl Pj Pz) Dg(Hb jD jE Jt Kr Ng Nl) Tv(li It kE nF Ng pF Uh) Nx(Ct Ib Je Jf Qx Ra Ue) bZ(aR li In JK IK Nj Nl) cE(bP Ct dL nF Nj Nm Pa) Fn(Et Ib iC Or Pz Vt) Is(bO bX Di Ra Rb Up) Kn(bW cG dH jF Nl nR) On(Ao Ch Dk Jd Mw Qy) Uf(Di jE Kr Nj Nm Or) jD(bA bQ Dc Ld Pz To) oN(Di kN mM Ng Qm Ut) Ne(aF bQ cG cV Gp) Ky(dG Kp Mt Nj Qa) Pa(cJ dF hA lh pF) nT(dF dH dM oP Qh) Ng(Ad dF Nv Tn) Ib(cL iC Ld Uv) Oh(aM aW dE Ra) oP(Mf Mu NN) Nm(Ad cG Cv) Nl(cL Kq oF) Pz(dF hA jF) St(Gp In Ur) Kc(dN jF Uc) Uh(Hb ml mM) Lx(Ha Ld) Mw(bQ Qh) Nj(cV oF) Ip(cG cL) Ir(Pk Ur) Kp(nR pF) Nv(li Ra) Pf(Fb Jd) dG(Og oH) dN(cL jU) 1K(cR cX) ChdF CtPg CvTo DcUp DiQe DkOk MrdL IdLd QaPk JiQm QyiC OrbW UujH aMnR aWqT cAdH cGjM cSqV dlhA iOpF} nL{aY(bF Cv Dc Jg Jp Kf Ky Lh Mz Nf nT Nv oH Ok To Tv Uh Uu Vp) oN(Ao Aw Hb Hu Jk kl Lj Nb nH nJ Nl Nt Oz Qx Qy Tt Ut) Uk(Ad Fy Ir Ji Kk Kq Ks Lh Nw Nx On St Tn Tv Uh) cE(Ap Co Cw In Iz Jd Je Mg Mh Nl Oy Pb Qx Qy) bF(aF aO As De dL Fa Iz Mk Mp Oh Qm Qy Tj) hB(aN cQ cX dE Dk Fr Ij kE mM Nb Nt Ua Vs) Ou(Ao Di Ir Jd Mt Mv My Nb Om Rg) Qz(bG Cq jH Jq Kk Lh Pg Qa Qh) cl(dF iJ Jl Ma oE Pf Pz Tr Uc) Tn(Ch dJ Hb Je Of Qu Ra Tv) bZ(dJ Ip Ne Nl Nt Oi Pz Ra) Kk(aM cG Hb jD Ky Pb Qh) dF(li kK mM Oz Ra Rf Vs) Ct(Lh Ma Nx Ok Qh Uc) Ib(cU Dk Jh Jl Lx Nq) Nv(As Fa li Ng Nt Po) Oi(Dc Dg Kl St Uf Uh) pF(Ch cX Nb Nf Nj Pd) Jp(cX dJ Fn Je Qy) Kn(Hb jH Nf Ng Oz) cV(Ip Kf Ki Mz Nf nT Nv oH) oH(dG dH dL dN Uf) Ma(dM Hb nF Ra) Uc(cX Fn In Mh) Uh(jH ml Or Oz) aM(Et Ip Lh Mt) Dc(cG Nf Ra) Dg(Ap li Jt) Mw(hC iA Uf) Tv(Cv Ky Oz) Is(Ml Nt Ny) St(Fp Ha Ik) Qh(In Ne nT) Ok(Pj Qx Ra) On(Co Cp De) bG(Ip Mh oQ) Bg(Ip Oh) Ng(Ad Hc) Tr(Nb Qw) Pz(cU Ra) Ko(Pj Ue) Nx(Ao Qy) Ny(Iq nF) Oz(Cv Kc) cX(iO nR) iA(Of Qu) AlHw AsLx ChiZ Fyli MnHb NIKq IrRb QaKr QwPf KynU LhjD RmUg OhdJ OrnH VtoP PgnF} nJ{aY(Cv Et In Is Kf Ky Ld Nb Nj nT Nw Nx Oh Ok Rg To Uh Vp) Uk(aM Dc Dd Dg Fw Ji Jn Kq Ma Mz Oz Pg Qe Uh) oN(aN aS cI Co dE li kN Md Nf Nj Qt Qy Rb To) cE(aM Bn bS cI eD Fw It Kk Mp nF Nl Oz Up) hB(aN Aw bS Cp cQ De Hc Jd kE Mu Nb Nq Oz) bF(Ao Di dL Hc Jk Kk mM Mv Nb Nf Oz) Uh(aM eD In Iq jD mW nF Oz Up) Kk(dE Iv jD lW Nb Ng Nj Oz) li(bZ Fw Ld Qh Tv Uc Vp) Kn(Ed It Iu Iv Oi pF qT) Ky(bL Db Dd Dg Qa Tv Vt) dF(bP bX cA Di NT Up) Ng(Ad Dc Ef hG Rg Tn) On(Ao Cp Ct De Dk Qz) Ou(Ch cZ De Jk kl nF) Dg(In Jt Mw Nt Oi) Et(aM cI cX Je Kr) Ok(Co Cp Cw dE Kr) bZ(In It Nq Nt Qz) Ne(Fy Qh Tn Vp) Nl(cV oE Vp Vt) Uc(Cp In Of Oi) Oh(bS cA iA Kj) pF(aN Ch Qu Qz) Mw(hC Kf Qh) Nj(cV Kq Tr) Pz(Aj cX To) Ld(aM Mn Oz) Vt(cl nR oH) cJ(aN dE Pa) oP(cV Je Kj) Cp(Pf Qa) De(Is Nv) Ha(St Vp) Nh(cV Tr) Tv(bP lh) In(cl Fw) Hb(Ji Nw) Ip(aM bG) lt(Dc Rm) Qz(Oz Qa) Nx(Bb Co) cG(bP cl) dG(mW oH) nR(dL Kj) jD(aM Ko) qT(BG) BnPg ChgL CtNv EdKc NmKf MaUs NdQh ToIs TnQu KeNw dMgP} oP{Cp(aM An aX bZ Dc dF Et Jy Kf Ks Mn Ms Nr Ok Qb Tz Ut) aN(aD Aw Bb cH Fw Hb kG Kj mP Ne Nf Nm nR Oa Pf Ra) Ap(aX cH Dg Et In kC kO mP mY nB nF Nk Nw) Cw(aI aM Dc Jp kC kl kO mS nU Oh Sr Uo Vp) Ra(aP bS Fw kC kl Ky mM Ne Nh nU Uo Vp Wm) Kj(Bg Ch In Jn mE nD nF nR nU Rm Tn Vp) As(aC aM aY cX Hv Mz nD nU Oa Qa Uc) aM(Ao cQ cV Ed Kk Mk mM Mz Pa Qz) aP(Ct Hv li Jv kO NU oQ Qw) Uk(cQ Ed Jr kO mM nF Oz Wm) Ct(bS cA Hv Hw kO Nm Pa) Fw(Ik

Figure 20 Continued

Ky Mk NF Oy Wm) Ch(bG Jl Jp kI Pf Tn) Ii(cA Dl Ed Pi Qh Rm) Qw(aY cV Ed In Ky Ou) Di(bB bZ nU Qh Ug) Nu(cV Je Ql Qy Rm) Mz(Bb bP cB Fb Hb) bG(aS Mv nF Vp Vt) aX(Hb Nm Nt Ub) bB(Gl mM nF Vs) cA(Bb mP Nm Qz) Mw(Ky Pg Qh) Oa(Ke Mp nH) aF(cV Nm Qa) bS(kC mP nF) kI(Bg Cs cV) Aw(dD kC) Bb(Et mY) Ed(Cv nI) Fb(Oz Vu) Ms(bP Or) Ib(Dg Mu) In(Co Je) Kk(bP Oi) mM(cH Kf) AonU GlPg MbaY NbOr HbKn IzJy JemY QzOz QhVs aDcQ cJnF} nR{qW(aE Ao As Bb BG bI bM Co Ct Ed Iz Je Qw Qz) Qw(bW cE cH In iO Ky Ng Nh Nn Pf Pj qT Uh) Ld(Ad aY bW cH dM Id Ij Jv Kr lM Lw nD Wm) Qz(Ed Jf Jn Mp Mx mZ Nh nT nU Oi Oy) Ch(Bc dN lW nD Nv Ok Pf Qe Sr Vv) Dk(aM Ax Dg Fw jU nH Nw Ok Pz) kI(Ad bC bS cZ Ki Kj Kk Kp Ra) Cp(Fa Fw Kf Pd Pz Qa Qe Up) qT(aE cQ Cu Jd Ke Kl Rf Vs) Nt(aJ bX cH Dc dL dM Ra) Ib(Ax dH Ok Qa Qh Uc Vo) Kk(As Ij Jk Kj Nf Uk Vs) Ne(cX Db Gp oH Rb Ub) Ng(aM Ap aS Db Di Dl) aN(cH Fw Kc lN Tt Up) Di(dG jU lN Mx) Nu(bX Kc Kf Kn) Mw(Kd Qh St Uf) aM(jP Nf Of Pa) cH(aL cZ jR nF) nH(Ad Bc cI cZ) nK(Ad cZ Ra Uk) Ii(Kn Vp Vt) In(Oa Qy Vt) Kc(dE Iz lM) Kj(nA Nl Pa) qV(bF bM dA) lN(Jd Je Qv) Bc(Nb Of) De(mZ Pd) Ef(iO Kf) Tt(Is Or) Kn(Hb Uk) Vs(aJ dG) Ph(jP jR) jI(aV Kl) kE(aJ dL) AjPz BgiO CtFw DlNm WmNj FbOa JkKf OrnA UhlM UpbP aClK bIlL bQjE nFoH} nF{Ji(Fb Gp In Je Ma Ms Mz Na Nt Pb Qz Uo Up) On(aW Co Ct De Dk Hq iH Ii In mP Ng) Uh(bX dF Jp Kk Ky Md mW Nf Qz Ra Up) Pg(Ii Jh mP Ms Nb Nt Oy Pd Pe Po Qz) Nv(Hw Ii Mk mP My Nj Om Pd Pe Ra) dF(Bn Ii Kk Mw Nb Ne Nl oH Qv Ra) Kn(bZ cG Jp Mp Ng nU Ok Qn Tr) bF(cH Ct De Hu Ii Iz Ne Oy qW) oH(CH cL dN Ne Ok Or Qa Qw) Nw(aY iH Jf Ms Na Or Pz Ra) Uk(Is Jn Jp Jq jT Kq nU Qe) In(cE cJ dM Kd Kf Lh Nx) Qz(Cu Fy Jq Lh Tn Tr Vp) Ok(Kr Ny Or Pk Qv Um) cJ(Jl Jp Jq Ml Pz Qn) Lh(aY Ii Mp Nt Pa) Or(bA cH Mz Ny Pk) cE(An Ct kI Ng Qv) iH(Jj Lx Pf Qn Qw) Ch(bZ Is Jp Ma) oN(Bg De Ef Mv) Et(aC bA Pj) Ma(kI Nc Pz) Tn(Fb Ii nA) Is(aF Ny Pk) Qw(hB Jp pF) Kc(Jq Mp Pf) Kk(Af Ij Jq) Ou(cQ Ct Nb) Nl(Mz oE) DcIi EfNg FykI MmlN MsPz MwNx TviO NyOy bAbX} kI{oN(aN Ao As Aw aY bS Co Cp Ct Dc De Dk Nq Pa Rb Rj Ua) aY(bF bZ Ib Lv Mz nO nT Nw On Pg Qh Qz Tv Vu tF) bZ(Hc jH Kr Mh Nl nO nU oQ Rj To Up) Tn(aM Ii In Mv My Nf Nj Nq Oi Qy) Ou(Ch jH mM Mv mY Nf Of Oz Pb Uk) Pf(aP cV dF gP iP Kk Ld Qx Qy Tj) bF(aN cD Je jH Kk Lj Mg mM Qt Up) cE(Aw Ct Cw Dc Di jH Mh Mw Nt Nu) hB(Ap cA Co De Dk Nl Nu Qt Vt) Tv(BG cV iJ Ma nY) Oa(Bg Hc jD Jy Kq Ok) Ib(Cq Dk Mf Mj Vp) jD(bG cG Cu Ko Vu) jH(aM cJ Kd Ko Rj) Ma(Ct Kk Uk Vt) dF(mM Mp Ne Nf) Ch(gL iZ Qz) Je(hA Oh On) cV(Al Ld Pa) Qa(bS oH) Qz(Bg Jp) Qh(Ii Nf) Jl(cI Ld) Kd(eD Lv) Ok(Jd Qy) bQ(Lj Uk) gP(Ax Nj) pF(bS Cv) CuIt DglN NgUt UcIn IrQg IsVp KoeD bGlM cliO dNoH} Ng{Ad(aJ Aw BA BC dG dH Ef Ib Jj Jl jT Kf Mt Mv nH Nm nU On Ph Pk qX Rf Ub) Pz(Aw bC bF Bg bQ bV bZ cG cL cR cS cT Dd Dg iB iO Or Rj Tn) nU(aN Ba bF cE gL Kc Ko Ou Tn To Uk Ut) My(aC cL cV cX Dc Dd Kf Or Ou Uu Vq) Rj(Ba Dg eF Et Is Jg Jp Ou Tn) Kf(Bc Hw iO Jp Ky mY nH) Ba(Jn Jp Kk Nc Nl Og) Et(Ef Hb hC Ky Or Pj) Dg(hC Is Jn kN nH) Nj(Bc bZ eF iJ iO) Ky(Dc Dd Jp Or Vq) nA(dF gL hG oH pF) oN(kC mP mS mY nD) Nc(bF Dc dF Ou) Uu(Bc cM Jn nH) Is(bC Ph Pk) Kk(Jp mP mU) Ou(gP Jn Ne) bF(bC mY nI) kE(cE dF Ef) Bc(Mt On) Dc(bC fR) Uc(qU rY) Tn(nK Qz) Ko(lN qX) Vq(Jp Uk) cV(Pa Qz) hB(Nd Nl) BoJn EfmZ KnjH NxmP bZmS cEnI cGqU nDiH} nA{bF(Ao Cp dE Di Hc Is Jh Ld Nt Qy Qz Wm) hB(Di Hu Iz Jh kE Kr Nm Nn Nt Of) Ou(De Di Ii Jd Kc Pf Pz Vv Wm) cE(Aw Cp Ct Dk In Is It Nb Nl) Ma(bW Ct Kc Or pF Qu Uk Vt) bZ(In Is It Nq nT Of Qu Qz) Tn(aM Ef kE Ky Nb Ua Vt) oN(Jk Kk Ne Nq Of Pa) pF(Kn nT Oh Pa Tv Vp) Ld(aY Bg In Pf) Is(Kd Qw Ra) Je(Nv Nx Pf) Ch(gL hG) Dk(dF Ok) Et(cI Pj) Ib(Nx Qd) Tv(Ih iO) St(Fb Ii) Qw(dF iH) Kk(Jl Pf) Oh(cQ oH) Or(Pg Ub) Uk(aY oH) cJ(In Tr) MwhC NjnW NlcV IpUh QziH OkcI VpaY bXjH dMgP} nH{Uk(cE Dc Et Ir Jn Jp Nh Ou Pz Rm Tv) cE(Ao aY bI Ip Ir Lj Mh Nt Oa Ra) bF(aS Ch Ct Jd Lj Po Qx Vt) cI(bB cG iO Jp Ok Qe Uh Vt) Qz(Dk iA Kn Ok On Pz Qa) Nl(aY cG Gp hB Tr Uh) Tv(aM aY Ii Ky Ne Vt) pF(Bc cQ In Nd Uh Vt) Kn(aY In jD Md nU) Ct(Ip Nv oN Pg) hB(Cp cQ Di Nj) Or(bC Ir Lv) Uh(Ip Mh mM) Ii(Dg Fy) Is(aM Ug) Qe(Fb Vs) Kc(cX Ou) Nx(aY Je) Oh(aW aY) oN(As Ef) BndF MhOu MtbC MwQh TnJk InKd HbLh IvNy PzjD JdOn QwiH LdmP PfdI bGoQ dNoH} Ib{Ou(Ad cV cX Dd Et Jn Kf Ki Kr Ky Nc Nj Nk Nl Nt Oz Pk Pz Qw) mW(Al aP bV dH Fa Id jD Jl Jt Mm Mx Nn Nq Uu) Is(Ik Ir Kr Ml Nt Rj) nU(In Ky Pa Qv Ul) jD(Kc Kn Ko Lh Mz) Ji(aX jH Kk Kr) nD(bF cE Ip Vp) kE(cG Qc Ut Vp) Dd(cV jF Ky) Nj(EF Jp) Qw(hB oH pF) Nx(kG kO mM) Dc(Kr Ky) Pz(cV Or) Rj(cE Cq) AdIk DgoH UcKr TvaX QbnT UvkF bFkC dIkN nOlK mYiB} nU{Uk(aM Et Fw Ip Nb Ne Nl Pz Ra) Nt(bF bX dF Kl Ql Sr Un) Ii(Dg Qh Sr Uh Vt Vu) Qz(aN aX Jn Ky mW Oz) Nb(Aj cT cX dF Ky) In(Al cI dM Pi Vt) Ra(Kk Nj Nl Qw) Nx(Ao Qx Qy Wm) aN(cE Kc Nl To) Mw(bF Kn Kq) Kk(aM Ed Ik) Ld(As Lz nI) Vs(Is Kf Qe) Ef(hB oH) Kc(cV mI) Kn(aM nI) Or(bX Kz) AscX BgqT ChpF DkOk EtKr KeNw UhmM dNoH} nI{Kk(aL bF cL In Jf Ky lW mP Nf Oi Tv Uf) cI(cE cG dF Et iO Nw Oh Ok Pf Pz) cE(aM aR Kc kE mM Or Qm Uk) Ld(hB Ky Oh Ou Pf Pz) bF(Cp De lM mZ Nt rA) Or(hB Lv Nc Nw Tv) Mw(Dg Pg Uf) Qz(cG oH Pg) Kf(In Nm Oi) Di(hB oN) Kc(cX jD) Ky(jY rA) Nv(Dk Je) Uk(cG Cv) NjdF TvIi HbJi KnlN KorA OhbX PfdI} mP{Ld(aM aY bG Fr Fw jI nN Og Oi Ra Vp) Ch(gL iZ oH Pf Tn) Kk(aM cA Mz Nl Ra) Vp(bF bS cA Ko nN) Is(bS De Di Um) Nx(Ed lN Qz Ra) Mw(bF Kq Mz) oN(Di Ef Vs) Mz(Nl nN) In(Cq Pi) Ip(bG Um) Nv(Mp Vs) cA(cE nT) eD(bX cI) DcQz DePg FbSt NeTn NloE TvaM JlmZ} nD{Ip(Af bA cG cJ cV In Uk) oN(As Bg De Je Mv Nq Ra) Nb(oE Ou Uh Vp) In(cE Kn Ld pF) Qz(Jl oE pF Tr) Mw(bF cE pF) Nl(bB nW Ou) It(Dc Kq Nv) Je(Et Nw Ok) Vp(Ii Jk Lw) iH(Ch Ky Vt) Nt(cE Ou) Uk(cE Ou) oE(Nj Qw) FbOh MacJ MdOr MvhB TtIs PzjD JdOn KnKy UheD} mZ{Uk(bF Jn Oh Ok oN Qe Qh Tn) Is(cX Kr Kz Oa Rb Um) Ra(bF bZ dF Ma Ou) Oa(dF Kq Ma oH On) Tn(Cw Jh Mw Qy) Qz(bF iA Jl Jn) In(Dc Pi Qh) Jl(Hu Mu Oy) Vu(cE cV Ok) Je(Nv Pg) Oh(cV oE) Ou(De Qw) Pa(aY oE) PoQh LzMz MwNv HubF RfOr} mM{Uh(cE dF Dg iO Is Ld Oz Pa Pf Pg Pz Qz Rj Uu) Kn(aY cV Ou pF Uf) Ok(aV bW Ra Uf Uk) Et(dM hB Uf Ug) Kk(cL dG Ij lW) On(Ch Ef Jd Ra) hB(kE Ld Qz) Ra(Nx oN) qT(bF cE) MmdF InKf HbJi QzNv OhbB OrdG bWoH} Qw{pF(cP dN kO Nj Nk oH Pz Rj Uk) gP(aC cJ cR dI iA Ij Is Ji) hB(Ed Ex kG Kr Mv Pz) Ou(Mf Nl Ub) iA(cP Nc Nk) kE(cE hC nW) oH(bC Nk Ub) eF(Mg Nj) ExNx LifR cPiJ dFkK iHkO iZkG} Jl{Ne(Hw Ii Il In Iq Jk Jr Ly Lz Mk Nf Nn Om Po) Nl(Hw Hx Ii Il Jk Md Nf Nn Om Oy) Nh(In Jr Lz Mk Po) Nc(In Js Ly Po) Nd(Ij Js Ly) Nj(Ct Js) LyOf IqIt OrkE PanT cImS} nK{Tv(aM As bG Ii Oi Ou Rf Uk) pF(Ef Nb Oh To Tz Vt) Or(dF dM eC Ky Vp) Ip(bG bZ Ky Tr) Uk(cJ hB Ir) bF(dE Ra Vt) dF(Bn Dk Mp) As(Lx Qa) Is(Ik Ml) Ou(Mh Nb) cV(Nj Pz) CpcE MaLd TobZ} fR{Mw(bB Cv Dc iH Is Ji Jp Nf) bR(aD An bC Dc Nf) Is(bL Jn Oi Po) Ld(bN dA Pe Po) aN(dB Dc kQ Na) Et(Nf oH Oi) Nf(Dc Nj) bF(aD aO) kQ(Kn Nw) oH(It Ur) CvOg aCaP bCbW} kE{hB(Aj Ao Hu Iz Mv Nt Ra Ss) Ok(Jd Oa Qt Qx Ra) Ch(bF iZ pF) In(Pi Ra Tn) Or(dM Ma oQ) aM(dF Is oN) Di(cE oN) aY(oF Vp) dF(Mp Mw) GpSt IsUg QzoF QxPf RjcE UkoN bFdL cGcQ} mY{Ou(Ch Kc Mw Nl Uk) bF(Ao Cp My Of) hB(Bg Cp De Mv) Kk(aY Ed Is) Nx(Je Uk) Or(In Pk) AdoN BndF ChpF CpOh EfbZ EdKn FbQa HaIs NfcE NlTr UbIp HbJi PzcV VpaY} Kf{hX(aM Dk Ij jE Jt Nt Nu Up Ut Vt Vv) jD(Jj Jk Js Nt Og Pb) Rf(eD jO) Of(gP Ou) lM(Ch Jj) AjjM InmI HbjH QzkG JkqX eDmT} Is{Aj(Ba bC cM Om Qc qX) Ct(Ml My Nt) mS(aM bP dM) kC(Pk Ur Vv) Ch(kO Og) Ou(Jk Po) MlKs MsIq TtmU IhkO JjPh JmnO} Pz{Ct(cV hB iC jH Or qX) hB(Bg Cp Mg Nj) eD(Aj Rf Ue) In(Or Ou) jH(Aj Ub) NtOu QzcV KrjD OrUk PhqX} mS{Or(cJ Ky Md Ul) Ip(aM cE cV) Ch(iH pF) Ef(bZ oN) Nb(cE Ky) Nl(nW Tr) MabP MvoN MwcE TvaM IrKy} jD{Kc(bS Ed Ic iJ Kr Rj Uk) Et(Aj Uk) Nt(Fa Ko) Kr(Dg Ko) bG(Nj nO) WmcJ NuJi NliJ KknO UhOz} qX{Oz(Aj cJ Dg Kn Ky oE Ou) Aj(Kc Kl Ko Lh) Mz(cC cJ Ky) ChJp KcPb KoPh KymE RfNw} mW{Qz(bW Id Ji Lw Mp Pf Qa Qh rA) Ch(cE Qe) IjLd HbNw KjoQ QmUh UkhA aJjH} jH{Pk(Fa jI Kn Lj) cJ(Mb Oa Wm) Kc(Pb Wm) Kr(Ko Oa) Vv(Et Mz) UkmH UhPb aJkK} Em{Or(cY Hw Ii In Kk Li Nk) Ly(cL Ky Ma) Kj(Kq Ok) GzaV NkLd LhOu} Nx{Ex(aN Ch cV Ed Hu Iz Kj Ks Nm Oi Ut Uv) Vq(Hw Ii)} kC{oN(Ef Jh Mv) pF(Di Kc oH) EtcI NbdF NloE IhRm IpKy KccV} oQ{Ii(Dc Ks Vu) In(cQ Dd) Or(Bo Di) AwMa NtOu MwbG JeKk aMcQ} kO{oN(Ef Je Mw) Uk(Et Ok) ChbF NloE IpUh IvNy QuhB dNoH} Ou{Nt(Mb Mm My Nc Rj) Nj(Hq Of) AdDk NlnB QzUt} nT{qT(bZ cV Kn Ko Rj Uh) Qa(Fb Qz) MviA}

Figure 20 Continued hB{Nj(gP Hu Jk Mv Nn) NlOf HugP iOkG} kK{qT(Gp Kn Ra) iC(Bn Kk) UhjR PkjI dFlK} In{Jn(Nc Ne Nl) Vq(Pi Ue) QamU KcmI} nO{Bg(lK lN) MphA NllN aMjE aYlK bPdF} Kk{lW(aM Ii Mp) OimU UkVq mErA} kG{Qz(cE cG) DgJt NeoN LdbF UkhA} Or{mE(Dc dM Qa) MyOf QmmT} rA{Aj(Dg gP Jg) JpVv RjmE} Nl{MzjF VthX eDiJ} Jj{oH(It Iu) NjgP} Nt{JnKy RmiO} Mw{oN(kN nB)} Ik{Vq(aX Ub)} Qa{FbmI UkmE} Qz{TnmH cXgP} Kc{WmhX eDlW} Ld{IimU PfkN} aC{bE(Aj cV)} lN{IdlW UkmH} ChkFoH DgJtjO NjOfiJ RfOaeD OhcQnN VtOzhX aLjIkP Constrained panels with 2 analytes, where 1.0E-8 >= 'AUC p-value' > 0. Contains 4 panels of 109,774 total panels evaluated. : Or(kI nJ) Ow(Ng nU)

Constrained panels with 2 analytes, where 1.0E-7 >= 'AUC p-value' > 1.0E-8. Contains 8 panels of 109,774 total panels evaluated. : Ow(Kr Mp nJ Rf) Or(kE nC) AjIs IboP Constrained panels with 2 analytes, where 1.0E-6 >= 'AUC p-value' > 1.0E-7. Contains 37 panels of 109,774 total panels evaluated. : Ow(cS Ct cV Gz Hw Ib Ii In Ky Nf Nt Of Oz Pb Pc Pk Po Pz Ql Ue) Or(mF nL oP) nC(cE cG dF) nF(Nv Nx) nL(bF Ou) AdNg NlJl QznR QwgP VpnD aCfR nJoN Constrained panels with 2 analytes, where 1.0E-5 >= 'AUC p-value' > 1.0E-6. Contains 75 panels of 109,774 total panels evaluated. : Ow(Aj aX bI bV cR cX Hb Ij Ik Jj Jo MF Mg Mk nC nF nI nR Oy Ph Qw Qx Rj Ub Uk Ut) oP(aM aN Aw Ct Cw mF Ra) mF(cG hB Kf Ld Tv) Ng(Ba cV hB Ou) Or(mE mT nH nU) kI(bF bZ hB oN) Jl(Nd Ne Nj) nR(Ch Ib Ld) nC(aY Dg Tv) nF(Lh On Pg) cE(nJ nL) ExNx MzmZ IbOu QwhB KknI LdmP aCbE bFnJ dFnL nAoN Constrained panels with 2 analytes, where 1.0E-4 >= 'AUC p-value' > 1.0E-5. Contains 163 panels of 109,774 total panels evaluated. : nC(Ba bF bZ cJ Cv dG dJ dM hB Is Kc Kf Kk Kn Ky Nv oN oP Ou pF Qh Tn Uc Uf Uh) Ng(bB Bc bF Bo cE Cu Cw Dc dF Dg Kf Or Tn Uu) mF(aY bF bZ cE dF Kd Kk Ko Nv Pa Qz Uh Uk) Is(Ct Hw Ib In Iq Ks Ms nL Ph) oP(Ao Ap As Ch Cp cQ Ed Fw Uk) Ou(Ct kI Mf nJ Nt Nu Of Qw) nF(bF dF Fr Ji Nw Ny Ok Uh) nL(cG hB Kn Nv oN pF Qh Tv) Ib(Cq cV Ji Ky Lh Nj Tn) nJ(aY bZ cG cJ dF Kk Ky) hB(nA Nj Nt Nu Of Ow) In(Jn Mt Nc Ne Qa) Ji(Iq Ms Ne Om) Ow(Ch Co nD Tj) Or(Ct Jk Of) cE(nH nI nK) fR(aN bR Nf) Aj(Ad qX) Lv(Nc Ne) Qa(Iq Qc) Jl(Ly Nc) Kk(nR nU) bC(aC bF) jH(Oa Pk) pF(kI Qw) MsMt MzqX NeHw TnnA KcjD KfhX NwOm NxmP UknU UhmM bFnI Constrained panels with 2 analytes, where 1.0E-3 >= 'AUC p-value' > 1.0E-4. Contains 579 panels of 109,774 total panels evaluated. : mF(aM BA cI cJ Cv Dc DG dH dM dN Fr Kc Kn Ky Lx nR Nw Oa ON oQ Ou Pe PF Pg Qh Qw Rg Rj St Uc Uf Vt) Is(Al aN Ch Co Ii Ij It Jn Jo Js Kg Kj Lu Lz Md Mk Ml Nc ND Ne Nf nH Nj nK Nl Og Om Qc Tv Ub Ug Up Ur Us) nC(aM bA Bc cL cU cV Dc dH dL dN Ib Ip Jg Jn Ko Kq Lh nR Nw Ny Oa Ok On Pa Pe Pf Pg Qz Rg St To Uk Vt) Ng(aJ Ap Aw bA bC Bg bQ bZ cG cL cT Dd dG dH eF Fa fP fR iJ iO Jg Kc Kn Kp Kq Ky Lh Mt Qh Qz Vq) Ou(Aj Ch Co cX Hw Ii Ik Jj Jn Jo Kr Ky Mg nA NF Og Oz Pb Pk Ql Qz Rj Ub Ue Ut) Nj(Aj aX bA bZ cV Et FR gP Hw iJ Ji Jn Jp Lh Lx Ma Ml Mt Nw On Pa Qa Qw Ub) Ib(Ad Dc Dd Ef Et Fa gP hB Jn Jp Jq Kf Lx Mt My Nk oH On Or Pz Qh Rj Uc Vv) nL(cV Dc Dg Jn Kf Kk Ko Ky Ld Lh Ma nR Ny Oa On oP Pf Pg Rm Tn Tr Uc Uh Uk) Ji(Aj Ct fR Hw Ii In Jo Js Jt Lu Ly Lz Md Ml Nc Nd Nf Nk Nl Ql Ub Ue) hB(Bg Ch Hc Hu Jk kE Mp Mu Mv Mw Nd Ne nH nJ Nl Nn Pk Pz Qu) Et(Aj Ct Hb Hw Jo Jt Kk Ks Ly Ms Nc Nd Ne nF Nk Nl Om Ue) Or(cV Ii Ky Nf Og Pk Pz Ql Qn Qw Qz Tv Ub) fR(aD An bC bX cA cX Dc In Mw Nd Og Oi Pz) nF(BA cE cG Jg Jl Jq Kk Kn Ma Mn Mz oN) nJ(cV DG dM dN Kf Kn Ko pF Tv Uh Uk Vt) Ct(BA cE cG dF Jl Jp Lx My On qX) Nc(cV dF Hw Jn Lh Ly Lz Ma Nw Ok Pa) Nl(bA Hw In Jn Lh Lv Lz Ma Ml Pa) Ky(Dd gP Ik Jj Nt nU Qw qX Ue Ut) Aj(bZ Dc Iu Jn Jp Mt Pz Qa rA) aC(aJ aX bA bZ dF dH dM My Qz) cV(Jj Ne Og oP Pk Pz Qw Qz Ub) Qa(Hw Ih Js Ly Lz Nd Nf Om) Nw(Iq Ly Lz Md Ms Nd Nk Po) Qw(Jp Nk nR nU oH oP Ub) Jn(Hw Ly Ms Nd Ne Nh Ut) Vq(Hw Ik In Og Ub Ue Uk) jH(cJ iC Mz Ra Uk Vt Vv) Jl(Iq Js Nf Nk Of Po) Kf(Hw jD nH Nt Og qX) Lh(Hw Ly mP Ms Nd Om) nU(cJ dM Kn Ra Uh Vt) oP(aY Je Jf Kj Oa Qy) dF(aO kE Mp nK Nt) kI(cE Dc Tn Tr Tv) Ne(Lz Ml Mt Pa) Nh(Hw In Lv Pa) Kc(hX nR qX rA) Og(bB cE cL Qn) jD(Fa Ow Uh Uk) Ly(Fr Ma Pa) Nd(On Pa Qe) In(Nx Oa Qe) Om(Fa Jg Ok) bC(bA cT cX) nR(iO Pe Uk) nA(bF bZ pF) nH(cJ Kn Tv) iC(bS cA Pk) Mt(Hw Ii) Jj(bI Dd) Jp(Ch Co) Jt(Dg Ok) Nv(mP nD) Of(Jg On) gP(Qz Rj) mM(cE oN) hX(Ow Vt) BcUb MzeD UeUh TvnK PzUk QcQe QxNx KklW NynD VpmY PgmP bIcG cJqX cQoQ iHiJ kEoN

Figure 20 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.4E1 | 5.3E1 | 7.5E1 | 7.1E1 | 5.1E1 | 5.3E1 | 2.0E0 | 5.0E0 | 4.4E2 | 2.0E2 | 965 | 33 | 171 | 33 | 0.47 |
| Ad | ug/mL | 2.5E-2 | 5.8E-2 | 5.8E-2 | 8.3E-2 | 7.7E-2 | 8.9E-2 | 6.8E-4 | 3.6E-3 | 3.7E-1 | 3.6E-1 | 255 | 27 | 103 | 27 | 0.64 |
| Af | ng/mL | 9.2E-1 | 9.5E-1 | 1.8E1 | 2.8E1 | 7.2E1 | 9.4E1 | 1.7E-3 | 1.7E-3 | 5.3E2 | 4.8E2 | 255 | 27 | 103 | 27 | 0.51 |
| Aj | ug/mL | 1.4E0 | 4.7E0 | 2.6E0 | 3.4E0 | 2.4E0 | 2.4E0 | 1.5E-3 | 3.8E-2 | 6.1E0 | 5.8E0 | 255 | 27 | 103 | 27 | 0.57 |
| Al | mg/mL | 9.0E-5 | 1.1E-4 | 2.5E-4 | 3.1E-4 | 4.2E-4 | 5.3E-4 | 2.5E-6 | 2.1E-5 | 1.9E-3 | 2.2E-3 | 255 | 27 | 103 | 27 | 0.55 |
| An | U/mL | 4.0E1 | 6.6E1 | 1.5E2 | 2.2E2 | 4.7E2 | 4.9E2 | 9.8E-4 | 6.1E-1 | 5.5E3 | 2.5E3 | 255 | 27 | 103 | 27 | 0.59 |
| Ao | pg/mL | 8.5E1 | 7.2E1 | 2.1E2 | 1.6E3 | 1.0E3 | 7.4E3 | 1.5E0 | 7.4E0 | 1.6E4 | 3.9E4 | 255 | 27 | 103 | 27 | 0.48 |
| Ap | ng/mL | 2.7E1 | 5.2E1 | 4.3E1 | 6.0E1 | 5.0E1 | 4.6E1 | 9.9E-1 | 1.8E0 | 3.3E2 | 1.6E2 | 255 | 27 | 103 | 27 | 0.63 |
| Ar | ng/mL | 6.5E-1 | 1.4E0 | 2.0E0 | 4.7E0 | 4.1E0 | 9.7E0 | 3.4E-3 | 8.4E-2 | 4.3E1 | 4.7E1 | 255 | 27 | 103 | 27 | 0.60 |
| As | ng/mL | 8.7E-3 | 8.7E-3 | 1.2E-2 | 1.1E-2 | 1.6E-2 | 9.9E-3 | 1.7E-3 | 1.7E-3 | 1.1E-1 | 4.2E-2 | 255 | 27 | 103 | 27 | 0.51 |
| Aw | pg/mL | 1.6E1 | 1.6E1 | 1.6E1 | 1.8E1 | 5.4E0 | 8.2E0 | 3.5E0 | 6.7E0 | 3.3E1 | 4.8E1 | 255 | 27 | 103 | 27 | 0.57 |
| Ax | ng/mL | 2.1E0 | 1.6E0 | 8.2E0 | 9.3E0 | 1.8E1 | 1.5E1 | 1.9E-2 | 4.9E-2 | 1.5E2 | 5.1E1 | 255 | 27 | 103 | 27 | 0.52 |
| Ba | ng/mL | 3.7E1 | 1.2E2 | 2.8E2 | 7.9E2 | 7.3E2 | 1.7E3 | 3.7E-1 | 1.2E0 | 8.1E3 | 8.1E3 | 255 | 27 | 103 | 27 | 0.62 |
| Bb | ng/mL | 2.6E0 | 3.7E0 | 5.3E0 | 1.4E1 | 8.5E0 | 4.7E1 | 4.1E-3 | 4.1E-3 | 6.6E1 | 2.5E2 | 255 | 27 | 103 | 27 | 0.58 |
| Bc | ng/mL | 3.3E1 | 4.7E1 | 9.7E1 | 1.1E2 | 1.8E2 | 1.8E2 | 1.1E-1 | 4.2E-1 | 1.0E3 | 8.9E2 | 255 | 27 | 103 | 27 | 0.55 |
| Bg | ng/mL | 6.4E-2 | 1.6E-1 | 4.4E0 | 2.7E0 | 2.2E1 | 9.4E0 | 5.3E-4 | 5.3E-4 | 2.5E2 | 4.9E1 | 255 | 27 | 103 | 27 | 0.58 |
| Bn | ng/mL | 5.6E-2 | 5.6E-2 | 8.5E-1 | 1.4E0 | 1.6E0 | 2.2E0 | 5.6E-2 | 5.6E-2 | 8.5E0 | 7.2E0 | 255 | 27 | 103 | 27 | 0.55 |
| Bo | ng/mL | 1.1E1 | 1.9E1 | 1.3E1 | 2.5E1 | 9.6E0 | 3.9E1 | 1.6E-2 | 1.6E-2 | 7.4E1 | 2.1E2 | 255 | 27 | 103 | 27 | 0.61 |
| Ch | uIU/mL | 9.0E-1 | 1.5E0 | 6.5E0 | 2.3E1 | 2.1E1 | 5.7E1 | 3.4E-3 | 3.4E-3 | 2.3E2 | 2.1E2 | 255 | 27 | 103 | 27 | 0.57 |
| Co | pg/mL | 3.1E1 | 4.6E1 | 9.1E1 | 4.1E2 | 2.1E2 | 1.7E3 | 3.9E0 | 5.4E0 | 1.9E3 | 9.0E3 | 255 | 27 | 103 | 27 | 0.60 |
| Cp | ng/mL | 1.9E1 | 2.4E1 | 2.5E1 | 3.5E1 | 2.5E1 | 4.3E1 | 6.0E-1 | 2.5E0 | 2.9E2 | 2.4E2 | 255 | 27 | 103 | 27 | 0.60 |
| Cq | ng/mL | 2.4E-2 | 2.2E-2 | 1.6E-1 | 1.2E-1 | 1.1E0 | 4.1E-1 | 8.0E-4 | 8.0E-4 | 1.7E1 | 2.1E0 | 255 | 27 | 103 | 27 | 0.48 |
| Cs | ng/mL | 4.5E1 | 4.7E1 | 2.1E2 | 2.1E2 | 4.0E2 | 3.9E2 | 2.7E-2 | 2.8E0 | 2.9E3 | 1.6E3 | 255 | 27 | 103 | 27 | 0.50 |
| Ct | ng/mL | 1.2E0 | 3.5E-1 | 2.6E1 | 4.6E1 | 8.2E1 | 1.3E2 | 1.1E-4 | 2.5E-2 | 6.2E2 | 4.7E2 | 255 | 27 | 103 | 27 | 0.46 |
| Cu | ng/mL | 2.1E-1 | 2.3E-1 | 4.2E-1 | 3.7E-1 | 9.2E-1 | 3.4E-1 | 9.6E-3 | 3.6E-2 | 9.2E0 | 1.4E0 | 255 | 27 | 103 | 27 | 0.56 |
| Cv | ng/mL | 4.6E0 | 8.7E0 | 2.4E1 | 2.4E1 | 7.0E1 | 4.8E1 | 5.6E-3 | 2.9E-1 | 5.3E2 | 2.4E2 | 255 | 27 | 103 | 27 | 0.59 |
| Cw | mIU/mL | 2.8E-2 | 4.1E-2 | 3.8E-2 | 5.5E-2 | 3.0E-2 | 5.2E-2 | 2.3E-3 | 2.8E-3 | 1.9E-1 | 2.4E-1 | 255 | 27 | 103 | 27 | 0.61 |
| Cx | ng/mL | 1.8E-1 | 3.2E-2 | 5.4E1 | 7.0E1 | 1.0E2 | 1.3E2 | 9.3E-5 | 9.3E-5 | 3.9E2 | 3.9E2 | 255 | 27 | 103 | 27 | 0.48 |
| Db | ug/mL | 8.2E0 | 8.3E0 | 9.4E0 | 1.0E1 | 8.8E0 | 7.9E0 | 5.3E-1 | 9.3E-1 | 1.0E2 | 3.2E1 | 255 | 27 | 103 | 27 | 0.54 |
| Dc | nmol/L | 1.8E-2 | 2.5E-2 | 5.7E-2 | 4.1E-2 | 1.3E-1 | 5.5E-2 | 5.2E-6 | 1.4E-3 | 1.2E0 | 2.3E-1 | 255 | 27 | 103 | 27 | 0.54 |
| Dd | ug/mL | 6.9E-2 | 1.5E-1 | 1.8E-1 | 1.7E-1 | 2.6E-1 | 1.7E-1 | 1.9E-4 | 1.9E-3 | 1.6E0 | 7.8E-1 | 255 | 27 | 103 | 27 | 0.57 |
| De | ng/mL | 3.4E-3 | 3.4E-3 | 5.6E-2 | 9.1E-2 | 1.1E-1 | 1.9E-1 | 3.4E-3 | 3.4E-3 | 5.9E-1 | 8.2E-1 | 255 | 27 | 103 | 27 | 0.51 |
| Dg | ng/mL | 2.5E1 | 5.5E1 | 3.9E1 | 5.5E1 | 3.8E1 | 4.3E1 | 2.8E-1 | 2.9E0 | 1.9E2 | 1.9E2 | 255 | 27 | 103 | 27 | 0.61 |
| Di | pg/mL | 1.6E0 | 2.0E0 | 2.0E0 | 2.6E0 | 1.8E0 | 2.7E0 | 1.8E-1 | 1.8E-1 | 1.3E1 | 9.2E0 | 255 | 27 | 103 | 27 | 0.54 |
| Dk | uIU/mL | 1.4E-2 | 1.2E-2 | 9.3E-1 | 1.4E-1 | 6.3E-1 | 5.1E-1 | 1.1E-4 | 1.1E-4 | 8.9E0 | 2.7E0 | 255 | 27 | 103 | 27 | 0.53 |
| Dl | ng/mL | 2.0E2 | 2.9E2 | 2.7E2 | 3.6E2 | 2.4E2 | 3.4E2 | 3.1E0 | 1.3E1 | 1.4E3 | 1.3E3 | 255 | 27 | 103 | 27 | 0.57 |
| Dp | ng/ml | 2.5E0 | 1.3E0 | 4.9E0 | 4.6E0 | 6.8E0 | 7.1E0 | 3.7E-3 | 3.7E-3 | 4.3E1 | 2.7E1 | 122 | 26 | 99 | 26 | 0.43 |
| Ef | ng/ml | 9.5E-2 | 1.9E-1 | 6.9E-1 | 8.6E-1 | 1.7E0 | 2.0E0 | 5.7E-4 | 1.1E-2 | 1.0E1 | 9.5E0 | 165 | 26 | 102 | 26 | 0.58 |
| Wm | % | 8.2E-1 | 4.9E-1 | 3.0E1 | 3.8E0 | 1.9E2 | 1.1E1 | 5.4E-2 | 5.4E-2 | 2.4E3 | 5.5E1 | 204 | 27 | 119 | 27 | 0.41 |
| Ed | pg/ml | 5.2E-1 | 5.2E-1 | 9.3E1 | 9.8E0 | 6.6E2 | 2.4E1 | 5.2E-1 | 5.2E-1 | 7.3E3 | 1.0E2 | 122 | 26 | 98 | 26 | 0.38 |
| Tj | pg/mL | 3.7E-1 | 3.7E-1 | 7.6E1 | 2.9E1 | 3.7E2 | 1.1E2 | 3.6E-1 | 3.7E-1 | 3.5E3 | 5.9E2 | 165 | 26 | 103 | 26 | 0.48 |
| Po | pg/ml | 1.3E-1 | 2.6E-2 | 8.0E0 | 8.2E0 | 2.7E1 | 2.0E1 | 8.0E-3 | 2.6E-2 | 2.7E2 | 1.1E2 | 359 | 43 | 189 | 43 | 0.49 |
| Et | ng/ml | 1.0E3 | 1.4E3 | 1.3E3 | 1.9E3 | 1.0E3 | 1.4E3 | 7.5E1 | 1.6E2 | 4.9E3 | 4.9E3 | 359 | 43 | 189 | 43 | 0.61 |
| Fa | ng/ml | 3.9E1 | 3.7E1 | 1.2E2 | 1.6E2 | 7.3E2 | 5.5E2 | 3.4E-2 | 3.4E0 | 8.0E3 | 2.8E3 | 120 | 26 | 98 | 26 | 0.55 |
| Ez | ng/ml | 3.7E0 | 3.5E0 | 1.6E1 | 1.1E1 | 3.9E1 | 1.8E1 | 1.3E-2 | 1.3E-2 | 3.0E2 | 6.6E1 | 122 | 26 | 99 | 26 | 0.48 |
| Fb | ng/ml | 2.3E1 | 2.8E1 | 2.1E1 | 2.3E1 | 1.2E1 | 1.2E1 | 1.0E0 | 8.1E-1 | 5.7E1 | 4.0E1 | 120 | 26 | 98 | 26 | 0.57 |
| Ex | ng/ml | 6.0E-2 | 1.0E-1 | 2.4E-1 | 3.7E-1 | 8.4E-1 | 1.0E0 | 3.5E-5 | 1.7E-4 | 8.9E0 | 4.9E0 | 126 | 22 | 69 | 22 | 0.60 |
| Fn | ng/ml | 2.1E-1 | 2.1E-1 | 8.5E0 | 3.7E0 | 3.8E1 | 7.1E0 | 1.1E-14 | 1.1E-14 | 4.2E2 | 3.2E1 | 122 | 26 | 99 | 26 | 0.46 |
| Fp | ng/ml | 9.4E0 | 1.3E1 | 2.0E1 | 2.6E1 | 2.6E1 | 3.3E1 | 6.0E-3 | 1.3E-1 | 1.4E2 | 1.2E2 | 380 | 43 | 189 | 43 | 0.52 |
| Fr | ng/ml | 2.5E4 | 3.7E4 | 9.9E4 | 1.1E5 | 1.7E5 | 1.5E5 | 6.4E2 | 1.9E2 | 8.4E5 | 6.0E5 | 464 | 43 | 193 | 43 | 0.54 |
| Fw | pg/ml | 7.1E-1 | 1.1E0 | 1.0E2 | 4.8E0 | 6.7E2 | 9.0E0 | 1.1E-14 | 1.7E-1 | 6.9E3 | 4.2E1 | 167 | 26 | 103 | 26 | 0.46 |
| Fy | ng/ml | 3.1E1 | 2.8E1 | 4.9E1 | 3.8E1 | 5.5E1 | 3.8E1 | 1.2E-1 | 1.2E-1 | 3.3E2 | 1.8E2 | 121 | 25 | 98 | 25 | 0.47 |
| Gl | pg/ml | 6.1E3 | 6.7E3 | 9.8E3 | 9.8E3 | 9.0E3 | 9.6E3 | 2.3E2 | 2.0E2 | 3.4E4 | 3.0E4 | 162 | 26 | 102 | 26 | 0.49 |
| Gp | U/ml | 1.8E0 | 8.2E-1 | 4.4E0 | 3.3E0 | 7.6E0 | 5.7E0 | 1.3E-3 | 5.7E-3 | 6.7E1 | 2.3E1 | 167 | 26 | 103 | 26 | 0.40 |

Figure 21

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Gz | ug/ml | 1.2E0 | 6.6E0 | 1.1E1 | 6.3E0 | 5.3E1 | 6.0E0 | 2.9E-16 | 1.5E-1 | 4.8E2 | 1.9E1 | 81 | 22 | 64 | 22 | 0.54 |
| Ha | ng/ml | 2.7E0 | 2.3E0 | 8.4E0 | 1.1E1 | 1.9E1 | 2.1E1 | 1.7E-2 | 1.7E-2 | 1.0E2 | 7.7E1 | 120 | 26 | 98 | 26 | 0.50 |
| Nm | pg/ml | 1.2E4 | 1.5E4 | 2.4E4 | 2.3E4 | 4.9E4 | 2.8E4 | 1.0E-9 | 1.0E-9 | 7.8E5 | 1.2E5 | 358 | 43 | 190 | 43 | 0.51 |
| Nn | pg/ml | 1.3E2 | 9.7E1 | 2.5E3 | 6.7E2 | 1.1E4 | 1.2E3 | 1.0E-9 | 1.0E-9 | 1.0E5 | 4.9E3 | 358 | 43 | 190 | 43 | 0.53 |
| No | pg/ml | 1.3E1 | 8.7E0 | 2.7E1 | 2.4E1 | 5.9E1 | 3.5E1 | 1.0E-9 | 1.0E-9 | 5.9E2 | 1.4E2 | 358 | 43 | 190 | 43 | 0.46 |
| Nq | pg/ml | 2.2E0 | 1.0E-9 | 2.1E1 | 1.2E1 | 8.4E1 | 5.0E1 | 1.0E-9 | 1.0E-9 | 1.2E3 | 3.3E2 | 358 | 43 | 190 | 43 | 0.42 |
| Nr | pg/ml | 4.7E-1 | 6.1E-1 | 1.6E1 | 1.3E1 | 7.0E1 | 3.4E1 | 1.0E-9 | 1.0E-9 | 9.8E2 | 1.7E2 | 358 | 43 | 190 | 43 | 0.51 |
| Ns | pg/ml | 1.0E-9 | 1.0E-9 | 8.9E0 | 6.9E0 | 4.5E1 | 2.7E1 | 1.0E-9 | 1.0E-9 | 6.8E2 | 1.3E2 | 358 | 43 | 190 | 43 | 0.50 |
| Nt | pg/ml | 9.4E1 | 1.0E2 | 1.2E2 | 1.2E2 | 9.2E1 | 7.5E1 | 1.0E-9 | 1.0E-9 | 5.9E2 | 3.4E2 | 358 | 43 | 190 | 43 | 0.54 |
| Nu | pg/ml | 1.7E1 | 4.3E1 | 4.9E1 | 6.5E1 | 8.8E1 | 7.3E1 | 1.0E-9 | 1.0E-9 | 8.9E2 | 2.6E2 | 358 | 43 | 190 | 43 | 0.57 |
| Lu | pg/ml | 1.0E4 | 1.0E4 | 1.5E4 | 9.0E3 | 3.2E4 | 5.8E3 | 6.7E2 | 1.4E3 | 3.9E5 | 2.1E4 | 360 | 43 | 190 | 43 | 0.45 |
| Lv | pg/ml | 1.0E-9 | 1.0E-9 | 1.1E1 | 1.4E1 | 2.2E1 | 2.0E1 | 1.0E-9 | 1.0E-9 | 2.4E2 | 7.5E1 | 360 | 43 | 190 | 43 | 0.55 |
| Lw | pg/ml | 1.0E-9 | 1.0E-9 | 1.4E-1 | 2.3E-1 | 1.8E0 | 1.5E0 | 1.0E-9 | 1.0E-9 | 3.2E1 | 9.9E0 | 360 | 43 | 190 | 43 | 0.50 |
| Lx | pg/ml | 1.0E-9 | 1.0E-9 | 1.1E2 | 1.6E2 | 4.2E2 | 3.6E2 | 1.0E-9 | 1.0E-9 | 6.2E3 | 1.8E3 | 360 | 43 | 190 | 43 | 0.54 |
| Ly | pg/ml | 1.0E-9 | 1.1E1 | 9.1E0 | 1.7E1 | 1.8E1 | 1.8E1 | 1.0E-9 | 1.0E-9 | 1.2E2 | 5.6E1 | 360 | 43 | 190 | 43 | 0.65 |
| Lz | pg/ml | 1.0E-9 | 1.0E-9 | 2.9E0 | 1.5E0 | 2.4E1 | 7.1E0 | 1.0E-9 | 1.0E-9 | 4.3E2 | 4.3E1 | 360 | 43 | 190 | 43 | 0.49 |
| Ma | pg/ml | 2.4E2 | 3.3E2 | 1.5E3 | 1.3E3 | 4.7E3 | 2.3E3 | 1.0E-9 | 1.0E-9 | 6.5E4 | 1.2E4 | 360 | 43 | 190 | 43 | 0.50 |
| Mb | pg/ml | 2.5E1 | 2.7E1 | 3.1E1 | 3.1E1 | 1.4E1 | 1.2E1 | 5.4E0 | 1.4E1 | 9.3E1 | 5.9E1 | 360 | 43 | 190 | 43 | 0.54 |
| Mc | pg/ml | 1.0E-9 | 1.0E-9 | 1.7E-2 | 5.8E-2 | 2.3E-1 | 3.8E-1 | 1.0E-9 | 1.0E-9 | 4.0E0 | 2.5E0 | 360 | 43 | 190 | 43 | 0.51 |
| Md | pg/ml | 1.0E-9 | 1.0E-9 | 6.2E-1 | 2.4E-1 | 5.2E0 | 1.2E0 | 1.0E-9 | 1.0E-9 | 6.8E1 | 7.3E0 | 360 | 43 | 190 | 43 | 0.51 |
| Me | pg/ml | 3.2E1 | 2.4E1 | 2.9E1 | 2.6E1 | 1.6E1 | 1.3E1 | 1.0E-9 | 4.2E0 | 1.2E2 | 5.5E1 | 360 | 43 | 190 | 43 | 0.42 |
| Mf | pg/ml | 1.0E-9 | 1.0E-9 | 3.7E-1 | 3.8E-1 | 1.6E0 | 1.3E0 | 1.0E-9 | 1.0E-9 | 2.0E1 | 7.7E0 | 360 | 43 | 190 | 43 | 0.54 |
| Mg | pg/ml | 1.9E0 | 3.3E0 | 6.4E0 | 7.1E0 | 1.1E1 | 9.5E0 | 1.0E-9 | 1.0E-9 | 8.8E1 | 3.5E1 | 360 | 43 | 190 | 43 | 0.55 |
| Mh | pg/ml | 1.0E-9 | 1.0E-9 | 1.1E0 | 3.4E-1 | 8.4E0 | 1.3E0 | 1.0E-9 | 1.0E-9 | 1.1E2 | 7.8E0 | 360 | 43 | 190 | 43 | 0.48 |
| Mi | pg/ml | 1.0E-9 | 1.0E-9 | 6.9E-1 | 1.0E-9 | 7.1E0 | 0.0E0 | 1.0E-9 | 1.0E-9 | 1.2E2 | 1.0E-9 | 360 | 43 | 190 | 43 | 0.49 |
| Mj | pg/ml | 1.0E-9 | 1.0E-9 | 5.2E0 | 1.9E0 | 3.1E1 | 5.6E0 | 1.0E-9 | 1.0E-9 | 4.6E2 | 2.9E1 | 360 | 43 | 190 | 43 | 0.50 |
| Mk | pg/ml | 6.5E-1 | 1.0E-9 | 1.6E1 | 1.5E1 | 9.9E1 | 5.4E1 | 1.0E-9 | 1.0E-9 | 1.7E3 | 3.3E2 | 360 | 43 | 190 | 43 | 0.46 |
| Ml | pg/ml | 1.0E-9 | 1.0E-9 | 9.1E0 | 3.2E-1 | 1.1E2 | 8.0E-1 | 1.0E-9 | 1.0E-9 | 2.1E3 | 2.8E0 | 360 | 43 | 190 | 43 | 0.48 |
| Mm | pg/ml | 4.0E2 | 5.3E2 | 8.0E2 | 9.2E2 | 9.7E2 | 1.6E3 | 1.0E-9 | 1.0E-9 | 6.0E3 | 9.9E3 | 360 | 43 | 190 | 43 | 0.51 |
| Mn | pg/ml | 4.8E0 | 4.4E0 | 1.0E1 | 6.1E0 | 2.5E1 | 6.4E0 | 1.0E-9 | 1.0E-9 | 3.5E2 | 3.3E1 | 360 | 43 | 190 | 43 | 0.46 |
| Mp | pg/ml | 1.0E-9 | 1.0E-9 | 9.7E0 | 5.3E0 | 2.2E1 | 1.6E1 | 1.0E-9 | 1.0E-9 | 1.8E2 | 1.0E2 | 360 | 43 | 190 | 43 | 0.44 |
| Mq | pg/ml | 1.0E-9 | 1.0E-9 | 2.8E0 | 4.1E0 | 1.7E1 | 1.5E1 | 1.0E-9 | 1.0E-9 | 2.1E2 | 6.5E1 | 360 | 43 | 190 | 43 | 0.50 |
| Mr | pg/ml | 1.0E-9 | 1.0E-9 | 1.4E1 | 2.4E1 | 8.7E1 | 7.2E1 | 1.0E-9 | 1.0E-9 | 1.4E3 | 3.1E2 | 360 | 43 | 190 | 43 | 0.54 |
| Ms | pg/ml | 3.8E2 | 4.3E2 | 5.6E2 | 5.2E2 | 7.1E2 | 5.3E2 | 1.0E-9 | 1.0E-9 | 5.6E3 | 2.5E3 | 360 | 43 | 190 | 43 | 0.50 |
| Mt | pg/ml | 1.0E-9 | 4.8E-1 | 1.1E1 | 3.5E0 | 6.3E1 | 1.2E1 | 1.0E-9 | 1.0E-9 | 8.7E2 | 7.0E1 | 360 | 43 | 190 | 43 | 0.51 |
| Mu | pg/ml | 1.0E-9 | 1.0E-9 | 1.5E0 | 6.7E-1 | 1.0E1 | 3.5E0 | 1.0E-9 | 1.0E-9 | 9.9E1 | 2.3E1 | 360 | 43 | 190 | 43 | 0.50 |
| Mv | pg/ml | 1.0E-9 | 1.0E-9 | 8.2E1 | 3.3E1 | 4.2E2 | 1.5E2 | 1.0E-9 | 1.0E-9 | 4.5E3 | 9.4E2 | 360 | 43 | 190 | 43 | 0.48 |
| Mw | pg/ml | 2.5E1 | 1.6E1 | 5.8E2 | 4.2E2 | 3.9E3 | 2.4E3 | 1.0E-9 | 1.0E-9 | 6.2E4 | 1.6E4 | 360 | 43 | 190 | 43 | 0.46 |
| Mx | pg/ml | 1.0E-9 | 1.0E-9 | 1.8E-1 | 1.6E-1 | 8.2E-1 | 5.7E-1 | 1.0E-9 | 1.0E-9 | 9.2E0 | 3.4E0 | 360 | 43 | 190 | 43 | 0.51 |
| My | pg/ml | 1.0E-9 | 1.0E-9 | 5.6E2 | 7.5E2 | 3.5E3 | 4.7E3 | 1.0E-9 | 1.0E-9 | 3.9E4 | 3.1E4 | 360 | 43 | 190 | 43 | 0.49 |
| Mz | pg/ml | 8.5E0 | 7.3E0 | 2.1E1 | 1.8E1 | 5.9E1 | 3.7E1 | 1.0E-9 | 1.0E-9 | 8.4E2 | 2.1E2 | 360 | 43 | 190 | 43 | 0.48 |
| Na | pg/ml | 1.0E-9 | 1.0E-9 | 5.7E-1 | 6.9E-1 | 1.8E0 | 1.9E0 | 1.0E-9 | 1.0E-9 | 7.8E0 | 7.2E0 | 360 | 43 | 190 | 43 | 0.53 |
| Nb | pg/ml | 1.8E0 | 1.6E0 | 4.6E0 | 4.2E0 | 1.6E1 | 1.2E1 | 1.0E-9 | 1.0E-9 | 2.3E2 | 8.1E1 | 360 | 43 | 190 | 43 | 0.47 |
| Nc | pg/ml | 4.5E2 | 1.7E2 | 6.7E2 | 4.2E2 | 8.4E2 | 5.7E2 | 1.0E-9 | 1.0E-9 | 9.2E3 | 1.8E3 | 360 | 43 | 190 | 43 | 0.39 |
| Nd | pg/ml | 3.1E1 | 9.3E0 | 2.6E1 | 1.7E1 | 2.0E1 | 1.7E1 | 1.0E-9 | 1.0E-9 | 8.4E1 | 5.5E1 | 360 | 43 | 190 | 43 | 0.36 |
| Ne | pg/ml | 4.9E2 | 2.7E2 | 6.3E2 | 3.4E2 | 6.4E2 | 3.9E2 | 1.0E-9 | 1.0E-9 | 7.0E3 | 1.5E3 | 360 | 43 | 190 | 43 | 0.34 |
| Nf | pg/ml | 1.0E-9 | 1.0E-9 | 2.9E0 | 1.8E0 | 8.8E0 | 7.0E0 | 1.0E-9 | 1.0E-9 | 8.2E1 | 4.4E1 | 360 | 43 | 190 | 43 | 0.43 |
| Ng | pg/ml | 2.1E1 | 2.6E1 | 1.1E2 | 1.0E2 | 2.3E2 | 2.0E2 | 1.0E-9 | 1.0E-9 | 1.6E3 | 1.1E3 | 360 | 43 | 190 | 43 | 0.48 |
| Nh | pg/ml | 7.7E1 | 3.8E1 | 9.8E1 | 5.6E1 | 8.7E1 | 5.1E1 | 1.0E-9 | 2.5E0 | 5.6E2 | 2.2E2 | 360 | 43 | 190 | 43 | 0.34 |
| Ni | pg/ml | 4.5E0 | 1.0E-9 | 7.4E1 | 1.0E2 | 1.1E2 | 1.7E2 | 1.0E-9 | 1.0E-9 | 7.1E2 | 7.1E2 | 360 | 43 | 190 | 43 | 0.51 |
| Nj | pg/ml | 9.0E0 | 2.4E0 | 1.2E1 | 8.1E0 | 1.2E1 | 1.1E1 | 1.0E-9 | 1.0E-9 | 8.3E1 | 4.6E1 | 360 | 43 | 190 | 43 | 0.35 |
| Nk | pg/ml | 2.2E1 | 1.5E1 | 3.6E1 | 2.9E1 | 4.0E1 | 3.8E1 | 1.0E-9 | 1.0E-9 | 1.8E2 | 1.7E2 | 360 | 43 | 190 | 43 | 0.44 |
| Nl | pg/ml | 5.2E1 | 1.6E1 | 7.0E1 | 3.5E1 | 8.2E1 | 4.2E1 | 1.0E-9 | 1.0E-9 | 1.1E3 | 1.5E2 | 360 | 43 | 190 | 43 | 0.33 |
| Tz | pg/ml | 3.7E3 | 5.2E3 | 7.5E3 | 7.3E3 | 1.1E4 | 6.9E3 | 7.4E1 | 6.3E2 | 8.8E4 | 3.3E4 | 124 | 27 | 98 | 27 | 0.57 |
| Ua | pg/ml | 3.5E3 | 3.4E3 | 3.0E4 | 1.2E4 | 1.9E5 | 1.9E4 | 3.5E2 | 4.8E2 | 2.1E6 | 6.4E4 | 124 | 27 | 98 | 27 | 0.48 |
| Ub | pg/ml | 5.8E2 | 5.7E2 | 8.7E2 | 7.5E2 | 1.2E3 | 7.9E2 | 1.0E-9 | 1.0E-9 | 9.8E3 | 3.3E3 | 124 | 27 | 98 | 27 | 0.47 |
| Ue | pg/ml | 3.1E1 | 2.3E1 | 3.5E1 | 2.8E1 | 2.4E1 | 2.9E1 | 4.2E0 | 5.1E0 | 1.2E2 | 1.5E2 | 124 | 27 | 98 | 27 | 0.37 |

Figure 21 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Uc | pg/ml | 7.8E2 | 6.9E2 | 1.6E3 | 1.3E3 | 3.3E3 | 1.8E3 | 3.3E1 | 8.9E1 | 2.9E4 | 9.6E3 | 124 | 27 | 98 | 27 | 0.49 |
| Ud | pg/ml | 1.0E-9 | 1.0E-9 | 3.4E0 | 1.0E-9 | 3.5E1 | 0.0E0 | 1.0E-9 | 1.0E-9 | 3.9E2 | 1.0E-9 | 124 | 27 | 98 | 27 | 0.49 |
| Hq | pg/ml | 1.1E0 | 1.5E0 | 1.1E1 | 7.9E2 | 5.9E1 | 5.2E3 | 1.0E-9 | 1.0E-9 | 9.5E2 | 3.4E4 | 360 | 43 | 190 | 43 | 0.51 |
| Hr | pg/ml | 1.3E2 | 1.2E2 | 8.3E2 | 7.2E2 | 1.6E3 | 9.5E2 | 1.0E-9 | 1.0E-9 | 1.2E4 | 3.7E3 | 360 | 43 | 190 | 43 | 0.53 |
| Hu | pg/ml | 7.9E0 | 1.8E1 | 3.5E3 | 1.4E3 | 3.5E4 | 8.4E3 | 1.0E-9 | 1.0E-9 | 6.3E5 | 5.5E4 | 360 | 43 | 190 | 43 | 0.49 |
| Hv | pg/ml | 1.3E0 | 2.1E0 | 3.4E0 | 4.1E0 | 1.5E1 | 7.1E0 | 1.0E-9 | 1.0E-9 | 2.5E2 | 3.5E1 | 360 | 43 | 190 | 43 | 0.58 |
| Hw | pg/ml | 7.2E0 | 6.7E0 | 2.5E1 | 1.6E1 | 1.1E2 | 2.6E1 | 1.0E-9 | 1.0E-9 | 1.7E3 | 1.5E2 | 360 | 43 | 190 | 43 | 0.51 |
| Hx | pg/ml | 7.2E0 | 1.2E1 | 6.0E1 | 2.0E1 | 5.0E2 | 2.6E1 | 1.0E-9 | 1.0E-9 | 9.3E3 | 1.5E2 | 360 | 43 | 190 | 43 | 0.57 |
| Ib | ng/ml | 6.9E-2 | 2.7E-2 | 6.9E-1 | 1.9E0 | 3.0E0 | 6.2E0 | 1.0E-9 | 1.0E-9 | 3.0E1 | 3.0E1 | 122 | 24 | 99 | 24 | 0.44 |
| Ic | U/ml | 2.2E2 | 2.2E2 | 3.1E2 | 4.7E3 | 1.4E3 | 1.9E4 | 2.9E0 | 2.2E1 | 1.5E4 | 9.3E4 | 122 | 24 | 99 | 24 | 0.68 |
| Id | U/ml | 6.2E-1 | 7.1E-1 | 1.0E0 | 1.6E0 | 1.2E0 | 2.7E0 | 1.0E-9 | 2.7E-1 | 6.9E0 | 1.2E1 | 122 | 24 | 99 | 24 | 0.58 |
| Tt | pg/ml | 1.6E2 | 1.6E2 | 1.6E2 | 1.8E2 | 4.4E1 | 5.2E1 | 8.0E1 | 1.1E2 | 3.0E2 | 2.9E2 | 114 | 21 | 92 | 21 | 0.60 |
| To | pg/ml | 1.6E0 | 1.8E0 | 1.9E0 | 2.0E0 | 2.6E0 | 1.9E0 | 1.0E-9 | 1.0E-9 | 2.3E1 | 5.1E0 | 119 | 23 | 95 | 23 | 0.55 |
| Tr | pg/ml | 2.8E0 | 2.7E0 | 4.1E0 | 4.5E0 | 4.7E0 | 4.1E0 | 3.5E-2 | 3.9E-1 | 2.9E1 | 1.3E1 | 118 | 21 | 94 | 21 | 0.53 |
| Tn | pg/ml | 2.1E1 | 4.3E1 | 5.9E1 | 9.4E1 | 1.5E2 | 2.5E2 | 2.6E0 | 7.4E0 | 1.5E3 | 1.2E3 | 119 | 23 | 95 | 23 | 0.62 |
| Tv | ng/ml | 1.2E1 | 1.2E1 | 2.0E1 | 3.1E1 | 4.8E1 | 6.6E1 | 1.0E-9 | 1.0E-9 | 4.9E2 | 3.2E2 | 119 | 23 | 95 | 23 | 0.53 |
| Ih | ng/ml | 5.7E1 | 4.5E1 | 2.0E2 | 1.8E2 | 3.6E2 | 2.9E2 | 1.0E-9 | 1.0E-9 | 2.5E3 | 1.3E3 | 360 | 43 | 190 | 43 | 0.48 |
| Ii | ng/ml | 7.0E1 | 6.4E1 | 2.7E2 | 1.8E2 | 8.1E2 | 3.9E2 | 7.5E-1 | 7.3E-1 | 8.4E3 | 2.5E3 | 360 | 43 | 190 | 43 | 0.48 |
| Ij | ng/ml | 7.0E1 | 7.4E1 | 2.0E2 | 1.3E2 | 7.3E2 | 2.2E2 | 2.1E0 | 1.0E-9 | 6.4E3 | 1.4E3 | 358 | 43 | 190 | 43 | 0.52 |
| Ik | ng/ml | 1.2E1 | 1.6E1 | 9.2E2 | 3.0E2 | 9.2E3 | 5.2E2 | 5.9E-1 | 8.8E-1 | 1.2E5 | 2.1E3 | 358 | 43 | 190 | 43 | 0.54 |
| Il | ng/ml | 3.3E2 | 2.9E2 | 1.4E3 | 8.2E2 | 3.0E3 | 1.9E3 | 1.0E-9 | 1.0E-9 | 1.2E4 | 1.2E4 | 354 | 43 | 190 | 43 | 0.47 |
| Im | ng/ml | 1.9E2 | 1.8E2 | 3.0E2 | 3.0E2 | 3.4E2 | 3.5E2 | 1.3E1 | 3.0E1 | 3.1E3 | 1.8E3 | 357 | 43 | 190 | 43 | 0.49 |
| In | ng/ml | 4.2E0 | 2.4E0 | 3.6E1 | 7.0E0 | 2.3E2 | 1.0E1 | 1.0E-9 | 1.0E-9 | 3.9E3 | 5.2E1 | 360 | 43 | 190 | 43 | 0.43 |
| Hb | ng/ml | 2.0E1 | 2.2E1 | 2.7E1 | 3.3E1 | 2.6E1 | 3.0E1 | 1.1E0 | 1.3E0 | 1.5E2 | 1.1E2 | 120 | 26 | 98 | 26 | 0.55 |
| Hc | pg/ml | 6.1E2 | 7.6E2 | 2.2E3 | 5.0E3 | 4.9E3 | 1.9E4 | 1.0E-9 | 2.2E2 | 3.6E4 | 1.0E5 | 120 | 26 | 98 | 26 | 0.55 |
| Hf | ng/ml | 1.2E2 | 1.7E2 | 3.6E2 | 2.7E2 | 5.3E2 | 3.7E2 | 1.0E-9 | 1.0E-9 | 2.5E3 | 1.3E3 | 120 | 26 | 98 | 26 | 0.51 |
| Io | ng/ml | 6.9E3 | 5.7E3 | 1.7E4 | 8.7E3 | 5.1E4 | 8.8E3 | 6.6E1 | 2.1E2 | 8.8E5 | 3.7E4 | 357 | 42 | 189 | 42 | 0.44 |
| Ip | ng/ml | 8.1E0 | 6.3E0 | 1.8E1 | 1.8E1 | 2.7E1 | 2.5E1 | 1.0E-9 | 1.4E-2 | 2.6E2 | 1.2E2 | 357 | 42 | 189 | 42 | 0.48 |
| Iq | ug/ml | 9.1E-2 | 1.0E-1 | 3.9E1 | 3.2E2 | 7.2E2 | 2.1E3 | 1.0E-9 | 1.0E-9 | 1.4E4 | 1.4E4 | 357 | 42 | 189 | 42 | 0.51 |
| Ir | ug/ml | 2.9E-1 | 4.4E-1 | 4.4E0 | 6.4E0 | 3.3E1 | 3.4E1 | 1.0E-9 | 1.0E-9 | 5.1E2 | 2.2E2 | 356 | 42 | 189 | 42 | 0.56 |
| Is | ng/ml | 1.3E0 | 1.8E0 | 6.4E0 | 4.4E0 | 3.1E1 | 5.8E0 | 1.0E-9 | 1.0E-9 | 5.5E2 | 2.2E1 | 357 | 42 | 189 | 42 | 0.53 |
| It | ng/ml | 1.9E0 | 2.9E0 | 2.6E1 | 1.1E1 | 1.3E2 | 2.7E1 | 1.0E-9 | 1.0E-9 | 1.2E3 | 1.5E2 | 357 | 42 | 189 | 42 | 0.58 |
| Iu | ng/ml | 1.9E2 | 3.5E2 | 1.6E3 | 1.5E3 | 5.0E3 | 4.1E3 | 1.0E-9 | 1.0E-9 | 2.9E4 | 2.4E4 | 357 | 42 | 189 | 42 | 0.55 |
| Iv | ng/ml | 1.1E1 | 1.2E1 | 8.5E1 | 3.8E1 | 8.5E2 | 7.6E1 | 1.0E-9 | 1.0E-9 | 1.6E4 | 4.5E2 | 357 | 41 | 189 | 41 | 0.53 |
| Iz | ng/ml | 1.2E2 | 1.4E2 | 4.2E2 | 3.5E2 | 9.7E2 | 5.7E2 | 1.5E0 | 9.4E0 | 8.4E3 | 2.7E3 | 120 | 26 | 98 | 26 | 0.54 |
| Rc | pg/ml | 5.0E3 | 5.9E3 | 6.4E3 | 7.9E3 | 5.0E3 | 6.0E3 | 1.9E2 | 1.0E3 | 3.0E4 | 2.2E4 | 122 | 26 | 98 | 26 | 0.55 |
| Rb | pg/ml | 7.5E-1 | 1.1E0 | 2.4E0 | 3.2E0 | 3.6E0 | 8.3E0 | 1.0E-9 | 1.0E-9 | 1.6E1 | 4.3E1 | 122 | 26 | 98 | 26 | 0.56 |
| Pz | ng/ml | 3.1E3 | 6.5E3 | 6.1E3 | 5.8E3 | 9.7E3 | 4.5E3 | 1.3E1 | 9.5E1 | 9.5E4 | 1.4E4 | 358 | 43 | 189 | 43 | 0.53 |
| Qa | ng/ml | 2.7E3 | 3.6E3 | 5.9E3 | 5.5E3 | 8.0E3 | 4.9E3 | 1.5E2 | 2.9E2 | 5.2E4 | 1.9E4 | 358 | 43 | 189 | 43 | 0.56 |
| Qb | ng/ml | 8.3E1 | 1.0E2 | 2.5E2 | 1.7E2 | 7.0E2 | 2.3E2 | 7.9E-1 | 8.7E0 | 8.3E3 | 1.1E3 | 358 | 43 | 189 | 43 | 0.52 |
| Qc | ng/ml | 1.9E2 | 1.8E2 | 4.7E2 | 3.8E2 | 9.5E2 | 4.6E2 | 8.1E-1 | 5.0E0 | 1.1E4 | 1.6E3 | 358 | 43 | 189 | 43 | 0.49 |
| Qd | ng/ml | 7.9E3 | 9.5E3 | 2.2E4 | 1.7E4 | 1.1E5 | 2.6E4 | 1.5E2 | 1.0E3 | 2.0E6 | 1.5E5 | 358 | 43 | 189 | 43 | 0.52 |
| Qe | ng/ml | 6.9E2 | 1.0E3 | 1.9E3 | 1.5E3 | 5.6E3 | 1.8E3 | 1.0E-9 | 7.9E1 | 9.7E4 | 9.3E3 | 358 | 43 | 189 | 43 | 0.54 |
| Jd | ng/ml | 4.3E-1 | 6.7E-1 | 7.5E0 | 5.1E0 | 5.9E1 | 1.8E1 | 1.0E-9 | 1.0E-9 | 6.5E2 | 9.1E1 | 122 | 26 | 99 | 26 | 0.57 |
| Je | ng/ml | 1.0E-9 | 1.4E-1 | 1.4E0 | 4.6E0 | 5.4E0 | 1.7E1 | 1.0E-9 | 1.0E-9 | 5.6E1 | 8.8E1 | 122 | 26 | 99 | 26 | 0.56 |
| Jf | ng/ml | 1.0E-9 | 1.0E-9 | 7.4E-1 | 1.4E0 | 1.9E0 | 2.8E0 | 1.0E-9 | 1.0E-9 | 1.2E1 | 8.6E0 | 122 | 26 | 99 | 26 | 0.56 |
| Jg | ng/ml | 3.7E2 | 7.2E2 | 6.8E2 | 7.9E2 | 1.0E3 | 8.2E2 | 5.8E0 | 3.8E0 | 1.0E4 | 4.0E3 | 360 | 43 | 190 | 43 | 0.56 |
| Jh | ng/ml | 2.3E0 | 4.1E0 | 2.4E1 | 4.4E1 | 9.5E1 | 2.4E2 | 1.0E-9 | 1.0E-9 | 1.2E3 | 1.6E3 | 360 | 43 | 190 | 43 | 0.51 |
| Ji | ng/ml | 4.6E1 | 4.3E1 | 6.6E1 | 7.7E1 | 7.0E1 | 7.6E1 | 1.1E0 | 4.6E0 | 5.3E2 | 3.8E2 | 360 | 43 | 190 | 43 | 0.54 |
| Sr | pg/mL | 3.2E2 | 3.2E2 | 7.5E2 | 1.1E3 | 1.3E3 | 1.7E3 | 1.0E-9 | 1.0E-9 | 9.8E3 | 5.5E3 | 121 | 26 | 98 | 26 | 0.53 |
| Ss | pg/mL | 6.2E4 | 1.9E5 | 1.2E5 | 2.0E5 | 1.4E5 | 3.4E5 | 9.5E3 | 1.1E4 | 7.1E5 | 1.8E6 | 121 | 26 | 98 | 26 | 0.59 |
| St | pg/mL | 1.7E7 | 1.9E7 | 4.0E7 | 4.5E7 | 5.3E7 | 4.9E7 | 7.8E5 | 1.6E6 | 4.1E8 | 1.9E8 | 119 | 25 | 96 | 25 | 0.55 |
| Ra | pg/ml | 1.0E-9 | 5.2E-1 | 6.8E-1 | 9.7E-1 | 1.3E0 | 1.5E0 | 1.0E-9 | 1.0E-9 | 7.3E0 | 4.9E0 | 122 | 26 | 98 | 26 | 0.61 |
| Qz | pg/ml | 1.1E1 | 1.0E-9 | 7.1E1 | 5.8E1 | 1.1E2 | 1.2E2 | 1.0E-9 | 1.0E-9 | 7.1E2 | 4.7E2 | 122 | 26 | 98 | 26 | 0.34 |
| Qy | pg/ml | 3.9E-1 | 5.9E-1 | 3.6E0 | 2.6E1 | 1.6E1 | 1.3E2 | 1.0E-9 | 1.0E-9 | 1.6E2 | 6.5E2 | 122 | 26 | 98 | 26 | 0.60 |
| Qx | pg/ml | 1.0E-9 | 1.0E-9 | 5.6E0 | 2.4E1 | 4.9E1 | 1.1E2 | 1.0E-9 | 1.0E-9 | 5.4E2 | 5.8E2 | 122 | 26 | 98 | 26 | 0.57 |
| Qw | pg/ml | 9.0E-2 | 1.0E-9 | 2.2E0 | 3.4E-1 | 1.1E1 | 9.7E-1 | 1.0E-9 | 1.0E-9 | 1.2E2 | 4.5E0 | 122 | 26 | 98 | 26 | 0.35 |

Figure 21 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Qv | pg/ml | 2.8E4 | 1.3E4 | 3.9E4 | 6.2E4 | 7.4E4 | 1.8E5 | 1.2E3 | 1.6E3 | 7.4E5 | 9.4E5 | 122 | 26 | 98 | 26 | 0.40 |
| Qu | pg/ml | 1.7E0 | 2.4E1 | 8.6E1 | 5.5E1 | 1.8E2 | 1.1E2 | 1.0E-9 | 1.0E-9 | 8.0E2 | 5.1E2 | 122 | 26 | 98 | 26 | 0.55 |
| Qt | pg/ml | 9.9E0 | 1.1E1 | 3.6E1 | 6.1E1 | 7.7E1 | 1.7E2 | 1.0E-9 | 1.0E-9 | 4.1E2 | 8.5E2 | 122 | 26 | 98 | 26 | 0.51 |
| Qh | ng/ml | 1.3E1 | 1.6E1 | 3.5E1 | 3.1E1 | 7.0E1 | 3.5E1 | 1.2E-1 | 1.0E-9 | 6.4E2 | 1.5E2 | 122 | 26 | 98 | 26 | 0.57 |
| Qg | ng/ml | 9.0E0 | 4.5E0 | 1.7E1 | 1.2E1 | 2.5E1 | 1.6E1 | 1.5E-1 | 5.1E-2 | 1.8E2 | 6.3E1 | 122 | 26 | 98 | 26 | 0.39 |
| Jj | ng/ml | 7.1E2 | 5.2E2 | 2.7E3 | 1.4E3 | 1.9E4 | 3.3E3 | 2.3E0 | 1.3E1 | 3.4E5 | 1.7E4 | 360 | 43 | 190 | 43 | 0.45 |
| Jk | ng/ml | 3.0E0 | 3.1E0 | 2.1E1 | 1.7E1 | 4.6E1 | 3.6E1 | 1.0E-9 | 2.0E-1 | 2.8E2 | 1.6E2 | 360 | 43 | 190 | 43 | 0.51 |
| Jl | ng/ml | 3.4E-1 | 4.8E-1 | 1.9E0 | 1.3E0 | 4.7E0 | 3.3E0 | 7.6E-4 | 1.6E-2 | 3.2E1 | 2.0E1 | 360 | 43 | 190 | 43 | 0.51 |
| Jm | ng/ml | 1.5E1 | 2.2E1 | 5.3E1 | 3.9E1 | 1.2E2 | 5.3E1 | 1.0E-9 | 4.1E-1 | 1.4E3 | 2.4E2 | 360 | 43 | 190 | 43 | 0.54 |
| Jn | pg/ml | 3.2E-1 | 2.4E-1 | 3.2E0 | 1.1E0 | 3.3E1 | 3.1E0 | 1.0E-9 | 1.0E-9 | 6.2E2 | 2.0E1 | 360 | 42 | 190 | 42 | 0.49 |
| Jo | pg/ml | 3.5E3 | 4.3E3 | 4.8E3 | 5.2E3 | 3.9E3 | 4.6E3 | 2.0E1 | 7.7E2 | 2.0E4 | 2.0E4 | 360 | 43 | 190 | 43 | 0.52 |
| Jp | pg/ml | 6.3E4 | 7.1E4 | 6.6E4 | 7.0E4 | 3.7E4 | 3.3E4 | 5.8E2 | 5.0E3 | 3.0E5 | 1.5E5 | 360 | 43 | 190 | 43 | 0.56 |
| Jq | pg/ml | 9.1E1 | 9.2E1 | 1.4E2 | 1.6E2 | 1.8E2 | 1.8E2 | 1.0E0 | 1.3E1 | 2.0E3 | 7.9E2 | 360 | 43 | 190 | 43 | 0.52 |
| Jr | pg/ml | 3.3E0 | 4.1E0 | 4.5E1 | 1.7E1 | 5.6E2 | 6.3E1 | 1.0E-9 | 1.0E-9 | 1.1E4 | 4.1E2 | 360 | 43 | 190 | 43 | 0.50 |
| Js | pg/ml | 1.2E1 | 1.2E1 | 6.5E1 | 2.2E1 | 5.4E2 | 4.7E1 | 1.0E-9 | 6.1E-1 | 1.0E4 | 2.9E2 | 360 | 43 | 190 | 43 | 0.47 |
| Jt | pg/ml | 2.2E3 | 2.8E3 | 2.8E3 | 3.1E3 | 2.2E3 | 1.8E3 | 2.2E1 | 3.7E2 | 2.2E4 | 6.6E3 | 360 | 43 | 190 | 43 | 0.57 |
| Ju | mIU/ml | 7.2E0 | 1.4E1 | 2.0E1 | 2.2E1 | 3.4E1 | 2.7E1 | 6.5E-2 | 1.7E-1 | 2.3E2 | 1.0E2 | 122 | 26 | 99 | 26 | 0.56 |
| Jv | mIU/ml | 9.3E0 | 1.0E1 | 3.1E1 | 3.7E1 | 6.1E1 | 5.8E1 | 1.0E-2 | 9.4E-3 | 4.4E2 | 2.2E2 | 122 | 26 | 99 | 26 | 0.52 |
| Jy | ng/ml | 1.7E-3 | 1.8E-3 | 2.3E-3 | 2.5E-3 | 4.7E-3 | 4.0E-3 | 1.0E-9 | 1.0E-9 | 5.2E-2 | 2.2E-2 | 122 | 26 | 99 | 26 | 0.50 |
| Kc | pg/ml | 2.1E1 | 3.8E1 | 3.9E1 | 6.1E1 | 4.4E1 | 6.1E1 | 1.0E-9 | 1.0E-9 | 1.7E2 | 1.9E2 | 121 | 26 | 98 | 26 | 0.63 |
| Kd | pg/ml | 1.0E-9 | 1.0E-9 | 1.9E2 | 2.7E2 | 6.7E2 | 6.3E2 | 1.0E-9 | 1.0E-9 | 4.8E3 | 2.4E3 | 121 | 26 | 98 | 26 | 0.56 |
| Ke | pg/ml | 9.5E3 | 1.2E4 | 1.3E4 | 1.5E4 | 9.6E3 | 1.2E4 | 3.4E2 | 1.3E3 | 5.9E4 | 5.0E4 | 121 | 26 | 98 | 26 | 0.54 |
| Kf | pg/mL | 5.5E0 | 9.0E0 | 6.3E0 | 8.8E0 | 5.7E0 | 6.7E0 | 1.0E-9 | 1.0E-9 | 2.6E1 | 2.2E1 | 121 | 26 | 98 | 26 | 0.61 |
| Kg | pg/mL | 9.9E2 | 1.3E3 | 1.7E3 | 2.6E3 | 2.4E3 | 3.1E3 | 7.7E1 | 1.3E2 | 2.2E4 | 1.3E4 | 121 | 26 | 98 | 26 | 0.57 |
| Ki | pg/ml | 6.5E1 | 4.9E1 | 7.2E1 | 4.9E1 | 5.2E1 | 3.2E1 | 1.0E-9 | 1.0E-9 | 2.9E2 | 1.5E2 | 121 | 26 | 98 | 26 | 0.34 |
| Kj | pg/ml | 9.3E2 | 1.1E3 | 1.5E3 | 1.7E3 | 1.6E3 | 1.5E3 | 6.6E1 | 9.4E1 | 1.0E4 | 5.0E3 | 121 | 26 | 98 | 26 | 0.55 |
| Kk | pg/ml | 6.8E0 | 6.7E0 | 1.2E1 | 1.4E1 | 1.8E1 | 1.6E1 | 1.0E-9 | 1.0E-9 | 1.6E2 | 4.8E1 | 121 | 26 | 98 | 26 | 0.50 |
| Kl | pg/ml | 1.7E4 | 2.8E4 | 2.4E4 | 3.3E4 | 2.3E4 | 2.9E4 | 3.5E2 | 1.0E3 | 1.1E5 | 1.1E5 | 121 | 26 | 98 | 26 | 0.58 |
| Kn | pg/ml | 1.5E1 | 4.1E1 | 5.4E1 | 8.6E1 | 1.1E2 | 1.1E2 | 1.0E-9 | 1.0E-9 | 7.3E2 | 3.8E2 | 121 | 26 | 98 | 26 | 0.61 |
| Ko | pg/ml | 3.0E2 | 4.9E2 | 3.9E2 | 5.3E2 | 4.0E2 | 4.7E2 | 1.0E-9 | 1.0E-9 | 1.8E3 | 1.5E3 | 121 | 26 | 98 | 26 | 0.58 |
| Kp | pg/ml | 2.7E2 | 3.6E2 | 3.2E2 | 4.0E2 | 2.9E2 | 2.7E2 | 1.0E-9 | 1.0E-9 | 1.7E3 | 9.8E2 | 121 | 26 | 98 | 26 | 0.59 |
| Kq | pg/ml | 2.8E2 | 3.5E2 | 4.2E2 | 6.7E2 | 9.3E2 | 1.4E3 | 5.1E0 | 8.8E1 | 9.8E3 | 7.1E3 | 117 | 26 | 95 | 26 | 0.62 |
| Kr | pg/ml | 3.6E-1 | 1.3E-1 | 2.4E0 | 1.8E0 | 4.8E0 | 4.3E0 | 1.0E-9 | 1.0E-9 | 3.5E1 | 2.1E1 | 117 | 26 | 95 | 26 | 0.47 |
| Ks | pg/ml | 1.5E4 | 1.2E4 | 2.0E4 | 1.5E4 | 1.9E4 | 1.2E4 | 3.8E2 | 3.2E2 | 1.1E5 | 5.0E4 | 117 | 26 | 95 | 26 | 0.44 |
| Kx | ng/ml | 1.0E-9 | 1.0E-9 | 4.4E-3 | 1.0E-2 | 8.5E-3 | 2.2E-2 | 1.0E-9 | 1.0E-9 | 5.1E-2 | 1.0E-1 | 120 | 25 | 98 | 25 | 0.52 |
| Ky | ng/ml | 7.7E-2 | 1.0E-1 | 3.2E-1 | 3.8E-1 | 6.9E-1 | 1.3E0 | 1.0E-9 | 1.0E-9 | 5.1E0 | 6.4E0 | 120 | 25 | 98 | 25 | 0.55 |
| Kz | ng/ml | 1.0E-9 | 4.7E-3 | 4.7E-3 | 3.2E-3 | 6.8E-3 | 3.5E-3 | 1.0E-9 | 1.0E-9 | 3.6E-2 | 1.4E-2 | 120 | 25 | 98 | 25 | 0.51 |
| Ld | pg/ml | 1.0E-9 | 2.2E0 | 3.6E0 | 3.6E0 | 9.5E0 | 4.8E0 | 1.0E-9 | 1.0E-9 | 6.9E1 | 1.9E1 | 119 | 26 | 97 | 26 | 0.60 |
| Lh | pg/ml | 1.0E4 | 1.4E4 | 1.8E4 | 2.0E4 | 2.6E4 | 2.5E4 | 1.0E-9 | 1.8E2 | 2.6E5 | 1.5E5 | 359 | 43 | 190 | 43 | 0.56 |
| Li | pg/ml | 2.5E3 | 3.1E3 | 1.3E4 | 1.5E4 | 7.2E4 | 3.8E4 | 1.0E-9 | 5.6E1 | 1.3E6 | 2.3E5 | 359 | 43 | 190 | 43 | 0.53 |
| Lj | pg/ml | 1.7E3 | 2.3E3 | 1.4E4 | 1.6E4 | 5.1E4 | 3.7E4 | 1.0E-9 | 1.0E-9 | 4.4E5 | 1.7E5 | 359 | 43 | 190 | 43 | 0.53 |
| Rm | ng/ml | 1.6E1 | 1.7E1 | 5.2E1 | 4.0E1 | 8.3E1 | 5.8E1 | 2.2E-1 | 1.4E0 | 4.0E2 | 2.5E2 | 121 | 26 | 97 | 26 | 0.50 |
| Rh | ng/ml | 1.3E2 | 1.2E2 | 4.7E2 | 2.2E2 | 1.6E3 | 2.2E2 | 4.7E0 | 7.5E0 | 1.7E4 | 8.5E2 | 121 | 26 | 97 | 26 | 0.48 |
| Ri | ng/ml | 1.0E-9 | 1.0E-9 | 4.3E0 | 3.5E0 | 1.0E1 | 1.0E1 | 1.0E-9 | 1.0E-9 | 7.4E1 | 4.1E1 | 122 | 26 | 98 | 26 | 0.42 |
| Rg | ng/ml | 1.0E-9 | 1.0E-9 | 3.2E-2 | 3.3E-2 | 2.6E-1 | 1.3E-1 | 1.0E-9 | 1.0E-9 | 2.7E0 | 6.9E-1 | 121 | 26 | 97 | 26 | 0.58 |
| Rj | ng/ml | 1.0E-9 | 1.0E-9 | 1.8E0 | 1.9E-1 | 7.6E0 | 5.9E-1 | 1.0E-9 | 1.0E-9 | 8.0E1 | 2.5E0 | 122 | 26 | 98 | 26 | 0.40 |
| Rf | ng/ml | 3.4E-1 | 3.9E-1 | 8.0E-1 | 5.8E-1 | 1.5E0 | 5.6E-1 | 7.8E-3 | 2.8E-2 | 1.4E1 | 2.0E0 | 121 | 26 | 97 | 26 | 0.50 |
| Ql | pg/ml | 5.0E0 | 5.5E0 | 1.1E1 | 5.8E0 | 1.7E1 | 7.5E0 | 1.0E-9 | 1.0E-9 | 1.2E2 | 3.6E1 | 122 | 26 | 99 | 26 | 0.43 |
| Qm | pg/ml | 1.7E0 | 1.0E-9 | 2.0E1 | 1.5E1 | 4.4E1 | 2.5E1 | 1.0E-9 | 1.0E-9 | 3.6E2 | 1.1E2 | 122 | 26 | 99 | 26 | 0.48 |
| Qn | pg/ml | 6.1E-1 | 5.6E-1 | 7.2E0 | 9.3E0 | 2.4E1 | 2.3E1 | 1.0E-9 | 1.0E-9 | 2.2E2 | 1.0E2 | 122 | 26 | 99 | 26 | 0.44 |
| Nv | pg/ml | 3.0E3 | 2.6E3 | 1.1E4 | 1.9E4 | 5.8E4 | 8.1E4 | 1.0E-9 | 7.5E1 | 1.1E6 | 5.3E5 | 362 | 43 | 190 | 43 | 0.52 |
| Nw | pg/ml | 7.1E3 | 9.5E3 | 1.2E4 | 1.3E4 | 2.1E4 | 1.6E4 | 8.6E1 | 7.4E2 | 2.1E5 | 8.9E4 | 362 | 43 | 190 | 43 | 0.56 |
| Nx | pg/ml | 1.2E2 | 2.2E2 | 3.6E2 | 4.8E2 | 6.8E2 | 9.0E2 | 1.0E-9 | 1.0E-9 | 7.4E3 | 5.3E3 | 362 | 43 | 190 | 43 | 0.55 |
| Ny | pg/ml | 5.2E0 | 2.9E0 | 9.8E1 | 6.1E1 | 1.3E3 | 3.1E2 | 1.0E-9 | 1.0E-9 | 2.5E4 | 2.1E3 | 362 | 43 | 190 | 43 | 0.47 |
| Oa | pg/ml | 1.6E2 | 1.3E2 | 4.0E2 | 4.1E2 | 7.6E2 | 6.5E2 | 1.0E-9 | 1.0E-9 | 4.8E3 | 2.7E3 | 122 | 26 | 99 | 26 | 0.48 |
| Wn | ng/ml | 1.2E1 | 1.2E1 | 9.2E1 | 6.7E1 | 3.0E2 | 1.7E2 | 2.2E0 | 1.5E0 | 1.8E3 | 6.1E2 | 35 | 12 | 29 | 12 | 0.46 |
| Tk | ng/ml | 1.3E2 | 8.7E1 | 3.8E2 | 1.8E2 | 7.3E2 | 2.0E2 | 1.9E1 | 5.8E0 | 4.2E3 | 5.3E2 | 37 | 12 | 30 | 12 | 0.36 |

Figure 21 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oe | pg/ml | 1.1E1 | 1.0E1 | 2.3E2 | 2.0E2 | 3.7E2 | 3.1E2 | 1.0E-9 | 1.0E-9 | 2.7E3 | 1.5E3 | 357 | 43 | 190 | 43 | 0.50 |
| Of | pg/ml | 1.6E2 | 2.1E2 | 4.0E3 | 9.4E3 | 1.5E4 | 3.4E4 | 1.0E-9 | 1.0E-9 | 1.8E5 | 1.6E5 | 360 | 43 | 190 | 43 | 0.51 |
| Og | pg/ml | 8.4E-2 | 8.4E-2 | 5.8E-1 | 1.6E-1 | 1.9E0 | 2.5E-1 | 1.0E-9 | 1.0E-9 | 2.0E1 | 1.4E0 | 360 | 43 | 190 | 43 | 0.44 |
| Oh | pg/ml | 1.9E0 | 2.7E0 | 2.2E1 | 1.2E1 | 1.2E2 | 4.1E1 | 1.0E-9 | 1.0E-9 | 1.4E3 | 2.6E2 | 360 | 43 | 190 | 43 | 0.56 |
| Oi | pg/ml | 2.0E0 | 2.4E0 | 6.3E0 | 4.9E0 | 1.1E1 | 7.7E0 | 1.0E-9 | 1.0E-9 | 8.6E1 | 4.2E1 | 360 | 43 | 190 | 43 | 0.51 |
| Ok | pg/ml | 2.9E2 | 4.9E2 | 3.9E2 | 6.7E2 | 3.7E2 | 7.0E2 | 1.3E1 | 2.7E1 | 2.8E3 | 3.1E3 | 360 | 43 | 190 | 43 | 0.62 |
| Om | pg/ml | 3.6E2 | 3.9E2 | 7.4E2 | 1.0E3 | 2.0E3 | 3.0E3 | 1.0E-9 | 3.7E1 | 3.0E4 | 2.0E4 | 360 | 43 | 190 | 43 | 0.52 |
| On | pg/ml | 1.3E2 | 1.9E2 | 2.5E2 | 3.4E2 | 4.5E2 | 5.6E2 | 1.0E-9 | 1.0E-9 | 4.5E3 | 3.3E3 | 360 | 43 | 190 | 43 | 0.57 |
| Or | pg/ml | 1.0E1 | 2.2E1 | 2.9E1 | 3.4E1 | 6.1E1 | 4.6E1 | 1.0E-9 | 1.0E-9 | 5.0E2 | 2.0E2 | 120 | 26 | 98 | 26 | 0.57 |
| Ow | pg/ml | 2.7E1 | 3.2E1 | 9.9E1 | 4.0E2 | 2.9E2 | 1.6E3 | 1.0E-9 | 1.0E-9 | 2.3E3 | 8.1E3 | 120 | 26 | 98 | 26 | 0.54 |
| Ou | pg/ml | 5.0E2 | 4.1E2 | 8.2E2 | 7.9E2 | 1.2E3 | 1.0E3 | 3.5E1 | 1.0E-9 | 9.4E3 | 4.4E3 | 120 | 26 | 98 | 26 | 0.48 |
| Ul | ng/ml | 1.0E-9 | 1.0E-9 | 1.2E0 | 7.3E-1 | 4.3E0 | 3.7E0 | 1.0E-9 | 1.0E-9 | 2.9E1 | 1.9E1 | 131 | 26 | 102 | 26 | 0.47 |
| Uo | ng/ml | 1.0E-9 | 1.0E-9 | 1.0E-1 | 1.1E-1 | 2.3E-1 | 2.0E-1 | 1.0E-9 | 1.0E-9 | 1.3E0 | 5.8E-1 | 131 | 26 | 102 | 26 | 0.50 |
| Uk | ng/ml | 1.0E-9 | 1.0E-9 | 4.7E-3 | 2.0E-2 | 1.1E-2 | 6.6E-2 | 1.0E-9 | 1.0E-9 | 9.9E-2 | 3.2E-1 | 131 | 26 | 102 | 26 | 0.50 |
| Um | ng/ml | 1.0E-9 | 1.0E-9 | 4.0E-1 | 9.3E-1 | 9.8E-1 | 1.3E0 | 1.0E-9 | 1.0E-9 | 6.8E0 | 4.0E0 | 131 | 26 | 102 | 26 | 0.57 |
| Uf | ng/ml | 4.1E-2 | 6.1E-2 | 1.0E-1 | 5.0E-1 | 1.4E-1 | 1.7E0 | 2.7E-3 | 3.6E-3 | 7.0E-1 | 8.6E0 | 131 | 26 | 102 | 26 | 0.59 |
| Uh | ng/ml | 1.6E0 | 1.9E0 | 2.7E0 | 3.4E0 | 2.7E0 | 4.4E0 | 3.2E-2 | 6.3E-2 | 1.5E1 | 2.1E1 | 131 | 26 | 102 | 26 | 0.52 |
| Un | ng/ml | 1.7E0 | 2.2E0 | 2.0E0 | 2.0E0 | 1.3E0 | 1.0E0 | 2.0E-1 | 2.6E-1 | 7.0E0 | 3.9E0 | 131 | 26 | 102 | 26 | 0.54 |
| Ug | ng/ml | 1.5E1 | 1.3E1 | 2.7E1 | 2.0E1 | 2.7E1 | 2.0E1 | 6.9E-1 | 1.8E0 | 1.3E2 | 6.8E1 | 131 | 26 | 102 | 26 | 0.41 |
| Ur | ng/ml | 1.7E-1 | 1.6E-1 | 1.2E0 | 6.2E-1 | 8.2E0 | 1.1E0 | 1.0E-9 | 1.0E-9 | 9.3E1 | 4.1E0 | 131 | 26 | 102 | 26 | 0.51 |
| Up | ng/ml | 1.0E-9 | 1.0E-9 | 6.9E-3 | 2.1E-3 | 3.2E-2 | 7.0E-3 | 1.0E-9 | 1.0E-9 | 3.3E-1 | 3.5E-2 | 131 | 26 | 102 | 26 | 0.47 |
| Us | ng/ml | 2.6E-3 | 1.0E-9 | 2.0E-2 | 3.6E-3 | 5.4E-2 | 6.7E-3 | 1.0E-9 | 1.0E-9 | 4.0E-1 | 2.9E-2 | 131 | 26 | 102 | 26 | 0.35 |
| Uv | ng/ml | 3.5E-3 | 1.7E-3 | 1.3E-2 | 9.8E-3 | 4.0E-2 | 3.1E-2 | 1.0E-9 | 1.0E-9 | 3.5E-1 | 1.6E-1 | 131 | 26 | 102 | 26 | 0.38 |
| Ut | ng/ml | 5.0E-1 | 6.5E-1 | 2.3E0 | 4.1E0 | 8.5E0 | 1.5E1 | 1.0E-9 | 1.0E-9 | 7.2E1 | 7.8E1 | 131 | 26 | 102 | 26 | 0.50 |
| Uu | ng/ml | 6.3E0 | 7.6E0 | 7.3E0 | 8.0E0 | 4.7E0 | 5.0E0 | 8.1E-1 | 9.8E-1 | 2.4E1 | 2.3E1 | 131 | 26 | 102 | 26 | 0.55 |
| Vp | ng/ml | 1.0E-9 | 1.0E-9 | 6.8E-1 | 2.1E-1 | 5.0E0 | 1.0E0 | 1.0E-9 | 1.0E-9 | 5.0E1 | 5.2E0 | 131 | 26 | 102 | 26 | 0.46 |
| Vt | ng/ml | 6.1E0 | 6.4E0 | 8.2E0 | 7.9E0 | 6.9E0 | 6.6E0 | 6.0E-1 | 7.0E-1 | 3.2E1 | 3.0E1 | 131 | 26 | 102 | 26 | 0.49 |
| Vu | ng/ml | 1.0E-9 | 1.0E-9 | 1.9E0 | 2.4E0 | 5.4E0 | 7.7E0 | 1.0E-9 | 1.0E-9 | 5.1E1 | 3.8E1 | 130 | 25 | 102 | 25 | 0.50 |
| Vq | ng/ml | 1.5E2 | 2.4E2 | 7.5E3 | 8.5E2 | 6.7E4 | 1.1E3 | 2.0E-1 | 2.6E0 | 6.8E5 | 4.3E3 | 102 | 22 | 82 | 22 | 0.61 |
| Vo | ng/ml | 2.6E1 | 2.5E1 | 2.5E1 | 2.4E1 | 4.3E0 | 3.9E0 | 1.1E1 | 8.2E0 | 3.5E1 | 2.8E1 | 131 | 26 | 102 | 26 | 0.38 |
| Vs | ng/ml | 1.0E-9 | 1.0E-9 | 6.0E0 | 1.4E1 | 2.6E1 | 4.6E1 | 1.0E-9 | 1.0E-9 | 2.3E2 | 2.2E2 | 127 | 26 | 99 | 26 | 0.53 |
| Vv | ng/ml | 2.2E0 | 3.4E0 | 5.7E0 | 4.0E0 | 1.0E1 | 3.9E0 | 1.0E-9 | 1.0E-9 | 8.1E1 | 1.4E1 | 130 | 26 | 102 | 26 | 0.51 |
| Oy | pg/ml | 5.4E-1 | 5.3E-1 | 7.9E0 | 7.6E0 | 3.9E1 | 3.8E1 | 1.0E-9 | 1.0E-9 | 4.0E2 | 2.5E2 | 360 | 43 | 190 | 43 | 0.47 |
| Oz | pg/ml | 1.4E-3 | 5.3E-2 | 2.3E-1 | 1.7E-1 | 3.8E-1 | 2.3E-1 | 1.0E-9 | 1.0E-9 | 2.6E0 | 9.0E-1 | 360 | 43 | 190 | 43 | 0.51 |
| Pa | pg/ml | 3.3E-1 | 3.2E-1 | 1.3E0 | 8.8E-1 | 5.6E0 | 2.3E0 | 1.0E-9 | 1.0E-9 | 8.6E1 | 1.4E1 | 360 | 43 | 190 | 43 | 0.50 |
| Pb | pg/ml | 1.0E-9 | 1.0E-9 | 1.6E0 | 2.0E-1 | 2.6E1 | 8.2E-1 | 1.0E-9 | 1.0E-9 | 4.9E2 | 5.3E0 | 360 | 43 | 190 | 43 | 0.49 |
| Pc | pg/ml | 2.4E-2 | 1.4E-1 | 4.2E-1 | 2.9E-1 | 1.2E0 | 3.9E-1 | 1.0E-9 | 1.0E-9 | 1.6E1 | 1.8E0 | 360 | 43 | 190 | 43 | 0.54 |
| Pd | pg/ml | 1.7E0 | 1.8E0 | 3.7E0 | 3.5E0 | 8.5E0 | 5.2E0 | 1.0E-9 | 1.0E-9 | 9.4E1 | 2.4E1 | 360 | 43 | 190 | 43 | 0.51 |
| Pe | pg/ml | 1.7E1 | 2.0E1 | 8.8E1 | 9.6E1 | 3.4E2 | 1.8E2 | 1.0E-9 | 1.0E-9 | 4.7E3 | 7.3E2 | 360 | 43 | 190 | 43 | 0.54 |
| Pf | pg/ml | 1.2E0 | 1.2E0 | 8.1E0 | 1.2E1 | 3.9E1 | 3.2E1 | 1.0E-9 | 1.0E-9 | 4.8E2 | 1.8E2 | 360 | 43 | 190 | 43 | 0.54 |
| Pg | pg/ml | 2.9E0 | 2.2E0 | 3.5E1 | 8.9E1 | 1.9E2 | 5.2E2 | 1.0E-9 | 1.0E-9 | 3.2E3 | 3.4E3 | 360 | 43 | 190 | 43 | 0.47 |
| Ph | ng/ml | 1.5E-1 | 1.7E-1 | 2.6E-1 | 4.3E-1 | 3.0E-1 | 6.9E-1 | 1.0E-9 | 1.0E-9 | 1.6E0 | 2.9E0 | 120 | 26 | 98 | 26 | 0.51 |
| Pi | ng/ml | 2.0E-1 | 1.3E-1 | 2.7E-1 | 1.9E-1 | 4.1E-1 | 2.2E-1 | 1.0E-9 | 1.0E-9 | 3.2E0 | 8.6E-1 | 120 | 26 | 98 | 26 | 0.41 |
| Pj | ng/mL | 4.5E0 | 5.3E0 | 5.1E0 | 5.4E0 | 3.3E0 | 3.2E0 | 3.8E-2 | 5.1E-1 | 1.6E1 | 1.5E1 | 120 | 26 | 98 | 26 | 0.53 |
| Pk | ng/ml | 8.1E-3 | 8.9E-3 | 1.2E-2 | 1.2E-2 | 1.2E-2 | 1.2E-2 | 1.0E-9 | 1.0E-9 | 5.9E-2 | 4.6E-2 | 120 | 26 | 98 | 26 | 0.51 |
| aA | mg/dL | 8.0E-1 | 8.0E-1 | 9.1E-1 | 9.6E-1 | 4.4E-1 | 5.7E-1 | 3.0E-1 | 3.0E-1 | 4.1E0 | 3.0E0 | 1529 | 54 | 315 | 54 | 0.50 |
| aC | mg/mL | 3.2E0 | 2.3E0 | 3.4E0 | 2.5E0 | 1.5E0 | 9.8E-1 | 1.1E0 | 1.1E0 | 8.9E0 | 5.9E0 | 262 | 26 | 110 | 26 | 0.30 |
| aD | ug/mL | 3.1E0 | 3.1E0 | 4.5E0 | 4.0E0 | 4.0E0 | 3.3E0 | 4.3E-1 | 1.1E0 | 3.5E1 | 1.5E1 | 262 | 26 | 110 | 26 | 0.45 |
| aE | mg/mL | 5.8E-1 | 5.5E-1 | 5.8E-1 | 5.6E-1 | 1.4E-1 | 1.1E-1 | 2.1E-1 | 3.5E-1 | 1.1E0 | 7.8E-1 | 262 | 26 | 110 | 26 | 0.44 |
| aF | ng/mL | 2.0E0 | 2.2E0 | 4.1E0 | 4.6E0 | 6.5E0 | 6.6E0 | 4.3E-3 | 4.3E-3 | 5.0E1 | 3.0E1 | 262 | 26 | 110 | 26 | 0.52 |
| aG | mg/mL | 1.3E-1 | 1.4E-1 | 1.6E-1 | 1.5E-1 | 9.4E-2 | 6.4E-2 | 1.7E-2 | 5.6E-2 | 5.4E-1 | 3.5E-1 | 262 | 26 | 110 | 26 | 0.53 |
| aH | ug/mL | 7.0E1 | 7.7E1 | 7.8E1 | 8.6E1 | 3.8E1 | 4.7E1 | 4.6E0 | 2.5E1 | 2.7E2 | 2.3E2 | 262 | 26 | 110 | 26 | 0.54 |
| aI | ug/mL | 1.9E2 | 1.9E2 | 1.9E2 | 1.8E2 | 6.0E1 | 5.8E1 | 2.8E1 | 7.7E1 | 3.7E2 | 2.7E2 | 262 | 26 | 110 | 26 | 0.47 |
| aJ | ug/mL | 2.4E0 | 2.5E0 | 2.9E0 | 3.2E0 | 1.9E0 | 2.1E0 | 8.5E-1 | 1.0E0 | 1.2E1 | 9.5E0 | 262 | 26 | 110 | 26 | 0.54 |
| aK | ng/mL | 1.8E0 | 1.4E0 | 2.7E0 | 2.0E0 | 2.8E0 | 1.9E0 | 2.8E-1 | 1.0E-1 | 1.8E1 | 7.5E0 | 262 | 26 | 110 | 26 | 0.44 |
| aL | mg/mL | 8.3E-1 | 7.9E-1 | 8.4E-1 | 8.2E-1 | 2.7E-1 | 2.8E-1 | 1.9E-1 | 2.9E-1 | 1.7E0 | 1.4E0 | 262 | 26 | 110 | 26 | 0.47 |
| aM | U/mL | 1.9E1 | 1.9E1 | 4.2E1 | 2.9E1 | 1.1E2 | 3.3E1 | 4.2E-2 | 4.2E-2 | 1.6E3 | 1.2E2 | 262 | 26 | 110 | 26 | 0.48 |

Figure 21 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aN | U/mL | 9.3E0 | 1.3E1 | 1.4E1 | 2.1E1 | 1.5E1 | 2.9E1 | 2.5E-3 | 2.5E-3 | 9.8E1 | 1.3E2 | 262 | 26 | 110 | 26 | 0.57 |
| aO | pg/mL | 2.9E1 | 9.1E1 | 3.0E2 | 4.5E2 | 8.5E2 | 9.1E2 | 6.0E-2 | 6.0E-2 | 6.6E3 | 3.9E3 | 262 | 26 | 110 | 26 | 0.57 |
| aP | ng/mL | 1.7E0 | 1.7E0 | 2.1E0 | 2.2E0 | 2.1E0 | 1.3E0 | 4.5E-1 | 7.9E-1 | 2.8E1 | 5.4E0 | 262 | 26 | 110 | 26 | 0.54 |
| aQ | ng/mL | 3.2E-1 | 3.0E-1 | 4.9E-1 | 3.6E-1 | 5.0E-1 | 3.0E-1 | 1.9E-2 | 6.3E-2 | 4.0E0 | 1.3E0 | 262 | 26 | 110 | 26 | 0.43 |
| aR | ng/mL | 1.7E0 | 2.2E0 | 2.3E0 | 2.9E0 | 2.3E0 | 2.7E0 | 1.8E-1 | 3.6E-1 | 2.1E1 | 1.3E1 | 262 | 26 | 110 | 26 | 0.58 |
| aS | ng/mL | 2.4E-1 | 2.0E-1 | 6.5E-1 | 4.7E-1 | 2.3E0 | 5.3E-1 | 4.2E-3 | 4.2E-3 | 3.3E1 | 2.1E0 | 262 | 26 | 110 | 26 | 0.54 |
| aU | pg/mL | 8.7E1 | 7.0E1 | 1.4E2 | 1.0E2 | 1.6E2 | 1.2E2 | 7.4E-2 | 6.5E0 | 1.3E3 | 5.8E2 | 262 | 26 | 110 | 26 | 0.41 |
| aV | ng/mL | 7.0E-1 | 5.8E-1 | 1.1E0 | 1.1E0 | 1.2E0 | 1.4E0 | 2.2E-2 | 9.2E-2 | 8.7E0 | 6.0E0 | 262 | 26 | 110 | 26 | 0.44 |
| aW | pg/mL | 1.7E1 | 2.2E1 | 1.9E1 | 2.1E1 | 2.4E1 | 7.7E0 | 7.2E-2 | 7.2E-2 | 2.4E2 | 3.4E1 | 262 | 26 | 110 | 26 | 0.63 |
| aX | ng/mL | 1.0E1 | 7.9E0 | 1.6E1 | 2.0E1 | 2.2E1 | 4.1E1 | 3.0E-1 | 2.5E0 | 2.2E2 | 2.1E2 | 262 | 26 | 110 | 26 | 0.46 |
| aY | pg/mL | 5.3E1 | 6.0E1 | 7.3E1 | 7.7E1 | 7.0E1 | 5.8E1 | 4.1E-1 | 4.1E-1 | 4.4E2 | 2.4E2 | 262 | 26 | 110 | 26 | 0.56 |
| aZ | pg/mL | 2.3E2 | 2.8E2 | 4.4E2 | 9.8E2 | 5.6E2 | 2.4E3 | 1.7E0 | 1.7E0 | 3.4E3 | 1.2E4 | 262 | 26 | 110 | 26 | 0.53 |
| bA | ng/mL | 6.8E0 | 1.6E1 | 2.4E1 | 3.8E1 | 6.9E1 | 5.4E1 | 3.0E-2 | 3.0E-2 | 7.1E2 | 2.1E2 | 262 | 26 | 110 | 26 | 0.64 |
| bB | ng/mL | 3.1E2 | 2.9E2 | 3.4E2 | 3.1E2 | 1.6E2 | 1.7E2 | 2.1E0 | 6.6E1 | 7.4E2 | 6.9E2 | 262 | 26 | 110 | 26 | 0.44 |
| bC | ng/mL | 3.4E2 | 3.5E2 | 5.2E2 | 7.2E2 | 6.0E2 | 1.1E3 | 2.7E1 | 1.4E1 | 4.0E3 | 4.7E3 | 262 | 26 | 110 | 26 | 0.52 |
| bE | mg/mL | 5.8E0 | 5.9E0 | 6.1E0 | 6.3E0 | 2.0E0 | 2.4E0 | 9.8E-1 | 1.9E0 | 1.2E1 | 1.2E1 | 262 | 26 | 110 | 26 | 0.50 |
| bF | pg/mL | 1.9E1 | 2.9E1 | 5.7E1 | 7.5E2 | 2.6E2 | 2.3E3 | 5.0E-2 | 4.4E0 | 3.3E3 | 1.1E4 | 262 | 26 | 110 | 26 | 0.64 |
| bG | ng/mL | 1.7E0 | 1.1E0 | 2.9E0 | 2.0E0 | 3.3E0 | 1.8E0 | 2.2E-2 | 1.1E-1 | 2.3E1 | 7.3E0 | 262 | 26 | 110 | 26 | 0.43 |
| bH | pg/mL | 5.7E-1 | 5.7E-1 | 5.1E0 | 2.7E0 | 1.8E1 | 4.1E0 | 5.7E-1 | 5.7E-1 | 2.8E2 | 1.4E1 | 262 | 26 | 110 | 26 | 0.45 |
| bI | ng/mL | 4.0E-3 | 4.0E-3 | 6.0E-2 | 5.4E-2 | 1.5E-1 | 1.1E-1 | 4.0E-3 | 4.0E-3 | 1.3E0 | 3.7E-1 | 262 | 26 | 110 | 26 | 0.52 |
| bJ | mg/mL | 2.6E0 | 2.6E0 | 3.0E0 | 2.8E0 | 2.2E0 | 2.0E0 | 2.5E-4 | 2.1E-2 | 1.3E1 | 9.0E0 | 262 | 26 | 110 | 26 | 0.48 |
| bL | pg/mL | 4.1E0 | 7.1E0 | 8.5E0 | 1.1E1 | 1.1E1 | 1.1E1 | 4.6E-2 | 4.6E-2 | 8.0E1 | 4.0E1 | 262 | 26 | 110 | 26 | 0.55 |
| bM | mg/mL | 1.5E0 | 1.9E0 | 1.9E0 | 2.2E0 | 1.3E0 | 1.5E0 | 9.2E-3 | 3.3E-1 | 8.8E0 | 8.4E0 | 262 | 26 | 110 | 26 | 0.61 |
| bN | ng/mL | 3.1E1 | 5.2E1 | 1.3E2 | 1.1E2 | 3.1E2 | 1.6E2 | 1.4E-1 | 4.9E-1 | 1.9E3 | 5.7E2 | 262 | 26 | 110 | 26 | 0.56 |
| bO | ng/mL | 4.0E-2 | 4.0E-2 | 1.1E1 | 1.6E1 | 2.4E1 | 2.3E1 | 4.0E-2 | 4.0E-2 | 1.9E2 | 7.3E1 | 262 | 26 | 110 | 26 | 0.55 |
| bP | mg/mL | 6.3E-1 | 4.6E-1 | 8.5E-1 | 6.0E-1 | 7.0E-1 | 4.3E-1 | 4.9E-2 | 9.7E-2 | 3.8E0 | 1.8E0 | 262 | 26 | 110 | 26 | 0.41 |
| bQ | pg/mL | 1.5E1 | 1.7E1 | 2.7E1 | 5.2E1 | 5.0E1 | 9.8E1 | 1.5E-1 | 4.4E0 | 4.8E2 | 4.0E2 | 262 | 26 | 110 | 26 | 0.52 |
| bR | ng/mL | 1.2E-2 | 1.2E-2 | 1.3E-1 | 7.6E-2 | 2.5E-1 | 1.0E-1 | 1.2E-2 | 1.2E-2 | 3.4E0 | 3.2E-1 | 262 | 26 | 110 | 26 | 0.44 |
| bS | pg/mL | 9.4E-1 | 9.4E-1 | 7.8E0 | 4.8E0 | 2.7E1 | 1.4E1 | 9.4E-1 | 9.4E-1 | 3.4E2 | 5.5E1 | 262 | 26 | 110 | 26 | 0.46 |
| bU | ng/mL | 1.6E-2 | 9.6E-2 | 2.1E-1 | 1.1E-1 | 2.3E-1 | 1.1E-1 | 1.3E-2 | 1.3E-2 | 1.8E0 | 3.6E-1 | 262 | 26 | 110 | 26 | 0.38 |
| bV | pg/mL | 4.7E2 | 4.3E2 | 5.7E2 | 5.3E2 | 7.2E2 | 3.3E2 | 1.6E2 | 2.3E2 | 1.2E4 | 1.5E3 | 262 | 26 | 110 | 26 | 0.45 |
| bW | pg/mL | 3.5E2 | 3.3E2 | 5.2E2 | 1.2E3 | 4.8E2 | 3.9E3 | 1.1E2 | 1.0E2 | 3.4E3 | 2.0E4 | 262 | 26 | 110 | 26 | 0.50 |
| bX | ng/mL | 1.8E-3 | 2.5E-5 | 3.0E-3 | 1.1E-3 | 3.7E-3 | 2.1E-3 | 2.5E-5 | 2.5E-5 | 2.0E-2 | 6.9E-3 | 262 | 26 | 110 | 26 | 0.36 |
| bZ | pg/mL | 2.5E2 | 2.8E2 | 8.0E2 | 9.9E2 | 3.3E3 | 2.2E3 | 1.5E-1 | 1.0E2 | 4.4E4 | 1.2E4 | 262 | 26 | 110 | 26 | 0.54 |
| cA | pg/mL | 6.0E-1 | 6.0E-1 | 2.0E0 | 2.7E0 | 3.5E0 | 5.8E0 | 6.0E-1 | 6.0E-1 | 1.5E1 | 2.5E1 | 262 | 26 | 110 | 26 | 0.51 |
| cB | ng/mL | 6.7E-2 | 3.1E-2 | 9.8E-2 | 4.3E-2 | 1.0E-1 | 5.3E-2 | 1.7E-3 | 1.7E-3 | 5.4E-1 | 2.2E-1 | 262 | 26 | 110 | 26 | 0.30 |
| cC | pg/mL | 4.6E1 | 4.8E1 | 4.9E1 | 4.5E1 | 3.6E1 | 2.0E1 | 1.0E0 | 1.0E0 | 3.7E2 | 8.4E1 | 262 | 26 | 110 | 26 | 0.48 |
| cD | pg/mL | 6.1E0 | 3.8E0 | 1.3E1 | 2.5E1 | 5.9E1 | 6.4E1 | 3.3E-1 | 3.3E-1 | 7.2E2 | 3.1E2 | 262 | 26 | 110 | 26 | 0.44 |
| cE | pg/mL | 3.1E1 | 4.6E1 | 1.1E2 | 4.5E2 | 2.8E2 | 9.2E2 | 1.2E-1 | 1.8E0 | 3.1E3 | 3.8E3 | 262 | 26 | 110 | 26 | 0.57 |
| cF | pg/mL | 1.4E1 | 5.3E-1 | 2.3E1 | 6.7E0 | 3.2E1 | 1.1E1 | 5.3E-1 | 5.3E-1 | 2.2E2 | 4.1E1 | 262 | 26 | 110 | 26 | 0.31 |
| cG | pg/mL | 4.2E1 | 3.5E1 | 6.7E1 | 1.1E2 | 9.1E1 | 1.4E2 | 9.6E0 | 1.7E1 | 1.1E3 | 5.6E2 | 262 | 26 | 110 | 26 | 0.50 |
| cH | uIU/mL | 2.8E0 | 2.6E0 | 5.6E0 | 5.4E0 | 8.3E0 | 1.0E1 | 8.6E-3 | 8.6E-3 | 8.7E1 | 4.2E1 | 262 | 26 | 110 | 26 | 0.44 |
| cI | ng/mL | 5.5E0 | 4.3E0 | 1.1E1 | 1.2E1 | 1.4E1 | 2.1E1 | 1.0E-3 | 3.2E-2 | 1.0E2 | 1.0E2 | 262 | 26 | 110 | 26 | 0.44 |
| cJ | ug/mL | 7.0E1 | 6.9E1 | 1.2E2 | 1.3E2 | 1.4E2 | 1.6E2 | 4.0E0 | 8.6E0 | 9.6E2 | 6.6E2 | 262 | 26 | 110 | 26 | 0.51 |
| cK | ng/mL | 3.8E-3 | 3.8E-3 | 6.9E-2 | 1.1E-2 | 2.1E-1 | 2.6E-2 | 3.8E-3 | 3.8E-3 | 1.7E0 | 1.2E-1 | 262 | 26 | 110 | 26 | 0.43 |
| cL | pg/mL | 1.9E2 | 2.2E2 | 2.7E2 | 6.3E2 | 4.7E2 | 1.0E3 | 2.5E1 | 3.6E1 | 7.1E3 | 4.2E3 | 262 | 26 | 110 | 26 | 0.58 |
| cM | pg/mL | 2.8E2 | 2.4E2 | 3.1E2 | 3.0E2 | 1.8E2 | 2.1E2 | 2.5E1 | 4.7E1 | 1.2E3 | 8.4E2 | 262 | 26 | 110 | 26 | 0.46 |
| cN | pg/mL | 1.2E2 | 1.2E2 | 1.2E2 | 1.4E2 | 4.2E1 | 6.8E1 | 3.8E1 | 5.7E1 | 3.0E2 | 3.5E2 | 262 | 26 | 110 | 26 | 0.57 |
| cO | pg/mL | 2.3E2 | 2.1E2 | 2.9E2 | 2.9E2 | 2.0E2 | 2.1E2 | 5.4E1 | 9.0E1 | 1.7E3 | 1.1E3 | 262 | 26 | 110 | 26 | 0.49 |
| cP | ng/mL | 2.4E3 | 2.8E3 | 2.5E3 | 2.8E3 | 8.7E2 | 8.7E2 | 6.2E2 | 1.4E3 | 5.7E3 | 5.1E3 | 262 | 26 | 110 | 26 | 0.62 |
| cQ | ng/mL | 3.9E-2 | 5.2E-2 | 1.2E-1 | 2.0E-1 | 2.1E-1 | 4.5E-1 | 2.0E-3 | 2.0E-3 | 1.5E0 | 2.2E0 | 262 | 26 | 110 | 26 | 0.55 |
| cR | ng/mL | 3.2E2 | 3.3E2 | 5.4E2 | 5.6E2 | 8.7E2 | 9.4E2 | 2.3E1 | 9.4E1 | 8.9E3 | 4.8E3 | 262 | 26 | 110 | 26 | 0.51 |
| cS | ng/mL | 2.5E2 | 3.3E2 | 4.2E2 | 4.3E2 | 4.6E2 | 2.9E2 | 4.1E1 | 5.0E1 | 2.7E3 | 1.1E3 | 262 | 26 | 110 | 26 | 0.56 |
| cT | ng/mL | 2.7E1 | 5.8E1 | 6.4E1 | 1.1E2 | 1.3E2 | 1.9E2 | 4.6E0 | 7.6E0 | 1.7E3 | 9.9E2 | 262 | 26 | 110 | 26 | 0.64 |
| cU | ng/mL | 5.6E1 | 5.2E1 | 7.3E1 | 6.1E1 | 6.8E1 | 4.1E1 | 9.2E0 | 9.0E0 | 7.7E2 | 1.5E2 | 262 | 26 | 110 | 26 | 0.46 |
| cV | ng/mL | 1.6E-1 | 1.5E-1 | 4.4E-1 | 2.1E-1 | 2.9E0 | 2.2E-1 | 2.5E-2 | 3.0E-2 | 4.7E1 | 1.0E0 | 262 | 26 | 110 | 26 | 0.44 |
| cW | mIU/mL | 5.1E-2 | 7.6E-2 | 2.0E-1 | 8.1E-2 | 9.3E-1 | 5.3E-2 | 3.7E-4 | 2.1E-2 | 9.7E0 | 2.1E-1 | 262 | 26 | 110 | 26 | 0.60 |

Figure 21 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cX | ng/mL | 9.7E-2 | 2.5E-1 | 1.3E0 | 1.2E0 | 4.3E0 | 3.8E0 | 2.3E-4 | 2.3E-4 | 2.8E1 | 1.9E1 | 262 | 26 | 110 | 26 | 0.53 |
| cY | ng/mL | 9.9E0 | 6.5E0 | 1.4E1 | 1.1E1 | 1.3E1 | 1.2E1 | 2.5E-1 | 1.3E0 | 8.3E1 | 5.3E1 | 262 | 26 | 110 | 26 | 0.41 |
| cZ | ug/mL | 1.5E1 | 1.7E1 | 1.6E1 | 1.8E1 | 7.5E0 | 7.5E0 | 2.3E0 | 6.6E0 | 5.7E1 | 4.2E1 | 262 | 26 | 110 | 26 | 0.57 |
| dA | pg/mL | 3.3E2 | 3.2E2 | 3.6E2 | 3.6E2 | 1.8E2 | 1.7E2 | 9.0E1 | 1.1E2 | 1.3E3 | 9.3E2 | 262 | 26 | 110 | 26 | 0.49 |
| dB | ug/mL | 1.7E1 | 2.2E1 | 1.9E1 | 2.0E1 | 2.0E1 | 8.6E0 | 2.1E0 | 2.8E0 | 2.5E2 | 3.2E1 | 262 | 26 | 110 | 26 | 0.64 |
| dC | nmol/L | 3.5E1 | 3.7E1 | 4.0E1 | 3.7E1 | 1.9E1 | 1.2E1 | 7.9E0 | 1.7E1 | 1.4E2 | 6.5E1 | 262 | 26 | 110 | 26 | 0.49 |
| dD | ug/mL | 3.8E1 | 3.2E1 | 3.9E1 | 3.4E1 | 1.1E1 | 9.3E0 | 1.3E1 | 1.6E1 | 7.6E1 | 5.1E1 | 262 | 26 | 110 | 26 | 0.37 |
| dE | ng/mL | 5.1E-1 | 4.6E-1 | 6.9E-1 | 5.5E-1 | 8.1E-1 | 5.1E-1 | 8.4E-3 | 8.4E-3 | 7.2E0 | 2.0E0 | 262 | 26 | 110 | 26 | 0.47 |
| dF | ng/mL | 2.1E2 | 2.3E2 | 2.6E2 | 3.1E2 | 1.8E2 | 2.3E2 | 7.5E1 | 1.2E2 | 1.2E3 | 1.1E3 | 262 | 26 | 110 | 26 | 0.55 |
| dG | ng/mL | 1.1E1 | 1.1E1 | 1.4E1 | 1.7E1 | 1.0E1 | 1.6E1 | 2.5E0 | 6.0E0 | 8.1E1 | 7.6E1 | 262 | 26 | 110 | 26 | 0.55 |
| dH | pg/mL | 7.5E0 | 7.2E0 | 1.2E1 | 1.4E1 | 2.8E1 | 2.1E1 | 4.0E-2 | 4.0E-2 | 3.1E2 | 9.7E1 | 262 | 26 | 110 | 26 | 0.50 |
| dI | pg/mL | 4.6E-1 | 4.6E-1 | 1.9E0 | 1.4E0 | 4.8E0 | 1.7E0 | 4.6E-1 | 4.6E-1 | 4.2E1 | 6.0E0 | 262 | 26 | 110 | 26 | 0.54 |
| dJ | ng/mL | 1.9E0 | 2.8E0 | 2.2E0 | 2.8E0 | 1.1E0 | 1.2E0 | 3.2E-2 | 1.1E0 | 5.9E0 | 5.2E0 | 262 | 26 | 110 | 26 | 0.65 |
| dK | uIU/mL | 2.0E0 | 1.6E0 | 2.6E0 | 2.9E0 | 2.6E0 | 3.9E0 | 2.8E-4 | 9.3E-2 | 1.6E1 | 1.5E1 | 262 | 26 | 110 | 26 | 0.47 |
| dL | ng/mL | 8.9E2 | 8.5E2 | 1.0E3 | 9.5E2 | 5.0E2 | 4.1E2 | 3.4E2 | 4.1E2 | 3.4E3 | 2.2E3 | 262 | 26 | 110 | 26 | 0.48 |
| dM | pg/mL | 9.7E2 | 8.4E2 | 1.2E3 | 1.1E3 | 1.0E3 | 7.8E2 | 3.5E2 | 3.9E2 | 1.2E4 | 3.6E3 | 262 | 26 | 110 | 26 | 0.44 |
| dN | ug/mL | 9.0E1 | 1.1E2 | 9.9E1 | 1.1E2 | 3.7E1 | 4.3E1 | 2.5E1 | 5.8E1 | 2.8E2 | 2.2E2 | 262 | 26 | 110 | 26 | 0.57 |
| dR | pg/mL | 1.8E3 | 1.6E3 | 2.5E3 | 2.1E3 | 2.4E3 | 2.0E3 | 1.9E2 | 1.4E2 | 1.5E4 | 8.6E3 | 150 | 25 | 104 | 25 | 0.46 |
| eF | ng/mL | 4.0E0 | 4.2E0 | 5.2E0 | 5.1E0 | 5.6E0 | 2.4E0 | 1.2E0 | 2.1E0 | 4.6E1 | 1.2E1 | 158 | 25 | 105 | 25 | 0.60 |
| eC | pg/ml | 3.0E2 | 3.0E2 | 3.7E2 | 3.1E2 | 2.5E2 | 1.3E2 | 9.9E0 | 1.6E2 | 1.4E3 | 7.1E2 | 105 | 25 | 97 | 25 | 0.46 |
| eD | pg/ml | 2.3E2 | 2.0E2 | 7.6E2 | 3.1E2 | 1.5E3 | 3.0E2 | 5.2E-1 | 4.5E1 | 8.3E3 | 1.1E3 | 81 | 26 | 74 | 26 | 0.46 |
| eT | ng/ml | 2.8E2 | 3.6E2 | 6.0E2 | 8.2E2 | 6.5E2 | 9.7E2 | 1.0E2 | 1.7E2 | 2.5E3 | 2.6E3 | 55 | 8 | 54 | 8 | 0.60 |
| eZ | ng/ml | 5.4E1 | 4.1E1 | 6.2E1 | 5.0E1 | 2.5E1 | 2.4E1 | 2.3E1 | 3.7E1 | 1.2E2 | 1.1E2 | 55 | 8 | 54 | 8 | 0.35 |
| fN | ng/ml | 2.1E-1 | 2.1E-1 | 3.9E0 | 1.5E0 | 9.2E0 | 2.8E0 | 2.1E-1 | 2.1E-1 | 5.4E1 | 8.1E0 | 55 | 8 | 54 | 8 | 0.43 |
| fP | ng/ml | 2.3E2 | 3.4E2 | 2.5E2 | 3.7E2 | 1.4E2 | 2.2E2 | 8.4E0 | 8.1E1 | 1.0E3 | 9.5E2 | 140 | 26 | 100 | 26 | 0.67 |
| fR | ng/ml | 1.2E5 | 1.2E5 | 1.7E5 | 2.3E5 | 1.3E5 | 1.8E5 | 3.1E4 | 6.5E4 | 7.7E5 | 5.8E5 | 202 | 7 | 60 | 7 | 0.60 |
| fY | ng/ml | 2.6E2 | 2.9E2 | 2.5E2 | 2.8E2 | 9.4E1 | 1.1E2 | 6.5E1 | 1.2E2 | 4.7E2 | 4.3E2 | 55 | 8 | 54 | 8 | 0.59 |
| gL | pg/ml | 6.3E4 | 7.1E4 | 7.0E4 | 7.7E4 | 3.5E4 | 3.3E4 | 1.4E4 | 3.3E4 | 2.0E5 | 1.5E5 | 150 | 25 | 104 | 25 | 0.58 |
| gP | U/ml | 2.7E2 | 3.0E2 | 2.8E2 | 2.7E2 | 9.5E1 | 7.9E1 | 8.5E1 | 8.4E1 | 8.0E2 | 4.4E2 | 157 | 25 | 105 | 25 | 0.53 |
| gW | ng/ml | 8.5E2 | 4.4E2 | 1.5E3 | 6.7E2 | 1.9E3 | 7.3E2 | 3.7E1 | 2.3E0 | 9.5E3 | 3.1E3 | 130 | 25 | 96 | 25 | 0.36 |
| tF | pg/mL | 1.6E3 | 2.6E2 | 2.0E4 | 3.4E3 | 5.4E4 | 6.9E3 | 1.2E1 | 1.8E1 | 3.2E5 | 2.9E4 | 105 | 25 | 97 | 25 | 0.38 |
| hA | ng/ml | 2.1E0 | 1.7E0 | 7.1E0 | 7.1E0 | 2.4E1 | 1.3E1 | 1.7E-2 | 1.7E-2 | 1.6E2 | 5.7E1 | 81 | 26 | 74 | 26 | 0.48 |
| nM | pg/ml | 1.0E-9 | 1.0E-9 | 1.9E2 | 1.0E-9 | 1.4E3 | 0.0E0 | 1.0E-9 | 1.0E-9 | 1.0E4 | 1.0E-9 | 53 | 18 | 51 | 18 | 0.48 |
| nN | pg/ml | 1.0E3 | 9.3E2 | 1.8E3 | 1.6E3 | 2.6E3 | 1.9E3 | 1.1E2 | 1.1E2 | 1.7E4 | 7.1E3 | 53 | 18 | 51 | 18 | 0.49 |
| nO | pg/ml | 3.2E1 | 1.7E1 | 4.9E1 | 3.3E1 | 4.9E1 | 3.7E1 | 5.5E0 | 6.5E0 | 2.4E2 | 1.4E2 | 53 | 18 | 51 | 18 | 0.32 |
| nR | pg/ml | 1.3E1 | 1.7E1 | 2.9E1 | 6.1E1 | 4.6E1 | 9.8E1 | 1.0E-9 | 8.6E-1 | 2.6E2 | 3.6E2 | 53 | 18 | 51 | 18 | 0.54 |
| nT | pg/ml | 1.1E2 | 4.2E1 | 3.7E2 | 8.4E1 | 1.2E3 | 1.2E2 | 1.0E-9 | 4.8E0 | 6.6E3 | 4.9E2 | 53 | 18 | 51 | 18 | 0.37 |
| nU | pg/ml | 1.4E1 | 6.7E1 | 5.3E2 | 1.2E2 | 2.3E3 | 1.8E2 | 1.0E-9 | 1.0E-9 | 1.3E4 | 7.5E2 | 53 | 18 | 51 | 18 | 0.67 |
| lW | pg/ml | 1.0E-9 | 1.0E-9 | 1.5E1 | 1.1E1 | 5.5E1 | 3.8E1 | 1.0E-9 | 1.0E-9 | 3.9E2 | 1.6E2 | 53 | 18 | 51 | 18 | 0.47 |
| lX | pg/ml | 1.1E3 | 1.1E3 | 1.1E3 | 1.2E3 | 5.5E2 | 4.9E2 | 2.3E2 | 3.3E2 | 2.6E3 | 2.2E3 | 53 | 18 | 51 | 18 | 0.55 |
| lY | pg/ml | 1.8E1 | 2.2E1 | 2.2E1 | 2.2E1 | 2.3E1 | 8.4E0 | 1.0E-9 | 9.7E0 | 1.4E2 | 3.8E1 | 53 | 18 | 51 | 18 | 0.60 |
| mE | pg/ml | 1.0E-9 | 7.0E-1 | 3.6E0 | 3.1E0 | 1.0E1 | 6.5E0 | 1.0E-9 | 1.0E-9 | 5.8E1 | 2.8E1 | 53 | 18 | 51 | 18 | 0.57 |
| mF | pg/ml | 1.0E-9 | 8.7E-1 | 1.8E0 | 1.6E0 | 3.3E0 | 2.2E0 | 1.0E-9 | 1.0E-9 | 1.5E1 | 6.5E0 | 53 | 18 | 51 | 18 | 0.56 |
| mH | pg/ml | 4.4E0 | 3.2E0 | 5.6E0 | 4.6E0 | 5.2E0 | 4.1E0 | 2.3E-1 | 1.4E0 | 3.2E1 | 1.8E1 | 53 | 18 | 51 | 18 | 0.45 |
| mI | pg/ml | 1.0E-9 | 1.0E-9 | 1.4E1 | 1.3E1 | 3.1E1 | 2.1E1 | 1.0E-9 | 1.0E-9 | 1.6E2 | 7.6E1 | 53 | 18 | 51 | 18 | 0.50 |
| mM | pg/ml | 1.8E1 | 2.8E1 | 4.3E1 | 8.6E1 | 5.9E1 | 1.6E2 | 1.0E-9 | 1.0E-9 | 2.3E2 | 6.5E2 | 53 | 18 | 51 | 18 | 0.58 |
| mP | pg/ml | 1.4E1 | 1.9E1 | 1.8E1 | 2.3E1 | 2.2E1 | 1.9E1 | 1.0E-9 | 1.0E-9 | 1.5E2 | 7.7E1 | 52 | 18 | 50 | 18 | 0.64 |
| mS | pg/ml | 1.8E3 | 2.0E3 | 2.1E3 | 2.1E3 | 2.3E3 | 7.3E2 | 1.0E-9 | 7.3E2 | 1.3E4 | 3.2E3 | 53 | 18 | 51 | 18 | 0.62 |
| mT | pg/ml | 5.3E1 | 7.8E1 | 1.5E2 | 1.8E2 | 2.8E2 | 2.3E2 | 9.7E0 | 1.7E1 | 1.4E3 | 8.0E2 | 52 | 18 | 50 | 18 | 0.54 |
| mU | pg/ml | 2.5E0 | 2.0E0 | 4.1E0 | 4.7E0 | 8.7E0 | 6.1E0 | 1.0E-9 | 8.2E-1 | 5.8E1 | 2.2E1 | 52 | 18 | 50 | 18 | 0.52 |
| mW | pg/ml | 2.0E3 | 3.0E3 | 2.6E3 | 3.2E3 | 1.7E3 | 2.0E3 | 3.1E2 | 8.9E2 | 1.0E4 | 9.8E3 | 52 | 18 | 50 | 18 | 0.63 |
| mY | pg/ml | 4.8E2 | 7.5E2 | 9.9E2 | 1.1E3 | 1.8E3 | 7.7E2 | 1.0E-9 | 1.5E2 | 1.1E4 | 2.6E3 | 53 | 18 | 51 | 18 | 0.68 |
| mZ | pg/ml | 1.8E2 | 1.5E2 | 3.1E2 | 2.9E2 | 2.9E2 | 3.4E2 | 1.0E-9 | 2.1E0 | 1.2E3 | 1.4E3 | 52 | 18 | 50 | 18 | 0.46 |
| nA | pg/ml | 1.3E0 | 5.5E0 | 1.6E1 | 1.1E1 | 6.7E1 | 1.7E1 | 1.0E-9 | 1.0E-9 | 4.4E2 | 5.7E1 | 52 | 18 | 50 | 18 | 0.71 |
| nB | pg/ml | 2.9E2 | 3.9E2 | 3.0E2 | 4.1E2 | 1.6E2 | 1.6E2 | 3.0E1 | 1.5E2 | 7.0E2 | 7.8E2 | 53 | 18 | 51 | 18 | 0.71 |
| nC | pg/ml | 1.0E-9 | 1.0E-9 | 8.3E3 | 1.6E3 | 5.0E4 | 4.9E3 | 1.0E-9 | 1.0E-9 | 3.7E5 | 2.0E4 | 53 | 18 | 51 | 18 | 0.49 |
| nD | pg/ml | 6.7E0 | 1.3E1 | 7.2E1 | 1.9E1 | 3.2E2 | 2.5E1 | 1.0E-9 | 1.0E-9 | 1.7E3 | 1.2E2 | 52 | 18 | 50 | 18 | 0.69 |

Figure 21 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nF | pg/ml | 1.0E-9 | 1.0E-9 | 7.7E0 | 7.4E0 | 3.9E1 | 1.5E1 | 1.0E-9 | 1.0E-9 | 2.4E2 | 4.7E1 | 53 | 18 | 51 | 18 | 0.62 |
| nH | pg/ml | 3.8E-1 | 1.8E0 | 2.1E2 | 2.8E1 | 1.4E3 | 8.0E1 | 1.0E-9 | 1.0E-9 | 1.0E4 | 3.3E2 | 52 | 18 | 50 | 18 | 0.58 |
| nI | pg/ml | 4.6E1 | 4.0E1 | 2.9E2 | 1.1E2 | 1.3E3 | 2.8E2 | 1.0E-9 | 1.0E-9 | 9.2E3 | 1.2E3 | 53 | 18 | 51 | 18 | 0.48 |
| nJ | pg/ml | 1.0E-9 | 1.6E0 | 1.0E2 | 2.3E0 | 7.1E2 | 3.5E0 | 1.0E-9 | 1.0E-9 | 5.2E3 | 1.5E1 | 53 | 18 | 51 | 18 | 0.76 |
| nK | pg/ml | 1.0E-9 | 2.7E1 | 1.2E2 | 3.7E1 | 5.4E2 | 5.4E1 | 1.0E-9 | 1.0E-9 | 3.2E3 | 2.2E2 | 52 | 18 | 50 | 18 | 0.64 |
| nL | pg/ml | 1.0E-9 | 1.0E-9 | 9.2E2 | 6.4E1 | 6.1E3 | 2.1E2 | 1.0E-9 | 1.0E-9 | 4.5E4 | 9.0E2 | 53 | 18 | 51 | 18 | 0.51 |
| hL | pg/ml | 1.8E4 | 1.5E4 | 2.4E4 | 2.1E4 | 2.2E4 | 2.0E4 | 1.0E-9 | 5.4E3 | 1.4E5 | 7.0E4 | 55 | 8 | 54 | 8 | 0.45 |
| hO | pg/ml | 1.6E4 | 1.5E4 | 1.7E4 | 1.5E4 | 3.2E3 | 1.7E3 | 1.1E4 | 1.3E4 | 2.8E4 | 1.8E4 | 55 | 8 | 54 | 8 | 0.35 |
| hP | ng/ml | 4.4E5 | 4.4E5 | 3.5E5 | 5.6E5 | 1.8E5 | 6.2E5 | 2.3E4 | 3.4E4 | 9.0E5 | 2.0E6 | 55 | 8 | 54 | 8 | 0.57 |
| wJ | pg/ml | 1.5E5 | 1.8E5 | 1.6E5 | 1.9E5 | 6.9E4 | 1.1E5 | 3.2E4 | 3.3E4 | 3.1E5 | 4.0E5 | 54 | 9 | 53 | 9 | 0.57 |
| wK | pg/ml | 3.4E4 | 5.4E4 | 4.2E4 | 5.6E4 | 2.5E4 | 4.2E4 | 5.2E3 | 8.1E3 | 1.1E5 | 1.3E5 | 54 | 9 | 53 | 9 | 0.61 |
| wL | pg/ml | 5.8E0 | 1.3E0 | 5.6E1 | 6.2E0 | 1.3E2 | 9.3E0 | 1.0E-9 | 1.0E-9 | 8.4E2 | 2.8E1 | 54 | 9 | 53 | 9 | 0.38 |
| wP | pg/ml | 2.8E4 | 2.9E4 | 4.2E4 | 4.6E4 | 4.0E4 | 4.2E4 | 1.1E3 | 6.3E3 | 1.6E5 | 1.4E5 | 54 | 9 | 53 | 9 | 0.54 |
| wQ | pg/ml | 3.5E1 | 6.7E1 | 6.3E1 | 7.8E1 | 7.8E1 | 6.3E1 | 1.0E-9 | 3.6E0 | 3.7E2 | 1.7E2 | 54 | 9 | 53 | 9 | 0.61 |
| hR | pg/ml | 2.9E4 | 2.4E4 | 3.0E4 | 2.5E4 | 1.2E4 | 9.3E3 | 1.8E3 | 1.1E1 | 5.8E4 | 4.3E4 | 79 | 24 | 72 | 24 | 0.38 |
| hV | pg/ml | 4.7E2 | 4.5E2 | 5.1E2 | 4.6E2 | 2.5E2 | 1.9E2 | 1.3E2 | 2.2E2 | 1.5E3 | 8.1E2 | 79 | 24 | 72 | 24 | 0.45 |
| hW | pg/ml | 1.5E3 | 1.8E3 | 1.8E3 | 2.1E3 | 9.5E2 | 1.5E3 | 5.7E2 | 7.1E2 | 4.8E3 | 7.7E3 | 79 | 24 | 72 | 24 | 0.59 |
| hX | pg/ml | 9.3E2 | 1.1E3 | 1.1E3 | 1.1E3 | 1.0E3 | 4.0E2 | 3.6E2 | 5.2E2 | 8.6E3 | 2.2E3 | 79 | 24 | 72 | 24 | 0.57 |
| iA | pg/ml | 1.4E2 | 1.4E2 | 4.0E2 | 2.0E2 | 9.0E2 | 2.1E2 | 1.1E1 | 3.0E1 | 7.1E3 | 9.5E2 | 105 | 25 | 97 | 25 | 0.48 |
| iB | ng/ml | 4.9E0 | 4.1E0 | 6.3E0 | 5.3E0 | 4.7E0 | 4.4E0 | 3.7E-2 | 3.3E-2 | 1.9E1 | 2.1E1 | 81 | 26 | 74 | 26 | 0.43 |
| iC | U/ml | 2.2E-1 | 1.8E-1 | 4.4E-1 | 2.4E0 | 8.3E-1 | 1.1E1 | 1.0E-9 | 1.0E-9 | 6.4E0 | 5.5E1 | 81 | 26 | 74 | 26 | 0.52 |
| tQ | pg/ml | 1.1E3 | 1.1E3 | 1.2E3 | 1.2E3 | 5.3E2 | 6.3E2 | 2.8E2 | 5.0E2 | 2.5E3 | 2.5E3 | 53 | 8 | 52 | 8 | 0.51 |
| tT | pg/ml | 1.7E1 | 2.1E1 | 1.8E1 | 2.0E1 | 9.7E0 | 1.2E1 | 7.4E0 | 5.4E0 | 6.9E1 | 3.9E1 | 53 | 8 | 52 | 8 | 0.57 |
| tS | pg/ml | 1.1E0 | 1.3E0 | 1.4E0 | 1.4E0 | 1.4E0 | 1.3E0 | 1.0E-9 | 1.0E-9 | 8.5E0 | 3.2E0 | 53 | 8 | 52 | 8 | 0.52 |
| tX | pg/ml | 8.6E-1 | 6.0E-1 | 1.1E0 | 9.5E-1 | 8.6E-1 | 7.6E-1 | 2.5E-2 | 1.6E-1 | 4.4E0 | 2.1E0 | 53 | 8 | 52 | 8 | 0.45 |
| tO | pg/ml | 3.9E0 | 4.4E0 | 4.7E0 | 5.3E0 | 3.1E0 | 3.6E0 | 1.0E-9 | 1.7E0 | 1.4E1 | 1.1E1 | 53 | 8 | 52 | 8 | 0.53 |
| tR | pg/ml | 2.2E-1 | 1.9E-1 | 2.9E-1 | 2.5E-1 | 2.9E-1 | 2.2E-1 | 1.0E-9 | 5.5E-2 | 1.5E0 | 7.1E-1 | 53 | 8 | 52 | 8 | 0.46 |
| tU | pg/ml | 8.7E0 | 8.9E0 | 1.1E1 | 9.7E0 | 7.1E0 | 4.6E0 | 1.6E0 | 3.0E0 | 3.1E1 | 1.7E1 | 53 | 9 | 52 | 9 | 0.48 |
| tN | pg/ml | 1.7E1 | 1.9E1 | 2.1E1 | 2.1E1 | 1.4E1 | 1.1E1 | 1.0E-9 | 9.4E0 | 8.0E1 | 4.5E1 | 53 | 9 | 52 | 9 | 0.50 |
| tV | ng/ml | 4.2E2 | 5.4E2 | 5.3E2 | 6.7E2 | 5.0E2 | 5.0E2 | 1.5E2 | 1.4E2 | 2.9E3 | 1.8E3 | 54 | 9 | 53 | 9 | 0.59 |
| iH | ng/ml | 1.5E5 | 1.8E5 | 1.5E5 | 1.8E5 | 4.4E4 | 5.2E4 | 7.1E4 | 5.1E4 | 2.4E5 | 2.7E5 | 105 | 25 | 97 | 25 | 0.69 |
| iJ | ng/ml | 5.1E4 | 5.7E4 | 5.2E4 | 5.9E4 | 2.2E4 | 3.2E4 | 5.5E3 | 8.6E3 | 1.0E5 | 1.5E5 | 105 | 25 | 97 | 25 | 0.56 |
| hB | ng/ml | 4.4E-1 | 4.3E-1 | 5.0E-1 | 6.9E-1 | 3.2E-1 | 6.2E-1 | 1.0E-9 | 2.0E-1 | 1.7E0 | 2.4E0 | 105 | 25 | 97 | 25 | 0.54 |
| hC | pg/ml | 3.7E3 | 3.4E3 | 5.7E3 | 7.1E3 | 7.5E3 | 1.0E4 | 1.0E-9 | 6.2E1 | 5.5E4 | 4.3E4 | 105 | 25 | 97 | 25 | 0.51 |
| hF | ng/ml | 1.0E-9 | 1.0E-9 | 4.7E1 | 1.0E-9 | 4.0E2 | 0.0E0 | 1.0E-9 | 1.0E-9 | 4.0E3 | 1.0E-9 | 105 | 25 | 97 | 25 | 0.48 |
| hG | pg/ml | 7.0E3 | 6.9E3 | 7.3E3 | 8.4E3 | 3.1E3 | 3.4E3 | 2.8E1 | 4.7E3 | 1.8E4 | 1.8E4 | 105 | 25 | 97 | 25 | 0.57 |
| iO | ng/ml | 3.8E5 | 4.0E5 | 4.1E5 | 3.8E5 | 1.9E5 | 1.7E5 | 1.1E4 | 6.4E4 | 1.1E6 | 8.6E5 | 105 | 25 | 97 | 25 | 0.46 |
| iP | pg/ml | 6.0E4 | 4.6E4 | 5.5E4 | 5.3E4 | 3.2E4 | 3.5E4 | 1.0E-9 | 1.3E4 | 2.5E5 | 1.9E5 | 105 | 25 | 97 | 25 | 0.44 |
| iZ | ng/ml | 1.6E3 | 1.7E3 | 1.8E3 | 1.8E3 | 7.5E2 | 5.9E2 | 4.7E2 | 6.5E2 | 5.1E3 | 3.1E3 | 105 | 25 | 97 | 25 | 0.52 |
| yH | pg/ml | 1.1E3 | 7.5E2 | 1.9E3 | 9.8E2 | 2.9E3 | 5.8E2 | 1.0E-9 | 1.6E2 | 1.5E4 | 1.9E3 | 54 | 9 | 53 | 9 | 0.41 |
| yK | U/ml | 1.9E1 | 4.7E1 | 4.8E1 | 4.6E1 | 8.2E1 | 3.6E1 | 1.0E-9 | 4.7E-1 | 3.8E2 | 1.0E2 | 54 | 9 | 53 | 9 | 0.61 |
| yJ | pg/ml | 3.4E4 | 3.2E4 | 4.6E4 | 4.4E4 | 3.4E4 | 4.3E4 | 1.7E3 | 7.1E3 | 1.6E5 | 1.4E5 | 54 | 9 | 53 | 9 | 0.44 |
| yD | ng/ml | 1.5E-2 | 1.7E-2 | 1.5E-2 | 1.7E-2 | 6.9E-3 | 8.4E-3 | 1.0E-9 | 5.4E-3 | 4.3E-2 | 3.2E-2 | 54 | 9 | 53 | 9 | 0.55 |
| wB | pg/ml | 8.1E3 | 8.3E3 | 9.5E3 | 8.4E3 | 7.2E3 | 5.3E3 | 1.7E3 | 2.7E3 | 4.1E4 | 2.1E4 | 54 | 9 | 53 | 9 | 0.47 |
| pY | pg/ml | 6.0E0 | 7.1E0 | 1.1E1 | 6.9E0 | 2.6E1 | 2.5E0 | 2.1E0 | 3.4E0 | 2.0E2 | 1.1E1 | 55 | 8 | 54 | 8 | 0.57 |
| rC | pg/ml | 1.9E3 | 1.7E3 | 2.3E3 | 2.1E3 | 2.2E3 | 1.9E3 | 9.3E1 | 2.5E2 | 1.5E4 | 8.4E3 | 78 | 25 | 72 | 25 | 0.49 |
| rB | pg/ml | 2.2E1 | 3.0E1 | 4.6E1 | 3.5E1 | 1.2E2 | 3.1E1 | 1.0E-9 | 1.0E-9 | 9.5E2 | 1.3E2 | 78 | 25 | 72 | 25 | 0.58 |
| zG | 2.5ng/ml | 2.2E-1 | 2.5E-1 | 4.8E-1 | 7.7E-1 | 7.5E-1 | 1.5E0 | 1.0E-9 | 5.1E-2 | 4.4E0 | 4.8E0 | 54 | 9 | 53 | 9 | 0.52 |
| zH | 2.3mU/ml | 1.1E-1 | 9.9E-2 | 1.2E-1 | 1.0E-1 | 6.9E-2 | 3.5E-2 | 1.0E-2 | 4.0E-2 | 4.4E-1 | 1.6E-1 | 54 | 9 | 53 | 9 | 0.44 |
| zI | 2.6ng/ml | 1.9E0 | 2.6E0 | 3.4E0 | 4.8E0 | 3.6E0 | 5.0E0 | 6.3E-1 | 1.5E0 | 1.6E1 | 1.4E1 | 54 | 9 | 53 | 9 | 0.64 |
| qA | ng/ml | 1.1E7 | 7.3E6 | 1.3E7 | 1.5E7 | 7.4E6 | 1.2E7 | 3.7E6 | 6.9E6 | 3.7E7 | 3.9E7 | 55 | 8 | 54 | 8 | 0.47 |
| qB | ng/ml | 6.1E5 | 4.5E5 | 8.3E5 | 8.2E5 | 5.9E5 | 9.0E5 | 2.1E5 | 2.7E5 | 2.9E6 | 2.9E6 | 55 | 8 | 54 | 8 | 0.40 |
| qC | ng/ml | 4.5E5 | 3.3E5 | 9.1E5 | 3.5E5 | 1.3E6 | 3.0E5 | 2.0E4 | 2.5E4 | 7.1E6 | 7.9E5 | 55 | 8 | 54 | 8 | 0.35 |
| qD | ng/ml | 1.6E7 | 1.3E7 | 2.0E7 | 1.2E7 | 1.0E7 | 4.5E6 | 1.2E6 | 6.2E6 | 5.2E7 | 1.9E7 | 55 | 8 | 54 | 8 | 0.27 |
| jD | ng/ml | 2.0E1 | 2.7E1 | 4.1E1 | 4.9E1 | 7.0E1 | 5.0E1 | 1.0E-9 | 1.0E-9 | 5.1E2 | 1.9E2 | 81 | 26 | 74 | 26 | 0.58 |
| jE | ng/ml | 1.0E-9 | 1.0E-9 | 8.5E0 | 3.8E0 | 2.1E1 | 8.3E0 | 1.0E-9 | 1.0E-9 | 1.2E2 | 2.9E1 | 81 | 26 | 74 | 26 | 0.47 |
| jF | ng/ml | 4.9E1 | 3.0E1 | 5.8E1 | 4.5E1 | 5.8E1 | 4.9E1 | 1.0E-9 | 1.0E-9 | 2.5E2 | 1.5E2 | 81 | 26 | 74 | 26 | 0.43 |

Figure 21 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jG | ng/ml | 4.4E3 | 4.8E3 | 4.4E3 | 4.7E3 | 1.9E3 | 2.1E3 | 7.6E2 | 1.5E3 | 8.9E3 | 8.6E3 | 81 | 26 | 74 | 26 | 0.54 |
| jH | ng/ml | 7.6E1 | 6.9E1 | 8.6E1 | 7.3E1 | 4.9E1 | 3.2E1 | 1.9E1 | 1.3E1 | 2.8E2 | 1.6E2 | 81 | 26 | 74 | 26 | 0.43 |
| jI | ng/ml | 6.3E1 | 7.5E1 | 6.9E1 | 7.4E1 | 3.5E1 | 2.0E1 | 1.9E1 | 2.8E1 | 2.5E2 | 1.1E2 | 81 | 26 | 74 | 26 | 0.62 |
| sK | pg/mL | 3.7E3 | 4.4E3 | 4.0E3 | 4.4E3 | 1.3E3 | 2.2E3 | 1.7E3 | 1.9E3 | 8.0E3 | 8.9E3 | 54 | 9 | 53 | 9 | 0.54 |
| sM | pg/mL | 7.3E4 | 8.9E4 | 7.5E4 | 8.6E4 | 2.1E4 | 3.2E4 | 3.3E4 | 4.3E4 | 1.5E5 | 1.4E5 | 54 | 9 | 53 | 9 | 0.62 |
| sO | pg/mL | 3.0E8 | 3.0E8 | 3.0E8 | 2.5E8 | 9.2E7 | 6.9E7 | 7.9E7 | 1.4E8 | 4.9E8 | 3.3E8 | 54 | 9 | 53 | 9 | 0.36 |
| wC | ng/ml | 1.6E0 | 1.5E0 | 2.2E0 | 1.9E0 | 2.3E0 | 1.1E0 | 2.5E-1 | 9.5E-1 | 1.5E1 | 4.2E0 | 54 | 9 | 53 | 9 | 0.54 |
| wD | ng/ml | 1.6E1 | 1.2E1 | 7.3E1 | 1.7E1 | 2.9E2 | 1.4E1 | 2.1E0 | 5.1E0 | 2.1E3 | 5.2E1 | 54 | 9 | 53 | 9 | 0.45 |
| wE | ng/ml | 4.9E1 | 4.5E1 | 5.3E1 | 4.3E1 | 2.5E1 | 2.5E1 | 7.0E0 | 4.0E0 | 1.4E2 | 8.9E1 | 54 | 9 | 53 | 9 | 0.40 |
| wG | ng/ml | 8.2E-2 | 1.2E-2 | 1.2E-1 | 5.8E-2 | 1.5E-1 | 1.1E-1 | 1.0E-9 | 1.0E-9 | 7.1E-1 | 3.3E-1 | 54 | 9 | 53 | 9 | 0.36 |
| wH | ng/ml | 1.9E-2 | 6.0E-3 | 1.6E-1 | 7.7E-2 | 4.9E-1 | 1.5E-1 | 1.0E-9 | 1.0E-9 | 2.9E0 | 4.0E-1 | 54 | 9 | 53 | 9 | 0.40 |
| wF | ng/ml | 1.7E-1 | 4.2E-2 | 2.5E0 | 2.7E-1 | 9.9E0 | 3.6E-1 | 1.0E-9 | 1.0E-9 | 5.7E1 | 1.1E0 | 54 | 9 | 53 | 9 | 0.51 |
| rA | pg/ml | 2.4E1 | 2.7E1 | 3.0E1 | 3.4E1 | 2.7E1 | 2.2E1 | 1.0E-9 | 1.0E-9 | 2.0E2 | 8.2E1 | 80 | 27 | 74 | 27 | 0.58 |
| qZ | pg/ml | 4.3E1 | 4.6E1 | 1.9E2 | 7.6E2 | 1.2E3 | 2.7E3 | 2.8E-4 | 7.2E-4 | 1.0E4 | 1.0E4 | 71 | 14 | 68 | 14 | 0.52 |
| qY | pg/ml | 2.9E1 | 1.8E1 | 5.1E1 | 3.9E1 | 7.4E1 | 4.7E1 | 8.7E-1 | 2.2E0 | 5.3E2 | 1.8E2 | 80 | 27 | 74 | 27 | 0.43 |
| qX | pg/ml | 5.4E1 | 7.5E1 | 6.0E1 | 8.8E1 | 3.8E1 | 5.7E1 | 1.0E-9 | 1.0E-9 | 1.8E2 | 2.1E2 | 80 | 27 | 74 | 27 | 0.65 |
| qW | pg/ml | 9.7E0 | 1.0E1 | 1.5E1 | 1.1E1 | 2.0E1 | 7.2E0 | 1.0E-9 | 1.0E-9 | 1.2E2 | 2.3E1 | 80 | 27 | 74 | 27 | 0.48 |
| qV | pg/ml | 2.2E3 | 1.7E3 | 2.8E3 | 2.6E3 | 2.0E3 | 2.0E3 | 2.3E2 | 1.7E2 | 8.5E3 | 7.1E3 | 80 | 27 | 74 | 27 | 0.46 |
| qU | pg/ml | 5.5E1 | 6.5E1 | 1.7E2 | 9.2E1 | 2.6E2 | 7.6E1 | 1.0E-9 | 1.0E1 | 1.4E3 | 2.8E2 | 80 | 27 | 74 | 27 | 0.52 |
| qT | pg/ml | 3.7E1 | 5.5E1 | 6.5E1 | 8.0E1 | 1.2E2 | 8.3E1 | 1.0E-9 | 5.6E0 | 9.0E2 | 4.4E2 | 80 | 27 | 74 | 27 | 0.65 |
| qI | ng/ml | 5.4E4 | 6.9E4 | 6.2E4 | 6.1E4 | 3.1E4 | 2.7E4 | 1.1E4 | 2.5E4 | 1.6E5 | 9.8E4 | 54 | 9 | 54 | 9 | 0.50 |
| qH | ng/ml | 6.6E4 | 6.6E4 | 7.2E4 | 6.9E4 | 3.8E4 | 4.5E4 | 1.5E4 | 2.3E4 | 1.8E5 | 1.6E5 | 54 | 9 | 54 | 9 | 0.44 |
| qG | ng/ml | 1.8E5 | 2.0E5 | 1.9E5 | 2.2E5 | 5.9E4 | 5.6E4 | 5.8E4 | 1.5E5 | 3.3E5 | 2.9E5 | 54 | 9 | 54 | 9 | 0.61 |
| jK | ng/ml | 1.6E3 | 1.9E3 | 1.7E3 | 1.8E3 | 5.3E2 | 4.8E2 | 5.5E2 | 7.6E2 | 3.5E3 | 2.8E3 | 81 | 26 | 74 | 26 | 0.58 |
| jL | ng/ml | 1.7E2 | 2.0E2 | 2.5E2 | 3.3E2 | 1.9E2 | 3.5E2 | 3.6E1 | 8.8E1 | 9.6E2 | 1.7E3 | 81 | 26 | 74 | 26 | 0.55 |
| jM | ng/ml | 7.1E4 | 7.5E4 | 7.3E4 | 8.3E4 | 4.0E4 | 3.9E4 | 3.9E2 | 2.4E4 | 1.9E5 | 1.6E5 | 81 | 26 | 74 | 26 | 0.57 |
| jO | pg/ml | 2.1E5 | 2.0E5 | 2.7E5 | 2.7E5 | 1.7E5 | 1.8E5 | 5.2E4 | 7.4E4 | 1.1E6 | 8.0E5 | 81 | 26 | 74 | 26 | 0.49 |
| jP | pg/ml | 2.2E5 | 2.3E5 | 2.5E5 | 2.6E5 | 1.5E5 | 1.7E5 | 3.6E4 | 6.6E4 | 9.1E5 | 9.2E5 | 81 | 26 | 74 | 26 | 0.50 |
| jQ | pg/ml | 2.8E3 | 3.0E3 | 3.7E3 | 3.4E3 | 3.1E3 | 2.4E3 | 4.2E1 | 2.6E2 | 1.3E4 | 1.0E4 | 81 | 26 | 74 | 26 | 0.49 |
| jR | pg/ml | 8.6E3 | 7.8E3 | 1.3E4 | 1.0E4 | 1.3E4 | 9.4E3 | 1.0E-9 | 7.2E1 | 6.8E4 | 3.4E4 | 81 | 26 | 74 | 26 | 0.47 |
| jT | pg/ml | 1.7E5 | 1.9E5 | 1.7E5 | 1.9E5 | 6.3E4 | 5.7E4 | 6.8E4 | 9.0E4 | 3.9E5 | 3.1E5 | 81 | 26 | 74 | 26 | 0.59 |
| xA | pg/ml | 3.9E0 | 1.0E1 | 1.5E1 | 2.8E1 | 5.4E1 | 4.6E1 | 1.0E-9 | 1.0E-9 | 3.9E2 | 1.4E2 | 54 | 9 | 53 | 9 | 0.62 |
| yE | pg/ml | 7.9E1 | 7.0E1 | 8.3E1 | 8.7E1 | 4.4E1 | 4.0E1 | 1.8E1 | 4.0E1 | 3.0E2 | 1.6E2 | 54 | 9 | 53 | 9 | 0.53 |
| tM | pg/ml | 3.9E1 | 3.3E1 | 4.2E1 | 3.6E1 | 2.1E1 | 2.0E1 | 1.0E-9 | 1.0E-9 | 1.0E2 | 6.1E1 | 54 | 9 | 53 | 9 | 0.43 |
| tL | pg/ml | 1.0E-9 | 1.0E-9 | 6.9E0 | 1.5E-1 | 3.6E1 | 4.6E-1 | 1.0E-9 | 1.0E-9 | 2.6E2 | 1.4E0 | 54 | 9 | 53 | 9 | 0.43 |
| jU | mIU/ml | 3.5E0 | 6.4E0 | 1.0E1 | 1.3E1 | 1.8E1 | 1.7E1 | 8.9E-2 | 6.3E-2 | 8.1E1 | 7.5E1 | 81 | 26 | 74 | 26 | 0.61 |
| jV | mIU/ml | 1.5E0 | 2.1E0 | 3.4E0 | 4.9E0 | 5.5E0 | 7.8E0 | 3.4E-2 | 1.1E-3 | 3.1E1 | 3.3E1 | 81 | 26 | 74 | 26 | 0.52 |
| jY | | 7.4E-4 | 7.5E-4 | 9.8E-3 | 6.7E-3 | 4.1E-2 | 1.9E-2 | 1.0E-9 | 1.0E-9 | 3.0E-1 | 9.4E-2 | 81 | 26 | 74 | 26 | 0.50 |
| kC | pg/ml | 9.7E1 | 1.2E2 | 2.3E2 | 1.2E2 | 5.6E2 | 6.4E1 | 2.9E1 | 3.6E1 | 3.5E3 | 2.9E2 | 53 | 18 | 51 | 18 | 0.53 |
| kE | pg/ml | 1.2E5 | 1.4E5 | 1.3E5 | 1.3E5 | 3.2E4 | 3.8E4 | 4.1E4 | 3.8E4 | 2.0E5 | 2.0E5 | 53 | 18 | 51 | 18 | 0.53 |
| kF | pg/mL | 6.0E1 | 5.6E1 | 7.4E1 | 6.7E1 | 7.1E1 | 2.5E1 | 2.7E1 | 3.8E1 | 5.1E2 | 1.4E2 | 53 | 18 | 51 | 18 | 0.52 |
| kG | pg/mL | 8.5E3 | 1.0E4 | 9.4E3 | 2.1E4 | 7.8E3 | 3.0E4 | 7.5E2 | 3.8E3 | 4.3E4 | 1.2E5 | 53 | 18 | 51 | 18 | 0.60 |
| kI | pg/ml | 2.0E2 | 1.7E2 | 2.4E2 | 2.1E2 | 1.5E2 | 1.3E2 | 7.9E1 | 8.8E1 | 8.7E2 | 5.5E2 | 53 | 18 | 51 | 18 | 0.40 |
| kK | pg/ml | 1.0E2 | 1.1E2 | 1.6E2 | 2.0E2 | 1.9E2 | 2.7E2 | 6.4E0 | 4.5E1 | 1.2E3 | 1.2E3 | 53 | 18 | 51 | 18 | 0.53 |
| kN | pg/ml | 9.2E2 | 9.8E2 | 1.4E3 | 1.3E3 | 1.9E3 | 1.1E3 | 2.4E2 | 2.4E2 | 1.3E4 | 3.9E3 | 53 | 18 | 51 | 18 | 0.52 |
| kO | pg/ml | 7.7E3 | 6.1E3 | 1.0E4 | 6.9E3 | 1.8E4 | 2.6E3 | 3.7E3 | 3.8E3 | 1.3E5 | 1.4E4 | 53 | 18 | 51 | 18 | 0.34 |
| kP | pg/ml | 4.8E3 | 6.2E3 | 6.8E3 | 6.5E3 | 6.1E3 | 2.7E3 | 8.6E2 | 2.7E3 | 3.3E4 | 1.2E4 | 53 | 18 | 51 | 18 | 0.58 |
| kQ | pg/ml | 4.2E3 | 3.8E2 | 4.9E3 | 4.4E3 | 2.6E3 | 2.1E3 | 5.6E2 | 1.6E3 | 1.4E4 | 9.3E3 | 105 | 25 | 97 | 25 | 0.43 |
| kR | pg/ml | 2.0E1 | 2.1E1 | 3.6E1 | 2.7E1 | 1.0E2 | 1.8E1 | 1.0E-9 | 5.1E0 | 1.0E3 | 6.9E1 | 105 | 25 | 97 | 25 | 0.53 |
| kS | pg/ml | 7.6E2 | 8.2E2 | 8.9E2 | 8.2E2 | 5.2E2 | 3.4E2 | 1.3E2 | 2.5E2 | 3.2E3 | 1.7E3 | 105 | 25 | 97 | 25 | 0.51 |
| pS | ng/ml | 1.8E5 | 2.1E5 | 2.1E5 | 2.4E5 | 9.0E4 | 1.4E5 | 9.7E4 | 1.0E5 | 5.0E5 | 5.7E5 | 54 | 9 | 53 | 9 | 0.56 |
| rZ | ng/ml | 1.0E-9 | 1.0E-9 | 7.1E-3 | 1.4E-2 | 2.0E-2 | 6.0E-2 | 1.0E-9 | 1.0E-9 | 1.1E-1 | 3.0E-1 | 78 | 25 | 71 | 25 | 0.48 |
| rY | ng/ml | 5.3E-2 | 5.4E-2 | 2.2E-1 | 7.8E-1 | 8.1E-1 | 3.6E0 | 1.0E-9 | 1.0E-9 | 6.3E0 | 1.8E1 | 78 | 25 | 71 | 25 | 0.46 |
| rX | ng/ml | 1.0E-9 | 1.0E-9 | 8.4E-2 | 1.1E-1 | 4.4E-1 | 4.8E-1 | 1.0E-9 | 1.0E-9 | 3.7E0 | 2.4E0 | 78 | 25 | 71 | 25 | 0.44 |
| lK | pg/ml | 7.5E1 | 6.6E1 | 1.6E2 | 1.7E2 | 1.9E2 | 3.0E2 | 1.0E-9 | 1.0E-9 | 7.4E2 | 1.3E3 | 81 | 26 | 74 | 26 | 0.45 |
| lL | pg/ml | 1.7E3 | 1.6E3 | 2.7E3 | 2.1E3 | 3.0E3 | 1.8E3 | 7.5E1 | 4.5E2 | 1.9E4 | 6.8E3 | 81 | 26 | 74 | 26 | 0.45 |
| lM | pg/ml | 1.1E3 | 1.3E3 | 2.2E3 | 6.9E3 | 3.0E3 | 1.2E4 | 1.3E2 | 2.7E2 | 1.6E4 | 4.4E4 | 81 | 26 | 74 | 26 | 0.56 |

Figure 21 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| lN | pg/ml | 1.0E-9 | 1.0E-9 | 6.9E0 | 1.5E0 | 2.2E1 | 2.9E0 | 1.0E-9 | 1.0E-9 | 1.5E2 | 1.2E1 | 81 | 26 | 74 | 26 | 0.41 |
| lO | pg/ml | 1.0E-9 | 1.0E-9 | 5.0E-1 | 1.0E0 | 4.5E0 | 3.6E0 | 1.0E-9 | 1.0E-9 | 4.0E1 | 1.3E1 | 81 | 26 | 74 | 26 | 0.53 |
| zA | ng/ml | 1.9E7 | 1.9E7 | 1.9E7 | 1.9E7 | 6.6E6 | 4.0E6 | 6.7E6 | 1.1E7 | 3.4E7 | 2.6E7 | 50 | 9 | 49 | 9 | 0.49 |
| rW | ng/ml | 1.7E-2 | 8.7E-3 | 2.7E-2 | 3.3E-2 | 3.2E-2 | 5.2E-2 | 1.0E-9 | 1.0E-9 | 1.7E-1 | 1.6E-1 | 54 | 10 | 54 | 10 | 0.47 |
| rV | ng/ml | 1.0E-9 | 1.0E-9 | 1.2E-2 | 2.9E-2 | 4.0E-2 | 8.9E-2 | 1.0E-9 | 1.0E-9 | 2.2E-1 | 2.8E-1 | 54 | 10 | 54 | 10 | 0.49 |
| rU | ng/ml | 1.1E-1 | 2.0E-2 | 1.8E-1 | 6.9E-1 | 2.7E-1 | 1.5E0 | 1.0E-9 | 1.0E-9 | 1.4E0 | 4.4E0 | 54 | 10 | 54 | 10 | 0.38 |
| rT | ng/ml | 6.5E0 | 4.8E0 | 6.8E0 | 5.2E0 | 4.2E0 | 2.5E0 | 7.3E-1 | 1.3E0 | 2.1E1 | 1.0E1 | 54 | 10 | 54 | 10 | 0.38 |
| rS | ng/ml | 3.5E0 | 5.1E0 | 5.8E0 | 5.5E0 | 6.6E0 | 3.3E0 | 7.6E-1 | 1.5E0 | 3.8E1 | 1.3E1 | 54 | 10 | 54 | 10 | 0.60 |
| sC | pg/mL | 5.8E3 | 8.2E3 | 9.5E3 | 1.2E4 | 8.6E3 | 1.2E4 | 1.7E3 | 2.3E3 | 4.4E4 | 3.9E4 | 54 | 9 | 53 | 9 | 0.55 |
| yL | pg/ml | 3.2E1 | 3.0E1 | 3.9E1 | 2.8E1 | 2.8E1 | 8.4E0 | 5.6E0 | 1.1E1 | 1.8E2 | 3.8E1 | 52 | 9 | 51 | 9 | 0.37 |
| rP | ng/ml | 9.5E1 | 1.1E2 | 1.6E2 | 2.0E2 | 2.2E2 | 1.2E2 | 1.0E-9 | 3.7E0 | 1.2E3 | 5.0E2 | 54 | 10 | 54 | 10 | 0.56 |
| rQ | ng/ml | 1.0E-9 | 1.0E-9 | 3.6E0 | 1.7E1 | 1.6E1 | 5.3E1 | 1.0E-9 | 1.0E-9 | 8.9E1 | 1.7E2 | 54 | 10 | 54 | 10 | 0.51 |
| rO | ng/ml | 2.5E-2 | 3.0E-2 | 4.8E-2 | 8.6E-2 | 8.5E-2 | 1.4E-1 | 1.0E-9 | 1.0E-9 | 4.4E-1 | 4.7E-1 | 54 | 10 | 54 | 10 | 0.55 |
| rR | ng/ml | 3.9E0 | 2.0E0 | 2.3E1 | 5.8E0 | 6.8E1 | 1.1E1 | 1.0E-9 | 1.0E-9 | 4.5E2 | 3.6E1 | 54 | 10 | 54 | 10 | 0.40 |
| rN | ng/ml | 6.6E-1 | 6.4E-1 | 7.4E-1 | 8.1E-1 | 4.4E-1 | 6.1E-1 | 5.1E-2 | 2.7E-1 | 2.1E0 | 2.3E0 | 54 | 10 | 54 | 10 | 0.51 |
| qO | pg/ml | 9.8E3 | 1.1E4 | 1.3E4 | 1.5E4 | 9.6E3 | 1.5E4 | 2.2E3 | 7.4E2 | 4.6E4 | 5.0E4 | 55 | 9 | 54 | 9 | 0.49 |
| qP | pg/ml | 3.6E2 | 3.6E2 | 4.4E2 | 5.1E2 | 3.0E2 | 5.5E2 | 1.0E-9 | 1.1E2 | 1.5E3 | 1.9E3 | 55 | 9 | 54 | 9 | 0.46 |
| qQ | pg/ml | 1.5E1 | 1.0E-9 | 1.7E1 | 7.3E0 | 3.8E1 | 8.7E0 | 1.0E-9 | 1.0E-9 | 2.8E2 | 1.9E1 | 55 | 9 | 54 | 9 | 0.38 |
| nW | pg/ml | 1.1E5 | 1.1E5 | 1.1E5 | 1.2E5 | 2.4E4 | 2.8E4 | 5.8E4 | 6.9E4 | 1.8E5 | 1.6E5 | 105 | 25 | 97 | 25 | 0.52 |
| nY | pg/ml | 1.9E3 | 1.6E3 | 2.2E3 | 2.1E3 | 1.4E3 | 1.3E3 | 6.5E2 | 6.6E2 | 9.9E3 | 5.3E3 | 105 | 25 | 97 | 25 | 0.47 |
| oO | pg/ml | 7.5E4 | 9.9E4 | 1.0E5 | 1.3E5 | 1.1E5 | 9.2E4 | 1.5E4 | 2.6E4 | 6.2E5 | 2.8E5 | 51 | 16 | 49 | 16 | 0.62 |
| oP | pg/ml | 1.1E5 | 1.7E5 | 1.3E5 | 1.8E5 | 7.7E4 | 9.7E4 | 2.4E4 | 6.3E4 | 3.6E5 | 3.6E5 | 51 | 16 | 49 | 16 | 0.67 |
| oQ | pg/ml | 2.5E3 | 3.0E3 | 2.9E3 | 4.6E3 | 1.7E3 | 3.3E3 | 9.3E2 | 1.6E3 | 1.0E4 | 1.2E4 | 51 | 16 | 49 | 16 | 0.65 |
| oE | pg/ml | 1.8E2 | 7.1E1 | 4.0E2 | 3.0E2 | 6.0E2 | 5.9E2 | 1.0E-9 | 1.0E-9 | 4.7E3 | 2.8E3 | 105 | 25 | 97 | 25 | 0.39 |
| oF | pg/ml | 7.4E3 | 9.4E3 | 1.7E4 | 2.7E4 | 3.0E4 | 3.7E4 | 6.4E1 | 6.5E2 | 1.7E5 | 1.4E5 | 105 | 25 | 97 | 25 | 0.58 |
| oH | pg/ml | 4.4E1 | 3.9E1 | 9.5E1 | 1.0E2 | 1.5E2 | 1.9E2 | 4.2E0 | 4.3E-1 | 8.6E2 | 9.9E2 | 105 | 25 | 97 | 25 | 0.50 |
| oK | pg/ml | 6.4E2 | 9.0E2 | 2.0E3 | 1.9E3 | 3.1E3 | 3.2E3 | 5.2E1 | 1.8E2 | 1.8E4 | 1.2E4 | 105 | 25 | 97 | 25 | 0.50 |
| oN | pg/ml | 4.9E2 | 5.3E2 | 7.8E2 | 8.6E2 | 1.8E3 | 9.1E2 | 1.5E2 | 2.6E2 | 1.8E4 | 3.7E3 | 105 | 25 | 97 | 25 | 0.58 |
| uL | ng/ml | 3.6E1 | 3.9E1 | 4.4E1 | 7.1E1 | 3.0E1 | 1.0E2 | 1.0E-9 | 2.4E1 | 1.6E2 | 3.4E2 | 52 | 9 | 51 | 9 | 0.54 |
| uO | ng/ml | 3.0E-1 | 1.8E-1 | 7.8E-1 | 5.7E-1 | 1.4E0 | 6.9E-1 | 1.0E-9 | 1.0E-9 | 9.3E0 | 2.0E0 | 52 | 9 | 51 | 9 | 0.49 |
| uM | ng/ml | 6.4E-1 | 5.9E-1 | 1.1E0 | 7.9E-1 | 2.2E0 | 3.6E-1 | 1.0E-9 | 4.7E-1 | 1.3E1 | 1.6E0 | 52 | 9 | 51 | 9 | 0.56 |
| uI | ng/ml | 7.7E-2 | 5.8E-2 | 1.4E-1 | 1.0E-1 | 1.9E-1 | 1.1E-1 | 1.6E-2 | 3.6E-2 | 1.1E0 | 3.9E-1 | 52 | 9 | 51 | 9 | 0.43 |
| uN | ng/ml | 1.5E1 | 1.5E1 | 1.7E1 | 1.7E1 | 6.7E0 | 6.7E0 | 7.7E0 | 8.1E0 | 4.1E1 | 3.0E1 | 52 | 9 | 51 | 9 | 0.50 |
| uG | ng/ml | 2.1E1 | 1.7E1 | 2.5E1 | 2.7E1 | 1.4E1 | 2.4E1 | 7.6E0 | 6.1E0 | 6.9E1 | 7.9E1 | 52 | 9 | 51 | 9 | 0.46 |
| uR | ng/ml | 2.3E0 | 2.7E0 | 3.9E0 | 2.8E0 | 8.6E0 | 1.3E0 | 9.9E-1 | 8.9E-1 | 6.4E1 | 5.5E0 | 54 | 9 | 53 | 9 | 0.58 |
| uP | ng/ml | 2.2E0 | 2.7E0 | 2.5E0 | 2.9E0 | 1.3E0 | 1.3E0 | 1.1E0 | 1.6E0 | 9.1E0 | 6.0E0 | 54 | 9 | 53 | 9 | 0.64 |
| uV | ng/ml | 2.3E-4 | 1.0E-9 | 1.6E-2 | 7.1E-3 | 4.0E-2 | 1.1E-2 | 1.0E-9 | 1.0E-9 | 2.0E-1 | 2.5E-2 | 54 | 9 | 53 | 9 | 0.45 |
| uT | ng/ml | 5.8E1 | 7.0E1 | 8.3E1 | 8.0E1 | 9.2E1 | 4.5E1 | 1.2E1 | 3.3E1 | 5.8E2 | 1.6E2 | 54 | 9 | 53 | 9 | 0.57 |
| uU | ng/ml | 1.7E0 | 1.4E0 | 2.0E0 | 2.3E0 | 1.2E0 | 1.9E0 | 5.2E-1 | 7.5E-1 | 5.6E0 | 6.0E0 | 54 | 9 | 53 | 9 | 0.46 |
| uW | ng/ml | 7.2E0 | 8.4E0 | 7.6E0 | 9.1E0 | 2.9E0 | 2.3E0 | 4.0E0 | 5.6E0 | 2.2E1 | 1.3E1 | 52 | 9 | 51 | 9 | 0.72 |
| vB | ng/ml | 2.6E0 | 3.3E0 | 2.7E0 | 3.8E0 | 1.2E0 | 1.6E0 | 6.9E-1 | 1.5E0 | 5.6E0 | 6.6E0 | 52 | 9 | 51 | 9 | 0.70 |
| vC | ng/ml | 1.0E-9 | 1.0E-9 | 3.0E-3 | 1.0E-9 | 2.0E-2 | 0.0E0 | 1.0E-9 | 1.0E-9 | 1.4E-1 | 1.0E-9 | 52 | 9 | 51 | 9 | 0.48 |
| uY | ng/ml | 7.4E-1 | 6.1E-1 | 1.2E0 | 1.1E0 | 1.1E0 | 1.0E0 | 8.7E-2 | 2.4E-1 | 4.9E0 | 3.0E0 | 52 | 9 | 51 | 9 | 0.46 |
| uZ | ng/ml | 5.8E-1 | 6.0E-1 | 8.2E-1 | 7.2E-1 | 1.1E0 | 5.6E-1 | 4.7E-2 | 2.7E-1 | 7.2E0 | 2.1E0 | 52 | 9 | 51 | 9 | 0.51 |
| uX | ng/ml | 1.1E1 | 1.5E1 | 1.3E1 | 1.5E1 | 7.2E0 | 5.5E0 | 4.0E0 | 7.5E0 | 3.3E1 | 2.3E1 | 52 | 9 | 51 | 9 | 0.64 |
| vA | ng/ml | 7.4E-2 | 7.2E-2 | 8.6E-2 | 7.6E-2 | 5.8E-2 | 3.3E-2 | 2.4E-2 | 3.0E-2 | 3.0E-1 | 1.4E-1 | 52 | 9 | 51 | 9 | 0.49 |
| vH | ng/ml | 1.2E-1 | 1.5E-1 | 1.6E-1 | 1.6E-1 | 1.4E-1 | 7.4E-2 | 1.5E-2 | 5.8E-2 | 8.0E-1 | 2.6E-1 | 54 | 9 | 53 | 9 | 0.60 |
| vI | ng/ml | 1.4E0 | 2.0E0 | 1.7E0 | 2.6E0 | 1.1E0 | 2.0E0 | 6.2E-3 | 1.2E-2 | 4.5E0 | 6.2E0 | 54 | 9 | 53 | 9 | 0.63 |
| vP | ng/ml | 4.3E2 | 4.4E2 | 5.1E2 | 5.4E2 | 3.9E2 | 5.1E2 | 7.0E1 | 6.7E1 | 2.0E3 | 1.7E3 | 54 | 9 | 53 | 9 | 0.48 |
| vT | ng/ml | 7.7E1 | 9.9E1 | 1.1E2 | 1.1E2 | 1.2E2 | 7.6E1 | 3.7E1 | 3.0E1 | 6.9E2 | 2.8E2 | 54 | 9 | 53 | 9 | 0.50 |
| vU | ng/ml | 1.0E-9 | 1.0E-9 | 2.3E1 | 3.3E1 | 3.5E1 | 4.3E1 | 1.0E-9 | 1.0E-9 | 1.3E2 | 1.2E2 | 54 | 9 | 53 | 9 | 0.56 |
| vQ | ng/ml | 3.5E2 | 3.5E2 | 3.6E2 | 3.9E2 | 1.5E2 | 1.9E2 | 6.7E1 | 2.1E2 | 8.1E2 | 8.4E2 | 54 | 9 | 53 | 9 | 0.50 |
| vO | ng/ml | 1.7E3 | 2.0E3 | 1.8E3 | 2.0E3 | 4.5E2 | 4.7E2 | 1.0E3 | 1.2E3 | 3.0E3 | 2.8E3 | 54 | 9 | 53 | 9 | 0.63 |
| vS | ng/ml | 1.3E3 | 1.5E3 | 1.3E3 | 1.4E3 | 3.6E2 | 5.9E2 | 1.0E-9 | 1.0E-9 | 1.8E3 | 2.1E3 | 54 | 9 | 53 | 9 | 0.64 |
| vV | ng/ml | 9.7E2 | 1.3E3 | 1.4E3 | 1.4E3 | 1.6E3 | 1.3E3 | 1.1E2 | 1.1E2 | 1.1E4 | 4.1E3 | 54 | 9 | 53 | 9 | 0.52 |
| vW | ng/ml | 1.4E2 | 1.0E2 | 1.8E2 | 1.2E2 | 1.4E2 | 5.6E1 | 4.3E1 | 7.7E1 | 6.7E2 | 2.5E2 | 54 | 9 | 53 | 9 | 0.40 |
| pF | pg/ml | 5.1E-1 | 3.2E-1 | 6.9E-1 | 8.4E-1 | 9.9E-1 | 1.6E0 | 1.0E-9 | 1.0E-9 | 9.4E0 | 7.8E0 | 105 | 25 | 97 | 25 | 0.43 |

Figure 21 Continued

Analyte panel data:

Unconstrained panels with 3 analytes, where 1.0E-9 >= 'model p-value' > 0. Contains 5 panels of 27,488,127 total panels evaluated. : Cw{BcqH bOqQ} ApNtjT JiaMnO QzdBqQ Unconstrained panels with 3 analytes, where 1.0E-8 >= 'model p-value' > 1.0E-9. Contains 165 panels of 27,488,127 total panels evaluated. : Cw{hO(aK aQ aU aV cl cJ cY dR gW hR Hu jE jM Kk Ko lK Nj Pe Pf Pg qO qP rW) Bc(qB vT zH tL xA) qG(Lx oK oN rY vU) rN(jF jY oN Pf xA) Hu(hL qC qH rU) Nq(fY qC qD) oK(fY Ic qO) oN(fY qO qP) aC(bE cZ) xA(cN cR) qQ(iJ iO) vP(aW rU) CuqX PoqA NoqH LxeZ StrT QzOu OfeD VvhR bOvT dCqD dJvS} iH{Ad(fN fY hL hO hP pY qA qB qC qD qG qH ql qZ rN rO rP rQ rR rS rT rU rV rW) Jt(qG rT rW) qQ(Nm Nn No) Ed(qT qX) qDtM} dJ{Et(rZ tO tR tS tU vP wD wG wJ wL wQ yD) nT(Kr Ks)} nT{nA(Kn Kq Tz Ur) Tr(Li Pf Uf) iP(Kc Kf Kk) Ba(Jy Vo)} Ap{Kk(rO rR rU) KiqG rBxA rUvP} Pz{qD(Na Qw Us) qC(Qw Qz)} nA{Jj(Ha Uv Vs) nO(Kq Tz)} nB{Kn(hC iP Ma) LvLd UbKc} Ad{Nt(eZ fY) Us(hO rU)} dB{Jt(tR tS) EtyD NowL} Qz{BoOu KihO} On{OuUs aMnO} NtJdeZ IqaCvB fPqDtM Unconstrained panels with 3 analytes, where 1.0E-7 >= 'model p-value' > 1.0E-8. Contains 746 panels of 27,488,127 total panels evaluated. : Cw{wJ(cR cS ED Ha hL hO iO jK jL jV Kr Lx Mp My Nd No Nq oK oN Pe Po pY qC QD Qe qV QY RA Ri rN St uY Vs Vv tF) St(tV uN uO uP uT uW uY vA vB vI vP vT vU vV vW wB wD wE wF wK wL wP wQ yD yJ yK yL zH xA) wQ(aW Cv dJ hL Ji Kr Ky Mp Nb No Nq Nw oK oN Oz Pb Qu qV Qy Rf Rh Rm Ue Uh Uk uY Vs Vv) uY(cN dR eD eT fY hV iH iJ iO iZ Jd jL jM jQ jR jT Kz lM Mn oF qA tT wK) No(hO tS vA vB vT wF wL wP yH tL) Vv(hA iC jM jO jT qT qX rZ wD) oN(rO rP rW tT uP uW uX vP wK) vB(Hu iO jL Kr Ld Nq Pb rN Vs) Nq(sM tN tO tR tT wK tL) oK(Ib qP sO tT tX uM vP) vA(Ez iH Ng oH rN Um Uo) iO(rT vT wD zA zI xA) uN(aW hL Kr Lx Po qD) Bc(qD qG rV uL wL) Ed(qG qT wB wK wP) hO(dA Nb tO vI vP) hL(tX vP vV yE) wK(Kr Lv Lx qQ) Hu(sM vT wF) dJ(aC jO qQ) wL(fY Mn Rh) tL(cW Mn oH) Mp(qG wB) Nj(rN sK) Js(qX uM) Us(Me qX) cR(qO rW) iJ(rU uL) qD(Ba Oe) qT(Cu Fw) xA(jK jL) vW(dA Lx) QduM QyqG KrwB LdrU RhrN OfqU aKqO iHqQ} iH{Ad(eT eZ pS qO qP qQ sC sK sM sO tN tO tQ tR tS tT tU tV tX uG uI uL uM uN uO uP uR uT uU uV uW uX uY uZ vA vB vC vH vI vO vP vQ vS vT vU vV vW wB wC wD wE wF wG wH wJ wK wL wP wQ yD yH yJ yK yL zA zG zH zI yE tM tL xA) Jt(qH qI qZ rN rO rP rQ rR rS rU rV sO tO tR tS tT tX uI uL uO uV uW uY uZ vA vB vP vQ vT vV wD wF wG wH wJ wL wQ yD yK zI xA) qX(bG dI Fw kS lN Ou qU rA) wQ(Aj Ap Hw Ip Kg Lh) Ap(uO uZ vQ wD) Hb(uO uY uZ vA) uL(No Nr Tz Um) uI(Jp Kc No Nr) Ed(tS uM yK) qQ(Al Nt Qz) Et(uY vA) Pf(rX rZ) wL(Hw Jm) uM(Bc Jd) vB(Dl Tz) FwqT NmuY NovV OnvA UnuU} Bc{Kz(pS rU sC sK sM sO tN tO tQ tR tS tT tU tV tX uG uI uL uM uN uO uP uR uT uU uV uW uX uY uZ vA vB vC vH vI vO vP vQ vS vT vU vV vW wB wC wD wE wF wG wH wJ wK wL wP wQ yD yH yJ yK yL zA zG zH zI yE tM tL xA) Hf(sK uT vB vS wF wH wL yD) Rb(uM wG yD yK zA) jY(tV uN vP wG) vW(Nt qD) KitV KrsO UswG cCuL} Us{On(ED Fw Gl Ic Iu jG Ly Me Nc Ne nY Pg Qz) Aj(uG uW wC wK tM xA) Ed(lM qT tN tO wQ) qX(Bb Dk Kq) Pz(hO qC) wQ(lM Uf) hR(Dk Jg) AdqD AprZ UcyD JtrP lMoN} nT{nA(Fa Ha Ib Kg Li Lx Pf Po Rg Ua Ut) nJ(Ba bF bW cD cE cG cL) mP(aM bL Co gL) Aa(cG dF dH) Ib(gL Kg) Id(Co Qy) KniP KqdJ VoPf cLmF gLmU} Ap{Kk(uN uY vB vQ vU vW zH xA) vW(gW Kr Og Oy St) Nt(hA wD wJ wK) wQ(dB dJ No) Ki(rP wJ) cC(qG qO) hA(Ks Nm) wD(iO Ue) xA(Ez St) QzOu} Qz{dB(tT wF wG wH wL wQ) Ou(Ba bF Et On Rc) On(Ex Gz In) qD(Hu Pz tM) ExFw} Kz{qQ(pS uG uL vV wE) qD(sM vH vW tM) EdzG FwvS NbvB JdtQ KcxA bPuP qCrX} Kr{Ad(tQ tU uL vU vW wF) Uf(tT vW wF wJ wK xA) JtvW VqrZ} In{On(Hc Ic Jd Kk Ou Ue Um) DcnJ NlOk NxUm NynA} dJ{BogW CvIc EdOn EttV GpLy HbwG KfwQ OkrZ UfwJ aCcF} qD{Hf(sC uW) Kk(uU vW) Pk(wC wG) AdNa MctM QwuP UmvW} Uf{wQ(cC Hf Qw Ue) MpwJ KkvI} Vq{iA(qU qX) rZ(dA Qv) FwqX qUrY} nO{Ba(aM As nF nI) IbKg NxaM} nB{Kn(cG Ib nF nR) Kk(iP Ub)} vW{St(Aj aO Mg) FwbW} Bb{UevB PaxA fPwJ} Db{NnwQ hOvI oKuX} Ed{On(aG cD) ExcD} Ad{eZ(Na Qw)} Bo{aC(bE cZ)} Et{aKqO iOwD} Um{UvzH iCvB} nJ{DcIv VsoO} AahBwD ArJjnA ExaKgW NtOkjT LvIbkG HuTtrU IscCwL QwOnOu KiiOwF Unconstrained panels with 3 analytes, where 1.0E-6 >= 'model p-value' > 1.0E-7. Contains 3,175 panels of 27,488,127 total panels evaluated. : Cw{qG(aW bG bI bM bQ cC cD cI cR cS CV dA dJ DK dL hC Hu IH iO Jd Kr Ld Nb Nj No nY Ow Pd Po QD Qe qV qW Rc Rg Rm rN Uh Vv) oN(eZ fN hO hP Ib pY qA qB qC qD qH qI qQ qZ rQ rR rS rT rU rV sC tN tX uG uM uR uV uY vI vU vV vW wD yD yH yL xA) wJ(aW Cu Cv Fw hC Hu Ih Jd Jh Js Jv Kj Kn Kx Ld Lj Ma Mf Mj Nb Nc Nf Nn Nr Oh Pg qT qW rU Uk Up Us Uv Vq tL Tj) Kr(eZ qD rN rQ rS rT rU rV sC tN tT uG uL uO uP uR uV uW vA vH vI vP vT vV vW wC wD wE wF wP yH zH tM tL xA) Vv(eD fY iB jD jE jF jG jH jI jK jL jP jQ jR jV jY lK lL lM lN lO Me qO qP qU Qz rT rW rY tO vP yD xA) rN(aK aU aV Bc bQ cE cG cJ cY Dd dF dL Ed Gl Hu iA jE Kk Ko Mp Mt Nb No Nq nY Oe oF oK Pe pF Pg qU Qz) uY(aJ aK bO cD cR Cv dA dJ eC Fa gP gW Hu Ic Jf Kk Ld Nh Nj No oE oH oK Qw qY rR Tz Ue uN wB wF) wQ(aZ Bc bG bL dB Ed Hu Id iH Ke Ko Ld Lx Mn Mt Ne Nt nY Ow Po Qm qQ qU qW Qx Rb Rg tQ Ur Vq) Of(hA hR hX iB iC jD jE jF jG jH jI jL jM jO jP jT jV jY lK lL lM lN qT qV qW qX rX rY rZ) Mp(eZ fY hO qA qD qO qP Qz rO rP rQ rR rS rT rU rV rW uN uO uW vI vP vV vW xA) qD(aI aN bA bQ cG cT dF EZ Hu iJ Ik iO Kk Ld oF Og Oy Pf Qu Qw Qz Rh Uo) tL(aK Cv dA dC dJ Hu Kk Nt Oe Oz QU Rf Rh rT St UM Uo Ur Vq vW xA) Ib(dR eD gL hA iA Ic iJ jM jP Ly Me oF qU qX Qz RB rC rX rY rZ tF) oK(eZ hP Ou qA qQ rO rP rQ rR rS rT rU rV rW sC uN uX vV vW wD yD xA) iO(hL hO qI qO qP qZ rP rU rV rW sO uM uO uV vA vI vP vQ vV wF wG) Nq(eT eZ fN hL hO hP jM jP jT pY qA qB qX rP rR rU rW tS vT wD) dJ(eD gW hA hL hO hR hX jP Ly qH qT qX rZ vB vT wH wL xA) hO(Bc bQ cW Gl gP iH iJ jF jT Ld Lx oF oH qX Uh Vt) St(sC sO tN tO tR tS tT tU tX uM uR uU uV vQ yE) rT(Cu Ed Ha Jd Js Lx Ma Nf Oh Pg Po Qd Qe Us Uv) hL(aM cW gP iH Ld Mn Nj No oF Qz tT uM Vq yD) xA(bO Cv Ed hC Hu iH Jd Jh Nd No Ri rU) Qz(Cu Ex Fw Gz Hu In Mc Ng Pg Uh Us) rU(aK Gl gP Kk Nj No nY oF Pf Vq) qX(Ed Fw iH In jM Ma Nm Nt Qu) Js(hA hR iC jM jT qT qU rZ) Rh(qA qB qC qH vA vB vT wF) Vq(hA qH sM vA vB vT wD wL) Ed(eZ rP rR rS rV uN vW) eD(Cu Ks Ng Nt Ou Us Uu) qC(Bc dC iJ Ld Oe Pb Qu) Fw(aC iC jM jT Ly rZ) vA(gP Hu Je Jf Kk rB) In(hA Ly Ne Nl Ou) Ld(qH qQ sM wF wG) wL(aK Hu oH Um Uo) vH(No oF Tz Um Uo) Nb(qH vB wD wG) qT(iA QU Us) qQ(aK Bc dA Jd) vT(aL bW Pb uG) Lx(uW wF wP) Ly(cD Nm Us) aC(aL cF cN) cR(qP tS vP) cU(fY qO qP) hA(cW Pf Tk) jM(Ic Ks rY) Bc(qZ vW) Po(fY rP) No(uU wK) Nt(jP jT) Ng(jP qU) Nj(rO rP) Qd(eZ vP) Qy(tT uN) Ou(Ic Qw) Pe(uG wK) qB(aK Kk) uM(cS Ma) CujT MeKs UeqU IjrZ KnnB OevO PbsM PfrR PguP aWvV dAzH nTmP iHvB} Vq{rU(Aa Ad Af aK AL AO Ap aQ aR aU aV bV bX cI cR Cs cU Cx cY Dc De Dg dJ Dl dR eD Et Fr Fw fY gL gP gW Hf hV Hw iC iH Iq Is jF jG JQ JR Jt Jv jY Kq Kz lK Mf Mm Mw My Ne Nm No Nq Nr Ns oE oH On Pj Pz qD qO qP qX Qz rB Rm rS rW sO St Tz Ue Uf uI Ul vB vH vP Vs vV yD yK xA tF) vB(Af aK aO AP aU Aw Ba Bb bC Bg bI bL cB cC Co Cp cX Db De dJ Dk Dl Ef Et Fa Gl Gp Ha Hb Hf Ij Ir It Jd Jf Jg Jh Jq Jt Kf Kl Ko Kr Kz Li Mb Me Mw Nj Nn Nv Ok Om Po Qg Ql Qm Qn Qz RB Rc rY rZ Tz Uc Ue Uh Un Uu uV uX vI Vv yH yK) xA(aK Al AN Ap aU Aw Ax Bb bQ bX cD cY De DK Dl Fp hG Hr iH IJ iP Jd Jg Jh Jq Jt Kl KQ Kz Li Mf Mj Mv Nj oN Pa Pc Pd Qt Qy rC rR rW sK sM Ue Uv vA wD wJ wQ yK tL) rZ(aF Ao aV aW BA Bg bM bP bW Ch cM cN cP cS De dJ dL Ed Et Fw Hb iA Jd Je Jf Js Ki Kz Mk Mp Mv Nj Nn Oe Of Oh Oi Om On Oy Pc Qd Qe qV Sr Tz uY vT wF wL wQ) vA(aC Ad aK Ap aQ aV Aw bX Cp cY De Et Is Iu Jh Jq Jt Ke Kf Kj Ko Kz Li No Ok On Pf Pj qO Qz rW Tz Uf yK) wQ(Ad Ap

Figure 21 Continued

Aw Ba bF bZ Cp cT Dg dJ dL Ef Et Hf Ib Jg Jq Jv Ke Kf Kl Kz Li Ma Mg Ms Oy Qz rY sO Uf Us yK) Kz(qQ tV uG uI uL uM uN uO uP uV
uW uX uY uZ vH vI vT vU wF wG wK wL yH yK yL zH tM tL) rY(Ar bS cL dF dJ Fn iA iC iO Oi Pc Qv qX Tz Ul Us uW vW) vT(aC aK aU
Aw bE Cp cY Dk dR Jt Li Mw Qz uO vU VV) vW(Ap aV Cp Dk Et hC Jg Jh Jt Kl Om Qu Ss) nO(Af bJ cK Cv dJ gL iP Kp Qn Uo tF) wD(Ba
cT Et Jg Jv Li qW Qz sO Us Vs) Jt(hO qB qC qD rS uI uR wJ wK) On(eT eZ fY hL hO pY qB qD wJ) yK(cG cM cO Et iA oN qU uM) Aw(pS
uM uX uY wF wH wL) hO(Dk Ef Ib Ma Of Pz Uf) Et(rO rP uT wJ wK yH) nT(dJ iP Iv Ny pF tF) qD(dE Pj qG qI qU Qz) hL(Cp Dk Ef Ib Mg)
jY(qG rO rR rS rW) iA(qT rB rW rX) qX(bM dH Ed qU) Tz(rO vl yH) Qz(uP uV vI) Us(uO wG wH) tF(lc nB qU) wL(De dJ vU) uM(Af Ba
Cp) Jd(vU zH) Jq(uG uX) hA(Of Oy) iH(vI vQ) wH(De dJ) rX(iO Pc) AdyH AorO NutL NjnB IsuI JvzG PjwJ bJkI cMsO gLnN nIiP hPqU}
Us{On(aH Aj Al Ao Bg bQ bX cD Cp Cu Cv Dc Dd Fb Fn Fy Gp hA HC Hf hR Hu iA IB iC Ih Ii Ik In Io Ip Iq Ir Is It Iv Iz Jd JI jK jL JM jO jP
Js jT Jv Jy Kd Ke Kf Ki Kk Kn Ko Ks Kx Ky Kz Ld Li lL lN lO Ma Mb Mc Mh Ml Mn Mp Mq Mv Mw Mz Nb Nf Ng Nh Ni Nj Nk Nl Nm No
Nq Nr Ns Nt Nw Ny Oe Of Oh Oi oK Om oN Ow Oz Pb Pc Pd Pe Pf Ph Pi Pj Pk Po Qg Qh Ql Qm Qn QT QU QW qX Ra Rb Rf Rh Rj rX rZ
Ss Ue Uh Uk Um Un Uo Ur Uv Vo Vp Vs Vv Tj tF) Dk(eC eD hA hO iB jM jP jT jY lN oK qG qQ qT qU rA rX rY rZ wQ xA tF) Ap(eD fY
hA hR iC jG jO jP jT qG qO qT qU qX rO rW rX rY vP wD xA) Ad(eT eZ fN fY hL hP hR lL lO Ly pY qA qB qC qT qX rO rP yH) qX(Aw Ba
Co Cp De Et Fa Jg Jh Jt Ng Of Ok Om Oy Pe Tv Vs) Jg(eD iP jG jI jM Ly nY qT qU Qz rX rZ tF) Kq(eD hR jM Ly Me qT qU Qz rX rZ tF)
Vs(hR jP jT qT qU qW Qz rA rX rY rZ) Ba(eD hA hR iA nY oN qU rX rZ tF) Aj(hO sC uL uU uX vS wG yJ) Nx(Ic In Iq Is Iu Ly Ou Qz)
qT(Bb Co Cp Jh Kg Ng Oy Tv) Uc(sC uG uW vS wC wG tM) rX(Co Fa Lh Nw Ok Om Oy) Ly(cD Dc Et Iu Jt Lh) rU(Dd iH Iq tN vP tL)
Bc(sO tO vI wP wQ) qD(Dc Ed Jt Kj wD) rZ(Fr Jd lM Ok Oy) Et(rP rV wQ yD) nA(Lx Nb Ny Ur) Dc(hO jL lO) Fa(eD qU rY) Jd(hO hR wC)
Qz(Bb Bo Ou) wQ(Ib Oy Vo) lM(bZ cO dF) De(uW wH) lO(Li Qh) AfzA CvIc EdwK FrhR IbtO JthO UfwJ OyjP} iH{qX(aA aC aD aE aF aG
aH aI aJ aK aL aM aN aO aP aQ aR aS aU aV aW aX aY aZ bA bB bC bE bF bH bI bJ bL bM bN bO bP bQ bR bS bU bV bW bX bZ cA cB cC
cD cE cF cG cH cI cJ cK cL cM cN cO cP cQ cR cS cT cU cV cW cX cY cZ dA dB dC dD dE dF dG dH dJ dK dL dM dN dR eC eD eF fP gL
gP gW hA hB hC hF hG iA iC iJ iO iP Iv iZ jE jF jG jH jI jM jP jR Js jV Kk kQ kR lK lL lM lO Mc Mf Nq Nu nW nY oE oF oH oK oN Ow PF
qT qV qW qY Ra rB Rg rX rZ Tz tF) Jt(pS sC sK sM tU tV uG uM uN uP uR uT uU uX vC vH vI vO vS vU vW wB wC wK wP yH yJ yL zG
zH yE tM tL) qU(Ad Ap bG bH bW cD cE cN cW dD Ed Fa Fr Fw iB iC Iq jL Li Lj lN Mf Om On Ou Pf qT Rg Tz) rX(bW cD cE cN Cv dD dJ
Ed iC jH jM Jy kR Li Mf Nr Nu Nw nY Ok Om Ou Pc qT qY Rg) Et(qG rV rW uL uO uZ vB wG wQ xA) qQ(Ex Gz Iq Jd Nq Nr Ns Nu Qu Ul)
Ed(On qV qW qY rA rP rQ rZ vH) Ou(qT qV qW qY rA rB rC rY rZ) rV(Ap Hb Jp Ok Om On Tz Un) rZ(bC bW cE jH lM nY Rg) vB(aC Ar
Hb Hw No Nr On) uY(Aj Hw Mg Om On Tz) qT(bG eD iA lN tF) uL(Hb Mg Om On Un) Ap(qG rT zI xA) wQ(Mg Nn Qz Uf) vA(Hw Jm Nm
Tz) Bc(rP uN uT) No(sM vP zH) On(uM uO uZ) bG(qW qY rA) nF(Af Ba Bo) lM(bZ dF hA) rU(Jp vP yK) Fw(qW rA) Ib(oP oQ) Qz(hL qD)
Om(uM uO) rC(cD jM) tL(Aj Hw) NtuI LxuT MgwG TzwL JjyK JoxA UnzH UuuZ PfrY nTmP qDyE qWlN} nT{nA(Ba cG cL Dp Ef Gl Hc
Hf Hq Iz Jd Je Jf Jy Kc Kd Ke Kf Kj Kr Ks Mn Mr Nr Nv Nw Ny Og Om Or Pd Pe Pg Qh Qt Qu Qx Qy Rf Rj Rm Sr Ss Tt Tv Uc Uf Up Uv Vs
Vu) mP(Ad Al aN Ao aP aQ AR As Aw BA Bb bF Bg Bn Bo bQ bU bV cE cG Ch cK cL Cp Cq cT dF dG Dk hG iP oE oF oK oN) nJ(aM bC
bM Bo bZ cH cM cN cO dF dG dH Di dL Ex Gz hB hC iO iP nF oF oN pF Qh Vs tF) cG(aM aS cE cV cY cZ gL iP iZ mF nD nF nI nK Nm Tr
Vo) Aa(AP Ba bZ cL dG gL hG Iz Kc Kk Kn Kp Ky Uf) Ex(aE dJ Ed Hc Ju Jv Nc Nl nU Oy Qw Qy Qz) cL(aM gL iZ kC nD nF nI nK Vo)
gL(Ba bW cE cH Ij nB Pf Ug) aM(Ba cE hB Mn mU nU oN) iP(Fn Fy Iz Kd Ko Kp Uf) Lx(aS Jv Jy nF nK pF) dJ(Ba cH cM Gz oQ Rj) dG(mF
nF nI nK Nm) Gz(Ed Hc kG Nc) nF(Ba Dg Li nU) Mu(cY cZ Tr) Id(Oy Pf Rg) Ij(Kg Kn St) nK(dH Li Mn) Ba(cZ mF) Ib(Iz Lh) Qy(Kd Lv)
Pf(Jv pF) mU(cI iZ) MpTr LiaS} Qz{Ou(Ad Ao Ar Bb cC cE Ch Co Db Dc Di Fr Fw Hf Hq Hu Ic In Iq Jd Je Jg Jh Jq Kf Ki Kl Kq Lx Ml Mu
Mv Of Ok Om Oy Pg Qg Qt Qw Qy Ss Uf) Ex(Ad AN Bb bF bM Bo bP cC cD Cv dD Dg dL Ed Et In Jd Jg Jq Mb Ml Mq Na nN nO Oh Oz Pa
Pc Qg Rc Ss Wm Tj) dB(tN tO tQ tR tS tU tV tX wB wC wD wE wJ wK wP yD) Gz(Ad bF Bo Ed Jd Jg Jq Mb Mq Na Oz Pc Rc Ss) In(Al Bo
Dc Dk Lh Mq Mr Nv Nx Ny Qb) On(As Ed Fw Nt Pg Ql Uc) Bo(Fw Hu Mc Pg Ue) qD(Hc Mw Pj Qw) Fw(Ap bF Lh) ArNr BbxA IcbF VsnF}
On{In(aC aG aH Al aN Ao aZ Bg bO bQ bX bZ cD cF cG cK cO CV Dc Dd dF dJ dL dM Ed Ez Fw Gl Ha iA Ib Iz Jy Ke Ki Kn Kx Ky Oa Qt
Qu Qw Ra Rm Tv Ub Uc Uk Ur) Ed(aC aH aN aU aV aW aZ bO bP bQ bX cA cC cE cG cH cL cO cV dA dF dG dL dM dN Ic Jn Nj Ou Qw
Ue Um) Uc(cD Ic It Ly Me Nc Ne Nj Ou Pg Ue) Fw(dJ Ic Ly Mp Nj Ou Um) Ic(dJ Nt Ou Pg Ql) Ly(cC cD dJ Ex) nO(Ex Gz Qu) NqQl NtOu
UeJl QwcD} dJ{Et(fN hR qG qZ rB rO rQ rU rV rW rX rY tQ tT tX uN vV wB wC wE wF wH wK wP zA xA) aC(Ad Aj Ap Ba Bo bU bX cB
Ch Co Dg Dl Ed Fw Gp) cF(aK aQ bF bU bX cK cU dD Fw) Ic(bX Ed Kq Ly Me Ml Of) Fw(bX cB gW Kq Ly) Ly(Bo bX cD Jg) Ed(Ex Kq
Ml) nO(Ex Gz Kq) hR(Ad Ap Jg) AprZ DgwQ ExcB GpgW JtwG KztX OkhA} nO{Ex(Ao Cv Di Kc Kk Lh Lv Me Nc Nd Nh Nl nN Nx Pk
Qw Rb) Ba(aA aS Bb bQ cE cV iP kC Ma mF nA nJ nK pF) Gz(Cv Ed gL Ld Lh Ly Me Nj Nl Nx Rb) nA(bF cE Fa Gl Lx Qt Up Ut Uv Vs)
aM(bF cE Lx Mx Nv oN) nJ(bF cE cG cL) iP(Kc Kf Kk Kn) As(bF cE oN) Lx(aS cV) Kn(Aa Ij) NlcM KsNx LiaS} Ad{Kr(sC sO uG uR uW
vA vI vO vP vQ vS vV wC wG yH yL zG zH) Gz(qG qH qI qQ qZ rN rO rP rQ rR rS rT rU rV rW) Ex(qG rN rO rP rQ rR rS rT rU rV rW)
Na(fN hL hO pY qB qC) Hf(eZ hO) aC(bE cZ) QwrU cCqG} Ap{Kk(qG qH qI qZ rN rP rQ rS rT rV rW sC tQ uZ vI vS wF yL zG tM tL)
Nt(jO jP qG qO rN vP xA) wQ(Mp Qw Ue) xA(hG Mn qW) Nm(jP Ly) No(qH vW) Ki(rN wK) aC(bE cZ) aK(qD vW) qG(Ex Qu) FwUm
HurU IciJ IktL OwrV PfrO cCqP} Ly{cD(Ar Ba bF Bo bX cC cE Db Et Ex Fw Gp In Mr Of Og Ok) Fw(aN bF bX cC cE cL cW Et Ex Nj) Et(Ii
In Ng Nm Og Oi) In(bF Ne Nh Nl Ok) Og(Ne Nh Nl Ok) Ok(Ii Ml Ng) cC(bX Gp) ExnN} Ex{Ed(aC aG aN aV bG bO bU bX cB cC cF dA dD
dL Mb nN) nN(aJ iO Me Nl nY pF) nJ(cR kI nB pF tF) aC(Aj Ef) BcrU DcrN EtqG FwcB MbnR RbcD LdkI dRgW nUpF} In{Nx(Ed Ha Qw
Ss St) Ok(Nc Ne Nh Nj) nA(Lx Nr Pe Po) Et(Ne Nh Nl) Mr(Ne Nh Nl) Ic(Cv Jm Nv) Is(aC Bo bX) Um(Kq Nv Ny) Jm(Kq Qg) LxnK TvOh
IutF} Kz{qQ(Bb Kc rQ sK tQ vO vP vQ wC wD wH yJ zG zI tM) Ed(pS qT uG vO wH) Nb(tX uI zH xA) Kc(vB wQ) xA(bC bM) CvpS
bPuG} Bc{Hf(sM tS tU tV uR vH vT wD wG wQ yJ) cC(qI sK zH tL) Gz(rQ rU) uN(Me Ue) DbzH NtwL RbtV PjqD aZyK jYzA} Uf{Kr(hA
rQ rT uI uO uT uW vS vT wD wL wQ yJ zG zI) cC(Ed wJ) dB(wJ wQ) rUvP} nB{Kn(Cu Dg Nm Ra To Ub Vo) Ub(Lh Nj tF) Aa(Kx Ut)
Lv(Ql Rg) Kk(Dl Vt) GznJ NjKi IdnA TvnR} Jt{dB(tN tO tT tU tX wC wJ wL zA) cC(qG qO qP rP uP uX) NaqD UetL HurU KrrV}
aC{bE(Ao Aw Ba Bb bF cB cF Ch Co Cp Dg) cZ(Ba Bb cB Ch Co) cF(Ba Bo) AlFw} nJ{Iv(Al Kf Kq Qh Tz Ut) kO(aG iP tF) Dc(Il Js) EdLu
GzkI QxtF VsiP jEqT} nA{Jj(Bo Cp Cq Dc Tt Ua Ur) Lx(Dd Ij Js nF) Ny(Ij Js) NrIl} qD{Qw(Dc Dd Iq Jm Kj Pk) Na(Dc Pj wC) Pj(Ik Nt)
yE(hG Um)} Ed{qT(Bo Db Hf Iq) Gz(mM nU) cW(hA jG) IccE KiqX bWvW} Et{Ic(Nm Ou) GzrO NtjT MnfY KkrU cCqO dBwQ}
Fw{Oh(Tn Tv) Pa(qT xA) GzMe KqUm cWjG} Qw{AjwQ BbxA MewC JmvA KihO UuqQ} Ml{Ok(Nd Ne Nh Nj Nl)} Gz{kI(Kk Ld) RbcD
aJnN} vW{DgKr NoJd MebW NgSt} Aa{Um(vB wG) KkkI} Cv{Hf(vB xA) IcbX} nF{PoLx MtlY tFoN} kG{Oi(jD jP) IbtF} Bb{NoqQ
KrvB} Nj{nR(cE oN)} Tt{hA(Tk Wn)} gW{BoaK PjrU} AoKrwF PoLxnK IcOucE IqStuW ItdBwL JdKitQ KfKkrU UggLnN mMjEqT

Unconstrained panels with 3 analytes, where 1.0E-5 >= 'model p-value' > 1.0E-6. Contains 19,302 panels of 27,488,127 total panels evaluated. :
Cw{hO(aA aC AD aE AF aG aH aI AJ AL aM AN AO AP AR AS AW AX aY aZ BA BB bC bE bF BG bH bI bJ bL bM BN BO bP bR bS bU
bV bW bX bZ cA cB cC cD cE cF cG CH cK cL cM cN CO CP CQ cR CS CT CU CV CX cZ DB DC DD DE dF DG dH DI DK DL dM dN Dp

Figure 21 Continued eC ED EF ET EZ Fa Fb FN FP Fr Fw FY gL Gp HA HB HC HF hG hL hP Hq Hr HV HW HX iA IB IC Id Ih Ii Ij Ik Il Im In Io IP Iq Is It Iu IZ
JD Je Jf JG JH Jl Jj JK JL Jm Jn JO JP JQ JR Js Jt JU JV JY Kc Kd Ke Kf Kg Ki Kj Kl Kn Kp KQ KR KS Kx Ky Kz Lh Li Lj IL IM IN IO Lu
Lv Lw Ly Lz Ma Mb Mc Md Me Mf Mg Mh Mi Mj Mk Ml Mm Mn Mq Mr Ms Mt Mu Mv Mw Mx My Mz Na Nc Nd Ne Nf Ng Nh Ni Nk Nl
Nm Nn Nr Ns Nt Nu Nv NW Nx NY Oa OE Of Og Oh Oi OK Om On Or Ou Ow Oy Oz Pa Pb Pc Pd pF Ph Pi Pj Pk Po pY Pz QA QB QC QD
Qe QG Qh QI Qm Qn qQ Qt Qu Qv Qw Qx Qy Qz Ra Rb Rc Rf Rg Rh Ri Rj Rm rN rS rT Sr Ss Tz Ua Ub Uc Ud Ue Uf Ug Uk Ul Um Un Uo
Up Ur Us Ut Uu Uv uY Vo Vp Vq Vs Vu VV xA Wm Tj tF) qG(aA aC AD aE AF aG aH al AJ aK AL aM AN AO AP aQ AR AS aU aV Aw
AX aY aZ BA BB bC bE bF Bg bH bJ bL BN BO bP bR bS bU bV bW bX bZ cA cB cE cF cG CH cJ cK cL cM cN CO CP CQ Cs CT CU cW
CX cY cZ DB DC DD DE dF DG dH DI Dl dM dN Dp dR eC eD EF EL Ez Fa Fb Fn FP Fr Fw Fy GL GP gW Ha HB Hc HF hG Hq Hr Hv Hw
Hx iA Ib Ic Id Ii IJ Ik Il Im In Io IP Iq Iu IZ JE Jf Jg Jh JI Jj JK JL JM Jn Jo Jp Jq Jr Js Jt JU Jv JY Kc Kd Ke Kf Kg Ki Kj Kk Kl Kn Ko Kp KQ
kR KS Kx Ky Kz Lh Li Lj Lu Lv Lw Ly Lz Ma Mb Mc Md Me Mf Mg Mh Mi Mj Mk Ml Mm Mn Mq Mr Ms Mt Mu Mv Mw Mx My Mz Na Nc Nd Ne Nf Ng Nh Ni Nk Nl Nm Nn Nq Nr Ns Nt Nu Nv NW Nx Ny Oa OE OF Og OH Oi Ok Om On Or Ou Oy Oz Pa Pb Pc Pe PF Pg Ph Pi
Pj Pk pY Pz Qa QB QC Qg QH qI Ql Qm Qn qO qP qQ QT QU Qv Qw QX qY QZ RA RB rC Rf Rh Ri Rj rO rP rQ rR rS rT rU rV rW rX Sr
Ss St tN Tz Ua Ub Uc Ud Ue Uf UG Uk Ul UM Un Uo Up Ur Us Ut Uu Uv uY vA vB vH Vo Vp Vs VT Vu wJ wL wQ zG tM tL xA Wm Tj
tF) wJ(Aa aZ BC BG bl bM bO bP bW cA cC cE cK cL cN CO cP dB dJ Dk Dl Dp dR eC EF Et Ez Fa Fb Fn FP Fr Fy GL Gp hB hC hF hG HR Hv hW Hx iA
iB iC Id Ih Ii Im In iP Iq Ir It Iu jD JE jF JG Jh jK Jl Jm Jn Jo jP Jq Js Jt JU JV jY Kc Kd Kg Ki Ko Kp KQ KR KS Ky IK IL IN Lx Ma Mg Mh
Mj Mk Mm Mp Mr Mt Mv Mx Mz Nb Nc Nf Ng Ni Nn Nq Nr Ns Nt Nu nW nY Oe Of Og Oh Oy Oz Pb Pe PF Pg Ph pY qB qC QD Qe Qg qH
qI Qn qP qQ qT QU qW QX Qy Qz rA rB RC Rf Rg Rh Ri Rj rN rP rU rV rW rZ sC sM tN tO tS tX Ub uG Uh uL UM Un UO Us UT UU UV
uX uZ vA vB vl VP vT Vu VV vW wD wP yH yK tM tL xA Tj tF) wQ(Ad aF aG aK aL AN aP Ar aS bC bE bF Bg bO bQ bS bW bX cA cC cE
cJ cK cL cN Co cP cR cS Cu cZ DE Dg Dk Dl dR eC EF EZ Fa FP Fr Fw Fy GL GP gW Ha hB HC hF hG Hq Hx iA iC Ih IJ Ik Il Im In IO IP
Iu IZ JZ Je Jg Jj JL JM Jn Jp Jr Js Jt Ju Jv Jy Kc Ki Kk Kl Kn KQ kR KS Kx Li Lj Lv Ly Ma Mg Mh Mk Mr Ms Mu Mw My Mz Na Nc Nd Nf
Ni Nj Nk Nl Nm Nr Nv nW OE oF Og OH Ok Ou Oy Pa Pc Pd Pe PF Pg Pi Pj Pz Qc Qd Qe QH qI Ql Qn QT Qw qX qY QZ RA rB RC Ri rN
rU rV rX Tz Ua Ub Uc Uf Ug Ul UM Un Uo UP Us Ut Uu UV vH Vo Vp vQ VT vU vW wC yL zG zH tL xA tF) rN(AD aE aF al AJ An aO
aQ AR aW aY aZ bA bF bG bN bO bR bV bZ cB cC cF cI cL cO cP CQ cR CS cT CU Cv cX dA dB DC dG dH Dl dJ dM dR eC eD eF FP Fr
Fw gL GP gW hA hB hC Hf Hq hR iB Id IH iJ Ik Im iO Ip iZ Jd Je Ji Jl jM Jn JO Js Jt Ju Ki kQ kR kS Ky Kz Ld Lx Ma Mh Mj Mk Mm Mn
Mq Mr Mw Nc Ne Ni Nk Nl Nn Nr Nt Nu Nv Nw Nx oE Og Oh Ou Ow Oy Oz Pb Pd Po Qd qH QI Qm qQ Qu qV Qw QX Qy RB RC RF Rg
Rm rS rT rU rV rW rX tO tS Tz Ub ul Uk uL UM uN UO Up Us Uv uW vP VT VV vW wB wD tF) Qz(aC Aj Al AN Ao Ap Ar As AW Ba Bg
Bo cD Ch Co Cp Cq Ct Cv Dc Dd Dg dJ Dl Dp Ed Ef Ez Fb Fn Fp Fy Gl Gp Hb Hc Hq Hw Hx Ic Ih Ii Ij Ik Il Ir Iz Ji Jj Jk Jl Jo Jp Jq Js Jy Ke
Kf Kg Ki Kj Kk Kl Ko Kr Ks Lh Lu Lv Lw Lx Ly Lz Ma Mb Me Mg Mh Mi Mj Ml Mw My Nb Nc Ne Nf Nh Ni Nj Nk Nl Nm Nn Nq Nr Ns
Nt Nu Of Og Oh Oi OK Om On Ow Oy Oz Pb Pc Pd Pe Pf Ph Pi Po pY QB qC Qd Qg QH Ql qQ Qu Qv Qw Qx Ra Rb Rc RfRg Rh Rj Rm
rP rT rU Ss Ua Ub Uc Ud Ue Uf Ug Uk Un Up Ut Uu Uv vA Vo Vp Vs VT tL xA Wm Tj) qD(Ad aG aJ aK AL aM aO Ar aU aV bE bF BG bl
bO bR bV bX bZ cE cI cJ cO cP cR CS Cv cW cZ Dc Dd dG dH dJ ED eF Fp Fw GI GP hA Hc Hq HR hW Hx iA iH JE JF jG jL jM jO Jp Js jT
jY Kl Ko kR Ky IM Ly Ma Mj Mn Mq Mt Mw Na Nb Nf Nj Nl No Nr Nt Nv Nx nY Of Oi oK Ow Oz Pb Pd Pe pF Pg Pk Po qA Qc qI qQ Qt
qU Qx Rb Rf Rg rP rT sC Ss Ub Uk UM uP Us Uv vI vP Vq VV vW yE tM xA) tL(aD aF aG al AL aM Ar aU aV aW bA bC Bg bl bL bQ bU
bW cC cD cF cG cl cJ cM cP CQ cT cY cZ dB Dc Dd dF Dg dR eC Ed Fp GI GP gW hC hG iH iJ Ik iO Je Jf Jg Ji Ju Kl Ko Ky Kz Ld Lx Mp
Mt Mu Nb Ne Nj Nu Nw nY oF Og oK oN Ou Ow Oy Pb Pd Pe Pf Pg qV QW QX Qy RB Rg Rm rO rP rR rS rU rV rX sO Tz Ue uG Uh Uk
uN uO uP Us uW vA vB vP Vs vT VV wB wD yD yH tM Tj) xA(AI aP aW aZ bC bG bl bM bW cA cC cL cM cO cP cS Cu dA dB dR eC cF
Ez fP Fw GL gP gW Ha hG hL Ih iJ Io iP Je Jf jM Jq Js Jv Kc Kd Kj Kk Kn Ko kQ kR kS Kx Ky Ld Lj Lx Ly Ma Mf Mg Mj Mn Mx My Nb
Nc Nf Ng Nj Nn Nq Nr nW nY OE oF OH Ow Pa Pb Pe Pg Po pS pY Qd Qe qI Qm qT QU qV QW Qx Qy RA rB rC Rf Rg Rh rV tQ Ue uG
Uh Uk Uo Up Us Uv Vs tM Tj tF) hL(AD al aK aN aS aU aV bA Bc bG bl bO bQ cF cG cl cJ cP cR cT Cv cY dA dB DC Dd dF dH Ed EZ
Fn Gl gW HR li iJ iP Jd JE Jf jG jL jM Jn JrjT Ju jY Kk Kn Ko kQ Kr Ky Lx Mk Mp Na Nb Nt nY Oe Og oK oN Oy Oz Pb Pe Pf Pg Ph Pk Po
Qh QI QU Qw Qx Qy Rb RfRh rQ rT sC tO tS uG Uh Uk Um UO uP uR Us uT uX vI Vv vW wB wD wF tM) qQ(Ad aG al An aU aV aW Bb
bl bU cC cF cG cl cJ cM cN cP cR cS Cu cW dB dC dF Dk dR eC Ed eF Ez Fw GI gP gW hG Hu Ih In iP iZ Je Jf jG jL jM Jo Js jT Jv Kk Kn
Ko kQ KR Ks Ky Lx Ma Mg Mn Mp Nf Nj No Nq Nr nW nY OE oF Og Oh Oy Pe Pf Pg Po Qd Qu Qw Qy rB RC Rf Rh rP Ue Us Uv Vp
Vv) rU(al Al aU aV aW Bc bO bQ cG cI cJ cP cR cS Cu Cv cY dA Dd dJ dR Ed eF Fn fP Fw gL gW hB hG iA iH li iP Jd Je jG jM Jn Js Ko kQ
Ky Lx Ma Mh Mj Mn Nb Nf Nn Nr Ny OE Og Oh Ow Oy Oz Pe pF Pg Po Qm qO qP QU Qw RB RC Rg Rh rW St tT Uh Uk Uo Us Ut Uv vA
vB vl vT VV wP) jM(aA AO As aV cA cC cD cE cH cS Ct CU cW dA dJ dN ED EZ Fb Fr hA hR hV hW hX iA iC Id iH Ij Ik In Io Jj jL JO jP
Ke Ki Kk Kr IL Ma Ml Mm Mp Nf Ng Nj Nm Nn Nt Oh oK oN Ou Pe Pg qB QH ql QI qT QU Qw RB rC Rh Rj rT rX rZ Ue Ug Us Uu Uv vB
wG wH tF) dJ(cF Ed fN Fw hV hW IB IC jE jG jK jL jQ jR jT jY IK IL IM IN IO oK qB qC ql qO qP qU qV QW qZ rA RB rC rF rV rX rY sC
sK sM tN tO tR tS tT tU tV tX ul uL uW uX vA vl vO vP vQ VV vW wB wC wD wE wF wG wK wP yD yJ yK zH zl yE) rT(aW Bc cR cS dR
Fw GL gP gW hG Hu IH iJ In Je Jf Ji jL JV Kj Kk Kn Ko Kx Ky Kz Ld Mg Mj Mn Mt Nb Ni Nj Nn No Nq Nr Nt nW nY OE oF Og oH Oy Pa
Pb Pe Pf Pk pY Qb qC Qm QU qV Qw Qy rB RC Rh rV Ub Ue Uh Uk Up Vs Tj tF) oK(Ed eT Ez fN Fw GI hA hR Hu In Kk Ks Lu Nf Pf Pg
pS pY qB qC qH ql Qu qZ sK sM tN tO tQ tS tU tV uG ul uL uO QU qV Qx Qy rB Rg rX tQ Ue Uh uI Uk uM Uo Ur Vs Vv) iO(eT eZ fN fY hP Ib Ic pS pY qA qB qC qH rO rQ rR rS sC sK sM tN tO tQ tR tS tT tU tV tX uG uI uL uN uP uR uT uU uW uX uZ vC vH vO vS vU vW wB wC wE wH wK wL wP yD yH yJ yK yL zG zH yE tM) No(eT eZ fN fY hP pS pY qA qB qC rO rQ rR rS rV rW sC sK sM sO tN tO tQ tR tT tV tX uG uI uL uM uN uO uP uR uT uV uW uZ vI vO vP vQ vS vU vV vW wC wD wE wG wH yD yJ yK yL zG zH zI yE tM) Ly(aC aG aH aN Ao As aV aX bF bO bP bX cC cE cF cJ cK cL cN cQ Ct CU cV cZ dA Dc dF dK dL dM Ef Ex Ez Fy Gp Hu Ic Ii Iz Jo Js Kk Ks Lu Mc Ml Ng Nj Nt Of Og Ou Ow Pg Ph Qw Uc Vv Tj) uM(aA aW cR Cu dA dR Ed Fw Gl gP gW Ha hG Hu IH iJ Im In Jd Je Jm Jo Kg Ki Kj Kk Ko Kr Ld Lx Mj Nb Nf Ni Nj Nn Nr nW oF Oh Pa Pc Pf Pg Pk Po Qb Qe Qm Qy RC rV Uh Up Us Uv Vu Vv) Ib(bX cZ cC Ed cF fP Fw gP gW hB hC hF hG hR Hu hV hW hX iB iC iH In iP iZ Jd jE jG jI jK jL jO jT jV jY kQ kR kS lL lN Mb Ml Nj nW nY oE oH Ou pF Pg qT qV QW qY rA Tt Uk Us) vA(aG bQ cR dR Ed fY gW hG iJ Ik Jd Ji Jm Kl Ko Ky Ld Lx Mg Mn Nb Nk Nt nW nY Oe oF oN Ou Ow Oy Oz Pb Pe Pf qO QU qV QW Qx Rb Rf Rg Rm Ub Uc Uh Uk uP Ur Us Vs Vv) Hu(Ic pS pY qB qI qX qZ rO rQ rR rS rV rW sC sK sO tN tO tQ tS tT uI uL uP uR uT uU uV uW vH vI vO vP vQ vS vU vV vW wC wD wE wG wH wK wP yH yJ yK yL zG zH zI yE tM) Kr(eT fN fY hA hP iC jP Me pS pY qA qB qC qH qI qO qP qU qX qZ rO rR rW sK sM sO tO tQ tR tS tU tV tX uI uT uU uX uZ vC vO vQ vS vU wG wH wL yD yJ yK yL zA zG zI yE) rV(aI aK aV aW bI bO bQ bV cC cG cI cJ cR cS CU Cv dA dC dF dL Fw iH iJ Jd jL Js Kk Ld Lx Ma Nb Nf Nj Nn nY Oe oF Oh Ow Pe Pf Pg Po QU qV Qw Qy Rh Us Uv Vv) qX(AO As aW Bg bO bZ cC cS cU dF Dg Ez Gl iA iC Ij Il Iu Iv jG Jk Jl Jn Jo jP Ke Ki Kk Kl Ko Ks Mj Mm Mq Mw Ng Nu Ou Pg Qb Ql qU Qw Tn Tr Uc Ue uG Uu vH Vs) qH(aK aM aU aV bC bE bO cI cJ cR cS Cv cZ dA DC Ed Gl iH iJ Jd Je Ji Js Kk Ky Lx Nt nY oF Ow Oz Pb Pe Pf Pg Po Qm QU qV RB Rc Rf Rg Uh Uk Uv Vv) Us(hA Hc hR hX iB IC jE jG jI jK jL jO jP jT lL lM lN lO Mb Nc Nx nY On Ou qO qU qW RA Rb rW rX rY rZ sO tO tS uG uL uO uX vP vV wD yD tF) Lx(fN hA qA qI qP rO rQ rR rS rW sC sK sM sO tN tO tS tT uG uL uP uR uT uU uV vH vI vO vP vQ vS vU vV wB wC wD yD yH yJ yK yL zG zH zI yE tM) Kk(eD In Me Ou pS pY qC qI qT qU qZ rO rQ rR rS rW sC sK sM sO tQ uG uL uP uR vH vI vP vQ vU vV vW wF wH wL yH yJ yK yL zG zH zI yE tM) Ed(eT fN fY hA hP iC iJ In jO jP jT pY qA qB qC qI qO qP qZ rO rQ rW rZ tN tO tS tT uG uL uO uT uV uW vI vP vV wD wF yD yH yK zG tM) Ic(aC Cv dR eD eF Fw Fy GL gP gW hB hF hG iA iH iJ Ik In iP jO jT kR kS Mc Me Ml Nm nW nY oE oF oH oN Pg QU Qw Rb Ue Vv tF) qB(aN aU aV Ba bQ cG cI cJ cP cT Cv DC Ez Gl iJ Ik Je Kl Ky Ld Nb nY Oe oF Og Ow Oy Pb Pe Pf Pg Qu Qw Rb Rg Ub Uk Um Uo Vv) Fw(eT eZ fY hA hR iA iB iJ iP jE jG jI jO jP jY kQ lL lN Me Ne Nj Nl nY Ou qO qP qU Qw Rb rO rQ rR rS rW Ue Um uN vP vW tF) oN(eT nF pS sK sM sO tO tQ tR tS tU tV uI uL uN uO uT uU uZ vC vH vO vQ vS wB wC wE wF wG wH wL wP yJ yK zA zG zH zI yE tM) Vv(eZ fN hP hV hW hX iJ jU nY pY qA qC qV qW qY rA rB rC rO rQ rR rS rX sO tT tU tV uG uN uO uT uV uX vQ vV wB wK tM tF) eD(As cA cC cW dA EZ fY iA iC Id iH IJ Ik In Io Js jT Ke Kl Ko Lu Ma Mc Nj Nm Pe Pg Ql qP Qu Qw Rb Uc Ue Um Uv Vo) hA(bC bW cA cE cN Cu Dp iH Ij Ik Io Jj Jo Kc Kj Ko Ks Lu Lw Ma Ng Nm Nt Oh Ou Pe Pg Qh Ql Qm Qu Qw Rc Rg Rh Ue Uf Vs Wn) rW(aI aW Bc bG cO cS Cu Cv Gl hB hC iA iH iJ Je Jf Js kS Ld Ma Nb Nj nY Oe oF Ow Pe Pf Po Qd QU qV QW Rh Uv tF) qC(aI aK aM aN bA bQ cG cS cT Cv dF EZ Gl gP Ik Je jL Kl Ky Nb nY oF Og Ow Oy Oz Pe Pf qU Qw Rb Rf Uk Uo uP) Js(eZ fY iB jE jF jG jH jI jK jL jO jP jQ jR jV jY lK lL lM lN lO qA qI qO qP qW rA rO rQ rR rS uN uP vP vW) In(aC gW Ha Hc hR iA iC iJ Is Iu jI jO jP jT lL lN Nc Nh Nj nY Oa oE On qT QU Qw Ra Rb Rm rZ Um Ur tF) Nb(pY qI qU qZ rO rQ rR rS rZ sC sM sO uG uL uU uV uW vH vI vO vQ vU vW wH wK wL yH yK zG yE tM) Bc(eT eZ fN fY hP pY qA qI qO qP rO rQ rR rS sK sM uI uX vO vP vU vV wB wC wD wF yK yL zA zI) aC(aD aH aI aS aV aW aX aZ bG bI bJ BO bP bU bW bX cA cB cE cJ cL cP cV cW dL Ex Gl gW Tj) qU(As cN Cu cW dA iB iC Id iH iJ JO Ko Ks Nm Oh Ou Pg pY qO qP Rj rO rQ rR rS Ug Uv vH wL) vH(bQ dR gP gW iH iJ Je Jf jY Ko Kz Mn Nj Nt nY Oe oH Ow Pe Pf Pg Qu Qw Qx Rh St Ub Ue) aW(qI qO qP qZ rO rQ rS rZ sC sO tO tS tT tX uG uP uW uX vI vW wB wC wD wH yD yK tM) pY(aK Ar bQ cG cJ cP dC dF Gl Je Ld Nj nY Oe oF Ow Pe Pf Pg Po Qu Qw Rb Rh Uk Um Uo) rO(cP cR cS Cv Gl iH iJ Jd Je Ld Ma Nr nY Oe oF Pe Pf Pg Po Qu Qw Rh St Uk Uv) qP(aI aK aV cC cG cJ cO cS Cu dC dL Gl hC iJ Je jL Ld Ma Nf oF oH Pf Po Uv tF) Me(Ez Fy Gz Iz Ki Ko Kz Ou Ph Ql Qu Qw Ua Uc Ue Uf Ug Uh Ut Uu Uv Vo Vp Vs) wL(bQ Cv dA dB dR gP gW iH iJ Jf Kl Ky Ld Nt nY Oe oF Pf Qu Qw Rf Ue Uh Tj) rS(cR cS Cu iH iJ Jd Je jL Ld Ma Nj Nn nY Oe oF Oh Pe Pf Pg Po Qu Qy Rh Uv) wD(aZ cA cN cS Cv IH Jd Kn Kx Ld Ma Nt oE Pe Po Qd Qe qV Qy Ue Uk) St(pS rQ sK sM tQ uG uI uL uX uZ vC vO vS wC wG wH yH zA zG zI tM) rR(bQ cR cS dR Gl iJ JE Ko Ld Ma Nj nY Oe oF Pe Pg Po Qu Qw Rh) qO(aI aV cC cJ cS Cu dA dC dL Gl gW hC iJ Ld Ma Nf oF Pf Po Qd Uv) Cu(hR hX iB iC jE jK jL jO jP lL lN qV qW qY rA RB rZ) iJ(cD Ou qI qZ rQ tQ uG uI uO uX vU wC wE yJ yL zA zG zH) vW(aK cN cS Ha Jd Nf Nn Oh Pe Pg Po Qd Qe Qy rY Uh Up Uv) Oe(eT fY hP pS qA rQ tN tO uG uL uV uX vU wK yH zG zI) eZ(aK cS dA Ha Ih Jd Je jL Ld Ma Nf Nn Oh Pe Pg Po rY) vP(aK aZ cC cS cU gW hC Jd Jv Ma Oh Pg Po Qe qV qW Qy) Qd(sC sO tS tT uG uN uP uW vI vV wK wP yD yH yJ tM) Ld(eT fN fY hP jP qA qI qZ rQ sO tS uI uL wH wP) wK(Ha Ju Kx Mt Nt oF Pg Po qV Qy Rm Uh Uk Up Vs) Ou(iC iH Ik jI jO jP lN Nf Nj qT Rb rY rZ tF) dA(hR jO jP qI qZ rZ tQ uL uO uP uV vU wE yD) rQ(cR cS Gl Je Ma Nj nY oF Pe Pf Pg Po Qu Rh) Nt(iB iC jK jL jO lL lN qT rZ uL wG wP yE) iH(qT qW qZ rX rZ sO uI uL uO uZ vQ wG wH) Qy(sC tN tS uG uL uP uW vI vV wB wF tM) yH(dR Gl gW hG Im Je nY Pe Pf Qm Rh Uh) jP(aK cW Ik Nj Nm Qu Qw Rf Rg Rh Ue Vo) Po(eT hP qI qZ tT uG uP uW uX vV tM) Of(hV hW jK jQ jR jU lO qY rA rB rC) cR(fY hP qI qZ sO tO vI vV yD yK) cS(eT fY qA qI rZ uN uP vI vV wB) uG(dR iB Jd Ko Nj Pa Pf Pg Rc Up) jO(As cA cN Ij Io Ng Qu Ue) rZ(cN Io Kj Ng Oh Ql Ue Vq) Ma(fY iC qT sO vS vV yD) Pe(qZ sO tQ uN uU wP tM) aK(fY gW qA qI qZ zG zH) uL(Kz Ow Pf Pg Qw Ue Vs) qV(tN tO tT vI vV yD) uN(Ha Nf Pg Qb Qe Up) Jd(sO vV wB yD zG) Je(eT hP tN uT yD) Rh(sM uP vS yJ tM) Pf(qZ tQ vU zG tF) fY(dC dG dL Nf oF) hR(Iu Kj oH Ql tF) Ue(rX rY sC sO) Pg(lN tQ tM tF) iC(cW Qu Qw Rg) qI(cG dC Gl Uv) oF(hP qZ wF wG) rY(Ij Kj Ng) rX(Fb Kj Ng) Gl(qZ wH) Nm(lN qT) Mt(sC wG) Nf(eT qA) Kp(sK zG) Vs(tO tT) cP(eT vU) cW(jG jI) gW(zG zH) nT(Aa cG) wP(Im nY) tQ(gP Pk) wF(Mn oH) jT(cA Qu) tM(Rc Rm) BanO UcOn IvqT RbcD QeuP JftO JjnA TkUh UoyL UvqZ VquI dLqA gLsO tFhP iAjL} iH{qU(aA aC aD aE AF aG aH aI AJ aK AL aM AN AO aP aQ AR AS aU aV AW AX aY aZ BA BB BC bE bF Bg bI bJ bL bM BN BO bP bQ bR bS bU bV bX bZ cA cB cC cF cG CH cI cJ cK cL cM CO CP CQ cR CS CT CU CV CX cY cZ dA DB DC Dd DE dF DG dH DI dJ DK DL dM dN dR eC eD eF Et Fn FP gL GP gW HA HB HC HF hG Hq hR Hu Hv iA Ib Ic Id Ih Ii IJ Il In IO IP Ir Is It Iu Iv IZ JD JE jF JG JH JI Jj JK JI JM Jn JO JP JQ JR Js JT jU jV jY Kd Ke Kf Kg Ki Kj Kk Kl Kn Kp KQ KR kS Ky Lh lK lL lM lO Lv Lw Lx Ly Lz Ma Mb Mc Md Me Mg Mh Mj Mk Ml Mm Mn Mq Mr Ms Mt Mu Mv Mw Mx My Mz Nb Nc Nd Ne Nf Ng Nh Nj NK Nl Nm Nn No Nq Nr Ns Nt Nu Nv NW Nx NY Oa OE OF Og OH Oi OK oN Or Ow Oy Oz Pa Pb Pc Pd Pe pF Pg Pj Po Qa Qc Qd Qg Qh Qm Qt Qu qV qW Qx QY Qz RA rB RC Ri Rj rX rY rZ Ss Ub Uc Uf Ug Uh Ul Un Ur Us Ut Vp Vq Vs Vv Wm tF) rX(aA aC AD aE aF aG aH aI aJ aK AL aM aN aO AP aQ aR AS aU aV AW aY aZ BA bB BC bE bF bG bH bI bJ bL bM bN bO bP bQ bR bS bU bV bX bZ cA cB cC cF cG cH cI cJ cK cL cM CO cP cQ cR cS cT cU cV cW cX cY cZ dA dB dC dE dF dG dH dI dK dL dM dN dR eC eD eF Et Fa Fb FP Fr Fw gL GP gW HA HB hC hF hG Hq hR Hu HV HW HX iA IB Ih Ii IJ Il Im In IO IP Iq Ir Is It Iu Iv iZ JD jE jF JG Jh JI Jj JK JL Jm Jn JO JP JQ JR Js JT jU jV jY Kc Ke Kg Ki Kk Kl Kn KQ Kr kS Lh Lj lK lL lM lN lO Lv Lw Lx Ly Lz Ma Mb Mc Md Mg Mh Mi Mj Mk Ml Mm Mn Mp Mq Mr Ms Mu Mv Mw Mx My Mz Na Nb Nc Nd Ne Nf Ng Nh Ni Nj Nk Nl Nm Nn No Nq Ns Nt Nv nW Nx Ny Oa OE OF Og OH Oi oK ON Or Ow Oy Oz Pa Pb Pd Pe pF Pg Po Pz Qa Qb Qc Qd Qe Qh Qm Qt qV QW Qx Qy Qz RA rB RC Ri rY rZ Sr To Tz Uc Uf Uh Ul Um Un Ur Us Vs Vt Vv Wm tF) qX(Ad Af Aj Al An Ao Ap Ar As Aw Ax Ba Bb Bc Bg Bn Bo Ch Co

Figure 21 Continued

Cp Cq Cs Ct Cu Cv Cx Db Dc Dd De Dg Di Dk Dl Dp Ef Et Ez Fa Fb Fn Fp Fr Gl Gp Ha Hb Hc Hf Hq HR Hu HV HW HX IB Ic Ih Ii Ij Ik Il
Im In Io Ip Iq Ir Is It Iu Iz JD Je Jf Jg Jh Ji Jj JK JL Jm Jn JO Jp JQ Jr JT JU Jv JY Kc Kd Ke Kf Kg Ki Kj Kl Kn Ko Kp Kq Kr Ks Kx Lh Li Lj
Lu Lv Lw Lx Ly Lz Ma Mb Md Me Mg Mh Mi Mj Mk Ml Mm Mn Mp Mq Mr Ms Mt Mu Mv Mw Mx My Mz Na Nb Nc Nd Ne NF Ng Nh Ni
Nj Nk Nl Nm Nn No Nr Ns Nt Nv Nw Nx Ny Oa Oe Of Og Oh Oi Ok Om On Or Oy Oz Pa Pb Pc Pd Pe Pg Ph Pj Pj Pk Po Pz Qa Qb Qc Qd Qe
Qg Qh Ql Qm Qn Qt Qu Qv Qw Qx Qy Qz Rb RC Ri Rj Rm rY Sr Ss St Tn To Tr Tt Tv Ua Ub Uc Ud Ue Uf Ug Uh Uk Ul Um Un Uo Up Ur
Us Ut Uu Uv Vo Vp Vs Vt Vv Wm Tj) rZ(aC aE aF aG aI Al aO Ap aW aX aZ Ba bB bF bJ bL bP cD cF cG cI cJ cL cN cR CV cW cY cZ dD
dI dJ dK dM dN eD eF Et Fa fP Fr Fw hA hR hX iC IJ Il In Io Ip Iq Ir Is It Iu Iv iZ Ji jL JM Jo Jp Jq Jr Js jV Jy Kq kR Lh Li IN Lw Lx Mc Mf
Mg Mk Mm Mn Mq Ms Mu Mv Mw Nb Nd Nf Nm Nn No Nq Nr Ns Nt Nu Nv Nw Nx Ny oE OF Oh Ok Om On Or Ow Pa Pc pF Pg Po Qh
QT qW Qx qY RC Tz Uf Uh Ul Ur Vq Vs Vv) qW(aA aC Ad aE aF aH aK AL aO Ap aQ AS aU aV aW aX aZ bA bC bE bH bJ bN bP bR bU
bV bW bX bZ cA cD cE cF cG cJ cK cM cN cQ cT cU Cv cW cX cY cZ dB dD dF dH dI dJ dK dM dR eC eD Et Fr hA hF iA iB IC Ij IO IP Iq
Ir Iv jH Jl jL jM Jq Js jV Jy Kk KQ kR kS Li IM Lw Lx Ma Mc Mf Mg Ms Nf Nl Nq Ns Nt Nu nW nY Of Ok Om ON Ow Pe PF Pg qT rA Rg
Tz Uf Ul Ur Vs tF) qT(aA aC Ad aE aF aH aJ aK Al aO AP aS aV aW aZ bA bC bH bJ bN bP bQ bR bU bV bW bZ cA cC cD cE cF cG cJ cK
cM cN cO cQ cS cT cU Cv cW cY cZ dB dD dE dF dG dH dI dJ dK dL dM dR eC eF Fr Gp hA hB hF iB iC In IO iP Iq Iv iZ jH jl jL jM jP Js
Kk KQ kR kS IL IM Ma Mc Mf nD Nq Nt Nu nW nY Of oK Om oN Ow Pe PF Pg qV qY RA rB Rg Tz Ur Us Vv) Ed(Ba Bo bW cE Ex Gz hR
Ic jL jT IM Ou pS qD qG qH ql qP qQ qZ rB rC rN rO rR rS rT rU rV rW rY sC sK sM sO tN tO tV UfuG uL uP uR uT uU uV uW uX vB vl
vO vP vQ VS vT vU vV vW wB wC wD wE wF wG wH wJ wK wL wP wQ yD yH yJ yL zA zG zH zl yE tM tL xA) qY(aA aH aK aS bA bH
bJ bW bZ cA cD cJ cN cQ cU cW cY dD dF dH dI dJ dR eC eD Fr Fw hA hR iA iB iC iP Iv jH jl jM Kk kQ kS IM IN Mc Mf Nu nY oN Ow Pf
Pg Rg Tz tF) qV(aH Ap bG bH bJ bW bZ cD cJ cN cU cW dD dF dI dJ eC eD Fr Fw hA iA iB IC Iv jH jM Kk kQ kS IM IN Mc Mf Nu nY Of
oN Pf Pg Rg Tz Ur tF) Ap(hA hO hR Ic nF Ou Pg qH ql qO qP qQ qZ rB rN rO rP rQ rR rS rU rW sO uG ul uL uM uN uW uX uY vA vB vC
vP vV wB wG wH wJ yD) rC(aE aW bG bW bZ cJ cN cR cS cU dF dI dJ dK eD Fw hA hR hX iC jG jH jl jL jV kS IL IM IN IO Mf Ms nY oN
Pf Rg tF) rU(Bc bX cC cl cW Dc Dd Dl Et Hb Hw Iq jH Jj Ki Ms Nm No Nq Nr Nu On pF qP Qz sC tS Tz uM Un vB vV wE wF wH wL xA)
Aj(hO qG qQ sC sK sM sO uG uL uM uT uU uV uV vA vB vH vP vQ vS vT vU vV vW wF wG wH wK wL yH yK zG zH zl yE tM tL xA) rY(Al aZ
bW cD cE cN Cv dD dI dJ Fw hX iC Io Ip jH JM Jy Li IM IN Mc Mf Nf Nq Nt Nu nY Ok Om On Rg Ur Vq) Et(fY pS qH ql qO qP qQ qZ rB
rN rO rP rQ rR rS rT sC sO uG ul uM uN uW uX vC vP vQ vV wC wD wJ wL zl tM) vB(Bc bW Dc Dd Ii Ij It Jd Jh Jj Jm Jp Jq Jr Kg Lh Mg
Mn Nm Nn Nu Nx Ok Om Qz rA Rc Uc Ug uM Un Ur Uu Vq) Lh(hL hO qQ rS rT rV sM sO tO tS uL uM uO uP uT uY vA vH vP vT vU
wD wF wH wJ wL yH zl tL xA) Qz(hO qG qH ql qZ rO rP rQ rR rT sC tX ul uO uP uT uY uZ vH vT vW wB wD wF wH wL yH yK zl tL
xA) Jj(qG qH ql qZ rR rS rT rV rW sK sM tS uM uP uV vA vl vP vS vT vW wB wF wH wL wQ yH zG zH tL xA) rA(aZ bH bW bZ cD cN cU
cW dD dF dH dI dJ eC eD Fr iA iB iC Iv jH kS IN Mf Nu nY oN Pf Rg Tz tF) rV(Ao Bc dC Dl Hw Ij Ik Iq Jd Jg Jh Ju Kf KJ Kq Mg Mn Nm Nn
No Nr Nu Pj Pk Qu Rc Uc UfUm Uu) IM(aF aH aK aO bG bQ bV cE cG cJ cL cO cT cU dD dG dH eD Fw hB hR iA iB jM jO jP IN oN Ou tF)
qQ(Bc Co Dl Hb Hw Ij It Iu Jg Jm Jp Jr Jt Kc Ki Ky Kz Md Mg Mn Mw Ok On Rb Rf Tn Uf Us Uu) uZ(Ao Dg Dl Hw Ij Iq It Jg Jh Jp Jq Kf Kl
Kq Mn Nd Nm Nn No Ok Om Qt Qu Rc Tz Uf Un) rB(bG bW cD cN dl eD Fw iC Iq jH jM Kq Li IN Lx Mc Mf Ms nY Ok On Pe Pf Rg Tz)
Bc(qD qG qH ql qP qZ rN rO rR rW sC sK sM uG uU vI vP vQ vV wF wG wK yK xA) uM(bC Dl Fw Hb Hw Ik Iq Ir Jg Jh Jp Jq Lx Mg Ni Nm
Nx nY Ok Rc Tz Uc Un Uu) On(eD Fw hA hL hO In nF qD qG qZ rT uG ul uN Us uW uX vC wG wL wQ) wQ(Co Dc Dg Fy Hb Ij Iq It Jm Jo
Jp Kf Kj Kl Mn Ms Nm No Om Qu) uY(Dl Ij It Jd Jh Jm Jp Jq Jr Kf Kj Kl Mn Nn Nx Ok Uc Uf Un Uu) uL(Dd Dl Hw Jd Jh Jp Jq Kg Kj Lx Nj
Nm Nu Nx Ok Pj Pk Uc Vq) eD(bW cE cJ cK cW dD hR Iq jH jL mP nl nK Nn Ou Pf Rg) uO(Ao Dl Ij It Jg Jh Jp Kf Mn Nm No Ok Qu Rc Tz
Uf Un) Tz(qH qZ rO rP rQ rR rT uG ul uN uW uX vC wG zH) nF(Aa Aw Cp dB Dg Di hA Ij jL jP Lw Lx Mu oN Pf) wL(bW Dc Dd Ij Ip Jp
Kg Kj Mg Nm Nn No Nr Nu Un) wH(aC Ar Aw Ch Ct Ef Hw jH Mg No Nu Of Qu Ur vO) vA(Dl Fy Ij Jh Jp Kg Mg Mm Nn Ok Om Rc Uc Uf
Un) xA(Ao Dd Hb Ij Ik Jg Jh Kg Kl Li Mg Ok Om Uf) uX(aJ Di Hb Jp Ju Lx Me Nm No Nr Ok Om Un) ul(Hb Hw Jh Nm Nn Nq Ns Nu Ok
Om Ul Um) Jp(hO qD qZ rO rT uG un uW vC wG zl) Jt(fY hL hO qC qD qO qP tN tQ wE zA) hA(Ba bW cE cW dD Fr Kq Lx Ok Pf Uf)
Hw(rR uN vQ wD wF wG yH yL zH zl) Om(qG qZ uG uN uW vC vP vQ vV wG) hR(aZ bW cN Cv Fw jL IN Pf Uf tF) Mg(qG sC sK uG vH
vQ wF tM tL) Hb(qG qZ rO rW uG uN uW vC wG) No(rR sK tT uN uV uW vI wF) Nu(qG rR tT vV wF zH tL) Qu(hO rT sC vW wD zl tM)
dD(iC jH jl jL jM IL IN) nO(Ba bW cE cH dB Li Pf) jP(kK IX lY mE mF nK nU) Dd(rQ rR wF yK yE tL) Nm(uG uN uW vC wG zl) Jm(In uP
wF yJ zH tL) Ou(Ba hX Ic jH jL IN) nT(bW cG cL mU nJ Pf) qG(Ao Co Fw jH Kg Kl) Jd(hO Ib qZ rT uV) Un(qZ uG uN uW vC) zH(Ms Nr Nt
Um Vq) Fw(jT Kq rW yK) Ok(uG uN uW vC) qD(Dc Kj Qw Um) jM(Ad Fr Kq nl) Ic(Ba Cv Gp) hO(Dc Nn Pz) IN(cK kO Pf) Ar(rP rR) Nr(uN
uW) Lx(yK zA) In(Al Iu) Uf(vQ wJ) Ur(wF yK) Us(Dk Jg) bG(jH jL) hL(Dc Nn) qC(Qc tM) tL(Kg Kj) MetX UcwG JovT KlvQ VquN bCrT
cQjH cWjl dFuT eCjL IYjD} Us{On(aA aC AD aE AF aG al aJ aK aL aM AN aO AP aQ AR aS aU aV AW AX aY aZ BA BB BC bE bF bG
bH bl bJ bL bM BN BO bP bR bS bU bV bW bZ cA cB cC cE cF cG CH cI cJ cK cL cM cN CO cP CQ cR CS CT cU cV cW CX cY cZ dA DB
dC dD DE dF DG dH DI dJ DK DL dM dN Dp dR eC EF Et EZ Fa FP Fr gL gP gW Ha HB hF hG hO Hq Hr HV HW HX Id IJ Il Im iO iP iZ
jD JE JF Jg JH Jj Jk Jl Jn Jo Jp JQ JR Jt JU jV jY Kc Kg Kj Kl Kp KQ KR kS Lh Lj IK IM Lu Lv Lw Lx Lz Md Mf Mg Mi Mj Mk Mm Mr Ms
Mt Mu Mx My Na Nd Nn Nu Nv nW Nx Oa oE OF Og oH Ok Or Oy Pa pF Pz Qa Qb QC QD Qe QV Qx QY rA rB RC Rg Ri Rm rY Sr St Tn
To Tv Tz Ua Ub Uc Ud Uf Ug Ul Up Ut Uu uX Vt Vu Wm) Ly(aE Al aN Ao Ap Ar Ba Bb bF Bo bP bQ bX cC cE CH cN Co Cp Cv DD Dg dJ
Dk Dl Fr Fw Gp Hq Hu Ib Ic Ii Iq Is Jd Je Jh Jm Jq Kf Kg Kl Kn Lx Mq Mr Mu Mv Mw My Nc Ne Ng Nl Nv Nw Ny Of Ok Om Ou Ow Oy Pg
Qt Qu Qx Qy Rc Ss Uc Uf Ur Us Vu) Dk(aC dR eF eZ fP gL gP gW hB hC hF hG hL hP hV hW hX iA iC iJ iO iP iZ jD jE jF jG jH jI jK jL
jO jQ jR jU jV kQ kR kS IK IL IM IO Me nW nY oE oF oH oN pF pY qA qD qH qO qP qV qW qY Qz rB rC rN rO rQ rS rT rV tS uW uX wD
wJ) Jg(Cv eC Fw gL gW hA hB hC hF hG hV hW hX iA IB IC iJ iO iZ jD jE jF jH jK jL jO jP jQ jR jT jU jV jY Kk kQ kR kS IK IL IM IN IO
Mb Me Ne nW Nx oE oF oH oK oN Ou pF qG qO qQ qV qW qY RA RB rC rY uM uY xA) Ap(Fw hL hO hV hW hX iA iB iJ iP jD jE jF jH jl
jK jL jM jQ jR jU jV jY IK IL IM IN IO Me Nx nY oK qD ql qP qQ qV qW qY QZ rB rC Rh rN rP rQ rR rS rT rU rV sC uM uO uW uY vS
vV wC wG wH wJ wK wQ yD zl tM tF) IM(Ad aE aF aI aO aS bA bG bQ bV cE cG Co cS cT cU Cv Dc dG dH eD Fa fP Fw HA hB hR iA Ii
Iu Jd Jk Jm jO jP JT Kq Li Lj IL IN Ma Ml Nc Of Oh oK Ou Pe Pz Qh qT uQ qX Rg Rj rX rY Tz Vs Vv Wm tF) Ad(eD hA IB IC jD jE jF jG
jH jl jK jL jM jO jP jQ jR jT jU jV jY IK IN Me Nx nY oK qD ql qP qQ qV qW qY QZ RA rN rQ rR rS rT rV rW rX rY rZ tN tO tQ vO vS vW
wJ wK yD yE xA) Nx(Aj Al cD Cv Dc Dd Dg Ed Et Fw Hc Hu Ik Io Ip Ir It Iv Jd Jk Jm Jt Kd Kf Kk Kl Kq Ks Mb Mc Me Mh Ml Nc Ne Nf Nj
Nl Oe Oh Oi Pg Pi Qg Ql qT Qu Qw qX Ra Rb Rj rX Ss Ue Uf Ug Uk Um Uv) Aj(pS qG qQ rO rU sK sM sO tN tO tQ tR tS tT tU tV tX ul uM
uN uO uP uR uT uV uY uZ vA vB vH vl vO vP vQ vT vU vV vW wB wD wE wF wH wJ wL wP wQ yD yH yK yL zA zG zH zl yE tL) Qz(Ao
Ar Ba bF Ch Co Cp Cv Dc Dg Et Ex Fr Fw Hc hL hO Hq Hu Ib Jd Je Jh Jt Lh Lx Mq Mr Mu Mv My Nb Ng Nv Nw Ny Of Ok Om Oy Pg qD
Qt Qx Qy Ut Vu wQ) qX(Ao Bg Bo Ch Cq Cv Dc Ed Fr Ha Hq Hu Ib Iu Iz Jd Je Jk Kf Kg Lh IO Lx Mk Mr Mu Mv Mw My Nd Nv Ny Pa Pd
Pg Po Qh Qt Qx Rc Tn Tt Tz Uc Ut Vq Vu) rX(aE Ao Aw Bb Bc bF Bg cE Cp Cv Dc dD Dc dl Et Fr Ha Hq Jd Je Jh Jt Lx Mq Mu Mv Mw Mx

Figure 21 Continued tO wD wK) Db(hA jO Me wK wQ) Mp(tT uW wD wK wQ) dB(tO wG wL) xA(Js Me Uv) wK(Ki Nt) UepS} Jd{Ki(hO Ib pS qG qI qQ rU rV sM ul uM uY wC wE yL zG zH xA) Ib(aZ bF bU bX cB cF Tt) Hf(hO vB) DbhO NovI RbrT UmzH dBzA} jP{mF(aO bL cE cG cW dF fP hC) nR(bG bI bL bQ cR cW iZ) cW(kP IX mM Of) mM(bC bG hI) bL(kO mZ) gL(kO mZ) kC(cG hG)} Hf{vB(aP bW cN cR De iO Ug uX) Cv(jY qU rX wQ) Me(bP cD cE dD) xA(Dk Jh kQ) hO(Aj Pz) KqjM PfqU aPwH oKuW} dB{wL(Hw Iq Is Kc Nm Nn Nr Ns Nt Nu) qX(bG eD iC IM qU rX) No(wF wH) Iq(wG wQ) FyuM NmwQ NtwH ItwG rZIM} Ib{Tt(Cv gL Hu Ik Jg Kf Kx Mg Ml Rb Ss Uk tF) kG(Dc gL) BabX JgKk} Db{hO(Aj Pz xA) wQ(Jl oH Vp) Me(Kq Ou) Li(jM qU) UbuL RbcD JgqG PfqU wHoK} Nt{jT(Ba Jg Ke Kf Kg Kq Nx) Uu(tU vP vW) Bb(qX vB) Kq(hA Me) QuwK} cC{Dd(hO rO rU xA) Pf(eD hR lN) Ub(wL yL) qG(Dk Jg) NmwQ MetL KqqX} mF{jE(cW Ih Ir Lx Mn Nn Nq Nr Pe Po Qa Qb Qe) PoLx} rU{vP(Bb Jr Kf) Iq(Na No) gW(vI wL) zA(aK aU) JrxA KKPj UmyK} bF{bX(aH aW aZ cF) cF(aH bG cV) nR(Nj Oi) aHcB eDkK} kO{kS(lM qX rA) bL(jH jK) PoLx HciP aOlM cSIK cWjG qXjQ} No{Bb(qH vS xA) Iq(rO rR yE) ljhL Jrvl UuvW jF Hw Hx Ih Ij Il Im Ip Is It Iu Jk Jl Jm Jn Js Lh Lu Ma Mf Mg Mh Mi Mj Mp Ms Mt Mu Mv Mw My Mz Nc Nm Nn No Nq Nr Nt Of Oi On Oz
Pa Pc Pd Pe Pf Pg Po Pz Qa Qb Qe) cF(AD aE Aj aM AN Ao Ap aQ AR AW aY aZ bA Bb bG Bn bO bP bQ bU bW bX cA cB cC cG Ch cl cK
cL cN Co CP cQ cT cU CV dC dD DE DG Di Dk Dl dM fP Fr Fw In On) dJ(aK aQ bF Bo cE cK cP cT eD Ef fP Gp Hc hV hW hX Is JD jF jH
jL jR Ki Kk Kq IL IM IN IO Ml nB nJ nO Of On Ou Qg qT qU qV QW qX qY Ra RB rC Rj rY Ss vB wG Tj) Nh(Et Hq Hu Hw Hx Ih Ii Ij Ik Il
Im Io It Jj Jk Jl Jm Js Lu Mc Me Mh Mi Mj Mk Mn Mp Mt Mv Nd Nf Ng Ni Nj Nm Nn Nr Nt Ny Of Oi Oz Pc Pf Pg Po Qa Qb Qe) nT(aJ aM
AP Aw aY bC bL Bo cM Cp dD Dg dL Ex fP Gz HC Id iO Ju Jv Kc Kk Kn Kz mP nJ nK qT Rg Ri Rj Ua Uf Ut Vs) nJ(bF cE cG cL hA hW hX
iC iO jD jF jH jl jM jP jQ jR jU jV jY kO IL IM IN IO nB nO oN oP oQ qU qX rA rB rC rX Up) In(Al Ar Ba bF Bo bX Co Cp Cv Dc Dd Et Ex
fP Ha Hc Jd Je Kg Ki Kn Kq Kx Mr nA Nd Nj nK Ph Rb St Tn Uf Um Ur Vs) Kz(nB pS qQ rQ sC tQ tR tX uG uL uM uV uX uY vB vH vl vO
vP vS vV vW wC wL wQ yJ yL zG zH yE tM tL xA) nB(Fn Fw Hc Ib Iz Kc Kg Ki Kx Ld Lx Nj Ow Ph Pk qT Qv Qy RA Rg Ri Rj Rm Tv Tz
Ua Ub Ug Ut Vt) bF(aH aN aW aZ bG bH bM Bo bQ bR bU bW cG cl cK cN cP cU cV dM Fw gW Ma Nj nR Qw Rb tF) Ap(hA hO hR iA Ib
jM Nj Ou qC qD qG qH qQ qU Qw rB rO rU rV rZ vW wJ wQ tL xA tF) Bo(aH aW Bg bU bX cB cE cK cL cP dR eF fP Fw gL gP iJ jM Me Nj
nY qU Qw qX Rb tF) On(aN As aZ bO bX cC cD Cq Cu cZ Dc dL dM Fy Ib Ki Kk Ks Qm Qu Rj Ue Vp Vv Tj) nO(aM bW cM dD dG Ex gL
Gz hB hC iO iZ Kd Kn Kq nA oF QT Qy Uf Ut Vq Vs) Qw(Ar Ba cD cE Ch Et Ex Hc hO Jg Kq IM Mv Nc Of Ou qC Rj Ss Uf vB wQ xA)
Et(Fw Fy Ib Ii Ij Il Kk Ml Mn Mp Nd Nf Ng Nj Nm Nn Nq Ny Og Ou Ra) Vq(hL hO iC jY Me Nj qX rO rY rX uM vA vT vW wD wL wQ yH
yK tL tF) nA(Ex Hu It Jj Jq Js Lu Lx Md Ml Mn Mr Nr Nx Ny Og Pf Po Vs Vu) Nj(Ar Ba bX cE Ch Cv Fw Hc Hq Io Ml Nd Ni nK Og Ou Uf)
cB(Ar aW aZ Ba bQ bW bX cK cN cP cT Cv cZ dD fP gW qX) Fw(bX cE cL fP gW Hc hG Kf Kq Lh Lx Nc qX Rb Um) Hf(eD hO Me qD qT
qU qX vB wH wQ tL xA) bX(aW aZ Ba bP Ch cL cT fP Ib Ml Of) nK(Hu Jn Js Lu Lx Mn Mr Nf Nr Og Vs) fP(bG bZ cD cO cS cU dF dH hO tF) qD(Db Dd Hb Iq Jt Na Pj Pk Um tM) Ib(Ad Ba Jd Jg Jt Kf kG oP) Iq(hO Nd qZ rU tV vB wD wL) cE(bG bU cK cU cV nR Rb tF) qX(aW aZ cC Db jE jF Ki lM) qT(Db kG kO mF nC nH nL) lM(bI cC cW DB iA) Ba(gW iJ kQ pF tF) Bc(uN vW wL zH tL) Me(Ki Ks Nd Uf uW) Ml(Ar Ki Kk Nd Um) Rb(bP cC cD dD Ex) Db(hO qU wQ xA) gW(aK Al Ch Gp) kO(cH cM iZ oN) Nd(Hq Nf Og) Kk(Ar Kc vI) dB(hR qU rX) oN(kN nN nR) Cv(Ki Rj) Ex(hO Mh) Gz(Mb Mh) Ue(vB xA) Kr(vB tL) Um(wL tL) Uf(wJ xA) aZ(hR wQ) cW(hA lN) rX(aW bL) ArNr NtHc LxlY NahO OfcD PkqC bWvW cGnR cLcU nNiZ

Constrained panels with 3 analytes, where 1.0E-9 >= 'model p-value' > 0. Contains 5 panels of 27,488,127 total panels evaluated. : Cw{BcqH bOqQ} ApNtjT JiaMnO QzdBqQ Constrained panels with 3 analytes, where 1.0E-8 >= 'model p-value' > 1.0E-9. Contains 151 panels of 27,488,127 total panels evaluated. : Cw{hO(aK aQ aU aV cI cJ cY dR gW hR Hu jE jM Kk Ko lK Nj Pe Pf Pg qO qP rW) Bc(qB vT zH tL xA) qG(Lx oK oN rY vU) rN(jF jY oN Pf xA) Hu(hL qC qH rU) Nq(fY qC qD) oK(fY Ic qO) oN(fY qO qP) aC(bE cZ) xA(cN cR) qQ(iJ iO) vP(aW rU) CuqX PoqA NoqH LxeZ StrT QzOu OfeD VvhR bOvT dCqD dJvS} iH{Ad(fN fY hL hO hP pY qA qB qC qD) Jt(qG rT rW) qQ(Nm Nn No) Ed(qT qX) qDtM} dJ{Et(rZ tO tR tS tU vP wD wG wJ wL wQ yD) nT(Kr Ks)} nT{nA(Kn Kq Tz Ur) Tr(Li Pf Uf) iP(Kc Kf Kk) Ba(Jy Vo)} Ap{Kk(rO rR rU) KiqG rBxA rUvP} Pz{qD(Na Qw Us) qC(Qw Qz)} nA{Jj(Ha Uv Vs) nO(Kq Tz)} nB{Kn(hC iP Ma) LvLd UbKc} Ad{Nt(eZ fY) Us(hO rU)} dB{Jt(tR tS) EtyD NowL} Qz{BoOu KihO} On{OuUs aMnO} NtJdeZ IqaCvB fPqDtM Constrained panels with 3 analytes, where 1.0E-7 >= 'model p-value' > 1.0E-8. Contains 611 panels of 27,488,127 total panels evaluated. : Cw{wJ(cR cS ED Ha hL hO iO jK jL jV Kr Lx Mp My Nd No Nq oK oN Pe Po pY qC QD Qe qV QY RA Ri rN St uY Vs Vv tF) St(tV uN uO uP uT uW uY vA vB vI vP vT vU vV vW wB wD wE wF wK wL wP wQ yD yJ yK yL zH xA) wQ(aW Cv dJ hL Ji Kr Ky Mp Nb No Nq Nw oK oN Oz Pb Qu qV Qy Rf Rh Rm Ue Uh Uk uY Vs Vv) uY(cN dR eD eT fY hV iH iJ iO iZ Jd jL jM jQ jR jT Kz lM Mn oF qA tT wK) No(hO tS vA vB vT wF wL wP yH tL) Vv(hA iC jM jO jT qT qX rZ wD) vB(Hu iO jL Kr Ld Nq Pb rN Vs) oN(rP rW tT uP uW uX vP wK) Nq(sM tN tO tR tT wK tL) oK(Ib qP sO tT tX uM vP) vA(Ez iH Ng oH rN Um Uo) iO(rT vT wD zA zI xA) uN(aW hL Kr Lx Po qD) Bc(qD qG rV uL wL) Ed(qG qT wB wK wP) hO(dA Nb tO vI vP) hL(tX vP vV yE) wK(Kr Lv Lx qQ) Hu(sM vT wF) dJ(aC jO qQ) wL(fY Mn Rh) tL(cW Mn oH) Mp(qG wB) Nj(rN sK) Js(qX uM) Us(Me qX) cR(qO rW) iJ(rU uL) qD(Ba Oe) qT(Cu Fw) xA(jK jL) vW(dA Lx) QduM QyqG KrwB LdrU RhrN OfqU aKqO iHqQ} iH{Jt(sO tO tR tS tT tX uI uL uO uV uW uY uZ vA vB vP vQ vT vV wD wF wG wH wJ wL wQ yD yK zI xA) qX(bG dI Fw kS lN Ou qU rA) wQ(Aj Ap Hw Ip Kg Lh) Ap(uO uZ vQ wD) Hb(uO uY uZ vA) uL(No Nr Tz Um) uI(Jp Kc No Nr) Ed(tS uM yK) qQ(Al Nt Qz) Et(uY vA) wL(Hw Jm) uM(Bc Jd) vB(Dl Tz) FwqT NmuY NovV OnvA UnuU PfrZ} Bc{Kz(rU sC sM sO tN tQ tV uL uM uN uT uX vB vO wB wL yD yJ zH zI xA) Hf(sK uT vB vS wF wH wL yD) Rb(uM wG yD yK) jY(tV uN vP wG) vW(Nt qD) KitV KrsO UswG cCuL} Us{On(ED Fw Gl Ic Iu jG Ly Me Nc Ne nY Pg Qz) Aj(uG uW wC wK tM xA) Ed(lM qT tN tO wQ) qX(Bb Dk Kq) Pz(hO qC) wQ(lM Uf) hR(Dk Jg) AdqD AprZ UcyD JtrP lMoN} nT{nA(Fa Ha Ib Kg Li Lx Pf Po Rg Ua Ut) nJ(Ba bF bW cD cE cG cL) mP(aM bL Co gL) Aa(cG dF dH) Ib(gL Kg) Id(Co Qy) KniP KqdJ VoPf cLmF gLmU} Ap{Kk(uN uY vB vQ vU vW zH xA) vW(gW Kr Og Oy St) Nt(hA wD wJ wK) wQ(dB dJ No) Ki(rP wJ) cC(qG qO) hA(Ks Nm) wD(iO Ue) xA(Ez St) QzOu} qD{Kz(sM vH vW tM) Qz(Hu Pz tM) Hf(sC uW) Kk(uU vW) Pk(wC wG) AdNa MctM QwuP UmvW} Kr{Ad(tQ tU uL vU vW wF) Uf(tT vW wF wJ wK xA) JtvW VqrZ} Qz{dB(tT wF wG wH wL wQ) Ou(Ba bF Et On Rc) ExFw InOn} Kz{qQ(pS uG uL vV wE) EdzG FwvS NbvB JdtQ KcxA bPuP qCrX} In{On(Hc Ic Jd Kk Ou Ue Um) DcnJ NlOk NxUm NynA} dJ{BogW CvIc EdOn EttV GpLy HbwG KfwQ OkrZ UfwJ aCcF} Uf{wQ(cC Hf Qw Ue) MpwJ KkvI} Vq{iA(qU qX) rZ(dA Qv) FwqX qUrY} nO{Ba(aM As nF nI) IbKg NxaM} nB{Kn(cG Ib nF nR) Kk(iP Ub)} vW{St(Aj aO Mg) FwbW} Bb{UevB PaxA fPwJ} Db{NnwQ hOvI oKuX} Ed{On(aG cD) ExcD} Ad{eZ(Na Qw)} Bo{aC(bE cZ)} Et{aKqO iOwD} Um{UvzH iCvB} nJ{DcIv VsoO} AahBwD ArJjnA ExaKgW NtOkjT LvIbkG HuTtrU IscCwL QwOnOu KiiOwF Constrained panels with 3 analytes, where 1.0E-6 >= 'model p-value' > 1.0E-7. Contains 2,399 panels of 27,488,127 total panels evaluated. : Vq{rU(Aa Ad Af aK AL AO Ap aQ aR aU aV bV bX cI cR Cs cU Cw Cx cY Dc De Dg dJ Dl dR eD Et Fr Fw fY gL gP gW Hf hV Hw iC iH Iq Is jF jG JQ JR Jt Jv jY Kq Kz lK Mf Mm Mw My Ne Nm Nq Nr Ns oE oH On Pj Pz qD qO qP qX Qz rB Rm rS rW sO St Tz Ue Uf uI Ul vB vH vP Vs vV yD yK xA tF) vB(Af aK aO AP aU Aw Ba Bb bC Bg bI bL cB cC Co Cp Cw cX Db De dJ Dk Dl Ef Et Fa Gl Gp Ha Hb Hf Ij Ir It Jd Jf Jg Jh Jq Jt Kf Kl Ko Kr Kz Li Mb Me Mw Nj Nn Nv Ok Om Po Qg Ql Qm Qn Qz RB Rc rY rZ Tz Uc Ue Uh Un Uu uV uX vI Vv yH yK) xA(aK Al AN Ap aU Aw Ax Bb bQ bX cD cY De DK Dl Fp hG Hr iH IJ iP Jd Jg Jh Jq Jt Kl KQ Kz Li Mf Mj Mv Nj oN Pa Pc Pd Qt Qy rC rR rW sK sM Ue Uv vA wD wJ wQ yK tL) rZ(aF Ao aV aW BA Bg bM bP bW Ch cM cN cP cS De dJ dL Ed Et Fw Hb iA Jd Je Jf Js Ki Kz Mk Mp Mv Nj Nn Oe Of Oh Oi Om On Oy Pc Qd Qe qV Sr Tz uY vT wF wL wQ) vA(aC Ad aK Ap aQ aV Aw bX Cp Cw cY De Et Is Iu Jh Jq Jt Ke Kf Kj Ko Kz Li No Ok On Pf Pj qO Qz rW Tz Uf yK) wQ(Ad Ap Aw Ba bF bZ Cp cT Cw Dg dJ dL Ef Et Hf Ib Jg Jq Jv Ke Kf Kl Kz Li Ma Mg Ms Oy Qz rY sO Uf Us yK) Kz(qQ tV uG uI uL uM uN uO uP uV uW uX uY uZ vH vI vT vU wF wG wK wL yH yK yL zH tM tL)

Figure 21 Continued rY(Ar bS cL dF dJ Fn iA iC iO Oi Pc Qv qX Tz Ul Us uW vW) vT(aC aK aU Aw bE Cp Cw cY Dk dR Jt Li Mw Qz uO vU VV) vW(Ap aV Cp Dk Et hC Jg Jh Jt Kl Om Qu Ss) wD(Ba cT Cw Et Jg Jv Li qW Qz sO Us Vs) nO(Af bJ cK Cv gL iP Kp Qn Uo tF) Jt(hO qB qC qD rS ul uR wJ wK) On(eT eZ fY hL hO pY qB qD wJ) yK(cG cM cO Et iA oN qU uM) Aw(pS uM uX uY wF wH wL) Cw(hA hL qH sM wJ wL tL) hO(Dk Ef Ib Ma Of Pz Uf) Et(rO rP uT wJ wK yH) q

Qa) Nj(li Ij Il Im Io Jl Mn Nf Ng Nm Ny Og Po) Nh(Ii Ij Il Im Io Jl Nf Ng Nt Ny Og Po) Ml(Ii Io Mn Mp Nc Nf Ng Nq Ny Og) Nd(li Ik Nf Ng Nm Nt Og) Nf(Io Mn nF) hA(cA cC Ks) MpIj cCyD} nF{oN(aO cD cH cV jP kN kO Lv mZ Nj nN Pa) Nf(Ba Lx Mr mZ Nv Nw Nx Ny Om Oy Po) lY(Fr Li Lx Ml Mn Nw Nx Oi Pf) Ba(aW bX cH Ct cW gP mS mZ) Lx(Iu Js Ml Ms mZ nK Oi) Bo(aV cH mS mZ oH tF) Ml(Mn Ne nK nU Po) Oi(Mr Nw Nx Ny) mZ(Id Mn Mt No) cH(Aw Di nI) Lv(Iz Rg) Mn(Nj nK) Kn(Il Rh) Nv(Iu Js) Ow(Ky Ql) DbcE NoMs LubX hCjK} Bc{Gz(pS sM uP uT vO vP vQ vU vW yH yL zH) Db(pS sK sO vB vH vT vW wQ yK tL xA) Ki(qB sO uM uN wC wF wQ yH tL xA) Kr(uN uU vW wF wG wL yK zH tL) Ue(sO uZ vB wF zH tL) jY(qO qZ tX uM yD yK) Qw(wF wL tL xA) cC(rV uG vW xA) uN(cB Ky Nj Um) Rb(rU tX wJ) Nt(tO yH) Me(sO wL) Na(sK vI) Hf(rQ rU) aZ(wQ yH) NuwG iAtV xArU} Qw{wQ(Co Dk Et Jh Jm Kf Of Om Oy) Ad(Ou rO rP tQ vW wJ yH) Jh(eZ uM vB vW wP zI xA) Me(rQ rU tQ tU wG xA) Ou(bF Bo Ch Et Jg Ss) Iq(hO qC rU rV xA) Pz(hL hO pY qB) xA(Cv Dk Ki Vt) Jt(rP rU wJ) cD(Hc Nx Rb) tL(Hw Jm Jr) Dc(hO qB) Ib(Jg Tt) Ki(qQ rU) BajP BbqQ QcqC JduM QueZ RjPf UkhO bLvB} Et{Nl(Ii Il Im Io Jl Ml Ng Nm Ny Og Po Qa) cC(hR jP qG qP wQ yD) Kk(Ib Nm Ou vI vQ) Ne(Ii Il Ml Og) Io(Ml Mp Nj Og) Ks(jM Me qQ tF) aK(rU uG vP vV) dB(tO wC wJ wL) iO(qO qP rV) qG(Kr Mp Uv) Ii(Nh Nj) iJ(rV yL) rU(gW Hu) GztM MpIj NdOg IkOu KrvW UvrV aUuG iAqT} aC{cZ(Aj Ao Aw bF bX cE cF Cp Dc dD De Dg Di Dl) cB(Al aX aZ bF bX cE cL cN Cv Dc) bX(aZ Ba bE bF Bo cA cE Ch) cF(aZ bF cA cE cL cN) bE(cE cT dD) Ch(aZ cN) BocN ExcD HfvB JdvW UfwQ bGcE nDqT} Uf{wJ(Bb Db Hf Js Ki Nd Nm Qd qW) cC(hA hR Me tO wD wK) Db(hA jO Me wK wQ) Mp(tT uW wD wK wQ) Kr(jO rU rZ wB zA) dB(tO wG wL) xA(Js Me Uv) wK(Ki Nt) UepS} nK{Ml(Hu Jj Jn Jr Js kG kO Lx lY mF Mn Mr Mz nC nH Nj nL Oi Oz Vs) Lx(Ij Im Iu Iv Jn Js Mq Qb) Js(Hv Mn Nr Nv) Vs(Ib Id Ub) Il(Cq Nr) BaMq NmMn} Ad{Gz(eZ hL jG pY sK sO vV vW yJ) Nt(eT hA iC jM jT pY) Ex(eZ lO pY qT uR) Kr(hO qO rQ rU rV) Db(eZ hO rV) Ib(aZ Ki) HfxA cCeZ} Jt{cC(fY pS qA rN uG wJ wQ yD yL zA) Ue(rR uM uZ wD wF wL yL) hO(Db Gz Kr Na Uv) dB(rN rU wQ yE) Kr(sO uL vB) rV(Db Hf) GzuR} Hf{vB(aP bW cN cR De iO Jd Ug uX) Cv(jY qU rX wQ) Me(bP cD cE dD) hO(Aj Jd Pz) xA(Dk Jh kQ) qU(Pf qT) KqjM OuqT aPwH oKuW} jP{mF(aO bL cE cG cW dF fP hC) nR(bG bI bL bQ cR cW iZ) cW(kP lX mM Of) mM(bC bG bI) bL(kO mZ) gL(kO mZ) kC(cG hG)} Ib{Tt(Cv gL Hu Ik Jd Jg Kf Kx Mg Ml Rb Ss Uk tF) Jd(aZ bF bU bX cB cF Ki) kG(Dc gL) BabX JgKk} Kr{Dd(sO tR tX vB vI wL) Kl(uP uW vW tM) Ao(vW wB) Bb(rR rV) Jg(eZ qG) CvsO HbrV KquW bWvW dBwH} dB{qX(bG eD iC lM qU rX) wL(Hw Iq Is Kc Nt) No(wF wH) Iq(wG wQ) NmwQ NtwH ItwG JdzA rZlM} qT{nD(aG bL cI cP gW iJ) iA(Kf Kg Lh Pa Tv) kO(aK dN kS) Js(Jr Kg) BbNt DbqU} Ex{gW(aU aV cD cY) nN(Iv Mh mW Nf) hO(Cv Jn kQ oN) xA(Dc Jh) TzsC JdyK KiuV} Db{hO(Aj Jd Pz xA) wQ(Jl oH Vp) Me(Kq Ou) Li(jM qU) UbuL RbcD JgqG PfqU wHoK} Ki{Jd(hO pS qQ rU sM uI uM wC yL zG) Jh(qG qQ uM uY zG xA)} Nt{jT(Ba Jg Ke Kf Kg Kq Nx) Uu(tU vP vW) Bb(qX vB) Kq(hA Me) QuwK} cC{Dd(hO rO rU xA) Pf(eD hR lN) Ub(wL yL) qG(Dk Jg) NmwQ MetL KqqX} mF{jE(cW Ih Ir Lx Mn Nn Nq Nr Pe Po Qa Qb Qe) PoLx} No{Iq(rO rR rU yE) Bb(qH vS xA) vI(Jd Jr) IjhL UuvW jFxA} bF{bX(aH aW aZ cF) cF(aH bG cV) nR(Nj Oi) aHcB eDkK} kO{kS(lM qX rA) bL(jH jK) PoLx HciP aOlM cSlK cWjG qXjQ} St{vW(Ba bW Dg Kl) aO(uM wB xA) IqzI IuwL KfxA} rU{vP(Bb Jr Kf) gW(vI wL) NaIq JrxA KkPj UmyK aUzA} Ml{Nl(Io Nc Ni Nk Og) Nh(Io Og) BaiA NeOg} bW{Mp(uN wD wG) vW(qC Up wG) AavV UexA RbvB} cW{hA(Kp Kx lM) eD(kI mH) lX(iC lK) PcrX lYjD} Bo{gW(Al aU aV bP cY dR) MeOu TnqX} nR{Vs(Lv nD Nj) Nl(cE oN) NmoN NjcG OicE} Na{Dc(hO qB) Pz(hO qC) BbqX KqjM} Um{zH(Jd tL) qC(Kf vU) AatL IvqB} kG{Oi(jE lK) LvOu IojT JjhV} Aa{uW(vB wG) aRmS rBkC} Po{Lx(lY nC nH nL)} cF{cE(bG bX cU) cLcU} oN{fP(hO qI) kN(aA cV)} Gz{Jj(vT yL) nNmW} Lu{KnnN VomZ nIiP} Pc{hR(hG To) rXoE} aZ{IswQ fYvB rZlM} iO{Hw(wF wL) KfzA} xA{BbPk TjPa MeoH} Mp{NnuW oHuN} Ue{NmwQ KjtL} Tt{MnqQ JsOh} Ik{HbqC HcdD} Rb{JdrT OgcD} Jr{IhuW JsvB} Kk{KfqC mIiP} Uk{wKjH yKrB} hO{NbfP PzUv} DdMetR GpaKgW NlcMlY OaWnbO UugLmZ aNmPqY aOnIlM aWkKlK bIkFlL bLnDjH cBcLcU

Constrained panels with 2 analytes, where 1.0E-6 >= 'model p-value' > 0. Contains 4 panels of 155,335 total panels evaluated. : iH(qU qX rX) OnUs Constrained panels with 2 analytes, where 1.0E-5 >= 'model p-value' > 1.0E-6. Contains 38 panels of 155,335 total panels evaluated. : Cw(aC hL hO jM qD qG qQ Qz rN uY wJ wQ tL xA) Ly(cC cD dJ Ok) nT(Ba cG cL dG) In(Ne Nh Nl) Qz(Bo On Ou) aC(bE Bo cF) Vq(rU rY) BanO LxnF UcOn NxUs cFdJ Constrained panels with 2 analytes, where 1.0E-4 >= 'model p-value' > 1.0E-5. Contains 241 panels of 155,335 total panels evaluated. : Qz(aN Ao Ap Ar Ba Bb bF cC cD Ch Co Cv dD dJ Ed Et Fw Gp Hq Hu Ic In Jd Jh Ki Kq Mc Ml Mv Ne Of Om Oy Pg qD Qg Rc Rj Us) Ly(aN Ap Ar aX Ba bF Bo bX cE Cw Db Et Fw Gp Ic In Ne Nh Nj Nl Og Us) Ic(Ar bF Bo bX cD cE cL Cv Cw dJ Et In Mc Ml Of On Ou Rb Uf Us) nF(Ba Bo Fr Jq Ml Mn Mr Mt No Nr Nv Nw Nx Ny ON Pf Po) Cw(eD hA hR Ib iC iJ In jO jP qU qX rU rV rZ vT tF) nT(bF bW bZ cE cH cN dF dH dJ gL hB iZ Kd oF oN Qy) Ok(Ii In Io Ml Mn Nd Ne Nf Ng Nh Nj Nl Ny Og) aC(Ad Aj Ap aZ Ba bF bX cB cE Ch cZ dJ Fw) iH(ED hR lM lN qQ rU rV uM vB wH) Ed(bW cD cE cN dJ Ex On qT) dJ(bU bX cB Fw gW hR rZ) nO(bF cE cG cH cL oN) On(Fw iA Ou Ql Qw) Vq(qD qU rZ vB xA) Ml(Ne Nh nK Nl) Us(lM lO qT qX) cB(bF cE cL Fw) cF(Ba bF Bo cE) nJ(jE qT Vs tF) Et(Io Ne Nl) In(Ad Kf Tv) Og(Ne Nh Nl) bX(bF cE) nB(Kk Kn) ApiJ BaiA BogW FwqT MeKz IbTt QwqD dBqX Constrained panels with 2 analytes, where 1.0E-3 >= 'model p-value' > 1.0E-4. Contains 801 panels of 155,335 total panels evaluated. : Us(Ad Ao Ap Bb Bo Cv Cw Dc Dd Dg Dk ED Et Hc hO hR Ib Is Iu Je Jg Jt Kf Kl Kq Lh Lx Mb Me Ml Mq Mr Mu Mv nA Nc Ne Ng nJ Nl Nv Nw Ny Of Ok Om Oy qD qQ qU Qx Rb rU rX Uf Ut uW uX Vs wQ zA xA) dJ(aK aQ bF Bo cE cK cP cT fP Gp Hc Is Jd Ki Kk Kq lM lN Ml nB Ne nJ Nl nO Of Ok On Ou Qg QW qX Ra Rb Rj Ss vB wG) Ic(aC aN AP aZ BA bG cN DD Ed Ex Fn fP Fw gL hB Hc hG Ib iH Jd Kc Kf Kq Kx Lu Lx Me Mv Ne Nx Ql Rg Rj Uk) In(Al Ar Ba bF Bo bX cF Co Cp Cv Dc Dd Et Ex fP Ha Hc Jd Je Kg Ki Kn Kq Kx Mr nA Nd Nj nK Ph Rb St Tn Uf Um Ur Vs) nT(aJ aM AP Aw aY bC bL Bo cM Cp dD Dg dL fP HC Id iO Ju Jv Kc Kk Kn Kz mP nF nJ nK qT Rg Ri Rj Ua Uf Ut Vs) nF(Ad Ap Ar Aw bF cE cG cL Cp Cw Dg Di Et Jg Ji Kk Kn Ko Lh Li Ms Mu Ne Nf NJ Nl Og Oi Ok Om Ow Pd Pe Qe Qz) Qw(Ap Ar Ba bF Bo cD cE Ch Cw Et Ex Hc Jg Kq lM Ly Mv Nc Ne Nl Of Ou Rj Ss Uf vB wQ xA) Nj(Ap Ar Ba bF Bo bX cE Ch Cv Cw Ed Et Fw Hc Hq Io Ml nB Nd Ne Nh Ni nK Og Ou Uf) On(aC aN As bX cC cD cF Cq Cu Dc dM Fy Ib iH Ki Kk Ks Qm Qu Rj Uc Vp Vv Tj) nO(aM bW cM dD dG gL hB hC iH iO iZ Kd Kn Kq nA nJ oF QT Qy Uf Ut Vq Vs) Ap(hA hO hR iA Ib iH jM Ou qC qD qG qU rB rO rU rV rZ vW wJ wQ tL xA tF) Fw(bF Bo bX cE cF cL Et fP gW Hc hG iH Kf Kq Lh Lx Nc Ne Nl Ok qX Rb Um) Ed(aC Ar aW bF bX cC cL Cw Et fP hB hG Ki nA nB Nc Ne Nl qX Uf Um) Et(Fy Ib Ii Ij Il Kk Ml Mn Mp Nd Nf Ng Nh Nm Nn Nq Ny Og Ou Ra) Vq(hL hO iC jY Ly Me qX rO rX uM vA vT vW wD wL wQ yH yK tL tF) nA(Ex Hu It Jj Jq Js Lu Lx Md Ml Mn Mr Nr Nx Ny Og Pf Po Vs Vu) Bo(aH aW Bg bU bX cB cE cK cL cP jM Me qU qX Rb tF) Ly(As Hf Jd Ki Ks Kz Ml Nc Nd Nf Ou Ow Ql Rc Rj Uf) bF(aH aW aZ bG bU cN cV gW iH Ma Ne nJ Nl nR Rb tF) bX(aW aZ Ba bP cB cF Ch cL cT fP Ib Ml Ne Nl Of) nJ(cE cG cL hA iO jl kO lM nB oN oP oQ rX Up) Cw(cF Fy gW jG Kk lN Mp oK Ou Ra Rb Ue Vv) Hf(eD hO Me qD qT qU qX vB wH wQ tL xA) Qz(aW bP cE cT qC qQ vW wJ wK wQ xA) cB(Ar aW aZ Ba bW cF cK cN cP Cv qX) nK(Hu

Figure 21 Continued

Jn Js Lu Lx Mn Mr Nf Nr Og Vs) Ok(Ij Il Jl Lu Mj Mp Nc Nm No Nq) nB(Kc Ld Lx Ow qT Qv rA Rj Tv Ub) qD(Db Dd Hb Iq Jt Na Pj Pk Um tM) cE(bG bU cK cU cV iH nR Rb tF) fP(bG bZ cD cF cO cS cU hO tF) Ib(Ad Ba Jd Jg Jt Kf kG oP) qX(aW aZ cC Db jE jF Ki lM) Ml(aC Ar iH Ki Kk Nd Um) Iq(hO Nd rU tV vB wD wL) Db(hO IM qT qU wQ xA) cF(Ad aW aZ cL cT dD) iH(Ba cD dD hO Ou tF) Bc(uN vW wL zH tL) Me(Ki Ks Nd Uf uW) gW(aK Al Ba Ch Gp) qT(kG kO nC nH nL) IM(bI cC cW dB iA) Ne(Ar Hq Il Io) Nh(Ij Il Io Nf) Nl(Il Io Nc Nk) Rb(bP cC cD dD) Kz(pS qQ rQ uG) kO(cH cM iZ oN) Nd(Hq Nf Og) Kk(Ar Kc vI) aC(cL cN Of) dB(hR qU rX) oN(kN nN nR) Ba(iJ tF) Cv(Ki Rj) Uc(vB xA) Kr(vB tL) Um(wL tL) Uf(wJ xA) aZ(hR wQ) cW(hA IN) hO(Ex Na) rX(aW bL) ArNr NtHc LxIY OfcD PkqC bWvW cGnR cLcU nNiZ

Unconstrained panels with 3 analytes, where 4.0E-15 >= 'AUC p-value' > 0. Contains 50,000 panels of 27,488,127 total panels evaluated. :
Cw{tL(aA aC AD aE AF aG aH al AJ aK AL aM AN AO AP aQ AR AS aU aV AW AX aY aZ BA BB bC bE bF BG bH bI bJ bL bM BN BO bP bQ bR bS bU bV bW bX bZ cA cB cC cD cE cF cG CH cI cJ cK cL cM cN CO CP CQ cR CS CT CU CV cW CX cY cZ dA DB DC DD DE dF DG dH DI dJ DK DL dM dN Dp dR eC ED EF Et EZ Fa Fb FN FP Fr Fw FY GL GP gW HA HB HC HF hG hL hO hP Hq HR Hu HV HW HX iA IB IC Id IH Ii IJ Ik Il Im In IO IP Iq Ir Is It Iu IZ JD JE JF JG Jh JI Jj JK JL JM Jn Jo JP Jq Jr Js JT JU Jv JY Kc Kd Ke Kf Kg Ki Kj Kk Kl Kn Ko Kp KQ KR KS Kx Ky Kz Ld Lh Li Lj IK IL IM IO Lu Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og Oh Oi OK Om ON Or Ou Ow Oy Oz Pa Pb Pc Pd Pe PF Pg Ph Pi Pj Pk Po pS Pz QA QB QC QD Qe QG QH qI QI Qm Qn qO qP qQ QT QU QV QW QX QY QZ RA RB RC Rf Rg Rh Ri Rj Rm rN rO rP rQ rR rS rT rU rV rW rX rY rZ sC sK sM sO Sr Ss St tN tO tQ tR tS tT tU tV tX Tz Ua Ub Uc Ud Ue Uf UG Uh uI Uk UL UM UN UO UP UR Us UT UU UV uW uX uY uZ vA vB vC vH vI VO VP vQ VS VT VU VV vW wB wC wD wE wF wG wH wJ wK wL wP wQ yD yH yJ yK yL zA zG zH zI yE tM xA Wm Tj tF) uY(aA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM CO CP CQ cR CS CT CU CV cW CX cY cZ dA DB DC DD DE dF DG dH DI dJ DK DL dM dN Dp eC Ed EF Et EZ Fa Fb FN FP Fr Fw FY GL GP gW Gz HA HB HC HF hG hL hO hP Hq HR Hu Hv HW HX iA IB IC Id IH Ii IJ Ik Il Im In IO IP Iq Ir Is It Iu Iv Iz jD JE JF JG JH JI Jj JK JL Jm Jn JO JP Jq Jr Js Jt JU JV JY Kc Kd Ke Kf Kg Ki Kj Kk Kl Kn Ko Kp KQ KR KS Kx Ky Kz Ld Lh Li Lj IK IL IN IO Lu Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pj Pk Po pS pY Pz Qa QB QC QD Qe QG QH qI QI Qm Qn qO qP qQ QT QU QV QW QX QY QZ RA RB RC Rf Rg Rh Ri Rj Rm rN rO rP rQ rR rS rT rU rV rW rX rY rZ sC sK sM sO Sr Ss tN tO tQ tR tS tU tV tX Tz Ua Ub Uc Ud Ue Uf UG Uh uI Uk UL UM UN UO UP UR Us UT UU UV uW uX uZ vA vB vC vH vI VO VP VQ VS VT VU VV vW wB wC wD wE wF wG wH wJ wL wP yD yH yJ yK yL zA zG zH zI yE tM xA Wm Tj tF) wQ(AA aC AD aE AF aG aH al AJ aK AL aM AN AO AP aQ AR AS aU aV Aw AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV cW CX cY cZ dA DB DC DD DE dF DG dH DI dJ DK DL dM dN Dp dR eC ED EF ET EZ Fa Fb FN FP Fr Fw FY GL GP gW Gz HA HB HC HF hG hO hP Hq HR Hu HV HW HX iA IB IC Id IH Ii IJ Ik Il Im In IO IP Iq Ir Is It Iu Iv IZ JD JE JF JG JH jI Jj JK JL JM Jn JO JP JQ JR Js JT JU JV JY Kc Kd Ke Kf Kg Ki Kj Kk Kl Kn Ko Kp KQ kR KS Kx Kz Ld Lh Li Lj IK IL IM IN IO Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nc Nd Ne Nf Ng Nh Ni Nj Nk Nl Nm Nn No Nq Nr Ns Nt Nu Nv nW Nx NY Oa OE OF Og OH Oi Ok Om On Or Ou Ow Oy Pa Pc Pd Pe PF Pg Ph Pi Pj Pk Po pS pY Pz QA QB QC QD Qe QG QH qI QI Qm Qn qO qP qQ QT QU Qv QW QX qY QZ RA RB RC Rg Ri Rj rN rO rP rQ rR rS rT rU rV rW rX rY rZ sC sK sM sO Ss tN tO tQ tR tS tT tU tV tX Tz Ua Ub Uc Ud Uf UG Uh uI Uk UL UM UN UO UP UR Us UT UU UV uW uX uZ vA vB vC vH vI VO VP VQ vS VT VU VV vW wB wC wD wE wF wG wH wJ wK wL wP yD yH yJ yK yL zA zG zH zI yE tM xA Wm Tj tF) rN(AA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV cW CX cY cZ dA DB DC DD DE dF DG dH DI dJ DK DL dM dN Dp dR eC ED EF ET EZ Fa Fb FN FP Fr Fw FY GL GP gW HA HB HC HF hG hL hO hP Hq HR Hu HV HW HX iA IB IC Id IH Ii IJ Ik Il Im In IO IP Iq Ir Is It Iu Iv IZ JD JE Jf JG JH JI Jj JK JL JM Jn JO JP JQ JR Js Jt JU JV JY Kc Kd Ke Kf Kg Ki Kj Kk Kl Kn Ko Kp KQ KR KS Kx Ky Kz Ld Lh Li Lj IK IL IM IO Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv NW Nx NY Oa OE OF Og OH Oi Ok Om On Or Ou Ow Oy Oz Pa Pb Pc Pd PF Pg Ph Pi Pj Pk Po pS pY Pz QA QB QC QD Qe QG QH qI QI Qm Qn qO qP qQ QT QU QV QW QX QY QZ RA RB RC Rf Rg Rh Ri Rj Rm rO rP rQ rR rS rT rU rV rW rX rY rZ sC sK sM sO Sr Ss St tN tO tR tS tT tU tV tX Tz Ua Ub Uc Ud Ue Uf UG Uh ul Uk UL UM UN UO UP Ur Us UT UU UV uW uX uZ vC vI VO VP VQ VS VT Vu VV vW wB wC wD wE wH wK wL wP yD yH yK yL zG zH tM Wm Tj tF) wJ(AA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ Cs CT CU CV cW CX cY cZ dA DB DC DD DE dF DG dH DI dJ DK DL dM dN Dp dR eC ED EF ET EZ Fa Fb FN FP Fr Fw FY GL GP gW Gz HA HB HC HF hG hL hO hP Hq HR Hu HV HW HX iA IB IC Id IH Ii IJ Ik Il Im In IO IP Iq Ir Is It Iu Iv IZ JD JE JF JG JH JI Jj JK JL JM Jn JO JP JQ JR Js JT JU JV JY Kc Ke Kf Kg Ki Kj Kk Kl Kn Ko Kp KQ kR KS Kx Ky Kz Ld Lh Li Lj IK IL IM IN IO Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Ne Nf Ng Nh Ni Nj Nk Nl Nm Nn No Nq Nr Ns Nt Nu Nv NW Nx NY Oa OE OF Og OH Oi Ok Om On Or Ou Ow Oy Oz Pa Pb Pc Pd PF Pg Ph Pi Pj Pk pS Pz QA QB Qc QD QG QH qI QI Qm Qn qO qP qQ QT QU Qv QW QX QZ RB RC Rf Rg Rh Rj Rm rO rP rQ rR rS rT rU rV rW rX rY rZ sC sK sM sO Sr Ss St tN tO tQ tR tS tT tU tV tX Tz Ua Ub Uc Ud Ue Uf UG Uh uI Uk UL UM UN UO UP UR Us UT UU UV uW uX vA vB vC vH vI VO VP vQ VS VT vW vW wD wE wF wG wH wK wL yD yH yJ yK yL zA zG zH zI yE tM xA Wm Tj) qG(AA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV cW CX cY cZ dA DB DC DD DE dF DG dH DI dJ DK DL dM dN Dp dR eC ED EF ET EZ Fa Fb FN FP Fr Fw FY GL GP gW Gz HA HB HC HF hG hL hO hP Hq HR Hu HV HW HX iA Ib IC Id IH Ii IJ Ik Il Im In IO IP Iq Ir It Iu IZ JD JE Jf JG JH JI Jj JK JL JM Jn JO JP JQ JR Js JT JU JV JY Kc Kd Ke Kf Kg Ki Kj Kk Kl Kn Ko Kp KQ KR kS Kx Ky Kz Ld Lh Li Lj IL IM IN IO Lv Lw Lx Ly Lz Ma Mb Mc Md Me Mf Mg Mh Mi Mj Mk Ml Mm Mn Mp Mq Ms Mu Mv Mw Mx My Mz Na Nb Nc Nd Ne Nf Nh Ni Nj Nk Nl Nm Nn No Nq Nr Ns Nt Nu Nv NW Nx NY Oa OE OF Og OH Oi Ok Om ON Or Ou Ow Oy Oz Pa Pb Pc Pd Pe PF Pg Ph Pi Pj Pk Po pS pY Pz QA QB QC QD Qe Qg QH qI QI Qm Qn qO qP qQ QT QU QV QW QX QY QZ RA RB RC Rf Rg Rh Ri Rj Rm rO rP rQ rR rS rT rU rV rW rX rZ sK sM sO Sr Ss St TN tO tQ tR tS tT tU tV Tz Ua Ub Uc Ud Ue Uf UG Uh Uk UL UM UN UO UP UR Us Ut Uu UV vA vB vC vH vI VO VP Vq VS VT Vu VV vW wD wE wF wG wH wK wL yD yH yJ yK zG zH zI yE tM xA Wm Tj tF) qD(aA aC AD aE AF aG aH al aJ aK AL aM AN AO AP aQ AR AS aU aV AW

Figure 21 Continued aX aY aZ BA BB BC bE bF BG bH bI bJ bL bM BN BO bP bQ bR bU bV bW bX bZ cA cB cC cD cE cF cG CH cI cJ cK cL cM cN CO CP cQ cR CS CT CU CV cW cX cY cZ dA DB Dc DD dE dF DG dH DI dJ DK dL dM dN dR eC ED EF ET EZ Fa Fb FN FP Fr Fw FY GL GP gW HA HB HC HF hG hL hO hP Hq HR Hu HV HW HX iA IB IC Id IH Ii IJ Ik Il In IO IP Iq Ir It Iu Iv IZ JD JE JF JG JH JI Jj JK JL JM Jn JO JP Jq JR Js JT JU Jv JY Kc Kd Kf Kg Ki Kj Kk Kl Kn Ko Kp kQ KR KS Kx Ky Kz Ld Lh Li lK IL lM lN lO Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pj Pk Po pS QA QB QC Qd Qe Qg QH qI QI Qm Qn qO qP qQ QT QU QV QW QX QY Qz RA RB RC Rf Rg Rh Ri Rj Rm rO rP rQ rS rT rU rV rW rX rY rZ sC sK sM sO Sr Ss St tN tO tQ tR tS tT tU tV tX Tz Ua Ub Uc Ud Ue Uf UG Uh uI Uk UL UM Un Uo UP UR Us UT UU UV uW uZ vA vB vH vI VO VP VQ VS vT VU VV vW wB wC wD wF wG wH wK wP yD yH yJ yK yL zG zI yE tM xA Wm Tj tF) xA(AA aC AD AF aG aH aI AJ aK AL AN Ao AP AR AS aV AW AX aY aZ BA bC bE bF BG bH bI bJ bL bM BN BO bP bQ bR bU bV bW cA cB cC cD cE cF cG CH cI cJ cK cL cM CO CP CQ cS CT CU CV cW Cx cZ dA dB DC DD DE dF dH DI dJ DK DL dM dN Dp dR eC ED EF ET EZ Ex EZ Fa Fb FN FP Fr Fw FY GL GP gW HA HB HC HF hG hL hO hP Hq HR Hu HV HW HX iA IB IC Id IH Ii IJ Ik Il Im In IO IP Iq Ir Is It Iu Iv IZ JD JE Jf JG JH JI Jj Jk JL JM Jn JO JP JQ JR Js JT JU JV JY Kc Kd Ke Kf Kg Ki Kj Kk Kl Kn Ko Kp KQ KR KS Kx Ky Kz Ld Lh Li Lj lK IL IM IN IO Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe PF Pg Ph Pi Pj Pk Po pS pY Pz QA QB QC Qd Qe Qg QH qI QI Qm Qn qO qP qQ QT QU QV QW QX QY QZ RA RB RC Rf Rg Rh Ri Rj Rm rO rP rQ rR rS rU rV rW rX rY rZ sC sK sM Sr Ss tN tO tQ tR tS tT tU tV Tz Ua Ub Uc Ud Ue Uf Ug Uh Uk UL UM UN UO Up Ur Us Ut UU UV uX uZ vA vB vH VO Vp VQ VS VT Vu VV vW wB wC wE wH wK wL wP yJ yK yL zG zH yE tM Wm Tj tF) hO(AA aC AD aE AF aG aH aI AJ AL aM AN AO AP AR AS aV AW AX aY aZ BA BB BC bE bF BG bH bI bJ bL bM BN BO bP bQ bR bS bU bV bW bX bZ cA cB cC cD cE cF cG CH cK cL cM cN CO CP CQ cR cS CT CU CV cW CX cZ dA DB DC DD DE dF DG dH DI dJ DK DL dM dN Dp dR eC ED EF ET Ex EZ Fa Fb FN FP Fr Fw FY GL GP Gz HA HB HC HF hG hL hP Hq Hr HV HW HX iA IB IC Id IH Ii IJ Ik Il Im In IO IP Iq Ir Is It Iu Iv IZ JD Je JF JG JH JI Jj JK JL Jm Jn JO JP JQ JR Js JT JU JV JY Kc Kd Ke Kf Kg Ki Kj Kl Kn Kp KQ KR KS Kx Ky Kz Ld Lh Li Lj IL IM IN IO Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv NW Nx NY Oa OE OF Og OH Oi OK Om ON Or Ou Ow Oy Oz Pa Pb Pc Pd pF Ph Pi Pj Pk Po pY Pz QA QB QC Qd Qe Qg QH qI QI Qm Qn qQ QT QU QV QW QX QY QZ RA RB RC Rf Rg Rh Ri Rj Rm rO rP rQ rR rS rT rU rV rX rY sO Sr Ss St tN tR tS tT tV Tz Ua Ub Uc Ud Ue Uf Ug Uh Uk UL UM UN UO Up Ur Us Uv uZ vA vB vC vH Vo VM VQ Vs VT Vu VV vW wB wD wE wK yD yH yJ yK zG zH yE Wm Tj tF) vT(AA aC AD aE AF aG aI aK AL aM AN AO aP AR AS aU AW Ax aY aZ BA Bb bC bE BG bI bL bM BN Bo bP bQ bS bU bV bW bZ cA cB cC cD cE CH cI cJ cK cL cM cN CO CP CQ cR CS CT CU CV cW CX cZ dA Db DC DD DE dF Dg dH Di dJ DK dL dM dN Dp dR eC ED EF EZ Fa Fb FN FP Fr Fw fY GL GP gW Ha HB HC HF hG hL Hq Hr Hu Hv Hw HX iA Ib IC Id IH Ii IJ Ik Il Im In Io IP Iq Ir It Iu IZ Jd Je Jf JG JH JI Jj JK JL jM Jn Jo Jp Jq Jr Js jT JU JV JY Kc Kd Ke Kf Kg Ki Kj Kk Kl Kn Ko Kp KQ KR KS Kx Ky Kz Ld Lh Li Lj IK IN Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Ne Nf Ng Nh Ni Nj Nk Nl Nm Nn Nq Nr Ns Nt Nu Nv Nw NX NY Oa OE OF Og OH Oi Ok Om ON Or Ou Ow Oy Oz Pa Pb Pc Pd Pe PF Pg Ph Pi Pj Pk Po pS Pz Qa QB QC Qd Qe Qg QH qI QI Qm Qn qO qP qQ QT QU QV QW QX QY QZ RA RB RC Rf Rg Rh Ri Rj Rm rO rP rQ rR rT rU rV rW rX rY rZ sC sK sM sO Sr Ss tN tQ tS tT tU tV tX Tz Ua Ub Uc Ud Ue Uf UG Uh uI Uk UL UM UN UO UP UR Us Ut UU Uv uW uX uZ vA vB vC vH vI VO VP VQ VS VU VV vW wB wE wF wH wK wL yD yH yJ yK yL zG zI yE tM Tj tF) uM(aA aC Ad aG aI aK aN aP aQ AR As aU aV aW Ax aY aZ BC bF BG bI bJ BN bO bP bS bU bW cA cB cC cE cF cJ cK cL cM cN CO cP CQ cR cS Cu CV Cx cY cZ dA dB Dc De Dg dJ Dk DL dM Dp dR eC ED EF ET EZ Fa Fb FN FP Fw FY GL GP gW Ha HB HC HF hG hL hP Hq HR Hu Hv Hw HX iA IB IC Id IH Ii IJ Ik Il Im In IO IP Iq Ir Is It Iu Iv IZ JD JE JF JG JH JI Jj JK JL JM Jn Jo JP JQ JR JT JU JV JY Kc Kd Ke Kf Kg Ki Kj Kk Kl Kn Ko Kp KQ KR KS Kx Ky Kz Ld Lh Li Lj IK IL IM IO Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv NW Nx NY Oa OE OF Og OH Oi Ok Om ON Or Ou Ow Oy Oz Pa Pb Pc Pd Pe PF Pg Ph Pi Pj Pk Po pY Pz QA QB QC Qd Qe Qg QH qI QI Qm Qn qO qP qQ QT QU QV QW QX QY QZ RA RB RC Rf Rg Rh Ri Rj Rm rO rP rQ tT Tz Ua Ub Uc Ud Ue Uf Ug Uh Uk UI Um Un Uo Up UR Us UU uZ vA vB vH vI Vo Vp Vq Vs Vt Vu Vv vW wL yH zH tM Tj tF) rT(aG aK aL aM Ao aP aQ Ar aU aV aW aX aY aZ Ba BC bE BG bH bI bJ bO bQ bV bW cB cC cD cE cF cG cH cI cK cL cM cN Co cP cR cS CT Cu CV cW cX cY cZ dA DB Dc Dd De Di dJ DK Dl dM dN Dp dR eC ED EF Et Ez Fa Fb Fn fP Fr Fw FY GL GP gW Ha HB HC hF hG hL Hq HR Hu Hv Hw Hx iA Ib IC Id IH IJ Ik Im In IO IP Iq Ir It IZ Jd JE JF JG Jh JI Jj JK JL JM Jn Jp Jq JR Js Jt Ju Jv JY Kd Ke Kf Ki Kj Kk Kl Kn Ko Kp kQ KR KS Kx Ky Kz Ld Lh Li Lj IK Lu Lv Lw Ly Lz Ma Mc Me Mf Mg Mh Mj Mk Ml Mm Mn Mp Mq Mr Ms Mt Mu Mv Mx My Nb Nc Ne Nf Ng Nh Ni Nj Nk Nl Nm Nn No Nq Ns Nt Nu Nv NW Nx NY OE OF Og OH Oi OK Om ON Or Ou Ow Pa Pb Pe PF Pg Ph Pi Pj Pk Po pS pY Pz QB qC Qd Qe QH qI QI Qm Qn qO qP qQ Qt QU qV QW QX Qy QZ RA RB RC Rf Rg Rh Ri Rj Rm rS rU rV rX rY sC sK Sr Ss tN tQ tU tV Tz Ua Ub Uc Ud Ue Uf UG Uh uI Uk UL Um Uo UP UR Us Ut UV uX vA vB vH vI Vo VP Vq Vs VV wC wD wG wL yH yL zG tM Tj tF) hL(AD aE AF aG aI aJ aK AL aM aN AO aQ aS aU aV aW AX BA Bb Bc bE BG bH bI bJ BN bO bQ bV bX cC cF cG CH cI cJ cM cO cP cQ cR cS cT CU CV cW Cx cY dA DB DC dE dF DG dH dI dJ DK DL dM Dp dR eC ED eF EZ Fb Fn fP Fw FY GL GP gW hA HB HC hF hG Hq HR Hu Hv Hx iA Ic Id IH Ii IJ Ik Il In IO iP Iq It Iu IZ Jd JE JfjG JH JI jK JL JM Jn jO Jp Jq Jr Js JT Ju Jv jY Kc Kd Ke Ki Kk Kl Kn Ko kQ KR KS Ky Kz Ld Li IK IM Lv Lx Ly Ma Me Mf Mg Mh Mj Mk Mm Mn Mp Mt Mu Mw My Na Nb Ne Nf Ng Ni Nj Nk Nl Nm No Nq Nt Nu Nv NW NY Oa OE OF Og OH oK oN Or Ow Oy Oz Pb Pd Pe PF Pg Ph Pj Pk Po pS pY qA qB qC Qd Qe Qh QI Qm Qn qO qP qQ Qt QU qV QW QX Qy Qz RB Rc Rf Rg Rh Rm rQ rU rV rW rX rY rZ sC sK sM sO Sr Ss St tN tO tQ tR tS tT tU tV Ub uL Um uN UO UP uR Us UT uU UV uW uX uZ vA vB vC vH vI vO Vp VQ VS Vt vU Vv wB wC wD wE wF wG wH wK wL wP yD yH yJ yK yL zA zG zH zI tM tF) vA(aG aK AL aM aP aQ Ar aU aV aW aY BA BC BG bH bO bQ bW cC cF cI cJ cK cM cN Co cP cR cS cT Cu Cv cW cZ dA Db dF Di dJ Dk Dp dR eC ED EF ET Ex eZ Fa Fb Fn FP Fr Fw FY GL GP gW Ha HB

Nb Ne Nf Nj Nn No Nq Nr Ns Nt Nu NW Nx nY OE oF OH oK oN Ou Ow Oz Pb Pe PF Pg Pk Po Qd QU qV QW QX Qy Qz RB Rf Rg Rh
Rm Tz Ue Uf Uh Uk Um Uo Up Ur Us Uv Vp Vq Vv tF) tS(Aa aK aV aW BC bI bL cC cM cR cS Cu Cv dA dB dJ dR Ed Fp Fw Fy Gl gP gW
Ha hC hG Hu Id IH Ij Ik iO Jd Je Jf Ji jK jL jM Jo jP Js Ju Jv Kd Ki Kk Kl Kn Ko Kr Ks Kx Ky Kz Ld Li Lj Lx Lz Ma Mh Ml Mm Mn Mp Mw
Nb Ne Nf Nj Nq Nr Nt Nu Nv nW Nx NY Oe oF Og OH oK oN Ow Oy Oz Pb Pe PF Pg Po Qd Qe Qh QU qV QW Qx Qy Rb Rf Rg Rh Sr St
Tz Ub Ue Uh Uk Um Uo Up Ur Us Ut Uv Vo Vq Vs Vv) sO(aK aV aW Bc cM cN cP cR cS Cu dA dJ dR eC Ed eF Ez Fb FP Fw GL GP gW
Ha hB hC hF hG Hu iA IH IJ Ik Im In iO iP lu iZ Jd Je Jf Ji JM Js JU Jv Kk Ko kQ KR kS Kx Ky Kz Ld Lx Ly Ma Mh Mn Mp Mt Nb Nf Nj
Nn No Nq Nr Nt NW nY OE oF OH oN Pb Pe PF Pg Pi Po Qd Qe Ql Qm qO qP QU qV QW Qy Qz RB Rf Rg Rh Rm St Tz Ub Ue Uf Uh Uk
Um Uo Up Ur Us Uv Vp Vq Vv tF) rW(Aa aI aK aU aW aZ Bc BG bQ bZ cC cE cG cO cP cR cS CU Cv dF dJ dL dR ED eF Ez fP Fw GL gP
gW hA hB hC hG Hu iA IH iJ iO IP Jd Je Jf jK jL jM Jo Js Ki Kk Kn Ko KR kS Ky Ld IM Lx Ma Mh Mj Mk Mn Mp Mt Mw Nb Ni Nj Nm Nn
No Nq Nt Nv nY OE oF OH oK oN Ow Oy Oz Pb Pe PF Pg Po Qd Qe Qt QU qV QW Qy Qz RB Rc Rf Rg Rh Rm St Tn Uk Uo Us Uv Vv Tj
tF) eZ(Ad Aj aK aN aU aW BC bF bI bQ cB cC cG Ch cI cJ cP cR cS CU Cv dA DC Dd dH dJ Dk dL dR eC ED Fn Fw Gl gP HA Hf hG Hr Hu
hX iA Id Ih Ik Im iO Iq Jd JE Jf Ji jK jL jM Jn Js jY Kk Kn Kr kS Ky Ld Lj Ma Mj Mk Mp Mv Nf Nn No Nq Nr Nt Nv nY Oa Oe oF Oh oK oN
Ow Pb Pe Pf Pg Pk Po Qd Qe Qm qU qV QW qX QZ RB Rg Rh rQ rX rY St Ud Uh Uk Uo Up Us Uv uZ Vv Tj) pY(AD aI aK aM aN Ar aU
aV bA Bc bF bQ bV bZ cE cF cG cI cJ cO cP cS cT cW cY dA DC Dd dF dG dH dJ dR Ed Ez FP Fw fY Gl gP gW hA hB hR Hu iA iJ Ik iO Jd
JE Jf jG jK jL jM Jp Js Kk Kl Ko kQ KR Ky Kz Ld Lx Ly Ma Mh Mj Mp Nb Ne Nf Nj Nl No Nq Nr Nt nY OE oF Og oH oK oN Ow Oy Oz Pb
Pe PF Pg Pk Po Qd Qm qP QU Qw qX Qz Rb Rf Rg Rh Uh Uk Um Uo Us Uv vl Vq Vv) vl(aK aU aW Bc bI cM cO cP cR cS Cu Cv dA dJ dR
ED Ex Fr Fw Gl gP gW hB hC hG Hu iA Id IH iJ Ik iO Iz Jd Je Jf Ji jK jM Js JU JV Ke Kk Kl Ko Kr KS Kx Ky Kz Ld IK Lx Ma Mh Mk Mm
Mn Mp Mt Mw My Nb Nj Nn No Nq Nt Nw nY Oe oF Og OH oK oN Ow Oy Oz Pa Pe PF Pg Pk Po Qa Qd Qe Ql QU qV QW Qx Qy Rf Rg
Rh Rm St Tz Ue Uh Um Uo Up Ur Us Vo Vq Vs Vv tF) uV(Aa aK aU aV aW Bc cF cM cP cR cS Cu dA dJ dR eC Ed eF FP Fw GL gP gW hB
hG hR Hu iA IH iJ Ik In iO Jd Je Jf Ji jK JL jM Js JU Jv Ki Kk Kl Kn Ko Kr kS Ky Kz Ld Lx Ma Mc Ml Mn Mp Mt Nb Nj Nn No Nq Nt Nu
NW nY Oe oF Og OH OK oN Ow Oy Oz Pb Pd Pe Pf Pg Po Qd Qe Ql QU qV QW Qx Qy Qz Rb Rf Rg Rh St Tz Ue Uh Um Uo Up Ur Us Uv
Vq Vs Vv) uU(aK aV aW aZ Bc bG cF cM cP cR cS Cv dA dJ dR eC Ed eF Fw GL gP gW Ha hF hG Hu iA IH iJ iO iP Jd Je Jf Ji Jl jM Js jT Ju
Kk Ko kQ KR kS Ky Kz Ld IK Lx Ma Mn Mp Mr Mt Nb Nf Nj Nn No Nq Nr Nt Nu nY Oe oF OH oK oN Ow Oy Oz Pb Pd Pe PF Pg
Po Qd Qe Qm QU qV QW Qx QY Qz RB rC Rf Rg Rh St Tz Ue Uh Uk Um Uo Up Ur Us Uv Vp Vq Vs Vv) rQ(aK Ar aU aV aW Bc bG bQ cE
cP cR cS Cu Cv dA dC dF dJ dR ED eF Ez FP Fw Gl gP gW hB hC hG hR Hu iA iH iJ Ik iO Ip Jd Je Jf Ji jK jL jM Js Kk Ko KR kS Ky Kz Ld
IM Lx Ly Ma Mh Mj Mn Mp Mq Mt Nb Nf Nj Nn No Nq Nr Nt Nu nY Oe oF Og OH oK oN Ow Oy Oz Pb Pe PF Pg Po Qd Qm QU QW Qx
Qy Qz RB Rf Rg Rh St Tz Ub Ue Uk Um Uo Ur Us Uv Vq Vv) wH(aK aV aW Bc bL bV cI cJ cM cP cR cS Cu Cv dA dB dJ dR Ed eF FP Fw
fY Gl gP gW hG Hu iA IH iJ Ik iO iZ Jd Je Jf Ji jK jM Jn Js Ju Ke Kg Ki Kk Kl Kn Ko Kr Ky Kz Ld Lu Lx Ma Mn Mp Mt Nb Nj Nn No Nq Nr
Nt Nu NW nY Oe oF Og OH oK oN Ow Oy Oz Pb Pe PF Pg Pj Po Qd Qm QU qV QW Qx Qy RC Rf Rh St Tz Ue Uh Uk Um Uo Ur Us Ut Uv
Vq Vs Vv) zI(aK aU aV aW Bc bQ cG cN cP cR cS Cu dA dJ dR eC Ed FP Fw GL gP gW hB hF hG hR Hu iA IH iJ Ik iP iZ Jd Je Jf Ji jK jM
Js Ju Jv Kk Ko Kp Kr kS Kx Ky Kz Ld Lx Ma Mh Mn Mp Nb Nj Nn No Nq Nr Nt Nu nW nY OE oF Og OH oK oN Ow Oy Pb Pe PF Pg Po Qd
Qe Qm QU qV QW Qx Qy Qz RB Rf Rg Rh St Tz Ue Uh Um Uo Up Ur Us Uv Vq Vs Vv tF) sK(Aa aK aU aV aW Bc bQ cM cP cR cS cY dA
dJ dR eC Ed eF fP Fw Gl gP gW hG hR Hu iA iB Id iH iJ Ik iO Jd JE Jf Ji jjM Js JU jV jY Ki Kk Kl Ko Kp Kr kS Ky Kz Ld IK Lx Ma Me Mg
Mm Mn Mp Mt Nb Nf Nn No Nq Nr Nt Nu nY Oe oF Og OH oK oN Ou Ow Oy Pb Pe PF Pg Po Qd Qe Qh QU QW QX Qy rC Rf Rg Rh St
Tz Ub Ue Uh Um Ur Us Uv Vq Vv) sC(Aa aK aW Bc cC cM cN cP cR cS Cv dA dD dJ dR eC Ed eF FP Fw Gl gP gW hG hR Hu iA Id IH iJ Ik
iO Ip Jd Je Jf Ji jL JM Jo Js JU Jv jY Kk Ko Kr KS Ky Ld Lx Ma Me Mn Mp Mt Nb Nf Nj Nn No Nq Nr Nt Nu nW nY Oe oF Og OH oK oN
Ow Oy Pb Pe Pf Pg Po Qd Qe Ql QU qV QW Qx Qy Qz rB Rc Rf Rg Rh St Ub Ue Uk Um Uo Ur Us Vq Vs Vv) uP(aK aU aV aW Bc bI bQ
cM cR cS Cu dA dJ dR Ed Ex Fw Gl gP gW hB hG hR Hu iA iB IH iJ iO Jd JE Jf Ji jjM Jn Js Ju jY Kk Ko Kp KR kS Ky Kz Ld IK Lx Ma Me
Mh Mm Mn Mp Mt Mw Nb Nf Nj Nn No Nq Nr Nt Nu nW nY OE OF OH oK Ow Pa Pe PF Pg Po Qb Qd Qe Qh QU QW qX Qy rB RC Rf Rg
Rh Ue Uh Um Uo Up Ur Us Uv Vq Vs Vv Tj) yK(aI aK aU aV aW aZ Bc cR cS Cv dA dJ dR eC Ed Ex FP Fw Gl gP gW hB hF hG Hu iA IH iJ Ik iO Jd Je Jf Ji jK jM Js jT Ju Kk Kl Ko Kr kS Ky Kz Ld Lx Ma Mn Mp Mt Nb Ne Nf Nj Nn No Nq Nr Nt Nu NW nY Oe oF Og OH oK oN Ow Oy Oz Pb Pe PF Pg Pk Po Qd Qe QU qV QW QX Qy Qz RB Rf Rg Rh St Tz Ue Uh Uk Um Uo Ur Us Vq Vs Vv) zH(aK aU aV aW Bc bI bQ cM cP cR cS Cu Cv cW dA dJ dR eC Ed Ex FP Fw GL gP gW hB hG Hu iA Id IH iJ Ik iO Jd Je Jf Ji jK jM Js jT JU Jv Ki Kk Ko Kr kS Ky Kz Ld Lx Ma Me Mn Mp Mt Nb Nj Nn No Nq Nr Nt Nu nW nY OE oF Og OH oK oN Ow Oy Oz Pb Pe Pf Pg Po Qd Qe QU qV QW Qx Qy Qz rB Rf Rg Rh Ub Ue Uh Um Up Ur Us Vq Vs Vv) yL(aI aK aV aW Bc bQ cC cE cG cI cM cO cP cR cS Cv dA dJ dR eC Ed eF fP Gl gP gW hB hC hF hG Hu iA Ic IH iJ iO iP Iq iZ Jd Je Jf Jj jK jM Js Ju jV Ki Kk Ko Kp kQ KR KS Ky Kz Ld Lx Ma Mh Mm Mn Mp Mt Nb Nj No Nq Nt Nv nW nY OE oF oK oN Ow Pe Pf Pg Po Qd Qe QU QW QX Qy Qz Rb Rf Rg Rh Tz Ue Uh Uk Um Uo Up Us Uv Vq Vv tF) sM(aK aV aW Bc cM cR cS Cu Cv dA dJ dR eC Ed Fy GL gP gW Ha hB hF hG hR iA iH iJ Ik iO iP Jd JE Jf Ji jL jM Js JU jY Kk Ko Kp KR KS Ky Kz Ld Lx Ma Mn Mp Mt Nb Nf Nn No Nr Nt Nv NW nY Oe oF OH oK oN Ow Pb Pe PF Pg Po Qd Qm QU qV QW Qx Qy Qz RB Rf Rg Rh St Tz Ub Ue Uh Uk Um Uo Ur Us Uv Vs Vv) pS(aK aV Bc cE cF cG cM cP cR cS cY dA dJ dR Ed Fp Fw fY Gl gP gW hA hG hR Hu iA IH iJ iO Jd Je Jf jK jM Jn Js JU jY Ki Kk Ko Kp kQ KR Ky Kz Ld lK Lx Ma Mn Mp Mt Nb Nj No Nq Nr Nt Nu nW nY OE oF Og oH oK oN Ow Oy Pe Pf Pg Po Qd Qe QU qV QW QX Qy Qz rB rC Rf Rg Rh St Tz Ue Uh Um Uo Ur Us Vq Vv tF) uR(aK aV aW Bc bQ cM cR cS dA dJ dR eC Ed eF fP Fw GL gP gW hB hF hG Hu iA Id IH iJ Ik iO Jd Je Jf Ji jL jM Js JU Ki Kk Ko Kp KR kS Ky Kz Ld Lx Ma Mn Mp Mt Nb Nj Nn No Nq Nt NW nY Oe oF OH oK oN Ou Ow Pe PF Pg Po Qd Qe QU qV QW Qx Qy Qz rB Rf Rg Rh St Tz Ub Ue Uh Uk Um Uo Ur Us Vq Vs Vv tF) uX(aK aW Bc cM cN cO cR Cu Cv dA dJ dR Ed eF Fp Fw Gl gP gW hF hG Hu iA IH iJ Ik In iO iZ Jd Je Jf jL JM Jo Js Ju JV Ki Kk Ko Kr Ky Kz Ld Lx Ma Mn Mp Mt Nb Ng Nj Nn No Nq Nr Nt Nu nW nY Oe oF OH oK Ow Oy Pb Pe PF Pg Po Qd Qe Ql QU qV QW Qx Qy Rb rC Rf Rh St Tz Ua Ue Uh Um Uo Ur Us Uv Vq Vs Vv tF) vQ(aK aW Bc bQ cE cM cR cS Cu dA dJ dR eC Ed eF FP Gl gP gW hB hG Hu iA iH iJ iO iZ Jd Je Jf Ji jK jM Js JU Jv Kk Ko Kp Kr kS Kx Ky Kz Ld Lx Ma Mn Mp Mt Nb Nj Nn No Nq Nr Nt Nu NW nY Oe oF Og OH oK oN Ow Oy Oz Pe PF Pg Po Qd Qe QU qV QW Qx Qy Qz rB Rf Rg Rh St Ub Ue Uh Um Uo Ur Us Uv Vq Vs Vv) wP(Aa aK aV aW Bc cR cS Cu Cv dA dB dJ dR eC eD Fw Gl gP gW Ha hC hG Hu Ic Id IH iJ Ik Im iO Jd Je Jf Ji jK jL jM Js JU Jv Kk Ko Kr Ky Kz Ld Lj Lx Ma Mn Mp Nb Nd Nj Nn Nq Nt Nu Nw nY Oe oF OH oK oN Pb Pe PF Pg Po Qd Qe Qm QU qV qW Qx Qy Qz Rb Rf Rg Rh St Tz Ub Ue Uh Uk Um Uo Up Ur Us Uv Vq Vv tF) vU(aK aV aW Bc bQ cM cP cR cS cW dA dJ dR eC Ed fP Fw Gl gP gW hB hC hG hR Hu iA IH iJ Ik iO iZ Jd Je Ji jM Js jT Kk Kl Ko Kr kS Ky Kz Ld Lx Ma Ml Mn Mp Mt Nb Nf Nj Nn No Nq Nr Nt Nu nW nY Oe oF Og OH oK oN Ou Ow Oy Oz Pb Pe Pf Pg Pk Po Qd Qe qO QU qV QW Qx Qy Rf Rg Rh Ub Ue Uh Um Uo Up Ur Us Vq Vs) wG(aK aW Bc bL bQ cM cR cS Cu Cv dA dB dJ dR Ed eF Fp Fw fY gP gW hB hC hG Hu iA IH iJ Ik In iO Jd Jf Ji jM Js jT Ju JV Kk Kn Ko Kr Kx Ky Ld Lx Ma Mn Mp Mt Nb Nj No Nq Nr Nt NW nY OE oF OH oK oN Ow Pb Pe PF Pg Po Qd Qe QU QW Qx Qy RC Rf Rh St Ub Ue Uh Uk Um Uo Us Uv Vq Vs Vv tF) qO(Aa aI aK aU aV aW aZ Bb

Figure 21 Continued

Figure 21 Continued vV wB wE wF wG wH wJ wK wP yD yJ yK yL zG zH zI) Kz(pS qB qG qH qI qQ qZ rN rP rQ rR rS rT rV rW sC sK sM sO tN tO tS tT tU tV
tX uG uL uN uP uR uT uU uV uY vC vH vO vP vQ vS vU vV wB wC wE wG wH wJ wP yD yH yJ yK yL zA zG zH zI yE tM) iA(qG qH qI qO qT
qV qW qX qY qZ rA rB rC rN rP rQ rR rS rT rV rW rX sC sK sM tN tQ tR tT tV uG uI uL uN uO uR uT uU uV uW uX uZ vI vP vS vU vV wE wF
wJ wK yD yH yJ yK yL zG zH tM) vU(Aa Ad Af Ap Ar Ax bI Bo bS bX cE cF cG cL cM Cs cX dF Dl Fn Hb hG iH Ij Io Iq It Jf Jq Jr Jt Jv Ki
Ky Lu Mp Nj Nn No Og Oi Ok Om pS Qv Qz Ra Sr Tz Ub Ue Ul Up Us Vo wH) hL(Ad Aj Ap Aw Ba Bg Ch Co Cp Ct Cu Dc Dk Fb fP Gz Ib
Iz Jd Jh Jk Jt jY Kf Kg Kj Kl Ko Lh Ma Mg Mw My Ng Nn Nr OF oK On Oy Pj Pz Qh qI Qu QV qY Qz rC rV Uf Uu) yK(Aa aH aI aM aP Aw
Ba Bb bQ bX cE cF cL cR dF dG dH DL dM hB iH Jd Jf Jq Jt Jv Ki Kk Kp Kr kS Ky Lx Mf Mp Mz Nu Pj Qn QV qW Qz Tz Ub uI Uk Ul Up
Us Vo zI) wG(Af aK An Aw Bc bU bX cF cG cL cM Cp cR cX De dF dJ Dl eC Fn Hb iH IO It Jd Jg Jq Jt Jv Ki Li Mj Mp My Nn Nt Nu Nw oE
oH On pS Qu Qv Qz tQ Tz Ue Uf Ul uW wJ) Jt(eT eZ hP pS pY qA qG qH qI qP qZ rN rP rQ rR rT rV rW sC sK sM tN tO tT tU tX uG uL uO
uP uT uU uV uW vI vO vP vV wC wE wF wH wJ yH yJ zG zH zI tM) Aw(eT hA qG qH qI qO qQ qZ rQ rR rS rT sC sK sM sO tR tT tU tV
tX uI uL uN uR uT uU uW vC vH vI vO vQ vS vV wB wE wJ wP yH yJ yL zA zG zH zI tM) cM(rN rP rT rV sK sM tN tO tS tT tU tV uG uI
uL uN uP uR uT uU uV uW uX uZ vH vI vO vP vQ vS vV wB wC wE wF wH wJ yD yH yJ yL zA zG zH zI yE tM) rV(Aa Af An Ap Ar bI bS
bX cG cR Db De dF Di Dk Dl hA hR iH Ij iO Iq It Jd Jq Jv jY Kf Kq Kr Ky Mb Mf Mp Mu Mz Nu Of Om qC qW Qz Tz Ul Up Us) yH(Af aK
Ap Ba bX cF Ch Cp cR cY Dk Dl dR fP gL gP hC Hw Jd Jf Jg Jh Jv Kp Mf Mp Ng Nj No Nu oF Om On Or Qz rB sO Uf Up Us Vs vV) Tz(qC
rP sC sK sM tN tO tQ tR tS tT tX uG uI uN uO uP uT uV uW uX vC vO vQ vS vV wB wC wE wF wH wJ wK wP yD yL zG zH zI yE) Qz(fN
pY qA qB qC qG qH qI qO qZ rN rP rQ rR rS rT rW sC sK sM tN tO tS tU uG uI uO uR vS wC wE wF wJ wK wL yL zG yE tM) iH(qI qZ rT rX
sC sK sM tO tV uG uI uL uN uO uP uR uU uW uX uY uZ vC vS vV wE wF wH wJ wP yJ zA zG zH zI yE) Aa(fY hP kI nB qH qI qZ rN rP rQ
rS rT rW sC sO tN tO tS tT uG uO uU uV vI vO vP vS vV wB wH wP yJ zG) hA(Ba bF Ch Co Cp dD Dk Ex Fr Iq Jh Mk Mv Ng Of Oy qB qG
QH qI qO qP qQ qZ rN rP rQ rR rS rT rW Tn) wJ(Ad Ap Ba Cp Cu Dg Dl dM fP Fy Gz Hf Ic Ij Iq It Jd Jg Jq Jv Kf Kg Kl Li Nd Ok Pz qW Uf
Up Us wF) Jv(qQ rP rW sK sM tO tQ tT tV uL uN uO uV uZ vC vI vO vP vS vV wE wF wK yD yJ yL zG zH zI) rT(Af Aj Ap bX Cp De Dl hP
hW Ij iP Iq It Jd jE jF Jg jP Jq jY Kl Kr Li IM IN qC Ul Uu) Jd(qA qB qC qI rN rS sC uI uL uN uO uP uR uT uU uV uW uX uZ vC vH vI vV
wE zG zI) qX(Bb bM bZ cC cG dF dH dJ dL Ed Fw Gp iC Iv jO Js jY Ki Kp Kr Oi To Us Vs tF) vI(Ad Af aU bI bX cE cF cG dF dJ dM iJ It Jq
Mp Na Oi On Qv Qw Ub Uf Uk Up Us) Us(rN rX sK sM tN tO tS tU tV uG uN uP uV uW uX uY uZ vH vP wF zG zI) qC(Ad bX Ch Cp Dc Dk
Fb Ib jY Kf Mg Of On Pj Pz Qc qI QV qW rC Uf) nB(aI aU Bc bJ bW cY cZ dJ iP Kc kE Kk Lv IX Me nA Nl nN oE oQ tF) uI(Ad Af aK Ap
aU aV bX Cp cY De Dk eC Ij Iq Is It Jh Jq Kf Oy Ue) Af(qH qI qZ rN rP rS rW sK sM uL uO uV uW uY vH vV yD zG zI) qB(Ad bS bX cL Dc
Dk Ib Ic jY Kf Ma Nn No Pj Pk Pz QV Uf) yL(An cC Cp cR dD hC hG Ih iJ iP Iq Jg Jh Jq kR kS Mf Ss Ue) wF(Ap Ba Bb Bc cD De iO iP Jg Jq
Li Mj Mz Nu oH rB Ue uW) qI(Bb De dJ dK Dl fY hW iB jD jE jO jY IM IN pY qA Ue Uu) rX(Ar aV bM cC cJ cR dA dJ dL dR iC iO Ng Pc
pF Ql Qw Ue) Dk(eT fN hP pS qH rR rS sK sM tO uL vH vS wH wP) tF(hR kC kE kG kI kN IW mE mH ml mT mZ nH nK nN) Jq(rN tO tS uL
uN uO uU uW uY uZ vC vV zG zI) nN(aJ bJ cQ Ed Ex gL Ic iZ Kk Ml Mt Oi oK oN) jY(bC eT eZ fN hP pY qH qO qP qQ qZ rN rP rQ) Ad(eT
eZ fN fY hP pY qA rP tO tT uO uV wK) Ba(pS qG qH qQ rS sK sM tU uY vH vO wH wP) Cp(qH qZ rP rS rW sK sM uL wE wH wP zI)
De(qG qH qZ tU uG uL uW uX uY uZ vH zI) zG(An cC cR Dl Hb hC hG Jf Kr Mz Om Pc) uV(bX cE cF cG cL Cs dF Dl Ki Ms Ul Up) Ap(qG
qH rP rR rS rW sC uX uY wE zI) uW(An bI Db dL Hf Kr Lx Me Mf Mp Rb) aK(jO qH qO qP rS sK sM vP vS wH) tO(cF cO dL iO Mz Nu Om
Qh qV tR) On(fN hP qA rP sM tN tT wK yD) sK(aV CT dJ Ef Hf Jh Ng Of) qV(eZ fY hP hR iC qA tN tT wK) dL(rP rR rW tN tT vH vV wK)
Ue(sM tS uG uX uY zH zI) Kr(pS rS sO vQ wE wH zI) bJ(kl IY mF mH mW mY nF) bX(hP pY qA qQ sM uR zH) rW(cG dF hP Ki kS Nj Or)
Ch(eT eZ fN hP sC tT) Ij(qG uT wB wK wP zA) qA(bS Dc Ib Pz qG rC) Ef(eT qH sM wH wP) Mp(rQ uO vH vV zH) Iq(qG rS sM uL wK)
cC(uL uZ vP vV zI) Dl(qG rS tS wK) Jg(qG rP tU uL) Of(eT qH sM wP) Om(uT vC wH zI) cG(qH rN uN vV) fY(cO cU dH dM) tN(cF Mz Nu
Pf) jO(dR gW Gz rN) kl(bE Gz Lv Nj) Qv(eT fN pY) Ki(tS tU tV) cR(lX nA rQ) hP(Kk rC Vu) hR(iC Qd Tk) iP(mF mH ml) wE(Co Li Nu)
wH(Bg Nu Or) rS(aV It IM) uY(cD Uu Uv) Pz(eT pY) Vs(nJ qH) dM(tQ tT) iC(Gz rC) iJ(uG uN) zl(Kf Li) sM(Hf Ul) qT(Ed Fw) jT(Ib Ic)
uL(Db eC) uO(aM It) pF(mI oQ) BbuU CtqH MeIY MfvV MzrQ SsrP OrvS PjwK blrN bMvH dFuN hGuG iOzH rCjG jDqG wP) wQ(Ad AO Ar Ax aZ Ba Bc bW cI Co Cu Db Dc Dd Dg Ed Et Fb Fy Gp Hb Hq Hw Ii Ij Ik In Io Iq Ir Is It Iu Iv Jg JH Jj Jk Jm Jo Jp Jv Kc Kf Ki Kj Kl Ko Kq Kr Ks Kx Kz Li Ma Mf Mg Mk Mm Mn Ms Mv Mw Nb Nd Ng Nm Nn No Nq Nr Ns Nt Nu Nx Of Ok Om On Pa Ph Pj Qa Qt Qu Qz Rc Rf Rg sO Sr Ss Tz Uc Uf Ug Uk Ul Um Ur Ut Uu Vo) xA(Ad Aj Ao Ap Ar Bb Bc Ch Co Cp Cs Cv Dc Dd Dg Dl Ed Ef Et Fw Fy Gp Hb Hf Hw Ib Ic Id Ij Ik In Ip Iv Iz Jd Jg Jh Ji Jj Jm Jc Jp Jq Jt Ke Kf Kg Ki Kj Kk Kl Kn Ko Kq Ks Kx Ky Lh Li Lx Me Mf Mg Mm Nd Nh Nm Nn No Nq Nr Nu Nv Nw Nx Ok Om On Pa Pf Ph Pi Pj Pk Qh Qu Qw Qz Ra Rc Ss St Tz Uc Uf Ug Uh Uk Un Ur Us Ut Uu Vo Vt) uX(Aa Ad AJ Ao Ap Bc bV Co Cv Dc Dd DG Di Dl Ed Et Fp Fw Fy Hb Hw Ij Ik In Io Ip Iq It Iv Jd Je Jg Jh Jj Jm Jn Jo Jp Jq Jr Jt Ju Jv Kc Kf Kg Ki Kj Kn Kq Lh Li Lu Lx Md Me Mg Ml Mn Mp Ms Mx Nd Ni Nm Nn No Nq Nr Ns Nt Nu Nw Nx Oa Ok Om On Ow Pe Pj Pk Po Qh Qt Qu Qy Qz Rc St Tz Uc Uf Uk Ul Un Ur Us Uu) uW(Aa Ad Aj Ao Ap Ar aZ Bc Dc Dd Dg Di Dl Ed Et Fw Fy Ha Hb hL Hu Hw Id Ij Ik Ip Iq It Iv iZ Jd Jg Jh Jj Jm Jo Jp Jq Jr Ju Kc Kd Kf Kg Ki Kj Kl Kq Kr Lh Lu Lx Me Mg Mn Mp Ni Nm Nn No Nq Nr Nt Nu Nv Nx Ok Om ON Pk Po Qb Qe Qh Qt Qu Qy Qz Rb Rc St Tz Uc Uf Uk Un Up Us Uu) uZ(Ad Aj Al Ao Ap Ax Ba Bc Co Cv Dc Dg Dl Ed Et Fa Fy Gp Hw Ib Ij Ik In Io Ip Iq Ir Is It Iu Iv Jd Jg Jh Jj Jm Jo Jp Jq Jr Kc Ke Kf Kg Ki Kj Kl Kq Lh Li Mf Mg Mm Mn Ms Mw Mz Nd Nm Nn No Nq Nr Ns Nt Nu Nv Nw Nx Ok Om On Pd Pj Qt Qu Qz Rb Rc Ss Tz Uc Uf Ul Un Ut Uu Vo) uO(Ad Aj Al Ao Ar Bc bW Co Dc Dg Dl Ed Et Fw Fy Gp Hw Ij Ik In Io Ip Iq Ir Is It Iu Iv Jd Jg Jh Jj Jm Jo Jp Jq Kc Ke Kf Kg Ki Kj Kl Kq Lh Li Mg Mm Mn Mp Ms Nd Nm Nn No Nq Nr Ns Nt Nu Nv Nw Nx Ok Om On Pd pF Pj Qh Qt Qu Qz Rc Ss Tz Uc Uf Ul Un Ur Us Ut Uu Vo) uN(Ad Aj Al Ao Ap Bc bW Cv Dc Dd Dg Dl Ed Et Fw Fy Hb Hu Hw Ij Ik In Ip Iq Ir Is It Iv Jd Jg Jh Jj Jm Jo Jp Jq Jr Jt Ju Kf Kg Ki Kj Kk Kn Lh Lx Mg Mn Mp Ms Nb Ni Nj Nm Nn No Nq Nr Nt Nu Nv Nx Ok Om On Oz Pe Pz Qa Qh Qu Qz Rc Tz Uc Uf Um Un Ur Us Uu) uY(Ad Aj Ao Ap Ba Bc Co Dc Dd Dg Dl Ed Fy Gp Hb Hw Ib Ii Ij Ik In Io Ip Iq Is It Iu Iv Jd Jg Jh Ji Jj Jm Jo Jp Jq Jr Jt Kc Ke Kf Kg Ki Kj Kl Kq Lh Lx Mg Mm Mn Ms Nd Nn No Nq Nr Ns Nt Nu Nv Nx Ok Om On Pa Pj Qh Qu Qz Rc St Tz Uc Uf Uh Un Ur Ut Uu Vo) uI(Ad Aj Al Ao Ap Ar Bc Dk Dl Ed Et Ex Fw Fy Hb Hw Ib Ih Ij Ik Ip Iq It Iv Jd Jg Jh Jj Jk Jm Jo Jq Jr Ju Kc Kf Kg Kl Kq Ky Lh Lx Md Mg Mn Mr Nb Nd Ni Nj Nm Nn No Nq Nr Ns Nt Nu Nv Nx Ok Om On Pb Pe Qu Qz Rb Rc Rf St Tz Uc Uf Uk Ul Un Ur Us Uu) wL(Ad Aj Al Ap Ar Bc bW Co Dc Dd Dg Dl Ed Et Fy Hb Hw Ib Ii Ij In Ip Iq It Jd JH Jj Jk Jm Jo Jp Jr Js Kc Kf Kg Kj Ks Lh Li Mg Mm Mn Ms Nd Nm Nn No Nq Nr Ns Nt Nu Nv Nx nY oH Ok Om On Pj Pz Qa Qh Qu Qz Rm St Tz Uc Uf Ug Un Ur) vA(Ad Aj Ao Ap Ar Bc bW Dc Dd Dg Dl Ed Fy Hw Ib Ii Ij Ik Ip Iq Is It Iv Jd Jg Jh Jj Jm Jo Jp Jq Jr Jt Kc Kf Kg Ki Kj Kl Lh Lx Me Mg Mm Mn Mp Ms Nd Nm Nn No Nq Nr Ns Nt Nu Nv Nx Ok Om Pj Qh Qt Qu Qz Rc Tz Uc Uf Ul Un Ur Ut Uu) Ad(eT eZ hL pS qC qD qG qH qI qO qP qZ rN rO rP rQ rR rS rT rW sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) Ed(eT fN pS qD qG qH qI qO qP qT qX qZ rN rO rP rQ rR rS rT rW rZ sC sK sM sO tN tO tQ tR tS tT tU tV tX uG uP uR uT uU uV vC vH vI vO vP vQ vS vT vU vV vW wB wC wD wE wF wG wJ wK wP yD yH yJ yL zA zG zH zI yE tM tL) Et(fY hL hP pS qD qG qH qI qO qP qZ rN rO rP rQ rR rS rT rW sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) Qz(hL hO nF pS pY qB qC qD qG qH qI qZ rN rO rQ rR rS rT rW sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) hO(Aj Ao Ap bX cI Co Cu Cv Dc Dl Ef Fn fP Hb Hq hR Hw Iq It Jd Jp Jt Ju jY Kf Ki Kk Kp Lh lK Mg Mn Mp Mw My Nb Nf Nj Nl Nm Nn Nx oH On Pe Pg Pj Pz Qu qV Qw qX QY rB RC rN rP rT rX sK Sr Uc Uf Um Ut wG yH) Tz(pS qD qG qH qI qU qX qZ rN rO rP rQ rR rS rT rW rX sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) Bc(pS qD qG qH qI qO qP qZ rN rO rP rQ rR rS rT rW sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) On(hL nF pS qC qD qG qH qI qZ rN rO rP rQ rR rS rT rW sC sK sM sO tN tO tQ tR tS tT tU tV tX uG uP uR uT uU uV vC vH vI vO vP vQ vS vT vU vV vW wB wC wD wE wF wG wJ wK yD yH yJ yK yL zG zH zI yE tM tL) Ap(fY hL hP pS qD qG qH qI qO qP qZ rN rO rP rQ rR rS rT rW sC sK sM sO tO tQ tR tS tU tV tX uG uP uR uT uU uV vC vH vI vO vP vS vT vU vV vW wB wC wD wE wF wG wJ wK yD yH yJ yK yL zG zH zI yE tM tL) Jj(pS qG qH qI qZ rN rO rP rQ rR rS rT rW sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) nF(Aa Af Aw Ba Bo cE cH dB Dg Di eD gW hR hW hX iB iC Ij iO jD jE jF jG jH jI jK jM jO jQ jR jT jU jV jY Kd Li lK lL lM lN lO Lw Lx Mm Mu Mz nB Nw Om oN Pf qT qU qV qW qY rA rC Rh rX rZ To Uf Vs) Aj(hL pS qG qH qI qZ rN rO rQ rR rS rT sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) Mg(pS qG qH qI qZ rN rP rQ rR rS rT sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) Lh(hL pS qD qZ rP rS rT rW sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) No(pS qG qH qI rO rR rS sC sK sM sO tN tO tQ tR tS tT tU tV tX uG uP uR uT uU uV vC vH vI vO vP vQ vS vT vU vW wB wC wD wE wF wG wJ wK wP yD yH yJ yK yL zA zG zH zI yE tM tL) Nu(pS qG qX rR rX sC sK sM sO tN tO tQ tR tS tT tU tV tX uG uP uR uT uU uV vC vH vI vO vP vQ vS vT vU vV vW wB wC wD wE wF wG wJ wK wP yD yH yJ yK yL zA zG zH zI yE tM tL) Jt(eT fY hL hP pS pY qA qB qC qD qH qI qO qP qZ rN rO rP rQ rR rS sC sK sM tN tQ tU tV uG uP uR uT uU vC vH vI vO vS vU vW wB wC wE wJ wK wP yH yJ yL zA zG zH zI yE tM tL) wG(Ao Ar aZ Ba bW Cp Cv Dc Dd Dg Dl Fy Hb Hw Ii Ij Io Ip Iq It Iv Jd Jg JH Jk Jm Jo Jp Jq Jr Kc Kf Kg Kl Mm Mn Nd Nm Nn Nr Ns Nv Nx Ok Om Qu Rc Ss Uc Uf Ug Un Ur Uu) Hb(fY hL pS qD qG qH qI qO qZ rN rO rP rQ rR rS rT rW sC sK sM sO tO tQ tR tS tV uG uP uT uU uV vC vH vP vQ vT vV vW wB wC wD wE wF wJ wP yD yH yK yL zA zI tM tL) Qu(hL pS qZ rN rS rT sC sK sM tN tO tQ tR tS tT tU tV tX uG uP uR uT uU uV vC vH vI vO vP vQ vS vT vU vV vW wB wC wD wF wK wP yD yH yJ yK yL zA zG zH zI yE tM tL) Un(pS qG qH qI qZ rO rP rQ rR rS rT rW sC sK sM sO tN tO tQ tS tV uG uP uR uT uU uV vC vH vI vO vP vS vT vU vW wD wF wJ wK wP yD yH yK yL zG zH zI yE tL) Dd(pS qD qG qI qZ rP rQ rR rS rT rW sC sK sM sO tS tU tV uP uR uT uV vC vH vI vO vP vQ vS vT vU vV vW wB wC wD wE wF wK yD yH yJ yK zG zH zI yE tM tL) Lx(nO pS qI rR sK sM sO tN tO tR tS tT tU tV uG uP uR uT uU uV vC vH vI vO vP vQ vS vT vV vW wB wC wE wF wJ wK wP yD yJ yK yL zA zG zH zI yE tM tL) Kg(hL pS qD qG rN rO rQ sC sK sM sO tO tR tS tT tV tX uG uP uR uT uU uV vC vH vI vO vP vQ vS vT vU vV vW wC wD wJ wP yD yH yJ yK yL zG zH zI tM tL) nB(eD gW hA hR hW hX iB iC jD jE jF jG jH jI jK jL jM jO jP jQ jR jT jU jV jY Kc Kk Kn lK lL lM lN lO Ou qT qU qV qW qX qY rA rB rC rX rY rZ To) Jm(pS rO rR rT sC sK sM sO tN tO tR tT tU tX uG uP uR uT uU uV vC vH vI vO vP vQ vS vT vU vV wB wC wF wJ wK wP yD yH yJ yK yL zG zH zI tM tL) zI(Ba bW Co Dc Dg Fw Hw Ii Ij In Ip Iq It Jd Jg Jh Jo Jp Jq Jr Jv Jy Kc Kf Kl Kx Mn Nb Nm Nn Nq Nr Nt Nv Nx Ok Om Rb Rc Ss Uc Uf Ur Us Uu) Ur(pS sK sM sO tO tR tS tT tV uG uP uR uT uU uV vH vI vO vP vQ vS vT vU vV vW wB wC wD wF wJ wK wP yD yH yJ yK yL zG zH yE tM tL) Ok(qD qG qH qI qZ rN rO rP rQ rR rS rT rW rX sC sK sO uG uP uR uT uU vC vH vO vQ vS vT vW wD wJ wP yD yH yJ yK zG zH yE tL) nI(gW hA hR hV hW hX iB iC jD jE jF jG jH jI jK jL jO jP jQ jR jT jU jV jY lK lL lM lN lO qT qU qV qW qX qY rA rC rX rY rZ) Om(qG qZ rS rT rW sC sK sM sO tO tR tS tT tU tV tX uG uT uU uV vC vH vI vP vQ vT vV vW wC wD wJ wP yD yK yL zA zH tM tL) uG(Ao Ar Cv Dc Dg Dl Fw Fy Hw Ij Ik Ip Iq It Jd Jg Jh Jo Jp Jq Jr Kf Kj Kl Kq Mn Ms Nm Nn Nr Nv Nx Qt Rc Uc Uf Uu) kO(eD gW hA hR

Figure 21 Continued hW iB iC jD jE jF jG jH jI jK jL jM jO jP jQ jR jT jU jV jY IK IL IM IO qT qU qV qW qX qY rA rC) Nm(qC qD qG qI qZ rN rO rQ rS rT sC
sK sO tX uP uT uU vC vH vI vQ vT vU vW wB wD wF wJ wP yH yJ yL zH tM tL) vC(Ao Dc Dg Dl Fy Hw Ij Ik Ip Iq It Iu Jd Jg Jh Jo Jp Jq Jr
Kf Kj Kl Kq Mn Nd Nn Nr Nt Nv Nx Rc Uc Uf Uu) jP(kC kE kF kG kI kN kP IW mH mI mM mP mS mT mU mW mY mZ nA nC nD nH nJ
nL nM nN nO nR nT oO oP oQ) sC(Aa Co Dl Fw Hw Id Ij Ik In It Jd Jg Jo Jp Jq Jv Kf Ki Ks Me Mn Ng Nn qC qD Qt Rc Ss Uc Uf Uu) Ms(pS
qG qH qI qZ rN rO rP rQ rR rS rT rW tQ tX uT uU uV vH vO vU vW wC wP yJ yK zG zH tM tL) Hw(pS qD qG rO rR rS rT sK tN tT tX uT uU
vH vP vQ vS vT vV wD wF wJ wP yD yH yL zH tM tL) rX(Cv hL Ib Io jM Jy kE kG kK Li lY mF mH mS mY nC Nf nJ Nr nU oQ Ou Pc Pf
qC qD qX Rg Vv) Fw(pY qG qH qI qP qT qU qW qX qZ rA rN rO rP rS rT rW uT vI vQ vS wD wJ yD yK yL yE tM) eD(Gz kF kG kK kP IW
IX IY mE mF mH mM mT mU mW nA nC nH nL nN nO nR nT nU oO oP qX) jH(kC kI kN IW mF mH mI mP mT mU mY nC nD nH nJ nL
nN nO nT nU qG tX uR vW yH yE tM) Jp(qD qG qH qI qZ rN rO rP rQ rR rS rT rW sO tQ tS uU vH vQ vT vU wB wD wJ yH zH) mF(hV hW
hX iC jD jE jF jG jM jO jQ jR jU jV jY IK IN qT qU KF kG Kn Ko Kp Lh Li Lw Lx Ma Mg Mn Mp Mt Mu Mv mW Ng nK Nq Nx Oh Oi On oP oQ Oy Qe Rg Ri Ss Tv Ua Uf Ut Vs) qT(aC aJ aK
aL An As aU aV Aw aZ Ba bG bL Bn Bo bS cA Ch cl cK cN cR cW cY Dc Dd De Di Dl dN dR eC gL hG HW Iq Jq kQ kR Lx Ng Nm oE oH
Pd pF Pz rY rZ Tz Ua Ub Ud Ue Uf Um Up Ur Ut Uv Vt Vu Wm) Ba(Aa aR AS aW aY Bb bR cD cl cN Co cZ eD Fr gL Hc Ic Io iZ Ju Jv Kc
Ko Kq Ks Ky Kz Lu lX lY Ma mF mM nB Nc NF nI Nj NK Nl Nm nO nU oH Oi pF Pj Qu Qy Ra Rc Rg Rj To Tr Ue Um Uv Vv) Aa(aJ AP Ar
Bg bL bW bX bZ cE cN Co dD dF DG dH dL Ed Ef Fa Fn fP Fy GL hB Hc Hf hG iZ Kf Kg Kj Kk Kl Ko Kp Kr Kx Ky Kz Ld oF oN Ql Qt Rg
Ss St Tv Ua Ue Um Uo Up Ut Vs) Lx(aE aS aY bU cN Cs cT cV cY cZ dE Ed Fb Fn Fw Fy gL Hc Ic Id IZ Jd Ju Jv Jy Kc Ke Kg Kk Kn Ks Ky
Kz pF Pi Qn Qw Qy Ra Rc Rf Rg Rj To Tr Tt Ua Uc Ue Um Uv Vo) Mu(aJ aK aL aS aV aY cl cV dR Ed Ez Fy gL Hb Hc Ic IZ Jd Ju Jv Jy Kc
Ke Kg Ko Kp Kq Ky Kz Ld Ou pF Pj Qu Qw Ra Rc Rg Rh Rj Rm To Tt Tz Ub Ue Uf Uu Uv Vt Vu) Uf(aE aR aS aV aW Bb Co cV cW Ed Fr
gL Hc Hr Hw Ic Id Ij Io It Jv Kc Ke Kg Ko Ky Li Lu Lv Ma mF Ml Mt My Nc nD Nj nK Nl Nm No Of Oh Oi Pa pF Qu Qy Rj To) Id(aE aP Bg
bL bS bW cD cM dF dG Ef Fn Fr gL hG Hu iJ iO Iq Iz Kf KG kK Kn Kp Kr Ky Kz Ld Lh Li ml Mp Mv mZ Ng nK Nn Nq nU Oh Pi Qd Qe Rj
Ua Um) Jv(AP Ar bF bL Bo cE DG Dk Fa Fr Gl hB Jg Ji Jp Jt Kn Ko Lh Li Ma Mn Mp Mt nD No Nr Nv Nx Ny ON oP oQ Pa Pd Po Qa Qe Qt
Sr St Tn Tv Ut) dG(aS Bo cD cl cV cY cZ gL Hc Ic iZ Kc Ko Lu lX Ma mF Mt Nc nD nF nl Nj NK Nl Nm nU Of Ou Qu Ra Rj To Tr Ub Vo)
Li(aS aW aY Cp cV Cx cY cZ Dk Dp Fb Fn gL Hc Ic iZ Kc Ke Kk Ks nD nK Oa Ow Qm Qw Qy Rj Tt Ub Uc Ue Us Uu Uv Vo) gL(Af bC bF
bW cE cH cN Dp Fr HC Ij Jy Kc Ko Kq Kr Lu Lw Mn Mp Mq nB nU Nw oN Ou Qt Qv Ra Ri Ub Ug Um Vs) cN(cW Fa Fr Hc Iz jL Kf Kg Kk
Kn Kq nK nU Or Ph Qa Qh Qx Qz Ra Rg Rj St To Tr Tz Ua Ut Vo Vu) Ij(Al Co Ed Fn Gl Hc Iz Kf Kg Kk Kl Kn Ko Kp Kx Ky Rg Rj Ss St Tv
Ua Ut Vs Vu) nK(Aw bZ cE Cp dF dH Fn Gl hB Hu Iz Kc Kk Kn Ko Kp Mn Or Ou Pj Ra Rj Ua Vs) Ju(Al bF cE Ji Kf Kn Lh Nc Nj Nk Nl Nr
Nx Oh oQ Pa Qa Qe St Uo Ut) cW(eD hR hV hW hX iB iC jH jK jM jP jR IK lL lN qV qX rA rC rX rY) Hc(aJ bL cO dH Di Io Iv Ji Kc Ks Lv
Ma mH Mp Nj Nm Nt oN Ri Ug) Tr(Ap bW cE Dg Di Dk hB iO Jd Ji Ma Mn Mp Mw Nq Nv On Ut Vs) Qy(Aw bF Bn bQ cE dF dH Fn hB Ji
Kn Ma Mn No Nv oP oQ Qe Ut) Oh(cH cM dL Dp Ed Fw Kc Ks oN Pi Ql Ri Rj Rm Ub Ud Vo Vu Vv) Vo(Ap bW cE Dg hB iJ iO Iz Ji Ma Mp
Nv Nx On Qe Qt Ss) iZ(bF bW cD cE cH Kq Lu Mn nU oF Qe Qh Rm Tz Um) mF(bZ cE Cp dH hB Iz Kf Kn Ko oF oN Ua Ut Vs) bL(hV hX
jH jI jK jP jT IL oN rB rC

Mp{uW(Aj Jq Nm Nn Uk) zA(Ad hG Kj) oH(uN vI) MgqA KjrV} Tt{Nb(qG qZ rN rQ rR rS rT rW) Mk(qG qQ) MnqQ WnhA} nC{iP(Kc Kn Ld) bP(hV rB) cR(lM rC) AsIK LxpF IojH aMrC cThX} Tk{jG(Co Jd Kg Qy rX rY) rZ(Ch lM) FwcF IvoF} Bo{Of(uW tM) eD(ml mY) mE( aW(bX rX) bL(rX vB) iO(oO wG) AauW CvUv G qQ qX rQ rR rV sC uM uT uW uX vQ vS wB wF wG wH wQ yD yH yL tL xA Tk) Ok(bO cV Fp Fr Gl Hq hR Ii Io Jl jT Kk Lu Mn Mp Ms Nf
Ng Nk Nm Nq Ny Pe qC qX rU Ue Uh wJ) Kz(Cv qB qG qO qZ rQ rZ sC tN tS tT tU ul uO uW uY uZ vA wB wD wF wH wK yE tL) bX(Ad
AN aZ BA bF Bg Bo bP cE dD fP Fw Gp Is Jg Jt Kc kO Lu Rb) Bc(qC rQ sO tO uG uM uT uU uX uY vB vH vS wC wD wQ yD yK zA zl yE)
Ue(Ad Kq mZ rX rY rZ sC sO tR uG uL uO uZ vS wH wL wP yL zH tM tL) jI(kC kE kF kK kN kP lW mE mH ml mM mP mT mU mW mZ
nM nN nU oO oP) Um(Ar Ba Cv Ex hO Kc Kq pS pY qC Qg tQ Ug uN vB vO wL yL tL xA) hR(As aZ bB bL cC Cv cW dD fP Fw Gp hG Il
Kc Kf Ml Pc To Uf Uk) qX(Bb Bo cC cW dD jE jF jR kG kO Kr lX mF mH mM nC nL nU Rj Tt) fP(aY bO cC cD cS cV dD eZ Fw hA Ib jM qC vW wL wQ) kO(bU cL cP Cv cW Dc dD gW hW iP lM oF Qy rA Ua Ut) Oh(Iz Kr Oa Ql Qx To Tv Ua Uc Ud Ul Un Up Vp tF) lY(dD IO iZ Ji Li Lx Ml Mt Nm Pf Qy Rj Ug Vo) hO(Ad bG Dc Dd Fn Gz Jd Jt Kf Lh Pj Pk Uf Uv) Ib(Aj Ba Co Dg Jt Kg Ko mZ oQ Qu Ss Tn Uf) bW(sK sM uL uN vA vB vU wG wJ wQ yH tL xA) Rb(aW bL bP cC Cv cW dD dM Ks Nt uX xA) Kr(sC sK sM tR tX vS wC yK yL zH tL xA) vB(Aw aZ cC cN De Ex Ir Jd Jq Na St Uk) Ba(gW hA iJ kI Na nY oE Po rZ Uv tF) nN(dD gL iO Kq Ks oF Ow Ql rA Rj Uf) vW(Ad Aj aO aP bC Fn hG Kf oH Qu Uf) cW(eD hA iC jG jH jM jY lM lN rX) Cv(kG Kk Ks Ql Ra Rj rX rY rZ) Nd(It Jp Jt Mb Mh Nc Nf Og Oz) cC(eD eZ lM qG rX uW uX wG tL) kI(cE cG cH dD iO Kc Kk Kn Qy) Ad(Gz Ii Nm qC Ra rU Vo xA) Fw(hG Is Kf Kq Nc Tn uM uW) Na(eT hL iB pY qB uL uR uX) Bo(gW hA jG qU Ra rZ xA) Kf(jM Kk qC Ra rV wJ wK) nR(bF cG cL Kn Qy Rg Ut) nD(Co Li Md Mu Nb Nf Vs) rA(lX mF mM mP nC nH nL) Ar(Nc Nr Nt Pc Uv Vo) Bb(qG qO qP qQ rV wJ) Kc(iC jY lL mI Ra tF) wQ(Aj aO Ex Gz Jq Uk) qC(Jp Jt Pj Qc Uf tM) Kq(Ik Ks Nm Ql Ra) tF(bL Gp mM mY nH) wL(aK fY Hw Jq uW) iO(mT mW mY oP oQ) xA(Jd Jr Pa Pk Vt) Ex(Mh Mp Ri Ss) Uk(fN uW wD yK) Uv(bF Kn Lx Nx) aO(uM wB tM tL) dD(cZ gW lX rX) mF(hW jE jQ Vs) Nt(Hc iB uW) Kk(Dg Jg Lh) Uf(uM vI wD) aZ(wE wG tL) gW(Al bP Gp) mZ(Id Ql Ra) nI(cM iP iZ) kG(cH Ml Ug) Mp(uX zA) Jd(eZ qQ) Jq(uZ wD) Jr(wD wF) Jt(wJ wK) Rj(jU Nx) nU(Lz oP) mS(Ug Vo) iA(Lh lM) jR(aK aU) kF(gL oN) rZ(bL Kg) rX(aF dE) rV(Hb Pj) oQ(Ma Nm) uW(rY Up) AamY DdtL NotO NuuX MbKs HvoP TtqQ RchA WnbG TkjG PkrU bFcV dMlM mMjE nHhW iJsO jPtM kNoN

Constrained panels with 3 analytes, where 1.0E-10 >= 'AUC p-value' > 0. Contains 32,373 panels of 27,488,127 total panels evaluated. :
nT{aM(Af aJ Ap Aw Ba bC bF bL bW bZ cE cG cH cL cM cN Cp dF DG dH dJ dM Dp eF Et fP Fr gL hB HC Hu Ib Ic Id Ij Il Is iZ Jd Jg jH Ji Jk Jl Jp Jq Ju Jv Kc Kd Ke Kk Kl Kn KO Kp Kq Ky Kz Ld Lh Li Lw Lx Ly Ma Me Ml MM Mn MP Mq Mt MU Mw Mx Na Nc nD Ne Nf NJ Nl No Nr NU Nv Nw Nx Ny oF Oh Om ON oP oQ Ou Pf Pg Pi Po Qa Qd Qe Qn Qz Rb rC Rg Ri To Ua Uf Ug Uh Ut Vq Vs) nA(Aw Ba bF bL Bo bW bZ cE cG cL Cp dF dG Dk Dp Ef Fa fP Fy Gl Ha hB HC Hf Hu Id Iz Jd Je Jf Ji Jq Jt Jy Kc Kd Ke Kf Kg Kj Kq Lh Li Lj Lu Lx Lz Md Mj Ml Mn Mq Mr Mu Mv Mw Nb No Nq Nr Nu Nv Nw Nx Ny oF Og Oh Om ON Or Oy Pa Pd Pe PF Pg Po Qh Qm Qt Qu Qx Qy Rc Rf Rg Rj Rm rZ Sr Ss St Tn Tr Tt Tv Tz Ua Uc Uf Uk Up Ut Uv Vp Vs Vu Tj) Ib(Ad Aj AP Aw aY Ba bC bF Bg bL bM Bo bW bZ cG CH cN Co cS cT Cw Dc dF dG Di dJ dM Ef Et Ez Fn fP Gl Hc hG Hu Id iH Ij iP IZ Jg Jh Ji Jj Jk Jp Jq Kc KF kG Kk Kl Kn Ko Kp Lh Lu Lv LW Ma Me mF Mg mH MM Mn mP Mq Mt Mv Mw Ng Nj nK No Nq Nx Oh Oi ON oO oP oQ Ou Oy Pd pF Qa Qe Qt Rg Ri Ss Tn Tv Tz Ua Uh Un Ut) Jv(Al AP Ar Aw Ba bF bL Bo bZ cE cG cH cL cM Co Cq Cw dF DG Dk dL Et Ex Fa Fn Fr GL hB HC hG Id Im Iz Jd Jg Jh Ji Jj Jk Jp Jq Jt Kd Kf KG Kl Kn Ko Kq Ld Lh Li Lv Lx Ma Mn Mp Mq Mr Mt Mu Mw Nc nD Nj Nl No Nq Nr Nv Nw Nx Ny Og Oh Ok ON oP oQ Ou Oy Pa Pd Pf Po Qa Qb Qe Qt Rc Sr Ss St Tn Tv Uf Uh Ut Vq Vs) dJ(Aa Af aJ aN Ap Aw aY Ba bC bF bH Bo bU bW cC cE cF cG cH cL cM CP cW Dc dD dF DG Dk dL Fa Fr hB hC hW hX Id Ij iO iZ Jg Jh Ji Jk Jl Kd Kq Li Lu Lw Lx LY Ma Mm Mn Mp Mq MT MU Mw mY nB NC Ne nH nJ nK No nU Nv NW Nx Ny oF Oi Om ON oO oP oQ Pf Po Qa Qe Qh Qt Rj Tz Ub Uf Ut Vs) iP(aJ Ap Ba Bg Bo bW bZ cE cG cH cL cN Cp dF DG dH Fn fP Fy Gl hA hB HC Iu IZ Jg Ji Jp Kd Kf Kg Kl Kn Ko Kp Kr Ld Lh Li Lu Lx Ma Mg mM Mn Mp Mu Nc Ne NJ Nl No Nv Nw Nx oF Ok ON oP oQ Pf Pi Po Pz Qa Qd Qe Qg Qt Rg Rj Ss St Ua Ue Uf Ug Um Ut Vq Vs) Id(aE Aj AP Bg bL bS bX bZ cA cD Ch cM cV Cw dF dG dH dL Ed Ef Ez Fa Fn gL Hc hG Hu iJ iO Iq Iv Iz Jk Jo Ju Kc KF KG KK Kn Ko Kp Kr Ky Ld Lh Li Ly Me Mg mI Mj Mk Ml Mt Mv mZ Ng nJ nK Nn Nq nU nY Oh Pa Pd Pf Pi Qa Qd Qe Rj Ua Um) Aa(Ad aJ AP Ar Aw AX aY Ba bF Bg bL BO bQ bS bW bX bZ cA cE cG Ch cL cN Co Cp Cq cR CU Cw Dc dD dF DG dH dL Ef Fn fP Fy GL hB hG iH iO iZ Kd Kf Kg Kj Kk Kl Ko Kp Ld nD oF oH oN Qt Ss St Tn Tv Up Ut Uu Vq Vs) Rj(aE AP Ba bF bL bW cE cG cL cM cN DG dM hB hC Hu Ij iO Is iZ Ji Jk Jq Ju Kd Kf Kk Ko Kp Li Lw Lx Ly Ma Me Mm Mn MP Mq Mu MW Mx nB nD Ne nJ NK Nl nU Nv Nw Nx oF Oh ON oQ PF Pg Qa Qe Qt Ri Uf Ut Vs) gL(Af Ba bC bF bW bZ cD cE cG cH cL cM cN dG dH dL Dp Fr hB hC Ij Il Io Ji Kd KO Li Lu Lw Lx mH MM Mn MP Mq MU Mw nB Nc nD Ng NJ nK Nm No nU Nv Nw Nx oF Oh ON oQ Ou Pf Qd Qc Qn Qt Ra Ri Ub Uf Ug Vs) Hc(aJ AS Ba bF bL Bo bW cE cG cL cN cO dF dG dH Di DK dL Dp Fn hB Hf Ij Io Iv Ji Jj Kd kE Kn kO Ks Li Lu Lv LW Lx Ma mH Mn MP Mq Mu Mw nF Nj Nk Nm Nt nU nY Oh ON oQ Pf Qd Ri Ub Uf Ug Uo Ut Vs Vv) nJ(Aw Ba bB bC bF bL bM Bo bQ bW bZ cD cE cG cH cL cM cN cO Cp Dc dF DG dH Di dL Fn HA hB hC Hf iO Jd jI Kc Kd Kf Kn lM mP nD nF nR oF oN Ou Ow pF Pi Qh QT qX Ri rZ Ss Tv Ua Uf Uo Up Us Ut Vs tF) cN(aA Ad Al aN Ba bF bU bW cE cH cM cW Dc dD dF Ex Fa Fr hC Hu Hw iZ Ji Jk jL Kg Kn Lh lO Lu mF Mn Mt Nc nD Ne nF nK Nl Nn Nr nU oF Oh oN oP oQ Pg Ph Po Qa Qe Qx Qz Ra Rg St To Tz Ua Ub Vo Vq Vu) nK(aJ Aw Ba bF bL Bo bW bZ cE cG cH cL Cp cS dF DG dH Di Fn fP Fw Fy hB Hf Hu Io IZ Jk Jq Kc Kd Kf Kk Kn Ko Kp Lh Li Lu Lx Mn mP Nj Nq nU Nv oF oN Or Pf Pi Pj qT Rg Ua Uf Um Up Ut Vs) iZ(Aw Ba bF bL Bo bW bZ cD cE cG cH cL cM dF dG dH Di Fr hB hC IJ iO Ji Kc Kn kO Li Lu Lx mM Mn Mp mS MU nU Nv Nw oF Oh ON oP oQ PF Pg Qc Qh Qt Qx Ra Rg Rm Tz Ua Ub Um Ut Vs) Ju(Al Ar bF bL Bo cE cG Cw Dc Fa Fn Ha hB Hu iH Io Ji Jm Jq Jt Kd Kf Kk Kn Kp Lh Lv Lx Ma mH Mt Nc Nj Nk Nl No Nr Nv Nx Oh On oQ Pa Pd Pe Pf Po Qa Qb Qe Rg Rm Sr St Tv Tz Uo Ut Vq) Kc(aE Ba bF Bn bW cD cE cG dG Di Dk dM Fr hB IJ iO Jl Ko Li Lu Lv LW Lx Ly mF Mn Mp Mq Mt MW My nB Nd nF nI Nm Oh ON oQ Ou Pf Pk Po Qe Qt Qx Ra Rg Ri Ub Vs) cG(AS aY cE cI cV cY cZ eD Hw Ij Io Iu jH Jy kC Ke Ky Lu lX Ma mF mP Mt nB Nc nD Ne nF nI Nj Nk Nl Nm No Of Oi Ou pF qT Qy Ra Rc Rg To Tr Ub Ue Uf Uh Uu Vo Vv) Ba(aJ aS aY Bb cD cY cZ eD Fy Hu Ij Io Iu Ko Kq Ky Lu lX Ly Ma mF mI Ml mM mP Mq nB Nc Ne NF nI Nj Nk Nl Nm No nU Ny Of OH Oi Qy Ra Rc To Tr Ub Ue Uv Vv) nD(aJ Aw Bg bL Bo bW bZ cE cH cL Cp Cw Dc De dF DG dH Di dL Fn Gl hB hC Iz Kf Kl Kn Ko Li Lx Mn mP Nv Ny oF oN Pf Pi Qa Qm QT Ss Ua Uf Up Ut Vs) mP(Ad Al Ao Ar As Aw Bb bF Bg bL Bn Bo bQ bU bV cE Ch Co Cp Cq CT Cw De dF Dk Fa Iz Kg Kn Kp mY oE oF oK oN Qt Qx Qz Rg Tn Tv Tz Uk Ur Ut Vs) qT(aK As Aw aZ bG bL Bn Bo bS bW cA Ch cK cL cW De Di Dl dN dR eC gW hG hW iH Io jF Jq jV kS nF Ng nI Nm oE Og oH Oy Pd Pz rX rY rZ Tz Up Vt Wm) Vo(aE AP bF bW cE cH cL DG Dk dM hB hC iJ iO Iz Ji Kd Kf Kg Kl Kn Ko Lh Li Lx Ma Mg Mm Mn Mp Mw Nv Nw Nx Oh On Ou Pd Pf Qd Qe Qt Ss Uc) Rg(aJ aS aW aY bF bW cE cH cM DG dH dM Dp Fn hB Ij In Ji Jj Lu Lv Lw mF mH Ml MM Mq mU MW nB Nc Nf Nj No Nx ON oQ Ou Qt Ri) nF(Ap Aw bF Bo bW bX bZ cE cH cL dF DG dH fP Fr Gl hB hC iH jI Jt Kd Ke Kf Kn Ko Li Lx Ne nU Nv Nw oF ON oQ Ou Ow Pf Qz Ss Uf) Vs(aE aS Bb Cu cV cZ dE eC Ij In Io Iv Jl Jn Jr Js Jy Kk Ky Lu Lv mF mI Ml mU Mz Nc Nj Nk Nl Nm Oh Oy pF Pi To Tr Ub Ue Us Vv tF) Ex(aD aE An aR aY bN bO cA cD cX dE Fy In iO Iv Jy Lv mF Mn Mz Nc Ne Nf Nj Nk No NY Pa Pb Pc pF Pj Pk Ra Rc Rf Sr Uh Um Uv) cE(aJ AS aY bL cV cZ Jy kC kG Kk Ky Lu Ma mF mI Mt mU nB Nc Ne nI Nj Nk Nl Nm nU oH Oi pF Qy Ra Rc To Tr Ub Ue Um) cH(aP bE bL bS bZ cI Co cZ dF dH Fn Fr Hu Il Io Iu Iz Jk kG Lh lX mF mI Mp Mt Mv Nc Ne Nj Nn nU oE OH oP Qe Ra Tr) Ij(Al Ap bL bZ Co Cw Dc dF Dg Ed Ef Fa Fn Gl iH

Figure 21 Continued

Figure 21 Continued rX(al Pc Vt) IL(Jd kF mW) Me(sO uW) Ib(kG oP) Ic(bX Cv) Ki(tR vS) Kl(vS xA) bW(sM vW) IY(jQ jR) mI(qV qY) qT(Fw nC) AjaC BogW
DlqI UbkG JdhA QzqQ QuhO JowE KfxA KgwK KjyD OmuM PjrV dDnH iBoQ jQkF jUoO} Qw{xA(Ad aP Aw Ba Bb bG bL Bo bW cN Cp
Cv Dd Dk Et Fw Hw iC Ij Ik iP Iq Jd jF Jg Jh jO Jq Jt Kf Ki Kl kQ IN Me Mf Nn Om Pa Pd Qz Ra Rc rU rY Uf uG Uu uX Vt tF) uM(Aw Ba
Bb bC Bg bW Cp Ef Et Fw Ib Iz Jd Jg Jh Jk Jm Jq Jt Kf Kl Kn Nv Ok Om On Qt Rc rU rX rY Ss Tz Un Uu uX wG) vB(Aj aP Aw Bb bL bW
cN Cp cR cZ De dH Fw Hw iC Ii Is Jh Jk jL Jm Kr Nb Ng Ni Nj Nv Rc Ue Ug Ur uX) tL(aC Aj Aw bC bW Dc Dd Hw Iq Is Jh Jj Jk Jm Jq Jr Kj
Kr Ne Ng Nh Nk Nn Nu oH Tz Ur uW uX) rU(Ad cW Ij iP Iq Is It Iu Jm Jp Jt Ki Kj Ky Me Nl Nn On Pj Qu Qz rZ uX vP vV wJ) wJ(Ad Bb Cp
Dk Et Fy Hw Ii Jg Jh Jq Jt Kf Kl Ok Om On Pj Qu Qz rV Uf Uu) hO(cB DB Dc Fn Hf Hq Iq Is Iu Kf Ki Me Mg Na Nc Nh Nl Pj Pz Rj Uk)
qC(cW Hu Iq Is Iu Jm Me Mg Nh Nn Ok On Pk Pz Qa Qc rX rY Uf uX wG tM) vW(Ad Aj bW Cp Ct Ef Et Hw Iz Jh Jj Jm Jt Of Om Qu Qz rY
Ss Uu uX) qQ(Ba Bb Dk Dl Ij Iq Jd Jg jL Jt Ki Mv Nn Qh Qz Rc Tt Uu) wL(Ad bL bW cM dB Hw Is Iu Jj Jk Jm Kj Pz Ug Uk Ur uX) eZ(Ad Aj
Ba Ch Dk Ef Ij Jh Om Qu Ss) uX(Aa bG cC iA Ju Lx Mp Nj oN vT) Jh(tS tV uN uY vA vT wB wP zl) vA(bW Hw Is Jj Jk Jm Kj Nn) Ad(rO rP
tO tQ wK yH yL) Me(pY qB rQ tQ tU wC wG) fY(cU Hb Jd Om tR tT tX) uW(Aa cC Di Fw Kr Lx Uk) Jm(pY qB tQ vH vT yH) Jt(rP tO tT
uG wK yH) Hw(pY tO wD yH yL) Jj(pY tN tO wF yH) hL(Fn Ij Mg Ng Pz) wK(Aj Kj Qu Qz Uf) yK(aZ bG cZ Jd Uk) qB(Dc Is Iv Ki Pz)
vP(Bb Cp Jd Om Uu) wC(bG iA Jd rY) jP(Ba Of On Vs) qO(Bb Jg jR Uu) Dk(qG rN tS) Ki(pS tR tV) tO(Et Ii Uf) rV(Ij Iq Uu) Ex(nN nR)
Ik(qG yL) Is(uL zH) Rc(ql tU) Pz(pY qA) Jg(qG sO) On(jM uG) bG(qP sC) wG(Aa Bb) wF(aC Ug) rN(Aj Kj) uY(Jq Uu) vI(Kk Ur) CptS EfwP
EdqT EtuG MstQ NjuL TzvH IvhP JdvV QuyH JksM KfrO KrsK bLwH bWvT jEtM jHpS jLuU} kC{jE(Aa aJ Ar Aw aY BA bF bL Bo bV bZ
cB cE cF cG cH cL cN cS dF dG dH Di dL dM hB hC hG Il Io Ir iZ Ji Jj Jq Li Lu Lx Mn Mr Ng Nj Nl No Nr Nu Nv Nw Nx Ny oF Og Oh ON
PF Po Qa Qd Qe Uf Ug Uh Ut) rB(Aa aD al aJ aM aY bA bB bC bF bL bN bV bW cE cF cG cH cJ cL cO cQ cR cS cT cV dD dF dG dH dK dM
eF hB hC hG Ij In iO Jn Js Ng Nu oE oF oN PF) IM(Aa Ad AO As aW aZ Ba Bg bZ cl cS Cu Dc dE dF dH Dl eC fP hB iA Ij Io Iq Iu Jk Jl Jn Jp
Js kQ Mh Mq Mx Ng Nm Of Uc Uf Un Up Vu Vv) jP(aF aJ aO aP Aw BA bF bL bQ bX bZ cB cE cL cN cS cT dD dF dG dH Di dM fP gL hB
hC Ji Lu Lx Mn No Ny oK oN PF Po Un Uo Up Ut) jD(aJ Al Ba bF bL Bn Bo cE cG cL cN Cp cS De dF dG Di hB hC hG Ij Il In Ji Jj Jn Jq Js
Lx Mn No Nw Og ON PF Tz Uf Uh Up Ut) qU(Aa aJ Al Ax aY BA bB bF bL bQ bV cE cG cH cL cN cS dF dH Di dM hB hC Ji Jj Lx Mn No
Nv Ny oN pF Uf Ug Uh Ut) hA(Aa Ao aW aZ Bg bM bP bZ cA cI Cu Dc dE dF Dg dH Dl hB iA Jp kQ Mh Mq Mx oF Uc Uf Um Un Up Uu
Vp Vu Vv) jM(Al Ba bF bL cE cG cL cN Di hB hC Io Ji Lx Mn pF Uf Up Ut) rX(Aa aD al aM cB cF cG cH cJ cL cN dD hG kR Lu Ng oE oF
Qc) eD(aJ Aw aY BA bW cE cG cL cS dF dG gL hB hC Mn oN pF) rZ(bZ cE cG cI dE hC iA Ij In Iu Jp Js Mx Ng Nm) qT(aY Ba bF bL cE cG
cL Di hB Lx Mn pF Uf) jY(Al Ax aY Ba bF bL Bo bQ cG cL Lx pF Ut) iC(Ba bF cG cI Jj Mn) jG(Bo hC Jj) hX(Aa iA) rY(hC Jj) EdcL IbnK
JnrA UpqV aWjF bPhV} vW{Kr(Aj AO Ba BB bW Cu Cv Dg Dk Dl Ed Et fP Fw Fy Hb hG Hw Ih Jd Jg JH Jj Jo Jp Kf Kg Kj Kl Kn Kq Lh Lj
Mh Mm Nm No Nr Ns Ok Om On Oy Pj Pz qC Qz sO Ss Uc Uf Ug Uu uX Vt zA tL) bW(Aa aC Af Aj bG cB cC cM DB Dk dL Ed Et Fw Hf Ih
Jd Jq Js Jt jY Kk Lx Me Mf Of Or Qb qC Qd Qe Qu Qy Qz rB rU rX rY St uN Up Uu Uv vI wG wL tL Tj) No(Ad Aj AO Aw Ba Bb Ch Cp Db
Dc Dg Dl Ed Fa Fb Fw Gp Hb Jd jL Kf Ki Kl Kx IN Ql Qn Qu Qz Rc Sr Ss Uf Un Uu Uv Vt) St(Ad Aj aO Ba bZ Cu Dg dN Ef Et Ez Hw Iq Is
Iz Jd Jg Jp Jt Kf Kj Kl Mg Mm Ng Nm Ok Om On Qu Qz Ss Uc Uf Uu uX zA) Qz(aO Aw Ba cC cR Db De Fw hG hL hO Ih Jd Jh Lj Me Mp
Nt Pg qC Qy rB Rc rY Ub Ue Uv wK zA tL) Ed(aC Ad aO aP Aw cR cW dN Et Fn Hf hG Hw Iq JP Kf Me Nj Nt Nu oH Ue uX vO zA) Me(aC
aH Aj aO bC cR dF Dk dN fP Fy gL Iq Jd Jp Mh Nm Nr qC rB Rf uX vO) Db(Ad Aj bC cI Cv Et Hw Jd Jg Jq Jt Mg Nr qC qQ Rg Ss Ub Uf Uu
uX) Fw(Ad aP Dc dN Et hG Hw Iq Is Iu Jd Jm Kf Ky oH Ue Ue Uk Um uX zA) Jd(aC aZ cC dN Ex hO Ih Lj Nt oH qC Rf rV Uf Um vO zA)
Ad(aW aZ cC dB Hf hO Kd Nt Qd Qe Rb) Et(aK aP Gl gW Hf Kk Ko Ow qI Rh Uv) Aj(cC cM Fn Hf hG Kk Nt rB) dN(Bb bl cD hL hO jH qC
tL) zA(Hc Hf Iq jL Qu Qy Up Uv) Ao(aP Ji Mn Nw Ue) Nt(Bb Qu Ss Uf Uu) cC(Dd Fb Qu Ub Ur) Hf(Cv Jt qQ uX) Kk(aO Jh Om qC) Uf(hG
Js Qd rB) Up(hG Hw Iq uX) Qu(cR hG rB) Um(Ba bM Kf) aP(fP Kg rY) oH(Jh qY vl) Fn(hO jH) Gz(Jj Lh) Hw(Kd Uv) Ki(bC Jh) qC(Jj Lh)
rY(dB Iq) FybU MgrB UbaC HuUu UkwG fPiC} Hf{vB(aC aE Aj aP Aw aZ Bb bC bE bL bM bW cE cI cL cN cR Ct Cv cZ De dH Dk Dp Ed
Et ht hA hO Hq Hw Ib iC IO Iq Is Jd Jh Jj JK jL jM Jq Jt Kc Kx Md Mm Nb No Nr Nv OE Of Oi Om oN pS qC Qn qQ rB rN Tz Ub Uf UG Uk
Un Ur uX vO vS Vt) xA(Ad Aj Bb bW cD cR Cv Dd Dk Ed Et Fw Hb hO Hw Iv Jd Jg Jh Jq Jt Kf Kl KQ Mh No Nr Ns Ok Om Pa pF qC Qz Rg
rU Uf tL) wH(aA aE Aj aP Bb bC bL bM bU bW cC cD cJ cM cN cR Ct Cv dB gL Hr Ih iO It Jd jK jL Ld Mh No qC Rc UG Uk Uu) hO(Ad Aj
aN Cv Dc Dd Dl Ed Et Hb Iq Jd Jt Ky Lh Ly Mh Nj oH Ok On Ph Pj Pz Qz Rb Rc rS rW tN tU Uk uV yH tL) uW(Aa Aj aZ Bb bC bP Cv Ed Et
Fw hL Ih iO Kf Kq Lx No Nr oK oN qC Qe qQ rY Ss Uk Vv tL) tL(Aj bC bW cR Ed Hw It Jj Jr Kj Nn Nt Nu oH On qQ rU Tz Uf Um Ur)
wJ(Ad Ao Bb bW Cv Ed Et Fw Jg Jh Jt Kq Ok Om Qz Uf) qC(qU qV Rb rT rX rY rZ sC uM uP uY wD tM) rV(Aa cR Et Hb Ij Jd Jt Kf Ok rY)
wL(bW Dc Hw Jd No nY oH oN Ub) Cv(qU rU rX ul uL vT wF yK) uM(Ad Aj Jd Jg Jh Jq Om Ss) uG(Ad Aj Et Hb Jt Kj Om On) Ed(eT jT qT
qX rZ tN wE) oN(tN tR tX uT uX wF zA) Jd(eZ qQ rT uY wB zH) wK(Aj Et Hw qQ Qz Uf) vT(aC Aj Ib UF Ug) uL(Et Jt Ok rY Ub) rT(Iq
Om Ss Uf) qQ(Bb Dl iO Qz) oK(tN tX uX zA) uY(Aj eT hG Jq) vA(bW Jj Ok Uf) Ad(eZ tQ uR) Et(qG rP uN) Kq(jM qU wC) rU(Dd Pj vP)
Tz(vH wC) Qz(hL yH) Tk(bG rZ) Om(vP vV) nK(Me Ml) yK(aZ Uk) wF(nY oH) qU(qT uX) tM(Aj Ss) DdrN FwqT UbvI JtrS JuuX KitR
WnrZ UfwD PcrX bWsM fYtX hGzH iOzA} mF{jE(Ad aJ Al AR AW Ax Ba bF Bg Bo cE cG Ch Cp cS Cu Dc DD dF DG dH dL fP gL hC hG
Hv Hw Hx Ih Ij Im Iq Ir Is Ji Jm Jn Jq Li Lj Lx Ma Mj Mn Mp Mr Nb Nk Nn No Nq Nr Nu Nv Ny oF Oh ON Pa Pe Pf Pg Po Qa Qb Qe Tz Ua
Uf Uo Up Ur Uv Vu) jP(Ad aF aJ Al Ao aP AR Aw aZ bA Bg Bn Bo bQ bZ cL cN Co Cp cS CT dD De dF dG dH Di Dk dL gL hB hG oF oK
oN Tz Ua Uc Uk Up Ur Ut Uu Uv Vp Vv) Ed(Ar Aw Ba Bo bX cE cL Cp Il Jq kO Lu Lx Mn Mt Mu Nn Nx ON oP oQ Pf Po Rj Uf Ut Vs)
rB(aD al aJ aL bL cB cE cG cH cJ cT dD dF dG dH fP hC hG iO oF) qU(AL Ar Ax aY bL Bo Ch Co cW Dc Dd gL gW hC Tz Up Ut Uv Vu)
hA(Aa AO As aW aY aZ bM bZ cV DB dH eC hB iA Uu Vv tF) qT(Al cW Dc Dd jF Jj Jq jV kS Ng Nm Nu Og Tz Ut Wm) IM(aM AO Ar As
aY Bg bZ DB dN eC iA Uu Vv) tF(dD Ex Fa Gz Kn Kq Lx oN Qt Ut Vs) jF(Ar aW Ch cW DB gL Po Ub Uo) rZ(aO bl bM bZ cE cG hC iA Js
qX) rX(aD al aL bA cB cG dD hG kR oF) Lx(Af iA ln Js pF Pi Po Vu) Ex(cH Iv kl nR pF Ri) Js(Al Dc Kn Tv Ut Vs) jD(Bo Ch cW Tz Ua Ut)
hX(aD aJ bL cB cW) IK(aF Ar aW cG Ub) In(Al Cq Dc Tv) eC(iC jG jO jY) eD(Aw Bo cW gL) jM(Al Co Dc Tz) Hc(kO Nt Ql) Kq(kQ Mz Ql)
Vs(Ib Rj Ub) aW(gW hR jY) jY(Al Tz Ut) Kk(Gz iP) Uf(bW jL) aY(iB lO) aZ(jI qV) cW(rC rY) BojG MzKn RaJj JqQm KrLi QlnI bVcL cEpF
cNjL dBhV gLqW hCrY} xA{Uf(aA aP aW bI bU cA cC cJ cL cN cR DB Ex Fn Fw Gl hG Hu iC Ih Io jM Js Ke Ki Kk Kr Kx Lv Ma Me Mn
Mp Nb Nj Nm No Nt Pa pS Qd qW Qz RB rC Rh Ri rU St Ue Uk Uv vA wL tL) Qz(aZ Bb Bo bW cR cX DB Dd Fw hG hO Hu Ic Ih IO iP Iq
jF jH Kd Ki kQ Lx Mn No Ns Nt Pa Pc Pk qC Qy Rb Rc rY Ue tL) Bb(aZ bW cC Fn fP hG Jj Kf Ki Lh Lj Ma Me Na Nc Nd Ne Nh Nl No Nt
Pa Pk qV qW rU St Ue Uk Um) Db(Aj bC bW cR Cv Dd Ed Et hB hO Jd Jg Jh Jq Jt Kl KQ Nn No oK Om qU rU) Et(aC aL aP bO bU cC dB
hO Hu iO jF jG qW qX rA RB St Ue) bW(Aa bG Bo Fw Jq Ki Me Mf Mp Mu Pc Pi Qy Rb Ue Up Uv) Pa(Bo cC Cs Ed Fw Ic jF Ki Kr Me Qg
Rc St Ue Up Tj) hO(Dd Ex Fn Iq Jj Jo Kf Ki Me Mm Na No Pk Ue Um Uv) St(Aj aO Bo Hb Hw Iq Jg Jq Jr Jt Kf Kl Om) Ki(aZ cE cL Cv iC iO
Iq Jh Kx Nb Nt rU Uk) cC(Ad Al Cv Dd Jd Jg Jh Jq Kj Mm Ok Um Vt) No(aO Bo Fw jF Jr jU Jv Kf Ky IN Ra) Me(aZ cE cR Cv Dd Iq Jd Jr
Mm oH Uk) rU(Bo Cv Dd Ic Jd Jr Kf Ky oH Pj Um) Nt(Aj Cv Jq Kl Qu Ra Uu Vt) Kf(Hu Ih iO Kk rB uG Um) Kr(Ao Ic Iv Jg Kl Kq Ok) Jh(aZ
dB jF qW rA Rb) Dd(aW Ex Gz iC Ue) Pk(fN iB iC jO qC) Cv(Kd Ky Nd Ri) Fw(Dc oH Ue tM) Lh(Gz iC qC Ue) Mn(Ao Hb Kg) Iq(aC Cs

Figure 21 Continued gL oK) lM(aX bQ fP) pF(Kn Mt) LxbV OgjT aNqY aXqX bFeD bLjL cIjI} Nu{tL(aP As cN Fb gL hG Jd Ra) Aj(wK tM) Qu(uG tM) wG(cA Kx) FnuX JdrV cBrN hGzH} bL{nU(jI jK jO lL rY) nH(jI jK jO lL) kK(eD jY qU) EdrZ PjwG lWhR lXrB nDrA} nD{Iv(Dc Hc Kn Kq Uv) Vs(Ml pF Rj Ub) DcJs EdaW MqQt InPe bZlM rArZ} mT{kQ(hA jG jI Kn Kq Ss) Ma(Gl Kn) EdUo NjdD UbVs JoUg bChA bZlM} mW{Tv(bZ In Mz) aW(jI qX) bV(Lx Nj) hC(eD iC) kQ(Kn Kq) LdaA RgtF aYiB} Jt{bU(rR uY wF tL) Hu(uR vI) rV(Ow Uv) AsrP NqhP QduW KsqQ aKqO} kK{eD(Ar bA cJ oN Ut) Jj(iC jD lL rY) Bg(hA lM) ArjK aWjT} Ed{On(bQ cD eZ rZ) qX(Bo hV Pa) uM(hG Nj) cErZ eDwL oHvI} Bb{fP(qQ uM uY) qG(dN jY Kg) Ow(rV uY) TnqX qWrW jYrN} nU{rC(aJ aM cR) In(Cq Pe) lK(aJ cN) AlJs BojV aWjI cRlM} kN{oN(aA bV cV tF) rB(aI cR dD) UojG UuhA aYeD dDrX} eZ{Ih(Is Jm Lh) Of(Bo Nq Pk) Ch(Hu Nq) JdqV fPqQ} lX{aK(hR hX rY rZ) cY(hA hW rZ) gL(eD iC) UolK} nH{cR(jU lM qV) jQ(qX rA) NvpF PajT aJlK dDtF oEoF} Mn{On(hP wL yL) Tt(qQ rV) Kg(hL wK) AdvI AowD} Jd{vI(Hu oH) DdyH OwuL aFzH cRqQ eFzA iAwC} kP{Uo(iC jG) dD(rB rX) VocH aWjI cEhA cRrB} uM{Ih(Al Rm) Jq(Pe Pg) Up(Dd hG) KphG aOcM} fP{iC(vT wD zI) hL(Iv pS) tXjM qloN} rV{Uv(Kg Kj Ok) HbOw JrwG JsPj KybG} Bo{Of(rN rP sC uW tM) mYjT} oO{MaKn VspF cTiC cYjR dGjM rCkQ} hG{Aj(yH zA) NmyH LxyL PcrZ} Dd{Up(wK yH) UvzA cRyH} Tt{Mk(qG qQ) NbqZ HvqQ} Pk{vS(cM hL) IkhP tXjG} aK{qO(Kj Pj) JqtL KxwG} fY{Ad(jR vP) HbvP PjjR} mY{lM(Bg Ct) AweD aWjI} Hw{UvwD wKzH jGwF} To{Pc(hR rX) MkrW} Ih{TvrO IsqQ JruW} Iv{HckE WnoF hPoH} aO{tM(cM Lx) FruW} iJ{AjzA OaWn sOrX} jY{pS(Jp Lh) CvtL} kI{LuKn UolK bPhV} In{TvqX lutF} Jh{IzwL oHvI} lW{CheD MaKn} QviCwD JpbGwK KxcJwG QlOnjM OaWnbO UveTuY PcrXoE qWoHuN Constrained panels with 3 analytes, where 1.0E-9 >= 'AUC p-value' > 1.0E-10. Contains 7,445 panels of 27,488,127 total panels evaluated. : nT{nF(aJ bB Bg bL Di dL eF hG iO Iz Jd Jq Kg Kl Kp Mn mP Nl nW Ny Oi Qe Qt Ri Ua Ut Vs) Ju(aJ As cH Co Dd Di dL Gl Im Ir Is Iz Kc Ko Mn Mr My oN Qh Ua) Jv(Ad aY Bn Dc Di Ip Is Jl Kk Kp Lw Ne nU oF Pe Pg Rg Ua Uc) Rj(Al aY bZ cH cO dF dH Di eF Il Jd Jl kG mM Mt No Nq Ou Up) Lu(aE aP Aw bF Bg bX bZ cH Co Cv Dc dM Fa Iz Kg Ld nY) Ib(Al bB bQ bS Dd dK Dp Jl Ke kK ml nA Ok Pz St Uc tF) iZ(Bg Co Lw Ma Mm Mq Mt Mw Nc Ne No Ny Ou Pa Qa Qd) Kk(cD cM Di Dk Fr hC Io Jl Jq Ko Mq Nd nl oN Ou) aY(bL bZ Co dF Fr Hu Iz Jd Kq Mk Mw My oP Oy Ua) nK(aP dM hC Mu Mv Nf nJ Nm Nu Nw Ny Oh On pF) iP(Aw cJ dD dL Fr Il Is lM Lw mS Mt Nf nU Oi) Nc(bC bF Bg Bo dD eF fP hB hC Id iJ Jd oF) aM(aP bE Bg dD Di iA iJ jI kF nB nR pF qX) bL(bC cM dJ Fr gL hC iO Mq Nv Nx Pi Pk Ua) cH(aJ Aw Bg bW cA cS Hc Kc Nk Nl Oy Ua tF) nD(aP bF cC cM Co fP hG Ml Mt Mu pF Po Qd) bW(aJ Ar cY Fn Iu kG Lh Nk Nm Oh Qe) cM(Al aP bF bZ dF iA Kn Ly mM nA Nx) Nl(bC cQ fP hC iJ Kl Ks Ky Ou Rg) Ug(Ap Cv dA Fr hC Jo Mt Nw Pd Po) iO(aW bA bZ Kz Mn Nj nR Ph Po Qa) Qt(aR aW cY Hc In Io Mq Nm oH) Oh(Ap bC bF cD cE dJ eF hC oF) Kn(Cu dH Fr Jj lW Ng Ra tF) Ri(Al Bg Kp Nn Pa Qd Uo tF) Vo(Cv Dc hA Jp Jq lM mS oN) cN(bV Iu kG Nj Nv Nx On Qb) Dg(cD cZ Nj Ou To Ub Uu) Fn(dM Jl Ly Mq My Nm Nw) Kc(Jq Ki Mk Nv Nw nY Ut) mF(aJ AP Fa hC Ke Tz) Dp(Hw Mg Qa Qe Qx Ua) Ij(Aj Bg Cq dH hG oN) Io(Ef Kg Pi Pk Rb Ua) Ut(iC mH Nk Ue Us tF) cZ(bF dD dF Jd Mq Nv) nA(Aa Bg Fr mP nJ oQ) hC(aQ bE Hu Kz nO Oi) oF(MT nl Nj nU Tz) On(aS Bb cA cD Uc) Um(Ar Jj Mq Nw Om) aJ(bF bH lX mS Qx) dF(cD cV Ma nB Oi) Mt(aS Fb hB Vv) Ne(aE bZ dL Id) Nk(bX hB Kq Pk) Ub(hG Ji lM Ss) Ra(dL Kf Kp Ma) Rg(bC dK lW nI) Ou(cV iH Kf Oy) dJ(aK Il kG pF) nB(Al cC iH pF) Bb(Ke Kg Ko) Ed(Mm Mw Vs) Gl(Ly nY Qy) Nj(bX Ez Ke) Ua(dM Mq Vv) Ue(Et Jo Mm) Id(aX oH Tv) Tr(Jp Mu Qe) Jy(Dk Jd oP) Uo(Ly Me nY) Pi(Jj Qa St) aS(Mq Nv Oy) bF(kG mS oH) cY(hB lM Mu) gL(Ny pF Po) lX(dD dL Uf) hG(jH mS qX) Ap(Qu Rc) Fy(Cv Vs) Tz(Jj Mz) In(Fa Kq) Hf(Kz Me) Iu(cE Vs) Iz(dK mH) Qe(bU Ks) Kg(dM lW) Ko(Of Uu) Kp(Jq Lw) Ow(aW Ly) aP(nU Qu) cC(iH mM) nJ(oP oQ) qX(hW jI) qT(jQ lN) rZ(aK nI) AacS AlmM AsNv AwBo AxjV BgKs CobC FbJk FrHb FwNn NmUc LvKl MaUu MgVv MmoH MpdA NdUk TooQ SsnU QxdH KrUs KzdK UfoO PhiJ aZhX bUcD cIhA dBiH dLkO fPlM rAjQ} Us{rX(aI aO bC cN Cq cW Dg dK Hb hG Ii Je Jo Jp Jt Kc Ke Kg Kl Lj Mg Mx Nb Nd Nq Pb Pg Po Uf Vp Vt Tj) qX(Cv cW Dg Fw Gp Ha Hb Hc Hu Iq Jm Kj Kl Lx Mg Mk Mr Nb Nq Nw oE Pa Pb Qy Rj Vp) hR(Ao Bb Bg Ch Cv Dg eF Ha Hb hG Ib Iz Jk Kg Kl Lh Mk Mu Mv Ng Nw Ny Po Qx Uf) qT(Bo bP Dc eD Iq Jd Je Jk Jm Kf Li lO Mg Nd Nv Ny Pe Po qU Uc Ut) nN(aJ bL cE Hc iZ KF Ko Ma Mp Mu Nv oF oN Pg Ua) On(cD Fw hC iA Ib In Iv Kk Nc Ne NJ Nl Qm Ra) qU(Cp Fr Iu Lh Li Lx Ng Nx Pe Qh Tn Un tL) lM(bV cG cS dG dN fP Ha Jk Li Lj Of Pe Rg) Ly(Ad Ap Cw Dc Dk Et Iu Kq Lh nA Nx Vs) xA(cX dK hP Hq Lx Mv Nl Ns Og Uk vO tL) qG(bP Fy Hw Ij jE Nv Om Oy Tn) vB(aC aP bL bM Hq Nj rB Un vS) rY(bC cE Ha Iq Nx oE oF Un) lO(aE Ef Iq Jd Kf Kl Li Ss) rV(Af Ip Kg oK Ph Qh Tn Tz) vS(Af aZ Ni OK Ph sK wD) eD(Cp Jh Kg Lh Ng Nv Om) rZ(aO bW cL dJ Jt Lx oF) vO(Al cM Cv Ij Me Mx Ou) Ba(nJ nY oK Qz rT tF) Nx(Iq Iv jT nR tO) nA(Aw bA Gp Id Ok) nJ(Co Iz Nb Po Ur) sC(bP Dg Kf Ks Uk) uN(aK cI Nb rB tN) uX(Ez Kz Mf Ow Uk) lY(Ex Hc Li Rg) nF(bF Jp Ko Nw) nK(iP Mu Oy Ph) wJ(Kq Nd Nm Pj) wG(dB Ok pS Ql) zA(bN bZ Hb Jr) uW(aC cE cI Pf) Cv(Ic nO qQ) Jg(iP Me tF) Kg(hX jL jT) Vs(mF nR uM) hP(bA cO Pb) zI(gL Kf Og) jP(Ib Mv Tn) tL(Nj rB Tz) uV(bP Nu qV) Dk(oK tF) Fa(jV mF) Jd(lL lN) Kq(nO Qz) Kx(nB wD) Lh(lL yD) Nv(Ic kI) Uk(qQ tO) eZ(Co Ct) nD(Lx mZ) qD(Hw Iv) jD(hO wC) rA(De Jh) pS(Kn Ou) rT(Ip It) uM(Ch Nq) vI(Ar bA) vV(Om Qn) AatO AdMe CqmT CwTk EdhW NorU NjvU IboQ QurO LdwD OkuL PhhL PjqQ bUqC cEhA cNuU dJwH nRjK lXlK wPoK jRqO} nA{Js(bA bQ bX cF cG Cs cT De Hv Ih Jd Je Md Nb Nu Oa Pg Qt Tn Tr) Mz(Ba bO cE cF cG Cq cR Jq Md Ml Mr No Og Pe Tz) In(bQ Co cT Dk Mj Mn Nb No Nu Oy Qb Qx Qy Rg St) Jn(aR bF cE cH Cp Kq Li Lx Md Ml Ny Po Tt Up Ur) aW(Hu Lh Ml Mr Mt Mu Mv No Nx Om Oy Pb Pf Tt) Nh(bA Bg Bo Dk Ha Iz Jd Je Ke Kg Pe Tn Ut) Iv(Cp Cq cR Dc Fa Ke Md Nr oF oN Po Tz Ur) iA(Ha Jh Kn Kq Ml Mv Ng Nw Of Pd Pg Ss) dJ(Li Ml Mv My Oy Qx Rj Tt Tz Ut Uv) kO(hW jQ jR Ke Kk Li Md Nr Om Po Ss) oN(Ib Ij Iu Jp Ma Mm nR Pd Pf Qb Vv) nO(Aa bW cM Cw dG Dk fP jI lM Lu) Po(Iq Iu jQ jU Mx nB nJ Vo tF) Mr(Im It Iu Jr lK Lu nJ Pg Qb) Og(Fw Hu Is It Mn nB Oy pF qU) Ij(aR cE Hc Kn No Nv Pe Ut) Kq(Dk Jr Jt Mm Mx nH Oi Uc) Lu(Jm jU lY Lz nB Ny Om) Nr(bZ Iu jP nJ Pi Qb) Lx(Gp Lj lK Ub Vv Wm) Iq(aL Cp fP Iz Ko Uv) Jr(Cq cR Dc Fa fP Ur) On(bP dE Mx nC Nf Ql) Oz(aL bX Cp Ny oF Pe) Fw(cH Cq nJ Tt Ut) Ma(aR cE cG Gl Ut) Ml(It nJ nU Oi Vu) Mq(cE Co Dk Qy Ut) Hu(Ao Bg Ez Ib Vv) Il(Bb Ha Iz Ke Pa) Jj(Lj Mv No Nx Pg) dE(Jk No Nq Rg Ua) It(dD Hc Nb nF) Li(Mx nH nJ nL) Ny(Iu nB Vv tF) Uv(kG mF nU Ub) Pe(jE jP nJ Up) bF(Im Of Pg Vp) Cw(Mc Pf Vv) Gp(Aa Gz Me) Mn(Aa jP lK) Nf(Jq Nw Nx) Id(eC Jy Ur) Ql(Jq Lv Ly) Nv(jP nC Uc) Om(bP jU Mx) Ex(cD hF) Md(Dc kG) Ub(dD Ly) Rg(cQ Vp) Of(Co Dk) Ut(Iu Mx) Pf(Gz Kn) nF(Na Qt) jE(hW Mb) jQ(jT rA) jU(Lh Nx) AoVp BgMv CpIb CqVu CtHc DdMt FrNm NnUd NuOi MmcE NbgL IznH RcRa QxVv QvmF QgkQ KskG NwjP UkUr PadD qTjR} nO{Ib(Aj Ch Dc dJ Fr iP Jg Jt Kp Kq Mn mZ Ng Oi oN Pd Pz Qa Ss Tz) iO(Al aM Ar aY cL dD gL Kc Kf Lu Mn Ne nR Qh Sr Ut) nK(Al bL gL hC Lv Mr Nf Nj Nm Nr Nx On Oz) Nl(AS bU cK Dg iP Ke Kf Kp nW Rj Ss) aM(bA bZ cM dC dF Fr iH kO lM nR oF pF) dJ(bB bX Jk Lu Mx Na Nj Ny Oh Om pF Tz) cM(Ar bZ cD Mf Mh Mt No Nr Ny oN Qb) iP(dF dG gL Jg Jh Lw Mg mP Mt No Qe) Nc(Ap Ar Bo bU cH cQ Kf Kl Qx Ua) Hc(bF cW dK kE kO Mw Nt Ql Ub) Kf(aS dK iZ Lu mF nI nY Ub Uu) nJ(Al Bo cD dD Dg hB iH Ou pF) Ij(Ar bF Co Cq Db Dc Ky Tn) iZ(Aa Al cL Dc Kn mS Mx Qx) As(bA Cp Kg Ly Mq Mw Uf) Kp(Af aY Mw Ne Oh oQ Qn) aS(Ne Nr Ny Om Qa Qb Uf) nF(Bo Ji Nw oF Ow Ss Uh) Kn(cQ Jv Mm nD nY tF) bW(Ar Nd Ne Ph Qa Rj) hC(aQ gL Lh Mf Oi Rm) qT(Aw hW jI Oy Pd Qc) Lw(Al cV cY Iz Rm) Tz(dG dK Lv lW Mp) Kc(Al dD Mx Ou Ut) Kg(dK Dp Jl Mw Ri) Kq(cV dE iH Me Tr) Uf(bI Db iH Pa Tr) bF(gL Jy Ly mI Ne) cL(cO cY Hw Lu nB) oN(aO aY gL Ma Nm) Nj(aE Dc dM Ke) Ub(Hu Iz Lh Ut) bU(Ax aY Bn mP) cH(Il Lu Ph Rj) nB(hB Qv Qy Ut) Ed(Mm Mn Mu) Lv(dD Fa Jd) Id(Co Hq mZ) Tv(dK

Figure 21 Continued

Mq mW) Ji(cK Kd Uu) Ou(cV Dd Io) cG(aA jH Nk) oQ(Ow Rg tF) Bo(mP Qt) Dc(Lu nD) Dk(aY Qu) Nm(Ap oP) Mu(Ar Vu) Ua(Cv mF)
Kd(iH nN) Lh(Bb Ko) Rm(mH mU) Ok(cY dR) Uh(Jp tF) aJ(nN rC) aV(dG hB) nl(hB jI) qX(hA jl) rZ(aK cY) oF(aH cl) AaGl ChjP DiKk
FamH FnaE NoQy LugL LyUo MwRj QdKr RabB QziH QumP KzcQ LdcW QlOh NxcD NypF bLjH bZmF dDmU dGkQ} qD{Iq(Ao As bX Cs dB dC Dd dH Hf iP Jd Jl Kr Mh Nr Oi rT Wm) Jt(aG cW dG fN Hc iO Kl Ks Mt Mu Ow qW Ri wC) Dd(dJ Ed Hx It Kp Me Mw Nq Oi Qt qV tU Uk) Ap(aU bl dF eF Hc hX Ks Ky Rj Uo Uv wC) Db(cG cl Hu It Kj Kq Mr Mt Pb Ph rT Vp) Ex(aR bF bG bX cR dH fN Fr Lu Mq Oa Ue) Jp(aC eZ fP Hu Nq Ow Qy rB Rj sC Uv wC) Hf(Aa bA cU Ju Nf Nr Ok Qy Uf Um) On(aN dB dC It Kk Ky qA qG Uc wC) Lh(bR dB dC Fa iO Ky Nu rT Uc) fP(bV cO cT dG Mx Nf uM Uv yH) Et(aI dC iO jG Mp Nq Uc wC) Kg(aK dB gW Hu No Nt wC wK) Kz(Bc cR dG dH Dk Dl St Uv) iH(dC Fn Hq Kp Kq Mr Uh Ut) yE(dC dJ dN gP Nj Oa qA uP) Gz(aJ Fr Hc kR Nn Pi qA) Mp(Bb Ij Mg Oh Qc sC wQ) Pz(Hu iO Ky Mw Nb rA Rb) Pj(dB Mt Nr oH Ue Uv wQ) qG(Ic iP Kc qV Rb Sr Ul) Nt(Dl Ic Nx Ph Rj uY) eZ(cF Hb Na sC uW wG) tM(bN bR Ij Nk Nu uU) It(Me Na sC Um vB) Kj(Og Rb Rh Uv wC) Uf(aN dB dG Hu Nq) wQ(Cu Ki Mu Rj Ua) Hb(aL Gl Ky Ss) Jd(dG Pa rT wC) Kf(Hu Je Oy qA) Ok(dB Mt Uc vP) Um(Ed Hc Iu Lu) sC(cC dB Nr vB) Ad(Hu Me Ue) Bc(jY qV Sr) Dc(dC dG Ky) No(Qd qW Sr) Nq(Bb Dk Ij) Hq(dC Ky Nr) Kk(dA qU qW) uM(cF Hc Ic) vW(cM gW qV) Cv(cB rZ) Nk(uW wC) Ip(uY wC) Qc(bR Uk) dG(Fn Sr) tX(Al fY) DlKr EdcS NnrT NuuW MeqU NaNj IkPh IvcF RbvB QdcC JurB KpdC PkpY aZyJ dJwG dLqA jHuP} nF{cH(bA bL cG Co Cp cS Cw fP gL Gp Hu kO Mp Mz Nj Nx oF oP Oy Pb Pf Uf Uo tF) Qz(aH aL Ar Aw Iz Jd Lu lY mM Mu oQ Pg Qb Rc Tz) mZ(Bo cE cJ Cw iH Lx Nj No Nv Og Oi) nB(dJ Ih Jg Li Ml Nh Nl Nu Pe Qa Qe) lY(Bo Fr Jq Kk Ms Nl Nu Ny Ok Vs) nJ(Bo cE cL Lh nI nL Po Uo Up Vu) iH(bC bX cD dH Ed hB Ko nI nN Qx) Nj(aL Ba bX cE Fr Mn Nw oP Ss) Ow(cD Fn Hu Js kG Oe Oy Pf Ud) Lu(cM Co dJ gL iO Kg Qy Rg) Ml(Al Ih Mn Mt Ne Qe Qt Vs) Nx(bP bX dJ Ic nK Oi Ql Ri) Lv(Ba fP Jg To Uf Vp) bB(cD Id Mt Nr Ny rX) dJ(aL Cv Ly Pa Qu Ss) jE(Aw bL jI Mn Ne oF) To(Dd Kc Kf Lh Mg) Kk(cF Ic mI Mt Nd) aW(Ba Ko Nv Oh Qt) cL(Db Gz Nd oH Pa) Ed(cM Lx Mm Pa) Gp(Ly Mb Me Oy) Mn(bX Ic lL Nf) Uo(gL Jp Mb mS) jI(aM As nM nU) qV(bS cA cG Uf) Bo(Is Qw tF) Fy(Ad Jg Kn) Ne(Jq Og Uv) In(Li oF Po) On(jD Na nK) Ug(gL Oy Tv) kO(bL Ms Mt) Ba(Mq mS) Lx(Cs Kn) Nf(mS Nw) Ic(Lh Qg) Og(Nl Qa) Oi(mY Nw) gL(Kc qW) iO(Ar Ir) rC(aD oE) lM(cR dB) oH(cE oF) AwlN DpJm NqnK MsNy MzKf IbRg TnUp TvQl IuNv QcQe JgkQ JiiC StJs RabX QwbF KoKy LhcD UhtF VsmF PdcM bPhA cGjU nMoN} Ap{wK(Il Im Kd Ko Li Mw Oe Og oH Pf qC Ql Rm Uc Uv tL) rZ(As aZ Hf Ij Io Kk Mn Na Nu Of Oi Or Pg Qw) vB(Db iO Iz Ji Ke Ko Mw Ng Nr Oe Qd Qz Uc Ut) rV(bB cR dC dF eF hR Jo Me Pg sO uM vW) tL(aI aU aV hG Hu Iq Og Pf rT Uo wD) rO(aV aZ Db Dg Fr Jn Kl Nj Nq Nw Uv) hR(Dg Ed Ez iA iH iJ Js Ql Uu tF) uM(fY Ih iO Iv Jl Kd Nb Pd Rf Ub) wD(Bc bG Fr hX Nq Qt rC Uk Uo) vW(Ih Im jG Lx Nv Qu Rb rU) hA(Dg Hf Jo Lu Mm Na Pg) qC(aU aV Bc iO jT Uc vP) jO(Ez iH Js Of qG Rj Uu) uY(aI Db fY qG tT wQ xA) cC(jG jM qU qX yL tM) wJ(aG cB cO dF dG iA) qT(Dg dJ Fw Js kG) Nm(jM jT qP qU) fY(cF Is jR Mr) wQ(aU Ij Nu xA) qX(Fw Hf Js Ks) sC(Lx Qu Qy vA) qO(aW Di hG Is) vT(Mn Nu Ri rU) iC(Hf Na rB) iH(Ib jM jT) qG(aS Ip Ut) tM(Id Mr Qu) rT(Js Md Ri) uL(aK Bc Rb) Ue(jP qU) Iq(uZ wL) Qd(wC yD) Qz(tO wE) Ky(rP xA) aZ(rW vV) hO(aI Ji) iA(Lu Pj) hG(qQ vH) qH(Ny Rf) jM(Db Na) jT(Ib Qw) yL(iO Mp) ExuN FrxA GzTk MntU MtuP HuyK IztT QuvV KzpY RhuI OetO UmhL VqqB PeyH aCcZ aVrN cFrP cMwB cOrW cUqP fNjG iJqU wGoH} nJ{iP(bF bP cE cG cL dD Iq Iz Kp Lx Ml nC nI Rj) oN(As bA bI cE Cu cV dG hW Jl mY Nm) Lx(aW bI bZ In Pi Qu Ra Sr Vu tF) iO(bF cE cL Jj Jr Js kQ Ml nH nU) jP(Ao Aw Bg Dk Et lM Mj Nx Uv) Iq(bS bX cE cG Fn Ib Kf Uf) Uc(bF Dk Md Mw Nv Po Qy) In(Cw Iz Kf Ph Qx Rj Tt) cL(Ed kQ Kr nL nR nU pF) Jn(Ax cG cH Cq rZ Ua) Kn(Gl Ko Mz nH Pi Pj) aW(Ed Li Oh Qh Qt Ra) tF(Aw Fr Nh Ni Nw Qx) iA(Hf Id Nv Qe Ql Qz) Dc(Jq Md nC nH Uv) Vu(aO Ax Cs Jq Lj) kQ(cG Ml nB nL Oi) pF(Ji Jq Mn No Uf) Ra(bF Jj Kp Ow) cE(bZ Ma Mq nR) dJ(aL bU kG kI) qX(eC Jj mF Tz) Lv(Ed Qm Ul) Mz(Kk Qy Ut) Ko(Kc nC nL) Qn(cH Is Jq) Up(eC Md Ur) rA(jF Mj Nx) Ba(Ez Mq) Bg(Ny Ut) Ma(cG Kf) Qy(nC nL) Qt(Ez Qu) Of(Ao Mu) Uo(Ly qU) Oz(Jy Ou) aM(jY qT) jD(cM oQ) jH(aJ Al) jM(As eC) lM(eF nU) ChHu CoJs EdJq FwNn GpNl NqUt NtHc MqKq NjaI UaJj TonH IjUv IlbF JijT KcdE RjlY aDrC aNrY aZhX bXnL cCrX cNlK gLjY oEoF} Qw{vB(aZ Ba bC cC Cv Ib Iu Md Mv Ne Nk Nn Oe Oy Ql Uk Un) wQ(bP Ed Gp Hf Ik Lu Nd Ph Pz qC rY Ut vU) uM(Af Aj aP bI cN Fa Lh Ms Ne Ni Nj qQ Uc) vW(aC Ba Dg dN Ed Fw Jo Rc Uc Uf zA) wL(Aj aP bC Dc Ng Nn Oy Qh Um Uu) rU(Dc Dd Dl Hf Kf Kz Ok Pk Sr yK) qC(Dl Hf Kj Lh Ma Pj rZ Sr yL) tL(Al Cp Et Ij Nl Nx Om wJ xA) qQ(cC cD dK iP It Iu Nm Ok On) vA(Aj Ii Lh Mg Nv Ok Uc Ur) wJ(Ao Co Fw Jo Kg Kj Ug) tO(Ed Fy Hb Nm Ok Om Pj) Cw(eD hA hR Ib jO jT) uX(cM dF Nu oK qU Qy) Jg(dJ fY qP wC yL) zH(Al cM fY hG Jj) wD(bW Cp Hq Jv Ky) wP(Aj Cp Iz Of) wG(aZ bL cR Jv) vT(aC Hw Jj Jk) Om(qO tT vV) eZ(Of qV qY) hO(Kj Ky Nx) wK(Et Ju On) jP(Ad lM Oy) rV(cC Qh rZ) uW(Ex oK Qy) Aa(fY rT) Bb(qX vV) Hw(rO wF) Qu(tQ wC) dJ(Kq sK) yK(oN Ur) pY(bC Kj) rY(Bc rN) yL(Jj On) vI(Cv oH) BawB DdqB EdEx LxnR NjwC QhjM UuzI VunB VqzG aPwH cMvO cZxA} Vq{hA(Aj Bb bQ cK Hc Hu Kd Kq Lh Mt Mu Mw My Nv Nw Ny Pb Pg Pz Rc Vs Tj) jY(aH Ar bB dD dL Fp Fr Ha Ii Js lN Lx Pe Po) jO(Ad bJ bS cJ cY Ki Oy qT rW rX) hL(Ao bR Fa Hb Jg Ml Uc Vv) iC(bC Fr Hq Je Of Tn Tt Vs) qX(aU bV Db jH lK Oe Pg qT) sK(Je Mp Oy qU qV rO) yL(bI cO Lu Rb sM vI) uW(bM Bn Di Or uP vU) tF(bV cK dL Ed Me) qB(aN cE It Jq Ul) uV(aM Ax Fn Jr zI) tO(Ao cR Hb oE) yH(cL Dg Je Mu) qC(bU Cu Kd Uk) vI(Cx Fn Hq Pj) Ki(eD jF jT) aK(jP jQ tX) dJ(lN qT tU) eT(Cp Ed Fw) nB(Ma Mk Uc) hP(cE cL dF) tT(dH qW wH) rV(Fn Im Qv) uL(Bn Jh Mz) uI(gL Ok Vs) vH(Nn Oh Qe) Gz(wK Tk) Qn(uM vU) cD(Ly vT) cF(uN Tk) dL(lN zG) tU(Li Uu) tN(cO tX) jG(cC dD) sM(Pf Uf) rA(Gp Iv) lM(dG hB) sC(Ad Vs) rR(Ct Ng) uY(iP Mw) AamI BaeZ BbvU DifY EddR ExhX MeIc MgtL MliA MypY IhzG IqtV SszI QvrT OfjT OwyK UkrP bIqT bPhR bSuN cJlN dMrX fNfP tQkS qZrZ qVjM kIpF} vB{Ue(Ad aZ Bg bI cE cR De hO Iq Jg Kc Md Mg Nu Nx nY) Db(aZ Bn Cx Ed Et Hw Mt rB Rc Sr Tz Ub Ug Un Ur) Nt(Aj Al aP cN Dl Fb Iq Kf Ki Kz Mc Nv Uc uX) Rb(aP cI cN cR Dc Ed Hw rB Rh rN sC Um uX) Qz(Bb bE Hu iC Ih Iq Nb pS Qu Rc Uk) dB(bG bH cK Fb Jq Kf Kr Nv Ok Ow Ut) dJ(Af Ao bH cB cF Nb On qY rB rY tL) Ex(Al Lh Mk Ml Mm Ok rV uV Vt) Kr(cE De iC Kn pS Uk Um wQ) aP(Et Hb Ih Iq Ky St Um vW) Me(aC bF Hu Jd Kx Lh uX) Iq(aZ Bb bE cN Oa Qb) Ki(aC bE cE Kc Nb) Um(cL cR hO Mf Uv) aZ(cI cQ jR Nj) bW(bG fY Jq Mu) cC(De Fy Kc Mm) iC(aK Ms Na sC) No(lN Rc Uv) Mp(Bc De Nn) Kz(aC jM oE) Gz(Ib Ur) Hu(hP Jg) Hc(Ef Oy) Jd(bL cR) Kk(aO vI) cN(Ed Mk) jH(aL Io) BbOw BcKf CpIz DeNr EtKe MmbU NaRc UcHf IpcR KcfY RhaO} nB{Ub(Dd Hc Kp Ly Mx Nr On Pf Qe) pF(Mn Mr Mt Nl No On qT qX rA) Kg(aH Ct Cu De Dl Ma Uc) Pk(aI As dN Hq Ji Pc Qa) Fw(Ax Co Hc mS Oy Ph) Vo(aS bX Ip Nv Ny Vu) hC(Ex Im Lx Nv Qv Vs) Nm(Ef Gl Ko lL Ut) Kp(Bo bW Cv Ko Vt) Ph(Jn Jr Js nR Pi) tF(Nd Nr Nv Nx oF) Al(Iv Jf Js Tj) Tr(It Iz Jk Pa) Ji(Ed jD jT Uu) Qy(aH Ar Jf lY) Kx(aA dA De mF) aS(hA Mt Oy Pf) dJ(An Iu Jq nN) iP(Nd Nx Pz qU) lK(aJ aQ dH dR) Lx(bV Jf Nj) Iz(aV Bo Dg) Ki(Dd On Pa) Ko(bW bZ nR) Ou(Nx Ow Pa) Vt(lX mZ Nx) bX(Hu Nc To) cV(hA Nc Nv) qX(JQ kS) Co(eD Jf) Cu(Kf Ut) Dc(cZ Lu) Gl(Ib Ma) Nj(nK Pf) Tz(aW Tj) Is(Ks Vv) Kz(aN bV) Rg(aH gP) Oh(aN bJ) Ug(cY Dd) bF(nR qU) iZ(jE kO) AacR AnlO ArTo DkKq ExgP FnGz NoRa MaUt MeHf NdgL UacY UcPz InVu HcRj IudI QbcZ JdNv SmR JqKy JsRm LhnY VvmS cIiO rAlM} Cw{qX(aO aW cA cC Ct Dc dF Dl eD Fb Fy hA Hu Ij Ik Il Iq jG Ki kS Mc Mj Mq Nu Ow Pg Qd Rb Rj Tn) qT(aW bG dG Gl Ij Iq Iu jD jP Kk Kr Mw Mz Nu Ow rB rX Tn Up) hR(aW cA cC dA eD In Iu Jj jP Ma Mc OH oK) iC(aO bI cJ Ez Ic Ij Ik Iv Jo Kp Ng Oh Pe Ql) jP(aU cW Hu Hx Ij Io Kr Mp Nj Nn Pg Qu Rg) eD(Ao dA Ez Ij Io Kk Ko Lu Nq Pg Uh Uv) hA(cD cE Cv Dp Ik jM Kr Lu Lx oK qU) rZ(aZ Bg cR Cv cY dA Il Nj Nr Pc Pf) jO(As cD dA Ed Im Ng QU Uu) qU(cD dA Jo Mc Nm Pg) In(Kk lL Ly Qz rY) jM(cS iA Iv Oh Ug) Tk(Ba cG Ic Uu) Ib(Fw Ic Me) jT(As aW cD) rY(Bg Io Ks) Pg(lN Qz) jL(iA Uu) rX(Ef Ua) FwaC NmlN NtjK MeKs IcOu WnjG UgnN dJlL mFjY} vW{Fw(aC Al cW fP gW hB Hf Jj JP Kk Nm Ns Ok) Db(Ed Is Jj Kq Ok Om On Qu rY Uc

Figure 21 Continued zA) Mc(Ad aP Aw Cv hG jH Jr Kx Lz Ok Uf) Kr(al bC dN eT Iq Ly Lz Nd Pc Qu) Qz(Bb Ed Lx Ow Rb Up uR uX vO) Et(aU Dg Ke Ks oH qG
qO rB) Um(Bc Cp gL Kl Qe Ss Uu tL) Ad(cR Ih It Js Mp Up Uv) Jd(Aj Hw jH Jj Kd Nd Uk) bW(aK bl Ha Jj Qa rR rV) Ed(cC iP Ne Rb rY Sr)
No(aP cM cN jH Qt Vs) Hf(Jj rY Ss Uu) Uf(aF cM cR wQ) Bc(hP Kg Pb) St(Iu Mw Tz) Kk(Jg Kf Ss) Uu(Lj Nk Ue) aP(Jt Om wG) cC(Dp Uc
Ug) qC(Fn fP uX) Aj(Mp Oi) Ao(Gl Nb) Nt(Ba Kl) Iq(Rf Rm) Jj(aH Uv) Kd(Jt uX) Ki(bE gL) aC(Nj Sr) aZ(gW wG) dN(rV Up) CuJs DdQe
FyGz NmUe MnKg KfaK KlhG bCwG cMjH cNfP} dJ{rZ(Ad AO Ba bX cF De Gp hW Ke lM Mk Ns To Uh Uk Ul Vs) Ed(bU bX hR Ic jD Ki Mb Ml Qv qW sK sM) wG(Aa cF Dd Dl Fw Kx rV Uk Un Ut) aC(Ba Bo bU bX cB Co Dg Fw Gp) nR(Ba Ic Jh Ke Mt Ok Po Qt Uh) hR(aI Cv cW Gp Kq Pa Qx qY) Kq(Ic Ly nD nL oO qX) eT(bG rX rY uG uU tL) Jd(eD hO lK qT rT) wQ(Ao As Cu Hf Pa) Ly(aQ Ic lY Qt) cF(aQ bU bX cU) nK(Aw Bo cW Gz) hO(Dd Hb Pz Uf) sK(Jh No Om Qz) Fw(bX cB gW) Ic(jD Mc Ml) nN(iZ jP Oh) wH(Kk Ml Nc) rU(Hb rX vP) Tt(qT rS) Jg(hA qI) Jt(hA qT) Kf(rV zI) On(iA jP) Pj(qC tO) Pk(hP pY) bW(uI wL) cB(Gp qX) cH(kG kI) xA(Ki Qz) BcrY UboQ KjtL KztT LdnL cWrX mIjR nIjF tXjH jPkN} xA{Uf(Aw bC bS cD Iq Ko Lx Pg Pk rY wK yH) Hf(aZ cI Dc Dg Iq Jj Lh Pd uG Uk wH) Qz(aW Ed Et Jh Md Qu qW rU rV wL yL) Kf(aK bO cC Db Js Kr qW rA Rb Ue tL) Bb(Et Ml Nb Ny Ow Rb tL) Bc(aW Bo cW Gp Nd Ne St) Et(aZ hG Ke Ko Ks Uv) Me(cX Ed iC Kx Nn qC) Ue(Hb Jp Kg Nd Nt rA) bW(As Jt Ky rZ Ua yH) Bo(Ed Jh Of rB Um) Dd(Fw Ki Nb rA) Um(Jh Pc Qe Uk) dB(Fy Jd Jq Pa) rU(Dg Fy Kc Ug) Fw(Cv hG iP) Nt(Ad Dk lN) Ic(cD cN cR) Ki(bC Io oH) cC(Nm Ph Pj) rB(Kx Pc Uk) Db(Hw St) Iq(Nd tV) Kz(bF bS) Ok(hO iC) Pk(cD cR) qW(Jq Vt) AoiO ArNo AwUa DecW DgSt FnjH IshO RaaC QviC QhPa JoKr JrtL KluG UkkQ} nN{Ug(Aj aM Db Hc iZ Kp Lx Mp Nn ON Oy Vs) Kn(Bo cQ Cu Id Jj Jn Jr Ma Mz Nm Pi tF) Ql(aJ bB cS gL Kf Ml Mp Nn Ow) iZ(Hf kO kQ Nn Oh oN Pa Pf Uo) Id(cG Co Fn Ib kG Mu Rg) Kc(cM cQ Di iO iP Mt Oh) Kk(aM Ic Il Js Ko Rj) Vo(cS Kl Nn Qd Qt Ss) Oh(aW cQ cS Ed Oa) jP(aZ Bg bP Ch Vp) oN(As Hu kO Nn Vv) Lu(bX dG Kg Uk) Bo(Nc Ra Ue) Dp(Ic Oy Rg) Fn(Ib iP nK) Nn(aN Cu iH) In(Kf Ph Ut) Ex(Is Ni) Ub(dG gL) Ue(Nx oP) Ic(bX kO) Kf(Jj Js) Kq(aM Pb) Rj(Di hC) Uf(aX kC) aJ(bL Nm) eD(Ch dB) iA(jH qV) BaKs CuhA FyOm LyaN MpUc NjdL IbKg OnUu VtqU VseC PfiH aKhX bMqT} nK{tF(Bo Gz Jg Kn Kq Ml Mr Mt Nr Pf Pk Qy Rj Vu) Lx(bM Fy iA Ik Im Jn Ml nH Nm Pe Pf Qa) In(Ih Jq Kk lM Ny Qa Tv Uv) Ed(cG Cp Fw Ib Io Mw Nv) Fw(Al dD Hc Md Qa Qt) Il(bF Ir Iz lM Ml Ph) Vs(It Jl Ly mU Ra Sr) Ib(Jq mI Mv Uk Uv) Js(Kk Ma nU Oh Up) Ml(nC Nj nL Ri) Iv(bF Cq Iz Uv) kO(Ic Nf Nm Ph) Mz(bF Mn Rj) Nj(bP lY Mn) Hu(Ik Pj Vv) Id(kG Mv Ua) Jn(Al Cq Ph) Ko(Aa Ma Nm) Ql(Ic Kz Pa) aW(Hc Nv Ny) Ar(Fy No) Lu(bX Cq) Me(iH jE) Mq(Aw Bo) Ir(Aa Pj) Ra(gL nI) Jl(lM rZ) jF(Nd Of) DbLy TjOy NmOk LvVu MacE MbrX MrpF NlfP IcUv JmjE JplM JqqU OhbP PbcR PjaR} Hf{wH(AW bE De Dk jE Jh Jj Jn Nb Qc Rh rV Ss uX wK tL) hO(Ax Bc dD Dg Dk Ef Jg Jp Kf Kg Mp Pk Qh Qu Sr Uf) tL(bG cC Dd eT Fw Jq Ki Lh Mg Mk Pb qU rV) wQ(aC aO Cu dB Fb Kq Mp Rc rU UR) wL(Dd hG Jj Kj On Ug Um) uW(Af bG bI cC Kx Po Qb) qQ(cR Dd Dk Ij Iq Jg) Cv(hA jY qT rV) Jg(qG qU rT uY) eD(cW Jd On qT) wJ(Hb Lh Nm Pj) wD(aZ bW cC Uk) Ed(hR jL qU) uY(Dl Jh Nv) Aa(rT sC) Hw(vA vT) Jd(qI qU) wG(Nb Uk) qT(bG Ou) rY(rN uG) rV(On Pj) uM(Ba Dl) DcqC RcqU SsuG LhwK hLuX yKrU} Bc{wG(aS bP Ih Il Kx Lx Mb Mw Pi Pj rB Ri Uc Uk Vv) sK(Cq Hr Il It Nk qV rX Uv uZ Vt wF) vI(aU cW Kd Kf Oi Pe Qv Uf Uk Wm) wF(aF aW Ih It Kd Mf Of Ow Up) yH(Of Or Pb qC Qu rB Um) tO(Ih Kd Mp Oi Qd Wm) rU(As iA Iq Nu Ph Pk) sO(Aa Kk Ow Qy wJ) uN(cL It rZ uL wJ) qC(fP Kf Pk rZ) rY(iH Ou Ue Vv) wL(bL hC uM) tV(Iv Lx Mt) zH(Ao Ow Qu) yL(cR Ij Ky) Aa(rW wP) Et(tT wD) Fw(rW wJ) Iq(rR sM) qB(fP Uf) jH(vT tL) rV(cR dH) uM(Kd Mr) NouL MpwD NjrR IjwC QmuZ UktL UmvU UvvH bGrQ} wQ{Uf(aA bG dE Fw Ip jG Mt Nt Qt Um Ut) cC(Cu Db Fw Fy Lh Mm Nn Ok Uk) Qz(aW Et Hx Ic Ir It Pa wL) Nt(Aj aO Cu Db Dg Pj) Kr(Co Cu Dl Ic Lh Nn) aZ(Ad Ed Fb Ok Rc Ut) dB(Ba Gp Ju Pj Ur Uu) Uk(It Mp Rb Um Ut) bG(Ip Ky Rf Rh Um) Db(bZ cA cE cL) Ue(Ao Fb Jp Kg) Ki(cA Fy Nm pS) Kz(Fb jL Ml Ug) fP(jM Mf qC Rc) Na(Ba Nm Ur) Aa(aF aO) Dg(No Uc) Et(Ez Rb) Ex(aI Tz) Gz(iC Og) Mf(aF bZ) Hb(aL No) Um(bE qT) AsUu BaHc BbMp DcFw NbPj IpUv IqtV ItRm JqNy KfaL RhaO UpuW iHiZ} Ed{qT(aG Aw Bb bL Dc Gp hG Ip Is It Iu Jq Kc Lx Nb Nj Pf Po Qa Qu rX Sr Tz Ue Ul Um Up) mF(bF cG cN Dc Dk Fr IO Iu Ji Li Mp Mw No Nv Qa Qt Ua tF) rZ(aP Ba bF Bo bW Db Kf lM Lx Nj Pf qX) nC(Fr Il Jq Lu Mu Uf) On(aG bO nR oO) cC(tN tS uZ wJ) iH(jL Kq Ou Pf) qX(Iq jR qW Ue) Ex(Hu Rj Um) wJ(Dc Ic Jt) wK(Hw Jp Nt) Bo(hR jM) Db(jL uL) Lx(aG hA) Ki(uV uX) cW(eZ iC) uW(Me Rb) ArQz NttO NjtM UerY IbTt KrsO PajT PflY cLnL cMkO fPhR} iH{hA(Ad Ba bW cN Cv Jd Li Lx Nn Ok Rg Uf Vs) lM(cJ dG eD iA iB Iv jM jP lN Nf Pg qU) eD(Al cE cK cW hR Jd Kp Ml Ul) hR(Gp Il Li IN Ml Pc Uf Vv) qC(cO Dg Dl Hq Ic Iu Jm Uo) IN(cK dD Fr Pg Rg) hL(Jg Jm Mm Nx) hO(dD iB Ij Li) jM(Ad Fr Ok On) jI(cW dD Jd) jP(Mk Of On) rZ(aZ bF cL) iC(Ad Jd) jH(bG cQ) sO(bA cM) qT(In Kx) uU(cC hG) vI(bV cT) AohP GzkI MamT MfzA IqjV PcrB PfnR aOwG cUfY dDlL yHjD qYyE qQoH} Kz{rQ(Ad Jh Jq Om oN Rc Uf Uk) wL(aC Jm Ne Oz Qh uO) tX(bE Hv Pb Qy Ra rC) rU(bM Fn Hu Jq Kg oN) uY(Ba Cx dH Ml Ql Uu) tR(Jy oK Ow Pg rC) rN(aY Di dL Kj Ml) lY(aM cM Ko Qy) hO(Aa Hb Ph Qz) tQ(Fb Iq Ir Lh) zA(oK oN pS qT) qQ(Aa iO Jd Qz) Ql(kG mF nL) qB(Jt Kc Kf) rT(Kx qO Uf) Me(Fw In) Nc(rR tL) Hu(qZ uN) Ug(vA wF) wJ(Et Mm) zG(Dk Ib) zH(jL rP) BnvS CxuM LxwH QeuG KcqC KjtL TkbW PbuX aKqO bFwG cQkO cWvU zIoN kSyL oHvP} Dh{wH(bL bO cC cR Ky Mn Rc Uk wF) wJ(Ad bC bW Fw Hb Jh Jq Nr) hO(Dk Ef Fn Ij Ju Kj Uu) qX(eD Iv jM jR Ou qU) eZ(cC Ih Qu qV rV) jM(cW Kq Ok Qh Uf) wK(Et Hw Mg qQ) wD(Ih Ki Rf Vp) qU(Li Pf qC tL) qG(Aj Dg jH Om) Mr(sC tM tL) hL(Kg Ph Pj) yK(aZ oN Uk) wB(Jh Nm Uu) rV(Aj Kj Ni) uL(Et Mg Nr) Ly(cD lY) iC(sC Uf) tL(Jr Mg) qQ(bO Ij) CvrX DdrU FwuW LxnR OmvV PfeD bCvT fYtX hAkC mFqT jRqO jTkF} Qz{Ou(Ad Ar Bb bF cE Et Ic Jd Kf Ki Qg) qQ(aW dF Hu Lx Nt Pz RB Ue Up Ut) wD(aZ Hw iC Ih Jr Kc Mu Nt Rb Uk) hO(aZ Dc eZ iO Jt Kf Nu Uv wJ) In(Al Ha Nx Ny On Qb Qx) wJ(aZ cU Hc Kc qU rU Uk) tL(cR Dd De Et Iq Nj) wK(aZ jU Kx Uk) wL(Iu Qh Um) tT(cU Et rU) Ar(Fw Nr) Gz(lY wH) Nj(rR vS) Ub(uM vI) tO(aZ rU) EtuG ExcU IbTt StyK KiuX UmqB bWvT dByE dLeT jFuI} cC{uX(Aa Hb Ju Kg Qv Uk tL) qG(Dl Fy Ik Nj rX Tt) yL(Et Iq Iu Jj Jm Nn) Kf(qA tO wD wG) Ok(hR jT rV rX) eZ(Kg Om On Qu) Tz(uM wC tL) wL(fY Iq Ug) wG(Aa bW Jq) zA(Iq Jq Mp) uW(bG Cv Up) Et(sC uG) Fy(tS uM) Kl(uG wJ) Kq(hR qX) Uk(qB wD) Pf(hR rZ) tN(Ip Kg) yD(Lh Pj) jT(Ba Uf) tL(Kr oH) qO(Aa Dk) qQ(Is Tn) AjqI AluY DduV DpwH NmuM LybX NjrV JgqP JhvP SstM QusC QhjM JmwF JvwD UuqA VtrW PhwJ wErU} Iq{hO(As aV eC hR iA Nm Nx On tV uY) wL(Ao bU bW Mv My Of oH Om tV uW) tV(Hx Jl Mt Nr Nu Pa rV wH) wD(Ao Et Ip Jj Jp Mh Ni Of) Et(qC tT uM uZ wF wK) rU(Dd Hb Ip Jm Nj Pk) sC(Ex Kd Mr Qa qC) uW(hL Jd Nr Qa) qC(aN Ky On) wH(Mn Qe Rf) tL(Cv Jp Mr) dL(eT zA) wF(On Up) NtyH MeuL MrwG JprR LhwJ cWhA dBqU iJzA rSoN} Ki{pS(Ad bX cM Jf Kj Lh On Ow qU) rU(Cv Kc Kp Mn No Ok sC uI) sC(Aj bG cE cL Et iC) Aj(qG uG tM) hO(Et Pk Uk) qQ(Et Kc Uf) Fw(qT qX) No(rR wF) Je(vO vU) Kr(tX yD) aZ(wK yK) bI(uR vO) iC(wD wG) tR(Fn iO) wH(Aw cE) rW(Nb Ok) uM(cR Om) uV(cL rA) EfrN ExuR NutL MmwJ UbvU JgqG OfuG UfrP PcrX aCwL bWvT gWqX iOrR} mF{jE(aF aP bA bL cB cH cL iZ) lK(Ba bQ dB dG gL hC hG) Vs(cH In nR pF Vp) qU(An Aw Cp Cs Ua) Lx(cM cV Rm) Ql(On Pa Rj) tF(oF Qy Rj) Ba(eD nR) Ch(eD jM) Nr(In jF) Js(Hc Nv) eC(jI rZ) hA(Ar oF) rB(cN kR) jD(Dc Di) qT(Aw Ny) jP(Bb Cq) jQ(aW Ub) ExRa NmoN MaoP InPe ItjY UtnR aZjV bMlM cBjF iAqV hCjG jIkO rArZ} Um{zH(aA dK Et Jh Ns Pc Qb rB rY vA wL Tj) wL(aD Aj bG nW Of rO Uf vI) qC(dH Et Pj qV rQ rU) vU(bI Bo bP eD Mr oK) Aa(hO uL uM uY) tL(Aj Kr Mf Nu) vA(Ba Kf Uk) Bb(qQ wJ) Fw(qT uL) In(Nx Ny) Qy(sO vP) wK(bP Uf) uN(Ue yH) vI(oK Pg) DkrR LxvS NahO IbJg QeuL QutQ KfrV PjrU jKkG kClM} nR{Vs(bJ dI Ic Kd lY mS Nc Nh Og ON Vp) Ex(bE bN Hu Is Nn No) Nx(bL bP Ql Qy Uf) Ba(Ik Kk Nl oN) Lu(Al gL Kd Kn) On(bL Fy Gp Ib) bF(Fn iO Nl pF) Tv(aW Lw Pf) cE(Aa As Dk) Lx(cA Cp) Ml(cG Qy) Nj(fP Uf) Kn(Lw Mm) Lh(cL Id) eD(cM dB) oN(kO Ou) AlIn LvIb JoUg RjcL VocG cHoP} kC{qU(Ar Bn bW bZ cQ dG dL oE Og Pf) jM(aJ bA dF dG hG Pf) rX(aJ aY bA bB bC bW) eD(Cp De Di Uh Ut)

Figure 21 Continued

Figure 21 Continued

Mb Md mZ Nd Nr Nx oK Oy Rb Rg Ur Ut Uv) Jn(Al Ba bL cG Co Cw Dk fP Iz Jq Kk Kn Mn Nr Nu Om Qu Ut) aW(Ha lz Jg Jh Jv lK Mw My
Nq On Pg Qx Qy Rc Rg Rj Ua Ut) dJ(Fa Iz Jh Jk Jv Mu Mw Ng Nq Of Og Pb Pf Pg Rc Tn Ua Ur) Js(bL Bo Ef Jk Jv Jy Lj Nf Pf Pi Qy Qz Rj
Rm Ss Vp Tj) It(Hu li mH Mn Mu Mv Mw My No Nr Nw Nx Oy Pf Pg Uv) iA(Gl Gp Iz Jv Ke Kk Mk Mw Oh Pb Qt Qx Rg Rj Uc Ur) Nf(Hu
Jh Jj kG kO mF Mk Mw My nC nL Nv Of Qx Rg) Hc(Cu Dc Dd dE kl kQ Mq Oi Pj Ub Ug Uu Vo Vu Vv) Iq(aR bF Bo cG Co Cw Gl Kn Kp
Kq Ml Nr Pe Ua Ut) Iv(Ba bF cE fP Jq Kn Ko Li Ml Mr Qt Qy Tn Tv Ua) Us(Cl Ml bP cG cL Cu De Fr Ii Jv Kk Ml No Qv Ss) Gp(eC kG Ml
Mz Nd Nj Ny Om oN Oy Pe Po Ur Uv) In(Bo cG Cp Ef fP Jd Je Jy Ml Og Qt Rm Ss Vs) Up(Cq Dc Ex Ha Jq kl Li Nd nJ Nr Nu Qz Ut) Mq(Ao
Aw Bb bQ cT dD Jd Jy Mu Mw Nb Qx) nL(Gl Ha Iz Kp Mn Mt Mv Nv Om On Qz Rj) kO(Ef Fa Kn Mr Mu Qg Qt Qv Rg Tn Tr Ua) Mz(Aw
Bb bR Co Cs fP hB Kk Li Qx Ss) Il(Ao Aw Bg bQ bX Dk Id Md Qx Rc Rg) Jq(lc jU nC nH nJ oP Oz Pf Rm Ug Vo) nO(Ao Ap bA bL bQ bU
cT Di hW oP pF) Ny(bI Jl Ks Of Oi Qm Qu Ug Vo Wm) Uv(Cu eC Oe Oi Oz Qb Qh Qw Rm Ug) dE(Fa Gl Iz Mn Nu Pf Qx Rj Ur Ut) nC(Gl
Ha Iz Kn Kp Mn Mt Nu Om Qz) Vv(bF bP Iz Jc kG Mv Po Rg Ut) nH(Ef Ha Kp Nv Om Qx Qy Rg Tz) Mx(bF Bo cE cH Cp lM Ml Qt) Rj(aR
Ba bM cL Hu kG kl Rc) tF(Jg Lh Mv Oy Qt Qv Rc Rg) Dd(Iz Kq Lh Nr Nv On Pf) Po(Ic Ks lK lY Nm Ub Ug) Lu(Gz jE jH kG lK IL Oh) Jj(Hq
Hu Lh IL Mn Nw oP) Og(nU oP Ou Pi Pj Rm Ub) Ut(Dc kI Na nF nU Pd Qb) Pg(Cq jP Ke Pd Qx Qy Vp) jQ(hA kG IM Lx Nr Oz qX) Bo(Kf
Nm Oz Pj Qb Ra) bM(Gl Mg Ml Oh Pf Uf) jU(Ji Mk Mu Mw Nw Oy) oN(Ks Ou Ra Tr Uc Uh) Ly(aM cQ Db lY Rc) Rg(Ez Mj nF Qv Qw)
Ur(Ct mF Na Oi Qz) Pe(Cu Md Oi Ub Ug) bZ(hA Hu Lh Mt Pf) cE(Et Iu Jl Qb Uu) nT(bC Co Hq lM mM) nJ(Gl Ha Iz Kp Qz) Lx(nU Ou Qw
Ug) Kq(lj kI nI· Pj) On(Nm Pj Uc Uu) Vp(Jd Je Jh Nq) Pi(bF Cq Mr Nx) jE(jl Nv Oh rZ) lK(aZ nY oE Om) Ar(Pj Pk Qh) Gz(aE aV Nk) Hu(aR
Ks lY) Id(kG Mv Qz) Qb(Bb bF Nv) Qx(Ml Of Qw) Kk(cQ mF Vu) Oz(cB cQ Li) Ba(Et Pf) Bg(Mu Oy) Cq(lj Wm) Nm(Mr oP) Nr(Qc Uu)
Mc(Aw iH) Md(Ki mF) Na(Cp Ke) Uc(Fa Mu) Tv(Im Rm) Iu(bF Nv) Jm(cB Mn) Oh(Ed Vu) Ug(Jy kG) AaqU AoOf CtUa CwJl DcMr DkoP
WmNb ExhB GlpF NonB MllY MwbF NdUk NgkG UbcQ TtnU RcVo SskQ RacB QtkI KnPj KrLi NxbP UuaR PaPf} nT{Jv(aJ bB Bg bX cS dD dM Dp iH Ir Iu Jm Kc Mm My Qd Qx Rj Tz Uo) Ug(Aj Al bE Co cY Dd Iz Kq lX Mm mZ Om Ow Pe Qt Qz Tn Ua Uc tF) nF(aP bC Cw Dk Et Ib iJ Kk mS Mt mU mY nB Nc Nu Nx pF Qa Rg St) aY(aM Aw Bo cC cD Di Dk hB Io Je Ji Ju kG Lu Mn Mv Nj Po Qe) Ju(bZ Cq Dg Dk Dp hC Jp Kg Ne Nq Ny Og Oy Qd Qt Uh Vs) Ks(Al Ao Co Cv Jd Jk Jt Kg Mb Mm Nw Oy Pg Rb St Ua) cM(Aw Ax bA cU Fr Is Iu Ma mY Nm Nr oF Pd Po Qa Qb) Vo(aJ Bg bZ Ip Iu Jd Jk Jl Jt Kq Mu Qa qV Tv Ua) nD(bC iJ Iq Jd Jq Mv mY No nU Nw oH Om On Pe Pg) nK(Aa dL eF hG iH iJ Ml Mr mU No Nx Om Pg Po Qd) Nj(cQ Cv dF Dk fP hB iJ lZ Jd Ki Kl nW Qy) lo(Dg dJ Dp Gl Ic Iz Ke Kp Kq Qm Qy Ri Ss Uh) Nl(aJ Ap bB Bg Bo bU cS dF dK eF Ez Fn Gl) Rj(aJ dC dD Dk Ez iJ Jp Kq mF mS Ok Qd Ua) iO(Ax bQ cI Cp Fn Fr iH kO Mt Ne No Tv) Ib(Cp Cq Jo Kr NU Og Pg Qb Tt Uo) Qt(Bb Fn Fy Iv mI Nc Nq Oy Pi Qd Ue) hC(aJ cD cY Jy Ld Lu ml mT Nf nI Nk) Ub(Ap bL Ef Jd Jl Kg Ma Nq Pg tF) Ra(aP bB bX dK dM Et iH Jp nL No) cZ(Ap Bo cW Gl Jg Kn mM nW Ou Uh) Nk(bC bU cN eF iJ Jd Ld Ou Rb) bF(dH Fy Ij jH kK Ma Mt Ne Oi) bL(cC dL iP Ly Mm No Oh Rb To) mF(Ar cS dD Di iJ jl Ld pF Tn) mM(Af As bU cD Fa Ou pF Tz Uc) Nm(Bg bX fP Ke Kq oF Rb Uh) Nc(aJ Ap bB bM cC dH Di Dk) Ri(aP bS Cw dE hG Iq iZ Jk) nY(Fa Kk Mg Po St Tn Tz Ua) Dp(Bg Fa Jo Kf Me Pg Tv) Qy(dJ Ij iP Lu mU nJ Qv) aJ(cD dR Fr hR Ij lY Qe) aS(Aw Bn Co Fa fP Jd lM) dL(Al Jk Lv Ly mS nN tF) Ji(Bb cD jD jT oH pF) Bg(bC Hb Oi Ql Tj) Di(Jy Ld lY Nf Qw) Fn(Fr iJ Jq Ld Pc) Ma(Ap bZ cD Kz pF) Ue(Jl Kq Mg Mx oP) Ou(Iv Iz Kz nU To) cH(Ar Kg Mk Qd rC) cN(Db lK Lw Mq Pe) dD(cD cY Ij Mm Oh) As(Aw bZ fP kG) Bb(Gl Jh Lh Ny) Dg(Ly Mk nB No) Fy(Dk Et Kq Mx) Lu(Cp Cw Kp oF) Mt(dH dK Fw Kk) Ne(bX cS Iz oN) Qe(bC dH iJ Uv) Jj(gL jE Kg Kk) Kn(An Hb Ko Kz) Um(Jl Mm Mx pF) Vv(dF Ko Ml Nv) Oy(bW Id Kc Tj) Pi(Al Pa Ph Tz) aM(aI bA bP kG) cV(Jd Lw Mq Nw) nU(bM mP nJ Us) iP(Cw hG iJ qV) qX(Aw Dc Ur Vp) kO(aP cS Kl nW) Bo(Kz lX Ly) Ij(aP Ar bS) Jy(Cw hG Kf) Kp(Mc Pa Pj) Kq(dE Ic tF) Rg(Id Nv Tj) Oi(Bn fP oF) Uv(Dk Ut Vs) cE(Hu jH Lh) hA(cR Cu dJ) nB(aP cD dM) iZ(Lh Nn Po) qT(jI kF mY) jP(Lx Mn Og) Al(jH Lw) Ap(Hb Nf) Co(Qz Tj) Cp(lY nI) Ed(lW Nn) Fr(Ko Qn) Ml(bZ cW) Mm(Iz Kk) Tz(Iv oN) To(dF oN) In(Kg Tv) Qd(aW dJ) Jp(Hb Vt) Ld(dK Uo) Oh(bZ iJ) Ut(eD lY) bB(Hu Ly) bC(iH kG) cQ(Ic Pg) rZ(cR kC) AarY AfcK AriJ BajD BnbU CvUo PoQz FamH NoaE NrbW LwiH MeVs MgPj MnKo MzQh NgIz SsKc QxdE JsPh KiNx KkNw OnbS OwnN UpmZ aUlX cWdH dGjH mIpF mYnJ hWrA kSIM} qD{Mp(Ao aS bI bX cF Co Cv Hb iO Ju Kc Ke Kk Ky Nm oH Pg qG Qh Uk uW tM) Bc(aN bI cB cF cV dB dC dG Et Iu Jt Mu Mw Nq Ok On Pi Uv) Lh(aI bQ cG dF Ed Gl Hc Hu iA Jl Js Ki Kr Mh Mw Mx Nv qG) Db(aN Bb dH Di Et gP Ic Ju Kf Kk Ky Mh Nj No Om qA Qc) Kz(Ad bA Bb cO Dc Dd Fn Ic Kg Mh Ml Nc Nf qT Rb Uf Uk) Kk(Ad Bb Dc Dd Dg dL fP Gz Hq Ic It Ju jY Kc qI vB) Hb(bI cC dB Fr fY gW Hc Hu iO Nv Ny Og Qc Uv wK) Et(cG eF eZ fY It Ky lM No Ri Rj sC Ss Uv) Jp(aK aN Bg Cv Ed eF It Iz Me Mt Qc Ss uY) Jt(aC eZ Fw gW hX iJ Nr Ny qV Qy sC uM zG) yE(aK aZ cN cV fY Iq Ky Nk Ok Qc Uk uT) Dc(aI bI iJ iO Kr Mt Mw Nt Rb Ua Uv) Kj(aN bI dB iO Ks Ky Mw Oy qG Ss uM) Uf(bF dF jG Ki Ky No Qu sC tR tT Uk) Pj(aN bG Dd fN hG Js Pe Pf qV Ua wK) Ap(aV Ez Fr Gl hR Ki Nu Pf vV yJ) Ex(cL Hq iA jO lM Mw Nq Pi Rg tF) Ok(aV bI eF fY hR iO It jG Kj tM) fP(Fr Ly Mh No Nx Pf qG Qu rT uT) Dd(Hc Kd Mn Nt Qy Rj Ue Ul zG) Hq(bG dB dH Fw Hu qA Uv uY tM) Pz(aZ cA dB Ez Kc Kp No Ua Uk) Kg(aI bI dC Fr Iq Ky RB Uv) On(dG Fr Hc Ik Iz jG Qu Rb) eZ(cC Ed Fn Fw hP Ij Kf oF) sC(aZ Cv Fr Jq Ky Mt Mv Mw) Ph(aK Kr Nq Nr qA rB Ut) qG(cF Fw Hv Ki Ky Nq Ua) Kf(gW Hf iO Mt Oi uY) Um(aN bR cU Mw Of Uk) bG(cI Ki QA uW wC) tM(aE Jq Mh Om rX Up) vW(bC cW dC Ii oF wC) qV(Hu iJ Iq rT uP) Nq(Iu Jm Nn Nx) Ic(aI cC Ky No) Hc(Ad Ef Jd Of) Hf(dH jY Nn qQ) Dl(bI iO Ky) Nu(Iq Sr uX) Me(cO Ly xA) Nx(cC Rb wC) Uv(aA bA jH) dB(Nn wH wQ) iH(Ch Ml My) qA(Aa Uk uU) uP(cC dG Ky) Al(wB zG) Ed(aG dC) Gz(bS Oh) No(Jv Nw) Nr(Ij uW) Nt(Aa Sr) Hu(Ao Ke) Iq(Rb Rf) It(dC dH) Jd(aC aN) Ss(qI wQ) bW(dH uL) iO(Iv tU) vP(aZ Uk) AdMw AsqU BbOi CvvB FndF MtSr IduM IjIk IpvU IuKy JowJ JqwC KruW aNcF bBwK gWtX} Us{Ly(Al Bb bF Bo cD Ch Co Cv Dg dJ Fr Iq Jt Kf Kl Lx Mq Mu Mv Ng nK Nv Ny Of Om Pg) qT(Ao Bg Ef Hb Hq hR iC jH Jq Kl Kx Mk Mr Mu Mw My Nx oE Pa Ph qW Qx Rc Tz Uk tF) nK(Ar bF bL bQ cG Co Cp Cw Dk Iu Kc lY Mv Nd nU Ny ON Pd Pe Pf Pg Qy Rg) eD(Al Aw Cv cW Et Ib Iq Iu Jt Lx Mu Nx Pe Pf Qt Rc Tz Uc Ur Ut Vq) hR(aE Aw Cq Dc Hq iJ Jf Jp Ke lO Nv Nx OF Pd qC Rc Tn Ur Ut Vq) On(aW Cv Fy Hu Ik Iu Mb Mc nN Nt Oe Pg Ql Qw Rb Rh Ue Uh Tk) rX(bP bQ bW cG cI cL Hc Hw Ji Kf Mk Pa Qy Qz rY Un Wm) qU(cW De Et Ha Iq Iz Kf Mq Mu Nv Nw Pd Po qX Ss Ut) qX(cT Db Dd hG Jf Jy Ke Li Mq Tz Uk Un Ur Tj) lO(Aj Al Cv Et Iu Iz Jk Jm Pf Rc Tz Uf Vq) rY(aP Cv cW dD hA Jp Li Lx Ou Pe Uf Vp) nN(aE aP bZ Fr gL Hu Jk Kk oQ Oy Rg) nF(Ap iJ iO Iz Jq Ke mZ Oh Pd Tv) Nx(Is kI Oe Oh Ou qW Qz Ra vO) rZ(cG dK Jo Jp Kf Mw Nw Pc) Me(Ap Bo Cv Dc Kq Kz Lh) nB(Dc Dd Ip It Nv Qb Qe) rV(bH bX cC Gp Jr Nb Ow) Ic(Ap Cw Dc Kf Kq Lh) Qz(Ar Bb Bo Cw Jg Ou) qC(Di Is jD Pb Qa Un) lM(Hb Ii Iv Ma Nc wB) Ap(iJ iP Ra tF) Ib(Ad Cw iB jT) In(tN tO uV vO) Jg(Nl Ou Ra Rb) Lh(iC jL nJ wJ) wP(cD Ki rC wK) wD(Cu dN Nn qY) qW(Iz Jt Li Tz) qG(aO Jo Pd qY) sC(Af Pf Rc uN) Ng(jL jM rA) Tn(hA jO nU) Jk(jH jM nD) Um(uL uN zH) mF(Ba cL Cp) tN(bP Or tX) yK(Dp uX Vt) tL(Fa Kr qV) uM(Cx Ez Mf) uV(Or Ph St) vU(jE Ni wG) Cv(hW jD) Cw(oK Rb) Nm(vV wG) Kq(dJ Nc) Pf(kI mT) bQ(vI zA) cW(jG jI) tF(Ok Vq) nR(cL Tv) nD(Cq Ml) nJ(Je Pg) hL(Cu Iu) hP(cI Iv) iC(Jd Jp) jT(Et Kf) xA(Ao Mh) pS(jY vB) qQ(Kg Uv) oQ(Ou pF) AllY ArvO AwlL BaNf BbrA LxhA MdvB MmwJ MveZ UeuN UcjM TrrS IqjV RbcD JfvS JmoP KkvI KsrT TkVs OguX UfjO OyjL PhtO aErO aJuU aOtM aZuW bAwB bCzA} nO{aS(Af Cp Di Fa Fr Hc Jd Kg MM Mx nB Pe Qn Rg Rj Ua) iZ(Bo bU bW bX cD cM Co dD iP Kg kO mU nB Nj nN oP) nF(bX eF hB hC Mn Mt Mw Ny Oi Om Ou Qa Qy Ut) As(Ap bQ dD Jq kG Kq Mm Mn Nw Ny Ok Ou Tv) Hc(cH cK cO Dp Ij Kc mP Mq Nj Nk Ug Uo Vv) bW(Al Ax bL cY Hq Iz Lu Mf Mx Nr Oh Rg Uf) aY(Ao Bg Bo Co hC kG Mw My Ny oF Om Qx) iP(aJ Bg cJ Is Iu Ma Mp Nd Oh Pz Qd) Kp(bA cG Cx Ij mP Nj Nm

Figure 21 Continued

Figure 21 Continued iC(Al As bZ dA dD Jd Kc Mj Ml Nn oK Pg Rc) jO(Aa bE cW Ez gL iH jL Ks Nm Pf Ql Rg Uc) jP(Al As cY Ed hG hX Ih jE jG Kc Ma Oh Pf)
hR(bO cR cS Fb Fy Ih jG Ks Mz Nm Nn) jT(cA cC Io kO Kr Ma Mp Nf Nj Nu oK) rZ(aV cE cL cS Iu jL Jy Kj Nm oK Uf) Ib(cZ Ed Hu In Kk
Ly Nj Nt Pg Rb) qU(Ed iJ Ma Nb rC Rj Ug) rY(Fw Iz Jk Js Nq Ow Rg) Ks(iB jI jK lN Ly rX) In(Ic Ne Nl Qw tF) rX(aW Kf Nq Pc Qw) Me(Ic
Kk Ue Uv) IN(iH Ke Kr Nq) Tk(bO Cu Uc) nN(Lu Uu Vv) jM(Io Mp Nf) Gl(aC oK) Ly(cD Fw) Qw(jL Ou) jG(dD Jo) lL(Ij Pg) GzwC NqlM
loiB JfnB VvmF cCjL cWjI} Qw{tL(Ba Ch Ct Cv Ef Ib iP Iu jO Kf Ms Nc On rX rZ Ss Ue Uf Uk) uM(Ch Cv hG Kz Mf Nb Ng Nl Nx Qu Ua
Vt wQ) wJ(Aj aZ Cv Dg Hb Iz Lh Li Ms Nm Ph rY) wL(aC Ch Ct Dd Ef Ib Ii Nm oH Or Uc) wQ(Al hB iZ Kc Mn Oe rV uR Vs Vt zA) On(cD
eD hA iC In jG Js Ou rV tQ) vW(Ao bC Ch Ib Jg Kf Nm Ok Tz Un) rU(Hw Nc Nk Nm Pz Rc Tt Uf tM) vB(Ch cL Ct Ef Hq Iz pS RB) qC(bW
Dg Fn Ms Nl Rj Um zA) qQ(Et Hr Is Ky Pj Pz rZ Ul) uX(cF Di Fw Jv qW Up vA yH) wG(aP bC cJ Hq Nu Rc Uk) uW(bl Jv Mp Nb Ni oN Qu)
eZ(Ao Bg Cp tV vI) wD(aZ cC iC Pd Uk) jP(Ch Cp Dk Jd Mw) hO(Kz Ne Nj Uv) tO(Aa Kf Kg Lh) wC(Ij Ik Mr Ni) Nm(vA yH yL) Qh(eD IM
lN) cW(eD hA jG) xA(cD Dc Mv) tM(Aj Mg Ss) rV(Nj Pj qW) Ba(hA jT) Rc(qX rX) Jg(Ib vP) Kj(hL qB) wH(Hf Kr) pS(eT jD) IM(cG rZ)
uG(Dk Kl) vI(oN Ub) AdjM AjvT AwrQ BcrX CowK ExkP FwqT IjyL ItyH QurO JvzA LhpY UrwF UuwB OytS PenB aPzI aZfN bWqB
dLqA iBtR} nN{Ks(bF Co cT HC Kg Kk Kq Lh Mg Mn Nv Nx Pa Pf) Vo(Bo bX cM dL hC hG Kc Kq Li Lx Mg Mu Nx ON) Ug(Ar Ba cM iH
iO Kf Md Ml Ms Mv Oh Oi Po Qt) Lu(bS dL gL hG Ib Ic iZ Kf Kp Kr IL oN Uf) Kn(Fr Fy Hb Ko Ml Mp mW nC Oh) Vs(aM iP Jj Js Ml Na nR
Ue Vp) Ic(aM cM Kc Li Mp Mu oQ Pf) Kk(Id iO Lx mU mW oQ Qt) Rj(aY Bo cL iO Jj Qt Uo) aM(Ed Hc Nf Nn Pc To Uf) Oh(cM Dp eC Gp
Up Vv) iZ(aZ cA cL eC nB Rg) Ar(Fn Fy jD jY IN) eD(Co nY Ur Ut Vt) oN(Fn Kc kN Ou Ql) Nn(cM Cp cW Db) Lx(cV iH Uc Ue) Ib(hG kF
Oi Uk) Id(cA Di Li Oy) In(Cq Gl Kq Tn) Jj(Iz Kd Kp Uf) Ow(bL Fy Hu Rg) Uu(aJ Lh Nx Pf) Fn(Kq Pc Ub) Nm(cS dL hG) Ly(cV Db iH)
Iv(Kf St Ut) Kc(dD Gp Js) Uf(Db Na nl) gL(dD kO Qy) jP(Ao Ct Dk) Co(qU Tj) Ex(Ne Qn) Nj(bP cS) Lh(Ao Hb) Rg(aY mP) Ql(Mu Pc)
Uk(cQ Di) Vv(hG Hu) IK(aK bP) BapF FamP FyJq MeQt MgPj NccM NldL UbhG UcPf VtjM dBiC} hO{Hf(cC cI Cu Fn hR Ij Kj Kk Kl Me
Mg Nf Nn Nx Om qC Uc Um) Iq(aX bG bR Ip jH Jp kQ Me Pe Pz rB rS rY) Ki(Aj Cv Dk It Jp Ju Kf Mg Ng Ok pS Qu Rj) fP(aU Bc bG Cv Jn
Ju Md No Oz Pd Pk vW) Kz(Aj aN cC Dc Ij Kp Nc Nl Uf Uk Uv) Ad(hG Ik iO Mt Nb Ow Pk Ue wJ) Db(Et Ib Je Kg Kl Kq Ok Ph Pj) Na(Ax
bX cR Fn Hw Jm Kg Nj Nn) Jd(As Me Nu Pj Pk Rb Ue Uk) Dc(aZ Kr Ow Pk Up vW xA) Et(al aU iJ Me oH Pk qP) Qz(aG cG Hq Nj Ow ul
yE) Jt(iO Kk Li Me Mp Pk Rb) Kf(aV hR Kr Mp Pe Pf Rb) Uv(Fy Ic Jp Kg Mg Pj Rc) Dd(As dB Kd Kr vW wJ) Fn(bG cF Mu Nu uM) Kg(aK
aU Mn Nb xA) Kk(Hq Kj Mg rP Uf) Pj(aK aU gW Um) xA(As Cv Nh Pa) Uk(Hq Ju vW) Pk(bG Of Qh) Gz(Hu Pe) Me(Pz yH) Lh(Gl Ow)
Um(dL Qu) Uf(al dB) uM(Fb Tz) CvcB NovS NqMg NbPz HqKy HuKj HbaK KrvB PhcJ aNiH dBrY} nB{Jf(Dc Ib Jq Mv On Pd Rm Vs)
tF(bU Co gL Is Nc Ne Nl Qa) hC(Iu Mn Nr Qa Qe Ua Uf Vu) iP(Ex hA Ip Lx Mr Nv oN) Gz(cE cG cL hB Hv Iv Ug) Ub(al Ar aV dA Dc Ir
Qa) Vv(Dd Hx iH Mt Mx Nv Qy) aS(dK Ex jQ IM Nv Qb) Fw(It Ji Pf Pz Ut) Iz(bW bZ Kl Ma Of) Kg(Lu Mw Ok To Tr) cZ(Im Jq Ny Qe Qh)
nR(Ba cE Ex St Vu) rA(eC hA Hw kG IO) Tj(Jq Oy Qb Qh) Nm(Dc gL Kc Lx) Nr(Fb iO Ke Nj) Qy(aI Lv Mt Nc) cV(Ly No Pf Qe) kQ(Gp Is
Lx Mt) Mw(Al Dc Qh) Nj(Lz Mn Pe) To(bF Gp Og) Tr(Nv On Pz) Ki(cB dA Rm) Ou(Ph Tv Ut) Vo(Aj Im It) aV(Ex Hu Nv) dl(Hu Iq Pf)
iH(dK Jy Qz) pF(Ir Is Qe) Dd(eD IO) Nl(Ar Db) Je(My Nv) Ko(bV Uu) Rm(Cs Mz) Ug(Mb Vu) Vt(It Nd) Pj(Ip Nx) bC(nl Uf) bW(Ua Vs)
dN(iB IM) qT(Dl qU) kO(bU Dc) Ajlb AlJn BoLx CuhA DglM ExmF NsUl MaKp MtRa NciO TzKs UcNy HwjT InQh IrOr IsbX KxbO LheD
LiPk UtaA PhmZ bHqV bVcL cNIK cPIO cWrX gLkF iZrY} cC{qG(Ao Ba cB Cp De Ef Fw Gp Mg Qt Ss Tr Up) wL(Et Hw iO Iu Jh Jm Jo Jq
Ns Uc) wQ(Dc Hb Hf Iq Jg Jq Ma Vo Vp) Ly(cN Fw Gp Is Iu Jg Ok On) Uf(jG jM qQ qT qX rX rZ) tL(It Ms Nn Nu Um uW Vt) vB(Jh Jq Kf
Kk Nj Nx Tz) Aj(qA rN sC uP tM xA) Ok(hA jM qX vP wJ yL) uW(Ed Fb Jv oN Qu Vt) vW(Dc Fw Ib Jj Nm rY) Et(hR jP jT IN rX) eZ(Dg Dk
Dl Jg Lh) qC(Ic Iq Lh Qc Um) qX(Bc Fw Gp Jd Jg) yL(Jo Mw Pj Ss Uc) On(eD iA IN uG) Pf(eD hA jT rX) wD(Db Hq iO Mm) wG(aZ iC iO
Jh) xA(Hb Jo Om Ug) tM(aO Mg Qu rY) rV(Hf Ij Kf Tz) rU(Dc rX rY sC) Ed(bX Ml uP) Iq(eD wF yH) hR(Ad Li Pc) yD(Jo Om Ph) qA(Dg
Dk Kl) qQ(It Pz Tt) uM(Cv Fa Un) Db(jL wB) Kg(jT tT) Ur(tU yK) wJ(Bb Kf) uX(Hf Kq) AafY CvlM DggO FwuP MmvP UbrQ HbqP IseD
PzpY QtwC JuwK KzrT WnbG UkwH PcrX PjvO bWuL hAnI iHjL oHuN} vW{Fw(aO bC bZ cR Cu Db Fn Ii It Lh Mg Mm Nb Ne Nn Nt Pa
Uf vO) St(Co Cp Ct dF Fb gL hG Jh Jq Nn Of uT) Me(Ao bB De Dg Et Hc Hv Mm uT yH zI) Qz(aW cl Et Js Kd Md Qd Qe qW rV) Kr(aC Bg
Co Is Lx Mg rV Ub Um yH) Db(Al Ba Dg Ef Jh Ki Lx Ni Nm) Ed(bX fP Jj Ki Ky Nh Nl Ok Um) Uf(aK Ih Kk Lj Qe Up Uv wG wK) Aj(aP aZ
cR dB Ez Lj rN rU) hG(aZ Jd Kp Mg Nm No Rm rY) zA(cN Iz Ki Kz Rc Uk Uu) Et(aL bl cQ fY Rf yD) Ad(aP Cs Na qC Rf) bW(hL Iq Nm No
wF) Jd(Ar rU rY tL) Qu(Kk qC rN Um) Fb(aW Nr qC) Hf(Is Jh Uc) Kf(Ih Lx rB) Um(bP Dk Jg) Uv(jH Lh rY) aZ(Dk jQ rY) dN(aW dB Nm)
Bc(aH jH) No(Ef jF) Nt(Ao Dg) Ki(Nr vO) Kk(aC Kl) iH(aX vI) wG(iC Kx) uX(Oa Uk) AxHw FnrU NqUu IhSr SsrB JjUp OfoH OnqC aKbC
dBIK} xA{Kf(dB Ed Fw hG Jl kQ Mn Mp Nt Nu qC qX) Bc(Aj dR hP Jd Kg Nb Nc Nl Pk Qd wG) Me(Aj cL Hu Jq Kq Lh Mh Nr Ok rB)
Ue(Ao bC bl Jg Kl Na Nm Om Ph) Cv(Af aW cB Md Na qW St tL) Qz(aP cD Jd Mp rB St Uk vB) Uf(aZ cE iO Nd qC Qe Up vH) bW(Ed Et
Hc Hr Kr Nj No rU) dB(bG Dd Hb Jo Lh Mm Nn Om) Ki(Kc No Ok pS uG Vt tL) Db(Ad Bb Cp hR Nr qW) Hf(Ik Kx IN Mm Ss yH) St(Ar Ba
Jh Kq Mm Nn) Dd(cN Jd Pc Qe yH) Et(cR Dg Qu Rh Ri) No(Hb Kl Rc Sr Uv) Um(aZ cN dR iC rA) Fw(fP Jr rZ uP) Jh(iO Kr Qu qX) Kz(Jg jR
Ok uX) Bb(As Jp rV) Bo(Jd Rh Ug) Nd(Jd Rb Uk) rU(Kl Kn Pk) Ad(aZ Mn) Rb(Hw Om) Kr(Dk Mm) Pc(Kk rA) hG(Aa Kx) jF(Jo Lh) AfNt
AjNa AoiC EzJg MnaO HuOk HbuG IqKd JdqW KlaZ OmrB PatF PkcN} vB{Ue(bP cL Cs Hw Ii Iz Jo Jp Kg Nb Nn rA rB Rc Uk Ur Uu)
Rb(Bb dB Hq Jh Kf Kk Lh Nb Nm Qe uG Un vO) Me(bE bL De Jq Jr Mm Nb Nr qC rB Um zl) Um(Bc bE bL Bn cA Db De Iq Pc rA Rc) Ex(aJ
Dd Dg Iu Jj jO Ky Nn pS qH) Kr(bA bO Dk Hq Ii Nb qC Qn rO) bL(Aw Dd Ip Kc Kk Ms Mw Of Ug) Db(Aj bQ cl cS Ib Kk Nb Nx) aP(Aa De
Ed Ki Kp Mf Pa Pc) Hu(Aw Bb Cp Iq lM Mf Ok) aZ(Al bX Fa Ki oH rB Ub) dB(Aw De Lh Mm Nr Nm iQ) Iq(bO Et Jd rA Rf uX) St(Aw Et
Hb Ii Kf) De(Fr Ki Na oH) Fw(cN cR Rh) Qz(rC wK yL) Uv(Bc Ug vO) Nt(IN Mf) Mp(Bb Un) Ki(iC Kx) Kk(iC Kc) bW(Aa Mb) cR(Na Up)
iO(Aw rY) AjrB AlQe BcEt FnjM FyGz MvHc KfjG KxeD UkfY UgbU gWrA qCtM} nR{Vs(aM Ar Ba cH cR Dd Hv iH Ik Im Ji Kc Kp Ld
Lh Ly Mh Mr Mt Nd Pd Pi Vv) cL(Hq Jg Jh Lu Ml Mr Mw My Nj Nl Nx ON Oy Pg) Ba(bP Ct dK Fy Kn Ly mS Qt Tv Uk Vo) Lu(Dc hB Kc
Kg Kk Qy Rg St Ua Ut) On(bl cA dl Fn Ic Kk Kn Ql Tv Ug) Uf(Ar bW Kn Ml Mr Mt Nl Nr Og) Tv(cN hC Id Ij iO Iv Js Mn) Ex(bL Cp Fp It
mM Ow) Nx(aW Fw Fy gL Gp Ug) Kn(Id IW Ml mP Ri) Ut(aW Ik Iv Lv mS) Fy(bF Kq Lx mM) Nj(dG hC jT nW) bF(iZ mS Pf) Gz(oQ Ph)
Lx(bl dA) Ic(oP Pf) Id(gL Rg) Qy(Lv No) Uh(gL tF) cE(dK mF) jH(As kS) BglK DbjT DcNv DkcG FwOh MncH NlfP QeaW JibP RgmW
OibQ VtlM VoiO aYoN bMqT dDrZ} Qz{Ou(bQ Ch cT Dc dD Di Ed Fr In Jh Jq Jt Kl Ko Lh Lx Mv Ng Og Ok Om Qt Qu Ss Tt) In(Ba bF Bo
Co Cq Cv Dc Dk Iu Jm Kq Lh Lx Mr Nv Po Tz) Ar(Ki Mh Nt Nu Oh Pg Ra Rj) wL(cR hW Jr Rh Ug Uk Ur wK) Fw(Bo Cv Ha Kq On Ra)
wK(aM As Hq Qy uU zH) wQ(De fP Na Ns rB uT) Pg(Ba bF Bo Kq On) tL(aZ Jq Ow qW Um) Ib(Ad Bo Jg On) rU(iJ iO Iq Pj) yL(cG iJ Iq pF)
cU(qO qP tO) bL(cB Hq iP) wD(bE Pa Vv) qQ(Mh Mr Tt) Aa(rV tO) Bo(Mc Ue) Cu(Kq On) Cv(bP Ic) Hu(sK yE) aZ(tT yK) eZ(hG Qv) ul(iC
Ih) DewE DiuX WmEx EddD GpRa GzkI NtjT MduR NbwG UctX IckO JrwF JtrV KzqB UktO VvfN bFbQ cWjG dCtT fYvP wJpF iOqC
zGjH} iH{hR(Ad Al aN aZ Bo bW cN dD Et Ic Jd jL Js Kq lM Ok Om) eD(Ad Bo bW Fr Hc Ic Kk Lx Mc Mn Ok Om On Qh Tz) jM(Ba Bo
cW Dc dl Et Jd jH Li Lx Qt Uf Ul Vs) Ed(Ba Fr Ib Ic Ij In Lu Lx Mm Rj Uf Vs Vv) qC(dC It Kg Ki Kj Kk Mh Mm Mn Mw My Rb) lM(bG cO
cU dH eZ hB jO Of wB) IN(Cv Gz Hc Iq Jd Mk Ml On Qh) hA(cE cW Ij Iq jL Lw Qh Rc) Ib(Ef Jg mZ On Tn Tt) hL(Hq Jk Li Mw Nv Ut)
jL(bG bV eC iA Nu) Fw(Hc Jt Kq On) rB(kO Mq Qh qT) In(Ad Jm On) jH(iP Jd Nf) wD(iC jO qH) Ic(jK Ou) eZ(hP vl) iB(cN Qh) jP(Ba Et)

Figure 21 Continued

AdOu MaoQ IvjK RamT OnPg UfjO PkzA aPuX mErX} Db{uL(Fy Hb Jg Jh Kj Kn Lx Om Pj qC rB Uu) rV(Dg Ed lj Jh Kg KJ Nr Pb Uu)
wJ(Ic Jo Kj Kn Lh Ly Nm Uk) qT(eD In Iv Js Ou Pf Vp) iC(cW dD Jd On qX wD) wH(aW It Mz Qe rB rO) qU(Ed jL Kq Lx Rc uX) jM(Ad dD
Et Fr Jg On) uW(Aa Ed Lx Ni Nr Up) qC(cW Hu Pz Qc rZ) wD(aZ Iu Jv Ky Nt) jL(Ad cW dD eC Ou) Uf(hA hR jO rZ) eZ(Aj Jg Om Ss)
qX(bP Hx In Kq) tL(Dd Nt rX Ur) wB(Ba On Rc) qG(Ik Nj Ss) Ly(bX cN) hL(Aj Dl) rZ(Pf qQ) rX(Ib kR) rT(Aa Iq) rS(Et Tt) sC(Rc Ss) uM(Fw Ni) DcqB NuuX MguG TzrQ QheD KlwK LijP UmtQ bCvA bWuT cUfY cWhA dDjG hGzH jRqP lMoN} Hf{qU(Ad Fa Hc Jh Ji Jq Jt Ok Om On Pf qX Tz) qC(bG Hb Ly Mp Nf On Ph Pz Qc qI qQ rS) wH(aJ Ba Cp dH Jg Jk Ki Nm rB rC) uW(Dk Mp Nb Qc Qu Qy Rc Up) tL(bL cM Dc hG jH Nx rX) eD(Ad Cv hG Ok Pf) wQ(Bb cA cE Kx uL) qX(Bb Bc bG Cv Kq) qQ(Kf Kq Mh Nn Qh) wL(bC Nr Qh rB) wD(bB gL Kf Kx) rZ(Bc Cv Pc Pf) dD(hA Mc rX) wJ(Fy Kg Kl) wK(Kg Ss Uk) qT(Bb Js Kq) uL(Fy Nr rB) uG(Dg Kl Mg) uX(Jv Mp vT) vA(Aj Kj Mm) Jp(rU uM) On(iC jM) cW(hA jG) hL(Dl yH) rV(Kq oK) AdiC AfuM CvhR DdyE TzrQ QhjM WnaN UurT PfhA PkrU bCsM tRoK iOwF zHoH wCrY rXoE} Et{wJ(aP cA Iq jG Ko Qm qT Qy rA Uh Uk) qG(Af bQ In Jl jY Ke Ow Qu Uh wQ tL) fY(aZ cA dB hV In Io Iu vP zH tL) wK(aU aZ bG Dg Ed Nt oH Uh) wQ(aF aP As cM Ow Qy Rf) rV(bI bL bO bQ Hc hR Rb) Ks(hA Ly qX rX rZ tF) bL(rZ tO wD wL tL) yL(cJ iO Iq Ow Ue) tT(aZ Ed Io Qd) In(jT Kk qO) eF(rP tO yD) pS(aU cG hR) rU(Nw oH Um) Fw(qT qX) Iq(wH tL) Li(uL yD) Ri(rN tM) dB(qX rX) fN(Nw Uk) rB(qC wB) wC(Dg Rb) rZ(Ed Vv) rP(Qy Uc) qP(Jl qW) uM(bW Ko) vT(aL St) AshR BcrR NtqT MeuL MnyD MpuX IhqQ JieZ JsjT KkTk UmwL UvvP aUrN bUwD cJwG cYuG dRqO iJzH oHvH} Ed{mF(bB cM cO dH Di fP Gl Id Jj Ko Kx Lv Mm mZ Ow Oy Tv) On(Ao aW cG dM iA iC iJ jT Uc Ue) qX(Ar Bb cB hG Kr Kz lK Pb Pc Qv) wJ(Dd Hw Ij It Jp Ju Kc Ki) Ex(Ic Ik Ml Mp Nf Nl Ul) rZ(cN hG Kg Kz Mm Pa Vs) nC(Id Ij Mn Mw Vs) qT(Ic Js Kf Pc Uf) Nt(lM sM tN tS) Io(mH mP mS mW) Ki(cE cL lM tN) Vs(mI nD nL) cW(hP rY vI) uM(dB Jq Tz) Ba(iA iJ) Ic(bX fP) Um(vU zH) Uf(aG wK) Vo(cE oQ) Pk(rU wK) hR(As Pa) tM(jE jY) vT(Bc bW) ArmW NjvU UcbX TroQ IjoO IumP SrtT QvcN aGcE dBwQ jPuY} wQ{aZ(As Bb bH cJ cL cQ dB Kr rX Um vS) Ki(Ba bS Fw hC iC Kp Kx Lh Pa vO) Kf(cJ cM Fw Jl Mp Qu St Uc yL) Kr(Ba bZ Ns Pc Ph Pz rV Tz Ul) Ue(bZ Ip Kj Na Ok Pj Pz Uk) Uf(aI bE bZ gL tT vI wK) bZ(Aa Ib Jl Lx Mn Ua) Uk(Ao cJ Ip rB wG) fP(cE dB iO Mt oN) Cu(jM Rb St) Ex(Pa tO tT) Nt(Ba cB Kg) Iq(eC Rm Vp) Jo(bU cJ Kz) bG(Dd Lh Ul) Aj(Mp Na) Bc(It sO) Hc(Ao Ef) Is(Kd Up) St(Dg Tz) Jr(aC rV) Kz(bB Nm) Um(cE Mf) AsJt BoOf LuRf MmcJ NaHb IpbW RbJj QviC JvaC cZjH dBqY oHvI} Bc{zH(aK aU cL cM fY Ih It oF rW Uv vI wJ) vT(aF Cq dN Il Jl Ml Ns Oa Qu rB Uf) vI(bI Bo dM Hu It Jp Ky Mr rY) rV(aG In Jt Ky Mp Ph Qm uM) wJ(dM Ic Kl Ok Pa rA Ul) yH(Cq Dd hG Il Jl sK Vt) sK(bL dN Kp qW Rj yL) sO(aG aI As Oi Pc sM) tO(Jl Or Qb qW Uk) tV(iJ Ly qC Qu Qy) uN(aS Bg cK dD dF) qB(Ad Gz Kz) wF(Bg dE Uk) Mp(rP uT) Pa(rX wD) dM(rS rW) yK(Mf Qe) wG(cH rO) rU(Fw Up) AavO AsvH BovU WmtT ExqA OfrY PcwD PhqC bFuI bLyL eFzA qXrX} qC{tM(aO bB fY gP Is Jm Kc Kf Lh lM Ms oE uW) Pk(aN cR Dk JD jY Ow RB sM) fP(bG bZ cI Jd Nb Nq rT uT Uv) Ad(As bI Hu Me Mw Ue Uv) Na(Ij Jm Kj Pj Qa sC) Iq(dB Hb iP Jd qV rT) Hu(Ao Kf Kg Kz) Kk(Kg qV qW rY) On(dB eZ jG Ky) Um(Bb bG Ij Ng) Me(Ly Mp qU) Jt(cW Mp Rf) Kf(Kr Mp qG) Kz(Ph Pj rQ) Uf(Nq Uc vV) yE(bW cF hG) Hb(qG Rh) Pz(bI dB) Ki(bG bI) Lh(tT Uv) DcaN NoQc IcwJ IkKg RbsC KruY dBuP rUvP} Fw{qT(aG As bG bL Bo cE hG Hw iC Ij Kf Kg Kn Kz Lh Nb Nn Ny Oa Of On Qb Rj Tv Ue Ul Vv) rZ(aP Ba bF hG Jq Nv Ok qX) qX(Co hV jR Ok Pc Tv) Nj(Ar cB Ly uM tM) wJ(dN Ic Jp Ky Nn) Kf(jT qG tT vT) aC(Al cB Dc Iu) hR(fP hG Ok Qa) Ly(aN cD Iu) Kk(uM uU vI) Oh(cF mZ nH) uW(Jr Ki Ky) Dc(jM uM) Ue(Kq On) Hw(tT wK) Ic(bX fP) Qa(jY nD) eZ(Fn Jp) ArUm BaiA NowK IbTt IsuM KccF OnbQ PacB PenD cRqG cWrY fPyD jYuG} rU{vP(Ao bB bN Fb Fy iC iO Kj Kx Rc) Iq(aK In iP jH Mh Qg St uM Vp) Ki(Aj bA Hq Lh Mm Pa rB Tr Ub) Jt(bU gW iJ iO Kd Kz No Rb) Kk(Dl Ij iZ Kc Om Pc vO) Hu(Ba It Jg Kl Nn uX) Kz(Jp Kp Ph Rf Tz Ug) Jp(Mp Ow tT Up) Pj(aU aV cQ Ue) dB(bH Ok rY yK) No(Aa Kf Nn) tM(cY Jd Kf) Bb(qP Uc) Dd(aK Na) Nm(Kr Nt) Hb(aK Um) Uf(iJ wK) aV(vI zI) yK(iO Kx) sC(Ky Rc) vV(Bo Jd) DlNa KgiJ KrOm OkgW aFrX fYwL wJjH oHvH} kO{Ic(Fr Is iZ Kf Mb mS mZ On Rg Rj St Tv) rA(aZ hW Jl Lh On pF Pg) cM(Al iZ Jm kP Nc oN Rg) Ml(aM bU Dc Gz iP Qx) iP(Lh Ne Nj oF qV) Ly(aN Qy Ss Tv) Me(bL Gl Qy Vs) Hc(Aa cQ Nm Ub) iZ(aA jQ mZ rC) qX(hW jE jF jR) jT(Aw Ba Ms Mu) oK(hR hX rB rY) Ch(jU jV qT) cR(hA qV rC) Dc(nD Nm) Tv(In iO) Oh(Oa Ud) cB(jG jP) jQ(bJ cK) LvQy NfRg RjnD VoiO aNlM aZhX bBeD bZjP cHoE dHrC gLlY} mF{tF(Ba Bo Gp Hc hW Iz Ke Pf Rg Ua) jE(aL aY bQ bZ cJ cT dB hB kR) Lx(Ij jF jP Ou Ra Vv) lK(aP aZ cE cT Up Vu) Vv(Hu Iz Jk Ua Vs) qU(aM aZ bB Bn eC) In(Hc Ua Ut Uv) Ql(Iu Kk Lh mZ) qT(aC Io oE Oy) Il(Al jT Kn) Js(Kf Nr Ua) Vs(Ma Mq Mz) hX(cH dG dH) rB(aP bA oN) Ba(pF Ra) Dc(jY Vu) jD(Cp De) rZ(dE Nh) rX(bB dG) AwjY BghA CqVu ExcQ NmoP MzQh UfeD UtjM aWlM aZjF hWiA} kC{rZ(aZ bP Iq Iv Jr Ma Of Oi Oz Pz) hA(Ct fP Iu Js Ng Nm Ue Uh) jD(aP bA Bg dD dH It Iu Po) jM(Aw aZ cB dH Lu Og oN Tz) rX(bF cE cV dG iO oN PF) jE(aP bW cO Ij Mp Mq oE) qU(Cp Cs Nx Po Tz Up) jP(dL Jq Mr Nr Nu Nx) lM(aP In Iv Jg Mu oF) iC(aZ cE No Uf) jY(hB Nj No Uf) eD(bQ dH) qX(dE Up) qV(Dc Vu) NoqT MeId ItrA OgrB} tL{Me(bL jH Js Ki Rf tR Uk) Nt(Ax cB Cu hG Ow Ra) Nu(bL Cu iO Kx oH Sr) Um(bM Nn Rb Ss Uk uN) Iq(aZ cI ON Rf) dB(Aj cF Jm jY Nn) Cv(Ba fP hG Of) No(Cu Fa Rc Uv) Jr(Jd Mp St zG) Kr(aZ cR Hw Tz) Uf(aF fY Kk Ow) Kz(Jm Mk Ne) bW(aC cM jY) iO(Ij Jt Kj) Fb(aF Ue) Ip(Ex Rb) Jq(dN Ow) bL(Jt Tz) AdMp DdaC MnOn MtKf UebC HbOw IsaZ KiKj aOcM} In{Ic(bX Cv Dc Jm Nv Nx Ny On Qa Qb) Ly(Ad Al Ar Ba bF bX cD cE) On(Al bX Gl Ib Jd Jy Um) Al(Ki Nl nU Rb rZ) Is(aC bG bX cK) Jm(hF Ki Kq tF) Um(Ha Kq Nv Qb) Dc(hG mS nU) Ex(Ad Jt Nh) Lx(nD nI nU) Iu(cB fP Kq) Qa(iA Ki tF) lY(Gz Hc Tz) Nl(fP Ok) Kk(Kf Lh) nD(Nr Po) ArNc BaiA CqnL CvKi HaLh TzmS UemZ TtqT VsmM bLrZ mEjT} Iq{tV(aW bI hL Hu Lx Mn Nq qQ Rm Vp wF) rV(Af Cv Gp Kc Kr rB Uv) uW(Ex Mp Pe Pg Qc Rm) wL(aW Hv Jp Ms Nn) wF(bU hC Jj Nt Nx) wD(bU Nt On Uk) qQ(cB Me Mr Nt) uY(bU cB eT Um) Um(qB yL) cW(jH jM) eD(dB qT) mE(qX rA) qG(Bb Up) rO(Hb Ih) uZ(bU cD) NmwJ NuwG MhrR MnhP MrvQ MtzA QbuX JjwC KrrT LhwH RfhL aZvV fYtX rBrQ rAkF} iO{wL(Ad Cu Dl Hb Is Iu Jo Jp Jt Kj Mg Nm Nt Uc) wF(Ao bX Dl Hb Ip jH Kj Nc Nm Ok Um Ur) wG(Ad aZ Dg Dl Kl Lh Ns On Rc Ri rX) zA(Ax Jg Ji Jq Kl Lu Ms Nj Nn Nx) wD(Ao fP It Jp) rV(Dg Dl Ij Kl) qQ(Kf Ki Qu) Ok(qO wJ) zH(Ms Um) uW(Kr rY) AwwH CowE ExlY GznD LxnI KfrO KlwJ bWvT mEjP mZiJ} dB{rX(dD jH Ji Jq Li lM Mc Ns Nw Ok qX Vt) uM(aO Cv Fa Mg Nj qY Ub) wH(Ba fY Ip Ky Rf) eD(lW mM Nn oP) qX(bG jH lN Vv) uX(bG Ju Na Up) wG(bC cL Uk) qU(On Pf Qh) qG(hP jH Kl) yL(Aj Hw Uc) Mg(rN uW) Is(qQ zH) Jr(tV wP) wJ(Dg Pj) wL(fP nY) iC(mM sC) lM(Nq Vv) AjtM NaqQ HqjL JgvP QueZ JmwF JuwC KruW UfyE aOwB mEhV} lY{Ly(aM As aW Kk Rg tF) Vo(aE dD Jk Mg Pf Rj) Uu(Ba hA On oQ Pf) gL(Io Ma Ou Ra Ug) Fr(Dk Hb Ke Ra) Nm(cM Kz Oi oP) Rg(bU Hb Id iZ) Vv(Mg Mt Oh Qy) Lx(Kc Po Uc) Me(cM dD Vs) Hc(kE Of Pf) Rj(dD Io Pf) tF(Kq Oh Pc) Aa(Tv Uk) Ba(Mq Nf) Gz(aE nD) Lu(Kc Ld) Ma(dD Qy) Nl(bU Kz) On(Nf Pj) Vs(nD pF) TzKz TvIj NxpF} mZ{Uu(cE cG cL Iz Jk Kc Kd Kk Ua Vs tF) Ic(Dc Jj Jq Lx Up) Ra(bF Fn Gp Og Uo) Ug(As cM gL gP Rh) Vo(cQ Is Ml mS Ss) Lu(Al Kc Kg Ql) Ib(Gl Jn Mn Vs) Oh(Hb Ke Qn Sr) Vv(Id Jk Pa Ua) jP(cN dE oK) Lv(Pj Qm) Nj(cQ Ou) Uc(Kq Lx) Id(Oi Ow) AaTv DkKq ExMn MaUt UbaH IvLd RjQl VsnD} Kz{rN(Aj Dd Ib Kg Mg Mr Ng) qQ(bM Ij iP Jt Uk Uv) zG(Ki Mp Nm Nx nY) Tk(aD Hb jV Ph) rQ(aZ Cp Kx Tz) uM(Lj tR tX yJ) wL(Mk Nc Nx) zH(cI jK wK) qB(Ad Hb Uf) uY(cX jO Mk) Me(Cv Kr) Ky(tS tX) tR(Gz qW) kG(iP Ub) zA(bH cO) rT(gW Jd) AjrR KjvH KltQ OkwJ bGtX eZqY fYvP wBoN jQuX} uW{Mp(aO Bb bC bF bI Cp Dg Hb Jh Kl Me Nb uN zH) Ex(aI Ao Ha Ic Jg Kn Nk Ns Rb) Aa(aK bJ Ha Na Nu oN Pz Um) Me(bW cL iC Qc Up) Rb(Aj Jq Lx No St) Kf(Gz Ih Qd Qy Uv) Gz(Mf Ok) Jq(Pe Qd) Kr(aO Mt) Up(Lx Mf) bG(cI No) FrrY NmNt MnOn NacR JtUv KdUk UfwK} Nt{iB(Ba Bb Bo Co Cp Dk Fa Jd Je Kg Ok Vs) Ba(eZ jP Ly sC wB wK) eZ(Ch Dl Ef Hb Uu) hA(Ad Jd Rc Uf) wK(Cu Cv Hb Kg) wL(Aj Cu Ij Uf) wG(Af De Uv) wJ(Hb Kg) yK(Uk Vt) jT(Cp Vs) uX(Or Up) AdjM AjuU AwwH CvqT

Figure 21 Continued

DksK DlrN NmsM LyaN TtqQ IjyH HcnC PzpY KiuV KqqX UutO} Ki{uM(Aj Bn Kf Mf Nr pS) Kf(rV uG wD wK) qX(Jf Kc Kk rA) pS(Dg Iu Jq Om) rN(Aj Dg Ng On) Ok(rV wJ yL) fY(Aa Bb vP) qG(Dg Fy Qu) sC(cA De Nb) vO(Jf Ow Pj) aZ(vP vV) tR(gL Um) zG(bW Jt) AdIb BbwJ ChtM CxzA MeyH MmtO JdqU KceD KxwK UfqB VvvS PjyL aNuV bCwD cLwG lMoN} wJ{Bb(bG Gz Ha Jo Kj Mf Mm Mp On Ph Pk qW) Kf(Dd Ih Js Lx Nr rO Up Ut) Na(Aj Dl Jq Jt Kq) Jt(As bW cA qX) Ok(Ql Rb Ri Uk) Kl(Hu Kk St) Dd(Jh Up) No(aO Dg) Mf(Ad Ic) Ih(Dc Fy) fP(iC Mt) rV(Jr Kc) AaIc IoPj IvhC JdUk JobI KnpS} nI{rZ(cW dE dF hB Ij Iv Qb tF) jE(bL cE dD jl Nj Nr pF) jM(aO hG Lx Mn Ur) rX(aL aM cJ) lM(Aa Ct Jl) Lu(jH lK) Mn(iC jP) Uh(qT qU) aZ(hA qV) hX(bB cL) iP(Ne Nl) rC(bZ cI) jV(Hu Nj) BajD LxtF TzqU UtqT VujY bIhW iZrB lKoK} Mc{sO(aK cM Rh Tz Uk Uo) wK(bB Jt Lh Mm) wL(Cv Dc Nn On) uL(aO Jt Mm rB) rV(Hb Kf Pj) vS(aZ Pk Uk) On(Uc uG) tT(Om Uf) tX(bO Ue) yH(qV rA) uR(Hu Nr) CvwD NatN UbkG IcoQ KnkI KsmM KxyK QlnC UmvI aOuG cJtR tOoH hBuT iPqG qUrW} No{vI(aK Al Ax Bo cF Fa Hb oH wE) vT(Aj aO bW Rc Uf Uu) uM(Aj Fa Ok Uf) wK(Aj Bo Dg) yH(Jp Jt Uf) zH(cR Um Uv) wF(bU Ky pY) Aa(rO wE) Kf(vA wP) wL(jF Uu) tO(Ok Pc) wD(Rb Uv) wG(Ir jR) BouV FbvA KxzG aOwP hRyD} Um{wL(Ib Jg Jh Kl Ny Pa Uk) zH(Af Mf oK pY Ue) uN(bI hL oK vA) vI(Jt Nb Oh Po) vS(Bo hL oK Qy) pY(Di Ef Uk) vA(Aw Jq lM) qB(Dc Na) uY(hA iC) BbvT UkwG UvrR bItQ bMsK dLuX fYvP hLpS jKuU} Uf{wK(aI Dg Id Iz Na Nb Nm Qe) iA(sC uX tM) vH(hG jD wD) aK(uM yH) aZ(vP wD) bL(rZ wG) cR(qO vV) fY(tX uY) hR(As Mp) tT(Qd uM) rP(bG Ex) qQ(iJ jG) RbrT StvT JstO KkvA KrjM aIhP aWtU bUvV dLqA eDnL gWqB} qT{iA(Ij Is Jm Li Ok On Pa Ph) Js(Co Cv Kx Qh Tt Tv) nL(jI jU rY rZ) nC(jF jI jU) aZ(lX mE) nU(Nu Pd) mP(bM kQ) mS(jF Uu) nD(Oy rZ) kF(Jl Jp) kG(cP Uc) oQ(bZ cR) AamE BbNa DlmH lXjM mUjQ nHjF} kF{eD(aQ bN Jj Vu) jH(Bg Ct eF) rA(Jn Js Mx) jO(Jj Lu Of) jP(Fp Mh Nv) Aj(jK lK) cI(jI qW) dD(jE qU) iP(lN qU) jT(Nj Nm) oN(cL mP) CujL UuqV aOqY aYrB bZlM cRjD eFlK fPjQ hAhB iAqX iJlN} Kf{wD(aK bL Kk Uv) Js(hR jM jT) rV(Rb Uc wK) rO(iJ Pc Pf) vP(aK Lx St) Nu(jT uG) Ib(rB Tt) Ih(qP uM) Qd(fY qA) tT(Lx Mt) CqwK MaoP MpuM IlrZ SttU KkhL TkjG aUuG bGrP eDuY fYiA yKoN} Uk{wK(Ao Jt Kl Nu Pk rY) yK(cG Cs dF fN Ut) wD(aO Ij jD Nu) fY(Ad Iv Jp) hA(cW rW vS) aK(fN sK) cG(vS zA) sC(jH Rc) uX(Mp Nu) ExhL IcqB JdvV KkvI KrzG yJrY rBwG} oQ{cV(jD jM Ma rZ Vo) cI(jH lL lN) eD(aY bI dl) rA(bZ Ng Nm) pF(bC Oh Uo) Ma(bX Kn) cH(lM Uu) tF(lN qW) rC(bI hB) lL(Ng Of) NmhA IbbJ KkkI NxjD aKlK aLjP dClO gPiC jTkQ} bW{mP(Ex Fa Kq Rg Vs) wL(cM eD Mw Ue) uM(Af Ex jH Mu) vT(fY Ip Jq rX) Ex(tS wH) Qy(sK yL) Or(tU wB) iJ(sO vI) wG(aZ Mw) MuyH KkvI KrzA UpwD PcrZ cGvU jYuY} aZ{yK(Cs Is Ur Vt) Ad(fN qG wD) Jt(fN wG) Kl(wK yD) mE(jH lM) hR(cH Ok) wF(oH qA) vI(Kk oH) DdyH IctT HbfY RbwD OneZ PjtO aUwG cIvS cLwK lXqX jHvP tMrY rXoE} jP{mH(Ad aI De Di Dk fP hB) mE(Ji Mn Mt Nj Nk) mI(Ad aF cB cF) kK(Lx Nw Nx Ny) On(As Rb) cW(Ip Tv) dD(kP mT) AakG NaVs UvnL aMoP dLkN} Kk{vI(Aj bI cU Fy Jg Jq Mp Om Pj qU rY uU) kI(aM cL Lx mU) hP(tR zH) tX(jY lM) vQ(Jg Kl) AjwL DewH UeuN KomT KrsO OyzH PctV bVmW} nL{rA(Ji Mj Nr Po) qX(aL Co jI Vp) Ur(hA lM) Vs(Ub tF) rC(cG cH) jH(gL Tz) jM(Bo Ut) jT(Ji On) ArqU LyKn MlQl TviP LipF VtjE bPrX cRhW iZlK} Na{uX(Di Mp oK oN) Kq(hR iC jG) hL(Il Jg uL) wK(Ad Jt Qu) dL(eT qA) pY(oK vH) uL(eT Mf) AdyH BahA EfeZ JquM cUfY jDpS jHqQ lMoN oHvI} oP{Ma(aI Ba cW oF Uv) Ib(dM iP Kp Mn Ny) Nm(aF cM Nx) pF(cH Oh Pa) Lv(Ld Ra) Nj(jT mE) AadM CvVo bIqY bPrA bZjH cRqU cWjQ fPjI} Uc{Ph(qQ rV vS) Ad(vO vS) Aj(uY wL) On(rY uZ) zH(Nm rB) rV(tR tX) yL(Nx Om) uN(bI Lh) AopS AwwH BbqX JdqQ JquZ KgqG KlsC PkvS eTuY mHqW} mS{Vo(bF Bo cE cG cL cR Ny oN Qy) iP(Jj Js Mz Nc Nx) Aa(cE cG Jy) Hu(Ao Hb) Ic(aN cQ) rB(cF oN) NmoN LuVv UcNy RaJj} nC{rA(Ji Lh Mj Nr Nx) Hc(Cu Iv Ql Vv) Ib(cG Mv Rg) qX(aL rB Vp) jT(Ji On Pa) rC(cG cH) AsjI CvjQ NdrZ TviP UrlM bPeD gLjH} Jd{Hu(qQ rV wG) eZ(Ih Kr Oa) uM(cB hG jH) cW(hA jG) zH(aG aK) ExIO MfuY MpqG IbTt IohA KrrQ KywC RfqQ PcvP bLrZ cJwG fYiZ jHpS} mI{jM(Aw BA hC oF oN) jE(Ar bL hC) lM(aO Cu Vv) Kc(aA Ic) aY(eD rX) rB(dC oF) jD(aL Ar) qV(aW Up) qU(Bo cF) AljY aJlK} mP{eD(aO bA bL bQ cE dD) lK(bL cE cT gL oK oN) Ez(Cq Nx Qx) qV(aN kQ) lL(Lu Og) AahA ArMa LxaP IbTt KnkQ NypF bIjQ} Kr{sO(dF Mt Nx Ub Un) qG(Dg Dl Hb Kg Ok) cI(tR tT) fP(eZ uT) uL(Fy Kn) uN(cW oH) AarV CowB MrtM HwwF LiqU qBuZ} On{iA(bO bP cD nY qX) Uc(eZ Ly Ne Nl) Ex(gW Ma rZ) Rb(eD qG uL) eZ(It Kd) LycD MnwD KsjM QljG UvrV} mH{jD(Ch Co Om Tz) Ng(hW jH rZ) Nm(jQ jT) bM(lM rC) rZ(Of Pz) rX(aL cR) DghA MhlK IojT UtjY hCjQ jHkQ} kG{Bg(hA jQ) Ur(jE qU) Vv(Lu Ow) cH(Gz tF) lK(cN Mh) AlqW CvRj DcjM FbMl LvPj UbKc IbmT aLhV eDoE jEqX rAjQ} mE{qX(Aa Iu jF Mx Qb) rB(cF cT Lu oN) rX(aJ cN hG) Ij(jT lK) rA(Il Iv) rY(cF hC) BojE VspF} mM{lM(aP Dg Oi) Ax(jL lK) Co(eD qU) Lv(Ib Ou) hR(aY cV) rB(bC dM) CujH DijL aMjM bZrC dDtF rAjR} Mp{zA(Af Bb Cp) eT(Bb pS) fP(pS uO) rV(Pj Tn) oH(tV wP) uX(Di Mg) DcwD NnvA JquZ KlrN hGzH} Tk{Gz(aD Cx Dl Ph) jG(cB Hb Mt Tt) bG(eC hG Qv) rX(bL Iu Ph) AlrY IkKg IvoK QybO} cW{hA(Al Cv Dd Ip Is Kc Kg Of Pf Qh Tv Vv) jM(Dc Kg) CojG KprZ PchR bGjH} nD{Vs(bZ cH Js kQ Mz Pi) Iv(Ko Tn Tv) jE(Aa Jj Nk) Js(Al Kn) jH(aJ cG) DcUp IlKn} Jt{wK(bL Gz Kd Kx Qd St) Qd(fN yD) bL(rV wL) uM(St Uc) AsrV UveT bUyL fYjR hGvH} mW{pF(Kn Lh Nr Nx) Gz(An bG) Kn(iA Ko) Rg(cV Mj) kQ(Lh Tz) AajE CoEz FatF ExIt NjcM} Rb{qG(Bb Ik rY) oH(tV uN wL) Ad(rT wK) HwwK JhuY JqsC OmtM PjrV hGzH rBuL rYuG} nH{rA(Mj Nb Nr Nx Po) iP(Iz Kp Rj) jH(aM Nj pF) jT(Ji Nx) CqIb IuUg gWqX} Ex{Dg(rP uG) tU(Nm rV) TjLy FbwH PzwL JgwD LiuG aCcD bGhL cIuO cYgW hPoN rBuL} nU{Js(Ha iP Kn Pe Tv) jH(Al As Ba gL Tz) rC(aD cH) AwiC UrqX cRhW} hG{uM(Aj Bb Mg Qy) Aa(fY uU) yH(Mg Mt) AjwB BbuU NuwL IvqB JquY PcrX} kK{eD(aY cG cM cT Og pF) lK(aK cI) AalM LuIL IbcR JjjK aNqY} mU{Nx(bV pF) bI(jF lL) jT(Jj Mn) NkjU OgeD aNjH aXqV cElM qXjQ} fP{Mt(wK wL) Hv(hL wD) Iv(hP qB) BbqO LxwK hLuM iCuT kPrZ} mT{kQ(Kd Nc Nj) Ib(Mn Tt) AlIv LvRg LyUo MacG KgUg QlPa} hR{As(Ad Ok Tt) Vv(Mg Tt) CvcX TodD PctF cMkP qVuP} Bb{Ow(qO qP) jY(uG tM) rW(Jf Pk) RftU aKqI qVqP} aC{cZ(Aj Aw cB Cp Dg) bE(Ba Bo cB Ch)} wL{bL(Dc Jp Pz) MnKg HwcM HcJh IsqU OfoH PaaK} kI{Kn(Aa Jj) LuKc LxOw MuVv NjoF NxPk bPlK jFqX} rZ{Pc(Ba gL Jf Vs) As(De lM) BaVv JsbL nMrA} uM{Jq(Fp Ha Mr Ny) St(Aj Cu Dg) FaIh JhoH} wG{Nu(bL cE iC It) Nb(Dd Pj) FybU QviC} Gz{Lh(hL tQ) AowC MllW MmrV JjwP cRrW} Tt{Ib(Hu Mg Ml qX) qQ(Hu Nb) aUqO} lX{eD(Ba Pf) qX(Dl Ub) cYlM eFrB jIjQ} Aa{jD(fY qG) AoqG DdqO aKeT jEoO} Ih{eZ(Ad Ij Kg) DdyH ItqQ OkfY} Pk{jG(qQ tR) vI(Ik Rh) DcqB cRvS} Cv{Ic(bX Ql Ug) cBwF iAlM} Hw{wF(bO cM) UpwK hLyL iJzH} Ok{hA(As Ql) QdeZ iAqX jYpS} Pj{rV(jM Nb Nj) NbrO jYpS} Ly{Gp(aV cD Nj) AdcD} St{AjyE IszG JqyK aOvH} Js{Tz(qU qV qX) LheZ} hL{Jp(bG pS) JjrX aOtM} kN{hA(Bg Dg) CtlK DkoN} oH{vI(dF Lx Nd Ub)} Ba{iA(Ic Ne) MnwH} Dd{UprO aFyH aKqO} Hb{NbrO UvrV bGrP} Wn{Dk(cG jG) OahA} mY{lM(Aj Dg) hCqX} wK{Kj(Nb Qd) AjIc} rB{BoqZ MgvA aIkP} rX{Pc(cR Tj) aOqG} zA{iJ(Jg Kl) MtSr} uY{QviC KlUv cMjH} Lx{QvuX LhtT} Mn{AdhP KgtO} Qy{JpvO wCrY} cI{bGrN cMzH} AskElK EzNgqX NqOmtT MlVsoO IojIkP RcRjqU JucRrV KciAlM KnlWpF KxaFwD LhjYrN VvaKjR

Constrained panels with 2 analytes, where 1.0E-8 >= 'AUC p-value' > 0. Contains 71 panels of 155,335 total panels evaluated. : Vq(hO nO qD qU rU rY rZ uM vA vB vT wL wQ tL xA) Cw(hL hO qD qG qQ rN rU rV uY vT wJ wQ tL xA) nT(Ba cG cL dG gL Hc Id iZ Kd oN) iH(qU qX rU rV rX uM vB wH) nA(Ex Lx Ny Og Vs) nO(Ba cE cG cH) nJ(jE rX Vs tF) nB(Kc Kk Kn) qD(Pk Qw Qz) Us(rU wQ) HfvB KzpS nFoN Constrained panels with 2 analytes, where 1.0E-7 >= 'AUC p-value' > 1.0E-8. Contains 43 panels of 155,335 total panels evaluated. : Vq(rO vW wD wG yK) nA(Md Ml Mr Nr Po) nB(Ed Ld Ow Qv) nJ(dJ jI nT qT) iH(eD hO lN qQ) Us(lM uW zA) Ap(qG vW) Cw(iC jM) Uf(wJ wQ) nO(oN Vs) ArQz BcvW DbwQ EdqT ExhO GzqD IbkG KzuG OnnF dJnT

Figure 21 Continued

Constrained panels with 2 analytes, where 1.0E-6 >= 'AUC p-value' > 1.0E-7. Contains 84 panels of 155,335 total panels evaluated. : nT(aJ bL bW cE cH cN hB Ib iO Ju Kc Kf Kz oF qT Rj Ua Uf) Us(hO nJ Nx On qD qQ qX rX xA) nO(bF cL dJ Kd Kn Qt Uf) dJ(aC cF Ed Ly vB) nA(Ed Hc Jj Om Uv) qD(Jt Lh Na vW tM) Cw(hR Ib qU qX) nB(Nj rA Rj tF) Vq(qX rX tF) nJ(lM Ra Rg) Ap(wJ xA) Bc(zH tL) Ex(Ed nN) Hf(wQ xA) Um(vl zH) DbhO FwqT Nlln HunK QzqC KrvB OwnF aCcF dBrX iHlM kOoN Constrained panels with 2 analytes, where 1.0E-5 >= 'AUC p-value' > 1.0E-6. Contains 172 panels of 155,335 total panels evaluated. : nT(aM bF bZ cM dF Dg dH dL eF Fn fP hC Iz Kk Kn Ko Rg Ri) nO(aM bW cM dD dG gL hB hC iO iZ Kq oF Qy Tz Ut) Qz(Bo Cv Cw dD Ic In Ki Kq Ou Qg qQ wJ xA) nF(Ba Bo cH Fr iH Kn Ko Mn Mt nJ Nx oF) nA(Hu It jI Jq Lu Nx Pf Ql Us Vu) Ly(aN bX cC Db Gp Ne Nl Us Vq) aC(Ad Aj Ap Ba bE Bo cB Cw Fw) dJ(cB gW hR Ic nB Rb rZ wG) nJ(hA iO iP kO oN oP Up) qD(Db Dd Iq Jp Pj Pz Um) Vq(hA hL hR iC jY) Cw(hA jO jP rZ) nB(Nr qT Tv Ub) kO(cM gL iZ qT) Me(Kz uW xA) On(iA Qw Uc) nK(Ed Lu Vs) Ap(hR rV) Ba(Nj nR) Bc(uN wL) Db(jL vB) Ne(In Ok) Ib(oP Tt) Iq(rU wL) Us(qT uX) iH(Ed hR) xA(Qw Uf) vW(bW dN) ArNj CvIc FwcB NmoP MpuW NhIn NlOk UevB HfqT KihO PkqC cFdD nNiZ nRoN oQpF oHvI Constrained panels with 2 analytes, where 1.0E-4 >= 'AUC p-value' > 1.0E-5. Contains 443 panels of 155,335 total panels evaluated. : nO(aJ Al Ap aY bA bL bU cW dF Dg dH Hc iH Iz jI Kc Kf Kg Kk Kp nA nJ qT Rg Tv Ua) nT(AP Aw aY bC Bo bU bX Cp dD hG iH iJ Jv mP nA Ou pF Qt Ut Vs) Ly(Ap Ar As aX Ba bF Bo cD cE Cw Et Fw Ic In Ki Kz Nh Og Ok Ql) Us(Ad Ap Cv Cw Dc ED hR Ic Jg Kq Lh lO Ne Oe Oh Ok qU Qz Rb) qD(Ad Ap Bc Dc Et eZ fP Hb Hf Hq Kf Ki Kj Kz Mp Ok On Uf yE) dJ(bU bX cK fP Fw Gp Jd kG Kq lM lN Ok Qg QW qX Qz Rj) Ic(Ap Ar bX Cw Dd Et fP In Kc Kf kO mZ Ne Nx On Ql Rg) nF(Ap bF cE Dg fP Jg Kc Kf Ms nB Nv Nw Ok Qe Ss To) nJ(Ba bF cE cL cM Fw gL In Kn kQ Lv Ml nB Nf Og Vu) Qw(Ad Ap Ar Ba Co Cw Et Ex Jh Ne Nl Nx qQ vB wQ) Qz(aN Ap Ba bP Ed Et Fw Gp On vB vW wK wQ) In(Ad Al bX Cw fP Ha Kf Kn Kq nA Tn Tv) Fw(cF gW iH nA Nl Oh On qX rZ vW xA) Ap(hA Ib iJ jM jO Kk rO rZ wQ tL) Ed(aC bX cC Ki mF Nj Oh On qX vW) nA(Gp hW jQ jR Js Mn Mz Qx Rg Rj) Hf(eD hO Me qQ qU qX uW wH tL) nB(Ba dK gL Lx Ml Mr Oi Pf qX) Bc(rU rV rY sK vl wF xA) Et(Ib Kk Ks Ne Nl qX Ue) Ki(Kc Me pS qT qX wQ xA) nN(aJ Fn Id Kk Kn oN Ug) Db(eD lM qU qX rV xA) Ml(iH Nd Nc Nh nK Nl) bX(aC aW cB cT Nj On) cF(Ad bF Bo cB cL iH) Nl(Il Io Nc Nk Og) Iq(hO qT tV vB wD) Vq(jG jO Mc oE yH) dB(jL lM qX rU vB) lY(Hc Kz Nf Oi Rg) nK(Jq Kk Lx Mn Nx) Nh(Il Nf Og Ok) Ib(Ad Jg Kf On) aC(Ch cL cN cZ) aZ(qX rX wQ yK) nR(cE Ex Tv Vs) qT(kG nC nH nL) kO(bL cH Hc iO) rU(Dd Jp Me Pj) Cw(eD jG lN) Nj(Ad bF Ok) Ue(On wQ xA) Kr(uW vW wQ) Kz(hO qQ Tk) bW(uM vT wL) cB(aW bF cN) oP(cH Ma pF) vB(bL Me Rb) Bo(hR jM) Na(hO uW) Ne(Il Og) Kk(Kc vl) Ok(Nc Nd) iH(Ad dD) xA(Bb Kf) kG(jl rA) rX(aW bL) BaiA CvUv NtKq JdvW JquM JnL TkbG UfwK aKgW fPhO iOwG kIoF Constrained panels with 2 analytes, where 1.0E-3 >= 'AUC p-value' > 1.0E-4. Contains 928 panels of 155,335 total panels evaluated. : Qw(aC Ao Bb bF Bo bX Ch cN cT Cv Dc Dg Di Fr hR In Jd Jg Jt Kf Ki Kq Lh Li lM lN Lx Ly Mm Nc Nj Nv Ok Oy QT Qu qX Qy Rj rX Ss Uf uM wL tL tF) In(aC Ap Ar Ba Bb bF Bo cB Co cT Cv Dc Dd Ed Ex Fa Hc Id iH Jd Jc Kg Ki Kj Kl Ko Kx mE Nc Nd Nj nK Ok qT Qx Ra Rb Ss St Tt Tz Um Ut) Us(Al Ar Ba Bb Ch Dd Dg Ef Et Fr Hc Is Iu Jk Jm Jt Kc Kf Kl Kn Ko Li Lx Mb Me Mg Mh Mu Nc nD Nf Ng Nj nK Nl Of Ra Tn Uf Vs tF) nF(Ad Aw bA bX cG cJ cL Cw dJ Ed Et GL hC iO Ji Kk kO Lh Li Lx Ml Ne Nf Nl NO Nr nT Ny Og oP oQ Pd Pf Qt Qz Tv Vs) dJ(Ad aK aQ aW Bo bR cP cT dD Ex Hc Is Jg Ki Kk Kl Lu Mh Ml Nc Ne NH nK Nl On oP Pc Ra Ss vS) Ed(Ar aW bF Bo bW cD cE cN Cv Cw Et fP hG hR Ic Iu Kf Kq Lh Nc Ne nJ Nl Pa qD Qv Rj rZ Ue) Nj(Ap Bo cB cE cF Ch cT Cv Cw Et Ex fP Fw Jd Ki Kq Ly Nd Ne Nf Nh nK oO oP qD Qg Rb Uf) Ic(aC aP BA bG Bo cD dD Ex Fn Fw gL hG hR iH Jd Kq Kx Lu Lx Me Ml nN Ou qD Rb Rj Uf) iH(Ap Ba bF bP bU bW cD cE Cv Et fP Hc Ib Jd Jg Kq Ly nB Nf Ok On Ou Pg Qz tF) hR(As aZ bB bL cC cW dB dD Et fP Fw Gp Hf hG Il Iq Kc Ml Ok Pc Qz To Uf Uk) nO(Ar Aw bC Bo bX bZ cN fP iP Ko mY nB nK nR nU oP oQ Ou pF QX) Et(Fw Fy iJ Io jM jT Lu Nc Nd Nf Ng Nh Nm Ny Ql qT Ra wJ wK wQ) Qz(aW Bb bF cC Ch Co cT Hq Jd Jh Mc Ml Mv Ne Om Pg Rc Rj tL) Ki(bX Cv Fw gL Hc Ib Jd Kx Ld Li lM Ml Nf On qU Ra Rb Rj rX) Ok(Ii Io Jl jT Kk Lu Mn Mp Nf Ng Nm Nq Ny qC qX rU Ue wJ) qD(bG cB cF It Kg Kk No Nq Nx Ph qG qV Rb Rj sC uM Uv vB) Ap(hO iA iC jG jP jT Ou qC qU Ra rU Ue Um uY vB Vo vT) bX(aZ Ba bF Bo bP cE cF dD fP Fw Is Kc kO Lu Ne Nh Nl) On(aC cC cD Gl hA iC jM jT Kk Ou qC Ql Ra Rj Um Uv) Cw(cF Fy gW iJ Kk Ne Nl oK Ra Rb Ue Vo Vv Tk tF) qT(aZ DB Iv Js Kg Kr Kx Kz Nt Og Oi Ql Rj Uk) Ib(Aj Ba Co Dg Jt Kg Ko mZ nA oQ Qu Ss Tn Uf) cB(Ar aZ Ba Bo bW cE cK cL cP Cv Ne qX rX vW) cF(aW aZ Ba cE cT fP Gp gW Kc Ne Nl rU Vq Tk) qX(Bb Bo cC cW dD Iq jE jF kG kO Kr nT Rj) vW(Ad Aj aO aP bC Db Fn fP hG Kf oH Qu Uf) nK(Fw Iv Kn Mz Nf Nm Nr Og Oi oN Ql tF) hO(Ad Dc Dd Fn Jt Kf Lh Me Pj Pk Um Uv) qC(Ad fP Hf Iq Jt Kf Me Pj Qc Um tM) Cv(Kk Ks Ne Nl Ql Ra Rb Rj rX rZ) Fw(fP hG Is Kf Kq Nc Ne Tn uM uW) nT(bA cS Dk dM mY nD nU nW Qy Ss) lY(Li Lx Ly Ml Mt Nm Pf Qy Rj Vo) kO(bU Dc dD hW iP oF Qy rA Ua Ut) Ba(gW hA iJ kl Ne Nl rZ Um tF) aC(aZ bF cE Is Mg Ml Ne Nl Pc) Bo(gW hA Ne Nl qU Ra rZ xA) Ly(Hf Ks Ml Nc Nd Nf Rj Uf) Rb(bP cC Db dD Hf Ks Nt xA) Um(Ar Kc Qg Ug vB wL tL xA) cW(eD hA jH jM lM lN rX) nB(bF cL Dc dD iO jE Mn) tL(aO aZ bW cC dB Dd Kr) Ad(Ii Nm Ra rU Ue Vo) Ar(Nc Ne Nl Nr Nt Pc) nN(dD gL Ow Ql Rj Uf) nJ(cH Kk Mn oQ Qx Ub) vB(aZ cN Dc Jq Na Uk) Ra(Kc Kf mZ Ne Vq) Kq(Ik Ks Nm Ql Ue) fP(cD cS eZ hA wQ) tF(bL Gp Kc mM mY) nR(bF cG Kn Qy Ut) nA(Hq jE jF nM Qy) kl(cG cH Kc Kk Kn) Nd(Iq Me Nf Og) Kf(jM Kk rV wJ) Uk(fN wD wQ yK) aO(uM wB wQ tM) cC(eD lM rX wG) dB(eD lN qU rZ) dD(cZ gW lX rX) mF(hW jE jQ Vs) wL(fY Hw Jq uW) xA(Jd Jr Pa Pk) Ne(bF Hq Io) Nl(bF Ql Rj) gW(Al bP Gp) mZ(Id Ql Ue) kG(cH Ml Ug) rV(Bb Hb Pj) uX(Mp Na Nu) Ex(Mp Ri) Nt(Hc uW) Nh(Ij Io) Iq(wF Tk) Kk(Dg Jg) Ks(Mb Me) Vq(dR lN) mM(jE rA) mS(Ug Vo) wJ(Bb bW) iA(Lh lM) oQ(Ma Nm) AjwQ DbjM LznU NauL HvoP TtqQ HflN RchA KgrZ KzrQ QlOh UfuM UpuW VsnD PkrU aKjR aZwG bFcV dErX dMlM nliZ iJsO jPtM kNoN

Figure 21 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.0E1 | 7.0E1 | 8.1E1 | 7.7E1 | 5.8E1 | 5.5E1 | 1.0E0 | 2.0E1 | 4.8E2 | 2.2E2 | 1595 | 17 | 266 | 17 | 0.48 |
| Ad | ug/mL | 3.8E-2 | 4.4E-2 | 9.4E-2 | 5.7E-2 | 4.1E-1 | 5.6E-2 | 2.7E-4 | 5.0E-3 | 8.5E0 | 2.0E-1 | 447 | 13 | 170 | 13 | 0.50 |
| Af | ng/mL | 1.2E0 | 3.3E-1 | 1.8E1 | 1.4E1 | 6.7E1 | 4.4E1 | 1.7E-3 | 1.7E-3 | 5.3E2 | 1.6E2 | 447 | 13 | 170 | 13 | 0.38 |
| Aj | ug/mL | 1.4E0 | 1.2E0 | 2.6E0 | 2.1E0 | 2.4E0 | 2.3E0 | 1.5E-3 | 3.2E-2 | 6.1E0 | 5.8E0 | 447 | 13 | 170 | 13 | 0.45 |
| Al | mg/mL | 8.7E-5 | 9.3E-5 | 2.5E-4 | 3.5E-4 | 4.1E-4 | 6.4E-4 | 2.3E-6 | 2.2E-5 | 1.9E-3 | 2.2E-3 | 447 | 13 | 170 | 13 | 0.55 |
| An | U/mL | 4.8E1 | 5.2E1 | 1.8E2 | 3.2E2 | 5.5E2 | 6.7E2 | 9.8E-4 | 7.4E0 | 7.8E3 | 2.5E3 | 447 | 13 | 170 | 13 | 0.60 |
| Ao | pg/mL | 9.2E1 | 5.7E1 | 5.1E2 | 1.1E2 | 3.5E3 | 1.5E2 | 1.5E0 | 7.8E0 | 3.9E4 | 5.8E2 | 447 | 13 | 170 | 13 | 0.37 |
| Ap | ng/mL | 3.3E1 | 4.2E1 | 4.7E1 | 5.6E1 | 5.0E1 | 5.2E1 | 8.4E-5 | 6.8E0 | 3.3E2 | 1.5E2 | 447 | 13 | 170 | 13 | 0.54 |
| Ar | ng/mL | 9.5E-1 | 2.3E0 | 1.2E1 | 3.9E0 | 1.9E2 | 4.5E0 | 3.4E-3 | 1.7E-1 | 4.1E3 | 1.5E1 | 447 | 13 | 170 | 13 | 0.65 |
| As | ng/mL | 8.7E-3 | 1.0E-2 | 1.6E-2 | 1.0E-2 | 6.1E-2 | 7.6E-3 | 1.7E-3 | 1.7E-3 | 1.2E0 | 2.9E-2 | 447 | 13 | 170 | 13 | 0.52 |
| Aw | pg/mL | 1.6E1 | 1.8E1 | 1.6E1 | 1.9E1 | 6.4E0 | 6.9E0 | 2.9E-2 | 1.1E1 | 5.1E1 | 3.4E1 | 447 | 13 | 170 | 13 | 0.63 |
| Ax | ng/mL | 2.1E0 | 4.2E0 | 1.6E1 | 1.4E1 | 6.3E1 | 1.8E1 | 1.2E-2 | 3.9E-1 | 7.7E2 | 5.1E1 | 447 | 13 | 170 | 13 | 0.61 |
| Ba | ng/mL | 6.1E1 | 4.5E1 | 4.1E2 | 6.8E2 | 1.1E3 | 9.8E2 | 3.7E-1 | 5.5E0 | 8.1E3 | 2.8E3 | 447 | 13 | 170 | 13 | 0.56 |
| Bb | ng/mL | 3.4E0 | 3.9E0 | 6.8E0 | 6.2E0 | 1.4E1 | 6.3E0 | 4.1E-3 | 4.1E-3 | 2.5E2 | 2.4E1 | 447 | 13 | 170 | 13 | 0.56 |
| Bc | ng/mL | 3.8E1 | 9.8E1 | 1.1E2 | 1.3E2 | 2.0E2 | 1.3E2 | 1.1E-1 | 4.2E-1 | 1.2E3 | 4.3E2 | 447 | 13 | 170 | 13 | 0.63 |
| Bg | ng/mL | 7.7E-2 | 5.2E-2 | 5.4E0 | 1.7E0 | 3.0E1 | 2.4E0 | 5.3E-4 | 5.3E-4 | 4.4E2 | 6.0E0 | 447 | 13 | 170 | 13 | 0.52 |
| Bn | ng/mL | 5.6E-2 | 5.6E-2 | 1.3E0 | 9.9E-1 | 3.3E0 | 2.1E0 | 5.6E-2 | 5.6E-2 | 5.8E1 | 7.1E0 | 447 | 13 | 170 | 13 | 0.43 |
| Bo | ng/mL | 1.2E1 | 2.1E1 | 1.4E1 | 1.9E1 | 1.9E1 | 1.3E1 | 1.6E-2 | 1.6E-2 | 2.8E2 | 3.7E1 | 447 | 13 | 170 | 13 | 0.62 |
| Ch | uIU/mL | 9.7E-1 | 1.2E0 | 1.7E1 | 2.2E1 | 1.0E2 | 5.9E1 | 3.4E-3 | 1.2E-1 | 1.8E3 | 2.1E2 | 447 | 13 | 170 | 13 | 0.57 |
| Co | pg/mL | 3.8E1 | 6.5E1 | 1.8E2 | 1.0E2 | 9.6E2 | 8.7E1 | 1.5E-1 | 8.1E0 | 1.7E4 | 2.3E2 | 447 | 13 | 170 | 13 | 0.60 |
| Cp | ng/mL | 2.1E1 | 2.8E1 | 3.0E1 | 3.7E1 | 6.7E1 | 2.6E1 | 6.0E-1 | 8.6E0 | 1.3E3 | 9.8E1 | 447 | 13 | 170 | 13 | 0.68 |
| Cq | ng/mL | 2.8E-2 | 3.1E-2 | 2.5E-1 | 6.0E-2 | 2.5E0 | 7.9E-2 | 8.0E-4 | 8.0E-4 | 4.9E1 | 2.8E-1 | 447 | 13 | 170 | 13 | 0.52 |
| Cs | ng/mL | 5.9E1 | 1.5E2 | 3.2E2 | 4.1E2 | 1.2E3 | 5.5E2 | 2.7E-2 | 5.8E0 | 1.8E4 | 1.6E3 | 447 | 13 | 170 | 13 | 0.64 |
| Ct | ng/mL | 6.1E-1 | 3.5E-1 | 3.2E1 | 6.3E1 | 9.9E1 | 1.7E2 | 1.1E-4 | 5.7E-2 | 6.2E2 | 6.2E2 | 447 | 13 | 170 | 13 | 0.52 |
| Cu | ng/mL | 2.4E-1 | 2.1E-1 | 5.5E-1 | 3.7E-1 | 3.2E0 | 3.8E-1 | 9.6E-3 | 5.3E-2 | 6.6E1 | 1.4E0 | 447 | 13 | 170 | 13 | 0.50 |
| Cv | ng/mL | 5.8E0 | 7.8E0 | 2.8E1 | 1.1E1 | 6.9E1 | 1.0E1 | 1.4E-4 | 5.7E-2 | 5.3E2 | 3.1E1 | 447 | 13 | 170 | 13 | 0.53 |
| Cw | mIU/mL | 3.0E-2 | 3.7E-2 | 5.4E-2 | 3.9E-2 | 3.2E-1 | 2.5E-2 | 1.5E-4 | 3.5E-3 | 6.8E0 | 8.2E-2 | 447 | 13 | 170 | 13 | 0.54 |
| Cx | ng/mL | 4.6E-1 | 1.3E-2 | 6.0E1 | 5.2E1 | 1.1E2 | 1.3E2 | 9.3E-5 | 9.3E-5 | 3.9E2 | 3.9E2 | 447 | 13 | 170 | 13 | 0.42 |
| Db | ug/mL | 7.6E0 | 8.2E0 | 9.6E0 | 1.0E1 | 1.1E1 | 1.1E1 | 4.5E-1 | 9.3E-1 | 1.4E2 | 4.1E1 | 447 | 13 | 170 | 13 | 0.51 |
| Dc | nmol/L | 1.9E-2 | 1.4E-2 | 8.6E-2 | 2.0E-2 | 6.7E-1 | 1.9E-2 | 5.2E-6 | 1.4E-3 | 1.4E1 | 7.4E-2 | 447 | 13 | 170 | 13 | 0.43 |
| Dd | ug/mL | 7.8E-2 | 3.9E-2 | 1.9E-1 | 6.7E-2 | 3.1E-1 | 6.7E-2 | 1.9E-4 | 1.9E-3 | 3.6E0 | 2.2E-1 | 447 | 13 | 170 | 13 | 0.37 |
| De | ng/mL | 3.4E-3 | 3.4E-3 | 7.6E-2 | 6.0E-2 | 1.5E-1 | 9.8E-2 | 3.4E-3 | 3.4E-3 | 9.2E-1 | 3.1E-1 | 447 | 13 | 170 | 13 | 0.50 |
| Dg | ng/mL | 3.4E1 | 3.8E1 | 4.6E1 | 5.1E1 | 4.1E1 | 5.5E1 | 1.0E-1 | 3.4E0 | 1.9E2 | 1.8E2 | 447 | 13 | 170 | 13 | 0.49 |
| Di | pg/mL | 1.9E0 | 1.5E0 | 2.2E0 | 2.1E0 | 2.1E0 | 2.6E0 | 1.8E-1 | 1.8E-1 | 1.3E1 | 9.0E0 | 447 | 13 | 170 | 13 | 0.44 |
| Dk | uIU/mL | 1.6E-2 | 1.5E-2 | 8.7E-2 | 3.9E-2 | 5.1E-1 | 6.1E-2 | 1.1E-4 | 1.1E-4 | 8.9E0 | 2.3E-1 | 447 | 13 | 170 | 13 | 0.50 |
| Dl | ng/mL | 2.4E2 | 2.0E2 | 3.2E2 | 3.2E2 | 2.9E2 | 3.9E2 | 2.5E0 | 1.3E1 | 1.6E3 | 1.4E3 | 447 | 13 | 170 | 13 | 0.45 |
| Dp | ng/ml | 2.5E0 | 2.8E0 | 6.4E0 | 8.6E0 | 1.5E1 | 1.3E1 | 3.7E-3 | 5.1E-1 | 2.0E2 | 4.4E1 | 262 | 13 | 160 | 13 | 0.55 |
| Ef | ng/ml | 1.3E-1 | 1.2E-1 | 8.6E-1 | 1.1E0 | 1.9E0 | 2.4E0 | 5.7E-4 | 1.8E-2 | 1.0E1 | 8.7E0 | 325 | 13 | 167 | 13 | 0.51 |
| Wm | % | 7.2E-1 | 4.9E-1 | 3.2E1 | 4.0E1 | 1.8E2 | 1.5E2 | 5.4E-2 | 8.5E-2 | 2.4E3 | 5.7E2 | 353 | 15 | 182 | 15 | 0.45 |
| Ed | pg/ml | 5.2E-1 | 5.2E-1 | 5.9E1 | 1.4E1 | 4.5E2 | 2.6E1 | 5.2E-1 | 5.2E-1 | 7.3E3 | 9.4E1 | 262 | 13 | 159 | 13 | 0.47 |
| Tj | pg/mL | 3.7E-1 | 9.3E-1 | 5.6E1 | 1.6E1 | 3.0E1 | 2.3E1 | 3.6E-1 | 3.7E-1 | 3.5E3 | 7.1E1 | 323 | 13 | 169 | 13 | 0.57 |
| Po | pg/ml | 5.4E-1 | 3.3E0 | 8.9E0 | 6.5E0 | 2.6E1 | 8.9E0 | 8.0E-3 | 2.6E-2 | 2.7E2 | 3.6E1 | 755 | 23 | 295 | 23 | 0.57 |
| Et | ng/ml | 1.4E3 | 1.4E3 | 1.7E3 | 1.7E3 | 1.2E3 | 1.3E3 | 7.5E1 | 1.6E2 | 5.0E3 | 4.7E3 | 754 | 23 | 295 | 23 | 0.50 |
| Fa | ng/ml | 4.0E1 | 8.6E1 | 1.3E2 | 1.0E2 | 5.6E2 | 8.3E1 | 3.4E-2 | 3.4E0 | 8.0E3 | 2.7E2 | 261 | 13 | 158 | 13 | 0.66 |
| Ez | ng/ml | 3.8E0 | 7.8E0 | 1.5E1 | 2.9E1 | 3.2E1 | 4.3E1 | 1.3E-2 | 1.3E-2 | 3.0E2 | 1.5E2 | 262 | 13 | 160 | 13 | 0.61 |
| Fb | ng/ml | 2.5E1 | 2.9E1 | 2.2E1 | 3.0E1 | 1.1E1 | 1.2E1 | 5.9E-1 | 4.0E0 | 5.7E1 | 4.5E1 | 262 | 13 | 158 | 13 | 0.69 |
| Ex | ng/ml | 7.8E-2 | 9.7E-2 | 2.2E-1 | 2.3E-1 | 6.9E-1 | 2.8E-1 | 3.5E-5 | 2.7E-3 | 8.9E0 | 8.2E-1 | 245 | 10 | 117 | 10 | 0.60 |
| Fn | ng/ml | 2.1E-1 | 2.1E-1 | 5.9E0 | 3.7E0 | 2.7E1 | 8.9E0 | 1.1E-14 | 1.1E-14 | 4.2E2 | 3.2E1 | 262 | 13 | 160 | 13 | 0.35 |
| Fp | ng/ml | 1.3E1 | 2.2E1 | 2.5E1 | 4.0E1 | 2.8E1 | 4.3E1 | 6.0E-3 | 1.3E-1 | 1.4E2 | 1.3E2 | 787 | 23 | 296 | 23 | 0.57 |
| Fr | ng/ml | 3.5E4 | 7.0E4 | 1.1E5 | 1.4E5 | 1.7E5 | 1.7E5 | 1.9E2 | 2.8E3 | 9.0E5 | 6.0E5 | 890 | 23 | 300 | 23 | 0.57 |
| Fw | pg/ml | 1.1E0 | 2.5E0 | 6.2E1 | 6.8E0 | 4.8E2 | 1.2E1 | 1.1E-14 | 1.7E-14 | 6.9E3 | 4.4E1 | 325 | 13 | 168 | 13 | 0.46 |
| Fy | ng/ml | 3.8E1 | 3.4E1 | 6.0E1 | 6.0E1 | 7.3E1 | 6.5E1 | 1.2E-1 | 1.2E-1 | 6.5E2 | 2.1E2 | 260 | 13 | 159 | 13 | 0.51 |
| Gl | pg/ml | 7.1E3 | 5.9E3 | 1.1E4 | 1.1E4 | 9.1E3 | 1.1E4 | 9.1E1 | 4.9E2 | 3.4E4 | 3.0E4 | 316 | 13 | 166 | 13 | 0.49 |
| Gp | U/ml | 1.5E0 | 3.0E0 | 4.1E0 | 3.3E0 | 7.0E0 | 3.2E0 | 1.3E-3 | 1.5E-2 | 6.7E1 | 8.9E0 | 327 | 13 | 168 | 13 | 0.50 |

Figure 22

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Gz | ug/ml | 1.4E0 | 8.2E-1 | 8.9E0 | 5.4E0 | 3.7E1 | 9.0E0 | 2.9E-16 | 1.5E-1 | 4.8E2 | 2.8E1 | 181 | 10 | 106 | 10 | 0.41 |
| Ha | ng/ml | 2.3E0 | 4.6E0 | 9.5E0 | 1.3E1 | 2.1E1 | 2.0E1 | 6.4E-3 | 1.4E-3 | 1.3E2 | 6.1E1 | 260 | 13 | 159 | 13 | 0.59 |
| Nm | pg/ml | 1.5E4 | 9.9E3 | 3.4E4 | 2.2E4 | 8.7E4 | 3.6E4 | 1.0E-9 | 1.0E-9 | 1.6E6 | 1.7E5 | 758 | 23 | 297 | 23 | 0.42 |
| Nn | pg/ml | 1.5E2 | 3.6E2 | 1.7E3 | 1.2E3 | 7.6E3 | 1.6E3 | 1.0E-9 | 1.0E-9 | 1.0E5 | 5.3E3 | 758 | 23 | 297 | 23 | 0.60 |
| No | pg/ml | 1.5E1 | 9.1E0 | 3.9E1 | 2.3E1 | 1.2E2 | 2.6E1 | 1.0E-9 | 1.0E-9 | 2.5E3 | 7.9E1 | 758 | 23 | 297 | 23 | 0.44 |
| Nq | pg/ml | 1.7E0 | 4.4E0 | 1.7E1 | 1.5E1 | 6.8E1 | 2.6E1 | 1.0E-9 | 1.0E-9 | 1.2E3 | 1.1E2 | 758 | 23 | 297 | 23 | 0.55 |
| Nr | pg/ml | 9.7E-1 | 1.6E0 | 3.1E1 | 7.3E0 | 1.9E2 | 1.1E1 | 1.0E-9 | 1.0E-9 | 4.1E3 | 4.3E1 | 758 | 23 | 297 | 23 | 0.49 |
| Ns | pg/ml | 1.0E-9 | 1.0E-9 | 7.1E0 | 1.9E0 | 3.5E1 | 7.8E0 | 1.0E-9 | 1.0E-9 | 6.8E2 | 3.7E1 | 758 | 23 | 297 | 23 | 0.51 |
| Nt | pg/ml | 1.0E2 | 9.7E1 | 1.3E2 | 1.3E2 | 1.1E2 | 1.1E2 | 1.0E-9 | 1.0E-9 | 1.7E3 | 5.0E2 | 758 | 23 | 297 | 23 | 0.49 |
| Nu | pg/ml | 2.0E1 | 4.3E1 | 5.3E1 | 7.1E1 | 8.9E1 | 7.6E1 | 1.0E-9 | 1.0E-9 | 8.9E2 | 2.4E2 | 758 | 23 | 297 | 23 | 0.56 |
| Lu | pg/ml | 1.0E4 | 9.9E3 | 1.8E4 | 8.1E3 | 6.5E4 | 4.7E3 | 3.5E2 | 1.7E3 | 1.3E6 | 1.9E4 | 761 | 23 | 297 | 23 | 0.39 |
| Lv | pg/ml | 1.0E-9 | 1.0E-9 | 1.1E1 | 2.7E1 | 2.1E1 | 4.5E1 | 1.0E-9 | 1.0E-9 | 2.4E2 | 1.9E2 | 761 | 23 | 297 | 23 | 0.60 |
| Lw | pg/ml | 1.0E-9 | 1.0E-9 | 4.3E-1 | 1.0E-9 | 4.1E0 | 0.0E0 | 1.0E-9 | 1.0E-9 | 8.0E1 | 1.0E-9 | 761 | 23 | 297 | 23 | 0.49 |
| Lx | pg/ml | 1.0E-9 | 6.4E1 | 1.8E2 | 1.6E2 | 9.3E2 | 3.0E2 | 1.0E-9 | 1.0E-9 | 2.2E4 | 1.4E3 | 761 | 23 | 297 | 23 | 0.61 |
| Ly | pg/ml | 1.0E-9 | 7.0E0 | 1.0E1 | 1.6E1 | 2.0E1 | 1.9E1 | 1.0E-9 | 1.0E-9 | 1.2E2 | 5.6E1 | 761 | 23 | 297 | 23 | 0.61 |
| Lz | pg/ml | 1.0E-9 | 1.0E-9 | 4.0E0 | 8.5E-1 | 3.2E1 | 4.1E0 | 1.0E-9 | 1.0E-9 | 6.0E2 | 2.0E1 | 761 | 23 | 297 | 23 | 0.48 |
| Ma | pg/ml | 2.9E2 | 3.7E2 | 1.3E3 | 1.6E3 | 3.6E3 | 3.1E3 | 1.0E-9 | 1.0E-9 | 6.5E4 | 1.2E4 | 761 | 23 | 297 | 23 | 0.48 |
| Mb | pg/ml | 2.5E1 | 3.6E1 | 3.1E1 | 3.5E1 | 1.5E1 | 1.6E1 | 4.1E0 | 1.5E1 | 2.1E2 | 7.5E1 | 761 | 23 | 297 | 23 | 0.56 |
| Mc | pg/ml | 1.0E-9 | 1.0E-9 | 4.3E-2 | 1.1E-1 | 6.1E-1 | 5.2E-1 | 1.0E-9 | 1.0E-9 | 1.3E1 | 2.5E0 | 761 | 23 | 297 | 23 | 0.52 |
| Md | pg/ml | 1.0E-9 | 1.0E-9 | 4.5E-1 | 1.0E-9 | 3.9E0 | 0.0E0 | 1.0E-9 | 1.0E-9 | 6.8E1 | 1.0E-9 | 761 | 23 | 297 | 23 | 0.46 |
| Me | pg/ml | 3.3E1 | 2.6E1 | 3.2E1 | 2.7E1 | 2.0E1 | 1.5E1 | 1.0E-9 | 1.0E-9 | 3.2E2 | 5.5E1 | 761 | 23 | 297 | 23 | 0.40 |
| Mf | pg/ml | 1.0E-9 | 1.0E-9 | 5.0E-1 | 5.8E-1 | 2.8E0 | 1.7E0 | 1.0E-9 | 1.0E-9 | 5.6E1 | 7.7E0 | 761 | 23 | 297 | 23 | 0.53 |
| Mg | pg/ml | 1.6E0 | 7.3E-2 | 7.0E0 | 6.4E0 | 1.2E1 | 1.3E1 | 1.0E-9 | 1.0E-9 | 9.2E1 | 5.5E1 | 761 | 23 | 297 | 23 | 0.47 |
| Mh | pg/ml | 1.0E-9 | 1.0E-9 | 1.5E0 | 9.3E-2 | 1.0E1 | 3.1E-1 | 1.0E-9 | 1.0E-9 | 1.6E2 | 1.4E0 | 761 | 23 | 297 | 23 | 0.44 |
| Mi | pg/ml | 1.0E-9 | 1.0E-9 | 9.4E-1 | 1.0E-9 | 1.3E1 | 0.0E0 | 1.0E-9 | 1.0E-9 | 3.2E2 | 1.0E-9 | 761 | 23 | 297 | 23 | 0.49 |
| Mj | pg/ml | 1.0E-9 | 1.0E-9 | 4.7E0 | 3.5E0 | 2.7E1 | 7.6E0 | 1.0E-9 | 1.0E-9 | 4.6E2 | 2.9E1 | 761 | 23 | 297 | 23 | 0.56 |
| Mk | pg/ml | 2.8E-1 | 1.0E-9 | 1.4E1 | 1.2E1 | 9.2E1 | 2.3E1 | 1.0E-9 | 1.0E-9 | 1.7E3 | 9.4E1 | 761 | 23 | 297 | 23 | 0.50 |
| Ml | pg/ml | 1.0E-9 | 1.0E-9 | 6.0E0 | 2.3E0 | 8.1E1 | 7.4E0 | 1.0E-9 | 1.0E-9 | 2.1E3 | 3.3E1 | 761 | 23 | 297 | 23 | 0.50 |
| Mm | pg/ml | 6.1E2 | 5.3E2 | 1.1E3 | 8.2E2 | 1.4E3 | 1.1E3 | 1.0E-9 | 1.0E-9 | 1.2E4 | 5.3E3 | 761 | 23 | 297 | 23 | 0.46 |
| Mn | pg/ml | 5.4E0 | 4.8E0 | 1.0E1 | 6.2E0 | 2.0E1 | 6.1E0 | 1.0E-9 | 1.0E-9 | 3.5E2 | 2.2E1 | 761 | 23 | 297 | 23 | 0.43 |
| Mp | pg/ml | 1.0E-9 | 1.0E-9 | 1.0E1 | 1.1E1 | 3.6E1 | 2.5E1 | 1.0E-9 | 1.0E-9 | 6.3E2 | 9.7E1 | 760 | 23 | 297 | 23 | 0.51 |
| Mq | pg/ml | 1.0E-9 | 1.0E-9 | 2.8E0 | 4.1E0 | 1.6E1 | 1.3E1 | 1.0E-9 | 1.0E-9 | 2.1E2 | 5.1E1 | 760 | 23 | 297 | 23 | 0.53 |
| Mr | pg/ml | 1.0E-9 | 1.0E-9 | 3.2E1 | 7.2E0 | 1.8E2 | 1.5E1 | 1.0E-9 | 1.0E-9 | 2.2E3 | 6.8E1 | 760 | 23 | 297 | 23 | 0.56 |
| Ms | pg/ml | 4.1E2 | 3.7E2 | 5.6E2 | 5.5E2 | 6.6E2 | 6.3E2 | 1.0E-9 | 1.0E-9 | 5.9E3 | 3.0E3 | 760 | 23 | 297 | 23 | 0.51 |
| Mt | pg/ml | 2.4E-1 | 8.8E-1 | 7.3E0 | 5.1E0 | 4.5E1 | 1.6E1 | 1.0E-9 | 1.0E-9 | 8.7E2 | 7.9E1 | 760 | 23 | 297 | 23 | 0.55 |
| Mu | pg/ml | 1.0E-9 | 1.0E-9 | 9.0E-1 | 4.6E-1 | 7.0E0 | 9.3E-1 | 1.0E-9 | 1.0E-9 | 9.9E1 | 3.6E0 | 760 | 23 | 297 | 23 | 0.59 |
| Mv | pg/ml | 1.0E-9 | 1.0E-9 | 5.8E1 | 7.0E1 | 3.1E2 | 1.8E2 | 1.0E-9 | 1.0E-9 | 4.5E3 | 7.0E2 | 760 | 23 | 297 | 23 | 0.57 |
| Mw | pg/ml | 3.8E1 | 3.2E1 | 4.0E2 | 2.1E2 | 2.8E3 | 4.0E2 | 1.0E-9 | 1.0E-9 | 6.2E4 | 1.4E3 | 760 | 23 | 297 | 23 | 0.52 |
| Mx | pg/ml | 1.0E-9 | 1.0E-9 | 2.2E-1 | 1.3E-1 | 9.1E-1 | 3.3E-1 | 1.0E-9 | 1.0E-9 | 9.6E0 | 1.2E0 | 760 | 23 | 297 | 23 | 0.52 |
| My | pg/ml | 1.0E-9 | 1.0E-9 | 3.9E2 | 2.2E2 | 2.7E3 | 4.7E2 | 1.0E-9 | 1.0E-9 | 3.9E4 | 1.7E3 | 760 | 23 | 297 | 23 | 0.51 |
| Mz | pg/ml | 1.1E1 | 6.1E0 | 2.6E1 | 3.0E1 | 7.9E1 | 5.9E1 | 1.0E-9 | 1.0E-9 | 1.3E3 | 2.1E2 | 760 | 23 | 297 | 23 | 0.46 |
| Na | pg/ml | 1.0E-9 | 1.0E-9 | 7.4E-1 | 1.2E0 | 3.2E1 | 2.5E0 | 1.0E-9 | 1.0E-9 | 4.2E1 | 7.2E0 | 760 | 23 | 297 | 23 | 0.60 |
| Nb | pg/ml | 1.9E0 | 2.1E0 | 4.0E0 | 3.4E0 | 1.3E1 | 3.6E0 | 1.0E-9 | 1.0E-9 | 2.3E2 | 1.4E1 | 760 | 23 | 297 | 23 | 0.54 |
| Nc | pg/ml | 3.4E2 | 3.0E2 | 5.8E2 | 4.9E2 | 7.5E2 | 5.5E2 | 1.0E-9 | 1.0E-9 | 9.2E3 | 1.8E3 | 760 | 23 | 297 | 23 | 0.49 |
| Nd | pg/ml | 2.9E1 | 8.5E0 | 3.0E1 | 1.6E1 | 9.0E1 | 1.6E1 | 1.0E-9 | 1.0E-9 | 2.1E3 | 5.2E1 | 760 | 23 | 297 | 23 | 0.35 |
| Ne | pg/ml | 4.5E2 | 3.4E2 | 5.9E2 | 3.9E2 | 5.9E2 | 3.7E2 | 1.0E-9 | 1.0E-9 | 7.0E3 | 1.5E3 | 760 | 23 | 297 | 23 | 0.40 |
| Nf | pg/ml | 1.0E-9 | 1.0E-9 | 2.9E0 | 2.4E0 | 1.1E1 | 9.2E0 | 1.0E-9 | 1.0E-9 | 1.6E2 | 4.4E1 | 760 | 23 | 297 | 23 | 0.47 |
| Ng | pg/ml | 1.9E1 | 9.0E-1 | 1.1E2 | 1.2E2 | 2.2E2 | 2.3E2 | 1.0E-9 | 1.0E-9 | 1.6E3 | 8.6E2 | 760 | 23 | 297 | 23 | 0.44 |
| Nh | pg/ml | 6.9E1 | 4.8E1 | 9.2E1 | 6.9E1 | 8.3E1 | 5.8E1 | 1.0E-9 | 2.5E0 | 5.6E2 | 2.2E2 | 760 | 23 | 297 | 23 | 0.43 |
| Ni | pg/ml | 1.0E-9 | 1.1E1 | 7.2E1 | 1.4E2 | 1.2E2 | 2.2E2 | 1.0E-9 | 1.0E-9 | 1.1E3 | 7.1E2 | 760 | 23 | 297 | 23 | 0.58 |
| Nj | pg/ml | 7.3E0 | 5.1E0 | 1.1E1 | 7.4E0 | 1.2E1 | 6.7E0 | 1.0E-9 | 1.0E-9 | 8.3E1 | 2.0E1 | 760 | 23 | 297 | 23 | 0.43 |
| Nk | pg/ml | 1.8E1 | 1.6E1 | 3.4E1 | 3.0E1 | 4.0E1 | 3.3E1 | 1.0E-9 | 1.0E-9 | 2.0E2 | 1.1E2 | 760 | 23 | 297 | 23 | 0.50 |
| Nl | pg/ml | 4.6E1 | 3.6E1 | 6.2E1 | 4.5E1 | 7.0E1 | 4.2E1 | 1.0E-9 | 1.0E-9 | 1.1E3 | 1.4E2 | 760 | 23 | 297 | 23 | 0.43 |
| Tz | pg/ml | 4.6E3 | 6.1E3 | 1.3E4 | 7.6E3 | 6.3E4 | 5.5E3 | 1.0E-9 | 1.8E3 | 1.0E6 | 1.9E4 | 264 | 13 | 159 | 13 | 0.57 |
| Ua | pg/ml | 3.7E3 | 3.9E3 | 2.0E4 | 1.7E4 | 1.3E5 | 2.7E4 | 1.0E-9 | 8.8E2 | 2.1E6 | 9.0E4 | 264 | 13 | 159 | 13 | 0.52 |
| Ub | pg/ml | 5.7E2 | 4.5E2 | 8.7E2 | 8.9E2 | 1.1E3 | 1.1E3 | 1.0E-9 | 1.2E1 | 9.8E3 | 3.3E3 | 264 | 13 | 159 | 13 | 0.47 |
| Uc | pg/ml | 3.1E1 | 1.6E1 | 4.0E1 | 2.3E1 | 4.0E1 | 2.9E1 | 9.8E-2 | 5.1E0 | 4.4E2 | 1.2E2 | 264 | 13 | 159 | 13 | 0.27 |

Figure 22 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Uc | pg/ml | 9.2E2 | 6.4E2 | 2.0E3 | 9.2E2 | 4.4E3 | 1.2E3 | 1.0E-9 | 8.9E1 | 5.7E4 | 4.7E3 | 264 | 13 | 159 | 13 | 0.37 |
| Ud | pg/ml | 1.0E-9 | 1.0E-9 | 1.8E0 | 5.3E-1 | 2.4E1 | 1.9E0 | 1.0E-9 | 1.0E-9 | 3.9E2 | 6.9E0 | 264 | 13 | 159 | 13 | 0.53 |
| Hq | pg/ml | 1.0E0 | 1.5E0 | 1.2E2 | 2.1E1 | 1.8E3 | 7.1E1 | 1.0E-9 | 1.0E-9 | 3.4E4 | 3.4E2 | 756 | 23 | 296 | 23 | 0.53 |
| Hr | pg/ml | 1.1E2 | 3.1E2 | 8.0E2 | 1.1E3 | 1.7E3 | 1.6E3 | 1.0E-9 | 1.0E-9 | 1.7E4 | 6.0E3 | 756 | 23 | 296 | 23 | 0.62 |
| Hu | pg/ml | 5.1E0 | 3.1E1 | 2.6E3 | 1.6E3 | 2.6E4 | 4.4E3 | 1.0E-9 | 1.0E-9 | 6.3E5 | 1.9E4 | 756 | 23 | 296 | 23 | 0.58 |
| Hv | pg/ml | 1.3E0 | 2.7E0 | 4.2E0 | 4.2E0 | 3.4E1 | 7.4E0 | 1.0E-9 | 1.0E-9 | 8.9E2 | 3.5E1 | 756 | 23 | 296 | 23 | 0.65 |
| Hw | pg/ml | 6.6E0 | 5.5E0 | 3.1E1 | 1.6E1 | 3.5E2 | 3.2E1 | 1.0E-9 | 1.0E-9 | 9.4E3 | 1.5E2 | 756 | 23 | 296 | 23 | 0.49 |
| Hx | pg/ml | 8.3E0 | 1.4E1 | 4.0E1 | 3.2E1 | 3.5E2 | 5.3E1 | 1.0E-9 | 1.0E-9 | 9.3E3 | 2.2E2 | 756 | 23 | 296 | 23 | 0.60 |
| Ib | ng/ml | 4.9E-2 | 2.1E-2 | 1.2E0 | 9.7E0 | 5.3E0 | 2.5E1 | 1.0E-9 | 1.0E-9 | 5.6E1 | 8.8E1 | 259 | 12 | 159 | 12 | 0.47 |
| Ic | U/ml | 2.2E2 | 2.2E2 | 1.1E3 | 1.9E3 | 7.3E3 | 5.9E3 | 1.5E0 | 2.2E1 | 9.3E4 | 2.1E4 | 259 | 12 | 159 | 12 | 0.46 |
| Id | U/ml | 6.8E-1 | 8.4E-1 | 3.0E0 | 9.4E-1 | 2.7E1 | 4.9E-1 | 1.0E-9 | 3.3E-1 | 4.3E2 | 1.9E0 | 259 | 12 | 159 | 12 | 0.55 |
| Tt | pg/ml | 1.6E2 | 1.6E2 | 1.7E2 | 1.7E2 | 5.4E1 | 4.4E1 | 4.3E1 | 1.1E2 | 4.4E2 | 2.4E2 | 246 | 10 | 153 | 10 | 0.48 |
| To | pg/ml | 1.6E0 | 2.3E0 | 1.9E0 | 1.9E0 | 2.3E0 | 1.6E0 | 1.0E-9 | 1.0E-9 | 2.3E1 | 4.7E0 | 254 | 11 | 156 | 11 | 0.56 |
| Tr | pg/ml | 3.3E0 | 2.6E0 | 6.6E0 | 3.6E0 | 2.1E1 | 3.6E0 | 1.0E-9 | 4.4E-1 | 3.1E2 | 1.3E1 | 251 | 10 | 155 | 10 | 0.44 |
| Tn | pg/ml | 2.8E1 | 4.1E1 | 8.2E1 | 3.8E1 | 2.5E2 | 2.1E1 | 2.4E0 | 7.4E0 | 2.3E3 | 7.6E1 | 254 | 11 | 156 | 11 | 0.54 |
| Tv | ng/ml | 1.2E1 | 1.2E1 | 5.2E1 | 1.3E1 | 4.5E2 | 1.4E1 | 1.0E-9 | 1.0E-9 | 7.1E3 | 4.1E1 | 254 | 11 | 156 | 11 | 0.43 |
| Ih | ng/ml | 6.8E1 | 6.4E1 | 2.4E2 | 1.4E2 | 4.3E2 | 2.1E2 | 1.0E-9 | 1.0E-9 | 3.6E3 | 7.5E2 | 760 | 23 | 296 | 23 | 0.46 |
| Ii | ng/ml | 9.1E1 | 4.7E1 | 2.4E2 | 1.4E2 | 6.3E2 | 2.2E2 | 1.0E-9 | 2.3E0 | 8.4E3 | 8.8E2 | 760 | 23 | 296 | 23 | 0.44 |
| Ij | ng/ml | 7.6E1 | 7.5E1 | 2.0E2 | 1.2E2 | 1.1E3 | 1.3E2 | 1.0E-9 | 5.6E0 | 2.4E4 | 4.9E2 | 750 | 23 | 294 | 23 | 0.51 |
| Ik | ng/ml | 1.1E1 | 1.1E2 | 9.1E2 | 3.3E2 | 8.9E3 | 4.7E2 | 5.9E-1 | 2.8E0 | 1.2E5 | 1.5E3 | 755 | 23 | 294 | 23 | 0.61 |
| Il | ng/ml | 3.2E2 | 4.9E2 | 1.3E3 | 7.3E2 | 2.8E3 | 8.7E2 | 1.0E-9 | 1.0E-9 | 1.3E4 | 3.2E3 | 744 | 23 | 295 | 23 | 0.52 |
| Im | ng/ml | 2.1E2 | 2.4E2 | 3.7E2 | 5.5E2 | 5.3E2 | 1.3E3 | 1.3E1 | 3.2E1 | 5.8E3 | 6.2E3 | 754 | 23 | 295 | 23 | 0.49 |
| In | ng/ml | 3.6E0 | 4.3E0 | 3.0E1 | 1.1E1 | 2.3E2 | 2.0E1 | 1.0E-9 | 1.0E-9 | 4.5E3 | 9.6E1 | 760 | 23 | 296 | 23 | 0.50 |
| Hb | ng/ml | 2.6E1 | 2.5E1 | 3.7E1 | 3.0E1 | 3.5E1 | 2.0E1 | 6.2E-1 | 4.1E0 | 2.1E2 | 6.8E1 | 264 | 13 | 159 | 13 | 0.48 |
| Hc | pg/ml | 6.3E2 | 8.3E2 | 3.4E3 | 3.7E3 | 1.3E4 | 6.3E3 | 1.0E-9 | 1.0E-9 | 1.0E5 | 2.0E4 | 264 | 13 | 159 | 13 | 0.58 |
| Hf | ng/ml | 1.5E2 | 1.7E2 | 3.5E2 | 3.1E2 | 4.9E2 | 3.9E2 | 1.0E-9 | 1.0E-9 | 2.5E3 | 1.2E3 | 264 | 13 | 159 | 13 | 0.51 |
| Io | ng/ml | 8.2E3 | 3.9E3 | 2.6E4 | 1.2E4 | 1.6E5 | 2.5E4 | 1.0E-9 | 3.0E2 | 4.0E6 | 1.2E5 | 752 | 23 | 296 | 23 | 0.36 |
| Ip | ng/ml | 8.8E0 | 5.7E0 | 1.9E1 | 2.5E1 | 2.4E1 | 3.7E1 | 1.0E-9 | 1.4E-2 | 2.6E2 | 1.4E2 | 752 | 23 | 296 | 23 | 0.50 |
| Iq | ug/ml | 9.6E-2 | 8.1E-2 | 1.9E1 | 5.9E2 | 5.0E2 | 2.8E3 | 1.0E-9 | 1.0E-9 | 1.4E4 | 1.4E4 | 752 | 23 | 296 | 23 | 0.47 |
| Ir | ug/ml | 3.4E-1 | 6.3E-1 | 3.7E0 | 1.0E1 | 2.7E1 | 4.7E1 | 1.0E-9 | 1.0E-9 | 5.1E2 | 2.2E2 | 751 | 23 | 296 | 23 | 0.58 |
| Is | ng/ml | 1.4E0 | 3.0E0 | 6.2E0 | 6.8E0 | 2.4E1 | 1.1E1 | 1.0E-9 | 7.6E-2 | 5.5E2 | 4.6E1 | 752 | 23 | 296 | 23 | 0.58 |
| It | ng/ml | 2.0E0 | 3.3E0 | 2.4E1 | 1.3E1 | 1.4E2 | 3.1E1 | 1.0E-9 | 1.0E-9 | 2.8E3 | 1.5E2 | 752 | 23 | 296 | 23 | 0.61 |
| Iu | ng/ml | 2.2E2 | 4.1E2 | 1.5E3 | 1.5E3 | 4.3E3 | 5.0E3 | 1.0E-9 | 1.0E-9 | 2.9E4 | 2.4E4 | 752 | 23 | 296 | 23 | 0.53 |
| Iv | ng/ml | 1.2E1 | 1.2E1 | 6.5E1 | 4.8E1 | 6.0E2 | 9.8E1 | 1.0E-9 | 1.0E-9 | 1.6E4 | 4.5E2 | 751 | 23 | 296 | 23 | 0.52 |
| Iz | ng/ml | 1.4E2 | 1.1E2 | 6.3E2 | 5.3E2 | 3.9E3 | 8.1E2 | 9.2E-1 | 2.1E1 | 6.2E4 | 2.8E3 | 264 | 13 | 159 | 13 | 0.53 |
| Rc | pg/ml | 6.1E3 | 4.3E3 | 7.3E3 | 7.5E3 | 5.5E3 | 6.6E3 | 1.9E2 | 1.4E3 | 3.0E4 | 2.2E4 | 261 | 13 | 159 | 13 | 0.47 |
| Rb | pg/ml | 8.6E-1 | 1.1E0 | 2.8E0 | 1.8E0 | 5.5E0 | 1.9E0 | 1.0E-9 | 1.0E-9 | 5.6E1 | 5.6E0 | 261 | 13 | 159 | 13 | 0.52 |
| Pz | ng/ml | 4.4E3 | 1.8E3 | 8.3E3 | 4.4E3 | 4.0E4 | 4.2E3 | 1.3E1 | 9.5E1 | 1.0E6 | 1.0E4 | 753 | 23 | 295 | 23 | 0.42 |
| Qa | ng/ml | 3.4E3 | 5.2E3 | 6.3E3 | 6.8E3 | 1.1E4 | 5.4E3 | 1.2E1 | 2.9E2 | 2.2E5 | 1.9E4 | 753 | 23 | 295 | 23 | 0.58 |
| Qb | ng/ml | 8.7E1 | 1.7E2 | 2.1E2 | 2.1E2 | 5.0E2 | 2.4E2 | 7.9E-1 | 8.7E0 | 8.3E3 | 9.1E2 | 753 | 23 | 295 | 23 | 0.57 |
| Qc | ng/ml | 2.1E2 | 3.5E2 | 4.4E2 | 5.1E2 | 7.6E2 | 4.9E2 | 1.0E-9 | 8.6E0 | 1.1E4 | 1.6E3 | 753 | 23 | 295 | 23 | 0.57 |
| Qd | ng/ml | 8.9E3 | 1.4E4 | 1.9E4 | 2.4E4 | 7.8E4 | 3.3E4 | 1.5E2 | 1.7E3 | 2.0E6 | 1.5E5 | 753 | 23 | 295 | 23 | 0.61 |
| Qe | ng/ml | 9.1E2 | 1.2E3 | 1.8E3 | 1.9E3 | 4.0E3 | 2.2E3 | 1.0E-9 | 1.2E2 | 9.7E4 | 8.1E3 | 753 | 23 | 295 | 23 | 0.52 |
| Jd | ng/ml | 9.0E-1 | 2.0E0 | 6.6E0 | 2.1E0 | 4.3E1 | 2.3E0 | 1.0E-9 | 1.0E-9 | 6.5E2 | 8.3E0 | 262 | 13 | 160 | 13 | 0.56 |
| Je | ng/ml | 1.0E-9 | 1.0E-9 | 2.1E0 | 1.3E0 | 7.8E0 | 2.3E0 | 1.0E-9 | 1.0E-9 | 8.8E1 | 7.7E0 | 262 | 13 | 160 | 13 | 0.50 |
| Jf | ng/ml | 1.0E-9 | 8.8E-1 | 1.0E0 | 1.8E0 | 2.2E0 | 2.5E0 | 1.0E-9 | 1.0E-9 | 1.2E1 | 8.6E0 | 262 | 13 | 160 | 13 | 0.65 |
| Jg | ng/ml | 5.0E2 | 3.6E2 | 7.7E2 | 7.5E2 | 9.2E2 | 7.4E2 | 1.0E-9 | 3.8E0 | 1.0E4 | 2.4E3 | 756 | 23 | 296 | 23 | 0.50 |
| Jh | ng/ml | 2.8E0 | 6.0E0 | 2.4E1 | 2.2E1 | 1.1E2 | 4.0E1 | 1.0E-9 | 1.0E-9 | 1.6E3 | 1.4E2 | 756 | 23 | 296 | 23 | 0.56 |
| Ji | ng/ml | 5.2E1 | 8.1E1 | 7.7E1 | 9.5E1 | 8.9E1 | 8.3E1 | 1.0E-9 | 4.6E0 | 1.3E3 | 3.4E2 | 756 | 23 | 296 | 23 | 0.59 |
| Sr | pg/mL | 3.9E2 | 3.0E2 | 9.8E2 | 9.9E2 | 1.8E3 | 1.5E3 | 1.0E-9 | 1.0E-9 | 2.1E4 | 4.2E3 | 259 | 13 | 159 | 13 | 0.47 |
| Ss | pg/mL | 9.4E4 | 9.3E4 | 1.5E5 | 1.1E5 | 1.9E5 | 9.0E4 | 2.7E3 | 1.1E4 | 1.8E6 | 2.0E5 | 259 | 13 | 159 | 13 | 0.43 |
| St | pg/mL | 2.6E7 | 4.8E7 | 4.8E7 | 8.6E7 | 6.1E7 | 1.1E8 | 1.0E-9 | 1.6E6 | 5.4E8 | 3.5E8 | 257 | 12 | 157 | 12 | 0.59 |
| Ra | pg/ml | 1.0E-9 | 5.2E-1 | 8.4E-1 | 1.1E0 | 4.1E0 | 1.5E0 | 1.0E-9 | 1.0E-9 | 6.4E1 | 4.9E0 | 261 | 13 | 159 | 13 | 0.66 |
| Qz | pg/ml | 1.0E1 | 9.0E0 | 6.0E1 | 1.1E2 | 9.9E1 | 1.7E2 | 1.0E-9 | 1.0E-9 | 7.1E2 | 5.5E2 | 261 | 13 | 159 | 13 | 0.54 |
| Qy | pg/ml | 4.4E-1 | 8.8E-1 | 9.8E0 | 5.0E1 | 5.8E1 | 1.2E2 | 1.0E-9 | 1.0E-9 | 6.5E2 | 3.9E2 | 261 | 13 | 159 | 13 | 0.66 |
| Qx | pg/ml | 1.0E-9 | 1.0E-9 | 6.6E0 | 2.8E0 | 5.1E1 | 6.3E0 | 1.0E-9 | 1.0E-9 | 5.8E2 | 2.1E1 | 261 | 13 | 159 | 13 | 0.55 |
| Qw | pg/ml | 1.0E-9 | 1.0E-9 | 1.9E0 | 1.1E1 | 9.3E0 | 3.6E1 | 1.0E-9 | 1.0E-9 | 1.2E2 | 1.3E2 | 261 | 13 | 159 | 13 | 0.46 |

Figure 22 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Qv | pg/ml | 2.3E4 | 2.1E4 | 3.6E4 | 3.7E4 | 7.8E4 | 4.4E4 | 6.0E1 | 3.5E3 | 9.4E5 | 1.7E5 | 261 | 13 | 159 | 13 | 0.51 |
| Qu | pg/ml | 7.8E0 | 1.6E1 | 8.6E1 | 7.6E1 | 1.8E2 | 1.3E2 | 1.0E-9 | 1.0E-9 | 9.8E2 | 4.1E2 | 261 | 13 | 159 | 13 | 0.51 |
| Qt | pg/ml | 1.0E1 | 9.3E0 | 5.0E1 | 3.5E1 | 1.3E2 | 6.1E1 | 1.0E-9 | 1.0E-9 | 1.0E3 | 2.0E2 | 261 | 13 | 159 | 13 | 0.51 |
| Qh | ng/ml | 1.6E1 | 2.4E1 | 3.8E1 | 3.8E1 | 6.6E1 | 4.3E1 | 1.0E-9 | 7.8E-1 | 6.4E2 | 1.5E2 | 261 | 13 | 159 | 13 | 0.53 |
| Qg | ng/ml | 7.8E0 | 1.1E1 | 1.6E1 | 1.6E1 | 2.6E1 | 1.7E1 | 5.1E-2 | 7.7E-1 | 2.2E2 | 6.3E1 | 261 | 13 | 159 | 13 | 0.57 |
| Jj | ng/ml | 6.3E2 | 5.0E2 | 1.8E3 | 9.1E2 | 1.3E4 | 1.4E3 | 1.5E0 | 1.2E1 | 3.4E5 | 6.8E3 | 756 | 23 | 296 | 23 | 0.44 |
| Jk | ng/ml | 3.0E0 | 2.2E0 | 1.9E1 | 2.7E1 | 4.1E1 | 5.5E1 | 1.0E-9 | 2.0E-1 | 2.8E2 | 2.2E2 | 756 | 23 | 296 | 23 | 0.50 |
| Jl | ng/ml | 3.8E-1 | 4.8E-1 | 1.8E0 | 2.5E0 | 4.6E0 | 5.6E0 | 7.6E-4 | 2.2E-2 | 4.0E1 | 2.0E1 | 756 | 23 | 296 | 23 | 0.51 |
| Jm | ng/ml | 1.6E1 | 2.4E1 | 5.9E1 | 5.6E1 | 1.4E2 | 6.8E1 | 1.0E-9 | 4.1E-1 | 2.1E3 | 2.4E2 | 756 | 23 | 296 | 23 | 0.56 |
| Jn | pg/ml | 4.0E-1 | 2.6E-1 | 3.2E0 | 5.9E-1 | 3.2E1 | 1.0E0 | 1.0E-9 | 1.0E-9 | 6.2E2 | 5.0E0 | 755 | 23 | 296 | 23 | 0.45 |
| Jo | pg/ml | 3.6E3 | 3.8E3 | 5.0E3 | 4.4E3 | 5.3E3 | 3.4E3 | 2.0E1 | 2.3E2 | 1.0E5 | 1.5E4 | 756 | 23 | 296 | 23 | 0.49 |
| Jp | pg/ml | 6.9E4 | 6.7E4 | 7.2E4 | 7.0E4 | 3.8E4 | 3.2E4 | 5.8E2 | 6.0E3 | 3.8E5 | 1.3E5 | 756 | 23 | 296 | 23 | 0.50 |
| Jq | pg/ml | 9.4E1 | 1.4E2 | 1.6E2 | 1.6E2 | 3.5E2 | 1.2E2 | 1.0E0 | 2.2E1 | 8.7E3 | 4.8E2 | 756 | 23 | 296 | 23 | 0.57 |
| Jr | pg/ml | 5.2E0 | 6.7E0 | 4.0E1 | 8.6E0 | 4.4E2 | 9.5E0 | 1.0E-9 | 1.0E-9 | 1.1E4 | 4.0E1 | 756 | 23 | 296 | 23 | 0.55 |
| Js | pg/ml | 1.3E1 | 8.5E0 | 5.5E1 | 1.9E1 | 4.0E2 | 2.8E1 | 1.0E-9 | 3.5E0 | 1.0E4 | 1.2E2 | 756 | 23 | 296 | 23 | 0.43 |
| Jt | pg/ml | 2.7E3 | 2.0E3 | 3.3E3 | 2.3E3 | 2.8E3 | 1.4E3 | 2.2E1 | 4.6E2 | 5.2E4 | 6.2E3 | 756 | 23 | 296 | 23 | 0.38 |
| Ju | mIU/ml | 9.1E0 | 5.3E0 | 2.0E1 | 9.3E0 | 3.1E1 | 9.5E0 | 4.8E-2 | 2.7E-1 | 2.3E2 | 2.9E1 | 262 | 13 | 160 | 13 | 0.41 |
| Jv | mIU/ml | 1.3E1 | 8.1E0 | 3.3E1 | 1.7E1 | 5.7E1 | 3.4E1 | 1.0E-2 | 9.4E-3 | 4.4E2 | 1.3E2 | 262 | 13 | 160 | 13 | 0.39 |
| Jy | ng/ml | 1.6E-3 | 1.8E-3 | 2.3E-3 | 2.2E-3 | 4.2E-3 | 1.3E-3 | 1.0E-9 | 1.0E-9 | 5.2E-2 | 4.4E-3 | 262 | 13 | 160 | 13 | 0.58 |
| Kc | pg/ml | 2.6E1 | 4.3E1 | 4.5E1 | 7.9E1 | 4.8E1 | 7.2E1 | 1.0E-9 | 6.9E0 | 2.7E2 | 1.9E2 | 264 | 13 | 159 | 13 | 0.65 |
| Kd | pg/ml | 1.0E-9 | 1.0E-9 | 3.3E2 | 5.3E2 | 2.4E3 | 1.2E3 | 1.0E-9 | 1.0E-9 | 3.8E4 | 3.7E3 | 264 | 13 | 159 | 13 | 0.57 |
| Ke | pg/ml | 1.3E4 | 9.6E3 | 1.6E4 | 1.3E4 | 2.2E4 | 8.5E3 | 3.4E2 | 2.2E3 | 3.2E5 | 3.1E4 | 264 | 13 | 159 | 13 | 0.47 |
| Kf | pg/mL | 7.4E0 | 8.9E0 | 7.8E0 | 8.5E0 | 7.4E0 | 6.8E0 | 1.0E-9 | 1.0E-9 | 7.8E1 | 2.1E1 | 264 | 13 | 159 | 13 | 0.54 |
| Kg | pg/mL | 1.2E3 | 1.1E3 | 2.0E3 | 1.7E3 | 2.9E3 | 2.2E3 | 7.7E1 | 3.0E2 | 2.7E4 | 8.5E3 | 264 | 13 | 159 | 13 | 0.47 |
| Ki | pg/ml | 5.9E1 | 8.8E1 | 6.8E1 | 9.6E1 | 5.2E1 | 7.1E1 | 1.0E-9 | 1.0E-9 | 3.8E2 | 2.9E2 | 263 | 13 | 159 | 13 | 0.66 |
| Kj | pg/ml | 9.8E2 | 7.6E2 | 1.7E3 | 1.4E3 | 1.9E3 | 1.5E3 | 3.0E1 | 2.1E2 | 1.5E4 | 5.2E3 | 264 | 13 | 159 | 13 | 0.43 |
| Kk | pg/ml | 6.8E0 | 1.7E1 | 1.2E1 | 2.5E1 | 1.6E1 | 2.3E1 | 1.0E-9 | 1.0E-9 | 1.6E2 | 6.4E1 | 264 | 13 | 159 | 13 | 0.66 |
| Kl | pg/ml | 2.1E4 | 3.3E4 | 2.8E4 | 3.3E4 | 2.6E4 | 3.3E4 | 2.3E2 | 1.0E3 | 1.6E5 | 1.1E5 | 264 | 13 | 159 | 13 | 0.51 |
| Kn | pg/ml | 3.0E1 | 3.0E1 | 8.1E1 | 5.3E1 | 3.1E2 | 6.5E1 | 1.0E-9 | 1.0E-9 | 4.9E3 | 1.9E2 | 264 | 13 | 159 | 13 | 0.48 |
| Ko | pg/ml | 4.1E2 | 3.2E2 | 5.2E2 | 7.0E2 | 5.2E2 | 8.3E2 | 1.0E-9 | 1.0E-9 | 4.1E3 | 2.5E3 | 264 | 13 | 159 | 13 | 0.52 |
| Kp | pg/ml | 3.4E2 | 2.8E2 | 4.1E2 | 4.5E2 | 8.4E2 | 3.6E2 | 1.0E-9 | 3.2E1 | 1.3E4 | 1.0E3 | 264 | 13 | 159 | 13 | 0.56 |
| Kq | pg/ml | 3.2E2 | 3.8E2 | 1.1E3 | 4.6E2 | 9.9E3 | 2.3E2 | 5.1E0 | 1.7E2 | 1.6E5 | 8.5E2 | 257 | 13 | 154 | 13 | 0.60 |
| Kr | pg/ml | 5.6E-1 | 1.0E-9 | 4.0E0 | 2.5E0 | 2.6E1 | 5.9E0 | 1.0E-9 | 1.0E-9 | 4.2E2 | 2.1E1 | 257 | 13 | 154 | 13 | 0.42 |
| Ks | pg/ml | 1.4E4 | 1.3E4 | 2.0E4 | 1.8E4 | 1.9E4 | 1.6E4 | 2.2E2 | 2.4E3 | 1.1E5 | 5.0E4 | 257 | 13 | 154 | 13 | 0.49 |
| Kx | ng/ml | 1.0E-9 | 6.8E-3 | 6.9E-3 | 8.1E-3 | 1.4E-2 | 8.3E-3 | 1.0E-9 | 1.0E-9 | 1.0E-1 | 2.7E-2 | 263 | 12 | 159 | 12 | 0.61 |
| Ky | ng/ml | 9.8E-2 | 1.6E-1 | 3.8E-1 | 3.9E-1 | 8.4E-1 | 6.3E-1 | 1.0E-9 | 1.0E-9 | 6.4E0 | 2.2E0 | 263 | 12 | 159 | 12 | 0.53 |
| Kz | ng/ml | 1.0E-9 | 1.0E-9 | 3.7E-3 | 3.5E-3 | 5.8E-3 | 5.4E-3 | 1.0E-9 | 1.0E-9 | 3.6E-2 | 1.4E-2 | 263 | 12 | 159 | 12 | 0.50 |
| Ld | pg/ml | 1.0E-9 | 3.6E0 | 3.7E0 | 4.4E0 | 9.2E0 | 4.5E0 | 1.0E-9 | 1.0E-9 | 8.4E1 | 1.5E1 | 264 | 13 | 158 | 13 | 0.66 |
| Lh | pg/ml | 1.3E4 | 1.2E4 | 2.1E4 | 2.2E4 | 3.3E4 | 2.2E4 | 1.0E-9 | 4.0E2 | 4.8E5 | 7.7E4 | 756 | 23 | 297 | 23 | 0.52 |
| Li | pg/ml | 3.2E3 | 4.9E3 | 1.7E4 | 1.7E4 | 6.6E4 | 4.8E4 | 1.0E-9 | 1.0E-9 | 1.3E6 | 2.3E5 | 756 | 23 | 297 | 23 | 0.52 |
| Lj | pg/ml | 2.9E3 | 2.6E3 | 2.4E4 | 1.6E4 | 6.8E4 | 3.7E4 | 1.0E-9 | 1.5E2 | 5.2E5 | 1.7E5 | 756 | 23 | 297 | 23 | 0.50 |
| Rm | ng/ml | 1.9E1 | 2.7E1 | 5.2E1 | 4.6E1 | 8.4E1 | 4.5E1 | 2.2E-1 | 1.4E0 | 6.5E2 | 1.6E2 | 256 | 13 | 158 | 13 | 0.60 |
| Rh | ng/ml | 1.3E2 | 1.7E2 | 4.0E2 | 2.3E2 | 1.4E3 | 2.4E2 | 4.7E0 | 7.5E0 | 1.7E4 | 8.5E2 | 256 | 13 | 158 | 13 | 0.50 |
| Ri | ng/ml | 1.0E-9 | 1.0E-9 | 4.4E0 | 3.9E0 | 1.6E1 | 9.7E0 | 1.0E-9 | 1.0E-9 | 2.2E2 | 3.6E1 | 257 | 13 | 159 | 13 | 0.50 |
| Rg | ng/ml | 1.0E-9 | 1.0E-9 | 5.0E-2 | 5.8E-2 | 3.0E-1 | 1.9E-1 | 1.0E-9 | 1.0E-9 | 3.0E0 | 6.9E-1 | 256 | 13 | 158 | 13 | 0.56 |
| Rj | ng/ml | 1.0E-9 | 1.0E-9 | 2.4E0 | 3.2E-1 | 1.8E1 | 8.1E-1 | 1.0E-9 | 1.0E-9 | 2.7E2 | 2.5E0 | 257 | 13 | 159 | 13 | 0.43 |
| Rf | ng/ml | 4.1E-1 | 6.1E-1 | 1.0E0 | 8.4E-1 | 1.8E0 | 7.7E-1 | 7.8E-3 | 3.3E-2 | 1.5E1 | 2.6E0 | 256 | 13 | 158 | 13 | 0.54 |
| Ql | pg/ml | 4.5E0 | 7.3E0 | 1.3E1 | 1.6E1 | 2.4E1 | 3.6E1 | 1.0E-9 | 1.0E-9 | 1.8E2 | 1.3E2 | 262 | 13 | 160 | 13 | 0.50 |
| Qm | pg/ml | 4.1E0 | 1.0E-9 | 2.2E1 | 9.8E0 | 4.0E1 | 4.1E1 | 1.0E-9 | 1.0E-9 | 3.6E2 | 3.6E1 | 262 | 13 | 160 | 13 | 0.40 |
| Qn | pg/ml | 6.1E-1 | 5.9E-2 | 7.4E0 | 9.8E0 | 2.4E1 | 2.8E1 | 1.0E-9 | 1.0E-9 | 2.4E2 | 1.0E2 | 262 | 13 | 160 | 13 | 0.42 |
| Nv | pg/ml | 3.8E3 | 3.2E3 | 1.0E4 | 1.5E4 | 4.5E4 | 3.5E4 | 1.0E-9 | 3.2E2 | 1.1E6 | 1.6E5 | 762 | 23 | 297 | 23 | 0.52 |
| Nw | pg/ml | 8.8E3 | 1.3E4 | 1.3E4 | 1.4E4 | 1.7E4 | 1.0E4 | 8.6E1 | 9.3E2 | 2.1E5 | 3.7E4 | 762 | 23 | 297 | 23 | 0.58 |
| Nx | pg/ml | 2.2E2 | 2.2E2 | 4.1E2 | 5.4E2 | 6.6E2 | 6.0E2 | 1.0E-9 | 1.0E-9 | 7.4E3 | 1.9E3 | 762 | 23 | 297 | 23 | 0.58 |
| Ny | pg/ml | 6.0E0 | 1.8E0 | 6.1E1 | 6.7E1 | 9.2E2 | 2.5E2 | 1.0E-9 | 1.0E-9 | 2.5E4 | 1.2E3 | 762 | 23 | 297 | 23 | 0.49 |
| Oa | pg/ml | 1.8E2 | 3.5E2 | 4.4E2 | 6.8E2 | 7.4E2 | 8.7E2 | 1.0E-9 | 2.5E1 | 4.8E3 | 2.7E3 | 262 | 13 | 160 | 13 | 0.61 |
| Oe | pg/ml | 4.2E1 | 2.3E1 | 2.7E2 | 2.6E2 | 7.9E2 | 3.9E2 | 1.0E-9 | 1.0E-9 | 1.9E4 | 1.3E3 | 755 | 23 | 296 | 23 | 0.50 |
| Of | pg/ml | 1.6E2 | 9.7E1 | 5.3E3 | 9.5E3 | 2.9E4 | 2.7E4 | 1.0E-9 | 1.0E-9 | 6.2E5 | 1.2E5 | 761 | 23 | 297 | 23 | 0.47 |

Figure 22 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Og | pg/ml | 7.9E-2 | 7.9E-2 | 4.6E-1 | 1.7E-1 | 1.5E0 | 2.4E-1 | 1.0E-9 | 1.0E-9 | 2.0E1 | 9.6E-1 | 761 | 23 | 297 | 23 | 0.47 |
| Oh | pg/ml | 2.5E0 | 4.2E0 | 2.0E1 | 1.1E1 | 1.5E2 | 1.9E1 | 1.0E-9 | 3.0E-1 | 3.5E3 | 8.8E1 | 761 | 23 | 297 | 23 | 0.61 |
| Oi | pg/ml | 2.4E0 | 1.0E-9 | 5.9E0 | 7.5E0 | 9.6E0 | 1.2E1 | 1.0E-9 | 1.0E-9 | 8.6E1 | 4.9E1 | 761 | 23 | 297 | 23 | 0.48 |
| Ok | pg/ml | 3.9E2 | 4.9E2 | 5.3E2 | 7.3E2 | 5.7E2 | 7.5E2 | 1.3E1 | 4.3E1 | 7.8E3 | 3.1E3 | 761 | 23 | 297 | 23 | 0.56 |
| Om | pg/ml | 3.8E2 | 4.5E2 | 8.2E2 | 6.9E2 | 2.6E3 | 8.9E2 | 1.0E-9 | 1.0E-9 | 5.1E4 | 4.2E3 | 761 | 23 | 297 | 23 | 0.53 |
| On | pg/ml | 1.8E2 | 2.1E2 | 2.8E2 | 3.1E2 | 4.2E2 | 3.4E2 | 1.0E-9 | 1.0E-9 | 4.5E3 | 1.2E3 | 761 | 23 | 297 | 23 | 0.52 |
| Or | pg/ml | 1.4E1 | 1.2E1 | 3.5E1 | 3.3E1 | 6.7E1 | 5.3E1 | 1.0E-9 | 1.0E-9 | 5.1E2 | 1.8E2 | 265 | 13 | 159 | 13 | 0.51 |
| Ow | pg/ml | 3.3E1 | 2.4E1 | 1.5E2 | 7.1E1 | 5.7E2 | 1.1E2 | 1.0E-9 | 1.0E-9 | 8.1E3 | 4.0E2 | 265 | 13 | 159 | 13 | 0.43 |
| Ou | pg/ml | 5.1E2 | 2.8E2 | 9.5E2 | 1.0E3 | 1.5E3 | 2.0E3 | 1.0E-9 | 1.0E-9 | 9.8E3 | 7.5E3 | 265 | 13 | 159 | 13 | 0.42 |
| Ul | ng/ml | 1.0E-9 | 1.0E-9 | 1.8E0 | 1.0E-9 | 8.3E0 | 0.0E0 | 1.0E-9 | 1.0E-9 | 1.0E2 | 1.0E-9 | 270 | 13 | 163 | 13 | 0.45 |
| Uo | ng/ml | 1.0E-9 | 1.0E-9 | 9.7E-2 | 1.3E-1 | 2.2E-1 | 2.3E-1 | 1.0E-9 | 1.0E-9 | 1.5E0 | 5.8E-1 | 270 | 13 | 163 | 13 | 0.52 |
| Uk | ng/ml | 1.0E-9 | 1.0E-9 | 8.5E-3 | 2.5E-3 | 2.7E-2 | 6.6E-3 | 1.0E-9 | 1.0E-9 | 3.2E-1 | 2.4E-2 | 270 | 13 | 163 | 13 | 0.44 |
| Um | ng/ml | 1.0E-9 | 1.0E-9 | 4.2E-1 | 6.5E-1 | 9.1E-1 | 1.4E0 | 1.0E-9 | 1.0E-9 | 6.8E0 | 4.0E0 | 270 | 13 | 163 | 13 | 0.48 |
| Uf | ng/ml | 6.5E-2 | 6.8E-2 | 1.8E-1 | 2.0E-1 | 6.4E-1 | 4.5E-1 | 1.3E-3 | 5.0E-3 | 8.6E0 | 1.7E0 | 270 | 13 | 163 | 13 | 0.52 |
| Uh | ng/ml | 2.1E0 | 2.0E0 | 3.4E0 | 3.0E0 | 3.7E0 | 3.4E0 | 1.3E-2 | 6.3E-2 | 2.1E1 | 1.3E1 | 270 | 13 | 163 | 13 | 0.48 |
| Un | ng/ml | 1.9E0 | 2.7E0 | 2.2E0 | 2.7E0 | 1.9E0 | 1.3E0 | 1.3E-1 | 8.5E-1 | 2.5E1 | 5.2E0 | 270 | 13 | 163 | 13 | 0.65 |
| Ug | ng/ml | 1.5E1 | 9.7E0 | 2.9E1 | 2.0E1 | 3.2E1 | 3.2E1 | 6.9E-1 | 1.8E0 | 2.1E2 | 1.2E2 | 270 | 13 | 163 | 13 | 0.36 |
| Ur | ng/ml | 1.5E-1 | 1.7E-1 | 8.9E-1 | 2.9E-1 | 5.8E0 | 4.8E-1 | 1.0E-9 | 1.0E-9 | 9.3E1 | 1.8E0 | 269 | 13 | 162 | 13 | 0.49 |
| Up | ng/ml | 1.0E-9 | 1.0E-9 | 1.4E-2 | 3.0E-3 | 1.5E-1 | 9.6E-3 | 1.0E-9 | 1.0E-9 | 2.4E0 | 3.5E-2 | 269 | 13 | 162 | 13 | 0.46 |
| Us | ng/ml | 2.9E-3 | 1.0E-9 | 2.6E-2 | 5.5E-3 | 1.1E-1 | 1.2E-2 | 1.0E-9 | 1.0E-9 | 1.7E0 | 4.4E-2 | 269 | 13 | 162 | 13 | 0.38 |
| Uv | ng/ml | 3.1E-3 | 1.9E-3 | 1.4E-2 | 2.1E-2 | 4.7E-2 | 6.1E-2 | 1.0E-9 | 1.0E-9 | 4.3E-1 | 2.2E-1 | 269 | 13 | 162 | 13 | 0.45 |
| Ut | ng/ml | 6.6E-1 | 3.4E-1 | 2.9E0 | 1.3E0 | 9.6E0 | 1.9E0 | 1.0E-9 | 6.8E-2 | 7.8E1 | 6.2E0 | 269 | 13 | 162 | 13 | 0.46 |
| Uu | ng/ml | 7.1E0 | 6.9E0 | 7.9E0 | 8.2E0 | 5.6E0 | 6.9E0 | 5.5E-1 | 1.2E0 | 4.0E1 | 2.3E1 | 269 | 13 | 162 | 13 | 0.48 |
| Vp | ng/ml | 1.0E-9 | 1.0E-9 | 5.6E-1 | 1.0E-9 | 4.6E0 | 0.0E0 | 1.0E-9 | 1.0E-9 | 5.0E1 | 1.0E-9 | 270 | 13 | 163 | 13 | 0.43 |
| Vt | ng/ml | 6.8E0 | 7.3E0 | 9.9E0 | 1.1E1 | 1.3E1 | 1.1E1 | 4.3E-1 | 1.7E0 | 1.6E2 | 4.2E1 | 270 | 13 | 163 | 13 | 0.54 |
| Vu | ng/ml | 1.0E-9 | 1.0E-9 | 2.1E0 | 1.2E0 | 5.4E0 | 1.8E0 | 1.0E-9 | 1.0E-9 | 5.1E1 | 5.3E0 | 264 | 13 | 162 | 13 | 0.52 |
| Vq | ng/ml | 2.7E2 | 9.7E1 | 4.3E3 | 1.0E3 | 4.8E4 | 1.7E3 | 2.0E-1 | 1.0E1 | 6.8E5 | 5.0E3 | 201 | 9 | 131 | 9 | 0.53 |
| Vo | ng/ml | 2.6E1 | 2.2E1 | 2.5E1 | 2.2E1 | 4.7E0 | 5.3E0 | 6.7E0 | 8.2E0 | 3.5E1 | 2.8E1 | 270 | 13 | 163 | 13 | 0.33 |
| Vs | ng/ml | 1.0E-9 | 6.3E-1 | 8.3E0 | 3.9E0 | 3.7E1 | 7.9E0 | 1.0E-9 | 1.0E-9 | 4.5E2 | 2.7E1 | 260 | 12 | 159 | 12 | 0.52 |
| Vv | ng/ml | 2.9E0 | 3.3E0 | 5.8E0 | 4.0E0 | 9.7E0 | 4.4E0 | 1.0E-9 | 1.0E-9 | 8.4E1 | 1.5E1 | 268 | 13 | 162 | 13 | 0.46 |
| Oy | pg/ml | 4.9E-1 | 3.3E-1 | 5.9E0 | 3.7E0 | 3.1E1 | 8.2E0 | 1.0E-9 | 1.0E-9 | 4.0E2 | 3.7E1 | 760 | 23 | 296 | 23 | 0.48 |
| Oz | pg/ml | 1.4E-3 | 1.5E-1 | 3.2E-1 | 2.1E-1 | 1.4E0 | 2.5E-1 | 1.0E-9 | 1.0E-9 | 2.9E1 | 8.2E-1 | 760 | 23 | 296 | 23 | 0.54 |
| Pa | pg/ml | 3.8E-1 | 1.9E-1 | 1.7E0 | 4.8E-1 | 6.5E0 | 7.4E-1 | 1.0E-9 | 1.0E-9 | 1.0E2 | 3.0E0 | 760 | 23 | 296 | 23 | 0.41 |
| Pb | pg/ml | 1.0E-9 | 1.0E-9 | 9.0E-1 | 1.3E0 | 1.8E1 | 5.8E0 | 1.0E-9 | 1.0E-9 | 4.9E2 | 2.8E1 | 760 | 23 | 296 | 23 | 0.49 |
| Pc | pg/ml | 4.2E-2 | 6.7E-2 | 3.6E-1 | 2.7E-1 | 9.3E-1 | 3.7E-1 | 1.0E-9 | 1.0E-9 | 1.6E1 | 1.4E0 | 760 | 23 | 296 | 23 | 0.51 |
| Pd | pg/ml | 1.9E0 | 1.4E0 | 5.4E0 | 2.4E0 | 3.2E1 | 2.6E0 | 1.0E-9 | 1.0E-9 | 8.4E2 | 9.4E0 | 760 | 23 | 296 | 23 | 0.45 |
| Pe | pg/ml | 2.1E1 | 2.9E1 | 1.2E2 | 7.4E1 | 4.8E2 | 1.0E2 | 1.0E-9 | 1.0E-9 | 6.7E3 | 3.8E2 | 760 | 23 | 296 | 23 | 0.54 |
| Pf | pg/ml | 1.6E0 | 3.4E0 | 1.2E1 | 8.9E0 | 6.3E1 | 2.0E1 | 1.0E-9 | 1.0E-9 | 1.5E3 | 9.9E1 | 760 | 23 | 296 | 23 | 0.51 |
| Pg | pg/ml | 3.3E0 | 2.3E0 | 4.8E1 | 2.6E1 | 3.7E2 | 5.3E1 | 1.0E-9 | 1.0E-9 | 7.7E3 | 1.9E2 | 760 | 23 | 296 | 23 | 0.49 |
| Ph | ng/ml | 1.8E-1 | 1.7E-1 | 3.5E-1 | 5.1E-1 | 5.7E-1 | 7.2E-1 | 1.0E-9 | 1.9E-2 | 5.4E0 | 2.2E0 | 265 | 13 | 159 | 13 | 0.55 |
| Pi | ng/ml | 2.0E-1 | 2.5E-1 | 5.8E-1 | 2.2E-1 | 5.0E0 | 1.7E-1 | 1.0E-9 | 1.0E-9 | 8.2E1 | 5.4E-1 | 265 | 13 | 159 | 13 | 0.48 |
| Pj | ng/mL | 5.7E0 | 4.3E0 | 6.4E0 | 5.0E0 | 4.5E0 | 2.5E0 | 3.8E-2 | 1.3E0 | 3.1E1 | 9.9E0 | 265 | 13 | 159 | 13 | 0.43 |
| Pk | ng/ml | 8.8E-3 | 8.9E-3 | 1.8E-2 | 8.6E-3 | 9.4E-2 | 7.1E-3 | 1.0E-9 | 1.0E-9 | 1.5E0 | 2.6E-2 | 265 | 13 | 159 | 13 | 0.45 |
| aA | mg/dL | 8.0E-1 | 9.7E-1 | 9.0E-1 | 1.2E0 | 4.3E-1 | 7.7E-1 | 2.0E-1 | 4.5E-1 | 4.1E0 | 3.0E0 | 2356 | 29 | 452 | 29 | 0.60 |
| aC | mg/mL | 2.9E0 | 2.4E0 | 3.2E0 | 2.6E0 | 1.4E0 | 1.2E0 | 7.7E-1 | 7.4E-1 | 8.9E0 | 5.1E0 | 466 | 13 | 180 | 13 | 0.39 |
| aD | ug/mL | 3.2E0 | 3.0E0 | 4.5E0 | 4.8E0 | 4.0E0 | 5.3E0 | 4.3E-1 | 1.1E0 | 3.5E1 | 2.1E1 | 466 | 13 | 180 | 13 | 0.47 |
| aE | mg/mL | 5.6E-1 | 5.5E-1 | 5.7E-1 | 5.9E-1 | 1.5E-1 | 2.0E-1 | 1.8E-1 | 3.5E-1 | 1.1E0 | 1.0E0 | 466 | 13 | 180 | 13 | 0.48 |
| aF | ng/mL | 2.2E0 | 1.9E0 | 3.8E0 | 4.0E0 | 5.4E0 | 8.0E0 | 4.3E-3 | 3.5E-1 | 5.0E1 | 3.0E1 | 466 | 13 | 180 | 13 | 0.43 |
| aG | mg/mL | 1.3E-1 | 1.3E-1 | 1.5E-1 | 1.6E-1 | 8.7E-2 | 1.0E-1 | 1.7E-2 | 6.9E-2 | 5.4E-1 | 4.2E-1 | 466 | 13 | 180 | 13 | 0.51 |
| aH | ug/mL | 7.5E1 | 7.9E1 | 8.0E1 | 9.8E1 | 4.3E1 | 5.4E1 | 4.6E0 | 3.5E1 | 2.9E2 | 2.3E2 | 466 | 13 | 180 | 13 | 0.60 |
| aI | ug/mL | 1.9E2 | 2.0E2 | 1.9E2 | 1.9E2 | 6.0E1 | 5.5E1 | 2.8E1 | 1.1E2 | 3.7E2 | 2.7E2 | 466 | 13 | 180 | 13 | 0.52 |
| aJ | ug/mL | 2.4E0 | 4.4E0 | 3.0E0 | 4.2E0 | 2.0E0 | 2.0E0 | 7.3E-1 | 1.5E0 | 1.7E1 | 7.6E0 | 466 | 13 | 180 | 13 | 0.71 |
| aK | ng/mL | 1.5E0 | 1.9E0 | 2.4E0 | 2.1E0 | 2.6E0 | 1.6E0 | 2.9E-4 | 4.5E-1 | 1.8E1 | 6.1E0 | 466 | 13 | 180 | 13 | 0.54 |
| aL | mg/mL | 8.0E-1 | 8.8E-1 | 8.1E-1 | 8.9E-1 | 2.7E-1 | 2.2E-1 | 1.9E-1 | 5.7E-1 | 1.7E0 | 1.4E0 | 466 | 13 | 180 | 13 | 0.59 |
| aM | U/mL | 2.2E1 | 1.3E1 | 5.1E1 | 2.7E1 | 1.1E2 | 3.9E1 | 4.2E-2 | 4.2E-2 | 1.6E3 | 1.4E2 | 466 | 13 | 180 | 13 | 0.39 |
| aN | U/mL | 1.3E1 | 1.7E1 | 2.0E1 | 2.8E1 | 2.6E1 | 3.4E1 | 2.5E-3 | 5.0E0 | 3.3E2 | 1.3E2 | 466 | 13 | 180 | 13 | 0.58 |
| aO | pg/mL | 2.6E1 | 4.3E1 | 2.8E2 | 4.3E2 | 7.5E2 | 1.1E3 | 6.0E-2 | 2.1E0 | 6.6E3 | 3.9E3 | 466 | 13 | 180 | 13 | 0.56 |

Figure 22 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aP | ng/mL | 1.6E0 | 2.0E0 | 2.0E0 | 2.5E0 | 1.8E0 | 1.3E0 | 4.5E-1 | 1.2E0 | 2.8E1 | 5.4E0 | 466 | 13 | 180 | 13 | 0.66 |
| aQ | ng/mL | 2.9E-1 | 2.9E-1 | 4.4E-1 | 4.4E-1 | 4.6E-1 | 3.3E-1 | 2.0E-4 | 6.9E-2 | 4.0E0 | 1.1E0 | 466 | 13 | 180 | 13 | 0.54 |
| aR | ng/mL | 1.8E0 | 1.9E0 | 2.8E0 | 1.7E0 | 3.3E0 | 8.3E-1 | 1.8E-1 | 3.6E-1 | 3.4E1 | 2.7E0 | 466 | 13 | 180 | 13 | 0.43 |
| aS | ng/mL | 2.6E-1 | 4.8E-1 | 6.4E-1 | 6.4E-1 | 1.8E0 | 5.4E-1 | 4.2E-3 | 4.2E-3 | 3.3E1 | 1.7E0 | 466 | 13 | 180 | 13 | 0.61 |
| aU | pg/mL | 7.5E1 | 7.8E1 | 1.3E2 | 9.7E1 | 1.5E2 | 5.8E1 | 7.4E-2 | 3.5E1 | 1.3E3 | 2.2E2 | 466 | 13 | 180 | 13 | 0.53 |
| aV | ng/mL | 6.1E-1 | 5.9E-1 | 1.1E0 | 7.4E-1 | 2.0E0 | 6.1E-1 | 7.6E-4 | 1.2E-1 | 3.3E1 | 1.9E0 | 466 | 13 | 180 | 13 | 0.47 |
| aW | pg/mL | 1.8E1 | 2.1E1 | 1.9E1 | 3.5E1 | 1.9E1 | 5.8E1 | 7.2E-2 | 7.2E-2 | 2.4E2 | 2.3E2 | 466 | 13 | 180 | 13 | 0.59 |
| aX | ng/mL | 9.8E0 | 6.1E0 | 1.5E1 | 2.8E1 | 1.9E1 | 4.7E1 | 3.0E-1 | 2.5E0 | 2.2E2 | 1.7E2 | 466 | 13 | 180 | 13 | 0.50 |
| aY | pg/mL | 6.0E1 | 8.8E1 | 7.7E1 | 1.1E2 | 8.6E1 | 9.5E1 | 4.1E-1 | 2.5E1 | 1.2E3 | 3.9E2 | 466 | 13 | 180 | 13 | 0.65 |
| aZ | pg/mL | 2.3E2 | 1.9E2 | 4.9E2 | 4.0E2 | 9.2E2 | 5.1E2 | 1.7E0 | 3.2E1 | 1.2E4 | 1.8E3 | 466 | 13 | 180 | 13 | 0.50 |
| bA | ng/mL | 8.4E0 | 1.7E1 | 3.5E1 | 4.5E1 | 1.0E2 | 4.9E1 | 3.0E-2 | 2.9E-1 | 9.4E2 | 1.4E2 | 466 | 13 | 180 | 13 | 0.67 |
| bB | pg/mL | 3.0E2 | 4.2E2 | 3.1E2 | 3.9E2 | 1.6E2 | 2.1E2 | 2.1E0 | 6.2E1 | 8.2E2 | 6.9E2 | 466 | 13 | 180 | 13 | 0.62 |
| bC | ng/mL | 3.5E2 | 5.2E2 | 6.2E2 | 7.1E2 | 8.2E2 | 7.5E2 | 2.7E1 | 1.4E1 | 4.7E3 | 2.7E3 | 466 | 13 | 180 | 13 | 0.56 |
| bE | mg/mL | 5.6E0 | 6.1E0 | 5.8E0 | 6.5E0 | 2.1E0 | 1.6E0 | 9.8E-1 | 4.0E0 | 1.3E1 | 1.0E1 | 466 | 13 | 180 | 13 | 0.62 |
| bF | pg/mL | 2.1E1 | 1.5E1 | 1.6E2 | 4.0E2 | 9.3E2 | 1.4E3 | 5.0E-2 | 4.4E0 | 1.1E4 | 5.0E3 | 466 | 13 | 180 | 13 | 0.39 |
| bG | ng/mL | 1.6E0 | 1.1E0 | 2.7E0 | 1.5E0 | 3.2E0 | 1.4E0 | 2.2E-2 | 2.9E-1 | 2.3E1 | 4.8E0 | 466 | 13 | 180 | 13 | 0.38 |
| bH | pg/mL | 5.7E-1 | 5.7E-1 | 5.0E0 | 3.6E0 | 1.5E1 | 5.8E0 | 5.7E-1 | 5.7E-1 | 2.8E2 | 1.7E1 | 466 | 13 | 180 | 13 | 0.46 |
| bI | ng/mL | 4.0E-3 | 4.0E-3 | 6.5E-2 | 5.3E-2 | 1.6E-1 | 9.7E-2 | 4.0E-3 | 4.0E-3 | 1.3E0 | 2.9E-1 | 466 | 13 | 180 | 13 | 0.51 |
| bJ | mg/mL | 2.4E0 | 2.5E0 | 2.7E0 | 2.4E0 | 2.1E0 | 1.1E0 | 2.5E-4 | 7.0E-1 | 1.3E1 | 4.1E0 | 466 | 13 | 180 | 13 | 0.50 |
| bL | pg/mL | 3.7E0 | 6.3E0 | 8.4E0 | 1.0E1 | 1.1E1 | 1.2E1 | 4.6E-2 | 4.6E-2 | 8.0E1 | 4.0E1 | 466 | 13 | 180 | 13 | 0.54 |
| bM | mg/mL | 1.8E0 | 2.0E0 | 2.1E0 | 2.2E0 | 1.4E0 | 1.2E0 | 9.2E-3 | 1.0E0 | 8.8E0 | 5.3E0 | 466 | 13 | 180 | 13 | 0.55 |
| bN | ng/mL | 4.6E1 | 2.3E1 | 1.3E2 | 1.2E2 | 2.8E2 | 1.7E2 | 1.4E-1 | 4.9E-1 | 1.9E3 | 4.7E2 | 466 | 13 | 180 | 13 | 0.44 |
| bO | ng/mL | 4.0E-2 | 4.0E-2 | 1.1E1 | 1.5E1 | 2.5E1 | 2.1E1 | 4.0E-2 | 4.0E-2 | 2.0E2 | 5.0E1 | 466 | 13 | 180 | 13 | 0.57 |
| bP | mg/mL | 5.4E-1 | 6.6E-1 | 7.7E-1 | 8.6E-1 | 6.9E-1 | 7.5E-1 | 4.9E-2 | 9.7E-2 | 4.8E0 | 2.9E0 | 466 | 13 | 180 | 13 | 0.55 |
| bQ | pg/mL | 1.6E1 | 1.2E1 | 6.2E1 | 3.8E1 | 6.3E2 | 8.5E1 | 1.5E-1 | 4.4E0 | 1.3E4 | 3.2E2 | 466 | 13 | 180 | 13 | 0.41 |
| bR | ng/mL | 1.2E-2 | 1.0E-1 | 1.3E-1 | 1.4E-1 | 4.5E-1 | 1.5E-1 | 1.2E-2 | 1.2E-2 | 8.7E0 | 4.9E-1 | 466 | 13 | 180 | 13 | 0.58 |
| bS | pg/mL | 9.4E-1 | 9.4E-1 | 7.1E0 | 4.6E0 | 2.8E1 | 1.3E1 | 9.4E-1 | 9.4E-1 | 3.9E2 | 4.8E1 | 466 | 13 | 180 | 13 | 0.47 |
| bU | ng/mL | 1.2E-1 | 7.0E-2 | 2.0E-1 | 1.3E-1 | 3.7E-1 | 1.5E-1 | 1.3E-2 | 1.3E-2 | 6.6E0 | 5.0E-1 | 466 | 13 | 180 | 13 | 0.44 |
| bV | pg/mL | 4.6E2 | 5.0E2 | 5.5E2 | 6.6E2 | 5.8E2 | 3.3E2 | 1.5E2 | 3.1E2 | 1.2E4 | 1.2E3 | 466 | 13 | 180 | 13 | 0.61 |
| bW | pg/mL | 3.4E2 | 4.1E2 | 6.4E2 | 5.6E2 | 1.7E3 | 5.1E2 | 8.4E1 | 1.8E2 | 2.5E4 | 2.2E3 | 466 | 13 | 180 | 13 | 0.58 |
| bX | ng/mL | 6.9E-4 | 2.5E-5 | 2.7E-3 | 1.8E-3 | 3.4E-3 | 2.3E-3 | 2.5E-5 | 2.5E-5 | 2.0E-2 | 6.9E-3 | 466 | 13 | 180 | 13 | 0.44 |
| bZ | pg/mL | 2.3E2 | 2.7E2 | 8.5E2 | 1.3E3 | 4.0E3 | 3.1E3 | 1.5E-1 | 1.1E2 | 5.8E4 | 1.2E4 | 466 | 13 | 180 | 13 | 0.54 |
| cA | pg/mL | 6.0E-1 | 6.0E-1 | 2.8E0 | 3.1E0 | 1.8E1 | 6.9E0 | 6.0E-1 | 6.0E-1 | 3.7E2 | 2.5E1 | 466 | 13 | 180 | 13 | 0.51 |
| cB | ng/mL | 5.7E-2 | 4.6E-2 | 9.0E-2 | 6.7E-2 | 1.0E-1 | 8.8E-2 | 1.7E-3 | 1.7E-3 | 5.7E-1 | 2.7E-1 | 466 | 13 | 180 | 13 | 0.40 |
| cC | pg/mL | 4.6E1 | 3.4E1 | 4.8E1 | 3.6E1 | 4.0E1 | 2.0E1 | 1.0E0 | 1.0E0 | 4.5E2 | 6.9E1 | 466 | 13 | 180 | 13 | 0.40 |
| cD | pg/mL | 5.6E0 | 4.2E0 | 1.3E1 | 3.6E1 | 4.9E1 | 8.4E1 | 3.3E-1 | 3.3E-1 | 7.2E2 | 3.1E2 | 466 | 13 | 180 | 13 | 0.50 |
| cE | pg/mL | 3.7E1 | 3.3E1 | 1.7E2 | 2.0E2 | 4.8E2 | 4.6E2 | 1.2E-1 | 2.6E0 | 3.8E3 | 1.7E3 | 466 | 13 | 180 | 13 | 0.48 |
| cF | pg/mL | 1.3E1 | 1.3E1 | 2.0E1 | 1.3E1 | 3.0E1 | 1.3E1 | 5.3E-1 | 5.3E-1 | 2.7E2 | 4.1E1 | 466 | 13 | 180 | 13 | 0.46 |
| cG | pg/mL | 4.5E1 | 3.7E1 | 1.1E2 | 7.6E1 | 5.1E2 | 9.0E1 | 6.4E0 | 1.7E1 | 1.0E4 | 2.8E2 | 466 | 13 | 180 | 13 | 0.44 |
| cH | uIU/mL | 2.8E0 | 3.3E0 | 5.8E0 | 6.8E0 | 1.1E1 | 1.1E1 | 8.6E-3 | 4.8E-1 | 1.6E2 | 4.2E1 | 466 | 13 | 180 | 13 | 0.51 |
| cI | ng/mL | 5.5E0 | 1.3E1 | 1.1E1 | 3.0E1 | 1.5E1 | 5.2E1 | 1.0E-3 | 3.5E-1 | 1.2E2 | 1.9E2 | 466 | 13 | 180 | 13 | 0.60 |
| cJ | ug/mL | 5.6E1 | 8.2E1 | 1.1E2 | 1.4E2 | 1.4E2 | 1.7E2 | 4.0E0 | 8.6E0 | 9.6E2 | 6.6E2 | 466 | 13 | 180 | 13 | 0.58 |
| cK | ng/mL | 3.8E-3 | 3.8E-3 | 5.1E-2 | 1.3E-2 | 1.8E-1 | 3.2E-2 | 3.8E-3 | 3.8E-3 | 1.7E0 | 1.2E-1 | 466 | 13 | 180 | 13 | 0.46 |
| cL | pg/mL | 2.0E2 | 1.7E2 | 3.7E2 | 4.9E2 | 1.3E3 | 7.7E2 | 1.6E1 | 1.2E2 | 2.4E4 | 2.9E3 | 466 | 13 | 180 | 13 | 0.53 |
| cM | pg/mL | 2.6E2 | 2.6E2 | 2.9E2 | 3.0E2 | 2.0E2 | 1.6E2 | 8.7E0 | 1.2E2 | 1.6E3 | 6.1E2 | 466 | 13 | 180 | 13 | 0.52 |
| cN | pg/mL | 1.2E2 | 1.6E2 | 1.3E2 | 1.6E2 | 6.5E1 | 5.3E1 | 3.8E1 | 9.5E1 | 1.1E3 | 2.7E2 | 466 | 13 | 180 | 13 | 0.75 |
| cO | pg/mL | 2.3E2 | 2.1E2 | 3.2E2 | 2.8E2 | 9.0E2 | 1.7E2 | 5.4E1 | 9.0E1 | 1.9E4 | 7.2E2 | 466 | 13 | 180 | 13 | 0.49 |
| cP | ng/mL | 2.5E3 | 3.1E3 | 2.6E3 | 3.1E3 | 9.1E2 | 1.1E3 | 6.2E2 | 1.7E3 | 5.7E3 | 5.0E3 | 466 | 13 | 180 | 13 | 0.63 |
| cQ | ng/mL | 5.3E-2 | 6.2E-2 | 1.5E-1 | 1.6E-1 | 3.0E-1 | 2.6E-1 | 2.0E-3 | 2.0E-3 | 2.2E0 | 8.5E-1 | 466 | 13 | 180 | 13 | 0.54 |
| cR | ng/mL | 3.0E2 | 3.2E2 | 5.2E2 | 3.8E2 | 8.2E2 | 2.9E2 | 2.0E1 | 9.4E1 | 8.9E3 | 1.0E3 | 466 | 13 | 180 | 13 | 0.49 |
| cS | ng/mL | 2.5E2 | 3.6E2 | 4.0E2 | 4.7E2 | 4.0E2 | 3.0E2 | 4.1E1 | 1.1E2 | 2.7E3 | 1.1E3 | 466 | 13 | 180 | 13 | 0.63 |
| cT | ng/mL | 3.3E1 | 7.0E1 | 8.4E1 | 9.5E1 | 1.9E2 | 9.3E1 | 3.7E0 | 7.6E0 | 2.1E3 | 3.1E2 | 466 | 13 | 180 | 13 | 0.62 |
| cU | ng/mL | 5.3E1 | 7.0E1 | 7.6E1 | 7.7E1 | 1.0E2 | 3.6E1 | 5.4E0 | 3.1E1 | 1.6E3 | 1.5E2 | 466 | 13 | 180 | 13 | 0.62 |
| cV | ng/mL | 1.8E-1 | 1.4E-1 | 4.0E-1 | 2.2E-1 | 2.2E0 | 2.0E-1 | 2.5E-2 | 8.8E-2 | 4.7E1 | 7.5E-1 | 466 | 13 | 180 | 13 | 0.45 |
| cW | mIU/mL | 5.3E-2 | 8.2E-2 | 1.5E-1 | 7.4E-1 | 7.0E-1 | 4.6E0 | 3.7E-4 | 1.0E-2 | 9.7E0 | 1.7E1 | 466 | 13 | 180 | 13 | 0.56 |
| cX | ng/mL | 1.1E-1 | 4.3E-2 | 1.2E0 | 4.1E-1 | 3.8E0 | 7.1E-1 | 1.5E-4 | 1.6E-4 | 2.8E1 | 2.4E0 | 466 | 13 | 180 | 13 | 0.46 |
| cY | ng/mL | 8.6E0 | 7.4E0 | 1.3E1 | 1.0E1 | 1.3E1 | 7.2E0 | 1.5E-1 | 1.6E0 | 8.3E1 | 2.3E1 | 466 | 13 | 180 | 13 | 0.49 |

Figure 22 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cZ | ug/mL | 1.5E1 | 1.9E1 | 1.6E1 | 2.0E1 | 7.4E0 | 6.1E0 | 2.3E0 | 1.3E1 | 5.7E1 | 3.1E1 | 466 | 13 | 180 | 13 | 0.69 |
| dA | pg/mL | 3.2E2 | 4.3E2 | 3.7E2 | 4.3E2 | 3.1E2 | 1.8E2 | 9.0E1 | 1.9E2 | 5.8E3 | 9.0E2 | 466 | 13 | 180 | 13 | 0.64 |
| dB | ug/mL | 1.7E1 | 2.2E1 | 1.8E1 | 1.7E1 | 1.6E1 | 1.0E1 | 9.4E-1 | 2.8E0 | 2.5E2 | 3.0E1 | 466 | 13 | 180 | 13 | 0.58 |
| dC | nmol/L | 3.5E1 | 3.2E1 | 3.8E1 | 3.8E1 | 1.8E1 | 2.1E1 | 7.6E0 | 1.7E1 | 1.4E2 | 7.9E1 | 466 | 13 | 180 | 13 | 0.46 |
| dD | ug/mL | 3.6E1 | 3.3E1 | 3.7E1 | 3.6E1 | 1.1E1 | 7.6E0 | 1.3E1 | 2.7E1 | 7.6E1 | 5.1E1 | 466 | 13 | 180 | 13 | 0.46 |
| dE | ng/mL | 4.8E-1 | 4.8E-1 | 6.1E-1 | 5.6E-1 | 7.0E-1 | 6.0E-1 | 8.4E-3 | 8.4E-3 | 7.2E0 | 2.0E0 | 466 | 13 | 180 | 13 | 0.48 |
| dF | ng/mL | 2.3E2 | 2.4E2 | 2.8E2 | 3.1E2 | 1.9E2 | 2.6E2 | 5.6E1 | 1.2E2 | 1.3E3 | 1.1E3 | 466 | 13 | 180 | 13 | 0.51 |
| dG | ng/mL | 1.1E1 | 1.7E1 | 1.5E1 | 1.9E1 | 1.4E1 | 1.2E1 | 2.2E0 | 7.0E0 | 1.8E2 | 5.2E1 | 466 | 13 | 180 | 13 | 0.67 |
| dH | ng/mL | 7.5E0 | 1.2E1 | 1.3E1 | 1.9E1 | 3.9E1 | 2.6E1 | 4.0E-2 | 2.2E0 | 6.7E2 | 9.7E1 | 466 | 13 | 180 | 13 | 0.60 |
| dI | pg/mL | 4.6E-1 | 4.6E-1 | 2.3E0 | 1.6E0 | 1.6E1 | 2.5E0 | 4.6E-1 | 4.6E-1 | 3.3E2 | 9.5E0 | 466 | 13 | 180 | 13 | 0.54 |
| dJ | ng/mL | 1.9E0 | 2.4E0 | 2.2E0 | 2.5E0 | 1.1E0 | 1.3E0 | 3.2E-1 | 9.4E-1 | 6.9E0 | 5.2E0 | 466 | 13 | 180 | 13 | 0.58 |
| dK | uIU/mL | 1.9E0 | 1.7E0 | 3.1E0 | 2.4E0 | 6.5E0 | 2.5E0 | 2.8E-4 | 4.2E-2 | 7.9E1 | 1.0E1 | 466 | 13 | 180 | 13 | 0.50 |
| dL | ng/mL | 8.8E2 | 1.2E3 | 1.0E3 | 1.1E3 | 5.9E2 | 3.2E2 | 2.6E2 | 5.7E2 | 4.8E3 | 1.6E3 | 466 | 13 | 180 | 13 | 0.62 |
| dM | pg/mL | 9.5E2 | 1.2E3 | 1.2E3 | 1.8E3 | 1.4E3 | 1.4E3 | 3.4E2 | 7.2E2 | 1.6E4 | 5.9E3 | 466 | 13 | 180 | 13 | 0.66 |
| dN | ug/mL | 9.4E1 | 1.0E2 | 1.0E2 | 1.2E2 | 4.1E1 | 5.3E1 | 1.6E1 | 5.8E1 | 3.3E2 | 2.2E2 | 466 | 13 | 180 | 13 | 0.63 |
| dR | pg/ml | 1.6E3 | 2.0E3 | 2.4E3 | 2.6E3 | 2.4E3 | 2.2E3 | 1.4E2 | 5.5E2 | 1.5E4 | 8.7E3 | 312 | 12 | 171 | 12 | 0.57 |
| eF | ng/ml | 4.1E0 | 4.3E0 | 5.0E0 | 5.1E0 | 4.2E0 | 2.2E0 | 1.2E0 | 2.1E0 | 4.6E1 | 8.6E0 | 324 | 12 | 172 | 12 | 0.56 |
| eC | pg/ml | 3.0E2 | 2.7E2 | 3.8E2 | 3.2E2 | 2.9E2 | 1.5E2 | 9.9E0 | 1.3E2 | 2.0E3 | 6.2E2 | 246 | 11 | 160 | 11 | 0.46 |
| eD | pg/ml | 2.1E2 | 2.6E2 | 5.0E2 | 3.0E2 | 1.1E3 | 2.8E2 | 5.2E-1 | 4.5E1 | 8.3E3 | 9.9E2 | 196 | 9 | 131 | 9 | 0.53 |
| fP | ng/ml | 2.6E2 | 3.3E2 | 2.9E2 | 3.3E2 | 1.7E2 | 2.4E2 | 8.4E0 | 8.1E1 | 1.0E3 | 9.5E2 | 298 | 13 | 163 | 13 | 0.54 |
| gL | pg/ml | 6.4E4 | 6.6E4 | 7.0E4 | 7.7E4 | 2.9E4 | 3.5E4 | 1.4E4 | 4.4E4 | 2.0E5 | 1.5E5 | 312 | 12 | 171 | 12 | 0.54 |
| gP | U/ml | 2.7E2 | 2.5E2 | 2.7E2 | 2.7E2 | 9.4E1 | 7.9E1 | 1.2E1 | 1.5E2 | 8.0E2 | 4.4E2 | 320 | 12 | 172 | 12 | 0.49 |
| gW | ng/ml | 6.1E2 | 9.8E2 | 1.3E3 | 1.3E3 | 1.7E3 | 1.5E3 | 3.1E-1 | 3.3E1 | 9.5E3 | 5.4E3 | 273 | 11 | 163 | 11 | 0.56 |
| tF | pg/mL | 1.5E3 | 1.0E3 | 1.2E4 | 1.6E3 | 3.8E4 | 2.0E3 | 1.2E1 | 1.8E1 | 3.2E5 | 5.8E3 | 246 | 11 | 160 | 11 | 0.41 |
| hA | ng/ml | 2.1E0 | 2.5E0 | 9.9E0 | 1.0E1 | 3.7E1 | 2.0E1 | 1.7E-2 | 1.7E-2 | 3.5E2 | 6.1E1 | 197 | 9 | 131 | 9 | 0.54 |
| nM | pg/ml | 1.0E-9 | 1.0E-9 | 7.7E1 | 1.0E-9 | 8.9E2 | 0.0E0 | 1.0E-9 | 1.0E-9 | 1.0E4 | 1.0E-9 | 133 | 8 | 101 | 8 | 0.49 |
| nN | pg/ml | 1.2E3 | 3.3E3 | 4.2E3 | 2.9E3 | 2.3E4 | 2.4E3 | 1.1E2 | 1.1E2 | 2.7E5 | 7.1E3 | 133 | 8 | 101 | 8 | 0.60 |
| nO | pg/ml | 2.6E1 | 2.8E1 | 4.5E1 | 4.8E1 | 5.3E1 | 4.8E1 | 3.5E0 | 9.6E0 | 3.1E2 | 1.4E2 | 133 | 8 | 101 | 8 | 0.50 |
| nR | pg/ml | 1.5E1 | 9.6E0 | 3.2E1 | 9.0E1 | 4.5E1 | 1.5E2 | 1.0E-9 | 8.6E-1 | 2.6E2 | 3.6E2 | 133 | 8 | 101 | 8 | 0.46 |
| nT | pg/ml | 8.0E1 | 7.0E1 | 2.0E2 | 1.2E2 | 7.9E2 | 1.5E2 | 1.0E-9 | 2.3E1 | 6.6E3 | 4.9E2 | 133 | 8 | 101 | 8 | 0.48 |
| nU | pg/ml | 2.9E1 | 1.2E2 | 2.5E2 | 2.0E2 | 1.4E3 | 2.4E2 | 1.0E-9 | 1.0E-9 | 1.3E4 | 7.5E2 | 133 | 8 | 101 | 8 | 0.71 |
| lW | pg/ml | 1.0E-9 | 1.0E-9 | 1.4E1 | 4.0E0 | 4.9E1 | 8.3E0 | 1.0E-9 | 1.0E-9 | 3.9E2 | 2.3E1 | 133 | 8 | 101 | 8 | 0.48 |
| lX | pg/ml | 9.5E2 | 8.9E2 | 1.0E3 | 9.6E2 | 5.8E2 | 3.7E2 | 1.2E2 | 5.1E2 | 2.6E3 | 1.5E3 | 133 | 8 | 101 | 8 | 0.49 |
| lY | pg/ml | 1.9E1 | 1.6E1 | 2.2E1 | 1.9E1 | 1.9E1 | 1.2E1 | 1.0E-9 | 4.8E0 | 1.4E2 | 3.9E1 | 133 | 8 | 101 | 8 | 0.44 |
| mE | pg/ml | 1.0E-9 | 1.0E-9 | 2.9E0 | 1.8E0 | 8.5E0 | 3.0E0 | 1.0E-9 | 1.0E-9 | 5.8E1 | 7.9E0 | 133 | 8 | 101 | 8 | 0.50 |
| mF | pg/ml | 1.0E-9 | 4.3E-1 | 2.4E0 | 1.2E0 | 9.4E0 | 1.8E0 | 1.0E-9 | 1.0E-9 | 1.1E2 | 5.4E0 | 133 | 8 | 101 | 8 | 0.51 |
| mH | pg/ml | 3.6E0 | 2.5E0 | 5.3E0 | 2.4E0 | 6.6E0 | 6.9E-1 | 2.3E-1 | 1.4E0 | 5.3E1 | 3.5E0 | 133 | 8 | 101 | 8 | 0.36 |
| mI | pg/ml | 1.0E-9 | 1.0E-9 | 1.5E1 | 1.3E1 | 3.1E1 | 2.7E1 | 1.0E-9 | 1.0E-9 | 1.8E2 | 7.6E1 | 133 | 8 | 101 | 8 | 0.46 |
| mM | pg/ml | 2.2E1 | 2.5E1 | 6.9E1 | 6.3E1 | 1.3E2 | 8.9E1 | 1.0E-9 | 1.0E-9 | 9.8E2 | 2.3E2 | 133 | 8 | 101 | 8 | 0.51 |
| mP | pg/ml | 1.4E1 | 2.3E1 | 1.8E1 | 2.7E1 | 2.2E1 | 1.7E1 | 1.0E-9 | 1.3E1 | 1.9E2 | 6.4E1 | 132 | 8 | 100 | 8 | 0.76 |
| mS | pg/ml | 1.6E3 | 1.9E3 | 1.8E3 | 1.9E3 | 1.6E3 | 8.8E2 | 1.0E-9 | 7.3E2 | 1.3E4 | 3.0E3 | 133 | 8 | 101 | 8 | 0.58 |
| mT | pg/ml | 5.4E1 | 3.9E1 | 1.3E2 | 1.3E2 | 2.2E2 | 2.7E2 | 9.7E0 | 1.8E1 | 1.4E3 | 8.0E2 | 132 | 8 | 100 | 8 | 0.42 |
| mU | pg/ml | 2.2E0 | 2.6E0 | 4.0E0 | 4.9E0 | 8.3E0 | 6.0E0 | 1.0E-9 | 1.3E0 | 6.8E1 | 1.9E1 | 132 | 8 | 100 | 8 | 0.58 |
| mW | pg/ml | 2.3E3 | 3.1E3 | 2.7E3 | 3.1E3 | 2.1E3 | 1.4E3 | 1.0E-9 | 1.4E3 | 1.8E4 | 5.4E3 | 132 | 8 | 100 | 8 | 0.63 |
| mY | pg/ml | 5.5E2 | 5.4E2 | 8.5E2 | 9.3E2 | 1.3E3 | 8.8E2 | 1.0E-9 | 1.5E2 | 1.1E4 | 2.6E3 | 133 | 8 | 101 | 8 | 0.54 |
| mZ | pg/ml | 1.7E2 | 4.9E2 | 2.9E2 | 6.2E2 | 3.0E2 | 4.7E2 | 1.0E-9 | 1.2E2 | 1.5E3 | 1.4E3 | 132 | 8 | 100 | 8 | 0.76 |
| nA | pg/ml | 1.6E0 | 3.9E0 | 1.0E1 | 1.0E1 | 4.3E1 | 1.9E1 | 1.0E-9 | 1.0E-9 | 4.4E2 | 5.7E1 | 132 | 8 | 100 | 8 | 0.58 |
| nB | pg/ml | 3.1E2 | 3.8E2 | 3.2E2 | 4.3E2 | 1.7E2 | 2.5E2 | 3.0E1 | 2.1E2 | 9.1E2 | 1.0E3 | 133 | 8 | 101 | 8 | 0.65 |
| nC | pg/ml | 1.0E-9 | 1.0E-9 | 2.5E4 | 2.5E3 | 1.5E5 | 7.1E3 | 1.0E-9 | 1.0E-9 | 1.5E6 | 2.0E4 | 133 | 8 | 101 | 8 | 0.36 |
| nD | pg/ml | 7.9E0 | 1.2E1 | 3.6E1 | 2.4E1 | 2.0E2 | 3.8E1 | 1.0E-9 | 3.1E0 | 1.7E3 | 1.2E2 | 132 | 8 | 100 | 8 | 0.65 |
| nF | pg/ml | 1.0E-9 | 8.3E0 | 4.5E0 | 1.5E1 | 2.5E1 | 1.9E1 | 1.0E-9 | 1.0E-9 | 2.4E2 | 4.7E1 | 133 | 8 | 101 | 8 | 0.75 |
| nH | pg/ml | 1.0E0 | 1.0E-9 | 2.2E2 | 4.1E1 | 1.3E3 | 1.2E2 | 1.0E-9 | 1.0E-9 | 1.0E4 | 3.3E2 | 132 | 8 | 100 | 8 | 0.36 |
| nI | pg/ml | 3.0E1 | 6.4E1 | 1.5E2 | 1.9E2 | 8.3E2 | 4.1E2 | 1.0E-9 | 1.0E-9 | 9.2E3 | 1.2E3 | 133 | 8 | 101 | 8 | 0.58 |
| nJ | pg/ml | 5.9E-2 | 1.6E0 | 4.1E1 | 2.9E0 | 4.5E2 | 5.0E0 | 1.0E-9 | 1.0E-9 | 5.2E3 | 1.5E1 | 133 | 8 | 101 | 8 | 0.70 |
| nK | pg/ml | 1.0E-9 | 1.0E-9 | 5.6E1 | 3.8E1 | 3.4E2 | 7.7E1 | 1.0E-9 | 1.0E-9 | 3.2E3 | 2.2E2 | 132 | 8 | 100 | 8 | 0.51 |
| nL | pg/ml | 1.0E-9 | 1.0E-9 | 5.9E2 | 1.1E2 | 4.1E3 | 3.2E2 | 1.0E-9 | 1.0E-9 | 4.5E4 | 9.0E2 | 133 | 8 | 101 | 8 | 0.38 |
| hR | pg/ml | 2.6E4 | 2.3E4 | 2.7E4 | 2.4E4 | 1.1E4 | 7.3E3 | 1.0E-9 | 1.4E4 | 5.8E4 | 3.7E4 | 187 | 9 | 127 | 9 | 0.41 |

Figure 22 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| hV | pg/ml | 4.4E2 | 5.1E2 | 4.6E2 | 4.5E2 | 2.4E2 | 2.4E2 | 1.0E-9 | 1.3E2 | 1.5E3 | 7.9E2 | 187 | 9 | 127 | 9 | 0.49 |
| hW | pg/ml | 1.6E3 | 1.7E3 | 2.1E3 | 1.8E3 | 3.0E3 | 7.6E2 | 1.0E-9 | 7.1E2 | 4.0E4 | 3.3E3 | 187 | 9 | 127 | 9 | 0.51 |
| hX | pg/ml | 9.0E2 | 1.1E3 | 1.0E3 | 1.1E3 | 7.3E2 | 3.2E2 | 2.5E0 | 6.0E2 | 8.6E3 | 1.5E3 | 187 | 9 | 127 | 9 | 0.58 |
| iA | pg/ml | 1.5E2 | 1.5E2 | 3.0E2 | 2.1E2 | 6.1E2 | 1.8E2 | 8.2E0 | 4.2E1 | 7.1E3 | 6.8E2 | 246 | 11 | 160 | 11 | 0.52 |
| iB | ng/ml | 4.8E0 | 7.2E0 | 6.1E0 | 7.5E0 | 5.0E0 | 5.6E0 | 3.3E-2 | 1.9E0 | 2.6E1 | 1.9E1 | 197 | 9 | 131 | 9 | 0.58 |
| iC | U/ml | 2.3E-1 | 3.5E-1 | 1.1E0 | 3.6E-1 | 4.8E0 | 3.1E-1 | 1.0E-9 | 1.0E-9 | 5.5E1 | 7.7E-1 | 197 | 9 | 131 | 9 | 0.51 |
| iH | ng/ml | 1.6E5 | 1.6E5 | 1.6E5 | 1.5E5 | 4.8E4 | 5.9E4 | 2.9E3 | 5.1E4 | 2.7E5 | 2.1E5 | 246 | 11 | 160 | 11 | 0.46 |
| iJ | ng/ml | 4.9E4 | 5.7E4 | 5.2E4 | 6.7E4 | 2.6E4 | 4.4E4 | 1.8E3 | 1.1E4 | 2.5E5 | 1.8E5 | 246 | 11 | 160 | 11 | 0.60 |
| hB | ng/ml | 4.5E-1 | 3.2E-1 | 5.6E-1 | 6.0E-1 | 4.5E-1 | 6.1E-1 | 1.0E-9 | 2.0E-1 | 3.2E0 | 1.9E0 | 246 | 11 | 160 | 11 | 0.42 |
| hC | pg/ml | 3.8E3 | 3.4E3 | 6.8E3 | 6.7E3 | 8.7E3 | 7.3E3 | 1.0E-9 | 6.2E1 | 5.7E4 | 2.0E4 | 246 | 11 | 160 | 11 | 0.51 |
| hF | ng/ml | 1.0E-9 | 1.0E-9 | 2.0E1 | 1.0E-9 | 2.6E2 | 0.0E0 | 1.0E-9 | 1.0E-9 | 4.0E3 | 1.0E-9 | 246 | 11 | 160 | 11 | 0.49 |
| hG | pg/ml | 6.8E3 | 8.7E3 | 7.2E3 | 9.9E3 | 3.0E3 | 4.1E3 | 2.8E1 | 4.8E3 | 2.0E4 | 1.8E4 | 246 | 11 | 160 | 11 | 0.69 |
| iO | ng/ml | 3.7E5 | 4.0E5 | 3.9E5 | 3.9E5 | 1.8E5 | 1.5E5 | 1.1E4 | 1.3E5 | 1.1E6 | 6.2E5 | 246 | 11 | 160 | 11 | 0.52 |
| iP | ng/ml | 4.8E4 | 5.5E4 | 5.6E4 | 5.0E4 | 5.6E4 | 2.1E4 | 1.0E-9 | 1.9E4 | 5.7E5 | 7.7E4 | 246 | 11 | 160 | 11 | 0.49 |
| iZ | ng/ml | 1.6E3 | 2.1E3 | 1.8E3 | 2.3E3 | 7.4E2 | 7.6E2 | 4.7E2 | 1.5E3 | 5.1E3 | 4.2E3 | 247 | 11 | 160 | 11 | 0.71 |
| rC | | 1.7E3 | 2.3E3 | 2.1E3 | 3.3E3 | 1.8E3 | 2.8E3 | 1.0E-9 | 2.5E2 | 1.5E4 | 8.4E3 | 187 | 10 | 127 | 10 | 0.61 |
| rB | pg/ml | 2.6E1 | 1.8E1 | 4.6E1 | 3.0E1 | 8.9E1 | 3.1E1 | 1.0E-9 | 1.0E-9 | 9.5E2 | 7.9E1 | 187 | 10 | 127 | 10 | 0.43 |
| jD | ng/ml | 3.2E1 | 1.8E1 | 4.9E1 | 2.2E1 | 6.3E1 | 2.6E1 | 1.0E-9 | 1.0E-9 | 5.1E2 | 8.4E1 | 196 | 9 | 131 | 9 | 0.35 |
| jE | ng/ml | 1.0E-9 | 1.0E-9 | 6.9E0 | 6.0E0 | 1.6E1 | 1.3E1 | 1.0E-9 | 1.0E-9 | 1.2E2 | 3.6E1 | 196 | 9 | 131 | 9 | 0.50 |
| jF | ng/ml | 3.9E1 | 1.6E1 | 5.2E1 | 5.1E1 | 5.8E1 | 6.4E1 | 1.0E-9 | 1.0E-9 | 3.5E2 | 1.5E2 | 196 | 9 | 131 | 9 | 0.46 |
| jG | ng/ml | 4.2E3 | 5.8E3 | 4.3E3 | 5.8E3 | 1.9E3 | 1.9E3 | 6.0E2 | 2.8E3 | 9.6E3 | 8.6E3 | 197 | 9 | 131 | 9 | 0.72 |
| jH | ng/ml | 7.4E1 | 6.7E1 | 8.4E1 | 7.5E1 | 5.1E1 | 3.0E1 | 1.3E1 | 4.3E1 | 4.3E2 | 1.3E2 | 197 | 9 | 131 | 9 | 0.46 |
| jI | ng/ml | 6.8E1 | 7.4E1 | 7.6E1 | 7.4E1 | 4.1E1 | 2.5E1 | 1.9E1 | 2.8E1 | 4.4E2 | 1.2E2 | 197 | 9 | 131 | 9 | 0.54 |
| rA | | 2.6E1 | 2.4E1 | 3.1E1 | 3.3E1 | 2.4E1 | 2.7E1 | 1.0E-9 | 2.6E0 | 2.0E2 | 9.3E1 | 197 | 10 | 131 | 10 | 0.50 |
| qY | pg/ml | 2.6E1 | 2.8E1 | 5.0E1 | 4.3E1 | 6.4E1 | 5.0E1 | 8.7E-1 | 3.4E0 | 5.3E2 | 1.8E2 | 197 | 10 | 131 | 10 | 0.52 |
| qX | pg/ml | 6.0E1 | 8.1E1 | 6.7E1 | 8.9E1 | 4.7E1 | 5.6E1 | 1.0E-9 | 1.3E1 | 2.5E2 | 1.8E2 | 197 | 10 | 131 | 10 | 0.62 |
| qW | pg/ml | 8.8E0 | 1.0E1 | 1.3E1 | 1.1E1 | 1.5E1 | 6.6E0 | 1.0E-9 | 1.0E-9 | 1.2E2 | 2.2E1 | 197 | 10 | 131 | 10 | 0.52 |
| qV | pg/ml | 2.2E3 | 3.7E3 | 2.8E3 | 3.6E3 | 2.1E3 | 1.9E3 | 1.7E2 | 1.4E3 | 9.6E3 | 7.1E3 | 197 | 10 | 131 | 10 | 0.64 |
| qU | pg/ml | 6.4E1 | 7.6E1 | 1.8E2 | 7.7E1 | 2.8E2 | 4.3E1 | 1.0E-9 | 2.2E1 | 2.1E3 | 1.7E2 | 197 | 10 | 131 | 10 | 0.49 |
| qT | pg/ml | 4.1E1 | 4.5E1 | 7.6E1 | 5.7E1 | 1.1E2 | 3.3E1 | 1.0E-9 | 2.3E1 | 9.0E2 | 1.3E2 | 197 | 10 | 131 | 10 | 0.55 |
| jK | ng/ml | 1.6E3 | 2.1E3 | 1.7E3 | 1.9E3 | 6.6E2 | 4.4E2 | 2.8E2 | 9.6E2 | 4.3E3 | 2.3E3 | 197 | 9 | 131 | 9 | 0.65 |
| jL | ng/ml | 2.0E2 | 2.1E2 | 3.0E2 | 2.7E2 | 3.0E2 | 1.8E2 | 3.5E1 | 9.6E1 | 2.1E3 | 5.7E2 | 197 | 9 | 131 | 9 | 0.51 |
| jM | ng/ml | 7.0E4 | 9.2E4 | 7.5E4 | 9.5E4 | 3.9E4 | 4.9E4 | 3.9E4 | 1.1E4 | 1.9E5 | 1.6E5 | 197 | 9 | 131 | 9 | 0.64 |
| jO | pg/ml | 2.1E5 | 2.0E5 | 2.6E5 | 2.9E5 | 1.5E5 | 2.3E5 | 5.2E4 | 1.3E5 | 1.1E6 | 8.0E5 | 197 | 9 | 131 | 9 | 0.50 |
| jP | pg/ml | 2.3E5 | 1.8E5 | 2.7E5 | 2.1E5 | 1.9E5 | 6.8E4 | 3.6E4 | 1.3E5 | 1.9E6 | 3.0E5 | 197 | 9 | 131 | 9 | 0.43 |
| jQ | pg/ml | 2.5E3 | 2.7E3 | 3.5E3 | 3.9E3 | 3.3E3 | 3.3E3 | 1.0E-9 | 6.4E2 | 1.8E4 | 1.0E4 | 197 | 9 | 131 | 9 | 0.56 |
| jR | pg/ml | 5.9E3 | 9.4E3 | 1.1E4 | 1.1E4 | 1.3E4 | 8.0E3 | 1.0E-9 | 2.0E3 | 9.0E4 | 2.2E4 | 197 | 9 | 131 | 9 | 0.56 |
| jT | pg/ml | 1.7E5 | 2.0E5 | 1.7E5 | 2.0E5 | 6.2E4 | 6.4E4 | 6.8E4 | 1.0E5 | 3.9E5 | 3.1E5 | 197 | 9 | 131 | 9 | 0.65 |
| jU | mIU/ml | 4.3E0 | 4.0E0 | 1.0E1 | 6.9E0 | 1.7E1 | 7.0E0 | 4.2E-2 | 3.0E-1 | 1.1E2 | 1.8E1 | 197 | 9 | 131 | 9 | 0.49 |
| jV | mIU/ml | 1.3E0 | 3.1E0 | 3.3E0 | 3.3E0 | 5.7E0 | 3.2E0 | 1.7E-3 | 1.1E-3 | 3.3E1 | 9.1E0 | 197 | 9 | 131 | 9 | 0.59 |
| jY | ng/ml | 7.3E-4 | 2.6E-3 | 6.3E-3 | 6.2E-3 | 2.8E-2 | 8.6E-3 | 1.0E-9 | 1.0E-9 | 3.0E-1 | 2.6E-2 | 197 | 9 | 131 | 9 | 0.63 |
| kC | pg/ml | 9.7E1 | 1.1E2 | 1.9E2 | 1.2E2 | 4.3E2 | 7.5E1 | 2.1E1 | 5.4E1 | 3.5E3 | 2.9E2 | 133 | 8 | 101 | 8 | 0.52 |
| kE | pg/ml | 1.3E5 | 1.3E5 | 1.3E5 | 1.3E5 | 4.0E4 | 2.7E4 | 1.2E4 | 1.0E5 | 2.3E5 | 1.8E5 | 133 | 8 | 101 | 8 | 0.52 |
| kF | pg/mL | 6.1E1 | 5.5E1 | 6.9E1 | 6.9E1 | 4.9E1 | 3.3E1 | 2.6E1 | 3.8E1 | 5.1E2 | 1.4E2 | 133 | 8 | 101 | 8 | 0.49 |
| kG | pg/mL | 9.1E3 | 8.2E3 | 1.2E4 | 1.6E4 | 1.3E4 | 2.3E4 | 7.5E2 | 4.2E3 | 1.2E5 | 7.1E4 | 133 | 8 | 101 | 8 | 0.50 |
| kI | | 1.9E2 | 1.7E2 | 2.2E2 | 1.8E2 | 1.4E2 | 7.9E1 | 4.4E1 | 8.8E1 | 8.7E2 | 3.4E2 | 133 | 8 | 101 | 8 | 0.42 |
| kK | pg/ml | 1.0E2 | 1.8E2 | 1.5E2 | 3.6E2 | 1.6E2 | 4.0E2 | 6.4E0 | 5.1E1 | 1.2E3 | 1.2E3 | 133 | 8 | 101 | 8 | 0.65 |
| kN | pg/ml | 9.9E2 | 8.6E2 | 1.5E3 | 8.6E2 | 2.2E3 | 5.1E2 | 7.6E1 | 2.4E2 | 1.7E4 | 1.9E3 | 133 | 8 | 101 | 8 | 0.38 |
| kO | pg/ml | 7.1E3 | 5.7E3 | 9.6E3 | 7.3E3 | 1.7E4 | 3.1E3 | 3.4E3 | 5.3E3 | 1.5E5 | 1.4E4 | 133 | 8 | 101 | 8 | 0.42 |
| kP | pg/ml | 5.8E3 | 4.2E3 | 7.2E3 | 5.5E3 | 6.2E3 | 2.6E3 | 8.6E2 | 3.0E3 | 4.8E4 | 9.4E3 | 133 | 8 | 101 | 8 | 0.43 |
| kQ | pg/ml | 4.1E3 | 4.7E3 | 5.2E3 | 4.9E3 | 3.8E3 | 2.0E3 | 5.6E2 | 2.3E3 | 2.5E4 | 9.1E3 | 246 | 11 | 160 | 11 | 0.54 |
| kR | pg/ml | 2.1E1 | 2.7E1 | 3.0E1 | 2.9E1 | 6.8E1 | 1.5E1 | 1.0E-9 | 1.2E1 | 1.0E3 | 5.6E1 | 246 | 11 | 160 | 11 | 0.60 |
| kS | pg/ml | 7.8E2 | 9.1E2 | 9.2E2 | 8.3E2 | 6.5E2 | 2.5E2 | 7.9E1 | 4.2E2 | 4.8E3 | 1.2E3 | 246 | 11 | 160 | 11 | 0.53 |
| rZ | ng/ml | 1.0E-9 | 1.0E-9 | 5.8E-3 | 3.3E-2 | 1.5E-2 | 9.4E-2 | 1.0E-9 | 1.0E-9 | 1.1E-1 | 3.0E-1 | 187 | 10 | 127 | 10 | 0.51 |
| rY | ng/ml | 6.1E-2 | 6.6E-2 | 1.4E-1 | 1.8E0 | 5.3E-1 | 5.6E0 | 1.0E-9 | 3.2E-2 | 6.3E0 | 1.8E1 | 187 | 10 | 127 | 10 | 0.59 |
| rX | ng/ml | 1.0E-9 | 1.0E-9 | 4.0E-2 | 2.4E-1 | 2.9E-1 | 7.6E-1 | 1.0E-9 | 1.0E-9 | 3.7E0 | 2.4E0 | 187 | 10 | 127 | 10 | 0.45 |
| lK | pg/ml | 7.9E1 | 5.2E1 | 1.7E2 | 1.2E2 | 3.1E2 | 1.6E2 | 1.0E-9 | 1.0E-9 | 3.3E3 | 5.0E2 | 196 | 9 | 131 | 9 | 0.43 |

Figure 22 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| lL | pg/ml | 1.5E3 | 2.1E3 | 2.1E3 | 3.1E3 | 2.3E3 | 2.3E3 | 1.5E1 | 8.1E2 | 1.9E4 | 7.7E3 | 197 | 9 | 131 | 9 | 0.69 |
| lM | pg/ml | 1.1E3 | 1.0E3 | 3.6E3 | 6.1E3 | 7.0E3 | 1.0E4 | 1.3E2 | 2.8E2 | 4.4E4 | 3.0E4 | 197 | 9 | 131 | 9 | 0.46 |
| lN | pg/ml | 1.0E-9 | 1.0E-9 | 4.3E0 | 3.2E0 | 1.5E1 | 5.4E0 | 1.0E-9 | 1.0E-9 | 1.5E2 | 1.3E1 | 197 | 9 | 131 | 9 | 0.49 |
| lO | pg/ml | 1.0E-9 | 1.0E-9 | 1.8E0 | 1.5E0 | 1.4E1 | 4.4E0 | 1.0E-9 | 1.0E-9 | 1.4E2 | 1.3E1 | 196 | 9 | 131 | 9 | 0.54 |
| nW | pg/ml | 1.1E5 | 1.1E5 | 1.1E5 | 1.2E5 | 2.6E4 | 3.7E4 | 3.6E4 | 6.9E4 | 2.0E5 | 1.8E5 | 246 | 11 | 160 | 11 | 0.53 |
| nY | pg/ml | 2.0E3 | 1.6E3 | 2.3E3 | 2.0E3 | 1.3E3 | 1.3E3 | 5.1E2 | 6.6E2 | 9.9E3 | 5.3E3 | 246 | 11 | 160 | 11 | 0.43 |
| oO | pg/ml | 8.7E4 | 1.1E5 | 1.2E5 | 1.2E5 | 9.5E4 | 7.4E4 | 3.3E3 | 5.6E4 | 6.2E5 | 2.8E5 | 123 | 8 | 96 | 8 | 0.56 |
| oP | pg/ml | 1.2E5 | 1.4E5 | 1.4E5 | 1.8E5 | 8.2E4 | 1.3E5 | 2.4E4 | 6.3E4 | 4.5E5 | 4.2E5 | 123 | 8 | 96 | 8 | 0.57 |
| oQ | pg/ml | 2.9E3 | 2.9E3 | 3.8E3 | 3.6E3 | 3.0E3 | 2.3E3 | 7.7E2 | 1.6E3 | 2.0E4 | 7.9E3 | 123 | 8 | 96 | 8 | 0.49 |
| oE | pg/ml | 1.3E2 | 6.7E1 | 3.9E2 | 1.6E2 | 5.8E2 | 1.9E2 | 1.0E-9 | 1.0E-9 | 4.7E3 | 6.3E2 | 246 | 11 | 160 | 11 | 0.38 |
| oF | pg/ml | 8.0E3 | 4.8E3 | 2.1E4 | 1.2E4 | 3.3E4 | 1.6E4 | 6.4E1 | 1.0E3 | 1.7E5 | 5.7E4 | 246 | 11 | 160 | 11 | 0.45 |
| oH | pg/ml | 4.0E1 | 1.0E2 | 9.3E1 | 1.0E2 | 1.5E2 | 5.9E1 | 4.3E-1 | 3.6E1 | 9.9E2 | 2.0E2 | 246 | 11 | 160 | 11 | 0.70 |
| oK | pg/ml | 8.5E2 | 1.1E3 | 2.0E3 | 1.4E3 | 3.0E3 | 1.3E3 | 5.2E1 | 1.8E2 | 2.5E4 | 4.8E3 | 246 | 11 | 160 | 11 | 0.53 |
| oN | pg/ml | 5.1E2 | 5.4E2 | 7.6E2 | 7.8E2 | 1.4E3 | 9.4E2 | 1.1E2 | 2.6E2 | 1.8E4 | 3.6E3 | 246 | 11 | 160 | 11 | 0.50 |
| pF | pg/ml | 5.1E-1 | 5.1E-1 | 1.1E0 | 7.9E-1 | 5.6E0 | 9.1E-1 | 1.0E-9 | 4.2E-2 | 8.7E1 | 3.1E0 | 246 | 11 | 160 | 11 | 0.50 |

Analyte panel data:

Unconstrained panels with 3 analytes, where 1.0E-6 >= 'model p-value' > 0. Contains 7 panels of 11,182,505 total panels evaluated. : Nm{rZ(nC nH nL nU) mZlM} nF{JtNw PbkK}

Unconstrained panels with 3 analytes, where 1.0E-5 >= 'model p-value' > 1.0E-6. Contains 76 panels of 11,182,505 total panels evaluated. : mZ{lo(hW hX iC jG jQ jR jU jV jY IK qT qX rA rB rY rZ) Nm(jO kK lK rZ) Jt(lK Nw qX) No(jY rZ) nCrY} nF{kK(Hv Io Jj Jt kC ml nC Nm Ny Pz) Jt(Jk Mn nR Nv) rZ(nC Nm No) Hv(nC nL) Nw(Et Pz) NmMj IoPb IsJn} Nm{kK(Hr iB jG nC nH nR Nw Pb rZ) rZ(kG ml mP mY) mP(Nw rY) nUqU} Ib{Uc(Qd Un) Ut(cN Qd) DkcN} Ue{McrB NiVs} Nw{PznH JtnR} nChXrY Unconstrained panels with 2 analytes, where 1.0E-4 >= 'model p-value' > 0. Contains 1 panels of 90,030 total panels evaluated. : NmkK Unconstrained panels with 2 analytes, where 1.0E-3 >= 'model p-value' > 1.0E-4. Contains 75 panels of 90,030 total panels evaluated. : nF(Hv Io Jt kC kK Li lL Mj Mv mZ nC Nf Nm nR Nw Pb Pz Qd) kK(Ih Io Jn Jt Mm Ng Of Pz) Jt(mZ nR nU Oh Ok Qd) No(jF jG jK jY lK) cZ(aC Fn Fp Hv Kk) Io(jG lL mZ nR) Ra(aJ cD cN Fn) Nm(jG mP mZ) Hv(cl Fn Vp) Ib(Dk Uc Ut) Ue(Qw Vs) Pz(nR oP) cN(cl Ex) mZ(jG lL) nC(rY rZ) DcJm FwhG TvKk JnnU aCbE nJIL Unconstrained panels with 2 analytes, where 1.0E-2 >= 'model p-value' > 1.0E-3. Contains 1,525 panels of 90,030 total panels evaluated. : nF(aA Et Fp Fr hA Hq HR Hu hV HW HX iB iC Ih Ii Ij IK Il Im In Ip Iq Ir Is It Iu Iv jD jE jG JH Ji Jj Jk Jl Jm Jn JO JP JQ JR Js jY kE kF kG kl kN kO kP Lh Lj lM lN lO Lu Lv LW LX LY Lz Ma Mb Mc Md ME MF Mg MH MI Mk Ml MM Mn MP Mq Mr MS MT MU MW Mx MY Mz NA NB Nc ND Ne Ng NH NI NJ NK NL nM NN NO Nq Nr Ns NT NU Nv Nx Ny Oe Of Og Oh Oi Ok Om On oO oP oQ Oy Oz Pa Pc Pd Pe Pf Pg Po Qa Qb Qc Qe qT qU qW qX qY rA rB rC rX rY rZ) Hv(Ad Af aG aH al aJ aK aL aM AN Ao aP aQ AR As aU aW aX aY bA bB bE bF bG bl bJ bM BN bO bR bV cB cD cG cJ cL cN cP Cq cS Cu CV CX dA Dc Dd dG dJ dM dN Ed Fb Fw Gz hG Ib iZ Jf jG Ju Jv Jy Kc Ke Ki KK Kr Ld mP mZ nC nl nL Oa oE oF oH Ou Pi Pk Qm Qn Qw Qy Ra Rj Sr Tv Uc Ue Ug Uk Ul Ur Us Ut Vo Vu Vv Tj tF) Fn(aA Af aJ aK aL aN aP AR aU aX aY bB bE bF bG Bn bR bV cD cl cJ cN cR Cs cX dA Dc Dd Di dM dN Dp dR Ez Fa Fb Fp Fr Fw gW hG Ib Ip It Jf Jm Jr Ju Jv Jy Kf Ki Kk Ld Lx Md Mj Mr Ms Mt Mv Nb Nc Ng Ni Nm Nx Oa Of Oh Ou Pc Pd Pe Qc Qd Qm Qw Qy Qz Ss Tv Uc Ue Ul Un Us Vo Vp Vv) Nm(eD Fb Fp hA hR hV hW hX iB iC jD jE jF jH Jl jK jL jM jo jP jQ jR jT jU jV jY kC kE kF kG kl kN kO kP IK IL IM IN IO Lv IW IX IY mE mF mH ml mM mS mT MU mW mY nA nB nC ND nH nl nJ nK nL nM NN nO nR nT nU Nw Oh Ok oO oP oQ Qd qU qV qX rC rY rZ Un) Ra(aA aK aL aM aN aP AR As aW AX aY bA bB bE bG Bn bR bV cl Cs cX cZ dA Dc Dd dG dH dJ dM dN Fa Fb Fp Fr Fw hG Ib Io It Jf Jh Jm Kc Ki KK Kr Ld Lj Lx Mb Md Mj Ms Mv Ni Nx Oa Of Oh Ou Ph Qc Qd Qw Qy St Tv Uc Ue Ug Ul Un Us Ut Vp) cN(aA aC Af aH aJ aL aM aN Ao aR aV bB bG BN bQ bU cB cC cF cG cK cO cP Cq Cx cZ Dc Dd Fb Fp Fw Gz Ib Jl Kk Ld Lw Ly Mb Md Mm Mn Mp Mt Nb Nd Ni Nx Ou Ow Pd Qc Qz Ss Tn Tr Uc Ue Uk Ul Us Ut Vp Tj) mZ(Et hA HR hV hW hX iB iC Ih Ij jD jE Jg jH jl jK jL jM Jn jO jP jQ jR jT jY kK kN Li lK lM IN IO Ma Mg mH Mj Mm mP Mt nB NC nD Nf Ng nJ nL No Nt Of Pb Pf Pz qT qU qV qW qX rA rB rC rX rY rZ) hG(Ad Af aK aL aQ aR As aU bB Bn bO bR cD Cu Cv Cx cY cZ Dc Dd De Di dR Ed Et Ex gW Gz hB Ib Id Ih Ip Je Jl Jm Jp Jy Kf Md Mj Mt Mv oE OF oH Ou Ow Pd Qw Qz Rb Sr Ss Uc Ue Ul Us Ut Vo Vp Vs Vv tF) cZ(aA aJ aN Ar aW Ax aY bA cB cl CP Cs Dc Dd dG dM Fa Fb Fr Ib Jf Jm Kc Ki Kq Ld Lj Lu Lx Ly Mb Mj Mr Mv Nb Nd Ni Nt Nu Nx Oa Oh Ou Pe Qa Qb Qc Qd Qw Qx Qy Qz St Ue Ug Un Vo Vp) kK(Et Hr Hr Ij Im Ir Iv jD JG Jj Jo Jp kF kl kN Li lL Lu Ly Ma Mc Mg mH ml Mn Mt Mx NC Nf nH NL No nR Nt Nu Ny Ok Om Pb Pc Pd Pf Pg Qa) aA(Af aH aL aM aR bB bE bG cl Cx Dc Dd Ex Fb Fp Gz lb Id Ik Iq Jn Jt Jy Kc Ki Ld Lv Ly Md Na Nd Ni oE Of Oh Ou Pa Qw Tn Tv Uc Ue Ul Us Vp) Jt(aJ Fp Fr Ib Ik Iq Is jG Ji Jm kN IL Lv Lx Ly mH Mj mP mS MU Mv mW NA nB nC ND nH NI nK nL Nn nO Nv Nw oP Po Qa rY Un) Io(aJ eD hA hR hV hW hX iB iC jD jE jF jH Jl jK jL jM jO jP jQ jR jT jU jV jY kN IK IM IN IO Lv mH mP nB nC nD nl oP rC rY rZ) Ib(aJ aR aX aY bE cD cl Cq Dc Dd Fb Fw Hw Jf Jh Ki Kj Md Mt Mw Ny oH Om Ou Pd Pg Pi Qc Qd Qm Tn Tr Tv Ue Ul Us Vp Vu tF) Pz(Fp iB jD jG jK jM jY kF kN IK IL IM Lv mH mP mU nA nB nC nD nH nl nK nU Oh oQ Qd qT qU qV qW qX qY rA rB rC rX rY rZ) No(eD Fp hA hR hV hW hX iB iC jD jE jH jl jL jM jO jP jQ jR jT jU jV IL IM IN IO qT qU qV qW qX qY rC rX rY rZ) Ue(aJ aX cl Ex Fb Fr Fw gW Gz Jm Ld Mv Ng Ni Nx Qd qT qU qV qW qX QY rA rB rC rX rY rZ Ua Un Vp) Kk(aH aJ aL Ao aR aX aY bB bE bF bG bR cD cG cl Dc Dd Fw Md Mt Pg Tn To Tr Tt Uc Ul Us Vp) Lv(Fp th li Iq Jn Jr Js Lu Ly Md Mh Mi Mn Mu Na Nd Ng Nj Nr Nt Ny Of Oh Oi On Pa Pd Pf) aJ(aH aM aR bB bG bO cl Dc Dd dL Ed Fw Jm Ld Ly Md Mm Nd Ni Nx Ny oE Ou Qz Sr Uc Vp) cl(aC aP aR Aw aX aY cB CP Dc Dd dG dH dN Fb Fr Jm Ju Ld Ly Mj Mv Nd Ni Nx) Fp(aR aX cD Dc Dd Fw Ih Iq Jn Lu Md Mh Nd Ni Nr Of Pa Pd Pf Tn Tv Vp) Of(Fb Ik Iq jG Ld IL Lu

Figure 22 Continued

Lx Ly mP Mu Na Nd Ni Oh Ok Qd qU rC rY rZ) Dc(Cp Fb Fr Is Kc Ld Mj Mv Nb Ng Ni Nx Oa Pe Qa Qc Qd St Un) Fb(Aj Ao aR bB cD Dd
Ex Fw Gz Kc Ld Mc Ss Uc Us Vo) Ni(Aa aH aR aX aY bB bE bG cD Dd Iq Md Nd Nj Oh Vp) Fw(Fa iZ Jf Kc Ld Nb Oa Pe Qd qV qX qY rC
St Un) Oh(Ih Ii Iq Jn Lu Ly Md Mh Nd Nr Ny Oi On Pa Pd) Qd(Dd Ed Id Jn Kr Nd Ny Pa Sr Tv Uc Us Vo Vp) Ld(aP aX aY bB bG cD Dd Md
Mv Qc Tr Tt Vp) iZ(cD Ed Ip Jm Mj Mv oE Ou Qw Qz Sr Vp tF) jG(Et Ij Ik Im In Jn Mc mP Mx Ng nR Nt Pd) IL(Et kN lY Mc mP nA nD Ng
nI nR NT) Dd(Al Cp Fr Jm Kc Ly Mj Mv Nx St) Nd(aX Iq Lu Lx Md Mu Na Nt Oi On) mP(jD Jn mH Mm mU Nf Pb Pf qU rY) rY(Et Jn Jp Mc
nH nL nR rX) Mv(Ao oE oF oH Tn Tv Uc) Uc(Fr Jm Mj Ng Qy Un) Jn(nD qU qV rC rX rZ) nR(Jg Mm qU qV rX rZ) Ly(aX aY bV cD Iq)
Kc(aR cD Ms Tr Vp) Et(iB jD jY lM) Fr(Kl Sr Tn Vo) Md(Mu Nv Ny Pb) rZ(Jp Mc nH nL) Mu(Iq Pa Pd) Uv(qX rB rX) Mj(Tv Vp) Qy(Ao Jh)
Jm(Ug Vo) aX(Nx Vp) nU(Ij Mx) qX(Or Ow) rX(nC nL) NtjT LuIq LxPa McmT mHnD qVnY

Constrained panels with 3 analytes, where 1.0E-6 >= 'model p-value' > 0. Contains 7 panels of 11,182,505 total panels evaluated. : Nm{rZ(nC nH nL nU) mZlM} nF{JtNw PbkK}

Constrained panels with 3 analytes, where 1.0E-5 >= 'model p-value' > 1.0E-6. Contains 57 panels of 11,182,505 total panels evaluated. :
nF{kK(Hv Io Jj Jt kC ml nC Nm Ny Pz) Jt(Jk Mn nR Nv) rZ(nC Nm No) Hv(nC nL) Nw(Et Pz) NmMj IoPb IsJn} Nm{kK(Hr iB jG mZ nC nH
nR Nw Pb rZ) mP(Nw rY) rZ(ml mY) nUqU mZjO} mZ{Jt(IK Nw qX) No(jY rZ) Io(IK qX) nCrY} Ib{Uc(Qd Un) Ut(cN Qd) DkcN}
Nw{PznH JtnR} McUerB nChXrY Constrained panels with 2 analytes, where 1.0E-4 >= 'model p-value' > 0. Contains 1 panels of 90,030 total panels evaluated. : NmkK Constrained panels with 2 analytes, where 1.0E-3 >= 'model p-value' > 1.0E-4. Contains 73 panels of 90,030 total panels evaluated. : nF(Hv Io Jt
kC kK Li IL Mj Mv mZ nC Nf Nm nR Nw Pb Pz Qd) kK(Ih Io Jn Jt Mm Ng Of Pz) Jt(mZ nR nU Oh Ok Qd) No(jF jG jK jY lK) cZ(aC Fn Fp
Hv Kk) Io(jG IL mZ nR) Ra(aJ cD cN Fn) Nm(jG mP mZ) Hv(cl Fn Vp) Ib(Dk Uc Ut) Pz(nR oP) mZ(jG IL) nC(rY rZ) DcJm FwhG UeQw
TvKk JnnU aCbE clcN nJlL Constrained panels with 2 analytes, where 1.0E-2 >= 'model p-value' > 1.0E-3. Contains 579 panels of 90,030 total panels evaluated. : cZ(aA aJ
aN aW aY bA cl cN CP Cs Dd dG dM Fa Fb Fr hG Ib Jf Jm Ld Ly Mb Mj Mv Nb Nd Ni Nx Pe Qc Qd Qz Ra St Ue Ug Vo) cN(bB bG cG Dc
Dd Fb Fn Fp Hv Ib Jl Kk Ld Lw Ly Md Mm Mt Nd Ni Nx Ou Pd Qc Qz Ss Tn Tr Uc Ue Uk Ul Us Vp) Ib(aR aX cD cl Cq Dc Dd Fb Fw Hv
Hw Jf Md Mt Mw Ny Om Ou Pd Pg Qm Ra Tn Tv Uc Ul Us Vp Vu) Jt(aA Fp Fr Ik Iq Is jG Ji Jm Lv Lx Ly mH Mj mP Mu Mv Na ND Ni Nn
Nv Nw Po Qa Un) Dc(aJ Cp Fb Fp Fr hG Hv Is Kc Kk Ld Mj Mv Nb Ng Ni Nx Oa Pe Qa Qc Qd St Un) Dd(aA aJ Al cl Cp Fb Fn Fp Fr hG Hv
Jm Kc Kk Ld Ly Mj Mv Ni Nx Qd St) Of(Fb Fp hG Ik Iq jG Ld IL Lu Lv Lx Ly mP Mu Na Nd Ni Oh Ok Qd rY rZ) Oh(aA Ih Ii Iq Jn Lu Lv Ly
Md Mh Nd Ni Nm Nr Ny Oi On Pa Pd Pz) aJ(aR bB bG cl Ed Fn Fw Io Ld Ly Mm Nd Ni Nx oE Ou Qz Sr Vp) kK(Et Hv jD jG Jj kF kN IL mH
ml nC Nf nL No nR Nt Ok Pb Pf) Fb(aA Aj Ao bB cD cl Fn Fw Hv Kc Ld Mc Nm Ss Uc Ue Us Vo) Fp(aR aX Fw Ih Iq Jn Lu Md Mh Ni Nm
Nr Pa Pd Pf Pz Tv Vp) hG(aR bR cD Di Hv Jy Md oE Ou Qw Qz Ra Sr Uc Vp Vv tF) Ue(aX cl Fr Fw Jm Ld Mv Ng Ni Nx Qd Qy Ra Ua Un
Vp) aA(aL bG cl Fn Iq Ld Lv Ly Md Nd oE Ou Ra Ul Us Vp) Qd(Ed Fw Jn Kr Nm Ny Pa Pz Ra Sr Tv Uc Us Vo Vp) mZ(Hv iC Ih Jg Jn Ma
Mm mP Nf Ng No Nt Pz qU qX) Fw(Fa Fn iZ Jf Kc Kk Ld Nb Oa Pe Ra St Un) Nm(Ji Lv mH Mu nB nC Nn nR Nw Ok oP Un) Kk(aL Ao aR
bB cD Md Mt Pg Uc Ul Us Vp) mP(Hv jD jG Jn mH Mm mU Nf Pb Pf Pz qU) iZ(cD Ip Jm Mj Mv oE Ou Qw Qz Sr Vp tF) Hv(aX bB cD jG
Kc nC nI Ra Uc Us) Ld(aX aY bB cD cl Fn Md Qc Ra Vp) jG(Et Ij Im Jn Mc Mx nR Nt Pz) Lv(Iq Jn Lu Md Mi Nd Pa Pz) Ni(bB cD cl Fn Iq
Md Nj Vp) Ra(aX aY Fr Kc Mb Mv Qc Vp) rY(Jn Jp Mc nH nL No nR rX) Uc(Fr Jm Mj Mv Ng Qy Un) Fn(aX cD Jm Md Ou Vp) cl(cB Ju Ly
Mv Nd Nx) nF(kN IN nB nK nM nT) rZ(Jp Mc nH nL No nR) Mu(Iq Md Nd Pa Pd) Fr(Kl Sr Tn Vo) Ly(aX aY cD Iq) Mv(Ao oH Tn Tv)
Kc(aR cD Ms Vp) nR(Jg Mm qV rX) Md(Nv Ny Pb) aX(Nd Nx Vp) Nt(jT IL) Mj(Tv Vp) Io(mH rC) Iq(Lu Nd) Qy(Ao Jh) Jm(Ug Vo) nU(Ij
Mx) nD(Jn mH) qX(Or Ow) rX(nC nL) EtlM LxPa McmT NglL qVnY Unconstrained panels with 3 analytes, where 1.0E-10 >= 'AUC p-value' > 0. Contains 611 panels of 11,182,505 total panels evaluated. :
Nm{kK(Fr hA Hr Hu Hv Hw HX iB iC Ih jD jE jF jG Ji Jk Jl jM JO jQ jR Js jV kE kN Lh lL lM lO Ma Mc mH Mj Mm MP Mu Mv MZ nB nC
nF nH nl nL Nn nR nU Nv Nw Ny Of Oh Om oP Pb Pc qT qU qX qY rB rC rY rZ) nH(hA hR hV iB iC jD jE jF jG jl jK jO jP jQ jR jT jY lK IL
lM IN qT qU qV qX rX rY rZ) mP(hA hX iB jE jG jl jM jO jU jV jY IL lM IN Nw qU qV rB rC rX rY rZ) rZ(kF kG kl kN kO kP lW lY mE
mH mM mS mT mU mW mZ nA nB nF nL oP) lM(kC kP mF mU mZ nB nD nF nl nR nU oP) mZ(iB jO jY Li lK Mj qU qV qX rB) IL(kF kG
kO mF ml mU nC nJ) nC(jY IK qU rX rY) rY(kG mM mU nL) nU(jY qU rB) iB(kF kG ml) Nw(nD nF) nR(jO qV) mM(rB rX) nL(jY lK)
rC(kF mU) jG(kF kG) MjnD LhnB qVoP qUoQ} mZ{Io(eD hA hR HV hW hX iB iC Is jD jE jF jG jH jl JK jL jM jO jP JQ jR jT jU jV jY kK
kN Li lK IL lM IN lO Lx mH Mj Mm Mn mP mS Mw nC Nv Nw Nx Oh Qa Qc Qd qT qU qV qW qX qY rA rB rC rX rY rZ) Jt(Fr hA Hv hW
hX iB iC Ii Is jE jG Ji jK JM JO jQ jU jY kK Li lK IL lM Mj Mm Mn Nv Nw Om Qa Qb Qd Qe qT qU qV qW qX rA rB rY rZ) No(hW hX jY
IK lM qT qX rB rY rZ) qX(Et Li Mj Mm Nn Qd qU) kK(Et jG Mm nF Ng) Qd(iC jG nF) Li(iC jG jR) nC(IK rY rZ) jO(Et jG Mm) Mj(Jn nF)
IK(Nf Of) lM(Et Mm) LyqU nOrZ mPrB nJlL} nF{nC(Fr Hu Hv Is Jk Jl Jt kK Lh Li Lx Mj Mp Mt Mu Mv Mw Nn Nw Oh Po Qd rY rZ) Jt(hA
Jk Jl kK Lh lL Mj Mm Mn Mp Mv Mw nL nR Nv Nw Pb rZ) nL(Fr Hu Hv Is Jk Jl kK Lh Mj Mp Mw Nn Nw Oh Po rY rZ) kK(Hr Hu Hv kl IL
Lu ml Mv nH No nR Nw Ny Pb Pc Pz) Mj(aA hA hX Iv jD IL Mx nB NH Pd Pz qU qY) rZ(Et Hu Io Iv Jn Mm nH No Pc Pz rX) Mv(hW hX IL
mP My Nq qU rB) Nw(Et Jn mP Om Pz) Pb(Hv jO IN qU rX) IL(kN Li nJ Nn Nx) hA(Et Io No Pc) No(jl jY) Mp(Mm qU) Is(Jn rX) Jk(Io Pz)
Pc(hX jY) NnqU HxjO mPrB} Jt{nR(Fr Hv iC Ii Is jD Ji kK IL Mj Mn Nw Nx Om qT qX rY rZ) IL(kK IY mH nA nB nl nK) rY(mP nC nH)
NwnD} rY{nC(hX Ih jV nJ No nU Pc) nL(hX Ih nl Pc) mP(Jp No) UenY IonR nJlL} rZ{No(kN kP mP nA) Pz(mP nC nH) Of(nC nH nL)
hX(nC nL) UenY IonR OrbL} IL{nJ(Et hW hX kE kN nC oP rB rC) Io(kK kN mH nR oP) JpkK} Ue{nY(qT qU qV qW qX qY rA rX) rB(Hw
Mc)} Pz{Nw(kK kN mP nC nH) rB(mP oP)} nU{Jn(Mj Qa Qb) Nf(jY qU) Of(jY qU)} Io{nR(jG qU qV rX) mHmP} rB{bL(Mc Ou Ow) MchG
JpmP} No{kK(jG qY) mPhX} qV{MbnY UtcH} rX{OrbL nChX} GzTvcN mHmPhV Unconstrained panels with 3 analytes, where 1.0E-9 >= 'AUC p-value' > 1.0E-10. Contains 410 panels of 11,182,505 total panels evaluated. :
Nm{kK(Et hV Ij In Io Ir jl Jj jK Jn jT jU kl kO lY Mb Me ml Mn MW Na ND Nh Nl Ns nT Nx On oO Oy Pa Pd Pz rA rX) mP(eD HR hV hW
iC jD jF jH jK jL jP jQ jR jT jU Lh IK lO qW qY rA) nH(eD hW hX jH jL jU jV lO nB qW rA rB rC) rZ(kC mF nD nl nJ nK nM nN nO nR nT oO
oQ) mZ(hX Io jK jU Qd qT rY) nF(jO Lh IL Mj Mv nB) lM(IX lY mE mM nK nT) nB(iB Jo Mj nC) IL(lY mT nL nU) nC(hA jQ jR) nU(jO Mj)
mU(jR qU) MunD mMhW nLrX rBkF jGkN qUoP} nF{kK(Et Hx Ih Jj Jk Jl Jn kC kF kN Ma Mj Mp Nd Nl nT Nv Oh) nC(hA Hr Hx Ik IL Lu
Ma nB Nv Nx On Pb Qa Qb Qc) Mv(Et hR HV Io Iv mZ nD nL Pz rC) Mj(Fp hR Hv Ih Il Mh Mt My nJ rY) Pc(hV iB jQ jR IL lM qV qY rY)
nL(hA Li Lx Mu Qa Qd) Io(Hx IL mZ Nw oP) mP(Hr jE IL Qb) Mx(Hv Jk Nw) Pb(mS Qd rY) rX(Jk Mu Ng) Nn(hX qW) No(hX lM) Ml(hA

Figure 22 Continued rZ) Hv(Nc nK) Jt(Ma Of) lL(Fr Il) MuPz NbrB HxqU LimZ hAnH rZlN} mZ{Io(Fr Hx Il Iq Ji Jm Js Jt Lh Lv lW Ly Md Mf Mp Mq Mu Mv mW nB nD Nf Ng nH nJ nL Nn Nr Ns Og Ok Om Pb Qb Qe) Jt(hR hV jD jF jH jI Jq jR jT jV kN Lh lN lO Lx Me mH mP mS Nn nU Oh Ok Pf Qc qY rX) qX(Hv Il Nf Ng Nx Pz) kK(iC Ih jM Jp) No(hV jO lL) rZ(Mb nH nL) lK(kO Ly Ng) Li(jL lL) NniC MaqU MbrB IhJn IljG PzlM JgJk nCrX} lL{nJ(aA hV Io jP jR Jt lW nH nI No Of oO oQ qU rX rZ) Io(kC kP lW lY mF nD nI nU) Jt(kP lX mE mF mP nD nT oP) Pz(kK kN) NgkK} Jt{nR(eD hX Jq My nB nU qW rA) mP(Hv Nw) nC(nU rZ) MnmH nLrY} mP{No(rB rX) mH(Hr jM) jG(Hv kN) rY(Et Pz) MmNw JprZ} Io{nR(hX jP jU mH) rY(cD mF)} nC{rY(Hv Ij qT) HvnK IjrZ IsPz} jG{kN(In No) EtkK MxnU} Pz{IsoP PbkK nLrZ} No{nDjY nIrZ} Ue{ExUn rCnY} nL{HvnK hXrX} NuIhkK MjSrrB MvTnoE QeJnnU UvrXnY PdnHhX Unconstrained panels with 3 analytes, where 1.0E-8 >= 'AUC p-value' > 1.0E-9. Contains 765 panels of 11,182,505 total panels evaluated. : nF{Mj(Fr iC Ii Im Io Iq Iu Jh Jp kC kN kO lM lN Mc Md Me Mg Mp Mv mY Nc nK Nl Nw Nx Ny Oh oQ Oy Pa Pb rX) kK(hA Io Iv Jp Js kO kP Lv Mc mF mH Mu Mw My nA nB nD Nf Nl nJ nK nM Nn Nt Nu Nx oP Oz Qe rC) Mv(hA iC JG jH Jn jO jP jV jY kN Me Mx nB Ng Nw Oy qW rX rY rZ) lL(Hu hW hX iB Iv kG lM Mk Ml Mn MW nB nL No Qd qU rY rZ) nL(Hr Hx Ik Jr Ma mP Mt Nm Nv Nx Ok On Pb Pe Qb Qc Qe) Pb(hR hV Io Iq jE jY Li lK mW nB Nw rC rZ) nC(Io Jm Mk Mn mP Nb Nm nN Nt Of Ok Pe Qe) Jt(Hv Hx Is Ji mP Mu mZ nB Ng Ny Oh oP) Nw(Hv Iv mU MZ nB nH No oP Qd) rZ(Ji Jp kN Lu Mb Mc nD Nf nO) Nn(hR Hv jH jP Me nB rB rX) mP(Hv kC lM Me mH qW qY rA) nB(Hv Is Jk Mx nH No Nt) Mp(Md Mx mY Nm Pz rX) Hv(Hu Is Jk Ma) Pc(jL jM jU rB) hA(Jn Jp On qU) rY(Hu Is Mk nH) No(hV hW jO) Pz(Is Jl oP) rX(Hx Mk Oh) Nm(iB lK) Io(Jl nR) Jk(Jg qU) mZ(jO lM) kO(Lh Lx) MxPg NghX HxlN NymW} mZ{Io(Et Hq Hr Hu Ii Ij Ik In Ip Ir It Iu Iv Jg Jh Jn Jo Jp Jr kC kG kI kO kP Lj Lw lX lY Lz Ma Mb Mc ME mF Mg Mh Mi Mk Ml Mr Ms MT mU Mx My Mz Na Nb Nd Ne Nh nl NK Nl nM nN No Nq nR Nt nU Of Oi On oP oQ Oy Oz Pa Pc Pe Po) Jt(eD Fp Hw Ip It Jk jL jP Js Lv Ly Lz Ma mI MU Mv Mw My nD Nf Ng Nr Nx Pe Po rC) qX(Ip Is Iv Jk kK kN Ly Lz Ma Mb Mk Nk Of Pb Pc rB rY) Nm(hA hR hV hW jF jL jQ jR Lh lL qW rA) rB(Et Il Jj Nc Oy Pe Pf Pz) kK(jD Jn Nf No Of Ok) Et(lK Nw qT qV) No(jK jQ jR qU) Nf(lL mP qU) Jn(lM Qa Qb) iC(Il Ly mP) lK(Jp Ma Pc) Qd(jD jM) Li(jD jM) rY(kO nL) lL(Hv Lz) LyjK OflM mHmP hXqV jGkG qUqT} Nm{kK(aA eD Hq hR hW Ii Ik Il Ip Is It Iv JH jL Jm JP Jq Jr jY kC kG lK lN Lv LW LX Ly Lz Md mF Mg Mh Mi Mk Ml Mq Mr Ms Mt mU Mx MY Nb Nc Ne Nf Ng Ni NJ NK nM NO Nq Nt Nu Oc Ok oQ Oz Pg Po qW) lM(kF kI mH mI mS mT nA nC nJ oO) lL(kN lW mS mW nA nB nO oO oP) mP(Hv Ji Mj Nn qX) iB(kN mU nJ nU oP) qU(kF mI nB nL nR) mM(hR hV hX iC) nC(jD jE jO lN) kF(hA Hr hX jM) nB(Ji Nn Pb) nD(jO Lh Ng) nL(hA jO qT) kG(hA jY rC) oP(iC Is Ji) rZ(kE lX) JtnR nUrX mUjO nHqY} Jt{nR(hA iB jG jH jI jK jL jM jO jP jQ jR jT jY lK lM lO Ly Me Mm Mw nD nJ nK Nv Oh On Qb Qe qU qV rX) lL(kC kG kN kO lW mM mS mT mU mW mY nC nM nN nO nU) Nw(mH nA) jD(nC nH) nUnL mPrC} No{jG(Hv Li lM Mj Mp) mP(hR jE jF rC) rZ(kG nC nH nR) jK(Mj Mp Pb) kK(Jj lL rC) nU(qU rB) rY(nH nL) MjjT PzjY cHqV jFqX kPlM} lL{nJ(hR iC jG Jp jY kP lY Me mF mH mM mY nL nN nR Nt qT) Io(mP nC nH nN nO oO oQ) PzoO OfmP} Pz{oP(Hv Nw Qa Qc) Mj(kN mH) Nw(nD nL) mP(Hr hX) kK(Ny Of) nRrB nCrY kNrZ} Io{nR(HV hW jQ jR kK lK rB rC) cD(rX rZ) mHoP} rY{nC(Iv Jn jU Mc mP qX) nL(Ij mP qT) OrbL UvnY} cN{Gz(Hv Ms Oi Ue) Ex(Ii Ue) Ib(Tr Ut) Ra(Md Vp)} nU{Ma(jY qU) Jn(jG rB) EtqU LzjY nCrX} mP{Mm(Hr hX) Jn(Mj Qb) JphW hVkN} qV{cH(My Mz On) nY(aK Uv) OrbL} rZ{Of(mY nO) nH(Jg Ma) OwbL} Mj{Pd(mH nD) TvKk JnnD} rB{Ue(nY Ou) McaP UvnY} Et{NwnB nHjY jGlM} Jg{kK(Ny Pb) NwnH} cZ{Fp(Hv Tv) MbHv} qX{OrhG UvnY} MvTntF NiUeQw TrKkbF IhkKkN Unconstrained panels with 3 analytes, where 1.0E-7 >= 'AUC p-value' > 1.0E-8. Contains 1,467 panels of 11,182,505 total panels evaluated. : nF{Mj(Hr hV Hw Hx Ip Ir jE JG JI Jj Jl Jm Jn JO Js jT kG kI kP lK lO Lw Lz Ma mF mH Mi Mk MM mP Mq MS mT MU MW Mz Na nD Nf Nj nM Nn Nq Ns nT nU Nv Oe Of Og Oi oO oP Pf Qa Qb Qe qV qW qX rB rZ) lL(eD hA hR Hv Hx In Iq Ir Ji JK jL Jn jO jQ jR jU jV jY kI kO lK Lv lW lY Lz Md Mp mU Mx mZ nA nD Nf NH Ni Nk Nr nT nU Nv Nw Og oO oP Pb Pz qT qV qW rB rC) kK(Fp Hw hX Ii Ij Ik Il In Iq Ir Is Iu jG Ji Jq Li Lj Lw Lx Md Me Mi Mk Mm Ms mU Mx Mz Nb Nc Ne Ng Nh Nj Nk Ns nU Oi Pa Pe Pf Pg Po Qb Qd rX) Mv(eD iB Ii Il Ip Iq Ir jD jE jI jK jL jM jT jU Lj lK lM lN Lu Md Mh Mm Mr mY nN Nr Nx Ok oO oQ Pb Pd Qd qT qX qY rA) Nw(aA Hu Hx Ii Ij Iu Jg Jp Jq kN kO Li Lu Md mF mH Mm Mq Mr mW nD nK Ns Nx Ny Oh Ok Pd Pe Pf) mP(eD Fp hV hW iC jG jH jI jL jQ jR jU jV lO Lx Ml Mw nB Ni Nm nT Pa qT qU qX rC rY rZ) Hv(Fr Hr Io Ip Iq Jn kO Li Lu mF mU mZ Ng nN Ns Nv Ny Oh Qd) Nn(hW iC jM jT jV kC kO mF Mx mY Ni Nj Nq Oh qY rC) rZ(Hw It Jj Li Md Mf Mg Mk Mn Ms Mx Ne Nj nM Of On) Pc(hR hW jF jG jH jI jO jT lO nB nC qW qX rX) Pb(Is jF jK Lh lM lO Lv lY Po Qa Qb Qe qV) Jt(Fr Hu JO Js kN Lx Nq Ok oQ Po Qd) nB(Hu Iv Li Mk Mm Mw Nf nL Ny Oh Qd) nC(Fp Ih Ji Js jY Me Mf Mz Nf Nq Oz) nL(Fp Io Jm Lu Mk Mn Nb Nf nN Of) Jk(kO Mg mS MY Nm Nq Pd rB) Mp(Et hR hX kO Lu lW mF nK) hA(Iv Li Lv Mc Mz Nm Pz rB) rX(Fr Iv Li Mw Nm Nv rY) No(iB jR lK qW rC rY) Is(hX Io jI kO nD) Fr(hX kO mF Pz) Lx(Ii lW mW rB) Mw(kO Mx Nm Pz) Oh(Jn kO Mx nK) Et(iB jO lM) Mu(hW Qb rB) Qd(Lu Pz rC) Li(Mx rA rC) qU(Ma mZ oP) Mk(jY rB) Ng(hR hW) Ny(lK mS) jE(Hx nU) oP(Ji lN) PokO LurB MxJl NflM NjLh IvhX QaJn NxmF nTmU lXjQ nHjY} mZ{Jt(Et Hr Hu Ik Il Im Iq Iv Jg Jj Jl Jn Jp Jr kF kG kO kP Lj Lu lW lX lY Md Mf mM Mp Mq Ms Mx mY NA nB nC Nl nJ nK nL No Nq nR Ns nT Of Og Oi On Oy Oz Pa Pc) qX(Fp Hr iC jG Jj Jn lK lL Lx lY Mf mH Mq Mr Mu Mv Mx Mz nC nH nJ NL Ns Nv Nw Ny Og Oh On oO Pe Pf Po qV rZ) Io(Fp Hw Ih Im Jj Jl kE kF Lu mI mM mY nA Nc Ni Nj nO nT Nu Ny Oe oO Pd Pf Pg Pz) Nm(eD Hr Hv iC Is jD jE jG jH JI Jk jM jP jT jV lN lO Oh qY rC rX) kK(Hr HV Ij kN Ly Ma Mc Mg mH Mn Mt Nl Pc rB) rB(Hw Ii Im In Jl Jn Li Mc Mz nJ Qd qU) qU(Et Il Jn Li Mk mP My nC Of) lL(lY Ma Mb My nA Nk Nx Of Qd) No(hA hR iB jG qV qW rC rX) Li(hV Jn jQ Mm Pz qT qW) qV(Hv Jj Mb mP nA nJ) Et(hX iB jU jY rZ) lK(Hr Mf Mm nL Pz) Mb(hR hW rX rY) mP(HV jR rX) Mj(Mt Pd Pz) Ng(Jg Mg Qd) Jn(Is Qe qT) jG(lM nJ Nn) Pz(Nw qT) Jp(jY lM) iC(Lv Nk) rY(nO Pc) LyqT MglM QdjR kOrZ} Nm{nC(eD hR Hv iB iC jF jG jH jI jK jL jP jT Mj MP nD nK nU Nx Pb qT qV qW qX) kK(Im Iq Iu Jg kF kP Li Lj Lu mE Mf mM mS mT nA nN Nr Og Oi Pc Pf Qb Qd qV) iB(lX lY mE mH mM mT mY nA nD nI nK nL nO nR oO oQ) kG(hR hW hX jD jQ lK qT qU qX qY rA rB rX) lL(kC kE kI kP lX mE mH mM mY nD nM nN nT) mP(Ip Is Jo Ly mH Mn Mu nL Ok Om Po qT) nB(Is jG Jk jO Jq Li lK mH Ng nL Oh rY) lM(jG kE kN kO lW mW mY nL nN nO oQ) jO(kN kP lX mF mI mM mS mY nI oP) nU(hA jD kO Lh lK nL qT qX rY) mU(hR hX iC jE jG jQ jY lK rB) nL(jQ Lh lN Mp Mv nD nK qX) oP(Io jD jG jP jV lK lO rY) nR(jG jK jU jV lK rY) Mj(jD jG mF nA nH) mM(jG jQ jR lK rC) kF(jH jU jY qV rY) nD(Jk lK qU rY) qU(mW nI oO) mI(jM rC) nK(lK rY) LhoO PbmW hAlY lXjR nAlK nHjM nIrY} lL{nJ(hA Hv iB Iq jD jF jH jL jM jO jQ jU kC kF kI kK kO lK lN lO lX Lz Ma mE Mm mP mS mT mU mW nA nB nD Nf Ng nK nM nO nT nU Pc Pd qV qW qX qY rA) Io(kI kO lX mE mM mT mU mW Mx mY nK nL nM nT qU) Jt(kE kF kI mI nH nL oQ) kN(Ih Im Jp Of Pd) No(kP mP nD nU) Et(kK nA) Pz(lY nC) Jp(mP nU) Of(kK nU) MamP NgnC} No{jY(Hv Io jT lK Ml Mn MP mT Mx nO nU qU rY rZ) mP(eD hA hV hW iC jQ jR lO Nw qU qW qY) jK(Hv Hx Mv Nv Nw Ny Oh Wm) rZ(lW mF mY nD nJ nL nU oP) lK(Hv kP Ng nR Of Oh rY) Hv(jF jT kK nB) jG(Mn Nw Oh Qd) nD(jO lM rY) jD(kK Li) rY(cD kN) NglM IojF JtnR nHrX hXkK jOkP} Jt{nR(hV Io It jE jF Jk Jl Jm Jo Jp Js jU jV kN kP Lh Li lN lW LX lY Mc Mf mH MP mS mU mW Mx nA nC nI Og Ok Pc Po Qa Qc Qd qY rC) Nw(nC nH nK nO nU) nU(Fr mH Mj qU) Mn(kN mI nD) mH(Me mP nD) nH(kK rX rZ) nC(nI nK) nL(nI rZ) MjnD mPhX} Pz{Nw(kF kI kO lW lX lY mE mF mH mM mS mU mY nA nI nR nT nU) kK(Hr HX Jk Jl kN Ma Mv nR Oe oP) Mj(kE kP mP nC nD nU oP) mP(Hv Is Jk mH Mu rC) oP(hX Io Ly Oh Qd rZ) rZ(kE kF nK nU) MuoO

AR Ax cJ Cs Ex Gz Ha Jm Lj Nf Nk Oa Ou Po Qe Vp Vv) Tn(AR bB cJ Fp Fr Je Jy Mv Nf Oa Ou Qb) Tt(bB bQ Cu Fp Jv Jy Ou) AlDd ToOu IpaL} Mj{Jn(kN kO lY mE mM mY nA nB nC nL nT oO oQ) Pd(dA jT kN mM mS mW mY nC nJ nL oQ) Tv(Aa Dd Fn iZ Kd Ld St tF) Pf(mT nC nD nH) jG(Ij In kN Mx) Fn(Dd Ng Us) Ni(bB bF Ib) aA(aH aL Tn) Ih(mH nI) Im(mH rC) Of(mM nB) Ut(rB rX) dA(Us Vp) DdKc EzUc TntF SrrX aKiZ nDjD} aJ{Sr(Dp Ex Fb Gz Jm Jy Ld Nx Qc Qd Un) Ex(Ii Ms Ni Tn Uc Us) Nx(bB Dd Et Mm Ng Of) Ou(Bn Dp Fw Oi Tv Vp) Ld(Dd Tn Tr Tv Vp) Gz(Ms Tr Uc Us) Uc(Ib Qw Qy) Tv(bB Fp Vv) Af(Ed Fw) Dd(Al Jm) Ss(Ed rX) bB(Ip Ni) bF(Tr Tt) UnVv aCbE} aA{Ex(Af aH Ic Id Ii Kr Ms Oe Of Oi Pa Tn To Tt Tv Uc Us Vo) Gz(aL Fw Ic Ms Oi Tv Uc) Jm(aH aL Ou Sr Tv Vo Vv) Sr(Fp Oh Qc Qd Un) bB(Nx Tn Tv Vp) Un(Vo Vv) aH(Ip Qc) aL(Ki Ld) AfJy CxFw DpVv FpTv aCbE} Mv{Tn(Ar dR eC Fr gW hB hC hF iO kR nY oK oN pF Ug) Ss(dR nY oE oF oH) Vo(dR Fb Ni oF) Tr(iA Ld oE) Tv(bB Fp oF) Sr(iJ iZ oH) Ng(Fb Fn) Uc(nY oE) Of(gW mW) oH(Ou Vv) AlDd EfrX ExIi LycG NibB JgmH LdUt aKoE} Et{Nw(jD jM jT kF kO mH mM mS mT mW mY nA nJ nT oP oQ) lM(Hr jD Ji Me Mm Ng nR Of) nH(hA hX jD lK lN qU rX) jG(Ip kN Mp nR Oh oP) nB(Ji Mn) nC(jD jY) qY(kF kG) FrSs nRlK nDjO jDoP} rX{nY(Ad Dd Jl Jn Mb Mg Mz On Ow Rb Sr Uc Uk Us) nH(Hr Jp Mk Nf Oh Pb) Sr(cD dJ iZ Qc) Uv(dJ Mr Ur) aP(Jp My On) iH(Kf Ou Vv) cD(Uc Vo) dJ(Ju Ow) nC(Jj nJ) nL(Hu Lu) AlFw KcOn LiUt VvdB} rB{Mc(aK aU Ax bG dB dE Fn iH iZ oH Ou Rb Um) Ou(cD Fw Hf iH Mz Us Uv) dJ(bF Hw Ow Uv Vv) Mz(cF Or Vv) Sr(Ju Oa Qc) Uv(Hw Up Ur) Pf(kN oP) FwOf LunI UknY VvcD} iZ{Jm(Dd Hw Ih Im In Je Jk Mc Ou Vp tF) Ip(aQ aR bB Ex Fw Jp Ou Vv tF) Sr(Oa Qd Un) Gz(Ms Nu) ExMs UnVv} cD{Uc(Ib Nx Oh qT qW Qy rA) Ly(Af aY cI) Ld(Af aY Tv) Vo(Fb qU Qy) Ni(Ib Jm) Sr(qW qY) Ki(Rj Tv) cI(To Tr) QyOf NxPd} Fr{Tn(Ad aH Dd Ib Id Ih Jv Kf Ld Sr Vo Vv) Uc(Ib Qw Qy) Tr(bF Cu Jv) Tv(bB Cu) AoIb MtVo QcSr} Jn{Oh(jG mH mS nB nD) nD(Jm kN Lx nL) jG(Ip kG Mp) Is(jT nB) Qb(mW nH) nI(hX nL) nK(hX nL) JqmS NwnJ nClN} Fb{Vo(Ax bR Ex It Oa Qc Qd Vp) Gz(aR Fw Ic Id Mg) Ex(Fw Mg) AoFw ApDg UcIb aPcG} Fp{Tv(aP bE Fn Jv Kc Ky Mu Pi Vp tF) Ny(aP bE dA dG dH) NidJ TtJv TntF} Tr{Ez(Aa bF Fw Id Jv Ld Of Og) Jv(Cp Kq Ld) Ld(bF Vs) IbJf SttF} Jm{Dd(Mb Mc Ni Ny Oe Tv Us Vp) Ni(bB Vv) Ii(Ar Gz) UvqW} Un{Ib(Ao Ou Uc Ut) Fn(Kf Ou Vv) Uc(Ez Qy) Ii(Ex Gz) Pj(aU Vp)} aP{On(qT qW qY rA) qU(Kc Mt Sr) oF(Ou Qz) AoCp MmNx TvLd VphB} jG{kN(Ih Ij Im Jj Li Lu Mr Nh Nn) AaIp MpOf JjkG nRnJ} dJ{qU(bF Or Ou Ow Uk) rA(bF Or Ow) OrqT OwrC OuqW bFqY} nC{Pd(hA lN) Pf(hX jY) nD(jQ lX) LunK HrnI IuhX OejD OflK} Uc{Ib(Kq Mr Ni Oh) Qy(Is Oh) Qw(Kq Oh) GzJh} Of{Ph(lK lM nJ) Wm(jK jL) Ny(lK mW) JknB OwrC} Jg{Nw(kN nD nL oP) Jk(mH nB) JioP PbIM} aC{bE(aW bA bV cI Cs Dd dM)} Or{Uv(qT qU rA rC) VoqY qUnY} nL{Pf(hX jY) MkjD HrnI HxnK PdhX} Tv{bB(Ez Qd) ArFn AxJv GzgL} nY{Uk(qY rA) qU(Mb Mz) OwqT} Fw{Al(qT qY) Qc(Ib qT)} Ao{Cp(bF Dd dH)} Nt{Ly(jT nB) McjY} Ib{Ut(bA Mr Oh)} Tn{AraX EzIc GzgL} Im{Pb(jM jT) IprC} Qd{Sr(Ar Ld) KorC} bB{NiKx TtaX aRdG} nD{Hr(kN Nc) MmNw} nH{jD(Mk Oe) PfhX} To{EzVo GzgL} nR{LyjD nJqU} qY{SrOa UrUv} AaIpIK DdQcKc WmNgjK ExIiJh NnPdmY TtLdbF OwVorC

Unconstrained panels with 2 analytes, where 1.0E-7 >= 'AUC p-value' > 0. Contains 4 panels of 90,030 total panels evaluated. : NmkK MjnF IomZ nJlL Unconstrained panels with 2 analytes, where 1.0E-6 >= 'AUC p-value' > 1.0E-7. Contains 8 panels of 90,030 total panels evaluated. : nF(kK lL Mp Mv Nw rZ) Jt(mZ nR)

Unconstrained panels with 2 analytes, where 1.0E-5 >= 'AUC p-value' > 1.0E-6. Contains 13 panels of 90,030 total panels evaluated. : nF(Fr hA Hv Is Jk Lh Lx Nn Oh) Ra(aJ cN) NmmP NojY Unconstrained panels with 2 analytes, where 1.0E-4 >= 'AUC p-value' > 1.0E-5. Contains 61 panels of 90,030 total panels evaluated. : nF(hV iB Io Jl JT jY Li mP Mu Mw mZ nB nN Po Qa Qb rY) cN(cI Ex Gz Hv Ib Qz Vp) Nm(jG mZ nB nC nD nL) Jt(mH mP nB nU oP) mZ(kK lL qU qV qX) Io(jG lL mH nR) No(jG jK lK) Pz(kK mP oP) Ue(Qw rB) cZ(Fp Hv) mP(jG mH) AoCp DcJm FbVo nCrY Unconstrained panels with 2 analytes, where 1.0E-3 >= 'AUC p-value' > 1.0E-4. Contains 466 panels of 90,030 total panels evaluated. : cN(aC Af Aj aK aL aN AR As aY aZ bB bG BN bO bQ bS bW cC cG cK Cp Ct Cv CX cZ Dc Dd dE Di dJ dK Dl Dp Ed Et Ez Fb Fp Fw Ic Id Io Ip Jm Kf Ki Ld Ly Mb Mc Md Mj Mm Mn Nd Ni Nu Nx Of Oh Ou Pd Pj Qc Qw Qy Sr St Tn Tr Uc Ue Uk Ul Us Vo Vs Vv) nF(aA Hr Hu HX Ip Iq Ji Jm jQ jR kC kO lM Lu Ma Me mF Mk mM Mn mS mU mW Nb nC Nf nH nK nL Nm Nv Nx oP oQ Pb Pe Pz Qc Qd Qe qU rA) Ue(aK aL Ao Ar aY cI cP cZ Dd dM Ex Fb Hv Jf Jm Kk Kq Ld Mc Mr Ms Nb Ni Nx qU qW qX QY RA rC rX rY St Ul Un Us Vp Vs) cZ(aA aC aJ AN Ar Ax bA Cs dD dG dM dN Fa Fb Fr Ip Jm Kk Ld Lj Lx Ly Mb Mj Mq Mr Mv Nb Ni Nt Nx Pe Qc Ra Un Vo) Io(eD hA hR hV hX iB iC jD jE jF jI jK jL jM jO jP jQ jR jT jU jV jY kN lK lM lN mP Na nB nC Nx oP Qy rC) mZ(Et Hv jG jK jM Jn jO jR jU Li lK lM mH Mm mP Nf Ng nJ Of Pz qT qW rB) Nm(hR jD jY kC kF kG kO lK lL lM lW mE mF mS mU mW nH nN nU oP qU) mP(Fp Hr Hv hX iC jL jM Jn kF kN lL lO Ma Mg Mm No Of Qb qU qY rB) aJ(Af aL aR bB bG Dc Dd Fw Hv Kf Ld Ly Nx Of Ou Sr Tv Vp Vv) Ra(aA aP Ar bA Bc bF Cs dG dM Fn Fp hG iZ Jm Oa Pe Qd Un) No(hR hV jD jF jM jP jT kK lL lM nB nU rC rX rY rZ) Hv(aP Ar aY bE bG cD dA dM hG nC nL Vp) Pz(jG jY kN mH nC nD Qd qU qW rB rC) Jt(jG kK kN lL nC nD nH nL Oh oO Qd) hG(aQ bB Dd Di Gz Qz Sr Vv tF) lL(Et kN lY mF nA nD Ng nI nT) Kk(aL Tn Tr Tt Tv Vo) aA(Af aH bB Cx Gz Vo) iZ(Ip Jm Mj Ou Sr tF) qX(jG Ju Or rC Uv) Dc(Cp Fr Qa Qd) kK(Et Ih Jp Ng) Vo(Fr Mv Qy) jG(Et Jn Nt) qV(aK cH nY) Dd(Cp Jm) Fb(Of Ou) Mj(dA Tv) Sr(Qd rB) dG(aH bB) rY(nH nL) EtlM EzTr FrTn MvTv NfnU LdaY UnPj aCbE bLrZ Unconstrained panels with 2 analytes, where 1.0E-2 >= 'AUC p-value' > 1.0E-3. Contains 3,526 panels of 90,030 total panels evaluated. : Ue(aA aC Ad aE AF aG aH aI AJ Al aM AN aO aP aQ aR AS aU aV aW AX aZ bA BB BC bE bF BG bH bI bJ bL bM BN BO bP bQ bS bU bV bW bX bZ cA cB cC cD cE cF cG CH cJ cK cL cM CO Cp CQ cR CS CT CU CV CW CX cY dA DB DC dD DE dF dG dH DI dJ DK dL dN Dp dR eC Ed EF Et Ez Fa Fn FP Fr Fy GI GP gW Gz Ha HB HF hG Hq Hr Hu Hw Hx iA Ib Ic IH Ii IJ Ik Il Im In Io Ip Iq Ir Is It Iu Iv IZ Je Jg Jh Ji Jj Jk Jl Jn Jo Jp Jq Jr Js Jt Ju Jv Kc Kd Ke Kf Kg Ki Kj Kn Kp kQ KR Ks Kx Lh Li Lj Lu Lv Lw Lx Ly Lz Ma Mb Md Me Mf Mh Mi Mj Mk Ml Mm Mn Mp Mq Mt Mu Mv Mw Mx My Mz Nc Nd Ne Nf Nh Nj Nk Nl Nm Nn No Nr Ns Nt Nu Nv NW NY Oa OE OF Og OH Oi Ok Om ON Or Ou Ow Oz Pa Pb Pc Pd Pe PF Pg Ph Pi Pj Pk Po Pz Qa Qb Qc Qd Qe Qg Qh Ql Qm Qn QT Qu qV Qx Qz Rb Rc Rf Rh Ri Rj Rm rZ Sr Ss Tn To Tr Tv Tz Ua Ub Ud Uf Ug Uh Uk Um Uo Up Ur Ut Uv Vo Vq Vt Vu Vv Wm Tj tF) cN(AA AD aE aF aG aH aI aJ Al aM An AO AP aQ aS aU aV AW AX BA Bb BC bE bF Bg bH bI bJ bL bM Bo bP bR bU bV bX bZ cA cB cD cE cF CH cJ cL cM CO cP CQ cR CS cT CU cV CW cY dA DB dC dD De dF DG dH dI Dk dL dM dN dR Ef Fa Fn fP Fr Fy GL Gp Ha Hb Hc Hq Hr Hu Hw Hx Ih Ii Ij Ik Il Im In Iq Ir Is It Iu Iv IZ Jd Je Jf Jg Jh Ji Jj Jk Jl Jn Jo Jp Jq Jr Js Jt Ju Jv Jy Kc Kd Ke Kg Kj Kk Kl Kn Ko Kp Kq Kr Ks Ky Lh Li Lj Lu Lv Lw Lx Lz Ma Me Mf Mg Mh Mi Mk Ml Mp Mq Mr Ms Mt Mu Mv Mw Mx My Mz Nc Ne Nf Ng Nh Nj Nk Nl Nm Nn No Nq Nr Ns Nt Nv Nw Ny Oa OE Og Oi Ok Om On Or Ow Oy Oz Pa Pb Pc Pe Pf Pg Ph Pi Pk Po Pz Qa Qb Qd Qe Qg Qh Ql Qm Qn Qt Qu Qv QX Rb Rc Rf Rg Rh Ri Rj

Tn Tv Us) Ik(jD Jj Ng Og Pd Pf) Sr(Ax bV Cs Pe Qa qY) Qy(cD Mg Rj Ug Us Vp) Ki(aY cD Rj Tr Tv Us) nJ(mH Mx nC nL nR Pb) rB(bL dJ Fw Ow Uv Vv) qU(Ad aK bL dJ Ju Uv) Ni(aL Ax bB bE bF) Kc(aK aL bN Qm Vp) nD(Hr kN mH Mm nL) qY(aK Or Ow Uv Vv) Nn(Ii Ny Pa Pf) Ng(hA iB lK nB) Tv(Ax Lj Pf St) Aa(jD jL lK) Bc(Id Ou Vv) Lu(Ji nC Ne) Mb(aH aL bE) Ib(aS cP Is) It(Js Jv Us) Jg(lM mH oP) Vp(Ax Cs Pe) dJ(rA rC rY) hX(nC nH nL) jK(Ij Pb Wm) Af(Aw Oa) Ex(Ii Us) St(Ug tF) Jv(Ax Cs) Nw(Ny Pf) Ow(qT rC) Ou(bV Jh) aK(rC rY) bB(cB dH) cI(cP cT) iJ(bR Qz) jD(Mx Pd) AwdN BaSs WmjM MeMh NbaL KdhB UvrA VvbV PbjT aRaY mHmU

Constrained panels with 3 analytes, where 1.0E-10 >= 'AUC p-value' > 0. Contains 300 panels of 11,182,505 total panels evaluated. : nF{Jt(hA Jk Jl kK Lh lL Mj Mm Mn Mp Mv Mw nC nL nR Nv Nw Pb rZ) Mj(hA Iv jD lL Mx mZ nB nC Nh nL Pd Pz qU) kK(Hu Hv kI lL mI nC nH nL Nm nR Ny Pb Pz) rZ(Et Hu Io Jn Mm nC nH nL Nm No Pc Pz rX) Nw(Et Jn mP nC nL Nm Om Pz) nC(Fr Hv Li Mp Mv Qd rY) Pb(Hv jO lN qU) hA(Et Io No Pc) nL(Hv Jk Mp rY) lL(kN Li nJ Nx) Mv(mP My Nq) Mp(Mm qU) Jk(Io Pz) NmlM NojI HxjO IsJn QdmZ} mZ{Jt(Fr Is Ji Jo kK Li lK lM Mj Mm Mn Nw Qb Qd Qe qT qX rB rY) Io(Hv Is kK Li lK mH Mj Mn Nw Oh Qd qX) No(jY lK lM qT qX rY rZ) qX(Et Li Mj Mm Nn qU) kK(Et jG Mm Ng Nm) Li(iC jG jR Nm) jO(Et jG Mm Nm) lM(Et Mm Nm) Qd(iC jG) nC(rY rZ) lK(Nf Of) LyqU MjJn nOrZ nJlL} Nm{kK(Hr Hv Hw Hx iB jG Jl Jo Ma Mj Mv nC nH nR Nw Ny Of Pb rZ) nH(hA jO jY lK qU rX rY rZ) rY(kG mM mP mU nC nL) nU(jY lM qU rB) mP(Nw qU rB) nC(lK lL rX) nL(jY lK rZ) kG(iB jG lL) nR(jO qV) kF(iB jG) LhnB NwnD nArZ nJlL} rY{nC(hX Ih Jt jV nJ No nU Pc) nL(hX Ih nU Pc) Jt(mP nH nR) mP(Jp No) IonR} nR{Jt(Fr Hv Ii Is Ji kK Mj Mn Nw Om rZ) Io(jG qU)} rZ{No(kN kP mP) Pz(mP nC nH) Of(nC nH nL) hX(nC nL) OrbL} rB{Mc(bL hG Ue) Pz(mP oP) bL(Ou Ow) UeHw JpmP} nU{Nf(jY qU) Jn(Mj Qb) Of(jY qU)} Nw{Pz(kN nC nH) JtnD} lL{nJ(Et kN) IokN JpkK} No{kK(jG qY)} qV{MbnY UtcH} IomHmP nChXrX Constrained panels with 3 analytes, where 1.0E-9 >= 'AUC p-value' > 1.0E-10. Contains 130 panels of 11,182,505 total panels evaluated. : nF{Mv(Et Hv Io Iv mZ nD nL Nm Pz) kK(Jj Jn kC kF kN nT) Nm(jO Lh Mj nB) Io(Hx mZ Nw oP) hA(Ml nC nH nL) Mj(Fp Ih Mt) Mx(Hv Jk Nw) nL(Li Lx Qd) Jt(Ma Of) Pb(nC Qd) mP(jE lL) NolM MuPz HxqU LimZ nBnC} mZ{Jt(Me mH nU Oh Ok) qX(Hv Nf Pz) Ng(Io lK) Ih(Jn kK) Li(jL lL) rZ(nH nL) NmQd LylK MaqU MbrB NfIo PzlM JgJk nCrX iCkK} Nm{nB(Jo Mj nC nH) mP(Hr iC Lh) nL(lL rX) MunD nUjO rBkF jGkN qUoP} Jt{nR(Jq nU) mP(Hv Nw) nC(nU rZ) MnmH nLrY} lL{nJ(jP lW No Of) Io(lW lY) kK(Ng Pz)} rY{nC(Hv Ij qT) Io(cD mF) mP(Et Pz)} jG{kN(In mP No) EtkK MxnU HvmP} Pz{IsoP PbkK nLrZ} Hv{nK(nC nL)} mP{MmNw JprZ} hX{PdnH nLrX} NuIhkK MjSrrB MvTnoE IjnCrZ IonRmH UvrXnY Constrained panels with 3 analytes, where 1.0E-8 >= 'AUC p-value' > 1.0E-9. Contains 222 panels of 11,182,505 total panels evaluated. : nF{kK(hA Io kO kP mF mH nA nD nI nJ nK nM oP) Jt(Hv Hx Is Ji mP Mu mZ nB Ng Ny Oh oP) Mj(Io kC kN Mc Me Ne Nl Pa) Mv(Jg Jn kN nB Ng Oy) mP(Hv kC mH nC nL) Nm(iB Mp nC nL) Pz(Is Jl Mp oP) Pb(Io Li nB nL) No(jO nB Nw) hA(Jn Jp qU) nH(nB Nw rY) lL(Hu Iv Qd) Mx(Mp Pg) Hx(lN rX) Jk(Jg qU) rZ(Jp Lu) IonR NwmZ} mZ{rB(Et Il Jj Oy Pf Pz) Nf(Jt kK lL mP qU) qX(Iv kN Of Pb Pc) kK(jD Jn No Ok) lK(Jp Ma Pc) Et(Nw qT) Io(Hr Me) Qd(jD jM) Jn(Qa Qb) Jt(Jk Ng) mP(iC mH) rY(kO nL) LzlL LijD jGkG qUqT} No{jG(Hv Li lM Mj Mp) jK(Mj Mp Pb) nU(qU rB) rY(nH nL) MjjT PzjY JjkK cHqV jFqX kPlM} Nm{Ji(mP nB oP) mP(Hv Mj) nD(Lh Ng) kF(Hr qU) NnnB IsoP nUiB mMiC jYkG} Jt{nR(jM lK Mm nK Oh On Qb Qe rX) nU(lL nL) nClL nHjD} Pz{Mj(kN mH) kK(Ny Of) HrmP HvoP nRrB kNrZ} rY{nC(Iv Jn jU Mc mP) nL(Ij mP qT)} qV{cH(My Mz On) nY(aK Uv) OrbL} Et{NwnB nUqU nHjY jGlM} Mj{Pd(mH nD) TvKk JnnD} Io{nR(Hv kK lK) mHoP} cN{Ib(Tr Ut) Ra(Md Vp)} nJ{lL(Jp lY Mc Nt)} Jg{kK(Ny Pb) nHrZ} Jn{nU(jG rB) QbmP} cZ{Fp(Hv Tv) MbHv} Ue{NiQw OurB} McaPrB MmHrmP MvTntF OrhGqX nUnCrX Constrained panels with 3 analytes, where 1.0E-7 >= 'AUC p-value' > 1.0E-8. Contains 370 panels of 11,182,505 total panels evaluated. : mZ{qX(jG Jj lL lY mH nC nH nL On) kK(Hv kN Ma Mg mH Mn Mt Pc) Nm(Hr Hv Is Jk Oh) Li(hV Jn Mm Pz rB) lL(Ma Mb nF Nk Of) Jt(Hr Iq nC On) rB(Hw In Jn Mc) Mj(Mt Pd Pz) Ng(Jg Mg Qd) mP(Hv qU qV) Pz(lK qT) jY(Et Jp) rY(nO Pc) MglM NkiC HvnF IsJn JjqV OfqU nJjG kOrZ} nF{Mj(Jj Jn mP Of Pf Qa rB) Jt(Fr JO Js kN Ok Qd) Nm(hA Jk mP Mw rX) Nw(Jg Jp Ok Pf) Et(iB jO lM) Hv(Io Jn Qd) Pz(hA Mw Qd) Jk(Mg Pd rB) mP(jG nT qU) kK(jG mU nU) Lu(Mp rB) Mx(Jl Li) Nf(lL nB) Jn(Oh Qa) rX(Iv rY) MchA MvmY lXjQ nBnL lNoP} mP{mH(Hv Jt Mm Nm Of Pd Pz) No(eD iC jQ jR Nw qY) Hv(Hr jL Mm Pz qU) nL(Nm rX rZ) Mm(jG qU) Nf(jD jG) Nw(Et Jg) nC(rX rZ) lL(Jp Ma) NmMu MjPz HrPd IorY PfrB iCkN} No{jK(Hv Hx Mv Nv Nw Ny Oh) Hv(jF jT jY kK nB) jG(Mn Nw Oh Qd) jY(Io Mn nU) lK(kP nR Oh) jD(kK Li) lL(kP nU) lM(nD Ng) nHrX kNrY} Nm{nC(Hv Mp nD nK nU Nx) nL(Mp Mv nB nD nK nU) nB(Is Jq mH) Mj(jD jG) mM(jQ jR) IooP nRlK nUkO nDqU jGlM} kK{Pz(Hr HX Jk Jl kN Ma Mv nR oP) Of(Jg lL Pb) jG(Iq Jj Lu) Ih(nR Nt) EtlL NgPb JpqY JtnH} Jt{nU(Fr mH Mj Nw qU) nR(Lh Li Ok Qd) nH(lL Nw rX rZ) mH(Me nD) nC(nI nK) nL(nI rZ)} rY{nH(Et hX Io Jn nJ Pc Pz) nL(Jn jU jV Mc) nC(iC kN) LynR} Hv{cZ(aN Nb Ni Qc) cN(Mb Vp) nC(nI rZ) DcJm bBhG nInL nJlL} lL{nJ(Iq Ma Nf Ng Pd) nC(Ng Pz) kN(Ih Pd) IoqU JpnU} Ra{aJ(bB cG cZ Kr) cN(cG Ib Pd Tn) aAaL aPcG} Jm{Dc(aA aJ cN hG iJ iZ Nb Ni) ExIi SriZ} rZ{nC(Ih Jn Lu nJ) nH(hX Io Jp) UeIp IjnL} nU{Jn(hX iC) jG(Jr Mq) EtjY MxiC PzkO nLrX} rB{Mc(aJ dJ Uv) bL(Or Vv) MrUe} qX{hG(Ad Jp Mt) Or(bL Ue) UccD} qV{nY(My Uk Us) aK(cH qW) MtcH} Mj{Tv(Ib Kc) TnKk IonR JnmH} cN{Ex(Mt Sr Tn) TrQw} Et{lM(nI Nw) jGkG} Ue{Qw(cZ Un) FbbB} Io{PzoP QnrX PbjG} Tv{FpKk MvLd} Pz{JkmH nClK} bL{MgqU OurX} LunCrX TrKkcD IvjGkN Constrained panels with 3 analytes, where 1.0E-6 >= 'AUC p-value' > 1.0E-7. Contains 647 panels of 11,182,505 total panels evaluated. : nF{Pz(Hv jY Li Lx Ma mP nB Nv Ny Of Oh Pb) nB(Jn kC kN mH mZ nD nK nM nT) Jn(Ih Ji Jm Js Mp Qb Qe) Jt(iB Jq Li lM nU Om On) Mv(Ij Im Jh Mg mW) mP(kO kP nD Nf Nx) nC(Iv kC mZ nK rX) Nm(Ji Ng oP rB) Jk(kC Me mZ Of) Mj(Ij Nr Nt) Nf(Hv mW Qd) hA(Ih lN nK) qU(Jl Lu nR) kK(jE mS mY) Et(Ji lL) Nn(jE jR) Me(oP Pb) Mx(Is Qb) Nw(Ih Nt) mZ(kO nL) nJ(oP Pb) NoQe McHu HrLi IuQb QdjG} mP{jG(Et iC Iq Jt lW Ly mU Of Pd) Hv(aA Et Io Jn Mx nC nL No) mZ(jE Ma Mg Mm nL Nm) iC(Et Jp mH Mm Pz rY) Jt(Fr Hr Nf Qb qU) Nm(Fr Jk Jq Ng) rY(kI Ma Of Ok) No(jD nB Po) Mv(Mg Pz) Jp(eD Nw) mH(jR Nf) qU(Et Ly) McIO MjNg HrPf IoNy NwOk PdlL kIrZ} cN{Ra(aR As bB bG Bn cZ Dc Fn Jl Lw Mb Mm Mt Ow Pa Pg Ul Us) Qz(Kr Md Mn Pd Tn Tr Uc Ue Us Vp) Hv(cI cZ Dc Jl Md) Ib(Dk Pd Tn Uc Vp) Qy(Pd Tr Uc Ut) Qw(Mn Uc Us) Dc(Mj Nx) Fb(bB Sr) aC(bE cZ) qX(Or Ow) FpcZ FrTn MyrX NgTr QdSr} mZ{Jn(Hv Nf Nw Oh Pf) rB(Ih Jp Mm Pd Pg) Pz(Hr jY Nf Qd) jE(Li Mb nJ qX) Mm(Hv Nw Qd) kK(Jj kF nC) rX(kO nL nO) Nm(Nf Qe) No(Hv nB) Mj(hV Jg) Mn(lM qX) Ng(Li lL) Qd(hW jL) rY(Ly nH) MbjG MgqV MzqT HvlK JgNw LijI OklM OnrZ} No{lK(Hx Me Mn Nf nH Nm Nw Pb) jY(jG Mc Ng Nm Oh) jT(Mp Nv Nw Pb) Io(jG jK nR) jD(kN kP Nw) kK(mH mI nC) lL(nA Ng nI) lM(nI Nm rY) jF(Li Nm) jG(hV Mx) MzjK nTjQ nHlN kNrX} Pz{nU(jY Mx nC nH nL qU rB) mH(Mp nC Oh oP Qd) nR(Io Is lK Mj) nH(hX jY kK rX) nC(Fr Mn Nv) jG(kK kN Oh) oP(Hr Nf rY) kK(Hv rB) kN(iB qT) rX(hG nY) IhQd QcqX} kK{Et(Hr Hv Ih jD nC nH Nw) Ng(Hr Hx nC nH nR) Hv(Ih Jn Jp) Jt(jG mH nC) Mc(jD mT) Ih(lL nC) Jg(Ma Mv) MmnH HrJj JnnC JpnR NwOk OfjG} cZ{Hv(aA An aW cI Fr Mj Nx Ue Vp) Fp(aA Dc dD Lu Nb Ni Qc Ra) Ue(Ex Mr Qy Un) Fr(Ss Vo) Un(Ao Pj) AfFa MjNi QcaN aCdM} nU{Mx(Fp Hr Hv jD Jt nC Nm Of) Jt(Hr jG Jo Mn nT) Jn(Hr nC nL) Jr(hX rB) jG(In

Constrained panels with 2 analytes, where 1.0E-7 >= 'AUC p-value' > 0. Contains 4 panels of 90,030 total panels evaluated. : NmkK MjnF IomZ nJIL Constrained panels with 2 analytes, where 1.0E-6 >= 'AUC p-value' > 1.0E-7. Contains 6 panels of 90,030 total panels evaluated. : nF(kK IL Mv Nw) Jt(mZ nR)

Constrained panels with 2 analytes, where 1.0E-5 >= 'AUC p-value' > 1.0E-6. Contains 5 panels of 90,030 total panels evaluated. : Ra(aJ cN) NmmP NojY HvnF Constrained panels with 2 analytes, where 1.0E-4 >= 'AUC p-value' > 1.0E-5. Contains 39 panels of 90,030 total panels evaluated. : Io(jG IL mH nF nR) cN(cl Hv Ib Qz Vp) mZ(IL nF Nm qU qX) Jt(mH mP nF nU) Nm(jG nB nC) No(jG jK lK) Pz(kK mP oP) cZ(Fp Hv) mP(jG mH) nF(Li nB) AoCp DcJm FbVo UeQw nCrY Constrained panels with 2 analytes, where 1.0E-3 >= 'AUC p-value' > 1.0E-4. Contains 163 panels of 90,030 total panels evaluated. : cZ(aA aC aJ aN bA cN Cs dG dM Fa Fb Fr Jm Kk Ld Ly Mb Mj Mv Nb Ni Nx Pe Qc Ra Ue Vo) cN(bB bG cG Dc Dd Fb Fp Ld Ly Md Mm Nd Ni Nx Ou Pd Qc Tn Tr Uc Ue Uk Ul Us) Ue(cl Fb Jf Jm Ld Ms Ni Nx Qy Ra Un Vp) aJ(aR bB bG Dc Dd Fw Ld Ly Nx Ou Sr Vp) mZ(Hv jG Jn Mm mP Nf Ng Pz) nF(kC nC Nf nK Nm Pb Pz Qd) hG(Dd Di Hv Qz Ra Sr Vv tF) iZ(Ip Jm Mj Ou Sr tF) No(jF kK nB rY rZ) Qd(Dc Jt Pz Ra Sr) mP(Hv Jn Mm Of qU) jG(Et Jn Jt Nt Pz) kK(Et Ih Jt Ng) Dc(Cp Fr Qa) Hv(cD nC Vp) Tv(Kk Mj Mv) Dd(Cp Jm) Fr(Tn Vo) Ra(aA Fn) Jt(nD Oh) dG(aH bB) qV(cH nY) rY(nH nL) EtlM EzTr FbOf NmoP MvVo NgIL IorC KkaL LdaY OrqX aCbE Constrained panels with 2 analytes, where 1.0E-2 >= 'AUC p-value' > 1.0E-3. Contains 470 panels of 90,030 total panels evaluated. : Dc(Al Ar Aw Ax Co cP Cs dG dN Fa Fb Fp hG Hv Ir Is Kc Kk Kq Ld Li Lx Mj Mv Nb Nx Oa Oh Pe Qb Qc Qe Rm Un) Dd(aA Al Aw bA Cs cZ Fb Fn Fp Fr Hv Is It Kc Kk Ld Lx Ly Mj Mv Nb Nx Oa Oh Pe Qa Qc Qd) Jt(aA Cp Fb Fr Ik Is Jm Kq Lv Lx Ly Mt Mu Mv Na Nd Nn Nv Nw Nx Ok Po St Un) Vp(aA aP Ax Cs dA Fa Fp Fr hG iZ Jm Kc Kk Ld Lx Oh Pe Qc Qd Qy Ra Un) Uc(Cp dG Ex Ez Fa Fb Fr Hv Ib It Jh Jm Kq Mj Mv Nx Oh Qd Qy Un) Qd(Ao bB cZ Fw Ih Jn Kc Kr Nm Of Oi Pa Pf Pj Qm Tv Ue Us Vo) Fb(aA Aj Ao bB cD Fw Hv Ib Ld Mc Ng Nm Ss Ug Us) Oh(Fw Ii Jf Kr Lu Na Nd Nm Ny Pa Pd Pz Sr Vo) Fr(aH Ao bB bG Ke Kl Pz Ra Sr Ss Ue Us) Mv(Ao iZ Kc Ng Nm Of oH Pd Ra Tn Ue Us) cZ(aW aY cl CP Fn hG Jf Nd Qz St Ug) kK(Hv Io jG Jj Jn IL mH Mm Nt Of Ok Pf) Un(Ad Ao aR Et Nm Ny Of Sr Ug Us Vo) aJ(cl Ed Fn Io Mm Nd Ni oE Qz tF) Lx(Fw Mh Nm No Pa Pd Pf Pz Sr) Hv(aX bB cl Fn jG Kc nl Ra Us) Kk(Ao aR bB cD cN Md Of Us Ut) Jm(Ao Fn Jf Ju Tv Ug Us Vo) Ld(aA bB cD cl Fn Md Qc Ra) Of(Ez hG Ik jG IL Lv Mu Nd) Nm(Ik Lv mH Mu Nn nR Ok) Ue(aX cD Ib It Tz Ua tF) aA(aL bG cl Lv Ly Nd Ou) aP(aR bG Mm Nd oE Ou tF) hG(aR Fw Jy Md oE Ou Qw) Qc(Fw Jf Kc Ra Sr Vo) mP(jD mU nC Nf nL Pd) mZ(iC Ih Jg Ma No Nt) Ra(aY cD Ib Kc Mb) Vo(Ba Ez Mj Nx Qw) bA(aH aL aR bB bG) cN(Fn Jl Lw Mt Ss) nF(kN lN nM nR nT) Fp(Lu Pa Pf Tv) Mu(Nd Ng Pa Pz) Mx(jD jG IL nU) Ik(IL Ng Pd Pz) Us(Ex Fa Mj Qy) cD(Fn Io Ly Qy) dA(aV cB Nd Ul) dG(aR bG cG Mm) nD(Jn mH nL No) rZ(Jp nC nH nL) Ao(Co Ok Qy) Cp(Ad Af aH) Lv(Lu Nd Pa) Qz(iJ iZ oH) aY(aR Jf Ly) jG(Aa Ij Im) Nt(jT IL) Pz(nR Ok) Sr(Cs Qa) Jn(nB nU) Ny(Nn Nw) dM(aR bG) nH(hX rX) iZ(Fw oE) rY(Jp rX) AfAw ArTn BaSs EtnB ExIi FnOu LuNa MgIL MjKr NdIq NibB TvSt ItJv JfKc JgIM OrqV OwqX tFoH mHnJ nChX

Figure 22 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 6.2E1 | 4.9E1 | 7.3E1 | 6.9E1 | 5.0E1 | 5.1E1 | 2.0E0 | 5.0E0 | 2.9E2 | 2.0E2 | 936 | 29 | 159 | 29 | 0.47 |
| Ad | ug/mL | 2.4E-2 | 5.9E-2 | 5.2E-2 | 8.8E-2 | 7.0E-2 | 9.0E-2 | 6.8E-4 | 3.6E-3 | 3.7E-1 | 3.6E-1 | 218 | 25 | 87 | 25 | 0.68 |
| Af | ng/mL | 8.9E-1 | 6.0E-1 | 1.6E1 | 2.5E1 | 7.0E1 | 9.4E1 | 1.7E-3 | 1.7E-3 | 5.3E2 | 4.8E2 | 218 | 25 | 87 | 25 | 0.53 |
| Aj | ug/mL | 1.4E0 | 4.8E0 | 2.6E0 | 3.5E0 | 2.4E0 | 2.4E0 | 1.5E-3 | 3.8E-2 | 6.1E0 | 5.8E0 | 218 | 25 | 87 | 25 | 0.58 |
| Al | mg/mL | 8.8E-5 | 9.6E-5 | 2.5E-4 | 2.4E-4 | 4.2E-4 | 3.8E-4 | 2.5E-6 | 2.1E-5 | 1.9E-3 | 1.4E-3 | 218 | 25 | 87 | 25 | 0.54 |
| An | U/mL | 4.1E1 | 6.6E1 | 1.8E2 | 1.6E2 | 5.5E2 | 2.3E2 | 9.8E-4 | 6.1E-1 | 5.5E3 | 9.1E2 | 218 | 25 | 87 | 25 | 0.57 |
| Ao | pg/mL | 8.1E1 | 7.2E1 | 2.3E2 | 1.7E3 | 1.1E3 | 7.7E3 | 2.8E0 | 7.4E0 | 1.6E4 | 3.9E4 | 218 | 25 | 87 | 25 | 0.52 |
| Ap | ng/mL | 2.6E1 | 4.3E1 | 3.6E1 | 5.4E1 | 3.2E1 | 4.2E1 | 9.9E-1 | 1.8E0 | 1.7E2 | 1.6E2 | 218 | 25 | 87 | 25 | 0.64 |
| Ar | ng/mL | 6.3E-1 | 1.4E0 | 2.3E0 | 4.0E0 | 4.7E0 | 9.9E0 | 3.4E-3 | 3.4E-3 | 4.3E1 | 4.7E1 | 218 | 25 | 87 | 25 | 0.55 |
| As | ng/mL | 8.6E-3 | 8.7E-3 | 1.3E-2 | 1.1E-2 | 1.7E-2 | 9.7E-3 | 1.7E-3 | 1.7E-3 | 1.1E-1 | 4.2E-2 | 218 | 25 | 87 | 25 | 0.50 |
| Aw | pg/mL | 1.5E1 | 1.7E1 | 1.6E1 | 1.9E1 | 4.9E0 | 8.0E0 | 5.0E0 | 6.7E0 | 3.2E1 | 4.8E1 | 218 | 25 | 87 | 25 | 0.62 |
| Ax | ng/mL | 2.2E0 | 1.5E0 | 9.2E0 | 6.5E0 | 1.9E1 | 1.1E1 | 1.9E-2 | 4.9E-2 | 1.5E2 | 4.8E1 | 218 | 25 | 87 | 25 | 0.47 |
| Ba | ng/mL | 4.2E1 | 1.6E2 | 3.5E2 | 7.5E2 | 9.5E2 | 1.7E3 | 3.7E-1 | 1.2E0 | 8.1E3 | 8.1E3 | 218 | 25 | 87 | 25 | 0.64 |
| Bb | ng/mL | 2.3E0 | 3.8E0 | 4.8E0 | 1.4E1 | 8.2E0 | 4.9E1 | 4.1E-3 | 3.0E-1 | 6.6E1 | 2.5E2 | 218 | 25 | 87 | 25 | 0.60 |
| Bc | ng/mL | 3.2E1 | 4.5E1 | 9.6E1 | 1.1E2 | 1.8E2 | 1.9E2 | 1.1E-1 | 6.1E-1 | 1.0E3 | 8.9E2 | 218 | 25 | 87 | 25 | 0.56 |
| Bg | ng/mL | 7.1E-2 | 1.7E-1 | 3.4E0 | 3.4E0 | 2.1E1 | 1.0E1 | 5.3E-4 | 5.3E-4 | 2.5E2 | 4.9E1 | 218 | 25 | 87 | 25 | 0.62 |
| Bn | ng/mL | 5.6E-2 | 5.6E-2 | 8.6E-1 | 1.4E0 | 1.6E0 | 2.2E0 | 5.6E-2 | 5.6E-2 | 9.7E0 | 7.2E0 | 218 | 25 | 87 | 25 | 0.55 |
| Bo | ng/mL | 1.1E1 | 1.9E1 | 1.2E1 | 2.5E1 | 8.8E0 | 4.0E1 | 1.6E-2 | 1.6E-2 | 4.4E1 | 2.1E2 | 218 | 25 | 87 | 25 | 0.64 |
| Ch | uIU/mL | 1.1E0 | 1.5E0 | 7.6E0 | 1.9E1 | 2.3E1 | 4.6E1 | 3.4E-3 | 3.4E-3 | 2.1E2 | 2.1E2 | 218 | 25 | 87 | 25 | 0.55 |
| Co | ng/mL | 3.0E1 | 4.6E1 | 8.0E1 | 4.2E2 | 2.0E2 | 1.8E3 | 3.9E0 | 5.4E0 | 1.9E3 | 9.0E3 | 218 | 25 | 87 | 25 | 0.63 |
| Cp | ng/mL | 2.0E1 | 2.4E1 | 2.4E1 | 3.6E1 | 2.5E1 | 4.5E1 | 6.0E-1 | 2.5E0 | 2.9E2 | 2.4E2 | 218 | 25 | 87 | 25 | 0.61 |
| Cq | ng/mL | 2.4E-2 | 3.2E-2 | 1.7E-1 | 1.6E-1 | 1.2E0 | 4.3E-1 | 8.0E-4 | 8.0E-4 | 1.7E1 | 2.1E0 | 218 | 25 | 87 | 25 | 0.55 |
| Cs | ng/mL | 6.0E1 | 7.3E1 | 2.4E2 | 2.0E2 | 4.4E2 | 3.0E2 | 3.9E-1 | 2.8E0 | 2.9E3 | 1.2E3 | 218 | 25 | 87 | 25 | 0.47 |
| Ct | ng/mL | 1.2E0 | 3.7E-1 | 3.1E1 | 6.9E1 | 9.4E1 | 1.6E2 | 6.2E-3 | 2.5E-2 | 6.2E2 | 4.7E2 | 218 | 25 | 87 | 25 | 0.50 |
| Cu | ng/mL | 2.1E-1 | 2.8E-1 | 4.2E-1 | 4.0E-1 | 8.2E-1 | 3.1E-1 | 9.6E-3 | 3.6E-3 | 9.2E0 | 1.2E0 | 218 | 25 | 87 | 25 | 0.60 |
| Cv | ng/mL | 3.9E0 | 6.4E0 | 1.6E1 | 2.5E1 | 5.3E1 | 5.0E1 | 5.6E-3 | 2.9E-1 | 5.3E2 | 2.4E2 | 218 | 25 | 87 | 25 | 0.58 |
| Cw | mIU/mL | 2.7E-2 | 3.7E-2 | 3.4E-2 | 5.5E-2 | 2.4E-2 | 5.2E-2 | 2.3E-3 | 2.8E-3 | 1.4E-1 | 2.4E-1 | 218 | 25 | 87 | 25 | 0.65 |
| Cx | ng/mL | 1.7E-1 | 3.2E-1 | 5.1E1 | 7.0E1 | 1.0E2 | 1.2E2 | 9.3E-5 | 9.3E-5 | 3.9E2 | 3.9E2 | 218 | 25 | 87 | 25 | 0.48 |
| Db | ug/mL | 7.3E0 | 1.0E1 | 8.3E0 | 1.1E1 | 5.7E0 | 7.3E0 | 5.0E-1 | 9.7E-1 | 3.9E1 | 3.2E1 | 218 | 25 | 87 | 25 | 0.64 |
| Dc | nmol/L | 1.8E-2 | 2.9E-2 | 5.7E-2 | 7.0E-2 | 1.4E-1 | 1.3E-1 | 5.2E-6 | 2.7E-3 | 1.2E0 | 6.3E-1 | 218 | 25 | 87 | 25 | 0.62 |
| Dd | ug/mL | 6.8E-2 | 1.5E-1 | 1.7E-1 | 1.8E-1 | 2.6E-1 | 1.8E-1 | 1.9E-4 | 3.7E-3 | 1.6E0 | 7.8E-1 | 218 | 25 | 87 | 25 | 0.60 |
| De | ng/mL | 3.4E-3 | 3.4E-3 | 6.0E-2 | 1.1E-1 | 1.1E-1 | 2.1E-1 | 3.4E-3 | 3.4E-3 | 5.9E-1 | 8.2E-1 | 218 | 25 | 87 | 25 | 0.53 |
| Dg | ng/mL | 2.5E1 | 5.0E1 | 3.7E1 | 5.2E1 | 3.4E1 | 4.1E1 | 2.4E-1 | 2.9E0 | 1.9E2 | 1.9E2 | 218 | 25 | 87 | 25 | 0.62 |
| Di | pg/mL | 1.7E0 | 2.0E0 | 2.0E0 | 2.6E0 | 1.8E0 | 2.4E0 | 1.8E-1 | 1.8E-1 | 1.3E1 | 9.2E0 | 218 | 25 | 87 | 25 | 0.56 |
| Dk | uIU/mL | 1.5E-2 | 1.8E-2 | 1.0E-1 | 1.6E-1 | 6.8E-1 | 5.2E-1 | 1.1E-4 | 1.1E-4 | 8.9E0 | 2.7E0 | 218 | 25 | 87 | 25 | 0.58 |
| Dl | ng/mL | 2.1E2 | 2.9E2 | 2.7E2 | 3.8E2 | 2.4E2 | 3.4E2 | 1.7E0 | 2.2E1 | 1.4E3 | 1.3E3 | 218 | 25 | 87 | 25 | 0.59 |
| Dp | ng/ml | 2.4E0 | 1.0E0 | 4.5E0 | 4.7E0 | 6.6E0 | 7.4E0 | 3.7E-3 | 3.7E-3 | 4.3E1 | 2.7E1 | 111 | 23 | 86 | 23 | 0.44 |
| Ef | ng/ml | 9.5E-2 | 1.9E-1 | 5.6E-1 | 1.0E0 | 1.3E0 | 2.1E0 | 5.7E-4 | 1.1E-2 | 9.4E0 | 9.5E0 | 143 | 23 | 86 | 23 | 0.63 |
| Wm | % | 7.0E-1 | 8.5E-2 | 3.4E1 | 3.5E0 | 2.1E2 | 1.1E1 | 8.5E-2 | 5.4E-2 | 2.4E3 | 5.5E1 | 173 | 24 | 101 | 24 | 0.41 |
| Ed | pg/ml | 7.1E0 | 5.2E-1 | 1.0E2 | 2.0E1 | 6.9E2 | 4.2E1 | 5.2E-1 | 5.2E-1 | 7.3E3 | 1.5E2 | 111 | 23 | 85 | 23 | 0.39 |
| Tj | pg/mL | 3.7E-1 | 3.7E-1 | 8.9E1 | 3.1E1 | 4.0E2 | 1.2E2 | 3.6E-1 | 3.7E-1 | 3.5E3 | 5.9E2 | 141 | 23 | 86 | 23 | 0.45 |
| Po | pg/ml | 2.6E-1 | 2.6E-2 | 7.7E0 | 1.0E1 | 2.5E1 | 2.1E1 | 8.0E-3 | 2.6E-2 | 2.7E2 | 1.1E2 | 316 | 36 | 135 | 36 | 0.50 |
| Et | ng/ml | 1.1E3 | 1.5E3 | 1.4E3 | 2.0E3 | 1.0E3 | 1.4E3 | 7.7E1 | 1.6E2 | 4.2E3 | 4.9E3 | 316 | 36 | 135 | 36 | 0.62 |
| Fa | ng/ml | 4.0E1 | 3.4E1 | 1.4E2 | 1.8E2 | 7.9E2 | 5.8E2 | 3.4E-2 | 4.9E0 | 8.0E3 | 2.8E3 | 109 | 23 | 86 | 23 | 0.54 |
| Ez | ng/ml | 5.0E0 | 3.6E0 | 2.4E1 | 1.2E1 | 7.6E1 | 1.8E1 | 1.3E-2 | 1.3E-2 | 7.1E2 | 6.6E1 | 111 | 23 | 86 | 23 | 0.48 |
| Fb | ng/ml | 2.3E1 | 2.9E1 | 2.2E1 | 2.5E1 | 1.2E1 | 1.2E1 | 1.0E0 | 8.1E-1 | 5.7E1 | 4.0E1 | 109 | 23 | 86 | 23 | 0.59 |
| Ex | ng/ml | 6.2E-2 | 1.1E-1 | 2.6E-1 | 3.6E-1 | 9.1E-1 | 1.0E0 | 3.5E-5 | 1.5E-4 | 8.9E0 | 4.9E0 | 102 | 21 | 53 | 21 | 0.57 |
| Fn | ng/ml | 2.1E-1 | 2.1E-1 | 9.2E0 | 2.8E0 | 4.0E1 | 5.0E0 | 1.1E-14 | 1.1E-14 | 4.2E2 | 1.9E1 | 111 | 23 | 86 | 23 | 0.43 |
| Fp | ng/ml | 1.0E1 | 1.2E1 | 2.1E1 | 2.5E1 | 2.7E1 | 3.1E1 | 6.0E-3 | 1.3E-1 | 1.4E2 | 1.1E2 | 333 | 36 | 136 | 36 | 0.51 |
| Fr | ng/ml | 2.5E4 | 5.2E4 | 9.7E4 | 1.3E5 | 1.7E5 | 1.6E5 | 6.4E2 | 1.9E2 | 8.4E5 | 6.0E5 | 398 | 37 | 137 | 37 | 0.59 |
| Fw | pg/ml | 8.5E-1 | 1.1E0 | 1.1E2 | 1.1E1 | 7.2E2 | 2.5E1 | 1.1E-14 | 1.2E-1 | 6.9E3 | 1.1E2 | 144 | 23 | 87 | 23 | 0.50 |
| Fy | ng/ml | 3.1E1 | 3.0E1 | 4.9E1 | 5.5E1 | 5.5E1 | 6.0E1 | 1.8E-1 | 1.2E-1 | 3.3E2 | 2.3E2 | 110 | 22 | 85 | 22 | 0.53 |
| Gl | pg/ml | 6.0E3 | 8.7E3 | 9.8E3 | 1.1E4 | 9.0E3 | 9.8E3 | 2.3E2 | 2.0E2 | 3.2E4 | 3.0E4 | 140 | 23 | 87 | 23 | 0.53 |
| Gp | U/ml | 1.8E0 | 8.5E-1 | 4.4E0 | 3.3E0 | 8.0E0 | 6.0E0 | 1.3E-3 | 5.7E-3 | 6.7E1 | 2.3E1 | 144 | 23 | 87 | 23 | 0.39 |

Figure 23

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Gz | ug/ml | 1.2E0 | 1.1E1 | 1.2E1 | 7.4E0 | 5.8E1 | 5.7E0 | 2.9E-16 | 1.6E-1 | 4.8E2 | 1.9E1 | 69 | 21 | 52 | 21 | 0.63 |
| Ha | ng/ml | 2.7E0 | 1.8E0 | 9.0E0 | 1.1E1 | 2.0E1 | 2.0E1 | 1.7E-2 | 1.7E-2 | 1.0E2 | 7.7E1 | 109 | 23 | 85 | 23 | 0.51 |
| Nm | pg/ml | 1.4E4 | 1.6E4 | 2.6E4 | 2.5E4 | 5.1E4 | 2.9E4 | 1.0E-9 | 1.0E-9 | 7.8E5 | 1.2E5 | 315 | 36 | 136 | 36 | 0.51 |
| Nn | pg/ml | 1.2E2 | 1.1E2 | 2.7E3 | 6.3E2 | 1.1E4 | 1.1E3 | 1.0E-9 | 1.0E-9 | 1.0E5 | 4.9E3 | 315 | 36 | 136 | 36 | 0.54 |
| No | pg/ml | 1.4E1 | 1.0E1 | 2.7E1 | 2.8E1 | 5.7E1 | 3.9E1 | 1.0E-9 | 1.0E-9 | 5.9E2 | 1.4E2 | 315 | 36 | 136 | 36 | 0.46 |
| Nq | pg/ml | 2.8E0 | 4.2E-1 | 2.2E1 | 1.3E1 | 8.9E1 | 5.4E1 | 1.0E-9 | 1.0E-9 | 1.2E3 | 3.3E2 | 315 | 36 | 136 | 36 | 0.42 |
| Nr | pg/ml | 6.0E-1 | 6.1E-1 | 1.4E1 | 1.4E1 | 6.9E1 | 3.7E1 | 1.0E-9 | 1.0E-9 | 9.8E2 | 1.7E2 | 315 | 36 | 136 | 36 | 0.52 |
| Ns | pg/ml | 1.0E-9 | 1.0E-9 | 1.3E1 | 7.2E0 | 7.8E1 | 2.9E1 | 1.0E-9 | 1.0E-9 | 1.1E3 | 1.3E2 | 315 | 36 | 136 | 36 | 0.51 |
| Nt | pg/ml | 9.9E1 | 1.2E2 | 1.4E2 | 1.3E2 | 1.3E2 | 7.6E1 | 1.5E1 | 1.5E1 | 1.5E3 | 3.4E2 | 315 | 36 | 136 | 36 | 0.52 |
| Nu | pg/ml | 2.0E1 | 4.3E1 | 5.2E1 | 6.8E1 | 8.8E1 | 7.8E1 | 1.0E-9 | 1.0E-9 | 8.9E2 | 2.6E2 | 315 | 36 | 136 | 36 | 0.56 |
| Lu | pg/ml | 1.0E4 | 1.0E4 | 1.6E4 | 9.2E3 | 4.2E4 | 6.1E3 | 6.7E2 | 1.4E3 | 5.6E5 | 2.1E4 | 317 | 36 | 136 | 36 | 0.46 |
| Lv | pg/ml | 1.0E-9 | 1.0E-9 | 1.1E1 | 2.0E1 | 2.2E1 | 4.5E1 | 1.0E-9 | 1.0E-9 | 2.4E2 | 2.6E2 | 317 | 36 | 136 | 36 | 0.55 |
| Lw | pg/ml | 1.0E-9 | 1.0E-9 | 1.3E-1 | 2.8E-1 | 1.8E0 | 1.7E0 | 1.0E-9 | 1.0E-9 | 3.2E1 | 9.9E0 | 317 | 36 | 136 | 36 | 0.51 |
| Lx | pg/ml | 1.0E-9 | 1.0E-9 | 1.2E2 | 1.8E2 | 4.3E2 | 4.0E2 | 1.0E-9 | 1.0E-9 | 6.2E3 | 1.8E3 | 317 | 36 | 136 | 36 | 0.55 |
| Ly | pg/ml | 1.0E-9 | 6.7E0 | 9.2E0 | 1.4E1 | 1.8E1 | 1.6E1 | 1.0E-9 | 1.0E-9 | 1.2E2 | 4.9E1 | 317 | 36 | 136 | 36 | 0.61 |
| Lz | pg/ml | 1.0E-9 | 1.0E-9 | 2.5E0 | 1.2E0 | 2.5E1 | 7.1E0 | 1.0E-9 | 1.0E-9 | 4.3E2 | 4.3E1 | 317 | 36 | 136 | 36 | 0.49 |
| Ma | pg/ml | 2.7E2 | 3.3E2 | 1.4E3 | 1.5E3 | 4.6E3 | 3.2E3 | 1.0E-9 | 1.0E-9 | 6.5E4 | 1.7E4 | 317 | 36 | 136 | 36 | 0.51 |
| Mb | pg/ml | 2.5E1 | 2.8E1 | 3.0E1 | 3.2E1 | 1.3E1 | 1.3E1 | 5.4E0 | 1.4E1 | 6.9E1 | 5.9E1 | 317 | 36 | 136 | 36 | 0.54 |
| Mc | pg/ml | 1.0E-9 | 1.0E-9 | 2.0E-2 | 4.6E-2 | 2.5E-1 | 2.8E-1 | 1.0E-9 | 1.0E-9 | 4.0E0 | 1.7E0 | 317 | 36 | 136 | 36 | 0.51 |
| Md | pg/ml | 1.0E-9 | 1.0E-9 | 5.0E-1 | 2.9E-1 | 4.0E0 | 1.3E0 | 1.0E-9 | 1.0E-9 | 6.5E1 | 7.3E0 | 317 | 36 | 136 | 36 | 0.51 |
| Me | pg/ml | 3.2E1 | 2.1E1 | 2.9E1 | 2.4E1 | 1.6E1 | 1.3E1 | 1.0E-9 | 2.4E-1 | 1.2E2 | 5.0E1 | 317 | 36 | 136 | 36 | 0.38 |
| Mf | pg/ml | 1.0E-9 | 1.0E-9 | 3.8E-1 | 1.6E-1 | 1.7E0 | 4.3E-1 | 1.0E-9 | 1.0E-9 | 2.0E1 | 2.2E0 | 317 | 36 | 136 | 36 | 0.55 |
| Mg | pg/ml | 2.2E0 | 4.0E0 | 7.3E0 | 7.4E0 | 1.2E1 | 9.5E0 | 1.0E-9 | 1.0E-9 | 8.8E1 | 3.5E1 | 317 | 36 | 136 | 36 | 0.56 |
| Mh | pg/ml | 1.0E-9 | 1.0E-9 | 9.0E-1 | 3.8E-1 | 8.0E0 | 1.4E0 | 1.0E-9 | 1.0E-9 | 1.1E2 | 7.8E0 | 317 | 36 | 136 | 36 | 0.51 |
| Mi | pg/ml | 1.0E-9 | 1.0E-9 | 7.8E-1 | 1.0E-9 | 7.5E0 | 0.0E0 | 1.0E-9 | 1.0E-9 | 1.2E2 | 1.0E-9 | 317 | 36 | 136 | 36 | 0.49 |
| Mj | pg/ml | 1.0E-9 | 1.0E-9 | 4.6E0 | 2.1E0 | 2.8E1 | 5.8E0 | 1.0E-9 | 1.0E-9 | 4.6E2 | 2.2E1 | 317 | 36 | 136 | 36 | 0.49 |
| Mk | pg/ml | 1.0E-9 | 4.6E-1 | 1.7E1 | 1.5E1 | 1.1E2 | 5.7E1 | 1.0E-9 | 1.0E-9 | 1.7E3 | 3.3E2 | 317 | 36 | 136 | 36 | 0.46 |
| Ml | pg/ml | 1.0E-9 | 1.0E-9 | 9.5E0 | 6.6E-1 | 1.2E2 | 2.1E0 | 1.0E-9 | 1.0E-9 | 2.1E3 | 1.2E1 | 317 | 36 | 136 | 36 | 0.51 |
| Mm | pg/ml | 4.6E2 | 4.7E2 | 8.4E2 | 9.7E2 | 9.7E2 | 1.7E3 | 1.0E-9 | 1.0E-9 | 6.0E3 | 9.9E3 | 317 | 36 | 136 | 36 | 0.48 |
| Mn | pg/ml | 4.9E0 | 4.9E0 | 1.0E1 | 7.0E0 | 2.6E1 | 6.9E0 | 1.0E-9 | 1.0E-9 | 3.5E2 | 3.3E1 | 317 | 36 | 136 | 36 | 0.49 |
| Mp | pg/ml | 1.0E-9 | 1.0E-9 | 1.0E1 | 9.1E0 | 2.3E1 | 2.9E1 | 1.0E-9 | 1.0E-9 | 1.8E2 | 1.5E2 | 317 | 36 | 136 | 36 | 0.44 |
| Mq | pg/ml | 1.0E-9 | 1.0E-9 | 2.9E0 | 4.4E0 | 1.8E1 | 1.5E1 | 1.0E-9 | 1.0E-9 | 2.1E2 | 6.5E1 | 317 | 36 | 136 | 36 | 0.52 |
| Mr | pg/ml | 1.0E-9 | 1.0E-9 | 1.6E1 | 2.7E1 | 9.3E1 | 7.7E1 | 1.0E-9 | 1.0E-9 | 1.4E3 | 3.1E2 | 317 | 36 | 136 | 36 | 0.54 |
| Ms | pg/ml | 4.0E2 | 4.2E2 | 5.5E2 | 6.1E2 | 7.0E2 | 7.3E2 | 1.0E-9 | 1.0E-9 | 5.6E3 | 3.3E3 | 317 | 36 | 136 | 36 | 0.51 |
| Mt | pg/ml | 1.0E-9 | 4.9E-1 | 1.1E1 | 4.1E0 | 6.7E1 | 1.3E1 | 1.0E-9 | 1.0E-9 | 8.7E2 | 7.0E1 | 317 | 36 | 136 | 36 | 0.55 |
| Mu | pg/ml | 1.0E-9 | 1.0E-9 | 1.7E0 | 9.1E-1 | 1.1E1 | 3.9E0 | 1.0E-9 | 1.0E-9 | 9.9E1 | 2.3E1 | 317 | 36 | 136 | 36 | 0.51 |
| Mv | pg/ml | 1.0E-9 | 1.0E-9 | 9.5E1 | 4.0E1 | 4.5E2 | 1.6E2 | 1.0E-9 | 1.0E-9 | 4.5E3 | 9.4E2 | 317 | 36 | 136 | 36 | 0.49 |
| Mw | pg/ml | 2.3E1 | 1.6E1 | 6.3E2 | 5.7E2 | 4.1E3 | 2.6E3 | 1.0E-9 | 1.0E-9 | 6.2E4 | 1.6E4 | 317 | 36 | 136 | 36 | 0.49 |
| Mx | pg/ml | 1.0E-9 | 1.0E-9 | 2.1E-1 | 2.2E-1 | 8.3E-1 | 6.4E-1 | 1.0E-9 | 1.0E-9 | 7.4E0 | 3.4E0 | 317 | 36 | 136 | 36 | 0.52 |
| My | pg/ml | 1.0E-9 | 1.0E-9 | 6.1E2 | 8.9E2 | 3.7E3 | 5.1E3 | 1.0E-9 | 1.0E-9 | 3.9E4 | 3.1E4 | 317 | 36 | 136 | 36 | 0.51 |
| Mz | pg/ml | 9.2E0 | 1.0E1 | 2.3E1 | 1.7E1 | 6.3E1 | 2.8E1 | 1.0E-9 | 1.0E-9 | 8.4E2 | 1.4E2 | 317 | 36 | 136 | 36 | 0.51 |
| Na | pg/ml | 1.0E-9 | 1.0E-9 | 5.3E-1 | 4.3E-1 | 1.7E0 | 1.5E0 | 1.0E-9 | 1.0E-9 | 9.6E0 | 7.2E0 | 317 | 36 | 136 | 36 | 0.48 |
| Nb | pg/ml | 1.9E0 | 2.1E0 | 4.9E0 | 4.6E0 | 1.7E1 | 1.3E1 | 1.0E-9 | 1.0E-9 | 2.3E2 | 8.1E1 | 317 | 36 | 136 | 36 | 0.49 |
| Nc | pg/ml | 4.8E2 | 1.4E2 | 7.1E2 | 3.6E2 | 8.7E2 | 5.0E2 | 1.0E-9 | 1.0E-9 | 9.2E3 | 1.8E3 | 317 | 36 | 136 | 36 | 0.34 |
| Nd | pg/ml | 3.0E1 | 9.2E0 | 2.6E1 | 1.7E1 | 2.0E1 | 1.8E1 | 1.0E-9 | 1.0E-9 | 8.4E1 | 5.5E1 | 317 | 36 | 136 | 36 | 0.36 |
| Ne | pg/ml | 5.2E2 | 1.8E2 | 6.7E2 | 2.9E2 | 6.7E2 | 3.3E2 | 1.0E-9 | 1.0E-9 | 7.0E3 | 1.1E3 | 317 | 36 | 136 | 36 | 0.29 |
| Nf | pg/ml | 1.0E-9 | 1.0E-9 | 2.8E0 | 1.1E0 | 8.7E0 | 2.9E0 | 1.0E-9 | 1.0E-9 | 8.2E1 | 1.3E1 | 317 | 36 | 136 | 36 | 0.45 |
| Ng | pg/ml | 3.8E1 | 4.2E1 | 1.5E2 | 1.1E2 | 2.9E2 | 2.0E2 | 1.0E-9 | 1.0E-9 | 2.3E3 | 1.1E3 | 317 | 36 | 136 | 36 | 0.49 |
| Nh | pg/ml | 7.7E1 | 3.4E1 | 1.0E2 | 4.8E1 | 9.1E1 | 4.2E1 | 1.0E-9 | 6.7E0 | 5.6E2 | 1.6E2 | 317 | 36 | 136 | 36 | 0.30 |
| Ni | pg/ml | 4.5E0 | 1.0E-9 | 8.0E1 | 1.0E2 | 1.3E2 | 1.5E2 | 1.0E-9 | 1.0E-9 | 7.1E2 | 5.9E2 | 317 | 36 | 136 | 36 | 0.52 |
| Nj | pg/ml | 8.9E0 | 2.4E0 | 1.2E1 | 7.9E0 | 1.2E1 | 1.1E1 | 1.0E-9 | 1.0E-9 | 8.3E1 | 4.6E1 | 317 | 36 | 136 | 36 | 0.34 |
| Nk | pg/ml | 2.4E1 | 1.4E1 | 3.7E1 | 2.7E1 | 4.1E1 | 3.9E1 | 1.0E-9 | 1.0E-9 | 2.0E2 | 1.7E2 | 317 | 36 | 136 | 36 | 0.42 |
| Nl | pg/ml | 5.6E1 | 1.5E1 | 7.3E1 | 3.0E1 | 8.5E1 | 3.8E1 | 1.0E-9 | 1.0E-9 | 1.1E3 | 1.5E2 | 317 | 36 | 136 | 36 | 0.29 |
| Tz | pg/ml | 4.8E3 | 5.2E3 | 8.4E3 | 1.5E4 | 1.2E4 | 3.4E4 | 7.4E1 | 6.3E2 | 8.8E4 | 1.7E5 | 113 | 24 | 84 | 24 | 0.54 |
| Ua | pg/ml | 3.8E3 | 4.0E3 | 1.3E4 | 2.2E4 | 2.5E4 | 4.0E4 | 3.5E2 | 4.8E2 | 1.4E5 | 1.8E5 | 113 | 24 | 84 | 24 | 0.55 |
| Ub | pg/ml | 5.3E2 | 5.6E2 | 7.9E2 | 7.7E2 | 1.2E3 | 8.0E2 | 1.0E-9 | 1.0E-9 | 9.8E3 | 3.3E3 | 113 | 24 | 84 | 24 | 0.52 |
| Ue | pg/ml | 3.0E1 | 2.4E1 | 3.2E1 | 3.1E1 | 1.9E1 | 2.9E1 | 4.2E0 | 5.9E0 | 9.5E1 | 1.5E2 | 113 | 24 | 84 | 24 | 0.44 |

Figure 23 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Uc | pg/ml | 8.9E2 | 8.4E2 | 1.8E3 | 1.8E3 | 3.4E3 | 2.5E3 | 6.1E-1 | 1.0E2 | 2.9E4 | 9.6E3 | 113 | 24 | 84 | 24 | 0.52 |
| Ud | pg/ml | 1.0E-9 | 1.0E-9 | 3.7E0 | 1.0E-9 | 3.7E1 | 0.0E0 | 1.0E-9 | 1.0E-9 | 3.9E2 | 1.0E-9 | 113 | 24 | 84 | 24 | 0.49 |
| Hq | pg/ml | 1.1E0 | 1.7E0 | 1.2E1 | 9.5E2 | 6.3E1 | 5.6E3 | 1.0E-9 | 1.0E-9 | 9.5E2 | 3.4E4 | 317 | 36 | 136 | 36 | 0.53 |
| Hr | pg/ml | 1.3E2 | 1.1E2 | 8.2E2 | 6.6E2 | 1.5E3 | 9.3E2 | 1.0E-9 | 1.5E1 | 9.7E3 | 3.7E3 | 317 | 36 | 136 | 36 | 0.51 |
| Hu | pg/ml | 1.4E1 | 7.4E-1 | 3.5E3 | 2.0E3 | 3.7E4 | 9.2E3 | 1.0E-9 | 1.0E-9 | 6.3E5 | 5.5E4 | 317 | 36 | 136 | 36 | 0.48 |
| Hv | pg/ml | 1.3E0 | 2.0E0 | 3.6E0 | 3.5E0 | 1.5E1 | 5.4E0 | 1.0E-9 | 1.0E-9 | 2.5E2 | 2.4E1 | 317 | 36 | 136 | 36 | 0.55 |
| Hw | pg/ml | 6.8E0 | 7.2E0 | 2.7E1 | 1.4E1 | 1.1E2 | 1.6E1 | 1.0E-9 | 1.9E-1 | 1.7E3 | 6.7E1 | 317 | 36 | 136 | 36 | 0.51 |
| Hx | pg/ml | 8.3E0 | 1.2E1 | 6.7E1 | 1.8E1 | 5.3E2 | 1.8E1 | 1.0E-9 | 1.0E-9 | 9.3E3 | 7.2E1 | 317 | 36 | 136 | 36 | 0.56 |
| Ib | ng/ml | 6.6E-2 | 5.5E-2 | 7.9E-1 | 4.9E0 | 3.4E0 | 1.3E1 | 1.0E-9 | 1.0E-9 | 3.0E1 | 5.2E1 | 109 | 22 | 85 | 22 | 0.54 |
| Ic | U/ml | 2.2E2 | 2.2E2 | 3.3E2 | 5.1E3 | 1.5E3 | 2.0E4 | 2.9E0 | 2.8E1 | 1.5E4 | 9.3E4 | 109 | 22 | 85 | 22 | 0.68 |
| Id | U/ml | 6.2E-1 | 7.1E-1 | 1.1E0 | 1.9E0 | 1.3E0 | 2.8E0 | 1.0E-9 | 2.7E-1 | 7.2E0 | 1.2E1 | 109 | 22 | 85 | 22 | 0.58 |
| Tt | pg/ml | 1.6E2 | 1.9E2 | 1.7E2 | 1.9E2 | 4.3E1 | 5.2E1 | 8.0E1 | 1.2E2 | 3.0E2 | 2.9E2 | 101 | 19 | 78 | 19 | 0.63 |
| To | pg/ml | 1.6E0 | 1.8E0 | 1.7E0 | 2.0E0 | 1.8E0 | 1.8E0 | 1.0E-9 | 1.0E-9 | 7.1E0 | 5.1E0 | 108 | 20 | 81 | 20 | 0.57 |
| Tr | pg/ml | 2.8E0 | 2.7E0 | 4.0E0 | 6.1E0 | 4.2E0 | 7.6E0 | 3.5E-2 | 3.9E-1 | 2.4E1 | 3.2E1 | 106 | 19 | 80 | 19 | 0.55 |
| Tn | pg/ml | 2.5E1 | 4.4E1 | 4.8E1 | 1.3E2 | 7.0E1 | 2.7E2 | 2.6E0 | 8.8E0 | 3.7E2 | 1.2E3 | 108 | 20 | 81 | 20 | 0.68 |
| Tv | ng/ml | 1.1E1 | 1.7E1 | 2.0E1 | 4.2E1 | 5.0E1 | 7.4E1 | 1.0E-9 | 1.0E-9 | 4.9E2 | 3.2E2 | 108 | 20 | 81 | 20 | 0.62 |
| Ih | ng/ml | 6.8E1 | 7.2E1 | 1.9E2 | 2.1E2 | 3.2E2 | 3.2E2 | 1.0E-9 | 1.0E-9 | 2.5E3 | 1.3E3 | 317 | 36 | 136 | 36 | 0.50 |
| Ii | ng/ml | 8.1E1 | 9.7E1 | 2.9E2 | 1.9E2 | 8.2E2 | 4.2E2 | 7.5E-1 | 7.3E-1 | 8.4E3 | 2.5E3 | 317 | 36 | 136 | 36 | 0.49 |
| Ij | ng/ml | 7.2E1 | 1.1E2 | 2.1E2 | 1.7E2 | 7.5E2 | 2.6E2 | 2.1E0 | 1.0E-9 | 6.4E3 | 1.4E3 | 317 | 36 | 136 | 36 | 0.58 |
| Ik | ng/ml | 1.1E1 | 1.5E1 | 1.0E3 | 3.6E2 | 9.8E3 | 5.9E2 | 5.9E-1 | 8.8E-1 | 1.2E5 | 2.1E3 | 316 | 36 | 136 | 36 | 0.55 |
| Il | ng/ml | 3.8E2 | 3.2E2 | 1.5E3 | 1.0E3 | 3.1E3 | 2.1E3 | 1.0E-9 | 1.0E-9 | 1.2E4 | 1.2E4 | 314 | 36 | 136 | 36 | 0.48 |
| Im | ng/ml | 1.9E2 | 2.3E2 | 3.1E2 | 4.4E2 | 3.5E2 | 6.0E2 | 1.3E1 | 3.0E1 | 3.1E3 | 3.2E3 | 316 | 36 | 136 | 36 | 0.55 |
| In | ng/ml | 4.2E0 | 2.4E0 | 3.5E0 | 7.9E0 | 2.4E2 | 1.2E1 | 1.0E-9 | 1.0E-9 | 3.9E3 | 5.2E1 | 317 | 36 | 136 | 36 | 0.43 |
| Hb | ng/ml | 2.0E1 | 1.8E1 | 2.6E1 | 3.4E1 | 2.4E1 | 3.3E1 | 1.1E0 | 1.3E0 | 1.3E2 | 1.1E2 | 110 | 23 | 86 | 23 | 0.53 |
| Hc | pg/ml | 6.9E2 | 7.5E2 | 2.0E3 | 6.7E3 | 4.7E3 | 2.1E4 | 1.0E-9 | 2.2E2 | 3.6E4 | 1.0E5 | 110 | 23 | 86 | 23 | 0.54 |
| Hf | ng/ml | 1.4E2 | 1.2E2 | 4.0E2 | 2.0E2 | 5.5E2 | 3.1E2 | 1.0E-9 | 1.0E-9 | 2.5E3 | 1.3E3 | 110 | 23 | 86 | 23 | 0.43 |
| Io | ng/ml | 8.4E3 | 6.1E3 | 1.8E4 | 9.7E3 | 5.5E4 | 8.7E3 | 6.6E1 | 2.1E2 | 8.8E5 | 3.3E4 | 315 | 35 | 135 | 35 | 0.45 |
| Ip | ng/ml | 9.7E0 | 7.7E0 | 1.9E1 | 2.1E1 | 2.6E1 | 2.3E1 | 1.0E-9 | 2.4E-2 | 2.6E2 | 8.3E1 | 315 | 35 | 135 | 35 | 0.52 |
| Iq | ug/ml | 1.1E-1 | 1.1E-1 | 4.4E1 | 4.3E-1 | 7.7E2 | 7.6E-1 | 1.0E-9 | 1.0E-9 | 1.4E4 | 3.9E0 | 315 | 35 | 135 | 35 | 0.54 |
| Ir | ug/ml | 3.2E-1 | 6.3E-1 | 3.2E0 | 1.4E0 | 2.1E1 | 2.7E0 | 1.0E-9 | 1.0E-9 | 2.4E2 | 1.6E1 | 314 | 35 | 135 | 35 | 0.58 |
| Is | ng/ml | 1.4E0 | 2.2E0 | 5.6E0 | 7.7E0 | 1.2E1 | 1.9E1 | 1.0E-9 | 1.0E-9 | 8.8E1 | 1.1E2 | 315 | 35 | 135 | 35 | 0.54 |
| It | ng/ml | 2.0E0 | 2.7E0 | 2.2E1 | 9.2E0 | 1.1E2 | 2.0E1 | 1.0E-9 | 1.0E-9 | 1.2E3 | 8.9E1 | 315 | 35 | 135 | 35 | 0.56 |
| Iu | ng/ml | 2.1E2 | 3.3E2 | 1.5E3 | 1.0E3 | 4.8E3 | 2.1E3 | 1.0E-9 | 1.0E-9 | 2.9E4 | 8.3E3 | 315 | 35 | 135 | 35 | 0.55 |
| Iv | ng/ml | 1.3E1 | 1.7E1 | 4.7E1 | 3.4E1 | 1.3E2 | 3.8E1 | 1.0E-9 | 1.0E-9 | 1.6E3 | 1.5E2 | 315 | 34 | 135 | 34 | 0.55 |
| Iz | ng/ml | 1.3E2 | 1.5E2 | 4.0E2 | 4.0E2 | 9.6E2 | 6.0E2 | 1.5E0 | 9.4E0 | 8.4E3 | 2.7E3 | 110 | 23 | 86 | 23 | 0.56 |
| Rc | pg/ml | 5.2E3 | 7.0E3 | 6.3E3 | 8.1E3 | 4.4E3 | 5.6E3 | 1.9E2 | 1.0E3 | 2.2E4 | 1.6E4 | 111 | 23 | 84 | 23 | 0.57 |
| Rb | pg/ml | 7.6E-1 | 9.7E-1 | 2.5E0 | 3.1E0 | 3.6E0 | 8.8E0 | 1.0E-9 | 1.0E-9 | 1.6E1 | 4.3E1 | 111 | 23 | 84 | 23 | 0.51 |
| Pz | ng/ml | 3.3E3 | 1.0E4 | 7.5E3 | 6.8E3 | 1.9E4 | 4.3E3 | 1.3E1 | 2.3E2 | 2.8E5 | 1.4E4 | 314 | 36 | 134 | 36 | 0.58 |
| Qa | ng/ml | 2.8E3 | 4.2E3 | 6.2E3 | 6.6E3 | 8.3E3 | 6.3E3 | 1.5E2 | 6.2E2 | 5.2E4 | 2.5E4 | 314 | 36 | 134 | 36 | 0.60 |
| Qb | ng/ml | 1.0E2 | 1.1E2 | 2.6E2 | 2.0E2 | 6.8E2 | 2.3E2 | 7.9E-1 | 1.6E1 | 8.3E3 | 1.1E3 | 314 | 36 | 134 | 36 | 0.53 |
| Qc | ng/ml | 2.5E2 | 1.9E2 | 5.2E2 | 3.7E2 | 1.0E3 | 4.3E2 | 8.1E-1 | 5.0E0 | 1.1E4 | 1.6E3 | 314 | 36 | 134 | 36 | 0.47 |
| Qd | ng/ml | 9.5E3 | 1.0E4 | 2.8E4 | 1.7E4 | 1.3E5 | 2.0E4 | 2.4E2 | 1.0E3 | 2.0E6 | 8.7E4 | 314 | 36 | 134 | 36 | 0.52 |
| Qe | ng/ml | 7.8E2 | 1.3E3 | 2.0E3 | 1.6E3 | 5.9E3 | 1.8E3 | 7.6E0 | 7.9E1 | 9.7E4 | 9.3E3 | 314 | 36 | 134 | 36 | 0.57 |
| Jd | ng/ml | 3.6E-1 | 7.8E-1 | 7.1E0 | 6.3E0 | 6.2E1 | 1.9E1 | 1.0E-9 | 1.0E-9 | 6.5E2 | 9.1E1 | 111 | 23 | 86 | 23 | 0.63 |
| Je | ng/ml | 1.0E-9 | 8.1E-1 | 1.4E0 | 5.4E0 | 5.6E0 | 1.8E1 | 1.0E-9 | 1.0E-9 | 5.6E1 | 8.8E1 | 111 | 23 | 86 | 23 | 0.62 |
| Jf | ng/ml | 1.0E-9 | 1.0E-9 | 8.1E-1 | 1.5E0 | 2.1E0 | 2.9E0 | 1.0E-9 | 1.0E-9 | 1.2E1 | 8.6E0 | 111 | 23 | 86 | 23 | 0.54 |
| Jg | ng/ml | 3.7E2 | 7.4E2 | 7.2E2 | 8.9E2 | 1.1E3 | 8.3E2 | 5.8E0 | 1.4E1 | 1.0E4 | 4.0E3 | 317 | 36 | 136 | 36 | 0.61 |
| Jh | ng/ml | 2.3E0 | 5.2E0 | 2.5E1 | 5.4E1 | 1.0E2 | 2.6E2 | 1.0E-9 | 1.0E-9 | 1.2E3 | 1.6E3 | 317 | 36 | 136 | 36 | 0.55 |
| Ji | ng/ml | 4.6E1 | 4.4E1 | 6.7E1 | 8.1E1 | 6.9E1 | 8.1E1 | 1.1E0 | 5.1E0 | 5.3E2 | 3.8E2 | 317 | 36 | 136 | 36 | 0.54 |
| Sr | pg/mL | 3.0E2 | 3.8E2 | 7.6E2 | 1.3E3 | 1.3E3 | 1.7E3 | 1.0E-9 | 1.0E-9 | 9.8E3 | 5.5E3 | 106 | 23 | 82 | 23 | 0.59 |
| Ss | pg/mL | 7.6E4 | 2.0E5 | 1.3E5 | 2.2E5 | 1.3E5 | 3.5E5 | 9.5E3 | 1.3E4 | 6.7E5 | 1.8E6 | 106 | 23 | 82 | 23 | 0.61 |
| St | pg/mL | 2.2E7 | 2.0E7 | 4.7E7 | 4.9E7 | 6.0E7 | 5.3E7 | 7.8E5 | 3.4E6 | 4.1E8 | 1.9E8 | 108 | 22 | 82 | 22 | 0.53 |
| Ra | pg/ml | 1.0E-9 | 1.0E-9 | 7.5E-1 | 6.9E-1 | 1.4E0 | 1.3E0 | 1.0E-9 | 1.0E-9 | 7.3E0 | 3.8E0 | 111 | 23 | 84 | 23 | 0.53 |
| Qz | pg/ml | 1.1E1 | 1.0E-9 | 6.9E1 | 4.7E1 | 1.1E2 | 1.1E2 | 1.0E-9 | 1.0E-9 | 7.1E2 | 4.7E2 | 111 | 23 | 84 | 23 | 0.33 |
| Qy | pg/ml | 4.1E-1 | 5.6E-1 | 2.9E0 | 5.5E1 | 1.5E1 | 1.7E2 | 1.0E-9 | 1.0E-9 | 1.6E2 | 6.5E2 | 111 | 23 | 84 | 23 | 0.61 |
| Qx | pg/ml | 1.0E-9 | 1.0E-9 | 6.4E0 | 2.6E1 | 5.1E1 | 1.2E2 | 1.0E-9 | 1.0E-9 | 5.4E2 | 5.8E2 | 111 | 23 | 84 | 23 | 0.52 |
| Qw | pg/ml | 1.8E-1 | 1.0E-9 | 1.4E0 | 4.0E0 | 3.7E0 | 1.8E1 | 1.0E-9 | 1.0E-9 | 3.0E1 | 8.6E1 | 111 | 23 | 84 | 23 | 0.36 |

Figure 23 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Qv | pg/ml | 2.3E4 | 1.2E4 | 3.7E4 | 5.9E4 | 7.7E4 | 1.9E5 | 1.2E3 | 1.6E3 | 7.4E5 | 9.4E5 | 111 | 23 | 84 | 23 | 0.38 |
| Qu | pg/ml | 5.1E0 | 2.7E1 | 7.9E1 | 7.5E1 | 1.7E2 | 1.4E2 | 1.0E-9 | 1.0E-9 | 8.0E2 | 5.1E2 | 111 | 23 | 84 | 23 | 0.58 |
| Qt | pg/ml | 1.2E1 | 1.3E1 | 3.0E1 | 9.3E1 | 5.9E1 | 2.1E2 | 1.0E-9 | 1.0E-9 | 3.8E2 | 8.5E2 | 111 | 23 | 84 | 23 | 0.55 |
| Qh | ng/ml | 1.5E1 | 2.3E1 | 3.7E1 | 3.6E1 | 7.2E1 | 4.2E1 | 1.2E-1 | 1.0E-9 | 6.4E2 | 2.0E2 | 111 | 23 | 84 | 23 | 0.59 |
| Qg | ng/ml | 8.9E0 | 4.7E0 | 2.6E1 | 1.1E1 | 1.0E2 | 1.3E1 | 1.5E-1 | 5.1E-2 | 1.0E3 | 5.8E1 | 111 | 23 | 84 | 23 | 0.39 |
| Jj | ng/ml | 8.4E2 | 6.8E2 | 2.9E3 | 1.7E3 | 2.0E4 | 3.5E3 | 2.0E1 | 1.3E1 | 3.4E5 | 1.7E4 | 317 | 36 | 136 | 36 | 0.48 |
| Jk | ng/ml | 3.3E0 | 5.8E0 | 2.4E1 | 2.3E1 | 5.0E1 | 4.1E1 | 1.0E-9 | 2.6E-1 | 2.8E2 | 1.6E2 | 317 | 36 | 136 | 36 | 0.57 |
| Jl | ng/ml | 3.7E-1 | 6.8E-1 | 1.9E0 | 2.6E0 | 4.7E0 | 5.6E0 | 7.6E-4 | 1.6E-2 | 3.2E1 | 2.0E1 | 317 | 36 | 136 | 36 | 0.57 |
| Jm | ng/ml | 1.9E1 | 2.6E1 | 5.1E1 | 3.7E1 | 9.4E1 | 4.3E1 | 1.0E-9 | 6.7E-1 | 1.0E3 | 2.2E2 | 317 | 36 | 136 | 36 | 0.53 |
| Jn | pg/ml | 3.8E-1 | 4.0E-1 | 1.9E0 | 1.5E0 | 7.0E0 | 3.8E0 | 1.0E-9 | 1.0E-9 | 6.2E1 | 2.0E1 | 317 | 35 | 136 | 35 | 0.52 |
| Jo | pg/ml | 4.0E3 | 4.4E3 | 5.0E3 | 5.7E3 | 3.7E3 | 4.9E3 | 4.2E1 | 7.7E2 | 2.0E4 | 2.0E4 | 317 | 36 | 136 | 36 | 0.52 |
| Jp | pg/ml | 6.6E4 | 7.4E4 | 7.0E4 | 7.5E4 | 3.4E4 | 3.1E4 | 2.1E3 | 5.0E3 | 2.1E5 | 1.5E5 | 317 | 36 | 136 | 36 | 0.56 |
| Jq | pg/ml | 9.2E1 | 7.8E1 | 1.4E2 | 1.8E2 | 1.6E2 | 2.1E2 | 2.6E0 | 1.3E1 | 1.1E3 | 7.9E2 | 317 | 36 | 136 | 36 | 0.51 |
| Jr | pg/ml | 3.8E0 | 4.1E0 | 1.8E1 | 2.1E1 | 6.6E1 | 6.9E1 | 1.0E-9 | 1.0E-9 | 7.9E2 | 4.1E2 | 317 | 36 | 136 | 36 | 0.50 |
| Js | pg/ml | 1.3E1 | 1.1E1 | 4.5E1 | 2.6E1 | 1.5E2 | 5.2E1 | 1.0E-9 | 1.0E-9 | 1.6E3 | 2.9E2 | 317 | 36 | 136 | 36 | 0.47 |
| Jt | pg/ml | 2.4E3 | 2.9E3 | 3.0E3 | 3.2E3 | 2.1E3 | 1.7E3 | 1.5E2 | 2.6E2 | 1.2E4 | 6.6E3 | 317 | 36 | 136 | 36 | 0.57 |
| Ju | mIU/ml | 7.2E0 | 1.7E1 | 2.2E1 | 2.4E1 | 3.6E1 | 2.7E1 | 6.5E-2 | 1.5E-1 | 2.3E2 | 1.0E2 | 111 | 23 | 86 | 23 | 0.58 |
| Jv | mIU/ml | 1.1E1 | 1.2E1 | 3.9E1 | 3.7E1 | 7.4E1 | 5.7E1 | 1.0E-2 | 1.2E-1 | 4.4E2 | 2.2E2 | 111 | 23 | 86 | 23 | 0.51 |
| Jy | ng/ml | 1.5E-3 | 1.9E-3 | 2.3E-3 | 2.8E-3 | 4.9E-3 | 4.2E-3 | 1.7E-4 | 2.2E-4 | 5.2E-2 | 2.2E-2 | 111 | 23 | 86 | 23 | 0.56 |
| Kc | pg/ml | 2.1E1 | 3.2E1 | 3.5E1 | 5.3E1 | 4.0E1 | 5.5E1 | 1.0E-9 | 1.0E-9 | 1.7E2 | 1.9E2 | 111 | 23 | 86 | 23 | 0.60 |
| Kd | pg/ml | 1.0E-9 | 1.0E-9 | 2.4E2 | 1.7E2 | 7.3E2 | 4.6E2 | 1.0E-9 | 1.0E-9 | 4.8E3 | 1.8E3 | 111 | 23 | 86 | 23 | 0.51 |
| Ke | pg/ml | 9.6E3 | 1.4E4 | 1.3E4 | 1.6E4 | 9.5E3 | 1.2E4 | 3.4E2 | 1.3E3 | 5.9E4 | 5.0E4 | 111 | 23 | 86 | 23 | 0.54 |
| Kf | pg/mL | 5.9E0 | 1.0E1 | 6.5E0 | 9.1E0 | 5.7E0 | 6.0E0 | 1.0E-9 | 1.0E-9 | 2.6E1 | 2.2E1 | 111 | 23 | 86 | 23 | 0.64 |
| Kg | pg/mL | 9.9E2 | 1.3E3 | 1.5E3 | 2.5E3 | 1.5E3 | 3.0E3 | 7.3E1 | 1.3E2 | 8.4E3 | 1.3E4 | 111 | 23 | 86 | 23 | 0.57 |
| Ki | pg/ml | 6.4E1 | 4.9E1 | 7.2E1 | 4.7E1 | 5.2E1 | 2.6E1 | 1.0E-9 | 1.0E-9 | 2.9E2 | 1.1E2 | 111 | 23 | 86 | 23 | 0.33 |
| Kj | pg/ml | 9.3E2 | 1.1E3 | 1.5E3 | 1.8E3 | 1.7E3 | 1.5E3 | 1.4E1 | 9.4E1 | 1.0E4 | 5.0E3 | 111 | 23 | 86 | 23 | 0.59 |
| Kk | pg/ml | 6.9E0 | 5.2E0 | 1.1E1 | 1.4E1 | 1.8E1 | 1.6E1 | 1.0E-9 | 1.0E-9 | 1.6E2 | 4.8E1 | 111 | 23 | 86 | 23 | 0.49 |
| Kl | pg/ml | 1.8E4 | 2.9E4 | 2.5E4 | 3.5E4 | 2.2E4 | 2.9E4 | 1.6E2 | 1.3E3 | 1.1E5 | 1.1E5 | 111 | 23 | 86 | 23 | 0.61 |
| Kn | pg/ml | 1.5E1 | 5.2E1 | 5.8E1 | 9.1E1 | 1.1E2 | 1.1E2 | 1.0E-9 | 1.0E-9 | 7.3E2 | 3.8E2 | 111 | 23 | 86 | 23 | 0.64 |
| Ko | pg/ml | 3.0E2 | 5.4E2 | 3.9E2 | 5.1E2 | 4.0E2 | 4.0E2 | 1.0E-9 | 1.0E-9 | 1.8E3 | 1.5E3 | 111 | 23 | 86 | 23 | 0.58 |
| Kp | pg/ml | 3.2E2 | 4.0E2 | 3.4E2 | 3.9E2 | 3.0E2 | 2.4E2 | 1.0E-9 | 1.0E-9 | 1.7E3 | 8.6E2 | 111 | 23 | 86 | 23 | 0.58 |
| Kq | pg/ml | 2.8E2 | 3.6E2 | 4.2E2 | 7.7E2 | 9.7E2 | 1.4E3 | 5.1E0 | 8.8E1 | 9.8E3 | 7.1E3 | 106 | 23 | 82 | 23 | 0.64 |
| Kr | pg/ml | 5.0E-1 | 1.0E-9 | 2.5E0 | 1.1E0 | 4.9E0 | 1.8E0 | 1.0E-9 | 1.0E-9 | 3.5E1 | 5.5E0 | 106 | 23 | 82 | 23 | 0.42 |
| Ks | pg/ml | 1.5E4 | 1.4E4 | 2.1E4 | 1.7E4 | 2.0E4 | 1.4E4 | 3.8E2 | 3.2E2 | 1.1E5 | 5.0E4 | 106 | 23 | 82 | 23 | 0.45 |
| Kx | ng/ml | 1.0E-9 | 1.0E-9 | 4.6E-3 | 1.0E-2 | 8.6E-3 | 2.3E-2 | 1.0E-9 | 1.0E-9 | 5.1E-2 | 1.0E-1 | 110 | 23 | 86 | 23 | 0.54 |
| Ky | ng/ml | 1.0E-1 | 1.0E-1 | 3.5E-1 | 4.8E-1 | 7.1E-1 | 1.3E0 | 1.0E-9 | 1.0E-9 | 5.1E0 | 6.4E0 | 110 | 23 | 86 | 23 | 0.56 |
| Kz | ng/ml | 1.0E-9 | 4.7E-3 | 3.7E-3 | 4.5E-3 | 6.3E-3 | 4.6E-3 | 1.0E-9 | 1.0E-9 | 3.6E-2 | 1.4E-2 | 110 | 23 | 86 | 23 | 0.61 |
| Ld | pg/ml | 1.0E-9 | 7.5E-1 | 4.0E0 | 3.3E0 | 9.9E0 | 4.4E0 | 1.0E-9 | 1.0E-9 | 6.9E1 | 1.9E1 | 108 | 23 | 85 | 23 | 0.57 |
| Lh | pg/ml | 1.1E4 | 1.6E4 | 2.0E4 | 2.2E4 | 2.9E4 | 2.6E4 | 1.0E-9 | 1.8E2 | 2.6E5 | 1.5E5 | 315 | 36 | 136 | 36 | 0.59 |
| Li | pg/ml | 2.6E3 | 4.6E3 | 8.5E3 | 1.2E4 | 2.3E4 | 1.7E4 | 1.0E-9 | 5.6E1 | 2.9E5 | 6.8E4 | 315 | 36 | 136 | 36 | 0.56 |
| Lj | pg/ml | 1.8E3 | 2.5E3 | 1.1E4 | 1.3E4 | 4.2E4 | 3.0E4 | 1.4E1 | 1.0E-9 | 4.4E5 | 1.7E5 | 315 | 36 | 136 | 36 | 0.53 |
| Rm | ng/ml | 1.7E1 | 1.8E1 | 5.8E1 | 4.8E1 | 8.8E1 | 6.5E1 | 2.2E-1 | 3.0E0 | 4.0E2 | 2.5E2 | 110 | 23 | 83 | 23 | 0.50 |
| Rh | ng/ml | 1.4E2 | 7.9E1 | 2.9E2 | 1.7E2 | 5.7E2 | 1.9E2 | 4.7E0 | 7.5E0 | 3.8E3 | 5.8E2 | 110 | 23 | 83 | 23 | 0.40 |
| Ri | ng/ml | 1.0E-9 | 1.0E-9 | 3.9E0 | 2.4E0 | 9.2E0 | 8.6E0 | 1.0E-9 | 1.0E-9 | 7.4E1 | 4.1E1 | 111 | 23 | 84 | 23 | 0.38 |
| Rg | ng/ml | 1.0E-9 | 1.0E-9 | 2.7E-2 | 5.6E-3 | 2.6E-1 | 1.6E-2 | 1.0E-9 | 1.0E-9 | 2.7E0 | 6.7E-2 | 110 | 23 | 83 | 23 | 0.55 |
| Rj | ng/ml | 1.0E-9 | 1.0E-9 | 1.7E0 | 2.9E-1 | 7.9E0 | 6.9E-1 | 1.0E-9 | 1.0E-9 | 8.0E1 | 2.5E0 | 111 | 23 | 84 | 23 | 0.45 |
| Rf | ng/ml | 3.6E-1 | 4.0E-1 | 8.3E-1 | 7.3E-1 | 1.6E0 | 9.0E-1 | 7.8E-3 | 2.8E-2 | 1.4E1 | 3.8E0 | 110 | 23 | 83 | 23 | 0.50 |
| Ql | pg/ml | 7.3E0 | 5.5E0 | 1.4E1 | 9.1E0 | 3.1E1 | 1.4E1 | 1.0E-9 | 1.0E-9 | 2.9E2 | 6.3E1 | 111 | 23 | 86 | 23 | 0.45 |
| Qm | pg/ml | 1.7E0 | 1.0E-9 | 1.9E1 | 1.9E1 | 4.4E1 | 3.0E1 | 1.0E-9 | 1.0E-9 | 3.6E2 | 1.1E2 | 111 | 23 | 86 | 23 | 0.50 |
| Qn | pg/ml | 6.1E-1 | 5.6E-1 | 7.5E0 | 9.2E0 | 2.6E1 | 2.0E1 | 1.0E-9 | 1.0E-9 | 2.2E2 | 7.5E1 | 111 | 23 | 86 | 23 | 0.49 |
| Nv | pg/ml | 3.5E3 | 3.3E3 | 1.3E4 | 2.2E4 | 6.3E4 | 8.8E4 | 1.0E-9 | 7.5E1 | 1.1E6 | 5.3E5 | 318 | 36 | 136 | 36 | 0.53 |
| Nw | pg/ml | 7.4E3 | 1.0E4 | 1.2E4 | 1.5E4 | 2.2E4 | 1.7E4 | 8.6E1 | 7.4E2 | 2.1E5 | 8.9E4 | 318 | 36 | 136 | 36 | 0.55 |
| Nx | pg/ml | 1.7E2 | 2.2E2 | 3.9E2 | 5.4E2 | 7.1E2 | 9.8E2 | 1.0E-9 | 1.0E-9 | 7.4E3 | 5.3E3 | 318 | 36 | 136 | 36 | 0.56 |
| Ny | pg/ml | 4.7E0 | 5.4E0 | 1.1E2 | 7.7E1 | 1.4E3 | 3.4E2 | 1.0E-9 | 1.0E-9 | 2.5E4 | 2.1E3 | 318 | 36 | 136 | 36 | 0.53 |
| Oa | pg/ml | 1.6E2 | 1.1E2 | 4.4E2 | 3.7E2 | 8.0E2 | 5.7E2 | 1.0E-9 | 1.0E-9 | 4.8E3 | 1.8E3 | 111 | 23 | 86 | 23 | 0.44 |
| Wn | ng/ml | 1.2E1 | 1.5E1 | 9.7E1 | 8.0E1 | 3.1E2 | 1.9E2 | 2.5E0 | 3.1E0 | 1.8E3 | 6.1E2 | 33 | 10 | 27 | 10 | 0.50 |
| Tk | ng/ml | 2.0E2 | 1.3E2 | 4.3E2 | 2.1E2 | 7.4E2 | 2.1E2 | 2.4E1 | 2.0E1 | 4.2E3 | 5.3E2 | 36 | 10 | 29 | 10 | 0.38 |

Figure 23 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oe | pg/ml | 9.7E1 | 4.3E1 | 2.7E2 | 2.5E2 | 4.2E2 | 3.5E2 | 1.0E-9 | 1.0E-9 | 2.7E3 | 1.5E3 | 314 | 36 | 136 | 36 | 0.51 |
| Of | pg/ml | 2.1E2 | 3.2E2 | 5.6E3 | 1.2E4 | 1.8E4 | 3.7E4 | 1.0E-9 | 9.7E0 | 1.8E5 | 1.6E5 | 317 | 36 | 136 | 36 | 0.55 |
| Og | pg/ml | 9.4E-2 | 9.5E-2 | 7.2E-1 | 3.2E-1 | 2.2E0 | 8.5E-1 | 1.0E-9 | 1.0E-9 | 2.0E1 | 5.0E0 | 317 | 36 | 136 | 36 | 0.46 |
| Oh | pg/ml | 2.0E0 | 2.8E0 | 2.5E1 | 1.4E1 | 1.2E2 | 4.5E1 | 1.0E-9 | 1.0E-9 | 1.4E3 | 2.6E2 | 317 | 36 | 136 | 36 | 0.56 |
| Oi | pg/ml | 2.9E0 | 2.7E0 | 7.2E0 | 5.2E0 | 1.1E1 | 8.0E0 | 1.0E-9 | 1.0E-9 | 8.6E1 | 4.2E1 | 317 | 36 | 136 | 36 | 0.49 |
| Ok | pg/ml | 3.2E2 | 5.4E2 | 4.3E2 | 6.9E2 | 3.9E2 | 6.1E2 | 1.3E1 | 2.7E1 | 3.1E3 | 3.1E3 | 317 | 36 | 136 | 36 | 0.64 |
| Om | pg/ml | 3.6E2 | 4.1E2 | 7.6E2 | 1.2E3 | 2.1E3 | 3.2E3 | 1.0E-9 | 4.6E1 | 3.0E4 | 2.0E4 | 317 | 36 | 136 | 36 | 0.55 |
| On | pg/ml | 1.4E2 | 2.2E2 | 2.8E2 | 3.8E2 | 4.8E2 | 5.9E2 | 8.4E-1 | 7.9E0 | 4.5E3 | 3.3E3 | 317 | 36 | 136 | 36 | 0.61 |
| Or | pg/ml | 1.0E1 | 2.5E1 | 3.1E1 | 5.4E1 | 6.4E1 | 7.7E1 | 1.0E-9 | 1.0E-9 | 5.0E2 | 3.4E2 | 110 | 23 | 86 | 23 | 0.64 |
| Ow | pg/ml | 2.8E1 | 4.4E1 | 1.0E2 | 5.3E2 | 3.0E2 | 1.7E3 | 1.0E-9 | 1.0E-9 | 2.3E3 | 8.1E3 | 110 | 23 | 86 | 23 | 0.60 |
| Ou | pg/ml | 4.4E2 | 7.4E2 | 8.4E2 | 1.2E3 | 1.2E3 | 1.6E3 | 1.0E-9 | 7.0E1 | 9.4E3 | 6.6E3 | 110 | 23 | 86 | 23 | 0.57 |
| Ul | ng/ml | 1.0E-9 | 1.0E-9 | 1.1E0 | 8.3E-1 | 3.7E0 | 4.0E0 | 1.0E-9 | 1.0E-9 | 2.2E1 | 1.9E1 | 119 | 23 | 88 | 23 | 0.47 |
| Uo | ng/ml | 1.0E-9 | 1.0E-9 | 1.1E-1 | 9.7E-2 | 2.4E-1 | 1.9E-1 | 1.0E-9 | 1.0E-9 | 1.3E0 | 5.5E-1 | 119 | 23 | 88 | 23 | 0.48 |
| Uk | ng/ml | 1.0E-9 | 1.0E-9 | 4.8E-3 | 2.3E-2 | 1.2E-2 | 7.0E-2 | 1.0E-9 | 1.0E-9 | 9.9E-2 | 3.2E-1 | 119 | 23 | 88 | 23 | 0.51 |
| Um | ng/ml | 1.0E-9 | 1.0E-9 | 3.8E-1 | 8.5E-1 | 9.8E-1 | 1.2E0 | 1.0E-9 | 1.0E-9 | 6.8E0 | 3.6E0 | 119 | 23 | 88 | 23 | 0.56 |
| Uf | ng/ml | 4.5E-2 | 6.3E-1 | 9.4E-2 | 4.9E-1 | 1.2E-1 | 1.8E0 | 2.8E-3 | 3.6E-3 | 6.6E-1 | 8.6E0 | 119 | 23 | 88 | 23 | 0.62 |
| Uh | ng/ml | 1.8E0 | 1.9E0 | 2.5E0 | 3.7E0 | 2.3E0 | 4.7E0 | 3.2E-2 | 6.8E-2 | 1.1E1 | 2.1E1 | 119 | 23 | 88 | 23 | 0.54 |
| Un | ng/ml | 1.6E0 | 2.2E0 | 1.9E0 | 2.1E0 | 1.2E0 | 1.1E0 | 2.0E-1 | 2.6E-1 | 7.0E0 | 3.9E0 | 119 | 23 | 88 | 23 | 0.56 |
| Ug | ng/ml | 1.4E1 | 1.5E1 | 2.7E1 | 2.3E1 | 2.7E1 | 2.0E1 | 6.9E-1 | 2.3E0 | 1.3E2 | 6.8E1 | 119 | 23 | 88 | 23 | 0.45 |
| Ur | ng/ml | 1.6E-1 | 1.6E-1 | 1.2E0 | 6.9E-1 | 8.6E0 | 1.2E0 | 1.0E-9 | 1.0E-9 | 9.3E1 | 4.1E0 | 119 | 23 | 88 | 23 | 0.55 |
| Up | ng/ml | 1.0E-9 | 1.0E-9 | 7.5E-3 | 8.4E-4 | 3.4E-2 | 2.3E-3 | 1.0E-9 | 1.0E-9 | 3.3E-1 | 1.1E-2 | 119 | 23 | 88 | 23 | 0.46 |
| Us | ng/ml | 4.4E-3 | 1.0E-9 | 2.1E-2 | 5.0E-3 | 5.6E-2 | 9.5E-3 | 1.0E-9 | 1.0E-9 | 4.0E-1 | 3.6E-2 | 119 | 23 | 88 | 23 | 0.35 |
| Uv | ng/ml | 3.2E-3 | 2.0E-3 | 1.2E-2 | 1.1E-2 | 3.1E-2 | 3.3E-2 | 1.0E-9 | 1.0E-9 | 2.3E-1 | 1.6E-1 | 119 | 23 | 88 | 23 | 0.42 |
| Ut | ng/ml | 5.3E-1 | 8.5E-1 | 2.3E0 | 5.2E0 | 8.9E0 | 1.6E1 | 1.0E-9 | 1.0E-9 | 7.2E1 | 7.8E1 | 119 | 23 | 88 | 23 | 0.56 |
| Uu | ng/ml | 6.9E0 | 7.3E0 | 7.8E0 | 8.0E0 | 5.1E0 | 3.7E0 | 8.1E-1 | 9.8E-1 | 2.6E1 | 1.4E1 | 119 | 23 | 88 | 23 | 0.55 |
| Vp | ng/ml | 1.0E-9 | 1.0E-9 | 7.4E-1 | 3.2E-1 | 5.2E0 | 1.1E0 | 1.0E-9 | 1.0E-9 | 5.0E1 | 5.2E0 | 119 | 23 | 88 | 23 | 0.53 |
| Vt | ng/ml | 6.1E0 | 6.2E0 | 7.6E0 | 8.0E0 | 6.1E0 | 7.4E0 | 6.0E-1 | 7.0E-1 | 3.2E1 | 3.0E1 | 119 | 23 | 88 | 23 | 0.48 |
| Vu | ng/ml | 1.0E-9 | 1.0E-9 | 2.3E0 | 3.2E0 | 6.0E0 | 8.2E0 | 1.0E-9 | 1.0E-9 | 5.1E1 | 3.8E1 | 118 | 22 | 88 | 22 | 0.53 |
| Vq | ng/ml | 1.2E2 | 3.3E2 | 5.5E2 | 8.9E2 | 1.2E3 | 1.1E3 | 2.0E-1 | 2.6E0 | 1.0E4 | 4.3E3 | 94 | 20 | 72 | 20 | 0.64 |
| Vo | ng/ml | 2.6E1 | 2.5E1 | 2.5E1 | 2.5E1 | 4.9E0 | 2.5E0 | 2.5E0 | 2.0E1 | 3.5E1 | 3.0E1 | 119 | 23 | 88 | 23 | 0.44 |
| Vs | ng/ml | 1.0E-9 | 1.9E0 | 6.5E0 | 1.7E1 | 2.7E1 | 4.8E1 | 1.0E-9 | 1.0E-9 | 2.3E2 | 2.2E2 | 116 | 23 | 86 | 23 | 0.57 |
| Vv | ng/ml | 2.7E0 | 4.1E0 | 6.0E0 | 5.4E0 | 1.0E1 | 6.0E0 | 1.0E-9 | 1.0E-9 | 8.1E1 | 2.6E1 | 118 | 23 | 88 | 23 | 0.54 |
| Oy | pg/ml | 5.5E-3 | 7.1E-1 | 8.7E0 | 9.2E0 | 4.2E1 | 4.2E1 | 1.0E-9 | 1.0E-9 | 4.0E2 | 2.5E2 | 317 | 36 | 136 | 36 | 0.50 |
| Oz | pg/ml | 4.5E-3 | 4.0E-2 | 2.2E-1 | 1.8E-1 | 3.7E-1 | 3.1E-1 | 1.0E-9 | 1.0E-9 | 2.6E0 | 1.5E0 | 317 | 36 | 136 | 36 | 0.50 |
| Pa | pg/ml | 3.4E-1 | 3.7E-1 | 1.3E0 | 1.0E0 | 5.8E0 | 2.5E0 | 1.0E-9 | 1.0E-9 | 8.6E1 | 1.4E1 | 317 | 36 | 136 | 36 | 0.54 |
| Pb | pg/ml | 1.0E-9 | 1.0E-9 | 1.8E0 | 2.4E-1 | 2.7E1 | 8.9E-1 | 1.0E-9 | 1.0E-9 | 4.9E2 | 5.3E0 | 317 | 36 | 136 | 36 | 0.51 |
| Pc | pg/ml | 4.4E-2 | 2.6E-1 | 4.3E-1 | 3.4E-1 | 1.3E0 | 4.3E-1 | 1.0E-9 | 1.0E-9 | 1.6E1 | 1.8E0 | 317 | 36 | 136 | 36 | 0.55 |
| Pd | pg/ml | 1.8E0 | 2.0E0 | 3.8E0 | 3.6E0 | 8.2E0 | 5.4E0 | 1.0E-9 | 1.0E-9 | 9.4E1 | 2.4E1 | 317 | 36 | 136 | 36 | 0.52 |
| Pe | pg/ml | 1.8E1 | 2.1E1 | 8.9E1 | 1.0E2 | 3.5E2 | 1.9E2 | 1.0E-9 | 1.0E-9 | 4.7E3 | 7.3E2 | 317 | 36 | 136 | 36 | 0.56 |
| Pf | pg/ml | 1.2E0 | 2.1E0 | 6.2E0 | 1.2E1 | 2.6E1 | 3.2E1 | 1.0E-9 | 1.0E-9 | 3.3E2 | 1.8E2 | 317 | 36 | 136 | 36 | 0.59 |
| Pg | pg/ml | 3.2E0 | 4.6E0 | 4.0E1 | 1.1E2 | 2.1E2 | 5.7E2 | 1.0E-9 | 1.0E-9 | 3.2E3 | 3.4E3 | 317 | 36 | 136 | 36 | 0.51 |
| Ph | ng/ml | 1.4E-1 | 1.8E-1 | 2.7E-1 | 3.6E-1 | 3.5E-1 | 6.2E-1 | 1.0E-9 | 1.0E-9 | 2.2E0 | 2.9E0 | 110 | 23 | 86 | 23 | 0.51 |
| Pi | ng/ml | 1.9E-1 | 1.5E-1 | 2.8E-1 | 2.4E-1 | 4.4E-1 | 2.6E-1 | 1.0E-9 | 1.0E-9 | 3.2E0 | 8.6E-1 | 110 | 23 | 86 | 23 | 0.46 |
| Pj | ng/mL | 4.4E0 | 5.4E0 | 5.1E0 | 5.4E0 | 3.3E0 | 3.4E0 | 3.8E-2 | 3.8E-1 | 1.6E1 | 1.5E1 | 110 | 23 | 86 | 23 | 0.53 |
| Pk | ng/ml | 8.1E-3 | 9.9E-3 | 1.1E-2 | 1.4E-2 | 1.2E-2 | 1.2E-2 | 1.0E-9 | 1.0E-9 | 5.9E-2 | 4.6E-2 | 110 | 23 | 86 | 23 | 0.57 |
| aA | mg/dL | 8.0E-1 | 8.3E-1 | 9.2E-1 | 1.0E0 | 4.3E-1 | 6.1E-1 | 3.0E-1 | 2.0E-1 | 3.2E0 | 3.2E0 | 1242 | 45 | 226 | 45 | 0.52 |
| aC | mg/ml | 3.1E0 | 2.2E0 | 3.3E0 | 2.5E0 | 1.4E0 | 1.0E0 | 1.1E0 | 1.1E0 | 8.2E0 | 5.9E0 | 221 | 23 | 91 | 23 | 0.31 |
| aD | ug/mL | 2.9E0 | 3.2E0 | 4.1E0 | 4.4E0 | 3.2E0 | 3.5E0 | 8.5E-1 | 1.1E0 | 2.8E1 | 1.5E1 | 221 | 23 | 91 | 23 | 0.50 |
| aE | mg/mL | 5.8E-1 | 5.5E-1 | 5.8E-1 | 5.6E-1 | 1.5E-1 | 1.0E-1 | 2.1E-1 | 4.4E-1 | 1.1E0 | 7.8E-1 | 221 | 23 | 91 | 23 | 0.45 |
| aF | ng/mL | 2.1E0 | 2.2E0 | 4.4E0 | 5.0E0 | 7.0E0 | 6.8E0 | 4.3E-3 | 4.3E-3 | 5.0E1 | 2.9E1 | 221 | 23 | 91 | 23 | 0.52 |
| aG | mg/mL | 1.3E-1 | 1.5E-1 | 1.5E-1 | 1.7E-1 | 7.8E-2 | 8.0E-2 | 5.0E-2 | 5.6E-2 | 5.0E-1 | 3.5E-1 | 221 | 23 | 91 | 23 | 0.58 |
| aH | ug/mL | 6.8E1 | 7.5E1 | 7.8E1 | 7.9E1 | 3.5E1 | 3.9E1 | 1.5E1 | 2.3E1 | 2.7E2 | 2.0E2 | 221 | 23 | 91 | 23 | 0.51 |
| aI | ug/mL | 1.8E2 | 1.9E2 | 1.9E2 | 1.8E2 | 6.0E1 | 5.6E1 | 5.8E1 | 7.7E1 | 3.7E2 | 2.7E2 | 221 | 23 | 91 | 23 | 0.48 |
| aJ | ug/mL | 2.5E0 | 2.5E0 | 3.0E0 | 3.4E0 | 1.9E0 | 3.3E0 | 9.0E-1 | 1.0E0 | 1.2E1 | 1.6E1 | 221 | 23 | 91 | 23 | 0.52 |
| aK | ng/mL | 1.8E0 | 1.2E0 | 2.7E0 | 2.3E0 | 2.7E0 | 2.3E0 | 8.4E-2 | 1.0E-1 | 1.8E1 | 7.5E0 | 221 | 23 | 91 | 23 | 0.43 |
| aL | mg/mL | 8.1E-1 | 8.0E-1 | 8.3E-1 | 7.8E-1 | 2.4E-1 | 2.6E-1 | 2.2E-1 | 2.9E-1 | 1.6E0 | 1.4E0 | 221 | 23 | 91 | 23 | 0.45 |
| aM | U/mL | 1.9E1 | 2.3E1 | 3.7E1 | 3.4E1 | 1.1E2 | 3.3E1 | 4.2E-2 | 4.2E-2 | 1.6E3 | 1.2E2 | 221 | 23 | 91 | 23 | 0.57 |

Figure 23 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aN | U/mL | 1.0E1 | 1.5E1 | 1.8E1 | 1.9E1 | 2.1E1 | 2.2E1 | 2.5E-3 | 2.5E-3 | 1.3E2 | 9.7E1 | 221 | 23 | 91 | 23 | 0.53 |
| aO | pg/mL | 3.9E1 | 7.5E1 | 3.7E2 | 3.5E2 | 9.9E2 | 6.5E2 | 6.0E-2 | 6.0E-2 | 6.6E3 | 2.4E3 | 221 | 23 | 91 | 23 | 0.52 |
| aP | ng/mL | 1.7E0 | 1.7E0 | 1.9E0 | 2.1E0 | 1.1E0 | 1.4E0 | 5.4E-1 | 7.9E-1 | 6.6E0 | 6.4E0 | 221 | 23 | 91 | 23 | 0.52 |
| aQ | ng/mL | 3.2E-1 | 3.0E-1 | 5.0E-1 | 3.2E-1 | 5.2E-1 | 2.8E-1 | 1.9E-2 | 6.3E-2 | 4.0E0 | 1.3E0 | 221 | 23 | 91 | 23 | 0.39 |
| aR | ng/mL | 1.6E0 | 2.3E0 | 2.4E0 | 3.4E0 | 2.5E0 | 3.0E0 | 1.8E-1 | 5.9E-1 | 2.1E1 | 1.3E1 | 221 | 23 | 91 | 23 | 0.62 |
| aS | ng/mL | 2.4E-1 | 2.1E-1 | 7.8E-1 | 4.6E-1 | 2.5E0 | 5.0E-1 | 4.2E-3 | 7.2E-2 | 3.3E1 | 2.1E0 | 221 | 23 | 91 | 23 | 0.53 |
| aU | pg/mL | 8.8E1 | 5.5E1 | 1.4E2 | 1.0E2 | 1.6E2 | 1.3E2 | 7.4E0 | 6.5E0 | 1.3E3 | 5.8E2 | 221 | 23 | 91 | 23 | 0.38 |
| aV | ng/mL | 7.3E-1 | 5.8E-1 | 1.1E0 | 1.1E0 | 1.1E0 | 1.5E0 | 3.1E-2 | 9.2E-2 | 8.7E0 | 6.0E0 | 221 | 23 | 91 | 23 | 0.43 |
| aW | pg/mL | 1.7E1 | 2.2E1 | 2.0E1 | 2.1E1 | 2.6E1 | 9.1E0 | 7.2E-2 | 7.2E-2 | 2.4E2 | 3.3E1 | 221 | 23 | 91 | 23 | 0.60 |
| aX | ng/mL | 1.0E1 | 8.2E0 | 1.3E1 | 1.9E1 | 1.2E1 | 4.1E1 | 3.0E-1 | 2.1E0 | 6.7E1 | 2.1E2 | 221 | 23 | 91 | 23 | 0.49 |
| aY | pg/mL | 5.0E1 | 6.0E1 | 7.2E1 | 8.3E1 | 7.1E1 | 6.2E1 | 4.1E-1 | 4.1E-1 | 4.4E2 | 2.4E2 | 221 | 23 | 91 | 23 | 0.59 |
| aZ | pg/mL | 2.2E2 | 3.1E2 | 4.8E2 | 1.2E3 | 7.2E2 | 2.6E3 | 1.7E0 | 1.7E0 | 5.4E3 | 1.2E4 | 221 | 23 | 91 | 23 | 0.55 |
| bA | ng/mL | 8.0E0 | 1.9E1 | 2.6E1 | 5.2E1 | 6.2E1 | 8.0E1 | 3.0E-2 | 3.0E-2 | 7.1E2 | 3.2E2 | 221 | 23 | 91 | 23 | 0.64 |
| bB | pg/mL | 3.1E2 | 2.6E2 | 3.4E2 | 2.7E2 | 1.6E2 | 1.2E2 | 1.6E1 | 6.6E1 | 1.0E3 | 4.9E2 | 221 | 23 | 91 | 23 | 0.40 |
| bC | ng/mL | 3.5E2 | 3.7E2 | 5.1E2 | 7.5E2 | 5.3E2 | 1.2E3 | 2.7E1 | 4.5E1 | 4.0E3 | 4.7E3 | 221 | 23 | 91 | 23 | 0.52 |
| bE | mg/mL | 5.6E0 | 5.4E0 | 5.9E0 | 6.0E0 | 1.7E0 | 2.6E0 | 1.9E0 | 1.9E0 | 1.3E1 | 1.2E1 | 221 | 23 | 91 | 23 | 0.47 |
| bF | pg/mL | 2.0E1 | 3.5E1 | 8.6E1 | 6.4E2 | 4.4E2 | 2.3E3 | 5.0E-2 | 9.1E0 | 5.0E3 | 1.1E4 | 221 | 23 | 91 | 23 | 0.67 |
| bG | ng/mL | 1.8E0 | 1.3E0 | 3.0E0 | 2.0E0 | 3.7E0 | 1.8E0 | 2.2E-2 | 1.1E-1 | 2.6E1 | 7.3E0 | 221 | 23 | 91 | 23 | 0.42 |
| bH | pg/mL | 5.7E-1 | 5.7E-1 | 5.4E0 | 2.3E0 | 2.0E1 | 3.5E0 | 5.7E-1 | 5.7E-1 | 2.8E2 | 1.1E1 | 221 | 23 | 91 | 23 | 0.43 |
| bI | ng/mL | 4.0E-3 | 4.0E-3 | 6.8E-2 | 6.1E-2 | 1.7E-1 | 1.1E-1 | 4.0E-3 | 4.0E-3 | 1.3E0 | 3.7E-1 | 221 | 23 | 91 | 23 | 0.53 |
| bJ | mg/mL | 2.2E0 | 2.7E0 | 2.5E0 | 2.9E0 | 1.9E0 | 2.2E0 | 2.5E-4 | 2.1E-2 | 1.3E1 | 9.0E0 | 221 | 23 | 91 | 23 | 0.55 |
| bL | pg/mL | 4.1E0 | 6.2E0 | 7.8E0 | 9.5E0 | 9.3E0 | 1.0E1 | 4.6E-2 | 4.6E-2 | 4.9E1 | 3.3E1 | 221 | 23 | 91 | 23 | 0.56 |
| bM | mg/mL | 1.5E0 | 1.8E0 | 1.8E0 | 2.4E0 | 1.2E0 | 1.7E0 | 9.2E-3 | 3.3E-1 | 7.1E0 | 8.4E0 | 221 | 23 | 91 | 23 | 0.63 |
| bN | ng/mL | 3.2E1 | 4.3E1 | 1.1E2 | 9.0E1 | 2.6E2 | 1.5E2 | 9.7E-1 | 1.4E-1 | 1.9E3 | 5.7E2 | 221 | 23 | 91 | 23 | 0.52 |
| bO | ng/mL | 4.0E-2 | 4.0E-2 | 1.1E1 | 1.4E1 | 2.4E1 | 2.3E1 | 4.0E-2 | 4.0E-2 | 1.9E2 | 7.3E1 | 221 | 23 | 91 | 23 | 0.51 |
| bP | mg/mL | 5.6E-1 | 4.6E-1 | 7.9E-1 | 6.7E-1 | 6.6E-1 | 5.6E-1 | 8.2E-2 | 1.3E-1 | 3.8E0 | 2.2E0 | 221 | 23 | 91 | 23 | 0.45 |
| bQ | pg/mL | 1.4E1 | 1.7E1 | 2.4E1 | 4.7E1 | 3.5E1 | 8.6E1 | 1.5E-1 | 5.1E0 | 3.2E2 | 4.0E2 | 221 | 23 | 91 | 23 | 0.56 |
| bR | ng/mL | 1.2E-2 | 1.2E-2 | 1.4E-1 | 4.6E-2 | 2.8E-1 | 7.5E-2 | 1.2E-2 | 1.2E-2 | 3.4E0 | 2.3E-1 | 221 | 23 | 91 | 23 | 0.37 |
| bS | pg/mL | 9.4E-1 | 9.4E-1 | 8.1E0 | 3.3E0 | 2.9E1 | 1.1E1 | 9.4E-1 | 9.4E-1 | 3.4E2 | 5.5E1 | 221 | 23 | 91 | 23 | 0.45 |
| bU | ng/mL | 1.6E-1 | 1.1E-1 | 2.1E-1 | 1.1E-1 | 2.6E-1 | 1.0E-1 | 1.3E-2 | 1.3E-2 | 1.8E0 | 3.6E-1 | 221 | 23 | 91 | 23 | 0.39 |
| bV | pg/mL | 4.7E2 | 4.5E2 | 5.3E2 | 5.4E2 | 2.5E2 | 3.2E2 | 1.7E2 | 2.3E2 | 1.6E3 | 1.5E3 | 221 | 23 | 91 | 23 | 0.47 |
| bW | pg/mL | 3.5E2 | 3.0E2 | 4.7E2 | 1.3E3 | 4.2E2 | 4.1E3 | 1.1E2 | 9.9E1 | 3.4E3 | 2.0E4 | 221 | 23 | 91 | 23 | 0.47 |
| bX | ng/mL | 3.1E-3 | 2.5E-5 | 3.2E-3 | 9.9E-4 | 3.8E-3 | 2.1E-3 | 2.5E-5 | 2.5E-5 | 2.0E-2 | 6.3E-3 | 221 | 23 | 91 | 23 | 0.33 |
| bZ | pg/mL | 2.5E2 | 2.9E2 | 7.5E2 | 6.0E2 | 3.2E3 | 6.9E2 | 1.5E-1 | 5.2E1 | 4.4E4 | 2.2E3 | 221 | 23 | 91 | 23 | 0.55 |
| cA | pg/mL | 6.0E-1 | 6.0E-1 | 1.9E0 | 2.0E0 | 3.4E0 | 3.8E0 | 6.0E-1 | 6.0E-1 | 1.4E1 | 1.6E1 | 221 | 23 | 91 | 23 | 0.50 |
| cB | ng/mL | 6.0E-2 | 2.8E-2 | 9.0E-2 | 3.9E-2 | 1.0E-1 | 4.2E-2 | 1.7E-3 | 1.7E-3 | 5.4E-1 | 1.4E-1 | 221 | 23 | 91 | 23 | 0.33 |
| cC | pg/mL | 4.6E1 | 4.8E1 | 4.9E1 | 4.8E1 | 3.9E1 | 1.8E1 | 1.0E0 | 1.0E0 | 3.7E2 | 8.4E1 | 221 | 23 | 91 | 23 | 0.52 |
| cD | pg/mL | 6.1E0 | 3.4E0 | 1.3E1 | 1.2E1 | 4.0E1 | 2.7E1 | 3.3E-1 | 3.3E-1 | 4.8E2 | 1.3E2 | 221 | 23 | 91 | 23 | 0.42 |
| cE | pg/mL | 3.1E1 | 4.7E1 | 9.3E1 | 4.4E2 | 2.7E2 | 9.4E2 | 1.5E0 | 1.8E0 | 3.1E3 | 3.8E3 | 221 | 23 | 91 | 23 | 0.60 |
| cF | pg/mL | 1.3E1 | 5.3E-1 | 2.4E1 | 5.7E0 | 3.6E1 | 1.0E1 | 5.3E-1 | 5.3E-1 | 2.2E2 | 3.6E1 | 221 | 23 | 91 | 23 | 0.30 |
| cG | pg/mL | 4.2E1 | 3.8E1 | 6.4E1 | 1.1E2 | 8.8E1 | 1.4E2 | 1.1E1 | 1.8E1 | 1.1E3 | 5.6E2 | 221 | 23 | 91 | 23 | 0.51 |
| cH | uIU/mL | 2.9E0 | 1.7E0 | 6.0E0 | 3.7E0 | 8.9E0 | 7.7E0 | 8.6E-3 | 8.6E-3 | 8.7E1 | 3.8E1 | 221 | 23 | 91 | 23 | 0.36 |
| cI | ng/mL | 6.0E0 | 4.2E0 | 1.1E1 | 1.2E1 | 1.3E1 | 2.2E1 | 1.0E-3 | 3.2E-2 | 9.4E1 | 1.0E2 | 221 | 23 | 91 | 23 | 0.41 |
| cJ | ug/mL | 7.2E1 | 6.5E1 | 1.2E2 | 1.0E2 | 1.5E2 | 1.2E2 | 4.0E0 | 1.2E1 | 9.6E2 | 5.5E2 | 221 | 23 | 91 | 23 | 0.48 |
| cK | ng/mL | 3.8E-3 | 3.8E-3 | 7.5E-2 | 6.8E-3 | 2.2E-1 | 1.4E-2 | 3.8E-3 | 3.8E-3 | 1.7E0 | 7.3E-2 | 221 | 23 | 91 | 23 | 0.42 |
| cL | pg/mL | 1.9E2 | 2.2E2 | 2.7E2 | 5.9E2 | 5.1E2 | 9.8E2 | 2.5E1 | 3.6E1 | 7.1E3 | 4.2E3 | 221 | 23 | 91 | 23 | 0.58 |
| cM | pg/mL | 2.9E2 | 2.7E2 | 3.2E2 | 3.0E2 | 1.8E2 | 2.1E2 | 3.7E1 | 4.7E1 | 1.2E3 | 8.4E2 | 221 | 23 | 91 | 23 | 0.44 |
| cN | pg/mL | 1.2E2 | 1.1E2 | 1.2E2 | 1.4E2 | 4.4E1 | 7.0E1 | 3.8E1 | 5.7E1 | 2.7E2 | 3.5E2 | 221 | 23 | 91 | 23 | 0.54 |
| cO | pg/mL | 2.3E2 | 2.1E2 | 2.8E2 | 2.7E2 | 2.0E2 | 2.0E2 | 5.4E1 | 1.2E2 | 1.7E3 | 1.1E3 | 221 | 23 | 91 | 23 | 0.48 |
| cP | ng/mL | 2.4E3 | 2.9E3 | 2.5E3 | 3.0E3 | 8.9E2 | 8.8E2 | 6.2E2 | 1.4E3 | 5.7E3 | 5.1E3 | 221 | 23 | 91 | 23 | 0.67 |
| cQ | ng/mL | 4.0E-2 | 3.9E-2 | 1.1E-1 | 1.9E-1 | 1.8E-1 | 4.7E-1 | 2.0E-3 | 2.0E-3 | 1.2E0 | 2.2E0 | 221 | 23 | 91 | 23 | 0.53 |
| cR | ng/mL | 2.8E2 | 3.0E2 | 4.3E2 | 5.8E2 | 4.6E2 | 9.9E2 | 2.3E1 | 7.8E1 | 3.8E3 | 4.8E3 | 221 | 23 | 91 | 23 | 0.53 |
| cS | ng/mL | 2.4E2 | 3.6E2 | 3.9E2 | 4.1E2 | 4.2E2 | 2.5E2 | 5.3E1 | 5.0E1 | 2.7E3 | 9.0E2 | 221 | 23 | 91 | 23 | 0.59 |
| cT | ng/mL | 2.8E1 | 6.2E1 | 7.4E1 | 1.7E2 | 1.5E2 | 3.2E2 | 4.6E0 | 8.4E0 | 1.7E3 | 1.3E3 | 221 | 23 | 91 | 23 | 0.62 |
| cU | ng/mL | 5.5E1 | 4.8E1 | 7.4E1 | 6.0E1 | 7.2E1 | 4.2E1 | 1.0E1 | 9.0E0 | 7.7E2 | 1.5E2 | 221 | 23 | 91 | 23 | 0.45 |
| cV | ng/mL | 1.7E-1 | 1.8E-1 | 4.9E-1 | 6.2E-1 | 3.2E0 | 2.0E0 | 3.4E-4 | 3.0E-2 | 4.7E1 | 9.7E0 | 221 | 23 | 91 | 23 | 0.48 |
| cW | mIU/mL | 4.6E-2 | 7.7E-2 | 2.2E-1 | 8.5E-2 | 1.0E0 | 5.5E-2 | 3.7E-4 | 2.1E-2 | 9.7E0 | 2.1E-1 | 221 | 23 | 91 | 23 | 0.65 |

Figure 23 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cX | ng/mL | 1.1E-1 | 2.7E-1 | 1.8E0 | 2.4E0 | 5.4E0 | 6.9E0 | 2.3E-4 | 2.3E-4 | 2.8E1 | 2.8E1 | 221 | 23 | 91 | 23 | 0.50 |
| cY | ng/mL | 1.0E1 | 6.1E0 | 1.4E1 | 1.1E1 | 1.4E1 | 1.3E1 | 4.4E-1 | 1.3E0 | 8.3E1 | 5.3E1 | 221 | 23 | 91 | 23 | 0.37 |
| cZ | ug/mL | 1.4E1 | 1.7E1 | 1.5E1 | 1.6E1 | 5.8E0 | 7.4E0 | 5.3E0 | 6.6E0 | 3.9E1 | 4.2E1 | 221 | 23 | 91 | 23 | 0.54 |
| dA | pg/mL | 3.3E2 | 2.9E2 | 3.6E2 | 3.5E2 | 1.6E2 | 1.7E2 | 9.0E1 | 1.1E2 | 1.3E3 | 9.3E2 | 221 | 23 | 91 | 23 | 0.45 |
| dB | ug/mL | 1.7E1 | 2.1E1 | 1.9E1 | 2.1E1 | 2.1E1 | 8.5E1 | 1.9E0 | 2.8E0 | 2.5E2 | 4.0E1 | 221 | 23 | 91 | 23 | 0.66 |
| dC | nmol/L | 3.4E1 | 3.8E1 | 4.1E1 | 4.0E1 | 2.0E1 | 1.3E1 | 9.1E0 | 2.3E1 | 1.4E2 | 7.3E1 | 221 | 23 | 91 | 23 | 0.54 |
| dD | ng/mL | 3.7E1 | 3.2E1 | 3.8E1 | 3.4E1 | 1.0E1 | 1.0E1 | 1.3E1 | 1.6E1 | 7.6E1 | 5.1E1 | 221 | 23 | 91 | 23 | 0.40 |
| dE | ng/mL | 4.8E-1 | 4.2E-1 | 6.7E-1 | 4.2E-1 | 8.3E-1 | 3.9E-1 | 8.4E-3 | 8.4E-3 | 7.2E0 | 1.4E0 | 221 | 23 | 91 | 23 | 0.42 |
| dF | ng/mL | 2.1E2 | 2.4E2 | 2.6E2 | 3.2E2 | 1.8E2 | 2.6E2 | 7.5E1 | 8.7E1 | 1.2E3 | 1.2E3 | 221 | 23 | 91 | 23 | 0.56 |
| dG | ng/mL | 1.1E1 | 1.1E1 | 1.3E1 | 1.6E1 | 8.4E0 | 1.5E1 | 3.1E0 | 6.0E0 | 6.4E1 | 7.6E1 | 221 | 23 | 91 | 23 | 0.53 |
| dH | pg/mL | 7.5E0 | 5.8E0 | 1.2E1 | 1.0E1 | 2.4E1 | 1.1E1 | 4.0E-2 | 4.0E-2 | 3.1E2 | 4.4E1 | 221 | 23 | 91 | 23 | 0.47 |
| dI | pg/mL | 4.6E-1 | 4.6E-1 | 1.9E0 | 1.5E0 | 4.4E0 | 1.8E0 | 4.6E-1 | 4.6E-1 | 3.4E1 | 6.0E0 | 221 | 23 | 91 | 23 | 0.54 |
| dJ | ng/mL | 1.9E0 | 2.5E0 | 2.1E0 | 2.6E0 | 1.1E0 | 1.1E0 | 3.2E-2 | 1.1E0 | 5.9E0 | 4.9E0 | 221 | 23 | 91 | 23 | 0.63 |
| dK | uIU/mL | 2.0E0 | 1.7E0 | 2.7E0 | 2.7E0 | 2.9E0 | 3.8E0 | 2.8E-4 | 9.4E-2 | 1.6E1 | 1.5E1 | 221 | 23 | 91 | 23 | 0.46 |
| dL | ng/mL | 8.8E2 | 8.3E2 | 1.0E3 | 9.6E2 | 4.8E2 | 4.5E2 | 3.4E2 | 4.1E2 | 3.4E3 | 2.2E3 | 221 | 23 | 91 | 23 | 0.47 |
| dM | pg/mL | 9.7E2 | 8.5E2 | 1.2E3 | 1.2E3 | 1.1E3 | 8.9E2 | 4.4E2 | 3.9E2 | 1.2E4 | 3.6E3 | 221 | 23 | 91 | 23 | 0.44 |
| dN | ug/mL | 9.0E1 | 1.2E2 | 9.7E1 | 1.1E2 | 3.4E1 | 3.7E1 | 2.5E1 | 5.9E1 | 2.4E2 | 2.0E2 | 221 | 23 | 91 | 23 | 0.60 |
| dR | pg/ml | 1.6E3 | 1.6E3 | 2.5E3 | 2.1E3 | 2.6E3 | 2.1E3 | 1.9E2 | 1.4E2 | 1.5E4 | 8.6E3 | 131 | 21 | 88 | 21 | 0.45 |
| eF | ng/ml | 4.0E0 | 4.6E0 | 4.6E0 | 5.3E0 | 2.6E0 | 2.4E0 | 1.5E0 | 2.9E0 | 1.8E1 | 1.2E1 | 138 | 21 | 88 | 21 | 0.63 |
| eC | pg/ml | 3.1E2 | 3.0E2 | 3.8E2 | 3.1E2 | 2.5E2 | 1.5E2 | 4.5E1 | 1.3E2 | 1.4E3 | 7.1E2 | 100 | 21 | 86 | 21 | 0.43 |
| eD | pg/ml | 2.3E2 | 1.8E2 | 7.7E2 | 3.3E2 | 1.4E3 | 3.3E2 | 5.2E-1 | 5.9E1 | 6.8E3 | 1.1E3 | 77 | 21 | 64 | 21 | 0.46 |
| eT | ng/ml | 2.7E2 | 3.7E2 | 5.6E2 | 7.9E2 | 6.1E2 | 9.1E2 | 1.0E2 | 1.7E2 | 2.5E3 | 2.6E3 | 51 | 9 | 49 | 9 | 0.63 |
| eZ | ng/ml | 6.1E1 | 4.0E1 | 6.4E1 | 4.9E1 | 2.6E1 | 2.3E1 | 2.3E1 | 3.6E1 | 1.2E2 | 1.1E2 | 51 | 9 | 49 | 9 | 0.31 |
| fN | ng/ml | 2.1E-1 | 2.1E-1 | 2.7E0 | 1.4E0 | 5.8E0 | 2.7E0 | 2.1E-1 | 2.1E-1 | 3.2E1 | 8.1E0 | 51 | 9 | 49 | 9 | 0.44 |
| fP | ng/ml | 2.3E2 | 3.9E2 | 2.7E2 | 3.8E2 | 1.7E2 | 1.7E2 | 8.4E0 | 8.2E1 | 1.0E3 | 7.4E2 | 127 | 22 | 88 | 22 | 0.70 |
| fR | ng/ml | 1.3E5 | 1.2E5 | 1.6E5 | 2.6E5 | 1.1E5 | 2.4E5 | 3.1E4 | 5.5E4 | 6.1E5 | 7.2E5 | 162 | 9 | 44 | 9 | 0.58 |
| fY | ng/ml | 2.5E2 | 3.2E2 | 2.4E2 | 2.8E2 | 8.9E1 | 1.0E2 | 6.5E1 | 1.2E2 | 4.2E2 | 4.3E2 | 51 | 9 | 49 | 9 | 0.63 |
| gL | pg/ml | 6.1E4 | 7.2E4 | 6.8E4 | 7.4E4 | 2.9E4 | 3.0E4 | 2.2E4 | 3.3E4 | 1.8E5 | 1.4E5 | 131 | 21 | 88 | 21 | 0.57 |
| gP | U/ml | 2.5E2 | 3.0E2 | 2.6E2 | 3.1E2 | 7.9E1 | 1.5E2 | 8.5E1 | 8.4E1 | 5.3E2 | 8.5E2 | 137 | 21 | 88 | 21 | 0.61 |
| gW | ng/ml | 7.0E2 | 5.4E2 | 1.5E3 | 7.9E2 | 1.9E3 | 8.3E2 | 3.7E1 | 2.3E0 | 9.5E3 | 3.1E3 | 109 | 20 | 79 | 20 | 0.41 |
| tF | pg/mL | 2.6E3 | 1.0E3 | 2.2E4 | 4.0E3 | 5.6E4 | 7.4E3 | 1.2E1 | 1.8E1 | 3.2E5 | 2.9E4 | 100 | 21 | 86 | 21 | 0.38 |
| hA | ng/ml | 2.3E0 | 1.6E0 | 7.4E0 | 7.6E0 | 2.4E1 | 1.4E1 | 1.7E-2 | 1.7E-2 | 1.6E2 | 5.7E1 | 77 | 21 | 64 | 21 | 0.44 |
| nM | pg/ml | 1.0E-9 | 1.0E-9 | 1.9E2 | 1.0E-9 | 1.4E3 | 0.0E0 | 1.0E-9 | 1.0E-9 | 1.0E4 | 1.0E-9 | 54 | 13 | 47 | 13 | 0.48 |
| nN | pg/ml | 1.1E3 | 8.5E2 | 2.1E3 | 1.6E3 | 2.7E3 | 2.0E3 | 1.1E2 | 1.6E2 | 1.7E4 | 7.1E3 | 54 | 13 | 47 | 13 | 0.44 |
| nO | pg/ml | 3.1E1 | 2.0E1 | 4.5E1 | 2.6E1 | 4.7E1 | 1.9E1 | 5.5E0 | 6.5E0 | 2.4E2 | 6.6E1 | 54 | 13 | 47 | 13 | 0.34 |
| nR | pg/ml | 1.6E1 | 2.2E1 | 4.5E1 | 6.6E1 | 7.3E1 | 7.7E1 | 1.0E-9 | 1.8E0 | 3.6E2 | 2.2E2 | 54 | 13 | 47 | 13 | 0.58 |
| nT | pg/ml | 8.5E1 | 4.0E1 | 3.5E2 | 6.2E1 | 1.2E3 | 6.8E1 | 1.0E-9 | 4.8E0 | 6.6E3 | 2.3E2 | 54 | 13 | 47 | 13 | 0.38 |
| nU | pg/ml | 2.9E1 | 6.0E1 | 5.1E2 | 6.7E1 | 2.2E3 | 7.0E1 | 1.0E-9 | 1.0E-9 | 1.3E4 | 2.6E2 | 54 | 13 | 47 | 13 | 0.62 |
| lW | pg/ml | 1.0E-9 | 1.0E-9 | 1.6E1 | 1.9E1 | 5.5E1 | 4.7E1 | 1.0E-9 | 1.0E-9 | 3.9E2 | 1.6E2 | 54 | 13 | 47 | 13 | 0.47 |
| lX | pg/ml | 9.5E2 | 1.1E3 | 9.2E2 | 1.2E3 | 4.4E2 | 5.5E2 | 2.3E2 | 3.3E2 | 1.9E3 | 2.2E3 | 54 | 13 | 47 | 13 | 0.64 |
| lY | pg/ml | 1.7E1 | 2.2E1 | 2.2E1 | 2.3E1 | 2.5E1 | 9.3E0 | 1.0E-9 | 4.2E0 | 1.4E2 | 3.8E1 | 54 | 13 | 47 | 13 | 0.65 |
| mE | pg/ml | 1.0E-9 | 1.0E-9 | 3.3E0 | 3.1E0 | 1.0E1 | 7.5E0 | 1.0E-9 | 1.0E-9 | 5.8E1 | 2.8E1 | 54 | 13 | 47 | 13 | 0.58 |
| mF | pg/ml | 1.0E-9 | 5.7E-1 | 1.4E0 | 1.5E0 | 3.0E0 | 2.3E0 | 1.0E-9 | 1.0E-9 | 1.5E1 | 6.5E0 | 54 | 13 | 47 | 13 | 0.62 |
| mH | pg/ml | 3.6E0 | 3.7E0 | 4.9E0 | 5.4E0 | 5.0E0 | 4.6E0 | 2.3E-1 | 2.0E0 | 3.2E1 | 1.8E1 | 54 | 13 | 47 | 13 | 0.57 |
| ml | pg/ml | 1.0E-9 | 1.0E-9 | 1.2E1 | 9.7E0 | 3.1E1 | 1.6E1 | 1.0E-9 | 1.0E-9 | 1.6E2 | 4.7E1 | 54 | 13 | 47 | 13 | 0.52 |
| mM | pg/ml | 3.0E1 | 3.1E1 | 5.2E1 | 1.0E2 | 5.9E1 | 1.8E2 | 1.0E-9 | 1.0E-9 | 2.3E2 | 6.5E2 | 54 | 13 | 47 | 13 | 0.56 |
| mP | pg/ml | 1.5E1 | 1.8E1 | 2.0E1 | 2.0E1 | 2.2E1 | 1.8E1 | 1.0E-9 | 1.0E-9 | 1.5E2 | 7.7E1 | 53 | 13 | 46 | 13 | 0.55 |
| mS | pg/ml | 1.8E3 | 2.0E3 | 2.2E3 | 2.2E3 | 2.2E3 | 6.0E2 | 1.0E-9 | 1.0E-9 | 1.3E4 | 3.2E3 | 54 | 13 | 47 | 13 | 0.61 |
| mT | pg/ml | 5.0E1 | 7.9E1 | 1.2E2 | 1.8E2 | 2.2E2 | 2.0E2 | 1.0E1 | 1.7E1 | 1.4E3 | 6.2E2 | 53 | 13 | 46 | 13 | 0.58 |
| mU | pg/ml | 2.5E0 | 2.0E0 | 4.2E0 | 4.4E0 | 8.5E0 | 5.8E0 | 1.0E-9 | 8.2E-1 | 5.8E1 | 2.2E1 | 53 | 13 | 46 | 13 | 0.51 |
| mW | pg/ml | 2.5E3 | 2.6E3 | 2.7E3 | 3.1E3 | 1.7E3 | 2.2E3 | 4.3E2 | 8.9E2 | 1.0E4 | 9.8E3 | 53 | 13 | 46 | 13 | 0.55 |
| mY | pg/ml | 4.7E2 | 8.9E2 | 1.0E3 | 1.2E3 | 1.8E3 | 6.7E2 | 1.0E-9 | 6.8E2 | 1.1E4 | 2.6E3 | 54 | 13 | 47 | 13 | 0.77 |
| mZ | pg/ml | 2.6E2 | 1.1E2 | 5.0E2 | 2.1E2 | 6.0E2 | 2.0E2 | 2.1E1 | 2.1E0 | 3.1E3 | 6.9E2 | 53 | 13 | 46 | 13 | 0.30 |
| nA | pg/ml | 1.3E0 | 5.0E0 | 1.6E2 | 9.4E0 | 6.6E1 | 1.4E1 | 1.0E-9 | 1.0E-9 | 4.4E2 | 5.4E1 | 53 | 13 | 46 | 13 | 0.67 |
| nB | pg/ml | 2.6E2 | 4.3E2 | 3.1E2 | 4.4E2 | 1.6E2 | 1.7E2 | 3.0E1 | 1.5E2 | 7.2E2 | 7.8E2 | 54 | 13 | 47 | 13 | 0.72 |
| nC | pg/ml | 1.0E-9 | 8.3E1 | 8.7E3 | 6.7E2 | 5.0E4 | 2.0E3 | 1.0E-9 | 1.0E-9 | 3.7E5 | 7.2E3 | 54 | 13 | 47 | 13 | 0.54 |
| nD | pg/ml | 7.2E0 | 1.2E1 | 7.0E1 | 1.3E1 | 3.1E2 | 8.5E0 | 1.0E-9 | 1.0E-9 | 1.7E3 | 2.6E1 | 53 | 13 | 46 | 13 | 0.63 |

Figure 23 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nF | pg/ml | 1.0E-9 | 1.0E-9 | 9.5E0 | 8.5E-1 | 4.0E1 | 3.1E0 | 1.0E-9 | 1.0E-9 | 2.4E2 | 1.1E1 | 54 | 13 | 47 | 13 | 0.48 |
| nH | pg/ml | 3.0E-2 | 5.4E0 | 2.1E2 | 1.4E1 | 1.4E3 | 3.1E1 | 1.0E-9 | 1.0E-9 | 1.0E4 | 1.2E2 | 53 | 13 | 46 | 13 | 0.68 |
| nI | pg/ml | 4.6E1 | 3.0E1 | 2.9E2 | 4.8E1 | 1.3E3 | 5.5E1 | 1.0E-9 | 1.0E-9 | 9.2E3 | 1.7E2 | 54 | 13 | 47 | 13 | 0.45 |
| nJ | pg/ml | 1.7E-1 | 1.1E0 | 9.9E1 | 1.5E0 | 7.0E2 | 1.6E0 | 1.0E-9 | 1.0E-9 | 5.2E3 | 6.3E0 | 54 | 13 | 47 | 13 | 0.69 |
| nK | pg/ml | 1.0E-9 | 3.0E1 | 1.2E2 | 2.7E1 | 5.4E2 | 3.1E1 | 1.0E-9 | 1.0E-9 | 3.2E3 | 9.6E1 | 53 | 13 | 46 | 13 | 0.65 |
| nL | pg/ml | 1.0E-9 | 2.5E0 | 9.3E2 | 2.0E1 | 6.1E3 | 3.9E1 | 1.0E-9 | 1.0E-9 | 4.5E4 | 1.4E2 | 54 | 13 | 47 | 13 | 0.56 |
| hL | pg/ml | 1.7E4 | 1.6E4 | 2.3E4 | 2.3E4 | 2.2E4 | 2.0E4 | 2.6E3 | 5.4E3 | 1.4E5 | 7.0E4 | 51 | 9 | 49 | 9 | 0.49 |
| hO | pg/ml | 1.6E4 | 1.5E4 | 1.7E4 | 1.5E4 | 3.2E3 | 1.8E3 | 1.1E4 | 1.3E4 | 2.8E4 | 1.8E4 | 51 | 9 | 49 | 9 | 0.42 |
| hP | ng/ml | 4.4E5 | 4.4E5 | 3.7E5 | 5.9E5 | 1.7E5 | 5.9E5 | 2.8E4 | 3.4E4 | 9.0E5 | 2.0E6 | 51 | 9 | 49 | 9 | 0.59 |
| wJ | pg/ml | 1.5E5 | 1.8E5 | 1.6E5 | 1.9E5 | 8.7E4 | 1.2E5 | 2.8E4 | 3.3E4 | 4.0E5 | 4.0E5 | 48 | 9 | 44 | 9 | 0.56 |
| wK | pg/ml | 3.4E4 | 5.4E4 | 4.3E4 | 9.9E4 | 2.7E4 | 1.6E5 | 5.2E3 | 8.1E3 | 1.2E5 | 5.0E5 | 48 | 9 | 44 | 9 | 0.60 |
| wL | pg/ml | 6.5E0 | 3.9E0 | 7.0E1 | 8.0E0 | 1.5E2 | 9.7E0 | 1.0E-9 | 1.0E-9 | 8.4E2 | 2.8E1 | 48 | 9 | 44 | 9 | 0.38 |
| wP | pg/ml | 2.8E4 | 4.3E4 | 4.3E4 | 4.9E4 | 4.3E4 | 4.0E4 | 2.8E3 | 6.3E3 | 1.6E5 | 1.4E5 | 48 | 9 | 44 | 9 | 0.59 |
| wQ | pg/ml | 3.4E1 | 6.7E1 | 6.0E1 | 7.3E1 | 7.7E1 | 6.1E1 | 1.0E-9 | 3.6E0 | 3.7E2 | 1.7E2 | 48 | 9 | 44 | 9 | 0.62 |
| hR | pg/ml | 2.7E4 | 2.2E4 | 3.0E4 | 2.5E4 | 1.1E4 | 1.0E4 | 1.8E3 | 1.1E1 | 5.8E4 | 4.3E4 | 75 | 19 | 62 | 19 | 0.37 |
| hV | pg/ml | 4.4E2 | 4.5E2 | 4.7E2 | 4.7E2 | 2.4E2 | 1.8E2 | 1.3E2 | 2.2E2 | 1.5E3 | 8.1E2 | 75 | 19 | 62 | 19 | 0.53 |
| hW | pg/ml | 1.6E3 | 1.8E3 | 2.1E3 | 2.2E3 | 1.6E3 | 1.6E3 | 5.7E2 | 1.1E3 | 1.0E4 | 7.7E3 | 75 | 19 | 62 | 19 | 0.54 |
| hX | pg/ml | 9.6E2 | 1.1E3 | 1.2E3 | 1.1E3 | 1.1E3 | 4.2E2 | 4.8E2 | 5.2E2 | 8.6E3 | 2.2E3 | 75 | 19 | 62 | 19 | 0.56 |
| iA | pg/ml | 1.7E2 | 1.4E2 | 4.2E2 | 2.0E2 | 9.2E2 | 1.9E2 | 1.8E1 | 3.0E1 | 7.1E3 | 9.5E2 | 100 | 21 | 86 | 21 | 0.46 |
| iB | ng/ml | 5.4E0 | 4.3E0 | 6.7E0 | 6.0E0 | 4.7E0 | 5.2E0 | 2.5E-1 | 3.3E-2 | 2.0E1 | 2.1E1 | 77 | 21 | 64 | 21 | 0.42 |
| iC | U/ml | 2.4E-1 | 1.8E-1 | 5.0E-1 | 3.0E0 | 8.7E-1 | 1.2E1 | 1.0E-9 | 1.0E-9 | 6.4E0 | 5.5E1 | 77 | 21 | 64 | 21 | 0.54 |
| tQ | pg/ml | 1.1E3 | 1.1E3 | 1.2E3 | 1.3E3 | 5.5E2 | 7.1E2 | 2.8E2 | 5.0E2 | 2.5E3 | 2.5E3 | 46 | 8 | 43 | 8 | 0.52 |
| tT | pg/ml | 1.5E1 | 2.1E1 | 1.7E1 | 1.8E1 | 7.4E0 | 9.8E0 | 7.4E0 | 5.4E0 | 3.9E1 | 3.3E1 | 46 | 8 | 43 | 8 | 0.56 |
| tS | pg/ml | 1.0E0 | 6.1E-1 | 1.1E0 | 9.8E-1 | 8.6E-1 | 1.1E0 | 1.0E-9 | 1.0E-9 | 4.0E0 | 3.2E0 | 46 | 8 | 43 | 8 | 0.46 |
| tX | pg/ml | 8.1E-1 | 5.2E-1 | 9.5E-1 | 7.4E-1 | 7.0E-1 | 6.1E-1 | 2.5E-2 | 1.6E-1 | 3.3E0 | 1.9E0 | 46 | 8 | 43 | 8 | 0.40 |
| tO | pg/ml | 4.0E0 | 4.4E0 | 4.4E0 | 4.7E0 | 2.5E0 | 2.9E0 | 1.0E-9 | 1.7E0 | 1.1E1 | 1.1E1 | 46 | 8 | 43 | 8 | 0.52 |
| tR | pg/ml | 2.1E-1 | 1.9E-1 | 2.5E-1 | 2.4E-1 | 2.1E-1 | 2.1E-1 | 1.0E-9 | 5.5E-2 | 9.1E-1 | 7.1E-1 | 46 | 8 | 43 | 8 | 0.47 |
| tU | pg/ml | 9.0E0 | 8.8E0 | 1.1E1 | 8.6E0 | 6.9E0 | 4.2E0 | 1.6E0 | 3.0E0 | 3.1E1 | 1.7E1 | 46 | 9 | 43 | 9 | 0.43 |
| tN | pg/ml | 1.7E1 | 1.5E1 | 1.9E1 | 1.6E1 | 1.0E1 | 9.2E0 | 1.0E-9 | 1.0E-9 | 5.4E1 | 2.8E1 | 46 | 9 | 43 | 9 | 0.43 |
| tV | ng/ml | 3.7E2 | 8.1E2 | 4.8E2 | 7.5E2 | 4.0E2 | 5.1E2 | 6.6E1 | 1.4E2 | 2.6E3 | 1.8E3 | 48 | 9 | 44 | 9 | 0.67 |
| iH | ng/ml | 1.5E5 | 1.9E5 | 1.5E5 | 1.9E5 | 4.3E4 | 5.0E4 | 7.1E4 | 5.1E4 | 2.4E5 | 2.7E5 | 100 | 21 | 86 | 21 | 0.75 |
| iJ | ng/ml | 5.1E4 | 5.1E4 | 5.3E4 | 5.9E4 | 2.0E4 | 3.3E4 | 8.7E3 | 8.6E3 | 1.2E5 | 1.5E5 | 100 | 21 | 86 | 21 | 0.54 |
| hB | ng/ml | 4.3E-1 | 4.8E-1 | 5.2E-1 | 6.6E-1 | 3.5E-1 | 5.5E-1 | 1.2E-1 | 2.5E-1 | 1.9E0 | 2.4E0 | 100 | 21 | 86 | 21 | 0.58 |
| hC | ng/ml | 3.6E3 | 4.2E3 | 5.9E3 | 8.2E3 | 7.5E3 | 1.0E4 | 1.0E-9 | 3.3E2 | 5.5E4 | 4.3E4 | 100 | 21 | 86 | 21 | 0.57 |
| hF | ng/ml | 1.0E-9 | 1.0E-9 | 4.9E1 | 1.0E-9 | 4.1E2 | 0.0E0 | 1.0E-9 | 1.0E-9 | 4.0E3 | 1.0E-9 | 100 | 21 | 86 | 21 | 0.49 |
| hG | pg/ml | 7.4E3 | 6.9E3 | 7.8E3 | 8.1E3 | 2.9E3 | 3.1E3 | 1.7E3 | 4.7E3 | 1.8E4 | 1.8E4 | 100 | 21 | 86 | 21 | 0.52 |
| iO | ng/ml | 4.1E5 | 4.0E5 | 4.2E5 | 3.9E5 | 2.0E5 | 1.8E5 | 1.1E5 | 6.4E4 | 1.1E6 | 8.6E5 | 100 | 21 | 86 | 21 | 0.45 |
| iP | ng/ml | 6.1E4 | 4.6E4 | 5.5E4 | 5.6E4 | 3.1E4 | 3.6E4 | 5.8E3 | 1.3E4 | 2.5E5 | 1.9E5 | 100 | 21 | 86 | 21 | 0.47 |
| iZ | ng/ml | 1.7E3 | 1.7E3 | 1.8E3 | 1.8E3 | 6.8E2 | 8.8E2 | 4.7E2 | 6.5E2 | 4.5E3 | 4.5E3 | 100 | 21 | 86 | 21 | 0.48 |
| yH | pg/ml | 1.2E3 | 7.5E2 | 2.0E3 | 9.8E2 | 3.0E3 | 5.8E2 | 1.0E-9 | 1.6E2 | 1.5E4 | 1.9E3 | 48 | 9 | 44 | 9 | 0.41 |
| yK | U/ml | 1.8E1 | 2.3E1 | 4.9E1 | 4.0E1 | 8.5E1 | 3.9E1 | 1.0E-9 | 1.0E-9 | 3.8E2 | 1.0E2 | 48 | 9 | 44 | 9 | 0.53 |
| yJ | pg/ml | 3.6E4 | 3.2E4 | 4.7E4 | 4.4E4 | 3.5E4 | 4.3E4 | 1.7E3 | 7.1E3 | 1.6E5 | 1.4E5 | 48 | 9 | 44 | 9 | 0.44 |
| yD | ng/ml | 1.5E-2 | 1.7E-2 | 1.5E-2 | 1.6E-2 | 5.8E-3 | 8.3E-3 | 1.0E-9 | 5.4E-3 | 2.9E-2 | 3.2E-2 | 48 | 9 | 44 | 9 | 0.53 |
| wB | pg/ml | 8.8E3 | 8.3E3 | 9.8E3 | 8.7E3 | 7.3E3 | 5.4E3 | 1.7E3 | 2.7E3 | 4.1E4 | 2.1E4 | 48 | 9 | 44 | 9 | 0.47 |
| pY | pg/ml | 6.0E0 | 7.1E0 | 1.1E1 | 7.5E0 | 2.7E1 | 2.9E0 | 2.1E0 | 3.4E0 | 2.0E2 | 1.2E1 | 51 | 9 | 49 | 9 | 0.60 |
| rC | pg/ml | 1.9E3 | 1.4E3 | 2.6E3 | 1.9E3 | 2.8E3 | 1.4E3 | 1.0E2 | 3.2E2 | 1.5E4 | 4.9E3 | 72 | 18 | 59 | 18 | 0.43 |
| rB | pg/ml | 2.2E1 | 3.0E1 | 5.5E1 | 3.4E1 | 1.4E2 | 3.0E1 | 1.0E-9 | 1.0E-9 | 9.5E2 | 1.3E2 | 72 | 18 | 59 | 18 | 0.59 |
| zG | 2.5ng/ml | 2.0E-1 | 2.5E-1 | 4.5E-1 | 7.8E-1 | 7.8E-1 | 1.5E0 | 1.0E-9 | 5.1E-2 | 4.4E0 | 4.8E0 | 48 | 9 | 44 | 9 | 0.57 |
| zH | 2.3mU/ml | 1.1E-1 | 9.9E-2 | 1.2E-1 | 1.0E-1 | 6.9E-2 | 3.5E-2 | 1.0E-2 | 4.0E-2 | 4.4E-1 | 1.6E-1 | 48 | 9 | 44 | 9 | 0.48 |
| zI | 2.6ng/ml | 1.8E0 | 2.6E0 | 3.2E0 | 4.8E0 | 3.3E0 | 5.0E0 | 6.1E-1 | 1.5E0 | 1.5E1 | 1.4E1 | 48 | 9 | 44 | 9 | 0.66 |
| qA | ng/ml | 1.0E7 | 7.4E6 | 1.1E7 | 1.6E7 | 7.3E6 | 1.2E7 | 3.7E6 | 6.9E6 | 3.7E7 | 3.9E7 | 51 | 9 | 49 | 9 | 0.57 |
| qB | ng/ml | 6.3E5 | 4.8E5 | 8.3E5 | 9.8E5 | 5.8E5 | 9.6E5 | 2.1E5 | 2.7E5 | 2.9E6 | 2.9E6 | 51 | 9 | 49 | 9 | 0.46 |
| qC | ng/ml | 4.8E5 | 3.7E5 | 8.2E5 | 3.5E5 | 1.2E6 | 2.8E5 | 2.0E4 | 2.5E4 | 7.1E6 | 7.9E5 | 51 | 9 | 49 | 9 | 0.37 |
| qD | ng/ml | 1.6E7 | 1.3E7 | 1.9E7 | 1.6E7 | 9.4E6 | 1.1E7 | 4.9E6 | 6.2E6 | 5.2E7 | 4.2E7 | 51 | 9 | 49 | 9 | 0.36 |
| jD | ng/ml | 2.2E1 | 4.9E1 | 4.4E1 | 5.7E1 | 7.2E1 | 5.0E1 | 1.0E-9 | 1.0E-9 | 5.1E2 | 1.9E2 | 77 | 21 | 64 | 21 | 0.64 |
| jE | ng/ml | 1.0E-9 | 1.0E-9 | 8.0E0 | 3.9E0 | 2.1E1 | 8.6E0 | 1.0E-9 | 1.0E-9 | 1.2E2 | 2.9E1 | 77 | 21 | 64 | 21 | 0.48 |
| jF | ng/ml | 3.5E1 | 2.9E1 | 5.0E1 | 4.0E1 | 5.8E1 | 4.7E1 | 1.0E-9 | 1.0E-9 | 2.5E2 | 1.5E2 | 77 | 21 | 64 | 21 | 0.46 |

Figure 23 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jG | ng/ml | 4.5E3 | 4.3E3 | 4.6E3 | 4.4E3 | 1.9E3 | 2.1E3 | 7.6E2 | 1.5E3 | 9.5E3 | 8.6E3 | 77 | 21 | 64 | 21 | 0.47 |
| jH | ng/ml | 7.9E1 | 7.3E1 | 8.6E1 | 8.2E1 | 4.5E1 | 5.0E1 | 1.9E1 | 1.3E1 | 2.3E2 | 2.5E2 | 77 | 21 | 64 | 21 | 0.45 |
| jI | ng/ml | 6.9E1 | 7.8E1 | 7.4E1 | 8.2E1 | 3.4E1 | 3.1E1 | 2.8E1 | 4.0E1 | 2.5E2 | 1.9E2 | 77 | 21 | 64 | 21 | 0.61 |
| sK | pg/mL | 4.2E3 | 4.1E3 | 4.3E3 | 3.8E3 | 1.6E3 | 1.5E3 | 1.7E3 | 1.9E3 | 9.2E3 | 6.2E3 | 49 | 8 | 45 | 8 | 0.44 |
| sM | pg/mL | 8.0E4 | 8.5E4 | 7.9E4 | 7.8E4 | 2.4E4 | 2.5E4 | 3.3E4 | 4.3E4 | 1.5E5 | 1.1E5 | 49 | 8 | 45 | 8 | 0.53 |
| sO | pg/mL | 2.8E8 | 2.6E8 | 2.9E8 | 2.5E8 | 9.9E7 | 7.1E7 | 7.9E7 | 1.4E8 | 4.9E8 | 3.3E8 | 49 | 8 | 45 | 8 | 0.38 |
| wC | ng/ml | 1.6E0 | 1.5E0 | 2.1E0 | 1.8E0 | 2.2E0 | 1.2E0 | 2.5E-1 | 5.7E-1 | 1.5E1 | 4.2E0 | 48 | 9 | 44 | 9 | 0.47 |
| wD | ng/ml | 2.0E1 | 1.7E1 | 8.1E1 | 2.0E1 | 3.1E2 | 1.5E1 | 2.8E0 | 5.1E0 | 2.1E3 | 5.2E1 | 48 | 9 | 44 | 9 | 0.48 |
| wE | ng/ml | 5.0E1 | 4.3E1 | 5.4E1 | 4.2E1 | 2.4E1 | 2.5E1 | 7.0E0 | 4.0E0 | 1.4E2 | 8.9E1 | 48 | 9 | 44 | 9 | 0.36 |
| wG | ng/ml | 9.6E-2 | 1.2E-2 | 1.3E-1 | 6.5E-2 | 1.3E-1 | 1.1E-1 | 1.0E-9 | 1.0E-9 | 4.8E-1 | 3.3E-1 | 48 | 9 | 44 | 9 | 0.38 |
| wH | ng/ml | 2.3E-2 | 6.0E-3 | 2.1E-1 | 8.1E-2 | 5.5E-1 | 1.5E-1 | 1.0E-9 | 1.0E-9 | 2.9E0 | 4.0E-1 | 48 | 9 | 44 | 9 | 0.37 |
| wF | ng/ml | 2.1E-1 | 4.2E-2 | 2.9E0 | 2.7E-1 | 1.0E1 | 3.6E-1 | 1.0E-9 | 1.0E-9 | 5.7E1 | 1.1E0 | 48 | 9 | 44 | 9 | 0.44 |
| rA | pg/ml | 2.4E1 | 2.7E1 | 2.7E1 | 3.4E1 | 2.2E1 | 2.4E1 | 1.0E-9 | 1.0E-9 | 1.2E2 | 8.2E1 | 74 | 20 | 61 | 20 | 0.59 |
| qZ | pg/ml | 4.3E1 | 8.3E1 | 2.1E2 | 9.6E2 | 1.3E3 | 3.0E3 | 2.8E-4 | 7.2E-1 | 1.0E4 | 1.0E4 | 63 | 11 | 54 | 11 | 0.59 |
| qY | pg/ml | 2.1E1 | 1.4E1 | 4.6E1 | 3.6E1 | 7.5E1 | 4.3E1 | 8.7E-1 | 2.2E0 | 5.3E2 | 1.6E2 | 74 | 20 | 61 | 20 | 0.46 |
| qX | pg/ml | 5.1E1 | 7.2E1 | 5.9E1 | 8.6E1 | 3.9E1 | 6.3E1 | 1.0E-9 | 1.0E-9 | 1.8E2 | 2.1E2 | 74 | 20 | 61 | 20 | 0.62 |
| qW | pg/ml | 9.4E0 | 7.0E0 | 1.2E1 | 9.7E0 | 1.3E1 | 7.6E0 | 1.0E-9 | 1.0E-9 | 7.1E1 | 2.3E1 | 74 | 20 | 61 | 20 | 0.46 |
| qV | pg/ml | 2.1E3 | 1.4E3 | 2.7E3 | 2.0E3 | 1.9E3 | 1.7E3 | 2.3E2 | 1.7E2 | 8.5E3 | 6.4E3 | 74 | 20 | 61 | 20 | 0.38 |
| qU | pg/ml | 4.5E1 | 7.6E1 | 1.3E2 | 1.0E2 | 2.2E2 | 8.3E1 | 1.0E-9 | 1.0E1 | 1.4E3 | 2.8E2 | 74 | 20 | 61 | 20 | 0.58 |
| qT | pg/ml | 3.8E1 | 5.7E1 | 6.4E1 | 8.5E1 | 1.2E2 | 9.4E1 | 1.0E-9 | 5.6E0 | 9.0E2 | 4.4E2 | 74 | 20 | 61 | 20 | 0.64 |
| qI | ng/ml | 5.8E4 | 7.2E4 | 6.4E4 | 6.5E4 | 3.2E4 | 2.5E4 | 5.4E3 | 3.0E4 | 1.6E5 | 9.8E4 | 48 | 8 | 46 | 8 | 0.55 |
| qH | ng/ml | 6.5E4 | 5.6E4 | 7.3E4 | 6.5E4 | 3.9E4 | 4.5E4 | 1.0E4 | 2.3E4 | 1.8E5 | 1.6E5 | 48 | 8 | 46 | 8 | 0.39 |
| qG | ng/ml | 1.8E5 | 2.2E5 | 1.9E5 | 2.2E5 | 6.2E4 | 5.8E4 | 3.1E4 | 1.5E5 | 3.3E5 | 2.9E5 | 48 | 8 | 46 | 8 | 0.62 |
| jK | ng/ml | 1.6E3 | 1.6E3 | 1.7E3 | 1.7E3 | 5.7E2 | 5.0E2 | 5.5E2 | 7.6E2 | 4.1E3 | 2.8E3 | 77 | 21 | 64 | 21 | 0.51 |
| jL | ng/ml | 1.8E2 | 2.1E2 | 2.6E2 | 3.5E2 | 1.9E2 | 3.7E2 | 3.6E1 | 8.8E1 | 7.9E2 | 1.7E3 | 77 | 21 | 64 | 21 | 0.56 |
| jM | ng/ml | 7.1E4 | 6.8E4 | 7.0E4 | 7.3E4 | 3.4E4 | 3.4E4 | 3.9E2 | 2.4E4 | 1.5E5 | 1.5E5 | 77 | 21 | 64 | 21 | 0.50 |
| jO | pg/ml | 2.2E5 | 2.1E5 | 2.8E5 | 2.6E5 | 1.5E5 | 1.4E5 | 5.2E4 | 7.4E4 | 7.7E5 | 6.2E5 | 77 | 21 | 64 | 21 | 0.46 |
| jP | pg/ml | 2.3E5 | 2.4E5 | 2.6E5 | 2.7E5 | 1.5E5 | 1.9E5 | 7.0E4 | 6.6E4 | 9.1E5 | 9.2E5 | 77 | 21 | 64 | 21 | 0.48 |
| jQ | pg/ml | 2.5E3 | 3.3E3 | 3.0E3 | 3.9E3 | 2.3E3 | 3.0E3 | 4.2E1 | 2.6E2 | 1.2E4 | 1.1E4 | 77 | 21 | 64 | 21 | 0.59 |
| jR | pg/ml | 6.5E3 | 7.9E3 | 9.5E3 | 1.1E4 | 9.9E3 | 1.0E4 | 1.0E-9 | 7.2E1 | 5.5E4 | 3.4E4 | 77 | 21 | 64 | 21 | 0.55 |
| jT | pg/ml | 1.6E5 | 1.7E5 | 1.7E5 | 1.8E5 | 6.9E4 | 5.6E4 | 6.8E4 | 9.0E4 | 4.5E5 | 2.8E5 | 77 | 21 | 64 | 21 | 0.58 |
| xA | pg/ml | 3.9E0 | 1.8E1 | 1.7E1 | 2.9E1 | 5.7E1 | 4.6E1 | 1.0E-9 | 1.0E-9 | 3.9E2 | 1.4E2 | 48 | 9 | 44 | 9 | 0.62 |
| yE | pg/ml | 7.8E1 | 6.6E1 | 8.2E1 | 7.9E1 | 4.9E1 | 3.7E1 | 6.4E0 | 4.0E1 | 3.0E2 | 1.6E2 | 48 | 9 | 44 | 9 | 0.47 |
| tM | pg/ml | 4.3E1 | 3.3E1 | 4.3E1 | 3.5E1 | 2.0E1 | 1.9E1 | 1.0E-9 | 1.0E-9 | 1.0E2 | 6.1E1 | 48 | 9 | 44 | 9 | 0.37 |
| tL | pg/ml | 1.0E-9 | 1.0E-9 | 7.8E0 | 3.0E-1 | 3.8E1 | 6.0E-1 | 1.0E-9 | 1.0E-9 | 2.6E2 | 1.4E0 | 48 | 9 | 44 | 9 | 0.48 |
| jU | mIU/ml | 3.8E0 | 6.7E0 | 1.0E1 | 1.4E1 | 1.7E1 | 1.9E1 | 8.9E-2 | 6.3E-2 | 8.1E1 | 7.5E1 | 77 | 21 | 64 | 21 | 0.63 |
| jV | mIU/ml | 1.6E0 | 2.2E0 | 3.5E0 | 5.4E0 | 5.4E0 | 8.5E0 | 2.1E-2 | 2.7E-3 | 3.1E1 | 3.3E1 | 77 | 21 | 64 | 21 | 0.52 |
| jY | ng/ml | 9.7E-4 | 4.3E-4 | 1.1E-2 | 7.3E-3 | 4.2E-2 | 2.1E-2 | 1.0E-9 | 1.0E-9 | 3.0E-1 | 9.4E-2 | 77 | 21 | 64 | 21 | 0.46 |
| kC | pg/ml | 9.7E1 | 1.2E2 | 2.4E2 | 1.1E2 | 5.6E2 | 5.7E1 | 2.1E1 | 3.6E1 | 3.5E3 | 2.1E2 | 54 | 13 | 47 | 13 | 0.47 |
| kE | pg/ml | 1.3E5 | 1.4E5 | 1.3E5 | 1.3E5 | 3.3E4 | 4.2E4 | 4.1E4 | 3.8E4 | 2.0E5 | 2.0E5 | 54 | 13 | 47 | 13 | 0.50 |
| kF | pg/mL | 6.6E1 | 5.6E1 | 8.0E1 | 6.5E1 | 7.0E1 | 1.8E1 | 3.2E1 | 4.0E1 | 5.1E2 | 9.2E1 | 54 | 13 | 47 | 13 | 0.44 |
| kG | pg/mL | 9.1E3 | 1.1E4 | 1.2E4 | 2.1E4 | 1.4E4 | 3.1E4 | 7.5E2 | 3.8E3 | 9.1E4 | 1.2E5 | 54 | 13 | 47 | 13 | 0.57 |
| kI | pg/ml | 2.2E2 | 1.8E2 | 2.4E2 | 2.3E2 | 1.4E2 | 1.4E2 | 5.4E1 | 9.2E1 | 8.7E2 | 5.5E2 | 54 | 13 | 47 | 13 | 0.40 |
| kK | pg/ml | 1.2E2 | 1.2E2 | 1.7E2 | 1.6E2 | 1.8E2 | 1.3E2 | 2.2E1 | 4.5E1 | 1.2E3 | 4.9E2 | 54 | 13 | 47 | 13 | 0.49 |
| kN | pg/ml | 1.0E3 | 1.2E3 | 1.5E3 | 1.7E3 | 1.9E3 | 1.2E3 | 2.1E2 | 4.4E2 | 1.3E4 | 3.9E3 | 54 | 13 | 47 | 13 | 0.62 |
| kO | pg/ml | 7.7E3 | 6.2E3 | 1.1E4 | 6.5E3 | 1.8E4 | 1.9E3 | 4.0E3 | 3.8E3 | 1.3E5 | 1.0E4 | 54 | 13 | 47 | 13 | 0.30 |
| kP | pg/ml | 5.4E3 | 7.0E3 | 6.7E3 | 6.9E3 | 5.5E3 | 2.6E3 | 8.6E2 | 2.7E3 | 3.3E4 | 1.2E4 | 54 | 13 | 47 | 13 | 0.60 |
| kQ | pg/ml | 4.3E3 | 3.8E3 | 4.9E3 | 4.4E3 | 2.3E3 | 2.1E3 | 5.6E2 | 1.6E3 | 1.2E4 | 9.3E3 | 100 | 21 | 86 | 21 | 0.42 |
| kR | pg/ml | 2.4E1 | 2.0E1 | 4.0E1 | 2.5E1 | 1.0E2 | 1.8E1 | 1.0E-9 | 5.1E0 | 1.0E3 | 6.9E1 | 100 | 21 | 86 | 21 | 0.44 |
| kS | pg/ml | 7.7E2 | 8.2E2 | 9.9E2 | 8.4E2 | 4.1E3 | 4.0E2 | 8.2E1 | 2.5E2 | 1.4E4 | 1.7E3 | 100 | 21 | 86 | 21 | 0.52 |
| pS | ng/ml | 2.0E5 | 2.1E5 | 2.2E5 | 2.4E5 | 9.5E4 | 1.4E5 | 7.5E4 | 1.0E5 | 5.0E5 | 5.7E5 | 49 | 8 | 45 | 8 | 0.55 |
| rZ | ng/ml | 1.2E-3 | 1.0E-9 | 7.9E-3 | 2.6E-3 | 2.1E-2 | 3.6E-3 | 1.0E-9 | 1.0E-9 | 1.1E-1 | 9.1E-3 | 73 | 18 | 58 | 18 | 0.46 |
| rY | ng/ml | 5.4E-2 | 4.7E-2 | 2.5E-1 | 6.7E-2 | 8.3E-1 | 1.1E-1 | 1.0E-9 | 1.0E-9 | 6.3E0 | 5.0E-1 | 73 | 18 | 58 | 18 | 0.38 |
| rX | ng/ml | 1.0E-9 | 1.0E-9 | 9.2E-2 | 1.7E-2 | 4.5E-1 | 6.7E-2 | 1.0E-9 | 1.0E-9 | 3.7E0 | 2.9E-1 | 73 | 18 | 58 | 18 | 0.42 |
| lK | pg/ml | 7.1E1 | 1.1E2 | 1.4E2 | 2.0E2 | 1.8E2 | 3.2E2 | 1.0E-9 | 4.1E0 | 7.0E2 | 1.3E3 | 77 | 21 | 64 | 21 | 0.53 |
| lL | pg/ml | 1.8E3 | 1.4E3 | 3.4E3 | 2.0E3 | 5.5E3 | 1.9E3 | 7.5E1 | 4.5E2 | 4.2E4 | 6.8E3 | 77 | 21 | 64 | 21 | 0.40 |
| lM | pg/ml | 1.0E3 | 1.5E3 | 3.3E3 | 6.7E3 | 7.5E3 | 1.2E4 | 3.9E1 | 2.7E2 | 5.1E4 | 4.4E4 | 77 | 21 | 64 | 21 | 0.58 |

Figure 23 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| lN | pg/ml | 1.0E-9 | 1.0E-9 | 7.3E0 | 1.2E0 | 2.2E1 | 2.1E0 | 1.0E-9 | 1.0E-9 | 1.5E2 | 5.0E0 | 77 | 21 | 64 | 21 | 0.40 |
| lO | pg/ml | 1.0E-9 | 1.0E-9 | 5.2E-1 | 6.3E-1 | 4.6E0 | 2.9E0 | 1.0E-9 | 1.0E-9 | 4.0E1 | 1.3E1 | 77 | 21 | 64 | 21 | 0.52 |
| zA | ng/ml | 1.9E7 | 1.9E7 | 2.0E7 | 2.1E7 | 6.8E6 | 6.0E6 | 6.7E6 | 1.1E7 | 3.6E7 | 3.3E7 | 44 | 9 | 40 | 9 | 0.54 |
| rW | ng/ml | 1.3E-2 | 6.5E-3 | 2.4E-2 | 3.4E-2 | 3.1E-2 | 5.5E-2 | 1.0E-9 | 1.0E-9 | 1.7E-1 | 1.6E-1 | 49 | 9 | 46 | 9 | 0.50 |
| rV | ng/ml | 1.0E-9 | 1.0E-9 | 9.2E-3 | 3.2E-2 | 3.7E-2 | 9.4E-2 | 1.0E-9 | 1.0E-9 | 2.2E-1 | 2.8E-1 | 49 | 9 | 46 | 9 | 0.53 |
| rU | ng/ml | 9.5E-2 | 4.1E-2 | 1.4E-1 | 7.7E-1 | 2.3E-1 | 1.6E0 | 1.0E-9 | 1.0E-9 | 1.4E0 | 4.4E0 | 49 | 9 | 46 | 9 | 0.43 |
| rT | ng/ml | 6.7E0 | 4.0E0 | 6.8E0 | 5.0E0 | 4.1E0 | 2.5E0 | 7.5E-1 | 1.3E0 | 2.1E1 | 1.0E1 | 49 | 9 | 46 | 9 | 0.35 |
| rS | ng/ml | 3.4E0 | 4.9E0 | 5.6E0 | 5.6E0 | 6.8E0 | 3.5E0 | 1.0E0 | 1.5E0 | 3.8E1 | 1.3E1 | 49 | 9 | 46 | 9 | 0.62 |
| sC | pg/mL | 5.6E3 | 8.9E3 | 8.5E3 | 1.3E4 | 7.1E3 | 1.2E4 | 1.7E3 | 2.3E3 | 3.2E4 | 3.9E4 | 49 | 8 | 45 | 8 | 0.64 |
| yL | pg/ml | 3.4E1 | 2.6E1 | 4.2E1 | 2.7E1 | 2.8E1 | 8.7E0 | 5.6E0 | 1.1E1 | 1.8E2 | 3.8E1 | 47 | 9 | 43 | 9 | 0.29 |
| rP | ng/ml | 7.7E1 | 1.3E2 | 1.7E2 | 2.2E2 | 2.3E2 | 2.2E2 | 1.0E-9 | 3.7E0 | 1.2E3 | 5.0E2 | 49 | 9 | 46 | 9 | 0.58 |
| rQ | ng/ml | 1.0E-9 | 1.0E-9 | 3.4E0 | 1.9E1 | 1.5E1 | 5.6E1 | 1.0E-9 | 1.0E-9 | 8.9E1 | 1.7E2 | 49 | 9 | 46 | 9 | 0.52 |
| rO | ng/ml | 2.5E-2 | 4.5E-2 | 3.9E-2 | 9.6E-2 | 7.1E-2 | 1.5E-1 | 1.0E-9 | 1.0E-9 | 4.4E-1 | 4.7E-1 | 49 | 9 | 46 | 9 | 0.61 |
| rR | ng/ml | 3.9E0 | 1.0E-9 | 2.2E1 | 5.3E0 | 6.6E1 | 1.2E1 | 1.0E-9 | 1.0E-9 | 4.5E2 | 3.6E1 | 49 | 9 | 46 | 9 | 0.38 |
| rN | ng/ml | 6.4E-1 | 6.7E-1 | 7.0E-1 | 8.3E-1 | 3.8E-1 | 6.5E-1 | 5.1E-2 | 2.7E-1 | 2.1E0 | 2.3E0 | 49 | 9 | 46 | 9 | 0.50 |
| qO | pg/ml | 9.7E3 | 1.2E4 | 1.2E4 | 1.6E4 | 8.2E3 | 1.6E4 | 2.2E3 | 7.4E2 | 3.9E4 | 5.0E4 | 50 | 8 | 47 | 8 | 0.52 |
| qP | pg/ml | 3.6E2 | 3.9E2 | 3.9E2 | 5.3E2 | 2.5E2 | 5.8E2 | 1.0E-9 | 1.1E2 | 1.1E3 | 1.9E3 | 50 | 8 | 47 | 8 | 0.49 |
| qQ | pg/ml | 3.1E0 | 1.0E-9 | 1.5E1 | 6.2E0 | 4.0E1 | 8.7E0 | 1.0E-9 | 1.0E-9 | 2.8E2 | 1.9E1 | 50 | 8 | 47 | 8 | 0.42 |
| nW | pg/ml | 1.1E5 | 1.3E5 | 1.1E5 | 1.2E5 | 2.5E4 | 2.6E4 | 5.8E4 | 8.2E4 | 1.8E5 | 1.6E5 | 100 | 21 | 86 | 21 | 0.61 |
| nY | pg/ml | 1.9E3 | 2.3E3 | 2.3E3 | 2.8E3 | 1.4E3 | 2.7E3 | 6.5E2 | 6.6E2 | 9.9E3 | 1.3E4 | 100 | 21 | 86 | 21 | 0.53 |
| oO | pg/ml | 8.2E4 | 8.9E4 | 1.2E5 | 1.4E5 | 1.1E5 | 9.4E4 | 4.0E4 | 2.6E4 | 6.2E5 | 2.8E5 | 52 | 11 | 45 | 11 | 0.58 |
| oP | pg/ml | 1.3E5 | 2.0E5 | 1.4E5 | 2.0E5 | 8.4E4 | 9.0E4 | 4.8E4 | 7.1E4 | 3.5E5 | 3.6E5 | 52 | 11 | 45 | 11 | 0.69 |
| oQ | pg/ml | 3.0E3 | 4.4E3 | 3.2E3 | 5.4E3 | 1.6E3 | 3.6E3 | 1.1E3 | 1.7E3 | 1.0E4 | 1.2E4 | 52 | 11 | 45 | 11 | 0.70 |
| oE | pg/ml | 2.1E2 | 1.4E2 | 4.6E2 | 4.6E2 | 6.4E2 | 7.3E2 | 1.0E-9 | 1.0E-9 | 4.7E3 | 2.8E3 | 100 | 21 | 86 | 21 | 0.46 |
| oF | pg/ml | 8.6E3 | 1.3E4 | 2.0E4 | 3.3E4 | 3.3E4 | 3.9E4 | 6.4E1 | 6.5E2 | 2.3E5 | 1.4E5 | 100 | 21 | 86 | 21 | 0.61 |
| oH | pg/ml | 4.2E1 | 2.7E1 | 9.3E1 | 9.7E1 | 1.5E2 | 2.1E2 | 4.2E0 | 4.3E-1 | 8.6E2 | 9.9E2 | 100 | 21 | 86 | 21 | 0.44 |
| oK | pg/ml | 6.2E2 | 9.8E2 | 1.9E3 | 2.2E3 | 3.2E3 | 3.4E3 | 5.2E1 | 1.8E2 | 1.8E4 | 1.2E4 | 100 | 21 | 86 | 21 | 0.55 |
| oN | pg/ml | 4.7E2 | 6.4E2 | 8.0E2 | 8.5E2 | 1.9E3 | 7.5E2 | 1.5E2 | 2.8E2 | 1.8E4 | 3.7E3 | 100 | 21 | 86 | 21 | 0.66 |
| uL | ng/ml | 3.8E1 | 3.5E1 | 4.1E1 | 7.5E1 | 2.4E1 | 1.1E2 | 1.0E-9 | 2.4E1 | 1.6E2 | 3.4E2 | 48 | 8 | 44 | 8 | 0.51 |
| uO | ng/ml | 3.5E-1 | 3.9E-1 | 8.5E-1 | 6.2E-1 | 1.5E0 | 7.2E-1 | 1.0E-9 | 1.0E-9 | 9.3E0 | 2.0E0 | 48 | 8 | 44 | 8 | 0.46 |
| uM | ng/ml | 6.3E-1 | 6.5E-1 | 1.2E0 | 8.1E-1 | 2.3E0 | 3.8E-1 | 1.0E-9 | 4.7E-1 | 1.3E1 | 1.6E0 | 48 | 8 | 44 | 8 | 0.57 |
| uI | ng/ml | 6.5E-2 | 6.9E-2 | 1.3E-1 | 1.1E-1 | 1.9E-1 | 1.2E-1 | 1.6E-2 | 3.6E-2 | 1.1E0 | 3.9E-1 | 48 | 8 | 44 | 8 | 0.52 |
| uN | ng/ml | 1.5E1 | 1.5E1 | 1.6E1 | 1.7E1 | 6.5E1 | 7.1E1 | 7.8E0 | 8.1E0 | 4.1E1 | 3.0E1 | 48 | 8 | 44 | 8 | 0.51 |
| uG | ng/ml | 2.2E1 | 1.6E1 | 2.5E1 | 2.7E1 | 1.3E1 | 2.5E1 | 9.8E0 | 6.1E0 | 6.9E1 | 7.9E1 | 48 | 8 | 44 | 8 | 0.40 |
| uR | ng/ml | 2.3E0 | 2.5E0 | 4.2E0 | 2.7E0 | 9.1E0 | 1.3E0 | 9.9E-1 | 8.9E-1 | 6.4E1 | 5.5E0 | 48 | 9 | 44 | 9 | 0.52 |
| uP | ng/ml | 1.8E0 | 3.0E0 | 2.2E0 | 3.1E0 | 1.3E0 | 1.2E0 | 1.1E0 | 1.8E0 | 9.1E0 | 6.0E0 | 48 | 9 | 44 | 9 | 0.78 |
| uV | ng/ml | 1.0E-9 | 1.5E-3 | 1.1E-2 | 1.1E-2 | 3.3E-2 | 1.3E-2 | 1.0E-9 | 1.0E-9 | 2.0E-1 | 3.1E-2 | 48 | 9 | 44 | 9 | 0.57 |
| uT | ng/ml | 6.2E1 | 7.8E1 | 8.8E1 | 8.6E1 | 9.6E1 | 4.2E1 | 1.2E1 | 3.3E1 | 5.8E2 | 1.6E2 | 48 | 9 | 44 | 9 | 0.60 |
| uU | ng/ml | 1.6E0 | 1.0E0 | 2.0E0 | 1.9E0 | 1.1E0 | 1.8E0 | 6.0E-1 | 6.3E-1 | 5.4E0 | 6.0E0 | 48 | 9 | 44 | 9 | 0.35 |
| uW | ng/ml | 7.5E0 | 8.4E0 | 7.9E0 | 9.2E0 | 2.8E0 | 2.5E0 | 4.0E0 | 5.6E0 | 2.2E1 | 1.3E1 | 48 | 8 | 44 | 8 | 0.68 |
| vB | ng/ml | 2.7E0 | 3.7E0 | 2.7E0 | 3.9E0 | 1.3E0 | 1.8E0 | 5.9E-1 | 1.5E0 | 5.6E0 | 6.6E0 | 48 | 8 | 44 | 8 | 0.68 |
| vC | ng/ml | 1.0E-9 | 1.0E-9 | 7.5E-3 | 1.0E-9 | 3.5E-2 | 0.0E0 | 1.0E-9 | 1.0E-9 | 2.0E-1 | 1.0E-9 | 48 | 8 | 44 | 8 | 0.47 |
| uY | ng/ml | 8.3E-1 | 6.1E-1 | 1.3E0 | 8.4E-1 | 1.2E0 | 8.7E-1 | 8.7E-2 | 2.4E-1 | 4.9E0 | 3.0E0 | 48 | 8 | 44 | 8 | 0.36 |
| uZ | ng/ml | 5.9E-1 | 5.6E-1 | 8.8E-1 | 5.4E-1 | 1.1E0 | 1.9E-1 | 1.4E-1 | 2.7E-1 | 7.2E0 | 8.5E-1 | 48 | 8 | 44 | 8 | 0.42 |
| uX | ng/ml | 1.1E1 | 1.4E1 | 1.2E1 | 1.4E1 | 6.7E0 | 5.7E0 | 3.6E0 | 7.5E0 | 3.3E1 | 2.3E1 | 48 | 8 | 44 | 8 | 0.65 |
| vA | ng/ml | 6.8E-2 | 7.2E-2 | 8.5E-2 | 8.1E-2 | 5.8E-2 | 3.2E-2 | 2.5E-2 | 3.0E-2 | 3.0E-1 | 1.4E-1 | 48 | 8 | 44 | 8 | 0.55 |
| vH | ng/ml | 1.2E-1 | 1.4E-1 | 1.7E-1 | 1.5E-1 | 1.6E-1 | 7.4E-2 | 1.5E-2 | 5.8E-2 | 8.0E-1 | 2.6E-1 | 49 | 8 | 45 | 8 | 0.56 |
| vI | ng/ml | 1.8E0 | 1.7E0 | 1.9E0 | 2.3E0 | 1.2E0 | 1.9E0 | 6.2E-3 | 1.2E-2 | 5.1E0 | 6.2E0 | 49 | 8 | 45 | 8 | 0.53 |
| vP | ng/ml | 3.8E2 | 4.8E2 | 4.4E2 | 5.6E2 | 3.2E2 | 5.0E2 | 7.0E1 | 6.7E1 | 1.5E3 | 1.7E3 | 48 | 9 | 44 | 9 | 0.55 |
| vT | ng/ml | 7.7E1 | 9.9E1 | 1.2E2 | 1.1E2 | 1.2E2 | 7.5E1 | 4.1E1 | 3.0E1 | 6.9E2 | 2.8E2 | 48 | 9 | 44 | 9 | 0.53 |
| vU | ng/ml | 1.0E-9 | 1.0E-9 | 2.3E1 | 2.6E1 | 3.2E1 | 4.2E1 | 1.0E-9 | 1.0E-9 | 1.0E2 | 1.2E2 | 48 | 9 | 44 | 9 | 0.48 |
| vQ | ng/ml | 3.4E2 | 3.5E2 | 3.4E2 | 4.0E2 | 1.3E2 | 2.0E2 | 6.7E1 | 2.1E2 | 7.0E2 | 8.4E2 | 48 | 9 | 44 | 9 | 0.57 |
| vO | ng/ml | 1.7E3 | 1.8E3 | 1.8E3 | 1.9E3 | 4.6E2 | 5.1E2 | 1.0E3 | 1.2E3 | 3.0E3 | 2.8E3 | 48 | 9 | 44 | 9 | 0.57 |
| vS | ng/ml | 1.3E3 | 1.6E3 | 1.3E3 | 1.4E3 | 3.5E2 | 5.9E2 | 1.0E-9 | 1.0E-9 | 1.8E3 | 2.1E3 | 48 | 9 | 44 | 9 | 0.65 |
| vV | ng/ml | 8.4E2 | 1.4E3 | 1.1E3 | 1.4E3 | 9.9E2 | 1.3E3 | 1.1E2 | 1.1E2 | 5.0E3 | 4.1E3 | 48 | 9 | 44 | 9 | 0.56 |
| vW | ng/ml | 1.5E2 | 1.0E2 | 1.7E2 | 1.2E2 | 1.3E2 | 5.6E1 | 4.3E1 | 7.7E1 | 6.7E2 | 2.5E2 | 48 | 9 | 44 | 9 | 0.38 |
| pF | pg/ml | 5.0E-1 | 4.1E-1 | 6.8E-1 | 1.0E0 | 1.0E0 | 1.8E0 | 1.0E-9 | 1.0E-9 | 9.4E0 | 7.8E0 | 100 | 21 | 86 | 21 | 0.50 |

Figure 23 Continued

Analyte panel data:

Unconstrained panels with 3 analytes, where 1.0E-9 >= 'model p-value' > 0. Contains 3 panels of 27,619,476 total panels evaluated. : Vq{rY(Ad Jv)} OnhLiH Unconstrained panels with 3 analytes, where 1.0E-8 >= 'model p-value' > 1.0E-9. Contains 70 panels of 27,619,476 total panels evaluated. : iH{Ad(eD fN fY hL hO hP iB jH jl jL jP jY pY qA qB qC qD qO qX) qX(aG aZ Ed Ic Iv IN rA) On(qG rB) EtqG QzqQ JprT OkrY aJsC} Cw{Ld(qG qH qQ) Nq(qO qP) hO(qO qP) rN(Fp Pf) BcqZ eZoK gPhL iOqQ} Us{Ad(qH rU) hR(Dk Kq) BcqZ UchX OkrY OnlM} kO{qT(hR hV oO oP rB) hWrA} Nt{qO(Ap Et) JtqG} dJ{KqnT Pkql bBwQ} AdNarU ApKkrR QzdBqQ VqgLrY Unconstrained panels with 3 analytes, where 1.0E-7 >= 'model p-value' > 1.0E-8. Contains 1,254 panels of 27,619,476 total panels evaluated. : iH{qX(aA aC aD aF aH aJ aM An aO aP aR As aW Ax bA BC bG bl bR bU bV bW bZ cA cB cC cD cF cK cM cO cP cQ CS cT cU CW cX dA DC Dd dF dG dH Dl dJ dL dM eC eD Et Fn Fp Fr Fw gW hA Hu Hv Hw iA iB iC II Iq iZ jD JE jF JH JI JK jL jP jQ jR Js jT jV jY Kg Ki Kk KQ Kr kS Ky Lj IK IL IM IO Ly Ma Mj Mm Mt Nc Nf Nj Nl Nn No Nq Nr Nt Nu Nx nY Of Ok ON Pd Pe pF qU qV qW QY Uk Vv tF) Ad(eT eZ hA hR hV hW hX iC jD jE jF jG jK jM jO jQ jR jT jU jV IK IL IM IN IO pS qG qH ql qP qQ qT qU qV qW qY qZ rA rB rC rN rO rP rQ rR rS rT rU rV rW rX rY sC sK sM sO uG ul uL uM uN uO uP uR uT uU uV uW uX uY uZ vA vB vC vH vI vO vP vQ vS vT vU vV vW yH yJ yK zG zH zI yE tM tL xA) qU(aD aG bM bW cE Di eD Fn Hv iB Ic Ij Il Iq jH JI jL Kk Kq Ky Li IK IN Lw Mm Ok On Pe qT Uf) rC(aD aV aW bC bW bX bZ cN cR cU dC Di dJ dK eD Et jL Jp Kq IN Lw Mm Nr nY Ok ON) qV(aA aD aG bG bW bZ Di eD hR iB Ic Ij Iv jl jL Kk Kq IN Lw Mm On Pd Pe) rB(bW Di eD Et jL Jp Jt Kq IN Lx Mm Mq Nr Nw Nx Ok Om Uf) Jp(rX rY sO ul uL uM uV uY uZ vB vO vS wB wE wF wH) eD(bU bW bX cE cK cW Ic Iq Jd Nn On qT qW qY rA) rY(bW cE Di Et hX Kq Lw Mm Nr Nw Nx On Uf Vq Vs) uY(Cw Et Hb Hw Jh Jt Kg Lh Mm No Nr Nt Nu Ok On) rZ(bC bW cE cG cW Di hA jH jL IK Mm Ok On Uf) sC(Bc Cs Cv Fn Ha Ju Jv Lj No Nr Qc Qd Us Vv) uZ(Ap Et Hb Ij Jt Lh Nn No Nq Nr Oa Ok On Us) Ic(hA hX iC jD jE jL Kq IK IM qT qW qY rA) qT(aG aJ bZ Di Ed Fw iA Iv jl Kk IN) jL(aA aG bU cC cK dC dD hR Iv Jd rX) rX(bW cE Et hV Ji IK Mm Nr Ok On) qY(aD aG Di iB Iv jl Kk IN Pe) No(uG uL uR uV vO vT vU yE) rA(aG Di Ed Fw iB jl IN) On(hA hR iB jY vH xA) qW(Di jH jl IN Pe) Jd(jH jl jY IL) lM(aD aF aG bZ) Ed(rW uM yK) Kq(hR iB jY) hA(bW cE cW) Dc(vB vT) Nn(hL qQ) Ml(hV IK) Oa(uV vW) Ok(hR vl) cK(IL IN) wH(Hr Lj) CwhL EthR FpwF HqwQ HutV QuiL KgvT UmuL PkuM aJuX bWjU qDtM} Cw{uY(aC AD aK Al aM aN aP aQ aS aU aV Aw aY bA BC bE bH bN bO bP bQ bW bX cB cN cP cT cU Cv cW cZ dA Dc Dd dH Di dJ dL dR eC eD eT Fb fP Fw fY GP gW hG Hr Hu hV iA Id iJ iO iP Iq Is iZ Jd Je Jf Jh jL jM Jp jQ jR jT Kk kR Ky Kz Ld Lj IM Mn Nc Nk No Nr nW nY oF oH oK Or Pf Pk qA Qg Qh qO qP Qw QY Qz rB Rh rN rW sC Tz Ub uG ul Um uN Uo uP Uu uV uX vl vP vV zH Tj tF) Nq(ql rO rR rW sM uO vB vl vP vV yH yK zH tL xA) Pe(sC uG uN uP uU uW vI vP yJ tM) No(vA vB vO vS vT vU yH tL xA) vI(cC hL hO jK oK QD qV Vv) Bc(uL uV uZ vT wF yJ xA) wQ(aN Dl Ky Nc Rb sK Uk) vB(aP cB dJ Hu Ld Pb Vs) Vv(qO qP qX rY vP vV) xA(cZ Hu jK jL Lj rN) wL(aK bC cW Hu Kk) vT(aL bW Hu jL Ld) tL(cW eZ Kl Ky) vH(cW nW Ub Um) vV(hL hO Ly qV) Ed(qG wB wJ) qD(qU sC uN) vP(hL hO qV) Po(sC uN) Ha(uP uW) Nr(rT uM) Ld(wF wH) dA(uP zG) wJ(cB Ly) rN(jF jY) GlwH NjsK UbuL HuwF dJjO hLuN hOrW iOuZ qGvU} Us{On(eD hA hR hW iC jD jF jG jL jO jP jQ jR jT jY IL IN qU qV qX rA rB rY rZ) Kq(eD hV hW hX jD jE jl jL jQ jR jY IL qX rB rY) Bc(sO tV uR wB wC wF wG wH wL wP yD) Ad(hO hR jF IO qQ sK sM vS yH) Dk(hV hW hX jY qQ rY rZ wQ) Jk(sC uX vB vP wG wH yK Tk) wD(aC bW Hq Hr Oe Of) Aj(sC uW vP wC tM) Jh(eZ uY vI vP wH) bW(uG uN vU xA) qD(rT sC sM vI) Vs(rB rY rZ) hR(Jg Qt Uc) wF(aC Ky No) Mg(vI vS) Jd(uY wC) Qh(IO qQ) Ok(rB rX) dN(uZ vW) wQ(Ed Ib) wH(Ct cZ) xA(Ap Mm) sC(bG Uk) EfuP UcvS TnlL TvnB IquZ IsyJ NyjY bCwG cRuY hArY} Ad{Kr(pS sK sM sO uG uL uP uY vH vO vP vQ vU vV vW wC wD wF wG wL yJ yK yL zG zH zI tM) Nt(rR rT rW uN vW yL yE xA) Na(sK sM uL uM wC zG) Hf(eZ jL uY) dB(wC wL)} Bc{Kz(sK sM tV uN uU uY uZ wF wJ wK wQ yD yJ) Hf(rY uT vB vS wF wH yD) Db(pS vB wF wH) uN(jY Nt Um) No(uL vT) Na(tV xA) fP(uX xA) vW(Nt qD) GzrY KrwF UptV aZuG cCuY} qD{Kz(sM uG uP uX vA vH vl vW yH tM) tM(fP Kr Me Wm) Hf(sC uW vI) Um(vU vW yE) Kk(uU vW) sC(Db Hc) uP(Ap Qw) NouW OnVq PjqG hGyE} No{Jd(ul uL uN uV uW uX vB vl vO vS vT vW zG tM xA) dB(tX wF wH wL) IcxA IqtQ QzwQ KzzG bWvT kRuY} uY{Nt(Al Ap Cu hG iO Jd kR Uh) Ap(cM Dg Kk) Hf(Hw Mm Pk) Kr(Hw Jp) Kz(bC Nb) Um(gL Uk) NacR} qT{kO(Fp Hw Ih Iq Jk Mt Qa Qb) Hw(nC nH nJ nL nU) IhnJ UmwQ} Kk{Ap(sK tV uN uP uU uZ vH xA) Et(Nm Nt pS vQ yL) KfyL} Kz{bC(uZ vH wF wG) Nb(uZ wF wG) zG(Ed hL) qQ(pS sM) JjyL aNwQ qCrX} Um{vB(aZ iC Kx Uk) bE(wF wL) vS(Fw wL) IktL QeyL PgzH qCvU} dJ{Et(Ic tQ tU) wQ(fP Kg Ph) IcKq HfwH JpqI OktQ PhwE PkwP} Vq{On(eT eZ fY hL hO pY qB) hL(Dk Ib Qh) cFrY} bW{xA(Ic Ki Nk Pk) vW(Ed Fw Oa) Hf(vB vT) MpuN} Kr{Dd(sO uX vQ vW wF tM) Jp(vS wB) AotM} dB{Hq(wG wH wL wQ) Qz(wF wG wH wL)} Db{hO(vI vP vV) NrvW bCvB} Nt{qG(Ap Kf) EtNl JdeZ JtrT} Hf{wQ(Rb Uf) wH(Hr Ld) KywF} nT{Ji(Ic Id) NjKq aMoN} Et{In(Ne Nl) aKvV} Qw{JhwP JmtL UfwQ} Ap{xA(Ez Ng)} Qa{eDmF rAkO} Qz{IcwJ NycC} Jj{mHIL iOwF} nJ{oN(aO bZ)} MtmHjU MwTvnB NaclyD NbfPwQ HwrAkO QvbCyL LjUnvW NyeDmF UfrUvP Unconstrained panels with 3 analytes, where 1.0E-6 >= 'model p-value' > 1.0E-7. Contains 5,154 panels of 27,619,476 total panels evaluated. : iH{qU(aA aC aE AF aH al AJ aK AL aM AN AO AP aQ AR AS aU aV AW AX aY aZ BA BB BC bE bF bG bH bl bJ bL BN BO bP bQ bR bS bU bV bX bZ cA cB cC cD cF cG CH cI cJ cK cL cM cN CO CP CQ cR CS CT cU CV CW CX cY cZ dA DB DC DD DE dF DG dH dI dJ DK dL dM dN Dp dR eC Ed eF Et FP Fr Fw gL gP gW HA hB hC HF hG Hq HR Hu hV HW HX iA iC Id iI Ik Im In iO IP Ir Iv iZ JD JE jF JG Jh Jj JK Jl jM Jn JO JP JQ JR Js JT JU jV jY Kc Kd Ke Kf Kg Ki Kj Kl Kn Ko Kp kQ KR kS Kz Lh Lj IL IM IO Lv Lx Ly Lz Ma Mb Md Me Mf Mg Mh Mj Mk Ml Mn Mq Mr Ms Mt Mu Mv Mw Mx My Na Nb Nc Ne Nf Nh Ni Nj Nk Nl Nm Nn No Nq Nr Ns Nt Nu Nv NW Nx NY Oa OE OF Og OH Oi oK Om oN Oy Oz Pb Pc Pd PF Pg Ph Pj Po Pz Qa Qb Qc Qd Qe Qg Qh Qm Qt Qu qV QW QY Qz rA RB RC Ri Rj Tn To Tz Uc Uh Uk Ul Um Un Ur Us Ut Vs Vt Vv tF) qV(aC aE AF aH aI AJ aK aL aM AN aO AP aQ AR aS aU aV AW AX aY aZ BA BB BC bE bF bH bl bJ bL bM BN BO bP bQ bR bS bU bV bX cA cB cC cD cE cF cG cH cI cJ cK cL cM cN CO CP cQ cR CS cT cU CV CW cX cY cZ dA dB DC DD dE dF DG dH dI dJ DK dL dM dN dR eC Ed eF Et Fn FP Fr Fw gL gP gW HA hB hC HF hG Hq Hr Hu HV HW HX iA iC Id iJ Ik Il In iO IP Iq Ir iZ JD JE JF JG JH Ji JK Jl jM jO JP JQ JR Js JT jU jV jY Ke Kf Kg Ki Kj Kl Kn Ko kQ kR kS Ky Lh Li Lj IK IL IM IO Lx Ly Lz Ma Md Me Mg Mh Mj Mk Ml Mq Ms Mt Mu Mw Mx My Nb Nc Ne Nf Nh Ni Nj Nk Nl Nm Nn No Nq Nr Ns Nt Nu Nv NW Nx NY Oa oE OF OH Oi OK Om oN Oy Oz Pb Pc PF Pg Ph Pj Po Pz Qa Qc Qd Qh Qm QT Qu QW QY Qz rA RB RC Rg Ri rX rY rZ Tz Uc Uf Uh Uk Ul Um Un Ur Us Vs Vt Vv tF) qX(aE Af al Aj aK AL aN Ao Ap aQ Ar aS aU aV Aw aX aY Ba BB bE bF Bg bH bJ bL bM BN BO bP bQ bS bX cE cG CH cl cJ cL cN Co Cp Cq cR Ct Cu CV Cx cY cZ DB dD DE Dg DK DI dN Dp dR EF Ez Fa Fb fP GL GP Ha HB HC HF hG Hq HR hV hW HX Ib Id Ih li IJ Ik Im In IO IP Ir Is It Iu Iz Jd Jf JG Jj Jl JM Jn JO Jp Jq Jr Jt JU Jv Jy Kc Kd Ke Kf Kj Kl Kn Ko Kp kR Ks Kx Kz Ld Lh Li Lu Lv Lw Lx Lz Mb Mc Md Me Mf Mg Mh Mi Mk Ml Mn Mp Mq Mr Ms Mu Mv Mw Mx My Mz Na Nb Nd Ne Ng Nh Ni Nk

Figure 23 Continued

Nm Ns Nv NW Ny Oa OE oF Og OH Oi oK Om Or Ou Ow Oy Oz Pa Pb Pc Pf Pg Ph Pi Pj Pk Po Pz Qa Qb Qc Qd Qe Qg Qh Ql Qm Qn QT
Qu Qv Qw Qx Qz Ra RB RC Rf Rg Rh Ri Rj Rm rX rY rZ Sr Ss St Tn To Tr Tt Tv Tz Ua Ub Uc Ud Ue Uf Ug Uh Ul Um Un Uo Up Ur Us Ut
Uu Uv Vo Vp Vs Vt Vu Wm Tj) rC(aA aC aE aF aG aH al aJ aK aL aM aN aO AP aQ AR aS aU aX aY aZ bA bB Bc bE bF bG bH bI bJ bL
bM bN bO bP bQ bR bS bU bV cA cB cC cD cE cF cG cH cI cJ cK cL cM cO cP cQ CS cT CV cW cX cY cZ dA dB DD dE dF DG dH dI dL
dM dN dR eC Ed eF Fb Fn FP Fw gL gP gW hA hB hC hF hG HR Hu hV HW hX iA iB IC IJ Il iO IP Iq Iv iZ JD JE jF JG JH Jl JK Jl JM jO jP
JQ JR Js JT jU jV jY Ke Kf Kg Ki Kk Kl kQ kR kS Ky Li Lj IK IL IM IO Lv Lx Ly Ma Mb Me Mg Mh Mj Mk Ml Mq Ms Mu Mw My Nb Nc
Ne Nf Ni Nj Nl Nm Nn No Nq Ns Nt Nu NW Nx Ny Oa oE OF OH oK Om Pa Pb Pe PF Pj Qa Qh Qm QT qW QY Qz rA rB Rc Rh Ri rX rY rZ
To Tz Uf Uh Ul Un Ur Vs Vt Vv tF) eD(aA aC aD aE aF aG aH aI AJ aK aL aM aN aO AP aQ aR aS aU aV aW aX aY aZ bA bB bC bE bF bG
bH bI bJ bL bM bN BO bP bQ bR bS bV bZ cA cB cC cD cF cG cH cI cJ cL cM cN cO cP cQ cR cS cT cU CV Cw cX cY cZ dA dB DC dD dE
dF dG dH DI dJ DK dL dM dN dR eC eF Et Fn fP Fr gL gP gW hA hB HC hF hG hR Hw HX iA iB iC IJ Il iO iP Iu Iv iZ jD JE jF JG jH jI JK
jL JM jO jP jQ JR Js JT jU jV jY Kf Kg Ki Kk Kl Kp KQ kR kS Ky Li IK IL IM IN IO Lw Lx Md Mg Ml Mm Mw My Nc Nf Nj Nm No Nq Nr
Ns Nt Nu nW Nx nY oE OF OH OK Om oN Oz Pd Pe PF Pz Qa Qh Qu Qz Rc rX rY rZ Tn Tt Uf Ul Um Vs tF) jL(aC aD aE aF aH al AJ aK aL
aM aN aO AP aQ aR aS aU aV aW aX aY aZ bA bB bC bE bF bG bH bI bJ bL bM bN BO bP bQ bR bS bV bW bX bZ cA cB cD cE cF cG cH
cI cJ cL cM cN CO cP cQ cR cS cT cU cV CW cX cY cZ dA dB Dc dE dF dG dH DI dJ DK dL dM dN dR eC Ed EF Et Fn fP Fr gL gP gW hA
HB hC hF hG hV HW hX iA iB iC iJ iO iP Iq It iZ JD JE jF JG jH jI JK jM jO JP jQ jR JT JU jV jY Kg Ki Kj KQ kR kS Ky IK IL IM IN IO
Mg Mh Ml My Nf Nj Nm Nn Ns nW nY Oa oE OF oH OK Om ON Oz Pd Pe PF Pg Qh qT Qu QW qY rA Rc rY tF) rB(aD Af aG al aJ AN Ap
aV aW aZ Ba bB BC bG bI bJ bM bN bR bU bV bX bZ cE cF cH cI cK cM cN CP cQ cR cU CV CW dB DC Dg dH dI dJ Dk Ed Fn FP Fr Fw
hA Hb hC HR Hu hV HW HX iB IC Id IJ Il iO Iq iZ JD JE jF JG JH Jl JK Jl JM jO jP JQ JR Js jT jU jV jY Kd Ke Kf Kg Kk Kl Kn Ky Lh Li
Lj IK IL IM IO Lw Ly Ma Mb Me Mf Mg Mh Mj Mk Ml Ms Mt Mu Mv Mw Mx My Nb Nc Ne Nf Nh Ni Nj Nl Nm Nn No Nq Ns Nt Nu Nv
nW NY Oa Of Oh oN Pa PF Pj Po Qa Qh Qm QT QY Qz Rb Ri To Tz UI Uh Ut Vs Vt tF) qT(aA aC aD aF aH aK aM An aO aP aR As aU
aV aW AX aZ bA bB bC bF bG bH bI bJ bL bM bN bP bR bS bU bV bW bX bZ cA cB cC cD cE cF cK cM cO cP cQ CS cT cU cV cW dB DC dE
dF dG dH dI dJ dL dM eC Et Fn Fp Fr gL hA hC hF HR Hu HV HW hX iB iC IJ Il In iO Iq Ir iZ JD JE jF jG JH Ji JK jM jO JP JQ jR Js JT jU
jV jY Kg Ki Kj KQ kR kS Ky Lj IK IL IM IO Lw Lx Ly Ma Mg Mj Mm Mt Nc Nf Nj Nl Nm Nn No Nq Nr Ns Nt Nu nW Nx NY Oa Ok ON
Oy Oz Pd Pe PF Pg Ph Qh qW QY Qz rA rX Uf Uh Uk Ul Up Ur Us Vs Vv Tk tF) rY(aD Af aG al aJ AN Ap aR as aW aZ Ba bB BC bF bG bI
bJ bM bR bU bX cD cF cG cH cI cK cL cN cP cQ CV CW DC Dg dl dJ dN Dp Ed Fn FP Fr Fw hA hC HR Hu hV HW Hx iB IC IJ Il In iO Iq
iZ JD JE jF JG JH Jl jK Jl JM Jn JO jP JQ JR JT JU jV jY Ke Kf Kg Kk Kl Kn Kp Ky Lh Li Lj IK IL IM IN IO Lx Ly Mf Mg Mh Mj Mq Ms Mt
Mu Mw Mx My Nb Nc Ne Nf Nh Ni Nj Nk Nl Nm Nn No Nq Ns Nt Nu Nv nW NY Oa oE OF Om PF Pj Qa Qh Qm Qt Qv QY Qz Ri rX To
Uh Ul Um Un Ur Ut Uv Vt) qW(aA aC aD AF aG aH aJ aM An aO aP AS aU aV aW aX aZ bA bB bC bG bH bI bJ bM bR bU bV bW bX bZ
cD cE cF cH cI cK cM cP cQ Cs cT cU cV cW cY dB DC Dd dF DG dH dI dJ dL dR Ed Et Fn Fp Fr Fw hA hC HR Hu HV HW HX iA iC IJ
Il iO Iq Ir Iv iZ JD JE jF jG Jh Ji JK jM jO JP JQ JR Js JT jU jV jY Kg Ki Kj Kk KQ kR kS Ky Lj IK IL IM IO Lw Lx Ly Ma Mg Mj Mm Mt
Mu My Nb Nc Nf Nj Nl Nm Nn No Nq Nr Ns Nt Nu NW Nx NY Ok ON Pd PF Pg Qh Qy Qz rA Uf Uh Ur Vs tF) qY(aA aC aF aH aJ aK
aM An aO aP AS aU aV aW aX aZ bA bB bC bG bH bI bJ bM bN bR bU bV bW bX bZ cA cD cE cF cI cJ cK cM cP cQ Cs cT cV cW cY
dB DC dF DG dH dI dJ dM dR eC Ed Et Fn Fp Fr Fw gL hA HR Hu HV HW hX iA iC IJ Ik Il iO Iq Ir iZ JD JE jF jG JH Ji JK jM jO JP JQ jR
Js JT jU jV jY Kg Ki Kj KQ kR kS Ky Lj IK IL IM IO Lw Lx Ly Ma Mg Mj Mm Mt Mu Nb Nc Nf Nj Nl Nm Nn No Nq Nr Ns Nt Nu nW Nx
NY Ok ON Oy Pb Pd PF Pg Qh Qy Qz rA rX rZ Uf Uh Ur Vs tF) rX(aA aD AF aG al aJ aN aR aU aV aW aX aY aZ bB bC bF bG bI bJ bL bM
bP bR bX bZ cA cC cD cF cG cH cI cJ cL cN cP cQ cR cT cV cW cZ dB dC dD dE DG DI dJ dN Ed eF Fn FP Fr gP hA hB hC HR Hu HW HX
iB IC IJ Il iO Iq iZ JD jE jF jG JH jl jK Jl jM JO jP JQ JR JT jU jV jY Ke Kf Kl Kn Kp Ky Lh Li Lj IL IM IN IO Lw Lx Ly Mg Mq Ms Mt Mu Mw
Mx My Nc Ne Nf Nh Ni Nj Nl Nm Nn No Ns Nt Nu NW Nx NY oE Om PF Qa Qh Qm Qt Qy Qz Ri rZ To Uf Uh Ul Um Un Uv Vs Vt)
rA(aA aC aD aF aH aJ aM An aO AP As aU aV aW aZ bB bC bG bH bI bJ bM bN bR bS bU bV bW bX bZ cD cE cF cI cK cM cP cQ Cs cT cU
cV cW cZ dB DC Dd dF DG dH dI dJ dL dR Et Fn Fp FrhA HR Hu HV HW hX iA iC IJ Il iO Iq Ir Iv iZ JD JE jF jG JH Ji JK jM jO JP JQ jR Js
JT jU jV jY Kg Ki Kj Kk KQ kR kS Ky Lj IK IL IM IO Lw Lx Ly Ma Mg Mj Ml Mm Mt Mu Nc Nf Nj Nl Nm Nn No Nq Nr Ns Nt Nu Nw Nx
NY Of Oi Ok Om ON Pd Pe pF Pg Qh Qy Qz Uf Uh Ul Ur Vs Vv tF) rZ(aA AD Af al aJ aN aV aW aX aZ bA bB bF bI bJ bM bR bX cF cH cI
cK cL cM cN cP cQ cR cV dC Dg dI dJ dM dN eF Et Fn FP Fr hB bC HR Hu hV HW HX iB iC IJ Il IO Iq iZ JD JE jF jG Jl jK jM JO JP JQ jR
JT jU jV jY Ke Kl Kq Ky Lh Li Lj IL IM IN IO Lw Lx Ly Mg Ms Mt Mu Mw My Nl Nm Nn No Nq Nr Ns Nt Nu NW Nx NY oE oF Om PF
Qh Qt Qy Qz Uh Ul Um Vs) IN(aA aD aG al aL aM aO aR aS aV aW bB bE bF bG bH bJ Bo bR bU bW bX bZ cA cC cD cE cH cI cJ cM
cN cP cQ cU cV CW cZ dB dC dD dH DI dJ Dk dL Et Fn fP Fr gW hR Hw iB Ic iJ iO Iq Iv Jd jH jI Jk jR Jt jY Ki KQ IK IL IM Lw Ml My Nf
Nn Ns nW Ok On Oz Pe pF Qh Qu Rc tF) iB(aD aG aL Ap Aw Ba bB bF bG bJ Bo bR bU bW bX bZ cA cC cE cH cK cM cN cP cQ cV CW cZ
dB DC dD dH DI dJ Dk Et Fr hC IC iJ Iq Jd Je jF Jg jH JK Jt Kf Kl IL IM IO Lx Ml Mm My Nf Nm Nn Ns NW Nx Oa Of Ok Oz Qh Qt Rc Tn
Uf Vs tF) IL(aD aG aL aM aR aS aV aZ bB bC bG bJ Bo bR bU bW bX cA cC cE cH cM cN cP cQ cV CW cZ dC dD DI dJ Dk Et Fn Fr hR
Hw IC Il Iq Iv Je Jg Jk Jt jY Ki Kq Ky IK IM Lw Ml Mm Nf Nn nW Ok On Pe pF Qh Rc Ss Tn Uf Ul tF) Ic(Ad aE Af bW cH Cv Cw Dc Dd Dk
Et hR hV hW Jd Je jF jG jH jI JK Jl jM jO JP jQ jR jT jU jV jY Kf Kr IO Lw Lx Ml Nb Nl Nw Nx Ny Of Ok On Oz Pf Qh Qt Qu Rc Rh Tz Uf
Ut Vs tF) IM(aA aH aM An aO aV bG bR bU bV bW bX cA cC cJ cK cM cN cO cQ cS cT cU cW cZ dC dD dF dG dH dJ dN hA hR iA Iq Iv Jd
jO jP jY Kk Kq kS IK Ml Nf Nq ON Pe pF tF) hR(aD aI aN Ap bB Bo bU bW bX cC cE cH cK cN cP cQ cU cV CW cZ dC dD Dg dI Dk iJ Il
Iq Jd jF Jg Jp Jt Kf Kl Li Lw Mh Ml Mm Nf Qh Rc Uf Vs tF) jY(aD aG Ap bB Bo bR bU bW HX iB iC IJ Il iO Iq iZ JD JE jF jG Jl jK jM JO JP JQ jR
JT jU jV jY Ke Kl Kq Ky Lh Li Lj IL IM IN IO Lw Lx Ly Mg Ms Mt Mu Mw My Nl Nm Nn No Nq Nr Ns Nt Nu NW Nx NY oE oF Om PF
Qh Qt Qy Qz Uh Ul Um Vs) jN(aA aD aG al aL aM aO aR aS aV aW bB bE bF bG bH bJ Bo bR bU bW bX bZ cA cC cD cE cH cI cJ cM
cN cP cQ cU cV CW cZ dB dC dD Di Fn Fr Hv lj lk Il lq Iv Jd Je Js
Kq Kr Ky Lw Lx Ml Mm Nf Nn Nq Ns Ok On Oz Pe Qz Rc Uf Vs) jH(aA aD aG bB bG bJ Bo bR bU bW bZ cK cM cN cP cQ cU cW cZ dD
Di Fn Fr lq Je Jg Jk Jt Kq Ml Nf Nn nW Ok On Oz Qh Qu Rc Uf tF) hA(aG aL bB bC Bo bR bU bX bZ cC cK cM cN cV cZ dD Et Fr Iq Jd Jk Kq
Lw Lx Ml Mm Nf Nn Ok Qh Qu Re Uf Vs) IK(aD aG bB bG Bo bR bU bW bZ cK cM cU cW cZ dC dD dH DI Ed Fr Iv Jd Je Kq Nf Ok On Oz
Rc tF) Ad(Fp Ik Il In Pf Rh tN tO tQ tR tS tT tU tV tX wB wC wD wE wF wG wH wJ wK wL wP wQ yD yL zA) jI(aD aG bB Bo bR bU bW
bX cK cM cP cW cZ dD Fn Iq Je Jg Jt Kq Ml Nf Nn nW Ok On Qu Rc) jO(aG Ap bB Bo bU bW cE cK cM cV CW dD Et Iq Jd Kl Kq Ml Mm
Nf Nn Ok On Qu Uf) On(Fp hO hV hW hX iC Iv jE jF jG jK jM jP jQ jR jT jU jV lO Pe Pf qD rT) Kq(Fp hV hW hX iC Ik jE jF jG jK jM jP jQ
jR jT jU jV lO Nf Pe Pf) Jp(qG qH ql qZ rN rO rP rQ rR rS rU rV rW sK tQ vH vI vP wC zl) iC(aD aG bR bS bU bW bX cK cM cW cZ dC dD
Iv Jd Je Ml Nf Ok Tk) hX(aN bB Bo bU bW bX cK Cw cZ Et iJ Jd Mh Ml Mm Nf Ok Rc) jF(aD aG aK aV bG bJ bU bW bZ cK dR Iq Jd Ml Nf
Nn Pe) jP(aG bU bW cK CW dD Et Iq Jd Jt Ml Nf Nn Of Ok Tn) hV(Ap bB bU bW cK cZ dD Et iJ Jd Jt Mh Mm Nf Ok) jU(aG bG bR bU
bZ cK cM cU cW lj Jd Lw Ml Mm Nf Uf) jK(aG bG bR bU bW cK cW dD Iq Je Ml Nf Ok tF) jQ(aG Bo bU bW cK cM cW dD Di Et Jd Ml
Nf Ok) hW(Ap bB bU bW bX cK Et Jd Mh Ml Nf Ok Rc) jV(aD aG bU bW cK cW dD Iq Jd Ml Nf Qu Rc) hL(Ap Co Dc Hb Jt Ju Kf Lh Nm

Tt Uc Uf Uh Ul Vs tF) rA(aE Af al Aj aK AL aN Ao aQ AR aS Aw AX aY BA Bb Bc bE bF Bg bL Bn BO bP bQ cA cB cC cG CH cJ cL cN CO Cp Cq cR cS Ct Cu Cv CX cY cZ dA Db dD DE DK Dl dM dN Dp eC EF Ez Fa Fb fP Fy GL GP gW Ha HB HC HF hG hO Hq Hx Ib Id Ih Ii Ik Im In Io IP Is It Iu Iz Jf Jg Jj Jl Jm Jn Jo Jr Ju Jv Jy Kc Kd Ke Kf Kl Kn Ko KP Kr Ks Kx Kz Ld Lh Li Lu Lv Lz Mb Mc Md ME Mf Mh Mi Mk Mn Mp Mq Mr MS mT Mv Mw Mx My Mz Na Nb Nd Ne Ng Nh Ni Nk Nv nW Oa OE oF Og OH oK Or Ou Ow Oy Oz Pa Pb Pc Pf Ph Pi Pj Pk Po Pz Qa Qb Qc Qd Qe Qg Ql Qm Qn Qt Qu Qv QW Qx Ra Rb Rc Rf Rg Rh Ri Rj Rm Sr Ss St Tn To Tr Tt Tv Tz Ua Ub Uc Ud Ue Ug Uk Um Un Uo Up Us Ut Uu Uv Vo Vp Vt Vu Wm Tj) qY(aE Af al Aj AL aN Ao Ap aQ AR Aw Ax aY Ba Bb Bc bE bF Bg bL Bn BO bP bQ bS cB cC cG CH cL cN CO Cp Cq cR cS Ct Cu Cv Cw CX cZ dA Db DD DE DK DL dN Dp EF Ez Fa Fb fP Fy Gl GP gW Ha HB HC HF hG Hq Hx Ib Id Ih Ii Im In Io IP Is It Iu Iz Jf Jg Jj Jl Jm Jn Jo Jr Ju Jv Jy KC Kd Ke Kf kl Kl KN Ko Kp Kr Ks Kx Kz Ld Lh Li Lu Lv IW IY Lz Mb Mc Md Me Mf MH Mi Mk Ml Mn MP Mq Mr Ms mT mU Mv MW Mx My Mz Na Nd Ne Ng Nh Ni Nk nO nR Nv Nw Oa OE OF Og OH Oi oK Om Or Ou Ow Oz Pa Pc Ph Pi Pj Pk Po Pz Qa Qb Qc Qd Qe Qg Ql Qm Qn Qt Qu Qv QW Qx Ra Rb Rc Rf Rg Rh Ri Rj Rm Sr Ss St Tn To Tt Tv Tz Ua Ub Uc Ud Ue Ug Uk Ul Um Un Uo Up Us Ut Uu Uv Vo Vp Vt Vu Vv Wm Tj) iC(aA aC aE aF aH al AJ aK AL aM AN aO AP aQ aR aS aU aV AW aX aY aZ BA bB bC bE bF bG bH bI bJ bL bM bN BO bP bQ bV bZ cA cB cC cD cE cF cG cH cI cJ cL cN cO cP cQ cR cS cT cU CV Cw cX cY dA dB Dc Dd dE dF DG dH DI dJ DK dL dM dN Dp dR eC Ed EF Et Fn fP Fr Fw gL gP gW hA hB HC hF hG HV HW Hx iA Ib Id IJ Il In iO iP Iq Is Iu iZ jE jF JG Jh Jl JK Jl JM Jp JQ jR Js JT JU Kf Kg Ki Kk Kl Kp kQ KR kS Ky Li Lj lO Lw Lx Ly Ma Mb Md Mf Mg Mk Mm Mp Mq mS MT Mu Mv Mw My Nc Nj Nl Nm Nn No Nq Nr Ns Nt Nu Nv NW Nx NY Oa oE OF OH Oi oK Om oN Oy Oz Pc Pd Pe PF Pg Ph Pk Po Pz Qa Qh Qt Qu Qw Qy Qz Rc Ss Tn Tz Uf Uh Ul Ut Vs Wn tF) qW(Aa aE al Aj aK AL a N Ao Ap aQ AR Aw Ax aY Ba Bb Bc bE bF Bg bL BN BO bP bQ bS cA cB cC cG Ch cJ cL cN CO Cp Cq cR cS Ct Cu Cv Cw CX cZ dA Db dD DE DK Dl dM dN Dp eC` EF Ez Fa Fb fP Fy GL GP gW Ha HB Hc HF hG Hq Ib Id Ih Ii Ik Im In Io IP Is It Iu Iz Jf Jg Jj Jl Jm Jn Jo Jr Ju Jv Jy Kc Kd Ke Kf Kl Kn Ko KP Kr Ks Kx Kz Ld Lh Li Lu Lv Lz Mb Mc Md Me Mf MH Mi Mk Ml Mn Mp Mq Mr Ms Mv Mw Mx mY Mz Na Nd Ne Ng Nh Ni Nk Nv Oa OE OF Og OH Oi oK Om Or Ou Ow Oy Oz Pa Pb Pc Ph Pi Pj Pk Po Pz Qa Qb Qc Qd Qe Qg Ql Qm Qn Qt Qu Qv Qw Qx Ra RB Rc Rf Rg Rh Ri Rj Rm rX rY Sr Ss St Tn To Tt Tv Tz Ua Ub Uc Ud Ue Ug Uk Um Un Uo Up Us Ut Uu Uv Vo Vp Vt Vu Vv Wm Tj) jE(aA aC aD aE aF aH aI AJ aK AL aM AN aO AP aQ aR aS aU aV AW aX aY aZ BA bB bC bE bF bG bH bI bJ bL bM bN bO bP bQ bR bS bV bX bZ cA cB cC cD cE cF cG cH cI cJ cL cM cN cO cP cQ cR cS cT cU CV CW cX cY cZ dA dB DC DD dE dF DG dH DI dJ DK dL dM dN Dp dR eC Ed EF Et Fn fP Fr Fw gL gP gW hA hB HC hF hG HV HW Hx iA IJ Il iO iP Iq Iv iZ Je jF JG Jh Jl JK Jl JM Jp JQ jR Js JT JU Kf Kg Ki Kk Kl kO KP kQ KR kS Ky Li Lj lO Lw Lx LY Md mF Mg mH Mm Mp MT Mu Mw My NC nH Nj nL Nm Nn No Nq Nr Ns Nt Nu Nv NW Nx NY Oa oE OF OH OK Om oN Oz Pd Pc pF Pg Pk Pz Qa Qg Qh Qt Qu Qw Qy Qz Rc Ss Tn Uf Uk Ul Vs Vv tF) rX(aC aE aH Aj aK AL aM An AO AP aQ Ar AS Aw Ax BA Bb Bc bE Bg bH BN BO bQ bS bU bV cB Ch cK cM CO Cp Cq CS Ct CU Cv Cw CX cY dA Db Dc Dd De dF dH DK DL dM Dp dR eC Ef Ez Fa Fb Fw Fy GL Gp gW Ha Hb Hc HF hG Hq Hv Ib Ik Im In Io IP Ir Is It Iu Iv Iz Je Jf Jg Jj Jk Jm Jn Js Ju Jv Jy Kc Kd Kg Ki Kj Kk Kn Ko Kp kQ KR KS Kx Kz Ld Lu Lv Lz Ma Mb Mc Md Me Mf Mh Mi Mj Mk Ml Mn Mp Mr Mv Mz Na Nb Nd Ng Nk Nv Oa Oe OF Og OH Oi oK oN Or Ou Ow Oy Oz Pa Pb Pc Pd Pe Pg Ph Pi Pj Pk Po Pz Qb Qc Qd Qe Qg Ql Qn QU Qv Qw Qx Ra RB Rc RfRg Rh Rj Rm Sr Ss St Tn Tr Tt Tv Tz Ua Ub Uc Ud Ue Ug Uk Uo Up Ur Us Ut Uu Vo Vp Vu Vv Wm Tj tF) jG(aA aC aD aE aF aH aI AJ aK aL aM AN aO AP aQ aR aS aU aV AW aX aY aZ BA bB bC hE bF bG bH bI bJ bL bM bN BO bP bQ bR bS bV bX cA cB cC cD cE cF cG cH cI cJ cL cM cN cO cP cQ cR cS cT cU CV CW cX cY cZ dA dB DC DD dE dF DG dH DI dJ DK dL dM dN dR eC Ed EF Et Fn fP Fr Fw gL gP gW hA hB HC hF hG HV HW Hx iA IJ Ik Il iO iP iZ Je jF Jg Jh Jl JK Jl JM Jp JQ JR Js JT jU Kf Ki Kk Kl KP kQ KR kS Ky Li Lj lO Lv Lw Lx Ly Ma Mb Md Mf Mg mH Mj Mk Mm Mp mS MT Mu Mv Mw MY Nc nF Nj Nl Nm Nn No Nq Nr Ns Nt NU NW Nx NY Oa oE OF OH OK Om oN Oy Oz Pd Pe PF Pg Pk Pz Qh Qt Qu Qy Qz Rc Ss Tn Uf Ul Vs Tk tF) jT(aA aC aD aE aF aH aI AJ aK aL aM AN aO AP aQ aR aS aU aV AW aX aY aZ BA bB bC bE bF bG bH bI bJ bL bM bN BO bP bQ bR bS bV bX bZ cA cB cC cD cE cF cG cH cI cJ cL cM cN cO cP cQ cR CS cT cU CV CW cX cY cZ dA dB DC DD dE dF DG dH DI dJ DK dL dM dN dR eC Ed EF Fn fP Fr Fw gL gP gW hA hB HC hF hG HV Hw Hx iA IJ Il iO iP Iq Iv iZ Je jF Jg Jh Jl JK Jl JM Jp JQ jR Js Jt jU Kf Kg Ki Kk Kl Kp kQ KR kS Ky Li Lj lO Ly Ma Md Mg Mk Mm Mp mS mT Mu Mv Mw MY Nc nF Nj Nl Nm No Nq Nr Ns Nt NU Nv NW Nx NY Oa oE OF OH oK Om oN Oy Oz Pd Pe PF Pg Pk Po Pz Qh Qt Qu Qy Qz Rc Ss Tn Uf Uh Uk Ul Vs Vv tF) hA(AA aC aD aE aF aH aI AJ aK aM AN aO AP aQ aR aS aU aV AW aX aY aZ BA Bb bE bF BG bH bI bJ bL bM bN bO bP bQ bS bV cA cB cD cF cG cH cI cJ cL CO CP cQ cR cS cT cU Cv Cw cX cY dA dB DC Dd dE dF DG dH DI dJ dK dL dM dN Dp dR eC Ed EF Fn fP Fw gL gP gW hB HC hF hG Hq HV HW Hx iA IJ Il iO iP Is Iv iZ Je jF Jg Jh Jl jK Jl JM Jp JQ jR Js Jt JU Ke Kf Kg Ki Kk Kl Kp kQ KR kS Ky Lh Li Lj lO Ly Ma Md Mg Mk Mn Mp Mq Mr mS Mt Mu Mv Mw MY Nc nF Ni Nj Nl Nm No Nq Nr Ns NT NU Nv NW Nx NY Oa oE OF OH oK Om oN Oy Oz Pd Pe PF Pg Pk Po Pz Qa Qt Qv Qy Qz Ss Tn Tt Tz Uc Uh Uk Ul Ut Uu tF) qT(aE Af al Aj AL aN Ao Ap aQ Ar aS Aw aY Ba Bb Bc bE Bg Bn BO bQ cG CH cI cJ cL cN Co Cp Cq cR Ct Cu Cv Cw CX cY cZ dA Db DD De Dg DK Dl dN Dp dR EF Ez Fa Fb fP Fy Gl GP gW Ha HB Hc Hf hG Hq Hx Ib Id Ih Ii Ik Im Io IP Is It Iu Iz Jf Jg Jj Jl Jm Jn Jo Jr Ju Jv Jy Kc Kd Ke Kf Kl Kn Ko KP Kr Ks Kx Kz Ld Lh Li Lu Lv Lz Mb Mc Md Me Mf Mh Mi Mk Ml Mn Mp Mq Mr MS Mu Mv Mw Mx My Mz Na Nb ND Ne Ng Nh Ni Nk nT nU Nv Nw OE OF Og OH Oi oK Om Or Ou Ow Pa Pb Pc Pi Pj Pk Po Pz Qa Qb Qc Qd Qe Qg Ql Qm Qn Qt Qu Qv Qw Qx Ra Rb Rc Rf Rg Rh Ri Rj Rm rY Sr Ss St Tn To Tr Tt Tv Tz Ua Ub Uc Ud Ue Ug Um Un Uo Ut Uu Uv Vo Vp Vt Vu Wm Tj) jF(aA aC aE aF aH al AJ aL aM AN aO AP aQ aR aS aU AW aX aY aZ BA bB bC bE bF bH bI bL bM bN BO bP bQ bR bS bV bX cA cB cC cD cE cF cG cH cI cJ cL cM cN cO cP cQ cR cS cT cU CV Cw cX cY dA dB DC DD dE dF DG dH DI dJ DK dL dM dN eC Ed EF Et Fn fP Fr Fw gL gP gW hB HC hF hG HV HW Hx iA IJ Il In IP Iv iZ Je Jg Jh Jl JK Jl JM Jp JQ jR Js Jt jU Kf Kl Kk Kl KP kQ KR kS Ky Li Lj lO Lw Lx Ly Ma Md Mf Mg MH Mj Mk Mm Mp mS MT Mu Mv Mw My NC Ni Nj Nl Nm No Nq Nr Ns Nt Nu NW Nx NY Oa oE OF OH OK Om oN Oy Oz Pd PF Pg Ph Pz Qh Qt Qu Qw Qy Qz Rc Ss Tn Uf Ul Vs tF) jM(aC aD aE aF aH aI AJ aK aL aM AN aO AP aQ aR aS aU aV AW aX aY aZ BA bB bC bE bF bG bH bI bJ bL bM bN BO bP bQ bR bS bV bX bZ cA cB cC cD cE cF cG cH cI cJ cL cM cN cO cP cQ cR cS cT cU CV CW cX cY cZ dA dB DC DD dE dF DG dH DI dJ DK dL dM dN dR eC Ed EF Et Fn fP Fr Fw gL gP gW hB HC hF hG HV Hw Hx iA IJ Il iO iP Iq Iv iZ Je Jg Jh Jl JK Jl Jp JQ jR Js Jt jU Kf Ki Kk Kl kO kP kQ KR kS Ky Li Lj lO Lw Lx LY Mg mH mI Mm Mp Mq mS mT Mu Mv Mw nB NC nH NJ nK nL Nm Nn No Nq Nr Ns Nt Nu NW Nx NY oE OF OH oK Om oN Oz Pd Pe pF Pg Pz Qh Qt Qu Qy Qz Rc Ss Tn Uf Ul Vs tF) rY(AA aC aE aF aH Aj aK AL aM AO aP aQ Ar aS aU aV Aw AX aY bA Bb bE Bg bH bL BN BO bP bQ bS bV bZ cA cB cC Ch cJ cM CO Cp Cq cR CS CT CU CX cY cZ dA DB DD DE dF dG dH DK DL dM dR eC EF Ez Fa Fb Fy GL GP gW Ha HB Hc HF hG Hq Hv iA Ib Id Ih Ii Ik Im Io IP Ir Is It Iu Iv Iz Jf Jj Jk Js Jv Jy Kc Kd Ki Kj Ko kQ KR KS Kx Kz Ld Lu Lv Lz Ma Mb Mc Md Me Mi Mk Ml Mn Mp Mr Mv Mz Na Nd Ng Oe Og OH Oi oK oN Or Ou Ow Oy Oz Pa Pb Pc Pd Pe Pg Ph Pi Pk Po Pz Qb Qc Qd Qe Qg Ql Qn QU Qw Qx Ra RB Rc Rf Rg Rh Rj Rm Sr Ss Tn Tr Tt Tv Tz Ua Uc Ud Ue Ug Uk Uo Up Us Uu Vo Vp Vu Vv Wm Tj tF) lO(aA aC aE aF aH aI AJ aK aL aM AN aO AP aQ aR aS aU aV AW aX aY aZ BA bB bC bE bF bG bH bI bJ bL bM bN BO bP bQ bR bS bV bX bZ cA cB cC cD cE cF cG cH cI cJ cL cM cN cO cP cQ cR cS cT cU CV CW cX cY cZ dA dB DC DD dE dF DG dH DI dJ DK dL dM

Mf Mg Mi Mj Ml Mp Mt Mz Na Nd Nf Ng Nh Nj Nk Nm Nn Nq Nr Og Oi Oz Po Qa Qb Qc Qd Qe) Nh{Fp Hu Hw Ii Ik Il Io Iq It Iu Ji Jm Js
Mf Mj Ml Mp Mz Nd Ng Nj Nn Nr Oi Po Qa Qb Qc Qd) Nj(Ax Fw Hw Hx Ii Il Io Iq Ir Iu Ly Mp Mz Nd Tj) dB(hR jY qU qX rX rY) No(tO tT)
Na(qX xA) Qd(qO qP) cC(bX hR) NcHx KkvQ PeuP bWxA iOuY qDqG} Na{Kq(eD gW hR hV hW hX iB iC jD jE jF jG jH jI jK jL jM jP jQ
jR jT jV IK IL IM IN IO rC rX rZ) On(aG Ax bX dE iA Kk pS qZ rN rR rT rW uG uL uP uY vH vW wC wK wQ yL zG tM xA Tj) qX(Ao Ap
Ba Bo Co Cp cW Di Ed Jd Je Kg Ki Nl Qt Qx Rc Ut Vs) Bc(qI qP qZ rO rP rQ rU sK uG uM vB vI vV wD yD yK) Iq(qZ rT rU tV uL uZ vB)
Jt(qZ rS rT sK uL wJ wK) Dc(qQ rN rU uY wQ tL) Vs(qU qV qW rA rY rZ) xA(Ap bW Jp Lh Mh) cW(qU qV qY rY) qD(rT uW wC wG)
uY(bC bW Jd Jp) Jp(rT rU) Lh(wJ wQ) bC(rT wG) bW(vT tL) nA(Lx Ny) TzvH IiwQ RcIL QhqQ NxqZ OmtT cErZ iOsC kFoN} Qw{Me(sM
tQ tR tU tV tX vA wB wC wF wG wL wP wQ xA) qQ(aX cC Dc Dk Hq Iu Jt Ng On Pi Qh Uu) wQ(Aj Ap bW dN Ib Jh Jk Jm Kf Kg qD)
xA(Ap Bb Bc bW Fw Iq Jh Jk Pk rA rY vQ) tL(BC bW Dc Hw Is Jj Jk Jr Kj) Ny(aM bG bX cC qV qX rY) Jh(fN qO uM uY vP yJ) Qy(Dc Ex Gz
Nj Nl Ss) Jj(tN tO wF wL yH zH) Iq(rT rU uY uZ vH) On(Iv Nj rY uG wC) qD(Ib sC uW tM) qO(Ap Bb Fw Om) Dc(rN rU uY) bC(vT wF
wG) rY(cW Nx Po) qP(Ap bG dB) Nj(Fr Ib) Jt(rN rP) cC(Dk Vs) wL(Hw Pz) ApwJ BcwF BgIb CheZ QtaW QhuY JkvB JrJs KjrN UuvW
aGqZ bWvT} Db{qX(cW Dd Di Iv Jd Kk Kq Nc Ni Nl qV To Tr Tt Uf Uk) Kq(eD hA hR iB iC jL jM jO jP jU jY IM qU qV) Rc(eD hA iC jD
jK jL jO jP jR jT jY IL IN) Bc(sO tV uG uN uT uY vH wE wK wL yD xA) Jd(eD hO iC jH jK jL jO jP jY IL qU qV) Nj(Ed Hc jL Ly On Qt qU
qV qW Uf) jL(cC cW dB Dc dD eC Jg Ju Qh) qU(bC cW Fn Ji Li Mm On Uf) cW(eD hA jO jP qV) Qh(eD jM jP IN) bC(qV rY rZ vW) aC(bE
bX cF) cE(bX hA rZ) hO(Aj Jt xA) qV(Kk Mm Uf) Ly(cN wQ) eD(On pF) wH(Fp Uk) uY(No Nr) DdwQ UfjO bWxA qDtM kFoN} dB{jL(bG
bR bU bX Dc Hq Iq Kg Nm No Nq Ns Nu Qh qU qV qX rC rX rZ Ul) Jp(tO tQ tR tS tT tU tV wB wC wD wE wF wG wH wJ wK wL wP wQ
yD) eD(bW bX Iq Jd Nm Nn Nq nR Ns Nu On Qh qX Ul) qU(bW Iq Kf Kq Li Lw Lx Mm nR On Qh qX Uf Vs) qX(aZ bG bU bX cF iC Iq jF
jH IN IO qW) rZ(bC bW cE cG hA Mm) Hq(wB wC wD wE yD) nR(iC jK jM jP IL) On(hA jU jY IN) Jd(jH jY IL) Qh(jH IL IN) Kq(hR Ik jY)
bX(cE iC IM) mU(hA jK IO) Mm(qV rY) wF(Bc Dc) jK(IW mH) ExqQ NnIL UfwQ bWvB cEhA rXIK} oN{dN(kC kG kI kK kN kO kP IW IX
IY mE mF mH ml mM mP mS mT mU mW mY mZ nA nB nC nD nF nH nl nJ nK nL nM nO nR nU oO) aO(kC kG kl kK kO kP IW IX IY mE
mH ml mM mS mT mU mW mY mZ nB nC nD nF nl nK nL nM nO nR nU oO) kF(aA aN As aY cM Dc eC gP Gz Hw iP jK KS Mt nC nH oP
oQ tF) jP(kE kl kO IX IY mF mH nB nO) tF(kN kO mF mM mZ nC nH nJ) kO(jK IL nH nJ) nN(aM aY nC) fP(hO qD) mP(aP bZ) ExqQ
MwnK NjnR aAnJ aMnO mZoO} Um{uY(aC Aj Ap Aw aZ bE bF bG cE cG cL hA Hq iC Ik iO Iq Kr Kx Ky Nb No Of pS Qe Rb Uf uI vQ
Vv) tL(Ap Aw aZ Bc bE bF bG cE cG Fb gL Hq iC Iq Kr Nb Of rU vQ) vQ(bI Ed Fw Kr Lx Mp Nf Nn Oh Pg Po qD Qe Up) qD(rQ tR tT uN
uU vS wQ yH yL tM xA) wL(aD Aw Fr Of Pf Uk vU) Qe(sM tR tS uU zH xA) Kr(sO tR uU vS yL) qC(Dk Kf vS) yL(Ha Lx Qb) tR(Lx Po)
wF(bF Uk) EdqZ MpwP JrJs UfvA UvuU VvvB PevU bWxA cAwG} Nj{Nh(Fp Hq Hu Hw Hx Ii Ij Il Io Iq Jm Js Lj Ly Mf Ml Ne Nk Nl Nn Nr
Oi Qa Qb Qc Qe) Nk(Ap Bo Dc De Di Ex Gz Hc Ib Kk Ne Nl Qt Qy Rh Ss Tn Vs) Ne(Hq Hw Hx Il Io Iq Js Lj Ly Mf Nn Of Oi Qb) Ed(Bo Ex
Fr Gz Id Jd Jl Kq Lw Lx Qt Tz Uf) Nl(Hq Hw Hx Il Io Iq Js Ly Mf Ni Qb) Tj(Bo Kq Ny Om On Ut Vs) On(As Ax Fw Ql Up) Up(Lx Mu Qt Ut)
Bo(Cv Fp Of) DcIl IkQt IvVs} No{Jd(pS sC sK sM sO tN tO tQ tR tS uG uM uO uP uR uT uU uY uZ vA vC vH vP vQ vU vV wC wD wE wF
wG wH wJ wK wQ yH yJ yK yL zH zI yE tL) Iq(qO qP qQ rR rT rV sK tO tR tS tT tX uR uV uZ vB vP vQ vS wD wE wF wH wL yH zH tM
tL) uY(dN Fw Jf Kr Ky) vW(Ap bW dF Kr Ql) xA(Ap bW Jv Uf) bC(vT wL tL) Ap(tU vU) Nn(tO tX) wF(Bc iO) vT(Jr Kc) ChtM NltX JvyE
mFhX} Kr{Uf(eZ pS qA rQ rU sC sK sM uG uL uN uO uP uT uW uY uZ vI vP vS vT vV vW wC wD wF wJ wK wL wQ yH yJ yK zG zH zI
yE tM tL) Dd(pS rQ rR rU sM tR tS uG uL uM uR uU uV uW uY vB vI vT vU wB wH wJ wK wL wP yD yL zH zI tL xA) Jp(uM yE tM tL)
Bc(sO uU wK) Jt(hO qD) DccF MmvB KqhW PjrV PkuY bWvW qCtM} Ap{Kk(pS qG qH qI qV rN rO rP rQ rS rT rU rV rW sO tQ tR uI uO
uX vB vS vU vW wF wP yJ yL zG zH zI tM tL) aK(eT eZ fN fY hL hP pY qA qG uY) qG(Af As Bn cC cF Ki qD Qn) xA(Hu Oy qW rN Uc)
qO(Qd qU Uc) wQ(Nk Pd) uY(aI iO) IktL LjvW VtfY cCqA gWqC wKqD jTrV} Ne{Hx(Hq Im Iq Jg Jq Jt Lx Ly Mf Ml Mr Nn Nv Nw Nx Ny
Of Om On Pg Po Pz Qa) Ly(Hq Hu Hw Iq Jm Js Mf Nh Nn Oi) Iq(Hw Ii Il Io It Js Nn Qb) Hq(Hu Hw Js Nn Nq Qb) Of(Hw Ii Il Nn Oi) On(Ii Il
Js Nn Oi) Nq(Jh My) IiLh JgOi JrJs bXcC jHkO} nA{Ny(Bg Bo Hv Iq It Iv Jn jP Jr Js kQ Mq Mx nB nJ Nq nU Of Oz Po Qc) Po(Fp Ik kO nC
nH nL Oi) Bo(Hw Ir Is Jq Mk Mw) kO(Jl Nv Nw Pe Pg Qb) Pe(Ik nC nH nL) Lx(bZ kF Oi) Nv(nC nH nL) ExIb} bW{xA(Ar As BG Ez Jj Lh
Nq Pc Pi Qh Qt Qu Qv Rb rZ Ue) Mp(tS uG uL uU uY uZ vB vW wD wG zG zH tM) vW(dL Ha qC qD Up) vT(Mu Mw Nk) tL(Nk Qt) uY(Mu
Rb) cChR cMuG iOuN} jP{nR(aC aF aH aI aL bB bE bN bX cB cE cG cH cI cO cW dD dF hG iJ iP oE) mF(cE Mr Nr Nv Ny Po) mH(Me Mr
Ny Po) mM(aG bL cJ) cW(IX Of) mZ(dE hG) NxIX} Bc{fP(uU uW uZ vH vP vV vW wJ yH yE tL) cC(qI sO tR tS tU uG uL) Gz(qZ rQ rU)
tV(iA Ki wF) uN(cF Hq Qv) As(sO uZ) Ex(qZ rY) jY(yD zA) AoxA RbwG QvuZ aZyK dNwF qVuY} bX{cC(aZ bF cE cF Is Ly Mt Nh Nl Ny
Vs) cE(aC aG aZ bG bR bZ cF cO cU) Bo(aC aZ cT Dc) bF(aC aG aO aZ) Dc(Gz Il) IkKq aCaZ cLdH} mH{cF(gW jE jF jM jQ jR IK) qV(qD
aG aX cW dH dM gP) IL(Ir Lu Me Mr Og) Me(jO jU jV) Mt(jF jV) aC(jK qW) IK(bP Wm) IM(aP dN) qUkO jVkS} Nl{Hx(Hq Im Iq Lx Mf Mr
Nw Ny Of On Pg) Iq(Hw Il Io It Js Ly Nk Qb) Nk(aX Mf Nn) On(Ii Io Js) Nq(Hq Jh) Oi(Cy Of) JrJs jHkO} Nh{Hx(Hq Hu Im Iq Lx Mf Mr
Nn Nw Ny Of Oi On Pg) Hq(Hu Hw Nn Nq) Iq(Hw Ii Il Io) On(Ii Nn) NqJh LyOi JrJs} Ik{Kq(aF aG aR aW aX aZ bG bJ bU cB cC cF cP cQ
cZ dC dL) AouM PonK RcnH KfaR NymZ} qD{tM(bM cF cM dN eT Ur vB) qG(Hb Jt Kc Kf) fP(eZ yE) wQ(Hc Lh) uP(Jt Nm) MevW IqJp
KfaK UfwK PkrT} mF{jE(Hw Ih Im Ir Nk Nr Ny Po Qa Qb) rB(Md Nr Pe) Lx(bZ Po) hX(Ir Md) qV(bZ iA) BokF aOlM} kO{rA(Aa Fp Ih rB)
Po(Lx Ny) Tv(nB nH) nK(Lx Ny) qX(Aa Qa) qU(eD Oi) IM(eC fP) KlnH OwnB bJjR bLjD hGlK} Kk{Kf(qC rO rU rV vQ) fR(dK Pe Pg Ua)
iP(nC nH nL) Uf(tV vI) IvOn KijQ OmvQ aOtR} Ny{Po(lY nC nH nJ nK nL nO nU) nK(Bg Fp Ij Iv nC Oi) nO(aM Ns) KenB} mZ{Lx(aA Ko
Po) aY(eD jK) cM(jD jU) IK(aK tF) IM(aP fP) MfOg IsKo cWjU cYjR nNrY} nB{Tv(aA aO aS bZ De kF nN Ph) Ow(Iv nN Pk) Kn(kC nL)
rA(Hw Jm)} uY{Ky(cC Hw Lh Pa) Jd(cC Ki Ue) Jh(Ez Ki) Jp(iO Ue) FpcS MddN HwUv IqaC} Bo{aC(aX bE cF cZ) cF(cI Dc) nJ(Mk tF)
EdqX TjTv TohR OwnN aKgW IYoH} cW{IX(iC jD jK jU IK qV) rY(Ed Fw Il Kp) EdqX FnhA mTjU mUrA} Iq{Pk(rU uZ) tV(Iv Pe) EdrV
FnqU NkuL QbqA QdwH RmqG aCvB dCuZ} nR{IL(bM bP bZ cC dH iA) aOlK cCjK} Kl{Jd(eD qV qX sM uP) Jh(hR qX)
EdqX FnqU UksC} Ex{Dc(aC rN) DkaC DlhL PoTn JdqI KqTk aKgW iOqQ} cF{Dc(aC Il) Hu(Jd Jg) Qh(Tk Wn) cE(bG dH) aCbE}
xA{Pk(aP bC bO Ed) Mm(cC qW) Uf(Js qW) EdPa} fP{IM(IY nC nL) wQ(Uk Vv) NbzI JdqQ iOwD} Kf{Js(qG qU qV qX rA) qC(aK gW)}
Gz{PoTn HuHc IjTk OnrN iOqQ} dN{vW(hL tL) PksM mPIM qCtM} nO{Tv(Dp Ib) aM(cG Jq) LxaA} nK{nL(Nv On Po) Lx(aP bZ)}
Fn{Rc(hA jY) LjvW bLqU} aZ{fY(rY vB) aKwG wQjH} cC{hR(Kq Mm Uf) KqjY} Ow{nN(lY Ql) IvmY} aO{IM(nl nJ) qVkG} nC{IL(Jn
Nk) KniP} iO{wF(Hw Lh) AowE} Hu{CheZ HqwG} Ib{oP(Cq Tv)} Qv{bC(vW wL)} Jp{NbwG bGqO} dH{IlOn mTqV} nJ{DcVu mErX}
nL{KniP bFjK} wQ{EzUf JuaC} uP{QdJt LhPe} AjTveZ EdHwvW LdbRfR aFqVkG aMmMjU

Unconstrained panels with 2 analytes, where 1.0E-7 >= 'model p-value' > 0. Contains 1 panels of 155,299 total panels evaluated. : iHqX Unconstrained panels with 2 analytes, where 1.0E-6 >= 'model p-value' > 1.0E-7. Contains 22 panels of 155,299 total panels evaluated. : iH(eD
hR iB jH jL jY IK IL IM IN qT qU qV qW qY rA rB rC rX rY rZ) qTkO

Figure 23 Continued

Unconstrained panels with 2 analytes, where 1.0E-5 >= 'model p-value' > 1.0E-6. Contains 48 panels of 155,299 total panels evaluated. : iH(hA hV hW hX IC jD jE jF jG jI jK jM jO jP jQ jR jT jU jV lO) Ne(Et Hx In Nj Nt Ok) Nh(Hx In Nj Nt) NI(Et In Nt Ok) Cw(qG Qz uY) nT(cG cL oN) Ic(dJ Qy) qT(nC nL) BoQz EtKk VqrY Unconstrained panels with 2 analytes, where 1.0E-4 >= 'model p-value' > 1.0E-5. Contains 452 panels of 155,299 total panels evaluated. : NI(Fp Fr Hq Hr Hu Hv Hw Hx IH Ii Ij Ik Il Im Io Iq Ir It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nm Nn No Nq Nr Ns Nu Nv Nw Nx Ny Oe Of Og Oh Oi Om On Oy Oz Pa Pb Pc Pd Pe Pf Pg Po Pz Qa Qb Qc Qd Qe) Ne(Fp Fr Hq Hr Hu Hv Hw Ih Ii Ij Ik Il Im Io Iq Ir It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Nf Ng Nh Ni Nk Nm Nn No Nq Nr Ns Nu Nv Nw Nx Ny Oe Of Og Oh Oi Om On Oy Oz Pa Pb Pc Pd Pe Pf Pg Po Pz Qa Qb Qc Qd Qe) Nh(Et Fp Hq Hr Hu Hv Hw Ih Ii Ij Ik Il Im Io Iq It Iu Iv Jg Jh Jj Jk Jm Jn Jq Jr Js Lj Lu Lv Lw Ly Lz Mc Md Mf Mg Mh Mi Mj Mk Ml Mm Mn Mp Ms Mt Mu Mv Mw Mx Mz Na Nc Nd Nm Nn No Nq Nr Ns Nu Ne Of Og Oh Oi Ok Om On Oz Pa Pc Pd Pe Pf Pg Po Pz Qa Qb Qc Qd Qe) Cw(aC cF eD eZ hL hO Ic iH jO jP Nj qC qD qQ qX rN rT rW rY sK vH vl vT wQ tL xA) iH(Ad Bo bU bW cE cF cH cM dD Et Fp hO iO Kq Ly Ml Nj On oQ Pe Pf rT wH tF) Ic(aC aP aR bG bX cE Cv Dc dD Et Ib Jd Jk Kq Nj oF On Qt Qz) Qz(cC Db Dc Et Gz Hf Ib Lj Nj On Qt Qy) bX(aC Ad aZ bF Bo cE dJ) Et(Io Ks Nd Nj Rh Us) cF(aC Ad bF Bo cE dJ) qT(nH nJ nO nT nU) Nj(Ad Bo Ed Ok) Hf(eD qU qV qX) Us(Dc IO On qQ) oN(kF mM nJ nN) Qw(Qt Qy xA) Um(uY wL tL) Ad(aC Nm) Ny(nA nT) dB(jL qX) BoaC DbqX NtKq TvIn KkfR KzuY VqrU dGnT Unconstrained panels with 2 analytes, where 1.0E-3 >= 'model p-value' > 1.0E-4. Contains 1,727 panels of 155,299 total panels evaluated. : iH(aA aC aD aE aF aG aH al a aK aL aM aN AO AP aQ aR aS aU aV aW aX aY aZ BA BB bC bE bF bG bH bI bJ bL bM bN bO bP bQ bR bS bV bX bZ cA cB cC cD cG cl cJ cK cL cN cO CP cQ cR CS cT cU CV cW cX cY cZ dA dB DC Dd dE dF DG dH DI dJ DK dL dM dN dR eC Ed eF eT eZ fN fP Fr Fw fY gL gP gW hB HC hF hG hL hP Hq Hu Hw iA IJ Ik Il In iP Iq Is Iv iZ Jd Je Jg Jh Ji Jk Jl Jm Jp Jq Js Jt Ke Kf Kg Ki Kk Kl Ko kQ KR kS Ky Lh Lj Lu Lw Lx Mb Mc Mf Mg Mh Mk Mm Mp Mq Mr MT Mu Mv Mw My NB Nc Nd Ne Nf Nh nJ Nk Nm Nn No Nq Nr Ns NT Nv NW Nx NY Oa oE OF OH OK Om oN oP Oy Oz Pb Pd pF Pg Ph Po pS pY Pz QA qB qC qD QG qH ql qO qQ Qt Qu Qv Qw Qx Qy QZ Rb Rc Rh rN rO rP rQ rR rS rU rV rW sC sM sO Tn tT Tv tX Ud Uf uG uM uN uO UP uR UT uU uV uW uY uZ vB vH vl vP VS vT vV vW wB wF wL wQ yD yH yK yL zG yE tM TL xA Wm Tj) Ic(AD aE AF aG aH al AJ aK AL aM aN AO Ap aQ Ar aS aU aV AW aX aY aZ BA BB BC bE bF bH bI bJ bL bM BN BO bP bQ bR bS bU bV bW bZ cA cB cC cD cF cG cH cl cJ cK cL cM cN CO cP cQ cR cS CT cU cV cW CX cY cZ dA DB dC Dd DE dF DG dH dl DK dL dM dN Dp dR eC Ed EF Fn fP Fr gL gP gW hB HC HF hG Hq Hu Hw iA Id iJ Ik Im In iO iP iZ Je Jf Jg Jh Jl Jp Jq Js Kc Kf Kg Ki Kk Kl Kn kQ KR kS Kx Ky Kz Ld Lh Lj Lu Lw Lx Mf Mg Mk Ml Mm Mn Mq Mr Mu Mv My Na Nb Nc Ne Nh Nk Nl Nm Nn Ns Nt Nv NW Nx NY Oa OE Of oH OK Om oN Or Ow Oy Oz Pb pF Pg Ph Po Pz Qa Qg Qh Qu QV Qw Qx Rb Rc Rg Rh Ri Rj Sr Ss Tn To Tv Tz Ua Uc Ud Uf Uh Uk Um Up Ur Us Ut Vq Vs Vu Wm tF) Cw(bX cK cN cP Ed eT fN fY gP gW hA hP hR Hu hV hW hX iA iB iC Id iJ In jD jE jF jG jH jI jK jL jM jQ jR jT jU jV jY Kk kQ Kr Ky IK IL IM IN IO Mp Nd Ne Nh Nl Nm Nt nW oH oK Or Ow Ph pS pY qA qB qH ql qO qP qT qU qV QW QY qZ rA rB rC Rh rO rP rQ rR rS rU rV rX rZ sC sM sO tN tO tQ tR tS tT tU tV tX uG ul uL uM uN uO UP uR Us uT uU uV uW uX uZ vA vB vC vO vP vQ vS vU vV vW wB wC wD wE wF wG wH wJ wK wL wP yD yH yJ yK yL zG zH zI yE tM Tj tF) Qz(Ad Ao Ap aR As AW Ax aZ BA Bb bF cE Ch Co CT CV dB Dd De Di dJ Dk Ex Fr Gp Hc Hq Hu Hv Ik Im In Ip Iq Is Jd Je Jg Jh Jk Jl Jp Jq Js Kf Kg Ki Kk Kl Kq Kr Ky Kz Lh Lu Lx Me Mf Ml Mu Mv My Na Nb Nc Ne Nh Nk Nl Ns Nt Nu Nx Oa Of Oh Ok Om Ow Oy Oz Pg Ph Qa Qg qQ Qu Qv Qw Qx Rc Rh Ri Rj Sr Ss Tn Tz Ua Uf Uk Up Us Ut uY vB Vq Vs Vu vW wJ wL wQ xA) Nj(Af Aj Ao Ap aR Aw Ba Bb Bc Bn bX cE cF Ch Co Cv Cx Db Dc Dd De Dg Di Dk DI EF Ex Fw gL GP Gz Hc Hq Hw Hx Ib Id Ij Il Im In Io Iq Iv Jd Je Jg Jq Jy Kg Ki Kk Kl Kn Kq Kr Ky Kz Lh Lj Lu Lv Ly Me Mf Mg Mt Nc Nd Nf Ni Nn Oa Of Og On Ow Pc Pg Qg Qt Qu Qw Qx Qy Rh Rj Ss Tn Uf Uk Um Up Us Ut Vq Vs Wm Tj) cF(Aa aE aG Aj Ao Ap aQ aR aU Aw aY aZ BA BB BG bJ bM Bn bQ bR bS bU bW bX cB cC cG cH cl cK cL cM cN Co CP cQ cR cT cU Cv cW DB Dc DD DE Dg dl Dk DI Et fP Fr Is Jd Jg Ne Nh Nl Ny Ok On) Bo(Ad aG Aj aK aO aQ aR aS aU aX aY aZ bA bC bF bG bM bO bR bU cB cE cH cl cK cL cN cP cT cU Cv cY cZ Db Dc Dd dE dJ Dl dR eD EF Et fP gL gP gW hA Hu Is kF Kk IL Ly mF mZ Ne NH nJ Nl nT Qw Tn Tj) Us(Ad eD hO hR Ib JD Je Jk Jl Kq Lh IL IM IN IO Ly Ne Nl On qT qU qV qX Qy rT rU rV rW rY sC Tn TV Ut uX uY uZ Vs wD wF wH wP wQ tL xA) Et(Aa aG bX cC Db dJ Ed Ez Fw Fy Gl Hf hR Hx iA Ib Id li Il In Js Ki Ko Kr Ky Kz Ly Me Mi Mn Mp Nc Nn Nq Oi Ph QI Qm Qw Qy qZ rB Ri Uh Up Tj) bX(Ao Ap aR Aw BA BB Bn bQ cB cC cG Ch cK cL cP cT DB Dc De Di fP Fr Is Jd Jg Ki Ly Mt Ne Nh Nl Ny Of Ok Om On Vq) oN(kC kE kG kl kK kN kO kP IW IX IY mE mF mH ml mP mS mT mU mW mY mZ nA nB nC nD nF nH nl nK nL nM nO nR nU oO oP oQ) dJ(aC Ad aQ aU bF bR bU cB cK cP ED Ef fP gW hR hW Is Jd jF jU Kq IL IM IN Ly Ok On qV QW qY rC rX rZ Tn) Db(aC cP eD hO iB iC JD jL jO jT jU jV jY IK IL IM IN IO Ly Ne Nl On qT qU qV qW rA rY uY) Nh(aA Fr Ip Ir Is Ji Jl Jo Jp Jt Lh Li Lx Ma Mb Me Mq Mr My Nb Ni Nv Nw Nx Ny Oy Pb) Qw(cE Dc Ib Jd Jk Nl On qG qO qP qQ rN rO rV tO tV uM uY vB wF wG wL wQ yL tL) dB(eD hR iC jF jH jQ jR jT jU jV jY IK IL IM IN IO qT qU qV qY rA rC rX rZ wH) Na(qQ qX qZ rO rQ rT rU rW sC tV uL uP uW uX uY vW wK wQ yL zG zl yE tM xA) aC(Aj Ao Ap Aw aX aZ Ba Bb bE bF bR bU cB cE Co CP cZ Dc Dd De Dg Di Ex) Kz(Hc hO Jd Kc Nl On pS sC sK sM ul uL uM uU uZ vH vQ wQ yL zG tL xA Tk) Hf(hA iC jD jL jO jT jY IK IL IM IN IO qT qW qY rA rX rY rZ uY wH) nT(aY bW cE cH cN dF Dg Ex hB hC Id Kd Kq Lx Nv Oh Ow PF Tv Uc) bF(Ad aG aO aZ bG bH bM bR bU bZ cB cH cl cK qT cU dE dH) mZ(cG cL iB Jq Lx Mp Mt mY nJ No Ny Og Oh oQ qT qX rA rY) Iq(fP hO hP Kk Ok qC qD qZ rT tV uZ vB wD wF wL yL zA) Ok(Aa aG aZ cC Hw Hx Il In Io Kk Ly Mp Mz Nc Nd) Vq(qG ql qQ qV qX rO rP rQ rR rS rT rV rW rZ) Ad(aZ cB cE cK cL cN cP cT dE In Kk Nt Rh) On(aG aR As aZ bO cC dE dH iA Kk Up Tj) cE(bG bR bU bZ cB cE cO cP cU dH rZ) Lx(kF kO IX mF mH nA nB nK nL nO) Jd(eZ Hu Ik Ki Kk Ne Nl Nt uY) nB(cG Kn Ny OH Ow qT rA Tv) kO(IL mY nH nJ Ny qU qX rA) Ap(eZ Kk qC qG uY xA) Ny(IX IY mF mY nK nO) fP(cC eZ hO Hu Iv wQ) Fn(eD jU IN qU qV) Nl(aA aX Ip Is Qy) In(Dc Kq Nc Tn Ut) aZ(qX sC vP vV wQ) cG(kF nC nH nJ nO) uY(bW Kr Ky Pk Rb) Ly(cC cT Gz Nc) Ne(aA Ip Is Qy) Kk(Jg Qy Tn uU) Po(mF nA nK) Nt(Hc Kf Tn) Mr(mF nA nK) Um(vA vB wF) bW(vW wL tL) cB(aG cK cP) cL(bR nH nO) Bc(uN wF) Ki(qV qX) Up(Dc Ut) Pk(qC xA) cW(eD hA) qD(uP tM) oQ(nO oH) BbcP BgIb DdQy GzRb NorO MnnK TohR IsbR OwnN UksC cCqX dNvW mFrX mYnC nDqT Constrained panels with 3 analytes, where 1.0E-9 >= 'model p-value' > 0. Contains 3 panels of 27,619,476 total panels evaluated. : Vq{rY(Ad Jv)} OnhLiH Constrained panels with 3 analytes, where 1.0E-8 >= 'model p-value' > 1.0E-9. Contains 64 panels of 27,619,476 total panels evaluated. : iH{Ad(fN fY hL hO hP jL jY pY qA qB qC qD qO) qX(aG aZ Ed Ic Iv IN rA) On(qG rB). EtqG QzqQ JprT OkrY aJsC} Cw{Ld(qG qH qQ)

Figure 23 Continued

Nq(qO qP) hO(qO qP) rN(Fp Pf) BcqZ eZoK gPhL iOqQ} Us{Ad(qH rU) hR(Dk Kq) BcqZ UchX OkrY OnlM} kO{qT(hR hV oO oP rB) hWrA} Nt{qO(Ap Et) JtqG} dJ{KqnT PkqI bBwQ} AdNarU ApKkrR QzdBqQ VqgLrY

Constrained panels with 3 analytes, where 1.0E-7 >= 'model p-value' > 1.0E-8. Contains 880 panels of 27,619,476 total panels evaluated. :
Cw{uY(aC AD aK Al aM aN aP aQ aS aU aV Aw aY bA BC bE bH bN bO bP bQ bW bX cB cN cP cT cU Cv cW cZ dA Dc Dd dH Di dJ dL dR eC eD eT Fb fP Fw fY GP gW hG Hr Hu hV iA Id iH iJ iO iP Iq Is iZ Jd Je Jf Jh jL jM Jp jQ jR jT Kk kR Ky Kz Ld Lj lM Mn Nc Nk No Nr nW nY oF oH oK Or Pf Pk qA Qg Qh qO qP Qw QY Qz rB Rh rN rW sC Tz Ub uG uI Um uN Uo uP Uu uV uX vI vP vV zH Tj tF) Nq(qI rO rR rW sM uO vB vI vP vV yH yK zH tL xA) Pe(sC uG uN uP uU uW vI vP yJ tM) No(vA vB vO vS vT vU yH tL xA) vI(cC hL hO jK oK QD qV Vv) Bc(uL uV uZ vT wF yJ xA) wQ(aN Dl Ky Ne Rb sK Uk) vB(aP cB dJ Hu Ld Pb Vs) Vv(qO qP qX rY vP vV) xA(cZ Hu jK jL Lj rN) wL(aK bC cW Hu Kk) vT(aL bW Hu jL Ld) hL(iH uN vP vV) tL(cW eZ Kl Ky) vH(cW nW Ub Um) Ed(qG wB wJ) hO(rW vP vV) qD(qU sC uN) Po(sC uN) Ha(uP uW) Nr(rT uM) Ly(vV wJ) Ld(wF wH) dA(uP zG) qV(vP vV) rN(jF jY) GlwH NjsK UbuL HuwF cBwJ dJjO iOuZ qGvU} iH{qX(aJ An bG bV bZ Cs cU dC dH Dl Et Fn Fp Fw Iq iZ Je JH jI Kg Ki Kk kS Lj Ly Mj Nl Nq Ok qU qV Qy) Jp(rB rY sO uI uL uM uV uY uZ vB vO vS wB wE wF wH) sC(Bc Cs Cv Fn Ha Ju Jv Lj No Nr Qc Qd Us Vv) uY(Et Hb Hw Jh Jt Kg Lh Mm No Nr Nt Nu Ok On) uZ(Ap Et Hb Ij Jt Lh Nn No Nq Nr Oa Ok On Us) qU(bW cE Fn Hv iB Il Ji Li Lw qT Uf) jL(aG bU cC cK dC dD Ic Iv Jd rZ) eD(bU bW bX cE cK cW Iq Jd Nn) No(uG uL uR uV vO vT vU yE) rC(aD bW bZ cR dJ nY oN) Ed(qT rA rW uM yK) On(hA iB jY vH xA) rY(hX Nw Nx Vq Vs) Ad(uO vI vU yH) Jd(jH jI jY lL) Kq(hR iB Ic jY) hA(bW cE cW rZ) rB(Jt Mq Nw Om) lM(aD aF aG bZ) qV(Kk Pd Pe) rZ(bC cG cW) Dc(vB vT) Nn(hL qQ) Ml(hV lK) Oa(uV vW) Ok(hR vI) cK(lL lN) wH(Hr Lj) EthR FpwF FwrA HqwQ HutV IchX QulL KgvT UmuL PkuM aJuX bWjU iAqT qDtM rXlK} Us{Bc(sO tV uR wB wC wF wG wH wL wP yD) Ad(hO hR lO qQ sK sM vS yH) Jk(sC uX vB vP wG wH yK Tk) wD(aC bW Hq Hr Oe Of) Aj(sC uW vP wC tM) Dk(jY qQ rY rZ wQ) Jh(eZ uY vI vP wH) On(hR hW rB rY rZ) Kq(jQ jY qX rY) bW(uG uN vU xA) qD(rT sC sM vI) Vs(rB rY rZ) hR(Jg Qt Uc) wF(aC Ky No) Mg(vI vS) Jd(uY wC) Qh(lO qQ) Ok(rB rX) dN(uZ vW) wQ(Ed Ib) wH(Ct cZ) xA(Ap Mm) sC(bG Uk) EfuP UcvS TnlL TvnB IquZ IsyJ NyjY bCwG cRuY hArY} Ad{Kr(pS sK sM sO uG uL uP uY vH vO vP vQ vU vV vW wC wD wF wG wL yJ yK yL zG zH zI tM) Nt(rR rT rW uN vW yL yE xA) Na(sK sM uL uM wC zG) Hf(eZ jL uY) dB(wC wL)} Bc{Kz(sK sM tV uN uU uY uZ wF wJ wK wQ yD yJ) Hf(rY uT vB vS wF wH yD) Db(pS vB wF wH) uN(jY Nt Um) No(uL vT) Na(tV xA) fP(uX xA) vW(Nt qD) GzrY KrwF UptV aZuG cCuY} qD{Kz(sM uG uP uX vA vH vI vW yH tM) tM(fP Kr Me Wm) Hf(sC uW vI) Um(vU vW yE) Kk(uU vW) sC(Db Hc) uP(Ap Qw) NouW OnVq PjqG hGyE} No{Jd(uI uL uN uV uW uX vB vI vO vS vT vW zG tM xA) dB(tX wF wH wL) IcxA IqtQ QzwQ KzzG bWvT kRuY} uY{Nt(Al Ap Cu hG iO Jd kR Uh) Ap(cM Dg Kk) Hf(Hw Mm Pk) Kr(Hw Jp) Kz(bC Nb) Um(gL Uk) NacR} qT{kO(Fp Hw Ih Iq Jk Mt Qa Qb) Hw(nC nH nJ nL nU) IhnJ UmwQ} Kk{Ap(sK tV uN uP uU uZ vH xA) Et(Nm Nt pS vQ yL) KfyL} Kz{bC(uZ vH wF wG) Nb(uZ wF wG) zG(Ed hL) qQ(pS sM) JjyL aNwQ qCrX} Um{vB(aZ iC Kx Uk) bE(wF wL) vS(Fw wL) IktL QcyL PgzH qCvU} dJ{Et(Ic tQ tU) wQ(fP Kg Ph) IcKq HfwH JpqI OktQ PhwE PkwP} Vq{On(eT eZ fY hL hO pY qB) hL(Dk Ib Qh) cFrY} bW{xA(Ic Ki Nk Pk) vW(Ed Fw Oa) Hf(vB vT) MpuN} Kr{Dd(sO uX vQ vW wF tM) Jp(vS wB) AotM} dB{Hq(wG wH wL wQ) Qz(wF wG wH wL)} Db{hO(vI vP vV) NrvW bCvB} Nt{qG(Ap Kf) EtNl JdeZ JtrT} Hf{wQ(Rb Uf) wH(Hr Ld) KywF} nT{Ji(Ic Id) NjKq aMoN} Et{In(Ne Nl) aKvV} Qw{JhwP JmtL UfwQ} Ap{xA(Ez Ng)} Qa{eDmF rAkO} Qz{IcwJ NycC} Jj{mHlL iOwF} nJ{oN(aO bZ)} MtmHjU MwTvnB NaclyD NbfPwQ HwrAkO QvbCyL LjUnvW NyeDmF UfrUvP Constrained panels with 3 analytes, where 1.0E-6 >= 'model p-value' > 1.0E-7. Contains 1,274 panels of 27,619,476 total panels evaluated. : iH{Ic(Ad aE Af bW cH Cv Cw Dc Dd Dk Et Jd Je Jk Jl Jp Kf Kr Lw Lx Ml Nb Nl Nw Nx Ny Of Ok On Oz Pf Qh Qt Qu Rc Rh Tz Uf Ut Vs tF) jL(aD Aj bG bR cM CW cZ Dc eC ED Ef Hb Hw It Je Jg Jk Jt Ju Kg Ki Kj Kl Kq Mg Nn Oa On Oz Pd Pe Pg Qu Qw) eD(Aj Bo Cv Cw Dc dD Fn Hc Hw jH Jk Ki Kk Ky Lw Md Mm My Ok Pe Qh Qu Qz Tn Tt Uf Ul Um) iB(Ap Aw Ba bU bX cP Cw Dc Dk Et Fr Jg Kf lM My Nw Nx Oa Of Ok Qh Qt Tn Vs) lL(Bo cE cW dD Di Hw Il Iq Je Jg Ky Nn Ss Tn Ul) hL(Ap Co Dc Hb Jt Ju Kf Lh Nm Ok Qy Uf) jD(bZ Ij Ik Il Js Kr Ky Lw Oz Qz Uf Vs) jY(cE cN Cv Dk Fr jF Kf Li Lx Ok Qt Rc) lM(An aO cU dC dF dH Iv Kk oN Pe rB) On(Fp hO Iv jP Pe Pf qD rT) hR(cU iJ Il jF Jg Kl Li) rB(Ap hX Kd Ke Li Mw qT) Ad(Fp Ik Il In Pf Rh) Jp(sK tQ vH vP wC zI) rY(Ap Bc Il Kp Nk Qy) No(tX wF wH wJ wL) Kq(Fp Ik Nf Pe Pf) nT(cG cL MP mU) jI(cW dD Jg Nn nW) sC(Hu Kx Ly Nb Nq) Ed(lK rO rR tS) Nm(hO qC qD uY) Ok(qG rW uO xA) qV(Hv Il Pf Pg) lN(cC cZ Hw Pe) Bc(rO rP wF) Et(jP Pe Pf) Oa(tX wB wQ) hA(bZ Nn Uf) jH(Je Jk Ml) qU(Jd Ny Uh) jO(Cw Kl Nn) Fy(uY xA) Nr(tX wF) Nt(wF wH) Jt(qC qD) Rh(oP oQ) Tk(iC qT) Um(uY tL) Vq(qI rU) cU(fY lK) nO(cG cL) jF(dR Pe) jP(Of Tn) jU(Ij Lw) qQ(Cw Ul) AphW ArwL BohX MpeT NflK IboP QcqC QzwQ QyqD KlPf LhvA OmqG bCrT bSiC cWjR nNoN hOvV} Cw{rN(Cs Dc Gl Hu iB jE Kk Ld Ly Nb Nj Nl No Nx Oa Oe Pe Pg Po qG Qw Qz Rb rT Uk vI VT) uY(bG Kd Ks Ma Ng Nt Pa qG Rm tN tS tT tX wB wD wF wJ wK wQ tM) Nq(qX tN tO tR tS tT tU tX uV vO wD wE wF wJ wK wQ yD) qG(Dk Hu Ib iZ jL Ju Ky Lx Mp No Po qD Rb Rm Uk Vq) No(qH rO tS tU uO wF wH wJ wL wP wQ) hL(aK cW dJ tN tS tT tX wF wJ wQ) eZ(aW Dk Fn Jd jL Kr Mp qC Uv) hO(aK cW gP gW tO tS tT Vt wJ) qX(aO Cu Ed Js Ma Mw Na Qw Us) dJ(eD hA Ic jP lL rY tT) wJ(eD jK jL jV pY qD Vs) qC(aK gP Oz Pb Rh tS) Ic(eD jO oK qU qV) Us(eD jL qT rT rY) qQ(Bc Hu iJ Qw Vq) Rh(jP qB Qz rY) Nt(Qz wQ tL) Nj(Nk Qz Tj) Vq(qH rU rY) Vv(qT rA rB) eD(cA Ik Kk) tS(Lj pY qD) Bc(rO rP) Ed(rR vI) Hu(qH rU) Uo(vH yL) Vs(wK wQ) dA(tO tR) fY(oK wL) gP(qD tQ) uP(QD) KkqV KrjP LdrU LjwP PewK PkrT aCbE aKqB aOjL bCyL cAjO cZvB iOxA qAoK jVvV vHvI} Us{rY(Ad Ba cE Et Jd Je Lh Mu Mw Nw Nx Ny Qt Uc) qX(Ad Dc Dk Je Jk Kf Kg Lh Of Ok Uc) Jk(hP qC rO rW tU vV yH tL) eD(Ba Jd Ok Po Qt Tn Uc Vs) hR(Ba Et Jd Je Kf Ny Ok Vs) rZ(Ba cE Jd Mu Nx Ok Qt) lO(Dc Jd Jt Kf Kl Rc) qQ(Dc Ef Fy Iq Jd Qz) Ad(qV rP uM uY zA) Bc(rP tQ tS tU zA) Et(qG qO Rh rP rX) On(eZ hO Iv Nj vS) Dk(hL hO qA rA) Ef(eZ hL hO qA) qU(Ba Kq Ny Qt) Ed(qT tN tO) Uc(hL hO jY) wH(Dp Oe Of) lL(Jd Jg Qt) Ap(qO rB) Dc(jL qT) Ib(hO Tk) Tn(eZ jO) Jl(Nj Qz) Kf(fY qO) sC(Oe Of) AjvV FytN LxnT IiwE IsUt JdeZ QhrV JtzA KgqT KjqH NxrX NyjD OkrA UkwF aJuX bWtS wQlM qCrT qDwD} Vq{rU(Ad aJ aK aR aU cI Dc Fr fY gL Hq hV Iq Is jG Jp jQ jR Jt Jv Mm My Nx Pj qD qO qP qU QZ Rm rW Tz Uf) rY(bS bX cW Hq Hx Iq It Jd Jp Jt Ju Kz Nn On Pj QV Qw Qz Uf) qI(aA aK aV Db dJ Dl dM Et Fn Jd Je Jt Jv On qD Qh qZ) qG(aO Ap Dg Et Jg jY Ke Kg Ko Kz lM On qD Qz Ul) rW(Af Ch dM Et hA iA jY Nj qV Qz tF) rO(Ad As Jp jY Nx Of Pj Qz Vs) Jt(qZ rR rS rT rV) rN(Ad Af Jd Je Up) qH(Ct Dk Of Vs) rT(Et Ij Kz) Ch(eZ rP) Qz(qZ rR) hL(Ef Oy) qV(qO rZ) jY(rR rS) IcbX TthA TvnO JvrV OnqO PjqZ tFnT} dJ{Ic(aC Ad Bo bU bX Cv cW Dc Dd Dk Jd Jp Kf Kr Ny Of Ok On Qh Qt Tn Tz) Et(hR Kk vI vP vV) Ad(cF hR hV tX) Qw(Dk Kq Qt) tX(Hb Kz Uf) aC(bX cF) tQ(Ap Ph) NtKq JprU JqnK OkhR cFcK} Nt{Ad(qG Rh tO tR tV tX uM vU wL wQ) Jt(rO rU rV sK uU uV wE wG yH) Et(Hc Ib Ic Nc Nh Rh) Ok(Ne Nh Nl xA) On(Ic Kk Qz) Bc(wF wL) uY(gL iZ) ApwD IcNv QzKq KfqO KgwQ PjqG mHrY} nT{cL(Db mF mM nA nH nI nJ Rj Vo) cG(aM mF mP nA nH nI Vo) mF(Bo dG Ex Lx Nv oN) oN(aO aY dN mP mU) Ji(Kc Ko Ut) Ny(aM nA Po) Tv(Dp Ib) Kn(cN mU) mP(Bo Dc) NjQt aRmU} In{Ne(Hq Im Iq Jq Lx Ly Mr Nj Nw Ny Of Ok On Pg Po Qa) Nh(Et Hq Iq Mr Nj Of Ok Qa) Nl(Im Iq Mr Of Ok On Qa) EtKk IcUt QzNy KffR} Ad{Na(jL rW tQ uY vH yL) Hf(hO jY qU qV tQ) Gz(eZ hL pY) Kr(rQ tQ tU) dB(jL tU zA) Ex(fY qD) Qw(tQ yL) DbjL NjlI cCtU} Et{Ne(Hx Ii Il Io Js Nn Oi) Nl(Hx Ii Il Io Js Oi) Kk(cC Iq Kr Oz Qy) Ic(Ib Nm Qy) LuQz NhHx HfqX aKvP cChR} Hf{Jd(eD jL lL qU) Kq(hA jY qU qV) Rc(hA jY

Figure 23 Continued

Figure 23 Continued bF Bg cW Ib Kg Lh Mu Nv Nx Of Om Oy Tv Ut) qT(Bb Co Cq Ib Je Jk Lh Ng Of Om Oy qD Tn Tv Ur) xA(Bc Dd Ed Iq Jd Jh Kf Ly Mh oH Ok qD Qz Uf uX) uY(aC Aj bW Ch Cp Ef Fy Hw Iq Mm Ng No Ok Qh) qD(Ib Kq qG qI qU rZ tR Uc uW vA vS tM) Ed(JI rW tT tU uV vO wF wG wJ wK zA) hR(Di Jt Kl Li Nv Nw Om Rc Tn Uf Ut) Aj(hL hO qG rT sK sM uG uP vS wG) Ib(Ad Ic qA Qz rS rT rV tO uV zA) Nj(Fr Lx Mu Nw Of Qt Tn Ut Vs) Jd(hO qI qU qV rA rT rU wG zA) Jh(rT rW tS uM uZ vV wB wD) Jk(Ic jH jL qV rA tN wE zH) Kf(hL qG qP rP rW vP vV wD) Of(JL jP lN rA uP vI vU) Uc(qV rN sC sK sM uP wG) hO(Iq Je Jt Oe Qh rW vV) Ad(Ik Jl Rh tQ uL yL) Bc(qH uG uN uU vV yJ) Qz(Kq Mu Qt Qy rU Ut) sC(Ct Ef Iq Ng Og Uf) Ic(Jl Mu Qt Qy Ut) Qh(eZ hL uX yL tL) rU(Dd Iq Ly Qw Rb) Dk(hP qG rV Tk) Ef(rN uM uW vI) Lx(jD mF nA qU) Jl(Ly Nl Nx Tv) Kg(jL qG tN tO) Om(eZ rA rB vP) Oy(jL rA wD wH) bC(vU vV yK tL) nT(cG cL Jq Nv) rX(hA Lh Nw qC) Cp(rA rT vI) Kj(rN tN vO) Ok(rP rW yD) Uf(vV wJ wK) Ut(Hu lL Tr) bG(qO qP rW) eZ(Ch Oc Qu) wH(aC Ii vS) qV(Jg Mu Qt) Tv(Kq Mh) Rb(qZ tX) Jt(rP sK) Og(vV wD) dN(uO uT) wP(dB Iu) tV(bA cI) qA(Oe Uu) qC(Pz Qc) qU(Mu Tn) jL(Co Cq) rZ(hA Mw) lL(Bg Po) uZ(bW Fb) ChvS CvwF FyyL MqrB NguM IkKq HbqO IqrT RcjY JerA KlhL NxjT UmtS cZwJ fYtX wDjO} Ic{dJ(aL AP aZ Bc bG Bn bR cF cP cT cY dD De Dg Hc Ib Il Im Je Jg Jh jI Jk Jl Kc Kg Kz Lh Mf Ml Mu Mw My Ne Nj Nl Nv NW Nx oF Om Or Qy Qz Sr Ss Tv Uh Vq Vs) bX(Ad Af aP aR aW aZ bA Bc bF cC cE cL cT Cv Dc Dd Jd Jk Kc Kf Kq Kr Nl Ny Of Ok Om On Oz Qh Qt Qy Rc Sr Tz Uk Vs) Et(aW aZ bG cC Cv Db gP iA iJ Ik In Js Kk Ko Kr Ks Kz Lu Nb Nj Nl Oz Pe Pg Ph Qm Qt Qz Rh) Ib(Cv Dc Dd Hu Id Ik In Jd Kc Kk Kx Ml Nb Ne Nj Nl Nt On Ow Ph Qw Uf Uk Up Wm) Nj(aP Bo Cv Db Dc De Fr Jd Je Jk Kq Lj Lu Lx Mu Nk Of On Qy Qz Ss Tz Vs) Cv(aP aR aW aZ bA bF bG bR cC cT dD dE fP Kr Kz Lu Nc Nm oF Qt Ua) Qy(Ad Dc Hu Id Ik Jd Jq Kc Kf Kx Nb Ne Nl Nt On Qw Tz Uf Uk Vq) aP(aF bG Dc Dd dE Ed Hu Ik Kf Kr Ml Nl Nt Of Pe Qz Tz) Dc(aZ bA bF bG cE cF FP gL iA In Kr Ky Qz) Dd(aC aR aW aZ bA bF bG bR cE cF dD nW oF) On(aR aZ bG bO cC dE iA In Js Kr Na Nm Qz) Jd(aR aZ bG bR bU cF Kz Ml Ne Nl Nt Qz) Kr(Ad aR jI Jk Kq oF Qa Qt qX Qz Tz) aZ(Ad Dk Kf Ny Of Ok Qh Qt Qz Vs) bG(cE cG cL Jp Kq Mw Qt Rc Tz Vq) In(Dk Jk Kq Mu Mw Ny Qa Tv) Qz(aW bA bF Bo cE cT dD Lj) Qt(Hu iJ Ik Nb Nt Qu Qw) Kf(aC aR aW bA cC dE iA) Vq(cF dE gP qV qX rY tF) aR(Dk Jk Of Oz Qh Rh) Kq(aI cC iJ Nt tF) Tv(aC bR dD Wm) Jq(kI mZ nA nK) xA(hG Lj Rb Uk) Nt(Ad Jk Lh) Hf(jL qV qX) Kc(bA cT Kz) Ny(aM cC nT) oF(iJ Nb Oz) Fn(eD qU) No(wJ wQ) Lx(mH mZ) Nk(Ne Nl) Rh(bR dD) Of(aC aJ) fP(Nb Nl) gW(aK Jh) rU(vP vV) AdNm DkcC EdaJ MlMw TohR IsmZ QhbR KnkC UpUt cWjG} nT{cL(aM aS bG bL Bo bX cP cW dC hC iO iZ KN kP lY mH mI mP mY nB nC Nd Nj nK nL nU nW oN Qh Qw) cG(Aa aS aV aY Ba Bg cE Cp Ct cY Db De iP jY Ke lX nC NJ nK nL Ow Qw Rj Tr Uf Uu) qT(aD aW aZ bI bL bO bR bX cA cD cI dN dR eC eF Hw Ih iP iZ kQ kR kS lL mZ Wm) oN(AA AS aV bW cN Cp Db Dd dJ Ke nH nJ oK Or tF) aM(dG hB Ji Jl Jq Lx Mn MP mU Nv On Qe Uh) mP(Ao bF bL Bn bQ Co cT dF dG Dk oK Tn Tv) Mp(aS cY dA Db dE dI dJ Kn Rj Tr Vo) mU(bF Bo bX Db Dc dG hC Kg Kk nY Tv) Lx(aS Cp cY Db dJ Jy Kc mH Tr Uf) mF(cE Dg hB Kq Li Mr Ny Pf Po) Ji(Gl Hb Ke Pj Rh Um Uu Uv) dG(aO aV aY bW nI Nj tF) Bo(aV aY dJ nA nJ) cN(cM cW jL nW Rj) Ny(iO mZ Nf nK) On(aY Cp Ib Uu) Ow(iP Lu nA Qv) Kq(Lv nA Nl) aY(Ex iJ mM) Ib(Lh Mt) cE(nH Rj) nA(Pg Po) AaOr CpNv ExNj TrJl TvIj cYhA dJhC nRiO nHpF} Qz{Nj(Db Et Fr Hq Hu Jd Je Jh Kq Lj Lu Lx Mu My Nk Of Om On Oy Qt Qx Qy Ss Ut Vs) Ib(Ad As Db Dc Dd Et Fw Hf Hu In It Iv Jd Js Ki Kr Ml Ne Nt Ph Rc Up Wm Tj) Qy(Ad As Dc Dd Et Hc Hf Hu Ik In Iq Jd Ki Kr Ky Kz Na Ne Nl Ns Nt Rb Rc Vq) Bo(As aW cC Ct Db Dc Dd dJ Hu Ik Im Jd Js Kk Lu Nk Nl Nt Of Rh Ua Tj) Db(Dc Et Fr Hu Jd Jl Jq Kq Lj Lu Ml Nl On Oz qQ Rc Ss) Et(cC dJ Hf Ik Js Kk Ko Kr Ks Nm Nt Rh) cC(Ad bU Dd Dk Jl Jq Mu Mw On Qt Vs) Nt(Ad Dc Jd qQ Qt uY vB xA) Hf(eD Hc Jd On qQ Qt qV qX) No(rO rQ tO uV uY zG xA) Hu(qQ Qt rU tV wJ xA) In(Cq Dc Dk Mw Tv Ut) dJ(Ad Dc Dk Jg Kq Ny) Qt(As Na Qu Qw Up) Ex(Kq Mu Ut) Ny(aW aZ dB) As(On qQ) Lj(Dc Iq) Up(Mu Ut) uY(aC Ky) vW(Kr Me) AdNm BbwJ NaOn JdKz JrJs KirU KqaW bWxA wQhB} dJ{bX(Ad aK aQ aU aZ bB bF Bo cE cF cK cP cY gW Is Jd Kq Ly Ml Mt Ne Nh Nl Ok On Qw rC Tj) cF(aK aL Ap aQ aU aZ bB bF Bo bR cI cM cP cT cU cY Db Dc Ef Gp Jd Kq Ok rY) Ad(aC aK aU cY gW jR Kk Nm qU qV QW Rh rY Tj) Qw(Bo Dc Et Jd Jg Mu Mw Ny On qQ Vs wH) Et(fN jT Ks qA qG Rh uN uY wQ xA) Jp(hR rO rY rZ tO tQ tX uV wQ) Kq(Fp Ik Kk Mf Na nH nO Pe) aC(Ap aX Bo bR bU cB Dc Dd) hR(Ap bB Bo Hb Jg Jt Kf Kl) Hf(eD jD qT qU qV qX) Bo(aK aQ Ef gW Tj) Db(jD qU qV qX wH) cW(eD hA lL qV rZ) Ap(eZ pY tT tX) Jd(bU jK lK lL) Ok(hA jY Kk rY) Pk(rU tX wG xA) bR(Is jF qV rY) nK(Lx Ny Po Tz) Vq(qX rU rY) lL(kF mW nR) Hb(pY tQ) Ph(tO tU) cB(rY rZ) lK(nB nH) DkTj NaOn IstT bWvB dCrC mMjP nIjR qXqW} Vq{rU(Af Al Ao aQ aV Bo bX cL Cs Ct Cu cZ Db dE dG Di Dk dM Dp Hf hX Ik Im Ir It Iu Jd Je Jr Js Ke Kn Ky Kz Ma Mg Mk Na Ng Oe Of Pb Pf Pg Po Pz qG Qh Qv Qw Qy Uk Vs) rY(aE aM cL cP cQ Cu Dg Fn fP Fw Ii Io Jr jT jV jY Ke Kn Ko Kq Ky Lh Li Mm Ms My No nW Nx Ny Of Og Oi qU qX To Tz Ul Up Ur) qX(cC Ct Ed Fw Hf iA Iv Ki Kz Of Oi) hO(Ch Dk Ef Ib Is Jd Jt Mw Qh) qG(Ij Jd Kf Na Om Qh Qm Up) qI(Ch cZ Kz Of Vs) rZ(cQ Jf Oi Qv) rT(Jd Jv Kc Qh) hA(Aw Dk Of) rV(Et Mz Pj) rO(Et Je Ke) Qh(fN rP) Kz(qQ rR) hL(Ch Jh) hP(Aa Jt) qC(Dk Pz) qU(Iq qD) rW(Ke Ko) JdiC JvqQ KkqV} Et{Kk(aR As aW Bo Db Ib Ik Il Iv Js Ks Lu Ml Na Nj Ns Rh Ri Ud Up vP zH zI Tj) Nh(Fp Hu Hw Ii Ik Il Io Iq It Jm Js Mp Nd Nj Nn Nr Oi Po Qb) Nj(Ed Fw Hx Ii Il In Io Iu Js Kr Ks Ly Ne Nl Nn Oi Rh Tj) Nl(Fp Hu Hw Iq It Iu Mp Nn Nr Po Qb) Nt(Ed Id Jd Kq qG qP Qt Qw Qy Ss) Ne(Hu Hw Iq It Iu Ly Mp Nr Po Qb) Nm(Ed Hc Ib Ki Kz Qw Qy Rh) Ib(Bg Ez Ik In Ks Qw Up) Hf(eD jL jO jP qU rA) Rh(cC Db Kr Ks Na Up) Ik(Ki Kr Ks Kz Qy) cC(bX jP jT qA) dB(hR jL qX rX) Qw(Lu Qy wQ) Nc(In Io) Ks(Hc Qy) aK(pS qO) tT(Nq qD) qG(Ex Gz) NaqZ NdIo HuxA aUuG aZvP dRqO wKqD} Kz{uY(Ap aZ Bb bW cL cR hO Jd Jh Kc Kx Md Nl Nt Pb pS qQ rU Uk Vv) vH(aZ bW hO Jk Kx Mm Nb Ne Om qQ Uf Uk Vv) pS(Dc eD Fy hL hO jI Ky Mp qV qW Rb rX) Ed(Nj rO tO uG uP uV vO wH yL zI) bC(sC sK vA vB vU wL yL tL xA) hO(Ap Kf sM tQ uU wG yL zG) qD(tR uL uM vS wK wQ yJ yE) sC(aZ cA cE cL iC Nb Uk Vv) Bc(rU sO tS tX uL wP tL) sK(cR Cv Jd Ni Nj oN) hL(rX uG vO vQ zI) qQ(uI vO vQ vS zG) uZ(cN iO Kc uL Vv) iC(wD wG wQ xA) Nb(tR uU vB) Kc(qG vT xA) Hu(tV tX) Jd(eD uP) Pb(yJ zI) wL(cZ Fp) iO(uU wF) zG(Jj Ky) yL(Cv No) ApeZ UkwG bWxA rNuU} Hf{qX(aF Ap aZ Bb cC cU cW Dg dH Di ED Fb Jd Je Jg Jp Jt Kc Kf Ki Ly Me Nj Nl Nx qU Rb Uk Vv) uY(bW Cv Dd hB Jd Jh Jj No Nr oH oK oN qD Um tF) qU(Bc bW Dg Ji Jt Kf Lw Mm Ny Ok On qD Uf) wH(aP bW cZ iO Ky Lj QD Rb Uk) Ad(hW rB rY uG uL uM wC yL zG) qV(Bc Jd Ly Me Mh Mm Nj Rb Uf) eD(Dg Dl Hc Ok On Pz qT) Bc(rU rX tT tV yJ) qD(rT uM vW yJ tM) jY(Cv Jd Jg Ok On) jL(cW Jg Jt Kq) Ed(qT rA xA) On(hA lM rB) bW(wF wL xA) Jd(eZ rY) Kq(rB rY) Um(wL tL) Pk(tQ uM) cW(hA jO) wF(iO Ly) lL(Jg Wn) DchO QwqQ JusC KljO bCrZ qCrT kFoN} Qw{Ad(pS qG Qy rB rN rY tR vW wC wJ wQ yH zG) wQ(Aj Ap bW dN Ib Jh Jk Jm Kf Kg Me qD) xA(Ap Bb Bc bW Fw Iq Jh Me Pk rA rY vQ) qQ(aX cC Dc Dk Hq Iu Jt Ng On Pi Qh Uu) tL(BC bW Dc Hw Is Jj Jk Jr Kj) Jh(fN qO uM uY vP yJ) Jj(tN tO wF wL yH zH) On(Iv Nj Nt rY uG wC) Iq(rT rU uY uZ vH) Ny(aM bX cC In rY) Dc(Qy rN rU uY) Mc(sM tU vA wC) qD(Ib sC uW tM) qO(Ap Bb Fw Om) Nj(Fr Ib Qy) bC(vT wF wG) rY(cW Nx Po) qP(Ap bG dB) Qy(Nl Ss) Jt(rN rP) cC(Dk Vs) wL(Hw Pz) uY(Nt Qh) ApwJ BcwF BgIb CheZ QtaW JkvB JrJs KjrN UuvW aGqZ bWvT} Nt{On(Ad bX Ed eZ Hc Jd Kq Ne Nl pS Qy rN Ss Tt uG Uk UP wC yL tM) uY(Aj Dc Ed Fb Fn fP Fy iJ Kj kQ Ky Qv Rg Um) Kq(cW Hc Ik Jd Kk Ly Ml Nc Ne Nj Nl Rb Rh) Ad(bX eZ fY Ib Id Lu Nj pS Qy rB wJ zI) Ap(eZ qP rN rR rT rW sC uL vP vV xA) Nl(Hq Jd Jg Jt Lh Ly Nk Of Pz) Ne(Hq Jd Jg Jt Ly Of Pg Pz) Bc(uL uZ vT wG zH tL) Nh(Hq Jq Ly Nj) Ok(qO qP vA yD) Ed(tU vB vW) Jd(uN uP vA) Kf(Kk qP rN) Dg(Ib qG) Jg(Kk qG) Ny(bX fP) Pj(rN wQ) MmwG QutM KjtL dBwH iOwF} qT{kO(Aa aK dN Hq Im In Ir It Iu Jm Jq Jr Jt kS Li Lj Lx Md Mr Nb nL Nn No Nr nU Ny Oe Pe Po Wm) nD(aG aW aY bC bF bL cE cG cI cL cP cR cX dB dF hB iJ jU pF) nL(dN Fp Ih Ir Iu jO jU jV Li Md Me mI Mt mZ nH Oe Pf) nC(dN Fp Ih Ir Iu jO jU jV lL Md Mt mZ Oe) nJ(dN Ii In Ir jO jU jV lL mZ Ny) nH(dN Ih Ii jO jU jV lL mZ Qa) nU(Ih Ii jO jU jV lL mZ Wm) Ed(Db

Figure 23 Continued

Iq) nR(bZ iA) mZ(jE jP) hX(nB nO) UmtL dBqU mErX mFjE} Nj{Nk(Ad Ap Bo Dc De Di Ex Gz Hc Ib Kk Ne Nl Qt Qy Rh Ss Tn Vs) Ok(Ax Fw Hw Hx Ii In Io Iq Iu Ly Mp Mz Nd Ne Nh Nl Tj) Ed(Bo Db Fr Gz Id Jd Jl Kq Lw Lx Qt Tz Uf) Ad(Bo Db Fp Fw In It Jm Js Lj Nm Tj) Nh(Hq Hx Il Io Js Ne Oi Qb) Tj(Bo Kq Ny Om On Ut Vs) Db(Hc jL Ly On Qt Uf) On(As Ax Fw Ql Up) Ne(Hq Hx Il Iq) Nl(Hx In Io Iq) Up(Lx Mu Qt Ut) Bo(Cv Fp Of) In(Kq Ut) DcIl IkQt IvVs nRoN} Um{uY(aC Aj Ap Aw aZ bE bF bG cE cG cL hA Hq iC Ik iO Iq Kr Kx Ky Nb No Of pS Qe Rb Uf uI vQ Vv) tL(Ap Aw aZ Bc bE bF bG cE cG Fb gL Hq iC Iq Kr Nb Of rU vQ) vQ(bI Ed Fw Kr Lx Mp Nf Nn Oh Pg Po qD Qe Up) wL(aD Aw Fr Of Pf Uk vU) Qe(sM tR tS uU zH xA) Kr(sO tR uU vS yL) qC(Dk Kf vS) qD(rQ uU xA) yL(Ha Lx Qb) In(Dk Ny) tR(Lx Po) wF(bF Uk) EdqZ MpwP JrJs UfvA UvuU VvvB PevU bWxA cAwG} Na{qX(Ao Ap Ba Bo Co Cp cW Di Ed Jd Je Kg Ki Nl Ok Qt Qx Rc Ut Vs) On(aG Ax bX dE iA Kk pS qZ rN uG uL uY vH wC tM Tj) Bc(qI qZ rP rQ rU uM vI yK) Iq(qZ rT rU tV uL uZ vB) Dc(qQ rN rU uY wQ tL) Jt(qZ rS sK uL wJ wK) xA(Ap bW Jp Lh Mh Ok) Ad(tR uG vQ yH zH) qD(rT uW wC wG) uY(bC bW Jd Jp) Jp(rT rU) Vs(rY rZ) bC(rT wG) bW(vT tL) nA(Lx Ny) wQ(Ii Lh) TzvH RcIL QhqQ NxqZ OmtT cErZ cWrY iOsC kFoN} dB{qU(Ad bW Iq Kf Kq Li Lw Lx Mm nR Ok On Qh qX Uf Vs) jL(bG bR bU bX Db Dc Hq Iq Kg Qh qX rC rZ Ul) eD(bW bX Iq Jd nR Ns On Qh Ul) qX(aZ bG bU bX cF Iq jF Ok qW) rZ(bC bW cE cG hA Mm) nR(iC jK jM jP IL) Ad(hR qC qV wQ) Ok(hR jY rX rY) Kq(hR Ik jY) bX(cE iC lM) mU(hA jK lO) Mm(qV rY) Jd(jH IL) Qh(jH lN) wF(Bc Dc) jK(lW mH) ExqQ OnjY UfwQ bWvB cEhA rXlK} Db{qX(cW Dd Di Iv Jd Kk Kq Nc Ni Nl qV To Uf Uk) qU(Ad bC cW Fn Jd Ji Kq Li Mm On Uf) jL(cC cW Dc dD eC Jd Jg Ju Kq Rc) Bc(sO tV uG uN uT uY vH yD xA) qV(Ad bC cW Jd Kk Kq Mm Uf) hO(Ad Aj Jd Jt xA) eD(cW Jd On pF) aC(bE bX cF) bC(rY rZ vW) cE(bX hA rZ) Ad(cF cZ) Ly(cN wQ) wH(Fp Uk) jO(cW Uf) uY(No Nr) DdwQ bWxA qDtM kFoN} Ok{Nh(Fp Hu Hw Ii Il Io Iq It Iu Jm Js Mp Mz Nd Nn Oi Po) Nl(Fp Hu Ii Io Ir It Iu Iv Jm Jn Js Mp Mz Oi Po Qb) Ne(Hu Ii Il Io Ir It Iu Js Mp Mz Nn Oi Po) No(tO tT) Nc(Hx In) Qd(qO qP) cC(bX hR) KkvQ PeuP bWxA iOuY qDqG} Ad{bX(aZ bA Bo cC cE cF cT Hu Ik In Nm) Ex(jY qG qH qO qZ rN rR rS rW) Gz(qG qH qI qQ rO rP rR rT rW) cF(aC aZ Bo cC Hu Nm) Kr(jH qO rB rU rY) In(Ib Ne Nm Rh) cC(eZ hR jL Rh) aZ(Lu Nm Rh) aC(bE cZ) NmHu NotM IkQy LjvW} Ny{nA(Bg Bo Hv In Iq It Iv Jn jP Jr Js kQ Mq Mx nB nJ Nq nU Of Oz Po Qc) Po(kO lY nC nH nJ nK nL nO nU) nK(Bg Fp Ij Iv kO nC Oi) Hx(Ne Nh Nl) In(bX mF Tv) nO(aM Ns) mF(jE jP) IkmZ KenB bXcC mHjP} jP{nR(aC aF aH aI aL bB bE bN bX cB cE cG cH cI cO cW dD dF hG iJ iP oE) oN(kE kI kO lX lY mF mH nB nO) mF(cE Mr Nr Nv Po) mH(Me Mr Po) mM(aG bL cJ) cW(lX Of) mZ(dE hG) NxlX} Iq{Ne(Hw Hx Ii Il Io It Js Ly Nn Qb) Nl(Hw Hx Il Io It Js Ly Nk Qb) No(rR rT rV sK uZ wE wL) Nh(Hw Hx Ii Il Io) Pk(rU uZ) aC(uY vB) tV(Iv Pe) EdrV FnqU NkuL QbqA QdwH JpqD RmqG dCuZ} Ap{Kk(qV tQ tR uI uX vU yL zG zH) qG(Af aK As Bn cC cF Ki qD Qn) xA(Hu No Oy qW rN Uc) No(tU vU vW) qO(Qd qU Uc) uY(aI aK iO) wQ(Nk Pd) IktL LjvW VtfY cCqA gWqC wKqD jTrV} bW{xA(Ar As BG Ez Jj Lh No Nq Pc Pi Qh Qt Qu Qv Rb rZ Ue) vW(dL Ha Kr No qC qD Up) Mp(tS uG uY wD wG) vT(Mu Mw Nk) tL(Nk Qt) uY(Mu Rb) cChR cMuG iOuN} bX{cC(aZ bF cE cF Is Ly Mt Ne Nh Nl Vs) cE(aC aG aZ bG bR bZ cF cO cU) Bo(aC aZ cT Dc) In(Dc Is On Tv) bF(aC aG aO aZ) Dc(Gz Il) IkKq aCaZ cLdH} Kr{Uf(eZ qA rQ rU sC uW uZ vV vW wF zH) Dd(rQ rU uR uU uY wB wH wL wP zI) Jp(uM yE tM tL) Bc(sO uU wK) No(uY vW) DccF MmvB JthO PjrV PkuY qCtM} oN{kF(aN As Dc eC gP Hw iP jK Ks Mt nC nH tF) tF(mF mM nC nH nJ) kO(jK lL nH nJ) nN(aM aY nC) fP(hO qD) mP(aP bZ) nJ(aA dN) oO(aO mZ) ExqQ MwnK aMnO} mH{cF(gW jE jF jM jQ jR lK) qV(aD aG aX cW dH dM gP) lL(Ir Lu Me Mr Og) Me(jO jU jV) Mt(jF jV) aC(jK qW) lM(aP dN) bPlK qUkO jVkS} Bc{fP(uW uZ vH vP vV wJ yH) cC(qI sO tS uG uL) tV(iA Ki wF) uN(cF Hq Qv) As(sO uZ) Gz(rQ rU) wF(dN No) AoxA RbwG QvuZ aZyK yDjY qVuY} nA{Po(Fp Ik kO nC nH nL Oi) Bo(Hw Ir Is Jq Mk Mw) kO(Jl Nv Nw Pe Pg Qb) Pe(Ik nC nH nL) Lx(bZ kF Oi) Nv(nC nH nL) ExIb} Ne{Hx(Hq Im Lx Mr Nw Of On) On(Ii Il Js Nn Oi) Of(Hw Ii Il Oi) Nq(Hq Jh My) Ly(Nh Oi) DcIn HqHw IiLh JgOi JrJs jHkO} Tv{In(aF cP Dk Kk Kq Mh mS Mw Uk Ut) nB(aA aO aS bZ De kF kO nN Ph) Ib(nO oP) AjeZ BoTj DpnO nHkO} mF{jE(Hw Ih Im Ir Nk Nr Po Qa Qb) hX(Ir Md No) rB(Md Nr Pe) Lx(bZ Po) qV(bZ iA) BokF aOlM} qD{tM(bM cF cM dN eT Ur vB) qG(Hb Jt Kc Kf) fP(eZ yE) wQ(Hc Lh) uP(Jt Nm) MevW KfaK UfwK PkrT} Nl{Hx(Im Lx Mr Nw Of On) In(Lx Ly Nw) On(Ii Io Js) Nq(Hq Jh) Oi(Ly Of) NotX NkaX JrJs jHkO} uY{Ky(cC Hw Lh No Pa) No(dN Fw Jf) Jd(cC Ki Ue) Jh(Ez Ki) Jp(iO Ue) FpcS MddN HwUv} kO{rA(Aa Fp Ih rB) Lx(nK Po) qX(Aa Qa) qU(eD Oi) lM(eC fP) KlnH OwnB bJjR bLjD hGlK} Kk{Kf(qC rO rU rV vQ) iP(nC nH nL) On(In Iv) Uf(tV vI) KijQ OmvQ aOtR} cF{Dc(aC Bo Il In) Bo(aC cI) Hu(Jd Jg) Qh(Tk Wn) cE(bG dH) DdIn IkKq aCbE} cW{lX(iC jD jK jU lK qV) rY(Ed Fw Il Kp) jU(mT mZ) EdqX FnhA mUrA} mZ{Lx(Ko Po) aY(eD jK) cM(jD jU) lK(aK tF) lM(aP fP) MfOg IsKo cYjR nNrY} No{bC(vT wL tL) Jv(yE xA) vT(Jr Kc) vW(dF Ql) ChtM JdtL UfxA iOwF} nR{lL(bM bP bZ cC dH eC hB iA) qV(dH iA) aOlK cCjK} Bo{aC(aX bE cZ) nJ(Mk tF) EdqX TohR InIs OwnN aKgW lYoH} Nh{Hq(Hu Hw Nn Nq) Hx(Mr Of) NqJh LyOi IiOn JrJs} Ki{Jd(eD qV qX sM uP) Jh(hR qX) EdqX FnqU UksC} Ik{Kq(aG aR aW cB cC) AouM PonK RcnH KfaR} xA{Pk(aP bC bO Ed) Mm(cC qW) Uf(Js qW) EdPa} On{In(aG aO bZ dH Ib) GzrN IldH nKnL} fP{lM(lY nC nL) wQ(Uk Vv) NbzI JdqQ iOwD} Kf{Js(qG qU qV qX rA) qC(aK gW)} nB{Ow(Iv nN Pk) Kn(kC nL) rA(Hw Jm)} Ex{DcrN DlhL JdqI KqTk aKgW iOqQ} dN{vW(hL tL) PksM mPlM qCtM} Fn{Rc(hA jY) LjvW bLqU} aZ{fY(rY vB) aKwG wQjH} cC{hR(Kq Mm Uf) KqjY} nK{Lx(aP bZ) nL(Nv Po)} iO{wF(Hw Lh) AowE GzqQ} Ow{nN(lY Ql) IvmY} aM{nO(cG Jq) mMjU} aO{lM(nI nJ) qVkG} nC{lL(Jn Nk) KniP} Dc{IncK VunJ} Hu{CheZ HqwG} Qv{bC(vW wL)} Jp{NbwG bGqO} nL{KniP bFjK} wQ{EzUf JuaC} qV{aFkG dHmT} uP{QdJt LhPe} CqIboP DdInQy EdHwvW GzIjTk LxaAnO mEnJrX

Constrained panels with 2 analytes, where 1.0E-7 >= 'model p-value' > 0. Contains 1 panels of 155,299 total panels evaluated. : iHqX Constrained panels with 2 analytes, where 1.0E-6 >= 'model p-value' > 1.0E-7. Contains 3 panels of 155,299 total panels evaluated. : iH(eD jL) qTkO Constrained panels with 2 analytes, where 1.0E-5 >= 'model p-value' > 1.0E-6. Contains 28 panels of 155,299 total panels evaluated. : Ne(Et Hx In Nj Nt Ok) Nh(Hx In Nj Nt) Nl(Et In Nt Ok) Cw(qG Qz uY) Ic(dJ iH Qy) nT(cG cL oN) qT(nC nL) BoQz EtKk VqrY Constrained panels with 2 analytes, where 1.0E-4 >= 'model p-value' > 1.0E-5. Contains 143 panels of 155,299 total panels evaluated. : iH(Ad Bo bU bW cE cF cH cM Cw dD Et Fp hO iO Kq Ly Ml Nj Nl On oQ Pe Pf rT wH tF) Ic(aC aP aR bG bX cE Cv Cw Dc dD Et Ib Jd Jk Kq Nj oF On Qt Qz) Cw(aC cF eD hL hO jO jP Nj qQ qX rN rY vH wQ tL xA) Qz(cC Db Dc Et Hf Ib Lj Nj On Qt Qy) Et(Io Ks Nd Nh Nj Rh Us) bX(aC Ad aZ bF Bo cE dJ) cF(aC Ad bF Bo cE dJ) Nj(Ad Bo Ed Nl Ok) qT(nH nJ nO nT nU) Nh(Io Nn Oi Ok) Nl(Hx Io Iq Nk) Hf(eD qU qV qX) Us(Dc lO On qQ) Qw(Qt Qy xA) Um(uY wL tL) oN(kF mM nN) Ad(aC Nm) Ne(Hq Iq) Ny(nA nT) dB(jL qX) BoaC DbqX NtKq TvIn KzuY VqrU dGnT Constrained panels with 2 analytes, where 1.0E-3 >= 'model p-value' > 1.0E-4. Contains 676 panels of 155,299 total panels evaluated. : Qz(Ad Ao aR As aW aZ bA Bb bF cE Co cT Dd dJ Fr Hc Hq Hu iH Iq Jd Je Jh Ki Kq Kr Ky Kz Lu Mu Mv Ne Nk Nl Nt Of Ok Om Oy Pg qQ Rc Ss Tn Us Ut uY Vq Vs vW wQ xA) Nj(Ao Ap aR Ba Bb bX cE cF Co Cv Db Dc De Gz Hc Hq Ib Id In Jd Je Jy Kk Kl Kq Kr Ky Kz Ly Nc Nd Qg Qt Qw Qy Ss Tn Uf Uk Up Us Ut Vs) Ic(Ad aJ bA bF Bo cG cL Db Dd De Fr Hc Hu Je Jg Kc Kf Kr Ky Kz Lj Lx Ml Mu Ne Nl Nv Of Ok Om

Figure 23 Continued

Or Oy Oz Ss Tn Tv Tz Uk Ut Vq Vs) iH(Dc Dd Di Dk Ed Hc Iq Iv Jd Je Jg Kk Kl Lj Lw mT nB Nc Ne Nf nJ nT Nx Ny Oa Of Ok oP Oz Qt Qu Rh sC Tn tX Uf uM Vs tM) Et(aG Bo bX cC cF Db dJ Ed Ez Gl Hf hR Hx iA Ib Ii In Js Ki Ko Kr Kz Ly Me Mn Mp Nc Nn Nq Oi Ph Qw Qy qZ Ri Uh Up) bX(Ap aR Aw Ba BB bQ cB cC cF cK cL cP cT Cw dB Dc Di fP Is Jd Jg Ki Ly Mt Ne Nh Nl Ny Of Ok Om On Vq) Us(Ad Cw Ib Jd Je Jk Jl Kq Lh lM Mu Nl Nx Of QT qV qX Qy rY sC Tn Tv Ut uY Vs wP wQ xA) dJ(aC Ad aQ aU bF Bo bR bU cB cK cP Ed Ef fP gW Is Jd Kq Ly Ok On qV QW rC Tn) Cw(cK cN cP gW Hu In Kk Kr Ky Mp Nd Ne Nh Nl Nm Nt Or Ow Ph Qw Qy Rh Up Tj) Bo(Ad bR cI cK cP Dc Hu Is kF Kk Ly mF mZ Ne NH nJ Nl nT Qw Tj) nT(aY bW cE cH cN dF Dg hB hC Id Kd Kq Lx Nv Oh Ow PF Tv Uc) cF(Ap Aw aZ Bb cC cK Db Dc fP Fr Is Jd Jg Ne Nh Nl Ny Ok On) mZ(cG cL iB Jq Lx Mp Mt mY nJ No Ny Og Oh oQ qT qX rA rY) bF(aC Ad aG aO bG bH bM bR bU bZ cB cH cI cK cP dE dH) Ok(aG aZ cC Hw Hx Ii In Io Iq Kk Ly Mp Mz Nc Nd) On(aG aR As aZ bO cC Db dE dH iA Kk Kz Qw Up Tj) aC(Ap Aw aX aZ Bb bE bR bU cB cE cP cZ Db Dc Dd) Ad(aZ cB cE cK cL cN cP cT dE In Kk Nt Rh) Jd(Db eZ Hu Ik Ki Kk Kz Ne Nl Nt Qw uY) cE(bG bR bU bZ cB cK cO cP cU dH Qw rZ) Iq(fP hO Kk qC qD tV uZ vB wD wF wL) Db(cP eD hO jL Ly Ne Nl qU qV uY) Kz(Hc hO Kc Nl pS uZ vH zG Tk) kO(IL Lx mY nH nJ Ny qU qX rA) Qw(Dc Ib Jk Nl qQ uY wQ tL) dB(eD hR lM qU qV rC rX wH) nB(Kn Ny OH Ow qT rA Tv) uY(Ap bW Hf Kr Ky Pk Rb) Lx(kF mF mH nA nK nO) fP(cC cZ hO Hu Iv wQ) Ap(eZ Kk qC qG xA) In(Dc Kq Nc Tn Ut) aZ(qX sC vP vV wQ) Ly(cC cT Gz Nc) Qy(Dd Kk Ne Nl) cG(kF nH nJ nO) mF(Mr Ny Po rX) nK(Mn Mr Ny Po) qX(cC Ki Na Vq) Fn(eD qU qV) Nt(Hc Kf Tn) Kk(Jg Tn uU) Um(vA vB wF) bW(vW wL tL) cB(aG cK cP) cL(bR nH nO) Bc(uN wF) Na(qZ xA) Up(Dc Ut) Vq(qV rZ) Pk(qC xA) cW(eD hA) nO(Ny oQ) nA(Mr Po) qD(uP tM) BbcP Bglb GzRb NorO NlaX TohR HfwH IsbR OwnN UksC dNvW mYnC nDqT oQoH Unconstrained panels with 3 analytes, where 3.3E-15 >= 'AUC p-value' > 0. Contains 50,000 panels of 27,619,476 total panels evaluated. :
Cw{rN(aA AD aE AF aG aI AJ aK AL aM AN aO aP aQ AR aS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV cW CX cY cZ dA DB DC DD DE dF DG dH DI dJ DK DL dM dN Dp dR eC ED EF ET EZ Fa Fb FN fP Fr Fw FY GL GP gW HA HB HC HF hG hL hO hP Hq HR Hu HV HW HX iA IB IC Id IH IJ Ik Il Im In IO IP Iq Ir Is Iu IZ JD JE JF JG JH JI Jj JK JL JM Jn JO JP JQ jR Js JT JU JV JY Kc Kd Ke Kf Kg Ki Kj Kk Kl Ko Kp KQ KR KS Kx Ky Kz Ld Lh Li Lj 1K IL lM IN IO Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Or Ou Ow Oy Oz Pa Pb Pc Pd Pe pF Pg Ph Pi Pj Pk Po pY Pz QA QB QC QD qG QH qI Ql Qm Qn qO qP qQ QT QU qV Qw QX QY QZ RA RB RC Rf Rg Rh Ri Rj Rm rO rP rQ rR rS rT rV rW rX rY rZ sC sK sM sO Sr tO tS tT Tz Ua Ub Uc Ud Ue Uf UG Uh ul Uk UL UM UN UO Up Ur Us Ut UU UV uX uZ vA vB vH vI VO VP VQ vS VT VU VV vW wB wC wD wE wH wJ wL wP wQ yH yK yL zG zH yE tM tL xA Wm Tj tF) qG(aA AD aE aF aG aH aI AJ aK aL aM aN AO AP aQ AR AS aU aV aW aX aZ BA bB BC bE bF BG bH bI bJ bM BN BO bP bQ bS bU bV bW bZ cA cB cC cD cE cF cG CH cI cJ cL cN CO CP cQ cR CS CT CU CV cW CX cY cZ dA Db DC DD DE DG dH DI dJ DK dL dM dN Dp dR eC ED EF Et Ez Fa Fb FN FP Fr Fw FY GL GP gW HA HB HC HF hG hL hO hP Hq HR Hu hV HW HX iA IB IC Id IH Ii IJ Ik Im In IO IP Iq It Iu IZ JD JE JF JG JH JI Jj JK JL JM Jn JO JP JQ Jr Js JT JU JV JY Kc Kd Kf Kg Kj Kk Kl Kn Ko Kp KQ KR KS Kx Ky Kz Lh Li Lj lK IL lM IN IO Lu Lv Lx Ly Ma Mb Me Mf Mg Mh Mj Mk Ml Mn Mp Mq Ms Mu Mv Mx My Mz Na Nb Nc Nd Ne Nf Ng Nh Ni Nj Nl Nm Nn No Nq Nr Ns Nt Nu Nv NW Nx NY Oa OE OF Og OH Oi OK Om ON Or Ou Ow Oy Oz Pa Pb Pc Pe PF Pg Ph Pi Pj Pk Po pS pY Pz QA QB QC QD Qe Qg QH qI Ql Qm Qn qO qP qQ QT QU QV QW QX QY QZ RA Rb RC Rf Rg Rh Ri Rj Rm rO rP rQ rS rT rU rV rW rX rY rZ sC sK sO Sr Ss St tN tQ tU tV Tz Ua Ub Uc Ue Uf UG Uh ul Uk uL UM UN UO UP UR Us uT UU UV uX uY uZ vA vB vC vH vI VO VP vQ Vs VT Vu VV vW wC wF wG wH wJ wL wQ yH yJ yK yL zA zG zH zI yE tM tL xA Wm Tj tF) uY(aA Ad aE AF aG aH aI AJ aL An AO Ap AR As aW AX aY aZ BA BB Bc bE bF BG bI bJ bL bM Bn Bo bR bS bU bV bZ cA cC cD cE cF cG CH cI cJ cK cL cM CO Cp CQ cR CS CT Cu CV cW CX cY DB dC dD DE dF DG dI DK Dl dM dN Dp Ed EF EZ Fa FN Fp Fr Fw FY GL gP gW Gz HA HB HC HF hL hO hP Hq hR Hu Hv HW HX iA IB IC IH Ii IJ Ik Il Im In IO Ip Ir It Iu Iz jD jE jF JG JH JI Jj JK JI Jm Jn JO jP Jq Jr Js Jt JU JV JY Kc Kd Ke Kf Kg Ki Kj Kk Kl Kn Ko Kp KQ Kr KS Kx Ld Lh Li lK IL lM IN IO Lu Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nd Ne Nf Ng Nh Ni Nl Nm Nn No Nq Nr Ns Nt Nu Nv Nx Ny Oa OE Of Og OH Oi Ok Om ON Or Ou Ow Oy Oz Pa Pb Pc Pd Pe pF Pg Ph Pi Pj Pk Po pS pY Pz Qa QB QC QD Qe qH ql Ql Qm Qn qQ QT QU QV QW QX qZ RA Rb RC Rf Rg Ri Rj rO rP rQ rR rS rT rU rV rX rY rZ sK sM sO Sr Ss tO tQ tR tU tV Ua Ub Uc Ud Ue Uf Ug Uh Uk UL UM Un UO UP UR Us UT uU Uv uW uZ vA vB vC vH VO Vp vQ VS VT VU Vv vW wC wE wF wG wH wL wP wQ yD yH yJ yK yL zA zG zI yE tM tL xA Wm) xA(aC Ad Af aG aJ aK AL aM AN aO AP Ar aS aU AW AX aY aZ Ba bC bE bF bG bH bI bN bO bS bU bW cA cB cC cD cE cF cG CH cI cL cM cN cP CQ cR cS CT cU CV cW cX cY dA dB DC Dd De dF dJ Dk Dl dM dN dR eC ED eF eT EZ FN FP Fw FY GL gP gW HA HB hC hF hG hL hO hP Hq HR hV hW Hx iA iB IC IH IJ Il Im IO IP Iq iZ JD JE Jf jG JH JI Jj Jk jL jM Jn jo JP jQ jR Js jT JU JV JY Kc Kd Ki Kk Kl Kn KR kS Kx Ky Kz Ld Lh lK IL IM IN IO Lx Ly Ma Me Mf Mg Mh Mj Mm Mn Mp Ms Mw Mx My Mz Na Nb Nc Nd Ne Nf Ng Ni Nk Nl Nr Nt Nu NW Nx nY Oa OE oF Oh Oi OK oN Or Ow Pa Pb Pc PF Pg Pk Po pS pY qA qB QC QD Qe Qg Qh Qm Qn qQ QT QU QV QW Qx QY Qz RA RB Rc Rf Rg Rh Ri Rj rP rR rU rW rX rY sC sK sM tO tQ tR tV Tz Ua Ub Ue Uf UG Uh ul Uk uL UM uN Uo uP Ur Us UU UV uX vH vQ Vs Vv wG wK wL wQ yH yJ zG zl tM tL Tj tF) tL(AD aG aI aK AL aM aN aP aQ AR AS aU aV Ax aY aZ Ba Bb BC bE BG bI bL bN bO bR bS bU bW cB cC cD cE cF cH cI cJ cL cM cP CQ Cs cT Cv cY cZ dA dB DC Dd Dg dJ DK DI dM dN dR ED eT Ez FN FP Fw fY GL GP gW Ha hG hL hO hP Hq HR Hu hV HW HX iA iB iC IH IJ Ik Im iO Ip IZ JD JE JF JG jH JI Jj jK JL jM jO JP jQ jR jT JU JV jY Kc Kk Kn Ko kQ KR Ks Kz Ld Lh Li Lj lK IL lM IN IO Lx Ly Mf Ml Mm Mn Mp Mr Mu Mw Na Nb Nc Ne Nf Ng Nh Nj Nk Nl Nn No Nq Nr Nt Nu NW Nx nY Oa Oe oF Og oH oK oN Or Ou Ow Oy Oz Pa Pb Pc Pd Pe Pf Pg Ph Pi Pj Pk Po pY qA qB qC QD Qh Qm qQ Qt QU QV QW QX Qy Qz rA RB rC Rf Rg Rh Rj Rm rR rS rT rV rX sC sK sM tQ tV Ua Ub Uc Ue Uf uG Uh uK uL UM Un Uo uP UR Us uT Uu UV uZ vA vB vH vI VP vQ Vs vT VV vW wC wJ wL yL zG tM Tj tF) wQ(aA aC aF aG aH aJ aK aL aM An aQ AR AS aU aV Ax aZ BB BC bE bF bG bH bL bN bR bS bW bZ cA cB cC cD cE cF cI cJ cL cM cP cQ cR Cs Cv cW cY cZ dA dB DC Dd DG dJ dK DL dN dR eC ED eT EZ Fb FN FP FY Gl gP gW HA hB hC hG hO hP Hq HR Hu hV hW HX iB IC Id IH Ij Ik Im In IO Ip Is It Iu iZ JD jE jF JG jH JI Jj jK jL jM jO JP JQ jR Js JT JU jV jY Kc Ke Kk Kl Kn Ko Kp KQ Kr Kx Ky Kz Ld Lj lK IL IM IN IO Lx Ly Me Mf Mh Mn Mp Mr Mu Mw Mz Na Nb Nc Nf Nh Ni Nj Nk Nl Nm No Nr NW Nx nY Oa Oe Og oH oI oK oN Or Ou Ow Oy Oz Pb Pc Pd Pe Pf Pg Ph Pi Pj Pk Po pY qA qB QC QD Qe qI Ql Qm Qn qQ QT QU QV QW QX Qy Qz rB Rf Rg Rh Rj Rm rS rT rV rX sC sM tQ tV Ua Ub Uc Ue Uf UG Uh uL UM Un Uo uP UR Us uT Uu UV uZ vA vB vH vI VO VP VV wC wL yH yL zG) hO(AD aE Af aG al aJ aK aM aN aO aP aQ AS aU aV aW aZ Ba bF bI bJ bM bN bP bQ bR bX cC cD cE cF cG Ch cJ cN cP cQ cS cT CV cW cY dA DB Dc Dd dF DI dJ Dk dM Dp dR eD eF eZ Fn fP Fr Fw fY gL GP gW HA hB HC hF Hq hR Hu HX iA Ib IH iJ Il Im iO iP Iq Ir Is It Iu iZ Jd Je Jf jG Jh Jj JL Jm Jn JO Jp jQ JR jT Ju JV Kg Kk Kl Ko Kq Kr Kz Lh lK IL lM Lx Ma Md Mg Mh Mm Mn Mp Mq Mr Ms Mu Mv Mw My Na Nb Nf Nj Nn Ns Nu nW NY OE oF Og OH Oi oK oN Or Ow Oy Oz Pa Pb Pc Pd Pe PF Pg Pi Pk

Fn fY Gl gW Ha Hu iO Jd Je jG jK jL jM jV Kk Kl Kr Ky Kz Ld Lj Ly Mp Nb Nf Nk No Nq Nr Nt nW Oe Og oK oN Ow Oy Oz Pb Pf Pg Pk Po Qd Qu Qw Qz Rb Rh Uk Um Us Vs Vv) qP(aK aW Bc bG cP cR cS cU dC Dd ED Gl gP hA hR Hu iO Je Jf jL jM jY Kn Kr Ky Ld Ly Ma Mj Mp Mw Nf Nl No Nr Nt nY Oa Oe oH oK oN Pb Pe Pf Po qB Qd qU qV Qw Qz Rb Rh tV Uk Uo Us Uv Vq Vv tF) uX(aK aM BC bW cB cM cP cW cZ dA dC dJ dR ED Fn Fp fY Gl Ha Hu Ik iO Jd Je jK jL jM Ju jV Kk Kr Ky Ld Lj lL Ly Mp Nb Nf No Nq Nr Nt nW Oe oK Pb Pe Pf Pk Po Qd Qw Qz Rb Rh Uk Um Us Vs Vv) tT(aK aN BC bW cW dA dC dR ED eT FN gP gW Ha Hr Hu iB iC iH iO jD jG jH jL jM jP jQ jR jU jV jY Kk Kr Ky Ld Lj lM lO Ly Na Nf No Nr Nt Oe Pe Pk Po pY qV Qw Qz Rb Rh Rj Uk Us Vs Vv) yK(aK BC bW cM cP cR Cv cW dA Dc dJ Ed Fn fY Gl gP gW Ha Hu Ik iO Jd Je jK jL jM Kk Kr Kx Ky Ld Lj lL Lx Ma Mp Nb Ne Nf No Nr Nt nW Oe oK oN Pb Pe Pf Pk Qd Qu Qw Qz Rb Rh Uk Um Us Vs Vv) wC(aK BC bW cM cP cW cZ dA dB Dc dJ ED Fp fY Gl gP Ha Hu iH iO Jd Je jK jL jM Js jY Kk Kr Ky Ld Lj Lx Na Nb Nf Nk No Nq Nr Nt nW Oe Pb Pe Pf Pg Pk Po Qd Qw Qz Rb Rh Ub Uk Um Us Vs Vv) uV(aK bC cM cP cW cZ dA dJ Ed Fn Fp fY Gl gP gW Ha hG Hu iH Ik iO Jd Je Jf jK jL jM Kk Kr Ky Ld Lj Lx Ly Mp Nb Nf No Nq Nr Nt nW Oe oK Oy Pb Pe Pf Pk Qd QU Qw Qz Rb Rh Ub Uk Um Us Vs Vv) tV(aK aU aV BC cI cJ cP cT cW cZ dA dJ dR Ed fY Gl gP gW Ha hR Hu iJ iO Jd jK jM jT jV Kk Ko Kr Ky Ld Lj lK Ly Mn Mp Nb Nj No Nq Nr Nt nW oH oK oN Pb Pe Pf Pg Pk qU qV Rb Rh Uk Us Vs) zH(aK BC cC cM cP cW dA Dc dJ Ed Fn Fp fY Gl gP gW Ha Hu Ik iO Jd jK jM jU Kk Kr Ky Ld Lj lL Lx Ly Mp Nb Nf No Nr Nt nW Oe Pb Pe Pf Pk Po Qd Qm Qt QU Qw Qz Rb Rf Rh Uk Um Us Vs Vv) uR(aK Bc cM cP cT cW cZ dA dJ dR Ed Fn Fp fY Gl gP Ha Hu Ik iO Jd Je jL jM jT jU Kk Kr Ky Ld Lj Lx Mp Nb Nf No Nq Nr Nt nW nY Oe oK oN Pb Pe Pk Po Qd Qm qV Qw Qz Rb Rh Uh Uk Um Us Vs Vv) vU(aK aW Bc cM cP cW cZ dA DC dJ dR Ed Fn Fp Gl gW Ha Hu Ik iO Jd Je jK jL jM Kk Kr Ky Ld Lj Lx Ly Ma Mp Nb Nf No Nq Nr Nt nW nY Oe oK oN Pb Pe Pf Pk Po Qd Qw Qz Rb Rh Uh Uk Us Vs Vv) wF(aL BC bW cB cP cT cW cZ dA dB dC dJ ED Fn fY Gl gP gW Ha iH Ik iO jG jK jL jM Kk Kr Ky Lj Ly Mp Nb Nf Nq Nr Nt nW Oe oH oN Pb Pe Pk Po Qd Qm QU qV Qw Qz Rb Rh Uk Us Vs Vv) uT(aK BC bW cB cM cW cZ dA dJ Ed Fn Fp fY Gl gP gW Ha Hu Ik iO Jd Je jL jM jU Kk Ko Kr Ky Ld Lj Lx Ly Mp Nb Nf No Nq Nr Nt nW Oe oK oN Pb Pe Pf Pk Qd Qu qV Qw Qz Rb Rh Uk Um Us Vv) vS(aK Bc cM cP cW cZ dA DC dJ dR Ed Fn Fp fY Gl gP gW Ha Hu iO Jd Je jK jM Jp Kk Kr Ky Ld Lx Ma Mp Nb Nf Nq Nr Nt nW Oe oK oN Pb Pe Pf Pk Po Qd Qu Qw Qz Rb Rf Rh Uh Uk Um Us Vs Vv) wH(aK BC cI cP cT cW cZ dA dJ Ed Fp fY gP gW Hr Hu hX iH Ik iO Jd jG jK jL jM Js Kk Ko Kr Ky Ld Lj Lx Ma Mp Nb Nf Nq Nr Nt Oe oK Pb Pf Pk Po Qd Qh Qu Qw Qz Rb Rh Uk Um Us Vs Vv) qH(aK aM aN Bc DC dJ ED Fn Fp fY gP HR Hu iO Je Jf jG jI jK jL jM Jp jY Kk Ky Ld Ly Mj Mp Nb Nf Nl No Nq Nr Nt nY Oe oK oN Pb Pe Pf Pk Po Qm qU qV Qw Qz Rb Rh Uk Us Vv) sO(aK BC bW cM cP cW cZ dA dJ dR Ed Fn Fp GL gP gW Ha Hu iO jK jL jM jV Kk Kr Ky Ld Lj Lx Ly Mp Nb No Nq Nr Nt nW Oe oK Pb Pe Pf Pk Po Qd Qu Qw Qz Rb Rh Uk Um Us Vs Vv) yE(aK BC cM cP cW dA dC dJ dR Ed Fn Gl gP gW Ha Hu iO Jd Je Jf jK jM jT jU Kk Kr Ky Ld Lj Ma Mp Nb Nf No Nq Nr Nt nW nY Oe oK Pb Pe Pf Pk Po Qd Qu Qw Qz Rb Rh Uk Us Vs Vv) rR(aK aU aV Bc cP cT dC dJ dR ED Fn Gl gP hR Hu iH iJ iO Jd JE jG jI jK jL jM Jp Kk Ky Ld Ly Mp Nb Nf Nj Nl No Nr Nt nW Oe oK oN Pb Pe Pf Pg Pk Po Qw Qz Rb Rh Uk Vq Vv) rO(aK Bc cP cT dC Dg dJ ED Fn Fp Gl gP Ha Hu Ik iO Je jK jL jM Kk Kl Kr Ky Ld Lx Ly Mj Mp Nb Nf No Nr Nt nY Oe oK oN Pb Pe Pf Pk Po Qd Qm Qu Qw Qy Qz Rb Rh Uk Us Vq Vv) yD(aK aN BC cP cW cZ dA dJ ED Fn Fp fY gP gW Ha Hu iO Je jK jL jM jU jV jY Kk Kr Ky Ld Lj Ly Nb No Nr Nt nW Nx Oe oN Pb Pe Pf Po Qd qV Qw Qz Rb Rh Ub Uk Us Vs Vv) vC(aK Bc cM cP cW cZ dA dC dJ dR Ed Fp fY Gl gP Ha Hu Ik iO Jd Je jK jM Kk Kr Ky Ld Lj Lx Mp Nb Nf No Nq Nr Nt nW Oe oK oN Pb Pe Pf Pk Qd Qu Qw Qz Rb Rh Uk Um Us Vs Vv) vO(aK BC bW cF cM cP cW cZ dA dC dJ dR Ed Fp fY Hu Ik iO Jd Je Jf jK jL jM Kk Kr Ky Ld Lj Lx Mp Nb Nf Nq Nr Nt nW Oe oK Pb Pe Pf Pk Qm Qu Qw Qz Rb Rh Uk Um Us Vs Vv) tN(aK Bc cW dA dC dJ ED Fn Fp fY Gl gP HA Hu hX iO Jd jI jK jL jM jQ jU jV jY Kk Kr Ky Ld Lj Ly Nb Nf No Nr Nt nW Oe oH oK Pb Pe Pk pY qV Qz Rb Rh Uk Us Vs Vv) qZ(aK bQ cT Cv dC dJ ED Ez Fn Fw gP Hu iO Je jG jK jL jM Jp Js Kk Kr Ky Ld Ly Ma Mp Nb Nf No Nq Nr Nt Oe oK oN Ow Pb Pe Pf Pk Po Qu Qw Qz Rb Rh St Uk Us Uv Vq Vv) wE(BC bW cP cW cZ dA dJ dR Ed fY Gl gP gW Ha Hu Ik iO Jd jK jL jM Jp Kk Kr Ky Ld Lj Lx Nj No Nr Nt nW Oe Pb Pe Pf qU Qw Qz Rb Rh Uk Us Vs Vv) wG(aK aV BC cW cZ dA dJ Ed Fn fY Gl gP Ha Hu iJ Ik iO jK jL jM jT jU Kk Kr Ky Ld Lj Nb Nf No Nq Nr Nt nW oK oN Pb Pe Pf Pk Qw Qz Rb Rh Us Vs) tO(aK aN BC bN bW cB cW dA dJ ED fN gP Ha Hu iC iO jK jL jM jU jV Kk Ky Ld Lj Ly Nb No Nq Nr Nt Oe Pe Pf Pk qV Qw Qz Rb Rh Uk Us Vs) tR(aK aU aV Bc bW cJ cW dA dJ Ed Gl gP gW Hu iO jK jL jM Kk Ky Ld Lj Nb Nj No Nq nW Oe Pb Pe Pf Pg qU Qw Qz Rb Rh Uk Um Us Vs Vv) tX(aK Bc cW dA dJ dR Ed gP gW Hu iH iO jL jM Kk Kr Ky Ld Lj Nb No Nr Nt nW Oe oH Pe Pf Qw Qz Rb Rh Uk Um Us Vs Vv) pY(AD aG aK aW bQ cG cP cS Cv cW Dc dF dJ gP gW iA iH iO Jd Je jL Kr Mh Mp oF oK oN Ow Oz Pb Pf qU qX Rh Uv) tU(aK Bc cB cW dA dJ Ed Fp fY gP gW Ha Hu Ik iO jL jM Kk Kr Ky Ld Lj Ma Nb Nr Nt Pb Pe Pk Qd Rh Uk Us Vs Vv) zA(Bc bW cW dA Dc dJ Ed Gl gP Ha Hu iO jL jM Kk Kr Ky Ld Ly No Nq Nr Nt Oe oK Pb Pe Qw Qz Rh Ub Uk Us Vv) fY(Ad aK aW cC cR cS cU dF dJ Dk eD gP iA iO Je jL Kr Mh Mp Nq oF oK oN Pb qU qV qW Rh rX rY Uv Vv) qA(aK aW cC cS dJ Dk eD gP jL Kr Lx Ma Mp Nf Nn Oh oK oN Oz Pa Pb qU qV rB Rc Rh rX Uh Uv Vv) qB(aG aK aU cC cS dA dJ gP gW iA iH iO Jd Je jL jT Kr Mp nW oF oK oN Oz Pb qU rB Rh Uv) eT(aK bI cP cS Dd dJ gP iH iO Je jL Kr Mh Mp nW oF oK oN Oz Pb qU Rh Uv Vv) fN(aK aW bI cN cS Dc dJ gP iA iO Je jL Kr Mp Nq oK oN Pb qU qW Rh Uv Vv) hP(Ad aK aW bI cJ cS dJ Dk gP iJ jL Kr Mp oF oK oN Pb Pe Pf qU qV Rh Uv) iH(eD hR hV iB jI jL jM jO lL lN qT qU qV qX qY rA rB rC rX rY rZ) rY(cW dJ Il Iz kC kO Kr mH Mj nB nC nI nL oO Qw Rh Us Uu Vq Vv) qX(aO Cu Ez Ic Iv Js Ma Mj Mw Na Nq Nt Qw Uc Us Vv) rB(Id kF mF mH mM nB nI nJ nU Rh Vv) eD(cA dJ Ic Id Ik Kk Lu Um Us) dJ(hR hV hW hX jO jP rX) mH(hV hX jD lK rC rX rZ) hW(kG kO nB nC nJ nL) qT(Ik Js nD nT Us Vv) jP(Ic Kr mF mM oP Rh) qU(Ib Ic Id Ik Kk) kO(hV hX rC rX rZ) hR(nC nL To Vv) rZ(Ij mF mM nR) Ic(jT qV qW) nT(cL mP mU) Kr(jO lL) Vv(jQ rA) rC(nC nL) jL(aO Us) IvrA KkqV VqhA cAjO mFjE} iH{qX(aA aC AD aE AF aG aH aI AJ aK AL aM AN AO AP aQ AR AS aU aV AW AX aY aZ BA BB BC bE bF BG bH bI bJ bM BN BO bP bQ bR bS bU bV bW bX bZ cA cB cC cE cF cG CH cI cJ cK cL cM cN CO CP CQ cR CS CT CU CV cW CX cY cZ dA DB DC DD DE dF DG dH DI dJ Dk DL dM Dp dR eC ED EF Et Ez Fa Fb Fn FP Fr Fw Fy GL GP gW HA Hb HC HF hG hO Hq HR Hu HV HW HX iA IB IC Id Ih Ii IJ Ik Il Im In IO IP Iq Ir Is It Iu Iv IZ JD JE JF JG JH JI Jj JK JL JM Jn JO JP JQ JR Js JT JU JV JY KC Kd KE KF KG KI Kj KK Kl KN KO Kp KQ KR KS Kx Ky Kz Ld Lh Li Lj lK lL lM lN lO Lu Lv LW LX LY Lz Ma Mb Mc Md Me MF Mg MH MI Mj Mk Ml MM Mn MP Mq Mr Ms Mt MU Mv MW Mx My MZ NA NB NC ND Ne Nf Ng NH NI NJ NK NL NM NN NO Nq NR Ns NT Nu Nv NW Nx NY Oa OE OF Og OH Oi OK Om ON oO oP oQ Or Ou Ow Oy Oz Pa Pb Pc Pd Pe PF Pg Ph Pi Pj Pk Po Pz Qa Qb Qc Qd Qe Qg Qh Ql Qm Qn QT QU QV QW Qx QY Qz RA RB RC Rf Rg Rh Ri Rj Rm rX rY rZ Ss St Tn To Tr Tt Tv Tz Ua Ub Uc Ud Ue Uf Ug Uh Uk Ul Um Un Uo Up Ur Us Ut Uu Uv Vo Vp Vs Vt Vu Vv Tk Wm Tj tF) rC(aA aC AD aE AF aG aH aJ aK aL AN aO AP aQ AR AS aU aV AW AX aY aZ BA BB BC bE bF bG bH bI bJ bL bM bN bO bP bQ bR bS bU bV bW bX bZ cA cB cC cD cE cF cG cH cI cJ cK cL cM cN cO cP cQ cR CS CT CU CV cW cX cY cZ dA DB DC Dd dF DG dH DI dJ dK dL dM dR eC ED EF Et Fb Fn FP Fr Fw gL GP gW HA HB hC hF hG hL hO HR Hu HV HW HX iA iB IC Ii IJ Ik Il Im iO Ip Iq Is Iv iZ JD Je JF JG JH JI Jj Jk JL JM JO JP JQ JR Js Jt Ju jY KC KE KF KG KI Kj KK Kl Kn kO kP KQ KR kS Ky Kz Lh Li Lj lK lL lM lN lO Lu Lv LW LX LY Ma Mb ME mF Mg MH mI Mj Mk Ml Mm MP Mq Ms MT Mu Mv MW Mx My mZ Nb NC Nd Ne NF Ng NH Ni NJ NK NL NM NN No Nq Nr Ns NT Nu Nv nW Nx NY Oa oE OF OH OK Om ON oO Ow Oy Oz Pa Pb Pc Pd Pe PF Pg Ph Pj Po Pz Qa Qc Qd Qg Qh Ql Qm qQ QT qU qV QW QY Qz rA RB Rc Rf Rg Rh Ri rX rY rZ St Tn To Tr Tt Tv Tz Uc Ue Uf

Figure 23 Continued rO rP rR rS rT rU rV rW sO tN tO tQ tR tS tT tU tV tX uI uO uP uR uT uV uW uX uZ vB vH vI vO vP vV wB wC wE wF wG wH wJ wK wL wP yD yK zA zI yE) bC(pS qH qI rT rV rW rY sK sM sO tN tO tS tT tV tX uG uI uL uM uN uO uU uV uW uX uZ vB vC vH vI vO vP vQ vS vT vU vV vW wB wC wF wG wJ wK wL wP yH yK yL zA zG zI yE tL) Ap(eD eZ fN fY hA hL hO hX jO jP jT qC qG qI qO qP qX rB rN rO rP rQ rR rS rT rV rW sK sM tS tX uM uO uP uW uX uZ vI vP vS vV wB wC wE wF wG wH wJ yJ zA tM) Dk(eD eT eZ fN fY hL hO hP hR hV hW hX iB jK jL jO jT jV jY lN pY qA qB qC qG qH qO qP qX rA rN rU rV rW rX rY rZ tN tS tT uP uX vI vP vT vU vW wB wH yE Tk) bW(pS sK sM sO tN tO tQ tR tT tV tX uI uL uM uN uO uP uT uU uV uW uX uZ vA vB vC vH vP vQ vS vT vV vW wF wG wH wJ wK wP yD yH yJ yK yL zG zH zI yE tM tL) rY(Ba cE cW eZ hA hL Je Jp kG kN Kq Lh lX mE mH mM Mq mT MU MW mY nC nD nJ nK nR Nv Nw Nx Ny Of Ok oP oQ qA qC Qt uO uZ Vq Vs vW wC yE tM) Ok(eD hR jT qC qG qH qO qP qT qU qV qW qX qZ rA rB rC rP rQ rR rS rT rU rV rW rX rZ sK sM tN tO tS tT uO uV vI vP vS vV wJ wK wP yD yL tL) rZ(Ba kC kF kI kK kN kO kP Kq Lh Lj lW lY mE mF mI mM mP mS mT MU mW mY mZ nA nC nH nI nJ nL nO nR nU Nx Ny Of oO oP oQ Oy Qt Tn Vs) Hw(rR sK sM sO tN tO tQ tR tS tT tU uI uM uN uO uT uU uV uZ vB vH vI vP vS vT vU vV vW wB wC wE wF wG wH wK wL yH yL zG zI yE tM tL) Kq(eD hA hR hV hW hX iB iC jD jE jF jG jH jI jK jL jM jO jP jQ jR jT jU jV jY lK lL lM lN lO qC qT qU qV qW qX rA rB rC rX) wH(aC Aw Ba bE Bg Bo Ch cI Cp cZ De dN Dp Fp Fy gL Hq Hr Ii Iq Jj Jm Jo jP Kg Lj Ly Ml No Of Og Oy Qz Rb Ua Ug Uk VS yL) oP(eD gW hA hR hV hW iB iC jD jE jF jG jH jI jK jL jO jP jQ jR jT jU jV jY lK lL lM lN lO qT qU qV qW qX qY rA rB rC rX) Kf(eT eZ fN fY hL hO hR lO qC qG qO qP qX rN rO rP rT rV rW sM tO tT uO uW uX vI vP vQ vS vV wE wG wJ wK wL yD zA tM) hO(Co Cu Dg Iq Je Kl Nv Oe Pz qO qX qZ rA Rc rS rT rW TN tO tT Uf uP UU uV uZ vI vP vS vT vV wP yH zH tL) Kg(qG qO qP qT qU qX rP rS rT rV rW tN tO tT tU tV tX uG uL uO uV uX vO vP vV wB wE wJ wK wL wP yD yE tL) Kj(pS qG qH qO qP qZ rN rP rQ rR rT rU rV rW sK tN tO tT uG uL uR uV uX vH vO vS vV wG wK wL yL zA tL) wF(aC Ar bE cI Cv cZ Dd dN Fp hC Hr Ii iO Jj Jm Ky Lj Lx Nk Nr Ns nY Oe oN Pe Rb Rh rU Ub Uf Ug uI Ur) oQ(eD gW hA hR hW hX iB iC jD jE jG jH jI jK jO jP jQ jR jT jU jV lK lL lM lN lO qU qV qX rB rC rX) Cp(eZ qG qO rQ rT rW sO tN tR tS uG uM uP uU uV uW uX vI vP vQ vU vV wB wC yH yK zA zG zH tM tL) Uf(pS qC rT tN tO tS tT tV tX uO uR uV uW uZ vI vO vP vV wB wC wE wG wJ wK wL wP yD zA yE tM tL) dN(sK sM sO tS tV uL uM uN uO uP uR uT uV uZ vC vI vO vP vS vT vV vW wB yH yJ yL zG zH yE tM tL) hA(Jg kE kG kK kN kO lW lX lY mF mI mP mS mT mU mW mY nA nC nD nF nI nJ nK nL nN nO nR nT Ny) wP(Ar aS cI cZ dB Dl hL Hu iJ Iq Iu Jm Kn Ky Lx No nY oH Om Pb qG Rm rT rX Tz Ub Um Uo Ur Vo) qC(Dl Hb Iq Jm Om Pz Qc qI qU qW Rc rS rT rV rX sK sM tO uM uP uV uW uX vP vS wC wG wK yL zA) Jg(eD eZ hP hR hV hW hX iC jG jI jK jL jM jO jP jQ jR jY lL lN pY qA qG qX rT vI vV) Om(eZ hR qG qO qP qX rT sM tN tS tT tV tX uI uO vH vP vS vV wB wC wG wL yD yH zA tL) qV(kC kE kF kI kN kO kP lW lY mF mH mM mP mS mT mU mY nC nI nL nR Nx Ny oO) Jm(rR sO tN tO tQ tS tT tV tX uI uN uO uU uV uZ wE wK yD yH yL zI yE tL) Rb(qH qO qP qZ rU tN tO tQ tR tS tT tV tX vO wB wC wG wK wL yD yH) bG(qG qO qP rN rP rS rT rV rW uP uV uW uX vI vP vQ vV yH zH tM tL) uZ(aC Al Ba Cu eT Fb FY hF hG jK jO jP jQ Kl Mm qO rX tN Ub wG) Ch(eZ uM uP uV uW uX vI vP vS vU vV wB wC wE wG yJ yK zA tM) nR(hR hV hW iB jE jF jG jK jL jM jQ jR jU jY lK lL lN qW rX) Iq(eZ hL hP qG rT rU sM tV tX uM uN uO uT uU vH wB wC wG) Ii(tN tO tR tS tT tU tV uO uV vB vP vV wB wE wG wK zA) Ny(eD hR hX jI jO jT jV jY lL nA nB nO nT qU qX rX) vV(aZ Fy Iz Jo Jq Kl Kx Mm Nx Og Oy rU tR Uk Vt Vv) Of(qX tN tS uP uW uX vB vI vP vQ vU vW wB wC Tk) hR(Ba kI kN kO lW mF mH mM mP mU mZ nB Qt Tn Vs) Kl(eZ fY hL qG qO rN rT sK sM uP vI vP wC tM) Ub(tO tQ tV uI uM uN uO uV vS yL zA zI yE) aC(tS tV tX uX vP vT vU vW wB wC wL yD yE) nT(cG cL jF Ji Jl Jq Lx Mp Nv oN Pf qT Ut) mH(hV hX jE jF jK jP jU lK lL qW rB rC rX) wG(cZ dJ Hb Hq Mh Mm Nb Nj Nm Pj Qw Qz Ug) qH(Je Jp kR Ly Nj Nl Nx Pj Ql Qw Qz Uk vT) Fy(nB qG rT sK sM tN tT uR uX vP yL yE) hW(Ba kC kI kO lW mI mM mZ nC nH nL nO) hX(kF lW mF mM mP mT mU mW mZ nB nO nU) wC(Ao Ct cZ Dg jY My Og Oy Qu Ss Tz uV) tL(hL jP Mm Nb Nc Nh Nj Nl Nn Oh Oz Pb) zA(cI dB hL Iz kR Mh Mm Nm Nx Pj Qz Tz) Lx(mF mY mZ nA nB nD nH nK nL nO yE) Tn(eD eZ jD jH jO lL lO nB nU qT qX) Lh(qX rA rT rX tN tO uL uO uV uX vS) Oe(eT eZ qA tS uP uW uX vI vP vQ wB) tV(bA cI cT cZ dB Dd Hu No oH Tz Ug) rB(kF kG mM mY mZ nB nJ nK nL nU Vs) yL(bX Cv Dd fY hB hL Jj No nY oN Um) Ct(tX uP uW uX vA vI vU vW wB yD) Nx(qX rX tN tO uP uV uX vB vO yK) Oy(tN tS tT uP uX vI vP vW wB wK) vS(cP cQ Dg Hb hL Je Jp Nj Nv Pk) tX(cI cZ fY gW kR Ly Mh Qz tN) rX(Ba kF kG kK mM Mu nB nU Vs) rT(Jp Ly Mm Ni Nj Nl Nv Qz Vq) Dg(hL pS qG qO rP rV sK sM) wB(Ba cZ Db Dp Hr jP lM Uk) rC(kE kG kO lW mI mM mT mW) rU(Dd Ly Mh Pj Qw Qz vP Vq) oO(jH jO jT jV lK lM lO qT) vP(aZ cZ fY Iz Mm Og Uk) hV(kG kO mE mM mP nB) wE(cI cZ Ly Qz Tz Um) yE(cI Jj Ky No nY Pe) uP(Ba bP Dp Iz Ua Vs) uX(aJ hL Ks Og tS Ur) Dd(rO rR rS rW tO) Vq(qG qI rN rO rW) fY(Hb tR uN wL zG) tN(hL Jo Og Ph qU) jF(lX mT mZ nD nO) uM(cI Iz Ms My Ua) vW(Dp Jj Lj No Qz) Ut(mF mS mZ nH) Pj(rP rV rW vO) cZ(wJ wK wL yD) qT(kE mP mW nD) qO(Ao Hb Ml tR) uN(cI gP hG Um) Ba(eZ qU vI) Mm(rW tO vI) Iz(vI wK tM) Qz(rN wJ yH) Qu(eZ qA uW) Jj(tS uO uR) Jo(tO tT uO) hL(sO uI uV) jM(mZ nB nJ) uU(hG Je Kk) Bg(eD lL) Dp(uR vT) No(vT wL) Ml(qA qP) Tz(tQ uI) Qt(lL qU) Oh(mZ nN) Um(tQ tS) Uu(cZ qA) nO(cG lO) mM(jE jP) kO(jE lK) uW(Mh Og) AouO AwvU NmuR LytO MyzG NjrV TvqX HbqP RclO QwtR JpsK JqnA KzpS UkwJ UgtS UrzI aZyK cIyD gWmT mYlM nBlN} mH{lK(Ad AF aI aK An Ao Ap aQ As aZ bA Bb Bc bF BG bJ bN bQ bR bW bX cB cE cF cG CH cN Co Cp Cq CT Cu CV DB Dc dD De Dg Di DK Dl dM Dp Ed Ef Ez Fa Fb Fw Fy Gl Ha HB HC hG Id Iz Jd Je Jf Jv Kc Ke Kf Kg Ki Kj Kk Kl Kn Ko Kq Kr Ks Ky Me nY oF oN Or Ou Ow pF Ph Pi Pk Qg Qh Ql Qm Qn Qt Qu Qv Qw Qx Qy Qz Ra Rb Rc Rf Rh Rj Sr St Tn To Tr Tv Tz Ua Ub Uc Ud Ue Uf Ug Uh Uk Ul Um Un Uo Up Ur Ut Uu Uv Vp Vs Vt Vu Vv Wm Tj) rC(aC aE AF aH aI AJ aK AL aM AN AO AP aQ aS aV Aw Ax aY aZ BA Bb bE bF BG bH bJ bL BO bQ bR bS bU bV bW bX bZ cA cD cE cF cG CH cK cM cN Co CP CQ CS cT CU Cv cY cZ dA DB dD De Dl dJ DK DL dM Dp Ef Fa Fb Fn fP Fw Fy GL Gp Ha HC HF hG iO iZ Jd Je Ju Kc Ke Kg Kk Kq kS Kz Me nW Oa oH oK pF Ph Qg Qh Qv Qw Qx Qz Ra Rb Rf Rg Ri Rj St Uf Ug Uh Ul Um Un Uo Up Ur Ut Uu Vo Vp Vt) gW(Aw Ax aZ Di Dl Ed Et Ez Fb Fn Fp Fw Fy Gl Gp Hb Hv Hx Ib Ic Ih Ij Il Im In Io Iq It Iv Jd Jg Ji Jj Jl Jm Jn Jp Jr Jt JU Jv Kc Kd Ke Kk Ko Kp Ks Kx Ky Lh Li Lj Lu Lx Ly Ma Mg Mh Mj Ml Mm Mn Mp Mq Mr Mt Mu Mx Mz Na Ng Nj Nl Nm Nn No Nq Nt Nu Nv Nw Oa Oe Of Og Oh Oi Or Ow Oz Ph Pi Pj Pk Po Pz Qa Qb Qc Qd Qe Ql Qm Qt Qu Qw Qx Rb Rf Ri Rj Rm Ss St Tr Tv Ub Uc Ue Uf Ug Uh Uk Um Un Up Ut Uv Vo Vp Vs Vt Vu Vv Wm) jP(AL AR Aw BA bF Bg bL Bn bQ cE cF cG Co Cp CT cW De dF Dp Ed Ef Ez Fa Fn Fw Fy Gp hB HC Hf hG Hw Ib Id Ir Jd Je Jf Jg Jl Jt Jv Jy Kf Kg Ki Kn Kr Ks Kx Kz Lx Md Mc Mr Mt Mw My Ne Nh Nl Nr Nt Nv Nw Nx Ny Oa oE On Pd Pe PF Pg Ph Pk Po Qa Qg Qh Qt Qv Qw Qx Qy Qz Rb Rc Rf Rg Rj Rm Ss St Tn To Tv Tz Uc Uf Uh Ul Um Un Uo Ur Ut Uu Vo Vp Vs Vt Vu Vv Tj) jQ(Ad Af aK Al Ap Ar Aw Ax aZ Ba Bb Bc Bg bJ BN bP cC cF cH Cp Cq Cs CT Cv Cx DB Dc Dd Dg Di DK Dp Ef Fa Fb Gl Gp Hb HC Hf hG Ib Ic Iz Jd Je Jf Jv Kc Kd Ke Kf Kg Ki Kj Kk Kl Kn Ko Kp Kx Kz Me Mt Oa Ou Ow pF Ph Pi Pj Pk Qg Qh Ql Qn Qx Qy Ra Rb Rc Rf Rg Rh Rm Sr Ss St Tn To Tv Uf Uh Uk Ul Um Un Uo Ur Ut Uu Uv Vo Vt tF) jR(Ad aK Al Ao Ap Ar aU Aw Ax aZ Ba BC Bg bJ bP cA cB cN Cu cY DB Dg dJ dK dL Ed Ef Ez Fb Fn Fw Gl Ha Hb hC Hf Id Iz Jd Je Jv Kc Ke Kf Kg Ki Kj Kk Kl Kn Ko Kp Kq Kr Ks Kx Ky Kz Me Oa Ou Ow pF Pi Pj Pk Qh Qm Qt Qu Qw Qy Rb Rc Rh Ri Rj Rm Sr Ss St Tv Uf Uh Uk Ul Um Un Up Ur Ut Uu Uv Vo Vp Vs Vu Vv Tj) jU(Ad aN aU aV Aw aX aY aZ Ba bG bL Bn bP cB cF Ch cQ cS cU cW cY cZ Di Dl dR Ed Fb Fw Fy GL Ha Hb Hf hG Id iP Iz Jf Ju Jv Kd Kf Ki Kj Kr KS Ky Kz Md Me Nb Nc Nk Nl nW oN Or Ou Pe pF Ph Pk Qg Qh Qn Qu Qv Qw Qz Ra Rf Rh Ri Rm Tn Tz Ug Uh Uk Um Un Uo Up Ur Ut Uv Vo Vp Vt Vu) rY(Af aI Ao Ap aZ bA Bg bL bM Bn bP bR bU bX cB cF

Figure 23 Continued kG(Ct Db Dp Fb Fw Gp Hf Kn Ks Ou Ow Pk Ql Qt Qv Ub) Ow(kE kF kI lW lX mE mI mY nC nF nM nO oQ) nR(cB cW dB dC Fw Hf Ju Jv Kn kR Ph Pk) kP(Aj bB cB cH cW dD Kn oF Or Qt St Uh) oO(Ad aI cB cW Dg Hf Kn Ou Pk Qt St) nU(dD Gp Hf Kf Kn Ql Qt St Tv Uo) nN(Ad Al Ar aZ Ha Pk Qu Rf St) mE(Al Aw cH Fw Gl Kf oF Qh Qt) oP(Ad aI cR Ke Kf Kn oF Pk St) oQ(Co dB Fb Hf Je Ju Kn oF St) Uo(kN lX mU mW mY nD nF nO) cB(kE mP mT mU mZ nC nH nK) lW(Co Kf Kn Ph Pi Pk Qt) nA(aI Md Ny Pe Po Tz Uh) nC(bL cL Db eF Kn Rm Tv) kN(Ct Dl Dp Gl Qg Qt Rc) dB(kF kI mU mW nH nO) mZ(bL cF dD dE oF Uh) lX(aI Di eF Ou Qy) mI(aI Al Aw Ou Qv) nO(cG Kf Kn Uh) nK(aI Me Pf Ur) mY(dJ oF Qt) kF(Fw Kn Pk) kI(cF Ou Qu) Oa(Tk Wn) mT(eF Pf) mW(cW nY) nD(aI cJ) AdHf ApxA NaKq TkbP OukE UkyK UhmU PkqD dDmP nFoF} Um{qD(Aa pS rQ rX rY rZ sK sM tN tO tQ tR tS tT tU tV tX uG uI uM uN uO uP uR uT uU uV uW vB vC vH vI vO vQ vS vT vV wB wC wD wE wF wG wH wJ wK wL wP wQ yD yH yJ yK yL zA zH zI tM tL xA) vQ(aC aD AJ aX Ba bE bG bI Cp Ct Di dL dM Ed Fr Fw Ha hC Hf Ib IZ Jd Jk Kf Kg Kj KR Lx Mf Mg Mp Ms Mw My Ng oE Of On Pg Po Qe qG Qh Qy Qz rO rY Uf uG Uk uN Up uU vT vU tL) tL(aC aD Af Ap Aw aX aZ bC bE bF bG cE Cp Ct cZ Db dJ dL dM dN Et Fb Fr gL Hc Hf Hq Ib iO Iq iZ Jk Kf Kp Kr Mg Mm Na Ng Oe Of Pf Qe rU sM tR tS tV Uf Uk uN uU vS vU wP yL zH) zH(aC Aw bE bG Bn bR Cp Ct De dM dN Ed Et Fb Fr Fw gL Ha Ib It Jd Kr Lj Lx Mf Mh Mj Mp Na Nf Ng Nk Nn Oe Of Oh pF Pg Po Qe rC rU tN tU Uf Uk Up uU Uv vU Tj) vU(Aw aZ bG bP cE Cp dL dN ED Fw Ha hL Ip Jd Kr Lx Mj Mp Mr Nb Nf Nr Oh oK Pe Pg Po pY Qb qC Qe Qy Uk Up Vv wL Tj) wL(aC aD Ap Aw bE bG Cp Ct cZ Di dL Fr gL Hf Ib Ik Iq Jk Kr Mg Ng Of Pf Qe Qz rU sM tR tS Uf Uk uN uU) uN(Aw aZ bC bF bI cE Cp Fw Ha Hq iC Jy Kr Kx Lx Mb Mp Nb oK Po qC Qe qO qX sM Uf Uk Up vA yL) uU(aA aD Aw bE bI Ed Fw gL Ik Jd Ji Kr Lx Mn Mp Nf pF Pg Po pY Qe Qy Uk Up Uv vI) dL(qH qO qP rN rQ rR rT rU rV uI uL uP uV vA vB vO wQ yH zI tM xA) vS(bI Ed hL Kr Lu Lx Mp Na Nf Oh oK Po Qb qC Qe Qz rU Up Vv Tj) yL(Di Ed Fw Ha Iq Kr Lx Mp Na Nr Pe Pg Po Qb qC Qy rU Up Tj) Qe(pS sM sO tR tS tV tX uM uO uP vO vW wJ wP yK zI tM xA) Uk(tS tT tV uG uT uV uX vA vT vV vW wD wF wG wQ yH yK) vB(AP bE bM cA cE cL dJ gL hA Kc Nb rA Vv) tR(Ed Kr Lx Mj Mp Na Nf Pg Po qC Un Up) uG(aZ bC cE cG cL Di gW hA iC Kx Nb Vv) tV(cE Ed Fw Ha Lx Na Po Qb Qy Up vH) Kr(pS sM sO tQ tS uM vW wP zI tM) Uf(uM uT uW vA vH vI vP vV vW zA) qC(Dk Kf rZ sM tS vW yH yE tM xA) wF(aZ bE bF cA cE gL iC iO pS tQ) xA(Ap bF bM bW dR gW Kx rU Vv) sM(bG Ed Fw Lx Pg Po Up vI) qZ(bG Ed Fw Iv Mp Po Qg) tS(Fw Lx Na Nf Po Up) vW(aC bE hA iZ Lj qH) Di(pS rN rR uI zG) bG(tU uZ vA vO wC) wP(Mp Po rU Up vA) Ed(pS sO vO zI) Hf(sO tQ wQ yJ) bF(uO vA wG wQ) Po(pS sO vO) Fr(vV zG zI) Lx(sO vO zI) Of(vH vP vV) wG(aZ cA cE) rU(iZ vO yJ) Aw(vH wK) tQ(Na rY) rR(Jd Uv) vA(bE gL) ApqG MfvH MpzI IquZ PgpS bPtM dJtX dRuO nRjP mErY mTjU jGvP} Hf{Ad(eD eT eZ fN fY hA hL hO hP iB iC jD jG jI jL jM jO jP jY lK lL lM pS pY qA qB qC qD qG qH qI qO qP qQ qU qV qW qZ rN rO rP rQ rR rS rT rU rV rW sC sK sM sO tN tO tR tS tU tV tX uG uI uL uM uN uO uP uR uT uU uV uW uX uZ vA vB vC vH vI vO vP vQ vS vT vU vV vW wB wC wD wE wF wG wH wJ wK wL wP wQ yD yH yJ yK yL zG zH zI yE tM tL xA) wH(aL aP aZ bC bW cA cI cJ cP Cv cZ dB Dc Dd dJ dR eC Ed Fp GL gW hB hL Hu hX iC Ih Im iO iP Jd jK jM kS Ky Lj Ly Mh Nb nW oE oF oH oN Pe qC QD Qh Qm Qz Rb Rh sK Ug Uk Ut vH Vv tL Wm) qD(Kq pS qU rT rX rY rZ sC sM tO tR tS tU tX uG uI uM uN uO uP uR uT uU uX vA vB vI vO vP vT vU vV vW wB wC wD wF wG wK wL wP wQ yD yH yJ yK zG zH zI yE tM tL xA) bW(sC sM sO tR tU uG uM uX uZ vA vB vO vP vQ vS vT vU vW wB wF wL wP wQ yK tM tL xA) nH(eD gW hA iB jD jE jF jG jH jI jL jM jO jP jQ jR jT jV jY lK lN lO qV qW qX qY rA) hO(Aj Dc gP Jd Jt Mh On rW tN tS uZ vI vP vQ vT vV wB wD wQ yH zH tL xA) hL(Dc Dl rY rZ sC sO tN tU uP uV uX vP vV wB wJ wL yH yK zH zI tM tL) wQ(aN aZ bB Dc Dd dJ Ed Et fN Hw iZ Ju Ky Ly Nx Po qC qQ qU Qz Uk) mZ(eD gW jD jE jH jK jL jM jO jP jR jT jV jY lM lN lO qV qW) mT(eD iB iC jI jK jL jM jO jP jU jY lK lL lN qU qV qW rA) Ju(sC tN uP uV uW uX vP vS wC wD wG wK yH tM tL xA) nC(hA hX jE jF jG jH jI jL jM jV lK qW qX rA rY) Rb(qQ tQ tT tU tX vB vU wB wD wF wL yH tL xA) Pk(pS sK sM tQ uM uP wC yL zG zI yE tM tL xA) Jd(cZ lL qI qQ qU qV rT uP uV vB wB wC wL) Ed(qX rA rS tU uP vB vW wB wE wJ yK xA) wF(Dc Dd Hw iO Ly Nr oE oH oN Qz) xA(Ap Dc Dd Et Ic Ly Mm qC Qz Uf) nK(jG jM jU jV lK lL Ow rA) wL(bC Dc gW Ky nY oH Qh Ub) tL(bC Dc Lh OH On qQ qV) Qz(qQ rT uL vB wD wJ yH) Wn(eD jG jO qU qV qW) qC(qU rT rX uM uW wD) rA(mP mU mW nB oO oQ) Uf(vT vV wD wE wJ) oQ(hW jY lK lM rZ) Iq(rT uZ vB vH) mP(iC jH jK jT) mU(iC jH jK jT) qV(Kq Nj qX Tk) sC(Jv Lv Po Uk) qQ(Dc Dd Qh uW) vP(aZ Om Uk Vv) vT(Hw jO Mm Nr) mF(hA jL rX) jY(Kq oO Rc) vB(bC Hw Ib) vI(Ap Et Om) Jp(uG uM) Tk(eD qU) On(uG vH) cI(tV yD) cW(qX rY) mW(iC jK) tX(fY gW) qG(Ap Hb) oO(hX rZ) oP(jP lL) uW(bC Po) vV(Om Vv) DcvS DdrU LyuM NjrT TzvH RchA KkuU KqqU LdnB LjvW OkqX OwnN cPuZ mErY mMhW nLrC yDoH kFoN} jP{nR(AD aE Af aG aJ aK aM aN AO AP aQ aR aS aU aV AW AX aY aZ BA Bb bC bF BG bH bI bJ bL bM Bn bO bP bQ bR bS bU bV bW bZ cA cC cD cF cJ cK cL cM cN cP cQ cR CS cT CU CV CX cY cZ dA dB DC DE DG dH DI dJ DK dL dM dN dR eC Ed eF Ez fP gL GP gW Ha hB HC hF iA Id iO IZ Jd Je Jv Kd Ke Kg KQ KR kS nW nY oF oH oK oN Or pF Qh Qz Rf Rg Rj Rm Sr Ss St Tv Uf Ug Uk Ul Up Ut Uu Vo Vs Vu Tj tF) mM(aI aM AO aP aR aV aW aZ Ba Bb bF bL bM Bo bV cC cE cG cJ Co Cq Cs CT DB dC De DI dJ Dk Dp Ef Ez Fy Hc Ib Id Kc Kg Kk Kn Kq KS oF oH oN Ou Qt Ss Uh Uk Uo Ur Ut Uv Vp Vs Vu Tj) mZ(As Aw Ba bF bJ bL Bo bX bZ cB cE cG CT Db dF dJ Ed Fb GL Gp hG Ir Ju Kc Kd Kg Kl Lx Me Mh Mr Mt Ne Nk Nu Nv Ny Oe Og Oh oN Or Ou Pa Ph Pi Po Qe Qt qX rA Rb Rc Tn Tv Uf Uo Up Vs) mF(Ad Al Ao Aw Ba Bb bF Bg cG Co Cp Cq Ct Dk Fy Gl Hc Ib Ir Jd Je Jf Jy Kf Kg Kn Kq Lx Mr Nr Nv Ny Ou Ow Oy Pd Pe Pg Po Qx Qy Qz Rb Rc Tn Tz Uc Ur Vp Vs Vu Tj) oP(aH Ao aW Ax aZ Ba bB bF bL Bo cJ Co Cq cR Cs cT Cu CV cW cZ DB Dc dH dI Dk Dl Dp eC Ef Fn Fy hB Jd Kd Kf Kn kQ Kr Oa oK Pk Qt Qy Tv Uh Uo) mE(Aa As Ba cE Dd Fn Kn Ko Kq Mt Nl Ny Oh oN Ow Pg Qm Qt Qy Rm Sr Ss Tv Uc Vs) lX(Bo cE cW dD hC Jd Je Kf Kn Kq Nv Nw Nx Ny Ok Ou Pg Qy Uo Ut Vp Vs) Tv(kF kG kK kP lW lY mI mP mT mU mY nC nD nF nH nJ nM nU oO oQ) kI(Ad Aw bL cF Fy Hc Jd Je Jf Kj Kl Kn Kq Qt Qu Qx Qy Tn Ut Vs) Uh(kE kF kG kN lW lY mS mU mW mY nA nB nD nF nI nM nO oQ) oN(kC kE kF kG kK lW mS mY nF nI nJ nK nL nM nN nU) Ow(kC kG kP mS mT nB nD nF nK nO nU oO) nA(Kp Mr Ny Ou Pg Po Qt Ur Uv Vs) nO(Bo dB Dp Fy Ib Jd Je Kj Qy) nC(Fn Ko Me Ny Pg Pi Rm Tn) nL(Kf Ko Ny Pg Qt Tn Ur) Bo(kF lY mI nI nJ) Kf(kK lY nH nI nN) mP(Gp Jf Kg Qt Tn) nK(Kn Mr Ny Pg Tn) Fn(kC kK lY nH) Ou(kE kN mU mW) mT(Jd Qt Qy Vp) nJ(Kg Ny Pg Vu) Kn(lW lY mI) oQ(Cs dI Kg) Iv(Tk Wn) St(kC kK) Ny(kN mI) nI(cG Uv) kG(dJ Gp) GzTk IquZ RckP JfnD KgmU KpkK KrwB RmnH UrlW PgmS dBwH} Nt{Jt(eZ fY hL pS qG qH qI qO qP qQ rN rO rP rQ rR rS rT rU rV rW sC sK sM sO tN tO tQ tR tS tT tU tV tX uG uI uL uM uN uO uP uR uT uU uV uW uX uZ vA vB vC vH vI vO vP vQ vS vT vU vV vW wB wC wD wE wF wG wH wJ wK wL wP wQ yD yH yJ yK yL zA zG zH zI yE tM tL xA) Ad(eT eZ fY hL hP pS qG qH qI qO qP qQ qV qZ rN rO rP rQ rR rS rU rV sC sK sM sO tN tQ tS tT tU uG uI uL uM uO uP uR uT uU uV uW uZ vA vB vC vH vI vO vP vQ vS vT vU vV wB wC wD wE wF wG wH wJ wK wP yD yH yJ yK zA zG zH zI tM tL) Ap(eZ pS qG qH qI qP qQ qZ rN rO rP rQ rR rS rT rU rV sC sK sO tO tQ tR tS tT tU tV tX uG uI uL uM uN uO uP uR uT uU uV uW uX uZ vA vB vC vH vI vO vP vS vT vU vV vW wB wC wE wF wG wH wJ wK wL wP wQ yD yK yL zA zG zI yE tM tL xA) Qz(qG qO qP qQ rO rR rW sC sM tO tS tU uG uI uL uM uN uO uW uX uZ vA vB vC vH vQ vT vW wE wF wG wH wJ wL wP wQ yL zG xA) On(eZ pS qC rN rR sC uG uI uL uM uO uP uU uX uZ vC vH vO vP vQ vU vV wC wL yH yJ yK yL zG zI tM tL xA) Pj(qG qH qI qO qP qQ qZ rN rO rP rQ rR rS rT rU rV rW tN tO tS uV uX vB vH vI wG wL wQ yL zG tL xA) Jd(eZ qG qQ rT sC tU uG uI uL uM uN uO uP uW uX uZ vA vB vC vP vQ vW wB wC yL zG yE tM tL xA) Ed(sC sO tS tU uG uI uL uM uN uP uW uX uZ vA vB vH vW wD wE wF wG zG tM xA) Uf(pS rT sC tO uG uP uU uW uX vA vP vT vV wD wG wJ wK wL wQ yL tM tL xA) Ok(qG qO qP rT rW uM uO uZ vA vB vP vV

Figure 23 Continued wL yD xA) Kf(qG qO qP rP rT sC tT uP vP wD wG wK wQ tL) Nm(rU tO tQ tR tS tT tX uL wE wL wQ) Jv(sC tT tV vV wG wK yD tM tL)
Kg(qG qO qP tO vP wK tM tL xA) Iq(rR rT tV uZ vB wG wL tL) uP(Ba Ef Et Kj Kl Lh Qu Uu) Rb(vB wF wG wH wL tL xA) Kj(qO rN wK
wQ tM tL) Uu(rT sC tU uW vP tM) wH(Aw DB Kr Uk) xA(Ao Id Mm Sr Vt) sC(Aj Ba Bf qD Qu) vB(Ib Id Lh Mm Sr) wQ(Cu Db Dg fP)
wF(dB Dd fP iO) qG(Dg Et Hb Jg) Ao(tT uO vW) Lh(uM vC wL) tM(Aj Dg Qu) Et(qP yD) Sr(rT tL) mF(hX jE) qD(uW uX) wC(Pk Qu)
qO(Hb Jg) MmwG IbtL JpyL UkvP PhtT mZrY} rY{mE(aD Af aI Aj Aw Ax bB Bn bO bU cF cH cJ Cq Cs cT Cu Cv cW Cx Dc Di Dp Ed eF Ez Fw Fy Gl Gp Ha Hb Hc iO Iz Jj Ju Kd Kg Kk Kl Kp Kr Ks Ky Nl Oa oF oN Or Ow Qg Qh Qt Qx Ra Rc Rh Rj To Uk Un Uo Ur Uv Vo Vs Vt Vv Wm) nB(aD aF aG aO AP aR As Bg bH bL bM BO bX cB cF cI cR cS cV Cx cZ dB dC Dd dJ Dl Ez Fa Fb Fn Gp Ha Hc iZ Jf Ju Kd Kf Kn KR oH Or Ou Pj Pk Qt Qx Qz RA Rb Rf To Tv Tz Uk Uo Ur Ut Uv Vt Vv Wm) mZ(aA aC aD aG aI aK aQ aV aW aX aY bA bE bF bG bJ bL bN bO bP bR bX cB cD cF cG cI cM cQ cS dA dB dC dD dE dL dR eF gW hC hG iB Iv kR lY nN nY oF Og oH Uk Uo Up Ut Uu tF) mF(aI An Ao Ap Ba Bg Ch Co Cp Ct cW De dJ Dk Fa Gp Hc Hw Jd Je Kd Kg Kq Kr Kx Ky Qg Ql Qy Rb Rc Rg To Ut Tj) cW(Ex kC kE kG kI kK kN Kp lW mI mM mS mT mW mY nA nC nD nF nH nI nJ nK nL nM nN nO nU oO oP oQ) Uo(kI kK kP lW lX lY mM mP mS nA nC nD nF nH nI nJ nK nL nM nN nO nR oO oP oQ) aW(kC kI kK kN kP lX mM mP mS mT mW nC nD nH nI nJ nM nN nO nR nU oP oQ) nC(Ad aI bB bR cH Cu Db Fw Gl Jf Ke Kf Ko oF oN Ou Pk Ql Qt Qx Rm St) Bo(kC kE kF kG kK kN kP lW lY mM mS nF nI nJ nL nM nN nO nU oP oQ) oQ(aI Aj bR cB Ct cZ dB dC Ez Fb Jf Kk oE Ow Ph Qt Qx) nL(Ad aI bB bR cH Cu Db Gl Ke Kf Ko oF oN Ou Qt Tv) Ow(kC kF kG kN kP lW lY mM mS mY nF nM nR oP) bR(kC kF kI kK kP mM mW nH nI nJ nU oO oP) dB(kI lW Mm mP mU nA nF nI nO nU oO Uf) aI(kC kE kF kG kI kK lW lX mT nK nO) cB(kI lW mM mP mS mU nA nD nR oP) oE(kC kF kG kN kP mM nH nJ nU oP) Uh(kE kN lW lX nF nH nM) mM(bZ Cp Ct cZ Kk Uu Vt) hC(kK kP lY mW nD nI nK) Qx(kC kN lW lY nR) Ou(lX lY nI nJ nU) dC(lW mP mU mW nR) oF(kC nD nH nI nK) Gz(Ad hL Ld qD) Rc(kE mS nI nR) dJ(Jp mY nJ Ok) oO(cJ cZ Jf Qt) oN(kC kF kG nH) Db(nR nU oP) cH(nA nH nO) lY(Jf Qg Vt) kN(Ct Fb Ph) Ad(Ex Kr) To(kI mI) Iq(hO qG) Qz(eZ wJ) Qt(lX mY) Uk(fY vP) Vs(kF kI) aZ(fY qO) bB(nH nK) cJ(kP nD) cZ(mP mT) nO(cG Dg) mS(Jf Qg) FbnR ExhO GplX NaKq KckG KkqC KrtM aDmY bXmT dDnF iOpY} dJ{Et(eT eZ fN fY hR pS pY qA qB qG qH qI qO qP qZ rN rO rP rQ rR rS rT rU rV rW sC sM tN tO tQ tR tS tT tU tV tX uI uN uP uR uT uV uW uZ vB vC vH vI vO vP vQ vS vT vU vV vW wB wC wD wE wF wG wH wJ wK wL wP wQ yD yH yJ yK zA zG zH zI yE tM tL xA) Jp(pS qD qG qH qI qZ rC rN rO rP rQ rR rS rT rU rV rW sC sK sM sO tN tO tQ tR tS tT tU tV tX uG uI uL uN uO uP uR uT uU uV uW uX uZ vA vB vC vH vI vO vQ vS vT vU vW wB wC wD wE wF wG wH wJ wK wL wP wQ yD yH yJ yL zG zH zI yE tL xA) tX(Al Ao Ap As bB bX Dc Dd Dg fP Ic Iq Jt Kf Kg Kj Kk Kl Kn Lh Mm Ok Ph Pj Pk Pz Qt Qu Qv Qz wG) Pk(hP pY qH rT rU tN tO tQ tR tS tT tU tV uN vB vS wB wC wD wE wF wG wH wK wL wQ yD zA xA) hW(kC kE kF kN lW lX lY mE mF mI mM mP mS mT nB nD nH nI nJ nK nL nM nR oP) hV(Ad kE kF mF mM mP mS mY mZ nA nB nF nH nI nJ nK nL nU) Ap(eT eZ fN fY pY qA qI rT tN tO tR tS tT tU uZ vI wQ) Ph(tN tO tR tS tT tU tV wB wC wF wG wH wJ wK wP yD) nH(Hc Jd jR Kk Kl Kq Ld Lh Mg On Sr Tn Tv) tQ(Ad Ao Dg Hb Hq Jt Kf Kg Mm On Pj qV Uf) rC(kI lX mE mF mP mS mY mZ nB nF nJ nN) tT(Ad Dg Hb Is Jd Kf Kg Kj My Ok On) nK(Jq jR Kq Lx Ny Pa Po Tv Tz Uc) wQ(Cu Db Dd Gz Hb Ic Jo Lh Qz Uf) nB(hR hX jK jQ Kq lK Ow rX rZ) nJ(hR hX jK jQ jR lK qV rX rZ) tU(Ad Ao Dg Hb Kf Kg Lh Ok Uf) lL(kE kG kN mM nC nN oO oP oQ) wG(bB Hb Hq Hw Ic Kg Qz Uf) wH(cF Db fP Gz Hq Ky Na Qz) oQ(gW jI jK jU jV lK lN qY) Ad(hR pY tN tR tS tV zA) Uf(tO tV wC wD wJ xA) vB(bW dN Jj Lh Ok qW) Kg(tO tR tS wE wF) mY(hR hX jK rX rZ) nC(jK jR Kq lK qV) Hb(pY tN tR tS) Qz(qQ wD wF xA) lK(kF kG lY mZ) oO(jI jU oN qY) Hw(wD wF wL) Ok(eZ hR xA) mS(hR hX rX) qV(mF nF nU) jR(lY mF nL) oP(jQ jV qY) Lh(tO wE) On(tS zA) bW(uG uU) bX(Ic wL) wB(Db fP) jK(nN nU) oN(kF nR) AotO KqnO WnjG bBwD dNvW eTtL mMjO nIjQ hGuU jHvS} Kr{Dd(pS qG qH qI qO qZ rN rO rP rQ rR rS rT rU rV rW sC sK sM sO tN tO tQ tR tS tT tV uG uI uL uM uN uO uP uR uT uU uV uW uX uZ vA vB vC vH vI vO vP vQ vS vT vU vV wB wC wD wE wG wH wJ wK wL wP wQ yD yH yJ yK yL zA zG zH zI yE tL xA) Uf(eZ fN pS qA qC rQ rT rU sC sK sM sO tN tO tQ tS tT tU tV tX uG uI uL uM uN uO uP uR uT uU uV uW uX uZ vA vB vC vH vI vO vP vQ vS vT vU vV vW wB wC wD wE wF wG wH wJ wK wL wP wQ yD yH yJ yK yL zG zH zI yE tM tL xA) Ad(eT eZ fN fY hL hO hP pS pY qA qB qC qD qO qP qZ rQ rR rU rV sC sK sM tN tO tQ tR tS tT tV tX uG uI uM uN uO uR uT uU uV uW uX uZ vA vB vC vH vI vP vQ vS vT wB wE wG wH wJ wK wL wP wQ yD yH yL zA zI yE tM tL xA) Jp(qH rQ rR rT rU rV sC sK sM sO tQ tR tS uG uI uL uM uP uT uU uV uZ vB vH vI vO vQ vT vU vW wE wF wH wJ wL wQ yD yH yJ yK yL zA zG yE tM tL xA) Jt(eT eZ fN fY hL hO hP pY qA qB qC qD rR rV sK sM sO uL uP uU uZ vB vH vW) Et(eZ qA rQ tT uI uL uP uT vB vI vP vS vU vW wB wD wK wQ yJ tM tL xA) Ap(eT eZ fN fY hL hO hP pY qA qB qC qD qG rV uZ vB vI vW yE tM xA) Qz(qQ rT sC sK tN tV tX uI uR uU uV vB vH vW wB wD wE wK zA yE tM) vW(Ao bW Dc Dg dN Ed Hw Jo Kg Kn Lh Lj Ly Nk Ok Pj qC qD) tM(aO bW Hb iZ Jd Kg Kl Ly Om pF Pj qC qD uU) Pj(qH qP qQ rO rS rU rV uL uU xA) wB(Ao bW Dc fP Hw Ic Jo Kg Lh qD) Ao(pS sM uP uT vH wF wQ xA) Kg(rV uL vB vP wE wQ tL xA) Dc(uP vU wF wH wL zA tL) Hb(qA qC rV uP vI tL) xA(bW Ic Jo Mm) uU(Kk Ly Mm qA) vB(Ed Hw Lh Mm) wH(cI Ug Uk) rA(kG nB nC) Jd(uV yE) Pk(vS wC) tL(Jo Kj) sC(dM Ju) EduW LyyE HwzA IcwQ IquZ JgeZ KluP KnwC bWvT cItT eTyL mMhX nCqX hWoQ} qD{tM(AF An Ao Ap As Aw Bb bM bW bX cF Ch cM Cq cS cV DB Dd De dN Ed Ef ET Ex Ez Fb Fn fP Fw Gz Ha hB Hc hG Hq Ib Ic Id iO Iq Jj Jp Jt Kc Kd Kf Kg Kj Kk kR Ld Me Ms Na nW Nx Oa oE On Ou Ow Pj Pk Qg Ql Qv Qx Qz Rb Rf Rg Rh Rj Rm Sr Ss Ub Ue Uf Uk Ur Uv uW vB Vp Vt vW wG Tj) Gz(Ad Dc eZ Ha Je pS qG rT rZ sC sM tO tS tT tU tV uG uI uL uN uO uP uT uV uW uZ vA vB vC vH vI vO vP vQ vT vU wB wC wD wF wL wQ yH yJ yK yL zA zG zH yE tL) Ex(Dc eZ Kq ON pS rT rZ sC tR tV tX uO uT uU uW uZ vA vH vI vS vT vU wB wD wE wG wH wQ yJ yK yL zG tL xA) uP(cF cI Cq Dd Dl Ed Et Fb Hq Ic In Ip Jd jH Jq Jt Ke Kf Kj Kp Ky Lh Na Nk Nm Pj Pk Qz rT Uf Up Vp vW zA yE) Pk(qG qI qU qV qW rO rQ rT rX sC sM uM vH vS vW wB wC wD wE wJ wK wL wP wQ yD yJ yL zG yE xA) vW(bW Db Dd dN Ed Fn fP hG Ic Iq Jd Jj Kf Kn Ky Lh Me Oa Pj Pz qA Qz Rj sC Un) sC(As Dc Dd eZ Hq Iq Jp Jr Jt Ju Kc Me Mn Na Nk Qy Rb rU Ue Uk yE) wQ(Al Ap As Cu Db Dd Hc Ip Iq It Kk Lh Mm Na Nk Pj Pz Qa Qu Ra) Lh(tN tO tQ tS tT tU vV wC wJ wK wL wP yD yJ zG) qG(Ap Dd Et Hb Ic Ij Jt Kc Kf Kg Ok Ph Pj Qz Sr) wK(Ap bB Dd Et Ic Jq Jt Kg Kj Kn Ph Pj Uf) Na(Aa qU rT rZ uG uW uX vA wC wG yL zH) Db(Ad qU rT vI wB wD wH yJ) Iq(gP Jp rT tV wB yJ yE Wm) tT(Ao Ap Et Kg Mm Ph Pj Uf) fP(bQ eZ Jd oN Uv yJ yE) Kk(tN tR tU vB yH yE) Hc(tR uM uW vU wG) Qz(qZ rT rW wC xA) eZ(Fn qV Tt wG) rT(Dd Hq Jd Jp) Al(tR tU wB) Ap(aK jQ yJ) dB(Ad Jt Nn) yE(cM qA Sr) Ic(wD wJ) Kf(aK jQ) Uf(wJ yJ) uW(Me Nk) DdyH EtaK FnaG TtRh JtcC UkyJ qAvB} dB{Qz(qG qO qP rO rQ rR rS rT rU rV tN tO tQ tR tS tU tV tX uG uI uL uN uZ vC vH vS vU wB wC wD wE wF wG wJ wK wL wP wQ yD yJ zA zI tL xA) Ad(eT eZ fY hL hO hP jL pS pY qA qB qC qG qQ qZ rN rU sK sM tO tQ tT tV uI vO wB wD wE wF wG wH wJ wK wP wQ yD yH yL zH zI) hA(kC kE kI kK lW lX lY mE mF mI mM mP mY nA nB nC nF nH nI nJ nL nM nN nO nU oO) mU(eD gW hV hW hX iB iC jD jG jK jL jM jQ jR jY lK lL lN qU qV qX qY rA rC rX) Jp(tN tO tQ tR tS tT tU tV tX wB wC wD wE wF wG wH wJ wK wL wP wQ yD zA) Hq(jL tN tO tQ tR tS tT tU tV tX wB wC wD wE wF wJ wK wP yD zA tL) jL(Jt kF kG kI kN kP Kq mM mS mT mZ nH nI Nn nR oO oP Tn) Et(qG tN tO tQ tR tS tT tU tX wC wF wJ wQ yD zA) nR(hV hW jD jK jM jO jU jY lL lM lN qV qX qY rZ) Uf(tN tO tS tT tV wB wF wG wH wJ wK wL wP wQ) hV(kF lW lY mF mM mP mW nD nF nO nU oO oQ) wH(bW Dc Dp Fn Fp Hr Hx Iq Is It Lj Nu On) Jt(hL qC qQ rN tR tS wC wG wJ wL wQ zA) bW(tS uG vB vT vW wD wF wG wL zA tL) wQ(Ap Dc Fn Hb Iq It Jo Ju Kf Kg Mm) Iq(sC tV tX uU uZ vB vH wF wL) kI(eD hW jK jY lN qV rC rX rZ) wL(Dc Ex

Figure 23 Continued fY Hw Is It Na Nr) oQ(hW jY IK IM qX rA rX rZ) IW(eD iC jK jY IN IO qV) hX(kC mF mW mZ nC nK nL) wF(Dc Dd Ex Hw iO Is Jd) Ap(tS vP wC wJ yD xA) Dc(hL tT tV wB zA) rX(mF mP mW mZ uM) oO(iB jK IK IN qV) Ju(tV wG wP zA) Jv(sC tV wP zA) mT(iC jT jU qV) hW(kF mW nB oP) Fn(qU wB wK) Pk(wC wP zA) mF(jF qV rC) mP(jK IO qV) yD(Ex Kg Ok) rZ(mW mZ nL) oP(jT qX rA) uM(Fy jD jY) Gz(eD Tk) Is(tT wK) It(tX wG) Jd(eZ zA) xA(Fy Mm) DbwB DdtV QhwK OnwC dNvW nOjE lXjR lYlM mMlL mWhR mZlK} Na{Ad(eZ jL pS qG qH qI qO qP qQ qZ rN rO rP rQ rR rS rT rV rW sC sO tN tO tR tS tT tU tV tX uG uI uN uO uP uR uT uU uV uW uX uZ vA vB vC vH vI vO vP vQ vS vT vU vV vW wB wD wE wF wG wH wJ wK wL wP wQ yD yH yJ yK yL zA zH zI yE tM tL xA) On(pS qG rN rO rT rW sK sM tT tU uG uI uL uM uP uT uU vH vO vP vQ vS vV vW wC wF wK wQ yH yL zG zI tM tL xA) wQ(aC Ao Ap bB bC bF bW bZ Dc Dd Dg Dk Et hB Hq Ii Jt Kc Kf Kg Kj Lh Ms Nm Ok Om Pz qU Uf Ug Uk Ur zI) Dc(qG qO qP qQ qZ rN rO rR rU rV rW tX vB vH vT vU wC wE wF wG wK wL yL tL xA) xA(Ap Bb bW Cv Dd Dk Ed Hw Ic iO Iq Jp Jt Lh Mh oH Ok qW Qz Rc Uf) Lh(rT tO tV uL vB vQ vS vV vW wB wE wF wJ wK yH) Jt(qG qQ qZ rN rP rS rT rU sK uL uN uW wJ wK) Kq(hX jL jM jO jU qU qV qW qX qY rA rC rZ) qQ(Ap cI Dd Dk fP iO Jg Ng nY Pz Qh Qz Uk) Iq(qG rT rU sC tU tV uL uT uW uZ vB vW) Ap(qG rN tT uM vA vP vT vW wJ wK wP) uL(Et Hw Is Jj Jk Jp Kj Nj Nx Ub Uc) bC(rT sC uW vB vH vQ wC wG yK tL) wC(cR Ha Hw iA Jd Om pF qC Qh) Jp(pS rS rT rU sK uM vH yL) Hw(rR tT uP vB wL yE tM) Qh(qG rT rV vH wL yL tL) bW(vA vB vH vT vU vW tL) Jd(eZ qI uM vB yK) tL(Dd Kj Ms oH qV) lL(nC nH nR oP oQ) rT(cR Et Jg Ok qC) Je(qH uU vQ yL) Uk(sC vP wF tM) qG(Dk Et Jg Kf) uX(Ju Ni qU vW) Ii(vB wB wE) cI(tV tX yD) nA(Bo Lx Ny) sC(iO Ju Jv) uW(Aa Po qC) Et(qZ tT) Kj(rN vH) Ld(tX vB) wF(iO Ug) BbqX DdrU DkqO MguN MszG TzvH TvnB PztU JkvB JuvS NxzI OmtT UouU UfvT dNvW kFoN} xA{bW(Ad Af Aj Al An Ao Ap Ar As Aw Ax Ba Bb BG Bn Bo Ch Co Cp Cq Cs Ct Cu Cv Db Dc De Di Dk Dl Dp Ed Ef Et Ex Ez Fa Fb Fn Fr Fw Gz Ha Hb Hc Hu Hw Hx Ib Id Ih Ik Il Ip Iz Jd Jg Jh Ji Jj Jk Jm Jo Jq Js Jt Ju Jv Jy Kc Kd Kf Kk Kl Kn Ko Kp Ks Kx Ky Lh Lx Ly Mb Me Mf Mg Mm Mn Mp Mu Mw Nh Nj Nm Nq Nx Oa Oi Ok Om On Or Ow Pa Pc Pe Ph Pi Pj Qb Qd Qe Qg Qh Ql Qn Qt Qu Qv Qx Qy Qz Ra Rb Rc Rg Ri rZ Ss Tz Ub Uc Ue Uf Uh Uk Ul Un Up Ur Ut Uu Uv Vo Vs Vt Vu Vv yH Wm Tj) Pk(aC aN AP aZ Bb bC bE bF bM bO cA cE cG cI cL cX Db dH dR Ed fN Fp gL gW hA hO Hq Hu iC Ih lO Iq Jh jO Kc Kk Ky Lj Ly Mp Nb Nk oE oH Ow pS qC qW Qz sK tQ Ue Uf UG uI Uk vH Vv wE yL zG) Ic(aC aN bC cN cR Cs dR eC Fn FP gP gW hF hG iA iO iP iZ Jh kQ kR Lj Ly Ma Nc Nl Nu nW oE oH oK oN Pa Qu Rb rU Uc Ue Uk Vv yD tF) Ap(Aj aL Ba cW Dl Ed hG Hu jG Kl Lj Mn Nd Nq Nr Oe Og Oy qG Qu qW Qz Rh Rj rN rR sK Uc uG uP) Uf(aK aP cC cZ Fn hG Hu Io Jj Js Lj Ma Me Mp Nb Nm Ow Pa Qd qW Qz Ue Uv vH tL) Qz(Bb cC dC Dd Fw Hu Io jF jU Me Nw qW uP) Hu(Ch Et fP Kf Kg Lh Ok) Dd(cC Db Gz Qd rU Ue) qW(Jd Jh Kf Mm Nk Uk) Gz(Cv Ed iO oE) Pa(Ed Fw Ha Qg) Et(aL aP Dg) Kf(Ez Kk Uc) Ok(aZ Qd Uc) Ao(aP Mn) Db(hO Mm) Ex(hO Ly) Uk(fP sC) AdaZ EdHw MmcC MnKg IoPj QvbC PhaP} mF{hX(Ad Al Ao Ar As Aw Ba Bb Bg Bn cB CH Co Cp Cq Ct Cv Dd De Dg Di Dk Dp Fa Fn Fy Gp Hc Ir Iz Je Ju Jv Kd Ke Kg Kl Ko Lx Md Me Mp Mr Nk Ny Ou Pa Pf Pj Po Qa Qe Qg Qh Qt Qv Qx Rb Rc Rg St Tn To Tz Uo Uv Vs Wm Tj) jE(Ad Al Ar Aw Ch Co Cp Cq Cu Dc Dd Dg Fa Fp Fy Ha Hw Id Ih Im In Ir Jf Jk Jt Ju Jv Kg Kj Kl Kn Ko Kp Li Lx Me Mn Mt Nc Nk Nl Nr Ny Oh On Ou Pa Pe Pf Pi Po Qa Qb Qe Qh Ql Qt Qu Rc Sr Ss St Tn Uc Uh Up Ur Ut) rX(aD aL aR aU cB Cq Cv cW cY cZ dC dD Dl gW hC Hv Ir kS Qt Qv Rc Uh Uo Ur Uv) eD(Bo Dc Fp Ih Ii Ir Jq Kf Lx Mn Mr Mt Nn Nr Nv Pf Po Qa Qb Qe Qt Tz Uv Vs) rZ(BA bF cB cE cG Ch Co Cp Cq cW Gl Jf Kq oN Qt Rc Uh) Bo(iB iC jD jH jK jM jO jQ jT kF lL lM lN lO qV qW rA) Lx(aO aP bV bW bZ cG dF dM Ed iA lM pF Wm) qV(aN aR aW aY Cu Db dE Fn Uo Up) Qa(jM jQ jR jV jY lM qU qY rA) Ex(aP bW cH Ib Iv nN Tj) hW(cT cW De Gp oN Rc Uo) qU(Al Dd Kf Kn Qt Rm Uv) Ir(hR iB jH jM jV lL) Vs(hV jF jH jV lL lN) jU(cW hC Kq oN Qt Uo) jY(Al Nr Qe Rm Sr Tv) jF(Db Gp Qt Uv tF) oN(aO dN jO kF tF) Rc(hR jG lK rC) jD(Jf Qt Ur Uv) Jm(gW iB lL) hV(Gp To Uo) jM(Dc Fn Hw) Ql(hR rC) Ny(kQ nA) eC(hA jG) jO(Gp Uo) lL(Mr Nr) lO(aY Fn) DbhA EdJq HwrA IdaR TvlN KdrC aWhR} oN{kF(AA Af aH aM aN AO AP AS aY bA Bb bC bG bI bJ bN bP bV bW cA cB cC cH cJ Cp Cu CV Cx cY Db Dc dF DG Dk DL dM dN eC Ex gP Gz Hb HW Ic Ih iJ Ik iO iP Iv Jp Kc kG Ko kP KQ KS Lj Lu Ma Mn mP MT nA nB nH nI nJ NK Nl nN nO Nw Nx Oi Ok oO oP oQ Pe pF Pg Rj Uh Uo Uv tF) aO(kC kE kG kI kK kN kP lW lX lY mE mI mM mP mS mT mU mW mY mZ nA nB nC nD nF nH nI nJ nK nL nM nN nO nR nU oO) dN(kC kE kG kI kK kN kP lW lX lY mE mI mM mP mS mT mU mW mY mZ nA nC nD nF nH nI nJ nK nL nM nN nO nR nU oO) hW(kE kG kI kN kP lW lX mE mI mU mY mZ nC nD nF nH nJ nK nL nM nN nR nU oQ) aA(kC kN kP lW mE mM mP mU mY nF nH nJ nM nN nO nU) nN(aM Ao aP aY eF Ex Gz lK Mw nC Nm Uu tF) oO(bZ cH cU Di Dl Mw mZ oK) aP(kN lW mM mP nB nJ nK) tF(kN mM mZ nH nJ nK nR) rZ(lY mT nB nI nJ oP) Ex(eZ qQ sC wP yE) Mw(nA nH nK nR oP) bZ(mP mY nI nJ nO) Gz(nB sC tO uV) nR(Ik Nj Nm) mM(Aa jO Tv) mY(iC jK jU) nJ(bV dG kQ) fP(hO qI) mZ(Ic Ko) jK(kC nL) IdnK aMnO bVkN cCnH cHoQ nCjO nDhR} Ex{hO(bQ cS Cv Dc Dk Dl Ef Fn gP Jk Jm Jt kQ Lx Md Mh Ns Pz Qh qO qP qZ rW sC tN tO tR tT Uk uO Uu vH vI vP vQ vV wD wF wJ wK wL wQ yH zH tL tF) Dc(hL qG qH qI qZ rO rP rQ rR rS rT rU rW sC tO tU tX uL uO uR uT uU uV uW uZ vA vB vS vT vU wE wG wL yD yH yK yL zG zH tM tL) Ad(eD eZ fN hV hW iC jE jF jG jH jI jK jL jM jO jR jU jV jY lK lL lM lO qA qB qH qU qV sK sM tQ tR tX uL uM uP vH wH Tk Wn) hL(Co Dl Kf Ng On pS Qh rZ sC sO tN uI uM uR uT Uu uZ vA vH vI vO vQ vS vT vU wC wD wE wG wH wJ wP wQ yD yJ zA zH zI tL) wQ(aN bW cZ Fp iZ Ly Of Pe qC Qz Rb rU Uf Ug uU vH) On(eZ qA qC qG rN sK uP vH wC) wH(cI Cp cZ Fp Ld Qh vH) Qz(qQ rT sC tO wD wE) Jd(eZ lL rT uV wC) Iv(kF mZ nI nJ) aP(mZ nA nJ nK) bW(vB vT wF yL) qG(Ap bG Et Kf) rT(Iq Mm qC Uf) Ly(tU wE wF) Rb(wE wL yH) Qh(uR wB tL) Ld(kI nO tX) iO(qQ sC wF) Ed(wE wJ) Om(eZ sK) Uk(wF wL) Uf(vV zH) cH(kF nH) cI(tT yJ) cW(tS tV) rU(vP vV) uZ(Iq jK) FpvB NbtL IbmT TvnO IkmZ PzqC JeqH JheZ JvsC KywL TkjG aYnN bCvT bHnA cZwB nHkC hPoK} Bo{nA(aA Ef hA Hw Ib Ii Ir Is It Iz Jm Jq jV Ky lL Mk Mv Mw Ng Ny Ou Ow Qn Qu Qy rA Rh Uu Uv Wm) jV(kC kF kG kK kN kP lW mE mI mM mP mS mT mW mY mZ nC nD nF nH nJ nK nL nM nN nO nR nU) kI(eD hA hV hW hX iB jD jE jG jH jI jL jM jO jQ jR jT lL lM lN lO qU qV qW qY rA rX rZ) mW(eD gW hA iB jD jE jF jG jI jK jL jQ jR jU jY lK lN lO qW qX qY) lL(kC kF kG kK kN lY mE mI mM mS mT mU mY nB nI nJ nL nN nO nR nU) mZ(eD gW iB iC jD jE jF jG jL jM jO jQ jT jY lM lN lO qV qY) rA(mI mM mP mS mT mY nB nC nD nH nJ nO nU) qX(kE mI mM mS mY nC nD nI nJ nL nU) lM(kC kG kN lY mI mM mT nI nK nL nR) hA(kF lY mM mP mT mY nC nD nL) lY(eD jG jK jM lK oH qV rC) mM(iC jG jL jM jR qW qY) mY(jG jL jR lK qW qY rC) mE(gW hR hW jG qW) mI(iC jG jQ jY qW) nJ(hX Mk oH qY rZ) lK(mS nC nH nK nN) lX(jL jR lN qW) jK(kC nI nL nN) hR(nF nM oP) hW(kK lW nB) Ow(kF nN) gW(nC nL) mT(iC lN) nI(qW rZ) nK(jG Mw) jO(kN kP) oH(kF nB) TvnN mPjM mSjL mUjG nLjH rCkG kCrZ} Gz{Ad(cT fN fY hL hO hP lM pS qA qB qC qO qP qZ rN rQ rS rV sC sK sM sO tN tQ tS tT tU tV tX uG uL uM uN uO uT uU uW uX vA vB vC vO vP vQ vT vW wC wD wE wF wH wJ wK wL wP wQ yJ yK zH zI tM tL) Tk(aE aL bG bM bP bU cC cF cH Cq cU Dk eD Et gW HA hR hW hX iC Iq jD jG jK jL jM jO jQ jR jU jV jY Li lK lL lM lN lO Nj nY Ok Qh Qn qV qY rA) hO(aD aE Dc Fn gP Jd Jt oF On Pz Qh rS rW tN tT vP vV wB wD wQ yH tL) wQ(aN bC bL bW Dc Fp iZ Jk Ky Nb Of Pi Rb Uf Ug Uk uL vH wC) hL(Dc Dl Ng On Qh uV uX yH yK zA zH tL) cI(qP rX tV tX wL yD yJ zG) nB(bW cG cL Jn Nv Ny Tv) qC(Jt Pz Qc uP uW wD tM) On(rN rP sM uG wC tM) Ld(kI nO tX wD wH) Wn(aE bM cH cU kR) bW(mE vA wF wL tL) wF(Dd iO Ky Uk) tL(Nb Nc oH Qh) qQ(iJ oK Qh Qz) Jd(eZ qU wC) Po(tN tO) Hr(vA wH) Qz(tX wD) iO(sC wD) qG(Ap bG) oF(nD oO) vB(aP bC) CpvI EdwL LyuW MlnH NbwG TzyL UbuL TvnO IqvH RbtX JeqH QuwC JtsK LhtS UfsC PeuP cLnK cRuZ cZwB gLwH lYoH jMrT} Ap{Kk(hP pS qG qH qI qZ rN rO rP rQ rS rT rU rV rW sC sM sO tN tO tQ tR tS tT tU tX uG uI uL uM uO uR uT uV uW uX vA vB vC vI vO vP vQ vS vT vU vV vW wB wC wD wE wF wG wH wJ wK

Figure 23 Continued

Figure 23 Continued uX vP vV wK) aK(pS tV tX uM vH yK tL) cC(hR sC tN tO vP vV wK) aP(vB vH vT vW tL) tL(fY Hr sC Ue) vP(aZ fY Qd rU) wK(As Pe qC)
vV(aZ Qd rU) sC(cZ Nb) uZ(cM Ue) vH(fY hG) NmwD HutV QdtO QvpS LjvW UvuW eDwL gWtX nRjK qCtM} fP{Nb(hO rT sC tR tX uM uT uZ vB vH vO vU vW wB wD wG wL wP yJ yK zI tM tL) wQ(aZ bC bF cE Hu Hv iC Ih IO Kc Kx Uk Vv) lM(kC mM mS nJ nN nR) Vv(fN vP wD zI) iO(uZ wD wE wF) tL(Cv Fp Hu Pb) Ed(qO qP rR) Lx(qQ wC yL) Pe(tR wC tM) aZ(vP vV wD) Iv(qQ rU) hO(hR Oz) qC(cZ tM) NqyL MdwC MppS IovT JdqQ LjvW UkzI dRvP mMhV hLuM rCoQ} nR{lL(aO aW aY bI Bn cC dC dE dF dM Ed Ef Ez Fn gP Hb Ky Qh Tr Up Vs) jK(aD aF aY Bn bV bZ De dH Ef Gp Hb Ic Ow Ri Ss) dH(iC jL jM jU lK lN qV) bZ(jG jH lM qV rA) dC(hV jO rC rX) jL(Ao Ib Id Ko) lK(Ao Bn Hb) Jf(hA rC) aO(lM qY) aY(eD qV) iA(lN qW) rX(Ct oE) AanO BnjQ DphX EzjG IbTv IcJi TrjU KsrA NyeD aGqV aMiB cWiC} Qv{bC(pS sC sK sM sO tO tQ tR tT tU tV tX uG uI uL uM uN uO uP uR uT uU uV uW uX uZ vA vB vC vH vI vO vP vQ vS vT vU vV vW wB wC wD wE wF wH wK wL wP wQ yD yH yJ yK yL zA zG zH zI yE tM tL) wD(aZ bF cA iC Uk) Uk(sC wQ) hX(kI mM) EduP NbsC OwnN nDqX qCtM} Ow{nN(aM bH cW eC eD hV Ic Iv Lu lY Ql Rj rX Uv) oQ(aP hX Ib Iv jK jT jU qV rA Rh) nU(hA hV Iv jD jE jM lN rC rX) oO(aW Fw iC jD jK jM Ky Oh qV) nF(jD jE jM lN qV) nJ(hV Iv qY rC rX) oP(hR iC Il jU) Iv(kG lY mY) mW(iC jU) hX(kK mM) jK(mP nK) rX(mE mI) eDkG hVkK rCkP} Ny{nA(Bg Dk Ef Ez Fp Ha Hv Ic Ij Ik In It Iv Jn Jr Js kQ Lj Mq Mv Mw Mx Nf nJ nO Nq nU Og Oi Po Qb Qc Up Vu) eD(kG kK kN lW mE mP mT mU mW nD nK nO nU) nK(Ad Bg Ef Hb Ib Ic Ik Ke kK kQ) Ic(kF kI mP) Ib(kG mT) kQ(mP mT) BgnJ UksC aMnO} Fn{lL(kC kF kI kK lX lY mI mP mS mY nI nK nN oO oP) vW(An dN Ed Fw Im Jj jO Lj rU) lY(hV jG jH jM jR lK qY rC) kK(iB jD jM jU jV lK qV qY) kC(hV jM jQ lK qY rC) mS(jH jM lK qY) nJ(iC jH jT jY) nK(jM jU lK) iB(mP nA) lK(lX nN) mTjU nIhX iOwF jMkF} Tv{nJ(hA jG jI jR jY lL lN qV qW rX) jY(kI mE mI mW nA nI nK) Ib(mT nF nK nO nU oP) nD(jG jQ lL lN qW rA) qU(mP mU mW nK oQ) lN(kG mE mI mP nU) In(lY mS mY nN) Dp(nN nO nU) nK(Ct lK Lu) eD(mU mW) eZ(Aj Qu) nO(hA Ij) mE(jM rX) mI(qW rX) jU(mP mU) JjnN nUjG nIjM} mM{hX(aW cJ Ct dN Ef Kj oH Rb Ug Uh Un Uu) Uu(hR hV jD jF jU rC rX) jO(aE aW aZ bP To Vs) jU(aD aO aY Cs Hb) Ct(hR hV rC rX) aM(iB jV lL qY) hA(aP bZ dC Ez) aY(eD jT lO) hV(dC Iz Ph) aG(jT qV) aW(lN rA) rX(aF Ef) lK(Ph Vu) IbjL aDjD aOlM cYjR} cC{Ad(eZ fN fY jL pY qA qB qG rN sM tN tO tQ tR tS tT tX yE) Dd(eZ qG rO rS rU rV rW tO tS uO vB) Ub(tO tR tS tT tU) Jt(eZ fY qA uP) Et(qA qO qP) Is(tN tX) Jd(eZ uP) Ok(hR yD) qG(Fy Kg) LxnA MmtO TneZ KfqO OaTk PkuX iOwF lLoQ} cW{lX(eD gW hA iB jE jF jG jI jK jL jO jQ jR jT jV jY lL lM lN qU) hR(kC kG lY nN oQ) oQ(gW jY lK qX) nN(jU rC rX) lY(jD qV rX) hV(kP mP mT) iC(kE kI oP) kC(jK qX rC) oO(gW jY rA) qC(Jt Tt) jR(mU oP) jU(mS mW) nKrC jYoP} vW{Lj(Ad Ao Cu Ic Jd Ju Jv Kc Kf Kg Kj Ky Pj Pk Qh Qu Ra Uu) dN(aN aZ bI Ed Fw hL Jd Ko Nk Pk qC rV Ub Up vH wL tL) Ed(Hw Jp Nj Pk zA) Oa(aZ bC Jd Mm Nb) Hw(Ax Fw) AobC ChHu UksC PkaC} oQ{lL(aW aZ dC eC hB Ma Mz Nw Qd) dC(gW hA jQ jY qX rX) iC(Dk To Uk Uu Vo) hA(bZ cS Iz Jf) rC(aO bZ Ct Uh) Ef(jH qX rA) aW(jD qU rA) jY(aP aQ Fb) gW(aA Uu) hX(cH Je) qV(dI To) JfqX KejI KnRh cGiB nOrA iAjF} Ic{wQ(aZ cJ dN Fp Lj Pe qC Ue Uk) wJ(Ed gL Lj Ly Nr Nu Uk) Jq(kF kI lW nA nK) Lx(kF kI nA nK) Uk(rS rW tT wK) Kn(kC lW nI) tT(aZ bC Vv) Ji(kF nO) rU(vP vV) UetL PeuP aPvB bCyK cMtN dAtV fYvP lWjL qVkE} Et{aK(pS qO uG vP vQ vV zG tL) qG(Aa bL Ez jH Md Mp Uv) gW(pS qB qC vP yL zH) qO(aZ dR Ih iO It Nm) vP(aL aZ Dg fY) tT(Hu Nq qC) iO(qP wD zA) rN(aU Gl Ks) qP(aZ dR) HuwG RfwQ TkjG aPvB aUuG} aZ{wQ(cI Dc Ip Is jH Kj Pj rT) Ad(qG qO qP rW vP vV) fY(sO tX vB wH wL) vP(Jd Jt Kf Kl) wG(aK cL My) qO(Jg Jt sO) oO(lK lL qV) Pk(rW vS) qP(Jt vB) JdrT cLsC gPvB jGoP} Pk{Ed(qZ rU rV rW uL uM vI vS) vS(cP hL Mp Ue Uk Vv wC) uM(aC Aw Fp Ih It Qe) Of(eZ rN uG uP) Uk(sC wG) MpwP bAtV bGwC dLuP dNsM fYvP iOwF qCrT} nK{Lx(aP bZ Hb Ib Ke nO) jU(Kf Kn Mz Ph Vu) lK(As Kf Kn Kp) Ez(cG hA Jq) Vu(Ib jV qV) Ik(Po Uv) rC(aW cG) qV(Ph Uu) CqEf GpjO RciC RbhA JqkQ OnnO UhjK aOlM} oP{Ib(cM Cq Fy gP Im iP Kf Kn On Ph St Tz) aW(jD jV qU) dC(jD lL rX) iC(bR Gp To) Rh(Kn oH) rA(bP Vs) jY(cR oF) BajH CtrC HblK KejI UhgW UucH eClL qVoH} nO{rA(Hw Lx Mk Mr On Oy Pb Po Qa) aM(cG Ji Jq Kq Lx Nv Nx On) nA(Lx Nv Po) Kq(Nd Nj) cG(hX lL) AaqV EfOn LxaA TzIb HwqX aOlM cElL cHrX} iO{wF(aC bX Hw Jo Kf Kg Lh Ms Nc Ne Nh Nl On sC) zA(Ad Jd Jt Kf On) wD(Kf Kg On) Ao(uZ wE) KgwE LhwL} lM{aO(kC kE kF kG kI kN kP lW lX lY mE mI mP mS mT mU mW mY nD nF nM nN nU) Iv(Tk Wn) dNmT} Uk{sC(aU cL hA Jd Js jY Mp Ut vB wE wF wL wQ tL) wQ(aO Bn jH wG) DdwG MewH cLuW gWtX mPjU wKjH qAwF} nA{Lx(bZ dH Ez Ij Iu Iv Mq Og Qb) Po(Ik Iv) Jq(kQ Oi) Vu(Dc jU) aM(lL rC) aW(hV rA) hA(Ez Rb) hX(cB cH) VsiC cJrX} cF{kI(jD jF jK jQ jU jY lK lL qV rX) Wn(Di Dk Ef Fw Ib Ng Oa Qh) Tk(Di Oa Qh Tr) qCtM} hX{cH(kC kE kG kI kN kP lY mP mS mU nI oO) nI(aW Dp Qt Rc) Dp(kN mE) AjkP CtkF UhmU aWnD cVmW} rC{kI(Cu Ed Pi Ql To) aW(kC lW nD nI) aM(kC nD nI) cR(nD nJ nU) Ct(kG kK) dC(lW mU) DlmI FblW HbmE UhnN} mP{jU(Kg kS Qx Qy Ug Ur Vu) Ez(hA rA) Rb(hA jV) Ju(jV jY) dC(hR rX) GpjO HblK JfjM UveD cJrX dHqV} mT{jU(aM aW bE cG cR cZ Fb Jv Kf Kn Ph Uh Vu) qV(aM aY Un) Ib(Hq Lx) EzhA OilL bXrX} qC{tM(bX De dN Ef Fb hB Jd Me Tz Ur) Kf(aK gW jQ qA qG) gW(Ok Pj) JdrT KpuP wGoH} lL{mE(Hv In Jj Js) nJ(bL cE Jn Nk) nD(bL Nk pF) oO(aW dC Mz) nU(bL rX) HbkG OikK VsnN} vB{aP(Ed Fy Jo Kg Kj Lh Mm Ok Pj) Aa(Lh uW) Ed(Hr Ue) Hu(Of tV) AoIk AsbC NbOk UeLh} rX{mE(cH Nc nJ Nk Nl qU) aW(kP nI nJ) dC(lW mU mW) cJ(mU nD) TokP hCkF} uP{Jd(As Rb Uc) Ed(Nj Ue) Qd(Jt Kj) Pc(Lh Ok) AdIh WmNb HqhL HwdL QeOn NxUp hRqV} wQ{bZ(Nk Nq Nr Ql Vs) Mm(cJ Rf) Nk(dN Kf) AoIk DdKp NbKg UcKf HqUp JuaC} oO{iC(aW bR cB cJ Uh) aW(jD qU) jR(aK cY) DleD FbjI RcqX KnRh UhhA cHjY} nD{rA(aW bL Ha Jf Ju Or Ou Qa Qh) Ju(jV jY) TjqX EzhA aWhR} qV{cM(mS nN) dH(lW mU) nU(Ou To) AamE aYmW bGqP nIiP tRoH} Jp{bG(qG qO qP rN sK wK) MppS NbwG HurU fYvP} Kf{qG(As Js Rb) aK(rV zA) qO(Ih Uc) IktL InfR rUvP} Dd{Me(rR sM yL) Fp(wF tL) AsyL MptV NbwG OfrN} nJ{rA(Aa Mk Ou Qa) DcVu LdiP UhtF aLqX bLjD} Kg{Mn(tO wF wL) GlrN IktL QdtO TkjG} Ok{Ih(qO qP) Qd(qG yD) NbqG UcrW PetT} mE{Aa(jE jM) Id(jL jY) hV(hC To) StjY} kC{hC(jK jY) QthR KniP aWjH bFjK gPhA} Hu{Ch(eZ wL) Jd(tV uN) HqwG JttV} mU{Ju(jV jY) EzhA JfrA QteD bLjL} kI{cB(hR hV) TrlK SseD VsiC bPjM} Ao{Ik(uM vH tL) MntM fYvP} Nb{sC(Pj Wm) AdwG TthO hGuU} Ib{kG(Dc Jq Oe) MtkN jLkF} Tk{jG(Co Di Hq) DijQ IvoF} fR{Tn(Kc Me Po) CsOr LdPe} nU{Ou(iC jU) StjT VpqX bLjO} mW{EzhA RbIO QteD JujY dChR} Wn{Oa(bO Tt) DkhA IvoF} On{Uu(lY nN) HawC PeyL} eZ{Kd(Ad Jd) TnQu JjwF} tM{Kj(Ih Pe Qd) EdNj} tL{AsbC FpcS GlLh} rU{KyvP aKtO wKqO} Ad{aNzA fYvP} Hb{fYvP jKkG} Is{QdtT QltV} Jd{RbrT dNyL} Jt{UeuZ QduW} WmbCyL EdPawJ PoeDkK GlLhwL IvOfrO RcnIiC QudNwF JqaMnN KnRhnF KslXjI aWhRkF

Unconstrained panels with 2 analytes, where 1.0E-8 >= 'AUC p-value' > 0. Contains 156 panels of 155,299 total panels evaluated. : Cw(eZ hL hO pS pY qC qG qI qQ qZ rN rO rP rQ rS rT rU rV rW rY sK sM tQ uG uI uL uM uO uP uR uT uU uV uW uY uZ vA vB vC vH vI vO vP vQ vT vV vW wB wC wJ wK wL wQ yH yK yL zG zH yE tM tL xA) iH(Ad eD hA hL hO hR hV hW hX iB iC jD jE jF jG jH jI jK jL jM jO jP jQ jR jT jU jV jY lK lL lM lN lO oQ qG qT qU qV qW qX qY rA rB rC rT rU rX rY rZ uM uZ vW wH tM) qT(kO mZ nC nD nH nJ nL nO nT nU) Vq(qI rN rU rW rY) Kz(pS sK sM vH) Um(vQ vU zH) nT(cG cL oN) nA(Lx Ny Po) Us(qQ wQ) rA(kO mZ) BcrY IcxA HfuY KnnB OwnN dNvW qUkO kFoN Unconstrained panels with 2 analytes, where 1.0E-7 >= 'AUC p-value' > 1.0E-8. Contains 76 panels of 155,299 total panels evaluated. : Cw(eD eT fN jP qA qB qD qH qP qU rR sC tT uN uX vS vU wD wH wP yD yJ zI) iH(eZ Ic nB oP qC qH rR rS sC tX uU uY vV tL) Kz(tR uL uU uY

Figure 23 Continued vS) Vq(qG rQ rT rV rZ) Um(tV uN uU yL) Us(qX sC uY) xA(Ap Pk Qw) bW(uY vW) nT(cE dG) qX(kO mZ) qT(lY nF) qG(Ap Et) BcwF IcdJ QwqQ NvnA dBjL dNuY nNoN mYkC qDuP Unconstrained panels with 2 analytes, where 1.0E-6 >= 'AUC p-value' > 1.0E-7. Contains 124 panels of 155,299 total panels evaluated. : iH(fY iO Jd Kq Ml Nj On qD qQ qZ rO rV rW sO uP uV vH vl vP wB wP wQ yD yK yL yE) Cw(fY hA hP j0 jT jY Kk lL qO qX rB sO tN tO tR tS tU tV tX wE wF wG) nT(aY Bo Ex Id Kq Ny Ou Qn) qT(kC kF mE mP mS mY nK nM) Us(On rY uX wD wF wP xA) uY(Ap Ky Pk Qz Um) Nj(Ad Ic nB Ok) Nl(Et In Nk Ok) Vq(qH qO qX rS) nA(Ir Jq On Pc) Ne(Et In Ok) oN(kO nH nO) Ap(eZ qO) Db(jL qX) Hf(qV wH) Iq(tV wL) Kz(uP yL) Um(sM tR) dB(jU rX) DdxA FnvW NtKq NauX NhIn QzqQ OwnF UfwQ bWtL mYnL mZiB nBrA Unconstrained panels with 2 analytes, where 1.0E-5 >= 'AUC p-value' > 1.0E-6. Contains 373 panels of 155,299 total panels evaluated. : iH(Bo bU bW cE cF cH cM cP Cw dB Dc dD Ed Et hP Hu Il In Iq Iv Jg Jk Jt Ki Kk Ly Mg Nf Nk Nl Nn Ok Pe Pf pS qB qI Qu Qz rN rP rQ sK sM tT uG uN uO uR uT uW vA vB vS vT vU wC wF wG wL yH yJ zG zH xA tF) Nl(Fp Fr Hw Hx Ic Ih Il Im Io Iq It Iv Jg Jm Jq Js Lu Lv Ly Lz Mf Mi Mj Ml Ms Mz Na Nc Nf Nh Nj Nn Nt Nx Og Oi On Pc Po Pz Qa Qb Qc Qd Qe) Cw(hR hV hW hX iB jD jE jH jK jL jM jQ lK lN lO qT qW Qz rA rZ zA) Us(hO jL jO lM lO qD qT qU qV rA rX uZ wB wC wH yL zA) Ne(Hw Hx Il Io Iq Jg Jm Js Nh Nj Nn Nt Oi Qb Qd) nT(bW cH cN Dg Gz hB hC Kf Ky mY Ow pF Tv Uc Uh) qT(Hf kI kK kN kP lW lX mH mM mT mW nA nB nI oO) dB(eD iC jD jM jT jY lL lM lO qV qX rY uP wH) Nh(Et Hx Il Iq Jm Js Nj Nn Nt Oi Ok) Qw(dJ On sC uU uW uX uY vB wF wQ yL) Qz(Bo Dc Ic Nj Qt Tn vB vW wJ xA) bW(uG uL uN vB vT wL yL tM) uY(Bc Db Ex fP Jp Kr Na Rb) Kz(qB tQ tX uG vQ zG Tk) nA(Mr No Nw Om Pd Pf Pg) nB(Ld Lx Ny OH Ow Tv) Db(eD hO qV wB wH wQ) Hf(eD qU qX rA rZ wQ) Iq(qC qD rT uZ wD wF) oN(mM nC nF nJ nR oQ) Na(qQ rT uP uW xA) Nj(Ed Fw gP Jd Kq) mY(kF kO nC nD nU) Um(pS tS uI zI) Vq(qP qQ qZ rO) dJ(aC bX cF qV) mH(lL qU rX rY) Ad(bX cF Nm) Ap(fY qP rN) Ex(hO mF On) Ic(bX Et Jk) mZ(Mt Oh rY) Bc(tV uN) Bo(kF nJ) Kk(Et uU) Uf(vV wJ) fP(hO wL) nO(cG rA) tM(Kr qD) uP(Hq Ms) NorO RcjY JdeZ KinH NynK UksC aCcF dNyL kOlL nWoO Unconstrained panels with 2 analytes, where 1.0E-4 >= 'AUC p-value' > 1.0E-5. Contains 1,187 panels of 155,299 total panels evaluated. : iH(aA aD aE aG aH aI AJ aL aM aN AP aQ aR aS aU aV AW aX aZ BA bB bC bF bG bH bI bJ bL bO bP bQ bR bV bX bZ cB cC cD cG cI cJ cK cL cN cO Cp cQ cR CS cT cU CV cW cX cY cZ dA dC Dd dE dF DG dH dI dJ DK dL dM dN dR eC eF eT fN FP Fr Fw gL gP gW HB HC hF hG Hr Hw Hx iA IJ Ik iP Is Iu iZ Je Ji Jl Jm Jp Jq Js Ke Kf Kl Kp kQ KR kS Ky Kz Lh Li Lj Lw Lx Mb Mf Mh Mj Mk Mm Mp mT mY Nc Ne NH nJ NO Nr Ns NT Nv NW Nx NY Oa oE OF Oh oK Om oN Oz Pc Pd pF Pg Po pY QA Qg qO qP Qt Qv Qw Rb Rc Rh Rj Ss TN tO tR tS tU tV Ud Uf uI UL Up Ut uX vC vO vQ Vs wD wE wJ wK zI Tj) Ne(Fp Fr Hq Hr Hu Hv Ic Ih Ii Ij Ik Im Ip Ir Is It Iu Iv Jh Ji Jj Jk Jl Jn Jo Jp Jq Jr Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Nf Ng Ni Nk Nl Nm No Nq Nr Ns Nu Nv Nw Nx Ny Oe Of Og Oh Om On Oy Oz Pa Pb Pc Pd Pe Pf Pg Po Pz Qa Qc Qe) Nh(Fp Fr Hq Hr Hu Hv Hw Ih Ii Ij Ik Im Io Ir It Iu Iv Jg Jh Ji Jj Jk Jl Jo Jp Jq Jr Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Nf Ng Ni Nk Nm No Nq Nr Ns Nu Nv Nw Nx Ny Oe Of Og Oh Om On Oy Oz Pa Pb Pc Pd Pe Pf Pg Po Pz Qa Qb Qc Qd Qe) Nl(bX Db dJ Hq Hr Hu Hv Ii Ij Ik Ip Ir Is Iu Jh Ji Jj Jk Jl Jn Jo Jp Jr Jt Lh Li Lj Lw Lx Ma Mb Mc Md Me Mg Mh Mk Mm Mn Mp Mq Mr Mt Mu Mv Mw Mx My Nb Nd Ng Ni Nm No Nq Nr Ns Nu Nv Nw Ny Oe Of Oh Om Oy Oz Pa Pb Pd Pe Pf Pg Qw) Nj(BA Bb Bo bX cF Ch cP Cu CW Db Dc Dg Dk Dl eF Et Ex fP Hc Ib In Jf Jg Jy Kf Ki Kl Kz On Pa Qg Qt Qu Qw Qy Rb Rm Ss Tn Tt Up Us Vs Wm Tj) Us(Ad Dc eD eZ hR hX Ib Is jT jU Kq lL lN Nx qC qG qH qW qY rC rN rT rU rW TN uN uP uU uW vI vU vV vW wG wL yE tL) dB(Ad bX eZ hA hR hV hW iB jE jF jG jH jI jK jO jP jQ jR jV lK lN On qT qU qY Qz rC rT tU uM wB wG wQ) Qz(Ad aR aW cW Db Dd dJ Dk Et Fr Gz Hf Jd Jk Ki Kq Kz Lu Nt On Qv Rh Ss Ua uN uP uU vS wD wQ) nT(Af aM Cx Dc dF dH Hc Hf iO Jq Kd Ko Lx nJ Nv nW Oh On Or Pf Qm Qt Ri Rj Tn Tz) Kz(Cv eZ hO Ic Kc qD tT tV uI uM uN uX uZ vO vP vU vV vW wC wL yJ yK zH zI tM) Db(aC Ad cF iB jD jF jG jT jU jY Kq lM lN Ly Ok On qQ qT qU qW qY rA rY sC) Ic(AP aR cL Cv Cw Dc Dd fP gP Ib Jg Kf Ki Kr Ok On Qy Rc Tn Vq wJ) Qw(Ad Cw Ib Jh Ki qG qO Qt qZ rT tN tR tV uM uP vS wD wG wJ yK tM tL) dJ(Ad bR bU cB Ed fP hR hW Jd jF Kq nC nH Ok qW qY rC rX tX vB wG) nB(Dc Im Iq Ir Ji Kk kO Lh Mr No Nr Nv Nx Oe ON Po Qb rY Ut tF) On(aG bO bX bZ cC cF cP hA iA Ib jM jT Kk mF nK nO Ph Ql Ri) Hf(Ad jL jO jY lL lN mZ qQ qW rX rY vB vT wB wF tL xA) Iq(eZ fP hO hP qG qZ rU sC uY vB wB wC wG wH wQ yL zA) oN(kC kE kN lW mE mF mI mP mW mY mZ nA nK nL nM nU oO) Cw(aC iC jF jG jI jR jU jV lM nW Ph qV qY rC Rh rX) cF(aG Ap aZ Bb bF bG Bo bX cC cI cW Dc dD fP rY Tk) Ad(aC aM bF cE cK cL cN cP Ex Ib In Kk Na Nt) mZ(hV hW Id Ik Ki lL Lx Ny Og Oi Qe qU rC rX) nA(Bo Im Lh Li Ma Md Mn Mp mY Nb Nr Nx Og Qb) bW(sO tR uM uU uX uZ vA vH vU wF wG wQ xA) uP(Jd Jp Lh Mp Mr My Ni Nx Of Pe uZ wL yL) bX(aC An Ap aZ bA bF cT cW Dc Is Ki Vq) Um(sK tQ vB vI vO vW wL wP yJ tM tL) mY(Ir Lx nH nI nJ nK nM nO Nv Ny Oh) Bc(sC sO uG uZ vW wG wL tL xA) Vq(hO hP jY qC qU rA rB rR rX) aC(Aj Ap bE Bo cB Dc Dd Ex uY) fP(eZ Iv qC qD qQ vW wQ tL) nO(Bo cE cL Lx Nv Ny oQ qX) qT(kE kG mI mU nN nR oP oQ) Pk(qC qD rU rV uM vS yL) nK(Ir Is Lx Mn Mr Mt Tv) rA(kG mF mM nC nJ nL nU) Na(Kq tV uL wQ yL zI) Ki(Jd nJ qV qX rC rY) Kk(Ap Dg Jg Kf Lh Tn) qD(gP Jp Jt sC vW yE) kO(iB jV lM nH nJ Oh) Et(Ks Nc qP qZ Rh) Uf(sC vH vP wK xA) mF(Bo Mt Ny Oh qU) uY(Dc Dd Jd Kf Ue) Gz(hO Ly Me Tk) Tn(Fp In Nb Nt) Ok(cC Me Nc Nd) aZ(vP vV wG wQ) cW(hA jU jY rY) mH(jE lN lO rZ) qC(Jp Jt Lh Tt) Kr(uU vW wB) oP(cH Ib Ow) Ap(wJ wQ) Bo(jQ qV) Dd(rN tL) Fn(eZ yL) No(rU tO) Nt(Jd Kf) Tv(nH nJ) Jp(rR rU) Lh(vB wQ) dN(tM tL) tF(mM nJ) lY(Mt Oh) rY(bR cB) UeuZ UveT aKjU lXlL nCqU hGuU sOqG Unconstrained panels with 2 analytes, where 1.0E-3 >= 'AUC p-value' > 1.0E-4. Contains 3,013 panels of 155,299 total panels evaluated. : iH(Aa aC AF aK Al An AO Ar As Ax aY Bb Bc bE Bg bM BN bS cA Ch Co Cq Ct Cu Cx Db De Di Dl Dp Ef Ez Fa Fb Fn Fy Gl Gp Gz Ha Hf Hq Hv Ib Id Ih Ii Im Io Ip Ir It Iz Jf Jh Jj Jn Jo Jr Ju Jv Jy KC Kd Kg Kj Kn Ko Ks Kx Ld Lu Lv lX Lz Ma Mc Md Me Mi mM Mn Mq Mr Ms Mt Mu Mv MW Mx My Mz Na Nb Nd nF Ng Ni Nm Nq nR Nu Oe Og oH Oi oO Or Ou Ow Oy Pa Pb Ph Pi Pj Pk Pz Qb Qc Qd Qe Qh Ql Qm Qn Qx Qy Ra Rf Rg Ri Rm Sr St To tQ Tr Tt Tv Tz Ua Ub Uc Ue Ug Uh Uk Um Un Uo Ur Us Uu Uv Vo Vp Vt Vu Vv zA Wm) Ad(aD aE aF aG aH aI aJ aK aL aN aO aP aQ aR aS aU aV AW AX aY aZ bA bB bC bE bG bH bL bM bN bO bP bQ bR bS bU bV bW bZ cA cB cC cD cG cH cI cJ cM cO cQ cR cT cU cV cW cX cY cZ dA dC dD dE dF dG dH dI dK dL dM dN dR eF eZ Fn FP GL gP gW Gz hR Hu Hw Hx iA Ic Id Ii Ik Il Iq It Iv jF JM Js Jt Ki Kr Ks Ky Kz Lu Ml Mp nB Nd Ne Nh Nk Nl nT Oi On Ph Po qC qD qG Qy rB Rh Rj rY Um Up Vq Tj tF) Qz(Aa aC aE aG Aj Al aM Ap aQ Ar As Aw aZ bA Bb bF Bg bX cB cC cF cH Co cP Cq cT Cv dC dD De Dg Di Dp Ed Ef eZ Fb Gl Gp Hq Hu Ib Il Im In Ip Iq Is Iu Iz Je Jg Jh Jm Jp Jt Ju Jy Kf Kg Kj Kl Kn Kr Lh Li Lj Me Mg Mq Mt Mu Nk Nl nT Nu Nv Oe Og Ok Or Oy Oz pS Pz Qa qC qD QG Qu qV Qy Rc Ri rR rS rT rU rV rW rY sC Sr tO Tt tX Tz Ur Us Ut uW uX uZ Vp Vq wE wF wG wH wK wL yL tL Tj) Nj(aD Af Al An Ao Ap aQ AR aU aW Ax bB Bc Bg Bn bR bU cB cH cI cK Co Cp cQ CT CV Cx cY dB Dd Dc Di dM Ef Fb Fn Fr GL Gp gW Gz Ha iA Id Il Im Iq jD Je jI Jl Jp Jr Jt Jv Kc Kd Kc Kn Ko Kp kQ Ky Lh Li Lx Ly Ma Mg Mi Mr Mt mY mZ Nc Nf Nk Nu NW Oa oF Og oN oQ Or Ou Ow

Figure 23 Continued

Figure 23 Continued cS cW dC dK dM dN Ez Hq Hw Iq Jd Jj Jp Ju Ki Kr Ky Lh Me Mp Mw My Nj Nx Oi On Pk qC Qv Qz tU Ue uM Ur vB Vo vT vV wQ tL)
wF(aC AO Ap As aW aZ cB cF Ch dB dN eD Et fP hC Hq Hw Iq Jj jP Kd Kg Ki Ky Lh Lj Mc Mp Ms My No Nx Oa Of Oi Pb Pc Pk Qd QV
Qz Rb rU tV Ue Uk Um uU Wm) wL(aJ As bR cF Ch dN eD Et Ha Hq Iq Jj Jp Kd Kg Kr Ky Lj Me Ms Nd No Oa Of Oi On Pe pY Qd QV qY
Qz tV Uk uU wG Wm) tV(aG As aU Bo cC cF cW dB Dd dM Ha Hc Hu iA Iq Iz Jl Kd Ki Ky Me Mr Nk No Nq Nt Oi Pe Pk Qv Rb Rj Uf Um
vW wG Wm) uZ(aG aO Ap As bG cC cF dN Et fP Ha Iq Kg Ki Kj Kr Lh Me Mu Nd No Nt Nu Of Pc QV tU Ue Uk Um vW Wm) tL(aC aG
AO Ap As bR cF dK dN Et Fp Hw Iq jO Jp Kg Kj Lh No Nt Oa Of Oi QV Qz sC Ue Um uU Wm) sO(aG As aZ cC cH cM dB dK Ex iA Iq Ki
Kk Kr Ky Me No Nt Oi Ow Qd Qv tU Ue Um Wm) rY(bR cC cF dB dJ Ic Il kG Ki Kp Ky lX lY My Na Of On Pa Pc Qz tU uG Uk Um Vs)
vW(AO aZ bJ Ch dN Et Fn Jp jT Kg Lj lM Ms No Oa OF qC qV Qz uT) vB(aO aP aZ bG bL cB cC dB dJ dN Iq Kp Kr Me Ms Nt Qz Ue Um)
rU(As aZ cC dB fP Kr Na No Nt Oi Pj Rb vP vV wG yK) uU(As aZ bG cC cM dJ hG Ki Kk Kr Qv Rb Rj rV rX Ue) wG(Af aJ As dN jY Nk No
Nt Nu Qu Rb Up) fP(qC qQ rQ rT uI uW vH vP vV wJ yH) uT(As bG cB cC dB iA Ki Kk Me Nt Wm) Na(qI qX qZ rP rQ rW uM vI yK)
uG(As aZ cC dB dJ Kr Pk Qd Ue) zH(As cF dN No Nt Oi Qv Um) aZ(rW vP vV wC wQ yH yK) cC(eZ qI qZ rP rQ tS uL) jY(rS tX uM uO wP
yD yK) vT(As dN Kg No Nt Oa qV) Qv(pS tQ wC wD yL zG) tO(As cF No Nt Oi Wm) Rb(qI rP rQ sC tX) uL(As dN Ki No Nt) Qz(rQ rS uM
yL) yH(As dN No Nt) Gz(qX rO rX) Iq(rV uM yL) Kr(wH wJ wK) dB(qI rX yK) dJ(rP tT tX) qC(Ex Tt tM) As(tN wC) No(yD tM) Nt(rO wD)
wH(dN Of) rW(bG dM) rV(Kg Ph) rP(Ki Mp) EtvV ExuR IcwJ JprR UkyK UpuW PkvI bFuI wPiA tUhB} No{vT(aC aO AP Ar aZ Bb bC bL bZ cR cS Cu dB dF dN Fa Fb fP IC Id jF Jn jO Jr JU Kc Kf Kg Kj KR Kx Ky lN oH Ql Qu qW tX Uf Uk Um Un Vt Vv) vW(Ad Aj AO AP aZ Ba bB bC bW bZ Ch Cp cS Cu dB dF dN Fa Fb Fn fP Fw gL gP Hb Je Jf Jr Kf Kg KR Kx Ky lN nW Ph Pk Ql Qu Sr Uf Uk Um Un) wF(aE aP aZ bC bH bW cF cM cP cR cS cZ dB dC dN gL IC iO Je JF Jr JU JV Kk Kr Kx Ky nW Pk qV qW Ra Uk Um Vv) tM(Ad Aj AO Ap Ba bZ Ch dM dN Ef Fa Hb Je Jf Ju Kg Kj Kr Mz Ph Qh Qu qV Uk Up Vs Vv) yL(aE aZ bC cM CS Cu Fa fP Hb Je Jp Jr Ju Kj KR Kx Ky Ph Pk Uk Um Ut Vv) tO(bC Ed Et Gz Hb Hq Ic Jp Jt Ju Ki Ky Lh lN Mm Nm Nx Ok Pj Qz Rb Rf Uf Vt) wQ(aZ Bb bW Co Cu Dg dJ fP Hb Ic Ju Ke Kf Kg Kp Kx Ky lN Pj qV Uf Uk Vv) tL(Ao Ap bC bQ bW Cu Ed fP Hb Id Jd Ju Kf Kg Kj Kq Pj Ql Rb Sr Uf Um) wL(aK bC bW cF Ch cS cZ dB Ed Ex Iq Je Jf Kj KR Ky Qh tT Um Vs) rU(Ad Ap Et Ic Iq Jd Jp Jt Jv lN Mm Nl Nn Ok Om On Qz Uk) uL(aP bC bW cR gL iO Jr Kq Kx Lh Nn Ok On qX rA Uk Vv) rO(Et Ic Ij Iq Jt Ju Lh Mm Na Nj Nn Ok Om On Qz) tX(bL cC dB dJ Kk kR Nc Nh Nj Nl Ql Sr Ub) Jd(eZ rQ rR tT tU tV uI uW uX vI vO vS) Iq(rR rT rV sK tV uZ wE zI yE) tU(Ap bW dJ Hb Jv Kf Qz Sr Uf) uM(Ap bW Cu fP Kf Kn kR Lh Uf) rN(Ad Ap Hb Kf Kj On Pj) vU(Ap Cp Cu Fy Ic Uf Uk) tV(Cs It Pk Ra Um wE) wH(aZ cZ dB Kr Ky Uk) vB(aP aZ bL bW dJ Ed) vS(Bb bL bW cI dJ qW) mZ(eD Ic Ik jP Uu) nA(nC nH nL nO Ny) wE(aZ Et Ii Lh Ok) yE(Cs Jv Ky Na Pk) uV(Gz Ic Pj Qz Uf) Uk(sC vP wD yK) bC(sO wG yH zH) rV(Nn Ok On Ph) Ad(sM tR zG) Qz(qQ rQ zG) Jp(rR sK yH) Jv(rQ sC wG) Um(sO vA zH) yK(aZ Kx Vv) vI(Cs cW Pk) Ap(qO wP) Nh(tS zA) Ic(rQ wJ) Ij(qG qQ) On(rR yH) Ph(qO sK) bG(uW wC) nK(Mn Ny) uP(dL Hb) NltR JevQ JuwG KgwP KnzG KyuT LhyH OktT PkrR aMnO aZvP fPqQ mErY hLrX sOkR kFoN} dJ{nH(Bo cG Dc dD Hc hV Ih Im Ir It Jd Jg Jn jQ jR Jt jU jV Kf Ki Kk Kl Kn Kq Ld Lh Lx Ly Mf Mg Ml Mr Mt Nd Nj Nv Nx Ny OH Ok ON Or Ow Pf Qa Qe Qh Qt Rc Sr Tn Tr Tv Tz Up Ut) tX(aD Aj Al Ap As bB bM bX cF Dc Dd Dg dN eT Fn fP Ic Iq Is Jd Jo Jp Jt Kf Kg Ki Kj Kk Kl Me Mm Ms Nk Nm Oa Pj Pk Pz Qt Qu Qv Qz tR Ub Ue Um vB wG) vB(An Ao Ap bR bW cF dN Et Hb Ic Iq Jj Jo Jp Kg Lh lM Mm Ms My Na Nr Ok Om Pk qW Qz Um) nK(Bo Fy hV Iq Jl Jq jR Kq Lx Ma Mp Nv Ny Oh Ow Pa Pg Po Qa Qb Tn Tr Tv Tz Uc Up Ut) Ic(aC Ad bU bX cP cW Dc DD Et Jd jl Jp Kq Mf Ml nW Ny oF Ok On Qh Tz wG wQ) tQ(Ao cF Dg Et Hb Hq Ij It Jp Jt Ke Kf Kg Mm Om Pj qV qW Ul) tT(Al Ap Cu Dg Hw Ij Iq Is Jd Kf Kj Mm My Om On Pz Um wG) Et(fN hR jT qA qG qO qP sC tU uN uP vl vP vU vV wQ) wG(aZ bB bW cS Dd eT Hq Hw Iq iZ Ju Kj Mm Na Pk Uf) nC(bH Bo hA Hc jK jM jQ jR Kq lO oN qV qW Tn) wQ(cS Cu Dd Gz Hq Jo Jp Kf Mm qV Qz Uf) eT(Jt rX rY rZ uG uU Uv uZ wL yE tL) wH(bU cB cF dB dN fP Hq Hw Ky Na Qz) Ap(eZ hR pY qG qI tN tU uP uZ vI) Jp(hR qI rO rU rY rZ tO uO uV yH) nL(hV jQ jR Kq Ny Qu QV Tn Tz) Ad(hR hV jR pY qU qV qW rY yD) Ok(eZ hA hR jT jY qI rY vI vW) nJ(Dc dD jK jQ jR Kq lK oN) hV(kE kF mM mS mY nA nI) rC(bX kI lX mE mS mZ nN) hR(Bo Hb Jg Jt Kl mY) rY(bR cB cF lW mY Qv) Hw(tN wD wF wL tL) Jd(eZ jK lK lL qI) bW(uG uU vW wL tL) fP(uT uZ vW wB wD) mM(jK jO jP lL oN) qV(cW mT nF nU rT) rZ(bB bR cB cF cW) Hb(fN pY qA rW) Uf(rT tO tV wJ) Pk(hP pY rU tV) Kg(qG tS wE) nR(hW jK oN) wL(bX Kj Um) jP(kG mZ oP) oO(jU nW oF) oQ(jU jV lK) Dd(rU tV) Fn(qU qW) Kf(fN tU) Kq(nO Nt) Ph(tO tU) cW(eD hA) eZ(Ao On) mT(jQ jR) mY(hX rX) hW(lX oP) wE(Jo rU) qI(Jt Nj) jK(mP nN) rT(cF Hq) uU(bX hG) LxnO PzqC QzjF NynA UmwF PjtO bBwD dNvW mZlK nIjQ jHvS qXqW jVoP} Ap{qG(Af aG aK As aU aZ bG Bn cC cF Cq cW Cx dB Dg Ez fN fP gW Hq Hu iA Id Iq Je Jf Ji Jl Jq Js JU jY Ki Kr Ky Li Lu Md Mp Mr Na Nb Nj Nm Nt Nu Oe Og Oi Ow Oy Oz Pe Pf Pk qC Qd Qn qQ Qu qY Qz Rb rX Uc Uh Uk Um Uv VT vW wQ tL) qO(aZ bN cC cF dB Dd dG dR hO hV iA Ih iO It Jl jR Ly Mn Mr Nu Nv Oa Qd Ql Qm QU qV qW Qz Rf rV Uc Uk Vp vW tF) eZ(Af cC Ch cM Dg fP Je Ji Kd Kr Md Mp Mv Nf Nk Nm Ns Nt Oi Pd Pg qC Qn rB Ri rO rV Tv Uv Vt tL) wQ(aN aZ cF dB Dl Ez Fp fY Ik JG jH Lj Mp Na Nk Nt Nv Oa Og Pd Pk Qu Qz Uc Ue Up uZ) qP(aZ cC cF cM dB hO iA Ih iO It jG Jl Mn Nt Nv Oa Qd QU qV qW Qz rV Uc Uk Vp tF) fY(aW cC dB dF Di gP iA Md qU rU rV rX Uv vB vP Vt vW tL) uP(aK aU aV cC cF Ki Ko Kr Nb Oy Pd Pe Pf qC Qd rW vT) vW(aM Fn Fp gW hR Hu Jg jQ Kr Lj Na Oa Oe Og Oi Oy Qz) qC(aK bP cW gW iJ Iq jQ jT Kk qA Rh tT Um wK tM) Na(jO qQ qX rB rY tT uM vH vI vT vV wJ wK wP) wJ(cF Dl Ed Ic jG Lj Nk Oa Pd Qn Qt Qz Uc) Nt(jT rN rR rT rW sC uL vP vV wC wK tM) Kk(qQ qV sM tQ tR uI uX vQ vU yL zG zH) Ik(qQ rR rV uM uZ vB wD wF wH wL tL) Kr(hA hW jP rB rT uZ vB vI wB yE tM) gW(hO qB qQ rR rU tV tX uN uZ tL) rN(aU aV cF jY Mr Oa Pe Pf rW) vB(aP Dg Hu jG Kl Og Oy Rh Um) vP(aL aZ cC dB Dg Lj Pd rU Uc) Pd(sK tQ tT vV wC wK tM) dB(fN hR hW jL rW rY vV) rV(aG hR Iq jQ jT Ow Pf) Dg(qI rT rW vI vV wE) Uc(qQ rW uM vI vT wD) Um(vA vH wF wL yL tL) aK(hO qB tT tV tX uZ) wK(aJ jY Pe Qn Qz) cC(hR hW qA vV) iO(wD wE wF zA) rW(Ez hG Oe qW) uZ(cM iJ Iq Ue) jG(tS vI vT) sC(Mn Pe Uh) rO(hR lK Pk) vV(Ez Oe rU) Dl(vI wD) aU(rR uG) nK(Ex Lx) iJ(sK sM) tM(Pe Vt) MnuW HutV IqhO QzwD RhtU OatT UhqA UveT aLwE mZjP wGoH jTtL} jP{mZ(Ad aK Ax BA bF bJ bL bQ bV bX bZ cB cE cF cG cH cO cS CT cW dF GL Gp hB hC hG Hw iA Ih Il Im Io Ir Ji Kc Kd Kl Li Lj Lx Me Mh Mj Mr Mt Nc Ne Ni Nj Nk Nl Nn Nr Nu Nv Nx Ny Oe Og Oh Oi ON Or Ou Pa Pe PF Pg Po Qa Qb Qe Qh Qt qX rA Rb Tn Tv Ue Uf Uo Up Vs tF) mM(aM aO aP aR aV aW aZ Bb bF bL bM Bo cE cG cJ Co Cq Cs Ct dB De dI Dk Dp Ef Ez Fn Fy Hc Ib iP Ir Jd Je Jf Kc Kg Kk Kn Kq KS oE OH oN Ou pF Qt Qx Qy Tn Uk Ur Ut Uv Vp Vs Vu Tj) oP(aH Ao aW Ax aZ bB bF bL bN Bo cJ Co Cq cR Cs cT Cu CV cW cZ dB dI Dk Dp eC Fn Fy hB Jd Kf Ki Kn kQ Kr Ne Oa oE oK Pk Qt Qy Tv Uo) mE(Aa As Ba Dd Et Fn Is Jd Ji Kn Ko Kq Lx Mt Nc Nk Nl Nx Ny Oh On Or Ow Pf Po Qe Qm Qt Qy Rc Rm Tv Uc Uf Vs) lX(cE cG cW dD hC Jd Je Jf Jg Kf Kn Kq Lx Mw Ne Nl Nv Nw Nx Ny Ok On Pg Po Qu Qx Qy Rb Rc Uo Ut Vp Vs) kI(Ad Aw cF cW Fa Fy Gl Ha Hc hG Jd Je Jf Ke Kj Kl Kn Mr Po Qt Qu Qx Qy Rb Tn Vs Tj) nO(Dp Fy Hc Ib Jd Je Jf Jy Ki Kj Kq Qt Qy Rb Tn Tj) nK(bX cG Hw Kn Lx Mr Nx Ny Oy Pb Pd Pg Po Qt St Tn) nA(Jd Kp Mr Nv Ny Ou Pd Pg Po Qt Ur Ut Uv Vp Vs) mT(Ao Ba cE Jd Je Jy Qt Qx Qy Ut Vp Vs) nL(bF cG dF hG Kf Kl Ko Mr Ny oN Pg Sr) nR(aD aR Cs cU dB Dg dN eC Gp kS pF) mP(Ct Gp Jf Kc Kg Ne Oh Tn Ur Ut Vp) nC(bX Gl Ko Kp Me Pg Rg Rm Tn) nJ(bL Et Mg Oa Pb Pg Vu) kC(cG Gl Ko Kp oN Qx St) lY(cE cG Gl Kf Kn St) mI(Bo Kn Nv Ny Po) kK(Fn Kf Kp St Uo) oQ(Cs dI Hw Kg Tv) oN(kE kF mS mY nN) Ou(kE kN mU mW) nH(Kf Me Pg Rm) Na(wB wQ tL) nI(cG Fy Uv) Tv(lW oO) dB(Tn wH) nN(Kf Ur) kG(Gp Ow) kN(Ib Io) EtcC FwvW FymW IquZ RckP KgmU KnmS KrwB UpuP bLnU qCtM} Na{wQ(aC Ao aZ bB bF bW bZ cE

Figure 23 Continued

Figure 23 Continued iH{Ic(aE bG cE cL dD Dk Fp Jk Jp kC Ke Kf Lj Lx mT Nb Nl Nv Ny oF Pe Ql Sr Ss Tn Ut tF) Ad(Aa Bo Fy Gl Hx Ii Iv Js Lu Ly Mp Ne Oy
Qc Qz St) Kk(Ap bU Cw Dc Dg Jd Jg Kf mT Om Uf tF) Pe(Dc Et Jq Jt Kl Lx Ml Nw Ny Om tF) Pf(Ap Cw Dc Ed Jd Jg Nj Qz Vs tF) Iv(Et Gz
Jd Kq mP mW Vs) On(iA In Lx Na nO Nt Pd) Nf(Dc Dk Ny Om Ut Vs) Qz(Bo Dc Jd Ml Ny Rc) Kq(Ed Gl Lj Nb qO) nF(Cx Jl Jq Mp To)
Fp(Jd Ny Ok Ut) eZ(aL dD Mk Mv) nO(aM hB pF Uf) qC(Tt Tz Uc Un) qQ(bV cC cK uP) Ml(Ly Nj Nl) cG(nH nJ nN) tF(cF nJ Wn) qD(Gz
Kc Ke) sO(oN qG uZ) oP(Af Lv Mb) Bo(mY Nl) Dc(Lj Po) Et(Hu Pd) Nj(cM Nk) Ik(Jg Kl) Pg(lW Ok) nN(cL Jq) pY(Fw Tj) qO(Jg Vv) oQ(Kn
oH) EdJl GziB LwoO NkNl HuNx InJk IzhL WnVs TkcF VqhO PdmU aCwL aUtT cEnJ cRuU dJnH iOwF xArZ} Iq{qC(Ad aN Ao bR cG cW
dF fP gP Ib Jt Ki Lh Me Mh My Pz Qz Rf vB wQ) rT(Af bJ bW Ez Hx In Io Kr Nf Pe Qc rR rU rY Uk Vv) tV(aU aV bA bW gP hO Ic Il Jm Js
Lx Po Ql Uf) qD(bQ Dp Et iA Ib Im Jt Me Mr) wD(Ap Bc hC Hr Ky Mp Of Qd sC) hO(aK aN bR bS Nj Pj uM uO) wF(aN dC jP Ma Of Rh sC
Um) vB(AP aZ Lj Of pS Qe Um) qG(Fn Kd Kf Om Qb Uf zA) hP(Bo dH Ed Hu Iv Kd) wL(aN cC Hr Mk Ne Ur) rV(aN Ao Cv Ha iZ Ph)
tL(Cv Dd Qz Uf Wm) sC(hL Qd Ql Uk Vv) qV(Cs Ed Fw Qw) uZ(Ih Ms Mt Nv) wH(Mv Nc Rh) qQ(cC iP Kz) uW(hL Qe Up) uY(Hv Me My)
qX(Cw Ed) xA(Ao Fn) rY(dJ uL) uP(Jd Jm) vH(cM Qu) AxvW BcwC DcnA EtrR NoqZ KisM KktR KrtX KyuM RfvS UmqB VqjO PerU PjuL
aCvT bWyL cClN nOnK hLsO} dJ{Ic(aL aZ bR cF cT Hc Jg Jk Jl Kf Kr Ne Nj Nl Qt Ss Tn Vs xA) nH(Ad bH Jq Kc Ko Li No Nr Nw Og oP
Ou St Vv) vB(Dd Fp hP Hr jH jP Lj Mg Nj On rU Uf) tX(Cu fY gP jH Ju Mh My qA) qV(bR bU bX hR Jd Jt qX) Qw(Bo Dk jD jI Qt Qu)
nL(Ed Ha Jq Qh Qt Uv) wQ(cF Hw Kj Oz sO Um) Kf(eT hR qC qG uY) nK(Nb Ou Qh Qn Tt) rC(Bc cI dC Jd Jt) Dc(nC qW Qz tT) On(qC rY
uP zG) wG(bR cF jH Vv) qI(Bc Dd Kg Uf) rZ(aI fP Nk oF) Ad(gW Qz rU) nO(Ji Jl Mp) hR(bB Dg Kq) wH(bR Ih jP) rY(Jt Lh oF) Et(jU Kk)
Kz(eD jF) Uf(fN vV) Vq(hA jY) eT(bG Dk) fP(hO rT) nC(bP Tv) nJ(iO Tn) tT(Qv Tz) sC(Bo rU) vS(bW My) AoxA CotQ NorO MmwF NaKq
HqwD JjvW JtuY KljO KyjD NynR OwnF UmsO aCcF bRrT bXqW cWlL dCuU mZjM hGtM} uY{Jp(aI aZ cM fY Hc In Ji Me Mt) fP(bQ Cv
Fp Mr Nu pS Ur uT Vv) Rb(aS cP Jq Lh qA rZ Uf uP) Jh(aC bG cM dB fY hG Qu Uv) aZ(Dd dN Is jQ Jt Qv Qw vV) Hw(aI aL As Ha kR Ks
rB) Bc(Fw Ic Ip Mp rZ wG) Dd(bG bL Kd Mp Uk Up) Ky(aP As bL jO Ki Mt) dN(aN cO Fp hO oN rU) Na(Js Mj Nv rO uX) Ue(Aj cC cM uL
uW) aC(bW Ju Ks Uv Vv) hG(Bb Mt Nr Pe rU) Nt(Jn jO rO Ub) Nk(aP Ch Kf qD) Ki(Aw Uk uP wQ) Kr(cR Kn Ns tL) Ok(aK aL Kk Ks)
Ap(bU oH rP) Nq(Aw Ch Qh) Jd(Bo dC Kd) Qw(iP Ne Oe) Pk(aL bN Cq) bW(jY Ss wL) Ha(Pa rZ) No(Hv Ub) Mn(Ao Kg) Of(cW Hc) bG(qA
sC) cC(Mm oH) cS(Ih It) dB(Nj Qh) uP(Ch Di) AdUv BoMs DcFw EtGl FnrZ NuRj MpbC HraG QvcA KfiJ KkaO LhOw OmaP UkgW aLjH
hPtM qVoH} dB{jL(Bo bU cD Dd Dk Ef Fn Hw Is Kl Ky lM My Na Of Pj Qz rZ) qX(bX Dc jF Jp Jt Kg Nl qU Rj Tn Uf Uk Vq) rX(bC bW bX
cE cH jH Ji Kq Ky qP rW sC) qU(Ap bW Di Jp Jt Kf Lw Qz Rj Vs) rY(bR bX cF Cw Hq Hx Je Ny qV uP) xA(bG Dd Jh Jo Jp Jt Kf Lh) eD(bW
Fn Is Kf My Pf Pz) qV(Ap Dd Fn Ic Ji On) jY(Ji Kf Lx Rc tM tL) rZ(bW cG Jp Kq Vs) sC(Ap Ju jV Mg Vv) uM(cK Ed Lh Nk Om) wH(bE Cp
lK Mk) On(qG rN uI) Uf(fN hO qQ) wQ(Ic Nk Oa) lK(vB wL tL) Fy(vB yL) Kf(fY rW) aZ(vV wG) mZ(jK jM) iC(bX wG) wF(Kc Rb) lN(mT
oP) uP(jH Mg) AprB BcrP DktS GzjO NnhO MmjU HqhL TnlL QcqC JrzA OkhR aJuX aQwL bGqO fYvB gWtX qDrT} Na{xA(aG Ao aP cC
cR cX Ib Mm qU qV rR uL) wQ(cL Nn qV Rb uT zG) qX(cB Ed Jd Kf Kg Qt) uL(Fy Ij Ly Mh My No) vH(Dg Fa Kf Kn Kq Nn) rT(Jk Kz Mm
Nk Nn) sC(bF Ha qC Qy Vv) uM(Bg Cp Fa Jg Jq) tL(hL hO Kl Ur) qQ(Jh Nm Rh Um) uX(cF dG Md qC) vT(Cv Fy Kc qH) Bb(qT rA vV)
Dk(qA rA Tk) On(eD iA qC) wC(aD Aj Dl) qZ(Jk Jp Lh) rY(bC Ok Vs) rQ(bC Jj Tz) rO(Jh Nj Om) vB(dH iC Mm) Dg(vW wK) Nm(tV wK)
Ni(wG tM) Kf(tT wJ) tQ(Jg Pk) wB(Bo Kr) qU(qO rW) qG(Ij Ik) rZ(Ap Vs) rU(iP No) CpvI CwjL DchO DirA EdqT MdzI MpuP HqwG HruW
HutV ImqD QaqC QzQt KgvW KltM UmrR aPwH aZtT cUqO eTyL mElL mPiB nKoN} Qw{vH(Aj Et Fn fP hG Ii Nb Ok Um) uM(Ba Kn Nb
Nj Qt Ss uX wL) sC(bI Fw iA iC Mr Ni Nj) rN(Ct jD No Of Oy Ua Vs) rY(Aw Jd Ok On Qt Vs) qO(Cp Ic Kl Oi tV Vv) pS(eT jD Kn Ou wF)
rZ(Jd Nx Ny qC tL) vB(Bb cL Nh Og rA) vW(Ao Et Jg Ok vO) eZ(bJ hP Mw vI) yL(cC Ik Ky Mp) Ef(fY tM tL) wQ(Ik Ky Nd) tO(Dd Nx qC)
rB(nN On uU) zH(Al hG Pz) wD(bF iC zG) wG(dE Ug zG) uX(rU Uh yH) Qt(jU qD) fY(Ap Jd) tS(Oe tR) tV(bI tM) tL(Fp hG) AdrX AjuG
DkwJ EtwK GzqD NurV LxmZ MgwL MpvO IkqP JqmH JyqG KiqX KxvV RmqZ UvqQ VqhL VvvP PhtT bEwF bFuW qBrT qVtM kOoN}
Ap{wQ(cC Ed hL Ih jM Nq qC Qn Rf Rj Um) eZ(As Fn jG jQ Me Of Or Ow Qd Rb) qO(aL cM Hx Ky Nq Qt Rb Rm Vt) qP(dG Ly Mr Nq Ql
Rh tV) vW(aN dN jG Ji Nk Nq qC) wJ(aN dN Ly Nq Pk Rj) rN(cC Fr Gl Ki Nv Vt) rW(aL aZ Dd Kl Qz) rV(aI aV Bc iO Jg) vB(aL Jg jQ Ss
Uc) fY(As Ky Nt qC) tT(hA hO lN Qz) sC(cC iA Ki Nb) vI(cC Ed iO Ow) Kz(eD jO jP) wK(Fp hL Nk) qG(Nq Ri vH) tM(Lj Oa uZ) rY(Bc kF
lX) vP(cM Ih Qd) hO(Kk Vq) qX(cC Nt) xA(aE Qn) oP(jI lK) uP(Lj Mp) uZ(iO Mn) vT(bW Rj) AsvV NbwG HqwD IkyL RhtL UmrR cMfN
dFqC} Cw{qX(aF As aZ Bc Cq Ct Dg eD Fb Gl Il Iu Lj Mp Ph Qb Qm qV rB Rj Tn) jO(aK aR As aZ cE Cu cW Dp Ez Iv jL Lv Nb Nt Of Ue
Uk Ut) rY(aO Ax cC Co dC Dp Ed Fn Fp Fw Hb Hr Iv Ko Pz Uc Wm) hA(bW cE Fn Iv Jd Ks Lw Ph Rh Uf) qU(aM An aY Iz Nc Nl Nm Nn
Oh Tk) eD(aM An As aW Bg In Ky Lv Md) jL(aG Ez iA jP Ju Ph rZ) jP(aM bX jE Kc kI mH) Nj(Ic Kk Rh Tj) lL(gW Lu Lv Ma) rA(Ed Qu Uc)
rZ(aZ bC Fw) Ic(gP Rh) Pg(lN qV) LulN HxrB RcjY KjhR KsqV RhjU TkjG aCcZ aKjR nUhW} mF{Lx(aJ dE Ef IB Ik In Iv jO kF Ky nO Qd
Up Uu Vs Vv tF) Ny(cR Ik Iv Ky nO Of qT qU Qz Up Ur tF) rX(cG Ed Fp Kd kO kR mE Nc Nl oF) jP(Ar Bn Jm On Pb Qa) rY(bP dC Fw iA
mH oQ) In(Cq Ir Nr Pe Po) eD(Al Is Pa Pd Pg) tF(Ex nW Qt rB Vs) jE(Jn Lj Mp Oy Pg) Ky(Bo bX Kn Qa) qT(Hw hX Mt mZ) Wm(cE Nv Po)
Ex(dN Ed nO) Ar(dE rZ) Dc(jD qV) Po(qU Tj) Nr(dE Ij) Jq(lL Vu) Nv(nO Of) Vs(bX Jv) rB(dF Pd) jY(Im Tz) oN(kN Nm) BoJu EdcL FyKq
MpjO MtUp IdOa TvnN IriO JdrZ KicH NxaO OnmM UrqU UuhA VujV PhrC cBhV cEnO hXhC} mZ{Ik(dD Gp Kq Mt Og Oh Qg Tn Uo Up)
oN(Aa bW dM Ez nF Pf Uf Uu) Lx(Cp dK Kk nI pF Uc Vt) Is(Hb Kk Ks nI Og Ql Uu) Ez(cL Ji Jq Kq Oh Tv) Ic(Ar Ma nR Po Sr Uh) Id(dK Iv
Ky Kz Mf nK) Ko(aY cG Lh On Ow Tz) jP(bM cY nJ Nw Pd) Tv(Aa cM Ir nH) Og(jO Mt Nl qT) Uu(aY hV Jg Kq) iP(Ir Mp Tz Wm) rY(Hr Iu
nA No) Ow(nF Pd Pf) aY(Aa bW nO) iB(Jm Lv mM) jD(Aa aN cB) Io(hA jL) Js(Ny rA) Ki(cL Ug) Oh(nA Vo) lY(lL Mz) hC(jK jY) qT(In Jn)
BooH TjMf GpIv MnnK MtjU NcjY NjdD NljT TnOi KeNy OerB OfUt bAjK cWjI eCrA rClL qXjO} qD{tM(aG aP bB cB cC cN Jq Kn My
Nq Of Om rX uU yE) sC(Bo It Mw Nm Ns Pj Ss vB) vW(aE bX dC Et Jt Mh Nj Of) wQ(Iu Jo Kg Pa Ph Qc yE) rT(aZ fP iP Kc Sr Uf) uP(Ao
As Cv Fw On rW) Gz(aD bQ iA Ib Rh) yE(aP bX cS Ms oH) Vq(gP Mq nY Qt) yJ(Al aZ Kj Mf) Jp(fP Ip jQ) Kf(aU tT vP) wJ(Jo Kg Pj) tR(bM
Nq Ue) qG(Hq Im Jd) vV(Cv Kg Pj) Aa(No Nt) Me(Ad Mh) Tt(cW Mk) Jt(aG Fn) Kz(Im Sr) Ok(vP xA) qA(rX vU) yL(Jj Ky) uW(Nq Rb)
DdaK ExdF NtgP MmxA NkvB IcsO IszG PzyH JdeZ QzaJ KcwG KjtT RhwH OmwK bWtU rUvP} xA{Uf(cL gW Ne Ng Nh Pe Pg pS qC rA
Rh tV wQ) Dd(As cN Cs Kf Kp Nh No Nt rR) Bc(Ez Jo Jv Lj Mm Nc Nh uT) Lh(aZ cA Fw Gl iC Nv qW uP) Mm(aP aZ bU cM hG hO Oa)
Ok(aL cE No Nw qC Rf zI) Um(cA Et hO jR Nt Qc qY) fP(bG Cv Hv Jh Kx Nd Nr) Ic(As bE Io Nr Pe qW) qW(Ao Fy Kj Pa Rb) Nt(Fy Hb Kn
Qy) Kg(IO Nr Ue) Fn(jO Nr qU) No(Kn Ph qX) Ed(Kf uP) Fw(Hw uP) Hu(Om On) Io(Hb Kf) Jh(cW Kz) Qz(aW Nk) Pa(An dN) bW(bB wQ)
CpNq DccC EtjF NrSr QvUk JoaP JpaZ KiiC KzuI} Nt{Kq(fP Hc Kk Ne Nh Nj Nk Nl qO tM tL) tL(bC Cu Ef fP Ic Kn nW oH Ph Ql) wF(bW
Cu Cv Fy gL Kj Kk Pz) On(Hc Ic jT Kk Qz) wQ(Aj Bb Dd Ki Ky) wL(Cu Dd Et Uk) wG(Ii It Nl Nn) wH(Ef Jk Ne Nh) uP(Dl Fw Li Mw)
Dk(qA qG qO) Hb(rN vP tM) vT(Bb dN Kf) Ad(Id Rh) Nl(Et rT) Ic(Jk rW) Iz(sC vW) Kl(qO rN) Ok(Ne Nh) eZ(Ch Om) yL(kR Nn) vA(Kj
Um) AovP BbqO LyrU MhtM IbqG PzyE JgKk SsvW QzQt JprT JvrQ KfjT KgTk KnwC KrwB LhqC OfvU UvqQ PhwD PkvS eDmH gPuN
nCrY nHjO tVoH} kO{nH(Bo cH Kn Og On Or Oz Tn Ut) nK(Jk Mj Ml Mn Nb Nr Nw Pe Tn) nA(Ii Jl Jt Ma Nb On Pe Tv) jO(Jg Jl Li Nu Ny
On Pg Po) Qb(eD iB jF jH jP jT qU) Ic(Is Kq Lh Ow Qa) eD(Lx Mg Mx No Po) nJ(Bo Ha mY Up tF) Tv(cP iP Ly nC) rX(aZ cM nW oF) Dc(jI
lM qX) mY(Mt Oi Ow) rY(Ba bP On) nW(Ik Nj Nl) Aw(jH rA) nC(Hc Tn) rC(Ir nU) jQ(As Cv) jT(Al Qe) jV(Lx Md) lL(kG mE) AdlK BblO

Figure 23 Continued

Figure 23 Continued nF(aD aM cG nW) cW(cB Ez Qd) oO(Kf Kn Qx) Kc(lX mI) Vv(fY tM) kG(Cp Hb) oP(Ct kR) oQ(iA Nd) AdIt AjkE AnnN UeuZ KibC KpnW KymI bAkI bBkC bXlX rUoH} oQ{rZ(bG cV hB Jc Kn oH St Tv) lL(dH iC kQ Nl Nn oN) hA(An Ct Fb Ph) bZ(jF qV Tv) iC(dI Nd oH) Ow(Gl kQ) AxjH DkjI NjjL TveD UumS bGjY cWrC dHqT lYoH} Gz{wQ(cA cL Cv Ih iO zG) Tk(Bb cW Il Ng) eD(cI cW Jh) hO(cY iA Pf) Nx(wH wL) Vp(kI nD) hR(iO oK) tO(Ly Pe) wD(cA cL) DcbX EdNj FnnD MnwF aKjR gWqO} Ic{wJ(Ad Aj Ib jK Lx Mm) Nj(Cx De Nk On) wQ(bL Oa Qd Rf) Rc(bG bX) Pe(wK tM) tV(iO Nr) DdQy FptL NbsC QhjI aPqB bCwG cRrW gLvP wPiJ iOvV} oP{Ib(Ad Dc Jq Ju My Nr oH) iC(aD aQ cJ cM cZ) lK(Ao Ef Iz Rh) jY(cG Rc) CthX EfjQ NnlL RbqT QlrA aGlN aMjU aPlM bHoH cYjI hBqY} Jp{cZ(rR wF zH tL) Ow(sK vH yL) pS(cF Ed Qv) Ue(sM vS) bG(uG uU) EdtT FwuM NqvS MpqG IovB ltvH NwyH PeyL aCtL aKzG aLwF iOrV tMrU} nR{rZ(bB bR cJ Dp Fw gP Pi Ql) Tv(Id mP mW Vs) lL(Iu Jj Mx Oz) hW(aI Qx To) Cp(jQ lK) BnhV EzrX MneD OwoN VvjK cSrC} Kf{qG(Af Jl jY Kd Qn Wm) Ik(aR cP rV) Js(qU qV rA) aK(rO wF yL) Fp(vT tL) rW(Jl Uc) HawK QdqP aUhO dLuP gWzA hLtT iOwE} nN{Ex(Hu Mv nU Rh) Wm(Jq ON) Uu(dF Lx Ow) Tv(Ct mP) Ki(Jj Mp) Uh(aY jK) rX(bB hC) oN(aN Ke) BoKn LxdC NjnW IoOw JqVo KyaM} Nb{sC(As cF iA Jd Kj qW Rb) wG(Fy Kg Mm Nn) vB(Ad dN Pj) qV(Bo tL) AdrW MsuP PztV QvtL PjwQ nUrA iOwF} Ed{wQ(hB Ki Ue) uP(Ms My Of) Dc(tV wJ) Dd(rU yH) Hq(rV wE) cS(tT uL) MmwJ NjrW IjqG RbuW PavT cWqX eDwL jRqO} mM{oN(Lv oH oK) tF(dD nW) hX(cW Ks) jU(As Vo) rX(cZ kR) lK(Un Uu) DijO IklL JuhW NxaP VujQ bVcL jErA rZpF} Ex{hO(Al bA Hr Oz) rU(gP oK oN) hL(Aj bG) wH(Nl sK) kF(bP Kc) oN(hP tN) DcqX FpwL JdjK JuwQ OnlM} Fn{eZ(Ad Ch Ml Nf tV) yL(Ad aG cF wQ) iO(sC uZ) AdeD NuwC IdqU JusC KqjU cWhA wQiZ rCkN tMrX} Hu{vB(dN Jd Jj Kg Mv vI) rU(Dd Hq Kj Pj) tV(Hq Mm Pj) wG(gL Om) IiwF OkrW dNvT kNoN} aP{vB(Ad Ao Hq Jd Jq Kn Ky On) mY(cE Nv Nx) Lx(mP mT) Hq(wD wH) aJ(wG tM) NktX KgqG} tL{bC(Kg Mp Ms Mu Of) dN(Kp Mt Nk) Mm(aK aU) Ue(Ad Jt) oH(Of qY) AsNn DdaC FpKg NuRb UcKj} uP{Hq(Ha Jd Mp Mr wL) Jd(cB jY) Of(Nq qQ) HaOn NmPe MpNl NjUp RbuZ QdOk QeKj KiuN dLeT} iO{wF(fY Ij Mm Nd oH pY) uZ(Ad bX Jt On) wG(Kg Qy) AouO MmzA OkwD PjrV zHsC} lL{lX(jI Lu Oi) mE(Il Is Qb) mP(aY bF Ny) Oz(kG nU) oO(bP eC) NknU IokP OhnD lYkC} Ki{qV(aS Fw Jh) Nk(Nj zG) Vv(qX rW) bC(sC uM) UbyL JdrC KcqX TkqU bFsC hGuU iZqG} Dd{rN(bG Ih jY) Up(rU tM) aK(qO tX) qW(qO rW) rR(Jd Pe) MntV OayH bGsC fYvP} On{eZ(In Ji Mp Rb) wC(Kd Pe Ql Uc) yL(Nq Ue) AxNj IhqG RbjM KdrN eDkF} qG{Jd(bG jY Kg) Hb(Ow Ue) Kg(Mn Mp) rX(Ao sO) BoOf RbOk QdPj bGdC} oO{iC(aX Gp Qx) Rc(jY rA) rC(cS dN) qV(cV dH) oN(Aw kR) JfhA aKlK} cW{Tv(hA jG jY) hA(cE Kx) rC(kF mY) NktV JjyL KgjG OfpS mShR} wQ{bZ(Bo Jl Mp Ua Vv) Nk(aO bF) Hq(dN Ql) AdaN IpbG QvcE} kN{oN(Aa cV dF gP) hW(Ct Nl Or) CthX IbtF OurZ UojG aMrC} fY{Ph(jF jR vP) tX(Rb Ub) vB(Kc rA) HbqO VvsO dRtT rUvV} nF{Ow(aW bP lY oH oN) oN(Di Lv Nl oH) TvKj iBqT} tM{Ch(Lj Lx) Pe(Nn Ph) qV(hR oH) AwqQ DcIh HaHw MrJd UphG} Ad{Nj(Il Nm) Rb(eZ sK) yL(Kd Qd) AstU UeuZ IkjF JsqV} mE{jY(Mt Nl Sr) rX(cR Jr Mt) eD(Is Oh) NljE VshW} mT{qV(cV iA tF) jU(aD pF) NjdD TzIb aWjO dNhA tFqW} nD{rA(Ne Nv Ny Pg) qX(aL bL) DcJs JqkQ bMjU} hG{uU(bC bL Hq Hv iJ Mn Mp Uh) IvqZ} Bo{Of(qA vI) aK(gW qV) kF(bF Dc) cItV rCkC} Me{hO(Ly Mh) wL(bC Dc) MmwK bAtV dLqA eDkI} Tk{cF(bG CX Ib Jg) ChjG DkhA TtbO} Ok{Pe(rU tV wK) rW(Qd Rf) NeIn ItqO aUrR} eZ{Jd(aH Mp Ns Ri Vt) ChMp EfEz TvKI} sC{jY(bF cE iC) Vv(cB Ri) EzNg RbbC UvuU} lY{AweD PoNy MvcT OwaM UucE aAcL hVhC} mP{aR(jU lK) TvkQ OiqT bFjU bZqV dMoN} mY{aA(cG Oh Pd) qT(rZ Uo) TvaO QlOw} kC{Kn(Ir Iv Pe Pg) QtrZ VshR dCrC} rU{qO(wJ yD yJ) vP(jH lN) IvhB wLqP} Mn{Kg(rN rW) Om(tR uW) MswL JotO} Ue{uZ(bA Jo Nm) HqwH JtsK bCvB} aK{vV(Ao Kg) FyqO KqjR VvwG tXyL} kG{rZ(Ct Ou Ri) NehW IbTt VsrC} nU{Gp(hW hX rZ) SthW NvrA} kI{rC(Ky Ph) rX(hC Ou) KshX} oH{tV(Fw qW) JhtN tRqY qWuN} aC{AswL NjvB JdwB JuvT} mW{Tv(Js Qh) MtIb bMjU} kK{Jm(qT rA) QaeD OijI} yL{eT(Mp Uv) ChNq dNhB} Nk{bC(wG wL) NlaX} Hq{RhwH hLuX wKqQ} Ik{Kq(aW bX) AorQ} fR{InOr LdcM aObF} nI{DlhX RfNy UvjY} kF{CsLx DphX RjcE} kP{IojO cGrZ dDhW} Dc{FwyD KdrN} Mp{MgqA dNuZ} To{hR(bB Gp)} Iv{MkrO KnlW} Wn{CtcF DijG} Ph{MyrN aUhO} mI{FbrC QvOw} wG{AauW VvaU} AsJdvQ ChNqvS NrliwE MmRiwJ HwQlwL IhKgqO QdPjtO QhUpqA JtUveT RhdNwF UubFmS aGmUqV Constrained panels with 3 analytes, where 1.0E-8 >= 'AUC p-value' > 1.0E-9. Contains 8,775 panels of 27,619,476 total panels evaluated. :
nT{Ib(Ad aM bF Bn Co Ez Fa iP Iu Jd kG Kp Mu Nj Ow Pd) Qt(aM aZ cV cX cY Dc dJ In Is Kn Ld Ma Ml nJ Pg Tz) Kf(bH gW Ii Ij Iv jD Ko lL lM nJ No Oi Qw rA Uu) bW(aY bA bL cN hC Hf Im Kn Ld nA Oh Pg Qb Qe Vp) dJ(bZ cF cM Cx Dc dH Fa hA Ij Kd Oh Qh Rj Un Vs) rA(cW cZ Jd Je Kn Lh Md Mp Mr Mw Ne Nw Qb Qh) Kd(cT iP Jq mM Mt Nw OH Or Pc Qb Qe Rj) Aa(aR bX bZ cR Jl mE Mp Mr Nr nU oF Pg) Dc(aM bC iO Ky Lu mF mH mY nB nD nJ Vs) Ky(aS bL cK Dd Ip Iu Ld Lh Mg Nl Uo) Or(Ad aE dF Hc Lu nL nW Ok Ou Ri Un) iP(Bo cJ dF iH Jl Jq Kc Ma Qa Rc Vt) Tn(cH dK jV lW mW nH nL pF Qw Rh) Jv(bF bL Kn Mt nJ No oP Po Uc Up) mF(bX Qa Qe Qu Qx Qy Rj Ss Up Uv) Bo(bJ Dg hB Jq Lw Me Nd Nv tF) aM(Ad Cv Cx Fa nJ nU nW oF Rj) dF(Ef iC iO jP jV lL Mm mZ nD) mH(aY bZ Ld Ou Qa Qn Rm Uf Up) Hc(bF cO Hu Ik Mx mY Pa Uf) Ri(Db Kn Nl Pa Qe qV Rj Uc) cH(cX Db dH Jq Ki Qe Qm qV) iO(bL dH Ir Is Jq Ld Ow Qd) Dg(Jq Lu mM nC Nk Nl Pg) Pf(aS Kk Mg mZ Ne nJ nU) cN(aC Cv Cw Jg kG No oK) iH(Mm mT mY nH Ou Pi Qd) Oh(dL Fb Mn mU Ne Ud) Ow(aJ bL Dk Jg nR Ok) Uf(Ip Ir Ml mM nJ Qb) Ut(aS Hb Lu mZ Qw Rf) bM(bA hC lN Lu mY Vv) nA(Ir Mn Mp Mr No Qm) pF(Db hC kP Mn nU qV) Po(Lx nK Nl Nv Rh) Uc(aV Ef Nc Tr Uu) Kn(aJ Hb jV lL Vs) Rj(cO Mq Qa Qd Qe) Ou(Bg bX nB Nl Vo) aY(iB kI Mm Mw Ok) bF(Ao Bg Jy lL nJ) bL(jL jO jY nW Pk) lX(aU dD hC Jq Mp) Lx(lL mI nK Ns) Mt(Cx Dp Kk mZ) Tz(Jj Li lW Nl) Nv(Fy mZ Ne nK) Pg(Dp nD Oi Us) nH(Fn Kl Rc St) Dd(dL Qn Rh) Dk(aS Nf Uu) Lu(dG Fy Rm) Mm(bH cV dL) Nj(dD Ny Tr) Ik(Ny Qg Rc) Qw(Cq cT Jk) Kc(jL jV Vq) Ki(Ld lW Nw) Vs(Ct Hu Nl) hA(aK gW Hb) hC(jL kO Rf) oQ(cV cY mY) Db(Ij Jq) Lw(aN Ld) Id(An Ef) Qa(Rh Vu) Qd(Us Vo) Qe(iJ Us) St(Hb jL) Kk(nB Qn) Ko(Ij Ok) Kp(Cx Qm) On(iC Oi) Uu(Jg Jp) Vq(bH Pc) mP(Uk Ur) jV(bA hB) CvmM EzNw FbKl ExJy FnQn LvJd MlHf MnnK MpNe MxbH IcIs TrIo InUp QbJu QvoH JqnD KgRh LieD cEqV cLjY dLtF dMiC nRiJ kCnW rXlL} Us{qT(Bb bF bP Ch Co Dp eD Ef Hq Kj Lj lL Mk Mr Mv My nA oE Om Pg qO qV Qx Uk uV Vp yH) qV(Aj aS Bb BC bW Ed gL hR Ic Iz Jl Ke Lj Lw Mm Mq Nc oE Qz) lO(aS bC cH Cv cW Dd Dp Ic Iu Ji Mm Mt Nj Nl Oi Om Pj Qu Qz Tz) qX(cT Di Ef Hb Ic Is Iu Jf Jm Jy Ke lL mP Nj Pe Pj Qa Rj Uf) rY(aP Bg cP dF eF fP Ha Hc Li Nn nW Pb Pd PF Vt) hO(aP Cq cW dB eF Fa Ij It Ju Ke Mg Mw Pe Qw Tz) Dc(bX Et Jl mT Ne Nj nY On Tk) eD(Al Aw bF Dd Hw Iq Jq Mv Tz) eZ(Fa Fr Ij Jj Ks Mk Nu Nv qC) qC(Fn Ha Ic Md Mu Pb Qd St) vP(bF cE Fw Hb Kx Ml Ph qU) vV(Cv dR Fw gW Hb iC Mf tX) Is(Ib Je Kq nB Of Oy Vs) On(An cV Hu Ib Kk Qz Rh) hR(dJ Jf Ke Nb Nq Rb yD) Tn(dJ Hu Nj nK Qz Rh) qD(aJ Kj Kp Ny Pj Ur) jD(Di dJ Ji Mr Mt yL) rW(aZ cU Ne qW rU yL) Ad(Ib iH Jl Nj Rh) lM(aO Iq oN Pz Rh) Ic(Ib Jl Mu Ut) Tv(iC mT mY mZ) nN(Ji Jl Pg Qa) nH(jK Mn nR Up) wG(cA cE iC Kc) qU(Kl Mq Uf tL) lL(Aw bF cE Ss) zA(dG lK uO wD) Qz(Ib Kq Qt) nB(Cq Dd Qb) hP(cW jT Oz) rA(Mk Mv Ng) jL(Cq Of Oy) Po(mY uW) Et(Kk Rh) Fy(nA oQ) Mt(lW mF) Ik(Kq qG) Jl(Kg Nx) Nv(nC nL) Oh(mM nJ) aP(vB wH) tS(eT Nn) tR(aU Pe) tV(Nr vI) wD(Kx Vv) yE(Nk Pz) uN(aG Qa) uZ(Aw Hr) BgrT DbwH FrNj NsyL MghL MqrB MrtL TzoQ HquX TrUt ImvW RcrC QuxA JoqG JroP KeqW KqnO NymP UuuP PgnA PhrV cIrX cLmY dHhA fPuO mTjU yHrU} Hf{eD(aS bB bL bX cH dB Dc dD dJ Dk Et Hw Iq Kf Kl Ns Qu Qw Tn Uf) hO(Cv cW Dg Dp Ef fP Hb Ib Jk Jp Kj Nv Qu Qw Qy Rb Uu) qU(cE Dl Hc Hw Id Ij Jq Kd Kn Lh Lw Qm Uf Uh uZ Vt) qV(aS aU bL Dl Fn Ij Il In Jh rA Rc Uh Vs xA) mZ(Bo cM Dc Ik iP Jq Ki Lx Ml mY nC oH) qQ(bN dH Ij Ju Jv Ky Mh Ok On Pj Pk Uf) Qz(Ad Dc Dk Fr Hc Jd Jk Kq On Qt Tn) qX(dB dH Fb Fw Jt Kg kI Kn Qg qW Vv) jL(cC Cw dB Dc Dl Ed Et Ju Nj On Rb) xA(bB cP Jo Jv Kg

Figure 23 Continued

Kl Kn lN) jY(Ap Bb dD Dl Kf Ny Vq tM) rT(bP bW Ip Jg Kq Me Om Sr) rZ(cL Di ll Ly Rb Uf Vs) rY(Ap cP Cw Iq On Uf tM) vB(cT eC Hq
Nl Qy Ug uX) vT(dN Hr Io Jk Kg Pe sC) hA(cE Dg Dk kC nL Vq) wB(hG Hq Jf Kr Of Oy) qD(Aa eZ Hb Mh Pj Qd) wF(cT Lj Nk Ns Rh tM)
tL(bL eC Kn Mr Pb qW) lL(Cw Hc Il Nj nW Ss) nB(jH kC kO Ou Uh) qT(Iv Ju lN Uk Vv) gP(hL qC uM zG) yD(aK Nb Pe Pg) eZ(Ao Et Om) mF(Lx Nx oN) nK(Jq kC nC) wQ(bF cA Jj) qC(Kf Qa rS) rA(Je lN mM) sC(cC Kq tF) uU(Al hG Je) uZ(iO jT oK) vP(bP cU Kx) Nr(wL yL) Mm(uL vA) Kj(uL wL) cH(mT rB) nJ(Ib kO) hL(Kq Qy) iZ(qG wD) jU(lY mE) rX(Dl Vt) uP(bP Jg) vU(oN Pe) vW(Im Ky) AddJ AphW LvuW NiuM UbzG HclN KfrB KgqG TkcF UkvV PhrV aKtX eTyL fNwD nNnW mSjG mToH nllK nLiC wKiJ tVoK} iH{Kq(bJ cC Cs dL dR Fw Hu In Ko Kr Ly Ml Na Nc nF Nj Nl nN Nr Pd Ph) Fp(aL Bo DD Dk Et Fr Jg Jt Ke Kf Lx Om Qa Qt Tn Uf Vs tF) Ic(bJ Bo bU bW Cw Ij Is Je Jg Ji Jl Ky Lw Mm Mw Nc Ne Nw Uf) Pe(Bo cE cH Dg Dk Gz Jg Ji Jp kC Ke Nj Nv Qa Tn Uf Ut Vs) Nf(Bo Et Hq iO Iq Jd Je Jh Mu Mw Nv Nx Ok Oy Pg Tn) Kk(Bo cH cM Dd Dk Ed Jp Jt Ke Ko lW Mb Tn Vs) On(cC Cs Ed Fw Il Js Lj Ml Mp Nj Qw Qz tF) Pf(Bo cC Dg Dk Hc Ke Kf Ko Ly Nl Om) Ml(bJ Fr gW Il iO Ne Pd Pg Rh Uf) Hu(Fr Gz Jd Jg Ke Ok Om Qu Ss Vs) Ad(cF Di Ed Io Nb Qv Rf Tj tF) Rh(Cw Et Jd Mg mT mY mZ nJ Qu) nO(aY cH cM cN hC Ky mP Qt Vs) Dc(Bo Im Jm Js Nr Pg Qw Vu) Ed(bW gW Gz Ik Ky Lw Uf Vs) Iv(Jt Ke Lx mM mU Nx Ok Qu) Qz(aL Dk Et Il Jg Jl Qu Vs) nF(Dg Dk Id Li Nw Ow Qt) Qw(Dk Jd Ny Qt Qu Vs) Il(Et Jt Nj Nl Rb) nJ(bH bN bW dK mT) Ik(Et Jt Qu Ss) Jd(bU cM Ly Nt) nN(Jl Ky nW Qd) Bo(mT Nj nK) Nl(bU cM In) tF(iO mM mU) nB(Gz Jq To) nH(kC kO Oz) tT(dJ rW uO) Tj(mM mZ) Po(Lx Vs) Nn(iO Ly) Nt(Hc Jt) Nj(bU Fr) Ny(nA nK) Uf(cC oO) mT(cB kQ) mY(cL kC) qO(cU Kx) AwoO EtNr FweT GzqG NbTt NcNk UeyK TneZ InJt IqiO KlPg KpqC WnOf aKyD aOwB bWoP mMkC mUiP wFnY} uY{Jp(aG Bg Fp Fw Hu Ij Ir Is Jn Kp Mn Mz Nk Nr Nv Pg Qy UP Vv) Uv(dN hG Ij Jj Jm Jo Jt Kj Kl Nr Om On qV rZ sC Ur uX) hG(Aj Ed Fw Hu Ky Nb Nk Uf Up vW yE) aC(Ad Af Dc Fb Fn It Je Kk Qv Uk) Rb(cT Hu Ly Pa Pe qC qD Tz uV) fP(bG bN cC iC Jh Oz Up yH tM) Nk(Ad aG Bc bL cW Jd Ki Uf) Hw(aK aZ Bc bG Gl iO jG Qm) Pk(cM cZ Fr jG Ji Me Mt qY) dJ(Ad Dd dN Fn Ik Kj Uf vB) sC(bF cC Fn iC Jd Kx Rj Uf) Aw(Bo cW dB Me Mp Ua Vs) Fw(Ad Dd Fn gW iP Is It) Ue(bA Cs Hq Kg Md No Nt) Jh(Bg Dl dN Fn Hc Kd Rj) Uk(aP cW Db Ky qA qO qP) iO(dN Ic Jo Kg Ki On Pj) aZ(Al Fb Me rY vP wG) cC(Kf Mg My Rj rU rX) Qv(cN Nr Vv wQ zG) Ky(Hq Jq Ms tV Ul) aP(Jd Kl Lh Lx On) bC(As bG Ip It Wm) dB(Is Jt Kj Nn rX) Bc(Ao Mu oF vI) Db(bQ bX Jq My) Dc(Ax Ez hO Ow) Nt(Js Mz Tz uX) Kf(jG Mp Up wJ) cS(cR Mt Pe wQ) rB(Aj Bo dN Kz) Ap(Ez Gp Js) Md(aG Fb Na) Me(bE Cv zI) Jd(Hu Ic Kk) bG(Fn iP Lh) oH(Et Mp Up) uX(Ed Iq Wm) Ez(Dd Mg) No(Jn Mz) Nr(aF Ki) Hq(bQ cR) Hc(aO Mv) Qh(Fp It) Kg(Gl Ik) Kr(Lj Pe) Rj(cR Ha) Ok(bE cJ) Uf(Jj Vo) Pa(Fb Oa) aG(aN Nl) cM(Et jO) wQ(Cu zI) rU(aU qP) uP(Ao Hv) AdKd AsJk BbdN PoNa FnUp MpiP IpqD JraF JtbU KcwG LhqC VvfY aOtM} Db{qV(Dc eZ Ic Jq Js Jt Lw Ly Mg Nb Nc Ni Oh Pe Qw Rc Ss Vs tM xA) qU(bC bP bW cE Dg Di Jq Jt Ke Lw Nc Ni Pf Ss Uh uZ Vs wB) hO(aF cJ Di Dp Ha Ij Is Jg Jk Kf Kn Md My Nb Ph Rb Uc) wB(aK Ao Ch CP Ef Hw Ih Lj Ms Nl Oy rS wC xA) wQ(Ap bF bN bZ cC cE cL Im Nb Po Qd vW zG) xA(Cp Dc Ic Jg Jp Jt Kf Nr Om qW Rb Um) vW(Et Hr Jd Ly Ni Ok Om Pk Qu rY sC tL) wH(aC aZ cC cR Gp Ih Jl Ld vH Vp wC) hL(Dg Ef gP Kq Lh Mh Ng Ph Qy rQ) jL(bP Dc Je Jv Nc Nl Nn Oh Oz Qw) Qz(Ad Dc eZ Jk Jq Kq On qC Qt) eD(cG Cv Lw My Oh Oi Pf Po qT) wD(aZ bF cC cE iC oE Uk zG) rY(bR hA Iq Jp nW On pF Vs) rV(Et Kg Kq Ok On sC) Kk(Ap Dg Jg Ok yD) eZ(Ao Dl Hb Jv Uf) wF(aC bN Fp Nt uP) qX(aZ Bo cC cF cU) vB(aP Hw Lh Nb Ug) Um(qC qD yH zH) Mm(jO qG vT) Lh(qC qD uL) nN(Jq Ky Ou) jP(Jp On Tn) sC(cE Mh Nn) Mr(rN vP) Nj(Ad eF) Uk(vV yK) nB(cL Qn) tX(cW vP) tR(aU cI) rB(Ap Li) qC(Nn uL) qD(Dp Pz) qG(iP iZ) jO(bC Cw) tM(oK Pc) tL(Kj oH) jU(bW mT) rZ(cG Di) qQ(Ky Ph) vU(hB nY) NrvT HuqZ TohR TvmW IquL IvrA RhoP NynO aCcF aKjR cCqA dLuP nKjI hGuZ} dJ{Ic(Bc bG Bn Bo Cv Cw De Dk Ib Il Is Je Jh Kz Lh Mu Mw My Nv Nw Or qV Qy Qz vS) Qw(bX Cw Dc jF Jp Mu Mw Ny On qV qW Rc Ss Tn) vB(Ad Cv Ii Jd Kf Mk Mv Nl Of Oy qV rX sO Vu) Ad(aC cF Gl Hu Jm Kk Ks Nm Nt Rh Tj) nH(aX bP cH cL Fr Id Ji Kd Pa Rm Tt) qV(aD aG bB bG bS cB dB Fn iB Kz rY) bX(aC aQ cF Ed eZ gW Is Kk Kq Ly) nC(cG cL Cq dD Ed Jg Ki Lx Mr Qv) nB(jE Ji jM Jq Lh Ou Pg Qn Ut) nK(Ha Im Is Iu Jk Lv Mn Qt Uv) cF(aQ bB cK Jd Kq uZ vS Tk) eT(bR dH Pj Qz wQ yH tM) hR(Cv Jh oF Pk To Uf Uk) wG(Bc Di pF qC rC rP Uk) qW(bB Dd Fw Jt Kf mF Qt) Kq(Ik jY Kk nR qU Qz) tQ(Hw Iq Jg Ky Mu Pc) qI(Bo Di Fn Fy Kz On) nJ(Bo Cu jM oH oP) tX(cS It oH pF qB) Bc(rX sO tV uT) aC(bU cB Cw Dc) tT(Ct Jm Mg Ms) rC(aD bS cW Ki) jF(bR cB On Qu) xA(Hb Kg Lh Mm) fP(qQ rY uO) nL(Lx Po Tv) rZ(Hw Ms nW) rT(Iq Kz Nj) Bo(gW Qz) Tn(jO nA) Jd(bU uU) Kf(jY pY) Vq(eD lN) wQ(As Ke) qX(Pi Pk) lL(Qt Qu) sC(Na Rb) oP(aI cH) CheZ DcEd NsjD NkrY HwyL IqtV PzqD QzNy JqnA JtuZ KkOk KzrQ LhqC OmfN OnjU UkwH PhpY PjrU nOhC mFjM} dB{qX(Ap As aZ bH Bo bU bW dE Di Fw Iv iZ Je Jg Kl Ky Na Nj qW qY Vv) qV(aU bG bW bX Dc Di Fw hR Il Jd Jt Kf Kk Lw My Nj Nl Qh rA Vs tF) qU(Cw Dd Fr Id Ij Is Je Jg Jh Kg Kl Lx Mt Nh Nl Pf qT Qu Ss Tn Vq) rY(As bC cK hX Ij Jg Jh Lh Lx Mq Mw Nw Nx Of pF Qt Tn Vt) jL(bR cW hR Iu Je jU Kc Mv Nj Oy Qu Qw) eD(Ba Dg fP Hw Ji Kz Lw pF Qz) wQ(Aj aO As bC Cu Ha Kl Qu Uk) hR(bB bW cE Gz Iq Jg Jp Kf Uf) rX(Ad bB Hx Il Jr Li Lw pF Uh) lM(aF aG aO bZ nC rZ vW wB tM) jY(bW Is Jg Ny Pf Qt Uf Vs) wL(aS aU Iu Jo Qy) xA(Jd Kg On Pa Ph) yL(dN Et hV lK sC) Qz(Ad Dc Dk Kq) bC(rC tU wG tL) hO(Hq Is Ju Lh) qD(Is Lh Qa Qd) wH(aZ fP Ip Ld) uM(Jj Ly Ow Ut) cE(hA lL wG) eZ(Ao Ch hP) wF(aG Al oH) tL(Hw jU Mm) rZ(Ap Ok Uf) vP(bG rU Uk) No(rO vS) hL(Ex uP) iC(kO vB) qC(yE tM) jP(Of tM) lL(Bo Ul) rW(Ok Pk) rN(Kg Mg) qP(bG Hb) qQ(It Qh) vW(Jj lK) EdqT GzjI MmvV TzwP HqyE IkKq IljH PzlN JdqI JufN KkOn KrwK LhvB PfhA aZsC bFwG bWrC cWjR dLuP hVzG tXqO jOvT} mZ{Lx(aG aN eD Ez hB Iu Kz mF mY No Ns Og Pd Pe Pf Vo) Mt(aN aP bH jO kO kQ Mp nA nB Ng Oh Or Uo) Tv(AO Dp Fy Id Ik iO Js Ks Ky mY Pd Pg) Ko(Dc Ex hA jU jV lK No Tn Uh Up) Oh(Fw iB In Iu Ky mY nB Nf nK Oz) Ic(bA bF dF Kf Ou Qb Qe Qn) Id(aG bG Hu nF nL Pe Pf Pg) Ki(Dc Hr Is Jq nH Ny oN Ut) Uu(cR Fn gL Ma Ml Or Ua Ut) Ik(aY iB Jq mY nK Qe) Ir(Aa lL nA nI nK qX) Ny(Ez NF Pe Uc Tj) nB(Im Ji Jq lL Nj Oi) qT(Iv Jj Jp Jr Lv Mm) Qw(Jk Oi Ug Uv Tj) oN(Hb Kk Pd Pe Vt) Dc(Ib Ky Lu Ue) Nk(eD jE jV lL) Is(Fy nA Nf Ue) jP(Co Kz Md Mw) jU(Io Kn nJ Ua) Nj(cM nK oP) Jp(jH qX rA) Jq(lY oQ Uc) Kq(Fy Hb tF) jK(Ar Qt Rc) jT(Fy Io Mh) No(Ex mF) Lv(rA Tz) Mn(iP jH) Mp(lY nK) Ib(Ut Vs) Oe(iC lN) Og(mY Oz) Ow(Pe Ql) nA(Oz Po) rY(Jj mF) rX(mI nK) AoOn CvlK DijY DlrA EzjH GpiP MejO MmqX TzaH TnaY HblL SteD QtjD OutF UojG VthA cLnH iCqU qYqV} xA{Bc(aN aW bB bG Ch dR eT Fn Gp hG hP lM Nb Qd rX sO Um) Uf(Af cJ cR Ed Gl Ha Ki Ky Nc Nq Ny qX sK uI) Ok(Aa aC bF cA cL dN iC lO Nv Uk uP Vv) Lh(aC bG cC cL cX Fp Mr No Nr Pg qX) cW(Ed Fw Ic Jd Jo Kc Kx Na Nk Uk Vv) aZ(Ao Dc Ed Iq Jh Kl Na No Pj Qv) Et(aC bC hG Ks Qu Rj sK Ue Uv) Kf(cC hG jF Js Kr Lj qC qT Rb) Ic(bF Ch cP jL Kx Ow Rh zG) Jp(bG Ed Hu qT qW Ue Uk Vv) Dd(aP Fn hO Hu Kx Nd Qe) Mm(As Cs dR Ed Hu qX uL) Um(cE Ha Hu iC Io Nr Pc) Na(dN hO Ij Jo Uk uW) No(aP cS hO Jf qT) Nt(Bb Dg fP Or rR) rU(Ap Ex Fn Kg Ky) Jd(cC Ez jO Nd) qW(bG Nr Nx Ug) Ad(Lj Mn rA) Hu(Nh Nl Ph) Jh(cC dC jF) Qz(Ma Nv Uk) Kg(qD qX rN) Ki(Ed Nk Uk) Kr(bB eT Ph) fP(Fw iC Ih) Hw(Kd Rj) Iq(Ma Nd) Pa(Oa uP) bC(Ex Jo) iP(Uk Vv) AobE ApQt CvqV EdNl EzOm FnaG FwtM GzbM NqqD MfdN JjrA KlaL KnaP KzbS bGsC bWuR} Iq{qG(cB Ef Ha iA Ic Ph Pj rX wF wP tL) tV(bC bV dG Ha Ij Im Ir Is Lj Mz) qV(Bo Fn iA Ic Kk Ko Ks Ow rV wF) tL(aR As cI cZ Jp Lh Mp Ms Mt Om) rT(It Iu Jl Mn Nv Qa Up uZ Vp yL) qD(cW Dl Ez Mv Nt oN Pz Tt Um) wF(cC Hr Hu Nc Nl Uk uL uW) rV(As jL Kc Kr Ky Qg Um Up) qC(cR Dk Ez Mf Nq Of Pj) vB(Fn Lh Me Mk Mv Nb Nl) hO(bJ Jp Mv Nm Nx Ok) hP(bI iA Lx Mr Pf Pj) wL(Ch Jp Ky Nc rB Uf) wH(aW Jj Ne Om yD) rU(Fp iP Lj Um uZ) sC(aZ bR iA iZ Qa) yL(Ao Fn Jp Ms Om) Cw(hA jO qT qU) wQ(aN iZ jH Rf) wD(Hv Jp Lj Vv) nB(dI Kk Nd) wG(Fp Nu qU) uP(dL Qa Up) vH(dC Ez Uf) Wm(pS uL) On(hA jM) Um(uM uN) cC(hR jL) cW(eD qU) fP(hL qQ) nA(Nv Og) tR(cJ Ki) wC(Of Om) rA(Ed mE) rR(Mt oN) uW(Ha Me) uZ(Mp Nn) EtKk ExqI FneZ FprQ FwqT GzuL NquO NhIn NlqU TvnH IhrO JpvS KyuN NyqQ UkfN

Figure 23 Continued dLzA gWtX hAqZ tUjH} Ic{Nj(aP Bn Cv Fr Hc Hu In Jd Je Jk Kq Kr Kz Lu Mu Ok Qw Ss Tn Tz) wQ(Ap bE bF bG bZ cM cZ gL Im Ki oH
Ow) bX(cC Cv Dc Jd Kf kK Nl Oz Qh Tz tF) wJ(bO Et Fn Fp fY Ih Jd Ok Qu Uu zI) Et(Ib iJ Kk Kr Lu Qy Rh Tk) nH(aY cG cL kO Ml Mn Tv)
Qz(aP bA Dc Kr Tz vV) Nl(Cv Ib Jd Nk Qy) Kr(aP Dc eT Jk qC) nC(Bb Kf Kn Lh Mr) tV(cJ Gl gW Ik Pf) Nm(Ad Cv Kq On) Nt(Ok Qt Qy
sC) Dd(aW nW oF) In(Ny On Ut) Qw(Ib qP vV) tT(cQ Lj Qc) qD(gP rW uX) kO(Ko Up Ut) Cv(cC Kz) Cw(Qy tF) Dc(aP Ky) Ed(qT qX)
Nb(fP wG) Kq(iJ nI) On(iA jM) Uk(qP yL) Oz(aR oF) bG(Ny qG) nR(cG jO) lW(jE jF) qC(Me vV) qV(Jd lY) tL(BC) sC(Lx Pg) oP(Dl Qn)
vB(cR Ue) PomH FneD NokI NrvW MnnK NeIb NgTk JfhR JhgW QyVq JkJm KfiA KkhP LjuM RhbR OwnJ UfwK PetS aKjR aPwD aZwG
cCuX cMzI mElN mMjF nLlK iZqO kNoN} vW{Ap(Ax Bc cW Ed Ez Im Kl Nb Nr Ny Qd qP sC sK) fP(cN Fn Ha Hu Ih Io Js Mj qC Qd Qe
rA wL) Bc(aN bZ hP Hv Kd Mv Oz Pe qY sO Uf) Ed(Ad Dd dF eD hG Jj jO Kf Nb Uf vO) Oa(bL Cv Hq Hw Jj Kf Lh Nl rN Vv zI) Fn(aC Ao
aZ Lz Mm Na oE Uk Um Vp) Kr(aC aN bC Cv Mg Pe Ub wJ wP) Uf(Ax dN Fp jQ Kk Me Pe wG) Nr(Fb Jp Nl Pk Sr Vs Vu) bC(As Et Kd Kg
Me Rb Wm) Nk(cP hG jP qW Qz) Na(Aj Ao Ef Uu) Qw(De Kl Uc zA) Kk(Lj lM qY wP) dN(Ih Jh Qb Rc) qD(bP cM cW Ii) wG(aP bF cL Kx)
Ad(Ih Qe Rf) Fw(bZ Is Pk) Hw(Cs Ow Up) Qd(Fy Jp Kz) Qz(bJ Lx Uv) Kf(Fp Pe qC) Lj(Ba Rb Rc) fY(dR Et Me) sC(bF Qu Vv) Nt(Dk Fy)
Jj(As Uv) Kg(aP Nb) Lh(Gz Pg) aO(Pk Uk) AncC EtKo FbdC HabZ NoUb UebI JdRf QviC JpPe KyqC UmaN aJuX aKbW jOtL lMoH}
nA{Jq(Af aR Cs Ez Gp Ki mE Nd nN Oa oN Rf) kO(Hx Ih Jk Mn Mp Mx Nr Nw Oh Ok Om Qe) nH(Lh Ma Md Mr Nb Nr Oh Pd Qa Tr) jP(Fn
Je Jf Nr Nx Pb Qx Qy Uk Tj) Lx(aG Fp kC Ma No Ph Qc rB Uu) Nv(Hv Ik Iu Iv Jn kF Mq Nq Of) nC(Ih Ii Jl Ke Mr Og Ok Qe Tr) nL(Ii Jl Ke
Ma Mr Oh Qa Tv) Ex(An CH Fa Of Qn Uu) Nr(Il In mF Mp nB nO rB) Uv(Gp Ik In Jj jY Oi oN) Tv(bZ Ct Gp Js Up Uu) Ny(aO Gp Jk jU Kr
Ub) Ik(dD Mr Om On Pg) Oi(Cu Kq Nw oN Tr) qT(Cp It Ky Mx Rf) Og(Is On Oz Pd) nO(Bo Ir Jl Ok) jU(Io Me Mr Mz) oN(Ez Hb Pj Uf)
Na(Nw Om Ut) Kq(Ct Ez kQ) nB(Im Pg Qb) Bg(Ut Vs) Ef(Fa qX) Mr(Is Mp) Pe(nJ Oz) BokF CqIn CtTn DcUp WmVs PoaW GpkQ NtrB
LuTz MdjO MnaA MzlL HxIr QllN UucE mErY mHqU} nB{oH(Ad bF cE Im Ir kC Lx nR Ou Ow Po Tt) Ny(aP Bg bV Ez Fa kF Ne nK Qm
Uf) Nj(Dc iC Im kO Mp Oe Pg Qb qY) Tn(aM aP aV De Dk Ef kF Lv Qv) Dc(Ez Fp Hu Ke kF Pk Uu) Gz(hB Ir Lx Nx Oh Pi Qb) jO(Hw Ir Jo
Mt Nk Pd Po) Kk(aM Hu Iv kS Lj nH) Ld(Aa Ax dN Hu Nk Uu) kF(cG Fy Im Kq Rm Ut) Uu(cL Im Ko Lh Nv) Lx(aV De Hb Ke) Oh(dI kC nL
nO) Oi(hX kO Nr Nw) qT(Ir mW nI qY) lL(cE cL nR Oz) Mw(Al Kq Uh) Tz(Ez kO Lv) Hw(hV jP jR) Rm(In jY Pk) Oe(hV iC Nd) Up(kE kO
Rf) Ut(aO Hu Ib) tF(Lh Ou Uh) rY(Mn Nt Oz) Ef(jM On) Po(kE mF) Tv(Ik Iv) Im(kE lX) Jq(bV Qm) Nx(gP hG) aP(bF Fy) bW(Id Mn) rA(Ez
pF) lM(Kf Qt) DdNd DkKq FnjY GpkQ NsTt NejU TrlN IrhV PziC JiOu KnRh RflK UhnN PakO PgrB aFqV cPjM} qD{yE(cC cV dC dN eT
gW iO jL jQ Nx Rj) Kz(bQ cO Dc Dl Ib Ij Kq Ml On qT) qG(Ao cF fP Nq Om Pi qV Um uW) eZ(Ap Dl hP Ib Kf Mv Qy rX) gP(Dd fP Jp Mp
Ok Pk Pz Uf) wQ(cS Hu Ii Jj Kf Mv Nx Ss) Jt(bP gW Kk Nm rT wJ yJ) Jp(aG aN cC jT Ow Uh) vB(cT Cv Hu Ip It Rb) vP(Ap aZ Jq Kg Ph Vv)
Im(Bc Ed fP No Pk) wG(Ez It oH Qu Vv) Dc(As Me Na Qw) Gz(cG hA Mu Mw) Pz(cC tR uM uX) Kf(aG gW qP wK) fP(Pb rX sC tL) yJ(Kc
Kg Kx Ky) rT(iO Kr Ok Uv) uP(bH bW dL Kg) Ex(Ar cS qQ) Lh(aK Ow qI) Vq(jT Mu Ur) Pj(aK qP uX) cW(Ap Et Ip) tT(Jo Jq Kn) rQ(Bc Kk
No) Ok(qP wK) jQ(Et Hb) tM(rW uX) sC(cF Uu) ApvV AsyL DdMw NorU NaQw UbrZ HqrB IbUm IpvU JowK KjuG KkqI KpaG PhaK
bWtR fYtX iOrY qAuU} wQ{Ap(aC Ax Jl Ky Ly Mj Mw Nf Oy Qm Qt qV rV Uk Uu) aZ(aV bH bX cL cQ Cu Fy It Kf Ok rX sC wG) Uk(cV
Dd Et hB Hq Mp Oa Pk rW yK) No(aN aO bF bG Ed jU Kl Mm Ut) Nk(aC Cp Fn hG Jv Kg nW qV) fP(cI hO iZ jM Ky Pe Pi qT) Uf(aI aL aV
Kk Nq qO qP) bZ(As Bc Bg Ez Fw Hc Iz) Et(Dg iC Ik Ko qC Qu) Nt(aC dN Fy Kl Kn Rj) Kf(As cF Dl Ih Qd Qu) Um(aN cG cL Hq vU yJ)
Lh(bG Fp Qm Rj uP) Cu(cC Ed Js Qd) Na(jH Mh Of) Ki(cE fN hA) aN(Kg Kl Oa) dN(Ul Vp Vv) qC(Al Ms Pj) Mm(jH Ky) Ue(Fw uZ) Hq(bL
cC) Hc(Ao Ct) It(bW Ed) Jv(As cC) Kz(Ih qV) Up(Dc uP) bB(cZ Kk) BcsO EfUa NsQz LyaO MgQt NbqV IkPh RbbC QdPj QwrV QvKx
QubW KgRf PkiZ bFcF hGuU} mF{Ex(bZ Ih It Kc Ky nJ Of oH pF Qw) jP(Fa Jg Ko Lj Mh Mj Nq Nw Pa pF) jE(Aa cF cG cH cQ Nq Nx oN
Pd) qU(Gl Ih Jv nH nJ Qh Sr Tn) Lx(Bg Cs jM oH Pi Qh rX) Po(Ha jO Js Kr Ky qT) Kq(cR Ez Hb kQ nN Tj) Ny(Ez iA jD kO Oa Qm) dE(bF
Ir Kn Mr Nx Tv) Uv(aM Ky Nt oP Up) rX(IL mH Mr Nk oQ) Qw(bF Nv Nx Qt) Vs(bH Ib Na Tj) jY(Gl Mr Mt No) Ed(jF Mn oN) Jq(cR Ql
Wm) Ut(bZ Jv Mj) eD(Ha Lh Rm) tF(aR jR Kn) qV(aO Kr Tr) Bo(Di nN) Ez(Nx oN) Nr(Iv nH) Mr(rB Ub) Id(Jy Pb) Tv(jD Mf) In(Nv Qa)
Jf(jF qT) Ky(Iu oN) Or(jL nN) hA(bZ Rb) jM(Ih Oh) jV(aW cW) kQ(No Qg) oP(Jv nO) CqEf CtQt LvlO HwjD SsjF RjaR NxaP OmrZ OuqT
UubF OyrB OzlL PbjO bQjU rAkS} nH{rA(Jl lL Mr Mt Mu Mv My nL Nw Om On Pd Pi Qe Qt Rm Ur) kO(cL Dc Fn Id Kf Ki nJ Ny Oe Oi oP
tF) lL(Aw Dd Gl Ih In Kg Kp lX Md Nv qX) jO(Ji Li Mx Nk Nu Nw Nx Oh Qb) Tv(cH Cu Ij iP kC Ma Up) cG(bV dH Gz hB kF Ki Ma)
Kn(aW Bo Ik Iv nJ nL) Ki(kC Ld Mh Ml Rc) Ny(dR Ik iO Js nK) Or(cH hA jK Pk qX) tF(cE Ib Jj mY) jP(Gl Ko Qa Rg) Bo(Kc lX Ml) Ex(An
kF Pk) Ik(aR oN Uv) Qm(eD Jq jU) Oi(jD Ko qU) hA(Gl Oh On) qX(Ha Qa Tz) As(jI jQ) Dc(nJ Qz) Ml(Gp Ow) Nd(Id Rc) Nk(jD jV) Ib(cE
On) aR(Gz Ub) cL(aG dH) nO(oP oQ) jH(Ne Qh) jK(Kc Kd) kC(Kk Uo) CpLx DdjI EfoN GliC NtrY MteD NjnW HwhX TtQz RajU QtlM
OhmY mErX mMqU} Bc{wG(bF cH Di dL Ed Jl Ky Mr Nf Nr Oa Pe Pj Qn qU Uc Uk uU Vt) rY(bB cW dC Di Fn It Jp Kf Nd qV Qw To tV
uN) tL(aN Hq Ih Kd Kp Mp Ms oF rP tV Uk Up) wL(aC aF aO Di dM Fn Fp iZ Mp Mw Qb) tV(aO bG Fw Kp Ms rV rX Ue Ul uZ) vB(aC aN
Ao Ap Et jH Mp Up uZ) sO(Ed Ha Ih Il Mp Uk Vv) uN(bO cL gW Kk Of Up Wm) vT(aO Fp Ha Kd Lj Nu Pe) uG(Ax Nj Rj rV rX uZ) yH(cF
Ha Lj Nk Oa) uZ(Ao Jp Kd Kk Mp) rV(dH Et Hb iZ) uT(aU cF dM Fr) tO(Ha Pc Qd) Lh(wC wD) aF(wF zH) zA(iA Mp) yL(Et Fn) rP(Uc Uv)
uU(It Jd) ChtM CwrB UewC QvrU KfqC UfvV aCuL bGrQ bZtU cBwH mTqV iZrS} nK{nL(Cq Ha Jl Jq Li Nv Nx oN Ow Pa Pd Pe Po Ut)
Ny(dE Jh Jn Jt Kc Ki Ky Mq Mw nC Nf nI Nj) Lx(aG Ct dN fP hG kQ Mv nC No Oi Ph Uu) Tv(Cu Fw Ij Kc Ki Lh nN Uu tF) kO(Mr No Nx
oN Pd Rm Tr Ut) nC(Ir Mr Mt On Ow Pd) kC(Ki oN Pe Po Rg Tt) Jq(aW cC Kc Ki tF) Ex(bW hG Rh tF) Id(cT Ki kQ Lj) Oi(Dc jU Rm Tt)
Ef(IO Nv Po) Mn(iC nI rY) Ik(Hq Ok oN) In(Cq Dc Ir) Uv(iC Ii jP) Uu(bF cG oN) Po(Iv kF) Hb(Kq oN) Ki(cL Mw) Nv(aP jP) jU(Lj Oa) lN(Kf
Kn) BoIs CqNg DcJs EzcL GljP NokQ MdrY MpcC MrRh MzqT NjTt NljY IrQc IuKy RbjT JujH RfUp NxnO UojK UfcG UreD PjaR mHlL}
qC{Pk(aG cW Dk Fn Je Jt Mh Mp Qh qU) tM(aO As bB cS Ii Jm Jt Ms oF) cW(Ad Hb Jd Kf Kr Qw Uf Vq) fP(bG bQ cT Jt Nb Ow Pb uT)
On(Ez Ik jG Mn Ow qG Ss) uP(cC cI Et Fn Jd Kf Na) Ap(Ik Je Mg vP wJ yJ) Pz(aG bI iO Me Nt Qw) Na(Dl Jt qV qW uL) Jd(aG bP gP Kf qA)
Ok(cC eZ Kz qG wJ) Me(Dc Jp Ly tT) Tt(Aj Nl Pb Ra) Qz(aP Cv gP Kc) Kf(bP eZ iO vP) Lh(aG aK Hu zG) Rh(Et Gz Hb Jt) Um(aF Ng Pj Sr)
Vq(Cv Fa Ha Qa) rT(aZ Jt Kz Rb) Jp(Iu Md sK) Dc(As Qw) Et(qG wK) aI(Ad Uf) gW(Ij Kg) tT(Ao Pj) vP(aZ rU) ExcG GzhO NotO MgJt
NkrZ QccC KitR KzaN dNyE hGuU} tL{Uf(aC aL jE Jj jQ Kq Li Ms Nl Pf qG rB tT) fP(bG cC cR dE Ik jM Md Mr Nj oH Ow Oz) bC(Ao Dd
Fb Ip Kr Nu Pk Qt Up) No(cS Dg Ef Kn nW Ph Un Uu) Ap(Fp Jg Og oH Pf Qz) Nt(Aj cS Js lN Qh Qy) Qz(Af bG Kf Ow uP) Qw(aQ Ct Fn Hr
Ju) Kr(Ki Nm On qV wB) Kj(aP Ik Rf Ue) Um(gW jO Kx Nb) aZ(bX oH qA vP) dN(Et Nj Nm Ub) Ad(Ik iO Uk) Dd(Ha Nk Uk) Fp(Ex Hb Ph)
Na(Hb Ib Kq) Kg(iO Nb oH) qV(Nl Pe Pf) Et(eZ iJ) Gz(Nw rV) Ue(Jp Lh) Hq(cC Ki) Kz(hW Nc) gW(Kf Uk) AoeZ AsJk CvOf EfNq ExcW
IscC JdaG JejO JpOw JuaC KiaN bWeF cSoN hGuU} Qw{eZ(Aj Ao Ap Ba Kq Of Om Rc Tn) rY(bF Bo Jg Jk Jp Jt Kq Lh Mu) wG(bS cA cL
Hv Kc Kx pS) tV(Hv iJ Kk Nb qP rT) uM(Fn hG Jg Nc Qu Tz) tX(aU jR Ml qP tN) Jy(rT sC uW vB) cW(hA hP pS rX) fY(Di Jg Kf Uu)
qO(bM Kx qT qY) vV(bI hO Jg Ph) Ad(aW Ib Nm) On(Ib Js Nt) yH(aC Hr Pz) qX(cC Dk Tt) yL(Ij Kk Uo) uX(oK Pe Uv) vH(Ip It Kg) Nj(Fr
Vs) Ss(rN wK) aF(uZ zH) fR(aM Tj) qT(Of Uk) tM(aO Ba) jU(mP rT) uP(Di Up) uW(Nb oK) vO(cG iA) AwrQ BoqV CprT CwjL DckO FnqU
NtQt MdzA IzrN RbsC QuqA KlwK NyrX UouN UvoP OzwF iJqH hCwE oQoH} Ap{cZ(aW Ax cJ Cv fY Il Iu Jd Jf Jq Lj Mk Mm Qv Wm)
fY(Af aZ cW Dd hA Iu Mn Nq Ns qO) qP(Dd Ez Je Ky Nu Qt Rb Rf) tM(As Fp iA Jl jY Nw Qd) qO(Di Ez Iu Jm Ks Nj Qe) vP(bW Jl Qt Qu

Figure 23 Continued qW rV Uk) wJ(Cx Ez Hq Nf qW sK) uP(dL Ih Jl Pg Qe Uv) vV(aL aZ Qd Qt Uc) wK(Ha Lj Uu uZ) rB(Ik Kk Nt Qz) tR(aU cJ Nb) rW(dC Jf qU) vB(Qz Ue Uk) vl(aL cM It) Fp(uM vT) Fr(sC uW) Lj(tU wP) hA(Lu Nm) tT(hL Nk) qA(Nf Vt) wE(cZ Dl) qG(dG uM) uZ{jT Rh) TohR QlsC OawP PehP aKjR aLyK nJoN hXwD jQuL} Vq{hA(bQ cW dD Di Fn Gz Ha Hc It Kl Lj Mr nY Ss Tz Tj) hO(Bn Ct dD Fb Ha hP Ih Lh Ng Nu Nv Pe Po Ql Vt) jY(Id Is It Je Jh jO Ki Mw Nb nY Pe Qh Tz Tk) hL(Cs Dg Fp Fr Im jl jQ Jr Mu nY Po Ut) hP(aU cG cW Hx Is Kq Mp Og Oy Vu) qU(aK aU Dc It jD Nj Nk Pg Ph) rX(Gz Kk Qv qX Tz) rB(Jp Ke Ko On) jO(Ad aU gW Oy) jP(Ad Cw Oy Tn) fY(cU Di Hb) tF(jQ jR rA) rZ(jG jU Vs) eD(gW Tt) eZ(Ct Of) iC(Ch It) qX(Lj Up) qV(Iv qY) AweT GzhR PcrV dRlL iAjQ jRqO} Nt{Kq(bX cF CW Jd Jk jQ Ki Mf Ml Nc Nf On Rh sC Ss) wL(Hw Ii Ij Ne Nx Qa Qh) yL(bC Dd Ij Ms Pk Qh Uk) uP(Ao Dk Hb Of Up uZ wF) vB(Ii lN Nl Nv Qy Vt) Ad(bX fP Ib Nj Qy) sC(bG Cp Hb Kx lN) Et(Hc Ne Nh qZ) Ib(Jt rT tU wH) tM(Ba Cp Ct Qh) Fy(uZ vP vT) On(Ed Jd Up) Uk(vV wD wG) wH(Cp Pz Uu) qG(Aj Ao Ph) qQ(Dk Lh Qh) uX(Na Nx Ph) Cw(Id lL) Ly(rV uL) Jp(uZ wF) Ok(jT Kk) aC(vT wF) eZ(Nv Qh) jP(kO lX) rT(fP Jg) AaqO BoQz ChwB NmrV NayE NlJd TtqX RbtO PzyH KnzG KzrQ NxrU bWwG iOuL} nL{rA(Jg Jl Jr Li lO ME Mr Mt Mv Of Oh Ok Om Ou Pb Qv Qx) lL(bA cS dF gL Ih lY Mh oK Ou) iP(Im Ir Ji Kc Ld Lh No Ny) jK(aY bB cG cH dF Ko pF Rm) jO(hG Hw Me Mx Nw Nx Pf Qb) Ny(Fy Gl In No pF Qm) qX(Ir jD mE Or Qa Qx) jP(cT Kp On Pj Qu Rg) tF(Bo Gp Ki oF) kO(Lx Ml Tv Up) cH(Ex jH Ki) nJ(Kn Tv Up) iC(Ir Mt Sr) jD(mH Nk Oi) Dc(Qz Vu) Nj(Bo jY) Id(cM Lj) On(pF rY) jH(Rj Tn) qV(bF cW) rZ(Nc Nk) lM(cR kS) oN(cU nC) LxIb ImiO HblO QyjV JqQm JteD RmjI cBlK mHrB} Na{rT(aP aX aZ bW hX Ib Ij jP Kx lN Og yE) On(cC cK hA iB jL lL lN) qX(Aw Co Et Jf Kl Nl Tn) qZ(Ii Jg Jj Nl Om) sC(cE cL Hq Kx qU) wK(Hb Jj Mm Ng) tM(Aj aO Ba qY) uM(Kl Kq Om Pk) Jd(lL qU qV) yL(aD bX Jf) vH(Js Kg nW) vP(Bb Kx qV) Cw(jO Tk) Ng(rO uL) Hq(qQ vB) Ib(Ad tS) Je(rA rY) Kq(Kk nO) cW(eD jL) eZ(Qh Uu) wL(Nn Ug) wB(Ao De) qA(cC qY) qU(Kf Tn) rQ(bW Ii) uX(Nu oK) BarZ DcjL DiuP NorR MmqQ NcvB RctN JgiB JjrO JouL JptS RhwF UmvA PeuW PhtT aGyJ bCqV bFwG cGnO cJwH cUrW mMlL hGzH yHqW jRqO} Cw{jO(aM Ao bE bJ Bo bW dA Fa Fp Hu iC Ij Js Ky Lj Mz Pe) qX(aG bO dC dE Fp Hx Ij jM Ky Nn Nv Oa Oi Po Qd Uk) jL(bl dH hA iJ Iv Ko Nq oF Pf rB Uc) lL(Bo Cu In Iu Ks Nm Qb) hA(aM An bC Kq Ky rZ) jP(aG As cH Mk Mp Ut) rY(aK bL Im Qd Qm St) Nj(Il Nk Ph Tk) hR(BO cR Il) rB(cH cW jM qT) rZ(bW cE Mj Qb) Qz(Kk Ph Rh) Tk(Ez Iv jY) eD(aG Iz mP) qV(dA Nb oF) Kk(oH Ow) Rh(iA oH) jY(Jd rC) NqiC loqU QuqT WnjG VvgW aKjQ} cC{eZ(Ba Cp Ct Cu Cv Dl Fy Jf Jv Ke Kl Kq Qh Sr Uu Vs) hR(bB bW Jd Jg Jo Jp Jq Ke Kl Pj Uh Vs) Is(eD lN pY tS uZ yL) qX(bX cB Jd Pj qV Tn) jL(bX cD Hq Kg Kn Pj) Qz(Bo Dk Jq Qt Tn) qA(Dg Kl Om Qu Uk) jY(Ji Jt Ny Rc Uh) qG(bU Jd Ju On) Kf(Kk uP vP) lL(lW mH Tn) yL(dN fP Mm) Hq(lN qQ) Kg(jT yD) On(Ed iA) Pj(rN tO) bX(eD Ly) qO(Mg Om) vB(Dp Ug) vP(rU Uk) AdRh FnqU MmrY TneD PzlN JdyE JvvV KktX VvsC PkuM dLuP dNtM fPrT mHjK iOwD} No{tV(Ax Bb cW Jt Kq Nm Nn oH Ul) wL(bL cB Cu fY Jp jQ Nn qW) wE(Ir Jp Jt Nn Nv Nx yL) tM(cF cP gL jP Ql Ss) rU(Aa Jq kR Nx rV Uf) uL(dN iC Jt jU nW wF) rO(Ed Hq Jg Nl Nx) rV(Ij Jt Nj vT) yL(Jf Jn Kn Qu) vS(cZ Dc Ef Kl) tO(aE Mg Ng) sO(cM cZ oH) wH(bL cB qW) wF(Jn Lj lN) Hq(qQ yE) Kk(tR yD) Vv(wD wG) eD(mE mH) tX(gW Nk) rQ(Kf kR) uM(Fb Qu) uP(aM Kl) AauW EftU ExkF NezA NltN UbtR RayE KgrN KonC OnkO PhqQ bZvU cRuZ yDoH rAvB} nO{aM(cJ Ex hB Kf Li Lw Ma Mm Ou Pd Qn qT Rc) cG(bV bZ Cp Ef Hw iA Ke Nl Ns oH Ow Tv) Kq(aS Cp Ef Hb Ik mH Ng Om) Ny(Ik iP mH Nf qX) Tv(aY Jl Mm Uh) Ji(bH Hc Ko Rf) Kn(bH cN lW Mp) Nv(Hc Ke Oi Uu) On(De iC mM Ns) lL(bL nR Oh Ou) Ex(bW Hc Hu) Lx(aV Ke Ow) qX(Io Mr Po) oQ(Jr Nj Pc) Bo(aS aY) Pf(Ns rB) cE(Bg Rj) cL(Aa oH) nR(iO rA) mH(Tz Ut) jP(cW Rg) oN(kI Nl) DgNj EfNx EtHb QerB QtoH JqaS LdiP OwbH OurA UhtF} nC{rA(Hu Jg Jk Jl Jr Jt lO Mp Mq Mv Mx Nh Nq Nw Of Ok Oy Qb) jO(Jl Kp Lh Mk Mq Mu Mw Ns Nv Nw Og) lL(dF GL jl lX mH Ou pF Qh) Ib(cE Jg Lx Mr oN) jK(bR bX cT Ou Vs) kO(Ad cH Kl nJ) rY(bO Jt Qa Qe) lM(bZ Ju kS oH) eD(Lh Mx On) mY(Oh Oi qX) iP(Kc Ld Lh) jD(Gl Oi qX) Tv(Js nJ) Hc(cH Oz) Ny(Ha iO) hA(Gl Lx) qU(aM Hw) kC(bP Qx) lN(Mt Oe) BotF DcQz EfOn EdjR ImiO IrqX JqQm KnnJ KpjQ aPcG bMjU cLiA gLlK jMoN} tM{Kr(Aj Ct cW dM Ef Ha lM Mg Mr My Nj Nr Oy Pe uZ wH) bW(aJ Ed Fw Ha Nn Or Qd vT wF) Ch(Ed hL Mp Nb Pe Pg wL) rU(aK Fn fP fY Pk Qz) Ha(Aj hG On rX tV) jY(bC Ed Fn Fw Mc) Pc(Aj Dc Fa Hb) Et(Dg Rj Up) Lj(Dc Hb Qh) Of(As bC Vv) Uk(Cq Ki Ri) fP(bC hL wL) Ed(Hq jE) Fn(bG qQ) Fw(dN Hq) Ih(Kf Uf) Jd(Id rX) DcIl DiUm PoUr EzNg LxaO MddN NbPh HwUp IsRm QzrY JlKf NvOn UfwJ aUqY aZrX hLhB tVoH iOwF} fP{hO(aK aV bG cR Fn iC iO Ju Kr Nj Rc) wL(aL bA bC bL cT Fp Jj Oz Pb qQ) qQ(Gl Hu Me Mn Nr Pk Po Rb Rf) uZ(eZ Hu Mn Nr Ue Vv) uM(Fp Fw Js pS Qe) qO(Aa Bb cU Uk) aZ(eZ qG sC) hL(Hv Nb uR) wD(cA Mp rA) uT(cE iO Qd) bC(vT yE) tX(cJ Kr) qG(Bb Ni) pS(dC oN) rU(Hu vV) yL(bQ Cs) rN(bV uU) vI(bG Fw) MdzG MpuO MtvH IheZ InrY JdrT TkjG aLwF bWzA cEvT cRvP dFzI dLuP dRqP fNiC tRjM} Kk{tR(Ba bZ Dc Jg jY Ki lM Pk wL) tX(bB bF gL Kz Pc Rb rY) uU(cL gW Kl Rj Ue uM tF) Et(cR Ib Js Lu Qz rB) On(As iA In Nj Rb To) tV(bB Dd dM Jo Ju Pk) vQ(Ad Fy Gp hP Jg Um) Kf(aR aW hO jE) wF(cE gL Kc Kx) rU(iP Jt wK yD) wH(aZ bF Ed) Bo(nF qV) Cp(tT wK) Nj(Jp Kq) Qz(Kq Tn) yL(Kg Pa) vB(aZ iZ) DdrR GzkI TonF RcjY JdqV JhtQ OyuV PhtS PkuN aCtT bPtU iCsC zGrY} Uf{vV(As bU Fn hG Hq Li Ma Me Nj rN Uk Vo Vv) tV(cJ Fr Gl hR jM Nr oH Pe Pf qP Rh vP) wJ(Af bG cF Ha Me Nk Of Oi qQ qY Uh) wK(Dl Ez jY Kp Nk) tT(dC Ed hL qQ vH) aZ(qP tO wG) eZ(Fn Mv Of) vH(aF cM Ik) vT(aF dN Um) Ki(qG rT) Ow(oQ wL) Uv(rW vP) cR(qO vP) hP(aI iJ) tO(Ez Uc) sC(Mr Rb) AsyL ExsK IhuW KzhO LiwL bLwG bUtU cBrN cFuX dCrY gWuM hGrT} nJ{rA(cZ Fw lL Mr Mt Mv My Ne Nh Nw Of Om On Pe Qe) lL(Ih Lx mH Nc Nl Po Qa Qe) Bo(bV hG Nd Ng Oz) Ef(bF Lx oN Vs) Iv(Gp Kf Ko Tv) kO(Cu Kr Oa Uv) Ex(Bg Ch Ib) Nj(cB nW oN) Ki(aY Ch Uo) Ow(nF Oi tF) qX(Hw Kn Tj) Tv(Ph Pi) Il(Dc Dd) Hb(jE Uh) Ny(Cs Oa) Vu(Is Qa) Vs(aP Mv) cG(aA aO) jD(Nk Nl) jP(Mn Ok) oN(As Cp) GptF IjKn OniC UtbZ PgjO PhqV mHjE nIhR} uP{dL(Ao Et Jp Ki Lh Ms Ne Nh Nj Om) Ed(aO As Ct dN jP jY Lh Mw Ur) Mp(Et Jd Kf Mr Nm Nn Nx Of) Jd(aY aZ bG Kd Lj Of Qd) Up(Ct dN Et Hq Kg Of Qh) Fw(cI Nx On rW) Jp(Jm Of Qe vH) Et(aV Hq Nb) Lh(Ha Mj Qc) Pe(Ex Ky Of) uZ(cF Hq qY) Aj(As Qe) Nm(Mr Of) Qb(Ms On) Qd(Dg Kl) Qz(hL Ni) Om(Ik Kr) NuNl MjHq MyKp JmNx KyrY NvOn cFuN qYvT qVlK} aZ{vP(bI cL Ct Ed Hq Jg jH JP Ki My Om pF Pk Ri rX) wG(Ad cI Dc jQ Ki Nu rW sC) vB(Ad bH cF cT Nk oH Ub Ug) sC(aU aV Fr Me wF yL) vV(Dc Dd Jp Qv rU) qO(bG Dc On Pj) Ad(tT vS yK) wH(aU cI jQ) rW(Dc Hb Kl) qP(Dk Hb Jh) Um(rQ vT) fY(Kf rQ) wD(cF dN) wF(gW qA) qX(Ki mE) qG(jH rY) DdyH MsyK JtsK OneZ aUwL bXrZ nRjL} kO{jP(Jg Kg Li Nu Oa On Qe) Tv(bX cM lY Me Nf nW) jO(hG Ji Mg Nv Nx Pf) jH(bJ cH Jg Ly tF) jK(bF bR cE cT Iu) lL(bP bQ hG lX mM) iP(Ld Lh Nw Qx) jV(It Jv Li mM) eD(Ii Jn Nx) Af(Jq Ny) Dc(mY Qz) Uu(Ad Jt) cM(Id lN) hA(hC Je) lY(Jl Oh) iB(lM mM) qV(cS cU) qU(kF kS) jT(Ms On) oN(cH Hc) MgiC MtnW HwmY TnQz IulM NyiO aLrA bFjY eCjE gLlN tFjI} Um{yL(bF bN Hq It Nd Ne Of rX Uk) iO(rR tV uG uZ vA vB wG zH) vQ(AW Me oK Pk Qd) zH(cB Nr Qb Qu) eZ(Jd qV qY) yJ(Dk Of Qy) rQ(bM Of Po) vA(iZ Qg Qz) vT(cE iC qT) Di(hO vH) Ng(rR vH) Qv(pS zG) aV(qO vP) wG(cL Ih) rU(iP pY) EtqG FbtQ MfvB MpqO NivU HquZ IlyH QurR KfrB UkfN VvuN bWwF cMuU cWeD gLsO gWrW hArZ wPoK qBqV} Kz{rU(bE Cs Cv Ed jM Nr oN Pe Uk Vv) hO(Cv dH Ef Et eZ Qu Rc Uu) rQ(Ad Dc jR Nr Pb qV Uk) eZ(Aj In Jh Md Rc) wL(Hq Mm Oz Qh uO) Tk(iZ Nj Oz Qn) Kf(jM qQ rB) rT(bM Jy oE) rN(dL dM Et) Fn(eD qQ) Kc(qX rB) rO(Cs Nr) uM(aN bN) NbqV IhtO HbqG RchR KpqQ LhuL WnbG UhuZ UgvA PbqO bLwF cItT cWeD dRvP hArZ iZuG} Pk{wC(Cq Fr Fw iA Il Im In Js Lj Lx Oa Rm vU) vS(CQ Fp Ih Jl Jp Kd Ky Mt Nk Pe) uM(Cq cZ Ha kR Mh Mt Oa Pe rU yL) rW(bO dR hO oN) tV(Ji Nb qG) yL(Jj qW Ur) vI(Mp Ow Rh) Fn(hO rO) dN(sK zA) tR(fY qP) pS(qV qW) rU(Dc Jt) sC(Po tQ) AocZ JiwP KrrQ NynI UkyK bCwG bGyH bWrT wKiZ iOzA qYqG} Kr{wH(bC Fp Ih Ii iO Lj Nr Om Ur vH) wB(dN Fy Jj Mg Nm oF qU qW) uZ(Dg Hq iO Jv Nk oH) Mm(rQ rT uL vH) Ok(rV rY uL uU) Jd(lL qI rY) Kf(hA lN qU) iZ(qG qO uR) qA(Aj Dg sO) Dc(cF Qz) eZ(Co Qz) rQ(Ju Lh) BbsC PouW EtrZ

Figure 23 Continued

LyuV UbtX HuvB JowE JtrB KiqX KjrU KnuL cWhA eTvS mEjF mMrA wJoN jDyL} bW{wF(cM cZ Hc jG Nq Ow rT Ss Uk) uN(aI aU aV dF fY iA jG Jl Md) vT(aC dK eF jH qT qV) fY(sO uG uM uX yD) yL(cM iJ Me Pd uM) wG(Hq It Ue uM) vB(Bg Ez Mw Ss) mP(Jg Ny On) tV(dF Mw Nr) Qz(rQ rU) aK(uX yD) uU(iJ jG) CtwP EtvP ExmS HqrY KirT LhvH OwmY aJtR aVyD cMuZ dHrV iOwD yHrW} Et{qG(cF Cq In Jq jY Mn Qn Qu Ri Tz Uh) qP(aL hO Io Jl Mn Nq Qd Uk) qO(fY Jl jR Qd Uk) Ks(eZ Ik rB vP) rN(cB gW iA Ri) Rh(iA Nj rB) vP(bC Dl Vv) Ik(vB yL) In(Ne Nl) Qz(Lu wK) cF(pS Tk) fY(Md Nm) hR(aW To) iO(wH yL) uG(cY lK) vH(aU hG) DlwK EdwJ GzsM UcrO KisK UhsC} Qz{Bo(Dc Ib Qy rZ Ua) Nj(Fr Ib Lj Qy rV) wD(bF iC Ih qT) Kq(aG Ex Nm) wH(aP pS vH) vB(bE Hq Ur) Qy(Dc Dd) wL(Mn Uk) wE(bE pS) qQ(Nv Rb) AdIb BbqO ExUt FnqU GzRc MdeZ NiyL UerQ TtmH IhrT InNy IouI IprU QvuO JuwK UvsC VvvS aGrV aLwG bCrW cGvO cMvQ cWhA dCrX wBqV rBuU qGjU pSrY} jP{mE(hC Jl Mq Mw Nh Nr Ns Nw) lX(Hc Ji Nh Pf Qe St Tj) mP(Ed Fn Kd Kn Qx Qy) mH(bX Jo Mh Nk oF) mT(Co Jf Qu Uk Tj) kI(bF cB Jy Ko Rg) mM(Ih Nk Oi Qu) Kl(kC kK) dF(kC nN) lY(hG Vs) nI(bL hC) kN(Nk Nx) MgnU NeoQ NhoP TvcW StmS iOwF} Uk{vP(Ad jD Ki Lh Me Ms Ri Wm) wG(aV cF cI cL oH Ub) vV(As jH Ny Oa Qv rU) sC(Ed hL Nn qP tO) Jp(qG rT vS) yK(Cs Ny Oa) wF(dC gW hG) vB(hG Ms qO) uW(cI Up) EdqT MpuX QvwH KgqG KiqX aKrQ cFwD cGrW fYhA gPhO gWwL iPqP sOqO} Kf{qG(In jU Li Lj Md Mp Oa Ow Qu Uv) iA(Ik qO qT qX Rh) vP(aK dR Ih Jl) Uc(vI vV wK) Uv(eT fY rV) qO(bN Js tF) Hu(rU vB) aK(uZ wD) gW(rU rV) rW(Js Qd) rN(Jl Pe) EdqX MdeZ NbsC IkbX ItqP RbfY RhrB OwrV aPvB eDnF nUiC iOvV} Gz{Tk(Ad Dd Dg Dl Ik In Jt Ly Nh Ph Qg St) hO(aQ bQ bX hR Hu Ns Pe uL) Nj(Ad eD Nk) cH(mE nD nU) oK(uV vV yL) Mn(sC uV) aK(jQ zG) hR(Jh To) oH(kE vH) vI(bM De) NbrT RbaE VvvV PeuV cLlY cReZ dRjR yLoN nWoO} nR{Tv(cG cL eD Jj Mm Uh) lL(cI Fw Ma Ph Rm Tn) lK(Ke Qn Tr tF) jK(aG Iz Ph) jY(cU Ju Qt) lN(aY cQ gP) oN(As Ef Uu) aD(jE jO) iB(eC Fn) lM(cW hC) EfOn EzjI ExoH HbjL RblO KshA aMjU bIjO cEqV dNqT} iO{wF(aF cB CS cV cW dC hG jH Kd Mw Nx Pa qA Ri wG) wL(Ad Dc Jj Mm Mw) wG(Ao eC Ed Hb) wD(bB cS Ms) zA(Kj Nj Nm) Jp(rR uL) Kg(tS uZ) AoqP DdtV MeuZ NhwH JtrV OnrR dNuL wElM} Jd{eZ(Af aN Ao hP jT Mv Of Qn Uv) rT(iC Kd Kx Oa Vv) Bo(lL rY) Nj(Il Ki) Qu(qI uU) cW(hA jY) tN(cJ Fp) qG(dN jH) vB(iC Kp) AsyL EzqX FruV NqfY MpzI RbqI KihR KyqV VvvV aUlK aWlL rUvP oHuU} Dd{tV(aK Bg Fr Hc Hu Nq Nr oH Ql qP Qy) yH(hL Qd Qe Up) rN(As bR Kd My) wG(cE Hq Ih) wF(aC bL Mn) Ib(kG oP) tO(Ed Ha) rU(Nq Qy) ExuV FwuM UerR RbqG QdyL UveT aPvB bLwL qWqP} On{Nj(Ed Ez Ph Up Tj) eZ(Js Nr Nv Oa Pe) Ex(aO bX Ly Qm) hA(Fn Io It mH) Hu(qG wL yL) Mn(hP yL) In(aG bZ) mM(mY rA) iA(Ik Iv) wC(Ed Fw) uG(Ha Il) NqvO MrrN QduX JsqG NvzG NwwL nUiC} mH{lL(bG hA jI kI mS nF nM pF) iB(Lj lO Mn Nf Qb) jE(jD Nd Nu) qU(mI Mm nD) Mg(eD jT) Tv(kQ Ma) hW(kF rY) hG(gW jR) LyQn NflO QbeD JjjO OhjV aYjQ bAjK bLjY dNqY mYrX kNrZ} rA{nU(cZ Fw Jl Kn Lx Md Mp Mu Ok Pd Pf Pg Qv) nD(Aw Ba Di Fw Io Ir Jl Nw Nx Po Qt Tz Uh) mE(jE Mt rY) Fw(cW Dc) mP(Ef Uc) kG(Ib jE) QtmM mIkS} Ad{Nj(Ax Fp In Jm Rh Up Tj) Nm(cF jE jH) Fn(jU qV) Nk(wJ zG) aW(hR jY) fY(jR qO) rY(Il Oi) BohP FwqV MnvO UcwG IbIn IhqG IkbX QutX KisM KotV LjyL TkcF VvvS aCcZ aLvB} Jp{rT(iC Ih Ji Qe) wL(cZ Nw Pe) qG(Rb rX Uv) rR(aU Js Nb) uM(Fb It Nr) vB(Nb pS Ue) Ow(vO wF) sK(It Ue) EdwJ MdeZ MpwK QdyL RmpS NwtV OfuG cBrY cMuU fYzG qTvV} Lh{vB(bF cE Gl iC Ik pS Uc) uM(Fp Ha Mr Nr Nv Qe) bG(qG rW vI) yH(It Nr Ny) Mn(wK wL) Mp(qG zI) wE(Nw Qd) yL(As Fn) IbnF IkwL JlyD aPmP aUvQ iAqG} oP{Ib(aQ aX bB Ha Hq Hw Hx iA Ii Jm Md Mn Nv Om Pd Pe Po Ur) Uu(Ao cI cU Of) jU(Nc Ne Nl) Nj(aI dD) MejO HuaL PcdC aAcX cHeC lYoH} nN{Ex(An Bg Ef Ik Ng Uu) oN(Hu Ih Ik kR Oh Rj) Ow(jK mY qY) Bo(Is Oh) Mp(aG Cp) Tz(Dp Lv) Tv(aM Ql) Uu(Ji Ny) CtKq WmhC GpKy LxKi MtIb KnaY} cW{rY(As Ki Me Or qV To) hA(Hv Kc Ky Of Rc) jU(Fn mM Of) Ex(hP vU) eD(Fn Tv) eZ(Of Tt) EdyL MphP TohR KptV aKgW aVjV bErZ mIqT qVkF} oH{tV(Hc Hq Me Nk qT Qy rU yE) wL(aC Kg qT qW rU) Mp(uU wP) tF(mM mY) nF(Id Qt) oQ(cH dC) BomS bXmU hGuU wFrU qWyL} Ow{nF(Bo cL Jj Lu Lx Ly Mr Mt mY Oa Oh Ud tF) mY(Ed Ir Ko Mm) kC(iP jK Qv) kG(Hb Ib) oQ(Nn Uu) mMjU} Fn{eZ(Ao JU Kd Ki vI) yL(dG Je Jl Md Ou) qU(aG Bb Rc) qV(aG Oz) HutV KieD PchR cFzG lXjQ mMiB mYqY rUvV} qG{Hb(bG Kd Qd Uv) Nj(Ih iZ qH) Kg(Ih Ki Ue) sO(iA Ju Ok) Ao(Hu wL) Ki(Fy Jh) rX(Hw Om) EzMg NrIj OkbG dNwL} Tv{mU(bZ Ed iA In pF) mW(bV jL Uu Wm) Bo(eD jO jY) lY(aM aO Ij) jE(mE mP) PimY bIeZ cHnU eDlW iPkF} mM{aP(cE cG jE qV) jO(cQ dE dI Ph) aG(hA jE jF) bZ(Lx qV) jU(Aa aF) kQ(Jq Ny) BokF MaoN VsqX aYlL dNhA} vB{aP(aJ Ip Ms Nu Uh) Ed(bL dN Hq) Ue(Ok Ug uZ) Hu(Ao Ii Mk) AaMm EzNg FpOk MsiC NkbL HrPj IpbC fYqO} Hq{Ed(tO uO wG) Ki(pS tV uG) wF(hG rB Rh) wG(jM Nc) wH(aC Ax) FwuO MswL NyqQ mPlL hOqO rBuZ lNrT} nU{qV(bJ hC Kq Qn Ri) lL(Kn Nl Oh Qa) qT(aD gP kS) aA(cL Lx) rB(Pf Qa) jO(Ny Qe) AajG aWqU} rU{vP(bC bF Fy iC jU Kc Ph) Ed(Hw Ue) Pj(aK gW) tX(qO qP) sC(aU qP) ExjM LyMe QdJt gWwF zIqO} kF{Bo(cH Ji Ml Nl Tn) Ex(Ik kN Mk Mn) lM(Aa aM Rj) Oi(hA Lx) cL(kN mY) MtqT VsiP cEmY} mE{rY(jV Mn Nc Nk qU qX) Id(lN Ni qY) rB(Mt Nc Qe) DcIn LxhA NkjE HxlL VsjY bRrX} lY{Uu(Jq Lx Nx Ny Tn) lM(aM aW bZ eC) jK(bF oN) IsaM JqkS NyrB VsiC aNqV hCjD} mP{jU(Je Ue Uv Tj) Gp(jK kQ) Jf(lK lL) CtlK EzqX UcNy IkqT JulO KgeD KnkQ NvaP dFoN} wG{Nb(Ao Ch Dc iP Ju Kj Ky) Ki(bF iC Kx) aK(bF iC) NnHu NuNl KxfY VvsC PjbL} Nj{Ed(Id Is Lx Pf Qt) Nk(cP Dc Ex Hc Kl) Tj(Kq Tn) MuUp NeOk IvKq dNvH} Ok{qO(aK dR In Jm) Ne(Hx Ii) Hu(tV wJ) In(Nh Nl) Qd(tO yL) oQ(hA lL) JlqP} Tk{cF(Bb Mz Pf Qg Qy Ue) jG(Ib jK Qg Uo) Ez(Dk Ng) MuIb IvKg} dN{yL(bN dG Hx uZ wB) uZ(Jr Oe Qy Up) Mt(wF wL) UbvA JtrV KovT} eZ{Uv(aO Oy Tt) Ch(In Up) Qh(Kd Up) EfNq ExrY MpIb TtUh TnKd JiOm SrOf} Ki{qX(gW iC Kx) Nk(sM tV) rY(hA In) sC(fN iC) LytR KcjQ aNuV bCrZ} hG{uU(Af As aU dD lK Oz Pe Qy uM zH) EduM NbtR bGuV} qV{Bo(aS aV) Dc(Fw Js) qX(Ed Fw) kC(aN cM) qP(Aa Uv) bGqA bPkI mShC} kG{Ib(lN Po Uv) Hb(jF lK) lN(Fb Oe) CpNy NlhW IheD IklL IojO} Ex{hL(Ct Cv Rc) hO(cJ iA Ug) Ju(sK vV) JkvA cAjO cIuZ} Jt{Qd(rO tV uX) Uc(uM uX) AawD MnhP RfqQ aLuZ eDkK fYqO} bC{Rb(wL yK) uW(Mp Nk) AsvT MesO QuwF JjwL UlyK PjrV cBrY} mS{Uu(cE Lx) aW(lM qU) hC(qT qX) QaeD KnlN aMlM bFlL jUoN} Dc{AsvH PofR FwqX MeuZ IbmT IlyD InbX KyhO WncF UveT} Vv{Ms(vP vV) cL(sC vS) qO(Pj sO) TtqX RivV cIsC iPrW} nF{oN(Fb Ib Pa) Cp(Lx Ny) qT(aA hX) BaCt KnkC OujE} Ph{fY(cA Mh Uv) Nb(rW sC) IkfR aKhO aPwE gWqO} kC{rB(Nv Pg) jK(aY cE) NljH KsjI OgiP cUoN hClL} rN{Kj(cB Kd Uc) My(bG iZ) Of(Bo Hu) EdjY KgaU} qT{nD(Ii Oe Oy) EdQh RbkK PimW mYrY nIiB} Mp{Mm(uW wJ) MguX IbeT NxzI cSqZ gPuN} aK{Ao(pS vP) Mm(tX vP) BolL dRwL iCtX} wF{Hw(aL Ql) aC(As Ua) AwNq aLjH dRfY} sC{Jv(Fp Kd) ChNq NbkR aUdR bGcI cLjY} hA{DemW EfmT NloQ IuWn KenD gPkK} kN{oN(aN iA) IblN HblL JjrB aYjT} Nk{bL(rY rZ) UeuZ cBrY jOvT} Hu{tV(Dg It) ChrW OfwL cMsO} In{Nl(Im Of Qa) Ne(Im Qa)} fY{vP(As pF) AovV JuKd PjqO} gW{tX(Hv Kx Rj) MmtV PanD} mU{Kn(aA Pf) CsjU EzjL NdTn} mY{Iv(Hc Oh) MnaA IbTt PerB} nI{DgKo JgUu VsiC aMjH aYjK} To{hR(dD Kq Pc) RcjY} Ik{Kq(aG cF) TteD KgvH} Qd{yL(Fy Kj) HwwL IiwE} Qv{wD(bE Kx) NbtV bLrY} Ky{wH(aP Hr) RcjY hOtR} fR{MeOr RbQg KcdK LdkQ} qX{Ed(Bo Qh) Tt(cA Iv)} uW{Aa(Nr Pe) EzNg aJaP} Ef{NqqA HcwB mTjU} Ih{IstX KgqP KnuM} Wn{BacF JsKg OaUr} qO{dR(Ao Pj) iZqW} oO{nW(Qt Vs) LjlL} oQ{MhUu NerY JllL} As{UbvQ OmwC} Ue{BbuZ KgvH} Hc{MvwB OfwH} Is{HauL RmhO} Jq{QnwJ aPuZ} Rj{cI(tR yD)} Uv{KpeT mTlN} Pe{NnyL MmwJ} aC{BocZ JuwD} nD{EdjU LdiP} jY{RcaW SrvH} rW{FwPa HbaL} CvQntV LweDmW NbPzrR IlcBrY IvgPhP RblWlO QbQhqA QglXlK NxUukP OfaPwH PfmIrB bGqWqP cShLvS

Constrained panels with 3 analytes, where 2.8E-8 >= 'AUC p-value' > 1.0E-8. Contains 4,830 panels of 27,619,476 total panels evaluated. : nT{Ib(Ap Ar bQ Gl Hc Jh kN Mr Mw Qx Rg Tr Tt Vv) dJ(aL bA bC bU cB dL Et Li nB Nx Uf) hC(aS dR Kd Lw mM mT NL Oi qX tF) Hc(aS

Figure 23 Continued

Figure 23 Continued lM(Iv mM Rh) Lx(kF rZ) Ni(rV sC) Kk(Kl wH) Pf(jO nO) cP(uT vH) cW(qQ uO) hO(Nm Qw) wQ(It rS) jL(Jp Ki) vP(Cp Kx) vT(aC jO) FwrA IdjD IkqG InqQ IvqZ SssC JtvB KfrB QnnA OkuL VvqT aYeD aZyK bWrT cLrZ nLqX qCwD} qC{Qz(aG aJ aK As bP Sr Um) wQ(Ip Kf Ki Mm No Qc) tM(eT fY Jp Pz uX vB) uP(Hq Ip Jq Jt Nm wG) Jd(Al Fn Ip sC Um) Pk(eZ Oz qW rB sM) fP(bV Dc Kk Pz uM) Et(cW gP jT Kk) Tt(Iu Kc Md On) Fn(Iq rT yL) Kf(cY qO Uv) On(iJ Mt Qw) Nn(rT wG) Ij(aK eZ) Iq(Cv Kk) Jp(aK rZ) Jq(wK yJ) AdqG DcKz NtwG NuuX IscC IvgW RbsC PzKp SrrT JtKk KisM KntT LhrX OkvP UmaN UfcG PjgP fYwL} Iq{rT(aH aW bP Jq Lw Mq Qn Rm tL) Et(jO uM vB yL tL) qV(cB Jd Ky Qv Qz) qG(Al eC Jd Rb rR) rU(aN Ez gP Lx Pj) sC(Is Mn Qg Rb) vB(bJ Nx Qc rB) Ne(In Ok qU) rR(cI Hr Um) vH(As bX Pj) Rh(uN wL) aZ(vP vV) qD(bR Jh) qZ(Nx Wm) tL(Ao Jj) rQ(bW Lj) BcrY FahP MeuL NlIn IhrV IruZ QgvI OfwH OkhA VqtF VvfN PhuO bCyL bJvW cCqX cMwF cWuN nOnA wLuW wQuR hCwC} nK{Tv(dE Jn Mj nJ Qb Up) Ny(iA iC It Kr Pi Vu) nL(Im Jk Mp No Tn Vs) Po(aW cC lX Nn rB) kC(Hc Jd Je Qx Qy) nC(Ih Oh Qe Tz) rB(Hw Nh Nt Qa) Jq(Ct kK Oi) cE(Ib rZ Uu) lM(aF aM dN) Ef(On Ut) Tz(Hb Oi) nO(Jl Mt) hC(hV jY) jK(cJ pF) kO(Rj Vp) lL(aX bF) BoHu CtVs DcEz FpUv MdeD MnkQ MrUu MujP IbcT IjIr IkNx KnPj UfoN aPcG bRlK gPhA mErY} Kk{Et(Bo Il Kr Ks Na Rh Up Tj) Cw(aW bX Kc Qy Rh Tj) On(bX dH Na Ql Qw Up) qV(Fn Jh Kc Kl Vt) Nt(Ad Dg Kf wL) rU(Hb Ok qD zI) Nj(Ad Kl Nk) Qz(Dc Jg Qt) Kc(bX Kz vB) Kf(eD iA jM) zG(Jo Oy Ph) yL(Ed Hb qY) vQ(Hw Pa rY) dN(uN vP) sO(Kr Vv) vB(bF Uk) DcbX DgNm NotV MgtL IbkG ToKq IttR JduP JpvU OyzH cWjG dMvO iCwG tXuN qDrT} cC{bX(cF hR iC lN Nh Nl Ok Vq) Qz(Dd Et Fr Jk Jl Vs) Ok(jY rB vV yL) hR(Bo Il Ju Lw) tM(Ch Ju On rY) uP(Fy Kj Nm Of) Hq(eD wD wF) qX(Bo Dc Ed) qG(Ao Mm Nj) Ly(On vW) Mp(nA nN) eZ(hP Nn) mT(hA qV) qA(Fn Jg) rX(sC Vt) lL(mP mU) vP(fP Om) AdQw FpKq FyuM MglN MmvB MujY NkNl UbqI HbqP JujL KfRh KzeD UkvV PjqO aJuX bWrT lYlM tLsC} nH{rA(aL cZ hW Jr Li Nq Of Ok) kO(Ad bF Hx Lx Ml Mn) Tv(aM Ct dC Fw Jn) mY(kF Mr nJ Nr) tF(bF Kn Rc) nA(Ii Uc Uv) jO(bL Mt Pf) oN(jK jM Nl) Ik(Kq Uh) Ny(Bg Dk) rB(cF dI) qX(jD Me) jU(gL Nh) rY(cT Qa) lL(hC Po) MlUo MtiC NdSr NjKi NlRc IbbF TnIv ImiO QehA QwcE KfnO KnPh LdiP OehW OnnL aGcG aMqU aPoP bBrC bLrZ bRjK cHnR cMqV dNlM} No{wL(Aj Bn Ib Ir Mz) wQ(aX Fn Fy Gl jV) tM(bB bC bG hG nW) rU(Ch Je Jf Kx Ms) rO(Iv Ky Li Mp qD) uL(hO Om qW tF) wE(Ed Jk Nc) rV(Et Na Nl) qQ(Ar Sr tL) Ba(vS vU) Hv(vW wF) tO(Mh Ph) tU(Ib Lh) tV(bI Im) yH(Dd Ii) wH(Ar cF) yL(cV Fy) uM(Ql Un) FwuP RbsC QvzG JktX JsvH KisM OnnL VqhP aPvS bBtL mErB nAkO nFoN iOuZ qXvB} qD{Kz(Et gP Hb Jk Mh Nn qG Qy) yE(aE aZ Jj Mf Nj Ok) wJ(Et Kn Nm Ph) It(rT uW wK) Jt(aP qA Um) gP(Jd Of Rb) wQ(jH Ua Uk) sC(aZ rX Ua) vW(hB jL qV) Et(Rh vV) Lh(Im Kr) On(As iO) Pk(Fn Qt) fP(Ow uM) qG(Ez Me) uP(Hx Mm) uW(Fr Ih) BcqV DiUm DlaG NmyJ NqvB NtwC NuuG MsuM MuTt HcqU PzaP JlVq JpcW KcwK KxwG UfaI bWyL eZqY} nO{aM(dH Hc Mq Oh Or Qt Tz) Ji(aO aS Bo Ou Tv) Nv(aO cY Hu Ki mH) qT(aD aG cQ kS Uv) Nj(cE cL Qt Uh) Ny(As aY Qy Uo) Lx(As Cs Is) Tv(Bo iJ Mp) Kq(Fy kO Nk) Ow(cL Nx Ud) cE(Ct Ef Kn) cG(aF aG Ma) nA(Pa Pb Qb) oQ(Et mY nU) Kc(Bo Jl) On(Og Uf) cH(cT Oh) cL(iA mM) DdIb WmMn JqUo LjaY NxUu mEqX rAlL} Nt{Kq(Hu Ik Kf Ly Rb) Et(Id Jd Rh) Ib(Qz wL wQ) Pz(rR tV yL) On(aG hA iA) uP(dL Ji Jq) Ad(Lu Qt) Mh(yH tL) Nj(gP Qt) Jd(lL Ne) Jg(Id Nl) Qz(Dc Fr) Lh(qG rO) dN(wD tL) eZ(Kl Uu) wL(Je jQ) wQ(bG bZ) wG(Jp Sr) wH(Dk Dp) wF(Ii Ph) uX(Di Om) AauW BbqX DlqG EfvP FwvW TteD HbrW IztM QyJt JvrV KitV NvrT VvsC bWyL gLwD} nA{kO(Fa Is Jg Md Mj Oz Pa Pf) nL(Mp Mx Ok Up Uv) Ef(Cq Kq Po Tn) Oi(Ma Oa Tv Ut) nC(Mt Tn Uc Uv) Lx(jU Mu Rf) rB(aL Nn Pd) Po(Gp Pe) Tv(Jj Ph) Il(oH Ow) Ir(Iv Lj) Ny(Cp Qu) On(jU Mq) Oy(jP jU) aR(Ez Pj) BomM CqJj CtVs FpUv NfPg IkOk HbKq IvQa JqQl NwkF OhmY aMqX bFrZ cVhA tFlL rYoF} Qw{rZ(Ad cE cW Fn On Po) Qy(Ad Dc Nl On) eZ(Cp Fn Jp) tO(Lx Pe tX) tL(Na Oy Rj) qO(cR dL gW) uM(Fb Na Rj) vH(Mg Pj Rm) vV(Af Lu zH) Qt(Ki vW) Kf(qU rB) mH(Lx Uv) qX(dC Lh) rY(Mw Nv) rN(Jo Mr) AdRh CwcN DpwL EtLu NjNk HbvP JdqV JgrB SsoP KltM OnhA PdtV aGqT cEwG iArV iCrT iPkO wDwH vTvO} aZ{sC(cY Dc hR rX Uf tL) qP(Dc Ed Kg Kl Pj) vP(Ao dN Fn Lh wH) wG(hR jR Pd Pk) vB(Fb jR Jt vV) wQ(gW jQ Mm) yK(Fp Lj My) wF(bW bX Nk) qO(Bb Ij Kg) cW(rY rZ) wL(gW oH) jH(kO vW) qG(Hb rX) AdhR EdqT MevV MytM NkwE KzrQ OkrZ PhfY bWvA bXrY cLrW dNtL gPuG mPjL nDrA rXrT} Vq{hA(aG Bo bS eF Hw Jt Lh Li Lx Nx Qv Rc) jY(Ch Di Dk eD Jg Jy lN Ne On Oy Qu Sr) hO(Dp eF Fp gP jI Ma nW) hL(Hq Nv oK Pe Uc) hP(aV Cq eZ Vt) iC(Je On rX Ss) qV(Aj aK cY) Tt(jO jT) iA(Jd jR) qU(In lN) lK(qX rX) FnrV TzrB IvnW aUjU} vW{Ed(bX cP Ne Nl uP uX) Kr(aS bA Hq Ms qH) Oa(cG Dd Jk Ne rX) fP(cL dC hO Pg) Ad(aN Ha Pe) Ao(aP Hu Nb) Fw(Hq Jp uX) Jd(bC Me sC) Uf(Mj qO Qv) Ax(Jp Ok) Bc(cW Ky) Et(jQ qG) Fn(Nm Ur) Qz(Aw rX) ChNr DcJs DdPe FpFy MeQy NaaO NkPk ImKf QeJp JjaH RjbC UvdN hGuU} Nj{Nk(Ba Bo Ed Ib Kq Qt Qu Qy Qz Ss Tn uL) Qz(Bo Cw Jd Kq Ss Vs) Ad(Fw Hu Iv Ml) Ed(Im Jq Vs) Tn(Il Iv nC) Qt(In nN Up) Cv(Fw Kz) Nl(Et Ok) Kq(Il Kr) Ny(lY oQ) qG(bG sO) DkGz TjOy FnyL FwPa NhOk JhcF KzqQ UkwG UfsC aCwH aInF cWjG nNoN rBuU lLoQ} nL{iP(Ip Ko Mr Ok On Pa Qe Tn) lL(aJ Dd jI lX mY nJ nR Ut) Ny(Dk Ez Fp Ij Iv Oi) rA(hW jD kG kS Mq Ur) Tz(jI qX rB) gL(jK lK qW) Cw(jD lN) Tv(aO Js) On(bW Ib) tF(nJ Uh) jH(aE bQ) oN(cH cM) BajP ColM DdjI PokO TnnC QvKn UvnJ aMqU bBqX cJjK} rY{Kr(Bc Ii Jt Kn qA Uf) Bc(Hq Mm rW Tt) iO(fY nD qA rW) Jd(cB Il Oi) Kz(Kp QG) cW(aN It Js) nC(Me mY Vp) Jp(Ky Up) Jt(aW Oi) mP(cG dD) tM(Ch Rb) AdJs DlOi MpzI TobR TvIn IlbX JgkO KpuP NymE UpnJ VpkG VvqO bUnD bWcF cZmW nUlL nFjI} nJ{tF(cJ Ib Kq mM nC Ok Up) kO(cM Ki oP Ow Tn) lL(nC nR oN qX) Iv(Al Kr Tn) Ut(Ef Na Nq) oN(cS Hb nC) Bo(aX kQ) Dc(Oi Up) Ny(bZ pF) Ow(Ki Ql) bF(aA Bg) rB(Mp Pf) rA(lO Ur) jP(Uk Uv) CoOf CsLx EfNv EzKq UuVs OzPj aMqU cLeC} Cw{Qz(Ib Ko Lu Qy) Tk(Mh Mu Mz Uv) hA(Bo Fa Io Lv) rA(dE It Iu Mw) jO(aU bC cD gW) Rh(iJ In Ne) jL(aF dF Up) qX(Ha iA) qT(Mw Qb) rZ(cA cL) lL(aR iJ) TjPh GlqU IjjU IknW QhjM KyiC WncG aCbE aKgW aVqV cNjY dRjF nCjD} Na{qX(Ao bC cF Ch Dd De Nx Qx Qy Ut) rT(bO Hr tV) Di(sC Tk) Nm(qZ tS) On(bX rB) cU(qP tT) qU(Qu qZ) tM(Ha Ss) tL(cW pY) uL(Mf Pj) EdrA FrQz MrwG NluM IbTk TteD TneZ QavH QhlN KqvV LduZ OevB OkiB UkqT bAtV hXzG iCsC jUuX} Et{Nl(Hw Hx Ii Js Oi rB) Ne(Hx Ii rB zA) qG(jG Kz qY wQ) rN(Dd Ky oH Rf) Rh(hR Qz vB) qZ(Ik jG Mn) fY(jF vV) rB(cW jT) qO(aL Vv) vP(Qu qW) AavB CquP NbuU NhIn UeuZ QdyD KdtM KrjU UoyL UkvV aVpS cJwQ iJsM oHvH} fP{qQ(Fa Hq Ki Ks Mr Qe Uk) hO(cT dF Ow uT wB) vH(Fp Md Nl Ub) eZ(iC Mk Of) yL(As Fp Ki) cR(qG qP) dG(rN uX) nR(jK lL) qO(gW vP) MpyK IvhL TkhB aKtX bCwH bVpS cEzI cJwQ cUqP hWtL iArN rAvV qVkG tMrX} Um{yL(Bo Jh Jp Kf Ph vH) rR(bI dM Ih Qz) Me(sO tQ yJ) wF(aC Lj vU) rU(Jt Kr Pj) qO(Kr Po pY) vQ(bA Js wL) yJ(Fr qW) zH(aN Jm) vA(Fp zI) vH(bF dN) AwuZ FnhO NrvI MfwQ IbpY KfqG bIvO bPrQ iOzA jKkC} nC{Ib(bF bQ Iz Jy Kg Nx) Kn(iO Qv Rh) lL(bQ cT Ut) lM(aM dN eC) As(jH jQ) Tv(Il Ph) Ki(cL nN) Oi(Hc Tn) iP(Im Uh) rA(cZ kG) qV(bR cW) lK(hG oN) BolX DdjI IkQt JekC NypF OktF aCqX bAjK bLjO gLjU gPhA} Uf{tV(eZ Ik Mn Nw Uc) tL(cU dC Hu Me) sC(As bG Uh vT) Uc(qQ wJ wK) wQ(aU Hu Jg) tM(As Ha rW) vH(jY rX Up) Qe(uP vP) wL(bL Md) LxmS LywJ NftT QyuW OipS PetO aKrU aUuG aWvP bGvV cZvT wKjM} vB{Hu(aC aO Aw Ch Jg Mm) Bc(aG Ez It Lh Mk) Io(Ad Ii Jd Jt On) Kr(bC Ib Jo Kf Kj) Lh(bE Ed Mj Ut) Jp(aP Fp vH) Mm(Fp Ue) Ok(Ik jM) aP(Jj Ur) HaIs NrJd NkbC UcsM aKiC bWcZ fYvP} Kz{hO(iC Jp Md Qh) rQ(Fw Io Kr Kx) eZ(hP Of qW) qB(Cv Kp rT) Dc(qO rN) In(On qG) Kf(jP qU) Tk(cF Di) rU(Hr Ly) rT(cL Pk) uZ(bI Mp) DdrN EduV MdrO RbqO KieD WniZ UvtL PhrV aYnN gWvP wQqU iPqG} dN{tL(Cv Hq Jt Ju Mm Nr Om qG) tM(aW hO Lx Mp Pe Pk qV) lM(lW lY mU) Ub(vH vQ) Jd(eZ hO) wL(aK Nk) wF(Md Mn) qV(mP mT) qG(Kf sO) uZ(Hc Ju) BcrU NhzA hAkP mMqU iOwD yLoK} Kf{qG(Fw Iu Ki Mr Nm Nu tL) rV(aU fY Mp Oy qO) rB(cW Kr Ks) rA(Ed Fw iA) qO(hO Nu Nv) Ik(aG cF) aK(jR vV) rR(aU Pe) AstM NuuP UbvQ UeuZ ItvP QdvV JlqP KytL OwrO} Uk{Fw(qO vP vV) Me(vV wF yK) wQ(Mk Ms Ny) sC(hR Rc uI) uW(Ed Jl Mj) Hu(rW vS) aG(qT uZ) yK(Ms rU) tM(Pe Up) oP(iC jP) BcuN FneZ GzhO JdwG JpvH RivV NyqP lYqV tTjD rBvP} uP{Kr(Aj aM Dg Jg uZ) Up(As Ch Dc Kj

Figure 23 Continued

Oy) Fn(bG Ki Nu) On(Nb Pg vH) dL(As Bc Jt) Aj(Mp Nu) Ed(Ad Me) Jd(Fp Ow) Lh(Mt Nb) Of(hL Jm) Pe(Mn tV) FwaU LxaO NiHq JsKg}
Qz{Dc(aR Ib Lj Lu) Ad(aW Nm Qy) Ib(Dd Ki) Tn(Ko Wm) Ih(sC wE) In(Qt Ut) Ou(pS yL) Vv(wE wQ) eZ(Ch Kd) BohA LuTt MduV MwrU
HrrR HvwG QyKi QvyL KqKr LjrZ cWjG fYqO wLwQ} kO{mY(Nl Ny Oh Qa Rj) Mt(Jr mS Qx) lL(aM bA eD) Tv(Fy Ug) iP(Hu Kl) qU(As cK) lK(dF Ut) lO(Ao oE) AdjD NrhV MnOn TnbX IkKq IslY IvKo JroN aNcH bJjI cGjH cTjP cYjQ} nN{Mp(aC aS aY Bo dI Qx Uo) Wm(bF Ji Mn Ny qT) Bo(Jq Mk) Or(cM nI) aY(oH Tz) oN(jK Jq) AsjI EfUt PoaM MwKq HwTv IlKn QhOw KicG KlUu KyUo OhnW UrrB kSlM} qV{mT(aO aP gP hB iJ) Fn(bL eZ tL) nR(dM hB Uu) nU(cJ oH Uh) Fw(qP rA) Nb(Ki wG) bG(cW qX) cF(kE mS) iA(kI lW) kG(Ao kS) HutL JdqG JsKi bRmS dKmP nFoH iOwF} Pk{vS(cH Fw Me Qy) eZ(Ef Fn Mk) zG(cM Oa Qh) wC(Jl Kd Nu) sC(dL Ha Lx) uM(Fw rO tR) hP(Bc Ik) yL(As Wm) NbwG UesM RbrU JhrW KyvI OwyJ aKuN fYqO rBuU} Bc{sO(fY It Nk Vo) yL(Lh Me Ms) uT(Mp Oi Pe) Up(rU uZ) Pj(rV vT) uL(Rf tV) uG(Ez wL) uU(aK Fn) AozH FbuM HatL ItwC KgrR KirC aFuZ aNrP rXrW vAvT} Jp{rR(fY Ky Lx Nw Uh) rT(Fw Qd Uc Vv) uM(Mf Qd Uc Up) wQ(aC aN) vS(Qy Uv) EdeZ NbsC UewF UcvH QeyL NwuN OwvU aKrU bLwL cBrN cZwD fYvV qTqP} mY{Oh(aO Ij In Js Oi) rB(Md Pf Po) Iv(Lx Ny) Ow(bH tF) cG(bZ tF) kF(oP oQ) AaIr IdaN ToaM TvkS IkNy HbKn KicH OihX PfaA aOcL nDrA lLoN} tM{Po(aO Ch Vu) Ju(Fp Kd Pc) rU(Cq Jd jH) Ef(Lx Vs) Kr(Ms Ns) On(Mr Pg) Pe(Jq tV) uU(As Rj) AdKd AorX EdMy LxVu QdKg QebW JdLj QhJs qWoH} nR{lL(Bg Dc Ub Uu Vv) lK(An As Bg Cs) aD(hA iC jY) qW(aG gP tF) jK(bC Ct Un) qT(aP dM) AojI AsjH IkcG aGlN cLoN tFiO mHrX} Ki{qX(aS Cv Io Pi Rj) sM(Ao Ch cQ hG) sC(cE cL Kx) cH(kP nU) FnhO FypS NrtR MgqG NgTk KruZ VvqT cWeD cZsO fYvP iPrU} mM{rA(eC iA jO Wm) lK(An Cs dH Vv) jO(bZ cF pF) jU(aG bW kS) Ub(rB rZ) cJ(jE jY) tF(cZ lN) LxaP aEjM bZjV hAiA qXoN} eZ{Fn(aG bG Mk Qu Up wF) Jd(cW dC Nk) Om(Af Md Qn) On(Il Lx Md) Qu(aN Ez) AdaN DiTn MpLh UewF TtbJ IjKr} Ok{Nl(Fp Hx Ii Jm Js Qb) Ne(Hw Js Nn) qG(Hu Js rV) EzqX MehR MnwJ NbwE RbyL QdvS JiTk PehP aUqO iOuZ} tL{qG(Ad aO Kg) Dc(As Me) Dd(Ed uO) Mm(Ky Oa) Ue(cS Hb) bC(cF Hq) bW(Ez Mv) FpPj NunW HwJd JvKr LhaC VvsC cMjO} cW{hA(bG Dd Is Kg Vv) Fn(jD qU) Tt(eD hL) rZ(aC Lj) EdrA NkwQ UbvI JduN KxjG OwyL VvvS aKiC mPhW jOkP} Ad{Ik(cF cK eD iA Ib jE) Nm(bX Fp Hu) In(aG bX) AsqG FnrB MerV MpzI KdzG VvvV aCbE aKqO cBrN} bW{Vv(vV yK) pS(cL Qv) rW(Pj rZ) yL(iO Ky) NqtV MuvI MwwQ HquM IpuX QtvA PdwF aGuZ cZuG iAvU tRvT} jP{kI(Al Ba Co dF hC Vv) oP(Nl Uv Vp) bF(lX mE) hG(kC nI) AwlX BoOf NloQ KrwH dFlY} On{In(Ex Ib Ne Nl qG) iA(Hu Nb) kF(Oi Wm) uG(Kd Pg) NkuL UeuZ ItqG RiUp NyyL cAhA} wL{bC(Mp Ms Oa) Hw(aK Rb) Lh(aP Ji) MmHr MsHu HqqA QaPe JoaK aCgP aUqW aVrU cBfY hPoH} rU{vP(cE Dg Kx Pj) gW(Iv tX) vV(Ju Ky) BgDd ExcS FnyL GzHu StKj JtjM KlKr zIqP} cF{Tk(Dp Ez Jt Ky Me Ua Vs) Wn(Jk Pf Ua) DcFp FnqQ NkNl cAsC oHuN} mP{Tv(bZ Ed kS pF) kQ(jM Jq Tn) aR(jK lL) rZ(bL cT) AfNy MtIb aGoN dDhV} nD{rA(cZ Li lL Lx Mr Nh) qT(Hv Iv Mn) qX(cG cJ) NehR JslL UorZ} iO{zA(Hb Ms Nx Pj) wF(It uW) kF(cG Lx) uZ(Hq Nn) AorV GzlL UpsC PhtT} Kr{uZ(aG bB Jq Ns) Kg(rS Tk) rQ(Kq Om) ItwB JuvA cErZ sCyL oHuU} aK{tX(bB bF cA Nk Pc zI) hO(Dd Kg) DcjR ExgW HbqO bBwQ dRuU} Jd{Jj(uM uZ) BoqU MpqI JlzA RfqQ UveT aVlK aWjY cVpS iZqO qYqG} Lh{uM(Ed Fw Qd) Lx(uL wE) Ow(hO vQ) MtwE IhqQ QeyD NvwJ jYvH} lY{Tv(Hb Mv) Jq(Cs kQ) rB(Pg Ut) BoMw LxkS OwoH UorZ UucG dClM} wQ{Mm(bZ qQ) Nk(bG jO) Hq(qQ Wm) CuyL MpzI IhbZ IpbF VvjH hGiZ} nU{rA(jD lL lO Vp) DcqT JtrB aWjU cGlN lXlL mEqX mHhW} nF{Ow(Il kC Nx Oe) Bo(cH Kn) aW(jU jV) LxoH NeNy KnPc} mT{Uo(Fn oH) eC(jG qY) LxbZ aWiC bAhV bXrB dDtF jUoE} kC{iP(Ky Nk Nx Oz) oN(cM lK) LxrB KncB qTkN nWoO} kG{Ib(Cq Oi Rm) hW(Nh Ua Vv) OwtF VvqT aMiB rAjO} sC{Jv(Lj Nb Pe) Vv(As uZ) AwNq PoRb HabG NbKg KxjY} oP{Ib(Qb Qx Tt Uv) Ct(Jr Tv) DlTo GzRh UtlK aPnW} oQ{hA(Is Lx Ny Uo) Ow(bO Fy) IvlL UhjD UulK kFkP} mH{jE(dK iB) qW(aE Ue) CpeD MmrZ aDjD hGjK qTkK} Dc{Me(uM yL) AsyL FwqT HafR NdmU NlIn UpqG} Gz{Tk(Cx Jg Ky) LyaE HuIz PzjM LdrT cRrW} Hq{qQ(Fn Oa) NlrT JluX UpwD fYvP qAwF qGrX} Jt{Nq(hP tV) AsrV QduL PetV hOwJ hGvH jYrN} Kg{Qd(qG qO vP) MnvH ItqG JiTk UvrV gWqO} kF{Bo(Hx Is Nf) Lx(aM nI) MthC NyOi cEjK} Nb{Tt(nW tF) BorZ EduW HbwG KjrR hGuG} eD{Fn(aG bL Tt) mU(Mp Og) IjmW UvnI} In{Mr(Ne Nl) PoNe NhQa IstX KcfR} Ph{qP(Ed Fw) UerV TvnI fYqO nWoO} mW{rC(aO dC) EzTv dIhX rBoH rZnY} As{iP(qG yL) UbyL OmqG aCvT} Mm{MeuW RfvT cBwJ cJtV nWoO} Vv{FpyK cIvS nIrB tTjH qWvP} bG{Tk(bO Lu) AoqG QvuX cIrN} Hu{tV(bX Jg) wG(bF Ii)} Ju{FnhO aCvU fYvP hGsM} Uv{AjeT AosM NdmU KyhO} Pj{aP(hO qQ) NlvH PerV} lW{CsJq FpNy KnKo QnaM} mE{Nh(rB rX) MerB IkKq} Dd{ExrT UevH QeuM} Mp{AluU KjrN sOqG} Hb{TvmS ItqO NwrN} Is{Ih(rO uL) nIiP} bC{MeyL NkwF aUsO} cA{MywG RcjY hGuU} fR{ToLd KccM aOcL} lX{aMlK hClM jRlL} wH{EfNq MnlM IiQd} kI{aPlM cBlK cQjM} kN{oN(dH eC) UghW} oO{LwnW MdlL NdoN} Ed{aGqZ sOoH} Ex{cIqI qQoK} Fn{NyqU cEhA} Fw{UeuZ IivP} Tt{IbkE KcqX} Ik{Kq(aR iA)} Rb{MevO gWtX} Kn{LjuM mIrX} Om{NqqP UeuZ} mS{AaaR bRjD} mU{aDrC cBhX} AoMnqZ ChdLqA EfHcvU NuSrvH NkdCtV NlRcjY JqOauM aYjKkK bFgWtX cYnIjR iChGuU wFqWoH

Constrained panels with 2 analytes, where 1.0E-8 >= 'AUC p-value' > 0. Contains 53 panels of 155,299 total panels evaluated. : Cw(hL hO qG qQ rN rY uY vH wQ tL xA) iH(Ad eD hO jL oQ qX rT uM wH tM) qT(kO mZ nC nD nH nJ nL nO nT nU) nT(cG cL oN) nA(Lx Ny Po) Kz(pS vH) Us(qQ wQ) Vq(rU rY) rA(kO mZ) BcrY IcxA HfuY KnnB OwnN dNvW qUkO kFoN Constrained panels with 2 analytes, where 1.0E-7 >= 'AUC p-value' > 1.0E-8. Contains 33 panels of 155,299 total panels evaluated. : iH(Ic nB oP sC tX) uY(bW dN Kz Us) qX(kO mZ Us) xA(Ap Pk Qw) Cw(eD jP) nT(cE dG) qG(Ap Et) BcwF IcdJ QwqQ NvnA UmyL UssC VqrZ bWvW dBjL nNoN mYkC qDuP Constrained panels with 2 analytes, where 1.0E-6 >= 'AUC p-value' > 1.0E-7. Contains 59 panels of 155,299 total panels evaluated. : nT(aY Bo Id Kq Ny Ou Qn) iH(iO Jd Kq Ml Nj On) uY(Ap Ky Pk Qz Um) Nj(Ad Ic nB Ok) Nl(Et In Nk Ok) Us(On rY wP xA) Cw(jO Kk qX) Ne(Et In Ok) nA(Ir Jq On) Db(jL qX) Hf(qV wH) Iq(tV wL) ApeZ DdxA FnvW NtKq NhIn QzqQ OwnF UfwQ VqqX bWtL dBrX mYnL mZiB nBrA Constrained panels with 2 analytes, where 1.0E-5 >= 'AUC p-value' > 1.0E-6. Contains 169 panels of 155,299 total panels evaluated. : iH(Bo bU bW cE cF cH cM Cw Dc dD Ed Et Iq Iv Jg Kk Ly Nf Nl Ok Pe Pf Qu Qz tF) nT(bW cH cN Dg hB hC Kf Ky mY Ow pF Tv Uc Uh) Qz(Bo Cw Dc Ic Nj Qt Tn vW xA) Db(eD hO qV uY wB wH wQ) Nh(Et Hx Nj Nn Nt Oi Ok) Iq(Ne Nl qC qD uZ wD wF) nB(Ld Ny OH Ow qT Tv) nA(Mr No Nw Om Pf Pg) uY(Bc fP Jp Kr Qw Rb) Nj(Ed Jd Kq Nc Nl) dB(eD lM qV qX wH) dJ(aC bX cF qV Qw) mY(kF kO nC nD nU) Nl(Hx Ic Io Nt) Hf(eD qU qX wQ) Us(lM lO qT qV) mH(lL qU rX rY) Ad(bX cF Nm) Ex(hO mF On) Ic(bX Et Jk) mZ(Mt Oh rY) Bc(tV uN) Bo(kF nJ) Ne(Hx Nt) Qw(On wQ) Kk(Et uU) Kz(zG Tk) Uf(vV wJ) bW(wL yL) nO(cG rA) tM(Kr qD) NorO NaxA HquP RcjY JdeZ KinH NynK UksC aCcF dNyL fPhO mMoN kOlL Constrained panels with 2 analytes, where 1.0E-4 >= 'AUC p-value' > 1.0E-5. Contains 393 panels of 155,299 total panels evaluated. : Nj(Ba Bb Bo bX cF cP Cw Db Dc Et fP Hc Ib In Jy Kl Kz Qg Qt Qw Qy Ss Tn Up Us Vs) iH(Dd Dk Fp Hc Je Kl Lj Lw mT mY Nc Ne nH nJ nO nT Nx Ny Oa Of Oz Qt Rh Tn Uf Vs) nT(aM Dc dF dH Hc iO Kd Ko Lx nJ Nv nW Oh On Or Pf Qm Qt Ri Rj Tn Tz) Ic(aP aR cL Cv Cw Dc Dd Ib Jg Kf Kr Kz Ne Ok On Qy Tn Vq wJ) Ad(aC bF cE cK cL cN cP Db dJ Hf Ib In Kk Na Nt Qw Qz Us) Qz(aR aW Db Dd dJ Et Fr Hf Jd Ki Kq Kz

Figure 23 Continued

Lu Nt On Ss wQ) dJ(bR bU cB Ed fP Jd Kq nC nH Nl Ok qW rC tX vB wG) nB(Dc Im Iq Ir Ji Kk kO Mr Nr Nv Nx Oe Po Qb rY tF) On(aG bO bX cC cF DB hA iA Kk nK nO Ph Ql Ri) bX(aC Ap aZ bF cF cT dB Dc Is Ki Nl Vq) cF(Ap aZ Bb bF Bo cC Db Dc fP rY Tk) mZ(Hf Id Ik Ki IL Lx Ny Og Oi Qe) mY(Ir nH nI nJ nK nM nO Nv Oh) aC(Ap bE Bo cB Cw Db Dc Dd) Qw(Cw Ib Jh Ki Nl Qt tL) fP(eZ Iq Iv qQ vW wQ tL) nO(cE cL Lx Nv Ny oQ qX) nK(Ir Is Lx Mn Mr Mt Tv) uP(Jd Lh Mp Of Pe uZ wL) Bc(sO uZ vW wL tL xA) Tn(Fp In Kk Nb Nt Us) nA(Md Mn Mp Nr Nx Og) qD(gP Jp Jt sC vW yE) Db(Kq Ly Nl qU sC) Kk(Ap Dg Jg Kf Lh) Us(Dc Ib Is Kq Nx) Vq(hO hP jY qU rX) qC(Jp Jt Lh Pk Tt) Et(Ks Nc qZ Rh) Kz(Cv hO Kc uZ) aZ(vP vV wG wQ) nJ(Ki kO rA tF) tL(Dd dN Hf Um) Jd(Ki Nt uY) Ok(cC Nc Nd) dB(hR qU rC) mF(Bo Mt Ny) mH(jE lN rZ) rA(nC nL nU) kO(jV nH Oh) rY(bR cB cW) vB(Iq Lh Um) Cw(Ph Rh) Fn(eZ yL) Gz(Ly Me) Ue(uY uZ) Hf(qQ xA) Kr(vW wB) Uf(vH xA) Pk(uM vS) oP(cH Ib) ApwQ BoqV DduY NorU NtKf MtlY NaKq NeHq NhIo TvnH IqhO KiqX UmwL UveT cWhA tFmM nCqU hGuU sOqG

Constrained panels with 2 analytes, where 1.0E-3 >= 'AUC p-value' > 1.0E-4. Contains 926 panels of 155,299 total panels evaluated. : Ad(aZ cB cT dE FP Hu Hx iA Ic Ii Ik Il It Iv Jm Js Ki Kr Ks Ky Kz Lu Ml Ne Nl nT Oi Ph qC qG Qy rB Rh rY Up Tj) bX(aR Aw Ba BB Bo cB cC cE cL cP Cw Di ED Et fP In Jd Jg Jh Kc Kf Kq Kr Lu Ly Mt Ne Nh nT Nx Ok Om Qg Qw rY) Us(Ap Cv Cw Dd Dk Ef Et Fr Hc Iq Jd Je Jg Jh Jk Jl Jt Kf Lh Ly Mu Ne Nh Nl Oc Of Ok Om Or Qt Qy Qz Tv Ut Vs) Qw(Ap aR aW bA Bo cC cN Co cT Db Dc Dd Et eZ FR Iq Jd Jg Jk Kq Nc Ne oP Qu qX Qy rY Ss Tn tF) dJ(aQ Bo cK cP Ef Et Ex gW Hc Is Jg Kf Ki Kl Ky Ly Mt mY nB Ne Nh nJ nT oF On Qg Rb Tn Tt uY vS) Qz(As aZ bA Bb bF cC Co cT Hq Hu Ib Iq Je Jh Kr Lj Mu Nk Nl Ok Oy qC qV Qy Rc Tt Ut Vq) nT(Aa bA bC bF bM cJ dD Dk dL dM Et Fr Ji Jt KN Li Mp Mt nU Nw oF Oi Pa Uf Vs) Ic(aC aJ bA bF bG Bo Db dD De Fr Iq Is Jd Je Kc Kq Ky Ml Nv oF Or Oz Qt Ss Tz) Tn(Db Dp Ed Fw Hu iA Ii Iq It Iv jP Js Ki Ks Ml Na nB Ne Pc Ph Qg Up Vu Wm Tj) fP(aG aO aV aZ bR bZ cC cS Db Dc Dd hR Hu Ik Is Ml Nt Oz qG rT rY uT uZ tF) Ki(bU cF Cv Dc Ed Et hR Ib In Iq Jh Kc Kq Ky NK Nt On Or Qt Qy uY xA) mZ(aY cL Ir Is Jq Ky Mn Mp Mr mY Nf NJ No Nr nU On oP oQ Or Ow Tv Ut) Et(aG aR cC Db Ed Gl Hf hR IB iJ jP Ko Kr Kz Ly Me nB Nd qC uP) On(aR As bR cK dH Ed eZ Hf kF kO Ks Kz mM Nd qC Rb Rj rY UP Tj) Nj(Ao Ap aR bR cK Co cT Cv De Gz Id Je Ky Ly mY Nc oQ Uf Ut) Db(cK cP Dg Ed eZ gW Id Is Jd Jg Ky Ne Nh Or Rb Uf vW xA) cC(bU cB ED eZ hR Is Kq lM lN Ly Ne Nh qV qX sC uP uY) cF(Aw cE cK Cw Ef Fr Is Jd Jg Jh Kc Kf Mg Ne Nh Nl Ok Vq) nB(cL Hw Ih Ip Jq lL lX Mn Mt Ne nJ Oi Ou Pg Qa Qv qX Tz) mF(Ir Kq Lx Mr No Nr Nv Nx oP oQ Pe Po rX rY Ut Uv Vs) Ok(aG aR eZ hA hR Js Kk Ly Mp nA qC qG rY uP xA) nO(aY cH hB hC Ji Jq Kq nH nK Nx Oh Ow Pf Tv Uh) mY(cE Jq Mp Mr nF Nr Nx oH Oi oQ Ow Pf Po tF) Cw(cP gW In Is Kr Ky Nd Ne Nl Or Qy Up Tj) Dc(cB cP Hf In Jm Kk kO Kr Ky Kz Lu Rm Up) Nt(Ap Hc Id Kg Kl Rb Tt tV uP uX wF wL yL) Nl(aR aX Bo bR Ed Jd Kz lY nH Qg Up xA) bF(aC aG bM bR bU cB cH cI cP dH nH nJ) rY(Ap Bo bW Iq Jd Jp Jt mE nJ nW Qv uP) Kk(aR Ba Cv Jd Jp Kc Kl Kq Li Uf Vq) Kz(Dd eD In Jg Kf Kq Ml Nc Ne qQ qV) aR(cB Ed Jd Jg Ly Ne nH nJ Rb Rh) qC(Ap Hf Jd Kf Nn Pz sC Um uP tM) Kq(Fp Hf Ik In Kr Ks Mp Ne Nm) aC(Aw aX aZ Bb bR bU cE cP cZ) kO(cM Hx iO Mt nC nK nU Oi Ut) Bo(cK cP Is Jd Ne nH qX rZ) nA(Ex Gp Is Mt Oh Oz Pb Uv) qV(cW Fn Fw Jd Ky qX uP Vq) xA(bG Hu Jp Kf Lh Pa Ue Um) Dd(Ib Ky Ph Qy rU tV Up) Ly(bA bR cT Hf Iq Me Nc) cP(Bb bR bU cB cK dB Hu) nK(Hf Jq Mp Nv Nx Po Vs) uY(As bG cM Fb Fn oH Uv) Ap(aG rB Rh rZ vW tL) Kf(Ik jM qG qU rB Rh) nH(Mn nC oP qU rA tF) rX(aW bB Bc dC nJ qD) uP(dL Ed Nb Nm Nu Om) Jd(Hu Ik Iv Ne Rh) Uk(rW vP vV wQ yK) Vq(iA lK Ml Ri tF) aG(Ba cB cE Jg lM) eZ(Ao Ch Om Qu Tt) qX(cB Ed Na nC nL) vB(dB Hu Mm qD Ue) Iq(iA lL Nd tF) Kg(qG Rh rN wQ) Lh(qD wJ wL zG) Um(Qg sO vH wF) aZ(qO sC yK tL) hR(bB Gp Jt To) tV(Hu Mm No Pe) Na(lL qT qZ) Ne(Cv Ed oP) Tt(Ik Lu Nb) aK(jR tX wL) bC(vW yL tL) cB(cE cK gP) cW(eD jR rZ) nN(Oh Qn Tv) lY(Jl Jq oH) nJ(cH oP Ow) kF(cG Ex Lx) sC(bG dB Vv) Di(iH jU) Gz(iH Rb) No(wE yL) Mm(wJ wK) Nc(In Nd) Uf(vW tL) bR(Is Jg) fY(Ph wL) nR(iO lL) nC(bP Hc) rB(Jp Jt) qD(qG wQ) qU(Fn nL) oQ(lL oH) BbLu EdqT TjJh MpzI NdfR HqwG HwwL HfhO QaJm QgbJ KnkC KrwH OavW bWjU cErZ iOwF wEyL jPtM oOoH Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Po | pg/ml | 6.9E-1 | 3.6E0 | 8.0E0 | 7.2E0 | 2.2E1 | 8.3E0 | 8.0E-3 | 2.6E-2 | 2.7E2 | 1.9E1 | 932 | 7 | 343 | 7 | 0.59 |
| Et | ng/ml | 1.4E3 | 2.6E3 | 1.7E3 | 2.5E3 | 1.2E3 | 1.6E3 | 7.5E1 | 3.9E2 | 5.0E3 | 4.1E3 | 931 | 7 | 343 | 7 | 0.65 |
| Fp | ng/ml | 1.3E1 | 1.4E1 | 2.5E1 | 2.5E1 | 2.8E1 | 2.9E1 | 6.0E-3 | 2.4E-1 | 1.4E2 | 7.2E1 | 965 | 7 | 344 | 7 | 0.49 |
| Fr | ng/ml | 3.9E4 | 4.4E4 | 1.1E5 | 2.7E5 | 1.7E5 | 3.0E5 | 1.9E2 | 2.5E3 | 9.0E5 | 6.0E5 | 1079 | 7 | 348 | 7 | 0.63 |
| Nm | pg/ml | 1.4E4 | 1.5E4 | 3.3E4 | 2.2E4 | 7.8E4 | 2.2E4 | 1.0E-9 | 1.0E-9 | 1.6E6 | 4.9E4 | 935 | 7 | 345 | 7 | 0.47 |
| Nn | pg/ml | 1.6E2 | 3.9E1 | 1.7E3 | 5.5E2 | 7.6E3 | 7.8E2 | 1.0E-9 | 1.1E0 | 1.0E5 | 1.9E3 | 935 | 7 | 345 | 7 | 0.45 |
| No | pg/ml | 1.6E1 | 8.7E0 | 3.6E1 | 2.7E1 | 1.1E2 | 5.0E1 | 1.0E-9 | 5.1E-1 | 2.5E3 | 1.4E2 | 935 | 7 | 345 | 7 | 0.37 |
| Nq | pg/ml | 2.0E0 | 1.0E-9 | 1.8E1 | 1.5E1 | 7.2E1 | 2.8E1 | 1.0E-9 | 1.0E-9 | 1.2E3 | 7.3E1 | 935 | 7 | 345 | 7 | 0.46 |
| Nr | pg/ml | 9.9E-1 | 3.5E-1 | 2.8E1 | 1.1E1 | 1.7E2 | 1.4E0 | 1.0E-9 | 1.0E-9 | 4.1E3 | 3.2E0 | 935 | 7 | 345 | 7 | 0.40 |
| Ns | pg/ml | 1.0E-9 | 1.0E-9 | 9.0E0 | 5.1E-1 | 5.1E1 | 1.4E0 | 1.0E-9 | 1.0E-9 | 1.1E3 | 3.6E0 | 935 | 7 | 345 | 7 | 0.51 |
| Nt | pg/ml | 1.0E2 | 9.7E1 | 1.3E2 | 9.9E1 | 1.1E2 | 5.8E1 | 1.0E-9 | 2.3E1 | 1.5E3 | 2.1E2 | 935 | 7 | 345 | 7 | 0.43 |
| Nu | pg/ml | 2.0E1 | 7.6E1 | 5.4E1 | 8.5E1 | 8.9E1 | 6.9E1 | 1.0E-9 | 1.0E-9 | 8.9E2 | 2.0E2 | 935 | 7 | 345 | 7 | 0.69 |
| Lu | pg/ml | 1.0E4 | 6.8E3 | 1.8E4 | 6.7E3 | 6.1E4 | 3.9E3 | 3.5E2 | 2.1E3 | 1.3E6 | 1.1E4 | 938 | 7 | 345 | 7 | 0.36 |
| Lv | pg/ml | 1.0E-9 | 1.0E-9 | 1.1E1 | 4.4E1 | 2.2E1 | 7.7E1 | 1.0E-9 | 1.0E-9 | 2.6E2 | 1.9E2 | 938 | 7 | 345 | 7 | 0.52 |
| Lw | pg/ml | 1.0E-9 | 1.0E-9 | 3.9E-1 | 1.4E0 | 4.0E0 | 3.8E0 | 1.0E-9 | 1.0E-9 | 8.0E1 | 9.9E0 | 938 | 7 | 345 | 7 | 0.56 |
| Lx | pg/ml | 1.0E-9 | 1.0E-9 | 1.4E2 | 2.9E2 | 4.1E2 | 5.2E2 | 1.0E-9 | 1.0E-9 | 6.2E3 | 1.4E3 | 938 | 7 | 345 | 7 | 0.55 |
| Ly | pg/ml | 1.0E-9 | 3.9E0 | 1.0E1 | 8.2E0 | 2.0E1 | 1.0E1 | 1.0E-9 | 1.0E-9 | 1.6E2 | 2.9E1 | 938 | 7 | 345 | 7 | 0.67 |
| Lz | pg/ml | 1.0E-9 | 1.0E-9 | 3.8E0 | 1.0E-9 | 3.0E1 | 0.0E0 | 1.0E-9 | 1.0E-9 | 6.0E2 | 1.0E-9 | 938 | 7 | 345 | 7 | 0.46 |
| Ma | pg/ml | 2.8E2 | 4.8E2 | 1.3E3 | 9.2E2 | 3.5E3 | 8.8E2 | 1.0E-9 | 2.2E0 | 6.5E4 | 1.9E3 | 938 | 7 | 345 | 7 | 0.56 |
| Mb | pg/ml | 2.5E1 | 2.1E1 | 3.1E1 | 2.7E1 | 1.5E1 | 1.3E1 | 5.4E0 | 1.4E1 | 2.1E2 | 4.7E1 | 938 | 7 | 345 | 7 | 0.38 |
| Mc | pg/ml | 1.0E-9 | 1.0E-9 | 4.1E-2 | 1.0E-9 | 5.6E-1 | 0.0E0 | 1.0E-9 | 1.0E-9 | 1.3E1 | 1.0E-9 | 938 | 7 | 345 | 7 | 0.49 |
| Md | pg/ml | 1.0E-9 | 1.0E-9 | 3.9E-1 | 1.0E-9 | 3.4E0 | 0.0E0 | 1.0E-9 | 1.0E-9 | 6.8E1 | 1.0E-9 | 938 | 7 | 345 | 7 | 0.47 |
| Me | pg/ml | 3.3E1 | 2.9E1 | 3.2E1 | 2.9E1 | 2.0E1 | 9.4E0 | 1.0E-9 | 1.3E1 | 3.2E2 | 4.2E1 | 938 | 7 | 345 | 7 | 0.44 |
| Mf | pg/ml | 1.0E-9 | 1.0E-9 | 5.2E-1 | 1.0E-9 | 2.9E0 | 0.0E0 | 1.0E-9 | 1.0E-9 | 5.6E1 | 1.0E-9 | 938 | 7 | 345 | 7 | 0.43 |
| Mg | pg/ml | 1.6E0 | 1.0E1 | 7.4E0 | 7.5E0 | 1.3E1 | 6.0E0 | 1.0E-9 | 1.0E-9 | 9.4E1 | 1.4E1 | 938 | 7 | 345 | 7 | 0.59 |
| Mh | pg/ml | 1.0E-9 | 1.0E-9 | 1.3E0 | 2.2E-2 | 9.4E0 | 3.8E-2 | 1.0E-9 | 1.0E-9 | 1.6E2 | 8.5E-2 | 938 | 7 | 345 | 7 | 0.47 |
| Mi | pg/ml | 1.0E-9 | 1.0E-9 | 4.8E-1 | 4.4E0 | 5.2E0 | 1.2E1 | 1.0E-9 | 1.0E-9 | 1.2E2 | 3.1E1 | 938 | 7 | 345 | 7 | 0.56 |
| Mj | pg/ml | 1.0E-9 | 1.0E-9 | 4.3E0 | 3.3E-1 | 2.4E1 | 8.8E-1 | 1.0E-9 | 1.0E-9 | 4.6E2 | 2.3E0 | 938 | 7 | 345 | 7 | 0.46 |
| Mk | pg/ml | 9.1E-1 | 1.0E-9 | 1.4E1 | 1.1E0 | 8.4E1 | 2.8E0 | 1.0E-9 | 1.0E-9 | 1.7E3 | 7.4E0 | 938 | 7 | 345 | 7 | 0.31 |
| Ml | pg/ml | 1.0E-9 | 1.0E-9 | 4.9E0 | 1.0E-9 | 7.2E1 | 0.0E0 | 1.0E-9 | 1.0E-9 | 2.1E3 | 1.0E-9 | 938 | 7 | 345 | 7 | 0.41 |
| Mm | pg/ml | 5.9E2 | 7.7E2 | 1.0E3 | 2.2E3 | 1.2E3 | 3.6E3 | 1.0E-9 | 1.9E1 | 1.1E4 | 9.9E3 | 938 | 7 | 345 | 7 | 0.53 |
| Mn | pg/ml | 5.5E0 | 1.4E1 | 1.0E1 | 1.4E1 | 2.2E1 | 1.1E1 | 1.0E-9 | 4.9E-1 | 3.5E2 | 3.3E1 | 938 | 7 | 345 | 7 | 0.69 |
| Mp | pg/ml | 1.0E-9 | 1.0E-9 | 8.9E0 | 2.0E1 | 2.9E1 | 3.7E1 | 1.0E-9 | 1.0E-9 | 6.3E2 | 1.0E2 | 937 | 7 | 345 | 7 | 0.55 |
| Mq | pg/ml | 1.0E-9 | 1.0E-9 | 2.7E0 | 8.8E0 | 1.6E1 | 2.3E1 | 1.0E-9 | 1.0E-9 | 2.4E2 | 6.2E1 | 937 | 7 | 345 | 7 | 0.54 |
| Mr | pg/ml | 1.0E-9 | 1.0E-9 | 2.5E1 | 6.5E-2 | 1.4E2 | 1.7E-1 | 1.0E-9 | 1.0E-9 | 2.2E3 | 4.6E-1 | 937 | 7 | 345 | 7 | 0.40 |
| Ms | pg/ml | 4.1E2 | 3.1E2 | 5.6E2 | 3.5E2 | 6.6E2 | 2.8E2 | 1.0E-9 | 1.0E-9 | 5.9E3 | 7.9E2 | 937 | 7 | 345 | 7 | 0.43 |
| Mt | pg/ml | 2.5E-1 | 1.2E0 | 6.8E0 | 1.5E0 | 4.1E1 | 1.5E0 | 1.0E-9 | 1.0E-9 | 8.7E2 | 3.6E0 | 937 | 7 | 345 | 7 | 0.57 |
| Mu | pg/ml | 1.0E-9 | 1.0E-9 | 1.2E0 | 1.1E0 | 1.0E1 | 2.1E0 | 1.0E-9 | 1.0E-9 | 2.3E2 | 5.5E0 | 937 | 7 | 345 | 7 | 0.57 |
| Mv | pg/ml | 1.0E-9 | 1.0E-9 | 6.8E1 | 6.4E1 | 3.1E2 | 1.2E2 | 1.0E-9 | 1.0E-9 | 4.5E3 | 3.1E2 | 937 | 7 | 345 | 7 | 0.54 |
| Mw | pg/ml | 3.8E1 | 7.4E1 | 5.0E2 | 4.2E2 | 3.2E3 | 5.5E2 | 1.0E-9 | 1.0E-9 | 6.2E4 | 1.4E3 | 937 | 7 | 345 | 7 | 0.62 |
| Mx | pg/ml | 1.0E-9 | 1.0E-9 | 2.4E-1 | 6.0E-1 | 1.3E0 | 1.3E0 | 1.0E-9 | 1.0E-9 | 3.2E1 | 3.4E0 | 937 | 7 | 345 | 7 | 0.58 |
| My | pg/ml | 1.0E-9 | 7.4E1 | 4.5E2 | 1.1E2 | 2.9E3 | 1.4E2 | 1.0E-9 | 1.0E-9 | 3.9E4 | 3.8E2 | 937 | 7 | 345 | 7 | 0.67 |
| Mz | pg/ml | 1.1E1 | 1.2E1 | 2.7E1 | 9.8E0 | 6.3E1 | 4.9E0 | 1.0E-9 | 3.5E0 | 1.2E3 | 1.5E1 | 937 | 7 | 345 | 7 | 0.45 |
| Na | pg/ml | 1.0E-9 | 1.0E-9 | 6.6E-1 | 9.9E-1 | 2.6E0 | 2.2E0 | 1.0E-9 | 1.0E-9 | 3.6E1 | 6.0E0 | 937 | 7 | 345 | 7 | 0.55 |
| Nb | pg/ml | 2.1E0 | 9.9E-1 | 3.8E0 | 3.1E0 | 1.1E1 | 4.0E0 | 1.0E-9 | 1.0E-9 | 2.3E2 | 1.0E1 | 937 | 7 | 345 | 7 | 0.45 |
| Nc | pg/ml | 3.4E2 | 7.7E1 | 5.6E2 | 3.0E2 | 7.2E2 | 4.9E2 | 1.0E-9 | 1.0E-9 | 9.2E3 | 1.3E3 | 937 | 7 | 345 | 7 | 0.41 |
| Nd | pg/ml | 2.9E1 | 9.6E0 | 2.7E1 | 1.4E1 | 4.4E1 | 1.4E1 | 1.0E-9 | 1.0E-9 | 1.2E3 | 3.4E1 | 937 | 7 | 345 | 7 | 0.33 |
| Ne | pg/ml | 4.4E2 | 7.6E1 | 5.7E2 | 2.6E2 | 5.7E2 | 2.9E2 | 1.0E-9 | 1.3E1 | 7.0E3 | 7.3E2 | 937 | 7 | 345 | 7 | 0.33 |
| Nf | pg/ml | 1.0E-9 | 1.0E-9 | 2.6E0 | 3.9E-1 | 9.4E0 | 1.0E0 | 1.0E-9 | 1.0E-9 | 1.6E2 | 2.7E0 | 937 | 7 | 345 | 7 | 0.44 |
| Ng | pg/ml | 1.9E1 | 1.0E-9 | 1.3E2 | 5.5E1 | 2.5E2 | 8.1E1 | 1.0E-9 | 1.0E-9 | 2.3E3 | 1.9E2 | 937 | 7 | 345 | 7 | 0.40 |
| Nh | pg/ml | 6.9E1 | 5.3E1 | 9.0E1 | 5.2E1 | 8.2E1 | 3.7E1 | 1.0E-9 | 1.1E1 | 5.6E2 | 9.3E1 | 937 | 7 | 345 | 7 | 0.37 |
| Ni | pg/ml | 1.0E-9 | 1.0E-9 | 7.2E1 | 1.1E2 | 1.2E2 | 1.8E2 | 1.0E-9 | 1.0E-9 | 7.1E2 | 4.8E2 | 937 | 7 | 345 | 7 | 0.52 |
| Nj | pg/ml | 7.5E0 | 2.7E0 | 1.1E1 | 6.2E0 | 1.2E1 | 6.2E0 | 1.0E-9 | 1.0E-9 | 1.1E2 | 1.7E1 | 937 | 7 | 345 | 7 | 0.39 |
| Nk | pg/ml | 1.7E1 | 1.4E1 | 3.3E1 | 2.2E1 | 3.9E1 | 2.3E1 | 1.0E-9 | 1.0E-9 | 2.0E2 | 6.9E1 | 937 | 7 | 345 | 7 | 0.48 |

Figure 24

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nl | pg/ml | 4.5E1 | 2.7E1 | 6.1E1 | 4.3E1 | 6.8E1 | 4.7E1 | 1.0E-9 | 1.0E-9 | 1.1E3 | 1.4E2 | 937 | 7 | 345 | 7 | 0.41 |
| Hq | pg/ml | 1.1E0 | 1.3E0 | 9.6E1 | 1.1E1 | 1.6E3 | 2.6E1 | 1.0E-9 | 1.0E-9 | 3.4E4 | 7.0E1 | 933 | 7 | 344 | 7 | 0.51 |
| Hr | pg/ml | 1.1E2 | 1.0E3 | 7.5E2 | 1.9E3 | 1.6E3 | 1.8E3 | 1.0E-9 | 6.9E1 | 1.7E4 | 4.6E3 | 933 | 7 | 344 | 7 | 0.77 |
| Hu | pg/ml | 5.3E0 | 1.0E-9 | 3.0E3 | 7.1E1 | 2.6E4 | 1.6E2 | 1.0E-9 | 1.0E-9 | 6.3E5 | 4.4E2 | 933 | 7 | 344 | 7 | 0.42 |
| Hv | pg/ml | 1.4E0 | 2.7E0 | 3.3E0 | 2.1E0 | 1.2E1 | 1.5E0 | 1.0E-9 | 3.0E-1 | 2.5E2 | 4.2E0 | 933 | 7 | 344 | 7 | 0.58 |
| Hw | pg/ml | 6.4E0 | 4.9E0 | 1.8E1 | 5.8E0 | 6.9E1 | 5.6E0 | 1.0E-9 | 1.0E-9 | 1.7E3 | 1.5E1 | 933 | 7 | 344 | 7 | 0.37 |
| Hx | pg/ml | 8.8E0 | 2.6E1 | 3.7E1 | 2.9E1 | 3.1E2 | 2.0E1 | 1.0E-9 | 1.0E-9 | 9.3E3 | 6.4E1 | 933 | 7 | 344 | 7 | 0.70 |
| Ih | ng/ml | 7.2E1 | 4.5E1 | 2.4E2 | 6.9E1 | 4.8E2 | 7.1E1 | 1.0E-9 | 1.5E1 | 7.4E3 | 2.0E2 | 937 | 7 | 344 | 7 | 0.42 |
| Ii | ng/ml | 9.5E1 | 5.7E1 | 2.4E2 | 7.8E1 | 6.6E2 | 9.5E1 | 1.0E-9 | 1.6E1 | 1.0E4 | 2.9E2 | 937 | 7 | 344 | 7 | 0.37 |
| Ij | ng/ml | 7.6E1 | 7.8E1 | 1.7E2 | 8.2E1 | 5.7E2 | 6.6E1 | 1.6E-1 | 1.0E-9 | 6.4E3 | 1.7E2 | 924 | 7 | 342 | 7 | 0.44 |
| Ik | ng/ml | 1.3E1 | 6.2E1 | 7.9E2 | 1.2E2 | 8.0E3 | 1.7E2 | 5.9E-1 | 5.0E0 | 1.2E5 | 4.8E2 | 932 | 7 | 342 | 7 | 0.57 |
| Il | ng/ml | 3.3E2 | 5.3E2 | 1.3E3 | 6.3E2 | 2.8E3 | 7.0E2 | 1.0E-9 | 1.0E-9 | 1.3E4 | 2.1E3 | 916 | 7 | 342 | 7 | 0.53 |
| Im | ng/ml | 2.1E2 | 1.2E2 | 4.0E2 | 2.6E2 | 7.6E2 | 2.5E2 | 1.3E1 | 8.3E1 | 1.5E4 | 7.1E2 | 931 | 7 | 343 | 7 | 0.42 |
| In | ng/ml | 3.3E0 | 2.4E0 | 2.1E1 | 4.4E0 | 1.5E2 | 4.0E0 | 1.0E-9 | 1.0E-9 | 3.9E3 | 1.1E1 | 937 | 7 | 344 | 7 | 0.46 |
| Io | ng/ml | 8.3E3 | 3.6E3 | 2.5E4 | 7.3E3 | 1.4E5 | 6.8E3 | 1.0E-9 | 1.3E3 | 4.0E6 | 2.0E4 | 928 | 7 | 344 | 7 | 0.40 |
| Ip | ng/ml | 1.0E1 | 4.8E0 | 2.0E1 | 2.1E1 | 2.4E1 | 2.4E1 | 1.0E-9 | 6.4E-1 | 2.6E2 | 5.8E1 | 928 | 7 | 344 | 7 | 0.53 |
| Iq | ug/ml | 1.0E-1 | 1.8E-2 | 3.0E1 | 9.4E-2 | 6.3E2 | 1.2E-1 | 1.0E-9 | 1.0E-9 | 1.4E4 | 3.0E-1 | 928 | 7 | 344 | 7 | 0.35 |
| Ir | ug/ml | 3.5E-1 | 6.0E-1 | 3.4E0 | 7.0E-1 | 2.4E1 | 5.1E-1 | 1.0E-9 | 2.0E-1 | 5.1E2 | 1.6E0 | 927 | 7 | 344 | 7 | 0.59 |
| Is | ng/ml | 1.6E0 | 5.7E0 | 6.4E0 | 6.4E0 | 2.2E1 | 4.9E0 | 1.0E-9 | 9.9E-1 | 5.5E2 | 1.3E1 | 928 | 7 | 344 | 7 | 0.70 |
| It | ng/ml | 2.0E0 | 7.7E-1 | 2.3E1 | 4.2E0 | 1.4E2 | 5.7E0 | 1.0E-9 | 1.0E-9 | 2.8E3 | 1.4E1 | 928 | 7 | 344 | 7 | 0.47 |
| Iu | ng/ml | 2.2E2 | 2.0E2 | 1.3E3 | 3.3E2 | 4.0E3 | 3.7E2 | 1.0E-9 | 4.0E1 | 2.9E4 | 1.1E3 | 928 | 7 | 344 | 7 | 0.49 |
| Iv | ng/ml | 1.3E1 | 6.9E1 | 6.0E1 | 5.0E1 | 5.4E2 | 4.0E1 | 1.0E-9 | 1.0E-9 | 1.6E4 | 9.2E1 | 927 | 7 | 344 | 7 | 0.65 |
| Pz | ng/ml | 3.8E3 | 1.0E4 | 8.1E3 | 7.4E3 | 3.7E4 | 4.5E3 | 1.3E1 | 6.1E2 | 1.0E6 | 1.0E4 | 929 | 7 | 342 | 7 | 0.61 |
| Qa | ng/ml | 3.5E2 | 5.6E3 | 6.3E3 | 7.0E3 | 7.4E3 | 5.0E3 | 1.2E1 | 1.8E3 | 5.2E4 | 1.6E4 | 929 | 7 | 342 | 7 | 0.63 |
| Qb | ng/ml | 9.7E1 | 2.1E2 | 2.1E2 | 2.1E2 | 4.8E2 | 1.1E2 | 7.9E-1 | 5.7E1 | 8.3E3 | 3.8E2 | 929 | 7 | 342 | 7 | 0.68 |
| Qc | ng/ml | 2.3E2 | 1.2E2 | 6.3E2 | 1.6E2 | 5.5E3 | 1.5E2 | 1.0E-9 | 2.7E1 | 1.7E5 | 4.8E2 | 929 | 7 | 342 | 7 | 0.35 |
| Qd | ng/ml | 9.2E3 | 9.9E3 | 2.1E4 | 2.7E4 | 7.7E4 | 3.3E4 | 1.5E2 | 2.3E3 | 2.0E6 | 8.7E4 | 929 | 7 | 342 | 7 | 0.58 |
| Qe | ng/ml | 9.2E2 | 2.2E3 | 1.8E3 | 3.1E3 | 3.8E3 | 2.8E3 | 1.0E-9 | 5.0E2 | 9.7E4 | 8.1E3 | 929 | 7 | 342 | 7 | 0.70 |
| Jg | ng/ml | 4.9E2 | 7.2E2 | 8.2E2 | 8.6E2 | 1.0E3 | 7.3E2 | 1.0E-9 | 5.9E1 | 1.0E4 | 1.7E3 | 933 | 7 | 344 | 7 | 0.55 |
| Jh | ng/ml | 3.0E0 | 2.4E0 | 2.7E1 | 1.5E1 | 1.1E2 | 2.5E1 | 1.0E-9 | 1.0E-9 | 1.6E3 | 6.8E1 | 933 | 7 | 344 | 7 | 0.56 |
| Ji | ng/ml | 5.3E1 | 1.0E2 | 7.7E1 | 1.5E2 | 8.0E1 | 1.2E2 | 1.0E-9 | 3.4E1 | 6.9E2 | 3.8E2 | 933 | 7 | 344 | 7 | 0.73 |
| Jj | ng/ml | 6.0E2 | 9.8E2 | 1.7E3 | 8.5E2 | 1.2E4 | 5.5E2 | 2.3E0 | 1.3E1 | 3.4E5 | 1.4E3 | 933 | 7 | 344 | 7 | 0.54 |
| Jk | ng/ml | 3.1E0 | 7.9E0 | 2.1E1 | 1.5E1 | 4.7E1 | 2.1E1 | 1.0E-9 | 6.2E-1 | 3.9E2 | 6.1E1 | 933 | 7 | 344 | 7 | 0.59 |
| Jl | ng/ml | 4.4E-1 | 5.7E-1 | 1.9E0 | 6.5E0 | 5.6E0 | 9.4E0 | 7.6E-4 | 1.1E-1 | 1.1E2 | 2.0E1 | 933 | 7 | 344 | 7 | 0.58 |
| Jm | ng/ml | 1.8E1 | 1.5E1 | 5.8E1 | 2.5E1 | 1.3E2 | 2.4E1 | 1.0E-9 | 2.6E0 | 2.1E3 | 6.2E1 | 933 | 7 | 344 | 7 | 0.48 |
| Jn | pg/ml | 4.0E-1 | 8.7E-1 | 2.5E0 | 7.4E-1 | 2.2E1 | 5.9E-1 | 1.0E-9 | 4.7E-2 | 6.2E2 | 1.5E0 | 932 | 7 | 344 | 7 | 0.59 |
| Jo | pg/ml | 3.6E3 | 4.7E3 | 4.7E3 | 5.1E3 | 3.8E3 | 4.6E3 | 2.0E1 | 9.0E2 | 2.4E4 | 1.3E4 | 933 | 7 | 344 | 7 | 0.50 |
| Jp | pg/ml | 7.0E4 | 9.8E4 | 7.4E4 | 8.9E4 | 3.8E4 | 2.5E4 | 5.8E2 | 5.1E4 | 3.8E5 | 1.2E5 | 933 | 7 | 344 | 7 | 0.67 |
| Jq | pg/ml | 9.4E1 | 1.5E2 | 1.5E2 | 2.4E2 | 2.1E2 | 2.3E2 | 1.0E0 | 4.0E1 | 4.0E3 | 7.5E2 | 933 | 7 | 344 | 7 | 0.69 |
| Jr | pg/ml | 5.2E0 | 1.2E1 | 3.3E1 | 1.6E1 | 3.6E2 | 1.5E1 | 1.0E-9 | 1.0E-9 | 1.1E4 | 4.0E1 | 933 | 7 | 344 | 7 | 0.67 |
| Js | pg/ml | 1.3E1 | 9.4E0 | 4.9E1 | 1.1E1 | 3.6E2 | 6.3E0 | 1.0E-9 | 4.5E-1 | 1.0E4 | 2.0E1 | 933 | 7 | 344 | 7 | 0.41 |
| Jt | pg/ml | 2.6E3 | 2.3E3 | 3.2E3 | 2.3E3 | 2.4E3 | 1.9E3 | 2.2E1 | 3.5E2 | 2.2E4 | 5.9E3 | 933 | 7 | 344 | 7 | 0.38 |
| Lh | pg/ml | 1.3E4 | 1.7E4 | 2.1E4 | 2.7E4 | 2.6E4 | 2.5E4 | 1.0E-9 | 4.6E3 | 2.6E5 | 7.3E4 | 932 | 7 | 345 | 7 | 0.60 |
| Li | pg/ml | 3.5E3 | 1.3E3 | 1.7E4 | 1.5E4 | 6.2E4 | 2.5E4 | 1.0E-9 | 5.0E2 | 1.3E6 | 6.8E4 | 932 | 7 | 345 | 7 | 0.49 |
| Lj | pg/ml | 2.8E3 | 3.9E3 | 2.3E4 | 3.2E3 | 6.4E4 | 3.0E3 | 1.0E-9 | 1.9E2 | 5.2E5 | 8.1E3 | 932 | 7 | 345 | 7 | 0.42 |
| Nv | pg/ml | 4.0E3 | 5.1E3 | 1.1E4 | 1.7E4 | 4.2E4 | 2.6E4 | 1.0E-9 | 1.3E3 | 1.1E6 | 7.1E4 | 939 | 7 | 345 | 7 | 0.59 |
| Nw | pg/ml | 8.9E3 | 1.1E4 | 1.3E4 | 1.7E4 | 1.6E4 | 1.6E4 | 8.6E1 | 3.4E3 | 2.1E5 | 5.0E4 | 939 | 7 | 345 | 7 | 0.59 |
| Nx | pg/ml | 2.2E2 | 1.1E3 | 4.1E2 | 1.0E3 | 6.4E2 | 6.4E2 | 1.0E-9 | 2.3E2 | 7.4E3 | 1.8E3 | 939 | 7 | 345 | 7 | 0.82 |
| Ny | pg/ml | 6.2E0 | 7.6E0 | 5.2E1 | 3.0E1 | 8.3E2 | 4.4E1 | 1.0E-9 | 1.0E-9 | 2.5E4 | 1.0E2 | 939 | 7 | 345 | 7 | 0.55 |
| Oe | pg/ml | 7.1E1 | 1.0E-9 | 2.9E2 | 2.9E2 | 7.4E2 | 4.4E2 | 1.0E-9 | 1.0E-9 | 1.9E4 | 1.1E3 | 930 | 7 | 344 | 7 | 0.46 |
| Of | pg/ml | 1.8E2 | 1.2E2 | 5.9E3 | 6.4E3 | 2.8E4 | 1.5E4 | 1.0E-9 | 1.0E-9 | 6.2E5 | 4.0E4 | 938 | 7 | 345 | 7 | 0.49 |
| Og | pg/ml | 8.2E-2 | 9.3E-2 | 7.1E-1 | 1.7E-1 | 4.7E0 | 2.0E-1 | 1.0E-9 | 1.0E-9 | 8.3E1 | 5.3E-1 | 938 | 7 | 345 | 7 | 0.46 |
| Oh | pg/ml | 2.6E0 | 4.2E0 | 1.8E1 | 5.0E0 | 1.4E2 | 6.6E0 | 1.0E-9 | 1.0E-9 | 3.5E3 | 1.9E1 | 938 | 7 | 345 | 7 | 0.49 |
| Oi | pg/ml | 2.6E0 | 3.6E0 | 6.3E0 | 6.0E0 | 9.8E0 | 7.1E0 | 1.0E-9 | 1.0E-9 | 8.6E1 | 1.9E1 | 938 | 7 | 345 | 7 | 0.53 |
| Ok | pg/ml | 3.9E2 | 9.8E2 | 5.4E2 | 1.4E3 | 5.7E2 | 1.8E3 | 1.3E1 | 1.4E2 | 7.0E3 | 5.2E3 | 938 | 7 | 345 | 7 | 0.66 |
| Om | pg/ml | 3.9E2 | 5.8E2 | 8.2E2 | 8.9E2 | 2.1E3 | 9.3E2 | 1.0E-9 | 1.0E-9 | 3.6E4 | 2.5E3 | 938 | 7 | 345 | 7 | 0.57 |
| On | pg/ml | 1.8E2 | 3.1E2 | 2.8E2 | 6.1E2 | 3.9E2 | 6.2E2 | 1.0E-9 | 8.9E1 | 4.5E3 | 1.7E3 | 938 | 7 | 345 | 7 | 0.69 |

Figure 24 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oy | pg/ml | 4.9E-1 | 4.7E-1 | 5.7E0 | 1.3E0 | 2.8E1 | 2.4E0 | 1.0E-9 | 1.5E-1 | 4.0E2 | 6.6E0 | 937 | 7 | 344 | 7 | 0.51 |
| Oz | pg/ml | 1.2E-2 | 1.0E-1 | 3.2E-1 | 2.0E-1 | 1.3E0 | 2.3E-1 | 1.0E-9 | 1.0E-9 | 2.9E1 | 6.0E-1 | 937 | 7 | 344 | 7 | 0.56 |
| Pa | pg/ml | 3.9E-1 | 3.6E-1 | 1.4E0 | 4.1E-1 | 4.9E0 | 2.8E-1 | 1.0E-9 | 1.0E-9 | 8.6E1 | 9.2E-1 | 937 | 7 | 344 | 7 | 0.47 |
| Pb | pg/ml | 1.0E-9 | 1.0E-9 | 7.4E-1 | 1.0E-1 | 1.6E1 | 1.3E-1 | 1.0E-9 | 1.0E-9 | 4.9E2 | 2.9E-1 | 937 | 7 | 344 | 7 | 0.51 |
| Pc | pg/ml | 5.4E-2 | 2.7E-1 | 3.5E-1 | 3.1E-1 | 8.4E-1 | 2.6E-1 | 1.0E-9 | 1.0E-9 | 1.6E1 | 6.4E-1 | 937 | 7 | 344 | 7 | 0.56 |
| Pd | pg/ml | 1.8E0 | 1.9E0 | 4.8E0 | 2.7E0 | 2.8E1 | 1.7E0 | 1.0E-9 | 9.3E-1 | 8.4E2 | 5.4E0 | 937 | 7 | 344 | 7 | 0.56 |
| Pe | pg/ml | 2.2E1 | 4.6E1 | 1.0E2 | 5.1E1 | 3.4E2 | 5.3E1 | 1.0E-9 | 3.7E0 | 4.7E3 | 1.6E2 | 937 | 7 | 344 | 7 | 0.55 |
| Pf | pg/ml | 1.6E0 | 2.4E0 | 1.0E1 | 1.3E1 | 5.7E1 | 2.8E1 | 1.0E-9 | 3.6E-1 | 1.5E3 | 7.7E1 | 937 | 7 | 344 | 7 | 0.56 |
| Pg | pg/ml | 3.5E0 | 5.1E0 | 4.1E1 | 2.1E1 | 3.3E2 | 3.0E1 | 1.0E-9 | 1.3E0 | 7.7E3 | 7.8E1 | 937 | 7 | 344 | 7 | 0.61 |
| aA | mg/dL | 8.1E-1 | 1.2E0 | 9.5E-1 | 1.3E0 | 4.9E-1 | 5.2E-1 | 2.0E-1 | 6.2E-1 | 4.2E0 | 2.3E0 | 2722 | 8 | 517 | 8 | 0.74 |

Analyte panel data:

Unconstrained panels with 3 analytes, where 1.0E-6 >= 'model p-value' > 0. Contains 5 panels of 287,980 total panels evaluated. : Ii{Nx(Hr Js Mz) HrOn} HrHwNx Unconstrained panels with 3 analytes, where 1.0E-5 >= 'model p-value' > 1.0E-6. Contains 55 panels of 287,980 total panels evaluated. : Nx{Js(aA Hr Hu Hw Ij Ik Is Ji Jt Ly Md Mf Mi Mk Mr Nb Ng Nr Nt Oy Qb Qc Qe) Ii(Fr Hw Ih Ij Im Io Jt Lj Lu Lv Mf Mk Ml Mr Ms My Nb Nr Nt Qc Qe) Ij(Jt Mk No Nt)} Hr{Ij(aA Lv Mk) Ji(Hw Ii Js) HwOn}

Unconstrained panels with 3 analytes, where 1.0E-4 >= 'model p-value' > 1.0E-5. Contains 392 panels of 287,980 total panels evaluated. : Nx{Ii(aA Et Fp Hq Hu Hv Hx Ik Il In Ip Iq Ir Is It Iu Iv Jg Jh Ji Jj Jk Jl Jm Jn Jo Jp Jq Jr Lh Li Lw Lx Ly Lz Ma Mb Mc Md Me Mg Mh Mi Mj Mm Mn Mp Mq Mt Mu Mv Mw Mx Na Nc Nd Ne Nf Ng Nh Ni Nj Nk Nl Nm Nn No Nq Ns Nu Nv Nw Ny Oe Of Og Oh Oi Ok Om On Oy Oz Pa Pb Pc Pd Pe Pf Pg Po Pz Qa Qb Qd) Js(Et Fp Fr Hq Hv Hx Ih Il Im In Io Ip Iq Ir It Iu Iv Jg Jh Jj Jk Jl Jm Jn Jo Jp Jq Jr Lh Li Lj Lu Lv Lw Lx Lz Ma Mb Mc Me Mg Mh Mj Ml Mm Mn Mp Mq Ms Mt Mu Mv Mw Mx My Mz Na Nc Nd Ne Nf Nh Ni Nj Nk Nl Nm Nn No Nq Ns Nu Nv Nw Ny Oe Of Og Oh Oi Ok Om On Oz Pa Pb Pc Pd Pe Pf Pg Po Pz Qa Qd) Jt(aA Et Fr Hr Hu Hw Ih It Iq Jm Jn Jp Lj Lv Lw Lx Ly Md Mf Mh Mj Mk Ml Mm Mn Mr Ms Mt My Mz Nb Nr Ns Nt Og Ok On Oy Pa Pz Qc Qe) Ij(aA Hr Hw Ih Io Iq Lj Lu Lv Lx Ly Md Mf Ml Mr Ms Mt Mz Nb Ng Nm Nr Nw Oe Og Oh Om Qc) Nr(aA Fr Hr Hw Io Iq Lu Lv Ly Mf Mi Mk Ml Ms My Mz Ng Nm Og Pf Qc Qe) Qc(aA Hr Hw Lu Lv Mk Mr Ms Mz Ng Nt Ok Qe) Hr(aA In Iq Jm Mk Ng) Mz(aA Mk Ng) Nt(Hw Ly) Mr(Io Ng) MkHw MsLj IhQe} Hr{Hw(aA Et Fr Ij Is Jl Jn Jp Jq Lh Lv Mm Ne Nv Ok Qb Qe) Ij(Ji Jp Mi Mr Og Ok On) Mk(aA Fr Ji On) Ii(Et Lv Nv Ok) aA(Lv Mm) NrJi QcQe} Ij{Mk(Fr Is Ji Lv Ly Mi My Ok On Qb Qe) No(Ji Ok On) Lv(Js Mr) Jt(Ok On) MrOk QcQe JiJs} Qc{Qe(Ih Ii Iq Jm Js Lj Lu Ly Mk Nr Ok) IiOn} On{Ii(Jt Ly Mr Mz) Mk(Ly Mz) MzHu} Ji{Js(Lu Ly Mk Qe)} FrLyMk Unconstrained panels with 3 analytes, where 1.0E-3 >= 'model p-value' > 1.0E-4. Contains 2,422 panels of 287,980 total panels evaluated. : Nx{Qc(Et Fp Fr Hq Hu Hv Hx Ih Ik Il Im In Io Ip Iq Ir Is It Iu Iv Jg Jh Ji Jj Jk Jl Jm Jn Jo Jp Jq Jr Lh Li Lj Lw Lx Ly Lz Ma Mb Mc Md Me Mf Mg Mh Mi Mj Ml Mm Mn Mp Mq Mt Mu Mv Mw Mx My Na Nb Nc Nd Ne Nf Nh Ni Nj Nk Nl Nm Nn Nq Ns Nu Nv Nw Ny Oe Of Og Oh Oi Om On Oy Oz Pa Pb Pc Pd Pe Pf Pg Po Pz Qa Qb Qd) Ih(aA Et Fp Fr Hq Hr Hu Hv Hw Ik Il Im In Io Iq Ir Is Iu Jg Jh Ji Jj Jk Jl Jm Jn Jo Jr Lh Lj Lu Lv Lw Lx Ly Lz Ma Mb Md Mf Mg Mh Mi Mj Mk Ml Mm Mp Mr Ms Mt Mu Mv Mw Mx My Mz Nb Nc Nd Ne Nf Ng Nh Nj Nk Nl Nm Nn Nq Nr Ns Nt Nu Nv Nw Ny Oe Of Og Oh Ok Om On Oy Oz Pa Pb Pc Pd Pe Pf Pg Po Qa Qb Qd) Nr(Et Fp Fr Hq Hu Hv Hx Ik Il Im In Ip Ir Is It Iu Iv Jg Jh Ji Jj Jk Jl Jm Jn Jo Jp Jq Jr Lh Li Lj Lw Lx Lz Ma Mb Mc Md Me Mg Mh Mj Mm Mn Mp Mq Mr Mt Mu Mv Mw Mx Na Nb Nc Nd Ne Nf Nh Ni Nj Nk Nl Nn No Nq Ns Nt Nu Nv Nw Ny Oe Of Oh Oi Ok Om On Oy Oz Pa Pb Pc Pd Pe Pg Po Pz Qa Qb Qd) Ij(Et Fp Fr Hq Hu Hv Hx Ik Il Im In Ip Ir Is It Iu Iv Jg Jh Jj Jk Jl Jm Jn Jo Jp Jq Jr Lh Li Lw Lz Ma Mb Mc Me Mg Mh Mi Mj Mm Mn Mp Mq Mu Mv Mw Mx My Na Nc Nd Ne Nf Nh Ni Nj Nk Nl Nn Nq Ns Nu Nv Ny Of Oi Ok On Oy Oz Pa Pb Pc Pd Pe Pf Pg Po Pz Qa Qb Qd Qe) Mk(aA Fp Fr Hu Hv Ik Il Im In Io Ip Iq Ir Is It Iu Jh Jl Jl Jm Jn Jo Jr Lh Lj Lu Lv Lw Lx Ly Lz Ma Md Me Mf Mg Mh Mi Mj Ml Mm Mp Mr Ms Mt Mu Mv Mx My Nb Nc Nd Ne Nf Ng Nh Ni Nj Nk Nm Nn No Nq Ns Nt Nu Nw Ny Oe Of Og Oh Ok Om On Oy Oz Pa Pc Pd Pe Pf Qb Qe) Jt(Fp Hq Hv Hx Ik Il Im Io Ip Ir Is It Iu Iv Jg Jh Ji Jj Jk Jl Jo Jq Jr Lh Li Lu Lz Ma Mb Mc Me Mg Mi Mp Mq Mu Mv Mw Mx Na Nc Nd Ne Nf Ng Nh Ni Nj Nk Nl Nm Nn No Nq Nu Nv Nw Ny Oe Of Oh Oi Om Oz Pb Pc Pd Pe Pf Pg Po Qa Qb Qd) Mz(Hq Hr Hu Hw Ik Il Im In Io Iq Ir Iu Jg Jh Ji Jj Jk Jl Jm Jo Lh Lj Lu Lv Lw Lx Ly Ma Mb Md Mf Mg Mh Mi Mj Ml Mm Mr Ms Mt Mv Mw My Nb Ne Nf Nm Nn Nq Ns Nt Oe Of Og Oh Ok Om Oy Pa Pb Pd Pe Pg Po Qe) Ng(aA Fp Fr Hu Hv Hw Ik Il Im In Io Ir Is It Iu Jm Jn Jr Lj Lu Lv Lx Ly Lz Md Mf Mg Mh Mj Ml Mm Mp Ms Mt My Nb Nc Nd Ne Nf Nj Nm Nn No Ns Nt Nw Ny Oe Of Og Oh Ok Om Oy Pa Pd Pe Po Qa) Mr(aA Fr Hr Hu Hv Hw Ik Il Im In Iq Iu Jg Jh Jk Jm Jn Jo Li Lj Lu Lv Lx Ly Md Mf Mg Mi Mj Ml Mp Ms Mt My Nb Nd Ne Nf Nh Ni Nm Nn Nq Ns Nt Oe Of Og Oh Ok Om Oy Oz Pa Pf Qe) Hw(aA Fp Hu Hv Ik Il Im In Io Iq Ir Iu Jg Jh Jk Jm Jn Jo Lh Lj Lu Lv Lx Ly Mb Md Mf Mg Mh Mj Ml Mp Ms Mt My Nb Nd Ne Nm Nn Nq Nw Oe Of Og Oh Ok Om Oy Oz Pa Pd Pe Po Qe) Nt(aA Fr Hr Hu Il Im In Io Iq Ir Iu Jl Jm Jn Lj Lu Lv Lw Lx Md Mf Mh Mi Mj Ml Mm Mp Ms Mt Nd Ne Nf Nh Ni Nj Nm Ns Nu Ny Oe Of Og Oh Ok Om Oy Pa Qe) Io(aA Fp Hr Hu Hv Ik Il Im In Iq Iu Jh Jk Jm Lj Lu Lv Lx Ly Md Mf Mh Mj Ml Ms Mt My Nb Nf Nn Of Og Om Oy Pa Pd Pe Po) Iq(aA Fp Fr Hu Ik Im In Jm Jo Lj Lu Lv Lx Ly Md Mf Mg Mi Mj Ml Ms Mt My Nb Ne Nm Oe Of Og Oh Ok Om Oy Pa Pd Qb Qe) Jm(aA Fr Hu Ik Im In Jn Lj Lu Lv Lx Ly Md Mf Mj Ml Ms Mt My Nb Nd Nc Nm Nw Oe Of Og Oh Om Pa Qe) Hr(Hu Ik Il Im Iu Jk Jo Lj Lu Lv Ly Md Mf Mg Mj Ml Ms Mt Nf Nm Nn Of Og Om Oy Pa Pd Pe Po) Ms(aA Hu Im In Ir Iu Jn Lu Lx Ly Md Mf Mh Mj Ml Mt Nb Nm No Of Pa Pd Pe) aA(Hu Im Ir Jn Lj Lx Ly Md Mj Mt Nb Nm Nq Nv Nw Of Oh Om Pa) Lu(Hu Im In Jk Lh Lv Lx Md Mj Ml Mt Nb Nn Of Oy Pa Pd Po) Im(Hu In Lj Lv Ly Md Mf Mj Ml Nb Nm Og Ok Pa Pd Qe) Lj(Hu In Jh Lv Ly Md Mf Mg Mj Mt My Nm Of Om Oy) Ly(Hu Ik In Md Mf Mj Ml Mt Nb Nm Of Oy Pd) Mt(Fr In Jl Lv Mf Mi Ml Nm Of Og On) In(Hu Lx Md Mf Ne Nm Of Om) Nm(Md Mj Ml Mm Ok Pa) Mf(Hu Mj Nd Of Om Pa) Lv(Lx Mj Of Pa) Of(Mj Ml Pa) Ik(Nd Pa) FrPa} Ij{Lv(aA Et Fp Fr Hq Hu Hv Hw Hx Ih Ii Ik Il Im In Io Ip Iq Ir Is It Iu Iv Jg Jh Ji Jj Jk Jl Jm Jn Jo Jp Jq Jr Jt Lh Li Lj Lu Lw Lx Ly Lz Ma Mb Mc Md Me Mf Mg Mh Mi Mj Ml Mm Mn Mp Mq Ms Mt Mu Mv Mw Mx My Mz Na Nb Nc Nd Ne Nf Ng Nh Ni Nj Nk Nl Nm Nn No Nq Nr Ns Nt Nu

Mf Ml Mz Nb Nd Ne Ng Nm Nt Om) Js(Et Jl Jn Jp Jq Lh Mi My Ne Nv Nw Pg Qa Qb) Ii(Et Is Jl Jn Jp Jq Lh Lw My Ne Nv Pg Qb) Is(Hw Im Io Ir Jm Jt Lj Lu Mj Mz Om) Et(Hw Ih Io Iq Lj Lu Mz Ng Nt Om) My(Hu Hw Ih Iq Jt Mz Nd Ne Om) Jq(Hw Ih Io Iq Jt Lj Lu Mz Om) Ne(Hw Ih Iq Lj Lu Mf Ml Nc) Iq(Ir Jl Jn Mi Qa Qb) Jl(Hu Hw Ih Mt Mz) Nd(Mb Mf Ml) Hw(Jn Ml Qb) Ih(Ir Jn Qa) Jp(Io Jt Mz) Mi(Mt Pa) LuJn MgNg QbLj

Constrained panels with 3 analytes, where 1.0E-6 >= 'model p-value' > 0. Contains 5 panels of 287,980 total panels evaluated. : Ii{Nx(Hr Js Mz) HrOn} HrHwNx Constrained panels with 3 analytes, where 1.0E-5 >= 'model p-value' > 1.0E-6. Contains 35 panels of 287,980 total panels evaluated. : Nx{Ii(Hw Ij Io Jt Lj Lu Mf Mk Mr My Nr Nt Qc) Js(aA Hu Hw Ij Ji Jt Md Mf Mk Ng Qe) Ij(Jt Mk No Nt)} Hr{Ij(aA Lv Mk) Ji(Hw Ii Js) HwOn}

Constrained panels with 3 analytes, where 1.0E-4 >= 'model p-value' > 1.0E-5. Contains 132 panels of 287,980 total panels evaluated. : Nx{Qc(aA Hr Hw Ij Jt Lu Lv Mk Mr Ms Ng Nr Ok Qe) Jt(Hr Hw Md Mm Mr Mt Mz Nr Ok Pz Qe) Hr(aA Ij In Iq Jm Mk Ng Nr) Nr(Fr Hw Ij Lu Ms Mz) Ij(Hw Lv Mr Mz Oh) Mz(aA Mk Ng) Nt(Hw Ly) Mr(Io Ng) MkHw MsLj IhQe} Hr{Hw(aA Et Fr Ij Is Jl Jn Jp Jq Lh Lv Mm Ne Nv Ok Qb Qe) Mk(aA Fr Ji On) Ii(Et Lv Nv Ok) Ij(Ji Jp Mi Ok) aA(Lv Mm) NrJi QcQe} Ij{Mk(Fr Is Ji Lv Ly Mi My Ok On Qb Qe) No(Ji Ok On) Lv(Js Mr) Jt(Ok On) MrOk QcQe JiJs} Qc{Qe(Ih Ii Iq Jm Js Lj Lu Ly Mk Nr Ok) IiOn} On{Ii(Jt Ly Mr Mz) Mk(Ly Mz) MzHu} Ji{Js(Lu Ly Mk Qe)} FrLyMk Constrained panels with 3 analytes, where 1.0E-3 >= 'model p-value' > 1.0E-4. Contains 607 panels of 287,980 total panels evaluated. : Hr{Ii(aA Fr Is Jg Jl Jn Jp Jq Lh Ly Mm Mn Mt Ne Nw Pg Qb Qd Qe) Nx(Hu Ih Il Im Iu Jo Md Mj Ml Mr Ms Mt Nf Nm Of Og Oy Pa Pd) Mk(Et Is Jl Jn Jp Lu Lv Ly Mi Mm Mn Mt My Ne Nv Nw Ok Qe) Hw(Hv Ir Jg Jk Ly Mi Mn Mt My Mz Nh Nu Nw Pg Pz Qa Qd) Ji(aA Ih Im In Iq Iu Jm Jt Mj Mr Ms Mz Nf Ng Nt Qc) Nr(aA Et Fr Is Jp Lv Lx Mi Mm Mt Ok On Qe) On(Hu Iq Jm Js Jt Md Mr Mt Ng Oy Qc) Lv(Ih In Iq Jm Js Lu Mf Mj Mr Qc) Iq(aA Fr Is Jp Mm Ok Qe) Qc(aA Et Is Jp Mm Ok Qd) Mr(aA Et Fr Lx Mi Ok) Js(Is Jq Mm Ok Qe) In(aA Is Mm Qe) Jt(Et Jp Mm Ok) Fr(Hu Ng Oy) Ih(Is Qe) Jm(Is Qe) aA(Ly Mf)} Nx{Hw(aA Hu Ih Io Jm Lj Lu Ly Mj Mr Ms Mt Mz Nb Ng Nm) aA(Ih Im Io Iq Jn Lj Lx Ly Mj Mk Mr Mt Nb Nt Om) Lu(Hu Jm Lx Md Mj Mk Mr Mt Nb Ng Nt Oy Pa) Mz(Hu Ik In Jm Jo Md Mf Mr Ms Nm Nt Of Oy) Ms(Ih Im Io Iq Mj Mk Mr Mt Ng Nt Pa) Mr(Ih Im Iq Jm Lv Ly Mk Ni Nm) Ng(Fr Ih Iq Jn Lj Ly Mk Pa) Nt(Im Io Iq Jm Mf Nd Nu) Ly(Ik In Mf Mj Mk Nb) Lv(Io Lx Mj Mt Pa) Lj(Hu Mk Mt Of Oy) Nm(Md Mm Ok Pa) Mf(Iq Nd Om) Mk(Ih Io Iq) Io(In Jm) FrMt NdIk ImQe} On{Js(Hu Hw Ii Ij Is Jt Lv Ly Mk Mr Ng Nr Nt Om Oy Qc) Jt(Hu Hw Iq Ly Md Mk Mm Mr Mt Mz Nd Nr Om Pa Qc) Qc(Hu Hw Ij Lv Ly Mk Ms Mt Ng Nr Om) Ly(Hu Hw Ik Mr Mt Ng Nr Nt) Mk(Ii Io Iq Lj Mr Nd Ne Nr) Mz(Ij Jh Md Mt My Ng Nr Oy) Ii(Hw Io Lj Lv Nq Om) Ij(Hw Mr Nr Nt Om) Nr(Hw Nd Om) MrMt} Ij{Mr(aA Fr Is Ji Ly Mi My Ni Qb Qe) No(Et Fr Is Jp Lh Mi Nv Qb Qe) Jt(Et Fr Is Ji Jp Lh Nv Qb Qe) Ok(Ii Js Lv Ly Mz Nm Nt Qc) Qb(Hw Ih Iq Js Lj Nr Qc) Qe(Ih Iq Js Lj Nr Nt) Is(Hw Ih Iq Js Qc) Lv(Iq Ly Mj Oh) Mi(Js Mt Nr) Ji(Ii Mz Nt) Lh(Ii Js) aA(Ly Mk) EtNt FrNr} Ly{Mk(aA Ji Jl Jp Lv Mi Mm My Ok Qe) Fr(Hu Ii Mr Mt Ng Nr Nt Oy) Ji(Ih Ii Jt Mr Mz Nr Nt Qc) Ok(Ii Ik Jt Mr Nr Nt Qc) Qe(Ih Ii Jm Js Nr) Mr(aA Lv Lx Mi) Et(Jt Nt) Mm(Jt Nt) Ih(Is Qb) aA(Nb Qc) NrMi IsJs} Ok{Mz(aA Hu Ii Jt Mk Mr Ng Nr) Mr(Fr Ii Io Jt Lv Ni) Qc(Ii Ji Jt Lv Qa Qb) Qe(Ih Ii Iq Js Jt Nr) Jt(Ii Lj Mm) Nt(Iq Nd) Lv(Iq Js)} Ji{Mz(aA Ih Ii Ik Mf Mk Mr Ms Ng Nr Qc) Ii(Fr Lj Lu Mr My Oy Qc) Qc(Js Lu Lv Mk Mr Ms) Lu(Mk Mr Nr) Js(Lv Mr) FrNr MmJt} Qe{Nr(Fr Ih Iq Mi Mk) Js(Ih Iq Jq Lv Mk) Ih(Jt Mk Mr) Qc(Ir Jt Mz) IiLj} Fr{Nr(Hu Ii Lv Mk Ne Ng) Mk(Ii Js Mr Ne Qc) Mr(Ii Ng) LvIi} Lv{Mm(Ih Ii Io Js Jt Mr Mz Qc) Js(Is Jq)} Qc{Iq(Is Qa Qb) Ih(Qa Qb) MkJl IsJs} Mk{MmJt IhQb} MmJpJt IqIsJs Constrained panels with 2 analytes, where 1.0E-5 >= 'model p-value' > 0. Contains 2 panels of 7,260 total panels evaluated. : Nx(Ii Js)

Constrained panels with 2 analytes, where 1.0E-4 >= 'model p-value' > 1.0E-5. Contains 3 panels of 7,260 total panels evaluated. : Nx(Ij Jt Nr)

Constrained panels with 2 analytes, where 1.0E-3 >= 'model p-value' > 1.0E-4. Contains 25 panels of 7,260 total panels evaluated. : Nx(Hw Ih Im Io Iq Jm Mk Mr Ms Mz Ng Nt Qc) Ij(Hr Lv Ly Mk Ok) Hr(aA Hw) Qc(Ok Qe) IhQe IiOn JiJs Constrained panels with 2 analytes, where 1.0E-2 >= 'model p-value' > 1.0E-3. Contains 104 panels of 7,260 total panels evaluated. : Lv(aA Hr Ih Io Iq Js Lu Ly Mf Mj Mk Mm Mr Mz Nr Ok Qc) Ji(Hr Ih Ii Ij Io Iq Jt Lj Lu Ly Mk Mr Mz Nr Nt Qc) Ok(Hr Ii Im Iq Js Jt Lu Ly Mk Mr Mz Nm Nr Nt) On(Hu Iq Js Jt Ly Mk Mr Mt Mz Ng Nr Qc) Hr(Ii Iq Ly Mk Mm Mr Nr Nx) Fr(Ii Ly Mk Mr Nr Qc) Qe(Ii Iq Js Lj Mk Nr) Nx(aA In Lj Mj Mt Pa) Ly(aA Mk Mm Mr) Is(Ih Iq Js Qc) Qb(Ih Nr Qc) Mi(Mr Nr) Qc(Qa Qd) Jt(Et Mm) MkJl IjaA Constrained panels with 2 analytes, where 5.0E-2 >= 'model p-value' > 1.0E-2. Contains 128 panels of 7,260 total panels evaluated. : Nr(Et Is Jl Jn Jq Lh Lx Mm My Ne Nv Pf Pg Qa) Js(Et Fr Jl Jn Jp Jq Lh Mi Mm Nv Nw Pg Qa Qb) Ii(Et Is Jl Jn Jq Lh Mm My Nv Pg Qb) On(Hw Ih Im Io Jh Md My Nt Om Oy Pa) Qe(Hw Im Ir Jm Jt Mj Mr Mz Pa) Is(Im Io Jm Jt Lj Mk Mr Mz) Qc(aA Et Jl Jp Jq Mm Ne Nv) Ih(Ir Jl Jn Jq Mm Ne Qa) Iq(Fr Jl Jn Jq Mi My Qb) Mr(aA Et Lx My Ne Ni) Fr(Hu Mt Ng Nq Pa) Mk(aA Mi Mm My Ne) Mz(Et Jl Jp Jq Mm) Jq(Hw Jt Lu Om) Io(Et Jp Mm) Lu(Et Mm) Mi(Mt Pa) Jl(Hu Mt) MgNg MyNd QbLj JiOm JpJt Unconstrained panels with 3 analytes, where 1.0E-8 >= 'AUC p-value' > 0. Contains 621 panels of 287,980 total panels evaluated. : Nx{Js(aA Et Fp Fr Hq Hr Hu Hv Hw Hx Ih Ii Ij Ik Im In Io Ip Iq Ir Is It Iu Iv Jg Jh Ji Jj Jk Jl Jm Jn Jo Jp Jq Jr Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Ny Oe Of Og Oh Oi Ok Om On Oy Oz Pa Pb Pc Pd Pe Pf Pg Po Pz Qa Qb Qc Qd Qe) Jt(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Lh Li Lj Lu Lw Lx Ly Lz Ma Mb Mc Md Me Mf Mg Mh Mi Mj Mk Ml Mm Mn Mp Mr Ms Mt Mu Mv Mw Mx My Mz Na Nb Nc Nd Ne Nf Ng Nh Ni Nj Nk Nl Nm Nn No Nq Nr Ns Nt Nv Nw Ny Oe Of Og Oh Oi Ok Om On Oy Oz Pa Pb Pc Pd Pe Pf Pg Po Pz Qb Qc Qe) Ii(aA Et Fr Hq Hr Hu Hv Hw Hx Ih Ij Ik Im In Io Iq Ir Is It Iu Iv Jg Jh Ji Jj Jk Jl Jm Jn Jo Jp Jq Jr Lh Li Lj Lu Lv Lw Lx Ly Lz Ma Mb Mc Md Me Mf Mg Mh Mi Mj Mk Ml Mm Mn Mp Mr Ms Mt Mv Mw Mx My Mz Na Nb Nc Nd Nf Ng Nh Ni Nj Nk Nm Nn No Nq Nr Ns Nt Nu Nv Nw Ny Oe Of Og Oh Oi Ok Om On Oy Oz Pa Pb Pc Pd Pe Pf Pg Po Pz Qa Qb Qc Qd Qe) Hr(aA Hu Hw Ih Ij Il In Io Iq Iu Jm Jo Lu Mk Mr Ms Mz Nf Ng Nm Nr Of Og Oy Pa Pd Qc) Qc(aA Hw Io Iq Lu Ly Mk Mr Ms Mz Ng Nm Nr Nt Oe Of Og Qb Qe) Nr(Hw Io Lu Mh Mk Mr Ms Mz Ng Nm Nt Of Og Om Oz Qb) Nt(Hw Ij Io Iq Lu Ly Ms Mz Nd Ng Nu Of) Mk(Ij Im Io Iq Lu Ly Mj Mr Ms Mz Ng Of) Ms(Io Lj Lx Mr Mt Mz Nm Pa) Mz(Hu Io Ng Nm Of Oy) Mr(Io Ng Nm Of Og) Ng(Lx Mj Nb) Nm(Mj Mt) Nolj LxIo NbHw LjOf} Hr{Hw(aA Et Fr Hv Ij Is Jg Jh Ji Jk Jl Jn Jp Jq Jr Lh Li Lw Lx Mm Mn Mq Mt Mx My Mz Ne Nh Nn Nv Nw Ok On Pe Pf Pg Pz Qa Qb Qd Qe) Ji(aA Ih Ii Iq Iu Jo Js Jt Lu Ly Mr Ms Mz Nf Nr Om) aA(Ii Ij Il Iq Lw Mm Mr Nd Ne Nf Nj Nr Qc) On(Hu Ii Iq Js Jt

Figure 24 Continued

Mk Mz Ng Og Oy) Fr(Hu Ii Jk Mk Nr Oy) Qe(Ii In Iq Jm Nr Pa) Ii(Et Jl Nv Ok) Mk(Ij Nw) LvIj LxMr Ihls IqJp JsNw} Ji{Js(Hu Hv Hw Ii Ik Io Is Iu Jg Jh Jj Jm Jn Jt Lj Lx Ly Ma Mb Md Me Mf Mh Mk Ml Mr Ms Mt Mz Nb Ng Nk Nm No Nq Nr Nt Nw Oe Og Ok Om Oy Qb Qc) Ly(Mk Nt)} On{Jt(Hu Ii Ij Lj Lx Mk Mr Nb Nq Nr Nt Qc) No(Hu Oy) LyIi} MkQcQe IqQbOk Unconstrained panels with 3 analytes, where 1.0E-7 >= 'AUC p-value' > 1.0E-8. Contains 365 panels of 287,980 total panels evaluated. :
Nx{Mk(aA Hu Hw Ih Il Iu Jm Lh Lj Lw Md Mf Mt Nk Nm Oe Og Om Oz Pa Pd Qe) Nr(Fp Hu Iq Jn Jo Ly Md Mf Mi Ml Mp Nb Nc Nd Ne Nf Nj Nk Oe Pc Qe) Mz(Hw Ij Ik Iq Iu Jk Jm Jo Lu Mf Mg Mr Nb Oe Og Om Qb Qe) Nm(Hu Hw Ih Ij Im Io Iq Jn Lj Lx Ly Md Ml Mp Om Pa) Ng(Ih Im Iq Jn Lj Ml Ms Mt No Nw Pa Pe) Hr(Jj Jk Lj Ly Md Mf Mg Mj Ml Mt Oe Om) Ms(Hu Hw Ih Iq Jn Mf Mj Nb Nq Og) Mr(Hw Ih Iq Lu Ly Nq Nt Oe Om) Io(Hu Hw Ik Iq Mf Mj Mt Nb Oy) Qc(Hu Jo Md Mg Mi Om Oy Pd Qa) Ii(Fp Il Ip Mq Mu Ne Nl) Nt(Im Lj Ne Nj Om Pa) Lx(aA Hw Iq Og Qe) Jt(Lv Mq Nu Qa Qd) Mt(Hw Lu Og) Nb(Iq Lu Of) Nq(aA Hw) Ly(Hu Ik) Iq(Mf Og) Js(Il Lv) MjOg IhQb LjOm} Hr{aA(Hu Ih In Jj Jm Jn Jq Js Lj Lu Ly Mf Mh Mj Ml Ms Mx Ng Nh Nu Of Og Om Oy Oz Pa Pc Qe) Hw(Il Ir Lu Lv Ly Ma Mg Mp Mu Mw Nd Nf Nj Nu Ny Oi Oy Pd Po) Ji(Ij Il In Io Mf Mj Mk Ml Ng Of Og Pd Qc) Fr(Iq Mj Ml Mr Mt Nf Of Og Pa Qc) On(Io Iu Lu Mr Ms Nf Nr Of Pg) Nr(Is Jp Lx Mt Nw Qd) Qe(Ih Il Js Lj Qc) Iq(Is Jl Qa) Jp(Ii Ng Qc) Et(Jt Ng) Mk(Jl Mm) Js(Is Jq) IhQb IiPg QcQd} Ji{Js(aA Hq Hx Ih Ij Il Im Ip Iq Ir Iv Jo Jp Jq Jr Li Lw Lz Mc Mi Mj Mm Mn Mp Mq Mv Mw Mx My Na Nc Nd Ne Nf Nh Ni Nj Nl Nn Ns Ny Of Oh Oz Pa Pb Pc Pd Pe Pf Pg Po Pz Qa Qd Qe) Nt(Hw Nu Om) Ly(Mr Qc) Mk(Io Qc) NoIj} On{Jt(Fp Jk Jq Lw Mj Mm Mp Mt Mz Nn) No(Ij Mk) Ii(Mk Mr) NtNu} Ii{Qe(Lj Qc)} EtLyJt Unconstrained panels with 3 analytes, where 1.0E-6 >= 'AUC p-value' > 1.0E-7. Contains 818 panels of 287,980 total panels evaluated. :
Nx{Nr(aA Et Hq Hv Hx Ih Ij Ik Im In Ip Ir Is Iu Iv Jg Jh Ji Jj Jm Jp Jq Jr Lh Lj Lw Lx Lz Ma Mb Mc Me Mg Mj Mn Mq Mt Mw Mx My Nh Ni Nl Nn No Nq Ns Nu Nv Nw Ny Oi Oy Pa Pd Pe Pg Po Pz Qa) Mk(Hv Ik In Ip Ir Is Jg Jj Jk Jl Jn Jo Li Lx Lz Ma Me Mg Mh Ml Mm Mp Mq Mu Mx My Nb Nc Nd Ne Nf Nj Nn Nq Ns Nt Nv Nw Ny Oi On Oy Pc Pe Pf Pg Po Qa Qb) Qc(Et Ih Ik Im In Ir Is Iu Jg Jk Jm Jn Lj Lv Lx Lz Ma Me Mf Mj Ml Mp Mt Nb Nd Ne Nf Ni Nj Nk Nn No Nq Ns Nv Nw Ny Oz Pa Pc) Nm(Hq Hv Hx Il Ir Is Jh Jm Jr Lh Li Lu Lz Mf Mh Mv Mw My Nf Ng Nn Nq Ns Nt Nv Nw Oe Of Og Oh Ok Pe Pg Po) Hr(Fr Hq Hx Ik Im Ir It Ji Jn Lw Lz Me Mh Mi My Nb Nd Ne Nh Nj Nn Ns Nt Nv Oh Oi Oz Pb Pc Pe Pg Po Pz Qe) Mz(aA Hv Ih Im In Is Jg Jh Jn Li Lj Lx Ly Ma Md Mj Ml Mp Mt My Nc Ne Nf Nk Nn Ns Oi Oz Pa Pd Pg) Ng(Fp Hu Hv Hw Ij Ik Il In Io Ir Iu Jm Lh Li Lz Mb Md Mf Mp My Nf Nn Nq Oe Oh Ok Om Pd Pg Po Qa) Nt(aA Hu Hx Ih Il In Ir Iu Jk Jl Jm Jn Jo Lw Md Me Mf Mj Ml Mm Mt Mx Nc Nf Nh Nk Og Oy Oz Qe) Ms(Ij Ik Im Ir Iu Jg Jk Jm Li Lu Ly Lz Ma Md Mh Ml Mp Nn No Nv Nw Oe Of Om Oy Pd Pc Pg Po Qa) Io(Hv Ih In Iu Jg Jh Jk Jn Lj Ly Mb Md Mg Ml Mp My Nf Nn No Of Og Om Pa Pd Pe Pg Po) Mr(Hu Ij Im Jg Jk Jm Jo Li Lj Lx Md Me Mf Mg Mh Mj Ml Mm Mp Mt Nb Nd Nn Oy Oz Pc) Iq(Hu Hw Ih Ik Im Jg Lu Ly Md Mg Mj Ml Mt Nq Oe Of Om Qb) Of(aA Hu Hw Ih In Jm Jn Lx Md Mf Mj Ml Mt Pa Pd) Og(Ih Ij Im Ir Iu Jn Lj Ly Mf Mp Nb Nq Pa Pe) Hw(Fp Hu Ih Ik In Jm Lj Ly Md Mj Nw Pa Pd) Om(aA Hu Ih In Jm Jn Mf Mj Ml Mt Nb Pa) Mt(aA Jo Lj Mf Ml Oe Oz Pc) Lj(Hu Lu Mg Oe Oy Qe) Lx(Fr Ih Jo Lu Ly) Lu(Hu Ik Mj) Ly(Mf Mj Nb) Nq(Jo Mf) Nb(aA Ih) Hu(Ih Mf) MjOe MpaA NdIk IjOh} Hr{aA(Et Fr Hq Hv Hx Ik Im Io Ir Is It Iu Jh Jk Jl Jp Jt Lh Lz Mc Md Mk Mp Mq Mt Mv My Mz Nc Nk Nl Nm Nn Nq Ns Nw Oh Oi Ok On Pb Pd Pe Pf Po Pz Qd) Fr(Hq Il In Iu Jh Ji Jm Js Lj Lu Md Mf Mh Ms Mv My Mz Nc Ng Nj Nn Nq Om Pc Po) Hw(Hu Ih Ik In Iu Iv Js Lz Mf Mh Mi Ml Mr Ms Mv Na Nl No Nt Oh Oz Pc Qc) Ji(Hu Hx Im Ir Jm Lj Lz Md Mg Mh Mt Nm Nn Nt Oe Oy Pa Pe) On(Ih Il In Jk Jo Ly Md Mg Ml Nm Om Pa Pd Qc) Jp(Ih Ij Io Jm Js Lu Ly Mr Mz Nf Pa) Qe(Hu Ij Iu Lu Mh Mj Mk Ml Mr Oy) Ly(Et Ii In Jm Ne Nf) Iq(Jq Nv Nw Ok Qb Qd) Qa(Ih Ii In Jm Nr Qc) Ii(Jq Lv Mt Nw) Ij(Mi Nf Og Qb) Nr(Jn Ne Nh) Et(Jo Lu) Ne(Ih In) Nf(Jq Nw) Is(In Qc) Ok(Jt Ng) LuJq MkIl MrNw HuJl QdJs} On{Jt(Hv Ik Im Io Ir Iu Jg Jh Ji Jn Jo Js Li Ly Lz Ma Mb Mf Mh Ml Mn Mv My Nc Nm No Ns Oe Oh Oi Oy Pa Pe Po) Mk(Jg Js Lj Ly Mp Mt Mz Nc Ng Nk Nq Nt Og Oh) Ii(Io Js Mz Nq Nt Om Qc) Nt(Hw Ly) NbHw JiJs} Ji{Js(Et Fp In It Jk Lh Lu Mg Mu Nu Nv Oi) Mk(Hw Ih Ij Im Jt Lu Mz Nr Om) Jt(Ly Mb Mr Mz Nr Nt Qc) Ly(Ii Ik Mz Nr) Nr(Hw Om) Nt(Lu Mz) LuQc MzOm IhQb} Mk{Ly(Et Is Jq Mm Ne) Qc(Is Qa) Qe(Ii Lj) FrNq IjQb JqJs} Et{Ly(Ii Nt) Jt(Ij Jq)} Qb{Ih(Nb Ne Qc) JqJs} Ii{Qe(Mr Ok) LyNv} Is{Qc(aA Js) JqJs} FrNqMr LyQcQe MmJtOk Unconstrained panels with 3 analytes, where 1.0E-5 >= 'AUC p-value' > 1.0E-6. Contains 1,852 panels of 287,980 total panels evaluated. :
Nx{Iq(aA Et Fp Hq Hv Hx Ij Il In Ir Is It Iu Iv Jh Ji Jk Jl Jm Jn Jo Jp Jr Lh Li Lj Lz Ma Mb Mc Me Mi Mp Mq Mu Mv Mw My Na Nc Nd Ne Nf Nj Nk Nl Nn No Ns Nu Nv Nw Ny Oh Oi Ok Oy Oz Pb Pc Pd Pe Pf Pg Po Pz Qa Qd Qe) Mr(aA Et Fp Hq Hv Hx Ik Il In Ir Is Iu Iv Jh Ji Jl Jn Jp Jq Jr Lh Lw Lz Ma Mb Mc Mi Mn Mq Mu Mv Mw Mx My Na Nc Ne Nf Nh Ni Nj Nk Nl No Ns Nu Nv Nw Ny Oh Oi On Pa Pd Pe Pg Pz Qa Qb Qd Qe) Io(aA Et Fp Hq Hx Ij Il Im Ir Is It Iv Ji Jl Jm Jo Jp Jq Jr Lh Li Lu Lz Ma Mc Mh Mi Mq Mu Mv Mw Mx Na Nc Nd Ne Nh Ni Nj Nk Nl Nq Ns Nu Nv Nw Ny Oe Oh Oi Ok On Oz Pb Pc Pf Pz Qa Qd Qe) Nt(Et Fr Hq Hv Ik Ip Is It Iv Jg Jh Ji Jj Jp Jq Jr Lh Li Lx Lz Ma Mb Mc Mg Mh Mi Mn Mp Mq Mu Mv Mw My Na Nb Ni Nl Nn No Nq Ns Nv Nw Ny Oe Oh Oi On Pb Pc Pd Pe Pf Pg Po Pz Qa Qb Qd) Ms(aA Et Fp Hq Hv Hx Il In Is It Iv Jh Ji Jl Jo Jp Jq Jr Lh Lw Mb Mc Me Mg Mi Mm Mn Mq Mu Mv Mw Mx My Na Nc Nd Ne Nf Nh Ni Nj Nk Nl Ns Nu Ny Oh Oi Ok On Oz Pb Pc Pf Pz Qb Qd) Mz(Et Fp Fr Hq Hx Il Ip Ir It Iv Ji Jj Jl Jp Jq Jr Lh Lw Lz Mb Mc Me Mh Mi Mn Mq Mu Mv Mw Mx Na Nd Nh Ni Nj Nl No Nq Nu Nv Nw Ny Oh Ok On Pb Pc Pe Pf Po Pz Qa Qd) Ng(aA Et Hq Hx Is It Iv Jg Jh Ji Jj Jk Jl Jo Jp Jq Jr Lu Lv Lw Ly Ma Mc Me Mh Mi Mn Mq Mv Mw Mx Na Nc Nd Ne Nk Ns Nu Nv Ny Of Og Oi On Oy Pb Pc Pf Pz Qb Qd Qe) Hw(aA Et Hq Hv Ij Il Im Ir Is Iu Jg Jh Jk Jn Li Lu Ma Mb Mf Mg Mh Ml Mm Mp Mx Nd Ne Nf Nj Nk Nl Nn No Ns Nv Oe Og Oh Oi Om Oy Oz Pb Pc Pe Pg Po Qa Qb Qe) Nm(Et Fp Fr Ik In Ip It Iu Iv Ji Jj Jk Jl Jo Jp Jq Lw Mb Mc Mg Mi Mq Mu Mx Na Nb Nc Nd Ne Nh Nj Nk Nl No Nu Ny On Oy Oz Pb Pc Pd Pf Pz Qa Qb Qd Qe) Qc(Fp Fr Hq Hv Hx Ij Il Ip It Iv Jh Ji Jj Jl Jp Jq Jr Lh Li Lw Mb Mc Mh Mn Mq Mu Mv Mw Mx My Na Nc Nh Nl Nu Oh Oi On Pb Pe Pf Pg Po Pz Qd) Of(Fp Hv Ij Ik Il Im Ir Is Iu Iv Jg Jh Jk Jo Li Lu Lv Ly Lz Ma Mb Mg Mh Ml Mm Mp My Nf Ni Nn No Nq Ns Nv Oe Og Oh Oy Pb Pc Pe Pg Po Qa) Om(Fp Hv Ij Ik Il Im Ir Iu Iv Jg Jh Jk Jq Jr Li Lu Lx Ly Lz Ma Md Mg Mh Mi Mn Mp My Nf Ni Nn No Nq Ns Nv Oe Og Oh Oy Pb Pc Pe Pg Po Qa) Lu(Fr Hv Ih Ij Im In Ir Iu Iv Jg Jh Jk Jm Jn Li Ly Ma Mb Md Mf Mg Mh Ml Mp My Nf Nn No Nq Ns Nw Oe Og Oi Oy Pa Pd Pe Po Qa Qd) Hr(Et Hv Ip Is Iv Jg Jh Jl Jp Jq Jr Lh Li Lv Lx Ma Mc Mm Mn Mp Mq Mu Mv Mw Mx Na Nc Ni Nk Nl No Nq Nu Nw Ny Ok On Pf Qa Qb Qd) Og(aA Fp Hu Hv Ik Il In Is Jg Jh Jk Jl Jm Lh Li Lz Ma Mb Md Mg Mh Ml My Nd Ne Nn Ns Nw Oe Oh Oi Ok Oy Oz Pd Pg Po Qa Qd) Mj(aA Et Hu Ih Ij Ik Im Iu Jg Jk Jm Jo Lj Lx Md Mf Mg Mi Ml Mm Mp Mt Nb Nd Nf Nk Nn Nq Ns Ny Oy Oz Pc Pd Qb Qe) Mt(Hu Hv Ih Ij Ik Im In Iu Jg Jk Jm Jn Lx Ly Lz Ma Md Me Mg Mi Mp Mq Nb Nf Nn Nq Ns Ny Oi Oy Pa Pd Pz Qb Qe) Lj(aA Et Ih Ij Ik Im In Iu Jg Jh Jk Jm Jo Lx Ly Ma Md Mf Ml Mp My Nb Nc Nf Nk Nn Nq Ns Nv Oi Oz Pd Qb) Ih(Ik Is Jg Jh Jk Jm Jn Ly Ma Md Mf Mg Mh Ml Mp My Nc Nd Ne Nf Nj Nk Nl Nn Nv Nw Oe Oy Oz Pa Qe) Mk(Et Fp Fr Hq Hx It Iv Jh Ji Jp Jq Jr Lv Mb Mc Mi Mn Mv Mw Na Nh Ni Nl No Nu Oh Ok Pb Pz Qd) Ly(Hv Ij In Iu Jg Jh Jk Jm Jn Jo Mb Md Mg Ml Ne Nf Nn No Nv Nw Oe Oi Oy Pa Pd Pe) Hu(aA Ij Ik Im Iu Jn Jo Lx Md Ml Mm Mp Nb Nd Nf No Nq Oe Oz Pa Pc Pd) Lx(Ij In Iu Jl Jm Md Mf Mg Mi Ml Nd Nf Ny Oe Oy Oz Pa Pc Pd Qb) Im(aA In Jm Jo Md Mf Mg Mi Ml Nb Nd Ne Nf Nn Oe Oy Oz Pa Pc Qb) Mf(Ij Jg Jk Jm Jn Md Mg Ml Mp Nb Nd Nn Nv Oe Oy Oz Pa

Hx Ir Jh Li Ma Mm Mw Nd Nj Nm No Ns Oi Oz Pc Pe Po Qa Qd) Oz(Et Hv Il Ir Jh Lh Li Ma Nf Ng No Ns Nv Nw Oh Oi Pe Pg Po) Pc(Et Il Ir Jh Lh Li Ma My Nf No Ns Nv Nw Oh Oi Pe Pg Po) Mm(Hv Io Iq Ir Mh My Mz Nf Ng Nm No Ns Pe Pg Po Qc) Nd(Et Il Ir Jh Lh Ma Mb Ne Nf No Nv Nw Ny Oi Pe Pg) Nv(Fr Hv Il Ir Jl Lz Ma Me Mh Nf Nj Ns Oi Pe Qb) Iq(Fr Ip Ji Jq Lv Lw Mh Mn Mx Nh Ni On) Nf(Et Ir Li Ma No Nw Ny Oh Oi Pg) Mr(Fr Ip It Jj Lv Ok Pb Pf Po) Qe(Ir Li Ms No Nw Oh Pe Po Qa) Ny(Hv Ir Jh Li Ma Oi Pe Pg Po) Io(Fr Ip Jj Lv Lw Me Mn Qb) Ng(Fr Ip Mu Nh Ni Nj Nl) Nm(Lv Ma Me Mn Ni Oi) Ir(Et Is Ma Ne Ns Qb) Pe(Et Mi Ne Nk Qb) Ms(Fr Ip Jj Lv) Il(Li Ne Nw Qb) Nt(Fp Lv Ok) Ma(Mi No Ns) Nw(Ji Lw Ne) Hr(Fp Mb) PoMe NoLw LvMz LzJh NeNl NjOi QcOk LiPf} Hr{Ly(Fp Hq Hu Hv Hx Ih Ik Il Ir It Iu Jg Jh Jj Jk Jl Jr Js Lh Lv Lw Lx Lz Ma Mb Md Mh Mi Mj Mk Mn Mp Mq Ms Mt Mu Mx Nb Nc Nd Ng Nj Nk Nl Nm Nn Nt Nu Nv Ny Of Oh Ok Om Oz Pa Pb Pc Pd Pe Pf Pg Pz Qa Qb Qd) Ij(Et Hq Hu Hx Ih Il Im It Iu Iv Jg Jh Jj Jl Jm Jo Jq Jr Js Li Lj Lz Ma Mc Md Me Mh Mj Mn Mq Ms Mv My Nc Ng Ni Nj Nk Nl Nm Nn No Nr Nt Nu Nv Nw Oe Of Oh Oi Ok Om Oy Oz Pa Pc Pd Pe Pf Pg Po Pz Qa Qc Qd) Qe(Hv Hx Ik Io Ip Iv Jg Jh Jl Jo Jp Jq Jr Jt Li Mc Me Mg Mi Mm Mn Mq Ms Mt Mu Mv Mw Mx My Na Nb Nc Nh Ni Nj Nk Nl Nm Ns Nt Nu Nv Nw Ny Oe Of Oh Oi Ok Oz Pb Pc Pf Pg Po Pz) On(Hv Im Ip Is It Iv Jg Ji Jl Jp Jq Jr Li Lx Ma Mc Me Mi Mn Mp Mq Mu Mv Mx Na Nb Nc Nh Ni Nk Nl No Nq Nt Nu Nv Nw Ny Oh Oi Ok Pb Pc Pf Po Pz Qa Qb Qd) Lu(Hu Hv Ih Ii Il Iq Ir Is Iu Jg Jh Jj Jl Jm Jr Lh Lj Lv Lw Lz Ma Md Mf Mh Mi Mj Mk Ml Mm Mt Mx Nd Ne Ng Nh Nk Nu Nv Og Oy Pa Pf Pz Qa Qb Qd) Jp(Hq Hx Ik Im Ir It Jk Jl Jo Jq Jt Lz Mc Md Me Mf Mg Mi Mm Mn Mq Mt Mx My Nc Nd Ne Nh Nk Nl Nn Ns Of Ok Om Oz Pb Pc Pd Pe Pf Pg) Lw(Hv Ih Is Iu Jl Jm Jn Jq Js Jt Lj Lv Lz Md Mf Mh Mi Mj Ml Ms Mt My Mz Ne Ng Nh Nu Nw Og Ok Oy Pa Pd Pf Qa Qb) Nf(Et Hv Ih Ii Il In Iq Iu Jj Jm Jn Lx Mf Mh Mk Ml Mn Mq Mr Mt Mu My Mz Nd Ne Ng Nh Nk Nr Nu Nv Pg Qa Qc Qd) Iq(Hv Il Jg Jh Jk Jr Lh Li Lv Lx Ma Mf Mh Mi Mk Ml Mm Mp Mq Mr Mu Mw Mx Nd Ng Nj Nn Nr Nu Oy Pd Pe Po Pz) Fr(Et Fp Hv Im Ip Iv Jj Jo Jr Lh Li Ma Mc Me Mi Mm Mn Na Ni Nk Nm No Nt Nu Nw Ny Oz Pf Pz Qa Qb Qd) Nr(Et Ii Il Ir Jg Jk Lv Mf Mi Mk Ml Mm Mn Mp Mq Mu Mx Mz Nc Nd Nj Nl Nn No Nu Oy Oz Pd Pf Po Pz) Jl(Hv Ih Il Is Iu Jn Jq Jt Lj Mf Mh Mi Mj Ml Ms My Mz Nd Ne Ng Nh Nj Nn Ns Nw Ok Om Pa Pd) Ne(Ii Ik Il It Jj Jm Jn Jq Js Lj Lv Lz Md Mj Ms Mz Ng Nh Nl Nv Nw Ok Pa Pd Pf Qc) Mr(Et Hv Ii Il Jj Jn Mi Mk Ml Mm Mp Mq Mu Mx My Mz Nd Ng No Nu Nv Og Pf Pg Qb) In(Hv Il Ir Lh Li Lx Mf Mi Ml Mm Mp Mq Mu Mz Nc Nd Nj Nl Nu Nv Ok Pf Pg Po} Ii(Hv Il Jh Li Lx Mf Mh Ml Mm Mp Mq Mu Mx Nh Nn Nu Oy Oz Pe Pf Pz Qc) Nw(Hx Io Ir It Jj Jk Jm Jo Jt Lj Lz Md Mf Mh Mt My Nd Of Og Om Pc Pg) Ok(Hu Hv Ih Iu Jm Lj Mf Mj Mk Ml Ms Mz Nd Nh Nj Nm Og Oy Oz Pa Pc Qc) Jq(Hu Hv Io Jm Jo Lj Lz Md Mf Mh Mj Mk Ml Nd Ng Nh Of Oy Pa Pd Qc) Nd(Hv Ih Ik Il Is Iu Jj Jn Mf Mh Mk Ml Mn Mp My Mz Ng Nv) Ji(Et Ip Lx Mb Me Mm Mn Mp Mq Nb Nc Ni No Nq Nv Qa Qb Qd) Nh(Hv Il It Iu Jj Jm Jn Js Lj Mf Mh Mj Mk Ml Ms Ng Qc) Mt(Hu Io Jj Jm Js Lj Mf Mh Mj Ml Mz Ng Oy Pa Pd Qc) Il(Hv Iu Jn Lj Mf Mh Ml Ms My Nu Nv Om Qa Qb Qd) Ih(Et Hv Ir Lh Mm Mn Mx My Mz Nj Nv Pf Pg Pz) Is(Im Io Ir It Jj Jm Lj Mf Mh Ml Ms Ng Og Pa) Jn(Iu Jj Lj Mf Mh Mj Mk Ml Ms Mz Ng Oy Pa Qc) Iu(Et Lh Mm My Mz Nj Nu Nv Pf Pg Qa Qb) Mk(Et Hv Lx Mi Mp Mu My Pf Pg Qa Qd) Ng(Lh Lv Ml Mm Mn My Mz Nu Pf Pg Qd) Js(Et Lh Mm Mn Mx My Mz Nv Pf Pg Qb) Qc(Hv Ir Lh Mu My Mz Nv Pf Qb) Pa(Hv Lx Mp Nv Pe Pg Qa Qb Qd) Oy(Et Lv Mu My Nv Pf Pg Qa) Ml(Hv Lv Mm Nj Pf Qa Qd) Jm(Hv Mz Nv Pf Pg Qd) Lj(Hv Li Pf Qa Qb Qd) Et(Ms Nm Oe Og Oz) Mm(Hv Mi Ms Oe Og) My(Ms Nj Og Oz) Mz(Jj Ms Qa Qd) Nv(Hu Jj Jt Og) Lx(Mh Pe Po) Qa(Jj Mh Mj) Pf(Mf Mh Mj) Mn(Jt Om) LvaA MfQd HqHw QbJj} Ji{Jt(Et Fp Fr Hq Hu Hv Hw Hx Ii Il In Io Ip Iq Ir Is It Iu Jh Jj Jk Jl Jn Jo Jp Jq Li Lu Lv Lw Lx Lz Ma Mc Md Me Mp Mq Mt Mv Mw Mx My Na Nf Nn No Nq Ns Nv Nw Oe Oh Om Pa Pb Pd Pe Pf Pg Po Pz Qa Qe) Mk(Fr Hu Hv Ik Il In Iq Ir Is Jg Jl Jm Jn Lw Lx Ma Md Mf Mh Mj Ml Mm Mp Mq Mt Mx Na Nb Nc Nd Ne Nf Nj Nk Nm Nq Ns Nw Oe Of Og Oh Ok On Oy Oz Pa Pc Pe Pf Qb) Nt(aA Hv Hx Ih Ii Im Iq Iu Jl Jn Lj Lz Md Mf Mj Ml Mr Mt Nd Nf Ng Nj Nq Ns Nw Of Og Oh Ok Oy Pa Pd Pf Qb Qe) Ly(aA Hv Hw Im In Io Iq Ir Iu Jg Jm Jn Lu Lz Md Mh Mp Ms Mt My Nc Nf Nm Nn No Nq Nw Oe Of Og Oi Oy Pa Pd Pe) Mz(aA Hu Hv Ih Ij Im Iq Iu Jg Jo Lj Lu Lx Md Mh Mj Ml Ms Mt Nb Ng Nm Nq Oe Of Oh Ok Oy Pd Qb Qe) Nr(aA Hv Ih Ii Ik Im Iq Is Iu Jg Md Mf Ml Mp Mr Nb Ne Nf Ng Nk Nm Nq Nw Oe Of Oy Qa) Om(aA Fp Ih Ik Im Io Iu Jn Mb Mf Mj Ml Mn Mt No Oh Ok) Mr(aA Ih Ii Im Jg Lj Lu Ms Ng Nq Oe Og Qb) Hw(aA Fp Ih Ik Im Mb Mf Mj Ml Mt No Ok) Qc(aA Ih Ii Lv Mf Mi Ml Ng Oe Oy Qa Qb) Io(Ii Ik Lj Mf Mj Ml Ms)(Ih Im Lj No Ok) Lu(Ik Im Mj Nb) Ii(Fr Oy Qe) Og(Ih Im Ok) Lx(aA Qe) Qb(Ij Im) FrNq NmOk JlJs} On{Ii(aA Fr Hq Hu Hv Hx Ih Ij Ik Im Iq Is Iu Jg Jh Jj Jl Jm Jn Li Lj Lu Lv Lx Lz Ma Mb Md Me Mf Mh Mj Ml Mp Mt Nb Nk Nm Nn Ns Nw Oe Og Oh Ok Oz Pa Pd Pf Pg Po Qd) Mk(aA Hv Hx Ik Ip Jh Jj Jk Jn Jq Jr Li Lx Lz Md Me Mf Mj Ml Ms Nd Nf Nh Nl Nn Ns Nu Oe Oy Oz Pa Pb Pc Po Qc Qe) Js(Hv Io Iq Jg Jk Jn Jq Lx Ly Mr Mx Nc Nd Ne Nj Nk Nm Nn Nt Oe Og Oy Oz Pc Qb Qc) Ly(Hu Ik Iq Jk Lj Lx Mf Mj Ml Mz Nm Nn Nr Og Oy) Nq(aA Hu Hw Lu Mr Ms Nm Nt Oe Og Om) Nt(Hx Io Iq Lu Mr Ms Mz Ne Nj Qc) Qc(Hu Hw Io Oe Og Om Qb Qe) Jt(Fr Hx Iv Lv Nd Nk Qd Qe) Nr(Hw Lu Ne Of Og Om Qb) Mr(Hw Io Lu Of Og Om) Hu(Jn Lj Mp Nm Og Om) Mz(Io Ng Oe Of) Lj(Hw Of Og Om) No(Md Mw Pg) Nb(Lu Ng Of) Lx(Io Og) Mp(Io Ng) MtOg IhQb} Qe{Qc(Fp Fr Hu Hv Hw Ik In Io Is Jh Jn Jp Jq Js Lz Md Mf Mh Mj Ml Mt My Mz Nd Nh Nj Nm Nn No Nq Og Oy Pd) Ii(aA Et Ih In Iq Jh Jl Jo Jq Js Lv Mb Mf Mh Mj Ml Mn My Mz Nq Nt Nv Oh Oy Pa Qa) Lj(Hu Hw Ij Iq Jk Jm Js Jt Lu Mf Ml Mt Mz Nb Nc Nd Ne Nj Nn Oe Of Oh Ok Om Oy) Mk(aA Fp Hw Im Io Ir Jl Jm Jq Js Lu Lw Mm Mr My Mz Nb Nd Ne Nh Nj Ok Pa) Nr(aA Iq Is Jm Lu Ly Mr My Nb Nc Nd Nh Nj Nq Oe Ok) Nb(aA Io Jn Jt Ml Mr Mz Nd) Nt(Iq Jm Ly Nd Ne Nh Pa) Mr(Iq Is Jm Ne Nq Pa) Ly(Iq Jm Mf Ml) Nq(aA Ih Jm) Jt(Et Fp Mm) Ok(Iq Mz Nm) Ne(Ih Js) FpIq NoIj} Ly{Mk(aA Fr Ii Ij Iq Jg Jh Jk Jl Jr Lh Lj Lu Mr Mx Nb Nc Nj Nl Nu Nw Ny Ok Pf Qa Qb Qd) Qc(Et Ir Jn Jq Jr Lh Lu Mb Mn Mz Ne Ok Pg Qa Qd) Is(Ih Ii Ik In Iq Jm Lj Mb Mf Mj Ml Mz Nb Nt) My(Hu Hw Ik Iq Js Jt Mr Ms Nb Ng Nr Nt Oy) Et(Hw Io Js Lu Mf Ml Nb Ng Nr Oe Og) Nt(Jn Jp Jq Lh Ne Nh Nu Nv Nw Pg Pz) Mr(Ir Jn Lh Lu Mb Mn Ne Nv Ok Pg) Ii(Fr Ir Jp Lh Mb Mn Mz Ok Pz Qb) Qb(Ih In Iq Js Lj Nb Nr) Jq(Ik Jt Lj Mf Mz Nb Nr) aA(Ik Lj Mb Mf Ml Nb Nr) Jp(Js Jt Lj Mz Nr) Mb(Hw Lu Ne) Nr(Lh Pg) Mn(Jt Lj) Nb(Fr Lu) NeIk InJn IqOk} Qb{Ih(aA Hu Hv Ij Ik In Io Iq Ir Iu Jk Jl Jm Jn Jo Jp Jr Js Lu Lw Lx Lz Mb Md Me Mf Mg Mh Mj Ml Mt Mz Na Nf Ni Nj Nl Nn Nq Ns Nt Nu Oh Oy Pa Pb Pd Pe Pf Po Pz) Qc(Fr Hu Ii In Is Jp Js Lj Lv Mf Mh Mk Ml Mr My Nd Ne Ni Pa Qd) Nr(aA Et Ii Is Jm Jp Jq Lu Mk Nd Nh Nj Nu) Ii(Et Fr Lj Lv My Nv Ok) Js(Jm Mm Mx My Ne Nh Ok) Iq(Fp Lj Mf Mk Ml Mr) Ok(Jm Lj Mr Mz Nm) Mk(Lj Lw Mm) Ij(Lj Mr No) Jm(Ml Mz Pa) EtJt FrNq} Is{Js(aA Fr Hu Hv Ih Ik In Iq Iu Jl Jn Jp Jr Lh Lj Mf Mh Ml Mn Mr Ms Mx Mz Nb Nc Ne Nf Nh Nj Nr Nt Nv Nw Pd) Qc(Fr Ii Io Iq Jt Lu Mf Mi Ml Mr Ms My Nr Nt Oe Og Qa) Nr(aA Ih Ii Jl Mf Ml Mr Ms My Og Oy Pg) Mk(Fr Im Io Iq Ir Iu Lw Mm Mr Mz) Mr(aA Ih Ii Iq Iu Jl Ms Mz) Mz(aA Ih Iq Iu Mf Ok) Nt(Iq Nu) Ih(Mb Ms) FrNq IiOy} Jq{Js(aA Et Hu Hv Ii Ik Iv Jn Jp Lh Lu Md Mf Mh Mi Ml Mm Ms Mt Mx My Mz Nb Nc Nd Ne Nf Nh Nj Nk Nl Nq Ns Nt Nu Oe Of Og Oy Oz Pc Pd Pe Pg Qa Qc) Jt(aA Ih Jp Mb Mf Ml Mn Mr My Mz Nr Nv Pz Qc) Mk(aA Hw Ii Iq Mz Nr Om Qc) Hw(Lj Mr Mz Nb Nr Nt Qc) Om(aA Lj Mr Mz Nr) Qc(aA Lu) NqaA NtNu LvIi} Mk{Fr(Lj Mp Mr Nb Nc Ne Nj Nk Qc) Jl(Js Jt Lu Mr Nd Nh Nj Nl No) Ng(Et Mg My Nv Ok) Nr(Lx My Ne Qa) Mm(Js Jt Lu Og) Ij(Hq Lh Ne Qa) Qc(aA Jp My Ne) aA(Lw Mx Ne) Et(Io Jt) Lx(Mr No) Mn(Hw Lu) Iq(Ok Qa) Pf(Lj Mr) NuLw MyIo IhQa} aA{Qc(Hu Hw Ii Ip Iq Ir Iu Jn Jo Jp Lh Lu Mf Ml Mr Mx Mz Nb Nd Ne Nh Nj Nl Nq Ns Om Oy Pd Pz Qa) Nq(Et Fr Jl Jn Mr My Pg) Nd(Ik Mb Mr Nt) Mx(Js Mr Nr) Nb(Hw Om) EtOm NrNc NtNu MbHw MmJt} Jt{Et(Hw Ih Ii Im Jn Jp Js Lu Lz Md Mf Mj Ml Mm Mr Ms Mz Nb Nc Ne Ng Nh Nj Nk Nt Og Om Oy Qa Qc) Ok(Ii Ij Lj Mb Mr Mz Nr) Qc(Jp Pz Qd) Nv(Ii Mr Nb) FrNb LvMm LwPz} Fr{Nq(Hu Lx Mf Mj Ml Nb Nn No Nt Oy) Nb(Hu Js Lu Mr Om) Hu(Lx No) Ii(Jm Mr)} Ok{Mr(Io Nd Ng Nq Og Pc) Nm(Iq Lx Mx Nq) Iq(Ir Jn Og) Lj(Og Om) NtNd} Qc{Qa(Ih Ii Iq Lj Lu Mi Mr Ne Nr) Qd(Mr Nt) IiNv IoJp IqIr} Et{Io(Hw Mr Og Om) Og(Js Mr Nr) Nt(Hw Nu)

Figure 24 Continued

Lu(Mr Nr) NgJs) Hw{Mn(Lj Mr Mz Nb) Nb(Jl Lv) NrMy} li{Nv(Js Mr Mz) NnJl} Nt{Nu(Jp Nv Nw)} Lv{Nb(Ij Lu)} Mn{IqJs LjOm} NoljLh Nrlqlr MrMyNg Unconstrained panels with 3 analytes, where 1.0E-3 >= 'AUC p-value' > 1.0E-4. Contains 11,374 panels of 287,980 total panels evaluated. :
Nx{My(aA Et Fp Fr Hq Hv Hx Ij Il In Ip Ir Is It Iv Jh Ji Jj Jl Jo Jp Jq Jr Lh Li Lv Lw Lz Ma Mb Mc Md Me Mg Mh Mi Mn Mq Mu Mv Mw Mx Na Nb Nc Nd Ne Nf Nh Ni Nj Nk Nl No Ns Nu Nv Nw Ny Oh Oi On Oz Pb Pd Pe Pf Pg Po Pz Qa Qb Qd Qe) It(aA Et Fp Hq Hv Hx Ij Ik Il In Ir Is Iu Iv Jg Jh Jk Jn Jo Jp Jq Jr Lh Li Lz Ma Mb Mc Md Me Mg Mh Mi Mj Mm Mq Mu Mv Mw Mx Nc Nd Ne Nf Nh Ni Nj Nk Nl Nn No Ns Nu Nv Nw Ny Oh Oi On Oz Pa Pb Pc Pd Pe Pf Pg Po Pz Qa Qb Qe) Mh(aA Et Fp Fr Hq Hv Hx Il Ip Ir Is Iv Jh Ji Jj Jk Jl Jp Jq Jr Lh Li Lv Lw Lz Ma Mb Mc Me Mi Ml Mn Mp Mq Mu Mv Mw Mx Na Nc Nd Ne Nf Nh Ni Nj Nk Nl Nn No Ns Nu Nw Ny Oh Oi Ok On Oz Pb Pc Pe Pf Pg Po Pz Qa Qb Qd Qe) Qd(Et Fr Hq Hv Hx Ih Ik Il Im In Ip Ir Is Iu Iv Jg Jh Ji Jk Jl Jn Jo Jp Jq Lh Li Lv Lw Lz Ma Mc Me Mi Mn Mp Mq Mu Mv Mw Mx Nb Nc Nd Ne Nf Nh Ni Nj Nk Nl Nn No Ns Nu Nv Nw Ny Oh Oi On Oz Pb Pc Pe Pf Pg Po Pz Qe) Et(Fr Hq Hv Hx Ik Il Im Ip Is Iv Jg Jh Ji Jj Jl Jo Jp Jq Jr Li Lv Lw Lx Lz Ma Mb Mc Me Mg Mi Mm Mn Mp Mq Mu Mv Mw Mx Na Nc Ne Nh Ni Nj Nk Nl No Nq Ns Nu Nv Nw Ny Oh Oi Ok On Pb Pd Pf Pg Po Pz Qa Qb Qe) Is(aA Fp Hq Hv Hx Ik Il In Ip Iu Iv Jg Jh Ji Jk Jl Jp Jq Jr Lh Li Lw Lz Ma Mb Mc Md Me Mi Mm Mn Mq Mu Mv Mw Mx Nc Nd Ne Nf Nh Ni Nj Nk Nl Nn No Ns Nu Nv Nw Ny Oh Oi Oz Pb Pc Pe Pf Pg Po Pz Qa Qb Qe) Lh(aA Fr Hq Hv Hx Ij Ik Il Im Ip Ir Iv Jg Jh Ji Jl Jp Jq Jr Li Lv Lw Lx Lz Ma Mb Mc Me Mi Mn Mp Mq Mu Mv Mw Mx Na Nc Ne Nf Nh Ni Nj Nk Nl Nn No Nq Ns Nu Nv Nw Ny Oh Oi Pb Pe Pf Pg Po Pz Qa Qb Qe) Oh(aA Fr Hq Hv Hx Ik Il Ir Iv Jg Jh Ji Jj Jl Jn Jp Jq Jr Li Lw Lz Ma Mc Me Mi Mn Mp Mq Mu Mv Mw Mx Na Nb Nc Nd Ne Nh Ni Nj Nk Nl Nn No Nq Ns Nu Nv Nw Ny Oe Oi Ok On Pb Pd Pe Pf Pg Po Pz Qa Qb) Hq(aA Fp Hv Hx Ik Il In Ir Iu Iv Jg Jh Jk Jl Jo Jp Jq Jr Li Lw Lz Ma Mb Mc Me Mg Mi Mm Mq Mu Mv Mw Mx Na Nb Nc Nd Ne Nf Ni Nj Nk Nl Nn No Ns Nu Nv Nw Ny Oi On Oz Pc Pe Pf Pg Po Pz Qa Qe) Qa(Fp Fr Hv Hx Ik Il In Ip Ir Iu Iv Jg Jh Ji Jk Jl Jp Jr Li Lw Lz Ma Mb Mc Md Me Mi Ml Mp Mq Mu Mv Mw Mx Nb Nc Nd Ne Nf Nh Ni Nj Nk Nn No Ns Nu Nv Nw Ny Oi Oz Pb Pc Pe Pf Pg Po Pz Qb) Fp(Fr Hv Hx Ij Ik Il Im Ir Iu Jg Jh Ji Jk Jn Jr Li Lv Lx Lz Ma Mc Md Me Mf Mg Mi Ml Mp Mv Mw Nb Nd Ne Nf Nh Ni Nj Nk Nn No Nq Ns Nv Nw Ny Oi Oy Oz Pb Pc Pd Pe Pf Pg Po Pz Qb Qe) Nc(aA Hv Hx Il Im Ir Iu Iv Jg Jh Jk Jl Jo Jp Jq Jr Li Lw Lz Ma Mc Me Mg Mi Mq Mu Mv Mw Mx Na Nd Ne Nf Nh Nj Nk Nl Nn No Ns Nu Nv Nw Ny Oi On Oz Pb Pc Pd Pe Pf Pg Po Pz Qb Qe) Ne(aA Fr Hv Hx Ip Iv Jh Ji Jk Jl Jp Jq Jr Li Lv Lw Lz Ma Mb Mc Me Mg Mi Mm Mn Mp Mq Mu Mv Mw Mx Na Nf Nh Ni Nj Nk Nn No Ns Nu Nv Ny Oi Ok On Oy Oz Pb Pc Pf Pg Po Pz Qb Qe) Jh(Fr Hv Hx Ik Il Ip Ir Iv Jg Ji Jj Jk Jl Jp Jq Jr Li Lv Lw Ma Mb Mc Me Mi Mm Mn Mq Mu Mv Mw Mx Na Nf Nh Ni Nj Nk Nl Nn No Ns Nu Nv Nw Oi On Oy Pb Pc Pf Pg Po Pz Qb Qe) Jr(aA Hv Ik Il In Ir Jg Jk Jl Jm Jp Jq Li Lw Lz Ma Mb Mc Md Me Mi Mm Mp Mq Mu Mv Mw Mx Na Nb Nd Nf Ni Nj Nl Nn No Ns Nu Nv Nw Ny Oi On Oy Oz Pc Pd Pe Pf Pg Po Pz Qe) Nk(aA Hv Hx Ik Il Im Ir Iv Jg Jo Jp Jq Li Lw Lz Ma Mc Md Me Mg Mi Mm Mp Mq Mu Mv Mw Mx Na Nb Nd Nf Nh Ni Nj Nl Nn No Ns Nu Nv Nw Ny Oi On Oy Oz Pc Pf Pg Po Pz Qe) Mv(aA Hv Hx Ij Ik Il In Ir Iv Jg Jk Jl Jm Jq Li Lw Lz Ma Mc Md Me Mg Mi Mm Mq Mu Mw Mx Na Nb Nd Nf Ni Nj Nn No Ns Nu Nv Nw Ny Oi Oy Oz Pc Pe Pf Pg Po Pz Qe) Mb(aA Fr Hv Hx Ij Ik Il Im Ir Iu Jg Jk Jn Li Lv Lx Lz Ma Md Me Mf Mg Mi Ml Mm Mp Mw Nb Nf Nh Ni Nj Nl Nn No Nq Ns Nv Nw Ny Oi Oz Pb Pc Pe Pf Pg Po Pz Qe) Hx(Hv Ij Il Ir Iu Iv Jg Jk Jl Jn Jo Jp Jq Li Lz Ma Mc Md Me Mi Mm Mq Mu Mw Na Nd Nf Ni Nj Nl Nn No Ns Nu Nv Nw Ny Oi Ok On Oz Pb Pc Pe Pf Pg Po Pz Qe) Pz(aA Fr Hv Ik Il In Ir Iv Jg Ji Jl Jo Jp Jq Li Lw Lz Ma Mc Me Mg Mi Mn Mq Mu Mw Mx Na Nd Nf Ni Nj No Ns Nu Nv Nw Ny Oi On Oz Pb Pc Pe Pf Pg Po Qe) Mc(aA Hv Ij Ik Il In Ir Iu Jg Jk Jl Jn Jo Li Lw Lz Ma Md Me Mg Mi Mq Mu Mw Na Nb Nd Nf Ni Nj Nn No Ns Nu Nv Nw Ny Oi On Oy Oz Pc Pe Pg Po Qc) Po(Fr Hv Il Ip Ir Iv Ji Jj Jl Jp Jq Li Lv Lw Lz Ma Mi Mn Mq Mu Mw Mx Na Nd Nf Nh Ni Nj Nl Nn No Ns Nu Nv Nw Oi Ok On Oy Pb Pe Pf Pg Qb) Me(aA Hv Il Im Ir Iv Ji Jl Jo Jp Jq Li Lw Ly Lz Ma Mi Mn Mq Mu Mw Mx Na Nd Nf Nj Nl No Nq Ns Nu Nw Ny Oe Oi On Oz Pb Pc Pe Pf Pg Qb Qe) Lz(aA Fr Hv Il Ip Ir Iv Ji Jl Jp Jq Li Lw Ma Mi Mn Mq Mu Mw Mx Na Nd Nf Nh Ni Nj Nl No Ns Nu Nw Ny Oi On Oz Pb Pc Pe Pf Pg Qb Qe) Mm(Fr Il Im Iu Iv Jg Ji Jj Jm Jo Jp Jq Lj Lu Lw Lx Ly Mf Mg Mi Mn Mp Mu Mw Mx Nb Nd Nh Nn Nq Nu Nv Nw Ny Ok On Pa Pb Pd Pf Qb Qe) Hv(Fr Il Ip Ir Iv Ji Jj Jl Jp Jq Li Lw Ma Mi Mn Mp Mq Mu Mw Mx Na Nd Nf Nh Ni Nj Nl No Ns Nu Nw Oi Ok On Pb Pc Pe Pf Pg Qb Qe) Pg(aA Fr Il Ip Ir Iv Ji Jj Jl Jp Jq Li Lv Lw Ma Mi Mn Mq Mu Mw Mx Na Nh Ni Nj Nl Nn No Ns Nu Nv Nw Oi On Oy Pb Pe Pf Qb Qe) Mw(Ij Ik Il In Ir Iv Jg Jk Jl Jp Jq Li Lw Ma Mg Mi Mq Na Nb Nd Nf Ni Nj Nn No Ns Nu Nv Nw Ny Oi Oy Oz Pb Pc Pe Pf Qe) Ip(aA Ij Ik Il Im In Ir Iu Jg Jk Jn Jo Li Lu Ma Md Mf Mg Ml Mp Nb Nd Nf Nj Nn No Ns Nv Nw Ny Oe Oi Oy Oz Pa Pc Pd Pe) Ok(aA Hu Ij Ik Il Im In Iu Jg Jk Jm Jn Jo Li Lx Ma Md Mf Mg Mj Ml Mp Nb Nd Nf Nj Nn Nq Nv Nw Ny Oe Oy Oz Pa Pc Pd Pe) Mu(aA Ij Ik Il In Ir Iu Iv Jg Jk Jm Jo Li Ma Md Mg Mi Mq Nb Nd Nf Ni Nj Nn No Ns Nu Nv Nw Ny Oi Oy Oz Pc Pd Pe Qe) Jq(aA Ik Il Im In Ir Iu Jg Jk Jo Li Ma Md Mf Mg Ml Mp Nb Nd Nf Ni Nj Nn No Ns Nu Nv Nw Ny Oe Oi Oy Oz Pc Pe Qe) Pb(aA Ij Ik Il In Ir Iu Iv Jg Jk Jo Li Ma Md Mf Mg Ml Mp Nb Nd Nf Ni Nn No Nq Ns Nv Nw Ny Oi Oy Oz Pc Pd Pe Qe) Na(aA Ik Il Im In Ir Iu Jg Jk Jm Jn Jo Li Ma Md Mf Mg Mp Nb Nd Nf Nn No Ns Nv Nw Ny Oe Oi Oy Oz Pa Pc Pd Pe) Jp(aA Ij Ik Il Im Ir Iu Jg Jk Jn Jo Li Ma Md Mg Mi Ml Mp Nb Nd Nf Nj Nn No Ns Nv Nw Ny Oi Oy Oz Pc Pd Pe Qe) On(aA Fr Ij Ik Il Im In Ir Iu Jk Jn Jo Li Ma Md Mg Mi Mj Mp Nb Nd Nf No Ns Nv Nw Ny Oe Oi Oy Oz Pc Pd Pe Qe) Mn(aA Ij Ik Il In Ir Iu Jg Jk Jo Li Ma Md Mf Mg Ml Mp Nb Nd Nf Nj Nn No Nq Ns Nv Nw Ny Oi Oy Oz Pc Pd Pe) Jj(aA Hu Ik Il Im In Ir Iu Jg Jk Jn Jo Li Lu Ma Md Mf Mg Ml Mp Nd Nf Nn No Ns Nv Nw Oe Oi Oy Oz Pa Pd Pe) Iv(aA Ik Il Im In Ir Jg Jk Jo Li Ma Md Mg Mi Mp Nb Nd Nf Nj Nn No Ns Nv Nw Ny Oe Oi Oy Oz Pc Pd Pe Qc) Nu(aA Ij Ik Il Im In Ir Iu Jg Jk Jn Jo Li Ma Md Mg Mi Nb Nd Nf Ni Nj Nn No Ns Nv Nw Ny Oi Oz Pc Pe) Nl(aA Ik Il In Ir Iu Jg Jk Jo Li Ma Md Mf Mg Mp Nb Nd Nf Nj Nn No Ns Nv Nw Ny Oi Oy Oz Pc Pd Pe Qe) Mx(aA Ij Ik Il In Ir Iu Jg Jk Jo Li Lx Ma Md Mg Mi Mp Nb Nd Nf Nn No Ns Nv Nw Ny Oi Oy Oz Pc Pe) Nh(aA Il Ir Iu Jg Jk Li Ma Md Mf Mg Ml Mp Nb Nd Nf Nj Nn No Nq Ns Nv Nw Ny Oi Oy Oz Pc Pd Pe Qe) Ni(aA Il In Ir Iu Jg Jk Jn Jo Li Ma Md Mg Mp Nb Nd Nf Nj Nn No Ns Nv Nw Ny Oi Oy Oz Pc Pd Pe Qe) Fr(Ij Ik In Ir Iu Jk Jl Jm Jn Jo Li Ly Ma Md Mf Mg Ml Nd Nf Nj No Ns Nw Ny Oi Oy Oz Pc Pd Pe) Lv(Ih Ik In Ir Iu Jk Jl Jm Jn Jo Li Lu Ly Ma Md Mf Mg Ml Nd Nf Nn Nv Nw Oi Oy Oz Pa Pc Pd Pe) Mq(aA Ik Il Im In Ir Iu Jg Jk Jo Li Ma Md Mg Mi Nb Nd Nf Nn No Ns Nv Nw Ny Oi Oy Oz Pc Pd Pe) Ji(aA Ij Ik Il In Ir Iu Jk Jo Li Ma Md Mf Mg Ml Mp Nb Nd Nf Nj Nn No Ns Nv Ny Oi Oy Oz Pc Pe) Lw(aA Ik Il Im In Ir Iu Jg Jk Jm Jn Jo Li Ma Md Mg Mi Nb Nd Nf Ns Nv Ny Oi Oy Oz Pc Pd Pe) Pf(aA Ik Il In Ir Jg Jk Jo Ma Md Mg Mi Ml Nd Nf Nj Nn No Ns Nv Nw Ny Oi Oy Oz Pc Pd Pe) Jl(aA Ij Ik Il Im In Ir Iu Jo Li Ma Md Mf Mi Nd Nf Nj No Ns Nw Ny Oi Oz Pc Pd Pe) Qb(aA Ik Jg Jo Li Ma Md Mf Mg Ml Mp Nb Nd Nf No Ns Nw Ny Oe Oi Oz Pc Qe) Mi(aA Il In Ir Jo Li Nd Nf Nj Nn No Ns Nv Nw Ny Oe Oi Oz Pc Qe) Nj(Il Ir Li Ma Md Mp Nb Nd Nf Nn No Ns Nw Ny Oz Pc Pe Qe) Il(aA In Ir Jk Jm Ma Nf No Ns Ny Oi Pe Qe) Qe(aA Ik Jo Ma Md Nd Nf Ns Ny Oi Oz Pc) Nw(Ir Jg Li Ma Mp No Ns Nv Ny Oi Pc) Li(Ir Jg Ma Nd No Ns Nv Oi Pe) Ny(aA Jo No Ns Nv Oe Oz Pc) Oi(Ij Ik Ir Jg Ma No Ns Pe) Pe(Ir Ma Nf No Ns) No(Ir Ns Nv) Nd(Ns Oz Pc) Nf(aA Ns) Jk(Jm Oy) MpPa JoaA OzPc} Hr{Mk(Fp Hq Hu Hx Ih Ii Ik Im In Io Ip Ir It Iu Iv Jg Jh Jj Jk Jm Jo Jr Js Jt Lh Li Lj Lv Lz Ma Mb Mc Md Me Mf Mg Mh Mj Ml Mn Mq Ms Mv Mw Mx Mz Na Nb Nc Ng Ni Nj Nk Nl Nm Nn No Nq Ns Nt Nu Nv Ny Oe Of Og Oh Oi Om Oy Oz Pa Pb Pc Pd Pe Po Pz Qb Qc) Il(Et Fp Hq Hu Hx Ih Ik Im Io Ip Ir It Iv Jg Jh Jj Jk Jm Jo Jq Jr Js Jt Lh Li Lw Lx Lz Ma Mb Mc Md Mc Mg Mi Mj Mn Mp Mq Mu Mv Mw Mx Mz Na Nb Nc Ng Ni Nj Nk Nl Nm Nn No Nq Ns Nt Ny Oe Of Oh Oi Ok Oy Oz Pa Pb Pc

Figure 24 Continued

Pd Pe Pf Pg Po Pz Qc) Nh(Et Hq Hu Hx Ik Im Io Ip Ir Is Iv Jg Jh Jk Jo Jr Jt Lh Lv Lz Ma Mc Md Me Mg Mi Mm Mn Mp Mq Mt Mu Mv Mw Mx My Mz Na Nc Nd Nj Nk Nl Nm Nn Nq Ns Nt Nu Nv Nw Ny Oe Of Og Oh Oi Om Oy Oz Pa Pb Pc Pd Pe Pf Pg Po Pz Qb Qd) In(Et Fp Hq Hu Hx Ih Ii Ik Im Io Ip Iq It Iu Iv Jg Jh Jj Jk Jm Jo Jr Js Jt Lj Lv Lz Ma Mb Mc Md Mc Mg Mh Mj Mn Mr Ms Mv Mw Mx My Na Nb Ng Ni Nk Nm Nn No Nq Nr Ns Nt Ny Oe Of Og Oh Oi Om Oy Oz Pa Pb Pc Pd Pe Pz Qc) Nd(Et Hq Hu Hx Ii Im Io Ip Ir It Iv Jg Jh Jm Jo Jr Js Lh Li Lj Lv Lx Lz Ma Mb Mc Md Me Mg Mi Mj Mm Mq Ms Mt Mu Mw Mx Na Ne Nj Nk Nn No Nq Ns Nt Nu Ny Oe Og Oh Oi Oy Oz Pa Pb Pc Pd Pe Pf Pg Pz Qa Qb Qc Qd) Mr(Fp Hq Hu Hx Ih Ik Im Io Ir It Iu Iv Jg Jh Jk Jm Jo Jr Js Jt Lh Li Lj Lv Lz Ma Mb Mc Md Me Mf Mg Mh Mj Mn Ms Mv Mw Na Nc Ni Nj Nk Nl Nm Nn Nr Ns Ny Oe Of Oh Oi Om Oy Oz Pa Pb Pc Pd Pe Po Pz Qc) Is(Et Hq Hu Hv Hx Ik Ip Iv Jh Jk Jn Jo Jp Jq Jr Jt Li Lz Ma Mc Md Me Mg Mi Mm Mn Mq Mt Mu Mv Mw Mx My Na Nc Ne Nj Nk Nl Nm Nn Ns Nt Nu Nv Nw Oe Of Oh Oi Ok Om Oy Oz Pb Pc Pd Pe Pf Pg Po Pz Qb Qe) Nf(Fp Hq Hu Hu Hx Ik Im Io Ip Ir It Iv Jg Jh Jk Jo Jr Js Lh Li Lj Lv Lz Ma Mb Mc Md Me Mg Mi Mj Mp Ms Mv Mw Mx Na Nb Nc Ni Nj Nl Nm Nn No Nq Ns Ny Oe Of Og Oh Oi Om Oy Oz Pa Pb Pc Pd Pe Po Pz Qb) Ne(Et Hq Hu Hv Hx Im Io Ip Ir Iv Jg Jh Jo Jr Jt Lh Li Ma Mb Mc Me Mg Mi Mm Mn Mp Mq Mt Mu Mv Mw Mx My Na Nc Nj Nk Nm Nn No Nq Ns Nt Nu Ny Oe Of Og Oh Oi Om Oy Oz Pb Pc Pe Pg Po Pz Qa Qb Qd) Jq(Et Hq Hx Ik Im Ip Ir It Iv Jg Jh Jj Jk Jn Jr Lh Li Lv Ma Mc Me Mg Mi Mm Mn Mq Mt Mu Mv Mw Mx My Na Nc Ni Nj Nk Nl Nm Nn No Ns Nt Nu Nv Nw Ny Oe Oh Oi Ok Oz Pb Pc Pe Pf Pg Po Pz Qa Qb Qd) Jl(Et Hq Hx Ik Io Ir It Iv Jg Jh Jj Jk Jo Jr Lh Li Lv Lx Lz Ma Mc Md Me Mg Mm Mn Mp Mq Mu Mv Mw Mx Na Nc Ni Nk Nl Nm No Nq Nt Nu Nv Ny Oe Of Oh Oi Oz Pb Pc Pe Pf Pg Po Pz Qa Qb Qd) Ml(Et Hq Hu Ih Ik Im Io Ir It Iu Jg Jh Jj Jm Jr Js Jt Lh Li Lj Lx Lz Ma Md Me Mf Mh Mi Mj Mn Mp Mq Ms Mu Mx My Mz Na Nc Ni Nk Nl Ns Nu Nv Of Og Oi Oy Oz Pa Pc Pd Pg Pz Qb Qc) Qc(Et Hu Ih Iq Iu Iv Jg Jh Jj Jk Jm Jo Jr Js Jt Li Lj Lw Lx Lz Ma Md Mf Mg Mh Mj Mm Mn Mp Mq Ms Mv Mw Mx Nc Ng Ni Nj Nk Nl Nn Nr Ns Nu Oe Of Og Oi Oy Oz Pa Pc Pd Pe Pg Po Pz) Mf(Et Hq Hu Hv Ih Io Ir It Iu Jg Jh Jj Jm Jr Js Lh Li Lj Lv Lx Lz Ma Md Me Mh Mi Mj Mm Mn Mp Mq Ms Mu Mx My Mz Nc Ng Nj Nk Nl Ns Nu Nv Og Oy Oz Pa Pc Pd Pg Pz Qa Qb) Jn(Hq Hu Hv Hx Ik Im Io Ip Ir It Jh Jk Jo Jp Jt Lv Lz Mc Md Me Mg Mi Mm Mn Mq Mt Mu Mx My Na Nc Ni Nj Nk Nl Ns Nt Nu Nv Nw Oe Of Og Ok Om Oz Pb Pc Pd Pe Pf Pz Qb Qd) Mh(Et Hu Hv Ih Io Ir Iu Jg Jh Jj Jm Jr Js Lh Li Lj Lv Ma Md Me Mi Mj Mm Mn Mp Mq Ms Mu Mx My Mz Nc Ng Nj Nl No Nr Nu Nv Of Og Ok Oy Oz Pa Pc Pd Pe Pg Po Pz Qb Qd) Lw(Et Hq Hu Hx Ij Ik Im Io Ir It Iv Jg Jh Jj Jk Jo Jr Lh Ma Mc Me Mg Mn Mu Mv Mx Nb Nc Ni Nj Nk Nl Nm Nn No Nq Ns Nt Nv Oe Of Oh Oi Om Oz Pb Pc Pe Pg Po Pz Qd) Pf(Et Hq Hu Hv Hx Ik Im Io Ir It Jh Jj Jk Jo Jr Jt Lv Lz Ma Md Mi Mm Mn Mq Ms Mt Mx My Mz Nc Ni Nj Nk Nl Nn Ns Nu Nv Nw Of Og Oh Ok Om Oz Pb Pc Pd Pe Po Pz Qb) Ii(Fp Hq Hu Hx Ih Ik Ip Iq Ir It Iu Iv Jj Jm Jr Js Jt Lj Lz Ma Mb Mc Md Me Mg Mi Mj Ms Mw Mx Na Ng Ni Nj Nk Nl Nm No Nq Nt Oe Of Og Oh Oi Om Oz Pa Pb Pc Pd) Nr(Fp Hq Hu Hx Ih Ik Im Io Ip It Iu Iv Jh Jj Jm Jo Jr Js Jt Lj Lz Ma Mb Mc Md Me Mg Mj Ms Mv Mw Na Nb Ng Ni Nk Nm Nq Ns Nt Ny Oe Of Og Oh Oi Om Pa Pb Pc) Lu(Fp Hq Hx Ik Im Io Ip It Iv Jk Jo Js Jt Li Lx Mb Mc Me Mg Mp Mq Ms Mu Mv Mw Na Nb Nc Ni Nj Nl Nm Nn No Nq Ns Nt Ny Oe Of Oh Oi Om Oz Pb Pc Pd Pe Pg Po) Hv(Et Hq Hu Hx Ik Io Ir It Iu Jg Jh Jj Jp Jr Js Lh Lz Ma Md Mj Mn Mp Mq Ms Mu Mx My Mz Nc Ng Nj Nk Nl Ns Nu Nv Nw Of Og Oy Oz Pb Pc Pd Pe Pz Qa Qb Qd) Iq(Fp Hq Hu Hx Ih Im Io Ip It Iu Iv Jj Jm Jo Js Jt Lj Lz Mb Mc Md Me Mg Mj Ms Mv Na Nb Nc Ni Nk Nl Nm No Nq Ns Ny Oe Of Og Oh Oi Om Oz Pa Pb Pc) Mm(Hu Hx Ij Io It Jh Jj Jm Li Lj Lz Ma Mc Md Me Mg Mj Mn Mt My Mz Nc Ni Nj Nk Nm Nn No Ns Nt Nu Nw Ny Of Oh Ok Om On Oy Oz Pa Pb Pc Pd Pe Pg) Ng(Hu Ih Ik Io Ir It Iu Iv Jh Jj Jk Jm Jr Js Li Lj Lx Lz Ma Md Mi Mj Mp Mq Ms Mu Mv Mw Mx Nc Ni Nj Nk Nl Nm Nn No Ny Oi Oy Pa Pb Pd Pe Qa Qb) Ok(Et Hq Hx Ik Io Ip Ir It Jh Jj Jk Jr Lv Lz Mc Md Mg Mi Mn Mt Mw Mx My Na Nb Nc Ni Nk Nl Nn Ns Nu Nv Oe Of Oh Oi Om Pb Pd Pe Pg Po Pz Qd) Lv(Et Fr Hq Hu Hx Ih Ik Im Io Ir Iu Jj Jk Jm Jp Js Jt Lj Lz Md Mj Mn Mq Ms Mx Mz Nc Nj Nl Nq Nu Nw Of Og Om On Oz Pa Pc Pd Pe Qe) Mt(Hq Hx Ik Im Ip Ir It Jh Jk Jo Jr Jt Lx Lz Mc Md Me Mg Mp Ms Mv My Ni Nj Nl Nm Nn Ns Nt Nv Oe Og Oh Oi Oz Pb Pc Pe Pg Po Qd) Iu(Hu Ih Ir Iv Jg Jh Jj Jk Jm Jr Js Li Lj Lx Lz Ma Md Mg Mi Mj Mn Mp Mq Ms Mu Mw Mx Nc Nl Nn No Og Oi Oy Oz Pa Pc Pd Pe Po Pz) Jm(Et Ih Ik Ir Iv Jg Jh Jk Jr Lh Li Lj Lx Lz Ma Mi Mj Mn Mp Mq Ms Mu Mv Mw Mx My Nc Nj Nk Nn Nu Og Oi Oy Oz Pc Pd Pe Po Pz) Ih(Hu Ik Iv Jg Jh Jj Jk Jr Li Lj Lx Lz Ma Md Mg Mi Mj Mp Mq Ms Mu Mw Nc Nk Nl Nn No Nu Ny Og Oi Oy Oz Pc Pd Pe Po) Qd(Hu Hx Ik Im Io Ir It Jj Jk Jo Jp Jt Lz Md Mi Ms My Nj Nk Nm Nn Ns Nt Nu Oe Of Og Oh Om Oy Oz Pc Pd Pe Po Qe) Mz(Et Hq Hu Io Ir It Jg Jt Lh Lj Lx Lz Md Mi Mj Mn Mp Mq Mu Mx My Nc Nj Nk Nu Nv Og Oy Oz Pa Pc Pd Pg Pz Qb) Jp(Et Fp Ip Iv Jg Jh Jr Lh Li Lx Ma Mb Mp Mu Mv Mw Na Nb Ni Nm No Nq Nt Nu Nv Nw Ny Oe Oh Oi Po Pz Qa Qb) Nw(Hq Ik Im Jh Jr Lh Li Lx Ma Mg Mi Mv Mw Mx Nc Ni Nj Nk Nl Nm Nn Nq Ns Nt Nu Ny Oe Oh Oz Pb Pc Po Qb) My(Hu Hx Im Io Ir It Jj Jk Jo Jt Lj Lz Md Me Mg Mi Mj Mq Mx Nc Nl Nm Nn Ns Nv Oe Of Om Pa Pc Pd Pe) Nj(Et Ik Io It Jh Jj Js Lj Lx Lz Ma Md Mi Mj Mn Mp Mq Ms Mu Nc Nk Nu Nv Og Oy Pa Pd Pg Pz Qa Qb) Lj(Et Fp Hu Ir Jg Jj Lh Lx Ma Mi Mn Mq Ms Mu Mx Nl Nu Nv Of Og Oy Oz Pc Pd Pe Pg Po Pz) Mj(Et Ir Jg Jj Lh Li Lx Mi Mn Mp Mq Ms Mu Mx Nc Nl Nu Nv Og Oz Pc Pd Pe Pg Po Pz Qb) Nv(Hq Hx Io Ir It Jk Jo Lz Md Mg Mi Ms Nc Nk Nm Nn Ns Oe Of Om Oz Pb Pc Pd Pe Pg) Js(Ir Jg Jh Jk Jr Li Lx Ma Mi Mp Mq Ms Mu Nc Nl Nn Nu Og Oy Oz Pc Pd Pe Po Pz) Jj(Et Hu Ir Jg Jh Jr Lh Lz Ma Md Mi Mn Mx Nc Nl Nu Om Oz Pa Pc Pd Pe Pg Pz) Ms(Ir Jg Jh Jr Lh Lx Lz Ma Mi Mn Mp Mq Mu Mx Nc Nk Nu Pa Pd Pg Pz Qa Qb) Qa(Hu Hx Ik Im Io Ir It Jk Jt Lz Md Ni Nk Nn Ns Nu Og Oz Pc Pd Pe Qe) Pa(Et Ir Jg Jh Jr Lh Li Ma Mi Mn Mq Mu Mx Nn Nu Og Oy Oz Pc Pd Po Pz) Ly(Im Io Ip Iv Jo Jt Li Mc Me Mg Mv Mw Na Ni No Nq Ns Oe Oi Po) Mi(Et Hu Ik Im Io Ir Lz Mb Md Mn Mq Mx Nc Nu Of Oy Oz Pc Pe Qb) Og(Iv Jg Jh Jk Jr Lh Lz Ma Mg Mn Mq Mu Mx Nk Nu Pd Pg Pz Qb) Et(Hu Im Ip Ir It Jk Lz Md Mg Nc Nl Ns Of Om On Pc Pd Qe) Ij(Fp Ik Io Ip Jk Lx Mb Mg Mp Mu Mw Mx Na Nb Nq Ns Ny Pb) Oy(Hu Jg Jh Jk Lh Li Lx Mn Mp Mq Mv Nn Nu Pd Pe Po Pz Qb) Nu(Hu Io Jh Jo Jr Lz Md Mn Mq Mx Nc Oz Pc Pd Qb) Mn(Hu Io It Jo Lz Me Nc Nk Nl Nm Of Oz Pc Pd) Pg(Hu Io Ir It Jo Jt Lz Md Mp Nk Pd Pe) Qe(Fp Im Lh Lx Ma Mb Mp No Nq Om) Hu(Jg Jh Jk Lh Lx Mp Mu Pz Qb) Qb(Io Ir It Lz Md Nk Pd) Mp(Lz Md Ns Pb Pd Pe) Mu(Ik Jk Md Nk Nn Pd) Lh(Im Io Jo Jt On Pd) Pz(Io Jo Jt Of Oz) Jg(Io Jo Jt Of Pd) Jh(Io Of Om On) Lx(Lz Md Pd) Mq(Lz Md Ns) Mb(Fr On) Mx(Io Lz) Nk(Nc Oz) FpJi IkOn} Ly{aA(Et Fp Hq Hu Hv Hw Hx Ih Ii Ij Il Im In Io Iq Ir Is It Iu Iv Jg Jh Jj Jk Jl Jm Jn Jo Jp Jq Jr Js Jt Lh Li Lu Lw Lx Lz Ma Mc Md Me Mg Mh Mi Mj Mm Mp Mq Ms Mt Mu Mv Mx My Mz Na Nc Nd Ne Nf Ng Nh Ni Nj Nk Nl Nm Nn No Nq Ns Nt Nu Nv Nw Ny Oe Of Og Oh Oi Ok Om On Oy Oz Pa Pb Pc Pd Pe Pf Pg Pz Qb Qe) Mb(Et Fr Hu Hv Ih Ij Ik Il Im In Io Iq Ir It Iu Jh Jk Jl Jm Jn Jp Jq Jr Js Jt Lh Lj Lv Lw Lx Lz Ma Md Me Mf Mh Mi Mj Ml Mm Mn Mp Mq Ms Mt Mu Mx My Mz Nb Nc Nd Nf Ng Nh Nj Nl Nm Nn Nq Nr Ns Nt Nu Nw Ny Oe Of Og Oh Oi Ok Om On Oy Oz Pa Pc Pd Pf Pg Pz Qa Qb Qd Qe) On(Et Fp Hq Hv Hw Hx Ih Ij In Io Ir Is It Iu Jg Ji Jj Jm Jn Jp Jq Jr Li Lu Lz Ma Md Mg Mh Mn Mp Ms Mt Mu Mv Mx Nd Ne Nf Ng Ni Nj Nk No Ns Nv Nw Ny Oe Of Oh Oi Om Oz Pa Pb Pc Pd Pe Pg Po Pz Qa Qd Qe) Ji(Et Fp Fr Hq Hx Ij Il Ip Is It Iv Jh Jj Jk Jl Jo Jp Jq Jr Lh Li Lv Lw Ma Mc Me Mg Mi Mm Mn Mq Mu Mv Mw Mx Na Nc Nd Ng Nh Ni Nj Nk Nl Ns Nu Nv Ny Oh Ok Oz Pb Pc Pf Pg Po Pz Qa Qb Qd Qe) Ii(Hq Hu Hv Hx Ik Im Ip Iq Iu Iv Jg Jh Jk Jl Jo Jr Lj Lu Lv Lw Lx Ma Mf Mg Mi Ml Mm Mq Mr Mt Mu Mx Na Nb Nd Ne Nf Nh Nj Nk Nl Nm Nn Nt Nu Nw Ny Oi Oy Oz Pa Pc Pd Pe Pf Po Qa Qc Qd) Et(Hu Hv Ih Ik In Iq Ir Is It Iu Jg Jk Jm Jn Jo Jp Jq Jr Li Lj Lx Lz Ma Md Mg Mh Mi Mj Mn Ms Mt My Mz Nd Ne Nf Nj Nk Nl Nn No Nq Ns Of Oi Ok Om Oy Pa Pc Pd Pe Pf Po Qa Qb Qe) Jq(Fp Hu Hv Hw Ih In Io Iq Ir Is It Iu Jk Jl Jm Jn Jp Lu Lx Lz Md Mh Mj Ml Mn Ms Mt My Nc Nd Ne Nf Ng Nh Nk Nm Nn No Nq Ns Oe Of Og Oh Oi Ok Om Oy Oz Pa Pd Pe Po Qb Qe) Qc(Fr Hu Hv Ih Ik In Ip Iq Iu Iv Jg Jh Jk Jl Jo Lv Ma Mf Mg Mh Mi Ml Mm Mr Ms Mt Mx Nb Nc Nd Nf Nh Nj Nk Nl Nn No Nr Nt Nu Nv Nw Ny Og Oy Oz Pa Pc Pd Pe Pf

Figure 24 Continued

Mf Mj Ml Mn Ms My Nb Nf Nt Pa Qc) Nr(Hv Iq Ir Lu Mf Ml Mr Ms My Mz Nd Ne Nh Nj Og Oy) Mr(Ii Io Iq Lj Lu Ms Mz Nd Ne Og Qc)
Mz(Ii Iq Lu Mf Ml Nt Of Og Qc) Qc(Ii Iq Jp Lv Mi Ms Og Qa) Ii(Fr Hv Lu Ml Oy) Nq(Fr Lu Lv) Nt(Iq Lu Nd) LuNb MsLj} Fr{Nq(Et Fp Hq
Hw Hx Ih Ij Ik Im Io Iq Ir It Iu Iv Jg Jh Jk Jn Jp Jr Js Lh Li Lu Lw Lz Mb Mc Md Me Mh Mi Mn Mp Mt Mu Mv Mw Mx My Mz Nc Ne Nf Nj
Nk Nl Nm Nr Ns Nu Nv Ny Oe Og Oh Oi Om Oz Pa Pc Pe Pf Pg Po Pz Qa) Ii(Fp Hu Ir It Iu Jj Jk Jn Jo Jp Lh Lj Lx Mb Mh Ml Mn My Nk Nn
No Nt Nu Nv Og Oy Pd Qa Qc) Nb(Ih Ij Io Iq Jk Lj Mf Mj Ml Ms Mt Mz Nd Nj Nn Nr Oe Of Og Oy Pa Pc Qc) Qc(Ir Jp Lu Nc Ne Nj Nt Og
Qa) Nt(Nc Nd Ne Nh Nj Nl) Mr(Hu Mp Nd Ne Nn) No(Ij Nn Oy) Lx(Ml Nn Oy) Nr(Nc Ne) Mb(Hw Om) Hu(Lj Mp) NeLj NeJs} Qc{Qa(Fp
Hu Hv Hw Ih Io Jm Jn Jp Js Lh Lv Lz Mf Mh Mj Ml Mt My Mz Nb Nd Nh Ni Nj Nk Nn Nq Nt Nu Oe Og Oh Oy Pa Pd Qd) Jp(Hu Hw Ii Iq Ir
Js Lu Lv Mi Ml Mr Ms Mz Nb Nd Ne Ng Nj Nq Nr Nt Og Om) Lu(Et Ir Jn Lh Lv Mn Mr My Mz Nb Ne Nu Nv Nw Pg Pz Qd) Qd(Io Js Lj Mf
Mi Ml Mz Nb Nq Nr Oe Og Oy) My(Hw Ii Ir Mr Ms Nd Ne Nj Og Om) Lh(Ii Io Js Ng Nr Og) Mn(Hw Iq Mi Nd Om) Ir(Ih Mi Ml Mr Nr) Og(Et
Jk Ne Nv Pz) Lv(Nb Nc Ne) Mi(Jn Pg) Ii(Jk Jl) Pz(Io Ng) MrNe HuJk} Nr{Ne(Et Hv Hw Ir Jk Jn Jp Lh Lu Lv Mb Mf Ml Mn Mr My Mz Nl Nv
Og Oy Pe Pg Po Qa) My(Fp Io Ir Jn Lu Me Ms Mt Nc Nd Ng Nh Nj Nk Nq Oe Of Og Om Oz Pc Pe Qa) Qa(Et Ih Ii Iq Lu Mf Ml Mr Mx Mz Nb
Nd Nh Nj Oy) Jp(Io Iq Lu Mz Nd Nj Og) Mn(Hw Iq Lu Nd Nh Om) Lh(Hw Ii Io Lu Nc Ng) Et(Hw Io Iq Ng Om) Pg(Ii Lu Nc Og) Nb(Pe Pf Po)
Jn(Iq Lu Nd) Ii(Jk Nv) Ir(Ih Lu) Og(Nv Pd) NtNu MbNd HwJr} Et{Js(Hv Hw Ii Io Iq Ir Jn Lu Mi Mr Nc Nd Ne Nj Nk Nm Oe Oz Pc Qa)
Lu(Hu Hw Ih Ii Io Iq Mj Ml Mt Mz Nb Ng No Nq Nt Oe Og Om) Io(Hu Ii Iq Mf Ml Ms Mz Nc Nj Nk Nq Nt Oe) Ii(Hv Hw Mr Mz Ng Og Om
Oy Qa) Hw(Lj Mr Mz Nb Ng Nm Og) Nt(Iq Nd Ne Ng Nj Om) Om(Lj Mr Nb Ng Nm) Og(Ih Ij Lj Mz) Ng(Lj Mr Mz) MrOe} Mr{My(Hu Hw
Ii Io Iq Js Lu Ms Nd Ne Nm Nn Om Qa) Jp(Ii Io Js Lu Mz Nd Ng Nq) Ne(Hw Lu Mz Nc Nk Nl Og) Nd(Ik Mb Mf Ml Mn Mz) Iq(Ir Jn Mn Qa)
Nu(Lw Mi Nt) Ii(Jl Pg Qa) Nv(Hu Lu Og) Lx(Lj No) Ih(Ir Qa) Jl(Hu Nq) LuJn MnOm NgPz HwJr QaJs} Ii{Nv(Hu Hv Hw Ih Io Iq Jn Lj Lu Lv
Md Mf Mh Mj Ml Ms Mt Nb Ng Nn Nq Ns Nt Oe Og Om Oy Pa) My(Hw Io Jn Om) Pg(Js Lj Lv Nt) Jl(Hu Nb Nq) Lv(Jp Ne) Mn(Hw Om)
MzJp QaLj} Js{My(Hu Ir Jn Nc Nd Nc Ng Nj Nk Nq Qa) Nc(Jn Jp Lh Mb Mn Mz Nv Pg Qa) Nb(Jp Lh Nv Nw Pg Qa) Jp(Io Jn Mx Nd Nj)
Mn(Hw Nd Nh Nj) Mx(Ir Lh) MbNd MmLh NcPg NhJn IqNv QaLj} Hw{Mn(Ih Io Iq Mb Mf Ml My Nd Ne Nh Nq) My(Hu Io Lj Nb Nc Nq
Nt) Nb(Jp Lh Nv Pg Qa) Mb(Lv Mi Nd) MlJr NeNl LjPg} Nt{Nd(Jl Jn Jp Lx Mb Ml Mm Mn My Nv Qa) Nu(Jl Jn Lh Lj Ml Mm Mn My Nh
Pz) LvMm IjLh IqQa} Jp{Mz(Hu Io Iq Nb Ng Nq) Nb(Io Iq Lu) NoIj NdIk NgLj} Mn{Om(Ih Io Iq Ml My Ne) NdIk IjIq} Nb{Lu(Jl Jn Nv Pg)
Iq(Ir Qa) IhQa} Ij{No(Ir Lv My Nv Nw) NqLv HqIq} Ne{Nl(Ml Og) Ih(Jn Qa) HuJl} Mb{Nd(Ih Lu Og)} Iq{Ir(Lj Ml) QaLj} Nq{HuJl IhQa} MlMyNg MxIhIr HuJlLj

Unconstrained panels with 2 analytes, where 1.0E-6 >= 'AUC p-value' > 0. Contains 5 panels of 7,260 total panels evaluated. : Nx(Ii Js Jt Nr) JiJs Unconstrained panels with 2 analytes, where 1.0E-5 >= 'AUC p-value' > 1.0E-6. Contains 15 panels of 7,260 total panels evaluated. : Nx(Hr Io Iq Mk Mr Ms Mz Ng Nm Nt Qc) Hr(aA Hw Ji) JtOn Unconstrained panels with 2 analytes, where 1.0E-4 >= 'AUC p-value' > 1.0E-5. Contains 22 panels of 7,260 total panels evaluated. : Nx(Hu Hw Ih Jm Lj Lu Lx Ly Mf Mj Ml Mp Mt Nq Of Og Om Pa) Hr(Fr On Qe) JiJt Unconstrained panels with 2 analytes, where 1.0E-3 >= 'AUC p-value' > 1.0E-4. Contains 102 panels of 7,260 total panels evaluated. : Nx(aA Et Hq Hv Hx Ij Ik Il Im In Ir Is It Iu Jg Jh Jk Jn Jo Jr Lh Li Lz Ma Mc Md Me Mg Mh Mi Mv Mw My Nb Nc Nd Ne Nf Nk Nn No Ns Nu Nv Nw Ny Oe Oh Oi Oy Oz Pc Pd Pe Pg Po Pz Qd) Hr(Ii Ij Il In Iq Is Jl Jp Jq Lu Lw Ly Mk Nc Nf Nh Nr Nw Ok) Ji(Ly Mk Mz Nr Nt Om Qc) Qc(aA Is Qb Qe) Qe(Ii Lj Mk) Js(Is Jq On) Jt(Et Jq) On(Ii Mk) FrNq NrIs LyaA IhQb Unconstrained panels with 2 analytes, where 1.0E-2 >= 'AUC p-value' > 1.0E-3. Contains 322 panels of 7,260 total panels evaluated. : Hr(Et Hq Hu Hv Ih Ik Im Io Ir It Iu Iv Jg Jh Jj Jm Jn Jo Jr Js Jt Lh Lj Lv Lx Lz Ma Mc Md Mf Mh Mi Mj Ml Mm Mn Mp Mq Mr Ms Mt Mu Mx My Mz Na Nc Nd Ng Ni Nj Nk Nl Ns Nu Nv Of Og Oi Om Oy Oz Pa Pb Pc Pd Pe Pf Pg Pz Qa Qb Qc Qd) Ji(aA Hw Ih Ii Ij Ik Im Io Iq Iu Jg Jn Lj Lu Lx Mf Mh Mj Ml Mr Ms Mt Nb Ng No Nq Nw Nx Oe Of Og Pa) aA(Hu Hw Ih Ii Ij Ik Im Io Iq Is Jn Js Lj Lu Mb Mf Mj Mk Ml Mr Mt Mx Mz Nb Nd Ne Nj Nq Nr Om) Nx(Fp Fr Ip Iv Jj Jl Jp Jq Lv Lw Mb Mm Mn Mq Mu Mx Na Nh Ni Nj Nl Ok On Pb Pf Qa Qb Qe) Ly(Et Hw Ii Iq Is Jp Jq Lh Lu Mb Mk Mn Mr My Nb Ne Nt Ok On Pg Qb Qc Qe) On(Hu Hw Io Iq Lj Lu Mr Mt Mz Nb Ng Nq Nr Nt Oe Of Og Om Qc) Mk(Fr Hx Is Jl Jp Jq Jr Lw Mn My Nd Ne Nh No Nu Nw Qa Qb) Qe(Hw Ih Io Iq Jm Js Jt Mr Mz Nb Nq Nr Nt Pa) My(Hu Hw Ii Iq Js Jt No Nr Qc) Is(Ih Ii Iq Iu Lj Mj Mr Mz Nt) Qb(Ii Iq Jm Js Lj Mr Nr Ok Pa) Jq(Hw Ii Lj Mr Mz Nr Nt Om Qc) Et(Hw Ii Io Js Lu Ng Og Om) Jp(Ii Io Js Jt Mz Nr Qc) Ok(Io Iq Jt Nd Nm Og) Fr(Ii Lx Nb No) Mn(Hw Jt Mr Om) Qa(Ih Js Nr Qc) Jt(Mm Nv Pz) No(Lx Mp) Mr(Nd Ne) Qc(Ir Qd) NnJl NrNe NtNu MbNd HwJr IiNv Unconstrained panels with 2 analytes, where 5.0E-2 >= 'AUC p-value' > 1.0E-2. Contains 874 panels of 7,260 total panels evaluated. : aA(Et Fp Fr Hq Hv Hx Il In Ip Ir It Iu Iv Jg Jh Jj Jk Jl Jm Jo Jp Jq Jr Jt Lh Li Lw Lx Lz Ma Mc Md Me Mg Mh Mi Mm Mn Mp Mq Ms Mu Mv Mw My Na Nc Nf Ng Nh Ni Nk Nl Nm Nn No Ns Nt Nu Nv Nw Ny Oe Of Og Oh Oi Ok On Oy Oz Pa Pb Pc Pd Pe Pf Pg Po Pz Qa Qb Qd Qe) Ji(Et Fp Fr Hq Hu Hv Hx Il In Ip Ir Is It Iv Jh Jj Jk Jl Jm Jo Jp Jq Jr Lh Li Lv Lw Lz Ma Mb Mc Md Me Mg Mi Mn Mp Mq Mu Mv Mw Mx My Na Nc Nd Ne Nf Nh Nj Nk Nl Nm Nn Ns Nu Nv Ny Oh Oi Ok On Oy Oz Pb Pc Pd Pe Pf Pg Po Pz Qa Qb Qd Qe) Ly(Fp Fr Hu Ih Ij Ik In Io Ir Jh Jl Jm Jn Jr Js Jt Lj Lv Ma Mf Mg Mj Ml Mm Ms Mu Mv Mx Mz Nc Nd Nf Ng Nh Ni Nj Nl Nm Nq Nr Nu Nv Nw Ny Oe Of Og Oy Oz Pc Pd Pf Po Pz Qa Qd) Mk(Et Hq Hv Hw Ii Ij Ik Io Iq Ir Iv Jg Jh Jk Jn Js Jt Lh Lj Lu Lx Ma Mb Mf Mg Mi Ml Mm Mr Mt Mu Mv Mw Mx Na Nc Ng Nj Nk Nl Nr Nv Oi Ok Oy Oz Pd Pe Pf Pg Po Pz Qc Qd) Is(Et Fr Hu Hv Hw Ij Ik Il Im In Io Ir It Jh Jk Jl Jm Jn Jt Lu Lz Ma Mb Md Mf Mh Ml Ms Mt My Nb Nc Nd Ne Nf Ng Nk Nm Nn Nq Ns Nu Oe Og Oh Oi Ok Om Oy Pa Pd Pe Pg) Qe(Fp Hu Hv Ij Ik Il In Ir It Iu Jk Jn Jq Li Lu Lx Lz Mb Md Mf Mh Mi Mj Ml Mp Ms Mt Mx My Nd Ne Nf Ng Nh Ni Nj Nm Nn No Oe Og Oh Ok Oy Oz Pc Pd Pe Pg Po Qa) Ne(Et Fr Hu Hw Ih Ii Ik In Io Iq Ir Iu Jm Jn Jp Jq Js Jt Lj Lu Lv Mb Mf Mh Mj Ml Mn My Mz Nc Ng Nk Nl Nt Of Og Ok Om On Pa Qb Qc) On(Hv Hx Ih Ij Ik In Ir Iu Jg Jk Jm Jn Li Lx Ma Md Mf Mh Mj Ml Mp Ms My Nc Nd Nh Nj Nm Nn No Ns Oh Oy Oz Pa Pc Pd Pe Pg Po) Jq(Hu Hv Ih Ik Im In Io Iq Iu Jl Jn Lu Mb Md Mf Mh Mj Ml Ms Mt My Nb Nd Nf Ng Nn No Nq Oe Of Og Ok Oy Pa Qb) Nr(Et Fp Fr Hv Iq Ir Jk Jl Jn Jr Lh Lu Lx Mn Mt Mw Nc Nd Nh Nj Nu Nv Nw Ok Pd Pc Pf Pg Po Pz Qd) Qb(Et Hu Hw Ij Il Im In Io Ir It Iu Jl Jn Lu Lw Lz Md Mf Mh Mj Ml Mt Mx My Mz Nb Nd Nt Oy) Qc(Et Fr Hv Jk Jl Jm Jn Jr Lh Lu Lv Mb Mi Mn Mz Nc Nd Nh Nj Nu Nv Nw Ny Ok Oy Pd Pe Pg Pz) Mn(Hu Ih Ii In Io Iq Jr Js Lj Lu Md Mf Mh Mi Ml Mz Nd Nh Ni Nn Of Og Pa) Ii(Ir Jk Jl Jn Jr Lh Lu Mz Nc Nd Nh Nj Nl Nu Nw Ok Oy Pd Pf Pg Pz Qa) My(Ih Ij Im Io Lu Mj Ml Mr Ms Mz Nc Nd Nf Ng Nj Nm Nn Nq Nt Om Pc) Ok(Hu Hw Js Lj Lu Lx Mf Ml Mr Ms Mz Nf Ng Nh Nj Nq Oe Of Om Oz Pc) Hr(Fp Hx Ip Jk Li Mb Me Mg Mv Mw Nb Nm Nn No Nq Nt Ny Oe Oh Po) Jp(Hw Ih Iq Lj Lu Mj Ml Mr Ms Mt Nb Nd Ng Nq Nt Og Om Pa) Mr(Et Fr Hx Ir Jr Lh Lu Nh Nu Nv Nw Pg Po Qa Qd) Nd(Et Fr Hv Ih Ik Jn Js Lj Me Mf Mh Ml Nt Nv) Js(Fr Ir Jl Jn Lh Mm Mx Nh Nv Nw Pg Pz Qd)
Lj(Et Fr Jr Lu Nc Nh Nv Nw Pe Pf Pg Po Qa) Iq(Et Fr Ir Jk Jn Jr Mb Nh Nu Nv Pg Qa) Nu(Hu Ih Io Lu Lz Md Mf Mj Ml No) Lu(Jn Lh Mb Nb
Nc Nh Nt Nv Pg) Hw(Hx Jh Mb Mg Mw Nb Nc Nh Pz) Fr(Hu Jt Mb Mp Nc Nn Nt Oe) Ih(Et Hv Ir Jn Jr Lh Nh Pf) Et(Ms Mz Nm Nt Oe Of)
Jt(Jl Lw Mg Nh Nw Pg) Nb(Hv Jl Lv Po Qa) Ng(Lh Mb Nh Nv Pz) Og(Mb Mm Nh Nv Pz) No(Jr Lw Mu Mx) Io(Jn Lh Nv Pz) Nq(Jl Lv Nv)
Ml(Iv Jr Nh) Mz(Lh Nw Qa) Nt(Nh Nw) Mf(Iv Jr) Qa(Mj Pa) Lh(Ij Im) LxOh MbMi MdHx HuJl NvOe PaPg

Constrained panels with 3 analytes, where 1.0E-8 >= 'AUC p-value' > 0. Contains 214 panels of 287,980 total panels evaluated. : Nx{Hr(aA Hu
Hw Ih Ii Ij Il In Iq Iu Jm Jo Jt Mk Mr Ms Nf Ng Nm Nr Of Og Oy Pa Pd Qc) Ii(Hw Ij Io Js Jt Lj Lu Mf Mk Mr My Mz Nr Nt Qc) Jt(Hw Ij Js Md
Mm Mr Mt Mz Nr Ok Pz Qc Qe) Mk(Ij Io Iq Js Lu Ly Mr Ms Mz Ng Qc) Nt(Hw Ij Io Iq Lu Ly Ms Mz Nd Nu) Js(aA Hu Hw Ij Ji Md Mf Ng
Qe) Ms(Io Lj Mr Mt Mz Nr Pa Qc) Qc(aA Hw Lu Mr Ng Nr Qe) Mz(Hu Ng Nm Nr Of Oy) Mr(Io Ng Nm) Nr(Hw Lu) No Ij NbHw LjOf}
Hr{Hw(aA Et Fr Hv Ij Is Jg Ji Jk Jl Jn Jp Jq Lh Mm Mn Mt My Mz Ne Nh Nv Nw Ok On Pg Pz Qa Qb Qd Qe) Ji(aA Ih Ii Iq Iu Js Jt Lu Mr Ms
Mz Nf Nr) On(Hu Ii Iq Js Jt Mk Mz Ng Og Oy) Ii(aA Et Fr Jl Nv Ok Qc) aA(Ij Iq Mm Mr Nr Qc) Fr(Hu Jk Mk Nr Oy) Qe(In Iq Jm Nr Pa)
Mk(Ij Nw) LvIj LxMr IhIs IqJp JsNw} On{Jt(Hu Ii Ij Mk Mr Nr Qc) NoOy Lyli} Ji{Js(Ly Mk Mr Qc) Ly(Mk Nt)} MkQcQe IqQbOk Constrained panels with 3 analytes, where 1.0E-7 >= 'AUC p-value' > 1.0E-8. Contains 117 panels of 287,980 total panels evaluated. : Hr{Ji(Ij Il
In Mf Mj Mk Ml Ng Pd Qc) Fr(Iq Mj Ml Mr Mt Nf Pa Qc) On(Iu Mr Ms Nf Nr Of Pg) Nr(Is Jp Lx Mt Nw) Qe(Ih Il Js Lj Qc) Hw(Ir Lv Ly Nu)
Nx(Md Mj Ml Mt) Jp(Ii Ng Qc) aA(In Ly Mf) Et(Jt Ng) Mk(Jl Mm) Iq(Is Qa) Js(Is Jq) IhQb IiPg QcQd} Nx{Mz(Hw Ij Ik Jm Jo Mf Mr) Ng(Ih
Iq Jn Lj Ms Pa) Hw(Io Mk Mr Ms Mt Nm) Mr(Ih Iq Lu Ly) Mk(aA Ih Lj) Ms(Ih Iq Mj) Nm(Md Pa) Lu(Mt Nb) NtIm LxaA LyIk MfIq}
Ji{Nt(Hw Nu Om) Ly(Mr Qc) Mk(Io Qc) Ij(Js No) QeJs} On{Jt(Mm Mt Mz) Ii(Mk Mr) Nolj NtNu} Ii{Qe(Lj Qc)} EtLyJt Constrained panels with 3 analytes, where 1.0E-6 >= 'AUC p-value' > 1.0E-7. Contains 153 panels of 287,980 total panels evaluated. : Hr{Jp(Ih
Ij Jm Js Ly Mr Mz Nf Pa) On(Ih Il In Jk Md Om Pa Pd Qc) Fr(Il Jm Js Ng Nn Po) Ii(Jq Lv Ly Mt Nw Qa) Ji(Hu Im Jm Nt Oy Pa) Qe(Iu Mj Mk
Mr Oy) Nr(Jn Ne Nh Qa) In(Is Ly Ne) Iq(Jq Ok Qb) Qa(Ih Jm Qc) Et(Jo Lu) Mi(Hw Ij) Ok(Jt Ng) MkaA MrNw Nelh HuJl ImNx IsQc QdJs}
Nx{Hw(Hu Ih Jm Lj Ly Mj Ng) aA(Mt Mz Nb Nt Om) Lu(Hu Lx Mj) Ly(Mf Mj Nb) Mr(Ij Im Jm) Lj(Hu Mt Oy) Nt(Jm Mf) Mz(In Md) Ij(Nr
Oh) NmOk LvQc MfOm Mslm NdIk Inlo} On{Ii(Io Js Mz Nq Om Qc) Mk(Js Lj Ly Mt Mz) Jt(Js Ly Pa) Nt(Hw Ly) NbHw} Ji{Ly(Ii Ik Jt Mz
Nr) Lu(Js Mk Nt Qc) Mk(Ij Mz) Jt(Mr Mz)} Mk{Ly(Et Is Mm) Qc(Is Qa) Qc(Ii Lj) IjQb} Ly{Et(Ii Nt) IiNv QcQe} Mr{FrNq IiQe} Qb{IhQc
JqJs} Jt{Etlj MmOk} IiQeOk IsQcJs Constrained panels with 3 analytes, where 1.0E-5 >= 'AUC p-value' > 1.0E-6. Contains 237 panels of 287,980 total panels evaluated. : Hr{Nr(Jl
Jq Lh Ly My Nv Ok Pg Qb) Ii(Is Jg Jn Lh Lw Mn My Qb Qd) Mr(Is Ly Mt Ne Nh Ok) In(Jn Jp Jq Mt Nh Qb) On(Jm Mj Mt Mw My Nn) Ih(Jn
Jq Mt Nh Qd) Jp(Hu Iu Mj Mk Oy) Ne(Iq Mf Mk Ml) Is(Il Iu Mj Mk) Js(Jl Jn Ok Qa) Mm(Jt Ly Nf) Ng(Jg Mg Qe) Iq(Et Ir Jn) Qc(Lu Lv Nw)
Jq(Jt Ms Mz) Fr(Jt Pd) Qc(Ir Mz) Jm(Jn Qb) Ok(Jo Lu) MkMt PaPf} Ly{Mr(aA Et Is Jp On Qe) Ii(Jn Jq My Pg Qe) Qc(aA Is Jp On Qb) Ji(Ih Lj
Mf Mj Nb) Mk(Jp Mn My Qe) Nb(Jp On Qe) Mm(Jt Nt) Is(Js Nr) Nx(In Ng) EtNm QbJm QeLj JqJs} Mk{On(Hu Hw Ij Io Lu Mr Ne Nr Om)
Ij(aA Is My Qe) Ih(Is Qb Qe) Lj(Ji Jl Lx) Nr(Is Qc) Lu(Et Jq) Frli MmaA MrJi IqQe IsJs QcQd} Nx{aA(Hw Im Io Iq Lj Mj Mr) Lu(Hw Jm Md
Ng Oy Pa) Ij(Hw Qc) FrNr MfNd MrNi IhQe IoIm} Qc{Qe(Ih Iq Jm Jt Lj Lu Nr Ok) Qb(Iq Lu Nr Ok) Ji(Mr Ms Mz) Is(Ih Lv) JtOk} Ji{Mz(Ii
Ik Mf Mr Nr) Nt(Ij Ms) Mr(Io Om) Hw(Lj Nb) Jt(Ij Lj) NrLu LvJs} On{Jt(Hw Iq Md Om) Hu(Js Mr Mz) Nt(Nd Om) Js(Is Ng) NoMy Hwli}
Qb{Nr(Ih Iq My) Mr(Ih Jm) EtJs JmLj} Qe{Nb(Iq Lu) NtNu JqJs JtOk} Fr{Nqli NtNu NbHw} Et{IsJs JtaA} NnMrJl Nrlqls NtNuOk JqJsOm Constrained panels with 3 analytes, where 1.0E-4 >= 'AUC p-value' > 1.0E-5. Contains 378 panels of 287,980 total panels evaluated. :
Hr{Ok(Hu Ih Ij In Iu Jm Mf Mj Mk Mz Oy Qc) Mm(Ih Ii In Iq Iu Js Lu Mr Ng Nr) Js(Et Lh Mn Mt Mz Ne Nh Nv Qb) Et(Ih Iu Mk Mr Ms Nr
Oy) Nr(Lv Mi Mn Mz No Pf) Mk(Jn Lu Ly Mi My) Ii(Mz Ne Nh Nu Pf) Qc(Jn Jq Ne Nv Qb) Jt(Jl Jp Mn Nv Qe) On(Im Nb Nt Po) Lv(aA Iq
Lu) Is(Im Jm Ng) Mi(Iq Mr) Mj(Jn Jq) My(Mr Oy) Ih(Ir Jl) Jm(Mt Ne) PoLx MfNd} Ly{Nr(Et Jp Jq Lh My On Pg Qb Qe) Ii(Fr Is Jp Lh Mn
Ok Qb) Et(Js Lu Mf Nb Ng Qc) On(Hu Ik Js Mf Mj Oy) Nt(Jp Jq My Nv Qe) Mk(aA Fr Ij Jl Ok) Qb(Ih In Iq Js Lj) Is(Ih In Jm Lj) Qc(Jq Ok Qa
Qd) Nb(aA Fr Lu) Jt(Jp Jq Mn) Mr(My Ok) Ji(Lu Ms) Nx(aA Nd) MyHw QeJm JpJs} Mk{Qe(Im Io Ir Js Mr Mz Ok) Is(Im Io Iq Mr Mz) Qc(Fr
Jp My On Qb) Fr(Lj Mr Ne) Nr(My Qa Qb) Iq(Ji Qa Qb) On(Md Nd Pa) Mm(Jt Lu) Mr(Jl Pf) Jq(Hw Om) Lj(Pf Qb) Etlo MgNg IhQa JIJs}
Qc{Qa(Ih Ii Iq Lu Mr Nr) Is(Fr Ii Io Iq Lu) On(Hu Hw Js Om) Qb(Fr Js Lv) Ii(Ji Nv) Qe(Js Mz) Jq(Hw Lu) LvJi IoJp Iqlr QdJt NxOk} Mr{Ii(Fr
Is Ji Nv) Jt(Et Jq Nv Ok) On(Hw Io Js Om) Iq(Is Qb Qe) Ji(Ih Lu Ms) Et(Io Lu) Jq(Hw Om) LvNx IhIs IjQb IoOk QeJm} Ji{Mz(aA Ih Ij Ms Ng
Ok) Nt(Iq Nd Ok) Lu(Jt Mj Nb) Ms(Im Io Lj) Fr(Ii Jt) Mf(Hw Om) Ml(Hw Om) MyJt IiOy} On{Nt(Iq Js Ms Ne Nj) Nr(Hw Lu Ne Om) Lj(Hu
Ii Of) Nq(aA Hw) Mz(Ng Of) LuNb LvIi NdJt HuOm JsOy} Qe{Lj(Ij Iq Jm Js Jt Ok) Ii(Iq Jq Lv Mh Mz) Iq(Nr Nt Ok) Jt(Et Mm) Nolj NrOk
NtNd ImNx} Jq{Js(aA Lu Mi My Ne Qa) Jt(aA Jp My Pz) Om(aA Mz Nr) Hw(Mz Nr) NtNu Lvli} Nx{Lv(Ij Io Lx Mj Mt) Fr(Mt Ng) aA(Ih Jn)
NmMm NeNl} Qb{Ij(Ih Lj No) Js(Mm My Ok) Ii(Lj My) MzJm IqLj} Jt{Et(Jn Jp Mm Oy) Ok(Ii Ij Lj Mz) LvMm} Nt{Nu(aA Et Is Jp) EtHw
NdOk} Is{Js(Fr Ih Iq) NrMy} Nq{Fr(aA Ml) MyaA} Nr{EtLu Iqlr} NoIjLh MbNdaA MzliNv Constrained panels with 3 analytes, where 1.0E-3 >= 'AUC p-value' > 1.0E-4. Contains 531 panels of 287,980 total panels evaluated. :
On{Ly(Hw Ih Jm Md Ms Mt Ng Of Pd Pg) Mz(aA Hw Iq Jg Jk Mr Ms Nr Om Oy) Ng(Hw Io Iq Lj Lu Mr Om Pa Qc) Mt(Hw Io Lj Lu Mr Nm
Nt Om) Nt(Ij Md Mw My Oy Pa) Om(Ih Io Iq Js Md Pa) Hu(Hw Ih Im Io Lu) Mr(Iq Nd Nn Oy) Hw(Ih Io Js Oy) Qc(Lv Ms Nr Of) Nr(Js Nd)
Mk(Ih Iq) Ms(Io Lj) Oy(Io Lj) NnLu NqMd NdIk NeIh HrJh} Mk{Js(Et Fr Jn Jp Lh Mp Nv Nw Ok Pg Qa Qb) Qc(Et Jk Jl Jn Lh Nv Nw Pf Pg)
Iq(Fr Ir Jk Jl Jn Nv) Ok(Ij Io Lu Nd Nm) Lv(Hr Ij Ly Mm) My(Hw Mr Nd Ne) Mz(Et Jl Jp Nw) Lj(Is Pe Po Qa) Nr(Fr Jl Pf) Io(Jp Mm Nv)
Mi(Ij Ly) Mn(Hr Ne) Mr(Et Qb) Ii(Jk Qb) Jl(Hu Hw) Jt(Nv Qe) Frlj Luls MmNe NgJk HrNv IhJn} Ly{Nr(Jl Jn Mm Mn Nv Pe Pf Po Qa) Js(Jn
Lh Mm Mn Nv Nw Pg Qa Qe) Fr(Hu Ik Jt Mr Nt Qc) Ih(Ir Jn Jp Jq Qa Qe) Hw(Is Jq Ok Qb Qe) Nt(aA Jl Lw Ok) Mm(Ii Mr Nb Qc) Qe(Ik In Jt
Mj) Lv(Ii Nb Qc) Jl(Ii Mr Qc) Ok(aA Jt Mf) Nv(Jt Qc) EtIk Lwli LxMr NgJp IjaA QaJm} Hr{Mi(Ih Ii Il Jm Js Md Mh Mj Oy Pa Pe) Jt(Is Jg Jn
Mt My Mz Pz Qd) Et(Hu In Jm Mj Mz Pd Qc) Lv(Ih In Jm Js Mf Mj Mr) Mm(Jm Mf Mz Nm Qc) Nn(Jm Oy) MjMx MrNi MyHu NcNk ImQe}
Qe{Ok(Ih Io Jm Js Ng Nt Pa) Jt(Ih Ij Ir Jq Lw Mr) aA(Ir Js Lj Mj Mz Qa) Ij(Mr Nr Nt Qc) Jm(Io Js Mz Pa) Nd(Ik Mb Mf) Ih(Js Mr Nr) Frli
NrMi NtMm MrNi Nblu NgLj ImJi IqJs IrQc} Nr{Ne(Et Fr Jq Lv Mn My Nv Pg) Lu(Is Jn Jp Jq Lh Mn) My(Ji Jq Nd Qa) Qb(Hw Ij Mi Pf)
Ii(Lh Nv Pg) Mn(Nd Nh) Io(Et Jp) Qa(Ih Iq) FrJi NdOk PgaA} Mr{Ii(Et Jl My Ok Pg Qa Qb) Iq(Ir Ji Jq Qa) Fr(Hu Nd Nn) Lu(Is Jn Jq) Ij(aA Is
Ji) My(Nd Ne) Hu(Jl Nv) Ih(Ir Qa) aA(Mm Ni) NtNu NeJq IoJp IsJm PzJt} Qc{Lu(Et Ir Jn Jp Lh Lv Mn Mz Nw Qd) Ii(Jk Lh Ok) Qa(Js Lv Ok)
Qb(Et Hw Ij) aA(Et Lv Mm) Ijls JiOk JqOm} Js{Is(Ij Lv Mm Ok) Qb(Fr Ij Iq Lw) aA(Et Jn Lh Mm) Mn(Nd Ne Nh) My(Jn Ne Qa) Jq(Fr Ij Lv)
Et(Lu Mi) NeJn} Jt{Ij(Is Jp Jq Lh My Nv Pz Qb) Mm(Is Ji Jn Jp Jq) Mn(Nd Ne Nh) My(Et Jn Jp) EtOk FrJq LwNv PzaA LjNw} Nt{Nd(Et Fr

Figure 24 Continued

Is Jl Jn Jp Jq Mm Mn My Nv Qb) Et(aA Iq Ne) Mm(aA Lv Nu) Ne(Fr Ok) Ij{Lh IqOk} Ii{Is(Fr Iq Lj Mz) Lu(Et Ji Jq) Lv(Nv Ok) Ji(Lj My) Jq(Fr Om) MzOk HuJl QaLj} Ij{No(Fr Ir Is Jp My Nv Nw Ok) IqQb} aA{Mz(Et Jq Mm Ok) EtIo NqMm NbNd IhJn IqJq} Lj{Ng(Et Ok) Hu(Fr Jl) Iq(Ir Qa) MsJq HwQb} Ji{Lu(Iq Ml Mt) FrLx NdIk IqOm} Ok{Mz(Iq Ng) Nd(Ik Mf) NmHw IrQb} Nb{Lu(Et Jq) FrNd HwNv} Lv{MbHw ImIs NxPa} Ih{Ne(Is Jn) JqOm} EtNmHw MzIsJm IqJqOm

Constrained panels with 2 analytes, where 1.0E-6 >= 'AUC p-value' > 0. Contains 5 panels of 7,260 total panels evaluated. : Nx(Ii Js Jt Nr) JiJs Constrained panels with 2 analytes, where 1.0E-5 >= 'AUC p-value' > 1.0E-6. Contains 14 panels of 7,260 total panels evaluated. : Nx(Hr Io Iq Mk Mr Ms Mz Ng Nt Qc) Hr(aA Hw Ji) JtOn Constrained panels with 2 analytes, where 1.0E-4 >= 'AUC p-value' > 1.0E-5. Contains 8 panels of 7,260 total panels evaluated. : Nx(Hw Ih Jm Lj Mj Mt Pa) JiJt Constrained panels with 2 analytes, where 1.0E-3 >= 'AUC p-value' > 1.0E-4. Contains 36 panels of 7,260 total panels evaluated. : Hr(Ii Ij Iq Ly Mk Nr Ok) Ji(Ly Mk Mz Nr Nt Om Qc) Qc(aA Is Qb Qe) Nx(aA Ij Im In) Qe(Ii Lj Mk) Js(Is Jq On) Jt(Et Jq) On(Ii Mk) FrNq NrIs LyaA IhQb Constrained panels with 2 analytes, where 1.0E-2 >= 'AUC p-value' > 1.0E-3. Contains 90 panels of 7,260 total panels evaluated. : On(Hu Hw Io Iq Ly Mr Mt Mz Ng Nr Nt Om Qc) Qe(Hw Ih Iq Jm Js Jt Mr Mz Nr Pa) Ii(Et Fr Is Ji Jq My Nv Qb) Mk(aA Fr Is Jl Ly My Ne) Ji(Ih Ij Io Iq Lj Lu Mr) Nr(Jq My Ne Qa Qb) Mr(aA Hr Is Ly Nc) Jp(Io Js Jt Mz Qc) Iq(Is My Ok Qb) Jq(Hw Mz Om Qc) Jt(Mm Nv Ok Pz) Et(Io Js Lu) Is(Ih Lj Mz) Qa(Ih Js Qc) Hr(Lv Mm) Qb(Js Lj) Ok(Ly Nm) NtNu IjaA QcQd Constrained panels with 2 analytes, where 5.0E-2 >= 'AUC p-value' > 1.0E-2. Contains 68 panels of 7,260 total panels evaluated. : Nr(Et Fr Jl Jn Lh Lx Nv Ok Pf Pg) Js(Fr Jl Jn Lh Mm Nv Nw Ok Pg) Qc(Et Fr Jl Lv Ne Nv Ok) Ih(Ir Jn Jq Ne On) Ii(Jl Jn Lh Ok Pg) Fr(Hu Iq Ly Mr) Mk(Ij Mi Mm Ok) Is(Im Io Jm Jt) On(Md My Oy Pa) Ly(Ij Lv Mm) Mr(Et My Ok) Lu(Jq Ok) Mz(Et Ok) Iq(Jn Jq) Qe(Ir Mj) MyNd HuJl

Figure 24 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.8E1 | 8.8E1 | 9.2E1 | 9.4E1 | 6.7E1 | 5.5E1 | 1.0E1 | 8.0E0 | 4.0E2 | 2.4E2 | 69 | 29 | 69 | 29 | 0.53 |
| Ad | ug/mL | 5.2E-2 | 4.9E-2 | 8.4E-2 | 8.9E-2 | 9.2E-2 | 1.0E-1 | 9.4E-4 | 3.9E-3 | 3.6E-1 | 3.5E-1 | 52 | 23 | 52 | 23 | 0.53 |
| Af | ng/mL | 1.5E0 | 9.2E-1 | 1.9E1 | 1.6E1 | 6.3E1 | 5.1E1 | 1.7E-3 | 1.7E-3 | 4.0E2 | 2.5E2 | 52 | 23 | 52 | 23 | 0.48 |
| Aj | ug/mL | 1.3E0 | 7.2E-1 | 2.7E0 | 1.8E0 | 2.7E0 | 2.2E0 | 4.1E-3 | 2.3E-3 | 6.1E0 | 5.8E0 | 52 | 23 | 52 | 23 | 0.43 |
| Al | mg/mL | 1.1E-4 | 8.3E-5 | 2.6E-4 | 3.3E-4 | 4.0E-4 | 4.4E-4 | 8.0E-6 | 7.6E-6 | 1.9E-3 | 1.5E-3 | 52 | 23 | 52 | 23 | 0.54 |
| An | U/mL | 7.8E1 | 4.8E1 | 2.3E2 | 3.0E2 | 3.7E2 | 6.5E2 | 7.7E-1 | 9.6E-1 | 2.0E3 | 3.0E3 | 52 | 23 | 52 | 23 | 0.43 |
| Ao | pg/mL | 1.1E2 | 9.7E1 | 2.1E2 | 1.7E2 | 5.2E2 | 1.7E2 | 6.7E0 | 9.9E0 | 3.8E3 | 6.5E2 | 52 | 23 | 52 | 23 | 0.52 |
| Ap | ng/mL | 3.4E1 | 2.5E1 | 4.5E1 | 3.8E1 | 4.6E1 | 2.7E1 | 8.4E-5 | 5.7E0 | 2.5E2 | 1.0E2 | 52 | 23 | 52 | 23 | 0.48 |
| Ar | ng/mL | 7.5E-1 | 2.2E0 | 4.4E0 | 5.2E0 | 9.6E0 | 7.7E0 | 6.7E-2 | 3.4E-3 | 5.1E1 | 2.8E1 | 52 | 23 | 52 | 23 | 0.59 |
| As | ng/mL | 7.7E-3 | 1.1E-2 | 1.4E-2 | 1.6E-2 | 2.2E-2 | 2.0E-2 | 1.7E-3 | 1.7E-3 | 1.3E-1 | 8.2E-2 | 52 | 23 | 52 | 23 | 0.57 |
| Aw | pg/mL | 1.7E1 | 1.8E1 | 1.7E1 | 1.6E1 | 5.5E0 | 5.7E0 | 9.3E0 | 2.9E-2 | 3.7E1 | 2.5E1 | 52 | 23 | 52 | 23 | 0.52 |
| Ax | ng/mL | 2.2E0 | 8.7E0 | 8.1E0 | 5.9E1 | 1.9E1 | 1.5E2 | 2.5E-2 | 1.2E-2 | 1.3E2 | 6.2E2 | 52 | 23 | 52 | 23 | 0.64 |
| Ba | ng/mL | 7.1E1 | 9.4E1 | 6.4E2 | 3.8E2 | 1.4E3 | 9.2E2 | 2.7E-1 | 6.3E0 | 7.5E3 | 4.4E3 | 52 | 23 | 52 | 23 | 0.49 |
| Bb | ng/mL | 4.2E0 | 5.0E0 | 5.7E0 | 6.6E0 | 5.4E0 | 6.3E0 | 4.1E-3 | 5.4E-1 | 2.0E1 | 1.9E1 | 52 | 23 | 52 | 23 | 0.53 |
| Bc | ng/mL | 3.4E1 | 5.1E1 | 1.2E2 | 6.7E1 | 2.3E2 | 5.8E1 | 2.2E-1 | 2.3E0 | 1.2E3 | 2.2E2 | 52 | 23 | 52 | 23 | 0.55 |
| Bg | ng/mL | 7.1E-2 | 1.2E-1 | 2.2E0 | 1.9E1 | 9.9E0 | 8.2E1 | 5.3E-4 | 2.6E-2 | 7.1E1 | 4.0E2 | 52 | 23 | 52 | 23 | 0.57 |
| Bn | ng/mL | 6.1E-1 | 5.6E-2 | 1.9E0 | 1.6E0 | 2.4E0 | 2.5E0 | 5.6E-2 | 5.6E-2 | 8.6E0 | 7.4E0 | 52 | 23 | 52 | 23 | 0.43 |
| Bo | ng/mL | 9.1E0 | 2.2E1 | 1.3E1 | 1.8E1 | 1.3E1 | 1.3E1 | 1.6E-2 | 1.6E-2 | 4.6E1 | 4.1E1 | 52 | 23 | 52 | 23 | 0.64 |
| Ch | uIU/mL | 1.2E0 | 6.1E-1 | 1.8E1 | 5.4E1 | 4.1E1 | 2.5E2 | 3.4E-3 | 1.2E-1 | 1.9E2 | 1.2E3 | 52 | 23 | 52 | 23 | 0.39 |
| Co | pg/mL | 3.6E1 | 5.6E1 | 4.1E2 | 1.2E2 | 2.3E3 | 1.9E2 | 1.5E-1 | 3.6E0 | 1.7E4 | 8.2E2 | 52 | 23 | 52 | 23 | 0.60 |
| Cp | ng/mL | 2.6E1 | 2.3E1 | 3.2E1 | 2.9E1 | 2.8E1 | 1.6E1 | 1.1E1 | 1.0E1 | 1.9E2 | 6.9E1 | 52 | 23 | 52 | 23 | 0.47 |
| Cq | ng/mL | 3.0E-2 | 4.6E-2 | 1.4E-1 | 9.2E-2 | 7.1E-1 | 1.1E-1 | 8.0E-4 | 7.8E-3 | 5.1E0 | 4.0E-1 | 52 | 23 | 52 | 23 | 0.63 |
| Cs | ng/mL | 8.2E1 | 3.0E2 | 2.6E2 | 1.4E3 | 5.4E2 | 3.7E3 | 1.3E0 | 1.3E0 | 3.0E3 | 1.8E4 | 52 | 23 | 52 | 23 | 0.63 |
| Ct | ng/mL | 4.1E-1 | 8.7E-2 | 4.3E1 | 2.8E1 | 1.2E2 | 9.6E1 | 1.1E-4 | 1.1E-4 | 6.2E2 | 4.6E2 | 52 | 23 | 52 | 23 | 0.41 |
| Cu | ng/mL | 2.6E-1 | 3.1E-1 | 4.1E-1 | 6.1E-1 | 6.4E-1 | 9.4E-1 | 9.0E-5 | 5.6E-2 | 4.5E0 | 4.5E0 | 52 | 23 | 52 | 23 | 0.57 |
| Cv | ng/mL | 6.2E0 | 1.2E1 | 2.3E1 | 3.1E1 | 4.8E1 | 6.5E1 | 2.6E-2 | 5.1E-2 | 3.1E2 | 2.9E2 | 52 | 23 | 52 | 23 | 0.53 |
| Cw | mIU/mL | 2.4E-2 | 3.4E-2 | 3.6E-2 | 3.7E-2 | 2.9E-2 | 2.7E-2 | 2.8E-3 | 4.1E-3 | 1.4E-1 | 1.0E-1 | 52 | 23 | 52 | 23 | 0.51 |
| Cx | ng/mL | 1.1E0 | 3.7E-2 | 6.5E1 | 7.6E1 | 1.1E2 | 1.3E2 | 9.3E-5 | 9.3E-5 | 3.9E2 | 3.9E2 | 52 | 23 | 52 | 23 | 0.45 |
| Db | ug/mL | 6.8E0 | 6.7E0 | 8.0E0 | 7.3E0 | 1.0E1 | 5.5E0 | 5.0E-1 | 1.0E0 | 5.9E1 | 2.1E1 | 52 | 23 | 52 | 23 | 0.56 |
| Dc | nmol/L | 2.4E-2 | 2.4E-2 | 8.0E-2 | 1.0E-1 | 2.3E-1 | 1.9E-1 | 3.0E-4 | 1.0E-3 | 1.6E0 | 7.7E-1 | 52 | 23 | 52 | 23 | 0.59 |
| Dd | ug/mL | 7.5E-2 | 1.4E-1 | 2.2E-1 | 1.8E-1 | 3.7E-1 | 2.1E-1 | 8.3E-5 | 3.3E-3 | 1.9E0 | 7.5E-1 | 52 | 23 | 52 | 23 | 0.52 |
| De | ng/mL | 3.4E-3 | 3.4E-3 | 1.0E-1 | 7.8E-2 | 1.4E-1 | 1.0E-1 | 3.4E-3 | 3.4E-3 | 6.2E-1 | 3.2E-1 | 52 | 23 | 52 | 23 | 0.47 |
| Dg | ng/mL | 3.7E1 | 3.8E1 | 5.1E1 | 4.5E1 | 4.8E1 | 3.7E1 | 1.0E-1 | 1.1E0 | 1.9E2 | 1.2E2 | 52 | 23 | 52 | 23 | 0.49 |
| Di | pg/mL | 1.7E0 | 1.4E0 | 2.2E0 | 2.3E0 | 2.1E0 | 2.0E0 | 1.8E-1 | 1.8E-1 | 7.8E0 | 6.0E0 | 52 | 23 | 52 | 23 | 0.52 |
| Dk | uIU/mL | 1.6E-2 | 1.7E-2 | 4.0E-2 | 5.3E-2 | 6.5E-2 | 8.1E-2 | 1.1E-4 | 5.8E-3 | 3.4E-1 | 3.3E-1 | 52 | 23 | 52 | 23 | 0.55 |
| Dl | ng/mL | 2.4E2 | 1.8E2 | 3.2E2 | 2.5E2 | 2.7E2 | 2.6E2 | 2.5E0 | 5.5E0 | 1.1E3 | 1.1E3 | 52 | 23 | 52 | 23 | 0.41 |
| Dp | ng/ml | 2.1E0 | 1.8E0 | 5.1E0 | 8.1E0 | 6.8E0 | 1.4E1 | 3.7E-3 | 3.7E-3 | 3.5E1 | 5.6E1 | 53 | 23 | 53 | 23 | 0.51 |
| Dr | pg/ml | 1.6E1 | 2.6E1 | 3.5E1 | 5.6E1 | 4.5E1 | 9.9E1 | 7.5E-1 | 7.5E-1 | 1.6E2 | 3.6E2 | 27 | 12 | 27 | 12 | 0.53 |
| Du | pg/ml | 1.2E0 | 1.2E0 | 1.6E3 | 2.2E3 | 5.5E3 | 5.8E3 | 1.2E0 | 1.2E0 | 2.6E4 | 2.0E4 | 23 | 11 | 23 | 11 | 0.56 |
| Ef | ng/ml | 1.6E-1 | 8.6E-2 | 7.7E-1 | 8.3E-1 | 1.5E0 | 2.1E0 | 5.7E-4 | 5.7E-4 | 8.6E0 | 9.4E0 | 52 | 24 | 52 | 24 | 0.48 |
| Wm | % | 4.9E-1 | 4.5E-1 | 2.1E0 | 1.1E2 | 4.3E0 | 3.0E2 | 8.5E-2 | 8.5E-2 | 2.7E1 | 1.0E3 | 55 | 25 | 55 | 25 | 0.53 |
| Ed | pg/ml | 5.2E-1 | 3.1E1 | 2.1E1 | 7.1E1 | 4.2E1 | 1.1E2 | 5.2E-1 | 5.2E-1 | 1.9E2 | 5.0E2 | 53 | 23 | 53 | 23 | 0.69 |
| Yf | ng/mL | 1.7E1 | 1.4E1 | 5.4E1 | 4.2E1 | 1.2E2 | 8.5E1 | 2.2E0 | 2.9E-1 | 5.9E2 | 2.9E2 | 23 | 11 | 23 | 11 | 0.43 |
| Tj | pg/mL | 3.7E-1 | 3.7E-1 | 5.1E1 | 2.4E1 | 3.2E2 | 6.5E1 | 3.6E-1 | 3.7E-1 | 2.3E3 | 3.1E2 | 53 | 24 | 53 | 24 | 0.61 |
| Po | pg/ml | 5.7E-1 | 2.6E0 | 8.7E0 | 1.3E1 | 2.3E1 | 2.6E1 | 2.6E-2 | 2.6E-2 | 1.8E2 | 1.4E2 | 78 | 33 | 78 | 33 | 0.58 |
| Ti | ug/mL | 5.3E0 | 5.2E0 | 5.9E0 | 5.1E0 | 4.7E0 | 4.3E0 | 1.9E-1 | 8.7E-3 | 1.7E1 | 1.4E1 | 40 | 15 | 40 | 15 | 0.46 |
| Em | ng/ml | 1.3E-2 | 2.9E-3 | 3.0E-2 | 3.6E-2 | 3.7E-2 | 6.0E-2 | 1.9E-16 | 8.4E-4 | 1.3E-1 | 1.9E-1 | 29 | 12 | 29 | 12 | 0.44 |
| Et | ng/ml | 1.6E3 | 2.3E3 | 1.8E3 | 2.3E3 | 1.1E3 | 1.3E3 | 1.5E2 | 1.8E2 | 4.4E3 | 5.0E3 | 78 | 33 | 78 | 33 | 0.60 |
| Eq | pg/ml | 2.5E2 | 1.4E2 | 3.4E2 | 1.9E2 | 4.2E2 | 2.8E2 | 1.0E0 | 1.0E0 | 1.8E3 | 1.0E3 | 23 | 11 | 23 | 11 | 0.41 |
| Th | ug/mL | 1.4E0 | 6.2E-1 | 1.6E0 | 1.2E0 | 1.1E0 | 1.4E0 | 1.3E-1 | 2.6E-3 | 4.6E0 | 4.2E0 | 40 | 15 | 40 | 15 | 0.31 |
| Fa | ng/ml | 3.1E1 | 8.7E1 | 7.1E1 | 3.5E2 | 1.2E2 | 8.6E2 | 1.5E0 | 5.9E0 | 7.5E2 | 3.7E3 | 50 | 24 | 50 | 24 | 0.69 |
| Ez | ng/ml | 5.3E0 | 4.1E0 | 2.9E1 | 1.3E1 | 1.0E2 | 2.0E1 | 1.3E-2 | 1.3E-2 | 7.1E2 | 8.8E1 | 53 | 23 | 53 | 23 | 0.49 |
| Fb | ng/ml | 2.4E1 | 3.0E1 | 2.1E1 | 2.8E1 | 1.1E1 | 9.4E0 | 1.0E0 | 5.9E-1 | 4.3E1 | 4.1E1 | 50 | 24 | 50 | 24 | 0.68 |
| Ex | ng/ml | 6.1E-2 | 1.4E-1 | 1.5E-1 | 1.4E-1 | 2.8E-1 | 1.1E-1 | 1.7E-4 | 1.5E-4 | 1.5E0 | 3.3E-1 | 31 | 17 | 31 | 17 | 0.61 |

Figure 25

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fc | pg/ml | 2.2E-1 | 2.2E-1 | 1.9E1 | 4.1E0 | 8.2E1 | 1.1E1 | 2.2E-1 | 2.2E-1 | 3.9E2 | 3.6E1 | 23 | 11 | 23 | 11 | 0.50 |
| Fd | pg/ml | 9.8E-1 | 1.4E1 | 8.7E2 | 1.0E3 | 1.9E3 | 2.7E3 | 9.8E-1 | 9.8E-1 | 8.2E3 | 9.2E3 | 23 | 11 | 23 | 11 | 0.52 |
| Fi | pg/ml | 2.5E-1 | 2.5E-1 | 8.5E1 | 6.4E0 | 3.8E2 | 1.8E1 | 2.5E-1 | 2.5E-1 | 1.8E3 | 6.1E1 | 23 | 11 | 23 | 11 | 0.52 |
| Fn | ng/ml | 2.1E-1 | 1.7E0 | 3.0E0 | 5.4E0 | 5.2E0 | 6.4E0 | 2.1E-1 | 2.1E-1 | 2.1E1 | 1.8E1 | 53 | 23 | 53 | 23 | 0.64 |
| Fp | pg/ml | 1.6E1 | 3.9E1 | 3.1E1 | 4.4E1 | 3.3E1 | 3.9E1 | 2.8E-1 | 3.0E-1 | 1.3E2 | 1.2E2 | 79 | 34 | 79 | 34 | 0.58 |
| Fr | ng/ml | 3.6E4 | 6.8E4 | 1.0E5 | 1.9E5 | 1.6E5 | 2.4E5 | 7.8E2 | 2.5E3 | 8.4E5 | 8.3E5 | 79 | 34 | 79 | 34 | 0.64 |
| Fw | pg/ml | 1.4E0 | 4.0E0 | 1.3E1 | 6.9E1 | 3.9E1 | 2.0E2 | 1.2E-1 | 1.2E-1 | 2.5E2 | 9.1E2 | 51 | 24 | 51 | 24 | 0.62 |
| Fy | ng/ml | 4.1E1 | 5.4E1 | 6.4E1 | 1.2E2 | 5.9E1 | 1.5E2 | 1.2E-1 | 2.7E0 | 2.0E2 | 5.3E2 | 52 | 23 | 52 | 23 | 0.56 |
| Gh | pg/ml | 1.2E1 | 3.9E0 | 9.3E1 | 1.1E1 | 2.7E2 | 1.4E1 | 2.9E-2 | 2.9E-2 | 1.2E3 | 4.6E1 | 22 | 11 | 22 | 11 | 0.44 |
| Gb | % | 4.2E1 | 3.2E1 | 4.5E1 | 3.8E1 | 3.1E1 | 3.8E1 | 4.5E0 | 4.0E0 | 1.0E2 | 1.4E2 | 23 | 11 | 23 | 11 | 0.41 |
| Gc | ng/ml | 7.7E1 | 1.3E2 | 2.0E2 | 1.5E2 | 2.8E2 | 1.3E2 | 6.9E0 | 9.7E0 | 1.2E3 | 4.7E2 | 29 | 12 | 29 | 12 | 0.54 |
| Gd | ng/ml | 2.9E1 | 3.1E1 | 3.5E1 | 2.8E1 | 1.9E1 | 1.7E1 | 8.0E0 | 3.7E0 | 8.1E1 | 5.8E1 | 26 | 12 | 26 | 12 | 0.41 |
| Gn | U/ml | 1.6E-1 | 2.6E-1 | 5.6E-1 | 1.6E0 | 8.3E-1 | 3.4E0 | 5.6E-3 | 5.6E-3 | 3.4E0 | 1.2E1 | 27 | 12 | 27 | 12 | 0.56 |
| Gl | pg/ml | 1.1E4 | 1.0E4 | 1.3E4 | 1.3E4 | 9.7E3 | 9.8E3 | 4.0E2 | 7.2E2 | 3.3E4 | 3.0E4 | 51 | 24 | 51 | 24 | 0.47 |
| Gp | U/ml | 1.2E0 | 5.6E-1 | 3.9E0 | 3.5E0 | 5.9E0 | 9.7E0 | 1.3E-3 | 1.5E-2 | 2.3E1 | 4.8E1 | 52 | 24 | 52 | 24 | 0.38 |
| Gz | ug/ml | 1.0E0 | 1.0E0 | 4.8E0 | 5.1E0 | 5.1E0 | 6.3E0 | 1.6E-1 | 8.9E-2 | 1.1E1 | 1.9E1 | 30 | 17 | 30 | 17 | 0.53 |
| Ha | ng/ml | 2.4E0 | 6.0E0 | 9.2E0 | 1.1E1 | 1.9E1 | 2.1E1 | 1.7E-2 | 1.7E-2 | 1.0E2 | 1.0E2 | 53 | 23 | 53 | 23 | 0.60 |
| Nm | pg/ml | 2.0E4 | 1.7E4 | 3.0E4 | 3.2E4 | 3.4E4 | 3.5E4 | 1.0E-9 | 1.0E-9 | 1.5E5 | 1.2E5 | 79 | 33 | 79 | 33 | 0.50 |
| Nn | pg/ml | 1.4E2 | 4.7E2 | 1.9E3 | 1.6E3 | 1.1E4 | 3.7E3 | 1.0E-9 | 1.0E-9 | 9.5E4 | 1.7E4 | 79 | 33 | 79 | 33 | 0.60 |
| No | pg/ml | 1.5E1 | 2.5E1 | 3.1E1 | 4.3E1 | 4.5E1 | 7.5E1 | 1.0E-9 | 3.3E-1 | 2.6E2 | 4.1E2 | 79 | 33 | 79 | 33 | 0.55 |
| Nq | pg/ml | 1.0E-9 | 4.0E0 | 1.7E1 | 2.3E1 | 7.8E1 | 5.5E1 | 1.0E-9 | 1.0E-9 | 6.7E2 | 2.4E2 | 79 | 33 | 79 | 33 | 0.60 |
| Nr | pg/ml | 1.6E0 | 5.9E0 | 2.2E1 | 2.7E1 | 9.1E1 | 6.3E1 | 1.0E-9 | 1.0E-9 | 7.2E2 | 3.1E2 | 79 | 33 | 79 | 33 | 0.57 |
| Ns | pg/ml | 1.0E-9 | 1.0E-9 | 1.6E1 | 1.1E-1 | 1.3E2 | 6.2E-1 | 1.0E-9 | 1.0E-9 | 1.1E3 | 3.6E0 | 79 | 33 | 79 | 33 | 0.49 |
| Nt | pg/ml | 1.5E2 | 1.5E2 | 1.7E2 | 1.6E2 | 1.2E2 | 8.7E1 | 1.5E1 | 2.3E1 | 8.8E2 | 4.3E2 | 79 | 33 | 79 | 33 | 0.48 |
| Nu | pg/ml | 2.8E1 | 4.3E1 | 8.0E1 | 7.9E1 | 1.1E2 | 9.1E1 | 1.0E-9 | 1.0E-9 | 6.3E2 | 3.4E2 | 79 | 33 | 79 | 33 | 0.52 |
| Lu | pg/ml | 1.0E4 | 1.0E4 | 1.8E4 | 1.0E4 | 6.3E4 | 6.9E3 | 7.1E2 | 1.4E3 | 5.6E5 | 3.6E4 | 79 | 34 | 79 | 34 | 0.50 |
| Lv | pg/ml | 1.4E0 | 1.0E-9 | 1.7E1 | 3.0E1 | 2.5E1 | 5.8E1 | 1.0E-9 | 1.0E-9 | 1.2E2 | 2.6E2 | 79 | 34 | 79 | 34 | 0.51 |
| Lw | pg/ml | 1.0E-9 | 1.0E-9 | 2.5E-1 | 1.0E-9 | 1.7E0 | 0.0E0 | 1.0E-9 | 1.0E-9 | 1.4E1 | 1.0E-9 | 79 | 34 | 79 | 34 | 0.49 |
| Lx | pg/ml | 1.0E-9 | 1.3E2 | 1.7E2 | 3.3E2 | 5.5E2 | 8.0E2 | 1.0E-9 | 1.0E-9 | 4.4E3 | 4.5E3 | 79 | 34 | 79 | 34 | 0.65 |
| Ly | pg/ml | 1.0E-9 | 1.0E-9 | 1.6E1 | 1.4E1 | 2.4E1 | 1.9E1 | 1.0E-9 | 1.0E-9 | 1.2E2 | 7.0E1 | 79 | 34 | 79 | 34 | 0.56 |
| Lz | pg/ml | 1.0E-9 | 1.0E-9 | 2.2E0 | 3.9E0 | 1.5E1 | 1.3E1 | 1.0E-9 | 1.0E-9 | 1.3E2 | 5.6E1 | 79 | 34 | 79 | 34 | 0.52 |
| Ma | pg/ml | 2.6E2 | 5.2E2 | 1.2E3 | 3.6E3 | 2.3E3 | 1.0E4 | 1.0E-9 | 1.7E1 | 1.5E4 | 5.2E4 | 79 | 34 | 79 | 34 | 0.51 |
| Mb | pg/ml | 3.2E1 | 3.0E1 | 3.8E1 | 3.7E1 | 1.9E1 | 1.7E1 | 1.4E1 | 1.4E1 | 1.1E2 | 6.4E1 | 79 | 34 | 79 | 34 | 0.47 |
| Mc | pg/ml | 1.0E-9 | 1.0E-9 | 2.1E-2 | 1.0E-9 | 1.9E-1 | 0.0E0 | 1.0E-9 | 1.0E-9 | 1.7E0 | 1.0E-9 | 79 | 34 | 79 | 34 | 0.49 |
| Md | pg/ml | 1.0E-9 | 1.0E-9 | 6.8E-1 | 1.6E-1 | 2.7E0 | 9.4E-1 | 1.0E-9 | 1.0E-9 | 1.6E1 | 5.5E0 | 79 | 34 | 79 | 34 | 0.47 |
| Me | pg/ml | 2.4E1 | 2.4E1 | 2.6E1 | 2.3E1 | 2.3E1 | 1.6E1 | 1.0E-9 | 2.4E-1 | 1.6E2 | 6.0E1 | 79 | 34 | 79 | 34 | 0.47 |
| Mf | pg/ml | 1.0E-9 | 1.0E-9 | 1.0E0 | 5.4E-1 | 4.3E0 | 1.2E0 | 1.0E-9 | 1.0E-9 | 3.7E1 | 5.0E0 | 79 | 34 | 79 | 34 | 0.55 |
| Mg | pg/ml | 1.6E0 | 1.3E0 | 7.4E0 | 7.0E0 | 1.2E1 | 1.1E1 | 1.0E-9 | 1.0E-9 | 5.9E1 | 3.9E1 | 79 | 34 | 79 | 34 | 0.50 |
| Mh | pg/ml | 1.0E-9 | 1.0E-9 | 7.6E-1 | 2.2E0 | 3.5E0 | 7.5E0 | 1.0E-9 | 1.0E-9 | 2.9E1 | 4.2E1 | 79 | 34 | 79 | 34 | 0.60 |
| Mi | pg/ml | 1.0E-9 | 1.0E-9 | 9.4E-1 | 1.0E-9 | 8.0E0 | 0.0E0 | 1.0E-9 | 1.0E-9 | 7.1E1 | 1.0E-9 | 79 | 34 | 79 | 34 | 0.49 |
| Mj | pg/ml | 1.0E-9 | 1.0E-9 | 3.2E0 | 8.2E0 | 1.1E1 | 2.2E1 | 1.0E-9 | 1.0E-9 | 8.1E1 | 1.1E2 | 79 | 34 | 79 | 34 | 0.57 |
| Mk | pg/ml | 4.3E0 | 5.3E0 | 2.4E1 | 8.5E0 | 1.5E2 | 1.1E1 | 1.0E-9 | 1.0E-9 | 1.3E3 | 3.8E1 | 79 | 34 | 79 | 34 | 0.51 |
| Ml | pg/ml | 1.0E-9 | 1.0E-9 | 2.7E0 | 1.5E1 | 8.9E0 | 6.1E1 | 1.0E-9 | 1.0E-9 | 6.4E1 | 3.4E2 | 79 | 34 | 79 | 34 | 0.50 |
| Mm | pg/ml | 6.3E2 | 7.8E2 | 1.0E3 | 1.1E3 | 1.2E3 | 1.3E3 | 1.0E-9 | 1.9E1 | 6.3E3 | 6.1E3 | 79 | 34 | 79 | 34 | 0.52 |
| Mn | pg/ml | 5.6E0 | 7.0E0 | 9.3E0 | 1.3E1 | 1.2E1 | 2.2E1 | 1.0E-9 | 1.0E-9 | 6.8E1 | 1.3E2 | 79 | 34 | 79 | 34 | 0.56 |
| Mp | pg/ml | 1.0E-9 | 1.0E-9 | 1.2E1 | 1.3E1 | 7.1E1 | 3.0E1 | 1.0E-9 | 1.0E-9 | 6.3E2 | 1.5E2 | 79 | 34 | 79 | 34 | 0.55 |
| Mq | pg/ml | 1.0E-9 | 1.0E-9 | 1.8E0 | 5.7E0 | 7.3E0 | 1.6E1 | 1.0E-9 | 1.0E-9 | 4.6E1 | 8.6E1 | 79 | 34 | 79 | 34 | 0.56 |
| Mr | pg/ml | 1.0E-9 | 1.0E-9 | 1.5E1 | 5.1E1 | 5.3E1 | 2.6E2 | 1.0E-9 | 1.0E-9 | 3.9E2 | 1.5E3 | 79 | 34 | 79 | 34 | 0.50 |
| Ms | pg/ml | 4.1E2 | 1.8E2 | 5.8E2 | 3.8E2 | 5.9E2 | 4.8E2 | 1.0E-9 | 1.0E-9 | 3.3E3 | 2.2E3 | 79 | 34 | 79 | 34 | 0.38 |
| Mt | pg/ml | 8.1E-1 | 1.6E0 | 6.0E0 | 9.2E0 | 2.0E1 | 2.4E1 | 1.0E-9 | 1.0E-9 | 1.4E2 | 1.0E2 | 79 | 34 | 79 | 34 | 0.59 |
| Mu | pg/ml | 1.0E-9 | 1.0E-9 | 3.4E0 | 6.5E-1 | 2.6E1 | 1.7E0 | 1.0E-9 | 1.0E-9 | 2.3E2 | 7.3E0 | 79 | 34 | 79 | 34 | 0.52 |
| Mv | pg/ml | 1.0E-9 | 1.0E-9 | 4.0E1 | 1.2E2 | 1.5E2 | 4.6E2 | 1.0E-9 | 1.0E-9 | 8.4E2 | 2.5E3 | 79 | 34 | 79 | 34 | 0.56 |
| Mw | pg/ml | 2.2E1 | 7.3E1 | 1.8E2 | 3.1E2 | 4.9E2 | 1.0E3 | 1.0E-9 | 1.0E-9 | 2.9E3 | 5.9E3 | 79 | 34 | 79 | 34 | 0.62 |
| Mx | pg/ml | 1.0E-9 | 1.0E-9 | 7.0E-1 | 3.0E-1 | 3.6E0 | 5.7E-1 | 1.0E-9 | 1.0E-9 | 3.2E1 | 2.1E0 | 79 | 34 | 79 | 34 | 0.54 |
| My | pg/ml | 1.0E-9 | 1.0E-9 | 1.3E2 | 2.6E2 | 5.1E2 | 8.5E2 | 1.0E-9 | 1.0E-9 | 3.6E3 | 4.6E3 | 79 | 34 | 79 | 34 | 0.54 |
| Mz | pg/ml | 1.5E1 | 1.7E1 | 2.6E1 | 3.4E1 | 4.5E1 | 4.0E1 | 1.0E-9 | 1.0E-9 | 3.0E2 | 1.5E2 | 79 | 34 | 79 | 34 | 0.58 |
| Na | pg/ml | 1.0E-9 | 1.0E-9 | 6.0E-1 | 8.4E-1 | 1.8E0 | 3.0E0 | 1.0E-9 | 1.0E-9 | 9.6E0 | 1.6E1 | 79 | 34 | 79 | 34 | 0.49 |

Figure 25 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nb | pg/ml | 2.0E0 | 3.0E0 | 2.7E0 | 3.7E0 | 3.3E0 | 3.3E0 | 1.0E-9 | 1.0E-9 | 2.3E1 | 1.7E1 | 79 | 34 | 79 | 34 | 0.63 |
| Nc | pg/ml | 1.6E2 | 3.0E2 | 3.6E2 | 4.9E2 | 4.4E2 | 4.9E2 | 1.0E-9 | 1.0E-9 | 1.8E3 | 2.1E3 | 79 | 34 | 79 | 34 | 0.59 |
| Nd | pg/ml | 7.0E0 | 6.5E0 | 3.0E1 | 1.6E1 | 1.4E2 | 2.0E1 | 1.0E-9 | 1.0E-9 | 1.2E3 | 9.4E1 | 79 | 34 | 79 | 34 | 0.51 |
| Ne | pg/ml | 2.8E2 | 3.7E2 | 3.8E2 | 4.5E2 | 3.4E2 | 3.9E2 | 1.0E-9 | 1.0E-9 | 1.5E3 | 1.7E3 | 79 | 34 | 79 | 34 | 0.56 |
| Nf | pg/ml | 1.0E-9 | 1.0E-9 | 1.4E0 | 2.6E0 | 5.0E0 | 8.9E0 | 1.0E-9 | 1.0E-9 | 3.5E1 | 5.1E1 | 79 | 34 | 79 | 34 | 0.56 |
| Ng | pg/ml | 1.7E1 | 7.2E0 | 9.1E1 | 1.0E2 | 1.4E2 | 2.4E2 | 1.0E-9 | 1.0E-9 | 6.2E2 | 1.2E3 | 79 | 34 | 79 | 34 | 0.46 |
| Nh | pg/ml | 4.2E1 | 5.4E1 | 5.8E1 | 6.0E1 | 5.4E1 | 4.7E1 | 1.0E-9 | 1.0E-9 | 3.4E2 | 2.2E2 | 79 | 34 | 79 | 34 | 0.55 |
| Ni | pg/ml | 2.2E1 | 1.2E1 | 9.4E1 | 9.6E1 | 1.2E2 | 1.5E2 | 1.0E-9 | 1.0E-9 | 5.7E2 | 5.7E2 | 79 | 34 | 79 | 34 | 0.48 |
| Nj | pg/ml | 3.5E0 | 3.0E0 | 7.3E0 | 6.3E0 | 8.3E0 | 7.0E0 | 1.0E-9 | 1.0E-9 | 3.6E1 | 2.9E1 | 79 | 34 | 79 | 34 | 0.47 |
| Nk | pg/ml | 1.7E1 | 2.2E1 | 3.0E1 | 3.6E1 | 3.5E1 | 4.8E1 | 1.0E-9 | 1.0E-9 | 1.7E2 | 2.0E2 | 79 | 34 | 79 | 34 | 0.53 |
| Nl | pg/ml | 2.4E1 | 4.0E1 | 3.8E1 | 4.7E1 | 3.8E1 | 3.8E1 | 1.0E-9 | 1.0E-9 | 1.9E2 | 1.4E2 | 79 | 34 | 79 | 34 | 0.59 |
| Hl | pg/ml | 1.3E1 | 2.9E1 | 2.4E1 | 5.7E1 | 2.8E1 | 7.7E1 | 1.0E-9 | 1.0E-9 | 9.7E1 | 2.3E2 | 23 | 11 | 23 | 11 | 0.61 |
| Ho | pg/ml | 1.7E1 | 2.7E1 | 2.4E1 | 2.5E1 | 1.8E1 | 8.9E0 | 8.1E0 | 7.6E0 | 8.7E1 | 4.0E1 | 23 | 11 | 23 | 11 | 0.62 |
| Hp | ng/ml | 1.3E0 | 3.3E0 | 1.9E2 | 8.3E1 | 3.7E2 | 2.7E2 | 4.2E-1 | 8.8E-1 | 8.9E2 | 8.9E2 | 23 | 11 | 23 | 11 | 0.61 |
| Tz | pg/ml | 7.2E3 | 6.2E3 | 3.2E4 | 3.1E4 | 1.4E5 | 8.2E4 | 1.0E-9 | 1.0E3 | 1.0E6 | 3.7E5 | 53 | 23 | 53 | 23 | 0.49 |
| Ua | pg/ml | 3.6E3 | 4.2E3 | 1.3E4 | 1.6E4 | 2.3E4 | 3.9E4 | 1.0E-9 | 8.4E2 | 1.2E5 | 1.8E5 | 53 | 23 | 53 | 23 | 0.51 |
| Ub | pg/ml | 6.9E2 | 5.6E2 | 9.3E2 | 8.7E2 | 1.0E3 | 9.3E2 | 1.0E-9 | 6.6E1 | 6.4E3 | 4.1E3 | 53 | 23 | 53 | 23 | 0.47 |
| Ue | pg/ml | 2.9E1 | 2.6E1 | 3.7E1 | 2.9E1 | 2.3E1 | 1.7E1 | 9.8E-2 | 8.8E0 | 1.0E2 | 7.4E1 | 53 | 23 | 53 | 23 | 0.41 |
| Uc | pg/ml | 9.6E2 | 9.6E2 | 1.6E3 | 2.1E3 | 2.0E3 | 2.8E3 | 1.0E-9 | 1.1E2 | 9.2E3 | 9.4E3 | 53 | 23 | 53 | 23 | 0.54 |
| Ud | pg/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 53 | 23 | 53 | 23 | 0.50 |
| Hq | pg/ml | 9.9E-1 | 1.3E0 | 3.7E2 | 1.2E1 | 3.3E3 | 4.1E1 | 1.0E-9 | 1.0E-9 | 2.8E4 | 2.3E2 | 78 | 33 | 78 | 33 | 0.57 |
| Hr | pg/ml | 1.0E2 | 1.4E2 | 4.8E2 | 8.2E2 | 9.3E2 | 1.5E3 | 1.0E-9 | 2.2E1 | 5.0E3 | 5.5E3 | 78 | 33 | 78 | 33 | 0.57 |
| Hu | pg/ml | 2.2E1 | 8.9E0 | 4.1E3 | 1.0E3 | 3.0E4 | 2.4E3 | 1.0E-9 | 1.0E-9 | 2.6E5 | 8.8E3 | 78 | 33 | 78 | 33 | 0.46 |
| Hv | pg/ml | 2.0E0 | 1.2E0 | 3.5E0 | 2.0E0 | 9.5E0 | 2.4E0 | 1.0E-9 | 1.0E-9 | 8.4E1 | 1.1E1 | 78 | 33 | 78 | 33 | 0.41 |
| Hw | pg/ml | 5.4E0 | 6.5E0 | 1.2E1 | 1.3E1 | 2.0E1 | 1.8E1 | 1.0E-9 | 1.0E-9 | 1.5E2 | 1.0E2 | 78 | 33 | 78 | 33 | 0.54 |
| Hx | pg/ml | 1.0E1 | 1.3E1 | 2.6E1 | 2.8E1 | 5.9E1 | 3.4E1 | 1.0E-9 | 1.0E-9 | 3.7E2 | 1.6E2 | 78 | 33 | 78 | 33 | 0.60 |
| Ib | ng/ml | 3.3E-2 | 2.7E-2 | 9.8E-1 | 2.3E0 | 3.4E0 | 1.1E1 | 1.0E-9 | 1.0E-9 | 1.7E1 | 5.2E1 | 49 | 23 | 49 | 23 | 0.43 |
| Ic | U/ml | 2.2E2 | 2.2E2 | 3.4E2 | 1.7E2 | 6.3E2 | 1.3E2 | 1.1E1 | 1.8E1 | 4.2E3 | 4.2E2 | 49 | 23 | 49 | 23 | 0.40 |
| Id | U/ml | 7.6E-1 | 8.9E-1 | 1.2E0 | 1.9E0 | 1.2E0 | 3.2E0 | 1.0E-9 | 5.6E-2 | 5.0E0 | 1.5E1 | 49 | 23 | 49 | 23 | 0.55 |
| Tt | pg/ml | 1.6E2 | 1.7E2 | 1.7E2 | 1.8E2 | 5.4E1 | 5.6E1 | 7.3E1 | 1.0E2 | 3.6E2 | 2.8E2 | 51 | 22 | 51 | 22 | 0.53 |
| To | pg/ml | 1.5E0 | 6.7E-1 | 1.8E0 | 1.3E0 | 1.9E0 | 1.5E0 | 1.0E-9 | 1.0E-9 | 6.5E0 | 5.1E0 | 52 | 23 | 52 | 23 | 0.44 |
| Tr | pg/ml | 2.6E0 | 4.7E0 | 1.0E1 | 1.0E1 | 4.3E1 | 1.4E1 | 1.0E-9 | 4.5E-1 | 3.1E2 | 5.4E1 | 52 | 22 | 52 | 22 | 0.59 |
| Tn | pg/ml | 2.4E1 | 4.3E1 | 7.9E1 | 1.5E2 | 2.5E2 | 4.0E2 | 2.4E0 | 1.1E1 | 1.8E3 | 2.0E3 | 52 | 23 | 52 | 23 | 0.63 |
| Tv | ng/ml | 1.1E1 | 1.2E1 | 1.7E1 | 5.2E1 | 2.2E1 | 1.6E2 | 1.0E-9 | 1.0E-9 | 1.3E2 | 7.9E2 | 52 | 23 | 52 | 23 | 0.52 |
| Ih | ng/ml | 9.3E1 | 1.3E2 | 2.2E2 | 2.4E2 | 3.5E2 | 2.8E2 | 1.0E-9 | 4.7E0 | 1.7E3 | 1.1E3 | 78 | 34 | 78 | 34 | 0.57 |
| Ii | ng/ml | 1.0E2 | 1.1E2 | 1.7E2 | 2.3E2 | 2.0E2 | 3.0E2 | 2.9E0 | 5.1E0 | 1.2E3 | 1.2E3 | 78 | 34 | 78 | 34 | 0.55 |
| Ij | ng/ml | 7.8E1 | 1.2E2 | 1.5E2 | 1.9E2 | 3.0E2 | 1.9E2 | 4.7E0 | 1.9E1 | 2.0E3 | 8.4E2 | 78 | 33 | 78 | 33 | 0.64 |
| Ik | ng/ml | 1.6E2 | 1.1E2 | 6.5E2 | 4.0E2 | 1.3E3 | 5.1E2 | 1.3E0 | 2.3E0 | 9.7E3 | 1.5E3 | 78 | 34 | 78 | 34 | 0.48 |
| Il | ng/ml | 4.1E2 | 5.5E2 | 1.1E3 | 1.9E3 | 2.3E3 | 3.5E3 | 1.0E-9 | 1.0E-9 | 1.2E4 | 1.2E4 | 78 | 34 | 78 | 34 | 0.55 |
| Im | ng/ml | 2.0E2 | 2.6E2 | 4.9E2 | 6.4E2 | 9.1E2 | 1.1E3 | 2.7E1 | 4.5E1 | 5.6E3 | 5.8E3 | 78 | 34 | 78 | 34 | 0.61 |
| In | ng/ml | 5.0E0 | 3.4E0 | 1.3E1 | 9.2E0 | 2.9E1 | 1.6E1 | 1.0E-9 | 1.0E-9 | 2.4E2 | 8.4E1 | 78 | 34 | 78 | 34 | 0.44 |
| Hb | ng/ml | 2.4E1 | 4.1E1 | 3.2E1 | 5.9E1 | 2.7E1 | 6.2E1 | 3.3E0 | 1.7E0 | 1.2E2 | 2.1E2 | 52 | 24 | 52 | 24 | 0.58 |
| Hc | pg/ml | 6.7E2 | 6.2E2 | 3.5E3 | 3.5E3 | 1.4E4 | 1.1E4 | 1.0E-9 | 1.0E-9 | 1.0E5 | 5.0E4 | 52 | 24 | 52 | 24 | 0.47 |
| Hf | ng/ml | 1.9E2 | 1.6E2 | 4.4E2 | 4.2E2 | 5.7E2 | 6.8E2 | 1.0E-9 | 1.0E-9 | 2.5E3 | 3.2E3 | 52 | 24 | 52 | 24 | 0.46 |
| Io | ng/ml | 7.7E3 | 7.9E3 | 1.5E4 | 1.5E4 | 2.7E4 | 1.8E4 | 1.0E-9 | 1.1E3 | 2.0E5 | 8.4E4 | 78 | 34 | 78 | 34 | 0.51 |
| Ip | ng/ml | 1.1E1 | 3.0E1 | 1.9E1 | 2.8E1 | 2.0E1 | 2.2E1 | 1.0E-9 | 1.8E-1 | 6.4E1 | 8.8E1 | 78 | 34 | 78 | 34 | 0.62 |
| Iq | ug/ml | 3.1E-2 | 1.7E-1 | 7.7E-1 | 9.4E-1 | 2.9E0 | 3.1E0 | 1.0E-9 | 1.0E-9 | 1.8E1 | 1.8E1 | 78 | 34 | 78 | 34 | 0.65 |
| Ir | ug/ml | 3.1E-1 | 8.9E-1 | 3.2E0 | 1.8E0 | 1.8E1 | 2.4E0 | 1.0E-9 | 5.0E-2 | 1.6E2 | 1.1E1 | 78 | 34 | 78 | 34 | 0.67 |
| Is | ng/ml | 2.1E0 | 4.6E0 | 6.4E0 | 1.3E1 | 1.4E1 | 2.1E1 | 1.0E-9 | 3.7E-1 | 8.8E1 | 1.1E2 | 78 | 34 | 78 | 34 | 0.72 |
| It | ng/ml | 1.8E0 | 2.7E0 | 2.6E1 | 1.4E1 | 1.3E2 | 3.7E1 | 1.0E-9 | 1.0E-9 | 8.3E2 | 1.8E2 | 78 | 34 | 78 | 34 | 0.55 |
| Iu | ng/ml | 1.0E2 | 2.4E2 | 9.0E2 | 1.3E3 | 3.3E3 | 4.2E3 | 1.0E-9 | 1.0E-9 | 2.4E4 | 2.4E4 | 78 | 34 | 78 | 34 | 0.58 |
| Iv | ng/ml | 1.8E1 | 3.2E1 | 4.9E1 | 4.3E1 | 1.1E2 | 4.2E1 | 1.0E-9 | 1.0E-9 | 7.7E2 | 1.6E2 | 78 | 34 | 78 | 34 | 0.58 |
| Iz | ng/ml | 1.5E2 | 1.1E2 | 3.4E2 | 3.0E2 | 4.3E2 | 4.1E2 | 8.3E0 | 8.8E0 | 2.3E3 | 1.7E3 | 52 | 24 | 52 | 24 | 0.49 |
| Yg | pg/ml | 2.6E2 | 3.8E2 | 1.2E3 | 8.2E2 | 2.6E3 | 8.1E2 | 2.6E1 | 1.5E1 | 1.2E4 | 2.3E3 | 22 | 11 | 22 | 11 | 0.55 |
| Yh | pg/ml | 2.1E2 | 6.9E2 | 3.9E2 | 5.9E2 | 5.0E2 | 4.5E2 | 1.0E-9 | 1.0E-9 | 2.1E3 | 1.4E3 | 22 | 11 | 22 | 11 | 0.67 |
| Yi | pg/ml | 2.7E2 | 7.5E2 | 3.7E2 | 3.1E3 | 4.2E2 | 7.6E3 | 1.0E-9 | 2.7E1 | 1.8E3 | 2.6E4 | 22 | 11 | 22 | 11 | 0.77 |
| Yk | U/ml | 1.0E-9 | 1.0E-9 | 3.0E-2 | 1.1E-1 | 8.7E-2 | 3.7E-1 | 1.0E-9 | 1.0E-9 | 3.6E-1 | 1.2E0 | 22 | 11 | 22 | 11 | 0.48 |

Figure 25 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yj | pg/ml | 1.2E2 | 2.9E2 | 3.3E2 | 3.7E2 | 8.6E2 | 4.2E2 | 1.0E-9 | 1.7E1 | 4.1E3 | 1.5E3 | 22 | 11 | 22 | 11 | 0.66 |
| Yd | ng/ml | 2.9E-1 | 2.0E-1 | 3.2E-1 | 5.3E-1 | 2.6E-1 | 8.1E-1 | 1.6E-2 | 7.9E-3 | 9.6E-1 | 2.3E0 | 23 | 11 | 23 | 11 | 0.45 |
| Wb | pg/ml | 3.3E4 | 3.2E4 | 4.1E4 | 4.5E4 | 3.1E4 | 3.0E4 | 1.0E4 | 1.4E4 | 1.6E5 | 1.1E5 | 22 | 11 | 22 | 11 | 0.53 |
| Vz | pg/ml | 1.9E0 | 3.5E0 | 2.3E0 | 5.2E0 | 2.0E0 | 5.9E0 | 1.0E-9 | 7.6E-2 | 7.6E0 | 2.1E1 | 22 | 11 | 22 | 11 | 0.70 |
| Si | ng/ml | 1.1E0 | 6.9E-1 | 2.6E0 | 1.2E0 | 3.5E0 | 1.3E0 | 7.8E-2 | 2.5E-2 | 1.3E1 | 4.6E0 | 23 | 11 | 23 | 11 | 0.39 |
| Sf | mIU/mL | 1.4E1 | 1.2E1 | 2.1E1 | 2.1E1 | 3.1E1 | 2.5E1 | 1.3E0 | 2.0E-1 | 1.5E2 | 8.3E1 | 23 | 11 | 23 | 11 | 0.49 |
| Sh | mIU/mL | 1.4E1 | 6.6E0 | 2.7E1 | 1.4E1 | 3.9E1 | 1.8E1 | 7.9E-1 | 9.0E-2 | 1.8E2 | 5.8E1 | 23 | 11 | 23 | 11 | 0.35 |
| Sj | ng/ml | 3.8E-1 | 4.4E-1 | 4.0E-1 | 4.6E-1 | 1.2E-1 | 1.1E-1 | 1.1E-1 | 3.4E-1 | 6.2E-1 | 7.2E-1 | 23 | 11 | 23 | 11 | 0.60 |
| Rc | pg/ml | 5.3E3 | 5.3E3 | 7.9E3 | 6.0E3 | 6.1E3 | 3.7E3 | 1.1E3 | 6.7E2 | 2.3E4 | 1.4E4 | 53 | 23 | 53 | 23 | 0.44 |
| Rb | pg/ml | 1.2E0 | 3.3E-1 | 3.5E0 | 1.9E0 | 4.7E0 | 2.8E0 | 1.0E-9 | 1.0E-9 | 2.0E1 | 9.4E0 | 53 | 23 | 53 | 23 | 0.43 |
| Zq | 2.6ng/ml | 3.5E2 | 3.0E2 | 3.9E2 | 3.2E2 | 3.0E2 | 2.7E2 | 7.4E1 | 3.7E1 | 9.7E2 | 9.7E2 | 23 | 11 | 23 | 11 | 0.43 |
| Zw | 2.5ng/ml | 6.2E0 | 4.7E0 | 9.8E0 | 1.4E1 | 1.2E1 | 1.8E1 | 2.4E-1 | 1.7E0 | 4.6E1 | 6.3E1 | 23 | 11 | 23 | 11 | 0.62 |
| Zx | 2.3mU/ml | 1.4E-1 | 9.4E-2 | 4.0E-1 | 3.2E-1 | 7.1E-1 | 5.4E-1 | 5.6E-2 | 5.0E-2 | 3.0E0 | 1.9E0 | 23 | 11 | 23 | 11 | 0.40 |
| Pz | ng/ml | 3.3E3 | 4.8E3 | 6.0E3 | 3.6E4 | 7.3E3 | 1.8E5 | 3.6E1 | 6.2E2 | 4.8E4 | 1.0E6 | 77 | 33 | 77 | 33 | 0.55 |
| Qa | ng/ml | 3.8E3 | 7.5E3 | 6.3E3 | 1.1E4 | 6.7E3 | 9.4E3 | 3.4E2 | 6.8E2 | 3.2E4 | 3.6E4 | 77 | 33 | 77 | 33 | 0.66 |
| Qb | ng/ml | 1.2E2 | 2.0E2 | 1.7E2 | 3.8E2 | 1.6E2 | 7.1E2 | 6.7E0 | 1.8E1 | 7.3E2 | 4.1E3 | 77 | 33 | 77 | 33 | 0.63 |
| Qc | ng/ml | 2.3E2 | 4.6E2 | 4.0E2 | 6.9E2 | 4.3E2 | 8.9E2 | 1.9E0 | 1.3E1 | 2.1E3 | 4.3E3 | 77 | 33 | 77 | 33 | 0.61 |
| Qd | ng/ml | 1.1E4 | 1.5E4 | 1.8E4 | 3.1E4 | 2.3E4 | 3.8E4 | 9.8E2 | 1.7E3 | 1.3E5 | 1.5E5 | 77 | 33 | 77 | 33 | 0.61 |
| Qe | ng/ml | 1.3E3 | 1.8E3 | 1.6E3 | 2.6E3 | 1.5E3 | 2.5E3 | 6.8E1 | 1.8E2 | 7.4E3 | 1.3E4 | 77 | 33 | 77 | 33 | 0.64 |
| Jd | ng/ml | 1.4E0 | 2.1E0 | 3.7E0 | 2.3E0 | 1.0E1 | 2.9E0 | 1.0E-9 | 1.0E-9 | 7.3E1 | 1.1E1 | 53 | 23 | 53 | 23 | 0.48 |
| Je | ng/ml | 2.9E-1 | 1.0E-9 | 1.6E0 | 7.4E-1 | 2.4E0 | 1.3E0 | 1.0E-9 | 1.0E-9 | 1.1E1 | 4.3E0 | 53 | 23 | 53 | 23 | 0.39 |
| Jf | ng/ml | 1.0E-9 | 1.0E-9 | 1.2E0 | 1.3E0 | 2.3E0 | 2.5E0 | 1.0E-9 | 1.0E-9 | 9.6E0 | 9.1E0 | 53 | 23 | 53 | 23 | 0.48 |
| Jg | ng/ml | 6.4E2 | 6.7E2 | 8.6E2 | 9.8E2 | 7.7E2 | 1.1E3 | 1.1E1 | 5.9E1 | 3.4E3 | 5.3E3 | 78 | 33 | 78 | 33 | 0.52 |
| Jh | ng/ml | 5.0E0 | 3.0E0 | 1.7E1 | 2.7E1 | 4.2E1 | 8.4E1 | 1.0E-9 | 1.0E-9 | 2.6E2 | 4.7E2 | 78 | 33 | 78 | 33 | 0.51 |
| Ji | ng/ml | 7.0E1 | 8.4E1 | 9.7E1 | 1.3E2 | 8.1E1 | 1.2E2 | 8.3E0 | 8.9E0 | 3.6E2 | 5.4E2 | 78 | 33 | 78 | 33 | 0.57 |
| Sr | pg/mL | 4.9E2 | 9.2E2 | 8.4E2 | 1.2E3 | 1.0E3 | 1.3E3 | 1.0E-9 | 1.0E-9 | 4.8E3 | 5.1E3 | 50 | 23 | 50 | 23 | 0.59 |
| Ss | pg/mL | 1.4E5 | 5.5E4 | 1.7E5 | 1.0E5 | 2.1E5 | 8.9E4 | 2.7E3 | 1.1E4 | 1.3E6 | 3.0E5 | 50 | 23 | 50 | 23 | 0.42 |
| St | pg/mL | 2.4E7 | 6.5E7 | 6.2E7 | 9.0E7 | 1.6E8 | 1.3E8 | 1.1E6 | 2.8E6 | 1.2E9 | 5.4E8 | 53 | 23 | 53 | 23 | 0.62 |
| Wc | ng/ml | 2.9E-2 | 1.0E-9 | 6.3E-2 | 2.0E-2 | 8.4E-2 | 3.9E-2 | 1.0E-9 | 1.0E-9 | 2.8E-1 | 1.2E-1 | 23 | 11 | 23 | 11 | 0.35 |
| Wd | ng/ml | 1.1E1 | 8.4E0 | 5.7E1 | 1.8E1 | 1.6E2 | 2.2E1 | 5.0E-1 | 3.5E0 | 7.9E2 | 6.7E1 | 23 | 11 | 23 | 11 | 0.50 |
| We | ng/ml | 4.9E-1 | 4.9E-1 | 7.0E-1 | 9.1E-1 | 8.5E-1 | 1.3E0 | 1.0E-9 | 1.0E-9 | 3.5E0 | 4.1E0 | 23 | 11 | 23 | 11 | 0.52 |
| Wg | ng/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 23 | 11 | 23 | 11 | 0.50 |
| Wh | ng/ml | 1.1E-2 | 8.4E-3 | 1.4E-1 | 6.6E-2 | 5.1E-1 | 1.6E-1 | 1.0E-9 | 4.3E-3 | 2.5E0 | 5.4E-1 | 23 | 11 | 23 | 11 | 0.54 |
| Wf | ng/ml | 1.0E-9 | 1.0E-9 | 2.1E-1 | 1.0E-1 | 5.4E-1 | 1.6E-1 | 1.0E-9 | 1.0E-9 | 2.4E0 | 4.7E-1 | 23 | 11 | 23 | 11 | 0.53 |
| Ra | pg/ml | 1.0E-9 | 1.0E-9 | 4.0E-1 | 5.1E-1 | 9.5E-1 | 1.5E0 | 1.0E-9 | 1.0E-9 | 3.4E0 | 6.5E0 | 53 | 23 | 53 | 23 | 0.53 |
| Qz | pg/ml | 1.1E1 | 1.1E1 | 4.4E1 | 6.0E1 | 6.2E1 | 8.8E1 | 1.0E-9 | 1.0E-9 | 2.0E2 | 2.8E2 | 53 | 23 | 53 | 23 | 0.55 |
| Qy | pg/ml | 4.3E-1 | 4.7E-1 | 1.3E1 | 2.3E1 | 6.1E1 | 1.1E2 | 1.0E-9 | 1.0E-9 | 4.3E2 | 5.1E2 | 53 | 23 | 53 | 23 | 0.47 |
| Qx | pg/ml | 1.0E-9 | 1.0E-9 | 5.9E-1 | 2.4E0 | 2.1E0 | 8.0E0 | 1.0E-9 | 1.0E-9 | 9.4E0 | 3.1E1 | 53 | 23 | 53 | 23 | 0.51 |
| Qw | pg/ml | 1.0E-9 | 1.0E-9 | 3.6E0 | 1.4E0 | 1.5E1 | 4.7E0 | 1.0E-9 | 1.0E-9 | 8.6E1 | 2.3E1 | 53 | 23 | 53 | 23 | 0.46 |
| Qv | pg/ml | 2.0E4 | 1.2E4 | 2.8E4 | 3.4E4 | 3.4E4 | 6.7E4 | 1.0E-9 | 8.5E2 | 2.3E5 | 3.3E5 | 53 | 23 | 53 | 23 | 0.43 |
| Qu | pg/ml | 7.8E0 | 1.0E-9 | 1.1E2 | 6.7E1 | 2.1E2 | 1.5E2 | 1.0E-9 | 1.0E-9 | 9.8E2 | 6.7E2 | 53 | 23 | 53 | 23 | 0.45 |
| Qt | pg/ml | 1.1E1 | 1.9E1 | 6.5E1 | 3.4E1 | 1.4E2 | 5.5E1 | 1.0E-9 | 1.0E-9 | 7.0E2 | 2.2E2 | 53 | 23 | 53 | 23 | 0.53 |
| Qh | pg/ml | 1.7E1 | 3.9E1 | 4.2E1 | 6.9E1 | 6.9E1 | 9.8E1 | 4.3E-1 | 4.9E0 | 3.3E2 | 4.6E2 | 53 | 23 | 53 | 23 | 0.67 |
| Qg | pg/ml | 8.1E0 | 8.1E0 | 1.6E1 | 1.2E1 | 3.1E1 | 1.3E0 | 1.3E-1 | 1.0E-9 | 2.2E2 | 8.1E1 | 53 | 23 | 53 | 23 | 0.48 |
| Jj | ng/ml | 6.4E2 | 5.6E2 | 9.6E2 | 7.0E2 | 1.2E3 | 8.6E2 | 4.9E0 | 6.8E1 | 7.7E3 | 4.1E3 | 78 | 33 | 78 | 33 | 0.43 |
| Jk | ng/ml | 2.5E0 | 3.0E0 | 2.3E1 | 3.0E1 | 6.0E1 | 5.1E1 | 1.2E-1 | 3.8E-1 | 3.9E2 | 2.0E2 | 78 | 33 | 78 | 33 | 0.58 |
| Jl | ng/ml | 5.3E-1 | 7.3E-1 | 2.1E0 | 4.3E0 | 4.7E0 | 9.0E0 | 1.1E-3 | 4.8E-2 | 2.0E1 | 4.0E1 | 78 | 33 | 78 | 33 | 0.58 |
| Jm | ng/ml | 2.0E1 | 4.3E1 | 4.9E1 | 1.3E2 | 8.5E1 | 3.5E2 | 1.0E-9 | 9.2E-1 | 6.1E2 | 2.1E3 | 78 | 33 | 78 | 33 | 0.63 |
| Jn | pg/ml | 4.6E-1 | 6.5E-1 | 1.5E0 | 1.2E0 | 4.8E0 | 1.4E0 | 1.0E-9 | 1.0E-9 | 3.9E1 | 6.6E0 | 78 | 33 | 78 | 33 | 0.58 |
| Jo | pg/ml | 4.2E3 | 4.5E3 | 5.2E3 | 5.3E3 | 4.3E3 | 3.9E3 | 4.8E2 | 2.6E2 | 1.9E4 | 1.6E4 | 78 | 33 | 78 | 33 | 0.52 |
| Jp | pg/ml | 7.9E4 | 8.2E4 | 7.8E4 | 8.8E4 | 3.2E4 | 4.4E4 | 2.8E3 | 1.6E4 | 1.7E5 | 2.1E5 | 78 | 33 | 78 | 33 | 0.52 |
| Jq | pg/ml | 1.1E2 | 1.4E2 | 1.9E2 | 2.1E2 | 4.6E2 | 2.3E2 | 5.4E0 | 2.2E1 | 4.0E3 | 1.1E3 | 78 | 33 | 78 | 33 | 0.60 |
| Jr | pg/ml | 6.5E0 | 7.2E0 | 1.4E1 | 1.3E1 | 2.7E1 | 1.6E1 | 1.0E-9 | 1.0E-9 | 1.8E2 | 4.9E1 | 78 | 33 | 78 | 33 | 0.54 |
| Js | pg/ml | 1.5E1 | 1.9E1 | 2.9E1 | 2.9E1 | 7.5E1 | 3.0E1 | 1.3E0 | 1.0E-9 | 6.1E2 | 1.2E2 | 78 | 33 | 78 | 33 | 0.59 |
| Jt | pg/ml | 2.7E3 | 2.8E3 | 3.2E3 | 3.0E3 | 2.1E3 | 1.9E3 | 2.8E2 | 2.6E2 | 9.7E3 | 7.5E3 | 78 | 33 | 78 | 33 | 0.48 |
| Xa | pg/ml | 6.1E-1 | 4.9E0 | 1.0E1 | 2.1E1 | 1.7E1 | 3.5E1 | 1.0E-9 | 1.0E-9 | 6.4E1 | 9.9E1 | 22 | 11 | 22 | 11 | 0.61 |
| Ye | pg/ml | 1.0E-9 | 1.0E-9 | 4.5E0 | 3.3E1 | 1.1E1 | 1.1E2 | 1.0E-9 | 1.0E-9 | 4.1E1 | 3.5E2 | 22 | 11 | 22 | 11 | 0.52 |

Figure 25 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Tm | pg/ml | 1.0E-9 | 1.0E-9 | 5.6E0 | 7.0E0 | 1.0E1 | 2.0E1 | 1.0E-9 | 1.0E-9 | 4.6E1 | 6.8E1 | 22 | 11 | 22 | 11 | 0.40 |
| Tl | pg/ml | 4.7E-1 | 1.1E-1 | 4.2E-1 | 3.6E-1 | 3.3E-1 | 5.6E-1 | 1.0E-9 | 1.0E-9 | 1.2E0 | 1.8E0 | 22 | 11 | 22 | 11 | 0.36 |
| Ju | mIU/ml | 8.4E0 | 1.2E1 | 2.2E1 | 1.8E1 | 3.5E1 | 1.8E1 | 1.7E-1 | 1.5E-1 | 2.0E2 | 6.0E1 | 53 | 23 | 53 | 23 | 0.54 |
| Jv | mIU/ml | 1.1E1 | 1.7E1 | 3.2E1 | 2.5E1 | 5.5E1 | 2.6E1 | 1.7E-2 | 8.2E-2 | 3.4E2 | 8.9E1 | 53 | 23 | 53 | 23 | 0.51 |
| Jy | ng/ml | 1.5E-3 | 1.6E-3 | 2.4E-3 | 2.7E-3 | 5.2E-3 | 4.4E-3 | 1.0E-9 | 5.3E-4 | 3.9E-2 | 2.3E-2 | 53 | 23 | 53 | 23 | 0.55 |
| Kc | pg/ml | 2.8E1 | 2.3E1 | 4.3E1 | 4.1E1 | 4.1E1 | 6.2E1 | 1.0E-9 | 1.0E-9 | 1.7E2 | 2.7E2 | 52 | 23 | 52 | 23 | 0.43 |
| Kd | pg/ml | 1.0E-9 | 1.0E-9 | 1.8E2 | 3.5E2 | 4.4E2 | 7.3E2 | 1.0E-9 | 1.0E-9 | 1.9E3 | 2.4E3 | 52 | 23 | 52 | 23 | 0.53 |
| Ke | pg/ml | 1.3E4 | 1.7E4 | 1.6E4 | 2.2E4 | 1.1E4 | 1.7E4 | 5.8E2 | 2.3E3 | 5.6E4 | 6.3E4 | 52 | 23 | 52 | 23 | 0.58 |
| Kf | pg/mL | 8.2E0 | 7.2E0 | 7.3E0 | 8.0E0 | 4.9E0 | 8.7E0 | 1.0E-9 | 1.0E-9 | 2.4E1 | 4.4E1 | 52 | 23 | 52 | 23 | 0.47 |
| Kg | pg/mL | 1.2E3 | 9.6E2 | 1.9E3 | 1.8E3 | 2.1E3 | 1.9E3 | 1.4E2 | 2.4E2 | 1.1E4 | 7.7E3 | 52 | 23 | 52 | 23 | 0.46 |
| Ki | pg/ml | 5.9E1 | 8.5E1 | 7.5E1 | 8.7E1 | 4.6E1 | 5.6E1 | 1.0E-9 | 1.3E1 | 2.5E2 | 2.5E2 | 51 | 23 | 51 | 23 | 0.58 |
| Kj | pg/ml | 9.5E2 | 7.7E2 | 1.5E3 | 1.3E3 | 1.2E3 | 1.4E3 | 7.8E1 | 3.3E1 | 5.6E3 | 6.1E3 | 52 | 23 | 52 | 23 | 0.42 |
| Kk | pg/ml | 6.8E0 | 1.0E1 | 1.0E1 | 1.5E1 | 1.0E1 | 1.6E1 | 1.0E-9 | 8.4E-1 | 5.0E1 | 5.5E1 | 52 | 23 | 52 | 23 | 0.61 |
| Kl | pg/ml | 2.1E4 | 1.6E4 | 2.9E4 | 2.6E4 | 2.9E4 | 2.3E4 | 2.1E2 | 7.0E2 | 1.6E5 | 9.0E4 | 52 | 23 | 52 | 23 | 0.47 |
| Kn | pg/ml | 3.0E1 | 3.0E1 | 5.6E1 | 9.0E1 | 6.7E1 | 1.5E2 | 1.0E-9 | 1.0E-9 | 3.6E2 | 6.3E2 | 52 | 23 | 52 | 23 | 0.54 |
| Ko | pg/ml | 2.1E2 | 4.0E2 | 4.1E2 | 5.4E2 | 4.5E2 | 4.9E2 | 1.0E-9 | 1.0E-9 | 1.5E3 | 1.6E3 | 52 | 23 | 52 | 23 | 0.58 |
| Kp | pg/ml | 3.6E2 | 3.6E2 | 3.7E2 | 3.8E2 | 2.1E2 | 2.6E2 | 1.0E-9 | 1.0E-9 | 8.4E2 | 9.8E2 | 52 | 23 | 52 | 23 | 0.50 |
| Kq | pg/ml | 3.0E2 | 4.5E2 | 4.6E2 | 6.2E2 | 4.7E2 | 7.2E2 | 7.0E0 | 2.5E1 | 2.1E3 | 3.6E3 | 50 | 24 | 50 | 24 | 0.61 |
| Kr | pg/ml | 5.7E-1 | 7.2E-1 | 2.1E0 | 2.5E0 | 2.9E0 | 4.4E0 | 1.0E-9 | 1.0E-9 | 1.2E1 | 1.9E1 | 50 | 24 | 50 | 24 | 0.50 |
| Ks | pg/ml | 9.7E3 | 1.7E4 | 1.9E4 | 2.1E4 | 1.8E4 | 1.8E4 | 2.7E2 | 9.9E2 | 5.0E4 | 5.1E4 | 50 | 24 | 50 | 24 | 0.54 |
| Ps | ng/ml | 1.8E2 | 4.0E2 | 4.4E2 | 1.5E3 | 7.0E2 | 3.6E3 | 4.1E-1 | 1.6E1 | 2.9E3 | 1.2E4 | 23 | 11 | 23 | 11 | 0.60 |
| Kx | ng/ml | 1.0E-9 | 8.5E-3 | 7.1E-3 | 1.5E-2 | 1.4E-2 | 2.0E-2 | 1.0E-9 | 1.0E-9 | 7.9E-2 | 6.5E-2 | 52 | 23 | 52 | 23 | 0.60 |
| Ky | ng/ml | 8.7E-2 | 1.5E-1 | 3.8E-1 | 4.6E-1 | 7.3E-1 | 6.4E-1 | 1.0E-9 | 1.0E-9 | 4.4E0 | 2.4E0 | 52 | 23 | 52 | 23 | 0.58 |
| Kz | ng/ml | 1.0E-9 | 1.0E-9 | 1.9E-3 | 4.4E-3 | 4.6E-3 | 6.2E-3 | 1.0E-9 | 1.0E-9 | 1.4E-2 | 1.4E-2 | 52 | 23 | 52 | 23 | 0.60 |
| Rz | ng/ml | 5.6E-1 | 2.9E-1 | 1.1E0 | 7.3E-1 | 1.4E0 | 9.9E-1 | 1.8E-2 | 1.7E-2 | 4.7E0 | 3.1E0 | 23 | 11 | 23 | 11 | 0.39 |
| Ry | ng/ml | 1.6E-2 | 1.6E-2 | 2.4E-2 | 2.9E-2 | 2.9E-2 | 2.9E-2 | 1.0E-9 | 1.0E-9 | 1.2E-1 | 9.2E-2 | 23 | 11 | 23 | 11 | 0.54 |
| Rx | ng/ml | 1.0E-9 | 1.6E-3 | 1.3E-3 | 1.7E-3 | 2.3E-3 | 1.7E-3 | 1.0E-9 | 1.0E-9 | 8.6E-3 | 3.9E-3 | 23 | 11 | 23 | 11 | 0.62 |
| Ld | pg/ml | 1.0E-9 | 1.0E-9 | 2.0E0 | 5.6E0 | 3.5E0 | 1.1E1 | 1.0E-9 | 1.0E-9 | 1.5E1 | 5.0E1 | 51 | 24 | 51 | 24 | 0.59 |
| Lh | pg/ml | 1.4E4 | 1.9E4 | 2.2E4 | 3.6E4 | 2.1E4 | 4.2E4 | 1.8E2 | 5.5E2 | 1.1E5 | 2.1E5 | 79 | 33 | 79 | 33 | 0.60 |
| Li | pg/ml | 3.0E3 | 1.4E4 | 1.2E4 | 4.8E4 | 2.4E4 | 1.6E5 | 1.7E2 | 2.6E1 | 1.3E5 | 9.2E5 | 79 | 33 | 79 | 33 | 0.68 |
| Lj | pg/ml | 3.4E3 | 6.7E3 | 2.1E4 | 4.7E4 | 6.9E4 | 8.0E4 | 4.1E1 | 1.0E-9 | 4.7E5 | 4.1E5 | 79 | 33 | 79 | 33 | 0.59 |
| Lp | pg/ml | 5.7E0 | 9.5E0 | 7.4E1 | 7.6E1 | 1.8E2 | 2.0E2 | 1.0E-9 | 1.0E-9 | 7.7E2 | 6.8E2 | 23 | 11 | 23 | 11 | 0.51 |
| Lt | pg/ml | 1.0E-9 | 1.0E-9 | 2.3E0 | 2.3E0 | 6.7E0 | 7.6E0 | 1.0E-9 | 1.0E-9 | 2.5E1 | 2.5E1 | 23 | 11 | 23 | 11 | 0.48 |
| Rv | ng/ml | 5.0E-4 | 9.8E-4 | 8.0E-4 | 1.6E-3 | 1.1E-3 | 2.6E-3 | 1.0E-9 | 1.0E-9 | 5.0E-3 | 9.2E-3 | 23 | 11 | 23 | 11 | 0.65 |
| Ru | ng/ml | 1.0E-9 | 1.0E-9 | 1.9E-2 | 3.8E-2 | 8.0E-2 | 1.0E-1 | 1.0E-9 | 1.0E-9 | 3.8E-1 | 3.5E-1 | 23 | 11 | 23 | 11 | 0.55 |
| Rt | ng/ml | 4.0E-2 | 5.2E-2 | 1.3E-1 | 9.1E-2 | 1.8E-1 | 1.1E-1 | 1.0E-3 | 1.3E-3 | 5.8E-1 | 3.6E-1 | 23 | 11 | 23 | 11 | 0.51 |
| Yl | pg/ml | 7.3E0 | 1.2E1 | 8.8E0 | 2.4E1 | 1.3E1 | 2.3E1 | 1.0E-9 | 1.0E-9 | 6.6E1 | 7.9E1 | 23 | 11 | 23 | 11 | 0.75 |
| Rm | ng/ml | 1.7E1 | 3.4E1 | 3.6E1 | 8.2E1 | 4.9E1 | 1.4E2 | 7.7E-1 | 1.2E0 | 2.5E2 | 6.5E2 | 52 | 22 | 52 | 22 | 0.61 |
| Rh | ng/ml | 1.6E2 | 1.1E2 | 2.6E2 | 9.6E2 | 3.3E2 | 3.6E3 | 3.6E0 | 2.5E1 | 2.0E3 | 1.7E4 | 52 | 22 | 52 | 22 | 0.44 |
| Ri | ng/ml | 1.0E-9 | 1.0E-9 | 3.5E0 | 4.3E0 | 7.4E0 | 1.0E1 | 1.0E-9 | 1.0E-9 | 4.5E1 | 4.5E1 | 52 | 22 | 52 | 22 | 0.48 |
| Rg | ng/ml | 1.0E-9 | 1.0E-9 | 5.1E-2 | 2.0E-1 | 2.7E-1 | 7.1E-1 | 1.0E-9 | 1.0E-9 | 1.9E0 | 3.3E0 | 52 | 22 | 52 | 22 | 0.64 |
| Rj | ng/ml | 1.0E-9 | 1.0E-9 | 1.0E0 | 6.5E-1 | 2.1E0 | 1.1E0 | 1.0E-9 | 1.0E-9 | 1.1E1 | 3.2E0 | 52 | 22 | 52 | 22 | 0.50 |
| Rf | ng/ml | 5.0E-1 | 5.6E-1 | 1.4E0 | 1.7E0 | 2.4E0 | 3.5E0 | 3.2E-2 | 1.8E-2 | 1.2E1 | 1.7E1 | 52 | 22 | 52 | 22 | 0.52 |
| Ql | pg/ml | 4.5E0 | 9.0E0 | 1.4E1 | 1.5E1 | 2.7E1 | 2.2E1 | 1.0E-9 | 1.0E-9 | 1.8E2 | 8.8E1 | 53 | 23 | 53 | 23 | 0.53 |
| Qm | pg/ml | 4.5E0 | 3.5E0 | 2.0E1 | 3.0E1 | 3.5E1 | 4.3E1 | 1.0E-9 | 1.0E-9 | 1.8E2 | 1.7E2 | 53 | 23 | 53 | 23 | 0.55 |
| Qn | pg/ml | 6.1E-1 | 6.1E-1 | 4.6E0 | 1.6E1 | 8.8E0 | 5.2E1 | 1.0E-9 | 1.0E-9 | 3.8E1 | 2.4E2 | 53 | 23 | 53 | 23 | 0.51 |
| Nv | pg/ml | 4.3E3 | 5.3E3 | 1.0E4 | 1.3E4 | 2.0E4 | 2.2E4 | 8.4E1 | 5.4E2 | 1.5E5 | 1.1E5 | 79 | 34 | 79 | 34 | 0.54 |
| Nw | pg/ml | 8.9E3 | 1.4E4 | 1.3E4 | 1.7E4 | 1.2E4 | 1.4E4 | 5.7E2 | 1.6E3 | 7.3E4 | 6.1E4 | 79 | 34 | 79 | 34 | 0.59 |
| Nx | pg/ml | 2.4E2 | 2.6E2 | 4.7E2 | 6.1E2 | 6.3E2 | 7.0E2 | 1.0E-9 | 1.0E-9 | 2.6E3 | 2.5E3 | 79 | 34 | 79 | 34 | 0.58 |
| Ny | pg/ml | 4.1E0 | 1.0E1 | 1.5E1 | 3.3E1 | 3.2E1 | 7.5E1 | 1.0E-9 | 1.0E-9 | 1.9E2 | 4.2E2 | 79 | 34 | 79 | 34 | 0.63 |
| Oa | pg/ml | 1.2E2 | 7.3E2 | 3.1E2 | 1.0E3 | 4.6E2 | 1.1E3 | 1.0E-9 | 4.9E0 | 2.3E3 | 4.5E3 | 53 | 23 | 53 | 23 | 0.68 |
| Op | pg/ml | 4.6E5 | 4.4E5 | 4.5E5 | 4.2E5 | 1.5E5 | 2.2E5 | 1.8E5 | 5.2E4 | 7.1E5 | 7.5E5 | 23 | 11 | 23 | 11 | 0.46 |
| Wn | ng/ml | 1.1E1 | 2.0E1 | 1.9E1 | 2.8E1 | 2.4E1 | 2.1E1 | 8.9E-1 | 4.8E0 | 1.1E2 | 6.2E1 | 19 | 8 | 19 | 8 | 0.69 |
| Tk | ng/ml | 1.5E2 | 1.2E2 | 3.2E2 | 2.0E2 | 5.4E2 | 2.3E2 | 1.4E1 | 3.1E1 | 2.3E3 | 7.7E2 | 20 | 9 | 20 | 9 | 0.44 |
| Oe | pg/ml | 2.2E1 | 5.3E1 | 2.6E2 | 2.9E2 | 4.9E2 | 4.5E2 | 1.0E-9 | 1.0E-9 | 3.4E3 | 1.6E3 | 79 | 34 | 79 | 34 | 0.53 |
| Of | pg/ml | 1.3E2 | 1.7E2 | 1.3E4 | 4.8E3 | 7.1E4 | 1.2E4 | 1.0E-9 | 1.0E-9 | 6.2E5 | 5.4E4 | 79 | 34 | 79 | 34 | 0.52 |
| Og | pg/ml | 8.7E-2 | 7.5E-2 | 4.0E-1 | 4.9E-1 | 1.3E0 | 1.2E0 | 1.0E-9 | 1.0E-9 | 1.0E1 | 5.0E0 | 79 | 34 | 79 | 34 | 0.45 |

Figure 25 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oh | pg/ml | 2.6E0 | 4.2E0 | 9.6E0 | 1.7E1 | 2.5E1 | 4.9E1 | 1.0E-9 | 1.0E-9 | 2.0E2 | 2.8E2 | 79 | 34 | 79 | 34 | 0.59 |
| Oi | pg/ml | 3.2E0 | 2.9E0 | 6.2E0 | 6.7E0 | 8.2E0 | 8.9E0 | 1.0E-9 | 1.0E-9 | 4.1E1 | 3.6E1 | 79 | 34 | 79 | 34 | 0.51 |
| Ok | pg/ml | 4.6E2 | 5.3E2 | 5.7E2 | 8.3E2 | 4.6E2 | 7.5E2 | 4.0E1 | 3.9E1 | 2.4E3 | 3.2E3 | 79 | 34 | 79 | 34 | 0.60 |
| Om | pg/ml | 4.6E2 | 6.2E2 | 1.2E3 | 9.1E2 | 4.1E3 | 1.0E3 | 1.0E-9 | 8.4E1 | 3.6E4 | 5.0E3 | 79 | 34 | 79 | 34 | 0.57 |
| On | pg/ml | 1.9E2 | 2.3E2 | 2.6E2 | 4.0E2 | 2.6E2 | 4.0E2 | 7.2E0 | 3.9E1 | 1.6E3 | 1.5E3 | 79 | 34 | 79 | 34 | 0.60 |
| Or | pg/ml | 1.2E1 | 2.3E1 | 4.0E1 | 7.9E1 | 7.7E1 | 1.3E2 | 1.0E-9 | 1.0E-9 | 4.4E2 | 4.5E2 | 52 | 24 | 52 | 24 | 0.59 |
| Ow | pg/ml | 4.2E1 | 4.6E1 | 1.5E2 | 3.1E2 | 4.8E2 | 7.0E2 | 1.0E-9 | 1.0E-9 | 3.2E3 | 3.0E3 | 52 | 24 | 52 | 24 | 0.53 |
| Ou | pg/ml | 5.6E2 | 3.3E2 | 1.0E3 | 2.1E3 | 1.5E3 | 3.5E3 | 1.0E-9 | 1.0E-9 | 8.1E3 | 1.1E4 | 52 | 24 | 52 | 24 | 0.46 |
| Ul | ng/ml | 1.0E-9 | 1.0E-9 | 8.9E-1 | 1.6E0 | 3.8E0 | 5.4E0 | 1.0E-9 | 1.0E-9 | 2.4E1 | 2.1E1 | 53 | 23 | 53 | 23 | 0.51 |
| Uo | ng/ml | 1.0E-9 | 1.0E-9 | 7.3E-2 | 3.1E-2 | 1.9E-1 | 9.4E-2 | 1.0E-9 | 1.0E-9 | 8.5E-1 | 3.3E-1 | 53 | 23 | 53 | 23 | 0.46 |
| Uk | ng/ml | 1.0E-9 | 1.0E-9 | 9.8E-3 | 3.3E-3 | 2.5E-2 | 1.5E-2 | 1.0E-9 | 1.0E-9 | 1.3E-1 | 7.1E-2 | 53 | 23 | 53 | 23 | 0.34 |
| Um | ng/ml | 1.0E-9 | 1.0E-9 | 1.7E-1 | 1.4E-1 | 3.2E-1 | 3.8E-1 | 1.0E-9 | 1.0E-9 | 1.3E0 | 1.4E0 | 53 | 23 | 53 | 23 | 0.41 |
| Uf | ng/ml | 7.2E-2 | 9.5E-2 | 1.6E-1 | 1.3E-1 | 2.2E-1 | 1.3E-1 | 1.1E-3 | 9.8E-3 | 1.1E0 | 5.3E-1 | 53 | 23 | 53 | 23 | 0.53 |
| Uh | ng/ml | 2.2E0 | 3.4E0 | 3.8E0 | 5.0E0 | 4.2E0 | 5.0E0 | 6.0E-2 | 1.9E-1 | 1.7E1 | 1.8E1 | 53 | 23 | 53 | 23 | 0.58 |
| Un | ng/ml | 2.2E0 | 2.1E0 | 2.5E0 | 2.4E0 | 1.5E0 | 1.3E0 | 4.6E-1 | 3.6E-1 | 8.0E0 | 5.1E0 | 53 | 23 | 53 | 23 | 0.48 |
| Ug | ng/ml | 2.0E1 | 1.1E1 | 3.0E1 | 1.9E1 | 3.3E1 | 2.3E1 | 1.2E0 | 2.5E0 | 1.8E2 | 1.1E2 | 53 | 23 | 53 | 23 | 0.38 |
| Ur | ng/ml | 9.6E-2 | 1.1E-1 | 3.0E-1 | 4.5E-1 | 5.1E-1 | 9.7E-1 | 1.0E-9 | 1.0E-9 | 2.8E0 | 4.5E0 | 52 | 23 | 52 | 23 | 0.50 |
| Up | ng/ml | 1.0E-9 | 1.0E-9 | 6.0E-3 | 2.9E-3 | 1.3E-2 | 9.7E-3 | 1.0E-9 | 1.0E-9 | 6.0E-2 | 4.5E-2 | 52 | 23 | 52 | 23 | 0.39 |
| Us | ng/ml | 6.5E-3 | 3.6E-3 | 2.0E-2 | 4.3E-2 | 3.5E-2 | 8.3E-2 | 1.0E-9 | 1.0E-9 | 2.1E-1 | 3.6E-1 | 52 | 23 | 52 | 23 | 0.49 |
| Uv | ng/ml | 3.1E-3 | 3.5E-3 | 9.8E-3 | 6.8E-3 | 2.4E-2 | 1.1E-2 | 1.0E-9 | 1.0E-9 | 1.5E-1 | 4.4E-2 | 52 | 23 | 52 | 23 | 0.49 |
| Ut | ng/ml | 6.0E-1 | 9.0E-1 | 2.2E0 | 3.0E0 | 3.7E0 | 5.2E0 | 1.0E-9 | 9.2E-2 | 1.7E1 | 2.4E1 | 52 | 23 | 52 | 23 | 0.59 |
| Uu | ng/ml | 7.1E0 | 5.2E0 | 7.9E0 | 6.4E0 | 5.1E0 | 4.6E0 | 4.5E-1 | 1.5E0 | 2.0E1 | 2.1E1 | 52 | 23 | 52 | 23 | 0.41 |
| Uw | ng/ml | 2.5E0 | 4.0E0 | 3.0E0 | 3.5E0 | 2.2E0 | 1.9E0 | 2.0E-1 | 8.2E-1 | 7.9E0 | 6.4E0 | 23 | 11 | 23 | 11 | 0.61 |
| Vb | ng/ml | 9.6E-1 | 8.9E-1 | 9.8E-1 | 8.9E-1 | 4.3E-1 | 5.2E-1 | 2.1E-1 | 2.6E-1 | 1.8E0 | 1.9E0 | 23 | 11 | 23 | 11 | 0.45 |
| Vc | ng/ml | 1.0E-9 | 1.0E-9 | 5.8E-4 | 1.0E-9 | 2.8E-3 | 0.0E0 | 1.0E-9 | 1.0E-9 | 1.3E-2 | 1.0E-9 | 23 | 11 | 23 | 11 | 0.48 |
| Uy | ng/ml | 1.2E0 | 1.5E0 | 6.9E0 | 1.1E1 | 2.0E1 | 2.2E1 | 3.1E-2 | 2.0E-2 | 9.9E1 | 6.4E1 | 23 | 11 | 23 | 11 | 0.49 |
| Uz | ng/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 23 | 11 | 23 | 11 | 0.50 |
| Ux | ng/ml | 1.9E2 | 1.6E2 | 2.3E2 | 1.9E2 | 1.5E2 | 1.4E2 | 9.9E0 | 2.0E1 | 5.3E2 | 4.6E2 | 23 | 11 | 23 | 11 | 0.43 |
| Va | ng/ml | 1.8E1 | 2.8E0 | 2.8E1 | 1.3E1 | 3.2E1 | 2.2E1 | 8.1E-1 | 1.2E0 | 1.2E2 | 6.2E1 | 23 | 11 | 23 | 11 | 0.32 |
| Vh | ng/ml | 1.1E-2 | 1.3E-2 | 1.6E-2 | 1.2E-2 | 1.8E-2 | 9.0E-3 | 5.2E-4 | 1.0E-3 | 7.6E-2 | 2.7E-2 | 23 | 11 | 23 | 11 | 0.48 |
| Vi | ng/ml | 3.0E-3 | 1.6E-2 | 1.1E-2 | 2.4E-2 | 1.9E-2 | 3.4E-2 | 1.6E-4 | 1.0E-9 | 7.5E-2 | 1.2E-1 | 23 | 11 | 23 | 11 | 0.60 |
| Vj | ng/ml | 5.5E1 | 1.4E1 | 4.4E2 | 4.2E1 | 1.7E3 | 5.3E1 | 6.5E0 | 4.2E0 | 8.4E3 | 1.7E2 | 23 | 9 | 23 | 9 | 0.32 |
| Vp | ng/ml | 1.0E-9 | 1.0E-9 | 6.1E-2 | 7.5E-2 | 2.1E-1 | 2.0E-1 | 1.0E-9 | 1.0E-9 | 1.2E0 | 7.4E-1 | 53 | 23 | 53 | 23 | 0.55 |
| Vt | ng/ml | 7.3E0 | 1.1E1 | 1.0E1 | 1.2E1 | 1.2E1 | 9.1E0 | 1.1E0 | 8.8E-1 | 6.5E1 | 3.8E1 | 53 | 23 | 53 | 23 | 0.61 |
| Vu | ng/ml | 1.0E-9 | 1.0E0 | 2.1E0 | 2.7E0 | 4.3E0 | 5.0E0 | 1.0E-9 | 1.0E-9 | 2.1E1 | 2.2E1 | 53 | 23 | 53 | 23 | 0.59 |
| Vq | ng/ml | 2.2E2 | 5.7E2 | 8.4E2 | 1.2E3 | 1.9E3 | 2.9E3 | 9.0E-1 | 1.8E1 | 1.1E4 | 1.2E4 | 38 | 18 | 38 | 18 | 0.61 |
| Vo | ng/ml | 2.6E1 | 2.5E1 | 2.5E1 | 2.4E1 | 6.0E0 | 5.3E0 | 2.4E1 | 4.9E0 | 4.8E1 | 3.1E1 | 53 | 23 | 53 | 23 | 0.43 |
| Vs | ng/ml | 1.0E-9 | 1.0E-9 | 4.7E0 | 2.8E0 | 8.9E0 | 5.1E0 | 1.0E-9 | 1.0E-9 | 4.2E1 | 1.5E1 | 53 | 21 | 53 | 21 | 0.45 |
| Vv | ng/ml | 4.3E0 | 1.5E0 | 5.9E0 | 4.0E0 | 6.4E0 | 6.4E0 | 1.0E-9 | 1.0E-9 | 2.8E1 | 2.6E1 | 53 | 23 | 53 | 23 | 0.39 |
| Vw | ng/ml | 4.5E1 | 2.6E1 | 4.2E1 | 2.9E1 | 1.8E1 | 1.8E1 | 2.5E0 | 4.4E0 | 7.0E1 | 6.6E1 | 23 | 11 | 23 | 11 | 0.29 |
| Oy | pg/ml | 4.7E-1 | 3.6E-1 | 3.5E0 | 4.6E0 | 1.2E1 | 1.3E1 | 1.0E-9 | 1.0E-9 | 9.9E1 | 5.5E1 | 78 | 34 | 78 | 34 | 0.46 |
| Oz | pg/ml | 2.4E-1 | 3.4E-1 | 7.5E-1 | 2.9E-1 | 3.3E0 | 5.5E-1 | 1.0E-9 | 1.0E-9 | 2.9E1 | 2.2E0 | 78 | 34 | 78 | 34 | 0.42 |
| Pa | pg/ml | 4.1E-1 | 4.5E-1 | 1.1E0 | 1.1E0 | 3.6E0 | 1.4E0 | 1.0E-9 | 1.0E-9 | 2.9E1 | 6.5E0 | 78 | 34 | 78 | 34 | 0.58 |
| Pb | pg/ml | 4.4E-2 | 1.0E-9 | 2.3E-1 | 9.4E-1 | 8.4E-1 | 2.0E-1 | 1.0E-9 | 1.0E-9 | 7.3E0 | 1.1E0 | 78 | 34 | 78 | 34 | 0.40 |
| Pc | pg/ml | 3.3E-1 | 3.2E-1 | 4.1E-1 | 3.7E-1 | 4.2E-1 | 4.0E-1 | 1.0E-9 | 1.0E-9 | 1.8E0 | 1.4E0 | 78 | 34 | 78 | 34 | 0.47 |
| Pd | pg/ml | 2.0E0 | 2.0E0 | 1.5E1 | 4.0E0 | 9.5E1 | 5.7E0 | 1.0E-9 | 1.0E-9 | 8.4E2 | 2.9E1 | 78 | 34 | 78 | 34 | 0.48 |
| Pe | pg/ml | 2.4E1 | 5.5E1 | 1.1E2 | 2.2E2 | 4.0E2 | 7.5E2 | 1.0E-9 | 1.0E-9 | 3.3E3 | 4.3E3 | 78 | 34 | 78 | 34 | 0.61 |
| Pf | pg/ml | 1.6E0 | 5.9E0 | 2.5E1 | 2.3E1 | 1.7E2 | 6.5E1 | 1.0E-9 | 1.0E-9 | 1.5E3 | 3.8E2 | 78 | 34 | 78 | 34 | 0.66 |
| Pg | pg/ml | 3.2E0 | 7.8E0 | 1.2E2 | 3.9E1 | 8.7E2 | 8.2E1 | 1.0E-9 | 1.0E-9 | 7.7E3 | 4.0E2 | 78 | 34 | 78 | 34 | 0.62 |
| Ph | ng/ml | 2.1E-1 | 1.8E-1 | 4.0E-1 | 3.1E-1 | 5.9E-1 | 4.8E-1 | 1.0E-9 | 1.0E-9 | 2.8E0 | 2.4E0 | 52 | 24 | 52 | 24 | 0.49 |
| Pi | ng/ml | 1.8E-1 | 2.3E-1 | 2.5E-1 | 3.0E-1 | 2.2E-1 | 3.1E-1 | 1.0E-9 | 1.0E-9 | 9.7E-1 | 1.4E0 | 52 | 24 | 52 | 24 | 0.54 |
| Pj | ng/mL | 6.7E0 | 5.7E0 | 7.8E0 | 6.5E0 | 6.0E0 | 4.5E0 | 1.3E0 | 3.8E-1 | 2.5E1 | 2.0E1 | 52 | 24 | 52 | 24 | 0.45 |
| Pk | ng/ml | 6.8E-3 | 1.1E-2 | 1.3E-2 | 1.4E-2 | 2.2E-2 | 1.1E-2 | 1.0E-9 | 1.0E-9 | 1.4E-1 | 3.9E-2 | 52 | 24 | 52 | 24 | 0.62 |
| aA | mg/dL | 8.9E-1 | 1.0E0 | 1.0E0 | 1.0E0 | 5.9E-1 | 5.6E-1 | 2.6E-1 | 4.0E-1 | 3.9E0 | 3.6E0 | 106 | 40 | 106 | 40 | 0.54 |
| aC | mg/mL | 2.2E0 | 1.9E0 | 2.4E0 | 2.1E0 | 1.0E0 | 1.0E0 | 8.7E-1 | 7.5E-1 | 5.5E0 | 4.8E0 | 55 | 22 | 55 | 22 | 0.40 |
| aD | ug/mL | 3.1E0 | 4.7E0 | 4.4E0 | 5.7E0 | 3.6E0 | 4.4E0 | 8.7E-1 | 7.5E-1 | 2.0E1 | 2.1E1 | 55 | 22 | 55 | 22 | 0.61 |
| aE | mg/mL | 5.3E-1 | 5.2E-1 | 5.5E-1 | 5.6E-1 | 1.5E-1 | 1.9E-1 | 2.5E-1 | 1.8E-1 | 1.0E0 | 9.3E-1 | 55 | 22 | 55 | 22 | 0.52 |

Figure 25 Continued

| Code | Units | Median | | Average | | Standard Deviation | | Minimum | | Maximum | | Number of Samples | | Number of Patients | | AUC |
|------|-------|--------|------|---------|------|--------|------|--------|------|--------|------|--------|-----|---------|-----|------|
|      |       | NonDis | Dis  | NonDis  | Dis  | NonDis | Dis  | NonDis | Dis  | NonDis | Dis  | NonDis | Dis | NonDis  | Dis |      |
| aF | ng/mL | 1.7E0 | 2.2E0 | 4.1E0 | 4.3E0 | 5.9E0 | 6.2E0 | 4.3E-3 | 3.7E-1 | 3.5E1 | 2.9E1 | 55 | 22 | 55 | 22 | 0.50 |
| aG | mg/mL | 1.5E-1 | 1.3E-1 | 1.6E-1 | 1.6E-1 | 8.1E-2 | 1.0E-1 | 5.1E-2 | 6.4E-2 | 3.8E-1 | 4.8E-1 | 55 | 22 | 55 | 22 | 0.48 |
| aH | ug/mL | 8.1E1 | 7.3E1 | 9.6E1 | 7.7E1 | 5.1E1 | 4.1E1 | 1.1E1 | 2.0E1 | 2.6E2 | 1.7E2 | 55 | 22 | 55 | 22 | 0.39 |
| aI | ug/mL | 2.0E2 | 1.5E2 | 1.9E2 | 1.6E2 | 6.1E1 | 6.2E1 | 4.8E1 | 7.5E1 | 3.4E2 | 3.2E2 | 55 | 22 | 55 | 22 | 0.30 |
| aJ | ug/mL | 2.4E0 | 3.5E0 | 3.1E0 | 3.6E0 | 2.3E0 | 1.9E0 | 7.6E-1 | 8.2E-1 | 1.6E1 | 7.9E0 | 55 | 22 | 55 | 22 | 0.61 |
| aK | ng/mL | 1.4E0 | 1.3E0 | 2.0E0 | 1.5E0 | 2.0E0 | 1.0E0 | 2.9E-4 | 4.7E-1 | 1.0E1 | 4.2E0 | 55 | 22 | 55 | 22 | 0.49 |
| aL | mg/mL | 7.8E-1 | 7.7E-1 | 8.1E-1 | 7.5E-1 | 2.5E-1 | 2.6E-1 | 3.0E-1 | 4.1E-1 | 1.7E0 | 1.5E0 | 55 | 22 | 55 | 22 | 0.43 |
| aM | U/mL | 2.6E1 | 2.8E1 | 3.8E1 | 5.2E1 | 3.6E1 | 4.9E1 | 4.2E-2 | 4.2E-2 | 1.4E2 | 1.4E2 | 55 | 22 | 55 | 22 | 0.56 |
| aN | U/mL | 1.9E1 | 1.7E1 | 3.5E1 | 2.7E1 | 5.5E1 | 2.5E1 | 2.5E-3 | 2.5E-3 | 3.8E2 | 8.5E1 | 55 | 22 | 55 | 22 | 0.47 |
| aO | pg/mL | 7.3E1 | 3.6E1 | 3.7E2 | 4.2E2 | 8.4E2 | 6.9E2 | 6.0E-2 | 6.0E-2 | 3.6E3 | 2.1E3 | 55 | 22 | 55 | 22 | 0.47 |
| aP | ng/mL | 1.7E0 | 1.7E0 | 2.0E0 | 2.1E0 | 1.2E0 | 1.4E0 | 7.8E-1 | 6.8E-1 | 6.4E0 | 6.5E0 | 55 | 22 | 55 | 22 | 0.50 |
| aQ | ng/mL | 2.9E-1 | 2.2E-1 | 4.9E-1 | 2.7E-1 | 4.7E-1 | 1.9E-1 | 2.5E-2 | 5.9E-2 | 2.0E0 | 9.2E-1 | 55 | 22 | 55 | 22 | 0.41 |
| aR | ng/mL | 1.7E0 | 1.6E0 | 3.2E0 | 2.4E0 | 4.5E0 | 2.4E0 | 4.5E-1 | 5.6E-1 | 3.0E1 | 1.1E1 | 55 | 22 | 55 | 22 | 0.46 |
| aS | ng/mL | 3.5E-1 | 4.8E-1 | 8.9E-1 | 6.6E-1 | 1.4E0 | 5.9E-1 | 4.2E-3 | 7.0E-2 | 6.2E0 | 2.3E0 | 55 | 22 | 55 | 22 | 0.54 |
| aU | pg/mL | 6.3E1 | 6.0E1 | 1.1E2 | 6.4E1 | 1.3E2 | 3.4E1 | 7.4E-2 | 2.0E1 | 7.0E2 | 1.6E2 | 55 | 22 | 55 | 22 | 0.46 |
| aV | ng/mL | 6.9E-1 | 4.4E-1 | 1.6E0 | 6.3E-1 | 4.4E0 | 4.4E-1 | 3.8E-2 | 9.1E-2 | 3.3E1 | 1.6E0 | 55 | 22 | 55 | 22 | 0.44 |
| aW | pg/mL | 2.1E1 | 1.5E1 | 2.0E1 | 1.4E1 | 9.1E0 | 1.0E1 | 7.2E-2 | 7.2E-2 | 3.7E1 | 3.1E1 | 55 | 22 | 55 | 22 | 0.34 |
| aX | ng/mL | 6.8E0 | 9.8E0 | 1.1E1 | 1.1E1 | 1.0E1 | 9.0E0 | 7.0E-1 | 1.1E0 | 4.6E1 | 3.1E1 | 55 | 22 | 55 | 22 | 0.49 |
| aY | pg/mL | 5.3E1 | 5.0E1 | 9.3E1 | 5.9E1 | 1.7E2 | 5.0E1 | 4.1E-1 | 4.1E-1 | 1.2E3 | 2.0E2 | 55 | 22 | 55 | 22 | 0.43 |
| aZ | pg/mL | 1.5E2 | 2.6E2 | 5.4E2 | 6.3E2 | 1.2E3 | 1.1E3 | 1.7E0 | 1.5E1 | 5.9E3 | 4.3E3 | 55 | 22 | 55 | 22 | 0.57 |
| bA | ng/mL | 9.4E0 | 2.1E1 | 5.9E1 | 6.7E1 | 1.4E2 | 1.2E2 | 3.0E-2 | 3.0E-2 | 9.4E2 | 4.3E2 | 55 | 22 | 55 | 22 | 0.55 |
| bB | ng/mL | 3.1E2 | 2.5E2 | 3.4E2 | 2.6E2 | 1.9E2 | 1.7E2 | 3.6E1 | 2.3E1 | 8.1E2 | 6.2E2 | 55 | 22 | 55 | 22 | 0.38 |
| bC | ng/mL | 3.3E2 | 3.0E2 | 7.2E2 | 5.4E2 | 1.0E3 | 8.3E2 | 9.8E0 | 5.0E1 | 4.7E3 | 4.0E3 | 55 | 22 | 55 | 22 | 0.47 |
| bE | mg/mL | 5.1E0 | 5.0E0 | 5.6E0 | 5.1E0 | 2.2E0 | 1.8E0 | 1.4E0 | 1.8E0 | 1.2E1 | 9.6E0 | 55 | 22 | 55 | 22 | 0.44 |
| bF | pg/mL | 2.1E1 | 3.3E1 | 2.7E2 | 4.5E2 | 1.4E3 | 1.4E3 | 2.1E0 | 6.2E0 | 1.0E4 | 6.3E3 | 55 | 22 | 55 | 22 | 0.61 |
| bG | ng/mL | 1.2E0 | 1.5E0 | 2.3E0 | 3.7E0 | 3.2E0 | 6.4E0 | 2.5E-1 | 2.7E-1 | 1.7E1 | 3.0E1 | 55 | 22 | 55 | 22 | 0.59 |
| bH | pg/mL | 5.7E-1 | 5.7E-1 | 5.1E0 | 3.4E0 | 1.7E1 | 4.7E0 | 5.7E-1 | 5.7E-1 | 1.2E2 | 1.9E1 | 55 | 22 | 55 | 22 | 0.57 |
| bI | ng/mL | 4.0E-3 | 4.0E-3 | 1.1E-1 | 5.1E-2 | 2.2E-1 | 1.4E-1 | 4.0E-3 | 4.0E-3 | 9.8E-1 | 6.2E-1 | 55 | 22 | 55 | 22 | 0.45 |
| bJ | mg/mL | 1.9E0 | 1.9E0 | 2.4E0 | 2.0E0 | 2.2E0 | 1.3E0 | 2.5E-4 | 2.8E-1 | 1.1E1 | 5.3E0 | 55 | 22 | 55 | 22 | 0.48 |
| bL | pg/mL | 1.7E0 | 3.0E0 | 6.2E0 | 4.2E0 | 9.5E0 | 3.9E0 | 4.6E-2 | 4.6E-2 | 3.5E1 | 1.4E1 | 55 | 22 | 55 | 22 | 0.55 |
| bM | mg/mL | 2.0E0 | 2.2E0 | 2.7E0 | 2.7E0 | 1.6E0 | 1.8E0 | 4.1E-1 | 7.1E-1 | 7.9E0 | 8.6E0 | 55 | 22 | 55 | 22 | 0.51 |
| bN | ng/mL | 6.4E1 | 2.3E1 | 1.6E2 | 5.1E1 | 3.4E2 | 8.1E1 | 1.4E-1 | 1.4E-1 | 1.9E3 | 3.7E2 | 55 | 22 | 55 | 22 | 0.34 |
| bO | ng/mL | 4.0E-2 | 4.0E-2 | 6.3E0 | 4.3E0 | 1.6E1 | 9.6E0 | 4.0E-2 | 4.0E-2 | 1.0E2 | 3.7E1 | 55 | 22 | 55 | 22 | 0.46 |
| bP | mg/mL | 4.8E-1 | 6.8E-1 | 6.5E-1 | 8.6E-1 | 7.1E-1 | 7.2E-1 | 1.3E-1 | 1.1E-1 | 4.8E0 | 3.1E0 | 55 | 22 | 55 | 22 | 0.63 |
| bQ | pg/mL | 1.6E1 | 2.3E1 | 2.7E2 | 4.6E1 | 1.8E3 | 5.2E1 | 1.5E-1 | 6.4E0 | 1.3E4 | 1.8E2 | 55 | 22 | 55 | 22 | 0.60 |
| bR | ng/mL | 1.2E-2 | 1.2E-2 | 2.5E-1 | 9.1E-2 | 1.2E0 | 1.2E-1 | 1.2E-2 | 1.2E-2 | 8.7E0 | 3.9E-1 | 55 | 22 | 55 | 22 | 0.51 |
| bS | pg/mL | 9.4E-1 | 9.4E-1 | 9.9E0 | 2.8E0 | 5.3E1 | 8.9E0 | 9.4E-1 | 9.4E-1 | 3.9E2 | 4.3E1 | 55 | 22 | 55 | 22 | 0.49 |
| bU | ng/mL | 1.3E-2 | 1.1E-1 | 2.6E-1 | 1.3E-1 | 9.1E-1 | 1.5E-1 | 1.3E-2 | 1.3E-2 | 6.6E0 | 6.3E-1 | 55 | 22 | 55 | 22 | 0.54 |
| bV | pg/mL | 4.5E2 | 5.2E2 | 5.3E2 | 6.5E2 | 2.4E2 | 5.8E2 | 1.7E2 | 3.0E2 | 1.4E3 | 3.1E3 | 55 | 22 | 55 | 22 | 0.55 |
| bW | pg/mL | 3.1E2 | 3.3E2 | 4.9E2 | 4.6E2 | 6.6E2 | 4.0E2 | 9.2E1 | 1.3E2 | 4.8E3 | 1.8E3 | 55 | 22 | 55 | 22 | 0.51 |
| bX | ng/mL | 2.5E-5 | 6.9E-4 | 1.8E-3 | 2.5E-3 | 2.7E-3 | 3.0E-3 | 2.5E-5 | 2.5E-5 | 1.1E-2 | 8.7E-3 | 55 | 22 | 55 | 22 | 0.57 |
| bZ | pg/mL | 2.5E2 | 2.9E2 | 1.5E3 | 2.8E3 | 7.8E3 | 9.0E3 | 1.5E-1 | 1.5E-1 | 5.8E4 | 4.3E4 | 55 | 22 | 55 | 22 | 0.58 |
| cA | pg/mL | 6.0E-1 | 6.0E-1 | 8.0E0 | 6.0E-1 | 5.0E1 | 0.0E0 | 6.0E-1 | 6.0E-1 | 3.7E2 | 6.0E-1 | 55 | 22 | 55 | 22 | 0.45 |
| cB | ng/mL | 4.9E-2 | 3.6E-2 | 8.5E-2 | 6.8E-2 | 1.1E-1 | 9.9E-2 | 1.7E-3 | 1.7E-3 | 5.3E-1 | 4.0E-1 | 55 | 22 | 55 | 22 | 0.45 |
| cC | pg/mL | 2.4E1 | 4.6E1 | 3.8E1 | 3.8E1 | 6.5E1 | 2.3E1 | 1.0E0 | 1.0E0 | 4.5E2 | 6.7E1 | 55 | 22 | 55 | 22 | 0.59 |
| cD | pg/mL | 3.3E0 | 4.7E0 | 1.1E1 | 8.1E0 | 2.7E1 | 1.1E1 | 3.3E-1 | 3.3E-1 | 1.4E2 | 4.5E1 | 55 | 22 | 55 | 22 | 0.59 |
| cE | pg/mL | 4.6E1 | 6.5E1 | 1.9E2 | 2.4E2 | 6.5E2 | 3.4E2 | 1.2E-1 | 1.2E-1 | 3.8E3 | 1.3E3 | 55 | 22 | 55 | 22 | 0.65 |
| cF | pg/mL | 9.4E0 | 5.0E0 | 2.0E1 | 1.1E1 | 4.6E1 | 1.4E1 | 5.3E-1 | 5.3E-1 | 2.7E2 | 5.0E1 | 55 | 22 | 55 | 22 | 0.47 |
| cG | pg/mL | 4.6E1 | 6.6E1 | 2.9E2 | 9.9E1 | 1.4E3 | 7.6E1 | 7.8E0 | 7.8E0 | 1.0E4 | 2.6E2 | 55 | 22 | 55 | 22 | 0.64 |
| cH | uIU/mL | 4.7E0 | 2.6E0 | 5.9E0 | 5.9E0 | 1.8E1 | 1.2E1 | 8.6E-3 | 8.6E-3 | 1.2E2 | 5.3E1 | 55 | 22 | 55 | 22 | 0.36 |
| cI | pg/mL | 6.0E0 | 9.9E0 | 1.5E1 | 1.9E1 | 1.9E1 | 2.5E1 | 7.1E-2 | 5.1E-1 | 6.6E1 | 9.4E1 | 55 | 22 | 55 | 22 | 0.57 |
| cJ | ug/mL | 7.2E1 | 5.6E1 | 1.4E2 | 1.1E2 | 1.6E2 | 1.5E2 | 1.1E1 | 7.2E0 | 6.9E2 | 6.2E2 | 55 | 22 | 55 | 22 | 0.44 |
| cK | ng/mL | 3.8E-3 | 3.8E-3 | 3.2E-2 | 3.8E-3 | 2.0E-1 | 0.0E0 | 3.8E-3 | 3.8E-3 | 1.5E0 | 3.8E-3 | 55 | 22 | 55 | 22 | 0.47 |
| cL | pg/mL | 1.7E2 | 2.0E2 | 7.7E2 | 6.0E2 | 3.3E3 | 1.5E3 | 1.6E1 | 3.1E1 | 2.4E4 | 7.4E3 | 55 | 22 | 55 | 22 | 0.58 |
| cM | pg/mL | 2.5E2 | 2.8E2 | 2.8E2 | 2.9E2 | 2.2E2 | 1.1E2 | 3.3E1 | 4.2E1 | 1.5E3 | 4.5E2 | 55 | 22 | 55 | 22 | 0.59 |
| cN | pg/mL | 1.2E2 | 1.2E2 | 1.4E2 | 1.3E2 | 1.3E2 | 3.5E1 | 4.3E1 | 7.3E1 | 1.1E3 | 2.1E2 | 55 | 22 | 55 | 22 | 0.53 |
| cO | pg/mL | 2.0E2 | 2.4E2 | 5.7E2 | 2.4E2 | 2.6E3 | 9.0E1 | 6.1E1 | 8.2E1 | 1.9E4 | 4.3E2 | 55 | 22 | 55 | 22 | 0.58 |

Figure 25 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cP | ng/mL | 2.8E3 | 2.3E3 | 2.9E3 | 2.5E3 | 9.7E2 | 8.0E2 | 1.1E3 | 1.4E3 | 5.5E3 | 4.5E3 | 55 | 22 | 55 | 22 | 0.38 |
| cQ | ng/mL | 6.5E-2 | 3.6E-2 | 1.6E-1 | 1.6E-1 | 2.5E-1 | 3.1E-1 | 2.0E-3 | 2.0E-3 | 1.4E0 | 1.3E0 | 55 | 22 | 55 | 22 | 0.43 |
| cR | ng/mL | 2.8E2 | 5.4E2 | 4.2E2 | 6.2E2 | 4.4E2 | 4.8E2 | 3.0E1 | 3.6E1 | 2.3E3 | 2.0E3 | 55 | 22 | 55 | 22 | 0.66 |
| cS | ng/mL | 2.7E2 | 2.5E2 | 3.2E2 | 4.8E2 | 2.1E2 | 5.9E2 | 7.0E1 | 1.1E2 | 9.4E2 | 2.6E3 | 55 | 22 | 55 | 22 | 0.51 |
| cT | ng/mL | 3.9E1 | 6.2E1 | 1.5E2 | 1.8E2 | 3.3E2 | 3.5E2 | 7.2E0 | 4.2E0 | 2.1E3 | 1.3E3 | 55 | 22 | 55 | 22 | 0.54 |
| cU | ng/mL | 7.0E1 | 6.3E1 | 1.1E2 | 1.0E2 | 2.2E2 | 9.6E1 | 1.4E1 | 1.7E1 | 1.6E3 | 4.2E2 | 55 | 22 | 55 | 22 | 0.53 |
| cV | ng/mL | 1.8E-1 | 2.4E-1 | 2.8E-1 | 8.4E-1 | 4.2E-1 | 2.0E0 | 3.7E-2 | 4.1E-2 | 2.5E0 | 9.7E0 | 55 | 22 | 55 | 22 | 0.67 |
| cW | mIU/mL | 4.2E-2 | 4.0E-2 | 6.3E-2 | 5.2E-2 | 5.9E-2 | 3.7E-2 | 1.0E-2 | 4.8E-3 | 2.7E-1 | 1.5E-1 | 55 | 22 | 55 | 22 | 0.50 |
| cX | ng/mL | 1.4E-1 | 1.2E-1 | 2.0E0 | 2.0E0 | 5.5E0 | 5.9E0 | 2.3E-4 | 2.3E-4 | 2.8E1 | 2.8E1 | 55 | 22 | 55 | 22 | 0.45 |
| cY | ng/mL | 7.4E0 | 8.0E0 | 1.3E1 | 8.2E0 | 1.4E1 | 4.2E0 | 1.5E-1 | 9.8E-1 | 6.1E1 | 1.8E1 | 55 | 22 | 55 | 22 | 0.48 |
| cZ | ug/mL | 1.5E1 | 1.2E1 | 1.6E1 | 1.3E1 | 7.1E0 | 6.3E0 | 3.1E0 | 4.5E0 | 3.7E1 | 3.1E1 | 55 | 22 | 55 | 22 | 0.35 |
| dA | pg/mL | 3.4E2 | 3.0E2 | 4.7E2 | 3.2E2 | 7.6E2 | 1.3E2 | 1.3E2 | 1.5E2 | 5.8E3 | 5.5E2 | 55 | 22 | 55 | 22 | 0.41 |
| dB | ug/mL | 3.9E0 | 1.9E1 | 1.2E1 | 1.6E1 | 1.1E1 | 9.9E0 | 1.8E0 | 2.2E0 | 4.0E1 | 3.0E1 | 55 | 22 | 55 | 22 | 0.59 |
| dC | nmol/L | 3.3E1 | 3.7E1 | 3.7E1 | 3.7E1 | 1.4E1 | 1.5E1 | 1.5E1 | 7.8E0 | 8.7E1 | 6.9E1 | 55 | 22 | 55 | 22 | 0.54 |
| dD | ug/mL | 3.6E1 | 2.8E1 | 3.6E1 | 3.1E1 | 1.1E1 | 1.1E1 | 1.3E1 | 1.4E1 | 5.7E1 | 4.8E1 | 55 | 22 | 55 | 22 | 0.35 |
| dE | ng/mL | 8.4E-3 | 8.4E-3 | 3.4E-1 | 2.5E-1 | 5.2E-1 | 3.6E-1 | 8.4E-3 | 8.4E-3 | 2.0E0 | 1.4E0 | 55 | 22 | 55 | 22 | 0.50 |
| dF | ng/mL | 2.5E2 | 3.1E2 | 2.9E2 | 4.0E2 | 1.9E2 | 3.1E2 | 8.6E1 | 7.5E1 | 1.3E3 | 1.2E3 | 55 | 22 | 55 | 22 | 0.63 |
| dG | ng/mL | 1.2E1 | 1.4E1 | 1.6E1 | 1.7E1 | 2.4E1 | 1.1E1 | 3.3E0 | 3.0E0 | 1.8E2 | 5.8E1 | 55 | 22 | 55 | 22 | 0.60 |
| dH | pg/mL | 7.5E0 | 8.6E0 | 2.2E1 | 1.2E1 | 8.9E1 | 1.1E1 | 4.0E-2 | 4.0E-2 | 6.7E2 | 4.9E1 | 55 | 22 | 55 | 22 | 0.59 |
| dI | pg/mL | 4.6E-1 | 4.6E-1 | 6.9E0 | 1.2E0 | 4.4E1 | 2.2E0 | 4.6E-1 | 4.6E-1 | 3.3E2 | 1.0E1 | 55 | 22 | 55 | 22 | 0.50 |
| dJ | ng/mL | 2.3E0 | 1.8E0 | 2.3E0 | 1.8E0 | 1.2E0 | 6.7E-1 | 3.7E-1 | 3.7E-1 | 5.1E0 | 2.9E0 | 55 | 22 | 55 | 22 | 0.37 |
| dK | uIU/mL | 1.6E0 | 1.1E0 | 2.5E0 | 2.2E0 | 3.6E0 | 2.2E0 | 4.0E-2 | 1.9E-1 | 2.1E1 | 7.3E0 | 55 | 22 | 55 | 22 | 0.49 |
| dL | ng/mL | 8.8E2 | 1.2E3 | 1.1E3 | 1.2E3 | 5.4E2 | 6.3E2 | 4.7E2 | 2.8E2 | 3.2E3 | 3.3E3 | 55 | 22 | 55 | 22 | 0.57 |
| dM | pg/mL | 1.1E3 | 1.1E3 | 1.1E3 | 1.3E3 | 5.9E2 | 6.7E2 | 4.2E2 | 3.7E2 | 3.3E3 | 3.1E3 | 55 | 22 | 55 | 22 | 0.56 |
| dN | ug/mL | 9.8E1 | 8.9E1 | 1.0E2 | 1.0E2 | 3.1E1 | 4.7E1 | 3.7E1 | 2.4E1 | 1.9E2 | 2.1E2 | 55 | 22 | 55 | 22 | 0.45 |
| dR | pg/ml | 1.7E3 | 1.2E3 | 2.3E3 | 1.6E3 | 2.2E3 | 1.4E3 | 1.7E2 | 3.4E2 | 9.8E3 | 5.3E3 | 54 | 21 | 54 | 21 | 0.42 |
| dU | pg/ml | 1.4E4 | 1.8E4 | 1.6E4 | 2.5E4 | 9.1E3 | 2.5E4 | 6.7E3 | 3.1E3 | 3.5E4 | 8.1E4 | 7 | 9 | 7 | 9 | 0.57 |
| eF | ng/ml | 4.3E0 | 4.0E0 | 4.7E0 | 4.7E0 | 2.0E0 | 1.9E0 | 1.6E0 | 2.0E0 | 1.2E1 | 8.7E0 | 55 | 21 | 55 | 21 | 0.48 |
| eC | pg/ml | 3.3E2 | 2.7E2 | 3.6E2 | 2.9E2 | 1.5E2 | 2.0E2 | 5.1E1 | 1.9E1 | 7.5E2 | 7.3E2 | 51 | 17 | 51 | 17 | 0.37 |
| eD | pg/ml | 2.1E2 | 2.7E2 | 6.1E2 | 9.3E2 | 1.3E3 | 1.3E3 | 5.2E-1 | 1.4E2 | 7.0E3 | 3.8E3 | 43 | 12 | 43 | 12 | 0.66 |
| cM | ng/ml | 3.3E0 | 2.8E0 | 5.8E0 | 2.8E0 | 5.3E0 | 1.9E0 | 1.5E0 | 6.9E-1 | 1.8E1 | 7.3E0 | 15 | 12 | 15 | 12 | 0.31 |
| eQ | pg/ml | 1.0E0 | 1.0E0 | 6.5E0 | 2.8E1 | 1.5E1 | 5.4E1 | 1.0E0 | 1.0E0 | 4.0E1 | 1.5E2 | 7 | 9 | 7 | 9 | 0.56 |
| fA | ng/ml | 2.4E2 | 1.1E2 | 3.1E2 | 3.1E2 | 2.5E2 | 4.0E2 | 6.8E1 | 7.0E1 | 8.3E2 | 1.2E3 | 7 | 7 | 7 | 7 | 0.39 |
| fB | ng/ml | 7.4E2 | 7.3E2 | 8.3E2 | 8.3E2 | 4.3E2 | 2.5E2 | 3.8E2 | 5.8E2 | 1.5E3 | 1.3E3 | 7 | 8 | 7 | 8 | 0.55 |
| fP | ng/ml | 2.7E2 | 2.8E2 | 3.0E2 | 3.6E2 | 1.6E2 | 2.0E2 | 2.7E1 | 1.3E2 | 8.7E2 | 8.6E2 | 52 | 21 | 52 | 21 | 0.58 |
| fR | ng/ml | 1.4E5 | 2.0E5 | 1.8E5 | 2.4E5 | 1.6E5 | 1.4E5 | 3.6E4 | 9.8E4 | 7.2E5 | 4.8E5 | 25 | 11 | 25 | 11 | 0.65 |
| gC | ng/ml | 2.0E2 | 2.8E2 | 2.5E2 | 3.0E2 | 1.3E2 | 8.8E1 | 1.3E2 | 1.8E2 | 5.9E2 | 4.5E2 | 16 | 11 | 16 | 11 | 0.68 |
| gL | pg/ml | 6.2E4 | 6.0E4 | 7.0E4 | 6.3E4 | 2.8E4 | 3.1E4 | 3.1E4 | 1.1E4 | 1.6E5 | 1.7E5 | 54 | 21 | 54 | 21 | 0.43 |
| gP | U/ml | 3.1E2 | 2.4E2 | 3.2E2 | 2.6E2 | 1.2E2 | 9.7E1 | 7.1E1 | 9.6E1 | 8.5E2 | 5.2E2 | 54 | 21 | 54 | 21 | 0.34 |
| gW | ng/ml | 5.3E2 | 5.2E2 | 8.6E2 | 1.1E3 | 1.0E3 | 1.3E3 | 2.3E0 | 1.9E2 | 4.2E3 | 4.3E3 | 47 | 12 | 47 | 12 | 0.58 |
| tF | pg/mL | 8.8E2 | 2.5E3 | 1.1E4 | 8.4E3 | 3.7E4 | 1.6E4 | 1.2E1 | 1.8E1 | 2.5E5 | 6.9E4 | 51 | 19 | 51 | 19 | 0.60 |
| gZ | ug/ml | 1.1E0 | 1.2E0 | 5.3E0 | 6.6E1 | 9.1E0 | 1.3E2 | 1.1E-1 | 4.3E-1 | 2.5E1 | 3.8E2 | 7 | 9 | 7 | 9 | 0.52 |
| hA | ng/ml | 2.1E0 | 4.2E0 | 1.4E1 | 6.6E0 | 4.7E1 | 5.5E0 | 1.7E-2 | 1.7E-2 | 2.9E2 | 1.6E1 | 43 | 13 | 43 | 13 | 0.67 |
| nM | pg/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 26 | 16 | 26 | 16 | 0.50 |
| nN | pg/ml | 1.4E3 | 2.2E3 | 6.0E3 | 4.0E3 | 2.0E4 | 5.0E3 | 1.2E2 | 2.8E2 | 1.0E5 | 2.1E4 | 26 | 16 | 26 | 16 | 0.65 |
| nO | pg/ml | 2.8E1 | 2.5E1 | 4.2E1 | 4.2E1 | 3.9E1 | 5.7E1 | 3.5E0 | 9.7E0 | 1.5E2 | 2.4E2 | 26 | 16 | 26 | 16 | 0.49 |
| nR | pg/ml | 1.3E1 | 2.1E1 | 5.7E1 | 1.4E2 | 1.6E2 | 2.4E2 | 5.5E-1 | 1.0E0 | 8.2E2 | 7.1E2 | 26 | 16 | 26 | 16 | 0.63 |
| nT | pg/ml | 8.2E1 | 8.9E1 | 1.1E2 | 9.6E1 | 1.3E2 | 3.5E1 | 1.0E-9 | 5.7E1 | 6.4E2 | 1.9E2 | 26 | 16 | 26 | 16 | 0.53 |
| nU | pg/ml | 3.0E1 | 3.8E1 | 1.1E2 | 9.1E1 | 2.9E2 | 1.2E2 | 1.0E-9 | 1.0E-9 | 1.5E3 | 4.4E2 | 26 | 16 | 26 | 16 | 0.53 |
| lW | pg/ml | 1.0E-9 | 1.0E-9 | 9.5E0 | 5.8E0 | 3.3E1 | 1.8E1 | 1.0E-9 | 1.0E-9 | 1.6E2 | 7.0E1 | 26 | 16 | 26 | 16 | 0.42 |
| lX | pg/ml | 1.1E3 | 6.9E2 | 1.1E3 | 8.1E2 | 5.7E2 | 4.1E2 | 1.2E2 | 1.9E2 | 2.3E3 | 1.6E3 | 26 | 16 | 26 | 16 | 0.34 |
| lY | pg/ml | 2.7E1 | 1.9E1 | 3.1E1 | 1.7E1 | 2.5E1 | 9.3E0 | 4.2E0 | 3.7E0 | 1.2E2 | 3.0E1 | 26 | 16 | 26 | 16 | 0.27 |
| mE | pg/ml | 1.0E-9 | 1.0E-9 | 3.6E0 | 1.8E0 | 1.1E1 | 3.2E0 | 1.0E-9 | 1.0E-9 | 5.7E1 | 9.2E0 | 26 | 16 | 26 | 16 | 0.48 |
| mF | pg/ml | 1.0E-9 | 2.7E-1 | 5.2E0 | 2.1E0 | 2.1E1 | 4.0E0 | 1.0E-9 | 1.0E-9 | 1.1E2 | 1.3E1 | 26 | 16 | 26 | 16 | 0.55 |
| mH | pg/ml | 3.2E0 | 2.7E0 | 5.5E0 | 4.4E0 | 1.0E1 | 4.8E0 | 3.2E-1 | 9.0E-1 | 5.3E1 | 1.9E1 | 26 | 16 | 26 | 16 | 0.45 |
| mI | pg/ml | 1.0E-9 | 1.0E-9 | 1.5E1 | 1.3E1 | 3.7E1 | 2.4E1 | 1.0E-9 | 1.0E-9 | 1.8E2 | 7.8E1 | 26 | 16 | 26 | 16 | 0.48 |
| mM | pg/ml | 3.6E1 | 4.3E1 | 9.1E1 | 5.7E1 | 2.2E2 | 7.4E1 | 1.0E-9 | 1.0E-9 | 1.1E3 | 2.9E2 | 26 | 16 | 26 | 16 | 0.52 |

Figure 25 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| mP | pg/ml | 1.5E1 | 1.5E1 | 1.8E1 | 1.5E1 | 2.2E1 | 9.7E0 | 1.0E-9 | 1.0E-9 | 1.2E2 | 3.8E1 | 26 | 16 | 26 | 16 | 0.51 |
| mS | pg/ml | 1.8E3 | 1.2E3 | 1.8E3 | 1.5E3 | 8.9E2 | 1.1E3 | 1.0E-9 | 1.0E-9 | 4.6E3 | 5.1E3 | 26 | 16 | 26 | 16 | 0.33 |
| mT | pg/ml | 4.3E1 | 5.9E1 | 1.0E2 | 6.6E1 | 1.9E2 | 3.8E1 | 1.6E1 | 1.9E1 | 9.7E2 | 1.4E2 | 26 | 16 | 26 | 16 | 0.54 |
| mU | pg/ml | 2.0E0 | 3.2E0 | 1.1E1 | 3.5E0 | 4.3E1 | 2.0E0 | 1.9E-1 | 1.0E-9 | 2.2E2 | 7.7E0 | 26 | 16 | 26 | 16 | 0.65 |
| mW | pg/ml | 2.5E3 | 2.2E3 | 2.9E3 | 2.2E3 | 1.3E3 | 1.3E3 | 1.1E3 | 3.7E2 | 5.6E3 | 5.7E3 | 26 | 16 | 26 | 16 | 0.38 |
| mY | pg/ml | 6.3E2 | 6.9E2 | 8.0E2 | 8.7E2 | 5.9E2 | 7.2E2 | 2.1E2 | 2.5E2 | 2.7E3 | 2.6E3 | 26 | 16 | 26 | 16 | 0.50 |
| mZ | pg/ml | 2.3E2 | 2.1E2 | 4.0E2 | 3.6E2 | 3.9E2 | 3.7E2 | 2.8E1 | 1.1E1 | 1.7E3 | 1.1E3 | 26 | 16 | 26 | 16 | 0.43 |
| nA | pg/ml | 1.7E0 | 4.8E-1 | 7.3E0 | 5.8E0 | 1.4E1 | 1.6E1 | 1.0E-9 | 1.0E-9 | 6.2E1 | 6.5E1 | 26 | 16 | 26 | 16 | 0.36 |
| nB | pg/ml | 3.2E2 | 3.3E2 | 3.6E2 | 3.6E2 | 1.7E2 | 1.8E2 | 9.7E1 | 3.8E1 | 8.2E2 | 6.9E2 | 26 | 16 | 26 | 16 | 0.51 |
| nC | pg/ml | 1.0E-9 | 3.7E1 | 8.7E2 | 1.1E5 | 3.4E3 | 3.8E5 | 1.0E-9 | 1.0E-9 | 1.7E4 | 1.5E6 | 26 | 16 | 26 | 16 | 0.57 |
| nD | pg/ml | 8.2E0 | 5.8E0 | 8.2E0 | 2.4E1 | 7.0E0 | 6.4E1 | 1.0E-9 | 1.0E-9 | 3.0E1 | 2.6E2 | 26 | 16 | 26 | 16 | 0.47 |
| nF | pg/ml | 1.0E-9 | 1.0E-9 | 1.2E0 | 1.7E0 | 4.4E0 | 6.9E0 | 1.0E-9 | 1.0E-9 | 2.1E1 | 2.7E1 | 26 | 16 | 26 | 16 | 0.50 |
| nH | pg/ml | 2.0E-1 | 8.8E-2 | 1.2E1 | 7.9E2 | 4.9E1 | 2.5E3 | 1.0E-9 | 1.0E-9 | 2.5E2 | 1.0E4 | 26 | 16 | 26 | 16 | 0.52 |
| nI | pg/ml | 1.7E1 | 4.8E1 | 6.0E1 | 6.3E1 | 7.6E1 | 9.0E1 | 1.0E-9 | 1.0E-9 | 2.6E2 | 3.5E2 | 26 | 16 | 26 | 16 | 0.48 |
| nJ | pg/ml | 3.0E-2 | 1.7E-1 | 1.3E0 | 8.7E0 | 3.2E0 | 3.3E1 | 1.0E-9 | 1.0E-9 | 1.6E1 | 1.3E2 | 26 | 16 | 26 | 16 | 0.50 |
| nK | pg/ml | 1.0E-9 | 1.0E-9 | 2.1E1 | 1.4E1 | 4.5E1 | 2.7E1 | 1.0E-9 | 1.0E-9 | 2.2E2 | 1.0E2 | 26 | 16 | 26 | 16 | 0.48 |
| nL | pg/ml | 1.0E-9 | 1.2E0 | 5.5E1 | 1.2E3 | 2.3E2 | 3.5E3 | 1.0E-9 | 1.0E-9 | 1.2E3 | 1.4E4 | 26 | 16 | 26 | 16 | 0.58 |
| hR | pg/ml | 2.4E4 | 2.4E4 | 2.4E4 | 2.6E4 | 9.0E3 | 9.9E3 | 3.6E3 | 1.6E4 | 4.9E4 | 4.3E4 | 42 | 12 | 42 | 12 | 0.54 |
| hV | pg/ml | 4.3E2 | 3.7E2 | 4.6E2 | 4.0E2 | 2.3E2 | 1.8E2 | 6.8E1 | 1.5E2 | 9.6E2 | 7.4E2 | 42 | 12 | 42 | 12 | 0.44 |
| hW | pg/ml | 1.6E3 | 2.0E3 | 2.3E3 | 2.2E3 | 2.0E3 | 8.0E2 | 2.2E2 | 1.1E3 | 1.0E4 | 3.5E3 | 42 | 12 | 42 | 12 | 0.61 |
| hX | pg/ml | 8.9E2 | 1.0E3 | 1.0E3 | 1.2E3 | 7.5E2 | 6.7E2 | 1.3E2 | 3.1E2 | 4.9E3 | 2.9E3 | 42 | 12 | 42 | 12 | 0.63 |
| iA | pg/ml | 1.3E2 | 1.5E2 | 1.8E2 | 2.7E2 | 1.7E2 | 2.9E2 | 5.8E0 | 1.5E1 | 7.9E2 | 8.7E2 | 51 | 19 | 51 | 19 | 0.55 |
| iB | ng/ml | 4.2E0 | 7.8E0 | 5.1E0 | 8.6E0 | 3.9E0 | 5.5E0 | 4.5E-2 | 1.6E0 | 2.0E1 | 1.9E1 | 43 | 13 | 43 | 13 | 0.70 |
| iC | U/ml | 2.0E-1 | 3.5E-1 | 4.5E-1 | 1.5E0 | 8.3E-1 | 3.3E0 | 1.0E-9 | 6.8E-2 | 4.8E0 | 1.2E1 | 43 | 13 | 43 | 13 | 0.64 |
| iH | ng/ml | 1.4E5 | 1.6E5 | 1.5E5 | 1.5E5 | 5.0E4 | 5.6E4 | 7.2E4 | 2.9E3 | 2.6E5 | 2.4E5 | 51 | 19 | 51 | 19 | 0.53 |
| iJ | ng/ml | 5.7E4 | 4.9E4 | 5.6E4 | 5.2E4 | 3.6E4 | 2.4E4 | 8.0E3 | 1.8E3 | 2.5E5 | 1.0E5 | 51 | 19 | 51 | 19 | 0.48 |
| hB | ng/ml | 3.7E-1 | 5.1E-1 | 4.6E-1 | 7.1E-1 | 2.7E-1 | 6.6E-1 | 1.2E-1 | 1.2E-1 | 1.3E0 | 3.2E0 | 51 | 19 | 51 | 19 | 0.69 |
| hC | pg/ml | 4.5E3 | 7.5E3 | 9.5E3 | 8.3E3 | 1.6E4 | 7.9E3 | 1.0E-9 | 4.1E1 | 1.1E5 | 2.7E4 | 51 | 19 | 51 | 19 | 0.50 |
| hF | ng/ml | 1.0E-9 | 1.0E-9 | 1.3E-2 | 5.0E-1 | 9.2E-2 | 2.2E0 | 1.0E-9 | 1.0E-9 | 6.6E-1 | 9.6E0 | 51 | 19 | 51 | 19 | 0.52 |
| hG | pg/ml | 6.8E3 | 6.6E3 | 7.6E3 | 6.8E3 | 3.6E3 | 2.4E3 | 2.3E3 | 3.6E3 | 1.9E4 | 1.2E4 | 51 | 19 | 51 | 19 | 0.44 |
| iO | ng/ml | 3.2E5 | 4.6E5 | 3.7E5 | 4.7E5 | 1.8E5 | 1.9E5 | 8.3E4 | 1.8E5 | 9.0E5 | 8.2E5 | 51 | 19 | 51 | 19 | 0.65 |
| iP | ng/ml | 4.5E4 | 5.3E4 | 5.0E4 | 5.0E4 | 3.8E4 | 2.2E4 | 2.4E3 | 1.0E4 | 2.2E5 | 7.7E4 | 51 | 19 | 51 | 19 | 0.54 |
| iZ | ng/ml | 1.7E3 | 1.9E3 | 1.9E3 | 1.8E3 | 8.2E2 | 6.1E2 | 8.8E2 | 9.8E2 | 4.5E3 | 2.7E3 | 50 | 17 | 50 | 17 | 0.48 |
| jB | ng/ml | 2.7E5 | 1.9E5 | 2.6E5 | 2.4E5 | 8.0E4 | 1.6E5 | 1.3E5 | 1.2E5 | 3.9E5 | 6.2E5 | 7 | 9 | 7 | 9 | 0.33 |
| rC | pg/ml | 1.5E3 | 1.1E3 | 2.3E3 | 1.3E3 | 2.7E3 | 1.1E3 | 1.0E-9 | 7.0E1 | 1.5E4 | 3.8E3 | 42 | 12 | 42 | 12 | 0.39 |
| rB | pg/ml | 2.5E1 | 4.0E1 | 3.9E1 | 5.9E1 | 4.8E1 | 7.1E1 | 1.0E-9 | 1.0E-9 | 2.9E2 | 2.5E2 | 42 | 12 | 42 | 12 | 0.58 |
| jD | ng/ml | 4.1E1 | 4.5E1 | 4.7E1 | 4.0E1 | 3.9E1 | 3.2E1 | 1.0E-9 | 1.0E-9 | 1.5E2 | 9.9E1 | 43 | 13 | 43 | 13 | 0.46 |
| jE | ng/ml | 1.0E-9 | 1.0E-9 | 6.9E0 | 5.2E0 | 1.2E1 | 1.5E1 | 1.0E-9 | 1.0E-9 | 5.2E1 | 5.6E1 | 43 | 13 | 43 | 13 | 0.46 |
| jF | ng/ml | 3.7E1 | 3.8E1 | 5.8E1 | 3.6E1 | 6.4E1 | 3.5E1 | 1.0E-9 | 1.0E-9 | 1.9E2 | 1.1E2 | 43 | 13 | 43 | 13 | 0.45 |
| jG | ng/ml | 4.8E3 | 4.5E3 | 4.7E3 | 4.5E3 | 2.0E3 | 1.9E3 | 1.2E3 | 6.0E2 | 9.6E3 | 7.1E3 | 43 | 13 | 43 | 13 | 0.49 |
| jH | ng/ml | 7.9E1 | 7.1E1 | 9.5E1 | 6.2E1 | 6.3E1 | 3.0E1 | 2.5E1 | 1.5E1 | 3.3E2 | 1.2E2 | 43 | 13 | 43 | 13 | 0.34 |
| jI | ng/ml | 6.9E1 | 9.9E1 | 7.6E1 | 9.5E1 | 3.0E1 | 4.0E1 | 3.5E1 | 5.0E1 | 1.9E2 | 1.7E2 | 43 | 13 | 43 | 13 | 0.65 |
| rA | pg/ml | 2.7E1 | 3.0E1 | 3.2E1 | 2.7E1 | 2.5E1 | 1.3E1 | 1.0E-9 | 6.9E0 | 1.1E2 | 4.8E1 | 43 | 13 | 43 | 13 | 0.48 |
| qZ | pg/ml | 4.4E1 | 4.9E1 | 6.9E2 | 1.1E3 | 2.5E3 | 3.1E3 | 4.8E-4 | 4.0E-3 | 1.0E4 | 1.0E4 | 31 | 10 | 31 | 10 | 0.53 |
| qY | pg/ml | 2.3E1 | 1.3E1 | 5.5E1 | 2.8E1 | 6.7E1 | 4.6E1 | 2.9E0 | 5.1E0 | 3.3E2 | 1.8E2 | 43 | 13 | 43 | 13 | 0.33 |
| qX | pg/ml | 5.9E1 | 6.8E1 | 7.0E1 | 7.4E1 | 4.5E1 | 3.7E1 | 1.0E-9 | 1.7E1 | 2.1E2 | 1.3E2 | 43 | 13 | 43 | 13 | 0.57 |
| qW | pg/ml | 8.3E0 | 1.0E1 | 1.3E1 | 1.1E1 | 1.5E1 | 8.9E0 | 1.0E-9 | 1.0E-9 | 8.1E1 | 3.1E1 | 43 | 13 | 43 | 13 | 0.52 |
| qV | pg/ml | 1.9E3 | 2.4E3 | 2.6E3 | 2.9E3 | 2.0E3 | 2.3E3 | 1.0E2 | 9.5E2 | 8.2E3 | 9.6E3 | 43 | 13 | 43 | 13 | 0.56 |
| qU | pg/ml | 7.0E1 | 1.2E2 | 1.7E2 | 2.0E2 | 3.4E2 | 2.3E2 | 1.0E-9 | 1.0E-9 | 2.1E3 | 7.9E2 | 43 | 13 | 43 | 13 | 0.59 |
| qT | pg/ml | 4.0E1 | 8.2E1 | 5.6E1 | 9.5E1 | 4.4E1 | 7.3E1 | 1.0E-9 | 6.9E0 | 1.8E2 | 2.6E2 | 43 | 13 | 43 | 13 | 0.67 |
| jK | ng/ml | 1.7E3 | 1.4E3 | 1.8E3 | 1.5E3 | 8.0E2 | 7.6E2 | 6.4E2 | 8.0E2 | 4.1E3 | 3.6E3 | 43 | 13 | 43 | 13 | 0.35 |
| jL | ng/ml | 2.3E2 | 2.1E2 | 3.3E2 | 2.8E2 | 3.5E2 | 1.8E2 | 4.8E1 | 1.3E2 | 2.1E3 | 7.0E2 | 43 | 13 | 43 | 13 | 0.50 |
| jM | ng/ml | 8.2E4 | 5.2E4 | 8.0E4 | 5.9E4 | 4.4E4 | 3.3E4 | 1.1E3 | 5.7E3 | 1.7E5 | 1.2E5 | 43 | 13 | 43 | 13 | 0.35 |
| jO | pg/ml | 2.3E5 | 2.6E5 | 2.5E5 | 3.1E5 | 1.1E5 | 1.5E5 | 7.7E4 | 1.4E5 | 5.7E5 | 6.4E5 | 43 | 13 | 43 | 13 | 0.62 |
| jP | pg/ml | 2.4E5 | 2.8E5 | 2.6E5 | 3.0E5 | 1.6E5 | 1.4E5 | 5.8E4 | 1.3E5 | 7.2E5 | 5.8E5 | 43 | 13 | 43 | 13 | 0.61 |
| jQ | pg/ml | 2.9E3 | 1.7E3 | 4.0E3 | 2.3E3 | 3.6E3 | 1.6E3 | 1.4E2 | 5.1E2 | 1.4E4 | 6.1E3 | 43 | 13 | 43 | 13 | 0.40 |
| jR | pg/ml | 7.0E3 | 3.4E3 | 1.2E4 | 7.4E3 | 1.2E4 | 9.8E3 | 1.0E-9 | 3.0E1 | 5.6E4 | 3.4E4 | 43 | 13 | 43 | 13 | 0.38 |

Figure 25 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jT | pg/ml | 1.9E5 | 1.6E5 | 1.9E5 | 1.8E5 | 7.5E4 | 7.7E4 | 7.7E4 | 7.5E4 | 3.8E5 | 3.5E5 | 43 | 13 | 43 | 13 | 0.42 |
| jU | mIU/ml | 4.8E0 | 4.1E0 | 9.0E0 | 1.1E1 | 1.3E1 | 1.5E1 | 6.2E-2 | 2.7E-1 | 6.7E1 | 5.3E1 | 43 | 13 | 43 | 13 | 0.49 |
| jV | mIU/ml | 1.5E0 | 1.1E0 | 3.2E0 | 2.2E0 | 5.5E0 | 2.9E0 | 1.7E-3 | 7.6E-2 | 2.6E1 | 1.0E1 | 43 | 13 | 43 | 13 | 0.47 |
| jY | ng/ml | 5.9E-4 | 2.7E-3 | 4.0E-3 | 6.3E-3 | 9.2E-3 | 7.9E-3 | 1.0E-9 | 1.0E-9 | 5.1E-2 | 2.4E-2 | 43 | 13 | 43 | 13 | 0.67 |
| kC | pg/ml | 8.9E1 | 8.8E1 | 1.7E2 | 2.9E2 | 2.1E2 | 6.7E2 | 2.1E1 | 3.6E1 | 9.8E2 | 2.7E3 | 26 | 16 | 26 | 16 | 0.45 |
| kE | pg/ml | 1.4E5 | 1.3E5 | 1.4E5 | 1.3E5 | 4.1E4 | 5.7E4 | 4.1E4 | 5.5E4 | 2.1E5 | 2.7E5 | 26 | 16 | 26 | 16 | 0.42 |
| kF | pg/mL | 6.5E1 | 7.3E1 | 6.7E1 | 7.3E1 | 2.7E1 | 2.7E1 | 2.8E1 | 3.4E1 | 1.5E2 | 1.3E2 | 26 | 16 | 26 | 16 | 0.58 |
| kG | pg/mL | 1.0E4 | 1.1E4 | 1.5E4 | 1.4E4 | 1.7E4 | 1.2E4 | 3.3E3 | 3.8E3 | 9.1E4 | 5.0E4 | 26 | 16 | 26 | 16 | 0.51 |
| kI | pg/ml | 1.9E2 | 1.9E2 | 2.0E2 | 1.9E2 | 9.3E1 | 9.5E1 | 4.4E1 | 1.0E-9 | 4.6E2 | 3.5E2 | 26 | 16 | 26 | 16 | 0.49 |
| kK | pg/ml | 9.3E1 | 1.0E2 | 1.3E2 | 1.9E2 | 1.1E2 | 1.8E2 | 2.9E1 | 2.9E1 | 4.6E2 | 5.9E2 | 26 | 16 | 26 | 16 | 0.56 |
| kN | pg/ml | 9.1E2 | 1.1E3 | 1.5E3 | 1.9E3 | 1.5E3 | 2.4E3 | 2.1E2 | 1.2E2 | 6.3E3 | 8.7E3 | 26 | 16 | 26 | 16 | 0.54 |
| kO | pg/ml | 7.2E3 | 5.9E3 | 7.6E3 | 1.6E4 | 3.0E3 | 3.5E4 | 3.4E3 | 3.8E3 | 1.8E4 | 1.5E5 | 26 | 16 | 26 | 16 | 0.43 |
| kP | pg/ml | 5.8E3 | 5.1E3 | 8.9E3 | 5.6E3 | 9.7E3 | 2.9E3 | 9.6E2 | 1.4E3 | 4.8E4 | 1.1E4 | 26 | 16 | 26 | 16 | 0.41 |
| kQ | pg/ml | 4.2E3 | 3.7E3 | 5.1E3 | 3.9E3 | 3.2E3 | 1.6E3 | 1.1E3 | 1.4E3 | 1.8E4 | 7.8E3 | 51 | 19 | 51 | 19 | 0.41 |
| kR | pg/ml | 2.2E1 | 2.0E1 | 2.4E1 | 2.8E1 | 1.5E1 | 2.2E1 | 1.4E-1 | 3.4E0 | 5.9E1 | 8.2E1 | 51 | 19 | 51 | 19 | 0.52 |
| kS | pg/ml | 9.7E2 | 8.7E2 | 1.3E3 | 9.7E2 | 2.0E3 | 7.1E2 | 8.2E1 | 2.9E2 | 1.4E4 | 3.0E3 | 51 | 19 | 51 | 19 | 0.40 |
| rZ | ng/ml | 1.0E-9 | 5.7E-3 | 6.1E-3 | 8.6E-3 | 1.3E-2 | 1.2E-2 | 1.0E-9 | 1.0E-9 | 7.9E-2 | 4.5E-2 | 41 | 12 | 41 | 12 | 0.62 |
| rY | ng/ml | 6.1E-2 | 8.2E-2 | 5.7E-1 | 1.1E-1 | 3.1E0 | 1.2E-1 | 1.0E-9 | 2.0E-2 | 2.0E1 | 4.4E-1 | 41 | 12 | 41 | 12 | 0.62 |
| rX | ng/ml | 1.0E-9 | 1.0E-9 | 7.7E-2 | 1.3E-2 | 4.8E-1 | 3.2E-2 | 1.0E-9 | 1.0E-9 | 3.1E0 | 1.1E-1 | 41 | 12 | 41 | 12 | 0.64 |
| lK | pg/ml | 1.6E2 | 6.8E1 | 2.6E2 | 8.7E1 | 5.1E2 | 8.9E1 | 1.0E-9 | 4.8E0 | 3.3E3 | 2.9E2 | 43 | 13 | 43 | 13 | 0.36 |
| lL | pg/ml | 1.4E3 | 1.8E3 | 3.2E3 | 2.8E3 | 6.4E3 | 1.9E3 | 1.5E1 | 1.9E2 | 4.2E4 | 6.3E3 | 43 | 13 | 43 | 13 | 0.62 |
| lM | pg/ml | 1.1E3 | 1.2E3 | 4.1E3 | 3.5E3 | 7.5E3 | 4.5E3 | 2.1E2 | 9.5E0 | 3.4E4 | 1.3E4 | 43 | 13 | 43 | 13 | 0.48 |
| lN | pg/ml | 1.0E-9 | 4.7E0 | 2.9E0 | 6.7E0 | 4.8E0 | 7.6E0 | 1.0E-9 | 1.0E-9 | 2.4E1 | 2.1E1 | 43 | 13 | 43 | 13 | 0.62 |
| lO | pg/ml | 1.0E-9 | 1.0E-9 | 2.9E0 | 2.6E0 | 1.9E1 | 9.3E0 | 1.0E-9 | 1.0E-9 | 1.3E2 | 3.4E1 | 43 | 13 | 43 | 13 | 0.53 |
| nW | pg/ml | 1.1E5 | 1.1E5 | 1.1E5 | 1.1E5 | 2.4E4 | 3.0E4 | 5.9E4 | 3.6E4 | 1.5E5 | 1.5E5 | 51 | 19 | 51 | 19 | 0.51 |
| nY | pg/ml | 2.1E3 | 2.8E3 | 2.6E3 | 3.0E3 | 2.0E3 | 1.9E3 | 1.0E3 | 6.3E2 | 1.3E4 | 8.1E3 | 51 | 19 | 51 | 19 | 0.58 |
| oO | pg/ml | 8.1E4 | 9.9E4 | 1.2E5 | 1.0E5 | 9.4E4 | 4.8E4 | 3.5E4 | 2.0E4 | 3.3E5 | 2.0E5 | 25 | 15 | 25 | 15 | 0.55 |
| oP | pg/ml | 1.2E5 | 1.8E5 | 1.5E5 | 1.8E5 | 1.1E5 | 1.2E5 | 4.8E4 | 5.6E4 | 4.5E5 | 4.6E5 | 25 | 15 | 25 | 15 | 0.59 |
| oQ | pg/ml | 2.8E3 | 3.4E3 | 4.4E3 | 4.0E3 | 4.4E3 | 2.2E3 | 1.6E3 | 7.7E2 | 2.1E4 | 8.4E3 | 25 | 15 | 25 | 15 | 0.56 |
| oE | pg/ml | 1.3E2 | 5.8E2 | 4.2E2 | 9.1E2 | 6.0E2 | 9.8E2 | 1.0E-9 | 5.4E1 | 1.9E3 | 3.4E3 | 51 | 19 | 51 | 19 | 0.71 |
| oF | pg/ml | 1.3E4 | 1.8E4 | 3.1E4 | 3.7E4 | 5.2E4 | 4.8E4 | 6.9E2 | 5.1E2 | 2.5E5 | 1.7E5 | 51 | 19 | 51 | 19 | 0.55 |
| oH | pg/ml | 4.9E1 | 3.4E1 | 9.2E1 | 5.1E1 | 1.0E2 | 5.3E1 | 6.2E0 | 6.3E0 | 4.8E2 | 1.8E2 | 51 | 19 | 51 | 19 | 0.37 |
| oK | pg/ml | 9.1E2 | 6.6E2 | 1.6E3 | 1.7E3 | 1.7E3 | 1.9E3 | 1.4E2 | 2.3E2 | 7.2E3 | 6.5E3 | 51 | 19 | 51 | 19 | 0.50 |
| oN | pg/ml | 5.6E2 | 5.0E2 | 6.7E2 | 6.2E2 | 7.1E2 | 4.4E2 | 2.0E2 | 1.1E2 | 5.3E3 | 1.8E3 | 51 | 19 | 51 | 19 | 0.47 |
| oW | pg/ml | 2.0E2 | 3.8E2 | 2.4E2 | 7.2E2 | 1.5E2 | 9.0E2 | 8.5E1 | 2.9E1 | 5.4E2 | 2.7E3 | 7 | 9 | 7 | 9 | 0.68 |
| oT | pg/ml | 3.7E2 | 3.0E2 | 4.3E2 | 3.3E2 | 2.3E2 | 1.2E2 | 1.9E2 | 1.3E2 | 7.7E2 | 5.4E2 | 7 | 9 | 7 | 9 | 0.40 |
| oV | pg/ml | 8.8E1 | 9.0E1 | 1.7E2 | 1.6E2 | 1.9E2 | 1.9E2 | 4.7E1 | 2.2E1 | 5.8E2 | 6.3E2 | 7 | 9 | 7 | 9 | 0.44 |
| oD | pg/ml | 1.8E4 | 1.4E4 | 1.7E4 | 1.6E4 | 4.1E3 | 7.4E3 | 1.1E4 | 9.3E3 | 2.2E4 | 3.3E4 | 7 | 9 | 7 | 9 | 0.38 |
| pF | pg/ml | 5.6E-1 | 5.0E-1 | 2.3E0 | 7.5E-1 | 1.2E1 | 6.0E-1 | 1.0E-9 | 1.0E-9 | 8.7E1 | 1.7E0 | 51 | 19 | 51 | 19 | 0.54 |
| pH | ng/ml | 7.2E0 | 1.1E1 | 1.3E1 | 1.0E1 | 1.3E1 | 5.4E0 | 4.7E0 | 1.2E0 | 4.2E1 | 2.0E1 | 7 | 9 | 7 | 9 | 0.57 |
| pI | ng/ml | 7.9E1 | 7.1E1 | 9.8E1 | 6.9E1 | 4.8E1 | 3.4E1 | 5.6E1 | 2.3E1 | 2.0E2 | 1.2E2 | 7 | 9 | 7 | 9 | 0.35 |
| pK | ng/ml | 4.6E-1 | 5.8E-1 | 5.7E-1 | 6.0E-1 | 2.4E-1 | 3.4E-1 | 2.6E-1 | 2.7E-1 | 8.5E-1 | 1.4E0 | 7 | 9 | 7 | 9 | 0.46 |

Analyte panel data:

Unconstrained panels with 3 analytes, where 1.0E-9 >= 'model p-value' > 0. Contains 2 panels of 24,406,229 total panels evaluated. : DrIkbP GnLxId Unconstrained panels with 3 analytes, where 1.0E-8 >= 'model p-value' > 1.0E-9. Contains 18 panels of 24,406,229 total panels evaluated. : Ik{bZ(Du HI Hp) aM(Lp Lt) UbTl} Fb{Vv(gW jH) EdqU} bZ{FiPd NgHl} BgVviB FnIlfR HxSicX ZqOwdD LibHmW LjcEkE UhVumM Unconstrained panels with 3 analytes, where 1.0E-7 >= 'model p-value' > 1.0E-8. Contains 119 panels of 24,406,229 total panels evaluated. : Ik{aM(Gh Ps Ru Rv Uy Va Vi Wc Wf Yg Yi Tl Xa Yf) bZ(Ux Vb Vi Yh Yi Yj) bP(Uw Vz Wb Tm) hB(Dr Gn)} Up{Dc(kI kP mS mW nA nB nR nT nU) nA(Ir Oa Rm) lY(Kq Nw) QamP VtnR} Vw{bZ(aA Aw Cq Hr Pd Rg Um) fP(Lx Oh Ow Pf Yi) Pz(bN Nn Rh) BgHx} Yi{lb(aI cZ eF) Vj(Ih Wc Ye) Ng(Bg bP) OzdJ} Fb{eF(eD IN qT) rB(kR kS) bNrY eDoK gLrC} bZ{Hl(Uf Uu Ux) ThGn YjeF RuPd} gP{Oa(Nj Ph) YjTl LdPb LjdJ} Ri{nU(Pf Vu) UhmM aClY} oE{Gc(Nc Pe) DrUb KomM} Oz{dJ(Mt Rt Yh)} dR{LijF OwVi nTmM} kE{bH(Tn Tr) ArLx} kQ{Oa(Pd Ph) LjaE} Bg{NghR VvrX} Is{NcVj IbbN} Yj{aH(Aa Tl)} Qa{DlYc IdmP} AlUkmW TrVvmZ WbKkRm ShRfOh LjbNiJ Unconstrained panels with 3 analytes, where 1.0E-6 >= 'model p-value' > 1.0E-7. Contains 1,099 panels of 24,406,229 total panels evaluated. : oE{Yj(Aa aC aH aI aS aX bC bE bU bX bZ Cs Ct cZ dD Dp eF Et Ex Fn Gc Gl Gp HB Hf iA Ij In Io iP Is Jq Ke Kr Ld Lh Li Lp Lu Lv Lx Lz Mf Mj Mk Ml Mm Mq Mt Mx Nn Nq Nw Ny Oa Oh Om Op Or Ou Ow Oy Oz Pa Pb Pc Pf Ph Pk Pz Qa Qb Qc Qd Qe Qg Qh Ql Qm Qn Qx Rt

Figure 25 Continued

Rv Sr Ss St Tz Ub Ue Ug Uh Un Ur Ut Uw Uy Vh Vi Vj Vo Vt Vu Vz Yl Zq Tl Wm Ti Yf) Ub(Du Eq Fc Fd Fi Gb Gh Hl Ho Hp Lp Lt Op Ps
Rt Ru Rv Rx Ry Rz Sf Sh Si Sj Uw Ux Uy Uz Va Vb Vc Vh Vi Vj Vw Vz Wb Wc Wd We Wf Wg Wh Yd Yg Yh Yi Yk Yl Zq Zw Zx Ye Tm
Tl Xa Yf) Yf(An bB cl Cp Cv Db Di Ed Gl Hl Ib Ip Ki Nc Nk Pz Rx Sh Ur) cP(Ux Vb Vh Vi Vj Wc Wd We Wf Yi) We(Af cl Nd nW Pb Ri Rj
Ut) Lj(aE Ar gP hG kQ Mb Nj Ph) Vi(Ed Gh Gl iO Pb Qc St Wb) Wf(cN Dl Fn Wb) Yg(Uc Vu Yi) Vj(cl dC Pz) Ib(Ps Uw) Sh(Ri Rj) Wd(dC
fP) Tm(Yi Th) Rz(Bb Ri) Vw(Cq Pz) mM(Li Pk) GbGl GcUh IsTk WbaA JeUw} Lj{dJ(aE Ar bN cP eC hC hG iJ lv Jq kQ kS Ma nW nY oF
oH oN Oz Pb Pd Rf Uk Un Up) gP(aE aG al AR bN cH cP cR dA fP hG iJ lk kQ Mb Nd Nj Nl Pb Ph) iJ(Aj Ar CP Cw dA Fr lk Jd Jo Jt kQ Mu
Ng No Nt Pd Ph Qy) Ar(aE aL aQ bN cV dA Fb hG Hx nY oH Uk) kQ(cJ dD eC Jd Ju Nj Nk Nl Oa Pb Ph St) Nj(aG bN cP cV dA eC nY oH)
aE(Ed hF hG iO kS oN) kE(cV Dk Tn Tr) Nl(bN cP nY) Ph(fP nY oH) mW(bH Rh) oH(Gn St) BgNg GznA NknY PzVw} Oa{kQ(aA aE Aw
bN Cp cQ dC dD dJ eC gP Hr Ib Ik Jd Jo Jt Mu Nd Nj Nk Nl Pb Pf Rf Rg Rh Ri Rj Rm Un Up) gP(aW bN bS cA cK cP cR dJ fP Ha Hb hG Ik
Jk Jo Nd Ng oH Pb Pd Qh Qy Up Tk) bN(aR aW cP Dc dJ hC iJ Ne Nj Nl nY oF Ph) Nj(eC kS nW nY oH oN) Ph(kS nW nY oH oN) Jd(hC nW
oH oN) Nk(iZ nA) Tk(aJ bU) Pd(aW dJ) eC(kP mM) nB(Af Bn) oH(Cp Dc) AxjH GzmS IkiJ VqnJ aQaW bHmY dDnD dJnW} Vq{nJ(aC bE
bO bQ bZ cF dD dK Ed Fa Fy Hx Ij Is It Jl Jn Js Ju Jv kN Kq Lx Lz Ma Mj Mq Mr Mt nC Ni Nk NN Nr Nt Nu Nw Oh On Ow Pb Pe Pf Pz Qa
Ql Qt Qx St Tn Tr Tt Us Uu Wm Tj) kC(aC bZ cT dD kN Lz Ma Mh Ml Oh Ow Qx Ra Tn Tr Tt Wm Tj) nA(dD Ed ll nL nN Oh Pf Pz Tr Tj)
aC(kK lY mM mU nD nU) mS(bJ Is Nw Tz) Or(lX nl) dD(kE kK) mM(Oh Ur) kP(bJ cF)} Ik{bZ(Fc Gn Op Ps Rt Ru Rv Rx Ry Rz Sh Uw Uy
Uz Va Vc Vh Vj Vw Vz Wc Wd We Wf Wg Wh Ye Yf) hB(Gc Hl Rt Rv Rz Uw Ux Uy Va Vb Vc Vh Vi Vj Vz We Wf Yd Yh Yi Yj Yl Zq Zw
Yf) aM(Eq Fc Hp Rt Rx Ry Rz Si Uw Ux Vh Vw Wc Wh Yh Yl Zq Zw Zx) Yi(bP dJ) dL(Uw Vh) ShSt RvcR} Yi{Vj(aJ aP aR bE bJ cE cG cl
cN cO cP cR cV dH dJ fP Fy nW oH oN pF) Ng(aG aM aN bZ cl cW dJ fR hB lp Jk kQ Qc Wd) Yg(al bZ hB iZ kQ oH oN tF) Ib(aH aM bB bC
cF dD) Rz(hB iO nW) oN(Fn lz Oy) Th(fP nW) iO(Kn Sr) kQ(Oy Pd) EfbZ IpbJ PzVw VshB aRbP} Vj{Tr(AA aD aE aG aR aY bH bX cE cG
cL cP CQ cW dC dD dH dl dL dN Rf Wb) fP(bA cT Oh Ow Qa) Hx(iO iP) Id(Js Lx) bZ(dD Ks) MacI QadC JskS PbaQ aChB cUoH}
Vw{Pz(Ax bZ Cs hB Ld Lx Lz Ma Mh Ml Nr Oh Ow Pe Pf Qx Ra Rf Tr Tt Wm) bZ(dC Hl Ho Hu Hx Ly Nb Vi) MflR TtfP OzdJ} Fb[jH(aU
Ba Ct jQ Mj Ng Vo) gW(aU eF Mu) Ed(qT qV) jU(lb Vv) kR(rY rZ) rX(gL kS) CtlM MhjP lnlN RbWn SsrC aKjQ} hB{Rz(aC aY Cq Ij Is Jm
Nn Oh Pz St Vs Vu Yj) Yj(Ef Ss Tm Tl Xa) Th(Ye Tm) Hl(Ch Ux) IbZw LimM} dJ{Oz(Ps Ru Rv Uw Ux Uy Uz Va Vb Vc Vh Vi Wc Wd We
Wf Wg Wh Yf) Ib(Is Qh) QabN UueM} Oh{Vi(hC hG iO iZ oF oN) oN(Gn Op Sf Sh) nA(Ex Gz Ib) Si(cP nW) mP(Ex Id) WfbJ RzhC bHkK}
Is{Ib(aQ dA jY IK) mS(nC nH nJ nL) Tk(aR cJ dN) mM(Uk Vs) WmbN GznA NcqT QygC UpkN cReM} fR{Mf(Du Fd Hl Hp Rt Rz Vh Vz
Wb Wd Wh Yg Zw Xa Th Yf) FnJe QaVi} Ow{Vi(bZ iO kS oF oH oK oN) oN(Gn Op Sf Sh) DlYe HrVa ldWf SiPd ZqiA RzhC} Fn{eC(kC
kO nA nC nD nF nH nJ nL) eM(aP cS Il) IlSi LimW PfkE} Up{Dc(lY nl nJ oO oP oQ) nA(Cq Ih Nw Vt) lY(Ok Qc) QamU NwnL VtkN}
Ti{lY(Nn Ny Pf St Vu) Nn(mU nB) Vu(mZ nl) EdnA LxmM IjmU JlmZ} Th{Wm(iO oH Qn) Vu(lY mW mZ) Pf(kE lY) NnkE IjmM VibZ}
bZ{Hl(Dg Jo Mg) Rx(Hr Hu Pd) HrUx ShaY QbVi LpPd} Tk{Fa(aH bE bN cL gP Ub) Mz(Bo dl gP)} Lx{Id(Ho Vz Wf Zw) Rz(hC nW)
RimW VvlM} Ng{Bg(jT IK Wm) Ef(jD jL jM) NnYe PzbN} Yj{aH(cA Ye Tm Xa) InTl XaaI eFoF} Vv{Bg(hX jK jP rZ) QdlN JylK}
bN{Wm(cZ Jq Qb) AxQb IbQa PzSs} mW{Li(cR dD Ri) bH(Ax Pe) JmUk} kE{Tn(bJ cR Ct Kj) Tr(Kj Qb)} Nn{Jh(Gn Ye) DiHp NtTm
VzPd} Pf{nD(aC bH Jf) NtTl} eC{Qv(mU mY) aPoQ cWmY} As{WdoH RvbE} Ed{ToeM VunD} Gb{St(Aw Hr)} Gz{EtnJ IlnA} Vz{HxIp
KkRm} Qa{ViiO bHnI} Ri{ConH QdmM} Wn{FaUb Mwlc} BbRzoF CvUgnR WmJqaW ExnAnK GnMxoH NcQggC NjSseM TrOymZ TnQwmM IjSicP ShRmiO Unconstrained panels with 3 analytes, where 1.0E-5 >= 'model p-value' > 1.0E-6. Contains 5,862 panels of 24,406,229 total panels evaluated. : Lj{gP(aC aD aF aH AJ aK aL aM AN aO aP aQ aS aU aV AW aX aY aZ bA bB bC bE bF bG bH bI bJ bL bM bO bP bQ bR bS bU bV bW bX bZ cA cB cC cD cE cF cG Ch cI cJ cK cL cM cN cO Cp cQ cS cT cU cV cW cX cY cZ dB DC dD DE dF dG dH dI dK dL dM dN Dp dR eC Ed EF Et Ez Fa Fb Fn Fp Fr Fw Fy Gp Ha HB HC HF Hq Hr Hu Hv Hw Hx iA Ib Ic IH Ii Ij Il Im In iO IP Iq Ir Is Iu Iv IZ Jd Je Jf Jg Jh Ji Jj Jk Jm Jo Jp Jq Jr Js Jt Ju Jv Jy Kc Ke Kf Kg Kj Kk Kl Ko Kp kR kS Kz Ld Lh Li Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc nD Ne Nf Ng Nh Ni Nk Nm Nn No Nq Nr Ns Nt Nu Nv NW Nx NY Oa Oe OF Og OH Oi OK Om ON Or Ou Ow Oy Oz Pa Pc Pd Pe PF Pg Pi Pk Po Pz Qa Qb Qc Qd Qg Qh Ql Qm Qn Qt Qu Qv Qw Qx Qy Qz Rc Rg Rh Ri Rj St Ua Ub Ue Uf Uk Um Un Uo Up Ur Us Ut Uu Uv Vu Vv Wm Tj tF) Ar(aA aC aD AF aG aH aI aJ aK aM AN aO aP aR AS aU aV AW AX aY aZ BA bB BC bE bF BG bH bI bJ bL bM BO bP bQ bR bS bU bV bW bX bZ cA cB cC cD cE cF cG CH cI cJ cK cL cM cN cO cP CQ cR CS cT CU cW CX cY cZ DB dC dD dE dF dG dH DI DK DL dM dN Dp dR eC Ed EF Et Fa Fn FP Fr Fw GL Gp Ha HB HC HF Hq Hr Hu Hv Hw iA Ib Ic iH Ii Ij Ik Il In IO IP Iq Ir Is It Iu Iv iZ Jd Je Jf Jg Jh Ji Jj Jk Jl Jm Jn Jo Jp Jq Js Jt Ju Jv Jy Kc Kd Ke Kf Kk KQ kR kS Ky Kz Li Lu Lv Ma Mb Md Mj Ml Mq Mr Ms Mv Mw My Mz Na Nd Ne Nf Ng Nh Ni Nn No Nq Nr Ns Nt Nu nW Nx Ny Oa oF Oh Oi OK Om ON Or Ou Oy Oz Pa Pb Pc Pd Pe PF Pg Ph Pi Pj Po Pz Qa Qb Qc Qd Qe Qg Qh Ql Qm Qn Qt Qw Qy Ra Rb Rf Rg Rh Ri Rj Rm Sr Tn Tz Ua Ub Uc Ue Uf Ug Um Un Uo Up Ur Ut Vp Vt Vu Vv Wm Tj tF) dJ(aA aC aG aH aI aK aN aP aQ aR aS aU AW Ax bA bB bF BG bH bI bJ bP bQ bS bW bZ cA cC cD cE cG CH cJ cK cL CQ cR cS cV CW cY dA dB dC dD dE dF dK dN dR Ed EF Et Ez Fa Fb Fn FP gL Gp Ha hB hF Hr Hu Hv Hw Hx iA Ib Ic iH Ii Ik Il In iO iP Iq Is iZ Jd Je Jg Jh Ji Jj Jl Jm Jn Jo Jp Jr Js Jt Ju Jv Jy Kd Kq kR Ld Lh Li Lu Lv Ly Mb Md Mq Ms Mu Mv Nb Nd Ne Nf Ng Nh Ni Nj Nk Nl Nm Nn Nq Nr Nt Oa oE Og Oh oK On Or Ou Ow Oy Pc Pe PF Ph Pi Pj Pk Po Pz Qa Qb Qc Qd Qe Qg Qh Ql Qm Qn Qt Qu Qv Qw Qx Qy Qz Ra Rb Rc Rg Rh Ri Rj Rm Sr Ss St Tn To Tv Tz Ua Ub Uc Ud Ue Uf Ug Uh Ul Um Uo Ur Us Ut Uu Uv Vo Vp Vt Vu Vv Wm Tj tF) iJ(aC AD aE Af aK Al AN AO AP aQ aR AS aU aV AW Ax BA Bc BG bJ bL Bn Bo bS bV cA cG CH cI cJ cK cN CO Cq CS Ct CU CV cW Cx cY dC DD DE Dg dH Di Dk Dl dN dR eC Ed Ef Ez Fn Fy Gl Ha Hb HC hF hG Hr Hu Ib Ic Ih Ii Ij Il Im In iO Ip Ir Is Iu Iv Iz Je Jg Jh Jk Jp Jq Jr Kg Kj Kl Kq kS Li Lv Mb Mf Mg Mm Mn Mv Mw ND Ne Nf Nh Nj Nk Nl Nm Nn Nq Nr Nv nW NY oE Of OH Ok ON Or Oy Oz Pb Pe PF Pj Po Pz Qe Ql Qt Qu Qw Rc Rh Sr Ss St Ua Uf Uk Un Up Ur Ut Vo Vv Wm tF) kQ(aA aD AF aG aH aI Aj aK AL AN aQ aR AS aU aV AW aZ bB bG BN bQ bR bS bU bX cA cB cF CH cL CP CQ cR cV Cw CX cY cZ dA dB DC Dd dF dG dI dR Ed eF Et Fa Fb Fn fP Fr HB Hc HF hG Hr Hu Hx iA Ib Ic Ik Il Im iO Iq Is Iz Jf Jg Jo Jp Jq Jr Jt Jv Jy Kc Kd Kg Kj Kk Ko Kr kS Lv Lx Ma Mb Mf Mg Ml Mm Mn Mq Mu Mw Mx My Nb Nc ND Ne Nf Ng Nh Nm Nr Nt nW nY Oe Of Og OH Oi Om oN Or Ou Ow Oy Oz Pd Pf Pj Pk Pz Qm Qn Qv Qw Qy Rf Rg Rh Ri Rj Rm Sr Uc Uf Uk Un Up Ut Wm tF) hG(AD Af aG Aj aK Al An Ao Ap aQ aR As aU aV Aw Ax Ba Bb Bc BG BN Bo bU cB cF CH cJ Co CP Cq cR Cs Ct Cu CV Cw CX cY dA DB DC DD De Dg Di Dk Dl dR eC fP Fr HB hF Hr Ib Ik Il iO Jd Jf Jo Jq Jr Jt Ju kS Mb Mm Mn Mu Mw ND Ne Ng Nh Nj Nk Nl nY Of oH Oz Pb Pd Pf Ph Qm Qn Qw St Uk Un Up Wm tF) bN(aE aG aH aI An aQ aR aS aU aV AW bB Bg CH cJ cP Cq cR cS Cu cV Cx cY dA DC dD Dk Ed Et Fa Fn fP Fw Hb hC hF Hr Ib Ic Il Is Jm Jq Jr Ju Jy Ko Ma Mb Nd Ne Nq nY Oa oE oF oH Ou Oz Pb Ph Pz Qc Qm Qn Qv St Uc Ue Uf Uk Up Ut Wm tF) Nj(aE aF aH aI aK aL aM aN aO aQ aR aS aU aV aW aZ bB bF bG bI bJ bL bM bQ bS bU bV bZ cB cC cD cE cF cJ cK cL cR cS cY cZ dB dC dD dE dF dR fP hB hC hF iA iH iO iP iZ kR kS nW oF oK oN pF tF) Ph(aE aG aI aL aN aO aQ aR aU aV bF BG bZ cJ cP cS cV cY dA dF dR eC eF gL Gp hB hC hF iA iH Il iO iP Is iZ Jy kR kS

Figure 25 Continued

Figure 25 Continued

Ml Qb Qd Rg) Ik(eD hR jD rY Vq) Vv(jD jO jP lL lM) Ct(jD lK lL rA) lM(Ld Li rX Vt) bN(eD rX rZ) eF(jO qW rZ) jQ(aU Ba cY) kR(hR hW hX) rY(jE kQ Mj) lb(jV lL) Ss(jD qT) Jt(jD qY) jO(Ba oK) MjjF MsrZ WncX OhkE eDiH hXkQ} bZ{Vw(aC Af An aY Bb bH cI cP cQ cR dH Dk Ef fP Gn Id Kj Kn Lv Mb Me Nd Nx Pb Rf Rh Ri Rj Rm Sr Ub Ur Ye) Ik(Dr Eq Fd Fi Gb Gc Gh Ho Lp Lt Sf Si Sj Vq Wb Yd Yg Yk Yl Zq Zw Zx Tm Tl Xa) Pd(Fc Hl Ho Op Ry Sf Sh Si Uw Uy Va Vh Vj Vz Wd We Wf Wh Yd Yj Zx) Vj(aC aY bE cI cP Et Fn Hl Ho Hx Id Lv Ms Oz Pb) Hl(Aj bC bE bl Ed Ef Kg Kj Kn Rx Th) Yj(Aj bE Ef Jo Mu Ng Ss UfTl Th) Rz(An aY bE bl dD II Kk Lv Ow Ut) Th(Gz Rx Wc Zx Tm) Ng(Lp Vi Yl Ye Tl) Ef(Ho Vq Wh Ye) Zq(aY bE dD Pc) Rx(aC Pe Pg Ss) Hr(Fc Uw Va) Fa(Tk Wn) Op(aY bE) Ux(Aw Um) Vi(Ed Oh) aC(Si Vh) EqId HoUf KnUy} Qc{jM(kC kE kF kG kI kK kN kO kP lW lX lY mE mF mH mI mM mP mS mT mU mW mY mZ nA nB nC nD nF nH nI nJ nK nL nM nN nO nR nT nU) mP(jE jG jH jI jK jO jP jY lK lL lM lN qT qU qV qX qY) lN(kC kN kO kP mM mS nA nC nD nF nH nI nJ nL nR) lY(iC jD jI jV jY lK qT qU qW qX rA) nD(iB jD jG jT jU jV jY lK lM qU Up) jT(kO mM nC nF nH nI nJ nL) IK(kE kG kI kN lX mE mZ nK) jU(kO nC nF nH nI nJ nL) jV(nC nF nH nI nJ nL) kN(jl qT qU rA) ml(jD jl qT) mM(jD jO jR) Wm(bN Th) Hr(Ux Va) nR(jH qU) nL(hA lM) qY(mE mZ) AxbN Gnlk HxSh VqnJ nNjH mHrA mTjP jFkI jRkP} bN{Qb(aQ Ar AW Bg Ch Co Cq cR CS Cu cV Dc Dg dJ Fa fP gP Hr Ib Ic iJ Jq Jv Ld IN Ne Pz Uk Ur) Fa(aY cP dJ Ed Fn hC lb Ic Jm kQ Pd Pz Ss Uk Un Wn Wm) Qa(aR aW Ax cP dA Fn gP Hr Ic Jt Ng Sr Ss Uk Un Wm) Wm(al cP dJ Et Hb Hx Ke Ld Lx Pz Qd Qe Qh Uh) Pz(Aj Ed Jq Jt Kj Ld rC Uk Vz) Ib(Et Ih lj Lx Qe Qh Rm) Ax(Et Hb Hx Jm Jq Qd) Ed(Et Hb Jq Ko) Lx(Hr Ic jH Ss) rC(Ic lh Mj Nd) Et(Fw Jt Ng) Jq(aW Cs qT) Li(dJ gP kQ) Uk(aW Ir Jm) Fw(Fn Tm) Nr(dA Pb) Mj(jF rZ) dJ(Qh Rm) HlOw IcWn RgcA PfnH} Ng{Bg(Aj Ax Cq Cs De Fa Fn Fy Gp Hb hV hW Hx iC Ij lq Ir lt Iu jF jH Jm Jq Ld Li lN Lx Lz Ma Mh Ml Mq Mt Nb Nj Nn Nr Of Oh Ow Oz Pd Ph Pz Qa Qb Qh Rh Sr Ss Tn Tr Tt Th) Ef(hA iC jE jF jG jl jK jO jQ jT lK lL lN) Pz(bF bJ bQ GP oH Tn Uk Ut Ti Th) gP(Fa Ld Li Lx Oh On Qa Tr) Yg(Nn Nr Oh Ow Pf Tj) lj(Fn Je Tr Uc Up) Pf(cA cK Yh Ye) Wm(Gp Qh Ut) Th(Qa Tn Tr) Nn(Gn Vz Yh) Nr(bS cA cK) Uc(iC jD jM) Il(Fi Vq Vz) Vq(kP Uk) dJ(Qa Qh) CqGp TrYe JeWd JqaW RgjE} Ik{aM(Dr Du Fd Fi Gb Hl Ho Op Sf Sh Sj Uz Vb Vc Vj Vz Wb Wd Wg Yd Yj Yk Ye Tm) hB(Du Fd Gb Gh Hp Lp Lt Ps Ru Rx Ry Sh Si Uz Vq Vw Wc Wd Wg Wh Yk Zx Ye Tm) bP(Gc Gn Hl Ps Rv Vh Vi Wh Yh Yl Zw Ye Yf) dL(Dr Hl Ps Rv Rx Wc Yd Yh) Vq(bQ cB cF cR dF Li nJ) Dr(bH cS dG gC iO) Gc(aY cS dG fR) Sh(Ps Qa Qh Ut) Tl(Bg Dc Hl) Rv(cS cU Il) Qa(Gn Sf) Wh(Cs Je) Rx(cO cR) aW(Jq Lx) gP(Fa Li) YfiO HlaP HrPs ljSi IpLp PzYe WecS QhdJ VibH} Up{Dc(kC kE kF kG kK kN kO lW lX mE mF mH ml mM mP mT mU mY mZ nC nD nF nH nK nL nM nN nO) lY(aC al cB dD nA oF Oz Pb Pc Pf Qa Qd Uh Vt) nA(Ax Fw Kk Li Lx Ok Qa Qb Tr Uc) Qa(mM nB nD nN nO nT nU Th) Vt(kF mW mZ nC nO nT oP) nO(Ij Jm Lx Qe Tn) Nw(kN mP mU nD) Kk(nD Vz Wb) mW(Jm Oe Qh) Ok(mP nD) ImP QdIN QenT KqkE OhmU PfnD eCoQ} Ow{Vi(al bF BG bQ eF fP gL gP hC hG iA iH iP iZ nW nY pF) Hl(al Ar bE bG bl bP cC dA eF fR Id Nm oN Rf Va) Si(aC cP cR dH Hr Mf Nx) Id(Gh Gn Ho Yh Zw) Wf(aR bJ Jt Kc Nt) Pd(Vb Wh Yh Ye) Gn(kS oH oK) Rz(fP hB oN) Hr(Gb Yl) Sh(Nx Rf) Vw(Cq Dk) CwWe TnkE YjeF VjkS} Vq{nJ(Ap Ax Cs Cu Cw Dg dR Et hB Ib Ih lm Jj Kp Ld Mf Mh Ml Mz nW oF OK oN Oz Ra Rf Rh Ri Ur Vu Ti Th) nA(Aj cF Gz lb lu lW lX Mf nK Nn Nr nY Pb Qa Vu) kC(Ib oF Pf Rf Rh Ri) dD(kF mW nD nU) lW(Ti Th) oH(Aj Ch) MffR QamM OhcR OzdJ aCnB} Vw{Pz(aA aC aN bA Bb bQ bV cD cT Cu dD Dr Fa Hx II Je Jm Js Kp Kx Kz Li Mf Mj Na Nf No Oy Oz Qa Qv Ru Uc Uk Un Uy Vu Wf Yl Tl Xa Tj) Hx(Al Cu Cw Dk Il) Qa(Aw Hl Hr ld) Lx(Ar hC ld) Wmal TrfP RxUw} Oh{Vi(al hB iA iH iP kS nY oH oK pF) oN(Ex Hl mM mW Rz Zq) Si(bE cN cR dH Pd) Vj(Ar Fr Id kS nW) kE(bH Em iZ Kd Kk) mP(Em Ib Ic Pj) Id(Wb Wf Yh) Rz(iA kS nW) Em(mU nA) Hl(al Va) bH(mF mW) dJ(gP Oz) NtLp MugP IbkK SfRf ZqiA YeiO} Qa{Th(Aw Fd Gz Oz Pb Ri Wm) Dl(Rv Rx Ry Wc Wf) Hl(li Jt Vh) Hr(Du Gb Vh) lb(kK mP nA) Vi(Aa bQ cE) nD(Ex Gz Hf) kE(Cv Kd Kk) Eq(Id kS) Vj(dD Fy) mP(Pj Un) mW(bH Rm) nA(Ex Gz) AwGb TimU GnNt ShRf QygP JtdJ RinT cWnB} bH{Pa(kK kO lY mH mS mW mY nD nH nl nK nN nR) mW(aJ dG Fr Kq Mt Nr oQ Pf St Tn) kE(Fy lj Kq Li Ny Ok On) Hr(mF nK nN nR) mF(Nv Ok On) Bo(kO nC) Em(mU nN) Tr(mE nL) TinN} Nn{Hp(Ao Ap Aw Ba Cp Cv Cw Hr) Th(Gh Gn Gz Tm Xa) Jh(Em Hl Ry Tl Xa) kE(An Em ld Ti) Tm(Je Kn No) Ib(mP nA) Vz(bP Ef) Qu(Ye Xa) Vi(dl dJ) Vj(bJ Nd) AjYe EmlY GnoH MugP HuSh WbPd JeXa UkdJ} Vv{Bg(eD hA hR hV hW iC jD jE jF jG jH jl jL jM jO jQ jR jT jU jV jY lK lL lM lN lO qX rY) Mz(eD jK jO lL lN) gW(cE Lx No) IjmM KqlN} Th{Wm(Et fP Hx ln Je Jq kC Ky Mj Mz Oz Pb pF Qd Yf) Pf(Co Gn Gz nH Oz Wc Zx Yf) Lx(mM Si Wc Yf) Oz(Ed ll Nr) Tr(Rx Wc) MaRx MufP PbiA} Fa{gP(aW aY cA Ch cP dJ dN Ef Mu Of Pb Pd Qy) kQ(Aw eC eM Jo Mu Pd Rg Rh Ri Rj Uk) Pd(aW cP dJ) MyTk IvdJ WneF PfnD aYmW} hB{Rz(An Ax dD dK Fy Hl Il Im Jq kR Ks Lx Mf Mn Nr Om Oz Pk Qe Uc Tj) Yj(Aa cA Mu Ye) Gn(Ib Vs) mM(Jq Kz) HuRx ZqKs QbVi} Wn{Bo(Ap Dg Dl Jt Ju Jv Kc Mg Mm Mz Na Nm Ok Ph Pj Qb Ue) gP(Ke Mw Mz Uh) Mw(Jd Jt) Pj(aK dR) aW(Ks Rb) eF(Ha Pe) MmaQ} Ib{Qh(aQ aV cY dA eC jE jQ jR jU) Rg(iB jD jG jP jY lK lL lN) Lx(cP eC lL) Hl(aH al) mM(Ij On) DkjU QdlN Whal eCoQ} Vj{Tr(aC aS bA bB bJ cl cY Li Nt Rh Ua) bQ(Cw Gn Nc Nd Pd Rz) Hx(Id ll Pf) Ma(Cq Li) cT(kS Pd) ArLx MffR PzaC OzdJ} nD{Ed(Pf Pz Qd Qe Qh Qt St Tn) Pf(aD aO Kp Vo Tj) Gz(Qe St) AsSt EmNb MmjH TnOf IjlM VtcV VumW PdjG nAjO nHqY} nA{Wm(Ed Ex Hq Na Vu) Tr(Ed Ex Gz Nx Oy) Ex(eC Pz Rf) Gz(Dc Pz Vu) Ed(Qz Ur) Emll LxSs VumW jMkF} kE{Tn(aC Aj dA dE Dg Or) Ny(bP Kr Pb) Ok(Ed Ml oO) Lx(dD Kk) Li(dR oH) Vu(Bo Ld) FyPf NtKq NcjI} Ri{Pf(lY mM mS nH nK) Co(kO nC nJ nL) Vu(mP mW nO) mM(Ij Ke Lx) Ex(mS nN) eM(Ed kR) KylY} Mf{fR(Dr Eq Fc Fn Gc Gn Lp Vs Yd Zq Tm) Si(Hx iH oH St) Rv(Gd Ug) HxVa} Lx{Id(Eq Hl Vi Yh) Ar(Si Vh Vi) No(Vh Wd) Hl(bP li) aW(Pd Uk) HbmM YjbJ SicP PbgP} Nc{jl(kG kK lY mH ml mY nN nO) qT(Ji Jq Js Mj Qd) gCkQ lWjY} Li{mM(dR eC Kq Tn Tr) nR(Af Bn) kQ(lY Pf) MeTk TrmZ Omll aCmW bSgP dEeC} Uk{mW(Oz Qe St Vt) Pk(lX nC) mM(Im St) WmcZ NrdA NdaN YjaH QbdJ JqaW VtmF} Oz{dJ(Dr Em Gc Gn Pf Yd) Mt(al aQ GP) bP(Vz Wb) LdgP nRqY} Hx{II(Gb Sh Si Va Zq) Gb(cX Pz) AxmW DlUy UbSj YjeF SiPf ZqcX} Tl{Il(Hr Ki Nt) Vj(al cE Pg) Ub(Id Ue) CvHp DlPz JeKi PaPd} Wm{cP(aV cZ dJ) kO(Ke Nw Vt) bE(Rx We) dA(Qb Qh) JqaY} Em{nN(aC bE dD Nk Pd) Jm(mS nJ) IpmE PflY clgC} Vu{mW(Ju Ua) nI(aO Or) BajE BnnR IpnO RzoF cBIY} eM{Fn(cR dG eC hF Mq oK) EdQz SskR cRdD} Qb{Id(Wf Yh) Vi(bQ oF) fP(gP Jd) SicR ShNx} aI{Hl(Mh Mu Oy) Tj(Fi Yf) PzRz RxaM PhnN} aW{Jq(Aj Aw Ax Cs Ed Ms) ArTk InlN} Tr{Oy(lY mF nJ) Jj(lY nK) TtmZ KgmU} gP{Ld(Pc Pd) Pb(Mt Pf) ArTk ChCq MqMu} Pz{Rz(bB dD) aC(Vh Tm) AjoH OymI} Je{Kk(Eq Gh) Va(Ip Rm) ZqNy KiVi} Jt{Rm(hA jE rC) Qh(dJ jE) DcjE} lN{mS(Jg Jm Ma Mm) Jp(nC nH)} Rx{AsbE HrdF HuaM SsbQ JmUg} mW{AxPd BnQh DcOy NyPb aUdR} Mx{Id(Vz Wb Yh) SiiZ} Vt{cV(nL nN) UnnR PfkP} aC{bP(Vz Wb Ye) UyiO} Ex{IplW RgnN NxoO} Nt{Xa(Il Pf) eFnN} Tn{Ajnl CtnO dAmZ} Ny{AnHp IdVz mPIM} Tk{ArbL CseF FrcP} Oe{jY(nB nK) lWjH} Va{AlHu ChNx HrOu} Pg{hAkK mPlM mZjU} bE{aM(Gh Rv) LvoP} eC{oQ(cW Qv) GzkC} lY{Pf(cB Ur) OkIK} Ba{jE(Qh Rg)} Dr{UxiO cIgC} Yf{TjRv PbdJ} Il{FnSj NdYl} Sh{GpRm KkRj} bQ{GnRt WdcR} nR{BnSt PcjL} mM{Hvjl ljUn} BbOyoP CvUgnN FrdDkG HuVibP IpZwbJ IuJkTm YgRmhG JgmZqY SsgCkQ JjPknT Unconstrained panels with 2 analytes, where 1.0E-5 >= 'model p-value' > 0. Contains 38 panels of 145,307 total panels evaluated. : Yi(kC kF kG kI kK kN lX lY mM mS mT mU mW mY mZ nA nB nC nF nH nI nJ nN nR nT nU) Lj(Ar bN dA dJ gP hG iJ kQ) Oa(bN gP kQ) BgNg YjoE Unconstrained panels with 2 analytes, where 1.0E-4 >= 'model p-value' > 1.0E-5. Contains 142 panels of 145,307 total panels evaluated. : Lj(aE aG aH aI aN aQ aR aU aV aW bB bS cA cH cJ cP cS cV cY dC dD dE eC fP Gp hF iO kS nW nY oE oF oH oN pF Ph St Uk Up Th tF) Oa(aQ aR aU aW bS cA cK cP cY dA dJ eC hF hG iO Jt kS Ng nW nY oE oH oN Pd Ph Uk) Yi(gC kE KI kO kP lW mE mF mH mI mP nD Ng nI nK

Figure 25 Continued nL nM nO oO oP oQ Vj Th) Is(Hv Hx Ih Ik In Jn Jr Js Jt kP IY Ms nC nH nL Nr Nt Wm) bN(Fa Li Pz Qa Qb Wm) Fb(jH jU qU rC) oE(Hl Vi We Yf) Ng(Cq Tn Ut) fA(cB dA nO) Th(Qa Wm) Fa(gP kQ) Vj(bZ Tr) Vq(nA nJ) Vw(bZ Pz) YfnN JqaW RzhB nOoW Unconstrained panels with 2 analytes, where 1.0E-3 >= 'model p-value' > 1.0E-4. Contains 1,008 panels of 145,307 total panels evaluated. : Oa(aA aC aD aE aF aG aH aI aJ aK aL aM AN aO aP Ar aS aV Aw AX aY aZ bA bB BC bE bF BG bH bI bJ bL bM Bn bO bP bQ bR bU bV bW bX bZ cB cC cD cE cF cG CH cI cJ cL cM cN cO Cp cQ cR CS CT cU cV CW CX cZ dB DC DD DE dF dG dH dI dK DL dM dN dR Ed eF Ez Fb Fn FP gL Gp Ha HB hC Hr Hu Hv Hx iA Ib Ic IH Ii IJ Ik II Im In Io IP Iq Ir Is It Iu Iv iZ Je Jg Jj Jo Jq Js Ju Jv Jy Kc kE Kf kP kR Lh Lj Lv Lw IY Ma Mb Md Mf Mg Mj Ml mM Mr MS MU mW MY nA nB Nc ND Ne Nj Nk Nl Nm No Nr Nt Nv OF Oi oK Ou Oz Pb Pe PF Pi Pj Po Pz Qb Qc Qh Qn Qt Qu Qv Rc Rf Rg Rh Ri Rj Rm Sr St Uf Ug Um Un Up Ut Vu Vv Wm Ti Th tF) Lj(aC AD AF AJ aK AL aM An AO AP AS Aw AX aY aZ BA Bb BC bE bF BG bH bI bJ bL bM Bn BO bP bQ bR bU bV bW bX bZ cB cC cD cE cF cG Ch cI cK cL cM cN CO Cp CQ cR Cs CT CU Cv CW CX cZ DB Dc Dd De dF DG dH DI DK DL dM dN Dp dR Ed EF Ez Fa Fb Fn Fw Fy GL Ha HB HC Hf iA Ib Ic iH iP Is IZ Jd Je Jf Ju Jv Jy Kc Kd Ke Kf Kg Ki Kj Kk Kl Kn Ko Kp Kq KR Kz Ld oK Or Ou Ow Pi Pj Pk Qg Qh Ql Qm Qn Qt Qu Qv Qw Qx Qy Qz Ra Rb Rc Rf Rg Rh Ri Rj Rm Sr Ss Tn To Tv Tz Ua Ub Uc Ud Ue Uf Ug Uh Ul Um Un Uo Ur Us Ut Uu Uv Vo Vp Vt Vu Vv Wm Tj Ti) Is(aI Aj aQ aV aW bN cA Ch cK cR Ct cV dA dJ Ed Ef Et Fa Fn Fp Fr gP Hq Hr Hu Hw IB IC Ii Ij Il Im Io Ip Iq Ir It Iu Iv Jd Je Jg Jh Ji Jj Jk Jl Jm Jo Jp JQ kC kE kF kG kI Kj kK kN kO Lh Li lK lN Lu Lv LW LX Ly Lz Ma Mb Mc Md ME MF Mg MH MI Mj Mk Ml MM Mn MP Mq Mr mS MT MU Mv MW Mx MY MZ NA NB Nc ND Ne NF Ng Nh NI NJ NK Nl NM NN NO Nq nR Ns nT NU Nv Nw Nx Ny OE Of Og Oh Oi Ok Om On oQ Oy Oz Pa Pb Pc Pd Pe Pf Pg Po Pz Qa Qb Qc Qd Qe QT Rc Sh Uf Uk Un Up Vs Vv Tk Th) bN(Ax Cs Ed Et Fn Fw Fy Hb Hr Hx Ib Ic Id Ir Jm Jq Jr Js Ke Kk Ko Ld Lx Nn No Nq Nr oE Qc Qd Qe Qh Qx rC Rg Rm Sr Ss St Uh Uk Ut Vt) oE(aW cE Fb Fn Gc Gn Jq kQ Ld Li mM Mt Nd Nr Oh Pa Pz Qb Qh Rg Rt Rz To Uy Vj Vq Vw Vz Wc Wd Wf Wh Yg Yh Yi Wm Th) Fb(eC ED gW hA hR hV hW hX jD jE jM jO jP jQ jV lK lL lM lN Ng qT qV qW qX qY rA rB rX rY rZ Ss Uk) Qb(aI aQ aU aV AW Ax cF cR cS cV cY dA dD dJ eC fP gP Ic Si Uk Up Wm) Fa(aP aQ aU aW aY bL cA cK cN cP cV cW dA dJ dN Gp Ik Ng oH Pd Uk Tk) Yi(aI aR bJ cP EF Ib Ii Ik iO Je Jh Kj Kn Mg Nt Pd Qt Ss Vw) Wm(aI aQ cP cZ dA dD dJ Ed Gp Hb Hx Jq Li oH Qa Qc Qd Uk Yl) Uk(aI aN aW Cq dJ Ed Il Ir Iu Jm Jq Lx Pz Qa) Ng(bQ Co Dk Fy Kq Qh Tr Tt Ua Uc Vq) Qa(aQ aR aW aY dA dJ gP mW Vj Vw Zq) Lx(aQ aV aW aY cA cP dA gP Yl) Li(bS dJ gP kQ mW Pb Ph Up) Ow(Hl Sf Sh Si Vi Vw Yl Zq) bZ(Eq Hl Mu Rx Rz Wd Yj Zq) Nn(dA dJ Gn Sh Vj Vz Tm) Oh(dJ gP Hl Sh Si Vj Yl) bH(mF mU mW nC nL nN nR) Ed(aQ aR gP Hx nD Th) Ik(Cs Dr Wh Yh Tl Xa) Vu(mM mW nA nD nI nO) lY(aI Ok Pz Qc Up Yl) Nr(aV bS cA cK dA) Hx(Ax Cs Hl Vj Th) Pf(cA cK Pb Si Vw) mM(hB Kq Ok St Tn) Yl(Ld lW Nd nN) gP(Ax Cs Ld Mh) mZ(Mz Ok Tn Tr) Tj(oD oV pI) Th(Ma Mj Oz) Mf(fR Si Va) Yj(nR oP Tl) Rg(bS cA cK) Vj(bQ Ma Oz) Vw(Cq Il Kk) dJ(Oz Qh Rm) Ax(oH Pd) Hl(aI bE) Vz(Kk nN) Sh(aI Rm) Wn(Bo Mw) Up(Ir nA) Uw(lX nJ) nO(eQ Tn) AjBg CskQ NcqT IlRz HbaW JeVa WcnA KqkE RvaC OrnN VqkC aQcY cAcE cReM dDdU Constrained panels with 3 analytes, where 1.0E-9 >= 'model p-value' > 0. Contains 2 panels of 24,406,229 total panels evaluated. : DrIkbP GnLxId Constrained panels with 3 analytes, where 1.0E-8 >= 'model p-value' > 1.0E-9. Contains 17 panels of 24,406,229 total panels evaluated. : Ik{bZ(Du Hl Hp) aM(Lp Lt) UbTl} Fb{Vv(gW jH) EdqU} bZ{FiPd NgHl} BgVviB HxSicX ZqOwdD LibHmW LjcEkE UhVumM Constrained panels with 3 analytes, where 1.0E-7 >= 'model p-value' > 1.0E-8. Contains 117 panels of 24,406,229 total panels evaluated. : Ik{aM(Gh Ps Ru Rv Uy Va Vi Wc Wf Yg Yi Tl Xa Yf) bZ(Ux Vb Vi Yh Yi Yj) bP(Uw Tm) hB(Dr Gn)} Up{Dc(kI kP mS mW nA nB nR nT nU) nA(Ir Oa Rm) lY(Kq Nw) QamP VtnR} Vw{bZ(aA Aw Cq Hr Pd Rg Um) fP(Lx Oh Ow Pf Yi) Pz(bN Nn Rh) BgHx} Yi{Ib(aI cZ eF) Vj(Ih Wc Ye) Ng(Bg bP) OzdJ} Fb{eF(eD lN qT) rB(kR kS) bNrY eDoK gLrC} bZ{Hl(Uf Uu Ux) ThGn YjeF RuPd} gP{Oa(Nj Ph) YjTl LdPb LjdJ} Ri{nU(Pf Vu) UhmM aClY} oE{Gc(Nc Pe) DrUb KomM} Oz{dJ(Mt Rt Yh)} dR{LijF OwVi nTmM} kE{bH(Tn Tr) ArLx} kQ{Oa(Pd Ph) LjaE} Bg{NghR VvrX} Is{NcVj IbbN} Yj{aH(Aa Tl)} Qa{DlYe IdmP} AlUkmW TrVvmZ WbKkRm ShRfOh LjbNiJ Constrained panels with 3 analytes, where 1.0E-6 >= 'model p-value' > 1.0E-7. Contains 933 panels of 24,406,229 total panels evaluated. : oE{Yj(Aa aC aH aI aS aX bC bE bU bX bZ Cs Ct cZ dD Dp eF Et Ex Fn Gc Gl Gp HB Hf iA Ij In Io iP Is Jq Kc Kr Ld Lh Li Lp Lu Lv Lx Lz Mf Mj Mk Ml Mm Mq Mt Mx Nn Nq Nw Ny Oa Oh Om Op Or Ou Ow Oy Oz Pa Pb Pc Pf Ph Pk Pz Qa Qb Qc Qd Qe Qg Qh Ql Qm Qn Qx Rt Rv Sr Ss St Tz Ue Ug Uh Un Ur Ut Uw Uy Vh Vi Vo Vt Vu Vz Yl Zq Tl Wm Ti Yf) Yf(An bB cI Cp Cv Db Di Ed Gl Hl Ib Ip Ki Nc Nk Pz Rx Sh Ur) cP(Ux Vb Vh Vi Vj Wc Wd We Wf Yi) We(Af cI Nd nW Pb Ri Rj Ut) Vi(Ed Gh Gl iO Pb Qc St Wb) Lj(aE gP hG kQ Mb Nj Ph) Ub(Fd Hp Rz Vw Zq) Wf(cN Dl Fn Wb) Yg(Uc Vu Yi) Vj(cI dC Pz) Ib(Ps Uw) Sh(Ri Rj) Wd(dC fP) Tm(Yi Th) Rz(Bb Ri) Vw(Cq Pz) mM(Li Pk) GbGl GcUh IsTk WbaA JeUw} Lj{gP(aE aG aI AR bN cH cP cR dA fP hG iJ Ik kQ Mb Nd Nj Nl Pb Ph) iJ(Aj CP Cw dA Fr Ik Jd Jo Jt kQ Mu Ng No Nt Pd Qy) dJ(aE Ar bN cP hG Iv Jq kQ Ma nW Oz Pb Pd Uk Un Up) Ar(aE aL aQ bN cV dA Fb Hx nY oH Uk) kQ(cJ dD eC Jd Ju Nk Nl Oa Pb Ph St) Nj(aG bN cP cV dA eC nY oH) kE(cV Dk Tn Tr) Nl(bN cP nY) Ph(fP nY oH) aE(Ed hG iO) mW(bH Rh) oH(Gn St) BgNg GznA NknY PzVw} Vq{nJ(aC bE bO bQ bZ cF dD dK Ed Fa Fy Hx Ij Is It Jl Jn Js Ju Jv kN Kq Lx Lz Ma Mj Mq Mr Mt nC Ni Nk NN Nr Nt Nu Nw Oa Oh On Ow Pb Pe Pf Pz Qa Ql Qt Qx St Tn Us Uu Wm Tj) kC(aC bZ cT dD kN Lz Ma Mh Ml Oh Ow Qx Ra Tn Tt Wm Tj) nA(dD Ed nL nN Oh Pf Pz Tr Tj) aC(kK lY mM mU nD nU) mS(bJ Nw Tz) Or(lX nI) dD(kE kK) mM(Oh Ur) kP(bJ cF)} Oa{gP(aW bN bS cA cK cP cR dJ fP Ha Hb hG Ik Jk Jo kQ Nd Ng oH Pb Pd Qh Qy Up Tk) kQ(aE Aw bN Cp cQ dC dD dJ eC Hr Ib Ik Jd Jo Jt Mu Nd Nj Nk Nl Pb Pf Un Up) bN(aR aW cP Dc dJ hC iJ Ne Nj Nl nY oF Ph) Nj(eC kS nW nY oH oN) Ph(kS nW nY oH oN) Nk(iZ nA) Tk(aJ bU) Pd(aW dJ) eC(kP mM) nB(Af Bn) nW(dJ Jd) oH(Cp Dc) AxjH GzmS IkiJ aQaW bHmY dDnD} Yi{Vj(aJ aP aR bE bJ cE cG cI cN cO cP cR cV dH dJ fP Fy nW oH oN pF) Ng(aG aM aN bZ cI cW dJ fR hB Ip Jk kQ Qc Wd) Yg(aI bZ hB iZ kQ oH oN tF) Ib(aH aM bB bC cF dD) Ik(bP dJ hB) Rz(hB iO nW) oN(Fn Iz Oy) Th(fP nW) iO(Kn Sr) kQ(Oy Pd) EfbZ IpbJ PzVw VshB aRbP} hB{Ik(Gc Hl Rt Rv Rz Uw Ux Uy Va Vb Vc Vh Vi Vj Vz We Wf Yd Yh Yj Yl Zq Zw Yf) Rz(aC aY Cq Ij Is Jm Nn Oh Pz St Vs Vu Yj) Yj(Ef Ss Tm Tl Xa) Th(Ye Tm) Hl(Ch Ux) IbZw PzVw LimM VjaC} Vj{Tr(AA aD aE aG aR aY bH bX cE cG cL cP CQ cW dC dD dH dI dL dN Rf Wb) fP(bA cT Oh Ow Qa) bZ(dD Ik Ks) Hx(iO iP) Id(Js Lx) MacI QadC JskS PbaQ cUoH} Vw{Pz(Ax bZ Cs Ld Lx Lz Ma Mh Ml Nr Oh Ow Pe Pf Qx Ra Rf Wm) bZ(dC Hl Ho Hu Hx Ly Nb Vi) MffR TtfP IkaM} Fb{jH(aU Ba Ct jQ Mj Ng Vo) jU(Ib Vv) kR(rY rZ) rX(gL kS) CtlM MhjP InlN RbWn SsrC aKjQ aUgW} Oh{Vi(hC hG iO iZ oF oN) oN(Gn Op Sf Sh) nA(Ex Gz Ib) Si(cP nW) mP(Ex Id) WfbJ RzhC bHkK} Is{Ib(aQ dA dJ jY lK) mS(nC nH nJ nL) Tk(aR cJ dN) mM(Uk Vs) WmbN GznA NcqT UpkN cReM} fR{Mf(Du Fd Hl Hp Rt Rz Vh Vz Wb Wd Wh Yg Zw Xa Th Yf) FnJe QaVi} Ow{Vi(bZ iO kS oF oH oK oN) oN(Gn Op Sf Sh) DlYe HrVa IdWf SiPd ZqiA RzhC} Fn{eC(kC kO nA nC nD nF nH nJ nL) eM(aP cS Il) IlSi LimW PfkE} bZ{Hl(Dg Jo Mg) Ik(Gn Wf Ye) Rx(Hr Hu Pd) Vi(Qb Th) HrUx ShaY LpPd} Up{Dc(lY nI nJ oP) nA(Cq Ih Nw Vt) lY(Ok Qc) QamU NwnL VtkN} Ti{lY(Nn Ny Pf St Vu) Nn(mU nB) EdnA LxmM IjmU JlmZ VunI} Tk{Fa(aH bE bN cL gP Ub) Mz(Bo dI gP)} Wm{Th(iO oH Qn)

Figure 25 Continued bN(cZ Jq Qb) BgNg JqaW} Lx{Id(Ho Vz Wf Zw) Rz(hC nW) RimW VvlM} kE{Tn(bJ cR Ct Kj) Th(Nn Pf) Tr(Kj Qb)} Ng{Ef(jD jL jM) Bg(jT lK) NnYe PzbN} mW{Li(cR dD Ri) bH(Ax Pe) ThVu JmUk} Ik{Uw(aM dL) ShSt RxaM RvcR VhdL} Vv{Bg(jK jP rZ) QdlN JylK} Nn{Jh(Gn Ye) DiHp NtTm} Yj{InTl XaaI aHcA eFoF} Qa{bN(dJ Ib) ViiO bHnI} Pf{nD(aC bH Jf) NtTl} cC{Qv(mU mY) aPoQ cWmY} eM{EdTo NjSs UudJ} mM{ThIj TnQw QdRi} As{WdoH RvbE} Gb{St(Aw Hr)} Gz{EtnJ IlnA} Vu{EdnD ThlY} bN{AxQb PzSs} BbRzoF CoRinH CvUgnR ExnAnK GnMxoH NcQggC HxIpVz IbQhdJ TrOymZ IjSicP ShRmiO Constrained panels with 3 analytes, where 1.0E-5 >= 'model p-value' > 1.0E-6. Contains 2,975 panels of 24,406,229 total panels evaluated. : Lj{iJ(AP aQ aR AW Ba bS cA Ch cK CO Ct DE Ef Ha Hc hG Ib Ic Im iO Ir Iz Jg Jp Kg Kq Mg Mm Mn Nk Nr nW oE Of oH Pb Pe Pf Po Qu Ss Up Ut Wm) aE(aQ aR aV aW Bc bN bS cA CP cS Ct cV dA eC Ib Ik Je Jo Jt mW Ng Nj Nl Oz Pb Ph Uf Uk Up) Ph(aG aI aN aQ bF BG bN bZ cP cS cV cY dA dJ Gp Il Is iZ Jy Ma Nd Nq Or Ou Tn Uk) hG(aG aQ aV bG bN cJ cV cY dA dC dR eC fP hB hF Hr Ib Jf Jq Mu Nd Ne Nk Pb Uk Up Wm) bN(aG aI aR aW cH cP cR cS cV dA Et fP Is Jq kQ Nd Ne nY Pb Pz Qv St Uk Wm) gP(aQ aW cA Ch dC dE Fr Hb Hu Ib Jq Mu nD Ne Ng Nk oH Oz Qv Qy St Uf Uk Up) dA(aW bP cP cS dC Ed Fb Ib Jr Jy Ma Mb Nd Nl nY Oz Pb Qv St Uk Un Up Wm) kQ(aL aQ Aw Bn cH Cx cY dC Fb Ib Ik Il Jq Mb Mu Nd Pd Un Up) oE(aP aR aW cP dC Fn Fr Jq mM Mw Nd Nk oF Qv St Uf Un Yj) dJ(aR Aw Bg bZ Ch dC Ic Ik iZ Jt Jy Nd Nj Nl Nq Oa Tn) kE(aI bF BG bH bZ Cq Cu dR Ef hB Kq oH Or Ou Uc) eC(aK aU aW cL cW dE Fb Ib Jd Ju Mb mW nD Nk Un) Ar(aG cZ Hb Ic Ik In Is Jq Kz Nd Oz Up Ut) aW(aG aH aI aQ aV cB cV cY fP Jq Ne Nl oH) nY(aQ aV Aw bS cV cY dC Jq lN Mu Mw Ne oH) cP(aI aQ aU aV cY Ju Nk Pb St Wm) Th(fP In iO Je kS Lu oH pF Up) Pb(aG aI aQ bB cV cY cZ dD) fP(Fr Ik Jd Nj Nl St Uf Vw) oH(cH Dc Ib Mb Qv Uf Un Wm) aQ(aR Mb Nj oF St Uf Un) cV(Dc Mb Nl Pz St Un Up) nD(bH iP Jy Or Qu Qw Tn) aR(aI cS Ed Nd Wm) mW(Aw cQ dD Rg Vu) Ik(aG Bg cS oF) aN(aI Nd Nj Uk) Mb(dB hF kS) Pg(bS cA cK) Fb(jH lM) Ma(cH Uf) Nj(aI iZ) Nl(bS dE) Uc(Jt Ng) Up(nA Us) bZ(Rx Vi) kS(Jq St) BgCp DcIs TiHx HakC NdaV IbiB ShNx PzUk WfcD RzhB RimS OwoN UncS VqnJ aImM aPoP cAcE cYoF dRjF} Oa{hG(Aj aQ Aw bN bS cA Ch cK Cp cY De dJ eC Ha Hb hF Hr Ib Ik iO Ir Jo Jt kS Mn Mu Ng Nh Nk Nl Nt Nv oE Of oH Pb Pd Pf Qu Qy Rm Uk Up Ut Wm) aW(aV Aw cB cP cR cV cY dA dB dJ eC Fn Gp Hb Ik In iO Je Jq Jt kS Ne Nj Nl oH oN Ph Uk) gP(Aj AR Aw aY bL Ch Cp dA DC DE Ib Iz Jt Mb Mu Ne Nk Nl oE Oy Pi Qu Uf Uk Vs) dJ(aR Aw bS cA cK cP Ha hC Ib Ic Ik In Iv Jt kS Ma Ng Nj oH oN Oz Pb Ph Uk Un Up) oH(Aj Ar Aw Ch cP Cw De Gn Ib Jt Kq Mb Nk Nl Ny Qh Qu Uf Un Up Wm) Pd(aN aQ aU bN bS cA cE cH cL cP cS cY dA iJ kE kP mW nY Up) cP(aQ aU Cp cS cY Ha Hv Ib Ik kS Ne Nj Nk Nl oE Pb Ph Wm) bN(Ar cR cS dA hF Hr Ib iZ nW Pb Pz Qv Uf Uk Un Up Wm) nW(aQ bS cA cK Cp cY Dc Ir Ne Nk Nl Qh Qu Un) eC(bS cA cK cW dE Fb Gl Ha Ib Im Ir Jt Ut) iJ(Aj cA Cp Cw De Ha Ir Jo Jt No Qu Ut) Ph(aQ aU bF BG bZ cS fP Il iZ) kS(aE aR Ir Jq Mb Nk Qh Qu Qy Th) Ik(aE aQ aR cS dA fP hC iZ oF) nY(bS cA cK Cp De Ha Ir Jt Nk) oN(cA Cp cY Fn Ib Ne Nk Up) Nj(aQ aR aU dA iO iZ Js) nB(aX Cx Ii Jt Nh Nk Up) kQ(cJ Cw Ic oE Qh Sr Uk) bH(kE kP mW nD nI nU) cA(aQ aR cE Ne Nl Un) Nk(iO kC kE kO mY) Jt(aE aQ Et iZ Pz) bS(aQ aR Ne Nl Pb) Cp(aR bF Bg fP) Uk(aN dA mM mW) Th(hC iO Je) Un(aQ cS hF) Up(iZ mS nD) Ha(aR hF) Ri(mS nU) Pf(kE mY) cK(Nc Nl) dE(aQ Gp) mW(Hr nD) iZ(Ib Jo) oE(aP Ir) AxlM BgNg FbjH IqhC PzVw JdfP LhkE aCnD aEiO bEnU} Yi{Ng(bR cP Ct Dk Em Ez Fr Gp HC Hu Ib Id Ij Il Is Iz Jd Je Jm Jr Js Ju Ko kR Li Me Mu Na Nd Nt Of OH oN Oy Ps Pz Qd Qh Qy Qz Rf Rv Rx Ua Um Ut Vb Vs Wc We Wh Ye Xa Ti Th) Vj(aC Ar aX aY aZ bC bG bO bP bX cA cH cL cQ cW dC dG Dp eF Ij iP Jf Jo Jp Js Kx Mp Nd Nm Oh Om Pd Qg Qy Rf Rv Sj Sr Ua Uh Vb Vh Wd Zq Xa) Th(aI bJ cV Gz Ic Ik Il iO Kn Og Oi Pg Ri Tm Yf) Ib(aG aP aY bE bP dJ iH kS nY oE oK oN Yc Xa) Ef(aH aI bF BG dR hB kQ oH oN) Kl(aG aH aI bJ bZ Du Gp Id Qh Rf) Ct(aM aN aY bO bP cP dJ oN) Rf(aM Kk Lx Ow Ss Uu) Oy(aH aN aY bO dJ oE) cP(aQ Gz Qt Ss Ug Uu) Ik(aG cI dL eF iO) Yg(aO fP iH nW) oE(fR nW Ri Yj) Mg(Il Je Na) Rz(hC kQ) bP(Dl Qt) FneF NtIl MuaI IzbZ TmaY KkKn RidA PbdJ aXiO dEfR} Is{Up(bN dJ lN lY mI mM mP mT mU mW nA Ng nN nO nR nT nU Qt) Ib(aV bH cH cP cR cY dB eC fP gP iO jD jE lL nA oE oN) bN(dJ Ed Hr Ic Jd Jt Lh Pz Qy Rc Ss Ua Uk Un Vs) Wm(cZ dA dJ Hx Ik Jt kO MS mY nA Nt Th) Ng(Bg dJ Fb Fn gP iC iJ Tr Un) nC(hA Iu JL jO lM Nj nU Pd) nD(Ed jU jV lK lM mS Pd qU qY) nH(hA Iu JL jO lM Nj nU Pd) nL(hA Iu JL jO lM Mv nU Pd) Ms(dJ Hv Ih In Jn Jr Nt) Ik(Jn Jr lN Sf Sh) jU(kC kF kI mP nI) Jt(dJ Et In Pz) gP(Ch Qy Uk Vs) lN(Cw Fb mS Vv) Jj(kP lY nT) mM(Em hB oE) qY(kC nI nT) kO(hA mS Pd) Fb(jH qU) Id(Eq Vw) Pz(In Vw) Jd(hB oE) Uk(aW dJ) iJ(Ch Qy) jI(mZ nU) BoTk CpHx NdJr IulY KeVj KnVa nIjV} oE{Yj(aF aG aM bH dK dN Je Ji Jj Jv Kj Ko Mg Mp Mr Nm Nx Oe Pj Rg Rh Rm Sf) Gc(bN cP Ef Et fR Id Ik Je Jp Nk Nt Pj Un Ut Vi Th) mM(Et Ij Im Jg Kq Mm Ok Pz St Tn Tr Uc Uh Ur Vq Vt) Yf(cA Ef Fn Hr Hv Id Je Jp Jv Mv Nj Nq Op Wf Tj) We(aG Bb dC fR iO Jf Kf Kk Ma Pk Pz Up Vv) Vi(Bo cI cQ Mx Nd Oh Ow Oz Pk Pz Qb Up) Yg(Ps Pz Rg Rh Ri Rm To Uw Vv Wd Wf) Wf(De dG Ik Je Mf nW Vs Wd Th) Up(eM Hl lW lY nU Tm Xa) Rz(Pk Pz Uc Ut Vu) Wm(cP Jq mP Th) Wd(hC Je Nd Pz) Vq(Ik mS nJ Pd) Tm(hC Je Rg) Ri(Wb Yk Xa) Pz(Ng Of) Jq(aW kE) Li(kQ Nj) cP(Gb Yh) DuPk FnaW GnGl NdVj HlOw IbQh WbUm VzcI ZqVu ZwnW JePs XaVv LdgP RucR} Qc{jM(kE kF kI kO kP lX lY mF mI mS mT nA nC nD nH nJ nL nT) mP(jE jG jH jI jK jO jP jY lK lL lM lN qT qU qV qX qY) lN(kC kN kO kP mM mS nA nC nD nF nH nI nJ nL nR) lY(iC jD jI jV jY lK qT qU qW qX rA) nD(iB jD jG jT jU jV jY lK lM qU Up) jT(kO mM nC nF nH nI nJ nL) lK(kE kG kI kN lX mE mZ nK) jU(kO nC nF nH nI nJ nL) jV(nC nF nH nI nJ nL) kN(jI qT qU rA) mI(jD jI qT) mM(jD jO jR) Wm(bN Th) Hr(Ux Va) nR(jH qU) nL(hA lM) qY(mE mZ) AxbN GnIk HxSh VqnJ nNjH mHrA mTjP jFkI jRkP} Fb{jH(Aj aK aQ aV bE bN bX cB cR cY dR Ed eF Ez gW Ik In jE JF Jg Jk Jo Jr Jt jU Kj Kl Kx Kz Mg Mh Ml Nc Of Oy Ph Qa Qb Qd Qg Ql Qx Rg Sr Ss Uk Up Us Vt) jU(aA aW Ba bN Ez Ik Jg kS lN) qU(bC Dl eF Gp iO Jq Ml Qb) eC(Ch Ib Ld Ng Qy Ss Vs) rC(bC cC Ib Ic Mj oK) lM(In Ld Li rX Vt Vv) Ng(Cq Ij Jq lK lL) lN(Mj Ml Qb Qd Rg) Vv(jD jO jP lL) jD(Ik Jt Ss) jO(Ba eF oK) jQ(aU Ba cY) Ib(jV lL) rZ(eF Ms) rY(jE kQ) CtlL MjjF UagW IkVq InqW SsqT JtqY WncX OhkE bVrB eDiH} bN{Qb(aQ aW cR cS cV dJ Fa fP gP Hr Ib Ic iJ Jv Ld lN Pz Uk Ur) Wm(aI cP dJ Et Fa Hb Hx Ke Ld Lx Pz Qa Qd Qe Qh Uh) Fa(aY cP dJ Ed Fn hC Ib Jm kQ Pd Pz Ss Uk Un) Qa(aR aW Ax cP dA Fn gP Hr Ic Jt Ng Ss Uk Un) Pz(Aj Ed Jq Jt Kj Ld rC Uk Vz) Ib(Et Ih Ij Lx Qe Qh Rm) Ax(Et Hb Hx Jm Jq Qd) Ed(Et Hb Jq Ko) Lx(Hr Ic jH Ss) rC(Ic Ih Mj Nd) Et(Fw Jt Ng) Jq(aW Cs qT) Li(dJ gP kQ) Uk(aW Ir Jm) Fw(Fn Tm) Nr(dA Pb) dJ(Qh Rm) MjjF HlOw IcWn RgcA PfnH} bZ{Vw(aC An aY bH cI cP cQ cR dH fP Gn Id Ki Kn Lv Mb Me Nd Nx Pb Sr Ub Ur Ye) Vj(aC aY bE cI cP Et Fn Hl Ho Hx Id Lv Ms Oz Pb Pd) Hl(Aj bC bE bI Ed Ef Kg Kj Kn Pd Rx Th) Yj(Aj bE Ef Jo Mu Ng Pd Ss Uf Tl Th) Rz(An aY bE bI dD Il Kk Lv Ow Ut) Th(Gz Rx Wc Zx Tm) Ng(Lp Vi Yl Ye Tl) Zq(aY bE dD Pc) Rx(aC Pe Pg Ss) Hr(Fc Uw Va) Ik(Dr Gc Vq) Ef(Vq Ye) Fa(Tk Wn) Op(aY bE) Ux(Aw Um) Vi(Ed Oh) aC(Si Vh) EqId HoUf KnUy} Ng{Bg(Ax Cs De Fn Fy Gp Hb hV hW Hx Ij Iq Iu Jm Jq Li Lx Lz Ma Mh Ml Mq Nb Nj Nn Nr Of Oh Ow Oz Pz Qa Qb Qh Rh Sr Th) Pz(bF bJ bQ GP oH Tn Uk Ut Ti Th) gP(Fa Ld Li Lx Oh On Qa Tr) Yg(Nn Nr Oh Ow Pf Tj) Ij(Fn Je Tr Uc Up) Pf(cA cK Yh Ye) Ef(hA jE lN) Wm(Gp Qh Ut) Th(Qa Tn Tr) Nn(Gn Vz Yh) Nr(bS cA cK) Uc(iC jD jM) Il(Fi Vq Vz) Vq(kP Uk) dJ(Qa Qh) CqGp TrYe JeWd JqaW RgjE} Qa{Up(lY mM nA nB nD nN nO nT nU Th) Th(Aw Fd Gz Oz Pb Ri Wm) Dl(Rv Rx Ry Wc Wf) Vw(Aw Hl Hr Id Pz) Hl(Ii Jt Vh) Hr(Du Gb Vh) Ib(kK mP nA) Ik(Gn Sf Sh) Vi(Aa bQ cE) nD(Ex Gz Hf) kE(Cv Kd Kk) Eq(Id kS) Vj(dD Fy) mP(Pj Un) mW(bH Rm) nA(Ex Gz) AwGb TimU GnNt ShRf QygP JtdJ RinT VqmM cWnB} Vq{nJ(Ap Ax Cs Cu Cw Dg dR Et hB Ib Ih Ik Im Jj Kp Ld Mf Mh Ml Mz nW oF OK oN Oz Ra Rf Rh Ri Ur Vu Ti Th) nA(Aj cF Gz Ib Iu lW lX Mf nY Pb) kC(Ib oF Pf Rf Rh Ri) Ik(bQ cB cF cR dF) dD(kF mW nD nU) lW(Ti Th) oH(Aj Ch) OzdJ aCnB} Ow{Hl(aI Ar bE bG bI bP cC dA eF Id Nm oN Rf Va) Vi(aI bF BG

Figure 25 Continued bQ iA iH iP) Si(aC cP cR dH Hr Mf Nx) Id(Gh Gn Ho Yh Zw) Wf(aR bJ Jt Ke Nt) Pd(Vb Wh Yh Ye) Gn(kS oH oK) Rz(fP hB oN) Hr(Gb Yl) Sh(Nx Rf) Vw(Cq Dk) CwWe TnkE YjeF VjkS} Ik{hB(Du Fd Gb Gh Hp Lp Lt Ry Yk Tm) bP(Gc Hl Vh Vi Yh Zw Ye) dL(Dr Hl Ps Rv Rx Yd Yh) Dr(bH dG gC iO) Gc(aY cS dG fR) Sh(Ps Qh Ut) Tl(Bg Dc Hl) Rv(cS cU fl) Wh(Cs Je) Rx(cO cR) aW(Jq Lx) gP(Fa Li) YfiO HlaP HrPs IjSi IpLp PzYe QhdJ VibH} Pz{Vw(aA aC aN bA Bb bQ bV cD cT Cu dD Dr Fa Hx Il Je Jm Js Kp Kx Kz Li Mf Mj Na Nf No Oz Qv Ru Ue Uk Un Uy Vu Wf Yl Tl Xa Tj) Rz(al bB dD) aC(Vh Vj Tm) nA(Ex Gz) AjoH DlTl EdnD GbHx OymI} Oh{oN(Ex Hl mM mW Rz Zq) Si(bE cN cR dH Pd) Vj(Ar Fr Id kS nW) Em(kE mP mU nA) Id(Wb Wf Yh) Vi(al kS nY) mP(Ib Ic Pj) kE(iZ Kd Kk) Hl(al Va) Rz(iA nW) dJ(gP Oz) NtLp MugP SfRf ZqiA YeiO UpmU bHmW} Up{lY(aC al cB dD nA oF Oz Pb Pc Pf Qd Uh) nA(Ax Fw Kk Li Lx Ok Qb Tr Uc) nO(lj Jm Lx Qe Tn) mW(Jm Oe Qh Vt) mP(Ir Nw Ok) nD(Kk Ok Pf) DcmY QdlN QenT KqkE NwkN VtoP ecoQ} Th{Wm(Et fP Hx In Je Jq kC Ky Mj Mz Oz Pb pF Qd Yf) Pf(Co Gn Gz nH Oz Wc Zx Yf) Nn(Gh Gn Gz Tm) Lx(Si We Yf) Oz(Ed Il Nr) Tr(Rx Wc) MaRx MufP PbiA} bH{mW(aJ dG Fr Kq Mt Nr oQ Pa Pf St Tn) kE(Fy Ij Kq Li Ny Ok On) Pa(lY mY nI nR) mF(Hr Nv Ok On) nN(Em Hr Ti) Bo(kO nC) Tr(mE nL) EmmU HrnR} Nn{Hp(Ao Ap Aw Ba Cp Cv Cw Hr) Em(Jh kE lY) Ib(mP nA) Vz(bP Ef) Jh(Hl Ry) Qu(Ye Xa) Tm(Kn No) Vi(dI dJ) Vj(bJ Nd) kE(An Id) AjYe GnoH MugP HuSh JeXa UkdJ} hB{Rz(An Ax dD dK Fy Hl Il Im Jq kR Ks Lx Mf Mn Nr Om Oz Pk Qe Uc Tj) Gn(Ib Vs) Yj(cA Mu) mM(Jq Kz) HuRx ZqKs QbVi} Wn{Bo(Ap Dg Dl Jt Ju Jv Kc Mg Mm Mz Na Nm Ok Ph Pj Qb Uc) eF(Fa Ha Pe) gP(Ke Mw Uh) Pj(aK dR) aW(Ks Rb) MmaQ MwJd} Lx{Ar(Si Vh Vi Vj Vw) Id(Eq Hl Vi Vw Yh) Ib(cP eC lL) No(Vh Wd) Hl(bP Ii) aW(Pd Uk) mM(Hb Ri) kE(dD Kk) YjbJ SicP SsnA VwhC PbgP} Fa{gP(aW aY cA Ch cP dJ dN Ef Mu Of Pb Pd Qy) kQ(Aw eM Jo Mu Pd Uk) Pd(aW cP dJ) MyTk IvdJ PfnD aYmW} Ib{Qh(aQ aV cY dA eC jE jQ jR jU) Rg(iB jD jG jP jY lK lL lN) Hl(aH aI) mM(Ij On) DkjU QdlN WhaI eCoQ} Tr{Vj(aC aS bA bB bJ cI cY Li Nt Rh Ua) nA(Ed Ex Gz Nx) Jj(lY nK) Li(mM mZ) Oy(mF nJ) TtmZ KgmU VwfP} nD{Ed(Pf Qd Qe Qh Qt St Tn) Pf(aD aO Kp Vo Tj) Gz(Qe St) AsSt EmNb MmjH TnOf IjlM VtcV VumW PdjG nAjO nHqY} Hx{Il(Gb Sh Si Va Vj Vw Zq) Vw(Al Ch Cu Cw Dk) Mf(Si Va) Vj(Id Pf) cX(Gb Zq) AxmW DlUy UbSj YjeF SiPf} Ri{Pf(lY mM mS nH nK) Co(kO nC nJ nL) Vu(mP mW nO) Ex(mS nN) eM(Ed kR) mM(Ij Ke) KylY} kE{Tn(aC Aj dA dE Dg Or) Ny(bP Kr Pb) Ok(Ed Ml oO) Li(dR oH) Vu(Bo Ld) FyPf NtKq NcjI} Wm{nA(Ed Ex Hq Na Vu) cP(aV cZ dJ) kO(Ke Nw Vt) bE(Rx We) dA(Qb Qh) JqaY UkcZ VwaI} Nc{jI(kG kK lY mH mI mY nN nO) qT(Ji Jq Js Mj Qd) VjbQ gCkQ lWjY} Li{mM(dR eC Kq Tn) nR(Af Bn) kQ(lY Pf) MaVj MeTk OrnI aCmW bSgP dEcC} Uk{mW(Oz Qe St Vt) Pk(lX nC) mM(Im St) NrdA NdaN YjaH QbdJ JqaW VtmF} Vv{Bg(eD jH jQ lN qX) Mz(eD jK jO lL lN) IjmM KqlN cEgW} Mf{fR(Eq Fn Lp Vs Zq Tm) Si(iH oH St) Rv(Gd Ug)} Tl{Il(Hr Ki Nt) Yj(aI cE Pg) Ub(Id Ue) CvHp JeKi PaPd} Vu{mW(Ju nA Ua) nI(aO Or) BajE BnnR GznA IpnO RzoF cBlY} gP{Ld(Oz Pc Pd) Mt(Oz Pb) ArTk ChCq MqMu QbfP PbPf} Em{nN(aC bE Nk Pd) IlnA IpmE JmnJ PflY cIgC} bQ{Vj(Cw Gn Nd Pd Rz) GnRt QbVi SsRx WdcR} aI{Hl(Mh Mu Oy) Tj(Fi Yf) MtOz RxaM PhnN} aW{Jq(Aj Aw Ax Cs Ed Ms) ArTk InlN} eM{Fn(cR dG hF Mq oK) EdQz SskR cRdD} Id{Mx(Vz Wb Yh) Qb(Wf Yh) VzNy} Jt{Rm(hA jE rC) Qh(dJ jE) DcjE} nA{Ed(Qz Ur) Ex(eC Rf) DcGz jMkF} lN{mS(Jg Jm Ma Mm) Jp(nC nH)} Je{Va(Ip Rm) EqKk ZqNy KiVi} Rx{AsbE HrdF HuaM JmUg UwVw} Oz{Mt(aQ Gp) dJ(Pf Yd) nRqY} mW{AxPd BnQh DcOy NyPb aUdR} Qb{SicR ShNx JdfP VioF} Vt{cV(nL nN) UnnR PfkP} Tn{AjnI CtnO dAmZ} Il{FnSj NtXa NdYl} Tk{ArbL CseF FrcP} Oe{jY(nB nK) lWjH} Va{AlHu ChNx HrOu} Vj{cT(kS Pd) CqMa} Pg{hAkK mPlM mZjU} bE{aM(Gh Rv) LvoP} eC{oQ(cW Qv) GzkC} nN{CvUg ExRg NteF} lY{Pf(cB Ur) OklK} Ba{jE(Qh Rg)} Dr{UxiO cIgC} Yf{TjRv PbdJ} Sh{GpRm KkRj} Ny{AnHp mPlM} aC{YebP UyiO} nR{BnSt PcjL} mM{HvjI IjUn} BbOyoP ExNxoO FrdDkG MxSiiZ HuVibP IpZwbJ IuJkTm YgRmhG JgmZqY SsgCkQ JjPknT Constrained panels with 2 analytes, where 1.0E-5 >= 'model p-value' > 0. Contains 38 panels of 145,307 total panels evaluated. : Yi(kC kF kG kI kK kN lX lY mM mS mT mU mW mY mZ nA nB nC nF nH nJ nN nR nT nU) Lj(Ar bN dA dJ gP hG iJ kQ) Oa(bN gP kQ) BgNg YjoE Constrained panels with 2 analytes, where 1.0E-4 >= 'model p-value' > 1.0E-5. Contains 91 panels of 145,307 total panels evaluated. : Oa(aQ aR aU aW bS cA cK cP cY dA dJ eC hG Jt Ng nW oH oN Pd Ph Uk) Lj(aE aI aQ aR aV aW cP cV cY eC Gp nY Ph St Uk Up Th) Is(Hv Ih Ik In Jn Jr Jt kP lY Ms nC nH nL Nr Nt Wm) bN(Fa Li Pz Qa Qb Wm) Ng(Cq Tn Ut Yi) oE(Hl Vi We Yf) Th(Qa Yi Wm) Fb(jH jU qU) Vj(bZ Tr Yi) fA(cB dA nO) Fa(gP kQ) Vq(nA nJ) Vw(bZ Pz) YfnN YiKl JqaW RzhB nOoW Constrained panels with 2 analytes, where 1.0E-3 >= 'model p-value' > 1.0E-4. Contains 386 panels of 145,307 total panels evaluated. : Is(aI Aj aQ aV aW bN cA Ch cK cR Ct cV dA dJ Ed Ef gP Ib Ic Jd Je lK oE QT Rc Sh Uf Uk Un Up Vs Vv Tk Th) bN(Ax Cs Ed Et Fn Fw Hb Hr Ir Jm Jq Jr Js Ko Ld Lx Nn Nq Nr oE Qc Qd Qe Qh rC Rg Rm Ss St Uh Uk Ut) oE(aW cE Fb Fn Gc Gn Jq kQ Ld Li mM Mt Nd Nr Oh Pa Pz Qb Qh Rg To Vj Yi Wm Th) Oa(Ar Gp Ha Ic Ik iZ Js kE kP mM mS mU mW mY nA nB ND Pb Up Ti Th) Wm(aI aQ cP cZ dA dD dJ Ed Gp Hb Hx Jq Li oH Qa Qb Qc Qd Uk Yl) Yi(aI aR bJ cP EF Ib Ii Ik iO Je Jh Kj Kn Mg Nt Pd Qt Ss Vw) Uk(aI aN aW Cq dJ Ed Fa Fb Il Ir Iu Jm Jq Lx Pz Qa Qb) Fa(aP aW aY cA cK cP cW dJ dN Gp Ik Ng oH Pd Tk) Ng(bQ Co Dk Fb Fy Kq Qh Tr Tt Ua Uc Vq) Qb(aQ aV aW Ax cV dA dJ fP gP Ic Si Up) Qa(aQ aR aW aY dA dJ gP mW Vj Vw Zq) Lx(aQ aV aW aY cA cP dA gP Yl) Li(bS dJ gP kQ mW Pb Ph Up) bZ(Eq Hl Mu Rx Rz Wd Yj Zq) Ed(aQ aR Fb gP Hx nD Th) Nn(dA dJ Gn Sh Vj Vz Tm) Yl(Ld lW lY Nd nN Oh Ow) Oh(dJ gP Hl Sh Si Vj) Ow(Hl Sh Si Vi Vw Zq) Vu(mM mW nA nD nI nO) Nr(aV bS cA cK dA) Ik(Cs Wh Yh Tl Xa) Pf(cA cK Pb Si Vw) lY(aI Ok Pz Qc Up) mM(hB Kq Ok St Tn) Ax(gP Hx oH Pd) Th(Hx Ma Mj Oz) Fb(eC jE lN Ss) Vj(bQ Hx Ma Oz) bH(mU mW nN nR) mZ(Mz Ok Tn Tr) Tj(oD oV pI) Mf(fR Si Va) Hl(aI bE Hx) Yj(nR oP Tl) Lj(Ic iZ Ti) Rg(bS cA cK) Vw(Cq Il Kk) dJ(Oz Qh Rm) gP(Cs Ld Mh) Sh(aI Rm) Up(Ir nA) Uw(lX nJ) nN(Or Vz) nO(eQ Tn) AjBg BoWn CskQ NcqT IlRz HbaW JeVa WcnA KqkE RvaC VqkC aQcY cAcE cReM dDdU Unconstrained panels with 3 analytes, where 0.0E0 >= 'AUC p-value' > 0. Contains 50,000 panels of 24,406,229 total panels evaluated. : Yi{Vj(AA aC aD aE aF aG aH aI aK aL aM AN aO Ap aQ Ar aS aU aV aW aX aY bA bB bF BG bH bI bL bM bN bO bP bQ bR bS bU bV bW bX bZ cA cB cC cD cF cH cJ cK cM CQ cS CT cU Cv cW cX cY cZ dA dB dC dD dE dF Dg dI DK dL dM dN Dp DR Du EF Em Eq Et Ex Ez Fa Fb Fd Fi Fn Fp FR Fw Gb Gc Gd Gh GL Gn GP Gz Ha HB HC HF hG Hl Ho Hp Hr Hu Hv Hw Hx iA Ib Ic Id iH Ii IJ Ik Il Im IO Ip Iq Ir Is It Iu Iv IZ Jd Je Jf Jh Ji Jk Jm Jn Jo Jp Jq Jr Js Ju Jv Jy KC Kd KE KF Kg KI Kj Kk Kl KN KO Kp kQ KR kS Kx Ky Kz Ld Lh Li Lj Lp Lt Lu LW LX Ly Lz Ma Mb Mc Md ME Mf Mg Mi Mj Mk Ml Mm Mp Mq Mr Ms Mt MU MW Mx MY MZ NA Nb Nc Nd Ne Nf Ng NH NJ Nk nL Nm Nn NO Nq Nr Ns Nt Nv Nw Nx NY Oa OE OF Og Oh Oi OK Om On oO Op oQ Ow Oy Oz Pa Pb Pc Pd Pe Pf Pg Ph Pi Pj Pk Po Ps Pz Qc Qe Qg Qh Qm Qn Qu Qv Qw Qx Qy Qz Ra Rb Rc Rf Rg Rh Ri Rj Rm Rt Ru Rv Rx Ry Rz Sf Sh Si Sj Sr Ss St To Tr Tv Tz Ua Ub Uc Ud Ue Uf Ug Uh Uk Ul Um Un Uo Up Ur Us Ut Uu Uv Uw Uy Uz Va Vb Vc Vh Vi Vo Vp Vq Vs Vt Vu Vv Vw Wb Wd We Wf Wg Wh Yd Yg Yh Yj Yk Yl Zq Zw Zx Tm Tl Xa Wm Ti Th tF Yf) nH(AA aC Ad aF aG aH Aj aL aM AN aO aQ AR aS aU aV AW aX aY BA bB Bc bF Bg bH bI bJ bL bM BN BO bP bR bS bU bW bX cA cB cC cD cE cG CH cK cL cO cP cQ CS Ct cU cW Cx DB dC dD DE DG DI dJ dL Dp dR Du EF Em Eq Et Fa Fb Fd Fi Fn Fp Fr Fw Fy Gc Gd Gh GL GP Gz Ha HC HF hG Hr Hu Hv Hw Hx Ib IH Ii iJ Ik Il Im In Io Ip Iq Ir It Iu Iv Iz Jd Jf Ji

Figure 25 Continued

Jj Jk Jn Jo Jq Jr Jt Jv Jy KC Kd kF KG KI Kj kK KN KO kP kQ kR KS Ky Kz Lp Lt Lu Lv LW Ly Mb Mc Md ME MF Mg mH MI Mj Ml MM Mn mP Mr mS MT MU Mv mW My Mz NA NB Nc ND Ne NF Ng Nh NI NJ NK NL NM NN NO Nq nR Ns NT Nu Nv Nw Nx NY Oa Oe Og oH Oi oK oN Oz Pa Pb Pc Pd Pe pF Pg Ph Pj Pk Po Qh Ql Qm Qy Rc Rg Rh Ri Rm Rv Rx Ry Rz Sf Sh Sj Tt Ua Uc Ue Uh Uo Ux Vo Vv Vz Wb Yg Yh Yk Yl Zq Zw Ye Tm Tl Xa Tj Th) nA(aC Ad aF aG aI aJ aK Al aM AP aR As aX bA bB bC bE BG bH bl bM BN bP bR bV bW cA cB cD ChcL CO Cp CQ cR Cs CT CU Cv CW cZ dA DB dC DD De dF dH dJ DK dL Dp DR Du eF Em Eq Ex Fa Fb Fd Fn fP FR Fy Gd GL Gn Gz HC hF HI Ho Hq Hu Hv Hw Hx iA Ib Ic Id iH Ii IJ Ik Il ln IO IP Iq Is It Iu IZ Jd Je Jg Jh Ji Jj Jk Jl Jn Jo Jq Js Jt Ju Kc KF Kg KK Kl KN KO KP Kq kR kS Kz Ld Lh Li Lj Lt Lv IX lY Mb Me Mf mH Mk Ml mM Mn Mr MT Mu MW Mx My mZ Nc ND Ne NF Nh NI Nk Nl NN nO Nq nT NW nY Oa oE Of OH Ok Om On oO Op oQ Ou Oz Pa Pd Pe Pf Pg Pj Pk Po Pz Qa Qc Qe Qg Qh Qt Qu Qv Qw Qx Qy Qz Ra Rc Rh Ri Ru Ry Rz Sj Sr Ss To Tr Tt Tv Tz Ua Ub Uc Ud Uk Ul Un Uo Up Ur Us Ut Uu Uv Uz Vc Vh Vo Vp Vs Vt Vu Vv Vz Wb Wd We Wg Wh Yg Yj Yk Yl Zq Zw Zx Xa Wm Tj Th Yf) Ng(AA aC aD aE aF aG aH al AJ aK aL aM aN aO aP aQ AR aS aU aV aW aX aY aZ bA bB bC bE bF bG bH bl bJ bL bM bN bO bQ bR bS bU bV bW bX cA cB cC cD cE cF cG cH cl cJ cK cL cM cN CO cP CQ cR cS CT cU cV cW cX cY cZ dA dB dC dD dE dF dG dH dl dJ DK dL dM dN Dp dR Du EF Em Ex Ez Fb Fd Fi FP Fr Gb Gh gL GP Gz Ha HC hF hG Hp Hu Hv Hx iA Ib Ic Id iH IJ Il iO IP Is It Iv IZ Jd Je Jf Jh Jj Jk Jm Jn Jr Js Ju Jy Kk KN Ko kS Lh Li Lu IW Mb ME MF Mg ml Mk Ms Mu Mw Na Nd Nc NJ nK nL Nn nO Nq Nr NT NU nW nY OE OF Og OH oK Oy Oz Pa Pb Pc pF Pg Pi Pj Ps Pz Qb Qc Qd Qh Qm Qn Qt Qw Qy Qz Rc Rf Rv Rx Ry Sf Si Sr Ss Tz Ua Ub Uc Ue Ug Uk Um Un Uo Ut Uv Uw Uy Va Vb Vh Vi Vp Vq Vs Vv Vw Vz Wb Wc Wd We Wf Wh Yg Yh Yk Yl Zw Ye Tm Tl Xa Wm Ti Th tF Yf) oQ(Aa aC aD aE aF aG aH al aJ aK aL aM aN aP aS aU aV aX aY bB bE bH bM bP bX cB cC cF cH cJ cL cM cN cO cQ cU cW cY dA dB dC dD dF dJ dM dN Dp Du Ed Ex Fb Fi Fn Fr Fy Gc Gl Gz Hb Hc Hr Ic Id Im In Io Ip Iq Ir Is Iv Jg Jn Jr Jt kC Kd KE kG kI Kj Kk KO kP Lj Lt Lv IW Ly Lz Mb ME MF Mg MH ml Ml MM mP mS mT mU mY Na NB Nh nI nJ nK nL nO Nr nT Nu Nw Oa Og Oi oO Op Or Oy Oz Pd Pe Pi Pz Qa Qb Qc Qh Qt Qu Qw Qx Qz Ra Rb Rc Ru Rv Ry Rz Sf Sj Ss Tn Tv Tz Ub Uc Ud Uf Ug Uh Uk Ul Um Uo Ur Us Ut Uu Ux Uz Vb Vc Vi Vp Vv Vw Wb Wc We Wf Wg Yd Yh Zw Wm Tj Ti Th Yf) ml(AD aE Af aG aH Aj AL aM aN As Aw aX bE bH bl bJ bM bN bO bP bR bS bU bW bX cA cF cG cJ cK cL Co cT Cw Cx dA dB dC dD DE dG dl dJ DL Dr Eq Et Ex Fc Fd Fi Fn Fy Gc Gh Gz Ha hB Hc hF Ho Hr Hx Ic Id Ih iJ iO Ir Is Iu iZ Je Jf Jj Jm Kd kE kG Kj Kn kO kP LW Ma Mb Mc Md mE Mg Mi MT Mu My Na nC ND nF Nh NI nK NL nM Ns nW Nx nY Of Oi Om oN oO Oz Pc Qe Qu Qv Qw Ra Rb Rc Rf Rj Rm Rt Ru Rv Rz Si Sj Ss Tn Tr Tt Ua Ud Ug Uk Ul Um Un Uo Up Ut Uu Uw Ux Uy Uz Vc Vh Vo Vp Vq Vs Vt Vu Vv Vw Wb Wg Yd Yg Yh Yk Zq Ye Tm Ti) nK(aA AD aE Af aG aH Aj AL aM aN aQ As aU aV Aw bB bE bH bl bM bN bO bP bR bS bU bW cA cC cF cG cJ cK cL Co cP Cs CT cU Cw Cx cY dA dB dC dD De dG dl dJ dL Dp Dr Ef Ex Fc Fd Fi Fn Fy Gh hB Hc hF Ho Hq Hr Hv Hx Ic Id IH iJ Ir Iu IZ Je Jf Jv Kd kE kG Kj Kn kO kP Lh Lj LW Ly Ma Mb Mc Md mE Mg Mi MT Mu My Na ND nF Nh NI NL nM nO Ns nT nW Nx nY Oi Om oN Pb Qe Qu Qv Qw Ra Rb Rc Rf Rg Rh Rj Ru Rv Si Sj Ss Tn Tt Ua Ub Ud Ug Uk Ul Um Un Uo Up Ut Uu Uv Uw Ux Uy Uz Vc Vh Vo Vp Vu Vw Wb Wc Wg Yd Yk Zq Ye Tm Ti) nI(aA AD aE Af aG aH AL aM aN Aw bB bE bH bl bM bN bO bP bR bS bU bW bX cA cC cF cG cJ cK cL Co Cq CT cU Cw Cx dA dB dC dD DE dG dl dJ DL Dr Eq Et Ex Fc Fd Fi Fn Fy Gc Gh hB Hc hF Ho Hr Hx Ib Ic Id Ih iJ iO Ir Iu IZ Je Jf Kd kG Kj Kn kO kP LW Ly Ma Mb Mc Md mE Mg Mi MT Mu My Na nC ND nF Nh Ni NL NM nN Ns nU nW Nx nY Om oN oP Oy Oz Pb Pd Pz Qe Qu Qv Qw Ra Rc Rf Rg Rh Rm Ru Rx Rz Si Sj Ss Tn Tr Tt Ua Ud Ug Ul Um Un Uo Ut Uu Uv Uw Ux Uy Uz Vc Vh Vo Vp Vq Vs Vu Vv Wb Wg Yd Yh Yk Zq Ye Tm Ti) nU(aC aE aF aJ aK AL aM AN aP aR aW aY bB bl bJ bN bO bP bQ bR bS cA cB cJ cK Co Cs CT CU cW cZ Dd De dF dL Dp Du Fb Fn Fp Fr Fy Gd gP hB hG Hx Ic Ih Ii Ij iO Ir Is It iZ Jf Jj Jl Jo Kc Kd Kg KN KS Kx Kz Ld Lh Lw Ly Ma Mc Md Mh Mi Mj Ml Mq Mt Mu Mx My Nd Nf Ni Nj NI nM Nn Ns Nt Ny oO OP Oy Oz Pd PF Po Pz Qd Qt Qu Qv Qw Qy Ra Rb Rc Rg Rh Rm Rt Rv Rx Rz Sr Ss Tr Tv Tz Ua Uc Ud Ug Uh Uk Um Un Uo Up Ur Ut Uu Uv Ux Uy Uz Vc Vi Vp Vu Vv Vw Wb Wc Wd Wf Wg Wh Yg Yh Yl Ye Tm Wm Ti tF Yf) mE(aA aD aE aG aH Aj AL aM As Aw aX bB bE bH bl bM bN bO bP bR bS bU bW bX cA cF cG cJ cK cL Co cP Cs CT cU Cw Cx dA dB dC dD De dG dl dJ dL Dp Dr Eq Et Ex Fc Fd Fi Fn Fy Gh hB Hc hF Ho Hr Hv Hx Ic Id IH iJ Ir Is Iu iZ Je Jf Kd kG Kj Kn kO kP Lt LW Ly Ma Mb Mc Md Mg Mi Mt Mu My Na ND nF Nh Ni NL nM Ns nW Nx nY Oe Oi Om oN oO Oz Pc Qe Qu Qv Qw Qz Ra Rc Rh Rj Rm Ru Rv Rz Si Sj Ss Tn Tt Ua Ub Ud Ug Uk Ul Um Un Uo Up Ut Uu Uv Uw Ux Uy Uz Vc Vh Vo Vp Vq Vt Vv Vw Wb Wg Yd Yh Yk Zq Ye Tm Ti) nL(aA aD aE Af aG aH Aj AL aM aN As Aw bE bH bl bM bN bO bP bR bS bU bW cA cB cF cG cJ cK cL Co cP Cq Cs cT Cw Cx dA dB dC dD De dG dl dJ dL Dp Dr Ef Eq Et Ex Fc Fd Fi Fn Fy Gh hB Hc Ho Hr Ib Ic Id Ih iJ iO Ir Is Iu iZ Je Jf Kd kG Kj Kn KO kP Lj LW Ly Ma Mb Mc Md Mg Mi MT Mu My Na ND nF Nh Ni NI nM Ns nT nW Nx nY Of Oi Om oN oO oP Oz Pb Qe Qu Qv Qw Ra Rc Rh Ri Rj Rm Rt Ru Rv Si Sj Ss Tn Tr Tt Ua Ud Ug Uk Ul Um Un Uo Up Ut Uu Uw Ux Uy Uz Vc Vh Vo Vp Wb Wg Yd Yk Zq Ye Tm Ti) oO(aC aF al aK aL aM aN aO aS aZ bA bB bC bE bF bJ bO bP bQ bV bZ cC cE cl cL cO cP cQ cR cW cY cZ dA dC dD dF dH dl dJ dM Du Em Fa Fd Fi Fn Gc Gd Gh Gl Ha Hb Hc Ho Hw Ij lk Il lm Ip Ir Is It Jd Jg Jh Jn Jq Jt Jv Jy KC KE KG Kj kK KI KO kP Kq Kx Kz Lh Li Lj Lp Lv IW IX Lz Mb Mg Mh Mj Mk Mm Mn mP Ms mU mW Na nB Nd Ni Nk Nl Nm nT Nx Of Og Ok On Or Ou Pd Pe Pg Pj Qb Qe Qm Qw Qx Ra Rb Ru Rv Sj Sr Ss Tn Tz Ub Uc Uk Um Up Ur Us Ux Uy Vi Vp Vt Vw Vz Wd Wf Yd Yh Yj Zq Tl Xa Wm Ti Yf) nD(aA aD aH AL aM aN Ao Ap Ar As aU Ba bE bl bJ bM bO bR bS bW cA cF cJ cK Co Cs cT cU Cv dA dB Dd DE dH dl dK dR Eq Fc Fd Ff Fr Fw Gh gL Gp HB Hc hF Hw Ic Id Ij Im Iv iZ Jd Je Jf Jh Jp Jq Kd KE Kj Kn kO Kp KS Ky Lh Lt LW IX Ma Mb Mc Md mH Mi Mj MM mP Mr Ms MT Mu Mw My mZ Na Nb Nd NF Ni Nj Nl NM Ns nT nY Oa oF oH Oz Pc Pf Pi Pz Qe Qu Qx Ra Rh Ru Rv Rz Si Ss Tt Tv Ua Ud Ug Uh Uk Ul Um Un Uo Ur Uu Uw Uz Vb Vc Vi Vp Vu Vw Vz Wg Wh Yd Yg Yk Yl Zq Ye Tm Ti) oP(aE aG aK aM aN aS aX bA bL bQ bZ cB cE cl cL cM cR cT cU cY dA dD dF dH dJ dK Dr Du Ed Eq Ez Fn Fw Gh Ha Hf Hl Ho Hr Hu Hv Hw Ib Ic Ij Ik Il In Ip Ir Is Iu Jd Jf Ji Jn Jo Jp Ju kC kG Ki Kj Kk Kn KO kP Kq Kx Ky Lh Lj Lt IX Ly Mf Mh Mk Mp mS MT mU Mv Mw MZ NB Nd Ne Ni NJ Nk NI nO Nr nT Nu Nv Og Ok On Or Ow Pd Pe Pg Pj Qb Qc Qe Qg Qh Qm Qz Rb Rc Rt Ru Rv Rx Ry Si Sj Tv Uc Ud Ug Ul Um Un Uu Uw Ux Uy Uz Va Vb Vc Vh Vi Vo Vs Vt Vv Vw Wc Wd Wg Wh Yg Yh Zw Ye Ti Th) lW(aD AL aM aN Aw bE bH bl bJ bM bN bO bP bR bS bU bW bX cA cF cG cK cL Co cP CT Cw Cx dA dB dC dD De DG dl dJ dL Dp Eq Et Ex Fc Fd Fi Fn Gh Hc hF Ho Hq Hr Hv Hx Ic Id IH iJ iO IP Ir iZ Je Jf Kd kE Kn kO kP LW Ly Ma Mb Mc Md Mi Mt Mu My Na nC Nd Nh Ni NI nM Ns nW Nx nY Oa Om oN Oz Pa Pc Qe Qu Qv Qz Rb Rc Rg Rh Rj Rm Rt Ru Rv Si Ss Tn Tr Tt Ua Ud Ue Ug Uk Ul Um Un Uo Up Ut Uv Uw Uy Uz Vc Vh Vo Vw Wb Wd Wg Yd Yh Yl Zq Ye Tm Ti) nM(aD aE aG aH aK aL aM aN aQ As aU aV Aw bE bH bl bJ bL bM bN bO bP bR bS bW bX cA cF cG cK Co cT Cx cY dA dB DD De dl dJ dL dR Et Fb Fc Fd Fi Fn Fr Fy gL Gz hB Hc hF Hr Ic Id iJ Ir iZ Je Jf Jh Kd Kk kO kP kQ Lw Ly Ma Mb Mc Md mH Mi mP Ms Mt Mu My Mz Na Nd Ne Nh Ni Nl nO Ns nW Nx nY oH oN pF Pz Qu Qz Ra Rc Rh Rm Ru Rv Rx Si Ss Ua Ud Ue Uf Ug Uk Ul Um Un Uo Ut Uu Uy Uz Vc Vh Vo Vp Vs Vv Wb

Rv Ry Sh Ux Uy Uz Va Vb Vc Vh Vi Vw Wc Wd We Wf Wg Wh Yg Yh Ti Yf) Ry(aA aC bQ dR Fw iA Ij Ld Lh Lx Lz Mf Mj Mq Mt Mw Nd Ni Nk Nq Oe oH oP Pf Vh) aC(Em Gb Gd Gn Ho Lt Ps Rt Ux Vh Wd We Wf Wh Yg) Ed(Ps Rt Ur Ux Vh Wd We Wf Wh Yg Ti Th) Pf(Fn Jf Op Or Ri Rz Sh Uy Vb Wb Ti Th) Up(Dc Et Ir Jm Kq Nw Ok Qe Qh St Vt) eC(cW dI Fn Ib Nk Nt Oe Qv Ri) Lx(Dr Lp Ri Yg Yh Ti) Nk(Fc Fi Ho Ru Rx Uy Va) Wb(Cq Ij Jm Nw Ok Uc) Sh(Co Ij Om Qe Qh Uc) Tn(cR cX Op Rz Ti) Vh(cB Fn Lv Pd Ri) Vi(bQ Fr Hr nY St) Jm(fR Rt Rx Yg) Dr(An Cq Pb) Tr(Kg Kj Oy) Zq(Im Qe St) We(bQ Nw Ub) Wf(Hx Lj Oz) Eq(Oz Pb) Mf(Ho Rx) Ib(Lh Wh) Ps(cX Mb) Nw(Sj Va) Ny(Fi Op) Vb(Cw Ma) Pg(IK qX) TiIm ExIu GndR NrYk NcjI HoJe UbfR UcUx YgLi SfSt KqOp RvnY} mP{Ry(aP aQ Bc bQ cR Cu Dk DR Fw Fy iA Ij Js Kq Ld Lh Lx Lz Mq Mt Mw Nb Nc Ne Nq Nr Oe oP Pf Qx Vh Yh) Nb(Dr Gd Gn Lt Op Ps Rt Ru Rv Sh Ux Uy Uz Va Vc Vh Vw Wc We Wf Wg Wh Yg Yh Yk Yf) Up(Dc dH Et Ih Iq Ir Jm Kk Kq Lx Mj Nw Ok Qd Qe Qh St Uc Vt Zw) Lx(Eq Fi Ri Vb Vi Vw We Wh Yg Yk Zq Yf) Pf(Fn Op Or Ri Rz Sh Uy Vb Wb Th) Ed(Ps Rt Ux Vh We Wf Wh Yg Ti) Wb(Cq Ij Jm Nw Ok Oz Uc) Sh(bQ Co Ij Qe Qh St Vi) Yg(Fn Li Lj Nr Oz) fR(Je Jm Mf Nk Ub) Tn(Aj Ib Op Rz) St(Gn Sf Vi Zq) We(bQ Nk Nw Ub) Wh(cQ Ib iO Oz) Vh(cB Gb Iu Ri) Nc(jI Vi Xa) Va(Dk Ip Nw) eC(Ex Fn Gz) Cq(Gd Zw) Cw(Rz Vb) Nr(Yh Yk) Tr(Oy Wc) Zq(Im Qe) Ps(cX NI) Op(Kq Ny) Vi(Nk Ub) DeQh DuNd ExIu GhMf GnbQ MaVb UcUx SiOm SjNw SrUk WcbA JmRt RvnY NvlM UyoP} mW{Li(aC aE aO aV Aw bE bX cB cE cG cM cQ cR cY dA Dg dH dR eC Ez Fa Fn Fw gP Jc Jf Ju Jv Kp Kr kS oF oH oN oV Ql Qw Rc Rf Rg Rh Ri Rj Rm Tn Ub Uk Up Us Vo Vt Vv Yh) Lj(aE aJ Aw bX CQ cR dC dG eC Gb Kf Ko Ql Rf Rg Rh Ri Rj Rm Uk Ye) Uk(aA Ih Ii Jm Jn Nl Oy Oz Pb Qb Qe Qh St Vt) Up(Bc Et Fr Ij Jm Nw Oe Ok Qe Qh St Vt) Ri(aJ aM Ax Fr Lx oO Pf Vh) St(Af As Bn Cp Dc Gn Lv) Ax(bX Hr Hx Pd Rg Rh) Jm(Dr fR Rt Rz Va Yh) Cq(Dr Sh Vo Yh) Hr(Lp Ps Tn Xa) Qb(eC fP Ho Rf) Oy(Cv Dc Tr Uc) Pf(Rz Yg Yh Yf) Fr(eC Rg Rj) Nk(pK Ry We) Wh(Fn Ng Rg) Vt(bQ cV fR) Pd(Tn Vi Wm) Ms(oD oV) Sh(Oz Rm) We(bQ Ub) Qh(Af Bn) cR(pK Tn) cQ(aE lW) BcpH DriO EdWf EqOz FaaY MfRx NbVi NcjI HoQx UcUx IbJk TrRz WbRm PclO PglK aUdR eCoQ} kC{eC(Aa aI dI Ed Ex Fn Gz iH kO nC nH nL Or Rh Vt) Ho(Kx Lz Ma Mh Mq Mx Pf Qx Ra Rf Rh Tr Tt Wm) bQ(Dr Gh Ps Si Wc Wd We Wh Yh Zw) Wm(aI Fn Ip Lp Qh Ri St Th) Si(Fy Ij Ma Mx Pf Qx Tn Tr) Lx(Lp Ri Rz Yg Yk Tl Xa) Ry(cR Dr Mq Qx Ra Rf Rh) Dr(As Cq iO Jm Lj) Wc(bA Bc cT Mh Tn) Lp(kN Ld Mq Qx Ra) Pf(Gn Ri Rz Vw We) Yf(Cv Dl Mf Nl) Tr(Eq Oy Rz Uy) Yh(Ih Jm Li Ny) Wh(Aj Ng Nl Oz) Up(Dc Nw Ok Vt) Gn(Nr St Tn) Mf(Rv Rx Xa) Mx(Rv Rx Wf) Nk(Hp Ru Vi) Sh(Jm Rm Uc) Lj(Ha Ri Uk) Rh(Fd Va Vw) Vh(Ib Lv Ml) Bo(aC bE) Cq(Gd Wb) Eq(Oz Tn) Nb(Vi Wf) Nc(jI Xa) Ij(Ps Tl) Zw(Iu Jm) Li(Rg Yg) Ru(Jm Nd) Ri(Co Cw) Rf(Ex Uy) Va(Je Vt) AxHp DcRt GhTn GcNw NrWe MaRz MhZx MlRv UcVw TtUy WbRm StVi UxaC VtcV} oO{aC(Em Fc Gb Gc Gd Gn Lp Lt Ps Ru Rv Ux Uy Uz Va Vb Vc Vh Vw Wc Wd We Wf Wg Wh Yd Yg Yh Zw Zx Ye Tm) Ri(aI Ao BG bL cE Ch CQ cU Dc Dk Ex gP Gz hF hG iA Ib iJ iP Kk nY oF Or Pf) bE(Dr Du Ex Lp Lt Rx Ux Wf Yg Yh Yk Tl) Mb(Du Eq Ex Ps Rx Ry Va Vh Wh Yd Yf) Jm(Fi Gn Rt Ry Sf Wb Yg Yk Ti) Dr(bQ Ed Hu Kk Nb Nd Om) Ry(Ij Jy Nk Nx Vh Wf) Mf(Ho Rx Wc Wh Ye) Yg(Ho Ib Ks Nx Og) Yh(Ks Ms Nx Ny Og) Up(Cq Kk Nw Ok Vt) Vi(bQ Nb Om Tn) eC(bG nH Oc Pa) Tr(Nt Oy Vv) Sh(Ij Qe Qh) Wf(bQ cY Iu) Nw(eQ oV pK) Eq(Nl Oz) Nd(Em Tm) Ho(bN Je) Ip(eQ fR) Wh(Fn Nl) Ks(Yk Zq) Nx(Gz Uy) dK(Rt Tm) ThPf GnSt NcXa UbRx UcVo IjOp WebQ} lW{Ip(Du Em Eq Ex Fc Fd Fi fR Gb Gc Gd Gn Gz Ho Hp Lp Lt Op Ps Rt Ru Rv Rx Ry Rz Sf Sh Si Ux Uy Uz Va Vc Vi Vw Wb Wc Wd We Wf Wg Yd Yk Zq Zx Ye Tm Tl) Cq(Dr Du Gd Sh Va Vw We Yh Zw Tm) Yh(bA bQ Dc Ij Jl Mx Ny Qh Rm) Nw(Gc Gn Lp Rt Si Sj Up Vi Zq) Jm(Dr Du Fi Rz Sh Wb Yk Yf) Yg(Fn Ij Li Lx Ok Qh Vt) Yk(Ij iO Ne Nl Pb Qh) Nk(Fd fR oD Ry Vi) aC(oD pH pK Rv Ux) Lp(Ij Ld Lx Mx) Dr(cE iO Mx) Nd(Ry Sh Vb) Uc(Gd Sh Vw) Tn(Gn Rz Uy) We(bQ cE Ub) Rv(Fn Hu Mf) Up(Dc Kq Vt) pK(aK aL aQ) Th(fR Pf) Nl(Ps Yd) St(Vi Zq) Xa(bQ Js) Rz(bQ On) Vh(dE Fn) DcRt YfLx EqOz FiIj MqUy NbVi NcjI NeYd UbfR IbWh TrOy WbRm ZwcW QbRx OklK VtcV aQoD} Mf{fR(dA Dr Em Eq Fc Fi Fn Gb Gc Gd Gh Gn Ho Lp Lt nH Op Ps Ru Rv Rx Ry Sf Sh Si Sj Ux Uy Uz Va Vb Vc Vh Vi Vs Wc We Wf Wg Wh Yd Yh Yk Zq Zx Ye Tm Tl Ti Th) Si(aI bV cD Et Hx iH nI nK oH Oz Qb St Tl) Hp(kK mT mY nC nF nH nL nM nR nU) Rx(aQ kK mE mI mY nK nL nR oQ Ug) Va(aG aH aI Hx nK oH Qw Rv Th) Ho(kI mF mY nF nK nU oP oQ) Rv(Gd mE mF mH mI Ug Uu) Xa(kK mE mF mI) dA(eQ oD oV pK) oQ(Dr Wc Wh Ye) oH(Eq Rt Sh Wd) Gh(mI nI nK) We(mF Ms nI) Ry(nH nI nL) nR(Rz Uy Vb) Wh(nF oP) Op(aH aI) cB(pH pK) nK(Wc Wf) oV(Bo gP) IdTl IneQ ShaH ZqaI RzoF VwbV} eQ{aK(An Ap Ar As Aw bA Bb cI Co Cs cT Cv Cw Dg Dl Hr Ni Nk) Fn(aF aO cX De eC Gl gP Hv kG Ml nC nH nL Pa Pb) dA(aY cI Cq cX hG Im Iq Jd Ks Li Nc Ne Pb Pk tF) cB(aO bA Bo cI Db hC Jp Ms Nk Nq tF) nC(aE aP bE cM cP cW Hb hG iZ kO) kQ(aC Hx Jj Ms Nc Nt oV Oy) Ip(bP cP Db Hc Mm Na Nt) aE(Ct Ha Hc Lj Mz Nk Pk) Ms(cR dB hG Mb My) eC(aV cW dI dJ Na) Nw(Db gP Jp Mm) aC(Bo Co Dl Mg) aI(Af Aj Ao Bn) nH(cM cP kI kO) hG(Ao Bo Cq gP) Cq(aV In) Nq(aV dR) Nk(Ih Iq) Ko(cI Dg) Pa(bA cT) gP(Lh Mb) AxcP BbNt CpNv NoLi LuNa HbcI HccU IqcR bEoK} Oz{dJ(Dr Du Em Eq Fd Fi fR Gb Gc Gd Gh Gn Hp Lp Mt Op Ps Ru Rv Rx Ry Sf Si Ux Uy Uz Va Vb Vc Vh Vi Vw Wc Wd We Wf Wg Wh Yd Yg Yk Zq Zw Zx Ye Tl Xa Yf) Eq(bP kF kI kN kO mE mF mI mT nB nC nF nK nL nM nR nU oP oQ) nI(Em Fi Gn Lp Lt Ry Sh Wf Wh Yg Yh Yk Zq) Wh(bJ Je kG Kn mH mT mY nC nH nL) mE(Du Em Lp Rx Wf Yh Yk Zq Tl) bP(Dr Gc Wb Wc Ye) mI(Du Rt Yg Yh Yk) Rx(kF kK kN mT) mF(Du Yg Yk Tl) nH(Em Wd Zx Tl) Sh(nK nL nR) kF(Rz Yh Zq) Wf(kK mT) nR(Af Bn) nK(Dr Wb) oP(Fd Zq) BopH ThTm YhkN RvmT bNrC} Jm{Rt(Ap kG kK kO mT mY nC nF nH nL nM nR nU oP oQ) Yh(kK kN mE mF mI nB nC nF Ng nH nK nL nM nU) Fi(kK kN mE mF mI mY nB nH nR nU oP oQ) Yk(kK kN mE mF mI mY nB nH nR nU oP oQ) Dr(kF kG mE mF mI nI nK nL nM nR nU) Yg(kK mE mF mT nB nC nH nL nU oP oQ) fR(kI kK kO mE mH mT mY nF nM nR) mH(Fd Gh Gn Ru Rx Sj Wb) kI(Du Gn Rx Ry Sf Up) Du(mE mF mI oP) Sh(kF kG nB nU) Rx(kG kK mT Ug) Sj(nC nH nL) Rz(kN nR oF) Rv(mY nC nL) Up(mT nB nU) oP(Eq Gn Sf) Fd(nB nR) BoTk WbkF SfoQ WenR RynI VbnB VwcS nCpH} Cq{Wb(kF kG kI kN kO mE mF mH mI mT nC nF nH nI nK nL nM nU) Gd(kG kK kN kO mE mF mI mT nB nC nF nH nI nK nL nM nR) Va(Hx Je kG kI kK kN mE mH mI nC nF nH nI nK nL nM nU) Vw(cS Hx Il Lx mE mF mI nH nK nL nR nU) Ux(Il kN kO mT nB nR oF oH) nI(Du Fa Qb Ry Sh Ug Uy Vo) kK(Em Lj Ml Rx Ry Sh Vb) mE(Dr Du Rz We Yh Zw) mF(Du Rz Sh We Yh Zw) mH(Du Ry Sh Wh Zw Yf) kI(Ry Sf Uy Zx) oQ(cB fR Ri Th) aK(oD oV pH) Dr(mI nK) Hp(aM bP) Sh(kO nB) YhmI SfmY WdoH WhmT RzoF LjkF bNrC cBpK fRnB tFoD} Tk{Fa(aF aG aJ aK aL aM aN aO aS aV aW aY bA bF bG bI bJ bL bM bN bO bP bQ bR bS bU bV bW bX cA cB cC cD cE cF cG cJ cK cN cO cP cR cS cU cZ dA dB dG dH dI dJ dK dL dM dN eF Fp gL hC hF hG kR Kz My oH) Bo(Al Cs Dp Ih Ir Kx Li Lj Qb Qc Qh Rm St) Mz(aA aW bJ bU cI cN dJ eF iP kS Kz Rg Up) Ar(aM aN bJ bP cF cL dI eF gP hC) gP(Fr Hb Lx Mp Po Vt) Li(Aa cJ eF Me My) Cs(bN cJ My) Kz(Cv Dp Mw) eF(Fp Ha) BbMy DpcB FrcP MeIr MtRb} Lx{Id(Eq Gh Ho Lp Lt Sf Sh Si Vh Vi Vw Wf Yh Zq Zw Ye Tl Yf) Th(Gh Gn Gz Rv Rx Sf Si Vi Wc Wd Wh Yg Yh Yk Yf) Ar(kK nB Rt Rz Si Sj Vh Vi Vw Wf Ye) No(Rv Si Uz Vc Vh Wd Wf Wg Wh Yg Yk) Vi(bP bS cA cK iO kQ kS nC nU) Yg(cP cR fP iZ Nt Uh) Rz(iA iO kQ kR kS oN) Zq(hC iA Il kR oN) Ri(kF mE mT nB nU) Hr(Du Si Va Vh) Yh(bJ cP mF Ms) Si(bE cP Je) Lp(mE mF mI) Fd(cP Rh) Gn(iO Pe) Nt(Rx Yk) Ib(iB lL) Ry(nB oQ) Op(hC oN) Vh(Cs Je) NjfR ShRf SsnB WfnF XacP YeVs VvlM VwhC bNjH} Up{Vt(kF kG kI kK kN kO mE mF mH mI mT mY nB nC nF nH nI nK nL nM nR nU oP oQ) Nw(kF kG kI kK kN kO mE mF mH mI mT mY nB nC nF nH nI nK nL nM nR nU oQ) Dc(kF kG kK kN kO mE mF mH mI mT mY nC nF nH nI nK nL nM oP) Ok(kF kI kK kN kO mE mF mI mY nB nC nF nI nL oP oQ) Kk(kK mT nR Rz Vi Wb) Et(kF mI mT nU) Uc(kI kK mT nI) Kq(kG kN mF mI) Rm(mI mT nI) nR(Ax Cv Di) Ih(kN nB) Qd(lN mF) nU(Iq St) oP(aC Cv) MzeD HokI IjmI IrnB QemT TmnI UhkN eCmY} Pf{Th(Ex fR Gc Gh Gn Gz kF kG kI kK kN mI nB nC nH nK nL nR nU oQ Rt Rx Sf Si Sj Uy Va Vh Vi Vw Wc Wd Wf Wh Yg Yh Zx Tm Tl

Figure 25 Continued

Yf) Rz(al bV iA iO mE mF nC nH nK nL tF) Ri(kI kK mE mF mH ml mY nC nH nK nL) nH(bN cR Dr Gn Yh Yf) Vw(cR iO Kf nB Rx) Fn(fR kF nR nU) Nt(Gh Tm Tl Xa) Ng(Wd Wh Yg Ye) Si(bE Hr Hx Yf) Vt(kF kO mY nU) Gn(mH ml nK) Uy(mE mH mY) cR(mY nU Wd) dA(oD pH pK) Zx(Mb Nx) Lp(mF mH) Op(bE nB) mT(Vi Ye) pH(Ip Jf) DrkO YfmF UbnU HrTl HufR HxZq eCnB} iO{Dr(aX Ch Ef Fn Hu Iz Jh Kc kG kI kN kO Mg Ms mY nB Nd nF Ng nM Rz Ss Uu Ux Vw Th) aC(Ps Rt Ru Rv Sh Si Ux Uy Uz Va Vb Vc Vi Vw Wd We Wg Wh Yh Zw Tm Yf) Rz(bQ Fy Ij Js Ld Ma Mt On Qx Ra Rh Tn Tr Tt Zw Wm) Vw(cT Hx Ld Ma Rh Tr) Zw(Ib nI oH Ss Th) Hx(Rv Vi Wf Zq) We(cT fR mF nR) nI(Ux Wh Yg Yh) Th(Lj Xa Wm) mE(Em Rt Wd) mF(Em Rt Yh) Hu(Rv Yf) Xa(Je Ub) Oe(fR Ux) Vi(cT oF) GnMa MspK IbPs TrZq YhSs ShRm WckN} eC{mY(Ar bS cA cK cV cW dE Fn Mr nI Nj Nk No Ri Tr Ut) cW(kO nB nC nF nH nL nU oD oQ oV pH pK) nH(aI Bo dI Ed Ml Na Or Rh Ss Vt) kO(aI aK Bo dI dJ Ed Na Or Rh Ri) nC(aI Bo dI Ed Na Or Rh Ss Vt) nL(aI Bo dI Ed Na Or Rh Ss Vt) pK(aK cI cR dI Fn Hr Na Nk) oQ(Fn hG Nk Nu Or Pa Ri) nF(aI Bo Ed Or Rh) oV(aQ aV dA Fn gP) oD(aI aK dI Na Nk) pH(aK dI Fn Na) mI(Ed Lj Qb) Pa(kI oP) nB(iA Or) GzbP LjnR} nR{Pb(Bn Eq gP hA iB jE jF jL jM jO jT lK lN lO) Ub(Em fR Rx Ry Uy Va We Yh) Bn(Dc Li Pc Qb Qe Qh St) Ri(aJ aM aO Ax bP Lj) Uy(cR Cx Hr Ki Oe Wc) Li(Af De We Yg Yk) Va(Cv Hr Nk Uc Vt) Pc(jH lK lL lM qY) Vi(cX Mx Nk Qb) Vt(aC Oy Pj Un) Af(Dc Pk St) Th(Dr Oy Wm) Ho(Je Rt Vs) We(bQ Ki St) Ry(aC Nk Oe) jH(Jg lK Oe) Cv(Sh Wb) De(Qh St) Fn(Vh Yg) Gn(aC Mx) Lv(Sj Vh) Nc(jI jY) Wh(Mb Vs) Rm(Sh Wb) GdUc TrOy IpRx YhNy YdJe XaKi YecX LpcR nUlK} pH{aK(aM Ap Ar As Ba Co Cv Cw Fp Li nC nH nK nL oK) Ms(bS cA cK dB Fa hG My Nk Nw Or) Ax(dA dJ Fn fP kQ No Or) Li(aQ aU aV cB dA In No) Nw(bR Co Mm Ne Ph Pi Pj) aV(Fa nC nH nL oK Pk) Co(aC aI aQ cY dR) dA(Fa Im nC nK nL) aQ(Ar bL Lj Mz) nC(cM cS Ip Lh) Bn(bE Dc Ny) Fa(aE Me Nf) Fn(aF Hv Ml) Bo(aC bE) Ip(Db oN) Oy(Ad kQ) Pk(dR Ky) AraU CpNv DctF EtgP FyNo IqkQ LhnH LjcB NycR cQdR} Vi{Nb(kF kG kI kN kO mE mF mH mI mT mY nB nF nI nK nL nM nU oP oQ) St(Aa Jt kF kG kI kO mI mT nF nH nI nK nL nM oP) Nk(kF kK mE mF mI mY nB nI nK nL nM) bQ(aM bP Ed kK mF mT nH oQ Qb) Je(Cw Ki Kk mF Ny) Hr(mF mT Ng nL) Th(Co Cp Wm) Mx(kQ kS oH) mF(cA Ub Yg) nC(Lh Pd Qe) Ng(Yg Yh) Qb(cS oF) aC(bP Co) aI(Ib Lj) bE(Ad Ao) nI(Ok Ub) kN(Ed Fn) FrnT MboQ HxIl RyoP aQcU} oD{aK(Ar As aY Bb cM Co Cv Ha Hr Jj Nc Of Ou Oy Pg Qm) Nk(aN Ax Bc bV Co cQ Cx Ip kQ Li nC) Fn(aF cX De Hv mI Ml nC nH Pb Pk) De(Ax bE Fa Js Li Pk tF) nC(aO cB dA Jf tF) Co(aO cY Iu Nj) nH(cB dA kO tF) Ax(aO Ih Kr) Db(cB Ip Nw) Hv(Ip mT Or) aC(Bo Ke Kk) Af(Dc On) Bn(Dc Ok) Cp(Nv Ok) Cu(aO kO) No(Li Lj) Pk(Ar Mn) cR(Bb kQ) dA(nK nL) BcJf BobE EdIp GlNl MmNw MsdB JvhG cBoK dHdR} oP{Uy(aC bE cM cN dK Dr Hx Ly Me Nb Nk Oy Um) Ry(aY bE dC dH dN Hx Ly Mb Me Pd Ub Um) Lv(bE Em Pk Vh Wc Wh Zw) Ho(bN dK Je Nl Tn Uh Yg) aC(Gd Lp Ru Tn Ux Va Yd) Ks(Fd Rt Sh Zq) Lj(aP Aw Rg Ri) Oy(Bb Kd Tr Th) We(bQ Ki Mb) Wf(bQ Mx Nb) Vh(aQ cY Fn) dK(Gn Rt Tm) Cv(fR Ug) Eq(Nl Pb) Yg(Ny Vt) AxRi DrNb EmIp GnbQ MbVa NcWh HrRu IbJk ShaY XaKi KkaO UnVt} Ng{Ef(eD hA hW iC jD jE jF jG jI jK jL jM jO jQ jR jT lK lL lN qU rC rY rZ) Bg(eD hA hV hW hX iB iC jD jE jF jR jT lK lL lN rY Xa) Uc(hR iC jL jM lL rZ Xa) Il(Fi Ps Wh Yd Yg Yk Yf) Ij(Eq Wd Yd Yg Yh) Yh(Ba bQ Nr Qh) Yg(Li nI Nr) Tr(Wh Ye) Wd(Je Lj) Wf(bA bQ) Rg(hA lN) AdeD BaVw GcoF NcXa HoTn ZqSt WhnI QhjE} oV{aK(Ar As Ax Bc Ct Cx Db Hr NC nH nK nL oK) kQ(aC Fr Fy Li Lj Nf Pk Po) Nq(Ax dR Fr Fy Iq Js Lj) Fn(cX Hv Lj Ml Pb) cB(cR Db Nc Nk Oy) Lj(cQ dA dL No) Ax(cW Mr No) cR(aV dA Ny) nH(cM Jf kO) Bo(aC bE) Co(aN bE) Cp(Nv Om) Dc(Af Bn) Ms(dB Mb) Ko(Ed mT) aA(dR Mx) nC(cM Jf) kO(Cu oK) AjaI DbIp DedR GlNl NoLi MhhG NkaQ HrPa HvmT NwPj OydA} nB{Ry(aP aQ bQ Fw Ih Ij Mx Nb Nk Oe) Lj(cB dA Eq kQ Lt Or Tr Yg Yh) Sh(Dc Ok Qb Qe Qh St Vh) Ed(Dr Rt Vh Wh Zw Ti) Nb(Dr Ux Vb Wc Wf) Uy(aP Fw Mq Mr Nw) Vh(Fn Iu Lv Ri) Zq(Qe Rm St) Rz(Cw Ij Tn) Op(Mx Ny Qe) Va(Mz Nw Vt) Nr(Yg Yh) Nc(jI Xa) Tr(Kj Oy) Wb(Nw Ok) Si(Mx Om) Li(Yh Yk) Oe(jI jY) BoQb CwVw DcRt GnSt UbfR IbWh IjVb WebQ} Rm{Wb(bP fR kF kG kK kN mE mF mH mI mY nC nF nH nI nK nL nM nU) Sh(Aa Du fR Gb Gp Hp Id Ii kN kQ mE mF nC nI nU Rf Um) Ti(kI kN mE mH mT mY oQ) Jt(hA jE jM lN rC Rt rY) Zq(mE mF nC nL nU Ug) bP(Gb Gc Vw Ye Tm) Va(Aa dJ Ip Je) Aa(Rt Vw) Yg(mE nU) Yk(mF nU) Si(bE cA) GbNc JvVw KkOp bNrC} pK{aK(aO Ap As cG Co cY Db Dg Dl kR Ms Ne oF Qm) Ms(Ao aV cW hG Jf Jo mF Mn My Nq) Ax(bS cK dA Ir Iv kO Li mY Nk) Fn(cD cX De Hv mI Ml nK) nC(bV cB cM cS Ip Jf tF) nH(cB cM Jf tF) Iq(cP kI nW) Nw(Jp Mm Nk) Cp(Nv Ok) Dc(Af Bn) Ip(bU Db) bE(Bo Kk) cB(Nc Nk) dA(nK nL) mT(cR Hv) NoLi NuPa aCaE hGnY kOoK} Rz{Ij(hC hF hG iA iH iJ iZ kS mH mI mY nK nW nY oF oH oK pF tF) Il(bA bQ cT cV dF Hx Kk mE Nf Tl) oF(As Bb cI Cv Hr Li Tr Ub Ut Vh) Tn(kF kG kO mH mI nC nH nI nL) Tr(hG iA iJ mI nH nK oK oN) Je(fR Kk Ny) St(cS hG) On(iZ kK) aI(Nc Wm) bQ(bP cS) oH(As Lj) FroQ TthG OkmE UtkF} Ib{Qh(hR hV hW iB jE jF jQ jR jU jY kI lL rC) Rg(iB jG jH jI jO jP jU jY lK lL lN lO) aI(Du Fd Hp Ps Si Ux Vh Wd Wf Wh Yg Zw) Wh(aH kG kK mH mY nC nI nK nL) Yg(mE mF nH nI nK nL) iB(Cs Fa Lj Mt) Zw(aH aQ oH) Vh(mH mI nK) Mj(jE jK) Tn(kI nU) jU(Dk Mz) MwjD LhnC NwlN OkhW} mF{Yg(As Et Im Ny St Tn Vt) Yh(Ij Im Mn Nr Ny Ry St) Ip(Dr Em Ex Lp Tm Tl) Yk(Ij Im Mm Ny Ok Pb) Vh(Cv dE Fn Iu Ri Ub) Wd(bQ cE oF oN Tr) We(aC bQ iP Ub) Rt(bQ Ok Tn Tr) Fi(Ij Im Ny) Gc(aC Nw) Tr(Oy Rx) Tn(Gn Rx) Zq(Ok St) Ry(cR Jy) Ux(aC Ed) DuOk EzWc FdNy GhJe GbRi NbWf NcjI HoQx IjLp YdPb UkVt} Hx{Vw(Ad Aj Al An As Aw Ba Ch Co Cu Cw cX Dc Dg Dk hF Ip) Il(Gb Op Sh Si Va Zq) Ip(Op Va Vb Wb Zw) cX(Gb Rv Rx Sj Zq) Va(Al Dc Dl Je) Ry(bP kI kN) Rv(Dl Je Ki) nC(Sj Vh Wh) Hp(Al Ur) Si(cQ Cx) Zq(Hv Je) Wc(bP dJ) Rx(aM bP) kQ(Op Sh) AnYf BbGb DlUy EmTh UbSj WeKi WhkK nLlK} oQ{Ry(aC bE cR Dr Ma Ni Nk Nx Tn) Mb(Eq Ux Wd We Wf Wh Yf) Ho(Je Tn Uh Yg Yh Yf) Wf(aK aU bE bQ cZ Fn) aC(Du Eq Ux Vh Tl Yf) Ri(bL cI Co Ct) Ub(fR Rx We) Yg(Jk Kk Og) Ks(Yh Yk Zq) Dr(Kk Nb) Rt(dK Nk) Nx(Uy Xa) Vh(cY Fn) Pd(Em Gb) EqNl GnSt TrOy IuZw YkPb WebQ PsUr LtbE RubJ} bE{We(Aj Al Ao As Ax Ch Cp Cs Cu Cv Cx Db Dc Dg Di Hr Ub Wm) Rv(Af Al aM Ar As Ax Cs Dc Hr Wm) Va(Af Al As Aw Bg Cu Dc) Ar(kO nC nH nL Rx) Si(Ax Cu Cw Nr) Al(Lp Uy Tl) Rx(As Ax Wm) Bg(Eq Wd) Gh(aM Wm) Ip(Lp Sh) Ry(kF kO) AnPs BokF CsFc} Vv{Bg(eD hA hR hV hW hX iB iC jD jE jF jG jH jI jK jL jM jO jP jQ jR jT jU jV jY lK lL lM lN lO qX rC rX rY rZ) Mz(eD hW jH jI jO lL lN rC) Kq(iC jF jH jI lN) eF(hR rC) qT(iA oH) jY(fP oK) lN(Qd Rg) JylK dRjQ} nC{Rg(Co Ru Sj Va Wb Yg Yh) Fn(Gc Ps Sj Wd Wh) Pd(Ps Ry Tr We Xa) Ij(jF jL lK lN) aC(Bo Gc Rv We) jI(lK Nc Pb qY) Ho(Mq Mx Qx) Ub(Lt Tl Xa) Hu(Sj Va Vh) Wh(Pb Rh Rj) Ri(Co Cw Vh) Wb(Rh Rj) Uk(Pk Uy) lK(Ok Pg) GnSt MwlM MxWf TrOy TncR ZqLh XaKi VtcV} Vh{Fn(kF kG kI kK kN mE mH mI mY nF nI nM) Ri(kF kN mE mH mI mY nK nU) Iu(kK kO mE mI nK nL) mI(dE Ed Ip Lv Ub) mT(aC aK aV cY dR) Ed(mY nH nK) bJ(kI mY nH) mE(Cv dE Ub) Lv(mH nK) aC(nF nL) kO(Op Ry) EfoH IdkK PdnH cYnF} nI{Ry(Bc cR Cv Dk Et iH Je Jy Nc Nd Ub Uc Yh) We(cR Ki Mb Nc Nk Ub) Gn(Nb Ok St) Pb(Yd Yk Yf) Ed(Qh Wf) Uc(Op Sh) Tn(Aj Ct) Ip(Ex Tm) Qb(Bg Ch) Li(Or Yg) Oy(Dc Tr) bJ(Va Wc) AsWh DkUy WmcB GcUs NcjI ShSt JpjH VtcV} Vw{fP(bQ cT Fy Il Im Ld Lj Lz Ma Mx Nr Pk Tr) Uc(kG kI kN mI mT mY nK nU) Dk(Ma Ml Qx Ra Rh Wm) Wm(aI iJ Kk) bV(Je Jf Nk) Ax(aI iJ) Il(bJ Rf) Ld(hC kS) Rh(Bg Kk) AnMa EzkG GcfR IdIm TrtF RiaM RjcS} bN{rC(Af Bg Bn Bo Cv Cx Dk Gl Hf Hv Ic Ih Il It Jf Jk Jr Lu Mb Mg Mj Mx Mz Nd Oe Qh Qn Qy Rh Rj Sr Tv Uc Ur Ut Uv Wm) rZ(Ih It Iu Mj Ur) Tm(Fw Im) BgrY MjjH UbTl JqqT} mE{Ip(Dr Ex Gc Lp Rx Sh Wd Zw Tm Tl) Yh(Dc Ij Im Nr Ny Ok Ph Ry St) Yg(Et Im Qh St) Ed(Ux Wf) Gc(aC Nw) Ij(Lp Yk) Zq(Ok St) Wd(cE Il) We(bQ Ki) AlDr DcRt FiIm NbWf NcjI NdRy UbfR UcSh TrOy YkPb JeVa UxaC VtcV} nK{Yh(Ij Li Nr Ny Ok Ry) Yg(Et Fn Ij Ok Pb) Nc(jI Ru Xa) Sh(Mm St Uc) Je(Gh Va Wc) Dr(Ip kG) Wm(aI Th) Ed(Vb Ti) Nk(Ry Va) Tr(Jj Oy) Lp(Ld Mq) Ru(Ne Nl) Nw(Gh Sj) AxHp EtRt FnWd NbWf YkPb WebQ WhbJ RycR OejY OklK VtcV} Th{Nr(Eq Gh Gn Gz Rv Rx Wc Zx Tl Yf) fP(Dr Ex Wd Zw Tm Tl) Ma(Gn Gz Rx Wc Tl) Wm(oH pF Qn Yf) Tr(Gz Rv Rx Wc) cS(Dr Zw Tl) Yf(Ax Cs) Wc(On Ut) Tm(bV Cu) fR(Gc kN) BgTl EtZq RxbQ} aC{bP(Gh Ho Rv Ry Ux Wb We Wf Yc Tm) We(cS cX kF kO

Figure 25 Continued nH nL) Rv(aM cS dJ dL Il kS) Bo(kO nF nH nL) aM(Du Gh Hp) Il(Sh Si) Ry(kF kO) Ux(mH ml) kG(Wh Yg) MmSi WbdL PsnL VakF}
fR{Ub(Hp kF kG kK kO mT mY nF nM nU) Fn(Af cX Il Je kR) Nk(kF kG kl ml mT) Ip(kG kN nH) Cx(Jq Qn) Qe(Rv Rx) We(Il pF) Wf(Ki
mT) Vt(kN mY) Aflq AsnL CvkI HoNw UckK JekN OcnU} kI{Ho(Je Rg Ri Rt Tn Tr Yg) Ip(Dr Em Zw Yf) Ry(Bc Dr Ub Zw) Gn(al Mx)
Nc(jl Xa) Uc(Op Sh) Ps(Ki Pd) Vt(cV Va) AxLp BbSi DcRt UbWe TrOy TnUt JglN WhbJ LjRi} mI{Yh(Ij Im Li Nr Ny Ry St) Im(Fi Yg Yk) Nc(iC jI) Uc(Oy Sh) Ij(Lp Yk) Ip(Dr Zw) St(De Zq) Vt(cV Va) EdTi FnYg GcNw NbWf TrOy YkPb WebQ JsXa OklK PglM} mT{Wf(bQ dR Kk Nb Ur) Wh(Kc Ki Nx Pb) We(bQ cR Nk) Pb(Eq Rv Wd) Gc(Us Uv) Uc(Gd Ux) dR(Gn Ux) AsSt BbVa MzYe NcjI NkRy HoQx TrOy KiPs RxOk PglK} kK{Ur(Eq Lp Rt Ru Ry We Xa) Sh(Qh St Uc) We(bQ Jl Ub) Rx(Pb Qb Tv) qY(Hq Iq Pg) St(Fi Zq) Lj(Dk Ou) CvLt CxHo DeQh EqPb FaNk ExIu GnGp NcjI} kO{Wm(Fn Ij Jq Ke Kq Lh Nw Ny On Uh Vt) Gn(Nw On St) Ri(Co Cw Ry) Ub(Ry We) Uc(Gd Ux) Va(Nx Vt) FiNy NcjI TrOy YgLi ShSt SjNw XaKi} nH{jI(Hv lK Nc Pb qY) Fn(Gc Ux Wh Yg) Pd(Ps Tr We) Co(Pa Rg) lK(Ok Pg) CwRi WmaI GnbQ MwlM NbWf NkRy HoQx UbWe TrOy IjjL ShSt WhPb PscX} nU{Fn(Dr Yg Zw) Li(Yg Yh Yk) jI(Ip Nc Om) Ub(We Xa) Ri(Ij Lj) Vt(cV Yg) Oy(Tr Uc) BbGd BcVa DlWh NbWf NdRy TnQw YhNy QbRx OfjY PgjE} nL{Ry(Nc Nd Nl Yh) Wh(bJ Oy Pb) Co(Rg Ri) Ed(Uy Wf) Fn(Wd Yg) Nc(jI Va) Ho(Qb Qx) Tr(Oy Pd) Xa(Ki Pd) CwRi MwlM YgRg YkPb JeVa VtcV} kN{Fn(Ps Rt We Yg) Gn(Mx Qb St) Ry(Pd Rg Ub) Vt(cV Un Uv) Li(Yg Yk) Vb(aY Nd) NcjI UbLt UcSh TrOy ZqSt QbRx LjRi OklK UybJ} mY{Ho(Je Mx Nw Qx Yg Yh) Ed(Qh Rt Ti) St(As Gn Zq) Yg(Cv Lv) We(bQ Ub) Ny(Gn Op) TrOy ShQh QbfP JglM RyNw LikQ LjOr} Hr{Va(aH aI Kk Lv Ny Ou Pg Qb) Tl(cE Gp Il kQ Nd) Gb(Qe St) Hp(Kk Ny) Rx(aI dF) GpTm IlUx KkRv RuaI} mH{Ry(cR Lz Mq) Gn(bQ St) Nc(jI Xa) Ho(Rf Rh) Ip(Dr Xa) Li(Yh Yk) Vt(cV Va) CvUg DuNd WmdR GcNw NbWf TrOy IjZq jEjI} kG{Dr(bQ Kk Nb nY) Tr(Jj Oy) Zw(An dR) We(bQ Ub) Ny(Fi Yh) DcRt NkRy HoQx TncR QbRx JgqY WfbQ OklK UkPk} lN{Rg(Ba jE Ki Mg Nm oH Oy Tt Ua) oH(Lj Lz Qb Sr) Fa(aR In Pb) BaKq CwMj LzpF KkrC LjnY} Mx{iZ(Gn Op Sh Si Zq) Gn(kS nY oH) Id(Wb Yh Zw) Wd(fP kS) Tm(cR oN) ArWb IlSi YgfP WfnF} Je{Kk(Eq Gh Lp Rt Rv Sh Si Va Xa) Ny(Gn Op Sh Zq) Tl(Cv Ki) Va(Ip Rg) AjWh SiQh} aI{Nc(Ru Sf Wd) Nj(Vb Wd Yg) Aj(Eq Wh) Yg(Ax Wm) Lj(Wf Zq) GnVa GlZw NkWd ShcD WhPb RxaM} Rx{Hu(aM cS cU cX) Qb(aQ cR kF) Qh(Ad Dl Sh) cX(Ld Mp) FnaM SsbQ QudF} nF{Wf(bQ dR Ed Nb) Dr(bQ Ed Kk) We(bQ Ub) GndR NcjI TrOy YgVt KiPs} kF{Ub(Lt Ry Wc) Nc(jI Xa) Ip(Dr Lp) NbWf UcSh TrOy YhNy YkPb UybJ VtcV} Il{Fn(Em Si Sj) Tl(Ki Nt Ub) Hu(Sh Zq) Ux(Aw Cv) ApWh NtXa} Lj{oH(Gn Lt Wf) gP(eD kQ) nY(jI lL) YfbP YhbJ ShNx WfcD dRjF} Hp{Cv(Jl Kk Kz Tl) Ny(An Ap Cw Di) AnQh AxhC DiJl} Si{Qb(cN cR fP Pd) Ij(cP Hu Ss) cZ(Ax Wm) DlSt NwcP} Nx{Va(Al An Ax Ch Dc Di Ip) Sh(cD Qb) bP(Wd Wf)} Id{Tl(Cv Dc Ip Ub) Zw(Ld Nw) Qb(Wf Yh) HoLd} Yg{Rg(bA cT oF) Qh(Bb Dc) UboF QbfP} Wd{fP(Dc Kk Nb Nl Qb) cR(bQ Tn)} aM{aY(Ps Yd Yk) Hu(Ru Rv) GhaL SjRg} rC{Dl(Ih Mj) Mg(Bg Uc) BaMz MjKg LipF} Wh{oH(Aj Ch) DgSt EfpF UboF TrKl} Kk{Sh(Rh Ri Rj) Wb(Rg Rh) GnGp} Pb{dJ(Ps Rt Yh Yk Yf) LdgP} Tm{Gp(Di Gn) Iu(Jk Qh) OraY} jE{Qh(Ba Jt) CvEd CwMj DcJt} Zw{oH(Ch Ef) IpbJ RidA} Tl{Ub(Gp Ue) CvIu PaPd} aW{rX(kS oH) LuhR HuRv} bP{Sj(Rg Rj) EqTr YkRj} Aj{YdaY WfiP YebQ} Oy{Yd(aY cX) TrnM} Aw{Gb(Qe St)} Ch{WfnY PsiA} Cv{Ed(rX rY)} Dl{MjjR ZqSt} Gn{GpQb RtbQ} Hu{AlVa RvcX} Yh{NrbJ SsRj} Sh{OncP OuaY} nM{NcjI UbWe} AsUxoH BgJghR CwMjeD EqTrdJ FaWfcD FdQbtF GhSsbQ MgiAqT MsZqJi MuJylK NdKpRv IpXabJ YkRgcT RyLdoN LirXpF Unconstrained panels with 2 analytes, where 1.0E-8 >= 'AUC p-value' > 0. Contains 134 panels of 145,307 total panels evaluated. : Yi(bP iO KJ Kn kO kP lW mE mF mH mI mP nD Ng nH nI nK nL nM nO nU oE Vj Th) nO(dU eM eQ fB gZ jB oD oT oV pH pI pK) oE(Gc Hl mM Rt Vi Wd We Wf Yg Yj Tm Yf) Fb(hW hX jH jU qU rB rC rY rZ) Uw(lW lX lY mS mZ nJ nT) dD(dU gZ jB oD oV pH pK) gC(Hl Ps Vi Wd We) Yl(lW lX lY nN) Oa(gP kC mS nD) oW(dA eC Fn Nt) Vz(lW lX nN) Vq(kC nA nJ) bZ(Vj Vw Yj) dU(aC nC Oh) fA(aV dA nC) fB(cQ hG mW) lY(Ok Up Wc) Hl(mU nR) Is(kP pH) nN(Wf Yf) nA(Vh Wc) hB(mM Rz) jB(Aj Ao) BoWn TjoV NkoD TrVj IkTl YjoP PzVw RymS LjgP OhpH VumW aKgZ cReM Unconstrained panels with 2 analytes, where 1.0E-7 >= 'AUC p-value' > 1.0E-8. Contains 56 panels of 145,307 total panels evaluated. : Oa(bN dJ Ic kQ kS mW mY nY oE) Fb(eD gW jE jQ lL lM qY rX) oE(Lj Rv Uw Uy Vj Vw Wc Wh) Is(lY nC nH) Yi(cP Ib Vh) nA(Ed Ru Ry) Nn(Gn Yj) Hl(aI bZ) Qa(bN Vw) gC(Gb Zw) FakQ MfVa NgQh YhnN YjnR QbbN QclY WhmZ RzbZ LjdJ NykE UwmM VjbQ VqlX Unconstrained panels with 2 analytes, where 1.0E-6 >= 'AUC p-value' > 1.0E-7. Contains 131 panels of 145,307 total panels evaluated. : Oa(cP kE kK lY mM mU nB nJ nT nW pH pI) oE(Gb Rz Ux Va Vb Vc Vh Vz Wb Yh Yl) Fb(hR hV jD lK lN Ng qV qX rA) Is(Ib lX MS mZ nL Nt nU) gC(Gh Ms nO Ru Rv Uz Vc Wg) Lj(aI cJ dA kQ kS nY oH) Vj(Lx Ma Nn Oz Qa) lY(aI iB Ry Uy Vi) Fa(cP gP lN Tk) Tn(kE mM mZ Ng) Yi(eF Mg Uu Vw) Yj(aH aI hB) Uw(kP nA nO) dD(eQ oT oW) pI(Nl Or Pk) Th(Qa Wm) Hl(nN oP) Kk(Rt Vi) Li(gP mW) Yl(Id kN) Rm(Sh Va) Oh(gP Si) Vw(cS Pf) dU(aK nH) eM(Ed Fn) nR(bH lK) nA(Va Yf) BgNg DgjB NnXa MffR MspK TrmZ IkYh IlVz ZqOw StmM PsmS RvaC VukC aEoW bNrC eCmY fAmT kQoT Unconstrained panels with 2 analytes, where 1.0E-5 >= 'AUC p-value' > 1.0E-6. Contains 320 panels of 145,307 total panels evaluated. : Is(fB gC Hv Hx Ik Il In Jj Jn Jo Jr Jt kE kN kO Li lN Lv mE mM mP mT mU mW nB nD nI nJ nN Nr nT oE Pd Uk Up Vv Tk Wm) Oa(aE aG aI aL aQ aW bB cJ cR cZ dA dD fP hG iJ iO kI kO lX mZ nA nO oH oN Pd Va tF) oE(aW Du Eq Fb Fn Gn Kx Li Lp Lt lW mP Ps Qh Ru Rx Ry Sh Uz Vq Wg Yk Zq Zx Th) Yi(aM aR aY bJ Ef Ik Jh Jo Kg Kj Kk Nt Pd Qt Rf Rh Ss Vv Yl Tl) Fb(Aj eC Ed hA iB Ik jF jI jM jO jV lO qT qW Ss) Lj(aE aG bN cP cZ dD eC fP hG Ic iJ iZ nW pI tF) lY(dD Gc jI Pz Ri Ru Rv Rx Vh Vq We) bN(Ed Et Fa Fw Lx Qd Qe Qh Uk) nN(aI bH cZ Dr Ex Kq Uw Yj Zx) Vq(kP mE mF mH mM mW nD nI) eC(kO Li mU nC nH nJ nL oQ) Qa(dJ Gn gP Si Up Vi Zq) Uw(kC mH mI mU nR oP) Vu(mP nA nD nI nO nU) Vw(bV Cu hB Il Kk Ma) Nn(Hl Rz Si Vi Vz) Uk(aW dJ Iq mW Qb) mS(Gh Ho jI Wh Xa) Wm(aI cZ nA Yl) Tn(nO nT nU Vj) Li(Bo dJ kQ oN) eQ(aE dA kE kQ) fB(dD Ma nC Oh) iB(nC nD nH nL) Fa(aY dJ mW) Lx(cO Si Vh) Ng(Cq Ut Yg) Hl(bE oQ Tl) Va(Ip Je Kk) aC(gZ oD We) gP(Cs hB Ld) kE(Fy Kq Ok) Fn(gZ oT) Nc(pI qY) Yj(Ow Tl) Si(Mf Ow) Uy(kC nR) Vi(Hr Th) Vj(Oh Pf) bH(jB mU) bZ(Rx Wd) lX(Pk Ry) mM(Kq On) mZ(Mz Ok) iO(Dr Zw) oW(Ip Ms) AxaI NrdA MwWn IcIr IkRv IlRz VzKk ShOz TlKi YlnC RieM VhnT aWrC cBdU dDpI nRqY mHjO nAjI hGoT Unconstrained panels with 2 analytes, where 1.0E-4 >= 'AUC p-value' > 1.0E-5. Contains 790 panels of 145,307 total panels evaluated. : Is(Aj aQ Ax bN Bo cR Ct cV dJ Dl Ed Ef Et Fb Fp Fr gP gZ Hq Hr Hu Hw Ic Ih Ii Im Iq Ir It Iu Iv Jg Jh Ji Jk Jl Jm Jp Jq Js kC kF KG kI Kj Lh Lj lK Lu LW Lx Mc Md Me MF Mg MH MI Mj Mk Ml Mn Mp Mq Mr Mt Mu Mw Mx mY NA Nc Nd Ne NF Ng NK Nl NM Nn NO Nq nR Ns Nu Nv Of Og Oh Ok Om On oQ oW Oy Oz Pa Pb Pe Pf Pg Po Pz Qa Qb Qc Qd Qe qT Rc Sh Si Uu Vj) oE(bN cE Cs Dr Em Ex Fa Fc Fd Gh gP Ho Hp Jq KE kF kG kI kO Ld lY mF nC nD nH nJ nL nO Nr Of Oh Op Pa Pz Qb Rg Sf Si Sj Ss To Uk Vs Yd Zw Ye Tl Xa) Oa(aC aH AR aV Ax bF cE cN cV cX cY dB dC eC Fb Gp hC Hv Ik iZ Js Jt kF kG kN kP mF mP mT Ng nI nK Nr Nt nU Oi Pj Rf Sr Uk Up Vv Vw Ti Th) Yi(aI Aj Ap Ba bI Ch cL Dg DL Eq Fn Hr Hx Id Ii Il Iu Je Kc Kf Ki Kp Ms mZ nA nJ Nm Nn Of oN Oz Qu Rc Si Sr Ug Uk Up Vz Wb Yg) bN(Ar

Figure 25 Continued

Ax HB Ir Ji Jm Jq Jr Ke Kk Ko Ld Li Nw Pz Qc Rg Rm rZ Sr St Uh Ut Tm Wm) Lx(aV aW aY bC bS cA cE cH cK cL cP cR dA dD dH Gn gP HI Ib Pj Uk Vw Yj Yl) Lj(aH aL aQ aR aV aW bB cB cR cV dB dC dU Fb Gp iO mW oN pF Ut Wb Th) Yl(Ax bP Ib Il kE Kk Ld mF MS mZ Nd Ng nJ nT Oh Ow Oy Rv Rx) Fa(aP aR aU aW bL cA cG cK cV dA dC dN hG Ip mU Pd pl Uk) Uk(al cE Cq cZ dD Fb Fn Ip Ir Li IX nA Qa Qe Qh) IY(Fr Hl Ip Ky mW Nn Ny Om On Rt St Ur Va Vt Vu) nN(bG cV dD eC Hb iJ Kk Ko oK oN Vt Yg Yk Zw) Qa(aW aY cP dA fR Gb Hl kE nA nT Rz Sh Yj) Li(cV dB Ed Ib Ic Ik Jd kE kS Nt Pb Up Vv) Th(Ed Gh Hx Ma Mj Nn Oz Rv Rx Vu Wc Tm) Kk(Eq Gh Rv Rz Sh Vj Wb Wc Wf Wh Yk Yf) Vw(al Ax bQ fP gC Hx Ip Ld Nn Ow Tr Wm) Fb(Dl iC iO jG jK jL jP jR JT jY) Ng(cE Co Dk gP Kq Tr Uc Uw Vq Wd Wh) Ir(cP dA dC gP Ih In Ms Rf Up Tk) Oz(Ax dJ Dr Ed Em Eq Gd Vz Wh Yh) al(Cs mM Op Rx Rz Sh Ss Va Wd Zq) lX(Gc lp jB oW Pz Qc Tn Va Vh Vu) Uw(gC Ik kF kN mE mP mT nB nI) Qh(Cp Ct dJ Ib mW Rx Sh Vj) aW(cR cV Ed hB Hx jE Jq Rg) kE(hB jB Nn Pf Qd St Tr Vu) pI(aC cQ dA Fn Je Mf mT tF) Vq(kF kl IW mS nB nO nT) gC(Ne Rt Uy Va Vh Wf Wh) gP(Ax Ch Ed jB Kx Mh No) nA(Dr jO Pf Tn Tr Up Uy) Cs(aG cJ cZ dJ Gp iB) Nn(EM Eq Gh Sh Zq) Hl(aH Gp hB oO Ow Va) Vz(cD fR mZ nU Pf Va) Qb(aQ cP dJ fP Rx Si) gZ(bE dR nC Nk Nw tF) mS(Fd IN Vi Vu We Tl) mW(Ax bH Jg Ok Tn Vt) Ed(dA dJ Ip Pb Up) Hx(Gb Si Vj Yj Zq) Ik(Gn hB Sh Wh Xa) eM(aQ cV Fw Jf Ss) mZ(Fr jl On Qd Yd) iO(dD Ps Vc Tm Xa) Fn(eQ fR jB pK) Yj(nI Oh oQ Pg) Vu(kK mM mY nJ) aK(eQ oD pH pK) nC(bH jB jl oT) nD(eC Ex Qc Tn) iB(kO nI nJ qT) Wm(cP kC oH) Nc(jH qT rX) Tl(Cv Pd Ub) Kx(dJ jH IN) Oh(cA cK cT) bE(Rv Va We) nT(oW Pz qY) hB(jF nO Of) Ax(cZ Iq) Bg(Aj Ch) Si(Ny Pf) Sh(Mf Qc) Rz(bQ oF) Ok(kP mM) bZ(Vi Yg) dU(cR Nw) eC(kC nF) fA(cl Ip) fB(kQ Pa) nR(Af Vt) nJ(Tn Wc) jB(Ad Hr) oW(aV Cv) AsIK CqVa YfTj FmT GnGp MxYh MzTk IcrC QcmP KiPs Rynl RxcX RmdJ RioO RglN NymM OwVj VocE VvhA nHjl qYkK kSrX Unconstrained panels with 2 analytes, where 1.0E-3 >= 'AUC p-value' > 1.0E-4. Contains 2,996 panels of 145,307 total panels evaluated. : Li(aG al Aj AL An aQ AR As aV aW aZ Ba Bb Bc BG bS bU bV bZ cA cB cC CH cJ Co cP Cq Ct Cu Cv cZ dA Db dD Dc Dk eF Ez Fa Fb Fn Fw Fy gL Gp Hb HF Hq Hr Hu Hv Hw Hx iA Id IH Ii IJ Il Im In IO IP Iq Ir It Iv IZ Je Jg Jj Jm Jn Jo Jq Jr Jy Ke Kk Ko KP Kq kR Ks Kx Ky Lj lN Lw lX lY Ma Mb Me Ml Mk mM Mq Mr mS MT mU Mx mY mZ nA nB Nc ND Nf Ng Nh nl Nj NK Nl NN NO NR Ns nT NU Nv nW nY Oa OF Og OH oK Or Ou Oz Pa Pd pF Pg Pi Pj Pk Po Pz Qa Qb Qg Qh Ql Qm Qn Qt Qu Qw Qx Qy Rb Rf Rg Rh Ri Rm Sr Ss St Tn Tl Tz Ua Uc Ue Uh Um Uo Ur Us Ut Vp Vt Tk Wm tF) Is(aA aD al aJ Al aM AO Ap aR aV aW aY Ba bB Bc bJ Bn bP bR bU bV cA cC cF cG CH cK cN Co CP Cs cU cX cZ dA dB Dc DD De Dg Dk dL dU eC eD eM Ez Fa Fd Fn fR Gb Gp HB hF Hl Hp iB IJ IO Ip Iz jB Jd Je jl jM JU Jv Ki KK Kl Ko Kp kQ Ks Ly Lz Ma Mb Mm Mv My Mz Nb Nh Ni Nj Nw Nx Ny Oa oD Oe Oi oN oO OP oV Pc Ph PI Pj pK Qg Qm Qn Qt Qu Qw QY Rb RX Rz Sf Sj Ss Ue Uf Ug Um Un Uo Us Va Vh Vq Vs Vw Zq Zx Ti Th tF) oE(aI Aj aN aP Ar As aU Ax aY Bb bF bH bQ bV cA Ch cl cP Cq cR Cv cY dD De dF Dp dR Ed Et Fi Fp FR Gd Gl Gz Ha HB Hc hG Ib Id Ij Ip Iq Ir Iu Iz Ji Jj Jr Js kC Kd KK KN Ko kP kQ Lh LX Ly Lz Mb mE Mg MH ml Mj Mp Mq Mr MS MT mU mW Mx mY mZ nA nB Nd nF Ng nl NK nM NN No nR nT nU Nw Nx Ny Og oH oO oP oQ Pf Pk Po Qa Qd Qe Qu Qw Qy Rb Rm Sr St Tn Tr Tv Ua Ub Ug Uh Um Up Us Ut Uu Vt Vu Vv Wm Tj) Oa(aA aK aM AN aP aS aU Aw aX aY aZ bA BC bE bG bH bI bJ bM Bo bP bQ bR bS bU bV bZ cA cB cC cD cF cG cH cK cL cM cO Cp CS cT cU Db Dd dF dI dL dN Dp dR DU Ed eM fA Fn Fp gL HB HF Hx IB iH Ii In IP Je Jj Jo Jq Jy Kg Ki kR Kz Ld Lj lL lM lN Lu Lv lW Ly mE Mg mH ml Ms My NC Nd Ne nF nH Nk nL NM nN No nR oF oK oP oQ Ow Oz Pb Pe pF Ph Pi Qc Rc Rj Rm Si Ss Ue Uf Ug Um Un Ut Wb Yh Yi Tk) Yi(AA aC Ad Af aG aH aK AN AW bB bC bE bG bR bU bV cA cD cl cO Cq cR cV Cw cX cZ dA dD dE dJ dN Dp Ez fR Fy gC Gd Gh Gp Hc Hp Hu Hw Ic In Ip It Iz Jg Jj Jn Jr Js Jt Jy kE Ko Ky Kz Ld Mb Mf Mh My Na Nc Oe Og Oi oO oP oQ Ow Ov Pc Ph Pi Pj Qb Qd Ql Qw Qz Rg Ri Rt Rv Rx Rz Sh Sj Tn Uc Uf Uw Va Vb Vo Vs Wc Wd Yd Zq Ye Tm) Fa(aC aE aF aG al aJ aK aM aN aO aQ aS aV aX bA bB BC bF bG bH bI bJ bM bO bP bQ bR bS bU bZ cB cC cD cE cF cH cl cJ cL cM cN cO cQ cR cS cU cW cX cY cZ dB dE dG dH dI dK dL dM dR eC eD eF Fb gL Gp iB Ii Ij Ik In iO Iq Ir Iv Jt kE lM mM mP Ms mZ nA nD Ng Nt oH oN Oz Pb Pj Rv Sr Um Up Yj Th) Lx(aC aD aE aF aH al aJ aK aL aN aO aP aQ aR aU bB bE bF bG bH bl bL bM bO bP bQ bR bU bV bW bX bZ cB cC cD cF cG cl cJ cM cN Co cQ cU cV cW cX cY cZ dB dF dG dl dJ dK dL dM dN dR eC Fd fR hB hG Ho Ic iO Iq Je kQ kS No nY oH Pb pF Rc Rf Rg Sh Sr Ss Uf Up Va Vi Vv Wb Wc Yg Yh Zq Ye Th) Ir(aC aE aF aG al aJ aM aP aQ aR aU aV AW aY Bc bL bM bP bU cA cB cE cJ cK cL cM cN cQ cR Ct cV cY cZ dB dD dE dG dJ dM dN eC Fb hG Hr Hv Hx Ib Ik Im Ip Iv Jj Jn Jr Jt kE kQ Mf Nc Nf nW oN Pb Pi Pj Qt Rg Rh Ri Rj Rm Ue Uf Ug Um Ur Us Ut Uu) Uk(aC aD aH Al aM aN aQ Ax bB cG cH CO cR cV dA Dc dF dG dH Ed Et Fw Fy gC gP Ha hG Hr Hu Hx Id Ih Ij Il iO It Iu Je Jl Jm Jq Jr Ki Kk kN Ko Kq Kz Lj lY Mf Mh mS Mz Nr Nw Ny Oh Ok Or Oz Pa Pe Pf Pk Pz Qc Qd Rg Rm Sr Tn Ut Vq Yh Tj) Qa(aE aG aI aN aP aQ AR aU aV bL bS cA cC cD cE cF cH cJ cK cN cO Cp Ct cW dC dD dE Dl eM Fb Fn Ho Hv Hx Ib Ic Ih Ip Jr Ki kQ IX LY mM mP mS mT mU mW mY mZ nB Nc nD nK nN Nt Oh Op Ow Ph Pj Qt Rg Sj Sr Va Vh Vv Ti) al(Aj aK aM aW aY bJ bN bP cA cR Ct dJ Ed eM Eq Ex Fn gP GZ Ib Ik iO Iq Jj Jr kC kE kG kl kO Kx Ld lW mF mU mZ nC nD nF Ng NH nJ nK nL nO Of Oy Pz Qb Qh Rg Rt Ru Rv Ry Si Sj Sr Ug Ux Uy Vb Vi We Wh Yg Tm) Fb(aC Ap aQ aU AW Ax aY Bc BN Bo cA cC CH cM cP CQ cR Cs Ct cV dA De Dg dJ Ef Fw GP Hx Ic In Iq Iz Je Jg Jq Kj Kl kQ Kz Ld Mf Mg Ms Mu Nn Oh Or OW Oy Oz Pd Pj Qb Rc Rg Ug Um Uu Vo Vv Tk Wm) Yl(Aj An Ar bZ Cp CS De dK Ed Ef Gn Hr Hu Hv Hx Ik iO Iu Je Jh Jo Jy kK Kl Kn Lj Lz mE Mf Mh Mx Na Nc Nl Nj Nk Nn NR Nu Oi oO Oz Pb Pf Pz Qx Ra Rc Si Ss Tr Tt Up Uu Va Vj Vq Zx Tl Tj Th) Ed(aC aE aF aN aP aR aU aV aY bS bU bW cA cE cH cK cP cR cV cW cZ dD dE dK dN dR fP Gd Hb Hl Ij jE Jq kE Kz Lj IX mP mW mY nD nl oH Qd Qh qT QU qV qW qX Qz rA rC Rg rY Um Uo Vt Vz Yh) IY(Ax bH bZ cB Co CQ cV eC Et Fw Gh Gp hB hG iA iC Ij Jg Jj jO jP Jq jY Kj Kq Lh Lp Mm Mn My Mz nA nR Nw oP oQ Or Pk Ps Qd Qh Qm Tn Ug Uh Us Ux Uz Vb Vc Vw Vz Wd Wf Wg Wh Th Yf) Lj(aC aF aK AN aO aP Ar aS aU aZ bC bE bF bG Bo bP bU bZ cC cE cG cH cN cQ cY Db dF dN Dp dR eF fA Fn gL hB hC Hf iH Ij In iP Iq Je Jy kR oK Pi Pj Rf Rh Sr Ug Vv Vw Yf) Qh(aC Aj aQ aV AW Ax Ba BC Bn Bo bS cA Ch cK cN Cs cV dA DD De Ef Fn Gn Gp Hp Hx Ik Iz Je Jo Jt mM Ms MU mZ nA nB nJ Of Oy Ph Si Up Uu Yg Yj Wm) bN(aW Bb Cq Cs cV Dc dJ eD Fn Fp Fy Hr Ib Ic Id Ih Ij Je jH Jj Jl Js Kd Lh Mj nN No Nq Nr Oh Ok On Or Pb Qm Qn qT rB Ss Tn Tr Tv Uc Um Ur Us Vq Vt Wn) Oh(aD aY aZ BA bC Bg bH bP bQ bR bZ cG cH cL cN cO cR Ct dG dH dJ Dl dM eM fR Gb gC Gn Hl Ho Ik kE kS nA oN pl Rx Sf Sh Up Va Vw Vz Wb Zq) Vw(Ad aH aM BA Bg Cq cR Cs cT cU dD Dk Dr Et Fw Fy Ij iO Jc Jl Jm Jy Kf Kq Mf Nd Nr oK On Oz Ql Qx Rh Rv Rx St Uc Vq Vu Zw Tl Tj) nN(aG bC bE cB cC cD CO Cq cW dA Dc dL dN dR Eq Fi Gb Gd GP hB hG iA iZ jI Nn Ok Or oV Ri Rv Rx Vh Vi Wb Wd Wh Yd Tm Tl) Ng(Ad aW Ba bF bQ bZ cG cR Cu cV Dc dF dJ dM Ez Fy Gp hB Iz Jy Ko Ps Qt Rg Rm Rv Sr St Tt Ua Uf Vi Yd Yh Zw Xa Th) Kk(Fc Fd Fi Hl Ho Hp kE lM lN Lp Op Oz pl Ps Rx Sf Si Sj Uw Ux Uy Uz Vb Vc Vh Wd We Wg Yg Yh Yj Zq Zx Ye Tl Xa) Cs(aE aH aL aN aZ bB bM Bo cB cC cE cP dA dB dD dF eC fP iJ Ik Ip Iq kQ lM lN mW Nl nW oN Oz Th tF) nA(cD eC Ex Fw Gz Hl Hx iC IK Lp nL Nn Ny Ok OW Ps Pz Qc qT Ri Rv Sr Ux Vb Vi Vt Wd We Wf Wh Yj Tj) Iq(Ad Af Aj Ap Ar aV aW Ba Bb Bg cA Ch Co Ct Cv cZ Db Dd De Di dJ Dl dU gC Ib Ky Kz Ly Ms Nc Ug Um) lX(Cq dU eQ Et fA Fr gZ Ij Jj Nn nT Ny Ok Or oT Ow pH pl Qd Ri Ru Rv Up Ux Vj Vt Wc Wd We Wh Zw) gP(AJ cH dF Fp Fw Ik Js Ke Lh Lz Mj Ml Mq Mu Nn Nr Nw Ny oP Or Oy Oz Pe Qb Qd Qy Tk Tj) Th(Ax Cq Dr Ex fP Fw gC Gz iA Il Je Jl Kx Ld Mu Mz Pb Ps Qb Si Tn Tr Uw Uy Yd Yh Tl Yf) dD(Ax cR fA Gb Gh Hl Ib mU nH nT oP Qb Rv Rx Rz Sh Si Va Vb Vj Vz Wc Wd Wh Yj Zq Tm Wm) mS(Dr eC Eq Gb Hp Hq Jg Lt Ma Na Nv Ny

Figure 25 Continued

Ok Om On Ri Uy Va Vh Vz Yd Yk Zq Zw Tm Wm Yf) aW(aQ Ax dB eC Et Fn Hb Hr iO jH Jj jK jM Jr Jt lK oT Pd Qb Qd Qm Qn rX rZ Vu Wn) Oz(Cu dG Du Fd Fn Fw Gb Gc Gh Gn Hl Ho Hp Rv Rx Si Sj Vi Wb Yg Yj Yk Zq Ye) gC(cR eC Em Eq Fd Fn Ho Lp Ri Rx Sh Ss Ux Vb Vz Wc Yj Yk Zx Ye Tm Tl Xa Yf) mW(aJ eQ fA Fr Hx jI Jp Js Nb Nn Ny oT oW Oy Pb Pz Qb Qc St Uc Ug Uw Vz Wm) Nn(Ba Ch dJ Dr Gz Ho Lp mM mT mU nU Op Rx Sf Wd We Yh Zw Zx Ye Tm Yf) Ik(Ax Cq cR Dr Gc Gd Gh Lp Ps Rx Sf Va Vh Vi Vj Vq Vz We Zw Zx Ye Tm) Qb(aE aV Bo bU cE cF cR cV dA dB eC eM Gn Gp Hl Ic kQ kS oH Up) Vj(aC bA Cq cT dF hB iO Ip Jm Js Ld Mf Mt Nd Nr oF Qd Tv Ut Vu) Va(aC bZ Dc Hr Hu Hx Jq Mj Mx nD nJ Nx Ny Or Ou Ow Vq Vu Zw) Ip(Hp Hx kC Lp lW mF nC nD nH nJ nL nT oO pH Qd Qe Si Wm) dJ(Ax eM Fp Fy Ld Mh Mx Nr Pb Qd Rg Sr St Tn Vq Vu Wm Tj) lN(As bB cE cZ Et Hb iB Jq Ke Ki Nc Ne Nl oH Qc Sr Uh Ut) oW(aC aP cB dN Hc hG Iv Iz kE kI kQ Me mM mT Na Nk Nw Oy) Ij(Fn fR Ib Jt kE kP Ms nC nH nL Qt Rg Si Ss Ug Uu Vv) hB(aC Aj aR Ch Eq Fn hG Ib Iu jD jE kG kP Mu Ss Vs Zq) eC(Ib Js kF kI kP Kx Ld lW mI mM nO nR nU oO oP pI) Vz(An bP iO Ms Mx nC Nd nJ NR Ny Ow Pb Rx Tj) eM(aV Bo cB cD dI Et hG kQ Mq Nl Oe Rc Tz Up Uu) mZ(cV Et Fy Jg Lh Nv Ny Om Or Qc Vi Vq Vt Vu Yg) jI(kF kK kP lW mH mI mP Nc nD nK nO nT nU qY) Mf(Eq Gb Gd Op oT Rt Rv Rx Sf Ux Vh Wc Tl) Hx(Gn Gp Hl Hv Je Op Rv Rx Sh Sj Wc Tj Ti) Yj(Et iO Ji kI Ky Ld Mq nU Ny oO Ou Pf Xa) bZ(Eq Ib Oy Sh Ss Vb Vh Wb Wc We Wh Zq Xa) Ms(Cq cR dU eQ jB Ke oD oT pH pI Pk Rm) Nc(eD hX iB jY qV qZ rA rB rC Rx Tl Xa) Tn(aR Ch De kG kP mI mP mT nI nR oQ Qt) Ny(Ba Gn kG kP lW nU oP Ph Rv Rx Sh Ti) bE(Gb Gh Hp pK Ps Ru Rx Si Vi Wc Wh Zw) iO(Hl Rt Ru Rv Rz Sh Uz We Wf Wg Yh Ye) Qc(Fn Hl kE mE mF mI mM mU nR oO Si) aC(eQ Hl nR oT pH pK Ps Rx Vi Wc Tm) nD(Co Fw jH jP qY St Ug Up Uw Vi Vt) pI(aK Ax Bo cB Co cR Dp kQ Kz Ne Nk) Cq(Aj bC bP Ct Fn Jj Kz oP Ug Ux) Pz(kI mI mM mP mT nB nK oO oQ Uu) Vq(cR kE kG kN kO mI mT mU nK Vh) cE(Ax bP Hr Ib Of Oy Rc Rg Ss Wm) fA(cB cQ gZ Hc kQ nH nL Nw Pa tF) Vu(kF kG kI mI nB nK nT Rz Vh) kE(bH Co Im Js Lh Nb On Or Ow) Ax(cJ cP dA dU Gp In Nl oH) Ib(bQ cG hA iB Mw Nw rB rC) Sh(aH cD Il Je Mn Nx Ow Pf) Uw(kG kI kK kO mF nC nH nK) aM(Gh Hl Ps Rv Rx Sj Yk Yf) cV(aN Kx Mh Pk Sr Uu Vs Vv) oT(aK cI cQ cX Je nH Nk nL) Fn(iA kN nC nH nL nR pH) Si(Je Mx Nw Qd Qe Rm St) aQ(aK aU cP cY gZ Jr Rx) mM(aH Dc dR Et Fr Vi Vt) nJ(Co Dr Fd Ri Ry Vh Wd) kP(Dc Et Fr Jg Qd qY Wh) Hl(aL bB cD cZ kK Pf) Tl(Di Id Je Jm Nl Pc) Up(Fw Jq kN Nr Qd Wn) bH(mF nH nL oO oP oQ) dU(cL dA dR Nk Ou Pa) fR(Et Im Nl Nw Pc Pf) nR(aO Bn jH jY Oy Pb) rC(Bn Cv Cx kS Pj Vv) Aj(cZ Fr oH Qd Ut) Co(fB kO nC nH nL) Rx(bA cT dF Jm Ug) Ok(kI lW mE mF nU) Ow(kK mP nO Vi Wf) Vt(kN mF nI nL oP) jB(cI cR mT nH Of) Wm(dA Gp Jq Qd) Zw(bJ bP Ii Iu) Ry(kI mP mU oP) Rg(Gp Jj kQ qU) Pf(Gn mH Vh Zx) gZ(bW dA Pk Tj) jH(Cx kF Nl Vv) qY(kF Kx Mb Nd) Et(nT Pj Zq) Gb(Qe Rm St) Yh(Pb Ss Ug) Je(Gd Rv Xa) aY(Mz Or Tm) bP(dF Dr Xa) cD(kN Wf Tm) eQ(cB cP hG) fB(Bo Pk Tj) nC(oV PK) iB(Aa kC lK) jE(cM cU Jy) Nl(eD qT) Ho(kI Ug) Zq(Rm St) Ss(aH bQ) Jt(On Tr) Ki(We Xa) Kx(aL gW) Rv(Hu Kp) Wn(Hf Rb) Vv(gW lL) Oy(bQ dF) aK(aU oV) dA(oV Po) dR(nT oD) kC(Dr Rf) kF(jP jQ) oH(Ar As) BahA CheF TiSt ExQd FroQ FwkK NrdL MxWb MzeD IlUx WdfP JjcR RzcS LdPb NwpH UyoP VimF PgqT hCrX lKlL

Constrained panels with 3 analytes, where 1.0E-10 >= 'AUC p-value' > 0. Contains 47,915 panels of 24,406,229 total panels evaluated. :
Hl{gC(aC aD aG aH aL aQ aU aV bF bG bJ bM bO bQ bW bX cB cD cI cT cW cY dA dE dF dJ dK dL dR Eq Fp Fy Gp Gz Ha Hc Ij Ik Io Is It Jd Jl Jm Jr Js Jt Ju Ke Kf Kl Kq Ld Lh Lv Lx Lz Ma Me Mf Mg Mj Ms Mw Mx Nd Nf Nh Nl Nm Nn Nv Ny Oa Oh Oi Ok Om On Oz Pa Pb Pd Pi Ps Pz Qb Qc Qd Qg Qh Ql Qm Rv St Tn Tv Tz Ua Ub Uc Ue Uh Uk Uo Vp Vs Vv Wh Zq Zw Tl) bZ(Ad aI Aj An Ap aX aY Ba BC bE bI bJ bP cC cD Ch CP Ct Cw cZ dA dB dD dH Dl Ed EF Eq Ez Fn Gl Hc Ib iH Ii In iO Iu Iz Jd Je Jg Jh Jt kF Kg KI Kj Kk Kl KN kP Lj Mg Ml Mu Mx mZ nJ nK Nm nN Nt Oe Of Oh Oi oN Ow Oy Oz Pb Pc Pd Qb Qt Qy Qz Rc Rj Rx Rz Ss Ua Uc Ue Ug Un Uw Ux Va Vh Vj Vo Vq Vs Vv Vw Wd Wh Yg Th) mU(aM Ao Ba bH bL bO cA cF Co cS cW Dd dK DR Et Ez Fa gL Gp Hc Ik Il Je Jp Jr kG Kk kR Kx Ky Lh lW Lz Mf Mg Mh Mj Mk Ml Mm Mn Mt Mw Mz nA Nb nC nD nJ Nk NN Nq nR nU Nw NY oE oF oH Ok Oz Pb Pd Pf Pz Qe Ql Qu Qx Ra Rf Rh Ry Tn Tr Ub Uc Ur Ut Va Vh Vi Wh Zw Tm Wm Tj) aI(aC Aj Ao Ap aW Ax bN bP Ch Cp cT cU cX De Dg Ed Ef Hx Ib Ik Je Js Kc kF Kg KI Kj kN Ld Lj Lx lY Lz Ma Mf Mh Ml mS Mu Mx My Na nD Ng Ni nJ Nl Nn Nr Oa oE Of Oh oO oQ Ow Oy Oz Pb Pf Pk Qa Qx Qz Ra Rh Ru Rx Ux Va Wd Yi Zq Wm Tj) nR(aF Aj aK aN aO aP aQ aU bB BN Bo bP bS bW cA cK cL cX dD De dH Du Fd Gp Ha Hp Ic Ik In Iu Je Ji Jo Kg KI Kj Kr Kx Li Lj Mp mS Mw Mx Nd nI Nj Nl Nw nY oH Or Oy Pb pF Ph Pi Qb Qn Qw Rx Sh Sj Up Us Uv Ux Va Vs Vw We Yl Th) bE(aH aJ aM aN aP bA bP bQ cD cE cM cT cU dF dL Ed Et Fa fR Fw hB Hx Il Im Is Js kF Kj Kk Kx Ld Lj Lx Lz Ma Mh Ml Mq Mx Na Nf NN No Nr Oa oE Oh oO oP Ow Pe Pf Po Pz Qa Qb Qx Ra Rh Rj Rm Rv Up Vq We Yi Tl) nN(aK aQ aU Aw bB bG bN bS cA cE cK cL cY dA Dk Dl dN dR Du Ez Fi Fn Ha Hp Hq iH Ik Iu Iv Je Jq Jy kC kI kQ Ky Lh Lz Mf mH Mp Mv Mz nA nB Nd NJ Nk Nq Nw nY oH Om Op Or pF Pz Qc Qd Tz Uc Vp Yd Yl Zx) oP(aK aN aU aW aY aZ bC bI bN bR bW cD cY dK Ed Em Ez Fc Fw Gz Id Ik Io Ir Iu Iv Jm Kd Kl Ko kP Lt Lv lW mE mF Mz Nb nC nH nI nL Nu Nx Oa Oz Pa Pb Qg Rx Sh Ul Uy Wb We) nA(aJ aP BA bF cE cH cO cT Cu Cw dF Em Fa Fy iA Jl Js Kj Kl Kz Li Lx Lz Ma Mh Ml Mt Mx Mz Nf nL Nn No Oa oF Ok oN Ow Pa Pf Pk Ps Qb Qe Qu Ry Ur Vi We Wh Yg Tl Xa) Ow(Aa aC aL Ap Ar bG bI bJ bN bP cC cS Cw cZ dA dB eF Hb iA Ic Id Ii iO Iu Js Jt Jy Ke Kf Lu Ms Nm No Nt oE Oh oN oQ Pd Pj Rf Si Sr Ug Uh Un Va Vt Vw Ye) Qa(Aa Ad aH aL aQ Ar aW aY bI bJ bN cC cP cZ dA Dg Du Ex Gb Gd Hp Ii Ik iO Iu Js Jt Kc Kf Ms Ng Nm No Nt oO Pj Rf Sr Ug Uh Un Up Uu Ux Va Vh Vw Th) Lx(aL aW bG bI bJ bN bP bS cA cC cD cP cS cZ Du eF iA Id Ii iO Iu Jr Js Jt Kn kO kP kQ mF mM mS mW mY nC nJ NT oQ Pj Rf Va Vh Vw Th) kP(aH aJ aP bA Cs Cu dF dL Et Ex Fa fR hB iA Im Is Jd Jl Jm Jn Jp Js Ke Kz Ma Mj Mn Mr No Nq nW Oa oE oF Qe Qh St Uh Uw Vh Vq Tl) mS(aA Bo bV cD cE Cq cT Cu Cw Ed Et Ez Fa fR Fy Ho iA iP Kl Ld lY Mj Mz Nd Nq Nv nW oF Ps Qu St Tr Tt Ua Uh Uk Vi Vv Wh Tl Xa) oQ(aH aK aL aQ aS aU aV aY aZ bF bG bJ cA cB cL cP cZ Hf Hq Ik Ir Iu Je Ji Ki Ky Mh Mp nB nC Nd nJ Nk nT Nw Oh Om Pd Qg Ry) oE(aH aX Bo bP cP cQ dR Ed Gl Ho In Jq kC kI Ky Ld Lz Mf Ml Mp Mq Mx Nd nJ Oh Or Ou Pk Pz Qb Qx Rt Uf Up Us Ux Vs Vw Wb Th) oO(aC aK aL aS bF bJ bN cA cB cV cY cZ dA dB dN Eq Hf Hq In Ir Iu Je Ki mH mW Nd nH nJ Nk Nm nT Nw Nx Oh Or Vp Yd Yl) aH(aC aM aW bP cU Ed Hx Ib Ik KC KG Ki Kj kN Ld lY Lz Mf Mx ND NJ Oa Oy Pb Pf Pk Qz Rz Ug Ux Va Wh) oF(aC Aj aR bI Ch cP EF Ib Ik iO Iz Kg kI lW mF Mu mZ nC Ng nI nJ nK nL Of Oy Oz Qt Qz Rz Ux Wd Wh Yg) hB(aC Aj Ap aX bC Ed Ef Fn Ib Iz Ju kE kO mF mM mT Mu mW nC Ng nJ nL Oy Qy Rz Uu Vs Vw Wd Zq) lY(aP cM cU Cw Ed Et Fw Gc In Iq Ji Ky Lh Ml No Nq NU Or Pf Pz Qc Qn Rv Ry We Yl Xa) kI(aL bV cD cE Cq Cu dF dG Ez fR Fy Is Jl Ks Ma Mj Mz Nd Ok oN Pa Ps Rf Tt Uc Up Vv Yg) nI(bF cE cG Cq Cu dF Fa iA Is Jl Jr Kq Lh Lv Ma Mz Nv nW Ok oN Or Oz pF Rm Vp Vu) nJ(aP cD cE cL Cu dF dG Ed Fa Fy Gp iA Ij Jj Ma Ml Mr nU nW Oa Ps Tr Uw Vh Vq Tl) Oh(aL bB bG bI bJ bP cC cS cZ dA eF Gd Ic iO Js Ng oN Rf Si Sr Ug Up Va Vw) Nn(bJ Hp Hx Ik In Jg Jh Kj Kn Mg mH mW My Nd Nt Qt Qu Ug Uu Ux Vw Tl Yf) nU(aA Aj aZ Ed Gp Ji Ke Kk Kx Li mE Mp Mq Mt Mx Nd Nw nY oH pF Pk Tz) Ik(aJ aP bA bB bO bP bQ cO cU dL iA Ij Jy kE Li mM Ps Qc Ut Tl) nD(aZ Ed Io Is Jq Lz Mj Ml Mp Nq Ny Om Ou Pf Qb Qd Qx Ur Vj Yl) Hx(aN aW bG bI bP cP cQ dH Dl Ex Gb Id iO kQ Rf Un Va Vw Th) Va(Is Jq Js KK Ld Lv Mp Mz Nw Ny Or Ou Pg Ps Qb Tz Vz) mW(Is Kx Li Lj Lp Lz Ml Mn Mx Nf Nq Oa Ql St Ur Vj Tl) mZ(cE Cu Ez Hq Is Jr Kq Ld Mx Nq Nv nW oH ON Or Tn) nC(Bo Dk Dp Fw Hb Ij Is Ji Jp Ke Kx Lh Nq Qc Uh Uw Wb) kK(aL aN dR Id Ir Iu lW Mt Nb oH Oz Pb Rj Ry Ur Us We) Tl(Dl Du Gp Hp Id Ii Il In iO Iu Je Ki Nd Ng Ug) nT(aP Cw dD dR Fw Ij Jn Js Lh Nf nY oH Oz Rm St) kC(aP Ax Cu Fy Ij Il Jn kN Mt Nr oN Pf Rh Ur Yf) Mx(Aa bB bG bP cS eF Id iZ kN kO kQ nB nY oH) lX(aP Bo

Figure 25 Continued cU Fw Gp Ji kS Ky Qc Ry Uw Vu Xa) kN(aX aZ Bo cD Ed Fn Fw iH Io Ke Mp Qb Tz) Is(bP Ii Jo mF ml mT mY nH nK Ug Up Uu) Ld(aL bG bP cZ eF iA Id Il iO kO mH oN) nB(Ih Jn Lj Mt Nr Oa Qb Qc Uh Vh) iO(aC cT Js Kc Ma Mh Mq Qx Tn Yi) Ed(aQ bF bQ cC cD cT dF mF mP) Ng(bQ Gp Ij Il Mt Pf Ps Tn Vi) Kk(Gp Hp Kc Kn mT nF Ug Up Vw) kE(bQ cD cE cL Cq Ma oN Pa Tt) Ug(cU Jm mM Oa Oz Qb Qc Rm) mE(cE cQ cU Et Fw pF Pz Qc) mF(cU Et Fw iA iH Pz Qc Vh) mT(dR Fr Mv Mz Nq On Ut Wh) mY(bA cT dD Fw Ma oN Tt Up) nL(Jp Lh Mj Nq nY Qc Qe Vj) Js(cZ eF kO lW nK nO oN) Pf(aL bJ bP dL Mg Nm Vw) aC(bV cD dL Il MM nO) bP(aL Ma Mn Ny Oz Yi) mM(aP dR lm nY St Vi) bQ(cF mH Oy Ss Vj) cZ(cT kF Ma Oa Yi) lW(cL Hq Lv Mp Or) St(Ii Jt Kf Nm) eF(bA cT Ma Yi) nO(bA Nb Oz Pk) mH(aP dR Nr Rf) nH(iA Jp Lh Tn) Qb(bN Iu Jy) Qc(Hr Nm Uu) On(Ii kO Vh) aL(aM Lz Qx) oH(Lj Oa Pk) Ma(Vj Vw) Mq(aR kO) Mt(kG nF) Pz(ml nK) Qh(Up Uu) Ny(Aa Je) aQ(cY Fw) cD(bO Tm) mP(nY Vi) AjBg ChtF GdMf Gpbl NmPs MgYi MnbN NdKp TrVw IiQe IlUx RxdF LjbG UpPg OydD OzdL dRnF} nA{Ry(aE AP aR aY Ba Bc bL bN bQ bZ cD CO Cq cR CS CT Cv Cw cX DB dE Dg Di Dl Dr Em Et Ez Fa hB Hc Hr Hv Hw Hx Ii Ip Is Je Ji Jj Jl Jm Jn kC kI kK kN Ld Li Lj LX Ly Lz Mf MH Mm Mq Mr mS Mt Mv Mx Mz Na nC Ne Nf Ni NK nL Nm nN Nr Nt OF Oi Ok On oP Ow Oy Oz Pb Pd Pf Pj Pk Ql Qt Qx Ra Rf Rh Rx Sr Uc Vh Vt Wh Yj Tm Xa Yf) Up(aJ aM aP aR Ax bA Bc bZ cN Cq cT Cu Cv dF dG dH Di dL dM Ed Fa Fn Fw Fy Ha Ho Hu Hx Ih Ij Im Ip Iq Is Jj Jl Jm Jn Jr Js Kj Kk Kn Ld Li Lj Lx lY Ma Mf Mh Mj Mr Mz Nk Nl nN Nr NW Nx NY oF Oh Oi Ok Ow Oz Pa Pf Pk Pz Qa Qb Qc Qd Qe Qh Qw St Tn Tr Tv Uc Uh Vt Vu Zw Wm) Yj(aH aP Ar bA bB bQ cD cE cL cM Cq cT CU Cw dD dF dG dM Fp Fr Fy Hx Ih Ij Ip It Jg Jj Jl Jn Js Kf kN Kq Kr Kx Ld Lx Lz Ma Mh ml Ml MM Mp Mq Mt mU Mz Na Ni nK nL Nn No Nq nU NW Ny Oa oP oQ Pa Pe Po Ps Ql Qn Qt Qu Qv Qx Ra Rv Sr St To Tr Uc Uf Va Vv Tl Xa Wm Ti) Oa(aA Af Ar Aw aX BN bS bU cA cl cK cN Cp cR cW CX dB De dH Dr Du Eq Fd Fi Gn hC HF Ib Ih Ii Ik Ip Ir Iu Iv kE kP kQ Kr Md Mf mM MS mW mY nD Nh Nj Nk Nl nT Or Pk Qz Rb Rg Ri To Tr Uk Un Uo Vz Yh Yl Zq Zw Wm) Wm(aC al aL bA bE bF bQ bR cB cC cD cE cJ cS cW cZ dB eC Ed Fc Fd Fi Fn Fr Fw Fy Gp Hf Hq Hx Ij Im Is Jd Jj Jk Kd Kz Ma MW Na NL Ny oE Oh Ow Pf Pi Pk Qh Qm Sf St Tn Tr Uk Uo Vu Vw Th) Uy(aR Ax cR cS cT CU dG dL Du Ez Fa Fp Fy gL Hx Ij It Jj Jl Jm Js Jv kO Kx Ld Lx lY Lz Ma Ml Mm Mr Mt Na nD nH Nj Nk nR Nu nW oF oO oP oQ Ql Qx Ra Rh Sh Tn Uc Tl Yf) Vq(aC Aj aR aW bA bF bl bQ bR cA cF cH Cw cY dB Em Fn Fy Hv Id iH Ir Iu Je Ju Jv Ki Kk Kr lW lX lY MF Mz Nb nC Nl Nw Nx oN Op Ow Oz Pb Pk Rf Rh Ru Zx Tj) Yf(aC aN aY bJ cA cl Cv cX Dd Fc Fn Hf Ho iJ Ik Je Jm Kd kE Ki Lp lX mE ml mS mT Nd Ne nH NK Nx Og oK Or Pa pF Ub Ul Vt Wd Yd Yk Yl Th) Vi(aO Ar bP bS bX cA Ch cK Cp cQ cX Ed Gn Gp Hf Hr Ib Ik Iu Jd Je Jv Ki Kr Mf mW Nb Ng nH Nj Nl Nq Og Oi Op Ow Qm Rt Sh Ub Um Ur Wb We Zq) Uw(Aj aN aY bE cA cF Ch cX Di Ef Fc Fw Id iJ Iu Je Jy Kd Lp Lv lW Mv Nc Nk Nl Nm Og OP Pa Pk Qb Qc Ru Rx Sh Ua Uf Ul Ur Vb Vs Yg Zx) Ru(aZ bL bP bR cB cH cM cR dB Du Et Gn Hr Hw Ih IP Ir Jo Kn LX Mr mY Mz nB NC Nd nH Ni Nk Nm Oi Qy Rm Rt Sr Ub Uf Tm) Tn(AF Aj AO Cp cR cW dA dE Ed Ef Eq Ez Hc Ib Iz Jh kE Li Lj Lp mM Mt Mv nC Ng nH nL Of Op Or Pb Pj Qw Ut Wd Yd Tj) Wc(aA aC aR aW bQ cF Em Fy Gz Ij It Je Jo Js Kc Kg Kx Ld Lx lY Mf Mh Mt mU nC nH Ni Nj Nu oE oK oN Qa Ri Ur Vp Wb Wh Zw) Vu(As Bo cW dA De Eq Fd Fi Gb Gh Hp Ib Il iP kE kO kQ mM Mv mW nC nH nI nJ nL nT Nx oE Or Pa Qn Rb Ri To Tr Un Us Vt Wb) Ps(AF Aj Al aO bP cA cQ Cx Dk Ed Hf Hr Id Ik Is Iu Jd Je Jv Lv Mb Ml mS mT mW NC nH Nk Nx Og Op Ou Qm Vs Yd Yg) Gz(As Ax Co dG Du Et Fp Fr Fy Ha hB Id Ih Ii Im Ip Kq lY Mr Nd Ni Nw Ny OE Oz Qe Qz Rg Rm Rt Tv Ub Uf Vh Vt Vz) Wd(aJ aS bA bV cE cH CT Cu dF dG Ed eF Ez Fr Fy Hc iP Is Jl Jn Mt mU Nd Nn Nt Nu oF oQ Qt Uf Vh Xa) Dr(Al aN bQ cD cJ cQ Ed Gl Ha Ij Im Ip kG Lj Lp mZ Nb Ne NL nN Nr nU Ny Pb Pc Pz Qc Rm Ul Yl Th) Va(aR Bc bJ cA cB cQ Dk Em Et iH iO Ip Ir Je Jo Kf Kk kO lX Mb Mf Mk Mr nB nC Ni Oi Om Pj Qy Sr Tm) Vh(Ad aF As Aw cF cT Ef Ib iO Jr Jv Kj Kn ml mT nC Nd Ne Nl nU oF Og Oy Pf Pj Qc Qm Qv Rx Si Uv tF) Lp(bZ Fy Ij Ip It Js Jy Kx Ld Lx Lz Ma Mh Ml Mq Mt Na Ni nK nL Qt Qx Ra Rh Yh Zw Th) We(aR aZ bA Bc bP Ch Cv dF fR Js Lj lX NB NC Nk No Nw Ny Ok Rm Sh St Vt) Tr(Af Aj Ao Ap Dl Du Ed Ib Iz Jt Lj Mg Mm Ms Ng Nt Nx Of Op Pd Qz Rb Ss Tt) Yl(aR bZ Co Cs Fy Ij Ip It Js Ld Li Lx Lz Ma Ml Mq Mt Na nC oF Qx Ra Tj) Wh(Aj As bQ bX dE Ed Ef Gl Ip Iz Jd Jh Lv mW Nc Ng nL Oz Pb Yd) eC(aI bH Bo cW dD dI dJ Ed Fn Is kO nC nH nJ nL Or oW Ri Ss Vt) Zw(Al An bF cQ Ed Fw Ha Ib Ip Iu Jm Lj mZ Ne nK nN Pb Pf Ul) Sh(cD Dc Ip Is Je Mm Nn Of Ok Oz Qa Qc Qh Rm Tv Uf Vt Ti) jI(Hv Hw Io jO Jr kK lK Mb Ml Mt mW Nc nD Ng Nt Oe Of Og) Lj(bL Cq cR dA Du Fi Fn Hf iZ Or pH Qz To Uk Un Yh Ti) lK(Et Hq Hx Iq jO jT kF nD Ng nI Nq nR Oe Of Om On Pg) Ib(Fr Is Jk Lx Nn Oh Ow Qa Qb Qd Qe Qh Rm Rt St Yg) Yd(Li Nm nN Pb Qt Qx Ra Rf Sr Tv Tz Uf Vj Vp Vt Vv) Ed(bI Nm Nn Of Pk Pz Qh Qw Qz Rx Uk Ur Ux Vt Yg) nN(bN cW Du Eq Fc Fd Fi Hp iJ Or Rx Vz Yg Yh Ti) Xa(As Cv Di Hr Ij Ip Js Lx Mf Nl Nn Ow To Th) Op(cD Is Nn Pk Qa Qb Qc Qe Qh Sr Uc Uf Uh Um) Em(Al As Bc Cv hB Ip Lx nK oE oK Pb Ub Tj) Gn(bQ Fy Ij Js Ma Mx Nr Oh Ok Pf Qb Qc St) Du(Ax Cq Ik nC Nd nK nL Ok Ow Ul Tj Th) Rt(dH Et Ho Ii Im Is Kn Nw Ny Ok Qe Tv) jO(Il kC kO lN lY nC nH nJ nL Nx Oe Oy) Qa(Bc cl cW Hf mW Pj Rb Rz Un Vb Zq) Rx(Cq Fy Is Nb Nr Nx Ok Qe Sr Tv Vt) oW(Db gP Hc Is mM Na Ne Nh Nu Of Oy) jM(Hu Jg Jm Jp jU kO nD Pc Pz qT) Ex(aN cA Cq Il Is Jm Kd ml Nj) Ho(Je Mf Mz Oh Pk Qt Qy Rf Rg) Vz(aN As Cw Fw Ij nL Nn Pf St) Vj(bA Ip Jn Ld Mq mT Ne Nl Nt) Yg(Al As Et mZ Nc Ng nK Oz) Wb(Ax Is Oz Qe Sr St Uc Uh) Rz(Cw Fy Ip Ma mZ NL Pf) Oh(Ba Ct Jd Kr Qy Rb To Vt) Cq(cC Cx Fa Kz Oy Ug Um) Lx(Fd Gb Gc Ri Ss Un Tl) Yh(aN Mn Nb nK nL No Ph) Si(Je Mz Nm Om Qb Qc Sr) Uk(Fa Ir Nr Nx Pk Qb Sr) Pf(cR Fa gC gL Jf Or Vo) Vw(Ax Ba Cu Ik oO Th) Pk(cB fA gZ Rv Ug Uo) lN(Io Jp kK kP Mm Qc) Bo(aC bE bH dD Qb) Co(Hp Pa Pd pH Ri) Eq(Ax Ha Oz Pb Qt) Zq(Ax Im nL Ok St) Wf(Bc Ij lX Nb nC) Tl(Ip Je Mf mS Nl) Lt(Bc Mf Nn Ow St) Oe(iC jG jH jY qY) Vb(BA Js Nt Qt) Ux(aC Cw Ik nY Uc) Fc(Qt Qx Ra Rh) Is(dB Fd Pd Th) Rb(Kk Nr oE Qe) Vt(Nx Ow Pj Un) fR(Ax Mf Qy To) qT(Hx Mz Nc Nu) pI(aV dA Fn Or) Tj(oV Pa Yk) Fi(Ij Im Ni) Gb(Je Nr Sr) Gc(bN Ms oE) Gd(Ij Ml Nr) Sf(Nn Qc Rf) Qb(Bn bU fP) Qh(Af Bn De) dU(cB dA nL) fA(cB nK Pi) qY(Hx Jh Oy) Bc(Fd Sr) Fa(cW Nk) Fw(bN Nk) Gh(Oz Qu) Uc(Af Nx) Sj(nL Ow) Pz(Pj Zx) Tm(aN Il) Li(Or Ri) Rv(Nu Oy) dD(Ip oV) nD(jP qU) iC(Nc nI) kQ(fB oT) AjSr AsSt AxHq CwRi TiIm FdIj MhQz MsOr HpOw HxqV TooE YkPb QcjT QecW QuYe KzPa UhbH UnbZ PgjU dAoT gCnH nOpK} lY{Up(aC al aV Ax aZ bF BG bH bQ bZ cA cB Co Cq Cs cV Cw cZ Dc dD Dk eC Et Fa Fp HB hC hG Hq iA Ib Ih Ij Il Im Ip Iq Ir Is Jj Jn Jp Jq Jr Ke kI Kk KN Ko Ky Lh Lj Lx Ma mE Mn mW Mz Nh Nk nO Nr Oa oE oF Ok On Or Ou Oz Pb Pc Pd Pf Pg Pk Pz Qa Qb Qc Qd Qe Qm Rm Sr St Tn Tr Uc Uh Vi) Ry(aE aH aN Ao bB bE bG bN bS bW bZ cA cK Cq Cv CX cY dD dH DL Du Fd Gc Ha Hb hG Hp Hq Hx iA Ik Il Iu Je Ji Ki kP Kq kR kS Lh Lx Lz Mb mH Mk Mm mP Mq Mr mS nB Nf Ni Nj Nk Nm nO Nw Nx Ny Oe On Op Or Pc Pz Qc Qd Qw Qx Rv Rx Tz Ub Uc Uw Yl Zx Xa) Wc(aC aH al aN aU aV bE bJ bQ bS cA cB cE cI cK cL Cs cV cW Cx dC dD dE dH DL dN Ed Fn Gc Gn Gp Ha hG Hp Hq lH Ii iJ Ip Ir Is Je Jq Ki Kk kP Kq Kr Ma mH Mj mM Mq MW Mz Nd Nf Nq Nw Om Or Ou Pz Qb Qc Qd Qe Qw Rg Ri Rx Tn Tr Ub Uc Yl Zx Xa) Ri(al aP Ar aZ bG bH bl Bo bQ bZ cA cB cQ Cw cZ dD dF dR Ed Fp Fw Gc Gp Hb iA Ib Ij Ir Is Jj Jn Jq Jr Js Ke kI Kj Kq Ky Lh mW Mz Nh Nw nY oE Oh Ok Or Oy Oz Pb Pc PF Pk Pz Qa Qb Qc Qd Qe Qm Si Sr Uh Vh Vt Zq) Va(Ao Bb bE bF bJ bL bX cA cP cZ dA dD Dk Ed eF Et Hq Ib iH iJ Is Jj Jq kC Kq Ky Lh Mf mH Mj Mn MW Mz Ni Nm nU Nw Ok On Ou Pc Pk Pz Qc Qd Qe Ql Qm Rx Tn Ub Uc Vt Vu Vz Yf) Rv(aC As aW bE bJ bX cF cl Cq Cv cX dE dK Ed Gl Gz Ho Hq Hu Ib Id Il Jg Jj kP kR Ky Lp Ma mE Mn mS mW Mz Ne Nl Nm NN Nr Nu nY Ok Om Or Pc Pd Pk Qb Qe Rx Tr Ub Uc Uy Tj) Gc(aC aI Al aR As bF bG bN bZ cB cE cJ cL cQ cX dD Dl Ed Fn Hq Ib Ik Il iO Ip Jk Jl Jm kP Lp Lx Mb mE Mf Ms MW Nb Nc Nd Ne Nl nN Nr nU Nw Oa oE Or Pb Pc Si Ue Vq Tj) Uw(aC Al An aW aY bV cB cO cP cQ Cv cX dE dG Ed Fc Fw Gl Gz hB Hq Ib Il Iu Jm Kd kG Ki kQ Lj Lp Ms mT Mv Mx nN Nw Nx Og Qb Ru Rx Sh Ub Uf Ul Uv Uy Vb Vs Vt Wd Yg Yh Th) Rt(aO BG cE Cq Cv dF Dk Et Fr HC Hu Ij Ik Il Is Jd Jl Jp Jy Lh Ma mE Mj Mn Mt Mu My Mz Nq nR nU Nv NY Og Ok

Ua Vv Wh) mY(Aw Cw dC Nb Qw) Mu(aG aH dA oK) Ii(dD Hu Ly Mb) Iz(aO bF bG kQ) Jo(Na Oe Qw Vp) Rh(aW dI Na Vp) bE(An Gn Ip Ub) nD(kE Ms Qe Uh) Aa(bC Ow Pc) Lx(Fy Js Om) Pz(dA Jt Nm) Qb(Ar Js No) Qu(aH cD Pg) Ki(nY Pg Pi) dL(Nb Oi Rj) Ch(oH oK) Gp(Ap Ba) Ua(bG oF) Hu(cX dI) Vz(Rv Va) Zq(aH Et) Kg(aC Nx) Kk(Iu Oi) Rg(cD kQ) Of(bF fR) Ow(Js No) Vv(Pg Rv) lW(Tr Ue) mI(aU Ne) CqbC CvkK CwQc EdfR EmaC EqbG GzmF MhiZ MyoF NaUf NdKp HokE TnkN InOz WbmU RcOe WdfP QhOm NxVa} mM{oE(Ad aF Ap Ar aS Ax Bb bH bI bL bX cD Co Cq Cu Cv Cw Dc Dk dN eM Et Fn Fr Gb Gc HB IJ Im Is It Jg Ji Jq Js Jt Kd Kf Kk Kl Kq Ld Lh Li Lj lW Lx Ma Mm mP Mq Mx Mz Nm Nn Nq Nr Ns nT Nv Ny Oa Of Oh Ok Om On Ow Oy Oz Pe Pf pI Pj Pk Ps Pz Qa Qd Ql Qm Qn Ri Rj St Tn Tr Uc Uh Uk Ur Ut Uw Vh Vt Vu Wf) Tn(aC aI aJ aR Ax aZ bE bJ cB Ch cR Cs Ct cX dD dJ dR Ef Et Fn fP HB Hc Ho Hr Hu Hx Ib Ik Il In Ip Is Iu Iz Jh Jj Jm Kc kE Kj Li Lj LX Ly My mZ ND Ng nJ Nn Nw Oa Of Oh Ok Oy Oz Pb Pd Pf Pz Qc Qt Qw Qz Rh Ss St Uh Uk Up Uw Vq Vs Vt Vu Vv Vz Wc) Vq(aI aJ aQ aU Ax aZ bI bQ cO Cs cV cY DD dG dJ dR eC Ex Fp Fr hB hC Hx iA Il Im Io Iq Ir Js Kc Kj Kk Ko kP Kq Ky Kz Lp Lt lW LX mE mF mH Ml Nb NN Nq Nu Nw Ok On oO Ow Oz Pb Pf Ps Qa Qb Qc Qv Ra Ry St To Ug Uh Uk Ur Uv Va Vo Tl Xa) Uw(aA aK Ao aQ aU aV bE bH bJ Co Cu cX cY dG Du Fb Fy Gd hC Hr Hu Ij Im iO iZ Jf Kc Kk Kq Ks Ld Lh Lj Lv lW LX Mj Ml Mq Mw nB Nn No Nr nY Oa oH oP oQ Oz Pb Pc Pd Pe Pf Pg Qa Qb Qe Rj Ry St Uy Vi Vo Vw Vz Yd Tl Tj Th) hB(Ax bH bN cB cC Du eC eF cQ Et Ex FA Fd Fn Fr Fy Gd Ha Ih Ij Im Iq Is Iu Jm Jn Jq Ju Ko Kp Kq Kz Li Lj Lx Ml Nf Nj Nl Nn Nq Nr nT Ny Oa Of Oh Ok Om On Oy Oz Pb Pd Pi Pk Qa Qb Qd Qe Qh Ri St Uy Vb Vo Vt Vu Vv Yl Tl) Oa(aC aI aL bE bQ bU cN Cq cR cV cX dD Dp dR eC Et Gp Hb Ho Hx Ij Ik Im In Ip Is Jg Kc kP Kq Lh lX Mm mS mU MY nB ND Ny Oh Ok On Oy Pd Pf pI Pz Qc Qh Ri Rv Uc Uk Uo Ux Vh Vi Vu Wd Wf Wh Yl Zw Zx) Vu(aI Ax Bo Cw dF Dg dJ dR Et Fd Gn Gp Hw Ij Il Ip Is Jg Kn Ko Kq Li Lj nD nI nR Ns Nv Nw Oh Ok On oO Pa Pz Qa Qc Qd Qm Ri Tr Uc Uk Up Ur Us Vj Wd Wh Yd Tl Xa) St(aA Af Al aO As AX bH Bn Bo cD cJ cV CX dB De dF dG Du eC Gn Ho Ib Il Jj kE Li Lj Lx nD Nh Nk Nl oP PF Pz Qw Rb Ri Rt Sh Si Sj Uk Un Uo Up Ux Wm) Vi(Aj aO cR Cv Dg Du Fn Gd Ha Hr Hu Hx iO Is Jj Jl Jt Ki Kj Kl Ko Lh Li Lj Lv Lx Mg mS Mx mZ Nc Nf Nt Oe Of Oy Oz Pb Pc Pd Pg Po Qa Ri Tt Uy Vt Tj Th) pI(cO Cs Ed eQ Fa Fp Ha hC Ir Je Jl Jq Js kN Kq Kx Ky Kz Ld Li Ma Mf Ml Mr Ms mT NB Ne Nf nJ Nk NN Nu nW Ny Oe Ok On OW Oy Pi Pk Po tF) Is(aI An Ax bN Bo cB cV dG eF eM Fd Gn Ha Ho Jd Je Jp Kd lK nC nH nL Ok pF Ql Qv Qw Rb Rf Ri Rm Rt Sf Sj Ue Uk Un Uo Up Ur Vb Vs Wm Ti Yf) Kq(aI Aj Ax bH cB Ct cX Ef Eq Gh gZ Ha Ho Hr Ib Ip Iu Jj kE Kj Li Lj Lv LX Mf Ms ND nN nT oT Pf Qw Rb Rg Ri Uk Un Uo Ut Wc Th) oW(aE AL aQ aV cB cC Co CV Cx cZ Dd dR hC Hu Ip Jj Kd Kn Ko Ld Md Me mP mT Mu ND nI Nq Ns Nv Nx Ny oH Ok Om oT oV tF) Ri(aI aZ bQ bZ Co Cw dF Et Ex Fr Fw Gp Ij Im Ir Jn Jq Js Kc Lh Li Lj Lx Mn No Nr Nw Ny Ok On oO oQ Pf Qa Qb Qc Qd Qe Qh) oT(cD cH cL Co cQ Cw Fr Fy Gp Ij Im Ir jB Je Js Kn Lj Ma MF Ms nH nJ nL NN Of Oh Om On Pa Pf Ph Pi) Qa(aC aI aY Bo CV cW dD dJ eC Fn fP Hb Hf Ho Ib iJ Ip iZ Kd Ko Nt oN Qm Qn Qw Uh Uk Un Up Vj Vz) Oh(aI An Bg cB cD Co cV dB eC Fb Fn Ib iJ Kc Kd Ko oD oN oV pH Qm Qn Qw Rv Tr Uh Uk Up Ux Vt Yl) Ij(aC aI bE bH cB cR dD Dr Du eC Fd Gh Gz Ib Op Pj Qh Qv Qw Qz Rg Ry Rz Uk Un Up Uy Vj Vv Vw) Uk(Al Dc Et Fa Ih Im Iq Ir Jm Jn Jq Js Kn Lj Lx Nb Nn Ny Ok On Oz Pf Pz Qb Qc Qh Rm Sr Vh) Li(aI bF BG bH bZ cE Ch Co Cq Cu cV dF Dk dR eC Ef gP Hc iA Jp Jy Ou oV Qw Tr Uc Yd) Im(aI Ax bN cB Du eC eF Gd Kj Op oV Ry Rz Sh Ue Ug Un Up Ur Uy Va Vb Vj Zq) Ok(aI aJ bH cD Cx Ed Fn Gd iA Ib Jj oD Pb Qc Qh Qx Qz Rf Rg Rv Sj Vz Yl) eC(aI Ax bZ cH Dc Ex Fn iA Ir Js Lj Lx Mj mY Nb Nn Nq Ny oQ Pf Qb Qh Sr) jB(aQ aV cB cC Cp Cs dG dR Fa Fp Hx Iz Jt Kl Kp Kz Ml mT nN Nu Nw Of Oy) Ax(aI bH Cq eM Et Fr Jk Jn Jp Jq Jr Nd Pd Pf Pz Qd Qh Rg Uc Vh Wh) Lj(aG aH aI bH cB Cq cV Dc dD dU fA fR Hb Ho iJ Ps Qh Rg Uc Yd Yl) Ny(aF cR dG Dr Du Fa fR Ib kE Op Oy Pb Qz Rt Sf Si Ug Up Vz Wm Yf) Nn(aI dD Fn Gz Hb Ib lK oV Qm Qn Qu Qw Rf Rt Tr Uh Up Vt Zw Yf) On(aI Aj bH Ct Eq Gn gZ Ha Ib lK Qw Rb Rc Si Up Uy Vj Vt Wm) Lx(aI bH bJ Dc dD Hb Ho iA Kc Ko Qw Ss Uh Up Vj Vt Yj) Pf(aI cB Dc Du eF Fa Fd Hb Ho Ke Ko Qh Qw Uy Vt) eQ(aE aL bM cB Et Hb hG In Ip Jq mW nI Nq oD Pa) aI(aJ Bc Cu dG Fa Fr Fy Ih Js nN Nr oQ Wm Tj) Qh(Bo Fp Ib Jj Nr Pz Rf Rh Sh Up Wm Yf) Ps(bH Fn Hr Ik iO Ip Lh Pb Pd Ub Vz) Yl(Bn cT Hx Lp Me Mh Mt oQ Pe Ra Yf) Ho(aP Js Ld Mf Mj Mx oO Po Qe Vj) Jm(eM Ex fA Gp Qv Ry Up Vj Wb Tl) Rv(bQ Fa Hx Mx Nb Nf Ow Oz Pk) Up(Et Fr Iq Ir Jn Jq Pz Qb Qe) dF(bH Et Hr Jj Jq Qw Rf Uh Vt) Jl(Gb Gh Rx Sf Sj Uy Vh Zx) Rm(aC Du Op Sf Sh Va Wh Zw) Yj(aU bJ dD Nh nY oH Tz) Oz(Cu Fn Gd Gp Vh Wd Wh) oD(Co Fa Fr Ml Ni Nk Pk) Dc(Jj Kz Ml Oy Ur Us) Et(Pj Qv Ue Ug Un Va) Uc(Jj Kj Kz Ml Oy Vo) Pz(bB Cs Fa Fn Gd Kz) Js(Gh Rt Si Uy Vz Wc) Vt(bQ eF Fr Gp Nr Va) fB(Cw Dg Fy Kn Of Pk) fR(Mx Nw Rf Sr Vj Vz) oV(Co Il Ir nJ nN Ow) Fd(Ld Mj Mq Ow Qx) Hx(Co Cw Ux Va Vh) Qc(iC jD jG lK Rf) Qd(Ib Qx Rf Rh Un) Gp(Cq Fa Ha Rf) Mx(Rt Ux We Zx) Tr(Jj Kj Pb Rg) Wh(bQ Kj Ng Rj) Lh(Ib Op Rx Yf) Vh(Ik nN oQ Si) aC(aH Gn nT Ry) fA(bQ cC Ir Kn) Th(Ma Mr Nr) Lp(Ik Ip Mj) Rt(Ld Mq Ow) Cq(Ml Nq) Yf(Rg Tj) Fa(Jg nI) Fr(Eq Ib) Gn(dR nY) Nr(Fn Hb) Zx(nN Ow) Qb(cV Rx) Qe(Rf Rx) Wc(dD Jn) Om(Ib Pb) Pk(gC gZ) bH(aH Pe) lK(nR Nv) AnDr BbGd CoJj CuIk WmUh ExIp FyRh NqjE MjRy NcjI NkpH HbnN IqUr JgKj WdbQ JnRj JqaJ XaiO LdUy OedU OwUx VwbZ PgjG aUdR dDnT dKgZ} nN{Dr(aG aH Al An Ao aR Ba BB bE BG bH bJ bQ cE CH cI cP cR cU cV cZ Db dC Di Dk Dl dN Dp Du Eq Fn hB Hu Hv Hx iA iH Ij Ik Il In Iu Iv Iz Jg Jk Jm Jp Jq Jr Jy kC kI kP Kq Ky Lv Lx Mf Mj Mn Mv Mw NB nH nJ nK Nq nR Nx Ny oF oH Oi Om On Op Or Ou Pf Qa Qc Qd Qn Qw Qz Ry Sf St Tn Tr Ub Uc Up Ur Uu Va Vp We Wf Yd Yg Yf) Uw(Af aK Ap Ar Aw bH bN Bo bS cA cK cO CP Cx cY dA dD DE dF DG DL dN Ex Fi fR Hr Hu Hx iA Id Ih Im Ir Iu Iv Je Jo kC Ki Kl Kn kP Kr Ly mH mP Mr mS mU mZ Nb Nc NJ Nk Nl Nm NO Nu Oe oN oP Oy Pd Pe Qu Rz Tv Ub Uf Up Ur Vi Vj Vs Yl Zq) Vz(aC aH aI aO Bb bF BG bH bQ bZ cE cJ Cq cR cS Cu dC dD Dk dL Ef Eq Fr HC Hu Ik Il iP Iz Jd Jh Jk Jl Jp Jy kC kI kK kO Kq kR Lh Ma Mj MT Mv Mw MY Mz Nd Nq nR nT Nx Om On Ou Oz Pb Qu Qw Qy Rj Rx Tn Tr Uc Ut Vo Vp We Wh Yg Zx) Wf(aI Aj aK Ap bE bG bJ bN bS bW cA cK cP cY dA De Dg Dl dN dR Fi Fn Gd Hb Hp Hv lH Ik In Ir Iu Iv Ji Jq Jt kC Kg kI KR Ky Lz Mf mH Mj Ml Mp Mq mS Mx Nj Nm nO NT Nw Oe oH Ou Oy Qa Qx Sh Tz Ug Ux) Zx(aE aJ Aw aY bE bJ bN bS cA cK cQ cR Cv cY dC dE dH dI dK dL dN Gn Hr Hu Hx iA Ih Ik Iu Iv Je Jj kE Ki kP Lv lX Ly Mb Me mP mS mU mY mZ NB Nc NJ Nl NT Nu Oe Oy Oz Ph Rg Sh Um Ur Vi Yg Tm Th) Yl(aE aR Aw bG bH Bn Bo cF cN Cq cW dC dD dG dH Di dL dR Du Et Fw hB Hr Hv Ij Ip Iv Jq Ks Ld Lh Lp Ly Ma mE mH Ml Mm mP Mq Ms mU mZ nB No Nr nT Nu Ny Oe Oz Pb Pc Pi Po Ql Qn Qx Ra Uk Um Uv Vi Vq Vu) bH(aI bN Bo cB cS cV eF Eq Fi Fn Gp Hb Hp Hw Id iJ Il In Iv Jj Jq Kd Kk Kn Ko Lp nD Ns Nt Nw Or Ps Qg Qn Qw Ri Sh Sj Ug Uk Up Ur Va Vb Vt Wc Yd Zw Ti Yf) Vi(aI BG bZ cE cV Dk dR Fn Fr hB Hc Hq iH In iO Iv Jl Jp Jq Lh Lv Ma Mj Mu Mv Mw My Mz Nb nJ Nq Nt Nv Nw Oe Of On Or Pf Ph Qc Rz Tn Vp Yd Th) Yd(Aj Aw aY bE bJ cF Cp Cv cW dH Dl dN Hr Hu Hx Ib Iv Ki Kl kP kR Lv lX Ly Me mP mS mU Nb Nc nD nI nJ Nk Nm Oe Ph Pi Ri Rz Um Vt Th) Fi(aI aR bG Dc dN dR Et Im Jg Jk Jp Jq Jr Jy kC kI Kq Lh Mj Mm Mn nB Nx Og Ok Om oN Oz Pb Pc Pz Qh Qn Rg Rj St Uc Ur Vp Vq Vu) Ri(aI aM aW BG Bo bZ cD cE Cu CW Dc dF dG dM dR Em Gc Gz HB iA iP Ke Kk Kn Kq Lx Nn Oh Qa Vh Vt Vu We Wh tF) Vq(aC Af aK aL bE bN bS cA cK cN cP cR cV CX cY dA Dd dH dL dN Du Id Iu nB nJ nO nT oH Or Pd Ph Rx Zq Ti) We(aC bF BG bZ cE Dk dR Fn iH iO Jl Jy Kq Ma Mb Mj Mu Mv My Nk Nq nR Nx Oe Of oK On Ou Tn Uc Vp Vu Th) Rz(BG bQ bZ dR Ez Fr hB HC Il Jg Jp Jy Kq Ma Mj Mn Mt Mz Nq Ny Ok On Ou Pz Qt Qw Qy Uv Vp Vu Th) Yh(aD aG aH aN Bb bJ bM cH cI cW Ez Fn Gb Ho It Jh Jk Jn Jv Kf Me mI nD nJ nK Qt Qy Uk Uu Uv Ti) Vh(aC bE bN bS cA cK cY dA dL Hr Ih Ik Ir Iu Iv Ki kP Mb Nj Nm No Nt Ub Zq) Yj(aG aK aQ aU cB cY Dk FR Gp It Jp Kr nL Nw Om Op Ou Pz Qc Qd Sf Zq) Up(aI Al bG Cu CV cZ Dk dR Et HB Iq Is Jm Kq OH Or Qa Qe Qh St) Zw(aR bJ bN cP cW cY dA dE dL Fn Iu Iv Je kC Ki kR Nd nJ Nk No Rx Ub) Vt(aI aL aS bE bF bG bZ cV dD dR eF GP hG iA iJ mW Oy Rx Un) Nt(aI bF BG bZ cE Cq Cu Dk eC EF eQ Hc iJ Ko Kq Or Wh) Rv(bN cA cY dK dL Hu iA Ih Ki kP Mb

Figure 25 Continued mY Nj Nl Nm nT Rg Ur) Ex(bN bS cA cK Ih Ik Ir Iu Iv Ly Mb Me nB NJ Nk No) Or(aI aY dD dU eC fA Hb Ho mP nD oN oV pI Uk Vu Ye) aI(Af aO As bB BN Fn Gn Hr Kr mI Nk No Ph) Rx(aK aR bN cZ Hu kP mH mS Nc Nd Oe Ug Uv) Zq(Cq cR Et Ih Iu Jm Jq Ki Lh Qh Qn Vu) bN(Gc Gz Is Jq Lp Ny Op Qm Sf Tn Uk Wh) Nk(cD cV eQ Fa fR Gz Hp Ko oD oN Sf) dU(aK cB dD Hb Hw In Jq mT Nw Om Pa) Is(aO bS cA cK lK Lp Ph Rt Vs Xa) pH(aE aK aQ aV dN Hw In Ip mW Nw) Fn(bG eC iA iJ Nn Oh Op Qa Ux) Iv(eQ Gz Hb Hf Kk Ko Lp Op Wh) Jq(Af Aw Bn cR Cx dD Fd Pj Tl) Tr(aC Af aY Bn Cp Dl Kl Ph) Yg(bJ Jg Jj mP Ng nl Rj Ub) oV(cB cP cQ dA dB kI Nq Tj) Du(aR Cv dR Oz Pb Qh Rg) Fd(Dc Jm kR Mj Qh Uc Vp) Hp(Cv Dc hC oN Pz Rg Ur) Tn(aE aO aY dN Hu kE nO) Hb(bG iJ kS Lu mI oN Vu) Op(Hr Ih Ik Iu Lv Nc nT) Cq(Af fR Gd Sh Wb Th) Gb(Dl Ik kP Nd Nm nT) Gc(bJ cY Nm nT Ur Us) Gn(aK bG cY Mj Om Ou) Wh(Dl Ik kP Mb Nm nO) Ps(cR dH Dl Ik Ki kR) iJ(Ct Lh mS nI Qu Th) oD(bS cK dH Ih Ir Mr) pI(aJ cM cP dA kQ tF) Bn(Dc Et Kq nR Uc) Eq(dN Hx kR mS Rj) Ho(Je kR Mf mS Ug) Xa(dR Ez Ki Lx St) Ye(kP Ni nT Nw oE) Vb(dL Ez fP oF Vu) Ux(aC bE hC kP Nm) Oy(Bg Cu cV dA Dk) jB(Ao Dg gP Mn nU) lK(Iq Jm Nn nR On) Yf(Bc Pd Pz Tj) Ti(hC Rg Rm Vu) Em(dH dN Hx Um) Sh(aR hC Nx oN) Kk(dD eC kP Pd) Kq(aO Qw Rg Ut) Uk(bG Cv dN hG) Uy(kR nB Nd nT) fR(hB kN Nx Uc) Et(Af gP Kr) Th(bG iA iH) Tm(cW Nd nJ) Lt(bE Hx oH) Rt(dR Uv Vu) Vw(dL hC nB) Ph(Co Ny Ok) eC(cW Oe Qv) Gh(nJ oH) Gd(hC nB) Nc(jH jI) Ib(Nx Om) Ik(Sf Si) Pz(jM qY) Wc(Ez iO) Wd(Nd Vu) Qu(bG cV) Tl(Mj Oz) Ry(bE dN) Vj(Ma Om) aP(gC gZ) eM(dA nO) kE(fA Ny) AfDc CpNv CvUg MfWb NljI SjkR QclM SrNw QhcA JmjM JtKo KsVu PgqX aEeQ aOcV aUdR cPoT fBkQ mWoN} nJ{Vq(aA aC aK aL aU aV AW Ax bB bE bF bI bJ bN bQ bR cA cB cC cF cM cO cR Cs cT CW cY cZ dA DD Dl Dr Em Et Fa Fb Fp Fr hC Hu Hv Id Ih Ij Ik Im Ir Iu iZ Jj Jm Jn Js Kc Kk KN Ko KP kS Lj Lx Mf MH Ml Mm Mz Nb nC Nm Nn Nr Nu nY Oa oE oF OH Ok ON Oz Pf Pk Pz Qa Qc Qe Qv Ra Ri Rj Rx Rz Sh Sr Ug Uh Uk Ur Uv Vh Vj Vu Wh Zw Yf) Wc(aA aC aD aH aI aK aL aQ aU bJ bL cB cL Cq cT Cu cV cX cY dD dF Dg Dk Ez Fa Fn Fy hB hC Hq Hu Ik Im It Je Kc kF KK kN Lv Mj Mp Mr Mt Mx ND nH nI Nk nR nU NY Oe oF OH OK Om oN Ou Pa Pd Ps Pz Qa Qb Ql Qt Ra Rf Ri St Tz Uc Vh Vi Vj Vp Vv Vz Wh Yk Tl Wm) Uw(aA Aj Al Ax bO cA cF Ch cI Cv cX dE Ed Ef Em Gl Ho Hx Ib Ii Ik Im iO Ip Iq Ir Is Iz Jd Jc Ki Kj Kq Ks Lj Lv lW lX Mf Ml Mn Ms mT Mv Mx MZ nC Ng Nk Nr Nw Nx Oa oP Pc Pe Pz Qa Qc Rj Ru Ry Sh Ss St Uu Uy Vs Yd Yj Zx Tj) Gh(AP Ax bL Co Cw Ez Fr Fw Gc Ih Ii Im It Je Jm Jn Js Ld Lj Lz Ma Ml Mm Mq Mz Nk Nm Nn Nr Ok Om On Ow Pf Ps Pz Qa Qb Qc Qt Qx Ra Rf Rh St Tr Tt Tz Uc Ue Uh Ur Uy Vi Vj Vv Wh Wm Tj Ti Yf) Tn(aC Ad Aj AO Ap Ba bN Ch Ct Cu Cw dE Ed Ef fR Hc Ib Iz Jd Jh Jj kC kE Kj Kl Ky Li Lj Lp Lv Mf Mm Ms Mt Mv Ng nO nR NT Nx Oa oE Of Or Oy Pj Qt Qw Rb Rc Ry Ss Ut Va Vt We Wh Yg Ye Th) Va(aF aQ aU aZ bJ bL bZ cB Cq cV cY Dc dR Fy hB Hx Ip Ji Js Kk Kq Ld Lh Mb Mf Mp Mq Mx Mz NC Nk nR Nx oH Ok Om On Or Ou Pg Qb Rf Ri Rm Sj St Tr Tv Vh Vu Vv Vz Yk Yl Tm Tl) Vi(Ad Aj Ax Ch Co cR cT dE Ed Eq Ik Ip Ir Iu Iv Iz Jd Jj Jt kF Kl Kj kP Lj Mf Ml Mx mZ Nd Nh Nj nK nL oK Oy Qy Rf Rg Rt Ry Rz Sh Si Ut Vz Wd We Yj Yl Zq Tj Th) Ry(aC aE bB bF bQ bZ cC cR dF DR Et Ez Fr Fy hB Hx Jl kN Kq Ma Mb Mf Mj Mm Mt Mz Ni Nr Ny oE oF ON Oz Pb Pf Pz Tr Tv Uf Uv Vh Vp Vv Zw) Oa(aI bN bU cE Cq cV dD dL Dr Du GP Ii Il In Ir Is Iv Jq Jy Ms mW Nj Nk Pf Ri Tr Ug Un Up Vh Vz Wf Yh Yl Zw Wm) eC(aI aK aV Aw bH Bo cW dD dI dJ Ed Ex Fn hB Is Jq kC kI Mf Ml Mp Mx Na nT OE Oh Or Pk Qb Qd Rh Ri Ss Ub Uc Vt) Wd(bQ cE Cu eF fP FR Fy hB Hc iA Jp kF kN Kq Ma Nq nR nW nY oE oF ON Oz Pf Pz Tr Uc Wh Yg) Yf(aC aI As bJ cB cE Cq Dd dE Fn Hq Hx Ik iO Is Jm Mb Mj Nn nR nU Ny Or Ow Oz Qh Uc Vp Vu Tj) Is(aO bR cB cR cX dB Hf iC lH Jd jE jU lX Mj mS nH nU Pd Rt Rx Sf Sh Si Sj Uy Yl Tl Th) Vh(aA aC aI As bN cB cR cV Hu Ib Ik Ip Jh Jm Kj Lj Ml Ms mT oQ Pb Ri Uk Uy Vb Vw Vz Tj Th) Vz(aH aN Ax bF bZ cD Ih Ij Il Js Lj Me Ml Mm Mx nC Nt Ny oE Ok Pa Qx Ra Rm Ru Rx Wm) Si(Ax Ij Im Je Ji Js Kq Mf Mm Mx nU Ny Ok Om On Ow Pz Qa Qb Qc Qe Rf Sr St Tz Uh Vt) Yl(Dr Fa Fy Im Ip kN Kq Lp Mj Mr nC Ni Nj Nt oE Oh oK On oQ Pd Pe Pz Ql Ru Tt) Uy(aI bB Cu dD dF Fr hB Jm kN Kq Ld Mj Mq Mr Mt Mz nR Nv Nw Ok ON Pz Tt) Tr(bH Ed Fd Gd Gn Jt kC Li Lj Nt Nx Op Oy Pd Qb Rz Sh Vb Vu Vw Wh Yj Ye) Dr(Al As Dd fR Fw hB Hq Ij Ik lP kG Nb nF nU Ny oE Ow Qc Rm Vu) Yh(aN bF Cq Fw Jm Mx Nb Nn Nr nU Nv Pf Ph Rm St Tj) Ps(aC Al cR dE Ed hB Io Ip Iu Ki kP Mb Mf Nr Oz Pb) Ru(aC cB Dc Et fR iO Jm Mr nW oE Ok Qe Qh Rm Vu Tm) Lp(bZ Fy hB Ip Jl Js Ld Lx Ma Mj Mq Mr Nw Pf Qa) Ri(Co Cw Ex Gb Gc iO Lj Lx Nr Qd Sf Uh Vu Zw Tl) Wh(As bQ Ed Ik Jm Ma mT Nc Ng Nl oF Oz Vu Ye) Vb(bQ dF Fy hB Il kN Kq Mt Nr oK ON Pz St) Ho(Ij Jm Js Mf Oh Pz Qa Qx Ra Rh Ug Vj Wm) We(aC Ax bQ bZ dR hB lX Mf Nb Nc Nd Nw Ye) Rv(Fa Fy hB Mb Mf Mx Nc Ni Nl nW Oz Pk Qe) Yg(aC As Dc Ib Jm Mf Ng Nq Oz Qa Rm St) fR(Ip Mf Mx Pz Qx Rf Sr Vs Vt Vu Wm Th) Ex(Al aN bN Cq Il Ip Kd Nn nU Pa Rg) Rt(Dc Ed Et hB Ij Jm Kk Nb Ny Ok Qe) Eq(Kq Ma Mz Nn On Oz Qa Uc Vp Vu) Yj(bF bQ iA Kq Ma Mr nU Nv nW St) Wf(Ax dR Ed Hx Kj Lj Nb oO oQ Rf) Vj(bQ Fy Ik Ip Jl Jm Ms Oz Qa Vu) St(Em Fi Gb Gc Gn Ib Up Ye Tl) Vw(bQ bZ Cu dF Fy Jl Ok oN Qa) Zw(Al Cq lP Iu Nb nU oE) Xa(As Ip Js Mf Nw Oz Qa Vu) Rx(bQ Nb Nn nU Pf Qe Tv Vt) Lj(aI cB Cq cV Jy Kq Or Yd) Du(bQ Cq Il nU Ok Pf Qc) Rz(bQ Ip Kq Ok On Pf Qt) Vu(Bo cV Gb Gn Kd Kk Ko) Fd(bZ Ma Nr Ok Pf Qa) Sh(Mm Ny Pz Qh Rm Uf) Ye(Qc Qg Qt Qu Rm Uc) Tl(Al Ik Il Ip Pb Pz) Up(Dc Iq Jm Lx Qa Qe) oE(Em Fn Gb Gc Rb Wm) Gn(bQ hB Nn Pf Qa) Bo(aC bE bH dD) Co(bH Ik Pd Rg) Tj(aI Jq Sf Yd) Et(cX gP hA Zq) Rm(Fi Gb Wb Zq) Ux(aA aC Mx Ow) iB(kP mS mW Nc) Wm(aI cB Jj) Fn(bQ dB Pf) Gc(Ik Jl Nn) Gd(Lx Pz Uc) Yd(Ax Vp Vv) Qa(aP cW Ib) Qc(jD jT jV) Em(hB Ip) Th(Nn Pf) Fi(Im Jm) Gb(Lx Tv) Hp(Je Qe) Wb(Jm Oh) Sf(Ib Nw) Pz(Op Tm) Rf(kC Sj) Ny(cR cX) Vt(dD Pf) bH(Cw Uh) cB(Mf Pk) fB(kQ Ma) pI(cR Or) ArbE AxZx CxOk DbaI DcGz EdQh FaMs FykC IjiC IpdD ZqQe JglM JqcX TmOw LtnC PimS fAgZ nOpK kQoT} Oa{nD(aC Af aI As bE bF Bg bH Bn bS bU bZ cA cE CH cK cN cP Cq cV CX Db dD dH Dk dL Ed Ef Eq Fd Gp Ha HC Hq Ih Ii Ik Il In Ir Is Iu Iv Je Jl Jt Jy kN kP KQ Kr Lu Lv Ly Ma Mf Mm Ms mW mZ Nj Nk Nm nO nT Om Or Ou Oy Oz Pd Pf pH Pj Pz Qt Qw Rg Ri Rx Tn Tr Ug Up Vu Wf Yd Yl Yf) kE(aC Af aI Ao bE bF BG bH Bn bS bZ cA cE Ch cK Cq cR Cu Cx dD Dk dR Ef fA fB Gp Ha hB Hc Hq Ih Ij Il In Ir Is Iu Iv jB Je Ji Jp Jq Jy kI Kk kP Kq Lh Lv Lx Lz Ma Ml mS mW mY Mz nB Nl Nj NK Nt Nw oH Oi Om On Or Ou Ow Pd Pf pI Pz Qa Qc Qd Qw Tn Uc Uk Wh Yl tF) gP(Aj AR AW aY bL bN bS cA Ch cK CP cR dA DC DE dJ dU fP Ha Hb hG Ib Ik Iz jB Jk Jo Jt kP kQ Mb Mu nB Nd Ne Ng nI Nj Nk Nl oE oH Oy Pb Pd PH Pl Qh Qu Qy Uf Uk Up Vs) mS(Af aI Ar Bg BN bS bU cA cB cK cN Cq cR cV dC dD dL Du Gz Ha Ho Hx Ih Ii iJ In Ir Is Iu Iv Jt kI kQ Kr Ms mW My nC nH Nj nL Nm NO Nt Or Oy Pa Pf Pz Ri Rx Tr Ug Uk Un Up Vb Vu Wm) pI(aH aJ aO Ar As aW aX Bn bS cA cK CP cR cW CX dB De dF dG dH dL Hf lH Ii Im Io Iq Ir Iu Jd Je Jn Jr Ki Kq Kr Li Mj Mn mW mY Nj Nl No nT nU Nv nW Ok Pc Pg Ph Tj) nB(Af Ar As aX Bn bS bU cA cB cK cR CX dH Fd Gn Ha Ih Ii In Io Ip Ir Iu Iv Jt kP Kr Li lX Nh Nj Nk Nl nO NT nU Pa Qu Ry Sh Sj Tr Ug Uk Um Up Wb Wf Yj Yl Zq Tl Ti) kP(aA aE Aw aX aY bH bL Bn bU Cq cR cT Db eC Gb Gc Gn hC hF Ho Hr Io Ip Is kC mI Mp Ms mU mW Na Og oN Pd Pf Qm Qu Rg Rt Rv Uk Uw Ux Uy Vb Vh Vq Wf Wh Zw Ye) mY(aC aI Aw bE Bg bH bS cA cK cN cP cR dC dD Dk Gc gZ hC hF Hr Ih In Is Iu Je kC kI kQ Mf mU mZ Nd Nj Nk No Nt Or Oy Pd Pf Pz Qa Qb Uk Up Uw Vh Vt Vu Yf) mW(aC Af Aw aY bH BN bX cN cQ cR dC dD De dI dU eC fB hC Hr Hu Hx Ik Ip Iu Lv mP mU mZ Nb Nd Nk Nt oN Oy Pb Pd Pg pH Rm Uk Up Vu) pH(aC aE Af aK aM aQ aV Ax BA cB cR cU Cx dA dD eC Gl Hb Hq iA Ip kC kF kG kI Ko LX My mZ nC nH nL nO nY Ou Oy Oz Qm) kQ(aE Aw bN cJ Cp cQ Cw dC dD dJ dU eC eM fB Gn Ib Ic Ik Jd Jo Jt MU Nd nU oD oE oT oV Pb Pd Pf Ph Sr Un Up Vi Wf) mU(Af aX Bn Bo CX Em Eq Ic Ii Ik In Ip Iu Jt Kc Nd nU Oh Or Ow Pf Pz Qa Qc Tr Ug Uk Up Wb Yl) bN(aR aW cP cR cS dA dJ hC hF hG Hr Ib iJ iZ jH jP jT kC Ne Nj Nl nW nY Pb Pd Ph Pz Uk Up Tm) hC(dJ Du Eq Fd fR Hp Ik Iq Lp lX nI nU Rt Rz Sf Si Ux Vi Vw Wd We Yg Ye Xa) Tk(aP aZ bX cB cF cJ cL dJ dM eC eF Fb Kk Kn Kz Ld Mc My nY oE Ou Ub Uk) dU(Af aK aM bU cH cY dB dD Hb Ii Jd Jo Jt Kc mE mF mI Ml mT My nK nO) kC(aE Af Bn bS bU cA cK cN Dr Ha Ir Iu Iv Kr Nd Nj Nk Pa Pz Rg Ri Wm) nW(aQ dJ Fi Gn Hu iO Jd

Fn(bQ cX iH) Mx(Eq Gh Yd) Vz(Nd nU Tt) Or(Im Ms pI) Oz(Fd Gb Ug) bE(Ar Bo fR) Qd(jT jV) Kr(Mj Qh) Rz(Ma Qt) Ru(cR Lh) Op(Kq On) Vt(bR cV) Pb(Eq Wh) Pd(jT Tr) cB(dU gZ) dA(gZ pI) eQ(cP mT) nK(jO jY) iB(mW Nu) pH(Ir nO) AIJj AnTm DbaI ThRg FiIm FwMs GcbQ MmWb MwZx NejP UcUx IkLp YdOm ZqOn ZwaN PzLt SrUg WeoF JqcX XaKi RvdK UwaW cQpI fBkQ fRkR nHjI} Yj{bZ(aC Ad aI Aj Ap aX aY bC bE bF bI bJ bO bP cA cE cG Ch cL cP Ct Cw cZ dA Dg dJ Ed Ef Eq Fn Gh Hq Hx Ib It Iu Iz Jh Jj KI Kj Kl Kn Mg MU mY Nb Nd Nf Ng nI nL Nm nU Of Og Oi oN Ow Oy Oz Pb Pc Pd Qt Rc Ri Rj Rx Rz Ss Ug Uk Uu Uw Ux Vh Vq Vs Vv Vw Wd Wh Yg Yk Zq Tl Th) nU(aM aP aQ Ar aU aW Bg bQ bV cD Co Cu cY Dc dD dF dG dJ Dk Fa Fb Fn hG Ih Ii Ij iO Ip It Jh Ji Jl Js Ke Kk Kn Kq Lh Mj Ml Mr Ms mU Mx Mz Nb Nd Nl Nq Nr nW Oe oH oO oP oQ Ou Pg Ps Qa Qd Qe Ql Qt Sr Tz Un Ut Uw Vh Vt Vz Yl) nI(Af aG aI aO aP As bB bF Bn cE cJ Cp cQ CU cV Cw dF dG dH Et Fa Ha iA iH In iO IP Ji Jq Js Kf KR kS Lv Ma Mm Mn Mz Nb nF nT Nu nW Ny Om oN oP Or Ou Oz pF Pg Po Qh Qn Ry Tn Uk Up Vp Vq We Yd Yl Xa) oP(Aa aC aE aL aN aU bB bC bG bV cF cI cO cW dA dI dK dN Fn Fp Gp Ha Ho Hv Hw Ib Ik Io It Jg Jk Kx Ky Lv IX Lz Mb Mc Mg MP Mv Na Nd Nf Ni Nl nO Or Pk Po Pz Qy Rx Sf Ss Ua Um Vq Xa Th) nR(aG aJ aQ Aw bC bE bG bM bW bX cI Cq Di Ed Fn Fw Gz Hb Hr Ij Io Jg Jk Jo Jp Js Ke Lh Lj Lp Ly Lz Mf mP Mr Mw Mx mY Nd Nw nY oH Op Ou Ow Ph Qb Qc Qd Rv Rx Tz Uh Uw Vw Vz Yl) oQ(aC aG aL bJ bL bM bO cE cH cI Eq Hq Ik In Iv Jg Jk Jn Jp Jt Kg Kj Kr Ly mI Mn mP mU mW NB Nd Nh nK nO Nq Nx Of Og Om Ou Pd Pg Qd Qm Sj Ub Up Vp Vs Wh Yd Yl) Tl(aI aL aO bB bE bG bQ cE dA dD dF Et gC Gd Gp Gz Hq Hv Hw Id Ik Il In iO Jy Kq Kx Lv Lx Ma Ms Mt Nd Nn Nq Nr Nw Og Oi On Ou Pf Pg Qh Rg Rv Ub Ug Uk Um Vi Vq) hB(aC Aj aX bE bO cA Ch Ef Fn Gh Ib Jd Jh Jj Jo Kc Mu Nd Nf Nj Og Oy Pd Qz Rz Sj Ss Uk Uw Ux Vq Vs Wd Wh) aI(Aj bP cA cE cL Cv dJ dL Fn gC Gh Ib kI kO Ld Lx mE Mr Mu nC Nd Ni Nj Og Oy Pb Pf Rv Ss Uk Xa) gC(aH aU aV bJ bX cV dA dK dR Ez Hu Io Jg Js Kf Ko Ld Ma Mg Mj Om Ou Pa Qm Qn Vz Yk) nT(aK aQ aU bB Cs cY dD dR Fr Ij Jd Lh Mn Mr Mt Mx No Nq Nw Ny oH Pe Po Tz) kI(aO Ba bV cE Cq Cu cV dF fR Hq Ih IP Jg Kf Ma Ok Ou Qd Tn Uc Vp Vq Xa) Uk(aH Et Hx Is Ji Kk Lx Nn Nw oF OH Ou Ow Pf Pg Qa Qb Qc Qe Qh Rm St) mY(aA aH aO Ba bQ Cq Cu dD dF Et Fy Gp iP Jg Ma oF Ok Pz Tn Tr Ua Vq Yg) Lx(Ar bJ bP bV cA cL cS dL eF Fy Gh iA Jo kS lW mF mI nW Pi Rv Ss) kC(cT dF dG fR It kN Ld Lz Mh Ml Mq Nn Nq Ok Pz Qx Ra Rf Vq Wm Yf) kN(aJ cD Fn Hq iH Io Jn Js Ke Ld Mq Mr Mx Nw Ow Qb Qd Tz Uh Yl) lW(dF dG dH Et hC Hq Hx Jq Js Lv Nw Ny Ok Ow Pg St Tn Uh Vq) Ow(Ar bJ cA cS eF fP Gh iA Ic Kx mW Nd nO Pd Rv Yk tF) mF(aH bF gP hC Hq iA Jp Jy Kr Ma nW Ny oN Pz St Tn Tz) nK(aP Cs Fa iA Ih Ij Js Mr No Nr Pe Pz Rf Tn Uw Vq Vu) mU(aA aK aU cB Cq dD dF Fr It Jg Jn Nh nY oF Pz Rx) oO(bJ bM cI cV dA Eq Hc Jd Kf mH Ms nL Qg Ub Wf) oF(Aj aR Ef Fn Ib iO mI Mu Ng Oy Rg Ri Rz Ss Wh) kK(aN bF bQ cY dR fR Gp iH Nr nY oH Qh Rx Uh) lX(aQ aU bB dR iA Ij kS Mn Mr Nq Ny Pz Rv) nF(aK aQ aU cY dD Fr Jd Kk Mt Nw oH Tz Uh) kE(Cq cV fR Ip Kq Mj Nd Ny Ri St Ua Vq) kF(aC bC bE cB cY dD Fn iH Mr Or Ou Qd) Hx(dI eF In kQ mW nO Oi Pd Pf Rv Va) aH(bO cA cL cS Cv Gh Ib Nj Og Ss Wh) mP(cE Cq cU Cw dF dH dR Ij Jl Ok Qa) nO(Cq Cw dF Jn Nb Nq Ok Uw Vq Xa) mE(bF cJ iO Ip Jp Mr Nb Ny Pz Qh) eF(bA bQ cT Ld Oh On Qa Vi Xa) mI(Ij It Js Mr Nb Nr Pz St Uh) Xa(Gd Ik In iO Nd Ng Ug) bJ(Im Mn Mt Nn On Pf Qa) mH(Cq dF Ij Mr Uc Uh Vq) mT(dD dR Fr Jd Jg Mt oH) nB(aJ aP Ih It Nn Oh Pz) nC(Dk Dp Et Fn Nq Qc Uw) Ss(bB cU dF hG Ky Pg) Rv(bE Fa Ik kP Ng Ug) Qa(Jo Kl Mg Ug Vh) bV(In Ld Mj Oh Ou) nL(As cJ dH Hq Mr) kP(aG Jn Ny Uc Vu) oH(Aj Ch cU Lj Mx) Ib(aO dD fR nY) Jo(Et Il Pf St) Ug(Cq Fw Ql Rm) mW(Jn Ld Lz Mq) Aj(BG nY) Ng(Mt On Vq) Oh(fP iA tF) Pg(cL Qx Rt) kG(dD Fr Mt) Aa(Et Im) Fn(cS Il) Mg(On Pf) Ik(Ij Ql) Tm(Gp Nn) aC(iO iP) kO(Nw Uh) EtPj MsJi NdKy LdiA QlaR NycL OgdL UuVq OynY bPdD dBfR dFnH} Vj{Oh(aC aI AR bF BG bH bJ bN bQ bZ CH cI cN Cq cS cV dA dD Dk EF Fr Hc Ic Id Ih Ik Il In Ip Is Jk Jl Jy kC Ki KK kO kS Kx Lu MT Mu Mv My Mz nB Nc Nd Nk Nl Nn Nq nR nT Nx Og ON oO oQ Oz Pb Pd Pf Rb Rf Rv Tn Tv Ua Ut Vi Vp Vu We Wf Yd Yl) bQ(aC Aj Al Ap aR Aw bJ cA cE cG cI cL cP cR Ct cV Cw dE dJ eF Fn fP Gh Gn Hr Hu Hx Ib Ic Ik Ip Iq Jd Jf Jh Ki Lu lW lX Mf Mu Nc Nd Nf Ng Nj Nk Nx Oe Og Ow Oy Oz Pb Pd Ql Qu Qy Rg Rz Sj Ss Tv Uk Vi Vq Vv Wh Zq) Qa(aA aC aE aM Ar Aw aY bA Bg bH bZ cH cN cO cQ cR dD Dg dH Du Fd fP Fy Hr Hx Ib Id Ik Iu Jo Jr Js Jt Ju Jy Ke Ki Kn KR kS Mf mP Mt mU nB Nc Nd Nm No NT oN Oz Pd Qe Qy Rv Sf Sr Ua Uk Up Wf Ye) bZ(aA aC aM aY bA Bb bJ bN cI cP CQ cT cV cW cY DC Di Dl dR fP Ho Hr Hu Hx Id Io Is Jk Jm Ki Kk KN Kr kS Li Lv Ly Mb Me mI mP Ms mU Nd Ng nT Ny Og oH On Ow Oz Pb Pc Rj St Tv Vu Ye Tj Th) Nn(aC Ap bA bJ cA cI Cq cT cV dA Dc dE Fn Hu Hx Ic Ik Ip Is Je Jh kC Kk Lv lX Mf Mg mH Mj Mp Mx Mz Nc Nd Nf Nk Nl nR Nx Ny Oe Or Ow Oz Pd Pg Ps Qb Rh Rz Sj Ss Tn Tv Tz Uc Vp Yd Yl Yf) Tr(aC aQ Ar aS aW bA bB Bg bJ bN cI Ct cY dA dB dC dl Dk Fr Hc Hr Hu Hx Ib Id Ij Ip Je Jk Jr Js Kk Ko Kp Li Mu Mw Nc Nm Nt Ny Oe Oy Oz Pd Qm Qy Rh Sj Ua Ut Vp Vu Wd Yl Ye Tm Tl Xa Th) Is(Aa aC Ad Ap bN bV cN cS cT Dc Dd fP Ic Id Ii Ik Iu Jo Jt Jv Jy Ke Kf Ki kP Kr Lx Lz Ma Ml Ms mY Nd Nk Nl Nm Nr nT Ow Oz Pd Pf Qv Qx Ra Rt Sh Sj Sr Tn Ug Uk Up Uu Uy Va Xa Wm) Lx(aC aI AR Bg bH bJ bS cA cI cK cO cP Cq cR cY dA dC dD dE dH dK Eq fP hC Id Ih Ip Ir Iu Je kC Ki Kk kQ Kr kS Kx Lp Mf Nc Nd Nk No nT oH Pd Pe Po Rf Rv Ua Ub Uc Vp Yl) Ma(aA aF AR aY Bg bH bJ bV cP Cq cW dC Di fP Fr Ho Hr Id Ij Ik iO Ip Je Jk Jm kE Ki Kk kS Li lW mE Mf MP Ms Nc Nd nT Oz Pb Pd Ps Qm Rh Tv Ua Ut Vu Yd Yl Zq Xa Th) Oz(aK aQ aU bA Bg bP bV cB cF CT cY dA dR Eq Gp Hc Hx Id Ip Je Jv Lv Me Ms Nc Nd Ni Nk Nl Oe OF oH Ow Pa Pc Pf Pj Pz Qv Rv Sh Si Ss Tn Tz Ua Ub Uc Ug Um Uo Wh) Ow(aI AR bF BG bH bJ CH cI Cq cR cS cV dA Dk Ef Fr Hc Id Il In Ip Jy Kk kS Lu Mu My Mz Nq nR Nx ON Pb Pd Pf Rf Tn Ua Ut Vi Vp We Wf Yl) Tn(aA aC Ap aR aY bF bI bV cG Ch cI Ef Hr Hx Id iO Je Jh Jm Ke Li lW Mf mI Mm mP Nd nK nT Om Pb Qx Ra Si Sj Zq Tl Wm Tj) Pf(aC aR bA bE bJ bX Cq cT cV cX dA dD dK Fn Hu Hx Ik Jl kC Kk mE Mf Mm Nc Nd nK Nm Ny oH Pd Ps Rh Rz Sj Vp Vw Yl Yf) Hx(Bg cF Ch Co Cq cS CU cX Fr Hb hF Id Ij Il Je Jf Jm Ki kQ kS Mf nC Nd Nk Pz Rv Tv Vu) cT(Ad aI aR BG bH Ch Cq cS Et Id Il Kk Kq KS Mf Mn Mt Mu Mz Nr Nx Og Pb Pc Pd Vu) bA(aC Bg bH Ch cS hF Il Ki KS Mt Mz Nr Nx oF Og Pb Pd) Js(aI Ar bF BG cV dA fP Fr hC Id kC Ki nT) Cq(Fy Gp Kc Ld Lz Mh Ml Nr Qx Ra Ug Xa Wm) Wm(aI cV dR Ik Kk Ny oH Qd Qh Vp Yl) Ld(BG dA Fr Id iO Ip Kk kS Pd Yl) aC(Ba Bg bV dF Fy hG iP Pz Uf We) dD(cM cU Ed fR Fy hB iP Je Nd Tv) kC(Ij It kN Lz Mh Ml Qx Ra Tj) Yl(Ax Lz Mh Na Nr Qx Ra Rh) Pb(cV cY dF dR hB Lv oF oH) Ip(mE mH mP mU Nr Rf Rh) Je(aS bV fR nR Ny oF Xa) Ez(fR Iu kG Nc Nd oQ) Fy(bJ cI cP cV fP Rv) Ij(Ap Ik lX mH nT Sj) Pz(bE lX mE mF mI nR) Uw(mF nC nI nO nT Sj) Nr(bJ cV Mz Nd Vp) Mx(Bg fP Id Il kS) Jm(Nd Nl nT Ug Uk) oH(Li Lj Nu oK Tj) Ik(fR kO Li Ra) cU(aQ cY dR lX) hB(Mf Nc Nl Rz) Ne(lX mP nT) Kk(Qx Ra Rh) On(bJ bV lX) Vu(kE nO Ug) cV(Mt Qx Ra) nR(aF dK Lv) mW(bH Hr Wh) oF(cI iO Qz) Et(bN nC) Gp(As Cu) Mf(bV dR) Nc(dF Qh) Nl(Ps Uc) Ib(bF dF) Il(bJ Hu) Kq(kE mF) Ok(nI nT) AaRm AjBg BaSj NkbV HokP IdNy TtbJ TvbN QbfP StUp XaiO KioO NwlW PdmU bEiP bHmT} kE{Tn(aC Aj aM aO aV bJ cA cB Ct cX cY dD Dg dJ dR Ed Fn Fp Gl hB Hu Ib Ij iO Iu Iz Je Jj Jk Jl Jq Jr Ke kI Kj Kl Kp Ld Lh Li Lj Lx Lz Mf mI Ml mP Mq MT MU Mv Mw Mx My Nd Ng Nn nO nR NT nU Nw nY Of oP oQ Or Ou Ow Oy Oz Pb Pc Pd Pf Pi Qb Qd Qx Qy Sh Ua Uk Ur Ut Vo Vs Vt Th) Kq(Af aO bH Bn De Dg Ed Fa Fn gP Hr Ib Iu Jj Jt Jv Ki Kj Kk Kr Li Lj Lv Lx mI Ml Ms Nb Ni Nj Nk Nt Nw Oe Oh Op Pd Pg Qb Qd Rc Ry Rz Uk Up Vb Vo Vt Vu Vw Vz Yl Ti Th) Yl(aR bA bZ Cs cT Cu Cw Dr Ez Fa Fr Fy gL hB Hc Hx Ij Il Im It Jl Jn Js Jy Ld Li Lp Lx Lz Ma Mg Mh Mj Ml Mq Mx Nb No nR NY Ok ON Pe Qt Ra Rf Rz St Ur Vi Wm) Lj(Ad aH aI Ao bF BG bH bQ bZ cA cB Ch Co Cq Cu cV Cw cY dA Dc dD dF Dk dR Ef Fn Fy hB Hc Iz Jy Kk Ko oH Or Ou oV pK Qu Qw Tr Tt Uc Uk Uv Uw Vp Yd) Ny(aD AF aG aM aO bH Bn bP bS cA cK cR Cx Dr eF Fa Gd Hu Ib Je Jk Kj Kp Kr Kx Mf Mj Ml Mr MU Mw Mx Nq nU nY Op Pb Ph Qy Ry Sf Vs Vz Wm Ti) Ij(aC aD aI aK bE bH cB Cq cR cV Dc dD Dl dR Ed eF eQ Fa Fn Fy gL gP Jv Kk Kp Op Or Pj Ry Sh Tr Uc Uk Up Us Vu Vv Vw Vz Wh Zq Tl Wm Tj Ti) Lx(aC Ad An aP Bb bE BG bH Bn bO cA CV Cw Dc dD Fn Fy Gc gP Kd Kg Kk Kl Kn Ko Mr Pk Qn Ry Si Tr Up Vs

Figure 25 Continued

Vt Vz Wf Ye Xa Yf) bH(aH Ax bA Cu Cw Dc dF Fr Fy hB Im Jg Jn Js Kk Kl Kn Ld Li Mt Mx Nb Nn NR Nv Ok On Pe Pf Qa Qd Qh Rf St Tt Uc Vu) eQ(al aN aP aV Bb Bo cB cQ Cv Dc Fn Hb hC hG In Jj Jq Kd Kg Kk Ko kQ Md Ms mT Mu mW Na Ns nU Nv Ok Om Pa Ph) Pf(aC An Ax cB Cv Cw Dc Du eF FA fB Fd Fn Fy gL Ha Ju Kd Ke Kk Kn Kp Ld Op Pk Qn Qw Tr Us Vb Vo Vt Vz) Qa(al An Bg bO Co CV CW dJ Fb Fn Fy gP Hf Id iZ Je Kd Kk Kn Ko oH Pb Qn Qy To Tr Vs) Oh(Ad al An aX bF Bg bL bO Ch Co Cp Cq Cu CV Cw dB Dc Fb gP Id iZ Kc Kd Kg Kk Kn Ko Vs) Vu(aH al Bb Bo Co Cv Cw Eq Fd Gn Gp Hc Jq Kd Ke Kj Kk Kn Ko Ld mP nO Nw oH Ok Qd Uh Ur Vs) St(aD Af aM aO Ar As bL Bn Bo Cx De Dr Ed gP Ib Kk Kr ml Or Ph Rv Sf Vt Vz Zq Xa Ti) Is(aD al An Ax Cv Ed Fn Fy Gd Ha Ip Kd Kk Kn Ms Mv Ok Qn Si Tr Va Vb Vs Vt Ti) Qd(Af aS Ax bN cT Ed Fy Ib Kk Kx Ld Ok Ow Pb Qv Qx qY Rf Rh Tr Un Up Va Wm Tj) oW(aV cB Cw dA dR Fn Hb hC Ip Jj Kd Ke kl Kk kN Ko Lh Md mT Mu Ns Nw Nx Oi Ok) Fy(Ed fA Fw Jo kl Kj Lh Lz Ml Mq Nw Or oT oV Ow pl Qb Qx Rv Tz Uk) Nb(al aM bl bX Dr Ex fA Fw Gc HB Ke Ky Ld Lp Or oT Ou Ow Pk Rv) On(Af Ap Bc Bn Bo Ct Dg Dl Ed Ib Kj Kr Or pH Rt Rv Rz Vb Vt Vw Vz) Li(bF BG bZ cE Ch Co Cu Dk dR Ef Hc Jy kQ oH Ou oV Tr Yd) Nn(al AN BO Cv Cw Fb HB Id Kc Kd Ke Kk Ko Qy Vz) Tr(Ct Ed Fw Jj Jo Js kl Kj Lh Lz Ml Or Ou Ow Qb Qx Tz) Ok(Ed Fw Kl Kj Kk Lz Ml Mq Nj oO Or Ow Pb Qb Qx Wm) Lh(Dr Ed fR Ho Ib Op Ru Rx Ry Sh Si Va Wh Yd Wm Yf) jB(Ax Cs dN Fp Ha Hr Jj Ju Jv kN mY Mz nB Nc) Nw(Ed Eq Ho Pb Pk Ry Uw Vi Vq Wb Wd We Wh) Qb(Bg bZ Co Cu cV Cw fP hB Rz Vi Wh) fA(cQ Fw Jo Kn Ky Ma mT nB Pa Ph Pk) Jq(Ax Fb oF oT Ow Pb pl Uk Wm Tj) Ow(cB Co Dc Fr Nv Om Uw We Yf) hB(Fn Gd Pk Ux Uy Vt Vw Vz Tl) oT(Ad Cw Je Ma Ms Ne Ni Pi) Ed(Cw Dc Jg Qh Uc Vq Wh) Fn(bQ bZ Cu dF Fr Nr Vi) Mj(Ax Cw Ry Uy Vw Vz Wb) Mx(Co Eq Rx Uw We Wh Yd) Qe(Cv Kd Kk Rx Sh Va Vs) Fa(aH al Gp Kk oH pl) Nr(bS cA cK Ke Or Th) Dc(Gp Lz Ml Qx Ur) Im(bS cA cK Or pH) Ry(aE Cq cR Mb Ri) Nq(Ax cA eF Kk) Kj(Jh Ma Uw Vi) Vt(aS bQ dR Ky) Pk(bQ Fr oV pl) nY(Du Lp Uw Tl) Nk(fB oD pK) Qc(jG qY Up) Wh(Ib iO Vb) Qh(Bo Rx Sh) Kk(Ml Oy Vq) oV(dR Ir Ky) Ax(Or Ou) Co(gC Jj) Cq(Op Uy) Fr(Ib Ld) Uw(Lv Vb) Vq(bE dR) Vw(bZ Cw) bQ(Rv Vb) gZ(nC tF) oD(Ni Tj) pl(Ky Pi) pK(Cs Fp) MfHo UbRu UcVo IkUx IrUr ZqRm JgOr KnfB LdPd OmPb PgjL alaM} pl{Or(aW bF bJ bQ bZ CS Db eM eQ Ez Fa Fp Ha Hv Hw Is It Jh Jo Jq Jy kC kK kN Ko Kx Ky Kz Lj lW Lz MF MH Ml Mq Mr Mt Nb nC Ne Nf Ng nH Nj NK NL Nn Nr nU Ny Of Oh oK Om oN oQ OW Pe Pk Po) Fn(Aa aR aW Ax aZ Ba bL Cs Ct Cw Cx DB eQ Ez Fa Fr Fy Hv Hw Ij It Je Js Jy kO Kz Li lW Lx Mf MH mP Mq Ms Mw Mz Nc nK nL Nn Nr Of oK oN oQ Pf Ql Tj) Pk(Aa Af aH aO As bB bG Bn cR Cx dA De Dg Dl dU eC eM fP iH Ii In Iq Ji Jo Jp Jt Ju Kf Ki Kr Ld Mj Mm Mn mT Nh nU Ny OF Ok oO Oy Tj) Nl(aN aW bL Bo cB cJ Co cQ cR Cw dA dC Dk eC Et Fa Hb Hv Hw iZ Jf Jq Kf kl Ko Ky Lh Lu Me mF Mg Mh My Mz Nk Nm Nq Nw Oh Ok tF) cQ(aH bH Cp cR Db dD dR eC Ed eF eQ fA Fr Fy Hr Iq Is Jf Jv kK kN Kr Li Ly Mh Mm Ms mT Nc Ne Nf Nh Nn Nu Of oO Oy Pi Tj tF) dA(aR aW Ba bM Co Db eQ Fa Fr Hv Hw Ir It Je Js Jy kl Kz Ld Li Lx Lz Mh mP nB nC Nf Ni NK nL oK oN oQ oV Pd Pf Po Tj) Ma(Af aG aH Ao Ap bB bH cA Ch Ct Cu dF Dg Dl dM Dp Hr iA Ip Jd Jg Jt Jv Kl Kr Lv Mj Mn MT Mv Nc Nh nU Of Pe Pg) Kz(aO Aw Bb bC bH Bn bU cA cl Cs DE dH Dp GP gZ HF Hr Hx iH Ip Jd Je Jn Jp kQ nC Nh Nj nL Nq oD oK Pg) Tj(aN aO aQ aV bF bM Bo cB cl cP Cq cS Cu cV Cx Dc dR dU Hb Jn kC lW Lx Me Mz Nv Nw oD Oh oK Qm tF) Fa(aJ aO aP Ar aV aW Bo cl Cs dB dG Di dL eF fP gP Hf hG iH Iq Jd kQ Kr Nh Nj Nk No Nq nW oO Oz pH) Mf(aZ bG cM Di eC gC gP Hc Jj Kk kN Kr Lz ml mT Na Ne Nh Nk Nt Nu Oe Of oO Oy Pi tF) Jf(Ax Ba Bo bZ Co Cq Cu Cw Ed kO Lj Ms mT mW NC Ne nH Ni NK nL oK PF Qm) cB(aR Ax Ba bM bZ Co Cs Ct Cu Cw DB Hw Jy kO Li Ml Ne Ni Nj nK oN oV Pf) Bo(Al aO cR Dp eQ Hc Hr In Iq It Jd Je Kp Lj nB Nc Ni Nu Oh Pd Pe Pf tF) Co(aK bU cl Cp cR cY De eF Hf Ih Ii Ik Ir Iu Jo Ki Kr Li mW Nq nT Ph) eF(Ar As bH cA cl Dp eC Fp gZ Ha Hr Ip Lj Mv Mz NC nH nL Nm oK) Nk(Aa Aj Ao aZ bZ cl Hc hF Iu Lx mF Mk nB Ne Nh Nu Of oO Oy Pi) Kk(AA aO aW bH cl cR CX Dp Hr Jd Je Ml Nh Ni oD Oe Oi) Lj(aJ aQ cW dB dL dU fP Hf iZ kQ Kr mF My nO Nq Nr Nu oO) tF(Ba bH cS Ct Cw Db Dp Ed GP gZ hF Hr Je kO Nc oK pF) cR(An bF Db gP Hq Ij Jh Jq Lx Na NB Nh nL Nv oO Qm) Fy(aH aO As bB Bn cl Cp CX De dU Iq kC Kr Nq nT) hG(aG aH bG eC Ed Fp iJ Io Iz Jd Je kN Mh nB Ne Oy) aV(AR aW Ba bM Cs Cw Hv Li mH Ni Nn oV oW Pf) mW(aD aO Ax cX Dp Jd kK Li Ml nB Ne Nf Ow Oy Po) eC(aA bR Dp Hf Hq Jd ml Mm Mn Nh Of Ph Pi Pj) kQ(Ed eQ Fr Ha In Iq Jm kK Li Ml Nf Ni Ow Po) cl(Ax bZ cO Ij jB Kq Ky Ld mH nB Ni oK Pd) mT(aF aN aZ dB Hw Kg Ko lW mF My Nm Oh Oi) Pi(aO bB bN bP cX dE Ip kR Mn Nq Nw Pg) cM(Ar Ax bZ Cq cS Cw Db Je kO Nc Ni nK) Nq(aC dD Iq Je kK Ms nB Nc Nf Oh) Ne(aN Hw Jh Ly Mb My Nm Nr Oh) Nh(aW cF Et Fr Ko Mz Nm Nw Oh) Ky(Ad Af aH Bn Cx Dg Dl Ki Of) Nc(aN dB Hw kF kl Ko Lh Nm) Ao(Cw jB Kn kS Ok Om On) aO(bZ Cu Js Kq Lx oN Pd) mF(Al bH Cv Dp Hr Jd Ni) Hf(Ar Ax Fp Li lW Oh) Jq(aH Aj Bn Cp Ki Kr) Ok(Af As bU Cx Db Pj) nT(Ar bL Fr Js Li Pd) Nu(aR dB kR Ni oK) Kr(Ax Ip Ir Mz Ph) aH(bZ Kl Ld Om Qm) bH(dB Hb Js Pd Qm) Li(bS cK Ih Ii) Ar(aJ dL oO) Ax(aJ aQ cP) Db(bV Cv Lh) Dp(aW mH Pd) Nm(Mm Nt Pj) Ni(dL Hc Na) Je(aN Lh Nr) Ko(Ed Jg Jv) Oh(dB iH oO) Oy(cW iZ Of) aA(Ed Iq kN) Af(Js On) Fr(bU iH) Mm(Mz Nw) Hr(dB Hb) Hc(Ba Mg) aY(nC nH) cX(kN Om) dD(bA oV) mH(Ip Jv) nB(dB iZ) kF(nC nL) AjNg BclX BnJs ChgC CtOw CukO FpcW HaaQ NtaR MliZ MsaN IqiH QmaG NwPj aKoD cPeQ dHoN nOmP} lX{Vq(aC Af al Aj bH Bn bR cA cB cP cQ cR Ct CX Dd Ed Fn Gc Hb Hu Hw Hx iH Ik Il In iO Ip Jj Jo Jr kF kO kP Lh Mf Ml mW Ne Ng Nk Nw Og Ou Ow Oy Pk Qa Qc Qv Ri Rt Sh Ue Ug Uk Ur Vo Vt Yg Yl) Uw(Ad Aj aO bV cA cB cC cS Cu cX Dg Dl Gh Ib iH Ip Je Jj Kg Kj Kn Kp Lj Lu Mf Ms mT Mv Mx nF Nn NT Oz Pb Pc Rx Rz Sh Uf Up Ux Uy Vb Vo Vs Vw Vz Yg Yh Yl Wm) Yl(aN Ao aP Ar As aV bA cR Cw Dl Et Ez fR Fy Gc Hc Hx Im In Jm kF Li Me mH Mj Mm Mr Nf Ni Nn No nT Nu Oh Ok Oy Oz Pb Po Ra Rf Rh Rz Uc Uk Up Va Vh Tl Th) Va(aC aH al Ao bB bJ cV dE Dk Gc Hu Ib Ik Is Ji Jq kS Ky Ma Mj Mq mT nB Ne nF Nk nT nU Nw Nx Ny Om Or Ou Rc Rv Rx Tz Ub Uc Uk Vp Vt) Wc(aC cl cU dD dF Dk Fn Hx Jl Js Ke kK Kq Ky Ld Lh Lv Lx Ma Mf Mj Mq Mx Nd Nw Ny Oh Om On Or Ou Ow Qa Tn Tr Uc Uk Vh Vv Vz Yd) Tn(aF aO cA Ct cV cW DE Ef Eq Gh Ib Il Iz Jh Jj Kj Ks Mt mW Ng Of oQ Or Oy Pk Rx Up Ut Vi Vt Vz Wd) Ry(aC aE al Ao aY bB bE cR dD Gc hC Hu Hx Ij Ik Ip Iv Ji Jy Ki Ly Mb Mf mP mU nB Nx Pd Pf Rv Ub Uk) Rv(aC aD As bH bM cR dD Fa Fn Hu Jm Kp Ky Lj Mf Ml Ne nH nY Oy Oz Pb Pd Pk Qb Qn Rf Ub Up Vz Tj) Vh(aR cR cV cW dE hB Hw Ii Ik Iu Jj Jt Kg Kj Kn Ko Lv Ml mT Ne nF nT Oz Rg Ri Rm Up Vs Zq) jB(Af aH Ao Ar bG bH bJ cl Co CX Db Fa gP Hr Io Jd Je Kz lW Ms Nc Ne Nh Nl Of Oh Pi Tj) Gc(aC As bA bQ bZ cL cR cU dF hG Ik Ip Jl Jm Lx mT Nb Ne Nw oF Ok Rh Si Ue Uk Vu Tj) Vz(aH Ao bZ cU Cw Dp Et hB Im Is Jg Ky Lx Ma Me Mm Nb Nn Nt NU Ok Pk Rc St Vv Xa) Rt(aO Cq dF Dk hB hG Ip Jl Jp Jr Lx Ma Mj Mn Nv Ok Ou Qa Qc Qd Qe Qh St Uc Vi Vu Vv) Gh(As Il Is Kq Ks Nn Oh Ok Pz Qa Qc Qd Qy Rb Tr Uf Ut Uv Vi Vp Vu Vv Wf) Sj(bF bQ Cq dD Js Kq Ky Lh Ma Mj Mz Nn nR Oh Ok Om Oz St Tr Uc Vp Vu Vv) Pk(bZ Cq Dp Ed Hw Ib Il Jj Jo Jt Ks nT Or Pa Pf Qa Rx Ug Uk Um Up Vu) Vi(Aj bS cA cK dE Fn Ib Ik Jt Kg Kj Ko Lx mT Nb Nn oQ Qa Qc Up) Is(fA fB Hu Hw Ip jR kO Lp Mv nC nH nL nT pH Ps Pz Si Zq) dU(Ar bL Cw Fa Ij Iq Ir Jq Ke Kq Ky Ma Mt Ny Ok On Ow) Qa(aO aU bL cV cW Fn Ho Ib iZ Or Ow Uk Un Up Vt Zq) We(bE bH cR dD Fn hB Hx iA Jj Jl Mf Nn oQ Pd Pz Rx) Wh(Aj Dp Fn Ib iO Iu Jj Kj mT nF Ng nT Pb Up Vs) Or(Ax eM Ij Im Iq Jg Li Lj Nn Nr Pz Ru Uk Up) Wf(bH Kg Kq kR Lj Mf Nq nY oQ Pf Pz Rf) Rx(As kK Kx Nn Oh Ok Ow Qc Qh Rf Rh Up) eQ(aE bV cB cP cW dA Hb iZ Ke kQ nO nW) fA(aN aW bV Fw kQ nK nL Nq oK oV Ow tF) oW(bV cB cW Fn hG iZ kl kQ Nr nW Nx oF) Up(Ij Ir Jr Kk Ko Kq Lx Qc Qd Qe Zw) Ps(cU dE Fn hB Ib Ik Iu mT Nk Nl) Lp(hB Ij Ip Js Ld Lx Mj Mq Qx Uk) Ri(aM bP cU dM Ed Ex gC Hx Kk Lj) Vt(Ed iA iJ Lu Ma Nn Nr Pf Si Wm) Vu(Fd Fi Gb Gn Ho Hp Sh Ux Wb Zq) Xa(cR Lx Mf Nc Nk Nl Nn oP Ub) Pz(Ed Gd Lt Nu Oy Sh Vb Zw) Uk(Ed Fc Ih Ru Sh Si Uy Wb) As(Fd Fi Hp Rz Wb Yh Zx) Fn(iA Pf Ux Vb Vw Yg Wm) Gn(bZ dR Gp hB Ij Pf Rg) Ib(Fr Ij Lh Qd Qe Wd) Si(Ji Oh Qb Qx Rh Tz) Cq(Ex Gp Ow Vb Vw) Lx(bL Fd Zq Ye Tl) Ip(Ex Oy Tm Tl Wm) Yd(Li Lj Ml Pb Rf) Rz(bZ hB Ij Ma Uc) Ru(bH Dk Ou Rg Ub) Uy(aH Ao iO Jy Pf)

Sr) Rh(Ad aM Ba Bg Dg fR hG lP kC Kf Kk Ou Qc Uc Us) Nn(bJ cR dJ Gc Gn Gp Gz hF Hr Ip Je Kf Kk nB Tm) bV(As Ip Is Je Jf Jy Ma Mf Nd Ni Nk Nm Pb Qm Tm) Rx(Ba bQ Ij Is Ld Ma Nd Oh Ps Tr Uf Uw Vq Vu) Kk(aG Ax Dr Hr Ma Mh Ml Nd Nr Oh Rf Rv Vq) Ma(An Aw bP cR hF Ho Hr Ip kC Kf Nd) Id(Ij Im Is Ji Jr Js Oh Ps Qe Rm St) Ip(Et Ld Lp Ml Nr Oh Ql Qx Ra Tr) Is(Aa Aj bP cR Ef Ib Ju Jv Sf Sh) Rm(Aa aM bP dJ Ju Jv Jy kS Sf Sh) Ax(aI Bg Et Gp iJ Nx Oh Ou Qc) Je(cU fR Ij Im Nd Nq Ny Tr Vi) Oh(Ar bH bJ cR dC hC hF kS) Tr(bP cR Ha hF Ux Wb tF) Bg(Aj Ld Lz Qx Ra Rf) Cs(aI Gp iJ Nd Qc Wh) bQ(Aw bP cR hF Hr Ri) nR(Aw aY dC Nd Nk) nB(Cw Fw Ih Ij Uw) hF(cT Js Ld Mx Nr) Tj(aI fR Ps St) Vu(bP mW nC nH) cR(cU Fw Im Nr) kS(cU Js Ld Mx) Ij(Cp kC Si) Qc(Aw Hr Rf) St(Gn Hr Jv) Jm(bP dL Ni) On(Ad Co Cp) oO(bH Nx Uw) As(Gp oH) Ba(Ng Rj) Dg(Dp Rj) Gc(fR Jy) Mf(aG aH) Nd(Ql Tl) Tv(Lz Qx) Ik(aM kI) Kf(kN Rv) Vq(Ed lW) Pb(kF oP) aI(Ni Nj) cU(aQ Ms) hC(Js Ld) AnNw AwoF CoVi EzkG NrkC NciA UcmY RvPk RfaM NxdL UwkK aYoK dKoP} jB{Ao(aC aH aI Aj aL aM aO aV Ba BB bE bH bJ bV cD cM CS cW cY dA Dp dR eM eQ Et fP gL Ha hG Hr In Iq Iz Jf Jh Kc Kf Ko Lj Lu Lx mE mF mH mI Mm Ms My NC Nd nH NK nL Nm Nu Of oP oT Oz Pb Pc Pd Pg Pj Pk Ql Qm Qn Tj) Dg(aC aL aM aO Ax bC bE bH bW cF Cs cY Dc Dd dK Dp dR dU eQ Et Fr Gp Hq Hr Hu Iq Is Iz Jf Jj Jm Js Jv Kj kO Kz Li Lj Lu mE Mv My Mz NC nH Nk Nm Nn Nu Ok On Or Oz Pd Pg Pk Qm Qn Tj tF) gP(aC aG Aj As Ax cA Ch cR Dp dR Ef eQ Fn Fr Fy Ha hC iJ Ip Iq Iz Jj Ju Jv Kk Kl kN Kp Lh Li Lv Nc Nk Nm Nw Oh Or oT Oy Pb Pk Qn) Hr(aC aL aV aZ bC bH Bo bW cB dA Db dR dU eC Gp Hc hF Ii In Is Jt Ly MF Mm mW nC Ne nH nL Nm nO Nw Oe Of Oh Oy Pa) nC(aC aH aO bH cE cG Ct Cu Dl Fa Hx iA Io Iq Ki Kl Kp Ky Lj Lv mT Nc Nl nR Of oK oP Oy Pd Pe PF) cI(aC Af aK aV bL cB cC CH Cs cX dD Fp Hc Hu Hx Iz Jj Jt Kl Ky Mg mT nL nO Nw Of Oh Or oT Oz) bH(aC aK aL aV Bo bW cB dA Db dU eC fB Gp Hc hF In Is Iz Jt Ly MF mW nH nL Nm Nw Oe Oh Pf) Aj(aV Ax aY Bc bE cB dK Hv Ip Is Jk Jv Jy Kj Kl kO Lj lW Lz Ms mU Na nB Nn nO Nt Nw Og tF) aK(dM eC Et hG Ii Jg Jt Kg Ko Kq kR kS Lh lW Me Mz Nc Nk Nw Pk) Af(aV Cx Fn Hu Ip Is Jl Jm kK kN mT Nc Nn Nt Nw Ny oH Qn tF) nO(Al aM Ar As Ax BA Bc BG bL bQ cT Dp Jv Nl oD Pb pK) Ms(aH Al Aw Ba Bg bU Ef gZ iH Io Ip Jd Jk Jp Jv Ng nK Of) nH(aH aO cG Hc iA Io Jy Ki Ky Lv Nc Nl nR Nu Of Oy Pd Pg) Db(aC aV Ba bE Ch Fa Ik Iq Iz Jf kO kP Ml Oh Oz Pg) Dl(Ax cB cM dA dR Gp Ip Is Jj Lj Mf Oh Qm Tj tF) Of(Al BC bW cR Cu Di Dp Gp gZ hF Ip Jp kQ Nk) Ap(aO Bb cB dK Hv Ip Is kO Lj Ml Nm Ok Pg tF) Nc(aQ aV cB dA fB Is Ky Lz Mf My Na Nw Pa) aC(bC bE Bn BO cS Di Gp gZ hF Jp oK) Oy(bB Bc Bo Cu Dp Gp gZ hF Ip Ml Nk) dD(aN bW cB cW Dp hG Hw Jf kG My Nr) Bn(bE cB dA Fn Hu kK Mr Nt Nw) Tj(Al eQ Hb hF Mf Ni Nt Oe Oi) Ad(aV Ax cM Cv Fa Fn kO Kp) As(aG Fa Ha Ip Kp Nw Oh Pk) Bg(cB eF Fn Gp Mf Nm Nu Om) Ct(bQ Gp hF Iq Jt Mf Nm Ow) Ax(hB Jt Mm Na Nm Nt Pj) Ba(bA dR hF Ly Mm Nm nY) Cx(cB Dc Fn Hx Jj Nt Nw) Ne(aU aV cB cY dA Ju Me) Mf(Al Cv Dp Jd Ni Nk) Ip(bU Ly Mm mT Oe oO) Is(aO Cu Dc Dk Jv Nq) dA(Bc Co cS Hw Io Jd) dR(Ar bB gZ hG Jd nK) Cp(Fn mT Nt Nw Qm) Hc(bC cR Dd Hv Nj) hG(Fr Hx kK oQ Ow) Cs(Jt Jy Kr Mm) De(Ha Iq Jv Or) Jp(cB fB Oh tF) mT(aS cX Gl Hv) hF(Al Cu Cv Di) Cq(cX Kj Ml) Dc(Io Jt nR) Dd(Fn Jy Lj) Nt(Bc oK Pf) Nu(Bo Ch gZ) Lz(Ni NK) nT(Ar Mz Ql) nL(Ky Lv lW) kO(Ar Co oK) Aw(Fn Oh) Cu(Mm Mq) Dp(eC Hf) Na(Ni Nk) Iz(Bc Ml) Pk(Ha Ky) aO(Jl Pf) cB(aH gZ) dK(Hw Or) AlJj BbJt BobE MmNk MtOh JdfB JedJ JoLi LdkF aleC aZcR cXkN tFgZ} mW{bH(aJ Ar Ax bA bQ bZ cD cH Cs Cu Cw dF dG eF Et Ex Fa Fp FR Fy Gp hB Hx iA Ih IJ Im Is It Jg Jl Jn Jp Js Ke Kf Kk Kl Ko Kq Ld Li Lj Lp Lx Mt Mz Nb Nn No Nq NR Nv Ny Oh Ok On oQ Oz Pa Pd Pe Pf Qa Qb Qc Qd Qe Qg Qh St Tn Uc Uh Uk Ur Vi Vu We Wm Yf) Vu(aF aJ aK aO aU aV Ax Bb bG Bo cB cH cU CV Cw cY dA dD dI dJ dR Fa Fn Gp Hu Hw Il Ip Is Jq Ju Kd Kj Ko Li Lj Lv Me mP Mv nI nO Nq Ns Nw oH Ok Pk Qd Qm Qn Ri Rt Ss St Tr Tz Ua Ub Uc Ue Uk Uo Ur Vo Yl) Uk(aM Ax aY Bc Cq dR Et Fa Fr Fw Ih Ii Ij Il Im Ip Ir Is Jm Jn Js Kn Kp Lh Li Lj Lx Mf Mt Mx Nb Nj Nl Nn Nr nT Nw Ny Oe Oh Ok Om Oy Oz Pb Pc Pf Pk Pz Qa Qb Qe Qh Ql Rm St Tn Uy Vq Vt Th) Vq(aQ aU aV bI bJ bQ cY DD dJ dR Fn Hr Hu Hx Id Io Iq Ir Iu Jm Jo Ju Kj Kk kP lW mE mF mH Ml oH Oy Oz Pb Pd Ug Ur Us Uv Vo) Li(aC Aw bE bX CQ cR dD Fn gP Hr Hx Is Iv Jp Ju Kp Mr Nb Nc Nj Nk Nl No Oe oN oV Pb Pd Pe pH Qc Ri Tn Tr Ub Vz Th) Up(aA aJ aM Ax Bc Fr Hu Hx Ih Ii Ij Im Ir Is Jl Jm Jn Ke Lh Lx Oe Oh Pz Qa Qb Qd Qe Qh Rm St Tz Vt) fB(Ad aF Aj Ap aZ cD cQ Dg dJ eM Fy Hv Ii Ij Il Iz Jt Kg Kl Lj Mg Mx Ng Nn Of Oi Ok Pi Pj Pk Qm Qn) Lj(aE aG aI Aw bX CQ cR dC dD eC fA Fn fP Gb gZ Hb hC iJ Ko Nb oN Ql Rg Rh Uc Um Vi Ye) Oy(Ad Ax Ba Bb Bc Bg Cv Cw Dc dJ Fn Fw Jg Jp Kk Nv Ny Om Qh St Tn Ua Ub Uc Uo Wh Wm) Qa(aC Aw aY bE cQ cR CV dD eC Fn Hx iZ Kr Nc Nk oN Pd Qw Rm Vi Vt) St(Af As Aw Bn Cp Cx De Dl Ed Fn Hr Hx Ib Jj Jt Ju Lv mI Nt Nu Rg Wm) Hr(aJ Ax Cs Gp Is Kq Ld Lp Ps Qc Qh Tn Uh Ur Vi We Tl Xa) Qh(Af BN De Ed Fn Hx Ib Iu Ju Kr Lv Nk Ri Vs Wm) Hx(Ax Bc Co Dc Fa lK Pk Rg Ri Ry Tn Uw Wh Wm) Pd(aJ Ax Cu dG Is Jg Nn Ps Tn Vi Xa Wm) oT(aF aO aZ bI bL cX Ip Je Ml Nm Nn Pk) eQ(aE aS cP Db eC Jk lW Lz mP Na nO) fA(cI cX Dp Il Jd Je lW mY Ne nK nL) Rg(bA Fr Jn Kj Nn Oh On Pa Tn Wh) Is(Ju lK Ms Oe pH Ql Rc Ut Wm) Oh(Aw bL eC Fn oN oV Qw Vi Vt) dU(Ax dD kK Ml Mz Nk Nn Nw tF) Tn(Aw bJ Hu Jj Lv Oz Pb Qw) Ri(aJ aM dL Fr Lx No oO Qe) Vt(Ax bQ fR Kj Nn Qv Ur Wm) Cq(Dr Kj Qb Rz Sh Ug Vo) Fa(Aw aY Kk mP mU Pf Rv) oV(Ax cX Il Je Nn Pk) Vo(Ij Lx Pf Rm Uc) Pb(bX Nv Ny Oe Om) dD(aM Lx oD pH pK) iB(jI lN nC nH nL) Ax(aC bE bX pH) Wm(Fn Jp Jq Lh) cR(Nn pK Qb We) eC(aM Fr oQ Qb) Fn(Fr Nn Oz) Lv(Kq Qx Uw) Nk(pK Ry We) Uc(Gd Kj Ug) Rm(Kj Sh Wb) bX(Cs gZ Oz) lK(Nf Ny Om) Yg(hB Pf) Wh(Ng Pc) Rj(aM Oe) Us(Gc Uw) aJ(mU Vi) aY(Ry We) oD(cX nO) GpHu NmJg NnoN LxSs UbXa IbJk TrRz VzfR RcOk QbfP QdKj JjPk JmUg KpPf NyOz UymE PclO aUdR tFgZ} Yl{mF(aN aR Ax bQ bZ CS CU Et Ez Fa Fr Fy Gc Ih Ij Il Im It Je Jl Jn Jy kC Kq Kx Ld Lj Lx Lz Ma Mf Mh Ml Mm Mq Mt Mx Ni Nj Nn Nr Nt Nu oF Oh OK ON Ow Oz Pb Pd Pe Pf Pj Pk Pz Qa Qt Qx Ra Rh Sr St Tn Uw Ux Vq Vv Zw Wm Yf) nT(Ax bZ Cs Dr Fa Ij Im In Is It Jl Jm Jn Js Jy Kx Ld Lj Lp Lx Lz Ma Mh Mj Ml Mm Mq Mx Na Nf No Nr Pb Pe Qa Ql Qt Qx Ra Rh St Tn Uc Wm) mE(Bc bZ Dr Et Fy Gc Ij Il Im It Jn Js kC kN Lj Lx Ma Mf Mh Mm Mx nC Ni Nj nK nL Nm Nr Nw oF Ok On Oz Pb Pe Pf Pz Qa Ql Sr St Vq Yf) lW(aE aR bA cD cH cP Et fP gL Hx Ih Im Is Jm Jn kF kI Kn Li Mf mH Mj Mm Mr Nd Nk Nt Oe Ok oN oQ Pb Ps Qt Uc Vu Yh) nC(aE aG An Aw aY CQ cR dC dD fP Ho Hr Hu Hx It Jg Jm Ly Me mP mU NB Nd Nx Or Oz Ql Rf Rh Ub Uk Up Uw Vq Vu) Lx(Ar bJ cP eF Fy Hr iO Jp kC Ke kK Kl Kn Kq kS mI mP Ms Mt Ng No Nt Om oN Rc Rf Si Sr Uh Vi Vv) kK(bQ bZ Cu Dr Ez hB Is It Jl Jn Js kN Ld Ma Mh Ml Mq Mt Ni Nj Oh On Ow Pb Qa Qx Ra Tn Uw Yf) mP(aJ bQ bZ Cu dG dL Ed Fr Fw Ij Il Lj Mh Ml Mt Nn nR Nu oN oQ Ow Qa Qt Rf Tn Va Tj Yf) nI(Ao Ap Ax Ba bL cR CS Cu Dg Dl Fa Gl Hp Je Li Nj Nk oK Oz Uc Um Uo Ux Wm) oQ(aY bH cG cN cQ cR dC dH Gb Hr Hu Kc Ks Lv Ly Me mU Nb Nx Oz Pd Po Rx Um Vi) Ow(aM Ar Aw bJ eF Gn Gz Hr Ke Ki kS Ms mU nB Nc Nd Ng No Rf Si Sr Vi Wf) Nd(aN CS Dr Fa Hr Hv Hx Id Il Je Lj Oh Oz Pf Rv Rx Uu Tl Wm) kN(aN aQ bI bR Di dR Io Iq Ir Iu kC Kf Ko Kr Li mH mI Ms Uk tF) bZ(aY bJ cG cP Di Fn Id kF Ki Kn mI mU nB Ng Ri Rx Uu Vi) nR(aO aY bE dC Hx Ib Id Ki KR Li Ly Mb Me mU Pb Rx Vs) nH(aA dC dD fP Hx It Jg Jm Kf Me Oz Pb Ql Rf Rh Rj Rm Vu) Oh(aM eF Gz Hr Ki Kn kS Ms nB Ng Rf Si Sr Uu Vi) mU(aP Ba Cs dL Ed Fw Il Lj Nk Nn Nr Nu Qa Wm Yf) nL(aA aG dC dD fP Ho It Jg Jm Me Mg Rm Uc Vu) kC(bJ bQ Cs Dr Ij Iu Js Ko kS Lz Nj oF Tn Yf) Wm(aI aL aY bE bO cC cZ cF Gz Ik iO Sr Th) Pz(bE bN kF kP mH mI nB Ng nK Sj Sr Uu) Ax(aI bE cC cZ Du eF Ik Ms nK Rf Sr) oO(bE cQ cR dC dH Hu Ki Nb Pd Pf Tj) Nn(Aj bJ EF Gn Gz Hr Ng Ss Vi) nB(aP Cw Fw Il Lj Nb Nr Nu Tj Yf) mH(Ij It Ma Nj Pf Tr Ur Vq) Nr(bJ eF Kn mI Ng nK Sr) nU(Aw Cs fP Hr Li Nc Nk) aY(aM bP cS Cu oK oP) mI(Ij Il It Mx Nj Vq) kO(Ba Cw Hx Ik Me Rj) Ld(eF Id Ik iO kS) kF(Bn Id Ko Oz Tr) Ng(Ij Ma Pf Tr) oP(dD Oz Pb Rx) Cs(aL cZ Ik) Il(Hr Ms Nc) Uu(Is Qt Vq) kP(Kf Nj Uc) Aj(bO Wh) Si(Mf Pf) Ra(eF iO) Vq(aW Rx) bH(kI mT) nO(Li Nu) mY(Fw Rh) kG(Cq Cv) ArLz AwGp EfIs ThTr FacP MsPf NjcD HvHx IkWh QxeF LjdA cRkI dDnK iAhB} Is{Tk(aJ AL aP aS aY bE bM Bo bR bU bV bW bX cB cC cF cG cL cR cU dG dI dJ dK eF Ez Fb gP hB iH Ik Js Kk Kr Kz Ld Li Me Mn My Qt Qv St Ub Uk Uo Up) nL(aA aO bH bR cB cR cX dB eC

Figure 25 Continued fA hA Hf Hr IH Iu Jd JL kO kP Mj Mk Ms Mv Nj Nk No nU oN Pd Pg Ph Vt Tj Th) nH(aA bH bR cB cR cX dB eC fB hA Hf Hr IH Iu Jd Jl kO kP Lp Mj Ms Mv Nj Nk No nU Pd Pg Vz Tj Th) nC(aA aO bH bR cB cR cX dB eC fA hA Hf Hr IH Iu Jd Jl kO kP Mj Ms Mv Nj Nk nU Pd Pg Tj Th) Ib(aQ aV bH bN cH cP cR cY dA dB dJ eC fP gP iO jD jE jY lK lL mP nR oN rC Uk Vv Th) Sh(aY bE Dl Du Id Ik Je kK Kn kO kP Mb mP Ms mY nB Nd Ng nI Oe oN oO Pd Rf Un Vh) kP(An bL Ct Gn Ho Hp Hu Jj Jk Kd Lj Mf Mk Ms mT MU Mx Nn Ns nU Op Up) lN(aW bN cO Cw Db Dd Fb Ic Ik Kg kK Nc Nd Ne Nl nO oH Tt Un Up Vv) kO(aO bR cB cX dB eC Gn gZ Hf Ih Jd Jl jU nU Pd pK Wm Th) pH(aA aC cF cN cR cT dM iH Ir Jd Je Jv Kk Lj oN Ou Pk Qm) Up(bN eD eM Gn Hr kN ml mP mT mU Ng nO nR nT nU oQ rX) Id(Em Eq Gd Gn Op Rt Rz Sf Si Sj Ux Vb Vh Wc Wf Tl) bN(Ed Hr Ic Jd Jt Lh Lj qT Qy rZ Ss Ua Uk Un Tm Wm) nU(Ih iJ Jj jY lK Lp Ms Pz Ql qT Qv Rt Rx Un Vu) Si(Af bE cA cN cR CX Ik Je Jo Pd Qn Ss) Ng(Bg Eq FB Fd Fi Fn gP iC iJ Tr Zq) Rt(Aa Ap bJ Dl Ef Hr Ke Ki Kn mE nK Om) Va(Aw De Dl Ef Gn Hr iZ Je Ki Kn Vi Yg) nT(eM Eq fR Jj Lp Op oV Pz Uk Uw Wc Wm) gZ(aK aP Ar Bn cM fA Fn Fw Im Iv Jk) Hp(Ad An Cu Dl Gn Hr Jv Nc Op Ur) fB(Af aJ bX dB Gl Ip Jk Ju Mv Ny) jE(Ao Ba Cw Fb kC nF nI Tt Ua Un) mT(Eq fR Ih jI lK Rm Uk Un Zq) oD(aK aL aP bE cU dL dR hG nO) Op(bE Kn mP mU mY nB nI Sr) nR(Af aO Bn lK Vi We Zq Ti) kC(dB eC iC jG jV Pd We Wm) Ef(Du Fd Fi iJ Sf Yh Ye) Rz(bP bV cS hG iO mF oF) dU(bE Ch dK Ip Jv kF Pa) eQ(Fr Jl Jn Mt Nf nO Nt) mU(lK Ql Qv Ry Wb Zq Ti) Kn(Fi Sf Wf Yh Tm Tl) fA(aV cQ Dp Ed nK Nq) mH(fR jF jQ jR Sj Vi) mP(Ed Or Pj qY Ry Wb) nI(Ha iC Mv Sf Wm Th) kK(aD Fa lK Uy Wb Tl) rX(Ic Kg Nc Nt Un Vv) pK(bE cU cW dL Fn Ih) Fd(mE mF ml Ms Nc) Gn(Ik Kg Ug Uu Vv) Zq(aI dD kR Ms Uu) Jt(Gc iC Ko Rx Tm) Uk(aW dJ gP nO oQ) eM(dI Ed Hf Jf Mj) oV(cI cN Mf Nq Tj) Wm(kF mY nO Th) Ik(Sf Yh Zx Ye) Yg(Aa cR fR Ms) Wd(Aa cR fP kS) Vi(aI bP Gb mE) mF(Ex Fi Lp qY) mI(Ks Rm Tv Vs) Fb(jH jQ qU) gP(Ch Ct Qy) mY(Ed Ps Sf) iJ(Ch Jd Qy) kF(fR qY Vq) oT(Ar Hf Nk) Cw(eD rZ) Gb(Aw Hr) Mb(lK qT) Nc(qT Wf) Tm(bP Iu) Ry(nB oO) Rx(cX Dl) Vh(bU Il) Vv(gW rZ) nO(jH Ju) nF(cC Eq) AjTi AorC EmUu ExlW GhNt GcJe WboO SfUn JdhB WeiO YebP LpmE WndN} Qa{Vi(Aa Ad aH aI aK aN aQ aR aU aW bF BG bJ bN bQ bZ cE cP cX cY dA dF dI dJ Dl Ex Gb gP Hb Id Ii Ji Jn Js Jt Ke kG kK Kn kO kP kS mE Ms mY nC nO NT oF Pj Qm Qv Si Up Va Zq Ti Th) Zq(aC aH aQ Aw aY bE bJ bN cQ cZ dD Du eF Gd gP Hr Hu Hx iA Id Ik In Iu Je Kl Kn Mj mP Ms mU NB Nd Ng Nx oN oQ Pd Qt Rf Ri Si Uk Up Vq) mU(Ar Bn Bo cB cP cV cW dA dJ Ez Fd Fn Gn gP Ib IP iZ Lp Nc No Op Or Qv Ri Rm Rt Rx Tr Uk Un Up Us Vb Wb Tl Xa Ti) Gn(aQ aY bE bJ bN cC cP Ex Fp fR GP Hp Id Ii Ik Jr Js Jt Kf Kn mP Ms mY Nm NO Nt Pj Rf Sr Un Up Vh Th) Si(aC Af aJ aR Aw aY bE bJ Bn cN cP dD dG dH Dl Hr Hx Id Ik Je Ki Ly Mf Nb nW Nx Pd Rf Ub Th) kK(aC aI aP bE bH cR cW dD dM Dr eF Ex Fd Fi gP Hf Ib Jd Je Op Ph Pi Pj Pk QY Rz Uy Tl) nT(aU aY Dr eM Eq Fn Ho Ib iZ Jj Nc Pk Pz Rb Ri Rv Rx Sj Uk Un Up Uw Uy Vq Wc) mI(aC aE aI aO bN bS cA cK cP dD De eC Hf Ib Kr Kx Rg Ri Rm Rz Un Up Th) nI(aO Aw bC bH bL Bn bU cA cR cW Ed Ex gP HF iZ Kr Nc Or Pj Uk Up Vq) Rz(aI Ar aY Bg bJ cN cS dJ gP hB hG Id iO Js Kn kS mE mF No Nt Sr) mP(Ex Fd Fn Gb Hf Ib Lp Nc Nt Op Ph Pi Pj Pk Ri Rt Un Vb Wb Tl Xa) nB(Af Bn cW Ed Eq Ex Fn gP Ib Kr Nc Rb Rt Ry To Tr Un Up Uy) Th(Aw Bc bU EM Fd Gz Ib Kn Ng Oz Pb Ri Sj Up Tm Wm) bN(aR aW Ax dJ Fn gP Ib Ic jF jT Ld Ng Ss Uk Un Tm Wm) Vh(Aw Cs Cv Di Hr Id Ip Je Ki Mf No Pz Rf Ub Um) Yg(aC Ar bE Bg bH bJ cX fP gP No Nt oN) eM(Ar cR dA dJ Ex Fn Jf Nj Nl To Up Ti) mY(aI cW dM Ed fP Hf hG Ho Hp Ib Op Rx) nO(aX Ct eC Fn Ib iZ Rb Ri Uk Un Up) No(Eq mT Op Rt Rv Rx Sh Va Wd Yd) Sh(aY cP Du Ik Nx oN oO Pd Rf) kP(Bo Cv Ho Hp iZ Rv Rx Vz Ye) Eq(cP hC Id Kl kS Ng nW) Wf(Aa bJ Dl Id Kn mT oP) Rx(aQ bJ Dl fR mF Nt nU) Op(aY bE oN oO oQ Rf Sr) Du(Cw Dg Dl Hr Kl mF) Gb(Aw Hr Hx Jt Ly Ri) Ng(Fd gP Ho Vb Wh Ye) Hp(Ar Cw Dg Hr Ub Ur) Ik(Ho Sf Vb Wh Ye Xa) Wd(Ar fP hC Js kS oN) Ry(Dl Id Iu Jt oO Up) cP(Ps Sf Va Ye Tm) Fn(Ex mT nU oQ) Id(Sj Vz Tl Yf) Ri(mT nU oQ Ti) Rf(Rt Sf Yd Zx) Up(kI mT nU oQ) nR(Af aO Bn We) kF(An Cq Cv Vq) Fb(jH lN qU) Ib(dA kI oQ) Vz(kC lW Ms) Rv(Dl fR Kn) Va(Aw Hr Je) aY(Em Fd Tm) Dr(kG nF) Nt(Fd Gh) Ho(Ii Nm) We(iO oN) Lp(mE mF) Un(mT nU) Vq(kC kO) fR(aE Ar) CwlN DgVb DlWc WmkO EmaC ExmE GcJt NcqT SfoO SjmH WhKl YeOy KzTk} Uw{lW(aK Ar bN bS cA cI cK cL cO Cs Cv cW dA DE Dg dH dK Dl Dp Ex fR Hp Hu Ib Ih Ip Ir Iu Iv Jd Je Jo Kr Li Lp Lu Mf Mr mT Mv Nc Nd Nj No NT oH Ow Pe Ph Rg Ri Rt Rz Ub Up Vb Vi Vp Vs Vt Vz Zq Xa Th) nT(Al aO Ar As aY bL cA cF cI Cq cS cU Ed Ef Em Ha Ho Ib iO Iz Jd Je Jv Ky Lj Lv Mb Mf Mk Mn Ms Mv Mx Nc Ne Ng Nm Nn NY Oh oP Ow Oz Pb Qb Qe Rm Ry Sh To Ua Uf Uu Uy Vs Wc Wd Yd Yg Zx Tj) mH(AN aW Bc cA cI cT Cv cX dE dK Ed Fc Ib Il iO Ip Je Jy Kd kR Lj Lp Lv Ml mT Mv Nb Nk Nr Nx Og Ou Pf Ub Uy Vs Vt Yd Tj Th) kC(Al aO Bc cA cI cT Cv cX dE dK Ed Ib Id Ip Ki Lj Lv Lz Ma Mf Mq Ms mT Mx Nc Nj Nk Nl Nw Ou Pg Qx Ra Ru Tn Vs Yd Wm Tj) oP(aK aU bB cW cY dD dE dJ Ed Eq Ha Hw Id Jo Jy Ky Lz Me mF Mk Ms Mv Na nC Nj nO Pj Pz Rx Ry Ss Tz Ua Ub Ue Uo Us Yh Th) kP(Al aS cB cI Cv dE Di Et Ho Hp Ib Id iO Ip Lj Lu Lv Mk Ms Mv Ng Nm Nw nY Ok Oz Pb Pc Qd Qw St Tz Ub Vt) mP(aG Aj cA cF cX Ef Gz Ib iJ iO Jd Jv Kl Lj Lv Mf Mg Ml mT Nc Ne Nk Nl Op Or Pk Qb Uf Uy Vb Wb Tj) nO(Aj bN bQ cB Fa Ha Ho iH iO Jm Kj Ky Li Lv Mg Ms Nb Nc Ne Nl Op Oy Pc Pk Qb Qy St Uf Vb Vu Yd) nC(aC bE bH bJ cR Dg Dl Gd Hx Jf Ki Kl Kn Kp nH Nt Nu Of Pc Pd Pe Pf Ps Ss Ub Uf Ux Vv Vz) mT(aK An aQ aU aV aY cQ cU cY dA dD dH Di Hx Id Lv Me mF Mh Ms nK oN Pb Pd Rx Ur Vu Vv) kF(Ao bB cB Cv cX dE Ho Ib Ip Ju Jy Lv Mv Nw nY Oc Og Oi Op Tr Ub Uy Tl Tj) Ik(aJ aM aN aY bP cF cM dG dI dL fR iJ iO Je Kk Rv Rx Sh Tl Th) mE(aW cA cI cO Cv dE Ib Ip Je Mf Mv Nk Ub Vs Vt Yg) mF(aO cI cO Cv dE Ip Je kR Mv Nc Nk Nl Ub Vs Vt Xa) mI(aW cA cI Cv dE Ip Je kR Mf Mv Nk Vs Vt Yg) mU(cX iJ iO Lj Lv Ms nY Qb Ry Uy Vb Wb Tj) nI(aO Ed Jd Jj Jv Lv Nl Op Or Qy Ry Sh Uf) nK(aW Gl Ib Ki kR Mv Nk Sh Vs Wd) kK(cB Hx Nw Sh Ss Ub Ux Vo Vz) nR(aO cB Ed Lv Nn nY Ow Ry) nH(aC Di Ed Hu Hx Lv Nu Ry) kO(Al Ax bE cI iO Vb Vt) kI(Al bE dK Ki Lv Uy) Ef(aI dD nY oF oH) Ng(aY cA Gh oF Rv) bH(bZ nL nU Oh Ow) nB(Al cB Lj Qb Ry) Ib(aH aI bI dD) hB(Je Mf Nc Nl) kG(bE dD dR Lv) Uu(Ip Je Rx) bZ(Aw Hr Ub) nU(aO Dg Dl) mY(bN Cu Ri) nL(dR oH Sh) kN(Mf Mv Nk) oO(Lj Ry Uy) Ch(iA oH) Th(cS Rx) Rz(Il oF) oQ(Uy Tj) AjoH SsbN aQcU} oT{cQ(aC Ad Aj aM aO aQ As aX bE BN bS bW cA cB cJ cK cN Cp cR CX dA Db DD dH dL eF Et GP hG Ik Io Iu Iv Jd Je Kc kO kP kQ Kr Lx mF Mj Ml nC NH Nj NK nL nR nT Nv Oy Pa Pg PH) kQ(aG Al aM Ax bH bM bN bX Cs cX dN Dp eQ Fa Fb Fr Fy Hc Hr In Iq Ir Jd Je Jf Jq kK Kp Kx Ky Kz Li Ms Mw Ne Nf Nh Nk Nl Nu Ny Oy Pa Pd Pe Pg Pi Pk Tj) hG(Aa aG aH Aj aO bG bH cI cX De Dl Dp gP gZ Hr iJ Jd Je Jg Jp Jt Ki Ly Mh Ml Mm Mn mT nB Nc Ne Nh nK NL Of Og oK Pj) Pk(Af aO Ar BN bS bU cA Ch cI cK cP Cx De dH dL Et gP iH Ii Ir Iu Iv Jd Jo Jp Jr Kr Ks Mj Mn Nj Nk Og PH) aO(aC aK bA bF Bo bW bZ Cq cT Cu Fw Fy Hq Iq Je Jl Js kK Kq Lv Ma mF Mq nC nH nL Ny Oh oK Om Ow Pf Qm) Je(aE aF aK aN aW bF bN Bo cP dA dB dH dN eF Hb Ip Iv Jf kF kI Ko Ly mF Nq nW nY Oh Or) mF(Al Bc bH cI cX dA Dp dU gP hF Hr Ip Jd Jn Jp Lv Nc Ni Nj Nk nL Oe oK Pg) nL(aF aP aW bF bN bV cI cU cW dU eF fA Fn Fw Ip Jf kF kI kO lW Nk Oi Or) nC(aA aF aJ aZ bN bQ bV cM cP dA Dp dU eF fA Fn Ip iZ Jn Oi Pg) aW(AN cB dA Dp gP Ip Jq Ms Ne Nh Nk Nt Nw Om Or Pa) cI(bN cH cL dB dH dK eF eM fA Hb Jq Mk NK pF) Pa(aA aH bB dA Dp Io Ip Jd Nh Nl oD Or Pg Tj) nH(aV bV cP dG eF Ip kF Kr Mj Nh oF Oi oQ Or) Lj(Ar bS bU cA cK cP De Ih Ir Iu Iv Nj Nk) Mf(Bn Bo cP dL eC gP Kr mT nK nW Oe Of) Jd(Ar bI cB Co eC fA Fy Ko Ma Mz Nm Nn) Oh(aF aJ Bn bU Cs De Hf Jl Jn Kr Nh nT) Tj(aI aK cP cS dA Gp Hb Jh kC kG Mh) Nk(aK Co Fy gP Li Mw Ne Nn oV Pi) Ip(Ed Il mH mT Nc Ne Nh nK Nl Pf) Ma(aF Ar Bn cA dA Iu Mj Mv Ou) eC(aQ aV dA dI Dp Hf Na Nh nT) Af(Fy Jq Js Ky Ny Of Om Pi) Co(aK Ar De Hf Ik Iv kP Nj) nK(aP cM cW dA Fn nO Oi Or) Bb(aK eF Mm Ne Nh Pj tF) Gl(Mm Ne Nh Nl Nu oO Pj) mT(aF aZ bl dH Ko Nm Of) De(cB Fy Ir Jm Ny Ph) Nq(cH dD dK fA Jq Nn) Ml(bV cB cP dA Hb Lu) Li(bS cA cK Hf Ih Ir) aK(Ad Ap Cw Dg Dl oD) Pi(cA dH Hf Iv Nj) aA(bQ dD Ed Mx Ow) Ax(aJ cP dL Kr) Cx(cB Jq Om Qn) Ne(aN Hw Ly Mb) Nh(Hv Ko Mz Nm) cX(cB Jq Mp oK) Fy(Bn bU kC) Jp(Ky Mz Ok) cA(gP Ir Nu) cP(eQ Ni Ow) gZ(cB fA tF) oK(aP kF kO) Hq(aF Pg) Js(Ar Mj) Kr(Jq Of) Or(aF

Hx) Nm(Gc Pz) Nr(bU Zx) Sh(aI Nx) Wh(bQ oF) nC(Fn Uk) iO(Uy Xa) YfMh EmHx EtZq FdSt MaRi TrYd IjmI YgOn SjPz WfoO PscS VhlW OyoP PbiA bHoQ} eQ{kQ(aC Aj aL Aw bE bH dN dR Ef Fn Hr Hu Hx iP Iv Iz Jj Ms mT Mw Na Nb Nc Ng Nt Nu oD Of Og oH oV Oy Oz Pa Pd Qm) aE(Bo bV cB cI cP cQ Ct Fp Ha Hc hG Ip Jv Lu Mk Mz nC nH NK nL Of oN Pf Pk Qm) dA(aO aY bH cI Cq cX Fw gP Ha HC hG Hw Im Jd Ju Ks Li Mf Ne Nl Ny Oz Pb tF) cB(aO bA bH Bo cI cT dH gP HC iA Jp Ki Ms Nb Nq Nu tF) hG(Ao Bo Cq Dc gP Hc Kk Ky Lv Lz Mf Ms Na nC Of Pf) cP(aJ aQ aV Ax bJ Ch Dc dR Ip Ms nC Nd nH Nw Pf) gP(aI Bb cS cZ dE Et Fn Hb Ip Kk Lh Lu Mb Nw) Nt(aS Bb cI Dd Fw Gl Ip Jg Jm Ko Ms Nm Ph) Fn(aO Bb cU cX Gl Hb In Ip kG mE My nL) aV(aO Aw aY bH cI Cq hC Hr iA Nh Nq) Na(Bb bV Gl Ip kG Lu Mb Nw) Pa(aA aS Aw bA cT dF Hc Nr) Ip(bP cI Hc Jp Mm Nu oO) aK(bA Bb cT Cv Hc Ni Nk) Bo(aD aL dN kO Me Nb) Ko(Ad Aj Ao cI Dg Jt) aI(Af Aj Ao Bn cI Dg) Cq(Hb In kF kI My) nC(cW dN Hb iZ nW) Ms(Jh kC kG Mb) Nk(aC Fr Ih Iq) Kk(aO cN cU De) cI(dN Hb In Me) nH(aP cW kI nW) Iq(aF cR Ou) Jq(Ao De Ji) aC(aR Lz Mg) bM(bA cR cX) Bb(oD Pj) No(Im Pf) Lu(dD Tj) Hc(cU cW) aM(Ax Dc) aO(aQ Hq) mT(cU Ly) AoHb ChNu CpOk DeaL DkkO MvNe luLi IzKp JpNw JyPk KlOf bEoK cWnL} kC{Wm(aC aI aL bH bQ cB cZ Dc dD dR Fd Fn Fr Fy Gp Ha Ho Ij Jp Kd Kn Lp Om On Pz Qh Rf Ri Ry St Tn Tr Uh Uk Uo Vt Vu) Dr(Al As bQ Cq Ha hB iO Jm Lx mH mT Nb Ne Nr oO oQ Pf Qc Ry St Vu Wc) Ho(It Kx Ld Lz Ma Mh Mq Mx Nn Pf Qx Ra Rf Rh Tj) Yf(bN cR Cv dD Dl Fn Mb Mf Nd Nh Nk Nl Pd Pj) Si(Fy Ij Js Lz Ma Mq Mx Nr Pf Pz Qx Ra Tn Vh) Wc(BA Bc cT Ez Fy Ma Mq Qt Tn Wh) Ry(It kN Ld Lz Ma Mq Pz Qx Ra Rf Rh) Lp(Ax It Js kN Ld Lx Lz Ma Mq Qx Ra) Wh(Aj Ml mT Nc Ng Nl oF Vt Vu) Uy(Ax Ij Js Ni Nr oF Pz Qt Rf) Tn(Eq Gh Gn kO nC nH nL Qw) Vh(bN cR Ib Ip Ko Lv Ml Va) Fd(Lx Mq Mx Qx Ra Rh Vu) Nr(bS cA cK Gn Qw Rg We) Pz(Ed Eq Sf Vb Wd Yd Tm) Ru(cR Jj Jm Mf Nd Nk Vu) Tj(Gb nC nL oD Pa Vi) Tr(Eq nC nH nL Nx Pd) Gn(Ij Ma Nn Pf Rh) Xa(Ip Lx Mf Nc Nl) Rf(nC nL Nx Pa Rt) Va(It Ld Lz Rh Vt) Bo(aC bE bH dD) Ij(Ps Sh Vi Tl) Zw(Ip Iu Jm Nn) Li(bS cA cK Rg) Ri(aZ Co Cw Qd) Fy(nC nH nL) Mx(Rv Rx Wf) Hp(Ax hB Nk) We(bQ hB Jl) Rt(Dc hB Rh) Eq(Ax Oz) Lx(Vi Tl) Ib(Vi Wd) Rv(Mf Ml) Nw(Gc Sj) bE(Ar Cw) cB(bH Pk) cX(Fn Jq) CoRg CxOk GdPf NnWf YhbQ SfkN JsTl RhPa} Mf{Si(aG aH aI aQ bE bG bJ bV cD cV dD dL Et Fn fP Gd Gp HB Hx iH Ij Il Im iO Je Ji Ke Kk Kq Lp Lx Mm Mn Mx Nh nI nK Nn Nq Nw Ny oF oH On Oz Pf Pi Ps Pz Qb Qc Qd Qe Qh Ql Rv Ss St Ug Tl Xa) Rv(aQ Dd Fa Gd Hf Hr Id Jt Jv Kg Kj lW mE mF mH mI Ms Nc Ng nK Nt Op Rt Sh Ug Up Us Uu Va Vh Vo) fR(Aa aI aQ aY dA dE dJ Eq Fn Gp iZ Je Jq Lp Lv Mm Mr Ne nH Qm Qn Vh Vs Wh Zq Tm) Va(aD aG aH aI aQ bJ cD cT cW dD Fn Hr Hx iH Ip Je Mk nI nK oH Pg Pz Qb Qw Us) Rx(aI aQ Gd Kg kK Ms Nc oO oQ Ug) Sh(aH aI cD Hx Il Mn oH oN) Xa(kK mE mF mH mI nC Ng) Op(aG aH aI bG cD Hx Pz) Vh(aH Et hB Lx oF Pf Pz) Wc(aQ mE mI nK oO oQ) We(Gd mE mF Ms Ng nI) Tl(Id Kn Lv Ms Nd Nt) oV(Bo gP Hf Oe Of Pf) Wh(kG mT nF Ng oF) cB(kO nC nH nL) Eq(bG Id oH) Gc(mE mF mI) Wd(fP Ng oH) Ry(nH nI nL) Rt(oH oQ Pg) Vi(aH mF oF) Ho(kI mY) Zq(aH hB) Wf(mI nK) Ye(oO oQ) oD(Bc Ip) pK(bE nC) DroQ DuoO EdGd YfmI GhnK NgYg WbKg SfaH VbnI UxhB PkpH} Lx{Si(aC Af Ar Aw aY bE bS cA cK cP Cs CX dD dE dH Ex Fd hC Hr Je kR Ly No Pe Rg Up) Vi(aI aM Ar bN bP bS cA cD cK cX dE dJ Id iO Iu kQ kS nC No nU oF oN) Fd(aS aY bI cG cP Di Gn Hr Ip Ke Kn No Nt Rf Rh Sr Uh Ye) Yg(aY Bg bH bP cR fP hC kS Ng No oN Qy Rh Ua Ye) Vh(aC Ar Ax Cs dE Ho Il Ip Je kS No Pz Sr) Zq(aI dD hC iA Il Je kR lW oN Pi Rg) Gn(aY Du iO Jr kQ kS No oN Pe Tv) Rx(aO bH bJ cR cX dH iO Nt Sr) Ib(bN cP iB jH jU jY lL qV) Op(aY bE cP hC nW oN Rf) No(Wc Wd Wf Wh Yk Tl) Id(Eq Ho Wb Wf Yh Zw) Sh(aY cP Je oN Rf Rg) Lp(bJ lW mE mF mI oN) nB(Ar Ry Ss Up Uy We) Yf(An aY Ki kS lW) Ng(gP Ho Wd Wh Ye) Xa(aY cP dA kS oN) Wf(bJ iO Kn nF) Ye(iO nC Vs Vv) Va(Aw Hr Je Rg) Ho(Ii Rt Up) Yk(aY kS Ub) Wd(fP kS Sr) Ry(oN oO oQ) Rv(Dl Hf Je) Ri(mT nU oQ) bN(jH Jt Ss) An(Fi Hp) Ar(Ps Rt) Du(Hr lW) Wh(dE oQ) Tl(mF Pe) Tk(gP Kz) Up(lN Sj) Vv(lL lM) aW(Pd Uk) bH(kK nC) hC(Ps Ux) DmI WmkO FilW GcmH HpHr IppH WboN SrUy SsmY WeiO RtkS PbgP dDkG} oD{aK(aC aY bG bV cC cE cG cL cM Co dD dF dH dM Fn Ha Hc Hx iA Im Jj Kg Kk Li Lv Ny Of Ou Oy Oz Ql Qm) Nk(aN Ax bB Bc bH Bo bV Co cQ cW Cx hG Hr Ip Jf Jy kG kQ Li lW Lz MY Na nB Nu nW Of) dD(aE AN aQ aV cB dA Ez Fn Hw Jf Kk Lh Mb mH My nI Nr) Ax(aO Ar aW bN bS cA cK De dH Hf Ih Ip Ir Iu Iv Kr) Tj(aF aI Bb Bc cU De dK GL gP Hb hG kI Mh Nb nY) dR(aE aN aY bE cP dH dL dN Hb iZ kF Kg Ko mF Nr) Bc(bE cB cF cR dM Fn Jf Ky Pk tF) De(aD bE Co Fa Fr Js Li Ok Pk tF) cR(As Bb Cw hG Ip Kp kQ Nb Og) aO(Co Cs Cu Cw nC nH oK Pf) Ip(aW Ed Hv Il Je nK oK) Li(Ar bS cA cK Ir Iu Nj) Pk(Af Ar bC Bn Ju Jv Mn) bH(aW bN cQ dB Hv mF Mz) Co(cY Hf Ir Iu Nj) Hr(aW bN dB Hv mF) aC(In Ke Kk Ko Nv) Pg(Bo Cw Dl oK) aL(cB dA Lz Na) tF(Ms nC nH oK) Af(Ky Nm On) Gl(Mm Ne Nl) Jv(aF Ko Nm) bE(aE Kk Oy) Al(aW dB) Ar(Js Nn) Bn(Js Ok) Hv(Fn Or) aI(bG Kr) cB(Ba Db) cX(Kk Om) BbMl CpOk CveF EdaF MsaU JfoK} Nn{Gn(bE bJ dJ Fn Gp Hp Hu Hw In It Je Jh Jo Kn kO mE mI My Na Nd Ng nI nK Nt oH oO Qt Qu Qw Ug Ur Uu Yf) Tm(Ad Ar aY bH bJ bN bP cI cO cP Di Dl gP Id Ih iO Jp Js Jt Kn Mt mY Nc nI No Nt Pj Si Sr Vi Ti) Yf(Aa Aj aM Ap Ch dJ Ef gL Hr Ki Kn mF Sh Ss Zq Tj) Vi(Aa aI bJ dI dJ dL Ed Ic Je Kk lW My oP Qb Sh) Sh(bE Gz Hr Hu Hx Je NB Nx Og Ri Rm Ss) Ye(Aj bJ cP Iz Jh Ng Oy Qt Qu Qz Ss) Hp(Ao Ap Aw Ba Cp Cv Cw Di Hr Ur) Yh(Aj bJ Ib Jo Kn mE Mg mI Ng) nB(Lp Lt Ry Sf Si Uy Vb Vt) Gh(Je Kn Ng Nt Qu Qw Ub) Zq(aI bJ Et Hu Hx Ss) Eq(bJ cR dJ gL Nc) Yg(mI Ng nI nK Rg) Wd(cR dJ mE Ng nK) Wf(bJ Je mH mT nF) Tl(Dl Hr No Ub) nU(Fn jI lK Ri) mT(Fn Gb lK Rx) oV(cQ kQ Nq Or) Em(bJ Hu Jh) Ho(kG kI mH) Zw(bJ Hu Kn) Xa(iZ Je Qu) mF(Du Fi Lp) pH(aV cV dJ) Dr(Aa kG) Sf(Hu Ss) Jh(Rv Ry) Wh(cP dJ) Kn(Fd Ps) mY(Ex Lt) kK(dD jH) AwUx EfRv FnoQ GcNt GzdA HxOp IbnH SiSs JeLp QuRx RynI PbgP fRkN} pH{dD(aO aW bB bF bQ Cs cW Cx dA Dc De dF dH Hf Iu Jo Jr kK Kq Kr Ks Mj Mn Nj Nk No) Ax(Ao aU bM Bo Cs cY dA dE dJ dR Fn FP Hw In Jo kI Kk kQ nI Nu Or Pj) Fa(aD aE aQ aU aV Bb cY dA dR Ha Hc Hw In Ip It Me Ms Na Nf nI) Nw(Bo bR cF Co dI mH Ml Mm Mn Ms nC Ne nH Nx Of Pf Ph Pi Pj Pk) Ip(cF Co Cu Fy Js Li Ma Mq nC nH oN Pd Pe Pf) dA(Co Ha Ih Im Ir Li Mr nC nK nL Pf Tj) Co(aI aK aL aQ cY dJ dR Jo oH) Ms(aO bS cA cK Et Hu Iz Kz Oy) Li(aK aQ aU aV cB cY dJ In oP) aV(Im nC nH nL oK Pf Pk) Tj(aP cB cS nC oV Pf) Nk(dL gP Jy Kr Ky Of) Ar(aK aQ aU cB dR) Dc(As Bo eF My tF) Pk(dJ dR fP Kk Ky) nC(cS Fr Jf Jm Lh) Et(Db gP Mm Na) Ny(Af Bn cR cX) Ok(As Bo gP Na) aK(aM Ap Cw Fp) cB(aM Fp Fw Ih) nH(Fr Jf Jm Lh) Ko(Ed Kj Kk) Pa(Ba iA Pb) aQ(bL Ha Mz) tF(Al Fw Pf) Ao(Kq On) Bo(bE Oz) Jm(In nL) Oy(Ad kQ) dR(cQ Mz) BakO BbKz BnbE CpKk FnHv JfPf JqKy} Ng{Yg(bQ Ez Fy Ij Il Je Ld Li lW Lz Ma Mh Ml Mt Nd nI nL Nr Pf Pz Qx Ra Rh Rv Tr Wm Tj) Wh(Ba cA cR Ez Gc Gh Hx Ij Il Je kG Ma Mt nI Nj Nr On Pf Pz Qe Rx St Tn Tr) Yh(BA bQ Gp Il Im Jm Me Nr Pf Pz Qc Tr Uc Vi) Wd(BA cT Gp Ij Il Ip Je Ma Mt Nr oF Pf Tr) Pz(bB bN bQ Gh Gp Ho Lt Tn Uk Ut Ye Xa Ti) Bg(Ax Dr Hb hV hW jT lK Qh Wm) Ef(hA jD jE jL jM lN rC rZ) Qh(cA cK dJ iJ jE Rx Tr Zq) Ye(bQ Fy Il Ma Mt On Pf Tr) Uc(iC jD jM Li rC rZ Xa) Ij(Eq Ex Fi Rx Si Wf Yd) Rv(aM bA cR cT Il Jm Kk) Cq(Gp jH jQ jT lK rC) Xa(cR Hr Je Nc Nk Ub) Ps(cF cR Fd Hr Id Je) gP(Fa Ld Li No On Tr) Ho(Mt Pf Qx Tn Tr) Dr(iO Jk Qc Qd) St(Sf Sh Vb Zq) We(aC bE cR dD) Wf(bA bQ cT oF) Vi(aY bQ Hr Qc) Jm(Fi Rt Uy) Rg(jL lN) cR(Ru Vh) oF(Gc Gn) AdeD AfjH YfPf FakQ ExQd FiIl NkpK IpLp YkhB ZqOn QeVb JqaW KxlN LiQn UvrX VujE nUjI nBIK nKjY} nI{Vu(aF aO Ar Ax bL Bn Bo cA cB Ct dA De Ed Eq Fa Fd Fi Gb Gl Gn Ii Il Ip Mv Or Qw Ri Ry Sh Vb Vs Vt Zq Ti) Ry(Bc bQ cB cR Cv Dk Et fR Gc Gn Hr iH Ip Je Jm Ki Mm Nc Nd Ne Oz Ru Ub Uc Vh Yh Tm Ti) Cq(Du Ex Fa Jj Oy Qb Ug Uk Um Uy Vo) Tn(Aj Ct Ed Gn Iz Jj Li Of Op Oy Qw) Qb(Bg bH Ch Co Cu Dk fP hF Uk) Oz(Em Gn Lt Or Sf Sh Wf Zq) bH(Em Fa Jj Pa Pe Pi Qe Tl) Ed(Pz Qd Qc Qh Rt St Vt) Ip(Dr Em Ex Sh Vi Zw Tm) We(cR Ki Mb Nc Nk Nl) Uy(Ao cR Cu Dk iH pF) Vh(Ap cB Dg Jt Nl Sh) Ok(Ap Dl Gn Sh Vi) Fa(bL gP Nk Pf) Wh(Aj As Ct Ib) iO(Rx Yg Yh Zw) lM(iB Jp Nv Ny) Dc(Gz Oy Up) Gn(Jl Lh Nb) Uc(Gd Op Sh) Ps(Al cR Nl) Or(Ax Li Vt) Vi(Nb Nc Ub) Pb(Yd Yk Yf) qY(Ij kI Mq) As(St Yh) Yg(Ib Jj) Qc(jV lN) Rm(Nt Up) Op(Lh Pz) Va(bJ Nk) Oy(Cu Dk) cB(Ux Wm) jH(Jp Oe) AxYf CtQh DeSt DriP GcUs NuiB MmSh UbLt TtTr YkcR WcbJ JlaO TmUp LigP OnhA PfgL

Dd dN Ez gP Jd Je Ju Up) aW(dB Hf Ic iH Ii Jt Kg Ks Ph Rj St) Mm(aI aK aQ aU cJ cY dJ eF Kz oF) Hf(bM cL dM gP Ph Qb Ue Up Vv) Ic(cC dM Hq Ir Iu Rg Up Us) My(Bb Hq Jl Nv Pe) Kx(bV Db Hq Rb Us) Hc(bM cL eF oF) Up(aK cH Dl Jl) Kz(Gl Rj Tk) eF(cH Jl Qy) Cs(Nr Pa) Vv(bM cP) FrcP MkRb HqKc TtJt QtcC JogP KrPa} oO{Ri(aI aM Ax bF bG bH bJ bL cE CQ CU Dc Ex Fw iP Jr Kk Ko Kq Me Mk nY Or Pk Vt) Ry(aP Fy Ij Jy Mb Nr Nx oP Ub Vh Wf) Eq(aY Ho Hr Hx Ly Mb Me Nx Pc Um) aC(Em Gd Gn Lp Lt Rv Ux Wf Yg Yh) Ho(bS cA cK dD dK Hf Iu Iv Nk) bE(Dr Du Ex Lp Lt Op Ux Wf Tl) Dr(aN cE dK dN Hu Id Om) Wf(aL bJ cY dD Fn Ir Iu) Nx(Fc Gz Lp Rt Uy Wb Yh) bH(Du Hp Lp Up Wb Wd) Mb(Ps Vh Wh Yd) Tj(Fd Vh Zq) Nd(Em Ye Tm) Yh(Ks Me Ms) Up(bF Cq Ou) dD(Gc Gn Uy) Gb(Iu Ki) Yd(aY dH) Sf(Jm St) Xa(Ez Nc) Ks(Du Zq) Nw(pK Wb) Op(Ij Kq) Vu(fR Lp) dK(Ru Tm) DpPs EmPd GccY GnaK UcVo YgOg YkUr UkOz} lW{Yk(aP bQ dH hB Ho Ij Iq Jm Lh Nb Nc Nc Nl Nr Nw Pz Rv Vt) Ps(Cv Dl Nd Ne Nh Nl Pz Ub) Qc(jD jI jQ jR lN Oe rA) Rv(cT Fn Hf Hu Hx Nc Nl) Uy(cE cT Lv Ma Mq Tn Tr) Dr(bJ cE Cq Mx Nb Nd) Fi(bQ hB Ij Jm Qh Vu) Yh(bA Cq dM Fn Ij Rg) Vh(dE Hu Jt Mb mT Ub) Nd(Fd Ry Vb We Xa) Lp(Hx Ij Js Ld Mx) Vt(aC eF Gp Yd Yg) Gn(cE Nw oF Tn) Pz(Gh Ry Ux Vb) Xa(bQ Js Mx Ub) Fn(Ux Yg Zw) Nc(Ry We Yd) Nk(Fd fR Tl) Ho(Mp Nw Or) Ip(Em Jj Oy) Jm(Du Wb Zq) Ri(aJ dF Ir) pK(aK aL bW) Dc(Hp Rt) Gc(aC Nw) Nl(Ry Yd) Zw(cW kG) We(cE Uc) Vu(Rt Wb) hB(Hp Zq) CqGd YfNb EtjR MnlN NeYd SjNw JsTl UxaC OycE jHkF} Si{Qb(aC bU cN cR dC dD dH fP hC Hr Hx Id Il Io Iv Je Ki kS Me Nx Pd Wf) bE(Ar Ax Bg cM Cq Cs Cu Cw Fw Ih Ij It Nr Oz Pf Rm Vu) Je(Hx Ij Im Js Kk Mj Mn Mw Mx Nq Ny Pf Qe Qh Rm Xa) Ij(aC Aj cP De Fn Hu Hx Kn Nt Pd Ss) Il(aC dD Fn Hu Hx Ld Mj Mx Nw Tz) Pf(aC dD Hr Hu Hx Nx Ss Yf) Nw(aC aY cN cP Id Oz) Mx(cR iZ mH Nx) Pz(aI kF kI nK) aC(Et Gc hB Mm) cZ(Ax Cs Oz Wm) Hx(cQ Cx Qc) St(cP Dl Ki) Rm(cA dI Ug) aI(Nj Pb Vu) kI(Bb Tr Vh) Qc(Hr Oz) Ji(aY Id) Ss(bQ Ut) Ny(Af Cx) dD(cM cX) DeQh DlQe UbXa PsPd LiNx UgOz} nL{bH(Bo Cw Dg eF Eq Et Fn Gp Ij Ip It Jg Jp Ke Kk Kl Ko Lh Nv Ok On Pk Ps Pz Qd Ru Rv Sr Tr Uc Uh Vh Vt Wh Yg Zq Xa) Pd(Co JG jT Rv Tr Vh Xa) Fn(Bg bQ bR dB Kq Wd Yg) Ri(aZ Co Cw hB Ke Qd Uh) dD(Bo dB Ip Sj Vt Wh) Nc(iB jF jP Ry We) Qc(jD jH jM jT jY) Et(cX gP hA Pj) Jq(CX Ho Tj) Bo(aC bE cR) Ed(Ru Uy Vh) Ij(jL jV jY) Ip(bR Db pK) Wh(bJ Oy Pc) Ry(Nd Nl Yh) lM(iB Jg Mw) Hx(lK Wd) Jm(Rt Sj) Lh(Eq Ho) Rg(Co Ru) Ny(cR cX) Vt(cV iJ) aC(Ps Vh) aI(Db Wm) jG(Lv Qd) ArbE CxOk YfbJ HrUh ZqRm PzqT JglN StaA WdhB NwUp PkcB aUdR dApK} oP{Ry(aJ aY bE dC dD dG dH dI dL dN Gb Hx Ki Ly Mb Me Oy Pd Ub Um Ur) Uy(aC bE bH cM cN dH dK dM Dr Hx Ly Me Nb Nk Nx Oy Pb Pd Um) Up(aC Al aY bH bJ Cv Dc dD Kk Ks Pk Vt) Lv(aC bE cC Em Ic Pk Vh Wc Wh Yh Zw) Ho(bE dD dH Nl Uh) Lp(aC bH cR Oz Pb) Oy(Bb Cv Ip Kd Tr) Eq(Jm Mb Oz Pb) bH(Bb Fc Kd Ru) Fn(Em Oz Vb) Uc(Gd Yh Yf) Ks(Fd Rt Zq) Vh(aQ cY dJ) Vt(bE Un Yg) aC(Kd Ru Tn) Dr(Qb Tj) Gn(dK Tj) Hr(Kd Ru) We(Ki Mb) Wf(bQ Tn) Ri(aE Ax) Vu(aP Vs) Oz(Fd Zq) Pb(Hp Yg) Pk(Ms Nt) aO(Kk St) cD(Nk Pd) CvUg FccR NcWh WcdD XaKi LtbE OpdK} Tk{Fa(aF aL aN aO aS aV aW bA bF bG bI bJ bL Bo bP bQ bR bS bU bW bX cA cB cC cD cE cF cG cK cO cP cU dA Db dG dH dI dJ dL eF Fp Ki Kk Kn KR Kz Ld Me Mn Mt My Ou Pb pF Rb Um Up) Mz(aW cN dD dJ eF Kz Li My Nl Nx Pc Pj Rg) Ar(aK aN bJ bP cF cL dI dJ eF gP hG) Kz(Cq Dp Ih Kx Mw Om Po Qh Tn) gP(Fr Ke Li Mp Po Sr Uh Vt) Li(bU cB cJ eF Me My) eF(Ax Fp Ha Ih Po) Bo(cD Dp Jm Mv) My(Bb Dp Po Vt) Mt(Db Rb Rj) Rg(bX fP Mw) Dp(cB Ld) Fr(aH cP) MeIr QeKr SrcR KxaA} oQ{Ri(Bb bH bJ bL cA cI cJ Co Cq Ct Dg Fr iP Kk Ko Mk Or Ph Pk Vu) Wf(aK aU bE bJ cB cZ Fn Hf Iu Mb Ms Nl) Ry(bE Fy Kg Ma Mt Ni Nr Nx Tn) Mb(Eq Ux Wd We Wh Yg Yf) Ur(Gb Gc Ps Rv Tm Yf) bH(Bo cS Fc Lp Up Uy) Ho(Dp Ip Nk Uh Yf) Xa(bE Ez Nc Nx Oz) Gb(cY dD dE Pd) Zq(Ki Ks Oz Vu) Lp(cR Ks Nx Oz) aC(Du Gc Ux Tl) Yf(bJ Ki Ss) Yg(Jk Og Rt) Up(Bb Jm Qe) Gn(cB dD) Tr(Kj Li) Sf(Jm St) Rg(Co Ex) Uy(dK Nx) Vt(bE kS) Pj(Gc Ok) aA(dA Kk) CqfR TiRm EmPd EqPc LvYd NkRt UbWe UcKj IpYe IuZw WcdD TmdK LtbE RubJ OpbQ PaaM PkgP} Rv{aC(aI aM aQ bP bV cD cE cR cS cX dJ dL Ed fP HF Il Je kS Nd Pi Tm) bE(Al aM As Ax bP bW Cs cX dN Ed Fa Gn Gp Hr Jv Nc Nd Ub Wm Tj) Hu(aI aM aN aW bF BG bP bQ cE cS cX Il Jy Ki Kk pF) Kk(Dl Hr Je Kl Nc Nl Pd Pe Pg Qu) Je(dD Fa Hx Mx Nd Oz Rg Ue) Qe(Dl fR Jt Nm Nt) Tj(kI mH oH Yf) St(Ap Dg Dl Jt) aI(Hr Nl Op Pg) Qb(Dl Ki Nc) aM(aL dD Oz) Fa(cP eF) Hx(Id kK) Kl(Ma Tr) Kp(Nd Pz) Pd(bA cT) nK(Nc Nl) NmJm MxmH HrcZ HfPk IpUu IqfR QubQ PbmT dDmY} Pz{mI(aC Aj dD Ed Gd Kj Kz Nc Op Oy Pk Qc Ry Sf Uu Vu Vv Tm) nK(Dr Gc Gd Gn jI Op Oy Ry Sf Uy Vb Wd Zw) Ux(aI bE Bg bU cV dA dD gP hF mH) Vb(Aa aI aX bI dD kF kG kI kO) Wd(aC aI bE dD dR mH oH) Eq(aC aI bE dA dR oH) kF(Du Fd Gh Op Ry Uy) Zq(aI bE dD Hx Kp) mE(Gd Op Ry Sf Tm) Gb(bE Hu Hx Oz) Vh(aC aI Hx Oz) Sj(Gd Jt Kp) Tl(Dl Nt Pd) Ry(kI kO mH) Op(aI bE kI) Up(kK kN mT) Ed(kI mY) Ye(aC Uu) mT(Gc Lt) AjoH DlrX GhmH SfOz ZwdA ZxaI WekO WfdD TmaC VunU qYkK} hB{Zq(aC aY bE dD Eq Hu iA Ip Je Ks Lu Mx Nu Oz Pb Pk Qb Qw Ss Ub Uu Vs Vu Wd) Vs(Dr Gn Ho Ps Ry Sj Vb Yh Zw Tm) Ux(As aY cP Dc Di Hr iA Ip) Wd(aC iA kO Nc Nl Ub) Uy(cP Iz Jg mY Qu Tm) Gn(dR Gp Hp Jd We) Sj(dH Ip Ki Pd Ub) Ef(Dr Vc Yh Zw) Eq(mH Nc Nj Nl) Tm(aY Di iA Tj) Hp(Hr Ip mH) Hu(Fc Ru Yk) Ye(Ao Ch Ip) Lp(mE mH Oy) Vv(jE jY rC) jF(jE Nb Nc) Gb(iA mT) Yg(Ks Oz) We(Ip Pb) Qu(Fc Ru) Tl(kF mH) Vb(aY kO) Vh(Nc Nl) ChWf DrSs YfTj FnVc ZwJh QbXa OzfR aWjE} pK{Ms(aK aM aN Ao aV Bo bS cK cQ cW hG Ii Il Jf Jo kF Ki Kr Ks Mn Nq Pc) Ax(Ar bS cB cK cY dA dE dH Ir Iu Iv Jo Kr Li mY Nj Nk) aK(aE aU bV cG cY dD dH Je Kp kR Li Ne Nh oF Qm) dD(aE aN cB Cs cW eF hG Jf Ko mH My Nr tF) Iq(aP cM cP Fn kI nW) Nk(Ch Fa Ip Iz Nw) bE(Bo Kk Kr Of) Tj(bJ dA Jh) Fn(cD Gp Hv) Pa(cM Ct Nu) Cp(Mz Ok) Nh(aU dR) Ip(bU nK) aC(Bc Kk) AfOn ArcY AsMy BoNu ChcR CscA DeOk JpNw JvcX NyPk OfaI aYtF dAnK hGnY} Gn{Gp(Ed Et Fn hF Hr Hu Hx Je Jj Jl Jm KK kN Kp Lp mY Nr oF Oz Qb Qc Qh Qn Qx Ra Rj Tz Ub Up Ur Uu Tm Wm) oH(cU Ed Im Ml Mx Nr Oz Pf Pk Qb) Mx(Id iZ kI kN kS nY oF) bQ(bP kF mH Rt Ss Ur Uu) Qc(aQ bE Gd Nm Ug Uu) St(Jt Kf kO mY Nm Nt) Pf(Ii Jo mH nK Nm Ug) dR(mH mT nF oF) Qb(Id Jy kN) bE(kF oF We) kO(Js Nw On) Hx(nU Um) Il(bX Jo) Je(fR Ny) Jm(kI Ug) dD(mT mY) MaVv IjmH QhUu NwnU aCkF aIkI aNkK aRoF} lN{Rg(aR Ba Ct Cw Ha jE Jg Jo Jt Kg Ki Kj Md Mg Mm Nc Nm Of oH Oy Pd Qn Tt Up Vs Vv) Fa(aR Ba cI Ha iB In Nk Pb Pd Up) Qd(aR As Ba bR Cw Kk nW oH Up Vv) Vv(Bg Ch Dk Jq Kq Lv Mz Ou Tn) Lz(bJ Ki kS oH oN pF Up) oH(Hb Kx Li Ml Qb Sr) In(As aW Cv Db) Cw(Lh Mj Ou) Qb(aR Kk nW) Kx(Nc Ni nW) Up(Jq Li rC) Ba(Kq Mz) Mj(As Kk) Jt(Qh Rm) aW(Jq rC) hC(Cs Hb) EtnU MzNc IcNw IonK QcmI JgkI KelM KkdR} nU{Pf(aI bE cB cR dD dE Fn Jf Ko Or Pk Rf Tn Tr Ub Vt Vu) jI(Hq Hx Ip Jm Mm Mv Nk Of Og Ok Om On) Up(Bc Et Iq Jm Nv Ny On Qe Qh St Vu) Ri(Fr Ij Js nY Qc Qd Qe Tn) Vu(Fi Ip Pa Tr Uc Wb We Zq) Tn(Ed Li Pb Qw Rh) Fn(Dr Gc Yg Zw) Ub(Gd Wh Yg Xa) Tj(Op Yh Zw) We(Ki Nc Nk) Wh(Aj bH Dl) Li(kQ Tr Yh) Nd(Op Ry) Uc(Ed Oy) Zq(Lh Rm) Rt(Jm Rg) Oe(fR Ry) BbGd BoHu DlPs MbjP HrWb TrRh WcdD WdbQ OfjY} aI{Zq(Ax cI Cv Fy Il Je Mx Ni Pf Pk Qb St Vu Tj) Wd(As bP cX dJ Fn Ip Nc Nd Nj Nk Nl) Wh(Aj Ao Ap Ef Ip Ni Nj Nk Oy Pb) Tj(Fc Fi kG mI Rt Wf Yf) Op(Nd Nj Nr Pf Pk Qt) Wm(kG kO nK Uy Yg) Ip(Fd kO Ru Yk Zx) Ux(As Bc Cq Cv Dc) Nj(Vb Vh Wf Yg) Hp(Ax Cs Cv Ur) Eq(Nc Oy Pb) Yg(As Ax Vu) Zw(Ao Fn Gl) Nc(Ru Yd) We(Ki Pb) Tm(aY bP) Vu(kG nK) AxYe BckG DuId EfVh NkWf UbTl HrRu QbmY PsVs bHkI} mT{Wh(aC Cq dD Dl iH Kc Ki Kk mH Nx Pb Pc Uv Vu) Up(Et Fr Iq Jl Jm On Qe Qh St Uc Vu) Wf(aQ bQ dR fR Hx Kk Oz Pb Ur Ut) Vh(aK aQ aU aV cY dR kS Uk) Gc(aQ cY Kk oH Us Uv Vu) bH(Dr fR Zw Tl Yf) Ux(bE dR oH Uc) Dr(Jk Kk Nd) Ye(Co Mz Pf) Vu(Fd Ip Ri) Pb(Eq Wd Yg) cR(Ps We Xa) Et(Eq Yg) Fr(aO Ri) Gb(dR Pf) Nk(Ry We) fR(dD Ub) lK(Nv Pg) FnWc TnVv YhdR ZwcY QchA QeUk KiPs} mE{Ip(Dr Gc Lp Wd Zw Zx Tm Tl) Qc(jI jP jR lK qY rA Yh) Zq(Et Ok Oz Qe Rm St) Wc(aC dD Je Nd Om Tr) Wd(bQ cE iH Il Tn Uc) Lp(Et Ij Oz Pf Ql) Gc(aC Nc Nw Ri) Yh(Cq Nr Ph Ry) Uy(Jy kN Ma Ni) Vh(Cv dE Ri Ub) Dr(Al Cq Il) Du(Jm Ok Oz) Vt(bI eF Wh) Cv(Ps Tl) Fi(Im Jm) Tr(bH Rg) We(Ki Uc) Jp(lK qY) Xa(Ij Nc) Rt(Dc Ok) Ux(aC Ed) Pb(Yd Yk) AjWh EtEx FnUk GhOm NdRy HocQ UbPs IlVb IrRi TlOz RuiH} kO{Wm(cB Et Fn Hx Ij Ip Jp Jq Js Ke Kq Lh Nv Nw Ny Om On Pf Qb Qd Qh St Tn Uh Vt) Ry(aC bE bH dN Mb Ri Vh) dD(Bo dB Ip Uy Vt

Of) Fr(iZ Ok) BoCq DcOr FiaO GdKf XanA OpOf} Ow{Wf(Hf Kf Uh Ti) Zq(Je Ks Nl) Yf(Jv Pj) Yj(Il It) CqnO FdOz GhUb MfVh IcVi IpSj YemW TmgP kEoE} Is{IN(aQ Aw Ou) Hr(Du Fd) Id(We Yh) CwkE FiMs GhVj NonC NsnU MfVa YgUg ZqUk JtdJ VsgP mUnL nAnD} Xa{Ub(bI cC Uu) mS(bL Mz Ql) Nn(Na Qw) Js(kC nD) cR(nH nJ) NkkC NlnT HrkP JlVj aCkO cAnD} Op{On(mP mU nB) aI(Rh Vq) bZ(mU nB) ChoH TjnF MfnL MjkE IjnO ImnB NvmP OknI OmnD aYnR cDkN} Tm{nD(aN bQ cE Mx) Vq(aN bI cP) Ip(Jo kP) dB(Pz Qc) AlUe FwnA NnJv NenI aYnR cDnJ} Va{Je(Ex Gz Hr Hu Hw Lv Mn Tz) Rm(aJ aQ bS cK) EtMf MpHr HuKk HxJf OuUm} oE{Vq(Ef Jh Nk Oz Ua) kE(bV Nq Om) Ex(Kn Ld) BomU CpGb WmcP KomM LikQ OzPa} Zq{lX(Js Kq Mj On) Vq(cZ Qd) nD(Ed Ij) EtUk NnQu NlnA IinR StQt JsmU KqmP} Rv{Il(Hr Ms Nm) Hf(Ki Pd) Us(cP Pk) EfQh FnNc NmMf MsQb YhPd YjUk JmUu KnOz} Yd{mS(Id Li lW Me Ml Om) Ed(mP mU) NnKl MlnJ MxmM NcOu} Oh{Sf(Hx Mb Uh) fP(Vh Vv We) BamY CqmM CtoO IlVi YhKn WhKl} Ye{Nb(kP lX) Pf(kP Mg) MsJi UbcD JlmM LimW NwmU OrkI bZmT} eM{Vq(aV cX dA Iu) Jf(nC nH) nT(Fy Nl) TjmU EmRc MfmI} Fa{kQ(Ch Of Oz Pb Sr) gP(dN Ef) WmcP VibZ OzdJ} lN{Mj(aW aY) Qb(hC Ic) Jv(jE Nc) AjBg CvrC MubZ InKx} Fd{mS(aU cY) NcQh IlJo JelW JslX KkUs OkmE bPnB} Nn{Yf(Gp Ip) Vi(Ou Qc) BanD FnYh WfKn UkdJ gPkE} Gb{Hr(Pz Qh) Rm(Jo Us) ChoF EdnD MzmU HuPf} Ps{Il(Kn Nt) Ki(Jh Kj) EfPd GpHr IdQg IuQu} Kz{Tk(Jl Jq Qe Tv Un) Cq(mP nI) IcWn} Ny{mS(nC nH nJ nL) IdYh WbmU JeVh VumM} Yj{aI(Pz Wh) EtJt HxSs IlLd IpUg UkcD} Sj{nT(bF Kq) lX(Jq Qn) IlPd PzKl OknC} Li{kQ(Mu Pf) AxlM FinU NrmW NcqT OkmM} Vv{jH(Jy Mt) GhbZ LvrC TnlK JqqT dRrZ} kE{Ij(Gd Sf) On(Aj Cx) WbOk KqUt cYdR} Cw{aC(kO nC nD) KxjH RioQ bHnC} Du{nA(mI Pa) IlnD JmUu OknK cEmU} Yg{AaSt AlQh CqUg PzaI JsfP UsbZ} Kk{Vi(Kj Pf Qx) Wf(Iu Kx) IlRt} Wd{fP(bA Fn Js Nr) RgbZ} Qh{jE(Jg Nv) StrC JpRt UkdJ} Ri{oQ(Bo iO) PghR eCmM gCpF} Wn{Me(Us Tk) MyRb IcPj JgJt} Pf{Vh(Hr Qw) FimF HuSf OygP} Wb{nC(aC Nx) MmmP JlmU} Zx{Pk(lX mF) TjnU HulW} Ux{ChVq WmQc IlIp RmcS} Vj{Cu(bE dK) DkcT TjdR} aW{FnUk MjjE InrC dRrX} bH{DcmW DgmF LdmU UsnR} fR{Mf(dI Mg) HbcX IvgC} mM{AxdR Balj CshB DcaI} Gd{MmnD PbnC bXgC} Pz{EmnD GhNt UuUw} Ok{CxoO DgnI PjhR} Oz{HaWh NdSf LdgP} bQ{Lt(mP mU) EdnD} eC{AwkO TooQ RgmY} rC{NqIc MgRg IiRm} Aa{MxWf JmRt} As{lK(Ba bC)} Cq{GpnO NtoP} Wm{cP(aI aV)} Fb{aAjV bBrA} Hr{Vi(Iu My)} Id{TzYh WcJs} Ij{SfmU WfKn} Je{ImVh SsWh} Sr{EdmP UkmW} We{KiNw UsaC} Vq{IzbZ RmgC} nR{FcOe KdOy} kO{DbaI FiFw} AxOrmP BaMzjK BobEoQ CpNvnT CsCxjH DlIhjR NrVunU MfOnVh NcLhqT IpWcUr KyTkVt RjVbbZ Constrained panels with 2 analytes, where 1.0E-8 >= 'AUC p-value' > 0. Contains 85 panels of 145,307 total panels evaluated. : Yi(bP iO Kl Kn Ng nH nU oE Vj Th) oE(Gc Hl mM Vi We Yj Yf) Uw(lW lX lY mZ nJ nT) Yl(lW lX lY nN) Oa(gP kC mS nD) oW(dA eC Fn Nt) Fb(jH jU qU) Hl(gC mU nR) Vq(kC nA nJ) bZ(Vj Vw Yj) dU(aC dD Oh) fA(aV dA nC) nN(Vz Wf Yf) lY(Ok Up Wc) Is(kP pH) fB(cQ hG) nA(Vh Wc) hB(mM Rz) jB(Aj Ao) BoWn TjoV NkoD TrVj IkTl YjoP VzlW PzVw WegC RymS LjgP OhpH VumW aKgZ cReM eQnO Constrained panels with 2 analytes, where 1.0E-7 >= 'AUC p-value' > 1.0E-8. Contains 34 panels of 145,307 total panels evaluated. : Oa(bN dJ Ic kQ mW mY) Is(lY nC nH) Yi(cP Ib Vh) Hl(aI bZ) Qa(bN Vw) Vj(bQ oE) gC(Gb Zw) FakQ FbjE GnNn MfVa NgQh YjnR QbbN QclY WhmZ RzbZ RynA LjdJ UwmM VqlX Constrained panels with 2 analytes, where 1.0E-6 >= 'AUC p-value' > 1.0E-7. Contains 77 panels of 145,307 total panels evaluated. : Oa(cP kE mM mU nB nW pH pI) Vj(Lx Ma Nn Oz Qa) Fa(cP gP lN Tk) Tn(kE mM mZ Ng) Is(Ib Ms nL Nt) Yi(eF Mg Uu Vw) Lj(aI dA kQ nY) lY(aI iB Ry) pI(Nl Or Pk) Th(Qa Wm) Fb(lN Ng) Hl(nN oP) Li(gP mW) Rm(Sh Va) Oh(gP Si) Uw(kP nA) Vw(cS Pf) eM(Ed Fn) gC(Gh Ms) nR(bH lK) BgNg DgjB YfnA MffR TrmZ IkYh IlVz YjhB ZqOw StmM PsmS RvaC aEoW bNrC eCmY kQoT Constrained panels with 2 analytes, where 1.0E-5 >= 'AUC p-value' > 1.0E-6. Contains 189 panels of 145,307 total panels evaluated. : Yi(aM aR aY bJ Ef Ik Jh Jo Kg Kj Nt Pd Qt Rf Ss Vv Yl) Is(Hv Ik In Jn Jr Jt Nr oE Uk Up Vv Tk Wm) bN(Ed Et Fa Fw Lj Lx Qd Qe Qh Uk) eC(Fb kO Li Lj mU nC nH nJ nL) Oa(aQ aW dA hG nA oH oN Pd) oE(aW Fb Fn Gn Kx Li Qh Th) Qa(dJ Gn gP Si Up Vi Zq) Lj(aE cP hG Ic iJ iZ pI) Vw(bV Cu hB Il Kk Ma) lY(dD Gc Pz Ri Rv Vq) Vu(mP nA nD nI nO) Wm(aI cZ nA Yl) Fb(Aj Ed Ik Ss) Hl(bE Nn oQ Tl) Tn(nO nT nU Vj) Uk(aW dJ mW Qb) Vq(kP mF mH mM) nN(aI bH Dr Zx) iB(nC nD nH nL) Fa(aY dJ mW) Ng(Cq Ut Yg) Si(Lx Mf Ow) eQ(aE dA kQ) gP(Cs hB Ld) mS(Ho Wh Xa) kE(Fy Kq Ok) Nn(Rz Vz) Tl(Ki Yj) Li(dJ kQ) Va(Ip Je) Vh(Lx nT) Vi(Hr Th) Vj(Oh Pf) bH(jB mU) bZ(Rx Wd) nR(qY Uy) lX(Pk Ry) mZ(Mz Ok) iO(Dr Zw) AxaI NrdA NcpI IcIr IkRv IlRz ShOz WeaC KqmM RieM UwoP aWrC mHjO nAjI Constrained panels with 2 analytes, where 1.0E-4 >= 'AUC p-value' > 1.0E-5. Contains 380 panels of 145,307 total panels evaluated. : Yi(aI Aj Ap Dg Dl Eq Fn Hr Hx Id Ii Il Iu Je Kc Kf Kp mZ nA nJ Nm oN Qu Rc Si Sr Ug Up Yg) bN(Ar Ax HB Ir Is Jm Jq Jr Ko Ld Li Nw oE Pz Qc Rg Rm St Uh Ut Tm Wm) Is(Aj aQ cR Ct cV dJ Ed Ef gP Ic Ih lK qT Rc Sh Si Uu Vj) Oa(AR cY eC Gp Ik iZ Js Jt kP Ng Uk Up Vw Ti Th) oE(cE Cs Fa gP Jq kE Ld Nr Of Oh Pa Pz Qb Rg To Uk) Uk(aI Cq cZ dD Fa Fb Fn Ip Ir Li Lx Qa Qe Qh) lY(Fr Ip Ky mW Nn Ny Om On St Ur Va Vt Vu) Lx(aV aW aY cA cP dA gP Hl Ib Pj Vw Yl) Ng(cE Co Dk gP Kq Tr Uc Uw Vq Wd Wh) aW(cR cV Ed Fa hB Hx jE Jq Lj Qa Rg) Yl(Ax bP Il Kk Ld Ms Nd Oh Ow Rv) Vw(Ax bQ fP Ip Ld Nn Ow Tr Wm) Th(Ed Hx Lj Ma Mj Oz Vu Tm) Fa(aP cA cK dN hG mU Pd pI) Qh(Cp Ct dJ Ib mW Rx Sh Vj) gP(Ax Ch Ed Ir jB Kx Mh No) Qa(aY cP dA Hl nT Rz Sh) Lj(aQ aR aV cV dU Gp mW) nN(bG cV dD eC Hb Kk Vt) dJ(Cs Ed Kx Oz Qb Rm) Hl(aH Gp hB Ow Va) Tn(lX mW nA nD nJ) Ik(hB Li Uw Wh Xa) eM(aQ Fw Jf Nn Ss) Ed(Ip Li Oz Pb) Vz(cD fR Pf Va) aI(Cs Op Sh Ss) lX(Gc Ip Pz Va) mW(Ax bH Jg Vt) mZ(Fr On Qd Yd) nA(Dr jO Tr Up) pI(cQ Je Mf tF) Wm(cP kC oH) Nc(jH qT rX) Ir(cP dA Up) Qb(aQ fP Si) Li(Ic Pb Up) Vj(Hx Kk Ow) Vq(kF mS nB) bE(gZ Rv We) eC(kC nD nF) mM(Ny Ok Vu) iB(kO nJ qT) hB(kE nO Of) lN(Kx mS Rg) Ax(cZ Iq) Bg(Aj Ch) Cs(cZ Gp) Fb(iO Jt) Nn(Eq Sh) Yj(nI oQ) Tl(Pd Ub) Rz(bQ oF) Vi(bZ mS) gZ(dR tF) nT(oW qY) kE(Qd St) AfnR AslK YfTj FnfR FrmT GnGp MzTk NegC HrjB IcrC YgbZ SiPf ShQc WcnJ WhOz KiPs KxjH RxcX OkkP VocE aVoW dDiO qYkK kSrX Constrained panels with 2 analytes, where 1.0E-3 >= 'AUC p-value' > 1.0E-4. Contains 849 panels of 145,307 total panels evaluated. : Vw(aH BA Bg Cq cR Cs cT cU Dk Et Fw Fy Ij Is Je Jl Jm Jy Kf Kq Nr Oh On Ql Rh Rv St Uc Vq Vu Tl Tj) Fb(aQ AW Ax aY bN cA cP Cs cV dA dJ Fw GP Hx Ic Iq Ir Je Jq kQ Ld Mf Ms Oh oW Pd Rc Wm) Ng(Ad aI Ba bF bQ cR Cu cV Dc dF dJ Fa Fy Gp Iz Ps Qt Rg Rm Rv Sr St Tt Ua Uf Vi Yh Zw Xa Th) Is(aI aV aW cA Ch cK dA eC Fd Hl Hp Jd Je Op Qt rX Rz Sf Uf Ug Un Va Vh Vs Zq Ti Th) Qh(Aj aQ aV aW bS cA cK cV dA dD De Ed Fn Gn Gp Ik Je Jt mM Ms Mu Of Ph Si Up Wm) aW(aI aQ Ax bN dB eC Et Fn Hb Hr iO Iq Ir Jj Jr Li lK oT Pd Qb Qd Qn rX rZ Vu) lY(Ax bZ cB cQ cV Et Fw Gp iA iC Ij Jg Jj jO jP Jq jY Lh Li My Mz Nw Or Pk Qd) bN(aI Cq Cs cV Dc dJ Fn Fp Hr Ih Ij jH Js Mj nN Nq Nr Oh Ok On qT Ss Tr Wn) Uk(Al aN aQ Ax dA Ed Fw gP Hr Hx Il Iu Jm Jq Lj Mh Pz Qc Rg Rm Sr Ut Vq) Yi(aC bE cX cZ dA dJ Gd Hu Ic In It Jt My Na Oe Qw Rg Ri Rz Sh Va Vs) oE(As Ax cI Cq dD Ed Hb Hc hG Ib Jr kQ Lx Lz Mb Mq Mr Mt Nd Nn Pf Wm) Qa(aQ aR aV eM Fn Ib Ic kQ mM mT mU mW Nt Pj Qt Sr Vh Vv Ti) dJ(Ax eM Fp Fy Iq Ir Ld Mh Mx Nn Nr Oh Qd Rg Tn Vq Vu Wm Tj) gP(aI aJ cH Fp Fw

Figure 25 Continued

Js Kc Lh Mj Ml Nn Nw Ny Oz Qb Qd Qy Tj) Ed(aI aN aR aU cR Hb Hl Ij jE Jq nD oH rC Rg Vz Yh) Yl(bZ CS Hr Lj Lz Mh Nc Nn Nr Pf Pz Qx Ra Vq Tj) IN(As bB cE cZ Et Hb iB Jq Ke Ki Kk Nc Ne Nl oH Qc) Lx(aQ Co Fd Ic kQ Pb Rc Sh Sr Ss Uf Up Vv Zq Th) al(Aj aY cA eM gZ Ib Ik iO Iq Ir Jr Ld Of Pz Rg) mW(aJ Cs Fr Hx Jp Js Nb Nn Ny Oy Pb Qb St Wm) Fa(cW Gp Ik Jt lM Nt oH Oz Rv Sr Um Up Th) Ij(Fn Ib kP lX Ms nC nH nL Qt Si Ss Uu Vv) Vj(bA Cq cT dF hB Js Ld Mt Nd Nr Tv Ut Vu) Li(aQ aR Bg bS cA cP dA dD Fn kP Ma Wm) Cs(cP dA eC Ik Iq kQ lM oH Oz Th) Ir(aQ aU aV cA cV cY dD eC Hx Ug) Sh(aH bZ cD ll Mn Nx Ny Oh Ow Pf) Th(Ax fP Je Kx Ld Mz Pb Ps Tl) Nn(Ba lX mM mT mU nN nU Tm Yf) Hl(aL bB cD cZ Hx Kk nA Oh Pf) Ib(bQ cE dD eC hA iB Iq Mw rB) Vz(bP gC iO Ms Mx Nd Nr Pb Rx) Oa(aU bS cA cK eM Nd Pb Ph Tk) Va(Dc Hr Jq Nx Or Ou Vq Vu Zw) hB(aC aR Eq hG Iu jE Mu Ss Zq) Cq(Aj bC Ct Ik Kz Ms Ug Ux) Ip(Hx Lp nC nD nH nJ nL Wm) Si(Mx Nw Oz Qc Qd Qe Rm St) oW(aP Hc Iv kE kl mM Na Oy) Qb(aV cV dA eM Gn Ic Up) Oh(aY Ba cR eM Ic oN Sf) nR(aC aO Bn jH Oy Pb Tn) mZ(Et Fy Lh Nv Om Vi Yg) Rx(aM aQ bA cT dF Ug) Up(eM Fw Jq kN Nr Qd) nN(cB cD dA Fi Or Yd) nA(eC iC lK nL qT Yj) Aj(cZ Fr oH Qd Ut) Ax(cP dA Gp Ik oH) Wm(dA dD Gp Jq Qd) Tn(aR Ch De mT Qt) Ss(aH bQ cE gC Yh) Tl(ld Je Mf Nc Nl) Rv(aM Hu Je Kp Mf) Oz(Cu dG Fn Fw Kk) bZ(Eq Oy Vb Vh Zq) jH(Cx kF nD Nl Vv) Et(mM Pj Yj Zq) Ms(cR Iq Ke Rm) Hx(Gn Hv Je Ti) Ik(cR Ps Vq Yc) St(Gb nD Zq Ti) aQ(aK aU cY Jr) eM(aV dI Mq Rc) nT(dD dR lX Vu) qY(jI kF Mb nD) Iq(aV cA Um) Zw(bJ Ii Iu) Lj(Ar cY Yf) Vh(nJ Pf Vu) Oy(bQ cE dF) cV(aN Kx Mh) fA(cB gZ nL) mM(aH Fr Vi) kP(Dc Qd Wh) oP(bH dD Uy) oT(cQ Je nL) Co(kE nH) Nc(iB Xa) Nl(eD qT) Ho(kI Ug) Pz(mI Uu) Jt(On Tr) Tm(aY cD) Ki(We Xa) Rz(cS Vu) Ld(eC Pb) Rg(Gp kQ) Wn(Hf Rb) cE(Hr Of) rC(kS Vv) IK(iB IL) pI(Kz Ne) AroH BahA DrkC PodA FnQc GbRm GdMf lIUx YjnU WdfP KxeC RymP LhkE RigC NyPh OraY OwVi PadU aKaU bWgZ cDkN cMjE cPeQ cRdD nDjP hCrX

Figure 25 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.1E1 | 4.7E1 | 9.9E1 | 5.6E1 | 9.0E1 | 4.3E1 | 1.0E1 | 8.0E0 | 4.0E2 | 1.4E2 | 24 | 8 | 24 | 8 | 0.38 |
| Ad | ug/mL | 1.5E-2 | 7.6E-2 | 3.4E-2 | 9.3E-2 | 3.2E-2 | 1.2E-1 | 1.9E-3 | 3.9E-3 | 9.7E-2 | 3.5E-1 | 18 | 7 | 18 | 7 | 0.67 |
| Af | ng/mL | 6.6E-1 | 6.0E-1 | 6.8E0 | 3.2E0 | 8.5E0 | 5.8E0 | 1.7E-3 | 1.7E-1 | 2.2E1 | 1.6E1 | 18 | 7 | 18 | 7 | 0.50 |
| Aj | ug/mL | 3.4E-1 | 5.2E-1 | 1.7E0 | 2.1E0 | 2.4E0 | 2.6E0 | 2.3E-3 | 2.1E-2 | 6.1E0 | 5.8E0 | 18 | 7 | 18 | 7 | 0.61 |
| Al | mg/mL | 9.9E-5 | 9.3E-5 | 1.1E-4 | 1.9E-4 | 1.3E-4 | 2.4E-4 | 8.0E-6 | 7.2E-5 | 5.7E-4 | 7.2E-4 | 18 | 7 | 18 | 7 | 0.60 |
| An | U/mL | 1.1E2 | 8.8E1 | 2.1E2 | 1.7E2 | 2.5E2 | 1.7E2 | 1.1E0 | 1.3E1 | 9.1E2 | 4.3E2 | 18 | 7 | 18 | 7 | 0.46 |
| Ao | pg/mL | 8.3E1 | 1.3E2 | 1.3E2 | 1.8E2 | 1.4E2 | 2.2E2 | 2.2E1 | 1.8E1 | 6.4E2 | 6.5E2 | 18 | 7 | 18 | 7 | 0.52 |
| Ap | ng/mL | 2.2E1 | 4.3E1 | 2.6E1 | 4.0E1 | 2.0E1 | 2.2E1 | 3.2E0 | 7.2E0 | 8.2E1 | 6.6E1 | 18 | 7 | 18 | 7 | 0.72 |
| Ar | ng/mL | 7.6E-1 | 3.5E0 | 3.1E0 | 5.1E0 | 5.6E0 | 6.0E0 | 6.7E-2 | 3.4E-1 | 2.1E1 | 1.4E1 | 18 | 7 | 18 | 7 | 0.56 |
| As | ng/mL | 3.7E-3 | 1.1E-2 | 8.8E-3 | 9.1E-3 | 1.0E-2 | 5.5E-3 | 1.7E-3 | 1.7E-3 | 3.3E-2 | 1.5E-2 | 18 | 7 | 18 | 7 | 0.58 |
| Aw | pg/mL | 1.7E1 | 2.0E1 | 1.7E1 | 2.1E1 | 3.8E0 | 5.5E0 | 8.2E0 | 1.4E1 | 2.1E1 | 3.0E1 | 18 | 7 | 18 | 7 | 0.73 |
| Ax | ng/mL | 2.6E0 | 3.1E0 | 4.7E0 | 9.5E1 | 5.4E0 | 1.6E2 | 2.5E-2 | 4.2E-1 | 1.6E1 | 3.7E2 | 18 | 7 | 18 | 7 | 0.63 |
| Ba | ng/mL | 6.3E1 | 5.7E2 | 3.5E2 | 3.1E3 | 5.9E2 | 3.8E3 | 2.7E-1 | 1.0E1 | 2.2E3 | 8.1E3 | 18 | 7 | 18 | 7 | 0.72 |
| Bb | ng/mL | 1.4E0 | 2.2E0 | 3.3E0 | 4.9E0 | 3.9E0 | 5.7E0 | 4.1E-3 | 8.4E-1 | 1.5E1 | 1.7E1 | 18 | 7 | 18 | 7 | 0.60 |
| Bc | ng/mL | 2.6E1 | 6.6E1 | 6.7E1 | 1.9E2 | 1.0E2 | 2.5E2 | 4.3E-1 | 2.3E0 | 3.6E2 | 6.9E2 | 18 | 7 | 18 | 7 | 0.63 |
| Bg | ng/mL | 5.7E-2 | 4.1E0 | 5.8E-1 | 6.1E1 | 1.2E0 | 1.5E2 | 5.3E-4 | 2.8E-2 | 4.2E0 | 4.0E2 | 18 | 7 | 18 | 7 | 0.77 |
| Bn | ng/mL | 4.5E-1 | 5.6E-2 | 1.8E0 | 7.0E-1 | 2.5E0 | 1.3E0 | 5.6E-2 | 5.6E-2 | 7.4E0 | 3.4E0 | 18 | 7 | 18 | 7 | 0.30 |
| Bo | ng/mL | 8.8E0 | 2.6E1 | 1.3E1 | 2.8E1 | 1.1E1 | 1.5E1 | 1.6E-2 | 5.6E0 | 3.4E1 | 4.8E1 | 18 | 7 | 18 | 7 | 0.79 |
| Ch | uIU/mL | 7.3E-1 | 1.1E0 | 1.1E1 | 1.7E2 | 2.9E1 | 4.5E2 | 3.4E-3 | 3.3E-1 | 9.8E1 | 1.2E3 | 18 | 7 | 18 | 7 | 0.60 |
| Co | pg/mL | 2.6E1 | 9.7E1 | 3.8E1 | 1.3E2 | 3.8E1 | 1.6E2 | 1.5E-1 | 2.1E1 | 1.3E2 | 5.0E2 | 18 | 7 | 18 | 7 | 0.79 |
| Cp | ng/mL | 2.3E1 | 3.1E1 | 2.6E1 | 4.3E1 | 1.1E1 | 2.4E1 | 1.1E1 | 1.8E1 | 5.0E1 | 7.7E1 | 18 | 7 | 18 | 7 | 0.74 |
| Cq | ng/mL | 3.1E-1 | 4.7E-2 | 6.6E-2 | 7.8E-2 | 1.2E-1 | 6.7E-2 | 8.0E-4 | 1.5E-2 | 5.2E-1 | 1.9E-1 | 18 | 7 | 18 | 7 | 0.69 |
| Cs | ng/mL | 1.0E2 | 5.3E1 | 3.1E2 | 1.4E3 | 5.1E2 | 2.3E3 | 1.3E0 | 8.8E0 | 1.8E3 | 5.1E3 | 18 | 7 | 18 | 7 | 0.56 |
| Ct | ng/mL | 1.8E-1 | 9.7E0 | 3.3E1 | 8.1E1 | 1.1E2 | 1.7E2 | 1.1E-4 | 1.1E-4 | 4.7E2 | 4.6E2 | 18 | 7 | 18 | 7 | 0.66 |
| Cu | ng/mL | 2.0E-1 | 6.4E-1 | 3.4E-1 | 7.6E-1 | 3.9E-1 | 5.6E-1 | 9.0E-5 | 1.9E-1 | 1.5E0 | 1.7E0 | 18 | 7 | 18 | 7 | 0.79 |
| Cv | ng/mL | 3.8E0 | 2.1E0 | 7.1E0 | 1.0E1 | 1.1E1 | 1.5E1 | 1.4E-4 | 3.1E-1 | 4.3E1 | 4.1E1 | 18 | 7 | 18 | 7 | 0.57 |
| Cw | mIU/mL | 1.8E-2 | 5.1E-2 | 2.6E-2 | 4.5E-2 | 2.2E-2 | 1.6E-2 | 2.8E-3 | 2.0E-2 | 9.1E-2 | 6.8E-2 | 18 | 7 | 18 | 7 | 0.84 |
| Cx | ng/mL | 8.1E-1 | 4.7E-3 | 7.1E1 | 9.5E0 | 1.1E2 | 2.5E1 | 9.3E-5 | 9.3E-5 | 2.8E2 | 6.6E1 | 18 | 7 | 18 | 7 | 0.34 |
| Db | ug/mL | 6.6E0 | 1.2E1 | 7.1E0 | 1.1E1 | 7.0E0 | 4.6E0 | 4.8E-1 | 5.9E0 | 2.3E1 | 1.9E1 | 18 | 7 | 18 | 7 | 0.70 |
| Dc | nmol/L | 1.4E-2 | 2.0E-2 | 5.4E-2 | 1.1E-1 | 1.4E-1 | 1.5E-1 | 6.0E-4 | 7.7E-3 | 6.3E-1 | 4.0E-1 | 18 | 7 | 18 | 7 | 0.66 |
| Dd | ug/mL | 4.8E-2 | 4.2E-2 | 8.4E-2 | 8.1E-2 | 8.6E-2 | 9.1E-2 | 8.3E-5 | 6.2E-3 | 3.1E-1 | 2.5E-1 | 18 | 7 | 18 | 7 | 0.44 |
| De | ng/mL | 3.4E-3 | 1.3E-1 | 1.0E-1 | 1.1E-1 | 1.4E-1 | 1.2E-1 | 3.4E-3 | 3.4E-3 | 4.7E-1 | 3.2E-1 | 18 | 7 | 18 | 7 | 0.54 |
| Dg | ng/mL | 1.5E1 | 4.4E1 | 2.4E1 | 4.6E1 | 2.2E1 | 3.2E1 | 9.3E-1 | 7.7E0 | 7.5E1 | 9.3E1 | 18 | 7 | 18 | 7 | 0.73 |
| Di | pg/mL | 1.3E0 | 2.3E0 | 1.8E0 | 2.6E0 | 1.6E0 | 1.6E0 | 1.8E-1 | 1.8E-1 | 5.2E0 | 4.6E0 | 18 | 7 | 18 | 7 | 0.66 |
| Dk | uIU/mL | 1.2E-2 | 7.7E-2 | 3.5E-2 | 9.9E-2 | 4.3E-2 | 1.1E-1 | 1.1E-4 | 8.9E-3 | 1.3E-1 | 3.3E-1 | 18 | 7 | 18 | 7 | 0.76 |
| Dl | ng/mL | 1.4E2 | 1.9E2 | 2.2E2 | 2.5E2 | 2.4E2 | 2.2E2 | 4.0E0 | 4.7E1 | 9.0E2 | 6.1E2 | 18 | 7 | 18 | 7 | 0.58 |
| Ef | ng/ml | 1.0E-1 | 1.3E0 | 4.4E-1 | 2.8E0 | 7.4E-1 | 3.7E0 | 5.7E-4 | 5.7E-4 | 2.4E0 | 9.4E0 | 18 | 7 | 18 | 7 | 0.71 |
| Wm | % | 8.4E-1 | 3.6E0 | 1.1E1 | 2.9E2 | 4.2E1 | 5.3E2 | 8.5E-2 | 8.5E-2 | 1.9E2 | 1.3E3 | 21 | 8 | 21 | 8 | 0.65 |
| Po | pg/ml | 2.2E0 | 3.1E0 | 6.4E0 | 1.5E1 | 9.2E0 | 2.3E1 | 2.6E-2 | 2.6E-2 | 3.6E1 | 7.0E1 | 30 | 10 | 30 | 10 | 0.62 |
| Et | ng/ml | 1.4E3 | 2.1E3 | 1.7E3 | 2.1E3 | 1.3E3 | 1.6E3 | 1.5E2 | 1.8E2 | 5.0E3 | 5.0E3 | 30 | 10 | 30 | 10 | 0.56 |
| Ex | ng/ml | 5.5E-2 | 1.6E-1 | 1.3E-1 | 5.8E-1 | 1.3E-1 | 1.1E0 | 1.7E-4 | 1.5E-4 | 3.3E-1 | 3.1E0 | 11 | 7 | 11 | 7 | 0.56 |
| Fp | ng/ml | 1.4E1 | 3.2E1 | 2.8E1 | 4.3E1 | 3.3E1 | 4.0E1 | 2.8E-1 | 4.0E0 | 1.2E2 | 1.0E2 | 30 | 11 | 30 | 11 | 0.61 |
| Fr | ng/ml | 4.3E4 | 3.3E5 | 1.4E5 | 4.0E5 | 2.4E5 | 2.9E5 | 7.8E2 | 7.9E3 | 8.4E5 | 8.9E5 | 30 | 11 | 30 | 11 | 0.80 |
| Fw | pg/ml | 5.1E0 | 9.4E0 | 3.0E1 | 1.6E1 | 6.2E1 | 1.7E1 | 1.2E-1 | 1.2E-1 | 2.5E2 | 3.9E1 | 18 | 7 | 18 | 7 | 0.56 |
| Gl | pg/ml | 1.2E4 | 1.8E4 | 1.4E4 | 1.7E4 | 1.1E4 | 7.6E3 | 6.3E2 | 4.9E3 | 2.9E4 | 2.6E4 | 18 | 7 | 18 | 7 | 0.55 |
| Gp | U/ml | 1.3E0 | 1.5E-2 | 3.6E0 | 2.1E-1 | 5.9E0 | 3.9E-1 | 1.5E-2 | 1.5E-2 | 2.0E1 | 1.0E0 | 18 | 7 | 18 | 7 | 0.16 |
| Nm | pg/ml | 7.1E3 | 6.4E3 | 1.5E4 | 5.5E4 | 1.9E4 | 1.4E5 | 1.0E-9 | 1.0E-9 | 7.4E4 | 4.4E5 | 30 | 10 | 30 | 10 | 0.55 |
| Nn | pg/ml | 2.0E2 | 1.3E3 | 4.4E3 | 3.1E3 | 1.7E4 | 4.1E3 | 1.0E-9 | 1.0E-9 | 9.5E4 | 1.3E4 | 30 | 10 | 30 | 10 | 0.72 |
| No | pg/ml | 1.4E1 | 3.2E1 | 3.1E1 | 1.4E2 | 3.8E1 | 2.9E2 | 2.4E-1 | 3.3E-1 | 1.5E2 | 9.5E2 | 30 | 10 | 30 | 10 | 0.59 |
| Nq | pg/ml | 5.9E-1 | 2.1E1 | 4.5E1 | 5.1E1 | 1.3E2 | 7.4E1 | 1.0E-9 | 1.0E-9 | 6.7E2 | 2.4E2 | 30 | 10 | 30 | 10 | 0.74 |
| Nr | pg/ml | 1.2E0 | 3.0E0 | 5.5E0 | 3.4E1 | 8.2E0 | 6.2E1 | 1.0E-9 | 1.0E-9 | 2.5E1 | 2.0E2 | 30 | 10 | 30 | 10 | 0.59 |
| Ns | pg/ml | 1.0E-9 | 1.0E-9 | 3.7E1 | 3.6E-1 | 2.0E2 | 1.1E0 | 1.0E-9 | 1.0E-9 | 1.1E3 | 3.6E0 | 30 | 10 | 30 | 10 | 0.51 |
| Nt | pg/ml | 1.5E2 | 1.9E2 | 1.8E2 | 1.9E2 | 1.7E2 | 1.4E2 | 1.5E1 | 3.3E1 | 8.8E2 | 4.3E2 | 30 | 10 | 30 | 10 | 0.51 |
| Nu | pg/ml | 2.2E1 | 3.2E1 | 8.2E1 | 9.1E1 | 1.1E2 | 1.1E2 | 1.0E-9 | 1.0E-9 | 3.8E2 | 2.9E2 | 30 | 10 | 30 | 10 | 0.54 |

Figure 26

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Lu | pg/ml | 1.0E4 | 4.6E3 | 2.7E4 | 1.0E4 | 1.0E5 | 1.8E4 | 1.6E3 | 1.3E3 | 5.6E5 | 6.1E4 | 30 | 10 | 30 | 10 | 0.32 |
| Lv | pg/ml | 1.0E-9 | 4.0E1 | 2.2E1 | 6.3E1 | 5.0E1 | 7.2E1 | 1.0E-9 | 1.0E-9 | 2.6E2 | 1.9E2 | 30 | 10 | 30 | 10 | 0.71 |
| Lw | pg/ml | 1.0E-9 | 1.0E-9 | 1.0E-9 | 2.1E0 | 0.0E0 | 6.8E0 | 1.0E-9 | 1.0E-9 | 1.0E-9 | 2.1E1 | 30 | 10 | 30 | 10 | 0.55 |
| Lx | pg/ml | 5.4E0 | 1.8E2 | 1.7E2 | 6.6E2 | 3.5E2 | 1.3E3 | 1.0E-9 | 1.0E-9 | 1.5E3 | 4.0E3 | 30 | 10 | 30 | 10 | 0.65 |
| Ly | pg/ml | 1.0E-9 | 1.0E-9 | 9.9E0 | 4.3E0 | 1.6E1 | 1.0E1 | 1.0E-9 | 1.0E-9 | 5.8E1 | 3.0E1 | 30 | 10 | 30 | 10 | 0.41 |
| Lz | pg/ml | 1.0E-9 | 1.0E-9 | 2.3E0 | 3.7E0 | 1.0E1 | 1.2E1 | 1.0E-9 | 1.0E-9 | 5.6E1 | 3.7E1 | 30 | 10 | 30 | 10 | 0.52 |
| Ma | pg/ml | 1.2E2 | 1.5E3 | 9.9E2 | 9.2E3 | 3.1E3 | 1.8E4 | 1.0E-9 | 3.9E1 | 1.7E4 | 5.2E4 | 30 | 10 | 30 | 10 | 0.67 |
| Mb | pg/ml | 2.7E1 | 4.7E1 | 3.6E1 | 4.1E1 | 1.7E1 | 1.6E1 | 1.8E1 | 1.9E1 | 6.9E1 | 6.4E1 | 30 | 10 | 30 | 10 | 0.58 |
| Mc | pg/ml | 1.0E-9 | 1.0E-9 | 5.5E-2 | 1.0E-9 | 3.0E-1 | 0.0E0 | 1.0E-9 | 1.0E-9 | 1.7E0 | 1.0E-9 | 30 | 10 | 30 | 10 | 0.48 |
| Md | pg/ml | 1.0E-9 | 1.0E-9 | 7.0E-1 | 1.0E-9 | 2.3E0 | 0.0E0 | 1.0E-9 | 1.0E-9 | 9.8E0 | 1.0E-9 | 30 | 10 | 30 | 10 | 0.43 |
| Me | pg/ml | 2.4E1 | 1.0E1 | 2.6E1 | 1.8E1 | 2.8E1 | 1.9E1 | 2.4E-1 | 1.4E0 | 1.6E2 | 6.0E1 | 30 | 10 | 30 | 10 | 0.44 |
| Mf | pg/ml | 1.0E-9 | 1.0E-9 | 1.5E0 | 6.2E-1 | 6.7E0 | 1.6E0 | 1.0E-9 | 1.0E-9 | 3.7E1 | 5.0E0 | 30 | 10 | 30 | 10 | 0.56 |
| Mg | pg/ml | 2.7E-1 | 3.1E0 | 3.1E0 | 9.9E0 | 4.8E0 | 1.1E1 | 1.0E-9 | 1.0E-9 | 1.7E1 | 2.7E1 | 30 | 10 | 30 | 10 | 0.70 |
| Mh | pg/ml | 1.0E-9 | 3.5E-2 | 3.4E-1 | 1.4E0 | 6.8E-1 | 3.7E0 | 1.0E-9 | 1.0E-9 | 2.6E0 | 1.2E1 | 30 | 10 | 30 | 10 | 0.62 |
| Mi | pg/ml | 1.0E-9 | 1.0E-9 | 1.0E0 | 6.9E0 | 5.7E0 | 1.9E1 | 1.0E-9 | 1.0E-9 | 3.1E1 | 6.1E1 | 30 | 10 | 30 | 10 | 0.58 |
| Mj | pg/ml | 1.0E-9 | 1.2E0 | 5.9E0 | 4.9E0 | 1.7E1 | 7.9E0 | 1.0E-9 | 1.0E-9 | 8.1E1 | 2.4E1 | 30 | 10 | 30 | 10 | 0.63 |
| Mk | pg/ml | 7.0E0 | 4.5E0 | 9.7E0 | 1.0E1 | 1.4E1 | 1.3E1 | 1.0E-9 | 1.0E-9 | 6.6E1 | 3.6E1 | 30 | 10 | 30 | 10 | 0.51 |
| Ml | pg/ml | 1.0E-9 | 1.0E-9 | 1.2E1 | 1.2E1 | 6.2E1 | 3.6E1 | 1.0E-9 | 1.0E-9 | 3.4E2 | 1.1E2 | 30 | 10 | 30 | 10 | 0.58 |
| Mm | pg/ml | 2.5E2 | 4.4E2 | 9.4E2 | 1.1E3 | 1.7E3 | 1.5E3 | 1.0E-9 | 2.7E1 | 7.7E3 | 4.5E3 | 30 | 10 | 30 | 10 | 0.54 |
| Mn | pg/ml | 4.7E0 | 7.6E0 | 7.1E0 | 1.2E1 | 5.9E0 | 1.1E1 | 1.0E-9 | 1.9E0 | 2.1E1 | 3.2E1 | 30 | 10 | 30 | 10 | 0.64 |
| Mp | pg/ml | 1.0E-9 | 6.4E0 | 1.6E1 | 2.1E1 | 4.1E1 | 5.2E1 | 1.0E-9 | 1.0E-9 | 1.7E2 | 1.7E2 | 30 | 10 | 30 | 10 | 0.59 |
| Mq | pg/ml | 1.0E-9 | 1.0E-9 | 1.6E0 | 1.7E1 | 5.2E0 | 4.5E1 | 1.0E-9 | 1.0E-9 | 2.4E1 | 1.4E2 | 30 | 10 | 30 | 10 | 0.60 |
| Mr | pg/ml | 1.0E-9 | 1.4E0 | 6.4E0 | 8.4E0 | 1.5E1 | 1.3E1 | 1.0E-9 | 1.0E-9 | 8.0E1 | 3.3E1 | 30 | 10 | 30 | 10 | 0.55 |
| Ms | pg/ml | 5.0E2 | 3.3E2 | 6.2E2 | 5.1E2 | 6.7E2 | 6.5E2 | 1.0E-9 | 1.0E-9 | 3.3E3 | 2.2E3 | 30 | 10 | 30 | 10 | 0.42 |
| Mt | pg/ml | 1.1E0 | 2.8E0 | 1.3E1 | 6.7E0 | 4.6E1 | 7.9E0 | 1.0E-9 | 1.0E-9 | 2.5E2 | 2.1E1 | 30 | 10 | 30 | 10 | 0.60 |
| Mu | pg/ml | 1.0E-9 | 1.8E0 | 8.3E0 | 3.2E0 | 4.3E1 | 3.4E0 | 1.0E-9 | 1.0E-9 | 2.3E2 | 8.3E0 | 30 | 10 | 30 | 10 | 0.76 |
| Mv | pg/ml | 1.0E-9 | 1.1E2 | 6.9E1 | 2.2E2 | 2.2E2 | 2.7E2 | 1.0E-9 | 1.0E-9 | 9.3E2 | 7.2E2 | 30 | 10 | 30 | 10 | 0.78 |
| Mw | pg/ml | 1.5E1 | 4.4E2 | 7.9E2 | 7.8E2 | 3.2E3 | 8.0E2 | 1.0E-9 | 1.0E-9 | 1.7E4 | 2.2E3 | 30 | 10 | 30 | 10 | 0.79 |
| Mx | pg/ml | 1.0E-9 | 1.0E-9 | 1.9E0 | 2.7E-1 | 5.9E0 | 4.3E-1 | 1.0E-9 | 1.0E-9 | 3.2E1 | 1.2E0 | 30 | 10 | 30 | 10 | 0.46 |
| My | pg/ml | 1.0E-9 | 1.0E2 | 2.5E2 | 3.5E2 | 8.3E2 | 4.4E2 | 1.0E-9 | 1.0E-9 | 4.1E3 | 1.2E3 | 30 | 10 | 30 | 10 | 0.68 |
| Mz | pg/ml | 1.8E1 | 1.9E1 | 4.0E1 | 4.5E1 | 5.5E1 | 5.8E1 | 1.0E-9 | 1.0E-9 | 1.8E2 | 1.6E2 | 30 | 10 | 30 | 10 | 0.53 |
| Na | pg/ml | 1.0E-9 | 1.0E-9 | 9.6E-1 | 1.1E-1 | 2.3E0 | 3.4E-1 | 1.0E-9 | 1.0E-9 | 9.6E0 | 1.1E0 | 30 | 10 | 30 | 10 | 0.37 |
| Nb | pg/ml | 2.7E0 | 4.5E0 | 3.4E0 | 7.3E0 | 3.7E0 | 8.0E0 | 1.0E-9 | 1.3E0 | 1.5E1 | 2.8E1 | 30 | 10 | 30 | 10 | 0.73 |
| Nc | pg/ml | 1.5E2 | 4.6E2 | 3.2E2 | 5.3E2 | 4.6E2 | 3.4E2 | 1.0E-9 | 1.3E2 | 1.8E3 | 1.1E3 | 30 | 10 | 30 | 10 | 0.74 |
| Nd | pg/ml | 1.0E1 | 1.0E1 | 1.8E1 | 2.4E1 | 1.5E1 | 3.2E1 | 1.0E-9 | 5.6E-1 | 4.7E1 | 1.0E2 | 30 | 10 | 30 | 10 | 0.52 |
| Ne | pg/ml | 2.7E2 | 3.2E2 | 3.4E2 | 4.2E2 | 3.3E2 | 2.8E2 | 1.0E-9 | 1.4E2 | 1.3E3 | 9.9E2 | 30 | 10 | 30 | 10 | 0.60 |
| Nf | pg/ml | 1.0E-9 | 1.0E-9 | 1.1E0 | 3.3E0 | 3.7E0 | 5.7E0 | 1.0E-9 | 1.0E-9 | 1.5E1 | 1.8E1 | 30 | 10 | 30 | 10 | 0.62 |
| Ng | pg/ml | 3.5E0 | 6.6E1 | 5.8E1 | 1.3E2 | 9.8E1 | 2.0E2 | 1.0E-9 | 1.0E-9 | 4.3E2 | 6.6E2 | 30 | 10 | 30 | 10 | 0.62 |
| Nh | pg/ml | 4.3E1 | 5.7E1 | 6.5E1 | 5.3E1 | 7.0E1 | 1.9E1 | 7.5E0 | 2.7E1 | 3.4E2 | 7.4E1 | 30 | 10 | 30 | 10 | 0.57 |
| Ni | pg/ml | 5.8E1 | 1.8E2 | 8.2E1 | 2.2E2 | 1.1E2 | 2.3E2 | 1.0E-9 | 1.0E-9 | 4.8E2 | 5.5E2 | 30 | 10 | 30 | 10 | 0.64 |
| Nj | pg/ml | 3.8E0 | 8.4E0 | 7.8E0 | 8.7E0 | 8.4E0 | 5.4E0 | 1.0E-9 | 1.0E-9 | 3.5E1 | 2.0E1 | 30 | 10 | 30 | 10 | 0.61 |
| Nk | pg/ml | 1.3E1 | 2.5E1 | 2.3E1 | 2.8E1 | 3.3E1 | 1.9E1 | 1.0E-9 | 2.6E0 | 1.7E2 | 6.4E1 | 30 | 10 | 30 | 10 | 0.67 |
| Nl | pg/ml | 2.3E1 | 4.6E1 | 3.3E1 | 4.7E1 | 3.2E1 | 1.8E1 | 1.0E-9 | 1.9E1 | 1.4E2 | 7.7E1 | 30 | 10 | 30 | 10 | 0.70 |
| Hq | pg/ml | 1.1E0 | 1.3E0 | 4.1E0 | 9.4E0 | 9.5E0 | 1.9E1 | 1.0E-9 | 1.0E-9 | 5.0E1 | 6.1E1 | 30 | 10 | 30 | 10 | 0.59 |
| Hr | pg/ml | 9.8E1 | 1.3E2 | 4.7E2 | 3.2E2 | 8.1E2 | 5.0E2 | 3.5E1 | 2.2E1 | 3.7E3 | 1.7E3 | 30 | 10 | 30 | 10 | 0.53 |
| Hu | pg/ml | 1.8E1 | 5.4E2 | 9.2E3 | 2.7E3 | 4.8E4 | 3.6E3 | 1.0E-9 | 1.0E-9 | 2.6E5 | 8.8E3 | 30 | 10 | 30 | 10 | 0.74 |
| Hv | pg/ml | 2.9E0 | 1.1E0 | 6.1E0 | 1.9E0 | 1.5E1 | 2.9E0 | 1.0E-9 | 1.0E-9 | 8.4E1 | 9.4E0 | 30 | 10 | 30 | 10 | 0.24 |
| Hw | pg/ml | 5.2E0 | 7.1E0 | 1.6E1 | 8.1E0 | 2.8E1 | 6.6E0 | 1.3E0 | 5.3E-1 | 1.5E2 | 2.0E1 | 30 | 10 | 30 | 10 | 0.47 |
| Hx | pg/ml | 1.6E1 | 2.9E1 | 3.8E1 | 2.9E1 | 6.5E1 | 2.2E1 | 1.0E-9 | 5.0E0 | 3.1E2 | 5.5E1 | 30 | 10 | 30 | 10 | 0.61 |
| Ih | ng/ml | 6.8E1 | 1.3E2 | 2.1E2 | 2.6E2 | 3.5E2 | 3.7E2 | 1.4E0 | 4.7E0 | 1.7E3 | 1.1E3 | 30 | 10 | 30 | 10 | 0.54 |
| Ii | ng/ml | 9.4E1 | 5.4E1 | 1.3E2 | 1.1E2 | 1.5E2 | 1.3E2 | 2.9E0 | 9.8E0 | 5.3E2 | 4.3E2 | 29 | 10 | 29 | 10 | 0.47 |
| Ij | ng/ml | 7.8E1 | 2.5E2 | 1.7E2 | 3.1E2 | 3.7E2 | 2.9E2 | 4.7E0 | 2.3E1 | 2.0E3 | 8.4E2 | 29 | 9 | 29 | 9 | 0.76 |
| Ik | ng/ml | 1.6E2 | 2.6E2 | 3.5E2 | 4.9E2 | 4.9E2 | 5.7E2 | 1.3E0 | 2.7E0 | 1.5E3 | 1.5E3 | 29 | 10 | 29 | 10 | 0.59 |
| Il | ng/ml | 2.2E2 | 6.5E2 | 8.7E2 | 2.1E3 | 2.3E3 | 3.7E3 | 1.0E-9 | 2.5E1 | 1.2E4 | 1.2E4 | 29 | 10 | 29 | 10 | 0.65 |
| Im | ng/ml | 1.7E2 | 7.0E2 | 4.8E2 | 1.4E3 | 8.3E2 | 2.1E3 | 2.7E1 | 5.6E1 | 3.4E3 | 6.8E3 | 29 | 10 | 29 | 10 | 0.69 |
| In | ng/ml | 2.5E0 | 1.5E0 | 1.4E1 | 5.4E0 | 4.3E1 | 9.2E0 | 1.0E-9 | 1.0E-9 | 2.4E2 | 2.9E1 | 30 | 10 | 30 | 10 | 0.39 |
| Io | ng/ml | 7.0E3 | 1.0E4 | 1.7E4 | 1.8E4 | 3.7E4 | 2.5E4 | 6.2E0 | 2.2E3 | 2.0E5 | 8.4E4 | 30 | 10 | 30 | 10 | 0.56 |

Figure 26 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ip | ng/ml | 1.0E1 | 3.0E1 | 1.9E1 | 3.3E1 | 2.1E1 | 3.1E1 | 1.0E-9 | 4.4E-2 | 6.1E1 | 1.0E2 | 30 | 10 | 30 | 10 | 0.64 |
| Iq | ug/ml | 7.6E-2 | 2.5E-1 | 3.0E-1 | 3.6E-1 | 5.5E-1 | 3.8E-1 | 1.0E-9 | 1.0E-9 | 2.1E0 | 1.2E0 | 30 | 10 | 30 | 10 | 0.63 |
| Ir | ug/ml | 3.0E-1 | 1.4E0 | 1.7E0 | 2.5E0 | 4.8E0 | 2.9E0 | 1.0E-9 | 8.4E-2 | 2.6E1 | 9.1E0 | 30 | 10 | 30 | 10 | 0.72 |
| Is | ng/ml | 2.3E0 | 1.2E1 | 1.5E1 | 1.8E1 | 2.8E1 | 1.4E1 | 2.9E-2 | 3.7E-1 | 1.1E2 | 3.9E1 | 30 | 10 | 30 | 10 | 0.74 |
| It | ng/ml | 1.3E0 | 4.9E-1 | 3.4E1 | 1.5E1 | 1.5E2 | 3.6E1 | 1.0E-9 | 1.0E-9 | 8.3E2 | 1.1E2 | 30 | 10 | 30 | 10 | 0.40 |
| Iu | ng/ml | 9.5E1 | 1.3E2 | 2.2E2 | 2.9E2 | 2.7E2 | 3.3E2 | 1.0E-9 | 1.0E-9 | 1.2E3 | 8.5E2 | 30 | 10 | 30 | 10 | 0.56 |
| Iv | ng/ml | 1.8E1 | 4.9E1 | 5.4E1 | 7.0E1 | 1.4E2 | 6.1E1 | 1.0E-9 | 1.9E0 | 7.7E2 | 1.6E2 | 30 | 10 | 30 | 10 | 0.69 |
| Pz | ng/ml | 2.1E3 | 1.0E4 | 3.5E3 | 7.0E3 | 3.5E3 | 4.1E3 | 3.6E1 | 6.5E2 | 1.0E4 | 1.0E4 | 29 | 10 | 29 | 10 | 0.72 |
| Qa | ng/ml | 5.3E3 | 1.3E4 | 8.9E3 | 1.3E4 | 1.0E4 | 9.5E3 | 3.4E2 | 7.2E2 | 3.6E4 | 2.8E4 | 29 | 10 | 29 | 10 | 0.64 |
| Qb | ng/ml | 1.5E2 | 1.7E2 | 3.3E2 | 2.2E2 | 7.5E2 | 1.7E2 | 1.1E1 | 2.9E1 | 4.1E3 | 6.0E2 | 29 | 10 | 29 | 10 | 0.52 |
| Qc | ng/ml | 2.5E2 | 5.9E2 | 3.7E2 | 8.4E2 | 4.0E2 | 8.5E2 | 2.7E1 | 1.7E2 | 1.4E3 | 3.1E3 | 29 | 10 | 29 | 10 | 0.77 |
| Qd | ng/ml | 9.3E3 | 2.5E4 | 2.3E4 | 3.8E4 | 3.6E4 | 4.3E4 | 9.8E2 | 3.4E3 | 1.5E5 | 1.5E5 | 29 | 10 | 29 | 10 | 0.66 |
| Qe | ng/ml | 9.4E2 | 3.2E3 | 1.6E3 | 3.0E3 | 1.7E3 | 2.1E3 | 6.8E1 | 2.8E2 | 6.0E3 | 6.0E3 | 29 | 10 | 29 | 10 | 0.69 |
| Jg | ng/ml | 3.6E2 | 9.5E2 | 8.3E2 | 1.5E3 | 1.3E3 | 1.6E3 | 1.1E1 | 1.1E2 | 6.8E3 | 5.3E3 | 30 | 10 | 30 | 10 | 0.69 |
| Jh | ng/ml | 4.9E0 | 4.1E1 | 2.2E1 | 6.1E1 | 4.9E1 | 6.1E1 | 1.0E-9 | 1.3E0 | 2.4E2 | 1.8E2 | 30 | 10 | 30 | 10 | 0.78 |
| Ji | ng/ml | 6.6E1 | 1.1E2 | 1.0E2 | 2.6E2 | 1.1E2 | 5.5E2 | 8.3E0 | 1.8E1 | 5.4E2 | 1.8E3 | 30 | 10 | 30 | 10 | 0.56 |
| Jj | ng/ml | 3.2E2 | 3.8E2 | 7.7E2 | 7.0E2 | 1.4E3 | 1.0E3 | 4.9E0 | 2.0E1 | 7.7E3 | 3.5E3 | 30 | 10 | 30 | 10 | 0.49 |
| Jk | ng/ml | 1.9E0 | 4.8E1 | 3.7E1 | 5.7E1 | 9.5E1 | 5.8E1 | 1.1E-1 | 6.5E-1 | 3.9E2 | 1.7E2 | 30 | 10 | 30 | 10 | 0.74 |
| Jl | ng/ml | 8.6E-1 | 2.7E0 | 2.1E1 | 6.1E0 | 9.8E1 | 9.3E0 | 1.1E-3 | 4.8E-2 | 5.4E2 | 2.6E1 | 30 | 10 | 30 | 10 | 0.67 |
| Jm | ng/ml | 1.6E1 | 3.4E1 | 4.0E1 | 4.6E1 | 6.0E1 | 5.0E1 | 1.0E-9 | 2.3E0 | 2.9E2 | 1.3E2 | 30 | 10 | 30 | 10 | 0.58 |
| Jn | pg/ml | 3.7E-1 | 7.9E-1 | 2.4E0 | 2.3E0 | 7.2E0 | 3.2E0 | 1.0E-9 | 1.0E-9 | 3.9E1 | 9.5E0 | 30 | 10 | 30 | 10 | 0.59 |
| Jo | pg/ml | 2.6E3 | 3.4E3 | 3.4E3 | 4.8E3 | 3.3E3 | 4.1E3 | 1.9E2 | 4.8E2 | 1.5E4 | 1.3E4 | 30 | 10 | 30 | 10 | 0.60 |
| Jp | pg/ml | 7.7E4 | 1.0E5 | 7.6E4 | 1.0E5 | 3.5E4 | 4.9E4 | 2.8E3 | 1.6E4 | 1.7E5 | 1.9E5 | 30 | 10 | 30 | 10 | 0.68 |
| Jq | pg/ml | 7.0E1 | 1.2E2 | 2.9E2 | 4.8E2 | 7.3E2 | 1.1E3 | 5.4E0 | 2.2E1 | 4.0E3 | 3.7E3 | 30 | 10 | 30 | 10 | 0.57 |
| Jr | pg/ml | 5.7E0 | 1.9E1 | 2.0E1 | 2.3E1 | 3.9E1 | 2.7E1 | 1.0E-9 | 1.0E-9 | 1.8E2 | 8.6E1 | 30 | 10 | 30 | 10 | 0.55 |
| Js | pg/ml | 1.4E1 | 1.3E1 | 4.1E1 | 2.6E1 | 1.1E2 | 3.6E1 | 1.3E0 | 1.0E-9 | 6.1E2 | 1.2E2 | 30 | 10 | 30 | 10 | 0.50 |
| Jt | pg/ml | 1.9E3 | 2.6E3 | 2.3E3 | 2.8E3 | 1.7E3 | 2.2E3 | 2.8E2 | 2.6E2 | 7.3E3 | 6.9E3 | 30 | 10 | 30 | 10 | 0.55 |
| Lh | pg/ml | 1.3E4 | 3.8E4 | 2.3E4 | 4.0E4 | 2.5E4 | 3.1E4 | 1.8E2 | 5.5E2 | 1.2E5 | 9.2E4 | 30 | 10 | 30 | 10 | 0.68 |
| Li | pg/ml | 1.8E3 | 2.0E4 | 6.9E3 | 3.3E4 | 1.3E4 | 4.0E4 | 2.6E1 | 3.7E1 | 6.3E4 | 1.3E5 | 30 | 10 | 30 | 10 | 0.74 |
| Lj | pg/ml | 2.3E3 | 6.8E3 | 7.6E3 | 2.1E4 | 1.7E4 | 3.5E4 | 1.0E-9 | 2.4E2 | 8.8E4 | 1.0E5 | 30 | 10 | 30 | 10 | 0.57 |
| Nv | pg/ml | 4.4E3 | 7.5E3 | 1.7E4 | 2.1E4 | 3.1E4 | 3.8E4 | 8.4E1 | 5.4E2 | 1.5E5 | 1.3E5 | 30 | 10 | 30 | 10 | 0.63 |
| Nw | pg/ml | 8.6E3 | 1.4E4 | 1.5E4 | 3.3E4 | 1.6E4 | 6.3E4 | 5.7E2 | 1.6E3 | 6.2E4 | 2.1E5 | 30 | 10 | 30 | 10 | 0.56 |
| Nx | pg/ml | 2.4E2 | 3.3E2 | 3.9E2 | 6.8E2 | 5.0E2 | 8.8E2 | 1.0E-9 | 1.7E1 | 1.9E3 | 2.8E3 | 30 | 10 | 30 | 10 | 0.60 |
| Ny | pg/ml | 1.5E0 | 1.4E1 | 2.6E1 | 4.0E1 | 4.7E1 | 5.8E1 | 1.0E-9 | 1.0E-9 | 1.9E2 | 1.8E2 | 30 | 10 | 30 | 10 | 0.69 |
| Oe | pg/ml | 5.5E1 | 4.6E1 | 2.2E2 | 2.7E2 | 3.4E2 | 5.1E2 | 1.0E-9 | 1.0E-9 | 1.4E3 | 1.6E3 | 30 | 10 | 30 | 10 | 0.49 |
| Of | pg/ml | 5.9E1 | 5.1E2 | 3.3E3 | 5.0E3 | 1.4E4 | 7.6E3 | 1.0E-9 | 8.6E0 | 7.6E4 | 1.9E4 | 30 | 10 | 30 | 10 | 0.71 |
| Og | pg/ml | 9.1E-2 | 6.2E-2 | 1.7E-1 | 1.1E0 | 2.4E-1 | 1.9E0 | 1.0E-9 | 1.0E-9 | 1.0E0 | 5.0E0 | 30 | 10 | 30 | 10 | 0.49 |
| Oh | pg/ml | 3.3E0 | 4.6E0 | 1.5E1 | 3.3E1 | 2.6E1 | 8.8E1 | 1.2E-2 | 1.9E-1 | 9.1E1 | 2.8E2 | 30 | 10 | 30 | 10 | 0.52 |
| Oi | pg/ml | 2.7E0 | 9.4E-1 | 6.1E0 | 5.8E0 | 8.4E0 | 1.0E1 | 1.0E-9 | 1.0E-9 | 2.7E1 | 2.8E1 | 30 | 10 | 30 | 10 | 0.43 |
| Ok | pg/ml | 3.5E2 | 5.3E2 | 5.8E2 | 7.6E3 | 6.9E2 | 2.2E4 | 4.0E1 | 3.9E1 | 3.0E3 | 7.0E4 | 30 | 10 | 30 | 10 | 0.62 |
| Om | pg/ml | 4.4E2 | 8.5E2 | 1.8E3 | 2.2E3 | 6.5E3 | 3.8E3 | 1.0E-9 | 8.4E1 | 3.6E4 | 1.3E4 | 30 | 10 | 30 | 10 | 0.65 |
| On | pg/ml | 1.7E2 | 5.2E2 | 3.3E2 | 1.4E3 | 4.6E2 | 3.0E3 | 7.2E0 | 4.8E1 | 2.4E3 | 9.8E3 | 30 | 10 | 30 | 10 | 0.71 |
| Oy | pg/ml | 2.2E-1 | 7.7E-1 | 2.2E0 | 7.6E0 | 7.4E0 | 1.7E1 | 1.0E-9 | 1.0E-9 | 4.0E1 | 5.5E1 | 30 | 10 | 30 | 10 | 0.60 |
| Oz | pg/ml | 2.5E-2 | 1.2E-1 | 2.8E-1 | 2.1E-1 | 3.8E-1 | 2.5E-1 | 1.0E-9 | 1.0E-9 | 1.5E0 | 6.2E-1 | 30 | 10 | 30 | 10 | 0.47 |
| Pa | pg/ml | 3.4E-1 | 4.4E-1 | 5.8E-1 | 1.3E0 | 7.9E-1 | 2.6E0 | 1.0E-9 | 1.0E-9 | 3.8E0 | 8.8E0 | 30 | 10 | 30 | 10 | 0.60 |
| Pb | pg/ml | 1.0E-9 | 3.5E-2 | 1.0E-1 | 1.0E-1 | 1.4E-1 | 1.3E-1 | 1.0E-9 | 1.0E-9 | 4.1E-1 | 3.2E-1 | 30 | 10 | 30 | 10 | 0.51 |
| Pc | pg/ml | 1.3E-1 | 5.0E-1 | 3.2E-1 | 5.2E-1 | 3.8E-1 | 5.2E-1 | 1.0E-9 | 1.0E-9 | 1.1E0 | 1.4E0 | 30 | 10 | 30 | 10 | 0.59 |
| Pd | pg/ml | 1.4E0 | 1.5E0 | 3.0E0 | 4.0E0 | 7.0E0 | 5.2E0 | 1.0E-9 | 2.9E-1 | 3.9E1 | 1.5E1 | 30 | 10 | 30 | 10 | 0.56 |
| Pe | pg/ml | 1.7E1 | 5.2E1 | 5.9E1 | 1.9E2 | 1.0E2 | 3.0E2 | 1.0E-9 | 1.0E-9 | 4.3E2 | 8.0E2 | 30 | 10 | 30 | 10 | 0.68 |
| Pf | pg/ml | 9.2E0 | 8.5E0 | 3.8E0 | 2.2E1 | 1.1E1 | 2.9E1 | 1.0E-9 | 4.7E-1 | 6.0E1 | 8.8E1 | 30 | 10 | 30 | 10 | 0.86 |
| Pg | pg/ml | 4.2E0 | 7.9E0 | 3.4E1 | 2.0E1 | 1.1E2 | 3.6E1 | 1.0E-9 | 4.0E0 | 6.0E2 | 1.2E2 | 30 | 10 | 30 | 10 | 0.68 |
| aA | mg/dL | 1.3E0 | 1.3E0 | 1.5E0 | 1.7E0 | 8.3E-1 | 1.0E0 | 4.0E-1 | 4.0E-1 | 3.9E0 | 3.6E0 | 43 | 15 | 43 | 15 | 0.53 |
| aC | mg/mL | 2.0E0 | 2.3E0 | 2.3E0 | 2.4E0 | 8.4E-1 | 1.3E0 | 1.3E0 | 1.2E0 | 4.0E0 | 5.1E0 | 18 | 7 | 18 | 7 | 0.50 |
| aD | ug/mL | 2.9E0 | 6.0E0 | 3.8E0 | 6.8E0 | 2.5E0 | 5.2E0 | 1.2E0 | 1.1E0 | 9.8E0 | 1.7E1 | 18 | 7 | 18 | 7 | 0.70 |
| aE | mg/mL | 5.0E-1 | 5.9E-1 | 5.2E-1 | 6.4E-1 | 1.1E-1 | 1.5E-1 | 3.8E-1 | 4.7E-1 | 8.2E-1 | 9.6E-1 | 18 | 7 | 18 | 7 | 0.81 |
| aF | ng/mL | 2.2E0 | 3.9E0 | 7.2E0 | 5.6E0 | 1.0E1 | 5.5E0 | 3.4E-1 | 6.3E-1 | 3.5E1 | 1.5E1 | 18 | 7 | 18 | 7 | 0.51 |
| aG | mg/mL | 1.3E-1 | 1.1E-1 | 1.5E-1 | 1.6E-1 | 7.7E-2 | 1.3E-1 | 7.0E-2 | 7.0E-2 | 3.1E-1 | 4.3E-1 | 18 | 7 | 18 | 7 | 0.45 |

Figure 26 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aH | ug/mL | 7.4E1 | 6.3E1 | 8.6E1 | 6.6E1 | 4.6E1 | 2.7E1 | 2.3E1 | 3.2E1 | 1.9E2 | 1.2E2 | 18 | 7 | 18 | 7 | 0.36 |
| aI | ug/mL | 1.7E2 | 1.8E2 | 1.8E2 | 1.7E2 | 6.1E1 | 4.7E1 | 9.1E1 | 7.5E1 | 3.0E2 | 2.2E2 | 18 | 7 | 18 | 7 | 0.46 |
| aJ | ug/mL | 3.9E0 | 5.5E0 | 4.4E0 | 6.8E0 | 3.4E0 | 4.6E0 | 7.6E-1 | 2.0E0 | 1.6E1 | 1.5E1 | 18 | 7 | 18 | 7 | 0.66 |
| aK | ng/mL | 1.5E0 | 1.4E0 | 2.0E0 | 1.3E0 | 1.9E0 | 4.2E-1 | 2.1E-1 | 4.4E-1 | 7.0E0 | 1.7E0 | 18 | 7 | 18 | 7 | 0.42 |
| aL | mg/mL | 7.8E-1 | 7.1E-1 | 8.2E-1 | 6.9E-1 | 2.5E-1 | 1.4E-1 | 4.5E-1 | 4.7E-1 | 1.3E0 | 8.2E-1 | 18 | 7 | 18 | 7 | 0.35 |
| aM | U/mL | 2.2E1 | 8.4E1 | 3.1E1 | 6.2E1 | 3.3E1 | 3.8E1 | 6.3E0 | 5.2E0 | 1.4E2 | 1.0E2 | 18 | 7 | 18 | 7 | 0.76 |
| aN | U/mL | 2.2E1 | 1.3E1 | 3.5E1 | 1.4E1 | 3.7E1 | 8.4E0 | 4.6E0 | 5.4E0 | 1.3E2 | 2.8E1 | 18 | 7 | 18 | 7 | 0.34 |
| aO | pg/mL | 1.2E2 | 2.4E2 | 5.4E2 | 9.1E2 | 1.0E3 | 1.3E3 | 6.0E-2 | 6.0E-2 | 3.6E3 | 3.5E3 | 18 | 7 | 18 | 7 | 0.60 |
| aP | ng/mL | 2.1E0 | 3.2E0 | 2.6E0 | 3.5E0 | 1.5E0 | 1.8E0 | 9.6E-1 | 1.3E0 | 6.4E0 | 6.1E0 | 18 | 7 | 18 | 7 | 0.66 |
| aQ | ng/mL | 3.0E-1 | 2.4E-1 | 4.7E-1 | 2.5E-1 | 4.0E-1 | 1.1E-1 | 7.2E-2 | 1.2E-1 | 1.3E0 | 4.5E-1 | 18 | 7 | 18 | 7 | 0.40 |
| aR | ng/mL | 1.7E0 | 2.3E0 | 2.6E0 | 2.9E0 | 2.6E0 | 2.5E0 | 4.5E-1 | 2.5E-1 | 1.0E1 | 5.9E0 | 18 | 7 | 18 | 7 | 0.51 |
| aS | ng/mL | 2.8E-1 | 3.3E-1 | 7.7E-1 | 1.8E0 | 1.3E0 | 3.1E0 | 4.2E-3 | 9.1E-2 | 4.9E0 | 8.7E0 | 18 | 7 | 18 | 7 | 0.63 |
| aU | pg/mL | 6.6E1 | 6.8E1 | 9.1E1 | 7.0E1 | 9.9E1 | 2.6E1 | 8.9E0 | 3.3E1 | 4.1E2 | 1.1E2 | 18 | 7 | 18 | 7 | 0.52 |
| aV | ng/mL | 7.0E-1 | 8.1E-1 | 7.7E-1 | 6.9E-1 | 5.1E-1 | 4.6E-1 | 5.0E-2 | 9.4E-2 | 2.0E0 | 1.4E0 | 18 | 7 | 18 | 7 | 0.46 |
| aW | pg/mL | 2.1E1 | 1.7E1 | 2.0E1 | 1.8E1 | 9.9E0 | 9.8E0 | 7.2E-2 | 7.7E0 | 3.3E1 | 3.4E1 | 18 | 7 | 18 | 7 | 0.40 |
| aX | ng/mL | 6.0E0 | 1.4E1 | 9.2E0 | 3.6E1 | 7.7E0 | 6.0E1 | 1.7E0 | 3.8E0 | 2.5E1 | 1.7E2 | 18 | 7 | 18 | 7 | 0.72 |
| aY | pg/mL | 5.2E1 | 7.8E1 | 6.5E1 | 1.1E2 | 3.5E1 | 7.0E1 | 2.5E1 | 3.2E1 | 1.5E2 | 2.0E2 | 18 | 7 | 18 | 7 | 0.74 |
| aZ | pg/mL | 1.3E2 | 1.7E2 | 1.0E3 | 2.7E2 | 1.8E3 | 1.8E2 | 8.8E0 | 8.3E1 | 5.4E3 | 5.4E2 | 18 | 7 | 18 | 7 | 0.60 |
| bA | ng/mL | 1.2E1 | 2.4E2 | 5.5E1 | 4.0E2 | 8.2E1 | 4.6E2 | 3.0E-2 | 1.7E1 | 3.2E2 | 1.3E3 | 18 | 7 | 18 | 7 | 0.83 |
| bB | ng/mL | 2.4E2 | 3.3E2 | 3.3E2 | 2.8E2 | 2.1E2 | 1.4E2 | 6.5E1 | 7.6E1 | 7.6E2 | 4.5E2 | 18 | 7 | 18 | 7 | 0.46 |
| bC | ng/mL | 3.2E2 | 4.3E2 | 5.6E2 | 6.8E2 | 6.0E2 | 6.7E2 | 9.8E0 | 1.3E2 | 2.4E3 | 1.8E3 | 18 | 7 | 18 | 7 | 0.58 |
| bE | mg/mL | 5.2E0 | 5.6E0 | 5.6E0 | 6.8E0 | 1.9E0 | 3.0E0 | 2.9E0 | 3.4E0 | 9.4E0 | 1.2E1 | 18 | 7 | 18 | 7 | 0.61 |
| bF | pg/mL | 2.2E1 | 4.0E1 | 5.6E1 | 9.3E2 | 7.5E1 | 2.4E3 | 2.1E0 | 1.1E1 | 3.0E2 | 6.3E3 | 18 | 7 | 18 | 7 | 0.62 |
| bG | ng/mL | 1.5E0 | 1.7E0 | 1.5E0 | 5.5E0 | 8.9E-1 | 1.1E1 | 4.1E-1 | 5.1E-1 | 3.3E0 | 3.0E1 | 18 | 7 | 18 | 7 | 0.59 |
| bH | pg/mL | 5.7E-1 | 5.7E-1 | 1.7E0 | 5.7E0 | 2.6E0 | 7.8E0 | 5.7E-1 | 5.7E-1 | 8.9E0 | 2.2E1 | 18 | 7 | 18 | 7 | 0.65 |
| bI | ng/mL | 4.0E-3 | 4.0E-3 | 1.2E-1 | 1.1E-1 | 2.9E-1 | 2.9E-1 | 4.0E-3 | 4.0E-3 | 9.8E-1 | 7.7E-1 | 18 | 7 | 18 | 7 | 0.48 |
| bJ | mg/mL | 1.9E0 | 1.9E0 | 2.2E0 | 2.5E0 | 1.9E0 | 1.4E0 | 2.5E-4 | 1.2E0 | 7.2E0 | 5.3E0 | 18 | 7 | 18 | 7 | 0.58 |
| bL | pg/mL | 1.8E0 | 5.5E0 | 3.8E0 | 5.5E0 | 4.3E0 | 4.1E0 | 4.6E-2 | 1.2E0 | 1.5E1 | 1.4E1 | 18 | 7 | 18 | 7 | 0.62 |
| bM | mg/mL | 1.8E0 | 2.4E0 | 2.3E0 | 2.8E0 | 1.9E0 | 1.3E0 | 5.0E-1 | 1.2E0 | 8.6E0 | 5.2E0 | 18 | 7 | 18 | 7 | 0.70 |
| bN | ng/mL | 3.1E1 | 2.7E1 | 1.2E2 | 2.6E1 | 1.9E2 | 2.1E1 | 1.4E-1 | 2.1E0 | 7.7E2 | 5.7E1 | 18 | 7 | 18 | 7 | 0.41 |
| bO | | 4.0E-2 | 4.0E-2 | 8.2E0 | 3.5E0 | 2.4E1 | 6.4E0 | 4.0E-2 | 4.0E-2 | 1.0E2 | 1.7E1 | 18 | 7 | 18 | 7 | 0.45 |
| bP | mg/mL | 4.5E-1 | 8.2E-1 | 6.8E-1 | 1.1E0 | 5.7E-1 | 6.9E-1 | 1.9E-1 | 4.3E-1 | 2.2E0 | 2.5E0 | 18 | 7 | 18 | 7 | 0.78 |
| bQ | pg/mL | 1.7E1 | 1.6E1 | 3.0E1 | 5.6E1 | 5.0E1 | 6.3E1 | 1.5E-1 | 4.9E0 | 2.2E2 | 1.6E2 | 18 | 7 | 18 | 7 | 0.56 |
| bR | ng/mL | 1.2E-2 | 1.2E-2 | 1.3E-1 | 6.6E-2 | 2.8E-1 | 9.3E-2 | 1.2E-2 | 1.2E-2 | 1.2E0 | 2.2E-1 | 18 | 7 | 18 | 7 | 0.47 |
| bS | pg/mL | 9.4E-1 | 9.4E-1 | 3.9E0 | 9.4E-1 | 1.2E1 | 0.0E0 | 9.4E-1 | 9.4E-1 | 5.4E1 | 9.4E-1 | 18 | 7 | 18 | 7 | 0.47 |
| bU | ng/mL | 8.3E-2 | 9.2E-2 | 2.2E-1 | 1.1E-1 | 4.1E-1 | 1.2E-1 | 1.3E-2 | 1.3E-2 | 1.7E0 | 3.4E-1 | 18 | 7 | 18 | 7 | 0.46 |
| bV | pg/mL | 4.9E2 | 9.6E2 | 6.2E2 | 8.3E2 | 3.3E2 | 3.6E2 | 1.7E2 | 3.7E2 | 1.4E3 | 1.3E3 | 18 | 7 | 18 | 7 | 0.66 |
| bW | pg/mL | 2.9E2 | 4.0E2 | 3.4E2 | 4.4E2 | 2.1E2 | 2.7E2 | 9.2E1 | 1.5E2 | 9.7E2 | 9.9E2 | 18 | 7 | 18 | 7 | 0.63 |
| bX | ng/mL | 2.5E-5 | 2.5E-5 | 2.5E-3 | 5.7E-4 | 3.6E-3 | 1.4E-3 | 2.5E-5 | 2.5E-5 | 1.1E-2 | 3.9E-3 | 18 | 7 | 18 | 7 | 0.37 |
| bZ | pg/mL | 2.9E2 | 1.6E3 | 6.0E2 | 7.4E3 | 8.4E2 | 1.6E4 | 1.5E-1 | 1.8E2 | 2.7E3 | 4.3E4 | 18 | 7 | 18 | 7 | 0.71 |
| cA | pg/mL | 6.0E-1 | 6.0E-1 | 1.1E0 | 6.0E-1 | 1.9E0 | 0.0E0 | 6.0E-1 | 6.0E-1 | 8.8E0 | 6.0E-1 | 18 | 7 | 18 | 7 | 0.47 |
| cB | ng/mL | 2.8E-2 | 4.0E-2 | 7.8E-2 | 4.2E-2 | 1.3E-1 | 3.1E-2 | 1.7E-3 | 1.7E-3 | 5.3E-1 | 7.9E-2 | 18 | 7 | 18 | 7 | 0.51 |
| cC | pg/mL | 3.3E1 | 3.8E1 | 3.5E1 | 4.3E1 | 3.7E1 | 1.3E1 | 1.0E0 | 2.8E1 | 1.4E2 | 6.7E1 | 18 | 7 | 18 | 7 | 0.59 |
| cD | pg/mL | 3.1E0 | 7.6E0 | 9.4E0 | 9.8E0 | 1.7E1 | 1.3E1 | 3.3E-1 | 3.3E-1 | 6.9E1 | 3.9E1 | 18 | 7 | 18 | 7 | 0.61 |
| cE | pg/mL | 5.8E1 | 5.7E1 | 9.1E1 | 2.5E2 | 1.4E2 | 4.5E2 | 1.2E-1 | 6.5E0 | 6.1E2 | 1.3E3 | 18 | 7 | 18 | 7 | 0.60 |
| cF | pg/mL | 5.3E-1 | 5.3E-1 | 2.2E1 | 2.3E0 | 5.0E1 | 4.6E0 | 5.3E-1 | 5.3E-1 | 2.2E2 | 1.3E1 | 18 | 7 | 18 | 7 | 0.34 |
| cG | pg/mL | 5.8E1 | 1.1E2 | 7.1E1 | 1.0E2 | 6.0E1 | 7.1E1 | 1.1E1 | 2.6E1 | 2.6E2 | 2.3E2 | 18 | 7 | 18 | 7 | 0.66 |
| cH | uIU/mL | 2.8E0 | 9.9E-1 | 5.0E0 | 1.1E1 | 6.0E0 | 2.0E1 | 8.6E-3 | 2.5E-1 | 2.0E1 | 5.3E1 | 18 | 7 | 18 | 7 | 0.51 |
| cI | ng/mL | 6.0E0 | 9.2E0 | 1.5E1 | 1.9E1 | 2.2E1 | 2.3E1 | 7.1E-2 | 1.2E0 | 8.8E1 | 6.6E1 | 18 | 7 | 18 | 7 | 0.61 |
| cJ | ug/mL | 8.1E1 | 7.3E1 | 1.5E2 | 8.2E1 | 1.6E2 | 5.3E1 | 1.7E1 | 3.1E1 | 6.2E2 | 1.9E2 | 18 | 7 | 18 | 7 | 0.43 |
| cK | ng/mL | 3.8E-3 | 3.8E-3 | 3.8E-3 | 3.8E-3 | 0.0E0 | 0.0E0 | 3.8E-3 | 3.8E-3 | 3.8E-3 | 3.8E-3 | 18 | 7 | 18 | 7 | 0.50 |
| cL | pg/mL | 1.9E2 | 2.1E2 | 6.8E2 | 2.5E2 | 1.7E3 | 1.4E2 | 4.8E1 | 1.5E2 | 7.4E3 | 5.6E2 | 18 | 7 | 18 | 7 | 0.58 |
| cM | pg/mL | 3.3E2 | 3.2E2 | 3.1E2 | 3.1E2 | 1.4E2 | 1.2E2 | 4.0E1 | 1.4E2 | 5.3E2 | 4.9E2 | 18 | 7 | 18 | 7 | 0.48 |
| cN | pg/mL | 1.4E2 | 1.6E2 | 1.4E2 | 1.7E2 | 5.0E1 | 5.8E1 | 4.6E1 | 1.0E2 | 2.6E2 | 2.8E2 | 18 | 7 | 18 | 7 | 0.60 |
| cO | pg/mL | 1.7E2 | 2.1E2 | 1.9E2 | 2.5E2 | 8.8E1 | 1.1E2 | 6.1E1 | 1.1E2 | 3.7E2 | 4.2E2 | 18 | 7 | 18 | 7 | 0.70 |
| cP | ng/mL | 2.5E3 | 4.3E3 | 2.6E3 | 3.7E3 | 7.4E2 | 1.4E3 | 1.7E3 | 1.4E3 | 4.4E3 | 5.1E3 | 18 | 7 | 18 | 7 | 0.73 |
| cQ | ng/mL | 7.9E-2 | 1.5E-1 | 1.1E-1 | 1.9E-1 | 1.3E-1 | 2.6E-1 | 2.0E-3 | 2.0E-3 | 4.8E-1 | 7.3E-1 | 18 | 7 | 18 | 7 | 0.58 |

Figure 26 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cR | ng/mL | 2.8E2 | 5.5E2 | 2.9E2 | 4.6E2 | 1.5E2 | 2.0E2 | 9.5E1 | 1.2E2 | 6.2E2 | 6.6E2 | 18 | 7 | 18 | 7 | 0.75 |
| cS | ng/mL | 3.1E2 | 6.3E2 | 3.2E2 | 6.7E2 | 2.0E2 | 3.8E2 | 8.1E1 | 1.9E2 | 8.3E2 | 1.3E3 | 18 | 7 | 18 | 7 | 0.78 |
| cT | ng/mL | 3.6E1 | 6.5E2 | 1.7E2 | 6.6E2 | 3.3E2 | 6.7E2 | 8.0E0 | 3.2E1 | 1.3E3 | 1.9E3 | 18 | 7 | 18 | 7 | 0.81 |
| cU | ng/mL | 8.7E1 | 5.4E1 | 9.8E1 | 1.0E2 | 5.9E1 | 8.4E1 | 1.6E1 | 4.3E1 | 2.1E2 | 2.3E2 | 18 | 7 | 18 | 7 | 0.44 |
| cV | ng/mL | 1.9E-1 | 2.6E-1 | 7.8E-1 | 5.5E-1 | 2.2E0 | 8.7E-1 | 4.1E-2 | 7.4E-2 | 9.7E0 | 2.5E0 | 18 | 7 | 18 | 7 | 0.67 |
| cW | mIU/mL | 3.9E-2 | 8.9E-2 | 4.9E-2 | 9.4E-2 | 3.1E-2 | 4.8E-2 | 1.0E-2 | 3.6E-2 | 1.3E-1 | 1.6E-1 | 18 | 7 | 18 | 7 | 0.81 |
| cX | ng/mL | 3.5E-1 | 7.3E-2 | 4.7E0 | 2.8E-1 | 9.8E0 | 3.8E-1 | 2.3E-4 | 1.4E-2 | 2.8E1 | 1.1E0 | 18 | 7 | 18 | 7 | 0.44 |
| cY | ng/mL | 8.3E0 | 8.1E0 | 1.0E1 | 7.6E0 | 8.1E0 | 4.1E0 | 1.1E0 | 1.5E0 | 2.9E1 | 1.3E1 | 18 | 7 | 18 | 7 | 0.47 |
| cZ | ug/mL | 1.5E1 | 1.9E1 | 1.5E1 | 1.8E1 | 5.2E0 | 6.1E0 | 6.2E0 | 7.0E0 | 2.5E1 | 2.6E1 | 18 | 7 | 18 | 7 | 0.67 |
| dA | pg/mL | 3.1E2 | 5.5E2 | 3.5E2 | 4.7E2 | 1.4E2 | 2.4E2 | 1.7E2 | 1.7E2 | 5.8E2 | 7.7E2 | 18 | 7 | 18 | 7 | 0.67 |
| dB | ug/mL | 1.2E1 | 2.3E1 | 1.5E1 | 2.3E1 | 1.2E1 | 4.7E0 | 2.6E0 | 1.6E1 | 4.0E1 | 2.9E1 | 18 | 7 | 18 | 7 | 0.73 |
| dC | nmol/L | 3.1E1 | 4.1E1 | 3.6E1 | 4.3E1 | 1.7E1 | 2.0E1 | 1.5E1 | 2.3E1 | 8.7E1 | 8.6E1 | 18 | 7 | 18 | 7 | 0.65 |
| dD | ug/mL | 3.7E1 | 3.1E1 | 3.6E1 | 3.6E1 | 1.0E1 | 1.5E1 | 2.0E1 | 2.2E1 | 5.2E1 | 6.4E1 | 18 | 7 | 18 | 7 | 0.48 |
| dE | ng/mL | 8.4E-3 | 4.4E-1 | 1.7E-1 | 1.2E0 | 2.4E-1 | 1.1E0 | 8.4E-3 | 3.4E-1 | 6.6E-1 | 3.3E0 | 18 | 7 | 18 | 7 | 0.86 |
| dF | ng/mL | 2.9E2 | 4.7E2 | 3.3E2 | 4.7E2 | 2.5E2 | 2.2E2 | 8.6E1 | 1.9E2 | 1.2E3 | 7.7E2 | 18 | 7 | 18 | 7 | 0.70 |
| dG | ng/mL | 1.6E1 | 2.4E1 | 1.6E1 | 2.2E1 | 7.4E0 | 8.3E0 | 3.3E0 | 1.1E1 | 3.3E1 | 3.2E1 | 18 | 7 | 18 | 7 | 0.68 |
| dH | pg/mL | 7.7E0 | 9.1E0 | 1.1E1 | 1.1E1 | 8.6E0 | 4.9E0 | 4.0E-2 | 6.6E0 | 3.0E1 | 1.9E1 | 18 | 7 | 18 | 7 | 0.52 |
| dI | pg/mL | 4.6E-1 | 4.6E-1 | 8.4E-1 | 1.9E0 | 8.8E-1 | 2.4E0 | 4.6E-1 | 4.6E-1 | 2.9E0 | 6.2E0 | 18 | 7 | 18 | 7 | 0.58 |
| dJ | ng/mL | 1.9E0 | 2.5E0 | 2.0E0 | 2.2E0 | 1.0E0 | 9.5E-1 | 3.7E-1 | 8.9E-1 | 4.0E0 | 3.4E0 | 18 | 7 | 18 | 7 | 0.57 |
| dK | uIU/mL | 2.0E0 | 1.2E0 | 3.0E0 | 1.7E0 | 3.7E0 | 1.1E0 | 4.0E-2 | 4.3E-1 | 1.6E1 | 3.1E0 | 18 | 7 | 18 | 7 | 0.43 |
| dL | ng/mL | 9.9E2 | 1.3E3 | 1.1E3 | 1.2E3 | 3.7E2 | 3.3E2 | 4.9E2 | 5.8E2 | 1.8E3 | 1.5E3 | 18 | 7 | 18 | 7 | 0.59 |
| dM | pg/mL | 1.3E3 | 1.2E3 | 1.5E3 | 1.9E3 | 7.7E2 | 1.2E3 | 4.7E2 | 7.1E2 | 3.3E3 | 3.6E3 | 18 | 7 | 18 | 7 | 0.57 |
| dN | ug/mL | 9.6E1 | 1.3E2 | 9.9E1 | 1.4E2 | 2.3E1 | 4.7E1 | 6.4E1 | 9.4E1 | 1.5E2 | 2.2E2 | 18 | 7 | 18 | 7 | 0.81 |

Analyte panel data:

Unconstrained panels with 3 analytes, where 1.0E-6 >= 'model p-value' > 0. Contains 2 panels of 409,920 total panels evaluated. : Fr{WmOh IiIv}

Unconstrained panels with 3 analytes, where 1.0E-5 >= 'model p-value' > 1.0E-6. Contains 152 panels of 409,920 total panels evaluated. : dE{aN(aK aL aO aS aY bA bC bF bN bX cE cF cG cL cR cS cY dB dF) cR(aF aP aW aZ bF bH bN bP bQ bU bW bX cF cN cT cX dJ dN) bW(aC aF aL aM aO aU aW bE bF bL bQ bU bZ cB cH cZ) bX(aG aH aR aW cE cL dB) cT(aC aF aW bE bL) dN(aH aU cE cY dL) aW(bA bJ cW) aK(bM cI) aQ(cH dK) aAaY aGbL aHbB aLbR aZcE bPcY} Hv{Im(Fr Ip It Ji Li Lv Lw Lx Mi Mn Mq Nm No Nw Ok On Pf Qc)} aM{bA(aN aS aW aZ bN bU bX cC cF cH cR dK) cT(aZ bH bX cS) aLcZ} aN{dN(aS aY bG bH cE cV dF) aYdB} Wm{Mx(Mu Mw) Js(On Pf) Oh(Jh Om)} Bg{Ao(Ar Ax Cs) Ef(Ax Cs)} Ir{Js(Il Ng) Frli MuMx} aE{cT(cR cX) bZcU} aK{bP(cC cS)} bA{aAcW bZcG} MwOhPf aQaUcF bLcTcX cCcRdN Unconstrained panels with 3 analytes, where 1.0E-4 >= 'model p-value' > 1.0E-5. Contains 756 panels of 409,920 total panels evaluated. : dE{cR(aA aC aD aE aG aH al aJ aK aL aM aO aQ aR aS aU aV aX aY bA bB bC bE bG bI bJ bL bM bO bR bS bV bZ cA cB cC cD cE cG cH cI cJ cK cL cM cO cP cQ cS cU cV cW cY cZ dA dB dC dD dF dG dH dI dK dL dM) bX(aC aE aF aI aJ aK aL aM aO aP aQ aS aU aV aX aY aZ bA bB bC bF bG bH bI bJ bL bM bN bO bQ bR bV bW bZ cD cF cG cH cI cJ cM cN cO cP cQ cS cT cV cW cX cY dD dF dG dI dJ dK dL) aN(aA aE aF aG aH aI aQ aU aV aX bB bG bI bM bQ bU bV bW bZ cB cH cJ cO cP cT cV cW dC dG dH dN) bW(aD aH aI aK aY bB bG bO cA cD cE cF cG cM cN cS cV cW cY dA dC dD dF dK dM) cT(al aL aM aO aY bF bG bO bQ bV bZ cA cB cD cE cF cH cS cW cZ dA dK) dN(aG aI aJ aK aL aP aQ aR aV aW aY bF bG bZ cH cX) bA(aA aF aI aL aM aP bF bG bO bZ cB cF dA) aL(aS aW aY bB bI bP cI cZ dK) aZ(aG aH aW aY bZ cF cG dF) bP(aK aY bZ cE cF) cI(aH aQ aU cY) aG(cA cF cW) aW(aQ aY cP) bR(aK bZ cS) cF(aQ bJ) dK(aH aK) aPaY bMcY bZcU cAcE} Pf{Oh(aA Fp Fr Hw Ii Im Ip Is Jg Jh Jk Jp Jq Jr Js Li Lu Lz Ma Mb Me Mf Mi Mj Mk Ml Mr Ms Mu Mv Mx My Mz Nb Nc Nd Nh Ni Nj Nk Nl Nn Nq Nr Nx Ny Oe Of Og Ok On Pa Po Pz Qa Qb Qc Qe) Qb(Fp Ii Im In Ir Iv Js Li Mr Na Nb Nc Nd Nk Nl Nn Nr Nt Oe Oi Qc Qe) Js(Ih Im Ir Is Iv Lz Mk Ml My Nc Ni Nj Nk Nl Nm No Nr On Pz Qe) Nc(Fp Fr Hv Ii Is Jg Mj Ml Mq Mr Mu Mx Nd Ns Oe Og Qc) Mx(Hu Im In Iv Mu Ni Nk Nr Pz) Lz(Ii Ji Li Ma Mp Mz Na Pg) Ml(Ii Li Ma Mp Mz Na Pg) Fp(Mf Mi Mj Ni Nk Pg) Ii(Fr Jh Jk Nf Of Pz) Mj(Im In Ni Nk) Og(Mk Ni Nk Oe) Mi(Ji Jq Po) Mr(Ni Nk) Lh(Fr My) Oe(It Mu) WmLj NsNl NdHv} Hv{Im(Et Fp Hq Hr Hu Hw Hx Ih Ii Ij Ik Il In Io Iq Ir Is Iu Iv Jg Jh Jj Jk Jl Jm Jn Jo Jp Jq Jr Js Jt Lh Lj Lu Ly Lz Ma Mb Mc Md Me Mf Mg Mh Mj Mk Ml Mm Mp Mr Ms Mt Mu Mv Mw Mx My Mz Na Nb Nc Nd Ne Nf Ng Nh Ni Nj Nk Nl Nn Nq Nr Ns Nt Nu Nv Nx Ny Oe Of Og Oh Oi Om Oy Oz Pa Pb Pc Pd Pe Pg Po Pz Qa Qd Qe) Wm{Ip Jg Jh Lv Mn Om On Pz Qc) Oh(Fr Mw) NdNi IiOn} aM{bA(aA aJ aK aL aO aP aQ aR aX aY bB bC bF bG bJ bL bO bQ bW bZ cB cD cE cI cJ cM cN cS cT cV cW cX cY dA dB dH dI dL dM dN) cT(aN aX cF cW cX) aYdN bXdF} Fr{Oh(Hx Ii Ij Im Li Lj Ma Mh Ml Nc Nl Nr) Ii(Li Mh) Og(Ni Oi) HuOi ItPg JtOm} Nc{Qc(Jh Mu Nb Nh Ni Nr Ns Pa Pc Pz) Li(Il Lz Ml Qb) Jh(Il Mx) IiJg} Mx{Ir(Hu In Js Og Oy) Mu(Iv Nr Qa) MvNk Nilj HuQe IvOn} aE{cR(aZ bB bX cC cF cU) cT(bG cC) aAbA aZcD bPbZ} Bg{Ax(Aw Bo Di Gl) Ao(Ap Dg Fp) Bo(Ba Cs)} Js{Ir(Ij Ik Md Mg Og Pg) Pz(Qc Qe) Nrls} dN{aN(bF bL bZ cG cH) cR(bL cD dB) bPcE} Ni{Og(Ij Io Nd Qc Qe) Nl(Ij Qc) Ijlt} Oh{Ma(Li Mw) Ij(Mv Nk) Qe(Mg Og)} Ex{Aw(Ax Cs) ArDg} Ii{Li(Jk Of) QcJh} bA{cX(bL bV) aWdB} bP{cF(aY dF) aKcW} Co{AoBc BoFw} Nl{Illv QcJh} cT{aDcR bJcX} BaCvGp MlNkJk InQbLi

Figure 26 Continued

Unconstrained panels with 3 analytes, where 1.0E-3 >= 'model p-value' > 1.0E-4. Contains 7,349 panels of 409,920 total panels evaluated. :
Pf{Nl(aA Et Fp Fr Hq Hr Hu Hv Hw Hx Ih Ii Ik Il Im In Io Ip Iq Ir Is It Iu Iv Jg Jh Ji Jj Jk Jl Jm Jn Jo Jp Jq Jr Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nm Nn No Nq Nr Nt Nu Nv Nw Nx Ny Oe Of Og Oi Ok Om On Oy Oz Pa Pb Pc Pd Pe Pg Po Pz Qa Qc Qd Qe) Og(Et Fp Fr Hq Hr Hu Hv Hw Hx Ih Ii Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Ml Mm Mn Mp Mq Mr Ms Mt Mu Mv Mw Mx My Mz Na Nb Nd Ne Nf Ng Nh Nj Nm Nn No Nq Nr Ns Nt Nu Nv Nw Nx Ny Of Oi Ok Om On Oy Oz Pa Pb Pc Pd Pe Pg Po Pz Qa Qb Qc Qd Qe Wm) Mj(aA Et Fr Hq Hr Hu Hv Hw Hx Ih Ii Ik Il Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mk Ml Mm Mn Mp Mq Mr Ms Mt Mu Mv Mw Mx My Mz Na Nb Nd Ne Nf Ng Nh Nj Nm Nn No Nq Nr Ns Nt Nu Nv Nw Nx Ny Oe Of Oi Ok Om On Oy Oz Pa Pb Pc Pd Pe Pg Po Pz Qa Qb Qc Qd Qe) Nk(Et Fr Hq Hr Hu Hv Hw Hx Ih Ii Ij Il Im In Io Ip Iq Ir Is It Iu Iv Jg Jh Ji Jj Jk Jl Jm Jn Jo Jp Jq Jr Jt Lh Li Lj Lu Lv Lw Lx Ly Lz Ma Mb Mc Md Me Mf Mg Mh Mi Mk Ml Mm Mn Mp Mq Ms Mt Mu Mv Mw My Mz Na Nb Nc Nd Ne Nf Ng Nh Ni Nj Nm Nn No Nq Nr Ns Nt Nu Nv Nw Nx Ny Oe Of Oi Ok Om On Oy Oz Pa Pb Pc Pd Pe Pg Po Pz Qa Qc Qd Qe) Fp(aA Et Fr Hq Hr Hu Hv Hw Hx Ih Ii Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mg Mh Mk Ml Mm Mn Mp Mq Mr Ms Mt Mu Mv Mw Mx My Mz Na Nb Nd Ne Nf Ng Nh Nj Nm Nn No Nq Nr Ns Nt Nu Nv Nw Nx Ny Oe Of Oi Ok Om On Oy Oz Pa Pb Pc Pd Pe Po Pz Qa Qc Qd Qe) Hv(Et Fr Hq Hr Hu Hw Hx Ih Ii In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mk Ml Mm Mn Mp Mq Mr Ms Mt Mu Mv Mw Mx My Mz Na Nb Ne Nf Ng Nh Ni Nj Nm Nn No Nq Nr Ns Nt Nu Nv Nw Nx Ny Oe Of Oi Ok Om On Oy Oz Pa Pb Pc Pd Pe Pg Po Pz Qa Qb Qc Qd Qe Wm) Oe(Et Fr Hq Hr Hu Hw Hx Ih Ii Il Im In Io Ip Iq Ir Is Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mk Ml Mm Mn Mp Mq Mr Ms Mt Mv Mw Mx My Mz Na Nb Nd Ne Nf Ng Nh Nj Nm Nn No Nq Nr Ns Nt Nu Nv Nw Nx Ny Of Oi Ok Om On Oy Oz Pa Pb Pc Pd Pe Pg Po Pz Qa Qc Qd Qe) Mu(Et Fr Hq Hr Hu Hw Hx Ih Ii Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mk Ml Mm Mn Mp Mq Mr Ms Mt Mv Mw My Mz Na Nb Nd Ne Nf Ng Nh Ni Nj Nm Nn No Nq Nr Ns Nt Nu Nv Nw Nx Ny Of Oi Ok Om On Oy Oz Pa Pb Pc Pd Pe Pg Po Pz Qa Qb Qc) Mx(aA Et Fr Hq Hr Hw Hx Ih Ii Ij Ik Il Io Ip Iq Ir Is It Iu Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mk Ml Mm Mn Mp Mq Mr Ms Mt Mv Mw My Mz Na Nb Nd Ne Nf Ng Nh Nj Nm Nn No Nq Ns Nt Nu Nv Nw Nx Ny Of Oi Ok Om On Oy Oz Pa Pb Pc Pd Pe Pg Po Qa Qb Qc Qd Qe Wm) Lz(aA Et Fr Hq Hr Hu Hw Hx Ih Ij Ik Il Im In Io Ip Iq Ir Is It Iu Iv Jg Jh Jj Jk Jl Jm Jn Jo Jp Jq Jr Jt Lh Lj Lu Lv Lw Ly Mb Mc Md Me Mf Mg Mh Mi Mk Ml Mm Mn Mq Mr Ms Mt Mv Mw My Nb Nc Nd Ne Nf Ng Nh Ni Nj Nm Nn No Nq Nr Ns Nt Nu Nv Nw Nx Ny Of Oi Ok Om On Oy Oz Pa Pb Pc Pd Pe Po Pz Qa Qb Qc Qd Qe Wm) Ml(aA Et Fr Hq Hr Hu Hw Hx Ih Ij Ik Il Im In Io Ip Iq Ir Is It Iu Iv Jg Jh Ji Jj Jk Jl Jm Jn Jo Jp Jq Jr Jt Lh Lj Lu Lv Lw Lx Ly Mb Mc Md Me Mf Mg Mh Mi Mk Mm Mn Mq Mr Ms Mt Mv Mw My Nb Nd Ne Nf Ng Nh Ni Nj Nm Nn No Nq Nr Ns Nt Nu Nv Nw Nx Ny Of Oi Ok Om On Oy Oz Pa Pb Pc Pd Pe Po Pz Qa Qb Qc Qd Qe Wm) Nc(aA Et Hq Hr Hu Hw Hx Ih Ij Ik Il Im In Io Ip Iq Ir It Iu Iv Jh Ji Jj Jk Jl Jm Jn Jo Jp Jq Jr Jt Lh Li Lj Lu Lv Lw Lx Ly Ma Mb Mc Md Me Mf Mg Mh Mi Mk Mm Mn Mp Ms Mt Mv Mw My Mz Na Nb Ne Nf Ng Nh Ni Nj Nm Nn No Nq Nr Nt Nu Nv Nw Nx Ny Of Oi Ok Om On Oy Oz Pa Pb Pc Pd Pe Pg Po Pz Qa Qd Qe Wm) Ii(Et Hq Hr Hu Hw Hx Ih Ik Il Im In Io Ip Iq Ir Is It Iu Iv Jg Ji Jj Jl Jm Jn Jo Jp Jq Jr Js Jt Lh Li Lj Lu Lv Lw Lx Ly Ma Mb Mc Md Me Mf Mg Mh Mi Mk Mm Mn Mp Mq Mr Ms Mt Mv Mw My Mz Na Nb Nd Ne Ng Nh Ni Nj Nm Nn No Nq Nr Ns Nt Nu Nv Nw Nx Ny Oi Ok Om On Oy Oz Pa Pb Pc Pd Pe Pg Po Qa Qc Qd Qe) Qb(aA Et Fr Hq Hr Hu Hw Hx Ih Ij Ik Il Io Ip Iq Is It Iu Jg Jh Ji Jj Jk Jl Jm Jn Jo Jp Jq Jr Jt Lh Lj Lu Lv Lw Lx Ly Ma Mb Mc Md Me Mf Mg Mh Mi Mk Mm Mn Mp Mq Ms Mt Mv Mw My Mz Ne Nf Ng Nh Ni Nj Nm No Nq Ns Nu Nv Nw Nx Ny Of Ok Om On Oy Oz Pa Pb Pc Pd Pe Pg Po Pz Qa Qd Wm) Js(aA Et Fr Hq Hr Hu Hw Hx Ij Ik Il In Io Ip Iq It Iu Jg Jh Ji Jj Jk Jl Jm Jn Jo Jp Jq Jr Jt Lh Li Lj Lu Lv Lw Lx Ly Ma Mb Mc Md Me Mf Mg Mh Mi Mm Mn Mp Mq Mr Ms Mt Mv Mw Mz Na Nb Nd Ne Nf Ng Nh Nn Nq Ns Nt Nu Nv Nw Nx Ny Of Oi Ok Om Oy Oz Pa Pb Pc Pd Pe Pg Po Qa Qc Qd) It(Et Fr Hq Hr Hu Hw Hx Ih Il Im In Io Ip Ir Is Iu Iv Jg Jh Ji Jj Jk Jm Jn Jp Jq Jr Jt Lh Li Lj Lu Lv Ly Ma Md Me Mf Mg Mi Mk Mn Mp Mq Mr Ms Mt Mv Mw My Na Nb Nd Ne Nf Ng Nh Ni Nj Nm Nn No Nq Nr Ns Nt Nv Nw Nx Ny Of Oi Ok On Pa Pb Pc Pd Pe Pg Po Pz Qc Qe Wm) Ni(Et Fr Hr Hu Hw Hx Ih Ij Il In Ip Iq Is Iu Iv Jh Ji Jj Jk Jl Jn Jo Jp Jq Jr Jt Lh Li Lj Lu Lw Lx Ly Ma Mb Md Me Mf Mg Mh Mi Mk Mm Mn Mq Mt Mv Mw My Na Nb Nd Ne Nf Ng Nh Nj Nm Nn No Nq Nr Nt Nu Nv Nw Nx Ny Of Oi Ok Om On Oy Oz Pa Pb Pc Pe Pg Po Pz Qa Qc) Lh(aA Hu Hw Hx Il Im In Io Ip Ir Is Iu Iv Jg Jh Ji Jk Jl Jn Jo Jp Jq Jr Li Lj Lu Lw Ma Mb Md Me Mf Mg Mh Mi Mk Mn Mp Mq Mr Ms Mv Mw Mz Na Nb Nd Ne Nf Nh Nj Nm No Nq Nr Ns Nt Nw Nx Ny Of Oh Oi Ok Om On Pa Pc Pe Pg Po Pz Qa Qc Qd Qe Wm) Pe(Et Fr Hq Hu Hw Hx Ih Il Im In Ip Iq Ir Is Iv Jg Jh Ji Jj Jk Jn Jp Jq Jr Jt Li Lu Lw Lx Ma Mb Md Me Mf Mg Mi Mk Mn Mq Mr Ms Mv Mw My Na Nb Nd Ne Nf Ng Nh Nj Nm Nn No Nq Nr Ns Nu Nw Nx Ny Of Oh Oi Ok Om On Pa Pg Po Pz Qc Qe) Mr(Et Fr Hq Hr Hu Hw Hx Il Im In Ip Iq Ir Is Iu Iv Jh Ji Jk Jn Jp Jq Jr Jt Li Lj Lu Lv Lw Ma Mb Md Mf Mi Mk Mm Mq Ms Mv Mw My Na Nb Nd Ne Nh Nj Nn No Nq Nr Ns Nt Nu Nv Nw Nx Of Oi Ok On Pa Pg Po Pz Qa Qc Qd Qe) Oh(Et Hq Hr Hu Hx Ih Ij Ik Il In Io Iq Ir Iu Iv Ji Jj Jl Jm Jn Jo Jt Lj Lv Lw Lx Ly Mc Md Mg Mh Mm Mn Mp Mq Mt Na Ne Nf Ng Nm No Ns Nt Nu Nv Nw Oi Om Oy Oz Pb Pc Pd Pg Qd Wm) Mf(Et Fr Hu Hw Hx Ih Il In Ip Is Jh Ji Jj Jk Jn Jq Jr Jt Lj Lu Lv Ma Me Mg Mi Mp Mq Mv Mw My Na Nb Nd Ne Nh Nj Nn No Nr Nt Nw Nx Of Oi On Oy Pa Pc Pg Po Pz Qc) Ji(Fr Hu Hw Il Im In Ip Ir Is Iv Jh Jn Jq Li Lw Lx Ma Md Mg Mk Mn Mq Mw My Na Nb Nd Ne Nf Ng Nh Nj Nm Nn No Nq Nr Nw Nx Of Oi Ok Om On Pa Pg Pz Qa Qc) Nw(Fr Hw Im In Ip Ir Is Iv Jg Jh Jq Li Lw Lx Ma Mb Md Mi Mk Mn Mq Mw My Na Nb Nd Ne Nf Ng Nh Nj Nm No Nq Nr Nx Ny Of Oi Ok Om On Pa Pg Pz Qa Qc Qe) Mi(Et Fr Ih Il Ip Is Jh Jj Jk Jl Jn Jr Jt Lu Lx Md Mk Mp Mq Mt Mw My Na Nd Ne Ng Nh Nj Nn No Nq Nr Nt Nv Of Ok Oy Pa Pc Pg Pz Qa Qc) Nr(Et Fr Hu Il Im Ip Is Jg Jh Jj Jk Jm Jn Jq Jr Lu Ma Md Mg Mk Mv Mw My Na Nb Nd Ne Ng Nh Nj Nq Nt Nx Of On Pg Po Pz Qa Qc) Nj(Et Hr Hu Ih Il Im Ip Is Iv Jh Jn Jp Jq Jr Jt Lu Lv Mk Mq Mt Na Nb Nf Nn No Nq Nt Nv Of Oi Pa Pb Pc Pd Pg Po Pz Qa Qd) Mk(Et Fr Hu Ih Il Ip Is Jh Jj Jk Jn Jq Jr Jt Lj Lu Lw Me Mg Mp Mq Mw Na Ne Nf Nh No Nt Of Oy Pc Pg Pz Qa Qd) Ip(Et Hw Ih Iq Is Jh Jl Jn Jq Jr Jt Lu Mp Mq Mw My Mz Na Ne Nh Nn No Nt Nv Oi Pg Po Qa) Jr(Et Hu Im Is Iv Jh Jn Me My Na Nb Nd Nh Nn No Nq Oi On Pd Pg Pz Qa) Fr(Et Hu Is Iv Jl Jn Jp Jt Lx Ms Mt Na Ng Nn No Nq Nt Nv Oi Pc Po) Nd(Et Hr Io Is Jh Jn Jp Jq Jt Lx Ms Mt Na Nf No Nt Nv Of Pg Qa) Nh(Et Im Is Iv Jh Jn Jq Md Mw My Nf Nn Nq Nu Nv Of Pg Po Pz) Pz(Et Hw Hx In Is Jn Jq Jt Na Ne Nn No Nq Nt Nv Pg Po Qa) Is(Et Il Ir Iv Jk Lv Ma Mw Na Ne Nt Nx Of Oi On Qc) Jh(Et Hw Jn Jt Mw My Na Ne Nn Nq Nt Nv Oi Po Qc) Po(Jn Li Lw Lx Mq Mw My Nb Ne Nm No Ok On) Et(Jp Ma Mg Mn Mw My Na Ne Nx Oi On Qc) Jn(Hw Hx Im Ir Ma Mw My Nq Nx Oi On Pg) Jq(Lw Mq My Na Nf Nm No Nx Oi Ok On Qc) Nn(Il Jk Mw My Nx Of Qa Qc Qd Qe Wm) Nt(Hu Im Jg Jk Mw My Nb Nx Of On Qc) Pg(Il Iv Jk Ma Na Of Oh Pa Qc) No(Im Lx Ma Mw My On Qc Qe) Mw(Jt Lx Ms Mt Na Nq Nv) Qc(Jt Mz Na Pc Qa Qd) Nv(Jk My Nb Nx Of On) Oi(Jk Lu Mq Of Pc Qa) Nq(Jk Mv My Na) Lw(Lu Lx Mp Mq) Iv(In Na Ne Qa) Of(Hw Na Ne Ng) My(Jt Na Pc) On(Jt Lu Mp) Ih(Im Ir) Qa(Ir Qe) Ok(Lu Mp) Nell NfHw NgJk JtNx} dE{bQ(aA aC aD aE aF aG aH aI aJ aK aL aM aO aP aQ aR aS aU aV aW aX aY aZ bA bB bC bE bF bG bH bI bJ bL bM bN bO bP bR bS bU bV bZ cA cB cC cD cE cF cG cH cI cJ cK cL cM cN cO cP cQ cS cU cV cW cX cY cZ dA dB dC dD dF dG dH dI dJ dK dL dM dN) aU(aA aC aD aE aF

Mw Mz Na Nb Nd Ne Nf Nl Nm No Nv Nw Nx Ny Of Og Oi Ok Pa Pe Pg Po Qd Qe) It(Hq Hu Ij Il Ip Is Jh Jk Jl Lv Ma Mj Mn Mu Mv Na Nb Nq Oi Om On Pz Qc Qe) Og(In Ir Iv Jh Jl Lv Ly Ma Me Mh Mi Mn Ms Mv Nb Nk Nl Om On Pz) Mx(Hu Ij Jh Jk Li Lx Mi Mj Mq Mv Nb Nn Nq On Pz Qc) Mu(aA Hq Il Iv Js Ly Mt Mv Na Nl Nn Nr Nu Oi) Jh(Ij Il Iv Jt Lv Ly Na Nn No Nt Oe Oi) Mi(Hq Hu Il Ip Jo Js Lj Of Oh Oy Pz) Mv(Hu Iv Js Me Mf Mj Nn Nr) Oh(Ij Is Jg Jk Mg Mn Pz Qc) Om(Et Ii Iv No Nw Ok) Ij(Js Lj Nn Pz Qb) Qc(Ih Js Mt Na Nl) Pz(Jt Mh Na Nl) On(Et Ii Jt No) Hu(Iv Lv Nl) Js(Im Mg Mn) Oi(Jk Of Oy) Nb(Hr Il) Lj(Li Mq) NnJk NqMj LyOy MnJt NfNk} Nl{Qc(Hq Hu Hv Ik Il Im Iv Jg Jk Js Li Lv Mb Mg Mh Mu Mv Nb Ne Nh Nj Nq Nr Ns Nx Of Og Oh Pa Pc Pz Qb) Jh(aA Hu Hv Ii Ij Ik Il Iv Jl Jq Js Li Lu Ma Md Me Mm Mp Mt Mu Mx Nr Og Oh Pa Pd Pe Pg Pz) Iv(Hq Hu Ij Jg Jk Mu Mv Mw My Ng Nq Nr Nx Of Og Pg Pz) Li(Hq Hu Il Jg Jk Lu Lz Ma Ml Mu Nh Nr Of Pg Pz Qb) Ij(Hu Jg Jk Lv Lz Ml Mu Mv My Ne Nr Oh On Pz Qb) Jg(aA Et Hv Ii Ik Il Js Mb Md Mt Mx Oh) Nr(Ik It Jk Js Mu Na Nh Og) Il(Ik Ir Mi Mu Nb Nh Nq On) Pz(Hv Js Md Mh Mx Nh Og) Oh(Is Lh Mv Mw Nq On Qe) Jk(Hu Lj Me Mh Mx Nh) On(Et Ii Ik Mp Mt) Mu(Mb Ml Mx Pg) Og(Ir Nb Nt Qe) Nh(Md Of Pd) Mv(Md Mx) Hv(Ma Ny) Ik(Nx Qe) MxIr NbOf} Mx{Mu(Hv Ih Ij Il Is Iu Jh Js Li Lj Lv Lx Lz Ma Mg Mh Mj Ml Nk No Oh On Pc Pd Pe Pz Qc Qe) Ir(aA Hv Ij It Jh Jk Jn Li Lu Mj Mv Mw Na Nb Ng Nk Nq Nr Nu Oi On Pz Qc Qd Qe) Qe(Hv Ii Ij It Iv Jh Js Li Md Mj Mv Nb Nq Nr Of Og Oh Oy Pc Pz Qb) Mj(Hu Hv Ij Iv Jh Li Lj Mv Mw Nq Nr Og Oy Qc) Ij(Hu Im In Jh Mv Nb Nk Nr Oh On Pz) Li(Il In Is Jh Ma Nk Nr On Pz Qc) Iv(In Is Jh Ma Mv Mw Nq Nr Qa) Nr(In Is It Jh Mi Og Qc) Nk(Jg Jh Jk Nb Nq On Pz) Hv(Is Jh Ma Mv Ny On Pz) Qa(Hu Jh Nb Og Oh Pz) Qc(Im Jh Nb Nq Pz) In(Ma Mg Pd Pe) Is(Jh Md Nb Oh) Lj(Jh Jk Mv On) Pz(Mw Nb Nq) On(Ii Jt Nv) LxHu Mdlm NbIl} bA{aM(aC aD aE aF aG aH aI aU aV bE bH bI bM bP bR bS bV cA cG cK cL cO cP cQ cU cZ dC dD dF dG dJ) cX(aA aD aE aN aP bC bE bF bG bJ bM bO bZ cA cC cE cF cH cV cW dB dC dK) cW(aD aJ aK aN aP aW bF bG bZ cE cF cH cN cP cR cS dH dI dK dM) aE(aH aI aL aN aZ bF bG bI bJ bZ cC cR cS dH dM) aD(aA aN bF bG bL bN bQ bZ cC cF cH cR cS dK) aN(aC aY bF bG bL bN bZ cC cQ dC dN) bP(bF bG bZ cF cH cS dM) bZ(aO aZ bF bV dC dN) cF(bH bL bV cC cQ dC) cS(aA aO bV cC cG dC) cG(bF bG cE cH) bL(aW dH dN) cC(aW cL cR) bF(aZ dN) aAaX bGdN bMdM bVcR dCdK} Oh{Ma(Hv Ij Im Ir Is Jh Lh Lj Mu Mv My Nb Nn Nq Nr Ny Og On Pe Qa Qc Qe) Mw(Ij Ir Is Jh Li Lj Lv Lx Mg Mh Mj Mv Nk Nq Nr Ny Ok On Pe Pz Qc Qe) Nq(Hv Ij Ir Is Jo Lh Li Lj Mg Mh Nf Nk Nr Ny On Pe Pz Qc Qe) Li(Is Jh Jk Jp Lu Mg Ml Mu Mv My Nr Ny On Pz Qb Qc Qe) Mv(Hv Ii Ir Is Iu Lj Mg Nk Nr Oy Qa Qc Qe) Ij(Hw Hx In Jh Js Mg Mi Mu Na Ne Nr On) Nr(Is Jh Lh Mi Mu Ny Og On Qc Qe) Mu(Hv Il Is Lj Mg Mh Pe Qc Qe) Jh(Is Lj Nk Qa Qc Qe) Mg(In Nb Qa Qc) Hv(Is On Qc Qe) Is(aA Jq Md) Nk(Jk Ny) Lj(Jk On) Og(Im Qa) IiOn} cT{aM(aA aD aE aF aH aJ aQ aU aW aY bB bC bE bF bG bJ bL bM bN bQ bU bV bW bZ cA cC cE cH cI cL cP cQ cR cV cZ dA dD dG dH dI dJ dK dL dN) cX(aC aD aQ aY bC bE bF bG bH bM bN bO bV bX bZ cA cC cE cF cH cI cJ cQ cU cV cW dB dC dK dN) aD(aE aN aR aX aZ bF bG bH bL bN bP bQ bR bW bX bZ cC cF cH cS dD) aE(aA aH aI aN aR aZ bF bH bI bJ bL bP bX bZ cE cH cL cS dH) cW(aA aN aW bF bG bZ cF cH cR) bP(aY bF bG bZ cH cS) bG(aF aZ cG dN) bF(aF bZ cG) cL(aY bL cC) aN(aY dN) bZ(aF cG) bNbX cSdC} Bg{Bo(aA Ad Af Aj Al An Ao Ap Ar As Aw Bb Bc Bn Ch Co Cp Cq Ct Cu Cv Cw Cx Db Dc Dd De Dg Di Dk Dl Ef Fp Fw Gl Gp) Cs(aA Ad Af Aj Al An Ap Ar As Aw Ax Ba Bb Bc Bn Ch Co Cp Cq Ct Cu Cv Cx Db Dc Dd De Dg Di Dk Dl Fp Fw Gl Gp) Ax(aA Ad Af Aj Al An Ap Ar As Ba Bb Bc Bn Ch Co Cp Cq Ct Cu Cv Cx Db Dc Dd De Dg Dk Dl Fp Fw Gp) Ef(Ap Ar Ba Bc Cu Cw Dg Dl) Ao(Ad Ba Co Cw Dl) Bc(Aw Ba Db Ex Gp) Gp(Ap Ar As Ba) BaCv CuGl} Nk{Ij(Et Hu It Iv Jg Jh Jk Jn Js Lu Lv Lz Mi Mk Ml Ms Mu Mv My Na Nb Nn Nr Ns Of On Pa Pg Pz Qb Qc) Li(Hq Il Jh Jk Lu Lz Ma Ml Mu Mv Nr Of Pa Pg Pz Qb) Jk(Hu Hv Ii Il Iv Lj Me Mf Mh Mj Mu Nn Nq Nr) Mv(Ii Il Iv Js Md Mf Mj Mr Nq Nr Nu Pa) Qc(Hq Hv Il Jh Js Mu Nb Of Og Pa Pc Pz) Og(Il Im Ir Lx Ma Nb Nr Pg Pz Qe) Il(Ir Iv Jg Jh Mi Mu Nb Nq) Jh(Hv Ii Js Md Nf) Pz(Hv Js Mh Nj) Of(Ir Iv Nb) Mu(Iv Ml) Na(Nf Nr) Hv(Ma Ny) Js(Im Ir) On(Ii Mp) NfNx} Ii{On(Et Hx Ik Il Is Iu Iv Jh Jk Jn Jr Js Jt Li Lu Mh Mu Mv Mw Mz Na Ne Nf Nr Nv Nw Nx Ny Of Og Pg Qc Qe) Mv(Hv Ir Iv Li Lw Lx Mh Mi Ng Nm No Nr Ok Qc Qe) Jh(Hv Ir Iv Li Lx Ma Mh Mi Nf No Og Oi Ok Qe) Li(Hq Jo Lu Lz Ma Ml Mu My Ng Nr Pz Qb Qe) Of(Ir Lx Mi Mq Nb No Pe Qe) Jk(Ir Lx Mg Mh Mi No Pe) Mg(Ir Mu Qc Qe) No(Hv Il Qc) Mu(Il Ir Iv) Hv(Ma Pz) Ir(Js Og) NrMi NbQc QeOg} dN{aN(aA aC aD aE aH aI aK aL aM aQ aX aZ bB bC bE bI bM bN bQ cC cD cJ cL cO cR cS cU cW cX cZ dA dB dC dJ dL) cC(aG aK aS aW aY bF bG bZ cE cF cH cS cX dL) bG(aE aM bP cB cD cM cQ cR cZ dA) aM(aS aX bH cE cO cP cR dL) bL(aG aK aW cF cO cS cX dL) bP(aH aY bF bZ cR cS dF) bZ(aO cB cD cM dA dD) cM(bF cH cR cS dL) cD(aD bF bX cX) dB(aG aW cX) aE(aH cR) aU(aH cE) bCcR bFcB cOdC} Hv{Ma(aA Hu Ij Ik Il In Ir Is It Iv Jh Ji Jl Jp Js Lh Li Lj Lw Md Mf Mk Ml Mq Mt Mu My Na Nb Ne Nm Nn No Nr Nx Ok On Pa Pd Pe Pg Pz Qc) Pz(Hw Ij In It Iu Jh Js Li Mh Mu Mv Na Nd Ne Og Qc) Nd(In Jh Lh Lv Mb Mj Mu Na Nb Pe) Jh(Hx Ij Ip Md Mw Nf Nq Qc) Qc(In Mu My Na Nb Oi) Na(Nf Nr Ny) Im(aA Qb) NnMw NrOg MtOn MuIl Mvlj NeNy} Js{Ir(aA Hu Im Is Jh Jk Jl Jm Ma Mp Mt Mu Mv Mw Nm Nq Nr Of On Oy Pd Pe Pz Qc) Pz(Hw Ij Is Li Lj Lx Ma Mh Mw Nq Nr Qa) Nr(Li Mi Mn Mp Na Nm On Qc Qe) Ma(Im Iv Li On Qc Qd Qe) On(Ij Im Lj Mh Ml Mt) Qe(Im Jh Mg Mh Og) Is(Li Md Mh Pe) Im(Md Qc) MkIj MvIv QcJh} aE{cR(aC aK aL aN aR aW aX aY bE bG bH bI bL bN bP bU bW bZ cB cD cE cH cN cP cQ cS cX cZ dA dB dD dG dI dK dM) aN(aL aX aY bV bZ cC cG cH cS dB) aL(aC aZ bP cZ dA) aZ(aG aQ aX bZ) bP(cE cF cS) aH(aX cZ) bZ(bX cN) cS(bG cU) aIcZ} Og{Nr(Hw Ij In Ir It Jh Li Lv Lw Ly Mh Mi Mk Mq Ms Mu Na Nb Nd Ne No Oe Oi Ok Qc Qe) Ir(Hw Hx Ij In Is Jn Jr Lu Ne Oe) Qe(Is Ms Mz Nn Oe Qb) Mh(Im Pz Qc) Ms(Im Nq Pz) Nb(Ma Oe) LuLi MjIn ImIt} Mu{Il(Hu Im Ir Iv Jk Li Lj Ly Ma Me Mf Mh Mj Mk Ml Mq Mv Mw My Nn No Nq Nr Qc) Qc(Ma Mg Mh Ml Mz Nn Nr Pc Pz Qb) Na(Iv Mh Nr Pe) Ma(Iv Jl Nq) Mg(Iv Ms) Li(Oe Qb) MhPz Nelv} Li{Qb(Ij Il Ip Ir Is Lh Lv Ma Mj Na Nr Oi Pg Pz Qc Qe) Ma(Lz Mf Ml Nn Pg Po) Pz(Lz Ml Na Nv Po) Nr(It Lz Ml Na) Ml(In Na) MjIn MkHq MvMy} cF{bP(aQ aS bF bG bH bZ cC cE cP cS cV cW cY dB dC) cC(aY bE bJ bW cB cI cR cX dA dG) aM(aA bH dA dG) cW(aC bU cD) dB(bW cR cX)} Qc{Jh(Io It Jt Mh Ml Mt Mz Ne Nn Nr Nt Nv Oe Pc Qb Qd) Nr(It Mv Na Pz) Nb(Nv Pc Qb) Pz(Jt Mh Ne) Mv(Nn Qb) Im(Ih It) MhQb MyPc} Gp{Cp(An Ao Ax Cs Cx Ef Gl) As(Ba Cx Ef) Ao(Co Ef) Aw(Ax Cv) Ba(Al Co) AjBo BcEf} Co{Ao(Aj Ap Ba Bn Bo Cp Cx Db Di Fw) Bo(Ct Di Fp) AwAx BaEf} Nr{It(Ij Il Ip Jh Jk Na) Mv(Ir Iv Ma Pz) Na(Ip Iv Mf)} Ax{Aw(Aj An Ar Cs Ct Db Fp Fw) Ar(Ba Cp) Ef(Di Fp)} aK{cW(aC aN aU bH dD) bP(aX bL bZ dB) bM(bZ cC) bWdB} Ij{Qb(In Mi Na Nb) Mv(It Ms Nn) Nv(Jh On) MjIn MlNa} aM{aZ(aA aY bV cQ dF) dK(aA cP) aLbE bVbX bZcU cSdA} On{Nv(aA Ik Il Im Jl Md Mp Mt Pg) MtJt} Bo{Ct(Ad Al Ch Ef) Fw(Al Ef)} Il{Nb(Na Pg) NqIt NeIv IrJn} bZ{aD(bP cZ) cU(bM bP) dAdC} dB{aW(bE bW) aDcR aYaZ} Aw{Bc(Ct Ex) ArCs} cS{dC(dA dG) bPcU} Ef{BcEx CsFp} Fw{BaCu DbDk} Md{Oe(Jh Mv)} Mj{In(Mg Of)} It{ImQe JkLj} cC{aDcR aNaY} NnMaMw NeIvJk aLbPcW Unconstrained panels with 2 analytes, where 1.0E-4 >= 'model p-value' > 0. Contains 11 panels of 11,937 total panels evaluated. : dE(aL aN bW bX cR cT) Pf(Nc Oh Qb) HvIm aMbA Unconstrained panels with 2 analytes, where 1.0E-3 >= 'model p-value' > 1.0E-4. Contains 174 panels of 11,937 total panels evaluated. : Pf(Et Fp Fr Hv Hw Hx Ih Ii Il In Ip Is It Jh Ji Jk Jn Jq Jr Js Jt Lh Li Lu Lw Lz Ma Md Mf Mg Mi Mj Mk Ml Mq Mr Mt Mu Mw Mx My Na Nb Nd Ne Nf Nh Ni Nj Nk Nl Nn No Nq Nr Nt Nv Nw Nx Oe Of Og Oi Ok On Pa Pc Pe Pg Po Pz Qa Qc) dE(aA aD aE aF aG aH aI aK aM aO aP aQ aR aS aU aV aW aX aY aZ bA bB bC bE bF bG bH bJ bL bM bN bP bQ bR bU bV bZ cA cB cC cE cF cG cH cI cJ cL cN cO cP cQ cS cV cW cX

Figure 26 Continued cY dC dF dG dH dI dJ dK dM dN) Nc(Fr Ij Jg Jh Li Mv Pz Qc) Bg(Ax Bc Bo Cs) Fr(Ii Mx Nn Oh) cT(aD aE aM cX) bA(aD cW cX) Gp(Ba Cp) Ni(Og Qc) Nl(Jh Qc) AwAx NrOg MaHv Mull NkIj aEcR aNdN Unconstrained panels with 2 analytes, where 1.0E-2 >= 'model p-value' > 1.0E-3. Contains 855 panels of 11,937 total panels evaluated. : Fr(aA Ax Ba Bg Bn Bo Et Fp Gp Hq Hr Hu Hv Hw Hx Ih Ij Ik Il Im In Io Ip Ir Is It Iu Iv Jg Jh Ji Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw My Mz Na Nb Ne Nf Ng Nh Ni Nj Nk Nl Nm No Nq Nr Ns Nt Nu Nv Nw Nx Ny Oe Of Og Oi Ok Om On Oz Pa Pb Pc Pd Pe Pg Po Pz Qb Qc Wm) Mu(aA Hu Hv Ii Ij Im Ip Ir Is Iv Jh Jl Jo Li Lj Lv Ly Ma Mb Md Me Mf Mg Mh Mj Ml Mn Mt Mv Mw Mx My Na Nc Ne Ni Nk Nl Nn Nq Nr Ny Of Og Oh Oi Pa Pc Pd Pe Pg Pz Qc Qe Wm) Li(Hq Hu Hv Ii Il Im In Is It Jh Ji Jk Jo Jp Js Lu Lv Lz Ma Md Mg Mk Ml Mn Mv Mw Mx My Na Nb Ne Ng Ni Nk Nl Nq Nr Nx Ny Oe Of Og Oh Oy Pa Pg Po Pz Qb Qc Wm) Jh(Hv Hw Hx Ii Ij Ik Il Im In Ip Ir Is It Iv Js Lj Lv Lw Ma Md Mg Mh Ml Mt Mv Mw Mx My Nd Ne Ni Nk Nq Nr Nt Oe Og Oh Oi Ok Pa Pc Pe Pz Qc Qe Wm) Pf(aA Hq Hr Hu Ij Ik Im Io Iq Ir Iu Iv Jg Jj Jl Jm Jo Jp Lj Lv Lx Ly Mb Mc Me Mh Mm Mn Mp Ms Mv Mz Ng Nm Ns Nu Ny Om Oy Oz Pb Pd Qd Qe Wm) Nc(aA Hu Hv Ik Il Im In Io Ir Is Iv Jk Jp Lh Lx Ma Mg Mw My Na Nb Nh Ni Nq Nr Ns Nt Nv Nx Ny Of Og Om On Pa Pd Pe Pg Qd Qe Wm) Mv(Hv Ii Ij Il Ip Ir It Iu Iv Js Lj Lv Lw Ma Md Mg Mh Mj Ml Mt Mx Nb Ne Ni Nk Nl Nn Nq Nr Oe Og Oh Oi Ok Pz Qc Wm) bA(aA aE aF aG aN aW aX aZ bF bG bH bJ bL bM bN bO bP bV bX bZ cC cE cF cH cL cP cQ cR cS cV dB dC dH dK dM dN) Qc(Hq Hu Hv Il Im In It Js Lv Ma Md Mg Mh Mi Ml Mw Mx Mz Na Nb Ne Nk No Nq Nr Of Og Oh Oi On Oy Pc Pz Qb Wm) Nl(Hu Ij Ik Il Ir Is Iv Jg Jk Lv Ma Mg Mw Nb Nh Ni Nq Nr Nt Nx Ny Of Og On Pe Pg Pz Qe Wm) Bg(Ad Aj Ao Ap Ar As Aw Ba Bb Bn Ch Co Cp Ct Cu Cv Cw Cx Db Dc De Dg Dk Dl Ef Ex Fp Gp) dN(aE aH aM aS aX aY bF bG bH bL bP bZ cC cD cE cH cL cM cO cP cR cS cT cX dB) Wm(Hq Hu Hv Ij Il Ip It Jk Ma Mg Mi Mn Mw Na Nb Ne Og Oi Om On Pz) Gp(Ad Aj Al Ap As Aw Ax Bc Bo Co Cs Cu Cv Cw Cx Dc Dg Dk Ef) cT(aF aN aZ bF bG bH bJ bL bN bP bX bZ cC cH cL cR cS cW dC) Og(Im In Ir Jp Lj Lx Ma Mh Mj Mw Nb Nk No Nq On Pe Pz Qe) Hv(Hu In Is Jk Mg Mw My Nb Nd Nq Nr Ny On Pe Pz Qe) Mx(Ij In Ir Is Jk Ma Mj Mw Nb Nq Nr Nr Pn Pz Qa Qe) Ba(Ad Al Ax Bo Ch Co Cs Cv Cw Cx Db Dk Ef Fw) cS(aD aE aM aY bL bP cC cN cP cW dA dB dC dG) dE(aC aJ bl bO bS cD cK cM cU cZ dA dB dD dL) Ni(Hu Ij Ip Is Jk Ma Mg Mn Mw Nq Ny Of On) Nk(Hu Il Ir Jg Jk Mg Nb Nq Nr Ny Of Pg Pz) Oh(Ij Is Ma Mg Mw Nq Nr Ny On Qa Qe) cW(aG aK aX aY bG bH bZ cE cF cO cR) Bo(Ad Al Ax Ch Co Cp Ct Ef Fw) Js(Ij Im Ir Is Ma Nr On Pz Qe) Co(Af Ao Ax Bc Bn Cs Cx Fw) Nr(It Jk Lw Mi Na Ne Ok) Pz(Hw Mh Mw Na Nb Ne Nq) aE(aH aL aN aX aZ bH bZ) Ij(Hu Hx It Mi Na Ne) bP(aK aL aY bZ cF dF) dB(aN aW aY cF cR cX) Ef(Ax Bc Bn Cs Cx) Dk(Ax Bn Cx Db) aM(aA aX aY cP) bZ(aD bM cP dA) Cp(Ax Cs Db) Mg(In Nb Nq) cC(bX cF cR) Aw(Bc Cs) Cw(Cx Fw) Ma(Hu Mw) Nb(Il Of) It(Im Nq) Jk(Lj Mh) On(Ii Mt) aD(aX cR) BcDb CuFw NoLu MsMw NeIv aNaY bGcP Constrained panels with 3 analytes, where 1.0E-6 >= 'model p-value' > 0. Contains 2 panels of 409,920 total panels evaluated. : Fr{WmOh IiIv}

Constrained panels with 3 analytes, where 1.0E-5 >= 'model p-value' > 1.0E-6. Contains 152 panels of 409,920 total panels evaluated. : dE{aN(aK aL aO aS aY bA bC bF bN bX cE cF cG cL cR cS cY dB dF) cR(aF aP aW aZ bF bH bN bP bQ bU bW bX cF cN cT cX dJ dN) bW(aC aF aL aM aO aU aW bE bF bL bQ bU bZ cB cH cZ) bX(aG aH aR aW cE cL dB) cT(aC aF aW bE bL) dN(aH aU cE cY dL) aW(bA bJ cW) aK(bM cl) aQ(cH dK) aAaY aGbL aHbB aLbR aZcE bPcY} Hv{Im(Fr Ip It Ji Li Lv Lw Lx Mi Mn Mq Nm No Nw Ok On Pf Qc)} aM{bA(aN aS aW aZ bN bU bX cC cF cH cR dK) cT(aZ bH bX cS) aLcZ} aN{dN(aS aY bG bH cE cV dF) aYdB} Wm{Mx(Mu Mw) Js(On Pf) Oh(Jh Om)} Bg{Ao(Ar Ax Cs) Ef(Ax Cs)} Ir{Js(Il Ng) Frli MuMx} aE{cT(cR cX) bZcU} aK{bP(cC cS)} bA{aAcW bZcG} MwOhPf aQaUcF bLcTcX cCcRdN Constrained panels with 3 analytes, where 1.0E-4 >= 'model p-value' > 1.0E-5. Contains 342 panels of 409,920 total panels evaluated. : Pf{Oh(Fp Fr Jk Jp Lz Ma Me Ml Mu My Mz Nd Nj Nq Qb) Qb(Ii Im In Iv Li Na Nc Nn Oe Oi Qc) Js(Ih Im Ir Iv Lz Mk Ml Nj Nk Nr Pz) Ii(Fr Jh Jk Lz Ml Nf Of Pz) Fp(Mf Mi Nc Ni Nk Pg) Ml(Li Ma Mp Mz Na Pg) Mx(Im In Mu Ni Nk Pz) Lz(Li Ma Mp Mz Pg) Mj(Im In Nc Ni) Og(Mk Ni Nk Oe) Mi(Ji Jq Po) Mr(Nc Ni Nk) Ns(Nc Nl) Lh(Fr My) Oe(It Mu) WmLj NdHv} dE{aN(aG aH aQ aU aV bW bZ cJ cT cV dH dN) bW(aH al aK bG cE cF cS cV cW dD) cT(aL aM bF bG bX bZ cA cB cF cH) dN(aG al aK aQ aR aV bF bG bZ cX) aZ(aG aH aY bZ cG dF) bA(aF aJ bF cF cR dA) bP(aY bZ cE cF) cl(aH aQ aU cY) bX(aK bC cY) aG(cA cW) aQ(aW cF) aY(aP aW) bR(aK cS) aHdK bMcY bZcU cAcE} Wm{Hv(Ip Jg Jh Lv Mn Om On Qc) Js(Fr Is Jh Jq Ma Om Pz) Oh(Ma Mu Mv Mw Nq On) Fr(It Mx) Oi(Hu Og) IiJh ItPg JtOm} Fr{Oh(Hv Ii Ij Li Lj Ma Mh Ml Nc Nl Nr) Ii(Li Lx Nc Nf Ni Nn No On Pe) Nc(JI Mx Pa) Ni(Mx Nr)} Nc{Qc(Jh Mu Nb Nh Ni Ns Pa Pz) Li(Il Lz Ml Qb) Jh(Il Mx) IiJg} Hv{Im(Iv Jg Jh Jn Jq Js Ma Mu Na Nd Pa Pz) MwOh NdNi IiOn} Mx{Ir(Hu In Js Og Oy) Mu(Iv Nr Qa) MvNk NiIj HuQe IvOn} aM{bA(aP aX bL bW dN) cT(aN aX cF cW cX) aYdN bXdF} aE{cR(aZ bB bX cC cF cU) cT(bG cC) aAbA aZcD bPbZ} dN{aN(bF bL bZ cG cH) cR(bL cD dB) bPcE} Js{Ir(Ij Md Mg Og Pg) Pz(Qc Qe) NrIs} Bg{Ao(Ap Dg Fp) Ax(Aw Bo Di) BoCs} Ni{Og(Io Nd Qc Qe) Nl(Ij Qc) IjIt} Oh{Ma(Li Mw) Ij(Mv Nk) Qe(Mg Og)} Ex{Aw(Ax Cs) ArDg} Ii{Li(Jk Of) QcJh} bA{cX(bL bV) aWdB} bP{cF(aY dF) aKcW} Co{AoBc BoFw} Nl{Illv QcJh} cT{aDcR bJcX} BaCvGp MINkJk InQbLi Constrained panels with 3 analytes, where 1.0E-3 >= 'model p-value' > 1.0E-4. Contains 1,812 panels of 409,920 total panels evaluated. : Wm{Hv(Et Fr Hu Ij Im Io Ir Is Iv Ji Jk Jn Jo Jp Jq Jr Lh Li Lw Lx Ly Ma Mg Mi Mp Mq Mu Mv Mw Mz Na Nb Nc Nd Ne Nf Nl Nm No Nv Nw Nx Of Og Oi Ok Pa Pe Pf Pg Po Qd Qe) It(Hq Hu Ij Il Ip Is Jh Jk Jl Lv Ma Mj Mn Mu Mv Na Nb Nc Nq Oi Om On Pf Pz Qc Qe) Og(Fr In Iv Jh Jl Lv Ly Ma Me Mh Mi Mn Ms Mv Nc Nk Nl Om Pf) Fr(Et Iv Jn Jt Lx Mf Mj Mt Na Nc Nn No Nr Nt Qa) Mx(Hu Ij Jh Jk Li Lx Mi Mj Mq Mv Nb Nn Nq Pf Qc) Nc(Hw Ij Il Li Lv Mi Mu Mv Nb Oi Om Pf Qc) Mu(aA Hq Il Ly Mt Mv Na Nl Nn Nu Oi) Mi(Hq Hu Il Ip Jo Js Lj Of Oh Oy) Oh(Ij Is Jg Jk Mg Mn Pf Pz Qc) Mv(Hu Iv Js Me Mf Mj Nn Nr) Jh(Jt Na Nn No Oe Oi) Qc(Ih Js Mt Na Nl) Om(Et Ii No Nw Ok) Nn(Ij Jk Pf) Js(Ij Mg Mn) Lj(Ij Li Mq) Oi(Jk Of Oy) Hu(Lv Nl) Pf(Lh Qb) NoOn NqMj LyOy MnJt NaPz NblI NfNk} Mx{Ir(aA Fr Hv Ij It Jh Jk Jn Li Lu Mj Mv Mw Na Nb Nc Ng Ni Nk Nl Nq Nr Nu Oi On Pz Qc Qd) Mu(Hv Ih Ij Il Is Iu Li Lj Lx Lz Ma Mg Mh Mj Ml Nc Ni Nk Nl No Oh Pe Pz Qc Qe) Qe(Hv Ii Ij It Lv Jh Js Li Mv Nb Nc Ni Nr Og Oh Oy Pz Qb) Mj(Fr Hu Ij Iv Jh Li Lj Mv Mw Nq Nr Og Oy Qc) Li(Fr Il In Is Jh Ma Nc Ni Nk Nr On Pz Qc) Nc(Im Is Jg Jk Mv My Nb Nq Nr On Pz) Ij(Fr Hu Im In Jh Nb Nk Nr Oh On Pz) Iv(Fr In Is Jh Ma Mv Mw Nq Nr Qa) Fr(Ii Im In Lj Lv Nk Nl Nn) Ni(Is Jk Mv Mw Nq On Qa Qc) Jh(Hv Is Lj Nk Nl Nr Qa Qc) Pz(Hv Mw Nb Nk Nq Qa Qc) On(Hv Ii Jt Lj Nk Nv) Nr(In Is It Mi Qc) Nb(Il Is Nk Qa Qc) In(Ma Mg Pd Pe) Mv(Hv Lj Nl) Nk(Jg Jk Nq) Is(Hv Md Oh) Qa(Hu Og Oh) Nl(Jg Jk) Im(Md Qc) NqQc LxHu HvNy JkLj} Oh{Ma(Hv Ij Im Ir Is Jh Lh Lj Mu Mv My Nb Nn Nq Nr Ny Og On Pe Qa Qc Qe) Nq(Hv Ir Is Lh Li Lj Mg Nc Nf Ni Nk Nl Nr On Pe Qc Qe) Mw(Ir Is Li Lj Lv Mg Mh Nc Ni Nk Nl Nr Pe Pz Qc Qe) Li(Is Jh Jk Jp Lu Mg Ml Mu My Nr Ny On Pz Qc Qe) Ij(Hw Hx In Jh Js Mg Mi Mu Na Nc Ne Ni Nl Nr) Nr(Is Jh Lh Mi Mu Mv Ny Og On Qc Qe) Mv(Hv Iu Lj Nc Nk Nl Qc Qe) Is(Hv Jh Jq Md Mu Nc Ni Nl) Mu(Lj Mg Mh Pe Qc Qe) Nl(Jg Jh Lh On Qe) Mg(In Nb Qa Qc) Jh(Lj Qa Qc Qe) On(Hv Ii Lj Nc) Nc(Jp Qe) Hv(Qc Qe) Og(Im Qa) NkNy JkLj} Nc{Pa(Hu Im Ir Is Jg Jh Jp Lh Li Lu Mu Mv Mw My Nb Nq Nr Ny On Pz Qa Qd Qe) Il(Im Io Ir Iv Jp Lx Mi Mu My Nb Nh Nq Nr Ns

Figure 26 Continued

Figure 26 Continued cG cH cI cJ cK cL cM cN cO cP cQ cR cS cT cU cV cW cX cY cZ dA dB dC dD dF dG dH dI dJ dK dL dM dN) aQ(aA aC aD aE aF aG aI aJ aM aN aO aP aR aS aU aV aW aX aY aZ bA bB bC bE bF bG bH bI bJ bL bM bN bO bP bQ bR bS bU bV bW bX bZ cA cB cC cE cG cI cJ cK cL cM cN cO cP cQ cR cS cT cU cV cW cX cY cZ dA dB dC dD dF dG dH dI dJ dK dL dM dN) aY(aC aD aE aF aG aI aJ aM aO aP aR aS aU aV aW aX aZ bA bB bC bE bF bG bH bI bJ bL bM bN bO bP bQ bR bS bU bV bW bX bZ cA cB cC cD cE cG cH cI cJ cK cL cM cN cO cP cQ cR cS cT cU cV cW cX cY cZ dA dB dC dD dF dG dH dI dJ dK dL dM dN) cE(aA aC aD aE aF aG aI aJ aM aN aO aP aR aS aU aV aW aX aZ bA bC bE bF bG bH bI bJ bL bM bN bO bP bQ bR bS bU bV bW bX bZ cA cB cC cD cG cH cI cJ cK cL cM cN cO cP cQ cR cS cT cU cV cW cX cY cZ dA dB dC dD dF dG dH dI dJ dK dL dM) cS(aA aC aD aE aF aG aI aJ aM aO aP aR aS aU aV aW aX aZ bA bB bC bE bF bG bH bI bJ bL bM bN bO bP bQ bR bS bU bV bW bX bZ cA cB cC cD cG cH cI cJ cK cL cM cN cO cP cQ cR cT cU cV cW cX cY cZ dA dC dD dF dG dH dI dJ dK dL dM dN) aG(aA aC aD aE aF aI aJ aM aN aO aP aR aS aU aV aW aX aZ bA bB bC bE bF bG bH bI bJ bM bN bP bQ bR bS bU bV bW bX bZ cA cB cC cD cG cH cI cJ cK cL cM cN cO cP cQ cR cT cU cV cW cX cY cZ dA dB dC dD dF dG dI dJ dK dL dM dN) dN(aA aC aD aE aF aI aJ aM aN aO aP aR aS aV aW aX aZ bA bB bC bE bF bG bH bI bJ bL bM bN bO bP bQ bR bS bU bV bW bX bZ cA cB cC cD cG cH cI cJ cK cL cM cN cO cP cQ cR cT cU cV cW cX cZ dA dB dC dD dF dG dH dI dJ dK dM) cY(aA aC aD aE aF aI aJ aM aO aP aR aS aU aV aW aX aZ bA bB bC bE bF bG bH bI bJ bL bM bN bO bQ bR bS bU bV bW bX bZ cA cB cC cD cG cH cI cJ cK cL cM cN cO cP cQ cR cT cU cV cW cX cZ dA dB dC dD dF dG dH dI dJ dK dM) aI(aA aC aD aE aF aJ aM aN aO aP aR aS aU aV aW aX aZ bA bB bC bE bG bH bI bJ bL bM bN bO bP bQ bR bS bU bV bW bX bZ cA cB cC cD cH cI cJ cK cL cM cN cO cP cQ cR cT cU cV cZ dA dB dC dD dF dG dH dI dJ dK dL dM) bX(aA aC aD aE aF aJ aM aN aO aP aS aU aV aX aZ bA bB bC bE bF bG bH bI bJ bL bM bN bO bP bQ bR bS bU bV bW bZ cA cB cC cD cG cH cI cJ cK cM cN cO cP cQ cT cU cV cW cX cZ dA dC dD dF dG dH dI dJ dK dL dM) aW(aA aC aD aE aF aJ aM aN aO aP aR aS aU aV aX aZ bB bC bE bF bG bH bI bL bM bN bO bP bQ bR bS bU bV bZ cA cB cC cD cG cH cI cJ cK cL cM cN cO cP cQ cU cV cX cZ dA dB dC dD dF dG dH dI dJ dK dL dM) cT(aA aD aE aJ aM aN aO aP aR aS aU aV aX aZ bA bB bC bF bG bH bI bJ bM bN bO bP bQ bR bS bU bV bW bZ cA cB cC cD cG cH cI cJ cK cL cM cN cO cP cQ cU cV cW cX cZ dA dB dC dD dF dG dH dI dJ dK dL dM) bA(aA aC aD aE aF aJ aM aO aP aR aU aV aZ bB bE bF bG bH bI bJ bL bM bN bO bP bQ bR bS bU bV bW bZ cA cB cC cD cG cH cI cJ cK cL cN cO cP cQ cR cU cV cW cX cZ dA dB dC dD dF dH dI dJ dK dL dM) aN(aA aC aD aE aF aJ aM aP aR aU aV aX aZ bB bC bE bF bG bH bI bJ bL bM bN bO bP bQ bR bS bU bV bW bZ cA cB cC cD cH cI cJ cK cM cN cO cP cQ cU cV cW cX cZ dA dB dC dD dG dH dI dJ dK dL dM) bH(aA aC aD aE aF aJ aM aO aP aR aS aU aV aX aZ bB bC bE bF bG bI bJ bL bM bN bO bP bQ bR bS bV bW cA cB cC cD cG cH cI cJ cK cL cM cN cO cP cQ cV cW cX cZ dB dC dD dF dG dH dI dK dL dM) bF(aA aC aE aF aJ aO aP aR aU aX aZ bB bC bE bG bI bJ bL bM bN bO bP bQ bR bS bU bV bW bZ cA cB cC cD cH cI cJ cK cM cN cP cQ cU cV cW cX cZ dA dB dC dD dF dG dH dI dJ dK dL dM) cR(aA aC aD aE aJ aM aO aR aS aU aV aX bB bC bE bG bI bJ bL bM bO bQ bR bS bV bZ cA cB cC cD cG cH cI cJ cK cL cM cO cP cQ cU cV cW cZ dA dB dC dD dF dG dH dI dK dL dM) bW(aA aD aE aJ aP aR aS aV aX aZ bB bC bE bG bI bJ bM bN bO bP bR bS bV cA cC cD cG cI cJ cK cL cM cN cO cP cQ cU cV cW cX dA dB dC dD dF dG dH dI dJ dK dL dM) bZ(aA aD aE aF aM aP aR aS aU aV aZ bB bC bE bG bI bJ bL bM bN bO bP bQ bR cA cB cG cH cI cJ cL cM cN cO cP cQ cU cV cW cX cZ dA dB dC dD dG dH dI dJ dK dL dM) bQ(aA aC aJ aO aP aR aS aU aV aX aZ bC bE bG bI bJ bN bO bP bR bS bV cA cD cG cI cJ cK cM cN cO cP cQ cU cV cX cZ dA dB dC dD dF dG dH dI dJ dK dL dM) dF(aC aD aE aF aJ aO aP aR aU aV aX aZ bB bG bJ bL bM bN bP bR bS bU cA cB cC cG cH cI cJ cK cL cM cN cO cP cQ cU cV cW cX cZ dB dC dI dJ dK dL) bC(aA aC aE aF aO aR aS aX aZ bB bE bG bI bJ bL bN bP bR bS bU cA cC cG cH cI cJ cK cL cM cN cO cP cU cV cW cX cZ dA dB dG dH dI dJ dK dL dM) aO(aA aF aR aS aU aV aX aZ bE bI bJ bM bN bP bR bU bV cA cD cL cM cN cP cQ cU cW cX dA dC dD dG dH dI dJ dL dM) aF(aA aC aJ aR aS aU aX aZ bE bJ bL bM bN bP bR bV cA cD cI cJ cM cN cP cU cX cZ dA dD dG dH dI dJ dL dM) cG(aA aE aP aR aS aU aV aX aZ bE bJ bL bN bO bP bR bV cA cI cN cO cP cQ cU cX cZ dD dG dH dI dJ dK dM) cH(aA aR aS aU aX aZ bE bJ bL bP bR bV cA cD cL cM cN cP cQ cU cX dA dC dD dG dH dI dJ dK dL dM) cV(aA aP aR aU aV aX aZ bB bE bJ bN bP bR bU cA cL cN cP cQ cU cX dD dG dH dI dJ dM) bG(aA aC aS aU aX bE bJ bL bO bP bV cA cD cL cN cP cQ cU cX dA dD dG dH dI dJ dM) aR(aA aE aS aV bE bI bL bM bN bP bR bV cA cB cI cJ cL cO cW dA dB dG dH dK dM) aZ(aA aE aM aS aU aV bJ bR bV cA cB cC cJ cL cM cN cO cP cQ cU dG dH dJ dK dM) aU(aA aS bL bM bN bP bR bV cA cC cI cJ cM cP cW dA dC dG dH dJ dK dM) dG(aJ aP aV aX bI bJ bL bP bU cA cL cN cW cX dB dH dJ dL dM) aS(aP aV aX bI bJ bP bU cA cI cN cQ cU cX dB dI dJ dK) bP(aA aV aX bE bN bR bU bV cA cL cP cQ cW dC dH dM) bU(aA aX bN bO bR bV cA cI cM cP cX dH dK dM) cW(aC aV aX bE bV cD cJ cL cN cO cP cQ dD dJ) cX(aA aE aX bE bN bV cJ cL cO cQ dH dK dM) dH(aJ aP bJ bL bO cC cN cQ cU dB dK dL) aX(aE aM bJ bM bR cA cB cD dI dK) bB(aA bR bV cI cP dB dD dK) bV(aP aV bJ cA cI cZ dJ) cL(aJ bJ bL cA cM dB dL) dK(aA aV bJ cJ cN cO dC) bE(aM bL cA cB cI dC) cQ(aD aM bM cB cD dD) aA(aP bJ cB dA dJ) cA(bL cM cN cU) cP(bN cC cJ dJ) dM(aJ aP bJ cB) aV(bO bR cI) bL(cN cO) bN(cI dB) cJ(bR cC) aEbJ cIdC cNdI dAdJ} Pf{Oh(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Om On Oy Oz Pa Pb Pc Pd Pe Pg Po Pz Qa Qb Qc Qd Qe Wm) Nc(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nd Ne Nf Ng Nh Ni Nj Nk Nl Nm Nn No Nq Nr Ns Nt Nu Nv Nw Nx Ny Oe Of Og Oi Ok Om On Oy Oz Pa Pb Pc Pd Pe Pg Po Pz Qa Qb Qc Qd Qe Wm) Qb(Et Fp Hq Hr Hu Hw Hx Ih Ii Ik Il Im In Ip Iq Ir It Iu Iv Jg Jh Ji Jj Jk Jl Jm Jn Jo Jp Jq Jr Js Jt Lh Li Lj Lv Lw Lx Ma Mb Mc Md Mf Mg Mh Mi Mj Mk Ml Mm Mn Mp Mq Mr Ms Mt Mu Mx My Mz Na Nb Nd Ne Nf Ng Nh Ni Nj Nk Nl Nn No Nr Ns Nt Nu Nv Nw Ny Oe Of Og Oi Ok Om On Oy Oz Pa Pb Pc Pe Pg Po Pz Qc Qd Qe Wm) Ii(aA Et Fp Fr Hq Hr Hu Hv Ih Ik Il Im In Io Ip Iq Ir Is It Iv Jh Jk Jl Jm Jn Jo Jp Jr Li Lj Lu Lv Lw Lx Ly Lz Mc Md Mf Mi Mj Ml Mm Mn Mp Mr Ms Mt Mu Mv Mw Mx My Mz Na Nd Nf Ng Nh Ni Nj Nk Nl Nm Nn No Nq Nr Ns Nt Nu Nv Nx Ny Oe Of Og Oi Ok On Oz Pa Pc Pg Po Pz Qa Qc Qd Qe) Mx(aA Et Fp Hr Hu Hw Hx Ih Il Im In Ir Iv Jg Jh Ji Jj Jk Jm Jn Jo Jq Js Lh Lu Lv Ma Mc Md Mf Mk Ml Mr Mu Nb Nd Ne Nh Ni Nk Nl Nn No Nr Nw Nx Ny Of Oy Pb Pc Pe Pg Pz Qc Qd Qe Wm) Nl(aA Et Fp Fr Hv Il Im Ip Is It Iv Jh Ji Jj Jk Jn Jq Js Lh Li Lu Lv Md Mf Mj Mk Ml Mm Mq Mr Mu Mw Na Nd Ne Nf Nh Ni Nj Nn Nq Nr Ns Nt Nw Nx Oe Of Og Om Pd Pe Pz Qa Qc Qe Wm) Lz(Et Il Ip Ir Is It Iv Ji Jj Jl Jm Jn Jp Js Lh Lu Lx Ma Mb Mf Mh Mk Ml Mm Mp Ms Mt Mz Na Nd Ni Nk Nm Nn No Nu Nv Nw Oe Of Ok Oz Pb Pc Pd Po Pz Qa) Nk(Et Fp Hu Ih Il It Iv Jh Ji Jj Jk Jn Jr Js Jt Lh Li Ly Md Mf Mj Ml Mp Mr Mu Mz Na Nd Nf Nj Nn No Nq Nr Ns Nt Nu Nv Nw Oe Og Pc Pd Pe Pg Pz) Oe(Et Fp Hu Ik Il Io Ip Ir It Iv Jh Ji Jk Jl Jn Jp Jq Jr Js Lh Li Lv Md Mf Mj Ml Mr Mu Na Ni No Nr Nv Nw Of Og Pc Pe Pg Pz Qa Qc Qe) Js(Fp Fr Hv Hw Ih Im Io Ir Is It Iv Jh Jr Lh Mf Mj Mk Ml Mw My Nd Ni Nj Nm No Nq Nr Nx Of Og Oi On Pg Po Pz Qa Qc Qe Wm) Fp(Hq Hu Hx Im Is It Iv Jh Jk Jm Jn Mf Mi Mj Mk Ml Mr Mu Nb Ne Ng Nh Ni Nq Nr Nu Oi Oy Pg Pz Qa Qd Qe) Ml(Et Il Ir Is Iv Ji Jn Lh Ma Mf Mj Mp Mz Na Nd Nh Ni Nm Nn No Nr Nt Nv Nw Of Oi Pb Pe Po Qc) Ni(Hv In Ip Iq It Iv Jl Jr Jt Ma Mf Mj Mq Mr Mu Mw Na Nj Nr Nt Nw Og Oi Pa Pe Pg Qc) Lh(Fr Il Im In Io Ip Is Lv Ly Ma Mi Mj Mp Mu Mw My Na Nd Ne Nj Oz Pe Qa Qc Qe Wm) Mj(Il Im In Is Jh Ji Jk Lu Ly Mk Mu Mv Na Nd Nh Nr Nw Ny Of Pz) Pe(Im In Ip Ir Iv Li Mf Mi Mk Mu Mw My Nd Nh No Nr Nu Oi Pg Qe) Mu(Hv Il Is Iv Jl Jn Jq Mf

Mg Mv My Nk Nl On Qd) Li(Hq In Is Jp Ma Mw My Nq Nx On) Mw(Is Lj Ma Mh Nk Nr) Is(aA Md Mx Nl Nr) Qe(Ma Mg Mv Mx Og) Lj(Jk Mv Nn Nq On) Nl(Jg Mv Nq) Mu(Ma Nr) Nk(Mv Nq) MgQa ImOg} Mx{Mu(Il Ir Iu Iv Li Lj Lx Mh Ni Nr Pz Qa Qe) Ir(Hu Jh Js Mv Nq Og Oy) Li(Hu Im In Ni On Pz) Qe(Hu Jh Og Oy Pz) Iv(In Mv Nq On) Nk(Jh Jk Mv) Nb(Is On) Nl(Jg Jh) Ij(Ni Pz) MjMw HuQa IiOn} Co{Ao(aA Af Aj Al Ap Aw Ba Bb Bc Bn Bo Ch Cp Cq Ct Cu Cw Cx Db Dc Di Dk Dl Fw) Bo(Ad Ax Ch Cq Cs Ct Cx Dd Di Ef Ex Fp Fw) Ef(aA Ba Bn Cx) BcEx BnCx} Nl{Iv(Hq Hu Ij Il Jg Jk Mu My Nr) Ij(Hu Jg Jh Ne Ni Pz) Il(Jg Jh Mu Nb Nh) Pz(Jk Js Li Og) Jh(Ii Md Mt Pg) Ni(Jk Li Og) Nr(Jk Og) Mu(Ik Pe) Nb(Hu Of) NuOf MdJg NhJk IkIr} cF{cC(aJ aN aP aU aW aY bE bJ bW cB cI cP cR cS cV cW cX dA dB dG dH dI dL dM) cW(aC aG aN bG bH bO bR bU cD cR) dB(aY bW cR cX) bU(cS dJ)] Nk{Ij(Et Hu Ir It Iv Jg Jh Jk Lu Lz Mu Mv Nb Ni Nn) Li(Hq Il In Lz Mv Na Nr Pg) Ju(Il Pa Pg) Jk(Ml Pz) NbIl IrOg JtOn} Ii{Li(Hq Il Jk Jm Na Nm Nr Of Pg Qb) Ir(Jh Js Mu Mv Of) Jk(Lx Mg No Pe) On(Jt Lu Mv Of) Mv(Iv Qe) Of(No Qe)} Js{Ir(aA Ij Ik Il Is Md Mg Mv Ng Nr Of Og Oy Pd Pg) Is(Li Ni Nr) Pz{Lj Qa Qe) NrOn MgQe Mvlv Nilj} Ax{Aw(Ad Aj An Ap Ar Bc Cs Ct Db Dd Ex Fp Fw) Cp(An Cs Ex Fw) Ef(Ao Di Fp) Dk(Cs Ex) DgEx} Bo{Ct(aA Ad Al Ao Ch Cp Cv Dg Di Dk Ef Fw Gl) Fw(Aj Al Cu Cw Db Ef) AdEx AjCx AlDd} cW{aK(aC aN aU bL cC cl cN cR dD) aG(bL cC dD) bG(aC bE) cU(cE cO) dK(bH cD) aHdD aLcZ aNaY} Il{Mu(Hu Ir It Iv Jn Ly Me Mf Mh Mj Ml Ms My Nb Ni Nq Qb) MjIn NbPg} dB{aW(aJ aS bE bJ bW cl) aK(aU bW cR) aD(aN cR) aY(aZ cL) bZ(bW cX) aNcS aZdF} Ni{Ij(It Jk Mj Mk Mr Na Og Pg) Og(Io Jp Nd Qe) Li(Oy Pa Po)} aD{cR(aX bN cC cD cX dA dG dM) bZ(cZ dD) aNcC aXdK} Ex{Bc(Aw Cu Dg Dk Ef) Cs(Aw Cp Dg Dk) ApDk AwFw] cC{aN(aY dG dH) aK(bM cS) bX(cR dF) aYbO cPdK} Fw{Cw(Ao Aw Bn Cx) AoEf AwCs BaCu DbDk} bZ{dC(bE cZ dA) aK(aU bM) cU(bM dL) bNbQ} Li{In(Ih No Qb) Nv(Hq Pz) MkMv NaQb} Cs{Aw(Ar Fp) Ef(Di Fp)] Db{Cx(Bb Cp Cq) AfBb} Ij{NrIt MsMv JhOe NvOn} cS{bL(aK aQ) bMcU dCdG} Og{Ir(Jn Jr) MsIm} dC{dK(aX bH) cHdG} Cw{Ef(Ao Di)} aK{aQaU bMdI} AwBcCt MdJhOe MuInIv aNaYbO Unconstrained panels with 3 analytes, where 1.0E-7 >= 'AUC p-value' > 1.0E-8. Contains 3,406 panels of 409,920 total panels evaluated. :
Pf{Fp(aA Et Fr Hv Hw Ik In Ip Iq Ir Iu Jg Ji Jj Jl Jo Jp Jq Jr Jt Li Lj Lu Lv Lw Lx Ly Lz Ma Mb Mc Md Me Mg Mh Mm Mn Mp Mq Ms Mt Mv Mw My Mz Na Nd Nf Nn No Ns Nt Nv Nx Ny Og Ok Om On Oz Pa Pb Pc Pd Pe Po Qc Wm) Na(Et Fr Hq Hr Hu Hw Hx Ih Ik Il Im Io Ir It Iu Jh Ji Jj Jl Jm Jn Jq Li Lj Lv Lw Mc Md Mh Mi Mn Mq Ms Mu Mv Mw Mx Mz Nd Ne Nm Nn No Ns Nu Nv Nw Nx Og Ok On Pb Pd Pe Po Qc Wm) Mx(Fr Hq Hv Ik Io Ip Iq Is It Iu Jl Jp Jr Jt Li Lj Lv Lw Lx Ly Mb Me Mg Mh Mi Mj Mm Mn Mp Mq Ms Mt Mv Mw My Mz Nf Ng Nm Nq Ns Nt Nu Nv Oe Og Oi Ok Om On Oz Pa Pd Po Qa) Nl(Hq Hr Hu Hw Hx Ih Ik In Io Iq Ir Iu Jg Jl Jm Jo Jp Jr Jt Lj Lw Lx Ly Ma Mb Mc Me Mh Mi Mn Mp Ms Mt Mv My Nb Ng Nk Nm No Nu Nv Ny Ok On Oy Oz Pa Pb Pg Po Qd) Pe(Fr Hq Hr Hu Hw Ih Ii Il Is It Jh Jj Jl Jn Jp Jt Lv Lw Lx Ly Lz Ma Mb Md Me Mg Mj Mp Mq Mz Nb Ne Nf Nj Nm Nn Nq Nw Ns Ny Of Ok Om On Oy Oz Pb Pz Qc Qd Wm) Mj(aA Et Fr Hr Hu Hw Ik Ir It Iu Iv Jg Jj Jn Jq Jt Li Lj Lv Ma Mb Md Mg Mh Mn Mr Mw My Nb Ne Ng Nn No Nq Ns Nt Nx Og Oi On Oy Pc Pd Po Qa Qc Qd Qe Wm) Nk(Fr Hq Hr Hv Hx Ij Ik Im In Io Iq Ir Is Jl Jm Jp Jq Lj Lu Lv Lw Lx Ma Mb Mc Mh Mi Mm Mq Ms Mt Mv My Nb Ne Nh Ni Nx Of Oi Ok Oy Oz Pa Pb Qa Qc Qd Qe) Ml(Hv Hw Hx Ih Ik It Iu Jj Jl Jm Jt Lu Lw Lx Ly Mb Mc Md Me Mg Mh Mi Mk Mm Mn Mq Mr Ms Mt My Nb Ne Nf Ng Nj Nq Nu Ok Om On Oy Oz Pc Pd Qa Qd Qe) Lh(Et Hq Hr Hu Hv Ih Ii Ik Iq Ir It Iv Jh Jj Jn Jo Jr Lw Mb Mc Md Mf Mh Mn Mt Nh Ni Nm Nn No Nr Ns Nt Nw Nx Of Og Oi Ok Oy Pb Pc Pd Pg Po Pz Qd) Mu(aA Et Hr Hu Hw Ih Ip Iq It Iu Jg Ji Jj Jp Jr Js Jt Lj Lu Lv Lx Ly Md Mh Mk Mm Mp Mr Mw My Mz Nd Ne Nh Nq Nu Ny Og Oi Oz Pb Pd Pz Qa Qc Wm) Lz(Hq Hr Hw Hx Ih Ik Im In Io Iu Jg Jh Jo Jr Jt Li Lw Ly Mc Md Mg Mn Mq Mr Mv Nb Ne Nh Nj Nq Nr Ns Nt Og Oi On Oy Pa Pg Qb Qc Qd) Oe(Fr Hq Hr Hw Hx Ih Im In Iq Is Jj Jt Lu Lx Ly Ma Mc Mi Mk Mp Mq Ms Mt Mv Mw Mz Nd Ne Nf Nn Nq Ns Nt Nu Nx Oi Oy Oz Pb Po Qd Wm) Nt(Fr Hr Hu Hx Il Ip Iq Ir Is It Jg Jn Lu Mc Md Mf Mi Mk Mn Mp Ms Mv Mw Mz Nd Ne Nj No Nq Ns Nw Nx Ny Of Oi Pb Pc Pg) Ni(Et Fr Hq Hu Hw Hx Ih Il Io Ir Is Iu Ji Jn Li Ly Mb Me Mm Mn Mp Mt My Mz Nd Ne Nh Nn No Nq Nu Nv Oy Pc Pd Po Qa) It(Fr Hv In Ir Is Iv Jh Jj Jm Jn Jq Jr Jt Lu Ma Mf Mk Mn Mq Mw My Nh Nj Nm Nr Nx Of Oz Pc Pg Po Pz Qc Qe) Mr(Et Hq Hr Hx Il Io Is Iu Jh Ji Jk Jp Jq Li Mb Md Mi Mk Ms Mv Mw My Nd Nv Nw Nx Of Pg Qa Qc Qd Qe) Js(Hq Hr Hu Ii Ik Il In Ip Iu Jg Ji Jj Jk Jm Jp Jt Li Lj Lu Ma Mb Me Mp Ms Mv Nb Ne Nh Nn Ns Ny Pb Qd) Nr(Et In Ip Iq Ir Iu Iv Jg Jh Jk Lu Ma Md Mi Mk Mp Mw Nd Ng Nm Nn Ns Nw Nx Ny Of Oi Oy Pg Po Qc Wm) Jq(Fr Hq Hu Hw Hx Ii Ik Il Im In Ir Iv Jg Jk Jt Li Lv Ly Me Mh Mk Nm No Ny Oi On Pg Po Pz Qc Qe) Oi(Hu Hw Il Io Ip Iq Is Iv Jj Jp Jr Jt Li Lv Lx Mf Mp Mq Ms Mv Mw Nn Nq Nv Nx Og Om Pg Qc Qe) Pg(Hr Hw Im In Ir Is Jh Ji Jj Jk Jn Jp Li Lu Ly Md Mk Nd Nh No Nu Nv Nw Ny Og Po Pz Qc Qe) Nn(Et Im In Iq Iu Iv Jt Li Lv Lw Ma Me Mi Mk Mp Ms My Nd Nj Nv Og Po Pz Qa Qd) Lu(Hq Hu Hw Il In Iq Is Iu Iv Jl Jm Lw Md Mh Mi Mw Mz Nd Ne Ns Nv Ny Om Pd Qc) Ii(Hw Hx Ij Iu Jg Ji Jj Jt Ma Mb Me Mg Mh Mk Mq Nb Ne Nw Om Oy Pb Pd Wm) Is(aA Et Hw Il Im Ji Jk Ma Mf Mi Mk Mw Nd Nh Nj No Nw Of Pz Qb Qc Qd Qe) Jn(Hq Hv Hw Hx Il Im In Jg Jr Li Ma Mb Mi My Nj No Nq Nv Nx Og Pb Pd Pz) Mf(Fr Hw Hx In Ip Jh Jj Jk Jp Jt Lj Ma My Nd Ne Nh No Pc Po Pz Qc) Li(Hx Il Iq Ir Iu Iv Ji Jl Lv Lx Ly Md Mk Mp Mz Ne Nh No Nv Ok Po) Mk(Ih Il Ip Ji Jj Jt Mt Mw Mz Ne Nf No Nv Nw Of Oy Pb Pc Pz) Iv(Fr Hx Ih Il Ir Jh Ji Jr Jt Me Mp Mq Mw Mz Nh Ns Nw Nx Po) Jt(Fr Il Ir Jk Ma Mn Mw Nd Nh Nm Nq Ns Nu Nx Ny Of) No(Fr Il In Ir Lx Mb Mi Mz Nj Nw Nx Ny Pz Qc Wm) Ji(Im Ir Jh Lv Lw Lx Mq Mw My Nb Nd Nf Nh Nj On) Po(Et Fr Il In Jj Jk Lv Lw Mw Nb Ne Of Og On) Nd(Il Lv Lx Ms Mt Mz Nu Nw Og Oz Pb Pc) Qc(Hr Hx Ih Ip Iq Jh Jl Mp Mq Pz Qa Qd) Mw(Et Jl Lx Mt Ne Ng Nh Nu Nw Nx Qb) Mp(Hw Il In Ip Jj Lv Md Ng Ny Qe) Nv(Im In Jh Jk Ma Me My Ne Ny Of) Et(Hw In Ma Mb Me Ne Nh Nq Of) Ip(Hv Il In Jl Jp Jr Ms Nj Ok) Qb(aA Fr Hv Ly Me Mv Nq Nx Pd) Nw(Fr Im In Mi Ne Ng Nh Nq) Og(Hr Il In Ir Ms Nh Pz Qa) Pz(Hv Hw In Jl Mt Nh) Mi(Jl Lx Mz Ok Pa) Il(Hx Lv Mg Ng Pd) Wm(Hu Mt Qa Qd) Nj(Lv Mt Of Oz) Jh(Hq Hv Hw Nh) Fr(Ms Mt Nq) Im(Mq Ne Nh) Nq(In Mv) Lx(Ok On) My(Jr Mt) Mz(Ir Lw) Ng(Jk Of) Hv(Nb Ny) Jl(In Qe) LvNh MaMs MgNc MqJm IrQa QdJr PcPd} dE{aS(aA aC aE aJ bA bE bF bL bM bN bO bR cB cO cP cV cW dF dG dH dL dM) aO(aC aE aJ aP bB bG bO bS bZ cB cC cG cH cI cJ cK cO cV cZ dB dK) cG(aF aI aJ bB bF bG bM cB cH cJ cV cW dA dB dC dL) cP(aM aP aR aV bJ bL cA cB cI cO cX dG dH dK) aF(aD aM aV bB bI bO bQ bU cB cQ cV dC dK) cH(aC aJ aV bI bM bN bQ bS cB cC cI cK dB) dG(aA bA bM bV cB cD cM cQ cU dD dF dI dK) dH(aG aV aX bE bM bR cA cB cI cW dF dI dJ) dM(aA bB bL bO cA cW cZ dA dC dF dI dJ dL) aR(aD aP aU aX aZ bB bG bU cC cM dJ dL) bC(aJ aM aP aV bA bM bO bV cB cD cQ dF) bZ(aC aJ aX bH bS bU bV cC cD cK dF) bQ(aD aE aM bB bL bM cB cC cL cW) aX(aC aD aU aZ bA bB cO dB dD) aV(aA bF bG bN cA cC cM dA) cI(aP aZ bG bJ cB cO cQ cW) cN(aD aE aM aU bJ bR bU cL) cV(aC bM cB cD cM cO dA dC) bE(aD aE aP aZ bU cZ dF) cA(aC bB bJ cJ cO cQ cX) aU(aH aJ bJ bO cU dL) bV(aJ bL bM dA dC dF) cW(aA aI bB bN bU cX) dK(aE aM bN bP cL cQ) bG(aZ bI bR cM dL) cO(aP bF bR cC cQ) dF(aM bI bO cD dD) aA(aM bL bO cC) bB(bO cE cL dA) bH(bU cU dA dJ) cX(aI bR cM dD) aZ(cD dB dI) bP(bI cB dL) cL(bS cK dD) cQ(bJ bL dI) aM(bU dI) aP(aJ dA) aEbU aGbO aIbF aQcD bAcM bJbR cBdA cSdB cYdL}
Nc{Qc(Et Fp Hr Ih Ii Io Ip Ir Is Ji Jj Jl Jm Jn Jo Jt Lj Lu Lw Lz Mb Mc Me Mf Mi Mk Mn Mp Mr Ms Mt Mw My Na Nd Ng Nl Nn No Nv Nw Ny Oe Oi Ok Om On Oy Oz Pb Pe Qa Qd) Fr(Fp Hq Hv Hx Ih In Io Ip Iq Ir Is It Iu Jk Jm Jo Jt Lj Lw Mb Mc Mg Mh Mj Mq Mv Mw My Na Nd Ne Ng Nh Nj Nl Nm Nt Nx Oe Og Oi Ok On Oy Oz Pb Pc Qb) Jh(Hu Im Ir Iv Jk Jl Jp Lj Lx Ly Md Mf Mj Mk Mr Mt Mu Mw Nb Nl Nn Nq Ny Oh Oi Pb Pd Pg Pz Qa) Jg(Et Hw Ik Im Io Iv Jl Jp Jt Lu Mh Ml Mm Mp Mt Nl No Nw Oe Oh Pe Pg) Wm(Ip Lu Mh Mi Mn Mw Nd Nh Nj Nk Nq Nu Om Oz Pg Pz) Jk(Hu Hv Ii Ij Il Im Me Mf Ml Nb Nh Ni Nj Pa) Li(Hu Im Jp Mg Mx Nd Nf Ng Nh Nq Nv Nx On Po) Mv(Hu Iu Iv

Figure 26 Continued

Jl Me Mh Mm Mp Mt Nn Pd Pe Pz) Pz(Hw Io Jr Js Mx Nb Nk Nq Pe Qd) Pa(Hu Im In Ir Lh My Nr Ny) Mu(Im Io Ir Iv Nr Pe Pg) Hv(Ir Is Jp Ns On Pe Pg) Il(Io Iv Jp My Nh Nx) Qe(Hu Js Mx Og Oh) On(Et Ii Jt Md Mt) Nb(Hu Mg Of Pg) Ij(Hu Hw Ir Nq) Oh(Im Mw Nq Ny) Nr(Io Na Nx) Og(Im Ir Lx) Mx(Im Is) Hw(Hu Of) Nq|i LuNw MwPg NkQd} dN{cC(aC aD aJ aL aO aR aU aW bE bI bM bO bS bV cA cG cJ cK dA dI dM) bZ(aF aH aM aQ aR aY aZ bG bH bI bJ bQ cE cJ cN cQ cU cV cZ dG) aN(al aP aR aU bJ bP bW cB cI cM dI dJ) bF(aC aG aM bJ cJ cL cP cU cZ dD dG) bH(aA aQ aS aU bN bW bX cL cW dK dM) cR(aC aI aP aY aZ bB bV cS cV dA dI) bL(aF aJ aQ aU bP bQ bV bX cV dH) bG(aA aC aE aG aS aX bE cW dK) aY(aA aJ aX bC bI cO dB dH) cH(aD aG aM aS cL cO cP dA) cE(aE aV aZ bA cG cQ dC) cD(al aS aZ bJ cF cL) cX(aF aL cM dF dK) dB(al aZ bJ bX cS) aG(aD bM bN bX) aM(aA aK bX cL.) bA(aA bC dC dM) aH(aF aZ dJ) cO(aQ aZ cL) bP(cG dL) aEaR aSdH aXdC bRcS} Fr{Ii(aA Fp Hr Ih Ik In Io Ip Iq It Iu Jj Jk Jl Jm Jn Jo Jp Jr Js Jt Ly Md Mf Mk Mm Mn Mp Mr Mt Mw My Mz Na Nb Ne Nj Nl Ns Nu Ny Of Og Oi Oy Pb Pd Po) Nn(Hx Ik Iu Jl Jn Lh Ma Mg Mh Mm Mu Mv Ni Nj Nk Nl Nq Nt Nx Ny Og Pa Pg Po Pz Qd Qe) Mx(Im Ip Ir Iv Mb Mh Mj Ml Ms Nl Nr Nv) Wm(Ip Lj Lx Me Ms Ni Nu Nv Of Oi Pe) Nl(Ik Li Lv Mb Md Mt Ni Pc Pg Pz Qc) Ni(It Jt Li Mf Mr Mu Na Nq Qc) Mh(Md Mp Mt Qc) Ex(Aj Ap As) Mt(Iv Ml Pz) Di(Cw Db) No(Li Pc) Nq(Pc Pg) Ir(It Nv) Js(Lj Pz) BaFw BcGp NrIm LvMd MsIl NkIj HvOi InIv QcPc NxOh} Wm{Mu(Fp Ih Ii Il Ip Jn Jo Jt Lj Lv Ly Na Nl No Oi Pe Pg Pz Qa Qb Qc) Jh(Ih Io Ip Jl Jn Jp Lh Lv Ml Mp Mt Nl Nt Nv Pe) Nl(Hu Ij Ik Ip It Iv Jg Li Mg Nf Pz) It(Et Ir Jp Mw Na Ne Nk Nr Qd Qe) Hv(Jo Jp Jt Me Mh Nk Of Og Qa) Pz(Et Jk Jn Ly Mv Na No Qc) Nb(Fp Nk No Oh Oy) Hu(Ip Lv Mk Na Oh) Qc(Lj Mt Na Nk Qb) Mg(Iv Jt Me Oh) Iv(Il Ma Mn) Nn(Mx Oh) Lv(Ih Js) Mv(Na Nr) Mw(Fp Il) Ni(Ij Ip) NtJg MeMy MiJo MsIj MtOm MxIs NkJk InOf IrOg NvOh OkOn} Qc{Ni(Hv Ij Ip Jh Jm Jr Li Mh Mr Mw Ne Nn Nt Of Oh Oy Oz Pb Pg Qa Qb) Mu(Hq Il In Jh Ly Mg My Na Nl Pb Pg Pz Qb) Nl(Ik Im Jg Jk Mb Mh Mv Nj Nn Ns Nx) Jh(Hv Hw In Io Js Ne Nv Pc Qb) Nk(Hv Js Li Mh Ml Nb Pa) Mx(Im Iv Lv Mj Pc Pz) Mh(Hx Md Mg Og Pc) Pz(Hw Hx Mz Nr Pg) Na(Hv Ma Nr Pe) Js(Ir Ma Nr Pc) Oh(Li Lj Mg Pc) Nb(Ii Nv Qb) Hv(In My Ne) Mv(Ii Nr) Qb(Li Pc) NoIi MlHu} Li{Ii(Ip Is Jh Jj Jo Lu Lz Ml Mn Mv My Ng Nk Ny On Pz Qd) Oh(Ij Il Im Jk Lh Mn Mu Na Ny Ok Om Qa Qe) Nk(Ir Jh Jk Lu Lv Ml Mx Of Pz Qb) Nl(Hu Il In Jh Jk Lu Ma Mu Nh Nr) Ni(Hv Js Lz Ml Mu Na Ng Nt Qb) Nv(Il Mu Mv Na Pg) No(Hq Is Lv Ma) Nr(Mx Nt Qb) Pz(Hw Na Oe) Lv(Mr Nt) Ma(Nn Qb) Hq(Ji Ok) Js(On Pg) MjMx MkOf MnMz MvIv NaPg InaA IpQb} cT{aE(aC aG aQ bA bC bP bQ bW cI cJ cN cY dB dJ dK) cW(aD aH aI aL aU bV cJ cO dH) cS(aG aO aU aZ bM cG cY dB) bZ(aG aN bL bV bX cC cY) aD(aG aQ aY bQ cL dH) cX(aG aW bP dG dL dM) aM(aK aR bQ cE dC) aZ(cC cU cV dB dC) bG(aI aN aX bB bJ) bF(aH aN cY) bN(cC cH cL) dC(aY bP cF) bL(cH dH) bM(cC cH) aYcG bHbV cEcV} Nl{Jh(aA Hu Ik Im Iv Jq Lu Ma Me Mf Mm Mu Nq Pa Pd Pe Pz) Jk(Ik Lj Lv Mb Me Mx Nb Nu Oh) Jg(Et Hu Ii Ik Js Mm Mt Nv) Pz(Iv Md Mt Mw Nh Nj Pa) Mu(Hu Ir Mb Ne Nr Of) Mv(Iv Md Mt Mx Pa) Of(aA In Iv Mh Pg) Nh(Ij Lu Pd) Ik(Nr On Qe) Hu(Nr Qe) Il(aA On) Ir(Js Og) NqIv LvIj MwOh HvNy ImJs} bA{aD(aK aP aR aW aY aZ bG bN bX cD cE dH) aE(aG aO aW bN bX cG cH cO cP) cX(aC aU aV aX bH bP bQ cS cZ) aA(aY bF bM bX bZ cF cQ) bL(aF aR bP bV cW) bZ(aZ bX cF cV dF) cC(aZ cR cS cW dC) aN(bB bV cH cV) cS(aP aZ cF) dC(aW bH cE) bV(bH cL) cQ(cB dB) cW(dH dM) bFcV bNbO bXcD cAdH cEcH} Hv{Mu(Il Ir It Jh Jl Lj Lw Md Mf Mh Mk Mt Mw Na Nd Ni Nq Oe Pz) In(Il Jj Jl Lv Lw Ma Md Mi Mk Mq Mx Na Nn Oh Pg) Pz(Jh Js Ma Mv Nb Ny) Na(Ih Lw Ma Nf No) Ir(Ii Mx Nd Og) Jh(Ii Ip Mw Nd) Oh(Ma Nq On Qe) Mv(Iu Mr Nk) Nb(Ma Nd) MwMx NkJk ItNy} Mx{Qe(Ii It Lv Mv Mz Nb No Nr Pc) Nb(Il Ir Jk Mw Nr Of Pz) Is(aA Im Jh Md Ni Nr Pz) Ir(Ii Jk Jn Jr Mw) Nk(Jg Nq On Pz) Iv(Im Ma Mw Nr) Pz(Mw Nq Qa) Jh(Ij Lj Ml) On(Jq Ms Nv) Ni(Jk Nq) Oh(Ij Qa) LvMw MdMt MjMu JkLj} bP{cS(aC aG aI aN aP aW bE bH bM bS bU cC cJ cK cQ cR cZ dC dL) cF(aA aC aF aK aM aN bI bQ bR bS cA cK cO dD dK) aE(aH bQ cG dF) aY(aL bU cW dB) cG(aK cP dC) aX(aL dD) bZ(bX cW) aDcR aHcW aKdI cEcP} Gp{Cp(Ad Al Ap Ar Ba Bg Co Cu Dc Di Dk Fw) Al(aA As Bc Bg Bo Cw) Ap(Co Cq Ct Cx Db Dk) Ba(Ad Bn Cq Ct De Fp) Bg(An Bn Cu Cv De) As(aA Aw Cu Cw) Ad(aA Bn Bo) Cw(Bb Cv Fw) Cu(aA Cx) AwBc BnDg BoEf CoGl} Oh{Mw(Hw Ii Ir Iu Jh Jp Md Mg My Na Nb Ni Ny Pe Qe) Nq(Ir Is Lh Mg Nf Qe) Mv(Ii Ir Is Iu Lh Ma) Ij(Hx Mi Ne Ni Nr Qe) Jh(Il Is Lj Nr Qa Qe) Ma(Is Lj Qa) Mu(Is Pe Qa) NnIs NrQe NkJk HwNy IiOn QaOg} Nk{Ij(Hw Jn Lv Lx Mk Ml Ms My Mz Na Ne Nr Ns Of On Pg Pz Qe) Jk(Ii Il Iv Lj Me Mf Mh Mj Mu Nb Ni Nn Nr Pa) Mv(Ii Mh Ml Mr) Mu(Iv Nr) Il(Iv Jh) Im(Js Og) NqPa MlJh NbOf IrJs PzOg JgJt} aE{aN(aG aH aL aS bF bQ cF cQ dA dG) aH(aC bG bH cS dA) cC(aQ cF cO cQ) aX(bZ cS cY) aZ(aC aL bV) bG(bV dA dG) bE(aQ bF) bZ(cD cQ) cE(cX cZ) cS(bJ dM) aGcZ aIdA aLbW aWdB bXcO cDcF cXdG} Js{Ir(Hu Im Jh Jk Jl Mp Mt Mw Nm Nq On Pz) Qe(Im Ma Ng Nr Pc) On(Im Iv Lj Ni Nv) Is(Im Mh) Pz(Hw Lx) NrMa} Mu{Il(Ii In Jg Jt Lj Lu Mi Mk Mm Mv Mw Na Ne Nn Nr Nt Pz) Nr(Mt Na Nn) Mg(Ml Mm) Ir(Jr Qb) Iv(Ii Na)} aM{aA(aL aU aY bU cX dH dM) aX(aY cF cW dK) bH(bX bZ cP) dA(aV cB dK) dG(bF dL) dI(aK aS) aYcL bEdK bXcE bZcP cCcQ} cW{aK(bB bE bH bR bU bW cB cD cM cO dB) bZ(aW cU dD) aG(bQ dB) cE(bX dA) cF(aA dA) aCaL aNbH bFdD} Co{Bo(aA Al Ar As Cw Dc Dk) Ao(An Ax Cs Cv Dc Ef) Aw(Ax Cs Fw) Cw(Di Fw) AdBc AfCx AxBg} cC{cF(aA aC aD aF aG bV cE cM cN cZ dF) cS(aY bX cI) aN(aK aS) aZ(cE dF) bXcO cEcL cXdF} Ii{Mv(aA Mh Ng No Oi Ok) On(Et Il Iv Jh) Ir(Jk Mg Og) Jk(Mh Ni) Of(Lx Nb) MgQe IvJh} dB{aW(aA aD aN aY cB cR cU dH dI) aN(aO cG) cF(bJ dG) cR(aV bX) aDaX aZbZ bWcS cXdK} Ij{Ni(Hw Hx Jo Lj Ne Pa) Mv(It Lv Nn) Na(Iv Pz) In(Iv Pz) IrJn} Bo{Aj(Af Bn Ct) Bg(Dc Fp) Ct(Cx Dl) Fw(Ba Dk) ArAx CpDb CxEf DgEx} Og{Ir(Hw In Is Md Ne Ni Oe) NrOi InIv IsQe} Ax{Bg(Cu Ex Fw) Ef(Ad Ct Ex) AdDk ArBa CpFp} Cs{Aw(An Ap Ct) Bg(Cw Ex Fw) CpDb EfEx} Fw{Cw(Al Ba Cv Dk) CuCx} aD{cR(bE cS cZ) aNbV bEbQ} Il{Nb(In Na) IrJn NvOn} Pz{Jt(Mw Nq) MhJr NjHw} cF{dC(dA dG) bFcZ bUdF} It{NqNi NrNa ImOe} On{Nv(Ik Pg) ImJt} Ao{Bg(Af Ex)} bL{cS(bG bN)} AlBcEx AnBaDc NqMaMw NrNiJk MgInIv aNaYbN cNcXdK

Unconstrained panels with 3 analytes, where 1.0E-6 >= 'AUC p-value' > 1.0E-7. Contains 6,764 panels of 409,920 total panels evaluated. : Pf{Is(Fr Hq Hr Hu Hx Ih In Io Iq Ir Iu Iv Jg Jh Jj Jl Jm Jn Jp Jq Jr Jt Li Lj Lv Lw Lx Ly Mb Mc Md Me Mg Mh Mm Mp Mq Ms Mv My Mz Ne Ng Nm Nn Nq Nr Ns Nu Nv Ny Og Ok Om On Oy Oz Pa Pb Pc Pd Po Qa) Li(Hq Hr Hu Hw Ih Ik Im In Io Ip It Jg Jh Jk Jm Jp Jt Lh Lu Lw Ma Mc Me Mf Mg Mh Mi Ml Mm Mn Mq Ms Mt Mu Mw My Nd Nf Ng Nj Nm Nq Nr Ns Nt Nu Nw Nx Ny Of Og Om On Oz Pb Pc Pd Pz Qc Qe Wm) Po(Hq Hr Hu Hw Hx Ik Im Io Iq Ir Iu Jg Ji Jl Jm Jn Jp Jr Jt Ly Ma Mb Mc Md Me Mg Mh Mk Mm Mn Mp Mq Ms Mv My Mz Nf Nk Nm No Ns Nt Nu Nv Nw Nx Ny Ok Oy Oz Pb Pc Pd Pe Pz Qa Qc Qd Qe) Pg(aA Et Fr Hq Hu Hx Ih Ij Ik Il Io Iq Iu Jg Jm Jr Jt Lj Lw Lx Mb Mc Me Mf Mg Mh Mi Mj Ml Mm Mn Mp Mq Ms Mt Mu Mv Mw Mz Nb Ne Nf Ng Nm Nq Ns Nx Of Ok Om On Oy Oz Pa Pb Pc Pd Qa Qd) Jq(aA Et Hr Ih Io Ip Iq Iu Ji Jj Jl Jm Jn Jr Js Lh Lj Lu Lx Lz Ma Mb Mc Md Mg Ml Mm Mp Mq Mt Mv Mw My Mz Nb Nd Nf Ng Nh Ni Nj Nn Nq Nr Ns Nt Nu Nv Og Om Oy Oz Pa Pb Pc Pd Pe Qd) Qc(Et Hq Hu Hv Hw Il Im In Ir Iu Iv Ji Jj Jk Jm Jn Jo Jp Jr Lv Lw Lx Ly Ma Mb Mc Md Mh Mi Mk Mn Ms Mt Mw My Nb Ne Nf Ng Nh Nm Ns Nu Nw Nx Ny Of Og Ok Om On Oy Oz Pb Pc Pd Qe) Lu(aA Et Fr Hr Hx Ik Im Io Ip Ir Jg Jh Jj Jk Jn Jo Jp Jr Jt Lh Lj Lv Lx Ly Mb Mc Me Mk Mm Mn Mp Mq Mv My Ng Nh Ni Nj Nn Nq Nu Nx Of Og Ok On Oy Oz Pa Pb Pc Pe Pz Qb Qe Wm) Ip(Hq Hr Hw Hx Ih Ik Io Iq Ir Iu Iv Jg Jj Jk Jm Jn Jo Lw Lx Ly Mc Md Me Mh Mi Mj Ml Mm Mn Mt Mv Mw My Mz Nb Nd Nf Ng Nh Nk Nm Nq Nu Nx Of Og Om On Oy Oz Pb Pd Pz Qe) Nr(Hq Hr Hv Hw Hx Ih Ik Il Ji Jj Jl Jm Jo Jp Jr Lv Lw Lx Ly Mb Mc Me Mg Mh Mm Mn Mq Mr Ms Mt Mv Mz Nb Ne Nf Nh Nj No Nq Nu Nv Og Ok Om On Oz Pa Pb Pc Pd Qa Qd Qe) Mp(Et Hq Hu Hx Ik Io Iq Ir It Iu Ji Jk Jl Jm Jn Jr Jt Lx Ly Mc Me Mf Mh Mi Mj Mk Mm Mn Mq Mr Ms Mt Mv Mz Ne Nh Nm No Ns Nu Nv Of Og Om On Oy Oz Pb Pc Pd Pz

Figure 26 Continued

Wm) Il(Et Fp Fr Hq Hr Hu Hv Hw Ih Ik In Io Iq Ir Iu Jg Ji Jj Jo Jr Lw Ly Ma Mb Mc Md Mf Mh Mi Mm Mn Mq Ms Mt Mw Mz Ne Nf Nh Nm Ns Nu Nv Nw Nx Ny Ok Om On Oz Pc Wm) Jk(Et Fr Hu Hv Hx Ih In Iq It Iu Iv Jh Ji Jm Jn Jr Lh Lx Lz Mc Md Me Mh Mi Mk Ml Mn Mq Mt Mu Mv Mw Mz Na Nd Ne Ni Nj Nn No Nq Ns Nt Nu Og Oi Oz Pa Pc Pd Pe) Nh(Fr Hq Hr Hu Hv Hw Hx In Iq Ir Iu Jl Jn Jp Lx Ma Mb Md Me Mi Mk Mm Mq Mr Ms Mt Mv My Mz Na Nb Nd Nf Ng Nn No Nq Ns Nt Nu Nv Nx Ny Oc Of Oi Pc Pd Qa Wm) Jn(Hr Hu Ih Ik Io Iq Iu Jh Ji Jj Jl Jm Jo Jp Js Jt Lv Lw Lx Ly Mc Md Me Mf Mm Mn Mq Mr Ms Mt Mz Ne Nf Ng Nm Nn Ns Nw Ny Of Ok Om Oy Oz Pa Qd Qe) Jr(Fr Hr Hu Hx Im In Iq Ir Iu Jg Ji Jm Jo Lw Ma Mc Md Mi Mj Ml Mn Ms Mt Mv Na Nd Nf Nj Nm No Nq Ns Nt Nu Nw Nx Ny Of Og Ok Oy Pa Pc Pd Pe Qa) Mw(Hq Hr Hw Hx Ih Im In Io Ir Iu Jg Jj Jm Lv Lw Ly Lz Mc Md Me Mf Mh Mi Ml Mm Mn Mq Ms My Mz Nj Nk Nq Ns Ny Of Og Ok Oz Pa Pb Pc Pd Pz Qa) It(Et Hq Hr Hu Hx Ih Ij Ik Jg Jl Jp Lj Lv Lw Ly Mb Mc Md Me Mg Mh Mi Mm Ms Mt Mv Mz Ne Nf Ng Nn No Nq Ns Nu Nv Ny Ok Om Oy Pa Pb Pd Qa Qd) Jt(aA Hr Hu Hv Hx Ik In Io Iq Jj Jl Jm Jo Jp Lh Lj Lv Lw Lx Ly Mb Mc Md Me Mh Mi Mq Mr Mt Mv Na Ne Ng Nj No Nt Nv Ok Om On Oy Oz Pc Pd Wm) Nd(Fr Hr Hu Hv Hw Hx Ih Im In Iq Iv Jg Jh Jj Jl Jm Lw Ly Mb Mc Md Mh Mi Mn Mq My Nb Ne Nf Ng Nm Nq Ns Nx Ny Of Oi Ok On Pd Pz Qa Qe) Nt(Et Hq Hw Ih Ik Io Iu Ji Jj Jl Jm Jo Jp Js Lj Lw Lx Ly Ma Mb Me Mg Mh Mm Mq Mt Na Nf Ng Nm Nu Nv Ok Om Oy Oz Pa Pd Pe Qa Qe Wm) Iv(Et Hq Hr Hv Hw Ik Im Io Iq Jg Jl Jm Jp Lv Lx Ly Ma Mb Md Mh Mi Mk Mm Mn Ms Mt Ng Nj No Nu Ny Of Og Ok Om Oz Pb Pc Pd Pz Qa Qe) Nn(Hq Hr Hu Hv Hw Hx Ij Ik Io Ir Ji Jj Jl Jm Jp Lx Ly Mc Md Mh Mm Mn Mq Mr Mt Mv Mz Nm No Nq Ns Nu Nw Ny Ok Om On Oz Pa Pb Pd) No(Hq Hr Hu Hw Hx Iq Iu Jg Jh Jl Jp Lj Lv Lw Ly Mc Md Mh Mm Mn Mr Nb Ne Nf Ng Nq Ns Nu Nv Of Ok Om On Oy Oz Pa Pb Pd Qd) Og(Et Hu Hw Hx Ih Jk Ji Jj Jo Jp Ly Ma Mb Md Mi Ml Mn Mq My Nb Ne Nf Ng Nj Nm Nq Nu Nv Nw Nx Ny Of On Oy Pc Pd Pe Qe) Oi(Fr Hq Hr Hv Hx Ih Ik Im In Ir Jh Jm Lj Ly Ma Mc Md Mk Mm Mr Mt My Na Nb Nf Nl Nm Ns Nu Ny Ok On Oy Oz Pa Pb Pc Pd Pz) Mr(Hu Ik In Iq Ir Jj Jl Jm Jo Js Lh Lj Lv Lw Ly Mc Me Mh Mm Mn Mz Na Nb Ne Nf Ng Nm Nq Ns Ok Om On Oz Pb Pd Pe Pz) Nv(Et Hq Hr Hu Hw Iu Jg Jj Jp Js Lh Lv Lw Lx Ly Mc Md Mf Mi Mj Mn Mq Mv Mz Nb Nf Nj Nq Ns Nu Ok Om Oz Pb Pc Pd Pe) Mu(Fr Hq Hx Ik Im In Io Ir Jh Jm Jo Lw Lz Ma Mb Mc Me Mg Mi Mn Mq Mv Nb Nf Nm Ns Nx Of Ok Om On Oy Pa Pc Qd Qe) Iq(Hq Hu Hw Im In Ir Jg Jj Jm Js Lv Lw Ly Lz Md Me Mf Mi Mj Mk Mq Mv Mz Nf Nm Nu Nx Ny Of Ok On Pb Pe Pz Qe) Nw(Fp Hq Hr Hu Hv Hw Hx Ih Io Iu Jj Jl Jm Jp Js Lw Ly Ma Mb Md Mn Mq Nb Nj Ns Nu Ny Of Ok On Oy Pa Pc Qa Qe) Ji(Et Fr Hq Hr Hu Hv Hw In Iu Jg Jl Jo Lh Ma Mb Mh Mm Mt Mz Ne Ng Nq Of Ok Om Oy Pa Pb Pc Pd Pe Qa Qd Qe) Mk(Fr Hr Hu In Ir Jh Jl Jm Jp Lh Lj Lx Ly Md Mf Mh Mi Mq Ms Mv My Na Nb Ni Nk Ns Nu Ok Om Oz Pa Qa Qd) Md(Et Hw Hx Ik Im In Ir Iu Jg Jh Jj Jm Jp Js Lv Ly Me Mf Mh Mi Mn Ms Mv Mz Ni Ns Ny Om On Pd Qe) Na(aA Hv Ij In Jo Jp Js Lx Ly Ma Mb Me Mg Mm Mt My Nb Nf Ng Nj Nq Ny Of Om Oy Oz Pa Pc Qa Qd Qe) Ni(Hr Ij Ik Im Jh Jj Jm Jo Lj Lv Lw Lx Mc Mg Mh Mi Ms Nb Nf Ng Nm Ns Ny Ok Om On Oz Pb Pz Qe) Hw(Fr Hu Hx Im Io Ir Iu Jg Jj Jl Jo Lh Lw Lx Ly Ma Mg Mi Mn Mt Mv My Mz Nf Nk Ns Nu Of Pd Qa) Et(Hu Hx Im Io Ir Iu Jh Jj Jl Jm Jo Jp Js Mf Mh Mi Mm Mq Mz Nb Nu Nx Ny Ok Om On Pa Pc Pe) Mj(Hq Hv Hx Ih Io Jl Jm Jo Jp Lw Lx Mc Me Mf Mi Mm Mq Ms Mt Mz Nf Nj Nm Nu Ok Om Oz Pa Pb) Pz(Hr Hu Io Ir Iu Jm Jo Lv Me Mh Ml Mm Mn Mq My Nb Ne Ng Nj Nq Ny Of Ok Om On Oy Pd Qe Wm) Js(aA Hx Jl Jo Lw Lx Ly Mc Mg Mh Mi Mm Mn Mq Mt Mz Nf Ng Nu Ok Om Oy Oz Pa Pc Pd Pe) Mf(Hq Hr Hu Hv Ik Im Iu Jl Jm Lv Mb Mc Me Mi Mn Ms Nj Nq Ny Of On Oy Oz Pa Qd Qe) Mq(Fr Hq Hr Ir Iu Jh Jj Jl Lh Lv Lw Ly Me Mh Mv My Mz Ne Nj Nu Ny Of Oz Pd Qe) Im(Hq Hu Hx Ih In Jj Jl Jp Lw Ly Ma Mc Mh Mi Ml Ms Ng Nj Ns Ny Ok On Pa Qe) Ne(aA Fr Hu Hv Hx Ir Jh Jl Jo Lv Ma Mm Mv My Nf Nq Ns Nx Ny Of Pb Pc Pd) Pe(Hv Hx Ij Ik Io Iu Jg Jm Jo Lj Mc Mh Mm Mn Ms Mt Mv Ng Ns Pa Pc Pd Qa) Mz(Fr Hq Hu Ik Iu Jj Jp Lh Lx Ly Mh My Ng Nl Nm Ns Nu Nx Ny Ok On Pd) Lh(Fp Hx Iu Jg Jl Jm Jp Lj Lx Me Mg Mm Ms Nb Nf Ng Nq Nu Ny Om Pa) Oe(aA Hv Iu Jg Jm Jo Lj Lw Mb Me Mh Mm Mn My Nm Ny Ok Om On Pa Pd) Mi(In Ir Jm Lv Lz Me Mh Mn Ms Nm Nq Ny Of Om On Pb Pd Qe) Jj(Hq Hu Hx In Ir Iu Ly Mc Mm Mn Nq Ns Nx Ny Oz Pd Qe Wm) Fr(Hu Hv Iu Jg Jl Jp Lx Ly Mh Ml Mm Nj Nm Pb Pc Pd) In(Hr Hu Ih Ir Jg Jh Jm Ma Ml Mt My Nj Ny Of Ok Pd) Ml(Hq Hr Hu Io Jg Jh Jo Jp Lj Mv Ns Nx Ny Pa) Ms(Hr Hx Iu Lv Me Mv My Nj Nq Nu Nx Ny Pb Wm) Nj(Fp Hr Jh Jl Jp Lx Me Mx Nb Nf Nq Ns Pb) Hx(aA Hr Io Ir Jm Lv Mb Mh Mt My Of Pb Qe) Lz(Hu Hv Lj Mx Nf Ng Nl Nx Ny Om Qe Wm) Nk(aA Iu Jg Jo Me Mg Mn Ng Nm Ny Om On) Nq(Jh Jl Lv Lx Ly Ma Mt My Ny Of Pc) Ir(Hq Hv Ih Jh Jl Mh Mm Nx Oz Pb Pc) Lv(Hu Ik Iu Jh Jl Ly Ma Me Mn Pd) Of(Fp Hq Hv Jg Jo Mg Nb Nu Oy) Pc(Hu Hv Ly Ma Mn My Nl Pb Qe) Me(Hq Jh Lw Mc Nf Ny Pd Qe) Ma(Hv Jl Jm Jp Mt Nu Pb) On(Hu Jp Mh Mn Ok Pa Pd) Lw(Jm Lx Nm Ok Pa Pd) Iu(Hu Jh Mv Ns Nx Pd) Qe(Hu Ih Jh Jp Lx Mt) Fp(Hr Ih Ij Io Nm) Hv(Jg Mv My Ns Pb) Nx(Ly Mh Mm Ng Nm) Qb(Ij Io Nm Qa) Jh(Ik Ly My Oz) Jl(Jp Nb Ny Pb) Pd(Nf Ok Oy Pb) Mv(Mh Mt Ng) Wm(Ih Lx) Ly(Jm Pb) Nb(Hr Nu) Ik(Lj Pb) Jp(Mn Om) Ok(Nm Pa) NsJm MgNl MyQa HuOy} dE{cN(aA aC aJ aP aR aX bB bE bI bM bN bO bP bS bV cB cC cD cI cJ cK cM cO cP cQ cU cX cZ dA dB dC dD dJ dL dM) bV(aA aC aD aE aM aS aX bE bI bN bO bR bS cB cD cK cL cM cO cP cQ cU cV dD dH dI dK dL dM) bU(aC aD aJ aU aV aZ bB bG bJ bL bQ cB cC cD cG cH cJ cL cO cQ cU cZ dA dB dC dD dI dJ) cP(aA aC aD aE aJ aX bE bI bM bO bR bS cD cK cL cM cQ cU cZ dA dB dC dD dI dL dM) bB(aC aM aP aS aU aZ bE bL bN bP cC cD cH cJ cM cQ cX cZ dG dH dI dJ dL) dM(aC aD aE aM aV aX bI bM bR bS cC cD cI cJ cK cL cO cQ cU dB dD dH dK) aU(aC aD aE aM aP aV bC bE bI bS cB cD cK cL cO cQ cX cZ dB dD dI) bP(aC aD aE aP bJ bL bM bS cC cD cI cJ cK cM cO cU cX dA dB dI dJ) aA(aD aE aJ bE bM bN bR bS cA cI cK cO cU cZ dB dC dD dF dH dL) cL(aC aE aF aP aX bE bF bI bR cB cC cD cI cQ cU cZ dA dH dI dJ) cW(aD aF aP bG bJ bL bM bR cA cC cH cM cU cV cZ dA dB dI dK dL) bE(aC aJ bJ bM bN bO bR cD cJ cO cU dA dD dG dI dJ dK dL) aX(aJ aP aV bI bL bN bO bS cI cJ cK cM cQ cZ dC dJ dL) bG(aD aJ aP bM bN bS cB cC cH cJ cK cO cV cZ dB dC dK) cX(aC aR aV bI bJ bL bM cB cC cD cI cU cZ dA dI dJ) dK(aD aP bL bM bR cA cB cD cI cV cZ dB dD dI dJ dL) cJ(aP aS bJ bL bN bO cB cH cV dA dB dG dH dI dL) dG(aC aD aE aM bN bO bR bS cC cI cK cZ dA dC) aR(aC aJ aM bJ bO bS cD cK cU cZ dC dD dI) cV(aD aE aJ bI bL bO bS cH cI cK cZ dB dL) bJ(aV bI bL bM bN cB cD cM cO dA dD dJ) cA(aE aP bM bN bO cB cD dD dI dJ dL) aS(aD aM bS cC cD cK cM dA dC dD) aV(aM aP bL cB cO cQ cU cZ dB dC) dH(aC aD aE bN bS cD cK cM cO dD) bL(aC aO aZ cD cI cM dB dC dJ) cG(aC aD aM bI bS cC cD cK cM) aE(aC aF cD cH cU dD dI dJ) cO(aF bO cH cU dA dB dI dJ) cQ(aP bN bR cM dB dC dJ dL) aF(aP bS cC cH cK dB) aZ(bI bM bN dC dD dL) bM(aP cC dI dJ dL) cH(aD aM aP bO cZ) dC(aC bC cC dA dI) bN(aM bR cM dI) cB(bO bR cC cM) dJ(bO bR cC cI) aD(aO bC bF) dA(aM bO dF) aP(bR cM) aMbF bCdD} Nc{Jg(Hr Hx In Ip Iq Iu Jh Ji Jn Jq Jr Js Lj Lx Ma Mf Mi Mj Mr Ms Mv Mw My Mz Nb Nd Ni Nj Nk Nn Nq Ns Nt Nx Og Ok Om Pd Pz Qe) Jh(Fp Hr In Ip Iq Is Iu Jm Jq Jr Js Jt Lh Ma Me Mg Mh Ml Mn Mp Ms Mv My Nk Ns Nu Nx Om Oy Oz Po Qb Qd) Mv(Hq Hr Hv Hw Ik Im In Is Jn Jp Js Lu Lv Lx Ly Md Mr Ms My Nb Nh Ni Nk Nr Ns Oe Oy Pg Qe) Li(Fp Hq Hw Ii Io Ip Is Ji Jn Jq Js Jt Mk Mp Mq Nb Ni Nm No Ns Nt Ny Oe Of Oh Ok Oy Pd Qd) Wm(Et Hu Ih In Is Iv Ji Jk Jo Jp Jq Js Lh Lw Lx Mp Mq My Na No Nr Nv Nw Ok Pd Qe) Jk(Fp Hw Ih Ik In Iq It Jj Ma Mb Md Mg Mh Mp Mu Nk Nn Ns Nt Nu Oh Pb Pe Qe) Mu(Ij Ik Jo Lj Ma Mb Me Mh Ml Mx Nb Ng Nh Ni Nm Of Pc Pd Pz Qe) Fr(Hr Ji Jj Jq Jr Lh Lx Ly Lz Mi Mn Nf Nw Of Om Po Qa Qd Qe) Ij(Im Io Is Iv Jp Lu Lv Lz Ml Ms Na Ne Nh Nk Ns Ny Qd Qe) Pz(Il Ir Is Iv Jl Jp Lu Md Mh Mw Na Nr Ny Og Pg Qe) Nb(Hv Im Lu Mw Mx My Nq Ny Og On Pa Pd Pe) Il(Hw Im Ir Is Jl Lx Na Nr Ns Ny On Qd Qe) Nq(Hu Hv Ik Im Jl Jo Mg Ni Nr Pd Pe) On(Hw Ik Im Lu Mj Mm Oh Pa Pe Pg) Nr(Hw Ip It Iv Nh Ny Of Pe) Lu(Ir Lw Lx No Nv Nx Ok Pe) Qe(Ii Ik Mp Nh Pc Qb) Pa(Lx Ma Mt Ni Pc Pe) Hu(Im Io Is Nk Nx) Qc(aA Mm Nf Nm Pd) Jp(Iv Lv Mg Nh Of) My(Ik Pc Pd Pe) Mx(Nn Ny Qa) Hv(Mn Nv Qd) Ii(Is Ny Pe) Ir(Ik Js Pg) Iv(In Nx Qd) Mw(Nh Nj) Im(Nh Of) Is(Ik Md) HwNy InPc QaOh QbPe} dN{bH(aC aF aI aJ aL aO aP aV aX aY aZ bA bB bE bF bG bJ

Figure 26 Continued

Figure 26 Continued bZ(aJ aZ bE dI) cF(bE cN dI) cQ(aN cR dK) cZ(aH bG cE) bV(aN bL) cW(aC aG) aZcR bCdI bEbF cXdF} bP{cF(aD aG aI aJ aP aR bC bE bJ bM bO bV bW bX cI cJ cM cN cQ cU cZ dG dH dI dJ dM) bZ(aG aJ aL aO aP aQ aU aX aY aZ bC bG bM bN bQ bR cS cY dA dB dC dD dI) cS(aF aJ aQ aU bC bJ bN bR bV bW bX cA cE cO cW cX dD dI dJ dM) aK(aF aG aI aN aO aP aQ aS aU aW aZ bM bQ cA cM cX cZ dC dG) dF(aD aN aR aZ bJ cW cX) cW(aG aS aX cG cY) aY(aD bR cJ dC) aL(aZ bC cX) aX(aC aD bO) cH(cP dB) aDbF aSdI aUcC cGcX} Nk{Jk(Fp Hu Hw Im Iq It Iu Jm Jn Jt Lu Lv Lz Ma Md Mg Mp Mt Mz Nh Nq Nt Nu Ny Of Oi Oy Pc Pe Pg Po) Mv(Ik II Ip Ir Iu Iv Jn Jq Js Md Mj Mt Na Nf Nr Nu Nx Oz Pa Pb Pc Pe Pg) Ij(Fp Ii Ik Im Iu Js Jt Ly Me Mf Mi Mw Ng Nh Nq Nt Nx Ny Pb Pc Qd) Js(Nq On Pe Pz Qe) Jh(Md Mm Oe Oh) Ny(Il Mx Oh Pa) Of(Im In Ir Qe) Nq(Il Jn Pc) Jg(Hv II Md) Og(Nb Pg Qe) Mx(Ir Nb) Pz(Jt Mh) MsMw NfNx HqIv QePc} Oh{Mw(Ij Ik Im In Ji Jj Jr Lh Ml Mq Ms Mv Mx Nq Nx Oi On Oy Pz) Ij(Hu Is It Jk Jp Js Ms Mt Na Nd Nj Nn No Nq Ny Pg Qa) Mv(Hv Ik Im Jp Mh Mz No Nq Ny Oi Ok On Qa) Is(Hv II Io Jr Lj Lu Mj Nb Ne Ni Pe Pg) Nq(Ma Md My Mz Ne Ni Nr Ny Pe Pz) Ma(Im In Ir Jk Lh Nn Nr Ny Pe) Qe(Mh Ng Ni Ny Pc Pz) Hv(Jh My Ny) Nr(Jk On) Js(Im On)} Mx{Nb(Hu Hv Ij Jh Jm Jo Ma Mg Mn Mv Nm Nx Ny Oy Qa Qd) Qe(Ih Ik Ip Iv Jk Jr Mg Mt Mw Nq Nw Of Oz Pb Qb) Ir(aA Ih In Is Jq Lu Md Mj Ng Oi Pz Qb) Jh(Hv Iv Ma Nr Oe Oi On Pz Qa) On(Hu Ij Jt Lu Lv Ml Nm Nx) Mv(Is Lv Ml Ng Ni Pz) Mj(Hv Is Iv Ny) Mw(Im Ma Ms Ni) Ij(Hu Im In) Is(Ii Iv Lv) Nr(It Jk) Im(Js Og) Pz(Hu Iv) NqMs} cW{aK(aF aG aI aX aY aZ bG bX bZ cQ cU cZ dA dG dI dM) aG(aF aN aZ bB bM cR cU cX dC) bG(aH aN aX bW bX cQ cS cU) cE(aN aZ bB cB cC cS cV cZ) cF(aY cI cM cN dD dM) cR(aH aL aX bW dB dK) aN(aA aH aL bV cG) cC(aX aY bH cQ cS) bW(aS bL cD dB) aI(cZ dD) aL(bE dA) bX(cD cO) cU(cG cS) dK(aC cN) aOdD aWdB aXbL aYaZ bBbZ} Hv{Mv(Fp Hx In Ir Jh JI Jm Lx Ml Na Nb Nw Ny Oz Pa Pg) Pz(It Jj Jo Lv Lx Mh Mj Mk My Ne Nh Oe Og Oi Oy Qe) In(Ik Jh Lz Mc Mj Ml My Ni Ns Pc Pd) Ma(Iv Jh Md Mh Mk Ml Nn) Jh(Hx Ij Ir Oe Oi) My(Lj Lv Ml Na) Ny(Jn Js Ne Nn) On(Js Jt Mt) Mw(Md Na) Nd(Me Mh) Ni(Jk Om) Ii(No Qe) LvNx IrOf IsJs QaQe} cC{cF(aH aK aO aQ aV aX bH bL bM bN bQ bU cD cH cL cO cQ dJ dK) cS(aL aN aQ aU bE bJ bZ cA cE cL cR cX cY dA dG dL) aN(aL bN cE cG cV dF) bX(aK aY bV cE dG) cR(aK aO bO cJ dB) aY(bM bU cL) bZ(aZ cP cX) aD(bV cQ) bM(al aX) aUbJ bUcP} dB{aW(aH aO aP aU aZ bG bX bZ cL cP cS cX dA dG) cS(aK aY bB bJ bN bR cB cP cU cX) cR(aG aU bN bW cM cP dJ dK) aN(aA aK bJ bZ cF cV dG) cX(aA aK aL aY cG dF) aK(bJ bM cB cL) bJ(bZ cI dK) aZ(aH cV) bW(aD dM) bX(cO dG) cPdK} Ij{Ni(Fp Hu Ih In Jh Lz Ml Mv Nj Pb Pc Qb) Mv(Ii Ir Iv Me Mk Nb Nj Nt Nv) Na(Hw Ir Mk Og Qb Qd) Hu(Hw In Ma) Js(Mk Qd Qe) It(Iv Pz) Qb(In Nb) On(Mz Ok) NnQe HxPz IrOg JhNv} Bg{Cw(Aj Ar Ax Bc Ch Cq Ct Cv Cx De) Cs(Af Al Ap As Ch Cu De) As(Bc Cx Db De Ex) Ax(Al Ar Bb Ch Ct) Db(Ap Ar Cx Gl) Ef(Ad Co Ex Fp) Bo(Ad Co Ex) AjDl ApaA CuDi} Js{Ir(Jm Lx Ma Nd Ne Nj Ny Pe Qa Qd Qe) Im(It Jm Ma Md My Og) Pz(Is Mh Mw Ne Nq Oy) Nr(Jk Mn Mp Nm) Is(Iv Jh Md) On(Ii Mh Ml) Ni(Io Qe) NmMv NbII QdLj QeJh} Og{Ir(Hx Ik Il It Ji Lu Ma Mp Ms Mt Mz Na Nb Nw Pg Qb) Qe(Ii Mh Ml Ms Mz Nn Oe Pz Qb) Ni(Hr Im Iu Jk Lj Ly Nq Qd) Pz(Hw Mh Ms) NqMs MhQd} Co{Bo(Af Aj An Ap Bb Bc Bn Cu Cv Db Dl Gl) Ao(Ad Ar As Dd Dg Fp Gl) Cx(Aw Cv Db De Di Dk Fw) Bc(Aw Dc Di Fp) Cv(Af Ba Bn Cq) Fw(Ba Ef) AdAx} Ii{Mv(Ip Is Lw Lx Mi Ml Mq Nb Nd Nm Nr Pz) Jh(Lx Ma Mh Ml Ne Oe Oi Qa) Jk(Iv Lj Ma Nr Oi Po) Qe(Hu It Pz) On(Mz Nw Nx) Of(Mi Nw) NaIr} aD{cR(aA aJ aN bZ cN cO dD dI dK) cZ(aH bF bG cE) aN(aX cS dA) bZ(bE bW dA) cS(bL bR) dK(bH cD) aHaX aLdA bEbF} Ax{Aw(Al Ao Bb Bn Cv Cx De Dg Di Dl Ef) Cp(Ad Aj Ar Db De) Ef(Aj An Cs De) Al(Bo Cs) AjBa ChCs DbDk} Bo{Ct(Af An As Bn Cq Cw Db Dd De Fp) Cq(Cx Fw) Cv(Ba Cx) Ef(De Di) Ex(Ap Cp) AlDb AoFw} cS{bL(aH aI bJ bM bX cF cU dA dC) dC(bE bW dA) aU(aK aQ) bX(bU cD) cR(bQ cF) aHbB} Db{Dk(Af Bc Bn Cs Cx Di) Aw(Bc Cs Fw) Cp(Af Bn Fw) Cx(Dc Dg) AfCq BbBn BcDd CwFw} bZ{bM(aX bF cD dI) bN(aZ cP cR cX) aZ(aY cX) cZ(aQ cF) dC(aU dG) aOdA bUbX} Iv{Ne(Il Jk Mv My Nr) Na(Il Ma Mv Nr) In(Mv Nq Pz) NqMv MyIl} Fw{Cw(Af Aj Bc Cp Dc Di Ef) Cu(Ad An Ao Ar As)} Nr{It(II Is Jk Ne Pe) Mv(Ir Ni Pz) NqNi NaIp} cF{cX(aA aJ aX dJ) cD(aA aJ bW) bH(cZ dC) aXbU} Ex{Ap(Al Aw) Ba(Bb Fp) Bc(Ch Cp) AfDk ArCp CxDg} dC{dA(aY bF bG cE dK) dG(bF bG cR) bGcZ} Cs{Cp(Aj Ar Fp) Aw(Aj Bn) AoEf ArBa} Cx{Ba(Cq Cv) Cp(Af Cw) AoEf BnCq CvCw} Mw{Ma(Ms Na Nn) Ms(Nn Nq) Jn(Ml Pz)} Il{It(Im Ir Nb Qe) NaIr JhOe JtOn} Mt{Jh(Oe Oi Qe) LxNa JtOn} Ni{Jk(Mh Mj) NdOf JtOn} Nv{On(Jt Nq Ny) JhPa} cX{aL(bW dG) aAdK bXdF} Cv{Ba(Dd Dl) AwBn} Ir{NoMv MgJt OeOy} Is{LwJq NbJr QeOy} Of{Mj(In Nb) HwPz} aQ{cZ(bF bG) aNbN} Ao{Cw(Al Ch)} Jk{MhIm ItLj} AnAwBc MdJhOi PzQeJt aLaNbN aYcLdL Unconstrained panels with 3 analytes, where 1.0E-5 >= 'AUC p-value' > 1.0E-6. Contains 10,474 panels of 409,920 total panels evaluated. :
Pf{Qa(aA Et Fr Hq Hr Hu Hv Hx Ik Il Im In Io Ip Iq Jg Jh Jj Jk Jl Jm Jn Jo Jp Jq Jt Li Lj Lu Lw Lx Ma Mb Mc Md Me Mf Mg Mh Mi Mm Mn Mp Mq Mt Mv Mz Nb Ne Nf Ng Nj Nm No Nq Ns Nu Nv Ny Of Oi Ok Om Oz Pa Pb Pc Pd Pz Qd) Ik(Et Fr Hq Hu Hw Hx Ih Im In Io Iq Ir Is Iu Ji Jj Jk Jl Jm Jo Jp Jr Lw Lx Ly Ma Mc Me Mg Mh Mi Mk Mm Mn Mq Ms Mt Mv Mw My Nb Nd Ne Nf Ng Nh Nj Nm No Nq Ns Nv Nw Nx Ny Of Ok Om On Oy Oz Pc Pd Qc Qe Wm) Mc(Et Fr Hq Hu Hv Hw Hx Ih In Io Iq Ir Iu Iv Jg Jh Ji Jl Jm Jp Lv Lw Lx Ly Ma Md Mg Mh Mi Mk Mm Mn Mq Ms Mt Mv My Mz Nb Ne Nf Ng Nh Nj Nm Nq Ns Nu Nw Nv Of Og Ok Om On Oy Oz Pa Pb Pc Pd Pz Qe) Lj(Et Hq Hr Hu Hv Hw Hx Ij Il Im In Ip Iq Ir Iu Iv Jg Ji Jj Jk Jn Jp Jr Li Lw Lx Ly Md Me Mi Mm Mn Mp Mq Mt Mw Nb Nd Ne Ng Nh Nj Nn Nq Nr Ns Nv Nw Of Og Ok Om On Oy Oz Pa Pc Pd Po Pz Qc Qd Qe) Mm(Et Hq Hr Hu Hw Hx Ih Im In Io Iq Iu Jg Jh Jk Jl Jm Jp Jr Jt Lv Lw Lx Ly Ma Mb Md Me Mf Mh Mi Mk Mq Ms Mt Mv My Mz Nb Nd Ng Nj Nm Nq Ns Nu Nv Nw Ny Of Og Ok On Oy Oz Pb Pc Pd Qc Qe) Nf(Et Fr Hq Hr Hu Hv Hx Ih Im In Io Ir Is Iu Iv Jg Jh Jj Jk Jl Jm Jp Jt Lu Lv Lw Lx Ly Ma Mb Md Mf Mg Mh Mi Mn Mp Mq Ms Mt Mw Mz Ng Nn Nq Ns Nu Nw Nx Ny Of Om On Oy Oz Pc Pz Qd Qe) Hq(Et Fr Hr Hu Hv Hw Hx Ih In Io Iu Jg Jk Jl Jm Jp Jr Jt Lv Lw Lx Ly Ma Md Mg Mh Mi Mk Mn Ms Mt Mv My Mz Nb Nd Ne Ng Nj Nm Nq Ns Nu Nx Ny Og Ok Om On Oy Oz Pa Pb Pc Pd Pz Qd Qe Wm) Ih(aA Et Fr Hu Hw Hx Iq Iu Jg Jh Ji Jj Jl Jm Jp Jr Jt Lu Lv Lx Ly Ma Md Me Mf Mh Mi Mm Mp Mq Mr Ms Mt Mv My Mz Nb Ne Nh Nj Nm Nn Nq Nu Nv Nx Of Og Ok Om Oy Oz Pc Pd Po Pz) Nm(Et Hu Hw Hx Im In Io Ir Iu Iv Jg Jh Ji Jj Jk Jl Jm Ju Lv Ly Ma Md Me Mf Mh Mk Mn Mq Ms Mt Mv Mw My Nb Nc Ng Nh Nj No Nq Ns Nu Nv Nw Ny Om On Oz Pb Pc Pd Pz Qd Qe) Lw(Et Fr Hr Hu Hv Hx In Io Ir Iu Iv Jg Jh Jj Jk Jl Jo Jp Lv Ly Ma Mb Md Mf Mh Mi Mk Mn Mp Ms Mt Mv My Nb Ne Ng Nh Nj Nq Ns Nu Nx Ny Of Og Oi Om On Oy Oz Pb Pc Pz Qe) Om(aA Fr Hu Hv Hw Hx Im In Io Iq Ir Iu Jh Jj Jk Jl Jm Jr Lv Lx Ly Ma Me Mf Mh Mn Mq Ms Mv Mw My Mz Nb Nd Ne Nh Nj Nq Ns Nu Nw Nx Ny Of Og Ok On Oy Pb Pc Pd Po Qe) Jg(Et Hu Hx Im Io Ir Iu Jh Jj Jk Jl Jm Jt Lv Lx Ly Ma Me Mf Mh Mi Mk Mn Mp Mq Mr Mt Mv My Mz Nb Ne Ng Nh Ni Nn Ns Nw Nx Ny Og Oi Ok On Oz Pb Pc Pd Pz Qc Qd Qe) Oy(Et Fr Hr Hv Hw Hx Il Im In Iq Ir Iu Iv Jh Jj Jk Jl Jm Li Lv Lx Ma Md Mi Mq Mr Ms Mt Mv Mw My Mz Nd Ne Ng Nh Nj Nn Nq Ns Nu Nv Nx Ny Ok On Pb Pc Qd Qe Wm) Io(aA Fr Hr Hv Im In Iq Ir It Iu Jh Ji Jj Jl Jm Jp Jr Lv Lx Ly Md Me Mf Mi Mk Mn Mq Ms Mt Mz Nb Ne Nh Nj No Nq Nr Ns Nu Nv Nx Ny Og Ok On Oz Pb Pc Pd Qe) Mv(Et Fr Hu Hx Ij Il Im In Ir Iv Jh Ji Jj Jl Jm Jn Jp Lh Li Lv Lx Ly Me Mf Mg Mi Mw Mz Nd Ni Nj No Ns Nu Nw Nx Ny Og Ok On Oz Pa Pb Pc Pd Pz Qc Qd Qe) Mh(Hr Hu Hv Hw In Iq Iu Jh Jj Jl Jm Jn Jo Jp Jr Lv Lx Ly Ma Mb Me Mf Mn Ms Mt My Nb Ne Ng Nh Nj Nq Ns Nu Nv Nw Ny Of Og Oi Ok Oz Pa Pb Pc Pd Qe Wm) Mg(Et Fr Hr Hu Im In Ip Iq Iv Jh Ji Jk Jn Jo Jp Jr Jt Lu Ly Mb Md Me Mf Mi Mk Mn Mp Mq Mr Ms Mt Mw Nd Nh Nn No Nq Nv Nw Nx Oe Og Oi Pc Pd Pz Qc Qe) aA(Et Hu Hv Il Im Ip Iq Ir It Iu Iv Jh Ji Jj Jk Jl Jr Lh Li Lz Mb Mf Mi Ml Mn Mp Mq Mr Mz Nd Nh Ni Nj Nn Nt Nu Nv Nx Ny Of Og Oi Pa Pe Po Pz Qc) Mt(Et Hr Hu Hv Im Iq Ir Is Iu Jh Jj Jl Jm Jo Lu Lv Ly Md Me Mf Mi Mn Mq Mr Ms Mz Nb Ne Ng Ns Nv Nw Nx Ny Of Og Ok On Oz Pa Pb Pc Pd Po Qd) Lx(Et Hr Hu Hx Il Im In Iq Ir It Iu Jh Jj Jl Jm Jo Jp Jr Lv Ly Ma Md Me

Bg) Mm(Hw Mw) Mr(Lj Ma) It(Lj Oe) AxEf BaDi CoCx CuFw MeNe MgJt MjIn NaIh NbJg IsaA QbOi} Qc{Mh(aA Fp Hr Hv Hw Ij Ik Io Ip
Iq Ir Is It Iu Iv Jl Jm Jn Jo Jp Jr Li Lu Lv Lw Lz Ma Mc Me Mi Mj Ml Mm Mn Mp Mq Mw Mx My Mz Ne Nj Nm Nn No Nq Nr Ns Nt Nx Ny
Oh Oi Ok Om On Oz Pa Pb Pd Po Qa) Jh(aA Fp Hr Hq Hu Hx Ih Ij Ik Il Ir Is It Iv Ji Jj Jk Jl Jm Jp Jq Jr Lj Lv Ly Lz Mc Mf Mg Mj Mm Mn Ms Mv
Mw My Nb Nf No Nq Nw Ny Of Og Om Oy Pa Pe Qe Wm) Mu(aA Fp Hr Ih Ii Ij Im Io It Jj Jk Jl Jm Jn Jo Jr Js Jt Lh Li Mm Mp Mq Mr Ms Mt
Mw Mx Nb Nf Nj Nm Nq Ns Nu Nw Oe Og Oi Om Pe Po Qa Qd Qe) Nl(Fp Hr Hw Hq Is Iu Iq Iu Jl Jm Jo Jp Jr Lj Lw Lx Ly Lz Ma Mc Mf Mj
Mk Ml Mm Mp Ms Mt My Nd Nf Ng Nm Nt Nv Ny Ok Om On Oy Pd Po) Pc(Hq Hr Hu Hw Hx Ih Ii Il Io Ip Ir Iu Jg Jk Jm Jt Lv Lw Ly Ma Mc
Mj Ml Mp Ms Mw Nd Nu Nv Nw Nx Oe Of Ok On Pg Pz Wm) Ni(Et Iq Ir Jg Jj Jo Jp Jq Lh Lj Lu Lv Lz Ma Mc Me Mk Mm Mp Ms Mv My
Nb Nd Nq Ns Nu Nv Nx Ny Oe Om Pd Pe Po Qe) Ne(Et Hq Hu Ih Ij Im It Jn Js Li Ma Md Mg Ml Mv Mw Mz Na Nb Nh Nq Nr Nx Pa Pe Qb
Qd) Nk(Hq Ik Il Im In It Iu Jg Jj Jn Ma Md Mg Mx Nh Nq Nr Ny Of Oh Pb Pe Qb) Li(Fp Hq Hr Hv Hw Ih Io Jn Jr Jt Lv Mb Mg Ml Ms Mx Nb
Nn Nv Oi Oz Qa) Mv(Hq Hv Ij Io Iu Js Jt Lh Lj Lv Mj Mr Mx Mz Oe Oi Oz Pb Pz Qa) Mz(Hq Hx In Io Lx Ma Md Mg Mi Ml Mw Na Nq Nr Pg Qb Qd) Hv(Hq Hu Hw Ii Io It Jm Js Lv Ma Mk Ml Mx Nn Nq Pg) Qb(Ij Il Im Ir Lj Lv Ly Mb Mg Nq Pe Pg Pz Qe) Nb(Hr Ih Il It Jn Jr Mj Nr Of Pg Pz Qd) Ii(Hu Il Jg Ma Mi Mq Nm Of Ok On Pe Po) Mx(Is Lj Ma Mg Mw Nn No Nq Oh Pe Po) Hq(Hx In Jm Js Jt Md Na Nv Oh Qd Wm) Pz(Et Il In Is Ji Jm Jr Lv Ny Oh Oi) Js(Ij In Is Iv Lv Lx Mb Mg Mj No) Ml(Hw Ih Lv Mc Mw Na Nq Og On) Na(Im Lx Mb Md Mg Nh Of Oh) Ma(It Jt Mf Mr Nn Pg Qa) Oh(Hw Hx Im Lx My Nn Ny) Wm(Fp Ij Mw Og Oi Qa) In(Ij Iv Lv Mj Qd) Og(Im Ir Mb Ms Oe) Nq(Jm Mj Mt Qd) Mg(Mb Mw Nn Nr) It(Il Iv Lj Mb) Mw(Ms Nn Qd) Hu(Hw Iu Oi) Im(Ih Jt Nt) Of(Hw Oi) NnIj NrNt LvPg MbOi MkQd IhLj JqOk} Li{Nk(Hx Ik Iu Iv Jg Ji Jl Jm Jn Jo Jq Jr Js Jt Lw Lx Ma Mc Mf Mg Mm Mr Ms Mw Mz Nb Nd Ne Ng Nm Nn Nq Nt Nu Nv Ny Oe Oi Om Oy Pb Pc Pd Pe Qd) Ni(Hq Hr Hu Hw Hx Ih Ik Il Io Ip Iq Is It Iu Jh Ji Jn Jp Jq Lv Md Me Mg Mm Mn Mp Mr Ms Mw My Nb Nd Nf Nh Nj No Nu Nv Nw Om On Oz Pg Pz) Pz(Fp Hu Il Io Iq Ir It Iv Jg Jh Ji Jq Lh Lz Mb Mc Md Me Mf Mg Ml Mp Mr Ms Mw Mz Ne Ng Nh Nm No Nx Ny Ok Om On Oz Pc Pd Pg Qa Wm) Na(Hq Hu Ij Ik Im Ip Ir Is It Jg Jh Jj Jk Jm Jq Lh Lu Lv Mb Md Mp Mr Mu Mw Nh Nj Nl Nn Nq Nx Of Og Ok On Pb Po Qa Qe) Ii(Fp Hv Ik Im Io Iq It Iu Iv Jg Jn Jp Jq Jr Js Lh Lj Lv Lx Mb Mc Mf Mm Mp Mq Ms Nf Nh Nl Nn Nq Ns Nu Oe Og Oy Pb Qa) Qb(Fp Ij Ik Il Io Ir Ji Jk Jl Jm Jp Jq Lz Me Mj Ml Mm Mp Mq Nd Nf Ng Nj Nm Nn Ns Nx Ny Oh Oy Oz Pe Qd) In(It Jh Jj Jn Jr Lh Lx Md Ml Mr Ms Mt Mz Ne Nf Nh Nj Nm Nn Nv Oe Of Og Oy Pg Po Qa) Mu(aA Et Ih Il Ir It Ji Jt Lh Lu Lv Mb Me Mk Ml Mm Mp Mr Nh Nn Nq Nt Nw Oe Of Oi) Ma(Fp Ir Is It Iv Lh Lu Lx Lz Mf Mp Mr Ms Mt Mx Nb Nv Nw Oz Pb Pc Pe Pg Po) Nl(aA Im Is It Jm Jo Jp Jq Md Mg Mj Ml Mp Mv Nb Ne Nn Nq Ns Nx Pa Pb) Lv(Hr Ip Jn Jt Lh Lx Md Mt Nd Nn Nw Og Oy Pb Pe Po Qa) Mn(Et Fp Ih Ji Jn Jq Lu Lz Md Ml Ms Mt Nn No Pe) Hq(Et Fp Hx Ih Iq Iv Jn Mt Nd Nh Nt Oi Pb Pe) No(Il Im Jg Jh Jk Jp Nb Nq Nx Ok On Pg Qd) Jh(Hv Md Ml Mp Mt Mw Nn Nt Oc Og Oi Po) Pg(Fp Ih Il Ji Jn Jq Ml Mp Oi Pe) Lu(Lz Ml Ne Nm Of Og Oh Oy Po) Nn(Is Jk Jp Mv Mw My Nx On) Nr(Hv Ih Il Lh Mt Ne Nv Qa) Mx(Il Ir Is Jg Mw My Nq Of) Oh(Fp Iq Lz Mb Md Mm Mz Nm) Mv(Hv Ih Ir Mf Mp Mt Of) Il(Fp Ji Js Ml Ne Wm) Nv(Ip Jk Mj My Nx On) Oy(Ir Ms Nb Oi Pd) Js(Im Ir Qd Qe) Of(Hw Jq Lz Ml) Jn(Is Mj Nq) Oi(Hu Jk Nx) Fp(Me Nb) Mk(Jo Mg) Ih(Ir Mj) Jt(Is On) aA(Im Ml) WmIt MeHv MpOn MsNg HuOe JiOk} Nl{Jh(Et Fp Hq Hx Ih In Io Iq Ir Is Jg Ji Jj Jm Jo Jp Jr Jt Lh Lv Lw Lx Ly Lz Mb Mc Mg Mi Mk Ml Mn Mq Mr Ms Mv Mw My Na Nb Nd Ne Nf Ng Nk Nm Ns Nt Nu Nw Nx Ny Oe Og Ok On Oy Oz Pb Pc Po Qa Qb Qe) Pz(Hq Hr Hu Hw Ih Il In Io Iq Ir Is It Iu Jl Jn Jp Jr Lh Lj Lv Lw Lx Ly Lz Ma Mc Mf Mm Mn Mp Mr Ms Mz Nf Ni Nm Nn No Nr Ns Nt Ok On Oz Pb Pd Qa Qb Qd) Mv(aA Fp Hu Ik Il Im In Ir Is Iu Jg Jk Jl Jn Jq Js Jt Lj Ly Ma Mb Me Mf Mj Mm Mr Mu Mw Nh Ni Nk Nn Nq Nr Ns Nt Nu Nx Of Og Oi Om) Hu(aA Et Hw Hx In Io It Iu Ji Jp Lh Lj Lw Lx Me Mg Mj Mm Mw My Mz Nd Nf Ni Nj Nk Nm Nn Nq Ns Nw Ny Of Og Ok Om On Pc Pd Pg Qd) Jk(Fp Hr Hw Ih Ir Jg Jl Lu Lz Md Mg Mj Mt Mu Na Ne Nk Nn Nq Nt Nx Ny Oe Oi Om Oy Pa Pc Pd Pg) Jg(Im In Ji Jn Ma Mf Mh Mj Ml Mr Mu Nb Nd Nf Nh Nn Nq Nw Nx Oe Of Ok Om Oy Pa Pc) Ij(Et Hw Il Im Ir It Lu Lz Ma Mb Md Me Ml Ms Mu My Nk Nn Nt Pe Pg Qb Qe) Nh(Hv Ii Ip Iv Lh Lv Mg Mt Mu Mx Nd Nf Nq Nr Ns Og Pa Pc Pe Pg) Of(Hr Hv Hw Il Lh Md Mg Ml Mw Mx Ne Nj Nk Nq Ns Nt Pa Pd Qd Qe) Ik(Il Im In Jl Lh Lu Lv Mj My Nb Ni Nt Nv Nx Oe Pe Pg Qa Qd) Mu(Ih Im Lj Lu Ma Md Mg Mh Mx Nb Nx Ny Pd Qe) Wm(Hw Is Jn Jo Lj Me Mi Mp Ne Nj Nq Nx Po) Il(Im Is Jl Lv Mi Mw Nr Nx Ny Pe Pg Qa Qe) Nr(aA Hv Is Js Mi Na Nb Nj Pd Pe Pg) Iv(Im Lu Ma Md Mg Ns Nx Ny Pe Pg) On(Hv Im Md Mx Mz Ni Nw Og Oh Pe) Nq(Jn Lv Mp Mt Ni Ns Pa Pe Pg) Lu(Ir Lw Lx Mq No Ok Pa Pe) Hv(In Ir Is Mw Pe Qd Qe) Is(Im Mt Mx Og Pa Pg) Lv(aA Ma Mw Ng Pe) Nb(Jj Mg Ng Og Pd) Ir(It Md Mx Ng Pa) Qe(Ii Js Nj Oh Pc) Pg(Mw My Ni Qa) Im(Mx Ne Nj) Nx(aA Md Pe) Mg(aA Ne) Ni(Pa Pe) Og(Lx Nt) Oh(Lh Qa) Pc(In My) MsMw} bA{cS(aD aF aJ aR aS aU aW aX aY bH bI bM bO bR bS bW cA cD cI cJ cK cL cN cR cT cU cV cW cY cZ dG dI dJ dL dM) cQ(aC aH aL aR aS aV aW aX aY aZ bB bC bI bQ bR bS bW bX cA cC cI cJ cL cM dC dD dJ) cW(aC aD aE aO aV aX aY bB bE bF bM bQ bR bU bW bZ cA cD cE cG cJ cM cN cO cU cY dF) dC(aD aE aH aI aO aP aS aU aV aX bI bM bN bO bS bV bX cA cK cN cT dH dL) aA(aQ aR aS aU aV bC bH bI bN bV bW cA cB cH cI cR cT cU dF dG dJ) aD(aC aL aO aU aV bC bI bJ bM bU bZ cA cI cL cU cV cY cZ dF dG dJ) aN(aG aQ aS aU aV bJ bM bP bR bS bU bW bZ cD cI cK cL cR cZ dL dM) bL(aH aK aL aO aQ aS bE bZ cA cC cI cK cP cY cZ dA dD dF dG dL) dN(aI aL aS aY bB bE bM bO bP bQ bV cD cF cL cU cZ dB dJ dK) bZ(aG aO aR aS aY bH bN cA cC cE cH cL cM cU dH dI dJ) aZ(aH aO aR aU bC bE bO bQ bV cB cE cF cR cV cX dA) bG(aI aQ aU bH bJ bM bQ bX cB cU cV cZ dF dH dI) aE(aF aP aS bU bW cD cM cN cU cV cZ dB dD dJ) bP(aC aL aS aU bH bQ bV cA cN cR cU dA dF dI) cC(aC aF aK aU aX aY bF bH bO cG cH cV dK dM) cF(aJ aK aU aV aY bB bE bM cA cL cU cZ dD dI) dH(aQ bF bJ bN bU cB cE cH cM cT cY dF) bN(aX aY bH bV bX cB cE cL dA dM) bF(bH bQ bX cA cE cH dI dJ dL) bV(aH aI aW bB bJ bO cN cU dL) bI(aJ aS bQ bX cA cB dI) bO(aU bR cE cH cI cR dI) cL(aK aW bH cD dB) aU(aQ aW cH dM) bM(aK aR bE dG) cX(aY cG cM dD) dB(bJ cN dM) aP(aF bQ) aX(aQ dA) cE(aW cV) dM(bW dL) aOcR aYcG bEbJ bQbX cHdF} dN{aY(aI aO aR aS aU aW bB bF bM bO bR bS bU bV bW cA cB cE cG cH cI cJ cK cN cV dC dF dG dI dL dM) cD(aA aC aP aQ aV aX bB bC bE bI bN bQ bS bU bV cB cG cJ cK cN cU cV cY dC dF dG dI dJ dM) bL(aA aE aV bC bE bI bM bN bR bS cA cB cI cJ cK cN cQ cZ dB dC dG dJ dK) dB(aA aF aJ aQ aR aU aX bP bU cF cI cL cW cY cZ dC dD dF dH dK dM) aG(aF aO aP aQ aX bB bE bO bR bS bW cA cF cJ cK cM cU dH dI dK) cO(aA aF aJ aP aR aW bC bE bJ bM bV cA cI cJ cP cT dA dG dL dM) aH(aA aD aO aP aX bB bC bI bM bR bS bV cJ cK cP cS dC dH dI) aM(aF aO aQ aU aW bI bJ bM bP bQ bR bW cF cV cY dF dG dI dJ) bG(aJ aP aQ bB bJ bS bU bV bW cA cF cH cI cK dF dH dJ dL dM) bH(aR aW bI bP bS bU bV cA cB cG cI cK cQ cU dD dF dG dL) bF(aA aE aL aR aX bC bI bW bX cG cH cS cY dC dF dI dK) cE(aA aD aQ aX bE bN bO bQ bS bU cA cI cK cW dI dL) cL(aD aQ aR aW aZ bJ bM cF cG cI cS cW dF dJ) cX(aA aI aQ bB bC bI bN cF cI cS cZ dC dH dJ) aK(aS aW aX aZ bJ bM bN bQ bX cW dH dI dJ) cH(aA aF aL aQ aX bZ cB cF cG cV dD dG dJ) cS(aD aS aV bJ bM bN bO bV cU cW cY dD) cT(aD aV bC bJ bN bP bX cM cW dC dM) bP(aD aE aI aO aQ bB bQ cV) dL(aS aV bC bJ bU bW cW cY) aE(aC aI aW aZ bQ) aS(aZ cF cW dD dI) aD(aR aW cM) aX(aL bZ dJ) aZ(aR bB cG) bZ(dJ dK) cF(cM dJ) dF(aP cV) aFaL aNdD aRcW bBbX bQcM} Mu{Il(Et Fp Hx Ih Ik Ip Is Iu Ji Jk Jl Jm Jo Jp Jr Lh Lx Lz Mg Mr Mt Ng Nh No Nu Nw Nx Ny Og Oi Oy Oz Pc Pe Pg Po Qa Qd Qe) Hv(Hq Ik Ip Iq Ji Jj Jm Jn Jo Jq Jr Lx Lz Me Mg Mp Ms Mv Mz Ne Nj Nm Nn Ns Nu Nv Nw Ny Of Pc Pd Pe Po Qb Qd Qe) Iv(aA Fp Hq Hu Hx Im It Jg Jk Jo Js Ly Lz Me Mf Mh Mj Ml Mm Mt Mw My Ng Ni Nn Nu Nv Oe Of Oh Pd Pe Pg Pz Qb) Ir(aA Ih Ik Im It Ji Jl Jn Js Jt Lh Ma Md Mf Mg Mh Mp Mw My Mz Ne Nh Ni Nn No Nr Nt Nw Ny Oe Pc Pg) Nk(Hu Ik Im Is Jg Jl Jo Lu Ly Ma Mb Md Mf Mg Mm Mn Nb Ng Ni Nq Ny Pc Pd Pe Qe) Ml(Io It Jh Jk Jm Jn Jr Lj Lu Md Mk Mv Na Nf Nh Ni Nr Ny Oh On Pa Pg Pz

Figure 26 Continued

Figure 26 Continued

Nh Of Pc Qe) Jk(Iv Jn Jt Ly Mi Mj Mt Na Nb Ng) Nb(Hq Ij Js Ma Mg Nu) Of(Ip Ir Mq Nf On Po) Ip(Ii Il In Na) Jo(In Iv Nf Ni) Nt(Lh Mi Om) Lu(Lw Mi Ok) Ma(Ih Mt Nr) Jg(Ih Il Jn) Js(Jr Nm Qe) Oi(Hq Na Oe) Nq(Iv Na) Me(Ij Om) Mn(Et Jn) Mt(On Qe) Pg(Mf Mi) PoLj LvJr MgJn IjIv llOn} bP{bZ(aC aF aI aS aV bB bE bF bH bl bO bS bU bV bW cA cB cC cD cE cG cH cI cJ cK cN cO cQ cR cV cX cZ dF dG dH dK) aK(aA aC aH aJ aR aV bB bE bl bJ bO bR bS bU bV bW bX cB cD cI cJ cK cN cO cQ cR cU cY dA dD dH dL dM) aL(aG bB bF bG bJ bM bQ cC cE cH cJ cM cV cZ dC dF dG) dF(aG aH aW aY bG bU bX cD cJ dB dH) cF(aO aU aV aZ bB cB dA dL) aY(aS aX bF bH bN bO cM) cC(aS bC bX cE cG cP cY) aD(aG bQ bV cE cO) bF(bC bU bX cZ) bG(bC bV cY dG) dB(aW bH bQ cR) aS(bL cM) cG(aZ cR) cP(aF dK) cS(aH cY) aUaX cEcM} Gp{Bo(Af An Ao Ap As Ax Ba Ch Cw Db Dc Dk Dl Gl) Cw(Ad An Ao Ap Bn Ch Co Ct Dc De Dl Fp Gl) Aw(An Ao Ba Bb Bg Co Db Dg Di Dk Dl Ef) Co(Ad Aj Ax Bg Ch Cq Cu Cv Dk Fw) Ef(Ad Aj Ar Ax Ch Cs Cu Cv De Dg) Ap(Ar Bn Cs Dd Dg Di Ex Fp Fw) Al(Bb Bn Cu Cx Db Dc Dk Gl) Bg(aA Aj Bb Cq Dd Di Dk Fp) Ba(Af Ao Ar Cs Db Dd Dl) Bc(Af Ao Cq Cx De Dg Dk) Bn(Ao Bb Ch Cq Dc De Fp) Cu(Ao Ar Ax Cq Cs Ct Gl) As(Ct De Fp Fw) Ax(Cs Ct Db) Cv(Ad Af Dl) Dg(Aj An Fp) Dk(Ao Db Di) Cx(Ch Cs) Gl(Aj Ct) AdAf BbDb DcaA} dB{aW(aC aF aI aK aV bB bH bL bM bN bO bQ bR bS bV cC cD cG cH cK cO cQ cV cY cZ dC dD dF dK dL dM) cR(aH aL aN aO aQ aZ bB bC bI bJ bL bR bU cA cB cI cJ cO cS cU cV cX dA dC dG dH) cS(aA aD aO aZ bE bF bH bL bU bX cC cF cQ cZ dA dC dG dH dL) aN(aJ aL aS bC bF bN bQ bW cH cI dF) cP(aH aI aY bF bG bQ bZ cE cF) aZ(aK aU bQ cE cG cI cO dG) aD(aG aK bH dA) bZ(bF cG cU cZ) cX(aF aO aS cI) aK(aF aP) aY(bJ cV) bH(bJ bM) bW(aL bO) cF(aH bN) cZ(aI cE) bXdF cLdG} Ij{Ni(Hr Ik Il Iq Jl Jr Lw Mc Md Mf Mg Mi Mm Mn Mq Ms My Mz Nb Nd Ng Nh Nm Nn No Nq Nr Nt Nx Of Ok On Oy Pz Qe) Mv(Et Fp Hq Hr Ik Il Io Ip Jh Jm Jn Jo Js Lh Lu Mb Mf Mh Mi Mn Mw Na Nd Ng Nh Nw Oe On Oz Pc Pz Qa Qb Qe) Jh(Hw Ii In It Lv Md Mh Mj Ms Mw Na Ne Nn Nu Pz Qb) Na(Hu Iq Lv Lz Mi Ml Mw Nb Nq Nr Oi On Qe) It(Hu Hx Im Ir Lu Mk Og Qe) Pz(Hw Jr Js Ne) On(Et Hx Jn Jt) In(Mj Of) MkHx MsMw NeHu IhIr IvJs} cC{cS(aD aF aG aH aI aO aS aV aW aX aZ bC bF bG bI bL bM bW cG cH cK cN cO cP cV dF dH dJ dK) cF(aI aL aR aZ bB bC bF bG bO bR bS bX bZ cA cG cJ cK cY dC dD) cR(aG aI aJ aL aN bH bM bU bZ cP dG dK dL) cP(aH aI aL aN bM bO bX cJ dF dJ) bJ(aK aY bZ cG cJ cY dF) bX(aG aH aQ bW cG cV dA) aN(aA aQ aU aW bV) bM(aL bW bZ cQ dI) bW(aK bN bU bZ) dG(aD aW cM cX) aD(aG cE) aJ(aK aW) aY(aZ dK) cX(aA dH) aKaP cEcV} Js{Ir(Et Hq Hr Hw Hx In It Iu Iv Jg Jj Jn Jo Jr Lh Lu Mf Mh Mj Ms My Mz Na Nb Nf Ni No Ns Nu Nx Ok Om Qb) Im(aA Io Jh Jk Jr Lw Mg Mi Mm Mn Mv Ng Nj Nm Of Oy Qa) Pz(Jj Jp Ml Mv My Nb Nj No Nr Ny Og On Pe Qd) Qe(Hu Is Lj Mh Mv Nm No Of Og On Oy) On(Il Ma Md Mm Mz Nb Og Pe Qa) Is(Hu Lj Ml Mv Nb No Pe) Qd(Ma Mg Mh Nm Nr) Jk(Ma Mh Ml Pe) Nr(Iv Jh Mi) Mv(Lj Ma Mk) Qa(Jh Ma) MnNi LjOf} Ii{Mv(Il It Ji Jj Lj Lv Ly Mg Mj Ne Ni Nj Nn Nw Ny Oe Pa Pe Po Qa) Jh(Ip Is Lj Ly Mw Nf Nj No Og Oy Pz Qd Qe) On(Ik Ir It Jk Jn Ly Mh Mw Na Nf Nv Qe) Qe(Hr Jo Mj Na Nf Nm Oy Pc Qb) Ir(Ih Il It Jn Nf Ng Oy) Nb(Il Jk Jo Ma Mg Ny) Jk(Fp Lw Mi Ml Mq) Of(Ji Lh Mq Pe Po) No(Il Lu) Nr(It Mi) Lx(Hu Mw) Is(It Ni) Pz(Mh Mw) NqNf MgIv MiNy IlPe} Bg{Cu(Aj As Bc Ch Ct Cv Cx Db Dd Ex Fp) Cw(Af Al Ap As Ba Bb Bn Co Dg Gl) Db(Ad Aj Ao Bb Bn Ch Cv Dg Fw) Ax(Bc Cx Dc Dd Dg Dk Dl) Cs(Ar Bb Co Ct Cx Dg Dl) Ex(aA Aw Dd Dg Dl Fw Gl) Bc(Bb Dd Dg Di Dl) Ch(Ad Ar Co Cv Dl) Cv(Ap Ar Dd Dg) Cx(Co Cq Dl) aA(Ar Ba Bn) Ao(Bb Dk) As(Ba Fp) Ef(Af De) AjCo AnDc ArDl DgFw} Og{Ir(Et Hr Im Iq Iu Iv Jh Jk Jl Jo Jq Jt Lj Lv Mc Mh Mi Mk Mm Mv My Nd Nj Nn Nr Nv Oi Om Pa Pd Pe Pz) Ni(Is Jh Lh Lx Ma Ml Mn Mp Mw My Na Ne Nj Oe Oi On Pa Pe Qa) Im(aA Hw It Mh Nv Oe Oi) Jh(Ip Ms Oe Oi Pc) Qe(Mm Nb Ne Pg) Nr(Hw In) Ml(Nb Qd) Ms(Lx On) NbOe} cS{bL(aL aN aS aY aZ bQ bU bW cB cD cP cX cY cZ dG dK dL) aD(aC aS bB bE bW cN cZ dD) dC(aJ aP bB cB cI cR cZ dI) cU(bJ bN cD cY dA dG dL) bQ(aQ aS aY cN cP dA) dA(aA aN bN bX cF) cN(aW aY bR cF) bG(bX dK) bN(cI cR) bR(aL aP) cF(aU cD) cY(aQ aY) aAaN aSbW bXcB cGdG cRdK} Fw{Cw(aA Ad An Ap Ar As Ax Bb Ch Cq Cs Cu Dc Dd Dg Dl Fp Gl) Cu(aA Aw Ax Bc Bn Co Cp Cq Cs Cv Db Dk Ef Ex Fp) Co(Al Ap As Ax Bb Bc Bn Cv Dc Gl) Ba(Al Cq Cv Dk) Bo(Ch Cp Cx Dg) Db(Ad Bb) Dk(Ax Bn) CpCs} aD{cR(aC aF aH aU aW aY aZ bH bR bV bW cF cH cQ dF) aX(aG aQ aU bL bN cF cQ cY dA dF) aN(aA aY bL bN bZ cG cH cQ) bZ(aC bM bO bX cN cQ cU) bN(aG cD cQ) cO(bX cZ dA) bF(dA dD) cF(bH dA) cZ(aG aL) dF(bE cX) bLbV bXcD} Jh{Il(Hw It Iv Nn Nq Oi Pg) Oe(aA Ip Iv Jl Ma Ml Pz) Md(Is Ly My Ne Nh Pz) Mt(Ir Is Ly Ma Mh) Oi(Im Ml Nq Pc Qb) Nt(Im Ir Ma Nr) Nv(Ip Ir On Qe) In(Iv Nq Pz) Lj(It Na Qb) Ma(Et Ms) My(Ik Ne) Pz(Jr Mh) NrIt LuNe MlIp NfHw IrJn} Bo{Ct(Ap Ar Aw Ax Ba Bb Bc Cs Cu Dc) Al(Ad Ar Bn Cs Cw Cx Ef Ex) Aj(Ad Ax Cs Db Dd Dg Ef) Co(Aw Cp Dc Dg) Ax(Cs Dk Ef) Db(Ad Ap Bc) Dd(Cp Dk Ef) Af(Cv Ef) Ar(Ba Cs) Bn(Cv Dk) Cx(Cw De) CsDg} It{Nr(Hu Hw Im Io Ip Lx Ma Md Mn Mv Mw Nb Nd Nq Ny Oe Pd Pg Qd Qe) Ni(Io Is Jk Mw Ny) Im(Jk Ma Mw Nq Of) Ir(Mv Mw Nq) Il(Lx Qa) Iv(Mv On) MaJk MdIs} Cx{Co(Ap Ax Cp Cq Cs Cu Dg Dl Fp) Cq(Ax Ch Cp Dd De Di Ef) Cw(Al An Ao Bc Di) Ex(Ad Aj Ap Dk) Ax(Aj Ch De) AdDb AfEf AoDk BaDe ChDc CuFp} Mv{Nr(Im Iv Lj Mh Ml Qe) Mh(Ik Jl Nd Oe Pz) Iv(Hw Iu Ni Oe) Il(Ir Nb Ng) Nn(Lj Qe) Ni(Ip Nd) Iu(Ir Ms) Pz(Hw Jt) Qb(Lj Ml) Oe(Lv Md) MjIn} bZ{bM(aO bH bJ bW bX cH cN cX dC dD) dC(aA aJ bB bW cI) bN(aN cI dA) aO(bW dG) bX(cD cZ) cF(bU dA) cP(bQ dL) aGdA aKcZ aQaU} Bc{Co(Af Ap Bn Ch Cs Db Dd Dl Ef) Ef(Ad An Ao Ct Db) Aw(Aj Ar Bn) Cp(An Ax Db) Db(Al Dl) Ex(Ad Ba) DdDk} Jk{Ni(Hw Iu Lj Mf Ml Mr Nd Ne Nn Nq Nt Oe Oi) Mh(Md Nq Pg Pz) Ml(Mj Ne) NrNa MaPg NbOf InIv QbLj NvOn} cF{bU(aY bL cO cR dG) cD(aP aY cX dA dM) cX(aP aU dA dF) cR(aU bN cN) bG(cZ dA) bH(dA dL) aNaY cEcZ dCdM} Ax{Aw(aA As Ba Cp Cq Cw Dc Gl) Cs(Ad Ba Co Cu Cw) Ba(An Ct) Cp(Cv Dl) Dk(Ao Fp) Ef(Ar Db) CoDi} Pz{Mh(Jq Md Mj Mw Ne Nt) Jt(Jp Ne On Qa) Nb(Jr Mj Nt) Nq(Jn Nh) Mw(Ms Nv) Qe(Jq Ne) NaJq IrJn} Cw{Bn(Ch Co Cp Cq Cv) Cp(Ao Dd Di Ef) Ar(Ao Ba) AdAl AfCq AwDd BaCv} On{Jt(Lj Mj Ml Mp Nq Nr Of Pd Pe Qb) Nv(Hu Im) NtNi LuMl NaIv} Db{Cp(Cv Dd De) Af(Ap Dc) Bb(Ba Di) Bn(Co Cq) Dk(Dd De) AwCt DiEf} Is{Md(In Jn Mh Mj Na Ni Pg Qb) Mj(aA In) MhMt NbNv JqOk} Mw{Ms(Il Im Mj Mt) Ma(Jl Jn Md) Na(Il Iv) NnNi NoIr InIv} Nb{Il(Ir Mf Mj Mt Ne Nq) Nt(Mg Nr) MaMt JrPd OeOf} aN{aY(bH cN cZ dG dL) bN(aX cG) dC(dA dG) aSdI} Ef{Ao(Ap Ct Cu) Co(Af Ap Aw) AnDc AwCs} Nq{Ni(Ip Mr Mt Pa) MjMs NaIv NeIl InOf} aQ{aU(bE bG bU cR) bL(aX bW dA) aZdF} cX{aL(aJ bE bL cZ dH) dK(cP dM) aHaX} Ex{Ap(Co Cp Cu) Ar(Ba Dk) AdBa BbDg} Na{Hu(Lj Ma) Ir(Ik Mp) Iv(My Pg) QbPe} Cs{Aw(Ad Al Ao As Dl) AnCp} Qe{Mg(Et Jt) Oy(Ni Oe) NtHu IlQb} dC{dA(cG cH dF) aX(aO cR) bFcZ} Ir{Jn(Im Pg) Oy(Mj Ni) HwOf} aY{aZ(bN dL) bO(cL cZ) bNcL} Bn{Co(As Di) AjDk AlCq} In{MfOf MjHu MqIl IvNy} Ba{Cv(An Ar Ct)} Iv{Lu(Mg Ne) MaMr} Of{MhIm MkLj NiHw} aK{aUbQ bHbM bLcP} bN{aL(bW dA) cIcR} bO{aXcR bFcZ} NrNtMi MaMdHu MhImOy NeIlaA NfHwNx NiJrPa bGcPdL bXcDdF

Unconstrained panels with 2 analytes, where 1.0E-7 >= 'AUC p-value' > 0. Contains 52 panels of 11,937 total panels evaluated. : dE(aG aH aI aK aL aN aO aQ aW aY bA bC bF bH bQ bW bX bZ cE cF cH cL cR cS cT cY dF dN) Pf(Fp Ii Lh Lz Ml Mx Nc Nk Nl Oh Qb) Fr(Nc Oh) bA(aM cX) bP(cF cS) cR(aE dN) BgBo NcQc HvIm cCdN cTcX Unconstrained panels with 2 analytes, where 1.0E-6 >= 'AUC p-value' > 1.0E-7. Contains 60 panels of 11,937 total panels evaluated. : Pf(Il Ip Is It Jj Jn Jq Js Jt Li Lu Mj Mp Mu Na Nd Ni Nn No Nr Nt Nv Oe Pe Pg Po) dE(aA aF aR aS aU aX bG bP bV cG cN cP cV dG dH dM) Gp(Ap As Cp Cw) Mu(Hv Il Qc) Fr(Ii Nn) aE(bA cT) dN(aN bZ) AoCo BoCt HvIn aMcT bAcF

Figure 26 Continued

Unconstrained panels with 2 analytes, where 1.0E-5 >= 'AUC p-value' > 1.0E-6. Contains 137 panels of 11,937 total panels evaluated. : Pf(Et Fr Hq Hu Hw Hx Ih Ik Im In Io Iq Ir Iu Iv Jh Ji Jk Jl Jm Jp Jr Lj Lv Lw Ly Ma Mc Md Me Mf Mh Mi Mk Mm Mn Mq Mr Ms Mt Mv Mw My Mz Nb Nc Nh Nj Nm Nq Ns Nu Nw Nx Ny Of Og Oi Ok Om On Oy Oz Pb Pc Pd Pz Qa Qc Qe) dE(aV aZ bB bE bJ bU cA cJ cO cQ cW cX dI dK) dN(aG aH aY bG bH bL cD cE) Nc(Jg Jh Jk Li Mv Wm) cT(bG bL bZ cS cW) Gp(Ba Bg Cu Cx) bA(aN bL cS dC) Nk(Ij Jk Li) Qc(Jh Mh Ni) aE(aX bZ cD) Bg(Ax Cw) Hv(Mv Na) bP(aK bZ) cC(cF cS) cW(aG bH) BoCo CwFw FrNi MwOh NlJh aMaX aWdB Unconstrained panels with 2 analytes, where 1.0E-4 >= 'AUC p-value' > 1.0E-5. Contains 166 panels of 11,937 total panels evaluated. : Fr(Bn Gp Hu Hv Il Js Md Mh Ml Ms Mt Mu Mx Nl Nq Pa Pc Pz Qc) Pf(aA Hr Hv Ij Jg Jo Lx Mb Mg Nf Ng Pa Qd Wm) dE(aE aM aP bL bM bN bR cD cl dA dB dJ) Li(Hq Ii In Lv Mn Ni No Oh Pz Qb) Nc(Ij Im Jp Mg Mu Nq On Pe Pz) cT(aD aZ bF bN cC cE cL dC) Nl(Hu Ij Jg Jk Mv Pz Qc) bA(aA aD bF bl bZ cQ cW) Hv(Ma Mw My Ny Pz Wm) Qc(Mv Mz Ne Nk Pc Pz) aE(aC aN aZ bH cC cS) aM(aA aY bH cP dG dN) Mu(Ir Iv Ml Nk Of) Mx(Ir Is Mw On Qe) Ij(Jh Mv Na Ni Oh) dN(bF cH cL cO dB) Bn(Co Dk Ef Gp) Co(Cx Fw Gp) Wm(It Jh Pz) cR(cC cS dB) Aw(Ax Gp) Bg(Cs Cu) Bo(Ef Gp) Cx(Cq Cw) Mv(Nk Oh) Ir(Js Og) bP(cW dF) CpDb CuFw MaHu NkJh ImJs IsOh aKcW aNdB bLcS Unconstrained panels with 2 analytes, where 1.0E-3 >= 'AUC p-value' > 1.0E-4. Contains 570 panels of 11,937 total panels evaluated. : Fr(aA As Bo Cx Db Et Fp Hq Hw Hx Ih Ij Ik Im In Io Ip Iq Ir Is It Iu Iv Jg Jh Jk Jl Jm Jn Jo Jp Jr Jt Lh Li Lj Lu Lv Lw Lx Ly Ma Mb Mc Me Mf Mg Mi Mj Mk Mm Mn Mp Mr Mw My Mz Na Nb Nd Ne Ng Nj Nk No Nr Ns Nt Nu Nv Nw Nx Ny Oe Of Og Oi Ok On Pb Pd Pe Pg Po Qa Qb Qd Wm) Mv(Hq Hr Hu Hw Hx Ii Ik In Ip Ir It Iu Iv Jj Jk Jm Js Jt Li Lv Ma Md Mf Mh Mk Ml Mn Ms Mu Mx Na Nb Nd Ng Nh Nj Nr Nt Nu Nv Ny Oi Pe Pg Pz Qe Wm) Li(Fp Hu Hv Ih Il Ir Is Jh Jk Jp Js Lu Ma Mb Me Mu Mw My Na Nb Nl Nq Nr Nv Nw Nx Ny Of On Oy Pg Qc) Qc(Hq Hu Hv Ij Il Im In Io It Jm Js Lv Lx Ma Mb Mg Ml Mw Mx My Na Nb Nq Of Oh Pe Pg Qb Qd) Hv(Fp Hu Ir Is Iv Jh Jp Jq Jr Lh Lv Lw Mi Mq Nb Nf No Nq Nx On Pe Pg Qe) Nc(Hu Il In Io Ir Is Lv Mw My Nb Ng Nh Nr Nv Nx Ny Of Pa Pd Pg Qd Qe) cW(aA aC aN aX aY bG bL bW bZ cC cE cF cN cO cQ cR cS dA dD dG dI dN) Mu(Im Jh Lu Ly Mb Me Mg Mh Ms Mx Nb Ng Ni Nj Nl Nr Pc Pg Pz Qe Wm) dN(aD aE aK aQ aR aS aX aZ bA bC bJ bQ cG cM cP cS cT cX dF dL) Gp(Aj Al Ao Bb Bc Ch Cq Ct Cv Db Dc Dd De Di Dl Ef Fp) Jh(Ik Il In Ip Lj Ly Md Mh Ml Mt Mx My Ne Oe Oh Oi Pz) aE(aG aH aL aQ aS aY bE bG bJ bP bV cE cF cO cQ dB dF) bA(aJ aL aP bE bG bO bP bQ bV bX cA cB cC cE dH dl) cS(aJ aM aP aQ aS aY aZ bQ cl cN cP cU dB dC dG) Nl(Ik Im Ir Is Iv Lv Nh Nq Nr Nx Of On Pg Wm) dE(aC aD aJ bI bS cB cC cK cM cU cZ dC dD dL) cT(aF aN aX aY bH bJ bM bP bQ bX cH cR dH) Mw(Il Jl Jn Ma Md Mh Ml Ms Na Oy Wm) Bo(Af Aj Al Ao Ch Cu Cw Db Dk Fw) Nk(Hu Ir Jg Nq Ny Of On Pg Pz) Ij(Hu Hw In It My Nb Pz Qd Wm) aM(bE bV bW cG cR dA dF dM) bP(aL bG bH cG cP cR dB) Bg(Ao Ap Ar Bc Cv Dg) Co(Af Ax Bc Cw De Ef) Cw(Af Ao Ax Bn Cs) Mx(Im Jk Nb Nq Pz) Ii(Is Mg Ny On Qe) Oh(Im Ma Nq On Qe) Nb(Il Is Of Oy) Jk(Mh Ne Ni Wm) aD(aX bH bZ cR) dB(aY bJ bW cP) Aw(Bc Cs Db) Bn(Ch Cp Cq) Cx(Af Cu Dk) Og(Im Ni Qe) Db(Bc Dk) Wm(Hu Lv) Nq(Jr Nf) Mh(Hu Pz) Il(In Ir) Is(Js Md) It(Im Nr) On(Js Jt) Oy(Ir Qe) aY(aN cC) bM(aK bZ) AfCq AxCp BaCv LuMg HwPz aQaU bZcX Unconstrained panels with 2 analytes, where 1.0E-2 >= 'AUC p-value' > 1.0E-3. Contains 1,809 panels of 11,937 total panels evaluated. : Jh(aA Et Fp Hq Hr Hu Hw Hx Ih Ii Im Io Iq Ir Is It Iu Iv Jg Ji Jj Jk Jl Jm Jn Jo Jp Jq Jr Js Jt Lh Lu Lv Lw Lx Lz Ma Mb Mc Me Mf Mg Mi Mj Mk Mm Mn Mp Mq Mr Ms Mv Mw Mz Na Nb Nd Nf Ng Nh Ni Nj Nn No Nq Nr Ns Nt Nu Nv Nw Nx Ny Of Og Ok Om On Oy Oz Pa Pb Pc Pd Pe Pg Po Qa Qb Qd Qe) Mw(aA Et Fp Hq Hr Hu Hx Ih Ii Ij Ik Im In Io Iq Ir Is It Iu Iv Jg Jk Jm Jo Jp Jq Jr Js Lj Lu Lv Lw Lx Ly Lz Mc Me Mf Mg Mi Mj Mk Mm Mn Mp Mq Mr Mt Mv My Mz Nb Nd Nf Ng Ni Nj Nk Nl Nn Nq Nr Ns Nt Nu Nv Nx Ny Oe Of Og Oi Ok Om On Oz Pa Pb Pc Pd Pe Pg Po Pz Qd Qe) Qc(aA Et Fp Hr Hw Hx Ih Ii Ik Ip Iq Ir Is Iu Iv Jg Ji Jj Jk Jl Jn Jo Jp Jq Jr Jt Lh Lj Lu Lw Ly Lz Mc Md Me Mf Mi Mj Mk Mm Mn Mp Mq Mr Ms Mt Nd Nf Ng Nh Nj Nm Nn No Nr Ns Nt Nv Nw Nx Ny Oe Og Oi Ok Om On Oy Oz Pa Pb Pd Po Qa Qe Wm) Mv(Et Fp Fr Ih Il Im Io Iq Is Jg Ji Jl Jn Jo Jp Jq Jr Lh Lj Lu Lw Lx Ly Lz Mb Mc Me Mg Mi Mj Mm Mp Mq Mr Mt My Mz Ne Nf Ni Nm Nn No Nq Ns Nw Nx Oe Of Ok Om On Oy Oz Pa Pb Pc Pd Po Qa Qb Qd) Mu(aA Hx Ih Ii Ij Ik Ip Iq Is It Jj Jk Jl Jm Jn Jo Jp Jq Jr Lh Lj Lv Lw Lx Lz Ma Mc Md Mf Mi Mk Mm Mn Mp Mq My Mz Na Nd Ne Nf Nh Nn No Ns Nt Ny Oe Oh Oi Om On Oy Oz Pa Pd Pe Po Qa Qb Qd) Nq(Et Hq Hr Hu Ih Ii Ij Ik Il Im In Io Ip Ir It Iu Iv Jk Jl Jn Jo Js Lj Lu Lv Lw Ma Md Mf Mg Mh Mi Mj Ml Mq Mr Ms Mt Na Nb Ne Ng Nh Ni Nn Ns Nt Nu Of Og On Oy Pa Pc Pd Pg Po Qa Qb Qe) Nc(aA Et Fp Hq Hr Hv Hw Hx Ih Ik Ip Iv Jl Jn Jo Jr Js Jt Lh Lj Lu Lw Lx Ma Md Me Mf Mh Mi Mj Ml Mm Mn Mq Mt Mx Mz Na Nd Ne Nf Ni Nj Nk No Ns Nt Nu Og Oi Ok Om Oz Pc Po Qa Qb) Li(Hr Hw Hx Ij Im Io Ip Iq It Iv Jg Ji Jj Jl Jm Jn Jo Jq Jt Lh Lx Lz Md Mf Mg Mh Mj Mk Ml Mm Mp Mr Ms Mt Mx Mz Nd Ne Nf Ng Nh Nj Nm Nn Nt Oe Oi Ok Om Oz Pb Pc Pd Pe Qa Qd Qe) Jk(Hu Hv Hw Hx Ii Ij Im In Io Ir Is It Iu Iv Jl Jm Js Jt Lj Lv Lw Lx Ly Lz Ma Mb Mc Md Me Mf Mg Mi Mj Ml Mq Ms My Na Nb Nh Ns Nu Ny Oh Oi On Oy Pa Pb Pc Pe Pg Pz Qe) Ij(Et Hr Hv Hx Il Im Iq Ir Is Iu Jg Ji Jj Jn Jp Jt Lh Lj Lv Lw Lx Lz Ma Mb Mc Md Me Mi Mk Ml Ms Mt Mx Nd Ne Nf Ng Nj Nn No Nr Ns Nx Ny Of Ok On Oz Pg Qb Qe) cS(aA aC aD aF aH al aK aL aN aR aU aW aX bB bC bE bG bH bI bJ bM bN bO bR bU bW bX bZ cA cB cD cE cF cG cJ cL cM cO cQ cX cY cZ dA dD dF dH dI dJ dK dL dM) cW(aD aE aH aJ aL aM aO aP aQ aS aU aV aW aZ bC bE bF bI bJ bM bN bO bQ bR bS bU bV bX cA cB cD cG cH cI cK cL cM cP cU cV cY cZ dB dC dF dH dJ dK dM) Hu(Fp Hw Ii Il Im In Ip Iq Ir Is It Iv Jp Lj Lv Lw Lx Lz Md Mg Mi Mj Mk Ml Mm Mn Mp Mq Ms Mx Na Nb Nd Ne Nf Nh Ni Nj No Oi Ok On Pa Pc Pe Pz Qa Qe) cT(aA aC aG aI aJ aK aL aP aQ aR aS aU aV aW bA bB bC bE bI bO bR bS bU bV bW cA cB cD cF cI cJ cK cM cN cO cP cQ cU cV cY dB dD dI dJ dK dL dM) Is(aA Et Hw Hx Ih Il Im In Ir It Jl Jn Jq Jr Jt Lj Lv Lw Lx Mh Mi Mj Ml Mp Mt Mz Na Ne Ni Nk Nn Nr Nv Oe Og Oi Ok Om Pa Pc Pd Pe Pg Po Qa Qb Wm) aE(aA aI aJ aK aM aO aR aU aV aW bB bC bF bI bL bN bO bQ bR bS bU bW bX cA cG cH cI cK cL cM cN cP cV cX cY cZ dA dD dG dH dI dJ dK dL dM) dN(aA aC aF aI aJ aL aO aP aU aV aW bB bE bI bM bN bO bP bR bS bV bW bX cA cB cF cI cJ cK cN cQ cU cV cY cZ dA dC dD dG dH dI dJ dK dM) Hv(Hx Ii Ip It Jg Ji Jj Jl Lj Lx Ly Lz Mc Md Me Mg Mh Mj Mk Mn Mp Mr Mx Mz Nd Ne Ni Nk Nl Nr Ns Nt Nv Nw Of Og Ok Om Pd Po Qa Qd) Pz(aA Ii In Ir It Iu Iv Jp Jq Js Jt Lh Lu Lv Lx Ly Mb Md Mg Mj Ms My Mz Na Nb Ne Nf Nh Nt Nv Ny Oe Of Og Oh On Oz Pg Qa Qd Qe) Fr(Af Aj An Ao Ap Ar Aw Ax Ba Bb Bc Bg Ch Co Cp Cq Ct Cu Cv Cw Dg Di Dl Ef Ex Fw Gl Hr Ji Jj Jq Lz Mq Nf Nh Nm Om Oy Oz Qe) Nb(Hq Hx Ii Ir Jn Jo Jr Js Lj Lu Ma Md Mf Mg Mh Mj Ml Mn Mr Na Ne Ng Nk Nl Nr Ny Oe Og Pa Pc Pe Qb Qd Wm) bA(aC aH aI aK aQ aR aS aV aW aX aY aZ bB bH bJ bM bN bS bU cH cI cJ cK cL cM cO cR cU cZ dA dB dG dK dM) bP(aA aD aH aI aJ aM aO aQ aS aU aX aY aZ bC bF bL bN bO bQ bR bU bV bX cA cB cC cE cH cO cY dC dI dK) Nl(aA Il In Io Ip Jl Jp Lh Lu Lx Ma Mg Mh Mj My Ne Nf Ng Ni Nj Nt Nu Nv Ny Og Pa Pd Pe Po Qa Qe) Cw(Ad Aj Al An Ap Ar As Aw Ba Bb Bc Ch Cp Cq Ct Cu Cv Db Dc Dd De Dg Di Dk Dl Ef Fp Gl) Co(aA Ad Aj Al An Ap As Aw Ba Bb Bg Ch Cp Cq Cs Ct Cu Cv Db Dc Dd Dg Di Dk Dl Fp Gl) Ir(Et Hq Hx Ih Ii Ik In It Jn Jq Jt Lu Lv Md Mg Mt My Na Ne Ng Nj Ny Of Oh Qb) Cu(aA Ad Af Aj Al Ao Ar As Aw Ax Ba Bc Bn Cp Cs Ct Db Dc Dd De Di Ef Fp) aM(aC aD aG aH aJ aK aL aP aQ aZ bX bZ cE cF cJ cN cO cQ cZ dB dH dI dJ) Qe(Hq Hr Ik Il It Js Mg Mh Mt Mz Na Ne Ni Nk Nn No Nt Of Oz Pb Pc Qb) Of(Fp Hw Ii Im In It Lh Lj Lv Lw Md Mh Mi Mq Mx Nf Ni No Pe Wm) Bo(Ad An Ap Ar Aw Ax Ba Bn Cp Cq Cs Cv Cx Dc Dd De Dg Di Fp) cP(aH aI aK aL aO aY bF bG bL bZ cC cE cF

Figure 26 Continued cG cH cJ cR dF dK) Nk(Ik Il Im Jp Lx Ma Mg Mn Nf Nv Nx Pa Pe Qd Wm) cR(aH aP aQ aX bE bL bN bX bZ cF cN dC dG dH dI) Lv(Hx Ii Im Io Iv Lj Md Ml Mr Nd Ng Ny Oy Pa) Bg(Ad Af An As Ba Bn Cx Db Dc De Dl Ex Fp) On(Et Hw Ik Il It Lu Md Mh Mp Mt Nv Og Pg) aD(aG aN aY bL bV cE cO cQ dA dB dF dI) Ef(Af Ao Ap Ax Bc Cs Cv Cx Db De Fw) Wm(Il Ip Jo Ma Mg Na Ne Nf Ny Oi Pg) Gp(aA Ad Af An Ar Ax Cs Dg Dk Fw Gl) Lu(Ip Lw Lx Mi Mq Nc Nm No Ok Pa Pe) bZ(aO aZ bJ bN bQ bW bX cC cZ dB dC) cC(aN bM bU bV bW bX cE cG dF dG) dB(aK aZ bH bM cF cI cO cX dA dG) Ba(Af Aj Al An Cp Cx Db Dc Dk) Ma(aA It Iv Js Jt Mx Na Ny Oy) Mg(In It Iv Md Mh Ml Mx Na Oe) Db(Ad Af Al Ap Bb Bn Cq Dg) Oh(Jg Jp Lh Nn Ny Om Pe Qa) aN(aJ aL aQ aS bN cD dF dG) aX(aC aQ aZ bM bN bO cF cX) aY(aZ bJ bM bN cF cL dK dL) Mx(Iv Jg Mj Nn Ny Pg Qa) My(Iv Mh Ml Na Nf Ni Pc) Aw(An Bn Ct Cx Dc Fw) Dk(Af Ao Ax Cs Dd Fw) Ne(Ik Im Jg Nh Ni Nr) Bn(Ad Al Ao Dc Dg) Ni(Io Ip It Na Nd) Im(Ih Ip Jn Mh Oy) Iv(Hq Il In Na Nr) Jp(Il It Md Nf Og) bL(aK aL bV bW cE) cF(bH bU cD dA dJ) cX(aA aL bV cV dF) Cp(Af Cs Cx Fw) Lx(Mt Nt Oy Pg) Jg(Li Jt Md Mh) Lj(Hq Il It Pg) Ny(Js Md Ms Nf) Pe(Hq Na Og Oy) dC(dA dF dG dI) Cx(Ch Dc Dg) Ex(Ap Bc Dg) In(Ng Oy Pc) Qd(Mh Ml Pc) bG(bX cZ dG) Qa(Js Og) Lh(Og Qb) bH(bM dL) bX(cD cO) dI(aS bM) AfDg DcDd Poli NrIp MqOy NaIl NfNx aZdF bFcZ bOdE Constrained panels with 3 analytes, where 1.0E-8 >= 'AUC p-value' > 0. Contains 1,603 panels of 409,920 total panels evaluated. : Wm{Hv(Et Fr Hu Im Io Ip Ir Is It Iv Jg Jh Ji Jk Jn Jq Jr Lh Li Lv Lw Lx Ly Ma Mg Mi Mj Mn Mp Mq Mu Mv Mz Na Nb Nc Nd Ne Nf Nl Nm No Nv Nw Nx Oi Ok Om On Pa Pe Pf Pg Po Qc Qd Qe) It(Fr Hq Hu Ij Il Is Jh Jk Jl Jo Lv Ma Mg Mn Mu Mv Nb Nc Nq Of Oi Om On Pf Pg Pz Qc) Oh(Ij Is Jg Jh Jk Ma Mu Mv Mw Nq Om On Pf Pz Qc) Fr(Et Iv Jn Js Jt Mt Mx Nc Nn No Nr Nt Qa) Mx(Hu Jh Lv Mu Mv Mw Nb Nq Pf Qc Qd Qe) Nc(Hw Ij Il Li Lv Mu Mv Nb Og Oi Pf Qc) Js(Ij Is Jh Jq Ma Mn Mv Om On Pf Pz Qc) Jh(Ii Jt Na Nn No Oe Oi) Mi(Hq Il Ip Lj Of Oy) Nl(Il Lv Mv Of Pf Qc) Oi(Hu Ij Jk Of Og Oy) Nn(Ij Jk Mu Mv Pf) Om(Et Ii Jt No Ok) Pf(Jn Lh Lj Qb) Mv(Ip Iv Me) Nk(Ij Nf Of) Mu(aA Nu) Qc(Ih Mz) NoOn MaJn MeOg MnJt MqLj NbIl} cT{aM(aN aW aX bF bG bN bW bX bZ cF cH cL cP cQ cR cW cX dE dI) bG(aD aE aF aG aH aL aO aZ bF bP cE cG cL cW cX dC dE dN) bZ(aD aE aF aL aO aZ bB bF bJ bM bP cG cL cX dC dE dN) bF(aD aE aF aL aO aZ bJ bP cG cL cX dC dE dN) aE(aI aN aR aZ bH bI bJ bX cC cH cS) cH(aD aF aZ bP cL cX dC dE dN) cX(aD bJ bO bV cC cF cV cW) aD(aN bH bN cC cR cS) bL(aZ bJ bN bX cL cS) dE(aL aN bX cA cB cF) aN(aY bN cC cW) cE(aF aZ bP cL) aY(aZ bP cL) cC(bJ bX cL) cS(bP bV dC) bH(cF dC) cR(aG cW) bNbX} Pf{Oh(Fp Fr Jk Jp Lz Ma Me Ml Mu Mw My Mz Nd Nj Nq Qb) Ii(Fr Il Jh Jk Jo Lz Mi Ml Nf Nk Of On Pz Qb) Js(Ih Im Ir Iv Lz Mf Mk Ml Nj Nk Nr Pz) Qb(Im In Iv Li Na Nc Nn Oe Oi Qc) Ni(Fp It Jr Mj Mr Mx Oe Og Pe) Fp(Mf Mi Nc Nk Pg) Mx(Im In Mu Nk Pz) Oe(It Mf Mu Of Og) Fr(Lh Nn Nr Nv) Mi(Ji Jq Mq Po) Ml(Ma Mp Mz Na) Et(Nd Nj Pz) Nn(Mw Nx Of) Lz(Ma Mp Mz) Mj(Im In Nc) Mk(Jn Jr Og) Mr(Nc Nj Nk) Ji(Ip No Nx) Lh(Mu Mw My) Ns(Nc Nl) Mf(Nw Pe) Nd(It Jn) Nk(Nf Og) Pz(Jt Nr) Jq(Lw Ok) MwJn HvIm IpIs QaQe NvOn} dN{aN(aE aH aY bF bG bL bZ cC cD cE cG cH cR dE dF) dE(aG aH aI aK aQ aR aV bF bG bZ cR cX) aM(aS aX aY bA bH cD cE cO cP cR dL) bL(aG aK aW bA cO cR cS cX dL) bP(aH aL aY bF bG bZ cE cH dF) cD(aD bF bG bX bZ cH cR cS cX) cM(aI aL bF bG bZ cE cH cS dL) dB(aG aK aW bF bZ cH cR cX) cE(aU cB cL cV cX dA) bG(bA cB cQ cZ dA) bZ(aO bA cB dA dD) cC(aG cF cR cX dL) aE(aG aH aL cR) aU(aG aH aK aL) bF(aO bA cB dA) cO(bR cX dC) aH(cV cX) aYcL aZcX bAcH bCcR} bA{aE(aA aN aZ bF bG bZ cC cR cS cX dH dM) cF(aD aM bG bH bL bP bV cC cQ cW dC dE) aN(aD aY bF bG bL bN cC cQ cW cX dC) aM(aP aS aW aX bL bU bW cC cQ dK) bP(aY bF bG bZ cE cH cS dC dM) bV(bF bG bZ cH cR cS cX) dC(bF bG bZ cH cR cS dK) bL(aW aZ cL cX dH) cC(aW bM bX cL cX) cG(bF bG cE cH cS) dE(aF aJ bF dA) aA(aX cL cS) aO(bF bG) aW(aX dB) aZ(bG cH) bM(bZ dM) cW(cP dK) aDcR cXdK} dE{aN(aG aH aQ aU aV bC bF bN bW bX bZ cE cJ cV dB dH) bW(aH aI aK aL bE bF bG cE cF cS cV cW dD) aZ(aG aH aI aY bZ cE cG cJ dF) bP(aY bF bQ bZ cE cF cG cH) cI(aG aH aK aQ aU aV bU cY) bX(aG aK bC cE cY) aQ(aW cA cF dK) bR(aI aK aL cS) aH(bB cA dK) aP(aY dG dH) aG(cA cW) aI(bB dK) bM(aK cY) cR(bQ cF) dG(aJ aU) aRdH aWaY bHdI bZcU cAcE} Fr{Ii(Hu Hv Il Ir Iv Li Lj Lv Lw Lx Ma Me Mg Mi Ml Mq Mu Mx Nc Nf Ni Nm Nn No Nq Nr Oh Ok On Pe Pz) Oh(Hv Ij Li Lj Ma Mh Ml Nc Nl Nr) Ni(Jl Js Md Mt Mx Nr Nt Og Pa) Nn(Hv Ij Li Md Mx Pc) Nc(Jl Md Mm Mt Mx Pa) Bo(Ct Ex Fw) Pz(Jt Nr Nv) Js(Ir Iv Nr) Mx(Lv Nk) AsGp BcEx NoIr MzQc NlIv HvIm} aE{aZ(aG aH aQ aX aY bH bZ cD cE cG cO cQ cR cS cY dB dF) aN(aQ aX aY bG bV bZ cC cD cG cH cS dB dF) cR(aX bB bE bX cC cF cN cU cZ dB dK) bP(aK aL bF bZ cE cF cS) aL(aC bE cZ dA dG) bJ(aX bZ cC cD cE) cC(aG aH aK cE) aX(aH aQ cX) bZ(bX cN) cS(bG cU) cZ(aH aI) bEcX bHcF} Nc{Li(Il Jk Lu Lz Ma Ml Mu Mv My Nr Pa Pz Qb) Pa(Is Jg Jh Mu Mv Mw Nq Pz Qa Qc Qd Qe) Mx(Ir Jg Jh Jk Mv Nq On) Qc(Jh Mu Nb Nh Ni Ns Pz) Ij(Jg My Ni Nr Oh Pz) Mv(Mf Mu Nq Oh) Hv(Io Jg Ny Pz) Il(Jh Mu Nb Nq) Jk(Iv Lj Nr) Jp(Hu Ik) Js(Im On) Og(Jh Nr) MpOn MsMw MyIv IiJg} Qc{Nl(Hq Hu Il Iv Jh Lv Nb Ne Nh Ni Nr Of Pc Pz) Mu(Hv Ma Mh Ml Mz Ni Nk Nn Nr Oh Pc) Ni(Ih It Iu Js Mx Na Nr Og Pa Pc) Jh(Ii Mh Mx Nk Nn Nr Nt Oh) Pz(Hv Js Jt Mh Nk) Oh(Ma Mv Mw Nq) Mx(Ir Nb Nr) Nk(Ij Pc) Im(Hv Js) MhQb IiLi} Mx{Mu(Hv Il Ir Iu Iv Li Lj Lx Mh Ni Nr Pz Qa Qe) Ir(Hu Jh Js Mv Nq Og Oy) Qe(Hu Hv Jh Og Oh Oy Pz) Li(Hu Im In Ni On Pz) Iv(In Mv Nq On) Nk(Jh Jk Mv) Nl(Jg Jh) Hv(Ny Pz) Ij(Ni Pz) Is(Nb Oh) MjMw HuQa IiOn} aM{bX(aA aY bV bZ cD cG cP dF) aZ(aA aX aY bH bV cQ dF) cF(aA aY bH cP dA dG dM) aK(aJ aX bH cZ dA dG) aL(bE bW cZ dA) aY(aN bE cZ dK) bZ(aA bB cU cZ) cS(aA cU dA dG) dK(aA bH cP) aOaX aSbE bFcZ bVcC cYdA} Oh{Mw(Hv Is Li Lj Ma Mh Nk Nr) Ij(Hw In Jh Mg Mv My Nk Nl) Li(In Is Jp Ma My Nq On) Lj(Jk Mv Nn Nq On) Nl(Is Jg Mv Nq) Qe(Ma Mg Mv Og) Nr(Is Mu) Nk(Mv Nq) MaMu MdIs MgQa ImOg} cF{bP(aL aQ aS aY bF bG bH bZ cC cE cP cS cV cW cY dB dC dF) cW(aC aG aN bG bH bO bR bU cD cR) cC(bE bJ bW cB cI cR cX dA dG) dB(aY bW cR cX) bU(cS dJ)} Hv{Im(Ip It Iv Jg Jh Ji Jn Jq Js Li Lv Lw Lx Ma Mi Mn Mq Mu Na Nd Nm No Nw Ok On Pa Pz) Pz(Hw Li Na Nd Nk Nl) Ni(Ij Ma Nd) Ii(Mv On) Ny(Na Nk) NnMw NdIn} Nl{Iv(Hq Hu Ij Il Jg Jk Mu My Nr) Ij(Hu Jg Ne Ni Pz) Ni(Jk Li Og) Il(Mu Nb Nh) Pz(Js Li Og) Nr(Jk Og) Md(Jg Jh) Of(Nb Nu) MtJh MuPe NhJk IkIr} Bg{Ao(Ad Ap Ba Co Cu Cw Dl) Ef(Ar Ba Bc Bn Cu Cw Dl) Ax(Ad Aw Bo) Bc(Db Ex) Gp(Ap As) BoCs CuGl CvCx} Ii{Li(Hq Il Jk Nr Of Pg Qb) Mv(Ir Iv On Qe) Jk(Lx Mg No Pe) Of(Ir No On Qe) Ir(Jh Mu) On(Jt Lu)} Js{Ir(Ij Il Is Md Mg Mv Ng Nr Of Og Oy Pd Pg) Is(Li Ni Nr) Pz(Lj Qa Qe) NrOn MgQe MvIv NiIj} bP{aK(aX bF bG bL bZ cP cS cV cW dB dK) cP(aL bF bG bZ) aL(bN cW) bZ(aD cU) aYdK cEcW cMdF cScU} Nk{Ij(Hu It Jg Jh Jk Lz Mu Nb Ni) Li(Hq Il Lz Mv Nr Pg) Mu(Il Pa Pg) MlJk NbIl IrOg JtOn} Co{Ao(aA Ap Ba Bb Bc Bn Bo Cp Cx Fw Gp) Bo(Ct Di Ex Fp Fw) Bc(Ex Gp) Ef(aA Ba)} Ex{Bc(Aw Cu Dg Dk Ef) Ax(Aw Cp Dg Dk) Cs(Aw Cp Dg Dk) AdBo ApDk AwFw} bZ{dC(bE cZ dA) aD(cZ dD) aK(aU bM) cU(bM dL) dB(bW cX) bNbQ} Bo{Fw(Aj Al Cu Db Ef) Ct(Ad Al Ch Ef) Aj(Cx Gp)} Ni{Ij(It Mj Mr Na) Og(Io Jp Nd Qe) Li(Pa Po) MuIl} Gp{Cx(As Cq Dg Dk) Ef(Ao As Bc Cp) Cv(Aw Ba)} Il{Mu(Hu Ir Iv Me Mf Mh My Nq) MjIn NbPg} cC{aN(aD aY dG dH) aK(bM cW) bX(cR dF) aDcR cPdK} dB{aD(aN cR) aK(aU bW) aW(bE bW) aY(aZ cL) aZdF} Aw{Ax(Ar Cs Ct Fw) Cs(Ar Fp Fw) BcCt} cW{aK(aC aN aU dD) aLcZ aNaY cDdK cEcU} Db{Cx(Bb Cp Cq) AfBb DkFw} Ef{Ax(Di Fp) AoFw CsFp CwDi} dC{dG(cH cS) dK(aX bH)} Li{Qb(In Na) PzNv} Og{Ir(Jn Jr) MsIm} aD{cR(aX bN cX)} Ax{Cs(Cp Dk)} aQ{aKaU bLcS} BaCuFw MdJhOe MuInIv aNaYbO bMcScU Constrained panels with 3 analytes, where 1.0E-7 >= 'AUC p-value' > 1.0E-8. Contains 561 panels of 409,920 total panels evaluated. : Mx{Nb(Il Ir Jk Mw Nr Of Pz Qe) Is(Jh Md Nc Ni Nr Wm) Iv(Fr Im Ma Mw Nr Qc) Pz(Mw Nc Nk Nq Qa Qc) Ir(Fr Hv Jk Jn Mw) Qe(Ii It Mv Nc Nr) Mj(Fr Li Mu Qc) Nk(Jg Li Nq On) Nl(Fr Jk Mv) Im(Fr Nc Qc) Lv(Mw Qc) Ni(Jk Nq) Ij(Jh Oh) Li(Nc Nr) Lj(Jh Jk) WmNn MdMt HvIn QaOh

Figure 26 Continued

Figure 26 Continued

Ne(Hu Nr) Im(Ih Og) In(Mj Pz) WmQa NqMz NkIl HqQd HuOi HwOf} Fr{Mj(Im In Wm) Iv(Jn Na Ne) Nq(Il Nr) Mh(Na Pz) Ms(Hr Og)
Nv(Nb Pg) WmMf NrMt MgJt MlOg IjQb IlPg IrJl} Nk{Og(Jg Lu Lx Nr) Mv(Me Mf Nq) Md(Is Ny) Il(Ir Na) Of(Iv Pe) EtOn LuPa MlJg
MwPg NbHq NfJh NjPz IjQb} Wm{Mv(Mf Mh Nq) Oi(Hq Na Oe) Lu(Lw Ok) Mn(Et Jn) Ip(Il Na) Jo(In Iv) PoLj MsMw MtQe OgPf} aM{dK(aJ bV cR dM) aL(aC aX dI) aZ(bE cE cG) cF(aJ bV dJ) cQ(aY bZ) aIcZ aKbE aSbW} aE{cX(aA aO bV cQ) aI(aX bE cC) bQ(cN cU) cC(aL bV) aSbI aZbF bGcF bJcH bXdF dGdH} Ni{Og(Lx Ma Mn Qa) Nq(Mr Mt Pa) Ij(Jr Mg Nh) Mu(Jl Pa) NnMw MdIs HwOf IrOy} Jh{Mt(Ir Is Ma) In(Ij Iv Nq) Nt(Ir Nr) Og(Ms Pc) EtMa NaIj NfHw IlPg QbLj QeNv} cC{aK(aJ aP bJ bW) bJ(aY bZ cJ) aW(aJ dG) cX(dG dH) aAaN aYaZ bWbZ} Na{Ij(Hu Lz Mi Ml On) Iv(Mw My Nq) MhMu MpIr MwIl HuLj QbPe} cF{aU(cR cT cX) bG(cZ dA) bU(bZ cR) cN(cR cS) cX(cD dA) cEcZ dCdM} In{Mj(Hu Ij Is Mv) Iv(Jk Mw Ny) Of(Ij Mf Nq) NrOg} On{Jt(Mp Nr Pd Pz) Ij(Hx Jn) Nv(Hu Jk) LuMl MpMu MsOg} dC{bZ(aA aJ bB bW cI) dA(aN cG cH dF) aOaX bFcZ} Fw{Ba(Al Cq Cv Dk) Cu(Aw Cp Db) BoCp} Ax{Cs(Ad Bo Cu Cw) Cx(Aj Ch Dc)} Md{Is(Mj Mu Pg Qb) Mh(Jk Mu) MvOe} cZ{cT(bF bG bZ) bO(aY bF) aIdB aLcX} Nb{Nt(Nr Pz) MaMt NeIl IsNv OeOg} Ir{Jn(Pg Pz) NoMw MjOy MuJl HwOf} aL{cX(aJ bL dH) bNdA cWdD} bA{cE(aZ cV) aObZ aUdM aYcG} bP{aFcP aZcG bCbG bXdF cEcM} Ef{Ao(Ap Ct) ApCo BcDb} Ms{NqMj LxOg MgMu MvIu} Ne{Il(aA Nq) LuIv IjPz} aQ{aU(bZ cR) bL(aX dA)} Bo{Cv(Af Bn) ArCs} Cx{AdDb AjEx ChDc} Mh{Im(Of Og Oy)} Mu{Il(Jk Pg) MtQe} Pz{NqJn MwNv JpJt} Lj{Qb(Jk Mv) MkOf} cW{aGbG aSbE aXdK} dN{aHaX bCdL cVdF} Ex{AdBc ArBa} Ma{MwJn JkPg} Mg{Qe(Et Jt)} Hw{NrOg NfNx} aK{aUbQ aZdB} aN{aSdI bNcG} bX{cD(bZ dF)} BbDbDi MkHxIj IsJqOk NwNxPf aObZdG aYbJdB cEcGcT cXdKdM

Constrained panels with 3 analytes, where 1.0E-4 >= 'AUC p-value' > 1.0E-5. Contains 960 panels of 409,920 total panels evaluated. :
Mx{Hv(Et Iv Jg Jk Jl Jr Lx Mi Nv On Pg Po Qa Qd) Nr(Ip Lv Lx Ma Mi Mj Mv Nq Qd) Ni(Ir Iv Jg Jp Ma Mn Ny Om Qa) Wm(Iv Lh Li Lx Mi Mq Ny Pg) Lv(Hx Im Io Ma Mn My Ny) Ij(Iv Jk My Nq Qc Qd Qe) In(Jk Mw Nn Nq Of On) Im(Hu Lx Oy Qa) Iv(Jg Jp Mn Ny) Nc(Jl Lx Mt) Qa(aA Og Oy) Li(Fr Ii Qe) Lj(Fr Jg Qd) No(Lu Oy) Nq(It Mj) Nk(Lx Nn) PoHu EtLu MdNy JsOn} Ii{Mw(Ir Lw Mg Mi Mq Nb No Ny Ok Qe) Jk(It Ji Lh Nm Nw Ok Pz Qc Qe) Ny(Lw Lx Mq Nf Nm No Ok On Pe) Hu(Ir Is Mi Mq No Ok Pe) Pz(Lx Mq Nb Nf No Pe) Mi(Is Jm Mg Ng Qa) Qe(Il Jg Lx Mq No) Of(Im Lj Ok Pa Qa) Lu(Lx Nm Ok Pa) No(Is Mu Pg) Jh(Nr Ok Pe) Wm(Nf Nv) Lx(Is Mu) Ir(Jg Nm) On(Jr Ni) PoNg LwQc MaIv MgQd MuPe NbIj IsJg} Wm{Js(Et Ip Jn Jo Jp Lh Mi Mq Nf Nv Nx Oi) Oh(Fr Jl Lx Mi Nx Ok Pg Qd Qe) Of(Hw Ji Li Lw Lx Nd Ok) Og(Fr In Jh Jl Mh Mn Mv) Mw(Hu Jn Mf Mu Nn Pd) Il(Lw Mq No Ok) Mv(Mu Nf Qc) Hq(Ip Iv Nk) Ij(Lj Ma Mi) Jo(Ly Mh Oi) Nq(Jn Mf) Nb(Na Oi) Is(Ih Jn) Oy(Ly Me) NmLu NnOm NoMn NrQc NuMi MfJk NdNf NeOi NjNk InIt} Hv{Ni(Io Ip Jg Mn Mw My Nv Ny On) Na(Ij It Iv Jn Mg Mq Nu Qa) Nl(Hu Io Lh Mj Nq Nv Nx) Oh(Jg Jp Lh Lx Om Qd) Hu(Is Nc Nd Nk Oi) Md(Jp Mi No Ok) Ne(Ir Nh Pe) Nk(Hx Lx Nv) Lv(Li Mw) Nd(Lh Nr) In(Mg Nq) Jh(Nf Og) Of(Iv Lj) NnQe NoPg LuOn MjNc MkIj HqLi IrNy QdJs} Js{Ij(Fr Hu Is Jh Jk My Nb Nr On) Ma(Fr Iv Jh Mp Ni Nm Pe Pz) Nr(Io Ip Jq Lh Lv Mv Nk) Nm(In Nb Nl Nq Qa) Nk(Jp Lh Ok Pg Qd) Iv(Jh Jk Mw My Nq) Nc(Is Lx Nt) Ni(Jp Nd Nq) Pe(My Nj Nl) No(Jk Pg) Mg(Nb Qa) Qc(Nq Of) Jh(Lj Og) On(Ih Mt) NtNl MnNb QdOh JkLj} Oh{Mg(aA Im Jp Lh Lj Lx Nb Nn Ny) Nl(Jp Nr Nt Ny Pe Qd) Nn(Lh Lx Nc No Pz) No(Jk Lu Og Qc) Nr(Jp Mi My Om) Ma(Ij Mp On) Im(Il Lx Mi) Lh(Nc Ne Og) Lj(Jg Jp My) Pe(In Lu Og) Qa(Ny Pc) LuLx NgIr NiNy JhOg JjJk} Nl{Ni(Io Ip Is Mw Nx Ny) Og(Iv Lh Lv Mj Pe Pg) Md(Jp Ne Ny Om) Lu(Ji Nm Nw) Nb(Ne Nx Pg) On(Jl Mb Pd) Mh(Im Ng) My(Mb Nj) Ir(Mp Pg) Lh(Pa Pc) Li(Lz Qb) NnMw NsIl MaIk MiIj QdPc} Iv{In(Hu Il Ma Mj My Ng Nr Of Oy Qb) Ne(Hu Jh Ma Nq Of Pz) Na(Jh Jk Md Mg Pz) Ma(Et Nk Oy Pg) It(Jh Jk Nq Nr) Jn(Jh Mu Mv On) My(Mv Nk) HwOf} On{Mt(Jq Lu Mh Mu Nk Nv) Mp(Fr Mh Na Nk Nt) Md(Jt Mh Nk Nv) Nk(Lu Nj Pg) Ij(In It Jr) Jt(Jl Mg Qc) Ma(Et Mz) Nv(Jl Pe) NoMw LuLj MhJi NiOf JqLi} Ir{Nk(Jj Md Nj Pa) Jn(Md Mw Nq Oy) Na(Md Mt Pg) Ne(Il Lu Of) Nq(Mv Qb) Is(Lv Oy) Jk(Nv Pg) MgJq MnMz MpIt MtIh NbJr NcOf NgJt HuOy} Og{Ms(In Jg Mu Mv Mw Nm Qa Qd) Nk(In Nq Ny Pe) Lu(Lx No Pe) Nr(Mk Na) NnQa NtNc MaQc MbNd MdJp MhMy MvLj NaPe HrPz} It{Il(Jp Li Lj Nk Nq) Nq(Ma Md Pz) Ni(Iq Pa Qe) Ma(Mw Pe) Is(Jq Mt) Qc(Hq Of) MhJk MwPz NaNc HwIj QePc LjOf} aD{dA(aG bG bQ cE cS) cZ(aK bQ cG dF) bE(aL bG cC) bZ(aX dG dM) aN(cD dF) aKaX bLcQ bPcG cCcO cDcF dDdF} Ij{In(Fr Lz Mi Mk Ml My) Fr(Ne Nv Pg) Qb(Hw Lv Qd) Lu(Lw Mi) Na(Mu My) Nb(Jr Nv) NrNe PzJn} Ni{Pa(Is Ma Mw My Ne Of) Nd(Hu Nj Oy) Nc(Hu Io) Of(Lw Ok) NrIs MaNa MrQe NgIp JrNw} Mh{Md(Jg Jh Mw Of Om) My(Il Ip Jo Na Of) Ng(Qd Qe) Jk(Na Oi) MuJo HwOf QdOy} Nk{Lu(Lw Mq Nf Ok) Nj(Im Lx Qe) Mi(Il Pg) Mv(Hu Mu) Mw(Mz Pa) NsIl NaNf QdPc} cF{aM(bW cR cZ) bG(bU cB dG) bU(aN bJ) cN(bZ cX) aLaU aSbI aXcW bFdA bLcB bRcS} Nr{Pz(Jh Mw Nq) Hu(Is Qe) Jh(Is Qe) Li(Lz Ml) Of(Im Lj) NnMw MaMv MtNb JkOi} Nv{Jk(Im Lx Mq Nb No) Lw(Fr Jh Mv) Nb(Il Jo Of) Ok(Fr Jh) NoPg PzPa} Il{In(Jh Li Mf Nq) Na(Jh Mi Nq) Lj(Lz Ml) NnMw NtLi MyJh NeNh} Mt{Pz(Lx Mw Nb Nq Qe) Nb(Is Mg Qe) Qe(Nq Qb) MuIs MvOi} aM{aK(aU bW) aL(aN aZ) cR(bX dI) aYcP aZcO bNcQ bWdF cGcZ dIdK} dC{bZ(cB dD dM) cZ(aI aO cG) dI(aS dK) bEcG bPbV bXcO cRdA} Lu{Ml(Lw Mi Nm Nw Ok) Lj(Ip Lw Ok) MdOm NaPe NeNh} cX{dK(aH aX aY) aL(aU cI) cC(cE cG) aHcI aSdI bXcO} Mj{In(Jh Jk Li Pd Pg Pz) Pz(Mu Qe) MyNc} Qc{Qb(Lx Ma No Oi) NnNq MaIs MgNb NeOf OeOy} Mp{Fr(Lw Lx Mi No Ok) Mi(Is Jh) NoMu} Na{Md(Lx Ma Mw) Nc(Ih Nt) EtMa MlLi MuPe} aE{dG(aQ aR bF) bJ(bF bV) aKdB bIbV bXcD} aN{aL(aJ cZ dA dG) bN(aA cS) aJaQ cWdF} aU{aK(bL cP cR cY) aL(cP cY) aQ(cA dK)} cC{aAdJ aKdG aZcG bJcE bWdK bXbZ cLdF} Fw{Db(Cq Dg) AdBo AlEx BaDc CoCt} Nn{Mw(Lv Mg Pz) MuNy MvIu JkLj} Qe{NoJh MdQb MeOy IhIm PzJn QaLi} Mg{Jt(Im Nq Qd) MfIn MsMw} My{Nc(Hu Mf Mu) LyPc MvJh} Of{Hw(Lj No Pe) LvPg MiLj} Cx{AjCs AwCv CtEx DbFr} Lv{MwJn QbLi JkPg} Ma{MfHu MlLi MuJl} Md{MvOi NeIs QbLh} bL{aW(aA aP) aQbE} Ax{BaCo BoEx} Cs{Fp(Ba Fr)} Mu{Pc(Hu Me)} Is{MqJq PzJt} Jh{MlLj NdNf} Oy{MfNb MkLi} aK{bGcZ bMcL} bP{bCdK cVdF} bX{bJcT cWdF} dB{aFaL aYdH} AjExGp AwDcDd CoCpEf LzMvLj aQbBbZ aSaZdI bAcEcL bGbOcZ cWdGdL Constrained panels with 3 analytes, where 1.0E-3 >= 'AUC p-value' > 1.0E-4. Contains 1,117 panels of 409,920 total panels evaluated. :
Ii{Nm(Hu Im Is Iv Jl Ma Mw Ng Of Pg Po Pz Qa) Lw(Hu Ij Ir Is Ma Nr Of Pz Qe) No(Hq Ij Ir Jm Ma Ng Nq Oy) Mi(Ij Il Ir Jg Jh Pg Pz Qe) Nb(Hu Ir Is Mn Ng Nq Nr Qe) Ok(Ik Ir Is Iv Ng Nr Pz Qe) Il(Im Jg Lx Mq Mw Ny Po) Jg(Ij Iv Lx Ma Nf Qa) Of(Is Iv Mw Nd Ny Qd) Mq(Ij Ir Is Ng Pg) Pe(Ip Jo Jr My Ng) Nf(Hu Im Nx Pg) Mg(Is Jl Pg) Lx(Ij Ng) Hu(Pa Qa) NqPz MnIv NgJi HvNv QdQe} Oh{Nr(Ji Lx Mg Mq Nb Nd Ne Nf Nm Nn No Nw Og Pa Qa) Wm(aA Et Jo Jq Jr Li Mj My Po Qa) Jp(Il Lx Md Mh Ni Nk Of Og Pe) Nn(Et Mj Mn Ni Nk Nl Ok) Lx(In My Ng Nk Nl Og Pz) Lj(Lv Mn Nv Nx Of Ok Pz) Hv(Mz No Nv Ok Qa) Nl(Mt Mz Nv Ok) Mg(Hw Jl Mj) My(Mh Mq Pc) No(Il In) Nb(Lh Ny) Ne(Jg Pe) Qd(Og Pc) LuOk MaOg MtOn NkNv OyPe} Js{Nr(Ji Lw Lx Mq Nd No Nw Ok Pa Pe) Ni(Et Mg Mw My Nm Ok Pe Pz Qa Qd) Wm(Ji Li Lw Lx Ne Ny Ok Pg Po) Iv(Il Jg Jp Mj Ny Of Pe Qa Qd) Nk(Io Lv Mj Mn Nt Nv Nx Qa) Nm(Li Lj Mj Nc No Pe) Ma(Is Mf Mw My Nq) Lj(Jg Mg Mn My Om) Pe(In Jp Mn Mw Nq) Nl(Lx Mj Ok) Ij(Im Nj No) My(Mh Ml) Qa(Hu Hv) NqIl MdJp MgIn MjMw JjOf} Mx{In(Hu Lx Ma No Nr Og Oy Pe Qa) Ni(Et Hx Jl My Nv Oy Pe Qb) No(Il Lv Md Of Og Pg) Qd(Hu Im Lv Mh Pc Pe) Nk(Jl Lh My Nv Po) Iv(aA Il Nn Of Oy) Lx(Lu Of Og Oy) Hu(Lh Lj Mq Pe) Wm(Ji Oi Pe) Nr(Ji Mq Nw) Lv(Jg Jp Lj) Mi(Ij Il Of) My(Ip Ma Pc) Hv(Ji Nw Ok) Lu(Pa Pd) Nl(Jl Nn) Ij(aA Fr) Im(Il Mq) Pe(Md Of) MjOg IhIt LhOy} Hv{Lu(Lw Mi Mq Nm No Nx Ok Pa) aA(Ip Lv Mg Mn Nk Nx Oi Ok) Of(Hw Mq Ni No Oi Pe Qe) Nr(Lv Lw Mq No Ok) Ni(Hx Nx Pg Qd) Nk(Io Jp Nx Qd) Md(Jg Jl Om) Mb(My Nx) Na(Jt Qd) Nd(Fp Pe) Nf(Nx Pa) Og(Jp Pe)

Figure 26 Continued

NoMt NsNl MeMy MgIr MnHw MpOn MrQe Ihlt} Ir{Jn(Hu Jk Jl Mp Mt Nb Ng Nr Pd Pe) Hu(Hw In Iu Jr Na Nt) Md(Hx In It Qb) Ih(aA Nr Pe Wm) Jr(Jk Mw Ni Nq) Nl(Jl Mt Pd) In(Mp Pg Qb) Nq(Mt No) Lu(Na Nk) Ma(Is Mz) Ne(Mp Pg) WmLj MeOy MhNg MvMy MwQb NaJl IlPg JqOk} It{Iv(Il Jp Mg Mw My Ny Of Pz) Qe(Hu Im Jl Md Mp Mt Pd Pg) Ni(Jp Pe Pg Qa Qd) Ij(Lz Mi Ml My Qb) On(Jl Mb Mp Pe) Mw(Il Pd Pg) No(Il Pg) Ma(Md Pz) Qd(Il Pc) Lj(Ip Pg) Pe(Jk Oe) NaNl NgNk IsPd} On{Mp(Hw Jh Jn Mv Ne Nv) Md(Na Ne Og Pg) Nr(Mb Mt Nt) Nk(Jl Mm Pe) Nv(Nb Of Pz) No(Im Lj) Mh(Jl Nw) Ml(aA Qb) Is(Jq Mz) NtPe LuOg LvJq MmOy MtNi ImNy QbPg} Og{Lu(Ji Lw Mh Mq Nj Nw Ok Pa) Ms(Hu Lh Li Ny Ok Pe) Ma(In Nb Nc Nl) Wm(Iv Om) Mb(My Nj) Lj(Fr Mk) NrMi MhJp MjOe MlMy NaIv NkIl HuOi} In{Mf(Hu Jk Pc Pd Pz) Mj(Jo Mg Nq Oy Pc) Mu(Ij Jk Of Pd) Il(Hu Mc Mi Mw) Ij(Jk Mg Nr) Nq(Jk Mg) Hu(Jk Of) Iv(Hq Lu) MhJo} aD{cZ(aF aI aY bB cF) bQ(aC cC cN dD) cY(aJ aU aV dG) aA(bZ cF) aS(bW dI) bN(aC bZ) aKdI aYcC bCcO bEcE cDcQ cFcN cHdG cVdF} Nr{Nt(Iv Jg Lw Mq Nm Pa) Iv(Hw Ih Nh Pg) Jt(Mn Nm Pz) Nq(Jn Mt) Hu(Im Oi) LuIs MiMt MwJn MyJh NjNk HwOf IjPg ImJk QaQe} dC{bE(aL aS bF cH dF dK) dF(bX cV cZ dI) dK(aA aJ bP dM) aJ(cE cF) bZ(aX bH) cO(aA cI) cZ(aL cE) aNbV aZcG bFcB} Nk{Lu(Ji Nm Nw Nx Pe) Md(Jp Lx Nv Om Po) Pa(Mi Nf Qd) Me(My Ng) Mh(Ng Ns) Jo(Iv Wm) Jp(Nj Pc) NtNa MlMy IoPc} Mh{Md(Jp Mg Mn My Ng Ny Qe) My(Hu Nl Pc Pd) Im(Il Jr Ng) Lu(Ip Nx) Mw(Jh Na) NsNl QaQe QbQd} Mi{Mp(Jk Mu Mv Nq Of) Mt(Is Mw Of) Ij(Hx Ne Qb) Wm(Mv Na) Lu(Lj Pa) Il(Ne Nv) Of(Md Pe) NoIm IsJl} Ni{Pa(Hx Mn Nd Ng Ny Om Qd) No(Jr Of Oy) Ng(Nd Nf Nw) Oy(Ly Ok) MdJp MgNl NaHx NfIo JrPe} bL{aK(aJ aP aX bM bW) aZ(bV cE cG cO) aI(cZ dA) aL(bE bW) bV(aN cX) aHaX aJaW aRbM aSbW cTcX} Nq{Mv(Is Lj Lx Pe Po Qa Qe) Wm(Mt Oi) Nn(Il Of) Mu(Ma Na) NmLu NoPe MjPz MsNf IlPg OfOi} Nb{Nv(Jp Ma Mn Mw Ny Pz) Oy(Hu Me Mu Nn) Qb(Is Lj Qe) My(Mv Ng) Ij(Jn Pg) MaPg OiPc} Wm{Lj(Ji Lh Qd) Lu(Ji Jq) Ih(Jr Qd) Jo(Li Lv) PoNo MtJl MwIu HuJk HxOm IvOy} Il{Pg(Iv Jk Mw Qe) No(Lu Na Nv) Im(Md Nc) Jn(Li Na) NtNl LuMq MwJh HxLi} aN{aP(aK bG cE cF) bG(aJ dA dL) aQ(dA dG) dE(aS aY) aJaK aMbA cEdA cGcP} Ma{Jt(Im Mg Pz) Et(Nx Pz) Lw(Jq Lu) Mz(Iv Nw) MfOy MyJh NaPg IsIv QaQe} cC{dA(bU cB dJ) aW(aP cJ) aZ(cJ dH) bW(aS bR) cX(aY bV) aIcZ bEbZ cGcL} Ex{Af(Bb Dg) Ba(Bg Cs) Bo(Cs Cu) Fp(Ef Fr) Fw(Aj Cv) ArDg AwCt CoDi} Qb{Lj(Hu Lv Ny Pz Qd) Qe(Jl Ne Pe Pz) Ij(Hx Lh) MlQd MtIs} aL{aM(dD dG dM) cX(aX dA dM) cZ(bF bG bM) aU(aY cR) cF(bR bU)} My{Ne(Ij Lv Mb Pc) Mv(Im Li) Iv(Jn Pc) FrJl NnNc LvMl MePc} No{Na(Jq Md Mp) Im(Lw Ok) Nv(Mv Of) IjJn IsJq PzJt QePe} Oy{Qe(Hu Mf Mj Mu Nn) Me(Im Mw Nl) NnJk LyIm MfMj} bX{dE(aH aW cR) cZ(bG cE) aKaM aQcO aZcX bZcB cDcR} Jk{Nv(Ji Lw Ok Pa Pe) Iv(Hw Pg) LxMp IjPg} cF{aZ(aS cD) aHbU aJbG aKaU bJcD bNcI bZcB cXdM} Na{Ms(Mg Pz) Pe(Lz Ml) LxMp MdIm MwPz NfHw} Is{Lw(Lu Mp) Mw(Jn Nn) PoLi NmJq MgJt MpOk} aM{bA(bN cH) aJcY aKaZ aRdG bEbG bWdK cScT} Lj{Ml(Hu Mv Of Qc) NmLu LzHu OfOi} aA{Oi(Mg Ng Of) AxCh aObZ aYdE bAcW} Ne{Iv(Hq Mw Nx) LuNx MuIj IkOe} dE{aF(cR cT) bP(cR cY) aUdN bUbW} Cx{Aj(Bc Dc) Ct(Bb Cv) ChCs} Md{Jp(Of Pc) LxNl NcOm IhIm} Hw{Nf(Of Pg) Hq(Iv Pe) IhOf} aK{aJcX aWbM aXdL bHcZ cLdG} bZ{bQ(bF bJ cX) cG(aY bA)} Ij{LvPg MkJr IhIm IoQc} Jt{Mg(Jp Qa) Im(Mn Ok)} dK{bP(aU cY) cX(aJ dH)} Ao{BgDg CtFr DdDk} Lx{Mp(Mu Nc) MtMu} Mv{MpNg MtOe NvOk} Nl{NtNj NuHq MeNg} Qe{Hu(Mj Mt) NnMg} Pg{Nv(Lw Ok) LvNg} cZ{aEbB aQcH bOcE} Af{AlBn DbDg} Ax{BgDi CsFr} Mw{NnNy NfPa} Iv{NsNc JpJr} aI{aUcP cWdA} aS{dI(bI cW)} aX{bGdL cLdF} AdCsDk ArBoDg AwCvFw NdImOf JiLhOk aCaEbB aFbAcE aGcRdF aHaUcP aZcJcO bNcVcX Constrained panels with 2 analytes, where 1.0E-7 >= 'AUC p-value' > 0. Contains 35 panels of 11,937 total panels evaluated. : dE(aK aL aN aW aY bA bH bW bX bZ cF cR cT dN) Pf(Fp Lz Ml Mx Nc Nl Oh Qb) Fr(Nc Oh) bA(aM cX) bP(cF cS) cR(aE dN) BgBo NcQc HvIm cCdN cTcX Constrained panels with 2 analytes, where 1.0E-6 >= 'AUC p-value' > 1.0E-7. Contains 20 panels of 11,937 total panels evaluated. : Gp(Ap As Cp Cw) Mu(Hv Il Qc) Fr(Ii Nn) Pf(Js Mj) aE(bA cT) dN(aN bZ) AoCo BoCt HvIn aMcT bAcF Constrained panels with 2 analytes, where 1.0E-5 >= 'AUC p-value' > 1.0E-6. Contains 41 panels of 11,937 total panels evaluated. : Nc(Jg Jh Jk Li Mv Wm) dN(aY bG bH bL cD) cT(bG bL bZ cW) Nk(Ij Jk Li) Qc(Jh Mh Ni) Bg(Ax Gp) aE(aX bZ) bA(aN cS) bP(aK bZ) cC(cF cS) BaGp BoCo CwFw FrNi MvHv MwOh NlJh aMaX aWdB bHcW Constrained panels with 2 analytes, where 1.0E-4 >= 'AUC p-value' > 1.0E-5. Contains 90 panels of 11,937 total panels evaluated. : Nc(Ij Im Jp Mg Mu Nq On Pe Pz) Nl(Fr Hu Ij Jg Jk Mv Pz Qc) Hv(Fr Ma Mw My Ny Pz Wm) Mx(Fr Ir Is Mw On Qe) aM(aA aY bH cP dG dN) aE(aN aZ bH cC cS) Qc(Mv Nk Pc Pz) bA(aD bF bZ cW) Bn(Co Dk Fr) Ij(Na Ni Oh) Li(Ni Pz Qb) cT(aD aZ bF) dB(aN cR dN) Aw(Ax Gp) Cx(Co Cq) Fr(Gp Md) Mv(Nk Oh) Ir(Js Og) dN(bF cO) BgCs BoEf CpDb CuFw WmIt MaHu MlMu NkJh ImJs IsOh aKcW bLcS bPdF cCcR Constrained panels with 2 analytes, where 1.0E-3 >= 'AUC p-value' > 1.0E-4. Contains 142 panels of 11,937 total panels evaluated. : Hv(Hu Ir Is Jh Jp Lh Lv Mq Nb No Nq Nx On Pe Pg Qc Qe) Nc(Hu Il Io Ir Is Mw Nb Nh Nr Nx Ny Of Pa Pg Qe) Nl(Ik Ir Is Iv Li Lv Mu Nh Nq Nr Nx Of On Pg Wm) Nk(Hu Ir Jg Nq Ny Of On Pg Pz) Mx(Im Jh Jk Mu Mv Nb Nq Pz) Oh(Im Ma Nq On Qc Qe) cW(aX aY bZ cE cF cR) Wm(Fr Hu Jk Mu Mw) Bc(Aw Bg Co Db) Nr(It Li Mu Mv) aD(aX bH bZ cR) Ii(Mv On Qe) Li(Lu Ma Mu) Og(Im Ni Qe) aE(aH aL aQ) aM(bE bV dA) bP(aL cG cT) Af(Cq Cx) Ax(Co Cp) Bn(Ch Cq) Bo(Al Fr) Dk(Cx Db) Mg(Mu Qc) Mh(Jk Pz) Mw(Ma Ms) Ij(In It) Is(Js Md) On(Js Jt) AwCs EfGp NiJk HwPz ImIt aNaY aQaU bMbZ bXcT Constrained panels with 2 analytes, where 1.0E-2 >= 'AUC p-value' > 1.0E-3. Contains 162 panels of 11,937 total panels evaluated. : Nl(Il Ma Mg Mw Nb Ni Nt Ny Og Pe Qe) Lu(Lw Lx Mi Mq Nm No Ok On Pa Pe) Hv(Jg Jk Mg Mj Mn Nd Of Om Qd) Og(Jp Mw Nb Nc Nq On Pe Pz Qc) Wm(Il Ip Ma Na Ne Of Oi Qc) Mx(Ij Iv Li Ma Mj Nn Ny Qa) Oh(Jg Jp Lh Mu Nn Ny Pe Qa) Ni(Hu Ip Is Mw Nq Of) Nk(Il Is Mg Nb Pe Qe) Ma(It Js Mu Na Nc) Ne(Hu Ij Ir Nh Nr) aM(aZ bX cF cQ dI) cC(aN bM bU bX cP) Cx(Ch Dc Dg Ef) Ax(Dk Ef Fr) Cs(Cp Dk Ef) Mg(In Nb Nq) Mh(Im My Of) Na(Il Iv Pe) Ii(Jh Jk Nb) Js(Pz Qa Qe) On(Md Mp Mt) bF(bP cP cZ) cF(bH dA dB) dF(aN aZ cX) Bg(Ba Ex) Bn(Ad Dg) Ml(Li My) It(Nq Qc) Iv(In Nc) aD(bV dA) aY(bP cL) bG(cP dG) bN(aN cR) bX(cD cO) dC(dA dG) BcEf MdJp HwOf HxIj JkLj aAcX aSdI bZcP

Figure 26 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 8.3E1 | 9.2E1 | 9.1E1 | 1.0E2 | 5.5E1 | 5.8E1 | 1.0E1 | 2.6E1 | 2.6E2 | 2.4E2 | 61 | 21 | 61 | 21 | 0.57 |
| Ad | ug/mL | 5.6E-2 | 6.2E-2 | 9.5E-2 | 9.8E-2 | 9.6E-2 | 9.1E-2 | 9.4E-4 | 9.4E-3 | 3.6E-1 | 3.2E-1 | 43 | 16 | 43 | 16 | 0.54 |
| Af | ng/mL | 1.6E0 | 7.9E-1 | 2.1E1 | 1.9E1 | 6.9E1 | 6.1E1 | 1.7E-3 | 1.7E-3 | 4.0E2 | 2.5E2 | 43 | 16 | 43 | 16 | 0.40 |
| Aj | ug/mL | 2.7E0 | 5.0E-1 | 3.0E0 | 1.6E0 | 2.7E0 | 2.1E0 | 4.1E-3 | 3.5E-3 | 6.1E0 | 5.8E0 | 43 | 16 | 43 | 16 | 0.37 |
| Al | mg/mL | 1.2E-4 | 1.6E-4 | 3.2E-4 | 3.3E-4 | 4.6E-4 | 4.1E-4 | 9.0E-6 | 7.6E-6 | 1.9E-3 | 1.5E-3 | 43 | 16 | 43 | 16 | 0.54 |
| An | U/mL | 7.5E1 | 5.0E1 | 2.2E2 | 3.6E2 | 3.9E2 | 7.6E2 | 7.7E-1 | 9.6E-1 | 2.0E3 | 3.0E3 | 43 | 16 | 43 | 16 | 0.45 |
| Ao | pg/mL | 1.1E2 | 9.8E1 | 2.2E2 | 1.6E2 | 5.7E2 | 1.5E2 | 6.7E0 | 9.9E0 | 3.8E3 | 6.0E2 | 43 | 16 | 43 | 16 | 0.54 |
| Ap | ng/mL | 3.9E1 | 4.1E1 | 5.2E1 | 4.4E1 | 4.9E1 | 2.8E1 | 8.4E-5 | 8.7E0 | 2.5E2 | 1.0E2 | 43 | 16 | 43 | 16 | 0.49 |
| Ar | ng/mL | 1.2E0 | 2.2E0 | 5.6E0 | 3.8E0 | 1.1E1 | 5.8E0 | 1.1E-1 | 3.4E-3 | 5.1E1 | 1.9E1 | 43 | 16 | 43 | 16 | 0.52 |
| As | ng/mL | 1.0E-2 | 1.0E-2 | 1.7E-2 | 1.8E-2 | 2.4E-2 | 2.3E-2 | 1.7E-3 | 1.7E-3 | 1.3E-1 | 8.2E-2 | 43 | 16 | 43 | 16 | 0.52 |
| Aw | pg/mL | 1.6E1 | 1.6E1 | 1.7E1 | 1.6E1 | 5.9E0 | 5.9E0 | 9.3E0 | 2.9E-2 | 3.7E1 | 2.5E1 | 43 | 16 | 43 | 16 | 0.49 |
| Ax | ng/mL | 2.7E0 | 7.7E0 | 1.3E1 | 5.2E1 | 3.0E1 | 1.5E2 | 4.9E-2 | 1.2E-2 | 1.5E2 | 6.2E2 | 43 | 16 | 43 | 16 | 0.60 |
| Ba | ng/mL | 1.0E2 | 7.8E1 | 6.9E2 | 1.9E2 | 1.5E3 | 2.7E2 | 3.1E0 | 6.3E0 | 7.5E3 | 1.0E3 | 43 | 16 | 43 | 16 | 0.47 |
| Bb | ng/mL | 5.7E0 | 6.4E0 | 6.4E0 | 8.2E0 | 5.3E0 | 6.9E0 | 4.1E-1 | 4.2E-1 | 2.0E1 | 1.9E1 | 43 | 16 | 43 | 16 | 0.56 |
| Bc | ng/mL | 4.0E1 | 5.6E1 | 1.4E2 | 6.7E1 | 2.4E2 | 4.9E1 | 2.2E-1 | 8.0E0 | 1.2E3 | 1.6E2 | 43 | 16 | 43 | 16 | 0.55 |
| Bg | ng/mL | 7.2E-2 | 1.1E-1 | 2.8E0 | 7.8E-1 | 1.1E1 | 1.3E0 | 5.3E-4 | 2.6E-2 | 7.1E1 | 3.7E0 | 43 | 16 | 43 | 16 | 0.52 |
| Bn | ng/mL | 7.0E-1 | 5.6E-2 | 2.0E0 | 1.2E0 | 2.5E0 | 2.2E0 | 5.6E-2 | 5.6E-2 | 8.6E0 | 6.5E0 | 43 | 16 | 43 | 16 | 0.39 |
| Bo | ng/mL | 9.6E0 | 1.7E1 | 1.3E1 | 1.8E1 | 1.3E1 | 1.4E1 | 1.6E-2 | 1.6E-2 | 4.6E1 | 4.1E1 | 43 | 16 | 43 | 16 | 0.63 |
| Ch | uIU/mL | 2.2E0 | 7.3E-1 | 1.8E1 | 9.1E0 | 4.2E1 | 2.6E1 | 3.9E-2 | 1.2E-1 | 1.9E2 | 1.1E2 | 43 | 16 | 43 | 16 | 0.37 |
| Co | pg/mL | 4.2E1 | 5.3E1 | 5.0E2 | 1.2E2 | 2.5E3 | 2.0E2 | 1.5E-1 | 1.6E1 | 1.7E4 | 8.2E2 | 43 | 16 | 43 | 16 | 0.52 |
| Cp | ng/mL | 2.8E1 | 2.3E1 | 3.6E1 | 2.9E1 | 3.0E1 | 1.7E1 | 1.1E1 | 1.0E1 | 1.9E2 | 6.9E1 | 43 | 16 | 43 | 16 | 0.42 |
| Cq | ng/mL | 3.1E-2 | 3.5E-2 | 1.6E-1 | 8.8E-2 | 7.8E-1 | 1.3E-1 | 8.0E-4 | 8.0E-4 | 5.1E0 | 4.0E-1 | 43 | 16 | 43 | 16 | 0.54 |
| Cs | ng/mL | 7.9E1 | 3.2E2 | 3.0E2 | 1.6E3 | 5.8E2 | 4.4E3 | 1.3E0 | 9.1E0 | 3.0E3 | 1.8E4 | 43 | 16 | 43 | 16 | 0.62 |
| Ct | ng/mL | 5.9E-1 | 6.9E-2 | 5.0E1 | 3.9E0 | 1.3E2 | 1.2E1 | 1.8E-2 | 1.5E-2 | 6.2E2 | 4.9E1 | 43 | 16 | 43 | 16 | 0.30 |
| Cu | ng/mL | 2.8E-1 | 3.3E-1 | 4.2E-1 | 6.1E-1 | 6.7E-1 | 1.1E0 | 3.5E-2 | 5.6E-2 | 4.5E0 | 4.5E0 | 43 | 16 | 43 | 16 | 0.56 |
| Cv | ng/mL | 9.1E0 | 1.1E1 | 2.8E1 | 4.1E1 | 5.2E1 | 7.7E1 | 2.6E-2 | 5.1E-2 | 3.1E2 | 2.9E2 | 43 | 16 | 43 | 16 | 0.53 |
| Cw | mIU/mL | 2.9E-2 | 3.4E-2 | 3.8E-2 | 3.7E-2 | 2.9E-2 | 3.0E-2 | 4.8E-3 | 4.1E-3 | 1.4E-1 | 1.0E-1 | 43 | 16 | 43 | 16 | 0.48 |
| Cx | ng/mL | 1.3E0 | 2.9E-2 | 6.7E1 | 7.5E1 | 1.1E2 | 1.4E2 | 9.3E-5 | 9.3E-5 | 3.9E2 | 3.9E2 | 43 | 16 | 43 | 16 | 0.44 |
| Db | ug/mL | 5.3E0 | 6.7E0 | 7.6E0 | 6.9E0 | 1.1E1 | 5.1E0 | 8.2E-1 | 1.1E0 | 5.9E1 | 2.1E1 | 43 | 16 | 43 | 16 | 0.58 |
| Dc | nmol/L | 3.1E-2 | 4.2E-2 | 9.3E-2 | 9.5E-2 | 2.5E-1 | 1.9E-1 | 3.0E-4 | 1.0E-3 | 1.6E0 | 7.7E-1 | 43 | 16 | 43 | 16 | 0.58 |
| Dd | ng/mL | 8.9E-2 | 1.5E-1 | 2.6E-1 | 1.9E-1 | 4.1E-1 | 1.8E-1 | 1.1E-3 | 3.3E-3 | 1.9E0 | 5.6E-1 | 43 | 16 | 43 | 16 | 0.51 |
| De | ng/mL | 3.4E-3 | 3.4E-3 | 1.0E-1 | 5.1E-2 | 1.4E-1 | 8.5E-2 | 3.4E-3 | 3.4E-3 | 6.2E-1 | 3.1E-1 | 43 | 16 | 43 | 16 | 0.40 |
| Dg | ng/mL | 4.3E1 | 3.9E1 | 5.8E1 | 5.0E1 | 5.0E1 | 3.7E1 | 1.0E-1 | 1.1E0 | 1.9E2 | 1.2E2 | 43 | 16 | 43 | 16 | 0.49 |
| Di | pg/mL | 1.8E0 | 2.3E0 | 2.2E0 | 2.5E0 | 2.2E0 | 2.1E0 | 1.8E-1 | 1.8E-1 | 7.8E0 | 6.0E0 | 43 | 16 | 43 | 16 | 0.55 |
| Dk | uIU/mL | 1.8E-2 | 1.5E-2 | 4.4E-2 | 3.6E-2 | 6.9E-2 | 5.8E-2 | 1.1E-4 | 5.8E-3 | 3.4E-1 | 2.4E-1 | 43 | 16 | 43 | 16 | 0.46 |
| Dl | ng/mL | 2.6E2 | 2.0E2 | 3.7E2 | 2.8E2 | 2.9E2 | 2.9E2 | 2.5E0 | 5.5E0 | 1.1E3 | 1.1E3 | 43 | 16 | 43 | 16 | 0.40 |
| Dp | ng/ml | 2.7E0 | 3.3E0 | 5.9E0 | 8.8E0 | 8.2E0 | 1.4E1 | 3.7E-3 | 3.7E-3 | 3.7E1 | 5.6E1 | 43 | 16 | 43 | 16 | 0.53 |
| Ef | ng/ml | 2.0E-1 | 8.5E-2 | 9.6E-1 | 5.4E-1 | 1.7E0 | 1.3E0 | 2.1E-3 | 1.3E-2 | 8.6E0 | 5.2E0 | 43 | 17 | 43 | 17 | 0.43 |
| Wm | % | 3.8E-1 | 5.9E-1 | 3.1E0 | 1.0E2 | 7.4E0 | 2.8E2 | 8.5E-2 | 8.5E-2 | 4.0E1 | 9.3E2 | 43 | 17 | 43 | 17 | 0.55 |
| Ed | pg/mL | 5.2E-1 | 2.8E0 | 2.0E1 | 7.1E1 | 4.1E1 | 1.3E2 | 5.2E-1 | 5.2E-1 | 2.2E2 | 5.0E2 | 43 | 16 | 43 | 16 | 0.62 |
| Tj | pg/mL | 3.7E-1 | 3.7E-1 | 6.2E1 | 2.3E1 | 3.5E2 | 7.4E1 | 3.6E-1 | 3.7E-1 | 2.3E3 | 3.1E2 | 43 | 17 | 43 | 17 | 0.58 |
| Po | pg/mL | 8.6E-1 | 2.0E0 | 1.0E1 | 1.2E1 | 2.6E1 | 2.9E1 | 2.6E-2 | 2.6E-2 | 1.8E2 | 1.4E2 | 61 | 24 | 61 | 24 | 0.51 |
| Ti | ug/mL | 5.9E0 | 6.8E0 | 6.3E0 | 6.0E0 | 5.1E0 | 4.5E0 | 1.9E-1 | 8.0E-1 | 1.7E1 | 1.4E1 | 30 | 8 | 30 | 8 | 0.52 |
| Et | ng/ml | 1.9E3 | 2.3E3 | 2.0E3 | 2.5E3 | 1.1E3 | 1.2E3 | 1.8E2 | 5.0E2 | 4.4E3 | 5.0E3 | 61 | 24 | 61 | 24 | 0.61 |
| Th | ug/mL | 1.4E0 | 8.1E-1 | 1.6E0 | 1.0E0 | 9.9E-1 | 1.2E0 | 2.0E-1 | 2.6E-3 | 4.6E0 | 3.9E0 | 30 | 8 | 30 | 8 | 0.26 |
| Fa | ng/ml | 3.1E1 | 8.8E1 | 8.8E1 | 4.4E2 | 1.4E2 | 1.0E3 | 1.5E0 | 5.9E0 | 7.5E2 | 3.7E3 | 42 | 17 | 42 | 17 | 0.69 |
| Ez | ng/ml | 7.0E0 | 2.5E0 | 2.2E1 | 5.8E0 | 4.6E1 | 7.7E0 | 1.3E-2 | 9.5E-2 | 2.4E2 | 2.5E1 | 43 | 16 | 43 | 16 | 0.37 |
| Fb | ng/ml | 2.5E1 | 3.2E1 | 2.3E1 | 2.8E1 | 9.0E0 | 1.1E1 | 2.7E0 | 5.9E-1 | 3.8E1 | 4.0E1 | 42 | 17 | 42 | 17 | 0.69 |
| Ex | ng/ml | 7.1E-2 | 1.4E-1 | 1.7E-1 | 1.5E-1 | 3.1E-1 | 1.2E-1 | 1.7E-4 | 1.7E-4 | 1.5E0 | 4.4E-1 | 24 | 12 | 24 | 12 | 0.62 |
| Fn | ng/ml | 2.1E-1 | 3.6E0 | 4.0E0 | 5.6E0 | 6.5E0 | 5.9E0 | 2.1E-1 | 2.1E-1 | 2.1E1 | 1.6E1 | 43 | 16 | 43 | 16 | 0.63 |
| Fp | ng/ml | 2.1E1 | 4.6E1 | 3.5E1 | 4.4E1 | 3.4E1 | 3.6E1 | 6.6E-1 | 1.6E0 | 1.3E2 | 1.2E2 | 62 | 25 | 62 | 25 | 0.58 |
| Fr | ng/ml | 4.2E4 | 5.8E4 | 1.1E5 | 1.6E5 | 1.5E5 | 2.2E5 | 1.9E3 | 2.5E3 | 7.2E5 | 7.9E5 | 62 | 25 | 62 | 25 | 0.57 |
| Fw | pg/ml | 8.5E-1 | 1.1E0 | 1.3E1 | 8.7E1 | 3.7E1 | 2.4E2 | 1.2E-1 | 1.2E-1 | 2.3E2 | 9.1E2 | 42 | 17 | 42 | 17 | 0.59 |
| Fy | ng/ml | 4.7E1 | 4.7E1 | 6.9E1 | 9.3E1 | 6.0E1 | 1.3E2 | 1.2E-1 | 2.7E0 | 2.0E2 | 5.0E2 | 43 | 16 | 43 | 16 | 0.51 |

Figure 27

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Gl | pg/ml | 9.8E3 | 1.0E4 | 1.2E4 | 1.3E4 | 9.3E3 | 1.0E4 | 4.0E2 | 1.7E3 | 3.3E4 | 3.0E4 | 42 | 17 | 42 | 17 | 0.50 |
| Gp | U/ml | 1.3E0 | 8.5E-1 | 3.9E0 | 4.3E0 | 5.5E0 | 1.1E1 | 1.3E-3 | 1.5E-2 | 2.3E1 | 4.8E1 | 43 | 17 | 43 | 17 | 0.40 |
| Gz | ug/ml | 1.2E0 | 9.8E-1 | 5.4E0 | 5.1E0 | 5.3E0 | 6.8E0 | 1.6E-1 | 1.3E-1 | 1.1E1 | 1.9E1 | 23 | 12 | 23 | 12 | 0.47 |
| Ha | ng/ml | 2.7E0 | 5.0E0 | 1.0E1 | 1.3E1 | 2.0E1 | 2.5E1 | 1.7E-2 | 1.7E-2 | 1.0E2 | 1.0E2 | 43 | 16 | 43 | 16 | 0.58 |
| Nm | pg/ml | 2.4E4 | 2.3E4 | 3.5E4 | 3.6E4 | 3.6E4 | 3.8E4 | 1.0E-9 | 1.0E-9 | 1.5E5 | 1.2E5 | 62 | 24 | 62 | 24 | 0.49 |
| Nn | pg/ml | 1.7E2 | 1.6E2 | 6.4E2 | 1.2E3 | 1.3E3 | 3.4E3 | 1.0E-9 | 3.3E0 | 8.0E3 | 1.7E4 | 62 | 24 | 62 | 24 | 0.52 |
| No | pg/ml | 2.1E1 | 2.3E1 | 3.4E1 | 4.4E1 | 4.7E1 | 8.2E1 | 1.0E-9 | 3.3E-1 | 2.6E2 | 4.1E2 | 62 | 24 | 62 | 24 | 0.52 |
| Nq | pg/ml | 3.1E-1 | 1.7E0 | 8.9E0 | 1.2E1 | 2.6E1 | 3.4E1 | 1.0E-9 | 1.0E-9 | 1.7E2 | 1.7E2 | 62 | 24 | 62 | 24 | 0.57 |
| Nr | pg/ml | 1.8E0 | 6.2E0 | 2.8E1 | 2.3E1 | 1.0E2 | 6.3E1 | 1.0E-9 | 1.0E-9 | 7.2E2 | 3.1E2 | 62 | 24 | 62 | 24 | 0.55 |
| Ns | pg/ml | 1.0E-9 | 1.0E-9 | 4.3E0 | 1.5E-1 | 1.9E1 | 7.3E-1 | 1.0E-9 | 1.0E-9 | 1.0E2 | 3.6E0 | 62 | 24 | 62 | 24 | 0.49 |
| Nt | pg/ml | 1.5E2 | 1.4E2 | 1.7E2 | 1.5E2 | 9.6E1 | 7.1E1 | 4.7E1 | 2.3E1 | 4.3E2 | 3.1E2 | 62 | 24 | 62 | 24 | 0.45 |
| Nu | pg/ml | 4.0E1 | 4.8E1 | 8.9E1 | 8.1E1 | 1.2E2 | 9.7E1 | 1.0E-9 | 1.0E-9 | 6.3E2 | 3.4E2 | 62 | 24 | 62 | 24 | 0.49 |
| Lu | pg/ml | 1.0E4 | 1.0E4 | 1.2E4 | 1.1E4 | 1.3E4 | 7.1E3 | 7.1E2 | 1.9E3 | 8.4E4 | 3.6E4 | 62 | 25 | 62 | 25 | 0.58 |
| Lv | pg/ml | 8.8E0 | 1.0E-9 | 1.9E1 | 1.8E1 | 2.7E1 | 3.5E1 | 1.0E-9 | 1.0E-9 | 1.2E2 | 1.6E2 | 62 | 25 | 62 | 25 | 0.46 |
| Lw | pg/ml | 1.0E-9 | 1.0E-9 | 3.2E-1 | 1.0E-9 | 1.9E0 | 0.0E0 | 1.0E-9 | 1.0E-9 | 1.4E1 | 1.0E-9 | 62 | 25 | 62 | 25 | 0.48 |
| Lx | pg/ml | 1.1E1 | 1.1E2 | 2.1E2 | 2.9E2 | 6.2E2 | 8.8E2 | 1.0E-9 | 1.0E-9 | 4.4E3 | 4.5E3 | 62 | 25 | 62 | 25 | 0.62 |
| Ly | pg/ml | 1.0E-9 | 1.1E1 | 2.0E1 | 1.7E1 | 3.2E1 | 2.0E1 | 1.0E-9 | 1.0E-9 | 1.6E2 | 7.0E1 | 62 | 25 | 62 | 25 | 0.52 |
| Lz | pg/ml | 1.0E-9 | 1.0E-9 | 5.7E0 | 1.6E0 | 2.9E1 | 7.3E0 | 1.0E-9 | 1.0E-9 | 1.9E2 | 3.7E1 | 62 | 25 | 62 | 25 | 0.49 |
| Ma | pg/ml | 4.0E2 | 5.7E2 | 1.4E3 | 8.8E2 | 2.5E3 | 1.3E3 | 1.0E-9 | 2.6E1 | 1.5E4 | 5.9E3 | 62 | 25 | 62 | 25 | 0.49 |
| Mb | pg/ml | 3.3E1 | 2.8E1 | 3.8E1 | 3.5E1 | 1.9E1 | 1.6E1 | 1.4E1 | 1.4E1 | 1.1E2 | 6.1E1 | 62 | 25 | 62 | 25 | 0.44 |
| Mc | pg/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 62 | 25 | 62 | 25 | 0.50 |
| Md | pg/ml | 1.0E-9 | 1.0E-9 | 8.9E-1 | 2.2E-1 | 3.3E0 | 1.1E0 | 1.0E-9 | 1.0E-9 | 1.6E1 | 5.5E0 | 62 | 25 | 62 | 25 | 0.46 |
| Me | pg/ml | 2.6E1 | 2.8E1 | 2.6E1 | 2.5E1 | 1.8E1 | 1.4E1 | 1.0E-9 | 1.2E0 | 7.2E1 | 5.3E1 | 62 | 25 | 62 | 25 | 0.50 |
| Mf | pg/ml | 1.0E-9 | 1.0E-9 | 6.7E-1 | 3.2E-1 | 1.6E0 | 9.0E-1 | 1.0E-9 | 1.0E-9 | 7.1E0 | 4.4E0 | 62 | 25 | 62 | 25 | 0.50 |
| Mg | pg/ml | 2.0E0 | 1.8E0 | 8.6E0 | 6.6E0 | 1.3E1 | 1.0E1 | 1.0E-9 | 1.0E-9 | 5.9E1 | 3.9E1 | 62 | 25 | 62 | 25 | 0.46 |
| Mh | pg/ml | 1.0E-9 | 1.0E-9 | 9.1E-1 | 2.3E0 | 3.9E0 | 8.5E0 | 1.0E-9 | 1.0E-9 | 2.9E1 | 4.2E1 | 62 | 25 | 62 | 25 | 0.55 |
| Mi | pg/ml | 1.0E-9 | 1.0E-9 | 1.2E0 | 1.0E-9 | 9.1E0 | 0.0E0 | 1.0E-9 | 1.0E-9 | 7.1E1 | 1.0E-9 | 62 | 25 | 62 | 25 | 0.48 |
| Mj | pg/ml | 1.0E-9 | 1.0E-9 | 2.4E0 | 7.7E0 | 7.5E0 | 2.4E1 | 1.0E-9 | 1.0E-9 | 3.8E1 | 1.1E2 | 62 | 25 | 62 | 25 | 0.54 |
| Mk | pg/ml | 2.7E0 | 4.3E0 | 3.1E1 | 6.3E0 | 1.7E2 | 8.3E0 | 1.0E-9 | 1.0E-9 | 1.3E3 | 3.6E1 | 62 | 25 | 62 | 25 | 0.50 |
| Ml | pg/ml | 1.0E-9 | 1.0E-9 | 3.1E0 | 2.2E0 | 9.9E0 | 5.0E0 | 1.0E-9 | 1.0E-9 | 6.4E1 | 1.9E1 | 62 | 25 | 62 | 25 | 0.49 |
| Mm | pg/ml | 7.4E2 | 8.7E2 | 1.1E3 | 1.2E3 | 1.2E3 | 1.3E3 | 1.3E1 | 1.9E1 | 6.3E3 | 6.1E3 | 62 | 25 | 62 | 25 | 0.51 |
| Mn | pg/ml | 6.7E0 | 7.1E0 | 1.0E1 | 1.4E1 | 1.3E1 | 2.5E1 | 1.0E-9 | 1.0E-9 | 6.8E1 | 1.3E2 | 62 | 25 | 62 | 25 | 0.55 |
| Mp | pg/ml | 1.0E-9 | 1.0E-9 | 1.4E1 | 9.3E0 | 7.9E1 | 2.0E1 | 1.0E-9 | 1.0E-9 | 6.3E2 | 9.2E1 | 62 | 25 | 62 | 25 | 0.55 |
| Mq | pg/ml | 1.0E-9 | 1.0E-9 | 3.9E0 | 6.1E0 | 1.7E1 | 1.8E1 | 1.0E-9 | 1.0E-9 | 1.2E2 | 8.6E1 | 62 | 25 | 62 | 25 | 0.53 |
| Mr | pg/ml | 2.3E-1 | 1.0E-9 | 1.8E1 | 6.4E1 | 5.9E1 | 3.0E2 | 1.0E-9 | 1.0E-9 | 3.9E2 | 1.5E3 | 62 | 25 | 62 | 25 | 0.45 |
| Ms | pg/ml | 3.9E2 | 3.2E2 | 5.5E2 | 3.7E2 | 5.2E2 | 3.9E2 | 1.0E-9 | 1.0E-9 | 2.2E3 | 1.5E3 | 62 | 25 | 62 | 25 | 0.41 |
| Mt | pg/ml | 9.0E-1 | 1.6E0 | 6.9E0 | 1.0E1 | 2.2E1 | 2.8E1 | 1.0E-9 | 1.0E-9 | 1.4E2 | 1.0E2 | 62 | 25 | 62 | 25 | 0.56 |
| Mu | pg/ml | 1.0E-9 | 1.0E-9 | 5.9E-1 | 4.9E-1 | 1.8E0 | 1.6E0 | 1.0E-9 | 1.0E-9 | 1.0E1 | 7.3E0 | 62 | 25 | 62 | 25 | 0.47 |
| Mv | pg/ml | 1.0E-9 | 1.0E-9 | 3.9E1 | 1.1E2 | 1.3E2 | 5.1E2 | 1.0E-9 | 1.0E-9 | 8.4E2 | 2.5E3 | 62 | 25 | 62 | 25 | 0.47 |
| Mw | pg/ml | 3.1E1 | 7.2E1 | 1.7E2 | 3.2E2 | 4.2E2 | 1.2E3 | 1.0E-9 | 1.0E-9 | 2.2E3 | 5.9E3 | 62 | 25 | 62 | 25 | 0.60 |
| Mx | pg/ml | 1.0E-9 | 1.0E-9 | 1.8E-1 | 2.2E-1 | 5.3E-1 | 5.2E-1 | 1.0E-9 | 1.0E-9 | 2.7E0 | 2.1E0 | 62 | 25 | 62 | 25 | 0.54 |
| My | pg/ml | 1.0E-9 | 1.0E-9 | 1.2E2 | 2.7E2 | 5.1E2 | 9.6E2 | 1.0E-9 | 1.0E-9 | 3.6E3 | 4.6E3 | 62 | 25 | 62 | 25 | 0.53 |
| Mz | pg/ml | 1.5E1 | 1.7E1 | 2.6E1 | 3.2E1 | 4.4E1 | 3.4E1 | 1.0E-9 | 1.0E-9 | 3.0E2 | 1.5E2 | 62 | 25 | 62 | 25 | 0.59 |
| Na | pg/ml | 1.0E-9 | 1.0E-9 | 3.4E-1 | 1.1E0 | 1.2E0 | 3.5E0 | 1.0E-9 | 1.0E-9 | 7.2E0 | 1.6E1 | 62 | 25 | 62 | 25 | 0.50 |
| Nb | pg/ml | 2.0E0 | 2.5E0 | 2.6E0 | 3.7E0 | 3.2E0 | 3.8E0 | 1.0E-9 | 1.0E-9 | 2.3E1 | 1.7E1 | 62 | 25 | 62 | 25 | 0.60 |
| Nc | pg/ml | 1.8E2 | 2.9E2 | 3.6E2 | 4.9E2 | 4.0E2 | 5.3E2 | 1.0E-9 | 1.0E-9 | 1.4E3 | 2.1E3 | 62 | 25 | 62 | 25 | 0.57 |
| Nd | pg/ml | 5.7E0 | 6.5E0 | 3.3E1 | 1.8E1 | 1.6E2 | 2.2E1 | 1.0E-9 | 1.0E-9 | 1.2E3 | 9.4E1 | 62 | 25 | 62 | 25 | 0.56 |
| Ne | pg/ml | 3.2E2 | 4.0E2 | 3.7E2 | 4.9E2 | 3.3E2 | 4.4E2 | 1.0E-9 | 1.0E-9 | 1.5E3 | 1.7E3 | 62 | 25 | 62 | 25 | 0.56 |
| Nf | pg/ml | 1.0E-9 | 1.0E-9 | 1.5E0 | 3.0E0 | 5.5E0 | 1.0E1 | 1.0E-9 | 1.0E-9 | 3.5E1 | 5.1E1 | 62 | 25 | 62 | 25 | 0.54 |
| Ng | pg/ml | 2.7E1 | 6.2E0 | 1.1E2 | 9.5E1 | 1.5E2 | 2.6E2 | 1.0E-9 | 1.0E-9 | 6.2E2 | 1.2E3 | 62 | 25 | 62 | 25 | 0.38 |
| Nh | pg/ml | 4.2E1 | 5.5E1 | 5.3E1 | 6.0E1 | 4.2E1 | 5.1E1 | 1.0E-9 | 1.0E-9 | 1.6E2 | 2.2E2 | 62 | 25 | 62 | 25 | 0.54 |
| Ni | pg/ml | 7.1E0 | 1.0E-9 | 9.7E1 | 8.8E1 | 1.4E2 | 1.4E2 | 1.0E-9 | 1.0E-9 | 5.7E2 | 5.7E2 | 62 | 25 | 62 | 25 | 0.47 |
| Nj | pg/ml | 3.2E0 | 2.9E0 | 6.7E0 | 6.2E0 | 7.9E0 | 7.4E0 | 1.0E-9 | 1.0E-9 | 3.6E1 | 2.9E1 | 62 | 25 | 62 | 25 | 0.50 |
| Nk | pg/ml | 1.6E1 | 2.7E1 | 3.1E1 | 4.2E1 | 3.5E1 | 5.4E1 | 1.0E-9 | 1.0E-9 | 1.2E2 | 2.0E2 | 62 | 25 | 62 | 25 | 0.55 |
| Nl | pg/ml | 2.3E1 | 4.2E1 | 3.8E1 | 5.0E1 | 3.9E1 | 4.2E1 | 1.0E-9 | 1.0E-9 | 1.9E2 | 1.4E2 | 62 | 25 | 62 | 25 | 0.60 |
| Tz | pg/ml | 7.0E3 | 6.0E3 | 3.6E4 | 1.0E4 | 1.5E5 | 1.6E4 | 1.0E-9 | 1.9E3 | 1.0E6 | 7.0E4 | 43 | 16 | 43 | 16 | 0.51 |
| Ua | pg/ml | 3.6E3 | 4.4E3 | 1.5E4 | 5.8E3 | 3.4E4 | 4.9E3 | 1.0E-9 | 1.4E3 | 1.9E5 | 2.1E4 | 43 | 16 | 43 | 16 | 0.51 |

Figure 27 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ub | pg/ml | 6.9E2 | 5.1E2 | 1.0E3 | 9.9E2 | 1.1E3 | 1.1E3 | 1.0E-9 | 6.6E1 | 6.4E3 | 4.1E3 | 43 | 16 | 43 | 16 | 0.46 |
| Ue | pg/ml | 3.7E1 | 2.9E1 | 4.8E1 | 3.2E1 | 5.3E1 | 1.9E1 | 9.8E-2 | 8.8E0 | 3.5E2 | 7.4E1 | 43 | 16 | 43 | 16 | 0.39 |
| Uc | pg/ml | 1.1E3 | 9.4E2 | 1.8E3 | 1.9E3 | 2.1E3 | 2.3E3 | 1.0E-9 | 1.1E2 | 9.2E3 | 8.3E3 | 43 | 16 | 43 | 16 | 0.50 |
| Ud | pg/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 43 | 16 | 43 | 16 | 0.50 |
| Hq | pg/ml | 9.6E-1 | 1.2E0 | 4.7E2 | 1.2E1 | 3.6E3 | 4.7E1 | 1.0E-9 | 1.0E-9 | 2.8E4 | 2.3E2 | 61 | 24 | 61 | 24 | 0.53 |
| Hr | pg/ml | 1.0E2 | 1.3E2 | 4.5E2 | 9.7E2 | 9.1E2 | 1.7E3 | 1.0E-9 | 3.9E1 | 5.0E3 | 5.5E3 | 61 | 24 | 61 | 24 | 0.58 |
| Hu | pg/ml | 3.5E1 | 3.1E0 | 8.3E2 | 6.2E2 | 3.9E3 | 1.8E3 | 1.0E-9 | 1.0E-9 | 2.9E4 | 7.9E3 | 61 | 24 | 61 | 24 | 0.36 |
| Hv | pg/ml | 1.7E0 | 1.1E0 | 2.6E0 | 2.0E0 | 2.9E0 | 2.4E0 | 1.0E-9 | 1.0E-9 | 1.8E1 | 1.1E1 | 61 | 24 | 61 | 24 | 0.43 |
| Hw | pg/ml | 5.8E0 | 6.1E0 | 1.3E1 | 1.2E1 | 2.5E1 | 2.1E1 | 1.0E-9 | 1.0E-9 | 1.9E2 | 1.0E2 | 61 | 24 | 61 | 24 | 0.50 |
| Hx | pg/ml | 1.1E1 | 1.6E1 | 2.0E1 | 3.0E1 | 4.9E1 | 3.7E1 | 1.0E-9 | 1.0E-9 | 3.7E2 | 1.6E2 | 61 | 24 | 61 | 24 | 0.62 |
| Ib | ng/ml | 6.0E-2 | 2.5E-2 | 1.8E0 | 7.3E-2 | 6.6E0 | 1.7E-1 | 1.0E-9 | 1.0E-9 | 3.9E1 | 6.8E-1 | 41 | 16 | 41 | 16 | 0.33 |
| Ic | U/ml | 2.2E2 | 2.2E2 | 3.6E2 | 2.1E2 | 6.9E2 | 1.4E2 | 1.2E1 | 1.8E1 | 4.2E3 | 5.4E2 | 41 | 16 | 41 | 16 | 0.48 |
| Id | U/ml | 8.4E-1 | 7.9E-1 | 1.4E0 | 2.1E0 | 1.4E0 | 3.8E0 | 1.0E-9 | 2.4E-1 | 5.0E0 | 1.5E1 | 41 | 16 | 41 | 16 | 0.53 |
| Tt | pg/ml | 1.7E2 | 1.7E2 | 1.7E2 | 1.8E2 | 5.6E1 | 5.5E1 | 7.3E1 | 1.0E2 | 3.6E2 | 2.8E2 | 43 | 16 | 43 | 16 | 0.55 |
| To | pg/ml | 1.6E0 | 6.6E-1 | 1.9E0 | 1.3E0 | 2.0E0 | 1.6E0 | 1.0E-9 | 1.0E-9 | 7.1E0 | 5.1E0 | 43 | 16 | 43 | 16 | 0.42 |
| Tr | pg/ml | 2.7E0 | 5.1E0 | 1.2E1 | 8.5E0 | 4.7E1 | 9.9E0 | 2.4E-1 | 9.2E-1 | 3.1E2 | 3.8E1 | 43 | 16 | 43 | 16 | 0.62 |
| Tn | pg/ml | 2.4E1 | 3.9E1 | 8.6E1 | 5.0E1 | 2.8E2 | 4.1E1 | 2.4E0 | 1.6E1 | 1.8E3 | 1.9E2 | 43 | 16 | 43 | 16 | 0.64 |
| Tv | ng/ml | 1.1E1 | 1.2E1 | 1.7E1 | 6.0E1 | 2.3E1 | 1.9E2 | 1.0E-9 | 1.0E-9 | 1.3E2 | 7.9E2 | 43 | 16 | 43 | 16 | 0.49 |
| Ih | ng/ml | 9.8E1 | 1.4E2 | 2.1E2 | 2.5E2 | 3.2E2 | 2.5E2 | 1.0E-9 | 4.7E0 | 1.7E3 | 9.0E2 | 61 | 25 | 61 | 25 | 0.60 |
| Ii | ng/ml | 1.0E2 | 1.2E2 | 3.4E2 | 2.8E2 | 1.3E3 | 3.4E2 | 8.7E0 | 9.8E0 | 1.0E4 | 1.2E3 | 61 | 25 | 61 | 25 | 0.58 |
| Ij | ng/ml | 8.5E1 | 1.0E2 | 1.5E2 | 1.3E2 | 2.4E2 | 7.8E1 | 2.1E1 | 1.9E1 | 1.8E3 | 3.2E2 | 61 | 24 | 61 | 24 | 0.60 |
| Ik | ng/ml | 2.2E2 | 1.2E2 | 7.3E2 | 4.0E2 | 1.4E3 | 5.3E2 | 1.6E0 | 2.3E0 | 9.7E3 | 1.5E3 | 61 | 25 | 61 | 25 | 0.45 |
| Il | ng/ml | 5.1E2 | 4.7E2 | 1.1E3 | 1.7E3 | 2.2E3 | 3.5E3 | 1.0E-9 | 1.0E-9 | 1.2E4 | 1.2E4 | 61 | 25 | 61 | 25 | 0.46 |
| Im | ng/ml | 2.2E2 | 2.5E2 | 5.3E2 | 6.2E2 | 9.6E2 | 1.1E3 | 5.2E1 | 8.7E1 | 5.6E3 | 5.8E3 | 61 | 25 | 61 | 25 | 0.59 |
| In | ng/ml | 5.6E0 | 3.3E0 | 1.1E1 | 9.1E0 | 1.4E1 | 1.7E1 | 1.0E-9 | 1.0E-9 | 7.0E1 | 8.4E1 | 61 | 25 | 61 | 25 | 0.43 |
| Hb | ng/ml | 2.7E1 | 5.9E1 | 3.4E1 | 6.5E1 | 2.4E1 | 6.2E1 | 4.2E0 | 2.6E0 | 9.2E1 | 2.1E2 | 43 | 17 | 43 | 17 | 0.62 |
| Hc | pg/ml | 8.7E2 | 5.9E2 | 3.7E3 | 7.0E2 | 1.5E4 | 8.9E2 | 1.0E-9 | 1.0E-9 | 1.0E5 | 3.9E3 | 43 | 17 | 43 | 17 | 0.36 |
| Hf | ng/ml | 2.6E2 | 1.9E2 | 5.8E2 | 3.3E2 | 7.5E2 | 3.4E2 | 1.0E-9 | 1.0E-9 | 3.2E3 | 9.9E2 | 43 | 17 | 43 | 17 | 0.42 |
| Io | ng/ml | 8.0E3 | 9.1E3 | 1.4E4 | 1.4E4 | 1.8E4 | 1.3E4 | 1.0E-9 | 1.3E3 | 1.2E5 | 5.4E4 | 61 | 25 | 61 | 25 | 0.51 |
| Ip | ng/ml | 1.3E1 | 3.0E1 | 1.9E1 | 3.1E1 | 2.0E1 | 2.2E1 | 1.0E-9 | 4.2E-1 | 6.4E1 | 8.8E1 | 61 | 25 | 61 | 25 | 0.66 |
| Iq | ug/ml | 3.0E-2 | 1.9E-1 | 8.7E-1 | 1.1E0 | 3.3E0 | 3.6E0 | 1.0E-9 | 1.0E-9 | 1.8E1 | 1.8E1 | 61 | 25 | 61 | 25 | 0.66 |
| Ir | ug/ml | 3.1E-1 | 7.7E-1 | 3.6E0 | 1.9E0 | 2.0E1 | 2.6E0 | 1.0E-9 | 5.0E-2 | 1.6E2 | 1.1E1 | 61 | 25 | 61 | 25 | 0.67 |
| Is | ng/ml | 1.9E0 | 3.5E0 | 6.0E0 | 7.0E0 | 1.2E1 | 8.1E0 | 1.0E-9 | 1.0E0 | 6.2E1 | 3.0E1 | 61 | 25 | 61 | 25 | 0.68 |
| It | ng/ml | 1.9E0 | 3.0E0 | 1.9E1 | 7.3E0 | 1.0E2 | 1.3E1 | 1.0E-9 | 1.0E-9 | 7.7E2 | 5.4E1 | 61 | 25 | 61 | 25 | 0.59 |
| Iu | ng/ml | 1.1E2 | 2.2E2 | 1.1E3 | 1.6E3 | 3.7E3 | 4.9E3 | 1.0E-9 | 1.0E-9 | 2.4E4 | 2.4E4 | 61 | 25 | 61 | 25 | 0.58 |
| Iv | ng/ml | 2.0E1 | 3.2E1 | 4.3E1 | 3.4E1 | 7.4E1 | 2.9E1 | 1.0E-9 | 1.0E-9 | 4.9E2 | 1.0E2 | 61 | 25 | 61 | 25 | 0.55 |
| Iz | ng/ml | 1.6E2 | 1.2E2 | 4.2E2 | 2.5E2 | 6.7E2 | 2.8E2 | 1.8E1 | 8.8E0 | 3.6E3 | 9.2E2 | 43 | 17 | 43 | 17 | 0.46 |
| Rc | pg/ml | 7.1E3 | 5.6E3 | 8.7E3 | 5.9E3 | 6.7E3 | 3.1E3 | 1.1E3 | 6.7E2 | 2.3E4 | 1.0E4 | 43 | 16 | 43 | 16 | 0.42 |
| Rb | pg/ml | 1.2E0 | 1.1E0 | 3.5E0 | 1.8E0 | 4.8E0 | 2.5E0 | 1.0E-9 | 1.0E-9 | 2.0E1 | 9.1E0 | 43 | 16 | 43 | 16 | 0.45 |
| Pz | ng/ml | 4.2E3 | 5.8E3 | 6.7E3 | 4.8E3 | 7.7E3 | 2.1E5 | 1.9E2 | 6.2E2 | 4.8E4 | 1.0E6 | 61 | 24 | 61 | 24 | 0.52 |
| Qa | ng/ml | 3.9E2 | 7.3E3 | 6.2E3 | 8.9E3 | 6.0E3 | 6.5E3 | 4.2E2 | 6.8E2 | 2.9E4 | 2.3E4 | 61 | 24 | 61 | 24 | 0.64 |
| Qb | ng/ml | 1.2E2 | 2.0E2 | 1.6E2 | 2.8E2 | 1.7E2 | 2.4E2 | 6.7E0 | 1.8E1 | 7.3E2 | 8.7E2 | 61 | 24 | 61 | 24 | 0.63 |
| Qc | ng/ml | 3.3E2 | 3.7E2 | 4.3E2 | 6.3E2 | 4.4E2 | 8.9E2 | 1.9E0 | 1.3E1 | 2.1E3 | 4.3E3 | 61 | 24 | 61 | 24 | 0.55 |
| Qd | ng/ml | 1.2E4 | 1.5E4 | 2.0E4 | 2.2E4 | 2.5E4 | 2.2E4 | 2.0E3 | 1.7E3 | 1.3E5 | 9.1E4 | 61 | 24 | 61 | 24 | 0.52 |
| Qe | ng/ml | 1.5E3 | 1.8E3 | 1.8E3 | 2.5E3 | 1.5E3 | 2.6E3 | 1.4E2 | 1.8E2 | 7.4E3 | 1.3E4 | 61 | 24 | 61 | 24 | 0.60 |
| Jd | ng/ml | 2.0E0 | 1.5E0 | 4.2E0 | 1.6E0 | 1.1E1 | 1.4E0 | 1.0E-9 | 1.0E-9 | 7.3E1 | 4.3E0 | 43 | 16 | 43 | 16 | 0.40 |
| Je | ng/ml | 2.9E-1 | 5.7E-1 | 1.6E0 | 1.2E0 | 2.2E0 | 1.5E0 | 1.0E-9 | 1.0E-9 | 7.0E0 | 4.3E0 | 43 | 16 | 43 | 16 | 0.49 |
| Jf | ng/ml | 1.0E-9 | 7.3E-1 | 1.6E0 | 1.5E0 | 2.8E0 | 2.1E0 | 1.0E-9 | 1.0E-9 | 9.6E0 | 7.7E0 | 43 | 16 | 43 | 16 | 0.53 |
| Jg | ng/ml | 7.6E2 | 7.7E2 | 9.9E2 | 1.1E3 | 7.9E2 | 1.2E3 | 1.3E1 | 5.9E1 | 3.4E3 | 5.3E3 | 61 | 24 | 61 | 24 | 0.49 |
| Jh | ng/ml | 5.4E0 | 2.6E0 | 1.8E1 | 2.7E1 | 4.6E1 | 9.6E1 | 1.0E-9 | 1.0E-9 | 2.6E2 | 4.7E2 | 61 | 24 | 61 | 24 | 0.45 |
| Ji | ng/ml | 7.0E1 | 8.5E1 | 1.1E2 | 1.3E2 | 8.6E1 | 9.6E1 | 1.3E1 | 2.2E1 | 3.6E2 | 4.1E2 | 61 | 24 | 61 | 24 | 0.60 |
| Sr | pg/mL | 6.0E2 | 8.7E2 | 8.7E2 | 1.2E3 | 9.4E2 | 1.3E3 | 1.0E-9 | 1.0E-9 | 4.8E3 | 5.1E3 | 40 | 16 | 40 | 16 | 0.58 |
| Ss | pg/mL | 1.6E5 | 4.8E4 | 1.9E5 | 9.7E4 | 2.4E5 | 9.1E4 | 2.7E3 | 1.1E4 | 1.3E6 | 3.0E5 | 40 | 16 | 40 | 16 | 0.39 |
| St | pg/mL | 2.7E7 | 5.3E7 | 7.5E7 | 8.5E7 | 1.8E8 | 1.3E8 | 1.1E6 | 3.4E6 | 1.2E9 | 5.4E8 | 43 | 16 | 43 | 16 | 0.63 |
| Ra | pg/ml | 1.0E-9 | 1.0E-9 | 4.2E-1 | 3.6E-1 | 9.8E-1 | 7.5E-1 | 1.0E-9 | 1.0E-9 | 3.4E0 | 3.0E0 | 43 | 16 | 43 | 16 | 0.57 |
| Qz | pg/ml | 8.5E0 | 1.0E1 | 3.9E1 | 5.4E1 | 6.1E1 | 8.4E1 | 1.0E-9 | 1.0E-9 | 2.8E2 | 2.3E2 | 43 | 16 | 43 | 16 | 0.53 |
| Qy | pg/ml | 4.4E-1 | 5.2E-1 | 4.2E0 | 5.0E-1 | 1.4E1 | 4.5E-1 | 1.0E-9 | 1.0E-9 | 8.6E1 | 1.3E0 | 43 | 16 | 43 | 16 | 0.44 |

Figure 27 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Qx | pg/ml | 1.0E-9 | 1.0E-9 | 3.8E-1 | 1.0E-9 | 1.8E0 | 0.0E0 | 1.0E-9 | 1.0E-9 | 9.4E0 | 1.0E-9 | 43 | 16 | 43 | 16 | 0.48 |
| Qw | pg/ml | 9.0E-2 | 1.0E-9 | 2.9E0 | 1.3E-1 | 1.1E1 | 3.3E-1 | 1.0E-9 | 1.0E-9 | 6.6E1 | 1.2E0 | 43 | 16 | 43 | 16 | 0.33 |
| Qv | pg/ml | 2.6E4 | 1.8E4 | 4.3E4 | 2.4E4 | 6.0E4 | 2.5E4 | 1.0E-9 | 8.5E2 | 3.3E5 | 8.4E4 | 43 | 16 | 43 | 16 | 0.39 |
| Qu | pg/ml | 7.8E0 | 5.8E0 | 1.1E2 | 4.6E1 | 2.2E2 | 7.8E1 | 1.0E-9 | 1.0E-9 | 9.8E2 | 2.9E2 | 43 | 16 | 43 | 16 | 0.46 |
| Qt | pg/ml | 1.1E1 | 3.3E0 | 7.0E1 | 1.2E1 | 1.5E2 | 1.5E1 | 1.0E-9 | 1.0E-9 | 7.0E2 | 4.8E1 | 43 | 16 | 43 | 16 | 0.41 |
| Qh | ng/ml | 1.6E1 | 3.9E1 | 4.4E1 | 7.0E1 | 7.5E1 | 1.1E2 | 4.3E-1 | 1.0E-9 | 3.3E2 | 4.6E2 | 43 | 16 | 43 | 16 | 0.68 |
| Qg | ng/ml | 7.5E0 | 8.2E0 | 1.6E1 | 9.7E0 | 3.3E1 | 8.1E0 | 1.3E-1 | 1.3E0 | 2.2E2 | 3.5E1 | 43 | 16 | 43 | 16 | 0.52 |
| Jj | ng/ml | 7.3E2 | 4.2E2 | 1.0E3 | 6.2E2 | 1.0E3 | 8.1E2 | 6.1E1 | 7.9E1 | 5.7E3 | 4.1E3 | 61 | 24 | 61 | 24 | 0.37 |
| Jk | ng/ml | 3.0E0 | 2.4E0 | 2.1E1 | 2.0E1 | 4.7E1 | 4.4E1 | 1.2E-1 | 3.8E-1 | 2.7E2 | 2.0E2 | 61 | 24 | 61 | 24 | 0.52 |
| Jl | ng/ml | 5.3E-1 | 5.9E-1 | 2.0E0 | 3.8E0 | 4.4E0 | 8.7E0 | 1.6E-2 | 7.8E-2 | 2.0E1 | 4.0E1 | 61 | 24 | 61 | 24 | 0.55 |
| Jm | ng/ml | 2.3E1 | 4.0E1 | 5.1E1 | 1.5E2 | 8.9E1 | 4.1E2 | 1.9E-1 | 9.2E-1 | 6.1E2 | 2.1E3 | 61 | 24 | 61 | 24 | 0.61 |
| Jn | pg/ml | 4.6E-1 | 7.8E-1 | 1.0E0 | 1.1E0 | 2.0E0 | 9.6E-1 | 1.0E-9 | 3.6E-2 | 1.4E1 | 3.9E0 | 61 | 24 | 61 | 24 | 0.61 |
| Jo | pg/ml | 4.9E3 | 4.8E3 | 5.8E3 | 5.3E3 | 4.3E3 | 4.0E3 | 4.8E2 | 4.8E2 | 1.9E4 | 1.6E4 | 61 | 24 | 61 | 24 | 0.47 |
| Jp | pg/ml | 8.2E4 | 8.2E4 | 8.2E4 | 9.0E4 | 3.1E4 | 4.1E4 | 1.4E4 | 2.6E4 | 1.7E5 | 2.1E5 | 61 | 24 | 61 | 24 | 0.52 |
| Jq | pg/ml | 1.1E2 | 1.4E2 | 2.1E2 | 2.0E2 | 5.2E2 | 2.3E2 | 1.1E1 | 3.0E1 | 4.0E3 | 1.1E3 | 61 | 24 | 61 | 24 | 0.58 |
| Jr | pg/ml | 6.7E0 | 8.0E0 | 1.4E1 | 1.2E1 | 2.1E1 | 1.3E1 | 1.0E-9 | 1.0E-9 | 1.1E2 | 4.9E1 | 61 | 24 | 61 | 24 | 0.55 |
| Js | pg/ml | 1.5E1 | 1.8E1 | 2.3E1 | 2.4E1 | 3.6E1 | 2.0E1 | 1.9E0 | 6.6E0 | 2.7E2 | 8.8E1 | 61 | 24 | 61 | 24 | 0.57 |
| Jt | pg/ml | 3.3E3 | 2.8E3 | 3.4E3 | 3.2E3 | 2.0E3 | 2.1E3 | 3.8E2 | 3.8E2 | 9.7E3 | 7.5E3 | 61 | 24 | 61 | 24 | 0.47 |
| Ju | mIU/ml | 9.3E0 | 1.1E1 | 2.4E1 | 1.7E1 | 3.7E1 | 1.7E1 | 1.7E-1 | 7.5E-1 | 2.0E2 | 6.0E1 | 43 | 16 | 43 | 16 | 0.53 |
| Jv | mIU/ml | 1.9E1 | 1.7E1 | 3.3E1 | 2.6E1 | 5.7E1 | 2.4E1 | 1.7E-2 | 8.2E-2 | 3.4E2 | 6.3E1 | 43 | 16 | 43 | 16 | 0.53 |
| Jy | ng/ml | 1.6E-3 | 1.6E-3 | 2.5E-3 | 1.6E-3 | 5.8E-3 | 5.4E-3 | 1.7E-4 | 5.3E-4 | 3.9E-2 | 2.6E-3 | 43 | 16 | 43 | 16 | 0.50 |
| Kc | pg/ml | 2.8E1 | 2.9E1 | 4.4E1 | 5.0E1 | 4.0E1 | 7.3E1 | 9.5E-1 | 1.0E-9 | 1.7E2 | 2.7E2 | 43 | 16 | 43 | 16 | 0.47 |
| Kd | pg/ml | 1.0E-9 | 1.0E-9 | 2.4E2 | 4.3E2 | 5.0E2 | 8.1E2 | 1.0E-9 | 1.0E-9 | 1.9E3 | 2.4E3 | 43 | 16 | 43 | 16 | 0.53 |
| Ke | pg/ml | 1.4E4 | 1.9E4 | 1.7E4 | 2.3E4 | 1.2E4 | 1.5E4 | 2.9E3 | 5.2E3 | 5.6E4 | 5.2E4 | 43 | 16 | 43 | 16 | 0.63 |
| Kf | pg/mL | 8.1E0 | 7.8E0 | 7.4E0 | 9.7E0 | 5.0E0 | 9.8E0 | 1.0E-9 | 1.0E-9 | 2.4E1 | 4.4E1 | 43 | 16 | 43 | 16 | 0.54 |
| Kg | pg/mL | 1.5E3 | 1.2E3 | 2.1E3 | 2.1E3 | 2.2E3 | 2.2E3 | 1.4E2 | 3.5E2 | 1.1E4 | 7.7E3 | 43 | 16 | 43 | 16 | 0.47 |
| Ki | pg/ml | 5.8E1 | 7.8E1 | 7.9E1 | 8.8E1 | 5.9E1 | 6.6E1 | 1.0E-9 | 1.3E1 | 2.8E2 | 2.5E2 | 42 | 16 | 42 | 16 | 0.55 |
| Kj | pg/ml | 1.3E3 | 7.7E2 | 1.7E3 | 1.4E3 | 1.3E3 | 1.5E3 | 7.8E1 | 1.5E2 | 5.6E3 | 6.1E3 | 43 | 16 | 43 | 16 | 0.40 |
| Kk | pg/ml | 5.9E0 | 1.2E1 | 1.0E1 | 1.8E1 | 1.1E1 | 1.8E1 | 1.0E-9 | 2.3E0 | 5.0E1 | 5.5E1 | 43 | 16 | 43 | 16 | 0.65 |
| Kl | pg/ml | 2.3E4 | 1.7E4 | 3.3E4 | 2.6E4 | 3.1E4 | 2.4E4 | 2.3E2 | 7.0E2 | 1.6E5 | 9.0E4 | 43 | 16 | 43 | 16 | 0.46 |
| Kn | pg/ml | 5.3E1 | 4.1E1 | 7.0E1 | 1.1E2 | 8.4E1 | 1.8E2 | 1.0E-9 | 1.0E-9 | 3.8E2 | 6.3E2 | 43 | 16 | 43 | 16 | 0.51 |
| Ko | pg/ml | 3.4E2 | 5.9E2 | 5.1E2 | 6.8E2 | 4.9E2 | 5.1E2 | 1.0E-9 | 1.0E-9 | 1.6E3 | 1.6E3 | 43 | 16 | 43 | 16 | 0.61 |
| Kp | pg/ml | 3.6E2 | 3.7E2 | 3.7E2 | 4.3E2 | 2.1E2 | 2.9E2 | 1.0E-9 | 1.0E-9 | 8.1E2 | 9.8E2 | 43 | 16 | 43 | 16 | 0.55 |
| Kq | pg/ml | 3.9E2 | 4.3E2 | 5.6E2 | 4.7E2 | 5.0E2 | 2.8E2 | 6.1E1 | 1.1E2 | 2.1E3 | 1.3E3 | 41 | 17 | 41 | 17 | 0.52 |
| Kr | pg/ml | 2.0E0 | 9.9E-1 | 2.7E0 | 3.0E0 | 3.0E0 | 5.1E0 | 1.0E-9 | 1.0E-9 | 1.2E1 | 1.9E1 | 41 | 17 | 41 | 17 | 0.44 |
| Ks | pg/ml | 1.5E4 | 1.1E4 | 2.2E4 | 2.1E4 | 1.8E4 | 1.8E4 | 2.7E2 | 9.9E2 | 5.0E4 | 5.1E4 | 41 | 17 | 41 | 17 | 0.50 |
| Kx | ng/ml | 2.8E-3 | 1.0E-9 | 9.5E-3 | 1.2E-2 | 1.6E-2 | 1.8E-2 | 1.0E-9 | 1.0E-9 | 7.9E-2 | 6.5E-2 | 42 | 17 | 42 | 17 | 0.50 |
| Ky | ng/ml | 7.6E-2 | 1.3E-1 | 4.0E-1 | 3.1E-1 | 8.0E-1 | 5.7E-1 | 1.0E-9 | 1.0E-9 | 4.4E0 | 2.4E0 | 42 | 17 | 42 | 17 | 0.54 |
| Kz | ng/ml | 1.0E-9 | 1.0E-9 | 2.0E-3 | 2.9E-3 | 4.7E-3 | 4.8E-3 | 1.0E-9 | 1.0E-9 | 1.4E-2 | 1.4E-2 | 42 | 17 | 42 | 17 | 0.57 |
| Ld | ng/ml | 1.0E-9 | 1.0E-9 | 2.9E0 | 5.0E0 | 5.3E0 | 1.2E1 | 1.0E-9 | 1.0E-9 | 2.5E1 | 5.0E1 | 43 | 17 | 43 | 17 | 0.52 |
| Lh | pg/ml | 1.8E4 | 2.0E4 | 2.5E4 | 3.7E4 | 2.4E4 | 4.4E4 | 1.0E3 | 3.8E3 | 1.1E5 | 2.1E5 | 62 | 24 | 62 | 24 | 0.59 |
| Li | pg/ml | 5.7E3 | 1.3E4 | 1.7E4 | 5.5E4 | 2.9E4 | 1.9E5 | 2.8E2 | 3.6E1 | 1.3E5 | 9.2E5 | 62 | 24 | 62 | 24 | 0.62 |
| Lj | pg/ml | 4.2E3 | 6.6E3 | 2.8E4 | 5.1E4 | 7.9E4 | 8.9E4 | 4.1E1 | 1.0E2 | 4.7E5 | 4.1E5 | 62 | 24 | 62 | 24 | 0.58 |
| Rm | ng/ml | 1.9E1 | 2.7E1 | 4.5E1 | 8.6E1 | 6.2E1 | 1.6E2 | 1.3E0 | 4.6E0 | 2.5E2 | 6.5E2 | 42 | 15 | 42 | 15 | 0.60 |
| Rh | ng/ml | 1.8E2 | 1.2E2 | 2.9E2 | 2.4E2 | 3.6E2 | 2.3E2 | 2.6E1 | 3.6E1 | 2.0E3 | 7.4E2 | 42 | 15 | 42 | 15 | 0.50 |
| Ri | ng/ml | 1.0E-9 | 1.0E-9 | 3.6E0 | 2.7E0 | 8.2E0 | 4.8E0 | 1.0E-9 | 1.0E-9 | 4.5E1 | 1.6E1 | 42 | 15 | 42 | 15 | 0.49 |
| Rg | ng/ml | 1.0E-9 | 1.0E-9 | 1.4E-1 | 5.2E-2 | 5.9E-1 | 1.6E-1 | 1.0E-9 | 1.0E-9 | 3.3E0 | 6.2E-1 | 42 | 15 | 42 | 15 | 0.58 |
| Rj | ng/ml | 1.0E-9 | 1.0E-9 | 1.6E0 | 6.3E-1 | 4.1E0 | 1.1E0 | 1.0E-9 | 1.0E-9 | 2.4E1 | 3.2E0 | 42 | 15 | 42 | 15 | 0.45 |
| Rf | ng/ml | 4.8E-1 | 5.6E-1 | 1.4E0 | 1.2E0 | 2.6E0 | 1.2E0 | 3.2E-2 | 1.8E-2 | 1.2E1 | 3.8E0 | 42 | 15 | 42 | 15 | 0.57 |
| Ql | pg/ml | 4.5E0 | 7.2E0 | 1.8E1 | 1.3E1 | 3.7E1 | 2.1E1 | 1.0E-9 | 1.0E-9 | 1.8E2 | 8.8E1 | 43 | 16 | 43 | 16 | 0.52 |
| Qm | pg/ml | 8.6E0 | 3.2E1 | 2.2E1 | 2.8E1 | 3.8E1 | 4.7E1 | 1.0E-9 | 1.0E-9 | 1.8E2 | 1.7E2 | 43 | 16 | 43 | 16 | 0.51 |
| Qn | pg/ml | 9.5E-1 | 5.6E-1 | 4.3E0 | 1.8E1 | 8.4E0 | 6.0E1 | 1.0E-9 | 1.0E-9 | 3.8E1 | 2.4E2 | 43 | 16 | 43 | 16 | 0.39 |
| Nv | pg/ml | 4.7E3 | 5.1E3 | 9.9E3 | 1.4E4 | 1.6E4 | 2.6E4 | 4.6E2 | 7.1E2 | 8.4E4 | 1.1E5 | 62 | 25 | 62 | 25 | 0.50 |
| Nw | pg/ml | 1.0E4 | 1.6E4 | 1.5E4 | 1.8E4 | 1.2E4 | 1.3E4 | 2.6E3 | 5.8E3 | 7.3E4 | 6.1E4 | 62 | 25 | 62 | 25 | 0.60 |
| Nx | pg/ml | 2.4E2 | 2.6E2 | 5.5E2 | 6.9E2 | 7.0E2 | 7.7E2 | 1.0E-9 | 1.0E-9 | 2.6E3 | 2.5E3 | 62 | 25 | 62 | 25 | 0.55 |
| Ny | pg/ml | 9.6E0 | 7.9E0 | 1.6E1 | 3.5E1 | 2.6E1 | 8.6E1 | 1.0E-9 | 1.0E-9 | 1.5E2 | 4.2E2 | 62 | 25 | 62 | 25 | 0.54 |
| Oa | pg/ml | 1.2E2 | 6.5E2 | 3.7E2 | 1.0E3 | 5.4E2 | 1.2E3 | 1.0E-9 | 4.9E0 | 2.3E3 | 4.5E3 | 43 | 16 | 43 | 16 | 0.64 |

Figure 27 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Wn | ng/ml | 1.3E1 | 2.7E1 | 2.4E1 | 6.9E1 | 2.7E1 | 1.1E2 | 3.8E0 | 1.2E1 | 1.1E2 | 3.4E2 | 16 | 8 | 16 | 8 | 0.73 |
| Tk | ng/ml | 1.6E2 | 1.2E2 | 3.8E2 | 1.4E2 | 5.7E2 | 8.7E1 | 1.4E1 | 3.7E1 | 2.3E3 | 3.0E2 | 18 | 7 | 18 | 7 | 0.36 |
| Oe | pg/ml | 3.5E1 | 1.0E-9 | 2.7E2 | 2.5E2 | 5.1E2 | 4.3E2 | 1.0E-9 | 1.0E-9 | 3.4E3 | 1.6E3 | 62 | 25 | 62 | 25 | 0.48 |
| Of | pg/ml | 2.1E2 | 8.2E1 | 1.5E4 | 4.6E3 | 8.0E4 | 1.4E4 | 1.0E-9 | 1.0E-9 | 6.2E5 | 5.4E4 | 62 | 25 | 62 | 25 | 0.45 |
| Og | pg/ml | 9.8E-2 | 6.5E-2 | 1.7E0 | 2.7E-1 | 1.0E1 | 8.0E-1 | 1.0E-9 | 1.0E-9 | 7.9E1 | 4.0E0 | 62 | 25 | 62 | 25 | 0.37 |
| Oh | pg/ml | 2.6E0 | 4.2E0 | 8.4E0 | 6.9E0 | 2.5E1 | 1.0E1 | 1.0E-9 | 9.0E-2 | 2.0E2 | 5.4E1 | 62 | 25 | 62 | 25 | 0.60 |
| Oi | pg/ml | 4.1E0 | 3.0E0 | 7.2E0 | 6.0E0 | 8.9E0 | 8.4E0 | 1.0E-9 | 1.0E-9 | 4.1E1 | 3.6E1 | 62 | 25 | 62 | 25 | 0.46 |
| Ok | pg/ml | 5.4E2 | 6.4E2 | 6.1E2 | 9.0E2 | 4.0E2 | 7.8E2 | 6.4E1 | 1.4E2 | 2.0E3 | 3.2E3 | 62 | 25 | 62 | 25 | 0.61 |
| Om | pg/ml | 5.4E2 | 5.9E2 | 1.4E3 | 8.8E2 | 4.6E3 | 1.1E3 | 1.0E-9 | 9.7E1 | 3.6E4 | 5.0E3 | 62 | 25 | 62 | 25 | 0.48 |
| On | pg/ml | 2.0E2 | 2.3E2 | 2.8E2 | 3.9E2 | 2.6E2 | 4.0E2 | 2.2E1 | 3.9E1 | 1.6E3 | 1.5E3 | 62 | 25 | 62 | 25 | 0.58 |
| Or | pg/ml | 1.2E1 | 2.3E1 | 3.9E1 | 6.2E1 | 8.0E1 | 9.5E1 | 1.0E-9 | 1.0E-9 | 4.4E2 | 3.5E2 | 43 | 17 | 43 | 17 | 0.60 |
| Ow | pg/ml | 3.9E1 | 5.4E1 | 1.0E2 | 1.0E2 | 2.3E2 | 1.3E2 | 1.0E-9 | 1.0E-9 | 1.5E3 | 4.9E2 | 43 | 17 | 43 | 17 | 0.53 |
| Ou | pg/ml | 5.6E2 | 3.8E2 | 9.6E2 | 2.0E3 | 1.6E3 | 3.5E3 | 1.0E-9 | 1.0E-9 | 8.1E3 | 9.6E3 | 43 | 17 | 43 | 17 | 0.47 |
| Ul | ng/ml | 1.0E-9 | 1.0E-9 | 1.7E0 | 1.3E0 | 5.9E0 | 5.2E0 | 1.0E-9 | 1.0E-9 | 3.4E1 | 2.1E1 | 43 | 16 | 43 | 16 | 0.48 |
| Uo | ng/ml | 1.0E-9 | 1.0E-9 | 8.3E-2 | 2.4E-2 | 2.0E-1 | 8.2E-2 | 1.0E-9 | 1.0E-9 | 8.5E-1 | 3.2E-1 | 43 | 16 | 43 | 16 | 0.43 |
| Uk | ng/ml | 1.0E-9 | 1.0E-9 | 1.2E-2 | 4.5E-3 | 2.7E-2 | 1.8E-2 | 1.0E-9 | 1.0E-9 | 1.3E-1 | 7.1E-2 | 43 | 16 | 43 | 16 | 0.32 |
| Um | ng/ml | 1.0E-9 | 1.0E-9 | 1.6E-1 | 1.9E-1 | 3.3E-1 | 4.4E-1 | 1.0E-9 | 1.0E-9 | 1.3E0 | 1.4E0 | 43 | 16 | 43 | 16 | 0.45 |
| Uf | ng/ml | 7.9E-2 | 9.9E-2 | 1.6E-1 | 1.3E-1 | 2.3E-1 | 1.2E-1 | 6.8E-3 | 1.7E-2 | 1.1E0 | 5.3E-1 | 43 | 16 | 43 | 16 | 0.55 |
| Uh | ng/ml | 2.6E0 | 4.4E0 | 4.3E0 | 5.3E0 | 4.4E0 | 4.3E0 | 3.0E-1 | 4.5E-1 | 1.7E1 | 1.5E1 | 43 | 16 | 43 | 16 | 0.60 |
| Un | ng/ml | 2.5E0 | 2.3E0 | 2.7E0 | 2.4E0 | 1.5E0 | 1.3E0 | 4.6E-1 | 7.4E-1 | 8.0E0 | 5.1E0 | 43 | 16 | 43 | 16 | 0.46 |
| Ug | ng/ml | 2.2E1 | 9.7E0 | 3.2E1 | 2.1E1 | 3.4E1 | 2.8E1 | 1.2E0 | 2.3E0 | 1.8E2 | 1.1E2 | 43 | 16 | 43 | 16 | 0.36 |
| Ur | ng/ml | 9.6E-2 | 1.1E-1 | 2.8E-1 | 5.2E-1 | 4.9E-1 | 1.2E0 | 1.0E-9 | 1.0E-9 | 2.8E0 | 4.5E0 | 42 | 16 | 42 | 16 | 0.49 |
| Up | ng/ml | 1.0E-9 | 1.0E-9 | 8.9E-3 | 3.8E-3 | 1.9E-2 | 1.2E-2 | 1.0E-9 | 1.0E-9 | 9.5E-2 | 4.5E-2 | 42 | 16 | 42 | 16 | 0.36 |
| Us | ng/ml | 5.3E-3 | 1.9E-3 | 2.0E-2 | 5.4E-2 | 3.7E-2 | 9.7E-2 | 1.0E-9 | 1.0E-9 | 2.1E-1 | 3.6E-1 | 42 | 16 | 42 | 16 | 0.49 |
| Uv | ng/ml | 4.3E-3 | 2.6E-3 | 1.1E-2 | 5.3E-3 | 2.4E-2 | 8.4E-3 | 1.0E-9 | 1.0E-9 | 1.3E-1 | 3.3E-2 | 42 | 16 | 42 | 16 | 0.43 |
| Ut | ng/ml | 7.9E-1 | 7.2E-1 | 2.4E0 | 1.8E0 | 3.5E0 | 2.3E0 | 1.0E-9 | 2.9E-1 | 1.4E1 | 8.9E0 | 42 | 16 | 42 | 16 | 0.50 |
| Uu | ng/ml | 7.1E0 | 5.2E0 | 8.1E0 | 6.9E0 | 5.2E0 | 5.0E0 | 5.7E-1 | 1.5E0 | 2.2E1 | 2.1E1 | 42 | 16 | 42 | 16 | 0.42 |
| Vp | ng/ml | 1.0E-9 | 1.0E-9 | 4.1E-2 | 6.2E-2 | 1.5E-1 | 1.9E-1 | 1.0E-9 | 1.0E-9 | 7.1E-1 | 7.4E-1 | 43 | 16 | 43 | 16 | 0.51 |
| Vt | ng/ml | 7.3E0 | 1.2E1 | 1.1E1 | 1.3E1 | 1.3E1 | 7.1E0 | 1.1E0 | 1.4E0 | 6.5E1 | 2.8E1 | 43 | 16 | 43 | 16 | 0.65 |
| Vu | ng/ml | 1.0E-9 | 3.6E-1 | 2.2E0 | 2.6E0 | 4.4E0 | 5.5E0 | 1.0E-9 | 1.0E-9 | 2.1E1 | 2.2E1 | 42 | 16 | 42 | 16 | 0.56 |
| Vq | ng/ml | 4.3E2 | 6.2E2 | 1.0E3 | 1.6E3 | 2.1E3 | 3.6E3 | 9.0E-1 | 1.8E1 | 1.1E4 | 1.2E4 | 29 | 11 | 29 | 11 | 0.58 |
| Vo | ng/ml | 2.6E1 | 2.5E1 | 2.6E1 | 2.3E1 | 5.1E0 | 5.5E0 | 1.0E1 | 4.9E0 | 4.8E1 | 2.9E1 | 43 | 16 | 43 | 16 | 0.36 |
| Vs | ng/ml | 1.0E-9 | 1.0E-9 | 4.7E0 | 1.7E0 | 9.1E0 | 4.0E0 | 1.0E-9 | 1.0E-9 | 4.2E1 | 1.4E1 | 42 | 14 | 42 | 14 | 0.40 |
| Vv | ng/ml | 4.7E0 | 2.1E0 | 6.0E0 | 2.5E0 | 6.6E0 | 2.6E0 | 1.0E-9 | 1.0E-9 | 2.8E1 | 9.6E0 | 43 | 16 | 43 | 16 | 0.34 |
| Oy | pg/ml | 5.3E-1 | 3.7E-1 | 3.8E0 | 3.2E0 | 1.3E1 | 1.0E1 | 1.0E-9 | 1.0E-9 | 9.9E1 | 4.9E1 | 61 | 25 | 61 | 25 | 0.42 |
| Oz | pg/ml | 1.8E-1 | 8.8E-2 | 8.4E-1 | 3.7E-1 | 3.7E0 | 6.2E-1 | 1.0E-9 | 1.0E-9 | 2.9E1 | 2.2E0 | 61 | 25 | 61 | 25 | 0.48 |
| Pa | pg/ml | 4.2E-1 | 6.1E-1 | 1.3E0 | 1.3E0 | 4.0E0 | 1.6E0 | 1.0E-9 | 1.0E-9 | 2.9E1 | 6.5E0 | 61 | 25 | 61 | 25 | 0.61 |
| Pb | pg/ml | 4.1E-2 | 1.0E-9 | 2.6E-1 | 1.1E-1 | 9.4E-1 | 2.3E-1 | 1.0E-9 | 1.0E-9 | 7.3E0 | 1.1E0 | 61 | 25 | 61 | 25 | 0.40 |
| Pc | pg/ml | 3.4E-1 | 3.4E-1 | 4.0E-1 | 3.6E-1 | 4.2E-1 | 3.8E-1 | 1.0E-9 | 1.0E-9 | 1.8E0 | 1.2E0 | 61 | 25 | 61 | 25 | 0.47 |
| Pd | pg/ml | 2.4E-1 | 2.4E0 | 1.8E1 | 4.4E0 | 1.1E2 | 6.3E0 | 1.0E-9 | 1.0E-9 | 8.4E2 | 2.9E1 | 61 | 25 | 61 | 25 | 0.48 |
| Pe | pg/ml | 3.1E1 | 5.5E1 | 1.3E2 | 2.4E2 | 4.4E2 | 8.6E2 | 1.0E-9 | 1.0E-9 | 3.3E3 | 4.3E3 | 61 | 25 | 61 | 25 | 0.58 |
| Pf | pg/ml | 2.3E0 | 4.4E0 | 3.2E1 | 2.1E1 | 1.9E2 | 7.4E1 | 1.0E-9 | 1.0E-9 | 1.5E3 | 3.8E2 | 61 | 25 | 61 | 25 | 0.56 |
| Pg | pg/ml | 2.9E0 | 6.8E0 | 1.4E2 | 3.9E1 | 9.9E2 | 8.7E1 | 1.0E-9 | 1.0E-9 | 7.7E3 | 4.0E2 | 61 | 25 | 61 | 25 | 0.61 |
| Ph | ng/ml | 2.0E-1 | 1.8E-1 | 3.9E-1 | 3.4E-1 | 6.2E-1 | 5.5E-1 | 1.0E-9 | 1.0E-9 | 2.8E0 | 2.4E0 | 43 | 17 | 43 | 17 | 0.50 |
| Pi | ng/ml | 1.9E-1 | 2.4E-1 | 2.6E-1 | 3.0E-1 | 2.3E-1 | 3.3E-1 | 1.0E-9 | 1.0E-9 | 9.7E-1 | 1.4E0 | 43 | 17 | 43 | 17 | 0.54 |
| Pj | ng/mL | 7.1E0 | 5.7E0 | 8.5E0 | 7.1E0 | 6.1E0 | 4.5E0 | 9.9E-1 | 1.8E0 | 2.5E1 | 2.0E1 | 43 | 17 | 43 | 17 | 0.44 |
| Pk | ng/ml | 8.7E-3 | 9.7E-3 | 1.5E-2 | 1.1E-2 | 2.4E-2 | 8.5E-3 | 1.0E-9 | 1.0E-9 | 1.4E-1 | 2.6E-2 | 43 | 17 | 43 | 17 | 0.52 |
| aA | mg/dL | 8.5E-1 | 9.0E-1 | 9.0E-1 | 9.0E-1 | 4.1E-1 | 2.8E-1 | 2.6E-1 | 4.0E-1 | 2.6E0 | 1.4E0 | 85 | 27 | 85 | 27 | 0.54 |
| aC | mg/mL | 2.2E0 | 2.1E0 | 2.4E0 | 2.3E0 | 1.1E0 | 1.1E0 | 8.7E-1 | 7.5E-1 | 5.5E0 | 4.8E0 | 46 | 16 | 46 | 16 | 0.45 |
| aD | ug/mL | 3.4E0 | 4.7E0 | 4.7E0 | 5.9E0 | 3.8E0 | 4.9E0 | 8.7E-1 | 7.5E-1 | 2.0E1 | 2.1E1 | 46 | 16 | 46 | 16 | 0.58 |
| aE | mg/mL | 5.6E-1 | 5.1E-1 | 5.7E-1 | 5.4E-1 | 1.7E-1 | 2.0E-1 | 2.5E-1 | 1.8E-1 | 1.0E0 | 9.1E-1 | 46 | 16 | 46 | 16 | 0.46 |
| aF | ng/mL | 1.6E0 | 1.7E0 | 3.2E0 | 3.6E0 | 3.7E0 | 4.6E0 | 4.3E-3 | 3.7E-1 | 1.8E1 | 1.8E1 | 46 | 16 | 46 | 16 | 0.47 |
| aG | mg/mL | 1.6E-1 | 1.5E-1 | 1.7E-1 | 1.7E-1 | 8.9E-2 | 1.1E-1 | 5.1E-2 | 6.4E-2 | 4.0E-1 | 4.8E-1 | 46 | 16 | 46 | 16 | 0.47 |
| aH | ug/mL | 9.4E1 | 7.7E1 | 9.9E1 | 8.2E1 | 5.3E1 | 3.9E1 | 1.1E1 | 2.0E1 | 2.6E2 | 1.7E2 | 46 | 16 | 46 | 16 | 0.40 |
| aI | ug/mL | 2.0E2 | 1.5E2 | 2.0E2 | 1.5E2 | 6.4E1 | 5.3E1 | 4.8E1 | 7.8E1 | 3.4E2 | 2.8E2 | 46 | 16 | 46 | 16 | 0.28 |
| aJ | ug/mL | 2.4E0 | 3.0E0 | 3.0E0 | 3.5E0 | 2.1E0 | 2.1E0 | 1.0E0 | 8.2E-1 | 1.3E1 | 7.9E0 | 46 | 16 | 46 | 16 | 0.58 |
| aK | ng/mL | 9.8E-1 | 1.4E0 | 1.9E0 | 1.7E0 | 2.1E0 | 1.2E0 | 2.9E-4 | 4.1E-1 | 1.0E1 | 4.2E0 | 46 | 16 | 46 | 16 | 0.55 |

Figure 27 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aL | mg/mL | 7.9E-1 | 7.7E-1 | 8.1E-1 | 7.5E-1 | 2.6E-1 | 2.7E-1 | 3.0E-1 | 4.1E-1 | 1.7E0 | 1.5E0 | 46 | 16 | 46 | 16 | 0.43 |
| aM | U/mL | 3.0E1 | 2.5E1 | 4.6E1 | 4.6E1 | 4.1E1 | 4.8E1 | 4.2E-2 | 4.2E-2 | 1.6E2 | 1.3E2 | 46 | 16 | 46 | 16 | 0.48 |
| aN | U/mL | 1.8E1 | 2.2E1 | 3.3E1 | 2.8E1 | 5.7E1 | 2.5E1 | 2.5E-3 | 2.5E-3 | 3.8E2 | 8.5E1 | 46 | 16 | 46 | 16 | 0.52 |
| aO | pg/mL | 4.9E1 | 1.9E1 | 3.0E2 | 4.9E2 | 7.0E2 | 8.3E2 | 1.6E0 | 6.0E-2 | 3.6E3 | 2.5E3 | 46 | 16 | 46 | 16 | 0.44 |
| aP | ng/mL | 1.6E0 | 1.7E0 | 1.9E0 | 2.0E0 | 1.1E0 | 1.6E0 | 7.8E-1 | 6.8E-1 | 5.4E0 | 6.5E0 | 46 | 16 | 46 | 16 | 0.46 |
| aQ | ng/mL | 2.8E-1 | 2.2E-1 | 4.7E-1 | 2.8E-1 | 4.7E-1 | 2.1E-1 | 2.5E-2 | 5.9E-2 | 2.0E0 | 9.2E-1 | 46 | 16 | 46 | 16 | 0.42 |
| aR | ng/mL | 2.0E0 | 1.4E0 | 3.3E0 | 2.3E0 | 4.7E0 | 2.6E0 | 6.2E-1 | 6.2E-1 | 3.0E1 | 1.1E1 | 46 | 16 | 46 | 16 | 0.40 |
| aS | ng/mL | 3.5E-1 | 4.8E-1 | 8.2E-1 | 6.6E-1 | 1.3E0 | 6.0E-1 | 4.2E-3 | 7.0E-2 | 6.2E0 | 2.3E0 | 46 | 16 | 46 | 16 | 0.56 |
| aU | pg/mL | 6.1E1 | 6.1E1 | 1.1E2 | 6.8E1 | 1.4E2 | 3.7E1 | 7.4E-2 | 2.3E1 | 7.0E2 | 1.6E2 | 46 | 16 | 46 | 16 | 0.50 |
| aV | ng/mL | 6.1E-1 | 3.6E-1 | 1.7E0 | 5.5E-1 | 4.8E0 | 4.6E-1 | 3.8E-2 | 9.1E-2 | 3.3E1 | 1.6E0 | 46 | 16 | 46 | 16 | 0.40 |
| aW | pg/mL | 2.1E1 | 1.5E1 | 2.0E1 | 1.5E1 | 1.1E1 | 1.1E1 | 7.2E-2 | 7.2E-2 | 5.4E1 | 2.9E1 | 46 | 16 | 46 | 16 | 0.37 |
| aX | ng/mL | 7.7E0 | 1.5E1 | 1.1E1 | 1.4E1 | 1.1E1 | 9.8E0 | 7.0E-1 | 1.4E0 | 4.6E1 | 3.1E1 | 46 | 16 | 46 | 16 | 0.60 |
| aY | pg/mL | 6.6E1 | 4.6E1 | 1.0E2 | 4.7E1 | 1.8E2 | 3.5E1 | 4.1E-1 | 4.1E-1 | 1.2E3 | 1.1E2 | 46 | 16 | 46 | 16 | 0.35 |
| aZ | pg/mL | 1.6E2 | 2.6E2 | 4.3E2 | 4.6E2 | 9.0E2 | 5.9E2 | 1.7E0 | 1.5E1 | 5.9E3 | 2.1E3 | 46 | 16 | 46 | 16 | 0.56 |
| bA | ng/mL | 1.1E1 | 2.4E1 | 5.9E1 | 5.8E1 | 1.5E2 | 1.1E2 | 3.0E-2 | 3.0E-2 | 9.4E2 | 4.3E2 | 46 | 16 | 46 | 16 | 0.52 |
| bB | ng/mL | 3.2E2 | 2.8E2 | 3.2E2 | 2.7E2 | 1.8E2 | 1.7E2 | 3.6E1 | 2.3E1 | 8.1E2 | 6.2E2 | 46 | 16 | 46 | 16 | 0.41 |
| bC | ng/mL | 3.4E2 | 2.8E2 | 7.4E2 | 6.2E2 | 1.0E3 | 9.5E2 | 4.6E1 | 1.2E2 | 4.7E3 | 4.0E3 | 46 | 16 | 46 | 16 | 0.48 |
| bE | mg/mL | 5.1E0 | 5.0E0 | 5.6E0 | 5.3E0 | 2.3E0 | 1.9E0 | 1.4E0 | 1.8E0 | 1.2E1 | 9.6E0 | 46 | 16 | 46 | 16 | 0.46 |
| bF | pg/mL | 2.0E1 | 3.9E1 | 3.1E1 | 2.1E2 | 1.6E3 | 5.3E2 | 2.5E0 | 7.7E0 | 1.0E4 | 2.2E3 | 46 | 16 | 46 | 16 | 0.65 |
| bG | ng/mL | 1.2E0 | 1.2E0 | 2.5E0 | 3.4E0 | 3.6E0 | 3.9E0 | 2.5E-1 | 2.7E-1 | 1.7E1 | 1.3E1 | 46 | 16 | 46 | 16 | 0.58 |
| bH | pg/mL | 5.7E-1 | 5.7E-1 | 6.0E0 | 3.6E0 | 1.9E1 | 5.1E0 | 5.7E-1 | 5.7E-1 | 1.2E2 | 1.9E1 | 46 | 16 | 46 | 16 | 0.55 |
| bI | ng/mL | 4.0E-3 | 4.0E-3 | 8.9E-2 | 5.7E-2 | 1.7E-1 | 1.6E-1 | 4.0E-3 | 4.0E-3 | 7.1E-1 | 6.2E-1 | 46 | 16 | 46 | 16 | 0.47 |
| bJ | mg/mL | 2.0E0 | 1.6E0 | 2.5E0 | 1.9E0 | 2.3E0 | 1.3E0 | 2.5E-4 | 2.8E-1 | 1.1E1 | 4.9E0 | 46 | 16 | 46 | 16 | 0.45 |
| bL | pg/mL | 2.2E0 | 2.4E0 | 6.6E0 | 3.9E0 | 1.0E1 | 3.6E0 | 4.6E-2 | 4.6E-2 | 3.5E1 | 1.1E1 | 46 | 16 | 46 | 16 | 0.53 |
| bM | mg/mL | 2.4E0 | 2.2E0 | 2.9E0 | 2.3E0 | 1.6E0 | 1.2E0 | 4.1E-1 | 7.1E-1 | 7.9E0 | 4.8E0 | 46 | 16 | 46 | 16 | 0.41 |
| bN | ng/mL | 6.7E1 | 2.3E1 | 1.7E2 | 5.1E1 | 3.6E2 | 8.9E1 | 6.5E0 | 2.1E0 | 1.9E3 | 3.7E2 | 46 | 16 | 46 | 16 | 0.29 |
| bO | ng/mL | 4.0E-2 | 4.0E-2 | 4.7E0 | 5.6E0 | 1.1E1 | 1.1E1 | 4.0E-2 | 4.0E-2 | 4.3E1 | 3.7E1 | 46 | 16 | 46 | 16 | 0.50 |
| bP | mg/mL | 4.9E-1 | 6.4E-1 | 7.1E-1 | 8.1E-1 | 8.0E-1 | 7.2E-1 | 1.3E-1 | 1.1E-1 | 4.8E0 | 3.1E0 | 46 | 16 | 46 | 16 | 0.58 |
| bQ | pg/mL | 1.7E1 | 2.3E1 | 3.1E2 | 4.2E1 | 2.0E3 | 4.6E1 | 1.5E-1 | 6.4E0 | 1.3E4 | 1.8E2 | 46 | 16 | 46 | 16 | 0.64 |
| bR | ng/mL | 1.2E-2 | 1.2E-2 | 2.7E-1 | 9.1E-2 | 1.3E0 | 1.2E-1 | 1.2E-2 | 1.2E-2 | 8.7E0 | 3.9E-1 | 46 | 16 | 46 | 16 | 0.50 |
| bS | pg/mL | 9.4E-1 | 9.4E-1 | 1.2E1 | 3.5E0 | 5.8E1 | 1.0E1 | 9.4E-1 | 9.4E-1 | 3.9E2 | 4.3E1 | 46 | 16 | 46 | 16 | 0.48 |
| bU | ng/mL | 1.3E-2 | 8.5E-2 | 2.5E-1 | 1.3E-1 | 9.7E-1 | 1.7E-1 | 1.3E-2 | 1.3E-2 | 6.6E0 | 6.3E-1 | 46 | 16 | 46 | 16 | 0.52 |
| bV | pg/mL | 4.5E2 | 5.2E2 | 5.0E2 | 6.8E2 | 1.7E2 | 6.6E2 | 2.3E2 | 3.0E2 | 8.2E2 | 3.1E3 | 46 | 16 | 46 | 16 | 0.57 |
| bW | pg/mL | 3.6E2 | 3.5E2 | 5.5E2 | 5.3E2 | 7.1E2 | 4.5E2 | 1.2E2 | 1.3E2 | 4.8E3 | 1.8E3 | 46 | 16 | 46 | 16 | 0.53 |
| bX | ng/mL | 2.5E-5 | 2.5E-5 | 1.7E-3 | 2.1E-3 | 2.5E-3 | 3.0E-3 | 2.5E-5 | 2.5E-5 | 8.8E-3 | 8.7E-3 | 46 | 16 | 46 | 16 | 0.52 |
| bZ | pg/mL | 2.5E2 | 2.9E2 | 1.7E3 | 1.0E3 | 8.6E3 | 1.6E3 | 2.4E1 | 5.7E1 | 5.8E4 | 5.6E3 | 46 | 16 | 46 | 16 | 0.60 |
| cA | pg/mL | 6.0E-1 | 6.0E-1 | 9.3E0 | 6.0E-1 | 5.5E1 | 0.0E0 | 6.0E-1 | 6.0E-1 | 3.7E2 | 6.0E-1 | 46 | 16 | 46 | 16 | 0.46 |
| cB | ng/mL | 5.0E-2 | 4.2E-2 | 8.1E-2 | 8.0E-2 | 9.2E-2 | 1.1E-1 | 1.7E-3 | 1.7E-3 | 3.7E-1 | 4.0E-1 | 46 | 16 | 46 | 16 | 0.46 |
| cC | pg/mL | 2.1E1 | 4.7E1 | 3.8E1 | 4.2E1 | 6.9E1 | 2.2E1 | 1.0E0 | 1.0E0 | 4.5E2 | 6.7E1 | 46 | 16 | 46 | 16 | 0.64 |
| cD | pg/mL | 3.3E0 | 4.3E0 | 1.0E1 | 8.4E0 | 2.9E1 | 1.3E1 | 3.3E-1 | 3.3E-1 | 1.4E2 | 4.5E1 | 46 | 16 | 46 | 16 | 0.61 |
| cE | pg/mL | 3.9E1 | 1.2E2 | 2.1E2 | 2.1E2 | 7.1E2 | 2.8E2 | 1.2E-1 | 1.2E-1 | 3.8E3 | 1.1E3 | 46 | 16 | 46 | 16 | 0.63 |
| cF | pg/mL | 9.4E0 | 5.0E0 | 1.8E1 | 1.3E1 | 4.0E1 | 1.6E1 | 5.3E-1 | 5.3E-1 | 2.7E2 | 5.0E1 | 46 | 16 | 46 | 16 | 0.48 |
| cG | pg/mL | 4.8E1 | 5.8E1 | 3.3E2 | 9.3E1 | 1.5E3 | 6.6E1 | 7.8E0 | 7.8E0 | 1.0E4 | 2.2E2 | 46 | 16 | 46 | 16 | 0.65 |
| cH | uIU/mL | 4.8E0 | 2.6E0 | 1.1E1 | 4.6E0 | 2.0E1 | 6.8E0 | 8.6E-3 | 8.6E-3 | 1.2E2 | 2.4E1 | 46 | 16 | 46 | 16 | 0.29 |
| cI | ng/mL | 5.8E0 | 1.1E1 | 1.7E1 | 1.8E1 | 2.3E1 | 2.1E1 | 8.0E-2 | 5.1E-1 | 9.4E1 | 6.4E1 | 46 | 16 | 46 | 16 | 0.52 |
| cJ | ug/mL | 6.3E1 | 6.0E1 | 1.3E2 | 9.4E1 | 1.7E2 | 1.0E2 | 1.1E1 | 7.2E0 | 6.9E2 | 3.4E2 | 46 | 16 | 46 | 16 | 0.49 |
| cK | ng/mL | 3.8E-3 | 3.8E-3 | 3.8E-2 | 3.8E-3 | 2.1E-1 | 0.0E0 | 3.8E-3 | 3.8E-3 | 1.5E0 | 3.8E-3 | 46 | 16 | 46 | 16 | 0.47 |
| cL | ng/mL | 1.7E2 | 2.0E2 | 8.7E2 | 2.4E2 | 3.6E3 | 1.7E2 | 1.6E1 | 3.1E1 | 2.4E4 | 7.6E2 | 46 | 16 | 46 | 16 | 0.54 |
| cM | pg/mL | 2.6E2 | 2.6E2 | 2.9E2 | 2.7E2 | 2.3E2 | 1.1E2 | 3.3E1 | 4.2E1 | 1.5E3 | 4.5E2 | 46 | 16 | 46 | 16 | 0.53 |
| cN | pg/mL | 1.1E2 | 1.2E2 | 1.4E2 | 1.2E2 | 1.5E2 | 3.0E1 | 4.3E1 | 7.3E1 | 1.1E3 | 1.7E2 | 46 | 16 | 46 | 16 | 0.52 |
| cO | pg/mL | 2.0E2 | 2.1E2 | 6.5E2 | 2.3E2 | 2.8E3 | 8.3E1 | 8.2E1 | 1.2E2 | 1.9E4 | 4.3E2 | 46 | 16 | 46 | 16 | 0.53 |
| cP | ng/mL | 2.9E3 | 2.4E3 | 2.9E3 | 2.7E3 | 9.7E2 | 1.1E3 | 1.1E3 | 1.6E3 | 5.5E3 | 5.9E3 | 46 | 16 | 46 | 16 | 0.39 |
| cQ | ng/mL | 6.2E-2 | 6.5E-2 | 1.5E-1 | 2.0E-1 | 2.7E-1 | 3.6E-1 | 2.0E-3 | 2.0E-3 | 1.4E0 | 1.3E0 | 46 | 16 | 46 | 16 | 0.47 |
| cR | ng/mL | 2.9E2 | 6.4E2 | 4.6E2 | 6.7E2 | 4.7E2 | 5.5E2 | 3.0E1 | 3.6E1 | 2.3E3 | 2.0E3 | 46 | 16 | 46 | 16 | 0.63 |
| cS | ng/mL | 2.6E2 | 2.5E2 | 3.2E2 | 6.2E2 | 2.1E2 | 8.3E2 | 7.0E1 | 1.4E2 | 9.4E2 | 2.6E3 | 46 | 16 | 46 | 16 | 0.53 |
| cT | ng/mL | 3.6E1 | 6.9E1 | 1.5E2 | 8.5E1 | 3.5E2 | 1.0E2 | 7.2E0 | 4.2E0 | 2.1E3 | 4.0E2 | 46 | 16 | 46 | 16 | 0.51 |
| cU | ng/mL | 6.5E1 | 5.9E1 | 1.2E2 | 9.6E1 | 2.4E2 | 1.0E2 | 1.4E1 | 1.7E1 | 1.6E3 | 4.2E2 | 46 | 16 | 46 | 16 | 0.48 |

Figure 27 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cV | ng/mL | 1.8E-1 | 2.8E-1 | 2.8E-1 | 3.7E-1 | 4.4E-1 | 2.4E-1 | 3.7E-2 | 4.1E-2 | 2.5E0 | 8.9E-1 | 46 | 16 | 46 | 16 | 0.73 |
| cW | mIU/mL | 4.2E-2 | 4.0E-2 | 7.3E-2 | 5.5E-2 | 7.3E-2 | 4.1E-2 | 4.8E-3 | 1.4E-2 | 2.9E-1 | 1.6E-1 | 46 | 16 | 46 | 16 | 0.49 |
| cX | ng/mL | 2.0E-1 | 5.3E-2 | 1.2E0 | 7.3E-1 | 3.3E0 | 1.3E0 | 2.3E-4 | 2.3E-4 | 2.1E1 | 4.4E0 | 46 | 16 | 46 | 16 | 0.39 |
| cY | ng/mL | 7.3E0 | 7.3E0 | 1.3E1 | 8.2E0 | 1.5E1 | 4.9E0 | 1.5E-1 | 9.8E-1 | 6.1E1 | 1.8E1 | 46 | 16 | 46 | 16 | 0.49 |
| cZ | ug/mL | 1.5E1 | 1.2E1 | 1.6E1 | 1.3E1 | 7.6E0 | 6.4E0 | 3.1E0 | 4.5E0 | 3.7E1 | 3.1E1 | 46 | 16 | 46 | 16 | 0.35 |
| dA | pg/mL | 3.6E2 | 3.2E2 | 5.0E2 | 3.1E2 | 8.2E2 | 1.2E2 | 1.3E2 | 1.5E2 | 5.8E3 | 5.5E2 | 46 | 16 | 46 | 16 | 0.37 |
| dB | ug/mL | 3.8E0 | 1.9E1 | 1.1E1 | 1.6E1 | 1.0E1 | 1.0E1 | 1.8E0 | 2.2E0 | 3.1E1 | 3.0E1 | 46 | 16 | 46 | 16 | 0.61 |
| dC | nmol/L | 3.4E1 | 3.8E1 | 3.7E1 | 3.8E1 | 1.3E1 | 1.6E1 | 1.7E1 | 7.8E0 | 7.7E1 | 6.9E1 | 46 | 16 | 46 | 16 | 0.54 |
| dD | ug/mL | 3.4E1 | 3.0E1 | 3.6E1 | 3.1E1 | 1.1E1 | 1.1E1 | 1.3E1 | 1.4E1 | 5.7E1 | 4.6E1 | 46 | 16 | 46 | 16 | 0.36 |
| dE | ng/mL | 8.4E-3 | 8.4E-3 | 3.8E-1 | 2.3E-1 | 5.6E-1 | 2.8E-1 | 8.4E-3 | 8.4E-3 | 2.0E0 | 7.0E-1 | 46 | 16 | 46 | 16 | 0.47 |
| dF | ng/mL | 2.3E2 | 2.9E2 | 2.9E2 | 3.9E2 | 2.0E2 | 2.9E2 | 1.0E2 | 7.5E1 | 1.3E3 | 1.2E3 | 46 | 16 | 46 | 16 | 0.65 |
| dG | ng/mL | 1.2E1 | 1.4E1 | 1.7E1 | 1.7E1 | 2.6E1 | 1.3E1 | 6.3E0 | 3.0E0 | 1.8E2 | 5.8E1 | 46 | 16 | 46 | 16 | 0.57 |
| dH | pg/mL | 8.0E0 | 9.4E0 | 2.4E1 | 1.2E1 | 9.8E1 | 1.1E1 | 4.0E-2 | 4.0E-2 | 6.7E2 | 4.9E1 | 46 | 16 | 46 | 16 | 0.56 |
| dI | pg/mL | 4.6E-1 | 4.6E-1 | 8.3E0 | 8.7E-1 | 4.9E1 | 9.0E-1 | 4.6E-1 | 4.6E-1 | 3.3E2 | 2.9E0 | 46 | 16 | 46 | 16 | 0.49 |
| dJ | ng/mL | 2.2E0 | 1.9E0 | 2.3E0 | 1.8E0 | 1.2E0 | 7.1E-1 | 5.6E-1 | 3.7E-1 | 5.1E0 | 2.9E0 | 46 | 16 | 46 | 16 | 0.38 |
| dK | uIU/mL | 1.6E0 | 1.2E0 | 2.3E0 | 2.2E0 | 3.3E0 | 2.1E0 | 1.8E-1 | 1.9E-1 | 2.1E1 | 6.5E0 | 46 | 16 | 46 | 16 | 0.50 |
| dL | ng/mL | 9.0E2 | 9.9E2 | 1.1E3 | 1.1E3 | 5.7E2 | 7.0E2 | 4.7E2 | 2.8E2 | 3.2E3 | 3.3E3 | 46 | 16 | 46 | 16 | 0.51 |
| dM | pg/mL | 1.1E3 | 1.1E3 | 1.1E3 | 1.3E3 | 6.0E2 | 6.9E2 | 4.2E2 | 3.7E2 | 3.3E3 | 3.1E3 | 46 | 16 | 46 | 16 | 0.57 |
| dN | ug/mL | 9.8E1 | 8.6E1 | 9.9E1 | 9.8E1 | 3.3E1 | 5.3E1 | 3.7E1 | 2.4E1 | 1.9E2 | 2.1E2 | 46 | 16 | 46 | 16 | 0.42 |
| dR | pg/ml | 1.6E3 | 1.4E3 | 2.4E3 | 1.9E3 | 2.4E3 | 1.5E3 | 1.7E2 | 3.4E2 | 9.8E3 | 5.3E3 | 44 | 16 | 44 | 16 | 0.48 |
| eF | ng/ml | 4.2E0 | 4.0E0 | 4.7E0 | 4.8E0 | 2.0E0 | 2.1E0 | 2.0E0 | 2.1E0 | 1.2E1 | 1.0E1 | 45 | 16 | 45 | 16 | 0.50 |
| eC | pg/ml | 3.3E2 | 2.2E2 | 3.5E2 | 2.4E2 | 1.5E2 | 1.6E2 | 5.1E1 | 1.9E1 | 7.5E2 | 4.9E2 | 41 | 13 | 41 | 13 | 0.31 |
| eD | pg/ml | 2.1E2 | 2.4E2 | 5.5E2 | 6.3E2 | 1.0E3 | 1.2E3 | 5.2E-1 | 1.4E2 | 5.5E3 | 3.8E3 | 33 | 9 | 33 | 9 | 0.58 |
| eM | ng/ml | 3.0E0 | 3.2E0 | 5.2E0 | 2.9E0 | 4.7E0 | 2.2E0 | 1.5E0 | 6.9E-1 | 1.8E1 | 7.3E0 | 12 | 9 | 12 | 9 | 0.34 |
| fP | ng/ml | 2.6E2 | 4.0E2 | 2.7E2 | 4.3E2 | 1.1E2 | 2.3E2 | 4.8E1 | 1.3E2 | 5.2E2 | 8.6E2 | 42 | 16 | 42 | 16 | 0.69 |
| fR | ng/ml | 1.1E5 | 1.7E5 | 1.8E5 | 2.4E5 | 1.8E5 | 1.4E5 | 3.6E4 | 9.9E4 | 6.9E5 | 4.8E5 | 19 | 8 | 19 | 8 | 0.68 |
| gC | ng/ml | 1.8E2 | 2.8E2 | 2.5E2 | 3.1E2 | 1.4E2 | 9.2E1 | 1.3E2 | 1.8E2 | 5.9E2 | 4.5E2 | 13 | 9 | 13 | 9 | 0.70 |
| gL | pg/ml | 6.1E4 | 6.0E4 | 6.6E4 | 6.5E4 | 2.5E4 | 2.4E4 | 1.1E4 | 2.1E4 | 1.6E5 | 1.3E5 | 44 | 16 | 44 | 16 | 0.48 |
| gP | U/ml | 3.1E2 | 2.4E2 | 3.1E2 | 2.5E2 | 9.4E1 | 1.0E2 | 1.7E2 | 9.6E1 | 6.5E2 | 5.2E2 | 44 | 16 | 44 | 16 | 0.29 |
| gW | ng/ml | 3.9E2 | 6.1E2 | 7.8E2 | 1.2E3 | 1.0E3 | 1.4E3 | 2.3E0 | 1.9E2 | 4.2E3 | 4.3E3 | 39 | 9 | 39 | 9 | 0.64 |
| tF | pg/mL | 6.3E2 | 3.2E3 | 1.2E4 | 5.7E3 | 3.9E4 | 6.1E3 | 1.2E1 | 1.8E1 | 2.3E5 | 1.7E4 | 41 | 14 | 41 | 14 | 0.61 |
| hA | ng/ml | 2.0E0 | 3.0E0 | 1.7E1 | 6.6E0 | 5.4E1 | 5.8E0 | 1.7E-2 | 1.7E-2 | 2.9E2 | 1.5E1 | 33 | 9 | 33 | 9 | 0.64 |
| nM | pg/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 20 | 12 | 20 | 12 | 0.50 |
| nN | pg/ml | 1.4E3 | 2.2E3 | 2.3E3 | 3.9E3 | 3.1E3 | 5.5E3 | 1.9E2 | 2.8E2 | 1.3E4 | 2.1E4 | 20 | 12 | 20 | 12 | 0.63 |
| nO | pg/ml | 2.4E1 | 2.4E1 | 3.8E1 | 4.6E1 | 3.4E1 | 6.5E1 | 3.5E0 | 8.1E0 | 1.4E2 | 2.4E2 | 20 | 12 | 20 | 12 | 0.50 |
| nR | pg/ml | 1.1E1 | 1.6E1 | 2.4E1 | 6.9E1 | 3.6E1 | 1.3E2 | 1.7E0 | 1.0E0 | 1.5E2 | 4.2E2 | 20 | 12 | 20 | 12 | 0.59 |
| nT | pg/ml | 1.1E2 | 8.7E1 | 1.0E2 | 9.1E1 | 8.9E1 | 4.2E1 | 1.0E-9 | 1.4E1 | 3.3E2 | 1.9E2 | 20 | 12 | 20 | 12 | 0.49 |
| nU | pg/ml | 3.0E1 | 1.1E1 | 5.6E1 | 5.9E1 | 5.9E1 | 8.1E1 | 1.0E-9 | 1.0E-9 | 1.9E2 | 2.2E2 | 20 | 12 | 20 | 12 | 0.48 |
| lW | pg/ml | 1.0E-9 | 1.0E-9 | 9.0E0 | 1.9E0 | 3.7E1 | 6.6E0 | 1.0E-9 | 1.0E-9 | 1.6E2 | 2.3E1 | 20 | 12 | 20 | 12 | 0.45 |
| lX | pg/ml | 1.2E3 | 5.2E2 | 1.2E3 | 7.1E2 | 6.0E2 | 4.4E2 | 1.2E2 | 1.9E2 | 2.3E3 | 1.6E3 | 20 | 12 | 20 | 12 | 0.25 |
| lY | pg/ml | 2.8E1 | 1.9E1 | 3.1E1 | 1.8E1 | 2.4E1 | 9.0E0 | 5.4E0 | 3.7E0 | 1.2E2 | 3.0E1 | 20 | 12 | 20 | 12 | 0.26 |
| mE | pg/ml | 1.0E-9 | 1.0E-9 | 4.5E0 | 2.5E0 | 1.3E1 | 4.3E0 | 1.0E-9 | 1.0E-9 | 5.7E1 | 1.3E1 | 20 | 12 | 20 | 12 | 0.48 |
| mF | pg/ml | 1.0E-9 | 2.7E-1 | 6.3E0 | 2.7E0 | 2.3E1 | 4.5E0 | 1.0E-9 | 1.0E-9 | 1.1E2 | 1.3E1 | 20 | 12 | 20 | 12 | 0.57 |
| mH | pg/ml | 3.4E0 | 2.3E0 | 6.2E0 | 3.6E0 | 1.1E1 | 3.2E0 | 3.2E-1 | 9.8E-1 | 5.3E1 | 1.1E1 | 20 | 12 | 20 | 12 | 0.41 |
| mI | pg/ml | 1.8E0 | 1.0E-9 | 1.5E1 | 1.4E1 | 4.0E1 | 2.7E1 | 1.0E-9 | 1.0E-9 | 1.8E2 | 7.8E1 | 20 | 12 | 20 | 12 | 0.46 |
| mM | pg/ml | 2.1E1 | 2.7E1 | 4.6E1 | 5.3E1 | 6.5E1 | 8.2E1 | 1.0E-9 | 1.0E-9 | 2.4E2 | 2.9E2 | 20 | 12 | 20 | 12 | 0.52 |
| mP | pg/ml | 1.5E1 | 1.5E1 | 1.4E1 | 1.4E1 | 8.2E0 | 1.0E1 | 1.0E-9 | 1.0E-9 | 2.9E1 | 3.8E1 | 20 | 12 | 20 | 12 | 0.49 |
| mS | pg/ml | 1.6E3 | 1.2E3 | 1.6E3 | 1.6E3 | 7.6E2 | 1.2E3 | 1.0E-9 | 6.4E2 | 2.9E3 | 5.1E3 | 20 | 12 | 20 | 12 | 0.38 |
| mT | pg/ml | 4.3E1 | 5.9E1 | 7.5E1 | 6.5E1 | 6.6E1 | 3.5E1 | 1.6E1 | 1.9E1 | 2.8E2 | 1.4E2 | 20 | 12 | 20 | 12 | 0.53 |
| mU | pg/ml | 1.9E0 | 3.2E0 | 2.5E0 | 3.2E0 | 2.2E0 | 1.9E0 | 1.9E-1 | 1.0E-9 | 1.1E1 | 7.7E0 | 20 | 12 | 20 | 12 | 0.68 |
| mW | pg/ml | 2.4E3 | 2.2E3 | 2.7E3 | 2.4E3 | 1.2E3 | 1.3E3 | 1.1E3 | 7.7E2 | 5.6E3 | 5.7E3 | 20 | 12 | 20 | 12 | 0.41 |
| mY | pg/ml | 5.9E2 | 6.3E2 | 7.3E2 | 8.6E2 | 4.7E2 | 7.2E2 | 2.1E2 | 2.5E2 | 2.2E3 | 2.5E3 | 20 | 12 | 20 | 12 | 0.50 |
| mZ | pg/ml | 2.0E2 | 2.1E2 | 3.3E2 | 5.1E2 | 2.9E2 | 7.9E2 | 2.8E1 | 1.1E1 | 1.1E3 | 2.8E3 | 20 | 12 | 20 | 12 | 0.45 |
| nA | pg/ml | 1.5E0 | 4.8E-1 | 6.0E0 | 6.7E0 | 1.4E1 | 1.8E1 | 1.0E-9 | 1.0E-9 | 6.2E1 | 6.5E1 | 20 | 12 | 20 | 12 | 0.39 |
| nB | pg/ml | 3.1E2 | 3.3E2 | 3.3E2 | 3.5E2 | 1.4E2 | 1.8E2 | 9.7E1 | 3.8E1 | 6.4E2 | 6.9E2 | 20 | 12 | 20 | 12 | 0.53 |
| nC | pg/ml | 1.0E-9 | 8.5E1 | 8.0E1 | 1.5E5 | 1.8E2 | 4.4E5 | 1.0E-9 | 1.0E-9 | 6.2E2 | 1.5E6 | 20 | 12 | 20 | 12 | 0.64 |
| nD | pg/ml | 7.9E0 | 3.6E0 | 7.1E0 | 2.9E1 | 5.2E0 | 7.3E1 | 1.0E-9 | 1.0E-9 | 1.8E1 | 2.6E2 | 20 | 12 | 20 | 12 | 0.49 |

Figure 27 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nF | pg/ml | 1.0E-9 | 1.0E-9 | 1.5E0 | 2.3E0 | 5.0E0 | 7.9E0 | 1.0E-9 | 1.0E-9 | 2.1E1 | 2.7E1 | 20 | 12 | 20 | 12 | 0.50 |
| nH | pg/ml | 2.0E-1 | 9.8E-1 | 1.8E0 | 1.1E3 | 3.0E0 | 2.9E3 | 1.0E-9 | 1.0E-9 | 1.2E1 | 1.0E4 | 20 | 12 | 20 | 12 | 0.57 |
| nI | pg/ml | 2.8E0 | 5.0E1 | 5.8E0 | 7.1E1 | 8.1E1 | 1.0E2 | 1.0E-9 | 1.0E-9 | 2.6E2 | 3.5E2 | 20 | 12 | 20 | 12 | 0.50 |
| nJ | pg/ml | 1.0E-9 | 8.4E-2 | 5.3E-1 | 1.1E1 | 8.3E-1 | 3.8E1 | 1.0E-9 | 1.0E-9 | 2.4E0 | 1.3E2 | 20 | 12 | 20 | 12 | 0.54 |
| nK | pg/ml | 1.0E-9 | 1.0E-9 | 1.3E1 | 1.4E1 | 2.1E1 | 3.0E1 | 1.0E-9 | 1.0E-9 | 6.4E1 | 1.0E2 | 20 | 12 | 20 | 12 | 0.49 |
| nL | pg/ml | 1.0E-9 | 1.0E-9 | 4.9E0 | 1.6E3 | 1.1E1 | 4.1E3 | 1.0E-9 | 1.0E-9 | 4.5E1 | 1.4E4 | 20 | 12 | 20 | 12 | 0.60 |
| hR | pg/ml | 2.4E4 | 3.1E4 | 2.4E4 | 3.0E4 | 1.0E4 | 9.4E3 | 3.6E3 | 1.6E4 | 4.9E4 | 4.3E4 | 32 | 9 | 32 | 9 | 0.67 |
| hV | pg/ml | 4.3E2 | 4.4E2 | 4.5E2 | 4.1E2 | 2.4E2 | 2.1E2 | 6.8E1 | 1.5E2 | 9.6E2 | 7.4E2 | 32 | 9 | 32 | 9 | 0.45 |
| hW | pg/ml | 1.6E3 | 2.4E3 | 2.2E3 | 2.8E3 | 1.7E3 | 1.6E3 | 2.2E2 | 1.1E3 | 6.7E3 | 6.4E3 | 32 | 9 | 32 | 9 | 0.67 |
| hX | pg/ml | 8.7E2 | 1.4E3 | 9.1E2 | 1.8E3 | 4.5E2 | 1.9E3 | 1.3E2 | 3.1E2 | 2.3E3 | 6.6E3 | 32 | 9 | 32 | 9 | 0.74 |
| iA | pg/ml | 1.2E2 | 1.5E2 | 1.7E2 | 2.8E2 | 1.6E2 | 3.1E2 | 1.2E1 | 1.5E1 | 7.9E2 | 8.7E2 | 41 | 14 | 41 | 14 | 0.57 |
| iB | ng/ml | 3.4E0 | 7.8E0 | 4.1E0 | 8.4E0 | 2.9E0 | 6.4E0 | 4.5E-2 | 1.6E0 | 1.4E1 | 1.9E1 | 33 | 9 | 33 | 9 | 0.69 |
| iC | U/ml | 1.9E-1 | 5.8E-1 | 4.3E-1 | 2.0E0 | 8.7E-1 | 3.9E0 | 1.0E-9 | 6.8E-2 | 4.8E0 | 1.2E1 | 33 | 9 | 33 | 9 | 0.67 |
| iH | ng/ml | 1.4E5 | 1.7E5 | 1.4E5 | 1.4E5 | 5.0E4 | 5.7E4 | 7.4E4 | 2.9E3 | 2.5E5 | 2.0E5 | 41 | 14 | 41 | 14 | 0.54 |
| iJ | ng/ml | 5.3E4 | 4.5E4 | 5.6E4 | 4.6E4 | 3.9E4 | 2.1E4 | 8.0E3 | 1.8E3 | 2.5E5 | 7.5E4 | 41 | 14 | 41 | 14 | 0.46 |
| hB | ng/ml | 3.6E-1 | 5.0E-1 | 4.5E-1 | 7.6E-1 | 2.8E-1 | 7.9E-1 | 1.2E-1 | 1.2E-1 | 1.3E0 | 3.2E0 | 41 | 14 | 41 | 14 | 0.69 |
| hC | pg/ml | 4.3E3 | 7.1E3 | 1.0E4 | 8.2E3 | 1.8E4 | 8.1E3 | 1.0E-9 | 4.1E1 | 1.1E5 | 2.7E4 | 41 | 14 | 41 | 14 | 0.49 |
| hF | ng/ml | 1.0E-9 | 1.0E-9 | 1.6E-2 | 6.8E-1 | 1.0E-1 | 2.6E0 | 1.0E-9 | 1.0E-9 | 6.6E-1 | 9.6E0 | 41 | 14 | 41 | 14 | 0.52 |
| hG | pg/ml | 6.7E3 | 5.9E3 | 7.3E3 | 6.5E3 | 3.2E3 | 2.7E3 | 2.3E3 | 3.6E3 | 1.9E4 | 1.2E4 | 41 | 14 | 41 | 14 | 0.42 |
| iO | ng/ml | 3.6E5 | 3.7E5 | 3.8E5 | 4.2E5 | 1.8E5 | 2.0E5 | 8.3E4 | 1.8E5 | 9.0E5 | 8.2E5 | 41 | 14 | 41 | 14 | 0.56 |
| iP | ng/ml | 5.0E4 | 5.5E4 | 5.3E4 | 5.0E4 | 4.1E4 | 2.3E4 | 2.4E3 | 1.0E4 | 2.2E5 | 7.7E4 | 41 | 14 | 41 | 14 | 0.53 |
| iZ | ng/ml | 1.6E3 | 1.9E3 | 1.8E3 | 1.7E3 | 7.1E2 | 5.9E2 | 8.8E2 | 9.8E2 | 4.3E3 | 2.6E3 | 39 | 13 | 39 | 13 | 0.46 |
| rC | pg/ml | 1.6E3 | 1.0E3 | 2.2E3 | 1.4E3 | 2.1E3 | 1.3E3 | 1.0E-9 | 7.0E1 | 1.1E4 | 3.8E3 | 33 | 9 | 33 | 9 | 0.39 |
| rB | pg/ml | 2.5E1 | 5.1E1 | 3.2E1 | 6.9E1 | 2.3E1 | 7.6E1 | 1.0E-9 | 1.0E-9 | 9.2E1 | 2.5E2 | 33 | 9 | 33 | 9 | 0.67 |
| jD | ng/ml | 4.1E1 | 2.4E1 | 4.6E1 | 3.5E1 | 3.7E1 | 3.1E1 | 1.0E-9 | 1.0E-9 | 1.5E2 | 9.9E1 | 33 | 9 | 33 | 9 | 0.42 |
| jE | ng/ml | 1.0E-9 | 1.0E-9 | 7.6E0 | 7.1E0 | 1.3E1 | 1.8E1 | 1.0E-9 | 1.0E-9 | 5.2E1 | 5.6E1 | 33 | 9 | 33 | 9 | 0.46 |
| jF | ng/ml | 3.7E1 | 3.8E1 | 5.8E1 | 3.7E1 | 6.6E1 | 3.6E1 | 1.0E-9 | 1.0E-9 | 1.9E2 | 1.1E2 | 33 | 9 | 33 | 9 | 0.45 |
| jG | ng/ml | 4.4E3 | 5.4E3 | 4.5E3 | 4.4E3 | 2.0E3 | 2.2E3 | 1.2E3 | 6.0E2 | 9.6E3 | 6.5E3 | 33 | 9 | 33 | 9 | 0.52 |
| jH | ng/ml | 7.5E1 | 7.1E1 | 8.3E1 | 6.6E1 | 5.5E1 | 1.7E1 | 2.5E1 | 3.6E1 | 3.3E2 | 8.7E1 | 33 | 9 | 33 | 9 | 0.42 |
| jI | ng/ml | 6.8E1 | 9.9E1 | 7.3E1 | 9.6E1 | 2.5E1 | 4.9E1 | 3.8E1 | 5.0E1 | 1.4E2 | 1.9E2 | 33 | 9 | 33 | 9 | 0.63 |
| rA | pg/ml | 2.3E1 | 2.0E1 | 3.4E1 | 2.4E1 | 2.8E1 | 1.5E1 | 1.0E-9 | 6.9E0 | 1.1E2 | 4.8E1 | 34 | 9 | 34 | 9 | 0.42 |
| qZ | pg/ml | 4.4E1 | 9.3E1 | 4.6E2 | 1.6E3 | 2.0E3 | 3.7E3 | 4.8E-4 | 5.3E-3 | 1.0E4 | 1.0E4 | 24 | 7 | 24 | 7 | 0.60 |
| qY | pg/ml | 2.6E1 | 1.1E1 | 6.3E1 | 1.2E1 | 7.6E1 | 6.4E0 | 2.9E0 | 5.1E0 | 3.3E2 | 2.5E1 | 34 | 9 | 34 | 9 | 0.27 |
| qX | pg/ml | 5.6E1 | 6.8E1 | 6.9E1 | 7.3E1 | 4.7E1 | 4.5E1 | 1.0E-9 | 1.7E1 | 2.1E2 | 1.3E2 | 34 | 9 | 34 | 9 | 0.54 |
| qW | pg/ml | 8.4E0 | 1.0E1 | 1.2E1 | 1.1E1 | 1.1E1 | 1.0E1 | 1.0E-9 | 1.0E-9 | 5.1E1 | 3.1E1 | 34 | 9 | 34 | 9 | 0.50 |
| qV | pg/ml | 2.2E3 | 2.4E3 | 2.7E3 | 2.9E3 | 2.1E3 | 2.6E3 | 1.0E2 | 9.5E2 | 8.2E3 | 9.6E3 | 34 | 9 | 34 | 9 | 0.50 |
| qU | pg/ml | 8.5E1 | 1.2E2 | 2.0E2 | 2.4E2 | 3.8E2 | 2.7E2 | 1.0E-9 | 1.0E-9 | 2.1E3 | 7.9E2 | 34 | 9 | 34 | 9 | 0.57 |
| qT | pg/ml | 4.1E1 | 7.7E1 | 5.8E1 | 8.4E1 | 4.8E1 | 6.2E1 | 1.0E-9 | 6.9E0 | 1.8E2 | 2.0E2 | 34 | 9 | 34 | 9 | 0.63 |
| jK | ng/ml | 1.8E3 | 1.5E3 | 1.8E3 | 1.6E3 | 7.4E2 | 8.9E2 | 7.2E2 | 8.0E2 | 4.0E3 | 3.6E3 | 33 | 9 | 33 | 9 | 0.37 |
| jL | pg/ml | 2.5E2 | 2.0E2 | 3.5E2 | 2.5E2 | 3.8E2 | 1.5E2 | 4.9E1 | 1.3E2 | 2.1E3 | 5.9E2 | 33 | 9 | 33 | 9 | 0.46 |
| jM | ng/ml | 6.4E4 | 5.2E4 | 8.0E4 | 6.1E4 | 4.8E4 | 3.6E4 | 1.1E3 | 5.7E3 | 1.7E5 | 1.2E5 | 33 | 9 | 33 | 9 | 0.39 |
| jO | pg/ml | 2.2E5 | 2.5E5 | 2.4E5 | 2.8E5 | 1.0E5 | 1.3E5 | 7.7E4 | 1.4E5 | 4.6E5 | 5.2E5 | 33 | 9 | 33 | 9 | 0.59 |
| jP | pg/ml | 2.5E5 | 2.8E5 | 2.7E5 | 3.7E5 | 1.6E5 | 3.4E5 | 7.4E4 | 1.3E5 | 7.2E5 | 1.2E6 | 33 | 9 | 33 | 9 | 0.59 |
| jQ | pg/ml | 2.8E3 | 1.7E3 | 4.0E3 | 2.4E3 | 3.9E3 | 1.9E3 | 1.4E2 | 4.6E2 | 1.4E4 | 6.1E3 | 33 | 9 | 33 | 9 | 0.42 |
| jR | pg/ml | 6.8E3 | 3.3E3 | 1.3E4 | 8.8E3 | 1.4E4 | 1.2E4 | 1.0E-9 | 3.0E1 | 5.6E4 | 3.4E4 | 33 | 9 | 33 | 9 | 0.39 |
| jT | pg/ml | 1.9E5 | 1.6E5 | 1.9E5 | 1.6E5 | 7.7E4 | 7.0E4 | 7.7E4 | 7.5E4 | 3.8E5 | 2.8E5 | 33 | 9 | 33 | 9 | 0.41 |
| jU | mIU/ml | 4.8E0 | 4.8E0 | 1.0E1 | 9.4E0 | 1.5E1 | 9.8E0 | 6.2E-2 | 8.2E-1 | 6.7E1 | 3.0E1 | 33 | 9 | 33 | 9 | 0.53 |
| jV | mIU/ml | 1.2E0 | 1.2E0 | 2.7E0 | 1.9E0 | 5.2E0 | 2.0E0 | 1.7E-3 | 7.6E-2 | 2.6E1 | 6.6E0 | 33 | 9 | 33 | 9 | 0.55 |
| jY | ng/ml | 4.2E-4 | 2.7E-3 | 3.8E-3 | 6.6E-3 | 9.6E-3 | 8.0E-3 | 1.0E-9 | 1.0E-9 | 5.1E-2 | 2.4E-2 | 33 | 9 | 33 | 9 | 0.72 |
| kC | pg/ml | 8.5E1 | 9.3E1 | 1.4E2 | 3.2E2 | 2.0E2 | 7.6E2 | 2.1E1 | 5.4E1 | 9.8E2 | 2.7E3 | 20 | 12 | 20 | 12 | 0.54 |
| kE | pg/ml | 1.4E5 | 1.2E5 | 1.4E5 | 1.3E5 | 4.3E4 | 4.4E4 | 4.1E4 | 7.5E4 | 2.1E5 | 2.0E5 | 20 | 12 | 20 | 12 | 0.39 |
| kF | pg/mL | 5.6E1 | 7.0E1 | 6.2E1 | 7.0E1 | 2.7E1 | 2.7E1 | 2.8E1 | 3.4E1 | 1.5E2 | 1.3E2 | 20 | 12 | 20 | 12 | 0.61 |
| kG | pg/mL | 9.7E3 | 1.1E4 | 1.2E4 | 1.5E4 | 8.8E3 | 1.4E4 | 3.3E3 | 3.8E3 | 3.6E4 | 5.0E4 | 20 | 12 | 20 | 12 | 0.53 |
| kI | pg/ml | 1.8E2 | 1.8E2 | 1.9E2 | 1.9E2 | 7.8E1 | 7.8E1 | 4.4E1 | 7.2E1 | 4.2E2 | 3.1E2 | 20 | 12 | 20 | 12 | 0.53 |
| kK | pg/ml | 9.1E1 | 7.5E1 | 1.2E2 | 1.6E2 | 9.6E1 | 1.7E2 | 2.9E1 | 2.9E1 | 4.6E2 | 5.1E2 | 20 | 12 | 20 | 12 | 0.49 |
| kN | pg/ml | 1.0E3 | 1.1E3 | 1.5E3 | 4.2E3 | 1.6E3 | 1.1E4 | 2.3E2 | 3.9E2 | 6.3E3 | 3.9E4 | 20 | 12 | 20 | 12 | 0.50 |
| kO | pg/ml | 7.0E3 | 5.9E3 | 7.0E3 | 1.9E4 | 2.2E3 | 4.1E4 | 3.4E3 | 3.8E3 | 1.3E4 | 1.5E5 | 20 | 12 | 20 | 12 | 0.45 |

Figure 27 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| kP | pg/ml | 5.6E3 | 5.3E3 | 9.6E3 | 5.8E3 | 1.1E4 | 2.9E3 | 2.1E3 | 1.4E3 | 4.8E4 | 1.1E4 | 20 | 12 | 20 | 12 | 0.43 |
| kQ | pg/ml | 4.2E3 | 3.5E3 | 5.1E3 | 3.9E3 | 3.4E3 | 1.8E3 | 1.1E3 | 1.4E3 | 1.8E4 | 7.8E3 | 41 | 14 | 41 | 14 | 0.40 |
| kR | pg/ml | 2.2E1 | 2.1E1 | 2.4E1 | 2.8E1 | 1.6E1 | 2.5E1 | 1.4E-1 | 3.4E0 | 5.9E1 | 8.2E1 | 41 | 14 | 41 | 14 | 0.50 |
| kS | pg/ml | 9.3E2 | 6.7E2 | 1.1E3 | 8.7E2 | 8.2E2 | 6.9E2 | 2.1E2 | 2.9E2 | 4.1E3 | 3.0E3 | 41 | 14 | 41 | 14 | 0.36 |
| rZ | ng/ml | 1.0E-9 | 6.9E-3 | 4.7E-3 | 9.4E-3 | 8.3E-3 | 1.4E-2 | 1.0E-9 | 1.0E-9 | 3.1E-2 | 4.5E-2 | 32 | 9 | 32 | 9 | 0.65 |
| rY | ng/ml | 6.1E-2 | 8.7E-2 | 8.0E-1 | 9.5E-2 | 4.1E0 | 5.2E-2 | 1.0E-9 | 3.2E-2 | 2.3E1 | 2.1E-1 | 32 | 9 | 32 | 9 | 0.68 |
| rX | ng/ml | 1.0E-9 | 1.0E-9 | 9.4E-2 | 4.6E-3 | 5.3E-1 | 8.5E-3 | 1.0E-9 | 1.0E-9 | 3.0E0 | 2.4E-2 | 32 | 9 | 32 | 9 | 0.66 |
| lK | pg/ml | 1.6E2 | 6.8E1 | 2.7E2 | 1.1E2 | 5.8E2 | 1.1E2 | 1.0E-9 | 4.8E0 | 3.3E3 | 2.9E2 | 33 | 9 | 33 | 9 | 0.40 |
| lL | pg/ml | 1.3E3 | 1.7E3 | 2.1E3 | 2.4E3 | 2.1E3 | 2.0E3 | 1.5E1 | 1.9E2 | 6.9E3 | 5.8E3 | 33 | 9 | 33 | 9 | 0.60 |
| lM | pg/ml | 1.1E3 | 2.6E3 | 2.9E3 | 4.7E3 | 5.3E3 | 5.0E3 | 2.1E2 | 2.4E1 | 2.9E4 | 1.3E4 | 33 | 9 | 33 | 9 | 0.61 |
| lN | pg/ml | 1.0E-9 | 4.7E0 | 2.7E0 | 7.0E0 | 4.9E0 | 8.0E0 | 1.0E-9 | 1.0E-9 | 2.4E1 | 2.1E1 | 33 | 9 | 33 | 9 | 0.66 |
| lO | pg/ml | 1.0E-9 | 1.0E-9 | 3.8E0 | 3.7E0 | 2.2E1 | 1.1E1 | 1.0E-9 | 1.0E-9 | 1.3E2 | 3.4E1 | 33 | 9 | 33 | 9 | 0.54 |
| nW | pg/ml | 1.1E5 | 1.0E5 | 1.1E5 | 1.1E5 | 2.3E4 | 3.7E4 | 6.5E4 | 3.6E4 | 1.5E5 | 1.9E5 | 41 | 14 | 41 | 14 | 0.46 |
| nY | pg/ml | 2.4E3 | 2.5E3 | 2.5E3 | 2.9E3 | 1.4E3 | 2.0E3 | 1.0E3 | 6.3E2 | 7.1E3 | 8.1E3 | 41 | 14 | 41 | 14 | 0.54 |
| oO | pg/ml | 8.3E4 | 9.6E4 | 1.2E5 | 1.0E5 | 9.0E4 | 4.7E4 | 3.8E4 | 2.0E4 | 3.1E5 | 2.0E5 | 19 | 12 | 19 | 12 | 0.56 |
| oP | pg/ml | 1.2E5 | 1.4E5 | 1.4E5 | 1.6E5 | 9.5E4 | 1.1E5 | 4.8E4 | 5.6E4 | 4.5E5 | 4.6E5 | 19 | 12 | 19 | 12 | 0.57 |
| oQ | pg/ml | 2.5E3 | 3.3E3 | 3.8E3 | 3.7E3 | 3.2E3 | 2.2E3 | 1.6E3 | 7.7E2 | 1.4E4 | 8.4E3 | 19 | 12 | 19 | 12 | 0.58 |
| oE | pg/ml | 1.1E2 | 4.0E2 | 3.1E2 | 6.9E2 | 5.2E2 | 8.1E2 | 1.0E-9 | 5.4E1 | 1.9E3 | 2.6E3 | 41 | 14 | 41 | 14 | 0.72 |
| oF | pg/ml | 9.7E3 | 1.7E4 | 2.8E4 | 4.0E4 | 4.8E4 | 6.2E4 | 7.8E2 | 5.1E2 | 2.5E5 | 1.8E5 | 41 | 14 | 41 | 14 | 0.55 |
| oH | pg/ml | 4.4E1 | 3.0E1 | 9.0E1 | 5.7E1 | 1.0E2 | 6.0E1 | 6.2E0 | 1.2E1 | 4.8E2 | 1.8E2 | 41 | 14 | 41 | 14 | 0.39 |
| oK | pg/ml | 9.5E2 | 7.8E2 | 1.7E3 | 5.2E3 | 1.9E3 | 1.4E4 | 1.4E2 | 2.3E2 | 7.2E3 | 5.3E4 | 41 | 14 | 41 | 14 | 0.52 |
| oN | pg/ml | 5.7E2 | 4.4E2 | 6.9E2 | 8.5E2 | 7.7E2 | 1.3E3 | 2.8E2 | 1.1E2 | 5.3E3 | 5.0E3 | 41 | 14 | 41 | 14 | 0.40 |
| pF | pg/ml | 6.0E-1 | 5.4E-1 | 2.7E0 | 7.9E-1 | 1.3E1 | 5.7E-1 | 1.0E-9 | 1.0E-9 | 8.7E1 | 1.7E0 | 41 | 14 | 41 | 14 | 0.57 |

Analyte panel data:

Unconstrained panels with 3 analytes, where 1.0E-8 >= 'model p-value' > 0. Contains 4 panels of 13,646,915 total panels evaluated. : Fb{gW(aU Vv)} Il{Is(hX lO)}

Unconstrained panels with 3 analytes, where 1.0E-7 >= 'model p-value' > 1.0E-8. Contains 13 panels of 13,646,915 total panels evaluated. : fP{gP(Ch Lj Mg Ng Oa Qb) QhUp} Th{AjUc CoCs OaeF} Fn{oE(Ex Gz)} FbgWkR Unconstrained panels with 3 analytes, where 1.0E-6 >= 'model p-value' > 1.0E-7. Contains 469 panels of 13,646,915 total panels evaluated. :
oE{Nt(kC kE kF kG kI kK kN kO kP lW lX lY mE mF mH ml mM mP mS mT mU mW mY mZ nA nB nC nD nF nH nI nJ nK nL nM nN nO nR nT nU oO oP oQ) Kr(kC kE kF kG kK kN kO kP lX lY mE mF mH ml mM mP mS mT mU mW mY mZ nA nB nD nH nl nJ nK nL nN nO nR nT nU) nO(bL bN bS cA cK lv Lv Lx Mh mM Mr Nd Nf No Pg Ph Po Tv Vu) mM(aX dL EF Et Fn Fr gL GP Jj kG Kq MZ Nq St Tn) oO(bN bS cA cK gP Iv Mh Nf Nk Ph) mS(bN Iv Mh Nk Ph Tv) lW(Nk Ph Tv) mP(Jt Pj Qn) dL(nC nH) gP(oP oQ) kE(Fn Tn) LumY LvmW MjkO QnnA nCnH} kE{Tn(aC aK aM aO aU aV bA bH bJ bQ bU bX cB cF cR cX cY dA dC dD dR Ed eF Fa Fb Fn Fr Hb hC hG Hr Hu Ik Iu Jf Jh Ji Jm Jo Jt Ju Jv Kj Kp kR kS Lj Lv lW lY Ma mE mF ml Ml Ms mW nK NN Nq Nt Nu nW nY Oa oF OH Pd Pe Pf Pg Pj Qb Qg Qm Qv Rc Ub Ug Uk Vo Vu Vv Tj) Fn(bA dF Fr Jj Kj Lu Lx Nd) eF(bJ Kk Lj Lv Nb Nt Ny Tr) Vu(Jg Kd Kk Nv Om Tr) Lx(al dD gP Un) gP(oO Qw St) Fr(Kd Tr) OkPj} Fn{Jj(kG kI kK kN lX mE mP mU mZ nC nH nI nK nL nN) nH(aC bQ bR dB iH Jr Nd) nL(aC al bQ bR dB iH Nd) nC(bQ bR dB iH Nd) lX(iJ Kj) ExeC LukG nTkS} gP{fP(Aj bN Ct Fa Ik Kj Mu Of Vv) oP(aI cZ Hc kP Ky Nd nO) Lh(kC nC nH nI nL) aI(ml nB oO oQ Qt) Ct(Fa Us) Ng(Ok On) mW(Hx Qw) ArLj LxnN NdoO HvmT OabN dEfR} nD{Tn(Ji Mm Pj) St(Ji Pj) Nx(dR Gl) HaUn MsQz TrPj QbfP QhKr VunO} Oa{Nt(kO lX mT nB nN) Th(kS oN) nT(Jj Kx) TioN PdmW bNfP} Vu{nO(aI cB eF Ip Nw) Tr(nC nH nL) mM(aI Uh) NwmW} eF{lY(Ef Hc Kl Ky Of Vt) NtnN QwkK JjlX KymM} fP{Lj(AR bN Po) bN(Qb Sr Wm) IsUp QbnA OzPa} Un{Vt(kF kN kP lY mT mY nC nR) QanU} nT{Tj(Jj Nt) dR(mM Qn) lX(Jf Ug) HaKx TnJj} Is{Il(hV iB jM rZ) NdhX JoiC} Th{iA(aO Mu) oN(Li Wm) AaaF} Lj{Ar(Et Hx) Ti(oF oN) aPoP} Fb{gW(cB Ct cY Ng)} Tr{Jj(ml mP) mU(Kg Kj)} lX{NliJ TvLi QacW JfaK} oP{Nt(cD Kd) Lv(al bE)} Ip{Kr(nC nH nL)} lY{cB(Nx Pj) QhKs} mW{LvbQ PabH aUdR} Ar{QwLi QhbN} nN{HbJo JjbN} mP{MmPj KxVo} nC{TncR LhbH} AaPehX NdcVnB JgKjmM JmUknO Unconstrained panels with 3 analytes, where 1.0E-5 >= 'model p-value' > 1.0E-6. Contains 1,472 panels of 13,646,915 total panels evaluated. :
Up{Dc(kC kE kF kG kI kK kN kO kP lW lX lY mE mF mH ml mM mP mS mT mU mW mY mZ nA nB nC nD nF nH nI nJ nK nL nM nN nO nR nT nU oO oP oQ) oE(kC kE kF kG kI kK kN kP lW lX lY mE mF mH ml mM mP mS mT mU mW mY mZ nA nB nD nH nI nJ nK nL nN nO nR nT nU oO oQ) lY(al aJ aZ bG cV dF dG Et lh Ip Is It iZ Je Kc Kp Kq Mb mE mM My Nq Nr NW oF Ok oO oQ Qa Qc Qh Qz St Uh) oO(aE Aw aY Bc bH Cv Di dN eC Hr Hx Iv Jm Mb mP mU nA Nb ND Oe Rf Rg Rh Ri Rj Rm Ub) nD(aJ bG Cv dF dG dM Fr Hf lh lp lr Jl Jm kF Kj Mb mY Nr Nx oF oQ Qa Qh Qz Uf) nA(aJ Cv lh lp lr Jl Jm Mb mU mY Nr Qa Qz Rm Uf) Jm(lW lX ml mM mU mZ nC nH nI nJ nL oP oQ) Cv(kE kG lW mE ml mU nC nH nL oP oQ) Ip(kC kF kO mT mY nC nF nH nJ nK nL) oQ(aE eC Mb Nd Nx Rh Ri Ub Uv Vt) Qh(aR aY bN cR lX mM nN oP) Is(cV kF kN kO ml oP) Mb(kF mE mF ml nK) Qa(mF mP mU nB nl) fP(bN Lj Oa Qb) mP(aJ dM lh lr) Bc(kP mW nO) Vt(nR oP) bN(cS Us) ArLj DinR EtkF ThOa FrkE TnlX IhnI lqoP JknO LikI NwmW WncH dJmH} gP{fP(aG aO aW Ax aY Ba bl cC cH cQ Cs Ed Ef Fp Fw gC Gl Hb Hc Hu lb lh Il lr Is Iu Iz Jh Kk Lx Ly Ma Mf Mh Ml Mm Mv Mx My Nw Nx oE Oh Oy Oz Pc Pd Qt Qy Vo Vs) Ct(Ax bQ bZ Cq Cs Cu dF dG FR Fw hB Is Ld Li Lj Lx Lz Mh Mp Mr Mt Mw Nr Nw Oa Oh Ok On oP Pe Pf Qh) bN(Ed Et hB Jn Jr Kf Kk Ko Li Lj No Pz Qa Qe Qh St Tr Uh Uk Um Us) Oa(al AR cA dA Dc Hb Ib Jj Ng oE Qt Qw Qy Rg Uk) Lj(al cS dA dl iZ Jj Kx oE Pk Qt Qw Rg

Figure 27 Continued

Uk) Ng(aI Bg bQ bZ Et Fa Ke Lx Mt Nw Tr) oP(Ch Hv Hx Ib Id Lv Oy Qt Qu Qy Vt) oE(aI Li Mr Mt Nn Pa) Fa(De Mu Mv Oy Qt) aI(aY kO
Mu Qy) fR(Fn Jj Pd Qt) gC(cW dE Lu Tj) Mg(Et Mw Ok) Ri(mM mT oO) Wn(Is Mw Mz) Ib(On Us) Qt(hB Kf) Rh(mW nR) eM(dE Mb) AjOk
CsmW JjnD LhkO} Ri{oQ(aG aQ bZ cB cJ cX dA dB dD eC eF IP iZ kK Kr Lx Ma Mj Mk mW Mz nD Ne Nl Nw oE Tr Ur Vt) oO(bG dM Ed
Fr Ib iP Kj Kk Lj Lx lY nA NC nH nL Nr Nx Oa oF Pa Pf Qn Tn Un Vu) Lx(kC kE kG kK kP lW IX mE ml mM mS mY mZ nB nC nH nL nU
oP) oE(kC kF kI kO lY mH ml mM mT nA nB nC nD nF nH nI nJ nL) Fr(kE kG kO IX lY mM mZ nC nD nH nI nJ nK nL nN nU oP) lY(aJ bG
bQ dF dM Gp hB pF Ue) oP(dF iP Li Lj No Oa oF Tn) nU(dF dM Nr Pa Tn Vu) mM(bQ cT dF Nr Ok Uh) aJ(IX mP nB nD nR) eC(kF kO nD
nJ) Ip(nC nH nL) bV(kG mP nR) hB(kN ml nB) kO(bQ Mw Ql) Tn(kE IX) Qa(nD nT) Lh(nH nL) Vu(kK mY) nN(Nw Qw) mS(bG Pa) ThOa
QdnH LikN LjmW dMlX} Wn{Bo(Aj Al Ap Bn Dc Dl Dp Fw Ih Io Iq Is Jm Kc Kl Kq Mw Mz Na Ng Nu Nv On Qb Qh Qu Qz Ue Vv) Mw(Af aO Bn bV Cv CX DB Dg Dl Ez fP Hf iH Jt Ks Ng Nv pF Rb) Hf(aM aO aY bF bQ bR bZ cC cE cF cI cN Is nY Us Vv) Hc(aL aO aW bA bZ cE dF Hq oF oN Ra Tn Us) Is(aO aY bV Cv Cw DB hB iH Na pF Qv) Db(Bb Kx Li Qz Vv) Us(Bb Me Tv Vt) Vv(cP fP kQ Qn) Pj(cC cH cP cX) Tn(Aj Dl Ng) Pa(cJ dB kR) Fb(cX Rb) Ra(bO Vt) Jl(aK Rb) BbKz CtMy FatF MldA IcVo TtJt LicX NxcH VtPf PefP} oE{Bn(kC kE kF kG kI kK kN kO kP lW lX lY mE mF mH mI mM mP mS mT mU mW mY mZ nA nB nC nD nF nH nI nJ nK nL nM nN nO nR nT nU oO oQ) lW(Ar bS cA cK De Iv Kr Nf No Rg Vs) mS(bS cA cK Ir Mr Nj No Po Rg Vs) nO(Ar cO Cq Dc Ha Nj Nk Rg Vs) Mj(kC nC nD nF nH nJ nL) Kr(kI nC nF nM oO oP oQ) oO(Ar Nj Rg Tv Vs) Af(mP nA nN) Ex(fP hB Nd) Pa(aE dA Qw) mM(Bg Cu Rh) Vq(Ax bN) BgkE CsaP DemI ThOa NkQh LjaE} bN{fP(cH Ed Hb Hr iA Id Il Jd Jm Jn Jq Jr Kc Kk Kn Ko Li Nn Nq Nr Ns Pz Qa Qc Qh Qm Qn Qw Qx To Tr Uc Ur Vq Vt Vv) cS(Il Jm Jr Li Lj Oa Pz Qh Qw Sr Tr Wm) Wm(aI bQ cZ Et Gp Is Ko Qh Uh) Hr(aI Gp Ko Lx Mt Uh) Qh(Al Bn Dc Dd De dJ) iJ(Ad Bb Cs Dc Is Lj) Uk(Ih Is Jm Pz) Ar(Lj Oa) Bn(Et Sr) De(Ko Vq) CukE DchG FwQw LxSs IsQx UraI} Tk{Mw(Ef Et Ez Fy Hc Hv Ic Ii Il Is Iu Iz Jg Js Jt Ju Kg Kl Kq Kr Ks Kz Ly Me Mg Mn Mt My Nc Ng Nn No Nr Nv Nx Ny Oe Oi Ok Om On Or Pg Qc Ql Qn Qu Rb Rj Ss To Ua Ug Ur Us Ut Uu Vo Vs Vt Vv) Is(Fb Kr Li Qn) Tn(Kq Ng Qu) Kr(Jn Li) Kz(Dp Ih) FbMn IrVs} Lj{Ar(aE aG aL aO aX dA eC Hb Iv Jj Kc Ke Mu My Pz Qw Tv Uk Ur Vv) fP(aE aW bM dA dJ eC hG Jd Ky Lx Nj Nk Nl St) oP(No Rg Rm) Nk(eC nY) aE(cS Kc) BgkE DeiJ PoeC ThoN PkdJ} eC{Fn(Gz kC kO nA nC nD nF nH nJ nK nL) Qv(mU mY nB nJ oQ) oQ(aP Ib nO Un) Nx(mI nI nO) Gz(Ip Nd) Ib(kP nB) mY(Ar Nk) nC(bG eF) kF(aK Un) FbgW ExIp NgTr QbfP JflX VunO nTnJ} kE{Tn(Al An Ao aQ Cu Dg dJ Ib Ic Kg nT Rg Ss Us Ut) Bg(Fr Li NN Oa Oh Qb Vu) Vu(Bb Cv Cw) Fr(Kk Rf) AfUa ArLx BnSt CvUg FnoQ QwbA eFlY} fP{Qb(aP aR cU dA dJ Jd Lv Ma Mu Nk Nt Pb Qe St Vv) Vv(Bb Is Lx Nn Qh) Jd(Is Oa Qh) Oa(aR Th) gC(bL Ne) MaIs NlcM IkSr} Fn{fR(aK bV cW dE Fr Hf Il Kq Uu) As(mU nH nL oQ) Db(nC nH nL) Jj(oO oQ) nH(Hf Na) UknC bQnK nLkS} Ug{Cv(kG kI lY mE mF mH mP mT mU mY nA nC nK nL nN nO nR nT nU oO oP oQ) DcoQ} eM{cV(aO cX Ef Io Kr Ld Lv Mj Nh Nl Ou Pj Tj) Lv(aK aQ cR dJ eF Na Pj) cR(aY Ij Is)} Th{Oa(bU Co HC iO Je Kn Lv Mu Ng oF) Co(Ax Nr) Cs(Mu Vv) WmpF MuOh aOiH cOiA} Is{Il(hW iC jE jF jH jI jK jL jP jQ jR) qZ(Qa Qe) ArJj WmdA NchX JojG cWgC} Un{Bc(kI mI mP nA nH nJ nN) Vt(kK mU nI oO oP oQ) Dc(mM nH) AlnH VunD} Fb{gW(AJ aQ cC dR Hc Jr Kk Ko kQ Lx nY Of Pa Qy)} Uk{Pz(aI aR Ng Pa) Al(mW nO) dA(Lx Qh) ArOa DcmM QbnT QwJm alaN} nD{Vu(Hw Mm No Uv) Aa(St Tn) AoTn DcPj DeQh MbMs IcKj KrbG} aI{Bc(mM mS nO oO) Lv(mM mU nU) AwnB DcmM} Lx{Ng(aE dA) Vv(aE aR) ArQw AwcH IbnA JtdA} Qh{dA(Jt Ng Wm) Bn(nH nR) ArMu CtnO} Oa{Af(lX nB oO) Ar(Hb Jj) BnlX KcnW} gC{cW(Ms Na Ne) LvdJ MtaY NedE cIcV} Vu{nO(Bo Ur Us) NonR UtnI dJmW} eF{mP(nH nL) KykK RjnH RfnC} Li{No(kN mF) oN(Kc oK)} Pa{bH(kI oP) TzQw RgnU} Ng{Bg(Hb Hc) OkhX} Ip{kO(nC nH nL)} Jj{mM(Al Dc) CqnT} fR{To(dE dH) LvOr} mP{Qa(Ib Id) SrKg} oP{Nt(Cq Fw) LvSs} Tn{UtlX nAnL} Il{MziB aYcS} Vq{AjbQ MwIb} nT{BnlX KkkS} nC{KmA nHnK} oO{UcVo UsbH} AxPdmW CxKgoQ DeExaY MgOkhX NdcHmI PzaAqY RfNxnU Unconstrained panels with 2 analytes, where 1.0E-4 >= 'model p-value' > 0. Contains 14 panels of 99,106 total panels evaluated. : fP(bN gP Lj Qb) gP(Ct Lj Oa) ArLj BgNg WmbN FbgW MwTk TnkE mMoE Unconstrained panels with 2 analytes, where 1.0E-3 >= 'model p-value' > 1.0E-4. Contains 222 panels of 99,106 total panels evaluated. : bN(aI cS Ed Et gP HB hF Hr iA Ib Ic Id iJ Jj Jm Jn Jr Kc Kk Ko Li Lj Lx Oa oE oK Pz Qa Qb Qc Qe Qh Qn Qw Qy Rc Sr Ss To Tr Uc Uh Uk Up Ur Us) fP(aO aW aY bM cC cH Ct dJ eC Fa Hb Hc Hr Hu Ik Il Iq Is Iu Jd Jm Jn Lx Mg Mu Ng Oa oE Of Oh Pd Pz Qh Up Vo Vv Wm) gP(aI Aj Cs Ed Fa Fw HB Kk Li Lx Mg Mh Mu Ng Nw oE Ok oO oP oQ Qt Qw Qy Uk Vs) hX(Iq Is Li Lz Mh Mj Mr Mt Mz No Pa) Lj(aE aI cS dA dJ eC iJ Qw Up Th) Ng(Ad Fb Hb Qh Tn Tr Uc Vq) Qw(Is Jm Li Lx Mu Qb Uk Th) Oa(AR dA De eC Up Th) Uk(aI aN Et Ip Jn nC Pz) Lx(aV aY cH dA eC Vv) Th(Cs Ed Mu oN Wm) oE(cE Nd nO Pa Vq) Ct(Hx Is Jn Qh) Fn(fR nC nH nL) Mu(bQ Hb Qh Us) Up(Is lY nD Qh) Mz(hA iB jL) Ip(nC nH nL) aY(aI Fa Jr) qY(aA Mb qV) Et(De Vv) Is(Hu Il) Ri(oO oQ) dA(Qb Qh) eM(cR cV) BoWn CqOy HbNx VunD VqkC eFkE nTlX Unconstrained panels with 2 analytes, where 1.0E-2 >= 'model p-value' > 1.0E-3. Contains 2,856 panels of 99,106 total panels evaluated. : fP(aA aC aD aE aF aG aH aI AJ aK AL aM AN AP aQ aR aS aU aV Aw AX aZ BA BB BC bE bF bG bH bI bJ bL Bn bO bP bQ bR bS bU bV bW bX bZ cA cB cD cE cF cG Ch cI cJ cK cL cM cN CO CP CQ cR CS cT cU CV CW cX cY cZ dA dB DC dD DE dF DG dH DI DK DL dM dN Dp dR Ed EF Et Ez Fb Fn Fp Fr Fw Fy GL Gp gW Ha Hf hG Hq Hv Hw Hx iA Ib Ic Id IH Ii Ij Im In IO Ip Ir It Iv Iz Je Jf Jg Jh Ji Jj Jk Jl Jo Jp Jq Jr Js Jt Ju Jv Jy Kc Kd Ke Kf Kg Ki Kj Kk Kl Kn Ko Kp KQ Kr Ks Kx Ky Kz Ld Lh Li Lu Lv Lw Ly Lz Ma Mb Mc Md Me Mf Mh Mi Mj Mk Ml Mm Mn Mp Mq Mr Ms Mt Mv Mw Mx My Mz Na Nb NC Nd Ne Nf NH Ni Nj Nk Nl Nm NN No Nq Nr Ns Nt Nu Nv Nw Nx Ny Oe Og Oi Ok Om ON Or Ou Ow Oy Oz Pa Pb Pc Pe Pf Pg Ph Pi Pj Pk Po Qa Qc Qd Qe Qg Ql Qm Qn Qt Qu Qv Qw Qx Qy Qz Ra Rb Rc Rf Rg Rh Rj Rm Sr Ss St Tn To Tr Tt Tv Tz Ua Ub Uc Ud Ue Uf Ug Uh Uk Ul Um Un Uo Ur Us Ut Uu Uv Vp Vq Vs Vt Vu Tj Th) gP(AA aD aJ aK aV aW Ax aY Ba bB bC bV cA cC CH cK cL cR cS cV cZ dA dB dD dF dI dJ dM eC Ef eM Et Ez Fb Fp FR gC Gp Hc Hf Hr Hu Hv Hx Ib Ih Ij Ik Il Im In Io Ip Iq Ir Is Iu Iz Jd Jh Jj Jn Jo Jr Js KC Kd KE KF kG kI Kj kK KN KO kP KR Kx Ky Kz Ld Lh Lv LW lX LY Lz Ma ME MF mH MI Mj Mk Ml mM Mn MP Mq Mr MS MT mU Mv MW Mx MY mZ nA nB nC ND Ne NF NH nI NJ NK nL nM NN NO Nq nR Ns nT nU Nv Nx Ny Oe Of Og Oh Om On Or Ou Ow Oy Oz Pb Pd Pe Pg Pi Qa Qb Qc Qd Qe Qg Qh Qu Ra Rc Rf Rj Rm Ss St Tv Ua Uc Ug Uh Um Uo Up Us Vo Vt Vv Wn Wm Tj Th) bN(Ad Aj Ap aQ aV AW AX aY Ba BB Bc bF Bg bM Bn Bo bQ bV cA cH Co Cq cR Cs Ct Cu cV cX dA Db Dc dF Dg Di dJ Dk Dp eC Ez Fa Fb Fn Fp Fw Fy Ha HC hG Hq Hu Hv Hw Hx IH Il iO iP Ir Is It Iu iZ Jd Je Jf Jg Jh Ji Jk Jl Jo Jp Jq Js Jt Ju Jv Jy Kd Ke Kf Kg Ki Kj Kl Kn Kp kQ kR kS Lh Mn Ms Mu Mw Ng Nm Nn No Nq Nr Ns Nt Nu NW Nx nY oF oH Ok oN Pa pF Po Qd Qg Ql Qm Qt Qu Qv Qx Qz Ra Rb Rf Rg Rh Ri Rj Rm St Tn Tt Tv Tz Ua Ub Ud Ue Uf Ug Ul Um Un Uo Ut Uu Uv Vo Vp Vq Vs Vt Vu Vv Th tF) oE(aE aI Aj aP aR aV aW aY Bb bF bM bQ bS bZ cC cH Cq Cs cY dA dD De dF dL Dp eC Ed Et Ex Fa Fb Fn Fw Gz HB Hc hG Hr Hx iA Io Ip Iq Is Iu Iv Jd Jj Jn Jq Jr Js Jt KC kE kF kG kI KK kN KO kP kQ Ky Li Lj Lv lW LX LY Lz Mb Md ME MF MH mI Mk Mm Mn mP Mr mS MT mU mW mY mZ nA nB nC nD nF Ng nH nI nJ NK nL nM NN Nq NR NT nU Nw Nx Oa Of Og oO Pe Pf Pz Qb Qh Ql Qn Qw Qx Qy Ss Tn To Tr Tv Ug Uk Un Up Ur Us Vu Vv Wm Th) Qw(aI Aj AR aW Ax aY Bb Bc bF Bn bQ bZ cC cH Cq CS Ct Cu cV CX De dJ Dp eC Ed Et Ex Fa Fb

Figure 27 Continued

Fn Fr Fw Gp Ha Hb Hc Hf Hq Hr Hx Ib Ic Ih Ij Il Im Io Ip Iq Ir It Iu Iv Jd Je Jj Jn Jq Jr Kc Ke Kf Kk Kn Ko Kq Kr Lv Ly Lz Md Mg Mh Mp Mr Ms Mt Mw nC Nd Nf Ng NN No Nq Nr Nw Nx Oa Of Og Oh Ok On Or Ou Ow Pa Pb Pd Pe Pf Pg Pj Pk Po Pz Qa Qc Qd Qg Qh Qn Qt Qv Qy Qz Rb Rc Sr Ss St Tn To Tr Tt Tv Tz Ue Ug Un Uo Up Ur Us Ut Vo Vv Wm) Lj(aG aH Aj aL aN aO aP aQ aR aU aV AW AX aY Ba bB bF bM Bn bS bU bV bZ cA cC cH cJ cK Cp cR Ct cV cX cY cZ DC DD DE dI Dk dN Ez Fn gL Gp Ha Hb Hc HF hG hX iA Ib iZ Jd Ju Kc Kk KQ kS Kx Ky Kz Ld nW nY oH oK oN Ou Ph Pi Pk Qh Qt Qv Qx QY Ra Rc Rf Rg St Uf Uk Un Us Vv Wm Ti) Uk(aE aQ aR aV aW aY bF bM bQ bS bZ cH cK cS cX cZ dA dD dE dF dJ eC Ed Ez Fa Fb Fn Fw Hb Hc Hf hG Hr Hx iA Ib Id Ih Ik Il Ir Is It Iu Jd Jl Jm Jq Kc KE Kk Kn Ko Kz Lh Li LX mE Mu MW nB Nd Ng nH nK Nm NN nO Nq Nw Nx Oa Of Oh Ok Ou Qa Qb Qc Qh Qt Qx Qy Rm Sr Tr Up Us Vq Vt Vu Vv Wm) qY(Et Fr hA Hq HR Hu Hw HX iB iC Ih Ii Ij Ik Il Iq Is Iu Iv Jh jI JL Jn Jo Jp Jr Jt jY Li IK IL IN Lu Lv Lw Lx Ma Md Me Mf Mh Mi Mj Mk Ml Mm Mr Ms Mv Mw My Mz Nc Nd Ne Nf Nh Nj Nk Nl Nn No Nq Ns Nv Nx Ny Oe Og Oi Ok Om Oz Pa Pb Pc Pd Pe Pf Pg Pz Qa Qb Qc qT qW qX rA rB rC rX rY rZ) Lx(aE aH aI Aj aK aM aN aO aP aQ aR aS aU AW aX BA bB bF bI bJ bL bM bQ bR bS bU bV bZ cA cC cG cK cL cM cN cO CP cQ cR cS CT cU cV cW cX cY cZ dB DD DE dG dH dI dJ dL dN dR Ez gW Hb Hc Hf hG hX IB Iz Jd Kc KQ kS IX oN Pj Qt Qu Qy Rc Rf Rg Ss Ua Up Ut Vo Vv Wm Th) Oa(aE aI Aj aL aQ aU aV AW AX aY bM Bn bS bV cA cH cK cN Cp cS Ct cV cX cY cZ Dc dD dE dI dJ Et Ez Fn Gp Hb Hc HF hG Hr Ib iJ Ik Ip Ir Iv iZ Jd Jj Jn Jo Jt Kc KQ kS Kx Lv IX Mj Mu Nd Ng Nj Nk Nt nW Nx nY Of oH oK oN Pb Pd Ph Qt Qy Rg Ua Ut Vv Wm Ti) Is(aI aV aY cH cV dA dJ eC Et Ez Hq Hr Hv hW Hx IB iC Ih Ii Ij Ik Im In Ip It Iv Jd jI Jj Jk Jm Jn Jo Jq Jr Jt Kk kP IK Lv Lw Ma Md Mf Mg Mi Mk Ml Mr Ms Mv Na NC Nd Ne Ng nH Nj NL Nr Ns Nt Nx Og Ok Om Oy Pb Pd Po Pz Qd Qt Qy rX Ua Vs Vv Tk Wn Wm) Ng(aE aI aO Ap aQ aV aW aX aY Ba Bb bF bM Bo bQ bV bZ cH Co Cq CS Cu cV cY dA Dc dF Dg dJ Dk Ed Ef Fa Fn Fw Fy Gp Hf iA Ic Id iJ Iz Kc Ke Kf Kg Kk KJ Kn Ko Kp Kq Ou Pk Ql Qn Qx Qy Qz Rb Rm Sr St To Tt Tv Tz Ua Uf Uh Uo Up Ur Us Ut Uu Vu Wm Th) Ct(Ad aI Al aO Ap aY Ba bF Bg bM bQ bZ cC Co Cq CS Cu cV cY Dc dF dJ Ef Et Fa Fb Fr Fw Gp Hb Hr Ih Ii Il Io Ip Iq Ir It Iu Jk Jl Jm Jq Kc Ke Li Ly Mq Mt Mu Mw Nn Nq Nv Nw Nx Of Oh Ok On Ou Pz Qa Qb Qc Rm Sr St Tn Tr Uc Us Ut Th) Th(Aa aF Aj AO Aw Ax aY aZ Ba Bc bI bS bU bV Ch cK cL Co cS cU cW dA De dJ eF Ez Fp Hc hF Hq Hr Hu Hx IB IH iJ Il Jk Kn Ko kS Li Lv Lz Ma Md Mk Mt Mv Nl Nt Nx Of Om Oy Oz Pb pF Ph Pz Qb Ql Qt Qu Qy Rc Ri Rm Ss Up Ur Ut Vv) Mu(aI aO aQ aV Ax aY bB bF Bg bM bZ cC cE cH Co Cq cR CS Cu CV cX cY cZ Dc dD dF dG dJ eC Ed Fa Fb Fw Gp Hc Hf Id Kc Ke Kf Kk Kn Or Ou Ql Qn Qy Ra Rm Ss Sr Tn Tr Tv Uc Ug Uh Uo Up Ur Ut Vv Tj) Up(AA aI aY Cs Ed Et Fa Fw hB Hr Ih Ip Ir Jn kC KE kF kI KK kN kO kP Li IW IX mE mF Mh mI mM mP mT mU mW mY mZ nA nB nC Nd nF nH nI nJ nK nL nN nO nR nT nU Nw Og Oh oO oP oQ Qa Qb Rm Us) al(Aj aK aN aU AW Ba Bb Bc bJ cA cG CS cW cX Dg eC Ed Fa Hb Hc hF Hr Iq Iu Jj Jn Jr Jt Kc kE kO Li Lv lY Mg mI mM Mn mS nC nH nO Nt Of Pd Pz Qb Qh Qt Qy Sr Ss Ur Vo Vv Wm) Hb(Aj AN AO Ap AR aS aV AW Ax aY Ba Bc Bn bV bZ cC cH Cp CS cV cX dA dD DE dF dJ Dl Ed Fa Fb Fw Hc Hr Ip Lv Mg Ms Nd Of Og Ou Pb Pd Pj Qt Qy Rc Us Vv Wm) eC(aV aW bF bZ cE cH Cs dA dD dF Ed Ex Fa Fb Fr Fw hB iA Ib iH Ip Ir Jr kC Kd Kk Kn KO Li Mh Mn Mr mY Mz nC nD nH nJ nL Nw Nx OK Pa Qb Qh Sr Ss Tr Us Vq Vv Wm) Vv(aO aR aY bF bQ bZ Co cS cX dF dJ EJ Fa Fb Fw Gp Hr Id Ij Ip Ir It Jj Jn Jq Jr Kc Ke Kk Lh Li Mw Nd Nw Og Oh Ok On Ou Qa Qb Qh Tr Tt Uh Wn Wm) Fa(Aj aP aQ AR aV Aw bL bM Bn cA cH cK cN cS cV cW cX dA De dJ dN Gp Hc Ib Ik Iv Jd Jj Kc KQ Kx Lv Nx Of oH Pb Pd Qt Qy Ss Ut Wm) hX(Aa Et Fr Hr Hx iB Ii Ip Ir Iu Iv Ji Jl Jn Jp Js jY Lh Mb Me Nc Nd Ne Nh Nj Nk Nl Nm Nn Nw Ny Oh Ok On Pe Pf Pg Po Pz Qa Qb Qd rX) Ip(Ed Ez Hq Hr Hu Hv Hx Ik Il Iq Ij Jm Jn Jo Jr Jt kO Lv IX IY Ms nA nD nJ Nr Ns Nt Og Pz Qa Qb Qt Qy Ss Ug Vo Vq Wm) aY(Aj Ba cC Cq CS cV Ed Et Ex Fb fR Fw Gz Hc Hf Hr Il Jj Kc Kq Kr Ks Mw Nx Or Pa Pd Qa Qh Qy Ug Uo Us Wm) Mz(eD hR hV hW iC jD jE jF jG jH jI jK jM jO jP jQ jR jT jU jV jY IK IL IM IN IO qV qX rB rC rX rY rZ) Hx(Af Aj Ar Aw Ax Ba Bb Bc Bg Bn CH Co Cp Cs CX Db De Dl hF hR iB iC Ir Jn IX Qy Ss Wm) iB(aA hR hW Il Io It Iu jD jI Jl jY Li IL IN Ly Me Mr Mt Nq Nw Nx Ok Pa Qa Qb qT qZ rB rX) Jn(Aj Bn dA De Ed Ez Hc Hr Hu Ik Jd Jj Jt Kj Kk Ms Nd Nr Nt Og Ok Pb Qb Qt Qy Rc Vo Wm) IX(eF Fn Hw iJ Il Jf Jj Jm kC kF Kj kO Kx Mf Ms nC ND nH nJ NL Pz Qc Rb Ri Tn Vu) Wm(aQ aR aV cC cH cX cZ dA dD dJ Et Gp Jj Jq Kc Ke Kk Mh Nd Nw oH Ok Qb Qh Qt) Hr(aR aV aW bC bM cH cS cV cZ dA De dJ Ez Fb Gp Ib Kc Ke Kk Qt Qy Ug Um) Qh(Aj aQ AR aV Bn cA cK Cp cV De dJ Ez Ib Jd Jj kE Of Oy Qt Qy) Et(Aj aR aW Bn Dg DI Ed Ez Hc Jd Kc Pj Qt Qy rB Rc Ss Ue Vo) Jj(aN aR aW Cs dA De Dp Ed Fb Fw Jd Jm nT Pz Qt Qy Rc Ur Us) Wn(cH cX Db Hc Hf Jl Kz Li Mw Nv Pa Pf Pj Ra Rb Rg Us Vt) Qy(aO bF bM bQ bZ cX dF Fb Ij Kc Ke Li Mw Nd Nn Ok Tn) nC(bH bR cB dB eF Jg Jm Kr lY Ms NA NK Ri Tn Vu) Fn(eM Ex Gz kC kE kO mE mZ nA nD nJ nK nN nO oP oQ) Qt(Fb Ij Ke Kf Li Mw Nn Nw Ok Ou Qa Rb Tn Tr Us) Qb(aE aQ aR aV aX cS cV De dJ Ez Hu Il Kc Pb) dA(Ed hB Iq Ir Jr Li Nn Nr Qa Tn Us Vu) Aj(Ad bF Bg bQ cC Fb Jq Ke Mw Ok On) De(cC Jp Jq Ke Kk Ko Li Ok Tn Tr Us) lY(eF Ib Kc Mf Ms Na Nd Pz Qc Ri Un) nD(cB eF Ex Gz Ms Na Pj Tn Un Vq) nH(bH cB dB eF Jm Ms NA Ri Vu) Ed(aR bM dJ eM Gz Hw Kc Ti) Ib(fR mP Mw nA Nn Pz Us Vq) Li(aR cS dJ Ez Kc IL oK Tk) Of(bF bQ bZ Cq Fb Tn Tr Us) Ke(AR Ba Cp Jd Nx Rc) Ok(Ap Cp Dg Dl Hc Hu Jt) Vu(kE kK mW nA nI nO nT) Vq(cX dJ Ik Jh kP nA Oh) eF(kK kP mM mP mZ nL nN) hB(aP aR aW dJ kE mM nO) rB(hR Nc Ne Nk Nl Og Pz) Fb(Aw Ch Ez Hc Ss Tk) bH(mU mW nL nR oP) Ms(kP nA nT oP) Jr(aQ aR aV dJ) Kk(aR cS Kc Lv) bQ(cA cK Hq kE) fR(dE Ik Lv Mj) nL(cB NA nK) Fr(hA hR mZ) Il(cS Iq Ir) Ri(mM nU oP) Tk(Kz Tn Vt) aK(aQ aV cY) eM(dJ Jf Lv) Cs(Ar cC) Ez(Mw Us) Na(kO nJ) Hu(Ir Ny) Jd(Nw Qa) Jq(Bn cX) Kc(Fw Hc) cB(kO nJ) gC(cW Ne) gW(aU cY) nA(Ex Gz) hR(Nd Pa) iC(Nk Nl) kE(Bg St) BccC MabZ MeIN Mw bN(Qb Sr Wm) Is Up QbnA OzPa} Un{Vt(kF kN kP IY mT mY nC nR) QanU} nT{Tj(Jj Nt) dR(mM Qn) IX(Jf Ug) HaKx TnJj} Is{Il(hV iB jM rZ) NdhX JoiC} Th{iA(aO Mu) oN(Li Wm) AaaF} Lj{Ar(Et Hx) Ti(oF oN) aPoP} Fb{gW(cB Ct cY Ng)} Tr{Jj(mI mP) mU(Kg Kj)} IX{NliJ TvLi QacW JfaK} oP{Nt(cD Kd) Lv(aI bE)} Ip{Kr(nC nH nL)} IY{cB(Nx Pj) QhKs} mW{LvbQ PabH aUdR} Ar{QwLi QhbN} n

Jj Jn Kc Ke Li Lx Mw Nd Nn Ok Qh Tn Th) Up(aY Cs Ed Et Fw hB Hr Ih Ip Ir Jn Ke Kk Li LX Mh nA Nd Nw Og Oh oO oP oQ Qa Qb Rm Us Th) Is(aI aV aY bN cH cV dA dJ Ez IB Ik Jd jI Jj Kk kP Ms nC nH nL oE Qt rX Ua Vs Tk) Qw(aI aR aY Bn bQ bZ cH Cq cV cX De Ed Fb Fw Hr Iq nC Ng NN Oa oE Pf Qa Qh Tr Us) Th(aF Aj bI bN bU Co cW dA eF fP Hc Hu Hx Ib iH Il Kn Lv Ma Mk Ng Nx oE Oz Ri) Qt(aI Et Fb Hb Hr Ij Ip Jj Jn Ke Kf Li Lx Mw Nn Nw Oa Ok Ou Qa Qh Rb Tn Tr Us) lX(eF Fn iJ Il Ip Jf Jj Jm kC kF Kj Kx Mf nC nD nH nJ nL Oa Pz Qc Rb Ri Tn) Qh(aI Aj aQ AR aV aY Bn cA cK Cp cV De dJ Ez Ib Jd Jj kE oE Of Oy) hX(Fr iB Iu Jl Js jY Lh Lj Lx Me Nc Nd Nn Nw Ny Oh Ok On Pe Pg Po Qd) Ng(aI Ap aY bF bQ bZ Co cS cV dJ Dk Ef Ke Kf Ko Oa Qn Tt Ua Us Ut) Lx(Aj aR Aw Ba Cp De Ez Hb Hc Hf IB Jd Kc Kq oE Qu Rc Ss Ua) aI(Aj aW bJ Ed Hb Hc Hr Jr Lv mM Mu Nt Oa oE Of Pd Pz Qb Ss Vo) aY(bN cC cS cV Ed Et Fb Hc Hf Hr Il Jj Kc Mu Mw Oa Or Qa Ug Us) De(Hb Hr Hx Jj Jn Jp Jq Ke Kk Ko Li Lj oE Ok Qb Tn Tr Us) Et(Aj aR aW Bn Dg Dl Ed Ez Hc Jd Kc Pj rB Rc Ss Ue Vo) Jn(Aj Bn dA Ed Ez Hc Hr Hu Hx Ip Jd Kj Kk Ms Og Rc Vo) Oa(aE aQ Bn Cp cS cX dJ Gp Hb Hr Jd Jj Kc KQ Mu Nj) nC(bH bR cB dB eF fP Jg Jm Kr lY NA NK Ri Tn Vu) oE(aE aW bF bQ dD Hb Hr Jq kQ Lj mS Mt Nn Og oO Pz To) dA(Ed HB Hr Iq Ir Jj Jr Li Nn Nr Qa Tn Us Vu) Ip(Ed Ez Hu Hx Il kO lY Ms nA nD nJ Ss Ug Vo) Wn(cH cX Db Hc Hf Jl Li Nv Pf Pj Ra Rb Us Vt) Hr(aW bM cZ dJ Ez Fb Gp Hb Ib Kc Ke Kk) Qh(aE aQ aR aV aX cS cV dJ Ez Hu Kc Pb) Jj(aN aR aW Dp Ed Fw Jm nT Pz Rc Ur Us) Lj(aR aV Dc dI Hf hG iZ Kc Ph Pk Rg St) Aj(Ad bF Bg bQ Fb fP Jq Ke Mw Ok On) bN(Ad bV cH cV dJ Fw Ih Il Mu Nx Ok) lY(cF Ib Kc Mf Na Nd Pz Qc Ri Un) iB(aA hR Hx Il jI lN Me Nx qY rB) Hb(aR cS Ed Fb Fw Lv Of Rc Us) nH(bH cB dB eF fP Jm NA Ri) Li(aR cS dJ Ez Kc IL oK Tk) Of(bF bQ bZ Cq Fb Tn Tr Us) Ed(aR bM dJ eM Gz Hw Kc) Mu(bF bZ Cq cV dF Kk Tn) Hx(Bn cH cX hF hR Ir Ss) Ke(AR Ba Cp Jd Nx Rc) Ok(Ap Cp Dg Dl Hc Hu Jt) hB(aP aR aW dJ kE mM nO) rB(hR Nc Ne Nk Nl Og Pz) qY(jI jY lN Nc Nj Pc rX) Fb(Aw Ch Ez Hc Ss Tk) Ib(mP Mw nA Nn Pz Us) nD(cB Ms Na Pj Tn Un) Vu(kE kK mW nI nO) nL(cB eF NA nK) Fn(eM kE nK nN) Jr(aQ aR aV dJ) Kk(aR cS Kc Lv) bQ(cA cK Hq kE) Il(cS Iq Ir) Ri(mM nU oP) aK(aQ aV cY) Ez(Mw Us) Fr(hA mZ) Na(kO nJ) Hu(Ir Ny) Jd(Nw Qa) Jq(Bn cX) Kc(Fw Hc) Vq(Ik kP) cB(kO nJ) eM(dJ Jf) fP(Ba nN) gC(cW Ne) gW(aU cY) nT(dR Ms) hR(Nd Pa) iC(Nk Nl) kE(Bg St) ArCs MabZ MelN MjfR MwSs MzrC TnTk QclW JljL KqNw PghA PjmP bHmW cAcE cVcX dBiH eFmZ

Unconstrained panels with 3 analytes, where 1.0E-10 >= 'AUC p-value' > 0. Contains 27,902 panels of 13,646,915 total panels evaluated. : oE{mM(AA aC AD aE AF aG aH aI AJ aK AL aM AN AO aP aQ AR aS aU aV aW Ax aY aZ BA BB BC bE bF bG bH bI bJ bL bM bN BO bP bQ bR bS bU bV bW bX bZ cA cB cC cD cE cF cG CH cI cJ cK cL cM cN CO CP cQ cR CS cT cU CV CW CX cY cZ dA DB DC DD DE dF DG dH DI dJ DK DI dM dN Dp dR eC Ed Ez Fa Fb Fn FP Fw Fy GL Gz Ha HB HC HF hG Hq Hr Hu Hv Hw Hx iA Ib Ic Id IH Ii IJ Ik Il Im In IO IP Iq Ir Is It Iu Iv IZ Jd Je Jf Jg Jh Ji Jk Jl Jm Jn Jo Jp Jq Jr Js Jt Ju Jv Jy KC Kd KE KF Kg KI Kj KK Kl KN KO KP kQ kR KS Kx Ky Kz Ld Lh Li Lj Lu Lv LW LX LY Lz Ma Mb Mc Md ME MF Mg MH MI Mj Mk Ml Mm Mn MP Mq Mr MS MT MU Mv MW Mx MY NA NB Nc ND Ne NF Ng NH NI NJ NK NL NM NN No NR Ns nT NU Nv NW Nx NY Oa Oe OF Og OH Oi OK Om ON oO oP oQ Or Ou Ow Oy Oz Pa Pb Pc Pd Pe PF Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Rj Rm Sr Ss To Tr Tt Tv Tz Ua Ub Uc Ud Ue Uf Ug Uh Uk Ul Um Un Uo Ur Us Ut Uu Uv Vo Vp Vq Vs Vt Vu Vv Wm Tj tF) nO(aA aC AD aE AF aG aH aI AJ aK aL aM AN aO aP aQ aR aS aU aV Aw AX aY aZ BA BB BC bE bF BG bH bI bJ bL BO bP bQ bR bU bV bW bX bZ cB cC cD cE cF cG cH cI cJ cL cM cN CO cP CQ cR Cs CT Cu CV Cw cX cY cZ dA dB DC dD dE dF dG dH dI dJ DK dL dM dN Dp dR eC Ed EF Ex Ez Fa Fb Fn FP Fr Fw Fy GL gP Ha HB HC HF hG Hq Hr Hu Hv Hw Hx iA Ib Ic Id IH Ii IJ Ik Il Im In IO IP Iq Ir Is It Iu IZ Jd Je Jf Jg Jh Ji Jj Jk Jl Jm Jn Jo Jp Jq Jr Js Jt Ju Jv Jy KC Kd KE KF kG KI Kj KK Kl KN KO KP KQ kR Ks Kx Ky Kz Ld Lh Li Lu Lv LW LY Lz Ma Mb Mc Md mE MF Mg mH Mi Mj Mk Mm Mn MP Mq MS MT MU Mv Mw Mx MY MZ NA NB Nc ND Ne nF Ng NH NI NJ NK Nl NM NN Nq NR Ns nT NU NW Nx nY Oa Oe OF Og OH Oi Ok Om ON oO oP oQ Or Ou Ow Oy Pa Pb Pc Pd Pe PF Pi Pj Pk Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tr Tt Tz Ua Ub Uc Ud Ue Uf Uh Uk Ul Um Un Uo Up Ur Us Ut Uu Uv Vo Vp Vq Vt Vv Wm Tj tF) mS(AA aC aD aE AF aG aH aI AJ aK aL aM AN AP aQ AR AS aU aV AW AX aY aZ bA BB BC bE bF BG bH bI bJ bL bM bN BO bQ bR bS bV bW bX bZ cA cB cC cD cE cF cG CH cI cJ cK cM cN cO CP CQ cR CS CT cU CV CW cX cY cZ dA DB DC DD DE dF DG dH DI dJ dK DL dM dN dR eC Ed EF Et Ez Fa Fb Fn FP Fr Fw gL GP Ha Hb hC HF hG Hq Hr Hu Hv Hw Hx iA Ib Ic IH IJ Ik Il Im IO iP Iq Ir Is It Iu IZ Jd Je Jf Jg Jh Ji Jj Jk Jl Jm Jn Jo Jp Jq Jr Js Jt Ju Jv Jy KC Kd KE KF KG KI Kj KK KN KO kP KQ kR kS Kx Ky Kz Ld Lh Li Lj Lu Lv LW LX LY Lz Ma Mb Mc Md ME MF Mg mH MI Mj Mk Ml Mm MP Mq Mr Ms MT MU Mv Mw Mx MY mZ NA NB Nc ND Ne NF Ng Nh nI NJ nK NL NM NN No Nq NR Ns nT NU Nv NW Nx NY Oa Oe OF Og OH Oi OK Om ON oQ Ou Ow Oy Pa Pb Pc Pd Pe PF Pg Ph Pi Pj Pk Po Qa Qb Qc Qd Qe Qg Qh Ql Qn Qt Qu Qv Qw Qx Qy Qz Ra Rb Rc Rf Rg Rh Ri Rj Rm St Tr Tt Tz Ua Ub Ud Ue Uf Ug Uh Uk Ul Um Uo Ur Ut Vo Vq Vt Vu Vv Wm Tj tF) oO(aA AD aE Af aG aI aK AL aM aO aP aR aU aV aW aX aY Ba Bc bF BG bH bN bQ bV bX bZ cB cD cE cH cM CO cP CQ Cs Ct cU CV cW cX cY cZ DC dD DE dH dJ dK dL dM dN Dp dR Ed EF Et Fn fP Fr Fy gL Gp Ha hB hC hG Hr Hx Ib Ic Ih Ii Il Im Io Ip Iq Ir Is It Iu Iv Iz Je Jf Jg Jl Jm Jn Jo Jr Js Kc Kd KE kF kG KK Kl KN KO Kp kQ kR Ks Kx Kz Li Lj Lv lW Lx LY Mb MF mH mI Ml Mm Mn MP Mr mT mU Mw MY MZ Nb Nc ND Nh Ni NJ Nk nL nN No Nq NR Ns Nu Nv NW Nx nY Of Og Oi OK oP oQ Pa Pe Pg Pi Po Pz Qa Qc Qh Qu Qw Qy Qz Rf Ri Rj Rm Ss St Tn Tr Tv Ua Ul Up Ut Uu Vs Vt Vu Vv Wm tF) mI(aE AF aN AO Ar bH bJ BN bS cA cD cG cK cL cO Cs Cx Db dH dL Ed eF Fn Fw gL gP Ha Hc Ib Ii Ik Il Io Ir It Iu Iv Jd Jm Jr Js Jt Jy Kc Kd kE Ks Kx Ky Ld Li Lj Lu Lv lW Lx Ly Lz MF Mg Mh Mj Ml Mm Mn Mp Mr Ms mW Mx My Na Nc ND Nf Nj NK Nl Nm NN No Nq nR nT Nu Nx Oe Of On Oz Pa Pe Pg Ph Po Qa Qb Qc Qd Qh Qy Ra Rb Rc Rg Rm To Tv Uc Ug Ul Un Ut Uv Vs Vu Vv) lW(Af aL aM aX aZ Bg bH BN bS cA cD cG cJ cK cO cZ DC De dH eC eF Fn fP gP Ha Hb Hc Hf hG Ib Ih Il Ir Is It Iu Iv Iz Jo Jr Js Jt Ju Kc kE Kr Ks Kx Li Lu Lv Lx Ly Lz MF MH Mp Mr Ms Mw MY nA Nb Nd Nf Nj Nm nN No nR Nu Nx Of Oy Pa Pe Pg Ph Po Qc Qh Qw Qy Qz Ra Rb Ri Rj St Tv Uc Uf Uk Up Ur Vv) Vq(aE aI aJ aL aO aP aQ Ar As Ax bN Bo bQ bS bZ cE cN Cp Cw cY dD De dJ DL dN dR Et Fn fP GP hC Hq Ib Ik Ip Ir It Iu Iv Jj Jo Jt Jy kC KE Ki kS Kx Lj Lv lX Ly Mb mH Mj mP mU Mw nA nC ND Nf NJ Nk NT NW Og Ow Pd Pk Po Qd Qw Qz Sr Tv Ub Vs Vv) mU(Af aN Ar aX Bg BN bS cA Ch cK cL Co De eF Fn fP gP Ha Hf Ib Ii Il In Is Iu Iv Jr Js Jt kC Kd kN kP Ks Ky Lv Lz Mf Mh Mn Mp Mr Ms mW My mZ Nc nD Nf NJ Nk Nm No Ns Nt Nu Nx Of Oi oN Or Oy Pa Pg Ph Po Qn Qw Qy Qz Ra Rb Rc Rg Ri Tv Ug Uv Vs Wm) mP(Aa Af Ao Ap Ar As BN bS cA cK Cx Dc De Dg Ed eF Et Ex Fn fP gP Gz hG Ib Ii Io Is Iu Iv Ji Jj Jo Jr Js Ks Kx Lu Lv Lz MF Mm Mn Mr Ms mW My nC nD Nj Nk Nm No Nt Nu Nx Of Or Oy Pa Ph Pi Qn Qw Qz Rb Rg Ri Ss Tv Ug Un Vs Vu Wm) kE(AF aX bN bQ bS bZ cA cK cV De dH dR EF fP Fr gL GP Ic iO It Iu Iv Jh Jj Jo Js Kc Kd kG kN Ks Lu Lv Lx Lz Mf MH Ms Mv My MZ Nd Ni Nj Nk Nm No Ns Nt Nv nW Nx Of oH oK oN Or Ou Pa Ph Qw Rg Ri St Tn Tv) nD(Af aN Ar aX bH BN bS cA cK cO Cs dA dD De dH dL eC Ex Fn fP gP Gz Ib Ih Ir Iu Iv Jr Js Jt Kr Ky Li Lu Lv Lz Mf Mh Mj Mp Mr Ms My Na Nb Nf Nj Nk Nm No nT Nx Oe Of Oy Pa Pe Pg Ph Pj Po Qn Qw Rg Rm Tv Ug Un Vs) Ex(aI Ax aY bA bN bQ bZ Cs Cu dD dF Ed fP Fr Fw gC hB Hq Ip Is Jl Kd kI Kk KN Ld Lh Li Lj Lx Ly Lz Me Mh Mj Mp Mq Mr Mt mZ nA Nd NN NR nT oF Ou Oz Pa Pb Pe Pf Pg Pz Qh Qw Qz Ra St Tr Tv Uc Us Vs Tj) nJ(AF aN Ar Aw AX bH BN bS cA Ch cK cM Cs dA dD De dH dL Fn fP gP Ha Ih Ir It Iu Iv Jr Js Kd Li Lv Lz Mf Mh Mj Mr My Na Nb Nf Nj Nk Nm No nT Nu Oe Of Oy Pd Pe Pg Ph Po Qw Ra Rb Rg Rm Tv Ug Vs) kN(AF aN aO Ar

Tz Ua Ub Vq Vt Vu) mU(aA Ad aE aJ Al aV aY Bc bH bZ cB cY dD dF dG dJ dM dR Et Fn Fr hB Hu Hx Ih Ii Ij Im Ip Ir Is Kk Li Ly Mb nI Nk Nr Nw Oa OH Ok Pd Pz Qa Qb Qe Qh Qw Ri Tr Ua Ub Uc Vt) nO(Ad aJ Al aM aP Bc bV Cv Dc dG Di dJ dM Et Ez Fr hB Hu Ih Ii Ij Im Ip Ir Is Kq Kx Li Lj Lx Mb Nd Nl Nr Nw Oa Ok On Pb Pz Qa Qb Qd Qe Qh Qw Rm St Tn Tz Uc Vq Vt Vu) mF(aJ Al Bc bG Cv dF dH dJ dM eC Et Fr hB Ih Ij Im Ip Ir Is It Jd Jl Jn Kn Ko Kq Kx Lx Me Nd Nk Nr Nv Nw Oa oF Oh Pa Pz Qb Qc Qe Qh Qw Qz Rm St Tn Ub Uc Uf Vq Vt Vu) kF(aC Ad aE aI aJ Al aQ Bc bG bM cB Cv cY Dc dJ dR eC Fr hB Hu Ih Ij Ik Im Is It Jk kE Kx Ky Ly Mm My Nd Nw Oa Oh Ok On Pb Pz Qa Qe Qh Qw Qz Rh Rm St Ub Uc Uh Vq Vt) kE(Ad aJ Al Bc BG bQ bZ Dc dJ eF Et Fn hB Ih Ij Im Ip Ir Is Jg Jk Jl Kk Kq Li Lj Lx Mb Nd Ni Nk Nr Nv NW Oe Ok On Pz Qa Qc Qd Qe Qh Qw St Tn Uc Vq Vt Vu) nB(aE aI aJ Al aY Bc bJ bM bZ Cv cY dH dJ dR eC Et Fn Fr hB Hf Hu Hx Ih Ip Ir Is It Jg Kx Ly Mb Me My Nb Nd nI Nk Nr Nw Oa Pa Pz Qh Qw Rb Ub Uc Uh Vo Vq Vt) nI(Aa aJ Al aM Ax Bc bG Dc dG Di dJ Et Fr hB Hu Ij Ip Ir Is It Jk Jl Kx Li Lj Lx Mb Mr Nd Nr NW Oa Oe Oh Pa Pz Qb Qe Qh Qw Qz Rm St Uc Uf Vq Vt Vu) nN(Ad aI aJ Bc bG Cv dF dG Et Fn Fr hB hC Hf Hu Hx Ih Im Ip Is It Jd Jg Jj Jk Jp Ke Kq Ly Mb Me Nd Nk Nt Nv Nw Oe Ok Pz Qa Qw Rb St Uc Uh Vq Vt) nT(Ad aJ Al Bc bJ bV bZ Cv dF dR eC Et Fr hB Ih Ij Im Ip Ir Is Jk Kk Kn Lx Mb Nd Nk Nl Nr Nw Oa Ok Pz Qa Qb Qe Qh Qw St Uc Vt) mM(Ad aJ Al Bc bG Di dJ Et Fr hB Ih Ij Im Ip Ir Is Kx Li Mb Nd Nr Nw Oa Oe Oh Ok Pz Qa Qe Qh Qw Rh St Tr Ua Ub Uc Vq Vt) mI(Ad aJ Al Bc bG Dc dJ Et Fr hB Hu Ih Ij Im Ip Ir Is Jm Nd Nr Nw Oh Ok Pa Pz Qa Qb Qe Qh Qw Rm St Tr Uh Vq Vt) mS(aJ Al Bc bG Cv dG dJ dM eC Et Fn Fr hB Ih Ip Ir Is It Li Lj Mb Nd Nr Nw Oa Oe Pz Qa Qb Qh Qw Tz Ua Uc Vq Vt) nJ(Ad aJ Al Bc Cv Dc dJ eC Et Ex Fn Fr hB Ih Im Ir Is Kk Li Lj Lx Mb Nk Nr Nw Oa Ok Pz Qa Qb Qe Qh Qw St Vq Vt) kN(Ad aJ Al Bb Bc bG Cv cY Dc dF dJ dM dR Et Fr hB Ih Ip Is Kx Li Lv Mb Nd Nw Oa Oh Ok oN Pz Qa Qh Qw St Vq Vt) nU(aA aJ Al Bc bG Cv Dc dJ Et Fr hB Ih Im Ip Is Mb Nd Nk Nr Nv Nw Nx Oa Pa Pz Qa Qh Qw Rm Ua Uc Vq Vt Vu) kO(Ad aE aI aJ Al Bc bG cB Cv Dc dF dJ eC Et Fn Fr hB Hu Ih Ky Mb Nk Nw Ok Pz Qa Qe Qh Qw Ri St Ub Vq Vt) nR(aJ Bc Ch Cv Dc dJ dM Et Fr hB Ih Ip Iq Ir Is Jk Li Lv Lx Mb Nd Nw Oa Oe Oh Pz Qa Qe Qh Qw Uc Vu) nK(Ad aJ Al Ax Bc bG Cv Dc Di dJ Et Fn Fr hB Hu Ih Im Ir Is Nd Nr Nw Oh Ok Pz Qa Qb Qh Qw Ub Vq Vt) mT(Al Bc Cv Dc Di dJ Et Fn Fr hB Ih Is Lx Mb Nd Nk Nr Nt Nw Oa Ok Pz Qa Qh Qw St Uc Uh Vq Vt) nL(Ad aJ Ax Bc bG Dc Di dJ Et hB Ih Im Ir Is Ky Li Mb Nd Nk Nr Nw Oh Ok Pz Qa Qb Qh St Vq Vt) mE(aJ Al Bc bG dJ Et Fn Fr hB Ih Im Ip Ir Is Lv Nd Nr Nw Oe Pz Qa Qb Qe Qh Qw Rm St Ub Vt) kI(aJ Al Ax Bc Cv Dc Di dJ Et Fn Fr hB Ih Ip Ir Is Lj Ly Mb Nr Nw Oa Ok Pz Qa Qh Qw Vq Vt) mW(aA aJ Ax Bc Cv Et Fr hB Hu Ih Ii Im Ip Is Jk Li Mb Nd Nr Oa Oe Pz Qa Qh Qw Uc Vq Vt) kP(Ad aJ Ba bV Cv dJ Et Fr hB Ih Im Ip Is Jg Jk Mb Nd Nk Nw Pz Qa Qd Qh Qw Tr Uc Vq Vt) kK(Ad aJ Bc dG dJ Et Fr hB Ih Im Ip Is Li Mb Nd Nr Nw Oa Pz Qa Qh Qw St Uc Vq Vt Vu) kC(Ad aJ Al Bc Cv Dc dJ Et Fr hB Im Ir Is Li Mb Nk Nr Nw Oe Ok Pz Qa Qh Qw Vq Vt) lW(Ad aJ Al Bc Cv Dc Et Fn Fr hB Ih Im Ip Is Jm Mb Nd Nw Pz Qa Qb Qh Tr Vq Vt) mH(aJ Bc Cv Dc dF dR Et Fr hB Ip Is Lx Ly Mb Nr Nw Oa Pz Qa Qh Qw St Uc Vq Vt) mZ(aJ Ax Bc Ch Dc dG Di dJ Et Fr hB Ih Ip Is Jd Ky Li Mb Nd Nw Pz Qa Qh Vq Vt) nC(aJ Al Bc Co dF dG Et Fr hB Ih Im Ir Is Lv Mb Nd Nw Ok Pz Qa Qh St Tr Vt) mY(aJ Al aY Bc Cv dJ eC Et Fn Fr hB Ih Ii Is Mb Nw Pz Qa Qh Qw Ub Vq Vt) nF(Ad aJ Al Bc Cv dJ Et Fn Fr hB Ih Im Is Mb Nk Nw Ok Pz Qa Qh Qw Vq Vt) kG(aJ Bc dG Et Fn Fr hB Ih Ip Is Ky Mb Nd Nw Oh Pz Qa Qh St Ua Vq Vt) nM(aJ Bc Cv Dc Et Fr hB Ih Im Ip Is Mb Nw Pz Qa Qh Qw Vq Vt) eM(bW cR dE dJ Ed Et gC IH Is Jm Lv Oa Oh Rc Rh Us) nH(aJ Bc bG dF dJ hB Ih Ir Mb Nd Nr Nw Pz Qa Qw Ub Vq) Wn(Bn cH Dl Hc Hf Ih Is Jl Jq Kc Kq Me Mz Ng Ni Vt) fP(bN Dc Ih Iq Is Iu Jm Li Lj Oa Qb Qh Sr) Qh(aI aR aY bN cR dA dJ eC gW kQ) Th(Ax Cs iH Lj Mj Oa oN Wm) fR(aY Fn Ip Iv Pd To) gC(iH Is kQ Lv oN Uk) bN(cS Ih Is Lx Us) Tk(Is Mw Mz Vt) Is(cV Qy) FbgW LiiZ} Ri{oO(AA aC aD aE AF aG aH aI AJ aK AL aM AN Ao AP aQ AR AS aU aV aW AX aY aZ BA bB BC bE bF Bg bH bI bJ bL bM BN BO bP bQ bR bS bU bV bW bX bZ cA cB cC cD cE cF cG cH cI cJ cK cL cM cN cO CP CQ cR CS CT CU CV cW CX cY cZ dA dB DC DD DE dF DG dH DI dJ DK DL dN Dp dR eC Ed EF Et Ex Ez Fa Fb Fn FP Fw Fy GL Gp Gz Ha HB HC HF hG Hq Hr Hu Hv Hx iA Ic Id IH Ii IJ Ik Il Im In IO iP Iq Ir Is It Iu Iv IZ Jd Je Jf Jg Jh Ji Jj Jk Jl Jm Jn Jo Jp Jq Jr Js Jt Ju Jv KC Kd KE KF KG KI Kj kK KI KN KO KP Kq KR KS Kx Ky Kz Ld Lh Li Lj Lu Lv LW LX Ly Lz Ma Mb Mc Md ME MF Mg MH MI Mj Mk Ml MM Mn MP Mq Mr MS MT MU Mv mW Mx MY MZ Na NB Nc ND NF Ng Nh NI NJ NK Nl NM NN NO Nq nR Ns NT NU Nv NW Nx NY Oa Oe Of Og OH Oi OK Om ON oP oQ Or Ou Ow Oy Oz Pb Pc Pd Pe pF Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Rj Rm Sr Ss St To Tr Tt Tv Tz Ua Ub Uc Ud Ue Uf Ug Uk Ul Um Uo Ur Us Ut Uu Uv Vo Vp Vs Vt Vv Wm Tj tF) oQ(aA aC AD aE AF aH aI AJ aK AL aM AN AO AP AR aS aU aV AW AX aY aZ BA BB BC bE bF BG bH bI bJ bL bM bN bO bP bQ bR bS bU bV bW bX bZ cA cB cC cD cE cF cG CH cI cJ cK cL cM cN CO CP CQ cR CS CT CU CV CW Cx cY cZ Db DC Dd dE dF DG dH DI dJ DK DL dM dN Dp dR eC Ed Ef Et Ex Ez Fa Fb Fn FP Fr Fw Fy Gl Gp Gz Ha HB HC HF hG Hq Hr Hu Hv Hw Hx iA Ib Ic IH Ii IJ Ik Il Im In IO iP Iq Ir Is It Iu Iv Iz Jd Je Jg Jh Ji Jj Jk Jl Jm Jn Jo Jp Jq Jr Js Jt Ju Jv Jy KC Kd KE KF KG KI Kj KK Kl KN KO KP KQ kR KS Kx Ky Kz Lh Li Lj Lu Lv LW LX LY Lz Mb Mc Md ME MF Mg MH MI Ml MM Mn MP Mq Mr MS MT MU Mv Mw Mx MY mZ NA NB NC Nd NF Ng Nh NI NJ NK nL NM NN NO Nq NR Ns NT NU Nv NW Nx NY Oa Oe OF Og OH Oi OK Om ON oP Or Ow Oy Oz Pa Pb Pc Pd Pe PF Pg Ph Pi Pj Pk Po Pz Qa Qb Qc Qd Qe Qg Qh Ql Qm Qn Qt Qu Qv Qw Qx Qy Qz Rb Rc Rf Rg Rh Rj Rm Sr Ss St Tn To Tr Tt Tv Tz Ua Ub Uc Ud Ue Uf Ug Uh Uk Ul Um Un Uo Us Ut Uu Vo Vp Vs Vv Wm Tj tF) lY(aC aG aI aK aM aP aQ As aV aW aX aZ bA bF Bg bI bJ bN Bo bQ bV bX bZ cB cC cE cT cV cX cY DB dC DD DE dF dG dK dM dN dR eC eF Ex Ez Fb Fn fP Fr Gz hB Hr Hx iH IJ Il Im IP Ir Jg Jj Jn Jo Jr Jv Kc Ke Ki Kj Ko Kp Kq KS Kx Ky Kz Lj Lu lX Ma mE Mf Ms MT MW My Mz Na Nc Nd Ne Nh Ni Nk Nl NR nU Nw Nx nY oF oH Oi Ok oP Ow Pa Pf Pk Pz Qa Qc Qd Qe Ql Qv Qy Rj St Tn Tv Tz Ug Uh Uk Ul Um Un Uo Us Uv) lX(Aa aM An aP aR Ax bG Bn bP bV bZ cG cI cQ dF dG dL dM Ex Fb Fr Gz hB Hx iH IJ Il Ir Jm kC kF Kj kO Kx Li Lj Lx Mj mM nA nC nD nJ nL Nr nT Nw Nx Oa Oh oP Pa Pf Pz Qa Qb Qe Ql Tr Tz Ue Uf Ug Uk Wm) mM(aI aJ aX aY aZ bA bG bQ bV bZ cB cC Co Cw dB dF dG dM dR eC eF Ex Gp hB Ij Im IP Ir Jg Jp Ke Kj Kq Lh Lj Mk Mn Nw oF On Ow Pa Pi Pz Qa Qc Qd Qe Qh St Tn Um Vu) oP(aJ aO bA bG bN bQ bV cC CH cN cT cY dR eC Ed Ha hB Hx Ij Jj Kj Lj Lv Lx Ms Mt Mx Mz Nb Nl NN Nr Nt Nx Oa Oh Ok Ow Pa Pc Pf Qa Qb Qg Qh Tz Ug Uk) nU(aJ aM bA bG bP bQ bV bZ cE cN cT dG Fw hB Ih Ij Jj kF Kj Kk Kx Lj Lu Mz nD Nr Nv Nw Nx Oa Oi Ok Pf Qa Qb Qh St Tr Uk Um) kO(aI aJ aP aZ Bo bR bV bZ cB Co Cw CX DB dF dG Gz hB iH IP Jj Kj kS Lh Lj Lu mS Na Nd Qa Qd Tn Tz Ug Uh Uk Um Uo) nN(aJ aM aW aY bG bM bN bV bZ cE dF dG dM Gz hB IJ IP Jj Ke Ly Mf mI Mz Ni Nk Nt Nw Ok Pa Pf Pz Qa Tn Uh Uk Um tF) nD(aM aX aZ bA bG bV bZ Co Cw dB dF dG dM Ex Gz hB iP Jj Kj Lj Lu Lx MS Nd Nr Nx nY Ok Ow Pa Qa Qb Qe Tn Uk Vu) eM(bL bP bV bW cH cR cS cV dI dJ dL Ed fP gC Hf Hv Il Iq Jf Js Lv Mj Mm Mq Mr Mz Nj Nn Pi Pk Qv Rc Rh Rj Us Vu) nJ(aJ aM aX aZ bQ bV bZ cB Co Cw cX dB dF dG Ex hB iH IP Jj Kj Lj Lx Mk mS Nr Nx Ok Pa Qa Tn) hB(kC kE kF kG kI kK kN kP lW mE mF mH mP mS mT mU mW mY mZ nA nC nF nH nI nK nL nM nO nR nT) bV(kC kE kF kI kK kN kP lW mE mF mH mI mS mT mU mW mY mZ nA nB nC nF nH nI nK nL nM nO nT) aJ(kC kE kF kG kI kK kN kP lW mE mF mH mI mS mT mU mW mY mZ nA nC nF nI nK nM nO nT) Fr(kC kF kI kK kN kP lW mE mF mH mI mP mS mT mU mW mY nA nB nC nF nL nM nO nR nT) Qa(gC kC kE kF kG kI kK kN kP lW mE mF mI mP mS mT mU mW nB nC nF nK nO nR Th) dF(kC kE kF kG kI kK kN kP lW mE mH mI mP mT mU mY mZ nA nC nF nI nK nR nT) Th(dI Ed Fa Fp Hb Hr Il Je Li Lj Lx Mj Mu Nx Oa Qb Tv Uv Vu Vv Wm) dG(kE kI kK kN kP mF mH mI mP mS mU mW mZ nA nB nF nI nL nO nR) dM(kC kE kF kG kI kK kN kP lW mE mF mH mI mP mT mU mZ nA nR nT) nR(aM aO aP Ax bP bZ cN Dc Di Li Lj Mk Nk Nn Oa Oh Pf Qb) mS(Aa aM eC Ex Gz iJ Il kC Lj Lx nA Nr Nx Oa Pf Uk Wm) Pf(kC kG kI kK kP mE

Il Im It Iv Jg Jq Ju Kp Kq Ks Ky Kz Ld Me Mn My Ni Nj Nt Oh Or Pc Pj Qu Qw To Vs) Tn(Ef Hc Hu Iz Jg Jr Jt Jy Kl Kq Kr Ks Kz Me Mm Mn Nc Ng Oe Of Ok Or Pf Pj Qu Ss Ug Uk Vt) Kz(Fa Fp Ha Ik Im Iu Jk Jm Jq Jr Lj Lx Mz Na Nr Oa Pc Po Qa Qh Tv Tz Vt) Fb(Hc Hu Jg Jt Kr Mc Mn Nt Qw Rb Ss Vo Vt) Vt(Iv Jq Kc Ky Lv Ml My Oh Pc Pf Qd Sr) My(Jr Lj Lx Mz Oa Pa Pe Pf Po) Iu(Hf Kn Kp Kq Kr Ks Me Pf Uk) Me(Hb Ir It Ke Pa Pf Tr) Vs(Ij Ke Lj Pa Uh Uk) Ld(Dp Fa Hq Ir Oa) Kr(Io It Ke Pa) Us(Ih Ik Tv) Fa(Sr Ul) Na(Ih Jq) Rb(Ke Mt) Rg(Hb Nc) MnPa NhTo HqKc HcJn IpSr JmKs JqQn} eC{mY(aK Bn bS cA cK cQ cV dE dH dI dJ Ib Ih Il Ir It Iu Iv Jr Kk KR ml mM Mr Na nI Nj Nk NO NT Nx Oi Pa Pg Ql Rg Rm Ss Tr Tv Ut Vs) Nx(kC kF kG kI kK kN kO kP lW lY mE mF mH mM mP mS mT mU mW mZ nA nB nF nH nJ nK nL nM nN nR nT nU oO oP oQ) bG(Ex Gz kC kF kG kK kK kO kP lW ml mM mS mT mU mW nA nB nF nI nJ nK nO nR nT oO) oQ(aJ aK Ar Bn bS cA cK De hG Ic Kr Ks mM mW Nk No Nt Nu Or Pa Pi Tr Uv) nJ(aK aV cB cF cY dA dI dJ fP Ib Ip Kx Ms Na Ni Nk nO Nt Oi Pa Pj Tr) Gz(bA bP bQ bZ Cu Ed fP Fw hB Ip Nd nO Nr nT Nw oN Ou Pa Qw Tr Tj) Ib(kC kF kI kN kO kP lW Lx mI mS mT mU MZ nF nH nL nR oP Qh) Qv(kC kF kN kO lY mE mF mH mS mT nA nF nH nI nL nN nT nU oP) Ex(bP bQ bZ cU fP Fw hB Ip mM Nd nO nR Nw oF oN oO Ou Tj) Pa(kF kK kN Lj mI mP mT mU nA nF nN nR nT nU oP) kO(aK Ar aV cF dI Ip Ms Na Ni NT Or Pj Tr Un) nL(Ar cB cF dI fP Ms Na Ni nO nT Or Pj) kC(Ar cB cF dI fP Ip Ms Na Ni nT Pj Tr) Lj(aE aR fP gL mW Nk nR oP Pk Po) Oa(aO aR bN bZ fP kN mW Nk nO nT) dI(kF mE mU nA nF nI nK) nT(Aa iH iJ nA nH Nt Wm) mM(Dc dF dG Fr hB St Tn) Lx(bN dA Jd nO Ss Vv) mW(aJ aM Fr kF nB Qa) Nk(kF mS mU nU Qh) nH(Ar cF Ms Na Pj) Nt(mS mU nN nU) fP(iH nA nF Qb) nB(Ez Kx Or Un) Tr(mP Ng nI) nO(Aa Tn Wm) mU(aK cV Oi) nA(aK cF Ip) nK(Fr Ip mI) kF(hG Kx Nu) Ed(mZ oP) Fb(gW Vs) Qw(mE mF) Li(Kc oK) nU(mI Oe) lY(Jf Un) ArnC FakQ FrmE MsmF IrbN QhJk PjmP cWkN} gW{Fb(AA aC AD aE AF aG aH AJ aK AL aM AN AO AP aQ AR AS aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp dR Ed Ef Et Ez Fa FP Fr Fw Fy GL Gp Ha HB HC HF hG Hq Hr Hu Hv Hw Hx iA Ib Ic Id IH Ii IJ Ik Il Im In IO IP Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp KQ KR KS Kx Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa Oc OF Og OH Oi OK Om ON Or Ou Ow Oy Oz Pa Pb Pc Pd Pe PF Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Rj Rm Sr Ss St Tn To Tr Tt Tv Tz Ua Ub Uc Ud Ue Uf Ug Uh Uk Ul Um Un Uo Ur Us Ut Uu Uv Vo Vp Vs Vt Vv Wm Tj tF) bN(Et Jl Jn Jy Kl Lx No Tn Tr) Lx(Jg Ng Om Vv) Vv(aO Et Pa) BgNg HqPg PakS} nA{Ex(aF aJ aM aN aP aY aZ Bb BG bQ bX bZ cJ CO cP cQ cR cS Ct CX dC dE dF dG dJ dM Dp Et Fa fP Fr Fw Gl hB Hq Hu Ib Ih Ij Ik Im iO Ir Jd Jl Kc Kd Kg Kj KN Kx Lu Ma mE Mf mI Ml Mm Mv Mw Mx My MZ nC nK NL nN nR nU Nw Nx Oa oF Og Oi oN oP Or Ou Pa pF Ph Pj Qc Qe Qg Qh Qm Qn Qw Rm St Tn To Tr Ul Ur Tj) Gz(Af Al aN aP aQ aZ bF bG bP bQ bX bZ cD cE cJ cP cQ cS cU CX dG dJ dM Ed Et fP Fw Hq Ib IJ Il Im Ip Is Kg Kj Kx mE Ml mY nC Ni nK Nl NN Nr Nw Nx Oa Pb pF Pz Qc Qe Qm Rc St Tn Tr Uc Ur tF) Ib(aJ aM cB dM Fa Fb Fr Ih Is Jf Jk Jl Jm Kj Lh Mt Mw Nl NN Nr Oa Oh Oi Or Qa Qe Qh Tn) Un(aJ AL aM Ax bH Cv Dc Fa Fr Ih Ip Ir Is Jm Kn Lx Oa Oi Qa Qe Vt Wm) Nx(aW aX bR cB cR Ct cW cX dA dB fP Hb Hf iZ Kr oN Qu Qw Rf To Tr Vt) Oa(Af aX Bn bU fP Jj Jt Kr Nk No Nt Qn) Ip(bR cM dB dD iH Jj Ms Uk Us Uv) Kr(aJ Ax bG dF Lj Nr oF Pa Pf) cB(bH Bn Hr Ki Nd No Nt Nu) Tr(Ji Jj Jt Ms Qz Uk) Tn(Aj Ao Ed fP Ut Wm) Qh(Af Bn De fP Ii) Pa(bH cR cX Or Rg) Pj(dB Et Mz Pz Qw) Ed(fP My Qw Qz) Rb(Jf Mb Nd Qz) Qn(Fa Ha Lj Vs) Af(Fw Sr Uc) Wm(Gp Ml Na) Lx(Ar Id Ss) bG(bH Hr Na) Aa(bM cD) Ms(Il Or) Nl(Jf Qv) Is(Ql Tz) Lj(cR fP) AlUk AnJj AsJm CqUg CtIc NtKx NdcV HqQz HrbH JdnJ OhfP OrPf cXiJ} gC{cW(aD AF aH aK aN aX aZ bL bR cC cJ cL cO cQ cX dA Db dD dF dH dJ Fa Gp Hb Hc Ih In Iq Jq Kc Lj Lv Ly Lz Mf Mj Ml Ms Mz Nc Ne Nh Nm Of Oh Or Oy Pa Pf Pk Qa Qe Qh Qu Qw Rb Ss St) Nc(aE aK aM aQ aU aV aY cB cP cR cU cV cY dA fP Hv Is Kr Lv Lz Me Mh Ms Mv Na Nb Ni No Nu oN pF Pk Ss To Tz Ub Uk Tj) Ss(aY bN dE Fb Hb Ip iZ Kg Kk Kn Lv Mr Mv Ns nW Oi oN Qn Qz Uk Vp) Na(bN cP cR Hc KQ Lv Mr Mt My Nl Og oN Oy Pb Pc Pd Qt Qu Uk) Ip(cR cV hB hF hG iH iJ iO iP kS nW oF oH oN tF) Gz(bB Ik Jr KQ Lv Mj Mr My oN Pb Qt Uk Un) Lv(cX Db dJ Ex fR Hb Ic Mv Oh Pa Ph) aY(Af Aj Bn Ch Ct Db Hc Ib Ic Or Oy) Ms(aN cP Ct fR Io Md Mj Mr Or Oy) cV(aH bB cP cX Is Mv Nh Nl To) dJ(hB hC iA Mj Mz Nl oF oN Pd) Qu(cE Ex Ib Iq kQ Nn Ow Sr) cX(fP Hb Kk Qm Rf Tt Uk) kQ(aC dD Nk Nt Nu Qh Rb) Is(Ex Jn Mr Nj Nt Qy) bL(Aw cR Db Hr Mt Mv) fP(Gp Iq Ly Nh Nl Qh) Un(aF aX Hc Oy Uk) cI(Hb hC Id Jj Kk) fR(aP cJ dH My Pd) Ex(My Nw oN Qt) No(Ih Iq Qa St) Mr(Al Hr Nl Tj) Mt(cL Kk Qd Qg) To(Ic Qt Uk Uo) cR(cE cL Nb Pa) Af(Kg Qm St) Id(bB Kl Kq) Iq(aE cP Tj) kS(Kk Nw Tr) Cx(Kg Qm) Mj(hB Ic) Nh(dA oH) Rb(oN Uk) Us(aE cP) BnSt DdHc MvOy NldE IbUk IccG IkKk QhcP OrbM aOhB} Jj{nN(Af aK aN Ao Ar aV bH Bn bS bU cA cB cK CO Cp cR cU cV cW CX cY dB Dc dD DE dH dJ fP Ip Jf Ju Kr Kx Oa Or Ph Qz Rg Tr Tv Ut Vv Tj) Tr(kC kF kG kI kK kN kO kP lW lY mE mF mH mM mS mT mU mW mY mZ nB nF nH nI nJ nK nL nM nO nR nT nU oO oP oQ) nT(Al aO aS aV aY cE cX dJ Dp Fa Fb Fw Iu Jm Kn Ko kS Kx Li Om Pk Qa Qc Ra Uc Ur Vp Vt Wm) Oa(Ar kG kN kO kP lW lY mE mF mH mI mM mS mT mU mW nB nC nF nI nK nL nM nO nR oP) dJ(kF kI kK kO kP lW lY mE mH mI mM mP mS mU mW mZ nB nH nI nJ nL nO nR nU oO oP) Is(Ar Ba bN cK Ct dA De hX Jd kO kP lW mE Qt Qy Vv Wm) cX(kC kF kO kP lW mI mS mT nB nF nH nI nJ nL oP) Al(kC kF kI kK mF mI mW nH nI nJ nK nO nU oP) nO(AF bH Cq Ip Kr Kx Ra Tn Ur Vt) mM(aY bA Dc dF Fb Kd Kn Qh St Vv) Tj(kK lY mF mP mT mW mZ nI nL) Ed(mI mP nH nI nJ nK nL oP) Ip(kO lW mE mF mH mI nJ) lY(aK aN Cx dD Ib Kx Pj) nB(Af An Ar Bn Cx Kr Kx) mI(AN cD Cx Fw Kd) mP(Cq Ib Id Kx Pj Ur) bN(Ad Dc fP Ih Qh) nI(Ao bH Dg Ju kS) mH(aV cY dR kS) An(kF mU mY) mW(bH Cq Vv) kP(Dc Jm Kx) Jf(kK mZ) kF(Cv Dc) kI(Bb Cq) AahX AfnL ArLj FrmZ MzjD JmnU KxlW aAqY aOoP cWmU dLoQ} Un{lY(aA aX aZ Bc cB Co cV Dc dD Fa Fp Fr Gp Ih Ij Ip Is Iu Jh Jn Kc Ke Kn Kr Kz Lh Lj Lx Lz mE Mf mS Mw My Nr Nv Nw Oa Om Pa Qa Qe Qw Ra St Tn Tv) Ip(kC kF kG kI kK kN kO kP lW mE mF mH mI mM mP mS mT mU mW mY mZ nB nC nF nH nI nJ nK nL nM nN nO nR nT nU oO oP oQ) Bc(kC kF kG kK kN kO kP lW mE mF mH mM mS mT mU mW mY mZ nB nC nF nH nI nK nL nM nN nO nR nT nU oO oP oQ) Dc(kC kF kI kK kN kO kP mE mF mH mI mM mP mS mT mU mW mY mZ nB nC nF nH nI nM nO nR nT nU oO oP oQ) Vt(kC kF kG kI kK kO lW mE mF mH mI mM mP mS mU mW mY mZ nB nF nI nJ nK nL nM nN nO nT nU oO oP) mP(aJ AL aM aP Ax bZ Di Fa Fb Fr Ih Ir Is Jm Kn Lx NN Oa Qa Wm) Nw(hF kF kI kN kO kP mH mS mT mU nB nH nI nK nN nT oP) nU(aA Al Ih Ij Is Jm Jn Ko Lx Oa Om Qe Qh Tn) Lx(kC kI kP mH mI mM mU nI nJ nK nL nO) Ax(kI mI mU mZ nH nK nL nO oP) Oa(kP mF mI mM mS mU nB nJ oP) mI(Al Ih Ij Lj Mw Qa Qe) nT(Co dR Ij Qa Qw Tj) Is(fP kF kI nN oP) mM(Et Fr Ij Om Tn) Al(kI kK oP) Ij(mE mF nH) Qa(kK mE nH) Li(kN mZ oP) mU(Cv Fr Kn) nB(Bb bH Cv) Lv(kN oP) Lj(fP nJ) kF(cB Jm) FrkK MxmT QbfP QwnN} Qh{bN(Ad Af Aj Al An Ao Ap Ar As Aw Ax Ba Bb Bc Bg Bn Bo bV CH Co Cp Cq CS Ct Cu CV Cw Cx Db Dc Dd De Dg Di dJ Dk Dl fP HF Hr iJ iO Kk Mu Nf Ng oP Ph Pk Qx St Uk Ur Wm) De(aV dA kC kF kG kI kK kN kO kP lW lY mE mF mH mI mM mP mS mT mU mW mY mZ nB nC nF nH nI nJ nK nL nM nN nO nR nT nU oO oP oQ) Bn(dA kC kF kG kI kK kN kO kP lW lY mE mF mH mI mM mP mS mT mU mW mY mZ nB nC nF nH nI nJ nK nL nM nN nO nT nU oO oP oQ) fP(Jd kF kN kO kP lW Ma mF mM mP mS MU Ng nJ Nk nM nN nR oO oQ Vv) mM(Ax cB cJ cV Ez hB Ib Iu Mf oQ Pz Qw Rg Rm Tz Uk Vs) Ar(bC Ct dA kK mP Mu mY nF Ng Of oP Qt Qw Uk) Ct(aQ aU aV bS cA cK cY dA iJ Jr kP Mu nO) Uk(dA dJ kC kG kN kO kP mW nJ nK nO nU) Af(kK mH mP nF nH nJ nO nR nT oP oQ) oP(aO It Js Kr Lv Nk Nm Nt Ut) Ib(dA kI kK mI mP mW nH nU) nN(bS cA cK Ih Iv No Nt) kK(bS cA cK Dc Jt Nk Nt) dA(Aj Cp Jt Ng Wm) nT(Js Ks Nt Tz Ut) oQ(dL Js Kr Nk Rm)

Figure 27 Continued

Ng(dJ iJ Tr) Tz(kI nJ nO) mP(Bo Dc Jt) mW(bH Lv Nt) Aj(iJ nO) Ks(kP mU) cV(Mu nU) fR(dE Mj) nR(aO bH) IY(Ii Uv) oO(Js Kr) BokP CoTi DckI WmnF NtmH IunU JtdJ UtmI} Nt{nN(aD aE aG aH AJ aL AP AS aV aW aX aY Bb Bc BG bJ bN BO bQ bV cB cD cO cR cS cV cW cY dB Dc Dg dK dL dM Dp dR Ed Ef Fa fP Ha HB hC Ic iH iJ Iz Jd Je Jf Jg Ju Jv Kd Ke Kf Kg Kj KI Kn Ko Kp Kq Ks Kx Ky Kz Ld oH Or pF Pj Qm Qu Qw Qz Rb Rf Rj Rm Ss St Tn Tr Tt Tv Ua Uc Uf Ug Uh Uk Ul Ur Ut Uu Vp Vt Tj tF) Kx(kC kF kG kI kK kN kO kP lW lY mE mF mH mI mM mP mS mT mU mW mY mZ nB nF nI nJ nK nL nM nO nR nT nU oO oQ) Oa(kC kF kG kI kK kN kP lW lY mE mF mH mI mM mP mS mU mW mY mZ nC nF nI nJ nK nL nM nO nR nT nU oO oP oQ) oP(Al bM cC Cq Dc Ed Ic Jy Kr Ky lY Qu Rb St Tn Tr Ul Uo Uv Vt tF) nT(aV aZ Bb bQ bV cB cY dR Fw hB Kd kQ kS Ow Uh Uk Uo) Fw(fR kI lY mE mF mH mU mY nB nH nK nL oQ) cB(kC kF kI kO mU mY nC nH nJ nL) mH(bV cY dR hB Kf St Uc tF) dB(kC kO mU nC nJ nL oQ) kK(bV dF dG hB St) Jg(lY mU nU) fP(Is Lj Qb) nR(Cq Pb Vt) mW(Dc hB tF) oQ(aE Tr Vt) Tn(kG nJ) fR(dE Il) lY(Pz Qc) mU(Tr Uo) AahX EtaW MzjD UcnU IshW StnJ dRnK mMhB} hX{Aa(eD Et Fp Fr Hq Hr Hu Hv Hw Hx Ih Ii Ij Il Im In Io Ip Iq Is Iu Jg Jh Ji Jk Jl Jm Jn Jo Jp Jq Jr Js Jt Li Lj Lu Lv Lx Ly Lz Ma Mb Me Mf Mh Mj Mk Ml Mm Mn Mq Mr Mt Mu Mv Mw Mx My Mz Na Nb Nc Nd Ne Nf Nh Nj Nl Nm Nn No Nq Nu Nv Nx Ny Oe Og Oh Oi Ok Om On Oy Oz Pa Pb Pc Pd Pf Pg Po Pz Qa Qb Qc Qd Qe qT rA) Is(Et hV Hx iB Ij Ik In Iq Iv jF Jk Jm Jo Jr Jt Li lK Lv Mb Mc Mf Mg Mj Ml Mr Ms Nc Nd Ng Nj Of Pa Pb rY rZ) Iq(aA Hr Jl jQ Li Lx Ly Lz Me Mh Mj Mq Mr Mt Nc Nn No Nw Nx Ny Ok Pe Po rZ) Li(eD hW Iu Iv jI Mb Me Mz Nc Nd Ne Nh Nj Nl Pa Pb Pz qU) Mj(hA Hu hW iB Iv Mb Me Nc Nd Ne Ng Nh Nj Nk Nl Pa qY) Iu(iB In Lj Lx Lz Me Mt Nc Nd Nj Nk Nw Og Pg qV qY) Pa(Hr iB Jl Lx Lz Mh Mr Mt Mx Nn Nw Ny Pe qV) Mz(hA iB Iv Lj lK Me Mg Nc Ng Of qV qX) iB(It Js Lj Lz Mh Mt Nn Pe) Nj(Lj Lx Lz Mh Mr Mt No) qY(Hr Hw Jl Mx Pe qV) Ok(hW Iv Mg Ng) No(Me Nc Nl) Lz(Mb Nd Pz) Js(Il Jn Nc) Lx(Nl Pb) Mb(Mh Qd) Lj(jL Nc) Nw(Hu Jr) FpIv MhNd NlPe} bN{fP(Ed Fw Ha Hb Hv iA Ib Ic Id Il Jm Jn Jq Kn Ko Li Lj Nn Nr Ns Oa Pz Qa Qb Qc Qe Qm Qn Qw Sr Tn Tr Uc Ur Vv Wm) Is(Ed Et hB hF Hr Ib Ic iJ Jo Jr Ju Jv Ko Qw Qx Qy Rb Ss St Ub Uk Uo Ur Wm) Uk(Ad aW Dc dJ Et Fa Ih It Jm Jn mY nB nK nN Oa Pz Rm Sr) cS(Ib Il Jr Ko Li Lj Oa Pz Qw Sr Ss Tn To Tr Uc Uh Wm) Wm(cZ dJ Et Gp Hb Ih Jn Ke Ko Nw On Uh) Ad(hF hG iA iH iJ Il iO Jr Jt Ss Ug) De(Et Id Jk Jn Ko Oa Pz Qa Qw Tn Uc) Ss(Ap Bg Cu Dc Et Fa Lx Pz Qa) Ar(Et Ke Ko Lj Oa Qa St Tn) Hr(dJ Ih Jn Ko Lx Pa Qa Uh) Qw(Cs Fw Ko Lj Lx nN Qa Sr) iJ(Bb Bg Cs Cv Dc Lj Lx Oa) Et(Af Aj Bn Cx Nx Pj) Jn(Ax Bn Cs Cv hF Ur) Ko(Aj Bn Cx Dl Nx) Oa(aX Bb bV Cu Gp) hB(Ky mM mS Nj nO) Lj(aX Cu oP Pk) Ms(mH nT oP) Na(kF kO oQ) Pz(Bn Jt mI) Qa(aE dA Ex) Ur(cZ Gp Kk) dJ(Ed Qn Rm) Dc(hG iO) Gz(mU nN) hF(On Uh) BbiO BnSr FakQ FrhG TofR JgnN LioK} bH{mW(aJ Ax bG bM cD cV dC dG Fr Gp Hr Hx iA Ih iJ Il Jn Kf Kj Kn Ko Kq Lj Lv Lx Mt nJ nL Nq Nr Nv Oa Ok On oQ Pe Pf Pg Qa Qb Qv Qz St Tn Vv) Pa(kC kF kG kI kK kN kO kP lW lY mE mF mH mI mM mP mS mT mU mY mZ nB nF nH nI nJ nK nL nM nN nO nR nT nU oO oQ) Hr(kC kF kG kI kK kN kO kP lW lY mH mI mM mP mS mT mU mZ nB nF nI nJ nM nN nO nT nU oP oQ) mU(aV bG bM Bo cB cV Ez Fr Gp In Kd Mz nO Qg Tn Tr) mF(bG bQ dR hC Jg Kk Nv Nw Ok On Pz) oP(bM cD Kd Lj Lv Ms Pf Tn Tr Us Uv) nR(Af Bn dF In Lj Nd Nr Nx Qa) nO(bG Fr hB Oa Pe Qa Qb Tn) cB(kC kO mY nC nJ nL oQ) bG(kK mP mS mZ nN nT) Nx(kK nI nU) Us(kF kO lY) mE(Ko Tr Uk) mM(dF hB St) nC(dB Ko Ur) In(mT mY) Qa(nI nT) kK(bZ Lu) oQ(Bo Tr) ExoO FrmT NrkF HwmY TnkP QvnB UhnJ UmU PfkI cSkN dFmS} Uk{nO(Al Ax bA Bc bG cB Cq Cv Dc Di dJ Fw Ha Ih Ij Il Ip Ir Is Iu Jk Jn Kn Ko Kx Lj Lx Mk Nd Ni Nl NN Nr nT Oa Oe Oh Oi Om Pb Pk Pz Qa Qb Qe Qg Rm St Tn Tr Uc Vt tF) Al(kC kI kK kO kP lW mE mF mI mM mU mZ nF nI nJ nK nN nT oO) mW(aA Bc Fa Ih Is Jm Kn Lj Mk Nl Oa Oz Qa Qb Qe St Vt tF) nB(aC aE cD cY dL Ik Is Kx Nd Nk Pa Pz Rg) kP(Dc Ij Ik Ir Is Jk Jm Nl Oa St Tr) mM(Et Ih Ip Ir Is Jm Kn Kq Qe St) nT(aK Ih Ij Oa Pa Qa Qb Vt) nK(cZ dR Fr Ip Is Nw oH St) mE(Cv Ip Is Jm Ut Vt Tj) Ip(kC kO nF nJ oO) Pa(lY mI mP mS nU) mU(cB dD Ir Nk Tr) Is(Ar dA Jd Mu) nI(Ih Jm Nl Nr) Pz(mS mT nJ) nN(bG Iv Nk) mF(Cv Oc Vt) mZ(Fr Jm Tn) kN(Li Lv Vt) Et(aW Vv) Lx(aR dA) Qb(aE dA) Nx(mS nU) nC(aA nL) CvmS NknL TrmI QzlY KnoO OakI aKkG} fP{Lj(aE aP AR aW bM dA dJ dL dN Hb hG Hv Ik Ip Is Jd kF kG kK kN kO kP Kq Ky lW Lx mE mF mH mI mM mP mS mU mW mY mZ nB nF nI nJ nK nM nO nR nT nU nY oP Pb Pk Po Pz St Vv) Qb(aP aR cU dA dJ fR Hc Jd kC kF kG kI kK kN kO kP Lv lW lY Ma mE mF mH mI mM mP mS mT MU mW mY mZ nB nF nI nJ NK nM nN nO nR nT nU Of oN oO oP oQ Pb Qe Qw St Vv) Oh(Jd kI kK kP lW lY mH mI mM mP mU mZ nB nL nR nT) Oa(AR aW aY Iv Jd Kc kP mM mY mZ nR Vv) nN(aO Hu Lv Mg Oy Qa Vv) Vv(Bb Is Lx Nn Sr) Pa(lY mI nH nU Oz) kP(Li Qa St Tn) Fa(aP aY Jd) Ik(Ex Gz Sr) cB(kO nJ nL) mZ(Fr Qa Tn) Is(Jd Jo) aO(nC oQ) mM(St Tn) ExHu LxJd QanI QenC JmfR NxnU} mM{hB(aO aQ aV aW aZ bG cB cC cS cU cV cX cY dB dJ dR Fa Fr Hc Ih Il Im Is Iu Jn Jq Kn Ko Kq Kz Li Lj Lv Mf Mw My Nk Nq Nr nT nU Oa OH oK Om Oy Pk Qb Qd Qe Qz Ra St Tn Vo Vt Vv) Ib(bQ Dc Et Fr Ij Is Jk Kq Lh Ok Om On St Tn) St(Af Al aO As Bn Ct cV De Mt Pz Qw Rg Rm) Tn(aC bJ bV cR Hu Ik Qw Rh Rj Ut) Qw(bA bF cT dF Jg Lj Nr Nx Pa) Oa(Bn bQ bV Kc My No oF) Dc(cB dB Hx Qg Tv Us) Fr(Rf Rg Rh Rm Ut) Ip(bG Ex Gz iJ Ms) dF(Hr Pd Rf Rg Rj) oF(Li Lj Lv Rf Vt) Is(Ql Tz Vs) Rg(Kq Pa Qa) Pj(Et Ok Uh) dR(aU nT Pk) Fa(aY bM) Lv(bG Kc) Lx(dD Vv) Uc(Jt Kj) Hx(Ad Cw) CvUg EtbV GpRf HabG NoLi MsPz NdcV IcKj QaRm QzLj QvJm QlaA cCoQ} lY{Ib(As aZ cB Fa Fr Gp Is Ke Lx Mt Mw My Pi Qa Qe Ur) Pa(aX cJ cV Jf Kj Kr Ks Or Pj Qw Rb Rg) Ex(bG Ip Mb My Nw oO oP Pz Qz Ut) Jt(Ap cB Cw Jg Kd Ko Nv Oa Tn Tr) cV(aZ CX Kr mW My Nd Nx Qn Us) Kx(cB Ez Gz Mf Ms Nm Oy Rb Ug) My(Ed Fw Gz Kd Kj Ms Rb Uv) Ks(Im Is Jm Lj Pk Sr St Tn) Ip(Gz iJ Ji Mf Mm Ms Na) Qz(Bo Gp Ms mT Na Rb Us) dD(Ez Il Kj MF oP Uv) Nx(aE aX dB Hb Ur Us) Gz(bG Mb Nw Pz) Rb(Jo Kc Nd Ug) Ms(dJ oP Pz) Is(Ql Qv Uv) St(De Ii Mt) Jo(Kd Tn Us) Kc(Lj Lv oO) mE(Bo Qw Us) Nr(De Tv) Na(bG Mb) Nd(Mf oO) Hc(bG oF) Kr(hB oF) Oa(mW Nk) Uv(Kz nO) Pj(Hb Ko) BaGp HanO NoLi LucB IcKj TnUt QwUs OubZ cXiJ} Oa{No(kC kF kI kK kN kO kP lW mF mH mP mS mT mW mY mZ nB nF nJ nK nM nN nO nR nT nU oO oP oQ) Nk(kC kI kN kO kP mF mH mS mT mU mW nB nF nO nR nY oP) Af(kI kK kN kO mP mU mW mY mZ nH nO nR nT oP oQ) mW(aC aY Bn cR dD Hr Hx mU Nu Qw Rg) oP(aC aP Bn De Ih Js Mj Rg Rm) Bn(kI kO mE mS nB nO nR) Jt(kI mP mS mU nB nI nO) Ar(aL Hb Ke kK mY Ti) De(aL Et iJ kI mS nI) Kc(iZ mP mU nT nW) nO(aX bU Ib Ip Kx) Ti(Co hC Kn oF) aC(kN mI mZ nT) aX(kP nB nI) mU(Ks Ql Ug) mY(Lu Nx oK) Gz(Mj mS) Ib(kI nU) Rg(nR oQ) nT(Pa Ug) kC(Js Nd) kN(aO Rm) kP(Kx Qw) MjkI NxnU OgdJ PjmP bZdA} mP{Pj(aJ aO Ax aZ bQ bV bZ cB cD cH cX dB dJ Et iA Ih Il Ip Is Jm Kn Kx Kz Lj Lx Mf Mk Mz Nk Nn Nw Oh Ok Pa Pz Qa Qc Qe Qw Sr Uh Vt tF) Ib(aJ bQ cB CX Fa Fr Is Iv Jf Kj Kn Kx Kz Lh Lx Mt mU Mw Nd Nl Nn Oh Qe Tj) Nx(aQ aX bR cB cF cX dB dJ gL Ic Id Qw Sr Tr Tj) Ex(bV cF cX Ip Kg Mb mU Nw oO) Gz(cF cX Ip Mb mU Nw oO oQ Qw) Sr(Af dM Jo Jt Kj Qa) Kx(Fa Jt Lj Pd Rc Vv) Id(aJ dM Ir Kj Lx) Ic(aJ Kg Kj) Pa(cX Or Rg) bG(Cx Hr) cX(iJ Il) nC(bR Jf) AacF EdMy NoLi MsIp NdcV TzIs TrJt TnUt HfQa QzLj KroF VvmW PiaJ} cB{kO(aC Af Aw Bn bU dD Dl Hr Ki mU Mz Nb Nd Ni Nl No Nu Pd Pj Rf Rg Sr) nJ(Af aY Bn bU Cv dD dJ Dl Hr Ip Ki Nd Nl No Nu Pj) nL(aE Af Bn bU dD Dl Hr Kr Lv Nd No Pj) nC(Aw dD Dl Hr Ip Kr Lv Nd No Nu Pj) Ib(kF kN kP mI mT mU nH nR nT) Bn(kC kF mY nF nH nK nT nU) Nx(kK mI mU mY mZ nB nU) kF(aC Af dD Iu Ki Nu Pj) oQ(Aw Ki No Rg Rj Rm) Af(kC mY nF nH nU) Nd(kC kI mI nB nK) mY(cG Ki Nk Pz) kN(Cq Ki Lv Wm) Nu(mU nK nN) Aw(mU nU) Lv(mW oP) mI(Kx Pz) nF(bU Nl) nH(Dl Pj) kC(Ki Kr) CwnU MsoP cVnK nRhB} oP{Lv(aC aK aL aO aS bE bQ bR cX cY cZ dA dB dD dM dR Ex gL Gp Gz Hf hG Ib Ic Id Kc Kx Ph Pi Pj Pk Sr Vv) Lj(aO Ar Aw cM cN cQ cR cY dD dH dN No Ph Rg Rh Rj Rm) St(Af aO Bn Dc Kr Nk Rm Ut) aO(bM Fr Kk Ms Nm Nv Tn) Hr(bG cD Gp Kd Uv) Li(bS cA cK No Rg) Rm(Nb Nn Nr Oh Qb) aY(Fa Ju Oy Rc Vv) Rg(Ax Nn Oh Pa) bM(Jt Pd Pg Vv) dD(Lx Nb Rc Wm) Ms(cU dJ Pb) Kr(Ax bG dR) Oy(Bb Kd Tr) Af(Dc Ua) Cv(Jo Jt) Ex(Hu Ip) Kk(kS Pd) Pa(aC Dl) cD(Pd Pg) GzMb NbRj IbJk TraC TnUt QbaP JqPj VtbE cXiJ} Is{Il(eD hA hR hV hW iB iC jD jE jF jG jH jI jK jL

Figure 27 Continued jM jO jP jQ jR jT jU jV jY 1K 1L 1M 1N qU qW qY rA rB rX rY rZ) Tz(kC kN kO mE mF ml mS mT mU mW mY nF nl nJ nK nO nR nT nU oO) Jo(cV hR hW iB iC jF jG jH jl jM jO jP jQ jR jU jV jY 1M qZ rX) Ib(dA kK kP lW mE mF ml nC nH nR nT nU) Ql(kC kK kO ml nl nJ nK) qZ(Ih jL Nc Nl) cV(Jd Nk Qw) nR(Af Bn Ut) iJ(Ct Ng Qy) oQ(Js Kr Rm) Ms(kG kP) Nx(iB mS) ml(Tv Vs) rX(Hw Jt) CtLv TiQy NgTr NjfR JdhB} Ip{Gz(kC kF kG kl kK kN kO mF mH ml mS mT mU mW mY mZ nB nC nH nK nL nN nO nR nT nU tF) Ex(fR kC kF kG kN kO kP lW mE ml mT mU mW mY mZ nB nC nH nJ nL nN nO nR nT pF Qt) Ms(kC kK kO mE mF mH mT nl nJ nK nL nT nU) fR(aY dC dE Hu Ik Jd Kx Mb Mj Mr Mz) nJ(bR Db dD iH Kr Na Ql Ur Us Ut Uv) iJ(mE mS nL nN nO nT nU) nC(bR dB fb iH Rb Us) kO(bR DB Kr Us Wm) Na(kC kP nF) nL(bR dB iH) Oy(lW ml) nK(Kr Ur) kC(bR Us) NxmU UgoO} Mz{hA(hR Hv hW Hx Il lv jD Jt Lx Me Mg Ng qY rB rC rX rY rZ) jL(aA Hx Il lv Jt Li Me Mg qT qY rB rX rY rZ) jD(Hu Il In Ji Jo Jt Ma Mm Ms Nc Ng Ni Pd) rZ(Jt Lv Ma Mg Mm Ng Ns Of Oz qY rC) iB(aA Il Jo Jt Mg Mm Nx Of rB) Ng(hR jV 1K 1L 1N lO rX rY) qY(lO Ma Mb Mm Nc qV rY) jV(Il lv Me Mg Of Qe) IL(Il Jo Jt Me Mg) IN(Iv Jo Mg Nc Nk) hR(Aa Jo Me Mg) rY(Aa Mg Mm Ns) Nc(qZ rB) jU(Il Pb) MalK NeqZ NlrB JoeD} nO{Lx(aC cR Ct Fy Ib iJ Jd Ra Rb Rf Rg Rh Rj Rm Ss Uf Um Ur Vv) Tn(Ad Aj aO bL Bn bV Ct Ef Ik Rf Rg Rh Rm Ut) hB(aO It Kr Ld Lv Nj Nk Oy) Li(aX bS cA cK No Rg Tv) Fr(aO Ct Ib Rf Rg Rm) Lj(cR Kr Kx Ld Rg Tv) Ha(Af Bn Kx Nk Nw) Ct(Qa Qb Qe St) bV(Lv Rb Vs Vt) Hx(Bc Dc Di) Kj(Cq Jm Vt) iJ(cX Dl nN) Af(nT St) Bn(St tF) Ue(Cv Vt) fb(Lh Mw) Rg(oQ Pa) Oy(Cw Tr) bG(Hr Lv) AxKr BgIk CqUg DiQg FaaY NdcV TzKx QaRj RfaJ OhbL aUdR} fR{dE(aY bl bX cJ cR dB dR gL Hu Hv Ib Ir Jf Jm Lx Mf Mj Mp Ms Ne Nj Nk Nl Ou To Ue) Mj(aC As aY bE bL cG Cv Dc Dd dH Hr Ik Im Jm Ki Ks Me Mf Ms Nw Nx Oe Pc Pd) Ib(aY Ii Il Kg Ks Lv Ms Nq Oe Ug) aY(aM Ar Bn Cq cS Jk Jv Or Rc) Lv(aW bL bZ cS cU Mu Qt) Ik(Ad An Ap Ba Bg Cw Di) To(dA dH lv Pd) Jd(Gz Me Qw) Ki(cV dA Mr) Pd(Lz Mg Ms) Hr(bL Pa) dH(Ms Ne) DdNj NkIq IlQw JmcS aAbP} mW{Lv(aC aW aZ bG bR bV cl Cs cX dB dE dG Ex Fa Fb Gp hB hC iA Kc Kj Kp kS Kx Kz nW oF oN Or St Tn Ug Vv) Lj(Aw cQ cR dD Fy Kx Qw Rf Rg Rm) Hr(Ax bG Gp iJ Ko Tn Vv) Qw(bA bl bQ Ed Ko Kr Qb) Rg(bA Fr Li Pa Qa Qb) Cv(Jo Oy Ug) Fr(Rj Rm Ut) Hx(Ax Bc Fa) St(Af Bn De) Pd(aJ iJ Wm) aY(Fa Ju Qa) Dc(aC Oy) Vv(Rf Uu) NoLi LxdD IbJk TrOy QaRm JgJt RhOh NxoN} nT{dR(Aa Af Aj As Bn Cp Cx De Ex Ib Ji Jt Kr Kx Nl Pj Qn Wm) Af(bG Cv Dc Gp hB Pz Ua) Ms(aQ cY Nk nU Nw Pz) Ib(bQ dB Lh Lx Tn Tj) Qa(Rf Rg Rh Rj Rm Ut) Tn(Aj kG Kj Rh Ut) Bn(aK bG Dc hB) Gz(aQ cY Mb) Lx(Oy Rh Vv) Tr(Jo Kj kS) Pz(Kj Oy Ug) Kx(Fa Lj St) Pa(kS Rg Rh) Ug(Nk Oe) DeSt ExaQ FraO NoLi NdcV IlJm KjVt KkkS KrhB LjcR RfOh NwPj UoaK cXiJ} nN{Qw(Ar bG Bn bS cA cK cV dD De dH iJ Ik Iu Jg Jo Js Kx Mn Mr Nk Nm No Nu Pa Pj Ql Rg Tv Us Vs) Bn(cD Dc Et Jg St Ua) Ex(lv Nk Rm Ut) Af(Et Jg Ua) Fr(Rg Rm Ut) Nk(cV Je Ug) Ib(Ke Lh Nw) Jo(Cv Kn Ko) Kr(bG hB Me) Pa(dD dL Rg) Gz(Mb Tv) Ns(Cp Qz) Nd(cV Gp) ll(Cv dD) Ko(Jt Ph) Vs(dL Qz) iJ(cX Mj) NoLi NrRg LyRb NlcV TrOy HbNx SrNw QubG JqPj} Ex{aY(Af Aj Ar As aX bJ Bn bP Cp Ct Cx dA De Ez Ik kC Kq mS Ne oO Rc Vo) oO(aA bE dG Hr Ic Ik Mb Nb Nk No Pd Rf Rg Rh Rj) Mb(mE mF ml nJ nK nR oQ) mS(dE dJ Iu Jm Lv Ua Uc) Al(mY nB nl) Lv(cX kC nJ) kP(Cv Jm Uc) Iu(kK mZ) mH(cY dJ) nJ(dE Nd) kO(Bb Hu) oQ(Rg Rm) Culk RcQw QaQt VsaN aKaQ cXnH} nU{Nx(aE aG aH bR cR cV cX dB Dg dN HB iJ Jg Kd Kk Kn Ko Kx Nv Ny oN Qm Qn Qw Rg Rh Rj Rm Sr Tr Ua Uc Uh Ut Vs Vt) Ib(aA Jk Ke Om Qa Tn) Ms(Jm Kx Mb Om Pz) Pa(Qw Rf Rh Rm) St(De Kx Ut) Jm(cV iJ Nm) Ic(Ax Kj) Tn(Rh Ut) bG(Lv Rb) ArLx NmKx NoLi NrRg NdcV TrRj OkPj} oQ{Kr(aA aE aY bM dJ Hb Ko Me Nw) Rg(aZ Bo Co dA Gz Kk Na Pi Ug) Af(aE Dc Kg Qm St Tr) Rm(aZ Bo Co Ez Kk Tr) Fr(aO Bn Ch Ib Ut) Gz(dJ Hu Nd) Tr(aC kS Rf) dL{Nk Qu Tv) Bn(bR St) No(Li Tn) Rh(dA Mj) Qn(Ns Vs) CxRf DbUt DcUg UcKj HrUs KkkS OrdD PaaM dAhC} Ib{Lh(kC kG kO kP mE mF mS mT mU mY nB nl nK nR) Qa(kI kK ml mU mY nB nH nJ) Lx(kF kl mS mT mU nH) nH(bQ Jk Mt Nd Nn) Mw(lW ml mS Rm) Fr(kI kK lW) Li(kI kN mZ) Tn(ml nJ) Ke(lW nl) kK(Jk St) kP(bQ dB) QbmI LjkI OkmS} Gz{Mb(Ed kC kl kK kN mE mF ml mS mT mU mZ nF nJ nK nR) oO(aY dC dH dN Ik Kr mU Nk Rf Rg) Hu(Ed Fw Nr Pf) Jm(kC kP mS nJ) kC(Cv Lx Pz) Al(kl nJ) cY(aK mH) mS(Ua Uc) EdLy PzmH QwcV RmkP NwmU VsaN cXnH dJnF} Li{No(kC kF kl kK kN kO kP lW mE mF ml mS mT mZ nF nl nJ nL nR oO) kN(aF aO Ar Bn bS cA cK dA De Ha Ih Jd Jr Pe Rg Rm Tv Ut) Ti(oF oN Vv) Qw(Ar Kc) nR(Af Bn) oN(Kc oK) MbqY OrnI bZdA} Qw{Tn(kC kF kK kN kP lW mE mF mH mS nL) Pa(kC kF kO ml mS nH nJ) bA(kF kK mZ nB nl nJ) Nx(kC kO mS mU nl) Ed(kl kO mS nB) Kr(kK mE mZ nK) Ar(Lj Lx) Us(kI mZ) LxJd JmcV KomZ LjkP PkkK dDnK} mU{Pa(aX Co cX Fa Kj Or Rg) dD(Ez Nh Nl Uo) Tn(cR cX Ut) Qa(Bo Ql Tz) Ax(Ql Qn) Bn(Fa St) Lv(bR dB) Nl(cV Ms) Tr(Jt Nx) Pz(Kj Rc) Ks(Jm Lj) Ut(Fr Qe) Pj(Mm Ok) aX(Lj Oh) DeSt LxQv NkUo UcUg aAdR} Lj{kK(bZ cS Kc oK oN Ou) Ti(Co dC hC Hx kS) kl(De Fy Kx Rg Sr) nR(bU No Rg Rm) Ar(Et Hx Ke) De(iJ nl) Kx(kG ml) Rm(kN mZ) aE(cS kN) aX(nB nl) dJ(Og Pk) iZ(Kc Vv) NknY QznB} St{Bn(kF kl kK kP mE mH ml mT nB nC nH nl nJ nK nL nR oO) Af(kC kl kK nH nl nJ nR) De(kI kK mE ml mY nB nl) kK(Nk Pj) AanJ AlkP WmmY KjmI aOnR} Pa{Rg(kC kF kl kN kO kP lW mE mH ml mS mT mZ nH nl nK nL nR oO) ml(cR Kj Or Rf Rh) Fa(kC nB) nH(Bc Dl) OrmF aMoO cRnK} Nd{cV(kF kG kK kN kO lW mH ml mS mT mY mZ nC nH nl nJ nL nR oO) ml(Ax cH iA Kc Qv) qY(hA hR Mk) hRrB} Tn{Ut(kC kG kl kP mE ml nl nJ nK nL) mZ(cR cY dA Il My Qz) kP(Ky Mf Rh) nl(Aj Tt) nJ(Pj Rc) kG(cR Nu) NgPz} Lx{Vv(aE aR dA hG iJ iZ oO) dA(Hc Jt Ng Sr Ss) Ar(kK mZ nB) Ng(aE aV iJ) Ut(kN mE) AwcH WmkO TioN SskP OfiJ} cX{iJ(kF kG kI kK kN kP lW mF mH ml mS mT mY mZ nI nJ nK nL nR) Ua(kO nC nH nJ nL) PzmI} Fr{Ut(kK mS mZ nl nR oO) mZ(cR Il No Rg Rm) Rg(kK mT nK) Rm(mT nL) WmkO NomT RbkP RfnL aOoO dDkG} Cv{Ug(kC kF kK kO kP lW ml mS nB nF nl nJ nM) Jo(kK mF mT nF nl) AakC UrmE} Pz{Ms(kF kl kP nF nH) kG(Af Aj Kj Kl) Ng(bF Gp Ti) ml(Kj Oy Vv) aA(iB qY) NunF RbmH rBqY} kK{Jt(Ad Dc Ua Uc) Vv(Bg bZ Lu) Pj(Et Mm Ok) Jf(Nk Nl) bG(Hr Pg) LuKp TrOy NxaO} kO{Wm(bQ Ij Lh Nw On Uh) aC(Bo Tr Us) Nx(Bb Vt) Alll BnNr HrUs PdcF PjdB bQcR} nR{Af(aA Dc Hr Lv) Bn(aO Jm Oz Pb) Oh(Kr Rg Rm) Ug(Cq Jm) Vt(Jt Pj) NraO} qY{Mb(aA hR Ms qT) Oi(aA rX rY) EtqV Nnll MelN MjrY NcqZ HxhR PclL} Nx{Vt(kC kF mY nB) iB(Iu Mt) oN(mT nC) CtnI HrKe HbmE RfkC} mH{dR(Aa Af An Bn Wm) cY(Lu Ms) AfDc ArHx HrbG TrJt VskS} qZ{Nl(Hr Iu Ji Mx Ns) Nc(Iq Iu jH Js) NsjO JljL hRiB} Ti{Rm(Ed Kn) aO(iA iH) aY(Cs Fp) oN(Ow Tj) AdAj CoQb DdVv} Pj{dB(kC kF kO nC nH nJ nL) Dc(mY nl) oO(Kg Tr) OkmY} bG{mS(Ct Hr Mf Wm) Bn(nC nH) Hr(ml nF) WmnC NanH} hB{Kr(kI ml nl) Af(kG ml) Mj(nC nH) mS(aF aO) Bnml} Hx{hR(Hu Ik Iq Iv Me Mg Ng Nj Nl)} Dc{oO(Af Cx Ug) MfkP JtnI UvnH dDmF} Fa{aY(AR De) bM(De kP) Bnnl RjkQ} Ng{Bg(aE dJ Hb Hc) aE(Nq Qa) TriJ} nC{Rm(Qa Qd) dB(Hr Lv) BoaC ColK NwbR} kN{Ut(Ir Nr) TrOy RmOh UrcS VtcV} ml{Qa(Rg Rm) MsKx JmKs aUdR} nl{Kr(dG Qa) DliJ TraC OybA} ll{iB(Et Mw Qb) JljL} Pd{cF(nH nJ nL) KkmE} mZ{AxRg BbOy TrJt ImUt} Bo{aC(nH nJ nL)} Ok{Jo(jL jO) JtjO} bQ{cR(kC nJ) LvmF} mE{AfUa HrKk TrRg} nB{CxiJ NmKx QvRf} kF{Us(aO Hr) TrOy} oO{LyRb KkkS KrNw} Cq{CtdI GpOy} No{Mw(nH nL)} Ms{NenL JmkP} Nk{cVkl dBmY} Iu{InjY aAjT} mS{BgIk WmGp} nK{AfUa KrNw} kG{CtKx JmKs} ArUeKe EthArB NadJnJ UcUgkP HqPgjD QaOfaE QcOelW JljLrX aUdRmF Unconstrained panels with 3 analytes, where 1.0E-9 >= 'AUC p-value' > 1.0E-10. Contains 9,245 panels of 13,646,915 total panels evaluated. : gP{oO(aC aD aL aN aQ As aU bB bL bP bV cF cH cJ cL cN Cp cS Ct Cw cX cY dF dG Dl dJ Ed Ef Fw Fy Hb Hq Id iJ Im iP Je Ji Jp Jq Jr Js Jy Kc Ke kG kl Kp Kq Lv Ma Mk Mx mZ nB Nc nD nl nJ Nq nR Nu nY oN oQ Oz Pa Pe pF Qe Qh Qv Qx Qy Rc Tt Tz Ua Uc Ud Uh Ul Ur Ut Vp Vv) fP(aE al aJ aK aR Bb bC bP bU bW cA cG cL cO cP cS cZ Dc dE dl dK Fr Gp Hf Hv Ij Io It Iv Iz Jm Jn Jt kF kP Ld Lv Lw Md mH Mi Mj Mp Mq Mr Ms Mz Na Nb Nd Ne NF Nh Nk Nl Nt Ny Oe Ok Pd Pe Pj Pk Qe Qh Sr Ss Ua Ug Um Vo Wm Tj) oQ{aJ aU aV aY aZ bA

RgkQ} Jm{Ks(mE mF)} aX{cZ(nJ nL)} bZ{QbdA RgcH} dR{mH(Jt Ph)} WmbQkI LvbRmE NadJnH NIJfmZ InIuIL IqaAjQ KdcRnL KrNwnJ UsVtnC

Unconstrained panels with 3 analytes, where 8.4E-9 >= 'AUC p-value' > 1.0E-9. Contains 12,853 panels of 13,646,915 total panels evaluated. : gP{fP(aC aF aH Al aM AN Ao Ap As aV aX bB bE bF bG bJ bL bM BO bQ bR bS bX bZ cB cE cI cJ cK cM cN Co Cp cR cT cU cV cW cX cY dA dB dD dF DG dH Di dJ Dk DL dM Dp eF Et Fb Fn gL Ha Hq Hr Ii In Jo Jq Js Ju Kd KE Kg Ki Kl Kp Kq Kx Kz Lu IX Mc mF ml Mk Mn Nc NI Nj NO Nq Nr Ns Nv Oi Om On Ou Ow Pa Pg Ph Qc Ql Qv Qz Ra Rc Rh St Tn Tr Tz Ul Uo Us Ut Uv) Oa(aA aE aG aH aL aO aQ Aw bE bF bQ bR bU bV bW cE cF cG cH cN cO cT cU dB dD dF Dk hC HF Hu Hv Hw iH Ii Il Ip Ir Is Iv Jg Jn Jt Jy Ke kF Ko kQ Lv Lw lY Lz Ma Mb Md Mi Mk Mn Mp Mt Mv Mw nA Nc Nd Ne nI Nk Nl Nm Nn Nq Nr Nt Nv Nw Nx Oi oN Or Oz Pd Pe Pg Pi Qg Qh Qn Qx Rc Rf Rh Ri Tr Tz Uc Ue Um Up Us Ut Vs Wm tF) gC(AD Af aI Aj aL An AO AR Aw bA Bb bC bH bJ bP bR bS bX cD cJ cL cM Co cQ cT Cu Cw CX cZ dF dG DI Dk dL dM dN Ez Hu Hw Jg Jj Jl Js Ju Kd Ki Kj Kn Ko Kp Li Lj Nm Nn Po Qc Qh Qm Qv Qx Qz Tr Tv Uc Ud Ue Uf Ug Ul Up Ur Us Uu Vo Vs Vt Vu Vv) aI(aH aW bC bE bQ bS cE cG cH cK cN CO cY Dd dH dI Dp dR Ez Fp Fr Fw Ha hC hF Hq Hr Ib Ij IP Iq Je Jg Jh Jm Jn Jr Js Jy Kc Kk Kn kS Li Mb Mm Mp Mt Mw Mx Nb Ni Nn Nq Ns Ny oF Og oH Ok Oz Pb Pd Pg Qa Qe Rb Rm Ss St Tn Tr Tv Ua Ug Ut Vo Vq Vt) oQ(aA aC aO Ar aS aW aX Ba bC bH bL bR bS bW cA cJ cK cO cS cT Cv cW cX dD dG dI Fb hG iJ Iu Jh Jq Ke kF kI Kp Ks Ld Lu Lv mE Mg mH Mk Mn Mr Ms Mt mU Mw mZ NB Ne Ng Ni Nx nY Of Oh oN Pb Pd Pf Pj Pk Qb Qe Ql Qm Rj Ss Tv Um Uo Ut Vu Tj tF) Lj(aL aQ bE bJ bL bM bR bV cC cE cH cJ cK cL Cp cT cY dE Fy gL Gp Hb Ik In iP It Iv Jd Jf Jn Jy kE Kl Lv Ly Me Mj Mn Mv Mw Nc Nd Nk Nl Nm Nn Nx Ny Om Or Qg Qh Qv Ra Rc Ss Tn Ua Uc Ug Uh Uo Up Ur Ut Uu Uv Vo Vs tF) oO(aF AJ aR Ba bJ bO bU bW bX cG Ch cP Cs cU Cv dC dD Dg dL dM Dp Fb gL hB Hc Ic Ih Ij Io Jg Jk Kd Kf kK kO Kz Lu LW Mc Mg Mi Mj Mq Mv Mw mY nA nH Ni nL nM NN nW oF oH Om Ou Pd Pg Qa Qg Tv Ue Uu Vo Wm Tj) nT(aE aP aZ bE bJ bV cH cL cP dA dM Gp Hc hG iA Ii Ik Im Ir Iz Jp Kc Kd Kf Ki kN kO kQ KS Lv mE mI Mk mU mY nD Nh nJ nK nL NN No Nr Oe Of oH oK Ou Pa Ql Qu Qy Rf Rj Tn Uh Uk Um Uo Up tF) Ct(aA aD aM aO aW aY bA Bb Bg bW Co cS cV cZ dE dH Et Fy Ii Ij Ip Ir It Iz Kd Kk Kn Kx Mb Mu My Mz Nd Ne nY Pa Pd Tn Uc Uh Ut Vu Th) Fa(AR Aw bE bM Bn bW cK cN cV cZ dI dJ Gp gW Hq Il Io Kj kP Kz Lv LX mM Mq My Pd Pk Qg Qw Ua Uo Ut Vs) bN(aJ Fw Hr Hv Ib Ic Ih Ir iZ Jd Je Jf Jk Jp Jq Jy kN Kp kR kS Lx mH NW oN Qu Ra Rf Tn Tt Ua Ut Vp Vu tF) mW(aA aD aP aW bR cH cZ dC Fp gL Hf hG iA Ib iP Je Jy kF Kq kR Kz Mj mU Mw NF Nh nR Pd Pz Ua Us Vo Wm Tj) Ng(aO aY cC cG Cs dG dM Ed Hb Id Io Jp Jl Jp Jq Jr Kd Kf Mj Mm Mn Nh Nn No Ny Om Or Qa Qg Qn Qw Tv Uc Vq) nO(aJ aS aZ bW bZ cQ cS dB Fb iA Ij Ip Is Je Jf Jl Jn Jv Kr Kx Lh Mk Mt Mz Nv Pz Qa Qz Rg Tr Uf Un Vq Vt) eM(aJ Al aV bB bL bU cB cC cE cN CU Cv cY Dc Dk Dp Ed Je Jr Js Jt Ki Kl Nr Qz Rc Tr Ug Ur Us Ut Vt) nD(bP bQ bV bW cN dF hC iA Ih iJ Ik Jl kC kO kR Kx Ky Mf nA nF nH nL nU Pf Rg Rh Um Wm) oE(bF bQ cE cU Ed Ha Hb Is Jl Js Ke Kf Kn Ld Lh Me Mj Nd Nw Po Qw Rm Tr Uk Uo Vu) kE(aF cM dK Hu Ir Je Kc Kd kN kP Mb Md Nn Nr Ns Oe Ou Qc Qe Ua Ug Vq Vu) kP(aG bB bQ dC dM Et hC Hw Ip It Jf Jl Kf Mt Qh Rf Rg Tn Tr Uf Un Vq) Uk(Aa cZ Ed Et Hx Ih kG Lh Li mE mF mM Mw nA nI nU Qa Qb Rm St) nL(aU cC cQ cY dE dR Hw Ik iP Jp Lv IX Ly Mb nF Oy Pz Rj Un Up) Mg(Aa Ad cC Hb Id Is Kf Ko Lh Mh Mj Mr Mt Nv Ny Qh Tv Th) Oy(Cq Cu Fw hB kC Lz mE Mh MP Mr nA nF nH Nn Nr Nw Oh) Ib(bA bZ Cu Dk hB Hx Jl Kf Ld MH Mr Mw mY No Po Ua) Qt(cC cV dF Ed Hu Hx Jj Kd Kk Mp No Nr Nw On Pe Qh Vt) lY(aR bG dE dF Hr iJ Ky Mb Ok Qg Rf Rg Rh Rj Rm Ug Vq) mU(aM aW bH cC cW dR Et Ha iA Jf Kx Me Mf Nw Rj St) Mu(cV cZ dF dG Hx Jj Mp Mt Nn Nw Oh Ok Pf Qh Us) nH(aU bQ cC cQ dE Hw Ik Il iP IX Oi Pa Pz Rj Un) kO(aQ bQ cC dB Hw Ik iP Is IX nF Nx Rj Un Up Vs) Lx(Aw cH cR eC Ef Ez Jd Ma Mh Mv Pd Ra Rg Ss) hB(Aj aW cA hG kC kK mE mF mH mI mY nI Of Vv) Aj(Ax Cs Et Fw Hx Ld Lh Mh Mr Mw Nv Uc) Ly(kC kF kG kK mF mI mM mS nA nF nJ nK) nR(aC cC cQ Et Hw kG Ky Mf Pa Pd Pz Vu) IX(cN cV dK Ha kR Lh nC Qb Rm Tr Wm tF) mP(dC dF dK Fr Iz Jl Jm Kn NN Nx Pa) Mb(kC kG kI kK kN mI mS mY mZ nA nB) Ok(Ap Ef Ik Jh Jt kN mI mS mY nI nM) Rj(kC kI mH mI mY nA nF nJ nK nN) Nw(cC cV Hf kF mE Ms nB Nx Ss Ue) Qy(aO cT Et Jl Ke Li Nr Tv Uo) Qw(dF Fw Lz Mp Mt nF Pa Qb Qh) Vs(cS cZ Jn Kc mM nA nB nY Qh) nN(cV cY iP Jf Lh Mz Nk Nn Tv) mS(iA iJ iP Kx Nn Nx Pa St Vq) mH(bZ cZ dE Il Jm Me Nn Ug) nA(aJ aQ dE iP Jp mY nF Pz) nJ(cC cN cY dE Ha Ik Un Vq) nK(aQ aU Et Jf Kx Mf Ri Up) fR(aA aU aW cC cO cU Io) mM(dM eF Jf My Qa Un Vq) mT(bP iA iP Pz Rg Rh Vq) mZ(Fr Ha Hc Ik Nn Oz St) kC(aU cC cX cY iP Jf Un) kF(dB Ip Jf Kx Lh Mf Ut) kK(aM bV bZ cD Hw Ip oF) Li(bS cS De gW Kc Rg) mF(dR Jm Lh Mf My Up) mI(Ha Ik Ip My Rh Vq) mY(aY cR dA Et Lh St) nB(bB bZ cB Iu Mf Rh) nC(aQ aZ dR Ik Nx Un) mE(dR Kx Lh Nn Un) kG(bV Jl Kp Kx Up) kI(dR Jf Kx Nt Pa) kN(Fn Ha Ip My Rh) Vv(Et Kd Kk Qh) nM(Ip My Nn Rh) nU(dE Ip Jf Jm) lW(bZ Jm My St) nF(iA Nx St Up) Of(bZ dG Hx) nI(cN Kx Nx) Cs(cA Rg) Th(aZ eF) Is(Jj Og) Qh(aV De) Ke(Jd Jh) Kk(aA cR) bQ(Lw Mi) oP(Ha Ue) EtaW NoJj QadA WnPj UgaY} oE{lW(aC aD aE aH aK aV aY bA bM bZ cH cP cT dA dD dG dJ Ez Fp Fy gL hB hC Hr Hv Hw Ii In iO iZ Jk Jm Jq Jv Jy kC KF Kg KK Kl kN kO Ld Lj Mk Ml Mn mU mW Mx mZ Na nB Nc Nh nJ Nn Ns NY Oa oH OK Om On oQ Ou Ow pF Pi Pj Qb Qt Rf Rm Ss Tn Ua Ue Un Uo Us Wm) mU(aC aG aH aR aU aW bA bB bI bJ bR bV bX cB cC cD cF cG cH cJ cN cO cR cS cT cZ dE dF dH Fp Fw gL Gp iH iJ Ik iO IZ Ji Jj Jm Jo Jy Kc Ke kI kK Kl kQ kS Lh Lw Ly Mb Mc Me mH Ml Mk Mm Mq Mv Mw Nd Ne Nh nM nN Nq nU oF Og OH Ow Pi Qb Qh Qt Uk Ul Ut) mI(aG aI aL aP aQ aR aV bB bI bL bO bQ bR bU cH cJ cP cQ cS cT cU dD dF dK dM Et Ez fP Gp hF hG Hq Hr Hv Hw iA iH iJ In Ji Jj Ju Jv Kk KQ Md mT Mu Mw nA Ne nF Nh nU nW nY Oa Og Ok Om oN Ou PF Qm Qu Qx Rj Ss Tr Ud Uk Us Vp Tj tF) oO(Aa aC Aj An Ao As aZ bA bC Bo bP bW cG cJ Cp cT Cw Db Dd dF DG dI Dl eC Fp Fw Gl Hc Hq Id iP Jd Ji Jk Jq Jv Jy kI Kq kS Ky Ld Lh Lu Lw Ma Mc mE Mi Mq Mt nB Nl NM oF Oh Oz Pb Pc Pj Pk Qb Qg Qm Qn Rh To Tt Ub Ue Uh Ur Tj) kO(aL aZ bA bB bW cE cF cJ cO cU cZ dG dI dM dN gL Gp hF hG Im Ip Jm Jq Jt Jy Kc Ke kF kN kP Kq kR Kz Ld Lu Lx Ly mF mH mP Ms Mw nI nN Nq Nr oQ Ow Uk Un Vu) nJ(aP aW aZ bA bB bO bW bZ cD cE cF cJ cN cU cY dI dM gL Gp hG Im Jj Jq Jt Kc kI kP Kq kR Ld Lx Mb mH mP Mw Nd nH nI nN nR oH oK Ow Pi Ql To Tr Uk Vu) Vq(Aa aU aV aY bF bJ bO bV cJ dA dC dG Ex Fy Hf Hv Im Iq iZ Jp Jr Kk Kn kR Li Md Mn Mr NB nH nI oF OK Pi Qe Qu Rb Rg Ua Uh Um Uo Up Ur Uv Vt) kC(aP aW bA bW cB cE cF cN cU cY dC dI dN gL hF Im Is Jj Jq Jt kI kP Lj Lu mH MP Ms Nd nI nN Ns Ow Qh Ql Qw Qz Rm Uk) kN(aP aR aW aY bA bL bO cE cH cM cR cS cT dE dG dH dI fP iJ Im Ji Jq Lu Ly Mb mH mP Ms Mw nI oK On Ow Pe Qy Uk) kP(aA aP aS bA bB cC cD cJ cU cV fP hF Hr Il Im In Iz Jo KG Kx lY mH Nf Nq nR Nx Ny Oa Og Ow Pe Ua Wm) mZ(aK aR bE cG cM cN cR cU dC dK FP Hf Ib Im Is Jj Jp Kz Lx mF mH Mt Nd Nq Ns Nv On Qw Rb Uf Vu Vv) kE(aC aN bF bO cP dD hB Id Ii In Jf Ji Ko Ly Ma mP nC Nf Nq nR Nu nY Oh Oi Pj Qn Ra Uk Un Ur Vu) nT(aP aU dR Ez Fb Hr IH Il In Iu Kx Lj Lu lX Ms Nf Nu On Pc Pd Po Qz Rh Rm To Tt Uk Vt) nD(aE bU bW cD cF cM cT cU cY dK gL Hr Il Im kI kR Kx Lx Mw nA nI nN On Or Ql Ra Uk Vu Wm) mP(aF bH bU cV cX dG HF iH Jf Jp Kd kQ Lx Ly Mh Mj Mx oK oN Qd Qh Ql Uh) kK(aI aU bG bZ dD dH dR gL Gp hF Ik It Jj Jp Kc Kd Ky Mw Nd Pa Qw Qz Ra Rm) Qh(cE Cw dA Dc fP Hc iJ Jt Kk lY mF Ng nH nI nM nU Ou Pa Qx St Wm) nN(aF aN bZ cO cS dH fP Hr Im Jo Ks Kz Mb Mw Nq Ns oK oN Pj Ut) kI(aF aP cF cO dL Ha Hr iJ Il Is Jj Jt Ky Li Nb Nd Nx Oa Qu Vu) bN(aI cE Co CS Cv Fa Hr Jr Kd Lx Nd Qw Tn Tz Uf Uh Us Vt) lX(bH dL fP Hf Ib Ii Il Ir Ks Kx Ky Mh Mp Mw Nd Or Rb Ut) mF(cG dR fP Ha Ih iJ Il Is Lx My Nb Nd Qz Ra Rb Ur Vu Wm) mH(aF aJ hF Hr Jd Jj kR Kz Mn Mw nA Nb Nd Ns oK On Qd To) nL(aN aP bL cD cR hC Il Jt Kd Kz Ld Lx Ms Mw Nx Uk Us Vv) oP(aO aX Ch Dc Hc Iu Jr Js Mp mS Nj Nu Nx Qn Qw Ra Rb Ut) Ex(Aa aX bG Cq Dc

Figure 27 Continued

Dk Fa It Kg Mn Nu Nv Nw Og Oh Po Tn) nB(aM dL Iu Jt Kd Ks Mp Pd Pg Qw Qz Rb Rj Ug Vu Wm) kG(aX bH cG fP Hc Ii Is It Jn Kx Mb
Nm Nx On Pe Qz) nR(bH dH eF Hc In It Js Kc Lx Mn Mw Nb Og oK Rg) mW(aO cQ dC dH dL gL Jj Mp mS Mw Oe Of Pe Pg Rj) nF(aX bH
bU cY fP Ha Hf Il Jr Mp Mr Nd Nx Qz Wm) kF(bH dG fP Hf Ir Is Jr Mj Mn My Nd Qz Rg Ug Wm) oQ(bH dL fP Ih It iZ Js Mb Mp Oi Qw Ra
Rg Wm) Is(al Ib iJ mT nA Nd nI nK nM Nt Qt Up Vv) lY(aE Ib Ik Jj Jr Kd Ks Kx Lu Lx Mp Nd Qw) mY(dD dG fP gL iJ It Ky Mj Nd Nf Nj Pa
Wm) nM(aF fP It Jj Ky Mn Nb Nd Nx Pe Qz Wm) nK(aP cO cY dH fP It Js Lu Mp Mr oH Uk) nU(aF bH dH fP Ib Jj Ky Ms Mw Qz Ug)
nA(cO Hf Hr Ii Ip Ky Mp Mr Nd Qw Wm) mT(bL Hf Hx Js Jt Kd Mn Po Ug Vu) nH(hF Kq Kz Ld Lx Ms Nq Pj Rc) Th(aO bM bR hG Ly Nr
Pa Qw) mE(Ha Ky Lu Nd Qz Ra Rb Uk) nl(aF fP Hf It Mp Qw Vu Wm) mS(li Kp Ks Or Tn Uu Uv) nC(bR Hb Ib iH Ks Ld Wm) Oa(aE AR Ir
Nj) Pa(aP bM iZ Uk) Gz(Nn Pz Qw) Nd(aR cE hG) aP(dM hB Pf) nO(Aa cW Oz) Nk(Li Rm) Pz(bF Uk) Vv(bF Tn) fP(aW Qb) AjTr CvUk
DeKk FaWn LxJd SrNw OfcE} Up{oQ(aF aP aR bB bC bI bL bS bV bX cA cC cD cF cG cK cP cU cV Dp Fa Fb Fy gL Ha HF hG Ib Ic Il In Io
iP Iz Ji Jn Jq Js Jt Jy KC Kf kG kK Kl kN kO Kp KQ Kz Ld LW Mc Mf Mg Mi Mj Mq MS Mu mW Mx mZ nB Nc NF NI NJ nM Nn nU Ow
Pa PF Qc Qd Qt Qu Qx Tt Tz Ud Us Wm tF) lX(AF aN aQ aY aZ bC bG bJ bO bP bZ cC cG cM cR cW dL Ed Fb Fy Ha HC iJ It Jh Jr Kc Kd
Ke Kj kK KQ KR Ld Lu Md Mh ml mP Mr mT Mu mY Mz Nb nI nJ Nn Ns Nt Ow Pd Pf Ph Qn Rb Rc Ue Um Ur Us Vv) nD(aC aX Ba cG cH
Cq cS cV Db dE Fp gL Ib Ik iO Iz Jh Jt kE Kl kP Kr Ks Kz lW Lz Me Ng Nj NO nT Om Ra To Tv Ut Vp Vs) nO(Ax bC bZ Cq dF dH eC Ha Iq
Iu Jg Jl Jn Kk Kn Lv Mw nB Nc Ni Oh Oi Pc Uu tF) kF(Bb bE cC cR dG Di dM Hb iO Jg Jp Jv Jy Kk Kq Lh Li Lv Oz Qb Qc To Tz Uv)
oP(Aa aM aO bV cU Dp Fy Ha Ke Ki Kk Mh mP Ms Mx nB nN Nu oH Or To Tr Uc Tj) Qh(Al Ar aS aV bA cA cF cK CP cQ cV cZ cM fR hF
Hr Mu Ng Og Qt Qy) nA(aZ Bg bM bQ bX cH cQ dE dR iH iO Kg Mt Ng nR nU oK Qd Rc Tz Ua tF) nB(aU bH bV cF Ed Ii Il Iv Jj Jk Ky Li
mU Oe Ok oO Qb Qc Qz St Uk) mP(Ad aV Aw iA Jd Jp kC kO Lu Lv Ly Mj Mt Mw mY nF nJ Nq Ub) kO(aQ bJ bV Di dN Ii Ij Ir It Jg Jk Kk
Li Me Nd Oe oF On) eM(aA bZ cS cX dG Hv Ip Iq Jf Jl Kp Ky Nn Oz Qd Ss Ua) nR(Al aP Ax bH cH cX dH eC Hr Ii Kk Lj Ok oN St) nT(Ax
aY bQ cY Di dJ Ii Jj Jp Kq Lj oH Qd Tn Tr) mF(Ad aI dG Hu Ii Jk Oe Ok On Pb Rb Sr Tr Tz) kE(Ax aY cP dF Iq Lv Mr Nb Ny OF Uf Uh Uu)
Is(aI aK aR cR gW Hc Jj Mu Ng Of Og Uk Vs) mS(Ad aM Ax dF Ii Jk Nk Oh Oi Pf St Tr Ub) nN(Al bV dN Hb Je Ko Kx Nr Pa Tn Tr Ua)
mM(dF Hu Jk Kk Kq Ky Lv Nk nW On Tn Tz) nL(Al bQ Ch dG dH Ij Kx Nn Oe Qz Tr Uh) kG(Ad Al bG dF dJ Im Ir Nk Nr Ok Qe Vu) kN(Fn
Ij Iq Ir It Jk Kk oF On Qe Uc Uh) fP(Al aR Bb Dd Hc Ip Jq Js Nn oO St) mH(Ad Al cY dG Fn Hu Ii Ir It Jk Oe) mU(Ax bV dH eC Iv Ke Kq Lh
nK Qd Uf) nJ(Ax bV Ij Jk Jl Jp Nv oO Pa Uh Vu) kC(aQ bQ bV dG Hu Ij Jk Jp Oa St Uh) kK(Al Ap Bb Dd dM Fn Ii Kk Ok Qe Tr) nC(Ad bG
bH bV Hu Hx Jg Li Nv Qb) nK(Jl Lh Li Lx nW Pa Pb St Uf Vu) ml(cD cH Di Jj Kj Nk NI Oe Ua) mY(Bb Jp Ke Oe Oh Qd Qe St Uc) nI(bP Fa
Fw Hf Im Jj Kn Qd Tz) kP(Al bM dR Ii It Kx Li Oi Ua) bN(Ax Cs Cu Dc Fw Qa Rm Uk) mE(Ad Hu Ij Kn Oa Oh Qz Tr) mW(Al Di dM Ij Ir
Kk Ua Ub) kl(Ad bG bV dF Lv On Ub Uh) fR(cG dE Hr Ij Ky Lv Mp) mT(Ad Ax Ib Jk Lv Oe Ub) mZ(Ir Kk Lv Lx Oa Oh Ok) nF(bV Ij Ir Jk
Jp St Uh) oO(aJ aW cU dG MI Ni Qg) nU(dG dM Kk Oe Qb Tz) nM(Ad Al Ir Qe St) Th(Aa iJ Mu Qb) gC(dE My Pd Qu) Ih(gW Og Tk) Lj(aI
Ar cR) Wn(Ic Qv Ue) IW(Ij Nk Vu) nH(aQ Pa Qb) Ng(Et Tr) Li(eC Kc) IY(Ch Cq) CtRm OaaE} bN{Qh(Aa aE aH aJ aK aL aO aQ aR aS aU
aV aX aY bO bP bQ bZ cA cL cQ cR cU cX cY cZ dB dE dG dM Ed Ez Fb Fn Fp Fw GI Gp Ha hB Hc hG Hq Hv Hw iA Id iH Ik Il iP Iz Jd Jk
Jr Js Ju Ke Kf Kg Kj Kp Kq kR KS Ky Lz Mg Ms Nd Nh Nj nO Nt Ny Oa Oe Of oH OK On Ow Oy Pb Pd Pj Pz Qt Qw Qy Rb Rc Tn Tr Tz Ug
UI Vo tF) fP(Ax aY cH Cs dJ Dp Ez Fn Fp Fy Hq Hu Hw iH iJ Is Iu Je Jf Jg Jh Ji Jo Jp Js Jt Ju Jv Jy Ke Kf Kg Ki Kj Kk Kp kQ Ky Lh Lx Nm
Nu Po Ql Qt Ra Rb Rc St Ti Tv Ua Ud Ue Uf Ug Um Uo Us Ut Uv Vo) Is(Dp eC Fy Ha hG Hu Hw Id iH Je Jh Jl Js Jt Kj Kk Kl Pz Qb Qc Ql
Qu Qv Ra Sr Tn To Tr Tv Ud Ue Uh Ut Uv Vs Vt Vu Vv tF) Oa(Af aI aL AO Ap Aw Ba bB Bg bM Bn Bo bZ Ch Cv cZ dA Dc Di Hv iO iZ Jj
Jr Kc Ko kS Kx IX nW nY oN Pk tF) Uk(Al Ap aR Ax Bc bZ Co Cs cZ Dd hF Hr iA Ic Id iJ Il Ir Jr Kk Lj IX Mw Nm Nn Nr Oh Ok Qw To Tr
Uc Uf Wm) Ad(Aj Et Ib Jd Jk Jn Jv Kc kQ kS Lj Ng Nm oH oK oN pF Po Qc Qg Qm Qy Rc Ri Tr Ua Ub Uf Uh Vq Vv Wm tF) Et(Al Ap As
aW Ba Bg Bo CH Co Cq Ct Cu Cv Cw Db Dd Di dJ Ed iJ Jr Mm Of Pc Qb Qn To Ug Us) Lx(hB hC Hv Ic Il Jd Jh Jp Jt Kc kS Ng Nt Qt Qx Qy
Rb Rf Ri Rj Rm Sr St Tn To Ub Uc Um Un) Qa(Aj aR aY Bc Bn Cs Ct Cu Db Dc Di Hc hF Ic Ij Jr Kk Of Qy Ur Wm) Ss(aI Aj aX Ba Bc Bn
bW bZ Co Cx dJ Dk Fw Ih Nq Ob oO Pn Tn Uc Uf) Qw(aI Ar AX aY Bg Bn bV cH Co Cu Dg dJ Fa Ir Lt Mt Pf Ty Wm) Jn(Af aI Aj Ao Ap Ba Bh
Bc Bo Co Cq cS Cw Cx Dd Dg Dk Ih iJ Kk) Ko(aI Ao As aX bV Ct Cw Db Dc gW hB hF iA Ih Ms Ng Pz Qb Uo Us) Wm(BB bF bZ Ij iO Ip iZ
Jm Jq Kk Mt My oH St Tn Ti) Vq(bJ Dg hF kE kF kI kK kS mF mM mU nI nU oF Pz Rc) Jr(AR Bb bM Bn bV bZ dJ gW Ih Lj Qb Tr Uc Ur)
Dc(eC hC iA Ib Ic kR nY Qg Qm Qv Rc Uf Um tF) Pz(Aj Bb Bc Cp Cs cV hF hG Ib iJ Of oK) al(eC Lj Nm nN Nq Qd Qn Qy Rb Rc Ug Ut)
De(Ib Ic Jm Kf Lj Qb Qe Rm St Tt Vs) cS(iA Ic Id Jj Jq Ke Kk Kp Tz Ub Ur) iJ(Ax Fa Fr Ih Js Li nN Qe Uh Um Ur) Tr(Aj aR Ax Bn bV Cs hB
hG Ih oK) gW(cY Hx iA iO Sr Uc Uf Us Ut) dJ(Fa hB Jl Jm St Uf Ur Us) hG(Ax Bg Cu Fa Fb hB Ip Li) Bb(hB hF Hx iA Ib oK Tn) Cs(eC Id
oK Sr Tn Tt Un) Hr(bM bQ bZ cH iA Ke Nw) Ih(Fn hB Id Kk Un Ur) Qb(Db Dg Di Hf iO Jj) Uh(Aj Ba Bn Cw Db pF) Fa(aY bM Hv Qn Un)
Tn(Aj Ao nD nN nO) Sr(Aj Ct Cu hF Ng) Jj(Al aW It Jm St) Bn(Jm Nq Uc Um) Ur(Hb Ke Nw Um) eC(Ex Li Mz oQ) Ar(Id Kk Qe) Bg(iH iZ
kQ) Th(Ed Mu Ri) Na(kC mY nN) hB(aW Jm Lj) Db(iH oQ) Nx(Hb Jq) Vu(kK mW) hF(cZ Fb) CviA DgRc ExaY FwnO LunD HxcH HcoK
StiO KeUn LjaG PfkN PjmP aKaV} Vq{nA(aC aF aG aK aO aQ aW bB bC bP bW bX cI cJ cU cV cZ dA dC dN Ed Fa Fy GI hG Hu Ih Il Is Iz
Jk kE kG Kk Kl Kp KQ Ky Lv mM mP Mr mS MT nD nH nI nJ NL nN nO nW Oz Pf Pg Qd Qg Qw Qz Rc Tz Uh Vv) kP(aF aW aZ cG cJ cR
cT dC dH Ha hC Hf hG Hu Ic Il iP Ir Jn Js kC Kg kl KK Kp kR Ky Ly Mb MH Mw Mx nJ nK Nt nW Oe Oi Ok On Pa Pc Pz Qm Qn Ra To Ue
Uh Vt tF) nD(aL aO aP bS cA cB cC cK cX cZ dB dJ fP Io Iq It Iv iZ Jl Kf KO Ky Ld IW IY mE Mg ml Mj Mw My NK Nq Oi Pa Qg Qu Qz
Ra Tv Ua Uf Vs) IX(aN bU cV cY dE dJ dL Hu Im Io Ir Is It Ji Jj Jm Js Kg Ks Li mE mM Mr Nd Nj Nk Nm No Pe Pg Pk Pz Sr Vs) nC(aC aI
aK aV bA cB cV cX dA Ib Kf Kk kO Kp kS ml Nd Nk QI Qv Tv Vo Vu Vv) nJ(aC aQ aU bE cB cV dD fP Ir Ji Kj Kp Ms Mw mZ Nd nW Pd
Qe QI Ue Uk) Ng(An Ar bI cB dJ Ib Iv Lv mP Nc oK On Pb Qc Qt Qw Tr Tv Ug Uo) mF(al aQ aV aX cB dD Ha Hu Ih Kc Ks IY Nk No Pa Pj
Qc Qm Vo Vv) mH(aE bR dA dD dJ Fn Gp Jf Ji kE Kj kS Mq Mu No Or Ow Ph Pj Po) mS(aK aQ aU aV bJ cF cY dA Fb Gp Hw Ir Ji Jt MI Nw
Qa Ss St Tv) lW(aI bS cA cK dD Hu Ih Jt Ju Kc kS Mj Nt Nw Ph Qc Vo Vs) IY(bJ cF cX Gp Ha Il Ju Kj Kp Nc No Ph Qc Qz To Tr Vo) Ib(aI
An bQ Et Fb Ip Jl mT mU mW nI nK nU oF Oh) nH(aK aV bA bE bG bQ dA fP Ir Ju kS Ms Or Tv Uk) kE(bA bR dD dF hB Hx Lx Mg Mw
Mz Or Ph Qa Qe Qv) Ip(aL An bJ cZ Ef Iz Jj Jo kS Oe Og Ug) Fn(kl kN mP mT mW mY nB nF nN nO nR) nT(dJ Hu Ir Jv Kc Nt Og oH Qc Qn
Sr) nl(bG bJ bQ cB cR cX eF Ir Ld Rc Vu) nO(cX Hx Ir Kn Nt oH Or Pj Qv Uf) mE(aI Ir Jt Kc Ld Nt Qc Qn Vo Vv) ml(al Ir Kc kS Ld Ml Nt
Nw Qc Vo) mP(aI aQ bJ dJ hB kS Mg Sr Uk Vo) mU(aK aY cB Jt Kn Nb Pj Qn Sr Ub) nN(dA dD Il Js Jt Ju Nd Pj Sr) mZ(aV bG cY Jm kl Mz
Qn Qv Vo) nK(aQ aV bG Kg kS Ld Nw Qn Vo) kF(cB cS eF hB Ju Jv Nt Pc Qn) Ik(An aX cS cV Jn oF oK oN) nR(aC dJ Jt Ld Mr Nt Pj Vv)
nL(aQ aV bG dA Jm Jt Nd Vo) mM(cV dR iH kS Nw Qc Vo) mT(aI dJ Ir kS oH Sr Uk) mW(bR cX dJ Io Ko Nt Pj) nB(bE Fb Kp oH Pd Qn
Vv) kG(aQ aV cB Jt kS Nu Uk) Aj(aO bI cV hB oN Ou) De(aI Et kS oF Us Vv) eC(dM Et fP Nw oF oK) nU(dA dR Jm Kc oH Sr) kO(aV bG
cX dB Jt Wm) kl(cY Kj Ml Nt Uk) fP(aC iO KI Ss) kN(cB Ma Nx oK) Jh(bZ Tn Uk) kK(aQ cB Ph) Qw(Fw Oh) cY(nF nM) dA(Mg nM) kC(Im
Jy) oF(Ef Pb) CpUk HxcX SsaO QtdD JttF VsdJ OybQ PjmY aliJ} Fn{fR(aE aP bB bC bP bQ bU bX cG cH cL cM cQ cT cU dB dC dJ GL Ic
Io Iz Jn Jr Js Kc Kd Kg Kj Ld Lj Ma Mb Mp Mt Mx Nj Nr Nt Nu Nv Oe Og Oh Om Ou Pe Po Pz Qd Qm Vo Vv Wm Tj) kE(Ad aW bW cB cD
cH Cs Cu Di dN Hc Ic Io Is It Jf kl Kk Kl kN kP KR Ky Lh IY Ma mH Mm Mr mU Mw My Mz nB NI Nq Nu oN Ou Pb Pg Po Qw Uc Un Ur)

Vv) dA(cS iJ nY) dJ(bZ dC oK) No(mF oQ) Kc(nW oN) Rg(bZ mZ) mW(cY dG) iJ(Jo Po) Wmkl EtKq GzMj Mbq

Fy nB Qb Ra) hC(Af Bn Ib Kr Nl) Fb(Jj Ns Qn Vs) Jm(cV oF Ql Qv) Li(bZ Kc oK Ou) Ba(Hx Rc Vo) Fa(bM oH Pa) Ua(Af Bn Ug) Ib(Co Jk Lh) Kr(Nq Nw On) bG(An cB Fy) dF(bH Ns Qn) nW(cB Ns Ur) Qd(Or Un) Jj(Al aM) Nx(Fy Qn) cE(Ju Rc) CwPj GpaM MsKn NiRi NkcV NloF ImQl IzKj QwcT JvOn KpPa} Wn{Bo(Ba Bb Cs Cw Cx Dg Dp Ed Gl Hb Hc Hw Id Ii Jg Jh Jl Jq Jt Kx Li Lj Lu Lv Ly Md Mg Mk Ml Mq Mw Na Nf Ns Nu Nw Nx Oi Ok Om On Pa Pe Pf Ql Qm Qt Qy Qz Ra Rb Rh Sr Ss Tv Ul Us Ut Wm Tj) Hf(An aS aW Ba BN bU cB Co Cs Dc De Dg Dl Fn Hb iJ It Iu Jf Jt Ke Kk Kp Kz Li Lj Mb Mg Mh Ml Mt Ng Nk Nm Oh Oi On Oz Pa Pf Pg Ph Pj Qb Qd Ra Rb Rj To Ug Um Ur Vv tF) Hc(aF aH aK aO aQ aU aY bF bN bQ bU bV cC cG cH cY cZ Db dH dJ Fb Hx Ir Jf kS Kz Li Mb Mu Mw Nk Nx Oh Ou Oz Pc Pj Pk Ra Rb Rg Tt Us Vv) Mw(aA Ad Ba Bg Bn cH Cv Cx Dc Dk eC Ef Et Ic iH Iz Jl Kq Lh Lx Mn Ng Nv Nw Nx Ny Of Ok On PF Pg Qu Qv Ss St Ua Ut Vt Vv) Nv(aK aL aQ aR aU aW bN cC cL cY cZ dA dJ Fa Hq Hx Il Is It Ke kQ kS Kz Mu Oh Oz Pg Pj Qe Ra Rg Tt Us Vv) Li(aA aO aX aZ cC cH cN cP cU dA dB dJ eC Fy Hb iH Il Iz Jq Jt Jy Ks Me Na No NY Pj Qu Qw Rb Us Vv) cX(aQ aR aW bN dA dJ Fb Fr Ha Hb Hq Id Ir Jl Ko Mu Ne Nk Nn Nx Oa Or Pa Pf Pi Pj Po Qv Qy Ra Sr Vv) Rb(aR AW Bb bN cC cH cN CP Cs dH Ef Ha It Jl Kc Mk Nn Oh Pf Pj Qh Qw Qz Rc Sr Tt Vs Vv) Jl(aQ aU aV bA bO bQ cM cY dA Db dC dJ dR Hq Ir Kp Kz My Pc Pj Ra Rg Us Vv) Vv(aF Bn cF cN cQ cR Cu dA Fb Hx Ko kQ Kz Mb Mp Na oE Pf Qv Tr Uk Vs) Rg(cC Db Hb Hw Ii Il Jo Ks Me Mr Ng Ni Nj Nx Oe Om Ql Qu Qv Ue Us) cH(bJ bZ cQ Hw Ir Is Ji Jt Ks Ma Mm Na Nx Or Ra Rj To Ur Us) Pj(aA Bn cN cP DB gL Hb Id kQ Kz Lu My Ng Ra Tt Us Vt) cC(aA Gp hF Hr Ic Jd Jp Kr Me Mh Or Pf Qt Rj Ur Vs Vt Wm) cN(aQ aV bQ dA dC fP Jn Ju Mu Nk Nx Oe Po Ql Qm Qv) Ra(aK aL Ba bH Dl Ha Hu Ic Kq Kr Me Of Qn St Vt) Us(bC bO Dd Gp Ha Ic Kq Ni Pf Qg Qz Um Ur Vs Wm) Hb(Aw aY bC cJ cL DB eC hF iH Kr Qc Qn Vs) Kz(An cB cI Gl Ic Lh Ml Mm Ou Pf Qu Qz Rj Tk) Db(An Gl Io Iq Kc Kf Mk Mt Pa Qw Qz Rj) aW(dB Id Iz Ks Ld Md Ng Nx Qu Qv Uk tF) dB(aY bF cB lP Jq Kc Kx Lj Ml Mm) eC(bF Dp Io Iq Is Kc Lj Pf Rj Sr Tr) Pa(aY bB cJ Cs fP iH Kr Vs Vt) Fb(Af Ba Bg Cx Iz Ks Ny) Sr(aX aZ Di iH Ng Qv) Qu(aQ cV dJ dR Na oE) Ks(aP bF cB Dp iP Kc) Ml(aO cJ Kr Nr Vt) Is(aA Al aO cL Ct) bF(aA Fy Ic iH Na) Me(aM aO bN cE) Ng(dA Ib Tn Vs) Rj(aZ dE Ki Qv) Fa(cP gL kQ) Il(bZ cB cQ) Nx(aK Jq Kn) aA(Ha Ip Lj) Cs(Kr Nr) Mm(aQ aU) Na(Kc Qz) Ue(dJ Vt) Ic(bN bZ) Qv(It Iu) Vs(Jj Pf) aO(bZ Fy) dL(Kg Pf) fP(bN Oh) AwSs MbVt HqIi TtIz ToaZ TnKl InPz JtdA KraM PekQ} Ri{lY(aC al aP As aZ bA bF Bg Bo bQ bZ cE DB DD De dF dM dR eC eF Fr hB Hr Ir Jj Jo Kc Ki Kj KS Kx Ky Lu lX mE Ms Mt mW My Nc Nd Nh Ni Nl NR Nx oF Ok oP oQ Pa Pf Pk Qa Qc Qe Ql Qy Rj Tn Tz Ug Uh Uk Um Un Uo Us Uv) oO(Af al Aj aR Ax bA bL bM Bn bZ cD cE CT cW De dF Ed Ex Ez Hq iA iJ Il iP Ir Ji Jj kC Kj kO Li Lj Lu Lx mF Mg mM Mu Mz Nb Nc nD Ng nl nJ nK Nl No Nu Nx Ny Oa Of Oh oQ Ow Pd Qa Qb Qn Rb Tr Ug Uk Um Uv Wm) oQ(aA AF al aO aW aX aZ bM bQ bX bZ cB cE cH cI cJ Co cP Cq Cx cY dF dJ dK eC Et Ex Ez Hw iH Il iP Jj Kc Ke kK Ko Ky LX mM Mp My Nb Nk nU Nw oE Or Pa Ql Qn Qt Qu Qw Qz Rj To Tr Uf Um) lX(aM An aR bG bP bZ dG dL dM Fb Fr iH iJ Il Ir kC kF Kj kO Kx Li Lj Lx Mj mM nA nC nD nJ nL Nr nT Nx Oa Oh oP Pa Pf Qa Qb Qe Tr Ue Uf Ug Uk Wm) mM(al aY aZ bA bG bQ bZ cB cC Co Cw dB dF dM dR eC eF Gp hB Ij Im Ip Ir Jg Jp Kc Kq Lh Lj Mn Nw oF On Ow Pa Pi Qa Qc Qd Qe Qh St Tn Um) oP(aO bA bG bN bQ cC CH cN cT dR eC Ed Ha Hx Ij Kj Lj Lv Lx Ms Mx Mz Nb Nl NN Nr Nx Oa Oh Ow Pa Qa Qb) eM(bP bV bW cH cR cS cV dI dJ dL Ed fP gC Hf Hv Il Iq Js Lv Mm Mq Mr Mz Nn Pi Pk Rc Rh Rj Us Vu) kO(al aP aZ Bo bR cB Co Cw CX DB dF iH Ip Jj Kj kS Lh Lu mS Na Nd oE Qd Tz Ug Uh Uk Um Uo) nU(aM bA bG cE cN cT Fw Ih Ij kF Kx Lj Lu nD Nr Nv Nx Oa Oi Pf Qa Qb Qh St Tr Um) nN(aW aY bG bN bZ cE dG dM Gz IJ lP Jj Ke Ly Mf ml Mz Ni Nk Nw Pa Tn Uh) nD(aX aZ bA bG Co Cw dB dM Ex Kj Lu mS Nd Nr nY Ow Qa Qb Qc Tn Vu) Th(dI Ed Fa Fp Hb Hr Il Li Lj Lx Mj Nx Oa Qa Qb Vu Wm) nJ(aX aZ bQ bV cB Co Cw cX dB Ex iH Ip mS Nr) nR(aO Ax bP Dc Di dM Li Lj Mk Nk Nn Oh Qb) mS(eC iJ Il kC Lj Lx nA Nr Nx Oa Pf Wm) nL(aZ cB Cw cX dB eC eF Fr hB iH Qw) nC(aZ bQ cB Cw CX dB Fr iH oE) gC(dC Kq Lv My Ne Oy Qt Qu Uk) ml(bQ dM Fw Ir Lx Nd Oh Pf Qa) kF(As bQ cB cX dB eC iP oF) kC(aX aZ Co Cw dB eC Ip) kI(al bQ dB fP Qw Uk) bZ(lW mE mF mH mT) dM(kK lW mE mF mH) eC(mU mY nA nF nH) mW(Ax Ha Ni Oa Oe) mZ(Ax Li Lj Lx Qw) Ir(lW mE mF mH) mU(iP Mz Uk Uo) nA(aZ Co Cw Ip) kN(Ax hB Li Lj) Ti(Lj Oa Qb) Pf(kP nK nT) oE(mH mT nB) Lx(kP lW) Ni(kK kP) Ip(mY nK) nH(cX hB) TnkG UknB PamF aYmT dGkK} oE{Ex(al Ax bA bQ bZ Cs Cu dD dF fP Fr Fw hB Hq Ip Jl Kd kl Kk KN Ld Lh Li Lj Lx Ly Lz Me Mh Mj Mp Mq Mr Mt mZ Nd Nn NR oF Ou Oz Pa Pb Pe Pf Pg Pz Qh Qw Qz St Tr Tv Uc Us Tj) nO(aK aU Aw bH bL cF CO Cq Cw Dc dE dH Fn Ha hC Ib Ih Ik Im Ir Is It Iu Jc Jr Js kP Kx Kz Lv Ma Mb Mn Mw Nd Nj Nk Nm Nq Oc Oy Pc Pi Qh Qy Rg Rm Uh Ur Ut Wm) oO(aX Bg bN cO Cs cY DE dH eF Ha Ib Ih Im Ip Ir Is It Iu Iv Jr Js Ks Kx Kz Li Lx mH Mr Mw Mz Nd Ni Nj Nk No Nx Oi Pa Pe Pg Pi Po Pz Qh Qy Tr Tv Vs) mS(Ar Ax bH bN bS cA cK cO Cs Dc DE dH Ha Ib Ih Ik Im Ir Is It Iu Jn Jr Js kP Kx Kz Li Lx Mr Mw Nd Nf Nj No Nq Pe Pg Ph Pi Po Qh Ql Qy Rg Rm Ut) mM(aH al An aW bl bQ bZ cD Ch dD Fn fP GL Gz hB Ic Ij Iz Jg Jh Jl Jn Kc kF kN Ko Ma Mf ml Mv My Nm nN nR Nv Ou Ph Qh Qw Qz Rh Vu) ml(Ar bN bS cA cK cO Cs dH Ha Ib Ik Ir It Iu Iv Jd Jr Js Kx Mr Nd Nf Nj NK No On Pa Pe Pg Po Qy Rg Tv Un Ut Vs) lW(bN bS cA cK cO Dc De dH Ha Ib Ih Il Ir Is It Iu Iv Jr Js Kx Li Lx Mh Mr Mw Nf Nj No Pa Pe Pg Ph Po Qh Qy Tv) mP(Aa Af Ao Ap As Cx De Ed eF Et Ib Ii Ji Jo Kx Lu mF Mm mW nC nD Nu Nx Or Qn Qz Un Wm) kP(Ar bN bS cA cK De dH Hf Ih Ir It Iu Iv Jr Js Lz Mf Mr Nk Nm No Oy Pg Ph Ra Rg Tv) nT(An bL Cq iJ Jj kC kO Lv Mb nA nD nH nJ nL Oy Pa Ra Vu Wm) nA(aX dD dL Fn Ib Ji Jt Mj nC Nx Qn Qz Uv) nD(aX dA dD dH dL Fn Jt Lu Mj Na Pj) Th(iA iH Il Lj Mb Oa oN Vu Vv Wm) nJ(aX dA dD dH dL Fn Mj Na Pd) kN(aO cW dF Hc kK Lv Mv oN Ut) kO(aX dA dD dH dL Fn Na No Pd) Pa(aE aR bN dA mU oQ Oz Qw) bN(fP Ik Is Li Qh Uc Ur) eM(aX dA Kr Lz Mn Pj To) mU(eF Ii In Ks Or Rc Uv) nC(aE Hx Mj Na nH Nx Rf) Lv(kl mE mF mW mZ oP) nL(aX dA dH Mj Na Pd) Fn(kC mE nF nl nK) mW(bH bL Hx Nt Vu) mZ(aO cO dF Kq Ut) nH(Af dA Mj Na Qn) Qh(Ky Nk Qc Qe) kC(dA dD dL Mj) kK(eF Lu Nx Vu) Nt(gC kG nN) Lj(aE aP Nk) nB(No Rg Rm) Bg(Aj nR) Is(Nm Qw) Nx(mY nU) aP(Cs Cu) dD(nl nK) mF(bH Hr) CvUg EdnN FbgC MjnF MnlX eFlY gLnR} nD{Vu(aC aK Ao Ar As aV bE Bo cV cY dA dD De dR eF Ez Gp Ha Hw Ii Il In iO Ji Jo kQ Kr Ks Kx Lu Lz MM Ms mW My Na NO NT Nx Oh Pa Pj Po Pz Ql Qn Qv Tr Ug Um Un Uo Ur Us) Pj(al An aZ bQ bU cB cD cN dB Dc dR Et Fr Fw Fy hC Ih Ij Is Jg Jj Jk Jm Jn Jq Js Kd Kq Lj Lu Lx Mf Ms Mt Mx Mz Nd Nr Ns Nv Oa Ok Pa Pf Pz Qa Qb Qe Qh Qn Rj Sr Tn Uh Um Vt) Tn(aC Ad Aj aO Ap bH Cp Cw Cx dD De Dg Dl Ed Ib Io Iz Jd Jf Ji Jo Jt Kg Kl Kq Kr Ky Lu Lv mM Mn Ms Mv NO Nt Nu On Oy Qw Rc Ug Un Ut Vv) Un(aJ aM Ax cN dM eF Fa Fp Fr Hr Ih Ir Is Jk Jl Kj Kn Kr Lj Lv Lx Mx nB Nn Nr nY Oa Oh Oi Pa Pc Pf Pi Qa Qb Qe Qh St Ug) Nx(aC aD aN AO bH bJ bR bX cB cM Ct Db dD eC Ed eF Fa Hc Hf Jd Je Jf Kp Kr Oa oN Pi Qw Rb Uk Vo Vv Tj) Qh(Aa Af Ar As Bn bS cA cK Dc De Ed Ii It Iu Ji Jo Js Jt Kq Kr Ks Lu MM Nj Nt Ql Qn Tv Tz) Ms(An bG dM eC eF Fb iJ Ip Is Jf Jl Jm Jp Kn Kx Mb Nc Nd Ne Nl Oa Oi Or Pz Qc St Tr Vv Wm) Kr(aJ bG bV dF dH hC Ib Ip Kj Lj mY nJ Nn Nr oF oQ Pa Pf Qa Qe Qv St) cB(bH Bn bU cR Cv dD dJ eC Fn Hr Ip Ki Lu Nd Nk Nl No Nt Rf) eC(aK aV bG cF dI dJ eF Fn Ip lX Na Ni nT Oi Qv Ss Tr Ua) Ed(bG bQ bZ eF fP Fr Gp Jj Kc kN Lu Ma My Nt oN) Ex(bZ cQ cX Fr Ik Jd Jl Jr My Mz nW oF oN St) Fn(aC aZ bQ bR cX dB Gz iH Kc kS Lu lX mZ Qc) Oa(Ar aX dD eF fP Ib Jo Js Jt Kc Lu Mm nO nT) Ug(al bG cE Fw Kx Lj Mn NN Of Pi Pk Rb Sr) Ip(al bR DB Jj kO lX Na No Oy Pd Uk) eF(Ao Cq Ji kl Lj Lv lX mZ Pa Pf Qb Wm) Lj(al aX fP Fy Kc oK Or Qn Us) Lu(aO Fa Jf Rb St Vv Tj) Ji(bQ dR Gp hC St Tr Uh) Pa(aC Dl Fa Jf Kj Or Vo) Ib(aZ bQ Mt Oi Qa Um) Gz(Kc Mv My oN St) Mm(al bG Kq St Vs) Jf(cD Im Nl Nr Pf) Jt(cD cE cT Fw Kd) Rb(bG Fr Nd Qa) bA(Id Jj Oy Qw) Nr(bS cA cK) Nt(Fw Qc St) Nu(Fw Qc Ql) Qa(dH Hf Sr) bQ(cR Jo Wm) Aa(Gp Kd) As(Jm St) Is(mS Tz) Jj(Al dD) Kj(Hq To) Qn(Rj Vs) bG(Na Ra) cX(al Ua) WmGp QbOr StmM OycT PfaC bRnC nTlX} lX{cF(Aj aK aQ aU aV Bn Ct cW Ed Ex Hx iA Ib iH iJ Ik Il kC kF kl Kj kO Li Lj Lv Mg Ms mZ nA Nc Ng nJ nK nT Nx Oa Of Pa Pf Rb Uk Ut Vt Vu Wm) Uk(Cq dE Dp Ed Fn Ih Iu Jf Jm Jn Kd Ko Kr

Figure 27 Continued

Figure 27 Continued

Pj Qn Qu Qw Rb Rj Sr Ss To Ua Ul Vo Vp Vt Wm Tj) Tn(Ef Hc Hu Is Iz Jg Jr Jt Jy Kl Kq Kr Ks Kz Me Mm Mn Nc Ng Oe Ok Or Pf Pj Qu Ss Ug Uk Vt) Is(Hf Ik Ip Jj Ki Ks Kz Ld Mb Me Mn Mp My Na Or Ou Ow Qc Qv Rg St Tr Uk Uo Us Uv Vs Vt) Kz(Ha Ik Im Iu Jk Jm Jq Lx Mz Na Nr Oa Pe Po Qa Qh Tv Tz) Li(Hu Il It Iv Jq Ju Kp Kq Me Mn My Oh Pc Pj Qu To Vs) Fb(Hu Jg Jt Kr Me Mn Nt Qw Rb Ss Vo Vt) My(Jr Lj Lx Mz Oa Pa Pe Pf Po Vt) Me(Ir It Iu Kc Pa Pf Tr) Vt(Iv Ky Lv Oh Pf Sr) Vs(Ij Ke Lj Pa Uh Uk) Iu(Kn Kp Pf Uk) Ld(Dp Hq Ir Oa) Kr(It Ke Pa) Ih(Na Us) Rg(Hb Nc) MnPa MtRb NhTo HqKc IkUs HcJn IpSr JmKs JqQn} bN{Qh(aI AI Ar cH cS cV Dc Dd De dJ hF Hr iJ Mu oP Pk Qx St Uk Ur Wm) Uk(Ad aI aW Dc dJ Et Fa Ih Is It Jm Jn mY nB nK nN Oa Pz Rm Sr) Wm(aI cS cZ dJ Et fP Gp Hb Ih Is Jn Ke Ko Nw On Uh) cS(Il Jr Ko Li Lj Oa Pz Qw Sr Ss To Tr Uc Uh) fP(Fw Hb iA Il Jm Jn Li Lj Oa Pz Qa Qb Sr Ur) Hr(aI dJ Ih Is Jn Ko Lx Pa Qa Uh) Is(hF Ib iJ Jj Jr Jv Qx St Ur) Ss(Ad Ap Bg Cu Et Fa Lx Pz Qa) De(Et Jk Ko Oa Pz Qa Tn Uc) Ad(hF hG iJ Il Jj Jt Ug) Ar(Ke Ko Lj Oa Qa St Tn) Qw(Fw Ko Lj Lx nN Qa Sr) gW(Et Jl Jn Jy Kl Tn Tr) iJ(Bb Cs Dc Lj Lx Oa) Ur(aI cZ Gp Jn Kk) Bn(Et Ko Pz Sr) Na(gC kF kO oQ) hB(Ky mS Nj nO) hF(aI Jn On Uh) Ms(mH nT oP) Lj(aX oP Pk) Oa(aX bV Gp) dJ(Ed Qn Rm) Dc(hG iO) Et(Nx Pj) Gz(mU nN) Pz(Jt mI) Qa(aE dA) FakQ FrhG NtnN TofR IhJj SraI KoNx LioK} nA{Ex(aM aN Bb Bg cP cS cX dE dG Et Fa Fr Fw hB Hu Ih Ir Jd Jl Kd kN mI Mx Mz nK nN Og oP Or Qe Rm Ul) Ib(aJ aM cB dM eF Fa Fb Fr Ih Is Jf Jk Jl Jm Kj Mt Mw Nl NN Nr Oa Oh Oi Or Qa Qe Qh Tn) Nx(aX bR cB cR Ct dA dB eF fP Hb Hf iZ Kr oN Qu Qw Rf To Tr Vt) Un(aJ AL aM Ax bH Cv Fa Fr Ih Ir Kn Lx Oa Oi Qa Qe Wm) Ip(aI bR cM dB dD Gz iH Ms Uk) Kr(Ax bG dF Lj Nr Oa oF Pa Pf) cB(bH Bn Hr Ki Nd No Nt Nu) Oa(aX bU fP Jt Nk Qn) Ed(eF fP My Qz Tn) Gz(Et Fw Is Kg Kj) Wm(Gp Ml Na Tn) Tr(Ji Jt Ms Qz) Rb(Jf Mb Nd Qz) Tn(Aj Ao Ut) Qh(Af Bn Ii) Qn(Fa Ha Lj) Aa(bM cD) Ms(Il Or) Nl(Jf Qv) Pa(cX Rg) Pf(eF Or) Pj(dB Mz) AfSr AsJm CqeF CtIc LxSs NabG TzIs HqQz JdnJ LjfP cXiJ} nN{Nt(aE aG aH aI Ap Bg cB cD dB Dc dR Ed Ef Fa fP Hb Ic iJ Jd Je Jf Jg Ke Kf Ko Kx Or Qh Qw St Tr Tv Ua Uc Uk Ul Ur Uu Vt tF) Jj(Af Ar aV bH Bn bS cA cB cK cO cR cV cW Cx cY DE dH dJ eF fP Ip Jf Ju Kr Kx Or Ph Qz Rg Tv Vv) Qw(aI Ar bG Bn bS cA cK cV dD De dH eF iJ Iu Jo Js Kx Mr Nk Nm No Nu Pj Ql Rg Tv Un Us Vs) eF(fP Hx Iv mP mU oN Ut) Nk(aI cV Ex Je Ug Uk) Qh(bS cA cK Ih Iv No) fP(aO Hu Lv Mg Oy Vv) Bn(cD Dc Et Jg Ua) aI(bB mI Mn Ph) Ex(Iv Rm Ut) Jo(Cv Kn Ko) Uk(bG Iv nO) iJ(Ip Mj nO) Af(Jg Ua) Ns(Cp Qz) Il(Cv dD) Ko(Jt Ph) Kr(bG Me) Un(Bc mP) Pa(dD dL) FrRm GpNd GzTv NrRg NucB LyRb IbKe SrNw QubG VsdL} hX{Is(Aa Hx iB Ij Ik In Iv jF Jj Jo Jt Li lK Mb Me Mg Mj Mr Ms Nc Nd Ng Nj Of Pb rZ) Iq(Aa Hr Jl Li Lx Ly Lz Me Mh Mj Mq Mr Mt Nc Nn No Nw Nx Ny Ok Pe Po rZ) Iu(iB In Li Lj Lx Lz Me Mt Nc Nd Nj Nk Nw Og Pg qV qY) Pa(Aa Hr iB Jl Li Lx Lz Mh Mj Mr Mt Nn Nw Pe qV) Aa(eD Hx Js Mb Mw Mz Nd Nf Nu Oi Pz Qb rA) Mj(Hu hW iB Iv Mb Me Nc Nd Ne Nh Nj Nk Nl) Li(eD hW Iv Mb Me Mz Nd Ne Nj Nl Pb Pz) Mz(iB Lj lK Me Mg Nc Ng qV qX) Nj(Lj Lx Lz Mh Mr Mt No) iB(It Lj Lz Mh Mt Nn Pe) qY(Hr Hw Jl Pe qV) Ok(hW Iv Mg Ng) No(Me Nc Nl) Lz(Mb Nd Pz) Lx(Nl Pb) Mb(Mh Qd) Nc(Js Lj) Nw(Hu Jr) FpIv MhNd NlPe JnJs LjjL} mP{Pj(aJ Ax aZ bQ bV bZ cB cD cH cX dB dJ eF Et iA Ih Il Ip Is Jj Jm Kn Kx Kz Lj Lx Mf Mk Mz Nk Nn Nw Oa Oh Ok Pa Pz Qa Qc Qe Qw Sr Uh Vt tF) Ib(aJ bQ cB CX eF Fa Fr Is Iv Jf Jj Kn Kx Kz Lx Mt mU Mw Nd Nl Nn Oh Qe Qh) eF(Aj Ao Ax Ch Cq Ct Dc Di Dk Ed Ef Ji Kj Mg Ng Nx Oa Pf Qn Wm) Un(aJ AL aM aP Ax bZ Fa Fb Fr Ih Ir Kn Lx Nn Oa Qa Wm) Nx(aQ aX bR cF cX dB dJ gL Ic Qw Tr Tj) Id(aJ dM Ir Jj Kj Lx) Kx(Fa Jt Lj Pd Rc Vv) Sr(Af dM Jo Jt Qa) Qh(Af Bn Dc De Jt) cX(Ex iJ Il Pa) Gz(oO oQ Qw) Oa(Af Jt Kc) Cx(aI bG) Ed(Jj My) nC(bR Jf) AacF WmaI TrJt HfQa QzLj JjUr KroF OhfP OrPa VvmW PiaJ} nO{Uk(Al Ax bA Bc bG Cq Cv Dc Di dJ eF Fw Ha Ih Ij Il Ip Ir Is Jk Jn Kn Ko Kx Lj Lx Nd Nl Nn Nr nT Oa Oh Oi Om Pb Pk Pz Qa Qb Qe Qh Rm St Tn Tr Uc Vt tF) Lx(aI cR Ct Fy Ib iJ Jd Rb Uf Un Vv) Tn(Ad Aj aO bH bL bV Ct Ef Ik Jj) Oa(Af aX bH Bn bU Ib Ip Jj Kx) aI(Al BC Cq Cv Dc Di hF Ur) hB(aO bH eF Ld Lv Nj Nk Oy) Ct(Fr Qa Qb Qe Qh St) Lj(cR Kr Kx Ld Rg Tv) Ha(Af Bn Kx Nk Nw) Jj(Al Cq Kr Ra Vt) Li(aX eF Rg Tv) Fr(Ib Rg Rm) Hx(Bc Dc Di) Kj(Cq Jm Vt) bH(Pe Qa Qb) bV(Lv Rb Vt) iJ(cX Dl Ip) Tz(Kx Qh) Ue(Cv Vt) bG(Hr Lv) AfnT AjQh AxKr BgIk BntF CqUg CwOy DiQg FaaY MwIb RbeF QbfP RgPa OhbL aUdR} gC{cW(Af aN aZ cL cO cX Db dD Hb Hc In Kc Ly Lz Mf Mj Ml Ms Ne Nh Nm Of Oh Or Oy Qe Qh Qu Rb Ss St) Ne(aE aK aU aV aY cU cV cY dA fP Hv Is Lz Me Ms Na No Nu oN pF Pk Ss To Tz Ub Uk Tj) Na(cP Hc KQ Lv Mr Mt My Nl Og oN Oy Pb Pc Pd Qt Uk) Ss(Fb Hb iZ Kg Kn Mr Ns Oi oN Qn Qz Uk Vp) Ms(aN cP eF fR Md Mr Or Oy) To(cV Ic Qt Uk Uo) Un(aF aX Hc Oy Uk) kQ(aC dD Gz Nu Rb) Mr(Gz Hr Nl Tj) Id(bB cI Kl Kq) cP(cV Iq Qh Us) fP(Gp Ly Nh Nl) fR(aP cJ dH Pd) Is(cV Ex Nt) kS(Ip Nw Tr) Gz(bB Pb) No(Ih Qa) Lv(Db Oh) Nh(cV dA) Ic(cG Mj) Rb(oN Uk) aY(Af Aj) cI(hC Jj) DdHc ExQu MtQg NlcV OrbM aOhB} mW{bH(aJ Ax bG bM cD dC dG eF Fr Gp Hx iA Ih iJ Il Jj Jn Kn Ko Kq Lj Lv Lx Mt nJ nL Nq Nr Nv Oa On oQ Pe Pf Pg Qa Qb Qh Qz St Tn Vv) Lv(aC aI aZ bG bR bV cB Cs cX dB dE dG eF Ex Fa Gp hB hC Kc Kj Kp kS Kx Kz oF oN Or Qh St Tn Ug Vv) Uk(Bc Fa Ih Is Jm Lj Oa Oz Qa Qb Qe Qh St Vt tF) Oa(aC aY cR dD Hr Hx Jj mU Nu Qw) Hr(Ax bG Gp iJ Ko Tn Vv) Lj(Aw cQ cR dD Fy Kx Qw) Qw(bA bI bQ Ko Qb) Hx(Ax Bc eF Fa) Rg(bA eF Li Pa) Dc(aC Nt Oy) Pd(aJ iJ Wm) aY(Fa Ju Qa) Bn(aI St) Cv(Jo Oy) Vv(Jj Uu) AfSt NtQh TzIs IbJk QaRm QbfP RhOh} oP{Lv(aC aK aL aO aS bE bH bR cB cX cZ dB dD dM dR eF Gp Hf hG Ib Kc Kx Ph Pi Pj Pk Qh Un Vv) Lj(aO Ar Aw bH cN cR cY dD dH dN No Ph Rg Rm) Nt(Al Cq Dc Ed Ic Jy Oa Qh St Tn Tr Ul tF) Oa(aC aP Bn De Ih Js Mj Nk No Rg Rm) aO(aI bM Jj Kk Ms Nm Nv Qh St Tn) bH(bM cD Kd Ms Pf Tr Us Uv) Kr(aI Ax bG dR Qh St) Li(bS cA cK No Rg Un) Rm(Nb Nn Nr Oh Qb St) aY(Fa Ju Oy Rc Vv) bM(Jt Pd Pg Vv) Ms(cB cU Pb) Hr(cD Kd Uv) Qh(It Nk Ut) Rg(Ax Nn Oh) Oy(Bb Kd Tr) St(Nk Ut) Vt(bE Un) Pd(cD Kk) aC(Pa Tr) dD(Lx Nb) AfUa CvJt EdJj ExHu IbJk QbaP JqPj PgcD} cB{kO(aC Af Aw bH Bn bU dD Dl fP Hr Ki mU Mz Nb Nd Nl No Nt Nu Pd Pj Sr) nJ(Af bH Bn bU Cv dD dJ Dl fP Hr Ip Ki Nd Nl No Nt Nu Pj) nL(Af bH Bn bU dD Dl fP Hr Kr Lv Nd No Nt Pj) nC(Aw bH dD Dl Hr Ip Kr Lv Nd No Nt Nu Pj) kF(aC Af dD Iu Ki Nt Nu Pj Un) mY(Af bH Bn cG Ki Nk Nt) kC(Af bH Bn Ki Kr Nd Nt) mU(bH Ib Nt Nu Nx) nH(Af Bn Dl Nt Pj) oQ(Aw bH Ki No Rg) nU(Af Bn Nx) mI(Kx Nd Pz) kN(Cq Ki Lv) Nt(kl nT) Ib(kP nT) nF(bU Nl) FbgW nRhB} nT{Jj(Al aS Dp eF Fa Fb Fw Iu Jm Kn Ko kS Kx Li Om Pk Qa Qc Ra Vp Vt) dR(Aa Af As Bn Cp Cx De Ib Ji Jt Kr Kx Nl Nt Pj Qn Un Wm) Nt(aV aZ bQ bV cY hB kQ kS Kx Ow Uh Uo) Uk(aK Al Ih Ij Oa Qa Qb) Af(bG Cv Dc Gp hB Ua) Ms(aQ cY Nk nU Nw Pz) Un(Co Ij Nw Qw Tj) Tn(Aj kG Kj Rh) Ib(bQ dB Tj) Pz(Kj Oy Ug) Qh(Ks Tz Ut) Pa(kS Oa Rg) Bn(aK bG) Lx(Oy Vv) Kx(Fa St) Ug(Nk Oe) kS(Kk Tr) FraO IlJm QaUt KjVt LjcR RfOh NwPj UoaK aIbB} fP{Lj(aE aP AR aW bM dA dJ Hb hG Hv Ik Jd kK kP Kq Ky Lx mY mZ nI nR nY Pb Pk Po Pz St Un Vv) Qb(aP aR cU dA dJ fR Hc Jd kK kP Lv Ma Mu mY mZ nI Nk Nt Of oN Pb Qe Qw St Un Vv) Oa(AR aW aY Iv Jd Kc kP mY mZ Vv) Qh(Jd kP Ma Mu Ng Nk Vv) Is(Jd Jo Nt Un Vv) Vv(Bb Lx Nn Sr) mZ(eF Fr Qa Tn) kP(Li Qa St Tn) Fa(aP aY Jd) Jd(Lx Oh) Pa(nH Oz) aO(nC oQ) IkSr QanI QenC JmfR NxnU} aI{kO(aC aO cG cI CX Dl Hr Io Ip Jt Kr Ld Mj Nt Pd Pj) mI(Al aO Cq CX Dl Ed Fw mZ Nd nK Nx Pa Vt) mS(Bc Cq Cv Di Nk Ub Ur) nB(bH Bn Bo Cp Cx Dl Hr) nC(bH CX Dl Hr Vt Tj) cX(kC nF nH nJ nL) Cx(kC nH nJ nL) nR(Bg Cu Dc Wm) nU(Cq Kx Lv Nx) Dl(nF nH nL) cI(mU nI nK) Lv(kN mU) Is(Qy Vv) Pz(Jt Uk) Kr(kF oQ) aO(kF mY) nL(Hr Tj) CqOy WmnH NtkI LxVv MuQh IpnJ JmUk bHmU} eF{mZ(aW bJ bM cD Cq iJ Jj Ju Kk Li Lj Lv Lx mI Ms Nc nL Nr Nt Oa Oe Pa Qw Uk Ut Vt) mU(Ax Ch Dc Ed Ez Gl Lj Nx Oa Pf Wm) kK(Dc Ky Lj Nc Nt Oa Oe Rh Ss Vt) Vt(lW mE mF mH mI) kP(aO Cq Li Ms Pf) nL(Aw Oe Ua) Ch(nB oO) Lv(kG nK) nI(Ed Wm) AxoO NtkI MskG NdmI JjnC LjnB bHoQ bJnK nRhB iOkO} Uk{kP(Al Dc Ij Ik Ir Is Jk Jm Oa Qh) nB(aC aE cY dL Ik Kx Nk Rg) Ip(kC kO mE nF nJ nK oO) mE(bH Cv Jm Vt Tj) Is(Ar dA Jd Mu) mF(Al Cv Oe Vt) mS(Cv Nx Pa Pz) nI(Al Ih Nl Nr) nK(dR Fr oH St) Qh(Ar dA dJ) mU(dD Nk Tr) Et(aW Vv) Lx(aR dA) Qb(aE dA) mZ(Fr Tn) kN(Lv Vt) oO(Al Kn) FbgW NxnU nCnL} Mz{hA(Hv Hx Iv jD Jt Lx Me Mg qY rX rY rZ) iB(aA Il Jo Jt Mg Mm Nx Of rB) jD(Il Jj Jo Ma Mm Nc Ni Nt Pd) jL(aA Hx Il Jt Mc Mg qT qY rY) rZ(Lv Mg Mm Ng Oz rC) lL(Il Jo Jt Mg Ng) lN(Iv Jo Mg Nc Ng) qY(Ma Nc qV) rY(Aa Ng Ns) Il(jU jV)

Figure 27 Continued

MehR MgjV NcrB lpfR PbjU bHmU} fR{Mj(aC As aY bL cG Cv Dc Dd dE dH Hr Ik Ip Ki Mc Mf Nx Pd) Ip(aY dC dE Ex Hu Ik Jd Kx Mr)
dE(bX cJ dR Ne Nk Nt To) aY(Bn Cq Ib Jk Jv Or) Ib(Kg Ms Oe Ug) To(dA dH Iv Pd) Jd(Gz Me Qw) Pd(Lz Mg Ms) Nj(Dd Is) Ik(Ad Di)
Ki(dA Mr) dH(Ms Ne) NtIl HrbL JmcS} Is{Ij(Ar cK Ct dA De Jd kP Qt Qy Vv Wm) Jo(cV hR hW iB iC jG jM jU rX) Il(hV iB jF jL jM jQ rZ) Tz(kO mY nF nJ nK) cV(Jd Nk Qw) nR(Af Bn Ut) mI(Ql Tv Vs) iJ(Ct Ng Qy) qZ(Ih jL Nl) oQ(Js Kr Rm) Nx(iB mS) rX(Hw Jt) CtLv NthW MskP NgTr IbdA JdhB} Qh{Ct(aQ Ar aU aV bS cA cK cY dA iJ Jr kP Mu) kK(Ar Bn bS cA cK De Ib Jt Nk Nt) dA(Aj Ar Bn Cp De Ib Jt Ng Wm) Ar(bC Mu Ng Of Qt Qw) De(aV mY nF nR) Ng(dJ iJ Tr) Af(nH nR) Ks(kP mU) cV(Mu nU) AjiJ BnnH BokP JtdJ KroQ aOnR} nU{Nx(aE bH cR cV hB iJ Jg Kd Ko Nv Ny Oa oN Qm Qn Tr Ua Uc Ut Vt) Un(Dc Ih Ij Jm Jn Ko Oa Om Tn) Ib(aA Jk Om Qa Tn) Jm(cV iJ Jj Ms Nm) Ms(Mb Om) Ic(Ax Kj) Tr(Jj Rj) St(Kx Ut) bG(Lv Rb) NmKx NrRg NtJg NdcV TnRh OkPj UrbH} mU{bH(aV bM Bo cV Ez Gp In Kd Pa Qg Tr) Oa(Af Jt Kc Ks Ql Ug) Pa(aX cX Fa Kj Or) Qa(Bo Ib Ql Tz) dD(Ez Nh Nl Uo) Ax(Ql Qn Un) Tr(Jj Jt Nx) Nt(dB Uo) Pz(Kj Rc) Lj(aX Ks) Un(Kn Vt) BnFa GzMb LxQv NkUo NlcV UcUg TncX IpNx QeUt JjcW OhaX aAdR} kK{Lj(bZ cS Kc oK oN Ou) Nt(bV dF dG hB St) Fr(Ib Rg Un Ut) Jt(Ad Dc Ua Uc) bH(bG bZ Lu Nx) Jf(Jj Nk Nl) St(Ib Nk Pj) Qw(bA Kr Tn) Vv(Bg bZ Lu) Gz(Ip Mb) Qa(Ib Un) Pj(Et Ok) bG(Hr Pg) ArOa CvJo LuKp UnVt} Ip{nJ(bR Db dD Ex iH Jj Kr Ms Na Un) kO(bR DB Jj Kr Ms Un Wm) Un(kP nC nH nI nK nL) nC(bR dB iH Rb) nL(bR dB iH Ms) Gz(kI mS nB) Na(kC nF) Oy(lW mI) JjlW KrnK UgoO bRkC mSiJ} Oa{De(aL Et iJ kI mS nI) Ar(aL Hb Jj Ke mY) kP(aX Jj Kx Qw) Jt(mS nB nI) mY(Lu Nx oK) kN(aC aO Rm) Af(nR oQ) Ti(Co Kn) Gz(Mj mS) No(kC nF) Kc(iZ nW) Un(mF nJ) aX(nB nI) BnmE NkkO IbkI JjnI aCmZ bZdA} oQ{Kr(aA aE aY bM dJ Hb Ko Me) Rg(aZ Bo Co Ex Kk Na Pi Ug) Rm(aZ Bo Co Ez Kk) Af(aE Kg Qm) Fr(Ch Ib Ut) Nt(aE dB Vt) dL(Jj Nk Qu) BnbR BobH DbUt DcUg NoTn UcKj HrUs OrdD PaaM dAhC} gW{Fb(aQ aV Aw aX cC Ct cV cY Dd dR Ed Ez Fp Fw Hq Ik Je Jf Jj Jk Jr Kk Ko Kz Lx Ng Of Pa Qa Qw Qy Rb Ss Ua Vv) Vv(Et Pa) BgNg PakS} Ex{aY(Af Aj Ar As aX bJ Bn Cp dA De Ez Ik kC Kq mS Ne Rc) Lv(cX kC mS nJ) oO(bE Nb No Rg) Al(mY nB) Iu(mS mZ) dE(mS nJ) kO(Bb Hu) CvkP QaQt VsaN cXnH} Li{kN(aF aO Ar Bn bS cA cK dA De Ha Ib Ih Jd Jr No Pe Rg Rm Tv Un Ut) Ib(kI mZ) Qw(Ar Kc) nR(Af Bn) oN(Kc oK) TioF NomF MbqY OmI UnmZ bZdA} Lj{Ar(Et Hx Jj Ke Qw) nR(bU No Rg Rm) kI(Fy Ib Rg Sr) Rm(kN mZ) aE(cS kN) aX(nB nI) dJ(Og Pk) iZ(Kc Vv) DeiJ NknY QznB QwkP UnmI} Lx{Vv(aE aR dA hG iJ iZ oO) Ng(aE aV dA iJ) dA(Hc Jt Ss) Ar(nB Qw) Ib(kI mS) Ut(kN mE) AwcH WmkO GzkC JdQw SskP OfiJ} bH{mF(bQ dR hC Jg Kk Nv Nw Ok On Pz) nR(Af Bn In) nI(Jj Nx Qa) Us(kF kO) Pa(kI mZ) TrmE QvnB UhnJ UmC PfkI cSkN} mI{Nd(Ax cH cV iA Kc Qv) Pz(cX Kj Oy Vv) Qa(Ib Rg Rm Un) Un(Ih Ij Mw) Pa(cR Kj Or) Ib(Mw Qb) DeSt JjKd JmKs} Tn{mZ(cR cY dA Il My Qz) nJ(Ib Nt Pj Rc Ut) kP(Ky Mf Qw Rh) kG(cR Nt Nu) nI(Aj Tt) NgPz QwnL} nR{Bn(aO Jm Oz Pb) Af(Dc Hr Lv) Nt(Cq Pb Vt) Oh(Kr Rg Rm) Vt(Jt Pj) aO(Nr St) CqUg FrUt NdcV TrJj} kO{Wm(bQ Fr Ij Lh Nw On Uh) aC(Bo Tr Us) Nx(Bb Vt) dB(Nt Pj) AlIl BnNr UacX HrUs PdcF bQcR} Jj{mH(cY dR kS) nB(Af An Bn) nI(Al Ed Ju) kI(Al dJ) kP(Dc Jm) CvkF EdnK FrnZ KxlW cXmT} qY{Mb(aA hR Ms) Nd(hA hR Mk) Oi(aA rX rY) Pz(aA rB) EtqV NnIl MclN MjrY HxhR PclL} Fr{mZ(cR Il No Rm Ut) mT(No Rg Rm) Ut(mS oO) IbkI RbkP RmnL RgnK dDkG} Un{Vt(kF kG mY mZ oO) Ax(kI nH nL) Dc(kF nH) BbnB BcnH LvkN QamE NwhF} Nt{dB(kC nC nJ nL) mH(bV cY dR Kf) Fw(kI nH) EtaW StnJ KxkI dRnK} Ib{Qa(kI mY nB nJ) nH(bQ Nd Nn) Mw(lW mS) Lh(kP nK) KenI OkmS dBkP} Nx{Vt(kC kF mY nB) iB(Iu Mt) CtnI HrKe HbmE RfkC mToN} Gz{Ed(Hu Mb) mS(Jm Ua) AlnJ FwHu RmkP VsaN cYmH dCoO} Ng{Bg(aE dJ Hb Hc) Pz(bF Gp) aE(Nq Qa) HxhR TriJ} Pj{dB(kC kF nC nH nJ nL) Dc(mY nI) KgoO OkmY} Hx{hR(Hu Ik Iq Iv Mc Mg Nj Nl) ArmH} nC{Rm(Qa Qd) dB(Hr Lv) BoaC CoIk MjhB UacX NwbR} nI{Kr(dG Qa) BnFa CvJo DcJt DeSt DliJ TraC OybA} mH{dR(Af An Bn Wm) cY(Lu Ms) RbPz VskS} mS{bG(Ct Hr Mf Wm) hB(aF aO) BgIk WmGp} Pa{Rg(kC kI kP) DlnH FanB OrmF aMoO} kN{Ut(Ir Nr) TrOy RmOh UrcS VtcV cXiJ} Qw{Us(kI mZ) EdkI JmcV KomZ bAnJ} nH{BoaC DcUv NoMw MjhB UacX PdcF} Fa{aY(AR De) bM(De kP)} Pz{kG(Aj Kj Kl) NunF aAiB} mE{Kk(Hr Pd) AfUa CvUr TrRg} nJ{BoaC NadJ UacX PdcF bQcR} nL{BoaC NoMw MsNe UacX PdcF} Ti{aY(Cs Fp) AdAj DdVv} Il{iB(Et Mw Qb) JljL} Jo{Cv(mF nF) Ok(jL jO)} Dc{MfkP UgoO dDmF} mZ{AxRg BbOy ImUt} qZ{Ns(jO Nl) JljL} Cq{CtdI GpOy} Iu{InjY aAjT} St{AlkP WmmY} Jm{MskP KskG} Kx{CtkG NmnB} Us{kF(aO Hr)} bQ{LvmF cRkC} nK{AfUa KrNw} rB{EthA NdhR} AaCvkC ArUeKe LyRboO NkdBmY QaOfaE QcOelW JtOkjO aUdRmF Constrained panels with 3 analytes, where 1.0E-9 >= 'AUC p-value' > 1.0E-10. Contains 2,637 panels of 13,646,915 total panels evaluated. :
gP{Ng(Ad Cu cZ Fw Hx Ij Is Iz Jj Jn Kk Kn Ld Lh Li Mh Mr Nq Nr Oh Pz Qh St Tn Uf Th) Ct(Ba cG Ed Iu Jl Jm Jn Kf Lh Ly Nx Pg Po Qc Qe Ua) aI(aK aU Bg cW Hb Lw Mg Mh Mi Mk Mv Nd Oy Qu Uk) Fa(bC cL dA Ef Hc Hw Jj Kq Mw Nf Of Og) bN(cV fR Hb Js Nq Nr Ok Qc Qg Qw Rm Ug) Qt(bA Cs cZ Fw Is Lh Mh Mr Nn Ok Tv) Lj(Aj dI Et Ez Hf Hq Hw Kc Kk Mg Po) fR(bC bL cG dD De Hq Ki Mp Pg) oE(Cu dF Fw Hx Kd Lx Nr Pf Us) kE(aW bB bV Cu Fr Kz Oi Uh) Aj(Id Kn nR Nw On Qh Vq) Mg(Cs Fw hB Kd Li Mw) Ib(Fw Lh Lx Mt Nw Tv) Oa(aY Bn Cp dN Ez Gp) Uk(Fw Jm Ke Kk Pz Qh) Th(aF Hx Il Nx Ri) Jj(Fw Li Mh Tv Vs) fP(Iz Jm Jn Ss Vo) Qy(Fr No Nw On) Qw(bZ Li Nn Pf) Of(bQ dF Is Ok) hB(aR Il Jn Ma) Qh(cV Ez Jk) Oy(dF Pf Tr) dB(kC nH nL) nD(aP dG Qe) kP(aH iA Qg) Cs(De gW) Lx(aY Ik) Mu(bQ Kk) Hu(nN nR) Nw(Un Vv) Wn(In Ra) cA(bQ Pg) nO(bV Nn) nF(nH nJ) EzUs MenN KeaR LhmU NxnA OkVv OrVs OwmP UuVq VtnR VukK bBmM cVlY dFgW} kE{Bg(aD bA DC Hr Jl Kf Ms Nr Nx nY Pc Ue) Qh(aX bS cA cK dH fP Ih Ip Ju Nw Qv) Tr(bG cP Jf Kj Kz Nu oE Or Rc) Vu(aK Ba Bo Ij Iz Ju Ko Lj Uh) Kk(bG Kj kN Ni oE oK Qe St) Oa(Ar bA bF Ip Mv Ni nR oF) Nv(Af dF Fb Jv Kc oF) Uk(bG cE Ij Jk Om Qc) Nt(aJ cD Cw Fa Gp) aI(dJ Jm mI Nr Qb) bA(Jm Jq Ju Qn Rc) Dc(Hx Ii Mz Or) Lv(cO oK oN Ou) Qa(cE Cv Kr oH) St(bH fP nD tF) hB(Kd Kp mI Vv) Nb(fP oK oN) Hx(Ad Cv eF) Pa(bQ Ha Us) oE(An Ch Qz) Ba(Fn Jt) Cw(bG Nu) Fr(dE Qz) Gp(Ha oQ) Nl(cV Jf) Ua(Jj Up) Kd(cP dF) Ny(Ju Or) On(Af Bn) bZ(lY Ok) nW(Ij Qn) AnNx CqbQ FbJq FnoP MtUp MxbG NiUs UcJt HrdF IbcT JgbH JlcE JmUv KjOf LioN cCeF dRnT} Wn{Us(aK bH cS cX Hr Hu Mn Mr Ng Qu Qv) Li(Af An Cx Ic It Mn Nv Vo) cH(bF cP Ii Kr Ly Ms Po Rg) cX(bQ cF Hx Iq Lj Nb Nl Up) Nv(Db eC Fr Ir Qy Uh Up) Ra(Bn fP Ng Pf Rg Uk) dB(cN dL Mt Qz Rg Tr) Ue(aN aW Hq Ic Vs) Hc(Co It Iu Pf Ur) Pj(Bb It Mp Mr Nc) Mw(Fn Hx Mr Qe) Hb(aA Hu Me Na) aW(aX fP iH Ii) cC(bC cP Na Up) Ml(cT Db Vs) Mm(bN cY dA) Il(bF cI Nx) Rg(bN Fy Nr) Oh(Ii Nx Qv) Vt(aL aZ kS) Vv(Cx Nh Tt) cN(Kr Ks Me) To(dE Uv) Hf(Ky Nt) Jt(aQ aR) Lj(NY) Pa(cT Qc) Pe(aA Vs) cP(bV Nx) dJ(Ii Ng) CtIb MeaL MvIn MxRb HwdH IcbQ SrKs StbF QvdL QuiA OkaU OzaO PfaN aAbN} nD{Tn(Af As Bn Dk Ef Et Ii kS Ml Nm Tt) eC(Ar dD fP nO Nt Nu oH Or Pj Un) Vu(aI hG Ip Iu Jf Jl Kd Lj Ml) Jt(bA bG Dc Gp iJ Sr St Uc) Kr(aI Ax cB dG Fr Jl Nq Qb) Ug(cD Ed eF Jm Lx Ms Nr Pa) Ip(Bc dA dD dH It lY oE) Pj(Id Im Jp Kn mP tF) Lu(Ao bH eF Un Vo) Pa(aX bR Gl Kc Kz) cB(Af cG fP Nu oE) Jo(Kd Ny Rb St) Un(bH Fw Ni Ra) Aa(bQ dR Vq) Nt(dB Qu Uo) Na(dJ Kj Wm) Qh(Nu Pg Vs) bH(mW Uh Uv) Ao(Bg hB) Bo(aC dD) Ed(oF Uk) Fa(Mm Qn) Ib(bA Nd) Rb(bQ Kj) Jf(bA lX) bG(Hc Tj) eF(Fw nK) oE(dC Pd) CxFn WmaC ExQd HaQn NrTv MmUh HxdI IiSt QadD QbaI QvJk JjKd KsLj VvmW} bN{Et(cS Hc hF Hr Ib Jt Lj Ng Oa Rc Ur) Uk(cH dA Dg Ip Iu Ko Lx Mn Qa Qb Ur) Wm(aW bQ bV dA eC Jr Lx Ok Pz Tr) Hr(fP Gp iJ Kk Mt Oa Tr Um) Pz(Af aI Ar gW Jj Jr Ng oE) eC(Ad fP Ih Lj Mr mY Qh Tr) Oa(aR dJ hF oK oP Qw) De(Jl Jp Jq Sr Us) Ih(fP hF Ib oE Qw) iJ(Co cS Cu Ip Qb) fP(Fa Ir nN Nx) Lx(hF Rc Ur) Tr(Ar hF Ng) Qh(dA dI nN) Lj(dJ Ko lX) Vq(Jh Mu Ng) Co(hG iH) Hb(cS Fw) Qa(dJ Pk) Qb(dJ Pk) Ss(Mw On) Jm(aI cS) Jr(aI Qw) Uh(Aw Ur) AdUp AjUc AxiZ BnJq CshG CuoE DcQx ExnN NqgW TnlX IsJd JjUr JnhB VuoP fRgC} lX{Oa(aY cR Cx Ik Il Kf Kr Ks mM Pj Qn Ue) Tn(Af Bn cR Fy Ik Iu Mf Or Oy Wm) Fn(Fp Fw Ib iH kF mP Pj Qa Qb) Jf(aH aI aQ cD

Figure 27 Continued cE cV Fp Lv oE) Pz(Bn Jj Ju Kj Or Pj Rc) Kj(Jm Kr Nj Pa Qz Vt) Kx(Hx Mf Qb Ra Vo Vv) Il(aQ Ne St Uk Vt) Jo(aU cY Pk Rb Tr) Bn(Cq Ct Mf Qa) Or(Cq Ij Vt Vu) cV(Lj Nx Qa Vu) nT(Ks Mq Ow Ql) Lx(aE cR hG) Tv(Dc Pf Vu) Jj(Bc Is To) eF(dK Ef Oy) Ib(Qd Ra) Tr(Nx Rb) Jm(iJ Uv) Uk(Fw Oh) Pj(An Et) aY(Ju Wm) AfRi MboE MyRb TzPk StUt KkUn KroP LjUg NxaK VtiJ VukK albW} Th{Wm(bI cK cL cU fP Hc Lv Lz Ma Md Mr Or Qu) iH(bB cO cW Jp Lv Ma Ne Nh Nl Qw Vv) Nx(eF Et fP Hx Mk oE oF Ql) Cs(Cp eF Fr Fy Je Mh Nb) Ri(aF aM bI Kk Lv Us) iA(bA bR Il Jl Jy Mn) Up(Hx Li Lx Qa Rm) Ng(Kf Li Lx Oh) Ko(Bb Cw Ed Ma) Ur(aA oE oN Qw) Vv(aK Fp It Iu) iJ(aF bU dA Nq) Co(Fa Ij Jl) Lv(Lj Mu Rm) Il(fP Je Ql) Pz(oE Of Om) bI(Ax Lj Oh) Aw(Nq Qa) Ed(Me Qw) Lx(Ao Kn) Mj(Cp hF) Mu(Fp Ld) Ib(Rm Us) Li(aF Qw) oE(Hx pF) oN(Hr Ow) AxeF MtQa IhIk IuKn JoRm KipF LjcU OzbG} eM{aV(cS fP Iq kR oH Qy Rm) Up(bP dI Pi Qa Qb Vo) dJ(Ao Je Jo Jy Kp Rb) Ri(aM aQ bB Fw Hc) Vq(Ha Kg No Of Pi) oE(eF Ii Ji Ju Ld) Jf(Aa dD Gz Hv) cR(Bb Hq Ul Uu) fR(Hf Ik Nc Nj) Nl(Hw Qw Vo) To(dB gC Jo) Rc(Nu Ph Ur) Qy(aQ aU Lz) Ju(CX Il) aI(Hr Ji Vv) dA(Oa Qa Ra) dI(Aj Nt Vv) Fa(Jr nW) Nn(Bn Ut) Rh(aX Hc) fP(Kr Pg) ArJl AsKn BoMz CpQd CxUa EdKo TjJs ExNw FwUt NtHv HrPz RbaQ aKoK bWdD} fP{Qb(aO Ar aV bM cH Fr Ik Jo Jq Ng Nl Oz Pz Ut) Oa(aP bM dA dJ Hb hG Hv Ik Ne Nk Nl Po) Up(aY Fa Ir Jn Lx Oh Oz Qa Rm) Lj(aN cH Ex Kx Nk Nl nW Qe) Vv(bM Ip Jm Jq Jr Li Oh Ok) Is(Ct Ma Ng Qy) Sr(Ct eC Jt Ut) Qh(Ar Ct Ik) Lx(Ik Nt) Jd(Nw Qa) cB(nA nC) eC(kO nB) kP(eF Nr) AaJt CqOy FabM MsgC NgPz TnnR IqdJ QemM JjaW JoVq PaoE dRnT} eC{nJ(aQ cS Cv dD Nu Or Pc) nL(aI cS dD Nt oK Un) nF(cF Ms Or Pj Un) oQ(cL kQ Nj oO Pj) Lj(kN mZ nT Qw) mI(Ed Kx mE Nd) kC(aK Nt Or Un) Lx(aR aW Ql) Ni(mS nA nK) Tr(kK Mm nA) mY(cW Ip Mt) nB(aI Jf oF) kO(dD Nu oK) Fa(aP Ss) Fb(Aj Qy) Oa(oH oK) nO(Hb Qa) mU(Ms Nu) mW(Lv Qw) WmnR NgQh IbIs IlkN LiNx UnnH PjkF aKnI aVnA mMnW} mM{St(bU cJ Ez Ip Jd Kx oP Pd pF Tz Ut) aI(bC Ij Im kO Kx Nd Ok Ur) eF(bM dN Ik Is Oz Vt) Qw(bG Ij Ny PF) Fn(dG Kc mE oF) Lx(Kc oF Qz Uk) Tn(dR Ip Pb Vv) hB(Ax Hx Kp Qa) Gp(Ha Jm nT) Ct(Fr Kq) Dc(bB Ue) Lv(bV dF) Ib(Mt Mw) Qh(dB pF) Jj(Ko Ua) Kc(Li Lj) Ok(Qz Un) AjJg FrPb IhUn ImUk HbVu IsUv LibZ UsVq dDnT} Uk{mW(bH Fr Hr Jk Lv Nn Oe Oh Oy Pb) mE(cB Cq cW dR Lv Nk Oe Tr) Qh(aR aV Jd Mu oE Up) Ip(Ex hG Mu Nx) aR(Et Is Nn Pz) nT(dR Lj Oh Pb) nK(bG cB cY Lh) nO(bH cM Fa) nB(dD dN Iv) Fn(mZ Pz) Lx(aW hG) Is(oE Qy) Sr(aI mP) Qw(Cq Jm) Vq(De Ua) dA(Ih Jm) gC(bR Nl) kP(eF Tn) NgPz JqNx KnmZ KxmT} oE{Ex(cE Dp Hw Kc Kf kG oN Rm) Qh(Ar De Ib Jd Of Qw Vv) Pa(aV dL Jq Mb Of) Is(Jd Og Qe Un) Vq(Aj Fp Ni Un) nT(cF nI nK Oa) nA(dA Ed mF Pj) mI(Dc dE Ql) nJ(aE bU dC) kN(cO nR Ou) Mb(bF cE) aP(Li Mt) mZ(Je Mv) kO(aE dC) ArLj EzmU HrmW PzcE QwkP NwUn NxoQ OfbF OrkK UslY UvmP UtlW bUnL} hX{Is(Lx Nl No Pe Po qU rX) qY(Lj Lz Mh Mr Mz Oi Pz) Me(Jl Mh Ok Pe Po Pz) Iq(Fp Lh Lj lK Nd Oh) Iu(Jl Mh Nn qU rZ) Nc(Lx Pe Pg qV) Pz(Lx Mt Nw Pg) Mr(Mb Nd Nl) Nj(Jl Pe Po) Lj(Iv Mb Pa) Nd(Nw Ok) Nl(Jl Mh) Pa(No Po) iB(jY Li) FrjD LzMz NfrZ NhHr JljL JtOk} oP{Lj(Bn bS cA cK cU dC dF dG dL Ha Ib Sr Tv Ut) Lv(Ar aY bG iJ Jd Je) Fn(aC Nm Qb Vv) Up(aC Ky nA Pd) aO(cD Kd Ko Pa) Vu(Iu Jr Ql) bH(Nb Oh Un) dD(Ch Jj Vt) Ms(aF cY) Qh(dH Iv) Kd(aC Pd) Kr(Li oH) Oa(Ir Pd) Oy(bM dJ) CqcB EdnA NtaI HrbM TnaC ImUt VqkF PjmP} nO{Lx(bH bL Bn De Kx) Tn(Af Hr kG Kx Pb) Oa(bV hB Kj Ld Ue) aI(Gp Ip Jm Nd Nj) eF(aO Bn Jj Nc Up) hB(aF cS Ik Vt) Ct(bG Jk Nd) Fa(Af Bn Rb) Up(Ke Mk Nn) Ax(cC Fn) Ha(Cp Cx) Ue(Ip Pz) Jj(Fb Ko) Vu(dB Uv) nT(bH Bn) AjSt FrUt TzJm UcKj IbLi RbQa UnlY} mP{Pj(cE cM dF hB Ij It Js Mw oF Pb Qz) eF(cX Ez Gl Lj Oh Pa Rc) Ib(aM aP Ih Oa Oi Qb) Up(Fa Hf Mz Ni NN) Nx(aO dA Qu Ut) Un(bH Hr Oh Qe) bG(Ao Bo cX) Cx(iJ oQ) Kx(bH Oa) Vu(mW Uv) WmbR FamW ExJj GzdG IdQb IiQh KriA OhOr} cB{nJ(Aw cR hB Kr Nk Pd) kO(cQ Cv eF hB Ip Nk) kF(Aw aY bE bH Ko) nL(Aw hB Pd To) kC(bU Cv dD Dl) lY(Ji mE Ms) mY(Aw bU Hr) nA(Af bU Pd) nC(Af cR hB) Di(kN mZ) Fn(kI nF) mI(dA Pa) mU(Hb Wm) oQ(dL Nt) AanI NukI LumS} Qh{Ct(aK aR aY cH Dc dE Hx Js Nj Up) Up(aE Aw cH cS DE) Ar(Ez Hx Ib Jj Oy) Ng(cA cK dE) Jj(dA Mu nT) nN(It Nk Tv) De(aI cC) Js(nF nR) dA(Ad Ik) AjaV BcnA CwaI WmkO ExQt MuQw JdhB KxnU LikN PjkK cWkP} lY{Kx(aZ Bo cV Kr Na Ql Ra Rc) Kc(Bo cQ cW Hq Us) Jt(aH cD cE Uc) Ib(Kr Tn Ug) Qz(cV Jj Kd) aI(Ad Ii Oy) Kd(Or Pj) Pa(Ez Kz) mW(Cs Kj) BnKy BoNx CtMy DcIi FnQv FwUs NrKs NtnR MfbG MlQw TnIl RbPz QcKr OrdD UvVu} nA{Ib(aP cN Kn Kr Kz Lj mU Mz Nd Nx Qb Ug) Vu(aK Bo dI Ez nJ Or Qv Qz Uv) Un(bZ Jl Nl nN) Lx(Jr Pj Qn) Fn(bR Ji) Kr(iA oQ) Nx(aE bH) Pj(Sr Vt) AaKd BcIp DlPa QncV UpkC bQcR} mW{bH(Dc hC Ij Jg kO Li Mf Oh Uu Wm) Vu(aF bM dI Iu Ky Mf Qa Ua) Lv(aM bZ Oa oK Qw Vo) Hr(bM St) Oy(Ad dJ) DcHx DkSt FabM FnOz HacY MsOa NdVv JmUg JoVt JubQ LieF LjaE UuPd} Is{Jj(dI Hc Ib nT Qw Qx) aI(Hr Jd Jo Mu Wm) iJ(Aj Jd Jo Of) cV(Ez Lv Vv) Ct(Nx Up) Wm(dA kP) gC(cP Hf) jI(Mb Qe) MjfR IbdB IlqV IvqZ JoqY KnTk KsmI UtkN VukP dAhB mSnJ} Up{mU(bP Hr Lv nL) nI(cP kF kO Ni) oQ(Bb Jj No) Ik(kO nR) aC(kO nB) fR(Ne Oe) gC(Kq Qt) nN(Ed Lh) AdNg NonB LvkK LxcH KkmT LicS LjaE RikF RfnC OaOg PbnR aOkN aQnT nJnW} aI{Pz(Af Aj Bn mS Of) mI(Il Ip Kx Oh) mS(bC Gp hF Ip) nN(Io Jo Ju) De(Lj Oa) Ur(nR Qt) kO(Mm nR) oO(Dc Ip) AjSr CpLj EdnU TjkC KlVq VvkF cInJ nCnH} nT{Jj(Dc Jg Nc Qg) Un(bZ Lh Nk Pz) Nt(dB Qn Tr) Vu(aV Hb Us) Ms(cX Tr) Tn(Ct Pb) Kj(Jm Uc) aY(Fa Qv) CxGp WmIp GzkC TraC TvLj QaiJ QbKx OrdR PjcY cXmI} gC{Ri(aK cP dE Jn Jr Pb Pd Qz) Ne(Fn Ha Ua Uc Ue Un Uo) fR(dG Ex Lu Mj) Mv(iJ iO) cW(Nq Ug) DbdE FncP NuoN LvhG UcHc RbQt PzkS OhiZ} Lx{Ng(aU aY cY dJ Hb hG Qw) Vv(aY bR cH dI mU Qw) dA(Hb Hr Oy Un) aR(Jj Qw Ss) cH(Jt Of) AjiJ FnmZ NtaW MjfR HcQw KcoN KqaY KsmU} Fn{nK(bI cY Fr Gp Ms) mZ(aM mT My Ug) kO(Gp Na Qc) Cx(kC nJ) aC(kC mU) nN(Kc Ma) oQ(No Un) AxkP FwGz MskG NanJ LikN bHmE} Ip{nJ(Bc cC dB Rb Sr Uf) fR(Hf Kq Nj) kO(dD Na Rb) nF(Ib Rb) WmkF ExKk UeoO IliB JjVv RinI UvmU dBkC lWiJ} Lj{iJ(Aj aR Cp No Qw) dJ(aR Iv Rg) aE(Kc oK) dA(bZ Pk) kK(bG oF) AraL BnnR DeEt GzKx NjKz JoiZ OrnB UgmU aXhG} nN{Qw(Af Ih Kr Mh Mk Ph) Ex(Ir Iu No) Bn(iJ Ko) eF(Gz Oe) CpKd CsJj CvJt EtKr NmKx NoSt InbH JoQm aXiJ} mI{Nd(Gp Hb Kj Oa Pi Pk Qc Rb Vv) Pa(dB Dl Fa Ib) Kx(Ha Oa) AxRg MzmZ HbNx QaaC QcOe QeUt JjLd} Tn{Ng(Ar dA dE dJ Pb) kG(cY dR Jo Un) nJ(Ed Ji Ky) Qw(De mZ) Kx(kP nU) AjdA AskP WmkO NooO OrmZ} qY{Mb(Hq lN Lw Md Mi Ns Oi Pd) aA(iB Iu Nf qT) lN(Ne Nl Oe) Mm(Et Nd) MaNd MzNj NcJn OiqV} Vu{nI(Bn Jj Jk Kx Po) nR(aO Kr Pg) kK(aC aU Iu) Oa(mY nU) kP(iJ Qw) HbIW KdnU KknJ cUmZ dImY} Vq{Ik(bV cF cJ dM) Ng(Gp Jo Ut) Aj(bO eF) De(aQ bQ) tF(Jo Qt) AanI CpoF MgkS UskP UtkK} fR{Mj(aO Hu Ky Mx Oz) Ib(Hu In Jq Ky To) Jd(aY Nt) AfaY CvIk MfMs NhdE HrUv HuTo} mU{bH(cE Ns Uv) Af(hC Ua) Qa(eF Un) AlIl BgOh BndF CxhC FaIn NudB IrUv QwKr QvJm KjdJ UgcE} Oa{Ar(Ct Et kI nU) De(aE Jj) kP(Lu Og) AjiJ MjnB MsnU JokI JsmS KckK RgbZ bUmH} eF{mZ(Hx Ko Pf Wm) kP(Aw Mf Qw) Pd(kO oQ) bJ(kK nL) GzkK TonJ QwnL nKoH} nR{Bn(Hr Ik Oy Qb Rg Rh) bH(Hf Qb Ug) Af(Jm Ua) ExHu QuNx JoVt KroF} Mz{jD(aA Ik Oz Pb) jV(hA Mk Nj) MaiB MdrY MsjF NjjL JjhA JolM rZlO} Ex{aY(dJ Ib Lv nC) Qt(Ih Nw On) kO(Al Bc) UbnC HunK IbJk cEnJ} oQ{Kr(bH dB Ly nI) Fr(Af Dk) dL(Pg Ut) NodB NtIc TrPd KkLd QlbH} kK{Cv(Jj Nx) Nt(aJ Dc) Qw(Ms Pj) FraO HrbZ StUt NxVv UnaM PdbG} Tk{Fb(Ld Mm Pj Qu) Hb(Ik Nd) FaFw HcOh IoLd RgOr} nI{As(Jm St) Jj(Dp Wm) AfFa DgiJ NnKr LubH UcJt NxaX} Ng{Wm(Et On) BgcH CvJn DciJ EfgW FriZ TrUt PzbQ} kN{Dc(cS Li) Ut(Im Oh) AxRg GzdR HrcS LicR UvVt} nU{Nx(Cv Fr On) Jg(Jt Pj) NdiJ IbSt} nH{Ms(Nc Nk) bG(Ur Wm) AjPa NadJ UnaM} nJ{dB(dJ Nl) CxRi MjhB KrNw NxVt aXcZ} kO{WmSt NtbR JjdD KdcR KrNw QlbH aXcZ} Vv{De(Et Ok) Ti(Ax Ed) BggW BnEt} mF{bH(bM dJ Uh) HrJg PzPd JmKs} nL{cR(Fr Kd) CxRi MjhB MsNk aXcZ} Jj{ArRm DeOn WmkC NnaR IhJd} mS{bG(Lv Uh Ur) NkhB OkPj} Il{BgmZ FrjD JmiB aYcS} Li{Qw(De Nx) dA(Kc oK)} mH{Nt(bQ cD) dR(Jt Ph)} kI{WmbQ NtKo NlcV IbOi} kP{AsSt DcRb WmGp RabV} Cq{Oy(dF Fb) CtcK} Ri{Cx(kC kF) UrkF} hR{Hx(lK Nf) NnJo} oO{FrbJ NdRb TrKj} Bo{aCkC bEkF} Dl{PzkG OkhG} Et{ArCs JtaW} Fa{KqaY aPhB} Nl{JfmZ dBkC} Un{QamY NwcS} bZ{QbdA RgcH} nC{GpHr NvcX} nF{MjhB PakS} AjBgdJ AsStmY MeNxiB MgOklL IqaAjQ JmKsmE UsbHnB dBmTiH

Figure 27 Continued

Constrained panels with 3 analytes, where 1.0E-8 >= 'AUC p-value' > 1.0E-9. Contains 3,832 panels of 13,646,915 total panels evaluated. :
gP{al(aW BC bQ bS cE cG cK cN CO cY dA dI Ed Ez Fw Hq Ib Jn Jy Kk Li Mm Ns Oz Pb Pd Pg Rm Ss Tn Ua) Fa(AR Aw Bn bW cK cN cR cV cZ dI dJ Gp gW Hq Il Io Kj Lx Mq My Pd Qg Qw Ua Uo Ut Vs) Ng(aY Cs dG dM Ed Hb Id Ip Jl Jp Jq Jr Kd Kf Mj Nn No Ny Om Qa Qg Qw Tv Uc Vq) Ct(aA aY Bg Co cS Et Fy Ii Ip It Kd Kk Kn Pa Tn Uc Ut Th) Mg(aA Ax Hb Id Is Kf Ko Lh Mh Mj Mr Mt No Nv Ny Qh St Tv) Oy(bA Cq Cu dG Fw hB Li Lz Mh Mp Mr Nn No Nr Nw Oh On Pe) oE(Ax bF bQ cE cU Ed Hb Jl Js Ke Kf Me Mj Nd Nw Qw Tr Uk) Qt(cC cV dF Ed Hu Hx Jj Kd Kk Mp No Nr Nw On Pe Qh Vt) Mu(cV cZ dF dG Hx Jj Mp Mt Nn Nw Oh Ok Pf Qh Us) Ib(bA bZ Cu Dk hB Hx Jl Kf Ld Mh Mr Mw No Po Ua) Aj(Ax Cs Et Fw hB Hx Ld Lh Mh Mr Mw Nv Uc) Lx(Aw bN cH Ef Ez Hu Jd Ma Mh Mv Pd Ra Ss) Uk(cZ Ed Et Hx Ih Jl Lh Li Mw Qa Qb Qy Rm) Lj(cJ Hb It kE Mv Nk Qv Ra Ul Uo Up Vs) Qy(aO aY cT Et Jl Ke Li Nr Tr Tv Uo) Qw(dF Fw Lz Mp Mt No Qb Qh) Oa(Hf Hu Iv Mv Nk Pd Up Vs) Nw(bN cC cV Jj Ms Nx Ue) Li(bS cS De gW Kc Rg) Vs(cS cZ Io Jn Ke Qh) nD(bW cN dF Jl Ky nU) Of(bZ dG hB Hx Wn) Ok(Ap Ef Ik Jh Jt) Vv(Et hB Kd Kk Qh) bN(aJ Fw Ih Ir) fR(Af Bn Ic Lh) Jj(Is Mr No) nR(aC Ch kG) mW(Db Fp kR) hB(aW cA hG) kE(Ax Ua Vu) Cs(cA Rg) Th(aZ eF) Qh(aV De) Ke(Jd Jh) Kk(aA cR) bQ(Lw Mi) lX(Db dK) mP(dF Nx) mZ(Hc Oz) nF(kO nL) EtaW MknO UeWn IsOg QadA KylY UgaY bHmU dBkO} bN{Uk(Ap aR hF Hr iA Il Ir Jr Mu Mw Nm Nn Nr Ok Qw To Tr Uc Up Wm) Ss(aI aX Ba bW bZ Co Fw Ih Nq Ok oP Tn Uc) Qw(aI aY bV cH dJ Fa Ir Li oE Pf Tr Wm) Oa(aI aO bZ dA Dc Hv iZ Kc lX Pk Up) Wm(bB bF bZ Ij Ip Jm Kk Mt Qa Ti) Qa(aR aY cH HF Jr Mu Up Ur) Ur(cS dJ Hb Ih Jr Ke Nw Um) gW(aU cY Hx iA Jr Uc Uf Ut) De(Jm Kf Lj Qe Rm St Tt) Fa(aY bM dJ Hr Hv iJ Qn) Pz(cV hF Ib iJ Of oK Rc) fP(Ax aY cH dJ Is Iu Lx) Ad(Aj Kc kE mS Ng Rc) Et(aW Mm Mu Of Qn To) Hr(bQ bZ cH Ir Ke oE) Ko(aX hF Ms Nd Ng Us) Up(Ax Cs Cu Dc Fw Rm) Jr(bV bZ dJ Ih Il) eC(aI Is Li Mz oQ) iJ(Ax Fr Ih Li nN) Wn(bH Ha Nx Vs) hB(aW dJ hG Jm) Ar(Id Kk Qe) Bn(Jm Nq Uc) Db(iH nC oQ) Lx(Hb Il Kc) Na(kC mY nN) Tn(aR nN nO) Rc(Dg Nd Vq) Qh(aR aV Nj) Jj(aW It Jm) cS(iA Jn oE) Dc(mM mS) Tr(aR bV) Sr(hF Ng) Qy(bZ Uc) Lj(aG aI) Nx(Hb Jq) oE(cE Nd) BbiA BgkQ CuhG EdTh ExaY FnIh FwnO HxcH HcoK IsVs JnbV JtOk KeUn UsdJ VqbJ PfkN aInN aKaV cZhF} eC{nD(aI aQ Bg cS Cv cY dA Kx Nk Pc Ub Uc Tj) Lj(Ar aV dA dJ Ha iJ Ju Nj nO oK Un) mY(aP De eF Ii Is kQ Ni Oe Pe Pz Un) Lx(aP fP hG Ii kQ oH Po Qv Un) kC(aI aV Bg cS dD dJ Kx Nk Nu) oQ(cQ Hf Iu Oi Pk Ql Qn Rg To) Fb(Ct Id Kk Ng Oa Qn Qw Wm) Qh(Ct dA De Jd Kk Mu Qw Ss) Oa(Ar Ax cS dA Kc kQ mZ) nO(Ha iJ Jm kF kO Pk Rb) nL(Al Bg bI dJ Kx Nk Pc) nJ(aI Bg oH oK Un Tj) kO(Bg cS Kx Oi Pc Ql) Tr(mE mU Of Qw Vv) mW(Jl Oi Qb Vu Vv) Ip(Il mP nF Wm) Wn(Jq Kx Mm To) nA(aI Ar Ms Na) kF(cY dJ Nt Ql) Ib(Ih Kn Nw) bZ(Ma nF nK) nR(Ji Nu Pj) Aa(Jt nI) Wm(kK kN) Ng(Bg Tn) Li(dE Up) Nx(Js Ke) nT(iA Tn) mF(Cv Dc) mM(aI Vu) mU(oH Ss) nB(Ks Pc) MzVv NinU IkkP IlIs HbmI PzkK OhkN OimP OmN UnmS PaPd bInF cHoK eFnK} Vq{Ng(Ar bI cB dJ Lv Nc oK Qc Qt Uo) nJ(bE dD fP Ji Kp Ms mZ nW Pd Ql) nC(aC aI aK cV Kk kO Kp mI Ql) Ik(An aX cS cV Jn oF oK oN) lY(Gp Ha mF Nc No Ph Qz To) mH(aE Gp Jf kE Kj No Or Ph) mF(aX Kc Ks Nk No Pa Qc) De(aI cZ kS oF Us Vv) lX(cV Hu Jj Kg Ks Pk) nH(aK bA bE fP Ju Or) kF(cS eF hB Ju Jv Pc) Qc(lW mE mI mM nT) mS(cF Gp Hw Ji Nw) nB(Fb Kp oH Pd Vv) Aj(aO bI cY oN) nN(Il Js Ju Sr) lW(Kc Nw Ph Vs) mI(Kc Ld Ml Nw) kE(bA Hx Mz Or) Ib(An Fb nK) nR(aC Mr Vv) nT(Hu Jv Og) kI(Kj Ml mZ) kN(Ma Nx oK) Cp(bO Uk) Mg(dA mP) dJ(mW Vs) nU(Jm oH) mE(Ir Kc) nI(eF Rc) nK(Kg Ld) EfoF WmkO FwQw MzmZ IomW JhUk RakP QtdD JttF OmO VomP PhkK aliJ aKmU dRmM} nD{Ri(bQ cB cX iH Oa Qd Ue Ug Uh Um) Kr(eF Ih Kx Li Mn Nw Ok Ow Qc) Ji(aZ bA bF bG cE Kd Kk Kn) Ug(Hq Mm Nu Ny Oh Pf Qh St) Pj(cC Ha hB Ir Kf Mw nN Oi) Un(Im Iu Li mY Nl oQ Tj) eF(dB iO mY Nm nN Nr Qa) Ms(Lx Nh Nj Nn oP Qa) Ip(aZ cC iH Mr Rb Sr) Oa(aC Gp Kx My Or Qn) Vu(Bn cD Fw mZ Og Tj) Pa(Ao aZ dD Dg Rb Vv) cB(Aa Aw Dc hB Lv Pd) Ed(aX Bg Nu Ou) Tn(Hr Ij Ik Tj) Jo(cE Fw Sr To) Jt(aI aY Kx Uu) Lj(bZ Jf oN Ql) Nr(Ld Ph Ql) Is(Ih Jn Pd) Qa(aC aP cN) St(Ao Or Qn) Qh(Nm No Or) Aa(aZ Bg) Mm(Rj Tr) Na(Fn mS) Ib(aM Qe) Pd(cF Tr) Pf(Or Ql) BgQb WmNx FbNt GpUr NuUk LuJd NdPi JfbF QwcT JjcD KjQn RflX OybZ aEoE aInB aXcZ dBdJ} kE{bQ(iJ Iu kF Nj nT nW Ok Ra Ua Uk) Bg(Aj Hx Ik Jv Nu Pb Pe Pg Ql) Vu(Aa aU bA bG cT Lv oE oH Qd) Kk(dF Jt Lu Ma nR oF Ok Pd) hB(kG Nl Oh Pa Qh Tr Vo) bG(Co Jv Kd Ok Qd Rg) Cv(dF Jt oF Qv Ue) Dc(bB cC It oH Pj) aI(aM Ij lY Mp nB) cE(Jo Pd Qe Ug Vv) Ua(aS bA Cx Nx) Kn(dF Fb Nx Pj) Nv(Cx Jt Kp Or) Uk(bA Ir Kq nB) Ba(Ib Qt Vv) Fr(Mh Mj Nb) Fy(bZ Lu nR) Ic(Ax Ip Kj) Qh(Is Ms Ns) Oa(Gp nT Pa) Ok(kN Nt Pb) dF(Kr Lj Om) nW(Bn Jj Ql) Cu(Kp Nb) Hu(bA cT) Ib(Mt Qd) Ip(bB Pj) St(bO Nh) Kq(Bn Kr) Qn(Jl Qa) Vo(Uc Uu) oQ(dH dL) AdNt AlkG AnFb ApJt AxkN FaGp NuoE LxLz MsKe MyTr NbUo NiUr QucT JjdI JnbA JqPj KdbV KjPa aDaY bHnR} Th{iH(aV bF bO cE cG dF eF fP Fr Hq Hu Md Nq Qu To Ut) iJ(aS cD cL dF Fr hF Hq oE oF Qy) Hx(aF bI cW Fp Ih Qw To Vv) Il(bU Co dA Fp Fw hF pF Qw) Ko(Aj Co Hr Ib Kn Lv Ng Tt) Cs(aV bM cE Nj Po Uh) Wm(aZ Bc bS Mt Ng Qy) iA(aF Fr Kq Mm pF Uf) oE(bM bO Li Nr Pa Qw) Co(Im Nn Nw Nx Ok) Vv(fP Fw gL Ql Tv) Ed(Ih Mj pF Pz) Lx(eF Hu Kq Ma) Mu(cW Hr Mb Mq) Ng(Cq Ef Sr Vu) Rm(Ik Ju Nt Om) Nx(bU dA Hu Lv) Aa(Jv Kn Rc) Ax(aY aZ bU) Lj(aY bV Pz) Aj(aN Ii) Cq(bG Oy) Mj(eF Hu) Ib(dA Et) Qa(Hu Nt) Qw(aF Fp) Li(kS Ma) Ri(cH Nr) DeVu FacW LvIh MkQl NlaF HcOe QbUp QyJl OwPb OydJ oKoN} Wn{Rg(dA Iz Ki Kn Rb Vt Vv tF) Hc(Cu Fn Hb Is Jj Mh Uv) cH(fP Jp kS nW Pf Tr Ue) Nx(cC Ic Jl Me St Tz) dJ(cC Mm Ok Ql Sr Uk) Ng(aE Aw Mv Oh Pz) Nv(Co Ky Nb Oa Tk) Vt(bV cN Mm My Oh) Na(aW aY Pj Rb) Hq(Fw Ic Ql Ul) Tt(Ad Dc Ic Ok) Ra(cP Ik Ld Ur) Qu(aG aR bV kS) dB(aP Oz Rj tF) Ni(bV cI Mb) Hb(Aa Cv Ks) Sr(bV Ii Uv) Qv(cP To Up) Li(aY bF Ki) Ok(aL aQ cY) Us(cP hF Jp) aW(Jt Ly Ql) cX(aU bF Rj) Ml(iH Me) Mm(aV cC) Tr(cV iH) Il(Pf Qz) Rb(Cq Pa) Jl(Kr Ql) Of(aG aR) Up(aK Ue) Ut(Fa Oh) Pj(Ao aQ) dA(cI Mt) AwBn CwVv CxMu DgDl FycE HatF NrPa MfaR MgVs MrbF HxaV PzOg StkQ JqKs JyPf KcOz LjcB cCcS} lX{Kx(Ct Jt Kj Kk Lx Ms Nb Nm Oy Pj Rb Rc Vu) Jf(aY cY Ib iJ Ip Ne Pf) Jm(kC nL Oy Ql Tz Ug Us) Il(Ib Is Jj Na Nb oE) Rb(bG iH Ip Nw Nx Qz) Lj(aE Bn bU Kr Ld Ph) Ri(aU bW dN Jj Qn Um) Fn(aQ dM Li nF oQ) Lx(cV Iv Or Pj Sr) Tn(Hw Iz Kq Pz Tv) Bn(bB Hx iJ mU) Oa(cW Ip Qw Vu) cV(Or Qb Qh Vt) nT(Jr Ju Ki Qz) Pz(Hx Nl Nt) Qa(Ib iZ Ut) Rf(kC nA nJ) Un(Ko Li Qe) mH(iH Ju Wm) iJ(cR Jy Tj) Ct(Fr Pa) Tr(aU Oy) Ip(Kr Na) Jj(In Pb) Kj(Ic Nk) Om(Qv Ug) Uk(nB Nn) Up(It Kq) Vt(Lu Ue) AfMf WmnH NuHw IbQb QecW RaoP KroQ LioK QlVu QnPj OraK VseF PaaU cBkC lYmF} fP{Lj(aY Dc De eM Kc kQ Ma Mj Mu Nj Ny Ph Qh Qx Uf Ut) Oa(bS cN cX DE dL Ha Kq Mu Ng Nj nW Pb Ph Pz Un) Qb(aW Ct Cv Jt Kc Kq oE Pd Ph Qd Qn) Is(Ik Il Jt Kj Lv Nk Nm Qw Uk Vs) Qh(aY dA Jt oE Of Ph Qy Ut Vs) Up(Al aR bE Dd Hc Ip Jq Js Nn) Vv(aW aY Ij Iq Ir Jn Js Nw Qn) Nn(Ct eM Jd Mu Oy Qt Qy) Sr(Aj Hu Ng Nt Of Pd) Ik(Fa Ih Ir Iu Mw) cX(kO nC nH nJ nL) Lx(Ma mZ Ng Of) Mu(Fa Oh Pa) aW(Ng oE Vo) eM(Jv Kj Kl) nN(Bn Il Vt) Ma(Ir Tn) Li(aR Jd) Oh(Nk Vs) kI(eF Gp) FaUt LvnK QamM QcmZ cBkC} Uk{aI(aN aR aW aY Fw Ip Is Lj mM Mu Oa Qb Qy Ur) Pz(aC cE dA dD De hG nN oE Qt Qw) Is(aE cJ cK dI dJ iJ Lv Nk Up) mW(Cv Iu Jn nB Nr Om Pc Tz Vv) aR(Fa Jn Mw Nw Ok Qa Tn) nO(Li Lv Nb Nj Tz Ur) Et(De Jd Ng Oa Pj) Mu(Jm Jn Jq Nw Tn) dA(Lj Nn Qa Rm Sr) aE(Fa Lj Lx Oa) Cv(nK nN oE) Ip(Hc Oa Vv) Qh(aN cK dE) dJ(Lj Lx nN) Qa(mM nI) Qw(Tr Ur) mE(Bc Hr) mU(dL Kn) nK(aV Nk) kP(Ad Uc) ArOa WmcZ LxcH MenB IhJd HfLj QyJn NwoO OenN PaoE bGmS} Qh{Mu(cH cK dA DD De iJ Kk Ng Qy Up) mM(aW Bc Bo Ct Hw Ii Ip Kj Ks Lx nT) Ct(aE De dJ Lv Ph Pk Qx Un Vv) Up(Cp cV eM hF Hr Ng Og Qt Qy) dA(aK Aw bZ Cw Dd Jo Lv Mg oE) Ar(aI aL cV cZ Qy Ua Vv) De(aL aQ aU cV cZ Et Jj) Ng(aE cH dI Fn Hf Ip Nj) oE(Cw Dc iJ Jt Qx St Wm) Aj(aR cK cY) Vv(aI dJ Jj) kP(cV Mf Qw) nN(Im Rg) nR(Dc Kr) mW(Hr lY) oP(Rm Vs) CpHx WmmY GzMj NtnJ IikK JjPb TkVt UtkN aKcY dEnU} Is{Up(aI aK aR cR gW Hc Hr Jj Mu Ng oE Of Og Vs) Jj(An aR bS cA cH Cp dE Pz Rc Vo) aI(Hq Jt Lv Mn Ng Nt oE Qw Uf) cV(Ct Jt Mu Ng Nl Pb Qt Qy Un) hX(Lj Lz Mh Mt Nn Og) Ct(cK cS Hx Kc Un) iJ(De Mg Nt oE Qt) Qy(bF bQ bZ Hf) Jt(dJ hW iB iC) rX(Nd Nm Nt Og) oE(Ib Nd Nt Vv) jI(iB In Iv) Il(kP rC) Qt(Ex Hf) aV(aK aU) hW(Ik Mb) qZ(Nj Nk) NtiC MuQw TnmM TvnN

Figure 27 Continued

JdcS QvmU RmmI RgoQ PjkK aAiB} mM{al(aY bZ Ha Nc Ni Nr oP Pd Qb Qc Vt) St(aX cR Il It Iu Js Nj Nk Nl Of) Vu(bG Bo Gp Jj Lj Me nA nR On Qd) Qw(bB Kq Lx Mw NN) Ri(cE Et Li Mz Nk Nv) eF(cD Ef Fn Im mU mZ) Jj(bV dI Kq Pk Uc) hB(Ij Ju Nj Nl Pd) Tn(aR Iu My Oy) Dc(cC Ez Mf) Vt(bG bQ dF) nT(aQ bG oH) Fn(bV dF) Qc(bH Rf) Jm(cV Ql) Ok(Ms oF) Un(Jn Kq) NtUh IdbV IjbH QzNy KcVs RgbG aCaH} Lx{dA(Aj Aw aY cH Ik Jo Kc Lv Mg Mu Nm Nt Of Pd Pj Po Rb Wm) aV(Aj Ct Hc Of Oy Ss) hX(hW iB Me Nd Nh qY) Jt(aE aI aR aY dJ) cH(Fy Kq Oy Pj Un) hG(Hr Mm Of Qw Ss) Vv(aP Hf Ip kQ) aE(Of Qt Qu Ss) aY(Aj Ct Hf Nt) Ng(aP Hf kS) dD(Kq Qt Ut) De(Hr Qw) Nt(aR kQ) Jd(cC oE) aI(Mu Of) mU(Ug Uv) ArIb MsnU SscY QwKq KrnI VunT PclL PdaW aUgW cTnO nKoH} lY{Ib(dD Kx Kz Mf Nc Pa Tv Us) Kc(cB Kd Kr Mf Oa Uv) Us(Ax aZ Dc Kj Nt Wm) Ks(aI dD Nx Ny Qb) Gp(Ct Jf Or Oy) My(Bn cQ cW mT) Rb(Ip mW oP Qc) Un(Ax Ha Pi Qd) Pj(aI Ip Ns Pz) cV(Na nO Ql Uv) Qz(cB dD Ql) Jo(aI Nv Ny) mW(Ax Qw St) Jt(Pz Uh) Uv(Nt Or) aZ(aI iJ) dJ(Lu Nx) BobG NuQc MfMs NaIk HwdD TnIz IiSr IlSt QwKx KroP RiVo OycE bXeF} hX{Mr(Hu hW Iu Me Mz Nc Ne Nh Pz) Nd(Lj Mt Mz No Ny Pe qY) Ok(hA Hu Ik Lz Mm Nj Nl) Mh(Hu Mz Nc Nh Nn Pz) No(hW Iu Mb Nk qY) Lz(Iv Me Nc Ne Nm) Mt(Iv Nc Nh Pb) Ng(Et Iu Jl Li) iB(Iq Nr Oh Qb) Po(Iu Nl qY) Iv(Nn Oh Qd) Pz(Iq Ny rZ) Lj(Me Ne Nl) Mz(jD Mj) Nc(Hr Oh) Iu(Nl Pe) qY(Hv rZ) NhJl NjNy HxJs IqlN NwjP PehW} oP{Ri(aY bJ cS cW cX Mk Nc nY oH Ql Vv) Ms(bS cA cK Hu Nj nU oN Rg Ut) Ed(aC aY Fn mP oH Pd) Lj(aC aE bE bU De Un) Oa(Ar aY Iv Pg Tv) Vu(Ar bS cA cK Nj) Qb(bH cR dH Ut) Kd(Jt kS Pj Vv) aO(bG cV kG Tr) Fn(bE Gp Kr) Ib(cC Li Mx) An(Ik kS) Lv(dE Rb) Vo(aY bM) MzdD ItSt JvaY KicB KrcZ UpmP VtaK VsPj} eM{To(aI bP cS Gp Jl Mq Nn Us Vo Vv) dI(bH Hx Js Ki Rc Ss Uu) Up(dG Ip Jl Kp Nn Ss) Na(Hc Jn Mb Nj Nl) Nl(aU Lz Nw) Hc(Ss Uo Us) Pz(aD dJ Fa) Ut(bV Jl Mq) dA(Ko Qg Vp) Ct(cE dJ) Mf(Lz Us) Jf(bU Lu) Jv(aN Mq) aQ(Ki Kr) aV(bW dE) AddJ DgaI EzHr MjbG NjUu HvOr IlRc KkLd LhcB OfUs VocS VvaE PjbW aOfR cEcT} nO{aI(bV bW Ha Kx Pb Ub Vt) Tn(cR hB Ib Mf Mg nJ) Oa(Aw cX dB Mu Na) bH(dF Hx Nr Pg Uh) hB(cB Ko Qb Ra Vv) Ue(Dc Uc tF) Lj(aX bL Rb) Up(Cq Iu Jn) Ax(Hx Ql) Ct(cC Jm) Wm(bG Ip) Ib(Ok On) AftF BaHx HaNl NnKr LvoF RbOh RabV JmbG RmQl aUcY bQnT dBiH} mU{bH(dR Fn Hw Ko Na Nw Uo) Oa(aS aX Cx Jo Nx Pa) eF(aJ hB Li oQ Pa Rc) Qa(Ar Ez Kr Qv Uv) Ri(cW Ez pF Tz) Nl(cB dR oH) Bo(bG Nx) Fa(mW Ql) Ug(Al Nb) Vo(Pz Uc) oF(Bn Kr) ApJt CxOk DcIi EdNw TjPa EzFr FnNa NrOr NcaI IbnH TrJo IvUp JmUv OeUs UtdF} nA{cB(Aa Aw cR Cv Lv Nk Nl Ri) Ed(bG bZ dF Fr Ma nR Nt) Un(aP dM Ha Mz Nn Oh) Ip(aV aZ dA Kr Na) Ri(aX dB iH Nx Qd) Ib(Cx Kx mY Qn) Wm(bQ Vu) Ez(bA Kx) Tn(Jh Or) Nx(aI Rb) AsSt BcQb BoaC CqFr CxOa MsOi NanJ NgIc JmPj} mP{Pj(aI bX Dc Fa Fr Hb iP Ke Ko Nd Nl oO Vv) Ib(aZ kS Mz nN Or Sr Ug Um) eF(Ba hB kI Li Qb Ss Un Ur) Up(Aw kC kO Mj nF nJ) Il(Al Ed) Jf(cX oE) Qv(Jm Nl) Or(Nx Pf) Vu(aF iA) AacB IdaP JiSr LjUn} nT{dR(cW cX Il Ks mW Nk Vu) Jj(Fr Ih Jn Pb Qb) Oa(Il In Ip Qc Ue) Tn(Ef Iz kS Kx) Af(aK aY Ms) Vu(iJ Ko Kx) Nt(Ez iP) Qw(dD Ql) Un(aY bQ) Oy(Cw Jg) Pa(aC cX) oE(iH Il) CtQb CxaK IbaZ TvLi JtaY KiaV LjUg UpcY} Mz{jD(Hq Lw Lz Md Mi Mk Mp Nm Pf Pg) lL(Jj Li lK Nc Nm Of Pc) jV(Hq hR Ik Jj Pd) hA(Li lN Mr Ms) rC(Iv Ma Nc Nj) Jt(hR lK lN) iB(Hx Nm rX) jL(Ik Nd Pc) Tk(Nh Oh) rB(Iv Nk) NcqT NdhR NllN} Lj{aE(De dJ Jo nC Ng) Ar(aX dN kK Up) kN(aO bH cR Ut) Up(aI cR iZ) dA(cS iJ nY) Af(nH nR) Mj(fR Gz) Kc(nW oN) Rg(bZ mZ) Tk(Ld Me) aI(Mn Pz) aR(Pk Qw) dJ(bZ oK) iJ(Jo Po) DeJj WmkI TiaY EtKq NooQ NxiZ cPgC oKoN} gC{Na(aK bB Ic Ik Ki Mj Nh Oz) Ne(bH bM cM Mf Qw) Ss(Aa Id Jq Nh Of) Hc(cF Mg Of) cP(Hr Oh St) Nu(Jr Pd) Ms(Hb Jf) Ic(Lz Ri) Up(My Pd) cW(Qb Qc) DbcV EzSr LvPk MeNl MnOy MrNk ToOu HbJi QmcI} mW{Hr(aJ bA cD iA Kj) Qw(Ha Oz Pb Pd Tn) Uc(Kj Oy Vu Vv) Nt(Cq Rm Vu) Lv(aF Ax Rg) Oa(Aw Nm Ug) Vv(aY Cv hB) bH(Kk Qc Qd) Rg(bG Nw) Vu(Hu Po) Pd(iA Ko) AwQb CqVo DlOk FrcR NcQa aUcY} Ri{nN(Il Kk Oe Ql Qz Rb Ug) nU(Gp Ir kO mY Ni Nn oF) nR(aY bH nB Vt Vv) kO(aX eF Mx Vo) nC(aX cE Uh) kF(aI aZ Mw) nJ(Qd Uh) kC(cB iH) kI(aQ aZ) PznI LdoQ OekP aPmI aXnL} Ng{Et(aW Bg De jY Up) Tr(aR Jn Qw Qx Up) Tn(aR Ip Jq Nj Qx) Pz(aI cV Fn Uo Ut) Jq(Ad Bg Fb) Gp(Ad Dc) iJ(Bb Ip) BgIq FbQn FrhR UcaI QbaE JljL OklN bFdJ bQcV} oE{Ex(aX bG Cq Dc Fa Nw Oh Tn) Ld(kO nH nJ nL) aP(dM hB Pa Pf) Nd(aR cE hG) Oa(aE aR Nj) Nk(Li Rm) Vv(bF Tn) Pa(bM iZ) AjTr DckP DeKk TomH PzbF RmlW OfcE dGkO} fR{To(aC bS Ik Ip Li Nm Pg) Mj(Ct Gz Ib Ly Qu Tj) Ip(Ms On Tn Uf) Ki(Fb Jd Jr Vu) Hu(cQ cX Pa) aY(bS cX Qy) Ib(Hr Qm) Up(Ky Mp) BobL MsJd HvIk aJcX} nN{Qw(cZ dL Im Jj Rm) Un(aW Ns Om Ul) Ug(An Bg Hr Oe) Kr(aI Jg Ly) Bn(hC nR) Fn(dR Ks) Nu(Hb Tr) Tn(Nk Rg) eF(Nb Nm) DbLy TrJo HbJt JeUp QzdD JjaX PaaY} aI{mS(bB Kx Nc Nd Nj Oe Vt) Pz(Ct De Ss) nR(bV bZ dM) kO(Na Nc Tj) Aj(aY Oi) Vv(Jr Sr) mI(Jm Tj) BbNt CqMu DioO MjnC IpkC KmL aOmZ cXkF} Qw{Li(aR bZ Jd Kq) Ex(cV Qd St) De(Fa Iq) Tn(Kq Qt) Ij(Jd Mu) mZ(Fr Or) nK(cZ Fn) kP(Dc Nr) AacX ArOh CqCt NukK IumH QaJd JjJm aKcY} Oa{Ar(Gp Hx Ur) De(Gz nY oH) aE(cS Kc Up) dJ(aR bZ Iv) kN(bH bU Ut) CpkI EtJt LunU JoiZ KckR KoTk NxmS OrmY UgoO PdmZ aOnR cSnW} mI{Pz(aC Dl Kz Uc) Kx(Ez Ib Pa Qb) Nd(Ur Us Uv) Ib(Ij Qe) Qc(Jj Ut) Un(Ir Qb) Pa(Ct Ha) BaGp TnIk QaJd KjaE RgOh QltF UpcH} oQ{dL(dB Pa Rm Tr) Nb(cB dA Kr) aE(Bn Fn It) bH(Hw Mr Ur) To(dR Nt) Kr(bR oH) cZ(Af Bn) AwBo BgOh FnmZ NocC NaaY IcnU aOeF} nJ{Ip(aZ dH Hf It Pd Pj Ug) Tn(Ef Iz Lv Vv) eF(cB dB mZ) Fn(Iu mS) Lv(cB dB) bH(dJ Gp) BodD MsKn IcKj JlUp NvcX} kK{Nt(aM aP Fa Fb nW) Vu(dE Gp Ha Pz) Fr(bH Kx Vv) Ib(bA Qe) St(Cp Jt) Pj(bQ Nk) eF(aM Rc) FaNx UvVt VobG VvhB PdbZ} Tk{Fb(Iu Jn Kl Kq Rj) Tn(Fy Hf Il Ny) Vt(It Jn Me) Fa(Md My) Tr(It Vo) Kz(Ij Pf) MeSr MsLi IhQn HfOh QdKr JnKs} qY{Mb(Mk Mm Pg rB) iB(Il jI jY Mm) lN(Hu Nc Nd Pc) qV(Nc Nf Oe) Jl(jL Mm) jY(hR Nj) MjNl MsOi NdlK IiJt IjOe} kO{Ip(aC aZ cC Hf iH Pd) Wm(dB dR Gp Jm Ke) cB(aE aY Kr) eF(dB mZ) FnmZ MjhB NadJ StRm NwbR UhbH UpaQ} nR{Af(Cq Oy Oz) Bn(Pc Pd Qe) Cx(bH Lv) Vu(De Jr) aO(Nt Oh) aY(Jt Rc) BobG LvUg HuKr IlhB QbRm} nI{Jj(Fa Ra Rc Vp) Fn(aC aZ dR) De(Jl Qa) Fa(Nd Up) Pj(Et Ha) BgQb FwUp NkVu JmKs JubQ OrVt} mZ{Fn(aJ eF Qz Um) Tn(aN aV Jf) eF(dR Fr Rc) Lv(Or Up) EdHb PzOy JgOr LiRg OhbH aOcV} iB{Nx(Et Ip It Ji Js Qd) Il(Fr Nr Ok Qa) aA(Iu Pa) lL(Hx Qb) NrJt JoOk hRrB jDjI} kN{Li(Af bH cU Kr Mr Po) Kj(Lv oN) Ut(Qe Vt) cS(An Ar) EdHb JjaF UnaO VucU OydJ PadB} Vv{Jr(aR aY cS cX dE) Ij(Ar Jd Qy) Ip(iJ oO) gW(bF dF) ArLi CqTi DeOn EtQn TnQt} aY{Ex(aV Ic Jd Mb Mw) Wm(kI Kz) Fa(dA dJ) Jr(dA Rc) AjFb TiIh KqNw aKaV} Et{Bn(aR Jt Pj) De(Hx Pj Us) kP(Ms Pj) ExUe MgjY NlrB IljO aRcX} Jj{Cq(dI Mu Oy) De(Ih Nn Us) Hr(aN aW) nC(Fb Tn) EdIp NknL IhdA} mS{hB(cU eF Ik Lv) Na(iJ Wm) Ib(dB On) RciJ RbPa JuNx UtdF VubG} kI{Pz(Ed Kj) Vu(Gl Qv) eF(bJ bM) AxKr DlPa FnMy NtdJ IbTn LiRg} Fa{bM(Ar Ct kQ Mu Qy) kQ(Gp Mu Nk Nt) DeiJ aPbV} cB{kF(Fn Ik Ir Kr) Ur(kC nC nL) kC(Aw Nu) DlnF cRnL} mH{dR(De Lu Nk Nx) Nt(aH aZ bG) AncY KxVt UnaW} Up{aQ(kC nH) kF(Bb Jp) ChnL CtRm IhOg IvnB KcLi} dB{nC(aC Jf Pd) dJ(kC nH) NtmY LvnL IbnB eFkC} nU{Un(Ir Ra Ua) Ib(Ic Ij) FyTn NuPz VucE} mF{bH(Me Tr) dR(Bc Cv) HrbQ IrRm RbPz PaeF} mY{Nx(aW bR Dc) Vu(Tz Uc) FnKs TraC KrdJ} Ip{nK(aV Bc bH Kk) Bc(kC nF) QclW} nH{cX(Nv Pa) BabG BoIk NtbR IbcH JgJt} nL{dJ(Hx Na) BobH FrNo IhJm JgJt NvcX} oO{Nd(Ax Fr) NtTo PzKj KphB RgaJ NvcX} Li{Jd(cS oK) MaoK KckQ NxdA aRcS} kP{Tn(Aw bV) AxIc DcOy MsOk UhVu} Ct{Cq(cA Lw) FrbM HxSr HbNx} dA{bZ(Hr Jn Wm) WmIq QbOg} Aj{AdcC DciJ FbQn OkhG} Oy{Cq(bQ Tn) PzlW bFdJ} mE{Fn(Dd Kk) HrTr KkbH} nC{BoIk GpbH HrUs VuaQ} jL{Jl(Ik Me Nl) MeiC} kC{WmSt KdNx KjPa PdcF} Ar{Ke(cC Hx) TnOf} Fr{MghR RmnK PbhA} Ok{CpHx DghG JtkQ} lW{Jm(Il Ks) IrRm} Aa{MbjI JocX} De{On(Hu Jd)} Ex{Qt(Dc St)} Mu{QaaE bQcV} Tr{NukG mTkS} Pz{RcnB KicV} Jn{CvUg OfhB} Oh{TiKn oKoN} Us{OemT bHnF} Pa{NsrX PclL} eF{nK(dR Fn)} qZ{MxNc NkIu} AwQlnB BoaCnF WmStkF MbHqhR MdMjrY TobZcH IvrBjR SraKcY

Figure 27 Continued

Constrained panels with 3 analytes, where 1.0E-7 >= 'AUC p-value' > 1.0E-8. Contains 4,951 panels of 13,646,915 total panels evaluated. :
gP{Qy(aH bA cE cG Cs dM Ed Fw Fy Hv Jm Jn Kd Kj Kk Lh Mh Mr Mt Mw Nn oF Oh Pe Qa Rm St Uh Us) Qt(aH Ax bB bF bL cG Cu dD Et
Hb Ih Jl Jn Jp Jr Kx Ld Mj Mw Oh Ou Qa Rm St Uk Uo Vu Th) Mu(bF bZ cC Cs Cu dM Fw Hb Hv Is Ke Ld Lh Li Lz Mh Mr Mw Nr Nv Ny
On Pa Pe Qw Tr Uk) Fa(aP aV Bg cG Ch Co Dk Ez Hb Hx Ik Iv Iz Jd Kk Ko kQ Ly Me Ns Nw oH Om Pb Po) Lx(aV Ba cA cK cL cV De dI
Fw Hb Hc Hf Il Iz Jh Jo Kc Kj Mw My Om Qu Ua Uu) Uk(aN aR aW cC cH hB Id Ir Jn Ld Ly Mh Ng Nn On Qc Qw Sr Tv Vq Vt Th) Aj(Dc
Fb Fr Hb Ii Ir Is Jl Ke Kf Kk Ko Li Mj Ny Qn Tr Tv Uh) Mg(aY Bg bQ cZ dF Ed Hx Ip Jl Kc Kg Nh Nx Oh Qn Qw Tr Uh Vq) Ib(Ax bF bQ dF
dM Ed Et Fy Ih Ij Jn Kk Mj Nn Oh Or Qa Rm Tn) hB(aP aZ cL cZ dA DE Ef Hx Ik Iz Jd Jo Mv Nw oN Pb Qw Ss) Ng(Ax Bb Co Cp Cq Dk Fb
Fy iA Kc Kg Ly Nx Qd Qe Rm Uo Ut) Of(bF Cs Lz Mh Mp Mr Mt Nn Nr Nw On Pf Qa Qh Tr Us) Kk(Bn cA cL cV dB De Hx Li Oz Pc Qa Qh
Ue Ug Uo) Ct(aJ Ha Hv iA Jk Jp Kg Me Nq oE oF Qb Ra Up) Nw(aY Ef Ez Hc Hx Jd Jh Jo Jt Lv Om Pc Ua Vs) Oy(Ax bQ bZ Cs Is Kf Ld Lh
Ok Qh Tv Us Th) Is(aV bN cA Ef Ez Jd Jo Mv Ua Ug Vv) Qw(aY bA Ed Mh Nr Oh Pe Qa St Tv Us) Li(cA cZ dA dE eC Ez Hw Iz Jo Kj oK)
Ok(aW cV De Ez Hc Il Jj Jo Kj Om Vs) Vs(bV bZ cR Et Il Nd On Qa Ug Us) al(aA aV Ax Ba bL bW Ch cR Ow) Cs(aY bN Ch dE Dk Iv Jj
Mv) Hx(cA dA De Ef Ez Jn Mv Ss) Ke(cC Ef Hc Nx Om Ue Vv) Kj(dA Fw Ko Lh Mh Mr Qh) aY(dF Ex Il Mr Ou Pe Pf) Ez(bQ dF Mh Mt Nr
Oh) Jj(aR cH Ed Ip Jm Us) Th(bI Hq Ma Mj Oz) Mp(cA cL dA dI oE) Lj(aE cH Ed Dp gW Hu) Vv(Ij Ip Jr Lh On) cV(aW Fw Ip Mh Qb) Mt(cA cL
dA dI) bZ(Lw Mi Mk Mv) kE(Db Ha kR Ky) oE(bL dM Nu Ra) De(Et Lh No) Hb(aA aJ Nx) Ss(bN Ld Qh) Ug(cH Ip Vq) cZ(aL Mh Mr)
dA(Lz Mr Qb) nO(dK Qg Uv) Aa(Jo Uu) Et(Bn Ue) No(cA Rg) Jh(Kn nR) Kd(aA Hu) Ld(bN cC) Lh(Ef Iz) Us(bC Uv) Pg(cK gW) aK(aV cY)
cH(Og Uo) dF(Ma Ut) dJ(Mh Mj) IY(bX Dp) nD(Kg nN) ChkN CqmW WmnF ExFw FyJo NncA MvaO IkIo JdQh RaaA bQcK cWnR dHmP
eCfP} bN{Qw(aW bQ bZ cV dI Ed fR hF Hr iJ Jm Jn Mu nK Nx Pz Qb Ur Th) Hr(aW bV cS cZ De dF Hb Ij Iq Jj Nd Nx Ok Qb Qc Sr Up)
Ss(bQ cH dG Ii IJ Ip Ir Jn Ko Nd Nn Nv oK Qe Sr Ur) Wm(aL aV aY dD Fa Hx Iq It IX Mn Ne Oa Qc Sr Us) Ko(bQ bZ cH cX dA Fa Hc iJ Jt
Kc Pk Rc Up Ur) iJ(Fp Fw Hf Kd Mh Mz Nw oE Qa St Tj) Pz(aR bV dA Hc Kc Kj Ms nO Nx Up) Up(Bb bV cR Et Kk Lj Nw On Tr) hF(aW
bQ Fr Jm Jr Ky Lj Mt Ok) De(Fy Kk Li Nn Nr Qd Qn Tr) Uc(aR eC Hc Mu Ng nO Of Rc) Oa(aE cH cX Hb Ne Nj Nl Ur) dA(Fw hB iA Li Lj
Lx Qb Tn) Et(aR cX Ih Kc Ms Vv) Lx(aV aY cH cR dJ Hf) To(bV cV Jj oE oP Qc) Ur(bB bQ bV gW Tr Uo) eC(Fb Fr Kk Mn oK Rm) Mu(Jr
Sr Tn Tr Uh) Jn(aX bQ bZ cH Hc) Lj(aE bV hG iZ nY) Nx(Jr Ke Uh Uk Th) dJ(cS Fw iA Ih Li) Ar(Jp Kd Li Qb) Tn(Ng oP Qt Qy) Rc(Ba Hb Ij
Ok) Qa(aO dI hG Jd) oK(cH Il Jr Uk) Th(Ax Fw iH) Us(bM Bn Gp) gW(Jd Kp Nn) nN(eF Ms nO) hB(aR cH dI) Co(kE nF) Cu(nO Uf) Fa(Hb
hC) Fw(mI Uk) Na(nJ nL) Nd(Kk Uk) Ib(dM Mw) Is(cV Un) Qe(Hc Pk) Sr(cR Jj) Jm(Al cV) Jq(Cx Qn) Kc(Li Vt) Rm(al Jj) Vq(Ef Kl) aX(Li
Qb) BbII BchG BnQn CsHv DcnO EdHb GznT TrOf IjJd RboP QybQ QhkE Kfdl KkaR VtaO aWfP b

Figure 27 Continued

Dp(Il Nc Or) Fb(It To Ug) Mz(Na Nl Pc) Tr(Jn Jt Mn) Me(Fy Jn) My(Ir Jq) Tn(Hw Rb) Hc(Hq Rg) Kr(Ir Pe) Kz(Rg Rm) MtVt IhIl IkUr ItVs IvPa JnOr KpVo} mW{Hr(bQ cT cV Kq Qz Uh) Pd(bM cD Dc dG Qz Tn) Vu(Bg Nq Qg Ss Tz) Aw(Kj Qa St) Li(bS cA cK) Fr(Lv oN) Kj(Cq Hx) aA(bH Ct) AfUa AxaC DcJt HaUo LvOu TndR StOe VtbQ} mZ{Fr(Ih Iq Kr Ly Lz Mh Nj Ur) Fn(dC dG Jr mY Or Vu) eF(bO Il Mf Tr Uo) Li(bS cA cK) Ct(Kx Pa) Mz(Il Ms) Tn(Iq Ly) Ut(Nr Vq) AxaC BgJf ChdD CqcB RmOh UrbZ} mU{Ug(Ax Cw Dc Ip Tr) Nr(bS cA cK Ks) Fn(aJ DB) Ib(aY Kn Nx) Ip(Ji Nl Qa) eF(cH Kj Qb) Dc(Hw Ql) Pa(cB Ha) BnhC EdMy HbKr QeUv QvKn JocE bCbH cBmI} nN{Tv(Dc dR Kk Nr) No(aW Ms Vu) Nk(cC cD eF) Bn(Ly Uc) Gz(Iv Rg) Hb(Pj Un) Ks(aY bH) Nw(Fy Kr) AfKo CpQn DeFn MfQl IlVs QzaY JoKk JqUn JuKx KdPh UgUu} nJ{Ip(aC cM Ih Ld Oy) cB(Dc Jh To Ur) Ex(Ib Kd Rg) dB(cV dD Ub) Tn(Ik Qt) bH(aZ Ql) cX(Bg Kd) CoRg CxOk GpHr NrKr NamS TrPd IhJm HbNx OybA eFiO} Aj{iJ(Ad Ip Nw Ok St) Vq(aV cT Nh oK) aY(Et On Tn Tr) aR(Et Tn Uc) Bg(cH oN) Fb(Hr Hx) Pz(bF oH) Jq(dF kS) TiKs EtaW LvOk QaaE StnI PanL} Jj{De(Jk Jm Li Ok) aR(Ed Ih Pz Qa) nI(aM Cv Jv Tn) dA(Qa Qb Rm) Mu(Al Us) Qt(Jk Ur) Jm(Jd Qy) aW(Et Ip) AnIh NknH QclW JgkP RmUt VtnC} Ct{Ar(Jk Li St) Cq(Mi Mu oK) Kc(Jk Li Oh) Nd(kG mI) Ih(aK aL) Nx(Ke Kg) aY(dF On) DciJ DeTn FnUo GpJm NtmT HxaW IcoO QaaE KxmI LioK bQcV} Mz{iB(Ik jV IL Ni Nj) lO(Jt Mb Me Oy) jD(Nd Ns Pa) Mg(jY lM) Nc(qV qX) rC(lK Ns) MnrY MslK NdhA NhjV NkqV PbrZ} kO{cB(cR Jh Jt To Ur) dB(aC dD dJ Lv Nl) Wm(aQ aY Nl) Ex(Ap Cv) BodD CoRg CxOk DcIl FnIu NabJ IpOy JgPd NvcX} De{Et(Dl Hr Iq Jt Mm Nn Ue) On(Hr Hx Ib Jt Qy) Vq(cV cY Hx Ik Uu) Tn(dA Qt) HrTr IhHb JtOk KecC} nU{Un(Iu Jg Nj Qb Rm) Cq(BG Gp) Ib(Jm Jn Nv) Nx(Hq Nn nR) Ms(Jn Me) NuJg HqbG HxdI QvRm JoNy KdPj KxVs} kK{Nt(BG Rm Tn Uh) Vu(Ib Ju Nw Ur) eF(Jm Kj Oy Tv) St(Ji Oe) AohB FrRm LuUs HrdF IcKj KpNx OybA} Li{Ar(dA Mu Of Qu Qy) Kc(dE Hc Mu Of Qy) oK(aO aR kP Un Ut) Nx(iB iZ) dA(cS Jo) KrnR PbjP} Vq{Ik(aN aV Fb Gl Nh Or tF) Jo(dF hB) dJ(aR Pd) AanH CpHx GlIb MgcB IzoF KcnW aEoO} nR{Af(Ax Im Nr oN Pc Pd) aO(cV Fn Of Ug) Bn(cS Oh) AwQb LvcB MsIl QaRm OhbH VuPe} iB{Il(Hx Ih It Iu Mt Nq Pa Qd rB) Hx(hR Mm) Nx(hR Nw) aA(Ih Qb) IUt PzrB JljL} kC{cB(Hr Nk Nl Pd Pj) dB(cV dD Lv) Wm(Tn Vu) Ip(Kr Uf) cX(Nv Ua) NadJ QnNx aXcZ aZbH} kP{Vu(Ax Cw dI Me Na Qd Uc) Ms(Fr Ij Nn) hB(Lz Mf Ra) eF(bL bM) AdMf CqUm KrbV} nL{Na(Al Nk) Jg(Pd Pe) bH(aZ Us) dB(cV dJ) BgcX BoIk CxOk GpHr GzbJ NtbR UbeF IhIm JscB} Et{Bn(Nt Vo) Jt(Ed rB) Pj(Kq Vs) aR(Mm Ss) AahA ArUe CqOy LvaW MgjV NcrB IblW QycX} dA{Qb(aE Aw Hr Jr Wm) Qa(Aw aY bZ Iv) bZ(Jr Nn Nr) Tn(aR Mg) HbNx KxkF} Ex{aY(Iz Jv Kj Mj Oy) Lv(Pa Qn) Ip(Ue Ug) CvkF TjMj IbSt IkdJ QtJk UtkI} mI{Pz(Kl Ld Uu) Kx(Rc St) BbJt DicB EdHb MtIb NdPb ToKj QaUt OycE cXtF nKhB} Tn{Qt(Ar Aw dJ Hf Hr kS Mu Of Ur) AsmT IbPz KynB OfaR} mF{Nx(eF Hb Ur Vt) bH(hB Kd Mt) Hr(Jp Nv) AxbE BbVu NrUt IuUn} mH{Nt(aV bM cB kS) dR(Ib Or) kS(An Kk) LuVt IpRb JmKs NxcY} kN{Oh(bH cD cR iZ oN) aO(cV Nv) BgcS HacW LvKz IbdB UnoN} Nw{aR(Ed Hr Wm) Qt(Hf Rb) ArUe BaaL JdcS SmK KqPj UnaW} mS{Nx(Cv Kd Kk Ky) hB(dH Iv Nj) CvUe NkdB RmdF VtbG} kF{cB(bM Iq Kk Nb) Un(dB Mw) Pd(Ko Us) DcNx NtdB KrdJ} Mu{cV(Cq Ih Pa To) DgDl LvbQ UeJq QbaE KcUn PacR} Hx{Cp(aW Fb Jn Ke On) hR(Aa Hv) ArCs BnJn IpSs} nI{Vu(Ha Ir Ju) Qa(Bn Rb) BgTt CweF NoOk LuVt KxdR} jL{Me(Fr Nq Qa) Jl(Iv lK Mg) qZ(Ir Mj) FrPb} kI{Qb(An bH Cv Wm) Ib(Ax Qe) CqQv HaPa aYeF} Nd{cV(Jm Qt Ss) hR(Iu Me) QcoO KklW aVmT} Gz{Ed(Me Po Qt) CxnF FwJk JfPa eFnC} Il{Ip(jQ lW oH) HroH IulO NyeD PajD} mE{Fn(aJ Fr Jr mT) Ur(aY bH) HrbM} Ok{Qy(Jt Pj) MmhG JojV JthA KqPj} lW{Pz(Ml Rb) NiQc IbQe IrRg KcVt} oO{Fr(Af cX) hB(aO Oh) MbRb IkQd} Cq{Oy(bF dJ eF Ke) UgaY} nC{cB(Pd To) cX(Bg Ns) bRcV} nH{Na(hB Nc) BgcX MjJg IhIm} nK{Fn(Dd Ul) IpaQ PzOy bQcR} Nl{hW(Ih Mj) QahR OgrB} Qb{aV(aE aK) BgnB OgdJ} mY{Pd(cB Tr) UrbH cBhC} lN{Me(eD Ms) MbMs InIu} Ns{qZ(Nc Ne Nh)} Hr{EzMt GpaW bFdJ} Ib{Mw(aY Iv) aKcY} Qa{Nt(aE nW) QyaE} Un{JmnM KecC dBnB} rB{MbMs NcOg IvjQ} Aa{Jt(cX hF)} Bn{cZ(Pz Sr)} Ti{KnVu RmcH} Of{DciJ TrRf} cY{SsaK aWgW} CvUgiJ WmIpoH FraOmT MeIqhW InIujI QybMbZ OraYcH

Constrained panels with 2 analytes, where 1.0E-7 >= 'AUC p-value' > 0. Contains 27 panels of 99,106 total panels evaluated. : gP(fP fR gC Oa) oE(mM mS nO oO) Ri(oO oQ Th) Up(lY oO oQ) Wn(Bo Hf) ThOa FbgW FnfR MwTk TnkE QhbN VqkC cReM cWgC eFlY nTlX Constrained panels with 2 analytes, where 1.0E-6 >= 'AUC p-value' > 1.0E-7. Contains 22 panels of 99,106 total panels evaluated. : gP(aI Ct Lj Ng) lX(Ip Jj Uk Up) fP(Lj Oa Qb) hX(Is Li) kE(eF St) WmTh EdeM QabN QhoE UkaI UpnD VukK Constrained panels with 2 analytes, where 1.0E-5 >= 'AUC p-value' > 1.0E-6. Contains 79 panels of 99,106 total panels evaluated. : bN(Et fP hB Jn Jr Ko Oa Pz Qw Ss Uh Uk Wm) gP(Fa Ib Kk Lx Mg Mu Qt) Th(Cs iH Lj Mu oN Qw) Ng(cV Fb Qh Tn Tr Vq) hX(Iq Iu Lx Lz Mj Pa) Vu(kE mW nD nO) lX(eF Fn Pz Ri) Is(Ct Jj Tk) Qh(Ct dA kE) Fn(kE nN) Ip(nD Uk) Qw(Li nN) Lj(dJ eC) Wn(Nv Rb) lY(Ri Un) qY(aA Mb) DeEt FaaY FbeC LxdA HxhR JfeM JjnT LiTk UgnD UpnA VqkP cBkO mMhB Constrained panels with 2 analytes, where 1.0E-4 >= 'AUC p-value' > 1.0E-5. Contains 191 panels of 99,106 total panels evaluated. : gP(Aj Cs Ez Fw hB Hx Jj Ke Kj Li Mh Mr Nw oE Of Ok Qw Qy Uk Vs) aI(Aj aY bN Ct Is Lj mM Mu Ng oE Of Qt Ss Vv Wm) bN(Ad cS cV Fa Hb Hr iA Kk Lj Lx oE oK Tr Ur) hX(Lj Me Mh Mr Mt No Nw Ny Ok Pe Po) Qh(Aj De eC Ez fP Mu Qy Uk Up Vv) Is(cV Ez Hu Il kP oE Qy Uk Up) Lx(aV aY cH eC Ez fP Ib Vv) Wn(cN cX Hc Jl Nx Ra Us Vv) oE(bF cE Jq Lj Nd Og Pa Uk) Ct(aY fP Iq Jn Oh Ok Tn) eC(Fa Ip Li mY Mz Oa oQ) Uk(cH cZ Et Jn Oh Qw) fP(aY cC Fa Iq Up Vv) Fa(bM dJ kQ Up) Ng(Ad Bg bQ Hb) cB(nC nD nJ nL) dA(Li Lj Qa Qb) Th(eF Hx Vv) Jj(aW Oa Rm) cV(aW Mu Qw) lX(Il Or Vq) qY(jY Nc qV) kE(bQ hB nW) Fb(Aj Qw) Fn(eM nK) Li(Ar Hc) Lj(aE aR) Vv(Et Jn) Pj(mP nD) gC(Ms Ne) MflY MjfR Mwlb MzrC TocH TnQt IlIp RieM OadJ UpoP VunI PahR aKcY nOhB Constrained panels with 2 analytes, where 1.0E-3 >= 'AUC p-value' > 1.0E-4. Contains 505 panels of 99,106 total panels evaluated. : Ct(Ad Bg bM bQ dF Fa Fb Fr Hx Ih It Iu Jk Jm Ke Lj LX Mw Nn Nv Oa On Ou Qa Qb Rm St) gP(aA aJ Ax aY bN cA Ch cV cZ Ed Et Hb Il Is Jn Kd Ld Lh Mj No Qa Qb Qh Rm Tv Ug Vv Th) Qh(aI AR aV aY bS cA cK Cp cV Dd dJ Ib Ik Jj Jo Mg mM nD Of Oy Qt Qw Ua) Uk(aE aR aW dA dJ Fa Fb Fn Ih It Jm Jq Kk Lx Mu nO Nw Oa Pz Qb) Is(aV bN cH dA eC fP IB Ik Jd jI lY Ms Qt Qv Qw rX Vs Vv) fP(aW bM cH eC Hb Hc Hu Ik Il Iu Jd Jm Mg Mu Ng oE Of Vo) lX(Bn Jf Jm kC kF Kj Kx Mf nC nD nH nJ nL Oa Pj Pk Rb Tn) Ng(Ap aY bF bZ Co dJ Dk Ef Fa Ke Kf Ko Ua Uc Ut Wn) Up(aY Et hB Ih Ip Ir Li Lj Lx Nw Oa Oh Qa Rm St Th) eC(aI aW bZ dF Fr Ir Jr kC Kk Kn kO nD nJ nL Nw Tr) Jj(aN aR cX De Dp Ed Fw Jm Qt Qy Rc Us Vv Wm) aI(aW bJ Hc Hr Jr Lv Nt Oa Pd Pz Qb Qw Qy Vo) Ip(cV Ed Ez Hc Hu Hx lY Ms nA nJ Ss Vo Vv) Li(aR Ba bS Cp De Ez Jd Kc oK Qt Qy Vv Wn) oE(aE aW bQ dD Hb Hr Lx Mt Nn Pz Qw To Vv) Fb(Aw aY Ez Hc Ik Mg Of Qt Qy Ss Vv Tk) Th(aF bU Co dA Ed Ib Il Lv Mk Nx Qy) Tn(Aj De Ib Iz Mu nD nO Of Oy Qy Tk) bN(bV cH dJ Ed Fw hF Ih Il nN Ok Us) lY(cV Ib Kc Kx My Na Nd Nt Pz Qc Qz) Et(Aj aR Bn cX Hc Pj rB Ue Vo Wm) Lx(Aj aR Cp Hc Jd Kq Qt Qw Rc Ss) Fa(aP cV dA De dN Gp Jd Kq Mu) hX(Jl Js Lh Nc Nd Nn Oh Pg Qd) Qw(Bn cH De Iq Lj Qa Qb Tr) Oa(aE AR dA Gp kE mW nO) Nw(cV Hc Hf Jd Kq Pj Vv) Wn(DB Hb Na Pf Pj Vt) Aj(Ad dF Jn Mw Ok On) aV(aK aU eM Lj Pa Qb) aY(cV Hc Il Or Qa Ug) dA(Ed Ir Jr Nn Nr Rm) De(Jp Ke Ko Tr Vq) Ok(Cp Dg Dl kE Vv) cV(Ba Ih Jn Pz Qt) iB(Il jI Nx qY rB) Lj(Ar iJ iZ Pk) Vv(bF Ij Ke Tr) kE(Bg Dc dF Kk) Nl(iC lN rB) bQ(Ez Ib Mu) nD(Kr Ms Un) hR(Nd Nn

Figure 27 Continued rB) hB(aR Of Pb) Wm(cH cZ) Ed(aR Hb) Ke(Hc Ue) Ri(nC oP) gC(cP Na) nT(dR Ms) mZ(eF Mz) qY(jI lN) CqOy DgDl EzMw FnnH LyIq NcrB NelN NkiC HxcH IbmP TrOf IkVq QaJd StmM QybZ JljL TkOh PghA aKaQ bFgW bHmW cBnA dBnC dJeM

Constrained panels with 2 analytes, where 1.0E-2 >= 'AUC p-value' > 1.0E-3. Contains 755 panels of 99,106 total panels evaluated. : Ke(Aj AR Aw Ba Bn Cp Ez Hr Ib Ik Jd Jt Kq Lv Mg Ms Nt Nx Of Qt Qy Rc Ss Un Up Vo Wm) dA(aK bF bQ bZ cC Cs dM Fb Ha HB Hr Ih Iq Iu Jj Jn Mg Tn Ue Us Vu Wm) dJ(bF cC Cs dF Ed Fw hB Hc Hr Hx Iq Is Jj Li Lv Mg Nx Og Qb Qt Ue Ug Us) Vv(aO aY bQ bZ cS cX dF Fa Hb Ir Jq Lh MW Nd Oa On Ou Qw Uh Ut) Et(Ap Ar aW aY Ct Dg Dl Ed Ef Ez Ib Iz Jd Kq Qt Qy Rc Ss Ua Ug) Ok(Ap Aw Ba Bn De Ef Hc Hu Iz Jd Kl Ng Og Pj Qt Qy Rc Ss Ua Vo) Up(Ax bZ cH Cs Dc Ed Fw Hb Hr Jn Kk Mh Mr Nd No Og Qb Qt Tv Us) Fa(Ar Aw Bn cN Ez Ib Ik Jj Lv mW Of oH Pd Qt Qy Ss Ua Ut Tk) Jn(Bn De Ez fP hB Hc Hr Hu Hx Ib Ip Kj Kk Ms Og Qt Vo Tk) aY(bN cC cS cZ Ed Hf Hr Is Jj Jr Kc Mu Mw Oa Qw Qy Uk Wm) eC(cE cH Cs Ed Fw gP hB iH Kd Mh Mn nA Nx Pa Qb Qw Us Wm) Ct(aO bF bZ Cq cS Fw Hb Hr Ip Jl Kc Mt Nq Pa Pz Us Ut) Aj(bF Bg bQ fP iJ Ip Is Iu Jq Li Mt Pz Tr Uc Vq Th) De(Fy HB Hx Jq Kk Lh Lj Lx Nn Nq Oa oE On Qa Qb) Qw(aR bQ bZ cX Ed Fw Hr Jm Mu Ng Nn Oa Pf Us) Qh(aQ Bn cH cX Hc Iz Jd Jk Jt Lv Nk Pd Vs Wm) Fb(Ch Ef Hb Hr Ib Jd Lv Nt Og Oy Qn Rc Ua) Qy(bF bM bQ cX dF Hx Ij Ip Lx Nn Nw Qa Uk) Qb(aE aQ aR aX cV Ez Hb hR Hu Nd Pb rX) Qt(bQ dD Ed Ij Ip Mw Nn Nw On Qa Tr Uk) Oa(aQ Bn Cp cS cX Hb Jd Kc kQ Mu nD Ng) Wm(aR cC dD fP Gp Hb Ip Is lX Nw oH) Th(bI bN cW fP Hc Hu Kn Ma Ng oE Oz) Ss(bF bQ bZ dF gP Li Mw Nn On Pz Tr) Ib(bF bZ Hx Ip Li nA Nn Nq Nw Qa) Uk(Fw Hr Hx Lj nC Nd NN Sr Wn) Tr(Ez Iz Jt kE Mg Nt Oy Ua Vo) Kk(aR Bn cS Hr Is Kc Lv Mu Vo) bZ(Jd kE Lv Ma Mu Nt Of Pd Vs) cX(cV Hx Jq Ko Li nC nH nJ nL) Lx(Aw Ba Hb Hf iB Kc Qu Ua) aV(Cs gW Ih Iq Ir Jr Li Qa) Ed(aI bM Gz Hw Is nD oP) Hr(aW cZ Ez fP Gp Hu Jj) Hb(aI aR cS Lv Mu Nx Rc) Jd(fR hB Ij Ip Mw Oh On) Tk(Ih Iu Iv Kn My Mz Pf) lY(Fr Gp Ks Pj Rb Us Uv) Cs(Ar bM dN Gp Ik Lv) Qa(aQ AR Ez Iv Pb) Li(cS Iz kN lL Pb Ua) Wn(cH cP Il Ks Mb Qv) aW(cC dB hB Hx Kc Lv) bF(cA Lv Mg Mu Of Oy) dF(cA Mu Of Oy Pb Ut) nR(Af aO Bn Nt Pb Pd) iB(aA hR HX lN Me) kE(bG bV Kc Kd Nv oF) Hu(Hx Ir Jm Ny Og) Tn(Bg Ch Cp Kq Ua) Hc(aO Fn Fr Is Mw) Pz(Bn Ez fP hB rB) Pg(hR lK lO Pd rC) aQ(aU cY eM Ir Jr) bQ(Bc Mg Of Oy Ua) nL(dB Fn Ip Jg Nk) Nr(bS cA cK dI) Iq(hW Il jI jP) Is(cS qZ Ua Vo) Lj(dI Hf hG Ph) Nw(cS Ez Un Vo) Oh(Aw cS Ez Kc) aR(Jr Ko Nn Ug) hB(aN aP hG Ky) Ba(fP Gp Ij) Bn(Hx Jq Sr) Fr(hA hX mZ) Ip(kO nH Ug) Ir(dD Hx Il) On(Dg hX Ua) aU(aK cY gW) cH(Aw Jj Uo) cZ(hF Ur Vo) gP(Jr Ko Ra) lX(cV iJ Qc) mH(cY dR Vq) mM(bV Dc oF) nC(bR Fn Vq) nD(Jf Rb St) rB(Ne Nk Og) qY(Nj Pc rX) jY(hX Nc Nk) oP(aC aO dD) Ch(aO Mw) Fw(Nt Oy) Nn(Cp Ez) Ly(Db Rb) Ng(cS Tt) Nl(mU qT) To(cV fR) Ri(gC nU) bN(Mu Nx) cC(cW dE) dB(dE iH) eM(bW dI) fP(nN Pd) gW(cE cY) nT(Af kS) iC(Nb Nc) oQ(dL Kr) AdMg ArSt CuOy HanO MelN MjhR MwOg NamU UeJq HqPb TvnN HfRc QclW JjUr JsjI JtKo aKdR kQoE

Figure 27 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.5E1 | 1.1E2 | 8.6E1 | 1.3E2 | 5.6E1 | 9.6E1 | 7.0E0 | 1.6E1 | 4.0E2 | 4.8E2 | 248 | 50 | 248 | 50 | 0.66 |
| Ad | ug/mL | 4.4E-2 | 7.6E-2 | 7.0E-2 | 3.4E-1 | 8.6E-2 | 1.4E0 | 6.8E-4 | 7.8E-4 | 5.4E-1 | 8.5E0 | 139 | 35 | 139 | 35 | 0.63 |
| Af | ng/mL | 1.3E0 | 6.7E-1 | 1.1E1 | 4.4E0 | 4.9E1 | 6.7E0 | 1.7E-3 | 1.7E-3 | 5.3E2 | 2.3E1 | 139 | 35 | 139 | 35 | 0.43 |
| Aj | ug/mL | 1.6E0 | 3.2E-1 | 2.5E0 | 1.6E0 | 2.5E0 | 2.3E0 | 1.5E-3 | 1.3E-3 | 6.1E0 | 6.1E0 | 139 | 35 | 139 | 35 | 0.37 |
| Al | mg/mL | 8.3E-5 | 1.2E-4 | 2.5E-4 | 3.7E-4 | 4.3E-4 | 4.9E-4 | 4.3E-6 | 7.6E-6 | 1.8E-3 | 1.8E-3 | 139 | 35 | 139 | 35 | 0.57 |
| An | U/mL | 5.8E1 | 9.0E1 | 2.1E2 | 4.3E2 | 5.8E2 | 1.3E3 | 2.8E-1 | 6.4E-1 | 5.5E3 | 7.8E3 | 139 | 35 | 139 | 35 | 0.59 |
| Ao | pg/mL | 9.1E1 | 1.4E2 | 6.0E2 | 3.5E2 | 3.9E3 | 7.9E2 | 1.5E0 | 4.1E0 | 3.9E4 | 4.5E3 | 139 | 35 | 139 | 35 | 0.61 |
| Ap | ng/mL | 3.2E1 | 4.7E1 | 4.7E1 | 6.5E1 | 5.5E1 | 6.2E1 | 2.0E0 | 4.4E0 | 3.3E2 | 2.4E2 | 139 | 35 | 139 | 35 | 0.61 |
| Ar | ng/mL | 5.6E-1 | 2.2E0 | 2.4E0 | 6.1E0 | 5.9E0 | 1.1E1 | 3.4E-3 | 3.4E-3 | 5.1E1 | 5.0E1 | 139 | 35 | 139 | 35 | 0.69 |
| As | ng/mL | 8.7E-3 | 1.0E-2 | 1.2E-2 | 4.6E-2 | 1.7E-2 | 2.1E-1 | 1.7E-3 | 1.7E-3 | 1.3E-1 | 1.2E0 | 139 | 35 | 139 | 35 | 0.51 |
| Aw | pg/mL | 1.6E1 | 1.7E1 | 1.7E1 | 1.9E1 | 5.8E0 | 7.6E0 | 2.9E-2 | 1.1E1 | 4.2E1 | 5.1E1 | 139 | 35 | 139 | 35 | 0.57 |
| Ax | ng/mL | 1.5E0 | 8.8E1 | 1.4E1 | 9.2E1 | 6.8E1 | 2.0E2 | 1.3E-2 | 1.0E-4 | 7.7E2 | 8.5E2 | 139 | 35 | 139 | 35 | 0.68 |
| Ba | ng/mL | 7.7E1 | 3.0E2 | 5.3E2 | 1.4E3 | 1.4E3 | 2.9E3 | 1.1E0 | 3.1E0 | 8.1E3 | 1.5E4 | 139 | 35 | 139 | 35 | 0.66 |
| Bb | ng/mL | 3.7E0 | 7.6E0 | 6.3E0 | 1.2E1 | 7.9E0 | 1.1E1 | 4.1E-3 | 3.5E-1 | 4.9E1 | 4.8E1 | 139 | 35 | 139 | 35 | 0.67 |
| Bc | ng/mL | 3.2E1 | 7.2E1 | 1.2E2 | 1.8E2 | 2.2E2 | 2.8E2 | 4.9E-1 | 2.9E0 | 1.2E3 | 1.0E3 | 139 | 35 | 139 | 35 | 0.63 |
| Bg | ng/mL | 1.1E-1 | 1.6E-1 | 4.6E0 | 1.2E1 | 1.9E1 | 6.7E1 | 5.3E-4 | 1.9E-2 | 1.5E2 | 4.0E2 | 139 | 35 | 139 | 35 | 0.58 |
| Bn | ng/mL | 5.6E-2 | 5.6E-2 | 1.3E0 | 2.4E0 | 2.1E0 | 9.8E0 | 5.6E-2 | 5.6E-2 | 8.6E0 | 5.8E1 | 139 | 35 | 139 | 35 | 0.48 |
| Bo | ng/mL | 1.3E1 | 1.7E1 | 1.5E1 | 1.7E1 | 1.1E1 | 1.2E1 | 1.6E-2 | 1.6E-2 | 5.0E1 | 5.3E1 | 139 | 35 | 139 | 35 | 0.57 |
| Ch | uIU/mL | 1.1E0 | 9.6E-1 | 3.3E1 | 3.8E1 | 1.7E2 | 2.0E2 | 3.4E-3 | 3.4E-3 | 1.8E3 | 1.2E3 | 139 | 35 | 139 | 35 | 0.46 |
| Co | pg/mL | 4.4E1 | 6.1E1 | 2.4E2 | 1.9E2 | 1.5E3 | 3.7E2 | 1.5E-1 | 8.1E0 | 1.7E4 | 2.1E3 | 139 | 35 | 139 | 35 | 0.63 |
| Cp | ng/mL | 2.2E1 | 2.2E1 | 2.7E1 | 6.9E1 | 2.1E1 | 2.1E2 | 6.0E-1 | 2.5E0 | 1.3E2 | 1.3E3 | 139 | 35 | 139 | 35 | 0.58 |
| Cq | ng/mL | 2.8E-2 | 4.2E-2 | 1.1E-1 | 1.6E0 | 4.8E-1 | 8.3E0 | 8.0E-4 | 8.0E-4 | 5.1E0 | 4.9E1 | 139 | 35 | 139 | 35 | 0.59 |
| Cs | ng/mL | 4.9E1 | 2.2E2 | 3.0E2 | 1.2E3 | 9.6E2 | 3.2E3 | 8.9E-1 | 8.3E-1 | 1.1E4 | 1.8E4 | 139 | 35 | 139 | 35 | 0.67 |
| Ct | ng/mL | 3.6E-1 | 2.3E-1 | 4.2E1 | 3.7E1 | 1.3E2 | 1.1E2 | 1.3E-2 | 1.1E-4 | 6.2E2 | 4.7E2 | 139 | 35 | 139 | 35 | 0.47 |
| Cu | ng/mL | 2.5E-1 | 3.8E-1 | 4.6E0 | 3.4E0 | 8.9E-1 | 1.1E1 | 1.9E-2 | 1.7E-2 | 9.0E0 | 6.6E1 | 139 | 35 | 139 | 35 | 0.64 |
| Cv | ng/mL | 4.1E0 | 1.3E1 | 2.5E1 | 4.7E1 | 6.5E1 | 9.2E1 | 2.0E-2 | 2.4E-2 | 5.3E2 | 4.7E2 | 139 | 35 | 139 | 35 | 0.59 |
| Cw | mIU/mL | 2.9E-2 | 4.7E-2 | 4.2E-2 | 2.4E-1 | 3.6E-2 | 1.1E0 | 8.9E-4 | 4.1E-3 | 2.3E-1 | 6.8E0 | 139 | 35 | 139 | 35 | 0.62 |
| Cx | ng/mL | 2.1E0 | 1.6E-2 | 5.3E1 | 3.9E1 | 1.0E2 | 9.0E1 | 9.3E-5 | 9.3E-5 | 3.9E2 | 2.8E2 | 139 | 35 | 139 | 35 | 0.40 |
| Db | ug/mL | 7.4E0 | 8.1E0 | 8.8E0 | 8.5E0 | 7.9E0 | 5.9E0 | 4.5E-1 | 8.8E-1 | 5.9E1 | 3.1E1 | 139 | 35 | 139 | 35 | 0.51 |
| Dc | nmol/L | 1.8E-2 | 6.3E-2 | 5.0E-2 | 6.0E-1 | 1.4E-1 | 2.4E0 | 5.2E-6 | 1.3E-3 | 1.6E0 | 1.4E1 | 139 | 35 | 139 | 35 | 0.68 |
| Dd | ug/mL | 6.3E-2 | 2.3E-1 | 1.6E-1 | 3.7E-1 | 2.5E-1 | 6.4E-1 | 4.8E-4 | 3.4E-3 | 1.6E0 | 3.6E0 | 139 | 35 | 139 | 35 | 0.63 |
| De | ng/mL | 3.4E-3 | 3.4E-3 | 7.8E-2 | 1.1E-1 | 1.3E-1 | 2.4E-1 | 3.4E-3 | 3.4E-3 | 9.2E-1 | 1.1E0 | 139 | 35 | 139 | 35 | 0.50 |
| Dg | ng/mL | 3.3E1 | 5.2E1 | 4.5E1 | 6.0E1 | 4.0E1 | 4.2E1 | 7.1E-1 | 1.9E0 | 1.9E2 | 1.5E2 | 139 | 35 | 139 | 35 | 0.61 |
| Di | pg/mL | 2.0E0 | 2.9E0 | 2.4E0 | 3.0E0 | 2.3E0 | 1.8E0 | 1.8E-1 | 1.8E-1 | 1.3E1 | 9.0E0 | 139 | 35 | 139 | 35 | 0.62 |
| Dk | uIU/mL | 1.4E-2 | 1.8E-2 | 5.2E-2 | 1.0E-1 | 1.7E-1 | 2.1E-1 | 1.1E-4 | 1.1E-4 | 1.6E0 | 9.8E-1 | 139 | 35 | 139 | 35 | 0.58 |
| Dl | ng/mL | 1.9E2 | 2.9E2 | 2.8E2 | 4.0E2 | 2.5E2 | 3.8E2 | 5.5E0 | 4.4E0 | 1.2E3 | 1.6E3 | 139 | 35 | 139 | 35 | 0.59 |
| Dp | ng/mL | 2.3E0 | 1.8E0 | 5.5E0 | 5.2E0 | 8.1E0 | 1.2E1 | 3.7E-3 | 3.7E-3 | 4.6E1 | 5.6E1 | 111 | 24 | 111 | 24 | 0.41 |
| Dr | pg/mL | 2.1E1 | 3.4E1 | 4.1E1 | 1.0E3 | 5.5E1 | 3.0E3 | 7.5E-1 | 7.5E-1 | 2.5E2 | 1.0E4 | 60 | 12 | 60 | 12 | 0.68 |
| Du | pg/mL | 1.4E2 | 4.4E2 | 9.7E2 | 3.2E3 | 2.9E3 | 7.7E3 | 1.2E0 | 1.2E0 | 2.0E4 | 2.4E4 | 48 | 9 | 48 | 9 | 0.60 |
| Ef | ng/ml | 9.5E-2 | 2.1E-1 | 7.8E-1 | 1.4E0 | 1.7E0 | 2.9E0 | 5.7E-4 | 5.7E-4 | 1.0E1 | 9.9E0 | 119 | 28 | 119 | 28 | 0.57 |
| Wm | % | 8.5E-2 | 4.5E-1 | 9.6E0 | 7.7E1 | 7.0E1 | 2.5E2 | 5.4E-2 | 8.5E-2 | 7.7E2 | 1.0E3 | 130 | 29 | 130 | 29 | 0.57 |
| Ed | pg/ml | 5.2E-1 | 2.9E1 | 2.6E1 | 8.7E1 | 4.0E1 | 1.4E2 | 5.2E-1 | 5.2E-1 | 1.9E2 | 5.0E2 | 111 | 24 | 111 | 24 | 0.66 |
| Yf | ng/mL | 1.5E1 | 2.0E1 | 4.7E1 | 9.2E1 | 9.4E1 | 1.4E2 | 2.9E-1 | 2.9E-1 | 5.9E2 | 3.5E2 | 51 | 8 | 51 | 8 | 0.54 |
| Tj | pg/mL | 3.7E-1 | 5.0E-1 | 3.9E1 | 3.5E1 | 2.3E2 | 7.9E1 | 3.7E-1 | 3.7E-1 | 2.3E3 | 3.1E2 | 119 | 26 | 119 | 26 | 0.58 |
| Po | pg/ml | 1.3E-1 | 5.2E0 | 8.0E0 | 2.2E1 | 2.6E1 | 4.5E1 | 8.0E-3 | 2.6E-2 | 2.7E2 | 2.2E2 | 293 | 61 | 293 | 61 | 0.66 |
| Ti | ug/mL | 3.0E0 | 6.9E0 | 4.5E0 | 8.0E0 | 3.9E0 | 5.3E0 | 1.2E-1 | 9.7E-1 | 1.6E1 | 1.8E1 | 73 | 11 | 73 | 11 | 0.70 |
| Em | ng/ml | 2.9E-3 | 2.6E-2 | 4.0E-2 | 1.9E-1 | 7.5E-2 | 4.5E-1 | 8.4E-4 | 8.4E-4 | 5.0E-1 | 1.9E0 | 73 | 19 | 73 | 19 | 0.59 |
| Et | ng/ml | 1.3E3 | 2.9E3 | 1.5E3 | 2.7E3 | 1.1E3 | 1.3E3 | 7.5E1 | 5.9E2 | 4.8E3 | 5.0E3 | 292 | 61 | 292 | 61 | 0.76 |
| Eq | pg/ml | 2.3E2 | 8.2E1 | 3.5E2 | 3.2E2 | 3.8E2 | 5.2E2 | 1.0E0 | 1.0E0 | 1.5E3 | 1.4E3 | 48 | 9 | 48 | 9 | 0.41 |
| Th | ug/mL | 1.2E0 | 1.6E0 | 1.7E0 | 2.0E0 | 1.5E0 | 2.0E0 | 1.2E-1 | 2.6E-3 | 7.5E0 | 5.9E0 | 73 | 11 | 73 | 11 | 0.49 |
| Fa | ng/ml | 3.9E1 | 7.5E1 | 9.5E1 | 2.3E2 | 3.6E2 | 5.1E2 | 2.6E-1 | 6.0E-1 | 3.7E3 | 2.5E3 | 107 | 24 | 107 | 24 | 0.68 |
| Ez | ng/ml | 3.4E0 | 5.3E0 | 1.4E1 | 2.3E1 | 2.7E1 | 4.4E1 | 1.3E-2 | 1.3E-2 | 1.6E2 | 2.0E2 | 111 | 24 | 111 | 24 | 0.59 |
| Fb | ng/ml | 2.5E1 | 2.7E1 | 2.2E1 | 2.6E1 | 1.2E1 | 9.8E1 | 6.6E-1 | 8.1E-1 | 4.3E1 | 4.1E1 | 108 | 24 | 108 | 24 | 0.58 |
| Ex | ng/ml | 5.7E-2 | 1.6E-1 | 1.7E-1 | 4.2E-1 | 3.3E-1 | 8.7E-1 | 3.5E-5 | 1.7E-4 | 2.2E0 | 4.1E0 | 82 | 23 | 82 | 23 | 0.69 |

Figure 28

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fc | pg/ml | 2.2E-1 | 2.2E-1 | 2.0E1 | 4.2E1 | 8.4E1 | 1.0E2 | 2.2E-1 | 2.2E-1 | 4.5E2 | 3.1E2 | 49 | 9 | 49 | 9 | 0.62 |
| Fd | pg/ml | 2.3E1 | 4.9E2 | 4.1E2 | 6.5E3 | 7.3E2 | 1.0E4 | 4.5E-1 | 9.8E-1 | 2.9E3 | 2.5E4 | 49 | 9 | 49 | 9 | 0.71 |
| Fi | pg/ml | 2.5E-1 | 6.9E0 | 8.4E1 | 1.3E2 | 3.0E2 | 2.0E2 | 2.5E-1 | 2.5E-1 | 1.8E3 | 5.3E2 | 49 | 9 | 49 | 9 | 0.68 |
| Fn | ng/ml | 2.1E-1 | 2.5E-1 | 3.7E0 | 4.8E0 | 7.1E0 | 7.2E0 | 1.1E-14 | 1.1E-14 | 3.7E1 | 2.7E1 | 111 | 24 | 111 | 24 | 0.54 |
| Fp | ng/ml | 1.1E1 | 3.1E1 | 2.1E1 | 3.6E1 | 2.5E1 | 3.3E1 | 6.0E-3 | 1.2E0 | 1.3E2 | 1.3E2 | 295 | 61 | 295 | 61 | 0.65 |
| Fr | ng/ml | 3.0E4 | 9.2E4 | 1.1E5 | 2.4E5 | 1.8E5 | 2.7E5 | 1.9E2 | 1.8E3 | 8.4E5 | 8.4E5 | 300 | 63 | 300 | 63 | 0.70 |
| Fw | pg/ml | 2.0E0 | 9.0E0 | 4.0E1 | 7.7E1 | 2.7E2 | 1.9E2 | 1.2E-1 | 1.2E-1 | 3.0E3 | 9.1E2 | 121 | 28 | 121 | 28 | 0.62 |
| Fy | ng/ml | 3.4E1 | 5.9E1 | 5.4E1 | 1.6E2 | 5.4E1 | 2.1E2 | 1.2E-1 | 1.5E0 | 2.8E2 | 6.5E2 | 111 | 21 | 111 | 21 | 0.64 |
| Gh | pg/ml | 3.5E0 | 7.8E-1 | 2.4E1 | 9.0E0 | 5.8E1 | 1.6E1 | 2.9E-2 | 2.9E-2 | 3.2E2 | 4.6E1 | 49 | 9 | 49 | 9 | 0.46 |
| Gb | % | 4.1E1 | 5.3E1 | 4.6E1 | 9.0E1 | 4.1E1 | 9.2E1 | 2.2E0 | 2.5E1 | 2.3E2 | 3.0E2 | 49 | 9 | 49 | 9 | 0.68 |
| Gc | ng/ml | 9.5E1 | 1.4E2 | 1.5E2 | 2.6E2 | 2.0E2 | 2.1E2 | 6.4E0 | 6.5E1 | 1.2E3 | 6.7E2 | 60 | 12 | 60 | 12 | 0.70 |
| Gd | ng/ml | 3.3E1 | 2.7E1 | 3.4E1 | 2.9E1 | 1.8E1 | 2.1E1 | 3.0E0 | 7.6E0 | 8.1E1 | 8.0E1 | 68 | 14 | 68 | 14 | 0.39 |
| Gn | U/ml | 2.1E-1 | 2.8E-1 | 1.3E0 | 9.8E0 | 4.0E0 | 3.3E1 | 5.6E-3 | 2.7E-2 | 3.0E1 | 1.1E2 | 59 | 12 | 59 | 12 | 0.56 |
| Gl | pg/ml | 8.9E3 | 1.3E4 | 1.2E4 | 1.5E4 | 9.5E3 | 1.1E4 | 9.1E1 | 5.2E2 | 3.2E4 | 3.2E4 | 121 | 28 | 121 | 28 | 0.59 |
| Gp | U/ml | 1.2E0 | 9.8E-1 | 2.6E0 | 1.6E0 | 3.6E0 | 2.4E0 | 1.5E-2 | 1.5E-2 | 2.0E1 | 7.8E0 | 121 | 27 | 121 | 27 | 0.41 |
| Gz | ug/ml | 1.5E0 | 9.7E-1 | 5.7E0 | 4.2E0 | 5.7E0 | 5.8E0 | 4.2E-2 | 1.0E-1 | 2.5E1 | 1.9E1 | 74 | 20 | 74 | 20 | 0.47 |
| Ha | ng/ml | 2.0E0 | 3.0E0 | 7.1E0 | 1.6E1 | 1.6E1 | 3.2E1 | 1.7E-2 | 1.7E-2 | 1.0E2 | 1.0E2 | 109 | 24 | 109 | 24 | 0.57 |
| Nm | pg/ml | 1.2E4 | 2.4E4 | 3.0E4 | 7.6E4 | 7.7E4 | 1.4E5 | 1.0E-9 | 1.0E-9 | 9.6E5 | 8.2E5 | 296 | 61 | 296 | 61 | 0.63 |
| Nn | pg/ml | 1.4E2 | 4.9E2 | 1.4E3 | 1.0E4 | 7.1E3 | 4.3E4 | 1.0E-9 | 1.0E-9 | 9.5E4 | 3.1E5 | 296 | 61 | 296 | 61 | 0.68 |
| No | pg/ml | 1.3E1 | 3.3E1 | 2.8E1 | 1.0E2 | 5.3E1 | 1.9E2 | 1.0E-9 | 1.6E0 | 5.6E2 | 9.1E2 | 296 | 61 | 296 | 61 | 0.71 |
| Nq | pg/ml | 1.4E0 | 6.6E0 | 1.9E1 | 4.9E1 | 6.9E1 | 1.2E2 | 1.0E-9 | 1.0E-9 | 6.7E2 | 6.3E2 | 296 | 61 | 296 | 61 | 0.62 |
| Nr | pg/ml | 1.2E0 | 5.7E0 | 1.9E1 | 6.8E1 | 7.6E1 | 2.0E2 | 1.0E-9 | 1.0E-9 | 9.8E2 | 1.4E3 | 296 | 61 | 296 | 61 | 0.65 |
| Ns | pg/ml | 1.0E-9 | 1.0E-9 | 9.0E0 | 1.2E-1 | 6.9E1 | 6.4E-1 | 1.0E-9 | 1.0E-9 | 1.1E3 | 3.6E0 | 296 | 61 | 296 | 61 | 0.48 |
| Nt | pg/ml | 9.8E1 | 1.4E2 | 1.3E2 | 2.2E2 | 1.0E2 | 2.7E2 | 9.8E-1 | 4.5E1 | 8.8E2 | 1.7E3 | 296 | 61 | 296 | 61 | 0.66 |
| Nu | pg/ml | 1.5E1 | 5.0E1 | 5.2E1 | 8.1E1 | 9.2E1 | 9.4E1 | 1.0E-9 | 1.0E-9 | 6.3E2 | 3.7E2 | 296 | 61 | 296 | 61 | 0.63 |
| Lu | pg/ml | 1.0E4 | 1.0E4 | 1.6E4 | 1.1E4 | 4.3E4 | 9.4E3 | 7.7E2 | 5.2E2 | 5.6E5 | 5.7E4 | 296 | 61 | 296 | 61 | 0.49 |
| Lv | pg/ml | 1.0E-9 | 9.9E0 | 1.3E1 | 3.4E1 | 2.5E1 | 5.3E1 | 1.0E-9 | 1.0E-9 | 2.4E2 | 2.6E2 | 296 | 61 | 296 | 61 | 0.62 |
| Lw | pg/ml | 1.0E-9 | 1.0E-9 | 4.1E-1 | 4.9E0 | 5.0E0 | 2.4E1 | 1.0E-9 | 1.0E-9 | 8.0E1 | 1.8E2 | 296 | 61 | 296 | 61 | 0.56 |
| Lx | pg/ml | 1.0E-9 | 1.7E2 | 1.4E2 | 8.6E2 | 5.1E2 | 2.9E3 | 1.0E-9 | 1.0E-9 | 6.2E3 | 2.2E4 | 296 | 61 | 296 | 61 | 0.72 |
| Ly | pg/ml | 1.0E-9 | 1.0E-9 | 9.4E0 | 7.7E0 | 1.8E1 | 1.5E1 | 1.0E-9 | 1.0E-9 | 1.1E2 | 6.0E1 | 296 | 61 | 296 | 61 | 0.48 |
| Lz | pg/ml | 1.0E-9 | 1.0E-9 | 3.3E0 | 4.4E0 | 2.8E1 | 1.4E1 | 1.0E-9 | 1.0E-9 | 4.3E2 | 6.2E1 | 296 | 61 | 296 | 61 | 0.54 |
| Ma | pg/ml | 3.6E2 | 1.2E3 | 1.9E3 | 4.8E3 | 5.4E3 | 9.3E3 | 1.0E-9 | 2.4E1 | 6.5E4 | 5.2E4 | 296 | 61 | 296 | 61 | 0.67 |
| Mb | pg/ml | 2.5E1 | 2.8E1 | 3.2E1 | 3.3E1 | 1.8E1 | 1.5E1 | 9.2E0 | 4.1E0 | 2.1E2 | 7.1E1 | 296 | 61 | 296 | 61 | 0.54 |
| Mc | pg/ml | 1.0E-9 | 1.0E-9 | 6.4E-2 | 1.0E-9 | 8.0E-1 | 0.0E0 | 1.0E-9 | 1.0E-9 | 1.3E1 | 1.0E-9 | 296 | 61 | 296 | 61 | 0.49 |
| Md | pg/ml | 1.0E-9 | 1.0E-9 | 6.6E-1 | 6.9E-1 | 5.6E0 | 3.8E0 | 1.0E-9 | 1.0E-9 | 6.8E1 | 2.9E1 | 296 | 61 | 296 | 61 | 0.52 |
| Me | pg/ml | 3.1E1 | 3.5E1 | 3.1E1 | 3.3E1 | 2.5E1 | 2.5E1 | 1.0E-9 | 1.0E-9 | 3.2E2 | 1.8E2 | 296 | 61 | 296 | 61 | 0.56 |
| Mf | pg/ml | 1.0E-9 | 1.0E-9 | 6.5E-1 | 5.4E-1 | 4.2E0 | 1.6E0 | 1.0E-9 | 1.0E-9 | 5.6E1 | 9.1E0 | 296 | 61 | 296 | 61 | 0.53 |
| Mg | pg/ml | 9.4E-1 | 1.8E0 | 6.2E0 | 1.1E1 | 1.2E1 | 2.4E1 | 1.0E-9 | 1.0E-9 | 9.2E1 | 1.5E2 | 296 | 61 | 296 | 61 | 0.55 |
| Mh | pg/ml | 1.0E-9 | 1.0E-9 | 1.1E0 | 1.7E0 | 7.8E0 | 6.1E0 | 1.0E-9 | 1.0E-9 | 1.1E2 | 4.2E1 | 296 | 61 | 296 | 61 | 0.56 |
| Mi | pg/ml | 1.0E-9 | 1.0E-9 | 9.1E-1 | 1.8E1 | 8.6E0 | 7.8E1 | 1.0E-9 | 1.0E-9 | 1.2E2 | 5.2E2 | 296 | 61 | 296 | 61 | 0.57 |
| Mj | pg/ml | 1.0E-9 | 1.0E-9 | 5.8E0 | 1.4E1 | 3.3E1 | 3.8E1 | 1.0E-9 | 1.0E-9 | 4.6E2 | 2.1E2 | 296 | 61 | 296 | 61 | 0.58 |
| Mk | pg/ml | 5.3E-1 | 3.7E0 | 1.6E1 | 1.6E1 | 9.9E1 | 6.6E1 | 1.0E-9 | 1.0E-9 | 1.3E3 | 5.0E2 | 296 | 61 | 296 | 61 | 0.53 |
| Ml | pg/ml | 1.0E-9 | 1.0E-9 | 9.7E0 | 1.7E1 | 1.2E2 | 7.9E1 | 1.0E-9 | 1.0E-9 | 2.1E3 | 5.1E2 | 296 | 61 | 296 | 61 | 0.49 |
| Mm | pg/ml | 4.6E2 | 1.0E3 | 9.7E2 | 1.8E3 | 1.3E3 | 2.1E3 | 1.0E-9 | 1.0E-9 | 1.0E4 | 1.0E4 | 296 | 61 | 296 | 61 | 0.65 |
| Mn | pg/ml | 5.3E0 | 1.1E1 | 1.1E1 | 1.3E1 | 2.6E1 | 9.6E0 | 1.0E-9 | 1.1E0 | 3.5E2 | 5.1E1 | 296 | 61 | 296 | 61 | 0.70 |
| Mp | pg/ml | 1.0E-9 | 6.6E0 | 1.0E1 | 7.6E1 | 4.1E1 | 3.1E2 | 1.0E-9 | 1.0E-9 | 6.3E2 | 2.4E3 | 296 | 61 | 296 | 61 | 0.63 |
| Mq | pg/ml | 1.0E-9 | 1.0E-9 | 2.2E0 | 5.5E0 | 1.4E1 | 1.8E1 | 1.0E-9 | 1.0E-9 | 1.8E2 | 1.0E2 | 296 | 61 | 296 | 61 | 0.54 |
| Mr | pg/ml | 1.0E-9 | 1.0E-9 | 1.6E1 | 1.7E2 | 8.9E1 | 5.7E2 | 1.0E-9 | 1.0E-9 | 1.4E3 | 3.4E3 | 296 | 61 | 296 | 61 | 0.60 |
| Ms | pg/ml | 3.4E2 | 2.5E2 | 4.9E2 | 4.1E2 | 5.6E2 | 6.5E2 | 1.0E-9 | 1.0E-9 | 3.3E3 | 4.7E3 | 296 | 61 | 296 | 61 | 0.44 |
| Mt | pg/ml | 1.0E-9 | 1.6E0 | 7.3E0 | 7.8E1 | 4.5E1 | 4.1E2 | 1.0E-9 | 1.0E-9 | 7.1E2 | 3.2E3 | 296 | 61 | 296 | 61 | 0.67 |
| Mu | pg/ml | 1.0E-9 | 1.0E-9 | 1.6E0 | 2.3E0 | 1.5E1 | 8.0E0 | 1.0E-9 | 1.0E-9 | 2.3E2 | 4.8E1 | 296 | 61 | 296 | 61 | 0.55 |
| Mv | pg/ml | 1.0E-9 | 1.0E-9 | 6.4E1 | 1.0E2 | 3.6E2 | 2.4E2 | 1.0E-9 | 1.0E-9 | 4.5E3 | 9.2E2 | 296 | 61 | 296 | 61 | 0.57 |
| Mw | pg/ml | 3.0E1 | 9.8E1 | 2.7E2 | 4.8E2 | 1.4E3 | 1.1E3 | 1.0E-9 | 1.0E-9 | 1.8E4 | 5.3E3 | 296 | 61 | 296 | 61 | 0.66 |
| Mx | pg/ml | 1.0E-9 | 1.0E-9 | 3.4E-1 | 8.7E-1 | 2.0E0 | 2.8E0 | 1.0E-9 | 1.0E-9 | 3.2E1 | 2.0E1 | 296 | 61 | 296 | 61 | 0.58 |
| My | pg/ml | 1.0E-9 | 1.0E-9 | 3.6E2 | 1.6E2 | 2.6E3 | 3.9E2 | 1.0E-9 | 1.0E-9 | 3.9E4 | 1.9E3 | 296 | 61 | 296 | 61 | 0.56 |
| Mz | pg/ml | 9.9E0 | 3.0E1 | 2.3E1 | 1.0E2 | 4.9E1 | 2.9E2 | 1.0E-9 | 1.0E-9 | 5.5E2 | 1.9E3 | 296 | 61 | 296 | 61 | 0.74 |
| Na | pg/ml | 1.0E-9 | 1.0E-9 | 6.8E-1 | 1.3E0 | 1.9E0 | 5.6E0 | 1.0E-9 | 1.0E-9 | 9.6E0 | 4.2E1 | 296 | 61 | 296 | 61 | 0.49 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nb | pg/ml | 2.1E0 | 3.3E0 | 3.5E0 | 1.0E1 | 1.1E1 | 3.0E1 | 1.0E-9 | 1.0E-9 | 1.5E2 | 2.1E2 | 296 | 61 | 296 | 61 | 0.61 |
| Nc | pg/ml | 3.5E2 | 1.0E2 | 5.3E2 | 3.8E2 | 7.5E2 | 5.8E2 | 1.0E-9 | 1.0E-9 | 9.2E3 | 3.2E3 | 296 | 61 | 296 | 61 | 0.41 |
| Nd | pg/ml | 2.8E1 | 2.5E1 | 2.8E1 | 6.3E1 | 7.2E1 | 2.7E2 | 1.0E-9 | 1.0E-9 | 1.2E3 | 2.1E3 | 296 | 61 | 296 | 61 | 0.54 |
| Ne | pg/ml | 4.4E2 | 3.5E2 | 5.4E2 | 4.3E2 | 5.7E2 | 5.3E2 | 1.0E-9 | 1.0E-9 | 7.0E3 | 3.6E3 | 296 | 61 | 296 | 61 | 0.42 |
| Nf | pg/ml | 1.0E-9 | 1.0E-9 | 2.4E0 | 5.9E0 | 8.7E0 | 2.3E1 | 1.0E-9 | 1.0E-9 | 8.2E1 | 1.3E2 | 296 | 61 | 296 | 61 | 0.49 |
| Ng | pg/ml | 1.2E1 | 9.6E0 | 9.3E1 | 7.7E1 | 1.9E2 | 1.2E2 | 1.0E-9 | 1.0E-9 | 1.6E3 | 5.3E2 | 296 | 61 | 296 | 61 | 0.53 |
| Nh | pg/ml | 6.3E1 | 5.2E1 | 8.3E1 | 6.1E1 | 7.6E1 | 7.2E1 | 1.0E-9 | 1.0E-9 | 5.6E2 | 5.1E2 | 296 | 61 | 296 | 61 | 0.39 |
| Ni | pg/ml | 9.4E0 | 1.0E-9 | 8.2E1 | 1.0E2 | 1.3E2 | 1.9E2 | 1.0E-9 | 1.0E-9 | 7.1E2 | 1.1E3 | 296 | 61 | 296 | 61 | 0.48 |
| Nj | pg/ml | 7.4E0 | 6.2E0 | 1.1E1 | 8.3E0 | 1.2E1 | 9.5E0 | 1.0E-9 | 1.0E-9 | 6.9E1 | 4.6E1 | 296 | 61 | 296 | 61 | 0.40 |
| Nk | pg/ml | 1.8E1 | 1.4E1 | 3.2E1 | 3.4E1 | 3.7E1 | 4.8E1 | 1.0E-9 | 1.0E-9 | 2.0E2 | 2.0E2 | 296 | 61 | 296 | 61 | 0.48 |
| Nl | pg/ml | 4.4E1 | 3.3E1 | 5.9E1 | 4.2E1 | 7.9E1 | 4.8E1 | 1.0E-9 | 1.0E-9 | 1.1E3 | 2.3E2 | 296 | 61 | 296 | 61 | 0.40 |
| Hl | pg/ml | 4.6E0 | 1.1E1 | 3.3E1 | 4.2E2 | 5.6E1 | 1.2E3 | 1.0E-9 | 1.0E-9 | 3.0E2 | 3.6E3 | 49 | 9 | 49 | 9 | 0.56 |
| Ho | pg/ml | 1.7E1 | 2.7E1 | 2.2E1 | 9.0E1 | 2.0E1 | 1.3E2 | 1.0E-9 | 7.6E0 | 8.7E1 | 3.9E2 | 49 | 9 | 49 | 9 | 0.68 |
| Hp | pg/ml | 1.6E0 | 4.0E0 | 9.4E1 | 3.0E2 | 2.7E2 | 4.4E2 | 1.0E-9 | 8.8E-1 | 8.9E2 | 8.9E2 | 49 | 9 | 49 | 9 | 0.68 |
| Tz | pg/ml | 4.0E3 | 6.5E3 | 6.7E3 | 1.1E5 | 8.5E2 | 4.2E5 | 1.0E-9 | 6.3E2 | 5.3E4 | 2.1E6 | 111 | 24 | 111 | 24 | 0.61 |
| Ua | pg/ml | 3.2E3 | 5.6E3 | 3.3E4 | 1.4E4 | 2.0E5 | 2.3E4 | 1.0E-9 | 9.1E2 | 2.1E6 | 9.9E4 | 111 | 24 | 111 | 24 | 0.59 |
| Ub | pg/ml | 5.8E2 | 4.0E2 | 9.0E2 | 5.9E2 | 1.2E3 | 8.3E2 | 1.0E-9 | 2.3E0 | 9.8E3 | 4.1E3 | 111 | 24 | 111 | 24 | 0.38 |
| Ue | pg/ml | 3.1E1 | 2.3E1 | 3.7E1 | 3.5E1 | 3.2E1 | 3.7E1 | 9.8E-2 | 4.5E0 | 2.7E2 | 1.4E2 | 111 | 24 | 111 | 24 | 0.43 |
| Uc | pg/ml | 7.0E2 | 8.7E2 | 1.1E3 | 4.5E3 | 1.3E3 | 1.2E4 | 1.0E-9 | 4.1E1 | 8.3E3 | 5.7E4 | 111 | 24 | 111 | 24 | 0.60 |
| Ud | pg/ml | 1.0E-9 | 1.0E-9 | 3.5E0 | 2.2E0 | 3.7E1 | 1.1E1 | 1.0E-9 | 1.0E-9 | 3.9E2 | 5.3E1 | 111 | 24 | 111 | 24 | 0.52 |
| Hq | pg/ml | 1.2E0 | 1.1E0 | 1.7E2 | 6.2E1 | 2.0E3 | 3.6E2 | 1.0E-9 | 1.0E-9 | 2.8E4 | 2.8E3 | 294 | 61 | 294 | 61 | 0.53 |
| Hr | pg/ml | 9.4E1 | 7.9E1 | 6.9E2 | 4.7E2 | 1.4E3 | 1.3E3 | 1.0E-9 | 1.0E-9 | 1.2E4 | 8.9E3 | 294 | 61 | 294 | 61 | 0.43 |
| Hu | pg/ml | 3.8E0 | 6.3E1 | 5.3E3 | 6.6E2 | 4.3E4 | 1.4E3 | 1.0E-9 | 1.0E-9 | 6.3E5 | 6.5E3 | 294 | 61 | 294 | 61 | 0.59 |
| Hv | pg/ml | 1.5E0 | 1.0E0 | 2.5E0 | 2.0E1 | 5.8E0 | 1.2E2 | 1.0E-9 | 1.0E-9 | 6.9E1 | 8.9E2 | 294 | 61 | 294 | 61 | 0.51 |
| Hw | pg/ml | 6.4E0 | 5.7E0 | 1.5E1 | 1.8E2 | 4.7E1 | 1.2E3 | 1.0E-9 | 4.6E-1 | 6.4E2 | 9.4E3 | 294 | 61 | 294 | 61 | 0.49 |
| Hx | pg/ml | 8.6E0 | 1.2E1 | 5.7E1 | 6.3E1 | 5.4E2 | 1.9E2 | 1.0E-9 | 1.0E-9 | 9.3E3 | 1.3E3 | 294 | 61 | 294 | 61 | 0.59 |
| Ib | ng/ml | 3.9E-2 | 2.8E-2 | 1.2E0 | 2.5E0 | 4.9E0 | 1.1E1 | 1.0E-9 | 1.0E-9 | 3.6E1 | 5.6E1 | 109 | 24 | 109 | 24 | 0.50 |
| Ic | U/ml | 2.2E2 | 2.2E2 | 3.7E2 | 2.9E3 | 9.6E2 | 1.3E4 | 2.4E0 | 2.5E1 | 8.6E3 | 6.5E4 | 109 | 24 | 109 | 24 | 0.60 |
| Id | U/ml | 5.5E-1 | 1.2E0 | 1.1E0 | 2.1E1 | 1.5E0 | 8.8E1 | 1.0E-9 | 2.7E-1 | 1.0E1 | 4.3E2 | 109 | 24 | 109 | 24 | 0.69 |
| Tt | pg/ml | 1.7E2 | 1.8E2 | 1.7E2 | 1.9E2 | 5.4E1 | 7.2E1 | 4.3E1 | 1.1E2 | 3.6E2 | 4.4E2 | 103 | 21 | 103 | 21 | 0.57 |
| To | pg/ml | 1.6E0 | 1.8E0 | 2.1E0 | 2.3E0 | 2.9E0 | 2.7E0 | 1.0E-9 | 1.0E-9 | 2.3E1 | 1.2E1 | 109 | 22 | 109 | 22 | 0.54 |
| Tr | pg/ml | 3.2E0 | 5.2E0 | 7.8E0 | 1.4E1 | 3.0E1 | 2.0E1 | 1.0E-9 | 3.9E-1 | 3.1E2 | 7.6E1 | 107 | 21 | 107 | 21 | 0.63 |
| Tn | pg/ml | 3.0E1 | 5.4E1 | 1.0E2 | 2.9E2 | 2.9E2 | 6.1E2 | 1.0E-9 | 1.3E1 | 1.8E3 | 2.3E3 | 109 | 22 | 109 | 22 | 0.67 |
| Tv | ng/ml | 1.2E1 | 1.1E1 | 1.7E1 | 4.1E2 | 1.8E1 | 1.5E3 | 1.0E-9 | 1.0E-9 | 1.1E2 | 7.1E3 | 109 | 22 | 109 | 22 | 0.52 |
| Ih | ng/ml | 5.9E1 | 1.9E2 | 2.1E2 | 5.2E2 | 3.8E2 | 7.4E2 | 1.0E-9 | 1.0E-9 | 2.5E3 | 3.6E3 | 295 | 61 | 295 | 61 | 0.64 |
| Ii | ng/ml | 7.5E1 | 1.1E2 | 2.0E2 | 3.4E2 | 4.9E2 | 7.6E2 | 7.3E-1 | 7.5E-1 | 5.2E3 | 4.5E3 | 295 | 61 | 295 | 61 | 0.60 |
| Ij | ng/ml | 7.2E1 | 1.4E2 | 1.8E2 | 6.4E2 | 6.0E2 | 2.4E3 | 2.8E0 | 9.5E0 | 6.4E3 | 2.4E4 | 292 | 60 | 292 | 60 | 0.72 |
| Ik | ng/ml | 1.1E1 | 1.4E1 | 1.5E3 | 1.9E2 | 1.2E4 | 3.9E2 | 5.9E-1 | 6.2E-1 | 1.2E5 | 1.5E3 | 292 | 60 | 292 | 60 | 0.53 |
| Il | ng/ml | 3.3E2 | 5.2E2 | 1.2E3 | 2.1E3 | 2.8E3 | 3.7E3 | 1.0E-9 | 1.0E-9 | 1.2E4 | 1.2E4 | 290 | 60 | 290 | 60 | 0.57 |
| Im | ng/ml | 2.0E2 | 7.0E2 | 3.4E2 | 1.3E3 | 5.2E2 | 2.3E3 | 1.4E1 | 2.2E1 | 6.0E3 | 1.5E4 | 291 | 61 | 291 | 61 | 0.75 |
| In | ng/ml | 3.8E0 | 2.2E0 | 2.1E1 | 9.8E1 | 9.4E1 | 5.8E2 | 1.0E-9 | 1.0E-9 | 1.1E3 | 4.5E3 | 295 | 61 | 295 | 61 | 0.46 |
| Hb | ng/ml | 2.1E1 | 4.3E1 | 3.1E1 | 5.3E1 | 3.1E1 | 5.0E1 | 4.8E-1 | 4.5E0 | 2.0E2 | 1.9E2 | 111 | 25 | 111 | 25 | 0.66 |
| Hc | pg/ml | 6.9E2 | 5.0E2 | 3.2E3 | 3.2E3 | 1.1E4 | 1.0E4 | 1.0E-9 | 1.0E-9 | 1.0E5 | 5.0E4 | 111 | 25 | 111 | 25 | 0.44 |
| Hf | ng/ml | 1.9E2 | 1.9E2 | 4.2E2 | 2.8E2 | 5.9E2 | 2.8E2 | 1.0E-9 | 1.0E-9 | 3.2E3 | 9.9E2 | 111 | 25 | 111 | 25 | 0.47 |
| Io | ng/ml | 7.6E3 | 1.8E4 | 1.9E4 | 2.2E4 | 4.9E4 | 2.4E4 | 1.0E-9 | 6.2E2 | 7.1E5 | 1.1E5 | 295 | 61 | 295 | 61 | 0.62 |
| Ip | ng/ml | 8.2E0 | 3.0E1 | 2.0E1 | 3.1E1 | 2.7E1 | 2.2E1 | 1.0E-9 | 1.6E-2 | 2.3E2 | 8.3E1 | 295 | 61 | 295 | 61 | 0.67 |
| Iq | ug/ml | 1.0E-1 | 1.9E-1 | 4.7E1 | 5.5E0 | 7.9E2 | 2.8E1 | 1.0E-9 | 1.0E-9 | 1.4E4 | 2.2E2 | 295 | 61 | 295 | 61 | 0.61 |
| Ir | ug/ml | 3.4E-1 | 1.2E0 | 4.4E0 | 1.5E1 | 3.4E1 | 5.3E1 | 1.0E-9 | 1.0E-9 | 5.1E2 | 3.7E2 | 294 | 61 | 294 | 61 | 0.68 |
| Is | ng/ml | 1.7E0 | 7.6E0 | 7.6E0 | 2.7E1 | 3.4E1 | 4.7E1 | 1.0E-9 | 3.3E-2 | 5.5E2 | 2.6E2 | 295 | 61 | 295 | 61 | 0.68 |
| It | ng/ml | 1.7E0 | 4.3E0 | 2.2E1 | 3.0E1 | 1.1E2 | 1.1E2 | 1.0E-9 | 1.0E-9 | 1.1E3 | 6.8E2 | 295 | 61 | 295 | 61 | 0.65 |
| Iu | ng/ml | 1.7E2 | 1.8E2 | 1.3E3 | 2.2E3 | 4.1E3 | 5.5E3 | 1.0E-9 | 1.0E-9 | 2.9E4 | 2.4E4 | 295 | 61 | 295 | 61 | 0.54 |
| Iv | ng/ml | 1.1E1 | 2.3E1 | 8.9E1 | 2.5E2 | 9.3E2 | 8.2E2 | 1.0E-9 | 1.0E-9 | 1.6E4 | 3.8E3 | 294 | 61 | 294 | 61 | 0.63 |
| Iz | ng/ml | 1.2E2 | 1.9E2 | 3.8E2 | 3.1E2 | 7.7E2 | 3.9E2 | 1.5E0 | 8.8E-1 | 6.1E3 | 1.7E3 | 111 | 25 | 111 | 25 | 0.53 |
| Yg | pg/ml | 2.4E2 | 1.7E3 | 1.7E3 | 1.6E3 | 7.4E3 | 1.3E3 | 1.0E-9 | 1.3E2 | 5.0E4 | 3.9E3 | 46 | 8 | 46 | 8 | 0.73 |
| Yh | pg/ml | 2.1E2 | 5.7E2 | 4.2E2 | 6.4E2 | 6.0E2 | 5.9E2 | 1.0E-9 | 1.0E-9 | 3.0E3 | 1.4E3 | 46 | 8 | 46 | 8 | 0.60 |
| Yi | pg/ml | 2.6E2 | 1.4E3 | 4.6E2 | 5.3E3 | 4.8E2 | 9.0E3 | 1.0E-9 | 2.4E2 | 2.0E3 | 2.6E4 | 46 | 8 | 46 | 8 | 0.85 |
| Yk | U/ml | 1.0E-9 | 1.0E-9 | 2.1E-1 | 3.3E-1 | 6.1E-1 | 6.0E-1 | 1.0E-9 | 1.0E-9 | 3.0E0 | 1.4E0 | 46 | 8 | 46 | 8 | 0.53 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yj | pg/ml | 1.5E2 | 9.4E1 | 3.2E2 | 1.3E2 | 5.3E2 | 1.0E2 | 1.0E-9 | 5.9E1 | 3.2E3 | 3.7E2 | 46 | 8 | 46 | 8 | 0.37 |
| Yd | ng/ml | 2.2E-1 | 1.9E-1 | 3.6E-1 | 6.2E-1 | 4.2E-1 | 8.8E-1 | 6.6E-3 | 1.7E-2 | 1.8E0 | 2.3E0 | 49 | 9 | 49 | 9 | 0.52 |
| Wb | pg/ml | 2.7E4 | 3.5E4 | 3.3E4 | 1.2E5 | 1.9E4 | 2.0E5 | 4.9E3 | 1.4E4 | 8.4E4 | 6.4E5 | 49 | 9 | 49 | 9 | 0.70 |
| Vz | pg/ml | 3.5E0 | 5.0E0 | 4.4E0 | 6.0E0 | 4.1E0 | 6.7E0 | 1.0E-9 | 7.6E-2 | 2.1E1 | 2.2E1 | 49 | 9 | 49 | 9 | 0.56 |
| Si | ng/ml | 1.2E0 | 1.9E0 | 1.8E0 | 2.7E0 | 2.5E0 | 2.1E0 | 8.6E-3 | 5.6E-1 | 1.0E1 | 6.0E0 | 49 | 9 | 49 | 9 | 0.69 |
| Sf | mIU/mL | 1.3E1 | 2.0E1 | 5.0E1 | 2.7E1 | 1.1E2 | 2.4E1 | 6.2E-1 | 6.7E0 | 7.2E2 | 8.3E1 | 49 | 9 | 49 | 9 | 0.57 |
| Sh | mIU/mL | 1.6E1 | 1.1E1 | 4.5E1 | 1.6E1 | 9.4E1 | 1.6E1 | 7.8E-2 | 4.2E0 | 5.7E2 | 5.8E1 | 49 | 9 | 49 | 9 | 0.46 |
| Sj | ng/ml | 4.4E-1 | 4.6E-1 | 4.2E-1 | 4.6E-1 | 9.0E-2 | 1.2E-1 | 2.5E-1 | 3.4E-1 | 6.6E-1 | 7.2E-1 | 49 | 9 | 49 | 9 | 0.58 |
| Rc | pg/ml | 6.5E3 | 7.6E3 | 7.8E3 | 7.5E3 | 6.2E3 | 3.8E3 | 3.9E2 | 1.1E3 | 3.9E4 | 1.5E4 | 111 | 24 | 111 | 24 | 0.54 |
| Rb | pg/ml | 7.5E-1 | 7.5E-1 | 2.7E0 | 4.2E0 | 4.2E0 | 1.1E1 | 1.0E-9 | 1.0E-9 | 2.0E1 | 5.6E1 | 111 | 24 | 111 | 24 | 0.53 |
| Zq | 2.6ng/ml | 2.4E2 | 4.0E2 | 2.8E2 | 4.7E2 | 2.1E2 | 2.1E2 | 1.4E1 | 3.0E2 | 9.7E2 | 9.7E2 | 48 | 8 | 48 | 8 | 0.76 |
| Zw | 2.5ng/ml | 4.8E0 | 5.3E0 | 8.6E0 | 2.0E1 | 1.1E1 | 2.5E1 | 1.4E-1 | 7.7E-1 | 5.9E1 | 6.3E1 | 49 | 9 | 49 | 9 | 0.60 |
| Zx | 2.3mU/ml | 1.2E-1 | 1.8E-1 | 2.7E-1 | 4.0E-1 | 5.0E-1 | 5.8E-1 | 3.2E-2 | 7.7E-2 | 2.9E0 | 1.9E0 | 49 | 9 | 49 | 9 | 0.66 |
| Pz | ng/ml | 3.2E3 | 1.0E4 | 5.4E3 | 6.9E3 | 6.1E3 | 4.7E3 | 1.6E1 | 4.0E1 | 7.0E4 | 2.5E4 | 291 | 61 | 291 | 61 | 0.62 |
| Qa | ng/ml | 3.3E3 | 9.0E3 | 6.2E3 | 1.5E4 | 7.4E3 | 2.9E4 | 1.5E2 | 2.9E2 | 4.2E4 | 2.2E5 | 291 | 61 | 291 | 61 | 0.68 |
| Qb | ng/ml | 1.0E2 | 2.0E2 | 2.1E2 | 3.8E2 | 4.0E2 | 5.8E2 | 7.9E-1 | 8.7E0 | 5.3E3 | 4.1E3 | 291 | 61 | 291 | 61 | 0.64 |
| Qc | ng/ml | 1.9E2 | 4.8E2 | 4.1E2 | 6.8E2 | 5.5E2 | 7.5E2 | 1.0E-9 | 1.0E-9 | 3.8E3 | 4.3E3 | 291 | 61 | 291 | 61 | 0.63 |
| Qd | ng/ml | 8.2E3 | 2.0E4 | 2.3E4 | 5.3E4 | 1.2E5 | 7.9E4 | 1.5E2 | 1.7E3 | 2.0E6 | 4.3E5 | 291 | 61 | 291 | 61 | 0.70 |
| Qe | ng/ml | 7.7E2 | 2.3E3 | 1.9E3 | 3.2E3 | 6.0E3 | 3.3E3 | 1.0E-9 | 8.8E0 | 9.7E4 | 1.8E4 | 291 | 61 | 291 | 61 | 0.68 |
| Jd | ng/ml | 8.4E-1 | 1.4E0 | 4.1E0 | 3.7E0 | 1.6E1 | 5.4E0 | 1.0E-9 | 1.0E-9 | 1.2E2 | 2.1E1 | 111 | 24 | 111 | 24 | 0.62 |
| Je | ng/ml | 1.0E-9 | 5.0E-1 | 1.8E0 | 1.8E0 | 5.2E0 | 2.8E0 | 1.0E-9 | 1.0E-9 | 4.6E1 | 1.1E1 | 111 | 24 | 111 | 24 | 0.57 |
| Jf | ng/ml | 1.0E-9 | 1.0E-9 | 1.3E0 | 7.6E-1 | 2.4E0 | 1.3E0 | 1.0E-9 | 1.0E-9 | 1.2E1 | 3.9E0 | 111 | 24 | 111 | 24 | 0.47 |
| Jg | ng/ml | 3.8E2 | 1.2E3 | 7.1E2 | 1.3E3 | 9.4E2 | 1.2E3 | 5.8E0 | 4.5E1 | 1.0E4 | 7.1E3 | 294 | 61 | 294 | 61 | 0.70 |
| Jh | ng/ml | 2.6E0 | 7.5E0 | 2.1E1 | 3.6E1 | 8.7E1 | 8.1E1 | 1.0E-9 | 1.0E-9 | 1.2E3 | 4.9E2 | 294 | 61 | 294 | 61 | 0.63 |
| Ji | ng/ml | 5.1E1 | 1.3E2 | 7.3E1 | 2.1E2 | 7.6E1 | 2.2E2 | 1.1E0 | 2.0E1 | 5.3E2 | 1.3E3 | 294 | 61 | 294 | 61 | 0.77 |
| Sr | pg/mL | 3.4E2 | 1.0E3 | 7.6E2 | 2.4E3 | 1.1E3 | 4.3E3 | 1.0E-9 | 9.2E1 | 4.8E3 | 2.1E4 | 110 | 24 | 110 | 24 | 0.70 |
| Ss | pg/mL | 9.3E4 | 6.8E4 | 1.5E5 | 1.2E5 | 1.9E5 | 1.3E5 | 2.7E3 | 7.8E3 | 1.3E6 | 5.7E5 | 110 | 24 | 110 | 24 | 0.46 |
| St | pg/mL | 2.3E7 | 8.2E7 | 5.6E7 | 1.5E8 | 1.3E8 | 3.4E8 | 1.0E-9 | 2.3E6 | 1.2E9 | 1.7E9 | 109 | 24 | 109 | 24 | 0.68 |
| Wc | ng/ml | 1.0E-9 | 1.0E-9 | 5.8E-2 | 2.8E-1 | 1.0E-1 | 6.0E-1 | 1.0E-9 | 1.0E-9 | 5.2E-1 | 1.8E0 | 49 | 9 | 49 | 9 | 0.52 |
| Wd | ng/ml | 9.3E0 | 1.8E1 | 2.7E1 | 1.0E2 | 5.9E1 | 1.7E2 | 1.0E0 | 3.5E0 | 2.9E2 | 4.1E2 | 49 | 9 | 49 | 9 | 0.71 |
| We | ng/ml | 2.9E-1 | 5.8E-1 | 1.0E0 | 3.5E0 | 1.7E0 | 7.4E0 | 1.0E-9 | 1.5E-1 | 9.7E0 | 2.3E1 | 49 | 9 | 49 | 9 | 0.66 |
| Wg | ng/ml | 1.0E-9 | 1.0E-9 | 3.3E-4 | 5.9E-2 | 2.3E-3 | 1.8E-1 | 1.0E-9 | 1.0E-9 | 1.6E-2 | 5.3E-1 | 49 | 9 | 49 | 9 | 0.55 |
| Wh | ng/ml | 9.7E-3 | 2.0E-2 | 4.4E-2 | 6.3E-2 | 9.8E-2 | 1.1E-1 | 1.0E-9 | 1.0E-9 | 4.2E-1 | 3.4E-1 | 49 | 9 | 49 | 9 | 0.64 |
| Wf | ng/ml | 1.0E-9 | 1.0E-9 | 9.4E-2 | 3.1E-1 | 2.1E-1 | 7.6E-1 | 1.0E-9 | 1.0E-9 | 1.2E0 | 2.3E0 | 49 | 9 | 49 | 9 | 0.45 |
| Ra | pg/ml | 1.0E-9 | 1.0E-9 | 4.1E-1 | 3.1E0 | 9.7E-1 | 1.3E1 | 1.0E-9 | 1.0E-9 | 3.8E0 | 6.4E1 | 111 | 24 | 111 | 24 | 0.52 |
| Qz | pg/ml | 9.8E0 | 1.0E1 | 5.3E1 | 4.5E1 | 8.8E1 | 7.4E1 | 1.0E-9 | 1.0E-9 | 4.5E2 | 2.3E2 | 111 | 24 | 111 | 24 | 0.48 |
| Qy | pg/ml | 3.8E-1 | 5.6E-1 | 8.2E0 | 3.2E1 | 4.7E1 | 1.5E2 | 1.0E-9 | 1.0E-9 | 4.3E2 | 7.3E2 | 111 | 24 | 111 | 24 | 0.58 |
| Qx | pg/ml | 1.0E-9 | 1.0E-9 | 2.9E0 | 7.2E0 | 1.8E1 | 2.3E1 | 1.0E-9 | 1.0E-9 | 1.9E2 | 1.1E2 | 111 | 24 | 111 | 24 | 0.55 |
| Qw | pg/ml | 1.0E-9 | 1.0E-9 | 3.0E0 | 1.6E0 | 1.0E1 | 4.7E0 | 1.0E-9 | 1.0E-9 | 6.6E1 | 2.3E1 | 111 | 24 | 111 | 24 | 0.47 |
| Qv | pg/ml | 1.9E4 | 1.0E4 | 3.2E4 | 5.3E4 | 4.9E4 | 1.9E5 | 1.0E-9 | 4.0E2 | 3.7E5 | 9.4E5 | 111 | 24 | 111 | 24 | 0.35 |
| Qu | pg/ml | 7.8E0 | 7.7E0 | 9.1E1 | 9.7E1 | 1.8E2 | 2.0E2 | 1.0E-9 | 1.0E-9 | 9.8E2 | 7.3E2 | 111 | 24 | 111 | 24 | 0.50 |
| Qt | pg/ml | 1.2E1 | 1.4E1 | 4.5E1 | 4.2E1 | 1.0E2 | 6.8E1 | 1.0E-9 | 1.0E-9 | 7.1E2 | 2.2E2 | 111 | 24 | 111 | 24 | 0.52 |
| Qh | ng/ml | 1.8E1 | 3.6E1 | 3.9E1 | 1.0E2 | 6.1E1 | 1.8E2 | 2.5E-1 | 3.3E0 | 3.4E2 | 8.0E2 | 111 | 24 | 111 | 24 | 0.64 |
| Qg | ng/ml | 7.6E0 | 5.1E0 | 1.4E1 | 1.0E1 | 2.7E1 | 1.7E1 | 1.5E-1 | 3.3E-1 | 2.7E2 | 8.1E1 | 111 | 24 | 111 | 24 | 0.42 |
| Jj | ng/ml | 5.7E2 | 2.5E2 | 2.1E3 | 4.8E2 | 2.0E4 | 4.8E2 | 2.3E0 | 8.7E0 | 3.4E5 | 1.9E3 | 294 | 61 | 294 | 61 | 0.36 |
| Jk | ng/ml | 2.6E0 | 4.7E0 | 2.0E1 | 3.0E1 | 4.9E1 | 5.2E1 | 1.0E-9 | 1.2E-1 | 3.9E2 | 2.4E2 | 294 | 61 | 294 | 61 | 0.59 |
| Jl | ng/ml | 4.6E-1 | 8.8E-1 | 1.6E0 | 1.7E2 | 3.7E0 | 1.3E3 | 1.2E-3 | 7.8E-2 | 2.0E1 | 9.9E3 | 294 | 61 | 294 | 61 | 0.65 |
| Jm | ng/ml | 1.8E1 | 3.5E1 | 6.2E1 | 9.2E1 | 1.4E2 | 2.7E2 | 1.0E-9 | 4.0E-1 | 1.4E3 | 2.1E3 | 294 | 61 | 294 | 61 | 0.57 |
| Jn | pg/ml | 3.1E-1 | 6.5E-1 | 3.5E0 | 2.8E1 | 3.7E1 | 1.2E2 | 1.0E-9 | 1.0E-9 | 6.2E2 | 7.3E2 | 294 | 61 | 294 | 61 | 0.66 |
| Jo | pg/ml | 3.6E3 | 4.7E3 | 4.7E3 | 7.6E3 | 3.9E3 | 1.4E4 | 2.0E1 | 2.4E1 | 2.4E4 | 1.0E5 | 294 | 61 | 294 | 61 | 0.54 |
| Jp | pg/ml | 6.9E4 | 9.2E4 | 7.0E4 | 1.0E5 | 3.5E4 | 5.2E4 | 5.8E2 | 2.8E4 | 1.9E5 | 3.8E5 | 294 | 61 | 294 | 61 | 0.71 |
| Jq | pg/ml | 9.2E1 | 1.5E2 | 1.5E2 | 4.6E2 | 2.0E2 | 1.2E3 | 1.0E0 | 5.6E0 | 2.0E3 | 8.7E3 | 294 | 61 | 294 | 61 | 0.61 |
| Jr | pg/ml | 2.8E0 | 1.3E1 | 5.7E1 | 2.7E2 | 6.3E2 | 1.2E3 | 1.0E-9 | 1.0E-9 | 1.1E4 | 7.4E3 | 294 | 61 | 294 | 61 | 0.67 |
| Js | pg/ml | 1.4E1 | 2.0E1 | 6.8E1 | 2.0E2 | 5.9E2 | 6.4E2 | 1.0E-9 | 2.7E0 | 1.0E4 | 3.0E3 | 294 | 61 | 294 | 61 | 0.68 |
| Jt | pg/ml | 2.3E3 | 3.3E3 | 2.8E3 | 5.9E3 | 2.2E3 | 8.7E3 | 2.2E1 | 1.5E2 | 2.2E4 | 5.2E4 | 294 | 61 | 294 | 61 | 0.66 |
| Xa | pg/ml | 1.0E-9 | 2.4E1 | 8.4E0 | 2.2E2 | 1.7E1 | 4.2E2 | 1.0E-9 | 2.9E0 | 9.6E1 | 1.2E3 | 49 | 9 | 49 | 9 | 0.82 |
| Ye | pg/ml | 1.0E-9 | 1.0E-9 | 4.7E0 | 8.0E-1 | 1.4E1 | 2.4E0 | 1.0E-9 | 1.0E-9 | 6.9E1 | 7.2E0 | 49 | 9 | 49 | 9 | 0.41 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Tm | pg/ml | 1.0E-9 | 1.0E-9 | 2.9E0 | 9.3E-1 | 4.6E0 | 2.8E0 | 1.0E-9 | 1.0E-9 | 1.8E1 | 8.4E0 | 49 | 9 | 49 | 9 | 0.40 |
| Tl | pg/ml | 1.1E-1 | 1.0E-9 | 3.1E-1 | 2.9E0 | 4.0E-1 | 8.2E0 | 1.0E-9 | 1.0E-9 | 1.8E0 | 2.5E1 | 49 | 9 | 49 | 9 | 0.45 |
| Ju | mIU/ml | 9.1E0 | 1.6E1 | 2.5E1 | 2.2E1 | 3.7E1 | 2.3E1 | 1.7E-1 | 1.9E0 | 2.3E2 | 1.0E2 | 111 | 24 | 111 | 24 | 0.60 |
| Jv | mIU/ml | 1.6E1 | 1.3E1 | 4.1E1 | 2.7E1 | 6.6E1 | 4.0E1 | 1.7E-2 | 1.1E0 | 4.4E2 | 1.8E2 | 111 | 24 | 111 | 24 | 0.49 |
| Jy | ng/ml | 1.6E-3 | 1.9E-3 | 2.2E-3 | 4.7E-3 | 3.7E-3 | 8.9E-3 | 1.0E-9 | 4.5E-4 | 3.9E-2 | 4.1E-2 | 111 | 24 | 111 | 24 | 0.56 |
| Kc | pg/ml | 2.2E1 | 4.6E1 | 3.7E1 | 8.2E1 | 4.4E1 | 8.4E1 | 1.0E-9 | 1.0E-9 | 1.9E2 | 3.2E2 | 111 | 25 | 111 | 25 | 0.67 |
| Kd | pg/ml | 1.0E-9 | 1.0E-9 | 1.6E2 | 2.2E3 | 5.8E2 | 7.7E3 | 1.0E-9 | 1.0E-9 | 4.8E3 | 3.8E4 | 111 | 25 | 111 | 25 | 0.58 |
| Ke | pg/ml | 1.2E4 | 1.9E4 | 1.4E4 | 4.1E4 | 9.2E3 | 6.3E4 | 6.7E2 | 3.5E2 | 5.5E4 | 3.2E5 | 111 | 25 | 111 | 25 | 0.73 |
| Kf | pg/mL | 5.7E0 | 8.9E0 | 6.3E0 | 1.3E1 | 5.0E0 | 1.6E1 | 1.0E-9 | 1.0E-9 | 2.2E1 | 7.8E1 | 111 | 25 | 111 | 25 | 0.67 |
| Kg | pg/mL | 9.3E2 | 1.0E3 | 1.8E3 | 4.0E3 | 2.6E3 | 8.6E3 | 7.7E1 | 1.3E2 | 2.2E4 | 3.6E4 | 111 | 25 | 111 | 25 | 0.52 |
| Ki | pg/ml | 5.9E1 | 6.4E1 | 7.0E1 | 7.8E1 | 5.3E1 | 5.3E1 | 1.0E-9 | 1.0E-9 | 2.9E2 | 2.5E2 | 111 | 25 | 111 | 25 | 0.56 |
| Kj | pg/ml | 8.8E2 | 7.3E2 | 1.4E3 | 1.7E3 | 1.4E3 | 3.1E3 | 6.6E1 | 3.3E1 | 8.8E3 | 1.5E4 | 111 | 25 | 111 | 25 | 0.45 |
| Kk | pg/ml | 6.8E0 | 1.5E1 | 1.2E1 | 2.5E1 | 1.4E1 | 2.0E1 | 1.0E-9 | 2.0E0 | 8.1E1 | 5.9E1 | 111 | 25 | 111 | 25 | 0.73 |
| Kl | pg/ml | 1.8E4 | 1.8E4 | 2.8E4 | 2.7E4 | 2.7E4 | 2.1E4 | 2.3E2 | 6.2E2 | 1.3E5 | 6.3E4 | 111 | 25 | 111 | 25 | 0.52 |
| Kn | pg/ml | 2.9E1 | 6.3E1 | 5.2E1 | 3.3E2 | 7.4E1 | 9.6E2 | 1.0E-9 | 1.0E-9 | 3.6E2 | 4.9E3 | 111 | 25 | 111 | 25 | 0.67 |
| Ko | pg/ml | 3.1E2 | 6.5E2 | 4.3E2 | 9.2E2 | 4.7E2 | 9.9E2 | 1.0E-9 | 1.5E2 | 2.2E3 | 4.1E3 | 111 | 25 | 111 | 25 | 0.72 |
| Kp | pg/ml | 3.4E2 | 4.4E2 | 3.5E2 | 9.8E2 | 2.4E2 | 2.6E3 | 1.0E-9 | 3.7E1 | 9.4E2 | 1.3E4 | 111 | 25 | 111 | 25 | 0.63 |
| Kq | pg/ml | 3.1E2 | 5.7E2 | 4.0E2 | 7.7E3 | 3.8E2 | 3.2E4 | 1.6E0 | 7.0E1 | 2.1E3 | 1.6E5 | 106 | 25 | 106 | 25 | 0.72 |
| Kr | pg/ml | 1.6E-1 | 2.1E0 | 1.8E0 | 2.0E1 | 3.5E0 | 8.3E1 | 1.0E-9 | 1.0E-9 | 2.3E1 | 4.2E2 | 106 | 25 | 106 | 25 | 0.61 |
| Ks | pg/ml | 1.4E4 | 1.7E4 | 2.0E4 | 2.2E4 | 1.8E4 | 1.8E4 | 5.1E1 | 4.2E2 | 7.9E4 | 5.1E4 | 106 | 25 | 106 | 25 | 0.53 |
| Ps | ng/ml | 1.2E2 | 1.2E3 | 4.2E2 | 3.2E3 | 1.3E3 | 4.1E3 | 1.6E0 | 3.5E2 | 9.0E3 | 1.2E4 | 49 | 9 | 49 | 9 | 0.93 |
| Kx | ng/ml | 1.0E-9 | 6.9E-3 | 6.7E-3 | 1.6E-2 | 1.5E-2 | 2.1E-2 | 1.0E-9 | 1.0E-9 | 1.0E-1 | 6.5E-2 | 110 | 25 | 110 | 25 | 0.69 |
| Ky | ng/ml | 1.1E-1 | 4.6E-1 | 3.6E-1 | 6.1E-1 | 7.8E-1 | 6.5E-1 | 1.0E-9 | 1.0E-9 | 5.1E0 | 2.7E0 | 110 | 25 | 110 | 25 | 0.71 |
| Kz | ng/ml | 1.0E-9 | 1.0E-9 | 3.7E-3 | 5.1E-3 | 5.8E-3 | 7.6E-3 | 1.0E-9 | 1.0E-9 | 1.6E-2 | 2.5E-2 | 110 | 25 | 110 | 25 | 0.54 |
| Rz | ng/ml | 3.4E-1 | 3.3E-1 | 8.4E-1 | 1.4E0 | 1.2E0 | 2.4E0 | 4.6E-3 | 1.7E-2 | 6.7E0 | 7.5E0 | 49 | 9 | 49 | 9 | 0.56 |
| Ry | ng/ml | 1.6E-2 | 2.3E-2 | 2.4E-2 | 6.5E-2 | 2.6E-2 | 1.1E-1 | 1.0E-9 | 8.5E-3 | 1.2E-1 | 3.5E-1 | 49 | 9 | 49 | 9 | 0.66 |
| Rx | ng/ml | 1.0E-9 | 3.5E-5 | 1.4E-3 | 2.1E-3 | 2.3E-3 | 2.7E-3 | 1.0E-9 | 1.0E-9 | 8.6E-3 | 7.6E-3 | 49 | 9 | 49 | 9 | 0.62 |
| Ld | pg/ml | 1.0E-9 | 4.8E0 | 2.8E0 | 8.4E0 | 7.7E0 | 1.2E1 | 1.0E-9 | 1.0E-9 | 6.9E1 | 5.0E1 | 111 | 25 | 111 | 25 | 0.71 |
| Lh | pg/ml | 1.0E4 | 2.8E4 | 1.9E4 | 5.4E4 | 2.5E4 | 9.3E4 | 1.0E-9 | 1.3E3 | 2.6E5 | 4.8E5 | 295 | 61 | 295 | 61 | 0.68 |
| Li | pg/ml | 3.0E3 | 9.1E3 | 1.5E4 | 5.5E4 | 8.0E4 | 1.4E5 | 1.2E1 | 3.7E1 | 1.3E6 | 9.2E5 | 295 | 61 | 295 | 61 | 0.71 |
| Lj | pg/ml | 2.3E3 | 1.0E4 | 1.8E4 | 3.8E4 | 5.3E4 | 7.5E4 | 4.9E1 | 8.9E1 | 4.3E5 | 4.1E5 | 295 | 61 | 295 | 61 | 0.67 |
| Lp | pg/ml | 1.1E1 | 9.5E0 | 6.8E1 | 3.5E2 | 1.8E2 | 5.5E2 | 1.0E-9 | 1.0E-9 | 1.1E3 | 1.4E3 | 49 | 9 | 49 | 9 | 0.53 |
| Lt | pg/ml | 1.0E-9 | 1.0E-9 | 1.7E0 | 1.0E-9 | 6.0E0 | 0.0E0 | 1.0E-9 | 1.0E-9 | 2.5E1 | 1.0E-9 | 49 | 9 | 49 | 9 | 0.46 |
| Rv | ng/ml | 5.0E-4 | 5.8E-4 | 1.3E-3 | 2.7E-3 | 2.6E-3 | 4.7E-3 | 1.0E-9 | 1.0E-9 | 1.6E-2 | 1.2E-2 | 49 | 9 | 49 | 9 | 0.52 |
| Ru | ng/ml | 1.0E-9 | 1.0E-9 | 1.1E-2 | 8.4E-2 | 5.3E-2 | 1.5E-1 | 1.0E-9 | 1.0E-9 | 3.1E-1 | 3.5E-1 | 49 | 9 | 49 | 9 | 0.65 |
| Rt | ng/ml | 7.5E-2 | 5.2E-2 | 1.2E-1 | 9.7E-1 | 1.3E-1 | 2.4E0 | 2.2E-3 | 1.3E-3 | 6.3E-1 | 7.4E0 | 49 | 9 | 49 | 9 | 0.53 |
| Yl | pg/ml | 1.1E1 | 2.6E1 | 1.7E1 | 4.4E1 | 1.7E1 | 6.7E1 | 1.0E-9 | 1.0E-9 | 7.9E1 | 2.2E2 | 49 | 9 | 49 | 9 | 0.65 |
| Rm | ng/ml | 1.8E1 | 5.4E1 | 3.9E1 | 9.6E1 | 6.2E1 | 1.4E2 | 2.2E-1 | 2.3E-1 | 3.4E2 | 6.5E2 | 110 | 24 | 110 | 24 | 0.60 |
| Rh | ng/ml | 1.7E2 | 1.8E2 | 4.8E2 | 9.5E2 | 1.7E3 | 3.5E3 | 7.5E0 | 2.5E1 | 1.7E4 | 1.7E4 | 110 | 24 | 110 | 24 | 0.52 |
| Ri | ng/ml | 4.1E-1 | 1.0E-9 | 4.4E0 | 1.0E0 | 8.6E0 | 3.3E0 | 1.0E-9 | 1.0E-9 | 4.9E1 | 1.6E1 | 110 | 24 | 110 | 24 | 0.32 |
| Rg | ng/ml | 1.0E-9 | 1.0E-9 | 8.6E-2 | 6.3E-2 | 4.6E-1 | 1.7E-1 | 1.0E-9 | 1.0E-9 | 3.3E0 | 6.2E-1 | 110 | 24 | 110 | 24 | 0.57 |
| Rj | ng/ml | 1.0E-9 | 1.0E-9 | 9.9E-1 | 1.2E1 | 2.1E0 | 5.5E1 | 1.0E-9 | 1.0E-9 | 1.1E1 | 2.7E2 | 110 | 24 | 110 | 24 | 0.44 |
| Rf | ng/ml | 3.5E-1 | 6.2E-1 | 7.6E-1 | 2.2E0 | 1.3E0 | 4.2E0 | 2.1E-2 | 5.5E-2 | 9.9E0 | 1.7E1 | 110 | 24 | 110 | 24 | 0.63 |
| Ql | pg/ml | 1.7E0 | 8.6E0 | 1.1E1 | 1.7E1 | 2.3E1 | 2.4E1 | 1.0E-9 | 1.0E-9 | 1.8E2 | 9.3E1 | 111 | 24 | 111 | 24 | 0.60 |
| Qm | pg/ml | 1.4E0 | 1.7E1 | 1.9E1 | 2.7E1 | 3.6E1 | 3.2E1 | 1.0E-9 | 1.0E-9 | 1.9E2 | 1.0E2 | 111 | 24 | 111 | 24 | 0.60 |
| Qn | pg/ml | 6.1E-1 | 8.5E-1 | 6.9E0 | 7.4E0 | 2.8E1 | 1.9E1 | 1.0E-9 | 1.0E-9 | 2.2E2 | 7.5E1 | 111 | 24 | 111 | 24 | 0.53 |
| Nv | pg/ml | 3.2E3 | 8.3E3 | 8.2E3 | 2.1E4 | 1.7E4 | 3.2E4 | 1.0E-9 | 1.6E2 | 1.5E5 | 1.6E5 | 296 | 61 | 296 | 61 | 0.71 |
| Nw | pg/ml | 8.3E3 | 1.9E4 | 1.2E4 | 2.9E4 | 1.6E4 | 3.8E4 | 1.9E2 | 4.5E2 | 2.1E5 | 2.2E5 | 296 | 61 | 296 | 61 | 0.79 |
| Nx | pg/ml | 2.1E2 | 5.4E2 | 3.9E2 | 7.6E2 | 5.9E2 | 8.0E2 | 1.0E-9 | 1.0E-9 | 3.5E3 | 4.1E3 | 296 | 61 | 296 | 61 | 0.65 |
| Ny | pg/ml | 5.6E0 | 2.0E1 | 1.0E2 | 1.3E2 | 1.4E3 | 3.9E2 | 1.0E-9 | 1.0E-9 | 2.5E4 | 2.8E3 | 296 | 61 | 296 | 61 | 0.73 |
| Oa | pg/ml | 1.3E2 | 5.5E2 | 3.7E2 | 1.0E3 | 5.9E2 | 1.2E3 | 1.0E-9 | 1.0E-9 | 3.0E3 | 4.5E3 | 111 | 24 | 111 | 24 | 0.70 |
| Op | pg/ml | 4.4E5 | 4.4E5 | 4.4E5 | 4.5E5 | 1.6E5 | 1.9E5 | 5.2E4 | 9.4E4 | 7.3E5 | 7.5E5 | 49 | 9 | 49 | 9 | 0.52 |
| Oe | pg/ml | 4.7E1 | 1.0E-9 | 2.5E2 | 1.9E2 | 3.8E2 | 3.4E2 | 1.0E-9 | 1.0E-9 | 2.3E3 | 1.3E3 | 295 | 60 | 295 | 60 | 0.44 |
| Of | pg/ml | 1.5E2 | 1.0E2 | 5.0E3 | 5.3E3 | 2.1E4 | 1.8E4 | 1.0E-9 | 1.0E-9 | 1.9E5 | 1.2E5 | 296 | 61 | 296 | 61 | 0.48 |
| Og | pg/ml | 7.7E-2 | 2.0E-2 | 4.0E-1 | 8.2E-1 | 1.6E0 | 1.5E-1 | 1.0E-9 | 1.0E-9 | 1.9E1 | 8.0E-1 | 296 | 61 | 296 | 61 | 0.37 |
| Oh | pg/ml | 2.4E0 | 5.5E0 | 1.4E1 | 3.0E2 | 9.3E1 | 2.0E3 | 1.0E-9 | 1.0E-9 | 1.4E3 | 1.6E4 | 296 | 61 | 296 | 61 | 0.64 |
| Oi | pg/ml | 1.8E0 | 2.6E0 | 5.1E0 | 4.6E0 | 8.1E0 | 6.1E0 | 1.0E-9 | 1.0E-9 | 6.7E1 | 3.1E1 | 296 | 61 | 296 | 61 | 0.52 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ok | pg/ml | 3.6E2 | 6.7E2 | 4.7E2 | 1.2E3 | 4.7E2 | 1.5E3 | 1.5E1 | 5.3E1 | 4.2E3 | 7.8E3 | 296 | 61 | 296 | 61 | 0.73 |
| Om | pg/ml | 3.9E2 | 6.1E2 | 8.0E2 | 1.9E3 | 2.2E3 | 6.6E3 | 1.0E-9 | 7.0E1 | 3.0E4 | 5.1E4 | 296 | 61 | 296 | 61 | 0.65 |
| On | pg/ml | 1.5E2 | 3.2E2 | 2.6E2 | 7.6E2 | 4.0E2 | 1.2E3 | 1.0E-9 | 1.6E1 | 4.5E3 | 8.5E3 | 296 | 61 | 296 | 61 | 0.74 |
| Or | pg/ml | 1.0E1 | 2.4E1 | 3.1E1 | 9.3E1 | 6.1E1 | 1.4E2 | 1.0E-9 | 1.0E-9 | 4.4E2 | 5.1E2 | 112 | 25 | 112 | 25 | 0.62 |
| Ow | pg/ml | 3.6E1 | 9.4E1 | 1.1E2 | 7.3E2 | 3.2E2 | 1.7E3 | 1.0E-9 | 1.0E-9 | 2.7E3 | 8.1E3 | 112 | 25 | 112 | 25 | 0.70 |
| Ou | pg/ml | 4.2E2 | 1.3E3 | 9.1E2 | 2.7E3 | 1.5E3 | 3.3E3 | 1.0E-9 | 1.0E-9 | 9.8E3 | 1.1E4 | 112 | 25 | 112 | 25 | 0.67 |
| Ul | ng/ml | 1.0E-9 | 1.0E-9 | 1.1E0 | 3.2E0 | 4.5E0 | 1.2E1 | 1.0E-9 | 1.0E-9 | 2.9E1 | 5.6E1 | 112 | 24 | 112 | 24 | 0.50 |
| Uo | ng/ml | 1.0E-9 | 1.0E-9 | 8.2E-2 | 4.1E-2 | 2.2E-1 | 1.4E-1 | 1.0E-9 | 1.0E-9 | 1.3E0 | 6.3E-1 | 112 | 24 | 112 | 24 | 0.46 |
| Uk | ng/ml | 1.0E-9 | 1.0E-9 | 6.9E-3 | 1.9E-3 | 3.4E-2 | 6.6E-3 | 1.0E-9 | 1.0E-9 | 3.2E-1 | 3.1E-2 | 112 | 24 | 112 | 24 | 0.41 |
| Um | ng/ml | 1.0E-9 | 1.0E-9 | 2.3E-1 | 2.3E-1 | 6.0E-1 | 6.4E-1 | 1.0E-9 | 1.0E-9 | 3.6E0 | 2.3E0 | 112 | 24 | 112 | 24 | 0.46 |
| Uf | ng/ml | 5.1E-2 | 9.9E-2 | 1.3E-1 | 4.0E-1 | 1.9E-1 | 1.0E0 | 1.0E-3 | 3.5E-3 | 1.1E0 | 5.1E0 | 112 | 24 | 112 | 24 | 0.66 |
| Uh | ng/ml | 1.9E0 | 5.9E0 | 2.9E0 | 7.0E0 | 2.9E0 | 4.5E0 | 3.6E-2 | 7.1E-1 | 1.5E1 | 1.8E1 | 112 | 24 | 112 | 24 | 0.80 |
| Un | ng/ml | 1.6E0 | 2.4E0 | 1.9E0 | 3.8E0 | 1.2E0 | 4.9E0 | 3.4E-1 | 7.1E-1 | 8.0E0 | 2.5E1 | 112 | 24 | 112 | 24 | 0.70 |
| Ug | ng/ml | 1.3E1 | 6.8E0 | 2.2E1 | 1.9E1 | 2.4E1 | 3.6E1 | 1.2E0 | 1.0E0 | 1.4E2 | 1.6E2 | 112 | 24 | 112 | 24 | 0.36 |
| Ur | ng/ml | 1.1E-1 | 1.0E-9 | 2.9E-1 | 7.1E-1 | 5.0E-1 | 1.9E0 | 1.0E-9 | 1.0E-9 | 3.0E0 | 7.3E0 | 111 | 24 | 111 | 24 | 0.39 |
| Up | ng/ml | 1.0E-9 | 1.0E-9 | 2.7E-3 | 1.1E-1 | 8.4E-3 | 4.8E-1 | 1.0E-9 | 1.0E-9 | 5.3E-2 | 2.4E0 | 111 | 24 | 111 | 24 | 0.54 |
| Us | ng/ml | 3.6E-3 | 1.0E-9 | 1.6E-2 | 9.0E-2 | 4.3E-2 | 3.4E-1 | 1.0E-9 | 1.0E-9 | 3.6E-1 | 1.7E0 | 111 | 24 | 111 | 24 | 0.45 |
| Uv | ng/ml | 3.1E-3 | 1.7E-3 | 1.5E-2 | 2.3E-2 | 4.5E-2 | 8.3E-2 | 1.0E-9 | 1.0E-9 | 3.5E-1 | 4.1E-1 | 111 | 24 | 111 | 24 | 0.45 |
| Ut | ng/ml | 6.8E-1 | 1.4E0 | 2.4E0 | 7.4E0 | 5.9E0 | 1.4E1 | 1.0E-9 | 1.0E-9 | 5.2E1 | 6.5E1 | 111 | 24 | 111 | 24 | 0.64 |
| Uu | ng/ml | 7.1E0 | 5.4E0 | 7.6E0 | 6.6E0 | 5.2E0 | 4.4E0 | 5.4E-1 | 8.1E-1 | 2.9E1 | 1.7E1 | 111 | 24 | 111 | 24 | 0.44 |
| Uw | ng/ml | 2.2E0 | 5.0E0 | 2.7E0 | 8.3E0 | 2.5E0 | 1.2E1 | 1.0E-9 | 1.7E0 | 9.8E0 | 3.9E1 | 50 | 9 | 50 | 9 | 0.76 |
| Vb | ng/ml | 1.1E0 | 1.1E0 | 1.1E0 | 1.5E0 | 4.3E-1 | 1.9E0 | 8.5E-2 | 2.6E-1 | 2.0E0 | 6.4E0 | 50 | 9 | 50 | 9 | 0.43 |
| Vc | ng/ml | 1.0E-9 | 1.0E-9 | 4.3E-3 | 1.0E-9 | 1.9E-2 | 0.0E0 | 1.0E-9 | 1.0E-9 | 1.1E-1 | 1.0E-9 | 50 | 9 | 50 | 9 | 0.46 |
| Uy | ng/ml | 1.3E0 | 1.5E0 | 6.2E0 | 1.7E1 | 1.7E1 | 2.5E1 | 8.7E-2 | 2.0E-2 | 9.9E1 | 6.4E1 | 50 | 9 | 50 | 9 | 0.57 |
| Uz | ng/ml | 1.0E-9 | 1.0E-9 | 8.7E-3 | 3.7E0 | 6.2E-2 | 1.1E1 | 1.0E-9 | 1.0E-9 | 4.4E-1 | 3.3E1 | 50 | 9 | 50 | 9 | 0.60 |
| Ux | ng/ml | 1.8E2 | 1.6E2 | 1.9E2 | 1.9E2 | 1.4E2 | 1.5E2 | 4.5E0 | 4.0E1 | 4.8E2 | 4.9E2 | 50 | 9 | 50 | 9 | 0.50 |
| Va | ng/ml | 1.5E1 | 3.2E0 | 2.5E1 | 9.9E0 | 2.9E1 | 2.0E1 | 3.1E-1 | 1.2E0 | 1.2E2 | 6.2E1 | 50 | 9 | 50 | 9 | 0.31 |
| Vh | ng/ml | 1.1E-2 | 2.2E-2 | 1.9E-2 | 1.1E-1 | 2.5E-2 | 2.8E-1 | 3.9E-4 | 3.5E-3 | 1.2E-1 | 8.6E-1 | 50 | 9 | 50 | 9 | 0.70 |
| Vi | ng/ml | 3.1E-3 | 4.3E-2 | 6.9E-3 | 2.5E-1 | 8.7E-3 | 5.9E-1 | 1.0E-9 | 1.6E-2 | 3.7E-2 | 1.8E0 | 50 | 9 | 50 | 9 | 0.94 |
| Vj | ng/ml | 2.7E1 | 8.9E1 | 5.4E1 | 1.6E2 | 6.7E1 | 2.0E2 | 1.4E0 | 1.4E1 | 3.4E2 | 6.5E2 | 50 | 8 | 50 | 8 | 0.78 |
| Vp | ng/ml | 1.0E-9 | 1.0E-9 | 1.2E-1 | 2.4E0 | 5.6E-1 | 1.0E1 | 1.0E-9 | 1.0E-9 | 3.9E0 | 4.9E1 | 112 | 24 | 112 | 24 | 0.61 |
| Vt | ng/ml | 5.6E0 | 1.1E1 | 7.2E0 | 2.0E1 | 6.1E0 | 3.1E1 | 5.6E-1 | 1.9E0 | 3.2E1 | 1.6E2 | 112 | 24 | 112 | 24 | 0.75 |
| Vu | ng/ml | 1.0E-9 | 3.6E-1 | 1.3E0 | 3.0E0 | 2.6E0 | 5.7E0 | 1.0E-9 | 1.0E-9 | 1.6E1 | 2.2E1 | 110 | 22 | 110 | 22 | 0.57 |
| Vq | ng/ml | 1.3E2 | 7.9E2 | 5.1E2 | 1.8E3 | 9.0E2 | 3.0E3 | 9.2E-1 | 6.5E1 | 5.0E3 | 1.2E4 | 90 | 18 | 90 | 18 | 0.67 |
| Vo | ng/ml | 2.6E1 | 2.5E1 | 2.5E1 | 2.4E1 | 5.4E0 | 6.5E0 | 4.9E0 | 1.9E0 | 4.8E1 | 3.1E1 | 112 | 24 | 112 | 24 | 0.47 |
| Vs | ng/ml | 1.0E-9 | 1.0E-9 | 4.5E0 | 2.5E1 | 1.2E1 | 9.7E1 | 1.0E-9 | 1.0E-9 | 8.9E1 | 4.5E2 | 111 | 22 | 111 | 22 | 0.49 |
| Vv | ng/ml | 2.9E0 | 2.6E0 | 6.0E0 | 6.6E0 | 1.0E1 | 1.0E1 | 1.0E-9 | 1.0E-9 | 8.4E1 | 4.4E1 | 112 | 23 | 112 | 23 | 0.50 |
| Vw | ng/ml | 3.6E1 | 4.3E1 | 3.4E1 | 4.4E1 | 1.8E1 | 2.2E1 | 2.5E0 | 1.1E1 | 6.7E1 | 6.9E1 | 50 | 9 | 50 | 9 | 0.66 |
| Oy | pg/ml | 4.8E-1 | 4.3E-1 | 6.7E0 | 2.7E0 | 3.3E1 | 6.4E0 | 1.0E-9 | 1.0E-9 | 4.0E2 | 3.3E1 | 295 | 61 | 295 | 61 | 0.45 |
| Oz | pg/ml | 3.1E-2 | 1.0E-9 | 3.5E-1 | 5.9E-1 | 1.7E0 | 3.6E0 | 1.0E-9 | 1.0E-9 | 2.9E1 | 2.8E1 | 295 | 61 | 295 | 61 | 0.39 |
| Pa | pg/ml | 3.8E-1 | 6.3E-1 | 1.4E0 | 7.3E0 | 6.1E0 | 3.2E1 | 1.0E-9 | 1.0E-9 | 8.6E1 | 2.3E2 | 295 | 61 | 295 | 61 | 0.62 |
| Pb | pg/ml | 1.0E-9 | 1.0E-9 | 1.8E0 | 1.1E0 | 2.8E1 | 5.4E0 | 1.0E-9 | 1.0E-9 | 4.9E2 | 3.2E1 | 295 | 61 | 295 | 61 | 0.42 |
| Pc | pg/ml | 5.4E-2 | 1.0E-9 | 4.0E-1 | 6.3E0 | 9.4E-1 | 4.2E1 | 1.0E-9 | 1.0E-9 | 1.4E1 | 3.3E2 | 295 | 61 | 295 | 61 | 0.45 |
| Pd | pg/ml | 1.6E0 | 2.4E0 | 6.6E0 | 8.1E0 | 5.0E1 | 1.8E1 | 1.0E-9 | 1.0E-9 | 8.4E2 | 1.2E2 | 295 | 61 | 295 | 61 | 0.57 |
| Pe | pg/ml | 1.9E1 | 6.1E1 | 9.5E1 | 6.6E2 | 4.0E2 | 2.2E3 | 1.0E-9 | 1.0E-9 | 4.7E3 | 1.5E4 | 295 | 61 | 295 | 61 | 0.71 |
| Pf | pg/ml | 1.3E0 | 5.8E0 | 1.4E1 | 2.9E1 | 9.4E1 | 7.4E1 | 1.0E-9 | 1.0E-9 | 1.5E3 | 4.3E2 | 295 | 61 | 295 | 61 | 0.70 |
| Pg | pg/ml | 3.3E0 | 1.1E1 | 6.9E1 | 1.5E2 | 5.4E2 | 3.8E2 | 1.0E-9 | 1.0E-9 | 7.7E3 | 2.2E3 | 295 | 61 | 295 | 61 | 0.70 |
| Ph | ng/ml | 1.4E-1 | 2.4E-1 | 3.4E-1 | 5.9E-1 | 4.9E-1 | 1.1E0 | 1.0E-9 | 1.0E-9 | 2.8E0 | 5.4E0 | 112 | 25 | 112 | 25 | 0.55 |
| Pi | ng/ml | 1.9E-1 | 3.5E-1 | 2.8E-1 | 3.8E0 | 3.8E-1 | 1.6E1 | 1.0E-9 | 1.0E-9 | 3.2E0 | 8.2E1 | 112 | 25 | 112 | 25 | 0.64 |
| Pj | ng/mL | 5.0E0 | 7.3E0 | 5.8E0 | 8.0E0 | 4.4E0 | 5.0E0 | 4.0E-1 | 6.6E-1 | 3.1E1 | 2.3E1 | 112 | 25 | 112 | 25 | 0.64 |
| Pk | ng/ml | 8.9E-3 | 1.0E-2 | 1.6E-2 | 7.3E-2 | 3.0E-2 | 3.0E-1 | 1.0E-9 | 1.0E-9 | 2.5E-1 | 1.5E0 | 112 | 25 | 112 | 25 | 0.53 |
| aA | mg/dL | 8.8E-1 | 1.0E0 | 9.9E-1 | 1.4E0 | 5.0E-1 | 9.3E-1 | 3.0E-1 | 5.0E-1 | 4.2E0 | 4.7E0 | 456 | 83 | 456 | 83 | 0.64 |
| aC | mg/mL | 2.2E0 | 2.1E0 | 2.6E0 | 2.6E0 | 1.3E0 | 1.4E0 | 7.5E-1 | 1.0E0 | 7.4E0 | 6.7E0 | 140 | 36 | 140 | 36 | 0.46 |
| aD | ug/mL | 3.0E0 | 3.4E0 | 4.7E0 | 4.7E0 | 4.9E0 | 3.9E0 | 7.5E-1 | 9.2E-1 | 3.5E1 | 1.8E1 | 140 | 36 | 140 | 36 | 0.49 |
| aE | mg/mL | 5.9E-1 | 5.3E-1 | 6.0E-1 | 5.6E-1 | 1.7E-1 | 1.7E-1 | 1.8E-1 | 2.2E-1 | 1.1E0 | 1.2E0 | 140 | 36 | 140 | 36 | 0.41 |
| aF | ng/mL | 2.1E0 | 3.0E0 | 5.0E0 | 5.3E0 | 8.0E0 | 6.3E0 | 4.3E-1 | 4.3E-3 | 5.0E1 | 2.9E1 | 140 | 36 | 140 | 36 | 0.53 |
| aG | mg/mL | 1.4E-1 | 1.2E-1 | 1.6E-1 | 1.4E-1 | 9.1E-2 | 6.2E-2 | 3.2E-2 | 6.8E-2 | 4.8E-1 | 3.2E-1 | 140 | 36 | 140 | 36 | 0.44 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aH | ug/mL | 7.6E1 | 5.7E1 | 8.1E1 | 6.4E1 | 4.2E1 | 3.1E1 | 8.9E0 | 1.1E1 | 2.0E2 | 1.4E2 | 140 | 36 | 140 | 36 | 0.38 |
| aI | ug/mL | 1.8E2 | 1.4E2 | 1.8E2 | 1.5E2 | 6.1E1 | 5.7E1 | 3.2E1 | 7.5E1 | 3.4E2 | 2.7E2 | 140 | 36 | 140 | 36 | 0.36 |
| aJ | ug/mL | 2.3E0 | 3.6E0 | 3.0E0 | 4.6E0 | 2.1E0 | 4.1E0 | 8.2E-1 | 1.4E0 | 1.4E1 | 2.3E1 | 140 | 36 | 140 | 36 | 0.64 |
| aK | ng/mL | 1.3E0 | 1.2E0 | 2.0E0 | 1.8E0 | 2.0E0 | 1.7E0 | 2.9E-4 | 1.0E-1 | 1.0E1 | 6.5E0 | 140 | 36 | 140 | 36 | 0.47 |
| aL | mg/mL | 7.4E-1 | 7.2E-1 | 7.8E-1 | 7.1E-1 | 2.5E-1 | 2.6E-1 | 2.2E-1 | 2.7E-1 | 1.7E0 | 1.4E0 | 140 | 36 | 140 | 36 | 0.43 |
| aM | U/mL | 1.7E1 | 2.4E1 | 3.5E1 | 8.5E1 | 5.1E1 | 1.8E2 | 4.2E-2 | 4.2E-2 | 3.5E2 | 8.2E2 | 140 | 36 | 140 | 36 | 0.61 |
| aN | U/mL | 1.4E1 | 1.9E1 | 2.3E1 | 3.7E1 | 3.7E1 | 5.8E1 | 2.5E-3 | 2.5E-3 | 3.8E2 | 3.3E2 | 140 | 36 | 140 | 36 | 0.58 |
| aO | pg/mL | 4.8E1 | 1.1E2 | 4.1E2 | 5.3E2 | 1.0E3 | 7.5E2 | 6.0E-2 | 5.0E0 | 6.6E3 | 2.4E3 | 140 | 36 | 140 | 36 | 0.60 |
| aP | ng/mL | 1.6E0 | 1.9E0 | 2.1E0 | 3.4E0 | 2.5E0 | 4.6E0 | 4.5E-1 | 7.8E-1 | 2.8E1 | 2.8E1 | 140 | 36 | 140 | 36 | 0.63 |
| aQ | ng/mL | 2.6E-1 | 2.3E-1 | 3.7E-1 | 2.8E-1 | 3.4E-1 | 1.9E-1 | 2.0E-4 | 5.1E-2 | 2.0E0 | 9.0E-1 | 140 | 36 | 140 | 36 | 0.45 |
| aR | ng/mL | 1.7E0 | 2.5E0 | 2.9E0 | 3.6E0 | 4.1E0 | 3.6E0 | 2.6E-1 | 5.6E-1 | 3.4E1 | 1.7E1 | 140 | 36 | 140 | 36 | 0.59 |
| aS | ng/mL | 3.7E-1 | 4.6E-1 | 1.0E0 | 9.1E-1 | 2.9E0 | 1.1E0 | 4.2E-3 | 6.0E-2 | 3.3E1 | 4.9E0 | 140 | 36 | 140 | 36 | 0.54 |
| aU | pg/mL | 6.7E1 | 5.9E1 | 1.0E2 | 9.1E1 | 1.1E2 | 1.0E2 | 7.4E-2 | 7.4E-2 | 7.0E2 | 5.1E2 | 140 | 36 | 140 | 36 | 0.46 |
| aV | ng/mL | 6.2E-1 | 3.6E-1 | 1.1E0 | 7.6E-1 | 2.8E0 | 1.1E0 | 7.6E-4 | 9.1E-2 | 3.3E1 | 6.0E0 | 140 | 36 | 140 | 36 | 0.43 |
| aW | pg/mL | 2.0E1 | 1.8E1 | 2.1E1 | 2.9E1 | 1.6E1 | 6.7E1 | 7.2E-2 | 7.2E-2 | 1.7E2 | 4.2E2 | 140 | 36 | 140 | 36 | 0.47 |
| aX | ng/mL | 8.3E0 | 7.6E0 | 1.4E1 | 2.6E1 | 2.2E1 | 5.6E1 | 3.0E-1 | 7.7E-1 | 2.2E2 | 3.1E2 | 140 | 36 | 140 | 36 | 0.51 |
| aY | pg/mL | 5.3E1 | 5.5E1 | 7.5E1 | 7.9E1 | 1.1E2 | 7.7E1 | 4.1E-1 | 4.1E-1 | 1.2E3 | 3.9E2 | 140 | 36 | 140 | 36 | 0.53 |
| aZ | pg/mL | 2.2E2 | 3.7E2 | 5.3E2 | 1.2E3 | 1.2E3 | 2.0E3 | 1.7E0 | 1.7E0 | 1.2E4 | 7.9E3 | 140 | 36 | 140 | 36 | 0.62 |
| bA | ng/mL | 1.0E1 | 4.6E1 | 4.8E1 | 1.8E2 | 1.1E2 | 3.1E2 | 3.0E-2 | 2.0E0 | 9.4E2 | 1.5E3 | 140 | 36 | 140 | 36 | 0.70 |
| bB | ng/mL | 2.9E2 | 2.3E2 | 3.2E2 | 2.4E2 | 1.8E2 | 1.4E2 | 2.1E0 | 1.2E1 | 9.5E2 | 5.7E2 | 140 | 36 | 140 | 36 | 0.37 |
| bC | ng/mL | 3.2E2 | 3.3E2 | 6.1E2 | 8.0E2 | 8.2E2 | 1.1E3 | 1.4E1 | 5.0E1 | 4.7E3 | 4.0E3 | 140 | 36 | 140 | 36 | 0.54 |
| bE | mg/mL | 5.2E0 | 5.0E0 | 5.5E0 | 5.5E0 | 2.1E0 | 2.6E0 | 1.8E0 | 1.3E0 | 1.2E1 | 1.2E1 | 140 | 36 | 140 | 36 | 0.47 |
| bF | pg/mL | 3.2E1 | 6.6E1 | 3.2E2 | 4.5E2 | 1.4E3 | 1.1E3 | 5.0E-2 | 8.9E0 | 1.1E4 | 6.3E3 | 140 | 36 | 140 | 36 | 0.66 |
| bG | ng/mL | 1.5E0 | 2.2E0 | 2.9E0 | 4.1E0 | 4.0E0 | 5.7E0 | 1.1E-1 | 1.6E-1 | 2.6E1 | 3.0E1 | 140 | 36 | 140 | 36 | 0.57 |
| bH | pg/mL | 5.7E-1 | 5.7E-1 | 6.6E0 | 4.7E0 | 2.6E1 | 6.0E0 | 5.7E-1 | 5.7E-1 | 2.8E2 | 2.3E1 | 140 | 36 | 140 | 36 | 0.55 |
| bI | ng/mL | 4.0E-3 | 4.0E-3 | 9.4E-2 | 8.5E-2 | 1.9E-1 | 2.1E-1 | 4.0E-3 | 4.0E-3 | 9.8E-1 | 8.8E-1 | 140 | 36 | 140 | 36 | 0.47 |
| bJ | ng/mL | 1.9E0 | 1.9E0 | 2.4E0 | 2.3E0 | 2.0E0 | 2.1E0 | 2.5E-4 | 2.5E-4 | 1.1E1 | 9.0E0 | 140 | 36 | 140 | 36 | 0.47 |
| bL | pg/mL | 4.0E0 | 3.9E0 | 9.5E0 | 8.5E0 | 1.2E1 | 8.6E0 | 4.6E-2 | 4.6E-2 | 6.0E1 | 3.2E1 | 140 | 36 | 140 | 36 | 0.53 |
| bM | mg/mL | 1.8E0 | 2.1E0 | 2.2E0 | 2.1E0 | 1.5E0 | 1.3E0 | 1.4E-1 | 1.6E-2 | 8.6E0 | 5.4E0 | 140 | 36 | 140 | 36 | 0.52 |
| bN | ng/mL | 3.5E1 | 2.7E1 | 1.4E2 | 5.6E1 | 3.1E2 | 8.5E1 | 1.4E-1 | 5.9E-1 | 1.9E3 | 4.4E2 | 140 | 36 | 140 | 36 | 0.42 |
| bO | ng/mL | 4.0E-2 | 4.0E-2 | 8.5E0 | 1.1E1 | 1.8E1 | 2.7E1 | 4.0E-2 | 4.0E-2 | 1.2E2 | 1.3E2 | 140 | 36 | 140 | 36 | 0.45 |
| bP | mg/mL | 5.2E-1 | 5.8E-1 | 7.4E-1 | 7.5E-1 | 7.0E-1 | 7.1E-1 | 4.9E-2 | 9.2E-2 | 4.8E0 | 3.5E0 | 140 | 36 | 140 | 36 | 0.52 |
| bQ | pg/mL | 2.1E1 | 5.2E1 | 1.5E2 | 6.5E1 | 1.1E3 | 5.7E1 | 1.5E-1 | 1.5E-1 | 1.3E4 | 2.2E2 | 140 | 36 | 140 | 36 | 0.69 |
| bR | ng/mL | 1.2E-2 | 1.2E-2 | 1.8E-1 | 7.2E-2 | 7.9E-1 | 1.1E-1 | 1.2E-2 | 1.2E-2 | 8.7E0 | 3.9E-1 | 140 | 36 | 140 | 36 | 0.45 |
| bS | ng/mL | 9.4E-1 | 9.4E-1 | 1.0E1 | 6.3E0 | 4.5E1 | 1.7E1 | 9.4E-1 | 9.4E-1 | 3.9E2 | 7.2E1 | 140 | 36 | 140 | 36 | 0.49 |
| bU | ng/mL | 6.9E-2 | 1.5E-1 | 1.9E-1 | 1.7E-1 | 5.9E-1 | 1.8E-1 | 1.3E-2 | 1.3E-2 | 6.6E0 | 6.5E-1 | 140 | 36 | 140 | 36 | 0.55 |
| bV | pg/mL | 4.7E2 | 5.9E2 | 6.1E2 | 7.2E2 | 9.7E2 | 4.5E2 | 1.6E2 | 2.7E2 | 1.2E4 | 2.2E3 | 140 | 36 | 140 | 36 | 0.63 |
| bW | pg/mL | 3.3E2 | 3.1E2 | 5.0E2 | 6.3E2 | 5.4E2 | 9.4E2 | 8.4E1 | 1.3E2 | 4.8E3 | 3.9E3 | 140 | 36 | 140 | 36 | 0.51 |
| bX | ng/mL | 1.5E-3 | 2.5E-5 | 2.7E-3 | 2.1E-3 | 3.3E-3 | 2.8E-3 | 2.5E-5 | 2.5E-5 | 1.3E-2 | 7.8E-3 | 140 | 36 | 140 | 36 | 0.45 |
| bZ | pg/mL | 2.7E2 | 6.6E2 | 1.9E3 | 2.5E3 | 7.1E3 | 7.1E3 | 1.5E-1 | 1.0E2 | 5.8E4 | 4.3E4 | 140 | 36 | 140 | 36 | 0.63 |
| cA | pg/mL | 6.0E-1 | 6.0E-1 | 4.6E0 | 2.0E0 | 3.2E1 | 4.5E0 | 6.0E-1 | 6.0E-1 | 3.7E2 | 2.1E1 | 140 | 36 | 140 | 36 | 0.49 |
| cB | ng/mL | 5.1E-2 | 3.2E-2 | 7.4E-2 | 7.6E-2 | 8.2E-2 | 1.1E-1 | 1.7E-3 | 1.7E-3 | 3.8E-1 | 4.3E-1 | 140 | 36 | 140 | 36 | 0.44 |
| cC | ng/mL | 4.1E1 | 4.7E1 | 4.6E1 | 4.3E1 | 5.4E1 | 1.2E1 | 1.0E0 | 1.0E0 | 4.5E2 | 1.1E2 | 140 | 36 | 140 | 36 | 0.53 |
| cD | pg/mL | 4.9E0 | 4.7E0 | 1.4E1 | 8.2E0 | 5.0E1 | 1.5E1 | 3.3E-1 | 3.3E-1 | 4.8E2 | 9.0E1 | 140 | 36 | 140 | 36 | 0.50 |
| cE | pg/mL | 5.4E1 | 1.1E2 | 2.6E2 | 2.9E2 | 6.3E2 | 4.3E2 | 1.2E-1 | 1.4E1 | 3.8E3 | 2.1E3 | 140 | 36 | 140 | 36 | 0.64 |
| cF | pg/mL | 5.3E-1 | 4.6E0 | 1.6E1 | 1.3E1 | 3.2E1 | 1.7E1 | 5.3E-1 | 5.3E-1 | 2.7E2 | 6.5E1 | 140 | 36 | 140 | 36 | 0.50 |
| cG | pg/mL | 5.2E1 | 1.2E2 | 1.8E2 | 1.8E2 | 8.9E2 | 2.0E2 | 7.8E0 | 2.4E1 | 1.0E4 | 1.1E3 | 140 | 36 | 140 | 36 | 0.68 |
| cH | uIU/mL | 3.7E0 | 2.3E0 | 7.9E0 | 6.3E0 | 1.8E1 | 1.2E1 | 8.6E-3 | 8.6E-3 | 1.6E2 | 5.3E1 | 140 | 36 | 140 | 36 | 0.39 |
| cI | ng/mL | 6.0E0 | 9.4E0 | 1.3E1 | 2.1E1 | 1.7E1 | 3.2E1 | 2.3E-1 | 3.2E-1 | 1.0E2 | 1.2E2 | 140 | 36 | 140 | 36 | 0.54 |
| cJ | ug/mL | 7.2E1 | 3.9E1 | 1.1E2 | 6.4E1 | 1.1E2 | 6.6E1 | 6.9E0 | 5.6E0 | 6.4E2 | 3.4E2 | 140 | 36 | 140 | 36 | 0.38 |
| cK | ng/mL | 3.8E-3 | 3.8E-3 | 2.4E-2 | 1.7E-2 | 1.3E-1 | 3.8E-3 | 3.8E-3 | 3.8E-3 | 1.5E0 | 2.1E-1 | 140 | 36 | 140 | 36 | 0.53 |
| cL | pg/mL | 2.1E2 | 2.2E2 | 5.7E2 | 4.2E2 | 2.2E3 | 5.3E2 | 3.1E1 | 6.7E1 | 2.4E4 | 2.8E3 | 140 | 36 | 140 | 36 | 0.60 |
| cM | pg/mL | 2.7E2 | 2.7E2 | 2.9E2 | 2.7E2 | 1.7E2 | 1.1E2 | 2.5E1 | 5.7E1 | 1.1E3 | 4.8E2 | 140 | 36 | 140 | 36 | 0.49 |
| cN | pg/mL | 1.2E2 | 1.3E2 | 1.3E2 | 1.3E2 | 9.2E1 | 4.3E1 | 3.8E1 | 7.9E1 | 1.1E3 | 2.7E2 | 140 | 36 | 140 | 36 | 0.57 |
| cO | pg/mL | 2.0E2 | 2.7E2 | 4.3E2 | 3.3E2 | 1.6E3 | 2.5E2 | 5.4E1 | 9.6E1 | 1.9E4 | 1.5E3 | 140 | 36 | 140 | 36 | 0.62 |
| cP | ng/mL | 2.5E3 | 2.3E3 | 2.6E3 | 2.4E3 | 9.6E2 | 9.1E2 | 6.2E2 | 1.0E3 | 5.6E3 | 4.7E3 | 140 | 36 | 140 | 36 | 0.46 |
| cQ | ng/mL | 5.3E-2 | 4.5E-2 | 1.3E-1 | 1.2E-1 | 2.1E-1 | 2.1E-1 | 2.0E-3 | 2.0E-3 | 1.3E0 | 8.7E-1 | 140 | 36 | 140 | 36 | 0.46 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cR | ng/mL | 3.0E2 | 4.3E2 | 5.7E2 | 7.1E2 | 8.0E2 | 9.0E2 | 2.0E1 | 8.6E1 | 7.7E3 | 4.8E3 | 140 | 36 | 140 | 36 | 0.57 |
| cS | ng/mL | 2.8E2 | 3.5E2 | 4.1E2 | 7.4E2 | 4.4E2 | 1.3E3 | 4.1E1 | 9.1E1 | 2.5E3 | 7.1E3 | 140 | 36 | 140 | 36 | 0.56 |
| cT | ng/mL | 4.4E1 | 1.0E2 | 1.2E2 | 3.0E2 | 2.4E2 | 4.6E2 | 3.6E0 | 1.1E1 | 2.1E3 | 1.5E3 | 140 | 36 | 140 | 36 | 0.64 |
| cU | ng/mL | 5.6E1 | 9.5E1 | 9.2E1 | 1.2E2 | 1.6E2 | 1.0E2 | 6.2E0 | 9.0E0 | 1.6E3 | 4.2E2 | 140 | 36 | 140 | 36 | 0.65 |
| cV | ng/mL | 1.8E-1 | 2.2E-1 | 7.4E-1 | 6.6E-1 | 4.0E0 | 1.7E0 | 2.5E-2 | 3.0E-2 | 4.7E1 | 9.7E0 | 140 | 36 | 140 | 36 | 0.55 |
| cW | mIU/mL | 4.8E-2 | 5.6E-2 | 9.1E-2 | 8.2E-2 | 3.8E-1 | 7.9E-2 | 4.8E-3 | 1.4E-2 | 4.5E0 | 3.9E-1 | 140 | 36 | 140 | 36 | 0.57 |
| cX | ng/mL | 1.6E-1 | 5.4E-2 | 1.7E0 | 2.3E0 | 5.1E0 | 7.1E0 | 2.3E-4 | 2.3E-4 | 2.8E1 | 2.8E1 | 140 | 36 | 140 | 36 | 0.45 |
| cY | ng/mL | 7.4E0 | 8.0E0 | 1.1E1 | 9.9E0 | 1.1E1 | 9.2E0 | 1.7E-1 | 6.0E-1 | 6.1E1 | 3.7E1 | 140 | 36 | 140 | 36 | 0.49 |
| cZ | ug/mL | 1.3E1 | 1.2E1 | 1.5E1 | 1.3E1 | 6.8E0 | 6.8E0 | 2.3E0 | 3.3E0 | 4.6E1 | 3.0E1 | 140 | 36 | 140 | 36 | 0.41 |
| dA | pg/mL | 3.1E2 | 3.4E2 | 3.9E2 | 3.8E2 | 5.0E2 | 2.1E2 | 1.0E2 | 1.1E2 | 5.8E3 | 9.3E2 | 140 | 36 | 140 | 36 | 0.51 |
| dB | ug/mL | 1.8E1 | 2.1E1 | 1.8E1 | 1.9E1 | 2.2E1 | 9.0E0 | 2.1E0 | 2.2E0 | 2.5E2 | 3.2E1 | 140 | 36 | 140 | 36 | 0.58 |
| dC | nmol/L | 3.4E1 | 3.6E1 | 3.7E1 | 3.7E1 | 1.7E1 | 1.4E1 | 7.8E0 | 1.5E1 | 1.4E2 | 6.5E1 | 140 | 36 | 140 | 36 | 0.52 |
| dD | ug/mL | 3.4E1 | 3.0E1 | 3.6E1 | 3.4E1 | 1.1E1 | 1.1E1 | 1.4E1 | 1.4E1 | 7.4E1 | 6.0E1 | 140 | 36 | 140 | 36 | 0.37 |
| dE | ng/mL | 4.1E-1 | 5.6E-1 | 5.5E-1 | 6.9E-1 | 5.7E-1 | 7.2E-1 | 8.4E-3 | 8.4E-3 | 2.7E0 | 2.9E0 | 140 | 36 | 140 | 36 | 0.56 |
| dF | ng/mL | 2.4E2 | 3.7E2 | 3.1E2 | 4.9E2 | 2.2E2 | 3.2E2 | 7.5E1 | 1.1E2 | 1.3E3 | 1.2E3 | 140 | 36 | 140 | 36 | 0.69 |
| dG | ng/mL | 1.1E1 | 1.5E1 | 1.6E1 | 2.1E1 | 1.9E1 | 1.8E1 | 3.0E0 | 4.8E0 | 1.8E2 | 8.7E1 | 140 | 36 | 140 | 36 | 0.61 |
| dH | pg/mL | 7.6E0 | 1.1E1 | 2.2E1 | 1.6E1 | 6.8E1 | 1.8E1 | 4.0E-2 | 4.0E-2 | 6.7E2 | 7.9E1 | 140 | 36 | 140 | 36 | 0.61 |
| dI | pg/mL | 4.6E-1 | 4.6E-1 | 4.1E0 | 2.4E0 | 2.8E1 | 3.7E0 | 4.6E-1 | 4.6E-1 | 3.3E2 | 1.9E1 | 140 | 36 | 140 | 36 | 0.56 |
| dJ | ng/mL | 2.0E0 | 2.2E0 | 2.1E0 | 2.2E0 | 1.1E0 | 1.2E0 | 3.2E-2 | 3.2E-2 | 5.6E0 | 4.4E0 | 140 | 36 | 140 | 36 | 0.53 |
| dK | uIU/mL | 1.5E0 | 8.4E-1 | 2.2E0 | 1.7E0 | 3.8E0 | 2.3E0 | 2.8E-4 | 1.4E-2 | 3.9E1 | 1.1E1 | 140 | 36 | 140 | 36 | 0.38 |
| dL | ng/mL | 8.7E2 | 9.5E2 | 1.0E3 | 1.2E3 | 5.4E2 | 8.7E2 | 2.8E2 | 4.3E2 | 3.4E3 | 4.8E3 | 140 | 36 | 140 | 36 | 0.55 |
| dM | pg/mL | 9.6E2 | 1.1E3 | 1.2E3 | 1.9E3 | 1.4E3 | 1.9E3 | 3.7E2 | 6.3E2 | 1.5E4 | 9.6E3 | 140 | 36 | 140 | 36 | 0.64 |
| dN | ug/mL | 9.8E1 | 1.1E2 | 1.0E2 | 1.2E2 | 4.0E1 | 5.5E1 | 2.4E1 | 4.7E1 | 2.8E2 | 3.3E2 | 140 | 36 | 140 | 36 | 0.59 |
| dR | pg/ml | 1.6E3 | 9.4E2 | 2.1E3 | 1.5E3 | 2.0E3 | 1.9E3 | 1.4E2 | 1.3E2 | 9.8E3 | 8.9E3 | 107 | 26 | 107 | 26 | 0.36 |
| dU | pg/ml | 9.9E3 | 1.4E4 | 1.5E4 | 1.5E4 | 1.7E4 | 1.2E4 | 6.9E2 | 3.1E3 | 8.1E4 | 3.5E4 | 26 | 7 | 26 | 7 | 0.54 |
| dX | ng/ml | 6.6E-2 | 8.2E-2 | 1.4E-1 | 1.2E-1 | 2.1E-1 | 1.3E-1 | 2.6E-3 | 2.6E-3 | 1.2E0 | 4.2E-1 | 46 | 15 | 46 | 15 | 0.51 |
| eF | ng/ml | 4.1E0 | 4.6E0 | 5.2E0 | 6.1E0 | 4.6E0 | 5.4E0 | 2.0E0 | 2.0E0 | 4.6E1 | 2.9E1 | 107 | 26 | 107 | 26 | 0.57 |
| eC | pg/ml | 3.0E2 | 2.3E2 | 3.7E2 | 3.2E2 | 2.7E2 | 4.0E2 | 9.9E0 | 1.9E1 | 1.6E3 | 2.0E3 | 95 | 22 | 95 | 22 | 0.35 |
| eD | pg/ml | 2.2E2 | 2.1E2 | 7.6E2 | 4.1E2 | 1.7E3 | 8.2E2 | 5.2E-1 | 5.2E-1 | 8.3E3 | 3.8E3 | 78 | 19 | 78 | 19 | 0.49 |
| eM | ng/ml | 2.6E0 | 3.2E0 | 4.5E0 | 6.5E0 | 6.0E0 | 7.6E0 | 6.9E-1 | 8.8E-1 | 3.9E1 | 2.6E1 | 61 | 18 | 61 | 18 | 0.58 |
| eP | ng/ml | 3.7E-3 | 3.7E-3 | 6.6E-1 | 2.8E0 | 1.6E0 | 7.3E0 | 3.7E-3 | 3.7E-3 | 8.6E0 | 2.8E1 | 46 | 15 | 46 | 15 | 0.55 |
| eT | ng/ml | 2.8E2 | 5.6E2 | 7.0E2 | 9.7E2 | 8.1E2 | 1.1E3 | 1.0E2 | 7.1E1 | 2.9E3 | 2.9E3 | 46 | 9 | 46 | 9 | 0.52 |
| eQ | pg/ml | 1.0E0 | 1.0E0 | 6.1E1 | 2.2E1 | 1.2E2 | 5.5E1 | 1.0E0 | 1.0E0 | 4.7E2 | 1.5E2 | 26 | 7 | 26 | 7 | 0.40 |
| eZ | ng/ml | 4.8E1 | 6.2E1 | 5.4E1 | 6.9E1 | 2.5E1 | 2.4E1 | 1.8E1 | 3.2E1 | 1.2E2 | 1.1E2 | 46 | 9 | 46 | 9 | 0.71 |
| fB | ng/ml | 5.5E2 | 6.7E2 | 6.3E2 | 7.5E2 | 2.6E2 | 2.9E2 | 2.6E2 | 3.9E2 | 1.3E3 | 1.3E3 | 24 | 7 | 24 | 7 | 0.65 |
| fN | ng/ml | 2.1E-1 | 2.1E-1 | 3.7E0 | 4.9E0 | 9.2E0 | 6.2E0 | 2.1E-1 | 2.1E-1 | 5.4E1 | 1.4E1 | 46 | 9 | 46 | 9 | 0.58 |
| fP | ng/ml | 2.7E2 | 2.7E2 | 3.2E2 | 3.4E2 | 1.9E2 | 1.7E2 | 1.8E0 | 9.5E1 | 1.0E3 | 7.7E2 | 103 | 24 | 103 | 24 | 0.53 |
| fR | ng/ml | 1.3E5 | 2.3E5 | 2.0E5 | 3.0E5 | 1.6E5 | 2.2E5 | 3.6E4 | 1.9E2 | 6.9E5 | 8.7E5 | 87 | 28 | 87 | 28 | 0.64 |
| fY | ng/ml | 2.6E2 | 2.5E2 | 2.5E2 | 2.4E2 | 1.1E2 | 9.0E1 | 3.6E1 | 1.2E2 | 4.8E2 | 3.8E2 | 46 | 9 | 46 | 9 | 0.47 |
| gC | ng/ml | 2.4E2 | 2.7E2 | 2.5E2 | 3.0E2 | 1.1E2 | 1.4E2 | 8.3E1 | 1.5E2 | 6.4E2 | 5.9E2 | 37 | 10 | 37 | 10 | 0.58 |
| gL | pg/ml | 6.4E4 | 7.4E4 | 7.2E4 | 8.8E4 | 3.5E4 | 4.4E4 | 1.1E4 | 4.3E4 | 1.9E5 | 2.2E5 | 107 | 26 | 107 | 26 | 0.62 |
| gP | U/ml | 2.8E2 | 2.8E2 | 2.9E2 | 2.9E2 | 1.3E2 | 9.0E1 | 1.2E1 | 1.3E2 | 1.1E3 | 5.2E2 | 106 | 26 | 106 | 26 | 0.53 |
| gW | ng/ml | 5.7E2 | 3.6E2 | 9.7E2 | 6.7E2 | 1.1E3 | 7.4E2 | 2.3E0 | 5.5E1 | 6.1E3 | 3.1E3 | 80 | 19 | 80 | 19 | 0.44 |
| gV | ng/ml | 2.0E1 | 2.5E1 | 2.1E1 | 2.3E1 | 6.6E0 | 1.0E1 | 1.0E1 | 8.1E-2 | 3.7E1 | 3.4E1 | 30 | 8 | 30 | 8 | 0.65 |
| tF | pg/mL | 1.3E3 | 1.0E3 | 1.4E4 | 4.2E3 | 4.3E4 | 6.7E3 | 1.2E1 | 1.8E1 | 2.8E5 | 2.4E4 | 96 | 23 | 96 | 23 | 0.49 |
| gZ | ug/ml | 8.0E-1 | 7.8E-1 | 4.3E1 | 3.0E1 | 1.2E2 | 7.5E1 | 8.7E-2 | 1.4E-1 | 4.1E2 | 2.0E2 | 26 | 7 | 26 | 7 | 0.51 |
| hA | ng/ml | 2.4E0 | 3.9E0 | 1.4E1 | 1.5E1 | 5.4E1 | 2.7E1 | 1.7E-2 | 1.7E-2 | 3.5E2 | 1.1E2 | 78 | 20 | 78 | 20 | 0.66 |
| nM | pg/ml | 1.0E-9 | 1.0E-9 | 1.0E-9 | 8.5E1 | 0.0E0 | 3.6E2 | 1.0E-9 | 1.0E-9 | 1.0E-9 | 1.5E3 | 58 | 18 | 58 | 18 | 0.53 |
| nN | pg/ml | 1.3E3 | 3.3E3 | 3.9E3 | 1.4E4 | 1.4E4 | 3.6E4 | 8.1E1 | 4.1E2 | 1.0E5 | 1.5E5 | 58 | 18 | 58 | 18 | 0.68 |
| nO | pg/ml | 2.4E1 | 3.0E1 | 3.8E1 | 3.9E1 | 4.9E1 | 3.2E1 | 4.0E0 | 9.7E0 | 3.1E2 | 1.4E2 | 58 | 18 | 58 | 18 | 0.57 |
| nR | pg/ml | 1.6E1 | 4.4E1 | 6.7E1 | 2.1E2 | 1.8E2 | 4.6E2 | 1.0E0 | 2.7E0 | 1.1E3 | 1.9E3 | 58 | 18 | 58 | 18 | 0.66 |
| nT | pg/ml | 7.0E1 | 9.2E1 | 1.0E2 | 1.6E2 | 1.0E2 | 2.2E2 | 1.0E-9 | 1.0E-9 | 6.4E2 | 9.2E2 | 58 | 18 | 58 | 18 | 0.56 |
| nU | pg/ml | 2.9E1 | 1.0E2 | 7.4E1 | 2.1E2 | 2.0E2 | 2.6E2 | 1.0E-9 | 1.0E-9 | 1.5E3 | 9.2E2 | 58 | 18 | 58 | 18 | 0.75 |
| lW | pg/ml | 1.0E-9 | 1.0E-9 | 1.1E1 | 8.3E0 | 3.2E1 | 1.9E1 | 1.0E-9 | 1.0E-9 | 1.7E2 | 7.0E1 | 58 | 18 | 58 | 18 | 0.48 |
| lX | pg/ml | 9.2E2 | 8.3E2 | 1.0E3 | 9.4E2 | 5.6E2 | 6.3E2 | 2.3E2 | 1.9E2 | 2.6E3 | 2.5E3 | 58 | 18 | 58 | 18 | 0.44 |
| lY | pg/ml | 1.9E1 | 1.7E1 | 2.1E1 | 1.9E1 | 1.8E1 | 1.3E1 | 1.0E-9 | 5.7E-1 | 1.2E2 | 4.5E1 | 58 | 18 | 58 | 18 | 0.49 |
| mE | pg/ml | 1.0E-9 | 3.5E-1 | 2.2E0 | 3.5E0 | 7.6E0 | 6.8E0 | 1.0E-9 | 1.0E-9 | 5.7E1 | 2.8E1 | 58 | 18 | 58 | 18 | 0.58 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| mF | pg/ml | 9.3E-2 | 6.4E-1 | 7.6E0 | 3.0E0 | 3.5E1 | 4.1E0 | 1.0E-9 | 1.0E-9 | 2.5E2 | 1.3E1 | 58 | 18 | 58 | 18 | 0.61 |
| mH | pg/ml | 3.2E0 | 2.7E0 | 5.5E0 | 4.7E0 | 8.6E0 | 4.6E0 | 4.0E-1 | 5.4E-1 | 5.3E1 | 1.9E1 | 58 | 18 | 58 | 18 | 0.51 |
| mI | pg/ml | 1.0E-9 | 9.9E0 | 1.1E1 | 4.4E1 | 2.7E1 | 1.1E2 | 1.0E-9 | 1.0E-9 | 1.8E2 | 4.6E2 | 58 | 18 | 58 | 18 | 0.64 |
| mM | pg/ml | 3.2E1 | 4.5E1 | 8.3E1 | 7.7E1 | 1.6E2 | 1.1E2 | 1.0E-9 | 1.0E-9 | 1.1E3 | 4.7E2 | 58 | 18 | 58 | 18 | 0.53 |
| mP | pg/ml | 1.5E1 | 1.6E1 | 1.7E1 | 6.9E1 | 1.7E1 | 1.9E2 | 1.0E-9 | 7.5E0 | 1.2E2 | 8.1E2 | 57 | 18 | 57 | 18 | 0.60 |
| mS | pg/ml | 1.6E3 | 1.7E3 | 1.8E3 | 1.8E3 | 1.0E3 | 9.2E2 | 1.0E-9 | 1.0E-9 | 5.1E3 | 3.5E3 | 58 | 18 | 58 | 18 | 0.52 |
| mT | pg/ml | 5.5E1 | 5.8E1 | 1.3E2 | 2.1E2 | 2.4E2 | 4.3E2 | 1.0E1 | 1.6E1 | 1.4E3 | 1.7E3 | 57 | 18 | 57 | 18 | 0.50 |
| mU | pg/ml | 2.2E0 | 3.1E0 | 6.8E0 | 4.6E0 | 2.9E1 | 5.2E0 | 1.0E-9 | 6.1E-1 | 2.2E2 | 2.3E1 | 57 | 18 | 57 | 18 | 0.60 |
| mW | pg/ml | 2.2E3 | 1.9E3 | 2.4E3 | 3.2E3 | 1.3E3 | 3.2E3 | 1.0E-9 | 3.7E2 | 6.2E3 | 1.1E4 | 57 | 18 | 57 | 18 | 0.50 |
| mY | pg/ml | 6.1E2 | 8.3E2 | 8.3E2 | 1.4E3 | 9.9E2 | 1.8E3 | 1.0E-9 | 1.9E2 | 5.6E3 | 8.0E3 | 58 | 18 | 58 | 18 | 0.65 |
| mZ | pg/ml | 1.9E2 | 1.5E2 | 3.7E2 | 3.8E2 | 4.8E2 | 4.5E2 | 1.0E-9 | 1.1E1 | 3.1E3 | 1.4E3 | 57 | 18 | 57 | 18 | 0.46 |
| nA | pg/ml | 1.5E0 | 3.0E0 | 7.0E0 | 6.8E0 | 1.4E1 | 1.3E1 | 1.0E-9 | 1.0E-9 | 6.5E1 | 5.7E1 | 57 | 18 | 57 | 18 | 0.51 |
| nB | pg/ml | 2.8E2 | 3.0E2 | 3.1E2 | 3.5E2 | 1.7E2 | 2.0E2 | 3.0E1 | 1.3E2 | 8.2E2 | 9.6E2 | 58 | 18 | 58 | 18 | 0.54 |
| nC | pg/ml | 1.0E-9 | 2.3E2 | 1.1E4 | 2.6E3 | 5.8E4 | 5.2E3 | 1.0E-9 | 1.0E-9 | 3.8E5 | 2.0E4 | 58 | 18 | 58 | 18 | 0.69 |
| nD | pg/ml | 6.7E0 | 8.9E0 | 1.3E1 | 1.6E1 | 3.4E1 | 2.6E1 | 1.0E-9 | 1.0E-9 | 2.6E2 | 1.2E2 | 57 | 18 | 57 | 18 | 0.57 |
| nF | pg/ml | 1.0E-9 | 1.0E-9 | 3.0E0 | 3.4E0 | 1.3E1 | 1.1E1 | 1.0E-9 | 1.0E-9 | 9.3E1 | 4.7E1 | 58 | 18 | 58 | 18 | 0.51 |
| nH | pg/ml | 1.0E-9 | 4.7E0 | 2.2E2 | 4.0E1 | 1.4E3 | 8.2E1 | 1.0E-9 | 1.0E-9 | 1.0E4 | 3.3E2 | 57 | 18 | 57 | 18 | 0.69 |
| nI | pg/ml | 4.6E1 | 1.0E-9 | 6.2E1 | 8.6E1 | 7.9E1 | 2.8E2 | 1.0E-9 | 1.0E-9 | 3.5E2 | 1.2E3 | 58 | 18 | 58 | 18 | 0.38 |
| nJ | pg/ml | 1.7E-1 | 8.8E-1 | 3.2E0 | 1.7E0 | 1.7E1 | 3.5E0 | 1.0E-9 | 1.0E-9 | 1.3E2 | 1.5E1 | 58 | 18 | 58 | 18 | 0.59 |
| nK | pg/ml | 1.0E-9 | 1.3E1 | 1.1E1 | 3.2E1 | 2.1E1 | 5.5E1 | 1.0E-9 | 1.0E-9 | 1.0E2 | 2.2E2 | 57 | 18 | 57 | 18 | 0.64 |
| nL | pg/ml | 1.0E-9 | 7.2E0 | 3.2E2 | 1.2E2 | 1.9E3 | 2.6E2 | 1.0E-9 | 1.0E-9 | 1.4E4 | 9.0E2 | 58 | 18 | 58 | 18 | 0.66 |
| hL | pg/ml | 1.7E4 | 2.6E4 | 2.1E4 | 2.7E4 | 1.5E4 | 1.6E4 | 2.6E3 | 7.9E3 | 7.2E4 | 6.0E4 | 46 | 9 | 46 | 9 | 0.62 |
| hO | pg/ml | 1.6E4 | 1.5E4 | 1.6E4 | 1.5E4 | 2.6E3 | 2.2E3 | 1.3E4 | 1.1E4 | 2.4E4 | 1.8E4 | 46 | 9 | 46 | 9 | 0.33 |
| hP | ng/ml | 4.4E5 | 4.4E5 | 4.5E5 | 6.5E5 | 3.7E5 | 8.2E5 | 1.7E4 | 3.4E4 | 2.6E6 | 2.8E6 | 46 | 9 | 46 | 9 | 0.51 |
| wJ | pg/ml | 1.5E5 | 8.8E4 | 1.8E5 | 9.4E4 | 1.2E5 | 5.5E4 | 1.1E4 | 2.3E4 | 5.8E5 | 2.3E5 | 47 | 10 | 47 | 10 | 0.26 |
| wK | pg/ml | 3.3E4 | 2.9E4 | 5.2E4 | 3.7E4 | 7.3E4 | 2.8E4 | 3.7E3 | 1.1E4 | 5.0E5 | 1.0E5 | 47 | 10 | 47 | 10 | 0.41 |
| wL | pg/ml | 6.7E0 | 6.5E-1 | 5.2E1 | 4.0E1 | 1.5E2 | 1.1E2 | 1.0E-9 | 1.0E-9 | 8.4E2 | 3.5E2 | 47 | 10 | 47 | 10 | 0.39 |
| wP | pg/ml | 2.4E4 | 4.9E4 | 4.1E4 | 8.2E4 | 4.5E4 | 9.0E4 | 1.1E3 | 1.8E4 | 2.1E5 | 3.0E5 | 47 | 10 | 47 | 10 | 0.68 |
| wQ | pg/ml | 3.1E1 | 3.7E1 | 6.6E1 | 3.4E1 | 1.0E2 | 2.2E1 | 1.0E-9 | 1.0E-9 | 5.1E2 | 6.6E1 | 47 | 10 | 47 | 10 | 0.46 |
| hR | pg/ml | 2.7E4 | 2.4E4 | 2.9E4 | 2.7E4 | 1.2E4 | 1.0E4 | 1.0E-9 | 1.4E4 | 5.8E4 | 4.5E4 | 73 | 18 | 73 | 18 | 0.43 |
| hV | pg/ml | 4.7E2 | 3.7E2 | 4.7E2 | 3.8E2 | 2.4E2 | 1.9E2 | 1.0E-9 | 9.5E1 | 1.2E3 | 7.4E2 | 73 | 18 | 73 | 18 | 0.40 |
| hW | pg/ml | 1.7E3 | 2.4E3 | 2.1E3 | 4.5E3 | 1.2E3 | 8.9E3 | 1.0E-9 | 7.1E2 | 7.3E3 | 4.0E4 | 73 | 18 | 73 | 18 | 0.64 |
| hX | pg/ml | 1.0E3 | 1.2E3 | 1.1E3 | 1.2E3 | 9.7E2 | 6.1E2 | 2.5E0 | 3.1E2 | 8.6E3 | 2.9E3 | 73 | 18 | 73 | 18 | 0.59 |
| iA | pg/ml | 1.5E2 | 1.9E2 | 2.4E2 | 3.0E2 | 2.8E2 | 2.5E2 | 1.5E1 | 5.6E1 | 1.8E3 | 8.7E2 | 96 | 23 | 96 | 23 | 0.60 |
| iB | ng/ml | 4.8E0 | 7.0E0 | 5.8E0 | 9.6E0 | 4.4E0 | 6.3E0 | 3.3E-2 | 2.4E0 | 2.4E1 | 2.3E1 | 78 | 20 | 78 | 20 | 0.70 |
| iC | U/ml | 2.7E-1 | 6.2E-1 | 1.3E0 | 8.3E-1 | 6.3E0 | 8.1E-1 | 1.0E-9 | 6.8E-2 | 5.5E1 | 3.2E0 | 78 | 20 | 78 | 20 | 0.71 |
| tQ | pg/ml | 1.3E3 | 1.7E3 | 1.4E3 | 1.7E3 | 5.4E2 | 7.4E2 | 3.7E2 | 8.4E2 | 2.5E3 | 3.3E3 | 44 | 9 | 44 | 9 | 0.58 |
| tT | pg/ml | 1.9E1 | 2.3E1 | 2.0E1 | 3.1E1 | 9.9E0 | 2.6E1 | 5.4E0 | 1.1E1 | 4.8E1 | 9.3E1 | 45 | 9 | 45 | 9 | 0.65 |
| tS | pg/ml | 1.1E0 | 6.9E-1 | 1.4E0 | 1.7E0 | 1.7E0 | 3.1E0 | 1.0E-9 | 1.0E-9 | 8.5E0 | 1.0E1 | 45 | 10 | 45 | 10 | 0.45 |
| tX | pg/ml | 1.0E0 | 1.6E0 | 1.4E0 | 3.4E0 | 1.3E0 | 3.6E0 | 2.5E-2 | 3.7E-1 | 7.0E0 | 1.0E1 | 45 | 9 | 45 | 9 | 0.64 |
| tO | pg/ml | 4.4E0 | 3.3E0 | 5.3E0 | 4.7E0 | 3.6E0 | 4.0E0 | 1.0E-9 | 1.7E0 | 1.8E1 | 1.5E1 | 45 | 10 | 45 | 10 | 0.40 |
| tR | pg/ml | 2.2E-1 | 2.2E-1 | 3.3E-1 | 4.3E-1 | 3.8E-1 | 7.5E-1 | 1.0E-9 | 1.4E-2 | 1.6E0 | 2.5E0 | 44 | 10 | 44 | 10 | 0.49 |
| tU | pg/ml | 9.9E0 | 1.3E1 | 1.2E1 | 1.9E1 | 1.1E1 | 2.2E1 | 2.2E-1 | 4.9E0 | 5.5E1 | 8.0E1 | 46 | 10 | 46 | 10 | 0.61 |
| tN | pg/ml | 2.0E1 | 2.2E1 | 2.8E1 | 4.8E1 | 2.6E1 | 5.0E1 | 1.0E-9 | 9.5E0 | 1.5E2 | 1.6E2 | 44 | 9 | 44 | 9 | 0.61 |
| tV | ng/ml | 5.4E2 | 9.5E2 | 7.3E2 | 1.1E3 | 5.7E2 | 8.2E2 | 5.3E1 | 3.9E2 | 2.9E3 | 3.1E3 | 47 | 9 | 47 | 9 | 0.66 |
| iH | ng/ml | 1.6E5 | 1.9E5 | 1.6E5 | 1.8E5 | 4.9E4 | 5.3E4 | 2.9E3 | 7.7E4 | 2.6E5 | 2.5E5 | 96 | 23 | 96 | 23 | 0.64 |
| iJ | ng/ml | 5.2E4 | 3.9E4 | 5.6E4 | 4.9E4 | 3.7E4 | 2.9E4 | 1.8E3 | 1.2E4 | 2.5E5 | 1.5E5 | 96 | 23 | 96 | 23 | 0.42 |
| hB | ng/ml | 4.3E-1 | 6.3E-1 | 5.6E-1 | 9.7E-1 | 4.0E-1 | 7.2E-1 | 1.2E-1 | 2.9E-1 | 2.3E0 | 3.2E0 | 96 | 23 | 96 | 23 | 0.75 |
| hC | pg/ml | 4.0E3 | 1.0E4 | 7.7E3 | 1.0E4 | 1.2E4 | 1.2E4 | 4.1E1 | 3.0E2 | 1.1E5 | 5.7E4 | 96 | 23 | 96 | 23 | 0.60 |
| hF | ng/ml | 1.0E-9 | 1.0E-9 | 4.2E1 | 1.0E-9 | 4.1E2 | 0.0E0 | 1.0E-9 | 1.0E-9 | 4.0E3 | 1.0E-9 | 96 | 23 | 96 | 23 | 0.49 |
| hG | pg/ml | 6.8E3 | 6.7E3 | 7.4E3 | 8.3E3 | 3.1E3 | 4.3E3 | 1.8E3 | 3.6E3 | 1.8E4 | 2.0E4 | 96 | 23 | 96 | 23 | 0.53 |
| iO | ng/ml | 3.8E5 | 3.2E5 | 4.3E5 | 3.8E5 | 2.0E5 | 1.9E5 | 1.1E4 | 9.8E4 | 1.1E6 | 8.2E5 | 96 | 23 | 96 | 23 | 0.43 |
| iP | ng/ml | 5.3E4 | 4.6E4 | 5.9E4 | 5.1E4 | 5.0E4 | 2.1E4 | 1.0E-9 | 2.1E4 | 4.4E5 | 9.7E4 | 96 | 23 | 96 | 23 | 0.46 |
| iZ | ng/ml | 1.6E3 | 2.0E3 | 1.8E3 | 2.3E3 | 8.4E2 | 1.0E3 | 6.6E2 | 1.1E3 | 5.7E3 | 4.6E3 | 94 | 23 | 94 | 23 | 0.67 |
| yH | pg/ml | 9.3E2 | 1.4E3 | 2.4E3 | 1.9E3 | 5.3E3 | 1.9E3 | 1.0E-9 | 7.0E2 | 2.5E4 | 6.8E3 | 46 | 9 | 46 | 9 | 0.64 |
| yK | U/ml | 1.9E1 | 2.8E1 | 4.0E1 | 4.0E1 | 7.3E1 | 4.3E1 | 1.0E-9 | 1.0E-9 | 3.8E2 | 1.4E2 | 46 | 9 | 46 | 9 | 0.59 |
| yJ | pg/ml | 3.3E4 | 4.0E4 | 4.0E4 | 4.3E4 | 2.8E4 | 2.3E4 | 1.9E3 | 1.1E4 | 1.4E5 | 8.2E4 | 46 | 9 | 46 | 9 | 0.56 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| yD | ng/ml | 1.3E-2 | 1.3E-2 | 1.3E-2 | 1.3E-2 | 5.9E-3 | 5.5E-3 | 1.0E-9 | 6.3E-3 | 2.8E-2 | 2.4E-2 | 47 | 10 | 47 | 10 | 0.51 |
| jB | ng/ml | 2.5E5 | 1.9E5 | 2.5E5 | 1.9E5 | 7.6E4 | 4.3E4 | 9.9E4 | 1.3E5 | 3.6E5 | 2.4E5 | 26 | 7 | 26 | 7 | 0.26 |
| wB | pg/ml | 8.7E3 | 2.2E4 | 9.8E3 | 2.1E4 | 6.9E3 | 1.1E4 | 1.7E3 | 5.3E3 | 3.3E4 | 4.2E4 | 47 | 10 | 47 | 10 | 0.80 |
| pY | pg/ml | 5.9E0 | 6.4E0 | 1.0E1 | 7.4E0 | 2.8E1 | 3.8E0 | 1.6E0 | 4.4E0 | 2.0E2 | 1.7E1 | 46 | 9 | 46 | 9 | 0.61 |
| rC | pg/ml | 1.5E3 | 1.0E3 | 2.3E3 | 1.7E3 | 2.4E3 | 1.7E3 | 1.0E-9 | 7.0E1 | 1.5E4 | 7.3E3 | 70 | 18 | 70 | 18 | 0.41 |
| rB | pg/ml | 3.0E1 | 5.9E1 | 4.8E1 | 7.4E1 | 6.3E1 | 8.4E1 | 1.0E-9 | 1.0E-9 | 3.9E2 | 3.2E2 | 70 | 18 | 70 | 18 | 0.58 |
| zG | 2.5ng/ml | 2.2E-1 | 3.8E-1 | 5.6E-1 | 6.3E-1 | 1.0E0 | 8.6E-1 | 1.0E-9 | 1.0E-9 | 4.8E0 | 2.7E0 | 46 | 9 | 46 | 9 | 0.59 |
| zH | 2.3mU/ml | 9.0E-2 | 8.5E-2 | 1.0E-1 | 8.4E-2 | 4.9E-2 | 2.6E-2 | 1.0E-2 | 4.4E-2 | 3.1E-1 | 1.2E-1 | 46 | 9 | 46 | 9 | 0.39 |
| zI | 2.6ng/ml | 2.1E0 | 3.4E0 | 4.2E0 | 6.0E0 | 5.8E0 | 5.9E0 | 5.4E-1 | 9.1E-1 | 2.7E1 | 1.6E1 | 46 | 9 | 46 | 9 | 0.62 |
| qA | ng/ml | 1.0E7 | 1.3E7 | 1.2E7 | 1.4E7 | 7.3E6 | 7.7E6 | 3.7E6 | 4.3E6 | 3.9E7 | 3.0E7 | 46 | 9 | 46 | 9 | 0.62 |
| qB | ng/ml | 6.9E5 | 5.7E5 | 8.3E5 | 9.9E5 | 5.5E5 | 1.1E6 | 1.9E5 | 2.4E5 | 2.9E6 | 3.8E6 | 46 | 9 | 46 | 9 | 0.44 |
| qC | ng/ml | 3.6E5 | 2.4E5 | 7.6E5 | 2.4E5 | 1.1E6 | 1.2E5 | 2.5E4 | 6.5E4 | 5.2E6 | 5.0E5 | 46 | 9 | 46 | 9 | 0.33 |
| qD | ng/ml | 1.6E7 | 1.4E7 | 1.8E7 | 1.4E7 | 8.9E6 | 5.1E6 | 1.2E6 | 1.0E7 | 4.5E7 | 2.6E7 | 46 | 9 | 46 | 9 | 0.38 |
| jD | ng/ml | 3.1E1 | 4.0E1 | 4.0E1 | 8.0E1 | 4.0E1 | 1.2E2 | 1.0E-9 | 1.0E-9 | 1.9E2 | 5.1E2 | 78 | 20 | 78 | 20 | 0.56 |
| jE | ng/ml | 1.0E-9 | 1.0E-9 | 5.7E0 | 5.9E0 | 1.2E1 | 1.1E1 | 1.0E-9 | 1.0E-9 | 6.2E1 | 3.5E1 | 78 | 20 | 78 | 20 | 0.51 |
| jF | ng/ml | 4.5E1 | 3.8E0 | 5.4E1 | 2.3E1 | 5.5E1 | 3.6E1 | 1.0E-9 | 1.0E-9 | 2.1E2 | 1.2E2 | 78 | 20 | 78 | 20 | 0.33 |
| jG | ng/ml | 4.4E3 | 4.2E3 | 4.6E3 | 4.3E3 | 2.0E3 | 1.8E3 | 6.7E2 | 1.5E3 | 9.6E3 | 7.9E3 | 78 | 20 | 78 | 20 | 0.47 |
| jH | ng/ml | 7.9E1 | 6.2E1 | 8.3E1 | 9.8E1 | 4.3E1 | 9.4E1 | 1.3E1 | 1.5E1 | 2.4E2 | 4.3E2 | 78 | 20 | 78 | 20 | 0.46 |
| jI | ng/ml | 7.3E1 | 9.8E1 | 7.5E1 | 1.2E2 | 3.2E1 | 9.6E1 | 1.9E1 | 4.4E1 | 1.9E2 | 4.4E2 | 78 | 20 | 78 | 20 | 0.68 |
| sK | pg/mL | 3.9E3 | 3.6E3 | 4.1E3 | 5.9E3 | 1.8E3 | 6.7E3 | 1.8E3 | 2.1E3 | 1.0E4 | 2.3E4 | 44 | 9 | 44 | 9 | 0.51 |
| sM | pg/mL | 7.2E4 | 7.9E4 | 7.8E4 | 9.3E4 | 2.9E4 | 4.3E4 | 3.9E4 | 5.1E4 | 1.6E5 | 2.0E5 | 44 | 9 | 44 | 9 | 0.64 |
| sO | pg/mL | 2.3E8 | 1.9E8 | 2.5E8 | 1.9E8 | 8.8E7 | 9.6E7 | 4.9E7 | 6.6E7 | 4.4E8 | 3.2E8 | 44 | 9 | 44 | 9 | 0.34 |
| wC | ng/ml | 1.5E0 | 1.7E0 | 1.9E0 | 1.7E0 | 1.4E0 | 1.2E0 | 3.6E-1 | 6.1E-2 | 6.5E0 | 4.3E0 | 47 | 10 | 47 | 10 | 0.51 |
| wD | ng/ml | 2.1E1 | 4.4E1 | 7.9E1 | 8.6E1 | 3.1E2 | 8.1E1 | 2.8E0 | 2.1E1 | 2.1E3 | 2.9E2 | 47 | 10 | 47 | 10 | 0.77 |
| wE | ng/ml | 4.9E1 | 4.1E1 | 5.1E1 | 4.7E1 | 2.0E1 | 2.0E1 | 8.1E0 | 2.0E1 | 9.4E1 | 8.9E1 | 47 | 10 | 47 | 10 | 0.41 |
| wG | ng/ml | 1.1E-1 | 5.8E-2 | 1.4E-1 | 1.5E-1 | 1.5E-1 | 2.3E-1 | 1.0E-9 | 1.0E-9 | 7.1E-1 | 6.8E-1 | 47 | 10 | 47 | 10 | 0.42 |
| wH | ng/ml | 3.3E-2 | 4.3E-2 | 2.3E-1 | 9.2E-1 | 6.6E-1 | 1.8E0 | 1.0E-9 | 1.0E-9 | 4.2E0 | 5.6E0 | 47 | 10 | 47 | 10 | 0.58 |
| wF | ng/ml | 1.8E-1 | 6.2E-1 | 2.4E0 | 1.8E0 | 9.3E0 | 2.0E0 | 1.0E-9 | 1.0E-9 | 5.7E1 | 4.7E0 | 47 | 10 | 47 | 10 | 0.64 |
| rA | pg/ml | 2.4E1 | 2.2E1 | 3.0E1 | 2.9E1 | 2.9E1 | 2.0E1 | 1.0E-9 | 5.8E0 | 2.0E2 | 7.2E1 | 75 | 20 | 75 | 20 | 0.52 |
| qZ | pg/ml | 4.6E1 | 6.6E1 | 5.8E2 | 3.6E2 | 2.2E3 | 8.9E2 | 2.8E-4 | 6.5E-2 | 1.0E4 | 3.4E3 | 57 | 14 | 57 | 14 | 0.53 |
| qY | pg/ml | 1.8E1 | 1.3E1 | 4.3E1 | 2.3E1 | 6.1E1 | 2.6E1 | 8.7E-1 | 2.1E0 | 3.3E2 | 9.8E1 | 75 | 20 | 75 | 20 | 0.41 |
| qX | pg/ml | 5.5E1 | 7.2E1 | 6.8E1 | 8.6E1 | 4.6E1 | 5.8E1 | 1.0E-9 | 2.3E1 | 2.3E2 | 2.1E2 | 75 | 20 | 75 | 20 | 0.57 |
| qW | pg/ml | 7.8E0 | 7.2E0 | 1.2E1 | 9.5E0 | 1.7E1 | 8.9E0 | 1.0E-9 | 1.0E-9 | 1.2E2 | 3.1E1 | 75 | 20 | 75 | 20 | 0.47 |
| qV | pg/ml | 1.7E3 | 2.1E3 | 2.4E3 | 2.7E3 | 1.9E3 | 2.3E3 | 1.0E2 | 1.7E2 | 1.1E4 | 9.6E3 | 75 | 20 | 75 | 20 | 0.52 |
| qU | pg/ml | 7.3E1 | 1.0E2 | 1.9E2 | 2.1E2 | 3.2E2 | 2.9E2 | 1.0E-9 | 1.0E-9 | 2.1E3 | 1.1E3 | 75 | 20 | 75 | 20 | 0.53 |
| qT | pg/ml | 3.9E1 | 4.4E1 | 6.6E1 | 6.2E1 | 7.6E1 | 4.7E1 | 1.0E-9 | 6.9E0 | 4.9E2 | 1.6E2 | 75 | 20 | 75 | 20 | 0.54 |
| qI | ng/ml | 6.2E4 | 5.9E4 | 6.3E4 | 5.9E4 | 3.1E4 | 2.6E4 | 1.0E4 | 2.5E4 | 1.6E5 | 9.8E4 | 43 | 9 | 43 | 9 | 0.48 |
| qH | ng/ml | 5.9E4 | 5.9E4 | 6.9E4 | 7.3E4 | 4.1E4 | 3.2E4 | 1.5E4 | 4.7E4 | 1.8E5 | 1.4E5 | 43 | 9 | 43 | 9 | 0.58 |
| qG | ng/ml | 1.9E5 | 1.7E5 | 1.9E5 | 1.7E5 | 7.3E4 | 4.8E4 | 3.4E4 | 9.9E4 | 4.2E5 | 2.3E5 | 43 | 9 | 43 | 9 | 0.41 |
| jK | ng/ml | 1.6E3 | 1.3E3 | 1.7E3 | 1.5E3 | 6.4E2 | 5.8E2 | 2.8E2 | 7.5E2 | 4.1E3 | 2.9E3 | 78 | 20 | 78 | 20 | 0.37 |
| jL | ng/ml | 2.0E2 | 2.4E2 | 2.7E2 | 2.8E2 | 2.1E2 | 1.5E2 | 5.6E1 | 1.2E2 | 9.6E2 | 6.3E2 | 78 | 20 | 78 | 20 | 0.58 |
| jM | ng/ml | 7.3E4 | 6.0E4 | 7.7E4 | 6.5E4 | 4.0E4 | 3.8E4 | 4.6E3 | 1.1E4 | 1.8E5 | 1.4E5 | 78 | 20 | 78 | 20 | 0.42 |
| jO | pg/ml | 2.3E5 | 2.2E5 | 2.8E5 | 2.5E5 | 1.7E5 | 1.3E5 | 6.0E4 | 9.8E4 | 1.1E6 | 6.5E5 | 78 | 20 | 78 | 20 | 0.45 |
| jP | pg/ml | 2.6E5 | 2.4E5 | 2.8E5 | 3.1E5 | 1.4E5 | 1.7E5 | 3.6E4 | 1.3E5 | 7.1E5 | 5.8E5 | 78 | 20 | 78 | 20 | 0.52 |
| jQ | pg/ml | 2.4E3 | 1.6E3 | 3.3E3 | 2.4E3 | 3.0E3 | 2.2E3 | 5.0E0 | 2.9E2 | 1.3E4 | 9.2E3 | 78 | 20 | 78 | 20 | 0.42 |
| jR | pg/ml | 5.9E3 | 4.2E3 | 1.1E4 | 8.0E3 | 1.3E4 | 1.1E4 | 1.0E-9 | 3.0E1 | 6.8E4 | 4.6E4 | 78 | 20 | 78 | 20 | 0.42 |
| jT | pg/ml | 1.8E5 | 1.5E5 | 1.8E5 | 1.5E5 | 7.3E4 | 5.3E4 | 7.1E4 | 7.5E4 | 5.5E5 | 2.5E5 | 78 | 20 | 78 | 20 | 0.36 |
| xA | pg/ml | 4.3E0 | 7.3E0 | 1.3E1 | 1.8E1 | 2.6E1 | 3.4E1 | 1.0E-9 | 1.0E-9 | 1.6E2 | 1.1E2 | 46 | 9 | 46 | 9 | 0.56 |
| yE | pg/ml | 8.1E1 | 9.1E1 | 8.2E1 | 1.0E2 | 3.3E1 | 4.2E1 | 6.4E0 | 6.3E1 | 1.5E2 | 2.0E2 | 46 | 9 | 46 | 9 | 0.62 |
| tM | pg/ml | 4.3E1 | 3.9E1 | 3.9E1 | 4.5E1 | 1.8E1 | 2.3E1 | 1.0E-9 | 1.6E1 | 8.3E1 | 9.9E1 | 46 | 9 | 46 | 9 | 0.53 |
| tL | pg/ml | 1.0E-9 | 1.0E-9 | 1.7E0 | 2.7E-1 | 9.9E0 | 6.1E-1 | 1.0E-9 | 1.0E-9 | 6.7E1 | 1.8E0 | 46 | 9 | 46 | 9 | 0.52 |
| jU | mIU/ml | 5.2E0 | 8.0E0 | 1.2E1 | 1.3E1 | 1.9E1 | 1.5E1 | 8.1E-2 | 1.2E0 | 1.1E2 | 5.3E1 | 78 | 20 | 78 | 20 | 0.57 |
| jV | mIU/ml | 1.9E0 | 1.7E0 | 4.0E0 | 3.7E0 | 5.7E0 | 4.6E0 | 2.7E-3 | 1.0E-1 | 3.2E1 | 1.8E1 | 78 | 20 | 78 | 20 | 0.48 |
| jY | ng/ml | 7.3E-4 | 3.5E-3 | 6.8E-3 | 1.0E-2 | 3.4E-2 | 2.1E-2 | 1.0E-9 | 1.0E-9 | 3.0E-1 | 9.4E-2 | 78 | 20 | 78 | 20 | 0.68 |
| kC | pg/ml | 1.0E2 | 9.2E1 | 2.0E2 | 1.3E2 | 3.9E2 | 1.3E2 | 2.1E1 | 3.6E1 | 2.7E3 | 5.9E2 | 58 | 18 | 58 | 18 | 0.43 |
| kE | pg/ml | 1.4E5 | 1.4E5 | 1.4E5 | 1.4E5 | 3.7E4 | 4.9E4 | 4.1E4 | 3.8E4 | 2.3E5 | 2.7E5 | 58 | 18 | 58 | 18 | 0.46 |
| kF | pg/mL | 6.6E1 | 5.9E1 | 6.8E1 | 7.1E1 | 2.3E1 | 3.1E1 | 2.7E1 | 4.0E1 | 1.5E2 | 1.4E2 | 58 | 18 | 58 | 18 | 0.48 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| kG | pg/mL | 8.5E3 | 8.9E3 | 1.1E4 | 2.3E4 | 9.8E3 | 3.8E4 | 1.3E3 | 1.1E3 | 5.8E4 | 1.6E5 | 58 | 18 | 58 | 18 | 0.54 |
| kI | pg/ml | 2.1E2 | 1.8E2 | 2.1E2 | 2.2E2 | 1.1E2 | 1.3E2 | 4.4E1 | 1.0E-9 | 6.7E2 | 5.5E2 | 58 | 18 | 58 | 18 | 0.49 |
| kK | pg/ml | 1.2E2 | 1.2E2 | 1.8E2 | 1.8E2 | 2.7E2 | 1.4E2 | 6.4E0 | 2.9E1 | 1.9E3 | 5.5E2 | 58 | 18 | 58 | 18 | 0.57 |
| kN | pg/ml | 1.2E3 | 8.2E2 | 1.5E3 | 1.7E3 | 1.5E3 | 2.3E3 | 7.3E1 | 3.8E2 | 1.0E4 | 8.7E3 | 58 | 18 | 58 | 18 | 0.42 |
| kO | pg/ml | 7.2E3 | 6.6E3 | 1.0E4 | 7.4E3 | 1.9E4 | 2.8E3 | 3.7E3 | 4.4E3 | 1.5E5 | 1.4E4 | 58 | 18 | 58 | 18 | 0.45 |
| kP | pg/ml | 6.4E3 | 4.5E3 | 7.1E3 | 5.2E3 | 4.4E3 | 3.4E3 | 9.6E2 | 2.7E4 | 1.5E4 | 58 | 18 | 58 | 18 | 0.36 |
| kQ | pg/ml | 4.4E3 | 4.3E3 | 5.3E3 | 5.6E3 | 4.0E3 | 4.3E3 | 5.6E2 | 1.4E3 | 2.5E4 | 2.2E4 | 96 | 23 | 96 | 23 | 0.52 |
| kR | pg/ml | 2.2E1 | 2.0E1 | 3.7E1 | 3.5E1 | 1.0E2 | 3.2E1 | 1.0E-9 | 2.9E0 | 1.0E3 | 1.1E2 | 96 | 23 | 96 | 23 | 0.52 |
| kS | pg/ml | 8.7E2 | 9.2E2 | 9.9E2 | 1.0E3 | 5.9E2 | 5.8E2 | 8.2E1 | 2.5E2 | 3.2E3 | 2.5E3 | 96 | 23 | 96 | 23 | 0.54 |
| pS | ng/ml | 1.6E5 | 1.2E5 | 1.9E5 | 1.3E5 | 1.0E5 | 5.5E4 | 7.5E4 | 6.8E4 | 5.7E5 | 2.6E5 | 44 | 9 | 44 | 9 | 0.23 |
| rZ | ng/ml | 1.4E-3 | 6.6E-3 | 6.5E-3 | 3.1E-2 | 1.5E-2 | 7.2E-2 | 1.0E-9 | 1.0E-9 | 9.4E-2 | 3.0E-1 | 71 | 18 | 71 | 18 | 0.65 |
| rY | ng/ml | 6.1E-2 | 7.3E-2 | 4.6E-1 | 1.1E0 | 2.5E0 | 4.2E0 | 1.0E-9 | 1.0E-9 | 2.0E1 | 1.8E1 | 71 | 18 | 71 | 18 | 0.58 |
| rX | ng/ml | 1.0E-9 | 1.0E-9 | 1.1E-1 | 1.6E-1 | 5.7E-1 | 5.6E-1 | 1.0E-9 | 1.0E-9 | 3.7E0 | 2.4E0 | 71 | 18 | 71 | 18 | 0.60 |
| lK | pg/ml | 6.0E1 | 5.2E1 | 1.5E2 | 1.1E2 | 1.8E2 | 1.5E2 | 1.0E-9 | 1.0E-9 | 7.4E2 | 5.0E2 | 77 | 20 | 77 | 20 | 0.41 |
| lL | pg/ml | 1.6E3 | 1.8E3 | 3.0E3 | 2.6E3 | 5.2E3 | 2.1E3 | 7.5E1 | 5.3E2 | 4.2E4 | 7.7E3 | 78 | 20 | 78 | 20 | 0.55 |
| lM | pg/ml | 1.2E3 | 2.0E3 | 3.7E3 | 8.7E3 | 6.5E3 | 1.6E4 | 2.1E2 | 9.5E0 | 4.2E4 | 6.7E4 | 78 | 20 | 78 | 20 | 0.56 |
| lN | pg/ml | 1.0E-9 | 1.5E0 | 3.1E0 | 4.1E0 | 6.9E0 | 6.3E0 | 1.0E-9 | 1.0E-9 | 4.3E1 | 2.1E1 | 78 | 20 | 78 | 20 | 0.58 |
| lO | pg/ml | 1.0E-9 | 1.0E-9 | 2.1E0 | 6.9E0 | 1.5E1 | 3.1E1 | 1.0E-9 | 1.0E-9 | 1.3E2 | 1.4E2 | 77 | 20 | 77 | 20 | 0.51 |
| zA | ng/ml | 2.1E7 | 2.1E7 | 2.2E7 | 1.9E7 | 6.7E6 | 4.8E6 | 9.1E6 | 1.1E7 | 3.6E7 | 2.5E7 | 46 | 10 | 46 | 10 | 0.42 |
| rW | ng/ml | 1.1E-2 | 1.5E-2 | 3.5E-2 | 1.8E-2 | 6.2E-2 | 8.0E-3 | 1.0E-9 | 7.4E-3 | 3.2E-1 | 3.3E-2 | 43 | 9 | 43 | 9 | 0.59 |
| rV | ng/ml | 1.0E-9 | 6.7E-3 | 1.1E-2 | 2.9E-2 | 4.6E-2 | 5.0E-2 | 1.0E-9 | 1.0E-9 | 2.8E-1 | 1.5E-1 | 43 | 9 | 43 | 9 | 0.70 |
| rU | ng/ml | 7.1E-2 | 1.3E-1 | 1.7E-1 | 1.6E-1 | 4.2E-1 | 1.3E-1 | 1.0E-9 | 1.0E-9 | 2.7E0 | 4.0E-1 | 43 | 9 | 43 | 9 | 0.64 |
| rT | ng/ml | 6.1E0 | 6.8E0 | 6.8E0 | 7.6E0 | 4.5E0 | 5.6E0 | 6.5E-1 | 1.0E0 | 2.1E1 | 1.8E1 | 43 | 9 | 43 | 9 | 0.54 |
| rS | ng/ml | 3.5E0 | 9.0E0 | 5.4E0 | 2.4E1 | 5.1E0 | 2.5E1 | 7.6E-1 | 2.0E0 | 2.5E1 | 7.0E1 | 43 | 9 | 43 | 9 | 0.79 |
| sC | pg/mL | 5.4E3 | 7.9E3 | 1.1E4 | 1.0E4 | 1.4E4 | 7.7E3 | 1.7E3 | 3.4E3 | 7.4E4 | 2.8E4 | 44 | 9 | 44 | 9 | 0.61 |
| yL | pg/ml | 2.9E1 | 4.1E1 | 3.3E1 | 2.0E2 | 2.6E1 | 4.6E2 | 5.6E0 | 1.2E1 | 1.8E2 | 1.4E3 | 46 | 9 | 46 | 9 | 0.67 |
| rP | ng/ml | 1.2E2 | 2.1E2 | 2.0E2 | 2.8E2 | 2.0E2 | 2.2E2 | 1.0E-9 | 1.2E1 | 8.0E2 | 5.0E2 | 43 | 9 | 43 | 9 | 0.60 |
| rQ | ng/ml | 1.0E-9 | 1.0E-9 | 3.5E0 | 1.9E1 | 1.9E1 | 5.6E1 | 1.0E-9 | 1.0E-9 | 1.2E2 | 1.7E2 | 43 | 9 | 43 | 9 | 0.53 |
| rO | ng/ml | 2.0E-2 | 4.0E-3 | 4.1E-2 | 3.0E-2 | 6.9E-2 | 4.8E-2 | 1.0E-9 | 1.0E-9 | 4.0E-1 | 1.2E-1 | 43 | 9 | 43 | 9 | 0.42 |
| rR | ng/ml | 3.9E0 | 1.0E-9 | 9.2E0 | 1.8E1 | 1.8E1 | 3.2E1 | 1.0E-9 | 1.0E-9 | 7.9E1 | 9.5E1 | 43 | 9 | 43 | 9 | 0.51 |
| rN | ng/ml | 6.3E-1 | 1.3E0 | 8.0E-1 | 2.8E0 | 5.3E-1 | 4.0E0 | 5.1E-2 | 3.4E-1 | 2.3E0 | 1.3E1 | 43 | 9 | 43 | 9 | 0.72 |
| qO | pg/ml | 8.2E3 | 1.0E4 | 1.2E4 | 1.2E4 | 1.1E4 | 9.3E3 | 7.4E2 | 5.4E3 | 4.8E4 | 3.5E4 | 44 | 9 | 44 | 9 | 0.55 |
| qP | pg/ml | 3.5E2 | 3.6E2 | 4.2E2 | 3.9E2 | 2.9E2 | 2.0E2 | 7.0E1 | 1.5E2 | 1.5E3 | 7.8E2 | 44 | 9 | 44 | 9 | 0.52 |
| qQ | pg/ml | 1.5E1 | 3.3E1 | 2.3E1 | 2.6E1 | 5.6E1 | 1.8E1 | 1.0E-9 | 1.0E-9 | 2.8E2 | 4.3E1 | 44 | 9 | 44 | 9 | 0.71 |
| nW | pg/ml | 1.1E5 | 1.1E5 | 1.1E5 | 1.1E5 | 2.7E4 | 3.4E4 | 5.8E4 | 3.6E4 | 1.9E5 | 1.7E5 | 96 | 23 | 96 | 23 | 0.49 |
| nY | pg/ml | 2.2E3 | 3.5E3 | 2.6E3 | 3.2E3 | 1.5E3 | 1.8E3 | 5.1E2 | 6.3E2 | 1.0E4 | 8.1E3 | 96 | 23 | 96 | 23 | 0.63 |
| oO | pg/ml | 8.8E4 | 9.8E4 | 1.0E5 | 1.3E5 | 6.3E4 | 1.1E5 | 1.5E4 | 3.3E3 | 3.0E5 | 4.0E5 | 53 | 16 | 53 | 16 | 0.54 |
| oP | pg/ml | 1.2E5 | 1.6E5 | 1.4E5 | 1.9E5 | 8.4E4 | 1.4E5 | 2.4E4 | 2.4E4 | 4.2E5 | 5.7E5 | 53 | 16 | 53 | 16 | 0.61 |
| oQ | pg/ml | 2.9E3 | 3.9E3 | 3.5E3 | 6.6E3 | 3.1E3 | 7.8E3 | 7.7E2 | 9.1E2 | 2.1E4 | 3.2E4 | 53 | 16 | 53 | 16 | 0.65 |
| oE | pg/ml | 1.9E2 | 4.6E2 | 4.3E2 | 8.6E2 | 5.4E2 | 9.8E2 | 1.0E-9 | 1.0E-9 | 2.6E3 | 3.4E3 | 96 | 23 | 96 | 23 | 0.63 |
| oF | pg/ml | 1.1E4 | 3.0E4 | 2.4E4 | 4.8E4 | 3.7E4 | 4.8E4 | 3.5E2 | 6.5E2 | 2.5E5 | 1.7E5 | 96 | 23 | 96 | 23 | 0.70 |
| oH | pg/ml | 4.0E1 | 2.3E1 | 8.3E1 | 5.3E1 | 1.2E2 | 7.8E1 | 4.4E0 | 4.3E-1 | 8.6E2 | 3.1E2 | 96 | 23 | 96 | 23 | 0.39 |
| oK | pg/ml | 8.4E2 | 1.3E3 | 1.7E3 | 1.5E3 | 2.0E3 | 1.4E3 | 8.8E1 | 1.8E2 | 1.2E4 | 5.9E3 | 96 | 23 | 96 | 23 | 0.52 |
| oN | pg/ml | 5.4E2 | 5.8E2 | 1.0E3 | 7.3E2 | 2.1E3 | 4.0E2 | 1.1E2 | 2.8E2 | 1.8E4 | 1.8E3 | 96 | 23 | 96 | 23 | 0.59 |
| oW | pg/ml | 2.0E2 | 4.6E2 | 2.9E2 | 1.9E3 | 2.2E2 | 2.7E3 | 2.9E1 | 9.3E1 | 8.5E2 | 7.6E3 | 26 | 7 | 26 | 7 | 0.76 |
| oT | pg/ml | 2.9E2 | 2.6E2 | 3.4E2 | 2.9E2 | 1.9E2 | 1.2E2 | 1.0E2 | 1.5E2 | 7.9E2 | 5.4E2 | 26 | 7 | 26 | 7 | 0.43 |
| oV | pg/ml | 1.1E2 | 7.0E1 | 3.1E2 | 1.5E2 | 5.0E2 | 2.2E2 | 1.4E1 | 1.0E-9 | 2.2E3 | 6.3E2 | 26 | 7 | 26 | 7 | 0.38 |
| oD | pg/ml | 1.5E4 | 1.6E4 | 1.5E4 | 1.7E4 | 5.6E3 | 7.5E3 | 6.6E3 | 9.3E3 | 2.5E4 | 3.2E4 | 26 | 7 | 26 | 7 | 0.52 |
| uL | ng/ml | 3.7E1 | 4.3E1 | 5.0E1 | 4.4E1 | 4.6E1 | 2.5E1 | 1.5E1 | 1.4E1 | 2.9E2 | 8.0E1 | 43 | 9 | 43 | 9 | 0.50 |
| uO | ng/ml | 3.8E-1 | 4.8E-1 | 8.2E-1 | 8.6E-1 | 1.5E0 | 8.5E-1 | 1.0E-9 | 1.0E-9 | 9.3E0 | 2.1E0 | 43 | 9 | 43 | 9 | 0.57 |
| uM | ng/ml | 5.3E-1 | 6.2E-1 | 9.3E-1 | 7.6E-1 | 2.0E0 | 7.6E-1 | 1.0E-9 | 1.0E-9 | 1.3E1 | 2.5E0 | 43 | 9 | 43 | 9 | 0.52 |
| uI | ng/ml | 7.5E-2 | 5.1E-2 | 1.1E-1 | 1.0E-1 | 1.1E-1 | 1.2E-1 | 1.6E-2 | 1.5E-2 | 5.8E-1 | 3.8E-1 | 42 | 9 | 42 | 9 | 0.43 |
| uN | ng/ml | 1.5E1 | 1.7E1 | 1.6E1 | 2.0E1 | 6.3E0 | 9.7E0 | 8.0E0 | 1.0E1 | 3.6E1 | 4.1E1 | 43 | 9 | 43 | 9 | 0.63 |
| uG | ng/ml | 1.8E1 | 1.9E1 | 2.2E1 | 3.4E1 | 1.5E1 | 3.9E1 | 1.2E0 | 6.5E0 | 7.9E1 | 1.3E2 | 43 | 9 | 43 | 9 | 0.58 |
| uR | ng/ml | 2.3E0 | 1.7E0 | 2.9E0 | 2.3E0 | 2.3E0 | 1.8E0 | 7.5E-1 | 9.1E-1 | 1.3E1 | 6.6E0 | 46 | 9 | 46 | 9 | 0.38 |
| uP | ng/ml | 2.2E0 | 2.7E0 | 2.4E0 | 3.1E0 | 9.9E-1 | 1.7E0 | 1.2E0 | 9.3E-1 | 6.0E0 | 6.1E0 | 46 | 9 | 46 | 9 | 0.64 |
| uV | ng/ml | 1.7E-3 | 1.3E-3 | 1.5E-2 | 8.0E-3 | 3.3E-2 | 1.4E-2 | 1.0E-9 | 1.0E-9 | 2.0E-1 | 4.3E-2 | 46 | 9 | 46 | 9 | 0.46 |

Figure 28 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| uT | ng/ml | 6.4E1 | 1.2E2 | 8.8E1 | 1.6E2 | 8.3E1 | 1.1E2 | 1.3E1 | 5.7E1 | 4.5E2 | 4.1E2 | 46 | 9 | 46 | 9 | 0.79 |
| uU | ng/ml | 1.8E0 | 1.7E0 | 1.9E0 | 3.8E0 | 1.2E0 | 6.0E0 | 5.2E-1 | 5.4E-1 | 6.0E0 | 2.0E1 | 46 | 9 | 46 | 9 | 0.54 |
| uW | ng/ml | 7.5E0 | 7.9E0 | 7.9E0 | 8.1E0 | 2.4E0 | 1.8E0 | 4.4E0 | 6.5E0 | 1.6E1 | 1.1E1 | 43 | 9 | 43 | 9 | 0.56 |
| vB | ng/ml | 3.0E0 | 3.2E0 | 3.4E0 | 2.9E0 | 2.3E0 | 8.4E-1 | 5.9E-1 | 1.3E0 | 1.0E1 | 3.8E0 | 43 | 9 | 43 | 9 | 0.50 |
| vC | ng/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 43 | 9 | 43 | 9 | 0.50 |
| uY | ng/ml | 6.1E-1 | 8.7E-1 | 9.1E-1 | 1.4E0 | 8.5E-1 | 1.3E0 | 6.8E-2 | 3.1E-1 | 3.8E0 | 4.4E0 | 43 | 9 | 43 | 9 | 0.65 |
| uZ | ng/ml | 5.8E-1 | 5.3E-1 | 7.5E-1 | 6.5E-1 | 8.1E-1 | 5.1E-1 | 1.0E-1 | 1.7E-1 | 4.9E0 | 1.9E0 | 43 | 9 | 43 | 9 | 0.46 |
| uX | ng/ml | 8.3E0 | 9.1E0 | 1.1E1 | 2.3E1 | 6.8E0 | 2.3E1 | 3.6E0 | 5.6E0 | 4.0E1 | 6.5E1 | 43 | 9 | 43 | 9 | 0.65 |
| vA | ng/ml | 6.3E-2 | 6.6E-2 | 7.4E-2 | 1.2E-1 | 4.5E-2 | 1.3E-1 | 2.4E-2 | 2.5E-2 | 2.7E-1 | 4.2E-1 | 43 | 9 | 43 | 9 | 0.56 |
| vH | ng/ml | 1.2E-1 | 1.1E-1 | 1.5E-1 | 3.4E-1 | 1.3E-1 | 6.0E-1 | 2.0E-2 | 4.7E-2 | 6.6E-1 | 1.9E0 | 44 | 9 | 44 | 9 | 0.50 |
| vI | ng/ml | 1.8E0 | 3.5E0 | 2.2E0 | 3.9E0 | 1.9E0 | 2.7E0 | 6.3E-3 | 1.2E0 | 1.0E1 | 1.0E1 | 44 | 9 | 44 | 9 | 0.77 |
| vP | ng/ml | 3.8E2 | 2.9E2 | 4.7E2 | 4.3E2 | 4.4E2 | 3.2E2 | 6.7E1 | 1.5E2 | 2.4E3 | 1.1E3 | 46 | 9 | 46 | 9 | 0.53 |
| vT | ng/ml | 7.2E1 | 8.2E1 | 8.5E1 | 9.9E1 | 4.0E1 | 5.2E1 | 4.1E1 | 4.6E1 | 2.4E2 | 1.8E2 | 46 | 9 | 46 | 9 | 0.55 |
| vU | ng/ml | 1.0E-9 | 1.0E-9 | 2.7E1 | 1.9E1 | 4.0E1 | 3.7E1 | 1.0E-9 | 1.0E-9 | 1.3E2 | 1.1E2 | 46 | 9 | 46 | 9 | 0.44 |
| vQ | ng/ml | 4.0E2 | 4.5E2 | 4.2E2 | 4.0E2 | 1.6E2 | 1.8E2 | 7.2E1 | 1.9E2 | 8.4E2 | 6.5E2 | 46 | 9 | 46 | 9 | 0.47 |
| vO | ng/ml | 1.7E3 | 1.7E3 | 1.8E3 | 1.8E3 | 4.3E2 | 6.0E2 | 1.1E3 | 1.0E3 | 2.9E3 | 3.2E3 | 46 | 9 | 46 | 9 | 0.47 |
| vS | ng/ml | 1.3E3 | 1.3E3 | 1.2E3 | 1.3E3 | 4.3E2 | 5.7E2 | 1.0E-9 | 1.0E-9 | 2.1E3 | 1.9E3 | 46 | 9 | 46 | 9 | 0.56 |
| vV | ng/ml | 9.1E2 | 8.2E2 | 1.1E3 | 9.1E2 | 9.8E2 | 5.3E2 | 1.0E2 | 2.3E2 | 4.6E3 | 1.7E3 | 46 | 9 | 46 | 9 | 0.51 |
| vW | ng/ml | 1.1E2 | 2.4E2 | 1.5E2 | 2.6E2 | 1.1E2 | 2.2E2 | 4.3E1 | 6.0E1 | 6.6E2 | 7.7E2 | 46 | 9 | 46 | 9 | 0.68 |
| pF | pg/ml | 5.9E-1 | 5.7E-1 | 1.7E0 | 9.0E-1 | 8.9E0 | 7.5E-1 | 1.0E-9 | 1.8E-1 | 8.7E1 | 3.5E0 | 96 | 23 | 96 | 23 | 0.57 |
| pH | ng/ml | 7.4E0 | 1.3E1 | 8.1E0 | 1.5E1 | 3.9E0 | 5.7E0 | 1.2E0 | 6.8E0 | 1.8E1 | 2.3E1 | 26 | 7 | 26 | 7 | 0.85 |
| pI | ng/ml | 7.0E1 | 4.6E1 | 7.7E1 | 5.8E1 | 4.6E1 | 2.9E1 | 2.3E1 | 2.5E1 | 2.0E2 | 1.1E2 | 26 | 7 | 26 | 7 | 0.40 |
| pK | ng/ml | 4.5E-1 | 4.0E-1 | 4.6E-1 | 4.6E-1 | 1.9E-1 | 2.0E-1 | 1.7E-1 | 2.7E-1 | 8.6E-1 | 8.3E-1 | 26 | 7 | 26 | 7 | 0.51 |

Analyte panel data:

Unconstrained panels with 3 analytes, where 1.0E-10 >= 'model p-value' > 0. Contains 25,582 panels of 35,191,980 total panels evaluated. : Nw{Nb(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Ps Pz Qa Qb Qc Qd Qe Rt Rx Uw Ux Uy Uz Va Vb Vc Vh Vi Vw Wc Wd We Wf Wg Wh) Im(aA Aj Et Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe Rx) In(aA Aj Et Fp Fr Hq Hr Hu Hv Hw Hx Ih Ii Ij Ik Il In Io Ip Iq Ir Is It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe Rx) Et(aA Aj Fp Fr Hq Hr Hu Hv Hw Hx Ih Ii Ij Ik Il In Io Ip Iq Ir Is It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) No(aA Aj Fp Fr Hq Hr Hu Hv Hw Hx Ih Ii Ij Ik Il In Io Ip Iq Ir Is It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Mt(aA Aj Fp Fr Hq Hr Hu Hv Hw Hx Ih Ii Ij Ik Il In Io Ip Iq Ir Is It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Ij(aA Aj Fp Fr Hq Hr Hu Hv Hw Hx Ih Ii Ik Il In Io Ip Iq Ir Is It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mu Mv Mw Mx My Mz Na Nc Nd Ne Nf Ng Nh Ni Nj Nk Nl Nm Nn Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Il(aA Aj Fp Fr Hq Hr Hu Hv Hw Hx Ih Ii Ik In Io Ip Iq Ir Is It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mu Mv Mw Mx My Mz Na Nc Nd Ne Nf Ng Nh Ni Nj Nk Nl Nm Nn Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Is(aA Aj Fp Fr Hq Hr Hu Hv Hw Hx Ih Ii Ik In Io Ip Iq Ir It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mu Mv Mw Mx My Mz Na Nc Nd Ne Nf Ng Nh Ni Nj Nk Nl Nm Nn Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Qa(aA Aj Fp Fr Hq Hr Hu Hv Hw Hx Ih Ii Ik In Io Ip Iq Ir It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mu Mv Mw Mx My Mz Na Nc Nd Ne Nf Ng Nh Ni Nj Nk Nl Nm Nn Nq Nr Ns Nt Nu Nv Nx Ny Oe Of Og Oh Oi Ok Om On Oy Oz Pa Pb Pc Pd Pe Pf Pg Po Pz Qb Qc Qd Qe) Qd(aA Aj Fp Fr Hq Hr Hu Hv Hw Hx Ih Ii Ik In Io Ip Iq Ir It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mu Mv Mw Mx My Mz Na Nc Nd Ne Nf Ng Nh Ni Nj Nk Nl Nm Nn Nq Nr Ns Nt Nu Nv Nx Ny Oe Of Og Oh Oi Ok Om On Oy Oz Pa Pb Pc Pd Pe Pf Pg Po Pz Qb Qc Qe) Qe(aA Aj Fp Fr Hq Hr Hu Hv Hw Hx Ih Ii Ik In Io Ip Iq Ir It Iu Iv Jg Jh Ji Jj Jk Jl Jm Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mu Mv Mw Mx My Mz Na Nc Nd Ne Nf Ng Nh Ni Nj Nk Nl Nm Nn Nq Nr Ns Nt Nu Nv Nx Ny Oe Of Og Oh Oi Ok Om On Oy Oz Pa Pb Pc Pd Pe Pf Pg Po Pz Qb Qc) Jg(aA Aj Fp Fr Hq Hr Hu Hv Hw Hx Ih Ii Ik In Io Ip Iq Ir It Iu Iv Jh Ji Jj Jk Jl Jm Jo Jp Jq Jr Js Jt Lh Li Lj Lu Lv Lw Lx Ly Lz Ma Mb

Pe Pf Pg) Li(aA Nv Nx Ny Oe Of Og Oh Ok Om On Oy Pa Pb Pc Pd Pe Pf Pg) Nv(aA Nx Ny Oe Of Og Oh Ok Om On Oy Pa Pb Pc Pd Pe Pf Pg) Nx(aA Ny Oe Of Og Oh Ok Om On Oy Pa Pb Pc Pd Pe Pf Pg) Ny(aA Oe Of Og Oh Ok Om On Oy Pa Pb Pc Pd Pe Pf Pg) Oe(aA Of Og Oh Ok Om On Oy Pa Pb Pc Pd Pe Pf Pg) Of(aA Og Oh Ok Om On Oy Pa Pb Pc Pd Pe Pf Pg) Og(aA Oh Ok Om On Oy Pa Pb Pc Pd Pe Pf Pg) Oh(aA Ok Om On Oy Pa Pb Pc Pd Pe Pf Pg) Ok(aA Om On Oy Pa Pb Pc Pd Pe Pf Pg) Om(aA On Oy Pa Pb Pc Pd Pe Pf Pg) On(aA Oy Pa Pb Pc Pd Pe Pf Pg) Oy(aA Pa Pb Pc Pd Pe Pf Pg) Pa(aA Pb Pc Pd Pe Pf Pg) Pb(aA Pc Pd Pe Pf Pg) Pc(aA Pd Pe Pf Pg) Pd(aA Pe Pf Pg) Rx(aF aO Dp) Pe(aA Pf Pg) Pf(aA Pg) PgaA} Ji{Et(aA Aj Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Nb(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe Ux) Ii(aA bA Fp Fr Hq Hr Hu Hv Hw Hx Ih Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Im(aA Aj Fp Fr Hq Hr Hu Hv Hw Hx Ih Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Jo(aA Fp Fr Hq Hr Hu Hv Hw Hx Ih Ij Ik Il In Io Ip Iq Ir Is It Iu Iv Jg Jh Jj Jk Jl Jm Jn Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe Wm) Jp(aA Aj Fp Fr Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Po(aA Fp Fr Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Pz Qa Qb Qc Qd Qe) Fp(aA Fr Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Pz Qa Qb Qc Qd Qe) Fr(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Pz Qa Qb Qc Qd Qe) Nm(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nn No Nq Nr Ns Nt Nu Nv Nx Ny Oe Of Og Oh Oi Ok Om On Oy Oz Pa Pb Pc Pd Pe Pf Pg Pz Qa Qb Qc Qd Qe) Nn(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl No Nq Nr Ns Nt Nu Nv Nx Ny Oe Of Og Oh Oi Ok Om On Oy Oz Pa Pb Pc Pd Pe Pf Pg Pz Qa Qb Qc Qd Qe) No(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nq Nr Ns Nt Nu Nv Nx Ny Oe Of Og Oh Oi Ok Om On Oy Oz Pa Pb Pc Pd Pe Pf Pg Pz Qa Qb Qc Qd Qe) Nq(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nr Ns Nt Nu Nv Nx Ny Oe Of Og Oh Oi Ok Om On Oy Oz Pa Pb Pc Pd Pe Pf Pg Pz Qa Qb Qc Qd Qe) Nr(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Ns Nt Nu Nv Nx Ny Oe Of Og Oh Oi Ok Om On Oy Oz Pa Pb Pc Pd Pe Pf Pg Pz Qa Qb Qc Qd Qe) Ns(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nt Nu Nv Nx Ny Oe Of Og Oh Oi Ok Om On Oy Oz Pa Pb Pc Pd Pe Pf Pg Pz Qa Qb Qc Qd Qe) Nt(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nu Nv Nx Ny Oe Of Og Oh Oi Ok Om On Oy Oz Pa Pb Pc Pd Pe Pf Pg Pz Qa Qb Qc Qd Qe) Nu(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nv Nx Ny Oe Of Og Oh Oi Ok Om On Oy Oz Pa Pb Pc Pd Pe Pf Pg Pz Qa Qb Qc Qd Qe) Lu(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nv Nx Ny Oe Of Og Oh Oi Ok Om On Oy Oz Pa Pb Pc Pd Pe Pf Pg Pz Qa Qb Qc Qd Qe) Lv(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nv Nx Ny Oe Of Og Oh Oi Ok Om On Oy Oz Pa Pb Pc Pd Pe Pf Pg Pz Qa Qb Qc Qd Qe) Lw(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nv Nx Ny Oe Of Og Oh Oi Ok Om On Oy Oz Pa Pb Pc Pd Pe Pf Pg Pz Qa Qb Qc Qd Qe) Lx(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nv Nx Ny Oe Of Og Oh Oi Ok Om On Oy Oz Pa Pb Pc Pd Pe Pf Pg Pz Qa Qb Qc Qd Qe) Ly(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nv Nx Ny Oe Of Og Oh Oi Ok Om On Oy Oz Pa Pb Pc Pd Pe Pf Pg Pz Qa Qb Qc Qd Qe) Lz(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nv Nx Ny Oe Of Og Oh Oi Ok Om On Oy Oz Pa Pb Pc Pd Pe Pf Pg Pz Qa Qb Qc Qd Qe) Ma(aA Hq Hr Hu Hv Hw Hx Ih Ij Ik Il In Io Ip Iq Ir Is It Iu Iv Jg Jh Jj Jk Jl Jm Jn Jq Jr Js Jt Lh Li Lj Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nv Nx Ny Oe Of Og Oh Oi Ok Om On Oy Oz Pa

Qd Qe) Hv(aA Hw Hx Ih Ij Ik Il In Io Ip Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Hw(aA Hx Ih Ij Ik Il In Io Ip Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Hx(aA Ih Ij Ik Il In Io Ip Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Ih(aA Ij Ik Il In Io Ip Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Ij(aA Ik Il In Io Ip Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Ik(aA Il In Io Ip Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Il(aA In Io Ip Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) In(aA Io Ip Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Io(aA Ip Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Ip(aA Iq Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Iq(aA Ir Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Ir(aA Is It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Is(aA It Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) It(aA Iu Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Iu(aA Iv Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Iv(aA Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Pz Qa Qb Qc Qd Qe) Pz(aA Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Qa Qb Qc Qd Qe) Qa(aA Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Qb Qc Qd Qe) Qb(aA Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Qc Qd Qe) Qc(aA Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Qd Qe) Qd(aA Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg Qe) Qe(aA Jg Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg) Jg(aA Jh Jj Jk Jl Jm Jn Jq Jr Js Jt Lh Li Lj Nv Nx Ny Oe Of Og Oh Oi Ok Om On Oy Oz Pa Pb Pc Pd Pe Pf Pg) Jh(aA Jj Jk Jl Jm Jn Jq Jr Js Jt Lh Li Lj Nv Nx Ny Oe Of Og Oh Oi Ok Om On Oy Oz Pa Pb Pc Pd Pe Pf Pg) Jj(aA Jk Jl Jm Jn Jq Jr Js Jt Lh Li Lj Nv Nx Ny Oe Of Og Oh Oi Ok Om On Oy Oz Pa Pb Pc Pd Pe Pf Pg) Jk(aA Jl Jm Jn Jq Jr Js Jt Lh Li Lj Nv Nx Ny Oe Of Og Oh Oi Ok Om On Oy Oz Pa Pb Pc Pd Pe Pf Pg) Jl(aA Jm Jn Jq Jr Js Jt Lh Li Lj Nv Nx Ny Oe Of Og Oh Oi Ok Om On Oy Oz Pa Pb Pc Pd Pe Pf Pg) Jm(aA Jn Jq Jr Js Jt Lh Li Lj Nv Nx Ny Oe Of Og Oh Oi Ok Om On Oy Oz Pa Pb Pc Pd Pe Pf Pg) Jn(aA Jq Jr Js Jt Lh Li Lj Nv Nx Ny Oe Of Og Oh Oi Ok Om On Oy Oz Pa Pb Pc Pd Pe Pf Pg) Jq(aA Jr Js Jt Lh Li Lj Nv Nx Ny Oe Of Og Oh Oi Ok Om On Oy Oz Pa Pb Pc Pd Pe Pf Pg) Jr(aA Js Jt Lh Li Lj Nv Nx Ny Oe Of Og Oh Oi Ok Om On Oy Oz Pa Pb Pc Pd Pe Pf Pg) Js(aA Jt Lh Li Lj Nv Nx Ny Oe Of Og Oh Oi Ok Om On Oy Oz Pa Pb Pc Pd Pe Pf Pg) Jt(aA Lh Li Lj Nv Nx Ny Oe Of Og Oh Oi Ok Om On Oy Oz Pa Pb Pc Pd Pe Pf Pg) Lh(aA Li Lj Nv Nx Ny Oe Of Og Oh Oi Ok Om On Oy Oz Pa Pb Pc Pd Pe Pf Pg) Li(aA Lj Nv Nx Ny Oe Of Og Oh Oi Ok Om On Oy Oz Pa Pb Pc Pd Pe Pf Pg) Lj(aA Nv Nx Ny Oe Of Og Oh Oi Ok Om On Oy Oz Pa Pb Pc Pd Pe Pf Pg) Nv(aA Nx Ny Oe Of Og Oh Oi Ok Om On Oy Oz Pa Pb Pc Pd Pe Pf Pg) Nx(aA Ny Oe Of Og Oh Oi Ok Om On Oy Oz Pa Pb Pc Pd Pe Pf Pg) Ny(aA Oe Of Og Oh Oi Ok Om On Oy Oz Pa Pb Pc Pd Pe Pf Pg) Oe(aA Of Og Oh Oi Ok Om On Oy Oz Pa Pb Pc Pd Pe Pf Pg) Of(aA Og Oh Oi Ok Om On Oy Oz Pa Pb Pc Pd Pe Pf Pg) Og(aA Oh Oi Ok Om On Oy Oz Pa Pb Pc Pd Pe Pf Pg) Oh(aA Oi Ok Om On Oy Oz Pa Pb Pc Pd Pe Pf Pg) Oi(aA Ok Om On Oy Oz Pa Pb Pc Pd Pe Pf Pg) Ok(aA Om On Oy Oz Pa Pb Pc Pd Pe Pf Pg) Om(aA On Oy Oz Pa Pb Pc Pd Pe Pf Pg) On(aA Oy Oz Pa Pb Pc Pd Pe Pf Pg) Oy(aA Oz Pa Pb Pc Pd Pe Pf Pg) Oz(aA Pa Pb Pc Pd Pe Pf Pg) Pa(aA Pb Pc Pd Pe Pf Pg) Pb(aA Pc Pd Pe Pf Pg) Pc(aA Pd Pe Pf Pg) Pd(aA Pe Pf Pg) Pe(aA Pf Pg) Pf(aA Pg) AjBa PgaA} Im{Oz(aA Et Fp Fr Hp Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Pa Pb Pc Pd Pe Pf Pg Po Pz Qa Qb Qc Qd Qe Sj Ye Xa) Mz(aA Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe Of Og Oh Oi Ok Om On Oy Pa Pb Pc Pd Pe Pf Pg Po Pz Qa Qb Qc Qd Qe We Wf Ye) Lv(aA Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe Of Og Oh Oi Ok Om On Oy Pa Pb Pc Pd Pe Pf Pg Po Pz Qa Qb Qc Qd Qe Wf Ye) Jl(aA Et Fp Fr Hq Hr Hu Hv Hw Hx Ih Ii Ij Ik Il In Io Ip Iq Ir Is It Iu Iv Jg Jh Jj Jk Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe Of Og Oh Oi Ok Om On Oy Pa Pb Pc Pd Pe Pf Pg Po Pz Qa Qb Qc Qd Qe Wf Ye) Et(aA Aj Fp Fr Hq Hr Hu Hv Hw Hx Ih Ii Ij Ik Il In Io Ip Iq Ir Is It Iu Iv Jg Jh Jj Jk Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe Of Og Oh Oi Ok Om On Oy Pa Pb Pc Pd Pe Pf Pg Po Pz Qa Qb Qc Qd Qe) No(aA Fp Fr Hq Hr Hu Hv Hw Hx Ih Ii Ij Ik Il In Io Ip Iq Ir Is It Iu Iv Jg Jh Jj Jk Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn Nq Nr Ns Nt Nu Nv Nx Ny Oe Of Og Oh Oi Ok Om On Oy Pa Pb Pc Pd Pe Pf Pg Po Pz Qa Qb Qc Qd Qe Ye) Mn(aA Aj Fp Fr Hq Hr Hu Hv Hw Hx Ih Ii Ij Ik Il In Io Ip Iq Ir Is It Iu Iv Jg Jh Jj Jk Jm Jn Jo Jp Jq Jr Js Jt Lh Li Lj Lu Lw Lx Ly Lz Ma Mb Mc Md Me Mf Mg Mh Mi Mj Mk Ml Mm Mp Mq Mr Ms Mt Mu Mv Mw Mx My Na Nb Nc Nd Ne Nf Ng Nh Ni Nj Nk Nl Nm Nn Nq Nr Ns Nt Nu Nv Nx Ny Oe Of Og Oh Oi Ok Om On Oy Pa Pb Pc Pd Pe Pf Pg Po Pz Qa Qb Qc Qd Qe) Ng(aA Fp Fr Hq Hr Hu Hv Hw Hx Ih Ii Ij Ik Il In Io Ip Iq Ir Is It Iu Iv Jg Jh Jj Jk Jm Jn Jo Jp Jq Jr Js Jt Lh Li Lj Lu Lw Lx Ly Lz Ma Mb Mc Md Me Mf Mg Mh Mi Mj Mk Ml Mm Mp Mq Mr Ms Mt Mu Mv Mw Mx My Na Nb Nc Nd Ne Nf Nh Ni Nj Nk Nl Nm Nn Nq Nr Ns Nt Nu Nv Nx Ny Oe Of Og Oh Oi Ok Om On Oy Pa Pb Pc Pd Pe Pf Pg Po Pz Qa Qb Qc Qd Qe Ye) Jj(AA Fp Fr Hq Hr Hu Hv Hw Hx Ih Ii Ij Ik Il In Io Ip Iq Ir Is It Iu Iv Jg Jh Jk Jm Jn Jo Jp Jq Jr Js Jt Lh Li Lj Lu Lw Lx Ly Lz Ma Mb Mc Md Me Mf Mg Mh Mi Mj Mk Ml Mm Mp Mq Mr Ms Mt Mu Mv Mw Mx My Na Nb Nc Nd Ne Nf Nh Ni Nj Nk Nl Nm Nn Nq Nr Ns Nt Nu Nv Nx Ny Oe Of Og Oh Oi Ok Om On Oy Pa Pb Pc Pd Pe Pf Pg Po Pz Qa Qb Qc Qd Qe) Jp(aA Aj Fp Fr Hq Hr Hu Hv Hw Hx Ih Ii Ij Ik Il In Io Ip Iq Ir Is It Iu Iv Jg Jh Jk Jm Jn Jo Jp Jq Jr Js Jt Lh Li Lj Lu Lw Lx Ly Lz Ma Mb Mc Md Me Mf Mg Mh Mi Mj Mk Ml Mm Mp Mq Mr Ms Mt Mu Mv Mw Mx My Na Nb Nc Nd Ne Nf Nh Ni Nj Nk Nl Nm Nn Oy Pa Pb Pc Pd Pe Pf Pg Po Pz Qa Qb Qc Qd Qe) Jt(aA Aj Fp Fr Hq Hr Hu Hv Hw Hx Ih Ii Ij Ik Il In Io Ip Iq Ir Is It Iu Iv Jg Jh Jk Jm Jn Jo Jq Jr Js Lh Li Lj Lu Lw Lx Ly Lz Ma Mb Mc Md Me Mf Mg Mh Mi Mj Mk Ml Mm Mp Mq Mr Ms Mt Mu Mv Mw Mx My Na Nb Nc Nd Ne Nf

Nv Nx Ny Oh Om Pa Pc Pd Pe Pf Pg Po Pz Qa Qb Qc Qe) Li(Aj Fp Fr Hq Hr Hv Hw Hx Ih Ij Il In Io Ip Iq Ir Is It Iu Iv Jg Jh Jl Jm Jn Jp Jq Jr Js Jt Lh Lu Lv Lx Ly Lz Ma Mb Mc Md Me Mf Mg Mh Mi Mj Mk Ml Mm Mn Mp Mq Mr Mt Mu Mv Mx Mz Na Nb Nc Nd Ne Nf Nh Ni Nk Nl Nm Nn Nq Nr Nt Nu Nv Nx Ny Oh Om Pa Pc Pd Pe Pf Pg Po Pz Qa Qb Qc Qe) Ok(Fr Hq Hv Hw Hx Ih Ij Il In Io Iq Ir Iu Iv Jg Jh Jk Jl Jm Jq Jr Js Jt Lh Lu Lv Lw Lx Ly Lz Ma Mb Mc Md Me Mf Mg Mh Mi Mj Ml Mm Mn Mp Mq Mr Mt Mu Mv Mw Mx Na Nb Nc Nd Ne Nf Nh Ni Nk Nl Nm Nn Nq Nr Nt Nu Nv Nx Ny Oh Om Pa Pc Pd Pe Pf Pg Po Pz Qa Qb Qc Qe) Ik(Fr Hq Hr Hv Hw Hx Ih Ii Il In Io Ip Iq Ir Iv Jg Jh Jk Jl Jm Jn Jo Jp Jq Jr Js Jt Lh Lu Lv Lw Lx Lz Ma Mb Mc Md Me Mf Mg Mh Mi Mk Ml Mm Mn Mp Mq Mr Mt Mu Mv Mw Mx Mz Na Nb Nc Nd Ne Nf Nh Ni Nk Nm Nn Nq Nr Nu Ny Oh Oi Pa Pc Pd Pe Pf Pg Po Qa Qb Qc Qe) Oi(Fr Hq Hr Hv Hw Hx Ih Ii Ij Il In Io Ip Iq Ir Is Iu Iv Jg Jh Jk Jl Jm Jn Jo Jp Jq Jr Js Jt Lh Lu Lv Lw Lx Lz Ma Mb Mc Md Me Mg Mh Mi Mk Ml Mm Mn Mp Mr Mt Mu Mv Mw Mx Mz Na Nc Nd Ne Nf Nh Ni Nk Nl Nm Nn Nr Nt Nu Ny Oh Pc Pd Pe Pf Pg Po Qa Qb Qc Qe) Fp(Hq Hv Hw Hx Ih Ij In Ip Is It Iu Iv Jg Jh Jk Jl Jm Jn Jo Jp Jq Jr Js Jt Lh Lu Lv Lx Ly Lz Ma Mb Mc Md Me Mf Mg Mh Mi Mj Mk Ml Mm Mn Mp Mr Mt Mu Mv Mw Mz Na Nc Nd Ne Nf Nh Ni Nk Nl Nm Nn Nq Nt Nu Nx Ny Oh Om Pa Pc Pd Pe Pf Pg Po Qa Qc) aA(Fr Hq Hv Hw Hx Ih Ii Il In Io Iq Ir Is Iu Iv Jg Jh Jl Jm Jo Jq Jr Js Lh Lu Lx Ly Lz Mb Mc Md Me Mf Mg Mh Mi Mj Ml Mm Mp Mq Mr Mt Mu Mv Mw Mx Na Nb Nc Nd Ne Nf Nh Ni Nk Nn Nq Nr Nt Nu Nv Nx Ny Oh Om Pa Pc Pd Pe Pf Pg Po Pz Qa Qb Qc Qe) Ii(Fr Hq Hr Hv Hw Hx Il In Io Iq Ir Iu Iv Jg Jh Jk Jm Jo Jp Jq Jr Lu Lv Lx Ly Lz Ma Mb Mc Md Me Mf Mg Mh Mi Mk Ml Mm Mn Mp Mq Mt Mu Mv Mw Mx Mz Na Nc Nd Ne Nf Nh Ni Nk Nm Nn Nq Nr Nt Nu Nv Nx Ny Oh Om Pa Pc Pd Pf Pg Po Pz Qb Qc Qe) It(Fr Hq Hr Hv Hw Hx Ih Ij Il In Ip Is Iu Iv Jg Jh Jk Jl Jm Jn Jq Jr Js Jt Lh Lu Lv Lw Lx Ly Lz Ma Mb Mc Md Me Mf Mg Mh Mi Mj Mk Ml Mm Mn Mp Mr Mt Mu Mv Mw Mz Na Ne Nf Nh Ni Nk Nl Nm Nn Nt Nu Nx Ny Oh Pc Pd Pe Pf Pg Po Pz Qa Qc) Ms(Fr Hv Hw Hx Il In Io Iq Ir Iu Iv Jg Jh Jl Jm Jq Jr Js Lh Lu Lx Ly Lz Ma Mb Mc Md Me Mf Mg Mh Mi Mj Ml Mm Mp Mq Mr Mt Mu Mv Mw Mx Na Nb Nc Nd Ne Nf Nh Ni Nm Nn Nq Nr Nt Nu Nv Nx Ny Oh Om Pa Pc Pd Pe Pf Po Pz Qa Qb Qc Qe) Jk(Hq Hr Hv Hw Hx Ih Il In Io Ip Ir Is Iv Jg Jh Jl Jm Jn Jo Jp Jq Jr Js Jt Lh Lu Lv Lw Lx Lz Ma Mb Mc Md Me Mg Mh Mi Mk Mn Mp Mr Mt Mv Mw Mx Mz Na Nc Nd Nh Ni Nk Nl Nm Nn Nr Nt Nu Nv Ny Oh Pa Pc Pe Pf Pg Po Qa Qb Qc Qe) Mz(Hq Hv Hw Hx Ih Ij In Ip Is Iu Iv Jg Jh Jl Jn Jo Jp Jq Jr Js Jt Lh Lu Lv Lw Lx Ly Lz Ma Mb Mc Me Mf Mg Mh Mi Mk Ml Mm Mn Mp Mr Mt Mu Mv Mw Na Nc Nd Nf Nh Ni Nk Nl Nm Nn Nt Nu Ny Oh Om Pc Pd Pe Pf Pg Qa Qc) Lw(Hq Hv Hx Ih Ij Il In Ip Is Iv Jh Jl Jn Jo Jp Jq Js Jt Lh Lu Lv Lx Ly Lz Ma Mb Mc Md Me Mf Mg Mh Mi Mk Ml Mn Mp Mr Mt Mu Mv Mw Mx Na Nd Ne Nf Nh Ni Nk Nl Nq Nt Nu Ny Oh Om Pc Pd Pe Pf Pg Qa Qc) Jo(Hq Hr Hv Hw Hx Ih In Ir Is Iv Jg Jh Jl Jm Jn Jp Jq Jr Js Lh Lu Lv Lx Lz Ma Mb Mc Md Me Mh Mi Mk Ml Mm Mn Mp Mr Mu Mv Mw Mx Na Nc Nd Nh Ni Nk Nl Nm Nn Nq Nr Nt Nu Ny Oh Pc Pe Pf Pg Po Qa Qc) Pb(Fr Hq Hw Hx Il In Io Iq Ir Iu Iv Jg Jh Jm Jr Js Lu Ly Lz Mb Mc Md Me Mf Mg Mj Mk Ml Mm Mn Mp Mq Mt Mu Mv Mw Mx Na Nb Nc Nd Ne Nf Nh Ni Nm Nn Nq Nr Nu Nv Nx Ny Oh Om Pa Pc Pd Po Pz Qb Qc Qe) Ip(Hq Hr Hv Hw Hx Ih Ij Il In Is Iu Iv Jh Jl Jm Jn Jp Jq Jr Js Jt Lu Lv Lx Ly Lz Ma Mb Mc Md Mg Mh Mi Mk Mn Mp Mr Mu Mv Mw Na Nf Nh Ni Nk Nl Nm Nn Nt Ny Oh Pc Pd Pe Pg Qa Qc) Oz(Fr Hq Hw Il Io Iq Ir Iu Jg Jm Jr Js Lh Lu Ly Lz Md Me Mf Mg Mj Mk Ml Mm Mq Mt Mu Mx Nc Nd Ne Nf Nh Ni Nk Nm Nn Nr Nt Nu Nv Nx Oh Om Pa Pc Pd Po Pz Qb Qc Qe) Is(Aj Hq Hr Hv Hx Ih Ij Il In Iv Jh Jl Jn Jp Jq Jt Lu Lv Lx Ly Ma Mb Mc Md Mg Mh Mi Mj Mk Mn Mp Mr Mu Mv Mw Na Nf Ni Nk Nl Nt Nx Ny Oh Pc Pd Pg Qa Yh) Jp(Aj Hq Hr Hv Hw Hx Ih Ij In Iv Jh Jl Jn Jq Js Jt Lh Lu Lv Lx Lz Ma Mb Mc Md Mg Mh Mi Mj Mk Mn Mp Mr Mu Ni Nk Nl Nm Nn Nt Ny Oh Pc Pd Pe Pg Qa) Hr(Hq Hx Ih Ij In Ir Iv Jh Jn Jr Js Lh Lu Lv Lx Lz Ma Mb Mc Md Mg Mh Mi Mk Mn Mp Mr Mu Mv Mw Na Nh Ni Nk Nl Nm Nr Nt Pc Pe Qc) Mw(Hq Hu Hv Hx Ih Ij In Iv Jg Jl Jn Jq Js Jt Lh Lu Lv Lx Ma Mc Mh Mi Mk Mn Mp Mr Mt Na Nb Nk Nl Nn Nt Py Pc Pe Qa) Mv(Hq Hu Hv Hx Ih Ij In Iv Jg Jl Jn Jq Js Jt Lh Lu Lv Lx Ma Mc Mh Mi Mk Mn Mp Mr Mt Na Nk Nl Nn Nt Pc Pe Qa Qc) Jn(Hq Hv Hx Ih Ij In Jh Jl Jq Jt Lh Lu Lv Lx Ma Mc Md Mg Mh Mi Mk Mn Mp Mr Mu Na Ni Nk Nl Ny Pc Pe Pg Qa) Nl(Hq Hv Hx Ih Ij In Iv Jh Jl Jq Jt Lu Lv Lx Ly Ma Mc Mg Mh Mk Mn Mu Na Nh Ni Nk Pc Pg Qa) Mk(Hv Ih Ij In Iv Jh Jq Js Jt Lh Lu Lv Lx Lz Ma Mc Mh Mi Mn Mp Nd Nk Nr Nt Nu Pa Qa) Lv(Hq Hx Ih Ij In Iv Jh Js Jt Ly Ma Mc Md Mg Mn Mr Na Nk Pc Pd Pg Qa Qc) Jl(Hq Hx Ih Ij In Jh Jt Md Mh Mn Mu Nk Ny Pd Pg Po) In(Hq Hv Ih Ij Iv Jh Js Jt Mh Mi Mn Mr Nt Qa) Hq(Ih Ij Jh Lx Mh Mi Mp Mr Nd Pe Qa) Hx(Ij Jt Lh Lx Mh Mr Mt Pe Qa) Jh(Hu Hv Ij Jq Jt Lh Mr Nk Qa) Md(Hv Ij Jq Jt Lh Mr Pe Qa) Aj(Ad cH Jg Ji Mn Mt Nw) Hu(Mj Mq Nb Nc Nf Om Qc) Nk(Ih Jt Mh Nc Qa) Pg(Lx Mi Mp Mr Pe) Po(Lh Lx Mr Pe) Ij(Mg Mp Ny Qa) Om(Hv Hw Jq Qa) Ma(Ih Mg Qa) Jt(Mb Mg Na) Pd(Mp Pe Pf) Mr(Mh Ny) Yh(Ow Tl) NnMu NtNa LdUy OwVi} Ok[Qd(Aj Fp Fr Hq Hu Hv Hw Hx Ih Ii Ij In Io Ip Iq Ir Is It Iu Iv Jg Jh Jk Jl Jm Jn Jo Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nu Nv Nx Ny Oh Oi Om Pa Pc Pd Pe Pf Pg Po Pz Qa Qb Qc Qe) Lj(Fp Fr Hq Hu Hv Hw Hx Ih Ii Il Io Ip Iq Ir Is It Iu Iv Jg Jh Jk Jl Jm Jn Jo Jq Jr Js Jt Lh Li Lu Lv Lx Ly Lz Mb Mc Md Me Mf Mg Mh Mi Mj Mk Ml Mm Mn Mq Mr Ms Mt Mu Mv Mw Mx My Na Nb Nc Nd Ne Nf Ng Nh Ni Nj Nk Nl Nm Nn Nq Nr Nt Nu Nv Nx Ny Oh Oi Om Pa Pc Pd Pe Pf Pg Po Pz Qa Qb Qc Qe) No(Fp Fr Hq Hu Hv Hw Hx Ih Ij Ik Il Io Iq Ir Iu Iv Jg Jh Jk Jl Jm Jn Jo Jq Jr Js Jt Lh Li Lu Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Nh Ni Nk Nl Nm Nn Nq Nr Nt Nu Nv Nx Ny Oh Oi Om Pa Pc Pd Pe Pf Pg Po Pz Qa Qb Qc Qe) Hr(Fr Hq Hu Hv Hw Hx Ii Ik In Io Iq Ir Iu Iv Jg Jh Jk Jm Jo Jq Jr Jt Lu Lv Lw Lz Ma Mb Mc Md Me Mf Mg Mh Mi Mj Mk Ml Mm Mq Mr Ms Mt Mu Mv Mw Mx My Na Nb Nc Nd Ne Nf Ng Nh Ni Nk Nl Nm Nq Nr Nt Nu Nx Ny Oe Of Oh Oi Om Oy Pa Pc Pd Pe Pf Pg Po Pz Qb Qc Qe) Pb(Fr Hq Hu Hv Hw Hx Ih Ii Ik Il In Io Iq Ir Iu Iv Jg Jh Jk Jm Jo Jq Jr Js Jt Lu Lv Lw Ly Lz Mb Mc Md Me Mf Mg Mh Mi Mj Mk Ml Mm Mq Ms Mt Mu Mw My Na Nb Nc Nd Ne Nf Ng Nh Ni Nj Nk Nl Nm Nn Nq Nr Nt Nu Nx Ny Oh Oi Om Oy Oz Pa Pc Pe Pf Pg Po Pz Qb Qc Qe) Jp(Aj Fr Hq Hv Hw Hx Ii Ik Il In Io Iq Ir Iu Iv Jg Jh Jk Jm Jq Jr Js Jt Lh Lu Lv Ly Lz Ma Mb Mc Md Me Mf Mg Mh Mi Mj Mk Ml Mm Mn Mq Mr Mt Mu Mv Mw Mx Na Nb Nc Nd Ne Nf Nh Ni Nk Nm Nq Nr Nt Nu Nv Nx Ny Oh Om Pa Pc Pd Pe Pf Pg Po Pz Qb Qc Qe) Oe(Fr Hq Hu Hv Hw Hx Ik Il In Io Ip Iq Ir It Iv Jg Jh Jk Jm Jo Jq Jr Js Jt Lh Li Lu Lv Lw Lx Ma Mc Mg Mi Ml Mm Mn Mp Mr Ms Mt Mw Mx My Mz Na Nb Nc Nd Ng Nj Nl Nn Nq Nr Nt Nv Ny Of Oh Oi Om Oy Pa Pc Pd Pe Pg Po Qb Qc Qe) Oz(Hq Hu Hv Hw Hx Ii Ik Il Io Iq Ir Iu Iv Jg Jh Jk Jm Jq Jr Jt Lu Lw Ly Lz Mb Mc Md Me Mf Mg Mh Mj Mk Ml Mm Mq Mt Mu Mv Mw Mx My Na Nb Nc Nd Ne Nf Nh Ni Nj Nk Nn Nq Nr Nt Nu Nx Ny Oh Om Pa Pc Pd Pf Po Pz Qb Qc Qe) Of(Fp Fr Hq Hu Hv Hw Hx Ih Ik Il In Io Ip Iq Ir Iv Jg Jk Jm Jn Jo Jq Jr Js Jt Lh Li Lu Lv Lw Lx Ma Mc Mi Ml Mn Mp Mr Ms Mt Mw Mx My Mz Nc Nd Ng Nj Nl Nn Nq Nr Nt Nv Ny Oi Om Oy Pa Pc Pe Pg Po Qb Qc Qe) Ns(Hq Hu Hv Hw Ii Ik Il In Iq Ir Iu Jh Jk Jm Jq Jr Jt Lu Ly Lz Mb Md Me Mf Mg Mh Mi Mj Mk Ml Mm Mq Mr Ms Mu Mv Mw Mx Na Nb Nc Ne Nf Ng Nh Ni Nj Nk Nm Nq Nt Nu Nx Oh Oi Om Pa Pc Pd Pe Pf Pg Po Pz Qc) Oy(Fr Hq Hu Hv Hw Hx Ih Ik Il In Io Iq Ir Iu Iv Jg Jh Jk Jm Jn Jo Jq Jr Js Jt Lu Lw Ma Mc Mg Mi Ml Mm Mn Mr Ms Mw Mx My Mz Na Nb Nc Nd Ng Nj Nl Nn Nq Nr Nt Nv Ny Oh Oi Om Pa Pc Pf Po Qb Qc Qe) aA(Fr Hq Hv Hw Ii Il Io Iq Ir Iu Iv Jh Jk Jq Jr Lu Ly Lz Mb Md Mf Mg Mh Mi Mj Mk Ml Mm Mq Mr Mt Mu Mv Mw Mx Nb Nc Nd Ne Nf Nh Ni Nk Nm Nq Nt Nu Nv Nx Ny Oh Om Pa Pd Pe Pf Pg Po Pz Qb Qe) Is(Aj Fp Fr Hq Hu Hx Ii Ij Il In Ip It Jg Jk Jl Jn Jq Js Jt Lh Li Lu Lv Lw Lx Ma Mc Md Mg Mh Mi Mj Mk Ml Mn Mp Mr Ms Mt My Mz Na Nj Nl Nn Nt Nu Nv Nx Ny Oi Pc Pd Pe Qa Qc) Li(Fp Hx Ih Ii Ij Ik Il In Ip It Iv Jg Jl Jn Jo Jq Js Lh Lv Lw Lx Lz Ma Mc Mg Mh Mi Mj Mk Ml Mn Mp Ms My Mz Na Nf Ng Nj Nl Nn Nv Ny Oi Pc Pd Pf Po Qa Qc) It(Fp Fr Hq Hu Hv Hx Ih Ii Ij Ik In Ip Jg Jl Jn Jq Js Jt Lh Lu Lv Lw Lx Ma Mc Mg Mi Mn Mp Mr Ms My Mz Na Ng Nj Nk Nl Nn Nv Oi Pc Pd Pz Qa Qb Qc) Mz(Fp Fr Hu Hv Hx Ih Ii Ij Ik

Wh Yd Yl Zx) aX(Vc Vj Wb Xa) Eq(Jl St) WbVt} Nv{Ns(Hu Lj Lw Mp My Ng Oe Oz Pb) Lj(Oe Oz Pb) My(Ij Mt) Oe(Oz Pb) NgJt} Jl{Hr(Ij Jq Jt) Ij(My Pb) Oz(Lx Ma) ChZq CxVa WbOw RuUr VjaY} Wb{Oh(aW bS Dd Gp Oi Qy) Ow(cB In Qh) RxRm} Ij{My(Fr Lh Lx) FrNg NsMp NdYh VcbM} Ke{dJ(eT hO qA qC) IzfN qAjT} Ns{Lx(Mh My) Mp(Lh Lj)} Mt{aX(Op Vh Xa) MyLh} Yh{Nq(Js Oh) Ow(Cu Dk)} Wf{Ny(bZ Ma Mv) GlUt} Va{DdJn QeaZ SrOr OwdL} Dr{GpRm UcLj VcPf} Uh{Tv(Ii Ur) NroN} Vj{DcbN IlOr QeaZ} Ed{FcTr MfXa} Lx{PoJt HqrS} Jn{WhOz QyYe} Lh{MaPb JoJt} Ru{JyaZ UrVu} Rm{MwYe RxNy} DcRtUt DuQeQv GdOwiZ GnOaVu NflIYj HpOzPf i

Figure 28 Continued

Mq Mt Mu Mv Mw Mx Na Nb Nc Nd Ne Nf Nh Nl Nm Nq Nr Nu Nx Ny Of Om Pa Pd Pe Pf Pg Po Pz Qb Qc Qe) Ip(Fp Hq Hr Hv Hx Ih Ii Ij Il
It Iv Jg Jn Jo Jq Jr Js Jt Lh Li Lj Lu Ma Mh Mi Mk Ml Mm Mn Mp Mr Ms Mt My Na Nc Nh Nk Nl Nm Nn Nt Nv Nx Of Oh Oi Pc Pd Pe Qa
Qd) Pb(Hq Hr Hw Hx Ii Il Io Iq Ir Iu Jh Jk Jm Jr Ly Lz Mb Mc Md Me Mf Mg Mh Mj Mk Ml Mq Mu Mv Mw Mx My Nb Nc Nd Ne Nf Nq Nr
Nu Ny Of Oh Oi Pa Pd Pf Po Pz Qb Qc Qe) Jl(Aj Fp Hq Hx Ih Il In It Iv Jg Jk Jn Jo Jq Js Jt Lh Li Lj Lu Lx Lz Ma Md Mj Ml Mm Mn Mp Ms
Mv Na Nd Nf Nh Nk Nl Nm Nn Nr Nv Ny Of Oi Pc Pd Pf Pg Po Qa Qd) Oy(Fp Fr Hr Hu Hv Hw Hx Ii Ik Il Io Ir Iv Jm Jo Jr Lj Lu Ly Lz Mc
Me Mg Mh Ml Mm Ms Mx My Na Nb Nc Nd Nf Ng Nh Ni Nk Nm Nq Nt Nu Ny Oh Oi Pa Pe Pf Qb Qc) Oe(Fp Fr Hr Hu Ii Il In It Iv Jq Jr Js
Lh Li Lj Lx Ma Mi Mm Mn Mp Mr Ms Mt My Na Ng Nh Nl Nm Nn Nt Nx Ny Om Pc Qb) Qd(Hr Hu Ih Ii Ij In It Jg Jn Jo Jq Jt Lh Li Lz Ma Mi
Mj Mm Mn Mp Mr Ms My Mz Na Ng Nk Nl Nn Nx Of Oi Pc Qc) Mz(Aj Hu Hx Ih Ii Ij Ik In It Jg Jn Jq Jt Lh Li Ma Mh Ml Mm Mn Mp Mr Ms
Na Nf Ng Nl Nn Nv Ny Om Pc Qa) Aj(aE Ap aQ Bc cH cJ Cu Cv Dg dJ Dl Fr Ij Ik iO Jq Ko Kq Ma Mi Ml Mm Mu Nk Nn Ns Nx Om Qa Uc)
Ik(Fp Hr Hu In Iv Jq Jr Js Jt Lh Lj Lx Ma Mi Mm Mn Mp Mt My Ng Nh Nl Nn Nt Nv Nx) aA(Fr Hq Hw Il Iq Iu Jh Jk Jo Jr Ly Mh Mq Mx Nb
Ne Ni Nr Oh Pa Pf Po Pz Qb Qe) Ng(Fr Ih In It Jn Jq Lh Li Ma Mg Mi Mm Mn Mp Mr Nl Nm Nn Nt Nx Om) Ij(Hr Hx Ii It Jg Jn Jo Jt Li Lj Mi
Mm Mn Mp Ms Na Nl Nn Of Oi Pc) In(Hu Ih It Jg Jn Jq Js Jt Lh Li Mi Mn Mp Nl Nv Nx Qa) My(Jn Jq Jt Li Lx Mi Mn Mp Mr Mw Nb Nn Nv
Nx) Uh(dR eF gL gP hB hG iA iH iJ iP kQ nY oH pF) Jg(Ih It Jn Jo Jq Lj Mn Mp Mw Nl Of Oi Qa) Jt(Fp Hu It Jn Jo Li Lj Mj Mn Mp Ms Na
Oi) Hu(It Jn Jq Lh Li Ma Mn Mp Nq Nx Qa) Jn(Hr Ii Lh Li Mm Mn Mp Ms Nn) It(Lh Li Mn Mp Na Nn Nv) Li(Hr Ih Jq Mn Mp Oi) Mp(Lj Mk
Pf Pg) Ns(Iq Jk Pz) Mr(Ii Mk Po) Nl(Mn Ne Nk) Lh(Hx Jo Po) Vi(Ow Uu Wf) Wm(Ji Nw) Ms(Ih Mn) Hr(Jq Qa) Ii(Jq Nv) Oi(Nn Ps) ThkR
MaIh MkPe JjOw NvOf NwoN} Vi{Mf(aA AF aG al Aj aK An AO aP aV Aw AX aZ BC Bg bJ bN bW bZ cG cH cJ CO cR cS cU cV cW cX
cY De Dl dM dN Ed Ef Et Ez Fb Fc FR Gc Gn Hf Hq Hu Hv Hw Ib Ik Il In Io Iq Ir Iu Jd Jh Ji Jj Jk Jm Jr Jt Kc Ke Kf Kg Ki Ko Kp Kz Ld Lv
Lx Ma Mb Me Mg Ml Mp Ms Mv My Mz Na Nd Ng Ni Nk Nm Nq Ns Nu Nw Nx Oa Oi Or Oy Pa Pd Pi Pj Qb Qh Qt Rc Rh Ru Rx Sh Sr Ss St
Ua Ue Uf Ug Uh Uk Us Ut Uv Uw Vb Vp Vq Vs Wd We Wf Yi Tl Xa Tj) cQ(aA Ad aE aG aH aK AN aQ aS aU aV Aw aX aZ BA BC bG bH
bI bL bO bR bS bW bX cA cB cC cD cE cF cK cL cM cN Co cT Cu Cv cY dB dC dD dF dI dK Fa Fc Fi Fr Fw Gb Gc Gd Gl Gp Gz Hq Hr Hw
Ii In Jh Ji Jm Jo Jr Jt Kc Kd Ke Ki Kq Ky Lh Lw Ly Mc Md Mg Mi Mj Mm Mp Mv Mw Mx Mz Nm Nt Om Ou Pa Pg Pj Pz Qb Qc Qd Qh Qu
Qy Qz Rb Rg Rv Ss St Tv Tz Ua Uc Ud Uf Uh Ul Um Un Uo Uv Uw Ux Uz Vb Vc Vo Vw Wg Yg Yh Yi Yk Zq Zx Xa) Ow(aA aN Ap AR Bc
bF bM Bn bU bV cA cI cK Ct cY Db Dd De dN Dr Du Fc Fi Fy Gc Gh Gn Hb Hf Hp Hq Hr Hw Ii Ij Il Jq Jt Kc Kj Kn Kq Ld Lh Lx Mj Mk Mt
Mz Nc Nk Nm Om Op Or Oy Pe Pg Pk Qe Rf Rh Rt Si Tn Ua Ub Uo Up Uw Vc Vh Vo Wb Yg Yh Yj Zq Wm) Oz(aD Al aO aZ bB bF bZ Cs
CT cV cX Dc dF Di dM Ex Fa Fp Fw Ib Id Ij It Je Li Lu Me Mj Mt Mx Mz Nk Nn Ns Nv Nx Ny Of Oi Om Or Ou Pa Pc Qc Qh Qn Rj Rx Tn
Uk Un Vp Vz We Wf Wh Yi Ti) Ld(Af Aj bX Co Dg Di Dk Dl Du Ed Ez Id Im Iz Je Kx Lv Mv My Nb Ng Oa Oh Oi Pc Qb Qz Ri Un Uw Ux
Vj Wf Wh Yg Yh Tm) Uu(aL aO aX bO cA cF cK cU Fb Gh Hw Ih Il Jh Jk Kc Ks Mm Mt Nd Nq Nr Oh Pd Ql Rc Rf Rm Ue Uv Vc Vt Wc Yk
Zq) Wf(aM aP aW cU Ed Ib Ir Kd Li Lu Mq Mr Mt Mv Nq Nr Nw Oa Pb Pc Pf Qb Qd Qe Uh) Is(Ad AF Aj Bg Im Jj Jq Lj Me Mj Ms Nc Nu Pc
Rc Sr Up Wc Yk) Yg(aU aW Co Ez Iu Jh Kc Kq Li Mi Mm Mt Mu Mv Nu Nm Qd Qy Uf) Wh(bJ cP Hv Ij Im Kd Ki Kq Li Mi Mp Mt Mv
Nq Oh Qy Si Ue Vq) Aj(aU CO De Hv Im Iu Kc Kq Mg Mi Mp Mt Mu Nq Qa Qy Uf) Bg(bW CO cZ Gc Hv Kc Kd Kq Mi Mu Pd Qy Uf)
Oi(bZ Fa Hv Ji Jn Js Kk Mq Mv Nn Oh Om Rh Ur) Zq(aX Ch Eq Ir My Ng Of Qb Rz Ss Vb Vw Wd) Qa(Af Dd Ex Hc Je Kd Nv Qw Rj Ur Uw
Zw) Qb(bW Gc Li Mg Mi Mp Mt Nn Pd Qy Uf) Je(aM aP aW cU Ed Ij Kd Oa Pb Pc Pf) My(aW Iu Jh Kc Kq Mi Mu Qy Rx Uf) Lj(Ax dM Ez
Hv Ih Iu Kz Mk Nu Ur) Mp(aW aX Ed Fw Im Nx Oa Qz) Vw(bJ bW Ho Mm Mq Mu Qy Uf) Ng(aX bJ De Jh Kq Pd Uc) Wd(bW cO Gc Hv Iu
Kq Mg) Vb(bJ bW Kq Mg Mt Nm Pj) Ef(De Ez Kq Mi Mq Qy) Ib(aK cA cK Fc Ii Vc) Vt(bL Fn It Mb Oa Uw) Kd(Eq Ex Js Kz Ur) Ch(cO Ez
Iu Kc) Nb(Et Ji Uh Ti) Li(Ao Jh Oy Qz) Oh(aF Ed Im Yk) Ct(aK cB Gc) Mq(aZ Jy Ss) Hc(Nn Pf Qe) Rz(bW Mg Qy) Rh(Bn Il Mh) Of(aK aQ
Sh) Ur(Jm Lp Oa) Fn(dM Nv) Lu(Rc Yk) Hv(Pb Vs) Im(Qt Ss) Qe(cL Ug) Kz(Jm Ru) Uv(Ji Lx) Vq(Jn Vs) Pa(Mk Qc) aW(Kg Kp) EdPc NnRc
NtRx MiJh IjVc IzOm QdPb SscS OaaG UfaX aFaZ} aA{Qd(Fr Hq Hr Hv Hw Hx Ih Ii In Io Iq Ir Is It Iu Iv Jh Jk Jm Jo Jq Jr Js Lu Ly Lz Mb
Mc Md Mf Mg Mh Mi Mk Ml Mq Mr Ms Mt Mu Mv Mw Mx My Nb Nc Nd Ne Nf Ng Nh Ni Nk Nl Nn Nq Nr Nu Of Oh Om Pa Pd Pe Pf Pg
Po Pz Qa Qb Qc Qe) Lh(Fr Hq Hv Hw Hx Ii Il In Io Iq Ir Iu Jh Jk Jm Jq Jr Lu Ly Lz Mb Mc Mf Mg Mh Mj Mk Ml Mq Mr Mt Mu Mv Mw
Mx Na Nb Nc Nd Ne Nf Nh Ni Nk Nn Nq Nr Nu Nv Nx Ny Oh Om Pa Pd Pe Pf Pg Po Pz Qa Qb Qe) Mn(Hq Hr Hv Hw Hx Ii Il Io Iq Iu Iv Jm
Jo Jq Jr Ju Ly Lz Mb Mc Md Me Mf Mg Mh Mi Mj Mk Ml Mp Mq Mr Mu Mv Mx My Na Nb Nc Nd Ne Nf Ni Nk Nn Nq Nr Of Oh Om
Pa Pd Pe Pf Pg Pz Qb Qe) Li(Fr Hq Hv Hw Ii Il Io Iq Ir Iu Jh Jk Jm Jo Jr Lu Ly Mb Mc Md Mf Mg Mh Mi Mj Mq Mr Ms Mt Mu Mv Mw
Mx Nb Nc Nd Ne Nh Ni Nk Nn Nq Nr Nu Of Oh Om Pa Pc Pd Pe Pf Pg Po Pz Qa Qb Qe) Ma(Fr Hq Hr Hv Hw Hx Ii Il In Io Ir Iv Jm Jo Jq Jr
Lu Lz Mb Mc Md Me Mh Mi Mk Mm Mp Mr Ms Mt Mu Mv Mw Mx Na Nc Nd Ne Nf Nh Ni Nn Nr Nu Ny Om Pc Pd Pe Pg Po) Jg(Hr Hv Hx
Il In Ir Iv Jm Jq Jt Lz Mc Md Me Mh Mi Mk Mm Mp Mr Ms Mt Mu Mv Mw Mx Na Nk Nl Nm Nn Nr Nt Nv Ny Oh Pc Pe Pg Po Qb Qc Qe) Mz(Hr
Hu Hx In Io Iv Jm Jo Jq Jr Lu Mb Me Mf Mg Mi Mr Mw My Na Nc Nd Nh Ni Nn Nu Oe Oi Om Oy Pc Pe Pf Pg Pz Qb Qc Qe) Ip(Fr Hr Hu Hx
Ih Ik Il In Io Iv Jq Lz Mg Mi Mr Mt Mw Nl Nr Nu Oe Oi Om Pe Pc Pg Po Qa Qb Qc Qe) Nj(Hx Ii Ik Iu Jr Jm Jq Me Mg Mi Mm Mr Mx Nk
Nq Nu Oe Oh Om Oy Pb Pe Pf Pg Pz Qb) Lv(Fp Fr Ih Io Is It Lx Me Mm Mw Nm Nr Ns Nt Nv Nx Oy Pb Qa Qc) Jl(Fp Hr Is It Js Jt Lx Mm
Nm Nn Ns Nt Nv Ny Oe Oy Pb) Lw(Fr Ih It Jt Mr Mt Nn Nr Ns Nt Nx Pb Po Qa Qc Qe) Lx(Fp Ik Is It Jn Js Jt Lj Nl Nm Nt Nv Nx Ny Oy)
Nv(Fp Hr Ih Ik Is It Jt Md My Nl Nm Nt Of Oi) Oz(Ih It Mm Mp Nn Nr Ns Og Om Po Ps Qa Qe) Is(Fp Fr Ik In Jt Mm Nt Ny Oy Pb Va Wf)
Jn(Fp Fr Jt Mm Mp Nm Nt Nx Ny Oe Oy Pb) Lj(Fr Ik It Js Mt Nl Nn Ny Oe Om Pb) Jt(Fr Hr It Ng Nn Nx Ny Oe Oy Pb) Jj(Fp Fr It Jm Nn Nr
Po Qe) Js(Fr Ik Mm Nm Ns Oe Oy Pb) Og(Ih It Mt Nr Po Pz Qb Qe) Fp(Mm Nm Ns Nx Ny Pb) Fr(It Ns Oe Oy Pb) Ns(Mt Nn Po Qa) Nx(It Ny
Oe Oy) Aj(Ji Nw) Nt(Ih Pb) Qa(Hp Oe) MtMy IjIl NyOe] Aj{Nw(aE Af aH Al aM An Ao Ap aQ Ar As AW Ax bA BB Bc Bg BN BO bR bS
cG Ch cI cL Co cP Cs Ct Cw Db De dF Dg Di Dl Fp Ii Io Iq Iu Jh Jk Lj Lx Mb Mc Md Me Mh Mj Mk Ml Mp Mq Ms Mw Mx My Na Nd Ne
Nf Ng Ni Nj Nk Nl Nm Nq Ns Nu Nx Ny Oe Og Oh Ow Pa Pd Pf Pg Uc Wm) Ji(aE Af aQ Ax Bb BC bF Bg BN cI cJ cL Co Cs Ct Dc Dd De
dF dK Dl dM Hx Ih Ij In Ip It Iv Jj Jk Jm Jn Jo Jq Jr Ko Kq Lj Lv Lx Mb Mc Md Mh Mi Mk Mm Mr Ms Mu Mv Mw My Mz Na Nb Nc Nd Ne
Nf Ni Nj Nn Nq Nr Ns Nv Oe Og Oi Om Oz Pb Pe Pf Pg Po Pz Qb Qc Qe Uc) Kq(aE Af Ap Ba bN Bo bR bS cA Ch cI cJ cP Ct Cx Dg dK Dl
Fw Hc Hq Im Is Iu Jj Jl Jt Kc Kd Kf Kg Kk Kp Ks Ky Ld Li Lj Lu Mb Mc Md Me Mg Mh Mk Ml Mm Mn Mr Mt Mv Mz Nd Ne Ng Nh Nj Nl
Nn Nr Ns Nx Of Og Oh Ou Oy Ph Pi Pk Qa Qv Ri Uc Uh Ti) Im(aE aN Ap aQ As aW bA BB Bc Bg bS cE cG cL cM Cp Cq cT Cv Cw Cx DD
De Di dK dN Hv Hw Ih Ik Il In Ir Iv Jh Jn Jo Jr Js Lh Li Lx Mc Mg Mu Nd Nf Ni Nj Nm Nn Nq Nr Nv Ny Oe Om Ou Pb Pe Pz Qa Qe Ye)
Et(aC aG aH al aJ aK aL aP aS aU aV aY bB bG bH bI bL bM bP bR bS bU bW bX bZ cA cD cE cF cK cN cO cV cW cX cY dA dB dC dD dG
dJ dN Kd Kn Ld Ou Ow Pi Vt Wm) Is(aE aH Ao aQ Ar bA BC bF Bg bR cE cP Cu Cx Dc De dF Dl Ik Il Ip It Jj Lh Lw Me Mh Mu Mx Mz Na
Ng Nh Nk Nm Nn Nq Nv Nx Ny Og Oi Om Ow Oz Qa Qc Qe Rx) Qd(Bc bF Bg cL Co Cu Dc dF dJ Dl Ik Il Ip Jj Jl Jo Jq Lh Li Lv Lw Mb Mg
Ml Mm Mr Mz Ng Nk Nr Nv Oe Og Om Oz) Jt(Ar aW bF bZ cE cH cI cL Co cR cT Cx Dc Ij Il Jj Lh Lx Mh Mr Mu My Mz Ni Nk Nn Nq Om
Pz Qc Qe) Ad(BA cJ Ih Ij Il Ip Jg Jj Lv Lx Mh Ml Mm Mr Mu Nr Nv Nx Oi Om Pe Pg Qc Qe) Jg(BA cT Fr Ih Ij Il Ip Js Lh Lw Ma Mi Mn Mz
Nn Nr Nx Oi Pe Qe) Ba(Dc Hv Ih Ij Jn Jo Jq Jr Mr Pb Pe Pz) Ma(cH Cu Ij Jl Mt Qe) Ij(Dg Fr Jj Jl Li) Dc(cJ Fr Li Mn) Mt(Bb bR Dg Mn)

Nb{Ld(Ux Uy Uz Vc Vh Vz Wb Wc Wd We Wf Wg Wh Yd Yl Zw Zx Ye Tm Tl Xa) Ur(Rt Rv Sh Si Vw Wh Yd Yg Yh Yi Zq Xa) Ow(Dr Gc Si Va Vh Vz Tm) Oz(Rx Si Xa Ti) Va(Lv Mp Ou) Bo(Yl Tm) Ti(Vt Yj) Ye(Ih Mq) Uf(Rz Vb) CuVb EqOm FdRx YdOu WbOh ZqUg YlPe} Kq{Ru(Ad aX aZ Iz Kg My Oy Oz Qu Qz Ss To Uu Ux Wf Wh) Wf(aW Bb Fc Gl Jm Kd Lj Lp Nn) Th(Bg Co Pb Tn) Ux(aN Il Ow Pf) Ch(Fc Gh Uh) Yi(aZ Vs) Zw(Oh Ow) Wh(Fc Nx) Rz(Nr Ow) EqNn GlWd IiUh IkWc YhRm KjKo LpOz} Jl{Ij(Hu Hx Ii Ik Lj Mk Oe Oz) Oz(Fr Hr Ip Lh Lj Mn Mp) Lx(Hr Ns Oe Oy Pb) Ma(Lj Ns Oy Pb) Mn(Lj Ns Oy Pb) Hr(Hv Hw Lj Lw) Wf(Jn Mw Nn Pf) Oy(Fr Mt) EqOw ExVj LwLj liKe JoKo LdUh LhPb} aZ{Nn(Fc Fi Gb Gh Hl Ho Lp Lt Op Rt Ru Rx Sf Si Sj Uw Ux Uy Uz Va Vb Vh Wd We Wg Yh Yi Yj Yk Zw Ye Tm Tl Xa) Yi(cS Mu Ni Nq Vu) TnYk QeTl} Uh{Tv(bN dJ Dp Ic In Jo Ld Oy Pb Ri Uu Wm) Uc(Ch Ii Jo Ng Of Oy Ur Uu) hB(aE CH dJ oN Ri) Mt(oN Oy Oz) Id(bN Ld Uu) Ch(eF Nn) MroN IiKn LddJ RiiB cHgL} Oy{Lx(Ih Io It Iv Js Lv Mm Mr Mt Mw Nj Ns) Ij(Lw Ma Mn Mw Nn Nq Nx Pe Po) Lh(Fr Jh Jn Lw Mp Mt) Fr(Jt Mr Mt) Ma(Ih Mr) Mt(Mn Ow) Ke(Ou Ow)} Ke{dJ(rW uG ul uR uW uX vA vU wE zI) Hu(rP rS uM vS wG wP yD) Il(Ii Jo) Ow(Ik Jo) cQ(vQ wD) rB(rR sK) DeeC JnrR cHoE} Wb{Ow(Al Bg Ch Hc Jy Ks Mf Oe Qc Rb Uc) Oh(cN Gc Il Kk Mf Rx Um Ti) Pf(Ld Mf Oz) NdIj IlLd JraW} Lh{Pb(Hr Ij Lj Lw Lx Mn) Hr(Ij Jn Lj Lw) Ma(Lj My Ng) Ij(Hx Ii Jo) Lw(Lj Ns) CtjT MnMy} Oz{Fr(Ij Ip Jt Ng) Ma(Fp Ih Lj) Mt(Eq My Ux) Lx(Ti Th) EdWd FcJr JnRx} Ld{Il(Vj Yj Zx Ye) Qh(Vb Vz Yh) Yk(Dc Nr) Va(Rm St) HpNy YjJm ZxOa} Ij{Fr(Hu Ik Pb) Mm(Lj My Ng) Lx(Oe Pb) My(Mi Mr) Lj(Lw Mp) NtIk} Ns{Mp(Fp Fr Jn Jt Lx Ma Mn Nt Ny) LxHx} Ny{Wf(Co Mt Nn Nq Tn Ut) Rx(Jr Oh) RzOi} Mt{My(Fr Lx Ma Mn) aX(Fi Rz Ux)} Ow{Dr(Jy Oi Pf) Eq(Ef Mu) IlVz OifR} Jt{Lx(Hr Ii) FpHr FrNg} wB{nW(dM qZ vH) CtdJ} Dr{NnVt RhPf OuaW} Ed{Cu(Fc Fi) TrZw} Yc{Mw(bA Jn) QyOa} Nn{aX(Sh Vb)} Ma{Lj(Lv Lw)} Yh{GnQe OhVu} Rm{ShRi ZqUu} Oa{DuaU WfJy} dJ{KnhX KprS} wD{AncO CtMe} JnRxVt aWjTrS

Unconstrained panels with 2 analytes, where 1.0E-8 >= 'model p-value' > 0. Contains 898 panels of 191,187 total panels evaluated. : Im(aA Aj Et Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Ye) Ji(aA Aj Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Nw(aA Aj Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe Wm) Et(aA Aj Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) On(aA Aj Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om Oy Oz Pa Pb Pc Pd Pe Pf Pg Po Pz Qa Qb Qc Qd Qe) Ok(aA Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Om Oy Oz Pa Pb Pc Pd Pe Pf Pg Po Pz Qa Qb Qc Qd Qe) No(aA Aj Fp Hr Hu Ih Ii Ij Ik In Ip Is It Iv Jg Jj Jl Jn Jp Jq Js Jt Lh Li Lj Lu Lv Lw Lx Ma Mi Mm Mn Mp Mr Ms My Mz Na Ng Nh Nj Nl Nm Nn Ns Nt Nv Nx Ny Oe Og Oh Oi Oy Oz Pb Pc Qa Qd) Jp(aA Fp Ih Ij Ip Is It Jj Jl Jn Jq Js Jt Lh Li Lj Lv Lw Lx Ma Mi Mn Mp Mr Mz Ng Nj Nn Ns Nt Nv Oe Og Oy Oz Pb Pe Qa Qd) aA(Fr Ij Ip Is Jg Jl Jn Js Jt Lh Li Lj Lv Lx Ma Mn Mz Nj Nv Nx Ny Qd) Jj(Fr Ij Is Jg Jl Js Jt Lh Li Lx Ma Mn Nt Nv Qa Qd) Qd(Aj Ik Jg Jl Lh Li Lw Ma Mn Mz Og Oz) Vi(cQ Ld Lj Mf Ow Oz Uu Wf) Is(Aj Li Og Uh Va Wb We) Og(Ij Jg Jl Lh Li Nv) Li(Jl Lv Lw Mz) Nv(Lj Ns Oe Oy) Aj(Jt Kq) Qa(Uh Ye) Ps(Oi Oz) LxOy Unconstrained panels with 2 analytes, where 1.0E-7 >= 'model p-value' > 1.0E-8. Contains 473 panels of 191,187 total panels evaluated. : Jp(Aj Fr Hq Hr Hu Hv Hw Hx Ik Il In Io Iq Ir Iu Iv Jg Jm Jo Jr Ld Lu Ly Lz Mb Mc Md Me Mf Mg Mh Mj Mk Ml Mm Mq Ms Mt Mu Mv Mw Mx My Na Nb Nc Nd Ne Nf Nh Ni Nk Nl Nm Nq Nr Nu Nx Ny Of Oh Oi Om Pa Pc Pd Pf Pg Po Qb Qc Qe) No(Fr Hq Hv Hw Hx Il Io Iq Ir Iu Jh Jk Jm Jo Jr Ly Lz Mb Mc Md Me Mf Mg Mh Mj Mk Ml Mq Mt Mu Mv Mw Mx Nb Nc Nd Ne Nf Ni Nk Nq Nr Nu Of Om Pa Pd Pe Pf Pg Po Pz Qb Qc Qe) Qd(bA Fp Fr Hu Ih Ij Il In Ip Is Iv Jn Jq Js Jt Lj Lv Lx Lz Mi Mm Mp Mr Ms Mt Mw Ng Nj Nl Nm Nn Nr Ns Nt Nv Nx Ny Oe Oi Oy Pb Pc Pe Qc Uh Vi Wm) Vi(Aj aW aZ Bg Ed Fn Gc Hc Im Is Je Ji Js Kz Li Lu Mp Mq Nb Ng Oa Of Oh Oi Pf Qa Qb Qc Qe Rc Rj Sh Ss Ur Vb Vt Vw We Wh) Is(Fr Iv Jg Jl Jt Lh Lj Lv Lw Lx Ma Mn Mz Nj Ns Nt Nv Oe Oy Oz Rt Rx Ur Vb Wc Wh Yd Yh Yk Zw Ye) Li(Hr Hu Ih Ij Ik In Ip It Jg Jn Jq Js Jt Lh Lx Ma Mi Mn Mp Mr Nj Ns Nt Nv Oe Oy Oz Pb Qa) Jg(Aj Fp Ih Ij Jl Jq Js Lh Lj Lv Lw Lx Mi Mp Mr My Mz Ng Ns Nv Oe Oy Qa) Nw(Aa Ad Af Ao aQ bA bN bS cH cI cJ Cs Cu Cx Dc De Di dJ dK Ed Ri Uh) aA(Fp Ih Io It Lw Mm Mp Mt Mw Nm Nn Nr Ns Nt Og Om Oz Po Qa Qb Qe) Nv(Fp Hu Ih Ij Ik Ip It Jl Jn Jt Lv Lw Mn My Mz Ng Nj Oz Pb Qa) Lh(Hr Ih Ij Jl Jn Jt Lj Lw Lx Ma Mn Mz Ns Oy Oz Pb Qa) Jj(Aa Dc Ip Jn Ke Ko Kq Mz Nn Nx Ny Po Qe Uh) Qa(Aj Du Ma Mn Mz Og Rx Uw Wb Wf Wh Zw) Jl(Hr Ij Jn Jt Lj Lw Lx Ma Mn Mz Oz) Og(Fr Js Jt Lx Ma Mn Mz Nt Om) Uh(hB Id Ji Kn Ld Mz Tv Uc Vt) Aj(Ad Dc Ij Ke Ko Mn Ok) Fr(Ij Js Jt Mz Oz) Kq(Rz Ux Wd Wf Wh) Ps(Ed Pf Rx Uu Va) Lx(Ij Jt Mz Oz) Ji(bA cI cT jO) Ma(Ih Lj Mz) Jt(Fp Lj Mz) Ij(Lj Oy) Wb(Oh Ow) MzjL IkKe Unconstrained panels with 2 analytes, where 1.0E-6 >= 'model p-value' > 1.0E-7. Contains 1,575 panels of 191,187 total panels evaluated. : Vi(aA Ad AF aH aK aM aN AO aP aQ AR AS aU Aw AX aY Ba BB Bc bG bJ bL BN BO bR bS bU bV bW bZ cA cB cC cE Ch cJ cK cL CO Cp CS Ct CU CV CX cZ DC Dd De Dg Dl dJ DK DL dM Dp Dr Ef Eq Et Ex Ez Fc Fp Fr Fw Fy Gd Gl Gp Gz Hb Hf Ho Hq Hr Hu Hv Hw Hx Ib Ic Id Ih Ii Ij Ik Il In Io Ip Iq Ir It Iu Iv Iz Jd Jg Jh Jj Jk Jl Jm Jn Jo Jp Jq Jr Jt Jy Kc Kd Ke Kf Kg Ki Kj Kk Kl Kp Kq Lh Lv Lw Lx Ly Lz Ma Mb Mc Md Me Mg Mh Mi Mj Mk Ml Mm Mn Mr Ms Mt Mu Mv Mw Mx My Mz Na Nc Nd Ne Nf Nh Ni Nj Nk Nl Nm Nn No Nq Nr Ns Nt Nu Nv Nw Nx Ny OE Og Ok Om On Op Or Ou Oy Pa Pb Pc Pd Pe Pg Ph Pj Pk Po Ps Pz Qg Qh Ql Qn Qt Qu Qv Qw Qx Qy Qz Ra Rb Rf Rg Rh Rm Rt Ru Rv Rx Ry Rz Si Sr St Tn To Tv Tz Ua Ub Uc Ud Ue Uf Ug Uh Uk Ul Um Un Uo Up Us Ut Uv Uw Ux Uy Uz Va Vc Vh Vj Vo Vp Vq Vs Vz Wc Wd Wg Yd Yg Yl Ye Tl Xa Wm Ti Th) Nw(aC aD aE aF aG aH aI aJ aK AL aM AN aO AP AR AS aU aV AW AX aY aZ Ba BB BC bE bF BG bH bI bJ bL bM Bn BO bP bQ bR bU bV bW bX bZ cA cB cC cD cE cF cG Ch cK cL cM cN CO CP CQ cR cS CT cU CV CW cX cY cZ dA DB dC DD dE dF DG dH dI Dk DL dM dN Dp Fy Hf Ic Id Iz Jd Je jF jO jP Ju Jv Kc Ke Kk Kn Ko Kq Kr Ks Ld Oa Ou Ow Qn Qv Ra Rc Rg Rj Ru Rx Sr Ss St Tv Tz Ub Uc Ud Uf Ug Uk Ul Un Uo Up Ur Us Uu Uv Vo Vp Vt Wc Ti Th) Is(Aa Af aH Al aQ Ar aW Ax bA BB bF BN bO bR bS cE CH cI cJ cP Cq Cs CT Cx dD De dF Di dJ Du Eq Fp Hr Hu Hv Hw Ih Ij Ik Il In Ip It Jn Jq Js Kc Ke Kk Ko Ld Lu Mc Mi Mm Mp Mr Ms Mt Mw My Ng Nl Nm Nn Nr Nu Nx Ny Of Oh Oi Om Pa Pb Pc Pe Pg Po Qa Ru Sh Ug Uk Us Uw Ux Uy Uz Vc Vh
Vj Vt Vw Vz Wd Wf Wg Yl Zq Zx Tm Tl Xa Wm) Uh(aA Ad Aj As bA Ch Cp Cq Cs Cu Cw Dc Dd dM dR Ed eF Fy gL Hv Hw iB Ij Ik Im In
iO iP Ir It Iv iZ Jl Jn Jp Jq Jr Js Jt Kd Ke Kf Kk Ko Kp Kq Kr Lh Li Lj Lv Lw Mj Ml Mr Ms Mt Na Nb Nf Ng No Nr nW Nx Ny Oa OE oF OH
Oi Om oN Pb Pe Pi Pk Ps Qe Ra Ri Rj Sr Un Up Ur Us Uu Vp Vv Wm) Li(Fp Fr Hq Hv Hw Hx Ii Il Io Iq Ir Iu Iv Jh Jk Jm Jo Jr Lj Lu Ly Lz
Mb Mc Md Me Mf Mg Mh Mj Mk Ml Mm Mq Ms Mt Mu Mv Mw Mx My Na Nb Nc Nd Ne Nf Ng Nh Ni Nk Nl Nm Nn Nq Nr Nu Nx Ny Of
Oh Oi Om oN Pb Pe Pf Pg Po Pz Qb Qc Qe) Nv(Aj Fr Hq Hr Hv Hw Hx Ii Il In Io Ir Iv Jh Jk Jm Jo Jq Jr Js Lh Lu Lx Ly Lz Ma Mb Mc Md
Me Mf Mg Mh Mi Mk Mm Mp Mr Ms Mt Mu Mv Mw Mx Na Nb Nd Ne Nf Nh Ni Nk Nl Nm Nn Nr Nt Nu Nx Ny Of Oh Oi Om Pa Pc Pd Pe
Pf Pg Po Qb Qc Qe) Qd(Aa aQ Bb cH cJ cT De dJ Hq Hr Hv Hw Hx Ii Io Iq Ir It Iu Jh Jk Jm Jo Jr Kk Ko Lu Ly Mb Mc Md Me Mf Mg Mh Mj
Mk Ml Mq Mu Mv Mx My Na Nb Nc Nd Ne Nf Nh Ni Nk Nq Nu Of Oh Om Pa Pd Pf Pg Po Pz Qa Qb Qe Ru Th) Qa(Eq Fi Fp Fr Gh Hp Hr Ij
Ik Ip Jl Jn Jq Jt Kk Ko Lj Lp Lv Lw Lx Mm Mp Mr Nj Nn Ns Nt Nx Ny Oe Oy Oz Pb Ps Rt Ru Rv Ry Sh Sj Ur Ux Uy Uz Va Vb Vc Vh Vj Vw
Vz Wc Wd We Wg Yd Yh Yl Zx Tm Tl Xa Ti Th) Ji(Aa Af aJ aM aN Ao aQ Ar aU aV aW Ax aZ Ba bF bN BO bR bS bV cD cE CH cJ Co cP Cs Ct Cu Cx Dc dD De dF Di dJ dK Dl dM Ed hB iB jE jF jL jP jQ jR jT Kj Kk Ld lN oF Ri Ug Uk Ur Us Uu Uv Vo Vt) Mz(Fp hB HR hX iB iC Ih Ij Ip jE jF jH jK Jn jO JQ jR Js jT jU jV Lj lN Lv Lw Mi Mm Mn Mp Mr Mt Nj Nl Nn Nt Ny Po rB Tv) aA(Hu Hv Hx Ii Ik Il In Iq Ir Iv Jj Jm Jo Jq Jr Lz Me Mg Mh Mi Mj Mk Mr Mx Na Nc Nh Nl Nu Oe Oh Oy Pb Pc Pe Pf Pg Pz Qc) Jg(Fr Hu Hv Hw Hx Ik Ip It Iv Jn Jo Jt Lz Ma Mg Mn Mt Mx Nj Nl Nn Nr Nt Nx Ny Of Oh Oi Oz Pb Pe Pg Po Qb Qc Qe) Lh(Fp Fr Hu Hv Hx Ii Ik In Ip It Iv Jo Jq Js Lv Md Mi Mm Mp Mr Ms Mt My Ng Nj Nl Nm Nn Nt Ny Oe Of Pc Pe Qb Qc) Ke(Af CH cQ dJ eC Et hB iH Ii iJ Il In Iz Jl Jo Jp Kj Kk Ko Ld Ms Ng oE OH Oi oN Ou Ow Oy Oz Pb) Lx(Fp Fr Gh Hq Hu Ih Ik Ip It Jn Jq Js Lj Lv Lw Ma Mi Mn Mp Mr My Nj Nl Nn Ns Nt Ny Oe Pb Pe Vc) Ma(Aj Fp Fr Hv Ij Ip It Iv Jn Jq Js Jt Lv Lw Mi Mn Mr Mt Ng Nj Nl Ns Nt Oy Oz Pb Pe Po Qb Qe) Fr(Aj Fp Hu Ih Ip It Iv Jl Jn Jq Lj Lv Lw Mi Mn Mp Mr Ng Nj Nl Ns Nt Nx Ny Oe Oy Pb Pe) Ij(Fp Hu Ik In Ip Jn Jq Js Jt Lv Lw Mi Mm Mn Mp Mr Mt My Nj Nn Ns Nt Oe Oz Pb Vb Vc Th) Jj(Bb Cu Fp Ih Ii It Jk Jm Jq Kf Kn Lj Lv Mm Mt Mw Nm Nr Om Ou Ow Pz Qb Uc Vt) Jl(Fp Ih Io Ip It Iv Jq Js Lv Mi Mm Mt Mw Nj Nm Nn Ns Nt Ny Oe Oy Pb Rx Ur Wf) Ps(cU Il Kq Nb Nn Nu Ow Qv Tz Ua Ug Ur Us Ut Uy Vb Vo Vs Vt Wc Wh Ye) Mn(Fp Ih Ip Jn Jq Js Jt Lj Lv Lw Mi Mr Mt Nl Ns Nt Ny Oz Pe Po) Kq(Ch Dr Eq Fc Fi Ik Iz Jo Kj Ng Of Oy Ru Sh Uw Vb Vc Vw Yd Th) Jp(Aa Ch Cs Hc Id Ii Iz Jh Jk Kc Kj Kk Kn Ko Ow Pz Vt Wm) Nb(Rt Rx Uw Uy Va Vb Vj Wd We Wf Wh Zq Tm Tl Xa Ti) Jt(Hr Ih Ip Jn Js Lv Mp Mt Nj Nn Ns Nt Ny Oz Po) Nt(Ih Ik Ip Jn Jq Js Lj Lv Lw Nj Ns Ny Oz) Og(Aa Ih Ip Jn Jq Lw Mr Mt Nn Nx Ny Po Qe) Im(Aa Eq Fd Gh Ux Uz Yd Yl Xa) Lj(Jq Js Lv Lw Mi Mm Mp Mr Nx) Aj(Ba Cu Fy Kn Mt Om Qe Uc) Ow(Dr Em Fd Gd Hp Lp Va Xa) Js(Ip Lv Lw Mm Mp Nj Oz) No(Kc oE oH oN Ur Vt) Jn(Lv Lw Mi Mm Mr Rx) Et(bA cI Cs Cu Wm) Mt(bR bS Lw My Oz) Ur(Dc Qe Tv Uc Vt) Lv(Ih Mm Nn Ny) Fp(Jq Lw Mm) Ny(Lw Mi Rx) Oa(Rx Zx Ti) Pf(Fd Vc Wb) Nn(Eq Sh) Wf(On Ut) AaOz WmJq NsMp LwMr XaLd KniB KoVt RmVa

Unconstrained panels with 2 analytes, where 1.0E-5 >= 'model p-value' > 1.0E-6. Contains 3,125 panels of 191,187 total panels evaluated. : Ke(aA aC Ad aE aH aI Al aM AN Ao Ap aQ Ar As AW Ax BA BB Bc bF Bg bL BN Bo bP bR bS bW bX cA cC cE cI cJ Co CP Cq Cs CT Cu CV Cw CX dA Db DC DD De dF Dg Di DK Dl dM Dp dR Ed EF eT fN FP Fr Fw Fy GL GP Hb HC HF hG hP Hq Hr Hu Hv Hw Hx iA Ib Ic Id Ih Ij Im IO IP Iq Ir It Iu Iv iZ Jd Jg Jh Ji Jk Jm Jn Jq Jr Js Jt Ju Jv Kc Kd Kf Kg Ki Kl Kn Kp KQ KR KS Kx Ky Kz Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Nh Ni Nj Nk Nl Nm Nn No Nq Nr Ns Nt Nu Nv nW Nx NY Oa Oe OF Og OK Om On Or Pa Pc Pd Pe PF Pg Ph Pi Pj Pk Po Pz QA QB QC Qd Qe Qg Qu Qv Ri Rj rR rS rW Sr Ss Tr Tv Tz Ua Ub Uc Ue Ug Uk Uo Up Ur Us Uu Uv Vo Vt yD Wm) Is(aC AD aE aF aG aI aJ aK aL aM AN AO AP aR AS aU aV Aw aX aY aZ Ba BC bE BG bH bI bJ bL bM Bo bP bQ bU bV bW bX bZ cA cB cC cD cF cG cK cL cM cN CO Cp cQ cR cS CU CV CW cX cY cZ dA DB DC Dd dE DG dH dI DK DL dM dN Dp Dr Ed Fc Fd Fi fR Gb Gd Gh hB Hl Ho Hp Hq Hx Ic Id Ii Io Iq Ir Iu Iz Je jF Jh JK Jm Jo jQ JR jT Jv Kf Kj Kn Kp Kq Kx Ky Lp Lt Ly Lz Mb Md Me Mf Mg Mh Mj Mk Ml Mq Mu Mv Mx Na Nb Nc Nd Ne Nf Nh Ni Nk Nq Op Ou Ow Pd Pf Ph Ps Pz Qb Qc Qe Ql Qy Ri Rj Rm Rv Ry Rz Sf Si Sj Sr Tv Tz Ua Ub Uc Ud Ue Uf Ul Um Un Uo Up Ut Uu Uv Vo Vp Vq Vs Yg Yi Yj Ti Th) Uh(aE Af aJ aM An Ao aQ Ar aW Ax bB Bg bL BN bR bS bV cA cH cI cM cQ CT Cv Cx De dF dJ DK Dl dN Dp Ef Et Fa Fn FP Fr Fw gP Ha hC HF hG Hq Hr Hu Hx iA Ib Ic IH Ii iJ Il Ip Iu Iz Jd Je Jf Jh jI Jk Jm Jo Jv Jy Kc Kg Ki Kj kQ kR kS Kx Ky Lx Ly Lz Ma Mb Mc Md Me Mf Mg Mh Mi Mk Mm Mn Mp Mq Mu Mv Mw Mx My Nc Nd Ne Nh Ni Nj Nk Nl Nm Nn Nq Ns Nt Nu Nv nY Of Og OK On Or Ou Ow Oy Oz Pa Pc Pd PF Pg Ph Po Qb Qc Qg Qh Ql Qt Qu Qv Qw Qx Qy Qz Rb Rc Rf Rg Rm Ss St Tn To Tr Tt Tz Ua Ub Ud Ue Uf Ug Uk Ul Um Uo Ut Uv Vo Vs Vu tF) Ji(aC AD aE aF aG aH aI aK AL An aO AP aR AS Aw aX aY BB BC bE BG bH bI bJ bL bM Bn bP bQ bU bW bX bZ cA cB cC cF cG cK cL cM cN cO Cp CQ cR cS cU CV CW cX cY cZ dA DB dC Dd dE DG dH dI Dk dL dN Dp dR eC EF Fy gL gP HA hC hF hG iA IC Id iH iJ iO iP IZ jD Je jG jH jI jK jM JU JV jY Kc Kg Ko Kp KQ kR kS lK lL lM lO nW nY Oa oE oH oK oN Ow pF Ph Qg Qh Qt Qu Qv Qw Qx Qy Qz Ra Rb Rc Rf Rg Rh Rj Rm Sr Ss St Tn To Tr Tv Tz Ua Ub Uc Ud Ue Uf Ul Um Un Uo Up Ut Vp Tj Th) Qd(AD aE Af aG aH aI aK AL aM AN AO Ap Ar AS aU aV AW AX aZ Ba bB BC bE bF BG bH bI bJ bL bM BN BO bP bQ bR bS bV bW bX bZ cA cB cC cD cE cG Ch cI cK cL cM CO CP CQ cR Cs Ct CU CV Cw CX cY cZ dA Db DC DD dF Dg dH DI DK Dl dM Dr Du Eq hB Kc Kj Kn Kp Ld oE oH Ou Ow Ps Ri Rx Sh Sj Sr Tv Ua Ur Us Ux Uy Va Vc Vt Wc Wd Wf Wg Yd Yi Yl Ye Xa Ti) Nw(Ef Ez Fa Fb Fc Fd Fn Fw Gb Gh Gl HA HB Hc Ho IB iC iH iJ iZ jD jE Jf jG jH jI jK jL jM jQ jR jT jU jV JY Kd Kf Kg Ki Kj Kl Kp Kx Ky Kz lK lL lM lN lO Lp Lt nW oE oF oH oN Op Or Ph Pi Pj Pk Ps Qg Qh Ql Qm Qt Qu Qw Qx Qy Qz Rb Rf Rh Rm Sf Sh Tn To Tr Tt Ua Ue Um Ut Uw Uy Uz Va Vb Vc Vh Vs Vu Vv Vw Wb Wd We Wf Wg Wh Yd Yi Yl Zw Tm Xa Tj) Jl(Aa Aj Du Eq Fc Fd Fi Ho Hq Hu Hv Hw Hx Ii Ik Il In Ir Jh Jk Jm Jo Jr Kc Kk Ko Ld Lp Lt Lu Ly Lz Mb Mc Md Me Mg Mh Mk Ml Mp Mr Ms Mx My Na Nb Nc Nd Ne Nf Ng Nh Ni Nk Nl Nq Nr Nu Nx Of Oh Oi Om Pc Pd Pe Pf Pg Po Ps Pz Qb Qc Qe Rt Ru Rz Sf Sh Si Ux Uy Uz Va Vb Vc Vj Vt Vw Vz Wb Wc Wd We Wg Wh Yd Yl Zq Zw Zx Ye Tm Tl Xa Wm Ti) Qa(Aa bA Bb Fc Fd Gb Hl Ho Hq Hu Hv Hw Hx Ih Ii Il In Io Ir It Iu Iv Jh Jo Jr Js Kc Kn Ld Lt Lu Ly Lz Mb Mc Md Me Mf Mg Mi Mj Mk Ml Mq Ms Mt Mw My Na Nb Nc Nd Ne Nf Ng Nh Ni Nk Nl Nm Nq Nr Nu Of OH Oi Om Op Ow Pa Pc Pd Pe Pf Pg Po Pz Qb Qc Qe Rz Sf Si Tv Ug Us Vt Yg Yi Yj Yk Zq Wm Yf) Ps(aM Ar aW aZ bB bQ bR Cu dR Fw Fy Gp hB Ij Im In Jp Jr Js Jy Kk Lh Li Lj Lv Lx Lz Ma Me Mh Mk Ml Mq Mr Mt Mz Ni Nk Nq Nr Oa OE oF Oh On Or Ou Pb Pc Pe Qx Qy Ri Rj Ru Sr Ub Uc Ud Ue Uf Uk Ul Um Un Uo Up Uv Uw Ux Uz Vc Vh Vj Vp Vq Vu Vw Vz Wb Wd We Wf Wg Yd Yg Yk Yl Zw Zx Tm Tl Xa) Vi(aC aD aE aG aI aJ AL An Ap aV bA bC bE bF bH bI bM bP bQ bX cD cF cG cH cI cM cN cP Cq cR cT CW cY dA DB dD dE dF dG dH dN dR Du EM Fa Fb Fd Fi fR Gb Gh Gn Ha hB Hl Hp Jf Ju Jv Kn Ko Kr Ks Kx Ky Lp Lt nT nU oF Pi Qm Ri Sf Sj Tr Tt Vu Vv Wb Yh Yi Yk Zq Zw Zx Tm Tj Yf) Mz(Aa Aj bA cH cJ dR eD eZ gL hA hO hP HV hW Hx iA iH iJ Io Ir It Iv iZ jD jG jI jM Jo jP Jr jY kQ kR lK lL lM lO Md Mh Ml Ms Mw My Nf Nh Nm Nr Ns Nu nW Nx oE oF OH oK Om oN Oy Oz Pb Pc Pe pF Pg Pz Qb qC Qe qT qW qY rC Ru rW RX rY rZ Tn To Tr Tt Wf Xa Wm) Ij(Fc Fi Gh Hr Hv Hx Ih Il Io Ir It Iv Jh Jk Jo Jr Kc Kk Lu Lz Mc Md Mh Mk Ml Ms Mv Mw Mx Na Nc Nd Ne Nf Ng Nh Nl Nm Nq Nr Nu Nx Ny Of Oh Oi Om Pa Pc Pe Pf Pg Po Pz Qb Qc Qe Rx Sj Ur Ux Uy Va Vh Vw Vz Wb Wc We Wf Wh Yd Yl Zw Zx Ye Tl Xa Ti) Lx(Aa bR bS Fc Hr Hv Hw Hx

Figure 28 Continued

Ii Il In Io Iq Ir Iu Iv Jh Jk Jm Jo Jr Lu Ly Lz Mb Mc Md Me Mf Mg Mh Mj Mk Ml Mm Mq Ms Mt Mu Mv Mw Mx Na Nb Nc Nd Ne Nf Ng Nh Ni Nk Nm Nq Nr Nu Nx Of Oh Oi Om Pa Pc Pd Pf Pg Po Pz Qb Qc Qe Wb Wh Xa) Im(aJ aN aQ aW bA bB bF bS CH cl cJ CT Cu cZ Dc dD De dF dJ Dr Du Fc Fi Gb Gd Hl Ho Hp Kk Ko Ld Lp Lt Op pH Rt Ru Rv Rx Ry Rz Sf Sh Si Sj Uw Uy Va Vb Vc Vh Vj Vt Vw Vz Wb Wc Wd We Wf Wg Wh Yi Yj Zw Zx Tm Tl Tt Th Yf) Fr(Hq Hr Hv Hw Hx Ii Ik Il In Io Iq Ir Iu Jh Jk Jm Jo Jr Lu Ly Lz Mb Mc Md Me Mf Mg Mh Mj Mk Ml Mm Mq Ms Mt Mu Mv Mw Mx My Na Nb Nc Nd Ne Nf Nh Ni Nk Nm Nn Nq Nr Nu Of Oh Oi Om Pa Pc Pd Pf Pg Po Qb Qc Qe) Kq(De Du Ed Ef Et Fd Gb Gc Gd Gh Gn Hl Ho Hp Ii In Jp Kk Kl Ko Ld Lj Lp Lt No Oi Om Op Rt Rv Rx Ry Sf Si Sj Ss Tn Tv Ur Uu Uv Uy Uz Va Vh Vo Vt Vz Wb Wc We Wg Yg Yh Yl Zw Zx Ye Tm Tl Xa Ti) Mt(Aa aV bA bQ bU cA cG cK cL CO Ct dA dH dI Eq Fd Fp Ih Ik Ip It Jn Jq Js Ko Lj Lv Mi Mm Mp Mr Nj Nn Ns Nt Nx Ny Oe Oy Pb Pe Po Rz Ux Vb Vc Vt Vz Wb Wf Wh Yd Ye Tm Tl Xa Wm) Ow(Aj Du Eq Fc Fi fR Gb Gc Gh Gn Hl Ho Id Ko Lj Lt No Op Oy Rt Ru Rv Rx Ry Rz Sf Sh Si Sj Uw Ux Uy Uz Vb Vc Vh Vt Vw Vz Wc Wd We Wf Wg Wh Yd Yi Yl Zw Zx Ye Tm Tl Ti Th) Jt(bA Hu Hx Ii Ik In Io Ir It Iv Jo Jq Jr Lu Lw Lz Mb Mc Mh Mi Mj Mm Mr Ms Mw Mx My Na Nc Nd Ng Nh Nl Nm Nq Nr Nu Nx Oe Of Oh Oi Om Oy Pa Pb Pc Pe Pf Pg Pz Qb Qc Qe) Jp(Af Ar Ax bA Bb cH cl cJ CT Cu Cx Dc De Dp Ed Hb Hf Jd Jf Jv Kd Kf Kg Ki Kl Kp Kr Kx Ky Kz Oa Or Ou Ph Pi Pj Pk Ql Qw Ri Rm Sr Ss Tv Tz Uc Un Ur Us Uu Vq Vs) Lh(Aj Hq Hw Il Io Iq Ir Iu Jh Jk Jm Jr Lu Ly Lz Mb Mc Me Mf Mg Mh Mj Mk Ml Mq Mu Mv Mw Mx Na Nb Nc Nd Ne Nf Nh Ni Nk Nq Nr Nu Nx Oh Oi Om Pa Pd Pf Pg Po Pz Qe Ur) No(Aa Af aQ bA Bb bS CH cJ Ct Cu Cx Dc dJ eC fP hB hC hF hG iA Ic iH iJ iO iP lZ Kj Kk Kn Ko kQ kR kS Ld nW nY oF oK Ou pF Ph Tv Tz Ug Uu Vc Vo Wm Ti Th) Js(Aa Aj Fp Hr Hu Hx Ih Ik Il In Io It Iv Jh Jn Jo Jq Lu Mc Mi Ml Mr Ms Mw My Na Ng Nl Nm Nn Nr Ns Nu Nx Ny Oe Oi Om Oy Pa Pb Pc Pe Po Qe Rx Va Wb Wc Xa) Et(Aa Af aM Ao Ap Ar aW Ax aZ Bb Bg bN bV CH cJ cP CT cU Cx Dc Dd De Dg Di dJ Dl dM Ed Fy hB Id IZ Kd Kj Kk Kl Kn Ko Ld Oa Tv Ug Ur Uu Vo Vt) Jg(Hq Hr Ii Il In Io Iq Ir Iu Jh Jk Jm Jr Lu Ly Mb Mc Md Me Mf Mh Mj Mk Ml Mm Mq Ms Mu Mv Mw Mw Na Nb Nc Nd Me Mf Nh Ni Nk Nm Nq Nu Om Pa Pc Pd Pf Pz) Jj(Ad Al Ao Ax BA Co Cs cT Cw Dd Dg Ed Fy Io Ir Iv Jo Kd Kk Kp Ks Ky Ld Lw Mi Mp Mr Nj Nl Nu Oa Oh Pe Pg Pi Pj Qc Qh Ri Rm Sr Tv Uf Un Vq) Ma(Aa Hu Hw Hx Ik Il In Ir Jo Jr Lu Lz Mh Mm Mp Ms Mw Mx My Nb Nc Ne Nf Nh Nm Nn Nr Nu Nx Ny Oe Of Oh Oi Om Pa Pc Pg Qc Vt) Nb(aA Du Eq Fc Fd Fi Gb Gh Hl Ho Hp Lj Lp Lt Op Ru Rv Ry Rz Sf Sh Si Sj Ux Uz Vc Vh Vw Vz Wb Wc Wg Yd Yi Yl Zw Zx Ye Th) Mn(Aa bA Cu Hv Hw In Ir It Iv Jr Lu Mh Mm Mp Ms Mw Mx Ne Ng Nh Ni Nj Nm Nn Nr Nu Nx Oh Om Oy Pa Pb Pc Pg Qb Qc Qe Vt) Qe(Aa bA Jn Jq Kk Lv Lw Mi Mm Mp Mr Nt Nx Oz Rx Us Uw Ux Uy Uz Va Vc Vj Vt Wb Wc Wd We Wf Wg Wh Yd Yl Ye Xa Ti Th) Jn(Aa Fp Ih Ip Iv Jq Lj Mp Mw Nj Nn Ns Nx Ny Oz Pe Po Ru Uw Uy Va Vb Vj Vz Wb Wc Wd We Wf Wh Ye Xa) Nt(Fp Hu Hx In Io Iq Ir It Ly Mi Mm Mp Mr Mw Na Ng Nl Nn Nx Oe Oi Om Oy Pb Pc Pe Po Qb Qc) aA(Hq Hr Hw Iu Jh Jk Lu Ly Mb Mc Md Mf Ml Mq Ms Mu Mv My Nd Ne Nf Ng Ni Nk Nq Of Oi Pa Pd) On(Aa Ch Ct Eq Iz Rt Rx Sh Ux Uy Va Vb Vc Vh Vw Vz Wb Wc Wc Wh Yd Yh Zw Ye Tl Xa Wm Th) Kn(dJ Dp eC ED hX iC Ik In jD jF jH jK JO jQ jR jT Ko IM oE Ou Tz Ur Vt) Pe(Du Fc Gh Ih Ip Lj Lv Lw Mm Nn Ny Og Oz Ru Sj Va Vb Vc Vz Wb Wf Wh Yd Yl Xa) Ny(Fp Ib Ih Ip Iv Jq Lj Mm Mp Mr Nj Nn Ns Nx Oz Vj Wf Wh Ye Xa Ti Th) Lv(Aa Fp Io Ip It Iv Jq Lw Mi Mp Mr Mw Nj Nl Nr Og Om Oz Po Qb Qc) Oa(Dr Du Gc Ho Op Rz Sf Sh Si Sj Ur Uw Vj Wb Wd Yd Yj Zq Ye Xa Th) Ko(Ch Ed Ik Il In Jo Kc Kj Kk Ld In Io Iq Ir It Ly Mi Mm Mp Mr Mw Qb rS Tz Uu Vo) Nn(Fd Fp Ih Ip Iv Jq Lj Lw Mi Mp Mr Nj Ns Nx Oz Po Vc Wb Xa) Lj(Ih Ip Iv Jo Mg Mw Nj Nl Nm Nq Ns Og Om Ou Oz Pc Pg Po) Vt(Aj bF bN Dp eC Ed Fy Gp Il In Kk Ld Mh OH Ri Tv Ug) Pf(Dr Eq Gb Gd Ho Hp Lp Rv Rz Sh Ux Uz Vz Wf Yi Yl Xa) Aj(Ap bA Bb Co dF Dg Ih Jq Kf Li Nx Ou Qc Sr Uf Un) Oh(Du Eq Fc Fd Gb Ho Kk Rx Ry Sh Vz Yd Zq Zx Xa Ti) Mi(Fp Ih Ip It Iv Jq Lw Mm Mw Nj Ns Og Oz Po) Aa(Hr In It Jo Lu Mk Nl Oy Pb Pc Po Qb Qc) Ih(Fp In Ip Jq Lw Mm Mp Mr Nj Nx Om Oz Po) Og(Dc Fp Ir Iv Jk Mm Mp Mw Nm Nr Pz Qb) Ip(Fp Iv Jq Lw Mm Mp Mr Mw Nj Oz Po) Ur(Cu Fy Il Ir Jq Mr Nr Ou Pi Rm Un) Jq(Iv Mm Mp Mr Mw Nj Nu Oz Po) Xa(Cu Ed Hx Il Oi Or Oz Rm St) Fp(Io Mp Mr Nj Nm Nx Om Oz) Nv(Iq Iu Mj Ml Mq Nc Nq Pz) Ed(Kk Ld Ru Uw Yd Yi Ti) Po(Lw Mr Nj Ns Oy Oz Pb) bA(cH Dc Li Oz Pb Qb Qc) Kk(dJ Il Oi Qc Sr Tz) Ld(Em Fy Sr Uw Wb Yi) Dr(Or Ou Tz Uc Ut) Cu(Gd Ik Rt Vb) Lw(Iv Mx Nr Qb) Li(rS Wm Ti Th) Om(Ns Oy Oz Wh) Dc(Jo Oe Va) Fy(cQ dJ In) Mp(Hq Nj Oz) Mr(Mm Oz Ru) Uc(Of Oy Va) Il(Id Vj) Yi(aZ Oz) Jr(Ru Rx) Ou(Oy Ru) Ut(Eq Sh) IN(kC kO) WmOk FdNq NsNx MmQb MwYe TnWf StVa RxRm cHhB cQqZ wBnW

Unconstrained panels with 2 analytes, where 1.0E-4 >= 'model p-value' > 1.0E-5. Contains 5,533 panels of 191,187 total panels evaluated. :
Ps(aA aC AD aE AF aG aH al AJ aK AL AN AO AP aQ aR AS aU aV Aw AX aY BA Bb BC bE bF BG bH bl bJ bL bM BN BO bP bS bU bV bW bX bZ cA cB cC cD cE cF cG CH cl cJ cK cL cM cN CO CP CQ cR CS CT CV CW CX cY cZ dA DB DC DD DE dF DG dH DI dJ DK DL dM dN Dp Dr Du EF EM Eq Et Ex Ez Fc Fd Fi Fn FP Fr Gb Gc Gd Gh GL Gn gP Gz Ha Hb HC HF hG Hl Ho Hp Hq Hr Hu Hv Hw Hx iA Ib Ic Id IH Ii iJ Ik IO IP Iq Ir It Iu Iv IZ Jd Je Jf Jg Jh Ji Jj Jk Jm Jn Jo Jq Jt Ju Jv Kc Kd Ke Kf Kg Ki Kj Kl Kn Ko Kp kQ KR KS Kx Ky Kz Ld Lp Lt Lu LW Ly Mb Mc Md Mf Mg Mi Mj Mm Mn Mp Ms Mu Mv Mw Mx My Na Nc Nd Ne Nf Ng Nh Nj Nl Nm No Ns Nt Nv nW Nx NY Of Og oH OK Om oN Op Oy Pa Pd pF Pg Ph Pi Pj Pk Po Pz Qb Qc Qe Qg Qh Ql Qm Qn Qt Qu Qw Qz Ra Rb Rc Rf Rg Rh Rm Rt Rv Ry Rz Sf Sh Si Sj Ss St Tn To Tr Tv Vv Yh Yi Yj Zq Wm Tj Ti Th) Ke(aD aF aG aJ aK aL aO aP aR aS aU aV aX aY aZ bC bE bG bH bl bJ bM bO bQ bU bV bZ cB cD cF cG cK cL cM cN cO cR cS cU cW cY cZ dB dE dG dH dl dL dN Dr EZ Fa Fb Fn fY gW HA hL hO hX iB iC jD JE JF jG jH jI jK jL jM jO jP jQ jR jT jU jV jY IK IL IM IN IO pS pY qD Qb Ql Qm Qn Qt Qw Qx Qy Qz Ra Rb Rc Rf Rg Rh Rm rN rO rP rQ rT RU rV sC sK sM sO St Tn TO tR tS Tt tU Ud Uf uG uI UL UM UN uO uP uR UT uU uV uW uX uY uZ vA vB vC vH vI vO VP vQ VS vT vU VV vW WB wC wD wE wF wG wH wJ wK wL wP wQ yH yJ yK yL zA zG zH zI yE tM tL XA Tj Ti Th tF) No(aC AD aE aF aG aH al aJ aK AL aM AN AO AP AR AS aU aV AW AX aY aZ Ba bB BC bE bF BG bH bl bJ bL bM BN BO bP bQ bR bU bV bW bX bZ cA cB cC cD cE cF cG cl cK cL cM cN CO CP CQ cR CS cT cU CV CW cX cY cZ dA DB dC DD DE dF DG dH Dl DK DL dM dN Dp Ed Ef Ez Fc Fy Gh Ha Hb Hc Hf IB Id Jd Je JF jH jK jO jQ jR jT Ju Jv Jy Kd Kf Kg Ki Kl Kp Kr Ks Kx Ky Kz Oa Or Pi Pj Pk Qg Qh Ql Qm Qt Qu Qv Qw Qy Qz Ra Rb Rc Rg Ri Rj Rx Sj Sr Ss Tn To Ua Ub Uc Ud Ue Uf Uk Ul Um Un Uo Up Us Ut Uv Va Vp Wb Wh Xa tF) Vt(aA aC aE Af aH al aL aO aQ Ar aU aW Ax aZ BA bB Bc Bg bL bQ bR bS bW bZ cA cE cG cH cl cJ cP CQ Cs CT Cu CX cY cZ dA Dc DD dF Di dJ dK dM DR Fp Fr Fw HB Hf Hr Hv Hx iB Ic Id Ih Ii Ij Ik Io Ip It Iv Jd Jf Jg Jm Jn Jo Jq Jr Js Jt Ju Jy Kc Kf Kp Kx Ky Lh Li Lj Lv Lx Ly Lz Me Mi Mj Ml Mm Mq Mr Ms Mv Mx Mz Na Nc Ne Ng Nh Ni Nj Nl Nn Nq Nr Ns Nt Nv nW Nx Ny Oa OE OF Og Oi OK On Ou Oy Oz Pa Pb Pe pF Pi Qb Qc Qg Qh Qy Rb Rf Rh Rj Rm Sr St Tn Tr Tt Tz Ub Uc Uf Uk Um Un Uo Up Us Ut Uu Uv Vo Vp Yi Xa Wm Ti Th) Mz(aE Af aH al aM AN Ap aQ Ar aW Ax aZ Ba BB bF BN bR bS cE cG cl cP cQ Cs CT Cu Cx dA Dc dD De dF Dg Di dJ dK Dl dM Dr Du Ed eF Eq eT Fc Fd Fi fN fY Gb Gc Gh gP hC hF hG HL Ho Hp Hq Hu Hw Ii Ik Il In iO iP Iq Iu Jh Jk Jm Kc Kk Kn Ko Kq kS Ld Lp Lt Lu Ly Lz Mb Mc Me Mf Mg Mj Mk Mq Mu Mv Mx Na Nb Nc Nd Ne Ng Ni Nk Nq nY Oe Of Oi Op Ou Ow Pa Pd Pf pS pY qA qB Qc qD qU qV qX qZ rA rN rO rS Rt Ry Rz Sf Sh Si Sj ul Ur uT Uw Va vI Vj Vz WB Wc Yd yH Yk YL Zq Zw Zx Ye Tm Tl Ti Th) Jp(aC AD aE aF aG aH al aJ aK AL aM AN AO AP aQ aR AS aU aV AW aX aY aZ Ba bB BC bE bF BG bH bl bJ bL bM BN BO bP bQ bR bS bU bV bW bX bZ cA cB cC cD cE cF cG cK cL cM cN CO CP CQ cR cS cU CV CW cX cY cZ dA DB dC DD dE dF DG dH DI dJ DK DL dM dN Ef Ez Fa Fb Fn Fy Gz Ha hB Ib Ic Je Ju Jy Ks oE oH Qg Qh Qm Qn Qt Qu Qv Qx Qy Qz Ra Rb Rc Rf Rg Rh Rj St Tn Tr Ua Ub Ud Ue Uf Ug Uk Ul Um Uo Up Ut Uv Vo Vp Vv Tl Xa)

Cx Dc De Du Ed Fc Fd Fi fR Gb Gd Gh Hl Ho Hp iB Id jO Kc Kj Ld lN Lp Lt Op rB Ru Rv Ry Rz Sf Si Sj Tv Ur Uu Uw Uz Vj Wd Wg Yg Yi Yj Yk Yl Zq Zx Tm Ti) Fy(aQ aW CH Ct Dp Dr Ed Em Gc Hb Ho Hv Ic Id Ik Jd Jo Jv Kc Kj Li Lu Ng Oa OE oH Oi Ou Ow Oy Pb Ph Qb Qc Qy rB Ri Rt Ru Rx Sh Sr Tv Tz Us Vj Vs Vz Wb Th) Lv(Aj Bb Dr Ed Hr Hu Hv Hw Hx Id Ii Ik Il In Iq Ir Jh Jk Jm Jo Kc Ly Lz Mc Me Mg Mj Mx Nb Nc Nf Nh Ni Nm Nq Ns Nu Nx Oe Oy Pa Pb Pc Pf Pg Pz Sr Tv Ur Wb Wm) Jq(Af Ax cI Cx Ed hB Hr Hx In Io Ir It jF JH jO jT Kc Ld Lw Lz Md Ms Mx Nd Nh Nl Nm Nq Nr Ns Nx Oe Om Ow Oy Pa Pb Pc Pf Pg Pz Qb Qc Ri Rj Sr Tv Ug Uk Us) Nt(Hq Hr Hv Hw Ii Il Iu Iv Jh Jk Jm Jo Lu Lz Mb Mc Md Me Mf Mg Mh Mj Mk Ml Mq Ms Mu Mv Mx My Nb Nc Nd Ne Nf Nh Ni Nk Nm Nq Nr Nu Of Pa Pd Pf Pg Pz) Jl(Bb Dp Dr Ed Gb Gc Gh Gp Gz Hb Hl Hp Ic Id Iq Iu Kf Kj Kp Kx Ky Mf Mj Mq Mu Mv Op Ow Pa Ph Pj Ri Rv Ry Sj Sr Tv Us Uw Vh Yg Yh Yi Yj Yk Th Yf) Pf(Du Fc Fi Gc Gh Hl Ih kP Lt lX Ma Mi Mm nK nL nU Op pH Rt Ru Rx Ry Sf Si Sj Uw Uy Va Vb Vh Vj Vq Vw Wc Wd We Wg Wh Yd Yh Zq Zw Zx Ye Tm Tl Ti) Ld(Aj bB bR cH Dc dF dJ Dr Fd Fw hB Ho iB Id Il Jd Kf Lh Mr Oa Ok Ou Pi Qc Qh Ri Ru Tv Tz Uc Uf Un Ur Uy Uz Vh Vq Vw Wc We Yd Yg Zq Zx Ye Th) Ih(Hr Hv Hw Hx Io Ir It Iv Jh Jo Lu Mg Mq Ms Mu Mv Mw Mx Nb Nh Ni Nk Nl Nm Nq Nr Ns Nu Oe Oy Pa Pb Pc Pg Pz Qb Qc Rx Ur Va Ye) Ed(dK Dr Fd Gb Gc Ho Id In Kc Lh Nx Ow Ql Ri Rt Ry Si Sr Tn Tv Uc Un Ur Ux Uz Vb Vc Vh Vj Vw Wc Wd We Wg Wh Yg Yl Zq Zw Zx) Oa(Aj dJ Eq Fc Fd Fi Gb Gh Gn Hl Hp In Lp Lt Oi Ow Rt Ru Rv Ry Ux Uy Uz Va Vb Vc Vh Vw Vz Wc We Wf Wg Wh Yg Yi Yl Zw Tm Tl) Po(Aj Fp Hr Hu Hv Hw Hx Ik In Io Ir It Iv Jh Jo Mm Mp Mw Mx My Nb Nf Ng Nh Nk Nl Nm Nu Nx Oe Om Pa Pc Pg Pz Qb Qc) Mi(Aj fR Gd Hq Hr Hu Hx Ii Ik Il In Io Ir Jh Mp Mr Ms Mx My Nc Nh Nl Nm Nr Nu Nx Om Oy Pb Pc Pg Pz Qb Qc) Tv(Aj aW cH cQ Cx dJ Dp eC Gp Hb Il In Ip Jo Li Ml oE Oi Ou Ow Oy Pb Pg Qb Qc Rf Ri Sr St Tz Un Us Ut Wm) Dc(aA aQ Ar Ax bF cH cI cJ Cs CT Cx dF Di dJ Fr Ik In Kc Kj Li Lw Oi Ok Ou Ow Qc Rt Rx Sr Ug Us Vj) Mr(Aj Hr Hx In Io Ir It Iv Kc Md Mh Mk Mp Mw My Nj Nl Nm Nr Ns Nu Nx Om Ow Oy Pb Pc Pg Pz Qb Qc Sr Wm) Lw(Aj Ar Ax Cs Hr Hv Hx Il Io Ir It Lz Mj Mm Mp Mw Nb Nh Nj Nl Nm Ns Nu Nx Om Oy Oz Pa Pb Pg Pz Qb Qc) Fp(Hr Hu Hv Hw Hx Ik In Ir It Iv Jh Jo Mg Ml Mw Nb Nh Nl Nq Nr Ns Nu Oe Oy Pa Pb Pc Pg Pz Qb Qc) Ma(Hq Hr Ii Io Iq Iu Jh Jk Jm kP Ly Mb Mc Md Me Mf Mg Mj Mk Ml Mq Mu Mv Na Nd Ni NK Nq Pd Pz) Ip(Aj Hr Hv Hw Hx Il In Io Ir It Jo Lz Mx Nb Nh Nl Nm Nq Nr Ns Nu Nx Om Oy Pa Pb Pc Pg Qb Qc Ur) Jt(Ar bF cI Ct dF Hq Hv Hw Il Iq Iu Jh Jk Jm Ly Md Me Mf Mg Mk Ml Mq Mu Mv Nb Ne Nf Ni Nk Pd Ur) Ow(cH Cs eP Ex Fw Gz hB Ik In Kc Kd Kf kO Li mF Mk Ng nU Oe Of Oi Sr Un Ur Vj Yg Yh Yj Yk Zq Yf) Id(Aj aQ cH cJ cQ Cx dD dJ eC Gp Hb Ik In jH jT Kc Li Nh oE Og oH Oi Ou Pi qC Ri Sr Tz Ur wP) Vi(eF fP gL gP hC hF hG iA iH iJ iO iP iZ kQ kR kS lY mY nB nK nN nW nY oH oK oN pF Yj tF) Om(Eq Gd Hu Ir It Iv Mm Mp Ms Mw My Ng Nj Nl Nu Oe Pb Qb Qc Ru Sh Ux Va Vb Vc Vw Wb Wd Wf) Sr(aQ CH dD dJ Dr Ik In Kc Li Ng Oe oH Oi Ou Ph Pi Ri Ru Tz Ug Ur Va We Ti Th) Ut(Fc Fd Gc Lp Oy Rt Ru Rx Uw Ux Uy Uz Va Vb Vc Vh Vw Wb Wd We Wh Yd Ye Tm Tl Ti) Yi(aW Bo cU Fw hB Hv Jo Li Mj Ml Mp Mq Nq Nv Or Ou Pc Qb Rh Rt Rx St Tz Va Yh) Ou(bS cA CH Cs Ct Em Fd Ho Hq Ik In Iz Kc Kd Lp Mk Ng Of Oi Qw Va Wb Yl) Aj(Ax Bc Bg cG Cw Dd Dl Ef Ez hB It Jk Kc Kd Kg Kp Mm Nq Nr Pz Qb Tn Vq) Nx(Hr Hu In Ir It Iv jF Mm Mp Mw My Nj Nl Nu Oe Oy Oz Pb Pz Qb Qc Ur) Mp(Dr Hv Io Ir It Iv Mk Mm Mw Nl Nm Nr Nu Oy Pb Pd Pz Qb Qc) Li(Bb cT dF Dr Du Fd Gd iB jF Lp Ri Ru Sj Tz Ur Vc Wb Yd Ye) Rm(Dr Ru Sh Uw Uy Uz Vb Vh Vj Vz Wb Wc Wd Wf Wh Yk Yl Zq Ye) Ur(Cq cT Dd Fw Hv Iq It Iu Iv Kd Kf Mj Ok Or Qh Tz Up Vq) Mm(Hv Hw Hx Ir It Iv Mj Mw Mx Nj Nl Nr Ns Oz Pb Pg Qc) St(Dr Eq Fd Gc Ho Oi Ru Rx Uw Uy Uz Vj Wb Wd Wg Ti Th) Og(Hx Ii Il Io It Jo Mg Mj Mx Nb Nj Nl Nu Oz Pa Pg Qc) hB(aE aQ aW bN Ch cP cQ dJ Dr eC Fd fP jO oH oN Ri Si) Un(cQ dK eC iB Ik Il In jT Ms oH Oi Ri Ug Va Ti Th) Uc(Ch Ct Gd In Jo Kc Kj Ng Oi Rx Ug Us Uu Wb) Dr(Co dR Fw Ky Mq Nb Nq oF Oz Qh Tn Vj) Kf(eC hX iB Ik Il In Jo Kj Oi Oy rB Tz) Kc(cH Cs dJ iB Il Kd Ml Nr Or Qc Tz) Oz(cT Fd Ho Ir Iv Lp Mw Nr Pg Qb Uw) Wb(Lh Mj Ml Mq Mx Nq Nr oE Or Tr) Fd(aW bZ Cx Il Jy Lz Ml Mq Qx) pH(aW aY Cx nI nK nN Nr oW Pa) Mj(Ru Uw Vc Vj Wf Zq Ti Th) Fw(Ru Va Vc Vj Vz Yl Tm) Tz(Fc Ho Ru Rx Uw Va Ti) Ri(hW iB qC rB rN rS wD) Nb(Gc Yg Yh Yj Yk Yf) Ok(bN cH cI Cs jO rB) Mw(lt Iv Nj Nl Ns) Il(Ho Sh Uw Vz Yl) Qb(Bb Nj Nm Ns Uw) Ru(aZ Hv Or Pg Vu) Vj(Jm Kd Pa Pi Qh) rS(aW iP Mf qZ vl) Tn(Ch Ng Vc Wh) Lh(iB jF jO Wm) Va(Ir Nr Qh Vu) cJ(aA Ar Cs Qc) lN(nC nH nJ nL) Bb(Ax Cs Jo) Nv(Wf Wh Wm) Or(Ho Vq Zq) cH(aA dF nY) Nq(Lq Sh) Nr(Fc Vc) Ir(Us We) Qc(cT dF) Vq(Hx Ug) Oy(Tr wB) aZ(Ry Uw) cZ(rR rY) iP(rN wD) qZ(aN dJ) AdJo AxMc BaCt CsTh EmKy FaiB FrPz GdaM MqYe MxZq NgUf Njlv NljF HuwB JgUu KprB Rjnl VcPg PjwD aAbB dFdH jljT rNnW Constrained panels with 3 analytes, where 1.0E-10 >= 'model p-value' > 0. Contains 4,042 panels of 35,191,980 total panels evaluated. :
Et{Oy(aA Fp Hx Ih Ij Im Ip Is It Jg Jh Ji Jl Jn Jp Jq Js Jt Lh Li Lj Lv Lw Lx Ma Mi Mn Mp Mr Mt Mw Mz Nb Nj Nl Nn No Nq Nr Ns Nv Nw Oe Of Og Ok On Oz Pa Pe Pf Pg Po Qa Qb Qc Qd Qe) Aj(Ad BA Bb cI cP cT Cu Cx Dc Dd Fr Ih Ij Il Im Ip Is It Ji Jk Jl Jm Jn Jp Jt Li Lj Lv Lw Ma Mi Mn Mr Mt Mz Nb No Nr Nw Nx Og Oi Ok On Qa Qc Qd Qe) Ng(aA Fp Fr Hx Ih Ij Il Im Ip Is It Jg Ji Jl Jn Jp Jq Js Jt Lh Li Lv Lw Lx Ma Mi Mn Mp Mr Mt Mw Mz Nb Nj Nl Nn No Ns Nt Nv Nw Og Ok On Oz Pe Qa Qb Qd) My(Fp Hx Ih Ij Il Im Ip Is It Jg Ji Jl Jn Jp Jq Js Jt Lh Li Lv Lw Lx Mi Mn Mp Mr Mt Mv Mw Mz Nb Nj Nl Nn No Nr Nv Nw Ok On Oz Pe Pg Qa Qb Qc Qd) Ns(aA Fp Hx Ih Ij Im Is It Ji Jj Jl Jn Jo Jp Jq Js Jt Lh Li Lj Lv Lw Lx Mi Mn Mp Mr Mz Nd Nj Nl No Nv Nw Oe Of Og Ok On Oz Pe Qa Qb Qc Qd) Jj(aA Fp Ih Ij Il Im Ip Is It Ji Jl Jm Jn Js Jt Lh Li Lj Lv Lw Lx Mn Mp Mr Mz Nj Nl No Nr Nt Nv Nw Oe Og Ok On Oz Pb Pe Pg Qa Qb Qd) Jo(Fp Hv Hw Ih Ij Im Ip Is It Ji Jl Jn Jp Jq Js Jt Lh Li Lv Lw Lx Ma Mi Mn Mp Mr Mz Nc Nj Nl No Nr Nt Nv Ok On Oz Pe Qa Qb Qd Qe) Og(aA Fp Ih Ij Il Im Ip Is It Jg Ji Jl Jm Jn Jq Js Jt Lh Li Lj Lv Lw Lx Mi Mn Mr Mt Mz Nb Nj Nl No Nv Nw Nx Ok On Oz Pe Qa Qb Qd) Pb(aA Fp Ih Ij Im Ip Is It Ji Jl Jn Jp Jq Js Jt Lh Li Lj Lv Lw Lx Mh Mi Mn Mp Mr Mz Nj Nl No Nr Nv Nw Oe Of Ok On Pe Pg Qa Qb Qd) Oe(aA Fp Hx Ih Ij Im Is It Ji Jl Jn Jp Jq Js Jt Lh Li Lj Lv Lw Lx Mn Mp Mr Mz Nj Nl No Nv Nw Oh Ok On Oz Pe Qa Qb Qd Qe) Of(aA Fp Ih Ij Im Ip Is It Ji Jl Jn Jp Jq Js Jt Lh Li Lv Lw Lx Ma Mi Mn Mp Mr Mz Nj Nl No Nv Nw Ok On Oz Pe Qa Qd) Oz(aA Fp Ih Ij Im Ip Is It Ji Jl Jn Jp Jq Js Lh Li Lj Lv Lw Lx Mi Mp Mr Mz Nj Nl No Nr Nw Oi Ok On Pe Pg Qa Qd) Oi(aA Fp Ih Ij Im Is It Ji Jn Jq Js Jt Lh Li Lj Lv Lx Mn Mp Mt Mz Nl Nn No Nv Nw Ok On Qa Qb Qc Qd) Hu(aA Fp Hx Ij Im Ip Is Jl Jn Jp Lh Li Lu Lv Lx Mn Mp Mr Mz Nn No Nq Nv Nw On Pe Qa Qb) Mz(aA Fp Hr Hx Ih Ij Is It Jl Jn Li Lj Lw Md Mp Mr Nj Nl No Ny Ok Om Qa Qd) Ik(Fp Ij Im Is It Iv Jn Js Lh Li Lv Lx Mh Mr Mt Nl Nv On Pe Po Qa Qd) Nj(aA Fp Ih Ij Im Is Jl Jn Jq Js Lh Lj Lv Lx Mi Mp Mr No On Qa Qc Qd) Lw(aA Fp Hr Ih Ij Is It Jl Jn Jp Js Lh Li Lj Mr Ms Nl No Qa Qd) Hr(Fp Hv Hw Hx Ij In Is Ji Jl Jq Js Jt Lh Mr No Nr Ok Pe Qa) It(aA Fp Is Jl Jp Lh Li Lj Mr No Nw Ok On) Nl(aA Fp Jn Jq Li Lj Lv Mn Ne Nw Ok On) aA(Fp Ij Im Ip Is Ji Jn Li Lj No Nw) Im(Ii Ji Lj Nm No Nw Ok Qd) Ms(Ih Ij Is Ji Mn Nw On) Mk(Jl Mp Mr On Pa Pe) Ii(Ij Ji Lh Mr On Pe) Lv(Ih Jn Li Mr) Is(Iv Lj No Ok) Ji(Jq Lj Md Om) Nw(Fp Lj Mv Mw) On(Jh Lj Mv Mw) Pd(Mp Pe Pf Pg) Mt(Hx Mv Ny) Hq(Lx Mp Nd) Ij(Jh Jl Mp) Fp(No Ok) Mg(Jt Lh) Jm(Lh Li) NnMu NoOk MrHx JlLi} Im{Oy(aA Fp Fr Ij In Jg Jh Ji Jl Jp Jq Js Jt Lh Li Lu Lv Lw Lx Ma Mi Mm Mn Mp Mr Mt Mw Mz Nb Nj Nn No Nq Nr Ns Nt Nv Nw Nx Oe Oh Ok On Pa Pc Pe Pg Po Qd Vi) Ye(Ap Ar As Bb Bn Cq Cu Db Dc De Ez Fc Fi Gc Gh Ic Ii Ik Is Jd Je Jk Jl Jm Jn Jr Kc Kr Ky Lv Mf Mg Mj Ml Ms Mz Nb Nd Ng No Nt Nu Oi Or Oz Pj Rz Si) Oe(aA Fp Fr In Is Jg Ji Jj Jl Jp Jq Js Jt Lh Li Lj Lv Lw Lx Ma Mi Mm Mn Mp Mr Mt Mz Nb Nj Nn No Ns Nt Nv Nw Nx Oh Ok On Oz Pa Pb Pe Qa Qd) Ns(aA Fp Fr Hu In Jg Ji Jj Jl Jp Jq Jt Lh Li Lj Lu Lv Lw Lx Ma Mi Mn Mp Mr Mt Mz Nb Nj No Ns Nt Nv Nw Nx Oh Ok On Oz Pb Pc Pe Qd) Pb(aA Fp Fr In Ip Ji Jj Jl Jp Jq Jt Lh Li Lj Lu Lv Lw Lx Ma Mi Mn Mp Mr Mt Mz Nb Ng Nj No Nr Nt Nv Nw Nx Og Ok On Pa Pe Qa Qd) Oz(aA Fp Fr Hp Hu In Ip Ji Jj Jl Jp

Figure 28 Continued

Jq Jt Lh Li Lj Lu Lv Lw Lx Ma Mi Mn Mp Mr Mz Ng Nj No Nr Nt Nv Nw Og Ok On Pe Qd Sj Xa) Ng(Fr In Jg Ji Jl Jp Jq Jt Lh Li Lu Lv Lw
Lx Ma Mi Mm Mn Mp Mr Mt Mz Nb Nj Nm Nn No Nt Nv Nw Nx Og Ok On Pc Pe) Hu(aA Fp Fr In Jg Jl Jp Jq Jt Lh Li Lu Lv Lw Lx Ma Mi
Mm Mn Mp Mr Mt Mz Nj Nn No Nq Nt Nv Nw Nx Ok On Pc Pe Qd) Ik(Fp Fr Ij Is Iv Jg Ji Jl Js Jt Lh Li Lu Lv Lx Ma Mi Mn Mp Mr Ms Mt
Nd Nj Nl No Nt Nu Nv Nx Ok On Pe Qa Qd) Og(aA Ij Ip Is Jg Ji Jj Jl Jp Jq Jt Lh Li Lv Lw Lx Mi Mn Mr Mt Mz Nb Nj Nm Nn No Nt Nv Nw
Nx Ok On Pc Pe Qd) In(Fp Hv Is Iv Ji Jl Jq Js Jt Lh Li Lj Lu Lv Lw Lx Mi Mn Mp Mr Mt Mz Nj Nl No Nt Nv Nx Ok On Pc Pe Qa Qd) Jp(aA
Aj Fp Ij Is It Ji Jj Jk Jl Jq Jt Lh Li Lj Lu Lv Lw Mi Mp Ms My Mz Nj No Of Ok On Qd) Nj(aA Fp Jj Jl Jq Jt Lh Li Lu Lv Lw Mi Mn Mp Mr Mt
Mz Nk Nn No Nt Nw Ok On Pe Qd) Hr(Hv Hw Ji Jl Jn Jo Jq Js Jt Lh Li Lw Lx Mi Mr Mz Nb No Nr Nx Ok On Pa Pe Qa) Jj(AA Fp Ij Ip Ji Jl Js
Jt Lh Li Lv Lw Ma Mn Mr No Nt Nv Nw Nx Ok On Qd) My(Fr Jg Ji Jl Jt Lh Lw Lx Mi Mr Mt Mw Mz Nb Nn Nq Nv Nw Nx Ok On Pa Pe)
On(Hx Ii Jh Jk Jo Lj Lv Lw Mk Ms Mv Mw Of Oi Ok Qd) Lw(aA Fp Jl Lh Li Lj Lu Lv Mr Mz No Qd) Ii(Ji Jl Js Jt Lh Mr Nb No Nv Nx Ok Pe)
Of(Fr Jg Ji Jl Jt Lh Ma Nt Nv Nw Nx Ok) Ji(aA Aj Jl Jo Jq Md Ms Nk Nw Om) Qd(aA It Jg Jl Lh Lv Ma Nv Ok) Jt(aA Aj It Jo Lh Lu Ms No
Nv) Hx(Lh Lx Mr Mt Mz Nb Nw Pe) Lv(aA Li Mr Mz No Ok Wf) Lj(Ma Mi Mm Mp Nn Nv Pc) Oi(Jg Nn Nt Ok Ps Sj Vi) Mn(aA Aj Lu Mr
Ms No) Jl(aA Ij Jk Lh Mk Wf) Ug(Rt Uw Uz Vh Vi Wg) Mz(Lh Md Mp Wc Wf) Is(Aj It Iv Ms Zw) Nw(aA Aj Ms Mv Rx) Vi(Mf Rc Vt We
Wf) It(Hv Ir Jn Qa) Lx(Hq Ij Mh) Ma(aA Fp Lu) Mk(Mr Pa Pe) Mp(Hq Jq Mr) Mt(Aj Mv Ny) Jo(Lh Nt Ok) Nk(Nc Nl) Ip(aA No) Sh(Kq Yd)
Wf(Nx Tn) Jk(Fr Nv) AdAj DcLp FibS FpMm MhMr MiMs NeNl SjKi JgJs QvPs LiNv OkaA} Ji{Oy(Fp Fr Ij Il Jg Jl Jp Lh Li Lu Lx Ma Mn
Mp Mr Ms Mt Mw Mz Nn No Nt Nu Nv Nw Og Ok On Oz Pa Pe Pf Qd) My(Fr Ij Ik Jg Jl Jo Jp Jq Lh Li Lu Lx Ma Mn Mr Ms Mt Mw Mz Nb
Nn No Ns Nt Nu Nv Nw Og Ok On Oz Pa) Og(aA Fr Ij Il Jg Jj Jl Jm Jo Jp Jq Li Lj Ma Md Mn Mr Ms Mz No Ns Nt Nu Nv Nw Ok On Oz Pb)
Oz(aA Fr Hx Ii In Jg Jj Jl Jo Jp Jq Li Lj Ma Md Ml Ms Mz No Ns Nw Ny Oe Ok Om On) Ii(bA Fr Ij Ik Il Jl Jt Lh Li Lj Lx Mr Ms Nl No Ns Nv
Nw Ok On Pe Qa Qd) Hr(Fp Fr Hw Ip Jg Jl Jp Jt Li Lj Lx Ma Mr Mz Nl No Nv Nw Ok On Pe Qa) Pb(aA Fr In Jg Jj Jl Jo Jp Jq Li Lj Lu Ma Md
Mr Ms No Ns Nv Nw Ok On) Ik(aA Fp Fr Ij Jg Jl Jq Li Lj Lu Lx Ms Nl No Ns Nt Ok Qa Qd) Nw(aA Aj Hu Hx Jj Jq Md Mh Ml Ms Mv Mw
Ng Ns Nx Ny Oe Of Om) On(Hu Hx Jj Jo Lj Md Ml Ms Mv Mw Ng Ns Nx Ny Oe Of Oi Om) Ns(aA Jg Jj Jl Jo Jp Jq Li Lj Lu Mp Ms Nd No
Ok) Md(Fr In Jg Jl Jp Li Lx Ma Mr Ms Mt Mz No Nv Ok) Hx(Fp Fr Jg Jl Jp Lx Ma Mr Mt Mz No Nv Pa Pe) Jo(Fr Ij Jl Jp Jt Li Lj Ma Mr Ms
Nl No Ok Wm) Om(Fp Fr Ij Jg Jl Jp Li Lx Ma Mr Mz No Nv Ok) Jg(Hu In Lj Ml Ms Mv Ng Ny Oe Of Oi) Jj(aA Fp Ij Il Jl Jq Li Lj Ms Nl No)
Fr(Hu Ml Mv Mw Ng Ny Oe Of Oi) Jq(aA In Is Jl Jp Lj Ms No Ok) Ng(Jl Jp Li Ma Mr No Nv Ok) Lj(aA In Jp Ma Ml Ms Oe Ok) Oe(aA Jl Jp
Lx Ms No Ok) Ma(Ml Ms Ny Of Oi) Nl(In Mz Ne Nh Nk) Nv(Hu Mv Nx Ny Oi) Mk(Jl Mr Pa Pe) Ml(Fp Li Lx Mz) In(Jl Li No Ok) Of(Jl Li
No Ok) Mr(Mh Ny Po) Ms(aA Jp No) Nb(Jl Pa Ux) Hq(Lx Mp Nd) Oi(Li Nt Ok) Pd(Mp Nd Pe) Ajt(Ba Jp) aA(Jp Nj) PoLx NnHu MtNy Islv
QcQd} Nw{Oy(aA Fp Hu Ij Is It Jg Jh Jl Jt Lh Lv Lw Mi Mp Mr Ms Mt My Nj Nl Nn Nq Ns Nt On Oz Pb Pe) My(aA Fp Ij Is It Jg Jj Jt Lh Lw
Mi Mr Mt Mw Nb Nj Nl Nn Nq Ns Og On Oz Pb) Ij(aA Aj Hr Fu Hx Ii Ik Jh Jj Md Mh Ml Ms Mv Mw Ng Ny Oe Of Og Om Pb) Oz(aA Fp Hu
Hx It Jj Lj Md Ml Ms Mv Mw Ng Nl Ns Ny Oe Og Pb Vi) Hr(Fp Hv Hw In Jl Jo Jq Jt Lj Lw Mr Mz Nl No Ok Qa) Ii(Hv Hw Is It Jl Jn Jo Jt Lh
Mr No Nt Ok On Pe Qa) Jj(aA Fp Hx Is It Jl Jt Lj Lv Mn Nj Nl Ns On Pb) Og(aA Fp Is It Jl Jm Jt Lw Nj Nl Nm Ns Ok On Pb) Ng(Is It Jg Jt Lw
Mn Mp Nj Nl Nm Nt Ok On Pb) Oe(aA Fp Hu Is It Jt Lj Ms Nj Nl Ok On Pb Qa) Aj(Il Is Jg Jl Jn Jo Jp Jt Mt No Qa Qd Qe) Md(aA Hv Hw In
Jo Jq Jt Lh Mr Mz Ok Pe Qa) Mh(Fp Hu Is It Jl Jt Lj Mr Nj Nl No Ns Pe) Ms(aA Is It Jt Lw Mn Nj Nl On Pb) Hu(aA Fp Hx Is It Lv Nj Nl Nn
On) Ns(aA Fp Hx Is It Mp Nl Ny Ok Pb) Mr(Hx Mk Ml Mv Mw Ny Of Pg Po) Nb(Ps Rt Rx Vi Wc Wd We Wf Wh) Hx(Fp It Jl Mi Nl Ok Pe)
Pb(aA Fp Hw It Nj Ok Qa) Po(Jl Lh Lx No Nt Pe) Mp(Hq Lj Mk Mv Mw Pg) Mv(Fp Is Lv Nn On) Lw(aA Fp Lj Nl) Mk(Jl On Pa Pe) Ml(Fp
Hv Mz Qa) Mw(Jt Lv Nn On) Rx(aF aO Dp Jn) Om(Hv Hw In Qa) Nj(aA Fp Lj) Of(Jt Ok On) Nl(aA Ne) It(aA Ny) Jn(Jr Js) Lj(Ok Vi) NnMu
NtIk MjJt MzNy NdHq Islv OiVi} Jj{Ij(aA Fp Fr Hr Hx Ip Is It Jg Jl Jn Jp Js Jt Lh Li Lj Lv Lw Lx Ma Md Mi Ml Mm Mn Mp Mr Mt My Mz
Nj Nl Nm Nn No Nt Nv Nx Ny Oe Og Oh Ok Oy Oz Pb Qa Qd) Jp(aA Fp Ih Ip Is It Jg Jl Jm Jn Jq Js Jt Lh Li Lj Lv Lw Lx Mn Mp Mr Mz Nj
No Ns Nt Nv Nx Ny Ok Oz Pb Po Qa Qd) Lh(aA Ih Ip Is It Jg Jl Jm Jn Js Jt Li Lj Lv Lw Ma Mn Mp Mz Nl No Ns Nt Nv Ny Og Ok Oz Pb Qa
Qd) Ok(aA Fp Ip Is It Jg Jl Jm Jn Js Li Lj Lv Mn Mp Mz Nj Nl Nn No Nr Ns Nv Og Oz Pb Qd) Li(aA Ih Ip Is It Jg Jl Jn Jq Js Jt Lv Lw
Ma Mn Mz Nj No Ns Nt Nv Ns Og On Oz Pb Qd) Nv(aA Fp Ip Is It Jg Jl Jn Jt Lj Lv Ma Mn My Mz Nj Nl No Ns Nt Oe Og Oy Oz Pb Qd)
No(aA Ih Ip Is It Jg Jl Jn Js Jt Lv Lw Mn Mz Nj Nl Ns Nt Nx Og Oz Pb Qd) Jg(aA Fp Ih Ip Is It Jl Jn Js Lj Lv Mn Mr Mz Og Oz Po Qa Qd)
On(Fp Hu Ip It Jn Lj Ms My Ng Nj Nl Ns Oe Of Og Oy Oz Pb) Qd(aA Ip Is Jl Jn Lv Lw Ma Mn Mz Nj Nt Nx Og Oz) Is(Fp Fr Jl Lv Lx Ma Mn
Mz Nj Nt Og Oz Yd) Jl(Jn Jt Lj Lx Ma Mn Mz Nn Nt Ny Og Oz) Ma(Ih It Jn Js Lj Nt Oz Qa) Mn(aA Ip Jn Js Mz Nt Po Qa) Nt(Ip Js Lj Mz)
Jt(Fp Mz) FrOz IpaA} On{Oz(aA Fp Hu Ii Ip It Jl Jo Jp Li Lj Lv Ms Mv My Ng Nj Nl No Ns Oe Of Og Oi Ok Oy Qd) Ii(Fp Hu Ih Ij Ip Is It Jl
Jn Js Jt Lh Li Lj Lw Mr Ms Nj Nl No Ns Ok Pe Qa Qd) Pb(aA Fp Hu Ip It Jl Jn Jp Li Lj Lw Ms My Mz Ng Nj No Ns Oe Of Og Oi Ok Qa Qd)
My(Fp Hr Ij Ip Jg Jn Jp Li Lj Ma Mk Mn Mt Mz Ng Na Nj No Ns Oe Of Og Oi Ok Oy) Ns(aA Fp Hr Hu Ik Jo Jp Li Lj Lw Mk Mp Ms Ng No Oe Of
Og Ok Oy) aA(Hu Ij Ip It Jn Li Lj Lw Ms Mz Ng Nj No Oe Of Og Oi Ok Qd) Oy(Fp Ij Ip Jg Jn Jp Li Lj Ma Mn Mt Mz Ng Nj No Oe Of Og)
Ms(Hu Ik Is It Jn Jo Lj Lw Mz Ng Nj No Oe Of Og Oi Ok) Hu(Fp Hx Ij Ip Jp Li Lj Md Nj Nn No Oe Of Og Ok) Og(Fp Hq Ij Ip Is It Li Lj Lw
Ng Nj Nm Of Ok) Oe(Fp Hq Is Jn Jo Li Lj Ng Nl No Of Ok Qd) Ik(Fp Ij Is It Li Lj Nj Nl Nt Ok Qd) Hr(Fp Hv Hw Jl Jq Jt Lw Mz Ok Qa) Jo(Ij
Ip It Jt Li Nj Ok Qd) Lj(Jk Lw Mw Ng Nj Of Oi Ok) Ng(Jg Li Lw Nm No Of) Oi(Fp It Li No Ok Qd) Of(Ip Li Ma Nj Ok) No(Lw Mw Nj)
Mk(Jl Mr Pe) Jk(Ij Li Qd) Jp(It Mv Mw) Fp(Lw Ok) Mz(Md Nj) Zw(Is Ow) Li(Lw Mw) AjJt EqNn NeNl NjQd ItOk} Ok{Oz(aA Fp Fr Hr Ih Ij
Ip Is It Jl Jn Jo Jp Js Lh Li Lj Lv Lx Ma Mn Mp Mr Ms Mz Ng Nl No Ns Nv Oe Of Og Pe Pg Qa Qd) Ns(aA Fp Hr Ij Is It Jg Jl Jn Jo Jp Js Lh Li
Lj Lw Lx Ma Mn Mp Mz Nd Nl Nn No Nv Ny Oe Of Og Oy Pb Qa Qb Qd) Og(aA Fp Ih Ij Ip Is It Jg Jl Jm Jn Jp Lh Li Lj Lw Lx Mn Mp Mr Mt
Mz Ng Nj Nl Nn No Nv Ny Pb Qa Qd) Hr(aA Fp Ih Ij Ip Is It Jl Jn Jp Js Lh Li Lj Lx Mn Mp Mz Nj Nn No Nv Pb Qa Qd) Pb(aA Fp Ij Ip Is It Jl
Jn Jp Lh Li Lj Lx Ma Mn Mp Mr Mz No Nv Oe Of Qa Qd) Oy(aA Fp Ij Ip Is It Jl Jp Lh Li Lj Lv Lx Mp Mt No Nv Pe Pg Qa Qd) aA(Ij Ip It Jg
Jn Jp Lh Li Lj Lv Lw Mn Mz Nj Nl No Oe Of Oi Qd) Jp(Fp Ij Is It Li Lj Lv Mp Ms My Mz Ng Oe Of Qd) Oe(Fp Ih Ij Is Jl Jn Lj No Qa Qd) No(Ip
Is It Lv My Ng Nj Of) Lj(Ij In Lw Ma Mp Mz Of) Of(Ij Is It Jl Qa Qd) Jo(Ij Is It Jl Js) Ik(Ij Is Qa Qd) Ng(Ij Is Jg) My(Ij Mt) Islv} Og{Ij(aA Fp
Fr Ih Ik In Ip Is It Jg Jl Jp Jq Jt Lh Li Lj Lv Lw Lx Ma Me Mi Mm Mn Mp Mr Mt Mz Nj Nm Nn No Ns Nt Nv Nx Ny Om Oz Pb Pc Po Qd)
Jg(aA Fp Ih Ip Is Jl Jn Jp Jq Js Lh Li Lj Lv Lw Lx Mi Mr Mz No Ns Nv Oz Pe Po Qa Qb Qd Qe) Jp(aA Fp Ih Ip Is It Jl Jq Js Jt Lh Li Lj Lv Lw
Lx Mr Mz Nm No Ns Nt Nv Oz Qa Qd) No(aA Ih Ip Is It Jl Jn Jq Jt Lh Li Lv Lw Mn Mz Nj Nm Ns Nv Nx Om Oz Pb Qd) Nv(aA Fp Ip Is It Jl
Jt Li Lj Lw Mn Mr Mz Nj Nm Ns Oy Oz Pb Qd) Is(aA Fr Jl Jt Lh Li Lw Ma Mn Mz Nm Nt Oz) Qd(aA Jl Lh Lw Ma Nm Nx Oz) aA(Ip Lh Li
Ma Mn Mz) Jl(Li Lw Nm Oz) Lw(Lh Li) MzLi} Vi{Mf(Hx Ih Ij Is Jg Jn Js Li Lj Lu Nb Nc Ne Nh Nl Nn Ny Of Oh Om Oz Pb Pc Ps Pz Qa Qd
Qe Tn Uy Va Vo Vt Ti) Oz(Ih Ip Iq Ir Is Jl Jn Jr Js Lj Lx Nb Nc No Nu Oh Pe Pf Pg Ps Qa Qb Qd Qe Rt Sr Tv Tz Ub Uc Ue Vh Vt) Ss(Iu Jh Li
Mg Mi Mp Mt Mu Ni Nn Nq Pd Qd Qy Uc Uf) Wf(Ih Ij Is Jn Js Lj Lx Mw Nm Oh Pe Sr) Lj(Hq Ii Mp No Oi Pc Rc Uc Ug Vt) Vb(Iu Li Mi Mp
Mu Nn Nq Pd Qy Nn(My Ng Oy Qu Vt Vw Wd Wh) Is(Nl Of Rt Va Vs Vt We Wh) Ii(Ij Ir Nb Qc Sr) Rc(Ih Mn Oh Pf) Qa(Oy Pc Qt We)
Li(My Ng Vw Wd) Mt(My Vw Wd) Uu(Uf Uk Ut) Vt(Oh Pb Up) Uc(Pb Vs) Oi(Hq Ps) Om(My Wh) Vw(Mg Pd) ThMq MjJs Ndlj QcUg QePc
WdQy} aA{Ij(Hr Hu Ik In Ip Jg Jl Jp Lh Li Lj Lv Lw Lx Ma Me Mm Mn My Mz Ng Nj No Ns Oe Oy Oz Pb Qd) Jp(Fp Ip Is It Jl Li Lj Lv Lw

Lv Mz Nj Ny Oz) Jn(aA Lv Mr Mz Nn Ny Po) Ny(aA Fp Lj Lv Mr Mz) aA(Lj Lv Mz Nj Nx) Nn(It Lv Nx Oz) Nw(Aa Cx Ow) Po(Mz Oz) Lv(Lj Mz) Ji(Cx Wm) Ko(Il Ow) Nx(Fp Lj) Ajlm UcUh dJvl} aA{Mz(Fp Fr Ih Is It Jl Jn Js Jt Lj Lv Lx Mm Mp Ms Mt Nl Nm Nr Ns Nt Nv Nx Ny Oz Pb Po Qa) Nj(Fp Fr Ih Io Is It Jl Jn Js Jt Lv Lw Mp Mt Mw Nm Nn Nr Ns Nt Nx Ny Og Oz Po Qa Qc Qe) Jg(Fp Hu Ih Ik Ip Is It Jl Jn Js Lh Li Lv Lx Mn Mp My No Nx Of Oi Oy Oz Pb Qa Qd) Ma(Fp Hu Ih Is It Jl Jn Js Jt Lh Li Lv Lx Mn Ng Nl Nx Oe Oi Oy Pb Qa Qb Qc Qe) Ip(Fp Is It Jl Jn Js Jt Lh Lj Lv Lx Mm Mp Nm Nn Ns Nt Nv Nx Ny Oy Pb Qd) Mn(Fp Is It Jl Jn Js Jt Lh Lv Lw Lx Nl Nm Nt Nv Ny Oe Oy Pb Qa) Lh(Hr Hu Ih Is It Jn Jt Li Lj Lv Mm Ng Nm No Oe Oi Oy Qd) Og(Fp Fr Jl Jn Js Jt Lj Lv Lw Lx Nm Nn Nt Nx Ny Om Qa) Oz(Fp Fr Is Jl Jn Js Jt Lj Lv Lw Lx Mt Nt Nv Nx Ny) Lj(Is Jl Jn Jt Lv Lw Mg Mm Mp Nm Ns Nt Nv Nx) Qd(Jl Jn Li Lv Lw Mm Nm No Ns Nx Oe Oy Pb) Li(Hu Is It Jn Jt No Nx Oe Oi Oy) Ns(Is Jn Jt Lx Mp Nt Nv Nx Ny) Lw(Fp Is Jl Jn Js Lv Lx Nv Ny) No(Is It Jl Jn Nm Nx) Nv(Hu Jn Ng Oe Oy Pb) Lv(Jn Js Jt Ny) Is(Nm Oe Rx) Lx(Oe Pb) FpJt QaYe JlJn PsRx NxPb} Aj{Im(aI Ba bC bF cH cJ Co Cu Dc dF Dg dJ Fr Ij Ip Jg Jl Jq Ko Lv Lw Ma Mb Mi Ml Mm Mr Mz Nb Nk No Nx Og Oi On Qd) Ji(Ad Ap aW bA cH cT Cu Dg dJ Fr Ik Il Is Jg Jl Jt Li Ma Mg Ml Mn Mt Nk No On Qa Qd) Nw(Ad Ba cH cJ Cu Cx Dc dJ dK Fr Ih Iv Li Ma Mg Mi Mn Mr Mu Nn Nr Om Oz Pb) Qd(aE Ap aQ bA Bb cH cJ cT Dg Fr Ij Is Jg Ko Ma Mn Mt No Nx Oi On Ow) Is(aW cH cJ Co dJ Fr Hx Ij Jt Ko Li Ma Mg Ml Mm Mt Ne On Pz Uh) Kq(aW bJ cH cQ De dJ Et Hx Ik Il Ip Jm Kn Ko Oi Ow Pb Ru) Jt(Ad Ap bA Bb Cu dF Dg Ip Jg Jl Li Lv Mn Nv Qa) No(Ad Ba Bb Dc Ip Jg Li Mg Mn Mt On Ow) Qa(Ad Ap Bb Dg Jg Ko Ma Mn Rx Uh) Ba(Ip Jl Js Li Mn Mt Oz Qb Qc) Et(aW AX bN cH cJ cL Ko Uc) Ad(Jl Li Ma Mi Mn Nn On) Jg(Cu Dc Jl Li Lv Mr On) Mt(Ap Dc Ij Ko On Oz) Ko(Il Jl Nn Ow Uc) On(cH Li Mn) Uc(Of Uh) Ke(Il Ow) ApJl DcMa FcUt WdPf} Og{Jg(Fr Hu Hv Hx Il Ir It Iv Jm Jt Ma Mn Mp Mt Mw Mx My Nb Ng Nj Nl Nm Nn Nt Nx Ny Om Pa Pg) Li(Ih Ip It Iv Jn Jq Js Jt Lh Lv Lx Ma Mi Mn Mr Mt Nb Nm Ns Nt Nx Ny Om Oz Pb Qa Qd) Lh(Fr Ih Ip It Jl Jn Jq Js Jt Lj Lx Ma Mi Mn Mz Nm Nn Ns Nt Nv Ny Oz Pb Qa) Is(Fp Ip Iv Lj Lv Lx Mg Mi Mm Mr Ms Mt Mw Nj Nn Ns Nu Nx Ny Om Pe Po Qd) Jl(Fr Ih Ip It Jn Jq Js Jt Lj Lx Ma Mn Mz Nj Nn Ns Nt Nx Ny Om Pb Qa) Qd(Fr Ip Jn Jq Jt Lv Lx Mi Mm Mn Mp Mr Mt Mz Nj Nn Ns Nt Ny Om Pe) Fr(Ih It Jn Jq Js Jt Lw Mn Mz Nt Nx Oz) Jt(Fp Ip Lj Lx Ma Mn Mz Nn Ny Oz Qa) Nv(Hu Ih Jn Lv Mi Mt Nt Qa) Lw(Js Lx Ma Nt Ny Qa) Mz(Ip Lx Ma Mn Nt Ny) Qa(Ma Mn Nm No Nx) Ma(Ih Lj Mr) Ip(Mn Nt Om) NoJs NtMn OmOz} Is{Yh(Ad Bo Cq Fw Im Iv Kf Kq Kz Me Mq Nc Nf Nl Nn Nt Nu Nv Nw On Ow Oz Pe Ql Rx Wb) We(Af aZ bM bO Cq Dr fR Hp Im Je Jy Kg Kq Ld Mv Nu Wb) Wb(aN aW aZ bN cX Eq Ms Nx Oz Ru Rx Ul Uu Uv Vs) Va(Af aN As aZ bM bO Cq dD dL Dr Ld) No(Hu In Iv Lv Lw Ms My Ng Nj) Li(Ik In Lw Ns Oe Oy Oz Pb) Rt(Ed Em Or Up Us Uv Vz Zw) Ye(bM Ed Je Ld Ps Qy Uo) Uh(Ch Jo Ld Oi Ur Uu Yd) Yd(bN Ed Nw Qy Vt) Zw(bN fR Gd Ld Uu) Oe(Fr Jg Lh Lx Nv) On(Hr Iv Jk Jo Oi) Oy(Fr Jg Lh Lx Nv) Dr(Up Ur Uu Yk) Ld(Uy Vb Wc Wd) Af(Yj Yk Zq) Ik(Lh Nt Qd) Ps(Rx Us Uu) Uv(Du Rx Vj) Eq(Qy Uo) Yg(Im Kq) Jg(My Ng) Wh(bM fR) Uu(Hp Vw) Vb(Bo dI) EdRv HrLh IqYk VzaW ZqKj KkdJ} Ps{Rx(aC aG aS Ax bA Bc bQ bR cN CP Cq cT Cu Dc Dg Ed Em Fd Fi Fy Gn Ha Hl Ho Hv Hx Ij Il In Iq Ir Iv Jl Jn Jq Jr Js Kd Kn Li Me Mi Mj Mr Mw Mz Na Nb Nd Nu Nw Ny Oa Oh Oi Op Or Oz Pa Pe Ph Pi Qv Qy Rb Ri Rt Sr Tv) Oi(aL aW aY bF bJ bN bQ bX cE cL dI Ed Ex Fw Fy Jd Kd Kr Mj Nt Oa Ow Us Ut Vv Yd Zw Tm Tl Xa) Va(aJ aK aR aZ bS Cx dB Ib Je Qn Rj Vq Ye) Oz(aK aL aZ bO bQ cL dD Fw Gp Im Om Ut Xa) Ye(aW Ed Im Jn Mf Nn Pf Qc) Uu(bQ Fy Gp Il Pf Qh Tr Uc) Gp(Ua Uv Vs Wd Yd) Ed(aU cY Il) Ur(Il Nb Qa) Pf(Us Uv Yl) Vs(bQ Kq) aW(Or Yl) aZ(Nn Qa) ChUt NbUg WfKk} On{Hr(In Ip It Jn Lh Li Lv Mr Mw Nj Nl No Oi Pe) Mz(Hx Ii Ik It Jo Li Lw Mv Mw Nl Ny Om) Jk(Fp Ip It Jl Jn Lv Lw Mr Nl No Qa) Jo(Fp Jl Jn Js Lv Lw Nl No Nt Qa) Mk(Fp Lw Mh Mp Mw Nj No Pa) Mr(Hx Md Mh Mv Mw Ny Pg Po) Ik(Ip Iv Jn Lv Mb Mh Qa) Mw(Hq Ij Jg Ma Mn Qd) Oi(Ip Jn Lw Nj Nl) Mv(Jg Ma Mt No) Hq(Lw Lx Mp Nd) Pe(Hx Md Pd Po) Nj(Fp Ip Nk) In(Ih Jt Li) Om(Hv Hw Jq) Lx(Pg Po) Mp(Pd Pg) Nk(Nc Nl) Yh(Ow Tl) NnMu MdJq HxLh IjJh LdUy PdPf} No{Oy(Ip Jh Jl Jn Jq Jt Lh Li Lx Ma Mi Mn Mp Mr Mt Mw Mz Nj Nn Nv Nx Om Pg Qa Qd) Oe(Ij Ip Jg Jl Jn Jt Lv Mz Nj Nv Pb Qa Qd) Pb(Ij Jn Jt Lh Li Mp Mz Nv Nx Qa Qd) Lw(Hr Ip Jl Lv Ms My Mz Ng Nj Qd) Jl(Hr Hu Ii Ip Mk My Mz Ng Nj) My(Ij Jg Lh Mt Mz) Nj(Ip Lv Mz Nk Qd) Hu(Ij Ip Jg Nn Nv) Ns(Jn Jt Li Qd) Ng(Ij Ip Jt Nv) Uh(iO nW oK oN) Hr(Jt Lh Mz) Ti(dR hB) Mp(Hq Pd) Ii(Jt Lh) Ij(Ik In) LvIp MdMz IkJg} Im{Ye(aC aK aQ aU aV bE bO bU bW cA cB cI cK cQ cU cV cY dC DK Ex Gb Ou Pc Qa Qc Qe Qh Qz Rc Rg Rh Rm Sj To Uc Ue Uh Us Uv Vc Vp Vq Vw Wd Wh Yl Zq Tj Ti Yf) Ug(Dr Fd Gn Hl Ho Tl Xa Yf) Wf(aI Kq Or Ou Tr Ut) Ij(Fr Jg Ma) Cu(Eq Wh) Mz(Sh Yg) Kq(Uw Ux) aU(Vz Wb) DrOu YfOi WhaH} Oy{Nv(Ij Jg Jh Jl Jt Lh Li Lj Lw Mi Mp Mr Mt Mw Mz Ns Oe Oz Pe Qd) Lx(Fr Ip Jh Jn Jt Lh Li Lw Ma Mz Nm Nn Nt Nx Ny Om Oz Qd) Jg(Js Lh Li Mp Mr Mt Mz Pe Po Qa Qd) Li(Ij Jl Lh Lw Mt Mz) Ij(It Mi Mm Mr) Qd(Jl Lh Ma) Lh(Ma Mn) ThKq} Kq{Wd(aD aN aY Ch Ed Fc Fw Nb Nd) Wh(aN aY Ch Fw Gl Lj Oa) Wf(aY Ch Ed Fw Nx Oa Po) Ru(Bg Co Ng Om Rz Tn) Ux(aW Ex Gl Jm Nb Nx) Ch(Fi Vc Wc Yg) Yh(Js Mx Oh Ow) Nb(Uw We Yg) Yg(Mx Oa) Yd(aZ cQ) Lp(Ur Uu) EqcF ThOz NnRz WcaZ} Qd{Oz(Fr In Ip Jg Jl Lh Li Lv Lw Lx Ma Mn Mp Mr Mz Nj Ns Nt Nv Oe Pe Qc) Ik(Fp Fr Ij Ip Jl Jn Lv Lx Mr Mt Nj Ns Nt Nv Pe) Ns(Jg Li Ma Mp Nv) Lh(Hr Ii Pb) Oe(Jg Ma Nv) WmNw MyJg RxUu} Qa{Ye(aX bM dD Du Ed Gl Ny Rt Uv) Du(aJ Ld Qv Ri Ug Ur Uu) bM(Hp Rx Va Wf Wh Yl) Wb(Dd Mf Oz Qt) Zw(bQ Ld Oi Qv) Jg(Ik Ng Oe) Oz(Fc Hl Ma) aJ(Rt Yd) aZ(Lp Rx) DrHp HlOi HrJl VzdG JoUh OpUu UxcE} Nb{Ur(Fd Op Rz Uw Ux Va Vh Wc We Tl) Ld(Uw Va Vb Vw) Un(Eq Rx Uw Vz) Vj(aH dE Ik Nw) Tl(aI Qv Ug) Bo(Yh Yi) Zq(cR Ng) Tm(Uh Vq) Ow(Uw Uy) Vb(bZ Ij) CuUx DuNw EtVh EqbZ HlOz TzRx SiUg WdaH WfKk RtOu} Mz{Kc(hR hV hX iB jK jL) Li(Hr Jl Lw Ns Oz Pb) Uh(hA hX iB jL lK lO) Qy(eZ hO hP qA qC) Jg(My Ng) bP(rS zH) cZ(yH tL) NsMp HrJl WbOw QwqC JkeZ KnhX NwjO aSrO aYuU cEyH cWuT dJvI hOhR} Jg{Ng(Fr Ih Ip Jl Jn Js Li Lw Lx Ma Mi Mn Mp Mr Nt Pe Po) My(Jl Lh Lx Mr Nv) Jl(Lj Ns Oe Oz) Lj(Lw Mp Oe) NsMp IhOe IjIk LdVa} Ji{Wm(Ii Ik In Jl Lv Mm Ms Ng Nw Oi) Ik(Af Ax bA cH cI Cx) Ii(cH cT Cu dM Uh) jT(cQ Ct oK) JobA VqiB dJjE} Li{Jl(Hr Ik Lw Mk Ns Oz Pb) Ns(Lv Lw Mn Mp Nv) Pb(Ij Lh Lv Lw Nv) Ik(Ij Lv Nt) Oz(Ip Lv Lw) LwHr HuIj} Ld{Il(Uw Vz Wf Yl Zq Xa) Dc(Va Vb Wc Wh Ye) Qh(Uy Wd Wh Yd) Ye(Jm Ny Rm) Uy(Uc Ut) TlNy} Nw{Wm(Ii Ik Lv Mm Ng Nm Oe) Aa(Oz Pb) Ex(Rx Xa) Wc(Ij Kd) bA(Oz Pb) CxIk EfRx IiSr YhPf SfUu} Nn{aZ(Du Eq Rv Vc Vz Wb Wc Wf Wh Yd Yl Zx) aX(Vc Vj Wb Xa) Eq(Jl St) WbVt} Nv{Ns(Hu Lj Lw Mp My Ng Oe Oz Pb) Lj(Oe Oz Pb) My(Ij Mt) Oe(Oz Pb) NgJt} Jl{Hr(Ij Jq Jt) Ij(My Pb) Oz(Lx Ma) ChZq CxVa WbOw RuUr VjaY} Wb{Oh(aW bS Dd Gp Oi Qy) Ow(cB In Qh) RxRm} Ij{My(Fr Lh Lx) FrNg NsMp NdYh VcbM} Ke{dJ(eT hO qA qC) IzfN qAjT} Ns{Lx(Mh My) Mp(Lh Lj)} Mt{aX(Op Vh Xa) MyLh} Yh{Nq(Js Oh) Ow(Cu Dk)} Wf{Ny(bZ Ma Mv) GlUt} Va{DdJn QeaZ SrOr OwdL} Dr{GpRm UcLj VcPf} Uh{Tv(Ii Ur) NroN} Vj{DcbN IlOr QeaZ} Ed{FcTr MfXa} Lx{PoJt HqrS} Jn{WhOz QyYe} Jo{CuEt JtLh} Ru{JyaZ UrVu} Rm{MwYe RxNy} DcRtUt DuQeQv GdOwiZ GnOaVu MaLhPb NfIlYj HpOzPf iPrSoF Constrained panels with 3 analytes, where 1.0E-8 >= 'model p-value' > 1.0E-9. Contains 7,327 panels of 35,191,980 total panels evaluated. : Vi{Wh(aF Ap aU bJ bW CO cP cS cU Cx Ez Gc Hv Ij Im Iu Jd Jh Ji Kc Kd Ke Kg Ki Kq Ld Li Lj Lx Mg Mi Mm Mp Mq Mt Mu Mv Nq Oh Pc Pd Pf Pj Qa Qd Qy Si Ue Uf Ut Vq Wd) Is(Ad aF Aj aY Bg Bn Bo Ch Ct cX Ex Ib Ii Il Im Iz Jj Jq Kl Li Lj Me Mj Ms Nc Ng Nk Nn Nu Nx Oa Oe Oy Pa Pb Pc Rc Ru Sh Sr Ss Ug Uk Up Ur Uv Vo Wc Yk) Oi(aP aU aW bZ cG cI Ez Fa Hv Ih Ii Iu Ji Jn Js Kd Ke Kk Kq Kz Ld Li Ma Mi Mn Mq Mt Mu Mv Mw Nf Nn Nq Oa Of Oh Om Oz Pf Qb Qd Qe Qy Rh Rm Uf Ug Ur) Qa(Af AJ aN aU aY Bc bS Ch Dd dM Ex gP Ha Hc Ib Ii Ik It Je Jm Kd Kl Lu Mj My Nv Pb Qv Qw Rc Rj Ru Ss Ug Ur Uv Uw Vs Zw Ye) Uu(aL aO aX bO cA cF cK cU dR eF Fb Fn Gh gL Hc Hw Ih Jf Jh Jk Kc Kd Ks Mm Mt Nd No Nq Nr Pb Pd Pj Ql Rc Rm Uv Vj Vt Vu Wc Yk) Oz(aD Al aO aZ bF bZ CT cV cX Dc dF dM dR Fa

Figure 28 Continued

Oy Pg Qc) Aa(Hr Oy Pa Po) Cx(Cu Jn Jr Mm) cI(cH cJ dJ Jn) Nn(Eq Iz Wf) bN(cH Jn Jr) jO(Ji Jr Qe) No(Iz oN) Hx(Cu Dc) Wh(Fw Ub) Ow(Ng Oy) Uh(Tv Uu) Pf(Wb Zw) oE(uI vA) AfJi AxMc CtIj DlJt WmcJ ThKd ExWc NroN NbTm HurS QedJ KoUu OuOy} Jg{Ng(Fp Hx Ik It Iv Jq Jt Lj Lv Mg Mm Mt Mw My Nb Nd Nj Nl Nm Nn Nq Nr Ns Nu Nx Ny Om Oy Oz Pa Pb Pg Qb Qe) Lj(Ij Ik Jq Jt Lh Lv Lx Mi Mn Mr My Nj Nn No Ns Nv Of Oi Oy Oz Pb Pe) Ns(Fp Ih Ij Jq Js Lh Lv Lw Lx Mi Mn Mr Nd Nv Oe Oy Pe Qb) Jl(Fp Hr Hu Ih Ij Ik It Jn Jo Lw Lx Mk Mn Nj Of Oi Pb) My(Fp Ih Ip Jn Jq Js Lv Lw Mi Mn Mp Nb Nx Pe Po Qb) Oy(Fp Fr Ih Ip Jn Jq Lv Lw Mi Mn Nb Nx Pa Pg Qb Qe) Lh(Hr Hu Ih Ii Ik Jo Lw Oe Of Oz Pb) Oe(Fp Ij Jn Js Lv Lx Mr Nv Po Qb) Fp(Ih Ik Jq Lw Mp Oi Oz Pb) Ih(In Lv Lw Of Oi Oz) Mr(Ii Lw Mk Oz Pb) Js(Ik Jo Lw Of Oi) Ld(Uy Vb Wd Wh Zw) No(Mn Mw Of Oi) Lv(Ik Of Ok Oz) Lx(Hq Ik Oz Pb) Ij(Hu Jo Of Pb) Nv(Hu Of Oz Pb) Mi(Ik Oz) NnHu MkPe MpHq} Kq{Ru(Ad Ao aX aZ Dg Hc Iz Kg Kp Ld My Oy Oz Qu Qz Sh Ss To Uu Uw Ux Wd Wf Wh) Wf(aN aW Bb Eq Fc Gl Ih Il Jm Kd Lj Lp Nb Nd Nn Nr Ny Pa Pf Us Vs Th) Rx(cQ eF fP gL gP iA iO iP iZ kQ kR Nb nY oE oF oH oK pF Uv Ux) Rz(aN bA bQ De Dk Eq Fw Gn Il Jm Kr Nb Nr Oe Ow Us Yd) Wh(Al aW Ed Fc Ih Im Jm Nb Nn No Nx Pf Us Th) Eq(Ao cA cK Im My Nn Ny Oz Po Uv) Uh(Ch De Ii Jo Ld Ng Of Oy Uu Uv) Ch(Fc Gb Gh Ik Ko Si Uw Yd) Wd(aW Gl Im Jm Nn Oa Us Vs) Th(Bg Co Om Pb Tn Uv) Fc(Iz Jd My oE oF Qz) Yd(fP My oE Ow Qz Vw) Ow(Dr Ng Ux Wb Zw) Ux(aN Il Oi Pf) Ko(Jo Kj Ng) Nb(Vw Ye) Nd(We Yh) Ik(De Wc) Il(Fi Sh) Yi(aZ Vs) Qz(Vw Tm) Oa(Du Gn) Oh(Wb Zw) Uu(Sf Tm) jT(Ng Of) EdGc YhRm ShJm SjPb WeNy JocQ LpOz NxUw OyPa} Nv{Oz(Fp Fr Hu Ih Ij In Ip It Jl Jn Jo Jt Lh Lv Lw Lx Ma Mi Mn Mp Mr Ms My Ng Nj Nt Of Pe) Oy(Fp Fr Hu Ih Ip It Jn Lv Ma Mm Mn My Nb Ng Nj Nm Nn Nq Nt Pa Pb Pf Po) Pb(Fp Hu Ij Ip It Jl Jn Jt Lh Lv Lw Lx Ma Mi Mn Mr My Ng Nj Nt Of Pe) Ng(Fp Fr Ij Ip It Jl Jn Lh Lj Lw Lx Ma Mi Mm Mn Mp Mr Nj Nm Nt) Hu(Fp Ij Ip It Jl Jn Jt Lh Lj Lv Lw Ma Mn Mr Nj Nn Nq Oe) Ns(Fp Ik It Jl Jn Jo Jt Lv Lx Ma Mi Mn Nj Nt Of) Oe(Fp Hq Ih Ij It Jl Jn Jt Lw Lx Ma Mn My Nj Nt) Lj(Ii In Jl Jt Lv Lw Ma Mm Mn Mp Nj) My(Jl Jt Lh Lw Lx Mr Nb Nj No) Jt(Hr Ii Ik Jo Of) Ik(Fp Ij Nt) Mk(Mr Pe) Hq(Lx Mp) Hr(Jl Lh) Ii(Mr No) FpLw IjJo} Uh{Ld(bA Cu Dc Dd dJ Ed eF Hv Ic Id Il Ji Jl Jn Jq Jr Kd Ke Kn Ko Mr Na Oi Pi Qe Ri Tv Uc Vp) Tv(Af aW bN Ch cQ Cx De dJ Dp eC Ic Ik Im In Jo Ko Of Oi Oy Pb Ri Rj Uu Vs Wm Tj) Uc(Ch Ii In Jo Kj Ng Of Oy Ur Uu) Ii(Cu Id Jq Ke Kn Mr Nr Qe) hB(aE aW CH dJ oN Ri) Mt(Ng Ns oN Oy Oz pF) Ch(eF gL Jl Nn Ou) Ji(iB Ik Jo Oi Uu) Ur(Id Ir Jl Mr Vt) Kn(dJ eC In Jo) oN(bA Mr Oh Pe) Id(bN In Uu) Ko(iB Oi Uu) aE(iZ oE oF) cH(eF gL nW) dJ(gL iZ Kk) Ri(iB iZ) Oi(Kk Qe) Vt(bN nW) bA(Ct nW) AxMc NocA NbXa TrOy WbOh OaiB} Jl{Ij(Hu Hx Ii Ik In Jk Jo Lj Lw Lx Ma Mk Mm Mn Ng Nj Ns Oe Of Oz Wf) Oz(Fp Fr Gh Hr Ih Ip Jn Js Jt Lh Lj Lw Mn Mp Mt Nn Nt Ny Sh) Hr(Fp Hv Hw In Ip Jn Js Lh Lj Lw Lx Ma Mn Nm Ns) Ma(Fp Ih Jn Lj Lw Ng Ns Oe Oy Pb) Lx(Hu Lw Mk My Nj Ns Oe Oy Pb) Wf(cQ Cx Fw Jn Mw Nn Pe Pf Sr) Lj(Jt Lw Mm Mn Ns Nt Pb) Ow(Dr Eq Oy Rz Yd Yh Zw) Ns(Jn Lh Lw Mn Mp) Oy(Fr Lh Lw Mn Mt) Jo(Jt Ko Lh) Vj(Ex Jm Kd) Pb(Fr Lh Mn) Lw(Jn Mn) Ii(Jt Ke) Rx(Im kQ) aW(Eq Rz) CxWh MkMp MtMy IkKe LdRu} Im{Sh(dR eF fP gL gP hB hC iA iP iZ kR kS nW nY oE oF oH oK oN Ou pF) Ye(Aa dA fP Fw hC iH Ld Mi Mu Nn nW Qy) iP(Fd Gc Hp Ry Sf Si Sj Vz Yd Yl Zx Tl) Eq(bF bQ dR Ef Lv Ou Vu) dR(Fc Rv Ux Vz Wb Yd) Wf(eF Jr Mj On Uc) Yl(bP Cu Dc Ib Ug) Oi(Fd Gh Kk Yd Xa) bS(Gh Sj Vw Yd Yf) Dr(oE oF Or Rg) Oz(Sf Yd Yj Yf) gP(Hp Sf Ux Xa) Lv(Ux Yd Zw) Wh(bP Lx Tn) oE(Gb Wb Zw) Gh(Ji Lx) We(Rb Ug) Ur(Rt Uz) aH(Vc Zw) CqLp DcVa FdQv HloF YiaZ WcUg XafP RzcE RvOr UxaI VwbP} Lh{Oy(Fp Fr Hr Ih Ip Jh Jn Js Jt Lj Lw Mi Mm Mp Mr Mt Mw Nn Nt Ny Om Oz Pb) Oz(Fr Hr Ih Ij Ip Jo Jt Lj Lv Lw Lx Ma Mi Mn Mp My Ng Ns) Hr(Fp Ih Ij Ip Jn Jq Js Jt Lj Lw Lx Mn My Ns Pb) Pb(Fp Fr Ih Ij Ip Jn Jt Lj Lw Lx Mi Mn My Ns) Ns(Ih Jn Jo Jt Lj Lw Lx Ma Mn) Ng(Fr Ij Jt Lw Ma Mn No) My(Fr Jn Lw Lx Ma Mn) Ij(Hu Hx Ii Ik Jo Lj) Jo(Js Lw Ma No Nt) Lj(Lw Ma Mm Mn) No(Hu Hx Po) Ii(Jn Jt Lw) Ma(Ih Lw) CtjT NtIk MpHq} Ow{Wb(Al aW Bg Ch CQ cV CX Du Ef Gp Hc Ik Jk Jy Ks Mf Mt Mu Ne Nq Oe Oh On Or Oz Pb Qc Rb Uc Ut Tl) Dr(eF gP Hc iA iJ iO iZ Jy kQ kR Nb nY oE Oi oN Pf Rb Uc Ut) Ke(Ct Ii Ik Iz Jo Ms Ng Of Oy) Yd(fP kR oH oK oN) Eq(bF Bg Ef Mu) Nb(Gc Si Vz Tm) iZ(Rz Sh Zw Ye) Vz(eF fP Il) Jo(Em Ji Ko) Oy(Kk Mt Pa) Gh(fP Ny) oF(Hp Sh) DuJn EdZx EmKk GbhG MwYe SjhC StVa XafP RzhB OifR} Nb{Tl(aH bM cE Dc dR Et gP iP iZ nY Ou Rj Vq Ti) Ur(Sh Si Yd Yg Yh Yi Zq Xa) Ti(Oz Tz Uk Un Vt Yj Tm) Tm(aH Bo cQ Ij Mp pF) Rx(Cu Fd Lx Oa Or Oz) Vb(Cu Et Ji Ma Uf Vq) Bo(Vh Yd Yl Xa) Eq(cG Nq Om Uf) Va(Ji Lv Mp Ou) Oy(Fr Ij No Wd) Ye(Ih Mq Mv) Cu(Vw Wd) Et(Ux Wf) Hl(Un Vq) Si(oE Oz) Rt(Lv Mp) Ug(Gc Zq) Vj(aX Oz) FiLd NoMy IjVz YdOu WbOh WdOm RzUf YlPe} Lx{Oy(Fp Ih iJ Io It Iv Jo Jq Js Lj Lv Mg Mi Mm Mp Mr Mt Mw Nj Ns Nu Pb Pe Pz Qe) Oz(Fc Ij Ip Jq Jt Lv Ma Mi Mr My Ns Pe) Ij(Hq Hu Hx Ik Lw Ng Nj Ns Oe Pb) Ns(Hx Jt Lw Ma Mn Mp Ny Pb) Jt(Hr Ii My Ng Oe Pb) No(Hq Mn My Po) Pb(Ma Mr Pe) My(Mt Pf) Hq(Ma Mn) Wb(hB kQ) Zw(iZ oF) AaFc DrkQ NtIk MhOk MkPe TlhB RxiZ} No{Ng(Jn Ma Mg Mm Mn Mp Nm Nn Nx) Mr(Hr Hx Ii Mh Mk My Po) My(Jq Jt Mi Mw Nn Nx) Hr(Hv Hw Ij Jq Nx Pe) dR(Fc Gh Lp Ru Ry Uy) In(Ih It Jn Js Jt) Mn(Hu Lj Ms) Mp(Hu Mk Pg) Nl(Ne Nk Oe) Ke(Ii Ik oN) Ur(fP oH oN) Pe(Ii Mk Po) Et(Iz oN) Ij(Jo Ms) Wf(Tn Ut) ThkR NnOi NtIk MaLj MtHx NcNk HuJn ItOe JoJt VtoH} Fr{Oz(Fp Ih Ij Ip It Iv Jn Jq Js Jt Lj Lv Lw Mn Mr Ng Nj Nl Ns Nt Oe Oy Pe) Oy(Ih Jn Jq Js Jt Lv Lw Mi Mn Mp Mr Mt Nx Pe) Ng(Jn Js Jt Lw Mn Mr Nt) Ok(Hu Ih Nj Nl Oi) Ns(Jt Lw Mn Mp) Ij(Hu Ik Oe Pb) Jt(Hr Oe Pb) NtIk LwLj MkPe MrPb MtMy IhOe} Ma{Lj(Ih Ij Ik Jq Jt Lv Lw Mi Mp Mr Nj Ns Nt Oy Oz Pb) Oy(Fp Ih Ij Jt Lv Lw Mr Mt Pe) Oz(Fp Ih Ip Jt Lv Mr Ns Nt Pe) Ns(Fp Ih Jt Lw Mp Nt) Ng(Ih Ij Jt Mr Nt) Ok(Lv Mg Nj Nl Oi) Pb(Fp Ih Ij Mr Pe) Fp(Ik Jt Lw) My(Ij Mr Mt) Ih(Lv Lw Oe) LwMr JoJt} Ji{Jo(aN aW bF cH cI cJ cT Cu dJ dM iJ Ko Ri Uc) Ii(aW dF dJ Ed Ke Ld Oa Ri Uc Vt) bA(cH Ct De dJ In Jq Oi Oz Pb Qc) jO(cJ dJ jE jF jK jQ jR lN Lu) Ik(bN cT De dJ dM) bN(iB jD jT) cI(cH dJ Et) cQ(jQ jR) DeoF WmNm LphG bIjT cHhB cJiB} Ij{Oy(Fp In Ip Jh Jt Lv Lw Mn Mw Nj Nn Nq Nt Nx Om Pa Pe Po) Mp(Hq Lj Mk My Ng Oz Pb Pd) My(It Lw Mi Mm Mr Mw) Lj(In Lv Lw Mm Pb) Mm(Ng Pb) Ik(Lv Nt) Vb(Mu Ni) fP(We Xa) FiLd NnHu MrHx NdWb WcaZ KiVc VhdR} Wb{Oh(aZ Bo bR bU cB cN cQ dB Et Gc Il Jf Kc Kd Kk Kl Ko Ld Mf Mh Mn Mt Nq Pi Ri Rx Ss Um Vc Ti) Pf(aK aQ fP Ld Lu Mf Mp oE Oz Ss) IlLd JnRj JraW} Ke{dJ(rW uG uI uR uW uX vA vU wE zI) Hu(rP rS uM vS wG wP yD) Il(Ii Ik Jo Kj Oy) Ik(cH Nn Oh) oE(cH De Yd) Ou(Of Oy) cQ(vQ wD) eC(De Hc) rB(rR sK) ChiJ EtIi JnrR cHoH sOjT} Mt{aX(Fi Rx Rz Sj Uw Ux Vb Vc Wc Wf Wh Zw) My(Jn Js Jt Mn Ns Nt Ny Oz) Ny(Eq Ok Wd Wf Wh) Oy(Jt Mn Ou Uc) Oz(bA Eq Ip Ux) Ok(Md Mv) DuOa NsMp JoKo XafP} Ny{Wf(Co gL Ni Nn Nq Tn Ut) Ok(In Lv Mp My Nj Oi) Rx(Je Jr oE oF Oh) Xa(Ib Oi Rj) Nn(Eq Wh) Ld(Hp Sj) Oi(Rz Wd) EfYe NsMp TmaW mUlK} Pf{Dr(kQ Ld Oa oN Rh Rm Sh Tz Uc Vb Vt) Vz(aZ fP iA Qe) Ed(Vc Yl) FdOz HpfP RvaZ OkPd} Nn{Eq(aX bF Hq Mj Ou) aZ(Yh Yi Yj Yk) Ko(Jo Kj Ng) aX(Sh Vb Tm) DrVt FdOz InOk UxaH} Ld{Va(Cq Qc Rm St) Il(Vh Vj Yj) Qh(Vb Vz Yh) Yk(Dc Nr) Zx(Ed Oa) Xa(Oi Qc) YhOn YjJm} Oz{Jn(Fd Rx Wd Xa) Lj(Jt Lv Mp Nt) Ip(Jt Mn Nt) Om(Eq We) EdWd FcJr FpJt NsMp XaRm} Et{Jo(Ax bA cI Cs cT Dc Dd Kn Tv) Oi(bA cI Cs) bA(Ct Of) DcIi EdFi IkcI} Ok{In(Nr Nt Qb Qe) My(Mv Nr Pe) Ik(Ih Mr Nj) Mk(Nd Pa) NtNa MsOi NcNk IiPe} Oa{Du(aU dR Rx) Dr(Nq nW) Gc(hB hG) Si(hB hG) Ye(Mw Qy) ShgL ZwOn WfJy} Ed{Cu(Fc Fi Xa) dR(Dr Vw Xa) Tr(Zw Yf) Ut(Wf Ye) GboF SihB XagP} Lj{Lw(Lv Mn Mr Nt) Jt(Hr In Lv Mn) DrOu NtIk LvMm SihB jTpS} nW{wB(dM Kr qZ vH) qZ(jD Up Ut) Ko(wD zA) UbrN OrwD} aZ{Yi(cS Mu Ni Nq Vu) CuWc TnYk QeTl RmVa} Ns{Mp(Fp Jn Jq Js Jt Mn Nt) NtMn} Ye{Mw(bA Jn Js Oh) MqIl IhhB QyOh OmiZ} On{Uu(Lp Ru Yh) WmNg ThOf YhbB} Jn{Rx(Ne Rj Vt) EqNq RjVa} Pe{DudR FcoH MkMp XafP VccE} rS{aW(cZ jT) IdOr KohO KpdJ} Dr{hB(Il Kd) IhoF OuaW} Rm{Va(Dd Rj) ShRi ZqUu} Ur{Uc(De Of) DcVa IlVt} Qe{GnYh RtbQ YlbM} Oh{Qy(Gd Rx) YhVu} Oy{MnMr WcOm OuPa} dJ{CtwB FyIn KnhX} Fp{Jt(Hr Ik)} Rt{IqUt JsgP} wD{AncO CtMe} jT{IdqH KncQ} CuKpRu DgTrZq EfEqSt FdaYhB GcbMoE MwTnWf IhYdOu IlJoKo VzJraW VtcWvP

Figure 28 Continued

Constrained panels with 3 analytes, where 1.0E-7 >= 'model p-value' > 1.0E-8. Contains 19,523 panels of 35,191,980 total panels evaluated. :
Vi{Kd(Ad Ar Ba Ch Cs Ct dC Dg Dp Ed Gc HB Hv Hx Id Ir Iz Ji Jj Jn Jo Jr Kf Kg Kj Kl Ky Li Lu Lz Mb Mh Mk Ml Mx My Nb Nc Nf Ng Nk Nq Nw Nx Of Ou Oy Pa Pf Ph Ps Pz Qc Qd Qg Ql Qx Rj Rm Rt Sh To Ux Vb Vj Vs Wd We Yg Tl) Qc(AF aG Aj aU aW Bg bJ bN Bo bW cB Ch cL CO Ct Cv cZ Dp Eq Ez Hf Hv Ib Iu Jj Kc Kf Ki Kq Kz Li Lu Mi Mq Mt Mu Nc Nf Ni Nk Nl Nn Nq Oe Oh Oy Pb Pc Pd Qd Qv Qy Rb Rj Rt Rx Sh Uf Va Vs We Tl) Of(aF aV aW aX aZ bC bO bW bZ cA cC cK CO cS cW cY dA De dK Ef Ez Ho Hq Hv Ii Ji Js Kg Kn Kq Mg Mi Mk Mq Mt Mu Mv Mx My Nd No Nq oF Ou Pb Pc PF Pk Ps Qd Qe Qy Rc Rh Rm Uc Uf Ut Uv Vc Vj Tj) Mp(Ad Ao bC bF bR cG Cp Ct Cx dC Dg Dk Ex Fn Hq Ib Ik Ir Iz Jn Jo Kf Kg Ki Kj Ko kR Li Lz Mh Ml Nc Nd Ne Nk Ns Oh Oy Pa Pc Pf Qe Qn Qu Qx Rt Rx Sh Sr Ua Uf Ux Uy Vo Vp Vt Vv Wc Yd Yg Yh Th) Oh(Af Aj aO aS aY Ba bE BG Bn Bo bV Co CT cZ Dd dM Dp Gc Gz Hc Ho Hv Ib Ih Ii Iu Kc Kl Kq Kz Mj Mq Mt Mu Nc Ng Ni Nk Oe Ok Pa Pb Pk Qd Qe Rh Rj Rt Rx Sh Ss Uf Uv Vo Vs Wc We) Nn(Ad Ao Aw Ba bC bW Co Cp cS Ct dC Dg Di Ed Fr Gl Hu Ib In Ir Jg Jh Jj Jo Js Kf Kg Kj Kl Lu Lz Mg Mh Ml Mu Mv Mx Nc Nt Nw Pb Pc Pz Qt Qx Rg Rh Rj Rm Tn Tz Ua Uv Vj Vs Th) Pb(aW aZ BO bW cB cJ cL CO Ct cU Fw Gc Gp Ib Ih Ir Iu Ji Jr Js Kq Li Mi Mk Mq Mt Mu Nc Nk Nl Nq Nw Oi Om Pd Pf Ps Qe Qy Rc Rh Rj Rx Sh Sr Tz Ub Uf Uh Ur Vu We Wh) aW(aU bB Bg dC Dg Dp Ed Ef Fa Fi Fp Gc HB Hv Hx Id In Ji Jj Jo Jr Kc Kl Ky Lu Lv Lz Mb Me Mk Ml Mr Mx Nb Nw oF Oy Pf Ph Ps Pz Qd Qg Qx Rm Tn To Ur Vs Vz Wd tF Yf) My(aF aU bC bJ Bo cB cJ cO cS Ct cZ De Ef Et Ez Fn Ib Ih Il Ir Ji Ke Kg Ki Kk Lx Mg Mm Mw Nb Nc Ni Nk Nw Oe Pc Pd Pf Pj Po Ps Rh Sr Ub Uc Uh Vj Vq Vt Vu Wd) Hv(Af aO aX aZ Cp Ct Cx dC De Di Eq Gl Hu Ib Il Ir Iz Jd Jm Kf Kj Kl Kp Lz Mh Ml Mx Nb Nl Nv Nx Oe Oy Pa Pc Pf Qb Qx Rj Rt Ru Rz Tn Ua Uv Ux Uy Vb Yg Th) Ib(Ad aQ aV aZ bO cB cE cI dJ eM fP Gh hB Hx iA iJ iO Iu Js Kn Kp kQ kR Ky Mi Mq Mx Nb Nr Nw Ny oF OK oN Pc pF Ps Qb Qd Rm Sh Tn Tz Ut Vb Vs Wh Zq) Js(AF aO Bn Bo Ch Ct CX Dd dM Ex Gl Ii Il Jm Kl Li Lu Mb Mi Mt Mu Nb Nc Nk Nl Nq Nv Nx Oe Ok Qn Qy Rj Rt Ru Rx Tn Uf Ur Uv Vp Vs Vt Wc We Zw) Nw(AF bJ BN Bo bV Ch Ct CX Di Dp eM Gl Hc Ih Iu Jm Jq Lu Mb Me Nc Nk Ns Nu Nv Ok Pk Qm Qn Qw Rj Rt Ru Rx Sr Tn Uk Up Va Vp Vq Vs We Yg Yk) Gc(aX Ba bC Bo bV De Di eM Gl Hc Hf Il Im Ip Iz Jd Kf Ki Kj Kk Lu Lx Mh Nb Nk Nl No Ns Nx Oi Oy Pe Pf Qe Rj Ru Rx Sr Ub Ul Uv Uy Vq Vs Yg Th) aZ(aO aU aX bE Bn bW Co cU Cx cZ dK Ed Ez Ho Ih Iu Jn Jy Kc Kq Kz Mg Mk Mu Mw Nb Nc Ni Nk Nq Oa Oe oH Pd Pj Qd Rc Rj Rx Sr Uf Ur Va Vq Wc Yk) We(aF aK aQ aU bO cA cB cK Co cU dA De dJ dK Ef Ez Fn Hu Ii Jh Ji Jn Jq Kg Kq Mg Mi Mt Mu Mv Mw Mx Nb Nq Pc Qe Ql Rm Sh Ua Uf Uv Vc Wc Yl) Oy(aF aO aX bJ bW cB CO Ef Ho Ih Ij Ir Iu Jh Jn Kc Kq Lu Mg Mi Mq Mt Mu Mv Mw Nc Nk Nq Ns Nu Om Pd Pe Pf Pj Ps Qy Rm Rx Sr Uc Ue Uf Vq) aU(aO Ax Ba Bn bV Ch cY dC Dp eM Eq Fn Fp Gl Ih Ij iZ Jn Kg Kl Lu Mh Mx Nb Nc Ng Nk No Nu Nx Oe Pe Pf Qd Rj Rt Rx Rz Ss Uv Vs Vw Wd) Mx(aF bE bJ bN Bo bW Co Ct cZ Hc Iu Kc Kq Li Lu Mb Mg Mi Mk Mq Mt Mu Nc Ni Nk Nq Ns Nu Nv Oe Pc Pd Pk Qy Rj Rv Rx Sr Uf Ur Vq) Mi(Ao bC Co Cp Dg Di Gl Hc Hu In Ir Iz Jg Jo Kf Kg Kj Kl Kp Lz Mg Mh Ml Mv Nl Nt Or Pf Qu Qx Rj Rt Tz Ua Uf Uv Ux Vj Vs) Sh(AF aO Ba bJ Bn Bo bV Dd Dp Ed eM Hc Ij Ip Ir Iu Lu Mb Nq Ns Nu Nv Oa oE Ok Pc Pe Pk Qb Qe Qh Qn Rj Rm Ru Rx Sr) Qb(aF aG aK aX bC bE bJ bN cL cS Cw cY cZ De dI Hc Ho iH Ii Kg Kq Mj Mk Mm Mq Nc Ni Nk Nl Oe Pj Qv Rc Rj Rv Ug Vj) Vs(aQ bW cB cJ Co Dc De Ez Ho Ih Ij Iu Ji Jl Ke Kq Li Lx Mg Mq Mt Mu Mz Nq Om Pd Pe Pf Ps Qy Rj Rm Si Ub Uf Uh Vu) Iz(aF Ap aX bW CO Cx De Ef Ho Ih Ij Ir Iu Jh Ji Ke Ki Lu Mg Mm Mq Mu Mv Mw Pd Pe Pf Pj Qa Qy Rx Si Ue Uf Vq) Tz(AF aO bJ Bn Cx cZ dK Il Iu Jm Li Mt Mu Nb Nc Ni Nk Nl Nx Oe Pc Qm Qn Qy Rj Rt Rx Sr Uf Up Uv Va Wc) Ji(Aj aO Bg Ch Ex Gl Ii Im Jd Jm Ko Lh Lp Nd Ng Nx Oa Ok Pa Pk Ps Qm Rc Ru Tn Ul Uy Vb Vh Vw Wc Wd Yd Th) Qd(Af aX bL Cp Dk Eq Fr Gl Hu Ii Ik Il Kl Lu Ng Nx oE Pa Pc Qn Qv Qw Rj Ru Rz Ua Ul Ur Uw Uy Vb Ye Th) Oa(Af aJ bC bW Co cU cW dA dI dK Ez GP Ho Ic iZ Kc Kq Lu Mg Mu nW nY OE Pd Qw Qy Rc Uh Vj Vq Ye) Uv(bB Bo Ct Et Fp Ir Iu Kq Li Lu Lv Mk Mt Mu Nc Nf Nk Nq Pa Pe Pf Pj Qe Qy Rj Rx Sr Uf Ur Vj Vq Tl) Pc(Ar bG BO Cs Ct cU Fp hB Ih Ir Jj Jl Jn Jr Kk Lx Mh Mz Nc Ng Nk Nl Nx oF Pe Pf Ps Pz Rj Rm Uc) Im(aG aJ aK aQ bB Bg bX cB dC Dl dM Eq Fn Ha Ii iP Jg Jj Mb Mw Ng Nt oE oF Qu Qz Uh Ux Vw Yg) Li(bC bL bW Cp cR Ct DC Ed eM Fn fP Fr Gl Jd Jm Kg Kj Kl Mv Nt oE Or Ps Qh Qt Qu Uw Vj Th) Jn(Af aG Bn Bo bS Ch Ct Cx Dd Dk dM Hu It Ki Lu Nc Nk Nv Ny Oe Pa Pf Qv Qw Rx Ug Uh Vp Ye) Rj(Ad aK aO aQ bO bP cA cB cE cK cU eM Fc Ii Jq Mq Nb Nd No Ny pF Ps Qe Rm Tn Vb Vc Vw Wc) Rx(aK aQ cA cB cK Dc eM Fc hB Hx Ii Jl Lu Mq Nb Nd Nf Nl No oE oF Qe Tn Uc Vb Vc Tl tF) Ur(aO Bg bO cB Ch Dc Di Ed Fw Hc Ik Il Ip Iq Ir Jd Nc Nd Ne Ng Nk Ns Nx Qh Rc Rm Ss Vt) Sr(Ad aQ aV cA cB cK Db dJ Fc Fn iP iZ Nd No nY oE oF pF Ps Rh Rm Tn Ug Vc Vw Wh Yl) Aj(aK Ao bE cC cL dK Ed Fn Hw Ih Jt Kj Mk Mm Mw Nb Pf Ps Ql Rh Ue Ut Vj Vu Wd Yk) Bg(aF aX bZ cB cJ cL cS Ho Hq Ih Kg Kk Kz Ma Mm Ni Pj Ps Qa Qe Rh Rm Uc Ue Vj Vq) Eq(aF aX bW cL CO cS cU cZ Ef Ez Ho Iu Kc Kg Kq Kz Mg Mq Mt Nl Nq Pd Ps Uc Uf) Hc(aJ Ar bJ bZ Fw Ha Il In Jy Kc Ke Ki Lx Mn Mq Mt Nu oH Pj Qy Si Un Ut Vq Yk) Ss(bC bU bZ cC cL cU dK IH Kg Kz Ma Mk Mm Mv Mw Nb Nk Pf Pj Ps Qe Qt Vj Vq) Ef(Ad aF aK aX bC bJ bW CO cS cZ Ho Jh Kc Kg Mg Mm Mt Na Pj Vj Vu Wh Yg) cU(bF Bo bQ bV Ch Ct Ex Gl Ih Ir Iu Lu Mb Nc Ns Nu Nv Nx Ok Pk Qe Rt Tn Vw) Mq(bM cS Dc Dd Ex Fr Fw Gl Gp Hu Ik Il Kl Mh Mu Nx Qt Qz Rz Ua Ul Yg Ye) Pf(Ad aK cA cE cK dK eM Fc Fn Gh Hf Ii Kp Kz Nc Nd Nf Ng Nl Tn Uc Vb Vc) Bo(Ad aK aQ aV cA cB cK Fc hB hC Ii kQ kS No oE oK oN pF Ps Rh Vc tF) Ed(bB bZ dM Fc Gn Hx Iu Kp Kz Mn Nb Nc oE oF Oi pF Pk Ps Rm Uc Wh Xa) Nq(Ao Aw aX Co Cp Di Gl Jd Jm Nb Nt Nx Pa Rm Ru Rz Tn Ux Uy Vw Yg Th) Ir(Ad aK cA cK Cv dI dJ iH Mk Mu Nd No Nr Ok Pa Qy Rc Rh Tn Ug Vc Wc) Qe(aY bM bS cB Ch cW dK dM Gn In It Kl Lu OE pF Qw Uk Uw Vb Vw Ye) Fn(aJ bN bP cB Ch Cw GP Ij Il iP Mb Mg Mj Nl oE Uh Vq Wh Ti) Nb(aI Ct dA Is Jk Ke Ki Kp Kz Lu Mk Nf Ng Oe Pa Pj Ry Ub Vq Tl) Rh(Af Ch Cx Di Lu Lz Mb Nc Nk Nv Nx Oe Pe Qv Qx Ra Rc Ru Vq Wm) Vw(aF bE bG cC Co De dK Jh Jt Kc Kg Kz Nc Nf Ni Nk Pe Uc Vj Vq) Lx(cA cK eM Gh hB hG iJ iZ kR kS Nd No oE oH oN Tn Vc Wc tF) Mt(Ao dC Fr Gl In Jg Jh Kf Kg Kj Kl Lu Nt Or Qu Qz Rz Ux Th) Ij(Ad aK eM Fc Gh hB iA iH iZ No Nr oE oF OK Tn Vb Wc tF) Qy(Co Gl Hu In Jg Jo Kg Kj Kl Lz Mh Ml Mv Nt Or Qu Qx Ua Ux) Is(aO bJ bV Cq dI dK Dp eM Kk Og Pk Rv Uy Vv Yd Yg Yh Ye) Vb(bG cS Dd dK Ez Hw IH Iv Jh Jo Ma Ni Om Si Vj Vq Vu) Pe(Ad aK cA cK Fc Gh Ii iP Nd No Nt nY oE Ok Pk Po Tn Vc) Ct(Ad aQ aV bO cA cK dK Fc Ii Nd No oF pF Ps Tn Vc Zq) Nf(aN cB Ex Fw Gl Gp Ic Il Jd Jm Ki Lj Nx Pa Ru Ul Th) Or(aF bJ BN Cx dK Ez Il Iu Jm Mu Nl Nx Oe Ru Uf Va) Ps(Af Bn Ch Cx Je Kl Lz Mh Ml Rc Rt Uh Us Va Vo Yg) Lj(bW cG cZ iH iJ iP iZ Kg Kj kR Lu nY oE oF pF tF) Mu(Co Gl Hu Jg Jh Kg Kj Kl Mh Ml Mv Qz Ua Ux Zq) Kq(Ad Ao aX Co Cp Gl Jd Jo Kf Kg Kj Kl Rc Tn Ux) Ch(aF bJ cZ dI Ho Jy Kg Kr Kz Mk Mw Om Pj Uc) Lu(aK cA cE cK Fw Ii iZ Nd nY oH Oi Va Vc Wh) Vq(cA cE cK Dg eM Ii Jo Nd Nt Ok Rz Ux Vc Wc) Nc(aK aQ cA cB cK Ii Mk Mn Nd pF Rm Ug Vc) Wd(aF bC cS cZ Ez Ho Kg Mm Mv Pj Vj Vu Yg) Tl(aN Dd Ex Fw Gl Il Jd Jm Nx Oi Ru Ul Th) Kz(aN Ex Gp Ki Kl kQ Mh Ml Nd Pa Ul Uy Yh) Uu(hB hC hG iA iH iJ iO kR nW oF oH Pk tF) cQ(Aa eM hB iA iH iO iZ nY oE oF oH oK tF) Ng(aQ bE cZ Ez Gp Kg Mk Mm Om Pj Ue Vj) Rz(aF bJ cO cS De dK Ez Ho Iu Mm Pd Pj) eM(aG bB bZ cG cJ Gp Je Mg Mn Oi Ub Wf) oE(cJ Fw Gp iZ Kk Mf Mn No Qa Ub Vt Yk) Nk(aK aQ Ii Mk Mn Nd pF Rm Ug Ux Vc) Rc(bM bZ Ki Kk Nl Oe Ph Rm Si Xa) Qa(aK aP cL cW Du fR pF Qn Yg Yh) Jm(Cs Fp Jj Kp Mk Mr Og Pa Ug Vt) Ux(aF bJ bW CO Iu Kc Mg Pd Uf) oF(aN Bn Ih Ki Kk Mf No Oe Oz Ub) Nx(cB dA Fp Jq Kp Lv Mk Ou Vj) Ow(fP hC hG iA iH iZ kR nW pF) dK(Hb In Jo Lz Mh Ml Qg Qx Rt) Nl(Hb Je Jr Kc Kl Mb Ph Yl) Ii(Di Ih Ip No Nr Nu Po Un) Wh(Bb De dI Ih Kk Mw Uh Vj) Qz(bW CO Kc Mg Pd Pj Uf) Ru(Kp Mk Mr Ou Pa To Ug Vj) Oi(bF CO Kp pF Pi Ut Xa) Vt(aF aY cX Dp hG Qn Ul Yd) bO(Af Cx Iu Mb Nu Nv Oe Rt) Yg(aX bW cO cS De Kg Mg) Kj(Co De Ho Iu Uc Uf Zq) Va(cB cV Dc Lv Mz Rm Uc) hB(Bn Dd Il Ki Mf Oe Oz) Gl(cB cO Ez Iu Uc Uf) Tn(Gp Ke Ki Kk Ub Uh) Hf(Je Kl Lz Mh Ml Qx) Rt(aK cB Dc Pa Qh Uc) aX(aF bW Co cS Iu Mg) Th(Cs Fp Mk Mr Vj)

Figure 28 Continued

Mf(hC nW oN pF tF) Uh(Nd Ok Pk Vc Wc) aO(bB bZ Kk Lv Mz) Mk(Di Jd Ne Uy) Ih(Ad aK Pa Ug) Zq(b

Qe) Ed(Gc Yd Xa Yf) Ny(Rv Rx Yl Zw) Eq(Mp Mq Mu) No(Fc Gh Wh) Zq(Dg fP Ux) Oa(Du Gc Rv) Vb(Hv Mi Un) Pi(Fc Gh Wh) Rz(Mi Nq) Vj(aX fP) FdPc HobM HpVt HxZw IkVq YhfP WhPe JnYl} Mt{Oy(Fp Hx lH iJ Ip Jn Js Kk Ko Lj Lv Lw Mi Mp Mr Nn Nt Ny oH Om Pb Pe Po Tn Tr Tz Vt) My(Fp Ih Io Ip It Iv Lj Lv Lw Mm Mr Mw Nj Nm Nn Nx Om Pb Po Pz Qb Qc Qe) Et(aV bA bQ bR bS cA cG Ch cK cL CO Ct dA De DG dH dI Iz) Jt(Hr Ik Ip Lj Lv Ng Nj Ns Oe Pb) Ux(bI Hq Hw Hx Il It St Vq Vu) Lw(Fp Ip Js Lj Mr Ns) aX(Eq Vz Wd Yg Yh Yj) Oa(Dr Ry Zw Ye Ti) Ny(Rx We Yg Ye) Eq(Jk Jm Ut) Ik(bS Js Nt) Vb(Hx St Vu) Pb(Ip Mr Ns) Lv(Lj Yd) Jq(Md Wm) Rz(bI Hq) Ld(Uy Wb) Oh(Du Zw) aZ(Yi Yk) DcJo MkPe MpLj HxVw YdOr QcbR WfJn KjKo OfOu} No{oH(aE bB CH cJ cQ Ct dJ Hc Ib Ic Ik Jo Kc Oe Of Oy Ph Qw Uf Up Us) oN(aE aG aH al aL aQ bB bF cE cH dJ hB Ik In Kc Ko oF Us) oE(aE aQ bS cP cQ dJ Et Kc Ko Of Oy Ph Rz Ur Ux Zq Ti) Ik(Cu Cx iO Kc Kj Kk Kn Ko Kp Ld Ou Ph Vt) Ur(cA cQ eC gP Ip nW Oi oK Pi Tv Uc Vt) Et(Ap Bg Ch Dg Dl oK) Jo(Dc iJ iO Kn Ko) Kc(cA eC Iz Ng Oi) hB(aE cQ dJ Hc Wf) Ch(eC iJ iO Ou) Ii(Dc Kn Tv Vt) Oy(iJ iO Ou Uc) nW(bS cH Uo Vt) Iz(Ko Ou Vt) Oi(Kk Ko Ld) Hc(iJ iO) Wh(Hq Nn) Vc(bZ cE) dJ(iH Kk) dR(Us Yk) DcVa TioF NqRz MvWf NgOu IneC KoUu} Ny{Rx(aW aZ bA bZ cQ Cs cT CU cV cZ Dc Ed Fd Fy Hx Ib Ih Iq Iu Jn Kz Lu Lv Mb Mk Mp Mq Ni Nl Nn Nu Oa Oi Or Pa Qe Qv Rj To Tz Uc Ur Vq Yi) Jt(Fp Hr In Jo Lj Lv Ng Nj Ns Oe) aW(Eq Rz Vb We Wh Yg Yj Yl) Nn(Rz Sh Vb Vw Wd We Ye) Lw(Fp Js Lj Lv Mr Ns Nt) Mf(Rt Va Wb We Yj Zw Xa) Nt(Ik Lj Ng Nj Ns) Wh(bZ Cu Ib Mk Rj) Lv(Ih Lj Mr Ns) Mi(Lj Nj Ns Oy) Wf(Ef Jy Mk My) Ye(bJ Mq Mw Nu) Eq(cS Ef Nq) Mp(Hq Lj Oy) Wd(Ib Mb Rj) Ti(Nk Nu) Gc(Rj Uu) We(Cu Mk) Xa(Cx Oe) Ld(Du Th) Vq(Va Wc) Oy(Mr Pe) IbjT SfRj ZqOi OfOu} Lj{Lv(Ih Ip Jn Jq Js Mi Mp Mr Mw Nj Nl Nm Nn Nq Ns Nt Nx Om Oy Pb Pe) Lw(Hr In Ip Iv Jn Js Jt Mi Mm Mp Nj Nl Nn Nq Ns Nx Oy Pa Pb Pe) Mp(Hq In Ip Iv Jn Jq Js Jt Mk Mm Mr Nj Nt Nx Om Oy Pb Pd) Nt(Hx In Ip Jn Jq Jt Mi Ml Mm Na Nj Nn Ns Nx Oe Pb) Mm(Ih In Ip Jn Jq Js Jt Mi Mr Nj Ns Nx Pb Pe Pg) Jt(Ip It Jn Mi Mj Mr Nj Ns Oe Oy Pb) Mi(In Jn Jq Nj Ns Oy) Mr(Hr Jn Pb) Nx(In Ns Pb) Wb(Oh Ou) Jq(Hr Nj) DuOu EtbA NqHu NsOm ZwOn WfUt dJwB tQjT} Ld{Xa(Al aW Ch Cu Du Fw Fy Jm Kd kQ kR Nn Nr Nx Pa Pb Pc Rb Ru St) Uy(dR hG iH iJ iP iZ kQ kS nW nY oK Qc St Tn) Wb(Al aW cB cF Gp Jm Nd Nn Nr Qc St) Ye(Al Cq Fy Jk Jn Ks Mw Pz Qc St Yi) Ru(Dk kQ Mr On Rb Uc Vu) Lp(bR eM Uc Ut Vq Yd) Il(Em Id Ur Yf) Kd(Uw Ux We Yd) kR(Fd Fi Yi Yf) Va(Jm On Uc) eC(Id nN Vt) tF(Fc Gh Ry) kQ(Fd Uz Yi) Ed(dJ Yd) Et(Jo Oi) Fi(hC Ut) Nr(Fc Vc) We(bX Fw) Wf(Tn Ut) Om(Wd Wh) CqZq DrGp EqNn FydJ MxZx YdOn ZwSt JmUw KoOi RxOa UrPi} Jn{Rx(bM bQ cE cL cV Dc dF Dr Fd Fy Gh Js Lv Mp Mq Mr Nc Nl Oa Oh On Or Ou Pi Ri Sj St Tz Uc Ug Un Ur Vq Vz Wf Yl Ye Xa) Wf(bQ bZ cE hB Jy My Nj Nn Nq Ou Tn Ut) Ye(bN Ed Ef Fw Jk Mq Nq Pe Qe Ri Vu) Jt(Fp Hr In Jo Lv Ng Ns Oe) Lv(Ih Lw Mm Mr Ns) Lw(Fp Mr Ns Nt) Mm(Fp Mr Ns) Rj(Du Em nI) Fd(Ug Ur) Nt(Ik Ns) Mp(Hq Oy) Mr(Oy Pb) Va(bS Hb) fP(Vj Zq) FcUg MkPe UxaZ} Et{bA(Af bO CH cI cP cQ Cx De Hq Hu Ii Ik Mg My Ng Oe Oy Pb Qc) Jo(Aa Ad aM As Bb bN cH CP CQ cU Cw Kd Kf Ko Oa Pi Vt) Oi(Ax bN bV cP cT Cx Dc dM Ed Kk Ko) cI(cH cJ Cu dJ Jq Jr Lw Mi Oe Of Qc) Ik(Ax bN Cs Cu Cx Wm) Wm(Jq Ng Nm Qc) Oe(bN Cs cT Dc) Ch(hB Ou pF) Ed(Fc Gh Vc) Ii(Cu Kn Oa) Ur(Pi Tv Vt) Ou(Ng Oy) CsMm CuOf DuOa XafP KlKo} Nn{Eq(aO Bg bQ cE cR Dc Du Ed Ef fR Jk Jr Ky Ml Nd Nq Oh Or Qt Rm Rt Tz Uc Ut Vp Xa) Dr(Ed Oa Or Qz Rm Sh Tz Vb) Jt(Hr Ip Jo Lv Ng Ns Oe Oy) Sh(aE Hb Oi Tz Uc Un) Oy(Fd Kn Mr Pe) aE(Ux Wd Wf Wh) Ns(Lv Mp Nt) Ko(Ch Ik Mg) Vc(cF Hb Tz) Vt(Du Hl Ry) Cu(Rz Vb) Dc(Rt Vb) Ed(Yd Yf) Lv(Ih Mr) Wb(Oh Or) Oa(Du Ti) ChoH LwMr NgXa YjfP StYe WfJr JoKn} Oa{Rx(aG aZ Dc Hx Jk Jr Jy Ks Ky Mv Ni On Ou Pi Rm Uc Ut) Gc(bF Bg bQ bZ cE Du Hq Il Jy Mv Ou Tn) Ti(hB hG Jy Ky Nq Oe Oh Ou Ut) Dr(bF bZ Gp Hq Lv Mv Ou Uc) Ye(Ef Jh Jy Mu Mv Nq Ut) Du(aG bB Cu Cw cY Nq) Cu(Gn Rt Zw) Zx(aG aZ Ur) Wf(Mv Tn Ut) Vj(fP Il nY) Gn(Mi Ou) Rt(On Ou) MgWb HlUc ZqfP tSnW} Jt{Fp(Ii In Ip It Jo Lv Lw Mj Mm Mp Ng Nj Ns Oe Oi Oy Pb) Lv(Hr Ih In Ip It Jo Ng Nj Ns Oe Oy Pb) Hr(Ih Ip Js Mp Mr Nj Ns Pe Po Qb) Nt(Ik In Ip Jo Na Ng Nj Ns) Ip(In Jo Ng Nj Ns Oy Pb) Mp(Hq Mk Ng Oy Pd) Po(Ns Oe Oy Pb) Mr(Ii Jo Oy) In(Ih Qb) It(Js Ng) Jo(Bb Js) Pe(Mk Oy) CtbA} Ed{Xa(Ch Dc Il In Jy Lv Oi On Ou Uc) Ru(Mv Nq Ou Uc Ut Vu Yd) On(Fc Fi Gn Rt Wf Yh Ye) Yi(dR Ha Ii Pc Ug Yl) Uc(Dr Gn Rt Va Ye) Tr(Fi Sh Vc Wf Wh) oE(Vj Wd Wh Yg) Dr(bF Hq Ou) Gn(Cu Rm Vu) Zx(Ba Ez Oh) Ko(In Oi Vt) Dc(Va Wc) Fc(Fy Lv) Gc(bQ tF) Oh(Wb Yd) CuRt LvVa TnWf ZqdR KkdJ RxRm UrVt VcbZ VhhB} Ur{Vt(bN Dc Fy Ir Iu Kn Ko Mr Nr nW oH Ou Pi Qe Rm Tv Uc) Uc(Af Ch cQ Il Ir Kn Ng Oy Pi Qe Tv) Tv(cQ Cx dJ Il Ip Pb Pg) Il(Id Ir Jq Kn nI) cQ(Fy Ir Kn Nr) Dc(Oi Rx) Kn(cC Ou) Rm(Rx Va) Pi(Kk Ko) AfJq ThQe WbOh LpVu} Oh{Wb(aK cM Co Ct dG dH dJ Eq Gl Ic Je Ki Lz Ml Pj Qx Uc Uu Vb Vo Vv Vw Yl) Dr(Jy Kk Qy Rx Ut) Du(Gz Jh Mu Mw) Eq(Ef Mu Nq) Yh(Cu Jh Mu) Ko(Ik Jo Oi) Rx(bS Pc) NqRz XaPc JyVc KkdJ} Ko{Jo(bA Cu Fy Js Kd Kn Mr Nr Oi Ou Pe Pi Vt) Vt(bN eC Ik Il Iz nW Oi Uu Vo) Kj(Dc Il Kn Ou Pi Uc) Oi(bN Kc Kk Ou Qe Ri) jT(uP vU wL) In(Fy Sr) Ou(Ch Oy) Uu(Pi Sr)} Ns{Mp(Hv Ih Io Ip Ir It Iv Lv Lw Mr Mw Nj Nl Nm Nr Nu Nx Om Pe Po Qb Qc Qe) Nt(Hx Ih Ik Ip Jq Js Lv Lw Mm Nd Nj) Fp(Lw Mm Nx) Js(Lv Lw Mm) ThOn LvIh} On{Wf(bM Bo Fw Gl Ih Ki Uv Zw) Eq(aW Mi Mp Mu Qy) Zw(Ih Of Qe Rj) Uu(Fc Fi Zx Tm) Va(aZ Ch cQ Dc) Ii(Id Vt) Yh(Mp Of) We(aY Uv) Kd(Rt Vh) Ug(Lp Ru) jO(Ng Oy) ThUk YkaZ WhKi OeVb} Pe{Wf(Bg dR In Mv Nq oH Tn Ut) Du(hB hC iA Nd oE) Oy(Lw Mm Mp Om) Hr(Ip Jq Lw) Wh(bQ cE Om) Mk(Lw Mm) Nd(Gh Vz) Yl(cF kQ) Vc(bM Ha) DcVa ThoE NqUx IlVz IpPb XaOi YedR} Js{Lw(Fp Hr In Ip Lv Mr Ms Nj Nt Oy Pb) Nt(Ik In Jo Nj) Lv(Ik Mm Nj Oy) Mm(Fp In Oy) Yh(Cu Mv Vu) Wb(aW Il Rx) Mp(Hq Oy) Rx(Jk St) EqNq QyYe} Va{Rm(aG bM Bo bS dI Dr Hb It Qv Ri Rx Vq Vt Wf) Dc(Mq Ql Qm Sr) St(aZ Mp Ou Uc) Qe(bM cE) EqUc TzVq IhaZ SihB} Nt{Ip(Ih Ik In Jo Jq Lw Nj Oy Pb) Ik(Fp Ih Jq Lv Mw Nj Po) Ih(In Lv Lw Nj Oe) Lw(Fp Pb) Mp(Hq Oy) NjJq} Mr{Lw(Fp Hr Ip Lv My Oy Pb) Lv(Hr Ih Mm Oy Pb) Oy(Ip Mm Mp Om) Ru(aZ Ky Ou) Mm(Fp My) Hr(Ip Jq) MkMp IpPb WfUt} Fp{Mm(Ih Ik Jq Lv Lw Oy Pb) Lw(Hr Ih Ip Lv Pb) Mp(Hq Jq Oy Pd) Nx(Oy Pb) LvIh HrJq OmOy} Ut{Wf(bL Ch De Dr Ih Ki Uu Uv) Ch(Dr Hp Rx Xa) Dr(cQ Ir Nx) We(Ir St) Uu(Sh Vc) IhYe YhoE} nW{Vt(cH sO tO tS uT vB vH vP vV yL tM xA) wB(Fn iA Lv rS) Id(wD wP) ChZq KdVj VuqZ} Yi{hB(Af aN aY bM Bn Ct fP Pb Us) aZ(aW bJ Co gL Mm Mw Qy) BoiZ MuaX QebM QyUu} Kn{Jo(dJ Il jH jT Uc) dJ(hO iB jI qB) iB(cQ Lz Vt) Ky(jO jT) Ou(Of Oy) NqOy HwhX jToK} Mq{Il(Eq Ux Vb Vz We Yj Xa) Ye(Cq Dc Jk Ks Rm St) Dc(Rx Wb Wc Yk) YjJm} Xa{Nq(Ch Ng) Qe(aZ bM) Sr(fP gP) Oi(Fw Pi) Vq(hC iH) NudC NgOm NiaZ TzRx HxIl ZqfP OraW} Dr{Ou(Gp Il Jm Pa Ru) Tz(aW Il) Om(Wd Wh) IlOr JrRu KyaW RxRm} Id{jT(sO tS uP uR vI vP vV yD zI tM) RirS PhwP dJvA} Zq{Ch(dR hB hC hG iO oE oF oH oN) YddR aXgL} Ru{Ni(aZ Jr Tz) aZ(Mu Nq) TzJy WbOu KjVu OmOy UnhB} dJ{Kk(Il Qe rS Sr Tz) Kp(uR wG) LuwB NgvI TvIn} hB{Eq(Kd Om) Si(Ch Kd) Vq(Vb Yh) EmnU MvUy bNcH} Ih{Lv(In Ip Lw Mm Nj Oy) CuVb WfOu} Ye{Mw(bW cT Hx Nd Pa Qb) Qy(Qe Rm)} Oy{Uc(Kk Pa Us) Om(Mi Mp Yd) NqTv} Cu{Rt(Jk Pa) Vb(Cx Qy) BbJo StWe} Rx{St(bA Jr oF) Rm(aE Ni Vz)} Eq{Nq(bA Jk Nd) MvSt JkbZ} Wb{Pa(Mk Nq) aW(Mj Or) MhUc} Jq{Hr(Ip Po) WmLv MpPd cQjT} Vt{bN(Dp Kk) cHoH iPvS yKjT} Qe{DuUg YdcE ZwbQ KkOi} Ri{wD(cW Lu) qCvB} Om{Uu(Gc Vc) WcaZ} cQ{qZ(iO Oe) FyIn} Bo{Tn(Vc Wf)} Uc{Of(In Us)} Il{Kf(Jo Kj)} Qv{DuRm GcSt} aW{IvrS YdJr} jF{NlnU TowD} AaHuuY DcKyRt NqShPa MpHqIp NiSfaZ TrIzuI JoVqnC RmUuUw aMbAgV

Constrained panels with 2 analytes, where 1.0E-8 >= 'model p-value' > 0. Contains 368 panels of 191,187 total panels evaluated. : Et(aA Aj Fp Hu Ih Ij Im Ip Is It Ji Jj Jl Jn Jo Jp Jq Js Jt Lh Li Lj Lv Lw Lx Mi Mn Mp Mr My Mz Ng Nj Nl No Ns Nw Oe Of Og Ok On Oy Oz Pb Pe Qa Qb Qc Qd) Ok(aA Fp Fr Hr Ih Ij Im Ip Is It Jg Ji Jj Jl Jn Jo Jp Js Lh Li Lj Lv Lw Lx Ma Mn Mp Ms Mt Mz Ng Nj Nl Nn No Ns Nv Nw Ny Oe Of Og On Oy Oz Pb Qa Qd Qe) Jp(aA Fp Ih Ij Im Ip Is It Ji Jj Jl Jn Jq Js Jt Lh Li Lj Lv Lw Lx Ma Mi Mn Mp Mr Mz Ng Nj Nn No Ns Nt Nv Oe

Figure 28 Continued

Og On Oy Oz Pb Pe Qa Qd) Im(aA Aj Fp Hu In Ji Jj Jl Jq Jt Lh Li Lj Lu Lv Lw Lx Ma Mi Mn Mp Mr Mz Ng Nj Nn No Ns Nt Nv Nw Oe Og On Oy Oz Pb Pe Qd Ye) On(aA Aj Fp Hu Ii Ik Ip It Ji Jj Jk Jo Li Lj Lw Ms My Mz Ng Nj No Ns Oe Of Og Oi Oy Oz Pb Qd) Ji(aA Aj Hr Ii Ik In Jg Jj Jl Jo Jq Li Lj Ma Md Ms My Mz No Ns Nw Og Om Oy Oz Pb Wm) aA(Fr Ij Ip Is Jg Jl Jn Js Jt Lh Li Lj Lv Lx Ma Mn Mz Nj No Nv Nw Nx Ny Qd) No(Aj Ip Is It Jg Jj Jl Jn Jt Li Lv Lw Mp Mz Nj Ns Oe Og Oy Oz Pb Qd) Nw(Aj Fp Hu Hx It Jj Lj Lw Ms My Ng Nj Nl Ns Oe Og Oy Oz Pb) Jj(Fr Ij Is Jg Jl Js Jt Lh Li Lx Ma Mn Nt Nv Qa Qd) Qd(Aj Ik Jg Jl Lh Li Lw Ma Mn Mz Og Oz) Vi(cQ Ld Lj Mf Ow Oz Uu Wf) Is(Aj Li Og Uh Va Wb We) Og(Ij Jg Jl Lh Li Nv) Li(Jl Lv Lw Mz) Nv(Lj Ns Oe Oy) Aj(Jt Kq) Qa(Uh Ye) Ps(Oi Oz) LxOy

Constrained panels with 2 analytes, where 1.0E-7 >= 'model p-value' > 1.0E-8. Contains 315 panels of 191,187 total panels evaluated. : Vi(Aj aW aZ Bg Ed Fn Gc Hc Im Is Je Ji Js Kz Li Lu Mp Mq Nb Ng Oa Of Oh Oi Pf Qa Qb Qc Qd Qe Rc Rj Sh Ss Ur Vb Vt Vw We Wh) Is(Fr Iv Jg Jl Jt Lh Lj Lv Lw Lx Ma Mn Mz Nj Ns Nt Nv Oe Oy Oz Qd Rt Rx Ur Vb Wh Yh Yk Zw Ye) Li(Hr Hu Ih Ij Ik In Ip It Jg Jn Jq Js Jt Lh Lx Ma Mi Mn Mp Mr Nj Ns Nt Nv Oy Oz Pb Qa) Qd(bA Fp Fr Ij Ip Jn Jt Lv Lx Mi Mm Mp Mr Nj Nn Ns Nt Nv Nx Oe Oy Pb Uh Wm) Jg(Aj Fp Ih Ij Jl Jq Js Lh Lj Lv Lw Lx Mi Mp Mr My Mz Ng Ns Nv Oe Oy Qa) aA(Fp Ih Io It Lw Mm Mp Mt Mw Nm Nn Nr Ns Nt Og Om Oz Po Qa Qb Qe) Nv(Fp Hu Ih Ij Ip It Jl Jn Jt Lv Lw Mn My Mz Ng Nj Oz Pb Qa) Lh(Hr Ih Ij Jl Jn Jt Lj Lw Lx Ma Mn Mz Ns Oy Oz Pb Qa) Jj(Aa Dc Ip Jn Ke Ko Kq Mz Nn Nx Ny Po Qe Uh) Nw(Aa Af bA bN cH cI cJ Cx dJ Ed Ri Uh) Jl(Hr Ij Jn Jt Lj Lw Lx Ma Mn Mz Oz) Og(Fr Js Jt Lx Ma Mn Mz Nt Om Qa) Aj(Ad Dc Ij Jp Ke Ko Mn Ok Qa) Uh(hB Id Ji Kn Ld Mz Tv Uc Vt) Jp(Ld Nl Nm Nr Ny Po Qb) Mz(Fr jL Jt Lx Ma Qa) Qa(Du Ma Mn Rx Wf) Kq(Rz Ux Wd Wf Wh) Ps(Ed Pf Rx Uu Va) Fr(Ij Js Jt Oz) Ji(bA cI cT jO) Lx(Ij Jt Oz) Lj(Ij Jt Ma) Wb(Oh Ow) FpJt MaIh IjOy IkKe Constrained panels with 2 analytes, where 1.0E-6 >= 'model p-value' > 1.0E-7. Contains 739 panels of 191,187 total panels evaluated. : Uh(aA Ad Aj As bA Ch Cp Cq Cs Cu Cw Dc Dd dM Ed eF Fy Hv Hw iB Ij Ik Im In Ir It Iv iZ Jl Jn Jp Jq Jr Js Jt Kd Ke Kf Kk Ko Kp Kq Kr Lh Li Lj Lv Lw Mj Ml Mr Ms Mt Na Nb Nf Ng No Nr Nx Ny Oa Oe Oh Oi Om Pb Pe Pi Pk Ps Qe Ra Ri Rj Sr Un Up Ur Us Uu Vp Wm) Is(Aa aQ bA Bb bR cH cI cJ cP Ct dJ Fp Ij In Ip Kc Ke Kk Ko Ld Mi Mm Mp Mr Ms Mt Nm Nn Ny Pb Pe Qa Ug Uk Us Vt Wm) Vi(Ch Ct cU Eq Hv Ib Ir Iz Jn Kd Kp Lz Mk Ml Mx My Nc Nf Nk Nn Nw oE Or Oy Pb Pc Pk Qx Rx Sr Tz Vs Yg Tl) Fr(Aj Fp Hu Ih Ip It Iv Jg Jl Jn Jq Lh Lj Lv Lw Lx Ma Mi Mn Mp Mr Ng Nj Nl Ns Nt Nx Ny Oe Oy Pb Pe Qa) Ma(Aj Fp Hv Ij Ip It Iv Jn Jq Js Jt Lv Lw Lx Mi Mn Mr Mt Ng Nj Nl Ns Nt Nv Oy Oz Pb Pe Po Qb Qe) Mz(Fp hB Hr Ih Ij Ip jF jK Jn jO Jq Js jU Lj Lv Lw Mi Mm Mn Mp Mr Mt Nj Nl Nn Nt Ny Po rB Tv) Lx(Gh Hq Hu Ih Ip It Jn Jq Js Lj Lv Lw Mi Mn Mp Mr My Nj Nl Nn Ns Nt Nv Ny Oe Pb Pe Qa Vc) Ij(Fp Hu Ik In Ip Jn Jq Js Jt Lv Lw Mi Mm Mn Mp Mr Mt My Nj Nn Ns Nt Oe Oz Pb Qa Vb Vc Th) Qa(Fp Hr Ip Jl Jn Jq Jt Kk Ko Lj Lv Lw Mm Mp Mr Nj Nn Ns Nt Nx Ny Oe Oy Oz Pb Ur Yh) Ke(Af CH cQ dJ eC Ii Il In Iz Jl Jo Jp Kj Kk Ko Ld Ms Ng oE Oh Oi Ou Ow Oy Oz Pb) Lh(Fp Hu Hx Ii Ip It Iv Jo Jq Js Lv Md Mi Mm Mp Mr Ms Mt My Ng Nj Nl Nn Nt Nv Ny Oe) Jj(aA Bb Cu Fp Ih Ii It Jk Jm Jq Kf Kn Lj Lv Mm Mt Mw Nm Nr Om Ou Ow Pz Qb Uc Vt) Jl(Fp Ih Io Ip It Iv Jq Js Lv Mi Mm Mt Mw Nj Nm Nn Ns Nt Ny Oe Oy Pb Rx Ur Wf) Ji(Aa Af bF bN cH dJ Ed hB jE jF jP jQ Kj Kk Ld lN oF Ri Ug Ur Us Uu Uv Vo) Jg(Hu Hv Hx Ik Ip It Jn Jt Mn Mx Nj Nl Nn Nt Of Oi Oz Pb Pe Po Qb Qc Qe) Mn(Fp Ih Ip Jn Jq Js Jt Lj Lv Lw Mi Mr Mt Nl Ns Nt Ny Oz Pe Po) Nw(Fy Ic Iz jO jP Jv Kk Ko Ou Ow Ru Rx Sr Tv Us Uu Vo Vt Wc) Kq(Ch Dr Eq Ik Iz Jo Kj Ng Of Oy Ps Ru Sh Uw Vb Vc Vw Yd) aA(Hx Ii Ir Iv Jm Jq Mg Mi Mr Nl Nu Pb Pe Pg Pz Qc) Nt(Ih Ik Ip Jn Jq Js Jt Lj Lv Lw Nj Ns Nv Ny Oz) Jp(Aa Ch Cs Hc Id Iz Kc Kj Kk Kn Ko Ow Vt Wm) Jt(Hr Ih Ip Jn Js Lv Mp Mt Nj Nn Ns Ny Oz Po) Og(Aa Ih Ip Jn Jq Lw Mr Mt Nn Nx Ny Po Qe) Qd(Aa aQ Bb cH cI cT De dJ Kk Ko Ru Th) Ps(cU Il Nn Nu Ow Qv Us Vo Vs Wc Wh Ye) Aj(Ba Cu Fy Kn Mt Nv Om Qe Uc) Lj(Jq Js Lv Lw Mi Mm Mp Mr Nx) Js(Ip Lv Lw Mm Mp Nj Oz) Nv(In Jo Jq Mi Mp Mr Of) No(Kc oE oH oN Ur Vt) Nb(Rx Vj Zq Tm Tl Ti) Jn(Lv Lw Mi Mm Mr Rx) Mt(bR bS Lw My Oz) Ur(Dc Qe Tv Uc Vt) Et(bA cI Cs Cu) Lv(Ih Mm Nn Ny) Im(Aa Eq Fd Yl) Fp(Jq Lw Mm) Ny(Lw Mi Rx) Oa(Rx Zx Ti) Ow(Dr Em Va) Pf(Fd Vc Wb) Nn(Eq Sh) Wf(On Ut) Li(Iv Nl) AaOz WmJq NsMp LwMr XaLd KniB KoVt RmVa Constrained panels with 2 analytes, where 1.0E-5 >= 'model p-value' > 1.0E-6. Contains 1,032 panels of 191,187 total panels evaluated. : Ps(aM Ar aW aZ bB bQ bR Cu Fw Fy Gp hB In Jr Jy Kk Li Lj Lv Lx Lz Me Mh Mk Ml Mq Mr Mt Mz Ni Nk Nq Nr Oa OE Oh Or Ou Pb Pc Pe Qx Qy Ri Rj Ru Sr Yk) Mt(Aa aV bA bQ bU cA cG cK cL CO Ct dA dH dI Eq Fp Ih Ik Ip It Jn Jq Js Ko Lj Lv Lx Mi Mm Mp Mr Nj Nn Ns Nt Nx Ny Oe Oy Ox Qa Vx Vt Wm) Jj(Ad Al Ao Ax BA Co Cs cT Cw Dd Dg Ed Fy Io Ir Iv Jo Kd Kk Kp Ks Ky Ld Lw Mi Mp Mr Nj Nl Nu Oa Oh Pe Pg Pi Pj Qc Qh Ri Rm Sr Tv Uf Un Vq) Mz(Aa Aj bA cH cJ eZ hO hP Hv Hx Io It Iv Jo Jr Md Ml Ms Mw My Nm Nr Ns Nu Nx Oh Om Oy Oz Pb Pc Pe Pg Pz Qb Qe Ru rW Rx Wf Xa Wm) Et(Aa bN bV CH cP cT Cx Dc Dl Ed Fy hB Id IZ Kd Kj Kk Kl Kn Ko Kq Ld Oa Tv Ug Uh Ur Uu Vo Vt) Mn(Aa bA Cu Hv Hw In Ir It Iv Jr Lu Mm Mp Ms Mx Ne Nh Nj Nm Nn Nr Nu Nx Oh Om Oy Pb Qb Qc Qe Vt) Vt(Aj bF bN Dp eC Ed Fy Gp Il Im In Jl Ke Kk Kn Kq Ld Ma Mh OH Ow Qa Qd Qe Ri Tv Ug) Ko(Ch Ed Ik Il Im In Ji Jl Jo Kc Kj Kk Kn Kq Ld Ng No Oh Oi Or Ou Ow Qb rS Tz Uu Vo) Uh(aM aW BN cA cH cQ cT dJ dK Fw Hx Ic Il jI Kc Mh Ni Nm Ok Or Ou Ow Rm Ud Vs tF) Nn(Fd Fp Ih Ip Iv Jn Jq Js Lj Lw Ma Mi Mp Mr Nj Ns Nt Nx Ny Oz Pe Po Vc Wb Xa) No(Aa aQ bA bS CH cJ Ct dJ eC Ic Iz Kj Kk Kn Kq Ld Ou Ow Ph Tz Ug Uu Vc Vo) Is(Dp Dr Ed Gd hB Ic Id Iz jF jK jQ jR jT Kj Kn Kq Ky Ow Ri Rj Sr Up Uv Vo Vs) Qd(bF cI dF Dr hB Kc Kj Kn Kp Ld oE oH Ou Ow Ri Rx Sr Tv Ua Ur Us Va Yi Ye) Lj(Ih Ip Iv Jn Jo Kq Mg Mw Nb Nj Nl Nm Nq Ns Ny Og Om Ou Ow Oz Pc Pe Pg Po) Lv(Aa Fp Io Ip It Iv Jq Lw Mi Mp Mr Mw Nj Nl Nr Og Om Oz Pe Po Qb Qc Qe) Im(aI aN aQ bA bF bS CH cI cJ CT Cu Dc dD dF dJ Dr Gd Ke Kk Ld pH) Jp(Ar bA cH cI cJ CT Cu Dc Dp Ed Kq Kx Oa Qw Ri Sr Ss Tv Tz Ur Uu Vs) Nt(Fp Hx In Ir It Ly Mi Mm Mp Mr Mw Na Ng Nx Oe Om Oy Pb Po Qb Qc Qe) Aj(Ap bA Bb Co dF Dg Ih Jl Jq Js Kf Lh Li Nx Ou Ow Qc Sr Uf Un) Ny(Fp Ib Ih Ij Ip Iv Jn Jq Js Ma Mm Mp Mr Nj Ns Nx Oz Pe Vj Xa) Aa(Hr In It Jl Jn Jo Js Lu Lx Ma Mk Nl On Oy Pb Qa Qb Qc Qe) Pe(Fc Gh Ih Ij Ip Jn Js Jt Lw Mm Og Oz Qa Sj Vc Vz Wh Yl Xa) Mi(Fp Ih Ip It Iv Jq Js Jt Lw Mm Mw Nj Ns Og Oz Po Qa Qe) Kq(De Ed Ef Gd Ii In Kk Kl Ld Oi Om Ss Tn Tv Ur Uu Uv Vo) Ij(Fi Gh Hr Ih It Iv Kc Kk Ms Ng Nl Nx Pc Po Ur Wb Wh) Ke(bR cA cI dK Ed Fy Kc qA Ri rS Ur Us Uu Uv Vo yD Wm) Qe(bA Jl Jn Jq Jt Kk Lw Mm Mp Mr Nx Oz Rx Us Vj Xa) Jl(Hu Kc Kk Ld Mp Mr Nl Nu Om Po Qb Qc Vj Wm Ti) Jt(bA In It Iv Jo Lw Mm Mr Ms Mw Ng Oe Oy Pb Qb) Xa(Cu Ed Hx Il Js Lx Oa Oh Oi On Or Oz Pf Rm St) Ih(Fp In Ip Jn Jq Lw Mm Mp Mr Nj Nx Om Oz Po) Kn(dJ Dp eC Ed hX Ik In Jo jT oE Ou Qa Tz Ur) Jn(Fp Ip Iv Jq Js Mp Mw Nj Ns Nx Oz Po Ye) Ur(Cu Fy Il Ir Jq Lh Mr Nr Oa Ou Pi Rm Un) Qa(bA Bb In Js Kc Ld Nm oH Om Ow Ug Us) Og(Dc Fp Ir Iv Jk Mm Mp Mw Nm Nr Pz Qb) On(Ch Ct Eq Iz Rt Rx Va We Wh Yd Yh Wm) Ip(Fp Iv Jq Lw Mm Mp Mr Mw Nj Oz Po) Js(Fp In Mr Ms Nm Ns Oe Oy Pb Rx Wb) Ji(eC Fy Ic IZ Jv Kc oE Ow Ph) Jq(Iv Mm Mp Mr Mw Nj Nu Oz Po) Fp(Io Mp Mr Nj Nm Nx Om Oz) Lx(bR bS Fc Iv Mh Mm Wb Wh) Ma(Hu Ir Jr Mp Mx Nx Oe Qc) Kk(dJ Ed Il Oh Oi Qc Sr Tz) Pf(Dr Gd Ho Hp Sh Ux Vz Yi) Po(Lw Mr Nj Ns Oy Oz Pb) Ld(Ed Em Fy Sr Uw Wb Yi) bA(cH Dc Li Oz Pb Qb Qc) Dr(Oa Or Ou Tz Uc Ut) Ed(Ru Uw Yd Yi Ti) Vi(eM hB nT nU oF) Fr(Hv My Qb Qc) Lw(Iv Mx Nr Qb) Yi(aZ Nw Ow Oz) Lh(Io Mk Ml Mw) Oa(Gc Vj Yd Yj) Om(Ns Oy Oz Wh) Cu(Ik Rt Vb) Dc(Jo Oe Va) Fy(cQ dJ In) Mp(Hq Nj Oz) Mr(Mm Oz Ru) Uc(Of Oy Va) Nw(iJ oE oN) Id(Il Ow) Jr(Ru Rx) Oh(Ho Ti) Ou(Oy Ru) Ut(Eq Sh) lN(kC kO) WmOk FdNq NsNx MmQb MwYe NbHl TnWf IlVj StVa RxRm LirS OwOy cHhB cQqZ wBnW

Figure 28 Continued

Constrained panels with 2 analytes, where 1.0E-4 >= 'model p-value' > 1.0E-5. Contains 1,910 panels of 191,187 total panels evaluated. : Ko(aA aM bA bB bF bN cA cH cQ CU Dc dD dF dK dM Fw Fy hB hO Hv iB Id iH Ir Iz Jq Jr Jv Kd Kl Kx Ky Li Lj Lv Lw Lx Mh Mj Ml Mr Ms Mu Mz Ne Nh Nj Nn Nr Oa OE oF Ph Pi Qe qZ rB Ri Sr Ss Tv Ug Un UR Us Vp wD wP) Kk(Aj aQ Ar bA cH cQ Cs Cu Dc eC Em Fw Fy Gp Hb Hv iB Id Ik In Iq Ir Iu Iv Jn Jq Jr Js Jt Kd Kf Kn Ky Lh Li Lj Lv Ly Ma Mh Mj Ml Mn Mr Mt Mu Mx Mz Na Nc Nh Nn Nr Oa On Or Ou Ow Oz Pi Pj Qb Qh Ri Tv Uc Un Ur Vq Wb) Jj(aH Ap aQ Ar bB Bc bF Bg bQ cE cG cH cJ Cp Cq Cx dF dJ Dl Em Ez Fa Fb Fw HB Hv Hw Hx Id Il Iq Iu Jd jF Jh Jr Ju Kc Kg Kr Kx Mg Mj Mv Mx Nb Ng Nh Nq Og Or Oz Pa Pc Pf Ql Rf St Tn Tz Ua Up Ur Ut Vp Xa Wm) Xa(aM aW aZ cQ cU Dc Dr Et Fw hB Hv Ih In Ir Iv Jh Ji Jp Jr Jy Kd Ke Lh Li Lj Lv Lz Mf Mi Mj Mk Ml Mp Mq Mr Mx Ni No Nq Nr Nu Nv oE Og Ou Pa Pb Pc Pg Pi Qb Qc Qh Ql Qx Rj Ru Rx Sh Sr Tz Uc Un Ut Vq Vt Vu) Kq(aC Ad Af aQ bA Bg bL bR bS cA cH cl cQ Cs Ct dJ Dp HB Hc Hq Ib Ic Id Im Jd Jh Jk Kc Kn Ky Md Mg Mh Mm Mn Mw My Nj Oa OE Og OH Ow Pb Ph Qa Qb Qc Qe Qu rB Ri Sr Tz Ua Ug Uk Us) Ld(Aj bA bB bR cH Cu Dc dF dJ Dr Fd Fw hB Ho iB Id Ij Il Jd Jn Jq Jr Js Kf Kn Lh Mn Mr Mz Oa Oh Ok On Ou Pi Ps Qc Qe Qh Ri Ru Tv Tz Uc Uf Un Ur Vh Vq We Yg Zq Ye Th) Vt(aQ bA bB bR cE cH cJ cQ Cs cT Cu Cx dF dJ dK DR hB iB Id Ij Ik Jq Ju Kc Kf Ky Li Lj Lv Mr Mz Nj Nr nW oE Og On Ou Pi Qc Qg Sr Tn Tz Uc Yi) Tv(Aj aW cH cQ Cx dJ Dp eC Ed Fy Gp Hb Ij Il Im In Ip Jo Jq Li Lv Ml Mt oE Oh Oi On Ou Ow Oy Pb Pe Pg Qb Qc Qe Rf Ri Sr St Tz Un Us Ut Wm) Qe(aQ Bb bF bN cJ CT Cu dF dJ Dr Fp hB Ih iJ Ip Iv jF jQ Kc Lj Mt Mw Nj Nl Nm Nn Ns Nu Ny Oc oH Om Ou Ow Oy Pb Pc Pe Po Ri Ug Vs) Id(Aj aQ cH cJ cQ Cx dD dJ eC Ed Gp Hb Ij Ik Im In jH Jl jT Kc Li Lv Mn Mt Nh Nn oE Og OH Oi On Ou Pi Qa qC Qd Ri Sr Tz Ur wP) Kn(aQ aW bB bF bR cA cE cH cQ dK dR hB Ic Il Im Jl Kc Kj Ky Li Lv Ml Mn Nn Oh Oi Or Ow Oy Oz Pb Ph Qb Qc rB Sr Uc Ug Us Vo Wm) Fy(aQ aW CH Ct Dp Dr Ed Em Hb Ic Ik Im Jo Jp Kc Kj Lj Lu Ng Oa OE oH Oi Ow Oy Ph Qc Qd rB Ri Rt Rx Sr Tz Us Vj Vs Wb) Mt(aH aQ aY Bb bN cF cH cJ Cu Cx Dc dG dJ Dp Ed HB Hu Hv Hx iB Ir Iv jF Kc Ky Ng Nl Nm oE Om Ow pF Qc Qw Sr Tz Uk Ur Yi) bA(Ad aM Ar Ax Bb bO cJ cQ Cs Ct Cx Dd Fr Hq Ih Ij Ik In Jl Jq Js Kc Lj Lv Lw Mi Ml Mm Mu Nj Nn Ns Oe Og Oi Ok On Oy Ur) Jq(Af Ax cI Cx Ed hB Hr Io Ir It jF jH jO jT Kc Lw Nl Nm Nr Ns Ow Oy Pa Pb Pe Pg Pz Qb Qc Ri Rj Sr Ug Uk Us) Ur(Cq cT Dd Ed Fw Hv Ih Im Ip Iq It Iu Iv Jn Jr Js Jt Kd Kf Li Lj Lv Mj Mz Nx Ok On Or Ow Pe Qh Sr Tz Up Vq) Aj(Ax Bc Bg cG Cw Dd Dl Ef Ez hB Ip It Jk Kc Kd Kg Kp Lj Lv Lw Lx Mi Mm Mr Nn Nq Nr Ny Oa Po Pz Qb Tn Vq) Om(Eq Gd Hu Ip Ir It Iv Jn Lw Mi Mm Mp Mr Ms Mw My Ng Nj Nl Nu Oe Pb Pe Po Qb Qc Sh Ux Va Vb Vc Wb Wd Wf) Ow(cH Cs Cu Dc Ed cP Et Fw Gz hB Ik Im In Jl Kc Kd Kf kO Li mF Mk Mr Mz Ng nU Oa Oe Of Oh Oi Sr Un) Dc(aA aQ Ar Ax bF cH cI cJ CT dF Di dJ Ik In Kc Kj Li Lw Mn Oi Ok Ou Qc Rt Rx Sr Ug Us Vj) Mr(Hr Hx In Io Ir It Iv Kc Md Mh Mi Mk Mp Mw My Nj Nm Nr Ns Nu Nx Oh Oy Pb Pc Pz Qb Qc Sr Wm) Mz(aH aQ Ax bB bF bN bR cI Cx dF dJ Dr Ed Kc Mx Nb Ou Pa Pf Qc qZ rS Rt uT Va vI wB yH Yk yL) Yi(aW Bo cU Fw hB Hv Ji Jo Li Mj Ml Mp Mq Nn Nq Nv Ny Oh Or Ou Pc Qb Rh Rt Rx St Tz Va Yh) Dr(Co dR Ed Fw hB Jl Ke Ky Li Lv Mn Mp Mq Nn Nq Nw oF Oh Oz Ps Qa Qh Rm Sr St Tn Uh Vj) Sr(aQ CH Cu dD dJ Ed Et Ik In Jl Kc Li Lj Lv Ng Oc oH Oi Ou Ph Pi Qa Ri Tz Ug Va) Nx(Ed Hr Hu In Ip Ir It Iv jF Lv Lw Mi Mm Mp Mw My Nj Nl Nu Oe Oy Oz Pb Pe Po Qb Qc) Cu(Ar dH Hq Ij In Jo Kc Li Lj Lv Mk Na Ns Of Og Oi Ok On Oy Oz Pb Qb Qc Vw Wc) Lw(Ar Ax Cs Hv Hx Io Ir It Mj Mm Mp Mw Nb Nj Nl Nm Ns Nu Oy Oz Pa Pb Pg Pz Qc) Ou(bS cA CH Cs Ct Em Et Fd Hq Ik Im In Iz Kc Kd Lp Mk Ng Of Oh Oi Qw Va Wb) Ip(Hv Hw Hx Io Ir It Jr Lz Mx Nb Nl Nm Nq Nr Ns Nu Oh Oy Pa Pb Pc Pg Qb Qc) Qa(aQ bF bN bR bS cE cH cI cJ cP CT dF dJ eC HB Ib Ic Kj Kp Ri Vs) Kc(cH Cs dJ Ed Et iB Il Im Jn Jr Js Kd Lj Lv Ml Mn Nr Oh On Or Qc Tz Uc) Mm(Hv Hw Hx Ir It Iv Jr Mj Mp Mw Mx Nj Nl Nn Nr Ns Oz Pb Pf Pg Po Qc) Pe(Fp Gd Hr Io Ir It Iv Mk Mp Mw Nj Nm Nr Ns Nu Oy Pb Po Pz Qb Qc) Ed(dK Gc Ij In Jl Lh Lv Mn On Ql Ri Tn Uc Un Vj Wh Yg Zq Zw Zx) hB(aE aQ aW bN Ch cP cQ dJ eC Fd fP Im jO Jp Lj oH oN Ri Si) Mp(Hv Io Ir It Iv Mk Mw Nl Nm Nr Nu Oy Pb Pd Po Pz Qb Qc) Fp(Ik Ir It Iv Jo Mw Nl Ns Nu Oh Pb Pc Pg Po Pz Qb Qc) Wb(Et Ji Ke Lh Li Lv Mj Ml Mq Mx Nq Nr oE Or Rm Tr Uc) Ny(Hv iB In It jF Mw Mx Nl Nm Nr Oe Oy Pb Pc Po Qb Qc) Og(Hx Ii Il Io It Jo Mg Mj Mx Nb Nj Nl Nu Oz Pa Pg Qc) Lx(aV bQ cA cK CO dA dH dI Gc kP lX mF nC nK oN) Lj(bF In Io It Jh Nh Nu Oh Pa Pb Pz Ri rS Uc Uw wB) Nn(Gd Hu Hv Ir It Ms Mx Nl Nm Oe Oy Pb Qb Qc Uz) Ih(Io Iv Jo Mw Nm Ns Nu Oe Oy Pb Pc Pg Rx Va Ye) Un(cQ dK eC Et iB Ik Il In jT Ms oH Oi Ri Ug Va) Im(iP Iz Kd Kj Kp Ky nK oF oH Ph Ri Ug Uu Vo) On(Af Ao aQ bS cH cI cJ De iB jO Kj lN rB Uu) Jn(Gd In Ms Nl Nm Nr Nu Oc Pa Pb Pc Pg Vq) Et(Ef Ic oF Or Ph Pi Ri Rm rS Ss Tz wD) Fd(aW bZ Cx Il Jy Li Lz Ml Mq Oz Qx St) Lv(Bb Hx Ir Nm Ns Nu Oh Oy Pa Pb Pz Wm) Mi(In Io Ir Nl Nm Nr Nu Oy Pb Pz Qb Qc) Mn(aJ Ar Ax aZ bN CH cI Cs CT dF) Uc(Ch Ct Gd In Jo Kj Ng Oi Rx Ug Us Uu) Kf(eC hX iB Ik Il In Jo Kj Oi Oy rB Tz) Jl(Bb Dp Gc Gp Hb Kp Kx Ky Pj Ri Us) Ru(aZ Fw Hv Ji Ke Mj Or Pg St Tz Vu) Vj(Fw Jm Jr Js Kd Mj Pa Pi Qh Rm St) Po(Hr Hu In Io It Iv Nl Nm Oe Qc) Ij(Aa CH cI Ct dJ Gd Kj Ug Vo) Is(eC Em iB jO kP nC nH nK nL rB) Oz(cT Ho Ir Iv Lp Mw Nr Pg Qb Uw) pH(aW aY Cx nI nK nN Nr oW Pa Pf) No(Fc Gh iB jF jK jO jQ Ri Ss) Qd(iB Ic Iz jF jK jQ jR jT) Ji(eZ rB rS rX wB wD Yd yL) Li(Bb cT dF Gd iB jF Ri Tz) Jr(jF jH jK jQ jR jT rB) Ri(hW iB qC rB rN rS wD) Nw(Em qC rB rS rZ wB wD) Ok(Aa bN cH cI Cs jO rB) Uh(eP hW kG mF nC nI nU) Tz(Fc Ho Rx Uw Va Ti) Mw(It Iv Nj Nl Ns) Il(Ho Sh Uw Vz Yl) Qb(Bb Nj Nm Ns Uw) Jp(bN bR dJ oE Tl) Jt(Ar bF cI Ct dF) Vi(lY mY nB nK nN) rS(aW iP Mf qZ vI) Tn(Ch Ng Vc Wh) Lh(iB jF jO Wm) Rm(Sh Yk Zq Ye) Va(Fw Ir Qh Vu) cJ(aA Ar Cs Qc) lN(nC nH nJ nL) Bb(Ax Cs Jo) Js(jF jQ Yh) Nv(Wf Wh Wm) Oa(dJ In Oi) Oh(Kp oH oN) Or(Ho Vq Zq) Ut(Oy We Wh) cH(aA dF nY) Aa(Fr Iv) Th(Cs Mj) Fw(Vz Yl) Nq(Eq Sh) Nr(Fc Vc) Ma(kP nK) Ir(Us We) Qc(cT dF) St(Oi Rx) Ke(hX Vs) Ps(Ki lW) Vq(Hx Ug) Oy(Tr wB) Pf(kP nK) aZ(Ry Uw) cZ(rR rY) iP(rN wD) qZ(aN dJ) AdJo AxMc BaCt TiMj EmKy FaiB MqYe NgUf NjIv NljF HuwB JgUu KprB RjnI VcPg PjwD aAbB dFdH jIjT rNnW Constrained panels with 2 analytes, where 1.0E-3 >= 'model p-value' > 1.0E-4. Contains 3,545 panels of 191,187 total panels evaluated. : Kc(aA aC Ad aE aH aI aQ Ar As Ax bB bF bS cA cE cJ Cp Cq cT cZ dD dF dM eC Em Fa Fp Fr Fw Gp Hb Hv hW hX Ih Ik In Ir Iv Jd jI jK Jt Jy Kf Kp Kr Ky Ld Lh Li Lw Lx Ma Mh Mj Mx Na Nb Nn Nv Ny Oa oE oF oH Oi Ok Oz Pe Pi Qb Qh Ra rB Rf Ri Rm rS St Tv Un Up Ur Ut Vp Wm) Ld(aA aH aI aJ aQ bF bS bV bZ cA cB cE cG cJ cQ Cs cT Cw Cx cZ dD Dk dM eC Fr Gp Hb Hf Hv Ic IH Ik Ir Iv iZ Jt Kd Kp Kx Ky Li Lj Lp Lv Lx Ly Ma mF Mh Mj Ml Mt Mu MW Mx Na Nh NN NR nU Nv Ny OE oF Oi Or OW Pe pI Pj Qb Rm Rt St Tn Up Ut Vp wB Yj) Dr(Ao aV aW aZ BA Bb bF bH bQ bW bZ cB cE cG Cp cS cT cU Dc dF Ef Et Fb Fd Fr Gp Ho Hq Hv Hx Ih Il In Ir It Ji Jk Jm Jn Jp Js Jy Kd Kk Lh Lj Lx Lz Ma Mg Mi Mj Mk Ml Mr Mt Mu Mv Mx Nd Nv oE Og Om On Pg Pi Qb Qc Qt Qv Qx Qy Ru Tr Ua Uf Um Un Uw Vq Vu Yd) Aj(AA aH aJ Ao Ar bB bF bQ bZ cE cH cJ Cp CS cT DK dM Ed Fa Fb Fw Hb Hv Hx Ii Il Io Iv Iz Jd Jh Jn Jo Jr Jy Kj Kl Kr Ks Kx Ky Mg Mh Mj Ml Mp Mu Mw Nb Nj Nm Nt oF Oh Or oW Pe Pg Ph Pi Pj Qh qZ Rf Ri Rm St Tr Tz Ua Up Ur Ut Uw Vp Vu wD Yi) Ow(aA aC aI aJ Ao aQ Ar aV aW Ax bA bB bR bS cA cE Ch cJ Co cQ Ct cZ dD dF dJ dM Dp Fa Hb Hv Hx iB Ij Il Iv IZ Jd Jn Jo Jr Js KP Kr Kx Ky Lh Lv Lx mE Mh Mj Ml Mn Ms My Nr oF Og Ok On Or Ou Pe pH Pi Qb Qc Qh Ri Rm St Tz Uc Ug Uk Up Vp Vq) Ur(Ad Ar As Ax Bb cE cH cJ Co Cp cQ Cs Cw dF dJ Dk Dl dM Em Fd Fp Fr Ha HB Hw iB In Jd Jg Jo Ju Kg Kp Kr Kx Lp Lw Lx Ma Mh Mi Ml Mn Mx Na Nb Nh nI Nj Nl Nm Nt Nv Ny OH Oi Om oW Pb Po Qb Qc Ql Ra Rf Ri Rj St Tn Uf Ug Us Ut Vp Vs Vu Yi Wm) Ri(Ar Ax bA bB cH cJ Cs cT Cu Dc dF dM Dp dR eZ Fp Fw Gc Gp Hb Hx Ih Ij Il In Iv iZ jF Jr Js Kd Kf Kp Kx Lh Lv Lx Mh Ml Mn Mr Mt Mz Ng Nj Nr Nv Nx Ny Oa oE oF Og OH Oi Ok On Or Ou Pe pH Pi Qb Qc rX Tn Tz Uc uT uX vB vI Vp Vq wB wP) Cs(aA Ad aH aI aQ aZ Ba bB bF bN cE cG cH cS cT Cu dF Di dJ dK Ed Fd

Figure 28 Continued

Fr Hb Ho iB Ic Id Ih Ik In Jg Jl Jq Jt Kd Kf Kp Kx Ky Lv Lx Ma Mi Mm Mu Nj Nv Ny Oe Og Oi Or Ph Qb Qc rB rS Ru Tz Uc Un Ut Uw Vj Vq Wb Ti) Tz(Ad Ar bA bB bF cE cH Cu Dc dF dJ dK Dl dM Em Fr Fw hB Ih Il Im In Ip Jd Jl Kd Kp Kx Lh Lj Lp Lv Lw Lx Ma Mh Mn Mr Mz Nh Nr Nv Nx Oa OE oF Og Oh Oi Ok On Ou Pe Pi Qc Ql Rf Tn Tr Uc Un Vj Vq Wd Zq Wm) Kd(aH al aQ Ar aW bA bB bF bR bS bZ cE cH cQ Cx dD dF dJ Dp eC Ed Fr Gp HB Hx Ik Il In Jd Jo Kf Kj Kp Kx Ky Lh Li Lj Lv Lx Ma Mh Ml Mm Mn Mz Nn Oa oE oF Oh On Or pH Qb Qc Ql Sr Uc Uf Ug Uk Uw Zq Wm) hB(bB Bg bR bS cJ Cu Dc De Ed Em Fw Gb Hb Hc Ho Hv Id Ih Ij Il Ip Iv Jl Jn Jr Js jT kE Kx Li IL Lp Lu mF ml Mr Ng nl nK NN nW Oa oE Oh Oi oW Oy Pb Pi Pj Qc Qh rB Ry Sr Tv Un Uy Uz Vc Vq Wb Ti Th) Fd(aH aM Ar aZ bB bQ bR CO cS cU Ef Et Ez Fr gL Gp Hq In Jh Jk Jp Kk Ky Lh Lj Lv Ma Mf Mg Mh Mk Mp Mr Mu Mv Mw Nd Ni Nk Nt Nu Nv oE Or Qc Ql Qv Qw Qy Ra Rj Rt Ru Rx Tr Uf Uh Va Vj Vq Vt Wm) iB(aA aM An Ar Ax bA bF bl cE cH cJ cP Cu cZ Dc dD dF Dl dM Et Ez Hb Id Ij Il Im Jd jl Jj Jl Js Kp Kq Kx Lj Lw Lx Lz Mh Mj Ml Mr Nh Nl Nr Nv Nx Oa Oh Or Ou Pi Pj Po Qa Qe Ql Rm Sr St Tv Uk Vq) Qc(aH al aM aO aQ Ar AX aZ Ba BB bF bN bV cE cG cH cl cU DD Di dJ dK dM Ed Gd Hv Hx Id Io It Iv Jo Kf Kp Mw Mx nC Nj nK Nl Nm Nr Ns NU Oa Ou Oz Pg Tn Tr Uc Un Uw Va Wb Wm) Ed(aQ Ar bA BB bF cE cH cJ cQ cT Dc dD dF dJ dM Em Ex Ez Fr Gp Hb Hx Ik Il Im iO Ip Jd Jg Jy Kf Kp Kx Ky Li Lj Lw Lx Ma Ml Mh Nv oE oF Og OH Oi Ok Or Ou pH Pi Qe Rb Rf Tr Ut) cH(aJ Ar Ax aZ Ba Bb bF cG cl cT CU dM dR Fa Fr gL Hb Ih iZ Jl Jq Js Jt Kf Kp Kx Ky Lh Li Lj Lv Lw Lx Ma Mi Mr Mu Nj nR nU Nv Oa oE oF Om Or Qb Qe Qh qZ St Tn Uc Un Vp wB tF) Kf(aA Af aM bA bB bF bR bS cA cE Ch cQ Ct Cu dD dF dK Dp Gp Hb Ij Iz jK Kx Ky Li Lj Lv Ml Mn Ms Mz Ng Nn Oa OE OF Og Oh Or Ou Pb Ph Qb Qe rS Ss Ug Uk Us Uu Vo xA) Lj(Ad aH al aL aQ aX aZ Ba BB bR cE cG cJ cL cT Dc dD dF Di dJ Dp Gb Gc Hb Ho lc Id Jd jF Jy Kp Ky oE oF oH Or pS Tn Ug Un Ut Vh Vj Vw Wb Wd Yd Yj Zq Zx) dF(aA aF aM Ax Bb bN bQ bR cE cl cO Cu Cx Dd dK Dp hA Hb Ho Ih Ij Ik In Jl Jn Jo Jq Jr Js Kk Ky Lv Lw Mi Mr nl Nj Ns Oa Oe Oi oN Oy Oz Pb Pi Qb rB Tv Wb) Uc(aA Af Ar bA cl cQ Cx De dK Dp eC Em Gp Hb Ib Id Ik Il Iz Kx Ky Li Lx Mh Ml Mn Nh Nj Oa Oe Og Oh Ph Pi Qb Qw rB Rf Rj Rt Ru Sr Ss Uk Ux Vb Vo Vs) Ou(aA Ar aW Ax bA bN bR cQ Cu De dJ dM Dp Gp Hb Hx Ij iZ Jo Jq Jr Js Kp Kx Ky Li Mh Mn Mr Ms Mt My Oa OE oW rB Rf rN rS St Ug Uk Un Us wD Wm) Qb(Ad aQ Ax aZ Ba bB bF bR bV cE cG cJ cP cT Dc dD Dg Di dJ Dl Ho Hv Id In Io It Iv Jo Kp Mw Nl Nu Oe Oh Oy Pb Pc Ru Rx Vj Vq Wb Yj Zq Wm) Un(aQ bA bB bF bN bR cE Ch cl cJ cT dD dJ Dp dR Gp Ic Im jH Jl JO Kj Li Lt Lv Mh Mn Mt Ng Nj nW OE oF Og Oh Oy Pb Pi qC Ru Sr Uu Wm) Oz(Ba bF Dc Fc Fi Gc Hp Hv Hw Hx Ii Io It Jh Jk Jo Lz Mj Mx Nb Nh Nj Nl Nm Nq Ns Nu Oh Pa Pc Pf Pz Ru Ry Uz Vj Vq Vw Wb Wd Yg Yj Zq Zx Ti) oF(aE bB Ch cJ cP cQ Cu Dc De eQ Fw Gb Gc Hb Id Ih Ij Ip Jj Jl Jq Kk Kx Lh Li Mr Mt Nh nl nN Ny oW pH Pj Qe Si Sr Tv Vc Vj Vq Wb Zq Ti) Oa(aQ BB bF bR bS cE cJ cQ Dc dK Dp dR Em Gp Hb Ic Id Ij Ik Il Ip Jd Jq Jy Kp Lh Lv Lw Ma Mn Mt Mz Oe Og oH On Pi Pj Sr tS Us) Ax(aA Ad aH al aQ Ar aZ Ba bB bF bN bQ cG cJ cS cT Cu Di dJ dK Du Fr Ih Ik In Jg Jo Lv Lx Mi Mm Mu Oe Og Oi pH rB Rg rS Vj Th) Wb(aH Ar As aW aZ bA bB bQ bZ cT cU Dc Ef Ex Fr Jh Jq Jy Kx Ky Lz Ma Mf Mk Mn Mp Mu Mv Ni Pa Pd Po Qh Ql Qv Qx Ra Ru Uw) Nr(bS Dp Hb Hv Id Io Ir It Iv Jd jF kP Ky lX Mw Nb nC Nj nK Nl Nm Ns nU Nx oE oN Oy Pa Pb Pc Pg Pz Tv Ug Uk Us) rB(aA aJ bG Dl dM Et Fa Id Im jI Jl Jp Jq Js Ke Kk Kr Lh Li Lw Mj Mt No Nv Nx Ny Qd rN Tv Uh uX vl Vp Vt wB wD) Bb(aA aJ aM Ar bB bN cl cJ cT Cu Cx dD Di dM Hx Ih Ik In Jn Jq Jr Js Lh Lw Lx Mh Mi Mj Ml Mr Nj Oe Og Oi Pe) Or(aW bA bR bS cA cQ dJ dK Em Fw Gb Gp Hb Ik Il Im In kG Kp Ky Li Lp mF Mh Mn Mr NN Oy Uw Vj Vw Yg Ti) rS(Ct cZ Dl Fa Fb Hb Hu Id Jj Jl jT jV Kk Kn Kp Kr Lu Lx Mh Nk No nW Ok Pj Qd qX Rf rN Uk Vt wB yL yE Wm) Ho(aA aH aM Ar aZ bA bB bQ bZ cT cU Ex Gp In Jy Kk Ky Lv Lz Mh Ml Mr Mv Nq Nu oE Pa Qx Ru Tr Ug Uh Ye) Vq(As aZ bB cT dK Dp dR gL Ik Im In Jo Jq Ko Kp Lp Lv Ml Mz oE Og OH Oi Qv Ru Tn To Tr Ux Va Vj Yl) pH(Af aN Ar BN Bo bR bU cA cF cJ De Fw Ir Li Lx Mb mI mZ Nb nC nH nL Nn No NU oE Of Oh Pe Sr Vs) Id(aI aW bA bB bF bN cA cE CT Cu dK dR eZ HX Ic jK Jq Lh lK Lx Mu Mz Pb Qe Tv Ug uR uU Vo vS) Uw(aA Af cQ cU Cx dR Ex Fp Gp Iv Jm Ky Lz Mf Mi Mk Ml Mn Mp Mr Mv Mw Mx Nd Nq Nu oE Oi Pa Pi Qv Uh) Sr(aC aE aI bA bB bR bS cJ cQ dK Dp dR eC Em Ic Il Im Jo Kj Mh Mn Ms Mz nI Nj oE Of Oh Oy Qe Uk) nU(aA aG aH bQ eC Hl Hu Im Ji Jn Jp Ky Lh Li Mh Mp Mt MU Mz No Nw On Pe Pg Ps Qd Yi Yl Ye Xa) Cu(aQ bF bN cI cJ cK cQ CT Cx dJ Dp Fr Hb Ib Kj Kp Kx Ky nI oE oN Ql Rf Rj Ug Uk Us Vo Yh) Dc(Dp eC Gd Hb HX Ii IZ Jg jH jT Jv Kp Kx Ky Lv Lx Ma Mm oE Oy Ph Uk Uu Vo Wc Yk Wm) Jj(aI aW aZ bZ cP dD Ha Hu IC jK jR jT Jy Lz Mu NC Ns oE oW Pb Qy rN Tr Tt vI Vu Yi) Ru(aH Cp Dk Ex Fp Ha Hb Hq Hx Jq Jy kI Kn Kr Ky Lv Mi Mp Mv Nq Nt Nu oE Pi Po Ql Tv Vt Tm) Lx(Ad aH aQ bN bU cF cG cJ cL cN CT dG Di dJ dK Dp hA Hb jF Kp Ky oE pF Qw Rg Uk Tj) Nj(Ar Hv Hw Hx Ii Io Iq Ir It Jk Jo Jr Mj Mq Mu Mx Nb Nl Nm Nq Ns Nu Oh Pa Pc Pf Pg Pz) Kk(aA bB bN bR bS cA cJ Dp Gc Ic jF jK Jv Kx Mi Mw Ne nN OE Rm Tn Ub Uf Uz Yi Yl Wm) wB(AN aW Bg bL Ch cP dJ Hc Hq iP Iz Jk Ko Kr Li Ma Me Mf My Ng Nm Nq oE oN Pj rW uR) Lv(aQ Ar bN bR cI cJ cT dJ Dp Em Gc Hb Hp Jd jF Kp Kx Ky Lp nK oW Uk Us Va Vj Wf Yi) Mr(aQ bF cJ dJ Dp Gc Gp Ha Hb Jd jF Kj KP Kx Ky oE Pj Ql Rf Rx Ug Uk Us Vj Wf Ye) Li(aQ aZ bF bN bQ bR cI cJ cO dJ Dp Hb iH jK jO Kp Ky oE oH pS Rf Rg Uk Us yL xA) aA(Ad aH aI aQ Ar bF Co Cx DD Dl Hb jF jH jK jQ jT kP nC nK nL oW Si Yd Yi Wm) Iv(Hv Hx In Io Ir It Jo Mx Nb Nl Nm Ns Nu Oh Pa Pb Pc Pg Pz Vb Vj Yd Zq Wm Ti) cT(Ad aJ aM Ar Ct Cx dM Em Fr Gc Ih Jg Jl Jn Jq Jt Lw Mi Mm Mu Pb Rx Va Vj) It(bA Hv Hx In Io Ir Jh Jo Mx Nb Nl Nm Nq Ns Nu Oh Pa Pb Pc Pg Pz Va Vj) Yi(aM bM bZ cQ Ct Gz Il In Ke Lz Mf Mx Mz Om Pb Qx Rj Ug Uh Ut Uu Uv Vu) Kp(bA bB cQ eC Fa Hb hX Ij Ik Il In Jq Kx Ky Mh Mt Mz Nn oE Oi pS Qe rW) aZ(Ar Fi Fr Gb Hl Ij Jl Lh Qe Rt Uz Vc Vh Wc Wd We Wf Wg Yl Zq Zw Tl Ti) jF(Et Ij Il Ip jI Jl Jp Jt Ko Lw Lz Md Mh Mj Ml Mn mW Nb Nv Oh Ok Qa Vt) Ar(Ad aE aH aQ Ba bB bN cG Dd dJ dK Fr Ih Ik Jl Jn Jq Jr Mi Oi Pi) Ky(aE bA bB Fc Fi Fw Gc Ij Il Jq jT Lh Lp mI Mn Mz nI Nn On Pe Ry) Mw(Hv Io Ir Jo Jr Ms Mx My Nb Nh Nm Nu Oh Oy Pa Pb Pc Pg Pz Wf) Og(Ad Ba Hu Hv Hw In Iq Jh Jm Jr Lz Mq Mu Mv Nh Nq Ns Oh Pc Pf) Vj(bA Cq Dd Dk Ha Hx Ir Jq Jy Ks Lp Mf Mx Pg Ph Rb Tv Vp Vt Vu) Lh(aQ cI cJ Dp eC lZ Kj nK oN Ph rZ Tv Ug Us Uu Uv Va Vo) Em(Fw Im Jn Ko Kq Mp Mt Nq oE Oh Pf Ph Qd Qv Qx Rj Uh Vt) Jq(aQ bF BN cJ dJ Dp eC eZ Ib iZ jQ Kj lN oE Rx Uf Va) wD(An Bg bH bS Ch Ct Ef Hb Iz Kn Mm Mz Nd Nm nW Nx rC To) Wm(Hb Ip Ir Jg Jn Jr Lw Mi Mj Mn Nb Nx Ny Om Pe Pi Po) Mt(eC Gp hA Hf iH Kj lO mT nC nK nL oH oN qW Tr Us Tj) Tv(aE Af aQ bB cJ Kj Mn oH Ph Pj Ql Rt Rx Va Vs Wc Ti) On(bR Co Dp Ef Kl Kx mM nK oE oN Ph Ss Ug Us Uv Vo Vs) oW(aD Af aL bM Cv hC Hv Ii Jo kI nD nH nL oH Oy Ug tF) Ir(Hv Hx In Io Lt Mx Nl Nm Ns Nu Oe Pb Pc Pg Rx Ry) Jl(aQ Ba bF bN bR bS cI cJ Ct dJ jK jL jO oE oH Qw) Pg(Hv Io kP Mp Mx nC nK Nl Nm Ns Nu Oy Pb Pz Vz) Ij(aQ bN cJ dD Dp Ib Ic Iz Kx Ph Uk Us Uu Vs) Hb(bA Fw Ik Il Jr Mh Ms Mz Nn oE Oh Oi Pc Qe) Zq(aC Ap aX Cq dR Fp hC Hv Hx Il Jm Nd oE Pi) nK(aH bQ Jn Jp Mh Mp Mz No Nv Nw Ny Pe Qa Qd) jK(dM Im Jp Js Ko Mh Mj Nl Nx Ny Oh Qa Qe Vt) Jt(bN bV cE Ch cJ Cx dM Gd Kj Ug Va Vb Th) Pi(bB cA Dp Ex Ik In Jd nI Rx Ug Uk Us Wc) nC(hR Im Ji Jn jY Lz Mh Mp Mz No Nw Pe Qd) Gc(dR Hx Il Jy Mj Ni oE Qv Tn Tr Va Vu) Nm(Hv Hx Io Jr Mx Nl Ns Nu Oh Pa Pb Pz) Lw(aQ bF bN bR bS cD cI cJ Cx dD dJ jH) Ih(aH aL aQ bB bF cE cG cJ Ct dD dJ Sh) Ok(bF Ch dK Dp Iz Kj rW Rx Ug Us Uu Vo) Io(Hv Jo Jr Mh Mx Nb Nl Ns Nu Nx Pa) Lp(bQ bZ cU Jy Ml Mp Nq Nu oE Tr Uh) Va(bA Dk Ef Jk Ke Mp Mv Nt Nv Pa Vt) dM(aH aI aQ bB bF cJ jH Mn pS qC rC) nI(bB bQ bZ eC Fw Kq Mz oE St Ug Um) qZ(aW bL Ch eC Ef Fw Hc Ic iP Pj pS) kP(Im Jn Mh Mp No Nw Oh Pe Ps Qa Qd) Js(aQ cJ Ct dJ jE jR jT qW Ug Us) iZ(aE aH aI bB cE cJ cZ dD dJ Si) Mn(bR bS Gd Kj Kx Ph Sh Ug Uk) Tn(cQ dJ Eq Ip Oi Oy Rt Sh Uu) Im(Dp Ex Ic Jd mF mY Qw Rb Vs) In(Ba Fa Kr Kx Om Pe Qh Rm Up) Rx(bA Cq Dk Hx Ji Ke Qh Vp Vt) Et(eC jO rN rR rW rX Ry rZ) Fr(aQ bN bO Ch cI cJ Dd dJ) Nq(Hu Nl Oy Rt Ry Uy Uz Wc) Mx(Mp Ns Nu Nx Om Pb Pz Yd) Il(Dp Jd Kx Ql Qw Rf Ug Uk) Nv(Af aQ bS Ct Cx Eq Iz jO) Nw(mF mI mP mY nL nT rW wQ) Oi(Ba cG Jd Kx Qh Rf Rm Uf) oE(bB cE Fw Gb Hp Qe Si Uz) Nl(Hx jI Ne Ns Nu Pe

Figure 28 Continued

Pz) Ye(Dk Jh Jk Mi Mu Ql Vu) Kq(eC hA jT lO mZ oN Vs) Nx(jl jO lN Ms Om rX rZ) bF(aJ aM Dd Jn Jr Mi Ml) Mz(Dp eC Kx mZ Us wJ) Sh(Cp Dk Ef Jk Jp Qh) Qd(eC eZ mF qC rX Vs) Oh(iJ Jd jO jQ Om Pe) Vu(Eq Gn Hl Rt Vb Tl) jT(aM Fa Mj Qa Qe Vt) Ba(Ch Ik Jo Ng Oe) Ko(eC eZ Gd hX qC) Pe(kC lO lX My Pc) bA(Dp Kx Pj Ug Us) bR(cG Ex Mi Pf Qe) cI(al bB cG Jg Mi) nN(iH oH Ps Yd Zx) jl(jH Mh Ny oO rZ) Po(Fc Gh Vc Wh) Nu(Hv Hx Ns Uz) Mm(Nb Ng Oy Pa) Ik(Ad Fa Jd Kx) Wf(Dk Jy Mu Tr) Jo(Cw Hr Pb Uf) Uh(mM mZ Uz Wg) Ut(cQ Ct Gd Of) Vt(eZ jQ Lt We) cJ(aJ aP Ex Rf) dJ(Jn Kx Rf Vp) oH(bB Fw Nn Uf) Ch(Jg Ma Uf) Eq(Ef Jk Mu) Fp(Yd Ti Th) Nb(My Oy Pb) Pz(Hv Ns Oe) Ps(kG kI mW) Ry(cU Mk Mp) Rm(Gp Us Yj) Ny(Ao lO rX) cG(cL dH hA) rC(Dl Ke Kn) uT(oN Pj uR) An(vl yL) Fa(hX Ti) Fw(Jd Kx) Nt(Vc Wh) Mh(nH nL) Mi(aH bS) Ng(Jd Tr) Is(eZ rX) Qa(Gp jQ) Qe(Ic jR) Jk(Tm Tl) Jr(eZ qW) Kr(tS xA) Om(Hr Rz) Ug(Dd Ip) aN(rN vI) cU(Gb Vc) eC(kN lW) CpWh CwGd FiMl FymZ GhJi NnKj NoVs MamY MpHx MvUy NkrN JhOy StOe QhUs TmPa KerY PfbS aEnY bBgV bNoQ bQmI bZeQ cEoN nDlN hLiP iHkG jYkO nWuX

Unconstrained panels with 3 analytes, where 0.0E0 >= 'AUC p-value' > 0. Contains 50,000 panels of 35,191,980 total panels evaluated. : Vi{Oh(aA aC AD aE AF aG aH aI AJ aK AL aM AN AO AP aQ AR AS aU aV Aw AX aY aZ BA BB BC bE bF BG bH bI bJ bL bM BN BO bP bQ bR bS bU bV bW bX bZ cA cB cC cD cE cF cG CH cI cJ cK cL cM cN CO CP Cq cR CS CT CU CV CW CX cY cZ dA DB DC DD DE dF DG dH DI dJ DK DL dM dN Dp Dr Du Ed Ef Em Eq Et Ex Ez Fc Fd Fi Fn Fp Fr Fw Fy Gb Gc Gd Gh Gl Gn Gp Gz Ha Hb Hc Hf Hl Ho Hp Hq Hr Hu Hv Hw Hx Ib Ic Id Ih Ii Ij Ik Il Im In Io Ip Iq Ir Is It Iu Iv Iz Jd Jf Jg Jh Ji Jj Jk Jl Jm Jn Jo Jp Jq Jr Js Jt Ju Jv Jy Kc Ke Kf Kg Ki Kj Kk Kl Kn Ko Kp Kq Kr Ks Kx Ky Kz Ld Lh Li Lj Lp Lt Lu Lv Lw Lx Ly Lz Ma Mb Mc Md Me Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oi Ok Om On Op Or Ou Ow Oy Pa Pb Pc Pd Pe Pf Pg Ph Pi Pj Pk Po Ps Pz Qa Qb Qc Qd Qe Qg Qh Ql Qm Qn Qt Qu Qv Qw Qx Qy Qz Ra Rb Rf Rg Rh Ri Rj Rm Rt Ru Rv Rx Ry Rz Sf Sh Si Sj Sr Ss St Tn To Tv Tz Ua Ub Uc Ud Ue Uf Ug Uh Uk Ul Um Un Uo Up Ur Us Ut Uu Uv Uw Ux Uy Uz Va Vb Vc Vh Vj Vo Vp Vq Vs Vu Vv Vw Vz Wb Wc Wd We Wg Wh Yd Yg Yl Zq Zw Zx Ye Tm Tl Xa Wm Tj Ti Th) Qe(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cM cN CO CP Cq cR CS CT CU CV CW CX cY cZ dA DB DC DD DE dF DG dH DI dJ dK DL dM dN Dp Dr Du Ed Ef Em Eq Et Ex Ez Fc Fd Fi Fn Fp FR Fw Fy Gb Gc Gd Gh Gl Gn GP Gz Ha Hb Hf Hl Ho Hp Hq Hr Hu Hv Hw Hx Ic Id Ih Ii Ij Ik Il Im In Io Ip Iq Ir Is It Iu Iv Iz Jd Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lp Lt Lu Lv Lw Lx Ly Lz Ma Mb Mc Md Me Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx Ny Oa Oe Of Og Oi Ok Om On Op Or Ou Ow Oy Pa Pb Pd Pe Pf Pg Ph Pi Pj Pk Po Ps Pz Qa Qb Qc Qd Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tv Tz Ua Ub Uc Ud Ue Uf Ug Uh Uk Ul Um Un Uo Up Ur Us Ut Uv Uw Ux Uy Uz Va Vb Vc Vh Vj Vo Vp Vq Vs Vt Vw Vz Wb Wc Wd We Wf Wg Wh Yd Yh Yl Zw Zx Ye Tm Tl Xa Wm Tj Ti Th) Aj(aA aC AD aE AF aG aH aI aJ aK AL aM AN AO AP aQ AR AS aU aV Aw AX aY aZ BA BB BC bE bF BG bH bI bJ bL bM BN BO bP bQ bR bS bU bV bX bZ cA cB cC cD cE cF cG CH cI cJ cK cL cM cN CO CP Cq cR CS CT CU CV CW CX cY cZ dA DB DC DD DE dF DG dH DI dJ DK DL dM dN Dp Dr Du Ed Ef Em Eq Et Ex Ez Fc Fd Fi Fn Fp Fr Fw Fy Gb Gc Gd Gh GL Gn Gp Gz Ha Hb Hc Hf Hl Hp Hq Hr Hu Hv Hw Hx Ib Ic Id Ih Ii Ij Ik Il Im In Io Ip Iq Ir Is It Iu Iv Iz Jd Jf Jg Jh Ji Jj Jk Jl Jm Jn Jo Jp Jq Jr Js Jt Ju Jv Jy Kc Ke Kf Kg Ki Kj Kk Kl Kn Ko Kp Kq Kr Ks Kx Ky Kz Ld Lh Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oi Ok On Op Or Ou Oy Oz Pa Pb Pc Pd Pe Pf Pg Ph Pi Pj Pk Po Ps Pz Qa Qb Qc Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tv Tz Ua Ub Ud Ue Uf Ug Uh Uk Ul Um Un Uo Up Ur Us Ut Uu Uv Uw Ux Uy Uz Va Vb Vc Vh Vj Vo Vp Vq Vs Vt Vu Vw Vz Wb Wc Wd We Wf Wg Wh Yd Yk Yl Zq Zw Zx Ye Tm Tl Xa Wm Tj Ti Th) Rc(aA aC AD aE AF aG aH aI aJ aK AL aM AN AO AP aQ AR AS aU aV Aw AX aY aZ BA BB BC bE bF BG bH bI bJ bL bM BN BO bP bQ bR bS bU bV bW bX bZ cA cB cC cD cE cF cG CH cJ cK cL cM cN CO CP Cq cR CS CT CU CV CW CX cY cZ dA DB DC DD DE dF DG dH DI dJ DK DL dM dN Dp Dr Du Ed Ef Em Eq Et Ex Ez Fa Fb Fc Fd Fi Fp FR Fw Fy Gb Gc Gd Gh Gl Gn Gz Ha Hb Hf Hl Ho Hp Hq Hr Hu Hv Hw Hx Ib Ic Id Ii Ij Ik Il In Io Ip Iq Ir Is It Iu Iv Iz Jd Jf Jg Jh Ji Jj Jk Jl Jm Jn Jo Jp Jq Jr Js Jt Ju Jv Jy Kc Kc Kf Kg Ki Kj Kk Kl Kn Ko Kq Kr Ks Kx Ky Kz Ld Lh Li Lp Lt Lu Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nc Nd Ne Nf Ng Nh Ni Nj Nk Nm Nn No Nq Nr Ns Nt Nu Nv Nw Nx Ny Oa OE Og Oi Ok Om On Op Or Ou Oy Oz Pa Pb Pc Pd Pe pF Pg Ph Pi Pj Pk Po Ps Pz Qa Qb Qc Qd Qg Qh Ql Qm Qn Qt Qu Qv Qw Qx Qy Qz Ra Rb Rf Rg Ri Rj Rm Rt Ru Rv Rx Ry Rz Sf Sh Si Sj Sr Ss St Tn To Tv Tz Ua Ub Uc Ud Ue Uf Ug Uh Uk Ul Um Un Uo Up Ur Us Ut Uu Uv Uw Ux Uy Uz Va Vb Vc Vh Vj Vo Vp Vq Vs Vt Vw Vz Wb Wc Wd We Wf Wg Wh Yd Yl Zq Zw Zx Ye Tm Tl Xa Wm Tj Ti Th Yf) Qa(aA aC AD aE AF aG aH aI aJ aK AL aM AN AO AP aQ AR AS aU aV Aw AX aY BA BB bC bE bF BG bH bI bJ bL bM BN BO bP bQ bR bS bU bV bW bX bZ cA cB cC cD cE cF cG CH cI cJ cK cL cM cN CO CP Cq cR CS CT CU CV CW CX cY cZ dA DB DC DD DE dF Dg dH DI dJ dK DL dM dN Dp Dr Du Ed Ef Em Eq Et Ez Fc Fd Fi Fn FP FR Fw Fy Gb Gc Gd Gh Gl Gn Gp Gz Ha Hb Hf Hl Ho Hp Hq Hr Hu Hv Hw Hx Ib Ic Ih Ii Ij Ik Il Im In Io IP Iq Ir Is It Iu Iv Iz Jd Jf Jg Jh Ji Jj Jk Jl Jm Jn Jo Jp Jq Jr Js Jt Ju Jv Jy Kc Ke Kf Kg Ki Kj Kk Kl Kn Ko Kp Kq Kr Ks Kx Ky Kz Ld Lh Li Lj Lp Lt Lu Lv Lw Lx Ly Lz Ma Mb Mc Md Me Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nw Nx Ny Oa OE Of Og Oi Ok Om On Op Or Ou Ow Pa Pb Pd Pe Pf Pg Ph Pi Pj Pk Po Ps Pz Qb Qc Qd Qg Qh Ql Qm Qn Qu Qv Qw Qx Qy Qz Ra Rb Rf Rg Rh Ri Rj Rm Rt Ru Rv Rx Ry Rz Sf Sh Si Sj Sr Ss St Tn To Tv Tz Ua Ub Uc Ud Ue Uf Ug Uh Uk Ul Um Un Uo Up Ur Us Ut Uv Uw Ux Uy Uz Va Vb Vc Vh Vj Vo Vp Vq Vs Vt Vv Vw Vz Wb Wc Wd Wf Wg Wh Yd Yg Yh Yl Zq Zw Zx Ye Tm Tl Xa Wm Tj Ti Th) Vt(aA aC AD aE AF aG aH aI aJ aK AL aM AN AO AP aQ AR AS aU aV Aw AX aY aZ BA BB bC bE bF BG bH bI bJ bL bM BN BO bP bQ bR bS bU bV bW bX bZ cA cB cC cD cE cF cG CH cI cJ cK cL cM cN CO CP Cq cR CS CT CU CV CW CX cY cZ dA DB DC DD DE dF DG dH DI dJ DK DL dM dN Dp Dr Du Ef EM Eq Et Ex Ez Fa Fc Fd Fi Fp FR Fw Fy Gb Gc Gd Gh Gl Gn Gp Gz Ha Hb Hc Hf Hl Ho Hp Hq Hr Hu Hv Hw Hx Ib Ic Id Ih Ii Ij Ik Il In Io Ip Iq Ir It Iu Iv Iz Jd Je Jf Jg Jh Ji Jj Jk Jl Jm Jn Jo Jp Jq Jr Js Jt Ju Jv Jy Kc Ke Kf Kg Ki Kj Kk Kl Kn Ko Kp Kq Kr Ks Kx Ky Kz Ld Lh Li Lp Lt Lu Lv Lw Lx Ly Lz Ma Mb Mc Md Me Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oa Oe Of Og Oi Ok Om On Op Or Ou Oy Pa Pd Pe PF Pg Ph Pi Pj Pk Po Ps Pz Qb Qc Qd Qg Qh Ql Qm Qn Qt Qu Qv Qw Qx Qy Qz Ra Rb Rf Rg Rh Ri Rj Rt Ru Rv Rx Ry Rz Sf Sh Si Sj Sr Ss St Tn To Tr Tv Tz Ua Ub Uc Ud Ue Uf Ug Uh Uk Ul Um Un Uo Ur Us Ut Uu Uv Uw Ux Uy Uz Va Vb Vc Vh Vj Vo Vp Vq Vs Vw Vz Wb Wc Wd We Wf Wg Wh Yd Yl Zq Zw Zx Ye Tm Tl Xa Wm Tj Ti Th) Oi(aA aC AD aE AF aG aH aI aJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cM cN CO Cp Cq cR CS CT Cu CV CW CX cY cZ dA DB DC DD DE dF DG dH DI dJ DK DL dM dN Dp Dr Du Ed Ef Em Eq Et Ex Ez Fc Fd Fi Fp FR Fw Fy Gb Gc Gd Gh Gl Gn Gp Gz Ha Hb Hc Hl Ho Hp Hr Hu

Figure 28 Continued

Figure 28 Continued

Gh Gl Gn Gp Gz Ha Hb Hf Hi Hl Ho Hp Hq Hr Hu Hx Ib Ic Id Ih Ii Ij Ik Il In Io Ip Ir It Iu Iv Iz Jf Jg Ji Jj Jk Jl Jm Jn Jo Jp Jq Jr Js Jt Ju Jv Jy Kd Kf Kg Ki Kj Kk Kl Kn Ko Kp Kr Ks Kx Ky Kz Lh Lp Lt Lu Lv Lw Lx Ly Lz Ma Mb Mc Md Me Mf Mg Mh Mj Mk Ml Mm Mn Mq Mr Ms Mt Mx My Mz Na Nb Nc Nd Ne Nf Ng Nh Ni Nj Nk Nl Nm No Nr Ns Nt Nu Nv Nw Nx Ny Oe Of Og Ok On Op Or Ou Oy Oz Pa Pb Pc Pd Pe Pf Pg Ph Pi Pj Pk Po Ps Pz Qb Qc Qd Qg Qh Ql Qm Qn Qt Qu Qv Qw Qx Qz Ra Rb Rf Rg Rh Ri Rj Rm Rt Ru Rv Ry Rz Sf Sh Si Sj Sr Ss St Tn To Tv Tz Ua Ub Uc Ud Ue Ug Uh Uk Ul Um Un Uo Up Ur Us Ut Uu Uv Uw Ux Uy Uz Va Vb Vc Vh Vo Vp Vq Vs Vu Vw Vz Wb Wc We Wf Wg Yd Yl Zw Zx Ye Tm Tl Xa Wm Tj Ti Th) Li(aA aC Ad aE AF aG aH al aJ aK AL aM AN aO AP aQ AR AS aU aV AW Ax aY BA BB BC bE bF bG bH bI bJ bL bM BN BO bP bQ bR bS bU bV bW bX cA cB cC cD cE cF cG cH cI cJ cK cL cM cN CO CP Cq cR CS CT CU CV CW CX cY cZ dA DB DC DD DE dF DG dH DI dJ DK DL dM dN Dp Dr Et Ex Ez Fc Fd Fi FP Fr Fw Fy Gb Gc Gd Gh Gl Gn Gp Gz Hb Hf Ho Hq Hr Hu Hv Hw Hx Ib Id Ih Ii Ij Ik Il In Io Ip Iq Ir It Iu Iv Jd Jg Jh Ji Jj Jk Jl Jm Jn Jo Jp Jq Jr Js Jt Ju Jy Kc Kd Kf Kg Ki Kj Kk KJ Ko Kp Kr Kx Kz Lh Lp Lu Lv Lw Lx Ly Lz Ma Mb Mc Md Me Mg Mh Mi Mj Mk Ml Mm Mn Mp Mq Mr Ms Mt Mu Mv Mw Mx Mz Na Nb Nc Nd Ne Nf Nh Ni Nj Nk Nl Nm Nn No Nq Nr Ns Nt Nu Nv Nw Nx Ny Oe Of Og Ok Om On Op Or Ou Ow Oy Oz Pa Pb Pc Pd Pe Pf Pg Ph Pj Pk Po Ps Pz Qb Qd Qg Qh Ql Qn Qt Qu Qv Qw Qx Qy Qz Ra Rb Rf Rg Rh Ri Rj Rm Rt Ru Rv Rx Ry Sf Sh Sj Sr St Tn To Tv Tz Ua Ub Uc Ud Ue Uf Ug Uh Uk Ul Um Un Uo Up Ur Us Ut Uv Uw Ux Uy Uz Va Vc Vh Vj Vo Vp Vq Vs Vz Wb Wc We Wg Yd Yl Zw Zx Ye Tl Wm Ti Th) Uu(aA aC AD aE Af aG aH aI aJ AL aM AN AO AP Ar As Aw AX aY aZ BA BB Bc bF Bg bH bI bL BN BO bP bQ bR bS bV bX bZ cA cC cD cE cF cG CH cI cJ cK cM cN Cp Cq cR Cs CT CU CV CW CX cY DB DC DD dE dF DG dH DI Dk DL dN Dp Dr Du Em Et Ex Ez Fa Fc Fd Fi FF FR Fw Fy Gb Gh Gl Gn gP Gz Ha Hb Hc HF Hl Hp Hq Hr Hw Ib Ic Id Ih Ij Ik Il In Io IP Ir It Iv IZ Jd Jf Jg Jh Ji Jj Jk Jl Jm Jn Jo Jp Jq Jr Js Ju Jv Jy Kc Kd Ke Kf Kg Ki Kk Kl Kn Ko Kp kQ KS Kx Ky Kz Lh Lp Lt Lu Lv Lw Ly Lz Ma Mb Mc Md Me Mh Mj Mk Ml Mm Mn Mr Ms Mt Mx My Mz Nb Nc Nd Ne Nf Ng Nh Ni Nj Nk Nl Nm No Nq Nr Ns Nt Nu Nv Nx NY OE Of Og OK ON Op Or Ou Oy Pa Pb Pd Pe Pf Pg Ph Pj Po Ps Pz Qb Qg Qh Ql Qm Qn Qv Qw Qx Qz Ra Rb Rf Rg Ri Rj Rm Rt Ru Rv Rx Ry Rz Sf Sh Si Sj Sr Ss St Tn To Tr Tt Tv Tz Ub Ud Ue Ug Uh Ul Um Un Uo Up Ur Us Uv Uw Ux Uy Uz Va Vb Vc Vh Vj Vo Vp Vq Vs Vu Vv Vw Vz Wb Wc Wd We Wg Yd Yh Yi Yl Zw Zx Tm Tl Xa Wm Tj Ti Th Yf) Oz(aA aC AD AF aG aH aI aK AL aM AN AO AP aQ AR AS aU aV AW aX aY aZ BA BB BC bE BG bH bI bL bM BN bO bP bQ bR bS bU bV bW bX bZ cA cC cF cG CH cI cK cM CO CP cQ cR CS CT CU CV CW CX cY cZ dA DB DC DD DE dF DG DI dJ DK DL dM dN Dp Dr Du Em Eq Et Ex Ez Fb Fc Fi Fp FR Fw Gb Gc Gd Gl Gn Gp Gz Hb Hc Hl Ho Hp Hq Hr Hu Hw Hx Ib Ih Ii Ij Ik Il In Io It Iu Iv Iz Jd Jf Jg Jh Ji Jj Jk Jm Jo Jp Jq Jt Ju Jv Jy Kc Kd Ke Kf Kg Ki Kj Kl Kn Ko Kp Ks Kx Ky Kz Lh Lp Lt Lu Lv Lw Ly Lz Ma Mc Md Me Mg Mh Mi Mj Mk Ml Mm Mn Mp Mq Mr Ms Mt Mu Mv Mw Mx My Mz Na Nd Ne Nf Ng Nh Ni Nj Nk Nl Nm Nn Nr Ns Nt Nv Nx OE Of Og Ok Om On Op Or Ou Ow Oy Pa Pc Pd Pf Ph Pi Pj Po Pz Qc Qg Qh Ql Qm Qn Qt Qu Qv Qw Qx Qy Qz Ra Rb Rf Rg Rh Ri Rj Ru Rv Rx Ry Rz Sf Sh Si Sj Ss St Tn To Tr Tt Ua Ud Uf Ug Uh Uk Ul Um Un Uo Up Ur Us Ut Uv Uw Ux Uy Uz Va Vb Vc Vj Vo Vs Vv Vw Vz Wb Wc Wd We Wf Wg Yd Yg Yh Yj Yk Zq Zw Zx Ye Tm Tl Xa Wm Tj Ti Th Yf) Mq(aA aC AD Af aG aH aI aJ aK AL aM AN AO AP aQ AR As aU Aw AX aY aZ BA BB BC bE BG bH bJ bL bM Bn BO bP bR bS bU bV bW cA cB cD cE cF cH cI cJ cK cL Co CP Cq cR CS CT CU CV CW CX cZ DB DC DD DE DG Di DK Dl dM dN Dp Dr Ef Em Eq Et Ex Ez Fd Fp Fr Fw Gb Gc Gd Gl Gn Gp Hb Hc Hp Hq Hr Hu Hv Hw Hx Ib Ic Ih Ii Ij Ik Il In Io Ip Iq Ir It Iu Iv Iz Jd Jg Jh Ji Jj Jk Jl Jm Jn Jo Jp Jq Jr Js Jt Ju Kd Kf Kg Ki Kj Kk Kl Ko Kp Kx Lh Lp Lu Lv Lw Lx Ly Lz Ma Mb Mc Md Me Mf Mg Mh Mi Mj Mk Ml Mm Mn Mp Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Ok Om On Or Ou Ow Oy Pa Pb Pc Pd Pe Pf Pg Ph Pk Po Ps Pz Qb Qc Qd Qg Qh Ql Qn Qt Qu Qv Qw Qx Qy Qz Ra Rb Rf Rg Rh Ri Rj Rm Rt Ru Rv Rx Rz Sh Sr Ss St Tn To Tv Tz Ua Ub Uc Ud Ue Uf Ug Uh Uk Ul Um Un Uo Up Ur Us Ut Uv Uw Ux Uy Uz Va Vb Vc Vh Vj Vo Vp Va Vb Vc Vh Vj Vo Vs Vv Vw Vz Wb Wc Wd We Wf Wg Yd Yg Yh Yl Zw Ye Wm Ti) Wf(aA aC AD aE aF aG aH aI aJ aK AL aM AO aP aQ aR aS aU aV AW AX aZ BA bB BC bE Bg bH bI bJ bL bM bN bQ bR bS bU bV bW bX bZ cA cB cC cD cE cF cG Ch cI cJ cK cL cM cN CO Cp CQ cR CS CT CU Cv Cw cY cZ dA DB DC DD DE dF DG dH DI dJ DK DL dM dN DR Du Ef Em Eq Et Ex Ez Fa Fb Fd Fi Fp FR Fw Fy Gb Gd Gl Gn Gp Gz Ha Hb Hf Ho Hp Hq Hr Hv Hw Hx Ib Id Ii Ik Il In Io Ip Ir It Iu Iv Iz Je Jf Jg Jh Ji Jj Jk Jl Jm Jo Jp Jr Jt Ju Jv Jy Kc Kd Kf Kg Kj Kl Kn Ko Kr Ks Kx Ky Kz Lh Lp Lt Lv Lw Ly Lz Ma Mb Mc Md Me Mf Mg Mi Mj Ml Mm Mp Ms Mt Mu Mx My Mz Na Nb Nc Nd Ne Nf Ng Nh Ni Nj Nk Nl Nm Ns Nt Nu Nv Nx NY oE Ok Om On Op Or Ou Oy Pa Pd Pf Pg Pi Pj Pk Ps Pz Qb Qc Qd Qh Ql Qm Qn Qt Qu Qv Qw Qx Qy Qz Ra Rb Rf Rg Ri Rj Rm Ru Rv Ry Rz Sf Sh Si Ss St Tn To Tr Tt Tv Tz Ua Ub Uc Ud Ue Uf Ug Uk Ul Um Un Uo Up Ur Ut Uv Uw Ux Uy Uz Vb Vc Vh Vo Vq Vs Vu Vv Vw Vz Wb Wc Wd We Wg Yd Yh Yl Zq Ye Tm Xa Wm Tj Ti Th Yf) Qb(aA aC AD AF aG aJ aK Al aM AN AO AP ApQ AR aS aV Aw AX aY aZ Ba BB BC bE bF Bg bH bJ bM BN BO bP bQ bS bU bV bZ cA cB cC cE cF cG Ch cJ cK cL cM cN CO CP Cq cR CS Ct CU CV CX cY cZ dA Db DC Dd DE Dg DI dJ DK Dl dM dN Dp Dr Ef Eq Et Ex Ez Fc Fp Fr Fw Fy Gc Gd Gh Gl Gn Gp Ha Hc Hf Hl Ho Hp Hq Hr Hu Hv Hw Hx Ib Ic Ih Ii Ij Ik Il In Io Ip Iq Ir It Iu Iv Iz Jd Jg Jh Ji Jj Jk Jl Jm Jn Jo Jp Jq Jr Js Jt Ju Jv Jy Ke Kf Kg Ki Kk Kl Kp Kz Lh Lu Lv Lw Lx Ly Lz Ma Mb Mc Md Me Mf Mh Mj Mk Ml Mm Mp Mr Ms Mt Mu Mv Mw Mx My Mz Na Nb Nc Nd Ne Nf Ng Nh Ni Nj Nk Nl Nm Ns Nt Nu Nv Nw Nx Ny Oe Of Og Ok Om On Op Or Oy Pa Pb Pc Pd Pe Pf Pg Pj Pk Po Ps Pz Qc Qd Qg Qh Qm Qn Qt Qu Qv Qw Qx Qy Qz Ra Rb Rf Rg Rh Ri Rj Rm Rt Ru Rv Ry Rz Sf Sh Sr Ss St Tn To Tv Tz Ua Ub Uc Ud Ue Uf Ug Uh Uk Ul Um Un Uo Up Ur Us Ut Uv Uw Ux Uy Uz Vb Vc Vh Vo Vq Vs Vu Vv Vw Wc Wd We Wg Yd Zw Ye Tl Wm Ti Th) Vb(aA aC AD AF aG aH aI aJ aK AL aM AN AO AP aQ AR AS aU AW AX aY aZ Ba BB BC bE bF BG bH bI bJ BN BO bS bU bV bW bZ cA cB cC cD cE cF cG Ch cJ cK cL cM cN cO CP Cq cR CS Ct CU CV CW CX cZ Db Dc Dd DE dF Dg dH DI DK DL dM dN Dp Dr Ef Et Ez Fc Fi Fp Fr Fw Fy Gb Gc Gd Gl Gp Hc Hf Hl Hq Hr Hu Hv Hw Hx Ib Ic Ih Ii Ij Ik Il In Io Ip Iq Ir It Iv Iz Jd Jf Jg Jh Ji Jj Jk Jl Jm Jn Jo Jp Jq Jr Js Jv Jy Kd Ke Kg Ki Kj Kk Kr Ks Kz Lh Lu Lv Lw Lx Ly Lz Ma Mb Mc Md Me Mf Mg Mh Mj Mk Ml Mm Mn Mr Ms Mt Mv Mw Mx My Mz Na Nb Nc Nd Ne Nf Ng Nh Ni Nj Nk Nl Nm No Nr Ns Nt Nu Nv Nw Nx Ny Oe Of Og Ok Om On Op Or Oy Pa Pb Pc Pe Pf Pg Pi Pj Pk Po Ps Pz Qc Qd Qg Qh Ql Qm Qn Qt Qu Qv Qw Qx Qz Ra Rb Rf Rg Rh Ri Rj Rm Rt Ru Rv Rx Ry Rz Sh Si Sr Ss St Tn To Tv Tz Ua Ub Ud Ue Ug Uh Uk Ul Um Un Uo Up Ur Us Ut Uv Uw Ux Uy Uz Va Vc Vh Vj Vo Vp Vq Vs Vu Vw Wc Wd We Wg Yd Zx Tl Xa Wm Ti Th) Mp(aA aC AD aE AF aI aM AN Ao AP AR AS aU aW Ax aZ Ba Bb BC bF BG bH bJ bL BN BO bP bQ bR bS bU bV bW bX cA cB cD cE cH cK cL Co Cp Cq cR CS Ct CU CV Cw CX cY cZ Db DC Dd De dF DG dH Di DK Dl dM dN Dp Dr Ef Et Ez Fc Fd Fi Fp Fr Gb Gc Gd Gh Gl Gp Hb Hf Hg Hr Hu Hv Hw Hx Ib Ic Ih Ii Ij Ik Il In Io Ip Iq Ir It Iv Iz Jd Jf Jg Jh Ji Jj Jk Jl Jm Jn Jo Jp Jq Jr Js Jv Jy Kd Ke Kg Ki Kj Kk Kr Ks Kz Lh Lu Lv Lw Lx Ly Lz Ma Mb Mc Md Me Mf Mg Mh Mj Mk Ml Mm Mn Mr Ms Mt Mv Mw Mx My Mz Na Nb Nc Nd Ne Nf Ng Nh Ni Nj Nk Nl Nm No Nr Ns Nt Nu Nv Nw Nx Ny Oe Of Og Ok Om On Op Or Oy Pa Pb Pc Pe Pf Pg Pi Pj Pk Po Ps Pz Qc Qd Qg Qh Ql Qm Qn Qt Qu Qv Qw Qx Qz Ra Rb Rf Rg Rh Ri Rj Rm Rt Ru Rv Rx Ry Sh Sj Sr St Tn To Tv Tz Ua Ub Uc Ud Ue Uf Ug Uh Uk Ul Um Un Uo Up Ur Us Ut Uv Uw Ux Uy Uz Va Vc Vh Vj Vo Vp Vq Vs Vu Vw Wc Wd We Wg Yd Yg Yh Yl Zw Yc Tl Wm Ti Th) Gc(aA aC Ad AF aJ AL aM AN AO AP AR aS aU AW AX aY BA Bb BC bF BG bI bJ bL bM BN BO bQ bR bV bX bZ cA cB cD cE cF cH cI cJ cK cL cN Co Cp Cq CS Ct CU CV Cw CX DB DC Dd DE Dg DI dJ DK DL dN Dp Dr Et Ex Ez Fc Fd Fp Fr Fw Fy Gd Gl Gn Gp Gz Ha Hb Hf Hl Hq Hu Hv Hx Id Ih Ii Ij Ik Il In Io Ip Iq It Iu Iv Iz Jd Jg Jh Ji Jj Jk Jl Jm Jn Jo

Figure 28 Continued bF Bg bP bQ bS bZ cB cE cV Dc dF dR Ef Fy Gh Hq Ik Il iP Jl Jp Jr Jy Kq Lv Ma Mt Mv Mz Nd Nn Nq nY oE Oh Oi On Or Ou Ow Oz Pf Qv Ri Sj Tr Uc Ug Ut Yd) Ji(aA Aj Et Fi Fp Gh Hq Hr Hu Ii Ik In Iu Jk Jo Jp Jq Lj Lu Lv Md Ml Ms My Mz Na Ng Nk Nm Ns Nx Of Og Oi Ok Om Oy Oz Pb Qc Qd Uw Ux Va Vb Vc Vh Vw Vz Wb Wc Wd Wh Yd Zw Xa Th) Oz(Dr Du Et Fc Fd Fi Gb Gh Hl Ho Lp Lt Og Op Rt Ru Rv Rx Ry Rz Sf Sh Si Uw Ux Uy Uz Va Vb Vc Vh Vj Vw Vz Wb Wc Wd We Wg Wh Yd Yg Yh Yi Yj Yk Zq Zw Zx Tm Tl Ti Th Yf) Oi(Du Et Fc Fd Fi Gb Gd Gh Hl Ho Hp Lp Lt Op Rt Ru Rv Rx Ry Rz Sf Sh Si Sj Uw Ux Uy Uz Va Vb Vc Vh Vj Vw Vz Wb Wc Wd We Wg Wh Yd Yi Yj Zq Zw Zx Tm Tl Xa Ti Th) bS(Du Fc Fd Gb Gh Hl Ho Hp Lp Lt Op Rt Ru Rv Rx Ry Rz Sf Sh Si Sj Uw Ux Uy Uz Va Vb Vc Vh Vj Vw Vz Wb Wc Wd We Wg Wh Yd Yg Yh Yi Yj Yk Zq Zw Zx Tm Tl Xa Yf) Or(Dr Du Fc Fd Fi Gb Gc Gh Gn Hl Ho Hp Lp Lt Op Rt Ru Rv Rx Ry Rz Sf Sh Si Sj Uw Ux Uy Uz Va Vb Vc Vh Vj Vw Vz Wb Wc Wd We Wg Wh Yd Yi Zw Zx Tm Tl Xa Ti) Mz(Aj Du Fc Fd Fi Gb Gh Hl Ho Hp Lp Lt Og Op Rt Ru Rv Rx Ry Rz Sf Sh Si Sj Uw Ux Uy Uz Va Vb Vc Vh Vj Vw Vz Wb Wc Wd Wg Wh Yd Yh Zw Zx Tm Tl Xa Ti Th) Qv(Dr Du Fc Fd Fi Gb Gc Gh Gn Hl Ho Hp Lp Lt Op Rt Ru Rv Rx Ry Rz Sf Sh Si Sj Uw Ux Uy Uz Va Vb Vc Vh Vw Vz Wb Wc Wd We Wg Wh Yd Zw Zx Tm Tl Xa Ti Th) Lv(Du Fc Fd Fi Gb Gd Gh Hl Ho Hp Lp Lt Og Op Rt Ru Rv Rx Ry Rz Sf Sh Si Sj Uw Ux Uy Uz Va Vb Vc Vh Vw Vz Wb Wc Wd We Wg Wh Yd Yh Zw Zx Tm Tl Xa) Ik(Du Fc Fd Fi Gb Gh Hl Ho Hp Lp Lt Op Rt Ru Rv Rx Ry Rz Sf Sh Si Sj Uw Ux Uy Uz Va Vb Vc Vh Vj Vw Vz Wb Wc Wd We Wg Wh Yd Yj Zq Zw Zx Tm Tl Xa) Ou(Dr Du Fc Fd Fi Gb Gc Gd Gh Gn Hl Ho Hp Lp Lt Op Ru Rv Rx Ry Rz Sf Sh Si Sj Uw Ux Uy Uz Va Vb Vc Vh Vw Vz Wb Wc Wd We Wh Yd Zw Zx Tm Tl Xa) aI(Du Fc Fd Fi Gb Gh Hl Ho Hp Lp Op Rt Ru Rv Rx Ry Rz Sf Sh Si Sj Uw Ux Uy Uz Va Vb Vc Vh Vj Vw Vz Wb Wc Wd We Wg Wh Yd Zw Zx Tm Tl Xa) iP(Dr Fc Fd Fi Gb Gc Gh Gn Hl Ho Hp Lp Lt Op Rt Ru Rv Rx Rz Sf Ux Uy Va Vb Vc Vh Vw Vz Wb Wc Wd We Wg Wh Zw Zx Tm Tl Xa Yf) Oh(Du Fc Fd Fi Gb Gh Hl Ho Hp Lp Lt Op Rt Rv Rx Ry Rz Sf Sh Si Sj Uz Va Vc Vz Wb Wc Wd We Wg Wh Yd Zw Zx Tm Tl Xa Ti Th) Wh(aK aU aZ bB bP Cw cY Dc Dd Et Hu Ij Jl Jq Jr Kk Ld Lh Lx Mj Mt Nb Nr Nx oE Ok Om On Ow Pf Pg Qh Tn Tr Uc Ut Vs) Ux(aG aH aJ aK aU bB bP bQ cE Cu cY Dc Dd dF dR Et Hu Il Jl Jp Ma Mt Nb Nq oE On Pf Qh Ri Tr Uc Vu) Xa(aG aH aJ aK aU aZ bB bP DC Dl gP Ha Hb Hu Ib In It Jl Ld Ng oE Og Ow Oy Pb Pc Pf Rg Rj Ur) Et(aA Aj Fp Gh Hq Hr Hu Ii In Ip It Jh Jk Jo Lj Lu Mm My Ng Nj Nk Nl Nm Ns Oe Of Og Oy Pb Vc) Sh(bB bF Bg Ch dR gL gP hC hF hG iH iJ Il iO iZ Jl Jp Jy kQ kR kS Nq nW oE oF oH ON Pf Uc) aZ(Du Fd Gh Hl Ho Rt Ru Rv Ry Sj Uw Uy Uz Va Vb Vc Vh Vw Vz Wc Wd We Wg Yd Yk Zw Zx Tm Tl Yf) Og(aA Fp Fr Ij In Ip It Jg Jn Jp Js Jt Lh Li Lj Ma Mn Mt Nj Nk Ns Nt Nv Nx Ok On Pb Qd) aH(Fc Fd Fi Gh Rz Sj Uw Uy Uz Va Vb Vc Vh Vw Vz Wb Wc Wd We Wg Yd Yi Zq Zw Zx Tm Tl) Jl(Fd Hl Hp Lp Rt Rv Rx Rz Uy Va Vb Vc Vj Vw Vz Wb Wc Wd We Wg Yd Zw Zx Tm Tl Ti) Aj(Ad BA cM Dc Dg dJ Fr Gh Ip Jg Jp Jt Kk Ko Kq Li Ma Mn Mt Nx On Qd Uc Yd) Dc(Rt Rx Ry Uw Uy Va Vb Vc Vh Vj Vw Vz Wb Wc Wd We Yd Yg Yj Yk Zw Zx Tm Tl) Yd(aK aU aX bP cY DR Hu Jr Js Kl Ld Nb Ng nY Ow Oy Pc Qh Qw Uu Vt) Zw(aG aK aU bB bP Cu cY dF dR gP Hu Jr Kq Ld Mf On Ow Pf Qh Tr Uc) Vw(aK aU bB bP cI Cu cY Dd Dr Fy gP Hu Ij Jp Jr Kq Nb On Qh Ri Uf) Gh(aG aJ aU bB cI Hb Hu Ij Jq Jr Ke Ki Kq Lx Mj Ow Pf Qt Tz Uh) Vz(aG aK bB bP cB Cu cY dR Hu Jp Jr Kq Ld Lx Mj Nb On Ow Pf Qh) Ug(Gc Gn Ho Ru Rv Ry Uw Uz Vb Wc We Wg Yg Yh Yi Yj Yk Tl Ti Yf) Rz(aG aJ aU bB bF bP bQ cE Cu cY dF Fy Jp Ma Mt On Ow Pf Ri) Vb(aK aU bB bP Cu Cw cY Dd Dr Fy Ij Jr Kq Mt Nb On Qh Rb Uc) Fd(aJ bB Dl dM Ha Ib In Lp Nq oE Ow Pb Pc Pf Rj Rx Ur) We(aG aK aU Cu cY Hu Jr Kq Ld Nb On Qh Rb Uc Ut Uu Vu) Rx(aK aU bA cB cT Cu Fy Jn Jq Jr Js Nb Ny oH Ow Uc) Uz(aG aJ aK aU bP Dl Hu Ib In Ld oE Ow Oy Rg Rj Ur) Dr(Fy Hp Ib Je Ki Kk Kq Ky Ld Ne Ow Tz Uc Ur Uu) bP(Fc Fi Gb Rv Va Vc Vj Wb Wc Wd Zx Tm Tl Yf) Hu(Fi Sj Uw Va Vc Wb Wc Wd Wg Zx Tm Tl Yf) Lp(Cu Hv Iv Jn Jr Js Kd Mi Mj Mx Nb oE) Vh(aG aK aU Cu cY Dl Ib Ld Oy Qh Ur Uu) Wd(aK aU bQ Cu cY Jp Mt Nb Om Qh Uc) Tl(aG aJ aK aU Dl gP Ib Ld Nb Oy Ur) Vc(aG aK aU bB cE Ij Kq Lx Pf Pg Qh) Va(aG aJ aK aU cV cY Mp Ow Qh Rm Uc) Sj(bB cI gP Hb Ij Lx Ng Pb Pc Uu) Rt(aJ Cu Dl dR Ib Jr Oy Uc Ur Uu) Yi(aG Dl Ha Ib Ld Oy Rj Ur Uu) Wc(aG aK aU cY Dl In Jr Ld Qh) Wb(aK bB cY Jr Ld Mf Ow Pf) Wg(aG aJ aK aU Dl Ib Oy Ur) Fi(bB cI Cu gP Ij Kq Lx) Gd(aM Cu dN kC Mt nY Pf) Uw(aG aK aU Jr Oy Qh Uu) pH(Af cJ Hq Il kE kF Ny) Hl(aJ Dl Ib Jr Uc Ur) Yj(aJ Dl gP Ib oE Oy) Ry(Cu Jq Jr Js Nb Uc) Uy(aG aK aU Ld Nb Qh) Yf(aJ cI Ib Oy Ur) Ti(Li Nb Oa Ow Vt) Gc(Ap Kq oH Ri Uu) Tm(aK aU cY Ld Nb) Du(aJ bB Jr Ow) Th(kC Li Pc Vt) Yg(cY Ib Oy Qh) Yh(aU bB cY Ib) Zx(aK aU Ld Ow) Rv(aJ Jr Pf Ri) Fc(Kq Lx Pg) On(Jk Of Oy) Kj(oO oP) Ok(Hr Of) Vj(Qh Ri) DlHo NbHp IbYk IzKo SfaJ ZqoH UrmE} Nb{Tl(Af aG aH AJ aK Ao aR aU aW aZ bB Bc bF Bg bM bP bQ bS bZ cB cE cG Ch cL CO cQ Ct CU Cx cY dA Dc Dd dF dI dM Dr Du Ed Et Ez Fc Fi Fy Gp Ha Hb Hl Hq Hu Ib Ii Ij Ik Il In It Je Ji Jl Jp Jy Kd Ke Ki Kk Kq Ks Ky Kz Ld Lh Lv Lx Ma Mf Mg Mi Mj Mm Mn Mp Mq Mt Mv My Mz Nn Nq Nu Nv Ny Oa Oe Og Oh Oi Ok Om On Op Or Ou Ow Oy Pa Pb Pc Pe Pf Pg Ph Qb Qc Qd Qe Qh Qt Qw Rb Rg Ri Rj Rm Rt Rx Ry Sj St Tn Tz Ub Uc Ue Uf Uh Un Ut Uu Vq Vt Vz Wf Yd Yl Ye Tm Xa Ti) Ti(aA Aj Ar aW aZ bR CH cQ Cs Ct dC dJ Du Ed Et hB Hu Id Ii Il In It Jg Ji Jj Jl Jo Jq Ke Kk Ko Kp Kq Ky Ld Li Lj Lp Lv Md Mf Mj Ml Mp My Mz Nf Ng Nk Nn No Nu Ny Oa Of Oh Oi Or Ow Oy Oz Pb Pc Pk Pz Qd Qv Qz Rh Rj Rt Rx Sr Tz Ua Ub Uc Ud Ue Uf Ug Uh Uk Ul Um Un Uo Up Ur Us Ut Uu Uv Uw Ux Uy Uz Va Vb Vc Vh Vj Vo Vq Vs Vt Vw Vz Wb Wc Wd We Wf Wg Wh Yd Yl Zq Zw Ye Tm Xa Wm) Rx(aH aI Ao As bB bI bQ bZ cE cG cL cO cT cU cV Dc dF Dk Ed Et Ez Fd Hb Hf Hq Hx Ih Ij Il It Ji Jn Jr Ke Kk Ko Kq Ks Ky Kz Ld Lh Lu Lx Ma Mf Mj Mq Mr Mt Mv Mz Nf Ng Ni Nn No Nq Nv Ny Oa Ok Om On Or Oz Pa Pe Pf Pg Po Qb Qc Qd Qe Qh Ql Qm Qt Qw Rm Sr St Tn Tr Tv Uc Uf Ug Uh Ur Ut Uw Vp Vq Vt Vv Vz We Yi Zq Tm Xa) Tm(aG aH aI aU aW bB bF bM bQ bS bZ cE cG cL cO cQ CU Cw Dc Dd Ed Et Ez Fi Fw Gc Gp Hb Hl Ib Ij Il In It Je Ji Jm Js Kd Ke Kk Ko Kq Ld Li Lu Lv Lx Ma Mb Mf Mg Mk Mm Mn Mp Mq Mt Mx Mz Nn No Nq Ny Oe Oh Om On Op Or Ou Ow Oz Pa Pd Pe Pf Pg Pj Qv Qw Rj Si Sr Tz Uf Ug Un Ur Wf Ye) Wf(aH aI bB bF Bo bQ bZ cG cQ CU Ed Et Ez Gz Hl Hq Hx Ij In It Ji Jl Jn Jr Js Ke Kz Ld Lv Lx Ma Mj Mk Mp Mq Mr Mt Mv Mz Nf Nh Nn No Nq Nv Ny Oh Om On Or Ou Ow Oz Pe Pf Pg Qd Tn Tz Ug Uh Un Ur Ut Vq) Vj(aI Aj aL aW aX aZ bF Bo bQ bZ cC cL cQ cR CT CU cV Dc dF Et Fd Fy Hf Hl Ij Il It Ji Jl Js Ki Kk Kq Ks Ld Lv Lx Ma Mb Mf Mp My Mz Ng Ny Oh Or Ow Oy Oz Pa Pf Pg Qh Qt Rm St Tv Tz Ug Uh Un Ur Vq) Vb(aG aH aI aW bB bF Bo bQ cG cL CO cS cU Cw Ed Et Ez Hl Ij It Ji Ke Kk Ko Kq Li Lv Lx Ma Mf Mg Mi Mm Mp Mq Mt Mv Nn Nq Oh Om On Ou Ow Oz Pd Pe Pf Pg Pj Ue Uf Ug Uh Un Ur Vq Zq) Ye(aH aP Bo bZ CU Ed Et Ez Fw Ih Ij It Jl Jn Ke Kk Kq Kz Ld Lx Mp Mq Mr Mv Mw Nf Nn Nq Ny Oa Oh Om Or Ou Ow Oz Pe Pf Qb Qd Qe Qy Rm Tz Uf Ug Uh Un Ur Ut Vq) Ow(Dr Eq Fc Fd Fi Gb Gc Gd Gh Gn Hl Ho Hp Lp Lt Op Rt Ru Rv Ry Rz Sf Sh Si Sj Ux Uz Va Vc Vh Vw Vz Wc Wd We Wg Wh Yd Yg Yh Yi Yj Yk Yl Zq Zw Zx Xa Th Yf) We(aH aZ Bo bQ bZ cQ CU Ed Et Ez Hl Hq Ij It Ji Jl Ke Kk Ld Lv Lx Ma Mf Mk Mp Mq Mv Nh Nn Nq Oh Om On Or Ou Oy Oz Pe Pf Pg Rm Tz Ug Uh Un Ut Vq) Wd(aI Aj aZ Bo bZ CO cQ cU Ed Et Ez Hl Ij Ji Js Ke Kk Ld Lv Lx Mb Mi Mp Mq Mu Mv My Ng Nn Nq Oh Om Or Ou Oy Oz Pd Pe Pf Tz Uf Ug Uh Ur Vq Zq) Rt(aI aZ bF bQ bZ cE cG cL CU dF Ed Et Ez Fy Ji Jl Jq Js Kk Ks Lv Lx Ma Mf Mp Mz Nn Nq Oh Om On Or Oz Pf Pg Sj Tn Tz Uc Uf Ug Uh Un Ut Vq) Hl(aW cU Ed Il Kk Kq Ld Lx Mp Nf Nn Nq Oa Oh Om Or Ou Oz Pf Qv Rj Tz Ub Uc Ue Uf Ug Uh Uk Un Ur Ut Uu Vh Vp Vq Vt Vu Vv Vz Wc Wg Yl Zq) Wh(aH aZ Bo bZ cQ CU Ed Et Ez Hq Ij It Ji Js Ke Kk Ld Lv Lx Mb Mf Mp Mq Mv Nn Nq Oh Om On Ou Oy Oz Pe Pf Pg Rm Tz Uf Ug Uh Un Ur Vq) Va(aH aI aZ Bo bZ cQ CU cV Dc Ed Et Hb Ij It Ji Js Ke Kk Kq Lv Lx Mf Mp Mq Mz Oh Om On Or Ou Oz Pe Pf Pg Qh Qm Rm Tz Uf Ug Uh Un Vq) Ux(aH aW aZ Bo bZ cG CO cQ cS cU Ed Et Ez Ij Ke Kk Ld Lv Lx Ma Mg Mm Mp Mq Nn Nq Oh Om On Or Ou Oy Oz Pe Pf Ug Uh Un Uu Vq Zq) Uh(Dr Du Eq Fc Fd Fi Gb Gc Gh Gn Ho Hp Lp Lt Op Ru Rv Ry Rz Sf Sh Si Sj Uw Uy Uz Vc Vh Vw Vz Wb Wc Wg Yd Yl Zq Zw Zx Xa Th) Oz(Eq Fc Fd Fi Gb Gh Ho Hp Lp Lt Op Ru Rv Ry Rz Sf Sh Si Sj Uy Uz Vc Vh

Figure 28 Continued

Vw Vz Wb Wc Wg Yg Yh Yi Yj Yk Yl Zq Zw Zx Xa Th Yf) Un(Dr Du Fc Fd Fi Gb Gc Gh Gn Ho Hp Lp Lt Op Rv Ry Rz Sf Sh Si Sj Uy Vc
Vh Vw Wb Wc Wg Yd Yg Yh Yi Yl Zq Zw Zx Xa Th Yf) Oh(Du Eq Fc Fd Fi Gb Gh Ho Hp Lp Lt Op Ru Rv Ry Rz Sf Sh Si Sj Uw Uy Uz Vc
Vh Vw Vz Wb Wc Wg Yd Yl Zq Zw Zx Xa) Lx(Du Eq Fc Fd Fi Gb Gh Ho Hp Lp Lt Op Ru Rv Ry Rz Sf Sh Si Sj Uw Uy Vc Vh Vw Vz Wb
Wc Wg Yd Yl Zq Zw Zx Xa) Ug(Dr Du Eq Fc Fd Fi Gb Gc Gh Gn Ho Hp Lp Lt Op Ru Rv Ry Rz Sf Sh Sj Uw Uy Vc Vz Wb Wc Wg Yd Yl
Zw Zx Xa) Uw(aH Aj aZ bB Bo bZ cQ Ct CU Ed Et Ez Ij Ji Jk Kk Lv Mb Mp Mq Nn On Ou Oy Pe Pf Pg Qv Ut Uu Vq) Ur(Dr Du Eq Fc Fi
Gb Gc Gh Gn Ho Hp Lt Ru Rv Ry Sf Si Sj Uy Uz Vc Vw Vz Wb Wg Yh Yj Yk Yl Zw Zx Yf) Zq(aH Aj Ap aX aZ Bo bW cU Dl Ed Gd li Ik Kf
Ki Kj Mh Or Ou Pf Pz Qt Qu Qv Qz Rz Ss Tz Uu Vw) Ld(Dr Du Eq Fi Gb Ho Hp Lp Ru Rv Rz Sj Uy Vc Vh Vz Wb Wc Wg Yd Yg Yh Yi Yj
Yk Yl Zw Zx Xa) Kq(Dr Du Fc Gc Gh Gn Hp Lt Op Ru Rv Sf Si Sj Uy Uz Vh Vw Vz Wb Wc Wg Yd Yh Yl Zw Zx Xa) Uy(aH al aZ Bo bZ cQ
CU Ed Et Ij Ji Ke Kk Lv Mf Mp Mq Nn Or Ou Pe Pf Pg Tz Vq Vt) Eq(Ao aW bQ cG cL CO cS Cu Ef Et Kk Ma Mp Mt Mu Mz Nn Nq On Ou
Pf Uc Ue Uf Vq) Vh(aH al Aj aZ Bo bZ cQ CU Ed li Ij Ji Ki Kk Lv Mp Mq Of Or Ou Oy Pe Pf Uu Vq) Vw(aH aZ Bo bZ cQ cU Ed Et Ez Ij Ji
Kk Lv Mp Mq Nn On Or Ou Oy Pe Pf Tz Uf Vq) Wc(aH al aZ Bo bZ CU Ed Et Ij Ji Js Kk Lv Mb Mp Mq Nn Ou Oy Pe Pf Pg Vq) Pf(Du Fc Fd
Gb Gh Ho Lp Op Ru Rv Ry Sf Sh Sj Uz Vc Wb Wg Yd Zw Zx Xa) Du(bZ cU Et Ji Js Kx Kz Lv Mf Mp Mq Nf Nn Oa Or Ou Pe Qv Tz Vq)
Ed(Dr Fd Fi Gb Gc Gn Hp Lp Ru Rv Ry Rz Sf Sh Si Sj Yd Yi Zx Xa) Yl(aH Bo bZ CU Et Ez Fw Ij Kk Mp Mq Mt Nu Or Ou Pd Pe Us Vq)
Xa(aH al aW aZ Bo bZ CU Et li Ij In Kk Mp Or Ou Oy Pe Rj) Mp(Fd Gb Ho Lp Ru Rv Ry Rz Sf Sh Vc Vz Wb Wg Yd Zw Zx) cU(Fd Gb Gh
Lp Op Ru Rv Ry Sf Sh Si Sj Vc Vz Wb Wg Yd) Vz(aH aW bZ Cu Et Fw Ij Il Kk Mq Mt Nu Ou Pe Vq) Or(Dr Fc Fi Gb Gc Gn Ho Lp Ru Ry Rz
Sh Wb Yd Zw) Kk(Dr Gb Gc Gn Ho Lp Ru Rv Ry Rz Sh Vc Wb Wg) Et(Aj Fi Lp Ru Sj Vc Wb Wg Yd Yh Zw Zx Th) Bo(Hp Lp Sj Vc Wb
Wg Yd Yg Yh Yj Zw Zx) Ou(Dr Fc Lp Op Ru Ry Sh Vc Wb Wg Yd Zw) Vq(Dr Gh Ho Lp Ru Rv Ry Rz Sf Sh Th) Vc(aH bZ Cu Ij Ji Lv Ma
Mq Nn Pe) Tz(Dr Fc Fi Gc Ho Ru Rv Ry Rz) Yd(aH bZ Cu Ij Kz Lv Mq Pe Qv) Wg(aH bZ Cu Ij Ji Lv Mq Nn Pe) Zx(aH al bZ Ij Kz Nq Pe)
Ru(aZ Ji Lv Mr Nq Qd) Wb(bZ Ij Lv Mf Mq) Zw(aH bZ Cu Ij Pe) Rz(bZ Cu Ez Nn Uf) Ry(bQ Ny Sr Vt) Th(Ji Li Vt) Mq(Hp Sj Uz) Sh(Lv Nn
Om) Lp(cL Ij Pe) Rv(bQ bZ Uf) Op(Nf Oa Uu) Fd(aW Qv) Gc(Rj Uu) Uz(aH Cu) FcKy MvHp MzjK SfRj SjPe JiJj} Kq{Ux(aD aE AF aG Aj
Al aM AN aO Ar Aw AX aY aZ bA Bb Bg bJ bL bM BN Bo bU bV cD cE cG Cp cQ Cs Ct Cw CX dA Db Dd De Di Dk Dp Dr Ed Ef Eq Ez Fc
Fw Fy Gc Gp Hr Hu Ib Ic Il Ir It lu lv Jd Je Jg Jj Jn Jq Js Kd Kf Kg Ki Kj Kk Kl Kp Kr Kx Ld Li Lj Lp Lu Lx Lz Ma Mb Me Mf Mh Mj Mk Ml
Ms Mt Mu Mv Mx Na Nc Nd Ne Ng Ni Nj Nk Nl Nn Nq Nr Ns Nu Nv Ny Oa Oe Of Oh Oi Ok Or Ou Ow Oy Pa Pc Pf Pk Po Qb Qc Qe Qh Qm
Qn Qt Qv Qw Qx Qy Ra Rc Rf Rj Rm Rt Ru Rx Ry Ss St Ua Uk Ul Up Ur Us Ut Uu Uv Uw Uy Va Vb Vh Vp Vq Vs Vt Vw Wc We Wh Yd
Ye Xa Wm Th) Aj(Ap aW BA bJ bN bX cA CH cP cQ cT Dc Dd De Dg dJ Dr Du Eq Et Fd Fi Fw Gb Gc Gh Hc Hl Ho Hp Hq Ic Id Ik Il Ip Iu
Jg Ji Jm Jr Kc Kd Kf Kk Kn Ko Kp Ks Kz Ld Lh Lj Lt Me Mh Mk Mt Mv Nd Nf Ni Nj Nl Nr Of On Op Ow Pb Pi Pk Qc Qe Ri Rt Ru Rv Rx
Ry Sf Sh Si Sj Uh Uo Ur Uw Uy Uz Va Vb Vh Vw Vz Wb Wc We Wg Yd Yh Yi Yk Yl Zq Zw Zx Ye Tm Tl Xa Ti Th) Ru(aA Ad Af Ao Ap
Aw aZ bM bW cA cK cQ cR Cs Dg Dr Ed Ef Fc Fi Gc Gd Gl hB Hx li Ik Iz Jd Jg Ij Jn Jo Jr Js Kc Kf Kg Kj Kl Ko Ky Ld Lj Lz Ma Mq Mr Ms
Mx Nd Nf Ny Oa oE Oh Oi Ok Or Ow Oy Pb Pc Ph Pz Qb Qx Rc Rh Rt Sh Ss To Tz Ug Ur Uw Vb Vc Vo Vs Vt Vw We Wh Yd Zw) Eq(aA
aC aK aN aU aW aX aY aZ bU cD cI cL cQ Cv Db Dg dK Ed Ex Fc Fw Gb Gc Gh Gl Hw li Ik Il Jm Kd Ko kQ Ld Li Lj Lv Mf Mq Mt Mu Mv
Mx Ng Ni Nn No Nv Nx Oa Oh Oi Ok On Ow Oy Pa Pb Pc Pf Po Qb Qn Rc Sj St Ul Ut Uu Uw Vb Wc Yd Tm Xa Th) Th(Aw Ax aY Bc Bg bJ
bL bR bU cE cF cG Ch Co cQ Cs Ct De Dr Ed Gl Hq Ij Kd Kl Ky Ld Li Lj Lu MY nB Ng Ns Nv Oa Of Oh Oi Pb Pd Ph Qe Qw St Ua Uk Um
Vs Vt) Ed(Dr Du Fc Fd Fi Gb Gc Gh Gn Hl Ho Hp Lp Lt Op Rt Rv Rx Ry Rz Sf Si Sj Uw Uy Uz Va Vb Vc Vh Vw Vz Wb We Wg Yd Yg Yl
Zw Zx Ye Tm Tl Xa Ti) Yd(aX bA Bg bW cQ cR cW DC Gc Gp Ik Je Jm Jn Jr Js Ld Lj Lu Lv Mp Mx Nd Ng Oa Oh Oi Or Ou Ow Oy Pa Pb
Qb Qh Rm Ss Tz Vb Vs Vt Vw) Oa(Dr Du Fc Fd Fi Gb Gc Gh Gn Hl Ho Hp Lp Lt Op Rt Rv Rx Ry Sf Sh Si Sj Uy Va Vb Vc Vh Vw Vz Wb
Wc We Yh Yl Zw Zx Ye Tm Tl Xa Ti) Oh(Dr Du Fc Fd Fi Gb Gc Gh Gn Hl Ho Hp Lp Lt Op Rt Rv Rx Ry Sf Sh Si Sj Uy Va Vb Vc Vh Vw Vz
Wb Wc We Wh Yl Zw Ye Tm Tl Xa) aZ(Dr Du Fc Fd Fi Gb Gc Gh Gn Hl Ho Hp Lp Lt Op Rt Rx Ry Sf Sh Si Sj Uw Uy Va Vb Vc Vh Vw Vz
Wb We Yk Yl Zw Zx Ye Tl Xa) Dr(aW aX Bg bL cB cQ Dg Ef Fn Fw Gl Je Jm Jn Js Kd Mf Mx Nd Ng Nx Oi Ow Pa Pf Qb Ss Uu Vs Vw)
Vb(aD Af aN aW aY cD De Ex Fw lh Ij Il Jm Jn Ld Lj Nd Nn Nx Oi Ow Pa Pb Pf Sr St Ul) Fc(Ap aW cA cK dR Ex Fw Gl Il Jd Jm Kl kR Lj
Mh Nd Ng No Nx Ow Oy Pf Uu Uv Vc) Vw(Ax bA Bg Ch Co Cs Iz Jd Jn Js Ld Li Lj Nd Nn Oi Ou Ow Oy Pf Ra Sr Ur Uu Wm) Ld(Du Fd Fi
Gc Gh Lp Op Sj Uw Uy Uz Va Vc Vz Wb Wh Yl Zw Zx Ye Tm Tl Xa) Oi(Du Fd Gb Gd Gh Gn Hl Hp Lp Rt Rx Ry Sh Si Sj Va Vh Vz Wb Yl
Xa) Ow(Du Fd Fi Gc Gd Gh Hp Lp Op Sh Si Uw Va Vc Vz Wb Wc Zw Ye Xa) Lj(Du Fi Gb Gc Gh Gn Hl Hp Lp Rx Ry Sh Si Sj Uw Wb Yg Zw
Ye Ti) Rt(aC aX bA cR Dc Jm Js Mx Ng Ny Oy Pa Qb Qh Rm Ss) Sh(aW aY bL Ex Gl Il Jm Mx Nd Nn Nx Pf Ul Uu Vs) Gc(Af aW aY Bg Gl
Jm Kd Kg Kl Ng Nx Uu Uv Vs) Uw(Ao aW Fw Gl Il Jm Js Li Mx Nx Pa Pf Sr Uu) Gh(Af aW Bg De Fw Gl Il Jm Kd Kl Mh Pf Us) Rx(Bg bW
cQ cR Iz Jn Js Mm Ng Ny Oy Rm) Uu(Du Fi Ho Hp Rv Sf Si Sj Vz Wc Zx Tm) Ti(Bg Ch Co cQ Iz Kd Li Ng Oy Pb Vs) Vc(aW Ex Fw Gl Ij Il
Jm Lx Mh No Nx) We(aY bL Ik Jn Mx Pa Pb Qb St Ul) Fi(aW Ex Fw Gl Il Jm No Nx Pf) Ye(Ao iZ Jm Jn Kg Nd Pb Qb Rm) Yh(bA bW Ch
My Nd Oz Qz Wf) Xa(cQ Gl Jd Ng Nx Oy Pb Vs) Gb(Af De Ex Il Jm Kl Vs) Wh(aW Ih Mx Nn Nx Pf Um) Ng(Gn jT Lp Sj Yi Tm) Wc(aX bA
Jm Kd Oy Ss) Rz(aY Ex Gl Li Lw Mt) Wf(dE Nn Pf Um Vu) Jm(Ry Si Vz Yl Tl) Lp(Bg Pb Rj Ug Vs) Va(bL cQ cW Nd Rm) Ch(Uh Wg Yk
Zq) Yg(Ij Jn Nd Yi) Zw(Js Mf Pf Rm) Pb(Fd Gn Sj Vh) Ao(Du Sj Tl) Bg(Du Sj Tm) Wd(aW Vu Wg) Uy(bL Kd oE) Em(Jj Kj) Gl(Fd Tl) Yi(aX
Kl) Wb(Mf Pf) Vz(aW Mx) Ry(Kd Nd) Oy(Sf Tm) GdPa IbjT IjVh JiiB WgQz JjcQ} Ow{Wb(aA aC AD aE AF aG aH aI AJ aK AL aM AN
AO AP aQ AR AS aU aV aW AX aY aZ BA BB BC bE bF BG bH bI bJ bL bM BN BO bP bQ bR bS bU bV bW bX bZ cA cC cD cE cF cG
CH cl cJ cK cL cM cN CO CP cQ cR CS CT CU CV CW CX cY cZ dA DB dC DD DE dF DG dH Dl dJ DK DL dM dN Dp Dr Du Ed Ef Em
Eq Et Ex Ez Fc Fd Fi Fn FP FR Fw Fy Gb Gc Gd Gh Gl Gn Gp Gz Ha Hb HC Hf Hl Ho Hp Hq Hr Hu Hv Hw Hx Ib Ic Id Ih Ii IJ Ik In IO Ip Iq
Ir It Iu Iv IZ Jd Je Jf Jg Jh Ji Jj Jk Jl Jn Jo Jp Jq Jr Js Jt Ju Jv Jy Kc Kd Ke Kf Kg Ki Kj Kk Kl Kn Ko Kp Kr KS Ky Kz Ld Lh Li Lj Lp Lt Lu Lv
Lw Lx Ly Lz Ma Mb Mc Md Me Mf Mg Mh Mi Mj Mk Ml Mm Mn Mp Mq Mr Ms Mt Mu Mv Mw Mx My Mz Na Nc Ne Nf Ng Nh Ni Nj Nk
Nl Nm No Nq Nr Ns Nt Nu Nv nW Nx NY Oa Oe Of Og Oh Ok Om On Op Or Ou Oy Oz Pa Pb Pc Pd Pe Pg Ph Pi Pj Pk Po Pz Qb Qc Qd Qe
Qg Ql Qm Qn Qt Qu Qv Qw Qx Qy Qz Ra Rb Rc RfRg Rh Ri Rj Rm Rt Ru Rv Rx Ry Rz Sf Sh Si Sj Sr Ss St Tn To Tr Tt Tv Tz Ua Ub Uc Ud
Ue Uf Ug Uh Uk Ul Um Un Uo Up Ur Us Ut Uu Uv Ux Uy Uz Va Vb Vc Vh Vo Vp Vq Vs Vt Vu Vw Vz Wc Wd We Wf Wg Wh Yd Yh
Yi Yl Zq Zw Zx Ye Tm Tl Xa Wm Tj Ti Th Yf) Dr(Al Ap As aW aZ BC bF BG bO bX bZ cB Ch CQ CU cV Cx Dc Dk DL Dp dR Du Ed eM
Fd Fi Fr Fw Fy gL Gp Gz hB Hc hG Hl Ho Hq Hu Hv Ij Ik In Iz Je Jf Jk Jl Jm Jn Jp Jr Ju Jv Jy Kd Ki Kk Kn Kp Ks Kx Lp Lu Lv Me Mh Mj
Mn Mp Ms Mt Mu Mv Mw Mz Nd Nj Nm Nn Nq Nr Nv Ny Oa Oe oF Og Oh Oi oK On Or Ou Oz Pb Pc Pd PF Pg Pi Qc Qd Qe Qh Qm Qu Qv
Qw Qy Rb Rm Rt Ru Rx Ry Sj Sr St Tn Tr Tz Ua Uc Um Ut Va Vp Vu Wc Vz Ye Tl Xa) Ny(Du Eq Fc Fd Fi Gb Gc Gh Gn Hl Ho Hp Lp Lt
Op Rt Ru Rv Rx Ry Rz Sf Sh Si Sj Uw Ux Uy Uz Va Vb Vc Vh Vw Vz Wc Wd We Wf Wg Wh Yd Yg Yh Yk Yl Zw Zx Ye Tm Tl Xa Ti Th)
JI(Eq Fc Fd Fi Gb Gc Gd Gh Gn Hl Ho Hp Lp Lt Op Rt Ru Rv Rx Ry Rz Sf Sh Si Sj Uw Ux Uy Uz Va Vb Vc Vh Vw Vz Wc Wd We Wf Wg
Wh Yd Yg Yh Yl Zw Zx Ye Tm Tl Xa) Va(aE Al Bg bM cQ Cu Dc Dd dH Dk Ed Hp Ih Ij Il Jh Jk Jm Jn Jp Jr Jy Ks Mu Mv Mz No Nt Oi On
Or Oz Pc Pi Qc Qd Qe Qh Qy Rb Rm St Tn Tz Uc Un Zx) Du(Ax Cq Cs Cu Dc Dd Ed Em Fp Fy Hv Ij Il Iv iZ Jn Jp Jr Js Kd Ki Mj Mr Mt Mx

Ng(Gb Zq) Yl(Fw Pe) Oa(Zx Ti) DcRt ThQd Filj GdbA TzYh YjfP WdaE RmVa} On{Uu(Dr Du Fc Fd Fi Gb Gc Gh Gn Hl Ho Hp Lp Lt Op Rt Ru Rv Ry Rz Sf Sh Si Sj Uw Ux Uy Uz Va Vb Vc Vh Vw Vz Wc Wd We Wf Wg Wh Yd Yl Zw Zx Ye Tm Tl Xa) Ed(Dr Du Eq Fc Fd Fi Gb Gc Gh Gn Hl Ho Hp Lp Op Rt Ru Rv Rz Sf Sh Sj Uw Ux Uy Va Vb Vc Vh Vw Vz Wc We Wf Wh Yd Yh Yl Zw Ye Xa) Wf(aE aZ bM Bo Fw Gl Hr Ih Jl Jn Ki Lj Ny Oa Pe Qv Ug Um Uv Va Zw Xa Th) Aj(Et Jg Jt Ko Li Mn Va Wc Wd Yd Yk Th) Oy(Et Hr Ii Ij jO Lj Mb Mn Nj Ns Og Th) Th(Ct Ky Li Lj Ng Ns Of Uk Vt We) Oa(Dr Du Gc Gn Rt Ry Yh Zw Ye Ti) Eq(aW Ef Li Mi Mp Mq Mt Mu Qy) Gl(Fd Gh Ho Rv Sh We Wh Tl Xa) aZ(Rt Ru Va Wc We Wh Yd Yk) Yh(Li Lj Mp Of Oh Qd Vt) Zw(Ih Ir Lj Of Oh Qe Rj) Uv(Rt Va Vb We Wh Tl Xa) Va(Ch cQ cW Dc Or) Ns(Jj My Oe Og) Yd(Lv Mp Of Vt) We(aY Kd Mq Ny) Wh(Bo Fw Ki Pe) Lj(Jj Og Rt Ti) Rt(Dc Kd Qh) Ch(Wd Zq) My(Hr Nj) Jj(Of Og) Ru(Ug Vt) Oe(Ux Vb) aW(Rz Vz) BoVc MqYe NgjO IjOg XaOi KdVh LpUg} Oa{Ti(aA aQ aW bF Bg bR Ch cQ cS Cu Cv Dp dR Ed Et Fr hB hG Il Jh Jl Jp Jy Ky Li Lv Ma Mt Mv Ni Nj Nq Nu Ny Oe Oi Ou Qd Qz Ub Uf Ug Ur Ut Vt) Nq(Dr Du Eq Fc Fd Fi Gb Gc Gh Gn Hl Ho Hp Lp Lt Op Ru Ry Rz Sf Sh Si Sj Vz Wf Yd Yl Zw Zx Ye Tm Xa) Gc(aZ bF BG bQ bZ cE Ch Co Du Hc Hq Il Jl Jp Jy Lv Ma Mt Mv My Ou Ri Tn Ut Zx) Dr(Ao bF Bg bZ Co CU Ef Gp Hq Il Jp Jy Lv Ma Mg Mn Mt Mv Om Ou Uc Ut Zx) Mt(Du Eq Fc Fi Gh Gn Hl Ho Op Ry Rz Sf Sh Sj Vz Wf Wh Yd Yl Zw Zx Ye Tl) Du(aG aU bB bZ Cu Cw cY Et Jp Li Mv Ou Qv) Ye(Cu Ef gL Hq Jh Jy Mu Mv Mw Qd Ua Uc Ut) Zx(aG aZ bQ Cu Dd dI Ur) Gn(Cu Hv Jy Mi Mv Ou) Wf(Ef Jl Jy Mv Tn Ut) Vc(bZ cE Ij Ma) aZ(Eq Ho Wd Yd) Mv(Eq Hl Op) Uc(Hl Rt Ry) Cu(Rt Zw) Il(Hl Vj) Si(bF Jy) Ou(Rt Ru) EfEq EtTh FcJy GhIj YdaG ZqfP ZwUt UhiB} Jl{Wf(aN aW aY Bb bJ Bo cP cQ cW Cx Ed Ex Fw Gc Gh Gp Hu Ic Ih Ij Il Jd Jh Jm Jn Jv Kd Ke Li Lj Mq Mr Mt Mw No Nq Nr Nu Nv Ny Oh Om Pa Pe Qc Qd Qe Qm Qw Qy Sr St Tz Uh Ut Zx) Cx(Eq Fc Fd Fi Gb Lp Op Rt Ru Rv Rz Sh Uw Ux Uy Uz Vb Vc Vh Vj Vw Vz Wc Wd We Wg Wh Yd Yk Yl Zw Zx Ye Tm Tl Xa) aW(Du Eq Fc Fd Fi Gh Hl Ho Hp Lp Lt Op Ry Rz Sf Sh Si Sj Ux Vw Vz Yd Yg Yh Yl Zw Zx Ye Tm Tl Xa) Li(Eq Fc Rt Ru Rz Uw Ux Vz Wd Wh Yd Yh Zw Ye Th) Ij(Rt Uw Va Vb Vc Wc Wh Yd Zw Th) Vj(Af Ch Ex Fw Il Jm Pa Ul Th) Gc(Ed Rj Ru Ur Us Uu Uv Yd) Ye(cQ Ed Jn Mq Mw Qd Qy) Rt(Dd Il Kd Mf Sr Uk) Ru(aZ Ed Mq Pc Vt) Yd(Gp Ke Pj Uh) Sh(Il Jv Oi Sr) Ed(Dr Xa Ti) Oi(Sf Wd Xa) Aj(Et Ko) Du(Mk Oh) Ti(cQ Lj) Lp(Rj Ur) EfZq EqMt SiUu ZwOh WhPe KdRy UhVa} Aj{Et(aA Ad Af Al Ao Ar AW Ax BA Bb bN BO cH cI Co cP CT Cu Cw Cx Dc Dd Di dJ Fr Fy Hq Hv Hw Ih Ij Il Ip It Iv Jg Jh Jk Jm Jn Jo Jp Jr Jt Kn Ko Lh Li Lj Lv Lw Lx Ma Mc Md Mg Mh Mi Mj Mk Ml Mn Mp Mq Mr Mt Mu Mv Mw Nj Nl No Nq Nr Ns Nt Nv Nx Ny Oe Of Og Oi Ok Om Ou Oy Pc Pe Pg Po Pz Qb Qc Qd Qe Uc Wm) Om(Eq Fc Fi Gb Gd Ru Rz Si Va Wc Wd Wh Yk Xa) Jg(Cu Dc Ij Jt Lh Li Ma Mt No Nx Qd Qe) Qd(Ad Ap Ba Dg Jt Ko Ma Mn Ru Uh) Uc(Dr Fc Kn Ko Ry Uh Va Wf Xa) Ut(Dr Fc Ho Va Wd Wf Yd Xa) Dc(Ap Ba Fr Li Ma) Qe(Ap Ba Dg Ma Uh) Jt(Ba Dg Fr Ma) Ad(Li Ma Mn) Ko(Il Lh Oh) Ru(Cu Ef Ou) Xa(Cu Nq) BaIp NmvI MtWe QcWd JpVq dJqZ} Ij{Vc(AA aE aH aZ bM bQ bZ cE cP Cu Ed fR Fw Gd Gz hB Hf Hq Ii In Jo Jt Ki Kk Kp Lv Lx Ma Mt Ni Nv Or Pg Pj Qc Qd Ug Uu Vb Vz) Vb(Aa bH Cu Gh Jk Jy kS Mi Mq Mt Mu Nd Ni Rh Uc Ut Vu Tj) Nd(Eq Rt Ry Va Vh Wc We Wh Yd Yl Zw Ye Tm Tl Xa) Wh(aA aE aZ Cu Hv Ii Ki Kk Mt Nv Om Qd Ri Um) Th(hB Ii Ml Ni Nk Oi Qd Ug Un Uv Vt Tj) Wc(Dc Fd Jn Jr Lv Ny Or Pg Pi Rh Tv Tz) Fi(aW Co Ez Hv Li Mp Mq Mt Mu Om Uf) Ii(Du Fd Uw Vz Yd Tl Xa) Va(aZ cV Dc Or Rm Tz Uc) Et(Jj Ng Og Oy) Fc(Ed Kk Lx Xa) Gh(aZ Kk Lx Um) Jn(Vz Zw Ye) Xa(cA cQ Oi) Ux(Mu Nq Tj) Cu(Vh Vw) Wf(In Ut) Jj(Lh Ok) TjRz GdnH YkOr VzkQ RtdR OgOk VhcQ} Ny{aW(Du Eq Fc Fd Fi Gh Lp Ry Rz Sf Sh Vb Vw Vz We Wh Yd Yg Yj Yl Zx Ye Tm Tl Xa Ti Th) Mf(Rt Va Vh Vj Wd We Wf Wh Yd Yj Zq Zw Ye Tl Xa Ti) Wf(Co Ef gL Il Jp Jy Lv Ma Mk Mt Mu My Ni Nq Ut) Ye(bJ Ef Ih Jn Li Mk Mq Mt Mw Nq Nu Qd Qe) Rj(Gc Rz Sf Va Vj Wc Wd Wh Xa Ti Th) Mt(Eq Rt Rz Vb Vh Vw Wd We Wh Yg) Mk(Ru Uy Vb Vw We Wh Yl Xa) Ti(Li Nk Nu Oe Oh Oi Vt) Xa(Af Cx Ib Mb Oe Oi Vq) Th(Ar Li Oe Oh Oi Vt) Wh(bZ Cu Ib Lx Ma Nq) Eq(cS Ef Ma Mv Nq) Wd(Ib Mb Oi Uu) Oi(Ho Rz Vj) Uu(Fi Gc Ho) Cu(Rt We) Lx(Gh Vc) Ib(jT Yk) Va(Oh Vq) NqRu LvYd MaRt YiOe WcVq WeUt JmVj UhiB} Ke{dJ(eZ fN fY hL hP pS pY qB qD qQ qZ rN rO rP rQ rR rS rT rU rV sC sK sM sO tO tR uL uM uN uO uP uT uU uV uY uZ vB vC vH vI vO vP vQ vS vT vV vW wB wC wD wF wG wH wJ wK wL wP wQ yD yH yJ yK yL zG zH yE tM tL xA) cQ(eT eZ fN fY hL hO hP hV hX iB iC jE jF jG jQ jT jY pY qA qB qC qD rN rS rW tS tV uM vS wC wF wP) qA(Al aQ bL Hw Jk Jn oE Ph Tz Ur) Hu(fN hP rT rU rV tT tV wC zI) oE(rN rR sK vA wD wG) fN(Ef Hc Ic Iv Jk) Il(Dr Jj Jo) rS(dC Fw Ko) Jn(hO uR) bL(sK vQ) eC(De jP) wC(bI Ri) wD(bQ nW) rR(aQ aV) FwhP NurW HceZ dDuZ eDwK wLjT} Jn{Rj(Dr Em Eq Fc Fd Fi Gb Gc Gh Gn Hl Ho Hp Lp Lt nI Op Rt Ru Rv Ry Rz Sf Sh Si Sj Uw Ux Uy Uz Va Vb Vc Vh Vj Vw Vz Wc Wd We Wf Wg Wh Yd Yl Zw Zx Ye Tm Tl Xa) Wf(aM Bg bN bQ bZ cE Co Hq Il In iZ Jp Jy Kk Lv Ma Mt Mu Mv My Ni Nj Nq Om Ou Pe Qd Qe Tn Ut) Ye(aM aP bN bZ cO Ed Ef Fw Jh Jk Jy Mq Mt Mu Mw Nq Nu Pe Qd Qe Ri Uf Va Vq Vt Vu Wh) Va(aG aZ bS cE Dc Hb Ib Lv Ou Vq) Ug(Fc Fd Fi Wh) Lx(Vc Wh Zw) Eq(Ef Nq) Vz(aW Il) Ou(Dr Yd) ZwbZ RzfP RtbQ YlPe UxaZ VhVq} Ed{Xa(bF Bg Ch Cu Fy Il In iP Jp Jy Lv Nd Ni Nj Nq oF Og Oi Ou Rb Rm Tr Uc Zx) Uc(Dr Eq Fc Fd Fi Gn Rt Ru Va Wc Ye) Tr(Fi Gc Gd Rt Sh Va Vc Wf Wh Yl Zw) Ru(Bg Jp Jy Lv Mv Nq Ou Ut Vu Yd) Dr(bF Hq Kk Lv Mv Nq Oh Ou Ut) Fc(Cu Et Fy Lh Lv Lx Ou Tn) Yi(Gn Ha Ii Ne Pb Pc Ug Yl) Gn(Cu Dc Jr Rm Ut Vu) Yd(Ez Li Ni Oh Qx) Vc(bZ Et Lx Ma Tn) Fy(Fi Gc Zx Yf) Ye(Mv Qd Ut Vu) Et(Fi Gh Si) Zx(Ba Ez Oh) Wf(Mv Tn Ut) Cu(Gd Rt) Gc(bQ tF) Ut(Eq We) Va(Lv Rm) GhLx SihB WhoE} Qd{Ru(Af aH aZ bP Cx Dr Eq Kj Oh Or Ou Pb Qv Sh Sj To Ug Ur Uu Ye Tm Xa) Th(Ar Ax Cs Dr Fy Kd Kx Li Mh Ml No Oe Oh Oi Qv Qx Ra Rf Wm) Du(Ax Cs Fy Ml oE Oh Qv Qx Ra Tr Uu) Dr(Hp Ib Jd Je Kx Qh Qv Rj Uy Ye) Ye(aA bL bN Js Mq Oh Pb Rm Va) Ti(Ar Kd Li Lj Oi Qv) Va(aZ bA bS Dc Hu Qw) Yh(Fy oE oF Oh Yi) Uu(Gc Op Ux Vh Zx) Il(Sh Ux Wf) Oh(Uy Zw Tl) aW(Gh Rz Sh) Eq(bF bQ) Lx(Vc Wh) Mt(Wd Wf) Xa(Oi Pb) Uh(iB Jj) jT(Kn rS) FyZw NrWh LvYd TnWf WdbQ QvLp KdUy} Uh{iB(aM An aW Ax bI bV cQ Cs dJ Ez Fa Iu Jd jP Kc Kf Kk Kn Ko Li Lj Mt No Nr Oh Om Qe Ri Vt Wm) Ko(hX iC jD jE jF jG jH jK jL jM jO jP jQ jR jT jV lK lM lN lO) No(gP Ii iO kS nW oE oH oK oN) hB(aE CH dJ Lp nW Ri Uy) nW(bA cH Id jI Kn Ra Vt) Jj(Dc Il Qe Ri Uc Wm) oN(bA Lx Mr Mt Nr Oh) Tv(bN eC Ii Pb) Ri(eF gL jI oE) aE(hG iZ oE oF) dJ(gL iZ Kk qX) Ch(eF gL Jp) Qe(Ti Th) IdkS KnjT RmVa RjnI cHgL} Mt{aX(Du Eq Fc Fd Gb Gh Hl Ho Hp Lp Lt Rt Ru Rv Ry Rz Sf Sh Si Sj Uy Uz Va Vb Vc Vj Vw Vz Wc Wd We Wf Wg Wh Yd Yg Yh Yi Yj Yl Zq Zw Zx Ye Tm Tl Yf) Ux(bI Hq Hw Hx Il It Qe Qt St Vq Vu) Eq(Hq Jk Jm Nv Oh St Ut) Oh(Du Vc Vz Wc Yd Zw) Vb(Dc Hw Hx St Vu) Yd(Lv Or Qh Tz) Ye(Hx Qb Qe Rm) Dr(Fn Or Tz) aZ(Vc Yi Yk) Zw(Qe Rm) We(Ng St) Rz(bI Hq) Va(Dc Rm) FwYl MxVz HxVw IhWh} Lx{Vc(aD Af aN aY bJ bM BN BO Cx Dd Dr Fc Fw Hx Ih Jh Jk Jm Mu Mw No Nq Nt Nu Qm Qu Qw Qy Sr St Uv) Nd(Du Fc Fd Gb Gh Hp Lt Rt Rv Ry Sh Va Vz Wf Yd Zw Xa) Gh(Aa aN aW bJ bM Cx Dd Fc Fw Ih Jm Kd No Qy) Wh(Dd Jh Jk Mq Mu Mw Nt Nv Om Qy) Dr(hB hC iZ nW Rh Uv) Fc(aN cA cK Fw hG Qy) Du(cA cK Rh) Zw(hG Jk) Wf(Mu Ut) rS(cL Oy) EqhB NqRz} No{Th(cA cK dR eF fP gL gP hB hC hG iA iH iJ iO iP kQ kR kS nU nW nY oE oF oH oK oN pF) Ti(dR eF fP gL gP hB hC hF hG iA iH iJ iO iP kQ kR kS Nd nW nY oE oF oH oK oN pF) dR(Du Fd Fi Hl Hp Rz Sh Ux We Wf Yd Zw Ye) Vc(bZ cE Hq Lv Ma Nq Ou) Wf(Jy Mu Mv Tn Ut) Wh(bQ Hq Mv Ut) oE(Fc Rz Ux Wd) Xa(gP iP Oi) Ou(Fc Gh) NqRz UroH PapH} Va{Rm(aA Af aG aJ aZ bC bM Bo bP bS Cu Cw Dc Dd dI Dr Fc Gc Hb Ib It Iu Li Lv Mg Mi Mp Mu Nq Om Ou Pa Pd Qv Qw Qy Ri Rj Uc Uf Ug Un Ur Vq Vt Wf Ye) Dc(Cx Fw Gc Ih Li Nt Nu Pe Qy Sr St) St(aU aZ Cu cV Lv Mp Oh Ou Uc) aZ(Ih Ir Iu Ut) Tz(Dd Il Vq) Oh(aE Dd Pi) Cx(Fd Uc) Lv(Ih Sr) Qe(bM cE) BaOr EqUc NdPe IhOu SrcV VqoH} Ut{Wf(aA aF aX aY bL bM Bo Ch De Dr Eq Ih Ik Il Ir It Jm Jo Kd Ki Lj Mq Mr Mw Nr Of Oh Pa Pb Pe Qb Ru Sr St Uu Uv Ux Th) Dr(aW aZ Ch cQ Il Ir Jm Lj Nx Oh Ss) Eq(aW Cx Li Nq Sr Vq) Ch(Gb Hp Vj We Xa) Uu(Sh Vc Wh Zx Xa) Sh(Bo Cx Il) We(Ir Sr St) Ti(Lj Qe) Th(Lj Qe) Ru(Jj Mr) Rt(Dc Iq) CxFd IhYe YhoE VhVq} Oh{Qy(Dr Du Eq Fc Fd Fi Gb Gc Gd Gh Gn Hl Ho Hp Lp Lt Op Ry Rz Sf

Figure 28 Continued

Sh Si Sj Vz Yd Yk Yl Zw Ye Xa) Dr(Gz Jy Kc Ki Kk Ou Qu Ri Uc Um) Du(Ef Gz Hv Jh Kc Li Mi Mu Mw Nq) Eq(Ef Jy Mu Nq) Yh(Cu Ef Jh Mu) Vc(Bo bZ dI Jy) Nq(Lp Rz Sh) Xa(Il Oi Pc) Pc(Fc Ti) AanK ThQe MwYe HobM IlVz JyRu YIPe} Qe{aZ(Uw Ux Uy Uz Vc Vh Vw Wc Wd Wf Wg Wh Yd Yj Yl Zq Zw Ye Tm Tl Xa) Ti(bR hB Nu Oi Qv Tz Ub Ug Uk Um Up Ur Uu Vt) Th(Li Nu Qv Ub Uf Ug Ur) bQ(Rt Ux Vb Vc Wf Wh Zw) bM(Uy Vj Yi Yl Ye Xa) Du(Qv Ug Uu Xa) Ye(aA Mq Mw Qy) cE(Ux Vc Yd) Dr(Hp Ug) GnYh HpaA RuUr} Pe{Wh(bF bM bQ cE Dc Hq Jk Jp Nq Nv Om Qh) Vc(aH bM bQ bZ cE Dc Hq Il Jp Ma Qh Qv) Wf(Bg dR In iP Jp Jy Mv Nq Tn) Yl(cF dK Il Jk kQ Ks Po) Gh(bM cE Du Il Nd) Vz(aK aU Il Nd oE) Xa(cQ gP Nd Oi) Ye(dR hB Nd nY) Th(cA oE pF) Du(Nd oF) Nq(Rz Ux) Mm(oW pI) DcWc DroE FccE UcUx} dJ{Kn(eD eZ hA hO hR hV hW hX iB iC jD jE jF jG jH jI jK jL jM jP jQ jR jU jV jY lK lL lM lO qA qB qC) Kp(pS uG ul uM uN uO uR uY uZ wG) wB(Ct Lj Lu nW) Kk(iB jY rS) NgvI ldwP RfrS} Il{Mq(Eq Fd Fi Gh Hl Rv Rz Sf Sh Sj Ux Vb Vh Vz Wc Wf Wh Yd Yj Yl Ye Xa) Vz(Cu Js Ky Li Vj) Xa(Hx Jj Or Ql Vt) Dr(Or Ou Tz) Jj(Et Ko Vq) Js(HI Rt Rv) Rt(Cu Uc) Ur(Fd nI) hB(Si Vc) DkSh EtOg HxYj UyVt} aZ{Yi(aW bJ bW bZ CO Cu De Ef Gz Ho Hv Jh Jy Kc Li Ma Mg Mi Mm Mp Mq Mw Qy Uf Yk) Ru(Co Cu Mr Mu Ni Nq) Ni(Fi Ry Sf Xa) Cu(Rt We Wh) TinU TnWf YkRm WcOm JyRy mZpH} Et{Jj(Fp Ip It Jm Js Lh Lj Mn Nj Nl Ns Oe Og Pb wC Wm) Og(aA Fp It Lj Ng Nj Nl Ns) Lj(Nj Ns Oe Oy)} Xa{Oi(bZ cU Fw Nv) aW(Hx Jr Mj Or) Og(Jm Nx Ru) cQ(aM Dr Hx) Nq(aX Ch) Sr(fP Or) Rm(Rj Sh) NudC UcVs JsPc NxOu aYhB} Ye{Mw(bA bW cT Hx Ih Js Mq Nd Pa Qb Tz) Mq(Al Fy Jk Jp Ks Qc Rm) Rm(Li Mi Mu Qy) QbJy QyJs} Dr{Ou(aW Fw Gp Ih Jm Kd Li Lj Pa Ru) Om(Qz Vw Wd Wh) Ky(aW Jm Ru) Nq(Kd Ru) GpOr MhUc HpRm TzaW} jT{Id(tS uM uN uP vB wL wP yD) Kn(aM cQ In Ky oK) Ko(vU wL) Lh(cQ Ct) Lj(rS tQ) Vt(uN vW) NgUn JqcQ} nW{wB(aN cZ dE iA Ko Lv Nm Qt Rj rS wP) Vt(rS tO tS uO uT vB vI zG tM xA) ldwP aWrS} Eq{Nq(BA cT Jk Js Nd Rm) Ef(Js Nv St) St(Mu Mv) Jk(bZ cS) Li(bF Hq) MqJp MwUc TnWf} Li{Du(Dc Lv Mj Or) Th(Jp Mj Ou St) rS(Fp Hu Iv Iz) TiSt LvYd SjfP KciB RzbF} pH{nL(Af Bn De nI) Pa(Ar bN Ni) Af(nN Nr) De(mZ nH) aW(Bo Jj) CxmU aYoE fPnK nCnl} Ru{Mr(Ky Mp Or Ou) Tz(Cx Jy Ni) Js(Jy Ni Nq) Vu(Kg Kj Or) MiOr LjOu OmOy} Cu{Rt(bL Jk Pa Qb Qh St) St(Vb Vh Wc We) Yh(Lj Rm) Vb(Ih Jh) VzaW} Lj{Du(Lv Ou Uc Vu) Ou(Rt Ti Th) iB(Kc Kn oH) TnWf VzPg} hB{Ch(Si Zq) Th(Jt Un) Kd(Sh Vc) Vq(Vb Yh) EmnU FcPi QceQ} Dc{Mq(Vb Vh Wc Yk) Rt(bQ dR Ky) Ur(Wc Yk)} Wf{Tn(bL Bo Jo Mw Qb Rt) MqJp IhOu OmPb} Kn{Hw(hV hX qA) cQ(iB jQ jR) KohX VtiB} Om{Uu(Gc Rz Vc) Oy(Wc Wh Yd) LzWh NgYi} Zq{Ch(hC iO oE oH oN) ApNr aXgL} Ri{wD(cW Lu oN) rS(aW Id) ShRm qCvB} aW{Or(Hp Yi) rS(cZ Iv) DkSh MjVz} Nq{Pa(Sh Yd) DuJs IhUx YiaX} Rm{Fw(Vz Yl) DuQv YkdI UuUw} Ou{Ih(Yd Zw) YdPi KfhX LpUr} Vq{Jp(Ch Jj Kj) JjeP JonC} cQ{qZ(Hu iO Iv) NrVz JjKo} iP{rS(bO cH wD) UmwB VtvS} Nv{Oi(Rt Tm) GcUu} Bo{NdYi TnVc} Fy{FwYI JkRt} Mq{DdUy YjJm} Ur{LpVu Pgnl} nU{ArTh NIjF} iZ{SibQ dKoD} GcStQv MuYiaX MwUcWe WcJsPc JmVjPi LhnKjF NxnChR VtiJqH jYkOIN Unconstrained panels with 2 analytes, where 1.0E-8 >= 'AUC p-value' > 0. Contains 3,939 panels of 191,187 total panels evaluated. : Vi(AA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP Cq cR CS CT CU CV CW CX cY cZ dA DB DC DD DE dF DG dH DI dJ DK DL dM dN Dp DR Du Ed EF EM Eq Et Ex Ez Fa Fb Fc Fd Fi Fn FP FR Fw Fy Gb Gc Gd Gh GL Gn GP Gz Ha HB HC HF hG Hl Ho Hp Hq Hr Hu Hv Hw Hx iA Ib Ic Id IH Ii IJ Ik Il Im In IO IP Iq Ir Is It Iu Iv IZ Jd Jf Jg Jh Ji Jj Jk Jl Jm Jn Jo Jp Jq Jr Js Jt Ju Jv Jy KC Kd KE Kf KG Kl Kj Kk Kl KN KO KP KQ KR KS Kx Ky Kz Ld Lh Li Lj Lp Lt Lu Lv LW Lx Ly Lz Ma Mb Mc Md ME MF Mg Mh Ml Mj Mk Ml Mm Mn MP Mq Mr MS MT Mu Mv MW Mx MY MZ Na NB NC Nd Ne Nf Ng NH Ni Nj NK NL Nm NN NO Nq NR Ns NT NU Nv NW Nx NY Oa OE OF Og OH Oi OK Om ON Op Or Ou Ow Oy Oz Pa Pb Pc Pd Pe PF Pg Ph Pi Pj Pk Po Ps Pz Qa Qb Qc Qd Qe Qg Qh QI Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tr Tt Tv Tz Ua Ub Uc Ud Ue Uf Ug Uh Uk Ul Um Un Uo Up Ur Us Ut Uu Uv Uw Ux Uy Uz Va Vb Vc Vh Vj Vo Vp Vq Vs Vt Vu Vv Vw Vz Wb Wc Wd We Wf Wg Wh Yd Yg Yh Yi Yj Yk Yl Zq Zw Zx Ye Tm Tl Xa Wm Tj Ti Th tF Yf) Ps(aA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR Du Ed EF EM Eq Et Ex Ez Fa Fc Fd Fi Fn FP FR Fw Fy Gb Gc Gd Gh GL Gn GP Gz Ha HB HC HF hG Hl Ho Hp Hq Hr Hu Hv Hw Hx iA Ib Ic Id IH Ii IJ Ik Il Im In IO IP Iq Ir It Iu Iv IZ Jd Je Jf Jg Jh Ji Jj Jk Jl Jm Jn Jo Jp Jq Jr Js Jt Ju Jv Jy Kc Kd Ke Kf Kg Kl Kj Kk Kl Kn Ko KP KQ KR KS Kx Ky Kz Ld Lh Li Lj Lp Lt Lu Lv LW Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv NW Nx NY Oa OE OF Og OH Oi OK Om ON Op Or Ou Ow Oy Oz Pa Pb Pc Pd Pe PF Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tr Tt Tv Tz Ua Ub Uc Ud Ue Uf Ug Uh Uk Ul Um Un Uo Up Ur Us Ut Uu Uv Uw Ux Uy Uz Va Vb Vc Vh Vj Vo Vp Vq Vs Vt Vu Vv Vw Vz Wb Wc Wd We Wf Wg Wh Yd Yg Yh Yi Yj Yk Yl Zq Zw Zx Ye Tm Tl Xa Wm Tj Ti Th tF Yf) Nw(AA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp Du Ed Ef Eq Et EZ Fa Fc Fd Fi Fp Fr Fy Gb Gh HA hB Hf Hl HO Hp Hq Hr Hu Hv Hw Hx IB IC Id Ih Ii Ij Ik Il Im In Io Ip Iq Ir Is It Iu Iv Iz Jd JE JF Jg Jh Ji Jj JK JL JM Jn JO JP JQ JR Js JT Ju Jv Jy Kc Kd Kf Ki Kj Kk Kl Kn Ko Kp Kq Kr Ks Ky Ld Lh Li Lj lK lM lN Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oa Oe Of Og Oh Oi Ok Om ON Op Ou Ow Oy Oz Pa Pb Pc Pd Pe Pf Pg Ph Po Pz QA Qb QC Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tr Tt Tv Tz Ua Ub Uc Ud Ue Uf Ug Uh Uk Ul Um Un Uo Up Ur Us Ut Uu Uv Uw Ux Uy Uz Va Vb Vc Vh Vj Vo Vp Vt Vv Vw Vz Wb Wc WD We Wf Wg Wh Yd Yg Yh Yi Yj Yk Yl Zq Zw Zx Ye Tm Tl Xa Wm Ti Th Yf) Im(aA Aj Du Eq Et fB Fc Fd Fi Fp Fr Gb Gc Gd Gh Hl Ho Hp Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Op Oy Oz Pa Pb Pc Pd Pe Pf Pg pH Po Pz Qa Qb Qc Qd Qe Rt Ru Rv Rx Ry Rz Sf Sh Si Sj Uw Ux Uy Uz Va Vb Vc Vh Vj Vw Vz Wb Wc Wd We Wf Wg Wh Yd Yg Yh Yi Yj Yk Yl Zq Zw Zx Ye Tm Tl Xa Ti Th Yf) On(aA Aj Du Eq Et Fc Fd Fi Fp Fr Gb Gh Hl Ho Hp Hq Hr Hu Hv Hw Hx Ih Ii Ij Ik Il In Io Ip Iq Ir Is It Iu Iv Iz Jg Jh Ji Jj Jk Jl Jm Jn Jo Jp Jq Jr Js Jt Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om Op Oy Oz Pa Pb Pc Pd Pe Pf Pg Po Pz Qa Qb Qc Qd Qe Rt Ru Rv Rx Ry Rz Sf Sh Si Sj Uw Ux Uy Uz Va Vb Vc Vh Vj Vw Vz Wb Wc Wd We Wf Wg Wh Yd Yg Yh Yj Yl Zq Zw Zx Ye Tm Tl Xa Ti Th) Mz(aA Ax eD ET eZ Fc fN Fr fY hA hB hL hO hP Hq HR Hu HV HW HX iB iC Ih Ij Ik Il In Ir It Iu Iv jD jE jF JG jH Jl Jj jK jL jM Jn jO JP jQ jR jT jU jV jY Kc Ld Lh Li Lj lK lL lM lO Lu Lw Lx Lz Mc Md Me Ml Mn Mp Mq Mr Ms Mt Mw My Na Nb Nd Nf Nj Nk Nl Nm No Nq Ns Nu Nv Ny Oe OF Og Oh Ok Oy Oz Pa Pb Pd Pe Pf Pg pS pY qA qB qC QD qG ql qT qV qW qY qZ rB rC rN rO rP rS Rt RU

Figure 28 Continued rW RX rY rZ sK sM sO uG Uh uI uL uM uN uR Us uT uW uX uZ VA vB vC vH vI wB Wf yH yK zH tL) Ji(aA Af Aj Ax bA Bn cI Cx De Et eZ Fp Fr hB Hq Hr Hu Hv Hw Hx iB Ih Ii Ij Ik Il In Io Ip Iq Ir Is It Iu Iv Iz jF Jg Jh Jj JK JL JM Jn JO JP JQ JR Js JT Lh Li Lj lN lO Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe OF Og Oh Oi Ok Om Oy Oz Pa Pb Pc Pd Pe Pf Pg Po Pz Qa Qb Qc Qd Qe Ri Ru rW Ug Uh Ur Us Uv Vo Wc Wm Th) Et(aA Aj bA cI Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe Of Og Oh Oi Ok Om Oy Oz Pa Pb Pc Pd Pe Pf Pg Po Pz Qa Qb Qc Qd Qe Uh Wb) Ok(aA Aj Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe Of Og Oh Oi Om Oy Oz Pa Pb Pc Pd Pe Pf Pg Po Pz Qa Qb Qc Qd Qe Uh) Ij(aA Aj Dr Du Eq Fc Fd Fi Fp Fr Gb Gh Hl Ho Hp Hr Hu Ik In Io Ip It Iv Jg Jj Jm Jo Jp Jq Jt Lh Li Lj Lp Lt Lu Lw Lx Ma Me Mi Mm Mn Mp Mr Ms Mt My Na Nd Nh Nj Nk Nl Nm Nn No Ns Nv Nx Ny Og Op Oy Oz Pb Pe Qd Rt Ru Rv Rx Ry Rz Sf Sh Si Sj Uh Uw Ux Uy Uz Va Vb Vc Vh Vj Vw Vz Wb Wc Wd We Wf Wg Wh Yd Yg Yh Yi Yj Yk Yl Zq Zw Zx Ye Tm Tl Xa Ti Th Yf) Uh(Ad Aj As bA bN Cp Cq Cu Cw Dc Dd dM dR Ed eF eP gL gP hB hC hF hG Hv Hw Hx iA iB Id iH iJ In iO iP Ir Is It Iv iZ Jj jK Jl Jn Jp Jq Jr Js Kd Ke Kk Kn Ko Kp KQ KR kS Ld Lh Li Lw Mj Ml Mr Ms Mt Na Nb Nf Ng Nl Nm No Nr nW Nx NY oE oF oH Oi oK Om oN Or Pb Pe pF Pi Pk Qa Qd Qe Ra Ri Rj Sr Tn Tv Uc Ud Up Ur Us Ut Uu Vp Vt Vv) Ny(aA Du Fc Fd Fi Gb Gh Hl Ho Hp Hq Hr Hu Ik In Iq It Ij Jp Li Lp Lt Lw Lx Mc Md Mi Mn Nr Nd Nn Nr Ns Of Og Oh Op Oy Oz Pa Pd Pe Pf Pg Rt Ru Rv Rx Ry Rz Sf Sh Si Sj Uw Ux Uy Uz Va Vb Vc Vh Vj Vw Vz Wb Wc Wd We Wf Wg Wh Yd Yi Yj Yk Yl Zq Zw Zx Ye Tm Tl Xa Ti Th Yf) Qd(Aj Du Eq Fc Fd Fi Gb Gd Gh Hl Ho Hp Ik Jg Jj Jp Li Lp Lt Ma Mn Nj No Nv Og Op Oy Oz Pb Rt Ru Rv Rx Ry Rz Sf Sh Si Sj Uw Ux Uy Uz Va Vb Vc Vh Vj Vw Vz Wb Wc Wd We Wf Wg Wh Yd Yh Yi Yk Yl Zq Zw Zx Ye Tm Tl Xa Ti Th Yf) Is(Aj Du Eq Fc Fd Fi Gb Gd Gh Hl Ho Hp Jj Jp Li Lp Lt Lx No Og Op Rt Ru Rv Rx Ry Rz Sf Sh Si Sj Ur Uw Ux Uy Uz Va Vb Vc Vh Vj Vw Vz Wb Wc Wd We Wf Wg Wh Yd Yg Yh Yi Yj Yk Yl Zq Zw Zx Ye Tm Tl Xa Ti Th Yf) Qa(Aj Du Eq fB Fc Fd Fi Gb Gh Hl Ho Hp Jg Jj Jp Kc Lp Lt Og Op Rt Ru Rv Rx Ry Rz Sf Sh Si Sj Uw Ux Uy Uz Va Vb Vc Vh Vj Vw Vz Wb Wc Wd We Wf Wg Wh Yd Yg Yh Yi Yj Yk Yl Zq Zw Zx Ye Tm Tl Xa Ti Th Yf) Lx(Du Fd Gh Hp Hr Ii In It Jg Jj Jp Jr Lw Mb Mc Mh Mi Mk Mn Nj Nn Nr Ns Oe Of Og Oh Op Oy Oz Pb Pe Pf Pg Qe Rv Rx Ry Rz Sf Sh Si Sj Uw Va Vb Vc Vj Vw Vz Wb Wc Wd Wf Yh Yj Yl Zw Zx Ye Tm Xa) Jl(Du Eq Fc Fd Fi Gb Gh Hl Ho Hp Jj Jp Lp Lt No Og Op Rt Ru Rv Rx Ry Rz Sf Sh Si Sj Uw Ux Uy Uz Va Vb Vc Vh Vj Vw Vz Wb Wc Wd We Wf Wg Wh Yd Yg Yh Yi Yj Yk Yl Zq Zw Zx Ye Tm Tl Xa Ti Th Yf) Kq(Aj Dr Du Eq Fc Fd Fi Gb Gc Gd Gh Gn Hl Ho Hp Iz Jj Lp Lt Of Op Rt Ru Rv Rx Ry Sf Sh Si Sj Uw Ux Uy Uz Va Vb Vh Vj Vw Vz Wb Wc We Wg Yd Yg Yh Yi Yj Yk Yl Zq Zw Zx Ye Tm Tl Xa Ti Th Yf) Pe(Du Eq Fc Fd Fi Gb Gh Hl Ho Hp Hr Lp Lt Lw Ns Op Rt Ru Rv Rx Ry Rz Sf Sh Si Sj Uw Ux Uy Uz Va Vb Vc Vh Vj Vw Vz Wb Wc Wd We Wf Wg Wh Yd Yg Yh Yi Yj Yk Yl Zq Zw Zx Ye Tm Tl Xa Ti Th Yf) No(Aj Fp Ho Hr Hu Ih Ik In Ip It Jg Jj Jp Kk Li Lj Lv Ma Mn Ms Na Ng Nj Nk Ns Nv Nx Oe Og Oy Oz Pb Qc Rx Ry Ur Uw Uz Va Vc Vh Vz Wb Wc Wd We Wg Yd Yi Yl Zw Zx Ye Tm Tl Xa Ti Th Yf) Oa(Dr Du Eq Fc Fd Fi Gb Gc Gh Gn Hl Ho Hp Lp Lt Op Rt Ru Rv Rx Ry Sf Sh Si Sj Uw Ux Uy Uz Va Vb Vc Vh Vj Vw Vz Wb Wc Wd We Wf Wg Wh Yd Yg Yh Yi Yj Yl Zq Zw Zx Ye Tm Tl Xa Ti Th) Nb(Du Eq Fc Fd Fi Gb Hl Ho Hp Lp Lt Op pH Rt Ru Rv Rx Ry Rz Sf Sh Si Sj Uw Ux Uy Va Vb Vc Vh Vj Vw Vz Wb Wc Wd We Wf Wg Wh Yd Yg Yh Yi Yj Yk Yl Zq Zw Zx Ye Tm Tl Xa Ti Th Yf) Jn(Du Eq Fc Fd Fi Gb Hl Ho Jj Jp Li Lp Lt Og Rt Ru Rv Rx Ry Rz Sf Sh Si Sj Uw Ux Uy Uz Va Vb Vc Vh Vj Vw Vz Wb Wc Wd We Wf Wg Wh Yd Yg Yh Yi Yj Yk Yl Zq Zw Zx Ye Tm Tl Xa) Qe(Aj Du Fc Fd Gb Hl Ho Hp Jj Lp Lt Op Rt Ru Rv Rx Rz Sf Sh Si Ur Uw Ux Uy Uz Va Vb Vc Vh Vj Vw Vz Wb Wc Wd We Wf Wg Wh Yd Yg Yh Yi Yj Yl Zq Zw Zx Ye Tm Tl Xa Ti Th) Nn(Du Eq Fc Fd Fi Gb Gd Gh Hl Ho Hp Jj Lp Lt Og Op Rt Ry Rz Sf Sh Si Sj Ux Uy Uz Va Vc Vz Wb Wc Wd Wf Wg Wh Yd Yi Yl Zq Zw Zx Ye Tm Tl Xa) Xa(aM aZ cQ cU dC Ed Fw hB Hx Ih Il In Jj Jy Ld Mt Nq nU Nv oE Og Oh Oi Or Ou Ow Oz Pf Qc Ql Rm Rx Sr St Un Ut Vt Vu) Ke(eC eT eZ fN fY hP Ik Jj Jp oH pS qA rR rS rW sK sO tO tS uO uU uW uZ vA vQ vS vT wC wD wH wJ wK wL wP wQ yD zG zl) Mt(Du Eq Fc Fd Fi Hp Lp Og Ru Rx Rz Sh Sj Ux Uy Va Vb Vc Vw Vz Wb Wc Wd We Wf Wh Yd Yh Yi Yl Zw Zx Ye Tm Tl Th) Oh(Du Eq Fc Fd Fi Gh Hp Lt Op pH Rv Rx Ry Rz Sf Sh Sj Uw Va Vc Vw Vz Wb Wc Wd We Wh Yj Yl Zq Zw Zx Ye Tm Tl Ti) Pf(Du Eq Fc Fd Gb Gd Gh Hp Lt Ns Op pH Rt Rv Ry Sf Sh Ux Uy Uz Va Vb Vc Vj Vz Wb Wd We Wf Wh Yl Zq Zw Ye Tm) Jp(aA Aj Ch Fp Hc Ih Ip It Jj Jr Js Kk Ld Li Lj Lv Lw Mp Ng Nj Ns Nt Nv Nx Oe Og Ow Oy Oz Pb Po Qb) Ut(Dr Eq Gh Gn Lp Rt Ru Rx Ry Rz Sh Sj Uw Ux Uy Uz Va Vb Vc Vh Vw Vz Wb Wc Wd We Wf Wg Wh Yd Ye) Rm(Dr Du Eq Fc Rx Sh Uw Ux Uy Uz Va Vb Vc Vh Vj Vz Wb Wc Wd We Wf Wg Wh Yk Zq Zw Ye Tl) Nv(Fp Hu It Jj Li Lj Mn My Ng Ns Nt Oe Og Oy Oz Pb Rt Ux Va Vb Vc Wb Wf Yd Yl Ye) Ow(Dr Du Em eP Gd Gh Hp kO pH Rx Si Uw Va Vb Vc Vz Wb We Wh Zx Ye Tm Tl Ti Th) Ed(Dr Gc pH Ru Ry Uw Ux Vc Vh Vj Vw Wd We Wh Yd Yg Yi Zq Zw Zx Ti) Li(aA Hr Hu Ik In Ip Jg Jj Js Lv Lw Mn Na Ng Nj Ns Og Oi Oy Oz Vt) pH(aW aY BN Cx De Kd ml mZ nH nI nK nL nN Nr nU Nx oW Pa) Jj(Aa Bb Dc Fr Jg Js Jt Ko Lh Ma Mn Nx oW Pg Uc Vq Vt) Yi(aZ Bo Fw hB iZ Ld Mq Nq nU Or Oz Pc Rj Va) Aj(Ad Ap Ba Dc Fr Jg Jt Ko Ma Mn Uc) St(Eq Ru Rx Rz Ux Uz Va Vh Wh Ye) Om(Eq Gd Rt Sh Vc Wd We Wf Yd Ye) Wb(Fw hB Ir Js Kk Ld Mq Mx oE) Og(Fr Ip Jr Jg Js Lh Mn Nx Pg) Cu(Rt Ru Rx Va Vb Wf Yd Th) Ko(eZ hO qC rS uR uZ wD wP) Jg(aA Fp Ip Js Lj Ng Qb) Va(Dc Fw Ih Js Sr Uc Vu) Vj(Dc Fy Il Ir Jm Pa Qh) hB(Dr Fd Fi Ho Lp oW Uy) Mn(aA Ip Lj Nh Nj Ns) Ld(Fd Fi Ho Lp Uy We) Fr(aA It Ng Nj Oz) Fw(Vc Vz Yl Zq Tm) rS(aW Id iP Lj Lu) Ih(Rx Uw We Ye) Js(Du Rx Wc Yl) aA(Ip Lh Ma Nj) Dc(Rt Rx Ur) Id(uR vS wP) Ye(Mw nU Vu) Kn(eD iB jK) Ru(Mr Nq Ou) Ri(uT wB wD) iP(hO rN wD) nW(qZ rN wB) oW(Jo nD Ug) Dr(Kk Qh) Fy(Rt Rx) Hl(nU Vu) Tn(Rt Wf) Il(Vz Yl) Lj(Ma Nx) Uw(aZ Oz) FcJr NqLp NsPg MxWd IrVz WenU VteC VqiB cQqZ nChR Unconstrained panels with 2 analytes, where 1.0E-7 >= 'AUC p-value' > 1.0E-8. Contains 1,349 panels of 191,187 total panels evaluated. :
No(aA Du Eq Fc Fd Fr Gd Gh Hl Hp Hq Hv Hw Hx Ii Il Io Iq Ir Iu Iv Iz Jh Jk Jm Jn Jo Jq Jr Js Jt Kc Lh Lp Lt Lu Lw Lx Ly Lz Mb Mc Md Me Mf Mg Mh Mi Mj Mk Ml Mm Mp Mq Mr Mt Mu Mv Mw Mx My Nb Nc Nd Ne Nf Nh Ni Nl Nm Nn Nq Nr Nt Nu Ny Of Oh Oi Om Pa Pc Pd Pe Pf Pg Po Pz Qa Qb Qe Rt Ru Rv Sf Sh Sj Uy Vb Vj Vw Wf Wh Yg Zq) Nv(aA Aj Fc Fd Fr Hq Hr Hv Hw Hx Ih Ii Ik Il In Io Ip Ir Is Iv Jg Jk Jm Jn Jo Jq Jr Js Jt Lh Lp Lu Lv Lw Lx Ly Lz Ma Mb Mc Md Mf Mg Mi Mk Mm Mp Mr Ms Mt Mv Mw Mx Nc Ne Nf Nh Ni Nj Nk Nl Nm Nn Nr Nu Ny Of Oh Oi Om Op Pa Pd Pe Pf Po Pz Qa Qb Qc Sh Uw Uy Uz Wd Wg Wh Yi Tm Tl) Li(Aj Fp Fr Hq Hv Hw Hx Ih Ii Il Io Iq Ir It Iu Iv Jh Jk Jl Jm Jq Jr Lh Lj Lu Lx Ly Lz Ma Mb Mc Md Mf Mg Mh Mi Mj Mk Ml Mp Mr Ms Mt Mu Mv Mw Mx My Nb Nc Nd Ne Nf Nh Nk Nl Nm Nn Nr Nx Oe Of Oh Om Pa Pb Pc Pd Pe Pf Pg Po Pz Qa Qb Qc Qe Ug Wb Yd) Uh(aA aE aM An Ax Bn bV cA CH cI Cs CT Cx De dJ dK Dr Ef Fp Fw Fy Hq Hu Ib Ic Ih Ii Ik Il Im Ip jI Jo Jt Kf Lj Lv Lx Ma Me Mh Mi Mk Mn Mq Ne Nh Nj Ns Oa Oe Of Og Oh On Ou Ow Oy Oz Ph Po Qb Ql Qz Rb Rm To Tr Ug Uk Ul Un Uv Vo Vu Wm tF) Jp(Ar Cs Fr Hq Hr Hu Hx Id Ik Il In Ir Iv Iz Jg Jq Kc Kj Kl Kn Ko Kx Lh Lu Lz Ma Mc Mf Mg Mh Mi Mj Mk Mm Mn Mq Mr Ms Mt Mx My Nb Nc Nd Ne Nh Nl Nm Nn Nq Nr Nu Oa Of Oh Oi Om Or Pa Pd Pe Pf Pg Qc Qe Ql Ur Vq Vt Wm) Ij(Gn Hq Hv Hw Hx Ii Il Iq Ir Is Iu Jh Jk Jl Jn Jr Js Lv Ly Lz Mb Mc Md Mf Mg Mj Mk Ml Mq Mu Mw Mx Nb Nc

CU Cv Dc Di dM fR Jl Jo Kc Kj Mh Mv Ri Sh) Mw(Aj Fd Fp Fr Gh Hl Hp It Iv Jn Jr Lv Ms Ns Nt Of Oz Pb Pc Po Ru Sh Vc Wc Tl) Ny(Ao Gn iB jE jH Jk JL jP Jq Jt jV jY lO Mg Mh Mk Mv Ni nK Om Ow Qb qW Ri) Om(Fc Fd Fi Fp Fr Gb Gh Hl Lp Lt Ns Op Oz Po Rv Ry Sj Uw Uy Wg Yl Zx Tm Tl) Kq(Bg cQ Ct Hc Ii In Jh Jk jT Mc mZ Nj Og oH Oy Ph Qw Ss Ua Ug Uu Uv Vo) Nt(Hx Ih In Io It Jn Jq Jt Lv Ly Mp Na Ng Nj Ns Oy Pb Po Qb Qc Vb Vj) wD(Aj aN Aw Ba Bb bH bS Ch Co Cs Fa Id jF Kc Kr oE oN Or Ph Pi qU Qy) Fw(Dr Du Fc Gb Gc Gd Hl Hp Lp nl Op Rt Rx Ry Rz Sf Sj Ux Uy Vb Vw) Ow(Aj bF bR Eq Ex fR Gz Hl kC Ky mF mM nC nl nU oF Oi Wc Yh Zq Yf) Oz(bA Fi Ho Hp It Jn Jt Mm Mp Nb Nl Nm Nr Nu Og Pa Qb Si Vq Yg Zq) Aa(Hx Ih It Iv Jl Jn Jo Lv Mb Mk Nb Nh Nl nU Nv Og Ok Oy Pc Qb) Po(Aj Hr Ih In Io It Iv Jn Jq Jt Me Mm Ns Oe Pb Pe Pz Qc Ru Wb) St(Aj Fc Fd Fi Gb Gh Hp nl Op Ry Sj Uy Wc Wd We Wf Yh Yj Zw Zx) nU(bW cH Du Eq Fi Hu Jr Lt Lz Mq Nj Ns Nv Oh Qc Ur Wf Yj Zx) Nr(Fd Hr It Lv Lw Mi Mm Nm Oy Pe Vb Vc Vj Yl Zq Tl Ti Th) Tn(Ch Gc Hp Pe Ru Ux Uy Vj Vs Vw Wb Wc Yd Yh Yl Zw Zx Ye) Jg(Hv Io Iu Jh Jl Jt Md Me Ml Mm Mu Mv Na Nf Nq Pc Pd Pz) Og(Fp li ll Jh Jk Jq Jr Lv Lw Mi Mj Mr Mv Nm Nq Oa Oh Pz) Jn(Aj Fp Ik In Jh Jt Lv Mp Nl Nm Nu Oe Oy Pb Pe Qb Qc) Ih(Du Eq Fc Fd Fi Fp Gh Io Lp Lv Mm Ru Rv Sf Sj Ur) Vj(AL bA bQ Cu Dd Hq Hx Ks Lp Mx oE Ok Ph Tv Uc) Fr(Hw Iq Iu Jh Jk Jm Jo Ml Na Nf Nq Oh Pc Pz rS) Uw(Bo cQ Cs Cx Dr Hx Il Iv iZ Mq Mx Oi Qc Qv Uu) Jt(Ct Hr It Iv Jo Jq Mp Mx Nh Nl Ns Pb Qb Qc) Ur(Bb Cq Id Jl Jq Li mW nR Nv Ou Qc Rm Tv Uf) rS(Ax Fb Iu Kn nW Oh Pj rC rT Uk uT wB wJ yL) Aj(Ao Ar Bc Bg bQ Cw Dd Jk Kg Kp Ou Qh Ri) Fy(cQ Dr Eq Fc Gc Gd In Sh Vb Vz Wb Wf Th) Va(aH aZ Gc Hv Hx It Jh Mq Mv Ok Or Qc Tv) Fp(Ik It Iv Jq Lv Mi Mp Nl Nm Pb Pz Ru) Mm(It Jl Jq Lv Mj Mp Mr Mx Nj Ns Pe Qc) Wb(aP bB bQ Ex Jr Ky Lv Mj Ou Qc Ql Qx) Kn(eC Ed hR hV hW iC jD jV oF Ou Ug Uv) Li(bA Ct Du Fd iH Kc Op Rt Sj We Th) Un(eC iB Ik jH jT Ms oH Oi Rx Ug Wc) Vu(Gc Gn Rt Sh Uy Vz Wc We Wh Yj Tm) Pe(Gd Il In It Lv Mj Mq Mu Nf Nm Wm) Cu(Hl Ry Rz Sf Sh Si Ux Vw Wc Zx) Id(eZ hP In jT oE qC tS Ug vQ xA) Zq(aX hC iZ Jm Jr Mj Nv oH Qh Tz) Ed(Eq Gd Ri Rx Sf Vz Yk Ye Yf) Qb(Gb Kc Ry Vh Yd Yj Zx Ye Tm) Qh(Gc nI Rx Sh Uy Vc Vz Wf Yk) uT(bL cQ dJ Hq Jk My Nq rC rW) Ar(bF cB cJ Dc dK Kc Nj Ok) Fd(gL iZ Jy Lz Mr oE Qx Qy) Jr(jH jO Ns Nu Rt Uy Wf Wm) Nv(bS Du Lt Ry Sf Sj Yh Wm) Vq(Dr Ik Ru Ux Wc We Yl Ye) Gd(aP bQ Ij Ky Nb Ok Ut) Jk(Eq Rt Ru Rx wB Ye Tm) Kc(Cs dF Hb Ij Jl rR rW) Ps(kC mF mY nA nH nl nR) aZ(Fi Rt Ru Ry Vw Wc Wf) bA(cH cQ Ct Cx gV Ij Pb) iP(eT hL qC tX uN uX wB) Dc(Ct Ik In Jo Sh Ug) Gc(dR Ky Mr nC oE Qv) Nq(Eq Hl It Sh Vc Tl) Tz(Fi Ru Ry Wc Yk Ye) Oh(bS Gz Ou Si Th Yf) oW(aD al bM Cv oH Uu) Mr(Fi Rv Si Vb Vc) Hx(Fi Op Ry Uy We) Ky(Dr Em Ex Gz Oa) Ok(De dK Rt Vo Th) nl(bZ eC oF Ug Um) iB(An Kf Kx Pj Ri) wB(aN Hu Nm Oy rB) Mq(Rt Ry We Ye) Sh(bQ Ef Hq Mv) Wf(Dk Mj Ou Uc) Jl(In Ms Ns Oe) dF(cH Cx dK oN) oE(Ho Lp Uy Vw) Ax(bF Wd Ti) Dr(Co cU Qc) Mx(Rz Vw Yl) Ij(Ct Ug Vo) Ye(Jh mU Mv) Kp(pS rB rW) Ri(qQ vB wP) Ou(bF cH rN) Ut(Yj Yk Ti) ml(hA jY Or) jl(oO oP oQ) oF(aE Fc Rt) vl(aN dJ Kr) Eq(bQ Co) Ex(bR Ru) Lv(Io It) Ho(aH Or) Hp(Rm Uc) In(Kx Pi) Si(fR iZ) Qc(cJ Ti) Kf(eD jK) Oa(Dp Ug) Vc(bQ cU) Vi(Jc mH) gV(aM aP) gZ(nH nL) mY(jF jY) lN(oO oQ) CscJ YfRm MpNj MvUy NgU

Lv mW Or Ou) On(Ad Ar Ii Jj Kj Lz Nx Qx Uv Vp We Yd Zw Th) cJ(aM Ax Cs Hp Js Ld Lz Mf Ml Oh Ow Qx Ra Wm) Af(As bB bO Cu dD gL Jr Mz nY Om Pg Tr Xa) Bo(Is Jq kG Mz nR nU Rb Uc Up Uz Vh Wg Tl) Ef(Ar Bg Ch iO Kj Lz Ml Mx Ng nU Sh Uc Vu) Or(bJ cO cS cU Ez Ld Mg Mi nN Nt Oh Ow Pa) Pe(dM Du Fi gP Ii Ik Is Jy kl kP nA nY Yl) Ar(bF Bg Ch Du Jk Jl Jp Mz Nd nU Ou) Th(bB bZ cO cS CU Et Jy Ky Mk Mr) Im(aJ aM cI cU gP kG kl kP mU nY Rg) Kf(As mW Mz Nb Om Uc Up Uz Vu Wg Tl) Uv(Cu Et Ij Is Je Jr Lh Mf Mn Ou Tn) Ng(Ao Aw Ez kP Mg Mu Mv Om Uf Xa) Sh(bF Bg Ch Jv kO kQ Mf Mv Ou Zx) Vu(aX Bg Ch De Jo Kj My Oy Ux We) Vw(bZ cS CU Et Ez Fi gL Io kG) Pa(Fp Jy Ky Ld Mk Mr Nb Nd Ou Rg) nU(Ad Bg Ch De Gn Hl kP Ml Ux We) Is(aA bN fR Ld No Ny Rm Yd Zw) Om(Iz Jj Kj Ko Lz My Oy Qx Rc) gP(aP Ax bG bO Dp Gh Jn No Of) Nb(aM Hp Ii kP Lp nN pF Vj) Nd(bB Et Fp Ky Kz Ld Nf Po) Ij(Fi Ii mE nC NH Zw Tj) Ow(aJ Ap Du Ik Iu Jy Rf Ue) cU(bM Dr kF kN Kr Vv Yl Zw) gL(aH aX bM Ch Hu My Qt Rz) Mf(aA Dr Jj Uk Wb We Zw) Mi(aC Gb Iu Jt Kr Lz Ue) Mz(Ad aY Lz Ml Nx Qx We) Xa(aM cQ cX dC Hu Oy Rc) eM(aK aU cE cL dB Qn Vp) Cu(Kj Kr mZ Nc Ux Vv) Mu(aC Hu Iu Kj Lz Oh) Uc(De Gd Iz Kj Oy We) Ld(aC aF dF Fi Tn Ue) bZ(iO kF Rc Rz Ux Vv) eF(aN dK Fc Hp Io Pd) mW(Ax Ct Dp Ex Ml We) Du(aM Fp Ml Oh Qx) Yd(Bg Jp Lh Lv Ou) Rf(Ax Cs Ml Oh Wm) Vp(Jl Jn Jr NY) iO(bG Ch cO Io Pd) kQ(Iv Iz Jj Oy Rc) Ez(aC aX Mx Qb) Hp(aA Dr Mw Ny) Tr(Ad Lz Rh Zw) Jp(Lz Nf nN Qx) Kr(Hv Hw Lw Qd) Yl(bO cX Io Mb) Nx(bB Jr Ky We) aM(bB Ju Ks Sf) kG(aX De Ml nB) kI(nC nH nL No) kS(aN aY Fc Jd) nY(bS Dk Hc No) Mv(Hu Kj Mx) Tz(bN cN dK) Jj(Hq Ks Ou) Oh(Fr Hu Jy) aH(bJ nK oH) cQ(Qx Ra Yi) cS(aX Qb Ux) nN(Gd kC Ky) Ch(Jy oH) Ct(bA Yi) Mb(nC nL) Mq(Ik Rb) Mw(bS Hu) Rc(dF Tn) Qc(Um Yj) Jr(Nc Tv) Ou(Cs Zx) aY(bB iA) bJ(aC bE) mY(dD Qu) AsGd AxTj DrbO WmHv EtTm FrMx LzJl MlKs MpIu MsNw NhbB IznW RbWe QanA JndM UfaX VqaA} Mz{hO(aV Aw aY Ba Bc bF Bg bH bJ bL bP bQ bR bS bU bX bZ cA cC cE cF cG CH cK cL cN CO Cp CQ cR Ct cU cW dA De dG dH dI dJ dL Ef hA hB Hc hP Hq hV HW hX Ib Il Iz Jd Je Jf Jk Jm Jo JY Kc Ko kS lK lO Lw Lz Ma Md Mg Mi Mk Mn Mp Mq Mu Mv Mw My Na Nd Ng Nq Ns Nu OE Of Om ON Or Ow Oy Oz Pa Pb Pd PF Pg Qt Qw RC Rg rO TN Tr Tt tU tX Tz Ua Uk Ul Up Ut Uv vB Vs wF yL yE tM Tj) qC(aV Aw Ba Bc Bg bH bL bN bQ bR bS bZ cA cG Ch cK cL cN CO Cp CQ Ct dA De dH dI dJ Ef hA hB Hc Hf hP Hq HR Hu hV HW hX IB Ik Il Iz Jd Jf Jh Jk Jm jY Ky lK lO Ma Mg Mi Mk Mn Mp Mq Mu Mv Mw Na Nd Ng Nq Ns Nu OE Of Om Or Oy Oz Pa Pd pF Pg Ql Qt Qv qW tN tU tX Tz Ua Ub Uk Ul Up uR Us uW vB vI Vs wF yH yE tL Tj) eZ(Aj aY Ba Bc Bg bH bL bN bP bS cA Ch cL cN cO Cp CQ Ct cW De dG dH dJ Dk dL Ef Fw hP Hq HR Hu hV Hw hX iA IB Ik Il In iP Iv Iz jF Jh Jl JM Jo lK Lu Mg Mk Mq Mr Mu Mv Mw My Nd Ng Nq Nt Nu NW Of oK ON Or Ou Oy Pd Ph qH Qt QW Rc sC TN Tt tU Tv tX Tz Ua Ub Uk Up Us Ut Uv uW vB vI vV vW wF wQ yH tL Tj) rS(Aj aV aW aX aY Ba Bc bF Bg bH bJ bL Bn bQ bR bS bU bZ cA cC cF cG CH cK cL cN CO Cq cR Ct cU cW dA De dG dH dI dJ dL Ef Ez hA hG hP Hq Hu hW Id Il In Io iP It Iv Jj jL Jy Kk Ko Li Lj lK lM lO Lu Mf My Nd Nh Nk Nt Nv NW oE Of ON Or Ou Ow pF Pg RC rW Ua Uk Ul Um Uv vI Vs wB yH yJ yL tL Tj) vI(aE aJ Al aP Ar As aY bL bP cH cN cW cZ dA eC Fw hG Hq Hu HW HX iB Ic Ih Ik Il In iP Ir Is It Iv iZ jD jF jI Jj JK Jm jO kR kS lK Me Mj Mk Mx Nd Nj Nn Nq Nt Nu Nv Oe oF Oh On Or pF Pg Ph Pk Qa Qc Qe qV QW rB RC Rg Ri Rm rW tQ Tz Uf Um Us wC) sO(aV aY Ba Bc bF BG bH bJ bL bP bQ bR bS bU bZ cA cC cF cG Ch cK cL cN CO CQ Ct cU cW dA dG dH dI dJ Dk dL dN Ef eT Fw hA hR Hu hV hX iA Il Iz jF Jk jM JY lK lO Nd Nt Nv oE oK oN Or Ow pF Pg Ph Qw RC Rg Tn Tr Ua Uk Ul Uv Tj) rW(Aa aV Ba Bg Ch Cq Ct cZ dA De Ef Hb Hq Hr Hw hX iB Ik Il In Iv Iz Jd Jj JK Jm jY Kc Ly Me Mg Mi Mk Mq Mu Mv Mw Mx My Nd Ng Nh Nk Nq Ns Nu Nw Of Oy Pd Pg Ql QW rO tQ tU Tz Ua Uk Up UR uW vB wB wF yH yK yE tL Tj) hP(aI Aj As bF Bg cE Ch Ct cZ dC Dk EF Fw hB Hc hR Hu HV hW hX Ib Ic Ii Ik Il In Iq Ir Iz jH Jj JK Jm Kj Kk Kn Ks Mg Ng nW Oe oF Og Oy Qc Qm Qt Qv Tv Ua Ue Ug Uh Uk uL uN UR Us Ut Uv wB wD yD zA) qZ(Al aV aY BG bH bL bP bQ bR bS bZ cA cF cG CH cK cL CO Cp cQ Ct cU cW dA dG dH dI dJ Dk eC Ef eT Fw Hc hR Ic iP Iz Kd Ko Ks Kx oE oK oN Or pF Ph Qy rC rO rQ tU tX Tz Ua uR uW vB vV wC wF wP tL) Rt(aF aN aW aY Ba bJ Cx Dc dK Ed Fd Fw Ha hB Hq Hu Ih Ij Il Im Jg Jk Jm Jn Kd Kq Ks Mt Mw Nb Ng nI nN Nr Nt Nu Nv Ny Oa Om On Pz Qa Qb Qc Qd Qe Qh Qy Rm Sr St Uh Ut Vq Vu Wf Yi Xa) Va(aN aY bJ bM BO cQ Cx Dc Dd Dr Ed Fw Gc Gp Ih Ij Ir It Iv Jk Jm Jn Js Ke Kq Li Mt Nb No Nr Nt Nu Nv Ny On Pe Pf Qb Qc Qd Qe Ql Qm Qy Rm Si Sr St Tz Uh Un Ut Vq Vt Vu Wf Xa) rO(Af Aj An aY bF Bg Bn cB cE Ch cJ Ct cZ Ef Fa Fn Gp HB hR hV hW HX Ib Ih Il It Iz Jj JK Jm jU Kc Kf Ki Kj Kn Kp Mj Mx Nd Nk Nv nY Oe Ow Qt Qw Qz Ra Ss Ua Uh Uk Us Vv) Rx(aA AF aN aY aZ bJ Cx Dc Dr Gc hB Hp Hx Ih Ij Im Ir It iZ Jh Jk Jm Jn Js Kz Li Lj Mq Mw Nb Nd nI Nl No Nu Ny Oa Oh On Oz Pb Pc Qb Qd Qe Ql Qy Rm Sr St Ut Vt Vu Wc Yi Xa) wD(aP Ba BC Bg bH bJ bL bP bQ bR bS bU bX bZ cA cC cG cK cL cN CO Cq Ct CU cW dA dG dH dI dL dN Ef Fw hA hV iA iP Iz jL JY Ko kS lK lO Nd oH oN Ow pF Pj RC Tj) Ru(aA Af Ar aZ bJ bM Bo Cs Cx Dp Dr Ed Fp Fw Gc Gz hB Is Iv Jn Jy Ke Kp Kq Kz Ld Li Mq Mr Mv Nf Nq Nu Ny Or Oz Pa Pc Pe Qa Qd Qe Ql Qy Rh Sr Ug Un Ur Ut Vj Vt Vz Wb Wf) yK(aV Bc Bg bH bJ bL bN bP bQ bR bS bU bX bZ cA cB cC cF cG Ch cK cN CO Cq cR Ct cW dG dH dI dJ Dk eC hA hG hR hX jF JY lK lO oE oN pF qD qT Qy rC Rg rN Ua Uk Tj) zH(aV Ba Bc bF Bg bH bJ bL bQ bR bS bU bW bZ cA cC cD cF cG Ch cK cL cN CO Cq Ct cU cW dA dG dH dI Ef hA Iz jH JY lK lO oE oN Ow pF Qw RC Rg Ua Uk Ul Uv Tj) wJ(aV aZ Ba Bc bF Bg bH bJ bL bP bQ bR bS bU bZ cA cC cF cG cK cL cN CO Cq Ct cU dA dG dH dI dJ Ef hA hX jF jL jM JY lK lO oE Ow pF Qw Qy rC Rg Tz Ua Ul Tj) uR(aE aI aJ aL aO aS aU aY bF Bo bP bW cE cG cW cY cZ Dg eC Ez Fw fY gW hB Id Ih iJ iZ jD Jf jK jO jQ jR Kc Kk Kn Ko Kp Ld Nd nW Pi Pk pY Qg qO Qy rC Ri Tr Ub uT) jL(Aj aM Ar CH cJ Cp cR Ct cZ dB dC Ef hB Ib Id Je jF Ji Jj jK Kc Ke Kj Kk Kn Ld Mh Ng Nl Nw Qt Qw Qy rB rN Tv Ua Ue Uh Uk uM uN uT uW uY Vt Vv wE wK yL zA) uW(aC aF aI aM aO AS bA bF bN Bo cE cT cZ Dd dF Dg eC gL Gp iP It jD jH jI jK jO jT Ju Jv Ke Kk Kn Kp KR kS Ld lL oF pF qD Qg qT qW qY Ri Tr Uf Uh Vo) Wf(aA aN Ar aW aY bJ bM Bo Cx Ed Fw Hu Ih Ij Il iZ Jh Jn Kd Ki Kk Ld Mq Mr Mt Mw Mx Nn No Nr Nu Nv Nw Nx Ny Oa Om Oz Pe Pf Qd Qy Sr St Ut Vt Th) jH(An Bg bN bP bR bS cA CH cJ cN CO Cp cR Ct dB De Ef Hf Ib Iz Jj Kp oH Qn Qt Qw Qy tQ tU Ua uG Uk Ur Us vB vS Vt VV vW wF yH yL tL xA) yH(aC aE aF aI aL An aO aP As bE bF cG cW cZ dD Dg eC Et iP Iv iZ jD Jf jO jQ jR Kc Ke Kk Kn Kp kR Ld lL Nd Oe Ou Ow Qg qY rA rB rC Uf Uh) rC(Aj aY Ba bL bQ bR bS cA cG CH cL CO Cp cQ Ct cZ dB Dl Ef Fb Iz Kc Kk Kn Or Ph Qw Rc tN tU Tv Tz Ua Uh Us uT vB Vq vV wE wF tL) wB(Al aP aY bL bN bP cH cN cO CS cW dA dG dL eT Fn gL Hw iB Ic Ih iP Ir jF Jk jT Me Mk Nm oK oN Or Ph qH qT qU Qw Rg Rm Tz vS) wE(aV aY Bc Bg bH bL bQ bR bS bU bZ cA cD cG cK cL cN CO Cq Ct cW dA dG dH dJ hA jM JY Ko lK lO oE oN pF Qw Qy Tj) wF(aF aI aM aO As bF bN Bo cE cZ Dd dF Dg dH eC jD jI jK jO jT Ke Kk Kn Kp kR kS Ld lL nW oF pF pY qD qT qW qY Ri Uf Uh) tL(aC aG aH aI Aj bB bF bN Bo cE dA eC Fn gL Gp Hb iB Id iP jD jK jO Kc Ke Kf Kk Kn Ko Kp kR lL pF pY Qg qQ rB Tr Uf Uh) vS(aD Aj Bc Bo Ch Cq Ct cZ dA Ef hA hB IB Il Iz Jk jM JY Kc Ko kR lK lO Nd Nw Qw Rc Ri Tn Tz Ua Uh Uk Ul Us Uv Tj) uT(aY Bc bH bJ bL bN bP bX bZ cK cN cO cU dA dG dH dJ dL eC eT Fw hA hR hV hX jF jM JY lO Nd Nj oE oK oN Or pF Tn) tQ(aM aQ aW bP cH cL cN CS Dd DK dL dN eC eD eT hG hR hV iP jO Kk Ko Kp lM oK Ou Ow qD qT qU Qx qY Rc) Yd(Bo Cx Ed Et Gc Gp Ij Ji Jn Kq Lh Li Mt Mw Nn No Nq Nw Om On Ow Pe Pj Qd Ql Qy Si Sr Uh Ut Vj Vq Vt Zq) yL(aG AJ aP bM bP cQ cW dJ dL dN eC eD Fw Gp iB Ic iP iZ jF JK jO jT lL Nd nW Ph qT qV qW Rg Ri tF) tU(aF aM aO aY bF bM Dd Dg dL gL hW iP iZ jI jO jT JU JV Ke Kl Kp Ld lM nW oK qD qT qU qY Ri Uf) rN(aP bP cW Dk dN Fw Gp Hq Hr Hu Hw Ih In iP jF JK jO Mj Nd Nk Nn nW On Or Ou Ow Ph qH qV qW Up Uv) vB(aC aF aI aM aO bF bN Bo cE cZ Dd eC gL hG iP jD jK jO jT kS lL nW oF qD qT qU qV qY rB Ri Uf) jT(bI bL Co Cp cQ Ct Dp Ez Jf Kj Ky Ng Oy Qt Qw sC Ss tN Tr tX Ua Uk Um Us vQ vV yE) jU(bP bS cA Ch cJ Cp Dc Ef Iz Jd Je Jj Jk Nd Ng Nl Oy Qt QW rB Tt Tv Ua Uk Ur) Wc(aN aW aZ Bo Cx Ed Fw Ij Iv Js Kd Kq Mt Mx No Nu Nw Ny Om On Pe Qy Sr St Vq) jK(Ar bX cI cR Ct

Figure 28 Continued dB iH Jj jO Ju Kc Kf Mh Mk Na Nb Ng Oy Qw tN tX Ua uG Vq vV) jO(bB Ct Et hB hR hW Ib Ji Jj Kj Lh Mh Ng Nl Nw Nx Qw rB tN Ua UG
Uk yE) hX(aH cH cJ cZ Dd Dl dN eC Hf Kc Ke Kf Kk Kn Kp Nl oH Qv Ri Uh Um wK zA) Yk(aA aZ Bo Cx Ed Fw Ih Ij Li lW Mt Mw No Nv
Nw Ny On Oz Pc Pe Qb Sr) hR(bL cH cJ Dd Dl dN eC Fb Kc Kf Kn Kp Ld Nl oH Or Ow Ph Qv Ri Uh wP) iB(Ar CH Cp cR eC Ib Je Kc Kk
Kn Ld oH qD Qu rU rV Uh uL Us yJ) vV(aE aF aI aL Ao cX cZ Id jQ jR Kc Kk Kl Kn Ld oH Qg qW rB Uf Uh) rB(aH Bn cH Cp cQ DB eC
Kc Kk Kn Ph qQ sC Uh Us vP Vq) Xa(Af aN aW aY aZ bJ Ed Hx Ld Oi Oz Pb Pc Ur Uu Vs Vt) qD(Ct Hf Hr Jk Jm Jo Mg My Nu Of Oy Ql
Qv QW Ua wC) Vj(aN aY Ed Fw Gl Il Jm Kd Lp Nb Ny Oa St Us Uv) Sh(aY Cx Fw Ih Im Ju Jv Mw Nn No Pf Qy Sf Sr) hW(bL bP bX cN dL
dN eC Kf oH Or Ut vW xA) pS(aY bP cN cS dL Hb Nh Nk Nt Ou Ow Rc Ub) yE(aJ eC iZ jF jl lL nW oK qT qV qY) rU(Bg Ch Cq Ct Ef Il Iz
Jm Tz Ua Uk) cH(hB jE qW rX rY rZ sM uG uU vO) tN(aF aI aO bF cE cZ Ke Kk Kp lL) Im(Aj Eq Hl Og Ry Uw Wh Yh Yl) xA(Bo cQ Dd eC
gL hG IL qV qW) zA(Bc cN dA hA jY IK oN Qw Qy) Fc(Bo Ed hB Lz mZ No Oz Pe) Uh(Dr hA hV IK IO mZ nl rQ) pY(Aj Hc Iz Jk Kj rX rY
Ut) Yh(Ij Ld Li Mq Nn Nw Ow) We(Jk nU Ny On Qy St Ut) Wh(Bo Cx Ih Ij No Nv Pe) rY(aV cB cK cZ dA Ke Tz) rV(Cq Ef Il Jm Kc Ks Tz)
vP(cZ jQ jR Qg qO qP qW) vW(aI Bo fP hB hG IM oF) Dr(Ed Kd Oa Ow Sr Vt) Wb(Li Lj Mf Mh Ow Pf) Vz(aW Fw Il Ow Pe Pf) Ji(jE jP lN
Og Om Oz) jF(Ng Nl Us wH wP tM) jY(bS Cq Qw Ua Uv wK) Et(Aj Jj Og rR wC) Th(Kz Ld Li Ql Ur) Kc(sK tX uV vT yD) Vb(aN bJ Cx Ih
Ij) eC(rX uX vA zl tM) hV(cJ Dl dN Kc Kf) wH(aP bP Dk dN Fw) IM(Cp cQ Ct oK rT) rQ(Fa Fw Jk Kn Up) uG(iP nW qV qW Ri) uU(Bo hB
hG Id Kk) Ed(Fd Gn Yi Ti) Eq(Mt Nn nU Qy) Gc(Oa Us Uu Uv) Zq(Af Aj Gl Uu) Zw(Cx Ih Ow Pe) Ld(hA lK lO ul) Vc(Bo Ij No Pe) wK(aF
cW IK oE) yD(bL cW IK oE) rR(cZ Kc Qg Ub) uX(aP dN Fw Hw) Ti(hB Nb Oa) Lj(Du Yj Tl) Nw(Hr jP Md) Vq(jE qT qY) hA(bF cE cG)
nU(Gn Hl Ye) nl(Rj Ur Us) wP(aY Nd Rc) tT(aP bP dL) wC(Kk Kp nW) wG(bX cB Kc) tM(bN oK qU) jV(Ng Oy Qw) lO(bE bF cZ) vA(aN Ic
Ph) Aj(Ap Jg) Gh(Pe Pf) Mw(Yg Ye) Lp(Oz Ur) Or(sK tR) mZ(pH Rz) tX(Kk IL) hB(Uy wQ) qA(Ch Hu) sM(Id Nt) oW(Jo Ug) uM(Iv Kf)
uI(oH qY) uP(aY Qy) uZ(hG oK) CtIL DuLi FwYl NnYg NbTl NgjE NljQ ljVh SiOw SjnN QgsC KsfN RyOa LtVt OpPf UwPe UxaZ aOeT
aWrT dJqQ dLtR nWvQ} Xa{Oz(aN aW aZ bJ Cp cQ CU Cx Db Dc Dk Ed hB Hc Hq Hv Hx Ic Id Ih Ij Il In Ir Is Jh Ji Jk Jn Jr Js Ju Jv Ky Ld
Lh Lv Ma Mb Mj Mk Mp Mq Mr Mt Mw Nd No Nq Nr Nt NU Nv Nw Ny oF Oh Oi Om ON Ou Ow Pa Pe Pf Pg Pi Qd Qe Ql Qm Qw Qy Rm
Sf Si Sr St Tr Tz Uc Un Ut Vq Vu Yi Yj Zx) Oi(aA As aZ bF bQ bZ cE cL cO cQ CU Du Ed Fc Fd Fn Fw Gz hB Hq Hv Hx Ih Ij Il Im Is Jh Jk
Jl Jn Js Jy Kq Ld Lv Lx Ma Mj Mp Mq Mr Mt mU Mw Nb NN No nU Nv Nw Ny Oa oE Oh Om On Or Ou Ow Pa Pe Pf Pg Qd Qe Ql Rj Rm
Rx Sr St Tz Uc Un Ut Vp Vq Vt Vu) Ed(aK aU aZ bF Bg bQ bZ CH cQ Cu Cx Ef Ez fP Gc Il In iP Is Jh Ji Jk Jl Jp Jr Jy Kk Kq Ld Lv Ma Mk
Mn Mt Mv Nd Ne Ni Nj Nn Nq oF Og On Or Ou PF Qh Qv Rb Rj Rm St Tr Uc Ug Ut Vq Vu Yd Zx) Ld(Al aW aX aY aZ bF bX Ch cQ Cu Cv
Du fP Fw Fy Gp Hc Hq Ih In Ip Iq Jk Jl Jm Jp Jy Kd Kk Ks Mj MW Mx Nn Nq Nv Nx Oa Og Oh Ou Pa Pe Pf Pg Qc Rb Rj Rm Rt Ru St Uc
Ul Ut Vq Vu We) aZ(aM As aW bB bJ bU cS cU Dp Ef eM Fw hB Hl Ho Hx Ih Il Im Ir Jh Jn Jy Kk Li MF Mi Mq Mr Mt Mu Mw Nb Nc Ni Nj
Nk Nl Nq Nr Ns Nu Ny oE Pb Pc Pe Pf Qc Qd Qe Ql Rx Sr St Va Wc Yk) cQ(aM aP aW Bo CU Dr Et Fw Fy hB Hx Ih Ij Il Im Jj Jl Js Jy Kq
Mq Mt Nf Ni Nl Nn No Nr nW Ny Oa Oh On Ow Pb Pe Pf Qe Ql Qx Ra Rj Rm Ru Rx Sh Sr St Ut Uu Va Vq Vt Vu Wc Yi) Nn(aH Aj Ap bM
Bo bS bW Co Dg eF Eq fP Hb Hx Ik Jj Jo Kg Kj Kk Kl Lx Lz Mg Mj Mx Nc Ng Nk Oh Or Ou Oy Pb Pc Qb Qh Qt Qu Qz Rj Rz Ss St Tz Uh
Uu Ux Vb Vq Vt Wh Ye Th) hB(AN aR aW aY bG bR bS Ct Dc Dd dG dR Ex fP Fw Gc Gp Hb Hc Ic Il Im Jd Ji Jm Kd Kk kQ kR Lj Lu Nx Of
Pa Qc Rj Ru Si St Uh Ul Um Uy Vq Vq Wf Th) nU(Ad aH aX bQ cE Ch cO dC De dF Dl Eq Gb Gd Gn Hb Hl In Jg Ji Jj Kl Kj kP Lh Mb Mp
MY Ng Nw Oh On Or Ou Oy Qm Qv Rj Ug Uh Ur Uu Vs Yl Ye) St(aF aU aW cO cU dl dR Ez Ib Ik Ji Kd Kq Kz Li Lv Me Mf Mk Mp Mq Mt
Ng Ni Nq Ns Nu oE Oh Or Ou Pb Pc Rc Rj Rx Sh Sr Uu Va Vq Vt Wh) Rm(Af Aj aM aW bN cD cM cU Dr Ik Ji Jj Jv Kd Kk Ky Me Ms Nc Ng
Ni Nl Nu oE Og Oy Pb Pc Qt Rc Rj Rx Sf Sh Sr Uh Uk Uu Vt Wh Yk Ye) On(aO Bg bJ bV Ch Ct Eq fP Hc Il Jm Kf Kl Mb Mf My Ng Nu Nx
oE Ok Or Pb Pc Rc Rj Ru Rx Sr Ss Tn Uv Vs Vt We Wf Wh Yg Yh) Ut(Af Aj aW Bg Bo Ch Ct dC Ef Eq fP Gl Hx Ib Jm Kd Kl Mb Mh Nc Ng
Ns Nv Of Or Oy Pb Qy Qz Rc Ru Rx Ss Uu Uv Vq We Yh Ye) Il(Aj aM Ar Bo Fn Fp Gz Hb Hv Hx Ji Jj Jo Ky Kz Lj Lv Mj Mq Mr Nf Nq Ny
Or Ou Qb Qe Ql Rh Rt Sh Tz Un Ur Uu Vt Vz) fP(aW bG bZ CU Fw Gp Ic Iv Jh Ji Jn Js Ke Kq Li Lv Lx Ma Mk Mp Mq Nu oF Oh Ow Pf Po
Qa Qd Qe Ql Rx Sr Uh Ur Vq) Pb(CU Fw Hv Hx Ij Im Is Jh Jl Jn Jr Js Lv Mp Mq Mt Nb Nd Nv Nw Oh Om Ou Pe Pf Pg Pi Qd Ql Sr Uc Un Vq
Vu) Rx(DC Fy Hx Ih Is Jh Jk Jl Jm Jn Jr Js kR Lv Mf Nb Nd Nw Oa Oh Or Pa Pi Qb Qd Qh Tz Uc Un Vu tF) Or(aW aY bE bJ bN Cx cZ dK Fc
Fw gL Ho Jh Jm Kd Mt Ni No Nt Nu Nx Pa Pe Pf Pi Qy Ru Rv Sr Ul Vq) Im(aG AJ aR dC Dl dM gP Ha Hb Ib Ik In It Lp Mf mY Ng oE Og
Oy Pc Qt Qz Rg Rj Ss Ur Wf Wh Yh) Pf(Aj aW Bg bM cE Ct dC eM Hx Kd Kl Mq Ng Of Oy Pc Rh Rj Sh Ss Un Uu Uv Ux Vc Vt Vz Wh Yh Yl)
Cu(Af Aj aX aY Bo Ct dC eM Eq Fw Gl Jo Kf Kl Lj mY Ng Nl Nx Pc Qc Qe Rt Sr Uu Uv Vb Vs Vt) Qc(AA Af bM bN cO cU Dr Hx Iv Jj Jl
Kq Me Mq Mt Ni No Nw Ow Ql Qv Rj Sr Un Uu Vq Vu) Ny(Af bJ Bn Bo bS Cx Dp Ib Ic In Iu Je Mb Mf Ns Nv OE Qn Rc Rj Ru Sr Vq Vt Wf
Wh) Hx(aW aY bZ cU Cx Dc Gp Ij Jm Jp Jy Kd KQ Lv Nq Nu Nx Ou Pa Pc Rj Sr Uh Ul) aW(Aj Ap aX dC Dk dR Ex Gz hC ln Jj kl Ky Lv
Mj Mq Nb Ng nW Oa Og Ou Ql Un Vt) Fw(Aj aM dC In Jj Jy Ki Kk Lv Mf Ms Ng Ni Nl Og Ou Pc Ql Rc Rj Un Uu Wh Yl) Pe(cA cK dC Fc
Gb Gh gP Ha Ik ln iP kC kl kO Mf mW mY nA No Og Pc Uv Vc Wh) Nq(Aj aX aY Ch Eq Jj Jm Kd Lj Nx Pa Qb Qz Ru Sh Sr Ul Uu Uv Ux Vt
Ye) Qd(Af Aj Cx Hu Ib Ik Kd My Ng Nx Oy Qz Rj Ru Ua Ul Ur Vs Wh Yh Ye) Rj(dC dR Ih Ir Is Kq kR Mr Mv Mw Nb nl Nv Nw Oa Qb Qe
Qh Tz Vu) cU(Af Aj aX aY bM bR bS cG dC dH Dr eM Ih Ik No Pc Pi Qe Uv Vc) Ij(cA dC Fc Gh hG Ik In kC Mf nA nD Ng nl No Oy Pc Uv
Wh Yh) Vu(Aj aX Ch De Eq Gl Mb Ng Oy Pc Rt Ru Sr Ur Uu Uv Vq Vs Wh) ln(aY Fc Ih Jn Kd Lj Nb No Nx Oa Oh Ow Pi Ru Sh Sr Vq Vt)
Kd(aM dC Ex hC Jj Jn Jr Jy Kq Ky Lx Mq Mt Mv Ni Ou Un) Vt(aN bF bZ Ch Du eM Jl Jn Jy Ks Lv Ma Mf Mt Mv Og Rb) Nw(Af bJ bN Bo
Cx Dp eM Jq Nc Ni Nk Nu Nx Pc Rc Wh) Kq(Aw dC eM Eq Kp Ng Nx Pc Qu Ru Ul Uv Vs We Yg) Jh(Aj aM aX eM Fa Ng Oa oE Oy Pc Qb
Sh Ss Uu) Sr(Ch dC Ik iP Jy Lv Mf Nv oE Og Ou Pc Qh Ug) Ru(dC Gz Hv Ji Jy Lv Lx Mr Mt Mw Og Ou Qe Ql Un) Is(Ad aY Bg dl Iz Ng Nx Oy
Qt Rt We Wh Yh) aX(Co cS Ef gL iO kG Li Mg Mq Mu Mv Ni Ow) Uc(Af Aj Bo Ch dC Eq Kl Oy Rt Uu Va Vs) Mf(aA Dr Du Mt nL No Nu
Sh Uh Vq Wb) Jm(Et Jy Ky Mk Mq Mr Og Ou Ql Un Vj) Nv(Af Aj Bo Ct Dp Lz Mh Nc Uu Vq Wh) Ow(Af Ch Cx Du Ik Jy nC Ng Ni Nj Og)
oE(aN aY bM Bo Gh Hb kR Qt Si Uh Un) Mt(Aw bV mY Ng Pc Uv Vb Vq Vz Wh) Nb(aM Bo Ii Kp mW Nu Oy Sh Uh Uu) Qe(Af bM Bo Cx
dl Dr Du Ha Ii Ye) Aj(bZ Ef Hq Iz Jy Mu Ni Ou Vq) No(cA cK gP iP nY Og Pc pF Vc) Ni(Js Mx Oa Oh Pa Qb Tz Uh) Jy(Ch Hv Nx Pa Qb Sh
Ss Ul) Uu(Dc Dk Ef Jk Nd Om Ou Pg) Pc(Ih Jn Js Lx Nd Oh Ql Tz) Du(Ex Js Li Mq Oa Oh Qa) Og(aY Lj Nx Oa Oh Qb Ul) Vq(dC eM iZ kR
Nd nY Qb) mY(bQ bZ cO cS Lx Ma Rz) Et(Af aY Cx dC Gl Nd) Fc(dR Jn Jr kR Tz tF) Jl(aN Bn Bo Nx Rt Ul) Ou(Af aY Gl Nx Pa Uv) aM(aD
aY Jn Nd Pa Pi) Lv(Af aY Nu Nx Vs) Ql(Dc Ik Mx Pa Qh) Oa(CH Cx Mk Nj) dC(Nu Qt Sh Uf Uh) iZ(Hb Ib Lu Uh Wf) Mq(Kk Ks Pa Ye)
Jk(Fp Lz Ml Qx) Om(Kg Oy Vs Wh) bJ(Jq Jr Kk Mj) Ch(Ef gL iO) Cx(Ik Sh Tz) Mr(Ib Ul Ye) Mw(Hu Ib Ye) Qh(Af Nl Rt) Oh(dH mF Vc)
dR(cY Dr Wh) oF(aN aY bM) Bo(kQ Nd) Dc(aP Rt) Ef(Eq Jj) Lx(Uv Wh) Mj(aY bN) Sh(Jn Ju) Qa(Ha It) Qx(Dd Pi) Lj(Bg bZ) Un(Nx Pa)
AaGp AfPg CoNg EqMv NrRh LzPi MpkR NdKz TzOe TrVs IhIk WfnY JjkQ cLeM nNkI} Rx{Rm(aA aE aH aM aZ BA Bc bM bQ bR cJ cM
cT Cu Dc dF dl Dk dN Dr Ed Fa Fd fR Fy Gz Ha hB hC Hf hG Hv Hx Ib Id Ij Im iZ Je Jf Jh Jj Jk Jl Jp Jq Jr Js Jy Ke Kk Kq Ks Ky Kz Ld Li Lj
Lx Me Mh Mi Ml Mq Mr Mt Mv Nb NC nH Ni Nk Nl NN No Nu Nv Nw nY Oa oE Oh On Ow Oz Pc Pe Pi Qd Qv Ri Ry Sr St Ub Ug Uk Un
Ur Ut Va Vj Vt Vz Yi Yj Yk Zq) Oa(aG aH Ao aZ BA bF BG bM bZ cE Cp cQ cT Cu cV Dc Dd Dk Dr Du Ef Fy Gc Hq Hx Ij Il Im ln Is Jh Ji
Jk Jl Jn Jp Jq Jr Js Jy kK Kq Kr Ks Kx Ky Ld Lv IY mF Mj Ml mM Mn Mp mS Mu Mv mW Nb nC Nd nH Ni NJ nR nU Nv Nw Nx Ny Og Oh

Yd(Ed Lv nI nL Uc Uu) Si(bR lX Ne nI Un Vt) Et(Aj Jj Ng Og Oy) Vj(Ap Dl Jm Or Pj) Jj(Ji Lh Ok Zq) Gd(nH nL nU) We(mI nU Ut) Uw(Jl Qa Qd) Fd(Ii lW) Gc(nH Uu) Zq(aH Kk) Zx(Ed Uu) Lp(nC Ug) Og(Ji Ok) oW(Jo Ug) AjJg CtjT EfwD HonU RvkC OpOu UpfB VveQ} Pf{Vz(aA aE aF Aj aO Ax aY aZ bA bR bS bU bZ cB cE cM Cp cQ Cu Dc Dd dH dR Ed eM Eq Fd Fw Fy Gc Ha Hb Ho Hp Hv Hx iA Ih Ik Il In Iq Ir It Iv Ji Jl Jm Jn Jp Jq Jr Js Jt Kd Kn Ks Li Lj Lp Me Mi Mr Mt Mx Na Nd Nj Ny Oa OH Oi oK oN Oz Pc Pe pF Pg Pi Qa Qb Qc Qd Qe Qh Rb Rm Sh Sr Ss St Tv Tz Ub Uh Un Up Us Ux Vc Vp Vq Vt Vu Wh Yl) Sh(AA aE bM bO bR Cp Cu cW Dd Dk Ed Ef Fd Fw Gb Gc Gz Ha Hb Hp Hv Hw Hx iA Ib Ih Il It iZ Ji Jk Jl Jn Jp Js Jt Ju Jv Ko Ks Ky Lx Ml Mn Mr Mt Mv Mw nD No Nt Nv Ny oH oK Om Pe Pg Pi Pk Qd Rb Rh Ri Rm Sf Sr St Tz Ua Ub Uh Un Ut Vc Vj Vq Vu Yg) Yl(Aj aO Ax aY aZ bR Cq Cu Ed fP Fw Fy Ha Ho Hp iA Ih Il In Iq Ir It Iv Jn Js Jt Kd kG kK Ld Lj Lp lW ME mF Mi Mr Mx Na nC Nd nH nJ nL No Ny Oa Oi Pe Pg Pi Qe Rb Sr Tz Ub Up Vp Vq Tj) Vc(aA Af Aj An aZ bM Cs Cu Dd dI Ed Fd Fp Fw Gb Gz Ha HB hC Hf Hp Hv Hx Ih Iv Jl Kl Kz Li Lj Me Mr Mt Mv No Oa Or Oz Pe Pi Pk Qd Qg Ri Sr Un Uu Vo Vq Vt Vu) Hp(aE Aj aW aZ bR bS cB cM cT cV dR GP Ik Jj Lu Lv lX Mp Mt nA nD Nn oE Oi Or Ow Oz Pa Pc Qv Qy Ri Rj Ss Uc Uf Ug Uh Um Uu Ux Vb Vj Vt) Eq(aA bO bW cO dI Ef Ez Hf Jh Jk Jy Kz Ld Li Mi Ml Mp Mq MT Mu Mv Nn Nq Nv Om Ow Pd Pi Qd Qy Rh Ri Ua Uf Ut Vj Vu) Ux(aE bJ bM Co Cu Ef Gb Gz Hb Ih Jh Ji Jk Li Mi Mp Mq Mt Mu Mv Ni Nq Om Qd Qy St Ua Uh Un Ut Vj Vq Vt Vu Zq) Fd(aA Af Aj aY aZ bJ bM Cv dR Fc Jk Jo kN kS Ld lW Mj Mq mY nL oH oK oN Oz Pc Qy Rh Ur Uu Uv Vj Vt) Vb(Aa Cp Cu Dd Dk Gb Ho Hv Hw It Iv Jt Ko Li Mi Mq Mr Nt Pe Pi Sr Ua Un Ut Vp Vu) Wh(Aa aE Dd Gb Gz Hb Ih Jk Jl Ld Mt Mu Mv No Nt Nv Pe Pi Pk Qd Ri Ua Un Vu) Rv(aE Aj aZ bR fP hC Ik Jl mW nB Nd Nv Ny Oa OH oN Or Pa Qv Tz tF) Gh(Aa aE bR bS Dd Ed Gb Gz Ha Hb Ih Lx No Nt nU Pe Pi Pk Ri Uh Un) Vj(Aj aX aZ Ch cS Dc Dg Ed Jl Jm Kl Ng Ny Oa Or Qb Rz Tz) Fc(Aa aE Dd Gz Hb nD No Nt Pe Pi Sr Un Vq) Gb(Aj cA cK hC Hf hG Nd Or Oz Rh Uu Uv) Zq(Ap Dg fP hC Kc Kg Kl Mg Mm Ng oK Uu) Gd(Gc Ko Oa Om oN Ow pF Qy Sr Un Vt) Ho(aA Aj aX aZ bM Kg Ld Or Oy Rh Uu) Zw(Hx Ih Jl Ld Ny Qa Qd Uc Un Vu) oV(Ad Aj Ii Jj Jo Kj Pz Ue Uu Vo) Du(Cs Fa Fp Js Kz Lj Mr Oa Qd) Yh(Cu Hb Hx Ji Jl Qd Tz Un Vu) Gc(Ed Hf Oa Or Ri Uu) Yg(kN nD Oz Pi Qd Uu) Rz(Jh Mq Nq Qd Ut Vu) Si(hC Hf iZ Rh Uu) Lp(bM Or Un Ur) Uy(Gz Ld Mv Vu) Aj(Ry Vq We) Ed(Yd Ti Yf) Yk(mI nD Oz) Op(Dd Hb Ji) Uh(eP mM nI) We(Ut Uu) Ld(eQ Uz) Rh(Uz Wc) Vw(fP Qd) nU(Hl jO) nD(Zx Tl) DdSf TiOa NgWd YjnH YdJi JoRt RyaZ LirS RiwD OweP UrnI UueQ dIfB hBoT} Nn{Wh(aA Ad aE aH aL As Ax bA Bn bS cF Cp Cs cT Cu Cv Cw Dc Dd Dk Em Et Fd Fy Gb Ha Hb Hl Ho Hv Hw Id Ih Ii In Ir It Iv Ji Jl Jn Jq Jr Jt Kd kI Kk Kn Ko Kp Kr Lh Li Lx Ml Mj Mq Mr Mt Mv nD Nl No Nr Nt Nv Nx Ny oH Ok Or Ou Pa Pd Pe Pg Ph Pi Pk Po Qa Qh Rb Rm Rt Tn Tv Uc Un Ut Uz Vp Vq Vs Vu Wc Yl Tl) Eq(aA aE aH aO aX aZ BA bF Bg bM bQ bR bW cE cR cT cU cV Dc Du Ed Ef Fd fR Fy hB Hq Hx iO Jh Jj Jk Jl Jm Jn Jp Jy kK Kn Ky Ld Lv Ma mI Mj Ml Mr Ms Mu Mv mW ND Ne Nq NU Ny oF OH Om oN Or Ou Pa Pi Qa Qd Qt Rm Rt Tr Tz Ua Uc Uk Un Ut Vp Vu Vv) Sh(aE aG aH Aj aR aX bM bS bW cF Cu cV Dc Dd Dk dL Du Et Fd Fy Gp Hb Hx Il Io Jl Jp Jq Jr Js Lv Lx Ml No Ny Oh Oi Om Or Ou Ow Pe Pg Pi Qd Qh Qm Rb Ri Rm Si St Tr Tz Uc Uh Un Up Ut Vq Vu Yd Yj Zq) Vb(Ad aE aL AX bA Cp Cq cT Cu Cw Dc Dd Dk Em Fd Fw Fy Gb Ho Hp Hv Hw In Ir It Iv Ji Jt Kd Kn Lp Mi Mj Mr mW Na No Nr Ny Pe Pi Rb Rm Rt Sr St Tv Uc Un Up Uz Vp Vs Vu Vv Tj) Vc(aA aH Aj aX bA bM Bo bP cF Ch cQ CU Dc Dd Ed Fd Hb Hu Hv Ib Ir Iv Ji Jq Js Kd Ld Lv Lx Me Mj Mr Mx Ng No Nr oF Oh Oi Or Ow Pe Pg Qb Qd Qh Sr Tv Tz Ug Uh Un Vq Wm) Rz(aE aG aH BA bM cE cT Dc Dk Ed Et Fd Fw Fy Gb Ho Hq Ih It Jk Jl Jm Jn Jp Jv Li Mi Mp Mr Mt No Nq Nu Nv Ny Ow Pd Pe Pi Qa Qd Qe Rm St Tv Uf Uh Un Ut Vq Vu Vv) Fd(aA Af aH Aj aM bM bR bW eF fP Gl Ik In Jj Jo Kg Kj Kl kP Ld Lz Mg Ml Nd Ne Ng Nk Nu Oi Or Oy Oz Pb Pc Qx Qz Rt Ss St Tz Ur Uv Yh Th) Ux(aE aG aH aI aL aM bM bR cE cF cM Cu Dk Et Gb Hq Ih It Jl Kn No Nu Nv Om Ou Rm St Uc Un Vq Vu Zq) Yh(Cu Dc Dk Hb Hx Ji Jl Jq Jr Js Lx Mj Mr Ny Oh Qd Qe Rm Tz Un Vu) Gd(bA Kd Kk Ko Kp Kr Ky nU Oi Or Ou Ow Qx Sr Uc Vp) We(Cu Dc Jq Jr mI nD nR nU Ny Rb Uc Vu) Rt(Aj bA Cu Dc Fy Jj Jl Kg Kj Oy Pi Tv) Uz(aH bM bW cQ Jj Kg Ld Nd Or Ou Oy Th) Wd(aE Aj Jl mI nD Ng No Ny Pe Un Vu) Du(Ax Cs Jr Js Lj Mj Oa Oh Qd Vt) Oy(Hl Ho Ry Uw Vh Wc Wg Yl Tl) Gb(Ap cQ Dg Dl Kg Mg Ng Or) Aj(Hp Ko Uw Vj Wc Yg Tm) Vz(aZ kC mF mW nA nD nU) Yl(aH aZ Ed Fw Ld Or Pe) Gc(Hf Jv kI Un Uu Vu) Ho(bW Jj Jo Kg Kj Qz) Zq(Dg fP Mg Nd Ng Qz) Tm(aX Jm Kd Oi Pa Qz) Yf(Ed kP Mx No Pe) Yg(Jl mI mW Ng Ny) Yj(aZ fP Jm Oz St) Zw(Jl Rm St Un Vu) Uw(cQ Kl Mg Ng Ss) Fc(Lx No Pe Un) Fi(Lx No Pe Un) Hp(aZ Ou Qz Uh) Yd(Ed Hb Ji Lv) Wc(cQ Kg Kj Ld) Lp(hB Jj Or Ug) Gh(Lx No Pe) Uy(Ld Ms Un) Vw(Cu Ny Ss) Ti(cQ Oa) Th(nU Qd) Hl(nB Vt) Zx(Ed Oa) Tl(fP mI) AnwD HbSj YkRm SihC SfcF WgcQ JmVj RyVt RvOr OpaG UheP UreQ VhmW bMfB wBnW} Ed{Yd(aH aM aQ aU Ax BA bQ Cs cT dK dN Ez Fa Gc gL Hx Ih Ir It Jh Jn Js Kd Kz Ld Li Lj Lz Mf Mh Mi Ml Mq Mr Mx Na Nd Nf Ni Nj NK Ny Oa Oh Oi Ow Oz Pc Pd Pe Pi Ql Qt Qv Qw Qx Ra Rf Vt Wm) Gc(aE aH aO aZ BA bF Bg bQ bZ cE Ch Co cS cT dF dR Ez fR hB Hc hG Hq Hx Ih Il Iz Jh Jk Jl Jm Kk Ky Lx Ma Mj Mr My Ni Nj No Nq Nr Nv Ny oE oF Om Or Pg Pi Qt Qv Qw St Tn Tr tF) Zx(aE aH aI aQ aU Ax BA bQ cT Cw dK Ez Fy Hx Ih Ir Jg Js Kk Kx Ky Kz Ld Li Lx Ma Mf Ml Mp Mq Mr Mv Na Nf Ni No Ny Oa oE Oh Ow Oz Pe Pi Ql Qt Qx Ra Rf Sj St Uf Vq Vt Zq Wm) Fi(Ad Ba Bg Co cS EF Et Fr iJ Il iO Iz Jd Jg Ji Kl Lh Lv Ma Mf Mg Mm Mt Ng Ni Of Ok Om Ou Ri Tn Tr Uc Uf Uw Ux Vq Vu Vv Wd Wh Zq Ti) Uw(Af aK aQ aU aZ bF Bg bQ bZ Ch cQ cU Cx cY dR Fc GP Ha Ii In iP kO kP Ld Mf nA Nd Ne Nl oE Og Oi Oz Pb Qv Ug tF) Vj(Al Bg bQ Ch Dk Fy hB Hc Hq Il Jk Jl Jm Jr Ks Lv Mf Mj Nd Nx oF Og Or Oz Pa Pg Ph Pi Qh Qt Rm St Tr Tt Uc Vq) Fc(Ad Co Cu Cw EF Et Fy Iz Jd Ji Jp Lh Lv Lx Mt Ni Nr Nx Ok Om Ou Pe Pg Rb Tn Tt Uc Vu Vv Wd Wh Yg) Gn(Ad bZ Cq Cu Dc Dk Gp Hv Hw iJ Ir Jl Jq Jr Js Mi nU Or Pi Qa Qe Qh Ra Rb Rm Tv Uc Ut Vu Vv Wg Yg) Vc(Ao Ba bF Bg bQ bZ cE cL Co cS cU dF Et hB Hq Il Iz Jd Jp Lh Lx Ma Mg My Nq Nr Om Pg Tn Tr Uf Zq) Yg(aG aH aU aZ bB bF Cx dR GP Ha hB Ib Ii In iP Mf Nd Ng nY oF Og Oi Oy Oz Pb Rj Ug Uu) Zq(aK aU bF Bg bW bZ Ch Et hB In Jm Mf Nd oE oF Og oH Oi Or Qv) Ti(bF Ez hB iO Jh Jl kI Kk Mt Nk Nv Ny Oa Oz Qd Qv Uc Wm) Wh(aQ aU aZ cV cY dR Et Gp Lx Mn oE Oi Ok Om Oz Tn Tr) Zw(aG bF Bg bZ Ch cS dR Gp iJ Nq Og Oz Tr tF) Yf(aM Ba Cu Fy Il Lx Ni Nj oF Pz Ra Vq Wm) Si(bF bQ bZ Ch Et hB iA iO Nj oE oF Og oK) bZ(Eq Fd Hl Ho Rt Ry Uz Vh We Wg Yl Tl) We(dR Ky Ld Mk Mt Nj nU Oi Qv Ut) Wd(aU aZ Gp Mf oH Oi Om Oz Pb) Rz(Co dR kI Ld oE oH Oi Or Oz) Yl(Ba bF gL Il Ma nR Pz Tr Tt) Vh(bF dR Gp hG In Nj Nl Ug tF) Fd(bF Ch cS Cx Gp Nj Nq Og) Eq(Ba cS Ef Mv Oz Uc Vu) Sh(aM Bg hB Il Nq nU Tr) Ux(aQ aZ dR Ld oE oH Oz) Gh(Co Et Lx Pz Tn) Gb(bF dR Nd oE tF) Gp(Hl Rt Uz Wg Tl) Wc(Et Ji Jq Om Uc) Op(Fa Hx Ml Oz) Vw(aQ kI oE Oz tF) Ry(dR Nd oE Og) Rt(Cu Dc Uc Vu) Il(Sf Vz Tm) Sj(aM Ih Ql) Du(Js Ow) Yh(oE Og) Yj(Mf Rm) Tm(Nd Tt) Vb(Cu dR) Vu(Hl Ho) EmLd MvUy YkRm RaeQ UheP gZnH hBpI rBqC} Pe{Wh(aG aH Al aO Ba bF Bg bM bQ bZ cE Ch Co Cu cV cY Dc Dd dF Du Ef Et Fy Gp Ha Hc Hq Il In Iz Jg Jk Jl Jm Jp Jy Kk Lv Lx Ma Mn Mt Mu Mv MY Ni Nq Nv Nx Ny Ok Om Ou Oz Pg Ph Qd Qh Qv Rb Ri Sj St Tn Tr Tz Ua Uc Uf Ut Vu Yd Yl) Vz(aK aU aV aW bF Bg bO bQ cB cF cQ CU cY dA Dc dK Ef Fy Gp Hq Ik Il In Je Jm Jp Jr Jy Kd kQ Ks Lj Mf Mn Mt Mv Nd No Nq oE Oh Oi Ou Pa Qc Qh Rb Sj Tr Uc Us Ut) Vc(aE aG aH aZ bF Bg bM Bo bQ bZ cE Ch cL cV Cx cY Dc Dd dF Du Et Gp Hq Il In Jk Jl Jm Jp Jy Kk Lv Ma Mt Nq Oh Om Ou Pg Qd Qh Qv Ri Rj St Tn Tr Uc Ug Uh Vu Yd Yl) Gh(aH aR aW aY aZ bF Bg bM bQ bS bZ cE Ch cQ Cx Dc Du Gp Ha Hq Id Il In Jm Jp Jy Kd Kk Kx Lj Lv Lx Mf Nd Nq Ny Oh Oi Om Ou Pa Qv Ri Rj St Tr Ug Uh Ul Yd Yl Th) Yl(aU aW aY bF Bg bN bU cA cF cK cQ CU Dc dK Fc Fw Fy Gc Gp Hq Ii Il In Jk Jm Jn Jp Jy Kd kQ Ks Kx lW Mt Mv No nU oE Oh Po Qa Qc Qe Ri Rm Sj Uc Ut Vu) Du(aK aU cA cB cK cL cQ Cu cV Fc Gc Jn Jr Js kR Ld Li Lv MF Mp Mq mY nC Nd nH NO nU Oa oF Oh oN Or Ow Oz Qd Qe Qv Rh Tz Uc Ug Uv Vb Yf) Fc(aE aH aW bF Bg bM bQ bZ cE Ch Cu cV dF dR Fy Gp Hq Il In Jm Jp kl Kk Lv Lx Ma Mt Mv mZ Ni Nj Nq Nr Om Ou Pg Qv Ri Rj Tr Uc Uh Vq Vu tF) Fi(aG aH aK aW bF bQ bZ cE cL Co cS Cu Cx Dd Ef Et Hq

Figure 28 Continued

Jk Jm Jp Ks Li Ma Mg Mi Mp Mt Mu Mv Nq Nv Om Ou Ow Qv Vq Vu) Vb(Ba bF bZ cS Cu Dc Ef Jk Jy Ks Ma Mi Mt Mu Mv Ni Om Rb Ri
Ua Uc Ut Vu Tl) Sj(Af bH bM Ch cQ Cx Il In Jn Jy Ld Ni Nq Oi Pb Pc Qd Rb) Yd(aA Af cA cK Lj Lv lX mY No Ou Oz Pb Po Uc Uu Uv Yh)
Gb(aE bM cE Dc Dd Et Hq Ks Ni Om Qg Qv Ri Uc Vu) Th(bU cA cF cK dA hB Ky oE oN Oz pF Qz Uk) Rz(bZ Co cS Ef Hq Jk Mt Mu Mv
nA Nq Om Vu) Ux(Cu Ef Hq Jk Jp Mu Mv Nq nU Uc Vu) Gn(fP iP kl kO kP nR Rb Uz Vu) Yh(Cu Dc Hq nR Ou Uc Us Ut Vu) Vw(Ba Cu Ef
Jk Mu Mv Ua Uf Vu) Eq(Ef Ik kC kl kO nA nU Oz) Vj(fP gP Ik Il Jm Oa Pa) Sh(bF Bg Ch Il Jy Mv) Wd(Mt Mu Mv mY Om Oz) Yf(Cu Jm Qy
Ri St) Zw(Fy Jl Oh Rm Tr) Zx(lX mY nN Oa Oz) Wc(Cu Dc Pi Tv Uc) li(Fd pl Rt Tl) Yg(dR Jk Ut Vu) Uy(hB hG kl Vu) oW(Jj Jo Kn Mm)
Gc(Kk Ri Ug) Gd(nU Ou Uc) Yk(Dc Qh Rm) Zq(Ap fP gP) Tl(cQ Ld Ug) Ry(aZ kl Og) Uw(Uc Us Vu) pl(Jj Mm Vo) Ti(hB hG) Yj(fP Jm)
We(dR Ut) Rt(Jk Jl) cQ(Uz Wg) eQ(aD bM) CuVh FdHa HlnU HqrS SihB LpUg UheP kOlN} Oa{Du(aG aK aM aO aQ aU AW Ba bB bQ bR bU bW bZ cB cC cF cG cK cL Co cS CU Cw Cx cY Dc Dd De dF dH Em Et Ez Fr Fw Fy Gc Gp hB hG Hq Hu Hv iA Ic iH iJ iO Iv Jd Jg Jh Ji Jl Jn Jp Jr Js Kc Kf Kg Kl Kk Kn Ko KP Lh Li Lx Ma Mg Mi Mj Mk Ml Mm Mn Mp Mq Mt Mu Nd Nq Nr Nu nY oF Oh Om Or Ou Ow Pd Pj Pk Pz Qd Qe Qh Qv Qx Ri Uf Un Ur Ut Uw Vj Vv Wd Yj Zq Tl) Vj(aH aJ aW aZ bF BG cE Ch Cx Dc Dd Fw Fy Hc Hq Il In Jk Jl Jm Jp Jy Kd Ks Kx Li Lj Lv Mf Nd Nj Nx Ny Oe Og Oi Or Ou Oz Pa Pg Ph Qh Ri Rj Rm St Tn Tr Tt Vq Yd Zx Tl) Zx(aG aH aU aW aZ bF bQ bS bW cE cL cO cS CU Cv Cw Cx Dd dI dK Ez Gc Gp Ji Kc Kg Ko Ld Li Ma Mg Mi Mk Mm Mp Ni nN Nu Oh Ow Oz Pd Pj Qg Ri Rj Uf Ur Vq) Gc(AO aZ bF BG bM bQ bZ cE Ch Co cS cU Ef Hc Hq Il In Jl Jp Jy Ky Lj Lv Ma Mv My nC Ni Nj Og Oi Om Ou Oz Ri Rj Tn Tr Ug Ut Vu) Op(aW cS Cx Dd De dI Ez hG Hv Jh Kc KG Kj kO lW Mg Mq Mu Mw nC Ni Nj oE Oz Pc Pi Qy Ri Uf Ur Vu) Ti(aA aU bF Bg bR cF cQ cS Cv Dp dR hB hG Il Jl Jy Ky Lv Ma Mt Mv Ni Nq Ny Oe Oi Ou Oz Qa Qd Ut) Yj(aJ aW bF Bg bN bQ bS Cx Dd dM Ib Il In It Jm Jp kG Ks Ld Ma Mf OE Og Oz Pc Ri Rj Vq Vu) Gn(Ad As Cq Cu Cw De eM Ho Hv Hw Jn Jr kC kI kO kP Lw Mi nH nR nU Ou Pi Ra Rb Uz Wg) Yd(Af aG aW aZ bJ cS cU Cx Fw Hu Ld Li Mi Mk Mp Mq Nu Oe Oh Oz Qy Ub Ur) Ry(Ad Cp Cu Dc Hv Jo Kd Kk Kr Mr Mt nC nH Om Ph Pi Qa Rb Uc Ut Vu) Sh(aI aM bS Ch Cx cY gP iP kG nA Nj nU nY oE Oi Or Oz Pc Qv Rj) Zq(Af aJ bF bZ Cx dL dM fP gP In iP Li nY oE Oi Or Oz Qv) Rt(Cu Fy iJ Jl mW nR Nv Nx Ou Ph Rb Tr Uc Ut Vu) Vw(aZ bS Cx dM gP In iP kC kI nY oE Oi Oz Pc Rj) Uw(Af aJ bM cQ dM gP Ii Ld mW Oe Oi Oz Qv Ur) Vc(bZ cE cG CH cL cU Hq Jd Ma My Nr Om Pg) Hl(Ad Ef iH Il iO kO Uc Vu tF) Wd(aZ bS gP Ha iP Og Oi Oz Rj) Gb(dR gP hB iP mW nY oE Oi) Rz(In kC kI mY Oi Or Oz) Eq(aJ aZ Ef nU Oi Oz) Yh(Ao bZ Cu Et Ut Vu) Zw(Bg Cu Mt Tn Tr Ut) nW(tN tO tU wC wD wP) Fc(dR hB Ky Lx mW) Ho(aH aZ Ha hB Rj) tS(dJ Hw iP Jk rB) jT(Et Ji wH wQ yD) Ld(Sj Ux Vh We) nU(Gd Lp We Yg) Yf(Cu Cx Vq) Wc(Cu Ji Vq) Wh(Jd Om Tn) Rv(aI bB Or) Oz(Sf Ux Yg) wD(aP Hw rB) Si(bF Hq) Sj(Jh Qy) Rj(Uz Wg) wC(cZ Ri) NiSf NjLt IiJi YgOi YkRm QaeQ WeUt UhiB UxaZ dJwB mFpI hCoW iPrS} wD{Ri(aP aV aW aY Bb Bg bH bL bN bO bP bQ bS bZ cA cG cH cK cL CO cS Ct Cv cW dA dG dH dI dN gW hA Hb Hq hR iP jG Jk jM jT jV Jy Ko kS Lj lK Lu Ma Me Mi Mk Mp Mu Mv My Nd Ng Nq Ns nW oE Of oH oK oN Or Ou Ow Oy Oz Pd pF Pg Pj qC qD Qw Qy Ra rB RC Rg Rj rS Tn Tr Tt tU Ua Ub Ul vB vI wF yH tL xA Tj) Ji(aP aV aY Ba Bc bF Bg bH bJ bL BN bQ bZ cG CH cK cL cN CO cQ Ct Cu cW De dF dG dH dI dJ Dk eC Ef eT Gl HA Hc Hw hX iA iP Iz jF Jh Jk jM Ko lO Nd nW oE oK oN Or Ow Ph qH Qy rB rW Tj) iP(aD Al aN Ar aV Bg bQ bZ Ch cO Ct Cu dA Et Fn Fr Fw HA Hb Hc Hq Hu Ik Iz Jj Jk jP jT Jv Kc Ko Kr lM Lu Mk Nd nW oE Of oN Oy pF Pj qB qC qT Qy rB Rh rS rV rW Um uO uR uT uZ vO wQ yD yL) nW(Aj Aw Ba Bc Bg bH bS Ch Co Ct Cu cZ dI Dk Ef Et Hb hL Iz JY Kc Kp Ky nY Ou Ow Ph Pj qD Qn Qu Qw Qy Rg Rj Tn Tr Tv Ua Ub Uh Uk Ul UP Ut Vs Vt VU Vv wB yE Tj tF) An(aV Aw bF Bg bH bL bQ bS bZ cA cE cG CH cL cN Co Cp Ct cW De dG dJ Ef hA Hq Hw Jh Jk Ko kS Lu Ma Mk Mu Mv Mw My Nq Nu Nv oE Of Om oN Oy Pb pF Pg rO Tn uI uR) Lu(Aj aN bH bS cT cZ dE dI eZ hA Hb hL iC jD jK jO jV jY Ko lL Nd Or qZ rA rB rC rS) Ko(aN bL bN cO cW dN gW hO Hw Jj Jk jV Kd Ma Ng oN Ou Ow rB rS uR uZ wQ xA) Me(Aj Ba Bg bH bS Ch De dI Dk Ef Ic Iz jY Ks Ou Ow Pk Us) Jk(aE Bb Co Cp Cq Db Et Ez Jd Kr Ou Pi Pj Ql Tn To Tr Tv) rB(aN Cs Ct Hb Jj Li Lj Mf Mt Or Ou Ow Qd Rf Rj Ur Vt) Pj(Aj aP bL Ef Hw iA Iz Jj Jt Mg Ng Or Oy rR xA) Ou(aN aP aV bL bQ bZ cQ Nu oE oN Pb qU rS uI) To(aP bL cL cW De hA Hq Hw Jj tS Ur vS) aN(Ba Bc Bg Ch Ct De Dk eC Ef Fw Iz) Kn(bL cO cW dJ Hw Jh oE oN yD) Db(Ef Iz My Ng Oy Qy uI uR) Et(Bg Ct cW Dk Ef hA Iz) Tr(cL De Ef Hq jO Of qH) bL(Bb Bc Hb Jd Kc Kp Uh) oE(Aj Bb Ct Hb Jd Kp Uh) Hq(Ax Bb Co Fa Tn) aP(Fy Id Jd St Vt) rS(aW Ch Li Lj Mf) Oy(Bb Fy Hb Kr) dJ(Aj Ct Hb Kk) uI(Ic Jd Kd Um) Ng(Ad Ap Ez) Tn(jD jO qH) Lj(Ha jT Kc) cW(cZ Id Uh) Ct(Uc Ur) Ef(jV Mn) Or(Id wQ) qZ(cQ Hw) qU(Aw Ow) AjEz BbhA CscO FabQ HboN QyjV JjUr KcbH} Rt{Dc(Ao aQ aW bB bF bQ bU bZ cK CO Cp cS CU De Dk dR Ef Ez Fr Fw Fy gL hB Hq Il iZ Jh Jl Jn Jp Jr Jy Kg Kk Ks Ky Li Lt Ma Mg Mi Mp Mq Mt Mu Mv Mw Na Ng Ni Nq Nr Nt Nu Nv NY oF Om Ou Oz Pg Qa Qd Ql Qv Qy Rb Ri Sr Tn Tv Ua Ub Uc Uf Ut Vj Vu) Jl(AF aK aU aW bA Bn bQ Cu Cw Cx Dd dK Ex Ez Fc Fi Fw Fy Gc Ho Hv Hw Ih Il Jh Jk Jm Jn Js Kc Kd kP Ks Ld Lh Li Lj Mf Mi Mt Mw No Nr Nt Nv Ny Om Oz Pa Pd Ph Qa Qb Qe Qh Qn Rm Sr St Tt Uh Uk Ul Ut Vq) Ny(bB Bg bQ bZ cB cE cL Co cS CU Dd dR Ef Et Ez Fy Gp Ho Hq Hv iH Il iO Je Ji Jp Jr Jy Ks Lv Ma Mf Mg Mi Mn Mt Mu Mv oF Om Ou Pd pF Pg Qh Rm Tn Tr Uc Uf Ut Vq Vu) Cu(aX aZ bL bM cD cQ cW Dd Di dR Fd fP Fw Gl Ih Il Io Jk Jn Ju Kd kP Ks Lj lW Mf Mx mZ Nd nN oE Oh Oz Pa Qa Qb Qc Qd Qe Qh Rm Rz Sr St Tt Ul Vb Vs Yh Th) Ut(aE aL aX aZ bA bH Dd Eq Fd Fw Fy Ik Il Iq Ir Jm Jn Js Kd Kn Lp mF mW Mx Nd Ng Nr Pa Pg Qe Qh Qz Rm Ss Tv Uy Vq Vt) Jn(aI bF bQ bZ cE cG cL Dd De dF dR Fy gP Hq Il iP Jk kI Ks Lh Lv Ma Mf Mv Nv Om Ou Pg Qh Tn Tr Uc Vu Yd) Qa(aP aR bP bQ bS cE Dd dG DL Dp dR Fy gP Ik Il kI kO Ks mU mW mY nA nD oF Or Ou Rb) Fy(cQ Dd dR Fw Ih Jk Jm Kk Mq Mt Mu nI Nv Oh Om Oz Qc Qe Rm Sr St Uc) Uc(Aj Fw Il Kd Ki Lj Lp Mw Mx No Nr Oz Pb Qb Qe Qh Rm Sr St Tj) Tn(Dd Fd Il Ir Js Kd lX mF mW mY nA nD oE Oz Pc Rm Ss Vc) Nv(Ax Il Jr Js Kd kI kO mF Mi mU mW Mx nA Nr Oi Qe Rm Vq) Om(Ax Cq Fd Il Jm Jr Mi Mr Mx Pg Qe Qh Qz Tv Wh) Qe(Ba bQ cE Cp dF Hq Jr Lv oF Ou Tt Yd) Vu(aX Fw Ih Il Jm Kd Lj Mx Qb Qh Rm Sr) Qh(hB Jy Kk Mq Mt Ni Nu Oz Ql Sr) Js(Bg dR Ef Il Jk Jy kI Ou Rb Tr) Pg(dR gL hB hG iZ Jk kP nI Oz) Ld(aW Jm kR nH nN Nu Uy) Jk(Jr Lx oF Oz Pi Sr) Oh(Dd kS nC nU oN pF) Ma(aZ kN kP nN nT) Il(Fd Hv Hx Or Tv) Qd(aL bQ kP Mf Oy) Pi(aI cE Kk Oz Rm) oF(Dd Fd Ih St Vq) Jr(Fw Kk Qc St) Ow(bM dL kR mW) Ou(Ir Kd Lj Mx) Tr(Iv Kd Mi) Jm(Hv Ji Mt) Rm(bQ cJ Qv) Cx(Jq Tz) Tv(hB oE) Ir(bQ dR) Jp(mW nH) Oz(Bo Cp) nU(aH Ji) nC(Lh Mf) hC(Kd Vq) FwRb NqbA MtKs IhdR IqKk aZbJ bZkN} Eq{Ut(AF aH aU aW bM bN Bo bW bZ cE cL CO cS CX dR Ef Et Ez Fc Gc hB Ho IH Il Iq Iu Jh Jm Kc Kd Ld Li lX Ma Mg Mi Mp Mq Ms Mt Mu Mv Ni Nq Nu Nx oE Ow Pd Qd Qv Qy Rj Rm Sr St Uc Uf Ug Uh Ur Us Uu Uv Vj Vq Vt Vu We) Nq(aH aJ aP aW BA bF bQ cE cL CT Cu Dc dF dM Ez fR Fw Fy hB Ih Ir Jg Jk Jl Jm Jn Jp Js Kl Ks Li Ma Mt mU Mx Nd No Nt nU Nv Ny OF Oh Ok Om oN Ow Pa Pd Pg Ph Pi Qa Qb Qd Qh Qu Rm Sr St Tn Tt Tz Uc Uw Vq) Mt(aE aX BA bI bQ cL cT cV Dc Du Ef Fy Gp hB Hq Hr Hv Hw Hx Ih Il Iq It Jk Jl Jm Jn Jp Jy Ks Mf Mj Mu Mv mW Nd Nv Ny Of Oh Oz Pa Pc Qa Qc Qd Qh Qt Ri Rm St Tz Ua Uc Vq Vu We) Om(aA Af Aj bZ cA cK Dp Ef eM Fc Gh hG Ii iO iZ Jn Jy kG Ky lW Ma nC Nd Ni NU oN Oy Oz Pb Qv St Ur Uv Vc Wc Yd) Ef(aH aW BA bQ Cu dF Fw hB Ih Jl Jn Js Lj Lx Mx nN No Nv Ny Oh Ow Oz Pa Qa Qb Qd Qe Rm Sr St Tn Tt) Mu(BA bQ cT Cu dF Fy Gp Ih Jl Jn Js Lx No Nv Ny Oh Ow Qa Rm St Tn Tr Tt) Qd(Ba bF bQ bZ cE cL cS CU dR Ez gL Gp hB Il Jp Jy Ks Ma Mk Mv oF) St(aW aX bQ bZ cL CO cS CU dI Ez iH Jh Ma Mv Qy Ri Uc Uf Vu) hB(Co Cp Cu Ho Hv Jh Kg Li Lx Mg Mi Mp Nt Pd Qy Qz Rz Si Uf Vq Vu) Vu(aA Bo bQ cE Fw Gn Ih Jn No Nr NU Nv Ny Qa Rm Sr Us) Jl(aW cL CO cS Li Mg Mi Mp Mv nN nU Ow Qy Uf Zq) Cu(aW Cx Fw Il Jm Jn Kd Li mZ nI nU Ny Oz Pc Wc) Nv(aW Co cS Ez Gp Il Ld Li Mq Mv NU Ow Sr Vq) Uc(Af Ar Bo Cx Jn Ld Li Mq Mw Ny Ow Sr Ur Vj) Jk(bZ cS cU Jn Ld Lz Ma Mk Mq Ow Ur Vj) Li(bF Dk Hq Jp Ma Mj oF oN Ou Tn Tr) Ny(aW bZ Co cS Ez iH Ma

Figure 28 Continued

Mg Mv nU Uu) Ow(bF Bg bZ Ch Dk Hc Hq Jp Nj Ou Tr) Jn(bQ bZ cE Co Ez Hq Ma Mv Uf) Qa(aJ bF bQ cE cS Ex Mv Nj) Mq(bF Hq Il Jp oF
Tn Tr) Jp(CO Ez Ld Mp nC) nU(aO Ba Ki Ky No Yg) Qy(Dc oF oN Tn Tr) bQ(Fw Ih Qe Rm Sr) Zq(bF dR iZ oF) No(kC Mv oE) Mp(gL iZ
Tn) Mw(bF bZ Ma) Ld(Hq iZ Jg) Oz(Ba Iz Ua) nC(Et Lh Oh) oF(Jd Jh Rz) Mi(bZ Tn) Mv(Qe Rm) Jy(Fw Oh) Vq(dR oE) BaQe CoRm CxTz
DkaW EziZ IlJd JhoN JmVj} hB{Si(aA Aj Ax aZ bA Ch Cq cT Cu Dc Dd De Fd Fw Fy Gd Ha Ho Hv Il In Ir Iv Jl Jn Jr Js Ki Lp Lx Me Mi Mr
Ms Mx Na Nj No Nr Ny Oh Pg Pi Qb Qd Qe Qh Ri Sh Sr Tv Tz Uu Ux Uy Vp Tj) Vc(Ax aZ bA Cp Cq Cu Dc Dd Fd Fi Fw Fy Gp Ho Hq Hv Il
In Ir Iv Jl Jp Jr Js Kd Kn Li Lj Lp Mi Mj Mr Mt Mx Na Nj Nl Nr Oh Om Pg Ph Po Qd Qe Qh Rm Sr Tv Tz Uf Uy Vp Vq) Ho(aE aH Aj aR aW
aX aY aZ bF Bg bL Bo bR bS bW Ch dG fP Gp Ih Ir Jm Kk kR Lj Lu No Ny oE Of oH Oy Oz Pa Pk Qb Qz Ri Rz Ss St Uh Um Ux Uy Vb Th)
Uy(aE aY bR Cu Di dR Et Gb Hb Hv Hx Ih It Iu Ji Jl Jq Ko Ky Kz Li Lu Mi Ms Mt Na Nt Om Pd Pg Pi Po Qd Qe Ri Rm St Tz Uf Uh Um Un
Vj Vq Zq) Fd(AF AN aW bG bJ Bn Bo bR bS Cx dG dH dR Et Gp Ic Jm Kd kQ Lj Lu Mt Mw Nq Nt oE Of Oz Pa Pj Qy Ri Sr St Uh Um Th)
Lp(aQ aR aU aW aY bG bR bS cQ dR Et Gp Hb Hx Ji Li Lu Lv Mp Mt oE Oz Pj Qm Ri Rj Sh St Uh Um Un Ur Vq Ti) oW(Af Aj aM aZ bW
dR Hb Il Iz Jr Kc kl nH Nm Of Oy Pa Qc Qz Ss Ue Ur Vv) Sh(Al Dd Fw Ha Ih Il Ir Jm Kd Ks Lu Nr Pg Ph Qh Rm Sr Ut) Fi(aE bR bS dH dR
Ih Jl kR Lu No Ny oH Pi St Um tF) Uh(aE CH dJ Fc Hp kE mF mU mZ nC nK nL nW Ri Yd) Ti(aZ Dc Ha Jl Kd Lj No Ny Qa Qd Qe Qh St) Th(Dd Ji Jt Kd Kn Li Qd Sr Un Vq) Gb(dR Il Jm Kd Lj Nr Pa Qb St Um) dU(Ef Kg Ld ml nH nK Ow Qu Uf) Fc(Ji Jn Jr No Pi Qc Tz tF) nW(hP rS tU uZ wQ yL zI xA) Zq(Al Ch Il Jm Kd Lj Nr) Uz(aW aY bR Lu Oz Pa Ri) nK(eC eQ fP gZ nI oV Um) pI(Fw Jd Ld Ow Rj St Um) Gc(aZ Lj Ny Qb Ri St) Vb(Cu Il Kd Mi Sr Vq) Du(Js Lj Nr Po Qe) Ry(aZ Ir Jp Lu Sr) Em(dR mE nU Ow) Rv(Ih Lj Qb Rm) Ux(Ap aW Li Vq) fR(nC nH nJ nL) mI(eC eQ pK Us) Il(Vj Yd Yl) Kd(Hl Uw Yh) Rz(Li Mi Uf) Ow(mE mF mZ) Gp(eP Hp) Ir(Lt We) Qc(eQ pK) Sr(Lt We) Jm(Vj Tm) Um(kE nI) Vq(Yh Zw) eC(lY nJ) iP(rS wQ) GnHa NoHp SfPi JijO WcRi NyVj OheQ UrkE VhaZ PaoT dJhO rBrR oFpK} Ld{Uy(Ad Ba bF Bg bR bU bX cB cF cK Co Cp cU Cx dF Dk Ef Gc Gp Hc Hq Iz Jg Jh Jk Jl Jp Jy kN Ko Ks Mj Mn Mt Mv My nC No Nq Nt nU Nv Nx Of Om Ou Oz Pz Qc Qd Qu Qw Qy Rb Rm St Tn Tr Tt Tz Ua Uf Vp Vq Vu Vv We) Lp(Ao bF Bg bQ bR bZ Co cU dF Gp Hc Jy kI Kk Lv Ma Md Mv My Nd Nq Nu Oi Or Ou Oz Ri Rj Uc Uf Ut Uu Uw Ux Vh Vq Vu Vv We Yd Zx) We(aC aL aW Ax aZ Bb bX cB Cp cQ Dd Fw Gp Ip Iq Ir Kd Ki Kn Lj Lx Mn Mt Mx No Nr Nx Oz Pa Sr Uh Vt) Uw(Al aW aZ bX cQ Dd Fw Gp Jm Kd Ks Lj lW Mw Mx Oh Oi Oz Pa Pb Pc Ph) oW(aD Aj bL cH Cv Gp Ii In Kc Kn kQ mE nD Ns Nx Of oH Oy Oz Ur) Zx(aA aX bX Fi Gp Ha Jm Js Lj lW Mx nC nH Oz Pa Ph Pi Qb Tv) Fd(aW bF Bg bQ cE Cx Gp Jm Kk kR Mn mW Nd Nq Oz Pc Qy Rj) Fi(bR Dc dR Fw Lx Md mW Nr oH Oz Pg Qe Qh Ua Uc Ut) Du(Fb Fw Jl Jn Js Kn Mt Mx Ny Oh Qd Qe Qh) Yh(Jl Jr Kn mF Mj mW Nv Om Qa Qd Uc Ut Vv) Uz(aW bF Co Gp Iz Kk kQ Mn Nd Nv Pz Qy) Em(aI bA bF cE dF Fw Il Jl Ow Uh Vq) Rz(cE Hq iA Jk Jp kK Mt nC nK Oi Om) eQ(Ax CH Gp kQ mE nK Nr oF Oh Pa) Vz(Il kN kR mE mF mT mW nO Qh Vu) Wh(IZ Jg Jk Nr Om Ph Pz Qa Tn) Th(Cu Fy Jl Jp kN nR nU Ny Qd) Gp(Gn Hl Ho Hp Ry Wc Wg Tl) eC(mM mW mY mZ nI nN nO nU) pI(bL CH Hr mW Pb Ql Uv) Yd(aX Kd kR Lj Mx Qb Uc) Zq(Al Il Jm Ks Oh Oi Rm) Zw(Jg kR Nv Om St Tn Ut) Vc(Lx No Nr Oh Om Ph Tn) dJ(tR tS tT tX Uh vI wB) Fc(kN Lx mW nO Nr Vp) Ho(bQ Kk kR Oz Pb Pc) Yg(aW bX Ki Oi Oz Pa) Vb(Dc Dd Jg Qh Rb Uc) Ux(Jg Kd Lj Mx nC Nv) Vh(Al Hq Il Jm Kd nC) Yk(Cp Cq kR Pg Rm) Sj(Jn Kd Nr Ny Qd) Ry(aZ cU hG kR mW) Hl(aZ Mt mW Nr) Op(lW nC nH nN) Yj(Al Fy Ks) Tl(mF nC nH) Uh(eP mM nI) dU(cH mZ nK) mE(Gc Lt pK) Gh(Nr oF) Gn(Cq kK) Sh(Al Lj) Qc(Gd pK) Wc(bQ kR) Wd(Jg Om) Yl(Fw Nv) mM(aH Jp) mZ(dR pF) iB(Ex Ji) kQ(lX oV) AjEt YfIl GbNr GcVu HpNy IqLt SfaZ JmVj TmmW eDtS nIoE wBnW} Vj{Jm(aA aC aM As Ax bA bO bQ Cq Cs cT CU Dc Dd dF dN Du Ex Fa Fd Fp fR Fw Fy Gz hC Hv Hx Id iZ Jl Jn Jq Jr Js Jv Jy Kd Ki Kk Kn Ky Lv Lx Me Mi Mj Ml Mq Mr Ms Mx Nf Ni No Nr Nv nW Ny oE Of Og Oh Om Or Oz Pa Pg Pi Pk Qa Qd Qe Qh Qv Qx Ra Rb Rm Sh Sr Tn Tr Tv Uc Un Ut Uu Vt Vu Yj) Il(aA aH Ap aX aZ bA cM cN Cs cT cV Dc dF Fa Fd Fn Fp Gh hC Hf Hv Hx Ih Iv Je Jk Jl Jn Jq Js Kz Lv Lx Me Mj Mr Mx Nf No Nv nW Ny oE Oh Oz Pa Pi Qb Qe Qh Rm Sf Sh Tv Tz Uc Uo Vp Vt Vu Vz) Ny(Af Al bJ bN cD cE Cx Di Fy Ib Je Ki Lv Lx Mb Mf Mh Ms Ns Nu OE oF Oh Oi Or Pa Qh Rj Rm Tr Uu Vq Vu) Pa(Af Bg Cu dJ Ef Gz Hf Hp Hx iZ Jl Jy Ki kQ Ks Me Mj Mr Mv Ni Oi Or Oz Pi Qd Qe Rb Ri Rm Uc Ut Vu) Jl(Af Aj aN aX aZ bN Ch De Di Dk Ex Fw Gl Ih Lj Oi Qn Rj Sr St Ul Us Uv Vs Yd Yh Th) Kd(Cu Fy hC Hx Kk Ks Lv Mf Mj Nv oE oF Or Pi Qa Qd Qe Qh Rm Tr Tv Uc Vq Vu) Rm(aA aH aZ bM bN Fw Gd Ik Ki Kk Lj Me Ms Nc Ng No Sh Uu Uv Uy Vs Yh Yk) Qa(aX cC dG Dl Ex fP Gl Ik Kl Kx Ng Oz Pb Pc Qt Qz Ua Uy Vs Yh Th) Dc(aA Af aW Cx fR Fw Gl iZ Jn Lj Me No Oz Pb Rj Si Us Uu Vs Yk) Qe(Af aH aW aY bM bN Du Ex Fw Ri Uu Uy Vs Yh Th) Fw(aZ fP Jr Jy Kk nW Oi Or Pb Pi Qh St) Jn(aH aZ bM cC Di Dl Du Ki Ks Ms Or Qh) Fy(Af aX aY bM Du fP Gl St Uv Yh) St(aL Jr Ki Mj oF Oi Qh Qv Uu) fP(Ax bA cT Ih Js Lx Mx oF Oh) Qh(aA Af aW bN iZ No Oz Sh) aX(gL iZ oE oF Pi Tn Tr Ut) Or(aW Ih Lp Mx Nr Oh Sr) aZ(Ir Kk Mf Mw Nr Tr) Oh(Al bM Du iZ kS) Pi(Al aW Lj Th) Aj(Jk Nv Tn) No(kQ Nd oE) Lx(bM Rz Uv) Mx(Jy Kk Ni) Tv(bN Cx Wc) Ks(aA Ir Vt) Oz(Al bA Vu) Ch(Nq Ut) Cu(Gl Th) Qb(bQ Jy) Lj(aH Pg) Lp(Lv oE) Uy(hC nW) aW(Fd Mj) iZ(bA Lu) oF(aY bM) BaNg DiUt DuJs GlPg NrcQ UcYd TnUv JkUu JrNx} Ow{Du(Ax bR bU Cp Cq Cs Cu Dc Dd Em Fd Fp Fw Fy Gz Ha Hp Hv Ih In Ir It Iv iZ Jn Jr Js Jt Kd Ki Kn Li Lj Lp Me Ml Mj mM Mr Mt Mv Mx Na nC Ne nH Ni Nj nO Nr Ns Oh Pg Pi Qa Qd Qe Qh Qv Ry Tv Up Uz Vp Tj) Yh(Al Dc Fy Il iZ Jh Jl Jp Jr Jy Ks mE mF Mj mT Mv MW My nO nR Nv Ny oH oN pF Qd Qh Rb Rm Tn Ua Uc Ut Vp Vu) Zw(Ad Bg Dk Ef fP Hc In Iz Jh Jl Jy Mt Mu My Ni Nq Nt nU Nv Om Qa Qd Rb St Tn Tr Ut Vu) Rz(aH bQ cE Cu Dk fR hC hG Hq Hu Iz Jd Jh Jl Jp Jy Mt Mu Mw Ni No Nq Nt Nv Qy Ut Vu) Hp(bF Bg DL Hc Ik In Jy kS Ni Nj Nq Og Oi Or Ou Qv Rf Ri Tn Tr Ut) Gd(Bg Dk eF Hc Il Jl Jp Jy Ko kR Mu No Nq nU Og Oi oN Qd Qy Tt Ut) eP(aE Aj Ch Gz Ic Jp Kc Ko Nc Ne Nl Oe Of Oi Uh Ur Uv) Sh(bF Bg Ch dL Ef Hu Mu Mv nO Nq Qy Ua Ut Zx) Yd(iA Jl Jp kS Mt mW nR nU pF Ut Uv Vu) Wc(Cp Cu Dc Fy nO Nr Pg Pi Rm Tv Tz Un) pI(Aj Co Ii Iz Kl Nx Uc Ue Ug Uv Vo Vv) Wh(Iz Jh Jk Jl kS Mu Mv No Nt Nv Ua) nU(Aj Fc Gn Ii Jj Jo Rv Ug Ur Vh We) mE(Dp fR Ii Jj Jo Ug Uh Uk Ur Vv Vz) Em(Aa Cw Ii In iZ Jo Kk Lu Ph Qz) Fd(Af Ch Cx hG Jy Mu Ni Nj Nq oF) eQ(Aj Jo Kj nC nH Ur Uu Vo Vv) Vz(bX Il Jg mT nO nR Oi Pg) Ux(Bg Jp Jy Mu Nj Nq Qy Tn) Zx(lW Ng nH Oz Pb Ue Uu) Wd(Jh kS Mu Mv Ng Oz Pb) Lp(aA hG Jy Ni Nj Nq Or) Vc(bZ hC hG Ni No Or Qv) fR(lW mF mY oH Oi oK oN) oV(Aj Kj Nx Om Ue Uv) Ko(Aj Jj pS rS uR) Vb(Dc Jh Uc Ut Vu) mF(Gh kC kP oO Ug) Nu(Fc Fi Gh Si) Aj(eM Qd Uc) Yj(fP Jm Oz) Ji(iB jO jT) Uz(Cx dL Nj) Vt(pS rO rS) oW(Cv Ug Ur) Ap(Uw Zq) Ti(eM hG) Gh(Nr Ny) Ng(We Yg) Hl(aA iZ) Ho(Ni Nj) Id(rS uR) Yk(nO Rm) Si(nO Nr) Qd(pS Th) Rv(mW Or) Yl(Fw nH) AfUw ChJp DpkC WmrS FctF GbhC MvUy YgJl SjkS WeUt JonR TlnC RyaZ RirN UgnI UrgC dJwB iZkO} Qa{Du(AD aE Af aG Aj aZ bC bG bM Bn Bo bQ Cx dI dM Gn Hc Hr iH Ii iJ iP Jj Ju Kl kN kP Kr Li lW lX lY Ma Mj Ml mY nB Nc Ni Nj Nk Nl nY OE Og Oy Pa Pb Qc Ra Rj Sf Sh St Uu Uv Vp Vs We Yh) Yh(aJ aP bC bQ bZ cE cL cO cQ cU Cx Dc dG dL dM Et Fy Gc gP Hb Hl Hu Id iH iP iZ Ji Jp kI KO kP Ks Lv lX mF mM Mn Mt mU mW nA Nd nY oE Ou Oy Oz Pj Qg Qt Qv Qw Ry Vu Yd Ti) Zw(aH aJ bF Bn bP bS cC cE cL Cu Cx dF dM Gn gP Ha Hu Ib iP kC kI kO kP lX mF Mt mU nA nD Oh Qw Rj Uh Ur Vq) Hl(fP Il iP kI kK kN kO kP lW lX mF nA nD nU nY oE Oi pF Ri Ua Uh Vq) eQ(Aj Cx Dp Fa Ha Iz Jo Kj Kl Kn Lu Nx Ou Pj Qh Qz Rc Rm Ug Ur Vo Vv) Yj(Af bN dG fP Ik Jm kC Kl kN kP lW mF mY nD oE Pb Pc Qt Uw Vs) Yd(Af aG aP bP bS cE Dd gP iP Ji kI kN Lv mW nY Op Ou Rj) We(Bg Cx Dd dL Il Jy Mv mW Nq nR Ou Rb Ut tF) Wh(aN Bo bQ cE Cx Dd dI dL Fc Ha Mt Ni Oe Uo) Ry(Ex Jm Kd Kl lX mY nN Nx Uu Uy Vs Yg Th) Fc(aJ Fi gP hG iP kG mI mY nA oE tF) Yg(aJ Bo bQ cE Cu Cx Dd dL Mt nC Oe) Uh(Aj iB Ii iO Jj kO nI nW oN Si Vh) Uw(aG aH bP cE Cu Mt Ni nU Rj tF) Aj(Ba Bb Dg Et Jg Ko oW Zx) Sj(aA Af aZ bM cF dI Pb Sr) Gn(kN nD oE Uu Uv Uz Vs) Th(dM Ko Ky Ni Un Ur) Fi(Bn cE cP Cx Dd hG) Gh(aW aZ Il kI Lx mW) Rz(bQ cE Co fP Mg Mt) Op(Dg Kl kN

Figure 28 Continued nL Uv Vs) IX(fB Gb Sf Sh Uy Vw) nI(Fb Kj oT Rj Ug Ur) oW(Co Cv Ii Jj Jo Ug) Vz(aW Il mW Oi tF) Dd(Vb Vh Wc Yk) Zq(Dl fP Ng Oy)
Tl(kO kP mY nA) mW(Ho Vh Wc Yl) Hp(aA Af bO) Sh(Jv nA nU) Zx(kN nN Uu) Wd(bM fP Mt) Vb(aG aJ bP) Vc(Bo cE dl) Ti(hG Uv)
Gb(fP kP) Gd(nU Qy) Lp(Kd Rj) Yl(aD nA) Vh(aJ cE) Vw(aG Cu) fB(Ks Ne) pK(Ii In) MiHo NcSf JojB RvfP RmpI UxaG eClW} Ji{jT(Ao Aw Ba bI bL bN bS Ch Co Cp cQ Ct dC De Ef eT Ib Ii Iz Jd Je Kj Kn oE oK oN Ph qH Ql Qt Qx Qy rR tN Uk UR Us uW vV wF wJ wK wL yD yH tL Tj) eZ(Aj bL cQ cS cW De dJ eT Gl Hq Hu Hw Ic Ii Ik iP Ir Iv Iz Jh Jk Jm Mu Nq Nu Nv nW oK Ph Qy Ri rR Up Vs wK wQ) jO(aM aQ cJ Ct cZ dJ hX iB Ic Ik jE jF Jj jK Jl jQ JR Ky lN Lu Mj Mx Nl nU Nx Ok Ql) Jj(aA Et Fp Il jK Jl jP Jq Li Lj lN Ms Nl No Ns Og Oz Pb Ri) Og(aA Et Il Jl Jm Jo Jp Jq Li Lj Ms My No Ns Nv Oy Oz Pb) Aj(Ad BA Dg Et Fr Il Jg Ko Ma Mn No Qd Ri rS Uc) iB(aQ bA bI bN CH cJ Cp cQ Dl Kk oK Ou Qg Uh) Yd(Cu Il Jk Jl Lv Mt Nv Ny Ou Qd Qh Tr Uc Ut) Jq(aA Et Ik In Jl Jp Lj Ms My Ns Ok Oz Pb wB) dJ(hL hX jE qC qQ qX qZ rS rW tR tX vI wB yL) jR(bL bS Cp cQ Ct De eC Ib Ic Ph Qx Ri rR) Et(Hr Ii Jo Lj Ms My Ng Ns Oe Of Oy Oz) Wc(aA aZ Jm nC nU Nv Ny Oh Pa Rm St Tz) jQ(bL bS Co Cp cQ Ct De Ic oK Ri rR) nC(Fc jY lN Vh Wd We Wh Yg Yh Yk) Ms(Ik Jo Jp Md Ns Oy Oz Pb) Yh(Cu Jl Jn nU Oh Qe Rm Ut) Jm(eT rS rW Sf Si vS Vz Tm) lN(jP kC kF kO nD nH nJ nL) rS(aW cH dC Hu Jk Mf Nv) vS(eD eT Jf Tz Ua Uk Ut) Ii(bA Il No oF Ri Uh) hX(aQ cH Ko Ql Tz Uo) jF(bL Cp eC mI mS nK) jK(bL Co cP Ct oE Qx) Jk(rN rW vI vQ yL) nU(Gn Ho Si Wc Yj) jD(bN Ct De oK wC) jP(bS oH Uh Uk Uo) Du(Ax Fy Ih Oh) Th(hG iZ oE Qd) Nv(rN rW uT Wh) aQ(rA rR rW vV) Fw(Vc Vz Wh) Hu(hP qB rT) Uy(hC hG iZ) cH(jE vQ wF) hA(bA cG oF) uM(Ir Iv Ks) Fc(dR oE) No(Ns Vc) Ik(Lj Ns) Yk(Ny Rm) Vz(aW Il) Jo(oW Wm) cQ(jE rC) lO(bA cT) rN(Hw nW) GhaW TzrR JgOf StVh WeNy QyVb JpOz KowF UsdR PhlK wGoE yLnW oFuR} rS{iP(aD aQ aV aW aX bA bO bV cH Cs cZ dC dJ Et eZ Fa gP Hc Hf Hu Hx Id Iu Iv jD jG Jj Jl jP jQ jR jT Kc Kf Kk Kn Ko Li Lj lM Mf Mh OE Pa qC qD qG Qm qP qZ RB rC Ri rN rW sC sM Uf Un vI Vt wB wJ yL Wm) Li(Al aQ aV aW Ax Bg bR bS Ch cL cM Co cS Ct Cv dA dJ eD Ef Fp Fw Hc hL Hq Hu Ic Ik Iv Iz Jj Jk Jo jY Kc Kg Ko kR Ks lL Ma Mf Mj Nq oN Or Oy Oz Pb Ph Qh qI Qw rB Ri Rm rR tS Ua Uk Up Ur Vs Vu) aW(Aj aK aQ aV bO Ch cL cM cZ Di dJ Et hO Hu hV Id In Iv Iz jD Jj jQ jR jV Kf Kn Kp lL Lx Ma Mf Ni nW Oe Oi Ou Pa qC qD qP qW qZ rB Ri rX tS uR uV vI vP vQ vV wB) Ko(aF bN bO bZ cU eZ Fb Hb Hu Iv Jj jT Kn Kp Lj Lx Lz Mg Mr Mt Ng nW oF Or Ou Pc Pz Qc qD Ri Sr Uh Uk uR vH Vs wB wF xA) Lj(Aj Al aQ aV Ax cJ cM cS cZ dJ Fp Fw Hq Iv Iz Jj jT Mf nW Ph qW rB Ri tS Up vQ) Jj(Ap Cs Dg Dl Et Fa Id Iu Jl Kf Kg Kr Lh Mh Ri Un vI Vt wB Wm) nW(aJ Fy Id iZ nY Ok Qd rN Un uX vI Vs Vt wB yL yE) vI(De cD Hu Id iO Iu Lu Lx Md Mf Ri Uk Vs Vt Wm) Lu(bA bO dF cZ Fa jD Lx Mt oF qD rW uT wB) Ri(cH dJ eZ hR Id jT lM Of Rc Uk Vt wB yL) dJ(Cs Et Fa Hb Jr Kk Kn Kr Mr Mt qX Rf) Mf(Fa jT Kp qZ Rf uR Vs wB wH yL xA) Vt(Gp Ib Iv Jk Jo jT Nk Or Ou Ur xA) Id(cL Fn Fw hO Ic Iv Jh Nk Of Ou) Lx(Bg cL Co Mk Nq Oy Pg Tj) Hu(Aa Et Kn Nx qX qZ uT wB) Wm(Ct Hb Ng Nk Ou Rf xA) Aj(Dg Dl Et Ez Iu Kl) Kr(Fw Iv Jo Of) Po(Hq Jk Oy) Qd(Iz jT rB) Ct(Dl Iu) Et(cQ rR) MduT MgIu MtaV HwJl JkUn JoKn KfOu RfeD cGcL} Wh{Ny(Ao Ap aU aW aX bQ bW bZ cG cL CO cS CU Cw dR Ez Fw Gp Hq Ib iH Jd Jh Jp Kc kG Kx Lh Lx Ma Mg Mi Mk Mt Mu Mv Ni Nq Nt Oe Oi Om Pd Po Qy Rj Rz Tn Uf Ut Vu Wd) Ut(aA aE Af aH aW AX aY bL bM Cs Cx dR Fw Hx Ih Ik Il It Jl Jm Kd Ki Li lW Lz mF Ml Mq Mt Mx nN No Nt Oz Pa Qu Qv Qx Ra Rm Sh St Uu Uv Vq Vu Th) Nv(Af Ax Cs Cu Cx dR Fy Gc Hx Ih Il It Jn Js Li Lj lW Lx mF Mk Ml Mq Mt Mv Mx No Nr Nt OE Oh Oz Pi Po Qv Qx Rf Rm Vq) No(bQ bZ Co Cp cS Cu Ef Fr Hq Jh Jk Jl Jp Jy kC Kk Lv Ma Mt Mu Mv Ni Nq Ou Oz Pd Pg Pi Qd Qh Tn Tr Ua Uc Vu Wd) Mt(aE aX bI bM cT Dc Dd Fr Fw Fy Hq Hw Hx Ih Il Ir It Jk Jl Jq Ki Lx Mv Mw Nr Om Pg Qh Qt St Vq Vu We) Lx(bM Dd Fc Fw Hp Hx Ih Iz Jh Jk Jl Jn Jy Mq Mr Mu Mw Ni Nt Nu Om Pi Qd Ql Qy Sr St Ua Un) Om(aA Af Aj aY aZ bL bN Bo bW Cs Cx Ih Jl Jn Li lY Lz Nt oE Oy Pb Qe St Ur Uu) Jl(Aa Cx Dd Fc Fw Ic Iv Jh Mi Mq nN Nr Nt Pd Si Wd Ti) Jn(Aj bQ cQ Ib Mv Oi Oy Oz Pa Pc Ph Qv Ug Uh) Nt(aZ Jr Lv Mj Oh Or Ou Qd Qh Rm Tz) Tn(AA Af aZ bM Li Lj Mq Oz Sr) Ih(bQ Cu Hq Jy Lh Lv Ou Pg Qh Vu) Mq(Al Dc Jk Jp Nr Ok Pg Ph) Jk(Ar Cs Kx Li Ml Oh Qx) Oz(aZ Dc Ir Mx Qh Sr Tz) Fw(bQ Et Kk Mv Pb Vu) Cu(aZ Bo cD mZ St) St(Aw bQ Jh Pd) Nr(Jd Qd Rh) Mx(Nu Rj Wd) Jp(nC nH nL) Oh(aE Iz Mu) Vu(nC Qv Us) bQ(nI Qd Un) Jd(Js Rm) Jh(aH Qh) Ur(Dc Qh) aZ(eM Mw) BoFy CwRm CxOk DdoE MuJs MvPa QdKx SrKk LhnC} Mt{Vb(aE AX bI Cp Cq Cu Dc Dd Em Fr Fy Hq Hw Hx Ih Il In Iq It Iv Jk Jm Jt Kn Kr Ks Mi Mr Ng No Nr Ny Of Pi Qc Qe Qh Qt Ra Rb Rm Sr St Uc Un Up Ut Vp Vq Vu We) Ux(aE An aS bI bJ bV Cu Dc Fy Hq Hw Hx Ih Il Ip It Jl Jm Mf Ne Ng Nk Of Oz Qc Qd Qe Qh Qt St Tr Uc Vq Vu We) Rz(aE aW aX Ba bI bJ Fy Hq Hv Hw Hx Ih Il It Jk Li Ng No Nq Nv Ny Of Om Qe Qh St Uf Ut Vq Vu We Zq) Vz(aW aX aZ bA bW cB cQ cR Fw Il Iq Ir Jm Jn Kd Lp Mx Nd nN Pa Qc Rm Th) Wd(aE aX bI Dc Hq Hw Hx Ih It Jk No Nv Ny Om Qd Qh St Ut Vu) We(Aj aZ Ch cQ Hq Kg Mg Ng nU Nv Ny oE Qz Rm Ss St Ut Uu Vt) Yd(aH bI cV Dc Fd Jl Jq Jr Lv Mp Or Ou Qd Qh Tv Tz Uc) Yh(aX Hx It Jl Js mW Ny Oh Oz Qd Qe Rm St Vu) Fd(Af Gl Ii Nk Oi Oy Pb Pc Uv Vs Wc Th) Vw(bI Cu Fy Hq Hw Hx Ih It Ny St Vq Vu) Zw(aX Dc Ih Ir Jl Js Oh Qb Qe Rm St) Wc(aX aZ bA cT Dc Pg Qh Tv Vq) Vc(aX aZ Bo Fw Gz Ki No Qh Vq) Du(Ax Jn Js Li Lj Oh) Fi(Fw Ih Ir No Qe Vq) Yg(aX Ih Jl mW Ny Qd) Yk(aZ Dc mW Rm Tz) Tm(aW aY Jm nN Pa) Th(Cs Hx Oy Uk) Yj(aX aZ fP Jm) Lp(Kj oE Ug Uu) Fc(dR Fw No) Zq(bW fP oE) Tl(aY Ex fP) Vh(Dc St Vq) nU(Gn Hl Ho) rX(kO mW nB) Aj(Et Jg) Gc(Uu Uv) Sh(Il Ut) Sj(aX Pb) Lt(mY Uv) Uh(iB oN) aV(rW vV) dJ(vI wB) nK(jF lM) YfaX FwYl GhNo NueZ RyaZ UwVu UyhC iHrB kClN} Ut{We(aA Ad aE aH Al aX aZ bA cD Ch cT Dc Dd Di Fw Ih Il Iq Ir Jl Jm Jn Kd Kj Kk Li Lj lW LX Mi mW Mx Na nC Nd Ne Nf No Nr Nt NU Nv Ny Oh Oz Qb Qe Qx Rb Rm Sr St Ud Us Uv Vq Vu Yh) Sh(Af aH Al aW aX bJ bM BN Bo cQ Ct CX Dd De Di Dp eM Et Ih Il Iq Ir Iu Jm Jn Ju Jv Kd Ki Kj Mb Ng No Ns NU Nx Oe Oi Or Pb Qh Qn Qv Rj Rm Sf Sr St Ul Ur Us Uu Uv Vq Yh) Yh(aH aM Ax Ch Cs Cu Di Et Hx Ih Iq Ir Jj Jl Jn Js kO Li Lj Lx mF Mq Mr Nu oE oF Oh Oz Qb Qe Rf Rm Sr Uu Vq Vt Vu Tl) Yd(aE aH Aj aZ bR bS cQ Dc Et Hb Ik Iq Jl Jr Lv Lx Or Ou Oy Oz Qh Qz Ss Tz Uc Uh Un Vq Vt) Vb(aE Ax Cu Cx Ih Il It Iv Kd Ml No Nr Nt Qx Ra Sr Vq Vu) Vc(Af Ax aZ Bo Cx De Ng No Nr Ns Of Oi Pb Qv Uu Vq) Fc(Aj aZ eM Hx Ik Js Kg Ng No Oy Oz Qu Qz Rm Ss) Ch(Gb Gc Hp Ry Uw Ux Vw Yg Zq) Fd(Af Cx Gl Nc Nx Oz Pb Us Uv) Yg(Ih lW mF nC nN No nU Ny) Kj(Gb Gc Ho nI nK pI Si) Ux(aW bN Cx Nt Nu Sr Vq) Tm(aW Gl Jm Nx Pa) Rz(aW fR Li Nt Vq) Zw(Ih Lx Oh Rf) Lp(Nc Oy Ug Ur) Th(Li Un Vq) Gc(aA bM Uu) Yk(aZ lX Rm) Vh(Ir nN Vq) Du(Lj oE) Gn(nB nU) Ho(Aj Kg) Wd(aE nN) Tl(Jm Kd) Nx(oV pI) Uu(Gb Zx) Uy(Mq Ur) AfUw FwYl GlZq IlVz YjLj QbRv SrVw OpnB bNfB dJqZ} No{Vc(aG aI aK aU aZ bB bF Bg bQ bZ cB cE Ch cL CO cQ cS CU cY dA Dc Ef Et Ez Fw Gp Hq Il In Jk Jl Jp Jy Kd Kk Lh Lv Lx Ma Mf Mg Mi Mj Mp Mu Mv My Nq Nr Oh Om Ou Pg Qd Qh Tn Tr Uc Uf Vq Vu Yd Zx) Fc(aW bQ bZ cE Co CU Ef Fw Hq Il Jk Jy kI Kk Lv Lx Ma mI Mu Mv Ni Nq Nv oE oF Om Ou pF Qd Tr Uc Vq Vu tF) Gh(aU aZ bZ cU Gp Hq Il In Kk Lv Lx Nq Oh Om Or Ou Qd) Fi(aW Co cS Cu Ef Ho Hq Jh kC Mi Mp Mu Mv Nq Om Vu) Rz(Co cS Ef gP iP Jh kC kQ Mu Mv Nq oE Om Vu) Th(Ch cK cS Ef kR Ky Ma Mv nU Qd Qy Vu) Sh(Ch Ef iJ Il Jl Jy kQ Mv Nq nU Ou Uc) Wd(gP iP Jh kC kQ Mu Mv oE oF Om Oz) Vb(cS Cu Ef Hq iH iJ Mv nU Uc Vu) Sj(hC In nW Oi Oz Pc Qd) Wc(Cu Dc Jr Js Pi Tv Uc) Uh(eP iB Ii iO nW oK oN) Ux(Ef Mu Mv Nq oE Uc Vu) Gb(Ef Hv Mi Om Uc Vu) Gc(Kk oE Or Ri Ug Vu) Yd(cA cK Lv lW Ou Oz) Ho(aZ kC kI kQ oE) Yk(aZ Dc Jl Qh Rm) Vw(Cu iH iJ iO kC) Ti(dR eC oE oF) Zw(nR oF Rm Tr) Zx(aK cA nN Oz) nU(Gn Hl Hp Yl) Si(iA kQ oE) Zq(Et Lv Ou) Uw(kC kO Oz) Aj(Et Jg) Gn(iH kI) Yg(Oz Vu) Op(lX Ou) dK(oV pI) gP(Yj Tl) jB(Ny Qz) CuVh DunY FdnW GdUc NdTm WenR OegV UgoW UroH UykR dJhO} nU{Hl(aG Al Ba Cw dF Et Fb Hw Hx Ih Ii It Jh Jk Jm Jn Kf Kn Ko Kp Ky Lh Li Lj Ma Mm Mn Ng nJ Nk Nv Oh Ok Op Ou Qe Qm Ry Tz Uh Un Up Uw Vt) Gn(aI Ar Cu Dk Fw Ha Hb Hx Jl Jn Jp Js Kk Lh Li Lj Mq Nf Nv Om Or Ou Oz Qd Qe St Tn Tz Uh Vu) We(aH aI Ao Ar Fa Fb Fw Jn Js Ko Ky Lh Li Lj Mn nJ Nv Oh Om Pg Qb Qd Qe Qh Qm Ry St Tn Tz Yg) Yl(aG Ar Ax bZ Cs Cu Cw Fw Fy Ih kC Ki Kp Kx Lj Lz Ma Mh Ml Nk nN Oh

Figure 28 Continued

Figure 28 Continued aA{dK(gZ oT pl) MfZx HlOu IpjB SioN RzmY UwcQ IXhR} wB{Ic(aN Me ul) AaPh Om Qa Qb Qc Qe Ur Vt) Aj(bA cG dF Fy Id Ih Js Lx Mt Nq Ny Pz Qc Sr Tn Tr Un Vq Vt) Qa(AA Ct Dr In Jn Js Jt Kj Ko Mm Nj Ns Nt Nx Ny Oy Ug Us) Ld(Ed Im Ji Jl Jr Ke Ko Kq Lx mU mW No Oh Pe pI Qd Ri Sr Vt) Jp(bA bN cH cJ Ct Dc Dp Ed hB Jt Kq Qw Ri Sr Ss Tz Uu Tl) Fr(Fp Hv Ih Jg Jl Jq Jt Lv Mi Mp Mr Nl Nt Pb Pe Qb Qc) Ir(In Io Ip Lt Mt Mw Nj Nm Nn Ns Nu Oz Pg Ry Ur Va We) Yi(bM In Jo Li Lz MI Om Ow Pb Qb Qx Rh Ug Uh Ut Uv Yh) Mz(bN cI Cx Fp Io Jq Kx Ky Om Qb Qe Ri Tv wJ Yk Wm) Kk(Ed Em Fd iB Ij Il jF Ji Kq Oh Ow Qc rB Ri Sr Vt) Oz(Aa Fd Fp Gc Ih Iv Jl Lv Nn Nt Nx Pf Po Qe Wd Zx) Qd(Aa bF cT hB jF Jl jT Lv Lw Mi Mp Mr Nn rS Us) Xa(aW Dc Hv Jh Ji Jr Ke Mk Mr Mx Ni Nu Pg Sh Uc) Ny(Fp Ib Ih jF jK Jn Js Mm Nt nU Nx Po Qc Qe Wm) Ur(Dd Ij Ip Jt Kf Kq Lx Nr Oa Oh Ok oW Sr St Uc) Lx(Aa aV bS Fc Hu Jl Jq Lv Nt Ow pH rS Wh) Ip(Fp Jn Js Jt Lv Mw Nm Nn Nt Nx Oy Pb Pg) Ko(Ed hX Ik Im Ji Jo Kj Ng Oi qZ rB Ri Ug) Mt(aA It Jn Js Jt Nj Nn Ns Nx Oe Pb Pe) Jg(Hu Hx Ik Jq Mi Mr Nn Nt Oi Pe Qc Uu) pH(aN Ar Ax Fw No oE OF Pe Ri Rj Sr) Js(Fp In Jt Kc Lv Nj Nm Ns Nt Oe Oy) Vt(dK II In Ky Nj oH Qe Qg Ri Ug Va) aA(Io It Jt Nm Nr Nu Nx Og Pg Pz Qe) Ji(Aa bF dJ Ed iZ Kc Ph rX wB) Ru(Fw Hq Hv Hx Jd Jr Ky Or Un) Og(Hx It Mm Mp Mx Nr Nu Qb Qc) Uh(aW cQ hW Kc kG mF mM nC Vs) hB(aE bN eC Em jO kE Kn Ow Ry) Nj(Fp Jl Jn Jt Mw Nn Po Qe) Ke(Ii Il In Kc Kj Oy Pb Us) Pg(It Iv Mw Mx Nu Pb Qc Wm) wD(Bg Ct Ef Iz Kn nW rB rC) Im(aQ bA bS cJ Ct dJ) Qe(Aa Ct Lw Nm Ns Nx) oE(Dr Gb Hp nI No Uw) Fp(Io Lw Mm Nt Uw) Nn(Hu It Ns Nx Oy) In(Ih Jt Kn Ow Vq) Zq(dR Hx Il Ki Qb) On(Ch De jO Vo Wm) Va(Dk Fd Jk Ou Vq) Kc(jK Kq Oa Oh) Rx(Hx Mr Ok Pi) Pf(nK Nl Nm Oh) Aa(Hr Ij Qc) Eq(Nv Tn Vu) Ho(aZ Oh Qb) Wb(Mf Nr oF) Sh(Dk Ih Tn) Jt(Li Lv Ng) Kq(Ef Jo Oi) Ps(kG nN nU) Nw(rZ wB wQ) Ow(kP mE Ng) Vj(Pi Qb Vq) Oy(Mw Po uT) Dr(oF Ou) Fd(bZ Ql) No(eC Ph) Nt(Ik Li) Jl(Hr Nv) Ye(Ef Mr) Tl(Jk Vu) Kr(rS tS) Ri(eZ qC) Or(jT Vw) Pe(Oh Pb) aZ(Wd Ti) cU(Hp Ry) cZ(rR rY) nI(Ky Rj) qZ(dJ eC) uT(oN Pj) AfUw CsTh CuYh NqUy MewB MmJn MwNl TnWh IhIj YjRm QcbA KnjT LpQl NvjO OmVb VicQ cHnY nNiH tTiP kClN kIoW rSvI nWuX

Constrained panels with 2 analytes, where 1.0E-5 >= 'AUC p-value' > 1.0E-6. Contains 1,268 panels of 191,187 total panels evaluated. : Jj(aA Al Ao Ap Ax Bc bF bQ Cs Cu Cx Dg Ed Ez Fa Fw Fy hB Hx Id Il Jd jF Jk Jo Jr Ju Kc Kd Kr Kx Ky Ld Mg Mj Mp nC Ng Nh Nl oF Og Oh Oz Pe Pf Pi Qc Rm rS Tr Tz Yi) Vt(aQ bA bB bF bR cE cJ cQ cT Cx dF Dp DR eZ Fy Gp hB iB Ij Ik Im jT Ju Kc Ke Kn Kq Lj Mh Mt Mz No Nr oE Og Oh On Ou Ow Pi Qa Qc Qd rB Ru Sr Tn We) hB(Aj aQ aW bB bS Ch cJ Dc De dJ Hb Hc Ij Il Ip Is Jn Jq Jr Js Kd Ko Ld Li Lj Lu mF mI nI Oh Oi oN Oy Pi rB Ri Tz Vc Vq Ti) Kk(Aj aQ Ar bR cQ Cs Cu Dc eC Gp Hb Id Ir jK Jl Js Jt Ke Ko Ky Lh Li Lj Mj Mn Mw Mx Mz Nr Oa Oi On Oz Pi Tz Ub Un Ur Vq) Ld(aI Aj bA bB bF bR cE cG cH Dc dF eC iB Id Ij Js Ky Mt NN Nr Ny Oa Ok On Ow Qc Qe Qh Rt St Tz Uf Un Vh Vq Ye) Ko(bN Ch cQ eC Et iB Il Iz Kc Ke Kl Lj Lx Ms Mz No Oa OE oF Oh Ou Ow Ph Qb Qd Qe Sr Ss Us Vo) Qe(bA bN Dr Fp Ip Iv Jn Jq Jt Kc Lj Lv Mi Mm Mp Mt Mw Nl Nn Nt Nu Oe Oy Pb Pe Po Ug Us Vs) Ip(Hx Ih Io It Iv Jq Jr Lw Lz Mi Mm Mp Mx Nb Nj Nl Nq Nr Ns Nu Oh Om Pa Pe Po Qb Qc) Lj(Fd In Io It Jh Jo Kc Mg Nb Nh Nn Nq Ns Nu oF Ou Pb Pe Po Pz Ri Ur Vj Wd Yd Yj) Nx(Aj Hr Ih Io Ir It jK Jn Lv Mm Mp Ms Mw Mx Nr Ns Nt Oe Om Oy Pb Pe Po Qb Qc) aA(cJ Fp Ih Ii Ir Iv Jm Jq kP Lv Lw Mg Mp Mw nC nK Nl Ns Om Pb Pe Po Qb Qc Uw) Et(Dr eC Ed Fd Fy Ic Id jF jO Kd Kl Kq Oa oF Or Ou Ow Ph Pi Rm rR rS Ss Tv) Nn(Aj Fp Ih Iv Jn Jq Js Jt Lv Lw Mi Mm Mp Mx Nl Nm Nt Oe Pb Pe Po Qa Qb Qc) Oz(bA Fi Ho Hp It Jn Jt Ke Mm Mp Mw Nb Nl Nm Nr Nu Og Om Pa Qb Vq Yg Zq) No(Aa aQ bS CH cJ Ct dJ Ic jK Kj Kn Kq oH Ou Ow Ri rS Ss Ug Uu Vo) Nt(Hx Ih In Ir It Jn Jq Jt Lv Ly Mp Mt Mw Na Ng Nj Ns Oy Pb Po Qb Qc) Is(aQ bA Bb cP Dr iB Iv jK Jl jR Ke Kj Mi Mp Mr Ms nL Pe Qa Ri Up Vo) Mt(Aa Fp Hx Ih Ik Iv jF Jq Lv Lw Mi Mm Mp Ng Nl Nm nU Om Po Qa Qc) Kq(Bg cQ Ct Hc Ii In Jh Jk jT mZ Nj Og oH Oy Ph Ss Ua Ug Uu Uv Vo) Aj(Ao Ar Bc Bg bQ Cw Dd Jk Jn Kg Kp Mw Ou Ow Po Qh Ri St wD Yi) Lx(Ax Bb bN bQ cG cJ cK dH dI dK Dr Gc KP mF nC nK Qw Ri Uk) Fp(Ih Ik It Iv Jn Jq Lv Mi Mp Mw Nl Nm Og Om Pb Pg Pz Qa Ru) Aa(It Iv Jl Jn Jo Jp Js Lv Ma Mk Mn Mz Nl Og Ok On Oy Qb) Po(Hr Ih In Io It Iv Jn Jq Jt Mm Ns Oe Om Pb Pe Qc Ru Wb) Mm(Ih Ir It Jl Jq Lv Mj Mp Mr Mx Nj Nr Ns Pe Pf Pg Qc) Qa(bA Bb bF bN bS cI cJ cP eQ Kn Lv Lw nK Nm Oe oH Vs) Og(Ii Il Jh Jk Jq Jr Lv Lw Mi Mj Mr Mv Nm Nq Oa Oh Pz) Im(aI aN bF Ch cI cT Dc dD dF Ex iP Iz Ke nU oH Ri) On(Af Ao aQ bS cH cJ Ct Ef Kj mM nC nK nU oN Us Uu) Mn(aJ Ax bA bS cH Cs Ct Cu Dc dM Jl Kc Kj Ri Sh) Ke(Ch cI cQ dK hX Iz Oi Ou Ow Ri Ru Uv Va Vo Yi) Lh(Hx Io Jl jO Jq Jt Md Ml Mr Mw Nl nU Ug Uu Va) Ur(Bb Cq Id Ih Jl Jq Li nR Nv Ou Pg Qc Rm Tv Uf) Ma(Hu Hv Jl Jq Jr Jt kP Lw Mi Mp Mr Nl Oe Oy) Ir(Hx It Iv Lw Mi Mp Mr Oe Pb Pe pH Qc Xa) Qd(aQ Bb cH cI cJ eZ Iz Kj Kn oH Ow Ri Wm) Yi(aM bZ Ct cU Hv Ji Mf Mj Mx Tz Uu Vu) Wb(aP bB bQ Ex Fy Ky Lv Mj Ou Qc Ql Qx) Jn(In Js Jt Lv Mp Mw Nl Nm Nu Oe Pb Pe) Vj(AL bA Dd Hx Js Ks Lp Mx Pg Ph Tv) Dr(Co cU Fw Fy Ky Nw Pf Qc Uw Vq Xa) Jp(bR cI cT Cu dJ nU oE Sh Tv Vs Xa) Jt(Ct Hr It Iv Jg Jo Mp Ns Ny Pb Qb) Fd(gL Jy Li Lz Mr Mw oE Qx Qy St) Nr(Hr It Lv Lw Mi Nm Oy Pe Pg Vc) Js(jF Jl Lw Mi Mp Mr Ms Pe Ug Yh) Kc(Ar Cs dF Hb Ij Jl Li Qb rW Sr) Uw(cQ Cs Cx Il Iv Mx Oi Qc Qv Uu) Gc(dR Ky Mr nC oE Qv Tn Va Vu) Un(eC iB Ik jH jT Ms oH Oi Ug) Pg(Hv Hx Ih Jq Nl Pz Ru Tv Vz) nU(cH Hu Lz Mq Nv Oh Ow Qc Uh) Mw(It Iv Jr Lv Ms Ns Pb Pe) Mz(bA bF cJ Ed Jo Kd Kp Oa) Ny(Ao iB Jl Jq lO nK Qb Ri) nI(bZ eC Fw oF Qh St Ug Um) wB(aN Hu iP Jk Nm Oy rB rS) pH(bR bU cA cJ Li St Ul Vs) In(Dc Fy Id Kx Pe Pi Sr) Xa(Iv Kd Li Lz Qx Ru Tz) Ow(bR Gz Ji Ky mF oF Oi) bA(cH cQ Ct Cx Ij Li Pb) wD(aN bH bS Ch qU Qy Uh) rS(Ax Fb Kn nW Pj Uk yL) Pf(Hw Jr kP Nb Oy Pb) aZ(Fi Rt Ru Ry We Wf) uT(bL Hq Jk My Nq rW) Dc(Ar Ct Ik Jo Ug) Id(eZ jT oE qC Ug) It(Io Lv Nq Pe Va) Ji(Fy Ic rB Yd yL) Ri(Ed iB Sr vB wP) oW(aD bM Cv oH Uu) Eq(bQ Co Jk Nq) Ij(Ct Gd Ug Vo) Sh(Ef Hq Nq Qh) Zq(aX hC Jm Tz) Jr(jH Ns Nu Wm) Ye(Jh Jk Mq mU) Kn(eC Ed Ou Ug) Va(Jh Mv Qc Tv) Vq(Ik Ru Ux Yl) Pe(Gd Lv Nm Wm) dF(cH Cx dK oN) iB(An Kf Kx Pj) Ar(cJ dK Nj) Ho(aH oE Or) Sr(oH Oi Ug) Jl(Jg Ns Oe) Kp(pS rB rW) Nw(Em nK rB) Ou(cH Oh rN) iP(hL tX uX) vI(aN dJ Kr) Ex(bR Ru) Lv(Ih Io) Tn(Ch Vs) Si(fR iZ) Rx(Jq Qh) Nv(bS Wm) Ok(dK Vo) Vu(Gn Rt) cJ(Cs Qc) jF(mY Nl) AxbF CuVw DkWf DpOa EmKy FycQ GdUt NsOm MpNj MvUy NgUf NkrN TzRu HvJg IhIo HcqZ YjQb JeVi JkTm KfjK LiiH LpoE OpnN OrmI VccU UzbZ aEoF nHhR tXnW jIoO Constrained panels with 2 analytes, where 1.0E-4 >= 'AUC p-value' > 1.0E-5. Contains 2,003 panels of 191,187 total panels evaluated. : Ld(aH aJ aQ bS bV bZ cA cB cJ cQ Cs cT Cu Cx cZ dD dJ dM Fr Fw Fy Gp Hb Ic iH Il Ir Jd Jn Jq Kc Kd Kf Kn Kx Lh Li Lj Ly Ma mF Mw Mx mZ Nh nI nR nU Nv OE oF Oi Or Ou Pi Pj Qb Ru Tn Uc Up Ut Vp wB) Jj(aH aI aQ Ar aW aZ bA bB Bg bZ cE cG cH cJ CP Cq Cw dD dF dJ Dl Em Fb Ha Hv Hw iB IC Iq Iu Jh jK Jq jR jT Lw Mi Mr Mv Mx Nb Nc Nq oE Or Pa Ql Qy Rf rN Tn Tt Tv Ua Up Ur UT Vp Vu) Aj(AA aH Al Ax bF bZ cJ Cs cT Dl dM Ef Ez Fa gL Hx Ii Il Ip Iq It Iz jB Jd Jh Jl Jo Kc Kd Kl Kr Kx Ky Lj Lv Mg Mi Mm Mp Nb Nj Nm Nr Nt nU Oa oF Oh Or Pg Pi Pj Qb Rm Ua UT Uw Vu wP) Kk(aA bA bB bN bS cA cH cJ dF Dp Fw Gc Ho Hv Ic Ik In Iq Iu Iv Jn Jq Jr Kd Kf Kn Kx Lp Ly Ma Mh Ml Ml Mr Mt mU Na Nc Nh Nn OE Or Ou Pj Qb Qh Rm rS Uc Uf Uz Vj Yl Wm) Qc(aH aQ Ax Ba bB bF bV cE cG cH cT Dc DD dF Di dK Fp hB Hx It Iv Jl Kc Kn Lv Mp Mw Mx nC Nj NL Nm Nu Om Oz Pa Pe Ry Un Vj Zq) Ko(aA aM bA bB bF cA cH cU Dc dD dF dK dM Fw Gd iH Ir jF jK Jl Jq Jr Jv Kn Kq Kx Ky Li Lv Mh Mj Ml Ne Nh Nj Nn Nr Or Tz Un Va Vp) Ri(Ar cH Cs dM Ex Fp Fw Gc Hb hW Id Ij In iZ jF Jq Jr Js Kp Kq Kx Lh Li Mt Nr Nv Oa Og OH Oi On Ou Ow Pe Pi Qa Qb Qe rX Tz Un) Ur(Ad Ar Ax BA cE cH Co cQ Cs cT dF dM Ed Fd Fr hB Iq Iu Jg Ju Kd Kp Kr Ma Mt Nh nI Nt Nx Ny oH Om Or Ow Pe Po Qh Tn Tr vI wB) Kq(aC Ad Af bA bL bS cA cH cI hB Hq IB Kl Kn Ky Lj Mg Mn My nI Oa OE Oh Om oN Ow Pb Qu rB Rz Tn Uk Us Vs Wd Wf Wh) bA(Ad Ar Bb bO cJ Cs Dc Dd Fr Gc iB Ih Ik In It Jq Js Jt Lj Lw Mi Mm Mt Mu No Ns Oe Og Oi Ok On Ow Oy pS Qb rB Rx uR) Ar(Ad aE aH aQ Ax aZ Ba BB bN cG cH cT Cu Dd Fd Fr Ho Hx Ik

Figure 28 Continued

In Jg jK Jl Jr Lv Lw Mi Nx oE Og Oi Ou Vp Wb) Kc(aC al aQ cE cH cJ eC Ed hW hX Id Ih Im jl Jq Lx Mt Mx Ny oE oF Ok On Or Ou Ow qC
Qh rB St Tz Un wB) hB(Bg bR cP Cu Ed fP Fw Hv Id Ih Im Iv Jl jT Kx IL Mr Mt Ng nN nW Oa oE oH Pb Pj Qa Qe Qh Sr Tv uZ Th) Ky(aE
Ax bR bS Cs Dd Fc Fi Ho Hx Ih Ij Il Im jT Kd Kn Li Lj Lp Lx ml Mn Mr Mt Nr Ny On oW Ry Uw Zq) Ow(al Ax bS cE dD dF dM iB Is Jl Jr
Kn Kp Kr Li Lj Mn Mr Ms Mt Nr Oe Oh Ok On Ou Pe pS Qa Qe Ug Vp) Jl(aA Bb Fp Gc Hu lo Ip It Jn Jq Jt Ke Kx Lv Lw Mi Mp Mt Mw Nm
Nt Nu Oy Pb Qa Qe rS Us Vt) Om(Dr Hr Hu Ih In Ir It Iv Jn Lv Lw Mm Ms Mw Mx Nj Nl Nt Nu Oe Oy Pb Pe Qa Qb Qe Rz Ug) dF(Ax Bb bN
bR dH Gc Ho Ij Jn jO Li Lj Lw Mn Mz nl Nj nK Oe Oi Oz Qd rB Si Vc Vj Wb) Sr(aC aE al aQ bR CH cl cQ dD d

Figure 28 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 8.1E1 | 8.1E1 | 9.4E1 | 7.5E1 | 6.8E1 | 4.2E1 | 7.0E0 | 1.6E1 | 4.8E2 | 1.5E2 | 286 | 9 | 286 | 9 | 0.43 |
| Ad | ug/mL | 4.7E-2 | 9.7E-2 | 1.2E-1 | 1.2E-1 | 6.6E-1 | 1.1E-1 | 6.8E-4 | 7.8E-4 | 8.5E0 | 3.5E-1 | 165 | 8 | 165 | 8 | 0.65 |
| Af | ng/mL | 1.2E0 | 1.4E0 | 1.0E1 | 3.0E0 | 4.5E1 | 4.1E0 | 1.7E-3 | 1.5E-1 | 5.3E2 | 1.2E1 | 165 | 8 | 165 | 8 | 0.45 |
| Aj | ug/mL | 1.1E0 | 7.5E-1 | 2.3E0 | 2.4E0 | 2.4E0 | 2.8E0 | 1.5E-3 | 1.3E-3 | 6.1E0 | 5.8E0 | 165 | 8 | 165 | 8 | 0.49 |
| Al | mg/mL | 8.3E-5 | 7.4E-4 | 2.6E-4 | 6.5E-4 | 4.3E-4 | 5.6E-4 | 4.3E-6 | 7.8E-6 | 1.8E-3 | 1.5E-3 | 165 | 8 | 165 | 8 | 0.64 |
| An | U/mL | 6.1E1 | 8.9E1 | 2.6E2 | 1.6E2 | 8.0E2 | 1.5E2 | 2.8E-1 | 2.2E1 | 7.8E3 | 4.6E2 | 165 | 8 | 165 | 8 | 0.61 |
| Ao | pg/mL | 9.4E1 | 3.9E2 | 5.3E2 | 9.7E2 | 3.6E3 | 1.5E3 | 1.5E0 | 4.1E0 | 3.9E4 | 4.5E3 | 165 | 8 | 165 | 8 | 0.65 |
| Ap | ng/mL | 3.3E1 | 1.0E2 | 4.7E1 | 1.2E2 | 5.2E1 | 9.7E1 | 2.0E0 | 4.4E0 | 3.3E2 | 2.4E2 | 165 | 8 | 165 | 8 | 0.71 |
| Ar | ng/mL | 7.0E-1 | 1.5E0 | 2.9E0 | 8.0E0 | 6.7E0 | 1.7E1 | 3.4E-3 | 2.2E-1 | 5.1E1 | 5.0E1 | 165 | 8 | 165 | 8 | 0.60 |
| As | ng/mL | 8.7E-3 | 1.7E-3 | 2.0E-2 | 6.2E-3 | 9.7E-2 | 6.6E-3 | 1.7E-3 | 1.7E-3 | 1.2E0 | 1.9E-2 | 165 | 8 | 165 | 8 | 0.38 |
| Aw | pg/mL | 1.6E1 | 2.3E1 | 1.7E1 | 2.3E1 | 6.2E0 | 4.6E0 | 2.9E-2 | 1.4E1 | 5.1E1 | 2.9E1 | 165 | 8 | 165 | 8 | 0.82 |
| Ax | ng/mL | 2.0E0 | 1.6E1 | 2.4E1 | 1.6E2 | 9.0E1 | 3.0E2 | 1.2E-2 | 1.0E-4 | 7.7E2 | 8.5E2 | 165 | 8 | 165 | 8 | 0.66 |
| Ba | ng/mL | 8.3E1 | 1.1E3 | 5.9E2 | 3.1E3 | 1.5E3 | 5.0E3 | 1.1E0 | 4.1E0 | 8.1E3 | 1.5E4 | 165 | 8 | 165 | 8 | 0.79 |
| Bb | ng/mL | 4.0E0 | 1.3E1 | 7.0E0 | 1.7E1 | 8.3E0 | 1.5E1 | 4.1E-3 | 3.5E-1 | 4.9E1 | 4.8E1 | 165 | 8 | 165 | 8 | 0.72 |
| Bc | ng/mL | 3.6E1 | 1.3E2 | 1.2E2 | 3.2E2 | 2.3E2 | 3.8E2 | 4.9E-1 | 2.9E0 | 1.2E3 | 9.9E2 | 165 | 8 | 165 | 8 | 0.68 |
| Bg | ng/mL | 1.1E-1 | 1.3E0 | 4.1E0 | 5.1E1 | 1.7E1 | 1.4E2 | 5.3E-4 | 3.1E-2 | 1.5E2 | 4.0E2 | 165 | 8 | 165 | 8 | 0.66 |
| Bn | ng/mL | 5.6E-2 | 3.5E-1 | 1.5E0 | 4.6E-1 | 4.9E0 | 4.6E-1 | 5.6E-2 | 5.6E-2 | 5.8E1 | 1.2E0 | 165 | 8 | 165 | 8 | 0.53 |
| Bo | ng/mL | 1.3E1 | 1.7E1 | 1.5E1 | 1.8E1 | 1.1E1 | 5.7E0 | 1.6E-2 | 9.7E0 | 5.3E1 | 2.6E1 | 165 | 8 | 165 | 8 | 0.62 |
| Ch | uIU/mL | 1.0E0 | 1.5E0 | 2.9E1 | 1.5E2 | 1.6E2 | 4.2E2 | 3.4E-3 | 5.9E-1 | 1.8E3 | 1.2E3 | 165 | 8 | 165 | 8 | 0.58 |
| Co | pg/mL | 4.7E1 | 1.1E2 | 2.2E2 | 4.3E2 | 1.3E3 | 6.9E2 | 1.5E-1 | 8.8E0 | 1.7E4 | 2.1E3 | 165 | 8 | 165 | 8 | 0.66 |
| Cp | ng/mL | 2.2E1 | 4.8E1 | 3.5E1 | 5.5E1 | 1.0E2 | 3.9E1 | 6.0E-1 | 1.1E1 | 1.3E3 | 1.4E2 | 165 | 8 | 165 | 8 | 0.74 |
| Cq | ng/mL | 3.0E-2 | 1.1E-1 | 4.0E-1 | 4.8E-1 | 3.8E0 | 8.1E-1 | 8.0E-4 | 8.0E-4 | 4.9E1 | 2.3E0 | 165 | 8 | 165 | 8 | 0.72 |
| Cs | ng/mL | 6.0E1 | 1.7E2 | 4.7E2 | 8.7E2 | 1.7E3 | 1.8E3 | 8.3E-1 | 5.7E0 | 1.8E4 | 5.1E3 | 165 | 8 | 165 | 8 | 0.62 |
| Ct | ng/mL | 3.1E-1 | 1.2E1 | 4.0E1 | 6.5E1 | 1.2E2 | 1.4E2 | 1.1E-4 | 1.1E-4 | 6.2E2 | 4.2E2 | 165 | 8 | 165 | 8 | 0.63 |
| Cu | ng/mL | 2.6E-1 | 2.6E0 | 8.8E-1 | 4.6E0 | 5.2E0 | 6.7E0 | 1.9E-2 | 1.7E-2 | 6.6E1 | 2.1E1 | 165 | 8 | 165 | 8 | 0.85 |
| Cv | ng/mL | 5.2E0 | 1.3E1 | 2.9E1 | 3.8E1 | 7.3E1 | 4.9E1 | 2.0E-2 | 1.0E-1 | 5.3E2 | 1.4E2 | 165 | 8 | 165 | 8 | 0.60 |
| Cw | mIU/mL | 3.6E-2 | 8.3E-2 | 8.3E-2 | 8.5E-2 | 5.2E-1 | 4.4E-2 | 8.9E-4 | 1.1E-2 | 6.8E0 | 1.5E-1 | 165 | 8 | 165 | 8 | 0.79 |
| Cx | ng/mL | 8.5E-1 | 3.8E-3 | 5.3E1 | 4.0E-1 | 1.0E2 | 6.3E-1 | 9.3E-5 | 9.3E-5 | 3.9E2 | 1.7E0 | 165 | 8 | 165 | 8 | 0.29 |
| Db | ug/mL | 7.5E0 | 7.4E0 | 8.8E0 | 8.5E0 | 7.7E0 | 3.7E0 | 4.5E-1 | 1.2E0 | 5.9E1 | 1.5E1 | 165 | 8 | 165 | 8 | 0.53 |
| Dc | nmol/L | 2.0E-2 | 1.7E-1 | 1.6E-1 | 2.9E-1 | 1.1E0 | 4.3E-1 | 5.2E-6 | 2.1E-3 | 1.4E1 | 1.3E0 | 165 | 8 | 165 | 8 | 0.79 |
| Dd | ug/mL | 7.1E-2 | 4.3E-1 | 1.9E-1 | 4.9E-1 | 3.6E-1 | 4.9E-1 | 4.8E-4 | 6.4E-3 | 3.6E0 | 1.5E0 | 165 | 8 | 165 | 8 | 0.69 |
| De | ng/mL | 3.4E-3 | 2.3E-1 | 7.5E-2 | 3.0E-1 | 1.4E-1 | 3.7E-1 | 3.4E-3 | 3.4E-3 | 9.2E-1 | 1.1E0 | 165 | 8 | 165 | 8 | 0.72 |
| Dg | ng/mL | 3.6E1 | 8.0E1 | 4.6E1 | 7.1E1 | 4.0E1 | 4.5E1 | 7.1E-1 | 1.9E0 | 1.9E2 | 1.2E2 | 165 | 8 | 165 | 8 | 0.66 |
| Di | pg/mL | 2.0E0 | 3.9E0 | 2.4E0 | 4.0E0 | 2.2E0 | 1.1E0 | 1.8E-1 | 2.7E0 | 1.3E1 | 5.4E0 | 165 | 8 | 165 | 8 | 0.78 |
| Dk | uIU/mL | 1.4E-2 | 3.2E-2 | 5.6E-2 | 1.9E-1 | 1.7E-1 | 3.4E-1 | 1.1E-4 | 6.6E-3 | 1.6E0 | 9.8E-1 | 165 | 8 | 165 | 8 | 0.63 |
| Dl | ng/mL | 2.0E2 | 3.4E2 | 2.9E2 | 4.2E2 | 2.8E2 | 3.9E2 | 5.5E0 | 4.4E0 | 1.6E3 | 1.1E3 | 165 | 8 | 165 | 8 | 0.58 |
| Wm | % | 8.5E-2 | 2.4E0 | 1.5E1 | 4.2E1 | 1.1E2 | 7.5E1 | 5.4E-2 | 8.5E-2 | 1.0E3 | 1.9E2 | 151 | 7 | 151 | 7 | 0.62 |
| Po | pg/ml | 3.0E-1 | 1.7E1 | 9.6E0 | 3.5E1 | 2.9E1 | 6.0E1 | 8.0E-3 | 2.6E-2 | 2.7E2 | 2.2E2 | 339 | 12 | 339 | 12 | 0.77 |
| Et | ng/ml | 1.4E3 | 3.1E3 | 1.7E3 | 2.9E3 | 1.2E3 | 1.5E3 | 7.5E1 | 5.9E2 | 4.8E3 | 5.0E3 | 338 | 12 | 338 | 12 | 0.72 |
| Fp | ng/ml | 1.3E1 | 2.6E1 | 2.4E1 | 3.3E1 | 2.7E1 | 3.5E1 | 6.0E-3 | 1.3E0 | 1.3E2 | 1.2E2 | 341 | 12 | 341 | 12 | 0.57 |
| Fr | ng/ml | 3.5E4 | 5.5E5 | 1.2E5 | 4.4E5 | 1.8E5 | 3.4E5 | 1.9E2 | 4.5E3 | 8.4E5 | 8.4E5 | 346 | 14 | 346 | 14 | 0.76 |
| Nm | pg/ml | 1.3E4 | 7.5E4 | 3.4E4 | 1.3E5 | 8.9E4 | 1.5E5 | 1.0E-9 | 1.0E-9 | 9.6E5 | 4.4E5 | 342 | 12 | 342 | 12 | 0.66 |
| Nn | pg/ml | 1.5E2 | 1.0E3 | 1.7E3 | 4.0E4 | 8.0E3 | 9.0E4 | 1.0E-9 | 1.0E-9 | 9.5E4 | 3.1E5 | 342 | 12 | 342 | 12 | 0.77 |
| No | pg/ml | 1.5E1 | 4.2E1 | 3.8E1 | 1.2E2 | 9.0E1 | 2.0E2 | 1.0E-9 | 1.6E0 | 9.1E2 | 7.0E2 | 342 | 12 | 342 | 12 | 0.70 |
| Nq | pg/ml | 1.9E0 | 2.1E1 | 2.0E1 | 1.3E2 | 7.3E1 | 1.8E2 | 1.0E-9 | 1.0E-9 | 6.7E2 | 5.9E2 | 342 | 12 | 342 | 12 | 0.72 |
| Nr | pg/ml | 1.6E0 | 1.1E1 | 2.3E1 | 1.6E2 | 8.3E1 | 3.9E2 | 1.0E-9 | 1.0E-9 | 9.8E2 | 1.4E3 | 342 | 12 | 342 | 12 | 0.68 |
| Ns | pg/ml | 1.0E-9 | 1.0E-9 | 7.8E0 | 3.0E-1 | 6.5E1 | 1.0E0 | 1.0E-9 | 1.0E-9 | 1.1E3 | 3.6E0 | 342 | 12 | 342 | 12 | 0.51 |
| Nt | pg/ml | 1.0E2 | 2.3E2 | 1.4E2 | 3.2E2 | 1.3E2 | 3.3E2 | 9.8E-1 | 6.4E1 | 1.7E3 | 1.2E3 | 342 | 12 | 342 | 12 | 0.75 |
| Nu | pg/ml | 1.7E1 | 9.7E1 | 5.6E1 | 1.1E2 | 9.3E1 | 8.3E1 | 1.0E-9 | 6.3E2 | 2.9E2 | 342 | 12 | 342 | 12 | 0.74 |
| Lu | pg/ml | 1.0E4 | 1.0E4 | 1.5E4 | 1.1E4 | 4.0E4 | 7.5E3 | 5.2E2 | 1.4E3 | 5.6E5 | 2.7E4 | 342 | 12 | 342 | 12 | 0.53 |
| Lv | pg/ml | 1.0E-9 | 4.7E1 | 1.5E1 | 5.9E1 | 3.1E1 | 5.1E1 | 1.0E-9 | 1.0E-9 | 2.6E2 | 1.8E2 | 342 | 12 | 342 | 12 | 0.82 |
| Lw | pg/ml | 1.0E-9 | 1.0E-9 | 5.2E-1 | 2.0E1 | 5.2E0 | 5.1E1 | 1.0E-9 | 1.0E-9 | 8.0E1 | 1.8E2 | 342 | 12 | 342 | 12 | 0.66 |
| Lx | pg/ml | 1.0E-9 | 4.8E2 | 2.5E2 | 7.8E2 | 1.3E3 | 8.5E2 | 1.0E-9 | 1.0E-9 | 2.2E4 | 2.8E3 | 342 | 12 | 342 | 12 | 0.80 |
| Ly | pg/ml | 1.0E-9 | 1.0E-9 | 9.2E0 | 3.9E0 | 1.8E1 | 7.6E0 | 1.0E-9 | 1.0E-9 | 1.1E2 | 2.4E1 | 342 | 12 | 342 | 12 | 0.44 |

Figure 29

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Lz | pg/ml | 1.0E-9 | 1.0E-9 | 3.5E0 | 4.2E0 | 2.6E1 | 1.4E1 | 1.0E-9 | 1.0E-9 | 4.3E2 | 4.7E1 | 342 | 12 | 342 | 12 | 0.55 |
| Ma | pg/ml | 3.9E2 | 5.1E3 | 2.1E3 | 1.2E4 | 5.4E3 | 1.7E4 | 1.0E-9 | 2.4E1 | 6.5E4 | 5.2E4 | 342 | 12 | 342 | 12 | 0.69 |
| Mb | pg/ml | 2.5E1 | 2.7E1 | 3.2E1 | 3.3E1 | 1.8E1 | 1.6E1 | 4.1E0 | 1.6E1 | 2.1E2 | 5.8E1 | 342 | 12 | 342 | 12 | 0.51 |
| Mc | pg/ml | 1.0E-9 | 1.0E-9 | 5.6E-2 | 1.0E-9 | 7.4E-1 | 0.0E0 | 1.0E-9 | 1.0E-9 | 1.3E1 | 1.0E-9 | 342 | 12 | 342 | 12 | 0.49 |
| Md | pg/ml | 1.0E-9 | 1.0E-9 | 6.8E-1 | 3.9E-1 | 5.5E0 | 1.2E0 | 1.0E-9 | 1.0E-9 | 6.8E1 | 4.0E0 | 342 | 12 | 342 | 12 | 0.54 |
| Me | pg/ml | 3.1E1 | 2.9E1 | 3.1E1 | 3.7E1 | 2.4E1 | 4.9E1 | 1.0E-9 | 1.0E-9 | 3.2E2 | 1.8E2 | 342 | 12 | 342 | 12 | 0.44 |
| Mf | pg/ml | 1.0E-9 | 1.0E-9 | 6.1E-1 | 9.0E-1 | 3.9E0 | 1.8E0 | 1.0E-9 | 1.0E-9 | 5.6E1 | 5.0E0 | 342 | 12 | 342 | 12 | 0.60 |
| Mg | pg/ml | 9.4E-1 | 8.8E0 | 6.2E0 | 2.7E1 | 1.2E1 | 4.7E1 | 1.0E-9 | 1.0E-9 | 9.2E1 | 1.5E2 | 342 | 12 | 342 | 12 | 0.61 |
| Mh | pg/ml | 1.0E-9 | 2.0E-2 | 1.2E0 | 1.9E0 | 7.6E0 | 5.2E0 | 1.0E-9 | 1.0E-9 | 1.1E2 | 1.8E1 | 342 | 12 | 342 | 12 | 0.61 |
| Mi | pg/ml | 1.0E-9 | 2.0E0 | 1.9E0 | 5.9E1 | 1.9E1 | 1.5E2 | 1.0E-9 | 1.0E-9 | 3.2E2 | 5.2E2 | 342 | 12 | 342 | 12 | 0.73 |
| Mj | pg/ml | 1.0E-9 | 9.8E-1 | 6.2E0 | 3.6E1 | 3.2E1 | 6.5E1 | 1.0E-9 | 1.0E-9 | 4.6E2 | 2.1E2 | 342 | 12 | 342 | 12 | 0.67 |
| Mk | pg/ml | 1.5E0 | 5.6E0 | 1.5E1 | 5.0E1 | 9.2E1 | 1.4E2 | 1.0E-9 | 1.0E-9 | 1.3E3 | 5.0E2 | 342 | 12 | 342 | 12 | 0.63 |
| Ml | pg/ml | 1.0E-9 | 1.0E-9 | 1.1E1 | 1.9E-1 | 1.2E2 | 6.6E-1 | 1.0E-9 | 1.0E-9 | 2.1E3 | 2.3E0 | 342 | 12 | 342 | 12 | 0.43 |
| Mm | pg/ml | 5.5E2 | 2.0E3 | 1.0E3 | 3.1E3 | 1.3E3 | 3.2E3 | 1.0E-9 | 1.0E-9 | 1.0E4 | 1.0E4 | 342 | 12 | 342 | 12 | 0.68 |
| Mn | pg/ml | 6.0E0 | 1.3E1 | 1.1E1 | 1.8E1 | 2.5E1 | 1.5E1 | 1.0E-9 | 1.1E0 | 3.5E2 | 5.1E1 | 342 | 12 | 342 | 12 | 0.71 |
| Mp | pg/ml | 1.0E-9 | 2.5E1 | 1.3E1 | 2.6E2 | 5.0E1 | 6.7E2 | 1.0E-9 | 1.0E-9 | 6.3E2 | 2.4E3 | 342 | 12 | 342 | 12 | 0.75 |
| Mq | pg/ml | 1.0E-9 | 1.0E-9 | 2.4E0 | 1.4E1 | 1.4E1 | 2.6E1 | 1.0E-9 | 1.0E-9 | 1.8E2 | 7.4E1 | 342 | 12 | 342 | 12 | 0.59 |
| Mr | pg/ml | 1.0E-9 | 5.4E0 | 3.2E1 | 3.6E2 | 1.8E2 | 9.8E2 | 1.0E-9 | 1.0E-9 | 2.2E3 | 3.4E3 | 342 | 12 | 342 | 12 | 0.62 |
| Ms | pg/ml | 3.2E2 | 3.2E2 | 4.7E2 | 7.1E2 | 5.3E2 | 1.3E3 | 1.0E-9 | 1.0E-9 | 3.3E3 | 4.7E3 | 342 | 12 | 342 | 12 | 0.48 |
| Mt | pg/ml | 2.7E-1 | 1.1E1 | 1.8E1 | 5.2E1 | 1.8E2 | 8.9E1 | 1.0E-9 | 1.0E-9 | 3.2E3 | 3.1E2 | 342 | 12 | 342 | 12 | 0.74 |
| Mu | pg/ml | 1.0E-9 | 1.0E-9 | 1.5E0 | 8.2E0 | 1.4E1 | 1.6E1 | 1.0E-9 | 1.0E-9 | 2.3E2 | 4.8E1 | 342 | 12 | 342 | 12 | 0.65 |
| Mv | pg/ml | 1.0E-9 | 1.9E1 | 6.5E1 | 2.5E2 | 3.4E2 | 3.5E2 | 1.0E-9 | 1.0E-9 | 4.5E3 | 9.0E2 | 342 | 12 | 342 | 12 | 0.69 |
| Mw | pg/ml | 3.7E1 | 5.9E2 | 2.7E2 | 1.4E3 | 1.4E3 | 1.9E3 | 1.0E-9 | 1.0E-9 | 1.8E4 | 5.3E3 | 342 | 12 | 342 | 12 | 0.77 |
| Mx | pg/ml | 1.0E-9 | 1.0E-9 | 4.1E-1 | 8.9E-1 | 2.2E0 | 2.0E0 | 1.0E-9 | 1.0E-9 | 3.2E1 | 6.6E0 | 342 | 12 | 342 | 12 | 0.59 |
| My | pg/ml | 1.0E-9 | 1.2E2 | 3.2E2 | 4.8E2 | 2.4E3 | 7.1E2 | 1.0E-9 | 1.0E-9 | 3.9E4 | 1.9E3 | 342 | 12 | 342 | 12 | 0.70 |
| Mz | pg/ml | 1.1E1 | 9.1E1 | 3.5E1 | 8.7E1 | 1.3E2 | 7.0E1 | 1.0E-9 | 3.5E0 | 1.9E3 | 2.0E2 | 342 | 12 | 342 | 12 | 0.80 |
| Na | pg/ml | 1.0E-9 | 1.0E-9 | 7.6E-1 | 1.5E0 | 2.9E0 | 2.6E0 | 1.0E-9 | 1.0E-9 | 4.2E1 | 6.4E0 | 342 | 12 | 342 | 12 | 0.57 |
| Nb | pg/ml | 2.2E0 | 5.1E0 | 4.0E0 | 2.7E1 | 1.2E1 | 5.9E1 | 1.0E-9 | 1.0E-9 | 1.5E2 | 2.1E2 | 342 | 12 | 342 | 12 | 0.69 |
| Nc | pg/ml | 3.1E2 | 1.2E2 | 5.1E2 | 4.4E2 | 7.4E2 | 5.8E2 | 1.0E-9 | 1.0E-9 | 9.2E3 | 1.6E3 | 342 | 12 | 342 | 12 | 0.45 |
| Nd | pg/ml | 2.7E1 | 3.8E1 | 3.3E1 | 4.4E1 | 1.3E2 | 4.3E1 | 1.0E-9 | 7.2E-1 | 2.1E3 | 1.5E2 | 342 | 12 | 342 | 12 | 0.63 |
| Ne | pg/ml | 4.2E2 | 4.0E2 | 5.1E2 | 6.4E2 | 5.4E2 | 9.9E2 | 1.0E-9 | 1.0E-9 | 7.0E3 | 3.6E3 | 342 | 12 | 342 | 12 | 0.47 |
| Nf | pg/ml | 1.0E-9 | 1.0E-9 | 3.1E0 | 7.1E-1 | 1.3E1 | 1.7E0 | 1.0E-9 | 1.0E-9 | 1.3E2 | 4.8E0 | 342 | 12 | 342 | 12 | 0.47 |
| Ng | pg/ml | 1.2E1 | 3.6E1 | 9.0E1 | 7.2E1 | 1.8E2 | 8.6E1 | 1.0E-9 | 1.0E-9 | 1.6E3 | 2.6E2 | 342 | 12 | 342 | 12 | 0.53 |
| Nh | pg/ml | 6.1E1 | 3.7E1 | 7.9E1 | 8.2E1 | 7.2E1 | 1.4E2 | 1.0E-9 | 4.5E0 | 5.6E2 | 5.1E2 | 342 | 12 | 342 | 12 | 0.38 |
| Ni | pg/ml | 1.0E-9 | 1.0E-9 | 8.5E1 | 7.0E1 | 1.4E2 | 1.4E2 | 1.0E-9 | 1.0E-9 | 1.1E3 | 3.7E2 | 342 | 12 | 342 | 12 | 0.43 |
| Nj | pg/ml | 7.2E0 | 5.5E0 | 1.1E1 | 6.6E0 | 1.2E1 | 6.5E0 | 1.0E-9 | 1.0E-9 | 6.9E1 | 1.7E1 | 342 | 12 | 342 | 12 | 0.39 |
| Nk | pg/ml | 1.8E1 | 1.0E-9 | 3.2E1 | 2.4E1 | 3.9E1 | 3.4E1 | 1.0E-9 | 1.0E-9 | 2.0E2 | 8.7E1 | 342 | 12 | 342 | 12 | 0.40 |
| Nl | pg/ml | 4.2E1 | 3.0E1 | 5.6E1 | 4.4E1 | 7.5E1 | 5.6E1 | 1.0E-9 | 1.0E-9 | 1.1E3 | 1.8E2 | 342 | 12 | 342 | 12 | 0.40 |
| Hq | pg/ml | 1.2E0 | 7.2E0 | 1.6E2 | 2.6E1 | 1.9E3 | 5.2E1 | 1.0E-9 | 1.0E-9 | 2.8E4 | 1.8E2 | 340 | 12 | 340 | 12 | 0.68 |
| Hr | pg/ml | 9.1E1 | 1.6E2 | 6.6E2 | 4.6E2 | 1.4E3 | 9.6E2 | 1.0E-9 | 1.0E-9 | 1.2E4 | 3.4E3 | 340 | 12 | 340 | 12 | 0.48 |
| Hu | pg/ml | 1.1E1 | 5.4E2 | 4.6E3 | 1.2E3 | 4.0E4 | 1.7E3 | 1.0E-9 | 1.0E-9 | 6.3E5 | 5.9E3 | 340 | 12 | 340 | 12 | 0.65 |
| Hv | pg/ml | 1.4E0 | 2.0E1 | 5.2E0 | 1.9E1 | 4.9E1 | 4.7E1 | 1.0E-9 | 3.8E-1 | 8.9E2 | 1.6E2 | 340 | 12 | 340 | 12 | 0.64 |
| Hw | pg/ml | 6.2E0 | 1.2E1 | 4.3E1 | 7.1E1 | 5.1E2 | 1.4E2 | 1.0E-9 | 4.6E-1 | 9.4E3 | 5.0E2 | 340 | 12 | 340 | 12 | 0.62 |
| Hx | pg/ml | 8.8E0 | 2.1E1 | 5.5E1 | 1.4E2 | 5.0E2 | 3.6E2 | 1.0E-9 | 6.8E0 | 9.3E3 | 1.3E3 | 340 | 12 | 340 | 12 | 0.72 |
| Ih | ng/ml | 6.3E1 | 2.9E2 | 2.6E2 | 5.7E2 | 4.6E2 | 6.8E2 | 1.0E-9 | 2.4E0 | 3.6E3 | 1.9E3 | 341 | 12 | 341 | 12 | 0.63 |
| Ii | ng/ml | 8.3E1 | 2.4E2 | 2.1E2 | 6.7E2 | 5.1E2 | 1.2E3 | 7.3E-1 | 7.5E-1 | 5.2E3 | 4.5E3 | 341 | 12 | 341 | 12 | 0.63 |
| Ij | ng/ml | 7.9E1 | 2.5E2 | 2.5E2 | 4.9E2 | 1.4E3 | 6.5E2 | 2.8E0 | 9.5E0 | 2.4E4 | 1.9E3 | 337 | 12 | 337 | 12 | 0.73 |
| Ik | ng/ml | 1.1E1 | 3.5E1 | 1.3E3 | 2.5E2 | 1.2E4 | 4.3E2 | 5.9E-1 | 6.2E-1 | 1.2E5 | 1.5E3 | 337 | 12 | 337 | 12 | 0.57 |
| Il | ng/ml | 3.6E2 | 8.8E2 | 1.3E3 | 4.1E3 | 2.8E3 | 5.3E3 | 1.0E-9 | 1.9E-1 | 1.2E4 | 1.2E4 | 335 | 12 | 335 | 12 | 0.60 |
| Im | ng/ml | 2.1E2 | 7.0E2 | 4.5E2 | 2.1E3 | 7.8E2 | 4.2E3 | 1.4E1 | 2.2E1 | 6.2E3 | 1.5E4 | 337 | 12 | 337 | 12 | 0.74 |
| In | ng/ml | 3.4E0 | 1.5E0 | 3.3E1 | 8.3E1 | 2.6E2 | 1.8E2 | 1.0E-9 | 1.0E-9 | 4.5E3 | 5.9E2 | 341 | 12 | 341 | 12 | 0.50 |
| Io | ng/ml | 9.4E3 | 1.5E4 | 1.9E4 | 2.2E4 | 4.6E4 | 2.8E4 | 1.0E-9 | 9.0E2 | 7.1E5 | 1.0E5 | 341 | 12 | 341 | 12 | 0.56 |
| Ip | ng/ml | 1.0E-9 | 3.0E1 | 2.1E1 | 3.4E1 | 2.6E1 | 2.1E1 | 1.0E-9 | 8.1E-2 | 2.3E2 | 7.1E1 | 341 | 12 | 341 | 12 | 0.68 |
| Iq | ug/ml | 1.0E-1 | 9.3E-1 | 4.1E1 | 4.9E0 | 7.4E2 | 7.2E0 | 1.0E-9 | 1.0E-9 | 1.4E4 | 2.1E1 | 341 | 12 | 341 | 12 | 0.70 |
| Ir | ug/ml | 3.7E-1 | 3.1E0 | 5.6E0 | 2.7E1 | 3.8E1 | 4.6E1 | 1.0E-9 | 3.5E-2 | 5.1E2 | 1.3E2 | 340 | 12 | 340 | 12 | 0.70 |
| Is | ng/ml | 2.0E0 | 2.9E1 | 9.4E0 | 5.7E1 | 3.4E1 | 7.6E1 | 1.0E-9 | 2.2E-1 | 5.5E2 | 2.6E2 | 341 | 12 | 341 | 12 | 0.77 |
| It | ng/ml | 2.1E0 | 3.8E0 | 2.3E1 | 5.1E1 | 1.0E2 | 1.6E2 | 1.0E-9 | 1.0E-9 | 1.1E3 | 5.5E2 | 341 | 12 | 341 | 12 | 0.58 |

Figure 29 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Iu | ng/ml | 1.7E2 | 9.7E2 | 1.3E3 | 6.2E3 | 4.1E3 | 9.3E3 | 1.0E-9 | 1.0E-9 | 2.9E4 | 2.4E4 | 341 | 12 | 341 | 12 | 0.57 |
| Iv | ng/ml | 1.3E1 | 2.4E1 | 9.8E1 | 6.9E2 | 8.8E2 | 1.5E3 | 1.0E-9 | 1.9E0 | 1.6E4 | 3.8E3 | 340 | 12 | 340 | 12 | 0.65 |
| Pz | ng/ml | 3.5E3 | 1.0E4 | 5.6E3 | 7.6E3 | 6.0E3 | 4.3E3 | 1.6E1 | 4.0E1 | 7.0E4 | 1.3E4 | 337 | 12 | 337 | 12 | 0.63 |
| Qa | ng/ml | 3.6E3 | 2.1E4 | 7.4E3 | 1.9E4 | 1.4E4 | 1.2E4 | 1.5E2 | 2.9E2 | 2.2E5 | 3.2E4 | 337 | 12 | 337 | 12 | 0.75 |
| Qb | ng/ml | 1.1E2 | 3.0E2 | 2.4E2 | 3.9E2 | 4.4E2 | 4.3E2 | 7.9E-1 | 8.7E0 | 5.3E3 | 1.6E3 | 337 | 12 | 337 | 12 | 0.62 |
| Qc | ng/ml | 2.1E2 | 7.0E2 | 4.5E2 | 6.9E2 | 6.0E2 | 5.1E2 | 1.0E-9 | 1.8E1 | 4.3E3 | 1.4E3 | 337 | 12 | 337 | 12 | 0.65 |
| Qd | ng/ml | 8.8E3 | 7.5E4 | 2.5E4 | 1.1E5 | 1.1E5 | 1.2E5 | 1.5E2 | 1.9E3 | 2.0E6 | 4.3E5 | 337 | 12 | 337 | 12 | 0.78 |
| Qe | ng/ml | 9.1E2 | 4.1E3 | 2.0E3 | 5.3E3 | 5.6E3 | 5.6E3 | 1.0E-9 | 5.7E1 | 9.7E4 | 1.8E4 | 337 | 12 | 337 | 12 | 0.67 |
| Jg | ng/ml | 4.6E2 | 1.8E3 | 7.8E2 | 2.1E3 | 9.5E2 | 1.9E3 | 5.8E0 | 4.5E1 | 1.0E4 | 7.1E3 | 340 | 12 | 340 | 12 | 0.73 |
| Jh | ng/ml | 2.9E0 | 3.3E1 | 2.2E1 | 6.0E1 | 8.6E1 | 8.2E1 | 1.0E-9 | 1.0E-9 | 1.2E3 | 2.9E2 | 340 | 12 | 340 | 12 | 0.74 |
| Ji | ng/ml | 5.7E1 | 3.1E2 | 9.0E1 | 3.0E2 | 1.1E2 | 2.4E2 | 1.1E0 | 2.3E1 | 1.3E3 | 6.9E2 | 340 | 12 | 340 | 12 | 0.76 |
| Jj | ng/ml | 5.3E2 | 1.4E2 | 1.9E3 | 3.7E2 | 1.8E4 | 4.0E2 | 2.3E0 | 8.7E0 | 3.4E5 | 1.0E3 | 340 | 12 | 340 | 12 | 0.31 |
| Jk | ng/ml | 2.6E0 | 5.4E1 | 2.0E1 | 7.1E1 | 4.8E1 | 7.8E1 | 1.0E-9 | 1.2E-1 | 3.9E2 | 2.4E2 | 340 | 12 | 340 | 12 | 0.72 |
| Jl | ng/ml | 4.8E-1 | 2.7E0 | 2.0E0 | 8.3E2 | 4.8E0 | 2.9E3 | 1.2E-3 | 2.5E-1 | 4.0E1 | 9.9E3 | 340 | 12 | 340 | 12 | 0.76 |
| Jm | ng/ml | 1.9E1 | 7.3E1 | 6.7E1 | 8.0E1 | 1.7E2 | 8.0E1 | 1.0E-9 | 4.0E-1 | 2.1E3 | 2.5E2 | 340 | 12 | 340 | 12 | 0.60 |
| Jn | pg/ml | 3.5E-1 | 1.5E0 | 7.3E0 | 2.2E1 | 6.2E1 | 6.8E1 | 1.0E-9 | 1.0E-9 | 7.3E2 | 2.4E2 | 340 | 12 | 340 | 12 | 0.71 |
| Jo | pg/ml | 3.8E3 | 5.1E3 | 5.1E3 | 8.9E3 | 6.6E3 | 1.0E4 | 2.0E1 | 2.4E1 | 1.0E5 | 3.6E4 | 340 | 12 | 340 | 12 | 0.59 |
| Jp | pg/ml | 7.1E4 | 1.1E5 | 7.4E4 | 1.2E5 | 4.0E4 | 3.8E4 | 5.8E2 | 6.7E4 | 3.8E5 | 1.9E5 | 340 | 12 | 340 | 12 | 0.80 |
| Jq | pg/ml | 9.6E1 | 2.6E2 | 2.0E2 | 4.5E2 | 5.4E2 | 4.8E2 | 1.0E0 | 1.3E1 | 8.7E3 | 1.7E3 | 340 | 12 | 340 | 12 | 0.74 |
| Jr | pg/ml | 4.4E0 | 3.0E1 | 9.0E1 | 2.4E2 | 7.6E2 | 7.0E2 | 1.0E-9 | 1.0E-9 | 1.1E4 | 2.4E3 | 340 | 12 | 340 | 12 | 0.77 |
| Js | pg/ml | 1.5E1 | 2.0E1 | 8.4E1 | 3.0E2 | 6.0E2 | 8.5E2 | 1.0E-9 | 2.7E0 | 1.0E4 | 3.0E3 | 340 | 12 | 340 | 12 | 0.66 |
| Jt | pg/ml | 2.4E3 | 4.7E3 | 3.1E3 | 1.0E4 | 3.5E3 | 1.3E4 | 2.2E1 | 1.5E2 | 5.2E4 | 4.1E4 | 340 | 12 | 340 | 12 | 0.70 |
| Lh | pg/ml | 1.3E4 | 3.5E4 | 2.3E4 | 7.5E4 | 4.2E4 | 1.2E5 | 1.0E-9 | 1.3E3 | 4.8E5 | 4.1E5 | 341 | 12 | 341 | 12 | 0.68 |
| Li | pg/ml | 3.5E3 | 3.0E4 | 2.0E4 | 9.0E4 | 9.1E4 | 1.3E5 | 1.2E1 | 3.7E1 | 1.3E6 | 4.1E5 | 341 | 12 | 341 | 12 | 0.67 |
| Lj | pg/ml | 3.0E3 | 9.7E3 | 2.1E4 | 2.4E4 | 5.9E4 | 3.8E4 | 1.0E-9 | 8.9E1 | 4.3E5 | 1.3E5 | 341 | 12 | 341 | 12 | 0.55 |
| Nv | pg/ml | 3.9E3 | 1.6E4 | 9.7E3 | 3.0E4 | 1.9E4 | 3.8E4 | 1.0E-9 | 1.6E2 | 1.6E5 | 1.2E5 | 342 | 12 | 342 | 12 | 0.78 |
| Nw | pg/ml | 9.6E3 | 2.7E4 | 1.4E4 | 3.3E4 | 2.2E4 | 2.5E4 | 1.9E2 | 4.5E3 | 2.2E5 | 7.8E4 | 342 | 12 | 342 | 12 | 0.78 |
| Nx | pg/ml | 2.2E2 | 9.3E2 | 4.3E2 | 9.1E2 | 6.3E2 | 8.0E2 | 1.0E-9 | 1.0E-9 | 4.1E3 | 2.3E3 | 342 | 12 | 342 | 12 | 0.68 |
| Ny | pg/ml | 6.5E0 | 4.2E1 | 1.1E2 | 1.3E2 | 1.3E3 | 1.9E2 | 1.0E-9 | 1.0E-9 | 2.5E4 | 6.1E2 | 342 | 12 | 342 | 12 | 0.77 |
| Oe | pg/ml | 2.9E1 | 1.0E-9 | 2.5E2 | 1.5E2 | 3.8E2 | 3.3E2 | 1.0E-9 | 1.0E-9 | 2.3E3 | 1.1E3 | 340 | 12 | 340 | 12 | 0.37 |
| Of | pg/ml | 1.3E2 | 1.7E2 | 5.1E3 | 3.4E3 | 2.1E4 | 7.6E3 | 1.0E-9 | 1.0E-9 | 1.9E5 | 2.4E4 | 342 | 12 | 342 | 12 | 0.55 |
| Og | pg/ml | 6.3E-2 | 7.3E-2 | 3.6E-1 | 7.8E-2 | 1.5E0 | 8.8E-2 | 1.0E-9 | 1.0E-9 | 1.9E1 | 3.2E-1 | 342 | 12 | 342 | 12 | 0.45 |
| Oh | pg/ml | 2.6E0 | 9.5E0 | 1.8E1 | 1.3E3 | 1.1E2 | 4.6E3 | 1.0E-9 | 1.0E-9 | 1.4E3 | 1.6E4 | 342 | 12 | 342 | 12 | 0.63 |
| Oi | pg/ml | 2.0E0 | 6.8E-1 | 5.0E0 | 3.9E0 | 7.9E0 | 5.6E0 | 1.0E-9 | 1.0E-9 | 6.7E1 | 1.6E1 | 342 | 12 | 342 | 12 | 0.45 |
| Ok | pg/ml | 3.9E2 | 1.5E3 | 5.4E2 | 2.0E3 | 6.5E2 | 2.1E3 | 1.5E1 | 5.3E1 | 7.8E3 | 7.0E3 | 342 | 12 | 342 | 12 | 0.73 |
| Om | pg/ml | 4.2E2 | 1.6E3 | 9.5E2 | 2.2E3 | 3.4E3 | 2.0E3 | 1.0E-9 | 7.0E1 | 5.1E4 | 5.6E3 | 342 | 12 | 342 | 12 | 0.76 |
| On | pg/ml | 1.8E2 | 9.6E2 | 3.0E2 | 1.7E3 | 4.4E2 | 2.4E3 | 1.0E-9 | 1.6E1 | 4.5E3 | 8.5E3 | 342 | 12 | 342 | 12 | 0.82 |
| Oy | pg/ml | 4.7E-1 | 1.4E0 | 6.1E0 | 6.2E0 | 3.1E1 | 1.0E1 | 1.0E-9 | 1.0E-9 | 4.0E2 | 3.3E1 | 341 | 12 | 341 | 12 | 0.56 |
| Oz | pg/ml | 7.0E-3 | 1.0E-9 | 3.3E-1 | 2.4E0 | 1.6E0 | 8.1E0 | 1.0E-9 | 1.0E-9 | 2.9E1 | 2.8E1 | 341 | 12 | 341 | 12 | 0.38 |
| Pa | pg/ml | 3.9E-1 | 6.7E-1 | 1.7E0 | 2.2E1 | 7.9E0 | 6.5E1 | 1.0E-9 | 1.0E-9 | 1.0E2 | 2.3E2 | 341 | 12 | 341 | 12 | 0.59 |
| Pb | pg/ml | 1.0E-9 | 1.0E-9 | 1.7E0 | 1.7E-1 | 2.6E1 | 5.5E-1 | 1.0E-9 | 1.0E-9 | 4.9E2 | 1.9E0 | 341 | 12 | 341 | 12 | 0.43 |
| Pc | pg/ml | 5.1E-2 | 1.0E-9 | 3.9E-1 | 3.1E1 | 9.0E-1 | 9.5E1 | 1.0E-9 | 1.0E-9 | 1.4E1 | 3.3E2 | 341 | 12 | 341 | 12 | 0.46 |
| Pd | pg/ml | 1.6E0 | 1.3E0 | 6.8E0 | 9.7E0 | 4.7E1 | 1.7E1 | 1.0E-9 | 1.0E-9 | 8.4E2 | 5.5E1 | 341 | 12 | 341 | 12 | 0.50 |
| Pe | pg/ml | 2.1E1 | 7.6E1 | 1.5E2 | 1.5E3 | 6.3E2 | 4.3E3 | 1.0E-9 | 1.1E0 | 6.7E3 | 1.5E4 | 341 | 12 | 341 | 12 | 0.72 |
| Pf | pg/ml | 1.6E0 | 1.6E1 | 1.6E1 | 3.2E1 | 9.3E1 | 4.4E1 | 1.0E-9 | 1.0E-9 | 1.5E3 | 1.5E2 | 341 | 12 | 341 | 12 | 0.72 |
| Pg | pg/ml | 3.9E0 | 4.9E1 | 7.6E1 | 3.1E2 | 5.2E2 | 4.6E2 | 1.0E-9 | 8.4E-1 | 7.7E3 | 1.3E3 | 341 | 12 | 341 | 12 | 0.75 |
| aA | mg/dL | 9.0E-1 | 1.2E0 | 1.0E0 | 1.9E0 | 5.4E-1 | 1.3E0 | 3.0E-1 | 5.5E-1 | 4.2E0 | 4.7E0 | 516 | 21 | 516 | 21 | 0.74 |
| aC | mg/mL | 2.2E0 | 3.8E0 | 2.6E0 | 3.5E0 | 1.3E0 | 2.2E0 | 7.5E-1 | 1.0E0 | 7.4E0 | 6.7E0 | 166 | 9 | 166 | 9 | 0.57 |
| aD | ug/mL | 3.0E0 | 3.2E0 | 4.7E0 | 3.5E0 | 4.8E0 | 1.8E0 | 7.5E-1 | 1.0E0 | 3.5E1 | 7.1E0 | 166 | 9 | 166 | 9 | 0.47 |
| aE | mg/mL | 5.7E-1 | 5.7E-1 | 5.9E-1 | 5.5E-1 | 1.7E-1 | 9.8E-2 | 1.8E-1 | 4.1E-1 | 1.2E0 | 6.9E-1 | 166 | 9 | 166 | 9 | 0.44 |
| aF | ng/mL | 2.2E0 | 3.8E0 | 5.0E0 | 6.1E0 | 7.8E0 | 5.6E0 | 4.3E-3 | 4.3E-3 | 5.0E1 | 1.5E1 | 166 | 9 | 166 | 9 | 0.60 |
| aG | mg/mL | 1.4E-1 | 9.0E-2 | 1.6E-1 | 9.6E-2 | 8.7E-2 | 2.4E-2 | 3.2E-2 | 6.9E-2 | 4.8E-1 | 1.5E-1 | 166 | 9 | 166 | 9 | 0.26 |
| aH | ug/mL | 7.2E1 | 5.6E1 | 7.8E1 | 6.1E1 | 4.1E1 | 2.0E1 | 8.9E0 | 3.2E1 | 2.0E2 | 1.0E2 | 166 | 9 | 166 | 9 | 0.41 |
| aI | ug/mL | 1.7E2 | 1.3E2 | 1.8E2 | 1.3E2 | 6.2E1 | 3.0E1 | 3.2E1 | 7.5E1 | 3.4E2 | 1.8E2 | 166 | 9 | 166 | 9 | 0.25 |
| aJ | ug/mL | 2.4E0 | 4.4E0 | 3.2E0 | 7.0E0 | 2.3E0 | 6.4E0 | 8.2E-1 | 2.2E0 | 1.4E1 | 2.3E1 | 166 | 9 | 166 | 9 | 0.79 |
| aK | ng/mL | 1.3E0 | 5.7E-1 | 2.0E0 | 1.7E0 | 2.0E0 | 2.1E0 | 2.9E-4 | 1.3E-1 | 1.0E1 | 6.5E0 | 166 | 9 | 166 | 9 | 0.42 |
| aL | mg/mL | 7.4E-1 | 4.9E-1 | 7.7E-1 | 5.8E-1 | 2.6E-1 | 2.2E-1 | 2.2E-1 | 3.2E-1 | 1.7E0 | 9.2E-1 | 166 | 9 | 166 | 9 | 0.28 |

Figure 29 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aM | U/mL | 1.8E1 | 4.7E1 | 3.9E1 | 1.5E2 | 7.8E1 | 2.3E2 | 4.2E-2 | 4.2E-2 | 8.2E2 | 6.8E2 | 166 | 9 | 166 | 9 | 0.73 |
| aN | U/mL | 1.4E1 | 2.3E1 | 2.6E1 | 2.5E1 | 4.3E1 | 2.5E1 | 2.5E-3 | 7.4E0 | 3.8E2 | 8.8E1 | 166 | 9 | 166 | 9 | 0.59 |
| aO | pg/mL | 5.3E1 | 1.8E2 | 4.2E2 | 8.4E2 | 9.9E2 | 9.2E2 | 6.0E-2 | 3.2E1 | 6.6E3 | 2.1E3 | 166 | 9 | 166 | 9 | 0.73 |
| aP | ng/mL | 1.6E0 | 4.3E0 | 2.2E0 | 6.5E0 | 2.4E0 | 8.3E0 | 4.5E-1 | 1.6E0 | 2.8E1 | 2.8E1 | 166 | 9 | 166 | 9 | 0.82 |
| aQ | ng/mL | 2.4E-1 | 2.5E-1 | 3.6E-1 | 3.4E-1 | 3.2E-1 | 2.5E-1 | 2.0E-4 | 5.2E-2 | 2.0E0 | 9.0E-1 | 166 | 9 | 166 | 9 | 0.52 |
| aR | ng/mL | 1.8E0 | 3.0E0 | 3.0E0 | 4.0E0 | 4.0E0 | 4.2E0 | 2.6E-1 | 5.6E-1 | 3.4E1 | 1.4E1 | 166 | 9 | 166 | 9 | 0.59 |
| aS | ng/mL | 3.7E-1 | 5.4E-1 | 1.0E0 | 9.1E-1 | 2.7E0 | 8.2E-1 | 4.2E-3 | 8.0E-2 | 3.3E1 | 2.6E0 | 166 | 9 | 166 | 9 | 0.61 |
| aU | pg/mL | 6.7E1 | 4.4E1 | 1.0E2 | 1.0E2 | 1.0E2 | 1.6E2 | 7.4E-2 | 7.4E-2 | 7.0E2 | 5.1E2 | 166 | 9 | 166 | 9 | 0.39 |
| aV | ng/mL | 6.0E-1 | 3.5E-1 | 1.1E0 | 5.9E-1 | 2.6E0 | 7.1E-1 | 7.6E-4 | 1.5E-1 | 3.3E1 | 2.4E0 | 166 | 9 | 166 | 9 | 0.38 |
| aW | pg/mL | 1.9E1 | 2.1E1 | 2.3E1 | 2.3E1 | 3.4E1 | 1.4E1 | 7.2E-2 | 7.2E-2 | 4.2E2 | 4.7E1 | 166 | 9 | 166 | 9 | 0.58 |
| aX | ng/mL | 7.5E0 | 3.5E1 | 1.3E1 | 7.7E1 | 2.0E1 | 9.9E1 | 3.0E-1 | 2.5E0 | 2.2E2 | 3.1E2 | 166 | 9 | 166 | 9 | 0.77 |
| aY | pg/mL | 5.3E1 | 6.6E1 | 7.4E1 | 1.1E2 | 1.1E2 | 1.2E2 | 4.1E-1 | 2.7E1 | 1.2E3 | 3.9E2 | 166 | 9 | 166 | 9 | 0.61 |
| aZ | pg/mL | 2.2E2 | 5.4E2 | 5.7E2 | 2.7E3 | 1.2E3 | 3.2E3 | 1.7E0 | 7.5E1 | 1.2E4 | 7.9E3 | 166 | 9 | 166 | 9 | 0.75 |
| bA | ng/mL | 1.3E1 | 1.2E2 | 6.4E1 | 2.8E2 | 1.4E2 | 4.6E2 | 3.0E-2 | 4.7E0 | 9.4E2 | 1.5E3 | 166 | 9 | 166 | 9 | 0.79 |
| bB | ng/mL | 2.8E2 | 1.7E2 | 3.1E2 | 2.0E2 | 1.8E2 | 9.0E1 | 2.1E0 | 7.6E1 | 9.5E2 | 3.8E2 | 166 | 9 | 166 | 9 | 0.32 |
| bC | ng/mL | 3.2E2 | 4.7E2 | 5.9E2 | 1.7E3 | 7.7E2 | 1.8E3 | 1.4E1 | 5.8E1 | 4.7E3 | 4.0E3 | 166 | 9 | 166 | 9 | 0.66 |
| bE | mg/mL | 5.2E0 | 5.1E0 | 5.5E0 | 6.3E0 | 2.1E0 | 3.5E0 | 1.3E0 | 2.6E0 | 1.2E1 | 1.2E1 | 166 | 9 | 166 | 9 | 0.51 |
| bF | pg/mL | 3.5E1 | 6.8E1 | 3.3E2 | 7.6E2 | 1.3E3 | 2.1E3 | 5.0E-2 | 1.4E1 | 1.1E4 | 6.3E3 | 166 | 9 | 166 | 9 | 0.68 |
| bG | ng/mL | 1.6E0 | 1.9E0 | 2.9E0 | 7.5E0 | 3.8E0 | 9.9E0 | 1.1E-1 | 1.6E-1 | 2.6E1 | 3.0E1 | 166 | 9 | 166 | 9 | 0.60 |
| bH | pg/mL | 5.7E-1 | 9.2E0 | 6.2E0 | 8.6E0 | 2.4E1 | 8.4E0 | 5.7E-1 | 5.7E-1 | 2.8E2 | 2.3E1 | 166 | 9 | 166 | 9 | 0.66 |
| bI | ng/mL | 4.0E-3 | 4.0E-3 | 9.5E-2 | 6.5E-2 | 2.0E-1 | 1.3E-1 | 4.0E-3 | 4.0E-3 | 9.8E-1 | 3.9E-1 | 166 | 9 | 166 | 9 | 0.49 |
| bJ | mg/mL | 1.9E0 | 2.2E0 | 2.4E0 | 2.7E0 | 2.0E0 | 2.4E0 | 2.5E-4 | 8.7E-1 | 1.1E1 | 8.9E0 | 166 | 9 | 166 | 9 | 0.55 |
| bL | pg/mL | 3.7E0 | 1.4E1 | 9.1E0 | 1.3E1 | 1.2E1 | 7.3E0 | 4.6E-2 | 3.2E0 | 6.0E1 | 2.4E1 | 166 | 9 | 166 | 9 | 0.72 |
| bM | mg/mL | 1.8E0 | 1.2E0 | 2.2E0 | 1.5E0 | 1.5E0 | 1.2E0 | 1.8E-2 | 1.6E-2 | 8.6E0 | 3.8E0 | 166 | 9 | 166 | 9 | 0.36 |
| bN | ng/mL | 3.4E1 | 2.4E1 | 1.2E2 | 5.5E1 | 2.9E2 | 7.6E1 | 1.4E-1 | 6.7E0 | 1.9E3 | 2.5E2 | 166 | 9 | 166 | 9 | 0.46 |
| bO | ng/mL | 4.0E-2 | 4.0E-2 | 9.6E0 | 4.0E-2 | 2.0E1 | 0.0E0 | 4.0E-2 | 4.0E-2 | 1.3E2 | 4.0E-2 | 166 | 9 | 166 | 9 | 0.33 |
| bP | mg/mL | 5.3E-1 | 4.9E-1 | 7.5E-1 | 6.2E-1 | 7.1E-1 | 4.7E-1 | 4.9E-2 | 9.2E-2 | 4.8E0 | 1.6E0 | 166 | 9 | 166 | 9 | 0.47 |
| bQ | pg/mL | 2.1E1 | 9.3E1 | 1.4E2 | 8.7E1 | 1.1E3 | 5.3E1 | 1.5E-1 | 2.2E1 | 1.3E4 | 1.6E2 | 166 | 9 | 166 | 9 | 0.79 |
| bR | ng/mL | 1.2E-2 | 1.2E-2 | 1.6E-1 | 8.3E-2 | 7.2E-1 | 1.4E-1 | 1.2E-2 | 1.2E-2 | 8.7E0 | 3.8E-1 | 166 | 9 | 166 | 9 | 0.46 |
| bS | ng/mL | 9.4E-1 | 9.4E-1 | 9.0E0 | 1.9E1 | 4.1E1 | 3.0E1 | 9.4E-1 | 9.4E-1 | 3.9E2 | 7.2E1 | 166 | 9 | 166 | 9 | 0.61 |
| bU | ng/mL | 7.8E-2 | 1.6E-1 | 1.9E-1 | 1.6E-1 | 5.4E-1 | 1.5E-1 | 1.3E-2 | 1.3E-2 | 6.6E0 | 4.1E-1 | 166 | 9 | 166 | 9 | 0.55 |
| bV | pg/mL | 4.8E2 | 6.6E2 | 6.2E2 | 8.5E2 | 9.0E2 | 5.5E2 | 1.6E2 | 5.1E2 | 1.2E4 | 2.2E3 | 166 | 9 | 166 | 9 | 0.74 |
| bW | pg/mL | 3.1E2 | 5.7E2 | 4.7E2 | 1.2E3 | 5.0E2 | 1.5E3 | 8.4E1 | 2.5E2 | 4.8E3 | 3.9E3 | 166 | 9 | 166 | 9 | 0.70 |
| bX | ng/mL | 2.5E-5 | 2.5E-5 | 2.6E-3 | 2.4E-3 | 3.2E-3 | 3.0E-3 | 2.5E-5 | 2.5E-5 | 1.3E-2 | 7.2E-3 | 166 | 9 | 166 | 9 | 0.49 |
| bZ | pg/mL | 2.7E2 | 1.8E3 | 1.8E3 | 6.8E3 | 6.5E3 | 1.4E4 | 1.5E-1 | 1.4E2 | 5.8E4 | 4.3E4 | 166 | 9 | 166 | 9 | 0.75 |
| cA | pg/mL | 6.0E-1 | 6.0E-1 | 4.1E0 | 3.6E0 | 2.9E1 | 6.9E0 | 6.0E-1 | 6.0E-1 | 3.7E2 | 2.1E1 | 166 | 9 | 166 | 9 | 0.55 |
| cB | ng/mL | 5.1E-2 | 1.7E-3 | 7.5E-2 | 6.2E-2 | 8.7E-2 | 1.0E-1 | 1.7E-3 | 1.7E-3 | 4.3E-1 | 2.6E-1 | 166 | 9 | 166 | 9 | 0.35 |
| cC | pg/mL | 4.3E1 | 3.5E1 | 4.6E1 | 3.3E1 | 5.1E1 | 2.4E1 | 1.0E0 | 4.0E0 | 4.5E2 | 6.7E1 | 166 | 9 | 166 | 9 | 0.41 |
| cD | pg/mL | 4.9E0 | 2.9E0 | 1.3E1 | 4.9E0 | 4.6E1 | 3.6E0 | 3.3E-1 | 8.8E-1 | 4.8E2 | 9.6E0 | 166 | 9 | 166 | 9 | 0.47 |
| cE | pg/mL | 6.0E1 | 1.5E2 | 2.7E2 | 2.6E2 | 6.0E2 | 3.8E2 | 1.2E-1 | 3.2E1 | 3.8E3 | 1.3E3 | 166 | 9 | 166 | 9 | 0.66 |
| cF | pg/mL | 2.5E0 | 5.3E-1 | 1.6E1 | 8.0E0 | 3.0E1 | 1.3E1 | 5.3E-1 | 5.3E-1 | 2.7E2 | 3.8E1 | 166 | 9 | 166 | 9 | 0.41 |
| cG | pg/mL | 5.3E1 | 2.2E2 | 1.7E2 | 3.1E2 | 8.2E2 | 3.2E2 | 7.8E0 | 4.0E1 | 1.0E4 | 1.1E3 | 166 | 9 | 166 | 9 | 0.81 |
| cH | uIU/mL | 3.2E0 | 5.7E0 | 7.4E0 | 1.3E1 | 1.7E1 | 1.8E1 | 8.6E-3 | 8.6E-3 | 1.6E2 | 5.3E1 | 166 | 9 | 166 | 9 | 0.57 |
| cI | ng/mL | 6.1E0 | 9.1E0 | 1.4E1 | 1.3E1 | 2.2E1 | 1.5E1 | 3.2E-2 | 1.1E0 | 1.2E2 | 4.1E1 | 166 | 9 | 166 | 9 | 0.50 |
| cJ | ug/mL | 6.8E1 | 3.1E1 | 1.0E2 | 4.1E1 | 1.0E2 | 4.9E1 | 6.9E0 | 5.6E0 | 6.4E2 | 1.7E2 | 166 | 9 | 166 | 9 | 0.28 |
| cK | ng/mL | 3.8E-3 | 3.8E-3 | 2.3E-2 | 3.1E-2 | 1.2E-1 | 6.8E-2 | 3.8E-3 | 3.8E-3 | 1.5E0 | 2.1E-1 | 166 | 9 | 166 | 9 | 0.55 |
| cL | pg/mL | 2.1E2 | 2.3E2 | 5.3E2 | 6.4E2 | 2.0E3 | 8.9E2 | 3.1E1 | 6.7E1 | 2.4E4 | 2.8E3 | 166 | 9 | 166 | 9 | 0.59 |
| cM | pg/mL | 2.7E2 | 2.5E2 | 2.9E2 | 2.4E2 | 1.7E2 | 6.4E1 | 2.5E1 | 1.2E2 | 1.1E3 | 3.1E2 | 166 | 9 | 166 | 9 | 0.41 |
| cN | pg/mL | 1.2E2 | 1.3E2 | 1.3E2 | 1.3E2 | 8.6E1 | 3.9E1 | 3.8E1 | 8.6E1 | 1.1E3 | 1.9E2 | 166 | 9 | 166 | 9 | 0.57 |
| cO | pg/mL | 2.1E2 | 4.4E2 | 4.0E2 | 5.5E2 | 1.5E3 | 4.2E2 | 5.4E1 | 9.6E1 | 1.9E4 | 1.5E3 | 166 | 9 | 166 | 9 | 0.75 |
| cP | ng/mL | 2.4E3 | 2.9E3 | 2.5E3 | 2.7E3 | 9.5E2 | 1.1E3 | 6.2E2 | 1.4E3 | 5.6E3 | 4.7E3 | 166 | 9 | 166 | 9 | 0.57 |
| cQ | ng/mL | 5.2E-2 | 9.1E-2 | 1.3E-1 | 1.6E-1 | 2.1E-1 | 1.7E-1 | 2.0E-3 | 2.0E-3 | 1.3E0 | 3.9E-1 | 166 | 9 | 166 | 9 | 0.57 |
| cR | ng/mL | 3.3E2 | 6.5E2 | 5.8E2 | 9.6E2 | 8.3E2 | 7.3E2 | 2.0E1 | 1.1E2 | 7.7E3 | 2.2E3 | 166 | 9 | 166 | 9 | 0.71 |
| cS | ng/mL | 2.8E2 | 1.2E3 | 4.1E2 | 1.8E3 | 4.2E2 | 2.2E3 | 4.1E1 | 1.4E2 | 2.5E3 | 7.1E3 | 166 | 9 | 166 | 9 | 0.78 |
| cT | ng/mL | 5.0E1 | 1.5E2 | 1.5E2 | 3.4E2 | 2.9E2 | 4.9E2 | 3.6E0 | 1.9E1 | 2.1E3 | 1.5E3 | 166 | 9 | 166 | 9 | 0.67 |
| cU | ng/mL | 5.8E1 | 2.2E2 | 9.3E1 | 2.1E2 | 1.5E2 | 9.5E1 | 6.2E0 | 9.8E1 | 1.6E3 | 3.9E2 | 166 | 9 | 166 | 9 | 0.90 |
| cV | ng/mL | 1.9E-1 | 1.9E-1 | 7.4E-1 | 5.1E-1 | 3.8E0 | 7.6E-1 | 2.5E-2 | 9.7E-2 | 4.7E1 | 2.5E0 | 166 | 9 | 166 | 9 | 0.58 |

Figure 29 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cW | mIU/mL | 4.8E-2 | 9.9E-2 | 8.8E-2 | 1.1E-1 | 3.5E-1 | 8.1E-2 | 4.8E-3 | 3.3E-2 | 4.5E0 | 2.9E-1 | 166 | 9 | 166 | 9 | 0.72 |
| cX | ng/mL | 1.3E-1 | 3.3E-2 | 1.9E0 | 1.1E-1 | 5.7E0 | 1.4E-1 | 2.3E-4 | 1.1E-2 | 2.8E1 | 4.1E-1 | 166 | 9 | 166 | 9 | 0.38 |
| cY | ng/mL | 7.6E0 | 3.3E0 | 1.1E1 | 8.5E0 | 1.1E1 | 1.1E1 | 1.7E-1 | 6.0E-1 | 6.1E1 | 3.6E1 | 166 | 9 | 166 | 9 | 0.38 |
| cZ | ug/mL | 1.3E1 | 1.1E1 | 1.5E1 | 1.4E1 | 6.8E0 | 7.8E0 | 2.3E0 | 7.0E0 | 4.6E1 | 3.0E1 | 166 | 9 | 166 | 9 | 0.41 |
| dA | pg/mL | 3.1E2 | 3.3E2 | 3.9E2 | 4.3E2 | 4.6E2 | 2.5E2 | 1.0E2 | 1.7E2 | 5.8E3 | 8.8E2 | 166 | 9 | 166 | 9 | 0.56 |
| dB | ug/mL | 1.8E1 | 2.0E1 | 1.8E1 | 2.1E1 | 2.0E1 | 5.3E0 | 2.1E0 | 1.5E1 | 2.5E2 | 2.8E1 | 166 | 9 | 166 | 9 | 0.63 |
| dC | nmol/L | 3.5E1 | 2.7E1 | 3.8E1 | 2.9E1 | 1.7E1 | 7.7E0 | 7.8E0 | 1.5E1 | 1.4E2 | 4.1E1 | 166 | 9 | 166 | 9 | 0.32 |
| dD | ug/mL | 3.4E1 | 2.9E1 | 3.5E1 | 3.0E1 | 1.1E1 | 7.1E0 | 1.4E1 | 2.2E1 | 7.4E1 | 4.3E1 | 166 | 9 | 166 | 9 | 0.32 |
| dE | ng/mL | 4.4E-1 | 9.8E-1 | 5.5E-1 | 1.1E0 | 5.7E-1 | 9.2E-1 | 8.4E-3 | 3.0E-1 | 2.7E0 | 2.9E0 | 166 | 9 | 166 | 9 | 0.71 |
| dF | ng/mL | 2.4E2 | 3.8E2 | 3.4E2 | 5.4E2 | 2.5E2 | 2.5E2 | 7.5E1 | 2.8E2 | 1.3E3 | 8.9E2 | 166 | 9 | 166 | 9 | 0.77 |
| dG | ng/mL | 1.2E1 | 1.6E1 | 1.7E1 | 2.4E1 | 1.9E1 | 1.9E1 | 3.0E0 | 6.7E0 | 1.8E2 | 6.5E1 | 166 | 9 | 166 | 9 | 0.67 |
| dH | pg/mL | 8.0E0 | 1.1E1 | 2.1E1 | 1.8E1 | 6.3E1 | 2.2E1 | 4.0E-2 | 8.3E-1 | 6.7E2 | 7.6E1 | 166 | 9 | 166 | 9 | 0.62 |
| dI | pg/mL | 4.6E-1 | 4.6E-1 | 3.8E0 | 4.4E0 | 2.6E1 | 6.2E0 | 4.6E-1 | 4.6E-1 | 3.3E2 | 1.9E1 | 166 | 9 | 166 | 9 | 0.63 |
| dJ | ng/mL | 2.0E0 | 2.2E0 | 2.2E0 | 2.2E0 | 1.1E0 | 1.2E0 | 3.2E-2 | 5.7E-1 | 5.6E0 | 4.0E0 | 166 | 9 | 166 | 9 | 0.52 |
| dK | uIU/mL | 1.3E0 | 5.8E-1 | 2.2E0 | 1.2E0 | 3.6E0 | 1.9E0 | 2.8E-4 | 1.4E-2 | 3.9E1 | 6.1E0 | 166 | 9 | 166 | 9 | 0.28 |
| dL | ng/mL | 8.7E2 | 8.4E2 | 1.1E3 | 1.2E3 | 6.3E2 | 6.1E2 | 2.8E2 | 5.8E2 | 4.8E3 | 2.3E3 | 166 | 9 | 166 | 9 | 0.56 |
| dM | pg/mL | 9.9E2 | 1.9E3 | 1.3E3 | 2.5E3 | 1.5E3 | 2.0E3 | 3.7E2 | 7.1E2 | 1.5E4 | 5.8E3 | 166 | 9 | 166 | 9 | 0.66 |
| dN | ug/mL | 9.9E1 | 1.4E2 | 1.0E2 | 1.3E2 | 4.4E1 | 3.6E1 | 2.4E1 | 6.6E1 | 3.3E2 | 1.7E2 | 166 | 9 | 166 | 9 | 0.69 |
| fR | ng/ml | 1.4E5 | 3.2E5 | 2.1E5 | 3.5E5 | 1.7E5 | 2.4E5 | 3.6E4 | 1.9E5 | 6.9E5 | 8.7E5 | 105 | 10 | 105 | 10 | 0.70 |
| nM | pg/ml | 1.0E-9 | 1.0E-9 | 1.0E-9 | 2.2E2 | 0.0E0 | 5.8E2 | 1.0E-9 | 1.0E-9 | 1.0E-9 | 1.5E3 | 69 | 7 | 69 | 7 | 0.57 |
| nN | pg/ml | 1.4E3 | 3.0E3 | 4.0E3 | 3.0E4 | 1.3E4 | 5.6E4 | 8.1E1 | 6.3E2 | 1.0E5 | 1.5E5 | 69 | 7 | 69 | 7 | 0.69 |
| nO | pg/ml | 2.4E1 | 4.3E1 | 3.7E1 | 5.1E1 | 4.6E1 | 4.3E1 | 4.0E0 | 9.7E0 | 3.1E2 | 1.4E2 | 69 | 7 | 69 | 7 | 0.67 |
| nR | pg/ml | 1.6E1 | 7.1E1 | 6.8E1 | 4.3E2 | 1.7E2 | 7.0E2 | 1.0E0 | 1.1E1 | 1.1E3 | 1.9E3 | 69 | 7 | 69 | 7 | 0.75 |
| nT | pg/ml | 7.3E1 | 1.1E2 | 1.0E2 | 2.8E2 | 9.8E1 | 3.3E2 | 1.0E-9 | 1.0E-9 | 6.4E2 | 9.2E2 | 69 | 7 | 69 | 7 | 0.61 |
| nU | pg/ml | 4.4E1 | 4.4E2 | 7.6E1 | 3.9E2 | 1.8E2 | 3.6E2 | 1.0E-9 | 1.0E-9 | 1.5E3 | 9.2E2 | 69 | 7 | 69 | 7 | 0.78 |
| lW | pg/ml | 1.0E-9 | 1.0E-9 | 1.1E1 | 6.4E0 | 3.0E1 | 1.4E1 | 1.0E-9 | 1.0E-9 | 1.7E2 | 3.9E1 | 69 | 7 | 69 | 7 | 0.48 |
| lX | pg/ml | 9.0E2 | 9.1E2 | 9.8E2 | 1.1E3 | 5.5E2 | 7.3E2 | 1.9E2 | 4.8E2 | 2.6E3 | 2.5E3 | 69 | 7 | 69 | 7 | 0.55 |
| lY | pg/ml | 1.9E1 | 1.4E1 | 2.0E1 | 2.0E1 | 1.7E1 | 1.5E1 | 1.0E-9 | 3.1E0 | 1.2E2 | 4.5E1 | 69 | 7 | 69 | 7 | 0.51 |
| mE | pg/ml | 1.0E-9 | 1.9E0 | 2.5E0 | 2.9E0 | 7.7E0 | 3.7E0 | 1.0E-9 | 1.0E-9 | 5.7E1 | 9.2E0 | 69 | 7 | 69 | 7 | 0.61 |
| mF | pg/ml | 2.7E-1 | 5.4E0 | 6.6E0 | 5.5E0 | 3.2E1 | 5.1E0 | 1.0E-9 | 1.0E-9 | 3.2E1 | 1.3E1 | 69 | 7 | 69 | 7 | 0.74 |
| mH | pg/ml | 3.0E0 | 3.3E0 | 5.5E0 | 3.6E0 | 8.2E0 | 2.3E0 | 4.0E-1 | 5.4E-1 | 5.3E1 | 6.5E0 | 69 | 7 | 69 | 7 | 0.49 |
| mI | pg/ml | 1.0E-9 | 3.4E0 | 1.2E1 | 8.4E1 | 2.6E1 | 1.7E2 | 1.0E-9 | 1.0E-9 | 1.8E2 | 4.6E2 | 69 | 7 | 69 | 7 | 0.65 |
| mM | pg/ml | 3.5E1 | 3.8E1 | 8.0E1 | 9.3E1 | 1.5E2 | 1.7E2 | 1.0E-9 | 1.0E-9 | 1.1E3 | 4.7E2 | 69 | 7 | 69 | 7 | 0.46 |
| mP | pg/ml | 1.5E1 | 1.6E1 | 1.7E1 | 1.5E2 | 1.6E1 | 2.9E2 | 1.0E-9 | 1.4E1 | 1.2E2 | 8.1E2 | 68 | 7 | 68 | 7 | 0.70 |
| mS | pg/ml | 1.6E3 | 1.6E3 | 1.7E3 | 2.0E3 | 1.0E3 | 1.0E3 | 1.0E-9 | 6.7E2 | 5.1E3 | 3.5E3 | 69 | 7 | 69 | 7 | 0.59 |
| mT | pg/ml | 5.7E1 | 5.6E1 | 1.2E2 | 4.2E2 | 2.2E2 | 6.6E2 | 1.0E1 | 1.6E1 | 1.4E3 | 1.7E3 | 68 | 7 | 68 | 7 | 0.58 |
| mU | pg/ml | 2.3E0 | 2.1E0 | 6.3E0 | 6.4E0 | 2.7E1 | 8.1E0 | 1.0E-9 | 6.1E-1 | 2.2E2 | 2.3E1 | 68 | 7 | 68 | 7 | 0.55 |
| mW | pg/ml | 2.1E3 | 3.8E3 | 2.3E3 | 5.2E3 | 1.2E3 | 4.5E3 | 1.0E-9 | 3.7E2 | 6.2E3 | 1.1E4 | 68 | 7 | 68 | 7 | 0.65 |
| mY | pg/ml | 6.5E2 | 6.5E2 | 8.5E2 | 2.0E3 | 9.4E2 | 2.8E3 | 1.0E-9 | 1.9E2 | 5.6E3 | 8.0E3 | 69 | 7 | 69 | 7 | 0.62 |
| mZ | pg/ml | 1.8E2 | 5.5E2 | 3.5E2 | 6.0E2 | 4.7E2 | 5.0E2 | 1.0E-9 | 6.6E1 | 3.1E3 | 1.4E3 | 68 | 7 | 68 | 7 | 0.68 |
| nA | pg/ml | 1.5E0 | 3.4E0 | 6.6E0 | 1.1E1 | 1.3E1 | 2.0E1 | 1.0E-9 | 1.0E-9 | 6.5E1 | 5.7E1 | 68 | 7 | 68 | 7 | 0.58 |
| nB | pg/ml | 2.9E2 | 3.0E2 | 3.1E2 | 3.8E2 | 1.6E2 | 2.8E2 | 3.0E1 | 1.3E2 | 8.2E2 | 9.6E2 | 69 | 7 | 69 | 7 | 0.54 |
| nC | pg/ml | 1.0E-9 | 7.0E2 | 9.4E3 | 4.1E3 | 5.3E4 | 7.4E3 | 1.0E-9 | 1.0E-9 | 3.8E5 | 2.0E4 | 69 | 7 | 69 | 7 | 0.72 |
| nD | pg/ml | 6.4E0 | 1.6E1 | 1.2E1 | 2.7E1 | 3.2E1 | 4.0E1 | 1.0E-9 | 1.0E-9 | 2.6E2 | 1.2E2 | 68 | 7 | 68 | 7 | 0.70 |
| nF | pg/ml | 1.0E-9 | 1.0E-9 | 2.5E0 | 8.6E0 | 1.2E1 | 1.8E1 | 1.0E-9 | 1.0E-9 | 9.3E1 | 4.7E1 | 69 | 7 | 69 | 7 | 0.60 |
| nH | pg/ml | 5.6E-1 | 1.1E1 | 1.9E2 | 6.3E1 | 1.2E3 | 1.2E2 | 1.0E-9 | 1.0E-9 | 1.0E4 | 3.3E2 | 68 | 7 | 68 | 7 | 0.71 |
| nI | pg/ml | 2.8E0 | 1.0E-9 | 5.5E1 | 2.0E2 | 7.5E1 | 4.5E2 | 1.0E-9 | 1.0E-9 | 3.5E2 | 1.2E3 | 69 | 7 | 69 | 7 | 0.48 |
| nJ | pg/ml | 1.7E-1 | 1.1E0 | 2.8E0 | 3.0E0 | 1.6E1 | 5.4E0 | 1.0E-9 | 1.0E-9 | 1.3E2 | 1.5E1 | 69 | 7 | 69 | 7 | 0.63 |
| nK | pg/ml | 1.0E-9 | 1.0E1 | 1.3E1 | 4.7E1 | 2.3E1 | 8.1E1 | 1.0E-9 | 1.0E-9 | 1.0E2 | 2.2E2 | 68 | 7 | 68 | 7 | 0.64 |
| nL | pg/ml | 1.0E-9 | 1.5E1 | 2.8E2 | 1.8E2 | 1.7E3 | 3.3E2 | 1.0E-9 | 1.0E-9 | 1.4E4 | 9.0E2 | 69 | 7 | 69 | 7 | 0.64 |
| kC | pg/ml | 9.6E1 | 1.1E2 | 1.9E2 | 1.3E2 | 3.6E2 | 7.9E1 | 2.1E1 | 5.9E1 | 2.7E3 | 2.9E2 | 69 | 7 | 69 | 7 | 0.53 |
| kE | pg/ml | 1.4E5 | 1.4E5 | 1.4E5 | 1.4E5 | 4.1E4 | 2.5E4 | 3.8E4 | 1.1E5 | 2.7E5 | 1.9E5 | 69 | 7 | 69 | 7 | 0.49 |
| kF | pg/mL | 6.2E1 | 7.6E1 | 6.7E1 | 8.7E1 | 2.3E1 | 3.7E1 | 2.7E1 | 5.2E1 | 1.5E2 | 1.4E2 | 69 | 7 | 69 | 7 | 0.67 |
| kG | pg/mL | 8.4E3 | 1.6E4 | 1.1E4 | 4.3E4 | 9.6E3 | 5.6E4 | 1.1E3 | 3.3E3 | 5.8E4 | 1.6E5 | 69 | 7 | 69 | 7 | 0.69 |
| kI | pg/ml | 2.0E2 | 1.5E2 | 2.2E2 | 1.9E2 | 1.2E2 | 9.4E1 | 1.0E-9 | 7.2E1 | 6.7E2 | 3.4E2 | 69 | 7 | 69 | 7 | 0.44 |
| kK | pg/ml | 1.2E2 | 1.1E2 | 1.8E2 | 1.8E2 | 2.6E2 | 1.7E2 | 6.4E0 | 3.4E1 | 1.9E3 | 5.5E2 | 69 | 7 | 69 | 7 | 0.53 |
| kN | pg/ml | 1.1E3 | 1.1E3 | 1.5E3 | 2.1E3 | 1.6E3 | 2.9E3 | 7.3E1 | 7.0E2 | 1.0E4 | 8.7E3 | 69 | 7 | 69 | 7 | 0.51 |

Figure 29 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| kO | pg/ml | 7.1E3 | 6.2E3 | 9.6E3 | 8.0E3 | 1.7E4 | 3.4E3 | 3.7E3 | 5.0E3 | 1.5E5 | 1.4E4 | 69 | 7 | 69 | 7 | 0.52 |
| kP | pg/ml | 5.8E3 | 4.9E3 | 6.8E3 | 5.9E3 | 4.3E3 | 4.5E3 | 9.6E2 | 1.6E3 | 2.7E4 | 1.5E4 | 69 | 7 | 69 | 7 | 0.42 |
| oO | pg/ml | 8.8E4 | 8.9E4 | 1.0E5 | 1.6E5 | 6.2E4 | 1.5E5 | 3.3E3 | 3.8E4 | 3.0E5 | 4.0E5 | 62 | 7 | 62 | 7 | 0.54 |
| oP | pg/ml | 1.3E5 | 2.0E5 | 1.5E5 | 2.3E5 | 8.8E5 | 1.8E5 | 2.4E4 | 5.0E4 | 4.2E5 | 5.7E5 | 62 | 7 | 62 | 7 | 0.65 |
| oQ | pg/ml | 3.0E3 | 4.0E3 | 3.6E3 | 9.9E3 | 3.0E3 | 1.1E4 | 7.7E2 | 2.0E3 | 2.1E4 | 3.2E4 | 62 | 7 | 62 | 7 | 0.67 |

Analyte panel data:

Unconstrained panels with 3 analytes, where 1.0E-8 >= 'model p-value' > 0. Contains 2 panels of 625,624 total panels evaluated. : MlQdOk aPcUdH Unconstrained panels with 3 analytes, where 1.0E-7 >= 'model p-value' > 1.0E-8. Contains 88 panels of 625,624 total panels evaluated. : Ml{Mi(Is Ji Jj Jp Jt Lv Mz Nj Nn Ok Pc Qa Qd) Qd(Fr Hv Jg Ji Jp Lv Ma Mm Nn On Pc) On(Jj Ng Ns Oe Of Og Oy Pb) Ji(Hv In Iv Lv Ma Mj Qa) Ok(In Lv Ma Nn Qa) Ma(Is Iv Jt) Lv(Is Jt) Lwls} Mi{fR(In Jp Li Nq Og Pd) Pc(Jp Lv Nf Nj Oi) Nn(Nf Oi) MaNj} On{Pb(Lv Lz Nf Nj No) Lv(Nf Nm Of) Mg(Nf Ng) NnOi LzOf NfOe} cU{dH(aA aJ aX cS)} Cx{Cu(aX cS) aZcS} Nn{NfOk QdOi} ImQdPc aAaXcX Unconstrained panels with 3 analytes, where 1.0E-6 >= 'model p-value' > 1.0E-7. Contains 1,172 panels of 625,624 total panels evaluated. : Mi{Pc(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jq Jr Js Jt Lh Li Lj Lu Lw Lx Ly Lz Ma Mb Mc Md Me Mf Mg Mh Mj Mk Mm Mn Mp Mq Mr Ms Mt Mu Mv Mw Mx My Mz Na Nb Nc Nd Ne Ng Nh Ni Nk Nl Nm Nn No Nq Nr Ns Nt Nu Nv Nw Nx Ny Oe Of Og Oh Ok Om On Oy Oz Pa Pb Pd Pe Pf Pg Po Pz Qa Qb Qc Qd Qe) Ml(aA Et FR Hq Hr Hu Hv Hx li Ij Il Im In Io Ir Iu Iv Jg Jh Jk Jl Jn Jo Jq Jr Js Li Lw Lx Ly Lz Ma Mb Me Mf Mg Mh Mj Mk Mm Mr Ms Mu Mv Mw Mx Nb Nd Ne Nf Ng Nh Nk Nm Nr Ns Nt Nu Nw Ny Oe Of Og Oh Om On Oy Oz Pb Pd Pe Pf Pg Po Qc) Nj(aA Fp Fr Hq Hr Hv Ih Ii Ij Ik Il Im In Io Is It Iu Iv Jg Jj Jk Jl Jn Jo Jp Jr Jt Lj Lv Lw Lx Ly Lz Md Mg Mh Mm Mp Mq Ms Mt Mu Mx Mz Nb Nc Nd Ne Nf Ng Nh Nk Nm Nn Nq Ns Nt Nu Nw Ny Oe Of Og Oh Ok Om On Oy Oz Pb Pd Pf Pg Pz Qd) Lv(Fp FR Hq Hr Hx Ih Ij Ik Il Im In Is Iu Jg Jj Jl Jo Jp Lw Lx Ly Lz Ma Md Mm Mr Mx Mz Nd Ne Nf Ng Nh Nk Nm Nn Oe Of Og Oh Ok On Oy Oz Pb Pd Pf Qd) fR(Fr Hr Hv Hx Ii Ij Il Ir It Ji Jj Jn Jo Jq Jr Jt Lj Lu Lw Ma Mb Md Mm Mq Mv Mz Na Nf Nm Ny Oh Om Pb Qa) Nf(Fr Hx Ij Il Im In Is Jg Ji Jk Jl Jp Jt Lw Ma Mg Mm Ms Mu Mv Mw Mz Nb Nq Nw Ok Om On Oz) Nn(Hq Il Im Iq Jj Jo Jp Lj Ma Md Mt Mx Mz Ok Pd Pf) Jp(Hq Im Lw Lz Ma Mm Mx Nm Of Pb Pd Pf Pz) Jg(Hq Lx Ma Md My Ng Of Og Oy Pb Pd Po) Ma(Hq Jj Jo Lw Ng Nk Ok On Pd Pf) Il(Hq Jj Lx Ly Ng Of Pb Pd Po) Pb(Jl Jt Lw Mw Ok On Oz) Of(Jk Lw Mw Ok On) Hq(Fr Jk Mm Pg) Hr(Jl Jt Ok On) Pd(Fr Lw Mg Mm) Md(Jt Lw Ok) Jl(Mx Pc Po) Ok(Jq Mz) On(Nm Po) MwOy NgJk} On{Nf(Fr Hq Hr Hu Hv Hx Ij Il Im In Ir Is It Iu Iv Jg Ji Jj Jk Jn Jo Jp Jr Js Jt Li Lw Lx Ly Lz Ma Mb Md Me Mf Mh Mj Mk Ml Mm Ms Mv Mx My Mz Nd Ne Ng Nh Nj Nk Nl Nm Nn No Nq Ns Nt Nu Nv Nx Of Og Oh Oi Ok Om Oy Oz Pa Pc Pd Pf Pg Po Pz Qa Qd) Pb(aA Hr Hv Ih Ij Il Im In Iq Iu Jg Jj Jk Jn Jo Jp Jq Jr Jt Li Lj Lw Ma Me Mf Mg Mh Mm Mt Mu Mw Mx Mz Nc Nk Nm Nn Nu Nv Nw Oe Og Oi Ok Om Pc Pf Pg Po Qa Qd) Lv(Hr Hu Im Iu Jj Jo Lw Ly Ma Md Ml Mm My Ng Nj Nn Oe Og Oi Oy Oz Pc Pf Po Pz Qd) Of(Hr Il Iq Jg Jk Jp Lj Lw Ma Me Mg Mh Mm Mt Mx Mz Nj Nm No Nw Oe Oi Pc Pf) Hr(Hv In Jj Jt Lw Ma Md My Ng Nj Nm Ns Oe Og Oi Ok Oy Qd) Ml(Hu Is Ji Jt Lw Ma Md My Mz Nj Nm Oi Ok Qa) Nj(Im Jj Lw Ma My Ng Nm Oe Og Oi Oy Po Qd) Nm(Jj Lw Ma Mm My Ng Oe Og Oy Pc Qd) Ma(Jj Jo Lw My Ng Oe Og Oi Oy Qd) Lz(My Ng Oe Og Oy Qd) Qd(Im Oe Pc Po Pz) Oe(Jj Md Mm Po) Oy(Mg Mh Mz No) No(My Ng) Md(Lw Oi) PoLi MgOg MhJj MzNg OiPc} Ml{Qd(aA Et Hr Hw Hx Ii Il Im In Ir Is It Iu Iv Jj Jk Jl Jo Jr Jt Lh Lw Lx Md Me Mf Mg Mh Mj Mk Mn Mp Mr Ms Mv Mw Mz Nb Nd Ni Nj Nk Nm Nq Nr Nt Nu Nw Nx Oe Og Om Oz Pa Pe Pf Pg Po Pz Qa) Ji(Fr Hu Hw Hx Ii Ij Il Ir Is Iu Jg Jj Jk Jl Jn Jo Jp Jr Js Jt Lx Me Mf Mg Mh Mk Mm Mp Mr Ms Mu Mv My Mz Nb Ne Nh Nj Nk Nl Nm Nn Nq Nr Nt Nu Oe Ok Om Oz Pa Pc Pe Pg Po) Ok(Fr Hv Ij Il Ir Is Iv Jj Jk Jl Jp Js Jt Lw Mf Mg Mj Mk Mp Mv Mz Nb Ne Nj Nq Ns Oe Oz Pc Pg) Jt(Fr Hv Im In Is Jj Jl Jo Jp Mz Ng Nn Oe Pc Qa) Is(Fr Jp Mg Mm Mz Nn Oe Oz Pc) Lv(Ir Iv Jl Ma Mj Mz Nb Qa) Qa(Jj Lw Ma Mm Nn Oe Pc) Ma(Jl Mj Mz Nb) Lw(Hv Iv Mj) Nnlv} Lv{Ok(Hr Hw Ij In Jo Md Mm Nf Nn Of Om Pb Pc) Nn(Il Im Is Jj Jl Jp Mz Oi Pc Qd) Mm(Il Is Jj Jl Mz Ng Qd) Pc(aA Im Is Jl Jp Mz Qd) Qd(Ik Il Im Lw Oz) Jj(Fr Il Is Jk Jl) Lw(Il Jl Jp) Ji(Im Pb) NfJi NgJg Islu} Ok{Pc(Hr Hw Il Jp Jq Ma Md Nf Of Om Pb Qd) Pb(Jk Jl Jt Mw Nb Nn Oz Pg Qa) Nn(Hr Jq Ma Md Mz Nj Oi) Nf(Ji Jt Mg Mp Nq Qa Qd) Of(Jk Mw Nq) Hr(Il Jl) MdMp} aX{Cx(al Bn cJ Cp Cq cU Dc) cK(Ax Bg Cu Dc Di Dk Fr) cJ(Ax Bg Cu Dc Dk Fr) dH(aA al aL cZ) cX(aO CU) Dd(aI aL) AxcB CqaL} Qd{Pc(Ik Il Iu Jl Jp Lj Ma Nj Nm Oi Pf Pz Qc) Im(Fr Jg Jp Lw Ma Mm Nn Oz) Mm(Ik Il Nm Pz) Il(Jj Lw Nn) Ma(Ik Lw)} cU{dH(aG aL BA bL bM bW dE FR) Fr(As aV bQ cE) bR(bS bW cS) As(Aw Cp) aA(cX dA) cS(bM cB) aGcN aJdG} Jl{Lw(Hr Ma Pb) Ji(Hr Nf Pb) Nn(Im Oi) Mg(Jj Ng) MaJj MwPb HrJt ImPc} Nf{Ji(Fr Hv Il Jk Jp Jt Ma Mv Nn) FrJt} cJ{Cu(As Cq Cx) Cx(aA aZ) FraZ} Nn{Oi(Is Jp Mz Nw) IlJj} Ma{LwJp NjaA JjJk JoJt} Mg{Ng(Jg Jk Jp)} Pc{IlJj ImJp IsOi} cS{AxcB CxaL aAcX} Jt{FrHr JiJq} CuCxdH LwIlJj aAbCcX Unconstrained panels with 3 analytes, where 1.0E-5 >= 'model p-value' > 1.0E-6. Contains 9,205 panels of 625,624 total panels evaluated. : Mi{Mm(aA Et Fp Fr Hr Hu Hv Hw Hx Ih Ii Ij Ik Il Im In Io Ip Iq Ir Is It Iu Iv Jg Jh Ji Jj Jk Jl Jm Jn Jo Jq Jr Js Jt Lh Li Lj Lu Lw Lx Ly Lz Ma Mb Mc Md Me Mf Mg Mh Mj Mk Mn Mp Mq Mr Ms Mt Mu Mv Mw Mx My Mz Na Nb Nc Nd Ne Ng Nh Ni Nk Nl Nm Nn No Nq Nr Ns Nt Nu Nv Nw Nx Ny Oe Of Og Oh Oi Ok Om On Oy Oz Pa Pb Pe Pf Pg Po Pz Qa Qb Qc Qd Qe) On(aA Et Fp FR Hq Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Mb Mc Md Me Mf Mg Mh Mj Mk Mn Mp Mq Mr Ms Mt Mu Mv Mw Mx My Mz Na Nb Nc Nd Ne Ng Nh Ni Nk Nl Nn No Nq Nr Ns Nt Nu Nv Nw Nx Ny Oe Og Oh Oi Ok Om Oy Oz Pa Pd Pe Pf Pg Pz Qa Qb Qc Qd Qe) Lw(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jq Jr Js Jt Lh Li Lj Lu Lx Ly Lz Mb Mc Me Mf Mg Mh Mj Mk Mn Mp Mq Mr Ms Mt Mu Mv Mw Mx My Mz Na Nb Nc Nd Ne Ng Nh Ni Nk Nl Nm Nn No Nq Nr Ns Nt Nu Nv Nw Nx Ny Oe Og Oh Oi Ok Om Oy Oz Pa Pe Pf Pg Po Pz Qa Qb Qc Qd Qe) Hq(aA Et Fp fR Hr Hu Hv Hw Hx Ih Ii Ij Ik Im In Io Ip Iq Ir Is It Iu Iv Jh Ji Jj Jl Jm Jn Jo Jq Jr Js Jt Lh Li Lj Lu Lx Ly Lz Mb Mc Md Me Mf Mg Mh Mj Mk Mn Mp Mq Mr Ms Mt Mu Mv Mw Mx My Mz Na Nb Nc Nd Ne Nf Ng Nh Ni Nk Nl Nm No Nq Nr Ns Nt Nu Nv Nw Nx Ny Oe Of Og Oh Oi Ok Om Oy Oz Pa Pb Pd Pe Pf Po Pz Qa Qb Qc Qd Qe) Jj(Et Fp Fr Hr Hu Hv Hw Hx Ih Ii Ij Ik Im In Ip Iq Ir Is It Iu Iv Jg Jh Ji Jk Jl Jm Jn Jo Jp Jq Jr Js Jt Lh Li Lj Lu Lx Ly Lz Mb Mc Md Me Mf Mg Mh Mj Mk Mn Mp Mq Mr Ms Mt Mu Mv Mw Mx My Mz Na Nb Nc Nd Ne Nf Ng Nh Ni Nk Nl Nm No Nq Nr Ns Nt Nu Nv Nw Nx Ny Oe Of Og Oh Oi Ok Om Oy Oz Pa Pb Pd Pe Pf Pg Po Qc Qd Qe) Pd(aA Et Fp Fr Hu Hv Hw Hx Ih Ii Ij Ik Im In Io Ip

Oi Pa) Ng(Jg Jk Mg) Jj(Jk Nt Pg) aA(Il Mg Nj) Og(Il Jg) NjPa Hvlm} Nn{Oi(aA Et Fr Hu Hv Hx Ij Il Im Ir Iv Jg Jk Jq Jr Jt Lx Ma Mr Nb Nj Nr Nt Nu Nv Om Pa Pe Pg Po Qa) Jp(Hv Il Im Is Iu Jj Jr Ma Me Mm Mr Mt Mx Mz Nf Ng Nj Nm Nr Nt Oe Oy Pa Pe) Im(Hv Il Is Jt Ma Mr Mz Nb Nf Nj Nk Nr Oz Pa Pe Pg) Is(Iu Jj Jr Ma Mh Nf Nj Nm Oe Og) Nj(aA Il Ma Mz Nr Nt Pa Pe) Nf(Il Jt Mz Nw Om Qa) Jj(Ij Jk Ma Mz Nt Pg) Jt(Hr Hw Jq Md Pb) Ma(Mr Mz Pa Pc) Mz(Mt Mx) NgJg IlOg} Jt{Ma(Hr Hv Hw Ij Im In Jj Jp Jq Md Na Nf Ni Nj Of Pb) Im(Hr Hv Hw Ij In Jo Jp Jq Md Na Nf Nj Ny Pb) Fr(Hw Ij In Jo Jq Md Na Nj Ny Of Om Pb) Nf(Jj Jo Jp Mv Mz Nq Nw Oe Om Oz Pg Qa) Pb(Jg Jj Jo Jp Mw Mz Om Pg) Md(Jj Jo Jp Mp Mz Pg) Hr(Hx Jj Jp Mz Pg) Jj(Hw Il Jq Na) Jo(Hw Jq Na) Mz(Jq Na) MwOf HwJp} Jj{Pg(Fr Hq Hv Il Im Is Iu Jg Jk Jp Ma Md Mg Mm Ms Mz Nf Nj Nk Nl Nt Nu Oe Of Oz Pb Pd Pf) Il(Fr Is Jk Jp Ma Mg Mm Mp Mv Mz Nt Nx) Ma(Hx Ir Is Iu Jg Jp Mz Nl Nt Nv) Jk(Is Jp Mg Mp Nj Nt Nu Oe) Nt(Is Jp Mg Nj Oe) Mg(Is Jp Mz) Fr(Is Nj) Nqls MmPe MpJp} Cx{Cu(aA aG As aU aV Aw aZ Ba bE bO bQ cB cC cD cF cK Cw dB dC DE Dg Di dJ dK FR) aZ(al aJ aP bC bL bW bZ Cq De Fr) aA(Af aU Aw bC cB Cw De) cJ(aP bA Dc De Fr) aP(cB dG dH) DdFr DefR DkdK aUbA cEcG} Fr{aZ(Al As aV Bn bO cE cN Cv cX dC dK) Is(Iu Mh Nf Ng Nj Nm Oe Of Oy) Nj(aA fR Im Ma Mp Mz Oe) cJ(Aj bC Bn cE) Cu(An As Bn) Dd(An As Bn) Nf(Hv Mz Qa) Ng(Jg Mg) MpHq NbPb IjOf aPdH bCcK} Is{Ma(Iu Jp Mh Mm Nj Nm Oe) Mm(Jp Mh Nj Nm Oe Pz) Mg(Iu Jp Ng Oe Og) Jp(Mp Nm Oe) Jg(Ng Og) fR(Ii Mx) MpNj MwOg} Ng{Jg(Hx Il Iu Jk Ma Mp Mz Nq Nt Pg) Mg(aA Il Mw Mz Nw Pa Pg) Mm(Pe Pg)} Jp{Mp(Hq Im Ma Md Nd Nj Nm) Im(Ma Mg Nj Oh Wm) Ma(aA Mm Nj) Nm(Mm Nt) WmMd NbPb} Mz{Ma(aA Im Iu Mm Nf Nj Nk Nl) Mm(Nm Oe) Mp(Hq Nj) Nf(Mg Nq) NjaA JgOg} Cu{cJ(Ad An bJ Bn Cw Dc dE) As(cK De dH) Bn(Aw De) Dc(cK dH) cXdE} aA{cX(aU aZ bO cB cG cJ dC dE) Nj(Mg Mp) bCcB cJdE nUmU nIkG} aP{dH(aI bF bG bM bQ bZ cB cG cO) dG(aI aL cB cX)} Pb{Nb(Im Jg Ma Mw Nj Om) Mw(Hu Oz)} aZ{cJ(Al Ax Bg Di Dk) DkdK bOcX} Mm{Pg(Jo Oy) NfQa PePf} Dk{dK(Af As Bn)} Mp{NjIm HqIl JgOi} De{AsAx BnbA} Jg{Og(Hx Il)} nU{mU(mW oQ)} MaNkNw MgNfQa cEcGcX Unconstrained panels with 2 analytes, where 1.0E-6 >= 'model p-value' > 0. Contains 12 panels of 16,069 total panels evaluated. : Mi(fR Lv Ma Ml Nf Nj Nn Pc) Ml(Ji Qd) On(Nf Pb)

Unconstrained panels with 2 analytes, where 1.0E-5 >= 'model p-value' > 1.0E-6. Contains 183 panels of 16,069 total panels evaluated. : Mi(aA Et Fp Fr Hq Hr Hu Hv Hw Hx Ih Ii Ij Ik Il Im In Ip Iq Ir Is It Iu Iv Jg Ji Jj Jk Jl Jn Jo Jp Jq Jr Jt Li Lj Lu Lw Lx Ly Lz Mb Md Me Mf Mg Mh Mk Mm Mn Mp Mq Mr Ms Mt Mu Mv Mx My Mz Nb Nd Ne Ng Nh Nk Nl Nm No Nq Ns Nt Nu Nv Nw Nx Ny Oe Of Og Oh Oi Ok Om On Oy Oz Pb Pd Pf Pg Po Pz Qd Qe) On(Hr Jj Lv Lw Ma Md Ml Mm My Ng Nj Nm Nn Oe Of Og Oi Oy Pc Po Pz Qd) Lv(aA Fr Is Ji Jj Jl Jp Lw Mm Mz Nn Ok Pc Qd) Ok(Hr Hw Ma Ml Mp Nf Nn Pb Pc Qd) Qd(Fr Il Im Lw Ma Mm Nn Pc) aX(CU CX Dc Fr) Lw(Fr Is Jl Jp Ma) cU(aA aG cS dE dH) Pc(Is Jl Jp Mz) Fr(aA aZ cS) Ml(Is Jt Qa) Cx(cS Cu) Jj(Jl Pg) DkcS NnJp NfJi Unconstrained panels with 2 analytes, where 1.0E-4 >= 'model p-value' > 1.0E-5. Contains 633 panels of 16,069 total panels evaluated. : On(aA Et Fp FR Hq Hu Hv Hw Hx Ih Ii Ij Ik Il Im In Io Ip Iq Ir Is It Iu Iv Jg Jh Ji Jk Jl Jm Jn Jo Jp Jq Jr Js Jt Lh Li Lj Lu Lx Ly Lz Mb Mc Me Mf Mg Mh Mj Mk Mn Mp Mq Mr Ms Mt Mu Mv Mw Mx Mz Na Nb Nc Nd Ne Nh Ni Nk Nl No Nq Nr Ns Nt Nu Nv Nw Nx Ny Oh Ok Om Oz Pa Pd Pe Pf Pg Qa Qb Qc Qe) Qd(aA Et fR Hr Hv Hx Ik Is It Iu Jg Ji Jj Jk Jl Jp Jt Lh Lj Lz Mg Mp Mr Mu Mv Mw Mz Nb Nd Nj Nk Nl Nm Nq Nr Nt Nu Nv Nw Oe Og Oh Oi Om Oz Pa Pe Pf Pg Pz Qb Qc) Fr(As aV bC Bn cJ CU CX dC dK fR Hv Im Ir Is Iu Iv Ji Jj Jl Jp Jq Jr Jt Ma Me Mg Ml Mm Mp Mz Nf Ng Nj Nk Nl Nm Nn Nt Oe Of Oh Ok Oy Oz Pc) Lv(Et Hv Hx Ij Il Im Iq Ir Iu Jg Jk Jq Jt Lx Ly Ma Mg Ml Mn Mp Mr Mu Mv My Nb Nd Nj Nk Nl Nm No Nq Nr Nt Nu Nv Nw Ny Oe Oh Om Oz Pa Pc Pg Po Qa) cS(aA Af aI Aj AL An Ar As Aw Ax aZ BA BB Bc BG bM BN BO bP bR bZ cB cF Ch cJ Cp Cq Ct Cu cX dB Dc DD DE dF dH Di Dl dM) Ok(Hv Ij Il In Is Iu Iv Jg Ji Jj Jk Jl Jn Jo Jp Jq Jr Lw Lx Md Mg Mk Mm Mv Mz Na Ni Nj Nk Nl Nq Nt Nu Nw Ny Og Oh Om Oz Pd Pg Po) Lw(aA Hv Hx Il Im Ir Iu Iv Ji Jk Mg Mj Mm Mr Mz Nb Nj Nk Nl Nn Nq Nr Nt Nu Nw Pa Pc Pe Pg Po) aX(aA aI AL An aO Ar Aw Ax BA Bb BG BO Ch cJ Co Cp Cq Cs Cw Dd De dF dH Di Dk) Ji(Hr Hv Hw Ij Il In Is Iu Jj Jk Jl Jn Jp Jq Ma Md Mm Mp Mz Nj Nk Nm Nn Oe Om Pb Pc) cU(aC aJ aP As aV aZ BA bJ bM bO bQ bR bU cB cC cD cE cJ cL cN CX Di dK fR) Nn(Hv Hx Il Im Ir Is Iv Jj Jl Jt Lx Ma Mr Mz Nj Nr Nt Nw Oi Om Pa Pc Pe Pg Po) Pc(aA Et Hv Hx Il Im Ir Iv Jt Lx Ma Mr Nj Nr Nt Nw Om Pa Pe Pg Po Qa) Jl(Hr Im Is Iu Jg Jo Jp Jt Ma Mg Ml Mm Mp Mz Nj Nm Oe Og Oh Oz Pb) Mi(Io Jh Jm Js Lh Mc Mj Mw Na Nc Ni Nr Pa Pe Qa Qb Qc) Mm(aA Hv Ij Il Ir Is Jp Jr Jt Ma Mz Nr Nt Nw Pe Pg) Is(Im Iu Jj Jp Ma Mg Mp Mz Nj Nt Oe Og Oh Pg) Jt(Hr Hw Ij Im In Jo Jp Jq Ma Md Na Nf Pb) Mz(Im Iu Jg Jj Jp Ma Mg Ml Mp Nj Nq) Jp(Im Iu Ma Mg Mp Nj Nt Oh Pg) aA(cB cJ CX kG Ma Mg Nj) Cu(An As Bn cJ cX dE dK) Jj(Il Jk Ma Mg Nt Nv Po) aP(cB CX dH) Ma(Ml Nw) Mp(Nj Nw) Jg(Ng Og) aZ(bO Cx) DkdK NtNj MjMl NbPb ImPg nUmU Unconstrained panels with 2 analytes, where 1.0E-3 >= 'model p-value' > 1.0E-4. Contains 2,015 panels of 16,069 total panels evaluated. : Fr(aC AD aE AF aG aH aI AJ aK AL aM AN AO AP aQ AR aS aU AW Ax aY BA BB Bc bE bF BG bH bI bJ bL bM bN BO bP bQ bR bS bU bV bW bX bZ cA cB cC cD cE cF cG CH cI cK cL cM cN CO CP CQ cR Cs CT CV CW cY cZ dA DB Dc DD DE dF DG dH DI dJ Dk DL dM dN Et Fp Hq Hr Hu Hw Hx Ih Ii Ij Ik Il In Io Ip Iq It Jg Jh Jk Jm Jn Jo Js Lh Li Lj Lu Lx Ly Lz Mb Mc Md Mf Mh Mj Mk Mn Mq Mr Ms Mt Mu Mv Mw Mx My Na Nb Nc Nd Ne Nh Ni No Nq Nr Ns Nu Nv Nw Nx Ny Og Oi Om Pa Pb Pd Pe Pf Pg Po Pz Qa Qb Qc Qe Wm) Is(aA Et Fp fR Hq Hr Hu Hv Hw Hx Ih Ii Ij Ik Il In Io Ip Iq Ir It Iv Jg Jh Jk Jm Jn Jo Jq Jr Js Jt Lh Li Lj Lu Lx Ly Lz Mb Mc Md Me Mf Mh Mj Mk Mn Mq Mr Ms Mt Mu Mv Mw Mx My Na Nb Nc Nd Ne Nf Ng Nh Ni Nk Nl Nm No Nq Nr Ns Nu Nv Nw Nx Ny Of Oi Om Oy Oz Pa Pb Pd Pe Pf Po Pz Qa Qb Qc Qe) Jp(aA Et Fp Hq Hr Hu Hv Hw Hx Ih Ii Ij Ik Il In Io Ip Iq Ir It Iv Jg Jj Jk Jm Jn Jo Jq Jr Js Lh Li Lj Lu Lx Ly Lz Md Me Mf Mh Mj Mk Ml Mn Mq Mr Ms Mt Mu Mv Mw Mx My Na Nb Nc Nd Ne Nf Ng Nh Nk Nl Nm No Nq Nr Ns Nu Nv Nw Nx Ny Oe Of Og Oi Om Oy Oz Pa Pb Pd Pe Pf Po Pz Qa Qb Qc Qe Wm) Mm(Et Fp Hq Hr Hu Hw Hx Ih Ii Ik Im In Ip Iq It Iu Iv Jg Jh Jj Jk Jm Jn Jo Jq Js Lh Li Lj Lu Lx Ly Mb Mc Mf Mg Mh Mj Mk Ml Mn Mp Mq Mr Ms Mt Mu Mv Mw Mx My Na Nb Nc Nd Ne Nf Ng Ni Nj Nk Nl Nm Nn No Nq Ns Nu Nv Nx Ny Oe Of Og Oh Oi Om Oy Oz Pa Pb Pc Po Pz Qa Qb Qc Qe) Mz(aA Et fR Hq Hr Hu Hv Hw Hx Ih Ii Ij Il In Ip Iq Ir It Iv Jh Jk Jn Jo Jq Jr Jt Lh Li Lj Lu Lx Ly Lz Mb Mc Md Me Mf Mh Mj Mk Mn Mq Mr Ms Mt Mu Mv Mw Mx My Na Nb Nc Nd Ne Nf Ng Nh Ni Nk Nl Nm No Nr Ns Nt Nu Nv Nw Nx Ny Oe Of Og Oh Oi Om Oy Oz Pa Pb Pe Pf Pg Po Qa Qe) Jl(aA Et Fp Hq Hu Hv Hw Hx Ih Ii Ij Ik Il In Io Ip Iq Ir It Iv Jh Jk Jm Jn Jq Jr Js Lh Li Lj Lu Lx Ly Lz Mb Mc Md Me Mf Mh Mj Mk Mn Mq Mr Ms Mt Mu Mv Mw Mx My Na Nb Nc Nd Ne Nf Ng Nh Ni Nk Nl No Nq Nr Ns Nt Nu Nv Nw Nx Ny Of Oi Om Oy Pa Pd Pe Pf Pg Po Pz Qa Qb Qc Qe) Nn(aA Et Fp Hq Hr Hu Hw Ih Ii Ij Ik In Io Ip Iq It Iu Jg Jh Jk Jm Jn Jo Jq Jr Js Lh Li Lj Lu Ly Lz Mb Mc Md Me Mf Mg Mh Mj Mk Ml Mn Mp Mq Ms Mt Mu Mv Mw Mx My Na Nb Nc Nd Ne Nf Ng Nh Ni Nk Nl Nm No Nq Ns Nu Nv Nx Ny Oe Of Og Oh Oy Oz Pb Pd Pf Pz Qa Qb Qc Qe) Ji(aA Et Fp Hq Hu Hx Ih Ii Ik Im Io Ip Iq Ir It Iv Jg Jh Jm Jo Jr Js Jt Lh Li Lj Lu Lx Ly Lz Mb Mc Me Mf Mg Mh Mj Mk Mn Mq Mr Ms Mt Mu Mv Mw Mx My Na Nb Nc Nd Ne Ng Nh Ni Nl No Nq Nr Ns Nt Nu Nv Nw Nx Ny Of Og Oh Oi Oy Oz Pa Pd Pe Pf Pg Po Pz Qa Qb Qc Qe) cU(AD aE AF aH aI aK AL aM AN AO Ap aQ aR aS aU AW Ax aY BB BC bE bF BG bH bI bL BN Bo bP bS bV bW bX bZ cA cF cG CH cI cK cM CO CP CQ cR cT Cu CV

Figure 29 Continued

CW cY cZ dA DB DC DD De dF dG dI dJ Dk DL dM dN) Lw(Et Fp Hq Hr Hu Hw Ih Ii Ij Ik In Io Ip Iq It Jg Jh Jj Jm Jn Jo Jq Jr Js Jt Lh Li Lj Lu Lx Ly Lz Mb Mc Md Me Mf Mh Mk Ml Mn Mp Mq Ms Mt Mu Mv Mw Mx My Na Nc Nd Ne Nf Ng Nh Ni Nm No Ns Nv Nx Ny Oe Of Og Oh Oi Om Oy Oz Pb Pd Pf Pz Qa Qb Qc Qe) Cu(aA aC AD AF aG aI AJ aK AL Ao AP Ar aU aV Aw Ax aZ BA Bb bC bE BG bH bI bJ bL bM bN BO bQ bR bV bW bZ cB cC cD cE cF cG CH cI cK cM cN Cp CQ cR Cs Ct Cv Cw cY cZ dA DB DC Dd De dG dH Di DL dN) cS(aC AD aE aF aG aH aJ aK aM aN AO AP aQ aR aS aU aV aW aX aY bC bE bF bH bI bJ bL bQ bS bU bV bW bX cA cC cD cE cG cH cI cK cL cM cN CO cP cQ cR Cs cT CV CW cY cZ dA Db dC DG dI dJ dK dL dN fR) aX(aC Ad aE AfaG aH AJ aM aN Ao AP AS aU aV aY aZ bB BC bE bF bH bJ bL bM BN bP bQ bR bS bV bW bZ cA cB cC cD cE cF cG cH cK cM cO cP cQ cR CT Cv cW cZ DB dC dD dE DG dI dK Dl dM fR) Pc(Fp Hq Hu Hw Ih Ii Ij Ip Iq It Iu Jg Jh Jj Jk Jn Jo Jq Jr Js Lh Li Ly Mb Md Me Mg Mj Mk Ml Mn Mp Mq Ms Mt Mu Mv Mw Mx My Na Nb Nd Ne Nf Ng Nk Nl Nm No Nq Ns Nu Nv Nx Ny Oe Og Oi Oy Oz Qb Qc Qe) Ok(aA Et Fp Hq Hu Hx Ih Ii Ik Im Io Ip Iq Ir It Jh Jm Js Jt Lh Li Lj Lu Ly Lz Mb Mc Me Mf Mh Mj Mn Mq Mr Ms Mt Mu Mw Mx My Nb Nc Nd Ne Ng Nh Nm No Nr Ns Nv Nx Oi Oy Pa Pe Pf Pz Qa Qb Qc Qe) aA(aC aD aG aI aL aM aP aZ bA bB bC BG bH bJ bL bO bQ bW bZ cG cO cR dA dB dC dD DE dH dK Et fR Hx Ij Il Im Ir Jg Jk Jt kF Lx Ml Mn MP mZ nl nK Nq nR Nt NU Nv Nw Oe Om Pg Po) Lv(Fp Hq Hr Hu Hw Ih Ii Ik In Io Ip It Iv Jh Jm Jn Jo Jr Js Lh Li Lj Lu Lz Mb Mc Md Me Mf Mh Mj Mk Mq Ms Mt Mw Mx Na Nc Ne Nf Ng Nh Ni Ns Nx Of Og Oi Oy Pb Pd Pf Pz Qb Qc Qe) Qd(Fp Hq Hu Hw Ih Ii Ij In Io Ip Iq Ir Iv Jh Jm Jn Jo Jq Jr Js Li Lu Lx Ly Mb Mc Md Me Mf Mh Mj Mk Mn Mq Ms Mt Mx My Na Nc Ne Nf Ng Nh Ni No Ns Nx Ny Of Oy Pb Pd Po Qa Qe Wm) Pg(Et Hq Hr Hu Hv Hx Ii Ir Iu Iv Jg Jo Jq Jr Jt Lx Ly Ma Md Mg Ml Mp Ms Mv Nb Nd Ne Nf Ng Nj Nk Nl Nm Nq Nr Ns Nt Nu Nw Oe Of Og Oh Om Oy Oz Pa Pb Pd Pe Pf Po Qa) Nw(Et Hv Hw Hx Ij Il Im Ir Iu Iv Jg Jj Jk Jr Jt Ly Md Me Mf Mg Mk Ml Mq Mr Mv Nb Nf Nj Nk Nl Nm Nq Nr Nt Nu Oe Og Oh Oi Om Oz Pa Pb Pe Po Qa) Ma(Et Hv Hx Ih Ij Il Im Ir Iu Iv Jg Jk Jq Jr Lh Lx Mg Mp Mr Mv Nb Nj Nk Nl Nm No Nq Nr Nt Nu Nv Nx Oe Oh Om Oz Pa Pe Po Qa) aP(aD aE aG aI aL aM aU aZ bA bB bC BG bH bM bN bO bP bR bV bZ cC cF cG cJ cN dA dB dC dD DE dG DI dK dL dN) Mp(Et Hq Hv Hx Ij Il Im Ir Iv Jg Jj Jk Jq Jr Jt Lx Ly Md Mg Mj Mr Mv Nb Nd No Nr Ns Nt Nu Nv Ny Om Pa Pe Po Qa) Jt(Et Hv Hx Il Ir Iu Iv Jg Jj Jk Jn Jr Lx Mb Mg Mn Mv Ni Nj Nk Nl Nq Nt Nu Nv Ny Oe Of Og Om Pa Pd Pe Po Qa) Im(Et Hv Hx Ij Ir Iu Iv Jg Jj Jk Lh Lx Mg Mj Mv Nb Nj Nk Nl Nq Nr Nt Nv Oe Oh Om Pa Pe Po Qa) Nt(Et Hv Hx Ir Iu Jg Jo Jq Lx Ly Mg Ml Nd Nf Ng Nk Nq Oe Og Oh Oi Om Oz Po Qa) Mg(Hv Il Ir Iv Jq Jr Lx Mj Mr Ng Nj Nk Nl No Nr Nv Oe Og Pa Pe Po Qa) aZ(al aJ AI aO Ap Aw BA BG Bn bW bZ cG cJ cR cX Dc De Di dK fR) Jj(Et Hx Ii Ij Ir Iu Iv Jg Jq Jr Lh Lx Mn Mv Nq Nu Nx Ny Om Pe Qa) Cx(aJ Ap aU Aw BA bC bO bZ cG cJ Cp Cw Dc DE dF Di fR) Jg(Hu Hv Ir Iu Iv My Nl Ns Oe Of Oh Oi Oy Pe Po Wm) bA(aC aG al bC Bg bJ bM bO bW bZ cB cT cX dE dK) Nj(Et Ir Jk Lx Nb Nq Nr Nv Oh Om Pa Pe Po Qa) aJ(aG al aL bC bG bM bO bZ cB cG cJ cX dE) Om(Iu Ml Nf Ng Nk Nl Oe Of Og Oh Pb) cJ(AI Ap Aw Ax Ba Bb Bg Dc De Di) Po(Hr Iu Ml Nf Oe Og Oh Oz) Ml(Hv Ir Iv Nb Nr Pe) Oe(Et Ir Jk Lx Nv Qa) bC(As Bg bO cX dE fR) dE(al aL bO bW cG) Et(Hv Il Iu Nk) Mw(My Og Oy) cG(As Bn cE) fR(Ao cX Nq) Nb(Nf Of) Qa(Nf Pb) dK(bG bZ) nR(mW nK) kG(mW nl) BabO BnDe WmMi NqIr JkOg PePf aLbE mFmP Unconstrained panels with 2 analytes, where 1.0E-2 >= 'model p-value' > 1.0E-3. Contains 3,322 panels of 16,069 total panels evaluated. :
aA(aE AF aH aJ aK Al aN AO Ap aQ AR AS aU aV AW Ax aY Ba Bb bE bF bI bM BN Bo bP bR bS bU bV bX cA cC cD cE cF CH cI cK cL cM cN Co CP CQ cT cV CW cY cZ Dc Dd dF DG DI dJ Dk dL dM dN Fp Hq Hr Hu Hv Hw Ih Ii Ik In Io Ip Iq It Iu Iv Jh Jj Jm Jn Jo Jq Jr Js kC kE kI kK kN kO kP Lh Li Lj Lu lW lX LY Lz Mb Mc Md ME MF MH mI Mj Mk mM Mq Mr MS MT MU Mv MW Mx MY NA NB NC ND Ne NF Ng NH Ni nJ Nk NL NM nN NO Nr Ns nT Nx Ny Of Og Oh Oi oO oP oQ Oy Oz Pa Pb Pd Pe Pf Pz Qa Qb Qc Qe) Nv(Et Fp Hq Hr Hu Hv Hw Hx Ih Ii Ij Ik Il In Io Ip Iq Ir It Iu Iv Jg Jh Jk Jm Jn Jo Jq Jr Js Lh Li Lj Lu Lx Ly Lz Mb Mc Md Me Mf Mh Mj Mk Ml Mn Mq Mr Ms Mt Mu Mv Mw Mx My Na Nb Nc Nd Ne Nf Ng Nh Ni Nk Nl Nm No Nq Nr Ns Nt Nu Nw Nx Ny Of Og Oh Oi Om Oy Oz Pa Pb Pd Pe Pf Pg Po Pz Qa Qb Qc Qe) bA(AD aE AF aH aJ aK AL aM AN AO Ap aQ AR AS aU aV aW Ax aY Ba BB Bc bE bF bG bH bI bL BN Bo bP bQ bR bS bU bV bX cA cC cD cE cF cG CH cI cK cL cM cN CO CP CQ cR Ct cV CW cY cZ dA DB dC DD dE dF dG dH dI dJ Dk dL dM dN fR) aZ(aC AD aE AF aG aH Aj aK aL aM AN Ao aQ AR AS aU aV aW Ax aY BB BC bE bF bH bI bJ bL bM bN Bo bP bQ bR bS bU bV bX cA cB cC cD cE cF CH cI cK cL cM cN CO CP CQ Cs CT CV CW cY cZ dA DB dC DD dE dF DG dH dI dJ Dk DL dM dN) Et(Fp Hq Hr Hu Hv Hw Hx Ih Ii Ij Ik In Io Ip Iq It Iv Jg Jh Jk Jm Jn Jo Jq Jr Js Lh Li Lj Lu Lx Ly Lz Mb Mc Md Me Mf Mg Mh Mj Mk Ml Mn Mq Mr Ms Mt Mu Mv Mw Mx My Na Nb Nc Nd Ne Nf Ng Nh Ni Nl Nm No Nq Nr Ns Nu Nx Ny Of Og Oh Oi Om Oy Oz Pa Pb Pd Pe Pf Po Pz Qa Qb Qc Qe Wm) Ir(Hq Hr Hu Hv Hw Hx Ih Ii Ij Ik Il In Io Ip Iq It Iu Iv Jh Jk Jm Jn Jo Jq Jr Js Lh Li Lj Lu Lx Ly Lz Mb Mc Md Me Mf Mh Mj Mk Mn Mq Mr Ms Mt Mu Mv Mw Mx My Na Nb Nc Nd Ne Nf Ng Nh Ni Nk Nl Nm No Nr Ns Nu Nx Ny Of Og Oh Oi Om Oy Oz Pa Pb Pd Pe Pf Po Pz Qa Qb Qc Qe) aJ(aC aD aE AF aH aK Al aM aN aO AP aQ aR AS aU aV AW Ax aY Ba BB bE bF Bg bH bI bJ bL BN bP bQ bR bS bU bV bW bX cA cC cD cE cF CH cI cK cL cM cN CO CP cQ cR cT cV cW cY cZ dA dB DC DD De dF dG dH DI dJ dK dL dM dN fR) Po(Fp Hq Hu Hv Hw Hx Ih Ii Ij Ik Il In Io Ip Iq It Iv Jh Jk Jm Jn Jo Jq Jr Js Lh Li Lj Lu Lx Ly Lz Mb Mc Md Me Mf Mh Mj Mk Mn Mq Mr Ms Mt Mu Mv Mw Mx My Na Nb Nc Nd Ne Ng Nh Ni Nk Nl Nm No Nq Nr Ns Nu Nx Ny Of Oi Om Oy Pa Pd Pe Pf Pz Qa Qb Qc Qe) Om(Fp Hq Hr Hu Hv Hw Hx Ih Ii Ij Ik Il In Io Ip Iq It Iv Jg Jh Jk Jm Jn Jo Jq Jr Js Lh Li Lj Lu Lx Ly Lz Mb Mc Md Me Mf Mg Mh Mj Mk Mn Mq Mr Ms Mt Mu Mv Mw Mx My Na Nb Nc Nd Ne Nh Ni Nm No Nr Ns Nu Nx Ny Oi Oy Oz Pa Pd Pe Pf Pz Qa Qb Qc Qe) bC(aC Ad Af aG aH aI Aj AL aM AN AO Ap Ar aS aV Aw Ax Ba BB Bc bG bH bJ bL bM Bn Bo bP bQ bR bU bZ cA cB cC cD cE cF cG Ch cJ cK cL cN CO Cp Cq cR Cs CT CV CW cZ dA DB DC DD De dF Dg dH DI DK DI dM) Pe(Fp Hq Hr Hu Hv Hx Ih Ij Ik Il Ip Iq It Iu Iv Jh Jk Jn Jo Jq Jr Lh Lj Lx Ly Lz Mc Md Me Mf Mh Mj Mk Mn Mq Mr Ms Mt Mu Mv Mw My Nb Nc Nd Ne Nf Ng Nh Ni Nk Nl Nm No Nq Ns Nt Nu Nx Ny Oc Of Og Oh Oi Oy Oz Pa Pb Pd Pz Qa Qe) Ba(Ad AF aG aI Aj aK AL aM AN AP Ar As aU Av Aw Ax aY BB Bc bE BG bH bJ bL bM Bn Bo bS bV bW bX bZ cB cC cD cE cF cG CH cM cO Cp Cq cR Cs Ct CW cX cY dB DC Dd DE dF Dg DI DK DI dM dN fR) Jg(Fp Hq Hr Hw Hx Ih Ii Ij Ik Il Ip Iq It Jh Jk Jm Jn Jo Jq Jr Js Lh Li Lj Lu Lx Ly Lz Mc Md Me Mf Mg Mh Mj Mk Ml Mn Mq Mr Ms Mt Mu Mv Mw Mx Na Nb Nc Nd Ne Nf Nh Ni Nj Nk Nm No Nq Nr Nu Nx Ny Oz Pa Pb Pd Pf Pz Qa Qb Qc Qe) aP(aC Ad AF aH Aj aK Al AN AO Ap aQ AR AS aV AW Ax aY Bb Bc bE bF bI bJ bL Bn Bo bQ bS bU bW bX cA cD cE CH cI cK cL cM CO CP CQ cR Cs CT CV CW cY cZ Db Dc Dd dF Dg dJ Dk DI dM fR) Mg(Fp Hq Hr Hu Hw Hx Ih Ii Ij Ik In Io Ip Iq It Iu Jh Jk Jm Jn Jo Js Lh Li Lj Lu Ly Lz Mb Mc Md Me Mf Mh Mk Ml Mn Mq Ms Mt Mu Mv Mw Mx My Na Nb Nc Nd Ne Nf Nh Ni Nm Nq Ns Nu Nx Ny Of Oh Oi Oy Oz Pb Pd Pf Pz Qb Qc Qe) Nt(Fp fR Hq Hr Hu Hw Ih Ii Ij Ik Il In Io Ip Iq It Iv Jh Jk Jm Jn Jr Js Lh Li Lj Lu Lz Mb Mc Md Me Mf Mh Mj Mk Ml Mn Mq Mr Ms Mt Mu Mv Mw Mx My Na Nb Nc Ne Nh Ni Nl Nm No Nr Ns Nu Nx Ny Of Oy Pa Pb Pd Pf Pz Qb Qc Qe) Im(fR Hq Hr Hu Hw Ih Ii Ik Il Ip Iq It Jh Jm Jn Jo Jq Jr Js Li Lj Lu Ly Lz Mc Md Me Mf Mh Mk Ml Mn Mq Mr Ms Mt Mu Mw Mx My Na Nc Nd Ne Nf Ng Nh Ni Nm No Ns Nu Nx Ny Of Og Oi Oy Oz Pb Pd Pf Pz Qb Qc Qe Wm) Qa(fR Hr Hu Hv Hw Hx Ii Ij Ik Il In Ip It Iu Iv Jh Jk Jm Jo Jq Jr Lh Li Lj Lx Ly Md Me Mf Mh Mj Mk Mn Mq Mr Ms Mu Mv Mw My Nb Nd Ne Ng Nh Ni Nk Nl Nm No Nq Nr Ns Nu Nx Ny Of Og Oh Oi Oy Oz Pa Pd Pf Pz Qb) cG(aC Af aG aI AL aM aO Ap Ar aV Aw Ax aY Bb bE bF BG bH bI bJ bL bM bN BO bP bQ bR bS bU bV bW bZ cA cB cC cD cF CH cJ cK cL cN CO Cp cR cT Cw cX dA DB DC Dd

Figure 29 Continued

De dG dH Dl dK dM fR) Mp(Fp fR Hr Hu Hw Ih Ii Ik In Io Ip Iq It Iu Jh Jm Jn Jo Js Lh Li Lj Lu Lz Mb Mc Me Mf Mh Mk Ml Mn Mq Ms Mt Mu Mw Mx My Na Nc Ne Nf Ng Nh Ni Nk Nl Nm Nq Nx Oe Of Og Oh Oi Oy Oz Pb Pd Pf Pz Qb Qc Qe) Nq(Hq Hr Hu Hv Hw Hx Ih Ii Ij Il Ip Iq Iu Iv Jk Jn Jq Jr Js Lh Li Lj Lx Ly Me Mh Mj Mk Ml Mn Mq Mr Mt Mv Mw My Nb Nc Nd Nf Ng Ni Nk Nl Nm No Nr Ns Nu Nx Ny Oe Of Og Oh Oi Oy Oz Pa Pb Qc Qe) Ma(Fp Hq Hr Hu Hw Ii Ik In Io Ip Iq It Jh Jm Jn Jo Js Li Lj Lu Ly Lz Mb Mc Md Me Mf Mh Mj Mk Mn Mq Ms Mt Mu Mw Mx My Na Nc Nd Ne Nf Ng Nh Ni Ns Ny Of Og Oi Oy Pb Pd Pf Pz Qb Qc Qe) Lx(Hr Hv Hw Hx Ih Ii Ij Il Ip Iq Iu Iv Jk Jn Jq Jr Lh Li Ly Me Mf Mh Mj Mk Ml Mn Mq Mr Ms Mu Mv Mw My Nb Nd Ne Nf Ng Nk Nl Nm No Nr Ns Nu Nw Nx Ny Og Oh Oi Oy Oz Pa Pb Pf Qe) Nw(Fp fR Hq Hr Hu Ih Ii Ik In Io Ip Iq It Jh Jm Jn Jo Jq Js Lh Li Lj Lu Lz Mb Mc Mh Mj Mn Ms Mt Mu Mw Mx My Na Nc Nd Ne Ng Nh Ni No Ns Nx Ny Of Oy Pd Pf Pz Qb Qc Qe Wm) Jt(Aa Fp Hq Hu Ih Ii Ik Io Ip Iq It Jh Jm Js Lh Li Lj Lu Ly Lz Mc Me Mf Mh Mj Mk Mq Mr Ms Mt Mu Mw Mx My Nb Nc Nd Ne Ng Nh Nm No Nr Ns Nx Oh Oi Oy Oz Pf Pz Qb Qc Qe) fR(aD aG al AL aM Ap aU Aw Bb BG bH bJ bM bN bO bS bW bZ cB cC cD cF CH cJ cM cN CO Cu DC dD DE dH Di dK dL Ji Jl Jp Jr Lv Mt Mu Mv Nu Ok Pg Qe) Pg(Fp Hw Ih Ij Ik Il In Io Ip Iq It Jh Jk Jm Jn Js Lh Li Lj Lu Lz Mb Mc Me Mf Mh Mj Mk Mn Mq Mr Mt Mu Mw Mx My Na Nc Nh Ni No Nx Ny Oi Pz Qb Qc Qe) bO(aC aG al AL aM aO Ap As Aw Ax aY BB bE BG bH bJ bL bM bQ bS bV bW bZ cB cJ cO Cp Cq cR cT CW cX dB DC Dd DE dH Di dK dM dN) bZ(aC aG al AL aM aN Ap As aU aV Aw Ax Bb Bc bG bH bJ bL bM Bn bQ bR bW cB cC cD cE cF cJ cM Cp Cq cR cT CW cX dB DC Dd DE dH Di dM) Cx(Af aG aH al aK AL aM AO aV Ax aY BB Bc bE Bg bL bM Bn Bo bQ bS bV bW cB CO Cq cR cT CV cW cY dB dC Dd DG dl DK dM dN) bW(aG al AL aM aO Ap Ar As aV Aw Ax Bb BG bM Bn Bo bP bQ bR bU cB cC cD cF cJ Co cR cT Cw cX dB Dc Dd De dF dH Dl DK dM) Nb(Hq Hr Hv Hx Ij Il Ip Iq Iu Iv Jj Jk Jn Jq Jr Li Ly Md Mf Mh Mj Mn Mt Mu Mv Mw My Ng Nk Nl Nm No Nu Nx Ny Oe Og Oh Oy Oz) Nj(Hv Hw Hx Ih Ii Ij Il Ip Iq Iu Iv Jj Jn Jq Jr Js Lh Li Mj Mk Ml Mn Mq Mr Mt Mu Mv Mw My Na Nd Nl Nm No Nu Nx Ny Oe Oz Qe) dE(aG Al aM aO Ap aU Aw Ax aY BB Bc BG bM bQ bV cB cC cD cJ cO Cp Cq cR cT Cw cX DC DD De dF dG Di DK dM dN) kG(kC kE kF kI kK kN kO kP IW IX IY mE mF mH ml mM mP mS mT mU mY mZ nA nB nC nD nF nH nJ nK nL nM nN nO nR nT nU oO oP oQ) Jk(Hr Hu Hv Hx Ij Il Ip Iu Iv Jo Jq Jr Lh Li Ly Me Mh Mj Ml Mn Mq Mr Mv Nd Nf Ng Nk Nl Nm No Nr Ns Nu Of Oh Oi Oy Oz Pa) mW(kC kF kI kK kN kO kP IW IY mE mF mH ml mM mP mS mT mU mY mZ nA nB nC nD nF nH nl nJ nK nL nM nN nO nT nU oO oP oQ) Jj(Hq Hv Hw Ih Ik Ip Iq Jh Jm Jn Js Li Mf Mj Mk Ml Mq Mr Ms Mt Mu Mw My Ng Nk Nl Nm No Nr Oe Oh Oz Pa Qb Qc Qe Wm) Iv(Hr Hv Hx Ij Il Ip Iq Iu Jq Jr Lh Li Ly Mj Mn Mq Mr Mu Mv Mw My Nd Nk Nl Nm No Nr Nu Ny Oe Og Oh Oi Oz Pa Wm) cJ(Ad Af aG Aj aM An AO Ar As Bc bG bH bL bM Bn Bo bS bV Ch Co Cp Cq Cs Ct Cv Cw cX Db Dd dF Dg DK Dl dM) Jq(Hv Hx Ij Il Ip Iu Jr Lh Li Mh Mj Mk Ml Mn Mr Ms Mt Mu Mv Mw My Nd Nf Nk Nl Nm No Nr Nu Oe Og Oh Oz Pa Qc) dK(aG al AL aM aO Ap Ar Aw Ax aY BB Bc Bg bL bM bQ bS cB cE cO Cp cR cT cW cX dB Dc dD De dF Di dM) Oh(Hu Hv Hx Ii Ij Il Ip Iu Jn Jr Lh Li Me Mj Mn Mr Mt Mu Mv Mw My Nk Nl Nm No Nr Nu Ny Oe Oz Pa Pc Qe) Cu(aE aH aM aN aO aQ aR aS aW aY bB Bc bF bP bS bU bX cA cL CO cP cT cV cW dD dF Dg dI dJ Dk dM) Di(aG al AL Ap Ar As aU aV Aw Ax BB Bc Bg bL bM Bn cB cO cT cW cX cY dB DC Dd De dF Dk) Iu(Hv Hx Ij Il Ip Jr Lh Li Me Mj Ml Mn Mq Mr Mt Mu Mv Mw My Nk Nl Nm No Nr Nu Nx Oe Og Oz Pa) Hv(Hx Ij Il Ip Iq Jr Lh Ly Mj Mn Mq Mr Mu Mv Mw My Nf Nk Nl Nm No Nr Nu Ny Oe Og Oz Pa) aG(al AL aM aO Ap Aw Ax aY Bb BG bH bL bM bQ bS bV cO Cp cR cW cX Dc De dF dl dM) Dc(AD Af al aL An Ap As aU aV Aw Bb Bg bJ bL bM Bn Bo cB cO cX cY dB dC De dF) Pa(Hr Hx Ij Il Ip Jr Ly Me Mf Mj Ml Mn Mt Mu Mv Nf Nk Nl Nm No Nu Ny Oe Og Oz Pb) Hx(Hr Ip Jr Li Ly Mf Ml Mn Mr Mu Mv Nf Nk Nl Nm No Nr Nu Ny Oe Of Og Oz Pb) Ap(al aK AL Ar aU aV Aw Ax bB BG cB cK Cp Cq cT cX cY dB De dF Dk) mP(kC kl kN IW mE mH ml mT mU mY mZ nA nB nC nD nF nH nl nK nL nN nR nT nU) De(Af al AL Ar As aV Ax Bb Bc BG bL bM Bo bV cX cY dB dC dF dl) Mv(Ij Il Ip Jr Lh Li Mj Ml Mn Mq Mr Ng Nk Nl Nm No Nr Nu Nx Oe Og Oz) Nr(Hr Ij Il Ip Jr Mj Mn Mu My Nk Nl Nm No Nu Nx Ny Oe Og Oz) Pc(Hr Ik In Io Jm Lj Lu Lz Mc Mf Mh Nc Nh Ni Of Pb Pd Pf Pz) aX(aD aF aK aQ aR aW bI bU bX cl cL cN cV cY dA dJ dL dN) Nu(Ij Il Jr Lh Mj Ml Mn Mq Mr Mu Nk Nl Nm No Ny Oe) Oe(Ij Il Jr Lh Li Mj Mn Mr Mt Mu Nm No Nx Ny Qc) Aw(Af al AL As aV Ax Bb Bg bL Bn cX cY dB dC) cX(al aL aM aO Bb bL bQ bV cR cW dC dF dM) Jr(Ij Il Lh Ml Mn Mu My Nk Nl Nm No Ny Wm) Bb(al AL aU aV Ax bB BG dC dF) Wm(Il Is Ji Jl Lv Mm Mv Mz Ok On) dF(aC Al aM As bJ bM Bn cE cR dC) Ax(al aL As aU aV Bg cB Cs cY) No(Ij Il Ml Mu Nf Nk Nl Nm Oz) Mr(Ij Ip Ly Ml Mn Nf Nm Ny Oz) Mz(Fp Ik Io Jm Js Pd Pz Qb Qc) mF(ml mT nM nN nR nT nU oP oQ) Il(Mj Ml Mn Mq Mu Nm Og Oz) aL(aC Al BG bH bJ cR dM) aM(al aO bG bJ bL bM cO dB) Mm(Io Lz Mc Md Nh Pd Pf) Ij(Ml Nf Nk Nl Of Og Oz) cB(Al bL bS bV dl dM) Ml(Ii In Jo Js Lh) Jp(Aa Jh Mb Mc Ni) bG(aC bM cR dC dM) cU(Aj Ar Cs Ct Dg) Nm(Mj Nk Nl Og) al(aC Al cR dM) nU(kl mM mZ nC) nK(ml nM nN oQ) Aa(Is Mi Qe) Nl(Mn Mu Ny) bQ(bM cC dH) nR(nC nH nl) mZ(ml nM nT) oQ(mE nB nl) As(Cp Cw) Bn(Cp Cw) Mw(Ng Of) Nf(Lh Mt) Oz(Mj Pb) aV(Al Dk) LyLh MuHu NkIp NyPb aUdM nTkI

Constrained panels with 3 analytes, where 1.0E-8 >= 'model p-value' > 0. Contains 2 panels of 625,624 total panels evaluated. : MIQdOk aPcUdH Constrained panels with 3 analytes, where 1.0E-7 >= 'model p-value' > 1.0E-8. Contains 83 panels of 625,624 total panels evaluated. : Ml{Mi(Is Ji Jj Jp Jt Lv Mz Nj Nn Ok Pc Qa Qd) Qd(Fr Hv Jg Ji Jp Lv Ma Mm Nn On Pc) On(Jj Ng Ns Oe Of Og Oy Pb) Ji(Hv In Iv Lv Ma Mj Qa) Ok(In Lv Ma Nn Qa) Ma(Is Iv Jt) Lv(Is Jt) LwIs} On{Pb(Lv Lz Nf Nj No) Lv(Nf Nm Of) Mg(Nf Ng) NnOi LzOf NfOe} Mi{Pc(Jp Lv Nf Nj Oi) Nn(Nf Oi) MaNj JpfR} cU{dH(aA aJ aX cS)} Cx{Cu(aX cS) aZcS} Nn{NfOk QdOi} ImQdPc aAaXcX Constrained panels with 3 analytes, where 1.0E-6 >= 'model p-value' > 1.0E-7. Contains 579 panels of 625,624 total panels evaluated. : On{Lv(Hr Hu Im Iu Jj Jo Lw Ly Ma Md Ml Mm My Ng Nj Nn Oe Og Oi Oy Oz Pc Pf Po Qd) Hr(Hv In Jj Jt Lw Ma Md Mi My Ng Nj Nm Ns Oe Og Oi Ok Oy Pb Qd) Of(Il Iq Lj Lw Ma Mg Mh Mi Mm Mt Mx Mz Nf Nj Nm No Nw Oi Pc Pf) Ml(Hu Is Ji Jt Lv Mm Mw Mz Md Mi My Mz Nf Nj Nm Oi Ok Qa) Nm(Jj Lw Ma Mi Mm Nf Ng Nj Oe Og Oy Pb Pc Qd) Ma(Jj Jo Lw My Nf Ng Nj Oe Og Oi Oy Pb Qd) Nj(Im Jj Lw My Nf Ng Oe Og Oi Oy Po Qd) Pb(Iq Lw Mg Mh Mt Mw Mx Mz Oe Oi Pf) Nf(Hv Jj Me Mi Nn Ns Og Oy) Lz(My Ng Oe Og Oy Qd) Oe(Jj Md Mm Po Qd) Oy(Mg Mh Mz No) Po(Li Mi Qd) No(My Ng) Md(Lw Oi) MgOg MhJj MzNg PzQd OiPc} Ml{Ok(Fr Hv Ij Il Is Iv Ji Jl Jp Jt Lw Mf Mg Mk Mp Mz Nq Ns Oe Oz Pc Pg) Jt(Fr Hv Im In Is Ji Jj Jl Jo Jp Mz Ng Nn Oe Pc Qa Qd) Qd(Is Jj Jl Lw Mj Mz Nb Nj Nu Oe Oz Pa Pz) Ji(Fr Il Ir Is Jk Jl Jp Nv Nb Ne Nn Nr Nu) Is(Fr Jp Mg Mm Mz Nn Oe Oz Pc) Lv(Ir Iv Jl Ma Mj Mz Nb Qa) Qa(Jj Lw Ma Mm Nn Oe Pc) Mi(Hq In Jg Ly Ma Nw) Ma(Jl Mj Mz Nb) Lw(Hv Iv Mj) NnIv} Mi{Nf(Fr Il Jg Ji Jk Jp Jt Lv Lw Ma Mv Mw Mz Ok Om Oz) Jg(Hq Lx Md My Ng Of Og Oy Pb Pd Po) Hq(Fr Il Jk Jp Lv Ma Mm Nj Pg) Nn(Jp Lv Mt Mx Nj Pd Pf) Ma(Jj Jo Jp Lw Nk Pc Pd) Il(Jj Lx Ly Ng Of Pb Po) Ok(Hr Jq Md Mz Of Pb) Lv(Ij Jo Jp Ly Nj) Lw(Jp Md Of Pb Pd) Jl(Hr Mx Pb Pe Po) Pd(Fr Jp Mg Mm) Mw(Of Oy Pb) Jt(Hr Md Pb) Jk(Ng Of) Jp(Nm Pf) fR(Fr Lu) OzPb} Ok{Lv(Hr Hw Ij In Jo Md Mm Nf Nn Of Om Pb Pc) Pc(Hr Hw Il Jp Jq Ma Md Nf Of Om Pb Qd) Pb(Jk Jl Jt Mw Nb Nn Oz Pg Qa) Nn(Hr Jq Ma Md Mz Nj Oi) Nf(Jl Jt Mg Mp Nq Qa Qd) Of(Jk Mw Nq) Hr(Il Jl) MdMp} Lv{Nn(Il Im Is Jj Jl Jp Mz Oi Pc Qd) Mm(Il Is Jj Jl Mz Ng Qd) Pc(aA Im Is Jl Jp Mz Qd) Jj(Fr Il Is Jk Jl) Lw(Il Jl Jp Qd) Im(Jl Qd) Nfji NgJg IsIu QdOz JlPb} aX{Cx(al Bn cJ Cp Cq cU Dc)

Figure 29 Continued cK(Ax Bg Cu Dc Di Dk Fr) cJ(Ax Bg Cu Dc Dk Fr) dH(aA aI aL cZ) cX(aO CU) Dd(aI aL) AxcB CqaL} cU{dH(aG aL BA bL bM bW dE FR)
Fr(As aV Bg cE) bR(bS bW cS) As(Aw Cp) aA(cX dA) cS(bM cB) aGcN aJdG} JI{Lw(Hr Ma Pb) Ji(Hr Nf Pb) Nn(Im Oi) Mg(Jj Ng) MaJj
MwPb HrJt ImPc} Qd{Pc(Lj Ma Nm Oi Pz) Im(Jp Ma Nn) Mm(Nm Pz) LwMa IIJj} Nf{Ji(Fr Hv Il Jk Jp Jt Ma Mv Nn) FrJt} cJ{Cu(As Cq Cx)
Cx(aA aZ) FraZ} Nn{Oi(Is Jp Mz Nw) IIJj} Ma{LwJp NjaA JjJk JoJt} Mg{Ng(Jg Jk Jp)} Pc{IIJj ImJp IsOi} cS{AxcB CxaL aAcX} Jt{FrHr
JiJq} CuCxdH LwIIJj aAbCcX Constrained panels with 3 analytes, where 1.0E-5 >= 'model p-value' > 1.0E-6. Contains 2,185 panels of 625,624 total panels evaluated. :
Lv{Jj(Hv Hw Hx Ih Ii Ij Im Iq Ir Iu Jg Ji Jm Jp Jq Jt Lw Ma Mg Ml Mn Mp Mv Mz Nd Nl Nq Nr Nt Nv Nw Ny Om Pc Pg Po Qd) Ml(aA Fr Hv
Hw Hx Ii Ij Il Im In Iq Iu Jp Jq Jr Js Lw Ly Mg Mp Mr Nd Nn No Nr Nw Oh Om Pa Pc Pe Pg Po) Ma(aA Hv Hx Im Is Iu Ji Jl Jp Jt Lw Mz Nd
Nj Nk Nl Nw Ok Pc Qd) Jt(Hr Hv Hw Ij Im In Jn Jo Jq Md Na Nd Nf Nj Nm Ny Of Om Pb) Im(Hv Hx Il Iu Jp Lw Ly Mg Mp Nb Nj Nk Nm Nr
Oh Pg) Ji(Hw Ij Il In Jq Md Mz Nk Nm Om Pb Pc) Ly(aA Hx Il Jl Mp Mz Nl Nt Nw Pa Pg) Ok(Hv Jp Jq Mg Mp Na Ni Nk Nm Ny Qd) Jl(Hr Iu
Jo Jp Mg Nm Oe Oz Pd) Mp(Hq Hx Il Jp Md Mz Nj Nw) Is(Fr Jp Jr Lw Mh Nm Oe Oz) Pc(Hx Il Ir Nd Nr Oi Pa) Lw(Fr Hv Hx Iu Mz Pa)
Jp(aA Iu Mm Nm Oh Oz) Fr(Mz Ng Nj Qd) Nm(Mm Mz Nw Qd) Nn(aA Hx Nr Pa) Mg(aA Nd Ng Nk) Mw(My Og Oy) Jg(My Og Oy) Oz(aA
Iu Nr) Nj(aA Nd) Qd(Lj Pf) Nw(Nk Oe) NbPb NfHx IlOh Irlu OfOm PfPg} Ok{Mg(Hr Hw Ij In Jj Jl Jo Jp Jq Md Na Ng Nj Nk Ny Of Og Om
Pb Pd Qd) Qd(Hr Hv Hw Ij Jn Jq Lz Ma Md Mp Mz Na Nj Nm Nn Nq Ny Of Pb) Ma(Hr Hw Jj Jk Jl Jp Lw Md Mm Mp Nf Ni Nj Nk Nl Of Pb)
Nq(Hr Hw Ij In Jj Jo Jp Jq Md Na Ng Nj Ny Om Pb Pd) Md(Fr Is Ji Jk Jl Jp Jt Lw Mm Mz Nb Nj Oe Oz Pg) Nf(Fr Hv Il Jk Jl Jp Lw Mv Mz Nb
Oe Oz Pg) Hr(Fr Hv Hx Is Iu Jk Jp Jt Mk Mp Nb Nj Pg) Hw(Jl Jp Jt Lw Mi Mp Nj Nn Oe Oz Pg Qa) Of(Fr Il Jg Jl Jp Mp Mv Nb Nn Pg) Pb(Fr
Hv Hx Il Jp Lw Mp Oe Oi Pe) Jq(Is Ji Jp Jt Lw Mp Mz On Pg) Pg(Ij In Jo Mm Ny Om Pd Pf) Nn(Il Jn Jp Jr Mx Om Pc) Nj(Fr Jk Jl Jp Mp Oh
Pc) Jt(Hv Ij In Jo Na Ny Om) Lw(Ij Il In Na Nm Om) Mi(Ij In Nm Ny Om Pd) Mp(Hq Jo Jp Nd Pd) Jl(Jo Ny Oe Pd Pe) Mm(Il Jp Nk) Jk(Jj Ny
Om) On(Lh Ny Om) Fr(Nk Oy) Mz(Ji Jp) Is(Ir Jr) Jg(Ng Og) NmJp MwOg IlJj OiPc} cU{Fr(aG aZ bF Bn bR bU cA cC cD cF cG cJ cK cL cN CO dA dB dE dG dI dK) As(aI aK aL aU aV Ba Bg bW cJ cM Cq cS Cu Cw Cx cY Dc Dd De dH Di dK) dK(aA aG aV aX aY aZ bM bP bQ bR bU cC cE cF cG cL cN dE dH Dk) aA(aG aX bJ bQ bR bV cB cJ cK cN cQ cS Cx dE dG dI dL) dH(aC aI Ap Aw Bb bG bQ bS cG cJ cM Cu cW CX Di) bR(aC aG aJ aL aP aX BA bL bM cM cX dE fR) cE(aG aI aJ aL Aw BG bL bM cG cS cX fR) aG(aX bA bM bQ cC cL cS CX dE) aL(aX bE bJ bQ cC cL cN cS dE) cS(aZ bQ cL CX dG dI dL) aJ(aZ bM bQ cB cN cX dL) aX(aI bQ bV cB cJ Cp dI) dE(aE aI cB cC Cp cX dC) aV(aC Al Aw Ba CX) bQ(aP Aw Ba cM) cJ(Ap Bn Cx Di) cN(aC aZ bM fR) Cx(aZ Dd) aP(cB dG) cC(bL bM) cL(aC bW) AwBn BacB aZcX} Jl{Pb(Fr Hr Ij Im Is Jg Jj Jp Jt Li Ma Mg Ml Mm Mp Mv Mz Nj Nm Nn Nq Nw Oe Om Pc Pg Qa Qd) Hr(Im In Is Jg Jj Jp Mg Mm Mp Mz Nj Nm Nn Oe Om On Oz Pc Po Qa Qd) Im(Jp Lw Lz Ma Mg Ml Mm Mp Nj Nm Oe Og Oh Oz Qd) Mg(Iu Jo Jp Ml Nf Nj Nm Oe Of Og Oy Pd Qd) Nn(Jj Jo Jp Lz Ma Ml Mz Nj Oe Oz Pc Qd) Ma(Ji Jo Jp Mm Mz Nj Nm Oe Oz Pc Qd) Mi(Hq Jo Lx Lz Mh Mk Mr No Of Oz Pd) Qd(Iu Jj Lj Lw Lz Mp Nj Nm Oe Oz) Pc(Jj Jo Jp Ml Mz Nj Oe Og Oi) Lw(Jj Jp Md Ml Nm Oe Of Oz) Ji(Jq Md Mz Nm Ny Of Pe) Oe(Jg Jj Ml Mm Nj Oz) Ml(Jj Jp Mz Qa) Mm(Lz Mz Nm Oz) Mp(Hq Jp Lz Nj) Jg(Ng Of Og) Jj(Nj Oz) Jp(Nm Oz) Jt(Jo Nf) NqMk LzLi} On{Po(Hu Hv Jj Jp Ma Md Me Mg Mp Mr My Mz Ng Nn Ns Og Oi) Ml(Hv In Ir Iv Jh Jn Jp Jr Js Mb Mm Mw Pc Pz) Pc(Hr Im Jj Ma Md Mm Mw My Ng Nn Ny Og) Md(Jj Jt Lz Ma Mg Mh Mi Mp Nj Nn) Mm(Hr Jj Lw Ma Ng Nj Og Oy Pz Qd) Oi(Hq Hx Ii Mk My Nb Nv Ny Oy Qd) Mi(Hq Jo Lx Mh Mt Ng No Pd) Mg(Hr Jj Jo Mv My Nb Oe) Ng(Jg Jq Mh Mt Mx Nn Nq) My(Jg Mh Mt Mx Mz Pf) Jt(Hw Jo Jq Na Nb Ny) Lw(Jp Oe Og Oy Qd) Mz(Hr Hu Ji Jj Nn) Ny(Hv In Ji Me Qa) Lz(Hu Jh Mp Mw) Mh(Hu Jh Ns Og) Mt(Hu Jj Ns Oy) Ma(Hq Im Nk) Oy(Iq Mw Mx) Mp(Hq Nv) Nk(Ii Jo) Hr(Hu Qa) Im(Jp Nn) Qd(Iu Oz) Jj(Il Nw) Og(Jg No) Pf(Pe Pg) NsLh NjPz JiJq JpOe} Ma{Lw(aA Fr Hv Hx Il Is Iu Jj Jk Ml Mr Mz Nb Nj Nk Nl Nr Nw Pa Pe) Ji(Hw Ij In Jj Jp Jq Md Mm Mz Ni Nj Nk Nl Nm Nn Of Om Pb Pc) Ml(aA Hv Hx Ii In Ir Jj Jp Js Mr Nj Nn Nr Nt Nw Pa Pc Pe) Jt(Hr Hv Hw Ij Im In Jj Jp Jq Md Na Nf Ni Nj Of Pb Pc) Pc(aA Hv Hx Im Ir Is Jj Jp Mr Mz Nj Nr Nw Oi Pa Pe) Jj(Hx Il Ir Is Iu Jg Jp Mz Nl Nn Nt Nv Pg Qd) Nn(Im Is Jp Mr Mz Nj Oi Pa Pe Qd) Mz(aA Im Iu Mm Nf Nj Nk Nl) Is(Iu Jp Mh Mm Nj Nm Oe) Qd(aA Iu Jg Nj Nk Nm) Jp(aA Im Mm Mp Nj) FrNj NbPb NgJg NkNw} aX{cX(aI aJ aL aP Ax aZ bA BG bL bO Cq Dc dF Di Dk dM FR) Cu(aC Ad An As Bn bV cB CQ Cw dA Dc Dg dH dN) Cx(aA aL aZ bA Bg bO bV cK cS Dd dF dH Di Fr) dH(aJ aO aP Ax bA BG bQ Dc dF Di Dk Fr) Ax(aU Aw bB Bg bV Cp dA De dI dK) cB(aA Al Ar Cq Dc Dd Di Dk Fr) Cp(aC aL As Bn bO cZ) Cq(aC aI As bM bO cZ) bV(aA aI aL bA cZ Fr) Al(aL aV bO cJ) dI(aA bA cZ Fr) Bg(bA bO Dd) Dc(aC aL) aA(aI cJ) cZ(Aw De) ArbB BccK BoDd CvaL DkdK FrbQ} cS{Cx(aA Ax bA Bb bM bN bO cB cJ Cp Dc Dd De Di Dk Fr) Cu(Ad An As BN cH cJ cK Cq Cw cX Dc dG dH dN) aZ(Af aI aL BG bO bR cB cH cX dD dH Dk) bM(Al Ax BG bO bR cB Cq cX DD dH Dk) cB(aA Aj AL Ar bA bG bO cX Dk dM) Ax(aI As Bb Bg bN bR Cs cX dG dH) cX(aL bA Bb bO cF Dc dD Di Dk) dH(aA aL aP bA bG bP Di Fr) aL(bH Bn cM dG) cJ(Aj Di Dk Fr) As(Cp Cq Dk) bO(aW bG) AfDe BbBg BnCp DkcK FrdG} Nn{Oi(aA Et Fr Hu Hv Hx Ij Il Im Ir Iv Jg Ji Jk Jq Jr Jt Lw Lx Mr Nb Nj Nr Nt Nu Nv Om Pa Pe Pg Po Qa) Im(Hv Il Is Jp Jt Mz Nb Nj Nr Oz Pa Pe Pg) Nj(aA Il Is Jp Mz Nr Nt Pa Pe Qd) Nf(Il Is Jp Jt Mz Nw Om Qa Qd) Is(Iu Jj Jp Jr Mh Oe Pc) Ml(Hv In Ir Jp Mz Nr) Qd(Iu Lj Lw Mx Pz) Ji(Il Jq Md Mz Nm) Jj(Ij Jk Mz Nt Pg) Jt(Hr Hw Jq Md Pb) Pc(Jp Nr Pa Pe) Lw(Il Jp Pa) Mz(Mt Mx) NmJp NgJg IlOg} Jt{Nf(Im Jj Jo Jp Lw Mv Mz Nq Nw Oe Om Oz Pc Pg Qa Qd) Im(Hr Hv Hw Ij In Jo Jp Jq Md Na Nj Ny Pb Pc) Fr(Hw Ij In Jo Jq Md Na Nj Ny Of Om Pb) Pb(Jg Ji Jj Jo Jp Lw Mw Mz Om Pc Pg) Md(Ji Jj Jo Jp Lw Mp Mz Pc Pg) Mi(Hv Hw Ij In Jo Jq Mz Na Ny) Hr(Hx Jj Jp Mz Pc Pg) Na(Ji Jj Jo Mz Pc) Hw(Ji Jj Jo Jp) Jq(Jj Jo Mz) MlOg MwOf IlJj JiNy} Qd{Mg(Im Iu Jj Jo Jp Ng Nj Nm Oe Pz) Jg(Jj Lj Mp My Ng Nm Oe Og Oi Pz) Nj(aA Fr Im Jj Jk Lj Mp Nq Oz) Lj(Fr Iu Jj Jp Li Mi Oe Pz) Oz(Fr Iu Jj Jk Jp Nr Oe) Fr(Lz Nm Oe Oy Pz) Nq(Iu Jj Nf Oe Pz) Lw(Hv Iu Jp Nm Oe) Mp(Im Iu Jj Jp) Nm(Im Ji Jp) Mw(My Og Oy) Lz(Oe Pa) Mi(Hq Lx) Pz(Im Jp) Ji(Jq Mz) Jj(Jk Nt) IifR IlIt JkOe PfPg} Ml{Qa(Et Fr Im Is Iv Jg Jp Jq Mf Mg Mj Mp Mz Nb Nj Nm Nw Om) Mz(Fr Hv Iu Iv Jg Jj Lw Mf Mg Mj Mm Nb Nj Oe Om Pc) Jj(Ij Is Jk Mj Nb Nt Om Pe Pg Po) Iv(Fr Jp Mg Mm Mp Nw Om Pc) Mj(Im Jp Nj Nw Om Pc) Lw(aA Hx In Nb Nr) Fr(Hv In Ir Js) Is(Mf Mp Nj Nu) Mw(Hu Oy) Hv(Mm Pc) NbPb} Ji{Md(Fr Hv Il Jg Jk Jp Mg Mp Nb Nk Nq Nt Pc Pg) Pb(Fr Hv Hx Il Jk Jp Nb Nr Nt Oz Pa Pc Pe Pg) Il(Hr Ij Jj Jq Mm Mz Ny Of Om Pc) Nf(Jg Mw Nb Nq Nt Oe Pa Pc Pg) Fr(Jq Mz Nj Nm Of) Jk(Jj Mz Ny Of Om) Jq(Hv Jp Mi Pc) Nm(Jp Mm Pc) Hr(Nr Pa Pe) Mz(Jp Mi) MwOf IvJr OiPc} Fr{Is(Iu Jj Lw Mh Nf Ng Nj Nm Oe Of Oy) Nj(aA Im Jj Lw Mp Mz Oe) cJ(Aj bC Bn cE Cx) Cu(An As Bn Cx) Dd(An As Bn Cx) aZ(Bn bO Cv Cx) Nf(Hv Mz Qa) Ng(Jg Mg Mi) Lw(Hv Im) LxMi MpHq NbPb IjOf IlJj OiPc aPdH bCcK} Pc{Im(Hu Hv Ij Il Ir Is Iv Mj Mr Mz Nb Nj Nr Nt Oz Pa Pe Pg) Is(Iu Jj Jp Mh Nj Oe Og) Oi(Jg Jp Mz Nt Nw) Jj(Ij Jk Nt Pg) Nj(aA Jp Mz) Il(aA Lw Og) Nf(Mz Qa) Jp(Lw Nm) MdQa MgaA PePf} Lw{Is(Ir Iu Jp Jr Js Nm) Hr(Hv Mr Nb Pa Pe) Pb(Hv Nb Oz Pe Qa) aA(Il Md Mg Nf Nj) Jp(Il Im Nm Pa) Md(Hv Nb Pg) Nf(Hv Nb Qa) Ng(Jg Jk Mg) Jj(Jk Nt) Og(Il Jg) NjPa HvIm} Cx{Cu(aG aU aV Ba bO cK Cw dC DE dK fR) aZ(aI aJ aP bC bL bW bZ Cq De) aA(Af aU Aw bC cB Cw De) aP(cB cJ dG dH) cJ(bA Dc De) DefR DkdK aUbA cEcG} Jj{Il(Is Jk Jp Mg Mm Mp Mv Mz Nt Nx) Jk(Is Jp Mg Mi Mp Nj Nt Nu Oe) Nt(Is Jp Mg Nj Oe) Pg(Mg Mm Nj Nu Oz) Mg(Is Jp Mz) NqIs MiNk MmPe MpJp} Mi{Jk(Jo Lx Oy Pb Pd Po) Mw(Md My Ng Og) Hq(Mg Mp Nk Nq) Is(Ir Iu Jr Js) Il(Hr Oy Pg) Jg(Jo Mt Om) Nb(Pb Po) Om(Of Pb) LyNk MgNg NeNl PfPg} Ng{Jg(Hx Il Is Iu Jk Mp Mz Nq Nt Pg) Mg(aA Il Is Mw Mz Nw Pa Pg) Mm(Pe Pg)} Jp{Mp(Hq Im Is Md Nd Nj Nm) Is(Mg Mm Nm Oe) Im(Mg Nj Oh) Nm(Mm Nt)

Figure 29 Continued

NbPb} Cu{cJ(Ad An bJ Bn Cw Dc dE) As(cK De dH) Bn(Aw De) Dc(cK dH) cXdE} aA{cX(aU aZ bO cB cG cJ dC dE) Nj(Mg Mp Mz) bCcB cJdE nUmU nIkG} aP{dH(aI bF bG bM bQ bZ cB cG cO) dG(aI aL cB cX)} Mm{Is(Mh Nm Oe Pz) Mz(Nm Oe) Pg(Jo Oy) NfQa PePf} Pb{Nb(Im Jg Mw Nj Om) Mw(Hu Oz)} Mp{Nj(Im Is Mz) Hq(Il Mz) JgOi} Og{Jg(Hx Il Is Mz) Is(Mg Mw)} Dk{dK(Af As aZ Bn)} Mg{Nf(Mz Qa) Is(Iu Oe)} aZ{cJ(Bg Di) bOcX} De{AsAx BnbA} nU{mU(mW oQ)} NqMzNf cEcGcX

Constrained panels with 3 analytes, where 1.0E-4 >= 'model p-value' > 1.0E-5. Contains 4,309 panels of 625,624 total panels evaluated. : cU{Cx(aJ Al AP aU BA Bb bJ bO bQ bR bU cA cB cC cD cE cF cK cL cN cO Cw dA Dc DE DI dJ dK Fr) cX(aC aM AP bA Bb bJ bM bO bP bQ bU cA cB cC cD cF cG cJ cL cN cO cR dA DI) Aw(Al aY bI bJ bR bU cA cC cD cF cG cK cL cN CO Ct dA dE dG dI) Bn(aI aK aL aU aZ BA Bb Bg bW cM Cp Cq Cu Cw cY Dc Dd De Di dK) aI(aC aY bJ bP bQ bR bU cA cC cD cF cG cK cL cN cO dA dG dI dK) Di(aG Al aZ bJ bM bQ bR bU cA cB cC cD cE cK cN cO dA dI dK) cM(aV aY bJ bP bU cA cC cD cF cG cK cL cN CO dA dB dG dI) bW(aV aY bP bQ bU cA cC cD cE cF cG cK cN CO dA dG dI) Cu(An bJ bQ bR bU cC cD cE cK cL cN Cq dA dB dG dI dK) aL(aC aJ Al aV aY bU cA cD cF cG cK CO dA dB dG dI) Ba(aG aZ bJ bM bU cC cD cE cF cG cK cL cN dA dG dI) De(aJ Al bJ bM bQ bU cA cD cE cG cK cL cN CO dA) bA(aC As aZ bJ bM bQ bU cB cC cD cE cF cN dA dG dI) Bb(aG Al bJ bQ bR bU cC cD cE cK cL cN dA dB dK) aE(aV bQ bU cA cD cF cG cK cN cO dA dG dI) Al(aA aG aK aU aZ bM bU cB cY dJ dK) bJ(aM aZ bM cJ Cp cY Dc Dd dK Fr) bQ(aC Ap Bg bL bM cJ Cp cW Dc fR) cL(aJ aU aZ bL bM cG cJ Cp dC) cN(AP bC bL cB cJ Cp cW Dc) Dd(Ad aG An bM Bo Cq Cw dE) cE(aC aO AP bO cB cJ Cp) As(aG aQ bC bO cB dE Dk) Bg(aA aJ aP bF bZ cC dE) dA(aJ AP BC Cp Dc) dK(aJ cA cB cD cO dB dI) bL(bU cD cK cO dG dI) cC(aJ aP aZ bH cW Dc) Ap(bR cK cQ dI) Dc(aG bU cK dG) aY(aC aM aX cW) bM(aV bO cB cJ) Cp(bU cK dG) aP(cJ dI dL) aZ(bO cD cJ) bC(cA cK dI) bH(bU cA cD) Co(aU cY) fR(dF dL) AxCs aCcB aJaV aUbP cWdG dBdC} Jj{Pc(Et Fr Hu Hv Hw Hx Im Ir Iu Iv Jg Jq Jr Jt Lh Lx Mg Mj Mn Mr Mv Nb Nj Nl Nn Nr Nu Nv Nx Ny Om Pa Pe Po Qa) Ma(Fr Hv Ih Ii Ij Im Iv Jm Jq Jr Lh Mg Mm Mn Mp Mr Mv My Nb Nj Nk Nq Nr Nu Nw Nx Ny Om Pa Pe Po Qa) Mg(aA Fr Hv Ij Im Ir Iu Iv Jg Ji Jr Jt Lw Lx Mj Mn Ng Nj Nk Nl Nn Nr Nu Nv Nw Nx Ny Om Pe Po Qa) Jg(aA Hv Ij Il Im Ir Is Iu Iv Jp Jr Jt Lw Mj Ml Mp Mz Nk Nl Nn Nq Nu Nx Oe Oh Ok Pe Po Qa) Nq(Hv Hx Ij Il Im Ir Iv Ji Jp Jq Jr Jt Lw Lx Mn Mz Nj Nl Nr Nu Nw Nx Ny Om Pe Po Qa) Iu(Fr Ij Im Iv Ji Jp Jr Lw Lx Mm Mn Mv Mz Nn Nu Nv Nw Nx Ny Ok Om Pe Po Qa Qd) Mp(Hv Hx Ij Im Ir Is Iv Ji Jq Jr Jt Lx Mv Mz Nj Nr Nu Nw Nx Ny Om Pe Po Qa) Il(Et Im Ip Ir Iv Jq Jr Lh Lx Mf Ml Mn Nj Nm Nu Nv Nw Ny Oh Om Oz Pe Po Qa) Nn(Hv Hx Ir Iv Ji Jr Jt Lx Mr Nb Nj Nl Nr Nu Nv Nw Nx Ny Om Pa Pe Po Qa) Jt(Fr Hv Ij In Ir Jn Jo Jp Jr Lx Mz Ni Nj Nu Nx Ny Of Om) Lw(Hx Ij Ir Iv Mj Mv Nk Nl Nr Nu Nv Ny Om Pe Po) Ml(Fr Hv Hx In Ir Iv Jo Js Lh Mv Mw Nr Nv Nw) Nj(Ij Im Ir Is Mv Mz Nv Nw Om Pe Po) Mm(Hx Ij Mj Mv Nk Nl Nx Om Po) Jp(Hw Ij Ir Is Nl Nr Om Pe Po) Nk(Fr Ij Is Ji Mz Nw Ok Om) Nl(Fr Ij Mv Mz Nw Om) Nf(Ij Mw Mz Om) Pb(Ij Mw Nb Om) Mv(Im Mz Ok) Oe(Is Nv Po) Fr(Jr Mz) Md(Ij Om) Qd(Lz Wm) NuIj MhIs MwOf ImLh JmOk OhOm OzPe} Ml{Nb(Fr Hu Hv Im In Ir Iv Jn Jp Jq Jr Js Lx Md Mf Mg Mm Mp My Nf Ng Nj Nn Ns Nt Nu Nw Oe Of Og Om Oy Pc Pe Pg Po) Iv(Et Im Ir Jg Jl Jq Jr Lx Mf Mj Mt Mu Mv Nj Nm Nq Nt Nu Nv Nx Oe Oh Oz Pg Po) Ma(Fr Hw Ih Ij Il Im Iu Jg Jk Jn Jq Jr Lh Li Mm Nk Nl No Om Pg Po) Nw(Fr Hv Hw In Ir Iu Jl Js Mf Mg Mp Mv Nj Nk Nm Nn Nr Nt Nu Oe Pc) Jp(aA Fr Hv Hw Hx Ij In Ir Jq Jr Mf Mz Nr Nt Om Pa Pe Pg Po) Nn(aA Hu Hx Ii Ij Jq Jr Js Mj Mr No Nt Om Pa Pe Po) Lw(Hw Ii Ij Ir Jn Jo Jr Js Lh Mr Nt Om Pa Pe Po) Lv(Et Jg Jk Jn Lx Mv Na Nj Nk Nq Nt Nv Ny) Om(aA Hv In Ir Jl Js Mp Ng Nr Nt Oe Og Pc) Fr(Hx Ij Jl Jn Jq Jr Me Mj Ng Nm Nr Nt) Mz(aA Im Ir Jk Mp Mv Nq Nr Nt Pe Pg Po) Mj(In Jg Jq Jr Mg Mm Oe Oz Pg Po) Ir(Iq Jg Mg Mm Mp Nt Oe Pc Pg Po) Jl(Ij In Jg Jq Lx Nj Nm Oz Pg Po) Hv(Et Im Jq Mg Mp Nm Nt Oh Po) Pc(Hx Ii Ij In Js Nr Pe Po) aA(Ij In Jg Nj Pg Po) Nr(Im Jg Jq Mg Mm) Nt(Jq Ly Nj Oe) Mm(Hx In Js) Pe(Lz Nj Pf) Pg(Mg Nj Oz) Mw(My Ng) In(Et Mg) PoOe MpHq NgJg} Nj{Ma(Et Hv Hx Im Ir Iu Jg Jk Jq Jr Lh Mm Mp Mr Mu Nb Nd Nq Nr Nt Nv Nw Oe Oh Om Pa Pe Pg Qa) Im(Hv Is Iu Jk Lw Mg Mj Mm Mu Mv My Mz Nb Nq Nr Nt Nv Nw Oh Om Oz Pa Pe Pg Po) Pc(Et Fr Hv Hx Ij Il Iv Jk Jr Jt Lx Mj Mr Nb Nn Nr Nt Nv Nw Om Oz Pa Pe Pg Qa) Jt(Hv Hw Ij In Jk Jn Jo Jp Jq Md Mp Nf Nn Nq Nw Ny Of Pb Pg) Jp(aA Is Iu Ji Jk Jl Jr Mz Nb Nq Nr Nt Oe Oh Pa Pg) Mp(Hq Hv Ij Il Jg Ji Jk Nb Nd Nr Nt Nw Om Pa Pe) Nn(Fr Hv Hx Ir Iv Ji Jr Lw Mr Nb Nw Om Oz Pg) Lv(Il Iq Jk Jq Ly Nb Nq Nr Nt Oh Om Pa Pe) Is(aA Ir Iu Iv Jl Jr Js Mg Mh Nm Nq Oe Oh) Lw(Hv Hx Jk Mj Mr Mz Nb Nq Nr Nt Om Pe) Oe(aA Et Mm Mz Nb Nt Nv Nw Om Pg Qd) Oh(Jk Jl Mz Nb Nt Nw Om Pa Pe Pg Qd) Nt(aA Hq Ji Jo Ly Mm Mz Nd) Nq(aA Ir Ji Jl Mz Nr Nw) Mg(Hv Mz Ng Nr Nw Pg) Ji(Hr Il Iu Jk Jl Pa) Mm(aA Jk Nb Pa Pe) Jl(Lz Mh Mz Og Oz) Nb(Hr Nf Of Qd) Ok(Ij Il Pg) aA(Il Jg Pg) Mw(My Og) Om(Of Og) FrJr NmNw MzJk PfPg} Jt{Jo(Hr Hv Ij Il In Ir Is Ji Jk Jn Jp Mg Mm Mp Mz Nn Nq Nt Nv Ny Om Pc Pg Po Qd) Of(Il Im Jg Ji Jk Jl Jn Jp Jr Lw Mg Mm Mp Mv Mz Nn Nq Nt Nw Om Pa Pc Pg Po) Om(Hr Ij Im Jg Ji Jq Lw Ma Md Mz Nn Ny On Pc Pg) Hv(Fr Hr Ji Jl Jn Jp Lw Mz Na Nn Ny Oe Pc Pg) Jl(Hw Hx Ii Ij In Ir Jq Md Na Nb Nm Ny Pe) Mz(Hw Ij Im In Ir Ji Jn Jr Nw Ny Ok) Ma(Fr Jn Mg Mm Ng Nk Nm Nn Nw Ny) Pg(Hw Ij Im In Jn Jq Na Ny Pd Pf) Hr(Il Ji Mp Mr Nw Pa Pe Po Qd) Qd(Hw In Jn Jq Jr Md Mx Na) Ny(Is Jg Jp Lw Nn Nq Nw Pc) Jn(Im Is Ji Jp Nn Oe Ok) Md(Jg Mw Nq Nw Oe Oz) Ij(Ji Jp Lw Nn On Pc) In(Ji Jp Lw Nn Oe Pc) Jq(Is Jp Lw Nw Oe Pc) Im(Fr Ir Jr Ni Nk) Na(Jp Lw Nn Oe) Hw(Lw Oe Pc Qa) Fr(Nm Oy Pd) Mp(Hq Pb Pd) Ir(Is Iv Ok) Qa(Ji Ok Pb) Jg(Ng Og Oi) Nm(Jp Nw) Jr(Is Iv) MgNg MmPb MwOg LhOn NwOe OiPc} Nf{Nn(aA Et Fr Hu Hv Hx Ii Ij In Ir Iv Jg Jo Jq Jr Lh Ma Me Mf Mr Mu Nb No Nt Nv Pa Pe Pg Po) Fr(Hx Ij Im In Ir Iv Jq Jr Me Mg Mp Nb Nl Nm Nt Nw Oe Oz Pg) Mz(aA Im Iu Jg Jk Jl Lh Lw Mp Mt Mv Mw Nb Nt Oe Oh Om Pg Qa) Qa(aA Im Jg Jl Jp Lv Ma Mp Mt Nb Nm Nq Nt Nw Oe Oh Om Pg) Om(aA Hv Is Jl Jp Lv Lw Mp Mt Nb Oe Og Oh Pc Pg Qd) Nb(Im Is Jl Jp Lv Ma Mg Mm Nw Oe Pc Pg Qd) Nw(Hv Il Jk Ma Mg Mp Nm Nq Nt Oe Pc Pg) Nq(Hu Im Ir Is Jl Jp Jr Lv Nt Pg) Lh(Im Is Lv Lw Ma Mg Mm Pc Qd) Pc(Hv Hx Ij Il Jq Nt Pg Po) Lw(Hx Ij Mr Mv Nr Nt Pe) Mg(aA Hv Is Mr Ng Pa Pg) Mw(Hu Lv Ma Mp Og Oy Qd) Jg(aA Is Ma Mp Mt Pg) Pg(aA Im Oe Oz Pf) Nt(Lv Ma Mm Oe) Mp(Hv Im Ns Pd) Mt(Is Lv Ma Qd) Mm(Hv Ij) Jp(Ij Jq) NmJl LvMv MaHx MhIs NvOe} Ji{Of(Hv Hx Iu Jg Mg Mk Mr Mv Nb Nq Nr Nt Nu Om Oz Pa Pc Pg Po) Nk(Fr Hr Hv Hw Ij Im In Jn Lw Mg Mm Mz Nm Ny Oe Om Pb) Ny(Fr Hv Hx Iu Jg Jp Mg Mr Nb Nq Nr Nt Ok Pa Pe Pg) Om(Fr Hv Jg Jl Jp Mg Mw Nb Nq Nr Nt On Pc Pg) Jk(Hr Hv Hw Ii Ij In Na Ng Nm Oe Og Oy Pd) Jl(Hw Hx Ii Ij In Jn Jo Lh Mr No Pd Po) Hv(Hr Hw Ij Il In Jn Jr Mm Mz Na Qa) Pd(Il Mg Mp Mr Nr Nt Oz Pa Pe Pg Po) Nm(Il Is Iu Lw Mg Mp Nt Nu Ok) Hr(Fr Hx Iu Jp Mr Nb Nt Oz Pg) Il(Hw In Jn Mp Na Oe Og) Jg(Jh My Og Oi Oy Pb) Pa(Hx Ii Lh Mz Oe Po) Nt(Ij In Jo Mz Na) Mw(Md My Og Oy Pb) Is(Ir Jn Jr Js Mx) Jp(Hw Ij Iu Jn Mm) Nr(Hw Jo Mz Na) Oe(Fr Iu Jn Mz) Nn(Jn Jr Pc) Md(Lw Mm) Mg(Ng Og) Iv(Ir Jn) Pg(Mz Pf) FrMm NqNg MpHq NeNl HwPc IuQd LhOn} Ma{Im(Hv Hx Ir Iu Jg Jk Jq Mj Mp Mr Nb Ni Nk Nl Nr Nt Oh Pa Pe Pg Po) Nk(aA Et Fr Hv Hx Jg Jk Jp Jq Mm Mr Nb Nm Nn Nr Nt Om Pa Pe) Oe(aA Hx Ir Iu Jg Jk Jq Mr Mz Nb Nr Nt Nv Nw Pa Pe Pg Po Qa) Nl(Et Fr Hv Hx Jg Jk Jp Jq Mm Nb Nn Nw Om Pc) Jg(aA Hu Hv Ir Iu Mp My Nr Ns Of Og Oi Oy) Mm(aA Hv Hx Il Ir Jr Mr Nb Nr Nw Pa Pe) Mp(Hq Hv Hx Ir Jk Jq Mr Nb Nr Pa Pe) Nn(aA Hv Hx Il Ir Nb Nr Nt Nw Pc) Jo(Ir Jk Mr Nb Nt Nv Pa Pe Pg) Lv(Ir Jq Mb Nb Nr Oz Pa) Of(Hx Jk Mw Nb Om Pa Pg) Pc(Il Iv Jq Nb Nt Pg) Oz(Nr Pa Pb Pe Pg) Mw(My Ng Og Oy) Hv(Iu Jp Nt Nw) Is(Ir Iv Jr Js) Jk(Hu Ng Og Oy) Nm(Jp Nw Pa) Pb(Hx Pe Qa) Pg(Hq Oy Pf) Fr(Ir Oy) Nb(Md Og) Iu(Ir Jp) Pa(Hq Jq) MgNg HwQa HxOg JlNw PePf} Cx{cJ(aJ Al Ap Aw Ba Bb BC Bn bO bV bZ cG Cp Cq Cw Dd dE dF Di dK fR) aA(aI aK aM aV aZ bB Bg Bn bO bZ cG Cp Cq Dc Dd dE Di Fr) aZ(Af aG aO aU Aw bA Bg bH Bn bO Cp Cw dE dF Di dK fR) De(aG aJ Ao aP As aV Ax bA bC bO bV cE Co Dc Dd dE) bC(aJ As aV bA Bb bO cB Cw dB Dc Dd dE Di FR) dE(aI aL aU aV bA bO cG Cp Dc dF Dk Fr) aV(Al aP

Figure 29 Continued

Aw BA cG Cq Dc Dd Fr) Di(aG aJ aL aP bA bO cG Dc) bO(Al aP Aw BA Cw Dc) cG(As bQ bR cD cL Dd dH) aP(aU Aw Bg Dd dL) aJ(Aw cB Cu) aU(Dc Dd dF) bA(aG bW cB) fR(Aw aX Cq) Fr(aM dC) AfAo DcdC DdbZ aLbE} Lw{Im(Iu Jk Mg Mj Mk Mr Mv Mz Nb Nk Nl Nr Nw Oe Og Oz Pe Pg Po) Hv(aA Hw Ij Il In Iu Jq Mg Mm Mz Na Nn Nt Nw Ok Pa Pg) Og(Hx Jk Mg Mj Mv Mw Nb Nu Om Pa Qe) Pb(aA Hx Ij Jo Lh Mr Nr Om Pa Pg Po) Oe(Et Ir Jg Jk Lx Nb Nt Nv Nw Pa) Md(Hx Ij Lh Mp Nr Om Pe Qa) Of(Jk Mr Nb Nr Om Oz Pe Pg) Pc(Hx Iv Mj Mr Nn Nr Pa Pe) Mm(Hx Il Mj Nb Nr Pe) Ok(Jk Jo Mz Ni Nk Ny) Nn(Mr Nr Nt Pe) Mp(Hq Nd Ns Pd) Ng(Il Mv Mw Nq) Hr(aA Hx Lh Nr) Oz(Hq Lz Ns Pd) Pg(Hq Oy Pd Pf) Nk(Et Mg Nw) Is(Iv Jn Mh) Qa(Hw Ij In) aA(Hw Jq Na) Nm(Jg Nw) Mw(My Oy) Mz(Iu Pa) Ny(Hx Nb) Pe(Pd Pf) NrMg NtHq Irlu IvJr JgOi} Fr{Ng(Hv Hx Ij Iu Jk Jr Mp Mw Nl Nn Nt Pg) Oy(Hv Ij Ir Jg Jl Mg Mw Nk Nt Pc Pg) Cu(Ad bQ Cp Cq Cw cX dB Dc dG dK) Of(Hv Hx Jg Jl Mc Mg Nb Nt Om Pg) As(aM Ax bA bC cB cG Cq De Di) Bn(aM bA bC cG Cp Cq dC De) Pb(Hv Hx Ij In Nr Oz Pe Qa) Dd(Ad bJ Bo Cp Cq Cw Dc) bC(aV bQ cB dA dB dH) Hr(Hx Jl Nb Nr Pe) cE(aG aL cB cG dC) Nt(Hq Jo Lx Ly) Og(Hx Ij Jg Mg) Nm(Im Jp Nw) Nk(Im Oe Oz) Ir(Is Iu Oe) cX(aA dC dE) Ax(cB dK) Md(Mp Qa) My(Jg Mw) Hq(Hx Pg) Hw(Hv Qa) Is(Jr Js) Pf(Pc Pg) aP(cK dG) dC(Aj Di) AdDc AfDc AlaV NnPc LyNl MmJr MpNd MzOe ImJp JgOi JlOz aLbE bQcG bWdH} Oe{Mm(aA Hv Hx Ij Il Im Ir Iv Jk Jp Jq Jr Mj Mr Nb Nr Nt Nv Nw Om Pa Po Qa) Lv(Et Il Iq Ir Iu Jg Jk Jq Lx Nb Nr Nt Nv Ny Om Pa Pe Pg Qa) Jp(aA Hx Il Ir Iu Jg Jk Jq Mg Mz Nb Nq Nr Nt Om Oz Pa Pg Po) Jg(aA Ir Is Iu Mp My Mz Ns Nt Ok Pa Pg) Nn(Hx Ij Il Jk Lx Nb Nr Nt Nv Po) Ok(Hv Ij In Is Jk Jn Jq Mz Ni) Mz(Iu Jk Mg Nq Nt Pa Pg) Nw(Iu Jk Mg Nk Nt Pg) Pc(Ij Jk Lx Nb Nt Nv) Pg(aA Hq Ly Mg Oz) Im(Nb Nv Po) Is(Iu Jl Jr) Mg(Ir Nr) Pb(Nb Qa) WmQd NtLy JlNv} aX{dI(aI aJ aL aO aP Ar BG bH bL bQ cH cS dF Di Dk dM) bV(aJ aO aP bE BG bO bP cH dD dF Dk dM) dH(bE bF bL bO bP bZ cG cH cO cS dD dG dM) cB(aJ aO aP bA bH bL bS cH dF dM) cH(aI aJ aL Aw Ax bB cJ Cp dF) bO(aA aO Aw aZ bG cJ Dd) Al(aC bN Bo cD dD Di) Ax(As aV bQ cQ dN) aA(aL bB bG dA Dd) dK(aL bG cZ dD dF) cJ(aL aO bA bG) Dd(aC bF dD) Dk(aU aV cQ) cZ(bH bJ cS) Cp(Ad Cw) Cq(aV bB) De(aC bA) aL(bH cM) AfBn AraU AwaC BgbQ BoCu aJbG aPbR} Jg{Og(aA Hv Hw Ij Im Ir Iu Iv Jk Jq Jr Mg Mj Mp Nb Nn Nr Nt Oh Pc Pe Pg Po Qe) Of(aA Hv Hx Ij Il Is Jk Lv Mp Mz Nb Nr Nt Pa Pe Pg) Oy(aA Hv Hx Il Is Jl Mp Mz Nn Nq Pg) My(aA Hx Il Is Jl Mp Mz Nn Nq Pg) Pb(aA Hx Is Mz Nr Oz Pa Pe Pg Qa) Mp(Hq Hu Im Md Mz Nd Ns) Ng(Hv Jp Mm Nv Oh Pc Po) Lv(Hu Nk Nm Ns Oh Oi) Oi(aA Is Jl Mz Oh) Nn(Hu Md Ns) Is(Hu Nm Ns) Mz(Im Iu) Jl(Jo Nm) aA(Hu Ns) ImOh OkOm} Mg{Ng(Et Hv Hx Ii Ij Im Ir Iv Jq Jr Lh Lx Mj Mm Mn Mp Mr Mv Nb Nk Nn No Nr Nt Nu Nv Ny Om Oz Pc Pe Po Qa) Og(Hx Il Im Ir Jp Lv Mw Mz Nb Nr Nw Om Pa Pc Pe Pg) Im(Hv Ir Mj Mz Nb Nk Nr Nw Pe) Is(Ir Iv Jo Jr Js Mh Nm Oi) Nw(Md My Nk Nm Of Pb) Pg(Hq Jo Of Oy Pf) On(Jh Mw Nv Om) Lv(Ir Ly Nr) Mz(Jl Jp Nk) Qa(Hw Md Pb) Mw(My Oy) Nb(Of Pb) Ir(Iu Jo) Jl(Ii Mh) Jp(aA Nm) Pc(Nr Oi) NtJo IlaA OzPb} Cu{dK(Ad Af An As aZ Bg bJ Bn Bo cH Cp Cq Cw cX dB Dc dE dL) cX(aG An As aZ bE bJ Bn BO cJ Cq dB) As(Ao Aw bC bV bW bZ Co dF) De(Ad Af An bJ Cp Cq Cw Dc) dH(Ad An aP bW bZ Cp Cq Cw) cJ(Af Bo cH Cp dB DL) cK(Ad bC Bn bW Cq Cw) bW(Bn Cq dB dG) Bg(Ad aZ dE) bC(cQ dA dB) Aw(Cp Cq) Ba(Af Ct) Bn(aU cG) Bo(cS dC) aV(Ad Cw) dG(aJ aP) AxCs CpcS CqbV CvaZ aLbE bOdB bQbZ} Is{Mh(Im It Iu Jp Mp Mz Nq Nw Oh Oz Po Qd) Ok(Hv Ij In Iv Jn Js Mz Na Ny Om) Qd(Ir Iu Iv Jn Jr Js Lz Mx Qb) Nm(Et Jl Mz Nt Nu Nw Pg) Jr(Im Jp Mm Mp Mz Oz Pc) Ir(Jp Mm Mp Nn Pc) Iu(Jl Mp Nt Oh Pg) Mw(My Ng Of Oy) Js(Mm Mp Nn Oz) Nq(Hu Ng Og) Nb(Hr Of Pb) Iv(Jp Lv Mm) Hr(Nr Pe) Jl(Og Oz) Pg(Pf Qb) NtJo MpHq MuHu LiLj OfOm OhOn} aA{cJ(Af Ap aZ bC BG bH bJ Bn bO bZ cS Di dL) cB(Al bG bH bJ bO bS bW bZ dE dK) bC(bB Bg bO bV dA dB dE dH) dE(aG aI aL bO bW cC dC) aZ(aI BG bO bW bZ) bZ(cE cX dC dH dK) cS(bG bR bV dB dG) De(Af Bn cX) Pg(Oz Pc Pf) nB(mP nT nU) Mp(Hq Nd) aL(bE bJ) bO(dB dC) cG(bJ dH) nK(kG nR) AwBn BgcX NnMx MuHu OiPc aDaI bGdK nUmM} Mw{Oy(Hx Il Im Jk Jl Jp Md Mm Mp Mz Nn Nw Ny Of Ok Pb Pg) Og(Il Im Ir Iu Iv Jl Jp Jr Mm Mp Mz Nn Nt Nw Po Qe) My(Im Jl Jp Mm Mp Mz Nn Nw Ok Pc Pg) Ng(Jk Jl Jp Lv Mm Mp Nq Ok Pb Pg Qd) Of(Hu Jl Jp Lv Mz Nb Ns Nt Pg Qa Qd) Pb(Hx Lv Mz Nr Pe Qa Qd) Md(Hu Mp) Ny(Hu Ok) MhOn OkOm} Lv{Ly(Hv Iu Jk Mr Nb Nd Nk Nq Nr Nu Nv Oh Om Oz Pe) Oz(Hv Il Iq Ir Jk Mr Nb Nk No Pa Pb Pe Pg Po) Og(Jk Mv Nb Nm Om Qe) Nk(Et Iq Jq Nm Om) Qa(Hw Ij In Md Pb) Jo(Hw Jk Nv Om Pg) Oh(Hv Nr Om Pa) Pb(Nr Ny Om Pe) Ng(Jk Nq Om) Hu(Jk Mu Nq) Nm(Et Nv) Of(Mv Nb) Pd(Pe Pg) Pf(Pe Po) IqIu LiLj} Pc{Oi(Et Hu Hv Hx Ij Il Ir Iu Iv Jk Jq Jr Lx Mj Mp Mr Mv Nb No Nu Nv Ny Om Pa Pe Pg Po Qa) Nn(Hv Hx Il Ir Iv Lx Mr Nb Nt Nw Oz Pg Po) Og(Hx Ij Jk Nb Nv Om Qe) Pb(Hx Nb Oz Pe Qa) Md(Hv Nb Om) Jk(Hu Ng Oy) Mm(Il Me) Qa(Hw Ij) Om(Ng Of) Pg(Oy Pf) EtIl NmNw NtJo MpOn} Mp{Hq(Hv Hx Im Ir Jk Lh Mr Nb Nk Nr Nt Nw Om Oz Pa Pe Pg Po) Nd(Hv Il Im Jk Jl Mr Mz Nr Nt Pa Pe Pg) Md(Hv Il Mz Nb Nt Nw Om Pg Qa) Im(Hv Ij Il Mz Nb Nr Om Pe) Om(Jo Ng Of Og Oy Pb) Jl(Jo Mk Mz Oz Po) Lz(Nr Oz Pa Pe) Pb(Oz Qa) NmNw NtLy NgJk} aZ{bO(aG aI aJ Al aO aP Aw Ba bC BG bH bL bW cJ DE Di dK) aJ(aI aL BG bZ cB cJ cN cX De) Bn(aI Aw Bg bW cG Cp De) cX(aO aP bA cJ cR De Di) dK(aI Ax BG Di) aP(BG cJ dH) bW(As cD cF dH) Al(bZ De Di) aI(Ba Di) bA(Bg bJ) AfDe CofR bGcJ bZcE} Mm{Nm(Ij Im Jk Nt Nv Nw Om Pe Pg Po Qa) Im(Hv Ij Jp Mj Nb Nk Nr Pg) Ng(Ij Il Jk Mv Nt Nv Om) Jp(Hv Il Jr Nt Pe Pg) Og(Hx Ij Il Nb Om) Pb(Hv Hx Nb Oz Qa) Me(Nk Nn Nw Pa) Nt(Hq Jo Nd) Qa(Hw Ij Md) Of(Nb Om Pg) Jk(Hu Oy) Pe(Iu Oy) Pg(Hq Pf) IlJr} cS{dH(aI aJ aO Bc bQ bZ cG cO dD dF dM fR) Dd(Ad An As BN Bo cH Cq Cw dB dL) bR(bA bP bZ dF dM) Bb(aC bG cK dD) Cp(Ad Af Aj Cw) dL(aI aJ cZ fR) As(Aw bN Dc) Bn(Aw Cq De) cX(bN bP cR) dG(aJ aP dF) Af(Aw Cq) Dc(Ad cK) bG(cC cE) AjCh BccK aIbN aMcH} Ok{Jk(Ij In Jo Jq Mz Na Ng Nm Og Pd) Il(Ij In Jo Na Ny Og Oh Om Pd) Mz(In Jl Jn Ni Ny Om Oz Pg) Jl(Hx Ij Jq Mr Nm Om) Nm(Et Nt Nu Nw) Hv(Jn Ny Pg) Iv(Ir Jr) Jq(Oh Oz) Pe(Pa Pf) Pg(Na Oy) PoPd MuHu MvOg NbNy NeNl IjOz IuJo JrJs} aP{dG(aG bA bB BG bO bV cG cJ cO dA dF dH dI dK) dH(Af aL Bg bN bO cX dA DE Di) cJ(BG bM bN bO cX dE Di dL) cB(Al BG bH cX dL) cX(bO bR dC dE dL) dL(aL bO dK) Bg(cE cK) De(Af Bn) bFcE bRbZ} Jp{Nm(Ij Im Ir Iu Jk Jq Mz Nw Om Pg Po) Oz(Iu Nr Pa Pb Pe Pg) Im(Iu Mj Nr Nt Pg) Of(Jk Nb Nq Om Pg) Ng(Jk Nq Nt) Hu(Jk Mu Nq) Og(Il Jk Nb) Pg(Hq Oy Pf) Qd(Lz Qc) Oh(Il Jl) Pb(Nr Pe) NtJo MzIu LiLj PePf} cJ{Di(aJ Ap As BA Bb bC bO bZ cX dE) dE(Aw Ax bA Bg Cp Dc De Dk) Bn(Aw cG Dc De) Bg(aJ bA bC) bO(Al Ap Ba) Ax(Cs dK) De(Af cX) aJ(bM dL) bA(Ap cT) AjBa AsbC DkdK} Nn{Om(Md Ng Of Og Oy) Pb(Hx Nb Oz Qa) Md(Hv Hx Qa) Ng(Il Jk Pg) Og(Hx Ij Nb) Oi(Mj No Ny) Nt(Hq Jo) Hu(Il Jk) Oy(Il Pg) Pe(Hr Pf) NbOf HwQa IrIu IvJr PfPg} Qd{Lz(Iu Lh Mr Nb Nr Oz Pe Pz) Wm(Ih Ii Ik Im Jo Js) Nm(Et Nt Nw Om Oz Pg) Iu(Jk Nt Pg) Nb(Hr Pb) Pz(Jk Nt) Oz(Pa Pb) MuHu HvLj HxQb IvJr PcPf} Jl{Pg(Hq Of Oy Oz Pd Pf) Nm(Jo Nw Of Og) Nq(Jo Ng Of) Nt(Jo Ly Lz) Mv(Ng Of) Hr(Hx Ij) Oz(Mz Og) NuLz MhNw MuHu NbPb HwQa JoOh LiLj OfOm} Pb{Nb(Ij Li Lx Lz Mv Mz Nu Nw Pg Po Qa) Oz(Li Mv Mz Nq Nw Om Pg Qa) Om(Mz Pe Qa) LzPe} aJ{cB(bC bG bM bO cX dE dG dL) aL(bE cX dG dL) cG(dG dH dL) De(Af Bn) aI(dG dL) dH(bQ bZ) bCcX cOdG} Im{Oh(Hv Mz Nb Nr Om Pa Pe) Nb(Hr Nk Of Og) Pg(Hq Ly Oy Pf) Mz(Iu Nk Nq) Nw(Iu Nk Nm) NtLy} bA{dE(aI bC bW cB cC cX) cT(aG cB cX dC) cX(aG bC cR) As(bC De) bW(cB dH) AfDe AwBn aMbJ bMdK} Of{Om(Hv Hx Il Jk Mz Nb Nl Nq Nr Nt Oh Pa Pe Pg) Nb(Mv Mz Pg) Jk(Mz Nw) PfPg} aL{bE(Al Ax BG bH Cs cX Di) dE(bW Cp cX Di) As(bC bW) BnDe} cG{Bn(Aw cE Cp Cq Dd Dc dH Di) cE(BG) cX(dE dH) AfdH} bC{As(aI bO Cp Cq dF) cX(bO cR dE fR) bO(dB dE)} Nw{Nm(Iu Nt Nu) Jk(Ng Og Oy) NqNg IlOg} Pg{Pf(Hq Lx Mz) Jo(Iu Nm) NqNg MdHq NvOn} dK{Dk(Aj Ax bM cX dB dE) bG(bM cR)} Mz{Ng(Jk Nq) Hr(Nb Pe) JkOg LiLj} As{Aw(Ax bO) AxbW DcDe DdbZ} Bn{De(aV Dc dF) AwbO} On{Qa(Hw Ij) Li(fR Lz)} Om{NqNg MdOh IlOg} nU{mU(kG mF nN)} bW{AxcB bQdH} cX{dE(aG bO)} NqHqHu NtLyHv NbHrQa nRmWnK

Figure 29 Continued

Constrained panels with 3 analytes, where 1.0E-3 >= 'model p-value' > 1.0E-4. Contains 4,807 panels of 625,624 total panels evaluated. :
Ml{Jq(aA Et Hw Hx Ii Ij Il Im In Ir Iu Jg Jj Jk Lh Lx Mg Mh Mk Mp Mr Mv Nj Nk Nl Nq Nu Oe Pa Pe Po) In(Hx Ii Im Iu Jg Jo Jr Lx Mf Mp Mu Mv Nj Nm No Nq Nr Nt Nv Nx Oh Pa Pe) Nr(aA Et Hr Ij Ir Iv Jr Js Lx Mf Mp Mt Mv Nj Nm Nq Oe Oh Oz Pb Po) Hx(aA Et Im Jg Jn Jr Js Lx Mf Mg Mp Mt Mv Nj Nm Nq Nt Nu Oe Oh Om) Jj(Et Hw Ih Ii Im Ip Jm Jn Jr Li Lx Mn Mr No Nu Nx Ny Pa Qe) Js(aA Et Ii Im Iu Jg Jo Jp Lh Lx Mg Mp Nq Nv Nx Oe Pa Pe Po) Ij(Et Ii Im Ir Iu Jg Jr Lh Mg Mp Mr Nb Nj Oe Og Oh Pa Pe) Pe(aA Et Hv Im Ir Jg Jn Lx Mf Mg Mp Mt Nv Oe Oh Om Oz) Pa(Et Hq Jg Jn Jr Lx Mf Mg Mv Nj Nm Nu Nv Oe Oh Om) aA(Et Hv Il Ir Jk Jr Lx Mf Mk Mn Nm Nt Nu Nx Oe) Jr(Et Ii Im Iu Jg Jk Lx Mg Mv Nj Nu Nv Om) Hv(Ir Iu Jg Lx Mf Nj Nq Nu Nv Nx Oe Pg) Ii(Im Jg Jn Jp Lx Mg Mm Mp Nj Oe Oh) Om(Hw Im Iu Mh Mr Nj Nk Nl Of Oh Oy) Ir(Et Im Iu Lx Mv Nj No Nq Nu Nv) Mg(Hw Il Jn Lh Mh Mr No Po) Nj(Il Iu Lh Lx Mv No Po) Et(Hw Il Iu Mh Mv Oe) Nt(Hq Im Jg Ne Po) Lx(Il Iu Mr Nl Oe) Jg(Iu Mr No Ns) Mp(Jn Nd Po) Mv(Hu Ng Oe) Im(Jo Lh Po) Nn(Hw Jo) Lw(Fp Me) Hu(Jk Mu) Jn(Mm Pc) Lh(Hq Nf) WmLv NmPg NoOe NsMw MafR MeNv MrJp NbOi NgJk JoPc NyOf} Oe{Nj(Hx Ij Il Im Ir Iu Iv Jg Jk Jq Jr Lh Lx Mg Mj Mr Mt Mu Mv My No Nq Nr Nu Ny Pa Pe Po Qa) Im(aA Hv Hx Ij Ir Iu Iv Jg Jj Jk Lh Lx Mu Mv Nk No Nq Nr Ny Oh Om Pa Pe Qe Wm) Jg(Hu Hv Hx Iv Jk Jq Jr Jt Lx Mg Mj Nb Nl Nm Nr Nu Oh Oy Pc Pe Po Qa) Pa(fR Hv Ij Ir Iv Jj Jq Jr Jt Lx Mg Mv Nm Nq Nu Ny Oh Om Oz Qa) Iu(Et Hv Hx Ij Iv Jq Jr Lx Mn Mp Mv No Nq Nr Nu Ny Om Pe) Mg(Hv Hx Il Iv Jk Jq Jr Lx Mj Mr Nb Nk No Nu Pe Po Qa) Ma(Et fR Ij Il Iv Jr Lh Lx Mp Nk Nm No Nu Ny Om) Nq(Hv Hx Ij Ir Iv Jq Jr Lx Nb Nf Nr Nu Pe Qa) Jj(Et Hx Ih Ii Ij Ir Lh Lx Nb No Nr Ny Qa Qe) Jk(aA Et Hu Ir Jq Jr Jt Lx Mp Nb Nm No Nr Qa) Nu(aA fR Hv Hx Ij Ir Jq Jr Nb Nr Pe) Mv(fR Hv Hx Il Ir Iv Jq Jr Nb Nr Pe) aA(Et Ij Il Ir Lx Nb Nf Om Po Qa) Nb(Et Hr Iv Jr Lx Md Of Qa) Nr(Iv Jq Jr Lx Ny Oh Oz) Om(Ir Iv Lw Nk Nl Oh Pb) fR(Et Jp Lv Mm Mt Ok Qa) Nf(Hx Ij Jq Lh Pe Po) Et(Hv Hx Il Jr Nk) Lx(Ir Iv Jt Oh Pe) Hx(Hr Iv Oh Pb) Qa(Hw Ij In Md) Jq(Il Iv Nk Pe) Jt(Ir Jr Po) Oh(Ij Il Pe) Oz(Pb Pe Po) Ny(Hv Iv) Nmll MwMy Nklj PbPe} Cx{dK(Af aI aL aV Aw Ax aY bA BB BC Bg bO bZ cB cG Cp Cq cR dB Dc Dd DE dF Di) Dd(aG aJ aK aL aM aO Ap Aw bB Bc Bg bL Bn bO bQ bW cB cW cY dC dE dF Di fR) bW(AL aM As aV Ax Bb Bg bO bP bR cB cD cF cK cR cT dB Dc dE dH Di) Di(aI Al Ap aU aV Ba Bb Bc bZ Cp Cq Cv Cw dC DE dF fR) cG(aJ Al bF bJ bO bU cA cC cF cK cN CO dA dB Dc dG dl) Cq(aG aJ aM Ap As aU bM bO bV cB cD cF cR Cv dB dE) aV(Af aO Ap Bb Bc Bn bQ bS bZ Cp Cw dF dI Dk dM fR) aJ(Af aL aM aU Ba Bb Bg bO bZ Cp Cw Dc dE Dk dL) Dc(aG aI aL aM Ap Aw Ba bB bZ cB cY dF fR) aU(Al Ap aQ Ax Ba Bb bO bV cT Cw dB dM fR) dE(aG aK aO Aw Ba Bb Bc Bg Bn bZ cB Cw cY) Bb(aG aI Al aM Ax bB bO bZ dB dC) aM(aI aL aO Aw bA bL bZ Cp dF) Al(aI aL bB bZ cB cR cY De) bO(Af aG Ap bE Cp dC dF fR) bA(aI aL Ap Aw bZ cT Cw) cB(Ax bS bV dI dM fR) Cp(aG Bc bV cR fR) bZ(aG As Ba cE dH) Ax(aG Ap Aw Bn) fR(aK Bn cD Co) Bc(Af Bg dC) Cw(aG bV dC) De(aL dC dF) Aw(As cE) bS(bR cD) AfbV ApBg BnaG aIbE bCcK cEdF} Nf{Nq(aA Et Hv Hx Ii Ij Il Iu Iv Jg Jq Lh Lx Ma Me Mf Mg Mr Mt Nb Nj Nl No Nr Nv Oi Om Oz Pa Pe Po) Mt(aA Et Hv Hx Ij Il Im Ir Iu Iv Jj Jp Jq Jr Lh Lx Me Mg Mv Mw Nj Nt Nv Nw Oz Pa Pc Pe Po) Jg(Hv Hw Hx Ij Il Ir Iu Jq Jr Lh Lx Me Mg Mj Mr Nb Nt Nv Oh Pa Pc Pe Po) Mg(Hx Ii Ij Il In Jk Jq Jr Lx Ma Me Mj Mp Mw No Nr Nt Nv Om Pe Po) Mp(aA Hx Ii Ij Il Ir Jk Jq Lh Ma Mr Mv Nb Nt Of Pa Pb Pe Pf Po) Jq(aA Hv Hx Il Jk Lh Mr Mv Mw Nb Nr Nt Nu Pa Pe Po Qa) aA(Hv Hx Ij Il Ir Lh Li Mv Mw Nm Nt Nx Oz Pe Po) Nt(Hx Im Lx Mv Mw Nb Nd Nj Om Oz Po) Lh(Hv Ij Jj Jp Mv Om Oz Pb Po Qa) Mw(Im Ir Lw Ng Ns Oh Pc Pe Qa) Nb(Ij Jj Lx Mv Nu Og Oz Pe Po) Om(Hx Il Ir Iu Ma Ng Nw Oz Po) Pe(Im Lz Mv Oz Pb Pf) Lw(Ii In Jo Li Me) Qa(Et Jj Mv Nj Oz) Nw(Hx Mv Nu Oh Oz) Im(Ii Jo Mr Pa) Oh(Hx Ij Mr Po) Nv(Hv Me Pa) Nm(Hv Pg) Ma(Ii Mr) Jo(Jj Pc) Oz(Pa Po) EtIj MvIr InPc IuPg} bW{Bg(aA Aj As aV Ax aZ bA Bb bM Bn bO bP bQ bR cD cE cF cJ cK dB Dc dE dH Di) aL(Al aV Ax aZ bJ Bn bQ bR bU cA cC cD cE cF cL cN CO cR dB dG dH DI) aZ(Al aM aV Ax bA bG bJ bP bQ bR bU cA cB cC cE cL cN cR cX dE DI) As(aI aM Ar Aw BA bG bO bZ cB cG Cp Cq Dc DD De dF Di Dk) bG(aV bJ bM bP bQ bR bU cA cB cC cD cE cF cL cO cR dE dH dI) bA(bJ bM Bn bP bQ bR bU cC cD cE cF Ct cX dA dB dG Dl) Ax(aA aV Bb bM bQ bR cD cE cF cJ cK Cs dB dE dG dH Di dK) Dc(aG aV bJ bM Bn bO bP cB cD cF cK dB dE dG dH) Di(aA Al aV Bn bO cB cD cK cX dB dH) aM(aG bJ bM Bn bO bP cX dB dE dL) cB(Al Ar Ba bM Bn bO bV cR dE dM) Cu(aV bQ bR cD cF cN dA dL) bO(Al bM Bn bP cF cX dB dE) dH(aA aJ aO bZ cG dF fR) Al(aA aV bM cD cJ) Bn(aA Cp Dd De dF) dB(aA Ba bM Dk) cG(bR cF cL) cX(cF cR dE) dG(aJ dF Fr) bM(cT dK) bZ(bR cE) dE(aI Dd) DkaV FrcK aJdL bNfR bScU cEdF} dE{cX(aI aJ aM aO aU Aw aZ Ba BB Bc BG bL bQ bZ cB cC cJ Cp cR DC dD De dF Di DK dM fR) Bn(aG aJ Al aO aP aU BA bC bF bG bL bQ bZ CO Cq Cp Cq DC Dd De Di dK dM) dK(aI aL Aw Ax bA BB Bc BG bM bQ bZ cB cJ Cp Dc DD dF) Bg(aA aI aJ aL aU aV Ax aZ bA Bb bC cG DC Dd De) al(aJ aM Aw Ax aZ Ba bC bG Cp Cq Dc Dd De Di dM) aL(aJ Al aM aP Aw Ax aZ bC bG bZ cC Cq Dc Dd De) aZ(aG aM aO Aw bA bG bQ cC cJ Cp Cq dF dM) cC(aJ aP bC bG bQ bV bZ cG cJ cT dF dM) aU(Al Ax Bb bG Cp Cq Dc Dd Di Dk dM) bG(aG aJ aM bC cB cD cJ dC De) Dc(aG aV bC cB cY dC De Di) cJ(aG aJ aM Ba bC bZ dF dM) aV(Al Aw Ba Cp Dd De Dk) aM(aG aJ aO bZ cO dF) cB(Ax bV Cq Di dM fR) Aw(aA aP Ax bA bC) De(aA aJ Ax bA dF) bC(aJ aO Cp dF) dC(aJ aP bZ dM) aG(aJ bA bZ) Cp(As Bn) DdbZ aPbR bQdH cEcG} Jj{Nj(Et Hv Hw Hx Ih Il Ip Iq Iu Iv Jm Jq Jr Js Lx Mj Mn Mq Mr Mt Mu Mw My Nb Nd No Nr Nu Nx Ny Oh Oz Pa Pq Qa Qc Qe) Nu(Hv Hw Hx Ii Im Iq Ir Iv Jm Jq Jr Lh Mj Mn Mr Mu Mv My Nb Nk Nl Nr Nx Oh Pa Pe) Nk(Et Hv Hw Hx Ih Ii Im Ip Iq Jn Jq Lx Mu Mv Mw My Nb Nm No Nq Nr Nx Ny) Nl(aA Et Hv Ii Im Ip Iq Jm Jq Jr Lx Mj Mn Mu Mw My Nb Ne Nm No Nx Ny) Mn(aA Hv Hx Im Ip Iv Jr Mp Mv My Nb Nr Oh Pa) Im(Hv Hx Ih Ii Jr Js Mj My Nb Nr Oh Pa Qe) Nx(Hv Hw Hx Iv Mr Mu Mv My Nb Nr Pa) Ip(Hv Hw Iu Jr Mr My Nb Nr Oz Pa) Jr(Et Ii Jm My Nb Nr Ny Oh Pa) Mw(Hq Hx Md Mh My Ny Oh) Hv(Et Iu Jm Nm Nw Ny Oh) Iu(Et Hx Jq Lh Mj Oz) My(Ih Iv Jn Jq Ny) Nb(Hr Jm Lx Md Mp) Nr(Jm Ny Oh Oz) Mv(Hx Ir Jq Nw) Pa(Jq Nm Oh Oz) Mm(Iq Jm Lh) Pb(Jo Ny Qa) Mr(Oh Oz) Hw(Jo Qa) LxOh MpLh HxIv PePf} aZ{cX(aG aI aL aM aN Aw Ba bC bG bL bQ bZ cC cG Cq CV cW DC dF dK dM fR) Bn(aG aJ Al aO aP aU BA bC bF bG bL bQ CO Cq Cw Dc Dd dF Di Dk) Al(aA aG aI aL aO aU aV bA bG cD cG dF fR) bJ(aA aI aL aM aO bQ cG CO Cp Cq Dd dF) As(aA bQ cG CO Cp Cq Cw De dF) Di(aG aJ aL aP aU BA Bg bZ fR) dK(aA Aw bA bB bQ bZ cJ cR dF) bG(aG aI Ap bA cC cD cE cR fR) cO(bQ bR cC cD cE cF cL cN dH) Af(aJ AO Aw Cp Cq Cw dF) Bg(aL aU Ax Ba bC cD cE fR) Cv(AP Bb Cp Cw Dc Dd) cG(cC cD cE cL cN cR dH) Ax(aG aI Ap aU Aw De) Co(aA aV cD cE cL) bA(aG aI Ch cJ De) cC(bH bL bQ bS bZ) Ba(aL aU bZ cD) cN(aP bQ dM fR) aO(aF cE cJ) aU(aQ Dc dM) Ch(aJ fR) Cq(cD cR) bH(aL cJ) bQ(cE dH) bZ(cJ Dd) AwaV DecL aAdC aldM aMcH bFcE bOfR} Jg{Of(Hw Ir Iu Iv Jp Jq Jr Lh Mg Mj Mk Mr Nl Nq Nv Nw Oh Om Oz Po Qa) My(Hv Im Ir Iu Jp Jq Jr Jt Mg Mw Nb Nl Nt Nw Oh Oi Pc Pe Po) Oi(Hu Hv Ir Iu Iv Jr Mg Mj Mm Nk Nl Nt Nw Pe Pg Po Qa) Oy(Im Ir Iu Jk Jp Jr Jt Mj Mw Nb Nl Nt Nw Oh Pc Pe Po) Pb(Hv Hw Ii Ij Il Jo Jq Lh Me Mj Mq Mr Nt Nv Nw Ny Po) Nm(Hx Ip Jq Jt Lx Mm Mp Nv Oh Pe Pg Po Qa) Ns(Hv Im Ir Iu Jp Jr Jt Mq Nl Nt Oh Pc Pg) Hu(Hv Il Im Iu Jk Jp Nl Nq Nw Oh Pc Pg Po) Im(Hv Ir Iu Iv Mj Nj Nk Nl Nr) Jh(Hv Hx Ij Il Jq Jt Nq Om Pg) Nj(Hv Jr Mj Nr Oh Pe) Qa(Hw Ij In Md Om) Md(Oh Pc Pg) Nt(Hq Jo) Hr(Pa Pe) Oh(Hv Iv) NqMv NeNl NkJq Irlu PePf} cX{bO(aG aJ AI aM aO Ap Aw BA bL bM bZ cG cJ cW DC De dF Di dK dM fR) cG(aG aJ As aV bF bJ bQ bR bU cA cC cD cF cL cN CO cR Dc Dl dK) Di(aA aG al aJ aL aP aU aV BA bC bZ DC De dF dK fR) bC(aG aL aO As Ba Bb bM cB cD cJ cT cV Dc dF dK) aJ(aM Aw Ba Bb bM bZ cJ cR dC De dL) De(aL aP As aV bA bV dC dK fR) aG(aM bL bZ cR cW Dc dF dI dK) bA(aC aI aP aU bL cB dC dK) cJ(Ax Ba Bb bZ cR Dc dF) dK(aI aL Ba bB cR dF) Dc(aU aV bZ dC) cR(al aL cW dF) aM(aO bL bZ) aU(Ax Ba dM) aV(Al Aw Ba) bQ(cC cE dH) cB(bS fR) cE(bZ dF) dC(cW dF) AwaA} dK{bM(aI aJ AI aP Aw Ax aY bB bC Bg bO bQ bZ cG cJ cR cT Dc dD De dF Di dM) Ax(aI aL Ap As aV Aw aY Ba BB bC BG bO cB cG Cs cY De Di) Bg(aA aL Ap BA Bb BC bO cJ Dc Di) bG(aJ aL AP bA Bb bC bO

De{Af(aG al aL aV Ba bV cT dF Di fR) Ba(Aj Ct) aLbJ aQaV} Ir{Iu(Et Jk Mv Nt Nu Om Pg Po) Jt(Hv Il Ji) NrJi MdOm LiLj} aX{cH(aG aH aM cZ fR) bH(aG aM dD) dI(cT dD) fR(cB dH) bFcE bRbS} Om{Oy(Il Jk Pa Pg) Md(Hv Mz Pg) PoJl LyNl MaIu HqPa JtPd} aL{bJ(aM Ba bH Dd Di) Di(aC Ap Ba) aC(bG bH) DdbE} Hq{Nt(Ma Nd Nw Po) Pg(Hv Lx Pa Po) LxMa NvPa} fR{Oi(Ma Mk Pa) cB(bH bS) AjCo MaMm IiJn aHaI cSdG} mW{nR(mE nB nI oP oQ) nU(mM nB) kG(nI nK) mPnB} Iv{Jr(Jp Lv Mz Nw) Js(Ji Lw Nn) MaNd MhNw} Pe{Pf(Et Ji Jt Lx Mz Nt Nw) Jt(Pa Pd)} Li{Lj(Ji Nw Ok Pg Po) LzPa JlPf} nK{oQ(kI nA nB) mP(kI mZ) nRnT nUnA} Md{Lw(Ii Me Mv) In(Nn Pc) WmJq} Nl{Ne(Et Jp Jt Mm Nt) OiPc} Jk{Oy(Nn Pg Po) MaJr MyNw PzJp} aM{bJ(aI aO dF Fr) bFcE} Aw{aV(Af dB) BaCt} Nu{Nk(Jq Ma) LyNw} Lz{Mj(Jp Ma) AaQd} Oi{Pc(Hw Lh) NtLy} Di{BbaG aIbE} Nw{WmMm NtLy} Oy{IuPg JhPc} nU{nNmP kGkI} BaaIcE BgaVdI EtMzNk NnMjMx NsMqJp LvMvMy HxIjJl mPnIkI

Constrained panels with 2 analytes, where 1.0E-6 >= 'model p-value' > 0. Contains 11 panels of 16,069 total panels evaluated. : Mi(Lv Ma Ml Nf Nj Nn Pc) Ml(Ji Qd) On(Nf Pb)

Constrained panels with 2 analytes, where 1.0E-5 >= 'model p-value' > 1.0E-6. Contains 87 panels of 16,069 total panels evaluated. : On(Hr Jj Lv Lw Ma Md Ml Mm My Ng Nj Nm Nn Oe Of Og Oi Oy Pc Po Qd) Lv(aA Fr Is Ji Jj Jl Jp Lw Mm Mz Nn Ok Pc Qd) Ok(Hr Hw Ma Ml Mp Nf Nn Pb Pc Qd) Lw(Fr Is Jl Jp Ma Mi Qd) Qd(Fr Im Ma Mm Nn Pc) aX(CU CX Dc Fr) cU(aA aG cS dE dH) Pc(Is Jl Jp Mz) Ml(Is Jt Qa) cS(Cx Dk Fr) Mi(Jp Mm) Jj(Jl Pg) CuCx FraZ NnJp NfJi Constrained panels with 2 analytes, where 1.0E-4 >= 'model p-value' > 1.0E-5. Contains 363 panels of 16,069 total panels evaluated. : Lv(Et Hv Hx Il Im Iq Ir Iu Jg Jk Jq Jt Ly Ma Mg Ml Mp Nb Nd Nj Nk Nl No Nq Nr Nt Nv Nw Oh Om Oz Pa Pg Po Qa) Lw(aA Hv Hx Il Im Ir Iu Iv Ji Jk Mg Mj Mm Mr Mz Nb Nj Nk Nl Nn Nq Nr Nt Nu Nw Ok Pa Pc Pe Pg Po) Nn(Fr Hv Hx Il Im Ir Is Iv Ji Jj Jl Jt Lx Ma Mr Mz Nj Nr Nt Nw Oi Om Pa Pc Pe Pg Po) cU(aC aJ aP As aV aZ BA bJ bM bO bQ bR bU cB cC cD cE cJ cL cN CX Di dK Fr) Ji(Fr Hr Hv Hw Ij Il In Iu Jj Jl Jn Jp Jq Ma Md Mm Mp Mz Nj Nk Nm Oe Om Pb Pc) Ok(Fr Hv Ij Il In Is Iu Jl Jp Jq Md Mg Mm Mz Na Ni Nj Nk Nq Ny Of Om Pg) Pc(aA Et Fr Hv Hx Il Im Ir Iv Jt Lx Ma Mr Nj Nr Nt Nw Om Pa Pe Pg Po Qa) Mm(aA Hv Ij Il Ir Is Jl Jp Jr Jt Ma Mz Nr Nt Nw Pe Pg) Jp(Fr Im Is Iu Jl Jt Ma Mg Mp Mz Nj Nt Oh On Pg Qd) aX(aA aI aL aO Ax bA BG bO cJ Cp Cq Dd dF dH Di) cS(aA aI aL Ax aZ bA BG bM bO cB Cu cX dD Di) Jl(Hr Im Is Ma Mg Ml Mp Mz Nj Oe Og Oz Pb Qd) Fr(aV bC cJ Cx Is Jj Jt Mz Ng Nj Nk Nl Oe) Jt(Hr Hw Ij Im In Jo Jq Ma Md Na Nf Pb) Mz(Im Iu Jg Jj Ma Mg Ml Mp Nj Nq On) Qd(Jg Jj Lj Mg Mp Nj Nq Oe Oz) Jj(Il Is Jk Ma Mg Nt Nv Po) aA(cB cJ CX kG Ma Mg Nj) Cu(An As Bn cJ cX dE dK) Is(Iu Ma Mg Mp Nj Oe) aP(cB CX dH) On(Hu Im Ns) Ma(Ml Nw) Mp(Nj Nw) Jg(Ng Og) aZ(bO Cx) DkdK NtNj MjMl NbPb ImPg nUmU Constrained panels with 2 analytes, where 1.0E-3 >= 'model p-value' > 1.0E-4. Contains 452 panels of 16,069 total panels evaluated. : Ma(Et Hv Hx Il Im Ir Iu Iv Jg Jk Jq Jr Lh Lx Mg Mp Mr Nb Nj Nk Nl Nm No Nq Nr Nt Nv Oe Oh Om Pa Pe Pg Po Qa) Im(Et Hv Hx Ij Ir Iu Iv Jg Jj Jk Lh Lx Mg Mj Mm Mp Mv Nb Nj Nk Nl Nq Nr Nt Nv Nw Oe Oh Om Pa Pe Po Qa) Mg(Hv Il Ir Iv Jq Jr Jt Lx Mj Mr Ng Nj Nk Nl No Nr Nt Nv Nw Oe Og Pa Pc Pe Pg Po Qa) Mp(aA Et Hq Hv Hx Ij Il Ir Iv Jg Jj Jk Jq Jr Jt Lx Md Nb Nd Nr Nt Nu Om Pa Pe Po Qa) Jj(Et Hx Ii Ij Ir Iu Iv Jg Jp Jq Jr Jt Lh Lw Lx Mn Mv Nq Nu Nw Nx Ny Om Pc Pe Qa) aA(aG aZ bC BG bO bZ cG dC DE Il Jg Jk Jp Lx Ml mP nI nK Nn Nu Oe Om Pg Po) aZ(aI aJ Al aO aP Aw BA BG Bn bW bZ cG cJ cR Cu cX Dc De Di dK fR) Cx(aJ Ap aU Aw BA bC bO bZ cG cJ Cp Cw Dc DE dF Di fR) Nj(Et Ir Jk Jt Lx Nb Nq Nr Nv Nw Oh Om Pa Pe Pg Po Qa) Jg(Hu Hv Ir Iu Iv Jt My Nl Ns Nt Oe Of Oh Oi Oy Pe) Jt(Hv Il Ir Jn Jr Lx Mz Nt Nw Ny Of Om Pg Po) Oe(Et Ir Jk Jp Lx Mm Mz Nt Nv Nw Om Pg Po Qa) aJ(aG aI aL aX bC bG bM bO bZ cB cG cJ cX dE) bA(aC aG aI bC Bg bJ bM bO bW cT cX dE dK) Mm(Hx Iv Jq Me Mj Mr Nb Om Pa Pc Po Qa) Ml(Hv Ir Iv Nb Nr Nt Nw Om Pe Pg Po) Pc(Ij Iu Jk Jq Jr Mj Nb No Nu Nv) Cu(Ad aG bJ Bo Cq cU Cw dB Dc) Om(Iu Nf Ng Nk Nl Of Og Oh Pb) cJ(AP Ax Ba Bb Bg Dc De Di) aX(aP bB bV cB cG cZ dK fR) Pg(Hq Ji Mz Nf Of Oz Pf) Et(Hv Il Iu Lw Nk Nn) bC(As Bg bO cX dE fR) aP(Bg bO De dG Di) cU(Al Ap Bb Bn Dc) dE(aI aL bO bW cG) Nn(Ij Jr Nb Qa) Jp(Ir Jq Nq Nr) Nw(Hv Iu Nk Nt) Mw(My Og Oy) Mz(Nf Nt Oh) cG(As Bn cE) Nb(Nf Of) Is(Jr Mh) Qa(Nf Pb) dK(bG bZ) nR(mW nK) kG(mW nI) BabO BnDe PoOh NmOk NqIr NtLy LwNv JiNy JkOg PePf aLbE cXfR mFmP Constrained panels with 2 analytes, where 1.0E-2 >= 'model p-value' > 1.0E-3. Contains 572 panels of 16,069 total panels evaluated. : dK(aG aI AL Ap Aw Ax aY Ba BB BC Bg bL bM bO bQ cB cG cJ cR CX Dc DE dF Di dM) Jj(Hv Hw Ih Ip Iq Jm Jn Js Li Mj Mq Mr Mt Mu Mw My Nb Nj Nk Nl Nm No Nr Oh Pa Qb Qc Qe) Oe(Hv Hx Ij Il Iu Iv Jq Jr Lh Li Mj Mn Mr Mt Mu Mv Nb Nj Nm No Nq Nr Nu Nx Ny Pa Pe Qe) dE(aG aM aO aU Aw Ax aZ Ba Bb BG bQ bZ cB cC cJ cO Cp Cq Cw cX DC Dd De dF Di dM) cX(aG aI aL aM aO Ap Ba Bb bL bO bQ bV bW bZ cG cJ cR cW DC De dF Di dM) Nj(Hv Hx Ii Ij Il Iq Iu Iv Jg Jq Jr Lh Mj Mq Mr Mu Mv My Nd No Nu Ny Oz) Oh(Hv Hx Ij Il Ir Iv Jk Jr Lx Mn Mp Mr Mv Nb No Nr Nu Ny Pa Pe Qa) bO(aG Al aM Ap Aw Bb BG bL bM bW bZ cG cJ Dc Dd De dF Di dM fR) bW(aG AL aM As Ax Bb BG bM Bn bP cB cF cR cT Cx dB Dc Di) Cx(Af aG aI AL aM aO aV BB Bc Bg Bn cB Cq cY Dd Dk) Di(aA aG aI aJ AL Ap As aU BA Bb bC bZ cG Dc De fR) Nu(Hv Hx Il Im Iu Jq Jr Lh Mj Mn Mr Nb Nk Nl Nq Nr Pa) Ax(aG aI aL Ap As aU aV Aw aZ Bb Bg cB Cs cY De) Jq(Hv Il Im Iu Iv Jg Jk Ml Mv Nk Nl Nq Nr Pa) aG(Al aM Aw aZ Bb bC BG bZ cG Cp Dc dF dM) Jr(Il Im Iu Jg Jk Ml Mn Mr Mv Nq Nr Pa) Bb(aI aJ aU aV bB bC BG bZ dC fR) aL(aC Al Ap aZ Ba bC bH bJ cR De dM) Nq(Hu Hv Iv Lx Nf Ng Nk Nr Pe Qa) Ml(Hx Ii Ij In Jo Js Lh Mr No Pa) aM(aJ aO bG bJ bL bM bZ cJ cO dB) Dc(Ap As aU aV Ba bC bZ dC fR) Nm(Hv Il Jg Jk Jt Nk Nl Og Pa) Im(Il Mk Mn Mr Mu My No Oz Qe) cJ(aO bC bG bH bL bM bS bV dM) Al(aA aI aV bZ cB cG De dF) De(Af aJ Ap As aV bA bZ) Iu(Hv Hx Ij Iv Lx Mn Mv) bC(aI aO aZ Ba bM cB cR) mF(mI mT nM nN nR oP oQ) Aw(aA Af aJ As aV Bn) Iv(Hv Hx Jk Mv Nb Pa) cB(bL bS bV dI dM fR) nK(kG mI mW nM nN oQ) Ij(Nf Nk Og Pa Qa) Jg(Lx Mj Nk Nr Qa) Oz(Mr Nr Pa Pb Pe) bG(aC bM cR dC dM) cG(bJ bM cC cD dH) As(bZ Cp Cw dF) Mv(Hv Nl Og Pa) Nb(Hr Lx Md Og) aI(aC Ba cR dM) aZ(bQ Co dF dM) Ap(aV bA Bg) Nl(Et Mn Mu) Qa(Hw In Md) Pb(Hx Ny Pe) bQ(bM cC dH) bZ(Ba cE Dd) Bn(Cp Cw) Co(aA fR) Lx(Pa Pe) Mw(Ng Of) Nf(Lh Mt) Hu(Jk Mu) Og(Hx Il) aV(Ba Dk) nR(nC nI) mZ(mI nM) BgaJ ChfR EtMg NgJk NkIp HvPa aCdF aUdM nUmM mPmW Unconstrained panels with 3 analytes, where 1.0E-8 >= 'AUC p-value' > 0. Contains 8,520 panels of 625,624 total panels evaluated. : cU{As(aA aC AD aE AF aG aH aI AJ aK AL aM AN AO AP aQ AR aS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT Cu CV CW CX cY cZ dA DB DC DD DE dF DG dH DI dJ DK DL dM dN FR) Cx(aA aC AD aE AF aG aH aI AJ aK AL aM AN AO AP aQ AR aS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT Cu CV CW cX cY cZ dA DB DC DD DE dF DG dH DI dJ DK DL dM dN FR) aA(aC AD aE AF aG aH aI AJ aK AL aM AN AO AP aQ AR aS aU aV AW

Figure 29 Continued

Figure 29 Continued bX bZ cB cC cD cE cF cG cH cI cK cO cP CQ cR Cs Ct cV cY cZ dA Db Dc DD dF dG dI dL dM) AI(aD aE Af aH Aj AN aQ AR aS aU aW AX aY aZ bE bF BG bH bM BN Bo bS bU bV bZ cB cC cD cE cF cG cH cK CO cQ cR Cs Cv cY cZ dA Db DD De Dg dI dJ dM dN) Bn(AD aE Af aH Aj aK aM AN aO aQ aR aS aU aX aZ bC bF BG bH Bo bP bS bV cC cD cE cF cG cH cK CO Cq Cs Ct Cu cV Cw cY cZ dA Db Dc DD De dF Dg dI dJ Dk dM) aX(aC AD aE Af Aj aM AN aO AR aS Ax aY aZ BC BG bI bM bN Bo bP bS bU bV cB cC cD cE cF cG cI cO Cq Cs Ct Cu Cv Cw cZ Db Dc DD DG dI Dk DL dM) cC(aC aD aE aF aH aK aM aN aO aQ aR aS aU aW aY aZ bC bE bF bG bH bM bP bS bU bV bX cD cE cG cH cI cK cP CQ Ct cV Cw cY cZ dA Dc dD dF dG dI dL dM dN) cD(aC aD aE aH aM AO aQ aR aS aU aW Ax aY aZ BC bE bF bG bH bM bP bS bV bX cE cG Ch cI cK CO Cq cR Ct cV Cw cY cZ Dc DD De dF DG dI dM) aD(aE Af aH aK aM aN aO aQ aR aS aU aW Ax aY aZ bC BG bH bM bU bV bX cE cF cG CH cI cK cO CQ cR Cs cV cY cZ dA DD De dF dI Dk dM dN) aO(aE AF aK aM aN aQ aR aS aU aW aY aZ BC bF bG bH bI bM bN bP bS bU bV bX cE cF cG cH cI cK cO cP cQ cR Cs cV cY cZ dA dD dI dM dN) aE(aC aH aK aM aN aQ aR aS aU aW Ax aY aZ BC bE BG bH bU bV bX cE cF cG CH cI cK cO cP cQ Cs cV Cw cY cZ dA dD dF dI dM dN) cO(aC aH aK aM aN aQ aS aU aW Ax aY aZ bC bE bG bH bI bM bP bS bU bV bX cF cG cI cK cP Cq cR Cs Ct cV Cw cY cZ Dc dD De dF dG dM) cY(Af aH Aj aK aM AN Ao aQ aU aW Ax aY Bc BG bH bM Bo bU bV cE cF cG Ch cI Co cR Cs cV Cw cZ Db dD De Dg dI Dk Dl dM dN) dD(aC Aj aK aM aN aQ aR aS aU aW Ax aY aZ BC bE bG bH bM bU bV bX cE cF cG cH cI cK Co CQ Cs cV cZ dA De Dg dI dM dN) bH(Af aH aK aM aN aQ aR aS aU aW Ax aY aZ bC bG bM bU bV bX cB cE cF cG cH cI cK CQ Cs cV cZ dA Dd dF dI dM dN) Cq(aC Af Aj AN aR aS aW Ax aY aZ Bg bM Bo bU bV cE cF cG cI cK cQ cR Cs Cu CV dA Db Dd Dg dI dJ dM dN) bC(Af Aj aK aM aN aQ aR aS aU aW Ax aY aZ bG bM bU bV cE cF cG cH cI Co Cs cV Cw cZ dA De dF dI Dk Dl dM dN) aH(aC Ad aK aM aN Ao aQ aR aS aU aW Ax aY BG bM Bo bU bV cE cF cG cI Co cQ Cs cV Cw dA Dc De dI dM) aU(Ad Af Aj aM An Ao aQ Ar aW Ax aY Bc BG bM Bo cE cF cG Ch cI Co Cs Cv Cw cZ Dc De Dg Dk Dl dM) cE(aC aK aM aQ aZ bE bF BG bM bS bV bZ cB cG Ch cI cK Co cR cV Cw Dc Dd De dF DG Dk dM dN) bM(aC aK aM aN Ao aQ aR aS aY bE bG bU cF cG cH cI cK cP cQ cR Ct cV Cw cZ dA De dI dM dN) cK(aC Aj aM Ao aS Ax aY Bc BG Bo bS bU cF cG Ch Co cR Cs Ct Cw dA Dc De dF Dg dI dM) dM(aK aM aN aQ aR aS aW aY aZ BG bP bU bV cB cF cG cH cI cQ Cs cV cZ dA dF dI dN) dA(aC aM aN Ao aW Ax Bc bG Bo bS bV cG cI Co cP cR Ct Cw cZ Dc Dd dF DG dI) aS(aC aM aN aR aW Ax bG bI bU bV bX cF cH cI cQ Cs cV cZ Dc De dF dI dN) cG(aC aM aQ aR aY aZ bE bG bP bS bU bX bZ cF cI Co cP cR Ct Cw Dc dF dI) Cw(Aj aN aQ AR aW Ax aY Bg bP bU bV bX Co Cs cV Dd De Dg dI Dl) bG(aK aM aN aQ aR aW aY aZ bF bU bV bX bZ cF cH cI cQ cV cZ dI dN) Ax(aM AN aR aW Bg bV Ch cI cP Cs Ct Cu cV cZ Dc De Dg) dI(aC aM aN aR aW aY aZ bE bS bU cI cP cR Ct cZ Dc dF dG) cI(aM aN aQ aR aW aZ bU bV bX cF cH cQ cV cZ dF dN) aZ(aC aM aR aY bE Bg bU cF cR Ct Cv De dF dN) cZ(aC aK aM aN aR aW bE bU bV cF Cs cV De dN) dF(Af aN aR aW aY bU cF CH cQ Cs cV dN) bV(Af aM aN aR aW aY Bg cQ Cs cV De Dg) Dc(Ad Aj aQ aY Bo bU cF Dd Dg dJ Dl) Dd(Ad An aY bE Bg Bo CH cQ Db) aM(aK aN aQ aR aW aY bU bX cP cV) bU(aC aN aW bE bS Co Ct cV De) cV(aN aW aY bX cQ Cs De dN) aK(Af Aj An aW cF Co Cs) Dc(An aQ aR aW aY Co) aC(aR aY bP cB cF) Ct(Aj cF Co cQ) aY(bE bI bS cR) Bg(bF bZ Cs) aQ(An Bc Co) bS(bP cB cF) Cu(An Dl) aN(cF Cs) dN(aW bX) AfBc AjAo BocQ cFcR} cS{bA(aA aC AD aE Af aG aI AJ aK AL aM An AO Ap aQ AR AS aU aV AW AX aY aZ Ba BB Bc bE bF BG bI bJ bL bM BN BO bP bR bS bU bV bW bX bZ cA cB cC cD cE cF cG CH cI cL cM cN CO CP Cq cR Cs CT Cv CW CX cY cZ DB DC dD DE dF DG dH DI dJ DK DL dM Fr) aA(aC aD aE AF aG aH aI aJ aK aL aM AN aO AP aQ aR AS aU aV AW AX aY aZ bB bC bE bF BG bJ bL bM BN bO bP bQ bR bS bU bV bW bX bZ cA cB cC cD cE cF cG CH cI cJ cK cL cM cN cP cQ cR cT CV cW CX cY cZ dA dB dC dD dE dF dG dH DI dJ dK dL dM dN) aL(aC AD aE Af aG aH AJ aK Al aM AN AO Ap aQ Ar As aU aV AW Ax aY Ba Bb Bc bE BG bH bJ bM Bn BO bP bR bS bX cC cE cF cG CH cL cM Co Cp Cq cR Cs Ct Cu Cv Cw CX cY DB DC Dd DE Dg dH Di dJ DK DL dM Fr) Cx(aC aD aE AF aH aI Aj aK Al aM aO aP aQ AS aU aV Aw AX aZ Ba BB bE bL bM Bn bO bP bR bU bW cB cC cD cE cG cJ cK cM cN Cp Cq CT Cu Cw cX cY cZ DB DC DD DE dF DG dH DI DK dM dN fR) Ax(AD Af aI Aj aR AS AW aZ bB bI bJ bM Bn BO bQ bR bS bU bV cB cD cE cH cJ cK cP cR Cs CT Cw cX cZ dB dF DI dK) Af(aD aE aG aH aI Aj AS AW aZ BB Bc bE bG bM Bn bO bP cB cD cG cJ cK cL cT Cv cZ DB dC dD dF dH DI dK dM) aZ(Ad aI Aj Al An aO Ap Ar As aU Aw Ba Bb Bc BG Bn Bo Ch Co Cq Cs Ct Cv Cw cX Db dD De Dg Di Dk Fr) As(aH aI aS aV bE bG bM bN bO bP cB cH cJ cK Cp Cq cT Cu cX cZ DD dE dF dH Di Dk Fr) Aj(Ad aE aH aI Aw Ba BB bE Bg bM bO bP cB cJ Cp Cq Cu cX cZ Dc dD dF Di Dk Fr) bM(aE aI aJ An aO aS Aw bG bL Bn bO bP bR cB Cp Cq cT cX cZ dB dD Dg dH Di dJ) cJ(Ad Al An Ao Ap Aw Ba Bb Bc Bn Bo Ch Co Cp Cq Cs Ct Cv Cw Db Dc Dg Di Dl) aI(Ad aJ An Aw Bb Bc bG Bn Bo Cp Ct cX Dc dE Di Dl dM) cX(aJ aP Aw Bb bL bO Cq cT Cu Dc DD dF Di Dk dM) bO(aE aJ Al aP AW Bb bG Bn Bo Dc Di dM) Di(aC aE aG bE Bn bP cZ dB dD dH) Bb(aC Ap bP Cq cT dB dD Dg dH) Cu(Ad An Bn Bo Cp Cq Cw Dc Dg) aP(aE aS bP cT cZ dG dH dL) Bn(aE Aw Cp cT cZ dF) cB(Ad Al Cq Db Dg) dB(Bc Dc Dd dM Fr) Bc(aS cT dD) Dc(Ad Dg Dl) aJ(aE bP dH) Aw(cZ dD) Dg(Ba Dl) aC(Dl Fr) dM(dD dH) AdDk CqCt} Lv{Mz(aA Fp Hq Hr Hu Hv Hw Hx Ih Ii Ij Ik Il Im In Io Iq Is It Iu Iv Jg Jh Jj Jk Jl Jm Jn Jo Jp Jq Jr Js Jt Lh Li Lj Lu Lw Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nw Nx Ny Oe Of Og Oh Oi Om On Oy Oz Pa Pb Pc Pd Pe Pf Po Pz Qa Qb Qc Qe) Jp(aA Fp FR Hq Hr Hu Hv Hx Ik Il Im In Io Is It Iu Iv Jg Jh Ji Jj Jk Jl Jn Jo Jq Jr Js Jt Li Lj Lu Lw Ly Lz Ma Mb Mc Md Mf Mg Mh Mi Mj Ml Mm Mp Mq Mr Mt Mu Mx My Na Nb Nd Ne Nf Ng Nh Ni Nk Nm Nn No Nq Ns Nu Nv Nw Nx Oe Of Og Oh Ok Om On Oy Oz Pa Pb Pc Pd Pe Pf Pg Pz Qb Qc Qd Wm) Mi(Fp fR Hr Hu Hv Hw Hx Ij Ik Io It Iu Jj Jm Jn Jo Jq Jr Js Lh Lj Lw Ly Lz Mc Md Me Mg Mh Mj Mk Ml Mp Mr Mt My Na Nd Ne Nf Ng Nh Nm Nn No Nq Nt Nu Nv Ny Oe Of Og Oi On Oy Oz Pa Pb Pd Pg Pz Qa Qc Wm) On(aA fR Hu Hv Hx Ii Ik It Iu Jg Jj Jo Jr Lh Lu Lz Me Mg Mh Mk Ml Mm Mt My Nb Nd Nf Ng Nj Nm Nn No Ns Nv Oe Of Og Oh Oi Oy Oz Pb Pd Pf Pz) Ml(aA Hv Hw Hx Ii Ir Is Iv Jg Ji Jj Jl Jq Jr Jt Lx Ly Lz Mj Mp Mr Na Nb No Nq Nr Nv Nw Ny Oe Of Ok Om Oz Pd Pe Po Qa Qd) Jj(Hq Hv Hw Hx Ih Ii Ij Il Im Iq Ir Is Jk Jl Jq Lx Ly Ma Mj Mn Mv My Nd Nq Nv Nw Ny Ok Om Pe Pg Po Qa Qd Qe) Nm(Hv Hx Im Is Jg Ji Jl Jq Mm Mp Mw Nv Nw Ok Om Qd) Pd(Hx Im Jg Jl Jr Li Mp Nn Nq Nw Ny Pe Pg Po Qd Qe) Oz(aA Hv Hx Il Ir Is Ji Jl Jt Nd Nw Ok Pg Qd) Pf(Hx Im Is Jg Ji Jl Nd Nv Nw Ok Om Pe Pg Qd) Qd(Fp fR Ik It Iu Jo Ly Nd Of Pz Qb) Is(Ii Ik It Iu Jo Ly Mh Nd Pz) Mp(aA Ik Jr Lx Md Nf Ng) Hv(Ik Jq Lw Ly Mm Nd Nw) Ne(Im Jg Jr Nw Ok Om) Iu(Ik Iq Ir Jl Jt Qa) Ji(Hx Ly Nd Og Oy) Nw(Il Jo Ly Nj Pz) Om(Jo Ly Nd Ng Og) Lw(aA Hw Hx Jr) Ik(Hx Im Jl Jt) Nn(aA Oi Pc) Mm(Mg Ng Oi) Nd(Jq Nj) Im(fR It) Pz(Jg Ok) Jo(Jl Nv) Pb(Ny Pe) NqOi LyHx MwOy NgJt} Cx{aA(aC Ad aE Af aG aH aI Aj aK AL aM AN AO AP aQ AR aU aV AW AX aY aZ Ba bB bC bE bF BG bJ bL BN BO bQ bR bW bZ cB cD cE cF cG CH cJ cL cM CO Cp Cq cR Ct cV CW cY dA DB DC DD DE dF Dg DI dJ DK dN Fr) aX(aC Ad Af aG aH aI AJ aK AL AN aO aP aR AS aV Aw Ax aY aZ bA bB bE bF BG bL bM BN BO bP bQ bZ cB cC cD cG CH cJ cK Cp Cq cT Cu cV cW cX cZ dB DC DD dE dF Dg dH Di Dk) cG(aD aI AJ aL aN Ao aP aR AS aV Aw Ax aZ bA Bg bO bP bQ bR bU bV cA cC cD cE cF cH cI cJ cK cL cM cN CO Cq cT Cu cW cX dB Dc dF Dg dH DI DK dL dN fR) Cu(aC aE Af aG aJ Ao AP As aU aV Aw Ax aY BA bC bE bH bJ BO bQ bR bV bZ cA cC cD cE cJ cK cL cN cQ cR Cs Cw cX dA dB DC DE DI dJ dK Dl FR) aP(Af aG aI aL aS aU aV Aw aZ bA bB bF Bg Bn bO bP bR cB cD cF Ch cJ cM Cp Cq dA dB dC dD De dF dG dH Di dK dL Fr) cJ(aG aJ Al Aw aZ BA Bb Bc bL Bn bO bV bZ Cp Cq cR Cs cT Cw Dc Dd DE dF Di DK FR) Fr(aD aI Aj aL As Aw aZ bA bB bO bR cB cD Cq cT dB dC DD Dg Di dK) Aw(aJ AL Ar aV Ax aZ bA bC bO bV cT DD dF Dk dM fR) bA(aG aI Ap aU aV aZ bC bO bW bZ cB Cp Cw cY De Di dK) dF(Ap aU aZ bC Bn bO bW cD

Figure 29 Continued cE cF cM Cq dB De dH Di dK) Di(aG aI aJ AL aZ bC bO cT Dc Dd fR) De(aJ aL aO aS Ax aZ bV Cq cT) aZ(Af aI aO bC Bn bW Cq dK) aL(Ap bC bE bW dK) Ba(Aj aV bO Dg) aI(Ap bC dE dK) aV(Al Cw Dc) bO(Cw Dc fR) dK(Ax Bc Dk) Bn(Ap Bb) aJcB cDfR} aX{aA(aC aE aG aH aI aK aL aM aN aO aP aS aV aW aY aZ bA bB bC bE bF bG bI bJ bL bM bN bO bP bR bU bX bZ cB cD cE cF cG cH cJ cN cP Cq cR cT cX cY cZ dB dD dE dF dG dH dI dJ dK dL dM) aL(Ad Af AJ Al An AP Ar As Aw Ax Ba Bb Bc Bg Bn Bo Ch cM Co Cp Cq Cs Ct Cu Cv Cw cX Db Dc Dd De Dg dH Di Dk Dl Fr) bG(aD aE aH aO aQ aS aV aY aZ bA bE bL bM bO bP bR bU cD cE cF cI cL cN cT cV cX dA dB dC dH dI dJ) aI(Af Aj Al An Ap As Aw Ax BA Bb Bc Bn Bo cH Cp Cq Cs Ct Cu Cw cX Db Dc Dd Dg Di Dk) cJ(Ad Af Aj Al An Ao Ap As Aw Ax Bb Bg Bn Bo Ch Cp Cq Cs Cu Dc Dd Dg Di Dk Dl) Cq(aC Af aH Aj As aV aZ bA Bb bE bM Bn bO cB cD cK Cu cX cZ DD dH Di) Dd(aC Ad Af An aO aR As Ax aZ bA bF bL BN Bo cH cK Cw cX dB dH) cX(aF aM aO As aU bA Bg bL Bn BO bQ bS Ch cR Cu Dg Di Dk) bA(Af Al As Aw Ax Bg bJ bV cB CH Cp Dc dH Dl Dk) Dc(aC Ad Af Aj Ap AS bO Cu dB dC dD Dg Di Dl) Ax(aC As Aw bB bO bV cB cH cK Cs cZ dA dH dI) Cp(aC Af Aj As Bn bO cH Cw cZ dD dH) Cu(aC Ad An Ap As Bn BO Cw Dg Dl) dH(aJ aO aP bQ cZ Di Dk) aC(Al Aw Ba Bb Cw Dk) bO(Al AW bM Di Dk) cH(aJ As Aw Bb Dk dM) dD(Al aP cM Di) Dk(cK dK) aP(dG dL) AwcZ aJdL aSbL} Qd{Jj(Fp Hq Hv Hw Ii Ij Ik Il Im Io Iq It Jg Jh Jk Jl Jn Jo Jp Jt Lh Li Lj Lu Lw Ly Lz Ma Mc Md Me Mh Mi Ml Mp Mq Mr Mt Mu Mw Mx Mz Nb Nd Ne Nf Nh Nj Nn No Nq Nr Ns Nv Nw Ny Of Og Oh Om On Oy Oz Pa Pb Pc Pd Pe Pf Pg Po Pz Qa Qb Qe Wm) Iu(FR Hv Jg Jk Jl Jt Lh Lw Ma Me Mi Mm Mp Mw Mz Nf Nj Nm Nn Nq Ns Nw Ok Om On Oz Pc Pf Pg Po) fR(Fp Hq Ii Ij Ik Io Iq Jo Jp Js Jt Li Lj Lu Mm Ng Nj Nm Nn Ns Nu Oe Of Og Oh Oi Oy Pf Pz Qe) Pz(Et Fr Hr It Jg Jk Jl Jp Lw Ma Mc Ml Mm Mp Mu Mw Nj Nn Nq Nw Ok Om On Oz Pc Pg) Ik(Hv Ii Iv Jg Jk Jp Li Me Mf Mg Mi Mp Mu Mw Nf Nj Nm Nn Nq Nu Of On Oz Pc Wm) Nm(Fr Jg Jp Lw Mm Nj Nn Nw Ok Om On Oz Pc) Pf(Fr Im Jp Lw Ml Nj Nn On Pc Pe Pg) Ml(Jp Nj Of Oy Oz) Wm(Ii Jo Jp) Nj(It Jp Qb) Jo(Nn On) LwIt} Fr{bA(AD aE Af aG aH aI Aj aL An Ao AR As aU Aw aZ bB BC bE bG bJ bM BN BO bP bQ bR bS bU bV cA cB cC cD cE cF cG cH cJ cK cN cO cP cR CT Cv Cw cX dA DB dC DE dF DG dH DI dK dL dM) cJ(aA AD Af aG Aj AL aP As aV Ax aZ bM Bn BO bP cB cE cF cI Co cT cX dB DC Dg Di dJ dK DL) Aj(aD AL As Aw Ax aZ Ba cB Cp Cq CT dB DC Dd dK) As(aA aC aI aL aS Aw Ax aZ bO Cq cT Cu dB dD Dg Di dK) aL(aA aD bE bJ Bn cD cE cF cT cX dB DG dH Di dK) dB(aA aD aZ bO Cq cT cX Db dC dK) aZ(Ad aI Dg dH dK) cT(Af cE cX dH dK) fR(Jp Jr Nj Oi Oy) Wm(Jp Nj Nk) dK(Ax bP Dk) Ad(Cq Dc) Dg(aG Ba) Pf(Pe Pg) aA(aI dG) aP(dG dH) AwBn cXdC} On{Pb(Fp Hu Hv Hx Ih Ii Im Io It Iu Iv Jh Jj Jo Jp Li Lz Mb Mh Mi Ml Mp Ms Mu Nc Ne Nj Nm Nn Nq Of Og Oh Oi Oy Oz Pz Qb) Of(Fp Hu Hv Ih Ii Io It Iu Jj Jo Jp Li Ly Lz Mb Mh Ml Mm Mr Nj Nm Og Oh Oy Oz Pc Qb) Mm(fR Hr Hv Ii It Iu Jj Jo Jp Ma Mb Mg Mi Ml Ms Mz Ng Nj Nn Og Oi Oz Pf Qb Wm) Nm(Hr Hv Ii Ip Iv Jj Jo Jp Ma Mb Mg Mi Ml Ms Mz Nj Nn Nt Nu Oe Og Oz) Nj(fR Iu Mh Ml My Nb Nc Nd Ne Oy Pd Pf Pz Qb Wm) Jp(Hv Jg Ml Ms Ne Ng Nn Nx Oe Og Pf Pz) Jj(Il Lz Mh Mi Ml Ms My Oh Pg Pz) Ml(aA Mb Ms Nw Og Pf Pz) Pf(Lw Ma Mi Ns Pe Pg) Ms(Im Mh Mz Ns Pz) My(Ii It Iu Jt Oh) Oy(Ii It Iu Jt Oh) Mi(Iu Jo No Pz) Og(It Iu Mb) Nu(fR Pz) Ng(Ma Mg) MbMh PzOh OefR} aA{cJ(Af aG aI AL aM AN aO aR As aV AW aY aZ bB bC bE bF BG bH bJ bL BN bO bP bQ bR bV bW bZ cB cD cF cG CH cI cL cN Co cP cQ cR cV cW cX cZ dB dD DE dF dG dH DI DK DL) nU(kC kG kO kP lW lX mF mH mM mS mU mZ nA nB nJ nL nM nO nT oO oP oQ) bC(aH aI aL aO bB bF BG bO bR bZ cB Ch cX dA dB dD) cX(aG aM aU aZ bO bZ cB cF cG dB dC dD DE dK) dK(aG aI aL BG bZ dD dF Dk) dE(aG aI aL bZ cB cD dD) De(Af aI aL Bn bO) aI(aM Ap aZ bJ) aL(Aw bE bJ bW) bZ(aZ cE dG dH) mF(kG kP mP nR) cG(bJ dH dL) kG(nF nI nK) Aw(Af Bn) aG(bO cD) nB(mP nT) bEdD bQdH nRnK} dK{Dk(AD AF aG aH aI AJ aL AN Ao aP aQ AR As aU aV Ax aY aZ BA BB Bc bF bJ bL bM BN BO bP bQ bR bS bU bV bW bZ cA cB cC cD cE cF cG CH cI cJ cK cL cM CO CP CQ cR Cs CT cV CW cX DB Dc dD dE dF DG dH DI DL dN fR) aL(aJ AP Ar Ax Bc bG bH bJ bL Bn Bo bS Cp Cq Cs cX Dc Dd Di dM fR) Ax(aG aH aI Aw aY bB BG bO bZ cB cG Ch cJ Cs cX De dF Di fR) bG(aJ aP aZ bA bM bO cE dF dM) aP(aI bP dD dG dH Di dL) aI(aJ aZ dM) Al(bO Di) Cu(Aj Dl) dF(Af Bn)} aP{dH(aG aH aI aL aO aU aV Aw bB bF BG bJ bL bO bQ bR bZ cB cD cE cF cG CH cJ CO cP cR cV cX cY dA dB dD De dF dG Di dL) dG(aG aH aI aL aO aS aV Aw bB bF BG bL bO bP bQ bZ cB cD cF cJ cX dA dD De dF Di Dk) dL(aI aL aQ aU aV Aw bB bC bN bO bR bW cB cD cF cG cJ cX dA dD Di) aL(aU Aw bC bE bJ bR bW bZ cB cF cN cR cX dB De Di) aI(aD As Aw aZ bC bN cF cN dE Di) cX(aG aZ bR cB cF cJ dA dC) cJ(Af Aw Bg Ch Di) cB(bG bH bO cF) Aw(Af Bn Ct) bGbR bZcE} Jp{Wm(Ii Im Io Ip Jg Ji Jj Jo Lh Lw Ly Ma Md Mg Mi Ml Mp Ms Mw Ne Nq Nt Nu Oe Ok Oz Pc) Mi(Et fR Hv Il Iu Jj Jk Jo Ml Mr Ms Ne Nf Ng Nh Nk Nm Nn Of Og Oz Pc Pd Pz Qc) Nn(fR Il Jj Jo Ml Ms Mz Nc Ne Ng Nh Nm Og Oi Pc Pd Pf Pz) Nm(Ij Jk Lw Ma Mm Mp Nq Nt Nw Om Pe Pg Po Qa) Mp(fR Jj Jo Ml Mz Ne Ng Nh Pz) Ji(Il Ml Ms Ne Nh Pf Pz) Jj(Hw Ij Il Ne Nh Pg Po) fR(Im Jh Li Mu Nu Oe) Lw(Hv Il Ne Nh) Nq(Ne Ng Nh) Oz(Hv Jk Pg) Ma(Ne Nh) Ml(Is Qa) Pf(Pe Pg) MgNg NeLi JkOf PdPg} aL{bW(Ad Af aK Al aM An aQ As Aw Ax Bc bG Bn Ch Co Cp Ct Cv De Dg Di Dk dN fR) De(aJ Al aQ BA bC bL Bn bS bV Dl dM dN) bE(aJ Al Ax bG bH Cp Cq Dc Dd Di Dk) Ap(Aw bC bJ bO cJ Cq cX dB Di Dl) Aw(bC bJ Bn bO cG cO dE dI fR) bC(aJ As Bg bL Bn Ch Cp Di) Di(bJ cG cJ dE) bJ(Ba cG) CucJ aQaU bLcC cGcX} Mi{Iu(Ij Il Im Ir Jk Jl Jm Mj Ml Ms Mz Nv Nw Ny Pe Pg Qa Qe Wm) fR(Hr Ii Ir It Jt Li Lj Lu Ma Ml Mu Mv Nm Nq Og Oi Pd) Pd(Jh Jk Li Lw Mf Mp Mu Mw Nn Nq) Wm(Ii Ik Jt Lj Mm Nj Nm Oe) Jl(It Jj Jo Ms Nm Pz) Pg(It Jj Jo Nm Pf Pz) Nm(Lx Nv Nw) Ms(Hr Ji Mz) Jk(Fp Ik Pf) Nn(Mg Oh) NqNg IlJj JoNv} cJ{Di(Af aG AJ Al aN As Ax aZ BA Bc bL Bn bO bV bZ cF cG Cu cX dB Dc dE dF Dk dM fR) Cu(Af Aj An As aV Ax bJ Bn BO bQ bV cF Cq Cw cX DB Dc dE Dg dH Dk Dl) Bn(Aw bA cG dF) Dc(bO cX dE) aZ(Aw Ch Dk) Ba(Aj cX) aJ(cX dL) bA(Af De) dE(Cp Dk) AlbO AwAx} Aw{Ax(Ad Af aI An aO AS aV aZ Ba bB Bg Bn BO bQ bR bU cA cC cD cG Ch cI cK cM Co CP Cq cR Cs cT CW dB Di fR) bO(Al Ar As aZ Bc bG Bn cX) Bn(Al aZ bA Bc dF Dk) As(Ar Bc Dk) Af(Al bA) Cu(Cp Cq) bG(aZ cE) cX(bA cG) BcaS} bA{De(Af aI Al An Ao As Ax aZ Bc BG bJ bM Bn bO bP cB cD cF CH cK CT cX dH Di dL) cX(aG aZ bC cB cG Di) bW(aI BG Ch dH) Di(aG bJ Bn) aI(bC bJ dE) cT(aG bB cB) Bg(aU bC) cG(bJ dH) AxCu bCbG bHcB} Nm{Nw(Hv Ij Il Im Ip Jk Jl Ma Mf Mk Ml Mp My Mz Nn Nq Nt Nu Oe Pg Po Qa) Mz(Jg Mp Nn Nq Nt) Pg(Lw Mm Ok Pf) Wm(Jg Ji) LwJl MpOk IsfR} fR{Oe(Is Jr Lx Mk Mr Mw Mz Nr Nt Nv Om Pa Pg Qa) Is(Ii Jj Ml Mm Of Oh Oz) Jr(Ma Ml Mp Mu Nq) Mm(Ji Om) Ii(Qa Qe) Oi(Mk Nt) MlMz JjJk aZcX} Jj{Pg(Im Ma Ml Mz Nx Om Oz Wm) Wm(Is Jg Jk Jl Mv Qa) Ml(Ij Jl Mz Po Qa) Il(Nv Nw Om Po) Ij(Hv Ma Nq) JlOz} cX{cG(aI Aj aO aQ aS bG bM bO cC cE cF cT dB dD Dg dH Di) Cu(bO dE Di Dl) aZ(aJ aO bQ dF) DecT aIdE} Pf{Pg(Im Jg Ji Lw Ma Mm Nw Ok Om Oz) Pe(Jg Lw Ma Mm Nw Ok Om) Ml(Is Qa) LwJl IlNw JkOk} Wm{Jr(Ml Mu Mw Mx Nn Nq Oe) Mm(Et Im Jg Ji Ok Om) Jg(Of Pz) IiPg IsOe} nU{mF(kI mH mU nA nI nJ nT oP) mU(mW mZ oQ) oQ(kG nA) mWnB} aI{aJ(aZ dG dL) bC(As Bb Di) aZ(bH Di) AdCu AxDe} Cu{As(bV bZ cK dH) AjAx BndF DlcK bOdB} Ml{Qa(Iu Pz Qb) Ms(Is Ji) MbIs} cG{Bn(Dg Di) aJ(dG dH) AfDi bGcE} Mz{Nn(Jo Ms Oi) NqJo LwMs} Il{Mm(Iu Jo Pz) PzNw} Pg{Pz(Lw Ok) IuOk JoOm} nR{mF(mW oQ) mWoP} Ms{Ji(Nf Pb)} Iu{LwJl IsOe} aO{aZ(bC bH)} AdDcDe AlDibO ApAxDl MaMwNg aJbZdG mFmHmP nDkCkG Unconstrained panels with 3 analytes, where 1.0E-7 >= 'AUC p-value' > 1.0E-8. Contains 6,044 panels of 625,624 total panels evaluated. : cU{Dk(aC Ad aE aH Aj aK AL aM AN Ao aQ aR aS aW Ax aY aZ Bc bE Bg bH bJ Bo bU bV cC cD cG CH cK CO cQ Cs cV Cw cZ dA Db Dc De dI dJ Fr) Bo(aD aE Aj aK aL AN Ao aQ Ar aS Ax aY aZ bB BG bH bM bP bU bV cA cC cD cE cG CH cI cL CO Cs Ct CV CW cZ dC dD De dI) cQ(aC Af Aj aK aM aN Ap aQ AR aU aV aW Ax aY Bg Bn bP bU bX cD cE cF cG CH cJ cK CO cR Cs Cw cY cZ dA Db Dc De

Figure 29 Continued

Figure 29 Continued mZ{kG mP nK} nA(mP nK nT) Nn(Oi Pc) Ma(fR Nj) bF(aZ dH) bJ(bO dD) nR(nF nI) DicM MwPb JkOz aUbG bOdB mFmT} bA{De(Ad aG aM aN aQ AR aU aV aY BB bL bN bR bS bU bV bX bZ cA cC cI cL cM cN Co Cp Cq CW cY dA Dc dE dG Dl dM dN) Di(Af aI Ap aU AW aZ bC Bg bO bW bZ cB cG cO dK) cX(aI aM aU bB bL bO bW cC cR cT dB dC dE dK) bW(aM bB bP cB cF cT dE dG dL) Aw(aV Ax bJ bO CT dE) aU(Af bG bJ Bn Ch cT dE) bZ(aZ bJ cB cC dE dH) bC(bB cB Ch cR cT) aI(Ap bE cT dK) cG(Af Bn cF cR) cB(bJ bS dE) Bg(aF Ap) dE(aG cC) bBbJ cOdH cTdK} cX{cG(aD Af aH aJ aN As aW Ax aZ bB bL BN Bo bP bQ bR bU bV cA cD cH cL cM cN cO cQ cV DC dE dF dI DK dL dM fR) Cu(Ad aG aV bC bE cD dB dK) aZ(aG bH Cq De Di dK) Ba(Aj bO Dg Dl) aJ(aG aI cB dC) dK(bG Dc dF dM) Aw(Al Ax) bC(aI dF) bO(Dc fR) AxDe DiaG aMdF dDdE} Mi{Iu(Hu Hx Ii Ip Is Jh Mn My Nb Nu Nx Om Pa Pb) Ms(Lw Mn Mw Nn Nq Nw Om) Jl(Ik Li Ml Ng No Og Oh) Pg(Fp Ii Ng Oy Oz Qb) Nm(Lh Nn Om Po) Oz(In Ne Nh Wm) Pd(Lx Ma Ml Nf) Pz(Jk Lx Nv) Pf(Im Nv Po) fR(Il Mq Oe) Wm(Og Oh) Lw(Hu Oh) Mz(It Ml) Ng(Jk Mu) NnNf MbJk MeIl MwOg NyPb} dK{Dk(aC aE aK Al aM aO Ap aS AW bC bE BG bX cN Cu Cv cY cZ dA dC Dd De dJ dM) bG(aG aH aI aV Bb Bc bL bP bV bW cD cG dH) Ax(aZ bF bL bN Bo bR cD cH cW dB) aI(Al Ar Bc Dc fR) aZ(aG aO Bg dF) aJ(bP dD) AjBg DcDi dFdH} Aw{Ax(aE Aj Ap AR aU aW aY bF bG bJ bP bW bX bZ cE cF cV dA Db Dc dD DE dF Dg dJ Dk dM) Bn(aI aN Ar bC bG bV bZ cG DD) bO(Af bC bP Cu Dk dM) Af(bC cG dF) Bc(cD cK dD) aI(aZ bC bV) Cu(Aj Dl) cE(dF Dk) AlDi AsbC aZbZ} Nm{Nw(Hw Hx Ih Ik Is Iu Jg Jh Jr Jt Lx Me Mg Mj Mn Mu Mv Ne Nf Nh Oi Ok Om Oz Pa Pb Qe) Mz(Et Ma Mg Mm Om Po) Jl(Im Mm Ok) Pg(Im Iu Oz) Nn(Is Ok) Il(Ji Mm) PoOk NjNv IsOe} Cu{bO(aG An Ao aQ As aV Ax bH bJ Bn Bo bQ bR bU cC cD cK cN Cq cY Dc DE dH Di Dl) Dl(aG aH aI aU aV dH Di) Ad(Bg De) As(bW dF) AlAx CpDe} Mz{Ms(Hv Jg Jt Mg Mp Nq Ok Om) Nn(It Ml Nf Nj Oh Oy Pz) fR(Ii Mm Nu Oh) Nq(Ng Pf Pz) Nj(Hv Ma Ml) Jo(Ma Mg Mp) Oz(Hv Pg) IsIu PzJg PfPg} Pg{Oz(Ji Jo Lw Ml Nf Nj Nw Ok) Pf(Et Is Jt Nt Po) Mm(Iu Jo Oy Pz) Lw(Ii It Oy) Ji(It Jo Oy) Im(Iu Oy) Jo(Nw Wm) NjPd PzNw} aI{De(aZ Bn bV cT dM) dE(aJ aZ Cp Dc Di) aZ(aH bJ Cv) aJ(aM bC) cG(Af Bn) AlDi ApAx aHfR aMbV bCdM} Is{Ml(Hr Io Jo Md Me Ng Nu Nw Oe Oz Pb Qb) fR(Iu Js Lh Mx Nn) Nn(Iu Pz) WmOf} aJ{dL(aU bO bW cB cD cG) cB(bM bO dH) aZ(aO dD) dG(aG dF) dH(bB bQ) AfDe} Wm{Nj(Im Jg Mm Ok) Mw(Ml Oe Oi) Jr(Ii Im Mm) Jg(Jo Oh) Jl(Ii Oe) NtOe} Ji{Ms(Hw Jl Jq Md Na Nj Om) Jo(Il Jk Jl) fR(Ii Oe) NdNj JlPf} cG{Af(Aj bO bV dB Dg dH) Di(Aj As bO Dg) Bn(Aj dH Dl) aOcE} Nw{Il(Ii Jo Ml Nj Oz) Pz(Jk Jl Nq) Jk(Ml Nj) NnOi NqJo} aZ{aO(aF aG bO bW Di) Di(aG bO) bH(bO dD) BgdN bGbW bQcN} fR{Jr(Md Mg Mm Nn Oi) Oi(Et Mw Nu) EtOe LxMl MwLh JoOm} mF{nU(kC kE kK mZ nL) mP(kI lW mI) oQ(kG mZ) nNmH nOnR} Ok{Pz(Jl Mp Nn) Ne(Nj Oz) Iu(Jl Mp) NnMs NhOz IlPf} Lw{Il(It Iu Qb) Ms(Hv Jl) IjPf PzJl} De{Ax(Aj aO Cs) Af(cT dF) AjDc} Di{Al(As cD) Dc(aG bO) AsDk AxCs} Jl{Oz(Oe Og) NnOi MaJo ImIu} nU{mU(kG mP nN nT) mZnI} Nj{Ne(Jg Mm) MaNd PzNv} Jo{Ij(Nq Om) MjIm HwOm} Pe{Pf(Et Nq Oz) NnPc} Nf{NnJr NqOi PzQa} Jg{Pz(Ne Pa) IlPf} mW{nR(kG nK) kGkN} Ap{Dk(Dg Dl)} As{CqbZ bCdF} Dc{AdbZ bOdE} Ml{Qa(It Oz)} Ir{Iu(Ma Nn)} Ny{Pb(Mp Nu)} nK{nBoQ kGkI} AxaOaU MmIlOy

Unconstrained panels with 3 analytes, where 1.0E-6 >= 'AUC p-value' > 1.0E-7. Contains 11,529 panels of 625,624 total panels evaluated. : Lv{Qd(aA Et Fr Hq Hu Hw Ih Ii Ij Il Im In Io Ip Iq Ir Is Iv Jh Ji Jk Jl Jm Jn Jq Jr Js Jt Lh Li Lj Lu Lx Lz Ma Mb Mc Md Mf Mg Mh Mi Mj Mk Mm Mn Mp Mq Mr Ms Mu Mv Mw My Na Nb Nc Ne Nh Ni Nk Nl No Nq Nr Nt Nv Nx Ny Oe Oh Oi Ok Pa Pb Pe Pg Po Qc Qe) Nv(aA Et Fp Hq Hr Hu Hw Ih Ii Ij Ik Il In Io Ip Iq Ir Is It Iu Iv Jg Jh Jl Jn Jr Js Jt Lh Li Lj Lu Lx Lz Ma Mb Mc Md Me Mf Mg Mh Mj Mk Mn Mq Mr Ms Mt Mu Mv Mw Mx My Na Nb Nh Nk Nl Nn No Nq Nr Nt Nw Nx Ny Oe Oh Ok Pa Pc Pe Pg Po Qb Qc Qe) Ny(aA Fp Hq Hr Hu Hx Ii Ij Ik In Io Ip Iq Is Iu Jg Jh Ji Jk Jl Jn Jo Jr Js Lh Li Lu Lx Ly Lz Ma Mc Md Me Mf Mh Mj Mk Mm Mn Mq Mr Ms Mt Mv Mw Mx My Nf Nh Nn No Nq Ns Nt Nw Nx Oe Of Og Oh Oi Om On Oy Oz Pa Pc Pe Pg Po Pz Qa Qb Qc Qe) Jq(aA Et Fp Fr Hq Hr Hu Hw Ih Ii Ij Il In Io Ip Ir Is Iu Iv Jh Jl Jm Jn Jr Js Lh Lj Lu Lx Lz Ma Mc Md Me Mf Mg Mh Mj Mk Mm Mn Mq Mr Ms Mt Mu Mv Mx My Na Nb Nh Ni Nk No Nr Ns Nt Nu Nx Oe Of Oh On Oy Pa Pb Pe Pg Po Pz Qa Qb Qc Qe) Jl(aA Et Hq Hu Hv Hw Hx Ih Ij Il In Io Ip Iq Ir Is It Iv Jg Jh Jk Jn Jr Js Jt Lh Li Lj Lu Lx Ma Mb Mc Md Me Mg Mk Mm Mn Mp Mq Mr Ms Mt Mu Mw Mx My Nb Nc Nd Ne Nf Nh Ni Nk Nl Nn No Nr Ns Nt Nu Oh Om Pa Pg Po Qb) aA(Et Fp Fr Hq Hu Hw Ih Ii Il In Io Iq Is It Iu Ji Jm Jn Jo Jr Js Jt Lh Lj Lu Lx Lz Mb Mc Md Me Mf Mg Mh Mm Mn Mq Mr Ms Mt Mx My Na Nb Ne Nf Ng Nh Nk Nm No Nq Nr Ns Nu Nx Of Oh Ok Oy Pa Pb Pf Pg Po Qb Qe) Im(Hq Hr Hu Hw Ii Ij In Io Ip Iq Ir Iu Jg Jk Jm Jn Jo Js Jt Lh Li Lj Lw Lx Ly Lz Mb Mc Md Mi Mj Mk Mn Mq Mr Ms Mt Mv Mw My Nb Nc Nf Nl Nn No Nq Nr Nt Nx Of Og Oh Oi Ok Om Oz Pa Pb Pc Pe Pg Po Qb Qe Wm) Nd(Et Fp Fr Hq Hr Hu Ih In Io Ip Iq Ir It Iu Jg Jh Jk Jn Js Li Lj Lu Lw Lx Lz Ma Mc Md Mf Mg Mh Mk Mm Mq Mr Mt Mu Mv Mw Mx Na Nb Ne Ng Nh Ni Nl Nm Nr Ns Nu Of Og Oh Oi Pb Pc Pe Pg Po Qa Qc Qe) Lx(Fp Hq Hr Hu Hv Hx Ii Ik In Iq Is It Jg Jh Jn Jo Jr Js Jt Li Lu Lz Mc Md Me Mf Mh Mj Mk Mm Mn Mq Mr Mt Mu Mv Mx My Ne Nf Ng Nh Ni No Nq Nr Ns Nt Nu Nw Nx Oe Of Oh Ok Om On Oy Pb Pc Pf) Om(Et Fp Hr Hw Ih Ii Ij In Io Ir Iu Iv Jg Jh Jm Jn Js Lh Li Lj Lu Lw Lz Ma Mb Mc Md Me Mf Mh Mi Mj Mk Mn Mp Mq Mr Ms Mt Mw Mx My Na Nb Ni Nn No Nq Nr Nx Oh On Pc Pe Pg Po Qa Qb Qc) Hx(Et Fr Hu Hv Hw Ih Ij Il In Ip Iq Ir Iu Iv Jh Jk Jm Jn Js Jt Lh Lj Lu Mb Mc Md Mf Mg Mj Mk Mn Mq Mr Ms Mt Mu Mv Mw My Nb Ng Nh Ni Nk Nl No Nr Nt Nx Oh Pa Pe Pg Po Qa Qb Qc Qe) Jr(Fp Fr Hu Ii Ik Il Io Ip Iq Iu Jh Jk Jn Js Lh Ly Mb Me Mf Mg Mj Mm Mn Mr Ms Mt Mu Mv Mx My Nb Nc Nf Ng Ni Nj Nk Nl No Nr Nt Nx Of Og Oi Oy Pa Pb Pc Pe Pg Po Pz Qa Qb Qe) Is(Et FR Hq Hr Hu Hw Ij Il In Ip Ir Jh Jk Jn Js Jt Lh Li Lu Lz Ma Mc Md Mf Mg Mj Mk Mm Mn Mq Mr Mu Mv Mw My Na Nb Nh Ni Nk Nl No Nr Nt Nx Oe Oh Oi Ok Pa Pe Pg Po Qc) Oz(Et Fr Hq Hr Hu Ih Ik Ip Iv Jh Jn Jo Js Li Lu Lw Mb Mc Md Mj Mk Mm Mn Mq Ms Mt Mu Mv Mw Mx My Na Ne Nf Ng Nh Ni Nj Nk Nl Nm Nn Ns Nu Nx Og Oy Pb Pc Pd Pf Qa Qb Qe) Ok(Et fR Hq Hr Il Iq Iu Iv Ji Jk Jm Jo Li Lj Lu Lw Lz Ma Mb Mc Me Mh Mi Mk Mm Mn Mp Mr Ms Mu Mw Mx My Nf Ng Ni Nj Nk Nn Nq Nr Ns Nu Nw Nx Of Oi Pa Pb Pg Po Qb Qe) Nu(Et fR Hq Hu Hv Ii Ij In Ip Iq Ir It Iu Jg Jh Jk Jt Li Lj Lz Mc Md Mh Mm Mn Mr Mt Mv Mw Mx My Na Nb Ni Nj Nk Nm Nn No Nq Nr Ns Nt Oe Oh Pd Pe Pg Po Qa Qe) Lw(Et Fp Hq Hu Ii Ij Ik Il Iq It Iu Jg Ji Jj Js Jt Ly Mc Md Me Mf Mj Mk Mn Mq Mu Mv Mx My Na Nb Nf Ni Nj Nm Nn No Nr Nt Nw Nx Oe Oi Oy Pb Pe Po Qc Qe) Ly(Et Fp Fr Ii Ik Il Iq Ir Iv Jk Jn Jo Js Jt Lh Lj Md Mj Mk Mn Mq Ms Mt Mu Mv Mw My Na Nb Nh Ni Nj Nk No Nq Nr Ns Nx Of Oi Oy Pb Pd Pe Pf Po Qa Qe) Hv(Et Hq Hr Ii Ij Il Io Iq Ir Iu Ji Jn Jo Lh Li Lj Mb Mg Mn Mq Mr Ms Mu Mv Mw My Nb Ng Nj Nk Nl Nn No Nq Nr Nt Nx Of Og Oi Oy Pa Pd Pe Pg Po Qe) Oe(Et Fr Hq Hu Hw Ik Il Iq Ir It Jg Jh Ji Jn Js Jt Lh Li Lz Mc Md Mj Mm Mn Mq Mt Mu Mv Mw My Ni Nl Nm Nn No Nq Nt Nx Of Oh Pd Pg Po Qa Qe) Jj(Fp Hr Hu Ik In Io Ip It Jh Jo Lj Lu Lz Mb Mc Md Me Mf Mh Mq Mr Mx Na Nb Nc Nf Ng Nh Ni Nj Nl Nm Ns Og Oh Oi Oy Pb Pc Pd Pf Pz Wm) Nw(Et Fr Hr Ih In Io Ip Ir Iv Jh Jm Jn Js Jt Lh Lu Mb Mc Me Mf Mg Mj Mk Mm Mq Mr Ms Mt Mu Mv Mw Mx My Na Nb Nc Ni Nl No Nt Oh Qa Qc) Ji(Et Fp FR Hr Hw Ih Ii Ij In Ir Iu Iv Jg Jt Lj Ma Mb Mg Mk Mm Mq Ms Mt Mu Mv Mx My Nb Nc Nl No Nr Nt Oh Pc Pd Pe Pg Qa Qb Qc) Jg(Fp Hq Hr Hw Ii Ij Ik Il In Ip Iq Ir Jm Jn Js Jt Lu Mc Mf Mh Mi Mn Mp Ms Ni Nj Nk No Nq Nr Nx Of Oh Pa Pb Pe Pg Po Qa Wm) Po(Fp Hq Hr Hu Ik In Iq It Jm Js Lj Lu Lz Md Me Mh Mk Mm Mn Ms Mw Mx Ne Nf Ng Nj Nm Nn Nq Nx Of Og Oi On Oy Pb Pz Qb) Jn(fR Hq Hr Hu Ik In Iq It Jh Li Lj Lu Lz Ma Mc Md Me Mf Mh Mq Mt Mx Nh Nm Nn Nq Ns Of Oh On Oy Pa Pc Pe Pf Pz) Mp(Hw Ii Iq Jh Jm Li Mc Me Mf Mh Mj Mn Mq Mt Mv Mw Mx My Nh Ni Nj Nn No Nq Nr Nt Nx Oh Pa Pb Pc Pf Pz Qb) Iq(Hq Hr Hu Ik In Ip Iv Jm Jo Li Lz Ma Md Me Mh Mi Mm Mn Ms Mx Ne Nf Ng Nn No Nq Nt Of Og Oy Pb Pc Qa) Ml(Hq Ih In Ip It Jh Jk Li Ma Mc Me Mf Mh Ms Mt Mx My Nf Nh Ni Nj Nk Nm Ns Oh Oi Pc Pf Qb) Mw(Fp Hq Hr Hu Ik In Ip Jh Jo Jt Li Lu Lz Mc Me Mf Mn Mr Mx My Ne Nh Nj

Figure 29 Continued

Nk No Nt Of Oh Pz) On(Fr Hw Ih Ij In Ip Ir Iv Jh Jk Js Lj Mb Mc Mj Mq Mu Mv Mx Na Nc Ne Nh Nl Nt Pg Qc) Mm(Hw Ij Ik Ir It Jk Js Jt Mc Mi Mj Mr Ne Nf Nh Ni Nl No Nq Nr Of Og Pb Pc Pg Qe) Pd(Et Hq Hw Ih Io Ip Ir It Jh Jk Jo Ma Mg Mn Mt Nb Ni Nk Nl No Nt Oh Pa Pz Qa) Ik(Et Fr Ii Ir Iv Jk Js Lh Ma Mg Mj Mn Mr Mu Mv Nl Nm No Nq Nr Pa Pe Qa) Ne(Et Fr Ii Iu Li Ma Mr Mv Na Nb Nj Nl Nn No Nq Nr Nt Pe Pz Qe) Mi(Et Hq Ih Ii Il Ip Iv Jh Jk Jt Li Ma Nb Nc Nk Nl Nx Pe Qe) Nq(Fp Hq Iu Jo Lu Md Mf Mr My Nb Ni Nn No Nt Oh Pa Pz) Fr(Fp fR Hw Jo Lu Nh Ni Nj Nk Of Og Oi Pb Pz) Nm(Fp Hq Hw Ii Js Lh Mn Nf Nh Nj Nn Nr Oi Oy) Pf(Hw Ih Jh Lh Li Mb Mn Mt My Nn Nt Pz Qe) Pg(Fp Ii It Jm Ma Mx Nf Ng Nj Of Og Oi Pz) No(Ij Il Li Ma Ng Nh Nj Nk Nn Og Pa Pz) Mr(fR Hr Ii It Lj Lz Me Mh Nn Of Og) Oy(Et Hw Iu Jk Jt Lh Li Ma Mq Mu Nt) Nj(Et Hq Hw Ij Ir Ma Mn Nc Nt Qa) Jo(Ii Il Ir Iu Lh Li Mn Mq Mv Qa) Ng(Et Iu Ma Mg Mq Mu Mv Nt Nx) Og(Hw Ij Il Ir Jk Nr Nt Qa Qe) Oi(Et fR Hw Iu Jt Li Mu Nt Pc) Nn(Fp Hu Hw Md Mj Ni Pe Pz) Hr(Hw Il Iu Li Mq Nr Pa Qe) It(Ii Ij Ir Iu Nb Nr Qa) Nf(Iu Li Ma Mq Nt Qa) Pz(Et Ij Ir Jk Nt Qa) Fp(Il Li Mv Nr Qe) Me(Il Jt Nr Pe Qe) Pb(Ii Iu Lh Na Qa) Ni(Iu Li Ma) Nk(Et Ma Nc) Of(Ij Mq Mu) Lu(Hq Li) Mn(Hw Ij) Nh(Jt Nl) WmMz MvLj MxPe IiJt IufR IvQa} Jp{Lw(aA Et Fp fR Hq Hr Hu Hw Hx Ii Ij Ik Is It Iu Iv Jh Ji Jj Jl Jm Jo Jq Js Lj Lu Lz Ma Mb Mc Md Me Mf Mg Mj Mk Mm Mn Mq Mr Mt Mu Mv Mw Mx My Na Nb Nc Nf Ng Ni Nk Nr Ns Nt Nu Nx Ny Oe Of Oh Om On Oy Oz Pb Pc Pe Po Qb Qd Qe) Mp(aA Et Fp Hr Hu Hx Ii Ij Ik In Io Ip Iq Ir Is It Iv Jg Jh Jl Jm Jn Jq Js Lh Li Lj Lu Lx Ly Mb Mc Me Mh Mj Mk Mm Mn Mq Mr Mt Mu Mw Mx My Na Nb Ni Nj Nk Nn No Nq Nr Nu Nv Nw Nx Ny Oh Ok Pa Pc Pe Pg Po Qb Qc Qd Qe) Jj(Et Fp FR Hr Hu Ih Ii Ik In Io Ir Iu Iv Jg Jh Jm Jo Jr Js Jt Lh Lu Lx Ly Lz Mb Mc Md Me Mf Mj Mm Mn Mq Mt Mu Mv Mw Mx My Na Nb Nd Nf Nj Nk Nm Nr Ns Nt Nu Nv Nw Nx Of Og Oh Oi Ok Oz Pa Pb Pc Pf Qa Qb Qe) Ji(aA Fp Hq Hr Hu Hw Hx Ih Ii Ik Im Io Iq Iu Iv Jl Jo Jq Li Lj Lu Lx Ly Lz Mb Mc Md Me Mf Mh Mi Mj Mk Mn Mq Mr Mt Mu Mw Mx My Mz Na Nb Nc Ni Nj Nk No Nq Nr Ns Nu Nv Nw Ny Oh Om On Oy Pb Pc Pe Po Qb Qe) Nn(Fp Hq Hr Hu Hw Ih Ii Ij Ik Ip Iq Ir Is It Iu Iv Jg Jh Jl Jm Js Jt Lh Li Lj Lu Lx Ly Lz Ma Mb Mc Me Mh Mj Mk Mn Mq Mr Mt Mu Mv Mw My Nb Ni Nj Nk No Nq Nr Nv Nx Ny Oh Ok Om Oz Pg Po Qa Qc Qd Qe Wm) Mz(FR Hq Hr Hu Hw Hx Il Im In Io Ip Is It Iu Iv Jg Jk Jl Jo Jr Li Lj Lu Lz Mb Md Mf Mg Mh Mi Mk Mm Mq Mu Mw My Nb Nc Nd Nf Ng Nh Ni Nj Nk No Ns Nt Nu Nw Of Oh Om Pa Pb Pc Pd Pe Pf Pg Po Qb Qd) Oe(aA Hq Hw Ih Ii Ij Ik Il In Ip Iq Ir Is Iu Iv Jg Jk Jl Jq Jr Jt Lh Lx Ma Mj Mk Ml Mm Mq Mr Mu Mw Mx Nb Nc Nd Nf Ng Nh Nk Nm No Nq Nr Ns Nt Nu Nv Nw Ny Oh Ok Om Oz Pa Pc Pd Pe Qb Qd Qe) On(aA Fp Fr Hu Hw Hx Ih Ii Ij Ik In Ip Iq Is It Iu Iv Jk Jl Jm Jn Js Jt Lj Lu Lx Ma Mc Me Mf Mg Mj Mk Mn Mq Mr Mt Mu Mx Na Nb Nd Nf Ni Nk Nt Nu Oh Pc Pe Qb Qd Qe) Wm(aA Hw Hx Ij Il In It Iu Iv Jk Jl Jm Jn Jq Jr Js Jt Lj Lx Mc Mf Mh Mm Mn Mq Mr Mt Mv My Na Nb Nd Ng Nh Ni Nj Nk Nl Nv Nw Nx Oy Pa Pd Po Pz Qb) Mi(aA Fr Ii Ij In Ip Iq Ir Is Jg Jl Jm Js Jt Li Lx Ly Ma Mb Mc Mf Mg Mj Mn Mq Mv Mw Mx My Nb Nd Nl Nr Nt Nv Nw Ok Om Pe Pf Pg Po Qa Qb Qd Qe) Im(aA Hv Hx Il In Is Iu Jl Jr Jt Lh Li Ma Mg Mj Ml Mu Mw Nb Nd Nf Ng Ni Nj Nq Ns Nu Nv Of Og Oh Oz Pa Pb Pd Pe Pf Po Pz) Ne(aA Et Hr Hv Hx In Is Iv Jk Jq Jt Lh Mf Ml Mq Mu Mv Mw Nb Ng Nj Nk Nl No Ns Nv Nw Of Og Oh Pb Po Qd) Oz(AA fR Hw Ik In Ir Iu Iv Jg Jq Jt Li Mj Ml Mr Mu Mv Mx Nb Nk Nq Nr Nt Nu Nw Ok Om Pa Pb Pc Pe Qa) Ml(FR Hv Ij Il In Ip Ir Iu Iv Jg Jl Ma Mf Mg Mm Mq Mw Nb Ng Nk Nm Nr Nt Nu Nw Om Pa Pc Pe) Nm(Aa Et Hr Hw Hx Io Ip Iq Ir Iu Iv Jl Jr Jt Lx Mf Ms Mu Mv Nf Ng Nk Ny Of Og Pf Pz) Pg(Fr Hq Hv Ii Iu Jg Jr Lh Li Ma Mm Nc Nf Ng Nj Nq Ns Nt Nu Of Og Oi Ok Oy Pb Pz) Ma(aA Hv Hx Il In Jk Jo Jr Nd Nf Ni Nj Nk Ns Of Og Oi Oy Pa Pb Pc Pd Pf Qb) Li(aA Hr Hv Hx Il In Jk Jo Jr Lz Mh Mw Nc Ng Ns Nu Of Og Pa Pb Pc Pd Pf Pz) Nq(aA Hq Hv Hx Ik Il In Io Jr Md Ms My Nc Nf Ns Oy Pa Pb Pd Pe Pf Po Qd) Hv(aA FR Is Jg Jk Jr Mg Mm Nh Ns Nt Nu Nw Of Og Om Pb Pc Qd) Jk(aA Hq In Io Iu Jo Jr Mm Mq My Nc Ns Nu Oh Oy Pb Pc Pd Pz) Qd(Hr It Me Ms Mw Nd Nf Ng Nh Nk Ns Og Oy Pc Pd Qa) fR(aA Ii In Io Is Iu Jr Mk Mv Mw Na Ng Nw Pa Pc Pd) Nh(Fr Iu Jg Jr Jt Mf Mq Mu Mv Nu Nw Oh Ok Om) Og(Hx Il Is Iu Jg Jl Jr Mg Mm Nt Om Pc Po) Ng(Fr Is Iu Jh Jr Mf Mu Mv Nt Om Pc Po) Pz(Ir Iu Jg Jl Jq Mg Nw Ok Pc Pe Qa) Of(Hx Is Jh Jr Mm Nb Nt Nu Pa Pe Po) Pf(Fr Ij Is Jg Mg Nt Nw Ok Om Pc Po) Fr(Et Il In Jo Mm Ms Oi Oy Pd) Jr(Is Iu Ms Mu Nd Nw Om Pc Po) Mm(Et Hx Jo Nf Nj Nk Oi Oy) Pc(Il In Jo Ms Nc Nu Pd Po) Mg(Il Jo Ms Nf Oi Pd) Jo(Hw Is Iu Nt Om) Po(Ii Nj Pd) Nu(Ly Pb Pe) Is(It Mh Nj) Nt(Il Oi) Hq(Lx Pa) Hw(Nj Qa) Hx(Hr Io) MsOm MuHu MwOy NcNk IjQa IlJg InPb IuJl} cU{dJ(aC AD Af aH Aj aK AN Ao Ap aQ aU aW aX aY bB Bc BG bH bJ Bo bP bU bW cB cD cF cG Ch cK CO cR Cs Cv CW cY cZ dA Db dD Dc Dg dI DL dM) cB(aD aE aH aK aL aM aN Ar aS aU aW Ax aZ bB Bc bE bF bG bM Bn Bo bP bX bZ cF cI cK Co CP CQ cR cV Cw cY cZ dA Dc DD dI Dk DI) DI(AD aE Af Aj aM An Ao AR aW Ax aY aZ Bc bE BG bH bJ Bo bP bS bX cC cE cF CH cI Co cP cQ Cs cV cZ Db DD Dg Dk dM) Dd(aE aF aH Aj aK aM aN aO AP Ar aS aU aW Ax aZ bB Bc bI bL bM bS bV bW bX cF cG Co cR Cs CV cZ dC dD DG dI) bS(aE aH Aj aK AN Ao aQ aR aS aU aW Ax aZ BC bE bF Bo bV bX bZ CH cI cP cQ Cs CV cY cZ Db De Dg Dk dN) dL(aD aH aK aL aN Ao aQ aR aU aZ bB BC bE bF BG bI bM bP bZ cF CH cI Co CQ cR Cs cV Cw Db Dc De dF dN) Cv(Aj aK aM AN Ao AR aW Ax Bc bE BG bH bP bU bX cF cG CH cI Co cQ cR Cs cV cZ Db De dF Dg Dk dM) aF(aC aK aM aN aQ aR aW aY Bb bE bG bM Bn bP bV cD cF cG cH cI cK Cp Cq cR cV Cw cY cZ Dc dD De dF dI dN) bF(aD aE aK aN aQ aR aU aW aZ bE bI bN Bo bV bX bZ cH cI cP CQ cV Cw cY cZ Db DC De dG Dk dM dN) Ao(aK Al aM aN aP Ar aW Ax aZ BC BG bH bN bP bV bX cG CH cI cQ cR Cs cV Cw Db Dc DG dM) bN(aC aE aH aL aN aR aS aU aW aZ bC bE bH bI Bo bP bV cF cI Co cP CQ cR cV cY cZ Dc dD dF dN) bZ(aD aH aM AN aQ aZ Bb bE bI bM Bo bP bV bX CH cQ cR cT cV CW cY cZ Db Dc dD De dF dM) Ar(Af Aj aK aM An aQ aW Ax aY Bc bG bJ bM bP bU bX cE cF cG CH Co cP cV cZ Db Dg dI Dk dN) Db(Af aK aM An aO aR aW Bc bG bH Bo bP bX cF cG CH cP cR Ct cV Cw cZ De Dg dI dM dN) bI(aC aH Aj aN aQ aR aU aW Ax aZ bC bE bG bH Bo bV bX cH cI Co cP CQ cV cZ dD dF Fr) Ad(aD aE aK aM An aQ aS Ax aY Bc bH Bo bQ bR bU bV cA cC cE cF cG Ch cO Cw dC dD dI) aC(aD Af Aj AN aW Ax bC Bg bH Bo bV bW bX cI Co cP cR cW Dc dF Dg dM Fr) dG(aD aE aH aK aM aU aZ bC bE bG bM bP bV cG cI cK CP Cq cR Ct Cw cY dN) cP(Aj aK An aR aW Bc Bg Bo bX CH cI cQ Cs cV cZ Dc dF Dg Dk dM dN) bE(Af Aj aK An aQ aU Bc Bg Bo bX Ch cQ cR Cs Ct Cw cY De Dg dN) bP(Af Aj aK An aQ aW Ax Bc Bg CH Co Cq Ct cZ Dc Dg Dk dN) Cu(aH aS aU Ba bM bQ bU cA cF cG cK Co cT dA dC Dg dI Fr) Ct(aD aH aK aN aO aS aU Aw bB bV cM cR CW DC dF) Af(Aj aM An aY aZ bM Bo bR bU cF cH cI cR Cw Dk dN) An(Aj aM aR aW aY bM cF CH cI Co cQ cV Dg dN) Bc(aM aR aY Bo bX cC cF cI Co cQ cR dF Dg dN) Bo(aM aR aW bC bX cF cR dF Dg dM dN) Ch(aM aN aR aW aY bG bM bR bX cF dN) Co(aM aR aW bG bM bV bX cF cH cZ dN) Dc(aK aO aR Cp Cq Cw cZ dD dF dM dN) Dk(aO bG bM bX cF cI cR dD Dg dM dN) Aj(aM aR aW bG bX cF cH cR dN) Dg(aM aN bM bX cC cF cR dF dN) aX(aK aQ aU cK cQ cR cY dN) dF(aH aM aQ Bg Cw cZ dD De) Cq(aK aL aQ cM CW Fr) aO(aH Ax Cw De Fr) Bg(aR bG cF cR) Cp(cQ Cw De) aM(cH cW dN) bX(Al Ap Cs) Ax(bG cE) De(aE cF) Fr(bG dD) cK(aU cY) cQ(aZ bC) cR(Cs dN)} cS{As(aJ aM AN AO Ap AR aU aW aX aY Ba bC bF Bg bH bI bJ bQ bS bU bV bW bX cA cC cD cE cF Ch cI cL cM cN CO cP cQ cR Ct CV CW Db De Dg dI dJ DL dN fR) Di(aF aK aM AN Ap aU AW aX Ba bB bC bG bI bJ bL bN Bo bS bU bW cA cB cC cD cG cH cI cL cM cN Co Cp Cs Ct Cu CV CW cY Dd dE dI dJ dK DL dM dN FR) Bb(aA aD aJ aM aN Ao aQ aR aU aW Ax aY BC bF bG bJ bL Bo bQ bS bU bV bW bX cA cC cE cF cG cI cM cN Co Cp cQ cR Cs Ct cV cW dA Db Dc dE dF dJ dK dM dN fR) bM(aC AD aM aR aU aV aW aY aZ Ba BC Bg bI bJ bS bU bV bW bX cA cC cD cE cG CH cM Co cP cQ cR CV cW DE Fr) Aj(aC aD aN Ao Ap aQ aS aU aX aY bF bI bJ bQ bR bS bX bZ cD cE CH cL cM cN Co cQ cR Cs Cv Db dC dG dK dL dM fR) Bn(aC aG aH aJ Al aN aP aW Bc bI bJ Bo bP bQ bV bX cB cD cG cH cM Co cQ Db DC dE Dg dH dI dK dM dN fR) bO(Ad aG aK aM Ao Ap aQ aS aU aZ Ba Bg bL bQ Ch cJ Co Cs Cv Cw cY cZ dB dC DD De dJ Dl FR) Aw(aC aD aF aG Al Ao Ar aS aV aW aX bB bL bN Bo bQ bU cC cD cE CT dB DC dE dF Dg Dl Fr) cZ(AD aG aK aM An AO Ap Ar aU bG bJ bP bS cC Ch Cp cR

Figure 29 Continued

CT Cv Cw cX cY Db DE Dl) aP(aC Af aG aK aL aM aW Ax bB bF bJ bL bV bW bX cA cD cE cH cJ cL cP cV cW dA dC dJ) Af(aF aM aN Ap aQ AR aU aX aY bN bR cA cC cl CO cR Ct Cu Cw De dJ Dl fR) cX(aM An Ap aS aW Ba bB Bc bP bQ bS cC cG Ch cJ Co cQ Cs Ct Cv Db DE Dg Fr) al(aD aE aH aK aM aN aO aQ aS bJ bN bP cC cE cH cR cT cY dB dC Dd dH dJ fR) aJ(aC aD aG aO aW aZ bB bE bF bG bL bQ bU bW cB cD cH cJ cL cN dA dC dJ dK) cT(Ad Al aM An aO Ap Ar aZ Bg bL cC Ch Cp cR Ct Cv Cw Db Dc Dg Dl dM) Dd(Ad aG aH An aR Ax bQ cB cE CP Cq cR Cw dC dE dH dK dN) aS(aE aG Al aM An Ap bG bJ bL Bo Ch Cp Cs Ct Cw Dk Dl Fr) Ax(aG Ap aQ aU aV aY bC bG bN bX bZ cG dC dD Dc dH fR) Cp(aA aD aE Ao aX Bo bQ cE cH cL Ct dC dD dE Dg dH) Cx(aN Ar aY bC bF Bg bl bS bZ cA cO cP cR Cv cW dA) dB(Al aM An Ap Ar Ba Bo Ch Cq Cs Ct Cv Dg Dl) dF(aE Ao Ap aZ bG Bo bP bR cE Ch Cv Cw dE) dM(aC aH aO aZ bB bG bL bU cD cH cJ dA dK) Dc(aC aD aQ aX bN Bo bQ cP dG dL) bG(aD aH aO bB bP bQ bU cJ dD dK) cB(aL An Ao Ba Bc bS Co Ct Dk Fr) aE(Al aO aW Bc bL Cs Dg FR) Bo(aC aH bB bE bP cK dC dN) Dk(aV cD cI cL Ct dD dE Dg) aA(Ad Al Ar Bc Cs Ct Cw De) aL(aF aX bL cI cJ cK cQ dN) Bc(aD Ap bB bP dG dL) Dg(aG bB bE bP cG) aO(bE bL bP cE dH) dD(An Ba cR Cs fR) Cq(aV bP bR cD) Fr(aD bR cK dC) aZ(aM cF cR Cu) bA(aF bH dA) Al(aV dE) Ao(aH bB) Ap(cG Dl) Ct(aC bP) AdbE ArcJ CubN DbbP bLcC bQcE bRbS} aP{cB(aD aE aG aJ aK Al aM aN aO aQ AR aS aV AX aY aZ bB bC bF Bg bJ BN bR bV bX bZ cA cD cE cG Ch cI cK cL cM cO cP cR cT cV cW cY dA dB dC dD dJ DK Dl dM) aI(aA aC aE aF aJ aK AN aO Ap aQ aR aU AX aY bB bF bG bH bI bL Bo bS bV bX cE Ch cJ cK cL CO CQ cT cV cW cZ Db dC dF Dg dI dJ Dk dM FR) cJ(AD aE aG Al aM An AO Ar aS aU BA BB Bc bF bH bJ bL bN bU bZ cH cI Co Cq Cs CT Cv Cw dA DB dC dD dE Dg dK Dl) Cx(aC aD aE aF AJ Al AN Ao Ap AR aW Ax Bb bC bH bI bJ Bo bS bV bW bX cA cC cE cL cN CO Cs Ct Cv cW cZ Db Dg dJ fR) cX(aA aD aE aH aK aO aU aV Aw bC bF BG bL bM bN bP bQ bU bV bZ cC cD cH cI cK cM cR cT Cu cV cW cY dB DE dF DI Fr) aL(aA aC aD aE aH aJ aK AN aQ aR AS aV aY aZ bA bI bM Bo bS bX cA Ch cL Co Cp cQ cT cW cY Db dC dF dI dJ dM) dL(aD aF aJ aM aN aR aS aY bA bE bG bH bI bM Bn bS bV bX cA cE cI cK cL cO cQ cT cW cZ DE dF dI Fr) Di(aE aG Al An As aV Aw AX aZ bA BG bN bP bR bU cF cG Ch cI cK cM cN cR cY dA dB Dc Dg Dk Fr) bO(aE aM aO aR aS aU aX aZ bA bB bF Bg bH bJ bL bM bZ cD cG CH cI cN cP cR Cu dC dD DE Fr) dG(aD AF aJ aK aM aW aY aZ bC bE bH bI bJ bM Bo bS bV bX cA cI cK cL cO cQ cT cW dC dI dJ dM) dA(aG aM aN aO aS Ax aZ bB bJ bL Bn bP bS bX bZ cD cH cN cR cT dB dC dD dE dK Fr) dH(aD Af aJ AN aY aZ bA bE bH Bo bS bV bX cC cK cM cT cW Db dE dI dJ dM dN) dK(aA aE Af aH aM aS aV Aw Ax bA bB bE bF bJ bQ bU bZ cD cF cG cM cZ dF dJ Fr) bG(aD aE aF aG aQ aU aV Aw aZ bA bB bC bJ bN bP bW cC cF cI cN cR dB dD dE) bR(Af aG aO aX aZ bA bC bF Bg bH bL bM bN bQ bZ cG Ch cN dD dE Fr) cF(aA aE aG aR aS Aw aZ bA bF bL bM bZ cD cG cH cM cP dB dD) dD(Af aM aU aV bB bC bM Bn bP bW bZ cA cD cH cL cP cR dB) Aw(Aj Al An Ao AS aV bA bB Bg bN bU Ch cP cR dB Dk) aG(aA aS aZ bB bN bP cD cH cI dB dE) bB(aA Af aS BN bP cD cH dB dE) Bg(aD Af As aZ Bn cD cE cK dC) cD(Af aS aZ bF bM bP Ch cN) cN(aO bF bP bQ cG cH dB) aE(aX bN bZ cH dB dE) bA(aU aX bJ bW bZ De) bP(aU bF bZ cP dB) Fr(aD As dB dC) bZ(aA As aZ) dB(aO bM dC) Af(bF Ch) AxCu ChaD DcaX DeaR aMcH aOaZ aSbC bFbM bNcR} On{Pz(aA Et Hq Hu Hw Hx Ih Ij Il In Io Iq Ir Is It Iu Jg Ji Jk Jl Jm Jq Jr Jt Lh Lj Lu Lw Lx Ly Lz Mb Mc Md Mc Mf Mh Mj Mk Mn Mq Mt Mu Mw Mx My Na Nb Nc Nd Ng Ni Nk Nl No Nq Nr Nv Nw Nx Ny Oi Ok Oy Pa Pc Pe Pf Pg Qa Qc Qe) Jj(Fr Hu Hw Hx Ih Ii Ik In Io Ip Iq Ir Is It Iu Iv Jg Jh Ji Jm Jo Jq Jt Lh Li Lj Lx Ly Ma Mb Mc Me Mf Mg Mj Mk Mn Mq Mt Mu Mv Mw Mz Na Nc Nd Ne Ng Nh Ni Nk Nl No Nr Ns Nu Nv Nx Ny Ok Pc Pf Qa Qb Qc Qe) Ml(Et Hq Hu Ii Ij Ik Il In Io Ip Iq Ir Is It Iv Jg Jl Jm Jn Jo Jq Jr Js Lh Lw Lx Ly Mc Me Mf Mj Mk Mn Mp Mt Mx Na Nb Nc Ne Nh Ni Nn No Nr Nt Oh Oz Pa Pg Qb Qe) Nj(aA Et Hu Hw Ih Ii Ij In Io Iq It Jg Ji Jl Jn Jr Js Lw Ma Mb Mc Mf Mg Mi Mk Mp Mq Mr Mt Mu Mw Mx Mz Ng Nn Nq Nr Nu Nx Oh Oi Pe Pg Qc Qd Qe) Og(Et Fp Hq Hu Ih Ii Im Io Iv Jl Lh Lz Mh Mi Mk Mp Mu My Mz Nb Nc Nd Nf Ng Ni Nl Nn Ns Nt Nu Oe Oh Oi Om Oz Pf Pg) Iu(Ih Il Im Io Ip Ir Is Iv Jl Jo Jt Li Ma Mb Md Me Mg Mk Mp Mq Mw Ng Nn Nq Ns Nt Nu Oe Oi Ok Pc Pe Pg) Of(Il Im Ir Jh Ji Jk Jl Jm Jq Lh Lj Lu Lw Lx Md Me Mf Mg Mi Mj Mk Mn Mv Nb Nh Nk Nt Nv Oe Om Pe Pg Qa) Hv(Fp Hq Hu Ii It Lj Lu Lw Ly Lz Mb Mi Mk Mp Ms Mx My Mz Nb Nc Ne Ng Nn Ns Nx Oe Oh Pa Pf Qb) Nm(aA Fp Ij Ik In Jh Jn Js Lu Mj Mr Mu Mv Mw Mx Na Nc Ne Nh Nl Nr Nw Oh Om Pa Pd Pg Po Qc) Mm(Ik In Ip Ir Is Jh Jn Js Lu Mj Mr Mt Mu Mv Mw Nf Nh Ni Nk Nl Nw Ny Om Pb Po Qa) Jo(Fr Hw Il Io Is Iv Li Mb Me Mk Mv My Nf Ng Nq Nr Nu Oe Ok Oz Pc Pe Pf) Pb(aA Fr Hr Ik Ip Is Jg Jl Jn Jr Jt Lh Mf Mk Mn Mv My Nv Om Qa Qd) Mi(Fp Fr Hx Ih Ik Lz Mh Mk Mr Ms Mt My Nc Ne Nh Oi Pd) Oy(Fp Hu Ih Io Lz Mh Nc Ne Nf Ni Nk Nn No Nu Nx Oi Pf) Ng(Fr Ii Io It Li Mf Mp Mv Nc Nu Oh Om Pa Qb) Oi(Et Hr Jg Li Mb Mp Ms Nb Ns Nt) Oz(Il It Ms Ne Nx Oh Pe Pf Qd) Mb(Hu Im Lw Mt Mz Nb Ns Pf) Ii(Il Md Ms Mz Nf Nk Pg Qd) Mh(aA Hx My Ns Nu Nw) Ms(Hr Ly Mw Nn Pf Qb) It(Iv Lw Mz Nf Ns Qd) My(Fp Hu Ih Io Lz) Mg(Ma Mp Nf Nn) Pf(Il Iv Mp Nn) Ns(Ik Lz Wm) Lw(aA Jm Pc) Nb(Ik Pc Qb) Pd(Im Pe Pg) fR(Mu Nk Oh) Lz(Nu Nw) Mz(Oe Qb) LyNe MkLi NiIm HrHw IvOe QaQd QbPg} aX{Dc(aD aJ aK Al aM AN aQ aU AW aY Ba Bb BC bF BG bJ bM Bn bQ bS bU bV bZ cA cC cE cF cG cL cM CP cQ cR Cs Ct CV CW cY dA Db Dd dE dF dG dH dI dJ dL dM dN) Cq(AD aG aK Al aM aN Ao Ap AW aY Ba bC Bg bI bQ bS bV bW bX cA cC cF Ch cI cL cM cN cQ cR Cs cT CV CW cY dA Db dC dE DG dI dJ DL dM dN) Cu(Af aG aM aN aR aU aV Aw Ax Bc bE bF BG bI bL bN bP bR bU cD cF cH cI cL cN Cp cT dA dB dC dF dH DI dK dL) Di(aE Af Aj AN aO Ap aR aS aV bB bG bL BN Bo bP bU cB cD cE cF cG cH cL cM cR DB dC dF Dg Dk) bA(Ad Aj aL aN AO aS aY aZ bB BC bF bH bN bP bR bS bW cC cF cG cI cJ cR Cs cT DB dC dE dJ dM) Dd(aA aD aE aG Aj aK Al aM aN Ap aU Aw Bb bR bS bU bX cA cC cF cI cL cN Cv dA dC dE dF Dg dK dL dN) cX(aE aK aR aS aW aZ Ba Bb bE bF bH bJ bN bZ cC cE cG cH cJ cL Cs cT Cv CW cY dB DE Dl dM Fr) Ax(aE Af aG Al aO aR aV Bb bE bF BG bL BN Bo bP bU bX bZ cA cD cG cM cN cT dB dC dF Dg) bO(Ad aG al AJ aM Ap aZ Ba Bc Bn cH cJ Cs Ct Cv Cw DB dD De Dg FR) dF(Af AJ aO AS Aw aZ bJ bL bM Bo cE cF cL cN Cp dB dC dE Dg dL dM) aO(AL An aS aW aZ bJ bM bS cE cF cI cJ Cp cR dB dC dE Dk dL dM) Cp(aH Al An Ap aS aV bE bG bL bM bN Bo bP cC cT dB dE Dg Dl) dD(Aj Ap aZ Ba Bc Bg Bn Bo Ch Cs Ct Cw Db Dg Dk dM FR) cZ(Ad Af Aj An Ap As Ba Bn Bo bV Cs Ct Cv Db De Dg) Dk(Ad Af Ap aU aV bB bE bL bV cB cD cT dC Dl) aA(aD As Aw Bn bW cA cC cK cM cO dN) aL(aU aZ bG bJ bL cJ dB dE dI dJ dM) aC(Ad Aj Ao Ar Bn Ch Co Ct Cv Db) aH(Af Aj Al An As Aw Bb Bo Db Dg) aZ(Al An As Bn Bo cH Cv Dg Fr) Aw(Af Al aV bE bL Bn cK dH) bG(aI aR aU bJ cM dG dK dN) aJ(aE aR bE bL cB cN dB) dH(Af An As Bb bL Bo dJ) aS(aE aQ bE cF cI cR) cH(aE aG Bc Cw Db Dl) cT(Af aI Al Bg Ch Fr) bL(aG bM bU cL dM) Al(aV bB bE cD) dB(bE bM bP dM) Af(bB cG cK) Cx(bV CO) aI(aU dC dE) cB(Ar Cs dM) bE(As cR) bR(bS dM) cF(aE bM) cK(Bb Bo) AjcG BaDg} Fr{Aj(aE Af aG aH aK aN Ao Ap aQ aU bB BC bF bM bN Bo bP bQ bU bV bW cA cE cF CH cL cM cN Co cQ Cs Cu cV dA Db dE dF DG DI Dk DL dM dN) aL(aE aG aI aM aN Ao Ap AR aU aW aY BB Bc bG bL bM bN bP bS bU bV bX cA cB cC cG CH cL cM CO Cp cQ CV CW Db dD De dI dJ Dk dM dN) dB(aG aJ Al aM AN Ao Ar aU aW bB bF Bg bL bN bQ bR bU bV bW bX cA cB cC cF cG Ch cN Co CP cQ cR Ct Cv dA dF Di dJ Dk dL dM dN) As(Ad aE Af aG aH aJ Al AN aQ Ar aU bB Bc bF Bg bL bM BN bP bQ bR bS bU cA cE cH cI cM Co Cp Ct Cv cW cX dA Dc Dk dL dN) Cx(Ad Af aK Al aM aN Ao aQ Ar aU Ba Bb BC bF bM bN bP bU bV bX cA cC Ch cI cK cL cN CO cP Cs Cv cY dA De dG Dk dM dN fR) cT(aA aD aE aG aN Ao Ar aU Aw bB bC bF Bg bL bM bN Bo bP bU bV cA cB cC cH cI cL cN Co cP Cq cR cV Cw dA dC dD dE dI dL) cJ(aC aE aI Ao Ap AR aS AW Bc bE bG bH bI bS bW bX bZ cA cH Cp Cq cR CV cZ De dI dM dN fR) dK(aC aD aE aG aH aJ Al Aw BB bM Bn Bo bR bV cB cE cG cK DC Dg dH dL) Dg(Af aH Al Aw BB bC bF Bn BO bR cE cK Cp Cw Dc dD dF dH Di Dl) aA(AD aE An aS Aw aZ bB bC Bn bP cE cF Cq dA dC dD dE dM fR) aD(aC Af Aw aZ bB Bo bR cB cD cE Cq cX DD Di) dC(Ad aI Al aS Ax bM Bo bP bR cB cE cF Dc dE) Di(Af aG aI Al Ax bB Bn bO cB cD Ch cX

Figure 29 Continued

Figure 29 Continued

BgdK CofR CuDl} Cu{cX(aC aD aE AF aH aI AJ aK Al aM AN AO Ap aQ AR AS aU AW Ax aY aZ Ba bB Bc bF bG bH bI bJ bL bM BN Bo bP bQ bR bS bU bV bW bX cA cB cC cE cF cG Ch cI cK cL cM cN CO CP CQ cR Cs cT cV CW cY cZ dA Db DC dD De Dg dH dI dJ Dk dM fR) bO(aC AD aE AF aH aI AJ aK Al aM aN aO Ap AR aS aU aW aY aZ Ba BB BC bE bF BG bI bL bM bN bP bS bV bW bX bZ cA cB cE cF cG Ch cI cL cM CO CP cQ cR Cs CT CV CW cZ dA Db dC DD dF DG dI dJ DK dL dM dN fR) Dl(aO aQ Ax bB bQ bV cB cC cD dB dC DE fR) dE(al aS Aw Ax bB Bg cB cD dB De Dg dH) Ad(cB Ch dB dH dK) Di(aG aI Aj As Ax) Bn(Aw cG De) dB(aV Ax cY) As(De fR) Cw(cK De) AnbZ ArAx aIdK} Mz{Nj(Et fR Hw Im Io Is It Iu Iv Jr Li Lj Lw Lx Ly Mf Mg Mi Mm Mp Mq Ms Mw Nc Nd Ne Nf Nm Nq Nu Nw Of Og Om Pf Po Qb Wm) Ml(Hr Hv Is Iv Jg Ji Jk Jl Jr Lw Lx Ma Mb Mf Mg Mh Mm Mp Ms Mu Mw Nk Nq Nt Nu Nw Oe Og Om Pc Pg Po Qa Wm) Nm(fR Im Ip Is Iu Iv Ji Jk Jl Jr Lw Lx Mf Mi Ms Mu Nu Nv Ok Pc Pg) Nn(fR Hv Li Mb Md Nc Ne Ng Nu Oe Og Pc Pd) Ms(Im Jk Jl Jq Ly Mm Mu Mv Mw Nb Nw Oe Pc) Jo(Hv Is Iu Jg Mf Mm Mu Mv Nt Om Pg Po) Pf(Hv Jg Jk Lw Ma Mg Nt Oe Pc Pe Po) Mp(fR It Jr Nf Ng Og Oh Oy Oz Pz) Nq(Hv Ii It Jr Nf Of Og Oi Oy) Og(fR Hv Jg Mi Mw Nu Om) Oe(Hv Iv Jr Nf Nw Wm) Mi(Ih Js Mr Nf Pd) Pz(Is Ma Mg Mm Nt) Oz(Hx Jk Jl Mr Po) fR(Io Li Mu Ns Oi) Hv(Lw Nu Om) Wm(Mw Oh) Mg(Nf Ng) LwIt MaNi MvNf NgOm IiPg IuJl} Aw{bO(aD aH aI aJ aN aS aV Ba bB Bg bJ bM Bo bQ bS bU bV bZ cF cG cK cL cM cN Cs cT Cv DB DC dD dE dF dH Di dJ Dl fR) Ax(aD aF aG aJ aK Al aM aN aQ Bb bE bL bM bS bV cB cL cN cO cQ Ct Cv cZ dG dH dI dL dN) Bn(aC aG aH aJ An aO aV bE Bg bL bQ bS cM Cq Cs cT cW cX cZ Db DC Di dM fR) Bc(Ad An aV bB Bo bP bU cF Ch cN cT Cw dA dB dH) Al(aD aI An AS aV bM Bo cD cE Cp Cq Ct Cw) Dk(An Ao aU aV bW cG Ch Cw cX Di) aV(Af As aZ bC bS bV cA cX) Af(aG aJ aZ bV DC) aI(aJ Ar cG dE dI fR) aZ(aN bC Cv cX dE) dD(Ar bV dE dF dM) cD(Ar bG bS bV) cX(As bC cT dF) Aj(Ba Dc) Ar(aS dB) As(bS dF) aJdH bVcM bZcE} Mi{Iu(Hv Hw Ih Ik Jg Jq Lw Lz Ma Na Nk Nn Nr Ns Nt Ok Oz Pd Qb Qc) Ms(Hv Is Jg Jq Li Ly Ma Ml Mp Mu Ne Nt Nu Nv Nx Oz Pc Wm) Pd(Hu Ii Im In Jl Jr Lz Mv Nr Nu Nv Ny Oz Pa Pe Pg Po) Jl(Fp Ih Ii Jm Lj Lz Me Mk Nf Nt Of Oi Oz Qb) Oz(Aa fR Hu It Nf Nv Nw Og Pa) Wm(Fp Hr Io Jo Lu Ml Nx Pb) Nm(Im Is Jg Jk Lw Mn Ny Qa) Nn(Ih Jh Li Ml No Og Oi) Ml(Hu Jr Nu Nv Ny Po) Ne(Jg Nj Nq Nv Nw Om) Lx(Jo Nf No Pb Pf) It(Ij Is Jk Mn Mu) fR(Hv Jn Md Nu Ny) Jo(Is Nw Ny Po) Og(Jk Lw Nq Pg) Nf(Jr Ny Pg) Ik(Il Mj Nr) Jg(Li Mg Pf) Jk(Io Me) Li(Nw Pc) Pf(Om Qa) Pg(Nr Pe) MaMg MfNg MwPb HrHx HuPc} dK{bG(aD aE aF Aj aM aN aQ aU aW bF bJ BN bU bX cA cH cI cK cL cO cP cT cV cW cZ dA dB DC dD dE dG Di dJ Dl fR) Ax(aE Af aM aQ aU aV bJ bM Bn bU bV bX cE cI cO Cp cR CV cZ dA Db Dc dD Dg) dF(aE aG aI aM Ar Bc bJ bL bM bN bO bP bS cE cF Cp Dc dD dE Di) aI(Af aG Ba Bn bS Cs cX dE Di) aZ(bL bO bQ bV bZ cF Cv dD Di) aJ(aG bO bQ cZ dH Di dL) cX(aG bL bO bQ Di fR) Bc(aH Bg Cq dD Di) Dc(Aj aO bO bV dD) dM(aH bO dD) Di(aG bO) Dk(bH bI) AfcG AlBo ArcB DdbZ} Nw{Nm(Et Fp Hq Hr Hu Ii In Io Iq Ir It Iv Jm Jn Jo Jq Js Lh Li Lj Lw Ly Lz Mb Mc Md Mh Mm Mq Mr Mt Mw Mx Nb Nd Ni Nj Nk No Nr Ns Nv Nx Ny Of Oh Oy Pc Pe Pz Qb Qc) Ml(Ij In Jl Jr Mb Mj Ne Nj Oe Pg Po Qa) Hv(Il Jk Ne Nj Oe Oz Pf Pz) Pz(Ij Ma Mp Mv Nn Nt Ok) Nj(Ma Ne Nh Nq Oz Pg) Pf(Ij Jl Ma Nn Nq Po) Il(Hr Of Og Pb Pd) Jk(Og Oi Oy Oz Pb) Mm(Mg Mp Nn Wm) Iu(Is Jl Mp Nt) Jo(Jl Ma Mp Nn) Nq(Ne Ng Oi) Pg(Ii Oy Pd) Ms(Ji Nn) fR(Jr Oe) MaNk IiJl} cX{cG(Ad aE aF aG aK Al aM An Ao AR aV aY Bb BC Bg bH bJ bW bX Ch cI Co CP cR Cs Cv CW cY cZ dA dG dN) aZ(aI Ap Ba bL bO bV bW bZ Co cR cV dC) Di(aI Al aV Ba bC bO cT DC dF fR) aJ(aM bB bC bO bR cM dG dL) dF(cB cC cE dC DE) fR(aI aM bC cB cD cM) Ba(Ad aI aV dB) dC(bQ bZ cW Dc) dE(aG aO bO cB) aM(aI aO bL) bC(aO Bb Dc) Ap(aI dD) aG(bO cW) aV(Al Dc) bQ(cC cE) cB(bV dM) CqDe bLbO} Is{Iu(Et Hv Im Ip Jg Jk Jl Jo Li Lw Ma Mg Mm Mp Ms Mu Nj Nk Nm Nq Ns Nt Nu Og Om Oz Pc Pe Pg Po) Ml(Hu Hv Hx Ih Im Jg Jl Jm Jr Lx Nc Nd Nf Nj Nn Nv Ny Of Og Om Oy Pd Pg Po) Nm(Ji Lw Ma Mm Mp Nj Nt Nu Om Oz Pc) Pz(fR Jg Lw Mg Mm Nj Nq Nt Nu Oe Pc) Jo(Ma Mg Mp Nn Nq Nt) Wm(Ii Ik Js Ns Oz) fR(Hr Nu Og Oi) Nn(Oi Pf) Mh(Me Ms) MsIv NjIt} aI{dE(Af aG aM Ax Bb bC bG bM bO bV cC cG cH cO cT dC Dd De dM) aZ(aC Al Ap Ar As Ba bC Bn bO bW bZ cC cR dM) Di(aG aJ Ap aR As Ax Ba Bn bV cG DC dI) aJ(aD aG bJ bN cG cI cR dB dC De dH) bC(Af Ax bM Bn Cp cR Dc) De(aD Al bO Dc dF) cG(aH As Ax cE dH) Ap(Al bO bV Dk) dI(aM As Bb Cp) Ax(aC aU bE) Ba(Aj Bn Dg) Dc(bE cI) aM(bW dF) cE(bQ bZ) CwcI} Pg{Oz(Fp Hv Hx Ii Im It Iu Iv Jg Jk Jq Jt Ma Md Mp Mr Ms Nb Ng Nk Ns Nt Nu Oe Of Og Oi Om Pa Pd Pe Pz) Pf(Iu Iv Jh Jl Jq Lx Ly Ml Mp Ms Nj No Nu Nv Oe Of Og Qa) Jo(Et Iu Jg Jq Lw Ma Mg Nm Nv Ok Po) Iu(Et Ir Ji Jt Mp Nt) Ji(Fp Ml Ms Nj Nm) Pz(Im Jg Nm Om) Oy(Ma Nm Nn Ok) Nj(Im Mm Ok) Oi(fR Jg Nn) Pd(Ma Mm) EtNm LwMl IiOk} Di{aZ(aJ Al Ba bC bJ bL bQ bW bZ cG cM cN DE dF) Al(Af aG Aj aV bB bM Bn bV cB dB dD) cG(Ax bP bQ cD cE cF cK dB dH Dl) Ax(As aU Ba bB bO bV cR De) Dc(Ad Aj aV cM cR dC dE Dl) bO(aG As Ba bC bV dE) aG(aJ Bn dE) As(bC bZ) AjBa BndF aEbV aJdL dDdE} Jl{Oz(Iu Jo Ml Ms Ng Nj Nm Of Po Pz) Nm(Et Iu Ji Ma Og Om Pz) Lw(Ii It Jo Ml Og Oh Qb) Im(Nj Og Oy Pf Pz) Ml(Jr Lx Nj Og) Iu(Hr Ji Ma Mm) Jo(Mg Mp Nn Om) Pf(Ma Og Ok Pe) Mg(Ma Ng) Mp(Mk Ng) Ji(Nj Og) NnPc MmPz OifR} cG{Af(aJ aO AS aV Ax bL bQ cD cH cK cL cM cN Cq cT dD dF) Aj(Ax bJ bL cH Cp Cq dH Dk) As(Ar Ax bC bO dH Dk) bO(bG bJ Bn dB dH) Ax(Cs dB Dl) Bn(aS bI dB) cE(bF Bg bZ) dH(Ad aO dE) AdDc DkaV aSbJ bRbS} aZ{aO(aN bJ bQ bV bZ cC cE cN cO Cq Cv dB dC) bO(aG bL bQ bZ Ch Co Cq De dN) bQ(aG bL cF cR dB dH dN) bZ(Aj As Cq dC) aG(bH bL dE) Aj(Bg Co) aJ(cF cN) bG(bC dN) bW(Bg Ch) AlDc BadD cNfR} fR{Oi(Ip Iu Lx Mm Mr Nb Nq Nr Pa Pf) Jr(Im Iu Js Li Mk Mv Mw Mx Pa) Nj(Lx Mk Mm Mw Om) Oe(Hq Iu Jn Nu Oz) Qa(Jo Mm Oh) Al(cB cD) Nt(Og Pb) Mw(Ml Oh) DccD NmJi NuLx MmOk NbPb bScB} Nn{Oi(Hx Jg Mr Nb Nr Nt Nu Nv Om Pa Pe) Pd(Jr Mj Mr Nb Ny) Pc(Mr Nf Nr Pa) Pf(Im Ok Pe) Nf(Ny Oh) Nj(Nd Nv) Jo(Ij Nv) Jr(Ml Ng) Pb(Ny Pa) WmJg MsJq NeOk} Nm{Ji(Jk Lx Ms Ne Nh Nu Po) Om(Hx Il Ms Nu Og Pe Po) Lw(Hu Ij Lh Nt Pe Po) Ok(Il Lh Nq Nv) Mm(Ij Po) Il(It Pf) Nv(Nt Oe) WmEt NqNg NrPf} Ml{Po(Ik Jm Jr Lj Ng Of Og) Ji(Hu Hv It Iu Mj Oh) Qa(Mb Nj Of Oy) Lx(Lj Mp Mw) Ny(Mw Nu Pb) Ok(Hv Ms Pf) Om(Mj Ne Ng) Pe(Oz Pf) LwHw MpJr} aJ{cB(aG Ax bC bG bS bZ cA cF cH dC dD dE dG) dH(aG aH bF bZ cF dD) dL(aG aV bB bR bZ) bO(aG dB) bQ(bR dG) aHdG aMdD} mF{nU(kO kP lW mS nC nD nH nM nN nR oO) nR(kN kP mH nC nH oO oP) mP(kC kP mU mZ nT oP) nM(kC kP) mH(mI oQ) nNlW nToP} Jo{Nv(Ji Jt Mp Nj Nq Nt) Om(Hv Hx Il Mj Ms Po) Ij(Jg Mm Mp) Po(Ma Nq) Im(Nb Nr) Jg(Hw Ne) WmJi MaHx MjMm MpIl} De{Ax(aR aS Bo bV cD cI cP cT dB dD) Af(Ba bV Cq) Bn(cT dD dF) Aj(Al Ba) AsdF DcDl} Wm{Jr(Hr Ik Io Jg Lw Ly Ma Md Mv Nu) Oe(Hx Jg Jn Ok) Mw(Hr Jm Ns) NjOm JgOi JiOh} Pf{Ok(Hx Ne Nq Pa Po Qb) Im(Mj Mw Nb Nq) Lw(Jk Po) Hx(Jg Ma) Qa(Nf Pb) Pe(Ji Nv) NeJg} Mp{Iu(Ir Nb Nr Ny) Oi(Jg Lu Mw Pd) Nf(Jr Lx Ng) Ng(Mu Ok) Jr(It Og) LwHu NjNv} Nq{Ng(Iu Jr Nf Ny) Ny(Oi Pb Pd) Nj(Nd Nv) Oi(Jr Nu) Ok(Ms Pz) IrIu} Lw{Mb(Hv Il Jk Pa Pe) Hu(Hv Ik Mr Pe) Pz(Il Jk) PoPb HvOi IiPe} Oz{Jk(Hv Hx Jt Og Ok Pe) Ms(Jt Ok) Il(Jg Ok) NfQa NjPe HvJg HxOg} Ji{Ms(Hr Hv Ij Lx Mn Nd Ny Qa) Il(Iu Pz) NeNj NfIt IuJk} bO{Dc(aG An aV bJ Bo cO cY dB) Al(aU dB) dE(aG Cp) cBdM} Om{Nj(Nd Ne Nh Og) Og(Hv Hx Ne) Ng(Jk Ne) IrIu} nU{oQ(lW mT nB nR) nT(lW nA nR) mU(mH oO) nHkG} Mm{Nj(Il Nh) Iu(Ir Pe) Pz(Ij Mj) NgJk} Pb{Qa(It Pz Qb) Ny(Li Oe) MwOy NbIm} cB{Ax(Ba bW) aO(bC dE) bV(Ba bS) AsbC} Jg{Pz(Ij Nh Ok) Og(Hv Hx) IrIu} nR{mW(lW mM oO oQ) nTnK oPoQ} aU{dF(Af As Bn) Ax(aK bB)} kG{nD(nJ oQ) mWmZ nIoQ nKkC} Dc{Dl(Ap bW) AjbW aVdE} Ng{Ma(Jk Jr Pe) ImJk} As{bZ(Ax Dd) bBbC} Nf{Qa(It Qb) JrLi} Nj{Im(Hw Nd) EtNe} Af{ApBn bCdF} Aj{BaBg DdbZ} Dk{AdAp aVdE} bM{aObC bWdD} BbCwDl NtIrIu NbImIt PzJkOk aMdBdF bGbWcT

Unconstrained panels with 3 analytes, where 9.4E-6 >= 'AUC p-value' > 1.0E-6. Contains 23,907 panels of 625,624 total panels evaluated. : Jp{Is(aA Et Fp Fr Hq Hr Hu Hw Hx Ih Ii Ij Ik Il In Io Ip Iq Ir Iv Jg Jh Ji Jk Jl Jm Jn Jq Js Jt Lh Li Lj Lu Lx Ly Lz Ma Mb Mc Md Me Mf Mg Mj

Figure 29 Continued

Mk Mm Mn Mq Mr Mt Mu Mw Mx My Na Nb Nc Nd Nf Nh Ni Nk Nl No Nq Nr Ns Nt Nu Nv Nw Nx Ny Oh Oi Ok Om Oy Pa Pb Pc Pd Pe Pg Po Qa Qb Qc Qd Qe) Po(aA Et Fp FR Hq Hr Hu Hv Hx Ih Ij Ik Il In Io Ip Iq It Iu Iv Jg Jh Jk Jm Jn Jq Js Jt Lh Li Lj Lu Lx Ly Lz Ma Mb Mc Md Me Mf Mg Mh Mj Mk Mm Mq Mr Mt Mu Mv Mw Mx My Na Nb Nc Nd Nf Nh Ni Nk No Nr Ns Nt Nu Nv Nw Nx Ny Oh Oi Ok Om Oy Pa Pb Pe Pg Qa Qb Qc Qd Qe) Nt(aA Et Fp Hq Hr Hu Hw Hx Ih Ii Ij Ik Im In Io Ip Ir It Iu Iv Jg Jh Ji Jk Jl Jm Jn Jr Js Jt Lh Li Lj Lu Ly Lz Ma Mb Mc Md Me Mg Mh Mj Mk Mm Mp Mr Mt Mu Mw Mx My Na Nb Nc Nd Nf Ni Nj Nk Nl Nn No Nq Nr Ns Nu Nv Nw Ny Oh Ok Om Oy Pa Pb Pc Pd Pe Qb Qc Qd Qe) Jr(aA Et Fr Hq Hr Hu Hw Hx Ih Ii Ij Ik Il In Io Ip Iq Ir It Jg Jh Ji Jl Jm Jn Jo Jq Js Lh Lj Lu Lx Ly Lz Mb Mc Md Me Mf Mg Mh Mj Mk Mm Mq Mr Mt Mv Mw Mx My Na Nb Nc Nf Ni Nk No Nr Ns Nu Nv Nx Ny Oh Oi Pa Pb Pd Pe Pf Pz Qa Qb Qc Qd Qe) Hv(Et Fp Hq Hr Hu Hx Ih Ii Ij Ik Il In Io Ip Iq Ir It Iu Iv Jh Ji Jl Jn Jo Jq Js Lh Lj Lu Lx Ly Lz Mc Md Me Mf Mh Mj Mk Mn Mq Mr Ms Mt Mu Mv Mw Mx My Na Nb Nc Nd Nf Ng Ni Nj Nk Nl No Nr Nv Nx Ny Oh Oi Oy Pa Pd Pe Pf Pz Qa Qb Qc Qe) Qd(aA Et Fp Fr Hq Hu Hw Hx Ih Ii Ij In Io Ip Iq Ir Iu Iv Jg Jh Ji Jk Jl Jm Jn Jq Js Jt Lh Li Lj Lu Lx Ly Ma Mb Mc Md Mf Mg Mh Mj Mk Mm Mn Mq Mr Mt Mu Mv Mx My Na Nb Nc Ni Nl No Nr Nu Nv Nw Nx Ny Oh Oi Ok Om Pa Pb Pe Pg Qb Qc Qe) Pc(AA Et Fp Fr Hq Hr Hu Hw Hx Ii Ij Ik Io Ip Iq Ir Iu Iv Jg Jl Jm Jn Jq Js Lj Lu Lx Ly Lz Mb Mc Md Me Mf Mg Mj Mm Mn Mq Mr Mt Mu Mv Mw Mx My Na Nb Nd Nf Ni Nk No Nq Nr Ns Nw Nx Ny Of Oh Ok Om Oy Pa Pb Pe Pg Qa Qb Qc Qe) Pg(aA Et Fp Hr Hu Hw Hx Ih Ij Ik Il In Io Ip Iq Ir It Iv Jh Jk Jl Jm Jn Jq Js Jt Lj Lu Lx Ly Lz Mb Mc Md Me Mf Mg Mh Mj Mk Mn Mq Mr Ms Mt Mu Mv Mw Mx My Na Nc Nl No Nr Nw Nx Ny Oi Oy Oh Om Pa Pe Qa Qb Qc Qe) Nq(Aa Et Fp Fr Hr Hu Hw Ih Ii Ij Ip Iq Ir It Iu Iv Jg Jh Jk Jl Jm Jn Jq Js Jt Lh Li Lj Lu Lx Ly Lz Ma Mb Mc Me Mf Mg Mh Mj Mk Mm Mn Mq Mr Mt Mu Mv Mw Mx Nb Nd Ni Nj Nk Nl No Nr Nu Nv Nw Nx Ny Oh Ok Om Qa Qb Qc Qe) Ma(Fp Fr Hq Hr Hu Hw Ih Ii Ij Ik Io Ip Iq Ir It Iu Iv Jg Jh Ji Jl Jm Jn Jq Js Jt Lh Li Lj Lu Lx Ly Lz Mb Mc Md Me Mf Mh Mj Mk Mn Mp Mq Mr Mt Mu Mv Mw Mx My Nb No Nr Nu Nv Nw Nx Ny Oh Ok Om Oz Pe Qa Qc Qe) Jk(Et Fp Hr Hu Hw Hx Ih Ii Ij Ik Il Ip Iq Ir It Iv Jg Jh Jl Jm Jn Jq Js Jt Lh Lj Lu Lx Ly Lz Mb Mc Md Me Mf Mg Mh Mj Mk Ms Mt Mu Mv Mw Mx Na Nd Nf Nh Ni Nj Nk Nl No Nv Nw Nx Ny Oi Ok Om Pe Pf Qa Qb Qc Qe) Mm(aA Fp Hq Hr Hu Hw Ih Ii Ij Ik Im In Io Ip Ir It Iu Iv Jh Ji Jl Jn Jq Js Jt Li Lu Lx Ly Lz Mb Mc Md Me Mf Mg Mh Mj Mk Mn Mq Mr Mt Mw Mx My Na Nb Nc Nd Ni Nl Nr Ns Nu Nv Ny Oz Pa Pb Pd Pe Pf Qb Qe) Hx(aA FR Hq Hu Ih Ii Ij Ik Il In Ip Ir It Iu Iv Jg Jm Jn Jo Jq Js Lj Lu Ly Lz Mb Mc Md Mf Mg Mh Mq Ms Mu Mx My Nc Nd Nf Ng Nh Ni Nj Nk Ns Nu Nv Nw Ny Oh Oi Ok Om Pa Pb Pd Pe Pf Pz Qa Qb Qe) Li(Fp Hq Hu Ih Ii Ij Ik Io Ip Iq Ir It Iu Iv Jg Jh Jl Jm Jn Jq Js Jt Lh Lu Lx Ly Mb Mc Md Me Mf Mj Mk Mn Mq Mr Mt Mu Mx My Nb Nd Ni Nj Nk No Nr Nv Nw Nx Ny Oh Oi Ok Om Oy Pe Qa Qb Qc Qe) Im(Et Fp Fr Hq Hr Hu Hw Ih Ii Ij Ik Io Ip Iq Ir It Iv Jg Jh Jm Jn Jo Jq Js Lj Lu Lx Ly Lz Mb Mc Md Me Mf Mh Mk Mn Mq Mr Ms Mt Mv Mx My Na Nc Nl No Nr Nw Nx Ny Oi Ok Om Oy Qa Qb Qc Qe) Ml(aA Et Fp Hq Hr Hu Hw Ih Ii Ik Io Iq Jh Jq Js Jt Lh Lj Lu Lx Ly Lz Mc Md Mh Mk Mn Mr Ms Mt Mu Mv Mx My Na Nc Nd Nf Nh Ni Nj Nl No Ns Nv Nx Ny Of Og Oh Oi Ok Pb Pd Pf Pz Qb Qc Qe) Oz(Et Fp Fr Hq Hr Hu Ih Ii Io Ip Iq It Jh Jn Jo Js Lh Lj Lu Lx Ly Mb Mc Md Me Mf Mg Mh Mk Mn Mq Ms Mt Mw My Na Nc Nd Nf Ng Ni Nj Nl Nm No Ns Nv Nx Ny Og Oh Oi Oy Pd Pf Pz Qb Qc Qe) Nu(aA Fp Fr Hq Hr Hu Hw Ii Ij Ik Il In Io Ip Iq Ir Iu Iv Jg Jh Jl Jo Jq Jt Lj Lu Lx Lz Md Mf Mg Mk Mq Mu Mv Mw Nb Nc Nd Nf Ng Nk Nm Nr Ns Nv Nw Og Oh Ok Om Pa Pd Pf Qa Qb) Ne(Fp Hq Hu Hw Ih Ii Ij Ik Il Io Ip Iq Ir It Jh Jl Jn Jo Js Lj Lu Lx Ly Lz Mb Mc Md Me Mh Mn Mr Ms Mt Mx My Na Nc Nd Nf Nh Ni Nr Nx Ny Oi Oy Pa Pd Pe Pf Pz Qa Qb Qc Qe) Pe(aA FR Hq Hr Hu Ih Ii Ik Il In Io It Iu Iv Jg Jh Jm Jn Js Jt Lh Lj Lu Ly Lz Mc Md Mg Mq Mt Mu Mw Mx My Nb Nc Nd Nf Ng Nh Ni Nk No Ns Nv Ny Og Oi Ok Om Oy Pa Qc Qe) Mg(aA Et Hq Hr Hu Ii Ij Ik In Io Ip Ir Iv Jg Jh Ji Jq Lu Lx Ly Mb Md Mh Mj Mp Mr My Nb Nc Nd Ni Nj Nk Nn Nr Ns Nw Nx Ny Oe Of Oh Ok Om Oy Pa Pb Qb Qe) Nh(aA Et Hr Hu In Io Ip Iv Jh Jl Jn Jo Jq Js Lh Lj Lu Lx Ly Lz Md Mh Mr Mw Na Nb Nc Nf Ng Ni Nj Nk Nl No Nr Ns Nv Nx Of Og Pa Pb Pd Pf Pz Qc Qe) Iu(aA Fp Fr Hq Hr Hu Ii Ij Ik Il In Io Ip It Iv Jg Jh Jn Jq Lj Lu Lx Lz Md Mh Mp Ms Mw Nc Nd Nf Nj Nk Ns Nw Of Oi Ok Om Oy Pa Pb Pd Pf Qa Qb) Nm(aA Fp Hq Hu Ih Ii Ik Il In Jh Jo Js Lh Lj Lu Ly Lz Mb Mc Md Mh Mj Mk Mn Mq Mt Mw My Na Nb Nc Nd Ni No Nr Ns Nx Oh Oi Oy Pa Pb Pd Qb Qc) Il(aA Et Hq Hr Hu Ii In Io Ip Iv Jl Jm Jn Jq Jt Lh Lj Lu Mf Mj Mq Mu Mv Nb Nc Nd Nf Ng Nj Nk Ns Nv Nw Of Oh Ok Om Pb Pd Pf Pz Qa) Oe(Et Fp Fr Hr Hu Io It Jh Jm Jn Jo Js Lj Lu Ly Lz Mb Mc Md Me Mf Mh Mn Ms Mt Mv My Na Ni Nj Nl Nx Of Og Oi Oy Pb Pf Pz Qa Qc) Fr(aA Hq Hu Hw Ij Ik Io Iv Ji Jl Js Jt Lh Lw Lz Md Me Mj Mk Mp Mr My Nb Nd Nf Ni Nj Nk Nn Nr Ns Of Og Oh Pa Pb Qb Qe) Mz(aA Et Fp Ih Ii Ij Ik Iq Ir Jh Jm Jn Jq Js Lh Lx Ly Mc Me Mj Mn Mr Mt Mv Nv Nx Ny Oi Oy Qa Qc Qe) Og(aA Hr Hw Ii Ij In Ip Ir Iv Jh Jq Jt Lh Lx Mf Mj Mk Mq Mu Mv My Nb Nc Nd Nk Nr Ns Nv Nw Oh Ok Pa Pb Qa Qb Qe) Jg(aA fR Hq Hw Ij Ik In Io Ip Iv Ji Jo Jq Jt Lj Lu Lw Ly Mb Mj Mq Ms Nb Nc Nd Ng Nk Of Oh Oi Pa Pb Pd Qb) Om(aA fR Hr Hw Ii Ik Io Iv Jl Lj Lu Lx Lz Mp Mq Nc Nd Ni Nj Nk Nr Ns Nv Nw Of Oh Oi On Oy Pa Pb Pd Qe) Of(aA Hw Ii Ij In Ip Ir Iv Jo Jq Jt Lh Lx Mf Mk Mq Mr Mu Mv My Nd Nk Nr Nv Nw Ny Oh Ok Qa) Nw(Ij In Io Iv Jl Lj Lw Lz Mb Mf Mq Ms Mu Nb Nc Nd Nf Ng Nj Nk Ns Oh Oi Oy Pa Pb Pd) Ng(aA Hw Ij In Ip Ir Iv Jj Jl Jn Jq Jt Lx Mq Mt My Nb Nd Nk Nv Oh Ok Pa Qa) fR(Et Fp Hr Ik Ji Jm Jn Jo Jt Lh Ly Md Mq Mr Mt My Nd Nf Ni Ns Nv Oi Ok Qc) Mf(aA Ij In Ir Iv Jo Jq Jt Mp Nc Nd Nf Nk Nn Ns Oi Ok Oy Pa Pb Pd Pf Pz) Nk(aA Ij In Io Ip Ir Iv Jq Lj Lx Mq Mu Mw Nd Ni Ns Ok Pa Pd Pf Pz Qa) Pz(aA Et Hw In Iq Iv Jj Jt Lx Mk Mn Mq Mu Mv Mw My No Nv Ny Oh Qb) Jo(Hq In Ip Iq Ir Iv Jq Lh Lx Mj Mk Mq Mu Mv Mw My Nb Nv Ny Oh Qa) aA(Hr Hw Ij In Ip Iv Jj Jl Me Mk Mq Mu Mv Mw My Nd Nj Ns Pa Pf) Lw(Ih Ip Iq Ir Jn Jt Lh Lx Ly Mh Nd Nj Nl No Nv Ok Pd Qa Qc) Oh(Hr Ij In Io Ip Md Mu Mw Nc Nd Nf Ns Oi Pa Pd Pf Qa Qb) Ji(Ii In Iv Jm Mk Ms Nc Nd Nf Nj Nr Ns Oi Ok Oy Pa Pd) Mu(Aa Ij In Ir Jt Ms Nc Nd Nf Ns Oi Ok Oy Pa Pd Pf) Qa(Hq In Iv Ji Lj Lz Md Mp Ms Nd Nj Ns Oi On Pa Pf) Ij(Hr Ii Io Ip Iv Ji Ms Nc Nd Nj Ns Oi Pb Pd) Jj(Ip It Jn Lj Mh Mr Ms Nc Ni Nl No Oy Pd Qc) Mq(Hr In Ms Nc Nd Nf Nj Ns Oi Pa Pb Pd Pf) Mw(Hq Hu In Ip Iv Nd Ns Ny On Pb Pd Pf) In(Hr Io Ip Ir Nc Nd Nf Ns Pa Pd Pf) Iv(Hr Io Ip Ms Nd Nf Nj Ns Oi Pa Pb) Ji(Ip Ir It Jh Jm Jn Js Mv Nl Pd) Pf(Aa Hw Ir Jq Jt Lx Mv Nb Nv Pa) Ms(Ip Iq Ir Jq Jt Mv My Nd Ok) Nj(Iq Ir Jq Lx Nc Nd Ny Ok) On(Hr Ir Jh Jq Ly Mv Nl Ok) Pa(Aa Hr Ip Lz Nd Nf Ns Pd) Mp(Hw Ih Jt Md Mv Nd Nl) Pb(Ii Lx Mr Nr Nv Ny) Ip(Fp Ik Nb Nd Ns) Jt(Ii Lh Nc Nd Oi) Ok(Et Io Mb Nd Oy) Nn(Jn Mx Na Nl) Jh(Hu Ns Oy) Pd(Mv Nb Nv) Oi(Lx Mv) AaMi LzMj NbLh NdJq NfNv Hrli} Lv{Qa(aA Et Fp FR Hq Hr Hu Hv Hw Ih Ii Ij Il Im In Io Ip Ir Jh Jk Jl Jm Jn Js Lh Li Lj Lu Lw Lx Lz Ma Mb Mc Me Mf Mg Mh Mj Mk Mm Mn Mp Mq Mr Mt Mu Mv Mw Mx My Na Nb Nc Ne Nf Ng Nh Nk Nl Nn No Nq Nr Ns Nt Nx Ny Of Oh Oi Ok On Oy Pa Pc Pe Pg Po Qb Qc Qe) Ir(aA Et Fp Fr Hq Hr Hu Hw Ih Ii Ij Il In Io Ip Iq Iv Jh Jk Jm Jn Jr Js Jt Lh Li Lj Lu Lw Lx Lz Ma Mb Mc Md Me Mf Mg Mh Mi Mj Mk Mn Mp Mq Mr Ms Mt Mu Mv Mw Mx My Na Nb Ne Nf Ng Nh Nk Nn No Nq Nr Ns Nt Nx Ny Of Oh Oi Ok Oy Pa Pb Pc Pe Pg Po Qb Qc Qe) Jk(aA Et Fp Fr Hq Hr Hv Hw Ih Ii Ij Il In Io Ip Iq It Iv Jg Jh Jm Jn Js Jt Lh Li Lj Lu Lw Lx Lz Ma Mb Mc Md Me Mf Mh Mj Mk Mn Mp Mq Mr Ms Mt Mw Mx My Nb Nc Ne Nf Ng Nh Ni Nj Nk Nn No Nq Nr Ns Nt Nv Nx Oe Of Oh Oi Om Pb Pc Pe Pg Po Qc Qe) Mn(Et Fp Fr Hq Hr Hu Ih Ii Il In Io Ip It Iu Iv Jh Jm Jn Js Jt Lh Li Lj Lu Lz Ma Mb Mc Md Me Mf Mg Mh Mj Mk Mm Mq Mr Ms Mt Mu Mv Mx My Na Nb Ne Nf Ng Nh Ni Nk Nl Nn No Nq Nr Ns Nt Nx Of Og Oh Oi Oy Pa Pb Pc Pe Pg Pz Qb Qc Qe) Ij(aA Et Fp Fr Hq Hr Hu Hw Ii In Io Ip Iq Iu Iv Jh Jm Jn Jr Js Lh Li Lj Lu Lx Lz Ma Mb Mc Md Me Mf Mg Mh Mj Mk Mp Mq Mr Ms Mt Mu Mv Mw Mx My Na Ne Nf Ng Nh Nk Nn Nq Nr Ns Nt Nx Oe Oh Oi Ok Oy Pa Pb Pc Pe Pg Po Qb Qc Qe) Et(Fp Fr Hq Hr Hu Hw Ih Il Im Io Ip Iq It Iu Iv Jg Jm Jn Jr Js Jt Lh Li Lj Lu Lx Lz Ma Mb Mc Md Me Mf Mj Mm Mp Mq Mr Ms Mt Mv Mw Mx My Nb Nc Nf Nh Ni Nl Nn No Nq Nr Ns Nt Ny Of Og Oh Pa Pb Pc Pe Pg Po Qe) Pg(FR Hq Hr Hu Hw Ih Il In Io Ip Iq Iu Jh Jn Js Jt Lh Li Lj Lu Lx Lz Mb Mc Md Me Mf Mg Mh Mj Mk Mp Mq Mr Ms Mt

Figure 29 Continued bU bV cA cD cM Cv dC Dd dH dI dK) aZ(Aj bE bS bV cD cE cF CH dB dC DD dE Dg dI) dK(Ad An aO Ar bB bH bS bZ cB cO Cq cW cZ
dB dD dG) Ap(aH Al aV Ax bB bF bG bV cF Cq cZ dB Dd Dk Dl) bO(al aL AO bB bH bS bV cA cB cR cT dB Dg Dk) aV(al aL Ao aQ Ax bB
Bc Bg cO Cs cT cW dl Dk) Dd(aL aU bL Bo bU bV bW cB cO cY dB dD Dg) Cq(aO aU bB BC Bo cB cM dB dC dD dE) dF(Aj Bc bF bH bl
bM bX cL cV cW Dg dJ) al(aC Ax bE bV bW cT Cv cX cY dC dM) bZ(aD aK Al Ax bB BC cE cG cM dE) bW(aO Ax bB bG bP bV cB cF Cv
dC) aO(Af aK Al aM Ax Bc cY dC) bV(Al bJ cZ dB dI dN) aU(BC bL cG cT dB dM) bB(Ax bS dE dl dM)
bC(bM cD cR Cv Dk) bL(Al cD Cv dC dE) cB(Al Bc cT dI dM) cG(aC bE bF bG dJ) Af(Aj bM Cs dM) Bc(Ao cY dC) Al(aK cC) CscY
dBdM} Jj(Jk(Et Fp Hq Hr Hu Hw Hx Ih Ii Ij Ik Im In Io Ip Iq Ir It Iu Iv Jg Jh Jm Jn Jo Jq Js Jt Lh Li Lj Lx Ly Lz Mb Mc Md Me Mf Mg Mh Mj
Mk Mm Mn Mp Mq Mr Mt Mu Mv Mw Mx My Na Nb Nc Nd Ne Nf Ng Nh Ni Nj Nm Nn No Nr Ns Nt Nu Nv Nw Nx Ny Oe Of Oh Oi Ok
Om Oy Pa Pb Pc Pd Pe Qa Qb Qc Qe) Nv(Et Fp Hq Hr Hu Ih Ii Ik In Io Iq It Iu Iv Jg Jh Ji Jm Jn Jo Jq Jr Js Lh Li Lj Lw Lx Ly Lz Mb Mc Md
Mf Mg Mh Mj Mm Mn Mq Mr Mt Mu Mw Mx My Na Nb Nc Nd Nf Ng Nh Ni Nk Nl No Nr Ns Nt Nu Nw Nx Ny Of Og Oh Ok Om Oy Pa Pb
Pc Pd Pf Pz Qa Qb Qc Qe) Is(Et Fp Hq Hr Hu Hw Hx Ii In Io Ip Iq Ir Iu Jg Jh Ji Jm Jn Jo Jq Js Jt Lh Lu Lw Lx Ly Mb Mc Md Me Mh Mj Mk
Mn Mq Mr Mt Mv Mx Na Nb Nc Ng Ni Nk Nl No Nr Ns Nt Nw Nx Ny Of Oh Ok Om Oy Pa Pb Pd Pf Qa Qb Qc Qe) Om(Et Fp fR Hq Hr Hu
Hw Ih Ij Ik Im Io Ip Iq Ir It Iv Jm Jo Jr Js Lh Lj Lu Lw Lx Ly Lz Ma Mb Mc Me Mf Mn Mp Mr Mt Mw My Na Nb Nd Nf Nj Nk Nm Nn No Nq
Nr Ns Nu Nw Oe Of Oh Oy Oz Pa Pb Pd Pf Qa Qb Qe) Po(Hq Hr Ii In Io Ip Iq Ir It Iu Iv Jh Ji Jm Jn Jo Jr Js Li Lu Lx Mb Mc Md Mg Mq Mr
Ms Mt Mu Mw Mx My Na Nc Ng Nh Ni Nk Nl Nm No Nr Nt Oe Of Oh Pa Pc Pd Pz Qa Qb Qc Wm) Nw(Hq Hu Hx Ih Ik Im Ip Iq Ir Iu Jg Jh
Jm Jo Jq Jr Jt Li Lj Lx Ly Lz Md Me Mf Mh Mi Mp Mu Mv My Nd Nf Nj Nm Nn Nr Ns Nt Nu Nx Ny Og Oi Ok Oz Pa Pb Qa Qe) Il(Fp Hu
Hw Hx Ih Ii Ik In Io Ip Ir Jh Jm Jn Jo Js Lj Lu Lz Mb Mc Mh Mj Mq Ms Mt My Nb Nd Nf Ng Ni Nj Nl Ns Oe Of Og Oh Pb Pc Pf Pz Qa Qe)
Im(Hu Hw Iu Jh Jq Jr Lh Li Lj Lu Lw Mb Mc Md Me Mi Mk Mp Mr Mw Mx Nb Nd Ne Nf Nh Nj Nm Nr Nt Nu Og Oh Oi Oy Pa Pc Pe Pf Qe)
Lx(Et Hv Hw Hx Ir Iu Jg Jq Jr Jt Mg Mj Mk Mp Mv My Nj Nn Nq Nt Nu Nx Ny Oe Ok Oz Pe) Ma(fR Ih In Iq Iv Jm Jq Jr Js Mi Mk Mn Ne Ni
Nk No Nr Nt Nx Ok Qa Qb Qe) Pe(Et Hv Iq Jg Jq Lh Mf Mk Mm Mn Mp Mu Mv Nf Nn Nq Nu Nx Ny Ok Pd Pf) Ny(Hu Hw Hx Jg Jq Jr Mj
Mk Ml Mp Mu Mv My Nj Nn Nt Nu Oe Qa Qe) Hv(Et Iq Ir Ji Jq Lh Mj Mk Mn Mw Nq Nt Nu Nx Oz Qa Qe Wm) Jq(Hu Hw Hx Lh Mk Ml Mp
Mu Mv My Ne Nn Nq Nu Qa Qe) Nq(Hw Hx Ii Iq Jm Jr Lh Mj Mn Nx Ok Qe) Ml(Et Hw Hx Ir Jg Ji Jr Mi Mj Mk Mn Mv) Ij(Ii Ip Ir Jm Mi Ms
Mt Nt Pd Qa Wm) Hw(Et Lh Mf Mk My Nj Nn Nx Oe Oz) Hx(Et Hr Lh Mf Mn Nt Nx Og Ok) Mj(Et Jg Lh Mg Mm Mn Mp Nx) Ok(Hu Lh Mk
Mp Nn Oz Qe Wm) Nt(Iq Mn Nd Ne Nh Oe) Mi(Lh Mn Ne Nh Nx Oz) Jr(Mm Mn Mw My Oe) Qa(fR Nu Nx Oz) Jg(Ir Ng Og Qe) Lh(Iq Mk
Ne Oe) Nn(Ir Mn Pc) Mv(fR Ne Nx) Ji(Ms Ne Nh) Jl(Nc Nk Nl) Oz(Ir Qe) WmJn EtNh MkNx MnHu NkPg InQd} bA{Di(AD aE AJ aK aM
aN AO aQ AR As Ax aY Ba BB Bc bE bF bH bl bM Bo bP bQ bR bS bU bV cA cE cH cI cL cN CP Cq Cs CV CW cZ dA DB dC DD dF DG
dJ DL dM dN fR) bZ(aD aE aF aH AJ aK AN aQ aR aS aU aV aW aY Bb bE bF bG bH bL bM bN bP bQ bR bS bU bV cA cG cH cI cK cL cM
cN cO Cp CQ cV CW cY cZ dA dC DG dI dJ DL) Aw(Ad aG aH aJ aK AL aN Ao aQ Ar aW BB Bg bI bL bN Bo bP bQ bR bS bU cA cC cD
cE cF cG Ch cK cL cN cO Cp CQ cR Cs CW dA dB Dc dD De dG dH dI DK fR) cX(aD aE aH aK aL aN Ao aR AS aV aW aY Bb bF BG bH
bl bM bN Bo bP bU bV bX cA CH cI cL cM Co Cp cQ cV Cw cZ dA Dc DD DG dH dI Dk dL dM dN) bW(AD aH aJ aK AN aO aQ aR aU aV
aW bC bH bl bL Bn bQ bU bV bX cA cG cJ cL cM cN CO cP Cs CW cY cZ dA dB Dc dF dI dJ Dk dM fR) bC(aE aH aJ aM An aZ Bb bH bI
BN Bo bP bU bV cA cC cF cH cL Ct cW cZ dA Dc dD dF dH dI DK dL dM)) bJ(aE aF aH aJ aK aO Ap aQ aV aY aZ bF bI bM bN bR cC cD
cF CH cM Co Cp Cu cW cZ dA dB dC dD dF dH) aG(aF aJ aL aM aN aO aU aY aZ bB BG bH bL bM BN bR cC cD cF cG CH cI cJ cO Cu
cW dB dH dN) al(Af aH AS aW aY Ba Bb bG bH bI bL bM bN bP bR bS cD cE cF cI cJ Cu cW dB DC dH dI dM fR) cT(aE aF aH aL aM aO
Ap aR aY bE bF bG bH bI bP bR bU cC cD cF cM cN CO Cp cR cY dD dG dH dL) dK(Af aJ aL aM Ax aY aZ bB Bc bH bI bM BN bO bP bS
cF cG Ch cI cJ cO cR Cu cW dB Dc dD De dF) aU(aJ aK aM An aO Ar As Ax aZ Bc bI bL bM BO bS cF cG cH CO Cq cR Cs Ct Cw dB Dc
fR) cB(aF Al aM An aO Ap aW aZ Bc bE Bg bM bQ bV cA cC cF cG cH cI cK Co Cu dC Dd dI dM dN) cG(aE aJ aL aM aO aV aW Ax aY bB
BG bH bL bN bP bQ cE CH cK cM cQ dB Dk dL) dE(aE aF aH aJ aO aV aW aZ bM bN bQ bR bU bX Ch cO Cp cQ cR Cu cZ dA dC dD dF
dH) bO(AF aJ aL aM aY aZ bB BG bL bM bN cC cF cJ CO cR Cu dB dC) cJ(Ad AJ aM Ao Ar Ax bG bH bL CO Cp Cq Cs Cv Cw Db DI)
cO(aL aV aZ bB bG bN bQ bR bU cC cN cR dA dB dl) cR(aF aM aW aZ bI bN cF cH Cp cQ cY dB dH) Ap(Af aV bL bU cD cF cH cK dB dD
De Dk) aZ(aO BG bH bL cC cF Co) De(bF bI Cu cV cZ dI fR) bB(Af aJ aM bG bH cC cF) Bg(Af aV aW bE Bn cC) bL(aL aM bR cD cF dH)
aV(Af Bn Ch Co Cu) bG(aC aF cD dB dC) cC(bH bQ dB fR) Bn(Co Cp cY) aM(aL cH dB) Af(Cp cY) Co(cD cF) aF(aO Ch) CudB bHcD
bQdH} Aw{cJ(Ad aE aF aG aK AN aO Ap aS Ba BB bC bG bI bJ bN bP bQ bR bS bU cB cC cD cE cF cG CH cI cK cL cM cN CO Cp Cq cR
CT cV CW cY Db dC dD dF dH dK DL dM fR) Bn(aD aE AF Aj aK aM Ao Ap aQ AS aU aW Ba BB bF bH bI bJ bM bN Bo bP bR bU bW bX
cA cD cE cF cH cK cN CO CP cQ Ct CV Cw cY dA dB Dc DG dH dI DL dN) Al(Ad aH AJ aL AO Ap Ar aU aZ BB Bc BG bJ bL bN bP bR
bU bV cC cF CH cI cK cM cN cP cR CV cZ dA DB dD dE dH dJ DK Dl dN fR) bO(Ad aE aF aG Aj aK aM An AO Ap aQ aR aY Bb bF bI bL
bN bR bW bX cA cB cC cD cE CH cI CO CP Cq cR cV CW cY dA Dd De dG dI dL dN) Ar(AD aE aF aH Aj An Ao aU aV aZ BB BG bL bN
Bo bP bR bU bX cB cG Ch cI cK cM cN Cq cT Cw cX dA Db dH Di DK Dl fR) Bc(aD Af aH aI aK aN aO aQ aU Ax aY aZ Ba Bb bF bL bQ
bR cA cC cE cI cL Co CP CV cX Db DC De dF DG Dk dL dM dN) bG(aD Af aI AJ aL aM aN Ap aV bC bF bP bQ bU bV cA cC cF cG cH cK
cL cM cP cT cV cX dC dD dG dH Di Dk DI) al(aD Af aN Ap aR As aV Bb bJ bL bW bZ cD cE cH cM cO Cs cT Cu cW cX DC Dd De dF Di
Dk dM) aL(aD aF aG aH Ao aS aW aY bB Bg bP bQ bR bX cF cH Co cP Cs CV cW dA Db Dc dH dJ Dk Dl) aZ(aG AJ An aO Ap As aU Ba
bH bJ bL Bo bW cD cF cH cK cM cN cR dB dC dD Di dK dN fR) cX(aG aH aJ aK aN Ap Ba Bb bL bP bQ bV bZ cM Cv cW dB DC dD dE Di
dM fR) Af(aK aN Ap As Ba Bb bS bW bZ cM Cq cT Cu cW dE Di Dk dM fR) dF(Aj aN aU aV Ba bJ bL bQ cD cG cK cM cT dC dE dH dI
DK) bV(Aj aK As Bb Bg bL bP bU cB cE cG cK cN Dc dH Di Dk) aJ(As aV Bg bN bP cD Ch cM Ct dD dE dG Di Dk dL) bC(aK aS aU Ax
BB bM Bo cB cD cZ dB dD Di) cG(Aj aN AS bL cD cE cH Cs dD Dg dH Di dM) Dk(AD Ap Bg cD cM Cp Cq cT dB dD dE fR) As(aG aN bL
bZ Cs Cu Dc DD Di dM fR) Dc(Ad aO aV Bo cD dB DD dE Di Dl) Ax(aC aH Ao bI cH cY dC Dd Dl) dD(Ba Bb bS bW bZ cO cW Di fR)
Cu(aG aV bJ Bo bQ dB dH Di) aV(aQ Cs cS dA dB dC dE fR) dM(bP cD cK cM dH Di) Dd(Ad An Cp Cq Cw) bS(bR cB cK) dE(aC aG cT)
fR(cD cM dC) Aj(bL bZ) Di(aG cT) bPbW bQcE bZdC cKdI} Qd{Oz(Et Fp Hq Hr Hu Hw Hx Ih Ii Ij Im In Io Ip Iq Ir Is Iv Jg Jh Ji Jm Jn Jq Jr
Js Jt Lh Li Lj Lu Lx Ly Ma Mb Mc Md Me Mf Mh Mi Mk Mm Mn Mp Mq Mr Mt Mu Mv Mw Mx My Na Nb Nc Ne Ng Nh Ni Nl No Nq Nr
Ns Nt Nu Nv Nw Nx Ny Oe Of Oh Oi Ok Om Oy Pd Po Qb Qc Qe) Nj(Et Hq Hr Hu Hw Hx Ii Il Io Ip Iq Ir Iv Jg Jh Ji Jk Jl Jn Jq Jr Js Jt Lh Lu
Lw Lx Lz Ma Mc Md Me Mf Mg Mh Mj Mk Mm Mq Mr Mt Mu Mw Mx Nb Nc Ne Nf Nh Ni Nk Nl Nn No Nq Nr Ns Nt Nv Ny Oe Oh Ok
Om Pa Pb Pc Pe Pg Po Qc Qe) Pf(Aa Et Fp Hq Hu Hx Ii Il Io Ip Iq Ir Is Iv Jh Jm Jn Jq Jr Js Jt Lh Lj Lu Lx Ly Lz Mb Mc Md Mg Mh Mj Mk
Mn Mq Mr Mt Mv Mx My Na Nb Nc Ne Nf Ng Nh Ni Nk Nl No Nr Ns Nt Nu Nv Ny Oh Oi Oy Pa Pb Pd Qa Qb Qc Qe) Ml(Et Hq Hu Hw Hx
Ih Ii Ij Im Io Ip Iq Ir Is Iv Jh Jk Jl Jq Js Lh Li Lj Lu Lx Lz Ma Mb Mc Mf Mg Mi Mj Mk Mm Mq Mr Ms Mt Mu Mv Mx Nb Nc Ne Nh Nl Nm
No Nq Nr Ns Nx Ny Oh Ok Pa Pe Po Qc Qe) Nm(Aa Hq Hu Ih Ii Ij In Io Iq Ir Is Jh Jn Jo Js Lu Mb Mc Mh Mj Mk Mn Mq Mr Ms Mt My Na
Nc Ne Nh Nl Nr Nx Ny Oi Pa Pe Qa Qc Qe) It(Fp Hr Hv Hx Ik Is Iv Jg Jk Jl Ly Ma Me Mf Mh Mm Mn Mp Mu Mw Nd Nf Ng Ni Nk Nq Ns Nt

Figure 29 Continued cB(Al bS) cR(dB dC) ApdH AxaU bCbM} bC{As(aO aS bG Cp dD Dk) bM(aS bB bF bG Cq cZ) Bb(aO aS bB Bg Dl) Dc(Ad Aj aO Dl) AfbB AjBa cBdM cRcZ} Lx{Mw(Hq Ik Io Lj Mb Pd Qb) Ik(Hq Jm Lj Mb Mc Md) Jm(Hq Lz Mc Md) Mq(Nf Pd) Li(Io Pd) NuNv MrLj QbQe} Iu{Ir(Et Im Mf Mg Mu Oe Po) Jt(Il Nv Pa Pe Po Qa) Jt(Il Nv Pe Po Qa) Po(Jq Nu) Qa(Nu Wm) Etll} Ma{Ng(Hx Ii Jh Mr Nb Nr Pa) Hx(It Mg Nf Nu Og Oy) Pd(Mj Nr Ny) Pz(Ny Po) NeNl Nilm Illt OfPe} Aj{Ba(aG bG bJ bL Ch Co Cq Dk Dl) Ap(Al Bg Ch dD Dk) bW(BG Ch) aU(Al Dc) BgCw} Og{Mw(Hx Jq Nt Nu Po) Hx(Jk Mm Nt Nu) Po(Lj Nf) Mm(Hv Il) HvNv lilm JkJq LiNy} cB{bV(Al As bL Bn dM) bS(aG aO As cT) dM(aG aO bQ) Ar(Ba bW) DkbW bQcE} dB{bQ(Bc bM cC cE) Al(aU aV cD) Dc(aG aV dC) Ax(aU cR) AfBa ApbG BcaM CqbM} Wm{Mw(Hw Lh Lu Ly Nf Nl Nx Pd) Oe(Et Ir Mr Qa) EtOf Mhlm liJn} Ax{aU(aG AS bF bJ cR) Ba(aO Dl) bB(bW cR) ApaS DgDl bQcD} Ng{Mm(Hu Hv Il Mw) Mg(Jk Nv Po) Jh(Ny Oh) Jk(Et Nt) PoLj MvMw} nR{mW(kP mH mS mZ nB nC nD nF nl) nK(kI oQ) nDkO nFoQ} Pz{Mm(Hv Ir Jk Pe) Et(Il Jk) Qa(Hw Ij) NtNv ImJt} Al{aV(Af bB Bo cD) cD(bL Bo) ApDl BbdD aOaU} bW{bG(As bM dC dD) bM(bB Cq) BgcT aMdD bQdH} kG{nD(nH nL oP) mZ(lX nK) nH(lY nL) oQ(nF nK)} Dc{Ad(aG aU Co) aV(aO bJ Bo) BoaG DlaU} Ap{dD(Af aS bG cH Dk) aS(bG Dk)} Hv{Nv(Ns Nu Oe Of Oi) NtOe MmOi} Nf{Po(Ik Lj Oe) MwOy LiNy} Im{Mj(Fp Hr) Pc(Hu Oi) IiIt} bQ{cE(bB bF cD) bJ(aS bM)} bV{bB(aM As Bn) Cp(As cD)} Nu{Oe(Hx Lh Nr)} Mm{Oy(Mj Pe) IlIt} As{ArCp DkaU} Ba{Dl(Af Bn)} Hr{Hx(Lh Li)} Hw{Qa(It Qb)} BbaMaO PoLjOf NtOiPc aQaUbG mYmZnl nDkCkF Unconstrained panels with 2 analytes, where 1.0E-7 >= 'AUC p-value' > 0. Contains 127 panels of 16,069 total panels evaluated. : cU(aA aD aE Af aG aH aI aJ aK AL aM aN aO AP aQ aR AS aU aV AW AX aY aZ BA BB BC bE BG bH bJ bL bM Bn bO bP bQ bR bU bV bW bX cA cC cD cE cF cG cH cI cJ cK cL cM cN cO CP CQ cR CS cT cV CW CX cY cZ dA dB DC dD DE dF Dg dH DI DK dM dN FR) cS(aA Af aL Ax bA Cx) Cx(aA aX cG Cu) Lv(Ji Jp Mi Mz) Qd(Ik Iu Jj) On(Mm Of Pb) aA(aX cJ nU) bA(De Fr) AwAx CucJ DkdK aXbG cGcX Unconstrained panels with 2 analytes, where 1.0E-6 >= 'AUC p-value' > 1.0E-7. Contains 89 panels of 16,069 total panels evaluated. : Lv(aA Hx Im Is Jj Jl Jn Jq Jr Lw Lx Ml Mp Mw Nd Nu Nv Nw Ny Oe Om On Oz Qd) cU(aC aF Aj An Ao Ar bF bI bN Bo bS cB Ch Co Cv Db Dd DL) aP(aI aL cB cS Cx dG dH dL) Fr(Aj aL As cJ cT Cx dB) Jp(Ji Lw Mi Mp Nn On Wm) On(Jj Ml Nj Nm Pz) cS(As Bb bM Di) Jj(Ij Jl Pg) Cu(bO cX) Cx(Aw dF) aX(Cq Dc) ApaL DicJ NmNw PzQd aAaG nUmF Unconstrained panels with 2 analytes, where 1.0E-5 >= 'AUC p-value' > 1.0E-6. Contains 219 panels of 16,069 total panels evaluated. : Lv(Et Fp Hq Hu Hv Ii Ij Iq Ir Jg Jh Jk Js Jt Lu Ly Mc Md Mm Mn Mq Mr Mt Mv Ni Nm Nn No Nq Nt Nx Of Ok Pd Pe Pg Po Qa) On(Hq Hv Ii Io It Iu Jg Jo Li Ly Mb Mh Mi Mk Mp Ms My Nb Nc Nd Ne Nn Ns Nv Nx Og Oy Oz Pa Pd Pf Qb) Jp(Hv Hx Im Is Jj Jk Jr Li Ma Ml Mm Mz Ne Nm Nq Nt Oe Oz Pc Pe Pg Po Qd) aP(aG Aw bB bG bO bR cF cJ cX dA dD Di dK) aA(aI Aw bC bZ cB cG cX DE dK Fr) aX(aL aO aS Ax bA Cp Cu cX Dd dF Di) cS(aI AJ Aw Bc bG Bn Dc dM) Cx(aJ BA cJ Cw Dc Di fR) Mz(Jj Ml Mp Ms Nj Nn Nq Oe) Aw(AL Ar Bn bO Dk Fr) cU(Ad bZ Ct Cu dG dJ) Qd(Ml Nj Nm Oz Pf) Jj(Is Jk Nv Om Po) dK(aL Ax bG dF Fr) bA(bW bZ cX Di) Cu(aG aV dE) Fr(dC Dg Di) Nn(Jr Nf Of) Mi(Iu Jl Pd) aL(bC bW De) Lx(Ik Jm) Mp(Jr Oi) Is(Iu Ml) Nw(Il Jk) Oz(Jl Pg) cG(Af Di) DccJ NqOi LwHu PfPg aIaJ aZbQ nTnU Unconstrained panels with 2 analytes, where 1.0E-4 >= 'AUC p-value' > 1.0E-5. Contains 785 panels of 16,069 total panels evaluated. : Cu(aC Ad aE AF aH aI Aj aK aL aM AN AO AP aQ AR AS aU AW Ax aY aZ Ba BB BC bE BG bH bI bJ bL bM BN Bo bP bQ bR bS bU bV bW bX bZ cA cB cC cD cE cF cG Ch cI cK cL cM cN CO CP CQ cR CS CT CV CW cY cZ dA DB DC DD De dF Dg dH DI dJ DK DI dM dN FR) Jp(aA Et Fp FR Hr Hu Hw Ih Ii Ij Ik Il In Io Ip Iq Ir Iu Iv Jg Jh Jl Jn Jq Jt Lh Lj Lu Lx Ly Lz Mf Mg Mh Mj Mk Mq Ms Mt Mu Mv Mw Mx My Na Nb Nc Nd Nf Ng Nh Ni Nj Nk No Nr Ns Nu Nv Nw Nx Ny Of Og Oh Oi Ok Om Pa Pb Pd Pf Pz Qa Qb Qe) On(aA Et Fp Fr Hu Hw Hx Ih Ij Ik Il Im In Ip Iq Ir Iv Jk Jl Jm Jn Jq Jr Js Jt Lh Lj Lu Lw Lx Lz Ma Mc Me Mf Mg Mj Mn Mq Mr Mt Mu Mw Mx Mz Na Ng Nh Ni Nk Nl No Nq Nr Nt Nu Nw Oe Oh Oi Ok Om Pc Pe Pg Qa Qc Qd Qe) Lv(Fr Hr Hw Ih Ik Il In Ip It Iu Iv Jm Lh Li Lj Lz Ma Mb Me Mf Mh Mj Mk Ms Mu Mx My Na Nb Nc Ne Nf Ng Nh Nj Nk Nl Nr Ns Og Oh Oi Oy Pa Pb Pc Pz Qb Qc Qe) Mz(Et fR Hr Hv Hx Im Is It Iu Iv Jg Jk Jl Jo Jr Li Lw Lx Ly Ma Mb Mf Mg Mi Mm Mn Mu Mv Mw Nf Nk Nm Nt Nu Nv Nw Nx Ny Of Og Om Oy Pb Pc Pf Pg Po Qd) aP(aA aE Af aH aM aO aS aU aV aX aY aZ bA bF Bg bJ bL bN bP bU bZ cD cG CH cI cM cN cP cR cT cY cZ dB dC DE dF Fr) cS(aE aG Al aM An aO Ap aS aZ Ba bL BO bQ Ch Cp Cq Cs CT Cv cX cZ DD dF Dg Dk FR) cG(aG aI AJ aL aM aO As Aw Ax bA bG bL bM Bn BO bV cE cF cL cT dB dD dE Dg dH Dk) aA(aH aL aM aU aZ bB bF bJ bO bQ bW cO cR dB dD Di fR kF kG Ma mF Mp mZ Nn Nq nR) Nw(Hv Hx Ij Jj Jl Jr Ma Ml Ne Nh Nj Nk Nq Nu Oe Og Oz Pf Pg Po Pz Qd) aX(aE Af aG aI AJ Al An As Aw Bg bM BO Ch cJ dD Dg Dk fR) Qd(Hr Hv It Iv Jg Jo Lw Ly Me Mm Nd Nn Nu Og Om Pc Pd Qb) Lx(Hq Io Jj Jr Lj Lw Lz Mc Md Ml Mp Mw Nj Nu Oe Of Pd) Aw(Af aI aJ As aV aZ bA bG bV bZ cJ cX Dc dF Di dM) Fr(aD Af aG aH aI aS aZ bB BO cB cD Cq cX dD Ng) bA(aG aI Ap aU bB bC bJ bO cB cO cR cT dE dK) Jj(Et Il Im Jq Lh Mn Nt Ny Ok Pe Qa Qe) Di(aG aI aJ AL Ax aZ Ba bC bV Dc) Is(It Jo Nj Nm Oe Of Og Oz Pf Pz) Jr(Im Lw Ma Mi Mw Nm Nq Nu Oe Wm) aJ(aG aL bO cB cF cJ cX dD dK dL) Jl(Im Iu Ji Jo Lw Ml Nj Oe Og) Nv(Hv Ji Mi Ml Nj Nm Nu Oe Og) Ny(Jh Li Lw Mp Mw Nn Nu Pb) Om(Hv Jo Ml Ne Ng Nj Nm Og) Pg(Ji Jo Lw Mi Nj Ok Oy Pd) aI(aM Ap aZ Ba bC DE fR) Po(Lj Ml Nj Oe Of Og Oz) cJ(Al Ax Ba Bb Bc Cp Dk) Mi(Hu In Ms Nn Og Oz) aZ(aO bO bZ De dF dK) Cx(Bb Bn bQ bV Cq) Ji(Il Ml Ms Ne Nm) Ba(Aj aL bO cX) Dc(aV bO dE dK) nU(kl mU mZ oQ) mF(mP nN nR oQ) Mp(Nf Ng Nu) Ok(Ne Oz Pf) aL(bE dE dN) dF(cX DE) dK(Al dM fR) Nt(Ml Oe) Mw(Pd Wm) Jg(Og Pz) Oz(Hx Pe) bO(bQ Cw) fR(cB cX) ApdD CpdE NnPc NqPd LwHw MlQa NjIm bQdB nRmW Unconstrained panels with 2 analytes, where 1.0E-3 >= 'AUC p-value' > 1.0E-4. Contains 1,958 panels of 16,069 total panels evaluated. : Is(aA Et Fp FR Hq Hr Hu Hv Hw Hx Ih Ii Ij Ik Il Im In Io Ip Iq Ir Iv Jg Jh Ji Jk Jl Jm Jn Jq Jr Js Jt Lh Li Lj Lu Lw Lx Ly Lz Ma Mb Mc Md Me Mf Mg Mh Mi Mj Mk Mm Mn Mp Mq Mr Ms Mt Mu Mv Mw Mx My Na Nb Nc Nd Ne Nf Ng Nh Ni Nk Nn No Nq Nr Ns Nt Nu Nv Nw Nx Ny Oh Oi Ok Om On Oy Pa Pb Pc Pd Pe Pg Po Qa Qb Qc Qd Qe) Nv(Fp Hq Hr Hu Hw Hx Ih Ij Ik Il Im In Io Ip Iq Ir It Iu Iv Jg Jh Jk Jl Jm Jn Jo Jq Jr Js Jt Lh Li Lj Lu Lw Lx Ly Lz Ma Mb Mc Md Me Mf Mg Mh Mj Mk Mn Mp Mq Mr Mt Mu Mv Mw Mx My Na Nb Nc Nd Ne Nf Ng Nh Ni Nl Nn No Nq Nr Ns Nt Nw Nx Ny Of Oh Oi Ok Om Oy Oz Pa Pb Pc Pd Pe Pf Pg Po Pz Qa Qb Qc Qd Qe) Qd(aA Et Fp FR Hq Hu Hw Hx Ih Ii Ij Im In Io Ip Iq Ir Jh Ji Jk Jl Jm Jn Jq Jr Js Jt Lh Li Lj Lu Lx Lz Ma Mb Mc Md Mf Mg Mh Mi Mj Mk Mn Mp Mq Mr Ms Mt Mu Mv Mw Mx My Na Nb Nc Ne Nf Ng Nh Ni Nk Nl No Nq Nr Ns Nt Nx Ny Oe Of Oh Oi Ok Oy Pa Pb Pe Pg Po Qa Qc Qe) Nw(aA Et Fp Fr Hq Hr Hu Hw Ih Ii Ik Im In Io Ip Iq Ir It Iu Iv Jg Jh Ji Jm Jn Jo Jq Js Jt Lh Li Lj Lu Lw Lx Ly Lz Mb Mc Md Me Mf Mg Mh Mi Mj Mk Mm Mn Mp Mq Mr Ms Mt Mu Mv Mw Mx My Nb Nd Nf Ng Ni Nn No Nr Ns Nt Nx Ny Of Oh Oi Ok Om Oy Pa Pb Pc Pd Pe Qa Qb Qc Qe) Fr(Ad aE aF aJ aK Al aN AO aQ Ar aU aV AX aY Ba Bb bC bF Bg bL bM BN bP bQ bR bU bV bW bX cA cC cE cF cG CH cI cK cL cM cN Co CP cR Cs Ct Cv CW cY dA Db Dc Dd dE dF dG dH Dk dL fR Hv Hx Ij Jj Jr Mi Ml Mz Ni Nj Nk Nu Oe Og Oi Oy Pf Pg) aA(aC aD aE AF aJ aK Al aN aO Ap aQ aR aV aW aY BA bE BG bH bL bM BN bP bR cA cC cD cE cF CH cK cL cM Co CP Cq Cu CW cY dC dF dH dI dL Jg Jl kP Lw Lx Mf Mg Mm mP Mu Mv Mw Mz nC Nj nK Oe Om Oz Pg Po) cG(AD aE aH aK Al AN Ap aQ AR aS aV aW aY aZ Ba BB BC Bg bH bJ bN bP bQ bR

Figure 29 Continued bU bW bZ cA cC cD CH cI cJ cM cN CO CP CQ cR CS Ct cV CW cY cZ dA Db DC De dF dG dI dK DL dM dN fR) Lx(Fp fR Hr Hu Hx Ij Im
Ip Iq Jg Jh Ji JI Jn Jq Lh Li Lu Ly Ma Mb Me Mf Mh Mj Mk Mn Mq Mr Mt Mu Mv Mx My Nb Ne Nf Ng Ni Nk NI Nm Nn No Nq Nr Ns Nt
Ny Og Oh Oi Ok Om Oy Oz Pa Pb Pe Pf Pg Po Pz Qa Qe) Om(Hq Hr Hu Hx Ik Il Im Ip Iq Ir Iu Iv Jh Jk Jl Jq Jr Js Lh Li Lu Lw Ly Me Mi Mj
Mk Mn Mp Mr Ms Mw Mx Nb Nd Nf Nh Ni Nk Nn No Nq Nr Ns Nu Nx Oe Of Oh Oi Oy Oz Pa Pb Pd Pe Pf Pg Po Pz Qa Qb Qe) Mz(Fp Hq
Hu Hw Ih Ii Ij Ik Il In Io Ip Iq Ir Jh Jm Jn Jq Js Jt Lh Lj Lu Lz Mc Md Me Mh Mj Mk Mq Mr Mt Mx My Na Nb Nc Nd Ne Ng Nh Ni Nl No Nr
Ns Oh Oi Ok Oz Pa Pd Pe Pz Qa Qb Qc Qe Wm) Aw(AD aG aH Aj AN aO Ap aS Ba BB BC bF Bg bJ bL bM bN Bo bP bQ bR bS bU bW cA
cC cD cE cF CH cK cM cN cO cP Cq Cs cT CV CW cZ dB dC DD dE dG dH dI DL fR) Po(Et Fp Hq Hr Hu Hv Hx Ii Ik In Ip It Jg Ji Jl Jm Jo
Jq Jr Lw Ly Lz Ma Mc Md Mj Mm Mn Mp Mw Mx Nd Nf Ng Ni Nl Nm Nn Nq Ns Nt Nu Nx Ny Oi Ok Oy Pb Pd Pf Pg Pz Qb) aP(aC aD aF
aJ aK Al AN aQ aR As aW Ax Ba Bb bC bE bH bl bM Bn Bo bQ bS bV bW bX cA cC cE cK cL CO Cp CQ cV CW Db Dc dI dJ Dk dM dN
fR) bA(aC aE AF aH aJ aL aM aO aV aW aY aZ Ba bE BG bH bI bL bM BN Bo bQ bR cC cD cF CH cJ cM Co Cp Cu cW cY dB DC dD dF
Dg dH Dk dN fR) Jl(Et Fp Hq Hu Hv Hx Ii Ip It Iv Jg Jm Jq Jr Jt Li Lj Ly Ma Mb Mg Mh Mp Ms Nc Nd Nf Ng Nm Nn No Nq Ns Nt Nu Of Oi
Ok Oy Pd Pe Pf Pg Pz) Di(aH aM aN aO Ap As aV aY BB Bc bL Bn bO bQ bZ cO Cp Cq cR cT Cv CW cX cY dC DD DE dF dI DK dM dN
fR) Mi(Hr Hv Hx Ik Im Ip It Jj Jk Lh Lw Mb Me Mf Ml Mn Mp Mr Mu Mv Mw Na Nb Ne Nf Ng Ni Nj Nm Nq Nr Nt Nu Nx Oe Oi Pb Wm)
Jr(fR Hr Ii Ik In Ip Iu Jg Jh Jj Jk Lh Lj Mc Mf Mg Ml Mm Mq Mt Mu Mv My Nb Nj Nr Nt Ny Of Pa Pc Pd Pf Pg Pz Qa) bQ(aD aE Af aG al aJ
aL As aV aX aY Bb bJ bL bM Bn bU bV cA cB cC cD cE cJ cM cR cW cX DC dD dE dH dK fR) aJ(aE aH aM aO aS aU aV aZ Ba bB bC bF
BG bJ bL bN bP bR bZ cD cH cM cR Cu dA dB dC DE dF dG dH) Ny(Hq Hr Ik Im In Io Jg Jk Jm Lj Ma Mb Mc Md Mf Mk Ml Mq Mt Mu Mv
My Ne Nm Nq Ns Oe Of Pd Pf Qa) aZ(aG Al aM Ao Ap aX Ba Bb bC Bg bH bJ bL bV bW cC CO Cp Cq cR Cv CX DC dD dE Dg dN fR)
Ji(Hr Hx Ir It Iv Jj Jk Jo Ly Mb Mk Mn Na Nd Nf Ng Nh Nj Nk Ns Nu Oe Og Oi On Pa Pb Pf Pz Wm) cS(AD aK Ao aQ Ar aU aW bB bE Bg
bP bS cB cC cJ Co cR Cw cY DB dC DE dJ dK Dl) Nu(Et Hx Ij Im Ip Iq Jg Jh Jj Jk Jn Jq Lh Lw Mj Mn Mt Mw Nb Nn Nq Nr Oe Ok Pe Pg Qa)
aX(Ad aH aM Ao Ap Ar Ba Bb Bc bL Bn cB cH Co cR Cs CT Cv Cw cZ DB dC De Dl dM) dF(Af aG al aM Ap As aU bB bC bJ bL Bn bO bR
bW bZ cB cC cD cE cJ cO Cp cR dB dC dH) Dc(aG al aK An aO Ap aU bB bC bJ Bn Bo bW bZ cD cL cO cR cX cY dB dC dD De dN fR)
Cx(Af aG al AL aO Ap aU aV bB BC bL bO bW bZ Cp cT cW cY Dd DE dl dK) Jg(Hv Hw Hx Ij Il Ip Jj Jo Jq Ml Ms Nd Ne Ng Nh Nj Nm Oe
Oi Pe Pf Pg Qa Wm) Pg(Et Hv Ii Im Ip Iv Jq Jt Ly Ma Ml Mm Mp Nd Nf Ng Nm Nt Oe Of Og Oi Pz) al(aC Al aR Ax Bb Bc bJ bL bO bS bV
bW bZ cO Cp cR CW cX dC dI dK dM) Jj(Hv Hw Hx Ik dM) Jj(Hv Hw Hx Ih Ii Ip Iq Ir Iv Jm Jn Ma Mj Mk Mv Mw My No Nq Nx Qc) cJ(Af aG Ap Ar As BG bL
Bn BO Ch Cq Cs Cw cX Db Dd DE fR) Nt(Hv Hx Ik Ip Jo Lw Ly Nd Ne Ng Nj Nk Nm Og Oi Ok Oz Pf Pz Qa) bZ(aG aL AS Ax bL bM bO
Cp Cq cT cX dB dC DD dE dK dM fR) Mp(Hu Hx Ik Im Jh Jq Lu Mb Mh Mj Ml Mv Nr Nx Og Ok Pd Pe) fR(aG aL aM aU bC bG bJ bO bR
cC cD cM dC dD De Mw Nb On) Nn(Hx Im Jn Jq Lw Ly Lz Mc Mj Mu Ng Ns Oe Oh Oi Pd Pe) Ok(Hu Hx Im Ip Jk Ml Nd Nh Nj Nk Nm Oe
Og Pa Pe Pz) Jp(Aa Hq It Jm Jo Js Mb Mc Md Me Mn Mr Nl Oy Qc) Jq(Hv Hx Ij Jk Li Lw Ma Mk Ml Mm Ms Nf Nj Nq Og) aG(aL aO Ba Bb
bL bO bV cO Cp cR cW cX dE dK dM) Lw(Hv Hx Ij Im Mj Mw My Nb Nr Pe Qa Qe) aL(aC Al Bb bJ bL bS CO Cp Cq cR dl) Ba(Af As aV
bG Bn Bo cD dB dE Dg Dl) Mw(Hu Ik Im Jn Mc Nj Ns Oe Og Oy Pf) Hx(Hr Ma Ml Mm Nj Nm Nq Oe Og Pb) Qa(Hv Ip It Iv Nf Nj Nm Oe
Oz Pb) Et(Hv Il Ml Nj Nk Nm Oe Oi Pz) Ij(Jo Ly Ma Ml Mm Nd Nj Nm Og) bO(aM bL bV cO Cp Cq DE dK) Al(aU aV bB Bo Cu cY dB)
Cw(Aj aV Bg Bn Ch cX Dl) Pe(Ma Ml Mm Nj Oe Pb Pf) bV(BB cB Cp cR De dK) Im(Lh Ml Nb Ni Nk Nl) nU(kG mH nC nR oO oP) Cu(aD
bF cH dG dL) Nq(Ml Ms Nf Ng Ni) Mm(Hv Il Mj Nj Nk) Oe(Ir Jn Jt Nb Nr) aO(Ap bC cX dE dK) dD(Bb bW DE dK) Cp(aV Bc cO cW) Lv(Io
Jo Mg Pf) Oz(Il Ir Iv Jt) cX(bL cW dE dK) mF(ml mT nM oP) kG(mW nC nH nK) bC(Bb bG bM) Ax(aU De) Nm(Hq Hv) Ma(Ni Nk) Mv(Ng
Pd) Jt(Ms Og) On(Md Nf) bG(aU bW) cB(bS dM) cO(aS dB) dK(Bc bL) nR(nK oQ) mZ(mP oQ) DecT DkdE Mtlk NbPb NjHw Irlu bBdM Unconstrained panels with 2 analytes, where 1.0E-2 >= 'AUC p-value' > 1.0E-3. Contains 3,934 panels of 16,069 total panels evaluated. : Fr(aC
aM An Ap aR aW Bc bE bG bH bI bJ bS bZ cO cQ cV cZ De dI dJ Dl dM dN Et Fp Hq Hr Hu Hw Ih Ii Ik Il Im In Io Ip Iq Ir It Iu Iv Jg Jh Ji Jk
Jl Jm Jn Jo Jq Js Jt Lh Li Lu Lw Lx Ly Lz Ma Mb Mc Md Me Mh Mj Mk Mn Mp Mq Mr Mt Mu Mv Mw My Na Nb Nc Nd Ne Nf Nh Nl Nm
Nn No Nq Nr Ns Nt Nv Nx Ny Of Oh Ok Om Oz Pa Pb Pc Pd Pe Po Pz Qa Qb Qe Wm) fR(aC AD aE AF aH AJ aK Al AN AO Ap aQ AR AS
aV aW Ax aY Ba BB bE bF Bg bH bI bL bM BN Bo bP bS bU bV bW bX cA cB cE cF CH cI cK cL cN CO CP CQ cR Cs cT cV CW cY cZ dA
DB Dd dE dF DG dH dI dJ Dk DL dM dN Iv Ji Lv Mi Mr Nr Nt Nw Om Pf Pg Qa) Et(aA Fp Hq Hr Hu Hw Hx Ih Ii Ij Ik Im In Ip Iq Ir It Iu Iv
Jg Ji Jk Jn Jo Jq Jr Js Jt Lh Li Lu Lw Lx Ly Ma Mb Mc Md Me Mf Mg Mh Mi Mj Mk Mm Mn Mp Mr Ms Mt Mu Mv Mw Mx My Nb Nc Nd
Ne Nf Ng Nh Ni Nl Nn No Nq Nr Ns Nt Nv Nx Ny Of Og Oh Ok Om Oy Oz Pa Pb Pc Pd Pe Pf Qa Qb Qe Wm) Ba(aC AD aE aF aH aK Al aM
AN AO Ap aQ AR aS aU aW Ax aY BB BC bE bF Bg bH bI bJ bL bM bN bP bQ bR bS bU bV bW bX bZ cA cB cC cE cF CH cI cK cL cM
cN CO CP CQ cR Cs CT CV CW cY cZ dA Db DC DD De dF dG dH dI dJ DK dL dM dN) Qa(aA Fp Hq Hr Hu Hw Hx Ih Ii Ij Ik Il Im In Io Iq
Ir Iu Jh Ji Jk Jl Jm Jn Jo Jq Js Jt Lh Li Lj Lu Ly Lz Ma Mb Mc Me Mf Mg Mh Mi Mj Mk Mm Mn Mp Mq Mr Ms Mt Mu Mv Mw Mx My Na Nb
Nc Ne Ng Nh Ni Nk Nl Nn No Nq Nr Ns Nt Nx Ny Of Og Oh Oi Oy Pa Pc Pd Pe Pf Pg Po Pz Qb Qc Qe Wm) aA(Aa Aj An Ao Ar AS Ax Bb bI
Bo bS bU bV bX cI cN cQ Cs CT CV cZ dA Db Dc Dd DG dJ Dk Dl dM dN Hr Hu Hv Hx Ij Il Im Ip Iu Ji Jj Jk Jq Jr Jt kN Lh Li lW IX Mb mE
mH Ml Mj Mk Ml Mn mT My nD nF nH nI nJ Nk nL Nm nN NT Nu Nv Nx Ny Og Ok oO Pc Qe) Pe(Fp Hq Hr Hu Hv Hw Hx Ih Ii Ij Ik Il Im
In Io Ip Iq Ir It Iu Iv Jh Ji Jk Jm Jo Jq Jr Js Jt Lh Li Lj Lu Ly Lz Mb Mc Md Mf Mh Mi Mj Mk Mn Mq Mr Mt Mu Mv Mw Mx My Nb Nc Nd Nf
Ng Ni Nk Nl Nm No Nq Nr Ns Nt Nx Ny Of Og Oh Oi Oy Pa Pc Pd Pg Po Pz Qc Qe) Cw(Ad aE AF aG aH aJ aK AL aM AN AO aQ AR AS
aU aW Ax aY aZ bA BB Bc bF bG bI bJ bL bM bN Bo bP bQ bR bS cC cD cE cF cH cI cK cM cN cO cP CQ cR Cs CT cV cW cY
dA DB DC dD dE dF dG dH dJ DK dL dM dN) Nt(Fp Hq Hr Hu Hw Ih Ii Ij Il Im In Io Iq Ir It Iu Iv Jg Jh Ji Jk Jm Jn Jq Js Jt Lh Li Lj Lu Lz Ma
Mb Mc Md Me Mf Mg Mh Mj Mk Mm Mn Mp Mq Mr Ms Mt Mu Mv Mw Mx My Na Nb Nc Nf Nh Ni Nl Nn No Nq Nr Ns Nu Nx Ny Of Oh
Om Oy Pa Pb Pc Pd Qb Qc Qe) Jq(Fp Hq Hr Hu Hw Ih Ii Ik Il Im In Io Ip Iq Ir It Iu Iv Jh Ji Jm Jn Jo Jr Js Lh Lj Lu Ly Lz Mb Mc Md Me Mf
Mg Mh Mj Mn Mq Mr Mt Mu Mv Mw Mx My Na Nb Nc Nd Ne Ng Nh Ni Nk Nm No Nr Ns Nx Ny Oe Of Oh Oi Ok Oy Oz Pa Pb Pc Pd Pf Pz
Qb Qc Qe) Ij(Fp Hq Hr Hu Hv Hw Hx Ii Ik Im In Io Ip Iq Ir It Iu Iv Jh Ji Jk Jl Jm Jn Jr Js Lh Li Lj Lu Mb Mc Md Me Mf Mg Mk Mn Mp Mq
Mr Ms Mt Mu Mv Mw Mx Nb Ne Nf Ng Nh Nn No Nq Nr Ns Nx Ny Oe Of Oh Om Oy Oz Pa Pb Pc Pd Pf Pg Po Pz Qb Qc Qe) dF(aC AD aE
aF aH Aj aK AL AN AO aQ AR aS aV aW Ax aY Bb Bc bE bF BG bH bI bM bN Bo bP bQ bS bU bV bX cA cF CH cI cK cL cM cN Co cP
CQ Cs CT cV cW cY cZ dA Db Dc DD DG dI dJ Dk DL dM dN) Dc(aC AD aE AF aH AJ AL aM aN Ao aQ AR AS aW Ax aY Bb Bc bE bF
BG bH bI bL bN bP bR bS bU bV bX cA cB cC cE cF Ch cI cK cM cN Co CP CQ Cs CT CV cW cZ dA Db Dd DG dH dI dJ Dk DL dM)
Im(Hq Hr Hu Hv Hx Ih Ii Ik Il In Io Ip Iq Ir It Iu Jg Jh Ji Jk Jm Jn Jo Js Jt Lj Lu Lv Lz Ma Mb Mc Md Mf Mh Mj Mk Mn Mq Mr Mt Mu Mv
Mx My Nc Nd Ne Nf Ng Nh Nm No Nr Ns Nx Oe Of Og Oh Oi Oy Oz Pa Pb Pc Pd Pf Po Pz Qe) aG(aC aD aE Af aH aI Al aM AN Ap aQ
aR AS aU aV aW Ax aY bB BC bE bF bG bH bI bJ bM BN Bo bP bR bS bU bW bX cA cB cC cD cE cF cH cI cK cL cM cN cP Cq Cs cT cY
cZ dA dB dC DD De dG dI dJ Dk dL dN) Ok(Fp Hq Hr Hv Hw Ih Ii Ik Il Io Iq Ir Iu Iv Jg Jh Ji Jm Js Jt Lh Li Lj Lu Lw Ly Lz Ma Mb Mc Md

Constrained panels with 3 analytes, where 1.0E-8 >= 'AUC p-value' > 0. Contains 1,733 panels of 625,624 total panels evaluated. : cU{Cx(aA aG aJ Al AP As aU aV aX aZ BA Bb bJ bO bQ bR bU cA cB cC cD cE cF cJ cK cL cN cO cS Cw dA Dc Dd DE dH DI dJ dK Fr) cX(aA aC aG aJ aM AP aV aX aZ bA Bb bJ bM bO bP bQ bR bU cA cC cD cE cF cG cJ cL cN cO cR cS dA dE dH DI) dK(aA aG al aJ Al As aV aX aY aZ Bb bJ bM Bn bP bQ bR bU cA cB cC cD cE cF cG cL cN cO Cu dB dE dH DI Dk Fr) As(aG al aK aL aQ aU aV Aw BA bC Bg bO bW cB cJ cM Cp Cq cS Cu Cw cY Dc Dd DE dH Di Dk Fr) bQ(aA aC aE aG al aJ aL AP Aw aX BA Bb Bg bL bM bW cJ cM Cp cS cW Dc De dH Di FR) cN(aA aC aE aG al aJ aL AP Aw aZ BA Bb bC bL bM bW cB cJ cM Cp Cu cW Dc De Di FR) cE(aC aG al aJ aL aO AP Aw BA Bb BG bL bM bO bW cB cG cJ Cp cS De Di FR) dH(aA aC aG al aJ aL AP Aw aX BA Bb bG bL bM bS bW cG cJ cM cS cW dE Di FR) aL(aC aJ Al aV aX aY bE bJ Bn bR bU cA cC cD cF cG cK cL cO cS dA dB dE dI) Fr(aG aV aZ bF bJ Bn bR bU cA cC cD cF cG cJ cK cL CO dA dB dE dG dI) Aw(Al aV aY bF bJ Bn bR bU cA cC cD cF cG cK cL CO dA dB dE dI) al(aC aX aY bJ Bn bP bR bU cA cC cD cF cG cK cL CO dA dE dG dI) cM(aV aY bJ Bn bP bR bS bU cA cC cD cF cG cK cL CO dA dB dI) bW(aV aY Bn bP bR bS bU cA cC cD cF cG cK cL CO dA dG dI) Ba(aG aV aZ bJ bM Bn bR bU cB cC cD cF cG cK cL dA dG dI) Di(aG Al aZ bJ bM Bn bR bU cA cB cC cD cJ cK cO dA dI) aA(aG Al aX Bg bJ bR bV cB cJ cK cQ cS dA dE dG dI dL) Cp(aX aY bJ Bn bU cA cF cG cK cL CO Cq dA dE dI) bA(aC aG aZ bJ bM Bn bR bU cB cC cD cF dA dG dI) Bn(aK aU aZ Bb Bg cJ Cq Cu Cw cY Dc Dd De) bR(aC aG aJ AP aX Bb bL bM bS cS dE fR) cL(aC aG aJ aU aZ Bb bL bM cG cJ cS dC De) Al(aG aU aV aZ Bb bM bO bU cB cY De dJ) aE(aV bU cA cD cF cG cK cO dA dE dI) cC(aG aJ aP aZ Bb bH bL bM cW Dc dE) Dd(Ad aG An bJ Bo Cq Cw dB Dc dE) aJ(aV aZ Bg bM cB dA De dG dL) De(bM bU cA cD cK CO) aP(Bg cB cJ dA dG dI dL) bJ(aM aZ Bb bM cJ cY Dc) cS(aG aZ bM cB dG dI dL) bL(bU cD cK cO dG dI) Bb(aG cD cK dA dB) Dc(aG aU bU cK dA) aX(aG aY bV cB dI) Ap(cJ cK dA dI) bC(cA Co dA dI) bM(aG aV bO cJ) dE(aG Bg cB dC) aC(aV aY cB) aZ(bO cD cJ) bH(bU cA cD) Bg(bF bZ) Co(aU cY) Cu(An Cq) aY(aM cW) fR(dF dL) AxCs BcdA bGbZ cWdG dBdC} Cx{cJ(aA aJ AI aP Aw aX aZ BA Bb Bc Bn bO bV bZ cG Cp Cq cS Cu Cw Dc Dd DE dF Di dK FR) aA(Af aI aK aM aU aV Aw aX aZ bB bC Bg Bn bO bZ cB cG Cp Cq cS Cw Dc Dd DE Di Fr) cG(aJ As aV bO bQ bR bU cA cC cD cE cF cK cL cN CO dB Dc dH DI dK) bA(aG aI Ap aU aV Aw aX aZ bC bO bW bZ cB cS Cw De Di dK) Cu(aG aJ aU aV aX Ba bO cK cS Cw dC DE dK FR) aZ(Af aI aO aP Aw aX bC Bn bW Cq cS De dF Di dK Fr) Di(aG aI aJ AL aP aX bC bO cS Dc Dd dF fR) aX(aI aL Bg Bn bO cK Cp Cq cS Dc Dd dF dH) cS(aL Ax Bb bM bO cB Cp Dc Dd De Dk) aP(aU aV Aw Bg bO cB De dG dH dL) Aw(aJ aV Ax bO Dd fR) dK(aI aL Ax Bc dF Dk) De(aJ aL Ax bV dF) bO(Ba Cw Dc dF fR) aV(AI Ba Cw Dc) Fr(dC Dd) aL(bE bW) dF(aU cE) aIdE aJcB cDfR} Lv{MI(aA Hv Hw Hx Ii Ir Is Iv Jg Ji Jj JI Jp Jq Jr Jt Lx Ly Mi Mj Mp Mr Mz Na Nb No Nq Nr Nv Nw Ny Ok Om On Pe Po Qa Qd) Jj(Hv Hw Hx Ih Ii Ij Il Im Iq Ir Is Jk Jl Jp Jq Ma Mi Mn Mv Mz Nd Nq Nv Nw Ny Om On Pg Po Qd) On(Hu Iu Jo Mm My Nf Ng Nj Nm Nn Oe Of Og Oi Oy Oz Pb Pf) Jp(aA Im Is Iu Jl Lw Ma Mi Mm Mp Nm Nn Oh Ok Oz Pc) Nm(Im Is Jg Ji Jl Mm Mz Nv Nw Ok Qd) Oz(aA Hv Il Ir Is Jl Pg Qd) Mz(Lw Ly Ma Mm Mp Nn Pc) Ly(Hv Hx Mi Nw Om) Nn(aA Mi Oi Pc) Iu(Iq Ir Is Jl) Jo(Jl Mi Nv Om) Pd(Jl Pe Pg) Pf(Pe Pg Qd) Lw(Hv Hx) Ng(Mm Om) Pb(Ny Pe) MdMp MhIs MiNf MwOy NdNj OgOm} aX{cX(aA aI aL aO bA BG bL bO Cq Cu Di Dk) dH(aA aJ aL aO aP Ax bA bG bQ cZ Di Dk) Cu(aC Ad An As Bn Bo cJ Cq Cw Dc Dg) Ax(As Aw bB bV cB cH cJ cK dA dI) Cq(aC aI aL As aV bM bO cB cZ) Cp(aC aL As Bn bO cH Cw cZ) aA(aI aL bB bG bO cB cJ dI) AI(aC aL bO cJ dD) Dd(aC aI aL bF Bo) Aw(aC bO cH cZ) bA(Bg bV cB dI) Dc(aC aL cJ) Dk(cJ cK dK) aL(cM Cv) bG(bO dI) cH(aI aJ) BgcJ} cS{cX(aA aL Ax aZ bA Bb bM bO Cu Dc dD Di Dk) Cu(Ad An As Bn Bo Cp Cq Cw Dc) aA(bG bR bV cB cJ dB dG dH) bM(Ax bG bO bR cB Cq dD dH) As(Ax bN Cp Cq Dd Dk) aZ(Af aI BG dD Dk) dH(aJ aL aP bA Di dM) Ax(aI bR cB Cs) Aj(cB cJ Cp) Bn(aL Aw Cp) Bb(aC dD) aL(bH cM) bA(bR cB) bO(aW bG) AdDc AfAw AIcB DddB DicJ aPdG} cJ{aA(Af aZ bC BG bH bJ Bn bO bZ cX dE Di dL) Cu(Af An As bJ Bn Bo Cq Cw cX dB Dc dE DI) Di(aJ aP As aZ BA bO bZ cX dE) Bn(Aw bA cG dF Fr) aP(Bg cX dG dL) Dc(bO cX dE) Fr(Aj aZ cE) Ax(Aw dK) Ba(Aj cX) Dk(dE dK) aJ(cX dL) AfbA AIbO CpdE} Qd{Jj(Il Jg Jk Jl Lj Lz Ma Ml Mp Nj Nq Oz Wm) Nm(Fr Jg Jp Lw Mm Nw Ok Om On Oz Pc) Iu(Jk Jl Lw Ma Mp Nn Nq On Oz Pg) Pz(Fr Jg Jk Jp Ml Mm Nn Nq On Pc) Wm(Ii Ik Jo) Ml(Jp Nj Oz) Pf(Pe Pg) IifR} aP{dG(aG aI aL Aw bB BG bO cB cX dA De dF dH Di dK Fr) dH(aI aL bF BG bO bQ bZ cB cG cO cX dA De Di Fr) dL(aI aL bB bO cB cX dA dK) cX(aZ bR cB dC) bG(bR cB dK) Aw(Af Bn) aLbE bHcB bZcE} aA{cX(aU aZ bC bO bZ cB cG dC DE) bC(bB Bg bO cB dA dB) bZ(aZ cE dH dK) dE(aG aI aL cB) De(Af Bn bO) bJ(aI aL cG) nU(mM mU nB) Aw(Af Bn) dH(bQ cG) dK(BG) nR(mF nK) mP(mF nB) kG(nI nK) aIaZ aLbE nTnB} On{Nm(Hr Jj Ma Mi Ml Nj Oe Of Og Pb) Ml(Jj Jp Mb Mm Nj Of Og Pb Pz) Mm(Hr Jj Ma Ng Nj Of Og) Nj(My Of Oy Pb Pz) Mh(Jj Of Pb) Lz(Of Pb) Mi(Jo No) Ng(Ma Mg) Pf(Pe Pg) IlJj JpOe OfPc OiPb} Jp{Nm(Ij Jk Lw Ma Mi Mm Mp Nn Nt Nw Om Pe Pg Po Qa) Mi(fR Ml Nf Nn Pc Pd) Jj(Hw Ij Il Mp Po) Ml(Is Ji Nn Qa) Nn(Oi Pc) Ng(Mg Nq) Pf(Pe Pg) LwIl JkOf OefR OzPg} dK{Ax(aI aL Aw aY bB BG bO cB cG Cs De Di Dk Fr) Dk(Af Aj As aZ bM Bn cX dB dE) aL(Ap bG bH bJ cX Di) bG(aJ aZ bA bM bO) AI(bO Di) aI(aZ dM) BndF} aL{bE(aJ AI Ax bG bH Dd Di Fr) bW(AI As Ax Bn Co Di) bJ(Aw Ba cG Di) Bn(Aw bC De) De(aJ AI) Di(Ap dE) bC(aJ As) AwdE FrcE aQaU} bA{De(Af As aZ bJ Bn CT cX) cX(aG aZ bC cB Di) Bg(aU bC bW) Bn(Aw Di Fr) bJ(aI cG Di) aG(cT Di) dH(bW cG) AfAw AsFr aIdE cBcT} Aw{Ax(Af As aV aZ Bn bO Cs) bO(AI As aZ Bn cX) Bn(aZ Bc dF) As(Ar Bc) Cu(Cp Cq)} Jj{Ml(Ij Jl Mz Pg Po Qa) Il(Mi Nv Nw Om Po) Ma(Ij Pg) Oz(Jl Pg) NqIj} Pf{Pg(Fr Im Ji Lw Ma Mi Mm Ok) Pe(Fr Jg Lw Ma Mm Nw Ok)} cX{cG(bO cC cE cF dH Di) aZ(aJ aO bQ dF fR) Cu(bO dE) FrdC aIdE} Nm{Nw(Im Jk Jl Ma Ml Mp Mz Nt Nu) LwJl MmPg} As{Cu(bV bZ cK dH Fr) Fr(Ax Cq Di) aIbC} aJ{aI(aZ dG dL) cG(dG dH) bZdG} Mi{Pd(Jk Lw Nn) LufR JlJo} nU{mU(mF mW oQ) mFkI mWnB} fR{Qa(Ii Oe) MkOi OePa} Cu{BndF DlcK bOdB} Di{AIbO BncG aIaZ} Ad{Dc(De Fr)} nR{mW(mF oP)} AjFrdC NnMzOi MaMwNg IsIuOe bGcEcG mFmHmP nDkCkG Constrained panels with 3 analytes, where 1.0E-7 >= 'AUC p-value' > 1.0E-8. Contains 796 panels of 625,624 total panels evaluated. : Lv{Ml(Et Fr Ij Il Im Iq Iu Jn Js Lw Mv Nd Nn Nt Pa Pg) Jj(Fr Iu Jg Ji Jm Jt Mg Mm Mp Nn Nr Nt) Ly(aA Jl Mp Mr Nd Nt Nu Nv On Oz Pg) Oz(Iq Iu Jk Mr Nb No Nr Pa Pe Po) Oe(fR Iu Jl Nb Nr Nw Om Pa Pe) Im(Hv Hx Jl Mp Nj Nk On) Ji(Il Jq Md Nf Nk Om Pb) On(Hr Lw Ma Md Pc Qd) Hx(Ma Mp Nf Nn Pc) Is(Iv Jr Lw Nn Pc) Om(Nf Nj Nk Of Pb) Ng(Fr Jg Mw Nq) Ma(aA Hv Nw) Nj(aA Jq Mi) Qd(Lw Nn Pc) Jo(Hw Jk Pg) Pb(Mw Nb Nr) Nm(Et Jt) Mp(Hq Nw) Jg(Og Oi) Pc(aA Mi) PoPf FrMz NqNf LwJl MmIl MwOg NdJt NkNw} Cx{Di(aV Ba Bb Bc bZ Cp Cq Cw dC De dK) fR(aU aV aX aZ bC Bn cB Cp Cq Dc) Dd(aI aP aV bO bZ cG De dF dK) bO(AI Bb Cp Cq DE dK) Dc(aG aU Aw bC De dK) cG(AI bJ dA dE dG) aJ(Af aL aZ dL) aV(Bn bQ dF Fr) dE(aL bA Cp dF) aZ(bH bL bZ) bC(Bb cB cJ) AI(bB dB) Fr(aX cS) bV(cB Cp) ApcJ AsAw AxaU CqcR CudH aMdF bAcT bNcS} cX{cG(aJ As aZ bQ bR bU cA cD cL cN cO Dc dE dI dK) bA(aI aU bL bO bW cR cT dC dE dK) aX(aJ aP Ax Dc dF fR) aL(bC bE bW DE) aZ(aG Cq De Di dK) Cu(aG bE dB dK) bO(aP Ba Dc fR) cB(aJ cS cU) Aw(aA Ax) dF(bC dK) BbcJ DiaG FraA aJdC cRcS dDdE dKdM} Jj{Il(Et Im Jg Ji Lh Lw Lx Ma Mg Mm Mp Mz Nn Nq Nt Nx Ny Oz) Ma(Hv Hx Jl Jp Mz Nv Pe Po) Jp(Is Jk Mg Nq Om Pe) On(Md Nf Nj Nw Oe) Nn(Ij Jl Mz Pg) Ml(Is Nv Nw Om) Mg(Jl Pg Qd) Ij(Jg Mp Nf) Qa(Nf Pb) NqMz LwJl MmPg NjNv IuQd} On{Pb(Iq Lw Ma Mg Mt Mw Mz Nf No Oe Pf) Ml(Hv Mi My Mz Ng Ns Oe Oy Pc Qd) Of(Iq Ma Mt Mz Nf No Oi Pf) Mm(Lw Nm Oe Oy Pc Pz Qd) Nm(Lw Nf Ng Oy Pc) Nn(Ng Oi Pc) Mi(Nf Ng) Nj(Im Og) Jo(Jt Mg) NqNg MyOi ImJp} Jp{Nm(Fr Im Is Ji Jq Mg Mz Nv Ok Pc) Ml(Hx Jr Mj Mz Pg Po) Im(Lw Mp Nn Pc Pg Qd) Mw(My Ng Of Og) Oe(Hx Mz Pg Po) Lw(Mi Nn Pa) Nf(Ji Nn Qa) Pb(Nb Pe Qa) Hq(Mi

Figure 29 Continued

Mp) Qd(Lz Oz) Jk(Ng Og) NqOf MmIl JlOz OiPc} bA{bW(bP cB cF dE dG Di) cB(bC bJ bS bZ dE) Di(aU aZ bO dK) dE(aG Aw cC De)
Ap(Bg cJ) Aw(bJ Ct) Dc(aG aX) al(bE dK) aU(Af Bn) bZ(cC dH) BgcJ aLbJ aPdG cOdH cTdK} aL{dE(aP cC Cp De dK) aJ(bJ dG Di dL)
bE(Bg Cs Cu) bJ(bQ bW De) dK(Al Bg bZ) Ap(Ax De) As(Aw bZ) Di(Ba Bn) aX(bV cH) bW(cF cR) cS(aZ dG) AlbC CocU aAdB aPbV}
aX{Dd(Bg bO cB dD) dH(al dD dF dM) Ax(aU Cp dK) cB(Al Cu Dc) Di(Al cK) bG(aJ bV) bO(aO Bg) cJ(cU Fr) AdCp AfBn CqbB DccK DeaC DkdI aAbV cHcZ} cS{Dd(bM Bn Bo cH) dH(Bc dF FR) Cp(Ad Af Cw) cB(Ar bG dM) cJ(Cu Dk Fr) As(Aw Dc) aJ(dG dL) bM(Al Dk) cK(Bb Bc) AfCq AxBg bGcE bRdM} cJ{Dc(Ad Af bJ Bn Bo dB) Aw(Af As dB dE) Cu(Ad Cp dL) aP(bG bM bO) Di(Bb bC) AfdF ApaA AxDe BabO BgaZ FrbC} cU{Cu(bR cC cD cE cL dB dH) Dc(bJ cG dA dI) dG(Aw cM Dc) Bg(aY cC) AlaK AnCw ApcQ AwbI BbbU CpDd aUbP bCcK} aA{cB(bG bH bJ bO bS bZ) dE(Aw bC bO) De(Ax Bg) cG(Af dG) NnOi MaNj MwPb JkOz aGbG bCdH bOdB bZdC nRnI} Nm{Nw(Fr Is Iu Jt Mg Nf Ok) Qd(Et Ji Jl Ma Nt Pg) Mz(Et Mm Po) Jl(Im Mm Ok) NjNv IlJi} aZ{bO(aO bH Di Fr) dK(Ax Bg dF) aI(bJ dE) cN(aP bQ) CvFr DiaG aFaO bGbW} aJ{dL(aU bO bW cB cG) dG(aG dF Fr) cB(bM bO) dH(bB bQ) AfDe aIdE} Qd{Iu(Is Lj Lz Mg Nt) Pz(Im Lz Mg Nt) NuMl NjOz JoJt} As{Fr(bC cB cG Dd) Cu(bW dF) Di(cG Dk) bC(Aw dF) CqbZ} Nn{Mz(Ml Nf Nj) Nf(Jr Mi) Iu(Ir Is) Oi(Jl Nw) PcPe} Pg{Oy(Fr Im Lw Mm) Pf(Is Jt Mz) Oz(Ml Nf) MmJo} Bn{Aw(aI bC cG DD) Fr(Cq dC) DeaI cGdH} aI{dE(Cp Dc Di) Al(Di dK) ArdK aHfR} De{Af(aP cT dF) Cu(Ad Cp) AxCs} Mi{NoJl MaPd MlMz MwOg NgJk IsIu} aP{dG(cG fR) bGdC bMdK bNdH} Ax{Aw(Ap dE) AlCu CsDi} Ma{Nj(Mz Nd) IrIu JlJo} Ml{Is(Nu Oe Oz) MzNj} Di{AlcD DcaG FrdC} Nq{MzNg NfOi PePf} Jl{Oz(Oe Og) JiJo} nU{mU(kG nN) mFkC} Af{AwbO cGdH} Bg{AdCu AjdK} Et{OefR PePf} Ny{Pb(Mp Nu)} mF{mPkI kGoQ} nK{nRmW nBoQ} BbbGdK CuDIdH DcbOdE FrbCdB

Constrained panels with 3 analytes, where 1.0E-6 >= 'AUC p-value' > 1.0E-7. Contains 1,186 panels of 625,624 total panels evaluated. : Jp{Oe(aA Il Ir Is Iu Jg Jk Jq Mm Nb Nq Nr Nt Om Oz Pa) Ml(Fr Hv Ij In Ir Iv Jl Ma Mf Nb Nr Nt Om Pa Pe) Ji(Hr Hw Iu Jq Md Mz Nj Ny Om Pb) Ma(aA Hv Im Lw Mi Nj Nk Nn Pc) Im(Iu Jl Jt Mg Mj Nj Oh) Nm(Ip Ir Iu Jl Jt Mf) Is(Jr Lw Mh Mp Nj Nn) Jj(Ir Iu Jg Jt Nr Nt) Oz(Iu Nr Pa Pb Pe) Pg(Hq Mm Nj Of Oy) Lw(Jl On Pc Qd) Mp(Jl Nj Ok Qd) Og(Hx Il Mg Om) Nn(Jl Nj Ok) Mz(Iu Mg Nj) Nt(Jo Ng) NqNf MiPf MmHv MuHu MwOy NbOf NeNl NgOm HwQa PzJk} Lv{Oe(Et Il Iq Ir Is Jg Jq Lx Nt Nv Ny Pg Qa) Ok(Hr Jo Ma Mm Mp Nf Ni Nk Nn Of Pb Qd) Im(Iu Jt Lw Ly Nb Nn Nr Oh Pc Pg Qd) Ma(Is Ji Jl Jq Ml Nd Nj Nk Qd) Ly(Il Jk Nb Nj Nk Nq Nr Pe) Ml(In Jk Nj Nk Oh Pc) Mg(aA Jl Nd Ng) Nk(Et Jg Jq Oz) Ji(Hw Ij In Pc) Fr(Is Nj Qd) Lw(Il Iu Jj) Mm(Is Jl Qd) Pc(Jj Nd Oi) Nt(Nf Nj) Mw(My Of) Qa(Nf Pb) Jg(Of Oh) Og(Jk Qe) PoOn NnJl MiHq MpNj NIJj QdLj OhOm OzPb} Cx{Dc(aI aJ Ap Ba bB bW bZ cY dC dE dF) aG(aZ Bb Bn bO Cp Cq Cw Dd DE) aJ(aM aU Ba bC Bg bO Cp Cw Dd) aV(Af aO bC bZ Cp Cq DE dK) Al(aI aU bW cR cY De) bO(Af Ap aZ bC bW dC) bV(Af aU aX bB Bn Cw) dE(aO Aw Bn cB Di Dk) Cp(aZ Bc cR dK) De(bC Co dC fR) Cq(bM cD Cv) Dd(aO bB fR) Di(Ap bW Cv) aM(aI bA Fr) bQ(As cC cE) Aw(cE dK) aZ(aU Cw) bC(dB Fr) AfBc AsbZ AxBn BbaI aKfR aLbA bScB bWcT} cX{Di(aA aI aL aP aV Ba bC bO DC dF dK fR) aZ(aI Aw aX Ba bL bO bW bZ cJ cR Cu cV dC) Cu(An As bJ Bn Bo Cq Fr) bO(aG aJ bL cJ dE dK) aV(Al Aw Ba cG Dc) bC(aJ aO Bb Dc fR) dC(bQ bZ cW Dc dF) dE(aG aO aP cB dF) aM(aJ aO bL cJ) cG(aG bJ Co cR) dK(aG aI bL bQ) cB(bV dM fR) cJ(Ax cR De) aJ(aL dL) aX(dM Fr) bA(aC Ap) bQ(cC cE) BgaA DeaP aGcW bPcS cEdF} Jj{Il(Fr Is Iv Jk Jq Jr Jt Mf Ml Mn Mv Nm Nu Ok Pe) Ij(Iu Lw Md Mg Mm Nj Nu Oe Pb Pc) Mz(Fr Iu Jg Mg Mp Mv Nf Nj On) Is(Jk Ma Mg Mp Nj Nn Nq Oe Pc) Ma(Ii Im Ir Jk Nw Ny On) Ml(Im Jk Lh Lx Nt Pe Qe) Po(Jg Lw Mp Nj Nn Nq) Nq(Im Ir Nw Ny) Hv(Im Nw Ny) Jl(Nj Oe Pc) On(Mg Mt Pc) Pg(Nj Nu Pc) Jk(Ji Mi) Nv(Nn Oe) NtQd MjIm HwQa OzPe} Ml{Mz(Fr Hv Is Iv Jg Jk Jl Lw Ma Mf Mg Mm Mp Nq Nt Oe Om Pc Pg Po Qa Qd) On(Hu In Ir Is Iv Jn Jr Js Lw) Qd(Hv Jg Ji Lw Mm Nn Oe Pc) Nw(In Jl Mj Nj Oe Qa) Nn(aA Is Jr Mi) Jl(Lw Lx Nj Oz) Mj(Ji Om) Ng(Fr Om) Nj(Is Qa) Hv(Ji Ok) Pe(Oz Pf) NuNy LwHw MaaA} bA{bW(As aZ bJ bM bR cC cD Ct) bC(As bJ bM dB dE) bJ(aM Bg bO cJ) dE(Bg bO cJ dK) As(Aw bZ cG) Bn(aI bB cB) cT(bO cJ dC) dK(Bg bZ cB) Al(aU Di) aI(aC aZ) bE(aL bG) cC(bL cG) cO(cD cF) ApdH aGbO aXcJ bZcE} aZ{bO(aA aG aI aP aX bL cS De dK) Di(aJ Al aP Ba bW bZ dK) aI(Al Ba Bn dM) dK(aA aL bQ bZ) Aw(Af aV dE) aO(bJ cE cJ) aP(BG dH) bW(aA aL Bg) cN(aJ fR) AlDe BnFr aAbJ aGdE bGcJ bQdH} aL{bW(aC Ba bP bR cC dB dE dH) bJ(bC bH Cq Dd dI dN fR) Di(aC Al As) bC(cR dE dK) Aw(Af dB) aX(cJ dI) bH(aA Ap) bZ(cE dE) AsDe BadB BnCp aJdE cBcS} cJ{aJ(BG bM bO dE dG) Ap(bG bO Di) As(cG Dc Dk) Bn(bV Cp De) Al(aV bM) Ba(dB dE) Bb(bG bV) Dc(An bZ) aP(bN dE) aX(aO bO) AjBg AxcY CucH DkdB bGdK} On{Mh(Mi My Ns Og Oy) Nj(Lw Ma Ng Oi Qd) Of(Il Lj Lw Mg Mi) Oy(Lz Nf No Oi) Lz(My Og) Mi(Mt Pd) Nf(Mg Og) Hr(Oi Pb) NbOi NkIi QdOz} aA{bW(Bg cB dE dH) dC(bG bO dB dE) Al(cB De Di) Af(aU bC) Nq(Nf Nj) bB(bJ dK) AwbJ BgdE BncG DdaX DiaG MgNg NjQd JgOi OzPg aDaI bCbV nMmF} Nm{Is(Fr Ji Lw Ma Mm Mz Nj Nt Nu) Nw(Lw Mm Nj Pc) Ji(Jk Jl Nu) Mm(Ij Po) Qd(Im Mg) Jl(Ma Og) Pg(Et Jo) NqNg NtNv LxMz} aI{dE(aM Aw Ax bC bG bO Dd De dK dM) Di(As Ba Bn dK) Ax(aC bE) Ba(Bn dK) aJ(aD dH) bC(Bn cR) cE(bQ bZ) cS(bN dH) AsdI} cB{aJ(AX bC bG bS dE dG) aX(aP Ar Di Dk dM) Al(aP fR) Ax(Ba bW) Fr(bC cE) bS(bV fR) ArdK BabV BgaP DkcS aObC bMcU bOdM} Aw{Bn(aJ aV cM Cq cT Cu Dc fR) aV(Af Al As bO bS) Af(aJ Dc) As(aP dF) bO(dB dE) AlbM AxaG BcBo CtcU bScD bZcE} Cu{cU(bQ bU cK dA dI) Fr(Ad An Bn Cp) De(As Bn Cw) Ad(dH dK) aX(dA dH) AnbZ AsfR BgdE BncG CwcK DlbQ bNcS} Nn{Oi(Hx Is Jg Mi Mr Nb Nr Nt Nu Nv Om Pa Pe Pg Qd) Pc(Jl Mr Nr Pa) JlJo NyPb OyPg PePf} Di{As(aP Ax bC bO bZ) Al(aG aV bM) Dc(Ad dC dE) bO(aG dE dK) aP(cK dA) cG(bQ cD) AxaU BndF aGdK} Iu{Is(Fr Jl Lw Ma Mg Mp Nj Nt Pc Pg) Ir(Fr Jg Mp Nq Nt Om Pg) NqNg MmPe QdJi JoPg} Mz{Nf(Mg Mi Mp Mv Nq Oe) Nj(Im Lw Mg Mp Nq) Og(Jg Mw Om) LwHv MgNg JlOz PePf} aP{Bg(cE cK dC) bR(aX bZ dE) dG(bV cO dI) aM(cH dL) dH(Af dE) bGcC bMbO bVdL cFdK} Jl{Mi(Lz Mk Of Oz Pd) Nj(Im Ji Oz) Mg(Jo Ng) Mp(Jo Mk) ImOg QdOz PfPg} cG{Af(aV bQ cD cK cL cN) As(Ax bC bO) bO(bJ dH) cE(Bg bZ) AxCs bRbS} Pg{Jo(Et Ma Mg Ok) Nj(Im Ok Pf) Ma(Oy Oz) Pf(Lx Of) JgOi OeOz OkOy} aX{Dk(aU aV bV) Al(aV cD) Ax(aV Bg) cZ(bV De) dH(bL Dc) aGcH bGdK bRbS} cS{Dd(Ad An Cq Cw) Ax(Bb bN dH) AfDe AjCh BbbG BgbM aOdH bRdF} Ng{Jk(Im Ma Mm Om) Fr(Mi Mp Mw) Nq(Jr Nw Ny) MpMu MwQd} dK{Ax(aV bM) Dc(bG bO) dE(bG dF) BcBg aJdL bMdF bOdM} Nw{Jk(Og Oy Pb) Ma(Nj Nk) Il(Og Pb) WmMm NqNj} Qd{Nj(Im Lj Mp) Oz(Jk Pa) MgJo PzLj OiPc} Jo{Is(Mg Nt) WmJi PoMa MpIj HwJg JtNv} De{Af(Ba bV) Bn(cT dF) AjBa AsdF} Pb{Mw(Mi Oy) Ny(Li Nq) PoLw NbIm} bO{aG(aJ Dc dE) AlaU AnDc CpdE} Dd{Fr(An Bo) cU(bM dG) AsbZ} mF{mP(kC mZ nT) nMkC mHmI} Og{Jg(Hv Hx) NjOm JkOz} aJ{bZ(dH dL) bBdL bQdG} fR{AlcD FrMi NuOe OiPa} Oz{Nf(Mi Qa) HvJk} cU{dG(aE Cp Cw)} dF{aU(Af Bn) aMdB} As{AxbZ bBbC} Fr{MiPd cEdC} aV{dE(Dc Dk)} nR{nTnK mWoQ} AfApBn AjBaBg MmIsPz MpJgOi JiPePf aObCbM nUnBoQ nDnJkG Constrained panels with 3 analytes, where 1.0E-5 >= 'AUC p-value' > 1.0E-6. Contains 1,942 panels of 625,624 total panels evaluated. : Ml{Nw(Fr Hv Hw Ir Iu Iv Js Ma Mf Mi Mp Mv Nb Nk Nn Nr Nt Nu) Jr(Fr Iu Iv Jg Jj Jk Lh Lx Mj Mv Nb Nm Nr Nu Om Pa) Jj(Et Hw Hx Ir Jg Jq Mi Mj Mk Mn Mv Ny) Mz(aA Im Ir Iu Jt Mj Mv Nb Nr Ok Pe) Po(aA Iv Jl Lw Mj Mp Nb Nj Nt Oe) Is(Fr Ji Lw Ma Mf Mi Mm Mp Pc Qd) Om(In Iv Jl Nb Nj Nr Og Pa Pe Qa) Ji(Il In Jk Jl Ne Nr Nu On Qa) Ok(Ij In Jl Jp On Oz Pg Qa Qd) Lx(Hx Iv Mr Nb Nj Oe Pa Pe) Hx(Fr Jg Lw Nn Nt Nu Oe) Qd(Fr Jl Ma Mi Mj Nb Pa) Jp(aA Hw Ii Jq Js Jt Mr) On(Jt Ma Md Mw Nf Oi Qa) Lw(Hv Mj Nb Nr Pe) Nj(aA Mi Nt Pe Pg) Oe(Iv Jl Nb Nr Nt) Mj(Jg Mm Nn Oz) Nv(Hv Ir Iv Pe) Nb(Im Nt Nu) Jl(Im Nm Nn) Nr(Mp Oz) Ma(Hv Pg) Ng(Jg Mv) Ir(Iu Nu) Qa(Et Jq)

Figure 29 Continued

NmPg NnPe LvMg MfaA MwOy HvNx IvOz JgPa JkJq} Jj{Ma(Ih Iv Jm Jq Jr Mi Mn Nk Nr Nt Nx Ok Om Qa) Im(Iu Jr Lh Mp Nb Nj Nr Nu Oh Pa Pc Qe) Nq(Hv Hx Jq Jr Lx Mn Nx Ok Om Pe) Jk(Lw Mg Mp Nj Nn Nt Nu Oe Ok Pc) Om(Lw Md Mp Nf Nj Nk Nn Oh Pb) Lx(Iu Jt Mg Mp Nj Nn Oe) Ny(Jr Mg Mp My Nj Nn Oe) Il(Ip Ir Nj Oh Pc Qa) Nw(Iu Mg Mp Mv Nj Nn) Pe(Jg Mm No Pc Pf) Is(Fr Jg Mh Nk Nt) Nx(Hv Hw Hx Mv My) Po(Iu Mg Oe Pc) Nu(Hv Hw Jq Mn) Nv(Iu Lw Mg Pc) Mj(Jg Mg Mm) Mn(Hv Hx Jr) Mz(Jt Nk Nl) Jq(Mp Mv My) Nn(Ir Pc) Jr(Fr My) Oe(Lh Nt) EtHv MvHx NjHw NlJp IrJg} Nj{Im(Hv Ij Is Lw Lx Mj Nn Nq Nr Nv Nw Om Po) Qd(Fr Jk Jl Ma Mg Nb Nn Nq Oe Oh Ok) Lv(Il Iq Jk Jt Nq Nr Oh Pa Pe) Jp(aA Iu Jk Jl Jr Nq Nt Oe Ok) Mz(aA Fr Jk Jl Nt Oe Oh Pc) Is(aA Ma Mh Mp Nn Nq Oe) Jl(Ma Mp Oe Og Ok) Nw(Mg Mp Nn Oe Oh) Il(aA Et Ji Ok) Nv(Ma Nu Oe Oh) Pa(Ji Jq Mm Om) Pe(Jg Lj Mm Pf) Jk(Ji Mm Ok) On(Md Nf Oe) Ma(Hx Pg) Hv(Et Jq) Om(Mp Nn) aA(Fr Pg) PoOe NtNd NyPb} dE{cX(aJ Aw aZ bB bL bQ cJ DC Di Dk fR) Dc(aG aL aU bC bW cB cY dC De dK) bO(aJ AL aZ bG cG cJ dC) Cx(aJ aZ Ba bZ Cq De Fr) cJ(aG aM Ax Bg De dF) aZ(aO bA bQ Cp dF) bG(aJ aL cB cC dC) aI(Ba Bg bW Cq) bZ(aG cC dC Dd) cB(Ax bV dM fR) aL(aM Cq Dd) aV(AI Aw Cp) cC(aA cG dF) dK(Ax Cu dD) aJ(aG dC) aP(Aw dC) DeaA DkcY cEcG} Cx{Bb(aJ Al aM aV bB bZ dB dC dK) Dd(aL Ap aU bL Bn bQ bW cB cY) Al(aK aL aO bL bQ bZ cB) aU(Ba Cq cT Cw dB Di dM) cB(bW Cq Dc dI dK dM) Cq(aJ Ap dB dK) aM(aO Aw Cp Dc) aV(Ap Bc dI Dk) bZ(aG aJ cE dK) Bn(cR Cv dB) bW(Ax bP cF) dC(Bc bV Cw) De(Ao As) bQ(cD dH) dK(bB dB) ApAx CofR DcaL DkaJ aIbE bFcG} bO{Al(aA aG aK aL AP aV bW bZ cB cG cX cY De) cX(aM aO Ap Bb bC bZ Cp cW dC De dF) As(bC Bg bZ Cp Dc De dF Dk) aZ(aJ Ba bC Bg cJ fR) bM(bA bC bW cG dK) Bg(aA bA cJ) aG(Aw Bb cG) aL(aC bE bJ) cB(bS bV cS) Bn(Cp Cw) Dc(bW dC) bA(bE dK) bG(cJ dC) bJ(bQ dF) ApDi AxDe aCaI aJbC aXdH bQcC bZcJ} Lv{Jt(Hr Hv Hw Jo Ma Md Na Nf Ny Of Pb) Ok(Hv Hw Ij In Jq Md Mg Na Ny Pc) Ma(Im Ir Iu Mb Nb Nl Nr Oz) Ly(Iu Mg Nl Oh Pa) Nf(Lh Mt Mv Nb) Il(Im Mp Nn Pc) Jg(Hu My Ns Oy) Qa(Hw Ij In) Og(Mv Nb Nm) Nn(Nr Pa) Lw(Fr Pa) Mg(Im Ir) Nk(Iq Nm) Hu(Mu Nq) Jk(Ng Oe) Of(Mv Nb) MzJi HvOh IrPc IvJr LiLj} Ng{Nq(Hx Jg Jl Jq Lw Lx Mv Nb Nt Nu Nv Ok Om Pa Po) Mg(Fr Jg Jk Mi Mw Nv Nw Om Pg Po Qd) Jg(Hv Hx Jp Mi Mp Mz On Pg Qd) Om(Il Iu Lw Mp Mw Nn Nu Pg) Fr(Hv Hx Iu Jr Nn Pg) Mw(Mi Mm Mp Mv Mz) Jk(Et Ji Nt Nw Oz) On(Lz Mh Mz No Pc) Mp(Mv Nt Nv) Mm(Il Pg) NmPg} aZ{aJ(aL bG bZ cB Ch cJ De) Bg(aA bA bC cD Di) cC(bL bQ bZ cG cX) bA(aG bG bJ dK) cD(Ba bQ Co Cq) cG(As bJ Bn cR) Di(aL aU fR) bG(aA aI fR) bW(aM cF cR) cS(bR cH dH) cX(aM bC cW) dF(Af bJ Bn) Al(aO aU) Ax(aI De) Co(aV fR) bQ(bJ cE) bZ(cE Dd) cJ(aP bH) cR(Cq dK) AwdK BnaO CvbL DecL} Nf{Mz(Fr Im Jg Jk Lw Ma Mw Nt Om Pc Pg Qa) Nw(Hv Hx Il Jk Ma Nn Nq Oe Pg Qa) Nn(aA Jq Mu Nv On Qd) Mp(aA Im Jq Mv Pd Po) Om(Hv Hx Og Pg Qa Qd) Nq(Hx Jr Lx Qd) Ji(Hv Jl Pa Pg) Mw(Mi Oy Qd) Oz(Nt Pe Po) Ma(Hx On) Mv(aA Mi) PoOe NsOn HvOk PfPg} As{Aw(aA aI aJ bL bZ cG Cu Dc DD Di) De(aA aI aP Ar Ax bV cJ Fr) Cp(aL aP bC bZ cJ dF) Di(BA bQ Dc Dd dF) bC(aA aO bZ cJ Cu) aL(CO dI dN) Ax(aU cJ dK) Cu(Ao Co dK) dF(bW Cw dK) Dd(aI cG) aU(bA Dk) cB(bS bV) DcbZ FraM aIbA bGbW bQcX} Og{Mw(aA Hx Is Jl Jq Jr Nt Nu Nw Ok Po Qd) Jg(aA Ij Il Is Jk Jl Jr Mi On Pg Qd Qe) Hx(Fr Jk Lw Ma Mm Nm Nn Nq Nt Nu Nw) Jk(Ji Jq Jr Lw Mz Ok) On(Lw Ma Mg No Pc) Il(Ji Lw Mm Om) Nm(Hv Pg) Nq(Jr Nw) Mg(Jl Mz) Om(Nk Qe) NbJp ImfR} Pb{Pe(Ji Lx Ma Mw Mz Nq Nu Nv Nw Ny Oe Om) Mw(Hu Hw Hx Jp Mr My Mz Nr Oz Pa) Ny(Hq Im Jk Jp Lw Lx Ma Nm Pc) Nb(Lw Lx Mi Mz Nw Oe Pg Po) Hx(Jp Lw Lx Ma Nn) Nw(Ij Oz Pa Qa) Mz(Jg Om Oz) Jp(Jt Nr Om) Pg(Jl Lw Ok) Pa(Ji Om) MxOn} cX{cR(aG aJ aL bC bQ Cq Dc dF) aG(Aw Bb bC bL Dc dF) Di(aJ Ap Bc bZ De) aI(aC Bb DC) aJ(Aw bM bZ De) bQ(aV bR cD dH) cJ(aO bL dF dM) dC(Aw bL bW) dK(Ba cW dD) Dc(aU bZ) De(bV fR) aC(aL dD) bC(cB cT) aLbL bScB bWcT cFcS} Bn{cG(aV Bg Cp Cq Dc Dd De dK Fr) De(aJ aP aS Ax bV cS Dc) aA(aI bB bC Bg cB Cq) Cp(aI bA bZ dF Fr) Dd(aI cJ Di Fr) dF(aK aV bC cY) Aw(aK aM Ba) Cq(cJ cS Di) bA(bC Bg bW) Dc(cY Di) cJ(Cw Dk) dI(aI aL) CubZ DifR} aX{dI(aI aJ aO aP bQ cZ dD dF dM Fr) cH(aM bB cB cJ dF fR) dH(bE Bg bP cG FR) bV(aI aO Cu dD dF) cB(aO bS FR) cK(Bc Bg Cu Fr) cQ(Ax Cu Dk) Al(bN Bo) aL(bH dK) ArbB AxDe CudN aAdA bGcJ} Jp{Ma(Is Iu Ji Jl Jt Mp Ok) Mm(Im Is Ji Jr Nt Pe) Mg(aA Is Oe Ok Qd) Of(Ij Jg Jt Ok Om) Im(Fr Nr Nt) Is(Ir Iv Pc) Nq(Hu Ok) Md(Mp Qa) Qd(Lj Qc) Ji(Ij Jn) Pc(Jl Ok) NmNu NsMq LzMj MpNd HuJk IlOh} Mz{Oe(Fr Iu Jg Jk Ma Mg Mm Nq Nt Pa Pg) Hr(Mr Nr On Pa Pe) Im(Lw Nk Nn Nq Pc) Nn(Jl Mt On) Ma(aA Nk Pc) Mp(Hq Jl Md) Of(Jg Jk Om) My(Mw On) Oi(Jg Pc) LwIu MgNk MuHu OnOy} Nm{Et(Is Jk Jt Lx Nt Nv Ok Om Po) Jg(Hx Is Jl Jq Jt Lw Nv Pg Po) Nt(Im Ji Lx Ok) Jl(Hr Is Jo Of) Ok(Jk Mi Nu) Mm(Nv Pe) Is(Mg Pg) NuNv NkJi NlNw ImLh IpOm} dK{bM(aI aJ AJ bA bQ bZ Cq dD) Ax(Ap Ba Bb bW) Cu(Af cH dB dL) cB(aA bS bV dM) Di(bC bZ cG) AI(aV dD) bA(bC cR) bG(Ap bC) dB(Bc Dc) dL(dF fR) AjBa ArbB aLcR cGdH} cG{Af(aY bU cA cC cE cF cO dA Dc dI) dH(Ax bG bS cS FR) AI(aA aV cD Di) cE(aG bA bL Fr) bG(bF cC cD) Ax(bQ cN) CqCu DcaG DibJ FrbQ aLbW} Oi{Nn(Et Fr Hu Il Ir Iv Ji Jq Jr Lx Mj No Ny Ok Po) Jg(Iu Jl Lw Mg Nt Nw Oh Qd) Pc(Is Mi Nt Nw Om) Ma(fR On) NqOm MdOn OzfR} Al{Di(aJ aU bW bZ De fR) aA(aG aI bB bC bZ) aV(bL bZ dB Fr) cB(aJ bA bV dF) De(Af cJ) aL(aP bZ) aU(aO dB) BbaI aPdA bLcD bWcJ} Oe{Jr(Jk Mr Nb Nr Nu Pa Pe) Nw(Iu Jk Jt Nk Pg) Nu(Hx Jg Nr Pe) fR(Im Ma Mt Ok) Hr(Jl On) Qd(Oz Wm) Jg(Hv Hx) LwJl LzOn OzPe} Jo{Nt(Jk Jl Jq Om Pg Po) Om(Iu Lw Mp Nl Nr) Ma(Ij Mi Nv On) Jt(Is Jl Pg Po) Nv(Iu Mg Nr) Jl(Jg Nq) Pg(Mp Nu) MiJk NkOn} bW{aL(aV bQ bU cA cD cL cO dG dI) bA(bQ bU dA dB dI) Cu(Cq dB dH) Bg(Aj cT) Di(aA Ax) bG(bM dB) dH(bQ fR) ArcB aAdB} On{Lz(Hu Li Mp Qd) My(Mt No Pc Pf) Oy(Iq Lw Ma Mt) Mp(Hq Nv Pc) Hr(Pc Qd) PoHv MaNk MhHu MiHq IsOh LifR NwOf} bJ{aI(aM Aw bC cT Dc Dd fR) aL(aM bZ cO Cp Cw dF) aA(aM bA De) Cu(cU De) Dc(aV Di) Dd(cJ Fr) BccJ bAbM} Aw{Dd(Ad An Cp Cq Cw Dc) Af(Ba Bb fR) dB(aA aV bA) bS(bR cK) AdDc AnaA AxdC aPdA aQaV cKdI} cJ{Ax(Ap Bb Bg Cs) Af(Cp Cq De) bG(bA bM cR) Ap(Aj bV) Bg(bC bV) Cp(Bo dB) bM(De dN) BbaJ aMcH} Cu{cS(cH cK dG dH dN) Fr(Cw dB Dc) aP(cK dH) aV(Ad Cw) AfBa AndH BodC CqbZ bCdB bEcH cUdG} aA{Af(aV bB cB Co Cq Cw cY) Ma(Lw Nk Nn Pc) Lw(Hv Il) ApdH DcdB PfPg nNmP} aI{Ba(Ax bC cE Ct) Dc(aD cZ dB) Di(aC bE) aM(cH dB) bC(aC dB) aDfR aGaH cSdL} Of{Om(Hv Hx Il Jk Pg) Jl(Ji Lw Nv Ok) Jk(Jr Nw) Pg(Lw Ok) FrHx MaPe} bA{cC(bH cO dB) Ap(cB cK) bE(Bg cB) bR(bZ cO) dH(bC cT) DebI aMdB bQcO} Fr{Oy(Hv Jl Pe Qd) AdDd AfDe AxcB HrHx QdOz aDaM aGcE aPcK cSdG} aJ{aG(bG bN) cO(dG dL) dH(cE dF) DebM aDaL aMcH bBdG bGdC bRbZ} Dc{Ad(aG aU bC) bZ(aG aV dC) Di(An aU) dB(aV dC) cKcS} Nn{Pc(Hx Is Lx Nb Nt Nw Ok Oz Po) MiMx PfPg} Oz{Is(Ir Iv Jl Jr Mh) Nr(Nw Qd) LxPa IvJk JlPg} Pe{Pf(Hr Im Is Jt Mg Mp Nt Pc) LwPd MmOy} aL{bH(aC cC cR) bC(aC dB) bS(cB dB) AfDe bQcE cUdG} aP{Af(aU Cp) dG(Cp Dd) DecK aDbR bCdA bFcE bGbV bMdH} cS{dH(bG bQ dD) Dd(bN dL) BbBg DkcK aMcH dLfR} mF{nR(mU nF nM) mZ(mI nM) kI(nN nT) mUoQ kGoP} cB{bS(aG aO dF) bC(dM fR) AxDi bHfR bLbV} Hr{Hx(Ji Li Lw Ok Om) Pg(Ji Ok)} Iu{Ir(Et Jk Lw Mg Po) MgJl IsOh} Nw{Hv(Im Lw Ma) MdQa MhIs MyJk} bM{bC(bB BG dF) Cq(bZ dB)} Pg{Mg(Oy Pf) Hq(Mi Pf) LwHv} Ax{Cs(bZ cR) aU(aG Bg)} nD{kG(nH nL) nRkO kCkF} Dd{Di(An Cq) aGbZ} Mi{Jl(Hq Mh) MgPd} Im{LwJl MaNi HuPc} cE{bZ(aG dC) DedF} mW{nR(nB nI) nUmZ} Wm{IiJi QdJs} fR{AfDe AjCo} kG{nUkI nHnL} BbDiaG CpbIcU NuMhIs LwHvQd IiJiJk aQaUbG

Constrained panels with 3 analytes, where 1.0E-4 >= 'AUC p-value' > 1.0E-5. Contains 3,023 panels of 625,624 total panels evaluated. : Ml{Jq(Fr Hv Ij Il Iv Jg Jl Lh Lx Mj Mk Mp Nb Nj Nn Nq Nr Nt Nu Pa Pe Po) Jj(Fr Hv Ih Ii In Ip Iq Jm Jn Jo Js Jt Ma Mt Mw Nb No Nr Nu Nx Qc) Om(aA Hv Hw Hx Im Ir Iu Js Lw Mh Mp Mr Nk Nl Nn Nt Oe Of Oh Oy Pc) Qa(Fr Im Is Iv Jg Jl Jt Lw Ma Mf Mi Mj Mm Mp Nb Nm Nn Oe Pc) Jr(aA Et Hx Ii Ij Il Im Ma Mg Mn Mr Nj Nl No Nv Oe) Nt(aA Fr Hq Hv Im In Ir Iv Jg Lw Ly Ma Ne Nn) Ma(Hw Hx Ii Ir Ji Jl Mi Mj Nb

Figure 29 Continued

Figure 29 Continued

Nw Po) Nv(Nb Nr Pa Pe) Ji(Jt Mg) Ok(Il Qd) MmPg MxOn MzNb IjNw} bC{dF(bJ bR cD cE cN dH dK) Fr(aV bQ cK dA dH) aJ(Bg bM cJ dG dH) aO(bR cE cR dB dH) bG(bR cB cD dB) al(dH dK) bJ(aS cZ) bM(cT dK) cB(Ba cR) CqdB DiaG aPdI cGcL} DdJ{Bo(aG al aV Aw bZ cG De dK) bJ(aO aV bA bZ cG cJ dF) Di) An(al aO bZ cG cJ dF) bZ(Ad cE Cp Cq Cw) Cw(al Di Fr) Ad(al Di) Cq(al Fr) CpFr aPdL bAcT} On{Oi(Hx Mk Nv Ny Pc Po Qd) Jt(Hw Ij Jq Na Nb Om) Mg(Jh Mv My Nb Om) Po(Jp Mi Qd) Ns(Lh Mt) Lz(Md Mw) Im(Nn Pc) Ny(Hv Pc) LwQd LxMi MdMh MwOy MzHu} Pg{Ok(Hv Hw Ij Iy Jq Md Mm Mz Na Ny) Im(Hq Jt Lw Ly Mm Nn Pc) Oy(Iu Jl Mw Om Pc) Pc(aA Nn Oi Pf) Hq(Lw Mm Mp) Md(Lw Om) NmJt LyMp JlPd} aL{cO(bQ bR cC cD cF cN dB) bZ(aC cC dH) dB(aM Cp Cq) An(Cp Cw) aD(aA dN) bG(aC bJ) bH(aG aM) bR(bS dI) cC(bS dI) AdCw BgaJ CocE aHfR} dK{bM(bB cG Di dM) aX(cZ dD dF) cR(aI bG dF) Bg(cJ Di) aM(bL cH) cG(bJ cF) cO(bP dB) AfAw AraG AxcY ChfR DebG bLcB bQdH bRbS bZcE} Jl{Mg(Ii Jp Mz Nm Ok Oy) Qd(Lw Lz Mp Nn) Pc(Jo Lv Mz Oi) Oh(Im Jo Jp) Mp(Hq Im) NmJt NnOz LwMd MiMx MmMz MwOy JqOk} Oy{Mw(aA Jk Lx Mj Mz Nu Po Qd) Jk(Hx Mi Mp Nv Om Po) Fr(Ir Jt Nk Nt Ok) Nn(Il Om) Nq(Hx Nw) IlOm} aA{Af(aK Ao Cp dC) aD(bB De) dH(bL cO) ApcK AxaU BacB BoaM CqbJ MpHq MuHu MwMy NkOm HwQa IlPc bFcE bRbS mPnI nJkO} Im{Nk(Fr Hv Nb Nq Nu Nw Om) Mz(Iu Mg Mp Oh) Nm(Et Fr Mm) Hv(Lw Mm Mv) Nn(Oi Qd) LwNw QdPc JkJr} cB{bS(bM bR bZ cJ dC dM) aX(bH bL dF) bV(aC bH dC) Ba(Aj dI) bA(aC Af) dM(bZ dI) ApAx DibL bHdC dLfR} aI{bJ(Bc Cp Cw dI) dI(bR cC dH) aC(bG dM) aD(aM Cw) bE(Ar bG) bH(aM dC) bS(bR dB) AfDe AxCs CpdB cEcO} Ax{Cs(aP aU bB fR) De(Af aG aJ bM) Bb(aG bB Di) Ap(aV Bg) Di(Bg dC) aX(bQ dN) dG(aP cS)} Jt{Jp(Hv Hw Ij Jn Jo Md Na Ny) Lv(Ij In Jn Jq) Nm(Mz Po) AaOz NnOi MbNd MdMz JkJo} Ok{Qd(Lz Mp Nn Nq Pc) Jp(Hw Jq Md Mm Mz) Oz(Hw Md Mz) Mg(Jo Nk) FrNk LvOm MpJo HvJn} cG{bH(bQ bR bU cC cD cF cL dH) aP(bQ cE) dH(bZ cO) AfbR ApDg BgbF aJcE aMbJ bMcC dGdM} Aw{aV(bZ cO dI) dB(Af cY dC) fR(Ad An Cw) bS(bQ cA) cD(cO dI) BaCt BcbJ bLcE} Pc{Oi(Et Fr Hu Jr Lx Nv Ny Pe Po) Nn(Fr Il Ir Lw) Lv(Nr Pa) QdLj} Oz{Nr(Jk Lx Mp Nv) Pa(Ir Mv Nu Om) Iu(Hv Nw Pe) Nk(Fr Jk) LxPe HvIp} aX{bV(aJ aP bE dM) cZ(bH bJ cS) dI(bL cT Di) AraU FrbQ aHcH bFdH bHdD} Jo{Nt(Et Fr Hv Ir Mm Mp Mv) Mg(Ij Po) Jk(Et Mp) Nv(Nm Pe) IjIu} bM{Cq(aG Ap aV) cJ(aO Bg bH) aJ(bR dD) aP(bV dC) bA(Bg Ch) bQ(cC dH)} cE{bQ(BG bL De) bA(bF Bg cO) bZ(aJ Cp Di) aJbF bGfR bLdF} Nn{Oi(Hv Ij Jk Qa) Lw(Hv Pe Qd) Mx(Mz Qd) MiMt QdLj} Nm{Mm(Jk Lh Nt Om Qa) Et(Il Qa) Nt(Ip Mp) HvJk} Mz{Md(Mw Nb Om) Qa(Hw Ij) EtNk LwPa MpNd IvJr LiLj} Nw{Nq(Hu Md My) Nk(Lw Mg) Hu(Jk Mu) MpHq MwMy HwQa} dB{dC(Bc bQ cO dM) aM(aJ cO) DkaV aUdM bVcC} Lv{Oh(Il Nr Pa) Mg(Nk Nr) MdQa MvMy HuJk} bJ{cJ(aM bQ Cw) dF(aM De) aScO bBbV bQdH} mF{kC(mI nN nT) nM(kG mH) nNmU lWmI mTkI} nK{kI(kF mP nN nU oQ) mZ(mP nM) kCkF} Bb{dC(BG Di) aV(bZ dF) aGbZ bBbV} Qd{Lj(Fr Hv Li) WmIh MuHu MwMy HxQb} bR{bS(bA bQ bZ dF) bP(aJ cS) bZcS} Ap{Bg(cJ Dg) aV(dF Dk) DgdF bVdH} Di{aU(aJ aQ) AfDe aCdD aVcO cKdI} fR{Af(Cp Cq) aHbB bNcC cSdG dHdI} Lw{Hv(Fr Il Mm Nt) MpPd} Hq{PoMp FrHx NqOi NtNd OmPa} Ba{AfCp AjaU CtDk bScD} bG{aCcJ aUdM bQcD cCcS} mE{mW(mZ nR) oQ(mZ nB)} Bg{DeaJ aUbV bAcT} Ly{NtHv MiNk MpJk} Iu{Ir(Mv Nu) MgQa} Jp{MdNb IvJr LiLj} cJ{bS(aG aM) DkbE} De{BcBo aQaV} Lz{Mp(Mj Nr)} Hu{MuNv JkOm} Jr{NuOh MmIl} Pe{Pf(Lx Oh)} aJ{aMdL aUbP} bA{AnCp ChbE} cS{cZdL dFdG} mZ{nMnC nTkI} nD{kG(kO nC)} DkaVdI MiNeNl bZdHdM mPmWnB

Constrained panels with 3 analytes, where 1.0E-3 >= 'AUC p-value' > 1.0E-4. Contains 3,316 panels of 625,624 total panels evaluated. : Oe{Ma(Et Il Ir Iu Iv Jg Jk Lh Lx Mp Mr Nb Nk No Nr Nu Nv Ny Om Pa Po) Im(aA Hv Ir Iu Iv Jg Jk Lx Mm Mu Mv Nj Nk No Nr Ny Om Pa Pe Po Qc) Nj(Hw Ij Iq Iv Jg Jk Jq Jr Lh Mm Mt Nd No Nr Nu Ny Pa Pe Qa) Jg(Hu Iu Jk Jq Jt Lw Mg Mj Mp My Nb Nl Ns Oh Ok Oy Pc Qa) Mm(Ij Ir Is Iv Jk Jq Mj Mr Nb Nr Nt Nv Om Pa Qa) Mg(Hv Hx Ir Is Iv Jr Lx Nu Pa Pe Pg Po Qa Qd) Nb(aA Et Hr Iv Jj Jk Md Mv Nf Nn Nq Of Qa) Iu(Et Hv Hx Ij Iv Ji Jq Mn No Ny Om Pe) Jk(aA Et Hu Ir Jt Lw Lx Nm No Nr Qa Qd) Pa(Hv Ij Ir Iv Jj Jt Lw Mn Mv Nm Nq Qa) Ml(Hv Ii Ij Il Jn Jo Jq Js Lh No Nx) Nq(Hv Ij Ir Iv Jq Nf Nr Pe Qa Qd) Ok(Hv Hw Ij Is Jn Jq Md Mz Ni Pb) Nk(Ij Ip Jh Jq Mp Nu Nx) Ir(aA Fr Jt Lw Lx Mv Om) Nr(Iv Jj Jq Mv Nn Oh) Nf(aA Ij Jq Jt Lh Mw) Qa(aA Hw Ij In Pb) Jt(Hv Hw Jn Md Na) Oh(Hx Lx Nu Ny Om) Lw(Et Nv Om Qd) Mv(Hv Iv Jq Pe) Il(aA Jq Nm Nn) Fr(Is Ji Qd) Mw(My Nl Pb) Ij(aA Nn Pc) Lx(Iv Pc) Ly(Lh Wm) Nl(Nu Om) Qd(Lj Lz) Jj(Ih Mt) PoOn EtaA MzJi IiOz IvNy JqPe OmPb} Ml{Ma(Fr Ij Il Iu Iv Jg Jk Jq Jt Lh Li Mr Nk Nl No Ok Om) Iv(Et Jg Jj Lw Mf Mm Mp Mt Mu Mv Nb Nj Nq Nr Nx Ok) Ij(aA Ii Ir Iu Lh Mg Mp Mr Nb Nn Nr Oh Pa Pc Pe) Ir(Et Hv Iq Jq Lw Mg Mp Mv Nb No Nq Nr Pc Pe) Nj(Hv Hw Hx Iu Jo Js Li Mt Mv Nb Nr Pa Qe) Jq(aA Et Hw Hx Ii Im In Iu Mg Mh Mr Mv Nk) Js(Et Jg Jk Jr Lh Lx Mm Mu Nr Nu Pe) aA(Et Hv Hx Il Jk Mn Nm Nr Nx Pe) Nb(Fr Hv Mf Mm Nf Nn Og Oi Oy) Jj(Fp Jh Li Mf Mr Mx Pa Qb) Ok(Fr Jt Lw Mf Mg Nq Ns Pc) Nm(Fr Hw Il Lh Mk Pa Qe) Et(Hv Hw Iu Mh Mv Nr) Ii(Lw Lx Mm Nn Nu Oz) In(Im Jr Jt Nn No Nu) Jn(Fr Hx Lh Mq Pa Pe) Nx(Il Iu Me Nk Nu Pa) Hv(Mp Nn Nq Pe Pg) Jt(Im Ji Jo Mi Nn) No(Iu Jg Mf Nn) Nr(Mf Mt Nq Pb) Hx(Hr Iu Mm Oh) Jr(Jo Li Lw Oh) Pe(Im Mp Oh Pc) Mg(Pg Po Qa) Mr(Jg Jk Mv) Mw(Mh My Ng) Hw(Ip Mn Mt) Pa(Jk Mf Mv) Nu(Il Iu) Lw(Fp Jo) Mi(Ly Pc) Jg(Iu Ns) FrMe MpHq MvOg NgJk NkIp NyOf} Nf{Jg(aA Hv Hw Ij Ir Iu Ji Jq Jr Lh Ma Mj Mp Mt Nn Nq Nt Nv Pa Po) Nq(Et Hv Ij Ir Jt Ma Mf Mr Mt Nb No Nr Nt Ok Oz Pe Qa) Fr(Hv Im Ir Is Iv Ji Jt Me Mp Nb Nl Nn Nt Ok Oz Qa) Jq(Hx Il Lh Mr Mt Mv Mw Nb Nr Nt Nu Oh Pa Pc Pe) Qa(Im Jl Jt Lw Ma Mg Mp Mt Mv Mw Nb Nm Oh Pc) Nn(Et Hu Ii Ij Il Ir Ma Mf Nb No Nt Ok Pe) Nt(aA Im Ji Ma Mm Mt Mv Mw Nb Nj Om) Mg(Hv Hx Ij Jl Lx Ng Ok Om Pe Pg Po) Nb(Is Jj Jl Lw Lx Mm Nu Oz Pg Po) Jt(Im Ji Jj Jl Ma Mv Nj Nw Pg Qd) Mp(Ii Ij Il Ir Lh Ma Ok Pb Pe) Mt(Et Hx Ij Lx Ma Mv Nv Oz Pe) Mw(aA Jj Jr Lx Ng Nu Og Pe) Mv(Hw Ir Ng No Ok Pa Pe) Ma(Ii Lh Mi Mr Ok Om) Ij(Et Hv Li Nm Og) Jk(Hx Li Ok Pe) aA(Li Lw Nm Oz) Po(Lh Oh Pc) Hv(Lw Mm On) Ok(Il Ji Mi) Nm(Hx Nr) Im(Ii Pe) Jo(Jj Lw) Lh(Is Oz) Nw(Oh Pc) Pa(Nv Oz) MeOn IuPg JhOh JiPc} Jj{Nj(Hx Ih Ii Ir Iu Iv Jr Jt Mg Mj Mp Mt Mu Mv My Nn No Nu Qc Qe) Nk(Hv Hw Hx Ip Iq Jg Jn Mg Mm Mt Mu Mv Mw My No Nu Ok Qc) Nl(Et Hv Iq Jg Jq Jr Mj Mm Mn Mu Mv Mw My Nn Nu Nx) Pc(Et Fr Hu Hv Hx Ir Iv Jg Jr Lh Ma Mn Mv Nt Nu Nx) Jt(Hr Hv Hw Ir Jq Md Mg Mp Na Nn Of Pb) Nu(Iu Iv Lw Mg Mr Mu Nb Nn Nr Oh Pa) Mg(aA Fr Iv Jg Ji Ma Ng Nr Nt) Iu(Fr Ip Iv Jg Ji Mm Mv Oz) Nb(Ip Jm Jr Md Mp Nn Nx) Nr(Ip Jm Jr Mp Nn Oz) Lw(Ir Iv Jg Ma Mv Nq) Mm(Iq Ma Mv Nx Om) Mw(Md Mh My Of Oh) Pa(Ip Jr Nn Nx Oz) Mr(Ip Nn Nx Oz) Oh(Hv Jg Jn Jr) Ma(Fr Nn Nq) Iv(Jg Mp Nn) Im(Ih Js) Ip(My Oz) Jo(Hr Hw) NqJg NdIk JmOk} bW{bQ(aV aZ bG bJ bR bU cA cC cF cG cL cO dF dI) dF(aV bJ bR cA cC cD cE cF cN CO dI) bG(aV bP cA cC cF cK cO cR dA dG dI) aZ(aV Ax Bn bR bU cA cB cL cN dI) cB(As Ba bM Bn bO cR cT Dc dE) Di(As aV Bg Bn cD cK dB dH) Ax(aA aV bM cF Cs dE dH) dB(aM Ba Bg bO Cq cT Dk) cG(bR bU cL CO dI) dH(aI aO Ba bV bZ cT) Bg(As Bb bP cJ Dc) bM(aM cT Dc dK dM) Bn(aA aI Ba Cp) Cx(aM As bR cR) bJ(aI aS Dc dD) bO(As bP cF dE) Dk(aV cD cK) bP(Al Dc dK) cF(aI bZ cX) Aj(Aw Dd) Fr(cK dG) aG(Al aM) cD(aI Ba) cX(cR dE) AsbZ BoDd DcdG aCdD aOcE bNfR} Pb{Qa(Fr Hx Im Jo Jt Lw Ma Mm Mp Mr Mw Nm Nn Nq Nr Oh Pa Pc Pe Pg) Jg(Hw Hx Ii Ij Ji Jq Lh Mi Mj Mr Nr Nt Nv Nw Oz) Oz(Et Fr Hx Ij Jk Jq Jr Mm Mn Nq Nu Ok Pe) Hx(Et Jq Mg Mm Mn Mu Nj Nm Oh Ok Pc) Mw(Ii Im Iu Jr Jt Lx Mp Nu Pg Po) Pe(Et Hv Ij Jk Ly Lz Mg Oh Pc Pg) Ok(Fr Jl Mi Mp Nb Nn Nq Oi) Om(Ir Jt Lw Mi Mp Mr Nt) Fr(Hv Ij In Ji Jl Jt) Ny(Et Hu Ij Mm Mn Nk) Hv(Jk Lh Mp Nm Pa) Lw(aA Ij Lh Pa) Nb(Ij Lz Nj Pc) Nm(aA Ij Lh) Nr(Et Jq Nx) Ji(Ma Nt Wm) Pa(Ij Jq Nx) Jl(Jp Lv) Jt(Nj Pg) MgPg MiIl MzJo} Of{Mw(Hx Im Is Jq Lh Lw Mk Mp Mr My Ng Nj Nl Nm Nr Nt Nu Nv Nw Ok Om Oy Pa Pe Pg Po Qd) Jg(aA Fr Hw Ir Ji Jq Jr Lh Ma Mi Mj Mp Nr Nt Nw Ok Om Pe Po Qa) Om(Fr Iu Ji Jt Lw Ma Mg Mm Mp Mr Nl Nn Nt Oh Pc) Ji(Fr Hv Hx Ma Mv Nq Nt Nu Pa Pe) Jt(Fr Il Ma Mv Mz Nq Nw Pg Po) Nb(Fr Is Lx Nt Nu Nw Pg Po) Jk(Hx Ij Mn Mp Nm Nx

Figure 29 Continued

Figure 29 Continued dC{BcBo CxdN DkdB bQcF cVcX} Mp{Nd(Jl Pg Po) EtIl} Nw{Mh(Iv Nb) MeMm NbNy} bE{aI(cJ cT) dD(CX)} mZ{mY(lW nC nH) mlnK} kI{mP(nC nI) nNnI nTnC} Af{AoCx DeaG cGdG} Cw{An(bA Di) AdDi} Mg{Pd(Mr Pc) QdJl} fR{De(aD dL) IiJn} nU{nK(kC nA) mFmM} kG{mW(nI nK) nRmF} Nq{Oi(Ij Jk)} Ns{LxMq MhMw} cR{cX(bB dM)} kC{kF(mF nC)} ApCuDg AraCal DkaKdB NnMjMx MeMmPa MzNbNy IlItQd aLcFdI nTnBoQ Constrained panels with 2 analytes, where 1.0E-7 >= 'AUC p-value' > 0. Contains 60 panels of 16,069 total panels evaluated. : cU(aA aG aJ Al AP As aV aX aZ BA Bb bJ bM Bn bO bQ bR bU cC cD cE cJ cL cN cS CX Dc dE dH Di dK Fr) Cx(aA aX cG cS Cu) Lv(Ji Jp Mi Mz) cS(aA aL Ax bA) On(Mm Of Pb) aA(aX cJ) AwAx CucJ DebA DkdK QdJj aXbG cGcX Constrained panels with 2 analytes, where 1.0E-6 >= 'AUC p-value' > 1.0E-7. Contains 48 panels of 16,069 total panels evaluated. : Lv(aA Hx Im Is Jj Jl Jq Lw Ml Mp Nd Nv Nw Om On Oz Qd) Jp(Ji Lw Mi Mp Nn On) Cx(aP Aw dF Fr) Jj(Ij Jl On Pg) On(Ml Nj Nm) aP(cB dG dH) Di(cJ cS) aX(Cq Dc) cU(aC cB) ApaL CucX FrcJ aAaG bMcS Constrained panels with 2 analytes, where 1.0E-5 >= 'AUC p-value' > 1.0E-6. Contains 107 panels of 16,069 total panels evaluated. : Lv(Et Hv Iq Ir Jg Jk Jt Ly Mm Nn No Nq Nt Ok Pg Po Qa) Jp(Im Is Jj Ma Mm Mz Nq Nt Oe Pc Pg Qd) aX(aL aO Ax bA Cp Cu cX Dd dF Di) Cx(aJ BA cJ Cw Dc Di fR) aA(Aw bC bZ cB cG cX DE) Mz(Jj Ml Mp Nj Nn Nq Oe) Jj(Is Jk Nv Om Po) On(My Nn Ns Og Oy) aL(bC bW De dK) aP(bO cJ cX Di) Cu(aG cU dE) Qd(Ml Nj Oz) bA(bW cX Di) dK(Ax bG dF) Aw(Bn bO) Is(Iu Ml) Jr(Mp Nn) Oz(Jl Pg) aI(aJ cS) DccJ DicG PfPg aZbQ bGcS Constrained panels with 2 analytes, where 1.0E-4 >= 'AUC p-value' > 1.0E-5. Contains 227 panels of 16,069 total panels evaluated. : aZ(aA aI aO aP Aw bO bZ cS Cu De dF Di dK Fr) Mz(Im Iu Jg Jl Lw Ma Mg Mm Nf Nt On Pc Pg) Jj(Et Il Im Jq Lh Lx Mn Nt Nw Ny Pe Qa Qc) Cu(Ad An As bJ Bn Bo Cq cS Cw dB Dc dK) Lv(Fr Il Iu Ma Nb Nj Nk Nl Nr Oh Pa Pc) Jp(aA Fr Ir Iu Jl Jq Jt Mg Nj Nr Oh Ok) aJ(aG aL Aw aX bO cB cG cJ cX Di) Nj(Im Is Jl Lx Nv Nw Om Pg Po) Oe(Is Jl Jr Lx Nt Nv Nw On Po) bA(aG aI Ap bC bJ bO cT dE dK) Di(aA aG aI AL Ba bC Dc) On(Hu Im Lw Ma Ng Oi Pc Qd) cG(aG As bM Bn bO cE dE dH) Ml(Ji Jl Nt Nw Om Po Qa) aX(aI aP Bg bO cJ fR) Ba(aI aL bO cJ cX) Qd(Jg Lw Mm Nn Pc) aA(bO kG Ma Mp Nn) cS(bO cX dD Dk Fr) dE(aI aL Cp Dc dF) Ji(Il Jl Nm Pg) Jr(Im Ma Nq Nu) mF(mP nN nR oQ) Aw(Af As aV) Cx(Bb Bn Cq) Dc(aV bO dK) Jl(Im Lw Og) Nw(Hv Ma Nk) Nn(Mi Pc) Mp(Lx Nu) Ng(Fr Om) Og(Jg Om) Pg(Lw Ok) aP(Bg De) cJ(Ax Bb) cX(dF fR) dK(Al dM) NyPb OzPe aIbC aLbE cBfR nRmW nUmU Constrained panels with 2 analytes, where 1.0E-3 >= 'AUC p-value' > 1.0E-4. Contains 410 panels of 16,069 total panels evaluated. : Jj(Fr Hv Hw Hx Ih Ii Ip Iq Ir Iv Jg Ji Jm Jn Jr Ma Mj Mv Mw My No Nq Nu Nx Qc) Cx(Af aG aI AL aO Ap aU aV aZ bB BC bO bW bZ Cp cY Dd DE dK) Oe(aA Et Fr Hx Ir Jg Ji Jn Mw Nb Nr Nu Ny Om Pe Pg Qa Qd) Lw(aA Hv Hx Im Is Mi Mj Nb Nn Nr Nt Nu Nv Nw Pe Po) aA(Al BG Co dC Jg Lx Mg Mm mP Nj nK Om Pg Po) aZ(aG aJ Al BA bC Bg bW cG Co cR cX Dc dE fR) Nj(Et Fr Hx Ij Jg Ji Jq Jr Mi Nt Ok Pe Qa) Im(Lh Lx Mp Nb Nk Nl Nn Nu Nv Nw Om Pg Qd) cX(aG aI aO bL bQ bZ cJ CW Dc dE Di dK) Mm(Hv Hx Ij Il Is Jq Jr Mj Nw Pe Pg Po) Ma(Hx Is Jl Jq Lx Nk Nv Pe Pg Po Qd) Mp(Hx Is Jl Jq Nr Nw Ok Om Pe Po Qd) bO(aG aM bL bZ cJ DE dF Di dK fR) Jr(Is Iu Jg Jk Mg Ml Mv Nr Pa Pc) Nn(Hx Is Jl Lx Nw Oi Om Pe Po) aG(Aw Bb bZ Cp Dc dE dF dK dM) Di(Ap As Bb bZ DE dK fR) Nu(Hx Jq Lh Mj Mn Nb Nq Nr) Jg(Hv Jq Lx Ng Nm Oi Pe Qa) Al(aI aL aU aV bB cG cY) Dc(Ap aU bC bW bZ dC fR) Fr(aV aX bC Is Mz Nk Qd) Ml(Hx Ij Jq Mi Ok Pe Pg) Nf(Ji Mi Nq Om On Pg Qa) aJ(aM bC BG bZ DE) bQ(As bJ bM cC dE dH dK) Mg(Is Jl Lv Nv Nw Qd) Ok(Is Jl Mz Nk Nm Qd) Pb(Hx Ji Nb Om Pe Qa) aI(aC Ax Bb cR dK dM) cJ(Ap BG bL DE) Lx(Nb Nq Oh Pa Pe) cB(aX bS bV cS dM) Nw(Iu Jt Nt Pc) Om(Iu Nk Of Oh) bC(aO Bb bM fR) bZ(As Dd dE dK) cG(bJ cC cD dK) mF(ml mT nM oP) Et(Hv Il Nk) Nq(Jq Ng Qd) Is(Jl Mh Pc) Og(Hx Ij Mw) aL(aC bJ cR) bA(aC Bg bM) dE(aO Aw Ba) Ax(aU De) Mz(Jt Oh) Hv(Jq Nm) Qd(Jl Lj) Ji(Hr Nk) Pg(Jt Of) dK(Bc bL) nK(kG nR) AsdF BaaV BgcS BnCw NtLy MdOn MwOy JkJq NvPc PePf aXcZ bGbW mWkG Constrained panels with 2 analytes, where 1.0E-2 >= 'AUC p-value' > 1.0E-3. Contains 501 panels of 16,069 total panels evaluated. : Im(Et Hv Hx Ij Il Ir Iu Jg Jk Jq Jt Ma Mj Mk Mn Mr Mu Mv My No Nq Nr Nt Oe Oh Oz Pa Pc Pe Po Qa Qe) Ma(Et Hv Il Ir Iu Iv Jg Ji Jk Jt Lh Mi Mp Mr Nb Nj Nl No Nr Nt Oe Ok Om Pa Qa) Oe(Hv Ii Ij Il Ip Iq Iu Iv Jk Jq Js Lh Mj Mm Mn Mr Mt Mv My Nm No Nq Nx Pa) Ok(Fr Hr Hv Hw Il Iu Jq Lw Md Mg Mm Na Nf Ni Nn Nq Of Pb Pc) Mp(Et Hq Hv Ij Il Ir Jg Ji Jj Jk Jt Md Nb Nj Nt Oh Pa Qa) cX(aL aM Ap BB BC bO bV bW cB Cp Cq cR cT dC De dM) Nj(Hv Iq Ir Jk Jt Lh Mj Mu My Nd Nn No Nq Nr Nu Ny) Pc(aA Et Fr Hx Ij Ir Ji Jl Jq Lx Nt Om Pe Pg Po Qa) Jg(Hu Ir Iu Iv Jt Mj My Nk Nl Nr Ns Nt Of Oh Oy) Jj(Iu Js Jt Li Mg Mr Mt Mu Nb Nk Nm Nn Nr Pa Qb) dE(aM Ax Bb BG cB cC cO Cq Cw dC Dd De dK dM) Ml(aA Hv Ir Iv Jn Js Jt Lh Li Mj Nb No Nr Nx) Ji(Fr Hv Hw Ij In Iu Jq Lw Md Mm Mz Nn Ny Om) bW(aG Al aM Ax Bg bM bO bP cB cF cR cT Di) Nn(Et Fr Ij Ir Jt Mr Nb Nr Nt Pa Pg Qa) Al(aG aK aO bL bM bO bQ bZ cB De dF) Mm(Ir Iv Jt Me Mi Mr Nr Nt Om Pa Qa) dK(Aw aX aY Ba BB Bg bM cB cJ cR) Mg(Et Ir Jq Lx Ng No Nt Pg Po Qa) Bb(aJ aV bB BG bO bZ dC fR) Nu(aA Hv Il Iu Mr Nk Nl Oh Pa) Jt(Fr Hr Il Lx Na Nf Nt Pb Po) Nq(Hv Ir Iv Lw Nk Nr Pe Qa) Oh(Hx Ij Jk Jr Ny Pe Po Qa) aM(aG aO bL bZ cJ cO Cx dB) As(Ax bC cO Cp Cw Dc De) Jq(Il Iu Iv Mv Nk Nr Pa) bM(aJ bB bO cJ Cq cT dN) cB(Ax bC bH bL cO Cx dI) Lw(Et Fr Il Ir Jk Mr) Ax(aG Ap aV Cs cY) Iu(Et Hx Ij Lx Mn) Jk(aA Iv Ng Nm Og) bO(Ap bC Bg Dd dM) cJ(aO aZ bH bV dM) Dc(Af aV Bn bZ) Mw(My Ng Of Pb) bG(aG aZ cR dC) Ba(bC bZ Dc) Cp(bL Bn Bo) Cw(Ad An bJ) Mv(Hv Og Pa) Nl(Et Fr Om) Ij(Nf Pa Qa) Il(aA Jr Nm) Oz(Mr Nr Pa) aL(aZ bH dM) aV(Ap Dd Dk) aX(bB cG dH) dC(bV dB dN) mZ(ml nM nN) nI(aA kG nR) Bg(Ap bV) Cq(Bn dB) Nk(Ip Nm) Qa(Hw In) Jr(Mn Mr) aC(dD dF) aU(Di dM) bC(aG cR) fR(Ch Co) BoDd CxDk MtNf HqPg HrOn HxIv bZcE cFcO nRnC mFmY

Figure 29 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.5E1 | 1.3E2 | 8.5E1 | 1.4E2 | 5.7E1 | 9.8E1 | 7.0E0 | 2.1E1 | 4.0E2 | 4.8E2 | 228 | 44 | 228 | 44 | 0.70 |
| Ad | ug/mL | 4.7E-2 | 8.1E-2 | 7.1E-2 | 3.8E-1 | 8.9E-2 | 1.5E0 | 6.8E-4 | 4.3E-3 | 5.4E-1 | 8.5E0 | 112 | 30 | 112 | 30 | 0.63 |
| Af | ng/mL | 1.3E0 | 6.0E-1 | 1.1E1 | 4.4E0 | 5.3E1 | 7.0E0 | 1.7E-3 | 1.7E-3 | 5.3E2 | 2.3E1 | 112 | 30 | 112 | 30 | 0.43 |
| Aj | ug/mL | 1.4E0 | 2.9E-1 | 2.5E0 | 1.4E0 | 2.5E0 | 2.2E0 | 1.5E-3 | 2.1E-3 | 6.1E0 | 6.1E0 | 112 | 30 | 112 | 30 | 0.36 |
| Al | mg/mL | 8.7E-5 | 1.2E-4 | 2.5E-4 | 3.3E-4 | 4.2E-4 | 4.8E-4 | 4.6E-6 | 7.6E-6 | 1.8E-3 | 1.8E-3 | 112 | 30 | 112 | 30 | 0.56 |
| An | U/mL | 6.3E1 | 9.5E1 | 2.4E2 | 4.9E2 | 6.4E2 | 1.4E3 | 6.1E-1 | 6.4E-1 | 5.5E3 | 7.8E3 | 112 | 30 | 112 | 30 | 0.58 |
| Ao | pg/mL | 9.1E1 | 1.2E2 | 7.1E2 | 1.8E2 | 4.4E3 | 1.8E2 | 2.8E0 | 5.4E0 | 3.9E4 | 6.9E2 | 112 | 30 | 112 | 30 | 0.60 |
| Ap | ng/mL | 3.1E1 | 4.6E1 | 4.1E1 | 5.5E1 | 4.4E1 | 4.6E1 | 2.0E0 | 6.4E0 | 2.9E2 | 2.1E2 | 112 | 30 | 112 | 30 | 0.61 |
| Ar | ng/mL | 5.3E-1 | 2.3E0 | 2.6E0 | 6.8E0 | 6.5E0 | 1.2E1 | 4.1E-2 | 3.4E-2 | 5.1E1 | 5.0E1 | 112 | 30 | 112 | 30 | 0.72 |
| As | ng/mL | 8.7E-3 | 1.1E-2 | 1.3E-2 | 5.3E-2 | 1.8E-2 | 2.2E-1 | 1.7E-3 | 1.7E-3 | 1.3E-1 | 1.2E0 | 112 | 30 | 112 | 30 | 0.53 |
| Aw | pg/mL | 1.6E1 | 1.6E1 | 1.7E1 | 1.8E1 | 6.0E0 | 8.0E0 | 2.9E-2 | 1.1E1 | 4.2E1 | 5.1E1 | 112 | 30 | 112 | 30 | 0.53 |
| Ax | ng/mL | 1.8E0 | 8.0E0 | 1.6E1 | 1.1E2 | 7.5E1 | 2.1E2 | 1.3E-2 | 1.2E-2 | 7.7E2 | 8.5E2 | 112 | 30 | 112 | 30 | 0.69 |
| Ba | ng/mL | 7.8E1 | 2.7E2 | 5.7E2 | 8.8E2 | 1.5E3 | 1.7E3 | 1.1E0 | 3.1E0 | 8.1E3 | 8.1E3 | 112 | 30 | 112 | 30 | 0.64 |
| Bb | ng/mL | 3.9E0 | 7.9E0 | 6.3E0 | 1.1E1 | 7.9E0 | 9.4E0 | 4.1E-3 | 6.8E-1 | 4.9E1 | 3.7E1 | 112 | 30 | 112 | 30 | 0.67 |
| Bc | ng/mL | 3.3E1 | 6.7E1 | 1.2E2 | 1.7E2 | 2.3E2 | 2.8E2 | 4.9E-1 | 5.6E0 | 1.2E3 | 1.0E3 | 112 | 30 | 112 | 30 | 0.63 |
| Bg | ng/mL | 1.1E-1 | 1.8E-1 | 8.8E0 | 1.3E0 | 4.2E1 | 2.2E0 | 5.3E-4 | 1.9E-2 | 4.0E2 | 8.0E0 | 112 | 30 | 112 | 30 | 0.58 |
| Bn | ng/mL | 5.6E-2 | 5.6E-2 | 1.2E0 | 2.7E0 | 2.1E0 | 1.1E1 | 5.6E-2 | 5.6E-2 | 8.6E0 | 5.8E1 | 112 | 30 | 112 | 30 | 0.47 |
| Bo | ng/mL | 1.3E1 | 1.8E1 | 1.5E1 | 1.7E1 | 1.1E1 | 1.2E1 | 1.6E-2 | 1.6E-2 | 5.0E1 | 5.3E1 | 112 | 30 | 112 | 30 | 0.56 |
| Ch | uIU/mL | 1.2E0 | 9.6E-1 | 5.0E1 | 4.2E0 | 2.2E2 | 1.0E1 | 3.4E-3 | 3.4E-3 | 1.8E3 | 5.0E1 | 112 | 30 | 112 | 30 | 0.40 |
| Co | pg/mL | 4.6E1 | 6.1E1 | 2.8E2 | 1.7E2 | 1.6E3 | 3.9E2 | 1.5E-1 | 8.1E0 | 1.7E4 | 2.1E3 | 112 | 30 | 112 | 30 | 0.63 |
| Cp | ng/mL | 2.2E1 | 2.2E1 | 2.8E1 | 7.4E1 | 2.1E1 | 2.3E2 | 6.0E-1 | 2.5E0 | 1.3E2 | 1.3E3 | 112 | 30 | 112 | 30 | 0.54 |
| Cq | ng/mL | 3.0E-2 | 3.8E-2 | 1.2E-1 | 1.8E0 | 5.3E-1 | 8.9E0 | 8.0E-4 | 8.0E-4 | 5.1E0 | 4.9E1 | 112 | 30 | 112 | 30 | 0.57 |
| Cs | ng/mL | 6.6E1 | 2.4E2 | 3.5E2 | 1.4E3 | 1.1E3 | 3.4E3 | 1.0E0 | 8.3E-1 | 1.1E4 | 1.8E4 | 112 | 30 | 112 | 30 | 0.67 |
| Ct | ng/mL | 3.6E-1 | 2.1E-1 | 5.0E1 | 2.7E1 | 1.4E2 | 8.8E1 | 1.5E-2 | 1.1E-4 | 6.2E2 | 4.7E2 | 112 | 30 | 112 | 30 | 0.45 |
| Cu | ng/mL | 2.5E-1 | 3.1E-1 | 4.1E-1 | 3.6E0 | 5.6E-1 | 1.2E1 | 2.8E-2 | 4.6E-2 | 4.5E0 | 6.6E1 | 112 | 30 | 112 | 30 | 0.62 |
| Cv | ng/mL | 3.9E0 | 1.3E1 | 2.2E1 | 4.7E1 | 6.0E1 | 9.7E1 | 2.0E-2 | 2.4E-2 | 5.3E2 | 4.7E2 | 112 | 30 | 112 | 30 | 0.59 |
| Cw | mIU/mL | 3.0E-2 | 4.5E-2 | 4.1E-2 | 2.7E-1 | 3.6E-2 | 1.2E0 | 8.9E-4 | 4.1E-3 | 2.3E-1 | 6.8E0 | 112 | 30 | 112 | 30 | 0.61 |
| Cx | ng/mL | 1.5E0 | 1.7E-2 | 4.7E1 | 4.5E1 | 9.4E1 | 9.6E1 | 9.3E-5 | 9.3E-5 | 3.9E2 | 2.8E2 | 112 | 30 | 112 | 30 | 0.42 |
| Db | ug/mL | 7.2E0 | 7.8E0 | 8.6E0 | 8.5E0 | 8.1E0 | 6.3E0 | 4.5E-1 | 8.8E-1 | 5.9E1 | 3.1E1 | 112 | 30 | 112 | 30 | 0.52 |
| Dc | nmol/L | 1.9E-2 | 2.7E-2 | 5.1E-2 | 6.8E-2 | 1.5E-1 | 2.6E0 | 5.2E-6 | 1.3E-3 | 1.6E0 | 1.4E1 | 112 | 30 | 112 | 30 | 0.66 |
| Dd | ug/mL | 6.3E-2 | 2.4E-1 | 1.7E-1 | 3.8E-1 | 2.6E-1 | 6.8E-1 | 4.8E-4 | 3.4E-3 | 1.6E0 | 3.6E0 | 112 | 30 | 112 | 30 | 0.64 |
| De | ng/mL | 3.4E-3 | 3.4E-3 | 8.5E-2 | 9.0E-2 | 1.4E-1 | 2.5E-1 | 3.4E-3 | 3.4E-3 | 9.2E-1 | 1.1E0 | 112 | 30 | 112 | 30 | 0.43 |
| Dg | ng/mL | 3.4E1 | 4.2E1 | 4.5E1 | 5.7E1 | 3.8E1 | 4.2E1 | 7.1E-1 | 2.3E0 | 1.9E2 | 1.5E2 | 112 | 30 | 112 | 30 | 0.59 |
| Di | pg/mL | 2.0E0 | 2.7E0 | 2.4E0 | 2.8E0 | 2.2E0 | 1.9E0 | 1.8E-1 | 1.8E-1 | 1.3E1 | 9.0E0 | 112 | 30 | 112 | 30 | 0.58 |
| Dk | uIU/mL | 1.5E-2 | 1.9E-2 | 5.9E-2 | 1.1E-1 | 1.8E-1 | 2.3E-1 | 1.1E-4 | 1.1E-4 | 1.6E0 | 9.8E-1 | 112 | 30 | 112 | 30 | 0.58 |
| Dl | ng/mL | 1.9E2 | 3.3E2 | 2.9E2 | 4.1E2 | 2.6E2 | 3.7E2 | 5.5E0 | 1.8E1 | 1.2E3 | 1.6E3 | 112 | 30 | 112 | 30 | 0.60 |
| Dp | ng/ml | 2.4E0 | 1.8E0 | 5.4E0 | 5.5E0 | 8.3E0 | 1.2E1 | 3.7E-3 | 3.7E-3 | 4.6E1 | 5.6E1 | 92 | 22 | 92 | 22 | 0.42 |
| Dr | pg/ml | 1.7E1 | 4.9E1 | 4.0E1 | 1.2E3 | 5.5E1 | 3.3E3 | 7.5E-1 | 7.5E-1 | 2.5E2 | 1.0E4 | 48 | 10 | 48 | 10 | 0.70 |
| Du | pg/ml | 1.4E2 | 7.0E2 | 1.1E3 | 3.6E3 | 3.2E3 | 8.1E3 | 1.2E0 | 1.2E0 | 2.0E4 | 2.4E4 | 40 | 8 | 40 | 8 | 0.63 |
| Ef | ng/ml | 9.5E-2 | 1.9E-1 | 8.3E-1 | 9.4E-1 | 1.8E0 | 2.3E0 | 5.7E-4 | 5.7E-4 | 9.5E0 | 9.9E0 | 99 | 25 | 99 | 25 | 0.56 |
| Wm | % | 8.5E-2 | 1.1E0 | 1.1E1 | 8.6E1 | 7.8E1 | 2.6E2 | 5.4E-2 | 8.5E-2 | 7.7E2 | 1.0E3 | 105 | 26 | 105 | 26 | 0.59 |
| Ed | pg/ml | 1.1E0 | 2.5E1 | 2.6E1 | 9.1E1 | 3.8E1 | 1.4E2 | 5.2E-1 | 5.2E-1 | 1.9E2 | 5.0E2 | 92 | 22 | 92 | 22 | 0.65 |
| Yf | ng/mL | 1.4E1 | 2.4E1 | 4.6E1 | 1.0E2 | 9.9E1 | 1.5E2 | 2.9E-1 | 2.9E-1 | 5.9E2 | 3.5E2 | 42 | 7 | 42 | 7 | 0.61 |
| Tj | pg/mL | 3.7E-1 | 5.0E-1 | 4.6E1 | 3.8E1 | 2.5E2 | 8.2E1 | 3.7E-1 | 3.7E-1 | 2.3E3 | 3.1E2 | 96 | 24 | 96 | 24 | 0.59 |
| Po | ng/ml | 1.4E-1 | 4.5E0 | 8.1E0 | 2.4E1 | 2.6E1 | 4.7E1 | 8.0E-3 | 2.6E-2 | 2.7E2 | 2.2E2 | 214 | 55 | 214 | 55 | 0.66 |
| Ti | ug/mL | 2.9E0 | 7.2E0 | 4.3E0 | 8.1E0 | 3.7E0 | 5.6E0 | 1.2E-1 | 9.7E-1 | 1.4E1 | 1.8E1 | 59 | 10 | 59 | 10 | 0.71 |
| Em | ng/ml | 1.3E-2 | 2.6E-2 | 4.8E-2 | 2.3E-1 | 8.2E-2 | 5.0E-1 | 8.4E-4 | 8.4E-4 | 5.0E-1 | 1.9E0 | 58 | 15 | 58 | 15 | 0.57 |
| Et | ng/ml | 1.3E3 | 2.9E3 | 1.6E3 | 2.7E3 | 1.1E3 | 1.3E3 | 7.9E1 | 5.9E2 | 4.3E3 | 5.0E3 | 213 | 55 | 213 | 55 | 0.75 |
| Eq | pg/ml | 2.0E2 | 5.6E1 | 3.7E2 | 2.4E2 | 4.0E2 | 4.9E2 | 1.0E0 | 1.0E0 | 1.5E3 | 1.4E3 | 40 | 8 | 40 | 8 | 0.33 |
| Th | ug/mL | 1.3E0 | 1.0E0 | 1.9E0 | 1.9E0 | 1.6E0 | 2.1E0 | 1.2E-1 | 2.6E-3 | 7.5E0 | 5.9E0 | 59 | 10 | 59 | 10 | 0.43 |
| Fa | ng/ml | 3.8E1 | 9.5E1 | 1.0E2 | 2.5E2 | 3.9E2 | 5.3E2 | 2.6E-1 | 6.0E-1 | 3.7E3 | 2.5E3 | 89 | 22 | 89 | 22 | 0.72 |
| Ez | ng/ml | 3.8E0 | 5.3E0 | 1.4E1 | 2.3E1 | 2.5E1 | 4.6E1 | 1.3E-2 | 9.5E-2 | 1.6E2 | 2.0E2 | 92 | 22 | 92 | 22 | 0.59 |
| Fb | ng/ml | 2.6E1 | 2.7E1 | 2.2E1 | 2.7E1 | 1.2E1 | 9.1E0 | 6.6E-1 | 8.1E-1 | 4.3E1 | 4.1E1 | 90 | 22 | 90 | 22 | 0.59 |
| Ex | ng/ml | 7.5E-2 | 1.7E-1 | 1.7E-1 | 2.7E-1 | 2.6E-1 | 3.2E-1 | 3.5E-5 | 1.7E-4 | 1.5E0 | 1.2E0 | 68 | 20 | 68 | 20 | 0.66 |

Figure 30

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fc | pg/ml | 2.2E-1 | 3.3E0 | 1.3E1 | 4.8E1 | 6.2E1 | 1.1E2 | 2.2E-1 | 2.2E-1 | 3.9E2 | 3.1E2 | 41 | 8 | 41 | 8 | 0.66 |
| Fd | pg/ml | 2.3E1 | 5.5E2 | 3.4E2 | 7.2E3 | 6.2E2 | 1.1E4 | 4.5E-1 | 9.8E-1 | 2.7E3 | 2.5E4 | 41 | 8 | 41 | 8 | 0.73 |
| Fi | pg/ml | 2.5E-1 | 3.1E1 | 6.2E1 | 1.5E2 | 2.9E2 | 2.0E2 | 2.5E-1 | 2.5E-1 | 1.8E3 | 5.3E2 | 41 | 8 | 41 | 8 | 0.68 |
| Fn | ng/ml | 2.1E-1 | 9.5E-1 | 4.2E0 | 5.2E0 | 7.6E0 | 7.4E0 | 1.1E-14 | 1.1E-14 | 3.7E1 | 2.7E1 | 92 | 22 | 92 | 22 | 0.53 |
| Fp | ng/ml | 1.1E1 | 3.2E1 | 2.2E1 | 3.8E1 | 2.6E1 | 3.3E1 | 6.0E-3 | 1.2E0 | 1.3E2 | 1.3E2 | 217 | 55 | 217 | 55 | 0.68 |
| Fr | ng/ml | 3.1E4 | 9.2E4 | 1.2E5 | 2.2E5 | 1.9E5 | 2.5E5 | 1.9E2 | 1.8E3 | 8.4E5 | 8.4E5 | 220 | 56 | 220 | 56 | 0.69 |
| Fw | pg/ml | 8.5E-1 | 1.2E1 | 4.3E1 | 8.6E1 | 3.0E2 | 2.0E2 | 1.2E-1 | 1.2E-1 | 3.0E3 | 9.1E2 | 99 | 25 | 99 | 25 | 0.65 |
| Fy | ng/ml | 3.6E1 | 5.7E1 | 5.6E1 | 1.6E2 | 5.7E1 | 2.1E2 | 1.2E-1 | 1.5E0 | 2.8E2 | 6.5E2 | 92 | 20 | 92 | 20 | 0.62 |
| Gh | pg/ml | 2.0E0 | 2.3E0 | 2.2E1 | 1.0E1 | 5.9E1 | 1.7E1 | 2.9E-2 | 2.9E-2 | 3.2E2 | 4.6E1 | 41 | 8 | 41 | 8 | 0.52 |
| Gb | % | 4.3E1 | 5.7E1 | 4.4E1 | 9.7E1 | 3.1E1 | 9.5E1 | 2.2E0 | 2.5E1 | 1.4E2 | 3.0E2 | 41 | 8 | 41 | 8 | 0.70 |
| Gc | ng/ml | 8.2E1 | 2.0E2 | 1.6E2 | 2.9E2 | 2.2E2 | 2.2E2 | 6.4E0 | 6.7E1 | 1.2E3 | 6.7E2 | 48 | 10 | 48 | 10 | 0.73 |
| Gd | ng/ml | 3.6E1 | 2.5E1 | 3.6E1 | 3.0E1 | 1.7E1 | 2.3E1 | 3.0E0 | 7.6E0 | 6.9E1 | 8.0E1 | 56 | 11 | 56 | 11 | 0.37 |
| Gn | U/ml | 2.2E-1 | 2.8E-1 | 1.4E0 | 1.2E1 | 4.5E0 | 3.6E1 | 5.6E-3 | 2.7E-2 | 3.0E1 | 1.1E2 | 47 | 10 | 47 | 10 | 0.55 |
| Gl | pg/ml | 9.2E3 | 1.0E4 | 1.2E4 | 1.4E4 | 9.5E3 | 1.0E4 | 9.1E1 | 5.2E2 | 3.1E4 | 3.1E4 | 99 | 25 | 99 | 25 | 0.57 |
| Gp | U/ml | 1.2E0 | 9.8E-1 | 2.4E0 | 1.7E0 | 3.2E0 | 2.4E0 | 1.5E-2 | 1.5E-2 | 1.8E1 | 7.8E0 | 99 | 25 | 99 | 25 | 0.42 |
| Gz | ug/ml | 1.5E0 | 9.7E-1 | 5.8E0 | 4.5E0 | 5.9E0 | 6.0E0 | 4.2E-2 | 1.0E-1 | 2.5E1 | 1.9E1 | 62 | 18 | 62 | 18 | 0.49 |
| Ha | ng/ml | 1.9E0 | 4.1E0 | 7.5E0 | 1.7E1 | 1.7E1 | 3.3E1 | 1.7E-2 | 1.7E-2 | 1.0E2 | 1.0E2 | 90 | 22 | 90 | 22 | 0.61 |
| Nm | pg/ml | 1.4E4 | 2.5E4 | 3.4E4 | 7.2E4 | 8.7E4 | 1.4E5 | 1.0E-9 | 1.0E-9 | 9.6E5 | 8.2E5 | 217 | 55 | 217 | 55 | 0.61 |
| Nn | pg/ml | 1.5E2 | 4.3E2 | 1.8E3 | 1.1E4 | 8.2E3 | 4.5E4 | 1.0E-9 | 9.5E0 | 9.5E4 | 3.1E5 | 217 | 55 | 217 | 55 | 0.66 |
| No | pg/ml | 1.5E1 | 3.3E1 | 2.8E1 | 1.1E2 | 5.1E1 | 2.0E2 | 1.0E-9 | 4.0E0 | 5.6E2 | 9.1E2 | 217 | 55 | 217 | 55 | 0.71 |
| Nq | pg/ml | 1.4E0 | 7.5E0 | 2.5E1 | 4.9E1 | 8.2E1 | 1.2E2 | 1.0E-9 | 1.0E-9 | 6.7E2 | 6.3E2 | 217 | 55 | 217 | 55 | 0.61 |
| Nr | pg/ml | 1.3E0 | 6.1E0 | 2.0E1 | 7.4E1 | 8.2E1 | 2.1E2 | 1.0E-9 | 1.0E-9 | 9.8E2 | 1.4E3 | 217 | 55 | 217 | 55 | 0.66 |
| Ns | pg/ml | 1.0E-9 | 1.0E-9 | 1.2E1 | 6.5E-2 | 8.1E1 | 4.8E-1 | 1.0E-9 | 1.0E-9 | 1.1E3 | 3.6E0 | 217 | 55 | 217 | 55 | 0.47 |
| Nt | pg/ml | 1.1E2 | 1.4E2 | 1.4E2 | 2.3E2 | 1.0E2 | 2.8E2 | 1.5E1 | 4.5E1 | 8.8E2 | 1.7E3 | 217 | 55 | 217 | 55 | 0.63 |
| Nu | pg/ml | 2.4E1 | 4.8E1 | 5.7E1 | 8.3E1 | 8.8E1 | 9.8E1 | 1.0E-9 | 1.0E-9 | 6.3E2 | 3.7E2 | 217 | 55 | 217 | 55 | 0.60 |
| Lu | pg/ml | 1.0E4 | 1.0E4 | 1.8E4 | 1.1E4 | 4.9E4 | 9.4E3 | 9.4E2 | 5.2E2 | 5.6E5 | 5.7E4 | 217 | 55 | 217 | 55 | 0.48 |
| Lv | pg/ml | 1.0E-9 | 6.8E0 | 1.5E1 | 3.2E1 | 2.8E1 | 5.1E1 | 1.0E-9 | 1.0E-9 | 2.4E2 | 2.6E2 | 217 | 55 | 217 | 55 | 0.59 |
| Lw | pg/ml | 1.0E-9 | 1.0E-9 | 5.4E-1 | 4.8E0 | 5.8E0 | 2.5E1 | 1.0E-9 | 1.0E-9 | 8.0E1 | 1.8E2 | 217 | 55 | 217 | 55 | 0.55 |
| Lx | pg/ml | 1.0E-9 | 1.7E2 | 1.6E2 | 9.2E2 | 5.8E2 | 3.1E3 | 1.0E-9 | 1.0E-9 | 6.2E3 | 2.2E4 | 217 | 55 | 217 | 55 | 0.72 |
| Ly | pg/ml | 1.0E-9 | 1.0E-9 | 9.8E0 | 8.4E0 | 1.9E1 | 1.5E1 | 1.0E-9 | 1.0E-9 | 1.1E2 | 6.0E1 | 217 | 55 | 217 | 55 | 0.49 |
| Lz | pg/ml | 1.0E-9 | 1.0E-9 | 3.2E0 | 4.9E0 | 3.1E1 | 1.4E1 | 1.0E-9 | 1.0E-9 | 4.3E2 | 6.2E1 | 217 | 55 | 217 | 55 | 0.57 |
| Ma | pg/ml | 4.5E2 | 1.2E3 | 2.4E3 | 4.0E3 | 6.7E3 | 7.3E3 | 1.0E-9 | 2.6E1 | 6.5E4 | 3.6E4 | 217 | 55 | 217 | 55 | 0.65 |
| Mb | pg/ml | 2.5E1 | 2.8E1 | 3.3E1 | 3.2E1 | 1.9E1 | 1.5E1 | 9.2E0 | 4.1E0 | 2.1E2 | 7.1E1 | 217 | 55 | 217 | 55 | 0.50 |
| Mc | pg/ml | 1.0E-9 | 1.0E-9 | 8.8E-2 | 1.0E-9 | 9.3E-1 | 0.0E0 | 1.0E-9 | 1.0E-9 | 1.3E1 | 1.0E-9 | 217 | 55 | 217 | 55 | 0.49 |
| Md | pg/ml | 1.0E-9 | 1.0E-9 | 5.9E-1 | 7.5E-1 | 4.7E0 | 4.0E0 | 1.0E-9 | 1.0E-9 | 6.5E1 | 2.9E1 | 217 | 55 | 217 | 55 | 0.51 |
| Me | pg/ml | 3.0E1 | 3.5E1 | 3.1E1 | 3.4E1 | 2.7E1 | 2.6E1 | 1.0E-9 | 1.0E-9 | 3.2E2 | 1.8E2 | 217 | 55 | 217 | 55 | 0.56 |
| Mf | pg/ml | 1.0E-9 | 1.0E-9 | 8.4E-1 | 5.1E-1 | 4.8E0 | 1.5E0 | 1.0E-9 | 1.0E-9 | 5.6E1 | 9.1E0 | 217 | 55 | 217 | 55 | 0.51 |
| Mg | pg/ml | 1.3E0 | 1.8E0 | 7.1E0 | 1.1E1 | 1.3E1 | 2.6E1 | 1.0E-9 | 1.0E-9 | 9.2E1 | 1.5E2 | 217 | 55 | 217 | 55 | 0.54 |
| Mh | pg/ml | 1.0E-9 | 1.0E-9 | 9.1E-1 | 1.9E0 | 7.6E0 | 6.5E0 | 1.0E-9 | 1.0E-9 | 1.1E2 | 4.2E1 | 217 | 55 | 217 | 55 | 0.57 |
| Mi | pg/ml | 1.0E-9 | 1.0E-9 | 1.2E0 | 1.9E1 | 1.0E1 | 8.2E1 | 1.0E-9 | 1.0E-9 | 1.2E2 | 5.2E2 | 217 | 55 | 217 | 55 | 0.56 |
| Mj | pg/ml | 1.0E-9 | 1.0E-9 | 5.8E0 | 1.5E1 | 3.3E1 | 4.0E1 | 1.0E-9 | 1.0E-9 | 4.6E2 | 2.1E2 | 217 | 55 | 217 | 55 | 0.57 |
| Mk | pg/ml | 1.3E0 | 3.7E0 | 2.0E1 | 1.8E1 | 1.2E2 | 7.0E1 | 1.0E-9 | 1.0E-9 | 1.3E3 | 5.0E2 | 217 | 55 | 217 | 55 | 0.53 |
| Ml | pg/ml | 1.0E-9 | 1.0E-9 | 1.2E1 | 1.9E1 | 1.4E2 | 8.3E1 | 1.0E-9 | 1.0E-9 | 2.1E3 | 5.1E2 | 217 | 55 | 217 | 55 | 0.51 |
| Mm | pg/ml | 5.5E2 | 9.4E2 | 1.0E3 | 1.8E3 | 1.2E3 | 2.1E3 | 1.0E-9 | 5.2E1 | 6.3E3 | 1.0E4 | 217 | 55 | 217 | 55 | 0.63 |
| Mn | pg/ml | 5.6E0 | 1.1E1 | 1.2E1 | 1.3E1 | 3.0E1 | 8.9E0 | 1.0E-9 | 2.4E0 | 3.5E2 | 5.1E1 | 217 | 55 | 217 | 55 | 0.69 |
| Mp | pg/ml | 1.0E-9 | 6.8E0 | 1.2E1 | 8.1E1 | 4.7E1 | 3.3E2 | 1.0E-9 | 1.0E-9 | 6.3E2 | 2.4E3 | 217 | 55 | 217 | 55 | 0.63 |
| Mq | pg/ml | 1.0E-9 | 1.0E-9 | 2.4E0 | 6.1E0 | 1.5E1 | 1.9E1 | 1.0E-9 | 1.0E-9 | 1.8E2 | 1.0E2 | 217 | 55 | 217 | 55 | 0.55 |
| Mr | pg/ml | 1.0E-9 | 1.0E-9 | 2.0E1 | 1.9E2 | 1.0E2 | 6.0E2 | 1.0E-9 | 1.0E-9 | 1.4E3 | 3.4E3 | 217 | 55 | 217 | 55 | 0.59 |
| Ms | pg/ml | 3.6E2 | 2.5E2 | 4.8E2 | 3.4E2 | 5.4E2 | 3.3E2 | 1.0E-9 | 1.0E-9 | 3.3E3 | 1.5E3 | 217 | 55 | 217 | 55 | 0.43 |
| Mt | pg/ml | 3.1E-1 | 1.6E0 | 9.0E0 | 8.5E1 | 5.2E1 | 4.4E2 | 1.0E-9 | 1.0E-9 | 7.1E2 | 3.2E3 | 217 | 55 | 217 | 55 | 0.67 |
| Mu | pg/ml | 1.0E-9 | 1.0E-9 | 2.1E0 | 2.5E0 | 1.8E1 | 8.4E0 | 1.0E-9 | 1.0E-9 | 2.3E2 | 4.8E1 | 217 | 55 | 217 | 55 | 0.55 |
| Mv | pg/ml | 1.0E-9 | 1.0E-9 | 8.4E1 | 1.0E2 | 4.1E2 | 2.4E2 | 1.0E-9 | 1.0E-9 | 4.5E3 | 9.2E2 | 217 | 55 | 217 | 55 | 0.56 |
| Mw | pg/ml | 3.0E1 | 9.8E1 | 3.3E2 | 5.1E2 | 1.7E3 | 1.1E3 | 1.0E-9 | 1.0E-9 | 1.8E4 | 5.3E3 | 217 | 55 | 217 | 55 | 0.66 |
| Mx | pg/ml | 1.0E-9 | 1.0E-9 | 4.0E-1 | 9.7E-1 | 2.3E0 | 2.9E0 | 1.0E-9 | 1.0E-9 | 3.2E1 | 2.0E1 | 217 | 55 | 217 | 55 | 0.60 |
| My | pg/ml | 1.0E-9 | 5.8E0 | 4.7E2 | 1.5E2 | 3.1E3 | 3.8E2 | 1.0E-9 | 1.0E-9 | 3.9E4 | 1.9E3 | 217 | 55 | 217 | 55 | 0.58 |
| Mz | pg/ml | 1.0E1 | 3.0E1 | 2.3E1 | 1.1E2 | 5.2E1 | 3.1E2 | 1.0E-9 | 1.0E-9 | 5.5E2 | 1.9E3 | 217 | 55 | 217 | 55 | 0.74 |
| Na | pg/ml | 1.0E-9 | 1.0E-9 | 5.3E-1 | 1.4E0 | 1.7E0 | 5.9E0 | 1.0E-9 | 1.0E-9 | 9.6E0 | 4.2E1 | 217 | 55 | 217 | 55 | 0.50 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nb | pg/ml | 2.1E0 | 3.5E0 | 3.7E0 | 1.1E1 | 1.2E1 | 3.2E1 | 1.0E-9 | 1.0E-9 | 1.5E2 | 2.1E2 | 217 | 55 | 217 | 55 | 0.63 |
| Nc | pg/ml | 3.5E2 | 5.6E1 | 5.4E2 | 3.5E2 | 8.0E2 | 5.7E2 | 1.0E-9 | 1.0E-9 | 9.2E3 | 3.2E3 | 217 | 55 | 217 | 55 | 0.38 |
| Nd | pg/ml | 2.6E1 | 2.5E1 | 2.8E1 | 6.7E1 | 8.4E1 | 2.8E2 | 1.0E-9 | 1.0E-9 | 1.2E3 | 2.1E3 | 217 | 55 | 217 | 55 | 0.56 |
| Ne | pg/ml | 4.4E2 | 3.4E2 | 5.4E2 | 4.3E2 | 6.0E2 | 5.4E2 | 1.0E-9 | 1.0E-9 | 7.0E3 | 3.6E3 | 217 | 55 | 217 | 55 | 0.41 |
| Nf | pg/ml | 1.0E-9 | 1.0E-9 | 2.3E0 | 6.5E0 | 9.0E0 | 2.4E1 | 1.0E-9 | 1.0E-9 | 8.2E1 | 1.3E2 | 217 | 55 | 217 | 55 | 0.51 |
| Ng | pg/ml | 1.8E1 | 1.7E1 | 1.1E2 | 8.2E1 | 2.1E2 | 1.2E2 | 1.0E-9 | 1.0E-9 | 1.6E3 | 5.3E2 | 217 | 55 | 217 | 55 | 0.51 |
| Nh | pg/ml | 6.0E1 | 5.2E1 | 8.3E1 | 6.2E1 | 7.7E1 | 7.5E1 | 1.0E-9 | 4.1E0 | 5.6E2 | 5.1E2 | 217 | 55 | 217 | 55 | 0.39 |
| Ni | pg/ml | 4.5E0 | 1.0E-9 | 8.5E1 | 1.0E2 | 1.3E2 | 1.9E2 | 1.0E-9 | 1.0E-9 | 7.1E2 | 1.1E3 | 217 | 55 | 217 | 55 | 0.47 |
| Nj | pg/ml | 6.3E0 | 5.9E0 | 1.0E1 | 8.2E0 | 1.1E1 | 9.7E0 | 1.0E-9 | 1.0E-9 | 6.8E1 | 4.6E1 | 217 | 55 | 217 | 55 | 0.43 |
| Nk | pg/ml | 1.8E1 | 1.2E1 | 3.1E1 | 3.3E1 | 3.6E1 | 4.9E1 | 1.0E-9 | 1.0E-9 | 2.0E2 | 2.0E2 | 217 | 55 | 217 | 55 | 0.48 |
| Nl | pg/ml | 4.3E1 | 3.1E1 | 5.8E1 | 4.2E1 | 8.4E1 | 4.8E1 | 1.0E-9 | 1.0E-9 | 1.1E3 | 2.3E2 | 217 | 55 | 217 | 55 | 0.40 |
| Hl | pg/ml | 2.1E1 | 7.0E0 | 3.9E1 | 4.7E2 | 6.0E1 | 1.3E3 | 1.0E-9 | 1.0E-9 | 3.0E2 | 3.6E3 | 41 | 8 | 41 | 8 | 0.50 |
| Ho | pg/ml | 1.8E1 | 2.7E1 | 2.4E1 | 9.8E1 | 2.0E1 | 1.3E2 | 1.1E0 | 7.6E0 | 8.7E1 | 3.9E2 | 41 | 8 | 41 | 8 | 0.65 |
| Hp | ng/ml | 1.6E0 | 5.5E0 | 9.0E1 | 3.3E2 | 2.7E2 | 4.6E2 | 1.0E-9 | 8.8E-1 | 8.9E2 | 8.9E2 | 41 | 8 | 41 | 8 | 0.70 |
| Tz | pg/ml | 3.9E3 | 6.5E3 | 6.0E3 | 1.2E5 | 6.2E3 | 4.4E5 | 1.0E-9 | 6.8E2 | 3.2E4 | 2.1E6 | 93 | 22 | 93 | 22 | 0.62 |
| Ua | pg/ml | 3.1E3 | 5.6E3 | 1.5E4 | 1.3E4 | 2.9E4 | 2.2E4 | 1.0E-9 | 9.1E2 | 1.4E5 | 9.9E4 | 93 | 22 | 93 | 22 | 0.59 |
| Ub | pg/ml | 5.3E2 | 4.0E2 | 8.5E2 | 6.2E2 | 1.2E3 | 8.6E2 | 1.0E-9 | 2.3E0 | 9.8E3 | 4.1E3 | 93 | 22 | 93 | 22 | 0.41 |
| Ue | pg/ml | 3.1E1 | 2.3E1 | 3.7E1 | 3.7E1 | 3.3E1 | 3.8E1 | 9.8E-2 | 5.9E0 | 2.7E2 | 1.4E2 | 93 | 22 | 93 | 22 | 0.44 |
| Uc | pg/ml | 7.6E2 | 8.7E2 | 1.3E3 | 4.6E3 | 1.5E3 | 1.2E4 | 1.0E-9 | 5.5E1 | 8.3E3 | 5.7E4 | 93 | 22 | 93 | 22 | 0.59 |
| Ud | pg/ml | 1.0E-9 | 1.0E-9 | 4.2E0 | 2.4E0 | 4.0E1 | 1.1E1 | 1.0E-9 | 1.0E-9 | 3.9E2 | 5.3E1 | 93 | 22 | 93 | 22 | 0.52 |
| Hq | pg/ml | 1.2E0 | 1.6E0 | 2.4E2 | 6.8E1 | 2.4E3 | 3.8E2 | 1.0E-9 | 1.0E-9 | 2.8E4 | 2.8E3 | 215 | 55 | 215 | 55 | 0.54 |
| Hr | pg/ml | 8.5E1 | 9.0E1 | 5.7E2 | 5.1E2 | 1.1E3 | 1.4E3 | 1.0E-9 | 1.0E-9 | 8.4E3 | 8.9E3 | 215 | 55 | 215 | 55 | 0.47 |
| Hu | pg/ml | 1.2E1 | 5.3E1 | 7.0E3 | 6.5E2 | 5.0E4 | 1.5E3 | 1.0E-9 | 1.0E-9 | 6.3E5 | 6.5E3 | 215 | 55 | 215 | 55 | 0.56 |
| Hv | pg/ml | 1.5E0 | 1.3E0 | 2.5E0 | 2.3E1 | 5.6E0 | 1.2E2 | 1.0E-9 | 1.0E-9 | 6.9E1 | 8.9E2 | 215 | 55 | 215 | 55 | 0.52 |
| Hw | pg/ml | 5.5E0 | 5.7E0 | 1.6E1 | 2.0E2 | 5.4E1 | 1.3E3 | 1.0E-9 | 5.1E-1 | 6.4E2 | 9.4E3 | 215 | 55 | 215 | 55 | 0.51 |
| Hx | pg/ml | 8.8E0 | 1.4E1 | 6.9E1 | 6.8E1 | 6.3E2 | 2.0E2 | 1.0E-9 | 1.0E-9 | 9.3E3 | 1.3E3 | 215 | 55 | 215 | 55 | 0.59 |
| Ib | ng/ml | 4.0E-2 | 2.8E-2 | 1.3E0 | 2.7E0 | 5.3E0 | 1.2E1 | 1.0E-9 | 1.0E-9 | 3.6E1 | 5.6E1 | 90 | 22 | 90 | 22 | 0.49 |
| Ic | U/ml | 2.2E2 | 2.2E2 | 4.1E2 | 3.2E3 | 1.1E3 | 1.4E4 | 2.4E0 | 2.5E1 | 8.6E3 | 6.5E4 | 90 | 22 | 90 | 22 | 0.60 |
| Id | U/ml | 5.4E-1 | 1.4E0 | 1.0E0 | 2.2E1 | 1.5E0 | 9.2E1 | 1.0E-9 | 2.7E-1 | 1.0E1 | 4.3E2 | 90 | 22 | 90 | 22 | 0.74 |
| Tt | pg/ml | 1.7E2 | 1.8E2 | 1.7E2 | 1.9E2 | 5.5E1 | 7.2E1 | 4.3E1 | 1.1E2 | 3.6E2 | 4.4E2 | 85 | 19 | 85 | 19 | 0.55 |
| To | pg/ml | 1.6E0 | 1.8E0 | 2.0E0 | 2.3E0 | 2.1E0 | 2.8E0 | 1.0E-9 | 1.0E-9 | 9.9E0 | 1.2E1 | 90 | 20 | 90 | 20 | 0.52 |
| Tr | pg/ml | 3.3E0 | 5.2E0 | 9.1E0 | 1.3E1 | 3.3E1 | 1.9E1 | 1.0E-9 | 3.9E-1 | 3.1E2 | 7.6E1 | 88 | 19 | 88 | 19 | 0.62 |
| Tn | pg/ml | 3.3E1 | 5.4E1 | 1.1E2 | 2.3E2 | 3.2E2 | 5.1E2 | 2.4E0 | 1.9E1 | 2.0E3 | 2.3E3 | 90 | 20 | 90 | 20 | 0.67 |
| Tv | ng/ml | 1.2E1 | 1.1E1 | 1.7E1 | 4.4E2 | 1.7E1 | 1.6E3 | 1.0E-9 | 1.0E-9 | 7.5E1 | 7.1E3 | 90 | 20 | 90 | 20 | 0.52 |
| Ih | ng/ml | 6.4E1 | 2.1E2 | 2.0E2 | 5.4E2 | 3.3E2 | 7.4E2 | 1.0E-9 | 1.0E-9 | 2.1E3 | 3.6E3 | 216 | 55 | 216 | 55 | 0.66 |
| Ii | ng/ml | 7.8E1 | 1.3E2 | 2.1E2 | 3.7E2 | 4.7E2 | 7.9E2 | 7.3E-1 | 2.3E0 | 5.2E3 | 4.5E3 | 216 | 55 | 216 | 55 | 0.62 |
| Ij | ng/ml | 7.7E1 | 1.4E2 | 1.9E2 | 7.0E2 | 6.5E2 | 3.3E3 | 2.8E0 | 2.5E1 | 6.4E3 | 2.4E4 | 214 | 54 | 214 | 54 | 0.72 |
| Ik | ng/ml | 1.1E1 | 1.4E1 | 1.9E3 | 2.1E2 | 1.4E4 | 4.1E2 | 5.9E-1 | 2.1E0 | 1.2E5 | 1.5E3 | 214 | 54 | 214 | 54 | 0.54 |
| Il | ng/ml | 3.6E2 | 5.5E2 | 1.2E3 | 2.0E3 | 2.7E3 | 3.6E3 | 1.0E-9 | 1.0E-9 | 1.2E4 | 1.2E4 | 212 | 54 | 212 | 54 | 0.58 |
| Im | ng/ml | 2.0E2 | 7.0E2 | 3.6E2 | 1.1E3 | 5.8E2 | 1.4E3 | 1.4E1 | 4.7E1 | 6.0E3 | 6.2E3 | 213 | 55 | 213 | 55 | 0.76 |
| In | ng/ml | 3.4E0 | 2.4E0 | 1.7E1 | 1.1E2 | 7.9E1 | 6.1E2 | 1.0E-9 | 1.0E-9 | 1.1E3 | 4.5E3 | 216 | 55 | 216 | 55 | 0.49 |
| Hb | ng/ml | 2.1E1 | 4.3E1 | 3.2E1 | 5.7E1 | 3.3E1 | 5.0E1 | 4.8E-1 | 6.7E0 | 2.0E2 | 1.9E2 | 93 | 23 | 93 | 23 | 0.69 |
| Hc | pg/ml | 7.3E2 | 5.0E2 | 3.6E3 | 1.3E3 | 1.2E4 | 2.8E3 | 1.0E-9 | 1.0E-9 | 1.0E5 | 1.4E4 | 93 | 23 | 93 | 23 | 0.42 |
| Hf | ng/ml | 2.0E2 | 2.6E2 | 4.4E2 | 3.0E2 | 6.2E2 | 2.9E2 | 1.0E-9 | 1.0E-9 | 3.2E3 | 9.9E2 | 93 | 23 | 93 | 23 | 0.47 |
| Io | ng/ml | 1.1E4 | 1.9E4 | 2.1E4 | 2.2E4 | 5.5E4 | 2.2E4 | 1.0E-9 | 6.2E2 | 7.1E5 | 1.1E5 | 216 | 55 | 216 | 55 | 0.61 |
| Ip | ng/ml | 9.3E0 | 3.0E1 | 2.1E1 | 3.2E1 | 2.8E1 | 2.3E1 | 1.0E-9 | 1.6E-2 | 2.3E2 | 8.3E1 | 216 | 55 | 216 | 55 | 0.67 |
| Iq | ug/ml | 1.1E-1 | 1.9E-1 | 7.2E-1 | 6.0E0 | 2.8E0 | 3.0E1 | 1.0E-9 | 1.0E-9 | 3.4E1 | 2.2E2 | 216 | 55 | 216 | 55 | 0.60 |
| Ir | ug/ml | 3.6E-1 | 1.3E0 | 2.0E0 | 1.7E1 | 1.1E1 | 5.6E1 | 1.0E-9 | 1.0E-9 | 1.6E2 | 3.7E2 | 215 | 55 | 215 | 55 | 0.69 |
| Is | ng/ml | 1.7E0 | 7.6E0 | 6.2E0 | 2.7E1 | 1.2E1 | 4.8E1 | 1.0E-9 | 3.3E-2 | 8.8E1 | 2.6E2 | 216 | 55 | 216 | 55 | 0.68 |
| It | ng/ml | 1.8E0 | 5.1E0 | 1.3E1 | 3.3E1 | 6.5E1 | 1.2E2 | 1.0E-9 | 1.0E-9 | 8.3E2 | 6.8E2 | 216 | 55 | 216 | 55 | 0.69 |
| Iu | ng/ml | 1.8E2 | 1.9E2 | 1.1E3 | 2.3E3 | 3.6E3 | 5.7E3 | 1.0E-9 | 1.0E-9 | 2.9E4 | 2.4E4 | 216 | 55 | 216 | 55 | 0.55 |
| Iv | ng/ml | 1.3E1 | 2.3E1 | 3.6E1 | 2.8E2 | 8.0E1 | 8.6E2 | 1.0E-9 | 1.0E-9 | 7.7E2 | 3.8E3 | 215 | 55 | 215 | 55 | 0.63 |
| Iz | ng/ml | 1.2E2 | 1.9E2 | 3.6E2 | 2.7E2 | 7.6E2 | 2.8E2 | 1.5E0 | 4.9E0 | 6.1E3 | 1.0E3 | 93 | 23 | 93 | 23 | 0.55 |
| Yg | pg/ml | 2.4E2 | 1.4E2 | 1.7E3 | 1.5E3 | 7.7E3 | 1.4E3 | 1.0E-9 | 1.3E2 | 5.0E4 | 3.9E3 | 41 | 7 | 41 | 7 | 0.71 |
| Yh | pg/ml | 2.1E2 | 3.6E2 | 3.6E2 | 6.1E2 | 4.8E2 | 6.3E2 | 1.0E-9 | 1.0E-9 | 2.1E3 | 1.4E3 | 41 | 7 | 41 | 7 | 0.59 |
| Yi | pg/ml | 2.4E2 | 1.1E3 | 4.7E2 | 5.9E3 | 5.1E2 | 9.6E3 | 1.0E-9 | 2.4E2 | 2.0E3 | 2.6E4 | 41 | 7 | 41 | 7 | 0.83 |
| Yk | U/ml | 1.0E-9 | 1.0E-9 | 1.8E-1 | 3.7E-1 | 5.8E-1 | 6.4E-1 | 1.0E-9 | 1.0E-9 | 3.0E0 | 1.4E0 | 41 | 7 | 41 | 7 | 0.56 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yj | pg/ml | 1.5E2 | 8.6E1 | 3.3E2 | 1.3E2 | 5.6E2 | 1.1E2 | 1.0E-9 | 5.9E1 | 3.2E3 | 3.7E2 | 41 | 7 | 41 | 7 | 0.38 |
| Yd | ng/ml | 2.1E-1 | 1.3E-1 | 4.0E-1 | 4.1E-1 | 5.2E-1 | 6.5E-1 | 6.6E-3 | 1.7E-2 | 2.3E0 | 1.9E0 | 42 | 8 | 42 | 8 | 0.46 |
| Wb | pg/ml | 2.7E4 | 3.4E4 | 3.4E4 | 1.2E5 | 1.9E4 | 2.1E5 | 6.3E3 | 1.4E4 | 8.4E4 | 6.4E5 | 42 | 8 | 42 | 8 | 0.66 |
| Vz | pg/ml | 3.7E0 | 5.5E0 | 4.7E0 | 6.4E0 | 4.3E0 | 7.1E0 | 1.0E-9 | 7.6E-2 | 2.1E1 | 2.2E1 | 42 | 8 | 42 | 8 | 0.57 |
| Si | ng/ml | 1.0E0 | 2.3E0 | 1.8E0 | 3.0E0 | 2.6E0 | 2.1E0 | 8.6E-3 | 5.6E-1 | 1.0E1 | 6.0E0 | 41 | 8 | 41 | 8 | 0.73 |
| Sf | mIU/mL | 2.0E1 | 2.0E1 | 5.6E1 | 2.7E1 | 1.2E2 | 2.6E1 | 7.8E-1 | 6.7E0 | 7.2E2 | 8.3E1 | 41 | 8 | 41 | 8 | 0.52 |
| Sh | mIU/mL | 1.8E1 | 1.0E1 | 5.1E1 | 1.0E1 | 1.0E2 | 5.1E0 | 7.8E-2 | 4.2E0 | 5.7E2 | 2.1E1 | 41 | 8 | 41 | 8 | 0.36 |
| Sj | ng/ml | 4.4E-1 | 4.4E-1 | 4.3E-1 | 4.5E-1 | 8.3E-2 | 1.2E-1 | 2.5E-1 | 3.4E-1 | 6.1E-1 | 7.2E-1 | 41 | 8 | 41 | 8 | 0.52 |
| Rc | pg/ml | 6.8E3 | 7.6E3 | 7.6E3 | 7.6E3 | 5.5E3 | 3.6E3 | 5.5E2 | 2.1E3 | 2.7E4 | 1.5E4 | 92 | 22 | 92 | 22 | 0.55 |
| Rb | pg/ml | 9.3E-1 | 7.5E-1 | 2.8E0 | 4.2E0 | 4.2E0 | 1.2E1 | 1.0E-9 | 1.0E-9 | 2.0E1 | 5.6E1 | 92 | 22 | 92 | 22 | 0.51 |
| Zq | 2.6ng/ml | 2.6E2 | 4.2E2 | 2.6E2 | 4.9E2 | 1.6E2 | 2.2E2 | 1.7E1 | 3.0E2 | 5.9E2 | 9.7E2 | 41 | 7 | 41 | 7 | 0.80 |
| Zw | 2.5ng/ml | 6.5E0 | 5.0E0 | 9.2E0 | 2.1E1 | 1.1E1 | 2.7E1 | 2.4E-1 | 7.7E-1 | 5.9E1 | 6.3E1 | 42 | 8 | 42 | 8 | 0.56 |
| Zx | 2.3mU/ml | 1.3E-1 | 1.6E-1 | 3.3E-1 | 2.2E-1 | 5.9E-1 | 1.9E-1 | 3.2E-2 | 7.7E-2 | 2.9E0 | 6.7E-1 | 42 | 8 | 42 | 8 | 0.58 |
| Pz | ng/ml | 3.3E3 | 1.0E4 | 5.7E3 | 7.1E3 | 6.5E3 | 4.7E3 | 1.6E1 | 3.3E2 | 7.0E4 | 2.5E4 | 212 | 55 | 212 | 55 | 0.61 |
| Qa | ng/ml | 3.5E3 | 9.0E3 | 6.4E3 | 1.6E4 | 7.4E3 | 3.0E4 | 1.5E2 | 6.8E2 | 4.2E4 | 2.2E5 | 212 | 55 | 212 | 55 | 0.68 |
| Qb | ng/ml | 1.1E2 | 2.1E2 | 2.0E2 | 4.0E2 | 2.9E2 | 6.0E2 | 7.9E-1 | 1.8E1 | 2.8E3 | 4.1E3 | 212 | 55 | 212 | 55 | 0.65 |
| Qc | ng/ml | 2.0E2 | 4.8E2 | 4.1E2 | 6.9E2 | 5.2E2 | 7.7E2 | 1.0E0 | 1.0E-9 | 3.8E3 | 4.3E3 | 212 | 55 | 212 | 55 | 0.63 |
| Qd | ng/ml | 9.3E3 | 2.0E4 | 2.6E4 | 5.4E4 | 1.4E5 | 8.2E4 | 2.4E2 | 1.7E3 | 2.0E6 | 4.3E5 | 212 | 55 | 212 | 55 | 0.70 |
| Qe | ng/ml | 8.1E2 | 2.3E3 | 2.0E3 | 3.2E3 | 6.9E3 | 3.3E3 | 7.6E0 | 8.8E0 | 9.7E4 | 1.8E4 | 212 | 55 | 212 | 55 | 0.70 |
| Jd | ng/ml | 8.6E-1 | 1.4E0 | 4.3E0 | 3.6E0 | 1.7E1 | 5.5E0 | 1.0E-9 | 1.0E-9 | 1.2E2 | 2.1E1 | 92 | 22 | 92 | 22 | 0.62 |
| Je | ng/ml | 1.0E-9 | 5.0E-1 | 2.0E0 | 1.9E0 | 5.7E0 | 2.9E0 | 1.0E-9 | 1.0E-9 | 4.6E1 | 1.1E1 | 92 | 22 | 92 | 22 | 0.58 |
| Jf | ng/ml | 1.0E-9 | 1.0E-9 | 1.4E0 | 8.3E-1 | 2.5E0 | 1.3E0 | 1.0E-9 | 1.0E-9 | 1.2E1 | 3.9E0 | 92 | 22 | 92 | 22 | 0.48 |
| Jg | ng/ml | 4.8E2 | 1.0E3 | 7.9E2 | 1.4E3 | 1.0E3 | 1.3E3 | 5.8E0 | 5.4E1 | 1.0E4 | 7.1E3 | 215 | 55 | 215 | 55 | 0.67 |
| Jh | ng/ml | 2.9E0 | 7.5E0 | 2.5E1 | 3.7E1 | 1.0E2 | 8.5E1 | 1.0E-9 | 1.0E-9 | 1.2E3 | 4.9E2 | 215 | 55 | 215 | 55 | 0.61 |
| Ji | ng/ml | 5.4E1 | 1.3E2 | 7.7E1 | 2.1E2 | 7.9E1 | 2.2E2 | 1.1E0 | 2.0E1 | 5.3E2 | 1.3E3 | 215 | 55 | 215 | 55 | 0.76 |
| Sr | pg/mL | 3.4E2 | 1.2E3 | 7.9E2 | 2.6E3 | 1.1E3 | 4.4E3 | 1.0E-9 | 9.2E1 | 4.8E3 | 2.1E4 | 91 | 22 | 91 | 22 | 0.72 |
| Ss | pg/mL | 1.0E5 | 6.8E4 | 1.5E5 | 1.2E5 | 1.9E5 | 1.4E5 | 2.7E3 | 1.4E4 | 1.3E6 | 5.7E5 | 91 | 22 | 91 | 22 | 0.46 |
| St | pg/mL | 2.4E7 | 8.2E7 | 6.2E7 | 1.6E8 | 1.4E8 | 3.5E8 | 1.0E-9 | 2.3E6 | 1.2E9 | 1.7E9 | 90 | 22 | 90 | 22 | 0.68 |
| Wc | ng/ml | 1.0E-9 | 2.1E-3 | 4.2E-2 | 3.2E-1 | 7.5E-2 | 6.3E-1 | 1.0E-9 | 1.0E-9 | 3.0E-1 | 1.8E0 | 42 | 8 | 42 | 8 | 0.57 |
| Wd | ng/ml | 9.5E0 | 1.6E1 | 2.2E1 | 1.1E2 | 4.7E1 | 1.8E2 | 1.0E0 | 3.5E0 | 2.9E2 | 4.1E2 | 42 | 8 | 42 | 8 | 0.67 |
| We | ng/ml | 3.0E-1 | 5.3E-1 | 9.6E-1 | 3.4E0 | 1.9E0 | 7.9E0 | 1.0E-9 | 1.5E-1 | 5.5E0 | 2.3E1 | 42 | 8 | 42 | 8 | 0.61 |
| Wg | ng/ml | 1.0E-9 | 1.0E-9 | 1.0E-9 | 6.7E-2 | 0.0E0 | 1.9E-1 | 1.0E-9 | 1.0E-9 | 1.0E-9 | 5.3E-1 | 42 | 8 | 42 | 8 | 0.56 |
| Wh | ng/ml | 1.0E-2 | 1.8E-2 | 3.2E-2 | 6.6E-2 | 7.1E-2 | 1.1E-1 | 1.0E-9 | 1.0E-9 | 3.5E-1 | 3.4E-1 | 42 | 8 | 42 | 8 | 0.62 |
| Wf | ng/ml | 1.0E-9 | 1.0E-9 | 1.2E-1 | 2.9E-1 | 2.3E-1 | 8.1E-1 | 1.0E-9 | 1.0E-9 | 1.2E0 | 2.3E0 | 42 | 8 | 42 | 8 | 0.39 |
| Ra | pg/ml | 1.0E-9 | 1.0E-9 | 4.1E-1 | 3.4E0 | 9.9E-1 | 1.4E1 | 1.0E-9 | 1.0E-9 | 3.8E0 | 6.4E1 | 92 | 22 | 92 | 22 | 0.54 |
| Qz | pg/ml | 9.4E0 | 1.0E1 | 5.1E1 | 4.8E1 | 8.8E1 | 7.7E1 | 1.0E-9 | 1.0E-9 | 4.5E2 | 2.3E2 | 92 | 22 | 92 | 22 | 0.49 |
| Qy | pg/ml | 3.8E-1 | 5.6E-1 | 9.6E0 | 3.4E1 | 5.1E1 | 1.6E2 | 1.0E-9 | 1.0E-9 | 4.3E2 | 7.3E2 | 92 | 22 | 92 | 22 | 0.59 |
| Qx | pg/ml | 1.0E-9 | 1.0E-9 | 3.3E0 | 7.9E0 | 2.0E1 | 2.4E1 | 1.0E-9 | 1.0E-9 | 1.9E2 | 1.1E2 | 92 | 22 | 92 | 22 | 0.55 |
| Qw | pg/ml | 4.5E-2 | 1.0E-9 | 3.6E0 | 7.6E-1 | 1.1E1 | 1.4E0 | 1.0E-9 | 1.0E-9 | 6.6E1 | 5.6E0 | 92 | 22 | 92 | 22 | 0.45 |
| Qv | pg/ml | 1.8E4 | 1.1E4 | 3.1E4 | 5.7E4 | 5.2E4 | 2.0E5 | 1.0E-9 | 4.0E2 | 3.7E5 | 9.4E5 | 92 | 22 | 92 | 22 | 0.40 |
| Qu | pg/ml | 8.0E0 | 7.7E0 | 1.0E2 | 7.5E1 | 2.0E2 | 1.6E2 | 1.0E-9 | 1.0E-9 | 9.8E2 | 7.3E2 | 92 | 22 | 92 | 22 | 0.48 |
| Qt | pg/ml | 1.5E1 | 1.4E1 | 4.9E1 | 3.9E1 | 1.1E2 | 6.5E1 | 1.0E-9 | 1.0E-9 | 7.1E2 | 2.2E2 | 92 | 22 | 92 | 22 | 0.49 |
| Qh | ng/ml | 1.8E1 | 3.6E1 | 4.2E1 | 1.0E2 | 6.3E1 | 1.9E2 | 4.3E-1 | 5.1E0 | 3.4E2 | 8.0E2 | 92 | 22 | 92 | 22 | 0.64 |
| Qg | ng/ml | 7.6E0 | 5.1E0 | 1.2E1 | 1.1E1 | 1.3E1 | 1.7E1 | 1.5E-1 | 3.3E-1 | 7.5E1 | 8.1E1 | 92 | 22 | 92 | 22 | 0.43 |
| Jj | ng/ml | 6.1E2 | 2.6E2 | 2.6E3 | 4.9E2 | 2.3E4 | 4.9E2 | 2.0E1 | 1.2E1 | 3.4E5 | 1.9E3 | 215 | 55 | 215 | 55 | 0.35 |
| Jk | ng/ml | 3.0E0 | 4.7E0 | 2.3E1 | 3.1E1 | 5.4E1 | 5.4E1 | 1.0E-9 | 2.4E-1 | 3.9E2 | 2.4E2 | 215 | 55 | 215 | 55 | 0.58 |
| Jl | ng/ml | 4.9E-1 | 1.0E0 | 1.8E0 | 1.9E2 | 4.0E0 | 1.3E3 | 1.2E-3 | 7.8E-2 | 2.6E1 | 9.9E3 | 215 | 55 | 215 | 55 | 0.64 |
| Jm | ng/ml | 2.2E1 | 3.5E1 | 6.0E1 | 9.7E1 | 1.2E2 | 2.8E2 | 1.0E-9 | 4.7E-1 | 1.0E3 | 2.1E3 | 215 | 55 | 215 | 55 | 0.57 |
| Jn | ng/ml | 3.6E-1 | 6.5E-1 | 1.7E0 | 3.1E1 | 5.7E0 | 1.3E2 | 1.0E-9 | 1.0E-9 | 5.8E1 | 7.3E2 | 215 | 55 | 215 | 55 | 0.65 |
| Jo | pg/ml | 4.2E3 | 5.1E3 | 5.1E3 | 8.0E3 | 3.9E3 | 1.4E4 | 2.6E2 | 2.3E2 | 2.4E4 | 1.0E5 | 215 | 55 | 215 | 55 | 0.53 |
| Jp | pg/ml | 7.1E4 | 8.7E4 | 7.4E4 | 9.9E4 | 3.5E4 | 5.2E4 | 2.1E3 | 2.8E4 | 1.9E5 | 3.8E5 | 215 | 55 | 215 | 55 | 0.67 |
| Jq | pg/ml | 9.5E1 | 1.5E2 | 1.5E2 | 4.8E2 | 1.7E2 | 1.3E3 | 5.6E0 | 5.6E0 | 1.1E3 | 8.7E3 | 215 | 55 | 215 | 55 | 0.60 |
| Jr | pg/ml | 2.8E0 | 1.2E1 | 2.6E1 | 3.0E2 | 1.5E2 | 1.2E3 | 1.0E-9 | 1.0E-9 | 1.9E3 | 7.4E3 | 215 | 55 | 215 | 55 | 0.66 |
| Js | pg/ml | 1.4E1 | 2.1E1 | 4.1E1 | 2.2E2 | 1.4E2 | 6.7E2 | 1.0E-9 | 3.0E0 | 1.6E3 | 3.0E3 | 215 | 55 | 215 | 55 | 0.68 |
| Jt | pg/ml | 2.4E3 | 3.4E3 | 2.9E3 | 6.0E3 | 2.0E3 | 9.0E3 | 1.5E2 | 4.1E2 | 1.3E4 | 5.2E4 | 215 | 55 | 215 | 55 | 0.65 |
| Xa | pg/ml | 3.1E-1 | 2.4E1 | 7.7E0 | 2.4E2 | 1.7E1 | 4.4E2 | 1.0E-9 | 2.9E0 | 9.6E1 | 1.2E3 | 42 | 8 | 42 | 8 | 0.85 |
| Yc | pg/ml | 1.0E-9 | 1.0E-9 | 5.4E0 | 9.0E-1 | 1.5E1 | 2.5E0 | 1.0E-9 | 1.0E-9 | 6.9E1 | 7.2E0 | 42 | 8 | 42 | 8 | 0.40 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Tm | pg/ml | 1.0E-9 | 1.0E-9 | 3.1E0 | 1.0E0 | 4.8E0 | 3.0E0 | 1.0E-9 | 1.0E-9 | 1.8E1 | 8.4E0 | 42 | 8 | 42 | 8 | 0.39 |
| Tl | pg/ml | 1.3E-1 | 1.0E-9 | 3.6E-1 | 3.2E0 | 4.2E-1 | 8.7E0 | 1.0E-9 | 1.0E-9 | 1.8E0 | 2.5E1 | 42 | 8 | 42 | 8 | 0.36 |
| Ju | mIU/ml | 1.1E1 | 1.6E1 | 2.7E1 | 2.3E1 | 3.8E1 | 2.3E1 | 1.7E-1 | 5.4E0 | 2.3E2 | 1.0E2 | 92 | 22 | 92 | 22 | 0.58 |
| Jv | mIU/ml | 1.9E1 | 1.3E1 | 4.5E1 | 2.8E1 | 6.8E1 | 4.1E1 | 1.7E-2 | 1.5E0 | 4.4E2 | 1.8E2 | 92 | 22 | 92 | 22 | 0.45 |
| Jy | ng/ml | 1.6E-3 | 1.9E-3 | 2.5E-3 | 4.1E-3 | 4.5E-3 | 8.5E-3 | 1.7E-4 | 4.5E-4 | 3.9E-2 | 4.1E-2 | 92 | 22 | 92 | 22 | 0.57 |
| Kc | pg/ml | 2.2E1 | 4.6E1 | 3.4E1 | 8.3E1 | 3.9E1 | 8.7E1 | 1.0E-9 | 1.0E-9 | 1.9E2 | 3.2E2 | 93 | 23 | 93 | 23 | 0.66 |
| Kd | pg/ml | 1.0E-9 | 1.0E-9 | 1.8E2 | 2.4E3 | 6.3E2 | 8.0E3 | 1.0E-9 | 1.0E-9 | 4.8E3 | 3.8E4 | 93 | 23 | 93 | 23 | 0.60 |
| Ke | pg/ml | 1.1E4 | 2.6E4 | 1.3E4 | 4.4E4 | 8.5E3 | 6.5E4 | 6.7E2 | 4.2E3 | 5.5E4 | 3.2E5 | 93 | 23 | 93 | 23 | 0.78 |
| Kf | pg/mL | 5.7E0 | 9.2E0 | 6.2E0 | 1.4E1 | 4.8E0 | 1.7E1 | 1.0E-9 | 1.0E-9 | 2.2E1 | 7.8E1 | 93 | 23 | 93 | 23 | 0.70 |
| Kg | pg/mL | 9.9E2 | 1.0E3 | 1.6E3 | 4.2E3 | 1.5E3 | 9.0E3 | 7.7E1 | 1.3E2 | 8.1E3 | 3.6E4 | 93 | 23 | 93 | 23 | 0.52 |
| Ki | pg/ml | 5.6E1 | 6.4E1 | 6.9E1 | 7.7E1 | 5.6E1 | 5.5E1 | 1.0E-9 | 1.0E-9 | 2.9E2 | 2.5E2 | 93 | 23 | 93 | 23 | 0.56 |
| Kj | pg/ml | 8.9E2 | 7.3E2 | 1.4E3 | 1.8E3 | 1.5E3 | 3.2E3 | 6.6E1 | 3.3E1 | 8.8E3 | 1.5E4 | 93 | 23 | 93 | 23 | 0.45 |
| Kk | pg/ml | 6.8E0 | 1.4E1 | 1.1E1 | 2.6E1 | 1.4E1 | 2.1E1 | 1.0E-9 | 2.0E0 | 8.1E1 | 5.9E1 | 93 | 23 | 93 | 23 | 0.72 |
| Kl | pg/ml | 1.9E4 | 1.8E4 | 2.9E4 | 2.7E4 | 2.8E4 | 2.0E4 | 2.3E2 | 1.6E3 | 1.3E5 | 6.3E4 | 93 | 23 | 93 | 23 | 0.52 |
| Kn | pg/ml | 2.9E1 | 6.3E1 | 5.3E1 | 3.6E2 | 7.8E1 | 1.0E3 | 1.0E-9 | 1.0E-9 | 3.6E2 | 4.9E3 | 93 | 23 | 93 | 23 | 0.69 |
| Ko | pg/ml | 3.1E2 | 7.4E2 | 4.4E2 | 9.7E2 | 4.9E2 | 1.0E3 | 1.0E-9 | 1.5E2 | 2.2E3 | 4.1E3 | 93 | 23 | 93 | 23 | 0.73 |
| Kp | pg/ml | 3.6E2 | 4.2E2 | 3.5E2 | 1.0E3 | 2.4E2 | 2.7E3 | 1.0E-9 | 3.7E1 | 9.4E2 | 1.3E4 | 93 | 23 | 93 | 23 | 0.62 |
| Kq | pg/ml | 3.2E2 | 5.7E2 | 4.3E2 | 8.2E3 | 5.0E2 | 3.3E4 | 1.6E0 | 1.4E2 | 3.6E3 | 1.6E5 | 88 | 23 | 88 | 23 | 0.72 |
| Kr | pg/ml | 3.7E-1 | 2.2E0 | 1.9E0 | 2.1E1 | 3.6E0 | 8.6E1 | 1.0E-9 | 1.0E-9 | 2.3E1 | 4.2E2 | 88 | 23 | 88 | 23 | 0.62 |
| Ks | pg/ml | 1.5E4 | 1.7E4 | 2.1E4 | 2.2E4 | 1.9E4 | 1.8E4 | 5.1E1 | 9.9E2 | 7.9E4 | 5.1E4 | 88 | 23 | 88 | 23 | 0.53 |
| Ps | ng/ml | 1.3E2 | 1.3E3 | 2.6E2 | 3.5E3 | 3.4E2 | 4.3E3 | 5.5E0 | 3.5E2 | 1.5E3 | 1.2E4 | 41 | 8 | 41 | 8 | 0.94 |
| Kx | ng/ml | 1.0E-9 | 8.8E-3 | 7.0E-3 | 1.8E-2 | 1.6E-2 | 2.1E-2 | 1.0E-9 | 1.0E-9 | 1.0E-1 | 6.5E-2 | 92 | 23 | 92 | 23 | 0.71 |
| Ky | ng/ml | 1.1E-1 | 3.5E-1 | 4.0E-1 | 5.9E-1 | 8.4E-1 | 6.7E-1 | 1.0E-9 | 1.0E-9 | 5.1E0 | 2.7E0 | 92 | 23 | 92 | 23 | 0.67 |
| Kz | ng/ml | 1.0E-9 | 1.0E-9 | 3.4E-3 | 5.6E-3 | 5.6E-3 | 7.8E-3 | 1.0E-9 | 1.0E-9 | 1.4E-2 | 2.5E-2 | 92 | 23 | 92 | 23 | 0.56 |
| Rz | ng/ml | 3.4E-1 | 3.2E-1 | 6.7E-1 | 1.4E0 | 8.5E-1 | 2.5E0 | 4.6E-3 | 1.7E-2 | 3.4E0 | 7.5E0 | 41 | 8 | 41 | 8 | 0.54 |
| Ry | ng/ml | 1.6E-2 | 3.2E-2 | 2.3E-2 | 7.1E-2 | 2.7E-2 | 1.2E-1 | 1.0E-9 | 8.5E-3 | 1.2E-1 | 3.5E-1 | 41 | 8 | 41 | 8 | 0.68 |
| Rx | ng/ml | 1.0E-9 | 3.5E-5 | 1.5E-3 | 1.9E-3 | 2.4E-3 | 2.9E-3 | 1.0E-9 | 1.0E-9 | 8.6E-3 | 7.6E-3 | 41 | 8 | 41 | 8 | 0.58 |
| Ld | pg/ml | 1.0E-9 | 4.8E0 | 3.1E0 | 8.9E0 | 8.2E0 | 1.2E1 | 1.0E-9 | 1.0E-9 | 6.9E1 | 5.0E1 | 94 | 23 | 94 | 23 | 0.72 |
| Lh | pg/ml | 1.3E4 | 2.8E4 | 2.2E4 | 5.7E4 | 2.8E4 | 9.7E4 | 1.0E-9 | 1.3E3 | 2.6E5 | 4.8E5 | 216 | 55 | 216 | 55 | 0.67 |
| Li | pg/ml | 3.3E3 | 1.0E4 | 1.0E4 | 5.9E4 | 2.8E4 | 1.4E5 | 1.3E1 | 1.9E2 | 2.9E5 | 9.2E5 | 216 | 55 | 216 | 55 | 0.74 |
| Lj | pg/ml | 2.3E3 | 1.2E4 | 1.5E4 | 4.2E4 | 4.6E4 | 7.9E4 | 1.0E-9 | 1.8E2 | 4.3E5 | 4.1E5 | 216 | 55 | 216 | 55 | 0.71 |
| Lp | pg/ml | 1.2E1 | 5.3E0 | 4.6E1 | 3.9E2 | 1.1E2 | 5.8E2 | 1.0E-9 | 1.0E-9 | 5.8E2 | 1.4E3 | 41 | 8 | 41 | 8 | 0.51 |
| Lt | pg/ml | 1.0E-9 | 1.0E-9 | 2.1E0 | 1.0E-9 | 6.5E0 | 0.0E0 | 1.0E-9 | 1.0E-9 | 2.5E1 | 1.0E-9 | 41 | 8 | 41 | 8 | 0.45 |
| Rv | ng/ml | 5.0E-4 | 3.8E-4 | 1.2E-3 | 2.9E-3 | 2.5E-3 | 5.0E-3 | 1.0E-9 | 1.0E-9 | 1.6E-2 | 1.2E-2 | 41 | 8 | 41 | 8 | 0.47 |
| Ru | ng/ml | 1.0E-9 | 1.0E-9 | 1.3E-2 | 9.4E-2 | 5.8E-2 | 1.5E-1 | 1.0E-9 | 1.0E-9 | 3.1E-1 | 3.5E-1 | 41 | 8 | 41 | 8 | 0.67 |
| Rt | ng/ml | 8.0E-2 | 5.1E-2 | 1.1E-1 | 1.1E0 | 1.2E-1 | 2.6E0 | 2.2E-3 | 1.3E-3 | 5.8E-1 | 7.4E0 | 41 | 8 | 41 | 8 | 0.48 |
| Yl | pg/ml | 1.1E1 | 2.6E1 | 1.7E1 | 4.7E1 | 1.7E1 | 7.2E1 | 1.0E-9 | 1.0E-9 | 7.9E1 | 2.2E2 | 42 | 8 | 42 | 8 | 0.63 |
| Rm | ng/ml | 1.7E1 | 5.4E1 | 4.0E1 | 1.0E2 | 6.3E1 | 1.5E2 | 2.2E-1 | 3.9E-1 | 3.4E2 | 6.5E2 | 91 | 22 | 91 | 22 | 0.62 |
| Rh | ng/ml | 1.7E2 | 1.7E2 | 3.1E2 | 9.8E2 | 5.2E2 | 3.6E3 | 7.5E0 | 2.5E1 | 3.8E3 | 1.7E4 | 91 | 22 | 91 | 22 | 0.49 |
| Ri | ng/ml | 4.4E-2 | 1.0E-9 | 3.7E0 | 9.6E-1 | 7.1E0 | 3.4E0 | 1.0E-9 | 1.0E-9 | 4.5E1 | 1.6E1 | 91 | 22 | 91 | 22 | 0.33 |
| Rg | ng/ml | 1.0E-9 | 1.0E-9 | 1.0E-1 | 6.6E-2 | 5.1E-1 | 1.8E-1 | 1.0E-9 | 1.0E-9 | 3.3E0 | 6.2E-1 | 91 | 22 | 91 | 22 | 0.53 |
| Rj | ng/ml | 1.0E-9 | 1.0E-9 | 9.9E-1 | 1.3E1 | 2.2E0 | 5.8E1 | 1.0E-9 | 1.0E-9 | 1.1E1 | 2.7E2 | 91 | 22 | 91 | 22 | 0.46 |
| Rf | ng/ml | 3.4E-1 | 6.7E-1 | 6.9E-1 | 2.3E0 | 1.2E0 | 4.3E0 | 2.1E-2 | 5.5E-2 | 9.9E0 | 1.7E1 | 91 | 22 | 91 | 22 | 0.68 |
| Ql | pg/ml | 1.7E0 | 8.6E0 | 1.2E1 | 1.8E1 | 2.5E1 | 2.5E1 | 1.0E-9 | 1.0E-9 | 1.8E2 | 9.3E1 | 92 | 22 | 92 | 22 | 0.61 |
| Qm | pg/ml | 2.2E0 | 1.7E1 | 1.9E1 | 2.8E1 | 3.6E1 | 3.3E1 | 1.0E-9 | 1.0E-9 | 1.9E2 | 1.0E2 | 92 | 22 | 92 | 22 | 0.61 |
| Qn | pg/ml | 6.1E-1 | 8.5E-1 | 4.9E0 | 8.0E0 | 2.3E1 | 2.0E1 | 1.0E-9 | 1.0E-9 | 2.2E2 | 7.5E1 | 92 | 22 | 92 | 22 | 0.57 |
| Nv | pg/ml | 3.7E3 | 7.8E3 | 9.3E3 | 2.1E4 | 1.9E4 | 3.3E4 | 1.0E-9 | 3.3E2 | 1.5E5 | 1.6E5 | 217 | 55 | 217 | 55 | 0.69 |
| Nw | pg/ml | 9.0E3 | 1.9E4 | 1.3E4 | 2.9E4 | 1.7E4 | 3.9E4 | 1.9E2 | 5.1E3 | 2.1E5 | 2.2E5 | 217 | 55 | 217 | 55 | 0.79 |
| Nx | pg/ml | 2.2E2 | 4.9E2 | 4.2E2 | 7.4E2 | 6.2E2 | 8.1E2 | 1.0E-9 | 1.0E-9 | 3.5E3 | 4.1E3 | 217 | 55 | 217 | 55 | 0.63 |
| Ny | pg/ml | 5.2E0 | 1.9E1 | 1.4E2 | 1.4E2 | 1.7E3 | 4.1E2 | 1.0E-9 | 1.0E-9 | 2.5E4 | 2.8E3 | 217 | 55 | 217 | 55 | 0.72 |
| Oa | pg/ml | 1.2E2 | 6.1E2 | 3.9E2 | 1.1E3 | 6.3E2 | 1.2E3 | 1.0E-9 | 4.9E0 | 3.0E3 | 4.5E3 | 92 | 22 | 92 | 22 | 0.72 |
| Op | pg/ml | 4.4E5 | 4.2E5 | 4.3E5 | 4.1E5 | 1.6E5 | 1.7E5 | 5.2E4 | 9.4E4 | 7.5E5 | 6.6E5 | 41 | 8 | 41 | 8 | 0.48 |
| Oe | pg/ml | 7.5E1 | 1.0E-9 | 2.8E2 | 2.0E2 | 4.1E2 | 3.5E2 | 1.0E-9 | 1.0E-9 | 2.3E3 | 1.3E3 | 216 | 54 | 216 | 54 | 0.44 |
| Of | pg/ml | 2.0E2 | 1.0E2 | 6.4E3 | 5.6E3 | 2.4E4 | 1.9E4 | 1.0E-9 | 1.0E-9 | 1.9E5 | 1.2E5 | 217 | 55 | 217 | 55 | 0.46 |
| Og | pg/ml | 8.3E-2 | 2.0E-2 | 4.5E-1 | 8.7E-2 | 1.8E0 | 1.5E-1 | 1.0E-9 | 1.0E-9 | 1.9E1 | 8.0E-1 | 217 | 55 | 217 | 55 | 0.36 |
| Oh | pg/ml | 2.6E0 | 6.4E0 | 1.7E1 | 3.3E2 | 1.1E2 | 2.1E3 | 1.0E-9 | 1.0E-9 | 1.4E3 | 1.6E4 | 217 | 55 | 217 | 55 | 0.64 |
| Oi | pg/ml | 2.5E0 | 2.7E0 | 5.4E0 | 5.0E0 | 7.5E0 | 6.3E0 | 1.0E-9 | 1.0E-9 | 4.2E1 | 3.1E1 | 217 | 55 | 217 | 55 | 0.51 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ok | pg/ml | 3.9E2 | 6.4E2 | 4.9E2 | 1.1E3 | 4.0E2 | 1.3E3 | 1.5E1 | 1.1E2 | 2.2E3 | 7.8E3 | 217 | 55 | 217 | 55 | 0.72 |
| Om | pg/ml | 4.1E2 | 6.0E2 | 9.1E2 | 2.0E3 | 2.5E3 | 6.9E3 | 1.0E-9 | 1.1E2 | 3.0E4 | 5.1E4 | 217 | 55 | 217 | 55 | 0.62 |
| On | pg/ml | 1.8E2 | 3.2E2 | 2.9E2 | 7.5E2 | 4.5E2 | 1.3E3 | 8.4E-1 | 2.6E1 | 4.5E3 | 8.5E3 | 217 | 55 | 217 | 55 | 0.72 |
| Or | pg/ml | 1.0E1 | 2.4E1 | 3.6E1 | 9.1E1 | 6.8E1 | 1.5E2 | 1.0E-9 | 1.0E-9 | 4.4E2 | 5.1E2 | 94 | 23 | 94 | 23 | 0.60 |
| Ow | pg/ml | 3.4E1 | 9.7E1 | 1.2E2 | 7.9E2 | 3.4E2 | 1.8E3 | 1.0E-9 | 1.0E-9 | 2.7E3 | 8.1E3 | 94 | 23 | 94 | 23 | 0.71 |
| Ou | pg/ml | 4.2E2 | 9.2E2 | 1.0E3 | 2.2E3 | 1.8E3 | 2.9E3 | 1.0E-9 | 1.0E-9 | 1.1E4 | 8.9E3 | 94 | 23 | 94 | 23 | 0.63 |
| Ul | ng/ml | 1.0E-9 | 1.0E-9 | 1.0E0 | 3.5E0 | 4.0E0 | 1.3E1 | 1.0E-9 | 1.0E-9 | 2.3E1 | 5.6E1 | 93 | 22 | 93 | 22 | 0.51 |
| Uo | ng/ml | 1.0E-9 | 1.0E-9 | 8.1E-2 | 4.5E-2 | 2.1E-1 | 1.4E-1 | 1.0E-9 | 1.0E-9 | 1.3E0 | 6.3E-1 | 93 | 22 | 93 | 22 | 0.47 |
| Uk | ng/ml | 1.0E-9 | 1.0E-9 | 7.8E-3 | 2.0E-3 | 3.7E-2 | 6.9E-3 | 1.0E-9 | 1.0E-9 | 3.2E-1 | 3.1E-2 | 93 | 22 | 93 | 22 | 0.42 |
| Um | ng/ml | 1.0E-9 | 1.0E-9 | 2.3E-1 | 2.5E-1 | 6.0E-1 | 6.7E-1 | 1.0E-9 | 1.0E-9 | 3.6E0 | 2.3E0 | 93 | 22 | 93 | 22 | 0.47 |
| Uf | ng/ml | 5.3E-2 | 9.9E-1 | 1.3E-1 | 4.2E-1 | 1.9E-1 | 1.1E0 | 1.0E-3 | 2.1E-2 | 1.1E0 | 5.1E0 | 93 | 22 | 93 | 22 | 0.68 |
| Uh | ng/ml | 2.2E0 | 6.8E0 | 3.0E0 | 7.2E0 | 2.7E0 | 4.6E0 | 3.6E-2 | 7.1E-1 | 1.3E1 | 1.8E1 | 93 | 22 | 93 | 22 | 0.79 |
| Un | ng/ml | 1.6E0 | 2.7E0 | 1.9E0 | 4.0E0 | 1.2E0 | 5.1E0 | 3.4E-1 | 7.1E-1 | 8.0E0 | 2.5E1 | 93 | 22 | 93 | 22 | 0.71 |
| Ug | ng/ml | 1.1E1 | 6.8E0 | 2.3E1 | 2.0E1 | 2.6E1 | 3.7E1 | 1.2E0 | 1.7E0 | 1.4E2 | 1.6E2 | 93 | 22 | 93 | 22 | 0.38 |
| Ur | ng/ml | 1.1E-1 | 1.0E-9 | 3.2E-1 | 7.6E-1 | 5.5E-1 | 1.9E0 | 1.0E-9 | 1.0E-9 | 3.0E0 | 7.3E0 | 92 | 22 | 92 | 22 | 0.39 |
| Up | ng/ml | 1.0E-9 | 1.0E-9 | 2.9E-3 | 1.1E-1 | 9.1E-3 | 5.1E-1 | 1.0E-9 | 1.0E-9 | 5.3E-2 | 2.4E0 | 92 | 22 | 92 | 22 | 0.54 |
| Us | ng/ml | 4.1E-3 | 1.0E-9 | 1.7E-2 | 9.6E-2 | 4.6E-2 | 3.5E-1 | 1.0E-9 | 1.0E-9 | 3.6E-1 | 1.7E0 | 92 | 22 | 92 | 22 | 0.44 |
| Uv | ng/ml | 3.2E-3 | 1.7E-3 | 1.3E-2 | 2.3E-2 | 3.4E-2 | 8.7E-2 | 1.0E-9 | 1.0E-9 | 2.3E-1 | 4.1E-1 | 92 | 22 | 92 | 22 | 0.43 |
| Ut | ng/ml | 7.4E-1 | 1.4E0 | 2.7E0 | 6.9E0 | 6.6E0 | 1.5E1 | 1.0E-9 | 1.0E-9 | 5.2E1 | 6.5E1 | 92 | 22 | 92 | 22 | 0.63 |
| Uu | ng/ml | 7.2E0 | 5.4E0 | 7.7E0 | 6.6E0 | 5.0E0 | 4.2E0 | 5.7E-1 | 1.7E0 | 2.9E1 | 1.7E1 | 92 | 22 | 92 | 22 | 0.43 |
| Uw | ng/ml | 2.3E0 | 4.5E0 | 2.7E0 | 8.5E0 | 2.2E0 | 1.3E1 | 1.0E-9 | 1.7E0 | 7.9E0 | 3.9E1 | 42 | 8 | 42 | 8 | 0.75 |
| Vb | ng/ml | 1.1E0 | 9.3E-1 | 1.1E0 | 1.5E0 | 4.2E-1 | 2.0E0 | 8.5E-2 | 2.6E-1 | 2.0E0 | 6.4E0 | 42 | 8 | 42 | 8 | 0.42 |
| Vc | ng/ml | 1.0E-9 | 1.0E-9 | 3.3E-3 | 1.0E-9 | 1.7E-2 | 0.0E0 | 1.0E-9 | 1.0E-9 | 1.1E-1 | 1.0E-9 | 42 | 8 | 42 | 8 | 0.46 |
| Uy | ng/ml | 1.3E0 | 1.3E0 | 5.9E0 | 1.9E1 | 1.7E1 | 2.6E1 | 8.7E-2 | 2.0E-2 | 9.9E1 | 6.4E1 | 42 | 8 | 42 | 8 | 0.57 |
| Uz | ng/ml | 1.0E-9 | 1.0E-9 | 1.0E-2 | 4.2E0 | 6.7E-2 | 1.2E1 | 1.0E-9 | 1.0E-9 | 4.4E-1 | 3.3E1 | 42 | 8 | 42 | 8 | 0.61 |
| Ux | ng/ml | 2.1E2 | 1.3E2 | 2.0E2 | 1.7E2 | 1.3E2 | 1.4E2 | 4.5E0 | 4.0E1 | 4.6E2 | 4.9E2 | 42 | 8 | 42 | 8 | 0.41 |
| Va | ng/ml | 1.5E1 | 3.2E1 | 2.6E1 | 1.1E1 | 3.0E1 | 2.1E1 | 3.1E-1 | 1.2E0 | 1.2E2 | 6.2E1 | 42 | 8 | 42 | 8 | 0.31 |
| Vh | ng/ml | 1.1E-2 | 2.3E-2 | 1.9E-2 | 1.3E-1 | 2.6E-2 | 3.0E-1 | 1.0E-3 | 3.5E-3 | 1.2E-1 | 8.6E-1 | 42 | 8 | 42 | 8 | 0.71 |
| Vi | ng/ml | 3.1E-3 | 3.4E-2 | 8.9E-3 | 2.6E-1 | 1.9E-2 | 6.3E-1 | 1.0E-9 | 1.6E-2 | 1.2E-1 | 1.8E0 | 42 | 8 | 42 | 8 | 0.93 |
| Vj | ng/ml | 3.1E1 | 1.0E2 | 5.8E1 | 1.7E2 | 7.1E1 | 2.2E2 | 1.4E0 | 1.4E1 | 3.4E2 | 6.5E2 | 42 | 7 | 42 | 7 | 0.79 |
| Vp | ng/ml | 1.0E-9 | 1.0E-9 | 1.0E-1 | 2.6E0 | 4.8E-1 | 1.0E1 | 1.0E-9 | 1.0E-9 | 3.9E0 | 4.9E1 | 93 | 22 | 93 | 22 | 0.60 |
| Vt | ng/ml | 6.0E0 | 1.1E1 | 7.4E0 | 2.1E1 | 6.3E0 | 3.2E1 | 5.6E-1 | 1.9E0 | 3.2E1 | 1.6E2 | 93 | 22 | 93 | 22 | 0.77 |
| Vu | ng/ml | 1.0E-9 | 3.6E-1 | 1.6E0 | 2.7E0 | 3.0E0 | 5.6E0 | 1.0E-9 | 1.0E-9 | 1.6E1 | 2.2E1 | 91 | 20 | 91 | 20 | 0.56 |
| Vq | ng/ml | 1.3E2 | 1.1E3 | 4.8E2 | 2.0E3 | 8.4E2 | 3.2E3 | 9.2E-1 | 1.0E1 | 5.0E3 | 1.2E4 | 75 | 16 | 75 | 16 | 0.71 |
| Vo | ng/ml | 2.5E1 | 2.5E1 | 2.5E1 | 2.4E1 | 5.8E0 | 4.5E0 | 4.9E0 | 1.1E1 | 4.8E1 | 3.0E1 | 93 | 22 | 93 | 22 | 0.48 |
| Vs | ng/ml | 1.0E-9 | 1.0E-9 | 4.3E0 | 2.7E1 | 1.2E1 | 1.0E2 | 1.0E-9 | 1.0E-9 | 8.9E1 | 4.5E2 | 92 | 20 | 92 | 20 | 0.47 |
| Vv | ng/ml | 3.3E0 | 2.6E0 | 6.0E0 | 6.5E0 | 1.0E1 | 1.1E1 | 1.0E-9 | 1.0E-9 | 8.4E1 | 4.4E1 | 93 | 21 | 93 | 21 | 0.49 |
| Vw | ng/ml | 3.7E1 | 4.9E1 | 3.3E1 | 4.4E1 | 1.7E1 | 2.3E1 | 2.5E0 | 1.1E1 | 6.7E1 | 6.9E1 | 42 | 8 | 42 | 8 | 0.66 |
| Oy | pg/ml | 5.2E-1 | 4.3E-1 | 8.3E0 | 3.0E0 | 3.8E1 | 6.7E0 | 1.0E-9 | 1.0E-9 | 4.0E2 | 3.3E1 | 216 | 55 | 216 | 55 | 0.46 |
| Oz | pg/ml | 4.1E-2 | 1.0E-9 | 4.0E-1 | 6.6E-1 | 2.0E0 | 3.8E0 | 1.0E-9 | 1.0E-9 | 2.9E1 | 2.8E1 | 216 | 55 | 216 | 55 | 0.39 |
| Pa | pg/ml | 3.9E-1 | 7.2E-1 | 1.5E0 | 8.0E0 | 6.8E0 | 3.3E1 | 1.0E-9 | 1.0E-9 | 8.6E1 | 2.3E2 | 216 | 55 | 216 | 55 | 0.63 |
| Pb | pg/ml | 1.0E-9 | 1.0E-9 | 2.4E0 | 1.2E0 | 3.3E1 | 5.6E0 | 1.0E-9 | 1.0E-9 | 4.9E2 | 3.2E1 | 216 | 55 | 216 | 55 | 0.42 |
| Pc | pg/ml | 1.4E-1 | 1.0E-9 | 4.5E-1 | 7.0E0 | 1.1E0 | 4.5E1 | 1.0E-9 | 1.0E-9 | 1.4E1 | 3.3E2 | 216 | 55 | 216 | 55 | 0.45 |
| Pd | pg/ml | 1.7E0 | 2.9E0 | 7.8E0 | 8.9E0 | 5.8E1 | 1.9E1 | 1.0E-9 | 1.0E-9 | 8.4E2 | 1.2E2 | 216 | 55 | 216 | 55 | 0.59 |
| Pe | pg/ml | 2.0E1 | 6.3E1 | 1.0E2 | 7.2E2 | 4.4E2 | 2.3E3 | 1.0E-9 | 1.0E-9 | 4.7E3 | 1.5E4 | 216 | 55 | 216 | 55 | 0.72 |
| Pf | pg/ml | 1.5E0 | 6.0E0 | 1.4E1 | 3.1E1 | 1.0E2 | 7.8E1 | 1.0E-9 | 1.0E-9 | 1.5E3 | 4.3E2 | 216 | 55 | 216 | 55 | 0.71 |
| Pg | pg/ml | 3.7E0 | 1.3E1 | 9.1E1 | 1.6E2 | 6.3E2 | 4.0E2 | 1.0E-9 | 1.0E-9 | 7.7E3 | 2.2E3 | 216 | 55 | 216 | 55 | 0.70 |
| Ph | ng/ml | 1.4E-1 | 2.4E-1 | 3.4E-1 | 6.1E-1 | 5.1E-1 | 1.2E0 | 1.0E-9 | 1.0E-9 | 2.8E0 | 5.4E0 | 94 | 23 | 94 | 23 | 0.56 |
| Pi | ng/ml | 1.9E-1 | 2.7E-1 | 2.8E-1 | 4.1E0 | 4.0E-1 | 1.7E1 | 1.0E-9 | 1.0E-9 | 3.2E0 | 8.2E1 | 94 | 23 | 94 | 23 | 0.63 |
| Pj | ng/mL | 4.9E0 | 7.4E0 | 5.8E0 | 8.5E0 | 4.6E0 | 4.9E0 | 4.0E-1 | 1.5E0 | 3.1E1 | 2.3E1 | 94 | 23 | 94 | 23 | 0.68 |
| Pk | ng/mL | 8.9E-3 | 1.1E-2 | 1.5E-2 | 7.8E-2 | 3.0E-2 | 3.1E-1 | 1.0E-9 | 1.0E-9 | 2.5E-1 | 1.5E0 | 94 | 23 | 94 | 23 | 0.55 |
| aA | mg/dL | 8.7E-1 | 1.0E0 | 9.8E-1 | 1.4E0 | 4.7E-1 | 9.1E-1 | 3.0E-1 | 5.0E-1 | 4.2E0 | 4.7E0 | 337 | 70 | 337 | 70 | 0.63 |
| aC | mg/mL | 2.2E0 | 2.1E0 | 2.5E0 | 2.4E0 | 1.2E0 | 1.2E0 | 7.5E-1 | 1.0E0 | 7.2E0 | 5.5E0 | 112 | 31 | 112 | 31 | 0.47 |
| aD | ug/mL | 3.0E0 | 3.6E0 | 4.5E0 | 4.9E0 | 4.2E0 | 4.0E0 | 7.5E-1 | 9.2E-1 | 3.1E1 | 1.8E1 | 112 | 31 | 112 | 31 | 0.51 |
| aE | mg/mL | 6.0E-1 | 5.1E-1 | 6.0E-1 | 5.6E-1 | 1.7E-1 | 1.8E-1 | 1.8E-1 | 2.2E-1 | 1.1E0 | 1.2E0 | 112 | 31 | 112 | 31 | 0.39 |
| aF | ng/mL | 2.1E0 | 2.9E0 | 5.2E0 | 5.0E0 | 8.4E0 | 6.5E0 | 4.3E-3 | 4.3E-3 | 5.0E1 | 2.9E1 | 112 | 31 | 112 | 31 | 0.49 |
| aG | mg/mL | 1.4E-1 | 1.3E-1 | 1.6E-1 | 1.4E-1 | 8.4E-2 | 6.5E-2 | 5.0E-2 | 6.8E-2 | 4.8E-1 | 3.2E-1 | 112 | 31 | 112 | 31 | 0.46 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aH | ug/mL | 7.4E1 | 5.9E1 | 7.8E1 | 6.5E1 | 3.9E1 | 3.3E1 | 1.5E1 | 1.1E1 | 2.0E2 | 1.4E2 | 112 | 31 | 112 | 31 | 0.40 |
| aI | ug/mL | 1.8E2 | 1.4E2 | 1.8E2 | 1.6E2 | 6.0E1 | 5.8E1 | 4.7E1 | 7.6E1 | 3.4E2 | 2.7E2 | 112 | 31 | 112 | 31 | 0.40 |
| aJ | ug/mL | 2.3E0 | 3.6E0 | 3.0E0 | 4.1E0 | 2.1E0 | 2.8E0 | 8.2E-1 | 1.4E0 | 1.4E1 | 1.1E1 | 112 | 31 | 112 | 31 | 0.64 |
| aK | ng/mL | 1.3E0 | 1.3E0 | 2.0E0 | 1.9E0 | 1.9E0 | 1.8E0 | 2.9E-4 | 1.0E-1 | 1.0E1 | 6.5E0 | 112 | 31 | 112 | 31 | 0.48 |
| aL | mg/mL | 7.3E-1 | 7.4E-1 | 7.6E-1 | 7.3E-1 | 2.3E-1 | 2.7E-1 | 2.2E-1 | 2.7E-1 | 1.7E0 | 1.4E0 | 112 | 31 | 112 | 31 | 0.48 |
| aM | U/mL | 1.5E1 | 2.3E1 | 3.3E1 | 7.2E1 | 4.9E1 | 1.6E2 | 4.2E-2 | 4.2E-2 | 3.5E2 | 8.2E2 | 112 | 31 | 112 | 31 | 0.62 |
| aN | U/mL | 1.5E1 | 1.9E1 | 2.4E1 | 4.0E1 | 4.0E1 | 6.2E1 | 2.5E-3 | 2.5E-3 | 3.8E2 | 3.3E2 | 112 | 31 | 112 | 31 | 0.58 |
| aO | pg/mL | 6.1E1 | 7.2E1 | 4.5E2 | 4.4E2 | 1.1E3 | 7.0E2 | 6.0E-2 | 5.0E0 | 6.6E3 | 2.4E3 | 112 | 31 | 112 | 31 | 0.56 |
| aP | ng/mL | 1.5E0 | 1.9E0 | 1.9E0 | 2.6E0 | 1.2E0 | 1.7E0 | 5.4E-1 | 7.8E-1 | 6.5E0 | 6.6E0 | 112 | 31 | 112 | 31 | 0.63 |
| aQ | ng/mL | 2.4E-1 | 2.2E-1 | 3.6E-1 | 2.8E-1 | 3.4E-1 | 2.0E-1 | 2.0E-4 | 5.1E-2 | 2.0E0 | 9.0E-1 | 112 | 31 | 112 | 31 | 0.45 |
| aR | ng/mL | 1.8E0 | 2.4E0 | 3.0E0 | 3.5E0 | 4.4E0 | 3.3E0 | 2.6E-1 | 6.6E-1 | 3.4E1 | 1.7E1 | 112 | 31 | 112 | 31 | 0.60 |
| aS | ng/mL | 3.9E-1 | 4.0E-1 | 1.2E0 | 8.7E-1 | 3.2E0 | 1.1E0 | 4.2E-3 | 6.0E-2 | 3.3E1 | 4.9E0 | 112 | 31 | 112 | 31 | 0.48 |
| aU | pg/mL | 6.7E1 | 6.2E1 | 1.0E2 | 1.0E2 | 1.1E2 | 1.1E2 | 7.4E-2 | 7.4E-2 | 7.0E2 | 5.1E2 | 112 | 31 | 112 | 31 | 0.50 |
| aV | ng/mL | 6.2E-1 | 3.7E-1 | 1.1E0 | 8.3E-1 | 3.1E0 | 1.1E0 | 7.6E-4 | 9.1E-2 | 3.3E1 | 6.0E0 | 112 | 31 | 112 | 31 | 0.45 |
| aW | pg/mL | 2.1E1 | 1.9E1 | 2.1E1 | 3.1E1 | 1.7E1 | 7.2E1 | 7.2E-2 | 7.2E-2 | 1.7E2 | 4.2E2 | 112 | 31 | 112 | 31 | 0.46 |
| aX | ng/mL | 7.7E0 | 7.0E0 | 1.1E1 | 1.3E1 | 1.0E1 | 2.1E1 | 3.0E-1 | 7.7E-1 | 5.4E1 | 1.1E2 | 112 | 31 | 112 | 31 | 0.46 |
| aY | pg/mL | 5.3E1 | 5.2E1 | 7.9E1 | 6.6E1 | 1.3E2 | 5.4E1 | 4.1E-1 | 4.1E-1 | 1.2E3 | 2.2E2 | 112 | 31 | 112 | 31 | 0.49 |
| aZ | pg/mL | 2.2E2 | 3.0E2 | 5.6E2 | 8.9E2 | 1.3E3 | 1.3E3 | 1.7E0 | 1.7E0 | 1.2E4 | 4.7E3 | 112 | 31 | 112 | 31 | 0.59 |
| bA | ng/mL | 1.3E1 | 4.0E1 | 5.0E1 | 1.4E2 | 1.1E2 | 2.3E2 | 3.0E-2 | 2.0E0 | 9.4E2 | 9.4E2 | 112 | 31 | 112 | 31 | 0.66 |
| bB | ng/mL | 2.8E2 | 2.7E2 | 3.0E2 | 2.5E2 | 1.6E2 | 1.5E2 | 3.6E1 | 1.2E1 | 8.1E2 | 5.7E2 | 112 | 31 | 112 | 31 | 0.42 |
| bC | ng/mL | 3.2E2 | 3.3E2 | 5.7E2 | 7.1E2 | 7.5E2 | 9.9E2 | 2.7E1 | 5.0E1 | 4.7E3 | 4.0E3 | 112 | 31 | 112 | 31 | 0.54 |
| bE | mg/mL | 5.2E0 | 4.8E0 | 5.2E0 | 5.2E0 | 1.8E0 | 2.4E0 | 1.8E0 | 1.3E0 | 1.2E1 | 1.1E1 | 112 | 31 | 112 | 31 | 0.47 |
| bF | pg/mL | 3.4E1 | 5.9E1 | 4.3E2 | 3.0E2 | 1.7E3 | 5.7E2 | 5.0E-2 | 8.9E0 | 1.1E4 | 2.2E3 | 112 | 31 | 112 | 31 | 0.64 |
| bG | ng/mL | 1.7E0 | 2.3E0 | 3.3E0 | 3.6E0 | 5.0E0 | 3.8E0 | 1.1E-1 | 2.4E-1 | 3.0E1 | 1.5E1 | 112 | 31 | 112 | 31 | 0.56 |
| bH | pg/mL | 5.7E-1 | 5.7E-1 | 7.6E0 | 4.6E0 | 2.9E1 | 5.9E0 | 5.7E-1 | 5.7E-1 | 2.8E2 | 2.3E1 | 112 | 31 | 112 | 31 | 0.53 |
| bI | ng/mL | 4.0E-3 | 4.0E-3 | 1.0E-1 | 8.0E-2 | 2.0E-1 | 2.1E-1 | 4.0E-3 | 4.0E-3 | 9.8E-1 | 8.8E-1 | 112 | 31 | 112 | 31 | 0.45 |
| bJ | mg/mL | 1.7E0 | 1.9E0 | 2.1E0 | 2.3E0 | 1.8E0 | 2.3E0 | 2.5E-4 | 2.5E-4 | 1.1E1 | 9.0E0 | 112 | 31 | 112 | 31 | 0.51 |
| bL | pg/mL | 4.2E0 | 3.2E0 | 9.1E0 | 8.1E0 | 1.1E1 | 8.7E0 | 4.6E-2 | 4.6E-2 | 4.9E1 | 3.2E1 | 112 | 31 | 112 | 31 | 0.51 |
| bM | mg/mL | 1.9E0 | 2.2E0 | 2.3E0 | 2.2E0 | 1.5E0 | 1.3E0 | 2.4E-1 | 1.8E-2 | 8.6E0 | 5.4E0 | 112 | 31 | 112 | 31 | 0.51 |
| bN | ng/mL | 4.0E1 | 3.1E1 | 1.4E2 | 5.3E1 | 3.1E2 | 8.4E1 | 1.4E-1 | 5.9E-1 | 1.9E3 | 4.4E2 | 112 | 31 | 112 | 31 | 0.40 |
| bO | ng/mL | 4.0E-2 | 4.0E-2 | 7.5E0 | 1.3E1 | 1.5E1 | 2.8E1 | 4.0E-2 | 4.0E-2 | 7.1E1 | 1.3E2 | 112 | 31 | 112 | 31 | 0.48 |
| bP | mg/mL | 4.9E-1 | 5.7E-1 | 6.9E-1 | 7.5E-1 | 6.4E-1 | 7.5E-1 | 8.2E-2 | 9.2E-2 | 4.8E0 | 3.5E0 | 112 | 31 | 112 | 31 | 0.52 |
| bQ | pg/mL | 2.1E1 | 5.2E1 | 1.8E2 | 6.1E1 | 1.3E3 | 5.6E1 | 1.5E-1 | 1.5E-1 | 1.3E4 | 2.2E2 | 112 | 31 | 112 | 31 | 0.67 |
| bR | ng/mL | 1.2E-2 | 1.2E-2 | 1.9E-1 | 7.3E-2 | 8.8E-1 | 1.1E-1 | 1.2E-2 | 1.2E-2 | 8.7E0 | 3.9E-1 | 112 | 31 | 112 | 31 | 0.47 |
| bS | pg/mL | 9.4E-1 | 9.4E-1 | 1.1E1 | 5.0E0 | 5.0E1 | 1.4E1 | 9.4E-1 | 9.4E-1 | 3.9E2 | 7.2E1 | 112 | 31 | 112 | 31 | 0.49 |
| bU | ng/mL | 3.4E-2 | 1.5E-1 | 2.0E-1 | 1.7E-1 | 6.5E-1 | 1.8E-1 | 1.3E-2 | 1.3E-2 | 6.6E0 | 6.5E-1 | 112 | 31 | 112 | 31 | 0.57 |
| bV | pg/mL | 4.6E2 | 5.5E2 | 5.3E2 | 7.1E2 | 2.6E2 | 4.8E2 | 1.8E2 | 2.7E2 | 1.6E3 | 2.2E3 | 112 | 31 | 112 | 31 | 0.60 |
| bW | pg/mL | 3.3E2 | 3.1E2 | 4.7E2 | 5.5E2 | 5.3E2 | 8.1E2 | 8.4E1 | 1.3E2 | 4.8E3 | 3.9E3 | 112 | 31 | 112 | 31 | 0.50 |
| bX | ng/mL | 1.5E-3 | 2.5E-5 | 2.6E-3 | 2.3E-3 | 2.9E-3 | 2.8E-3 | 2.5E-5 | 2.5E-5 | 1.2E-2 | 7.8E-3 | 112 | 31 | 112 | 31 | 0.47 |
| bZ | pg/mL | 2.7E2 | 3.6E2 | 2.3E3 | 1.3E3 | 8.4E3 | 1.8E3 | 1.5E-1 | 1.0E2 | 5.8E4 | 7.4E3 | 112 | 31 | 112 | 31 | 0.60 |
| cA | pg/mL | 6.0E-1 | 6.0E-1 | 5.0E0 | 2.0E0 | 3.5E1 | 4.7E0 | 6.0E-1 | 6.0E-1 | 3.7E2 | 2.1E1 | 112 | 31 | 112 | 31 | 0.50 |
| cB | ng/mL | 4.1E-2 | 4.6E-2 | 6.3E-2 | 8.0E-2 | 7.0E-2 | 1.1E-1 | 1.7E-3 | 1.7E-3 | 3.7E-1 | 4.3E-1 | 112 | 31 | 112 | 31 | 0.49 |
| cC | pg/mL | 4.1E1 | 4.8E1 | 4.7E1 | 4.5E1 | 5.8E1 | 2.8E1 | 1.0E0 | 1.0E0 | 4.5E2 | 1.1E2 | 112 | 31 | 112 | 31 | 0.55 |
| cD | pg/mL | 4.9E0 | 5.2E0 | 1.6E1 | 9.1E0 | 5.6E1 | 1.6E1 | 3.3E-1 | 3.3E-1 | 4.8E2 | 9.0E1 | 112 | 31 | 112 | 31 | 0.53 |
| cE | pg/mL | 6.3E1 | 1.3E2 | 2.7E2 | 2.9E2 | 6.8E2 | 4.2E2 | 1.2E-1 | 1.4E1 | 3.8E3 | 2.1E3 | 112 | 31 | 112 | 31 | 0.64 |
| cF | pg/mL | 5.3E-1 | 8.6E0 | 1.6E1 | 1.3E1 | 3.4E1 | 1.7E1 | 5.3E-1 | 5.3E-1 | 2.7E2 | 6.5E1 | 112 | 31 | 112 | 31 | 0.52 |
| cG | pg/mL | 5.2E1 | 9.4E1 | 1.9E2 | 1.4E2 | 9.9E2 | 1.1E2 | 7.8E0 | 2.4E1 | 1.0E4 | 4.1E2 | 112 | 31 | 112 | 31 | 0.66 |
| cH | uIU/mL | 3.7E0 | 2.2E0 | 8.9E0 | 5.0E0 | 2.0E1 | 9.0E0 | 8.6E-3 | 8.6E-3 | 1.6E2 | 3.9E1 | 112 | 31 | 112 | 31 | 0.37 |
| cI | ng/mL | 5.9E0 | 6.9E0 | 1.1E1 | 2.1E1 | 1.6E1 | 3.3E1 | 2.3E-1 | 3.2E-2 | 9.4E1 | 1.2E2 | 112 | 31 | 112 | 31 | 0.54 |
| cJ | ug/mL | 6.5E1 | 4.8E1 | 1.0E2 | 7.0E1 | 1.1E2 | 6.9E1 | 6.9E0 | 7.2E0 | 6.4E2 | 3.4E2 | 112 | 31 | 112 | 31 | 0.43 |
| cK | ng/mL | 3.8E-3 | 3.8E-3 | 2.3E-2 | 1.8E-2 | 1.4E-1 | 4.0E-2 | 3.8E-3 | 3.8E-3 | 1.5E0 | 2.1E-1 | 112 | 31 | 112 | 31 | 0.54 |
| cL | pg/mL | 2.1E2 | 2.2E2 | 6.4E2 | 3.6E2 | 2.5E3 | 3.6E2 | 3.1E1 | 1.1E2 | 2.4E4 | 1.5E3 | 112 | 31 | 112 | 31 | 0.60 |
| cM | pg/mL | 2.6E2 | 2.8E2 | 2.9E2 | 2.8E2 | 1.8E2 | 1.1E2 | 4.2E1 | 5.7E1 | 1.1E3 | 4.8E2 | 112 | 31 | 112 | 31 | 0.52 |
| cN | pg/mL | 1.1E2 | 1.3E2 | 1.3E2 | 1.4E2 | 1.0E2 | 4.2E1 | 3.8E1 | 7.9E1 | 1.1E3 | 2.7E2 | 112 | 31 | 112 | 31 | 0.59 |
| cO | pg/mL | 2.0E2 | 2.4E2 | 4.7E2 | 3.2E2 | 1.8E3 | 2.6E2 | 5.4E1 | 1.3E2 | 1.9E4 | 1.5E3 | 112 | 31 | 112 | 31 | 0.61 |
| cP | ng/mL | 2.5E3 | 2.2E3 | 2.6E3 | 2.4E3 | 1.0E3 | 9.3E2 | 6.2E2 | 1.0E3 | 5.6E3 | 4.7E3 | 112 | 31 | 112 | 31 | 0.44 |
| cQ | ng/mL | 5.2E-2 | 3.5E-2 | 1.3E-1 | 1.2E-1 | 2.1E-1 | 2.2E-1 | 2.0E-3 | 2.0E-3 | 1.3E0 | 8.7E-1 | 112 | 31 | 112 | 31 | 0.44 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cR | ng/mL | 3.0E2 | 3.8E2 | 5.4E2 | 6.8E2 | 8.3E2 | 9.4E2 | 2.0E1 | 8.6E1 | 7.7E3 | 4.8E3 | 112 | 31 | 112 | 31 | 0.56 |
| cS | ng/mL | 2.6E2 | 3.0E2 | 3.8E2 | 4.6E2 | 4.0E2 | 4.8E2 | 8.0E1 | 9.1E1 | 2.5E3 | 2.4E3 | 112 | 31 | 112 | 31 | 0.54 |
| cT | ng/mL | 5.0E1 | 1.0E2 | 1.4E2 | 2.9E2 | 2.6E2 | 4.5E2 | 4.2E0 | 1.1E1 | 2.1E3 | 1.5E3 | 112 | 31 | 112 | 31 | 0.62 |
| cU | ng/mL | 5.8E1 | 8.0E1 | 9.8E1 | 1.1E2 | 1.7E2 | 9.4E1 | 6.2E0 | 9.0E0 | 1.6E3 | 4.2E2 | 112 | 31 | 112 | 31 | 0.60 |
| cV | ng/mL | 2.0E-1 | 2.2E-1 | 8.9E-1 | 6.4E-1 | 4.5E0 | 1.8E0 | 3.4E-2 | 3.0E-2 | 4.7E1 | 9.7E0 | 112 | 31 | 112 | 31 | 0.50 |
| cW | mIU/mL | 4.8E-2 | 4.5E-2 | 9.6E-2 | 7.2E-2 | 4.2E-1 | 7.2E-2 | 4.8E-3 | 1.4E-2 | 4.5E0 | 3.9E-1 | 112 | 31 | 112 | 31 | 0.54 |
| cX | ng/mL | 1.8E-1 | 6.3E-2 | 2.0E0 | 2.7E0 | 5.7E0 | 7.6E0 | 2.3E-4 | 2.3E-4 | 2.8E1 | 2.8E1 | 112 | 31 | 112 | 31 | 0.46 |
| cY | ng/mL | 7.1E0 | 8.9E0 | 1.1E1 | 1.1E1 | 1.2E1 | 9.5E0 | 1.7E-1 | 6.0E-1 | 6.1E1 | 3.7E1 | 112 | 31 | 112 | 31 | 0.52 |
| cZ | ug/mL | 1.2E1 | 1.2E1 | 1.4E1 | 1.3E1 | 5.7E0 | 7.0E0 | 2.8E0 | 3.3E0 | 3.0E1 | 3.0E1 | 112 | 31 | 112 | 31 | 0.43 |
| dA | pg/mL | 3.1E2 | 3.5E2 | 3.8E2 | 3.8E2 | 5.4E2 | 2.1E2 | 1.0E2 | 1.1E2 | 5.8E3 | 9.3E2 | 112 | 31 | 112 | 31 | 0.52 |
| dB | ug/mL | 1.9E1 | 2.1E1 | 1.9E1 | 1.9E1 | 2.4E1 | 9.5E0 | 2.1E0 | 2.2E0 | 2.5E2 | 3.2E1 | 112 | 31 | 112 | 31 | 0.55 |
| dC | nmol/L | 3.4E1 | 3.6E1 | 3.8E1 | 3.9E1 | 1.8E1 | 1.4E1 | 7.8E0 | 1.5E1 | 1.4E2 | 6.5E1 | 112 | 31 | 112 | 31 | 0.55 |
| dD | ug/mL | 3.4E1 | 3.0E1 | 3.5E1 | 3.2E1 | 1.0E1 | 1.2E1 | 1.4E1 | 1.4E1 | 7.4E1 | 6.0E1 | 112 | 31 | 112 | 31 | 0.39 |
| dE | ng/mL | 4.0E-1 | 4.8E-1 | 5.3E-1 | 5.8E-1 | 5.6E-1 | 5.6E-1 | 8.4E-3 | 8.4E-3 | 2.7E0 | 2.4E0 | 112 | 31 | 112 | 31 | 0.54 |
| dF | ng/mL | 2.4E2 | 3.7E2 | 3.2E2 | 4.8E2 | 2.2E2 | 3.3E2 | 7.5E1 | 1.1E2 | 1.3E3 | 1.2E3 | 112 | 31 | 112 | 31 | 0.65 |
| dG | ng/mL | 1.2E1 | 1.5E1 | 1.6E1 | 2.0E1 | 2.0E1 | 1.7E1 | 3.0E0 | 4.8E0 | 1.8E2 | 8.7E1 | 112 | 31 | 112 | 31 | 0.61 |
| dH | pg/mL | 7.3E0 | 1.1E1 | 2.1E1 | 1.5E1 | 7.1E1 | 1.5E1 | 4.0E-2 | 4.0E-2 | 6.7E2 | 7.9E1 | 112 | 31 | 112 | 31 | 0.63 |
| dI | pg/mL | 4.6E-1 | 4.6E-1 | 4.5E0 | 1.9E0 | 3.1E1 | 2.4E0 | 4.6E-1 | 4.6E-1 | 3.3E2 | 8.4E0 | 112 | 31 | 112 | 31 | 0.56 |
| dJ | ng/mL | 1.9E0 | 2.2E0 | 2.1E0 | 2.2E0 | 1.1E0 | 1.3E0 | 3.2E-2 | 3.2E-2 | 5.1E0 | 4.4E0 | 112 | 31 | 112 | 31 | 0.55 |
| dK | uIU/mL | 1.5E0 | 8.8E-1 | 2.4E0 | 1.9E0 | 4.2E0 | 2.4E0 | 2.8E-4 | 2.9E-2 | 3.9E1 | 1.1E1 | 112 | 31 | 112 | 31 | 0.41 |
| dL | ng/mL | 8.7E2 | 1.0E3 | 1.0E3 | 1.2E3 | 5.5E2 | 8.9E2 | 2.8E2 | 4.3E2 | 3.4E3 | 4.8E3 | 112 | 31 | 112 | 31 | 0.56 |
| dM | pg/mL | 9.5E2 | 1.2E3 | 1.2E3 | 2.0E3 | 1.5E3 | 2.0E3 | 3.7E2 | 6.3E2 | 1.5E4 | 9.6E3 | 112 | 31 | 112 | 31 | 0.65 |
| dN | ug/mL | 9.7E1 | 1.1E2 | 1.0E2 | 1.2E2 | 3.6E1 | 5.7E1 | 2.4E1 | 4.7E1 | 2.2E2 | 3.3E2 | 112 | 31 | 112 | 31 | 0.58 |
| dR | pg/ml | 1.5E3 | 1.0E3 | 2.1E3 | 1.6E3 | 2.1E3 | 2.0E3 | 1.4E2 | 1.3E2 | 9.8E3 | 8.9E3 | 89 | 24 | 89 | 24 | 0.38 |
| dX | ng/ml | 5.2E-2 | 8.2E-2 | 1.4E-1 | 1.2E-1 | 2.4E-1 | 1.3E-1 | 2.6E-3 | 2.6E-3 | 1.2E0 | 4.2E-1 | 33 | 12 | 33 | 12 | 0.53 |
| eF | ng/ml | 4.1E0 | 4.4E0 | 4.8E0 | 5.1E0 | 2.2E0 | 2.7E0 | 2.0E0 | 2.0E0 | 1.2E1 | 1.5E1 | 89 | 24 | 89 | 24 | 0.54 |
| eC | pg/ml | 3.1E2 | 2.4E2 | 3.8E2 | 3.3E2 | 2.7E2 | 4.1E2 | 7.1E1 | 1.9E1 | 1.6E3 | 2.0E3 | 81 | 21 | 81 | 21 | 0.35 |
| eD | pg/ml | 2.2E2 | 1.8E2 | 7.3E2 | 4.3E2 | 1.5E3 | 9.0E2 | 5.2E-1 | 5.2E-1 | 7.0E3 | 3.8E3 | 67 | 16 | 67 | 16 | 0.48 |
| eM | ng/ml | 2.7E0 | 3.2E0 | 3.7E0 | 7.0E0 | 2.9E0 | 8.2E0 | 6.9E-1 | 8.8E-1 | 1.2E1 | 2.6E1 | 47 | 15 | 47 | 15 | 0.59 |
| eP | ng/ml | 3.7E-3 | 3.7E-3 | 6.7E-1 | 2.6E0 | 1.6E0 | 7.9E0 | 3.7E-3 | 3.7E-3 | 8.6E0 | 2.8E1 | 33 | 12 | 33 | 12 | 0.51 |
| eT | ng/ml | 2.8E2 | 5.6E2 | 6.8E2 | 9.7E2 | 8.0E2 | 1.1E3 | 1.0E2 | 7.1E1 | 2.9E3 | 2.9E3 | 40 | 9 | 40 | 9 | 0.51 |
| eZ | ng/ml | 4.5E1 | 6.2E1 | 5.5E1 | 6.9E1 | 2.6E1 | 2.4E1 | 1.8E1 | 3.2E1 | 1.2E2 | 1.1E2 | 40 | 9 | 40 | 9 | 0.69 |
| fN | ng/ml | 2.1E-1 | 2.1E-1 | 2.2E0 | 4.9E0 | 4.5E0 | 6.2E0 | 2.1E-1 | 2.1E-1 | 2.1E1 | 1.4E1 | 40 | 9 | 40 | 9 | 0.61 |
| fP | ng/ml | 2.8E2 | 2.8E2 | 3.3E2 | 3.4E2 | 2.0E2 | 1.7E2 | 1.8E0 | 9.5E1 | 1.0E3 | 7.7E2 | 87 | 23 | 87 | 23 | 0.53 |
| fR | ng/ml | 1.4E5 | 1.9E5 | 2.0E5 | 2.7E5 | 1.5E5 | 2.0E5 | 3.6E4 | 1.9E2 | 6.3E5 | 6.8E5 | 69 | 23 | 69 | 23 | 0.61 |
| fY | ng/ml | 2.5E2 | 2.5E2 | 2.5E2 | 2.4E2 | 1.1E2 | 9.0E1 | 3.6E1 | 1.2E2 | 4.8E2 | 3.8E2 | 40 | 9 | 40 | 9 | 0.48 |
| gC | ng/ml | 2.3E2 | 2.4E2 | 2.5E2 | 2.7E2 | 1.2E2 | 1.2E2 | 8.3E1 | 1.5E2 | 6.4E2 | 4.8E2 | 30 | 8 | 30 | 8 | 0.56 |
| gL | pg/ml | 6.2E4 | 7.4E4 | 6.9E4 | 8.4E4 | 3.1E4 | 3.6E4 | 1.1E4 | 4.3E4 | 1.6E5 | 1.7E5 | 89 | 24 | 89 | 24 | 0.62 |
| gP | U/ml | 2.7E2 | 2.8E2 | 2.8E2 | 2.9E2 | 1.3E2 | 8.9E1 | 1.2E1 | 1.3E2 | 1.1E3 | 5.2E2 | 88 | 24 | 88 | 24 | 0.54 |
| gW | pg/ml | 5.2E2 | 3.4E2 | 8.8E2 | 6.8E2 | 1.1E3 | 7.7E2 | 2.3E0 | 5.5E1 | 6.1E3 | 3.1E3 | 65 | 18 | 65 | 18 | 0.45 |
| tF | pg/mL | 1.3E3 | 1.1E3 | 1.5E4 | 4.4E3 | 4.6E4 | 6.8E3 | 1.2E1 | 1.8E1 | 2.8E5 | 2.4E4 | 82 | 22 | 82 | 22 | 0.48 |
| hA | ng/ml | 2.5E0 | 4.2E0 | 1.6E1 | 1.6E1 | 5.8E1 | 2.9E1 | 1.7E-2 | 1.7E-2 | 3.5E2 | 1.1E2 | 67 | 17 | 67 | 17 | 0.67 |
| nM | pg/ml | 1.0E-9 | 1.0E-9 | 1.0E-9 | 1.1E2 | 0.0E0 | 4.1E2 | 1.0E-9 | 1.0E-9 | 1.0E-9 | 1.5E3 | 50 | 14 | 50 | 14 | 0.54 |
| nN | pg/ml | 1.2E3 | 3.6E3 | 4.3E3 | 1.8E4 | 1.5E4 | 4.0E4 | 1.1E2 | 4.1E2 | 1.0E5 | 1.5E5 | 50 | 14 | 50 | 14 | 0.70 |
| nO | pg/ml | 2.2E1 | 2.9E1 | 3.8E1 | 3.4E1 | 5.2E1 | 2.0E1 | 4.0E0 | 1.2E1 | 3.1E2 | 8.9E1 | 50 | 14 | 50 | 14 | 0.59 |
| nR | pg/ml | 1.6E1 | 4.4E1 | 6.8E1 | 2.2E2 | 1.5E2 | 5.0E2 | 1.0E0 | 2.7E0 | 8.2E2 | 1.9E3 | 50 | 14 | 50 | 14 | 0.65 |
| nT | pg/ml | 7.3E1 | 9.6E1 | 1.0E2 | 1.7E2 | 1.1E2 | 2.3E2 | 1.0E-9 | 2.3E1 | 6.4E2 | 9.2E2 | 50 | 14 | 50 | 14 | 0.58 |
| nU | pg/ml | 3.0E1 | 1.0E2 | 8.2E1 | 1.8E2 | 2.2E2 | 2.4E2 | 1.0E-9 | 1.0E-9 | 1.5E3 | 9.2E2 | 50 | 14 | 50 | 14 | 0.76 |
| lW | pg/ml | 1.0E-9 | 1.0E-9 | 1.2E1 | 1.1E1 | 3.4E1 | 2.1E1 | 1.0E-9 | 1.0E-9 | 1.7E2 | 7.0E1 | 50 | 14 | 50 | 14 | 0.51 |
| lX | pg/ml | 9.0E2 | 7.4E2 | 9.5E2 | 9.7E2 | 5.1E2 | 7.1E2 | 2.3E2 | 1.9E2 | 2.3E3 | 2.5E3 | 50 | 14 | 50 | 14 | 0.47 |
| lY | pg/ml | 1.8E1 | 2.1E1 | 2.1E1 | 2.1E1 | 1.9E1 | 1.4E1 | 1.0E-9 | 5.7E-1 | 1.2E2 | 4.5E1 | 50 | 14 | 50 | 14 | 0.55 |
| mE | pg/ml | 1.0E-9 | 3.5E-1 | 2.4E0 | 3.8E0 | 8.2E0 | 7.4E0 | 1.0E-9 | 1.0E-9 | 5.7E1 | 2.8E1 | 50 | 14 | 50 | 14 | 0.58 |
| mF | pg/ml | 1.4E-1 | 4.0E-1 | 8.9E0 | 1.3E0 | 3.7E1 | 2.2E0 | 1.0E-9 | 1.0E-9 | 2.5E2 | 6.5E0 | 50 | 14 | 50 | 14 | 0.50 |
| mH | pg/ml | 3.2E0 | 4.0E0 | 5.3E0 | 5.5E0 | 8.4E0 | 4.9E0 | 4.0E-1 | 9.0E-1 | 5.3E1 | 1.9E1 | 50 | 14 | 50 | 14 | 0.58 |
| mI | pg/ml | 1.0E-9 | 2.2E1 | 1.1E1 | 5.5E1 | 2.8E1 | 1.2E2 | 1.0E-9 | 1.0E-9 | 1.8E2 | 4.6E2 | 50 | 14 | 50 | 14 | 0.68 |
| mM | pg/ml | 3.8E1 | 6.1E1 | 9.3E1 | 9.3E1 | 1.7E2 | 1.3E2 | 1.0E-9 | 1.0E-9 | 1.1E3 | 4.7E2 | 50 | 14 | 50 | 14 | 0.54 |
| mP | pg/ml | 1.4E1 | 1.7E1 | 1.7E1 | 8.3E1 | 1.8E1 | 2.1E2 | 1.0E-9 | 7.5E0 | 1.2E2 | 8.1E2 | 49 | 14 | 49 | 14 | 0.61 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| mS | pg/ml | 1.6E3 | 1.9E3 | 1.7E3 | 1.8E3 | 9.7E2 | 9.8E2 | 1.0E-9 | 1.0E-9 | 5.1E3 | 3.5E3 | 50 | 14 | 50 | 14 | 0.55 |
| mT | pg/ml | 7.0E1 | 6.0E1 | 1.4E2 | 2.5E2 | 2.5E2 | 4.8E2 | 1.0E1 | 1.7E1 | 1.4E3 | 1.7E3 | 49 | 14 | 49 | 14 | 0.51 |
| mU | pg/ml | 2.1E0 | 3.4E0 | 7.5E0 | 5.1E0 | 3.2E1 | 5.6E0 | 1.0E-9 | 1.2E0 | 2.2E2 | 2.3E1 | 49 | 14 | 49 | 14 | 0.66 |
| mW | pg/ml | 2.2E3 | 1.9E3 | 2.4E3 | 2.9E3 | 1.3E3 | 2.7E3 | 1.0E-9 | 8.9E2 | 6.2E3 | 1.1E4 | 49 | 14 | 49 | 14 | 0.48 |
| mY | pg/ml | 6.0E2 | 9.5E2 | 8.6E2 | 1.4E3 | 1.0E3 | 2.0E3 | 1.0E-9 | 1.9E2 | 5.6E3 | 8.0E3 | 50 | 14 | 50 | 14 | 0.65 |
| mZ | pg/ml | 1.9E2 | 9.4E1 | 3.9E2 | 2.5E2 | 5.2E2 | 3.5E2 | 1.2E1 | 1.1E1 | 3.1E3 | 1.2E3 | 49 | 14 | 49 | 14 | 0.34 |
| nA | pg/ml | 1.5E0 | 3.9E0 | 7.1E0 | 4.5E0 | 1.5E1 | 5.3E0 | 1.0E-9 | 1.0E-9 | 6.5E1 | 1.9E1 | 49 | 14 | 49 | 14 | 0.54 |
| nB | pg/ml | 2.7E2 | 3.5E2 | 3.0E2 | 3.8E2 | 1.7E2 | 2.1E2 | 3.0E1 | 1.5E2 | 8.2E2 | 9.6E2 | 50 | 14 | 50 | 14 | 0.60 |
| nC | pg/ml | 1.0E-9 | 2.3E2 | 1.3E4 | 1.9E3 | 6.2E4 | 3.1E3 | 1.0E-9 | 1.0E-9 | 3.8E5 | 9.1E3 | 50 | 14 | 50 | 14 | 0.68 |
| nD | pg/ml | 6.7E0 | 7.5E0 | 1.3E1 | 1.1E1 | 3.7E1 | 9.7E0 | 1.0E-9 | 1.0E-9 | 2.6E2 | 2.8E1 | 49 | 14 | 49 | 14 | 0.56 |
| nF | pg/ml | 1.0E-9 | 1.0E-9 | 3.4E0 | 9.6E-1 | 1.4E1 | 3.6E0 | 1.0E-9 | 1.0E-9 | 9.3E1 | 1.3E1 | 50 | 14 | 50 | 14 | 0.49 |
| nH | pg/ml | 1.8E-1 | 4.7E0 | 2.6E2 | 2.7E1 | 1.5E3 | 4.3E1 | 1.0E-9 | 1.0E-9 | 1.0E4 | 1.2E2 | 49 | 14 | 49 | 14 | 0.70 |
| nI | pg/ml | 4.6E1 | 1.0E-9 | 6.3E1 | 1.3E1 | 8.0E1 | 2.6E1 | 1.0E-9 | 1.0E-9 | 3.5E2 | 7.9E1 | 50 | 14 | 50 | 14 | 0.30 |
| nJ | pg/ml | 1.7E-1 | 1.1E0 | 3.6E0 | 1.1E0 | 1.9E1 | 9.5E-1 | 1.0E-9 | 1.0E-9 | 1.3E2 | 3.0E0 | 50 | 14 | 50 | 14 | 0.59 |
| nK | pg/ml | 1.0E-9 | 1.8E1 | 9.8E0 | 2.5E1 | 2.0E1 | 3.0E1 | 1.0E-9 | 1.0E-9 | 1.0E2 | 9.6E1 | 49 | 14 | 49 | 14 | 0.66 |
| nL | pg/ml | 1.0E-9 | 7.2E0 | 3.7E2 | 9.2E1 | 2.0E3 | 2.0E2 | 1.0E-9 | 1.0E-9 | 1.4E4 | 7.3E2 | 50 | 14 | 50 | 14 | 0.68 |
| hL | pg/ml | 1.7E4 | 2.6E4 | 2.1E4 | 2.7E4 | 1.4E4 | 1.6E4 | 2.6E3 | 7.9E3 | 7.2E4 | 6.0E4 | 40 | 9 | 40 | 9 | 0.64 |
| hO | pg/ml | 1.6E4 | 1.5E4 | 1.6E4 | 1.5E4 | 2.5E3 | 2.2E3 | 1.3E4 | 1.1E4 | 2.4E4 | 1.8E4 | 40 | 9 | 40 | 9 | 0.35 |
| hP | ng/ml | 4.4E5 | 4.4E5 | 4.6E5 | 6.5E5 | 3.9E5 | 8.2E5 | 1.7E4 | 3.4E4 | 2.6E6 | 2.8E6 | 40 | 9 | 40 | 9 | 0.51 |
| wJ | pg/ml | 1.5E5 | 8.8E4 | 1.8E5 | 9.4E4 | 1.2E5 | 5.5E4 | 1.1E4 | 2.3E4 | 5.8E5 | 2.3E5 | 41 | 10 | 41 | 10 | 0.27 |
| wK | pg/ml | 3.2E4 | 2.9E4 | 5.3E4 | 3.7E4 | 7.8E4 | 2.8E4 | 3.7E3 | 1.1E4 | 5.0E5 | 1.0E5 | 41 | 10 | 41 | 10 | 0.42 |
| wL | pg/ml | 6.7E0 | 6.5E-1 | 5.7E1 | 4.0E1 | 1.5E2 | 1.1E2 | 1.0E-9 | 1.0E-9 | 8.4E2 | 3.5E2 | 41 | 10 | 41 | 10 | 0.38 |
| wP | pg/ml | 2.8E4 | 4.9E4 | 4.4E4 | 8.2E4 | 4.8E4 | 9.0E4 | 1.3E3 | 1.8E4 | 2.1E5 | 3.0E5 | 41 | 10 | 41 | 10 | 0.66 |
| wQ | pg/ml | 3.9E1 | 3.7E1 | 6.9E1 | 3.4E1 | 1.0E2 | 2.2E1 | 1.0E-9 | 1.0E-9 | 5.1E2 | 6.6E1 | 41 | 10 | 41 | 10 | 0.45 |
| hR | pg/ml | 2.7E4 | 2.9E4 | 2.9E4 | 2.9E4 | 1.1E4 | 1.0E4 | 1.0E-9 | 1.4E4 | 5.8E4 | 4.5E4 | 62 | 15 | 62 | 15 | 0.48 |
| hV | pg/ml | 4.4E2 | 4.3E2 | 4.4E2 | 4.1E2 | 2.2E2 | 1.9E2 | 1.0E-9 | 9.5E1 | 9.6E2 | 7.4E2 | 62 | 15 | 62 | 15 | 0.47 |
| hW | pg/ml | 1.8E3 | 2.4E3 | 2.1E3 | 5.1E3 | 1.2E3 | 9.7E3 | 1.0E-9 | 1.2E3 | 7.3E3 | 4.0E4 | 62 | 15 | 62 | 15 | 0.67 |
| hX | pg/ml | 1.0E3 | 1.1E3 | 1.2E3 | 1.1E3 | 1.1E3 | 4.7E2 | 2.5E0 | 3.1E2 | 8.6E3 | 2.0E3 | 62 | 15 | 62 | 15 | 0.57 |
| iA | pg/ml | 1.7E2 | 2.2E2 | 2.6E2 | 3.2E2 | 2.9E2 | 2.5E2 | 1.5E1 | 6.2E1 | 1.8E3 | 8.7E2 | 82 | 22 | 82 | 22 | 0.60 |
| iB | ng/ml | 4.9E0 | 7.3E0 | 6.1E0 | 9.9E0 | 4.5E0 | 6.6E0 | 3.3E-2 | 2.4E0 | 2.4E1 | 2.3E1 | 67 | 17 | 67 | 17 | 0.69 |
| iC | U/ml | 3.1E-1 | 5.8E-1 | 1.4E0 | 8.6E-1 | 6.8E0 | 8.7E-1 | 1.0E-9 | 6.8E-2 | 5.5E1 | 3.2E0 | 67 | 17 | 67 | 17 | 0.68 |
| tQ | pg/ml | 1.4E3 | 1.7E3 | 1.4E3 | 1.7E3 | 5.5E2 | 7.4E2 | 3.7E2 | 8.4E2 | 2.5E3 | 3.3E3 | 38 | 9 | 38 | 9 | 0.57 |
| tT | pg/ml | 1.9E1 | 2.3E1 | 2.0E1 | 3.1E1 | 1.0E1 | 2.6E1 | 5.4E0 | 1.1E1 | 4.8E1 | 9.3E1 | 39 | 9 | 39 | 9 | 0.65 |
| tS | pg/ml | 7.7E-1 | 6.9E-1 | 1.1E0 | 1.7E0 | 1.1E0 | 3.1E0 | 1.0E-9 | 1.0E-9 | 4.9E0 | 1.0E1 | 39 | 10 | 39 | 10 | 0.49 |
| tX | pg/ml | 1.0E0 | 1.6E0 | 1.3E0 | 3.4E0 | 1.3E0 | 3.6E0 | 2.5E-2 | 3.7E-1 | 7.0E0 | 1.0E1 | 39 | 9 | 39 | 9 | 0.67 |
| tO | pg/ml | 4.4E0 | 3.3E0 | 5.0E0 | 4.7E0 | 3.3E0 | 4.0E0 | 1.0E-9 | 1.7E0 | 1.8E1 | 1.5E1 | 39 | 10 | 39 | 10 | 0.42 |
| tR | pg/ml | 1.9E-1 | 2.2E-1 | 2.8E-1 | 4.3E-1 | 3.2E-1 | 7.5E-1 | 1.0E-9 | 1.4E-2 | 1.6E0 | 2.5E0 | 38 | 10 | 38 | 10 | 0.52 |
| tU | pg/ml | 9.2E0 | 1.3E1 | 1.1E1 | 1.9E1 | 1.1E1 | 2.2E1 | 2.2E-1 | 4.9E0 | 5.5E1 | 8.0E1 | 40 | 10 | 40 | 10 | 0.64 |
| tN | pg/ml | 1.9E1 | 2.2E1 | 2.6E1 | 4.8E1 | 2.7E1 | 5.0E1 | 1.0E-9 | 9.5E0 | 1.5E2 | 1.6E2 | 38 | 9 | 38 | 9 | 0.64 |
| tV | pg/ml | 5.4E2 | 9.5E2 | 7.0E2 | 1.1E3 | 5.0E2 | 8.2E2 | 5.3E1 | 3.9E2 | 1.8E3 | 3.1E3 | 41 | 9 | 41 | 9 | 0.67 |
| iH | ng/ml | 1.6E5 | 1.9E5 | 1.6E5 | 1.8E5 | 5.0E4 | 5.4E4 | 2.9E3 | 7.7E4 | 2.6E5 | 2.5E5 | 82 | 22 | 82 | 22 | 0.62 |
| iJ | ng/ml | 5.3E4 | 4.1E4 | 5.7E4 | 5.0E4 | 3.8E4 | 2.9E4 | 1.8E3 | 1.2E4 | 2.5E5 | 1.5E5 | 82 | 22 | 82 | 22 | 0.42 |
| hB | ng/ml | 4.5E-1 | 6.3E-1 | 5.7E-1 | 9.7E-1 | 4.1E-1 | 7.4E-1 | 1.2E-1 | 2.9E-1 | 2.3E0 | 3.2E0 | 82 | 22 | 82 | 22 | 0.73 |
| hC | pg/ml | 4.6E3 | 1.0E4 | 7.7E3 | 1.1E4 | 1.3E4 | 1.2E4 | 4.1E1 | 3.0E2 | 1.1E5 | 5.7E4 | 82 | 22 | 82 | 22 | 0.62 |
| hF | ng/ml | 1.0E-9 | 1.0E-9 | 4.9E1 | 1.0E-9 | 4.4E2 | 0.0E0 | 1.0E-9 | 1.0E-9 | 4.0E3 | 1.0E-9 | 82 | 22 | 82 | 22 | 0.49 |
| hG | pg/ml | 6.8E3 | 6.7E3 | 7.7E3 | 8.2E3 | 3.2E3 | 4.4E3 | 1.8E3 | 3.6E3 | 1.8E4 | 2.0E4 | 82 | 22 | 82 | 22 | 0.49 |
| iO | ng/ml | 4.0E5 | 3.2E5 | 4.5E5 | 3.8E5 | 2.0E5 | 1.9E5 | 1.0E5 | 9.8E4 | 1.1E6 | 8.2E5 | 82 | 22 | 82 | 22 | 0.39 |
| iP | ng/ml | 5.4E4 | 4.5E4 | 6.1E4 | 5.0E4 | 5.3E4 | 2.1E4 | 7.1E3 | 2.1E4 | 4.4E5 | 9.7E4 | 82 | 22 | 82 | 22 | 0.44 |
| iZ | ng/ml | 1.6E3 | 2.1E3 | 1.8E3 | 2.3E3 | 7.9E2 | 1.0E3 | 7.5E2 | 1.1E3 | 5.7E3 | 4.6E3 | 80 | 22 | 80 | 22 | 0.68 |
| yH | pg/ml | 9.1E2 | 1.4E3 | 2.6E3 | 1.9E3 | 5.7E3 | 1.9E3 | 1.0E-9 | 7.0E2 | 2.5E4 | 6.8E3 | 40 | 9 | 40 | 9 | 0.64 |
| yK | U/ml | 1.7E1 | 2.8E1 | 4.2E1 | 4.0E1 | 7.8E1 | 4.3E1 | 1.0E-9 | 1.0E-9 | 3.8E2 | 1.4E2 | 40 | 9 | 40 | 9 | 0.59 |
| yJ | pg/ml | 3.3E4 | 4.0E4 | 4.1E4 | 4.3E4 | 2.9E4 | 2.3E4 | 1.9E3 | 1.1E4 | 1.4E5 | 8.2E4 | 40 | 9 | 40 | 9 | 0.56 |
| yD | ng/ml | 1.3E-2 | 1.3E-2 | 1.3E-2 | 1.3E-2 | 6.1E-3 | 5.5E-3 | 1.0E-9 | 6.3E-3 | 2.8E-2 | 2.4E-2 | 41 | 10 | 41 | 10 | 0.50 |
| wB | pg/ml | 8.7E3 | 2.2E4 | 9.8E3 | 2.1E4 | 7.1E3 | 1.1E4 | 1.9E3 | 5.3E3 | 3.3E4 | 4.2E4 | 41 | 10 | 41 | 10 | 0.80 |
| pY | pg/ml | 5.9E0 | 6.4E0 | 1.1E1 | 7.4E0 | 3.1E1 | 3.8E0 | 1.6E0 | 4.4E0 | 2.0E2 | 1.7E1 | 40 | 9 | 40 | 9 | 0.61 |
| rC | pg/ml | 1.4E3 | 1.1E3 | 2.2E3 | 1.8E3 | 2.6E3 | 1.8E3 | 1.0E-9 | 7.0E1 | 1.5E4 | 7.3E3 | 59 | 15 | 59 | 15 | 0.45 |
| rB | pg/ml | 2.9E1 | 3.8E1 | 5.1E1 | 6.8E1 | 6.9E1 | 9.1E1 | 1.0E-9 | 1.0E-9 | 3.9E2 | 3.2E2 | 59 | 15 | 59 | 15 | 0.52 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| zG | 2.5ng/ml | 2.2E-1 | 3.8E-1 | 5.9E-1 | 6.3E-2 | 1.1E0 | 8.6E-1 | 1.0E-9 | 1.0E-9 | 4.8E0 | 2.7E0 | 40 | 9 | 40 | 9 | 0.59 |
| zH | 2.3mU/ml | 8.8E-2 | 8.5E-2 | 9.8E-2 | 8.4E-2 | 5.0E-2 | 2.6E-2 | 1.0E-2 | 4.4E-2 | 3.1E-1 | 1.2E-1 | 40 | 9 | 40 | 9 | 0.42 |
| zI | 2.6ng/ml | 2.1E0 | 3.4E0 | 4.2E0 | 6.0E0 | 5.8E0 | 5.9E0 | 5.4E-1 | 9.1E-1 | 2.7E1 | 1.6E1 | 40 | 9 | 40 | 9 | 0.63 |
| qA | ng/ml | 8.9E6 | 1.3E7 | 1.1E7 | 1.4E7 | 7.2E6 | 7.7E6 | 3.7E6 | 4.3E6 | 3.9E7 | 3.0E7 | 40 | 9 | 40 | 9 | 0.66 |
| qB | ng/ml | 7.2E5 | 5.7E5 | 8.3E5 | 9.9E5 | 5.7E5 | 1.1E6 | 1.9E5 | 2.4E5 | 2.9E6 | 3.8E6 | 40 | 9 | 40 | 9 | 0.44 |
| qC | ng/ml | 3.6E5 | 2.4E5 | 6.8E5 | 2.4E5 | 9.4E5 | 1.2E5 | 2.5E4 | 6.5E4 | 4.7E6 | 5.0E5 | 40 | 9 | 40 | 9 | 0.34 |
| qD | ng/ml | 1.6E7 | 1.4E7 | 1.7E7 | 1.4E7 | 7.7E6 | 5.1E6 | 7.0E6 | 1.0E7 | 3.7E7 | 2.6E7 | 40 | 9 | 40 | 9 | 0.39 |
| jD | ng/ml | 3.7E1 | 4.7E1 | 4.3E1 | 6.4E1 | 4.1E1 | 7.6E1 | 1.0E-9 | 1.0E-9 | 1.9E2 | 2.9E2 | 67 | 17 | 67 | 17 | 0.57 |
| jE | ng/ml | 1.0E-9 | 1.0E-9 | 4.9E0 | 5.9E0 | 1.2E1 | 1.2E1 | 1.0E-9 | 1.0E-9 | 6.2E1 | 3.5E1 | 67 | 17 | 67 | 17 | 0.52 |
| jF | ng/ml | 4.2E1 | 7.7E0 | 4.9E1 | 2.6E1 | 5.3E1 | 3.8E1 | 1.0E-9 | 1.0E-9 | 1.9E2 | 1.2E2 | 67 | 17 | 67 | 17 | 0.38 |
| jG | ng/ml | 4.4E3 | 4.2E3 | 4.6E3 | 4.1E3 | 2.0E3 | 1.8E3 | 6.7E2 | 1.5E3 | 9.6E3 | 7.9E3 | 67 | 17 | 67 | 17 | 0.43 |
| jH | ng/ml | 7.9E1 | 6.3E1 | 8.2E1 | 9.8E1 | 4.5E1 | 9.5E1 | 1.3E1 | 3.3E1 | 2.4E2 | 4.3E2 | 67 | 17 | 67 | 17 | 0.48 |
| jI | ng/ml | 7.3E1 | 9.6E1 | 7.9E1 | 1.2E2 | 3.3E1 | 1.0E2 | 3.8E1 | 4.4E1 | 1.9E2 | 4.4E2 | 67 | 17 | 67 | 17 | 0.63 |
| sK | pg/mL | 4.1E3 | 3.6E3 | 4.2E3 | 5.9E3 | 1.9E3 | 6.7E3 | 1.8E3 | 2.1E3 | 1.0E4 | 2.3E4 | 38 | 9 | 38 | 9 | 0.50 |
| sM | pg/mL | 7.3E4 | 7.9E4 | 7.9E4 | 9.3E4 | 3.1E4 | 4.3E4 | 3.9E4 | 5.1E4 | 1.6E5 | 2.0E5 | 38 | 9 | 38 | 9 | 0.62 |
| sO | pg/mL | 2.3E8 | 1.9E8 | 2.5E8 | 1.9E8 | 9.1E7 | 9.6E7 | 4.9E7 | 6.6E7 | 4.4E8 | 3.2E8 | 38 | 9 | 38 | 9 | 0.35 |
| wC | ng/ml | 1.5E0 | 1.7E0 | 1.9E0 | 1.7E0 | 1.3E0 | 1.2E0 | 3.6E-1 | 6.1E-2 | 6.5E0 | 4.3E0 | 41 | 10 | 41 | 10 | 0.50 |
| wD | ng/ml | 2.1E1 | 4.4E1 | 8.7E1 | 8.6E1 | 3.3E2 | 8.7E1 | 2.8E0 | 2.1E1 | 2.1E3 | 2.9E2 | 41 | 10 | 41 | 10 | 0.75 |
| wE | ng/ml | 5.0E1 | 4.1E1 | 5.2E1 | 4.7E1 | 1.9E1 | 2.0E1 | 8.1E0 | 2.0E1 | 8.9E1 | 8.9E1 | 41 | 10 | 41 | 10 | 0.39 |
| wG | ng/ml | 1.2E-1 | 5.8E-2 | 1.3E-1 | 1.5E-1 | 1.2E-1 | 2.3E-1 | 1.0E-9 | 1.0E-9 | 4.8E-1 | 6.8E-1 | 41 | 10 | 41 | 10 | 0.41 |
| wH | ng/ml | 3.3E-2 | 4.3E-2 | 2.5E-1 | 9.2E-1 | 7.0E-1 | 1.8E0 | 1.0E-9 | 1.0E-9 | 4.2E0 | 5.6E0 | 41 | 10 | 41 | 10 | 0.57 |
| wF | ng/ml | 1.8E-1 | 6.2E-1 | 2.7E0 | 1.8E0 | 9.9E0 | 2.0E0 | 1.0E-9 | 1.0E-9 | 5.7E1 | 4.7E0 | 41 | 10 | 41 | 10 | 0.63 |
| rA | pg/ml | 2.4E1 | 2.2E1 | 2.7E1 | 3.1E1 | 2.1E1 | 2.1E1 | 1.0E-9 | 5.8E0 | 1.1E2 | 7.2E1 | 64 | 17 | 64 | 17 | 0.55 |
| qZ | pg/ml | 4.7E1 | 9.1E1 | 6.7E2 | 4.2E2 | 2.4E3 | 9.5E2 | 2.8E-4 | 3.2E-3 | 1.0E4 | 3.4E3 | 48 | 12 | 48 | 12 | 0.59 |
| qY | pg/ml | 1.5E1 | 1.3E1 | 4.0E1 | 2.5E1 | 5.9E1 | 2.8E1 | 8.7E-1 | 2.1E0 | 3.3E2 | 9.8E1 | 64 | 17 | 64 | 17 | 0.45 |
| qX | pg/ml | 5.5E1 | 6.8E1 | 6.6E1 | 8.8E1 | 4.3E1 | 6.3E1 | 1.0E-9 | 2.3E1 | 1.7E2 | 2.1E2 | 64 | 17 | 64 | 17 | 0.57 |
| qW | pg/ml | 7.7E0 | 7.0E0 | 9.4E0 | 9.4E0 | 8.8E0 | 9.6E0 | 1.0E-9 | 1.0E-9 | 3.6E1 | 3.1E1 | 64 | 17 | 64 | 17 | 0.47 |
| qV | pg/ml | 1.6E3 | 1.6E3 | 2.3E3 | 2.5E3 | 1.8E3 | 2.4E3 | 1.0E2 | 1.7E2 | 1.1E4 | 9.6E3 | 64 | 17 | 64 | 17 | 0.50 |
| qU | pg/ml | 7.7E1 | 9.2E1 | 1.9E2 | 2.2E2 | 3.3E2 | 3.2E2 | 1.0E-9 | 1.0E-9 | 2.1E3 | 1.1E3 | 64 | 17 | 64 | 17 | 0.52 |
| qT | pg/ml | 3.8E1 | 4.3E1 | 6.7E1 | 6.5E1 | 7.9E1 | 5.0E1 | 1.0E-9 | 6.9E0 | 4.9E2 | 1.6E2 | 64 | 17 | 64 | 17 | 0.55 |
| qI | ng/ml | 6.3E4 | 5.9E4 | 6.5E4 | 5.9E4 | 3.2E4 | 2.6E4 | 1.0E4 | 2.5E4 | 1.6E5 | 9.8E4 | 37 | 9 | 37 | 9 | 0.47 |
| qH | ng/ml | 5.9E4 | 5.9E4 | 7.1E4 | 7.3E4 | 4.2E4 | 3.2E4 | 1.5E4 | 4.7E4 | 1.8E5 | 1.4E5 | 37 | 9 | 37 | 9 | 0.57 |
| qG | ng/ml | 1.8E5 | 1.7E5 | 1.9E5 | 1.7E5 | 7.3E4 | 4.8E4 | 3.4E4 | 9.9E4 | 4.2E5 | 2.3E5 | 37 | 9 | 37 | 9 | 0.43 |
| jK | ng/ml | 1.5E3 | 1.3E3 | 1.7E3 | 1.4E3 | 6.5E2 | 5.2E2 | 2.8E2 | 7.5E2 | 4.1E3 | 2.9E3 | 67 | 17 | 67 | 17 | 0.33 |
| jL | ng/ml | 1.8E2 | 2.6E2 | 2.7E2 | 2.9E2 | 2.1E2 | 1.5E2 | 5.9E1 | 1.2E2 | 8.1E2 | 6.3E2 | 67 | 17 | 67 | 17 | 0.61 |
| jM | ng/ml | 7.1E4 | 5.5E4 | 7.4E4 | 6.4E4 | 3.9E4 | 4.0E4 | 4.6E3 | 1.1E4 | 1.7E5 | 1.4E5 | 67 | 17 | 67 | 17 | 0.41 |
| jO | pg/ml | 2.3E5 | 2.5E5 | 2.8E5 | 2.5E5 | 1.5E5 | 1.4E5 | 7.6E4 | 9.8E4 | 7.7E5 | 6.5E5 | 67 | 17 | 67 | 17 | 0.44 |
| jP | pg/ml | 2.7E5 | 2.5E5 | 3.0E5 | 3.1E5 | 1.5E5 | 1.6E5 | 6.1E4 | 1.3E5 | 7.1E5 | 5.5E5 | 67 | 17 | 67 | 17 | 0.49 |
| jQ | pg/ml | 2.2E3 | 2.3E3 | 3.1E3 | 2.6E3 | 2.8E3 | 2.3E3 | 5.0E0 | 2.9E2 | 1.3E4 | 9.2E3 | 67 | 17 | 67 | 17 | 0.45 |
| jR | pg/ml | 5.7E3 | 3.8E3 | 9.9E3 | 8.6E3 | 1.1E4 | 1.2E4 | 1.0E-9 | 3.0E1 | 5.6E4 | 4.6E4 | 67 | 17 | 67 | 17 | 0.44 |
| jT | pg/ml | 1.9E5 | 1.5E5 | 1.8E5 | 1.4E5 | 6.2E4 | 4.3E4 | 7.1E4 | 7.5E4 | 3.5E5 | 2.2E5 | 67 | 17 | 67 | 17 | 0.31 |
| xA | pg/ml | 5.2E0 | 7.3E0 | 1.4E1 | 1.8E1 | 2.8E1 | 3.4E1 | 1.0E-9 | 1.0E-9 | 1.6E2 | 1.1E2 | 40 | 9 | 40 | 9 | 0.54 |
| yE | pg/ml | 8.1E1 | 9.1E1 | 8.0E1 | 1.0E2 | 3.3E1 | 4.2E1 | 6.4E0 | 6.3E1 | 1.5E2 | 2.0E2 | 40 | 9 | 40 | 9 | 0.64 |
| tM | pg/ml | 4.3E1 | 3.9E1 | 3.9E1 | 4.5E1 | 1.8E1 | 2.3E1 | 1.0E-9 | 1.6E1 | 8.3E1 | 9.9E1 | 40 | 9 | 40 | 9 | 0.53 |
| tL | pg/ml | 1.0E-9 | 1.0E-9 | 2.0E0 | 2.7E-1 | 1.1E1 | 6.1E-1 | 1.0E-9 | 1.0E-9 | 6.7E1 | 1.8E0 | 40 | 9 | 40 | 9 | 0.50 |
| jU | mIU/ml | 5.4E0 | 6.7E0 | 1.2E1 | 1.3E1 | 2.0E1 | 1.5E1 | 8.1E-2 | 1.2E0 | 1.1E2 | 5.3E1 | 67 | 17 | 67 | 17 | 0.53 |
| jV | mIU/ml | 1.9E0 | 1.9E0 | 4.1E0 | 3.7E0 | 5.7E0 | 4.8E0 | 2.7E-3 | 1.0E-1 | 3.2E1 | 1.8E1 | 67 | 17 | 67 | 17 | 0.46 |
| jY | ng/ml | 7.4E-4 | 2.7E-3 | 7.8E-3 | 1.1E-2 | 3.7E-2 | 2.3E-2 | 1.0E-9 | 1.0E-9 | 3.0E-1 | 9.4E-2 | 67 | 17 | 67 | 17 | 0.65 |
| kC | pg/ml | 1.1E2 | 9.2E1 | 2.1E2 | 1.3E2 | 4.1E2 | 1.4E2 | 2.1E1 | 3.6E1 | 2.7E3 | 5.9E2 | 50 | 14 | 50 | 14 | 0.42 |
| kE | pg/ml | 1.5E5 | 1.4E5 | 1.4E5 | 1.4E5 | 3.7E4 | 5.4E4 | 4.1E4 | 3.8E4 | 2.3E5 | 2.7E5 | 50 | 14 | 50 | 14 | 0.41 |
| kF | pg/mL | 6.9E1 | 5.3E1 | 7.0E1 | 7.2E1 | 2.3E1 | 3.5E1 | 3.5E1 | 4.0E1 | 1.5E2 | 1.4E2 | 50 | 14 | 50 | 14 | 0.42 |
| kG | pg/mL | 8.9E3 | 8.6E3 | 1.2E4 | 2.4E4 | 1.0E4 | 4.2E4 | 1.9E3 | 1.1E3 | 5.8E4 | 1.6E5 | 50 | 14 | 50 | 14 | 0.49 |
| kI | pg/ml | 2.1E2 | 1.9E2 | 2.2E2 | 2.3E2 | 1.1E2 | 1.4E2 | 4.4E1 | 1.0E-9 | 6.7E2 | 5.5E2 | 50 | 14 | 50 | 14 | 0.50 |
| kK | pg/ml | 1.2E2 | 1.2E2 | 1.5E2 | 1.7E2 | 1.5E2 | 1.2E2 | 2.1E1 | 2.9E1 | 9.1E2 | 4.9E2 | 50 | 14 | 50 | 14 | 0.58 |
| kN | pg/ml | 1.2E3 | 7.5E2 | 1.7E3 | 1.3E3 | 1.9E3 | 1.7E3 | 2.1E2 | 3.8E2 | 1.0E4 | 7.0E3 | 50 | 14 | 50 | 14 | 0.36 |
| kO | pg/ml | 7.2E3 | 7.0E3 | 1.1E4 | 7.4E3 | 2.0E4 | 2.5E3 | 3.8E3 | 4.4E3 | 1.5E5 | 1.3E4 | 50 | 14 | 50 | 14 | 0.45 |
| kP | pg/ml | 5.9E3 | 4.5E3 | 6.9E3 | 5.6E3 | 4.4E3 | 3.7E3 | 9.6E2 | 1.6E3 | 2.7E4 | 1.5E4 | 50 | 14 | 50 | 14 | 0.40 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| kQ | pg/ml | 4.7E3 | 4.3E3 | 5.6E3 | 5.6E3 | 4.2E3 | 4.4E3 | 5.6E2 | 1.4E3 | 2.5E4 | 2.2E4 | 82 | 22 | 82 | 22 | 0.48 |
| kR | pg/ml | 2.4E1 | 2.2E1 | 4.0E1 | 3.7E1 | 1.1E2 | 3.2E1 | 1.0E-9 | 5.5E0 | 1.0E3 | 1.1E2 | 82 | 22 | 82 | 22 | 0.53 |
| kS | pg/ml | 8.6E2 | 9.4E2 | 9.8E2 | 1.0E3 | 6.0E2 | 5.9E2 | 8.2E1 | 2.5E2 | 3.2E3 | 2.5E3 | 82 | 22 | 82 | 22 | 0.54 |
| pS | ng/ml | 1.6E5 | 1.2E5 | 2.0E5 | 1.3E5 | 1.1E5 | 5.5E4 | 7.5E4 | 6.8E4 | 5.7E5 | 2.6E5 | 38 | 9 | 38 | 9 | 0.23 |
| rZ | ng/ml | 1.6E-3 | 8.2E-3 | 7.1E-3 | 1.7E-2 | 1.6E-2 | 2.8E-2 | 1.0E-9 | 1.0E-9 | 9.4E-2 | 1.1E-1 | 60 | 15 | 60 | 15 | 0.61 |
| rY | ng/ml | 6.4E-2 | 6.9E-2 | 5.4E-1 | 1.0E-1 | 2.7E0 | 1.2E-1 | 1.0E-9 | 1.0E-9 | 2.0E1 | 5.0E-1 | 60 | 15 | 60 | 15 | 0.54 |
| rX | ng/ml | 1.0E-9 | 1.0E-9 | 1.3E-1 | 3.2E-2 | 6.2E-1 | 7.8E-2 | 1.0E-9 | 1.0E-9 | 3.7E0 | 2.9E-1 | 60 | 15 | 60 | 15 | 0.59 |
| lK | pg/ml | 6.2E1 | 6.8E1 | 1.4E2 | 1.2E2 | 1.7E2 | 1.6E2 | 1.0E-9 | 2.3E0 | 7.0E2 | 5.0E2 | 66 | 17 | 66 | 17 | 0.45 |
| lL | pg/ml | 1.5E3 | 1.8E3 | 3.1E3 | 2.4E3 | 5.6E3 | 2.0E3 | 7.5E1 | 5.3E2 | 4.2E4 | 7.7E3 | 67 | 17 | 67 | 17 | 0.52 |
| lM | pg/ml | 1.1E3 | 2.6E3 | 3.8E3 | 1.0E4 | 6.8E3 | 1.8E4 | 9.5E0 | 2.6E2 | 4.2E4 | 6.7E4 | 67 | 17 | 67 | 17 | 0.63 |
| lN | pg/ml | 1.0E-9 | 1.0E-9 | 3.1E0 | 4.0E0 | 7.3E0 | 6.5E0 | 1.0E-9 | 1.0E-9 | 4.3E1 | 2.1E1 | 67 | 17 | 67 | 17 | 0.57 |
| lO | pg/ml | 1.0E-9 | 1.0E-9 | 2.4E0 | 8.1E0 | 1.6E1 | 3.3E1 | 1.0E-9 | 1.0E-9 | 1.3E2 | 1.4E2 | 66 | 17 | 66 | 17 | 0.52 |
| zA | ng/ml | 2.1E7 | 2.1E7 | 2.2E7 | 1.9E7 | 6.5E6 | 4.8E6 | 1.0E7 | 1.1E7 | 3.6E7 | 2.5E7 | 40 | 10 | 40 | 10 | 0.40 |
| rW | ng/ml | 1.1E-2 | 1.5E-2 | 3.5E-2 | 1.8E-2 | 6.5E-2 | 8.0E-3 | 1.0E-9 | 7.4E-3 | 3.2E-1 | 3.3E-2 | 37 | 9 | 37 | 9 | 0.60 |
| rV | ng/ml | 1.0E-9 | 6.7E-3 | 9.3E-3 | 2.9E-2 | 4.6E-2 | 5.0E-2 | 1.0E-9 | 1.0E-9 | 2.8E-1 | 1.5E-1 | 37 | 9 | 37 | 9 | 0.71 |
| rU | ng/ml | 7.1E-2 | 1.3E-1 | 1.6E-1 | 1.6E-1 | 4.4E-1 | 1.3E-1 | 1.0E-9 | 1.0E-9 | 2.7E0 | 4.0E-1 | 37 | 9 | 37 | 9 | 0.66 |
| rT | ng/ml | 6.1E0 | 6.8E0 | 6.8E0 | 7.6E0 | 4.7E0 | 5.6E0 | 6.5E-1 | 1.0E0 | 2.1E1 | 1.8E1 | 37 | 9 | 37 | 9 | 0.54 |
| rS | ng/ml | 3.5E0 | 9.0E0 | 5.3E0 | 2.4E1 | 5.1E0 | 2.5E1 | 1.1E0 | 2.0E0 | 2.5E1 | 7.0E1 | 37 | 9 | 37 | 9 | 0.80 |
| sC | pg/mL | 5.4E3 | 7.9E3 | 1.1E4 | 1.0E4 | 1.5E4 | 7.7E3 | 1.7E3 | 3.4E3 | 7.4E4 | 2.8E4 | 38 | 9 | 38 | 9 | 0.62 |
| yL | pg/ml | 2.9E1 | 4.1E1 | 3.4E1 | 2.0E2 | 2.7E1 | 4.6E2 | 5.6E0 | 1.2E1 | 1.8E2 | 1.4E3 | 40 | 9 | 40 | 9 | 0.67 |
| rP | ng/ml | 1.2E2 | 2.1E2 | 2.1E2 | 2.8E2 | 2.1E2 | 2.2E2 | 1.0E-9 | 1.2E1 | 8.0E2 | 5.0E2 | 37 | 9 | 37 | 9 | 0.59 |
| rQ | ng/ml | 1.0E-9 | 1.0E-9 | 4.1E0 | 1.9E1 | 2.1E1 | 5.6E1 | 1.0E-9 | 1.0E-9 | 1.2E2 | 1.7E2 | 37 | 9 | 37 | 9 | 0.53 |
| rO | ng/ml | 2.0E-2 | 4.0E-3 | 4.1E-2 | 3.0E-2 | 7.2E-2 | 4.8E-2 | 1.0E-9 | 1.0E-9 | 4.0E-1 | 1.2E-1 | 37 | 9 | 37 | 9 | 0.41 |
| rR | ng/ml | 3.9E0 | 1.0E-9 | 1.0E1 | 1.8E1 | 1.9E1 | 3.2E1 | 1.0E-9 | 1.0E-9 | 7.9E1 | 9.5E1 | 37 | 9 | 37 | 9 | 0.51 |
| rN | ng/ml | 6.2E-1 | 1.3E0 | 7.5E-1 | 2.8E0 | 5.2E-1 | 4.0E0 | 5.1E-2 | 3.4E-1 | 2.3E0 | 1.3E1 | 37 | 9 | 37 | 9 | 0.74 |
| qO | pg/ml | 8.0E3 | 1.0E4 | 1.2E4 | 1.2E4 | 1.1E4 | 9.3E3 | 7.4E2 | 5.4E3 | 4.8E4 | 3.5E4 | 38 | 9 | 38 | 9 | 0.56 |
| qP | pg/ml | 3.3E2 | 3.6E2 | 4.2E2 | 3.9E2 | 3.0E2 | 2.0E2 | 7.0E1 | 1.5E2 | 1.5E3 | 7.8E2 | 38 | 9 | 38 | 9 | 0.52 |
| qQ | pg/ml | 1.5E1 | 3.3E1 | 2.4E1 | 2.6E1 | 6.0E1 | 1.8E1 | 1.0E-9 | 1.0E-9 | 2.8E2 | 4.3E1 | 38 | 9 | 38 | 9 | 0.72 |
| nW | pg/ml | 1.1E5 | 1.1E5 | 1.1E5 | 1.1E5 | 2.6E4 | 3.4E4 | 5.8E4 | 3.6E4 | 1.8E5 | 1.7E5 | 82 | 22 | 82 | 22 | 0.51 |
| nY | pg/ml | 2.2E3 | 3.4E3 | 2.6E3 | 3.2E3 | 1.6E3 | 1.8E3 | 5.1E2 | 6.3E2 | 1.0E4 | 8.1E3 | 82 | 22 | 82 | 22 | 0.61 |
| oO | pg/ml | 9.1E4 | 9.8E4 | 1.1E5 | 1.2E5 | 6.3E4 | 1.0E5 | 2.0E4 | 3.3E3 | 3.0E5 | 4.0E5 | 45 | 12 | 45 | 12 | 0.52 |
| oP | pg/ml | 1.3E5 | 1.6E5 | 1.5E5 | 2.0E5 | 7.6E4 | 1.5E5 | 4.2E4 | 2.4E4 | 4.1E5 | 5.7E5 | 45 | 12 | 45 | 12 | 0.62 |
| oQ | pg/ml | 3.1E3 | 4.2E3 | 3.8E3 | 6.8E3 | 3.2E3 | 8.2E3 | 7.7E2 | 9.1E2 | 2.1E4 | 3.2E4 | 45 | 12 | 45 | 12 | 0.67 |
| oE | pg/ml | 2.1E2 | 5.6E2 | 4.7E2 | 8.9E2 | 5.6E2 | 9.9E2 | 1.0E-9 | 1.0E-9 | 2.6E3 | 3.4E3 | 82 | 22 | 82 | 22 | 0.61 |
| oF | pg/ml | 1.3E4 | 3.1E4 | 2.5E4 | 4.9E4 | 3.6E4 | 4.9E4 | 4.3E2 | 6.5E2 | 2.5E5 | 1.7E5 | 82 | 22 | 82 | 22 | 0.68 |
| oH | pg/ml | 3.9E1 | 2.3E1 | 8.7E1 | 5.5E1 | 1.3E2 | 7.9E1 | 4.4E0 | 4.3E-1 | 8.6E2 | 3.1E2 | 82 | 22 | 82 | 22 | 0.40 |
| oK | pg/ml | 8.6E2 | 1.3E3 | 1.6E3 | 1.5E3 | 1.9E3 | 1.4E3 | 8.8E1 | 1.8E2 | 1.2E4 | 5.9E3 | 82 | 22 | 82 | 22 | 0.53 |
| oN | pg/ml | 5.5E2 | 5.8E2 | 1.1E3 | 7.5E2 | 2.2E3 | 3.9E2 | 1.1E2 | 3.3E2 | 1.8E4 | 1.8E3 | 82 | 22 | 82 | 22 | 0.60 |
| uL | ng/ml | 3.5E1 | 4.3E1 | 4.7E1 | 4.4E1 | 4.7E1 | 2.5E1 | 1.5E1 | 1.4E1 | 2.9E2 | 8.0E1 | 38 | 9 | 38 | 9 | 0.53 |
| uO | ng/ml | 4.1E-1 | 4.8E-1 | 8.6E-1 | 8.6E-1 | 1.6E0 | 8.5E-1 | 1.0E-9 | 1.0E-9 | 9.3E0 | 2.1E0 | 38 | 9 | 38 | 9 | 0.56 |
| uM | ng/ml | 5.4E-1 | 6.2E-1 | 9.8E-1 | 7.6E-1 | 2.1E0 | 7.6E-1 | 1.0E-9 | 1.0E-9 | 1.3E1 | 2.5E0 | 38 | 9 | 38 | 9 | 0.51 |
| uI | ng/ml | 7.2E-2 | 5.1E-2 | 1.1E-1 | 1.0E-1 | 1.2E-1 | 1.2E-1 | 1.6E-2 | 1.5E-2 | 5.8E-1 | 3.8E-1 | 37 | 9 | 37 | 9 | 0.44 |
| uN | ng/ml | 1.5E1 | 1.7E1 | 1.7E1 | 2.0E1 | 6.5E0 | 9.7E0 | 8.0E0 | 1.0E1 | 3.6E1 | 4.1E1 | 38 | 9 | 38 | 9 | 0.63 |
| uG | ng/ml | 1.8E1 | 1.9E1 | 2.2E1 | 3.4E1 | 1.5E1 | 3.9E1 | 1.2E0 | 6.5E0 | 7.9E1 | 1.3E2 | 38 | 9 | 38 | 9 | 0.58 |
| uR | ng/ml | 2.2E0 | 1.7E0 | 2.9E0 | 2.3E0 | 2.4E0 | 1.8E0 | 7.5E-1 | 9.1E-1 | 1.3E1 | 6.6E0 | 40 | 9 | 40 | 9 | 0.39 |
| uP | ng/ml | 2.1E0 | 2.7E0 | 2.4E0 | 3.1E0 | 9.7E-1 | 1.7E0 | 1.2E0 | 9.3E-1 | 6.0E0 | 6.1E0 | 40 | 9 | 40 | 9 | 0.66 |
| uV | ng/ml | 1.7E-3 | 1.3E-3 | 1.6E-2 | 8.0E-3 | 3.5E-2 | 1.4E-2 | 1.0E-9 | 1.0E-9 | 2.0E-1 | 4.3E-2 | 40 | 9 | 40 | 9 | 0.46 |
| uT | ng/ml | 6.4E1 | 1.2E2 | 9.2E1 | 1.6E2 | 8.8E1 | 1.1E2 | 1.3E1 | 5.7E1 | 4.5E2 | 4.1E2 | 40 | 9 | 40 | 9 | 0.78 |
| uU | ng/ml | 1.7E0 | 1.7E0 | 1.8E0 | 3.8E0 | 1.1E0 | 6.0E0 | 6.0E-1 | 5.4E-1 | 6.0E0 | 2.0E1 | 40 | 9 | 40 | 9 | 0.56 |
| uW | ng/ml | 7.8E0 | 7.9E0 | 8.1E0 | 8.1E0 | 2.4E0 | 1.8E0 | 4.4E0 | 6.5E0 | 1.6E1 | 1.1E1 | 38 | 9 | 38 | 9 | 0.53 |
| vB | ng/ml | 3.0E0 | 3.2E0 | 3.6E0 | 2.9E0 | 2.4E0 | 8.4E-1 | 5.9E-1 | 1.3E0 | 1.0E1 | 3.8E0 | 38 | 9 | 38 | 9 | 0.47 |
| vC | ng/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 38 | 9 | 38 | 9 | 0.50 |
| uY | ng/ml | 6.1E-1 | 8.7E-1 | 8.9E-1 | 1.4E0 | 8.7E-1 | 1.3E0 | 6.8E-2 | 3.1E-1 | 3.8E0 | 4.4E0 | 38 | 9 | 38 | 9 | 0.67 |
| uZ | ng/ml | 5.8E-1 | 5.3E-1 | 7.6E-1 | 6.5E-1 | 8.5E-1 | 5.1E-1 | 1.0E-1 | 1.7E-1 | 4.9E0 | 1.9E0 | 38 | 9 | 38 | 9 | 0.47 |
| uX | ng/ml | 8.1E0 | 9.1E0 | 1.0E1 | 2.3E1 | 6.6E0 | 2.3E1 | 3.6E0 | 5.6E0 | 4.0E1 | 6.5E1 | 38 | 9 | 38 | 9 | 0.68 |
| vA | ng/ml | 6.3E-2 | 6.6E-2 | 7.3E-2 | 1.2E-1 | 4.3E-2 | 1.3E-1 | 2.9E-2 | 2.5E-2 | 2.7E-1 | 4.2E-1 | 38 | 9 | 38 | 9 | 0.56 |
| vH | ng/ml | 1.2E-1 | 1.1E-1 | 1.5E-1 | 3.4E-1 | 1.3E-1 | 6.0E-1 | 2.0E-2 | 4.7E-2 | 6.6E-1 | 1.9E0 | 38 | 9 | 38 | 9 | 0.49 |

Figure 30 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| vl | ng/ml | 2.1E0 | 3.5E0 | 2.4E0 | 3.9E0 | 1.9E0 | 2.7E0 | 6.3E-3 | 1.2E0 | 1.0E1 | 1.0E1 | 38 | 9 | 38 | 9 | 0.74 |
| vP | ng/ml | 3.6E2 | 2.9E2 | 4.7E2 | 4.3E2 | 4.5E2 | 3.2E2 | 6.7E1 | 1.5E2 | 2.4E3 | 1.1E3 | 40 | 9 | 40 | 9 | 0.54 |
| vT | ng/ml | 7.1E1 | 8.2E1 | 8.1E1 | 9.9E1 | 3.6E1 | 5.2E1 | 4.1E1 | 4.6E1 | 2.4E2 | 1.8E2 | 40 | 9 | 40 | 9 | 0.56 |
| vU | ng/ml | 1.0E-9 | 1.0E-9 | 2.3E1 | 1.9E1 | 3.5E1 | 3.7E1 | 1.0E-9 | 1.0E-9 | 1.2E2 | 1.1E2 | 40 | 9 | 40 | 9 | 0.46 |
| vQ | ng/ml | 4.0E2 | 4.5E2 | 4.1E2 | 4.0E2 | 1.6E2 | 1.8E2 | 7.2E1 | 1.9E2 | 8.4E2 | 6.5E2 | 40 | 9 | 40 | 9 | 0.48 |
| vO | ng/ml | 1.7E3 | 1.7E3 | 1.8E3 | 1.8E3 | 4.4E2 | 6.0E2 | 1.1E3 | 1.0E3 | 2.9E3 | 3.2E3 | 40 | 9 | 40 | 9 | 0.49 |
| vS | ng/ml | 1.3E3 | 1.3E3 | 1.2E3 | 1.3E3 | 4.5E2 | 5.7E2 | 1.0E-9 | 1.0E-9 | 2.1E3 | 1.9E3 | 40 | 9 | 40 | 9 | 0.56 |
| vV | ng/ml | 8.7E2 | 8.2E2 | 1.0E3 | 9.1E2 | 9.9E2 | 5.3E2 | 1.0E2 | 2.3E2 | 4.6E3 | 1.7E3 | 40 | 9 | 40 | 9 | 0.53 |
| vW | ng/ml | 1.1E2 | 2.4E2 | 1.4E2 | 2.6E2 | 8.5E1 | 2.2E2 | 4.3E1 | 6.0E1 | 4.5E2 | 7.7E2 | 40 | 9 | 40 | 9 | 0.68 |
| pF | pg/ml | 6.0E-1 | 5.6E-1 | 1.9E0 | 8.8E-1 | 9.6E0 | 7.7E-1 | 1.0E-9 | 1.8E-1 | 8.7E1 | 3.5E0 | 82 | 22 | 82 | 22 | 0.54 |

Analyte panel data:

Unconstrained panels with 3 analytes, where 1.0E-10 >= 'model p-value' > 0. Contains 8,015 panels of 32,874,593 total panels evaluated. :
Nw{Et(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Ns(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Ms(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Mv(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mw Mx My Mz Na Nb Nc Nd Ne Nf Ng Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) My(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Ng Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Ng(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Hu(aA Fp Fr Hq Hr Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Hx(aA Fp Fr Hq Hr Hv Hw Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Im(aA Fp Fr Hq Hr Hv Hw Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) It(aA Fp Fr Hq Hr Hv Hw Ih Ii Ij Ik Il In Io Ip Iq Ir Is Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Ji(aA Fp Fr Hq Hr Hv Hw Ih Ii Ij Ik Il In Io Ip Iq Ir Is Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Jj(aA Fp Fr Hq Hr Hv Hw Ih Ii Ij Ik Il In Io Ip Iq Ir Is Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Li(aA Fp Fr Hq Hr Hv Hw Ih Ii Ij Ik Il In Io Ip Iq Ir Is Iu Iv Jg Jh Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Lj(aA Fp Fr Hq Hr Hv Hw Ih Ii Ij Ik Il In Io Ip Iq Ir Is Iu Iv Jg Jh Jk Jl Jm Jn Jo Jp Jq Jr Js Jt Lh Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Og Oh Oi Ok Om On Oy Oz Pa Pb Pc Pd Pe Pf Pg Po Pz Qa Qb Qc Qd Qe) Og(aA Fp Fr Hq Hr Hv Hw Ih Ii Ij Ik Il In Io Ip Iq Ir Is It Iu Iv Jg Jh Jk Jl Jm Jn Jo Jp Jq Jr Js Jt Lh Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Oh Oi Ok Om On Oy Oz Pa Pb Pc Pd Pe Pf Pg Po Pz Qa Qb Qc Qd Qe) Oy(aA Fp Fr Hq Hr Hv Hw Ih Ii Ij Ik Il In Io Ip Iq Ir Is Iu Iv Jg Jh Jk Jl Jm Jn Jo Jp Jq Jr Js Jt Lh Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Oh Oi Ok Om On Oz Pa Pb Pc Pd Pe Pf Pg Po Pz Qa Qb Qc Qd Qe) Oz(aA Fp Fr Hq Hr Hv Hw Ih Ii Ij Ik Il In Io Ip Iq Ir Is Iu Iv Jg Jh Jk Jl Jm Jn Jo Jp Jq Jr Js Jt Lh Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Oh Oi Ok Om On Pa Pb Pc Pd Pe Pf Pg Po Pz Qa Qb Qc Qd Qe) Pb(aA Fp Fr Hq Hr Hv Hw Ih Ii Ij Ik Il In Io Ip Iq Ir Is Iu Iv Jg Jh Jk Jl Jm Jn Jo Jp Jq Jr Js Jt Lh Lu Lv Lw Lx Ly Lz Ma Mb Mc Md Me Mf Mg Mh Mi Mj Mk Ml Mm Mn Mp Mq Mr Mt Mu Mw Mx Mz Na Nb Nc Nd Ne Nf Nh Ni Nj Nk Nl Nm Nn No Nq Nr Nt Nu Nv Nx Ny Oe Of Oh Oi Ok Om On Pa Pc Pd Pe Pf Pg Po Pz Qa Qb Qc Qd Qe) aA(Fp Fr Hq Hr Hv Hw Ih Ii Ij Ik Il In Io Ip Iq Ir Is Iu Iv Jg Jh Jk Jl Jm Jn Jo Jp Jq Jr Js Jt Lh Lu Lv Lw Lx Ly Lz Ma Mb Mc Md Me

Jl Jm Jn Jq Js Jt Lh Lx Lz Mn Mp Mr Ms Mw My Mz Nc Nj Nl Nn No Ns Nv Oe Og Ok On Oz Pb Po Qa Qb Qd Qe) aA(Fp Hu Ih Ij Ip Is Jn Lw Ms My Mz Ng Nj Nl Ns Oe Og Oi Oy Oz Pb Th) Og(Fp Ih Ij Ip Is Iv Jn Jq Js Mr Mz Nn No Ns Ok On Oz Qb) Oe(Fp Ih Ij Is Iv Jn Js Nn No Ns Qa Qb) No(Aj My Ng Ns Oy Oz Pb Th) Is(Hu Ms My Ng Ns Oy Oz Pb) Fp(Ik My Ns Oy) Ij(Ms My Ng Oy) My(Mt On) Oy(Lx On) NgIh} Li{Jj(aA Fp Fr Hq Hr Hu Hv Hw Hx Ih Ii Ij Ik Il In Io Ip Iq Ir Is It Iu Iv Jg Jh Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Og(aA Hu Ih Ii Ij Ik Il In Ip Ir Is It Iv Jg Jl Jm Jn Jp Jq Js Jt Lh Lv Lw Lx Lz Mb Mc Ml Mn Mr Mt Mw Mz Nb Nl Nm Nn No Ns Nv Nx Ny Ok On Oz Pb Pe Pz Qa Qb Qd Qe) Ik(aA Hu Ih Ij Ip Iq Ir Is It Iv Jl Jn Jq Js Lj Lw Mn My Mz Ng Nl No Ns Oe Oi Ok On Oy Pb Qa Qd) Ok(aA Hr Hu Ih Ii Is It Jo Lj Mc Mj Mk Ms My Ng Ns Oe Of Oi Oy Oz Pb) aA(Hu Ih Ij Ip It Lw Md Mn Mv My Mz Ng Nj Ns Oe Oi Oy Oz Pb) Is(Hu Ij Il In It Lw Mk Ms Mv My Ng Ns Oe Oi Oy Oz Pb) Pb(Ih Ij Ip It Jl Lw Mz No Ns Oe On) Ns(Ih It Jl Lw No On) Ng(Ih Ij Jg Lw On) Ih(Hu Oe Oi Oy) On(Hu My Oe Oy) Ij(Hu My Oy) JlOy} Jj{On(Fp Hu Ij Ip Is It Jn Lj Ms My Ng Nl No Ns Oe Og Ok Oy Oz Pb) Ij(aA Ip Is It Lh Lj My Nn No Og Ok Oy) Ok(Ip Is It Lj Nn No Og) It(Aa Lh Nn No Nv) Is(Lh Lj No) Lj(Lh Nv) Nolp} Og{Ij(aA Is Jg Jl Lj No Ok On) Is(Jg Lj No Ok On) Lj(Jg Ok On) It(Ok On) NsOn} Ij{aA(Hu Lj My Oy Pb) My(Mt On) Oy(Lx On)} Lj{On(Ik Ns Oe Oy) Ok(aA It Oe)} No{Ti(aK aU cY Vt) Th(Ke Vt)} Ch{ThKq KeOw} GcNeaA Unconstrained panels with 3 analytes, where 1.0E-9 >= 'model p-value' > 1.0E-10. Contains 13,525 panels of 32,874,593 total panels evaluated. :
Ji{Nm(Fp Fr Hq Hr Hu Hv Hw Hx Ih Ii Ij Ik Il In Io Ip Iq Ir Is Iu Iv Jg Jh Jk Jl Jm Jn Jp Jr Js Jt Lh Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nn Nq Nr Nt Nu Nv Nx Ny Of Oh Oi Ok Om On Oz Pa Pc Pd Pe Pf Pg Po Pz Qa Qb Qc Qd Qe) Lv(Fp Fr Hq Hr Hu Hv Hw Hx Ih Ii Ij Il In Io Ip Iq Ir Is Iu Iv Jg Jh Jk Jl Jm Jn Jp Jr Js Jt Lh Lu Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Ng Nh Ni Nj Nk Nl Nn Nq Nr Nt Nu Nv Nx Ny Of Oh Oi Ok Om On Oz Pa Pc Pd Pe Pf Pg Po Pz Qa Qb Qc Qd Qe) Mq(Fp Fr Hq Hr Hu Hv Hw Hx Ih Ii Ij Il In Io Ip Iq Ir Iu Iv Jg Jh Jk Jl Jm Jn Jo Jp Jr Js Jt Lh Lu Lw Lx Ly Lz Ma Mb Mc Md Me Mf Mg Mh Mi Mj Mk Ml Mm Mn Mp Mr Mt Mu Mv Mw Mx Mz Na Nb Nc Nd Ne Nf Ng Nh Ni Nj Nk Nl Nn Nq Nr Nt Nu Nv Nx Ny Of Oh Oi Ok Om On Oz Pa Pc Pd Pe Pf Pg Po Pz Qa Qb Qc Qd Qe) Nu(Fp Fr Hq Hr Hu Hv Hw Hx Ih Ii Ij Il In Io Ip Iq Ir Is Iu Iv Jg Jh Jk Jl Jm Jn Jp Jr Js Jt Lh Lu Lw Lx Ly Lz Ma Mb Mc Md Me Mf Mg Mh Mi Mj Mk Ml Mm Mn Mp Mr Mt Mu Mv Mw Mx Mz Na Nb Nc Nd Ne Nf Nh Ni Nj Nk Nl Nn Nq Nr Nt Nv Nx Ny Of Oh Oi Ok Om On Oz Pa Pc Pd Pe Pf Pg Po Pz Qa Qb Qc Qd Qe) Ly(Fr Hq Hr Hu Hv Hw Hx Ih Ii Ij Il In Io Ip Iq Ir Iu Iv Jg Jh Jk Jl Jm Jn Jo Jp Jr Js Jt Lh Lu Lw Lx Lz Ma Mb Mc Md Me Mf Mg Mh Mi Mj Mk Ml Mm Mn Mp Mr Mt Mu Mv Mw Mx Mz Na Nb Nc Nd Ne Nf Ng Nh Ni Nj Nk Nl Nn Nq Nr Nt Nv Nx Ny Of Oh Oi Ok Om On Oz Pa Pc Pd Pe Pf Pg Po Pz Qa Qb Qc Qd Qe) Mx(Fp Fr Hq Hr Hu Hv Hw Hx Ih Ii Ij Il In Io Ip Iq Ir Iu Iv Jg Jh Jk Jl Jm Jn Jp Jr Js Jt Lh Lu Lw Lx Lz Ma Mb Mc Md Me Mf Mg Mh Mi Mj Mk Ml Mm Mn Mp Mr Mt Mu Mv Mw Mz Na Nb Nc Nd Ne Nf Ng Nh Ni Nj Nk Nl Nn Nq Nr Nt Nv Nx Ny Of Oh Oi Ok Om On Oz Pa Pc Pd Pe Pf Pg Po Pz Qa Qb Qc Qd Qe) Nf(Fr Hq Hr Hu Hv Hw Hx Ih Ii Ij Il In Io Ip Iq Ir Iu Iv Jg Jh Jk Jl Jm Jn Jo Jp Jr Js Jt Lh Lu Lw Lx Lz Ma Mb Mc Md Me Mf Mg Mh Mi Mj Mk Ml Mm Mn Mp Mr Mt Mu Mv Mw Mz Na Nb Nc Nd Ne Ng Nh Ni Nj Nk Nl Nn Nq Nr Nt Nv Nx Ny Of Oh Oi Ok Om On Oz Pa Pc Pd Pe Pf Pg Po Pz Qa Qb Qc Qd Qe) Nj(Fp Fr Hq Hr Hu Hv Hw Hx Ih Ii Ij Il In Io Ip Iq Ir Iu Iv Jg Jh Jk Jl Jm Jn Jp Jr Js Jt Lh Lu Lw Lx Lz Ma Mb Mc Md Me Mf Mg Mh Mi Mj Mk Ml Mm Mn Mp Mr Mt Mu Mv Mw Mz Na Nb Nc Nd Ne Ng Nh Ni Nk Nl Nn Nq Nr Nt Nv Nx Ny Of Oh Oi Ok Om On Oz Pa Pc Pd Pe Pf Pg Po Pz Qa Qb Qc Qd Qe) Nt(Fp Fr Hq Hr Hu Hv Hw Hx Ih Ij Il In Io Ip Iq Ir Is Iu Iv Jg Jh Jk Jl Jm Jn Jp Jr Js Jt Lh Lu Lw Lx Lz Ma Mb Mc Md Me Mf Mg Mh Mi Mj Mk Ml Mm Mn Mp Mr Mt Mu Mv Mw Mz Na Nb Nc Nd Ne Nh Ni Nk Nl Nn Nq Nr Nv Nx Ny Of Oh Oi Ok Om On Oz Pa Pc Pd Pe Pf Pg Po Pz Qa Qb Qc Qd Qe) Lw(Fp Fr Hq Hr Hu Hv Hw Hx Ih Ii Ij Il In Io Ip Iq Ir Iu Iv Jg Jh Jk Jl Jm Jn Jp Jr Js Jt Lh Lu Lx Lz Ma Mb Mc Md Me Mf Mg Mh Mi Mj Mk Ml Mm Mn Mp Mr Mt Mu Mv Mw Mz Na Nb Nc Nd Ne Nh Ni Nk Nl Nn Nq Nr Nv Nx Ny Of Oh Oi Ok Om On Oz Pa Pc Pd Pe Pf Pg Po Pz Qa Qb Qc Qd Qe) Me(Fp Fr Hq Hr Hu Hv Hw Hx Ih Ii Ij Ik Il In Io Ip Iq Ir Iu Jg Jh Jk Jl Jm Jn Jo Jp Jr Js Jt Lh Lu Lx Lz Ma Mb Mc Md Mg Mh Mi Mj Mk Ml Mm Mn Mp Mr Mt Mu Mv Mw Mz Na Nb Nc Nd Ne Nh Ni Nk Nl Nn Nq Nr Nv Nx Ny Of Oh Oi Ok Om On Oz Pa Pc Pd Pe Pf Pg Po Pz Qa Qb Qc Qd Qe) Mg(Fp Fr Hq Hr Hu Hv Hw Hx Ih Ii Ij Ik Il In Io Ip Iq Ir Iu Iv Jg Jh Jk Jl Jm Jn Jp Jr Js Jt Lh Lu Lx Lz Ma Mb Mc Md Mf Mh Mi Mj Mk Ml Mm Mn Mp Mr Mt Mu Mv Mw Mz Na Nb Nc Nd Ne Nh Ni Nk Nl Nn Nq Nr Nv Nx Ny Of Oh Oi Om On Oz Pa Pc Pd Pe Pf Pg Po Pz Qa Qb Qc Qd Qe) Mj(Fr Hq Hr Hu Hv Hw Hx Ih Ii Ij Il In Io Ip Iq Ir Iu Iv Jg Jh Jk Jl Jm Jn Jo Jp Jr Js Jt Lh Lu Lx Lz Ma Mb Mc Md Me Mf Mh Mi Mk Ml Mm Mn Mp Mr Mt Mu Mv Mw Mz Na Nb Nc Nd Ne Ng Nh Ni Nk Nl Nn Nq Nr Nv Nx Ny Of Oh Oi Om On Oz Pa Pc Pd Pe Pf Pg Po Pz Qa Qb Qc Qd Qe) Ni(Fp Fr Hq Hr Hu Hv Hw Hx Ih Ii Ij Il In Io Ip Iq Ir Iu Iv Jg Jh Jk Jl Jm Jn Jp Jr Js Jt Lh Lu Lx Lz Ma Mb Mc Md Mf Mh Mi Mk Ml Mm Mn Mp Mr Mt Mu Mv Mw Mz Na Nb Nc Nd Ne Nh Nk Nl Nn Nq Nr Nv Nx Ny Of Oh Oi Ok Om On Oz Pa Pc Pd Pe Pf Pg Po Pz Qa Qb Qc Qd Qe) Iu(Fp Fr Hq Hr Hu Hv Hw Hx Ih Ii Ij Il In Io Ip Iq Ir Iv Jg Jh Jk Jl Jm Jn Jp Jr Js Jt Lh Lu Lx Lz Ma Mb Mc Md Mf Mh Mi Mk Ml Mm Mn Mp Mr Mt Mu Mv Mw Mz Na Nb Nc Nd Ne Nh Nk Nl Nn Nq Nr Nv Nx Ny Of Oh Oi Ok Om On Oz Pa Pc Pd Pe Pf Pg Po Pz Qa Qb Qc Qd Qe) Jk(Fp Fr Hq Hr Hu Hv Hw Hx Ih Ii Ij Ik Il In Io Ip Iq Ir Iv Jg Jh Jl Jm Jn Jo Jp Jr Js Jt Lh Lu Lx Lz Ma Mb Mc Md Mf Mh Mi Mk Ml Mm Mn Mp Mr Mt Mu Mv Mw Mz Na Nb Nc Nd Ne Nh Nk Nl Nn Nq Nr Nv Nx Ny Of Oh Oi Ok Om On Oz Pa Pc Pd Pe Pf Pg Po Pz Qb Qc Qd Qe) Js(Fp Fr Hq Hr Hu Hv Hw Hx Ih Ii Ij Il In Io Ip Iq Ir Iv Jg Jh Jl Jm Jn Jp Jr Jt Lh Lu Lx Lz Ma Mb Mc Md Mf Mh Mi Mk Ml Mm Mn Mp Mr Mt Mu Mv Mw Mz Na Nb Nc Nd Ne Nh Nk Nl Nn Nq Nr Nv Nx Ny Of Oh Oi Ok Om On Oz Pa Pc Pd Pe Pf Pg Po Pz Qa Qb Qc Qd Qe) Lh(Fp Fr Hq Hr Hu Hv Hw Hx Ih Ij Il In Io Ip Iq Ir Is Iv Jg Jh Jl Jm Jn Jp Jr Jt Lu Lx Lz Ma Mb Mc Md Mf Mh Mi Mk Ml Mm Mn Mp Mr Mt Mu Mv Mw Mz Na Nb Nc Nd Ne Nh Nk Nl Nn Nq Nr Nv Nx Ny Of Oh Oi Ok Om On Oz Pa Pc Pd Pe Pf Pg Po Pz Qa Qb Qc Qd Qe) Nq(Fp Fr Hq Hr Hu Hv Hw Hx Ih Ij Il In Io Ip Iq Ir Iv Jg Jh Jl Jm Jn Jp Jr Jt Lu Lx Lz Ma Mb Mc Md Mf Mh Mi Mk Ml Mm Mn Mp Mr Mt Mu Mv Mw Mz Na Nb Nc Nd Ne Nh Nk Nl Nn Nr Nv Nx Ny Of Oh Oi Ok Om On Oz Pa Pc Pd Pe Pf Pg Po Pz Qa Qb Qc Qd Qe) Nr(Fp Fr Hq Hr Hu Hv Hw Hx Ih Ij Il In Io Ip Iq Ir Is Iv Jg Jh Jl Jm Jn Jp Jr Jt Lu Lx Lz Ma Mb Mc Md Mf Mh Mi Mk Ml Mm Mn Mp Mr Mt Mu Mv Mw Mz Na Nb Nc Nd Ne Nh Nk Nl Nn Nv Nx Ny Of Oh Oi Ok Om On Oz Pa Pc Pd Pe Pf Pg Po Pz Qa Qb Qd Qe) Mi(Fp Fr Hq Hr Hu Hv Hw Hx Ih Ij Il In Io Ip Iq Ir Iv Jg Jh Jl Jm Jn Jp Jr Jt Lu Lx Lz Ma Mb Mc Md Mf Mh Mk Ml Mm Mn Mp Mr Mt Mu Mv Mw Mz Na Nb Nc Nd Ne Nh Nk Nl Nn Nv Nx Ny Of Oh Oi Ok Om On Oz Pa Pc Pd Pe Pf Pg Po Pz Qa Qb Qc Qd Qe) Jm(Fp Fr Hq Hr Hu Hv Hw Hx Ih Ij Il In Io Ip Iq Ir Iv Jg Jh Jl Jn Jp Jr Jt Lu Lx Lz Ma Mb Mc Md Mf Mh Mk Ml Mm Mn Mp Mr Mt Mu Mv Mw Mz Na Nb Nc Nd Ne Nh Nk Nl Nn Nv Nx Ny Of Oh Oi Ok Om On Oz Pa Pc Pd Pe Pf Pg Po Pz Qa Qb Qc Qd Qe) Jr(Fp Fr Hq Hr Hu Hv Hw Hx Ih Ij Il In Io Ip Iq Ir Is Iv Jg Jh Jl Jn Jp Jt Lu Lx Lz Ma Mb Mc Md Mf Mh Mk Ml Mm Mn Mp Mr Mt Mu Mv Mw Mz Na Nb Nc Nd Ne Nh Nk Nl Nn Nv Nx Ny Of Oh Oi Ok Om On Oz Pa Pc Pd Pe Pf Pg Po Pz Qa Qb Qd Qe) Mb(Fr Hq Hr Hu Hv Hw Hx Ih Ij Ik Il In Io Ip Iq Ir Iv Jg Jh Jl Jn Jp Jt Lu Lx Lz Ma Mc Md Mf Mh Mk Ml Mm Mn Mp Mr Mt Mu Mv Mw Mz Na Nb Nc Nd Ne Nh Nk Nl Nn Nv Nx Ny Of Oh Oi Om On Oz Pa Pc Pd Pe Pf Pg Po Pz Qa Qb Qc Qd Qe) Mh(Fr Hq Hr Hu Hv Hw Hx Ih Ii Ij Il In Io Ip Iq Ir Iv

Oy Oz Pa Pb Pc Pe Pf Po Pz Qa Qc Qd Qe) On(aA Fp Hq Hu Hv Ih Ik Ip Ir Iv Jg Jm Jn Jq Js Jt Lw Lz Mh Mk Mr Ms My Mz Ng Nj Nl Nm Nn No Ny Oe Of Ok Oy Oz Pb Pg Qa Qb Qd) Ok(aA Fp Ih Il Ip Iv Jg Jl Jm Jn Jq Js Jt Lh Lw Lx Mn Mz Nl Nn No Nr Ns Nv Ny Oz Pb Po Qa Qb Qd Qe) Is(Fp Fr Ip It Jp Jt Lh Lw Lx Ma Mm Mn Mw Mz Nm Nn Nv Ny Oz Pz) No(Ih Ip It Jg Jt Lw Ns Oz) Lj(aA Jl Jq Jt Lw Nv) aA(Ip Jg Lh) FpJt IhJg ItNv} Lj{Ok(Fr Hr Hu Hv Hx Ih Ii Ij Ik Il In Io Ip Iq Is Iu Iv Jg Jl Jn Jo Jp Jq Lh Lu Lw Lx Lz Ma Mb Mc Md Mf Mg Mh Mi Mj Ml Mm Mn Mp Mr Ms Mt Mw My Mz Na Nb Nc Nd Ng Nj Nk Nl Nm Nn No Nq Ns Nv Ny Of Oi On Oy Oz Pa Pb Pc Pe Pf Pg Qb Qc) On(aA Hu Ii Ij In Is It Iv Jk Jo Jq Jt Lu Lw Mc Mi Mj Mp Ms My Ng Nj Nk Nl No Of Oi Oz Pb Pc Qc) Is(aA Ij Ik In Jg Jp Lw Ma Mm Mn Mp No Ns Oe Oz Pb) aA(Ik Ip It Jg Jt Lh Lw Ma Mg Mm Mn Nj Ns Oe Oz) Ij(Mm Mp Oe) NsMp IkQd NvOe} No{Ns(aA Ip Is It Mp Ok On Oz Pb) Th(aQ Iu Kc Kd Kg Ld Qy) Is(It Ms My Oe Oy Oz Pb) Aj(Kc Ke Ko Kq Ow Uh) Ok(It My Oe Oy Oz Pb) Ch(Kc Ke Ow Uh) Ti(bV Ow Qv Uh) Oy(Ij Kc On Ow) Ke(Hc Ik Ph) My(Ij On) Uh(Ii In) NgJg IpOz ItaA KcdJ UrVt} On{Oy(Fp Ip Is It Jg Jn Lx Lz Mr Ms Mt Nn Ns Oe Of Ok Oz Pe) Oe(aA Hu Ih Is It Ms My Ng Ns Pb) Ns(aA Hu Is It Ms My Ng) Ms(Hu Is It Ng Of Pb) My(Fp Is It Jg Mt Of) Ng(Is It Jg Oz) ItaA} Ij{aA(Ik Ip It Jk Lh Lw Me Mk Mm Mn Ms Ng Nj Ns Oe Ok Oz) Oy(Fr Is Jg Jl Lh Mi Mm Mp Mr Mt Nn Nv Ok Pe Po) My(Is Jg Jl Lh Lx Ok)} Ok{It(aA Fp Hr Jo Jp Lx Mc Ms My Ng Nn Ns Oe Oy Oz Pb Qb) aA(Ip Ms Nj Ns Oe Oy Oz Pb) Is(Ms My Ns Oe Oy Oz Pb) IhOe} Ke{Ow(Aj Bg Ct De Hc Hq Jo Mk Ms Of Oy) cH(dK gL iH oE oH oN) Ch(bN dK Nn Ri)} Mz{qC(Jk Mv My Of Om Oy) eZ(hV Jk Ng Of) qD(Jm Mg Ng Oy) ChjO cHhB hOhR} aA{Ip(It Mn Nj Oz) It(Lh Mn)} Th{Kq(Bg My Of) Aa(Lx Qa)} Is{Jg(My Oe) AjAp NnOe} Ch{TiKq NnUh KoOw} AaTiLx JoKnjT

Unconstrained panels with 3 analytes, where 1.0E-8 >= 'model p-value' > 1.0E-9. Contains 18,655 panels of 32,874,593 total panels evaluated. : Im{Ye(aA aC AD aE AF aG aH al Al aK AL aM AN AO AP aQ AR AS aU aV AW AX aY aZ BA BB BC bE bF BG bH bl bJ bL bM BN BO bP bQ bR bS bU bV bW bX bZ cA cB cC cD cE cF cG CH cl cJ cK cL cM cN CO CP CQ cR CS CT CU CV CW CX cY cZ dA DB DC DD DE dF DG dH DI dJ DK DL dM dN Dp Dr Du Ed Ef Em Eq Et Ex Ez Fc Fd Fi Fn Fp FR Fw Fy Gb Gc Gd Gh Gl Gn Gp Gz Ha Hb Hc Hf Hl Ho Hp Hq Hr Hu Hv Hw Hx Ib Ic Id Ih Ii Ij Ik Il In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Op Or Ou Ow Oy Oz Pa Pb Pc Pd Pe Pf Pg Ph Pi Pj Pk Po Ps Pz Qa Qb Qc Qd Qe Qg Qh Ql Qm Qn Qt Qu Qv Qw Qy Qz Rb Rc Rf Rg Rh Rm Rt Rv Rx Ry Rz Sf Sh Si Sj Sr Ss Tn To Tv Tz Ua Ub Uc Ue Uf Ug Uh Un Up Ur Us Ut Uu Uv Uw Ux Uy Va Vb Vh Vi Vo Vp Vq Vs Vt Vw Vz Wb Wc Wd We Wf Wh Yd Yl Zw Zx Xa Wm Ti Th) Sh(aA aC aD aE AF aG aH al AJ aK aL aM AN aO AP aQ AR AS aU aV Aw aX aY aZ BA BB BC bE bF bH bJ bL bM Bn bO bP bQ bS bV bW bX bZ cB cC cD cE cF cG CH cJ cK cL cN CP CQ cR cS CT CU CV cW CX cY cZ dA DB DC DD DE dF dH dJ DK Dl dM Dp Dr Ed Eq Et Ex Ez Fc Fd Fn Fr Fw Fy Gh Gl Gn Gp Ha Hb Hc Hf Hp Hq Hu Hv Hx Ic Ij Ik Il Io Ip Iq Ir Is Iu Iz Je Jf Jg Ji Jk Jl Jm Jn Jo Jq Jr Js Ju Jv Jy Kc Ke Kf Kg Ki Kl Ko Kq Ks Kx Ky Kz Ld Lh Lt Lu Lv Lx Ma Me Mf Mg Mh Mj Mk Mn Mp Mq Ms Mu Mv Mw Mx My Mz Nc Nd Nf Ng Ni Nj Nk Nl No Nt Nu Nv Nw Nx Ny Oa Og Oh Ok Om On Or Ou Ow Oy Oz Pa Pb Pc Pd Pe Pg Ph Pi Po Ps Pz Qa Qb Qc Qd Qe Qg Qh Qm Qn Qt Qu Qv Qw Qy Qz Rf Rg Rh Ri Rj Rm Rt Sf Si Sj Sr Ss Tn To Tv Tz Ua Ub Uc Ue Uf Ug Uh Un Up Ut Uu Uv Ux Uy Va Vb Vi Vp Vq Vs Vt Vw Vz Wc Wf Yd Yl Zw Zx Xa Wm Ti) Pz(Fr Hq Hr Hv Hw Hx Ih Ii Ij Ik Il In Io Ip Iq Ir It Iu Jg Jh Jk Jm Jn Jo Jp Jr Js Lh Lu Lv Lw Lx Ly Ma Mb Mc Md Me Mf Mg Mh Mi Mj Mk Mm Mn Mp Mq Mr Mt Mu Mv Mw Mx My Mz Na Nb Nc Nd Ne Nf Nh Ni Nj Nk Nl Nm Nn Nr Nt Nu Nv Nx Ny Of Oh Oi Om On Oz Pa Pc Pd Pe Pf Pg Po Qa Qb Qc Qe) Qe(Fr Hq Hr Hv Hw Hx Ih Ii Ij Ik Il In Io Ip Iq Ir It Iu Jg Jh Jk Jm Jo Jp Jr Js Lh Lu Lv Lw Lx Ly Ma Mb Mc Md Me Mf Mg Mh Mi Mj Mk Ml Mm Mn Mp Mq Mr Mt Mu Mv Mw Mx My Na Nb Nc Nd Ne Nf Nh Ni Nj Nk Nl Nm Nn Nq Nr Nt Nu Nv Nx Ny Of Oh Oi Om On Oz Pa Pc Pd Pe Pf Pg Po Qa Qb Qc) Ij(Fr Hl Hq Hr Hv Hw Hx Ih Ii Il In Io Ip Ir It Iu Jg Jh Jm Jn Jo Jp Jr Js Lh Lv Lx Ly Ma Mb Mc Md Me Mf Mg Mh Mi Mj Mk Ml Mm Mn Mq Mr Mt Mu Mv Mw Mx Na Nb Nc Nd Ne Nf Nh Ni Nj Nk Nm Nn Nq Nr Nt Nu Nv Nx Ny Of Oh Oi Om On Oz Pa Pc Pd Pe Pf Pg Po Qa Qb Qc We) Mg(Eq Fr Hq Hr Hv Hw Hx Ih Ii Ik Il In Io Ip Iq It Iu Jg Jh Jk Jm Jo Jp Jr Js Lh Lv Lx Ly Ma Mb Mc Md Me Mf Mh Mi Mj Mk Ml Mm Mq Mt Mu Mv Mw Mx My Na Nb Nc Nd Ne Nf Nh Ni Nj Nk Nl Nm Nn Nq Nr Nt Nu Nv Nx Ny Of Oh Oi Om Oz Pa Pc Pd Pf Pg Po Qa Qb Qc Ux) Mq(Fr Hq Hr Hv Hw Hx Ih Ii Ik Il In Io Ip Iq Iu Jg Jh Jk Jm Jo Jp Jr Js Lh Lv Lw Lx Ly Ma Mb Mc Md Me Mf Mh Mi Mj Mk Ml Mm Mp Mt Mu Mv Mw Mx My Na Nb Nc Nd Ne Nf Nh Ni Nj Nk Nl Nm Nn Nq Nr Nt Nu Nv Nx Ny Of Oh Oi Om Oz Pa Pc Pd Pe Pf Pg Po Qa Qb Qc) Qb(Fr Hq Hr Hv Hw Hx Ih Ii Ik Il In Io Ip Iq It Iu Jg Jh Jk Jm Jo Jp Js Lh Lv Lx Ly Ma Mb Mc Md Me Mf Mh Mi Mj Mk Ml Mm Mn Mp Mt Mu Mv Mw Mx My Na Nb Nc Nd Ne Nf Nh Ni Nj Nk Nl Nm Nn Nq Nr Nt Nu Nv Nx Ny Of Oh Oi Om On Oz Pa Pc Pd Pf Pg Po Qa Qc) Om(Eq Fr Hq Hr Hv Hw Hx Ih Ii Ik Il In Io Ip Iq Iu Jg Jh Jk Jm Jo Jp Js Lv Lw Lx Ly Ma Mb Mc Md Me Mf Mh Mi Mj Mk Ml Mm Mn Mp Mt Mu Mv Mw Mx Na Nb Nc Nd Ne Nf Nh Ni Nj Nk Nl Nm Nn Nq Nr Nt Nu Nv Nx Ny Of Oh Oi Oz Pa Pc Pd Pf Pg Po Qa Qc We Wf) Ly(Fr Hq Hr Hv Hw Hx Ih Ii Ik Il In Io Ip Iq It Iu Jg Jh Jk Jm Jo Jp Js Lh Lv Lw Lx Ma Mb Mc Md Me Mf Mh Mi Mj Mk Ml Mm Mn Mp Mt Mu Mv Mw Mx My Na Nb Nc Nd Ne Nf Nh Ni Nj Nk Nm Nn Nq Nr Nt Nu Nv Nx Ny Of Oh Oi Oz Pa Pc Pd Pf Pg Po Qa Qc) Wf(aH al aK As aU Ax bA bB Bc bJ Bn bP bV Ch Cq Cs Cu cY Db Dc dG Dk dM Ex Fd Fn Fy Hv Id Is Jd Ji Jj Jn Jq Jr Js Ke Kk Kq Kx Ld Lh Lv Lx Mj Mr Mx Mz Nv Nw Nx Ny Ok Or Ow Pa Pb Pc Pg Pi Pk Po Ps Qa Ry Tn To Tv Uc Ut Uw Vi Vp Vs Vt Yl Xa) Me(Fr Hq Hr Hv Hw Hx Ih Ii Ik Il In Io Ip Iq It Iu Jg Jh Jk Jm Jo Jp Js Lh Lv Lw Lx Ma Mb Mc Md Mf Mh Mi Mj Mk Ml Mm Mp Mt Mu Mv Mw Mx Na Nb Nc Nd Ne Nf Nh Ni Nj Nk Nl Nm Nn Nq Nr Nt Nu Nv Nx Ny Of Oh Oi Oz Pa Pc Pd Pf Pg Po Qa Qc) Io(Fr Hq Hr Hv Hw Hx Ih Ii Ik Il In Ip Iu Jg Jh Jk Jm Jo Jp Js Lh Lv Lw Lx Ma Mb Mc Md Mf Mh Mi Mj Mk Ml Mm Mn Mp Mt Mu Mv Mw Mx My Na Nb Nc Nd Ne Nf Nh Ni Nj Nk Nl Nm Nn Nq Nr Nt Nu Nv Nx Ny Of Oh Oi Oz Pa Pc Pd Pf Pg Po Qa Qc) Nq(Eq Fr Hq Hr Hv Hw Hx Ih Ii Ik Il In Ip Iq It Iu Jg Jh Jk Jm Jo Jp Jr Js Lv Lw Lx Ma Mb Mc Md Mf Mh Mj Mk Ml Mm Mn Mt Mu Mv Mw Mx Na Nb Nc Nd Ne Nf Nh Ni Nj Nk Nl Nm Nr Nt Nu Nv Nx Ny Of Oh Oi Oz Pa Pc Pd Pf Pg Po Qa Qc) Ml(Fr Hq Hr Hv Hw Hx Ih Ii Ik Il In Ip Iq It Iu Jg Jh Jk Jm Jo Jp Js Lv Lw Ma Mb Mc Md Mf Mh Mi Mj Mk Mm Mn Mp Mu Mv Mw Mx Na Nb Nc Nd Ne Nf Nh Ni Nj Nk Nl Nm Nn Nr Nt Nu Nv Nx Ny Of Oh Oi Oz Pa Pc Pd Pf Pg Po Qa Qc Rv) Iu(Fr Hq Hr Hv Hw Hx Ih Ii Ik Il In Ip Jg Jh Jk Jm Jo Jp Js Lh Lv Lx Ma Mb Mc Md Mf Mh Mi Mj Mk Mm Mn Mp Mt Mu Mv Mw Mx My Na Nb Nc Nd Ne Nf Nh Ni Nj Nk Nl Nm Nn Nr Nt Nu Nv Nx Ny Of Oh Oi Oz Pa Pc Pd Pf Pg Po Qa Qc) Jg(Aj Fr Hq Hr Hv Hw Hx Ih Ii Ik Il In Ip Iq Jh Jm Jo Jp Lh Lv Lw Lx Ma Mb Mc Md Mf Mh Mi Mj Mk Mm Mn Mp Mt Mu Mv Mw Mx Na Nb Nc Nd Ne Nf Nh Ni Nj Nk Nm Nn Nr Nt Nu Nv Nx Ny Of Oh Oi On Oz Pa Pc Pd Pf Pg Po Qa Qc) Pg(Fr Hq Hr Hv Hw Hx Ih Ii Ik Il In Ip Iq It Jh Jk Jm Jo Jp Js Lv Lw Ma Mb Mc Md Mf Mh Mi Mj Mk Mm Mn Mt Mu Mv Mw Mx My Na Nb Nc Nd Ne Nf Nh Ni Nj Nk Nl Nm Nn Nr Nt Nu Nv Nx Ny Of Oh Oi Oz Pa Pc Pd Pf Po Qa Qc) Nm(Fr Hq Hr Hv Hw Hx Ih Ii Ik Il In Ip Jh Jk Jm Jo Jp Js Lh Lv Lw Lx Ma Mb Mc Md Mf Mh Mi Mj Mk Mm Mp Mt Mu Mv Mw Mx Na Nb Nc Nd Ne Nf Nh Ni Nj Nk Nn Nr Nt Nu Nv Nx Ny Of Oh Oi Oz Pa Pc Pd Pf Po Qa Qc) Na(Fr Hq Hr Hv Hw Hx Ih Ii Ik Il In Ip Jh Jm Jo Jp Js Lh Lv Lw Lx Ma Mb Mc Md Mf Mh Mi Mj Mk Mm Mt Mu Mv Mw Mx My Nb Nc Nd Ne Nf Nh Ni Nj Nk Nn Nr Nt Nu Nv Nx Ny Of Oh Oi Oz Pa Pc Pd Pf Po Qa Qc) Jh(Fr Hq Hr Hv Hw Hx Ih Ii Ik Il In Ip Iq It Jk Jm

Qe) Jq(Fp Fr Hq Hr Hv Hw Hx Ii Il In Io Iq Iu Jg Jh Jk Jl Jm Jp Jr Js Jt Lh Lu Lv Lw Lx Ly Lz Ma Mb Mc Me Mf Mg Mh Mi Mj Mk Ml Mm Mn Mp Mq Mr Mt Mu Mw Mx Na Nb Nc Nd Ne Nf Nh Ni Nj Nk Nl Nm Nn Nq Nr Nt Nu Nv Nx Ny Of Oh On Pa Pc Pd Pe Pf Pg Po Pz Qa Qb Qc Qd Qe) Oe(Fp Fr Hq Hr Hv Hw Hx Ii In Io Iq Iu Jg Jh Jk Jm Jo Jr Js Lh Lj Lu Lv Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn Nq Nr Nt Nu Nx Ny Of Oh Om Pa Pc Pd Pe Pf Pg Po Ps Pz Qb Qc Qe) Lw(Fp Fr Hq Hr Hv Hw Hx Ii Io Iq Iu Jg Jh Jk Jm Jp Jr Js Jt Lh Lu Lv Lx Ly Lz Ma Mb Mc Md Me Mf Mg Mh Mi Mj Mk Ml Mm Mn Mp Mq Mr Mt Mu Mv Mw Mx Na Nb Nc Nd Ne Nf Nh Ni Nj Nk Nm Nn Nq Nr Nt Nu Nv Nx Ny Of Oh Om On Pa Pc Pd Pe Pf Pg Po Pz Qa Qb Qc Qd Qe) Jl(Fp Fr Hq Hr Hv Hw Hx Il In Io Iq Iu Jg Jh Jm Jp Jr Js Jt Lh Lu Lv Lx Ly Lz Ma Mb Mc Md Me Mf Mg Mh Mi Mj Ml Mm Mn Mp Mq Mr Ms Mt Mu Mw Mx Na Nb Nc Nd Ne Nf Nh Ni Nj Nk Nl Nm Nn Nq Nr Nt Nu Nv Nx Ny Oh Om On Pa Pc Pd Pe Pf Pg Po Pz Qa Qb Qc Qd Qe) My(Fp Fr Hq Hr Hu Hv Hw Hx Ii In Io Iq Iu Jh Jk Jm Jo Jr Js Lj Lu Lv Ly Lz Ma Mb Mc Md Me Mf Mg Mh Mi Mj Mk Ml Mm Mp Mq Ms Mu Mv Mw Mx Na Nc Nd Ne Nf Ng Nh Ni Nj Nk Nl Nm Nn Nq Nr Nt Nu Nx Ny Of Oh Om Oy Pa Pc Pd Pe Pf Pg Po Pz Qa Qb Qc Qd Qe Vi) Ij(Fp Fr Hq Hr Hv Hw Hx Ii Il Io Iq Iu Jg Jm Jp Jr Js Jt Lh Lu Lv Lx Ly Lz Ma Mb Mc Md Me Mf Mg Mh Mi Mj Mk Ml Mm Mn Mp Mq Mr Mt Mu Mx Na Nb Nc Nd Ne Nf Nh Ni Nj Nk Nl Nm Nn Nq Nr Nt Nu Nv Nx Ny Oh Om On Pa Pc Pd Pe Pf Pg Po Pz Qa Qb Qc Qd Qe Th) On(Fp Fr Hq Hr Hv Hw Hx Il In Io Iq Iu Jg Jh Jm Jp Jr Js Jt Lh Lu Lv Lx Ly Lz Ma Mb Mc Md Me Mf Mg Mh Mi Mj Mk Ml Mm Mn Mp Mq Mr Mt Mu Mx Na Nb Nc Nd Ne Nf Nh Ni Nj Nk Nl Nm Nn Nq Nr Nt Nu Nv Nx Ny Oh Om Pa Pc Pd Pe Pf Pg Po Pz Qa Qb Qc Qd Qe) Ms(Fp Hq Hr Hu Hv Hw Hx Ii Il In Iq Jg Jm Jo Jp Jr Js Jt Lh Lj Lu Lv Lx Ly Lz Ma Mb Mc Md Me Mf Mi Mj Ml Mm Mp Mr Mt Mv Mw Mx Na Nb Nc Nd Ne Nf Ng Nh Ni Nj Nk Nl Nm Nn Nt Nv Nx Ny Of Oh Om Oy Pa Pc Pd Pe Pf Pg Po Pz Qa Qb Qc Qd Qe) Il(Fp Hq Hr Hv Hw Hx Ii In Iq Jg Jh Jk Jm Jo Jp Jr Js Jt Lh Lj Lu Lv Lx Ly Lz Ma Mb Mc Md Me Mf Mg Mi Mj Mk Ml Mm Mn Mp Mr Mt Mu Mv Mw Mx Na Nc Nd Ne Nf Nh Ni Nj Nk Nl Nm Nn Nq Nt Nv Ny Of Oh Pa Pc Pd Pe Pf Pg Po Pz Qa Qb Qc Qe) Ng(Fp Fr Hq Hr Hu Hv Hw Hx Ii Io Iq Iu Jh Jk Jm Jo Jr Js Lj Lu Lv Ly Lz Ma Mb Md Me Mg Mh Mj Mk Mq Mt Mu Mv Mx Na Nb Nc Nd Ne Nf Nh Ni Nj Nk Nl Nm Nn Nq Nr Nt Nu Nx Ny Of Oh Om Oy Pa Pc Pd Pe Pf Pg Po Qa Qb Qc Qd Qe Vi) Jp(Fp Fr Hq Hr Hv Hw Hx Ii In Jh Jk Jm Jo Jr Js Jt Lh Lj Lu Lv Lx Ly Lz Mb Mc Md Mf Mg Mi Mj Mk Ml Mm Mn Mp Mr Mt Mu Mv Mw Mx Na Nc Nd Ne Nh Ni Nj Nk Nl Nm Nn Nq Nt Nv Ny Of Oh Pa Pc Pd Pe Pf Pg Po Qa Qb Qc Qd Qe) In(Fp Hq Hr Hv Hw Hx Jg Jh Jk Jm Jo Jr Js Jt Lh Lj Lu Lv Lx Ly Lz Mb Mc Md Mf Mi Mj Mk Ml Mm Mn Mp Mr Mt Mu Mv Mw Mx Na Nb Nc Nd Ne Nf Ni Nj Nl Nm Nn Nt Nv Nx Ny Of Oh Om Pa Pc Pe Pf Pg Po Pz Qa Qb Qc Qd Qe) Mn(Fp Hq Hr Hv Hw Hx Ii Iq Jh Jk Jo Jr Js Jt Lh Lj Lu Lv Lx Ly Lz Mb Mc Md Mf Mg Mi Mj Mk Ml Mm Mp Mr Mt Mu Mv Mw Mx Na Nc Nd Ne Nh Ni Nj Nk Nl Nn Nq Nt Nv Ny Of Oh Pa Pc Pd Pe Pf Pg Po Qa Qb Qc Qd Qe) Hu(Fp Fr Hq Hr Hv Hw Hx Ii Io Iq Iu Jh Jk Jm Jo Jr Lj Lu Ly Ma Mb Md Me Mf Mg Mh Mi Mj Mk Mm Mq Mt Mu Mv Mx Na Nb Nc Nd Ne Nf Nh Ni Nj Nk Nm Nq Nr Nt Nu Nx Ny Of Oh Om Pa Pc Pd Pe Pf Pg Po Pz Qc Qe) Oy(Fp Fr Hq Hr Hv Hw Hx Io Iq Iu Jk Jm Jo Jr Lj Lu Ly Lz Ma Mb Md Me Mf Mg Mh Mj Mk Ml Mm Mq Mu Mv Mx Na Nc Nd Ne Nf Nh Ni Nj Nk Nm Nq Nr Nt Nu Ny Of Om Pc Pd Pf Pg Pz Qa Qc Qd Qe Vi) Lj(Fp Hq Hv Hw Hx Ii Jg Jo Jr Js Jt Lh Lu Lv Lx Ly Lz Ma Mb Mc Mf Mi Mj Ml Mm Mp Mr Mt Mv Mw Na Nb Nc Nd Ne Nf Ni Nj Nk Nl Nm Nn Nt Nv Nx Ny Oh Pa Pc Pe Pf Pg Po Pz Qa Qb Qc Qd Qe) Jt(Aj Fp Hq Hr Hx Ii Jh Jk Js Lh Lu Lv Lx Ly Lz Mb Mc Md Mf Mg Mi Mj Mk Ml Mp Mr Mu Mv Mw Na Nc Nd Ne Nf Ni Nj Nk Nl Nn Nq Nv Ny Of Om Pc Pd Pe Pg Po Qa Qb Qc Qd Qe) It(Fp Fr Hr Hv Hw Hx Io Iq Iu Jg Jh Jm Js Lu Ma Md Me Mg Mh Mj Mk Mm Mq Mt Mu Mv Mx Na Nb Nc Nd Nf Nh Nm Nq Nr Nt Nu Nx Ny Oh Om Pa Pc Pe Pf Pg Po Pz Qe) Nl(Fp Hq Hr Hv Hw Ii Jk Jo Jr Js Lh Lu Lv Lx Ly Lz Mb Mc Md Mf Mi Mj Mk Ml Mm Mp Mr Mt Mv Mw Na Nh Ni Nj Nk Nn Nv Ny Of Pc Pe Qa Qb Qc Qd Qe) Jo(Hv Hw Ii Jg Jr Js Lh Lu Lv Lx Lz Ma Mb Mc Mf Mi Ml Mm Mp Mr Mv Mw Na Nb Nc Nd Nf Ni Nj Nm Nn Nt Nv Nx Ny Pa Pe Pg Pz Qa Qb Qd Qe) Ih(Fp Fr Hx Io Iq Iu Jg Jh Jm Js Me Mg Mh Mq Mt Mu Mx Nb Nf Nm Nq Nr Nt Nu Nv Nx Ny Oh Om Pa Pe Pf Pg Po Pz Qa Qd Qe) Ns(Fr Hq Hr Io Iq Iu Jh Jk Jm Ma Md Me Mg Mh Mj Mk Mt Mu Mx Na Nb Ne Nf Nh Ni Nk Nm Nq Nr Nu Of Oh Om Pa Pd Pf) Vi(Aj aX aZ Bg bH bM Bo bU Ch cQ dE Eq Fr Hc Ib Ik Lx Mf Mh Mu Of Oh Ow Qt Rz Ss Uh Uu Uw Ux Vb Vw Ti Th) Js(Du Hq Hr Ii Jk Lu Lv Ly Lz Mb Mc Md Mf Mj Mk Ml Mm Mp Mr Mv Mw Nc Ne Nh Ni Nj Of Pc Pd Qb Qc Qd) Mc(Fp Hv Ii Jk Jr Lh Lu Lv Lx Lz Mf Mi Ml Mp Mr Mv Mw Nc Nj Nn Nt Nv Ny Of Pe Qa Qb Qc Qd Qe) Mv(Hv Jg Jr Lh Lu Lv Lx Lz Mb Mf Mi Ml Mm Mp Mr Mt Mw Nb Nc Nj Nn Nt Nv Pa Pe Qa Qb Qd Qe) Ps(Af aN Ao aW aX aY aZ Bg bM Bn bU cC Ch Dd De Dg Du Ef Eq Ez Fc Gl Ib Kl Rx Us Uu Uv Vs) Mr(Hq Hr Hx Ii Jh Jk Lv Ly Lz Md Mf Mh Mj Ml Mp Mw Nc Ne Nj Nn Ny Of Po Qb Qd) Qb(Hq Hv Ii Jk Jr Lh Lu Lv Lx Lz Mb Mf Mi Mj Ml Mp Nc Ni Nj Nt Of Pe Qc) Qd(Hq Ii Jk Jr Lh Lu Lv Lx Ly Lz Mb Mf Mi Mj Ml Mp Nc Ne Nj Nn Of Pd Qc) Pb(Hq Hr Io Iq Iu Jg Jh Jk Jm Md Me Mg Mh Mj Mk Mq Mu Nh Nq Nu Oh Pd Pz) Lv(Hq Ii Jh Jk Jr Ly Lz Mb Mf Ml Mw Nc Nj Of Pc Pd Qa Qc) Lz(Ii Iq Jr Lh Lx Mi Mp Mw Nc Nj Of Pa Pe Qa Qc Qe) Mp(Hq Hv Jk Jr Md Mf Mk Nc Nj Nq Of Pd Pf Pg Qa) Lh(Hr Ii Jk Md Mf Mj Mk Ml Mw Nc Nj Of Po) aX(Fd Gb Hp Rx Rz Sf Sh Vw Vz Wd Wh Tl Xa) Lx(Du Hq Jk Ly Md Mk Ml Mw Nj Of Po) Nc(Jk Jr Ly Mf Mk Ml Ne Ni Nk Of Qa) Pe(Hr Ii Jk Mj Ml Nj Of Pd Po) Th(aA aZ bM Dc Ed Is Tv Tz) Mf(Hv Jr Lu Mi Mw Mx Nj Qa) Qa(Hr Ii Jk Mj Ml Nj Of) Nw(Aj De Du Rx Yd Wm Ti) Du(Is Jr Oh Ow Tz) Mi(Jk Md Mk Nj Nq) Nv(Eq Ii Jk Md Of) Ny(Eq We Wf Ye Ti) Ml(Fp Hv Jr Of) Mw(Jg Lu Nb Nj) Nt(Jk Mk Nj) Hr(Hv Hw Jr) aZ(Fc Vc Ti) Aj(Ad rS) Ch(Et Ke) Eq(Ba Jk) Nd(Hq Mk) Nj(Jr Mb) Ld(Lp Uy) Rt(Dc Is) Ow(Dr Wb) Pd(Pf Pg) WmJi NnJk Mjlq HqrS PzOf] Et{Aj(aA AD AF al Al aM AN AO Ap Ar As aW bA Bg BN BO bU cB cD CH cL Co CP CQ Cs CT Cu CV Cw Cx cZ Dc Dd Dg dJ Dl dM Fp Fr Fw Hq Hr Hu Hv Hw Id Ii Ik Il In Ip Ir Iu Iv Jg Ji Jj Jk Jl Jm Jn Jo Jp Jq Jr Js Ke Kf Kg Kn Ko Kq Ld Lh Lu Lv Lx Ly Ma Mb Mc Md Me Mf Mg Mh Mi Mj Mk Ml Mn Mp Mq Ms Mu Mv Mw Mx My Mz Na Nb Nc Nd Ne Nf Ng Ni Nj Nk Nl Nm Nq Ns Nt Nu Nv Nx Ny Oa Oe Of Og Oh Oi Ok Om On Ow Oy Oz Pb Pc Pd Pe Pf Pg Po Pz Qb Qc Sr Vt) Js(Fr Hq Hr Hu Hv Hw Hx Ih Ii Ij Ik Il In Io Ip Iq Ir Iv Jg Jh Jk Jl Jm Jn Jp Jq Jr Jt Lh Lu Lv Lw Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nn Nq Nr Nt Nu Nv Nx Ny Of Oh Oi Ok Om On Oz Pa Pc Pd Pe Pf Pg Po Qa Qb Qc Qd Qe) Jn(Fr Hq Hr Hv Hw Hx Ii Ij Ik Il In Io Ip Iq Ir Iu Iv Jg Jh Jk Jl Jm Jo Jp Jq Jr Jt Lh Lu Lv Lw Lx Ly Lz Ma Mb Mc Md Me Mf Mg Mh Mi Mj Mk Ml Mm Mn Mp Mq Mr Mt Mu Mv Mw Mx Na Nb Nc Nd Ne Nf Nh Ni Nj Nk Nl Nm Nn Nq Nr Nt Nu Nv Nx Ny Of Oh Oi Ok Om On Pa Pc Pd Pe Pf Pg Po Qa Qb Qc Qd Qe) Mz(Fr Hq Hr Hu Hv Hw Hx Ii Ij Ik Il In Io Ip Iq Ir Iu Jg Jh Jk Jl Jm Jo Jp Jq Jr Jt Lh Lu Lv Lw Lx Ly Lz Ma Mb Mc Md Me Mf Mg Mh Mi Mj Mk Ml Mm Mn Mp Mq Mr Mt Mu Mv Mw Mx Na Nb Nd Ne Nf Nh Ni Nj Nk Nm Nn Nq Nr Nt Nu Nv Nx Ny Of Oh Oi Ok Om On Oz Pa Pc Pd Pe Pf Pg Po Qa Qb Qc Qd Qe) Iv(Fr Hq Hu Hv Hw Hx Ii Ij Ik Il In Io Ip Iq Ir Iu Jg Jh Jk Jl Jm Jp Jq Jr Jt Lh Lu Lv Lw Lx Ly Lz Ma Mb Mc Md Me Mf Mg Mh Mi Mj Mk Ml Mm Mn Mp Mq Mr Mt Mu Mv Mw Mx Na Nb Nc Nd Ne Nf Nh Ni Nj Nk Nl Nm Nn Nq Nr Nt Nu Nv Nx Ny Of Oh Om On Pa Pc Pd Pe Pf Pg Po Pz Qa Qb Qc Qd Qe) Ok(Fr Hq Hu Hv Hw Hx Ii Ij Ik Il In Io Ip Iq Ir Iu Jg Jh Jk Jl Jm Jp Jq Jr Jt Lh Lu Lv Lw Lx Ly Lz Ma Mb Mc Md Me Mf Mg Mh Mi Mj Mk Ml Mm Mn Mp Mq Mr Mt Mu Mv Mw Mx Na Nb Nc Nd Ne Nf Nh Ni Nj Nk Nl Nm Nn Nq Nr Nt Nu Nv Nx Ny Oh Oi Om On Pa Pc Pd Pe Pf Pg Po Pz Qa Qb Qc Qd Qe) Ij(Ch Fr Hq Hr Hv Hw Hx Ii Il In Io Ip Iq Ir Iu Jg Jk Jl Jm Jp Jq Jr Jt Lh Lu Lv Lw Lx Ly Lz Ma Mb Mc Md Me Mf Mg Mh Mi Mj Mk Ml Mm Mn Mp Mq Mr Mt Mu Mw Mx Na Nb Nc Nd Ne Nf Nh Ni Nj Nk Nl Nm Nn Nq Nr Nt Nu Nv Nx Ny Oh Oi Om On Oz Pa Pc Pd Pe Pf Pg Po Pz Qa Qb Qc Qd Qe) Ih(Ch Fr Hq Hr Hv Hw Hx Ii Ik Il In Io Iq Ir Iu Jg Jh Jk Jm Jp Jq Jr Jt Lh Lv Lw Lx Ly Ma Mb Mc Md Me Mf Mg Mh Mi Mj Mk Ml Mm Mn Mp Mq Mt Mu Mv Mw Mx Na Nb Nc Nd

Figure 30 Continued

Ne Nf Nh Ni Nk Nm Nq Nr Nt Nu Nv Nx Ny Oh Om On Pa Pc Pd Pe Pf Pg Po Pz Qa Qb Qc Qd Qe) Ms(Fr Hq Hr Hu Hv Hw Hx Ii Ik Il In Io Ip Iq Ir Jg Jl Jm Jo Jp Jr Jt Lh Lu Lv Lw Lx Lz Ma Mc Md Me Mf Mg Mh Mi Mj Mk Mm Mp Mq Mt Mw Mx My Na Nb Nc Nd Ne Nf Ng Ni Nj Nk Nl Nm Nr Nt Nu Nv Nx Ny Of Oh Oi Om Pa Pb Pc Pd Pe Pf Pg Po Qa Qc Qd Qe) Oz(Fr Hq Hr Hu Hv Hw Hx Il In Io Iq Ir Iu Jh Jm Jo Jp Jq Jr Jt Lh Lu Lv Lw Lx Ma Mc Md Me Mf Mg Mh Mi Mj Mk Ml Mn Mp Mq Mr Mt Mu Mv Mw Mx Na Nb Nc Nd Ne Nf Nh Ni Nj Nm Nn Nq Nr Nt Nu Nv Ny Of Oh Oi Om On Pa Pb Pc Pe Pf Pg Po Qa Qb Qc Qe) My(Fr Hq Hr Hu Hv Hw Hx Ii Ik Io Iq Ir Iu Jg Jh Jk Jm Jo Jp Jr Jt Lu Lv Lw Ly Lz Ma Mc Md Me Mg Mh Mi Mj Mk Ml Mm Mn Mp Mq Mu Mv Mx Na Nc Nd Ne Nf Ng Nh Ni Nj Nk Nl Nm Nq Nr Nt Nu Nx Ny Of Oh Oi Om Oy Pa Pb Pc Pd Pf Pg Qc Qd Qe) Qd(Ch Fr Hq Hr Hu Hv Hw Hx Ii In Io Ip Ir Jh Jk Jl Jm Jo Jq Jr Jt Lh Lu Lw Lx Lz Ma Mc Md Mf Mg Mh Mi Mj Mk Mn Mp Mr Mt Mu Mv Mw Nb Nc Nd Nf Ni Nj Nk Nl Nn No Nr Nt Nu Ny Of Oh Oi On Pa Pb Pc Pd Pe Pf Pz Qa Qb Qc) Oy(Fr Hq Hr Hu Hv Hw Hx Ii Ik Io Iq Ir Iu Jg Jh Jk Jm Jo Jp Jr Jt Lu Lv Lw Ly Ma Mb Mc Md Me Mf Mg Mh Mi Mj Mk Ml Mm Mq Mu Mv Mx Na Nd Ne Nf Ng Nh Ni Nj Nk Nm Nq Nr Nt Nu Nx Ny Of Oh Oi Om Pa Pb Pc Pd Pz Qc) No(Ef Fc Hv Hw Io Iq Ir Iu Jg Jl Jp Jr Jt Kc Kj Kl Ks Lh Lv Ly Ma Mb Me Mf Mg Mh Mi Ml Mm Mq Mr Mt Mx Na Nb Nd Ne Nf Nh Ni Nk Nm Nq Nr Nt Nu Nv Nx Ny Oh Om On Pa Pe Pf Pg Ph Pz Qc Qe Uh Ur Us Uu Wm Ti) Ng(Hq Hr Hu Hv Hw Hx Ii Ik In Io Iq Ir Iu Jh Jk Jm Jo Jp Jr Lu Lv Ly Mb Mc Md Me Mf Mg Mh Mj Mk Ml Mm Mq Mu Mv Mx Na Nb Nd Ne Nf Nh Ni Nj Nk Nm Nq Nr Nt Nu Nx Ny Of Oh Oi Om Pa Pb Pc Pd Pg Pz Qc Wm) Qa(Fp Fr Hq Hr Hu Hv Hx Ii Ik Il In Io Ip Iq Ir Jh Jk Jl Jm Jo Jq Jr Jt Lh Lu Lw Lx Lz Ma Mc Md Mf Mg Mh Mi Mj Mk Mn Mp Mr Mt Mu Mv Mw Nb Nc Ne Nh Ni Nj Nk Nl Nn Nr Of Oh Oi Om On Pc Pd Pe Pf Qb Qc) Ns(Fr Hq Hr Hw Hx Ii Ik Il In Io Iq Ir Iu Jg Jh Jk Jm Jo Jp Lu Lv Ly Ma Mb Mc Md Me Mf Mg Mi Mj Mk Ml Mm Mq Mu Mv Mx Na Nb Nc Nf Nh Ni Nj Nk Nm Nq Nr Nt Nu Nx Ny Of Oh Oi Om Pa Pc Pd Pf Pg Po Pz) Pb(Fr Hu Hv Hw Hx Il In Io Ip Iq Ir Jm Jo Jp Jq Jr Jt Lh Lu Lv Lw Lx Lz Ma Mc Me Mf Mh Mi Mn Mp Mq Mt Mw Mx Na Nb Nc Nd Nf Ni Nj Nl Nn Nr Nt Nu Nv Nx Ny Of Oh Oi On Pa Pc Pf Pg Po Qb Qc Qe) Nl(Fr Hq Hr Hu Hv Hw Ik In Io Ip Iq Ir Jh Jl Jm Jo Jq Jr Jt Lh Lu Lv Lw Lx Lz Ma Mc Mf Mg Mh Mk Mn Mp Mr Mt Mv Mw Nb Nc Ne Nf Nh Ni Nj Nk Nn Nr Nv Ny Of Oi On Pc Pe Pf Pg Po Qb Qc Qe) Qb(Hq Hr Hv Hw Hx Ii Ik Il In Io Ip Iq Ir Jh Jk Jl Jo Jq Jr Jt Lh Lu Lw Lx Lz Ma Mc Md Mf Mh Mi Mk Mn Mp Mr Mt Mu Mv Mw Nb Nc Ni Nj Nk Nn Nr Nt Of Oh Oi On Pc Pd Pe Pf Qc) Hu(Fr Hv Hw Hx Il In Io Ip Iq Ir Jg Jl Jm Jo Jq Jr Jt Lh Lu Lw Lx Lz Ma Mc Mh Mi Mn Mp Mr Mt Mu Mw Mx Nb Nc Nf Nj Nr Nt Nv Ny Of Oh Oi Om Pa Pc Pe Pf Pg Po Qc Qe) Fp(Fr Hw Hx Il In Io Iq Iu Jg Jk Jp Jr Lh Lu Lv Lx Ly Ma Me Mg Mh Mj Mm Mq Mt Mu Mx Na Nb Nd Ne Nf Nh Nk Nm Nq Nr Nt Nu Nv Nx Ny Om On Pa Pd Pe Pg Po Pz Qe) Nn(Ch Fr Hq Hr Hv Hw Ik In Ip Iq Ir Jh Jk Jl Jm Jo Jq Jr Jt Lh Lu Lw Lx Lz Mc Md Mf Mg Mh Mi Mk Mn Mp Mr Mu Mv Mw Mx Nc Nj Nq Nr Of Oi Pc Pd Pe Pf Qc Qe) Oe(Hr Ii Ik Io Iq Iu Jg Jh Jk Jp Lu Lv Lw Ly Ma Mb Md Me Mf Mg Mh Mi Mj Mk Ml Mm Mq Mu Mv Na Nb Nd Ne Nf Nh Ni Nk Nm Nq Nu Nx Of Oi Om Pd Pz) Mr(Hq Hr Hx Ik Ip Jh Jk Jm Jq Jr Jt Lu Lv Lw Lx Lz Mc Md Mg Mh Ml Mn Mp Mt Mv Mw Nb Nc Nj Ny Of Oh Oi On Pc Pd Pf Pg Po Qc Qe) Nc(Hq Hv Hw Ik Io Ip Ir Jl Jo Jq Jr Jt Lh Lu Lw Lx Lz Mc Mh Mk Mn Mp Mt Mw Mx Ne Ni Nj Nk Nr Of Oi On Pe Pf Po Qc Qe) Jq(Hr Ik Il Ip Jh Jl Jm Jo Lh Lu Lx Lz Mc Md Mf Mh Mi Mn Mp Mt Mv Mw Mx Nb Nj Nr Nt Of Oi Om Pa Pe Pf Qc Qe) Of(Hv Hw Il In Ip Ir Jl Jm Jr Jt Ke Lh Lu Lw Lx Lz Ma Mi Mn Mp Mt Mw Mx Nj Nr Nt Nv Ny Pa Pe Pf Po Qc Qe) Jl(Hq Hr Hv Hx Ii Ik Ip Jk Jo Jr Jt Lu Lw Lx Lz Mc Mf Mg Mh Mk Mn Mp Mt Mv Mw Nb Nj Oi Pc Pd Qc Qe) Lz(Hq Hv Hw Ik Il In Ip Ir Jm Jo Jr Jt Lh Lu Lw Lx Mc Mf Mk Mn Mw Nb Nj Ny Oi On Pc Qc Qe) Og(Hr Iu Jh Jk Jo Jp Ly Mb Md Me Mf Mg Mj Mk Ml Mm Mu Mv Na Nd Ne Nh Ni Nk Nq Nu Oi Pd Pz) Ip(Hq Hr Hv Il Ir Jo Jr Jt Lh Lu Lw Lx Mf Mh Mn Mp Mt Mw Nb Nj Nr Nt Oi On Pe Pf Qc Qe) Ch(aA BA bO cl cP Di Ed Id Is Ji Jj Kn Ko Kq Ld Lj Mn Mt Oa Ou Ow Qc Qe Sr Tv Uh) Jo(Hv Hw Il In Ir Jm Jr Lh Lw Lx Mh Mi Mn Mp Mw Nj Nr Nt Nv Ny On Pe Po Qe) Lx(Hv Hx Ik Ir Jr Jt Lh Lw Md Mk Mp Mv Mw Nj Ny Oi Pe Pg) Ed(Du Fi Gc Gn Ho Hp Ps Rt Rx Sh Uw Vh Vi Yd Yl Tl Xa) Lh(Hr Hx Ii Md Mk Mv Mw Nj Oi) Pe(Hq Hr Hx Ii Ik Md Mv Nj Pd) Mp(Hq Hv Ir Jr Mk Nj Pd) Mw(Ik Ir Lu Mh Nj Oi On) Qe(Ik Lw Mc Nj Oi Pd Qc) Ps(aY Ef Ez Gl Kl Vs) Ir(Hr Io Is Mn Nj) Wm(Ji Jj Lj Nw) Ik(Iq Mh Mt Qc) Jt(Hr Lu Mg Oi) On(Jh Mk Mv Oi) De(Ke Nw) Dr(Kd Th) Mk(Nr Pa) Hr(Hv Hw) Yd(Ny Oa) Pd(Pf Pg) AaJj BgNw MdIn MnOi MtMv NdHq IlQc IsPz WbOw ShaY LdLp LjVi} Ps{Uu(aK Al aO Ap aS aU aW AX aY aZ BA Bb bG bH bL Bo bQ bV cB cD cE Ch cl cL cM cN Cq cR cT cU Cv Cw CX cZ DC Dd dF Di dK Dr Ed Ex Ez Fc Fi Fw Fy Gh Gp Hu Ib Ic Ih Ij Il Ir Is Jg Jk Jm Jn Jp Ju Jv Jy Kd Kf Ki Kk Kn Kp Lh Lj Lp Lv Lx Mf Mg Mh Ml Mn Mr Ms Mt Mx Nb Nd Ne Ni Nn No Nr Nt Nu Nv Nx Ny Oe Og Oh Ok Om Ow Oy Pa Pc Pe Pf Pz Qa Qb Qc Qe Qh Qu Qy Rm Ru Rx Ry Sf Sr Ss St To Uc Ug Uh Uk Ul Us Uv Uy Va Vh Vi Vq Vs Vz Wd Wh Zx Ti Th) Rx(aA AF aG al Aj An AO aR AX aY aZ bF BG bH bL Bn Bo bU bZ cB cD cE cG CH cM cN Co cR cS Cu cV cW dA dD De Dg Di Dk dM Ed Ef Em Eq Ez FR Fw Gh Gl Ha Hc Hq Ih Ii Ir Iv Iz Jd Jl Jp Ju Jy Ke Kg Kj Kl Ko Lj Lu Lv Ma Mh Ml Mm Mn Mu Mv Mx My Mz Ng Ni Nk No Nq Nx Oa Of Og Oh Ok On Op Ou Ow Pe Pg Qb Qn Qt Qu Qw Qz Rb Rf Ri Sf Sh Si Sr Ss Tn Ua Uh Us Ut Uv Uw Va Vb Vp Vs Vt Vw We Wf Wh Yd Zx Wm Th) aW(Aj Ar aX aZ Ba Bg Bo Ch Cs Ct Dg Dp Ed Ef Eq Fd Fn Fp Gd Gh Hb Hf Ij Iv Iz Jg Jj Jo Ke Kg Ki Kj Kl Ks Kx Ld Lj Lp Lx Lz Mh Ml Mq Ng Nw Oa Or Ow Oy Pa Pe Ph Po Qb Qg Qu Qx Rg Rv Rz Sh Ss Tv Tz Uh Ur Us Ux Vb Vo Vs Vt Vw Yl) Vs(aC aF aK Ao Ap aU aX bC bG Bo bQ bW bZ cG cL cN CO cS Cu Cw cY dl dK dM Fc Fi Gp Hc Ho Hw Ib Ij Il Jo Kc Kd Ke Kg Kq Lx Mf Mg Mi Mm Mn Mt Nm Nn Nw Oe Oi Ow Oz Pf Pj Rc Rj Rz Si Uf Uh Uk Vq Wf Ti) Ch(aF Ao Ar aU aX bG bJ cJ CO cU De dI Ef Ez Fi Gp Ho Hv Ij Iv Jd Je Jh Ji Kc Kd Ke Kg Kj Kq Kz Ld Lx Ma Mf Mg Mi Mm Mp Mq Mt Mu Nn Nq Oe Om Ow Pd Po Qd Qy Qz Rz Tn Uf Uh Ut Wf Ti) Ed(Af aG aH aJ aK aQ aR aU aZ Ba Bn bP bQ bS cN CX cY Dc Dk Gp Gz Ha Hc Hp Hu Ib Ic Ij Je Jl Ki Lu Lx Ma Mf Mg Nv Oe Oi Or Ow Oz Qn Qw Rj Sh Uh Vp Vq Wf Ye Ti) Ow(Ad Af Aj Ao Aw aX aY aZ BG Bn Co Cp cS De Dg Di Ef Eq Ez Fc Gl Hc Hu Ib Iz Jo Kg Kl Nc Ng Nl No Oi Oz Pb Qt Qw Rz Sh Ss Ua Ue Uv Ux Vo Wb Wd Wh Yd Zw Zx) Uh(Al aY aZ Bb Bg bO cH dK Ef Ex Ez Fc Fw Gl Ih Il Jd Ji Jm Kd Kl Kx Lj Lp Mh Ml Ms Mx Nb Nd Ne Nn Nr Nx Oa Oi Pa Pe Qm Qn Ru To Uk Un Uv Uy Va Vw Yd Tm Th) Lj(aC Af aG aJ aP bM Bn Bo bS bX cE cN Cx Dd dI Dk dM Fc Ha Hb Hc Ib Ih It Jl Ld Lp Mj Mx Oi Oz Pa Pc Qn Qv Qw Ri Rj Rv Sh Ug Un Ur Vp Vt Wf Ye) Us(aF Bb bG Bn cM cP cQ cU Dd DK Fc Fi Hc Ho Hp Hv Ib Ij Il Is Kd Ki Lu Lx Mf Mt Nc Nn Oi Om Oz Pf Pi Qv Qw Rc Sh Si Sr Uk Vq Vt Ti) Pe(aD Af aN aR aY aZ bM Bn bS Cx Dd dG Dk Du Ex Ha Hc Ib Id Oe Oi Oz Pc Qn Qt Qw Rj Ua Vp Wf Ye) Ef(aU bZ CO CU dI Gp Hv Kd Ke Kg Kq Lx Ma Mg Mi Mp Mq Mt Mu Nn Nq Om Pd Qy Uf Wf) Va(Af aR aZ bM Bo bS Cx dB dG Dk Hc Hu Ib It Jl Oe Oi Oz Pc Qn Qt Qw Rj Vp Vq Vt Wf Ye) Gp(Aj Ao aX aY Bg Bn cS De Dg Eq Ez Fr Gl Hc Iz Kl Ng No Qt Rz Ss Ua Uv Ux Wd Wh Yd) Ij(Ad Aj aN aY aZ BG bM Bo De Dk Fc Gl Kf Kr Mj Nl Of Rt Up Uv Vb Vh We Yd Zw) Bo(aY Cv Di Ez Fw Il Jd Jm Kd Kl Mh Ms Mx Nb Nq Nr Oh Pa Ru Sr Ss To Uy Th) Fw(Af aH Ar Bn Cv Hb Hc Hu Ib Jk Ki Ld Oe Oi Oz Qv Qw Rj Sh Ur Wf Ye) Bg(aK Aw aZ bF bQ cE cL Co dK Fi Il Is Kd Kq Lx Mf Mt Nn Oe Oh Om Pf) Oa(Af aG aJ Bn bS Cx Dd Ha Hc Ib Jl Oe Oi Oz Qn Qv Qw Rj Vp Wf Ye) Oi(aA aF Ar aY cV Gh Iv Jy Lv Mh No Og Qn Sr Vb Vo Wf Yd Zw Th) Nn(Aj aX aZ De Dg Eq Hc Hu Iz Kl My Ng Qw Rz Sh Ss Ua Vt Wf) Lx(Aj aN aY Bn De Fc Gl Hc Iz Kl My Qw Ss Uv Wf Wh Yd Wm) Oe(Eq Hc Iz Kl Ng No Qt Qz Rc Sh Sr Ss Vb Vt We Wh) Ld(aY Bb Ez Jm Jy Kd Lp Mh Nr Pa Ru To Ul Uy Th) Kl(Ap bQ cU Cw dK Ib Il Ma Mt Nt Pd Rj Rz Ti) Ur(aY Ir Jd Jm Kd Lp Mh No Nr Pa Ru To Th) Eq(aF aU Fc Kd Kq Mi Mt Mu Om Ph Qy Rz) Ar(aY Bb dK Ex Il Jm Jy Kd Ru Ul Th) Mh(bG dI Fc Hc Oz Pa Qv Qw Rj Rv Vt) Hc(aA bO Jn Ml Mx Nb Pf Qa Vi Wc) Aj(bQ cL dK Il Is Kd Mf Om Sr) aZ(bG bO cU Oz Qa Sh Sr Vo Wh) Dk(Is Jn Js Ml Mx No Qa Qx) Kd(Bb Gd Iz Kj Lp Nw Rt Ux) aY(aM Is Ji Jj Kx Lp Nw Po) No(aK aU Ha Ib Qn Vp Ye) Pf(aN Bn Iz My Qw Wf) Nw(Jd Jm Ms Ru To) Fc(Gd Ml Oh Ux)

Jk Jm Jn Jo Jq Mp Mr Mt Nr Nt Nx Ny Om Pf Pz Qb Qe) Mn(aA Fp Ih Ii Iv Jg Jl Jn Lx Mm Mz Nl Nm Nt Ny Po Qa Qe) Ip(Fp Fr Ih Ii Il Jg Jl Jn Jp Lx Ma Mw Mz Nt Ny Oz Po Qa) Qa(aA Fc Fp Ik Jg Jn Jq Ma Mm Nm Nx Oe Og Oz Pb Uh) Jg(aA Fp Ih Il Iv Jl Jn Lx Mr Mw Mz Og Po Qb Qe) Fp(aA Ih Ii Jl Jn Jp Jq Ma Mm Nm Nx Ny Pz) Jn(aA Fr Jl Lx Mm Mw Mz Ny Po Pz) aA(Ii Lx Ma Mm Mz Nm Nx Ny Pz) Ih(Fr Lx Ma Mm Nm Ny Po) Ke(CH Dc dJ Ko Ky Ph) Nw(jO jP jT Jv Ky Uh Wm) Uh(Ko Nr Ri Tv Ur) Jl(Lx Mm Nm Ny) Xa(aW aY Kd) Nm(Iv Po) Mz(Ii jT) FrOz FwKo MmIv IiOg IlNy JijT KdVi KfuM KqRu LdLp dJvI} Nw{Wm(aA Fp Hq Hu Hv Hw Ii Ij Ik In Ip Iq Ir Is It Iv Jg Ji Jk Jl Jm Jn Jo Jp Jq Jr Js Jt Lj Lv Lw Ly Mb Mc Md Me Mi Mj Mk Ml Mn Mp Mr Ms Mt My Mz Na Nb Nc Nd Ne Nf Ng Nh Ni Nj Nl Nm Nn Nr Ns Nu Nx Oe Of Og Oi Ok Om Oy Pb Pc Pe Pg Qa Qc Qd Qe) Rx(aF Aj AO bF BG bZ CH cV dA Ed Ef Eq Fr Hc Hq In Iz Jl Jp Jy Kr Lj Lv Mf Mv My Nq Oa Og Op Ou Qu Qw Rb Rg Sr Ua Us Ux Wf Yd Zx) Yd(aW bQ Cq dK Fw Gc Gp Ij Is Jf Jo Jt Kg Mt Nb Nm Nn Nr Nt Oe On Or Pe Pg Ph Pj Pz Sr Ub Ut Vi Ti) Aj(Ad Ba bN cH Hq Hu Hv Hw Ij Is Jg Jh Ji Jl Jm Jn Jo Jp Jq Jr Js Mt Nn Oz Pz Qa Qc Qd Qe Qv) Ch(bN Ed Ez Ic Ij Jg Jh Ji Jp Jt Jv Kq Qa Qd Qe Qv Qy Ri Sr St Tv Ua Uc Uf Uh Ur Us) Mg(Fr Io Iq Iu Lv Ly Ma Mb Mj Mq Mt Nb Ne Nf Nh Ni Nk Nm Nq Nr Nv Nx Oh Om On) Ru(aA aJ Ar aY aZ bM Bo Dd Dr Ed Fp Gz Hl Hp Iv Ld Mk Mq Nt Nu Pk Ub Vz Wb Zw) Aa(Hq Hr Hu Hx Ii It Jm Jn Jo Jq Lu Md My Og Oz Pa Pb Pc Pe Po Qa Qb Qc Qe) Nf(Fr Io Iq Iu Lv Ly Ma Mb Mj Mq Mt Nb Nc Nh Ni Nk Nm Nq Nr Nv Nx Om On) Nk(Fr Io Iq Iu Lv Ly Ma Mb Mj Mq Mt Nb Ne Nh Nm Nq Nv Nx Om On) aY(Gb Rt Rv Uw Ux Uy Uz Va Vb Vc Vh Vi Vw Wc Wd We Wf Wg Wh Th) Iu(Fr Io Iq Ma Mb Mj Mq Mt Ne Nh Ni Nm Nq Nr Nv Nx Oh Om On) Nh(Fr Io Iq Lv Ma Mj Mq Mt Nb Ne Ni Nm Nq Nv Nx Om On) Ma(Fr Io Iq Mb Mj Mq Mt Ne Ni Nm Nq Nv Nx Om On) De(Ed Hv Jn Jr Jv Kq Mt Qa Qd Qe Tt Tv Uc Uh) Nv(Fr Io Iq Ly Mb Mj Mq Mt Ne Ni Nm Nq Nx Om) Us(dJ dK Gh Hl Jv Lp Ry Si Tv Uy Va Tm Th) Mq(Fr Iq Lv Mt Ne Nm Nq Nx Om On Uy Th) Ed(dJ dK Fd Gh Gn Mj Rt Si Va Vz) Nx(Fr Io Iq Ly Mb Mj Mt Ne Nq Om) Wf(aZ Bb Fw Ih Jn Kx Nb Pe Uk) cH(bN cI iJ nW oE oN Tn To Tv) Th(Ba gL Ld Mw Ng Nt Oe Sr) Fr(Iq Mb Mj Ne Nm Nq Om) Fw(Eq Ho Rt Rv Ux Zx) Ne(Io Iq Mj Nm Nq Om) jO(Hq Hu Ji Jm Nl Qe) Tv(dJ Md Of Ph Uh) Ij(Hc Rt Vh We Zw) Jv(bN cI dK Fy Ju) Vi(Bg Dk Hc Lj Sr) Nb(Rt Sh We Zx) Nl(iB jD jP jT) Uh(Bg dJ dK Ri) Uy(Kd Ld Nt Ub) Va(aD aZ bM Dd) Du(Ih Oa Pe) Nq(Mj Mt Ni) Xa(Ex Fc Po) Tm(Nu Ub Ur) Om(Iq Mt On) Hp(aW dK) Hu(jT rS) Hc(Jh Qa) Lp(Ld Ur) Of(Kq Uc) On(Iq Mt) bN(Fc Vt) jP(Ji Jr) oE(uI vA) ArTi DrKd EqNn NroN HqjT IcdK TrdJ IhZw WbaW SfUu QaPh WhPe QuUx} Lj{Is(Fp Fr Hq Hr Hu Hv Hw Hx Ih Ii Il Io Ip Iq Ir It Iu Iv Jh Jk Jl Jm Jn Jo Jq Jr Js Jt Lh Lu Lv Lx Ly Lz Mb Mc Md Me Mf Mg Mh Mi Mj Mk Ml Mq Mr Ms Mt Mu Mv Mw Mx My Mz Na Nb Nc Nd Ne Nf Ng Nh Ni Nj Nk Nl Nm Nn Nq Nr Nt Nu Nv Nx Ny Of Oh Oi Om Oy Pa Pc Pd Pe Pf Pg Po Pz Qa Qb Qc Qd Qe) aA(Fp Fr Hq Hr Hu Hv Hw Hx Ih Ii Il In Io Ir Iu Iv Jh Jk Jl Jm Jn Jo Jp Jq Jr Js Lu Lv Lx Ly Lz Mb Mc Md Me Mf Mh Mi Mj Mk Ml Mp Mq Mr Ms Mt Mu Mv Mw Mx My Mz Na Nb Nc Nd Ne Nf Ng Nh Ni Nk Nl Nm Nn Nq Nr Nt Nu Nv Nx Ny Of Oh Oi Om Oy Pa Pb Pc Pd Pe Pf Pg Po Pz Qa Qb Qc Qd Qe) Vi(aG aJ aK aQ aU bB bC bG Bo bQ bS bX bZ cB cE cG cI cJ cL cP cQ Cs Cu CW cY dA Dd dJ DK dM fR Gc Gp Ha Hb Hc Hp Ib Ic Ij It Je Ji Ke Ko Kx Ld Lp Lu Lv Ma Mf Mg Mp Nv Oi Ou Oz Pd Qv Qw Ri Rj Sh Si Sj Uf Ug Uh Un Ur Vq Vt Wc Wf Ye Ti) On(Fp Fr Hq Hr Hv Hw Hx Ih Il Io Ip Iq Ir Iu Jg Jh Jl Jm Jn Jp Jr Js Lh Lv Lx Ly Lz Ma Mb Md Me Mf Mg Mh Mk Ml Mm Mn Mq Mr Mt Mu Mv Mw Mx Mz Na Nb Nc Nd Ne Nf Nh Ni Nm Nn Nq Nr Nt Nu Nv Nx Ny Oh Om Pa Pd Pe Pf Pg Po Pz Qa Qb Qd Qe) Og(Fr Ih Ii Ik Ip Ir It Iv Jh Jn Jo Jp Js Lh Lv Lx Ma Mg Mi Mm Mn Mp Mr Mt Mw Mz Nb Nm Nn Nq Ns Nt Nx Ny Om Pc Pe Pz Qa Qd) Ij(Fr Hu Ih Ik In It Jg Jl Jp Jq Jt Lh Lu Lw Lx Ma Mi Mn Mr Ms Mw My Nc Nd Nj Nl Nn Ns Nv Oh Oy Oz Pb Pc) Ok(Fp Hq Hw Ir Jh Jk Jm Jr Js Jt Lv Ly Me Mk Mq Mu Mv Mx Ne Nf Nh Ni Nr Nt Nu Nx Oh Om Pd Po Pz Qa Qd Qe) Jt(Ih Ik In Ip It Jl Jo Jp Lx Ma Mn Mp Ms Mz Ng Nn Ns Nv Oe Oi Oy Oz Pb) Jp(Ih Ik It Iv Jl Jq Lh Lw Lx Mi Mm Mp Mr Nn Ns Nt Nv Oe Oz Pb Pc) Jg(Hu Ih Ik It Iv Jl Jq Lh Lw Lx Mi Mp Mr My Ng Ns Oe Oi Oy) Jl(Ih Ik It Lw Ma Mm Mn Mp Nn Ns Oe Oz Pb) Mm(Ih Ik It Iv Jq Lh Mr Mz Ns Nv Oe) Mp(Hq Ih Ik It Iv Jq Mz Nv Oe Oz) Ik(Jq Lh Lw Lx Ma Mi Nn Nv Pe) Ld(Du Gb Rz Sh Ux Vb Vw We) Nv(Hu It Lw Ns Oy Oz Pb) Lh(It Lw Ns Pb) Oe(Ih Jq Nn) aZ(Gb Vw Wd) CuDu DrUc WmJi TiKq NsLx LwMr MaIh MtMy KePh RzaX bNpS} Ok{aA(Fp Fr Hq Hr Hu Hv Hw Hx Ih Ii Ik Il In Io Iq Ir Is Iu Iv Jg Jh Jk Jl Jm Jn Jo Jp Jq Jr Js Jt Lh Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Ng Nh Ni Nk Nl Nm Nn Nq Nr Nt Nv Nx Ny Of Oh Oi Om On Pa Pc Pd Pe Pf Pg Po Pz Qa Qb Qc Qd Qe) It(Fr Hq Hu Hv Hw Hx Ih Ii Ij Ik Il In Io Ip Iq Ir Is Iu Iv Jg Jh Jk Jl Jm Jn Jq Jr Js Jt Lh Lu Lv Lw Ly Lz Ma Mb Md Me Mf Mg Mh Mi Mj Mk Ml Mm Mn Mp Mq Mr Mt Mu Mv Mw Mx Mz Na Nb Nc Nd Ne Nf Nh Ni Nj Nk Nl Nm Nq Nr Nt Nu Nv Nx Ny Of Oh Oi Om On Pa Pc Pd Pe Pf Pg Po Pz Qa Qc Qd Qe) Og(Fr Hq Hr Hu Hv Hw Hx Ii Ik In Io Iq Ir Iu Jh Jk Jo Jp Jr Lu Lv Ly Lz Ma Mb Mc Md Me Mf Mg Mh Mi Mj Mk Ml Mm Mp Mq Mr Ms Mt Mu Mv Mw Mx My Na Nb Nc Nd Ne Nf Ng Nh Ni Nj Nk Nm Nq Nt Nu Nx Oe Of Oh Oi Om Oy Pa Pc Pd Pe Pf Pg Pz Qc) Is(Fp Hq Hr Hu Hx Ih Ii Ij Ik Il In Ip Jh Jk Jn Jo Lh Lu Lw Lx Lz Mc Md Mj Mk Mn Mp Mv Mw Mz Na Nc Ng Nj Nl Nn Of Oi Om Pd Qb Qc) Pb(Fp Fr Hr Ih Ij Ip Iv Jn Jp Js Lh Lx Ma Mn Mp Ms Mt My Mz Nn Nr Ns Nv Ny Oe Of On Pf Po Qa Qb Qd) Oe(Fp Fr Hr Ij Ip Iv Jg Jl Jn Jo Jp Jq Js Lx Ms Mt Nc Nl Nn Ns Nv Ny On Oz Po Qa Qb Qd Qe) Ns(Fp Hr Ih Ip Jn Jo Jp Lx Mn Mp Ms Nc Nd Nl Nn Nv Ny On Oy Oz Qa Qb Qd) My(Fp Fr Hr Ih Ip Jg Jn Js Lh Lx Mn Mt Mw Nb Nn Nv Ny On Oz Qa Qb Qd) Ms(Fp Hr Ih Ij Ip Jn Jo Jq Js Lh Lx Mn Mz Nn Ny On Oy Oz Qa Qb Qd) Oy(Fp Ih Ip Jg Jn Js Lh Lx Mp Mt Nn Nv Ny Pf Po Qa Qb Qd) Hr(Fp Ih Ij Ip Jn Js Lx Mz Nl Nn Nv Ny On Oz Qa Qb) Jo(Fp Ih Ij Ip Iv Jn Js Lh Nl Nn Nv On Oz) Oz(Fp Ih Ip Jn Lx Ng Nn Pf Qb Qd) Ng(Ih Ij Ip Jg Jn Jt Nn On) Fp(Hu Ih Ik Ip Jn Mc Oi) Ip(Ih Jn Lx Nn Qb) Ij(Hu Hx Ik Of) Nn(Hu Ih Jn) Qd(Ik Il) On(Hu Of) McJn YdKe} On{Oy(aA Fr Hq Hr Hu Hv Hw Hx Ih Ii Ik Il In Io Iq Ir Iu Iv Jh Jk Jl Jm Jo Jp Jq Jr Js Jt Lh Lu Lv Lw Ly Ma Mb Mc Md Me Mf Mg Mh Mi Mj Mk Ml Mm Mn Mp Mq Mu Mv Mw Mx My Mz Na Nb Nc Nd Ne Nf Ng Nh Ni Nj Nk Nl Nm Nq Nr Nt Nu Nv Nx Ny Oh Oi Om Pa Pb Pc Pd Pf Pg Po Pz Qa Qb Qc Qd Qe) My(aA Fr Hq Hr Hv Ih Ik Ip Iq Ir Iv Jh Jk Jl Jm Jn Jo Jp Jq Js Jt Lh Lu Lw Lx Lz Ma Mc Md Me Mg Mh Mi Mk Ml Mm Mn Mp Mr Ms Mv Mw Mz Na Nb Ng Nj Nk Nl Nm Nn Nr Nt Nv Ny Om Oz Pa Pb Pc Pd Pe Pf Pg Po Pz Qa Qb Qc Qd Qe) Ng(aA Fp Fr Hq Hr Hu Hv Hw Ih Ij Ik Io Ip Iq Ir Iu Iv Jl Jm Jn Jo Jp Jq Jr Js Jt Lh Lu Lw Lx Lz Ma Mc Me Mg Mh Mi Mj Mk Mm Mn Mp Mr Mt Mw Mz Na Nc Nd Ne Nj Nk Nl Nm Nn Nt Ny Of Pa Pb Pc Pe Pf Po Pz Qa Qb Qc Qd Qe) Og(Fr Hr Hw Hx Ii Il In Io Iq Iu Jh Jk Jl Jo Jp Jr Lh Lu Lv Lx Ly Ma Mb Mc Md Me Mf Mg Mi Mj Ml Mm Mn Mp Mq Mt Mu Mv Mw Mx Na Nb Nc Nd Ne Nf Nh Ni Nk Nq Nr Nt Nu Nv Nx Oh Oi Om Pa Pc Pd Pe Pf Po Pz Qc Qe) Oe(Fp Hq Ij Ik Ip Iq Ir Iv Jh Jk Jl Jn Jo Jq Jr Js Jt Lx Lz Mc Md Mk Mn Mv Mw Mz Nj Nl Nn Ny Of Oz Pc Pd Pg Po Qa Qb Qc Qd Qe) Ms(aA Fp Hq Hr Ih Ij Ik Ip Ir Iv Jk Jn Jo Jq Js Jt Lw Lx Lz Mc Md Mh Mk Mn Mr Mu Mz Ne Nj Nk Nl Nn Oi Oz Pc Pg Qb Qd) Ns(Fp Hr Hv Hx Ih Ii Ij Ik Ip Ir Iv Jk Jn Jo Jr Jt Lu Lw Lx Lz Mc Mh Mk Mn Mp Mv Mz Nc Nd Nj Nl Of Oi Oz Pb Qa Qd) Hu(aA Fp Ij Ip Is It Iv Jn Nn Of Oz Pb) It(Fp Ii Ik Is Jk Jo Of Oz Pb) aA(Fp Ij Ip Md Mz Nj Of Oz Pb) Is(Jk Mk Of Oz Pb) Ch(Ke oN Uh Wd) Pb(Fp Ij Ip Of) Ik(Fp Qd) Ld(Lp Uy) Of(Ij Oz) EqNn GlSh MkPe} Ld{Lp(Af aG aH aM Ap aZ Bo bR bU bX cB cE cF cK cL cN cP Cs Cu Cv CW Db DC Dd dH dN Dr Ed Fp fR Fw Gc Gn Gp Hq Hr Ih Ij Io Ir Is Iv Jd Jg Ji Jk Jl Jp Ke Kf Ki Kk Kl Kn Ko Kp Kq Ks Md Mq Mt Mv Nb Nn Nq Nr Nu Nv Ny Oe Oh Pe Pk Pz Qa Qb Qc Qd Qe Qh Qv Ri Rj Sr St To Uf Un Ur Uu Uv Ux Vh Vi Vq Wf Zx Ye Xa) Uy(Ba bQ Cw Dc Ed Fw Gc Gp Ih Ij Io Ir Is It Jg Jk Jn Ko Nb Ny Oh Pe Qa Qc Qe Qh St Tz Uc Ut Vh Vi Vq Xa) Fw(Dr Eq Fc Fd Fi Gb Gh Hl Ho Hp Op Rv Rx Ry Sh Si Sj Uw Ux Uz Va Vi Wb Wc We Wh Yl Zw Ye Tm Tl Xa) Nb(Dr Du Eq Fc Fi Gc Gh Rt Ru Rx Rz Sf Uw Ux Va Vb Vh Vw Vz Wb Wd We Wh Yd Zw Zx Tl) Vi(aO aX aY Bb Bg bH Ch cR cS Dk Ef Eq Jd Jm Jy Kd Ky Mx Nx Ou Pa Sr Ss Uv Yd) Ru(Cu Dc Dr Ed Hv Ij Is It Iv Ji Jn Ke Kn Mr Ny Oh Pe Qa Qd Qe Qh Tz Un Xa) Ij(Dr Eq Fc

Figure 30 Continued

Fi Gh Gn Hl Hp Rt Rx Ry Va Vb Vh Vw Wc Zw Ye Tm Xa) Ed(Du Eq Fc Fi Gh Gn Ho Op Rt Ux Va Vb Vw Zw Zx Ye Tl Xa) Yd(Dc Ih Is Jg Ke Ko Lx Nr Ny Pz Qe Qh St Uc Uh) Xa(aW aX aY Bb Ch dK Jm Kd Nr Nx Pa Qc Ul Th) Nr(Dr Eq Fc Fd Hp Rx Rz Vz Wf Yl Zw Ye) Dc(Dr Eq Fc Gh Ry Va Vb Vw Wd Wh Zw) Ny(Du Eq Fc Hp Rx Vw Wd Wf Ye Tl Th) Jg(Eq Fi Gh Sh Ux Va Vz Wh Zw Zx) Zw(Ih Is Lx Nv Oa Pe Qa Qb) Kd(Gc Gn Uw Ux Vh We Wf Ye) Eq(Is Jk Oh Om Qb Qh St) Gh(Ih Is Oh Qa Qb Qe Qh) Uh(cH dJ Id Ko Qa Ri Tv) Bb(Rt Rx Vh Wf Ye) Fc(Jn Oa Qa Qh) Ye(Al Cq Jm Pa) Ry(aZ Ir Is Vq) Du(Jn Oh Pe) Fi(Ih Jk Jn) Ji(Aj Ch Jo) Wd(Is Qa Qh) Ke(CH De) Oa(Gc Gn Rx) Dr(aW Jm) Wb(aW Th) Vz(Iv Qh) Uv(Fd Ho) IlWf IsRt QaWh StVa WeQh} Vi{Ch(Ao Ap aU aW aX bC bJ bW CO cQ cS De Ef Ez Gc Hv Ij Iu Jd Jh Kc Kd Ke Kg Kq Lx Mg Mi Mm Mp Mq Mt Mu Na Nn Nq Om Pd Pj Qd Qy Qz Rz Uf Ut) Hc(aJ aM aP aW bJ bP cL cQ Db Ed Fn Hq Hw Ih Ij Is Iv Jn Js Kc Kk Lx Mf Mt Mw Nn Nr Oa Oh Om Pe Pf Pg Qa Qg Rx Sr Ub Ue Vq Wh Xa) Bg(aU aW Co cQ Cx De Ij Is Kc Ki Lx Mi Mp Mt Mu Mv Nn Nq Oh Om Qd Qy Rx Ue Vq Wd) Pe(aD aP aZ bM bP bS cP cW Dd Dk Ha Hu Ib It Lu Oy Oz Qt Qw Rj Uh Ur Uu We Wf Ye) Eq(Ap aU aW bC bW CO De Ez Hv Jh Kc Kg Mg Mi Mp Mu Nn Om Pd Qy Qz Rz Uf) Of(Ap aU bZ cL Dd Fi Gc Ho Hq Hw Ij Is Kc Kd Lx Mf Mg Nn Om Pf Uc Ue Vq Vt) Lx(aO aY bF bG cH Dk Ed In Jl Jp Ky My Nx Qw Rb Sr Tn Wf Yd Zx) Wf(bP cP cQ cV Cx Fn Ih Ij Is Jn Js Ki Kk Mw Nn Oh Rx Sr Uu) Uu(aS bG Cw Dl Hw Ih Ij Jt Kf Nm Om Si Uc Ue Vq Vt Ti) Qw(bP cQ Fn Hq Ih Jn Kk Mw Nn Om Pf Qa Xa) Ed(aQ bZ fR Gp Hb Ij Lu Ma Ne Oz Si Ug) Dk(Fn Ir Is Jn Js Ke Kq Qa Qd Qe Rh) Ef(aW Co Kc Mi Mp Mu Nn Om Qy Ue Uf) Nn(Aj aX Iz Mv My Ng Qu Rz Sh Ss) Ij(AD bF bG cH Lu Og Rb We Zx) Sr(aF aZ bM cL cW Is Lu Mp Oh) Aj(bJ Gc Ho Hw Om Qd Vq) Lu(Fn Fw Gp Ki Kk Oa Rx) Sh(aW cP Ih Oh Pf Rm Ti) Oa(aG Bn cN Pj Uh Vq) bG(cQ Cx Ki Mn Oh Pf) My(Kd Mt Om Qd) We(Kq Mi Om Qa) Ke(Gl Nx Ru Uv) aX(Ap Ez Mt Uf) cQ(bF cH Jp Rb) Kz(aW Uv Th) Vt(Bo Ih It) aZ(aF Ap Iv) Ad(Mi Vq) Bn(Fn Tz) Og(Oz Uh) ApUx ArBb BoOz DeMp PoUv EzSs FrMt GpJp MjJs UaaU IhUh IsaY IzOm YdJi KxaW VbPd} Ij{aA(Fp Fr Hl Hp Hq Hr Hv Hw Hx Ih Ii In Io Iq Ir Is Iu Iv Jg Jh Jl Jm Jn Jo Jp Jq Jr Js Jt Lu Lv Lx Ly Lz Ma Mb Mc Md Mf Mg Mh Mi Mj Ml Mp Mq Mr Mt Mu Mv Mw Mx Mz Na Nb Nc Nd Ne Nf Nh Ni Nk Nl Nm Nn Nq Nr Nt Nu Nv Nx Ny Of Oh Oi Om Pa Pc Pd Pe Pf Pg Po Pz Qa Qb Qc Qd Qe Rv Sh Sj Vh We Wf Zx Ye Xa) Og(Hq Hr Hv Hw Ii Il In Io Ir Jh Jk Lu Lv Ly Mb Mc Md Mf Mg Mh Mj Mk Ml Mq Mu Mv Mx Na Nb Nc Nd Ne Nf Ng Nh Ni Nj Nk Nq Nr Nt Nu Oe Of Oi Pd Pg Qb) Oy(Fp Ih Ip Iq Jh Jp Jq Jt Lu Lw Lz Ma Mn Mw Mz Nb Nd Nl Nq Ns Nx Om Pa Pb Pc Pg Qd) We(aE aZ bF bL bR bS bZ dH Du Hb Hc Jl Jo Ke Kq Ny Of Pi Qm Rh Ri St Um Vc Tj) Vb(aC aE aS bE bJ bM Bo cZ dI Ed fR Hf Iv Mu Nc Wb) My(Fr Jp Jt Mi Mm Mp Mr Mw Mz Nb Nn Nv Pa Pe Po) aZ(Fc Gb Hl Op Rt Rv Rz Sf Sh Vh Vw Wc Wd Zw Xa) aE(Eq Hl Ho Ry Rz Uw Ux Uy Vz Yl Zx Tl) bM(Du Gb Hl Sh Uw Vc Wb Yd Xa) Ed(Fd Fi Sh Va Vz Yd Yl) Sh(Dd Hf Ii Ki Pe Rc) Eq(Kq Mq Qd Rh Tj) Th(Ar fR Sf Un Wb) Is(Hu Ms Oe Pb Rt) Vh(Hx Jo Pi Rh Un) Ng(Fr Jg Mm Wd) Xa(Jo Mm Nl Uu) Rt(Hv Lx Or Tz) Ch(Kc Ke Uh) Hl(Bc Ny Vt) Hu(Fr Lx Nn) Rh(Fc Rx Zw) Of(Uc Uh Wh) Aj(Wd Wh) Fd(Bo Uu) Hc(Kk Ko) Wb(bA dE) Vz(Nd Nh) Oa(Rv Zw) AdDu TjUx LxPb NbZx YdUu SjJo} Pe{Du(aD aE aH Ba bM Bo bP bQ cD cE cJ cL cN cT cV dB Dc Dd dF dH Dk Em Fw Gn Ha Hl Hr Io Is Jn Ke Kk Kq Ky Lv Lx Mk Mp Mt Mz Nd Nf Nk Nv Ny Oa Oh Oi Oz Pg Ph Pi Pk Qg Qh Qt Qv Rc Ri Rv Rx Ry Sj Ud Ug Uk Um Ut Vb Vs Vt Wf Yl Zx Ye Xa Tj) aD(Eq Fc Fd Fi Gb Gh Hl Ho Hp Lp Lt Op Rt Ru Rv Rx Ry Rz Sf Sh Si Sj Uw Ux Uy Uz Va Vb Vc Vh Vw Vz Wb Wc Wd We Wf Wg Wh Yd Yl Zw Zx Ye Tm Tl Xa) bM(Eq Fc Fd Fi Gb Gh Hl Ho Hp Lp Lt Op Rt Ru Rv Rx Ry Rz Sf Sh Si Sj Uw Ux Uy Uz Va Vb Vc Vh Vw Vz Wb Wc Wd We Wf Wg Wh Yd Yl Zw Zx Ye Tm Tl Xa) Yl(Al aN aW aY bA Bb Cs Dc dE Di dK Ex Fc Fp Fw Gp Ha Il Jm Kd Nd Nf Ni Nx Pa Po Qn Ru To Ul Uy Tm Th) Ha(Dr Fd Gn Hl Ho Hp Rt Rv Rx Ry Rz Sh Si Sj Uw Ux Va Vb Vh Vw Vz Wb Wd We Wh Yd Zx Tl) Bo(Hp Ru Ry Sf Si Uy Vw Vz Wb Wd Wf Wh Ye Tl) Vz(aN aW Cs Dc dK Fp Gp Il Kd Nd Qn Uh) Gn(Hc Qw Qx Ra Rj Uz Wf Wg Ye Wm) Sh(aN aX aY bQ cE cL Dd Ks Ph) Ye(aA aE aH Ny Oa St Ua) cE(Eq Rt Rv Rz Ux Vb Zw) Dc(Hl Rt Wb Yd) We(Jk Qa St Uu) Wf(aA aE aH Ny) Th(Dr Gh Oz) aZ(Va Wh Xa) Fc(aH bU) Sj(Af aY) Rz(aX Uu) Uh(Dr Wb) bX(Ru Uy) ChKe EqbQ MpYd HlcD IsOg WdaX UxVt} Ke{Ch(aA Af aM Ap aQ Ar aW Ba bB bJ bO bP bR cD cH cI cL Db De dJ dM dR eC Ed Ez Fr Fw GL hB Hf Hq Hr Hu Hv Hw Hx iA Ic iJ Ik Il Is Jd Jg Jh Ji Jk Jl Jm Jn Jo Jp Jq Jr Js Jt Ju Jv Kc Kf Kg Kk Ko Kp KQ Kr Ks Kx Ky Ly Ma Mc Md Mg Mh Mm Mn Mq Ms Mt Mu My Na Nd Ne Nh Nl Nq Nr Nt Oa oE OH Ou Oy Oz Pa Pb Pc Pd Pf Pg Ph Pk Po Pz Qa Qb Qc Qd Qe Qv Qy Rb Rh Sr St Tn To Tr Tt Tv Tz Ua Uc Uf Uh Uo Ur Us Wm) cH(Aj aM aW bN cI cQ De dM dR eF gP hB HC hF hG iA iJ Ik iO iP iZ Jo kQ kR kS Md Ms nW nY OF oK Oy pF Tn To Tv) dJ(De dK eT hO Ms Of qA qC rW uG uI uR uW uX vA vU wE zI) De(aM bR cX eC Ed Hu Ik Kc Kk Ms oE Tv Uh) Mz(rO uI uR vV wC wK Yd) Hu(rP rS uM vS wG wP yD) cQ(jP oE rN rW vB vQ wD) Dr(aW Fw Il Pa Ru Th) Of(bR iJ Il Ko Pa Uc) Ph(Ax Kc Mh Ms Oh Qa) Rx(bN fR Nb St Xa) Th(Ar hB Wm) Nn(Ef Hc Oy) aE(oE wK yD) qA(cJ Jn jT) Bg(Il Pa) Nb(We Zx) Yd(Lx Oh) Kg(fN Ru) Oy(Mt Pa) eC(dM Hc) rB(rR sK) oE(Hx rN) AjKo NrVz IzfN JnrR JorS KjdK RuaA aQwK aWiH cJrW yDwC} Is{Og(aA Hr Hu Hx Ih Ii Ik Il In Io Ir Iv Jl Jm Jn Jq Js Lu Lz Mc Md Me Mg Mi Mk Mp Mr Ms Mt Mu Mx My Na Nb Nc Nd Ne Ng Nh Ni Nj Nl Nr Ns Nt Nu Nx Oe Oh Oi Om Oy Pb Pc Pf Pg Po Qa Qb Qc Qd Qe) Rt(Ao Ar aY BG bL Ch Dd Dr Ed Eq Fd Fw Gp Hc Kl Nb Pi Pk Sr Yd) Oe(aA Fp Fr Jn Jp Jt Lh Lx Ma Mm Mn Mt Mz Nm Nv Ny Oz Pb Pz Qd) Ns(Fp Fr Jg Jp Lh Lx Ma Mm Mn Mp Nn Nv Ny Oz) Yd(bJ Cv Ji Nt Oz Qy Rv Uh Un Ur Vt) Oy(Fp Fr Jg Jp Lh Lx Ma Mm Mn Nn Nv) Pb(Fp Fr Ip Jp Lh Lx Ma Mm Mn Nn Nv) My(Fr Jp Lh Lx Mm Mn Mt Nn Nv) Oz(Fp Fr Ip Jp Lh Lx Ma Mn Nn) Sh(Af aY bM cE Dd Hu Jv Nu) It(aA Fr Jp Lh Lx Mn Nn) Eq(Jh Kq Mq Mu Nt Qy) Ms(Jg Jp Lh Mm Mn Nn) Ng(Fr Jg Lh Mm Nn Nv) Hu(Fr Jg Lh Nn Nv) aA(Ip Lh Mm Mn Nj) Dr(Ed Kd Up We) Wb(aY Bg Dk Uu) Fc(Af Gd Nu) Uu(Hp Vw Zw) Aj(Dg Ko) Ch(Ko Uh) Fp(Ik Mm) aY(Vb Xa) jT(Jk Jm) ArTh DeKc WmJi EdGn IkLh KkdJ UxbJ} Mz{yH(aI aM bF cE cW cZ fP gP hC iJ iO iP nW nY oH Or pF qG qO qT qU qV qW qX qY qZ rA rB) cH(dR eF gL gP hC hF hG iA iH iJ iO iP iZ jL kQ kR kS nW nY oE oF oH oK oN pF Tv) vI(aG aN Ar bJ bN Bo cB cW dJ Dk eC Fw hG kS nW Or Ph qT rW) wB(aL Ao Ar bE bL bN cF cN cW dD dJ Or Pk qG qT rB) tL(cW cZ fP iA kS oK oN Or qH qT qW qX qZ tF) uR(aS hB iJ oE oF qG qP qT qV qW rB rC) aA(Ip It Jg Jn Jt Lh Ma Mn Nj Og Oz) Or(rN uL uM vS wD wE wJ wK yD yL) rO(aS Bg Cq Ct Ef Iz Kk Ou) Qy(eZ hO hP qA qB qC qD) cW(uT vS wE wJ wK yD zA) uW(dH dK eC qT qY qZ rC) eZ(Ba Ct Mu Oy Qw Up) uI(aM bF cE dH qT qY) qC(Bg Ct Ef Jm Qw) wE(aY Bc bL cK rC) hR(Kc qG qH qI) wF(bF dH qT qY) Og(Jg Jt Nn) rW(Iz Mk vB) aY(uU wD) bP(rS zH) qD(Ct Ua) qT(tU yE) ChjT JkrN bLyD rCuL qOvP} Qa{Rt(aD aJ aP aR aZ bM bP bS Dc Dd Dk Hc Hu Ib Oz Qt Qw Uh Vq Wf Ye) Fc(aH Aj aZ Bo bX Dr Eq Fr Gd Hb Hc Oy Oz Ug Ur Uu Ye) bM(Fd Hp Lp Ru Rx Sf Sh Va Vh Wb We Wf Yl Zx Ye Xa) aZ(Fi Gb Ho Op Rv Rz Sh Wd We Wf Yd Zw Zx Tl) Bo(Du Eq Rz Sh Sj Uw Wd We Wf Wh Yd Zw) Wf(aA aY bJ De Ed Mw Nu Ny Us Uv) Sh(aN Dd Du Ed Ju Jv Uu Uv Zw) Aj(Ap Ba Ko Rx Rz Uh Vb) We(aN Bn cD Dd Du Us Zw) Ye(aA aY Bn Ed Rg Us Uv) Hl(aW Dk Ex Hc Kd Qt) Yd(aJ Dd Hb Ji Uh) Uh(Ch Ii Of Wb) aA(Hp Oe Og Ti) Dr(Ib Kd Ru) Du(Dk Hc Uu) Eq(Bn Om Rz) Ch(Ko Ry) Jg(Ng Og) Uu(Op Zw) aD(Rx Vb) AfSi DkWb WhdI JtOg RuUr UwaG} Kq{Ch(Aj bN Dr Du Eq Fc Fd Fi Gb Gc Gh Gn Hl Ho Hp Ko Lp Lt Nn Op Rt Ru Rv Rx Ry Rz Sf Sh Si Sj Uh Uw Ux Uy Uz Va Vb Vc Vh Vw Vz Wb Wc Wd We Wf Wg Wh Yd Yl Zw Zx Ye Tm Tl Xa) Eq(aW aY BA cL dK Ed Fc Fw Jg Jy Nb Nn Nx Ny Og Oh Om Ou Pa Pf Ru) Wf(An aW aY Bb dE Ed Fc Fw Kd Lp Nn Nx Oa Pf Po Ru Uy Th) Ru(Aj Bg Ef Fr Hc Iz My Of Oy Qu Sh Tn Uu We) Aj(Ap aW cH De fN Fw Ko Ky Lp Tm Th) Lp(Bg Ef Hc Iz My Sh Ur Uu) We(cD Ed Fw Jm Nb Nr Ny) Sh(aW aY Fw Jm Pa To) Bg(Ho Tm Ti) Th(Ef Qw Tn) Ed(Gn Ye) Fc(Jy Uu) Og(Rx Ye) Ux(aW Nx) DeFd TmUu OfUh} aA{Ip(Fp Fr Hu Ih Ik Jg Jn Jp Js Jt Lh Lv Lw Lx Lz Ma Md Mm Ms Mt Mw My Nc Ng Nl Nm Nn Ns Nt Nv Nx Ny Oe Oy Pb Pc Qb Qd) It(Fp Fr Ik Jg Jl Jp Js Jt Lv Lw Lx Ma Mm Ms Mt Mw Nj Nm Nn Ns Nv Nx Ny Og Oz Pb Po Qd) Og(Fp Jn Js Jt Lx Ma

Figure 30 Continued

Mm Mn Nm Nn Nv Nx Ny Pz Qd Qe) Lh(Hu Ik Jn Lw Md Mn Ms My Ng Nj Ns Oe Oy Oz Pb) Ns(Jg Jn Jt Lx Ma Mm Mn Nm Nn Nv Ny)
Nj(Jg Lx Ma Mm Mn Nm Nn Ny Qd) Oe(Jg Jt Lx Nn Nv Pz Qd) Mn(Jn Ms Oy Oz Pb) Lx(Fc Oz Pb Zw) Jg(Hu My Ng Oy) Oh(Gb Ho Rx Si)
Ji(Ch Ru Wm) Oz(Ma Nn Qd) Oa(Gc Ti) Pf(Sh Si) FpMm NnHu NgJt IkQd} Ji{cH(cI dR gL hB hC hF hG iA iH iJ iO iP iZ jT kQ kR kS nW
nY oE oF oH oK oN pF Tn To Tv) Wm(li Ik ln Ip Iq Ir Jl Jm Jp Mh Mj Mk Mp Mr Mt My Na Nd Ne Ng Ni Nk Ns Oi Oy Qd) Ch(Ba bN Ed gL
hB iA iJ Jp Kk Ko oF Qy Ri Tv Ua Uc Uh Ur Us) jT(Ba bI bZ Co Cp Hc li JO jP Mg oK Qu Qw Qy Ut Vv) Ed(Fi Gn Va Yd Xa) Aj(Ap Ba jP
Ko) Th(Dr fR) Yd(Jk Ny) Rt(Jm Oa) dJ(jE jO) AaOg DeUh NbUx UcOf IzjP RubM bNIL cWwD} Oa{aG(Dr Du Fc Fd Gb Hp Op Rt Rv Rx Sj
Va Vh Vw Vz Wb Wc Wd Wh Yd Zw) Gc(aZ bM BO cE Cq dD dI Dr Iq Jo Uo) Dr(cE Cw Gp Mg Mm Pf Pj Rx Si Ti) aZ(Fc Fi Gb Ho Rx Rz
Ux Vw Wd) Bo(Gb Ho Si Uw Wd) Gb(Hb Qv Uh Ye) Si(Af dI Iq) Sh(aC cE Sr) Zw(Cu Ic Vq) Rx(bM Pi Qm) Fc(Hb Ur) Gn(Hw Pi) Wb(Mg
Ti) Vw(Hc Oz) CwDu DdLp NbRy HIVq JhWf YeaC RzaX RvaH OpdI VccE} Lx{Yd(aC bE bJ bM Bo Dd Gb Gc Jh Mh Mu Mv Nt Pj Qd Ql
Qm Qy Wb) Wb(aD aW aY Bb Bn Ed Fw Jy Kd Ky Og Sr) Fc(aH bM bN BO Dr Ed Hp Je Ny) Zw(bJ bM Dr Hp Je NI Nt Ny Uo) Ed(Dr Gb
Va Vz Yl Tm Xa) bM(Fi Ho Si Wf Zx) Oy(Jg Jt Nn Nv) aY(Vw Xa Ti Tm) Dr(Kd Or Sr) Fw(Vz Yl) My(Jg Ns) Hq(rS rT) Wf(Mw Ny) Og(It Jt)
DdSh ThRg HpUs VzaD WdUv JkRt} Eq{Nn(aE aX aZ Ba cE Cu Dk Jk Nv Ny Om Qd Qt St Ua Un) Om(Ba Dr fR Iv Mq Nt Nu Sh Us Uu Va
Xa) Mt(aX Hq Hw Hx It Nv Ny Qt St) St(CO Ez Jh Pd Rz Uf) Nv(Ap aW Ez Mg Pd Rz Uf) Ny(aW Cw Ez Mg Pd Rz Uf) Mq(Ba Bb Ed Fw Ph)
Nb(Ez Mp Pd Uf) Oh(Jd Nt Qy) Ba(Ed Mp) Ez(cE Ed) MgcE QyPf JlaW} Ed{Xa(aK aU aZ Ba bC bM Bo bQ cW cY Dc Gz Hc Mf Ne Oi Pd
Qv Sh Uh Vq Vt) Ba(Fc Fi Gb Lp Si Ux Yl) Ye(Ef Ez Ih Mq Mr Pd Vq) Dr(Nb Oh Pf Vt) Fi(Cu Pd Vq) Sh(Ih Om Tn) Ru(aG Ne Vt) Oz(Wd
Wh Zw) Ez(Rz Ux) Gn(Dc Om) Oh(Gb Rv) Pd(Fc Ho) DuPo WfJn} Og{Jg(Fp Ip It Iv Jl Jn Jq Js Lh Lw Mr Nn Ns Nv Po Qb Qd Qe) Jt(Fr Ih Ip
It Jl Lh Nn Ns Nv Ny Po Qb Qd Qe) Nv(Fp Ih Ip Iv Jn Lw Ns Oz Pb Qd) Nn(Ih Ip It Iv Lh Mr Qd) It(Fr Jl Jp Lh Om Qd) Ih(Fr Ip Lh Ma) Qd(Ik
Ip Lh)} Uh{Ch(BA dM Id Jq Kf Kg Kn Ko Mr Mt Nr Oh Om Qd Ri Tn Tv Uc) Tv(bN cH De dJ Ic Of Ri Ur Wm) Ko(bN De dM Ri Uu) Of(Ny
Om Uc) dJ(Kk Kn Oh) Dr(Nd Pf) Id(bN Ri) NroN NbTl WbOh KkRi VtbN cHgL} Ny{Wf(aW bJ bZ Fr Ma Mt Ni Nn Pf Ut) Sh(aW cL Cw Kd
Nn Rx Uk) Uu(Fi Gc Ho Rz Si Ux Wd) aW(Lp Rz Ux Vb Vz Yl) Nn(Rz Ux We Wh) Rx(Iu Kx Pd Ur) We(Cw Mt Pd) ArTi ChRz XaOz YebJ
RvOh} Aj{Om(Du Gh Hp Rt Rx Si Va Vh Vw Vz Wb Wd We Wh Yd) Wd(Fw Pf Qc St) Jt(Ap Ba Mt Nn) Ko(Jl Mt Nn Qd) Ba(Qd Qe) dJ(qZ
vI) ApCu NmvI HoSt UcOf QdRu} Nn{aX(Fd Gb HI Hp Op Rt Rx Sf Sh Sj Vb Vw Wb Wd Zw Tl Xa) aZ(Fc Gb Hp Ry Yd Zx) Sh(aE cE Io
Nv) Vt(Dr HI Wb) ChKo NgJg UxaE} Nb{Tl(aJ Bo bS Hc Ib It Lu Oz Qv Qw Rj Ug Ur Uu Vq Wf Ye) Bo(Fd Ry Uw Vz Wc Xa) Mp(Rt Yd)
Mq(We Wh) ChTi FcOh ZxOu WfKk RuUn UfUx} Oh{Wb(aF aW aY Bb bG Bo dJ Ic Jg Kd Mj Or Qy Uk) Dd(Rt Sh) Gb(Af bM) Qy(Gd Yd)
AanK DrKd NtZw HpbG RtPi Vcdl} Sh{Fw(Hx Ih Mq Mv Nf Oz) Dd(Jn Js Pf Rm) Jv(Fy Ih Xa) Sr(cE Ih) Js(aY Bo) Ju(Om Ut) MtaX SfUt
JncE NvOe OmbN} Dr{Tz(aW Bb dK Kd) Qd(Kd Ru Th) Fw(Kk Rm) Kd(Bo Js) Pf(Hc Vt) UcUu RuRh OmUv OraW} Xa{Un(aW Fc Fw Kd
Nx Pa Ru) aX(Ap aW Ez Mq Mt) Bo(Fw Sr) Oz(aZ Sr) ChUt} Uu{Gc(bQ Nv Om) Qd(Ru Rx Vz) Jn(Fc Ux) Vw(Rm St) FdQy GbOm HpUc
IhRx SiNv} aZ{Sr(Rz Vw Wb Wd Wh) Vq(nD nI Va) Iv(Ru Uy) Ry(Ez Mq) FcQx IuVa QdRu} Wf{Jn(aM Mw Nc Nj Nl) Mw(bA cT} Fwlh
GlUt NvOz} Mq{Dd(Lp Ru Uy) Ch(Fd Uw) Jm(We Ye) LpUr UyaX} Ng{Jg(Ih Js Lh Nv Qd) Jt(Fr Nv) UnjT} Qd{Ch(Ko Ru Rz) Ik(Fp Jg Lh)
ArTh} Rt{Dc(aQ Ut) Om(Bg Ch) DdJn DpJs} dJ{Kp(pS rS yK) wB(Ct Lu) KkrS} wD{An(cO cW) iP(qT rS) BbbL CtMe} Mt{aX(Op Rv Yd)
MyJg HqUx} Vq{Jo(nC nL) AxHl CsnH} aW{rS(cZ jT) WbJs NvUx} cQ{qZ(Hc iO Iv) KnjT} Sr{Yl(Pf Ri) OrVa} Ko{Ch(bN Nq) VtbN}
wB{nW(dM qZ vH)} Fc{JnaH RmUr} Uc{Of(Jq Ur)} Kn{jT(Ct Ph)} ApNvUx PoRubM ExNclK FplkJt NsItJp LuWbPf IhJgOe HcWdJn
YdOmOy VtbNcH iPrSoF Unconstrained panels with 3 analytes, where 2.4E-8 >= 'model p-value' > 1.0E-8. Contains 9,805 panels of 32,874,593 total panels evaluated. :
Li{Qa(Fp Fr Hq Hv Hw Hx Io Iq Ju Jg Jh Jm Jr Js Lh Lu Lx Ly Ma Mb Md Me Mg Mh Mi Mk Mm Mq Mr Mt Mu Mw Mx Na Nb Nd Ne Nf
Nh Ni Nk Nm Nn Nq Nr Nt Nu Nv Nx Ny Oh Om Pa Pc Pd Pe Pf Pg Po Pz Qb Qc Qd Qe) Jr(Fp Fr Hq Hv Hw Hx Ii Io Jg Jh Jk Jm Js Jt Lh Lu
Lx Ly Ma Mb Md Me Mg Mh Mi Mj Mk Mm Mq Mr Mt Mu Mw Mx Na Nb Nd Ne Nf Nh Ni Nk Nm Nn Nq Nt Nv Nx Ny Of Oh Om Pa Pc
Pd Pe Pf Pg Po Pz Qc Qe) Nv(Fp Fr Hq Hr Hv Hw Hx Iq Jh Jm Js Lh Lu Lv Lx Ly Lz Mb Me Mf Mg Mh Mi Mj Mk Ml Mm Mp Mr Mt Mu
Mw Mx Na Nc Nd Ne Nf Nh Ni Nj Nk Nm Nn Nq Nt Ny Oh Pa Pc Pd Pe Pf Pg Po Pz Qb Qc Qd Qe) Fp(Hq Hr Hv Hw Hx Ii Jg Jh Jk Jo Js Lh
Lu Lv Lx Ly Lz Ma Mb Md Mf Mi Mj Mk Mm Mp Mr Mt Mu Mv Mw Na Nc Nd Ne Nf Ni Nj Nk Nm Nn Nt Nx Ny Of Oh Pa Pc Pd Pe Pf Pg
Pz Qb Qc Qd Qe) MI(Hq Hr Hw Hx Ii Iq Jg Jh Jk Jm Lu Ly Lz Ma Mb Md Me Mf Mg Mh Mi Mj Mk Mm Mp Mq Mt Mu Mw Mx Na Nb Nd
Ne Nf Nh Ni Nj Nk Nm Nn Nq Nr Nt Nx Ny Oh Om Pa Pc Pd Pf Pg Po Pz Qc Qe) Hv(Hq Hx Ii Jg Jh Jk Js Jt Lh Lu Lv Lx Ly Lz Ma Mb Md
Me Mg Mi Mj Mk Mm Mr Mt Mu Mw Mx Na Nb Nc Nd Ne Nf Nh Ni Nj Nk Nm Nn Nt Ny Of Oh Om Pa Pc Pd Pe Pf Pg Po Pz Qc Qd Qe)
Mf(Fr Hq Hr Hw Hx Ii Iq Jg Jh Jk Jm Lx Ly Lz Ma Mb Md Me Mg Mh Mj Mk Mm Mq Mt Mu Na Nb Nd Ne Nf Nh Ni Nk Nm Nn Nq Nr Nt
Nu Nx Ny Of Oh Om Pa Pc Pd Pe Pf Pg Po Pz Qc Qe) Nc(Fr Hq Hr Hw Hx Ii Io Iq Jh Jm Lu Lx Ma Mb Md Me Mg Mh Mi Mj Mm Mq Mt
Mu Mw Mx Na Nb Nd Nf Nh Nj Nl Nm Nn Nq Nr Nt Nu Nx Ny Oh Om Pa Pc Pd Pe Pf Pg Po Pz Qc Qe) Nj(Fr Hq Hr Hw Hx Ii Io Iq Jg Jh Jk
Jm Lu Ly Ma Md Me Mg Mh Mj Mk Mm Mq Mt Mu Mx Na Nb Nd Ne Nf Nh Ni Nk Nm Nn Nq Nr Nu Nx Ny Of Oh Om Pa Pc Pd Pf Pg Po
Pz Qc Qe) Mp(Fr Hr Hw Hx Ii Io Iq Jg Jh Jm Lh Lu Lv Lx Ly Ma Mb Me Mg Mh Mi Mj Mm Mq Mt Mu Mw Mx Na Nb Nd Ne Nf Nh Ni Nk
Nm Nn Nr Nt Nu Nx Ny Oh Om Pa Pc Pe Po Pz Qc Qe) Lh(Fr Hq Hw Hx Io Iq Jg Jh Jm Js Lu Lv Lx Ly Ma Mb Me Mg Mh Mi Mm Mq Mr Mt
Mu Mx Na Nb Nd Ne Nf Nh Ni Nk Nm Nn Nq Nr Nt Ny Oh Om Pa Pc Pd Pe Pf Pg Pz Qc Qe) Lu(Hq Hr Hw Hx Ii Iq Jg Jh Jk Jm Lv Lx Ly Lz
Ma Mb Md Me Mi Mj Mk Mm Mr Mt Mu Mx Na Nb Nd Ne Nf Ni Nk Nm Nn Nt Nx Ny Of Oh Pa Pc Pd Pe Pf Pg Po Pz Qc Qe) Lv(Fr Hr Hw Hx
Io Iq Iu Jg Jm Lx Ma Md Me Mg Mh Mi Mj Mk Mm Mq Mt Mu Mx Na Nb Nd Ne Nf Nh Ni Nk Nm Nn Nq Nr Nt Nu Nx Ny Oh Om Pa Pe Pf
Pg Po Pz Qe) Qb(Fr Hw Hx Io Iq Iu Jg Jh Jm Ly Ma Md Me Mg Mh Mk Mm Mq Mt Mu Mw Mx Na Nb Nd Ne Nf Nh Nk Nm Nn Nq Nr Nu
Nx Ny Oh Om Pa Pc Pd Pf Pg Po Pz Qd Qe) Lx(Fr Hr Hw Hx Ii Io Iq Jg Jh Jm Js Ma Mb Me Mg Mh Mi Mj Mm Mr Mt Mu Mx Na Nb Nd Ne
Nf Nh Ni Nk Nm Nn Nq Nt Nx Ny Oh Pa Pc Pd Pe Pf Pg Pz Qc Qe) Lz(Fr Hq Hr Hw Hx Jg Jh Jk Jm Ly Ma Mb Md Me Mg Mh Mj Mk Mm
Mq Mt Mu Mx Na Nb Nd Ne Nf Nh Ni Nk Nm Nn Nq Nr Nt Nu Nx Ny Oh Om Pc Pd Pf Pg Po Pz) Mc(Fr Hq Hr Hw Hx Io Iq Iu Jg Jh Jm Ly
Ma Mb Md Me Mg Mh Mj Mk Mm Mq Mt Mu Mx Na Nb Nd Ne Nf Nh Ni Nk Nm Nn Pa Pc Pd Pf Pg Po Pz) Mi(Fr Hq Hr
Hw Hx Ii Jg Jh Jm Js Ly Ma Mb Me Mg Mh Mj Mm Mr Mt Mu Mw Mx Na Nb Nd Ne Nf Nh Ni Nk Nm Nn Nt Nx Ny Of Pc Pd Pe Pf Pg Po Pz
Qc Qe) Qd(Fr Hr Hw Hx Io Iq Iu Jg Jh Jm Ma Md Me Mg Mh Mk Mm Mq Mt Mu Mw Mx Na Nb Nd Nf Nh Ni Nk Nm Nq Nr Nt Nu Nx Ny
Oh Om Pa Pc Pe Pf Pg Po Pz Qe) Mv(Fr Hq Hr Hw Hx Ii Iq Jh Jk Jm Ly Ma Md Me Mg Mh Mj Mk Mq Mu Mx Na Nd Ne Nf Nh Ni Nk Nm
Nq Nr Nu Nx Ny Of Oh Om Pc Pd Pf Pg Po Pz Qc) Mw(Hq Hr Hw Hx Ii Iq Jh Jk Ly Ma Mb Md Mg Mj Mk Mm Mt Mu Mx Na Nd Ne Nf Nh
Ni Nk Nm Nn Nq Nt Nx Ny Of Oh Pa Pc Pd Pe Pf Pg Po Pz Qc Qe) Pe(Fr Hq Hw Hx Jg Jh Jm Js Ly Ma Mb Md Me Mg Mh Mm Mr Mt Mu
Mx Na Nb Nd Ne Nf Nh Ni Nk Nm Nn Nq Nr Nt Ny Oh Om Pc Pf Pg Pz Qc Qe) li(Hq Hr Hw Hx In Jg Jh Jk Ly Ma Mb Md Mj Mk Mm Mt
Mu Mx Na Nb Nd Ne Nf Nl Nk Nm Nn Nt Nx Ny Of Oh Pa Pc Pd Pf Pg Po Pz Qc Qe) Nt(Hq Hr Hw Hx Jh Js Jt Ly Ma Mb Md Me Mg Mh Mj
Mm Mr Mt Mu Na Ne Nf Nh Ni Nk NI Nn Nq Ny Of Oh Pc Pd Pf Pg Po Pz Qc Qe) Mr(Fr Hw Io Iq Iu Jg Jm Ma Mb Me Mg Mm Mq Mt Mu

Nn Nx Oe Pe Pf Qd Vt) Lj(Hu In Ir Iv Jn Lh Lu Lv Lx Ma Mg Mi Mr Ms Mw Mz Nc Nl Nm Ny Pc Pz) Ow(dJ Fi Hp In Iz Jo Lt Ng Qw Ru Si Uz Vc Vj Wc Wg Yg Yh Yi Yj Zq Yf) Oe(Fp Hu Iv Jg Jl Jq Js Lh Lv Lw Lx Mm Ms Mz Nc Nl Nn Nv Ny Qa Qb) aA(Fp Ih Jg Js Jt Lh Lv Md Me Mm My Nc Ng Nl Nm Nn Ny Oi On Qb Qd) Aj(Ba Bc cH Dg Hf Ic Iz Kj Mg Or Pk Qv Qy Ri Uo Ur) Hc(Ap aQ bS cH Hb Ji Kf Ld Me My Ou Qd Us Vi Vt) Kc(Af aQ bN cH Cp cQ Ef Hb Hq Ic Jk Ko Nr Ur Vt) Ch(Ez Hf Ic iO Kf Kp Ld Pj Ri Sr Tn Tv Us) My(Ih Ik Jl Jn Jq Jt Lh Lw Mw Mz Nb Nn Nv) Zq(aK aU aX bM cD Dc Gp Ib Jy Mv Oh Ss Vw) Vt(bN cH dK Ik Iz Jk Ko Of Ou Rt Wc We Yh) Ms(Fp Ik Iv Jg Jq Js Lh Lw Mw Mz Nn) Nj(Fp Hu Ij Iv Jn Jt Lw Mp Mz Ng On) Ih(Fp Hu Ij Ik Jn Lu Lv Lw Mz Oi On) Ip(Ij Il Iv Jn Jt Lw Mn Nc Nl On Ur) Ur(bN cH dK In Ji Pi Qv St Tz Uc) Vj(aD aK aU bM cD dK Gp Jy Nd Pa) Ns(Iu Jh Jk Mb Mu Nf Nr Pz) Ij(Hp Hx Jk Lw Md Mv Of Yf) Ik(Jn Jt Kk Ko Ng On Qa) Jj(Hb Kf Kg Kk Kp Ld Ph) dR(Fc Gh Lp Ru Ry Uy Vi) aK(Yg Yh Yi Yj Yk Yf) aU(Yg Yh Yi Yj Yk Yf) Ng(Jn Lh Lw Mm Nv) Hu(Jg Jn Jt Nn Nv) dJ(Ld Qw Ss To Us) Yh(aG Ld Mp) Ji(Kj oN Up) Wf(Im Qd Tr) Of(Kq On Uc) Du(Ld Pe) Yf(Mg Vq) Mk(Jl Pe) Sh(Gp Tr) Jo(Hb Pj) Rx(Vs Yi) Om(Vw Yg) cH(iO oH) WmIn GnVu LuVi MdMz NcNk NeNl TvcQ IlQd SjLd JkOn XagP} Nw{Ch(Hf Hq Hu Hv Hw Hx Id iJ Is Jj Jl Jm Jn Jo Jq Jr Js Ke Kg Ly Mn Mt Nn Oa Oz Po Pz Qb Qc Qt Qu Ra Rg Rh Tn Tt Tz Ul Uo Up Vp Vt Wm) Aj(aA Cu Dc dJ Ed Hr Hx Id Ih Ir It Iv Jj Jk Jv Kg Ko Kq Ly Mb Mg Mi Mn Mr Nr Oh Om Oy Pb Pc Pe Pf Pg Po Qb Ri Sr Uc Uh Vt Wm) Wm(dK Fr Hr Hx Ih Il Io Iu Jh Lh Lu Lx Lz Ma Mf Mg Mh Mm Mq Mu Mv Mw Mx Nk Nq Nt Nv Ny Oh On Oz Pa Pd Pf Po Pz Qb Uh Us) Rx(cE dR eF fP gL gP hB hC hF hG iA IH iJ Im iO iP iZ kQ kR kS nW nY oE oF oH oK oN pF Vu) Aa(Hv Hw Is Jg Jh Ji Jk Jl Jp Jr Js Jt Lh Lj Ms Nb Nc Nl Ns Oe Of Om Pd Pf Pg Pz Qd) Yh(aA aW Ba bJ Ct Ih Ij Im Lx Nn Nr Nt Nu Oh Ow Pe Ps Qa Ru Sr Ub Va Yi Tj Ti) Jv(aQ aW dJ Ed Fw Hf Ic Ij Im Ji Jm Ko Lj Ly Mj Mt Nl Nr Oa Oi Ow Ri Sr Tv Uh) cH(aA Ed gL hB hC hF hG iA iH iO iP iZ Jj kQ kR nY oF oH oK pF Ri Tr Tt Uh Us) De(Hw Id Im Is Jh Ji Jj Jl Jo Jq Js Jt Oz Pe Po Qb Qy Sr Tn Ul Vt) Uh(aA bN Ed Hq Ic Id Ik Ld Lj Mj Mk Mp Ms Mt My Nr Oa Oi oN Qa Us) Ed(aQ Bg bN Ii iJ Ik Jj Jk Ky Ld Nd Oe Oi oN Ow Pb Us Yi Ye) Us(Id Ir Is Iu Ji Mt Nr oN Pb Pi Qa Qe Up Vt Ti) jO(Hv Hw Hx Jk Jn Jq Jr Js Jt Mz Oy Pg Qa Qc Qd) Th(aQ Ax hB Hx Ij Kd Mv Nn Ow Pe Qv Ub) Ow(Ao Hc Iz Jd Jo Lj My Oa oN) Tv(Af aW BN Hc Ii Nv Vp) Ru(bN eF Hc Hf Kl Kr Kz Nf) Bg(Jh Ji Jp Jt Mt Qy Ri) Yd(aY gL Jh Pd Tt Yi) Wf(GL Jm Kd Uv Tm) jT(Jr Lj Ne Oa Oy Qe) Jj(bN dJ Kg Ko Ri) aY(Sh Vj Zx Ti Yf) dK(Jd Ju Oa Tz Vt) Fw(Hl oN Sh Vj) Hc(Hv Hw Jn Sr) bN(Hv Id Jn Jr) jP(Hq Hu Js Qe) Of(Id Up Vp) Vi(eF fP Qw) cI(Hu Jn Oz) Yf(aZ Nb) Ti(Kd Oe) Nl(jK lN) Tt(Sh Zw) Im(Rv Yg) Sr(Ii Va) Lt(kQ kR) Ri(Oi rN) Oa(iJ Oi) aW(Eq Vz) BoYj DugL EzNg GhhG NeIc YiaZ SfhB ShPh ZqKr ZwPe JoKg XakR UudJ OzbA} Ok{Is(Fr Hv Hw Io Iq Ir Iu Iv Jg Jl Jm Jp Jq Jr Js Jt Lv Ly Ma Mb Me Mf Mg Mh Mi Ml Mm Mq Mr Mt Mu Mx Nb Nd Ne Nf Nh Ni Nk Nm Nq Nr Nt Nu Nv Nx Ny Oh On Pa Pc Pe Pf Pg Po Pz Qa Qd Qe) Fp(Hq Hv Hx Ii Ij In Io Iv Jg Jh Jm Jp Jq Js Jt Lw Lx Ly Ma Mb Md Mj Mk Ml Mm Mn Mp Mw Mz Na Nc Ng Nj Nl Nn Ny Of Om On Pc Pf Qa Qb Qc Qd) Oe(Hq Hu Hv Hw Hx Il Io Iq Ir Jm Jr Jt Lh Lz Ma Mc Mm Mn Mp Mr Mw Mx My Mz Ng Nr Of Om Oy Pe Pf Pz Qc) Jn(Hu Hx Ih Ii Ik In Jp Lu Lw Lx Ma Md Mj Mk Mn Mp Mw Mz Nc Nl Nv Ny Of Oi Om On Pf Qa Qb Qd) Pb(Hu Il Io Iq Ir Iu Jg Jl Jm Jo Jq Lu Lw Lz Mc Mm Mr Mw Na Nc Ng Nl Nm Oh Oi Om Oy Pe Pg Qe) Hr(Fr Il Io Iq Ir Iu Iv Jl Jp Lh Lw Lz Ma Mc Mm Mn Mp Mt Mw Nc Ng Nr Oy Pc Po Qd Qe) Oz(Fr Hu Ij Io Iv Jl Jp Js Lh Lz Ma Mc Mn Mp Mt Mz Nc Nl Nr Nv Ny Of On Oy Pe Pg Qa) Ms(Hu Iv Jg Jl Jp Jt Lw Lz Mc Mi Mp Mr Mt Mw Nc Ng Nl Nr Nv Of Om Pc Po Qc Qe) Ns(Fr Hu Ij Iv Jg Jl Jq Jr Js Jt Lh Lw Lz Ma Mc Mt Mw My Mz Ng Of Po Qe) Ih(Fr Hu In Iv Jg Jp Lh Lu Lx Lz Ma Mc Mn Mz Nj Nl Ny Of Oi On Qb Qd) My(Il Iv Jh Jl Jo Jp Jq Lw Ma Mc Mp Mr Mz Nc Nq Nr Om Pf Po Qe) Ng(Fr Iv Jl Jp Js Lh Lw Lx Ma Mn Mp Mw Nc Nl Nv Ny Po Qa Qb Qd) Ip(Hu Hx Ii Ij Il Jp Js Mc Mn Mt Mw Mz Nc Nl Of On Qa Qd) Jo(Io Ir Jg Jl Jt Lx Ma Mm Mn Mp Mr Mz Nc Nm Nr Ny Qa Qd) Oy(Fr Iv Jl Jp Ma Mn Mr Mw Mz Nc Nl Nr Pe Pg Qe) Nn(Iv Jh Jk Lx Mc Mk Mz Nc Nl Of Oi Qb Qd) Qb(Hu Ii Iv Ma Mc Mj Mk Mz Nc Nl Of) Ij(Ii Jh Jk Lx Md Mk Om Qd) Qd(Mc Mj Mz Of Oi Qc) Lx(Hq Hu Mz Nl) Qa(Ik Mc Mj Of) Ch(Ke Uh) Mk(Mp Pe) Mz(Nc Nl) Js(Mc Of) aA(Nf Nu) AjIm WmJi MpHq NcNk NeNl HuNv IvOf YhPe LdLp RiUh PdPf} Jj{Is(Hq Hu Hv Hw Hx In Iq Ir Iu Jh Jk Jr Lu Lv Ly Mb Md Mf Mh Mi Mj Mk Ml Mq Mu Mx My Na Nb Nd Ne Ng Nh Ni Nk Nq Of Oh Oi Oy Pa Pd Pe Pg Qc) Aa(Fr Hr Hu Hv Hw Hx Ii In Iq Jg Jp Jr Jt Lv Lw Ly Lz Ma Mc Mg Mm Mp Mr Ms Mu My Nm Nq Nr Nt Oh Om Oy Pb Pc Pe Pg Pz) Nn(Fr Hw In Io Iq Iu Jp Jr Ke Ko Lu Lw Lz Ma Mc Mf Mg Mi Mm Mp Mt Mv Mx Na Nb Nd Ng Nr Nu Pa Pc Pf Pg Qb Qc) Jt(Ii Ik Iv Jg Jm Jp Jq Lu Lv Lz Mc Mp Ms Mx My Ng Nj Nl Nr Nt Oe Pb Pe Pf Pg Pz) Lj(Fp Hx Io Iq Iu Jr Lu Lz Mb Mk Mq Ms Mv Mx Na Nf Nh Ni Nr Nu Oe Of Qb Qc rS) Qa(Fr Ih Ii Il Iv Jl Jp Js Lw Lx Mc Mp Mr Mw Mz Nj Nl Ns Nt Ny Po Pz) Qd(Fr Iv Io Jp Jq Lw Lz Mc Mi Mp Mz Nc Nj Nm Ns Nt Oe Ow Pb Pc Pe Po) It(Hv Io Jr Lv Lw Lz Mc Mi Mx My Nl Ns Nu Og Oh Oz Pe Pg Uh) Nv(Io Iu Jh Jk Ly Mb Mh Mq Mu Na Nf Nh Ni Nq Nx Oi Om Pa Qc) Js(Ii Ik Lv Lw Lz Mp Mr Ms Mt My Nj Nl Ns Nt Nx Oe Pc Qe) Mn(Fr Ir Jm Jq Ma Mr Ms Mt Mw Nh Ns Oz Pb Pz Qb) Jg(Hw Ii Jm Jq Lz Mp Mx Nl Ns Nt Ny Oe Oz Pb Pe) Uh(Dd Fw Hw Ji Ke Kf Kg Kn Ld Mr Mt Oh Uc Wm) Lx(Fp Ii Iv Jq Mm Mr Mz Nl Nm Ny Oz Pb Pz) Nm(Ii Il Ip Jn Mr Mw Mz Ny Qb Qe) Ji(De Ed jP Jv Ko Ld Ow Qy Ri Us) Mm(Ii Il Ip Mr Mz Ny Po Qe) Ke(bN cQ dK Fw Il Jm Ld Ms) Mw(aA Fp Ih Ii Jl Nt Ny) Mz(Fp Ih Jl Nl Nt Ny Po) Ip(Iv Mr Mt Nl Og Pz Qe) Jn(Ih Ii Jp Ma Mr Og Qe) aA(Fr Jm Nj Po Qb Qc) Ma(Ii Iv Jl Qb Qe) Ny(Ii Iv Mr Nt Og) Po(Jp Oz Pb Pz) Fr(Fp Iv Nl Pb) Jl(Ih Jp Oz Pz) Ko(bN Ed Il Im) Ow(cH Kf Kn) Ii(Ms Pb) DeKq FiOa FpLw IhJp ImSh QeOg KnjT NxjP dJqZ} Im{Ye(dR eF Fa Fb fP gL gP hB hC hF hG iA iH iJ iO iP iZ kQ kR kS nW nY oE oF oH oK oN pF Qx Ra Ri Rj Ru St Tr Tt Ud Uk Ul Um Uo Uz Vc Vj Vu Vv Wg Yg Yh Yi Yj Yk Zq Tj Yf) Sh(Ao Ax Di dR EF Fb fP Gc gL gP hB hC iA Ib iP Iv iZ Kj Kk kR kS Mm Nb nW nY oE OF oH oK oN Op PF Pk Rz Tr Tt Vu Vv Wb Yg Yh Yi Yk Yf) Wf(An Cp Cw eF Hw Ij Ir Iv Kr Lw Mi Ml Mq Mt Nb Ni Pd Qw Qx Ra Tr Ud Un Us Uz Vv Wg Yi Yj Zq Yf) Ch(Du Fd Hl iO Jp kC Lt Mn mW Ow Ps Rt Uh Uw Va Vj Vz We Wh Yj Zq Zx Tm Tl) Aa(Fp Hr Ii In Is It Jn Jt Md Ms My Nc Ne Nl Ns Oe Of Oz Pc Qb Qd) Zq(aG AJ aR aX aZ bS Eq Fr Hc Hu Ib Iz Mu Qt Qu Qw Qy Qz Ug Ux) Aj(Ap Bb Cu De dJ Ij iO Jp Jq Kf Kn Ld Ma Mr Nd Nn Nx On) Qw(Gb Rt Ru Rv Uw Uy Uz Va Vb Vh Vj Wc We Wg Wh Yi Yj Yf) iP(cH Fd Gc Ho Hp Ry Sf Si Sj Vz Yd Yl Zx Tl) Yf(aG aH aZ bS Hc Hu Ib Oy Ug Uh Ur Uu) Yg(aG aZ bP Dc Fy Hc Is Lx Oy Qh Ug We) Yj(aG aZ bS Hb Hc Hu Ib Mw Oy Qt Ug Uh) Yh(aG aZ Hc Is Ji Lu Lx Oh Ow Oy Ug) Vj(aX bP bS Dc Dp Hu Ik Qt Qu Ri Vt) Yi(aG aH aZ Bo bS Hc Oy Ug We) Yk(aG aH aZ Bo Hc Oy Qv Ug We) dR(Eq Fc Rv Ux Vi Vz Wb Yd) Ld(Fd Rt Uh Uz Wb Wc Xa) gP(Hp Sf Ux Vi Xa) Ke(cH Of Oy Ph) bS(Hl Rz Si Yd) oE(Dr Gb Wb Zw) Eq(Cu Lu Vu) Fd(aJ bX Dk) Ji(De Vz Th) Tl(aH Oz Ug) oF(Dr Hl kO) Hu(Uw Wd) Pz(Ml Nq) We(Vu Vv) Xa(fP It) Kj(mF oP) Uh(Ri Tv) Ur(nK Vi) cH(iO oH) CqHl DdHp GbMy NgiO UaPs WbOh SiaH KkdJ RtPg} Ow{Wb(aA aK aN AR aU bM bS cF cK cW cZ dA dI dM dR Du eF Em Fa Fb fP gL GP hB hC hF hG iA Ic iH iJ In iO iP iZ Je Jf kQ kR KS Kz Ld Lt Lw Ly Lz Mc Md Mi Mj Mq Mr Mu Mv My Nf Ni nW nY oE oF oH oK oN Or Oy pF Qd Ra Rb Rj Sj St Tr Tt Ud Um Uo Us Uz Vc Vi Vj Vu Vv Wc Wf Wg Yg Yh Yi Yj Zq Ye Wm Yf) Dr(aA AD aN Ap As aU aV Bc bM cI cW cY Dk Du eF Em Fa Gb Gc GP Gz Hb Hf iA Ic Id iJ IO Iu IZ Je Jf Ji Ju Jv Kc Ke Kf Kj Ko KQ kR Ks Lt Lu Lw Me Mf My Nm nY oE oN Oy Ps Qy Rg Rh Rm Rt Sf Sj St Tn Uh Um Vc Vh Vi Vj Vu Vv Yh Yi Yj Zx Ye Tl Xa Wm Yf) Yh(aA aX cM Cu Dk Ed Gb Gd Hb Hp Hx Ij Is It Kq Ks Me Mr Nb Ny On Pe Pk Ps Qa Qd Sr Un Vi) Ke(aF aM aO Aw Ax bN bZ cQ Dk Dp Fw Ii In Jv Kg Ko Mn Mv OE Oi Oz Ur Us Ut Th) Vi(dR eF gL Ld Mv My Oy Tt Vb Vu Wf Wm) Hp(aA bM Dl Gl Ld Mg Mm oF Oy Vu Yd) Ch(aA Id Is Kn Mt Nn Nv Vj) Gd(Aj Fw Gl Ko Kp Oi Pa Uv) Yd(fP Gc Kq kR oH oK oN Pe) Ny(Bg Hc Oy Sj Yg Zx Th) Aj(Em Fc Is Kf Lj Vt) Ti(aY bG bR Oa Pc Vt) Zq(aA Dg Ed Kl Mm Vo) Ps(eF Jq Us Vv Yg Ye) Th(aY bG Iv Pc Vt) Yi(aA Af aZ bM Kg) Sh(iZ Nt Nu Nv oF) Ed(Sj Vj Yj Yf) Vz(eF fP Kd Lp) Of(Cq Kn Kq Tv) bM(Rz Yl Xa Yf) Bg(Ko Pa Uh) Du(Cs

Oa(Af aH aX aZ bM Bn Bo Cx De Ip Oe Qw Rx) Nb(Aj aX aZ Bo cR Eq Ng Oy Rz Ss Ux Wd) Ed(aQ BA bQ cT De Ki Lx Oh) Qa(Af Ao Bg Co Kl Ng) Ij(aZ bM Kg Mm Nl) Oh(aY bM Dg Gl Kl) Pe(aD Ao aX bM Du) Fw(aZ Gd Qv) aX(Ar Ih Nn) Dg(cT Pf) Gd(Jm Pa) Gl(Js Lx) Ny(aW Ib) aZ(Ih Ks) AjPf CqKj EqbQ ThJv LxbM} Uh{Qa(bN De dJ Ic iO Jk Jo Ko Mj nW oN Ri Tn Tv Ur Us Vs Yh) Ri(aM Ax bA cH dM gL hB iZ Jq Kf Kn Ml Mr Ra Uc Vt) Ch(Cp cT Cu Dc Hw It Jh Jl Jp Lh Ma Nq Pe Sr Ur) Tv(aE Af aW Ii Jo Ko Ou Oy Rj Us Uu Uv) Id(Aj De dJ Ic Ko Ur Us Uu) Ko(Aj Bg dK Ed Oh Vt) cH(dM eF hB iO oF Tn) Aj(Kf Kn Kq Uc) Mt(Bg oN Oy Oz) bN(iO Kf Kk Kn) De(Kf Kq) Of(Cq Jq) aE(hB iZ) dJ(dM hB) AxMc BgTn DrFw LxMk} Og{Nn(Fp Ir Jl Jn Jq Js Lw Ns Nv Ny Oz Pe Po Qa Qe) Qd(Fp Ih Il Jl Jn Jq Lw Mn Mr Nm Ns Nx Ny Oz) Lh(Fp Ip Iv Jn Js Lw Ns Nv Ny Oz Pb Qa) Nv(Hq Hu Ir Jq Js Mn Mr Nm Oy Qa Qe) Jg(Ir Jt Lx Lz Mn Mw Mx Ny Pe) Ih(Fp Jp Lx Mm Mn Ny Om Po) Ip(Fr Js Lx Mn Mw Qa) Jt(Jn Jp Js Mn Mt Mw) Fp(It Jq Lw Mm Nm) Qa(Aa It Jq Mn Ns) Fr(Iv Jq Js Oz) It(Mn Po) MrNy} Vj{Oa(Af aZ bM Bn Bo cD Cx Dd De Du Fc Fw Ip Ne Rj Rx Us Uv Vq Zw Tl) Pa(bM dJ Dr Hf Hp Iv Ny Pi Uo Wb) Pe(aD aX bM Dc Di Ha Jm Th) Ch(Ba Kq Om Qa Qd Ut Vq) Ed(BA cT Fy Ir Oh Rm) Pi(aN aW aY Fw Jm Ru Th) Qa(aX aZ bM De Ex Fc) aX(Fw Lx Mt Nb Nn) Ru(Fd Hf Me) aZ(Ij Nb Qe) Fw(Hx St) Gl(Js Oh) Lx(Uv Yd) DcNu ThHa MmIj NbZx JlaY RmUu NycD} Yi{aZ(aF Ap aU aW bC bE bJ bW CO cS cZ De dN Ed Ez Fc Fi Gc Hf Ho Hv Iv Jd Jh Kc Kd Kg Kj Kz Mg Mi Mm Mp Mq Mt Mu Mw Nn Pd Pj Rz) Ed(Af aG aH bM Bn Bo bX CQ cW Cx Gn Hb Hc Hl Ii Ij Ne Oz Pa Pc Rt Ug Vt Yl) Bo(aY Di Fw Ha Nb Nd Ne Pe Sr Th) Pe(aD Af bM Gn) Ch(Kq Mq) BgKq FwYl IjbM YgQd KgaW} Ij{Oy(Ii Ik In Ir It Iv Jn Jo Jr Js Lv Me Mg Ms Mu Mv My Nc Nf Nj Nr Nt Ny Oe Oh Oz Pf Qa Qe) My(Fp Jq Lw Lz Mn Nq Pb Pc Qd) Yh(bM Hv Id Lx Mp Qa Uc) Kc(Aj Hc Jo Of) bM(Sf Si Yg Yf) Ed(Sf Yk Yf) Th(Al Nk Rv) Lx(Oe Of) Hu(Jl Nv) Ik(Fp Qd) We(fP Hx) Jp(Ch Ng) Pb(Fr Jl) AjMt BoSh DrNh NsMp MkPe MnMs NbHl TrOf QdOe XafP UuVb VhdR} Pe{Yh(aD aG bM Bo bQ cE cL Dc Fy Gn Ha Lu Mp Ou Uc Vs Wc) Gn(Ib Qt Vu Vv Yg Yj Yk Yf) Du(dR Fb Fd Gp Yj) Yg(aD Ba bM Bo Qd) Yf(aD bM Bo Ha) Wf(cW Jn Mk Ua) Xa(fP Ha It Ye) Yj(aD bM Bo) Vz(Fw Jm Jy) Ye(cW Ed Fb) Th(Qz Uk) Ha(Fi Lp) Yk(aD bM) Sh(cD Jm) Zw(Dc Oh) Ru(Ug Ur) FcoH GhKd HlcE JgOy WeQg WhaE} Kq{Rx(eF fP gL gP iA iO iP iZ kQ kR nY oE oF oH oK pF) Aj(Ba Bg bN dJ Hc Hx Kf Kn Lu Me My Nd Of Qv) Ch(De Hf Ik Jp Nh Oh Tv Yg Yh Yj Yk Yf) Fc(dR Ef fP gP oE oF oH) Yd(aZ fP iZ Lu oE) Th(bG Hq Jy Uv) Of(jT Ko Tm) Mv(Lp Ru) Yh(Js Oh) Ye(iO kQ) fP(Tm Xa) EqJn GniO YgOa LpiP} Aj{Jt(bA bN CH cL Dg dM Fr Nv Om Qd) Ko(Ba bN Fw Ir Iu Kg Kn Nr Oh Vt) Ap(Dc Jn Jq Jr Mr Mt Qd Qe) Ad(Ba bJ bN De Mt Nn Qd) Om(Op Wc Yh Xa Yf) Qa(Aa Bb) BaVt MUg KfVq RzNv} Yh{Qa(Bo Cu Dd Dk Dr Gc Gp Hb Hc Hl Ib Ic Lu Oi Oz Pd Qv Qw Sh Ug We Wf Ye Ti) Js(bE Bo Jd Nq Qd Vu) Lx(aS bJ cO Qd) Oh(Jh Qd Qy Vu) Bo(Nb Oa) Ed(Gn Ye) Nn(aX aZ) OaaG} Lx{Oy(Ip It Jn Jp Lh Mn Ny) Zw(Af Ed iZ oF) Dr(Ic kQ) Yf(bM Ed) Mh(Fc Ns) Ng(Jg Jt) Wb(hB kQ) AfFi BnVz DuaS FdbM IkQd ShNy TlhB RxiZ} Ny{Rx(dR fP gP iH iJ iP iZ kS nY oE oF pF) aW(Si Yg Yj Ye) dR(Fd Rt Xa) Ye(gL Nn) ArTh CwRt FcOh WhUr WfgL} Id{jT(Kj qG qH ql qZ rN rO rP rQ rR rS rT rU rV rW) rS(dJ Fw Of Or) ChNn HwrR} Jg{Ng(Fp Fr It Jl Jn Mp Mw Po Qb Qe) My(Fp Ih Js Lh Mr Nv) Oy(Fp Js Nv Po) QaOe} Ed{Tr(Gd Hl Rt Va Xa) dR(Dr Vw Wh Xa) Gn(Vu Vv Yg) Ba(Ye Yf) GboF YgOz YjOh SihB XagP} Nn{Ch(Hb Kk Ri Tv Uc Vt) Eq(Ef Jl Pi) aZ(Sh Yj Yk) Qd(Ik Oe) aX(Rz Yj) MrOy NgJt IhOe} Qa{Aa(Lu Oi) Bo(Uy Yg) Yf(aZ bM) Fc(dR Hl) Hc(Ko Yj) Wf(Af Jq) Rt(fP gP) DrkQ ThUn HlUk KkdJ UybM} Oa{Gc(hB hG Wb) Dr(Ic nW) Gb(Cx Rx) Gn(Mi Vu) Si(hB hG) aG(Yk Zx) BoYg DudR YfRx Hllc YjaW ShgL} Nv{Oe(Ih It Jt Ns Pb) Oy(It Jt Mr Mt) It(Ns Pb) Sh(oE Oz) Wf(Ih Jn) MtMy IkQd UrmZ} Nb{Tl(dR gP iP iZ nY) Bo(Yg Tm) Mq(Wf Ye) Om(Eq Wc) ArTi IhYe SioE TmpF} Mt{Eq(bl Ng Om Vu) My(Ih Jt Lh) GbaX XafP} Qd{Ik(It Ma Mm Oe) ChYf NrYg RufP jTpS} Pf{Dr(kQ oN Sh) fP(Hp Vz Wb) WboE VziA} nW{qZ(jD Up Ut) Ko(wD zA) UbrN OrwD} Ch{Jp(Kg Ko) TiNq MqYg StWd} Fp{Jt(Ng Oe Oy) NsMp ItJp} Ur{TvcH LpVu RmmZ VtbN dJqZ} Ih{DroF FrOe MsLh YehB} Kn{dJ(eD jO) jT(eD Of)} Wf{Jn(Fw Jl Qy)} Ko{KjdK cWzA hOrS} hB{Dr(Il Kd) FdaY} It{FrNg MsJp} Xa{RxaZ cUfP} Ye{MqPa OmiZ} Rt{DcMw JsgP} Oh{BoFd LuWb} CtLhjT FaFwSh GcbMoE NsMpJp UeOfUs TvVqjM SibQiZ JIRxkQ KciPwD KrPhwB KzmZoP RfdJrS Unconstrained panels with 2 analytes, where 1.0E-8 >= 'model p-value' > 0. Contains 565 panels of 182,582 total panels evaluated. : Im(aA Et Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Sh Ye) Ji(aA Et Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Nw(aA Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe Wm) Li(aA Et Fp Hq Hr Hu Hv Hw Hx Ih Ii Ij Ik Il In Ip Iq Ir Is It Iv Jg Jh Jj Jk Jl Jn Jo Jp Jq Jr Js Jt Lh Lj Lu Lv Lw Lx Ly Lz Ma Mb Mc Md Mf Mg Mi Mj Mk Ml Mm Mn Mp Mr Ms Mt Mu Mv Mw Mx My Mz Na Nb Nc Nd Ne Nf Ng Nh Ni Nj Nk Nl Nm Nn No Ns Nt Nv Nx Ny Oe Of Og Oh Oi Ok On Oy Oz Pa Pb Pc Pd Pe Pf Pg Po Pz Qa Qb Qc Qd Qe) Et(aA Aj Fp Hu Hv Ih Ij Ip Ir Is It Iv Jj Jl Jn Jo Jq Jr Js Jt Lh Lj Lw Lx Lz Mh Mn Mp Mr Ms Mw My Mz Nc Ng Nj Nl Nn No Nr Ns Oe Of Og Ok On Oy Oz Pb Pe Pf Qa Qb Qc Qd Qe) Jj(Aa Ij Is Lh Lj Nn No Nv Ok On) No(Is It Ns Og Ok Oz Pb Uh) On(Lj Ms My Ng Ns Oe Og Oy) Ok(aA Fp Is It Lj Og Pb) Lj(aA Ij Is Jt) Ij(aA Og) ChKe IpaA IsOg WbOw Unconstrained panels with 2 analytes, where 1.0E-7 >= 'model p-value' > 1.0E-8. Contains 336 panels of 182,582 total panels evaluated. : Et(Ch Fr Hq Hr Hw Hx Ii Ik Il In Io Iq Iu Jg Jh Jk Jm Jp Lu Lv Ly Ma Mb Mc Md Me Mf Mg Mi Mj Mk Ml Mm Mq Mt Mu Mv Mx Na Nb Nd Ne Nf Nh Ni Nk Nm Nq Nt Nu Nv Nx Ny Oh Oi Om Pa Pc Pd Pg Po Pz) No(aA Aj Fp Hc Hu Ih Ij Ik In Ip Ir Iv Jg Jl Jn Jp Jq Js Jt Kc Ke Lh Lj Lu Lv Lw Lz Mm Mn Mp Ms My Mz Nc Ng Nj Nl Nn Nv Ny Oe On Oy Pc Qa Qb Qd Ur Vt Ti Th) Ok(Fr Hr Hu Ih Ij Io Ip Iv Jg Jl Jn Jo Jp Jq Js Lh Lx Lz Ma Mc Mn Mp Ms Mt Mw My Mz Nc Ng Nl Nn Nr Ns Nv Ny Oe Of On Oy Oz Pf Po Qa Qb Qd Qe) Is(aA Fp Fr Ij Ip It Jg Jp Lh Lx Ma Mm Mn Ms Mz Nn Ns Nv Ny Oe On Oy Oz Pb Qd) Lj(Fr Ih It Iv Jg Jl Jp Jq Lh Lw Lx Ma Mi Mm Mn Mp Mr Mz Nn Nt Nv Og Ps Qd Vi) Ke(Af Aj aM Bg cH De dJ dK eC Hc Ik Jj Jo Kj Ld Ms Of Ow Oy Ph Uh Us) aA(Fp It Jg Jn Js Jt Lh Lx Ma Mm Mn Mz Nj Nm Nn Nv Ny On Qa Qd) Li(Fr Io Iu Jm Me Mh Mq Nh Nq Nr Nu Om) Nw(Aa Aj bN CH Ed Jv Ri Tv Uh Us Th) Jj(Ii It Jg Js Jt Ko Lx Mn Ny Qa Qd) On(Fp Hu Ih It Of Oz Pb Qd) Uh(Id Ji Ko Ld Ps Qa Ri Tv) Og(Jg Jt Lh Nn Nv Qa Qd) Aj(Ad Im Ji Jt Kq) Ow(Dr Eq Hp Sh Vi) Ps(Rx Us Uu Vs) Aa(Im Ji Qa) Ch(Ji Kq) Ij(My Oy) Wf(Qa Vi) IkQd IUp JiUs LdLp Unconstrained panels with 2 analytes, where 1.0E-6 >= 'model p-value' > 1.0E-7. Contains 1,140 panels of 182,582 total panels evaluated. : Ke(aA Ad aE aF aJ Al AN AO Ap aQ Ar As AW Ax BA BB Bc bF bG bl bJ bL BN BO bP bQ bR bS bX bZ cA cD cI cJ Co CP CQ Cs Ct Cu Cv Cw CX Db Dc Dd Dg dH Di Dk DL dM Dp DR Ed Ef Et Fp Fr Fw GL Gp HB Hf Hq Hr Hu Hv Hw Hx iA Ib Ic Id IH Ii IJ Il Im In IO Ip Iq

Nh Ni Nk Nq Nu Of Oh Oi Om Oy Pa Pc Pd Pe Pf Pg Vt) Im(cH De Dr Du Fc Fi Gb Gh Hl Ho Hp kC Kk Ko Ld Lp Lt mF Op Rt Ru Rv Rx Ry Rz Sf Si Sj Uw Uy Uz Va Vb Vc Vh Vj Vt Vw Vz Wb Wc Wd We Wf Wg Wh Yd Yi Yj Yl Zw Zx Tm Tl Xa Ti Th) Pe(Eq Fd Fi Fp Gb Gh Hl Ho Hp Ih It Jg Jj Jn Jp Lh Lp Lt nI Nn Nv Op Rt Rv Rx Ry Rz Sf Si Uw Ux Uz Va Vb Vc Vh Vj Vw Wb Wc Wd We Wg Wh Yd Yh Yi Zq Zw Zx Tm Tl Th) Is(CH De Eq Fc Hc Hq Hv Hw Id iO Iq Iu Jm Jo Jr jT Kk Ld Ly Mb Mj Ml Mq Mu Mx Nf nK nL Nq Ow Pa Qw Ru Rv Rx Sf Us Va Vt Vz Wb We Wf Yh Zw Zx Ye Xa Wm Ti) Js(Fc Fp Fr Ih Ik Ip It Iv Jg Jl Jn Jp Jt Lh Lv Lw Lz Ma Mm Mn Mp Mr Ms Mt Mw Mz Nj Nl Nm Nn Ns Nt Nv Ny Oe Oy Oz Pb Po Qe Rt Ru Rv Rx Sh Va Wb Wd Wf) Mz(dR eZ Fp Fr gL hB hO hP iA IH iJ iO Ip It Iv iZ Jg Jl Jn Jn jO Jp JT kQ Lh Ma Md Mm Mn My Nn Nv nW Ny oE oF oH oN pF qC Tv) Nn(Aj Ch Fp Fr Hu Hv Ik Ip Ir Jg Jl Jn Jp Jq Jr Lh Lv Lw Lz Mn Mr Ms Mt Mx My Ng Nj Nl Ns Nt Nv Ny Oe Oy Oz Pb Po Qb Qe Vt) Lj(Fp Hq Hr Hu Il Io Iu Jk Jm Kc Ly Lz Mb Md Me Mf Mh Mj Mk Ml Mq Mv Mx Na Ne Nf Ng Ni Nk Nr Nu Of Oi Ow Oy Pd Qb Qc Vt Ti) Oa(Du Et Fc Fd Fi Gb Gh Gn Hl Ho Jj Lp Lt Op Rt Ru Rz Sf Sh Si Sj Uw Vh Vj Vw Vz Wb Wd Wf Yd Yj Yl Zq Zw Zx Ye Tl Xa Th) Ow(Bg Du Fc Fi fR Gc Gh Gn Hl Id Ko Lt Op Oy Rt Ru Rv Rx Sf Si Uw Vb Vc Vh Vt Vw Wd We Wf Wg Wh Yh Yi Yl Zx Ye Tm Tl Yf) Lh(Fp Fr Hu Hv Ik Ip Ir Iv Jg Jl Jn Jo Jp Jq Jr Jt Lw Lz Ma Mm Mn Mp Mr Mt Mw My Ng Nl Nv Ny Oe Oy Oz Qb Qc Qe) Et(Af Ao Ax bA bN cH cP Cs CT Cu Dc De Dg dM Ed Ef Hc Id IZ Kc Kd Kj Kk Kl Kn Ko Ld Tv Uu) Nv(Aj Hv Ik Ip Iq Ir Iv Jg Jk Jl Jn Jp Jq Jr Jt Lw Lz Mn Mp Mr Ms Mw Nj Nl Of On Oz Qb Qe Sh) Ih(Ip It Iv Jl Jn Jq Lv Lw Lz Mm Mn Mp Mr Ms Mt Mw Nj Nl Nm Ns Nt Ny Oe Om Oz Po Qe Rx Sh) Jt(Fr Ip Jg Jl Jn Jo Jp Jq Lv Lz Ma Mm Mn Mp Mr Ms Mt Mw My Ns Ny Oe Oy Oz Pb Po Qb Qe) Vt(Aj aQ Ax cH Cs dJ dK Dp Ed Gp Jj Jq Kk Kn Ld Li Mh Mn Mt Nr Oh Qe Ri Sr Tv Tz Us Xa) Jp(Ch Ip Ir Iv Jl Jn Jq Ld Lw Lz Mn Mp Mr Ms Mx Ns Nt Ny Og Oz Pb Po Qb Qe) Fp(Fr Ik Ip Ir Iv Jg Jl Jn Lw Ma Mi Mn Mp Mr Mt Mw Nm Ns Ny Oz Pb Pz Qe) Ny(Fc Hc Ib It Iv Jl Jq Lp Mr Ns Rt Ru Rx Rz Sh Vj Wd Wf Ye Xa Ti Th) Jj(Bb Dc Ir Iv Jk Jo Jq Kf Kn Ld Mp Mr Mt Nr Nx Om Pf Pj Sr Vq) Fr(Aj Hu Ip Ir Iv Jl Jn Jq Lw Mn Mr My Ng Nl Ns Oe Oy Oz Pb) Jg(Ip Ir It Iv Jl Jn Jq Lz Mp Mr Ms My Ns Oe Oy Po Qb Qe) Aj(Ap Ba Bb Cu Dc Fy Id Kn Li Mn Mt Ok Qe Uc Uf Vq) Ed(Dr Gb Kk Kn Ko Ld Si Uw Vh Wd Yi Zq Zw Ti) Og(Ii Ip It Iv Jn Jq Ma Mm Mn Mr Mt Mw Nt Qb) On(Ch Iu Mb Mj Mq Na Nb Nf Nu Nx Om Pz Sh Wf) Jl(Ip Jn Ma Mm Mn Mt Mw Nm Ns Oe Oz Pb Qe) Kq(Bg De Dr Ef Hc Iz Ng Oy Sh Ux We Zx Th) Oh(Fc Gb Ho Ko Lp mM mU mZ nI Sh Si Zq Xa) It(Ip Iv Jq Ma Mm Mn Mp Mr Mt Mw Po Qe) Jn(Ip Iv Jq Ma Mm Mn Mr Po Qe Rx Sh) Ld(Dr Fd Fi Ho Id Ru Uy Wb Wc Wf Yi) Id(aQ bN CH dJ jT Kk Ko Ur) Mn(Ip Ir Iv Jq Mr Ms Mt Po) Kn(dJ eD iB jO jQ jT Tz Ur) Sh(Fw Om Pf Rm Sr Ut Xa) Ko(bN Ch Jo Kc Kj Qb Tz) Iv(Ip Ma Mm Mt Mw Qe) Xa(Bo Fw Kd Oz Sr Un) Li(Dr Eq Fd rS Wb Wm) Ur(Dc Fy Ir Jq Qe Tv) Ch(Kf Sr Tn Uf Zq) Nb(Hl Vj We Wf Ti) Qe(Jq Ma Ti Th) Wf(Mr Mw Om Ut) Mt(Eq Ip My) Po(Oy Pb) Yi(aZ Bo) Jq(Ip Wm) DrTz EqOm ThUn FdMq NsMp MaQb TvcH IoIr KfOf KkdJ VjPa aWrS cQqZ wBnW

Unconstrained panels with 2 analytes, where 1.0E-4 >= 'model p-value' > 1.0E-5. Contains 4,996 panels of 182,582 total panels evaluated. :
Vi(aA aC AD aE AF aG aH al aJ aK AL aM AN AO AP aQ aR AS aU aV Aw aX aY BA BB BC bE bH bI bJ bL bM BN bO bP bQ bR bS bU bV bW bX cA cB cC cD cE cF cG cI cJ cK cL cM cN CO CP CQ cR CS CT CU CV CW CX cY cZ dA DB DC DD DE dF DG dH DI dJ dK DL dM dN Dp Dr Du Ef EM Et Ex Ez Fc Fd Fi Fp FR Fy Gb Gc Gd Gh Gl Gn Gp Gz Ha Hb hC HF Hl Ho Hp Hr Hu Hw Hx iA Ib Ic Id iH Ii iJ Ik Il In IO Ip Iq It Iu iZ Jd Je Jf Jg Jh Jk Jl Jm Jo Jq Jr Jt Ju Jv Kc Kf Kg Ki Kj Kk Kl Kn Ko Kp Kq KR Ks Ky Lh Lp Lt Lv Lw Ly Ma Mb Mc Md Me Mf Mg Mj Mk Mm Mn Mr Ms Mt Mu Mv Mw Mz Na Nb Nc Nd Ne Ng Nh Ni Nj Nk Nl Nm Nq Nr Ns Nt Nu Nv nW Ny oE oH Oi OK Om ON Op Or Ou Oy Pb Pc Pd Pf Pg Ph Pi Pj Pk Pz Qc Qg Qh Ql Qm Qn Qu Qv Qy Qz Ra Rc Rf Rg Rh Ri Rj Rm Ru Rv Rx Ry Rz Sf Si Sj St To Tr Tv Ua Ub Uc Ud Ue Uf Ug Uk Ul Um Uo Up Us Ut Uv Uw Ux Uy Uz Va Vc Vh Vj Vo Vp Vs Vw Vz Wb Wc Wd We Wg Wh Yd Yl Zq Zw Ye Tm Tl Xa Wm Tj Ti tF) Vt(aC Ad aE AF aH al aK aL aM AO Ap Ar As aU aV AW aY aZ BA BB Bc bF BG bL bM Bn BO bP bQ bR bS bV bW bX bZ cA cD cE cG Ch cI cJ cL Co CP CQ CT Cu Cv Cw CX cY cZ dA Db Dc DD De dF Dg dH Di Dk Dl dM DR eC Ez Fa Fp Fr Fw Fy HB Hc Hf Hq Hr Hu Hv Hw Hx Ic Id Ih Ii Ik Il In Io Ip Iq Ir It Iu Iv Jd Je Jf Jg Jh Jk Jl Jm Jn Jo Jp Jr Js Jt Ju Jv Kc Kd Kf Kg Kj Kp Kq Kr Kx Ky Lh Lu Lv Lw Lx Ly Lz Ma Mb Mc Md Me Mf Mg Mi Mj Mk Ml Mm Mp Mq Mr Ms Mu Mv Mw Mx My Mz Na Nb Nc Nd Ne Nf Ng Nh Ni Nj Nk Nl Nm Nq Ns Nt Nu Nv nW Nx Ny Oa OE OF Og oH Oi Ok Om On Ou Oy Oz Pa Pb Pc Pd Pe Pf Pg Pi Pj Pk Po Pz Qb Qc Qg Qh Qm Qt Qu Qv Qw Qx Qy Qz Ra RB Rc RfRg Rh Rj Rm Ru Ss St Tn To Tr Tt Ua Ub Uc Ud Ue Uf Ug Uk Ul Um Un Uo Up Ut Uu Uv Vo Vp Wf Yi Wm Ti Th) Ps(aC aD aE aG aJ Al An AO Ap aQ aR AS aV Aw BA Bb BC bE bF bH bI bJ bP bR bU bV bW bX bZ cA cB cC cF cG cI cK cL cM CP Cq cR cS cT Cv cW cY cZ dA DB DC DD dE dF dG dH dJ dL dM dN dR Du eF Em Fa Fd Fi fP FR Fy Gb gL Gn gP Gz Ha hC HF hG Hl Ho Hr Hw iA Ic Id iH Ii iJ iO IP Iq It Iu iZ Jf Jh Jl Jp Jt Ju Jv Jy Kc Kf Kg Kn Ko Kp kQ KR KS Lt Lv Lw Ly Mc Md Mv Mz Nd Nh Nj Nm Ns nW nY oF oH OK oN Op Ou pF Pg Pi Pk Qh Ql Qm Rf Ri Rm Ry Sf Si Sj Tn Tr Tt Ub Uc Ud Um Uo Up Uw Uz Vc Vh Vu Vv Vz Wb Wg Yh Yi Yj Yk Zq Zw Tm Tl Tj Yf) Is(aE AF aH al aM aN Ap aQ AR aW Ax aY BA BB Bc bF BG BN bO bR bS bV bZ cB cE cI cJ cP CQ Cs CT Cx Dg dJ Dk Dl dM Dp Dr Du eC Ed Ez Fd Fi Gb Gc Gd Gh gL Ha HB Hf hG Hl Ho Hp iA Ib Ic iH iJ iP IZ Jd Je Jf jK jO jP Ju Jv Kd Kf Kg Ki Kj Kl Kn KP KQ kS Kx Ky Lp Lt ml mZ nC nH nl nW nY Oa oE oF oH oN Op Ou pF Ph Pj Pk Qg Qh Ql Qm Qt Qu Qv Qy Qz Rb Rc Rf Rh Ri Rj Rm Ry Rz Si Sj Sr Tn To Tr Tt Tv Tz Ua Ub Ud Ue Uf Ug Uk Un Uo Up Uu Uv Uw Ux Uy Uz Vb Vc Vh Vj Vo Vq Vs Vv Vw Wc Wd Wg Wh Yi Yj Yk Yl Zq Tm Tl Th) Uh(Aa aC aD aF aG aH al aK AL aN AO Ap aQ aR aS aU aV Aw aX aY aZ bB bC bE bF bG bH bl bJ bL bM BO bP bQ bR bS bU bW bX bZ cA cB cC cD cE cF cG cJ cK cL cN CO cP cQ cR cS Ct cU cV cW CX cY cZ dA DB dC dD DE Dg dH DI Dk dL Dp eC Ef eP Fb Fn fP Gl GP HA Hb Hc HF hG Hr Ib iC iH Io Iq Iu Iz jD JF JH jl JK Jm jO jP jQ jR jT Ju jV JY Ki Kj Kl kQ KS Kz IK IL IM IO Lu Ly Mc Mf Mg Mm Mp Mu Mv Mw mZ NC nH nL Nq nY Of Oz Pc pF Pj Qm Qn Qt Qu Qv Qz Rc Rg Ss St To Tt Ua Ub Ue Uk Vo Vs Vu Xa Tj tF) Et(aC AD aE aF aG aH al aJ aK AL aM AN aO AP aQ AR AS aU aV AW aX aY aZ Ba BB BC bE bF bG bH bI bJ bL bM Bn BO bP bQ bR bS bU bV bW bX bZ cA cB cC cD cE cF cG cJ cK cL cM cN CO Cp CQ cR cS cU CV CW CX cY cZ dA DB dC DD dE dF dG dH DI dJ DK DL dN Dp DR Fa Fb Fw Fy GL Gp HB hC Hf iA Ic iH iJ iO iP Jd Je Jv Kf Kg Ki Kp KQ KR KS Kx Ky Kz Lp nW nY oE oF oH oK oN Or Ou Ow pF Ph Pi Pj Pk Qh Ql Qt Qu Qw Rf Ri Rm Sh Sr Ss Tz Ug Uk Un Up Ur Us Uv Vo Vp Xa Th) Id(aA aE AF al aM aU aW Ax bA BB Bg bL bO bR bS cA cE cJ cQ Cs CT Cu Cx Dc dD De dK dM Dp dR eC Ed Ez Fw Gp Hb Hc Hv Hx Ic Ih Ij Ik Il Im In Io Ip Iv Jd Jj jK Jl Jm Jn Jp JQ Jr Js Jv Kc Kd Kf Kg Kj Kl Kn Kp Kq Kx Ky Lh Li Lj IK IL Lu Lx Me Mh Mi Ml Mn Mr Ms Mt Mu Mx Na Nc Nd Ne Ng Nh Nj Nl Nn Nr Nv Oa OE OH Oi Ok On Ou Oy Pb Pe Ph Pi Pj Qa Qb QC Qd Qe Qh Qw Qy Rf Ri rR rS Sr Tv Tz Uf Ug Uo Up uR Us Uu vS wP) Ke(Aa Du eD Eq Ex eZ Fc Fd Fi fY Gb Gc Gh Gn hA HL HO Hp iB iC jD jE jF jG jH jI jK jL jM jQ jR jU jY IK IM IN IO Lp Lt Op pS pY qB qC qD rB rN rO rP rQ rR RT rU RV rW RY Rz sC Sf Si Sj sK sM sO tO tR tS tU uG uI uL uM uN uO uR uT uV UW UX UY uZ VA VB VC VH vI VQ vS vT VU vV vW Vz WB Wc WD WE Wf WH wJ wK wL wP wQ yD yH Yi Yl zA zG zl Zw Zx Ye Tm TL XA tF) Js(Aj Du Eq Fd Fi Gb Gh Hl Ho Hp Hq Hr Hu Hv Hw Hx Ii Il In Io Iq Ir Iu Jh Jk Jm Jo Jq Jr jT Kc Kk Ko Ld Lp Lt Lu Ly Mb Mc Md Me Mf Mg Mh Mi Mj Mk Ml Mq Mu Mv Mx My Na Nb Nc Nd Ne Nf Ng Nh Nl Nk Nq Nr Nu Nx Of Oh Oi Om Op Pa Pc Pd Pe Pf Pg Pz Qb Qc rB Ry Rz Sf Si Sj Ur Uw Ux Uy Uz Vb Vc Vh Vj Vw Vz Wc We Wg Wh Yd Yh Yl Zq Zw Zx Ye Tm Tl Xa) Qd(aE Af aN Ap aQ Ar aW Ax BA Bb Bc bF Bg bN bO bS bV cE cI cJ cP Cs CT Cx Dc Dd dF dJ dM Dp Dr eC Ed Ef Eq Fc Fd HB Hc Hf

Figure 30 Continued

Figure 30 Continued bN Ch cQ dJ Dp eC Gp Hb In Ip Ml Nk Of On Ow Oy Pg Pj Qb Rf Tz Un Us Vq Vs Wm) Ip(Hv Iq Ir Jr Lv Lw Lz Ma Mi Mm Mp Mr Ms Mw
Mx Nc Nj Nl Ns Nt Oz Pb Pf Qb Ur) Kc(aA Aj Ax CH Cs Cu Dc dJ Fw Hb iB Jr Kd Ml Mr Na Nr On Ow Pi Qb Tz Un) Ow(aA Aj Ax cH Cs
Dc Fw Gz Kd Kf mE Mk My Ng Of Qw Un Ur Vj Yg Yj Yk Zq) Ma(Aj Ch Hv Iq Ir Jr Lv Lw Lz Mp Mr Ms Mw Mx Ng Nl Ns Nt Oy Oz Pb
Qc) Fw(Dr Eq Fd Gb Hb Ru Ry Si Ur Uw Ux Va Vc Vj Vz Wb Yi Yl Zq Zw Tm) Kf(aA aM Bg bN cQ Ct De eC Hc In Jo Kj Ng oE Oy Qb rB
Tz Ur Uu) Mr(Aj Lv Lw Mk Mm Mp Mw My Nm Ns Oy Oz Pb Pz Qb Ru Ur Wm) On(Bg cH Eq Hc Iz mZ oN Qw Rt Ur Ux Va Yd Zx Tl Wm
Th) Ur(Ax bA Cu Dd Fd Iu Kd nl Nr Ok Pi Rm Tz Uc Un Vq) Mm(Aj Hv Ir Jr Lv Lz Mp Ms Mx Nl Ns Nt Oe Oz Qb) Pf(Eq Fd Gb Ho Hp Lp
Og Oz Si Ux Vz Wb Wf Zx) Dr(Ez Kd Mp Mq Or Ou Qh Qx Rm St Ut Vj Vq) Qb(Gb Ir Lw Mp Ms Nl Nm Ns Nt Oe Oz Vw Zq) cH(aA Fy gL
HB iB nY oF Qh Rf Tn Tz Un) Mq(Eq Gd Lp Ru Ux Uy Uz Wb Wc Wf Yi Ye) Aj(Aa Ax Dg Dl Kg Kp Om Pj Pz qZ Un) Ch(Dc Fy Hb Jd Jh
Kx Ok Tz Uc Un Ut) Og(Ir Jk Lw Mi Mp Mx Nm Nr Nx Pz Qc) Wf(Cu Hv Ir Jr Kd Mx Nr Pg Tn Un) Fd(Ar aW Bo Cx Lz Ml Oz Qx Vj)
Mw(Ir Jr Lv Lz Mp Ms Nl Ns Nt) Tz(Fc Ho Ru Sh Va Wd Zq Ti) Vj(bA cT Dc Fy Kd Mx Nr Pi) Mx(Ho Sh Wb Wd Wh Zq) Ir(Lt Mp Nm Oz
Sh Us) aA(Aa Dc Hb Pj Si Yi) Cu(Rt Sh Ux Vb Th) Fy(cQ dJ Rt Sh Us Th) hB(aE cQ dJ eC Yi) Ar(Lp Yi Ti Th) Mp(Hq Lp mZ nl) Zq(aX aZ Gd
Nr) St(nI Ru Va Ti) Om(Gd Oy Ux We) Un(eC jT Va Ti) Vq(aZ Ml Ri Va) iP(qZ rN rS wD) Dc(De Rt Us) Lz(Ho Nm Oz) Ru(aZ Hv Kz) Aa(Ik
Iu) Ax(Ti Th) Yi(Rh Rt) Wb(Ml Qx) Jr(jT rB) Rm(Rx Va) Pj(dM wD) bA(Oz Qc) nl(nK Pa) wB(Kr Nm) qZ(aN bL) CsTh WmOk EqUt NsNt
MfrS NgUf NlIB TnSh KprB RyaZ RfdJ cLmZ rNnW Unconstrained panels with 2 analytes, where 1.0E-3 >= 'model p-value' > 1.0E-4. Contains 10,887 panels of 182,582 total panels evaluated. :
Id(aC AD aG aH aJ aK AL AN AO AP AR AS aV Aw aX aY aZ Ba BC bE bF bG bH bI bJ bM Bn Bo bP bQ bU bV bW bX bZ cB cC cD cF
cG cl cK cL cM cN CO CP Cq cR cS cU CV CW cX cY cZ dA DB dC Dd dE dF DG dH DI Dk DL dN Dr eD EF eT eZ Fa Fb FN FP Fr Fy GL
gP gW HA hB hC Hf hG hL hO hP Hq Hr Hu Hw iA IB iC iH Ii iJ iO iP Iq Ir It Iu IZ jD JE JF JG JH jl jk jL jM JO jP jR Jt JU jV JY Ki kQ KR
KS Kz lM IN lO Lv Lw Ly Lz Ma Mb Mc Md Mf Mg Mj Mk Mm Mp Mq Mv Mw My Mz Nb Nf Ni Nk Nm Nq Ns Nt Nu nW Nx Ny oF oK
Om oN Or Oz Pa Pc Pd PF Pg Pk Po pS pY Pz qB qD Qg qH Ql Qm Qn qO qP qQ QT QU QV qW QX qY QZ RA RB Rc Rg Rh Rj Rm rN rO
rP rQ rT rU rV rW rY rZ sC sK sM sO Ss St Tn TO TR tS Tt tU Ua Ub Uc Ud Ue uG ul Uk UL UM UN uO uP UT uU UV uW uX uY uZ vA
vB vC vH vI VO VP VQ Vs vT vU vV vW wB wC wD wE WF wG wH wJ wK wL wQ yD yH yJ yK yL zA zG zH zI yE tM tL XA Wm Tj Ti
Th) Xa(aC AD aE AF aG aH al aJ aK AL AN AO AP aQ aR AS aU aV Aw Ax BA BB BC bE bF bH bI bJ bL bM BN bO bP bQ bR bS bU bV
bW bX bZ cA cB cC cD cE cF cG cH cl cJ cK cL cM cN CO CP Cq cR CS cT CU CV CW CX cY cZ dA DB DC DD DE dF DG dH DI dJ DK DL
dM dN Dp dR Du EF Em Ex Ez Fi Fn FP FR Fy Gb Gc Gd Gh GL Gn GP Gz Ha HC HF hG Hl Ho Hp Hq Hr Hu Hw iA Ib Ic iH Ii iJ Ik Il In
lO IP Iq It Iu IZ Jd Je Jf Jg Jh Jk Jm Jo Jp Jq Jr Js Jt Ju Jv Jy Kc Kf Kg Ki Kj Kl Kn Ko Kp kQ KR KS Ky Lp Lt Lu Lv Lw Ly Ma Mb Mc Md Me
Mf Mg Mk Mm Mn Mr Ms Mu Mv Mw My Mz Na Nc Nd Ne Nf Ng Nh Ni Nj Nk Nl Nm Nq Ns Nt Nu nW nY OE OF Og oH OK Om oN Op
Ou Oy Pc Pd pF Pg Ph Pj Pk Pz Qc Qg Qh Qm Qn Qt Qu Qv Qw Qy Qz Ra Rb Rc Rf Rg Rh Ri Rj Rt Rv Ry Rz Sf Si Sj Ss Tn To Tv Ua Ub Uc
Ud Ue Uf Ug Uk Ul Um Uo Up Ur Us Ut Uv Uw Ux Uy Uz Va Vb Vc Vh Vj Vo Vp Vu Vw Vz Wb Wc Wd We Wf Wg Wh Yd Yi Yl Zq Zw
Zx Ye Tm Tl Wm Tj Ti Th) Kq(aC Ad aE AF aG aH al aJ Al aM AN AO AP aQ AR AS aU aV AW aX aY aZ BA BB BC bF bG bH bI bJ bL
bM Bn BO bP bQ bR bU bV bW bX bZ cC cD cE cF cG cl cJ cK cL cM cN CO CP Cq cR CS cT CU CV CW CX cZ dA DB DC DD dE dF
DG dH DI DK DL dM dN Dp dR Du eF Em Ez Fa Fi Fn FP Fy Gb GL Gn GP Ha hB hC HF hG Ho Hp Hr Hu Hv Hw Hx iA Ib Ic IH Ii iJ Il IO
IP Iq Ir It Iu Iv iZ Jd Je Jf Jg Jh Jl Jm Jn Jp Jq Jr Js Jt Ju Jv Jy Kd Kf Kg Ki Kp KR KS Kx Ky Kz Lh Li Lv Lw Lx Ly Lz Ma Mb Mc Md Me Mf
Mg Mi Mj Mk Ml Mm Mn Mp Mq Mr Ms Mt Mu Mv Mw Mx MZ Na Nb Nc Nd Ne Nf Nh Nl Nj Nk Nl Nm Nn Nq Nr Ns Nt Nu Nv nW Nx
NY Oe oF Og OK Om On Op Or Ou Oz Pa Pb Pc Pd Pe PF Pg Pi Pj Pk Po Pz Qb Qc Qe Qg Qh Ql Qm Qn Qt Qu Qv Qy Qz Ra RB Rc Rf Rg
Rh Ri Rj Rm Rv Sf Sj Sr To Tr Tt Ua Ub Ue Uf Ug Uk Ul Um Un Uo Ut Uw Uy Uz Vc Vh Vj Vo Vq Vs Vw Wc Wg Wh Yg Yh Yi Yj Yk Zq
Tm Wm Tj Yf) Kn(aC AD aE aF aG aH al aJ aK AL AN AO AP aR AS aU aV Aw AX aY aZ BA Bb BC bE bF BG bH bI bL bM Bn BO bP
bQ bR bS bU bV bW bX bZ cB cC cD cE cF cG cl cJ cK cL cM cN CO CP Cq cR CS cT CU CV CW CX cY cZ dA DB DC DD dE dF DG dH
DI Dk DL dN Dr EF eT Ex EZ Fa Fb FN FP Fr FY GL GP gW Ha hC HF hG hL hO hP Hq Hr Hu Hv Hw Hx iA Ib IH Ii iJ Il IO IP Iq Ir It Iu Iv
IZ Je Jf Jg Jh Jk Jm Jn Jq Jr Js Jt Jy Kd Kf Kg Ki Kl Kp KR KS Kz Lh Lu Lv Lw Lx Ly Lz Ma Mb Mc Md Me Mf Mg Mh Ml Mj Mk Mm Mp
Mq Mr Ms Mt Mu Mv Mw Mx My Mz Na Nb Nc Nd Ne Nf Ng Nh Ni Nj Nk Nl Nm Nq Nr Ns Nt Nu Nv nW Nx NY Oe oF Og oH OK Om
ON Or Ou Pa Pb Pc Pd Pe PF Pg Pi Pk Po pY Pz qA qB qC qD Qg Qh Qm Qn Qt Qu Qv qW QX Qz RA RC Rg Rj Rm rS rX Ss St Tn To Tr Tt
Ua Ub Ud Ue Ul Um Up Ut Vo Vp Vq Vs Vv wD Tj) Ko(aC AD aE AF aG aH al aL AL AN AO Ap aQ aR AS aU aV AW aX aY aZ Ba BB
BC bE bF bG bH bI bJ bL bM Bn BO bP bQ bR bU bV bW bX bZ cB cC cD cE cF cG cl cJ cK cL cM cN CO CP Cq cR cS CT cU CV CW
CX cY cZ dA DB dC DD dE dF DG dH DI dJ Dk DL dN Dp DR EF EZ Fb FN fP Fr Gd GL GP Ha hC HF hG hL hO Hq Hr Hu Hw Hx iA IB
Ic iH Ii iJ Il IO iP Iq It Jd Je Jf Jg Jh JK Jm JT Ju JY Kg Ki Kp kQ KR kS Lu Lv Ly Ma Mb Mc Md Me Mf Mg Mi Mj Mk Mm Mn Mp Mv
Mw Mx My Na Nb Nc Nd Nf Ni Nj Nk Nm Nq Ns Nt Nu nW Nx NY Of Og oH OK Om oN Ou Oz Pa Pb Pc Pd PF Pg Pg Pk pS Pz QC Qg Qh
Ql Qm Qn Qt Qu Qv Qx Qy QZ Ra RB Rc Rg Rh Rj Rm rN rW rY Sh sO St Tn To Tr Tt tU Ua Ub Uc Ud Ue Uf Uk Ul Um UO Up uR UT Uv
uX uY uZ vl Vp VQ VS wB wC wD wE wF wP yD yH yK yL zA xA Wm Tj Th) Sr(aA aC Ad aE AF al aJ aK AL aM aN Ao Ap AR As aU aV
AW Ax BA BB Bc bF bG bL BN BO bR bS bX bZ cA cl cM Co CP CQ Cs CT Cu Cv Cw CX cY cZ dA Db DC DD De dF Dg Di DK DI
dM Dp dR Du eC Ef Em Eq Ez Fa Fc Fi Fn Fp Ff Fw Fy Gb Gc Gh gL Gn Gp Ha hB Hf HI Ho Hp Hq Hu Hv Hw Hx Ib Ic IH Ii Ij Ik Il Im IO
IP Iq Ir It Iv IZ Jd Je Jf Jg Jh Jk Jl Jm Jn Jo Jp Jr Js Jt Ju Jv Kd Kf Kg Ki Kj Kl Kp kQ kS Kx Ky Lh Lp Lu Lv Lw Lx Lz Ma Mc Me Mh Mi Mj
Mk Ml Mm Mn Mq Mr Ms Mt Mv Mx My Mz Na Nb Nc Nd Ne Nf Nh Nl Nj Nk Nl Nm Nn Nr Ns Nt Nu Nv nW Nx Ny Oa oE OF Og Oh OK
Om ON Op Or Ou Oy Oz Pb Pe Ph Pi Pj Pk Po Pz Qb Qc Qe Qg Ql Qn Qt Qu Qv Qy Qz Ra Rb Rf Rh Rj Rm Rv Rz Si Sj Ss St Tn To Tr Ua
Ub Uc Uf Ug Uk Ul Un Uo Up Us Ut Uv Uy Vc Vh Vj Vo Vp Vq Vs Vw Wc Wg Wh Yd Yi Yj Yl Zq Zw Zx Ye Tm Wm Yf) Qe(aC AD aE
AF aG aH al aJ aK AL aM AN AO AP AR AS aU aV AW AX aY aZ Ba bB BC bE bF BG bH bI bJ bL bM Bn BO bP bQ bR bS bU bV bW bX
bZ cA cB cC cD cE cF cG cl cJ cK cL cM cN CO CP CQ cR CS Ct CU CV CW CX cY cZ dA Db DC DD dE dF Dg dH DI DK Dl dM dN Dp
DR Du eC Ed Ef Eq Ez Fd Fi Fw Gb Gc Gh gL Gp hB Hc Hf Ho Hp Hq Hr Hx iA Ic iH Ii Il In iO iP Iu IZ Jd Je Jf Jh JK Jm jQ Ju Jv Kd Kg Ki
Kj Kl Kp kQ Ks Kx Ky Kz Lp Lt Lu Ly Mb Md Me Mf Mg Mh Mj Mk Ml Mq Mu Mv mZ Na Nb nC Nd Ne Nf Ni Nk nL Nq Nu nW Oa oE
OF Oi oN Op Ou Pd pF Pg Ph Pj Pk Qb Qc Qg Ql Qm Qt Qu Qv Qw Qy Qz Ra Rb Rc Rf Rg Rh Ri Rj Rm Rv Ry Rz Sf Si Sj Ss Tn To Tr Tt Tz
Ua Ub Uc Ud Uf Ug Uk Ul Un Uo Up Ut Uu Uv Uw Uz Vb Vc Vh Vp Vq Vs Vw Vz Wb Wc We Wg Wh Yh Yi Yj Yl Zq Zw Zx Tm Wm Yf)
Tv(aA aE AF aG aH al aJ aK aM Ao Ap aQ Ar aS aU aW AX aY BA BB Bc bE bF BG bI bJ bL Bn BO bR bS bV bW bZ cA cB cG cJ Co cP
Cq Cs CT Cu CV CX Dc De dF Dg Di dK DI dM DR Ex Ez Fp Fr Fw Fy gL Gn Ha hB Hc Hf Hq Hr Hu Hw Hx Ib Ic Ih Ii Ik Il IO Iq It Iu IZ Jd
Jf Jg Jk Jl Jm Jn Jo Jp Jr Js Jt Ju Jv Jy Kc Kd Kf Kg Ki Kj Kk Kl Kp Kx Ky Kz Lh Lu Lv Lw Lx Ly Lz Ma Mc Md Mf Mg Mh Mi Mk Mm Mn
Mp Mq Ms Mt Mw Mx My Nc Nd Ne Nf Ng Nh Ni Nl Nm Nn Nq Nr Ns Nt Nv Nx Ny Oa OE oF Og oH Oi Ok Om Or Ou Oz Pb Pd Pf Ph Pi

Figure 30 Continued oN) jT(aD aM An hW jI Ky Mj) Ho(aH Bo Ex Mj oE Or) Iq(Ik II Io Nj Ns Pz) Si(aP fR oE oF Uu Va) Rf(aQ cJ dK Nh Oe Oi) Uf(Bg oH Oi Uu Ux Th) rB(aJ aP Dl Kr Mj rN) IN(kC kO nF nH nJ nL) Uw(bM Bo Kz oE Uu) rN(aN Jk Lu Nk Ou) Bb(aM Bg bN bV) Gc(dR dX oE Uu) Tn(Bg cQ Ng Rt) Qc(nC nL Ns nU) Vu(Hl Va Vb Tl) nN(iH Nh oF oH) mZ(bQ bZ cO hA) Bo(Gb Yg Yh) Ti(Ha Mj oF) Th(Jd Mj Ql) li(Ms Ns Oe) Pz(Ms Ns Oe) Ps(eM Fb tF) Of(Up Vp Vs) Pd(Ux Vb Ye) cL(nC nK nL) Cq(Rt Tl) Em(Ky oE) Gb(bQ Or) Mv(Fc Uy) Jd(Ng Oi) Uu(Vh Yg) aN(rW vl) bR(ml nL) oF(aE cQ) uT(oN uR) AnyL BaCt BgOu CwVb DlrC GdaM GpeM HaRx MjWd NhiB HcJh YeQl KrtS UzoE aWiH bBoH bImI bNoQ cGhA eCnU fRnK hLiP nWuX

Constrained panels with 3 analytes, where 1.0E-10 >= 'model p-value' > 0. Contains 1,414 panels of 32,874,593 total panels evaluated. : Im{Oy(aA Et Fp Fr Ij Iq Ir Is Iv Jg Ji Jl Jn Jq Jt Lh Li Lu Lv Lw Lx Lz Mi Mj Mn Mp Mr Mt Mw Mz Nb Nn No Nr Ns Nv Nw Ok On Pa Pc Pe Po Qd) Pb(aA Et Fp Fr Ip Ir Is Iv Ji Jj Jl Jn Jq Jr Jt Lh Li Lj Lu Lv Lw Lx Lz Mi Mj Mn Mr Ms Mz Ng No Nr Ns Nv Nw Oe Og Ok On Pe Po Qa Qd) Ng(Et Fp Fr Ij Iq Ir Is Iv Jg Ji Jl Jp Jq Jt Lh Li Lu Lw Lx Lz Ma Mi Mm Mn Mp Mr Mt Mz Nb Nn No Ns Nv Nw Ok On Pa Pc Pe Po Qd) Ns(aA Et Fp Hu Ir Is It Iv Ji Jl Jn Jq Jr Jt Lh Li Lj Lu Lw Lx Lz Mn Mp Mr Ms Mz Nc Nl No Nw Oe Og Ok On Pe Pf Qd) Hu(aA Et Fp Fr Ij Iq Ir Is Iv Jg Ji Jl Jn Jq Jr Jt Lh Li Lu Lv Lx Lz Mn Mr Mt Mz Nn No Nv Nw Oe Ok On Pe Qd) Og(aA Et Fp Ij Ip Iq Ir Is It Iv Jg Ji Jj Jl Jq Jt Lh Li Lj Lw Mn Mr Mt Mz Nb Nm No Nw Ok On Pa Pe Qd) Oe(aA Et Fp Iq Ir Is Iv Ji Jj Jl Jq Js Jt Lh Li Lj Lx Mr Mz Nl Nn No Nt Nv Nw Ok On Pa Pe Qa Qd) My(Et Is Iv Jg Ji Jl Jq Jt Lh Li Lw Lx Mi Mr Mt Mz Nb No Nv Nw Ok On Pa Pe Po) Ms(Et Fp Ir Is It Iv Ji Jl Jq Jt Lh Lw Lz Mn Mr Mz No Nw Ok On Pe Qd) Jj(AA Et Fp Ij Ip Is It Ji Jl Jt Lh Li Lj Mc Mn Nn No Nw Ok On Qd) Lj(aA Et Is Ji Jl Jq Jt Li Lu Lw Mi Mp No Nw Ok On Qd) Jk(Et Is Iv Ji Jl Jt Li Nn No Nv Nw Ok On Qd) Ji(aA Et Ii Ik Jo Jq Li Lu Md Mv Nw Om) Li(aA Et Ik Is It Mc Mv Nw Oi Ok) Nw(aA Hx It Md Mv Mw Oz Qc) Et(aA Aj Fp It Jo No Of) Oz(aA Is Iv Jl No Qd) aA(Ip It Mn Nj Ok) Fp(Ik Jq Jt Lw) Mk(Jl Mr Pa Pe) Hr(Iv Jt Ok) Hx(Iv Mr Pe) On(Mv Mw Of) Ch(kO Ti) Ii(Mr Pe) It(Iv Ok) Jo(Jt Ok) NoIs LuJt MdMz MtMv NcNk NeNl} Nw{Md(aA Et Fp Hv Hw Ih Ij In Ir Is It Iv Ji Jn Jq Jt Li Lw Mp Mr Ms Mz Nc Nl No Oe Ok Oz Pb Pe Qa) Ji(aA Hu Hx Ii Jh Jj Jq Lj Ml Ms Mv Mw My Ng Ns Nx Ny Oe Of Og Om Oy Oz Pb Qc) Oz(aA Fp Hu Hx Is It Iv Jj Li Lj Ml Ms Mv Mw My Ng Nl Ns Ny Oe Og Oy Pb Qc) Ns(aA Et Fp Hx Is It Iv Jj Li Lj Mp Ms My Nc Nl No Ny Oe Og Oy Pb) Oe(aA Et Fp Hu Ih Ij Is It Iv Jn Jt Li Lj Mv Nc Nl No Ok Pb) Jj(aA Et Fp Hx Ij Is It Iv Jn Jt Li Lj Mn Ms My Nl Ny Pb) Oy(aA Et Fp Hu Ij Is It Iv Jt Li Mp Mr Ms Mv Nl On Pb) My(aA Et Fp Ij In Is It Iv Li Mr Mt Mw Nb Og On Pb) Ng(aA Et Ih Ij Is It Iv Jg Jn Jt Li Lw Mn Nc Nl Pb) Mw(aA Et Fp Ij Ir Is Iv Jt Li Mr Nl Nn No Ok) Pb(aA Fp Hu Ij Ir Is It Iv Li Lj Ms Mv Og Ok) Hx(aA Fp Hu Ij In Ir Is It Iv Mr Nl Ok Pe) Og(aA Fp Ih Ij Is It Iv Jm Jt Li Lj Lw) Om(Hv Hw Ij In Ir Iv Jn Jo Jq Jt Ok Qa) Ii(Hw Ir Is Iv Jo Jt Lh Mr No Ok Pe) Ms(aA Fp Ih Ij Is It Jn Li Lj Mn) Mv(aA Fp Ij Is It Iv Li Mr Nl Nn) Hu(aA Et Fp Ij Is It Iv Li Nn Ny) Of(Et Hv Ij Ir Iv Jn Jt Mr Ok) Jh(Hv Hw Ij Is Jn Jt Ok Qa) Mk(Is Iv Jl Mr Pa Pe) Ml(Hv Ij In Jn Mr Qa) Ny(Fp Ij In It Iv Mr) Po(Lh Mr No Pe) It(aA Et Li Lj) Pg(Mp Mr Nd Nt) Li(aA Ik Oi) Et(Fp Lj) Hq(Mp Nd) Hr(Hw Iv) aA(Lj Nj) NnMu MhMr NbIv NeNl IjQc} Ji{My(aA Et Fr Ij Is It Jg Jj Jl Jp Jq Li Lu Lx Ma Mr Mt Mw Nb Nn No Ns Nv Og Ok On Pb) Li(aA Hu Ii Ik It Jj Jo Jq Md Ml Ms Mv Mw Ng Ns Oe Og Oi Om Oy Pb) Oy(Et Fr Ij Is It Jl Jq Lu Lx Ma Mr Mt Nn No Og Ok On Pe Pf) It(aA Et Ii Ik Jj Jo Jq Md Ng No Ns Oe Og Ok Om Pb) Et(Hr Hu Jj Jo Lj Md Mv Ng Ns Oe Of Og Om Pb) Ns(aA Is Jj Jq Lj Lu Mp Ms Nd No Oe Og Pb) Om(Fr Hw Ij In Jg Jp Lx Ma Nn No Ok On) No(Ii Jj Jo Jq Md Ml Ng Oe Oz Pb) Og(aA Ij Is Jj Jm Jo Jq Lj Ms Ok) Md(aA Fr Lx Ma Mr Mt Nn Ok Pe) Is(Hu Ii Jo Jq Ng Oe Oz Pb) Ok(Hr Ii Jo Jq Ng Nx Oe Pb) Mr(Hx Ii Mk Mv Ny Po) Ik(Fp Jq Lj Lu Nx Oe) Pb(aA Jj Jq Lj Ms Oe) aA(Jj Jq Lj Ms Oe) Fr(Hu Ii Mv Ng) Jl(Ii Jo Mk Nx) Nl(Jo Ne Nk) Hq(Lx Mp Nd) Jj(Jq Lj Ms) Pe(Hx Ii Mk) Nn(Mv Ng) Iv(Hr Jo) Jq(Lj Ms) Pa(Ii Mk) Pd(Nd Pf) FpMl MaMv NcNk NgJg JoJt LjOe} Li{Ik(aA Et Hu Ih Ij Ip Iq Ir Is It Iv Jj Jl Jn Jq Lj Lw My Ng No Ns Oe Og Oi Ok On Oy Qa Qd) Jj(aA Et Ih Ij Ip Is It Jl Jn Jq Lh Lw Mn Mz No Ns Og Ok On Oz Pb) Og(aA Et Ih Ij Ip Is It Iv Jl Jq Jt Lw Mn Mz No Ns Ok On Oz Pb) aA(Et Hu Ip It Lw Mv My Mz Ng Nj Ns Oe Oi Ok Oy Oz Pb) Et(Hu Ih Is It Jo Ms My Ng Ns Oe Of Oi Oy Oz Pb) Ok(Hr Hu It Jo Mc Mj Ms My Ng Ns Oe Oi Oy Oz Pb) Is(Hu It Lw Mk Ms Mv My Ng Ns Oe Oi Oy Oz Pb) Pb(Ih Ij Ip It Jl Lw Mz No Ns Oe On) Ns(Ih It Jl Lw No On) Ng(Ih Ij Jg Lw On) Ih(Hu Oe Oi Oy) On(Hu My Oe Oy) Ij(Hu My Oy) JlOy} Et{Jj(aA Fp Ih Ij Il Ip Is It Iv Jl Jm Jn Js Jt Lh Lj Mn Mr Mw Mz Nc Nj Nl Nn No Ns Oe Og Ok On Oz Pb Qa Qb Qd Qe) Og(aA Fp Ih Ij Ip Is It Iv Jn Jq Js Lj Mr Mz Nn No Ns Ok On Oz Qb) aA(Fp Hu Ij Ip Is It Jn Lj Ms My Mz Ng Nj Ns Oe Oy Oz Pb Th) Oe(Fp Ih Ij Is It Iv Jn Js Lj Nn No Ns Qa Qb) It(Fp Ik Is Jo Lj Ms My Mz Ng No Ns Oy) Is(Hu Lj Ms My Ng Ns Oy Oz Pb) No(Aj My Ng Ns Oy Oz Pb Th) Oy(Fp Ij Lj Lx On) My(Fp Ij Mt On) Fp(Ik Ns) Ng(Ih Ij) NsLj MsIj} Jj{On(Fp Hu Ij Ip Is It Jn Lj Ms My Ng No Ns Oe Og Oy Oz Pb) Ij(aA Ip Is It Lh Lj My Nn No Og Ok Oy) Ok(Ip Is It Lj Nn No Og) It(Aa Lh Nn No Nv) Is(Lh Lj No) Lj(Lh Nv) NoIp} Og{Ij(aA Is Jg Jl Lj No Ok On) Is(Jg Lj No Ok On) Lj(Jg Ok On) It(Ok On) NsOn} Ij{aA(Hu Lj My Oy Pb) My(Mt On) Oy(Lx On)} Lj{Ok(aA It Oe) On(Ns Oe Oy)} No{Ti(aK aU cY) Th(Ke Vt)} Ch{ThKq KeOw} GcNeaA Constrained panels with 3 analytes, where 1.0E-9 >= 'model p-value' > 1.0E-10. Contains 1,090 panels of 32,874,593 total panels evaluated. : Et{Ng(Fp Il Ip Iv Jg Jl Jn Jq Js Jt Lh Lw Lx Lz Mi Mn Mp Mr Mt Mw Mz Nc Nl Nn Ns Nv Og Ok On Oz Pe Po Qa Qb Qd Qe) Oy(Ih Il In Ip Iv Jl Jn Jq Js Lh Lz Mn Mp Mr Ms Mt Mw Mz Nb Nc Nl Nn Ns Nv Ok Oz Pe Pf Pg Po Qa Qb Qd Qe) Ns(Ih Ij Ip Iv Jl Jn Jq Jr Js Lx Lz Mn Mp Mr My Mz Nc Nd Nl Nn Ok On Oz Pe Qa Qb Qd Qe) My(Ih Il In Ip Iv Jl Jn Jq Js Lh Lx Mr Mw Mz Nb Nn Nv Og Ok Oz Pe Po Qa Qb) Aj(Ax Ba Bb Bc cI De Ih Ij Is It Jt Li Lj Mr Mt Nn Nr Nw Qa Qd Qe) Oe(Il Ip Ir Jl Jq Lx Mr Mt Mw Mz Nc Nl Nv Ok On Oz Pb Pe Qd Qe) Og(Il In Ir Jl Jm Jt Lh Lw Lx Mn Mt Mw Nb Nl Pe Po Qa Qd Qe) Ms(Fp Ih Iv Jn Jq Js Mn Mr Mz Nn No Ok On Oz Qb) Pb(Fp Ih Ij Iv Jl Jn Js Mr Mz Ok Pe Qa) Oz(Fp Ih Ip Iv Jl Jn Lz Nl Ok Qd) No(Ch Fp Hc Hu Ij Is Iz Jo) Ij(Hu Ih Ik Jh Jo Mv Of) Mz(Ih Iv Jn Nc Nl) Hu(Fp Jn Nn On Qb) Jo(Iv Js Jt Mr Ok) Ch(bN Im Ke Nw) Of(Is Iv Ok On) Fp(Ih Is Oi) Mk(Mr Pe) Hr(Iv Ok) LxHq MrIi IhOi} Li{Oy(Ip It Iv Jg Jh Jn Jp Jq Jt Lh Lw Lx Mn Mp Mr Mt Mz Nb No Nv Pe) My(Ih Ip Iv Jg Jl Jp Jq Jt Lh Lw Lx Mn Mr Mt Mz Nb No Nv Oz) Ng(Ip It Iv Jl Jn Jp Jq Jt Lh Mn Mw Mz No Nv Og Oz) Oe(Ij Ip Ir Iv Jl Jn Jp Jq Jt Mz No Nv Oz) Hu(Ip It Iv Jl Jp Jq Lw Mn No Ns Nv Pb) Oi(Ij Ip It Jl Jn Jq Jt Lw Mz On Oz Pb) Oz(Ip Ir Iv Jl Jq Lw Mz No Ns On) Ns(Ip Iv Jn Jp Jq Mn Mp Nd) Ms(Ih Ij Ip Jq Lw Mn No On) It(Jl Jp Jq Lw Mz No On) Jo(Ij Ip Iv Jl Jt On) Pb(Ir Iv Jn Jp Jq Mr) Mk(Iv Jl Mr Pa Pe) Mz(Hx Lw Md Mv Om) On(Jk Mv Mw Of) Th(No Ny Un) Ip(Jq Lw No) Ij(Jk Mv) Iv(Hr Lw) Jq(Md Om) AaJj NeNl JkJl} Jj{Ij(Fp Fr Hu Hx Ih Jg Jl Jn Jp Jt Lx Ma Md Ml Mm Mn Mp Ms Mw Mz Nl Nm Nv Ny Oe Of Oz Pb Po Qd) It(aA Fp Fr Ii Ip Is Jg Jl Jp Js Jt Lj Lx Ma Mm Mn Mw Mz Nm Po Qa Qd) Lh(aA Ih Ip Iv Jm Jn Js Jt Mn Ms Mw Mz Nn No Ns Og Ok Oz Pb Qa) Lj(aA Ih Ii Ip Jg Jl Jp Jq Js Jt Lw Ma Mi Mm Mn Mp Nn No Nx Ny) Ok(aA Fp Ih Jn Js Mm Mn Ms Mw Nl Ns Nv Ny Oe Oz Pb Qa Qb) Is(Aa Fp Fr Ip Jg Jp Jt Lx Ma Mm Mn Mw Mz Nm Nn Nv Ny) Nv(Fp Ip Jn Jt Mn No Ns Oe Og Oy Oz Pb) No(Jn Jt Mn Nj Nm Ns Ow Oz Pb Uh) Aa(Nw Qa Qc) Nn(Ih Ip Jt) Ip(aA Mn) WmJi FpJt KeOw} Og{Ok(aA Fp Ih Il Ip Jg Jm Jn Js Lh Lw Lx Mn Mz Nl Nn No Nr Ns Nv Ny On Oz Pb Qa Qb Qd) Ij(Fp Fr Ih Ip It Jp Jt Lh Lw Lx Me Mm Mn Mp Mr Mt Mw Mz Nn Ns Nv Pb Qd) Is(Fp Fr Ip It Jp Jt Lh Lw Lx Ma Mm Mn Mw Mz Nm Nn Nv Ny Oz Pz) On(aA Fp Hq Hu Ih Ip Jm Lw Ms My No Oy Oz Pb) No(Ih Ip It Jg Jt Lw Ns Oz) Lj(aA Jl Jq Jt Lw Nv) aA(Ip Jg Lh) FpJt IhJg ItNv} Im{Jk(Fr Ij Iq Jp Jq Js Lh Lv Lw Lx Mi Mj Mn Mr Mt Mz Nc Nl Nr Nt Pe Qa) My(Fr Ij Iq Jp Lv Mj Mm Mn Mp Mw Nn Nr Nt Nx Pc) Oy(Jp Jr Js Mm Nl Nt Pf) It(Ik Jp Jr Lu Mn On) Ms(Ip Iq Js Nn Pc) Hx(Lx Mt Mz Nb Pa) Oz(Ip Ir Lz Mr Pe) Lu(Iq Lw Mn) Ik(Ij Lz Nt) On(Ii Jh Mk)

Figure 30 Continued

Aj(Ad Nw) Nn(Mu Oi) Lx(Hq Mv) Hr(Ir Pe) Pf(Hq Pd) LzJq MwNb NjNk liLh KjkN Urml} On{Oy(Fp Ip Is It Jg Jn Lx Lz Mr Ms Mt Nn No Ns Oe Of Ok Oz Pe) My(Fp Is It Jg Lj Mt No Ns Oe Of) Ms(Hu Is It Lj Ng Ns Oe Of Pb) Oe(aA Hu Ih Is It Ng Ns Pb) Lj(aA Hu Is It Ng Of Pb) Ns(aA Hu Is It Ng No) Ng(Is It Jg Oz) ItaA} No{Is(It Lj Ms My Ns Oe Oy Oz Pb) Th(aQ Iu Kc Kd Kg Ld Nw Qy) Ns(aA Ip It Mp Ok Oz Pb) Aj(Kc Ke Ko Kq Ow Uh) Ok(It My Oe Oy Oz Pb) Ch(Kc Ke Ow Uh) Ti(bV Ow Qv) Ke(Hc Ik Ph) Nw(Hc Jv Us) Oy(Ij Kc Ow) Uh(Ii In) Mylj NgJg IpOz ItaA KcdJ UrVt} aA{Ij(Ik Ip It Jk Lh Lw Me Mk Mm Mn Ms Ng Nj Ns Oe Ok Oz) Lj(Ip Is It Jg Jt Lh Lw Ma Mg Mm Mn Nj Ns Oz) Ok(Ip It Ms Nj Ns Oe Oy Oz Pb) Ip(It Mn Nj Oz) It(Lh Mn)} Ok{It(Fp Hr Jo Lx Mc Ms My Ng Nn Ns Oy Oz Pb) Is(Ms My Ns Oe Oy Oz Pb) Lj(Mc Ns Oz Pb) Ij(My Oy) IhOe} Ij{Oy(Fr Is Jg Jl Lh Mi Mm Mp Mr Mt Nn Nv Pe Po) My(Is Jg Jl Lh Lx) Lj(Mm Mp Oe)} Ji{jT(Bg Ch cQ Ct De Ef Iz Qt Ua) Nn(Hx Ml Mw) Ma(Hx Ml Ny) Wm(Jo Ms) Jg(Mv Mw)} Ke{Ow(Aj Bg Ct De Hc Hq Jo Mk Ms Of Oy) Ch(bN dK Nn Ri) cH(dK oE oH)} Mz{qC(Jk Mv My Of Om Oy) eZ(hV Jk Ng Of) qD(Jm Mg Ng Oy) ChjO NwOm hOhR} Is{Lj(Jg Jp Lw Ma Mm Mn Mp Ns Oe Oz Pb) Jg(My Oe) AjAp NnOe} Th{Kq(Bg My Of) Nw(Ar Iv) AaQa} Ch{Ow(Ko Nw) NnUh} Lj{NsMp NvOe} Nw{AaOy AjJt} JoKnjT Constrained panels with 3 analytes, where 1.0E-8 >= 'model p-value' > 1.0E-9. Contains 8,174 panels of 32,874,593 total panels evaluated. : Ps{Uu(aK Al aO Ap aS aU aW AX aY aZ BA Bb bG bH bL Bo bQ bV cB cD cE Ch cI cL cM cN Cq cR cT cU Cv Cw CX cZ DC Dd dF Di dK Dr Ed Ex Ez Fc Fi Fw Fy Gh Gp Hu Ib Ic Ih Ij Il Im Ir Is Jg Jk Jm Jn Jp Ju Jv Jy Kd Kf Ki Kk Kn Kp Lh Li Lj Lp Lv Lx Mf Mg Mh Ml Mn Mr Ms Mt Mx Nb Nd Ne Ni Nn No Nr Nt Nu Nv Nx Ny Oe Og Oh Ok Om Ow Oy Pa Pc Pe Pf Pz Qa Qb Qc Qe Qh Qu Qy Rm Ru Rx Ry Sf Sr Ss St To Uc Ug Uh Uk Ul Us Uv Uy Va Vh Vi Vq Vs Vz Wd Wh Zx Ti Th) Rx(aA AF aG aI Aj An AO aR AX aY aZ bF BG bH bL Bn Bo bU bZ cB cD cE cG CH cM cN Co cR cS Cu cV cW dA dD De Dg Di Dk dM Ed Ef Em Eq Ez FR Fw Gh Gl Ha Hc Hq Ih Ii Im Ir Iv Iz Jd Jl Jp Ju Jy Ke Kg Kj Kl Ko Li Lj Lu Lv Ma Mh Ml Mm Mn Mu Mv Mx My Mz Ng Ni Nk No Nq Nx Oa Of Og Oh Ok On Op Ou Ow Pe Pg Qb Qn Qt Qu Qw Qz Rb Rf Ri Sf Sh Si Sr Ss Tn Ua Uh Us Ut Uv Uw Va Vb Vp Vs Vt Vw We Wf Wh Yd Zx Wm Th) aW(Aj Ar aX aZ Ba Bg Bo Ch Cs Ct Dg Dp Ed Ef Eq Fd Fn Fp Gd Gh Hb Hf Ij Iv Iz Jg Ji Jj Jo Ke Kg Ki Kj Kl Ks Kx Ld Li Lj Lp Lx Lz Mh Ml Mq Ng Nw Oa Or Ow Oy Pa Pe Ph Po Qb Qg Qu Qx Rg Rv Rz Sh Ss Tv Tz Uh Ur Us Ux Vb Vo Vs Vt Vw Yl) Vs(aC aF aK Ao Ap aU aX bC bG Bo bQ bW bZ cG cL cN CO cS Cu Cw cY dI dK dM Et Fc Fi Gp Hc Ho Hw Ib Ij Il Jo Kc Kd Ke Kg Kq Li Lx Mf Mg Mi Mm Mn Mt Nm Nn Nw Oe Oi Ow Oz Pf Pj Rc Rj Rz Si Uf Uh Uk Vq Wf Ti) Ch(aF Ao Ar aU aX bG bJ cJ CO cU De dI Ef Ez Fi Gp Ho Hv Ij Iv Jd Je Jh Ji Kc Kd Ke Kg Kj Kz Ld Li Lx Ma Mf Mg Mi Mm Mp Mq Mt Mu Nn Nq Oe Om Ow Pd Po Qd Qy Qz Rz Tn Uf Uh Ut Wf Ti) Ed(Af aG aH aJ aK aQ aR aU aZ Ba Bn bP bQ bS cN CX cY Dc Dk Et Gp Gz Ha Hc Hp Hu Ib Ic Ij Je Jl Kj Lu Lx Ma Mf Mg Nv Oe Oi Or Ow Oz Qn Qw Rj Sh Uh Vp Vq Wf Ye Ti) Uh(Al aY aZ Bb Bg bO cH dK Ef Ex Ez Fc Fw Gl Ih Il Im Jd Ji Jm Kd Kl Kx Lj Lp Mh Ml Ms Mx Nb Nd Ne Nn Nr Nx Oa Oi Pa Pe Qm Qn Ru To Uk Un Uv Uy Va Vw Yd Tm Th) Ow(Ad Af Aj Ao Aw aX aY aZ BG Bn Co Cp cS De Dg Di Ef Eq Ez Fc Gl Hc Hu Ib Iz Jo Kg Kl Nc Ng Nl No Oi Oz Pb Qt Qw Rz Sh Ss Ua Uc Uv Ux Vo Wd Wh Yd Zw Zx) Lj(aC Af aG aJ aP bM Bn Bo bS bX cE cN Cx Dd dI Dk dM Fc Ha Hb Hc Ib Ih It Jl Ld Lp Mj Mx Oi Oz Pa Pc Qn Qv Qw Ri Rj Rv Sh Ug Un Ur Vp Vt Wf Ye) Us(aF Bb bG Bn cM cP cQ cU Dd DK Fc Fi Hc Ho Hp Hv Ib Ij Il Is Kd Ki Li Lu Lx Mf Mt Nc Nn Oi Om Oz Pf Pi Qv Qw Rc Sh Si Sr Uk Vq Vt Ti) Ef(aU bZ CO CU dI Et Gp Hv Kd Ke Kg Kq Li Lx Ma Mg Mi Mp Mq Mt Mu Nn Nq Om Pd Qy Uf Wf) Pe(Af aN aR aY aZ Bn bS Cx Dd dG Dk Du Ex Ha Hc Ib Id Oe Oi Oz Pc Qn Qt Qw Rj Ua Vp Wf Ye) Va(Af aR aZ bM Bo bS Cx dB dG Dk Hc Hu Ib It Jl Oe Oi Oz Pc Qn Qt Qw Rj Vp Vq Vt Wf Ye) Gp(Aj Ao aX aY Bg Bn cS De Dg Eq Ez Fr Gl Hc Iz Kl Ng No Qt Rz Ss Ua Uv Ux Wd Wh Yd) Bo(aY Cv Di Ez Fw Ij Il Im Jd Jm Kd Kl Mh Ms Mx Nb Nq Nr Oh Pa Ru Sr Ss To Uy Th) Ij(Ad Aj aN aY aZ BG bM De Dk Fc Gl Kf Kr Mj Nl Of Rt Up Uv Vb Vh We Yd Zw) Bg(aK Aw aZ bF bQ cE cL Co dK Fi Il Is Kd Kq Li Lx Mf Mt Nn Oe Oh Om Pf) Fw(Af aH Ar Bn Cv Hb Hc Hu Ib Jk Ki Ld Oe Oi Oy Oz Qv Qw Rj Sh Ur Wf Ye) Im(Af aG aH aJ aZ bS cI Cx Hc Hu Ib Ki Oi Oz Qn Qt Qv Qw Rj Sh Vp Wf) Li(Af aN Ao aX aY aZ bM Bn bU cC Dd De Dg Du Eq Ez Fc Gl Ib Kl Oe Uv) Oa(Af aG aJ Bn bS Cx Dd Ha Hc Ib Jl Oc Oi Oz Qn Qv Qw Rj Vp Wf Ye) Oi(aA aF Ar aY cV Gh Iv Jy Lv Mh No Og Qn Sr Vb Vo Wf Yd Zw Th) Nn(Aj aX aZ De Dg Eq Hc Hu Iz Kl My Ng Qw Rz Sh Ss Ua Vt Wf) Lx(Aj aN aY Bn De Fc Gl Hc Iz Kl My Qw Ss Uv Wf Wh Yd Wm) Kl(Ap bQ cU Cw dK Et Ib Il Ma Mt Nt Oe Pd Rj Rz Ti) Ld(aY Bb Ez Jm Jy Kd Lp Mh Nr Pa Ru To Ul Uy Th) Oe(Eq Hc Iz Ng No Qt Qz Rc Sh Sr Ss Vb Vt We Wh) Ur(aY Ir Jd Jm Kd Lp Mh No Nr Pa Ru To Th) Eq(aF aU Fc Kd Kq Mi Mt Mu Om Ph Qy Rz) Ar(aY Bb dK Ex Il Jm Jy Kd Ru Ul Th) Mh(bG dI Fc Hc Oz Pa Qv Qw Rj Rv Vt) Hc(aA bO Jn Ml Mx Nb Pf Qa Vi Wc) Aj(bQ cL dK Il Is Kd Mf Om Sr) aY(aM Et Is Ji Jj Kx Lp Nw Po) aZ(bG bO cU Oz Qa Sh Sr Vo Wh) Dk(Is Jn Js Ml Mx No Qa Qx) Kd(Bb Gd Iz Kj Lp Nw Rt Ux) Pf(aN Bn Iz My Qw Wf) No(Ha Ib Qn Vp Ye) Nw(Jd Jm Ms Ru To) Fc(Gd Ml Oh Ux) Gl(bB cU Et Rc) Vt(Il Nr Ru Yd) Oz(Ml Mx Vb Vw) dK(Jo Kj Ss Vo) Af(bO Gh Qa) Sr(bM Ki Ug) Qw(aL Hu Jn) Rj(dN Ml Mx) Gh(bP Ye) Mw(Ib Ua) Hp(Ss Wh) We(Is Mf) Lp(To Uy) Ny(Qn Vp) Vo(aN cX) aX(Mt Pd) CxaA DcOm EtEz ThIv LuYe MlSh IbVw IlRt YdKe QaaN SsbQ WdcL WhVp WfKk RuPa OhbG} Ow{Wb(aC aE AF aG aH aI aJ AL An AO Ap aQ aS aV aW AX aY aZ bA BC bF BG bH bJ bL Bn Bo bP bQ bR bV bW bX bZ cB cE cG CH cI cJ cL cM Cp CQ cR cS Ct CU CV Cw cX cY DB Dc DD dE dF Dg dH dJ DK DL Dp Dr Ez Fd Fn FR Fy Gc Gd Gh Gl Gn Hc Hl Ho Hq Hr Hu Hv Ib Ih Il Im Ip Ir Iu Jd Jg Ji Jj Jk Jl Jm Jo Jp Jq Jt Ju Jv Jy Kd Ke Ki Kj Kk Kn Kp Kq Kr Ky Lp Lu Lx Ma Mb Me Mg Ml Mm Ms Mt Mw Mx Mz Nb Ne Ng Nk Nl Nm Nn Nq Nr Ns Nt Nu Ny Oa Of Oh Ok On Ou Oz Pa Pc Pd Pe Pf Pg Ph Pk Pz Qh Qw Rc Ru Rx Rz Sh Si Ss Ua Ub Ue Uf Ul Ur Vq Vt Vw Vz Wd Yd Yl Zx Tm Xa) Dr(Aj aL An Ao aW aY aZ BA bB bC Bg bO bW bX Ch Co cQ cT Cw CX dE Dg Di Dl Dp Ed Ef Eq Ex Ez Fc Fd Fi Fn Fw Fy Gh Gl Ha Hc Hl Ho Hp Hv Ib Il Im Jd Jh Jm Jo Jy Kd Kg Ki Kk Kl Kn Kp Kr Kx Li Lj Lp Lv Mg Mh Ml Mm Mp Ms Mx Nb Ng No Nq Nr Nx Oa Oe Of Oi On Op Ou Pa Pd Po Qa Qb Qg Qh Ql Qm Qn Qt Qu Qw Qz Rc Rf Ru Rv Rx Ry Rz Sh Si Sr Ss To Tv Tz Ua Ub Ue Uf Ug Uk Ul Un Ur Ut Uu Uv Uw Ux Uy Va Vb Vo Vp Vq Vs Vt Vw Vz Wd We Wh Yd Yl Zw Tm Tj Ti Th) Vi(AD AF aI AJ AO aS aV Aw aX aY aZ Ba bB bF BG BN bZ cE cG CH Co cS cV cY Dd De dF Dg Di Dk Ed Ef Eq Ez Fr Gl Hc Hq Hu Iz Jo Jp Jq Jy Kg Kl Kr Ky Li Lj Lv Ma Mg Mk Ng Nl No Nq Nx Of On Ou Pk Qt Qu Qw Qz Rz Sh Sj Sr Ss Ua Uc Uf Ut Uu Uv Ux Vo Vs Vt We Yd Zw Zx) Eq(aA aC Af aY Ba bE bH bM BO cE Cq Cu Cx dD dI Dk Ed Ef fR Hp Ib Im Iz Jd Je Jh Jj Jk Jy Kg Kq Ld Lx Mh Mr Mu Mw Nb Ni Nj No Nq Nt Nu Nv Ny Qd Ql Qm Qy Rc St Un Wd Yd) Ke(Af Ao cH Co Cp dJ Ef Fr Gl Hr Hu Hx Ib Ik Iz Jd Jh Jk Kj Lj Mj Mp Mw My Ng No Nq Oa Om ON Pb Ph Qw Yd) Hp(Af Aj Ao aX aY aZ BG Ch cP De Dg Ed Ez Fc Hc Jo Kg Ki Kl Kr Ng Nl Qz Rx Sh Ub Uu Uv Ux Vb Vo Vs Zw) No(Bg Ct Fd Gd Gh Gn Hc Hq Lp Of Rt Rx Rz Sf Sh Ur Uw Ux Vb Vw Vz Wd Wf Wh Yl Zw Zx Ye Tl Xa) Ed(Du Fc Fi Gb Gh Gn Hl Ho Op Rt Rv Rx Rz Sh Ux Va Vb Vh Vz Wc Yd Yl Zw Ye Tm Xa) Ny(Ch Du Fc Gh Hl Lp Of Rt Rv Rx Ry Rz Sh Uw Ux Vh Vz Wd We Wf Wh Yd Yl Zw Ye Tl) aA(Fc Fd Fi Gd Gn Hl Ho Lp Op Ru Rx Ry Rz Sh Si Ux Uy Va Vb Vw We Wh Yd Zw Ti) Yd(Aj aX aY bF Dd dH Gb Hb Ih Jk Jl Ko Nb Nt Nw Oz Pb Pc Pi St) Sh(Af aX aY bJ bM BO Dd dI fR Hu Ib Im Je Kq Ld Mh Mu Qy Uo) Zw(aE aX bJ bM bO Hx Im Je Kq Ld Nb Nt Nu Nv On Qd Qy Un Uo Vz) Ux(aC aH bE bJ bM BO Im Je Kq Mu Nb Nv Qy) Ch(Em Et fR Hb Ji Jp Kc Kf Kk Kq On Qd Uh) Af(Fd Gb Ho Lp Uw Uy Uz Vh Wc Wh Yl Xa) bM(Fd Fi Gn Ho Lp Rt Uy Va Vh Wh) Aj(Et Gb Ko Kq Nw Qd Vw Wd) Vz(aX aZ Im Nb Oi Pe Sr Ub) Nb(Fc Hl Rt Uw Vh We) Jj(Fw Ko Lj Nw Uh Vq) Ld(Fd Ho Lp Uy Vh Wh) Rt(aX Fd Pe Pi Pk) Nw(Bg Hq Mk Ng Oy) Du(Ax Fw Li Pe) Kg(Fd Lp Si Sj) Rz(Bo fR Kl Qy)

Figure 30 Continued

Vw(aX Dg Gl Kl) Gb(Jo Kl Ma) Gd(iZ Pe Qy) Va(aX dL Un) Bg(Jp Wd) Dd(Sf Vh) Im(Rv Wf) Jo(Em Fd) Oy(Mt Pa) Pe(Hl Yl) aX(Sf Xa)
AaTh MwWf HxRx RyaZ} Im{Sh(aA aC aD aE AF aG aH al AJ aK aL aM AN aO AP aQ AR AS aU aV Aw aX aY aZ BA BB BC bE bF bH
bJ bL bM Bn bO bP bQ bS bV bW bX bZ cB cC cD cE cF cG Ch cJ cK cL cN CP Cq cR cS CT CU CV cW CX cY cZ dA DB DC DD DE dF
dH dJ DK Dl dM Dp Dr Ed Eq Et Ex Ez Fc Fd Fn Fr Fw Fy Gh Gl Gn Gp Ha Hb Hc Hf Hp Hq Hu Hv Hx Ic Ij Ik Il Io Ip Iq Ir Is Iu Iz Je Jf Jg Ji
Jk Jl Jm Jn Jo Jq Jr Js Ju Jv Jy Kc Ke Kf Kg Ki Kl Ko Kq Ks Kx Ky Kz Ld Lh Lt Lu Lv Lx Ma Me Mf Mg Mh Mj Mk Mn Mp Mq Ms Mu Mv
Mw Mx My Mz Nc Nd Nf Ng Ni Nj Nk Nl No Nt Nu Nv Nw Nx Ny Oa Og Oh Ok Om On Or Ou Oy Oz Pa Pb Pc Pd Pe Pg Ph Pi Po Pz Qa Qb
Qc Qd Qe Qg Qh Qm Qn Qt Qu Qv Qw Qy Qz Rf Rg Rh Ri Rj Rm Rt Sf Si Sj Sr Ss Tn To Tv Tz Ua Ub Uc Ue Uf Ug Uh Un Up Ut Uu Uv Ux
Uy Va Vb Vi Vp Vq Vs Vt Vw Vz Wc Wf Yd Yl Zw Zx Xa Wm Ti) Wf(aH aI aK As aU Ax bA bB Bc bJ Bn bP bV Ch Cq Cs Cu cY Db Dc
dG Dk dM Ex Fd Fn Fy Hv Id Is Jd Ji Jj Jn Jq Jr Js Ke Kk Kq Kx Ld Lh Lv Lx Mj Mr Mx Mz Nv Nw Nx Ny Ok Om Or Pa Pb Pe Pg Pi Pk Po
Qa Ry Tn To Tv Uc Ut Uw Vi Vp Vs Vt Yl Xa) Eq(aG aH aJ aK aR aU Ba bP bQ bS cE Ch cL Co cY Dc Dd Ez Hu Ji Kc Ke Kg Kq Ld Li Mg
Mi Mp Mt Mu Mv Nn Nq Nw Om Pd Qt Qw Qy Ri Rz Sj Uf Ug Uh Wd) Ch(Fc Fi Gb Gh Ho Hp iJ Ji Ke Ko Lp Nw Op Rv Rx Ry Rz Sf Si Sj
Ux Uy Vb Vh Vw Wb Wc Wd Yd Zw) Ye(aG aK bC bE bG bM bP bX cB cC cJ Cv cZ dl DK Je Jk Kx Li Mp Nc Nv Nw Pd Qd Qw Ug) Aj(Ba
cH Dg Gb Ho Is Jg Ji Jt Ke Kk Ko Mb Mm Mn Mt Nk No Si Vb Vh Wc Wd) We(aZ Cp Cq Cu Dc Dr Hv Ij Jq Jr Js Ke Kq Kr Mz Nb Om Pe Pi
Tv Vi Vp Vs) aG(Du Fc Fd Gb Hl Ho Lp Op Rt Ry Rz Uw Uy Uz Vh Vi Wc Wg Yl Zw Tl Xa) aZ(Du Fc Fd Fi Gb Hl Ho Rt Ru Rv Ry Uw Uz
Vb Vh Vi Wc Wd Wg Yl Tl Xa) Qw(Du Fd Fi Gh Gn Hp Ry Sf Si Sj Ux Vi Vw Vz Wd Yd Yl Zw Zx Tl Xa) Hu(Du Fd Fi Gb Gh Hp Ry Sf Si
Sj Ux Vi Vw Vz Yd Yl Zw Zx Tl Xa) Ux(aH aU bP bS cE Cw Dd Ez Ji Kg Kq Ld Mg Nw Oz Pd Uf Vq) Fd(aH Bo bS cI Ha Hc Ib Oy Oz Qv
Rj Ug Ur Uu Vp) aH(Du Fi Gb Gh Ho Rv Uy Uz Wb Wc Wh Yl Zw Xa) bS(Du Fi Ho Ry Sf Sj Vb Vh Vw Vz Yl Zx Tl Xa) Hc(Dr Gb Ke No
Rt Ru Uw Uz Vi Wg Yl Tl Xa) Ug(Dr Gn Hl Ho Rt Uw Uz Vh Vi Wc Wg Yl Xa) bP(Hl Ho Hp Lp Rt Rv Rz Vb Vw Wd Yl) Aa(Ji Jo Lu Mk
Nw Og Oi Oy Qc) Xa(Hb Ib Oy Oz Qt Rj Ua Ur Uu) Ld(Dr Fi Ho Lp Rv Uy Wh Yl Zw) Hl(Dc Ij Is Ji Lx Oh Ur) Rt(Dc Is Ji Lx Oy Ur Uu)
Vi(Dk Lu Oy Qt Uh Uu Vt) Sj(cI Hb Kl Qt Ss Uu) Rv(aU Is Ji Lx Ml Oh) Ur(Dr Uz Wc Wg Tl) Oy(Uw Uz Wg Yl Tl) Vz(aK aU Lx Oh) Uu(Si
Uw Vh Wc) Dr(Hp Vt Vw) Du(Nw Qt Ua) Dc(Lp Ry) Gh(Hb Qt) Gb(Iz Uh) Lx(Yd Zw) Ua(Zx Tl) Ji(Uw Vh) Rz(aX Ri) Yl(Ib Uh) Nw(Uw
Yd) CuWh DeKe TiNo FcLu IzWd SfQt ZwOh ZxVt RubM} Vi{Lj(aG aJ aK aQ aU bB bC bG Bo bQ bS bX bZ cB cE cG cI cJ cL cP cQ Cs
Cu CW cY dA Dd dJ DK dM Et fR Gc Gp Ha Hb Hc Hp Ib Ic Ij It Je Ji Ke Ko Kx Ld Lp Lu Lv Ma Mf Mg Mp No Nv Nw Oi Ou Oz Pd Qv Qw
Ri Rj Sh Si Sj Uf Ug Uh Un Ur Vq Vt Wc Wf Ye Ti) Ch(Ao Ap aU aW aX bC bJ bW CO cQ cS Dc Ef Ez Gc Hv Ij Iu Jd Jh Kc Kd Ke Kg Ld Li
Lx Mg Mi Mm Mp Mq Mt Mu Na Nn Nq Om Pd Pj Qd Qy Qz Rz Uf Ut) Hc(aJ aM aP aW bJ bP cL cQ Db Ed Fn Hq Hw Ih Ij Is Iv Jn Js Kc Kk
Li Lx Mf Mt Mw Nn Nr Nw Oa Oh Om Pe Pf Pg Qa Qg Rx Sr Ub Ue Vq Wh Xa) Li(Aj aX aZ Bg bH bM Bo bU cQ dE Eq Fr Ib Ik Ir Lx Mf
Mh Mu My Ng Of Oh Oy Oz Qt Rz Ss Uh Uu Uw Ux Vb Vw Ti Th) Bg(aU aW Co cQ Cx De Ij Is Kc Ki Ld Lx Mi Mp Mt Mu Mv Nn Nq Nw
Oh Om Qd Qy Rx Ue Vq Wd) Ld(aO aX aY Bb bH cR cS Dk Ef Eq Fw Jd Jm Jy Kd Ky Lp Mx Nx Ou Pa Sr Ss Uv Uy Yd) Pe(aD aP aZ bP bS
cP cW Dd Dk Ha Hu Ib It Lu Oy Oz Qt Qw Rj Uh Ur Uu We Wf Ye) Eq(Ap aU aW bC bW CO De Ez Hv Jh Kc Kg Mg Mi Mp Mu Nn Om Pd
Qy Qz Rz Uf) Of(Ap aU bZ cL Dd Fi Gc Ho Hq Hw Ij Is Kc Kd Lx Mf Mg Nn Om Pf Uc Ue Vq Vt) Lx(aO aY bF bG cH Dk Ed In Jl Jp Ky My
Nx Qw Rb Sr Tn Wf Yd Zx) Wf(bP cP cQ cV Cx Fn Ih Ij Is Jn Js Ki Kk Mw Nn Oh Rx Sr Uu) Uu(aS bG Cw Dl Hw Ih Ij Jt Kf Nm Om Si Uc
Ue Vq Vt Ti) Ed(aQ bZ Et fR Gp Hb Ij Lu Ma Ne Oz Si Ug) Qw(bP cQ Fn Hq Ih Jn Kk Mw Nn Om Pf Qa Xa) Dk(Fn Ir Is Jn Js Ke Kq Nw Qa
Qd Qe Rh) Ef(aW Co Kc Mi Mp Mu Nn Om Qy Ue Uf) Nn(Aj aX Iz Mv My Ng Qu Rz Sh Ss) Ij(AD bF bG cH Lu Og Rb We Zx) Sr(aF aZ bM
cL cW Is Lu Mp Nw Oh) Aj(bJ Gc Ho Hw Om Qd Vq) Lu(Fn Fw Gp Ki Kk Oa Rx) Sh(aW cP Ih Oh Pf Rm Ti) Oa(aG Bn cN Pj Uh Vq) bG(cQ
Cx Ki Mn Oh Pf) No(aK Gp Uh Vt) My(Kd Mt Om Qd) We(Kq Mi Om Qa) Ke(Gl Nx Ru Uv) aX(Ap Ez Mt Uf) cQ(bF cH Jp Rb) Kz(aW Uv
Th) Vt(Bo Ih It) aZ(aF Ap Iv) Ad(Mi Vq) Bn(Fn Tz) Yd(Ji Nw) Og(Oz Uh) aY(Is Nw) ApUx ArBb BoOz DeMp PoUv EzSs FrMt GpJp MjJs
UaaU IhUh IzOm JjKd KxaW VbPd} No{Uh(aW Bg bN cH cQ Ct De dJ dK Gl Hc Ic Ik iO Ir Iz Jk Jo Kc Kk Ko Ld Mj Ng Nv NW Of oK oN Ou Oy Ph Pk Qw Ri Up Ur Us Uu) Ti(aA aG aQ aV aZ Ba bM Bo cB cE CW dA dJ dR hB Is Kk Ld Lv Ma Mg Nb Nn Oa Oh Qa Qd Rh Ri Tz Ub Uc Um) Ke(Af Bg cH Cp cQ Cu De dJ Dk Ef Fr Gl Hu Ii In Iz Jj Jk Jo Jv Kc Kj Lh Mj Mr Ms Ng Nv Of ON Oy Po Us) Vt(Aj Ch dJ Dr Fc Gn Ii In Jj Lp Ru Rx Ry Si Sj Us Uy Va Vh Vz Yd Yl Zw Tm Xa) Th(aG Ap aU aX cS Cw dA dJ Ij Jh Ji Ko Kq kR Ma Mg Mu Mv Nn Pj Qd Uf Un Ur) Kc(Bg bL bS Ct De Et Fr Hc Ii Ik In Iz Jj Jo Kj Lu Ng Nv Nw Of Oi Ou Ph) Aj(Ad Ap Bb Ez Hb Ho iO Jd Jg Ji Jt Kf Kg Kk Kl Kn Kp Ld Nw Pj Uc Uf) Nw(Ch Ha Hf Ic Iz Kj Kl Ks oN Ph Qw Rb Rm Ru Rx Sj St Ur Ut Uy Vs) Lj(Ij Ip It Jg Jl Jp Jt Lw Mm Mn Mp Nj Nn Ns Nv Oe Og Oz Pb) Pb(aA Ij Ip It Iv Jl Jn Jt Lw Ms Nj Oe Og On) Sh(aU aW Ba Bb bQ cE cL dK Hq Jg Kd Pf Ph) Oy(aA Ih Ip It Jg Jl Jn Jt Lw Nj Ns Nv Oz) Ms(Ih Ij Ip It Jn Jt Mn Nj Ns Ok On Oz) Rx(aE bQ cE cL Dc Js Ld Lx Ma Mp Pi Uc) Oe(aA Ih Ij Ip It Jn Jt Nj Ns On Oz Qd) aK(Fc Fi Hp Lp Ry Sf Ux Uy Vb Wb Yd Tl) aU(Fc Fi Hp Ry Sf Sj Uy Wf Yd Zx Ye Tl) Og(aA Iv Jl Jn Jq Lh Mz Nj Nm Nv Qd) Ch(Hb Jd Ji Kg Kk Ko Kq Qy Uf Ur) Et(Ef Fc Kj Kl Ks Ph Ur Us Uu) Gp(Fc Fi Ho Rz Sf Ux Vb Wd Wh) Ng(Ih Ij Ip Is It Jt Ok On Oz) Hc(dJ In Jd Jj Jp Kk Ko Mh Ur) Nj(aA Ih Ip Is It My Ns Oz) Fc(aQ aZ cW cY Lu Lx Oh) Wf(Bb Hq Ih Nn Om Pf Qa) aA(Hu Ip Jn Lw Mz Ok Oz) Ij(Hl Hu Ik Sj We) Zw(cL Is Ld Lx Mp) Wd(aX bM cD cW Ss) Ye(Ho Nn Om Qa Qd) Ko(In Iz Jj Jo Kj) Vq(Gn Hp Vh We Xa) Rz(aX bM cD Ss) Ld(Lp Ru Uy Tm) Om(Eq Uw We Wh) Vb(cL CW dK) Fi(bM cW cY) Ns(Jn Lw Nc) My(Ip Jg Mt) Ho(aZ bM cW) Hu(Ip Is On) It(Ip On Oz) Si(Bo bQ cE) Ur(cQ dJ Ph) Uy(aG cY Mp) Jj(Aa Pj) Vw(Pd Uf) Oz(Iv Jl) aG(Du Lp) CxSj MgXa MpRu HrOk TvcH IsRt JiUs KkdJ VacL} Ld{Lp(Af aG aH aM Ap aZ Bo bR bU bX cB cE cF cK cL cN cP Cs Cu Cv CW Db DC Dd dH dN Dr Ed Et Fp fR Fw Gc Gn Gp Hq Hr Ih Ij Io Ir Is Iv Jd Jg Ji Jj Jk Jl Jp Ke Kf Ki Kk Kl Kn Ko Kp Kq Ks Li Md Mq Mt Mv Nb Nn Nq Nr Nu Nv Nw Ny Oe Oh On Pe Pk Pz Qa Qb Qc Qd Qe Qh Qv Ri Rj Sr St To Uf Un Ur Uu Uv Ux Vh Vq Wf Zx Ye Xa) Uy(Ba bQ Cw Dc Ed Fw Gc Gp Ih Ij Io Ir Is It Jg Jk Jn Ko Li Nb Nw Ny Oh On Pe Qa Qc Qe Qh St Tz Uc Ut Vh Vq Xa) Fw(Dr Eq Fc Fd Fi Gb Gh Hl Ho Hp Op Rv Rx Ry Sh Si Sj Uw Ux Uz Va Wb Wc We Wh Yl Zw Ye Tm Tl Xa) Nb(Dr Du Eq Fc Fi Gc Gh Rt Ru Rx Rz Sf Uw Ux Va Vb Vh Vw Vz Wb Wd We Wh Yd Zw Zx Tl) Ru(Cu Dc Dr Ed Hv Ij Is It Iv Ji Jn Ke Kn Mr Nw Ny Oh Pe Qa Qd Qe Qh Tz Un Xa) Ij(Dr Eq Fc Fi Gh Gn Hl Hp Rt Rx Ry Va Vb Vh Vw Wc Zw Ye Tm Xa) Ed(Du Eq Fc Fi Gh Gn Ho Op Rt Ux Va Vb Vw Zw Zx Ye Tl Xa) Yd(Dc Ih Is Jg Ke Ko Lx Nr Ny Pz Qe Qh St Uc Uh) Xa(aW aX aY Bb Ch dK Jm Kd Nr Nx Pa Qc Ul Th) Nr(Dr Eq Fc Fd Hp Rx Rz Vz Wf Yl Zw Ye) Dc(Dr Eq Fc Gh Ry Va Vb Vw Wd Wh Zw) Ny(Du Eq Fc Hp Rx Vw Wd Wf Ye Tl Th) Jg(Eq Fi Gh Sh Ux Va Vz Wh Zw Zx) Zw(Ih Is Lx Nv Oa Pe Qa Qb) Kd(Gc Gn Uw Ux Vh We Wf Ye) Lj(Du Gb Rz Sh Ux Vb Vw We) Eq(Is Jk Oh Om Qb Qh St) Gh(Ih Is Oh Qa Qb Qe Qh) Uh(cH dJ Id Ko Qa Ri Tv) Bb(Rt Rx Vh Wf Ye) Fc(Jn Oa Qa Qh) Ye(Al Cq Jm Pa) Ry(aZ Ir Is Vq) Du(Jn Oh Pe) Fi(Ih Jk Jn) Ji(Aj Ch Jo) Wd(Is Qa Qh) Oa(Gc Gn Rx) Dr(aW Jm) Et(Aj Ch) Th(Nw Wb) Vz(Iv Qh) Ke(cH De) Uv(Fd Ho) IlWf IsRt WbaW QaWh StVa WeQh} Jj{Lj(Aa Fr Il Ir Iv Jh Jk Jm Jn Jo Lv Lx Mg Mr Mt Mw My Mz Nb Nc Nl Nm Nq Ns Nt Og Om Oz Pc Pe Pg Po Pz Qa Qd) Nn(AA Fp Ii Ir Iv Jg Jl Jm Jn Jq Js Lx Mn Mr Mz Nj Nl Ns Nt Nv Ny Oe Og Oz Pb Po Pz Qa Qd Qe) Aa(Fp Ij Il Ip Iv Ji Jl Jm Jn Js Lh Lu Lx Mk Mn Mt Mw Mz Nb Nc Nl Nv Ok On Oz Po Qb Qd Qe) Js(aA Fp Fr Ih Ip Is Jg Jl Jn Jp Jt Lx Ma Mc Mm Mn Mw Mz Nm Ny Og Oz Pb Po Pz Qd) Jt(aA Fr Ih Ip Jl Jn Lx Ma Mm Mn Mr Mt Mw Mz Nm Ns Ny Og Oz Po Qa Qb Qd Qe) Is(aA Ii Jl Jn Ko Lw Mt Nj Nl Nt Oe Og Oz Pb Po Pz Qa Qd Uh Yd) It(Ih Il Iv Jk Jm Jn Jo Jq Mp Mr Mt Nr Nt Nx Ny Om Pf Pz Qb Qe) Mn(aA Fp Ih Ii Iv Jg Jl

Figure 30 Continued

Figure 30 Continued

Figure 30 Continued cU(bF oN) hC(Bn Oe) AdKq DcRt EqdK Thlv FrNn NocP MgaX MhRh MpQz MuZq ZxKi QagP Qbi My Ng) Jv(Ax cI De Ju Ko Lj Ms Nd Nn Ri Tv) Ik(aF aW Ax dM Hx Ko Lj Ms Oa Wm) De(cA Il Ko Kx Oa oH Ri Uc Vt) Nn(Cp Hq Ii Iz Jk Mg Mv Ng Yh) Mj(Ax Ed Is Lj Mh Ms Oa Qa Wm) Pb(aW bA cI dM hB Kc Kk Ms Ri) cH(aA Ic Il In Qv Ri Ur Uu Vt) Ng(aE Hx Kc Ko Pz Ri St Wm) Tv(AF aW bL Bn Cp Ii Vs) Yd(bA cT Is Js Oa Pa Tr Yi) Ii(fN Fw Ji Jm Lj Oa Qa) Af(cX dM Kc Ko Ms Nd) Dr(Ed Jm Kd Nr Oa Pf) Hu(cI hP tN tQ tT tX) Il(Cp Hq Iz Jk My Qw) jT(Ch Jk sO wL wQ yD) oH(aW bI Ed Hx Oa Wm) Ms(aF Ic Ky Md Wm) Ko(Cp Ct Ed Iz Jt) Rx(Ih Ne Nl Ny Oa) Lj(Ic Ky Pk Ri St) qA(Hw Iq tS Tz vS) Mk(Mh Mt Pa Pf) aE(aW cI Ct iZ) hB(fP oN Ru Uy) jP(Ch cJ Ef Jk) Ax(Du Mc St) Mt(Hq oN Oz) Mz(tQ uW yH) Nb(Rt Ux Wd) aF(cI cX dM) Ed(Gn Ru) Mh(Lh oN) Ne(Ic Nl) Ij(Vh Yh) Kc(Ky Md) Ur(Ky Vt) cI(Ju Wm) fN(Ic Iv) DkJl DpVt GpeP NroN HqPa YhPe YiaZ QaJk StOa KkOi aQdM jOvT rPvQ} Jj{Uh(Ad As aW Ax BA bN CH Cp Cq cT Cu Cw Dc Dd dJ dK dM Ed Et Fw Hv Hw Id Ij Il Im In iO Ip It Iv Ji Jl Jn Jo Jq Jr Js Jt Kd Kf Kg Kk Kn Kq Ld Lh Li Lj Lw Mh Mi Ml Mr Mt Mz Na Nb Nf Nh Nm Nn Nx Ny Oa Oh Ok Om On Pb Pd Pe Pf Pg Pi Pz Qd Qe Qy Ra Rj Rm Sr Uc Uf Ul Um Un Up Us Vp Vt Wm) Ko(aM aQ aW bA bJ bN CH cP cQ cT Cu De dK eC Ed Et Hw Ij Il Im Ip Iu Ji Jl Jm Kc Kg Kn Ld Li Mh Mr Mt Ne Nh Nn Nr Oh Pi Qa Qd Ri Vq Vt) Nm(Fr Hv Hw Ii Il Ip Ir Jm Jn Jo Jq Lv Lx Lz Ma Mi Mp Mr Mt Mw Mx Mz Nc Nl Nr Ns Nt Nx Ny Og Oz Pb Pe Pf Pg Qb Qd Qe) Mn(Fr Hv Il Iq Ir Jm Jo Jp Jq Jr Lu Lv Lw Lz Ma Mc Mp Mr Ms Mt Mw Mx Ne Nh Nj Nr Ns Nx Og Oz Pb Pe Pf Pz Qb Qc) Mm(Fr Hv Hw Ii Il Ip Ir Jm Jq Jr Lv Lx Lz Mr Ms Mt Mw Mx Mz Nj Nl Nr Ns Nt Nx Ny Og Oz Pb Pe Pf Pg Po Qb Qe) Ow(Ax Bb Bg CH Dc Ed Em Et Id Ij Im Is Ji Jl Kc Kd Kf Kn Kq Ld Li Mr Mz Nn Oa Oh Ok Oy Pj Qa Qd Qe Vt) Fp(Fr Il Io Ir Iv Jk Jm Jo Lw Lx Mg Mi Mp Mr Mt Mw My Mz Nc Nj Nl Ns Nt Og Om Oz Pb Pe Pf Pg Po Qb Qe) Jn(Ih Ii Il Iv Jm Jo Jp Jq Lv Lw Lz Ma Mi Mp Mr Ms Mt Nc Nj Nl Nr Ns Nt Nx Og Om Oz Pb Pe Pf Pg Qb Qe) Ip(Hv Hw Io Ir Iv Jk Jo Jq jT Lv Lw Lz Mp Mr Mt Mx Nb Nc Nj Nl Nr Nx Og Om Pb Pe Pf Pg Pz Qb Qe Wm) Ny(Fr Hv Ii Ir Iv Jg Jo Jp Jq Lv Lw Lx Lz Ma Mp Mr Mt Mw Mz Nj Nl Ns Nt Nx Og Oz Pe Po Pz Qa Qb Qe) Mz(Fr Ih Il Iv Jl Jm JO JP Jq Lx Ma Mp Mr Mt Mw Nc Nl Nr Nt Nx Og Oz Po Pz Qa Qb Qd Qe) Ih(aA Ii Iv Jl Jo Jp Jq Lv Mg Mp Mr Mt Mw Ng Nj Nl Nr Nt Nx Og Om Oz Pe Pf Pz Qb Qe) Jl(aA Fr Ii Io Iv Jm Jp Jq Ma Mt Mw Nj Nl Ns Nt Oe Og Oz Pb Po Pz Qa Qb Qe) Lx(Ii Ir Iv Jm Jo Jp Jq Ma Mp Mr Mw Nc Nj Nl Ns Nt Nx Og Oy Oz Pb Pe Pz) aA(Fr Jm Jo Jp Jq Lv Lw Mg Mt Mw Nj Nl Nr Ns Nt Og Om Oz Po Qb Qc Qe) Ii(Fr Iv Jg Jp Jt Ma Ms Mw My Nl Ns Nt Oe Oy Oz Pb Pf Po Pz Qb Qe) Ji(bN bO CH cI De dJ Ed Gl iJ jK jO jP Jv Ky Ld Qy Ri Ur Us Vt) Fr(Hv Ir Iv Jm Jq Lw Mr Mw Nc Nj Nl Ns Nt Nx Og Pb Po Qb Qe) It(Hv Io Ir Lv Lw Lz Mc Mi Mx My Nl Ns Nu Og Oh Oz Pe Pg) Qe(Iv Jo Jp Jq Ma Mp Mr Mw Nj Nl Ns Nt Nx Og Oz Pb Po Pz) Po(Io Iv Jp Jq Ma Mw Nc Nl Ns Nx Og Oz Pb Pz Qb Qd) Ma(Hv Il Iv Jm Jq Mr Mw Nl Ns Nt Nx Oz Pb Qb) Jg(Hw Jm Jq Jt Lz Mp Mx Nl Ns Nt Oe Oz Pb Pe) Jp(Iv Jm Jq Jt Lz Mp Mr Mw Ns Nt Nx Oz Pb Qb) No(Hb Ic iO Kf Kg Kk Kn Kq Ld Ph Qv Ri Us) Et(bN cI cP De Ed Kk Kn Ld Oa Ri rS Vt) Qb(Iv Jo Jq Mg Mp Mr Nl Nt Nx Og Oz Pz) Pz(Iv Jm Jq Jt Mr Mw Nt Nx Og Oz) Ij(Ch cP Fc Hc Kc Ld We Th) Jt(Lv Mp My Ng Nl Oe Pb Pf) Mw(Iv Jm Jq Mr Nl Nt Nx) Im(cH De dJ Fi Ld Si Vq) Js(Lw Ms Nj Nl Nt Oe Qa) Is(Hc jT Kc Ld Pj) Qd(Nj Ns Oe Pb Wm) Qa(Iv Nj Nl Ns) Kq(Ch De Fw Lu) jT(Kn Lh Nx Oh) Jm(Iv Nt Og) Fw(Ld Xa) Nn(Eq Kn) Oa(Fi Rx) dJ(Kn qZ) jP(Lh Nx) rS(Li Lj) WmJq FcXa NsMp MtIv UcOf KfcQ RiVq OgOm VtbN} Uh{Ch(aA Ad Ar As BN bV Cp Cq cT Cu Cw Dc Dd dF dK dN Ed EF Fr Fy gL hB Hv Hw Im In It Iv Jh Jl Jn Jo Jp Jr Jt Kc Kd Kj Kk Kp Kr Ld Lh Li Lw Ma Mi Mj Ml Mq Mu Mw Mz Na Nb Nf Nm Nq Nt Nv Nx Ny Ok Ou Pb Pe Pi Pk Po Qe Ra Sr Ua Uf Ul Un Up Ur Us Ut Vp Vt) Ri(aA Ad aE aM Ar As aW Ax bA Bg bN bV cH Cq Cs cT Cu Cw Dc Dd dJ Dl dM Ed Fw hB Hv Hw iB Ic Ij Im In Ir Is It Iv iZ Ji Jn Jq Jr Jt Kc Kd Kf Kn Kp Kq Kr Li Lj Lw Ml Mr Mt Mz Na Nb Nf nI Nm Nr Nx Ny Oa Oh Ok Pe Pi Pk Qa Qe Ra Rj Sr Uc Ul Un Up Vp Vt Wm) Ld(aA Ad aM aW bA bN bV Cq cT Cu Cw Dc Dd De dK dM Ed Fw Hf Hv Hw Ic Ij Im In Ir Is It Iv Ji Jn Jq Jr Js Jt Kd Kf Kn Kp Kq Kr Li Lj Lp Ly Me Ml Mr Mz Na Nr Ny Oa Oe Oh Oi Ok Pi Pk Qd Qe Ra Sr Uc Ul Up Vp Vt Wm) Qa(aW BG bN cH De dJ dK dM Dr Hc Ic Ik iO Ir Jk Jo Kc Kj Kk Ko Mj Mk mZ Ng nW Ou Oy Pk Qg Qw Up Ur Us Uu Uv Vh Vs Yh) Ko(aA Aj aM aW bA Bg cH cI cT dJ dK Ed iB Ic Id Ik Im Ir Is iZ jP Jv Kn Mt Ng Nr Oa Oh Ow Tv Ur Vt Wm) bN(bA cH Cu Dc Dd dM hB Hv Ij iO Is It Ji Jn Jq Jr Kd Kf Kk Kn Kp Lw Mr Mt Nr Oh Ok Pe Uc) Tv(aE AF Aj aW BG bL cM cQ Dp eC Et Hc Ii Im Jo Mz Ou Ow Oy Pk Rj Uu Uv Vs) dJ(aA Ax bA cI Cs cT dM Fy gL hB Id Im Is iZ Ji Jq Kc Li Lj Mh Mr Mt Nr Oa Qd Qe) Aj(BA Cu Et Fy Hw Id Is It Ji Jq Jt Kf Kg Kn Kq Mr Mt Nr Oh Ok Sr Uc Vt) Id(aE Af aQ aW bG cH De dK dM Ed Ic In iO Kc Kk kS Of Ou Ow Ph Rj Ur Uu) Ji(Af aW Bg cH dK dM Gl Hc Ic Ii Ir Jo jP Jv Kj Ms Of Ou Ur Us Uu Wm) Is(Bg cH De Hc Ic Ii iO Jo Kc Kk Mj mZ Pk Qg Up Ur Us Uu Vs Wm) Kn(Af De Dp eC Ed Gl Hc Ic Ii Im JO jP jT Of Oh Ur Uu Uv Wm) Mt(bF Bg bR bS Co Hq Mk Nd Ng Ns Of oN Oy Oz Pd pF Qw Wm) Of(Ad Cp Cq Cu Dc Hw Jq Kf Lw Mr Nr Pb Pe Up Vp) Bg(bA Ij Jl Kf Kq Nr Ny Om Ow Pa Tn Tr Uc) No(aE aF bG bS eC Gb Rv Rz Uy Vs Wd Wh Xa) Im(Dr iO kF Kk mZ nC nH nL Uz Wg Yj Yf) oN(bA Cu dF Fy hB Jl Kq Mr Oh Ok Pe) Kf(De Hc Ii Jo Ou Oy Ur Uu Wm) Kk(aA De Ed Ic Lj Oa Oh Oi Wm) cH(aA cI dK dM hB iZ Oh Qd Tn) Nr(bS Jo Kc Mk Oy Qw Ur) Jq(De Ii Lj Ur Uu Wm) Dr(Cq Fw Lx Nb Oa) Uc(De Oy Ur Us Uu) Pe(Du Ho mZ Yd Yl) aE(hB iZ Lj oE oF) Ny(Hc Ii My Oy) Ow(Lj Mk Oa Oy) Ur(bA Ir Mr Vt) nW(bA Kq Ok Vt) Ax(Ic Mc Rg) De(Kq Ok Qd) Uu(Ir Sr Vt) hB(Fi Lp Uy) Wm(Mr Qd) Mz(jP lL) Nb(Tm Xa) Li(Mc Th) Oh(Ic Vt) Oy(Mr Om) aA(iO Kc) CtbA EtLj LxMk HqPa IjHc IrUs YdKq XafP KdiO OuPi VumZ aQdM} No{Aj(aE aQ Ba Bc bO cH Cv Dc Dg dJ Dl Ic Ij Ip Is Li Lu Mg Mm Mn Mt Nk Ns oH Ok Om On Pz Qd Qv Qy Ri Uo Ur Vq) Vt(aQ bL bN bS cH cJ cQ Ct dA dK Dp Et Ha Hc Ic Ik Iz Jk Kc Kk Ko Ld Me Mj nW Of oH Ou Ow Oy Qw Ri Yh) Hc(aF Ap aQ bN bS bX cE cH dK Hb Ic iO Is Jh Ji Kf Kp Kq Ld Me My Ou Ph Qd Qy Ri Tv Uo Us) Ow(bS cH Co cQ De dJ Hr Ik In Iz Jo Ko Lj Mk My Ng Nv Oe ON Ou Ph Qw Tv Vj Yh Zq) Ko(Ad Bg bN bS Cp cQ Ct De dJ Ef Ik Jt Jv Kc Kl Ks Ng Nt Of Oi Oy Ph Qw Ss Us) Ch(Ez Hf Ic Im iO Is Jg Jp Kf Kp Ld Mg oH Pj Qd Ri Sr Tr Tv Uc Us Wd) Kk(aQ Bg bN bS cH cQ Ct De Ic Ik In Iz Ji Jo Lu Ng Nv Of Oi Oy Ph Qw) Et(Bg De Ib Ic Jv Ld oE oK oN Qt Qu Qw Ru Rx Ss Ug Ut Uv Uy Vs Yh) Oy(Hb iO Jd Jq Kf Kg Kq Ld Lh Lv Lx Mp Mr Ms Mt Mw Mz Nn Qd Qy Uf) Wf(aV bQ bZ cY Fb hB Im Is Jk Jn Kd Ma Nv Qd Rh Tn Tr Ua Uc Xa) Kc(aQ bN cA cH cQ cS Ef Hb Hq Ic Jk Jv oH Qw Ss Tz Uk Ur Us Ut) Ji(De Ef Iz Ju Jv Kj Ld oE oN Ou Ph Qw Ri Rm St Up Ur Uv) Th(aF cB cC cJ cW cY Ez Gb Ha Mp Qz Vj Vq Vu Zq Ti) Ur(aE aF bN bO bS cH cP dK eC fP In Ip oH oN Pi Qv) Ld(bS cH cQ dJ Du Hf Ic Ik Of Sj Uo Us Vw Yh Ye) Ij(Hp Hr Ii Jk Lx Mk Mn Of Po Sh Vh Xa Yf) Ye(Bb bQ cY Ez Hq Ih Kd Kq Li Mp Mq Pd Pf) dJ(Hb Iz Kj oH oN Ou Qu Qw Ss Tz Ug Us Uu) My(Jl Jn Jq Jt Lh Lw Mr Mw Mz Nb Nn Nv) Ng(iO Jd Jn Kg Lh Lw Mg Mm Mn Nv Uf) cQ(Ha iO Jd jT Ju oE oH Ou Qw Ri Us) Ti(aD aE aH dF Jl Ju Kq Mf oE oF) Vj(aD aK bM cD Dc dK Gp Jy Nd Pa) Mp(Hq Mk Pd Qw Vw Wh Yd Yh Tm) Hb(cH Ii Ik In Iz Jo Kj Of Us) Mz(Hx Md Mn Nl oE oH oN Tv) Zq(aK cD Ib Jy Oh Uu Vw) Jg(Fp Hu Ms Mv Mw Oe Qb) Xa(bS gP Ib Je Oi Oz Rj) Of(iO Jd Kf Kq On Tv Uc) dR(Fc Gh Lp Ru Ry Uy Yk) Sh(bF Gp Is Ma Om Tr) Rx(Is Lu Oh Rm Vs Yi) oN(aE aQ bB bF cE cH) Tv(aE aF aW cJ Ip) We(bQ Is Kq Pd Uf) Rz(aZ Dc Nn Oh Pd) iO(bL cH Ct Ik oE) Fp(Jp Jt Mn On) Mk(Jl Mr On Pe) Hu(Jn Jt Nn Nv) In(Ic Qw Uo Us) Iz(Ap Jd Jp Kq) Sj(aQ aW Li Oh) Qd(Ha Mn Qw Us) Wd(aZ Dc Ib Om) Oe(Iv Jl Nv Qa) Vq(Hl Yj Zw Yf) oH(cH Ic Uf Us) Eq(Kq Nn Pd) Gb(bM cW Oh) Ho(cE Ug Wm) Yd(aG aW Kd) Kj(dK Kf Pj) Vb(Kd Pd Uf) Fc(aG aI) Gn(Pi Vu) Md(Jq On) Mg(Hl Yf) Ms(Lh Lw) Nk(Nc Nl) Hp(bQ cY) Hq(Lx Nd) Ii(Lh Mr) Ik(Jd Ph) Yi(aK aU) Si(Ed Ri) Zw(bQ Oh) Qw(Im Uf) Jn(Lj Mn) Kq(Bg Vw) Ru(aQ cY) Om(Vw Yg) bS(Ou Ph) DuPe EfQy EmIb LuUs MaLj MeHf NeNl YhaG YjaU JkOn JoPj KdLp UyaQ UxcW} Ow{Ch(aA Ap Bb bN bS cA Dc dJ Dk dM Ef Ex Fr Fw Gb Gd Id Ij Im Is Jg Jh Jl Jq Kd Kn Kp Ld Li Lj Mn Mr Mt Mu Mw Nl Nn Nq Ns Nv Oh Ok Om Qa Qe Rf Sr Tv Ur Vj Vq Vt Vw) Hp(aE aM aW bM bN Ct Dl Ef Fw Gl Iq Iu Kd Kf Kj Kx Ld Ma Mg Mj Mk Mm OF Oy Oz Pb Pc Qt Rf Ru Us Va Vu We Yd Yh Ye) Dr(AD aN As aU bM cI cW eF Em Fa gP iA iJ iO Iu iZ Ji kQ kR Lw Me Mf My nY oE oN Oy Vj Vu Vv

Figure 30 Continued

Yh Yi Yj Yf) Gd(aF aU aW aY aZ bC Bg bM Co dK eF Fw Gl Hv Il Im Je Kc Kd Kk Ko Kp Ld Mf Mg Nr Nt Ny Oi Pa Uv Yh) Yd(aE aF aO
Bg bQ bR bZ cL fP Gc Gz Hx Jh Jn Kq kR Ma Mv oH oK oN Pe Qd Qu Qy Rz Sj Ub Un Vt tF) Yh(aA aX cM Cu Dk Ed eF Gb Hb Hx Ij Im Is
It Iv Jl Kq Ks Mc Mr Nb Ny On Pe Pk Qa Qd Sr Un Vq) Aj(Ad cH Cu Dc Em Fc Fd Fw Id Im Is Ji Kf Kn Li Lj Nn Ok Qa Qc Rt Uc Vt) Sh(aE
aJ aV dD dL Fw Gb Gz It iZ Jd Jh Ju Jv Lx Mw Nt Nu Nv oF Pe Ur) Of(Cp Cq Cu Dc Id Ij Kd Kf Kk Kn Kp Kq Mt Om Tv Uc Vt) Oy(bA Et Ji
Jp Kf Kk Kn Ko Lx Mr Ny Pe Tv Vt) Bg(Et Ji Jl Kk Ko Kq Lx Mt Ny On Pa Qd Vt) Zw(Af Ih iZ Jl Jm Jn Kl Mr Oa Pe Qa St) Rz(Af bM hB Im
iZ Je Kq Ld Mw Nt Nu Nv) Ng(Em Et fR Ji Jp Ko Kq Lj Mt Qd Wd) Eq(bJ hB hC hG Hu iZ Mt oF Ua Uo) Vz(Bb eF fP Fw Ih Il Jn Kd Lp Nr)
Ld(Em Gb Ux Uz Va Wc Yl Ye Xa Yf) Ux(aE dD iZ Mh Nt oF Rc Un Uo) bM(Gb Ry Uz Wc Yi Yl Xa Ti Yf) Zq(aA Dg Ed Kl Mm Uu Vo Wb) Em(aA aF Je Kg Kj Kk Kl) Fd(aY aZ Bo Cq Gl Iq Uv) Xa(aY Co fP Gl Kg Lv Uv) Lp(Bo Cq dD Iq Jo Ur Uv) Va(aE aY bO fP Hb St Uo) Du(Cs Fp Hv Lj Me Oa) Rv(aY Co dH iZ oF Sr) Rt(Af fP Hv Ij Me Sr) Gb(aZ Dg hG Kg Uu) Ko(Hc Iz Jo Lj Vt) Af(Vc Yi Yk Yf) Lj(Et In Oe Vt) Ny(Ct Hc Ib Yg) Vj(aA aX Ed Nb) Fc(aZ Hx Pi) Yi(aA aZ Kg) Sj(bN hC oH) aY(Op Uz Zx) iZ(Wf Wh Ye) Ct(Id Kn) Ed(Yj Yf) Th(Ij Iv) Mk(Kk Lx) Hl(Oa Sr) Yg(Qd Wb) Jo(Ji Kn) Kg(Ho Yk) Vt(bN Ur) aA(Yj Yf) fP(Gh Wd) CoMt FaWb HqJl TvcH HcKf OifR VchB} Im{Wf(aA Ad aG aM An Aw Cp cQ Cv Cw Dd dN Dr eF Em Et Gb hB hC hG Hw Ib Ij In Ir Iv Jh Jl Jo Jt Kd Kn Ko Kp Kr Li Lw Md Mi Ml Mq Mt Mw Na Nb Nf Ni Nm Nr oF On Ou Pd Qx Ra Rb Rj Rt Sr Tr Ud Un Up Us Uz Vh Vv Wc Wg Yi Yj Zq Tl Yf) Aj(Aa aE aN Ap aQ As aW Bb bC cE cJ cL Cu Dc De dF dJ Fc Fd Fr Hl Id IJ iO Jo Jp Jq Kf Kg Kn Kp Ld Li Ma Mr Nd Ne Nn Nx Oh Ok On Rt Uw Uz Vq We Wg Wh Yl Zq Tl Xa) Sh(dR eF Fb fP gL gP hB hC iA iP iZ kR kS nW nY oE oF oH oK oN pF Tr Tt Vu Vv Yg Yh Yi Yk Yf) Ch(Di Hb iO Is Jd Jp KC kE Kf Kk kN Kp Kq Ld Ma mF Mn Mt mW Nn oH Tv Vj Yj) Eq(aQ aZ Cu Cw De dR Et gP Ho iO iP iZ kR Lu Lv Ma Nu oE Ou Oz pF Qv Vu) Zq(aG aJ aR aX aZ bS Fr Hc Hu Ib Iz Mu Qt Qu Qw Qy Qz Ug Uu Ux) We(Ad aG Hc In Ji Jn Mi Pd Uc Ug Un Up Uz Vu Vv Yg Yi Yk Xa) Ux(aG aJ aK bC cY Dc dR Et gP iJ iP Li Mi Mp Mt Nn nY oE Qv) iP(cH Du Fd Gc Ho Hp Ry Sf Si Sj Uw Vb Vw Vz Yd Yl Zx Tl) Ji(De Ef Fc Hc Jv Kj Ld Qw Us Vz Yd Yh Th) Dr(Ef Ib Iz oE oF Or Rg Ss Tz Uu Wm) Ld(cH Fd Gb Gc Rt Uz Wb Wc Yi Yk Xa) Uu(Gb Gc Uz Yg Yh Yi Yj Yk Zw Yf) Vj(aX bS Dc Dp Hu Ik Qt Qu Qw Vt) Fd(Af aJ bP bX Dk Oi Rx Ua) Xa(Bo bX fP gP It Iz Mw Vt) dR(Fc Rv Vz Wb Yd Yg Yh Ye) Ib(Rt Uw Uz Wg Yj Tl Yf) Yi(aG aH Bo bS Qw Rj Ug) Ur(kE kF mE mZ nI nK Vh) cH(cI iO kC kO mF oH oP) oF(Hl kC kN kO mF mU Ye) Hc(Hl Ho Kf Ry Vh Wc) Yg(bP Dc Fy Is Lx Qh) Yj(bS Hb Hu Mw Qt Qw) Ug(Fc Gb Ru Ry Yk Tl) Yf(aH bS gP Hu Qw) Kj(kC KO mF oP) Hl(Cq Mi Oy Up) Is(Aa Vz Yd Yh) Wh(aG aZ Cw Pd) Ye(nW oK Ri Uk) Vb(aG Cw Dd Ij) oE(Gb Rv Wb Zw) De(Et Kk Mt) Du(aJ gP Pe) Ng(iJ iO Ko) Yh(Lu Lx Oh) Yk(aH Bo Qv) Wd(aG Hu Mi) Tl(aH bP Oz) Yl(bM cT Pc) Oy(Kf Vh Wc) Et(Bg Ef) Th(Li Oz) Hp(Dd gP) Iz(Ho Ko) Wb(aU Oh) Sf(gP Hb) Sj(Oi Oz) Kk(dJ Oi) Rx(cT Dc) Rv(aG Qx) Uz(bX Rj) AaOe CqLp GhbP GbMy IjVz SiaH ZwJs WcQv QwUw JoKo RtPg VwcI nKkC} Is{Rt(Ad AF Aj An As Ax bA bM Bn cH Cp Cq Cs Cu Cv Cw dA Dc Em Fc Gb gL Gn gP hB hC hG Hl Ho Hw Id Iv Kd Kn Kq Lj Lw Me Mi Nt Ny oE Pe Ph Ra Rz Sh Ub Up Uz Vt Wg Yh Yj Yl Xa) Oy(AA Ip It Jn Jt Lw Mp Mr Mt Mw Mz Nj Nm Nt Nx Ny Om Oz Pc Pf Po Pz Qa Qd) aA(Fp Fr Hu Jg Jn Jp Jt Lw Lx Ma Me Ms Mw Mz Nm Nn Ns Nv Ny Oz Pb Pz Sh Wf) Aj(Ad Ba Bb cH Dl iO Jg Ji Jp Jt Kc Kf Kg Kk Kn Ld Li Mm Mn Nn On Vq) Ms(Aa Fp Fr Ip It Jn Jt Lw Lx Ma Mt Mw Mz Nj Nm Nv Ny Oe Oz Pb Pz Qd) My(Fp Ip Jn Jt Lw Ma Me Mg Mw Mz Nb Nj Nm Nt Nx Ny Oz Po Pz Qd) Nj(Fp Fr Hr Hu Ip Jn Jp Lx Ma Mw Mz Nm Nn Ns Ny Oe Pb Qd) Lw(Fp Hr Hu Ij Ip It Jn Jp Ma Mz Ng Nm Ns Ny Oe Oz Pb) Hu(Fp Ip Jn Jp Jt Lx Ma Mm Mn Mt Mw Mz Nm Ny Oz Po) Yd(aF aY bG bN Bo Hc Kq Li Mj Mt Of Pc Pe Pj Sh Zq) Oz(Aa Ij It Jg Jn Lz Mm Mt Mw Mz Nm Nv Ny Pf Qd) Yh(aF Ar bJ Bo Ed Iv Kz Ld Mq Nf Nn Pe Sr Us) Pb(It Jg Jn Mt Mw Mz Nm Ns Ny Pf Po Pz Qa Qd) Ch(Ap Hf Ic Ji Jp jT Kc Kq Nn Sr Ur Us Wb) Ns(Ij Ip It Jn Jt Mt Mw Mz Nm Oe Po Qd) Ng(Ij Jp JT Lx Ma Mn Mt Mw Nm Ny Pz) Sh(aE aZ dI hB Iq Jq Ld Nb Ny Uo Wb Zw) It(Fp Ij Ip Jg Ma Mm Mz Nv Oe) Ld(cH dJ Fc Ux Vb Wf Yg Ye) Mk(Fr Ij Lh Lx Mp Nv Pe) Zw(Ar Dr hB Iv Nf Oa Pe) Ko(Bg De Hc Jo Kj Of Uu) Oe(Aa Ip Iv Jl Mw Po Qa) Mz(Jg Jp Lx Ma Mm Mn) We(Bo hG Mq Nb Ny Pe) Aa(In Jo Li Lu Og) Et(Bg cI Dc Ef Hc) Eq(hB hG Nn Qz Rz) Fp(Jg Jp Ma Mn On) Hr(Ij Ip Lh Nv On) Va(aY Bn Ed hG Wf) Hc(Dr Jp Wb Xa) Ip(Ma Mn Mw Nn) Zq(Af aY Gl Kj) Jg(Jh Mw Of Oi) Ur(mZ nL Ru Vt) De(Ji Li Vj) Ed(Fc Rv Xa) Hx(Ij Lh Nv) Jk(Fr Ij Nv) On(Jh Mv Mw) Dr(Oa Uu) Du(hB Mf) Jo(Lh Pj) Ye(hG iZ) Kc(dJ Ph) Oi(Fr Nn) Us(Ji lX) aY(Sf Vw) cH(iO Tv) BgWd PoLx NuWf MdNv MmJn NcNk NeNl UcOf IjIk WbLi VzaW SrRv RxhG UvVj UuUx PdPf nInK} Mz{tL(aI aO bN cK eD eZ fY hA hL hO hP hW hX iB jD jF jG jH jI jK jL jM jO jP jR jT jU jY Kc lK lL lM lN pF pY qA qB qC qD qU rC Ri) yH(aC aO bN cK dH dK eZ fY hL hO hP hW iB jG jH jK jL jM jO jP jQ jR jT Kd lL lM pY qA qB qC qD Ri) hR(cH qA qC rO rS rT rU rW sC sK tO uG uO uR uV uW uX uZ vA vI vP vS vW wC wJ yJ zA zH tM xA) wB(aH bB bJ bX dA Dk dL eC eT hA hL hV hX jF jL jT lK nW oK Ph qB Qt qU Um) Qy(rO rS rT rU sO uL uP uR uT uU uW uZ vB vH vI vO vS vT vU zI tM xA) Og(Fp Fr Ih Ip It Jn Jp Js Lh Lx Ma Mm Mn Nm Nv Ny Om Pz Qa Qd Qe) aA(Fp Jp Js Lw Lx Mm Nl Nm Nn Ns Nv Nx Ny Oe Pb Pz Qa Qb Qd) hO(Bg Cq Ct Ef Jk Mk Mv Mw My Of Om Oy Qw Tz uG uW vI) eZ(Bg Ch Dk Ef hX Iz Jm Mq Mv My Nq On Ua uI uR wF) qC(Ch Cq hV hX Mk Mw Ng tU Ua uG uR uW vB vI wF zH) vI(aM aY hW Ic jF jH jI jL jT lL Oe qB Rg Um Un) Lj(Ip It Jg Lw Ma Mi Ml Mn Nl Nn Ns Oz Pb Pc) qD(Ef Jk My Of Qw sC uG uI uR uW vB) rO(Bn Ch hX Il Jk Mx Qt Ub Ur Vv) vS(cK hA hP jL jY lK lO oN pF rC) wE(hA hP jL jY lK lO oE oN pF) rW(Bg Ch Ct Ef Il Jk Jm My uW) Ok(Hx Md My Nc Nl Oe Oy Oz) rU(Bg Ch Cq Ct Ef Il Iz Jm) jT(Bg Ct Ef Ng Qw Ua uR) Ch(gL hB iA jI jU Tv) jO(Bg Ct Ef Ji Nl Ua) lM(Cp cQ Ct Ef Kc uR) On(Md Mv Nl Of Pb) cH(hV hW hX rY sM) hP(In Iv rX wG wJ) rV(Bg Cq Ct Ef Jm) Nn(Eq It My Oy) sO(bP cW hV lK) jU(Bg Ef Qw Ua) zA(hA jL oN Or) uR(dL qO qZ Uf) uW(aM bF bN cE) Dk(qZ rN tQ) It(Fr Jp Lx) Jg(My Ng Oy) tU(eC jI lL) lK(uL uT wK) Li(Du Th) Oy(Lx Nv) wD(cW hA) lL(Ua uI) oN(cE wJ) AjAp FpJt NsMp NtrS MtMy TvUs KchV LduI aMwF aWiH aYuT cKuL cLmZ wKoE tNqZ yJjL jFtM qYvB qWvV} Ji{jT(aF Aj AO AW aZ bL bN cE cO cS dJ Dk Ez Fr Gl Ib Jd Je Jh Jm Kj Lj Mk Ml Mn Ms My Ne Ng Nl Nq Oa Om ON Ou Oy Ph Ql Qx Uk Up Ur Us Vu Tj) Aj(Ad aW bA Bb bN bO cH cI cT De Dg dJ dM Ed Fr Jg Jt Jv Kc Kk Li Mg Ms Mt Nk Nn Qd Qy Ri Uc Us Vq Vt Wm) Ch(aQ bA bF bO cE cI cL cT De dM Ez Fb Hf Ic Id Ik iZ Jh JO jP jR Ju Jv Kc Kq Li Mn Ms Mt Na Nn Nq Oe) De(aA aM bA bN cT dM Ed Et hB Ik iZ Jo Ju Jv Kc Kk Ko Ld Li Ms Mt OE oF Qd Qg Rb Ri Uc Ur Us Vt) Us(aA aE An Bg bN cH dJ dK dM Ed Fw Hc Id Ir Iu Jo Ju Jv Ko Ld Lj Mr Ms Of Qg Tv Ur Vt Wm) Ld(Af Bg bN cH dJ Ed Fw Hc Hf Ic Ii Ik Iz Jv Kj Ms Ng Oi Oy Qw Ri Ur Uu Uv Vt) Jo(Aa bA bN cH cI cT dM Ed iJ iO jP Jv Kc Kf Kk Ko Qy Ri Tv Vq Vt) bN(aA cH Gl hB Id Ik iO iZ jD jO jP Ju Jv Kj Kk oF Ri Uv Vt) jO(aQ cH cJ Ic Iz jE jF jK Jm jP jQ jR Li Lu Mx Nl Ph Vv) Ed(dJ dK Fc Gl Ii Ik In Kk oH Rt Ru Tv Ur Wc Ye) jP(bL bS cJ dJ Ef Hc Jm lN Ou Ph Qw Tz Ua Uk Ur) dJ(aA cI hB iZ Kj Kk Qw Tv Uu Uv Vt) cH(aA bA dM iB Ii Ik Qg Ri Ur Uu) Bg(Et iJ Ik iO Mt oF Qy Ri) Ms(Aa Ef Gl Jv Kj Qw Qy Ur) aA(Af bO Hc iJ oN Ph Th) Aa(Ii It Jq Lu My Oy) Kj(dK dM Et Fw Ko Ri) aW(hB iH iZ oE oF Tv) Jv(cI dK Kk Ko Ri) Of(Kq oF Qy Ri Tv) dM(Ef Hc Ik Iz Ur) oN(cE dF dH hB oF) Ng(iJ iO Qy Ri) aE(hB iZ oE oF) cI(aQ Et Ik Ju) Hc(Et Ko Ri) Ur(Fw Tv Vt) Oy(iJ iO oF) Dr(Oa Ru) Ef(Et jR) Th(hB Li) Ii(bA Vt) Ik(Af Cx) Yd(Nv Pa) wD(bL Nd) CpjR MtQw NbZx YhQa ShaY KoUu LphG RiPh NveZ VtdK cQhB} Og{Jg(Fr Hu Hv Ii Il In Ir Jm Jp Jr Jt Lx Lz Mi Mn Mp Mt Mw Mx My Nb Ng Nm Nx Ny Om Oy Oz Pa Pe Pf Qc) Nn(Fp Hu Hv Ir Jl Jm Jn Jp Jq Js Lw Lx Mn Mt Nb Nj Nl Nm Ns Nt Nv Nx Ny Oz Pb Pe Po Pz Qa Qb Qe) Lh(Fp Fr Ip Ir Iv Jl Jm Jn Jp Jq Js Lw Lx Ma Mm Mn Mr Ms Mt Mw Nm Ns Ny Om Oz Pb Pz Qa Qb Qe) aA(Fr Ih Ii Il Io Ir Jl Jm Jo Jp Jq Lv Lw Me Mg Mr Mt Mw Nj Nl Nr Ns Nt Om Oz Pb Po Qb Qc) Qa(Aa Fp Fr Ih Ip It Iv Jl Jn Jp Jq Lw Lx Ma Mm Mn Mr Mt Nm Ns Nv Nx Ny Om Oz Pb) Qd(Aa Fp Fr Ih Iv Jl Jn Jq Lw Lx Ma Mm Mn Mr Mt Mw Nm Ns Nx Ny Om Oz Pe Po)

Figure 30 Continued

Figure 30 Continued aN aQ aX cP dI Dr Du Fc GI HI iZ Je Jn Jq Lh oF Qy Wb Yd Zw) We(aD aH aJ cE cP Cx dG dL Dr Ed Ex Fc Ko Nt Om Oz Rx Uv) Fc(Af aJ
cF De dR fP HI My oH Qu Qw Sh Ua Ux Vj) Hc(Dr Et Gn Kk Ko Op Rx Vw Wb Yj Tl) Zq(Af Ao aX Bg bM Eq KI Ng Uu) Ye(Af Bo dD iZ Jq
Lh Nu oF Ok) Oe(Aa Jg Jp Jt Lh Nn Nv Pb) Bo(Fi Uy Uz Vc Vw Wg Yg) Rt(fP gP iP nY Oi Ua Ur) Aa(Jo Lu Mk Oi Oy Ti) Hl(Bn fP gP Ib Qw
Uk) Eq(bM Dd Jh Kq Qy) Ok(Jo Mj Ng Of Oz) Vj(aX aZ bM De Ex) Dr(kQ Qw To Th) Jg(Ik My Ns Oy) De(Gb Kc Rv) Th(Li Oz Un) Sh(aY
cP Us) Ko(Jo Kj Of) Rx(fP gP oH) On(Hr Jk Pb) bM(Yg Yi Yf) Af(Sj Wh) Yd(Oz Rj) Zw(fP Oh) Ux(aD Bn) aX(Rz Wd) DkHp EdGn YfaZ
TiLi FpIk NsMp LxOy MtMy NgJt ItJp WbQw SiUu WcUv KkdJ LpUr RvUs YlaD UwaJ} Lx{Oy(Aa Fp Fr Ih iJ Ip It Jh Jl Jn Jp Js Lh Lw Ma Mm Mn Mr Mt Mw Nm Ns Ny Om Oz Pz Qd) Wb(aO Bg cH Dk Fc hB Hc Ic Jl Jm kQ Li Lu Lv Mj My Nx Oi Or Wf Zw Zx) It(Aa Hq Iv Jl Jp Jq Jt Mn Mr Ms Nn Ns Oe Oz Pb) Zw(Af aY bN BO dD dI Ed Hx Ih iZ Mh Nv oF) Fc(aE Af dD fR Hx Mh Nb Nu Oz Rt St Xa) Yd(aG aN Dl Dr Jk Jt Ko Kq Mt Nu Un Vj) Pb(Ip Ir Iv Jl Jt Lh Mr Ns Oe On) Dr(Ic kQ Ky Lp Qn Rg Ru Us) Oe(Ih Iv Jg Jl Jt Nn Qd) Ns(Hx Jl Jt Mh Mp) My(Jt Mt Nb Nn Nv) Hp(aD aW aY Kd Uv) Yh(aS bJ cO Hw Qd) Rt(aE Dd Ih Mw Ny) Bo(Fd Lp Ry Uy) Ok(Hq Hu Ng Po) Du(aS hB iZ) Zq(aY Ed Gl) bM(Fd Gh Yf) Aa(Jo Oz) Ng(Jg Jt) Vz(aW Bn) Wf(Je Qy) Uv(Rv Vj) hB(Vc Tl) AfFi EdYf GlVw HqOn IpOz ShNy RxiZ VjaX} Kq{Rx(bF Bg EF fP Fr gL gP Hc iA iO iP iZ kQ kR Mv My nY Oa oE OF oH oK pF Wf tF) Eq(aD Ap Bb cD Ex Gp Ho Ic Ih iO Jm Jn Kd Li Mt Nr Nt Oa Or Tt) Of(cE cH Cq De dJ Et Fc Jp jT Kk Ko Lp Nv Oh On Pa Tv Tm) Th(aY bF bG bZ Dr Hq Iv Iz Jy Li oE Oy pF Sh Uv) Fc(Ao Bg dR Ef fP gP Hc Li Mv My oE oF oH) Wf(aN Gl Il Jm kQ Nb Nr Pa To Vs) Ru(Ao Dk Ed fP iP Mv oH Qw Ut Ux) kQ(Gd Ng Uw Ux Wd Wh Ye) We(Al Il Jk Lp Mx Pa) Yd(aZ fP iZ Lu oE) Sh(Dd Ed Il Jv Nr) Lp(Dk Fr iP Mv Qw) Uy(fP hB iP nY oH) De(Et Kc Kk Tv) Xa(Ef fP My) Bg(Du Yi) Ti(Li Oa) Fd(Us Uv) Yh(Js Oh) Wd(Ed iZ) iO(Gn Ye) DuLi YgOa SiUu ZxaZ TmfP JyRt KjKo UvVw UwkR} Ed{Yi(Af aG aH aZ bM Bn Bo bX CQ cW Cx dR Gn Hb Hc Hl Ii Ne Oz Pa Pc Rt Ug Ur Uu Vt Yl) Xa(aQ bF bS cE cQ Cu Cx dK dR Ez gP Hb Ib It Kx Lu Ma Nd Oh Op Oz Qw Rj Tr We Wf Ye) Et(De Fc Hl Op Sj Va Wc Wh Yh Ye Th) Zq(aQ BA bQ cT De Di dR Ki Oh) Dr(aK aQ aU dR Kk Mp Om) Oh(Sh Si Vj Wb Wd Yj) Gn(On Vu Vv Yg Yh) Vj(bA cT Fy Ir Rm) Ba(Gc Ye Yf) Tr(Hl Rt Va) Si(bQ hB Ni) Sh(Jg Ma Rm) Uu(Uw Yg Yh) Ti(Li Oa) Ez(Fi Yl) Gc(Nb tF) Wh(dR oE) Wf(Ih Mr) Ko(dK Vt) Ru(aQ Mp) Vw(aQ dR) CuFc EqPd GboF NbOp YgOz YhYe YdLi WdoE KkdJ YlPf UrVt VhhB} Oa{Vj(Af aZ bM Bn Bo cD Cx Dd De Du Fc Fw Ip Ne Rj Rx Us Uv Vq Zw Tl) Rx(Ba bO cE Dd dI Du Gb Hb Hx Nb Ny Ur Zq Xa Yf) Dr(aU aW Bo Et Gn Ic Kc Kd Li Mp Mt nW Om Uf) Ti(Af Ar aZ Bo Cv hB Id Oe Oh Qd Un Vt) Zq(Af aH aX bM Bn Bo Cx De Ip Oe Qw Uu) Du(aQ aU Dd dR Et Gc Li) Hl(aW Ic Kd Mg Nm Pd) Ye(Jd Jh Mt Mw Nt Qy) Gc(Af Cv hB hG Wb) Gn(Cw Hv Mi Vu) Bo(Yg Yh Xa) Yj(aW Dd Rj) Si(cE hB hG) Wf(Jd Mt Nt) Eq(aZ Rz) Wb(Pj Vq) Ur(Fi Zx) aG(Yh Yk) CvFc CxGb DeEt ShgL RvPf RuUn tUnW} Ok{Ng(Fp Fr Jp Lh Lw Ma Mn Mp Mr Mw Nc Nl Nr Nv Ny Pb Qb Qd) Oy(Fr Jl Jp Lz Ma Mc Mi Mn Mr Mw Nb Nc Nl Nr Oz Pa Pg Qe) Jo(Aa Jg Jt Ma Mm Mn Mp Nc Nm Nr Ny) My(Jl Lw Ma Mc Mi Mp Mr Nq Nr Ns) Of(Jg Jn Mp Nc Nl Nm Nv Oz Qb Qd) Oz(Fr Lz Mc Mt Nl On) Mk(Mp Mr Nd On Pa) Mt(Hx Md Mv Ns) Mc(Js Nc Oe) Pd(Mp Pf Pg) Ns(Lz Ma) Mr(Hx Ii) Nc(Ip Nk) Hq(Mp Nd) Hu(Fr Nv) Qd(Hr Mj) Oe(Mn Mw) ThLi MdJq MsNv NeNl IvrW JgOi} Ny{Wf(aP CO cS Cu Cw Ez gL Ih Io Mk Mq Mr Mv Om Pd Po Tn Uf Xa) Rx(dR fP gP iH iJ iP iZ kS nY oE oF pF) Ye(Ap aW Ez gL Mg Mq Nn Pd) Sh(dK Hq Ma Mt Pd Pf Ph) aW(Hl Si Vw Yg Yj Zq) We(Jo Mg Mi Om) Eq(Ap Co Uu) Ib(Rz Zq Xa) Ur(Ho Wh Yk) dR(Fd Rt Xa) Cw(Rt Yd) Th(Nn Uf) Fc(Kx Oh) My(Mt Rz) Ng(Jg Jt) Hc(Et jT) Lp(dK Kd) Vj(cD Pa) nK(mF oQ) TiVt NsMp HujT WdLi XaVq KoOf} Nn{Eq(aO Bg Dc Ef Hq Jl Jn Mj Mp Mq Oh Ou Pg Pi) Sh(aG aZ Ba bM cF Cu Dd Fr Fw Hb It Pg Un) Oy(Ih Ip It Iv Jg Jl Jt Lh Mr Mt Nb Nv Po) aZ(Op Ux Vz Yh Yi Yj Yk Yl) It(Hu Iv Jl Jp Ms Ns Oe) My(Jg Jt Lh Mr Mt Nb) Oe(Ih Iv Jl Jn Jt Qd) aX(Rv Vj Yh Yj Zq) Ip(Hu Ms Oz Pb) Ns(Ih Jt Qd) Wf(aE Jl Jn) Ms(Ih Jt) Ng(Jt Ko) GbVt HuNv WbQu} Nv{Oy(Fp Ih Ir It Iv Jg Jh Jn Jt Lh Lw Lz Mn Mp Mr Mt Mw Nb Ns Oe Po Qd) Ns(Fp Hu Ih It Jn Jt Lz Mp My Ng Oe Oz Pb Qd) It(Fp Hu Ik Jt Ms My Ng Oe Oz Pb) Oe(Fp Hu Ih Iv Jn Jt Oz Pb Qd) Uu(Gb Sh Uw Vc Vh We) My(Jg Jt Mr Mt Nb) Fp(Hu Ik Pb) Sh(Af oE Oz) Eq(Co oE) Hc(Ru Va) Wf(Ih Jn) NgJn ZxOz JoJt UrmZ UxPd} On{Jk(Fp Ih Ip Iv Jl Jn Lz Mr Nl Qd) Of(Fp Ip Mr Mv Qd Tv Uc Yh) Iv(Hr Hx Ii Jo Mk Oz Pb) Lz(Hq Ik Ip Mk Oz Pb) Oz(Fp Ih Ip Mv Qd) Mk(Jl Mp Mr Pa) Hr(Hv Ir Jn Jt) Oi(Fp Ih Jn Qd) Pb(Ih Ir Jn Qd) Mr(Hx Ii Mv) Eq(aW Om) Th(Bg Qw) Nl(Ne Nk) Yh(bG dR) Jo(Ip Jt) AdnK DcRt WmNg FcUu MdJq MpHq MtMv YddR ShaY QcQd XafP RxoH PdPf cHoN} aZ{Yi(aF Ap aU aW bC bE bJ bW CO cS cZ De dN Ez Fc Fi Gc gL Hf Ho Hv Iv Jd Jh Kc Kd Kg Kj Kz Li Mg Mi Mm Mp Mq Mt Mu Mw Pd Pj Qd Qy Rh Rz Uf) Zq(Fw Ih Ks Nb Qe Rm Sr) Li(Eq Hp Rx Ry Vz Yd Yh) Ru(Jd Kz Mq) Qe(Rt Vj) Sr(Fc Uw) MqUy NbVj IhVa YkUf XaRx KkVq} Oh{Wb(aO bF bR bS cE Dd Gb Gc Gp Ih Kc Li Lu Oe Oz Pc Pd Pi Pj Rx Si Um Vt Ti) Zq(aY bM Dg Gl Kl Uu) Yh(Jh Mu Qd Qy Vu) nL(aE aF Mf mU) Bo(Fd Gb Vc) Dr(Kk Qy Rx) Eq(Jh Mq Om) Fc(aY Oz Pi) Vt(bN dJ Ur) Ti(aY bM) Zw(Qd Qy) Li(Rt Th) nC(aE mU) GbUu GlVj MwWf HobM UcOf KkdJ aFmZ nKkC} Nb{Zq(aX Bo cR Eq Ng Oy Rz Ss Uu Ux Wd) Tl(aK bM Dc dR gP iP iZ Je nY Qt Vt) Bo(Sj Vh We Yg Yh Yi Tm) Ti(Ar hB Id Li Of Vt) Wf(Et Jn Mq Oz Un) Mp(Ru Ux Wd We) Mq(Eq Wd Ye) We(Mv Om Un) My(Fr Jg) Si(oE Ur) Ye(Ih It) Vj(aX Zx) EqOm FcJs GbOy ShRm TmpF LpUr RtcL} It{Jp(Aa Fp Ih Ip Iv Jl Jq Jt Lh Lz Mp Mr Ms Ng Oe Oy Oz Pb) Fr(Hu Ih Ik Iv Jq Jt Mn Ms My Ng Ns Oe Oy Oz Pb) Lh(Ih Ik Jo Ms Ng Ns Oy Pb) Fp(Ik Jl Jq Jt Mm) Jl(Mn Ns Oz Pb) Aa(In Jo Li) My(Jg Mt) ThLi NsMp MnMs NgJg} Li{Th(aH Ax bA Bo cT Cu Dd Et Fy Hb Hf Hx Ir Iv Jl Jq Js Lv Mj Mp Mq Ms Mv Nu Qd Qe Qh Qn Qu Rc Rm Sr St) bM(Fd Sj Yi Zw Ti) Aa(Jo Ns Oy Oz) aX(Rt Rv Yh Yj) Eq(cE Hq St) Ti(Jl Qd) rS(Fp jT) AfFd DeEt DuJl WmJq} Jg{Ng(Fp Fr Ip Iv Jl Jn Jp Jt Lw Lz Ma Mn Mp Mr Mw Po Qb Qe) My(Fp Ih Ip Jl Jq Js Lh Mr Po Qb Qd Qe) Oy(Fp Ih Jl Js Lh Mp Mr Mt Po Qb Qd) Oe(Fp Jl Js Qb Qd) Ns(Fp Ih Mp Qd) Ih(Fp Ms Oi) FpIk} Vt{bN(dJ Dp Et Kk Kn Kp Me Mn Ri Tv Ur) nW(cH sO uT vB vH vP vV yL xA) Et(De Jo Ng Of Ur Us Uu) Ur(Ir Iu Kn Ko Nr Tv) Wf(Ih Jn) Xa(aN Fc) Ko(dK Of) cH(oH Tv) jT(uN yK) vV(jR qO) MtOy UcOf YibM JnRx KndJ cWvP iPvS} Qd{Oe(Fp Ih Jl Jn Jt Lh Ma Oz Pb) De(bA cT Et Kf Kk Ko Mn Tv) Ns(Lh Mn Mp Oz) Oz(Ip Jl Mr) Ik(Ma Nt) Yg(Nr Yi) Yh(cT Js) Lh(Oy Pb) Ru(fP Iz) aW(Eq Sh) jT(Kn pS) AaLu DknC EfEt MnMs MtMy NgJt KkdJ OpUu cHoH} Ih{Fr(Ms Ng Ns Oe Oy Oz Pb) Ma(Fp Ms Ng Ns Oe Oy Pb) Lh(Ms My Ng Ns Oe Oy Pb) Fp(Jp Jt Mm Oe) Jp(Ms Ns Oe) Ye(hB Iv Mq) Sh(Hq Ju) Jt(Ng Oe) BoUw DroF GcUu MmOe MnMs MtMy UrmZ} Mt{My(Fp Fr Jn Jp Js Jt Lh Mn Ns) Eq(bG bI Ng Om Oz Vq Vu) aX(Gb Rt Vj We Wf Zw Zx) Oy(Aa Jt Kf Ko Lh) Et(Bg De) AaOz FrVb NgJt UcOf JoKo XafP UxcH} Om{Eq(Ax Bo Cs Cu hB hC Jl Jn Jv Mr Ni Nr Pf Qx Ra Ru Rz St Yd Wm) Sh(Af aY bL Bo Mw) Dr(Kl Uu Vb Wd) Uu(Wb Yh Zq) BgYd HcRu WfOy YeiZ} Et{Of(bA Id Kn Pi Tv Uc Up) iZ(bN cH cP cQ dJ eC Ri) Jo(Aa Kd Kn Pi Tv) De(Kk Qe Tv) cI(Bg cH Oe) Xa(aY fP) AaLu BgOe PoMv ThIv IdUu HcbA KreP} Id{jT(bL cQ Ct Kj Ng qH qI rZ) dJ(rS sM sO uG vA wB) rS(Fw Of Or uR) vS(cS Jh Jk uR) nW(wD wG wP) Ph(uU wP) bN(cH uR) HwrR OrwC qPvV} Vj{Pa(bM dJ Dr Hf Hp Iv Pi Uo Wb) Pi(aN aW aY Fw Jm Ru Th) Fw(aX Hx St) Ru(Fd Hf Me) fP(Jn Pf) DcNu ThHa GlJs JlaY RmUu} Jt{Fp(Hr Hu Ip Jo Jp Ms My Ng Ns Oe Oi Oy Oz Pb) Ng(Ip Jl Jp Lh Ma Mp Po Qb) ArTh FrOy NsMp QbOe JoLh} Wf{Jn(bH bN cO Fw hB Iv Jk Jl Mq Ni Qy Ri Rj Wb Wh) Mw(Fy Jl Jr Js Tn) Fw(Hx Mr) MrPa UvUt} Aa{Lu(Jl Jn Oz Qb Qc Qe) Qc(Jo Mk Nc Oi Oy) Qe(Jo Mk Oe Oi Oy) Qb(In Oe Oi) MkOz HuuY} jT{Kn(cH Dp eD Jk Kj Ml Of Oy Ur) Fa(Ef Jk Oy) Ko(uP vU wL) Lh(Ct Qt Vu) Un(cQ Of)] Zq{Gd(Fw Jm Pa Ru) Uu(Dc Rm St) Dg(cT Pf) aX(Ar gL) CqKj EqbQ ThIv FwQv GlJs YddR} Sh{Fw(Fa Kz Rm Tm Xa) Dd(Lz Ml Mq) Rm(aY cE Ri) Ut(Jv Uv) DrPf JncL} Xa{Ar(aW Kd Ru) fP(cU Sr Ut) Un(aY Jm) Vq(hC iH) aX(Kd Mg) FcTz SrgP} Mq{Ye(Jn Kd Lp Pa) Dd(Ry Vb We) Eq(Dc Jk Jm) JmUx LpbP} Of{Uc(Hb In Jp Kk Kn Ko Nh Pa Sr Us) TvPg dJqZ} nW{qZ(jD Up Ut Vu) Ko(wD zA) wB(Fn Kr) UbrN OrwD UncH aWrS} Bo{Yi(aY Di Fw Ha Nd Ne Sr Th) Js(Yh Zw) CxFd} Pf{Dr(Ha kQ

Figure 30 Continued oN) Wb(bG fP oE) Vz(fP iA tF) EqJd HpfP} Js{Yh(bE Jd Nq Vu) Rt(Cx gP) FcOz FrNg VzaW} Ur{Kn(dJ jO) Lp(Cu Vu) FdJn TvcH RmmZ PanI dJqZ} hB{Dr(Il Kd) EqKd FdaY MvUy SiVa RuUn VbVq} dJ{Kk(Qe Tz) Kp(rW zG) NgvI KnjO RfrS} Ns{Mp(Fp Jn Jp Lh) Fp(Jp Mm)} iP{wD(jU Jv Kc) MurN aWrS iBvS} Fr{Oz(Ip Iv Ng) MrOy IvPb} Ko{Jo(Fw Kn) KjdK cWzA hOrS} Ru{CuUu DrPo QebM JdaX KzUn} Ms{Lh(Jn Mn Pb) MnIp} St{CwVb EqMg RxoF cLmZ} aW{CuUx YiKg VzJn rBrS} Th{Ar(Qe Tz) AxUn} Ic{KnjO KrwB dHuI} Sr{VzaU UuUw cHoH} Rt{Dc(Iv Mw) CxTv} bQ{Hb(Fc Yd) SiiZ} An{wD(hR Md)} Eq{BaQz UtdR} Fp{MmIk JpPb} Fw{YiYl WhOz} Jl{JkrS RxkQ} Jn{HcWh LhOy} eC{oO(nC nH)} wC{jV(Kk Kp)} oE{DuUt GcbM} CxFdVa PoMnOy MpnInK TvVqjM KrPhwB KzmZoP RmUuUw OecQqZ

Constrained panels with 2 analytes, where 1.0E-8 >= 'model p-value' > 0. Contains 199 panels of 182,582 total panels evaluated. : Et(aA Aj Fp Hu Ih Ij Im Ip Ir Is It Iv Ji Jj Jl Jn Jq Js Li Lj Lx Lz Mr Ms My Mz Nc Ng Nl Nn No Ns Nw Oe Of Og Ok Oy Oz Pb Pe Qa Qb Qd Qe) Im(aA Fp Hu Iq Ir Is It Iv Ji Jj Jl Jn Jq Jr Js Jt Lh Li Lj Lu Lw Lz Mn Mr Ms Mz Ng No Ns Nw Oe Og Ok On Oy Pb Pe Qd Sh Ye) Li(aA Hu Ih Ik Ip Is It Iv Ji Jj Jl Jq Lw My Mz Ng No Ns Nw Oe Og Oi Ok On Oy Oz Pb) Nw(aA Fp Hu Hx Ih Is It Iv Ji Jj Lj Md Ms Mv Mw My Ng Nl Ns Ny Oe Og Oy Oz Pb) Ji(aA Ik Is It Jj Jo Jq Lj Ms My Ng No Ns Oe Og Om Oy Pb Wm) Jj(Aa Ij Is Lh Lj Nn No Nv Ok On) No(Is It Ns Og Ok Oz Pb Uh) On(Lj Ms My Ng Ns Oe Og Oy) Ok(aA Fp Is It Lj Og Pb) Lj(aA Ij Is Jt) Ij(aA Og) ChKe IpaA IsOg WbOw Constrained panels with 2 analytes, where 1.0E-7 >= 'model p-value' > 1.0E-8. Contains 212 panels of 182,582 total panels evaluated. : Lj(Fr Ih It Iv Jg Jl Jp Jq Lh Lw Lx Ma Mi Mm Mn Mp Mr Mz Nn No Nt Nv Og Ps Qd Vi) Is(aA Fp Fr Ij Ip It Jg Jp Lh Lx Ma Mm Mn Ms Mz Nn Ns Nv Ny Oe On Oy Oz Pb Qd) Ok(Hr Ih Ij Ip Jn Jo Lx Mn Ms My Mz Ng Nl Nn Ns Ny Oe Of On Oy Oz Qa Qb Qd) No(aA Aj Hc Hu Ih Ij Ip Iv Jn Jt Kc Ke Ms Ng Nj Oe On Oy Qd Ur Vt Ti Th) Ke(Af Aj aM Bg cH De dJ dK eC Hc Ik Jj Jo Kj Ld Ms Of Ow Oy Ph Uh Us) aA(Fp It Jg Jn Js Jt Lh Lx Ma Mm Mn Mz Nj Nm Nn Nv Ny On Qa Qd) Jj(Ii It Jg Js Jt Ko Lx Mn Ny Qa Qd) Nw(Aa Aj bN CH Ed Jv Ri Tv Uh Us) On(Fp Hu Ih It Of Oz Pb Qd) Uh(Id Ji Ko Ld Ps Qa Ri Tv) Og(Jg Jt Lh Nn Nv Qa Qd) Aj(Ad Im Ji Jt Kq) Ow(Dr Eq Hp Sh Vi) Ps(Rx Us Uu Vs) Aa(Im Ji Qa) Ch(Et Ji Kq) Ij(My Oy) Wf(Qa Vi) ItJp JiUs LdLp Constrained panels with 2 analytes, where 1.0E-6 >= 'model p-value' > 1.0E-7. Contains 482 panels of 182,582 total panels evaluated. : Uh(aA Ax bA CH Cs Cu Dc Dd dJ dM Ed Et Fy Hv Hw Ij Im Is It Jj Jn Jq Jr Jt Kc Kd Kf Kk Kn Kp Kq Lh Li Lj Lw Ml Mr Mt Mz Na Nr Oa Oh Ok Pe Pi Qd Qe Ra Sr Uc Up Vp Vt Wm) Ps(Aj Ar aW aZ Bg Bo Ch Ed Fw Gp Ij Im Ji Kd Kl Ld Li Lx Lz Mh Ml No Nw Oa Oe Oh Oi Ow Oz Pe Pf Qw Qx Rc Rj Sh Sr Ss Ur Va Vo Vt Wf) Qd(Aa Aj Fp Ih Ij Ip It Iv Jg Jl Jn Jp Jq Jt Lh Lx Ma Mn Mr Ms Mz Nn Ns Nv Oe Oy Oz Pb Wm) Ji(Af bA Bg bN cH cI De dM Ed Ef Gl Hc iZ jO jP jT Ju Jv Kc Kj Kk Ko Ld Qw Ri Ur Uu Uv Vt) aA(Fr Ih Ii Io Jj Jl Jm Jp Jq Lv Lw Lz Mp Mt Mw Nl Nr Ns Nt Nx Og Oz Pb Po Pz Qb Qc Qe) Lj(Aa Ip Ir Jn Jo Js Lv Mg Mt Mw Nb Nl Nq Ns Nx Ny Oh Om Oz Pa Pc Pe Po Pz Qa) Aa(Et Fp Is It Jl Jn Js Li Lu Lx Mk Mt Nc Nl Nn No Og Oy Oz Po Qb Qc Qe) Ij(Aj Fp Hc Hl Hu Ih Jl Jp Lh Lx Lz Ms Nn Oe Pb Rt Sh Vb Vz Wb We Xa Th) Nw(Bg bO cI De dJ Ic Id iJ jO jP jT Ld Oa oE oN Ow Ru Rx Vi Vt Wf Yd) Jj(Fp Fr Ih Ip Jl Jm Jn Jp Kq Ma Mm Mw Mz Nm Nt Ow Po Pz Qb Qe) Ke(aF bN bR cQ Dr Ed Ic iJ Jv Ng Oa oE Ri Ur Uu Vt Wm Th) No(Ch Hb Ic Kk Ko Ld oH oN Ou Ow Ph Qw Sh Uo Us Wf) Vi(BG Ch Ed Hc Im Ld Li Oa Of Pe Qw Sh Sr Uu Vt) Is(Aj Hu Jn Kc Ko Lw Mt Mw My Nj Nm Rt Sh Ur Yd) Lx(Fc Ih It Iv Jl Jt Og Oy Wb Yd Zw) Qa(Fc Hl Jg Jt Ns Oe On Sh We Yh Ye) Ih(Fp Fr Jg Jp Jt Lh Ma Nn Nv Og) Nv(Fp Hu It My Ng Ns Oe Oy Pb) Og(Fp Fr Jl Js Mz Ny Om Po Qe) Ow(Ch Em Fd Gd Lp Rz Ux Zw) On(Aj Ip Iv Jk Jn Lz Mv) It(Fp Fr Jl Jt Lh Nn) Pe(Du Sh Vz Wf Yl Xa) Fp(Jp Jq Jt Mm) Nn(Eq Iv Jt Sh) Im(Ch Eq Fd Ux) Oa(Dr Gc Rx Ti) Vt(bN Et Ko Ur) Aj(Jg Kf Ko) Kq(Eq Of Wf) Lh(Ms Ns Pb) Ed(Ru Xa) Et(Bg cI) Ng(Jg Jt) Ld(Ye Xa) ThLi NbTl UcOf WbOh WfJn Constrained panels with 2 analytes, where 1.0E-5 >= 'model p-value' > 1.0E-6. Contains 954 panels of 182,582 total panels evaluated. : Vi(Aj Ar aW Ax aZ bF Bo bZ cH Dk Eq Fn Fw Hq Hv Ih Ir Iv Iz Ji Jj Jn Jp Js Jy Kd Ke Kx Kz Lu Lz Mh Ml Mp Mq Mx My Nf Nx oE Og Oh Oz Po Qb Qd Qx Rb Ss Tn Tz Uh Un Ur Vb Zx) Uh(Ad aE Aj aM Ar As BN bV Cp Cq cT Cw dK Dr eF Fa Fw hB iB Ic In iO Ir Iv iZ Jl Kg Kr Kx Mh Mj Ms Nb Nf nI Nm Nn Nx Ny Om Ow Pb Pk Rj Ud Un Ur Us Uu) Nn(Aj Ch Fp Fr Hu Hv Ip Ir Jg Jl Jn Jp Jq Jr Js Lh Lv Lw Lx Lz Mn Mr Ms Mt Mx My Mz Ng Nj Nl Ns Nt Nv Ny Oe Oy Oz Pb Pe Po Qa Qb Qe Vt) Qa(Aj Fp Fr Hb Hc Hu Ih Ij Ip It Iv Jl Jn Jp Jq Kc Kk Kn Ko Ld Lh Lx Ma Mm Mn Mp Mr Ms Mw Mz Nj Nm Nv Ny Oy Oz Pb Qw Tv Ur Us Vt) Ij(Aa Ch Fr Ik Ip Iq Ir It Iv Jg Jn Jq Js Jt Kc Lw Ma Mi Mm Mn Mp Mr Mt Mw Mz Ng Nl Ns Nv Ny Of Oz Po Qe Ur Vh Vt Yh Yj Yf) Lx(Fp Hq Hu Ip Iq Ir Jg Jn Jp Jq Jr Js Lh Lw Lz Ma Mi Mm Mn Mp Mr Ms My Mz Nj Nl Ns Nt Nv Ny Oe Oz Pb Pe) Js(Fc Fp Fr Ih Ip It Jg Jl Jn Jp Jt Lh Lw Ma Mm Mn Mp Mr Ms Mt Mw Mz Ns Nv Ny Oe Oy Oz Pb Qe Rt Rx Sh) Vt(aA Aj aQ Ax cH Cs dJ dK Dp Ed Gp Im Is Jj Jq Kk Kn Ld Li Lj Mh Mn Mt Nr Oh Ow Qd Qe Ri Sr Tv Tz Xa) Ih(Ip It Iv Jl Jn Jq Lv Lw Lz Mm Mn Mp Mr Ms Mt Mw Mz Nj Nl Nm Ns Nt Ny Oe Om Oz Pe Po Qe Rx Sh) Jt(Fr Ip Jg Jl Jn Jo Jp Jq Lh Lv Lz Ma Mm Mn Mp Mr Ms Mt Mw My Mz Ns Nv Ny Oe Oy Oz Pb Po Qb Qe) Et(Ao Ax bA bN cH cP Cs CT Dc De dM Ed Ef Hc Id IZ Kc Kd Kj Kk Kl Kn Ko Ld Oa Tv Uu) Jp(Ch Ip Ir Iv Jl Jn Jq Ld Lh Lw Lz Mn Mp Mr Ms Mx Mz Ns Nt Ny Og Oz Pb Pe Po Qb Qe) Ps(aY bG Bn cU Cx Ef Eq Gh hB Hc Ib Iz Jj Ke Ki Kx Mx oE Oy Qb Qv Rt Ru Ua Wh Yg Ye) Fp(Fr Ik Ip Ir Iv Jg Jl Jn Lh Lw Ma Mi Mn Mp Mr Mt Mw Mz Nm Ns Ny Oz Pb Pe Pz Qe) Jj(Bb Dc Ir Iv Jk Jo Jq Kf Kn Ld Mp Mr Mt Nr Nx Oa Om Pe Pf Pj Sr Vq) Lh(Hu Ip Ir Iv Jg Jl Jn Jo Jq Lw Lz Mn Mp My Mz Ng Ny Oe Oy Oz Qb Qe) Fr(Aa Aj Hu Ip Ir Iv Jl Jn Jq Lw Mn Mr My Mz Ng Nl Ns Oe Oy Oz Pb) Is(CH De Hc Id iO jT Kk Ld nK nL Ow Qw Us Va Wb We Wf Yh Zx Wm) Jg(Ip Ir It Iv Jl Jn Jq Lz Mp Mr Ms My Mz Ns Oe Oy Pe Po Qb Qe) Nv(Aj Ip Ir Iv Jl Jn Jq Lw Lz Mn Mr Ms Mz Nj Nl Of Oz Qe Sh) Qd(CH De jT Kk Kn Ko Ld Mm Ow Qw Ru Tv Ua Ur Us Ti Th) Aj(Ap Ba Bb Cu Dc Fy Id Kn Li Mn Mt Ok Qe Uc Uf Vq) Mz(eZ hB hP Ip It Iv Jl Jn jT Ma Md Mm Mn My Ny Tv) It(Ip Iv Jq Ma Mm Mn Mp Mr Mt Mw Ny Og Pe Po Qe) Sh(Fw Jn Ke Kq Nw Ny Oh Om On Pf Rm Sr Ut Xa) Jl(Ip Jn Ma Mm Mn Mt Mw Nm Ns Ny Oe Oz Pb Qe) Ed(Dr Gb Kk Kn Ko Ld Si Uw Wd Yi Zq Zw Ti) Og(Ii Ip Iv Jn Jq Ma Mm Mn Mr Mt Mw Nt Qb) Id(aQ bN CH dJ Ji jT Kk Ko Ld Ow Ur) Ke(fN jO jP jT lL qA rS Ru Rx Vs wC Yd) Kq(Bg De Dr Ef Hc Iz Ng Oy Ux We Zx Th) Ny(Hc Ib Iv Jq Mr Ns Rx Rz Vj Wf Ye Xa) Ji(cT dJ eC Ic jE lN Ou Ph Ru Vs Th) Jn(Ip Iv Jq Ma Mm Mn Mr Pe Po Qe Rx) Ko(aA bN Ch Im Jo Kc Kj Oh Ow Qb Tz) Ld(Dr Fd Fi Ho Im Ru Uy Wb Wc Wf Yi) No(Bg bO cH De eC iO jT oE Vj Vs) Mn(Ip Ir Iv Jq Mr Ms Mt Po) Ur(Dc Fy Ir Jq Kn Qe Tv) Ch(Kf On Sr Tn Uf Zq) Im(cH De Dr kC Kk mF) Iv(Ip Ma Mm Mt Mw Qe) Wf(Mr Mw Nb Om On Ut) Xa(Bo Fw Kd Oz Sr Un) Oh(Gb Ho mM mU mZ nI) Li(Dr Eq Fd rS Wb) Aa(Mq Ms Ne Ok) Kn(dJ jO jT Tz) Oa(Si Vj Yj Zq) Mt(Eq Ip My) Nb(Hl Vj Ti) Jq(Ip Qe Wm) Lj(Kc Ow Ti) Nw(Dr eC Yh) Po(Oy Pb) Ma(Qb Qe) Yi(aZ Bo) Ow(Bg Oy) DrTz EqOm ThUn FdMq NsMp TvcH IoIr KfOf KkdJ VjPa PenI aWrS cQqZ wBnW Constrained panels with 2 analytes, where 1.0E-4 >= 'model p-value' > 1.0E-5. Contains 1,711 panels of 182,582 total panels evaluated. : Mt(aV bF Bg bQ bR bS bZ cA cG cH cK cL CO Ct dA De dH dI Ed Fd Hb Hu Hv Id Iq Ir Jg Jn Jp Jq Jr jT Ko Lw Lz Ma Mi Mm Mp Mr Ms Mw Mz Nj Nl Nm Ns Nt Ny Oe Ow Oy Oz Pb Pe Po Qb Qw Sh Tz Ur Ux Wf Xa Wm Ti Th) Ko(aJ aM Ax bA Bg bS cA cH Cu Dc dK dM eC Fa Fw

Figure 30 Continued

Fy hB Hc Ih Ij Ik In Ir iZ Jl Jp Jq Js Jv Kd Kk Kl Kn Kq Kx Ld Li Lj Lx Mh Ml Mr Ne Ng Nh Nn Nr Oa OE oF Oi Or Pi Qe Qw Rf Ri rS Sr Ss Tv Ug Un Ur Us Uu) Jj(Ad Ax BA Co Cu Dd Ed Ez Fa Fb Fw Fy Hb Hv Hw Hx Id Il Io Iq Jd jK Jr jT Kc Kd Kg Kk Kp Ks Kx Ky Lv Lw Lz Mg Mi Mx My Nb Nc Ng Nj Nl Nq Nu Oh Ou Oz Pa Pg Pi Qc Qh Rf Ri Rm Tv Tz Uc Uf Un Xa Wm) Xa(aA Aj aM Ar aW aX aY aZ BG Ch CU Dr Et Fc HB Hv Hx Ih Iv Ji Jl Kq Kz Li Lj Lz Mh Mi Ml Mp Mq Mx Nn Nr Nv Ns Oi On Or Pa Pf Pi Po Qb Qd Qe Ql Qx Rm Ru Rx St Tz Uh Uu Vq) Ld(aA Aj bB bR cH Cu Dc dJ Em Fw Fy Hb Ij Jd Jl Jn Jq Jr Js Kf Kn Kq Kx Lh Li Lj Mr mZ Nh NN Oa Oh Ok On Pi Pj Qe Qh Ri Sr Tv Tz Uf Un Uw Uz Vh Vq We Zq Th) Kq(aA bN bS cA cH cQ Ct dJ eC Ed Fr Fw Gd Hq Id Ik Im Jk Jo Kc Kj Kk Kl Kn kQ Lj Lu Mh My Oa oE OH Oi oN Ow Ph Qw Rt Ru Ss Tn Tv Tz Ur Us Uu Uv Vt Yd) Qe(aQ bA Bb bN CH cT De dJ Fr Hb Hl iJ Ip Ir jT Kc Kf Kk Lw Lz Mi Mm Mn Mp Mr Ms Mw Mz nI Nj Nl Ns Nt Ny Oe oH Ow Oy Oz Pb Pe Po Rt Ru Tv Us Vj Wf) Id(aE aF aW bS cA cJ cQ dK dR eC Ed Fw Hb Ic Ij Il Im In jK Jp jQ Kc Kn Li Lj IK IL Mn Nh Nn oE Of OH On Qa qC Qd Ri rS Tv Tz uR Us vS Vt) Jq(Aj Ed hB Io Iv Jl jO jT Kc Kk Lz Ma Md Mm Mp Mr Ms Mw Mx Mz Nc Nj Nl Nm Nr Ns Nt Oa Ow Oz Pb Pe Pf Po Pz Qb Qw Ri Ru Sr Tv Uf Ug Uo Us Vq) Kn(aA Af aM aQ Ar aW bB bN cA CH cQ dK dM Dp eC Hb Hc Ij Im In Is Jo Jp Kc Kj Kk Kx Ky Li Lj Ml Nn Oa oE Of Oh Ow Oy Qb rB Sr Us Uv Wm) Mz(cH Hr Hx Iq Ir Jr Kc Lv Lw Lz Mi Ml Mp Mr Ms Mw mZ Nc nl Nj Nl Nm Nr Ns Nt Of Oy Oz Pb Pe Pf Po Pz Qb qZ rB rS rW vl wB Wf) Kc(aA Aj Ax CH Cs Cu Dc dJ Ed Fw Hb iB Im Iv Jl Jn Jp Jr Js Kd Lh Li Ml Mn Mr Na Nn Nr Oa Oh On Ow Pi Qb Qd Sr Tz Un Vt) Kk(aA Aj aQ Ar Ax bN CH Cu Dr eC Fw Hb Ij Ir Iu Jn Jp Jr Js Kf Kx Li Lj Mr Nh Nn Oa Oh Oi Ow Pi Pj Qb Qc Ri Sr Tz Vq) Ur(Ax bA Cu Dd Ed Et Fd Fw Ih Im Ip Iu Jl Js Jt Kd Kf Lh Li Lj Mr nI Nr Nv Oa Oh Ok On Ow Pi Rm Sr Tz Uc Un Vq) Mn(Bg CH Hv Hw Iq Jg Jr Lu Lv Lw Lz Ma Mi Mm Mp Mw Mx Nc Nh Nl Nm Nr Ns Nt Ny Oy Oz Pb Pe Pf Qb Qc) Tv(Aj bN Ch cQ dJ Dp eC Ed Gp Hb Ij Im In Ip Li Lj Ml Nk Of Oh On Ow Oy Pg Pj Qb Rf Sr Tz Un Us Vs Wm) Ny(Fr Hv Ip Iq Ir Jg Jn Jr Lv Lw Lz Ma Mi Mm Mp Ms Mw Mx Ng Nj Nl Nt Oa Oe Oy Oz Pb Pe Po Qb Qc) Is(aF Bb Bg bN cI cP Ct dJ Dp Dr eC Gd HB Ic jK Kf Kj Kx ml mZ nC nH nl Pj Sr Up Uu Vs Vv) Im(aN aQ bA Bg bS cI Ct dJ Gd HB Hc Ic iO iP Kf Kj kN kO kP Kx nK oF oH Ou Ow Qw Ri Tz) Iv(Hr Io Jl Lv Lw Lz Mp Nj Nm Nr Ns Nt Nx Om Oz Pb Pc Pf Po Pz Qb Qc Ru Uw Vb Wf Zq Ti Th) It(Hv Iq Ir Jn Jr Lv Lw Lz Mi Ms Mx Nb Nl Nm Nr Ns Nt Nx Om Oz Pa Pb Pc Pf Pz Qb Qc Sh) Po(Du Hu Io Ip Ir Jl Jr Lw Ma Mm Mp Mr Ms Mw My Ng Nl Nm Ns Nt Oe Oz Pe Pz Ru Wb) Kf(aA aM Bg bN cQ Ct De eC Ed Hc In Jo Kj Lj Ng oE Oh Ow Oy Qa Qb Qd rB Tz Uu Vt) Li(Bb bO bQ bZ CH cO Dc De Du Ed Gd iB Ic jO jT Ow Qw rB Rg Ri Sr Tz Un Us Yi) Ma(Aj Ch Hv Ip Iq Ir Jp Jr Lv Lw Lz Mp Mr Ms Mw Mx Ng Nl Ns Nt Oy Oz Pb Pe Qc) Ip(Hv Iq Ir Jr Lv Lw Lz Mi Mm Mp Mr Ms Mw Mx Nc Nj Nl Ns Nt Oz Pb Pe Pf Qb) Sr(Aj aQ Bg cH dJ Dr Ed Et Gd Hb Hc In Lj Ng Oe oH Oi Ow Qd Qw Ri Tz Uu Va) Jn(Fc Iq Ir Jr Lv Lw Lz Mi Mp Ms Mw Mx Nl Ns Nt Oe Oz Pb Pc Pf Pz Qb Ye) Vt(Ar bA bS cE Ch cl cT DR eC Fy Kx nW Oa oE Of oH On rB Ru Uf Wf Yi) Aj(Aa Ax Dg Dl Ih Jl Jp Js Kg Kp Lh Lj Mm Mr Oa Oh Om Ow Pj Pz qZ Un) Qd(aQ bA Bb bN cl cT dJ Dr eC Eq HB Hc Kj Kp oE oH Ri Sh Yd Yi Ye) Lj(Fc Fd Gb Hb Ho Ic Jd Qy Ri rS Tz Uc Un Us Uw Vw wB Wd Yi Zq) cH(aA Ed Fy gL HB iB Ij Jp Nn nY Oa oF On Ow Qh Rf Tn Tz Un) Dr(Et Ez Fw Kd Lx Mp Mq Oh Or Ou Qa Qh Qx Rm St Ut Vj Vq) Qb(Fr Gb Ir Jl Lw Mm Mp Mr Ms Nl Nm Ns Nt Oe Oz Pe Vw Zq) Jp(Bg Ed Fr Hc Hv Iz Kx Lv Mi Ng Nj Nl Nr Oa Oe Ow Oy Wm) Ch(Dc Fr Fy Hb Jd Jh Jt Kx Lh Nv Oa Ok Qa Tz Uc Un Ut) Ow(aA Ax Cs Dc Ed Fw Kd mE Mk My Ng Oa Of Oh Qa Qw Un) Jg(Hu Hv Iq Jr Lv Lw Mi Mw Mx Nl Nt Of Oi Oz Pb Qc) Jl(Hb Ir Lw Ms My Nl Nt Oy Pj Pz Qc Sh Vj Wf Wm Ti) Et(cQ Fy hB Ic Kx Lp Ph Qw Ri Sh Tz Ug Un Us Th) Mm(Hv Ir Jr Lv Lz Mp Mr Ms Mx Nl Ns Nt Oe Oz Pe) Mr(Lv Lw Mk Mp Mw My Nm Ns Oy Oz Pb Pz Ru Wm) Og(Ir Jk Lw Mi Mp Mx Nb Nm Nr Nx Pe Pf Pz Qc) Oh(Ed Fp Hb Ic jT Kd nC nK nL oH oN Vq Wd Ti) Ij(Bg Ct De Ed Gd Ib Iz Kj Oa Qw Ug Us Vs) Wf(Cu Hv Ih Ir Jr Kd Mq Nn Nr Nv Pg Tn Un) Pe(Fr Gd kC kE kO Mk Mw mZ Nm Ns Oy Oz Pb) Vj(bA cT Dc Ed Fd Fw Fy Js Kd Mx Nr Pi) Qa(Bb De eC Ib jT nI oH Ou Pj Ri Vs) Ed(Bb dK Gc Hb Lh Ok On Rf Un Yg) Fd(Ar aW Bo Cx Lz Ml Nn Oz Pf Qx) Fp(Io Iq Jr Ms Nc Nj Nl Nt Nx Pc) Fr(Hv Jr Lz Mp Ms Mx Nc Nj Nt) Lx(bS bZ kE lX mZ nI nK nL Qw) Mw(Ir Jr Lv Lz Mp Ms Nl Ns Nt) Ji(eZ Lp rB rS Sh WB wD Yd) On(Bg Eq Hc Iz mZ oN Qw Yd Th) Fw(Hb No Ru Si Vz Yi Yl Zq) Mq(Eq Gd Lp Uy Wb Wc Yi Ye) Tz(Fc Ho Ru Sh Va Wd Zq Ti) Ke(rB rW rY uM Va vT yD Yi) Nw(mI nC nl nK nL rB rS rW) Pf(Eq Gb Ho Hp Oz Ux Vz Wb) No(aQ bS Ct dJ jK jO Tj) Lh(Hr Hx Ii jO jT Md Nm) Ir(Lt Mp Nm Oz Pb Us) Uh(eP mZ nC nH nL Vs) nl(Js Mp nK Ns Oy Oz Pb) Vj(cQ dJ Rt Sh Us) Yi(aA Ar hB Rh Rt) Oa(dJ Em Hb Oe Oi) Va(lh Rm St Un Vq) Dc(aA De Rt Us) Zq(aX aZ Gd Nb) Ru(aZ Hv Kz St) Om(Gd Oy Ux We) hB(aE cQ dJ eC) iP(qZ rN rS wD) Nn(Gb Kd Wb) Lz(Ho Nm Oz) Mp(Hq Lp mZ) Sh(Mx Nb Tn) Js(jT rB Yh) Nv(Eq mZ Wm) Vq(aZ Ml Ri) Pj(aA dM wD) Ax(Ti Th) Wb(Ml Qx) Jr(jT rB) Un(eC jT) aA(Hb Si) bA(Oz Qc) wB(Kr Nm) qZ(aN bL) ArLp CsTh EqUt NsNt MfrS MyNb NgUf NliB IhYe YkPs Kpr Ql Qy Ra Rf Rh Rt Ru Rx St Uf Uh Us Ut Va Vt Wf Zq Wm) Mt(aQ Ax aY Bb bN bU cF Ch cQ cU dG dJ Dp eC Gd Gp hA iB iH Jd jK jO Kf Kx Ky lK lO Lv Mv mZ Ng nI nL Oa oE oH oN pF Pj qW rB Rf Sr Tr Tv Uk Un Us Yi Tj) Sh(aH bA cE Co Cp Cq Cw Dd Dk Ef Gc Hq Il Iz Jd Jg Jh Jk Jq Jr Jt Ju Jv Kd Ko Lh Mj Mn Mp Mv Mz Nr Nt Ok Ou Pa Pg Ph Pi Qh Ru Si St Uc Uf Vs Yg Yi Zq) Jj(Al Ao Ap aQ Ar Bc cE CP Cq Cs cT Cw dF Dg dJ Dl Em Fi Ha Ho iB Ic iO Iu jF Jh Ju Kr Lp Mj Mq Nh Ns oF Og Pc Ql Qy rN rS St Tn Ua Up vl Vp wB Yi) Ch(Aa Ad Ap Ar Ax BA Bb Co Cu Cw dF Ed Ef Ez Fa Ih Jg Jl Jq Js Kd Kg Kp Ky Mm nN Nq Oh Om Ou Pj Qb Qc Qh Qy qZ Rf Ri Rm St Tr Tt Ua Uw wB wD Yi) Kx(aA Ax bA Bg bS cA Cs Cu dJ dM Ed Fw Gb Ho lj lk Iv Jl Jq Jr Js Kd Kf Kp Lh Lp Ml Mn Mr MZ Na nC Ng nL Nn Nr Nv Oe Ok On Pi Pj Qy Ri Wb Ti) Oa(AA aE aQ bA Bb bN bR bS bX cA cE cJ cQ cT Cu dK dM Dp Ed Fy Ic In iO Jd Kd Kf Kp Lh Lw Mr mZ Nh nI Nn oF oH Ok On Pi Pj Qg Ri Sr Tv Un Us) Zq(Af aH Ar bA bM Cq Cu Dg dR Eq Ex Fp Ha Hv Hx Il It Jm Kd Ki Lp Lz Mh Mi Mj Ml Mm Mq Mr oE Or Oz Pa Pg Pi Pk Po Qh Rf Rm Tv Uu Ux Vo Wb) Ri(Ar Ax bA Cs Cu dM Ed eZ Fa Fw hW Ih iZ Jp Js Kd Kf Kp Kq Lh Ml Mn Mr Nn Nv OH Ok On Pi Pj Qb qC Qe rB Rf rN rS rX Tv Un uT vI wB wD) Ed(aQ Ar Ax bA Bc Cs cT dJ dM Em Ez Fy Ih Im In iO Ip Jd Je Jg Js Kd Kp Lu Lw Lx Ml Mm Mn Mz Nh Nn Nv Nx oE oH Om Pi Pj Qe Ql Rb Uf) Ar(AA aE aQ Ax bA Bb bN bO cJ Cu De dJ Gb Ho iB Ic Ih Jd Jp Jq JT Jv Kd Kf Mn nI nN Pi Pj Ru Tv Uc Un Up Uw Uz Wb Wc We) Qb(Ax BA Bb cT Cu dJ Dl Fc Fy Gc Ho Hv Iq Jr jT Kd Kp Lv Lz Mi Mw nC nH nI Nj nK Nx Pb Pc Pj Ru Uf Vj Wb Wd Yi Yj Wm Ti) Un(aQ Ax Bg bN cl cJ cQ Cs dJ dK Dp dR Fw Gp Hc iB Ic In jO Jp Lt Mh Ms Ng Nn OE Of OH Oi Ou Qw Ru Ug Us Uu Yi Wm) Pj(aJ aM aP Ax bA Cs Cu dF dG eP Fa Fw gL Hv Iv iZ Jn Jp Jq Jr Kd Lj Lx Mr Mz Nh Nr Nv oE oF Pe Qe rS Tn Ug uT Vp wB) Mp(Em Eq Hp Hv Io Iq Jr Lv Lw Lz Mk Ms Mx Nj NL Nm Nr Nt Nx Om Oy Oz Pb Pd Pe Pf Pz Qc Ru Ry Uw Uz Va Wb Wc Yi) Ax(AA aE aQ bA Bb bN bQ bZ cE dJ Ho Ic Ik Jd Jp Jq Jt Kd Kf Kg Lw Mc Mn Mu nI Nn Oe Oi On rB rS Sr Vj Wd Wf) Yi(aH aP aS aU aW bM cU Fc Hv Iv Ji Jo Kd Kj Kz Lz Ml Mx Nn Nv Of Om Or Oz Pf Qx Rx St Uh Uu Uv Vb Vu Wf Yh Tl) Og(Bb Hv Hv Hw Hx Il In Io Iq Iu Jh Jm Jo Jr Lv Lz Mg Mj Mq Mu Mv My Nc Nf Nh Nj Nl Nq Ns Nu Oh Oz Pa Pc Pg) Om(Bg Hc Hu Ip Iq Ir Lv Lw Lz Mi Mr Ms Mw Mx My Ng Nj Nl Nm Ns Oe Oz Pb Pc Pf Qc Qw Rt Wb Yd Ye Tl Wm) Fy(aF aQ Bg bN Ct Dc dK Dp eC Em Fc Hc Ic Id In Jo Jv Kj Lj Lu Ng oE oH Oy Ph rB Rx Sr Tv Vs Wf Th) Kd(aQ bB bN bR bS Cs dJ dK dM Dp eC Hc In Jd Lh Li Lj Lx Ma Mh Mm Mn Nv Ny oE Of qZ Sr Uf Tl Wm) rB(aA aJ aP Cs cZ Dl dM Fa Id Im Is Jl Ko Kq Kr Lh Lw Mj No Nv Nx Ny Oh Ok On Qd rN Tv Uh wB wD) Cu(aA Bb Bg bN bZ cl Cs Ct De Dp Eq Gd Hc iZ Jd Jp Lj Mn mZ Nn oE Of OH oN Qc Qw Rf Us Uv) Wf(bA Cp Cq Dk Et Ex Hx Id It Jd Jh Jq Jt Lh Mi Mj Ml Nt Ok Pa Pi Qx Tv Uc Uw Vp Vs Vu Xa) Kf(bS cA dJ dK dM Dp Gp hX Ij Ik Iz Jp Jq Ky Li Ml Nn Oe Oi Ou Qw rS Sr Ss Ug Uk uM Us xA) nI(cL Fw Ij Ir Ji Jn Kq Lh Li lN Mh mP nC nL NN No Ny oE On Pf Pg Pi Qc Qd Rj Sr Um Vt) Lz(Em Fi Gb Hv iB Ii In Io Ir Jr jT Lp Lv Lw Mr Nj Nl Nr Ns Nt Nx Pb Pf Pz Qc Ry Wb Wc) rS(Cs Dl Et Fa Fb Jl jV Kn Kp Kr Lu Lx Mh No nW Ok Ou Qd qX qZ Rf rN uX vI Vt wB yL yE) aA(Ad aF Ap aQ Bb bI bN cQ Cx eC Gc Ho Ic iO jK jT Kg Kp nK Ru Ry Uf Uw Vh Wm Ti Th) Nr(bS Hc Ip Iq Ir Jd Jr Lv Lw Mi Mm Mr Ms Mw Nl Nm Ns Nt oN Oz Pb Pe Qw Rf Tv Us) Lj(aE aH aQ bA BB bF bN cE cJ cL dF dJ Hf iB iO jK jT Kg Kp oF oH Ou pS Vj Yj) Sr(aE aF aM aN bN bS cJ cQ dK dR eC Em Fw Ic Im Jp Mh Mr Of Oh Ok Oy Ph Pi Qe) Vj(aX Cq Cs Dd Ha Hx Ir It Iv Jm Jq Jr Lp Mj Mr Mz Ok Pg Ph Qh Rm St Tv Vp Vt) Oz(cT Fc Fi Gc Ho Hp Iq Jr Lp Lv Lw Mi Mw Mx Nl Nm Nt Nx Pg Pz Ru Ry Si Uw Wd) Pf(Gd Hv Iq Ir Jr kE kN Lv Lw Mi Mm Mr Mw Mx Nj nK Nl Nm Ns Nx Oy Pb Pe Tv Ti) jT(aD aM An dM Et Fa hW Ih Ij Im jI Jl Ko Ky Lw Mh Mj Ml Nl Nv Nx Ny Ok On Vt) Nn(bA Bg bN CT dJ dM Gd Hc IZ Jv Kj Lp oF oH Pi Qw Tv Ux Uz Vc Wc) On(bN bO bZ cI Ct De Dp Ef iZ jO Jv Kj Kl mM nK nL oE Ou Ss Us Uu Vs Yh) Nm(Hv Hw Iq Jr Lv Lw Mi Mm Ms Mw Mx Nb Nc Nj Nl Ns Nt Nx Pa Pb Qc wD) Lx(aV Bg bQ bR cA cG cK cL CO cU dA dH dI kN Ky lK oN pF Rg Uk Tj) Li(aQ bA bN cI dJ Dp iZ kF Kp mZ nL oE oH oN Ph pS tT tX Vs wB yL xA) Tv(aE aF aQ aW bL De Fw Gn Hc Jp Js Lh oE Qc Rt Ru Rx St Va Ti Th) Uh(EM fR Gb Hl Ho Hp hW Lp nK Rt Ru Ry Uw Uz Vh Wc Wd We Wg Tl) Mr(Bb Dp eC Hc Hr Hx Io Ir Jd Md Ms Nj Nt oE Pc Qc Rf Rx Us Ye) Lw(Hv Io Iq Ir Jr Lv Mi Mm Ms Mw Mx Nl Ns Nt Pa Pb Pe Pz Qc) Jq(bA Bb bN cI Cs cT De eC Fa Hc iZ jP Jv Ky oE oF Oy Va Vs) Nx(Ip Iq Ir jK Jr Ms Mw Mx My Mz Nl Ns Oe Oy Pb Pz Qc wD Wm) Ok(Bg bN cI cP De Dp eC Hc Ic iZ jO Kj Qw Rf Rt rW Rx Us Th) wB(AN cP Et Hq Hu iP Jk Ko Ma Me My Ng Nq Nw oE oN Oy rW) Lh(Bg eC Hc iZ jP Jv Kj Lp mZ nC nK nL oN Ou Qw Us Uu Wb) Ru(Cs Ex Fp Ha Hx Jr Mi Mj Mv Mz oE Or Ou Pg Pi Ql Wb Tm) bA(aS Bb bl bO Ct Dp Ho Ih Ij Jp Mn Oh Pb Qa Rt Rx Va Wb) Nt(Eq Gd Hx Ik Iq Ir Jr Ms Nj Oe Oy Pb Pe Pz Qc Vb Th) Mw(Hc Hu Hv Iq Lu Mi Mm Mx My Ng Nj Oe Oy Pb Pz Qc Ye) aZ(Fc Fi Gb Gc Ho Lp Rt Uw Uz Vb Vh Vw Wc Wd We Wg Ti) Ir(Hx kP Lv Mx Nj Nl Ns Oh Pb Pc Pz Qc Rx Ry Va We) Bg(Bb dF Jg Jl Jt Nv Ny Oh Ou Qa Tn Uc Uf Ut wD) Mh(Bb Gb Ho iB JD jI jK Lp Mm nC nH nK nL nN) Pe(bQ eM Hr Io lO Lv Ms My Nc Nj Nl Pc Pz Qc Qw) mZ(bQ bZ cO hA Iv Kq Nw Ny Pg Pi Qa Qd Qe Rm St) qZ(aW bS Ct dJ eC Ef Hc Ic Id Iz Ko oN Ph pS qA) Nv(De Hc Iz jO Kj mM nK oE oN Ou Qw Us Ux Ti) Oh(Bb bN bO cI dJ eC Em iB iJ jK jO Jv Qw Us) Pa(Ho Ip kC kO kP Mz nC nF nH nJ nL Va Wb Tl) iZ(aE aH aQ bB cE cJ dD dJ eC Ij Ip Mm Mn Ti) Et(eC Eq Fc jO rN rR rW Ry Ux uY Wb wD Yd) Nl(hW Iq jF jI jK Jr Lv Mi Mx Ne Ns Pz Qc) Qa(aQ bN cI cP CT dJ jK kC kE kN kO mF) Fw(Dp Em Fa Jd Kp Ky oE oH Ql Rf Uf Uk) Qe(cP eC Hc Ic iO jK jQ Kp nC nL Qw Vs) Kq(aM aQ bL bZ cI dM Em Ic Mv Qu Ua Vs) Lp(aH aU aW Bo Ez Kz Mk Ml oE Or Ql Qx) Ny(Ao Gc iB jK kP lO mF nC nK nL oF Wm) Jl(Bb De Dp eC Gc Hc Iz oE oH Qw Us) Jp(bN bO cI Cs cT De dJ Fa oE Qw Rf) wD(An bS Ct Db Ef Kn Ko Mz Nd Nw Ou) Aa(aJ aM aP bN bV dF dM oF Vt Wm) Eq(Ba Co Ez Jd Jh Mg Pd Rz Tn Uf) Th(Fp It Jd Js Jt Ko Mj Ql Uf Ut) Mi(Gd Jr Ma Mm Nj Ns Pb Pz Qc Vb) Ho(aH Bo Cs cT Ex Ml oE Or Qx St) Ij(Ao bN cI dJ Ic iO Jv Ph Uk Uu) Lv(Io Iq Jr Mx Nc Ns Pb Pz Qc) Qd(eZ jK jO jQ kE mF nK nL Vs) Js(Bb bN cI jF jK mU nL qW Us) Kp(bN eC Fa iB lL Of pS rW zG) Pi(Dp Jd Of Rf Rt Ry Uf Us Tl) oF(aE cQ Id Ih It nN Si Wb Ti) Mm(Hu Hw Iq Ng Nj Oy Pb Qc) Im(Em jK Jv Qt Ua Ug Uu Vs) Jt(bN cI CT dM Gd Hc Vb) Bb(aM bN bV Cs dF dM Ml) Ns(Ii Iq Jr Mq Mx Pz Qc) Mn(aJ bN cI cT De dM Qw) Mz(eC Hc Hv Jo Mx yH Wm) Uc(eC Hc Ng Oy Qw Us Va) Wb(bQ cT Ex oE Or Pd Ql) Ji(Fc Gd nC nL rW Rx yL) Uu(Gc Jg Si Uf Uw Vh Yg) Ti(Fa Fp Ha Mj Pg Ut) Gb(Bo bQ Ml Or Qx St) It(Rx Ry Uy Va Vb Ye) Pz(Hv Iq Jr Ms Mx Oe) Qc(cT Ip Mx nC nL nU) Ko(Gd hO iB qC rN uR) Rf(aQ cJ dK Nh Oe Oi) Vt(Em eZ iB Lt Va Tl) nK(cL fR Jn No Pg St) lN(kC kO nF nH nJ nL) Wm(Ip Iv Jg Jn Jr) Fa(dJ iB In jO lL) Fc(Hx Jr Mv Rm St) Gc(cT dR Hx Iv oE) Nw(kP mP nN nT wQ) Uf(Cs Ml oH Oi Ux) Uw(bM Bo Fp Kz oE) Vu(Hl Va Vb Tl Xa) dF(aF bZ De dH oN) dM(eC jK lL pS qC) rN(aN Jk Lu Nk Ou) Ma(Hu Nc Nj Oe) Si(aP fR oE Va) Ke(eM eP Gd Yh) Rt(Cq Jr Pg Tn) Of(Up Vp Vs Xa) cZ(qX rR rW rY) nN(iH Jn Nh oH) mI(bI bR Hx Iv) Em(Ky oE Qx) No(kE kP lX) Ye(Pd Ql Rm) cT(Rx Va Vs) nL(bR cL St) Bo(Yg Yh) Fi(Ml Qx) Ng(Jd Tn) Nj(Iq Mx) Ii(Ms Oe) Hc(Jh Ut) Ip(Hw jK) Is(eM eZ) Jn(Gd nC) Rm(Sf Us) Oi(Jd St) Vb(Cw Pd) aN(rW vI) uT(oN uR) AnyL BaCt CqTl CsIc PoQw GpeM HaRx MlRv MvUy NbOy NhiB HpQx HxRy TncQ IhUs IoIq YdUt VzPg JrjK XaRj KnVs UzoE UxPd aWiH bBoH bNoQ cGhA cLnC eCnU hLiP nWuX

Unconstrained panels with 3 analytes, where 0.0E0 >= 'AUC p-value' > 0. Contains 50,000 panels of 32,874,593 total panels evaluated. :
Ps{Us(aA aC AD aE Af aG aH aI AJ aK AL aM AN AO AP aQ AR AS aU aV Aw AX aY aZ BA bB BC bE bF Bg bH bI bJ bL bM bN BO bP bQ bR bS bU bV bW bX bZ cA cB cC cD cE cF cG CH cI cJ cK cL cN CO Cp Cq cR CS CT CU CV CW CX cY cZ dA DB DC dD DE dF DG dH DI dJ DL dM dN Dp DR Du Ed Ef Em Eq Et Ex Ez Fc Fd Fi Fn FP FR Fw Fy Gb Gc Gd Gh GL Gn GP Gz Ha Hb hC Hf Hl Hq Hr Hu Hx Ic Id Ih Ii Ik Im In Io IP Iq Ir It Iu Iv IZ Jd Je Jf Jg Jh Ji Jj Jk Jl Jm Jn Jo Jp Jq Jr Js Jt Ju Jv Jy Kc Ke Kf Kg Kj Kk Kl Kn Ko Kp Kq KR Ks Kx

Figure 30 Continued

Ky Kz Ld Lh Lj Lp Lt Lv Lw Ly Lz Ma Mb Mc Md Me Mg Mh Mi Mj Mk Ml Mm Mn Mp Mq Mr Ms Mv Mw Mx My Mz Na Nb Nd Ne Nf Ng Nh Ni Nj Nk Nl Nm No Nq Nr Ns Nt Nu Nv Nw Nx NY Oa Oe OF Og Oh Oi Ok On Op Or Ou Ow Oy Pa Pb Pc Pd Pe pF Pg Ph Pj Pk Po Pz Qa Qb Qc Qd Qe Qg Qh Ql Qm Qn Qt Qu Qx Qy Qz Ra Rb Rf Rg Rh Ri Rj Rm Rt Ru Rv Ry Rz Sf Sh Si Sj Ss St Tn To Tv Tz Ua Ub Uc Ud Ue Uf Ug Uh Ul Um Un Uo Up Ur Ut Uu Uv Uw Ux Uy Uz Va Vb Vc Vh Vi Vj Vo Vp Vq Vs Vu Vv Vw Vz Wb Wc Wd We Wf Wg Wh Yd Yj Yl Zw Zx Ye Tm Tl Xa Wm Tj Th) Oz(aA aC AD aE AF aG aH al AJ aK AL aM AN AO AP aQ AR AS aU aV AW AX aY BA BB BC bE bF BG bH bI bJ bL bM BN BO bP bQ bR bS bU bV bW bX bZ cA cB cC cD cE cF cG CH cI cJ cK cL cM cN CO CP cQ cR CS CT CU CV CW CX cY cZ dA DB DC DD DE dF DG dH DI dJ DK DL dM dN Dp DR Ed Ef Em Eq Et Ex Fc Fn Fp Fr Gb Gc Gd Gh Gl Gn Gp Hb Hc Hf Hl Ho Hp Hq Hr Hu Hv Hw Hx Ib Ic Ih Ii Ij Ik Il In Io Ip Iq Ir Is It Iu Iv IZ Jd Je Jf Jg Jh Ji Jj Jk Jl Jm Jn Jo Jp Jq Jr Js Jt Ju Jv Jy Ke Kf Kg Ki Kj Kk Kl Ko Kp Kr Ks Kx Ky Ld Lh Li Lp Lt Lu Lv Lw Lx Ly Lz Ma Mb Mc Md Me Mf Mg Mi Mj Mk Ml Mm Mn Mp Mq Mr Ms Mt Mu Mv Mw My Mz Na Nb Nc Nd Ne Nf Ng Nh Ni Nj Nk Nl Nm Nn No Nq Nr Ns Nt Nu Nv Nw Nx Ny Oa Oe Of Og Oh Oi Ok Om On Or Oy Pa Pb Pc Pd Pf Pg Ph Pk Po Pz Qa Qb Qc Qd Qe Qg Qh Ql Qn Qt Qu Qv Qw Qx Qy Qz Ra Rb Rc Rf Rg Rh Ri Rj Rm Rt Ru Rv Rx Ry Rz Sf Si Sr Ss St Tn To Tv Tz Ua Ub Uc Ud Ue Uf Ug Uh Uk Ul Um Un Uo Up Ur Ut Uu Uv Uw Ux Uy Uz Vc Vh Vi Vj Vo Vp Vq Vs Vt Wb Wc Wd We Wf Wg Wh Yd Zw Ye Tm Xa Wm Tj Ti Th) Lj(aA AD aE aF aH al Aj aK AL aM AN AO Ap aQ AR AS aU aV Aw AX aY aZ BA BB BC bE bF BG bH bI bJ bL bN bO bP bQ bR bU bV bW bZ cA cB cC cD cF cG CH cI cJ cK cL cM CO CP CQ cR CS CT CU CV CW cX cY cZ dA DB DC dD DE dF DG dH DI dJ dK DL dN Dp DR Du Ed Ef Em Eq Et Ex Ez Fd Fi Fn FP Fr Fw Fy Gb Gc Gd Gh Gl Gn Gp Gz Hc Hf Hl Ho Hp Hq Hr Hu Hv Hw Hx Ic Id Ii Ij Ik Il Im In Io Ip Iq Ir Is Iu Iv Iz Jd Je Jf Jg Jh Ji Jj Jk Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lt Lu Lv Lw Ly Lz Mb Mc Md Me Mh Mi Mj Mk Ml Mm Mn Mp Mq Mr Ms Mt Mu Mv Mw Mx My Mt Mu Mv Mw My Mz Na Nb Nc Nd Ne Nf Ng Nh Ni Nj Nk Nl Nm Nn No Nq Nr Ns Nt Nu Nv Nw Nx Ny Oa Oe Of Og Oh Ok Om On Op Or Ou Ow Oy Pb Pd Pe Pf Pg Ph Pi Pj Pk Po Pz Qa Qb Qc Qd Qe Qg Qh Ql Qm Qt Qu Qx Qy Qz Ra Rb Rc Rf Rg Rh Rm Rt Ru Rx Ry Rz Sf Si Sj Sr Ss St Tn To Tv Tz Ua Ub Uc Ud Ue Uf Uh Uk Ul Um Uo Up Ut Uu Uv Uw Ux Uy Uz Va Vb Vc Vh Vi Vj Vo Vq Vs Vv Vw Vz Wb Wc Wd We Wg Wh Yd Yl Zw Zx Ye Tm Tl Xa Wm Tj Ti Th) Ed(aA aC AD aE aF al Aj aK AL aM AN AO AP Ar AS aU aV Aw AX aY bA BB BC bE bF BG bH bI bJ bL bM bN BO bR bU bV bW bX bZ cA cB cC cD cE cF cG CH cI cJ cK cL cM CO CP CQ cR CS CT CU CV CW cZ dA DB dC DD DE dF DG dH DI dJ dK DL dM dN Dp Dr Du Ef Em Eq Ex Ez Fb Fc Fd Fi Fn Fp FR Fw Fy Gb Gc Gd Gh Gl Gn Hb Hf Hl Ho Hq Hr Hv Hw Hx Id Ih Ii Ik Il Im In Io Ip Iq Ir Is It Iu Iv Iz Jd Jf Jg Jh Ji Jj Jk Jm Jn Jo Jp Jq Jr Js Jt Ju Jv Jy Kc Kd Ke Kf Kg Kj Kk Kl Kn Ko Kp Kq Kr Ks Kx Ky Kz Ld Lh Li Lp Lt Lv Lw Ly Lz Mb Mc Md Me Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe OF Og Oh Ok Om On Op Ou Oy Pa Pb Pc Pd Pe Pf Pg Ph Pi Pj Pk Po Pz Qa Qb Qc Qd Qe Qg Qh Ql Qm Qt Qu Qv Qx Qy Qz Ra Rb Rc Rf Rg Rh Ri Rm Rt Ru Rv Rx Ry Rz Sf Si Sj Sr Ss St Tn To Tr Tv Tz Ua Ub Uc Ud Ue Uf Ug Uk Ul Um Un Uo Up Ur Ut Uu Uv Uw Ux Uy Uz Va Vb Vc Vh Vi Vo Vs Vt Vw Vz Wb Wc Wd We Wg Wh Yd Yg Yl Zw Zx Tm Tl Xa Wm Tj Th) Uh(aA aC AD aE AF aG aH al AJ aK aL aM AN AO AP aQ AR AS aU aV Aw AX BA bB BC bE bF bG bH bI bJ bL bM BN Bo bP bQ bR bS bU bV bW bX bZ cA cB cC cD cE cF cG cI cJ cK cL cM cN CO CP cQ cR CS CT CU CV CW CX cY cZ dA DB DC DD DE dF DG dH DI dJ Dk DL dM dN Dp Dr Du Em Eq Et Fd Fi Fn Fp FR Fy Gb Gc Gd Gh Gn Gp Gz Ha HB Hc Hf Hl Ho Hp Hq Hr Hu Hv Hw Hx Ib Ic Id Ii Ij Ik In Io Ip Iq Ir Is It Iu Iv Iz Jd Jf Jg Jh Jj Jk Jl Jn Jp Jq Jr Js Jt Ju Jv Jy Kc Ke Kf Kg Ki Kj Kk Kn Ko Kp Kq KS Ky Kz Ld Lh Li Lt Lu Lv Lx Ly Lz Ma Mb Mc Md Me Mf Mg Mi Mj Mk Mm Mn Mp Mq Mr Mt Mu Mv Mw My Mz Na Nc Nf Ng Nh Ni Nj Nk Nl Nm No Nq Ns Nt Nu Nv Nw Ny Oe Of Og Oh Ok Om On Op Or Ou Ow Oy Pb Pc Pd Pg Ph Pi Pj Pk Po Pz Qa Qb Qc Qd Qe Qg Qh Ql Qt Qu Qv Qw Qx Qy Qz Ra Rb Rc Rf Rg Rh Ri Rj Rm Rt Rv Rx Ry Rz Sf Sh Si Sj Sr Ss St Tn Tv Tz Ua Ub Uc Ud Ue Uf Ug Ul Um Uo Up Ur Ut Uw Ux Uz Vb Vc Vh Vi Vj Vo Vp Vq Vt Vz Wb Wc Wd We Wf Wg Wh Yd Yg Yh Yk Yl Zw Zx Ye Tl Xa Wm Tj Ti) Ow(aA aC aD aE aF aG aH al aJ aK AL aM AN aO AP aQ AR AS aU aV Ax BA BB BC bE bF bG bH bI bJ bL bM bN BO bP bQ bR bS bU bV bW bX bZ cA cB cC cD cE cF cG cH cI cJ cK cL cM cN cO cP CQ cR Cs CT CU CV CW CX cY cZ dA DB DC DD dE dF dG dH dI dJ DK DL dM dN Dp Dr Du Ef Ez Fd Fi Fn Fp FR Fw Fy Gb Gc Gd Gh Gn Gp Gz Ha Hb Hf hG Hl Ho Hp Hq Hr Hv Hw Hx Ic Id Ih Ii Ij Ik Il Im In Io Ip Iq Ir Is It Iu Iv iZ Jd Je Jf Jg Jh Ji Jj Jk Jl Jm Jn Jp Jq Jr Js Jt Ju Jv Jy Kc Kd Ke Kf Ki Kj Kk Kl Kn Ko Kp Kq KR Ks Kx Ky Kz Ld Lh Li Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nd Ne Nf Nh Ni Nj Nk Nm Nn Nq Nr Ns Nt Nu Nv Nw Nx Ny Oa Oe Of Og Oh Ok Om On Op Or Ou Oy Pa Pc Pd Pe Pf Pg Ph Pi Pj Pk Po Pz Qa Qb Qc Qd Qe Qg Qh Ql Qm Qn Qu Qv Qx Qy Qz Ra Rb Rc Rf Rg Rh Ri Rj Rm Rt Ru Rv Ry Sf Si Sj Sr St Tn To Tv Tz Ub Uc Ud Uf Ug Uk Ul Um Un U'o Up Ur Ut Uw Uy Uz Va Vb Vc Vh Vi Vp Vq Vs Vt Vw Vz Wc We Wf Wg Yl Ye Tm Tl Xa Wm Tj Ti Th) Oi(AD Af aG aH al AJ aK Al AN Ao AP aQ aR AS aU aV AW aX aZ BA BB BC bF BG bH bJ bL bM BN BO bP bQ bR bV bW bZ cB cC cD cE CH cI cJ cK cL CO CP CQ cR CS CT CU Cv CW CX cZ Db DC DD DE dF DG DI dJ DK DL dM Dp Dr Du Ef Em Eq Et Ex Ez Fc Fi Fn FP Fr Fw Gc Gd GL Gp Ha hB HC HF HI Hq Hr Hu Hv Hw Hx Ic IH Ii IJ Ik Il Im In IO IP Iq Ir Is It Iu IZ Jd Jg Jh Ji Jj Jk Jm Jn Jo Jp Jq Jr Js Jt Jv Kd Ke Kf Kg Ki Kj Kk Kl Kn Ko Kp Kr kS Kx Ky Kz Ld Lh Li Lp Lt Lu Lw Lx Ly Lz Ma Mb Mc Md Me Mf Mg Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe OF OH Ok Om ON Op Or Ou Oy Pa Pb Pc Pd PF Pg Ph Pj Pk Po Pz Qa Qb Qc Qd Qe Qg Qh Ql Qt Qu Qv Qw Qx Qy Qz Ra Rb Rc Rf Rg Rh Ri Rj Rm Rt Ru Rv Rx Ry Rz Sh Si Sj Ss St Tn To Tv Tz Ua Ub Uc Ud Ue Uf Ug Uk Ul Um Un Uo Up Ur Ut Uu Uv Uw Ux Uy Uz Vc Vh Vi Vp Vq Vs Vt Vw Wc Wd We Wg Wh Yh Zx Ye Tm Tl Xa Wm Tj Ti) Vs(aA AD aE Af aG aH al AJ AL aM AN aO aP aQ AR AS aV Aw Ax aY aZ BA BB Bc bE bF Bg bH bI bJ bL bM BN bO bP bR bS bU bV bX cA cB cC cD cE cF CH cI cJ cK cM cO CP CQ cR Cs CT cU CV cW CX cZ dA DB DC DD DE dF DG dH Di dJ DK DL dN Dp Dr Du Ef Em Eq Ex Ez Fd Fn Fp FR Fw Fy Gb Gc Gd Gh GL Gn gP Gz Ha Hb Hf Hl Hp Hq Hr Hu Hv Hx Ic Id Ih Ii Ik Im In Io IP Iq Ir Is It Iu Iv Iz Jd Je Jf Jg Jh Ji Jj Jk Jl Jm Jn Jp Jq Jr Js Jt Ju Jv Jy Kf Ki Kj Kk Kl Kn Ko Kp Kr Ks Kx Ky Kz Ld Lh Lp Lt Lu Lv Lw Ly Lz Ma Mb Mc Md Me Mh Mj Mk Ml Mp Mq Mr Ms Mt Mu Mv Mw Mx My Mz Na Nb Nc Nd Ne Nf Ng Nh Ni Nj Nk Nl No Nq Nr Ns Nt Nu Nv Nx Ny Oa Oe Of Og Oh Ok Om On Op Or Ou Oy Pa Pb Pc Pd Pe pF Pg Ph Pi Pk Po Pz Qa Qb Qc Qd Qe Qg Qh Ql Qm Qn Qt Qu Qv Qw Qx Qy Qz Ra Rb Rf Rg Rh Ri Rj Rm Rt Ru Rv Rx Ry Sf Sh Sj Sr Ss St Tn To Tv Tz Ua Ub Uc Ud Ue Ug Ul Um Un Uo Up Ur Ut Uu Uv Uw Ux Uy Uz Va Vb Vc Vh Vi Vj Vo Vp Vt Vw Vz Wb Wc Wd We Wf Wg Wh Yd Yl Zw Zx Ye Tm Tl Xa Wm Tj Th tF Yf) Mh(aA aC Ad AF aG aH al AJ aK AL aM AN Ao Ap aQ AR aS aU aV Aw AX aY aZ Ba BB BC bE bF Bg bH bJ bL bM BN bQ bR bS bU bW bZ cC cE cG Ch cJ cK cL cM cN CO CP CQ cR CS Ct CU cV Cw CX cY cZ dA DB Dc Dd DE Dg Di dJ DK Dl dM dN Dr Du Ef Eq Et Ex Ez Fi Fp FR Fw Gb Gc Gd Gl Gp Gz hB Hf Ho Hq Hr Hu Hv Hw Hx Ib Ih Ij Ik Il Im In Io Ip Iq Ir Is It Iu Iv Iz Jd Jg Jh Ji Jj Jk Jl Jm Jn Jo Jp Jq Jr Js Jt Ju Jv Kc Kd Ke Kg Ki Kj Kk Kl Kq Kr Ks Ky Kz Lh Li Lp Lt Lu Lv Lw Lx Ly Lz Ma Mb Mc Md Me Mf Mg Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe Of Og Oh Ok Om On Op Oy Pb Pc Pd Pe Pf Pg Pi Pj Po Pz Qa Qb Qc Qd Qe Qg Qh Qn Qt Qu Qx Qy Qz Ra Rb Rc Rf Rg Rh Ri Rt Ru Rz Sf Sh Sr Ss St Tn To Tv Tz Ua Ub Uc Ud Ue Uf Ug Uk Ul Um Un Uo Up Ut Uv Uw Ux Uy Uz Va Vb Vc Vh Vi Vj Vo Vp Vq Vw Vz Wb Wc

Mx Nf Nh Nj No Oa Oe Of Og Om Oz Pa Pc Pd Pg Ph Pj Po Qa Qb Qc Qd Qe Qh Ql Qn Qy Qz Rb Rh Ri Ru Rx Sf Si Sr Ss Tn Tz Ue Uf Uh Uk Ul Up Uu Uv Uy Va Vb Vq Vs Wd Yd Zw Tl Xa Th) Oa(aC aD AF AJ aK Ap aQ Ar aU aW aX aY aZ Bb bC bF bJ bM Bo bS bW bX cE CH cJ cL CO cP cQ Cv CW Cx cY cZ Dd De dG dI dJ DK dM dR Ed Et Ex Ez Fc Gb Gc Gn Gp Ha Hb Hl Ho Hv Hw Ib Ic Ii Ij iP It Iu Iv Iz Je Jh Ji Jj Jk Jl Jy Kc Kd Ke Kg Kj Ko Kq Kz Lp Lu Lx Mg Mi Mj Mk Mm Mp Mq Mt Mu My Na Nm Nn Nq Nv Nw Nx nY OE Of Og Oh Oi Om Or Oy Oz Pa Pc Pd pF Qv Qy Rb Rj Rt Rv Rx Ry Rz Si Sr Ss Tn Ue Uf Ug Uk Un Ur Uu Vj Vp Vt Wd We Zw Ye Ti) Of(Ad aF aG As aV AW BA Bb bE bF Bo bQ cD cE CH cM CP CQ cR CU Cv CW Cx Dc dJ dK Ed Ef Eq Et Ez Fw Fy gP Hl Hv Ib Ic Id Ih Il Im In IP Iq Ir Iv Iz Jd Jh Ji Jk Jm Jn Jq Jr Js Jt Ke Kf Kk Kn Ko Kq Kr Ks Lu Lw Mk Ml Mn Mq Mx Mz Nb Nf Ng Ni Nm Nr Nt Nu Nv oE oF Og Oh Ok ON Ou Pb Pg Ph Pi Pk Po Pz Qa Qb Qc Qd Qe Qh Ql Qu Qx Qz Ra Rb Rh Rj Rm Rv Rx Sr St Tn Tv Tz Ub Uh Uk Un Up Ur Ut Uu Uz Vj Vp Vs Vt Vu Wg Wh Yi Yl Xa Ti) Ed(aE Af aG aH Aj aK Ap aU aW aZ BA BB bC bF Bn Bo bQ bS bX cD cG CH cL CO cT Cx cY dB Dc Dg DK dN Dr Ez Fc Fi Fr Fy Gb Gc Gd Gn GP Gz Hx Ib Ic Ih Im iP Ir Is Iu Ji Jj Js Jy Kc Kd Ke Ko KQ Kz Lu Lz Md Mf Mg Mh Mi Ml Mm Mn Mp Mq Mt Mu .Mv Mx My Na Nb Nc Nf Nh Nl Nm Nn Nv Nw Nx nY Oe Og Oh Ok Om oN Or Oy Oz Pa Pd Pf Pj Po Qa Qh Qx Qy Ra Rb Rj Rm Rt Ru Ss St Tn To Uf Uh Ur Uu Vq Vt Wb Zq Ye Tl Xa Wm Ti) Uu(aC aF Ao Ap aU aW Ba Bb bC bE bF bl bJ bW bZ cC CH Co cP cZ Dd De Dg Dk Et Ez Fc Fn fP Fw Gb Gc Gd GP hF Ho Hq Hx Ii Il Im IP Iq Ir Is It Iu Iv iZ Jf Jg Jh Ji Jk Jn Jp Js Jy Kc Kd Ke Kg Ko KQ kS Kz Lu Lx Mf Mg Mi Mm Mp Mq Mt Mu Mw Mx My Na Nf Ng Nj Nk Nm Nn No Nv Nw Nx nY oE Og Oh oK ON Or Oz Pd PF Pg Pj Po Pz Qa Qb Qc Qd Qe Ql Qt Qy Qz Rb Rh Rm Rz Sr St Tn Tz Uc Uf Uh Uk Un Ut Vh Wd Zx Xa) Nw(aD aF al Aj aO Ar aW aZ bF bL BN bZ cE CH cV dK dR Ef Ex Fr Fw Gh GL gP Hq iA Ih Ij Im In Iv Iz Jl Jm Jp Jq Jy Kd Kr Ky Lv Mf Mh Ml Mx My Nb No Nt Nu Nv Nx oE oF Og Oi On Or Ou Oz Pa Pd Qn Rb Rg Ru Ss Tn Ub Uk Ul Up Us Uy Va Vp Vs Zx Th) Lu(aF aH aJ aM An AP Ar aS aU aW Ax aZ Ba Bb bJ Bn BO bQ bW cC cE Ch cJ cO cQ Cs Ct cU cV dE Dk dL Eq Fc Fi Gc Gh Gl Ha hB Ib Ih Ir Iv iZ Js Kd Ke Kq Kx Mh Ml Mq Mt Mx No Nr Nu Nx Ny Pj Po Qa Qb Qe Qg Rj Rx Sj Uh Vt We Yd Zx) Ch(aF aH aK Ao Ar Bb bC cJ Ct cU cY cZ Dg dK Et Fn Gb Gp Hf Ho Ib Ih Il Im Ir Is Iv Jd Je Ji Jn Js Ki Kj Kk Ko Kz Ma Mf Mn Mr Mv Mw Mx Nm Oe Oh Oz Pf Po Qa Qb Qe Qz Rh Rj Rx Rz Si Sr Tn Ub Uc Ue Uh Un Ur Vq Vt Vu Wd Ti) Vt(aA aF Aj aP Ar aW Ax aY bF bL bN cH cM Ct Dk eM Gh Ib Ij Is Iv Jk Jn Jp Js Jy Ki Kz Lx Lz Mb Mh Ml Mq Mx My Nf Nn Nr Nx Oc Og Oh Oy Oz Pd pF Qb Qu Qv Qx Ra Rb Rg Rt Ru Sr Tn Uh Up Ur Us Va We Yd Zx Wm Ti) My(aF Ao Ap aU aW aX Bb bC bJ bW CO cP cQ cS De Ef Ez Fn Gc Ib Ij Im Ir Is Iu Jd Jh Ji Js Kc Ke Kg Ki Kk Kz Mg Mm Mp Mq Mv Mw Nm Nq Oh Oz Pd Pf Pj Po Qa Qd Qe Qy Rx Si Sr Ue Uf Uh Vq Wd) Uh(aA aD aE aI aP Ar Ax bA Bc bF bZ cD cH cZ Dk DR eF fP gP Ha hB hC hF hG Hq iA iH iJ In iO iP It Iv Jn Jp Js Jy kR Mq Mx Nb Nc Nl nW Nx nY oE oF Og Oh Oi Qa Qb Rb Ru Sr Tn Uv Yd Zx) Im(Ad aH AJ AR aU aZ bF bM Bo bP bS bU bX cF cH Ef Eq fP Fr Hb Ib Ij iP Is Iz Jg Ji Jj Jk Js Jy Ke Kx Lx Mp Mu Mw Oh Oz pF Pz Qt Qu Qv Qz Ss Tn Tz Ua Un Ur Ux Vb Wh) No(aG aQ aW aZ Bb bM Bo bQ bS cB cE cJ cL cP cQ CW cY Dd DK Et Gc gP Hp Ib Ij It iZ Je Ji Kd Ke Lx Mf Mg Mi Mp Nn nY Oh Om Oz Pd pF Qy Rj Si Uf Ug Ur Vq Ye Ti Th) Sr(aD aE aG aH Aj aK aQ Ar aU bA bF Bo cD cE cP cT cV cX cY Dc dF Fn Gp Ih Ii Ji Jj Jq Js Jy Ke Kk Lv Mx Nl Og Oz Pg Qh Rb Rh Rt Sj Ss Tz Ug Ur Vb Vw We Yl Xa Wm Th Yf) Aj(aF Ap aU aW aX bC bE bW cL CO cZ De Ez Fi Fw Gc gL Hv Ih Ij Iu Iv Jd Jh Ji Js Jt Kc Kd Ke Kg Kj Kq Mg Mi Mp Mq Mt Mu Mw Nm Pd Pj Qa Qy Qz Rz Si Ue Uf Wd Zq) Mp(aF AO Ar AX aY aZ bF bL Bn cE cG cH cV De Di Dk Eq fP Fr Gl hG Hq iA Ij Iv Iz Jp Kj Mh Ml Mv Mx Nb Nx oE Oh Oz Qb Qu Qz Ss Tn Ua Uv Ux Vp Vs Wd We) Ke(Ad Ao Ar aW Ax aY bF bL cH Cp De Di Ef Eq Ex Fr Fw Hq Ib Iz Jd Jm Jp Jy Kd Kj Ko Mh Mx Nl Og Ou Oz Pa Rb Rx Ua Ux Uy Wd We Yd Yh Zx Th) Oh(aA aF aN aO aS aW aY Bb bE bF bJ Bn Bo cE cP cV cZ Dd dF Dk Gb Hq Iv Jl Kd Mi Mj Mq Nt Nx Og Oz Pd Qy Rb Rh Rt Rv Tn Ur Uv Vp Zx) Iz(aF Ap aU aW aX Bb bC bW Co De Ef Ez Gc Hv Ih Iu Jd Jh Ji Kc Kd Kg Kq Mg Mi Mq Mt Mu Mv Nq Pd Qa Qd Qy Si Ue Uf Wd Zq) Lx(aD AF aS aW bM Bn Bo bZ cE cV Dd Dr Fc Fr Hq Iv Jy Kd Lv Mf Mj Mn Og Oi Ok On Ou Rg Rh Rt Tr Up Uv Vp Zw) Qa(Ad Af Ar aY aZ bF bM Bn Bo cH dR fP Fr iH iP iZ Jp Jy Mj Nv oE Og On Oy Oz Qt Rb Ss Tn Ur Us Uv Uw Vp Vs) Dk(aM aP Ar Ax aZ cF cJ cQ dL Hb Ih Ij Is Ji Jq Kk Kz Mj Mq Mr Mx Nf Ny Or Oz Po Qb Qe Rm Si Tz Un Vb Yl) Mq(aX aZ bM Bo cR cS Dd Di Ef Eq Fr Fw Hu Jd Jm kQ Mh Mu Mx Ng Oy Pa Qt Qz Ss Ua Uv Ux Uy Wd We Wh Th) aW(Ar aZ bF cH dR Eq fP Fr gL HB hC iA Id iJ iP Iv Jj Jp Js Jy Kg Kj kS nW nY oE Og Qb Qu Ss Tz Ux) Ji(aY bF bZ cH De Ef Fr Gl Hq Ih In iO Iv Jm Jp Jy Mx Nx Og On Pa Rb Ru Tn Ut Uv We Zx Th) Bo(bF bR cH Di eF Fn fP Fw Ha Ih iJ iO Ir Jn Jp Js Kn Mx Mz Nb Nd Ne nW oF Og Qb Qe Vq) Ar(aE aY bF cP Dc Dd Ex Gp Ih Ij Ir Is Jk Jm Jt Kd Nm Og Oz Pa Ru Si Ul Uv Uy Vq Th) Iv(bM cP cQ Gp Ib Ij Ik Ir Is Jd Jm Kd kQ Nx Oy Oz Pa Qh Ru Ss Uv Uy Vb Vw We Ti Th) Qb(Ap aU bC bJ bW cO Cw cZ dI dK dR Kd Mg Mi Mt Nc Nn Pd Qy Rv Uf Ur Vp Zx) oE(aM cQ Ct cU Gc Ib Ir Is Js Jv Kd Ki Mf Nc Nk Nl nY Oi Qc Rc Rj Rx Yd) Ij(aA aZ bM bZ cP Em Hq Ih Jp Jy Mf Mn Nx On Pk Rh Rt Tn Ur Uv Vb) Ux(Ap aU bC bJ bW Co Ez Gc Ho Hv Kc Kg Mg Mi Mu Nn Pd Qy Rz Uf Zq) bF(aH bZ Ct cU Et Gc Gp Ib Is Kd Ki Kk Ma Mf Mn Pf Rj Rx Ub Ur Ti) aZ(aY bJ Bn cV Dl Ez Fc Ih Kd Mg Mi Na Nm Nn Pd Pj Qy Uf Vq Zx) Eq(Ap aX bC bW dK Ez iH Kc Kd Kg Mt Nm Qd Qz Rz Si Uf Vq) Mf(cH eF eM fP gP hF hG iA iH iJ iO kQ kR kS nY oH oK Tn) Mx(aF aU bC cZ Mg Mi Mj Nn Oz Pd Qy Rb Rv Uf Un Ur Vq We) Fr(Ap aU bW Co Ez Jd Kg Mg Mi Mu Nn Om Po Qd Qy Rx Uf) Ib(cH dR gP hC hF hG iH iP iZ Jy kS nW nY Og oH Tn) Oz(Ax bZ cH Fw hF hG Hq Ih iP Jp Js Jy nW Rb Tn Zx) eF(bJ bQ bZ cO cU dK Ez Gc Ho Iu Ma Mn Mt Nm Pf) Mi(aX Co De Hu Jh Kg Kj Mv Qu Qz Ss Ua Uv Wd) Is(aF aO Bn cV Jl Nx Rb Rt Tn Up Vp We Yd Zx) Kz(aN Em Fw Gl Jd Jm Jy Mh Nx Pa Ru To Uy Th) cH(aH cJ cU Et Gc Gp Kd Kk Mn Nn Rj Rx Ur Vq) Ef(Ap aU bC bJ bW Ez Iu Kg Mg Mt Pd Pj Qd) dR(cU Fn Gl Jk Nc Oy Pf Pz Qe Rj Rx Ub Wh) Ss(Ap bE bJ cZ gL Ih iO Iu Mg Nn Pd Uf) We(Cp Dd Hv Jq Js Jt Mw Nm Pd Po Qd Si) Js(aY Bn cP Dd Jl Kd Rt Ur Uv Vp Zw) cQ(bZ eM gL Hq Jy oF Og oK oN Tn Zx) aX(Ap aU bC Ez Mg Mu Nn Pd Qy Zq) cU(bZ fP gP iP Jy kR Og oK Tn) iO(bC Co Gc Ho Kc Mg Mm Nq Rx) Po(aY bM Ex Jm Kd Pa Ru Th) Zx(Gc Ki Lz Ml PF Qx Tz) Ur(fP Fw Ih Jp kQ Nb Pa Th) Vq(Ax hB Jj Jo Rb Rt Vb Vs) Nn(cS Hu kS oF Qz Ua Vb) Qy(Hu Mu Mv Qu Qz Ua Wd) nY(bS Fn Il Ki Mg Mn Rj) Gp(eM gL hC iJ Jp Og) Hv(Ad Mh Ml Oy Qu Uv) Ih(Oy Qt Rc Rj Ug Ye) Mv(aU Co Mt Mu Uf) Nf(Fw Jm Kd Uy Th) Tz(aF aY cV Jl Vp) Hq(aU cG cL Om Pf) Kk(fP Jy Nx Og Tn) Rx(hG iZ Jy kS Og) Vb(Ap Gc iH Iu Nm) pF(Ba Pz Rc Ub Wh) Fn(aY Jl Jy Vp) Jj(Fi Fw Jm Uk) Uf(Co Qu Ua Wd) Pd(Dg Ng Qu Wd) eM(aG aU bZ cG) gL(Mn Oy Ub Ti) Rb(Ir Kd Qe) Kx(aY Ex Nx) Og(Et Oy Rj) Om(Nx Ua Uv) fP(bZ Mn Nq) kS(cP Kd Ki) oN(Jk Mn Pf) Dc(Rt Us) Fw(Hx Rt) Gc(Jp Jy) Qd(Ua Ut) Kq(Ad Uv) Un(aY Nb) aU(De Uv) cL(cE kR) iH(aH Pf) AxcP BbJg TihB LvNx MhRh SiaA QegP JniP JpKi TlKd KgKj OenW VjPa aOoF cGkR} Nw{Th(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR Ed Ef Et Ez Fn Fp Fr Fw Fy GL Gp Ha HB HC Hf Hq Hr Hu Hv Hw Hx Ib Ic Id Ih Ii Ij Ik Il Im In Io Ip Iq Ir Is It Iu Iv IZ Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp Kq Kr Ks Kx Ky Kz Ld Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx NY Oa OE OF Og Oh Oi Ok Om On Or Ou Oy Oz Pa Pb Pc Pd Pe Pf Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Sr Ss St Tn To Tr Tt Tv Tz Ua Ub Uc Ud Ue Uf Ug Uh Uk Ul Um Un Uo Up Ur Us Ut Uu Uv Vo Vp Vs Vt Wf Yd Xa Wm Tj Ti) Yd(aA AD aF aG aH aI Aj aK Al AN AO AP aQ AR aU AW AX aY aZ BA BB BC bE BG bH bJ bL BN BO bP bR bU bV bW

Figure 30 Continued bX bZ cB cC cD cE cF cJ cK cL cN CO CP CS CT CU CV CW Cx cZ Db DC DD DE dF DG dJ DK Dl Dp DR Du Ed Ef Et Ex Ez Fc Fd Fi Fp
Fr Fy Gb Gd Gh Gl Gz Ha Hc Ho Hp Hq Hr Hu Hv Hw Hx lb Ic ld Ih li Ik Il lm ln lo lp lq lr It lu lv Iz Jd Je Jg Jh Ji Jj Jk Jl Jm Jn Jp Jq Jr Js Ju
Jv Jy Kc Kd Ke Kf Ki Kj Kk Kl Kn Ko Kp Kq Kr Ks Kx Ky Kz Ld Lh Lj Lp Lt Lu Lv Lw Lx Ly Lz Ma Mb Mc Md Me Mf Mg Mh Mi Mj Mk
Ml Mm Mn Mp Mq Mr Ms Mu Mv Mw Mx My Mz Na Nc Nd Ne Nf Ng Nh Ni Nj Nk Nl Nm Nn No Nq Ns Nu Nv Nx Ny Oa Of Og Oh Oi Ok Om Op
Or Ou Oy Oz Pa Pb Pc Pd Pf Pi Pk Po Pz Qa Qc Qd Qe Qg Qh Ql Qm Qn Qt Qu Qw Qx Qy Qz Ra Rf Rg Ri Rm Ru Rz Sf Sh Si Ss Tn To Tv
Tz Ua Ub Uc Ue Uf Ug Uh Uk Ul Us Va Vh Vo Vq Vw Vz Wb Wc Wd We Wf Yg Yh Yl Zq Zw Zx Ye Tm Tl Xa Wm) Wf(aA AD aE AF aG
aH Aj AL aN AO aP AR As aV aW AX BA BC bF BG bH bJ bL bM BN Bo bQ bR bU bV bW bX cD cE CH Co CP Cs CT CU Cv Cw Cx dA
Db DC Dd DE dF dH DI dK DL dM dN Dp Dr Ed Eq Et Ex Ez Fc Fp Fr Fy Gb Gh Gl Gp hB Hq Hr Hu Hv Hw Hx Id Ii Ij Ik Il In Io Ip Iq Ir Is
It Iu Iv Jd Je Jg Jh Ji Jj Jk Jl Jm Jo Jp Jq Jr Js Jt Jv Kd Ki Kk Kn Ko Kp Kr Ky Ld Lh Li Lj Lp Lu Lv Lw Lx Ly Lz Ma Mb Mc Md Me Mf Mg
Mh Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns Nt Nu Nv Nx
Ny Oa Oe Of Og Oh Oi OK Om On Op Or Ou Oy Oz Pa Pb Pc Pd Pf Pg Ph Pi Pk Po Pz Qa Qb Qc Qd Qe Qg Qh Ql Qm Qn Qt Qu Qv Qw Qx
Qy Qz Ra Rb Rc Rf Rg Rh Ri Rj Rm Rt Ru Rv Ry Sh Sr Ss St Tn To Tv Tz Ua Ub Uc Ud Ue Uf Ug Uh Uk Ul Um Un Uo Up Us Ut Uu Uv Uw
Ux Uy Uz Va Vb Vc Vh Vo Vp Vq Vs Vt Vw Vz Wb Wc Wd We Wg Wh Yh Yl Zw Ye Tm Xa Wm Ti) Ti(AA Ad aE AF aG aH Aj aK AL
AN Ao AP aQ Ar As aU aV AW Ax aY aZ BA BB Bc bF BG bJ bM BN Bo bQ bR bU bV cD cE cF CH cl cJ cK cN Co Cp Cq Cs CT Cu Cv
Cw Cx cY DB Dc Dd DE dF Dg DI dJ DK Dl Dp DR Ed Ef Et Ez Fn Fp Fw Fy GL Gp Ha HB Hc Hf Hq Hr Hu Hv Hw Hx Ic Id Ih Ij Ik Il Im In
Io Ip Ir Is It Iu Iv lZ Jd Je Jf Jg Jh Jj Jk Jl Jm Jn Jq Jr Js Jt Ju Jv Jy Kc Kd Ke Kg Kj Kk Kl Kn Ko Kp Kq Kr Ks Kx Ky Kz Ld Li Lj Lu Lv Lx
Ly Lz Ma Mb Me Mf Mg Mh Mi Mk Ml Mn Mq Mr Ms Mt Mu Mv Mw Mx My Mz Na Nb Nc Nd Ne Nf Ng Ni Nj Nk Nl Nm No Nq Nr Ns Nt
Nu Nv Nx NY Oa OE OF Og Oh Oi Ok Om On Or Ou Oy Oz Pb Pc Pd Pe Pf Pg Ph Pi Pk Pz Qa Qb Qc Qd Qe Qg Ql Qm Qn Qv Qw Qx Qy
Qz Ra Rb Rc Rf Rg Rh Rj Sr Ss St Tn To Tv Tz Ua Ub Uc Ue Uf Ug Uh Uk Ul Um Un Uo Up Ur Us Ut Uu Uv Vp Vs Vt Wm Tj) Ru(aD aE
AF aH Aj AL aM AN aO aQ aR As aU Ax BA BB BC bF BG bJ bL BN bO bP bQ bV bX cB cD cE CH cJ cK cL Co Cp Cq cR CS CT cV cW
Cx cZ DC De DG dH DI DK dL dN Dp dR Du Ef Em Eq Ex Ez Fc Fd Fi Fn fP Fr Fw Fy Gb Gc Gd Gh GL Gn GP Ha Hb Hc Hf hG Ho Hq Hr
Hu Hv Hw Hx iA Ib Ic Id Ih Ij Ik Il Im In Iq Ir Is It Iu Iz Jd Je Jf Jh Ji Jk Jm Jn Jp Jq Jr Js Jt Ju Jv Jy Kc Kd Ke Kf Kg Ki Kj Kk Kl Kn Ko Kp
Kq Kr Ks Kx Ky Kz Li Lj Lp Lt Lu Lx Lz Mb Me Mf Mg Mh Mi Mj Mk Ml Mm Mp Mr Ms Mt Mu Mv Mw Mx My Na Nb Nc Nd Nf Ng Nh
Ni Nj Nk Nm Nn Nr Nv Nx NY Oa Oe oF Og oK Om oN Op Or Ou Oz Pa Pc Pd Pe pF Ph Pi Pj Po Qa Qb Qd Qe Qg Qh Ql Qm Qn Qu Qv Qw
Qy Qz Ra Rf Ri Rv Rx Ry Rz Sf Sh Si Sj Sr Ss St To Tv Uf Ug Uh Uk Ul Um Uo Ur Us Ut Uu Uv Uw Ux Uy Va Vb Vq Vs Vt Wc Wd We Yl
Zw Zx Ye Tl Xa Wm Tj) Im(aA Aj Et Fc Fd Fi Fp Fr Gb Gh Hl Ho Hp Hq Hr Hu Hv Hw Hx Ic Ih Ii Ij In IP Iq Ir Is It Iu Iv Iz Jg Jh Ji Jj Jk Jl Jm
Jn Jo Jp Jq Jr Js JT kE kP Lh Li Lj Lp Lt Lu Lv Lw Lx Ly Lz Ma Mb Mc Md Me Mf Mg Mh Mi Mj Mk Ml Mn Mq Mr Ms Mt Mu Mv Mw Mx
My MZ Na Nb Nc Nd Ne Nf Ng Nh Ni Nj NK NL Nm Nq Ns Nv Ny Oe Of Og Oh Oi Ok ON Op Oy Oz Pa Pb Pc Pd Pe Pf Pg Po Pz Qa Qb Qc
Qd Qe Qt Qw Rt Rv Rx Ry Rz Sf Sh Si Sj Tn To Tr Tv Ur Us Uy Uz Va Vb Vc Vh Vj Vw Vz Wb Wc Wd We Wg Wh Yi Yl Zw Zx Ye Tm Tl
Xa Wm Yf) Rx(aA Af al aP AR aV aW AX aY aZ bA bH bJ bL bN Bo cB cD cE Ch cN Co cR CS cT cZ dC De Dg Dl dM DR eF Ex Fp Fw Fy
Gb Gl Gz Ha hB hC Hp Hw Hx iA IH Ij iP Ir It Iu Iv Jj Jm Jn Js Kd Ke Kj Kl kR Kz Ld Lp Lu Lx Lz Ma Mh Mi Mk Ml Mm Mn Mq Mr Mw
Mx Na Nb Nf Nr Nt Nu nW Ny oE OH Oi oN Oz Pa Pd Pe Pi Pk Po Qa Qb Qn Qx Ra Rf Sh Ss St Tn Ub Ul Up Uu Uv Uy Va Vp Vs Vt Xa Tj
tF) Oz(aA Et Fp Fr Gh Hq Hr Hu Hv Hw Hx Ih Ii Ij Ik Il In Io Ip Iq Ir Is It Iu Iv Jh Ji Jj Jk Jl Jm Jn JO Jp Jq Jr Js JT Lh Li Lj Lp Lu Lv Lw Lx
Ly Lz Mb Mc Md Me Mf Mg Mi Mj Mk Ml Mm Mn Mp Mr Ms Mt Mv Mw Mx My Mz Na Nb Nc Nd Ne Nf Ng Nh Ni Nj Nk Nl Nm Nn No
Nq Nr Ns Nt Nu Nv Ny Oe Og Oh Oi Ok On Oy Pa Pb Pc Pd Pe Pf Po Pz Qa Qb Qc Qd Qe Xa) Us(Aj AO Ax Bg bN Ch cl cJ dJ dK dM Dr Du
Eq Fc Fd Fi Gb Gc gL Gn Hc Ho Hp Hq Hu Ic Ir Ji Jj jT Jv Kc Kd Ke Kf Kx Li Lj Lt Lx Mc Mh mM My Nc Nh Nl Nj Nl No Ns Oa OE Oi oN
Op Oy Pi Qe Rt Rv Rz Sf Sh Sj Sr Tt Tv Uf Uw Ux Uz Vb Vc Vh Vj Vw Vz Wb Wc Wd We Wg Wh Yh Yl Zw Zx Ye Tl Xa) Jj(aA bO Ed Et
Fp Hc Hf Hq Hr Hu Hv Hx Ic Ih Ii Ij Ik Il In Io Ip Iq Is It Iv Iz Ji Jm Jn JO jP Jr Js JT Kc Kk Kn Ko Lh Li Lj Lu Lv Lw Lx Lz Mc Mf Mg Mi Mj
Mn Mr Ms Mt Mw Mx My Mz Nb Nc Ng Nj Nl Nm Ns Ny Oa Oe Og oN Oy Pb Pc Pe Pf Po Qa Qb Qc Qd Qe Ri Vt Wm) Ij(Aj Eq Et Fc Fp Gb
Hc Hl Ho Hq Hr Hu Hw Hx Ii Il It Jg Jh Jm Jn Jo Jp Jq Jr Js Lh Lj Lp Lu Lx Mc Md Mf Mi Mj Mk Ml Mq Mv My Na Ng Nh Nj Nl Ns Ny Og
Op Oy Pa Pb Pe Po Pz Qb Qc Qe Rv Ry Sf Sh Si Tn Uw Ux Uy Va Vb Vc Vw Vz Wb Wc Wd Wg Wh Yl Zx Ye Tm Tl Xa) It(aA Et Fp Hq Hr
Hu Hv Hw Hx Ii Ik Il In Is Jg Jh Ji Jk Jl Jm Jn Jo Jp Jq Jr Js Jt Lh Li Lj Lu Lv Lx Lz Mc Md Mf Mh Mj Mk Mn Ms Mv Mw Mx My My Mz
Nf Ng Ni Nj Nk Nl Nq Ns Ny Oe Og Oi Ok Om Oy Pa Pb Pc Pd Pe Pf Pg Po Pz Qa Qb Qc Qd Qe Ux Uy Va Yh) jT(Bg CH Dp Ed Et hA Hq Hr
Hu Hv Hw Hx Ic Id Ih Ik Ip Is Jd Je Jg JH Ji Jk Jl Jm Jn jO JP Jq Jr Js Jt Kc Kn Lh Li Lj Ly Mk Ml Mn My Mz Na Nd Ne Ng Nh Nl No Oa Oh
Om Oy Pf Pg Po Pz QA Qb Qc Qd Qe Qt Qu Qv Qy rA Ri Ua Vt Vu Vv Tj) Lj(Du Et Fc Fp Gb Hq Hr Hu Hv Hw Hx Ih Ii Ik Il In Io Is Jg Jh Ji
Jk Jl Jm Jn Jo Jp Jr Js Jt Kc Li Lu Lw Lz Ma Mc Md Mf Mh Mj Mn Ms My Nc Ng Ni Nj Nl Ns Ny Oe Og Oi Ok Oy Pa Pb Pc Pd Pe Pf Pg Po
Pz Qa Qb Qc Qd Qe Ur Vw Wb Wc) Li(Aj Du Ef Eq Fc Fi Fp Fr Gb Hq Hr Hu Hx Ii Ik Il Jh Ji Jk Jm JO Jp Lp Lu Md Mh Ms Mv Mw My Nc
Nd Ng Nj Nl Ns Ny Oe Og Oy Pb Pc Po Qa Qb Qc Qd Rt Rv Sf Sh Si Uw Ux Uy Uz Va Vb Vc Vh Vw Wb Wc Wd We Wg Wh Zx) Ed(Aj Bg
Ch De dK Dr Du Eq Fc Fi Gb Gc Gl Gn Hc Hl Ho Hp Ii Ir Iz Jk Kc Lp Lt My Nl nW OE oN Op Qu Ri Rv Ry Rz Sf Sh Sj Tv Uw Ux Uy Uz Vb
Vc Vh Vj Vv Vw Wb Wc Wd We Wh Yh Yj Yl Zq Zw Zx Ye Tm Tl Xa Yf) jO(Et Hq Hr Hu Hv Hw Hx iB Ic Id Ik Jg Jh Ji JK Jl Jm Jn Jo JP Jq
Jr Js Jt Lh Lu Mk Mz Ne Ng Nh Nl Oa Oh Oy Pb Pc Pd Pe Pf Pg Po Pz Qa Qb Qc Qd Qe Qt Qy Ri Ua Um Ur Vv) No(Du Eq Fc Fd Fi Gb Gh
Hc Hl Ho Hp Iz Kc kE Ks Lp Lt oN Op Rt Rv Ry Rz Sf Sh Si St Tn Ur Uu Uw Ux Uz Va Vb Vc Vh Vw Vz Wb Wc Wd We Wg Wh Yh Yl Zw
Zx Ye Tm Tl Xa) Pe(Eq Fc Fd Fi Gb Gh Hl Ho Hp Ii kE Lp Lt Mk My mZ nl Ns Op Pb Rt Rv Ry Rz Sf Sh Si Sj Uw Ux Uy Uz Va Vb Vc Vh
Vw Vz Wb Wc Wd We Wg Yg Yl Zw Zx Ye Tm Tl Xa) My(Et Fp Hq Hr Hu Hv Hw Hx Ih Il In Ip Is Jg Jh Ji Jk Jl Jm Jn Jo Jp Jr Js Lh Lu Mn
Ms Mw Nc Nj Nl Ns Oe Og On Oy Pa Pb Pc Po Pz Qa Qb Qc Qd Qe Tt Wm) Va(aE aH aN aV aW BA bJ bL Bn BO cB cD cT cW dC dl DreF
Ex Fc Fw Gh Gl Ih Iv Jm Ju Jv Kd Kr Ld Mx Nb Ng Nt Nu Ny Og Or Pd Qu Sr Tv Ub

Figure 30 Continued rW) Ef(hA iB iC jD jE jF jG jH jI jK jL jM jO jP jQ jR jT jU jV jY lK lL lM lN lO qA qB qD vS) Ua(hA iB iC jD jE jF jG jH jI jK jL jM jO jP jQ jR jT jU jV jY lK lL lM lN lO rU rV rW vS) Uh(hA hR iB iC jD jE jF jG jH jI jK jL jM jO jP jQ jR jT jU jV jY lK lL lM lN lO) Qy(eT fN fY hL jT pS pY rN rP rQ rR rV rW sM uG uN uX uY vA vQ vW yJ yK yE) hP(As Ct Hc hR Ii Ik In Iq Ir Iz Jk Ke Ks Mg Ng Oe Of Oy Qc Qv uL Us) Qw(jD jE jF jG jH jI jK jL jO jP jQ jR jT jU jV jY lM lN qD rW) jT(Cp cQ Ct De Iz Ji Jj Kj Kn Ng Nh Nl Qt Qu sC uI Us wF) qD(Ba Cp Ct hR hV hX In Iz Jk Mu Mv My Oe Of Oy Qt wF) rW(Cq Ct hX Il In Jk Jm Mg Mu Mv My Ng Nq Of Oy uI Uk) cW(pS sK sO uG uL uM uN uO vT wD wE yJ yK yL zA zH) uI(aO dH dK eC It Iv jO Kk Kp qW qZ rB rC) hR(Cp eT fN fY hL Kn oH pY qA qB qZ yK) Ke(eT fN pS qA rQ rR sK uV vT wF yD) Ct(fN jO jP lL pY qA qB rU rV vS) rN(Cp cR Dk Fw Hw In Kk Nt Ou) qZ(bL cQ dJ Dk eC Or Ph wF) uL(bL cK dA hA lO oE oN pF) Nt(fN pS rP rQ rS sM sO) Jk(pY qA qB rQ rU rV sO) Li(Du Fc Rt Rx Yd Ti Th) vS(Aj Bc bL dA oE oN Uk) rU(Ba Cq Il Iz Jm Uk) vV(aF bP cZ Kk qW rB) Hc(hA jL jU lK lO) wF(aO cE dH lL rC) lM(Cp cQ Iz Qt Us) rV(Cq Il Iz Jm Uk) yL(eC Fw hA nW qT) Nl(hX jK jL jO) Jj(jK jO jP lN) bL(sO uT wJ yJ) wK(cK hA pF rC) qB(My Ng Of Oy) lL(Cp Kk Kn tU) vB(eC qT qY rB) Ed(Ru Xa Ti) Or(sO uT vH) fN(In My Of) qA(Ng Of Oy) jF(sO tQ wH) wE(dA jL kS) Eq(Kq Nn) Th(Ar Ij) Iz(jU jY) Sh(Ij Nn) Ji(jO jP) Wf(Kq Mw) Kn(eD jO) bP(pS sO) cR(rS rT) eC(rX yE) mZ(cL Mt) wJ(hA oE) hX(oH zA) tU(oK qY) rB(sC vP) jL(hB zA) uG(jK nW) BoRu NdwD InpY IsRt WbOh cKyD cZrR hWoH iByJ hGuZ oNuT} Ij{Th(AA aE Af aH Aj aK Al aM Ao AP aQ AR aU aV aW AX aZ Ba BC BG bJ bM Bo bR bU bV bW cF Ch cM CQ cR CS Ct Cu Cv cY Dd De Dg Di dJ Dk Dl dN Dp Dr Ed Et Ez Fc Fp Fr Fw hB Hc Hf Hl Hq Hr Hu Hv Hx Id Ih Ii Ik Il In Iq Is It Iu Iv Jd Jh Ji Jj Jk Jl Jm Jn Jo Jp Jq Jr Js Jt Ju Jv Kc Kd Ke Kg Kj Kk Ko Kq Kx Ky Kz Lh Li Lj Lu Lv Lw Ly Ma Mb Md Mf Mg Mh Mi Mj Mk Ml Mm Mn Mp Mq Ms Mt Mu Mv Mw Mx My Na Nb Nc Nd Ne Nf Ng Nh Ni Nl Nm Nn Nq Ns Nt Nu Nv Ny Oe Of Og Oh Oi Ok Om On Or Oy Oz Pa Pb Pc Pd Pf Pg Ph Pk Po Pz Qb Qc Qd Qe Qg Qh Ql Qt Qu Qv Qw Qx Qy Qz Rb Rc Rh Ri Rj Rm Rt Rv Rx Sh Sr Tv Tz Ua Ub Uc Ue Uf Ug Uh Uk Ul Um Un Up Ur Us Ut Uu Uv Vb Vo Vp Vs Vt Vz We Wm Tj) Sh(aE Af aH Aj AL aN Ao Ar As AW aY bA Bb Bc bF bG bJ bL bN bQ bZ cD CH cI cL cN cP CQ CT Cu cW Cx Dc DE dI dM Dp Dr Ed Fc Fn fR Fw Fy Gb Gd Gl Gn Gz Hb Hc Ho Hq Hr Hu Hx Ic Ih Il In Ip Iq Is It Jd Je Jj Jk Jl Jm Jn Jo Js Jt Ju Jv Kd Kf Kg Kj Kk Kp Kq Lj Lp Lv Mb Mc Mk Mm Mp Mq Mt Mw Mx Na Nb Nd Ne Nh Nk Nl Nm Nn Nu Nv Ny Oc Of Oh Oi Om Or Ou Oz Pa Pd Pf Pg Ph Pi Pj Pk Qc Ql Qn Qv Rb Rh Ri Rt Ru Rx Sf Si Sj Uk Um Up Us Uu Uv Va Vb Vz Wb Yd Zw Zx Ye Wm) Vb(aA Af Ap Ar aU aW aY aZ Ba BC bG bN bQ bW cE cL Co Cq cR Cu Cv CW Dd Dr Ez Fp Fw Gb Gd Gz Hu Ih Ik In Io Je Jf Jh Jk Jo Ju Kc Kd Ke Kq kS Li Me Mg Mh Mi Mn Mp Mq Mt Mw Nb Nh Ni Nj Nk Nn Nq Nt Nu Nv Om Pb Pd Pf Pi Pk Qz Rt Rv Rz Sf Ua Uf Un Uo Up Vh Vt Vz Wc Wh Ti) We(aH aM bM cI Cp Cu Dc Ed Fd Hv Ih Is It Je Jk Jq Jr Ki Me Mi Mp Mq Mr Mt Mu Mw Nb Nd Nt Nu Nv Ok Om Or Pa Pd Pg Qh Rc Rm Rt Tv Uc Uu Vp Vs Vt Vz) Ed(Dr Du Eq Fc Gb Gc Gh Gn Hl Ho Hp Lp Lt Op Rt Ru Rv Rx Ry Rz Sf Si Sj Uw Ux Uy Uz Vc Vh Vj Vw Wb Wc Wd Wf Wg Wh Yh Yj Zq Zw Zx Ye Tm Tl Xa) Wb(aA aE Aj aK As aU aW aZ bG Ch cP cT cV Dc dJ Fd Fn Fw Hf Ih In Ip Is Jj Js Kd Ke Ki Kk Lj Lu Mh Mk Mp Nd Nh Oh Pa Pd Pk Qn Rb Rh Tz Uu) Vz(aA Aj aW aY aZ bA Bb bG bM bU cB CH dE dJ Em Fn Gp Hc Ih In Ip Jj Jm Jn Jo Kk kQ Lj Mk Mp Nb Ne Nk Nx Ny Pa Pd Pf Pk Rc Rh Sj Uu Vh) aA(Du Eq Fc Fd Fi Gb Gh Ho Lp Lt Op Rt Ru Rx Ry Rz Sf Si Uw Ux Uy Uz Va Vc Vj Vw Wc Wd Wg Wh Yd Yg Yh Yi Yl Zq Zw Tm Tl Ti Yf) Rt(aD aE bM cX Dp dR Fn Hf Ih Jj Jk Jn Jo Jq Js Kk Lv Me Mp Nb Nd Nv Ny Oh Om Pa Pg Pi Qb Qd Qh Qn Qv Rh Rm Uc Uu Vt Yf) aZ(Du Eq Fd Fi Gh Ho Hp Lp Lt Ru Rx Ry Si Sj Uw Ux Uy Uz Va Vc Wf Wg Wh Yd Yh Yj Yk Yl Zx Ye Tm Tl Yf) bM(Eq Fc Fd Fi Gh Hp Lp Lt Op Ru Rx Ry Rz Sf Sj Ux Uy Uz Va Vj Vw Wc Wd Wf Wg Wh Yj Yl Zw Zx Ye Tm Tl) aE(Du Fc Fd Fi Gb Gh Hp Lp Lt Op Ru Rx Sf Si Sj Uz Va Vc Vh Vw Wc Wd Wf Wg Wh Yd Yg Yh Zw Tm Xa) Uu(Dr Du Gb Gc Ho Hp Lp Ru Rv Sf Si Uw Ux Uy Uz Vc Vh Vw Wc Wd Wf Wg Wh Zw Zx) Eq(aU Ba CO Ez Hf Ih Jd Jh Li Mi Mp Mt Mu Nn Nv Om Pd Qc Qy Qz Rz Ua Wd) Hl(aW bG Dc Di Fd Fw Ih Jm Jn Kk Lp Nc Nd Nl Nx Pa Pk Qb Ru Vq Yh) Xa(Ad Af aY cF Dg Fd Gd Hc Hf Kd Kk Kl Mp Mq Nb Of Oz Pa Pi Qm Yh) Fc(Aj Bo Dc Ih Is Jj Jl Jn Jo Ke Kk Mp Nb Ny Of Or Pk Qn Tz Tj) Fd(AD Af aN bG cP Gn Hr Hu In Jj Jo Nk Nl Rb Um Ur Va) Jo(Du Ho Hp Rv Rx Ry Rz Sf Wc Wd Wf Wh Yj Yl Zw Ti Yf) Yh(cT cV Cx Dc Is Jj Ke Kk Lv Om Po Qd Qn Sj Tz) Vh(Bc bG Ih Ke Mp Pa Pk Qd Qe Ri Tz Um Vq Vt) Wf(Bo Jl Jn Ki Kk Mr Nb Nv Ny Of Qd Ri Um) Zw(Ih Is Jj Jl Jn Kk Mp Nv Ny Pi Pk Tz) Sf(Aj aX aY cI Gl Ih Jm Ny Of Pa Pk) Gn(Ha Hf Je Nc Ne Nh Nl Pi Pk Qn) Jj(Du Hp Ji Li Rv Ux Uy Va Vw Wh) Dr(aD cP Fn Hp Kk Nc Ne Nl Rh) Ti(Ar Ch Id In Li Lj Nk Vt) Ux(Kq Mp Mq Nb Om Pd Qd Qy) Yd(bG Hv Is Kk Lv Mp) Sj(Af aY bG Je Ny Of) Ho(Aj Ch Kg Of Rh) Ye(Hv Ih Mp Mq Ny) Kk(Gb Gd Op Rv Zx) Rh(Fi Si Va Wc) Ch(jT Wd Zq) Du(Hf Hv Nl) Gc(Nc Ne Nl) Mp(Ru Uy Va) Tz(Rv Va Wc) Rx(Ih Ke Ny) Vc(hB Hf Rb) Bo(Uy Yi) Gb(Gd Nm) Yj(cF Pk) Zx(Jl Ki) Wd(Kg Ny) Rv(Ih Ny) Yl(Nl Rb) Of(Uz Wg) jT(Ct Ji) GdKo MqVw NbTl HpIn HcWh HfRu YgQd ZqaX KiOp LpUr} Ed{Xa(aC AD aE AF aG aH aI AJ AL AN AO AP aQ AR As AW AX aY bA BB Bc bE bF BG bJ BN bP bS bU bV bW bX bZ cD cF cG Ch cI cL cN CO cP CQ cR CS CT cU CV Cw CX cZ DB dC Dd DE dF DG DI dJ DK Dl dM dN Dp Dr Du Ef Em Ex Ez Fc Fd Fi Fn Fp FR Fw Fy Gb Gc Gd Gh Gl Gn Gp Ha Hb Hf Hl Ho Hp Hq Hr Hu Hv Hw Hx Ib Ic Id Ih Ii Ik Il In Io IP Iq Ir Is It Iu Iv Iz Jd Je Jf Jg Jh Jj Jk Jl Jm Jn Jp Jq Jr Js Ju Jv Jy Kc Kd Ke Kg Ki Kj Kk Kl Kn Ko Kp Kq Kr Ks Kx Ky Kz Lh Li Lj Lp Lv Lz Ma Mb Md Me Mg Mh Mi Mk Ml Mm Mn Mp Mq Mr Ms Mt Mu Mv Mw Mx My Na Nb Nc Nd Nf Ng Nh Ni Nj Nk Nl Nm Nn Nq Nr Nt Nu Nv Nx Ny Oe OF Oh Ok Om On Op Or Ou Oy Oz Pa Pb Pc Pf Pg Ph Pi Pj Pk Po Qh Ql Qm Qn Qt Qw Qx Ra Rc Rf Rh Rj Rm Ru Rx Ry Rz Sf Si Sj Sr Ss St Tn To Tz Ua Uc Uf Ug Ul Un Ur Uu Vh Vp Vs Vz Wb Wc Wf Wh Yd Yi Yl Zw Ye Tm Tl Wm Tj Ti Th) Ru(aE aH aK Ao aQ aU aZ Ba bM bX bZ Cp cQ cW cY Dc dR Et Ez Fw Gd Gp Hb Hq Hv Hx Ih Is Iu Jd Ji Jj Jq Js Ke Kk Kq Kz Li Lu Lv Ma Md Mi Mp Mq Mr Mv Nb Nc Nf Nq Oh Om On Ou Oz Pg Qd Qh Qm Rh Rm Si St Tn To Tz Uc Uf Ug Un Ut Vq Vs Vz Yd Tm Tj) Oh(Du Eq Fc Fd Fi Gc Gh Gn Hl Ho Hp Lp Lt Op Rt Rv Rx Ry Rz Sf Sh Si Sj Uw Ux Uy Uz Va Vb Vc Vh Vj Vw Vz Wb Wc Wd We Wf Wg Wh Yd Yl Zw Zx Ye Tm Tl Ti Yf) Kq(Dr Du Fc Fd Fi Gb Gc Gh Hl Ho Hp Lp Lt Op Rt Rv Rx Ry Rz Sf Sh Si Sj Uw Ux Uy Uz Va Vb Vc Vh Vw Vz Wb Wc Wd Wg Wh Yd Yi Yl Zw Zx Tm Tl) Ba(Dr Du Fd Gc Gh Gn Hl Ho Hp Lt Op Rt Rv Rx Ry Rz Sf Sh Sj Uw Uy Uz Va Vb Vc Vh Vj Vw Vz Wb Wc Wd We Wf Wg Wh Yd Zw Zx Ye Tm Tl Yf) Dr(aK Aw bA bQ cL Cp cQ cY Dc Et Ez Fy Gp Hv Ih Iq Ir Ji Js Kd Ke Li Ma Mf Mp Mq Mt Nc Nn Om Oz Pf Qd Qt Rm Si Tn Uc Uh Ut Vs) Et(Eq Fc Fd Gb Gh Hl Lp Lt Op Rv Ry Rz Sf Si Sj Ux Uy Uz Va Vb Vc Vj Vw Vz Wb Wc Wd We Wf Wg Wh Yh Yi Zw Zx Ye Tm Th Yf) Ez(Du Eq Fc Fd Fi Gb Gc Gh Gn Hl Op Rx Ry Sh Si Uy Uz Vc Vh Vw Vz Wg Yd Yh Yl Zx Ye Tl Yf) Li(Du Eq Fc Fd Fi Gb Gh Gn Ho Op Rv Rx Sh Si Sj Ux Va Vb Vz Wc Wf Yd Yi Yk Yl Zw Ye Ti Th) Is(Eq Fc Fd Fi Gb Hl Ho Lp Op Rv Rz Sh Si Va Vj Vz Wb Wc Wd We Wf Yd Yl Zw Zx Ye Tm) Yi(Aj aQ bZ cE cP dE dI Gd Gp Ha Hx In Ji Jj Ki Kp Lu Md Mp Nc Nl Sh Vs Zw Tj Yf) Si(Ax Bc bQ bZ Cs cT Fy Ih Js Lz Ma Ml Nb Nc Ni Nk Nn Oz Pf Qx Ra Rf Rh Tr Wm) Sh(Fy Ih Ir Jg Ji Js Jt Ma Nn Ny On Oz Pf Pz Rm St Tr Uc Ut Uw Zq Ti) Gn(Cu Cw Fy Ih Ir Js Ke Mq Ok On Qe Qx Rm Tn Tr Tv Uc Vs Vt Vv Yh) Ye(Fy Ji Jn Ke Mg Nn Ny Om On Pz Qd Ql Qt Rm Tn Uc Ut Uw Wd Wh Yg) Fy(Du Fc Fi Gb Gc Hl Rt Rz Vz Wb Wd Wf Yd Yl Zw Zx Tm Yf) Zq(Af bF Bn bQ bV cC Ch Cx Di Gd Jm Kc Nb Nl Oi Pf) Uw(Af aQ aZ Bo bQ Cx dR Hc Nb Ne Oz Ug Ur Uu Vt Wf) Ji(Fc Ho jO jT Lp Op Rt Rx Uy Vh Wc We Wh Yl Th) Ih(Gb Gc Hl Hp Lp Rt Rv Rx Sj Wd Wf Yd Tm Ti) Nn(Eq Fd Fi Rx Rz Ux Vb Vw Vz Yd Yl Yf) Ti(aQ Ar Gd Jl Ke Kk Lj Mt Nb Ny Vt) Rt(cT Cu Dc Js Ke Om On Pd Rm Tn Uc) Oz(Fd Gb Gh Ry Rz Ux Vh Vw Yd Yl) Nb(Gb Gc Op Va Vh Wc We Wf Tl) Pf(Fd Gb Rv Vc Vj Vz Wb Yd Yl) Wf(Hx Js Mq Mr Ny On Tn Ut) Js(Du Fc Gb Gc Rv Rz Wd) cT(Gb Gc Rv Rz Va Wd Wh) Gd(Ax dK Kk Qx Tn Vh) aQ(Rx Ux Vb Vw We Wh) Fc(Cw Ni On Tr) Wh(aH aZ Hc oE) Ke(Va Yd Yl Th) Vt(Uy Yl Zw Tl) Fi(Mg On

Kz(Cu Mt Nq Tz Un Vt) Tz(Ni Nt Ql Rv) Hc(Cu Nv Ou Ut) Un(Hf Jn Ky To) Bo(Ha Mr Vu) Fw(Hx Jj Oz) Qe(bM Hl Ur) Gd(Om Zq) Ur(Fd
Pg) Vt(aA Mv) PoaA GbOr MpMr HbfR OmOy) Fw{Oz(Fd Fi Hl Hp Rx Ry Sf Vz Wc Wd Wh Yl Zw Zx) Yl(Ax Cs Fy Ih Lz Na Nr Nt Pd Rf)
Hx(Fc Rx Ye) Yi(Bo Cq Pa) Vz(Et Mt Na) Zq(De Gd Kc) Vj(cF Jl) nl(Qw Ur) BoYg DuPo EtHl GdVh SiaA JnYe RvRm RtOn} Ih{Rx(aH bA
bM cT Dc Fd Hb Hx Jj Jq Kz Mp oE Oz Pi Pk Tz Un) Ye(aA Bo Iv Jd Ky Mt Nv Qd Ut) Bo(Du Fd Ho Uw) Ux(Mp Mt Rj) Oz(Lp Lt Sf) Fc(aH
Or) HbVa IvWh YdOu VzPf WeOm LtVt RjUz UrmZ} Jn{Fc(Bo Hb Oz Rj Ss Ug Ur) Bo(Fd Fi Ho Rx) Rj(ml mZ nl Rv) Rx(Mp Qw Vt)
Vq(Rv Vh Zw) We(Hv Om) Wh(Hc Oz) Ur(mZ Yf) Va(Dd Hb) fP(Rv Rz) DiVj FdOz FiJj VzaW} Sr{aH(Fc Gn Rx Rz Sf Va Wd) Ug(Fd Uw
Vz Wh) Rt(Dc Pg Qh) Oz(Sf Vh We) Bo(Fd Uw) Vz(aU Pf) Va(Dc Mp) HlVu IbnI SfcD} Ti{aA(aQ Ar Ax Dc Id Jl Qd Qe Vt) Ar(Dc Jl Qd Qe
St Tz) hB(Dc Jl Kd Qd Qe) Ax(Un Vt) QdKj QebM JlaY} nW{Vt(rS tO tS uO uT vB vl zG tM) wB(aN iA Ko Lv Nm Qt Rj rS wP) qZ(bS Mi
wL) JlRx aWrS bArN dHtU} Kn{Ph(jl jO jP jQ jR jV) Hw(hR hV hW hX qA) eD(bN cS Tz) jO(cH Ic Ur) Jo(iB jl) EteP JkjQ UrVt cHiB}
Rt{Dc(dR Hx Jr Ky Nf Ng Nt Nv Tv Ut) Cu(Jm Pa Qb) Fd(aW Pf) Iv(Pa Qh) Vq(aA Nv) NrMp NtQh IrbQ JlKd} Pf{Wb(bF bG dR Hc Qw)
Fd(Af aY Bo) Vz(bF iA Ir) fP(Rv Vw Zq) FcHx GbbM GdVt HbYd ZqKl ZxPi UnUx} Vq{Vb(aA hB Nt) Cs(nC nL) Jj(Ko Ri) Jo(nC nL) Va(oH Tz) aA(Rv Wc) GdKk MtUx HlKd TvUr IvYe YhhB} rS{iP(aW bO cH dC hB Hf Hx Oe rN wB) aW(Iv qW rB Ri wB) Jj(Ap Et) IdRi KoKp} Nv{Ur(mZ nI nK nL) Yd(dR Lu Oz) Hc(Va Yi) nK(Jj nI) PoYh GbMh MpmZ ZxOz QwVa UxPd} Qd{Yh(Fy oE oF Yi) Dk(nC nL) Du(Ar oE) Nr(Uw We) Ye(Kr Us) YdcT KdUy cZwC} St{We(Cu Mi Mt Om) Fc(Jr Po) Rx(bA cT) Pd(Ux Vb) nI(Ib nK) MpVa cLmZ nKkC} Bo{Yi(Af aS cH cV Cx Mn Nl Rx Vt) Fd(Cx Qx) DiYg HaUw QeRv} On{Ad(mZ nK nU) Hc(Rx Va) Yh(dR Po) Pd(Ux Vb) BgnU FcdR UajO TvOf RxoH} cQ{qZ(bL cB Et Fp Hf Hq Hu iJ Ir Jk Jp Kd Oy Qc)} Om{We(aA Jl Rm Uv) Bg(Yd Tm) Zx(Oy Oz) YfOf MhWb YhOy LpUr} wD{An(aV Md oN) Ri(cW Lu oN) iP(Ar Pj wQ) LujD HqdH JtPj} Mt{Ux(bI cH Hw Hx It Oz Vu) Yd(Lu Tz) FrVb ItYe} Zq{Gd(Mx Pa) Jm(Ar Kj) Kl(bA cT) bM(Mh Mx) DeQb EfJl VoPa} Pa{Vj(Gd Pk Wb Yd) Wb(Mk Po) HlKz UnVa UrnI} Jj{Et(It wC) Jm(Fi Wd) Lh(jO jP) RxRm NxjP} aA{Qe(Hp Ye) CxFd EtUy GcKk JmVj RxRm cLmZ} Fc{Po(aH bM) TzOz HbbQ IraH YiJo PihB} Ur{Fd(Cx Jm Nr) Rm(mI mZ nI) DcnI} Va{Rm(Hc Qw) Un(bA cT) TzHb QbaG aScT} Nt{Tz(Uy Yd Zw) Vb(Dc Oz Qh)} Rx{Jl(Hc kR Lu Og) VtcT PihB} bM{Po(Lp Uy) Qe(Lp Yl) MxVj nKoP} eP{Et(Kg Uk) Gp(Ri Vt) AaFy PjcT} Ar{Jk(Fd Uz Wc Wh) LpaG} Id{Or(rN rW uG) bNqC cJjP} nI{nK(cL Mp Pg Tz) UscL} Iv{mZ(cL Mp) BaVb OkrW} aW{CuUx FdKj HxYe YiJo} hB{Il(Si Vc) EmnU KdVc} iP{rN(Al Mu) UmwB iBvS} Nl{NkjK mYjQ qXkI} Jm{PoWb McVj YjKz} Ut{oE(Du Yh) IrWe} Ph{AawB KprB KrvT} fR{oQ(nC nL) SiOz} Cu{LpOf VbaY} Et{It(Ng Og)} Mp{AxDu NrmZ} Nd{Kz(Wb Yd)} Wd{BgRm MxOy} Ko{MavS VtbN} bA{LurR UvVj} bQ{GbQb HbYd} PoYhJk FaaVrW FdaYbZ GccTdX GpkEoQ NuQeYe MwHcYi LhmPjO RiqCvB UscLmZ VtiJqH

Unconstrained panels with 2 analytes, where 1.0E-8 >= 'AUC p-value' > 0. Contains 3,622 panels of 182,582 total panels evaluated. : Nw(AA aC AD aE AF aG aH aI AJ aK AL aM AN AO AP aQ AR AS aU aV AW AX aY aZ BA Bb BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC Dd DE dF DG dH DI dJ DK DL dM dN Dp Du Ed Ef Eq Et EZ Fa Fb Fc Fd Fi FN FP Fr Fy Gb Gh GL Gp HA HB HC HF hG Hl HO Hp Hq Hr Hu Hv Hw Hx iA IB Ic Id IH Ii IJ Ik Il Im In IO IP Iq Ir Is It Iu Iv IZ JD JE JF Jg JH Ji Jj JK JL JM Jn JO JP JQ JR Js JT Ju JV JY Kc Kd Ke Kf Kg Ki Kj Kk Kl Kn Ko Kp KQ KR KS Kx Ky Kz Ld Lh Li Lj lK lL lM lN lO Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Nl Nj Nk Nl Nm Nn No Nq Nr Ns Nt Nu Nv nW Nx NY Oa OE OF Og OH Oi OK Om ON Op Or Ou Ow Oy Oz Pa Pb Pc Pd Pe PF Pg Ph Pi Pj Pk Po Ps Pz QA Qb QC QD Qe Qg Qh Ql Qm Qn Qt Qu Qv Qw Qx Qy Qz Ra Rb Rc Rf Rg Rh Ri Rj Rm rS Rt Ru Rv rW Rx Ry Rz Sf Sh Si Sj Sr Ss St Tn To Tr Tt Tv Tz Ua Ub Uc Ud Ue Uf Ug Uh Uk Ul Um Un Uo Up Ur Us Ut Uu Uv Uw Ux Uy Uz Va Vb Vc Vh Vi Vj Vo Vp Vs Vt Vu Vv Vw Vz Wb Wc Wd We Wf Wg Wh Yd Yg Yh Yi Yj Yk Yl Zq Zw Zx Ye Tm Tl Xa Wm Tj Ti Th Yf) Ps(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR Du Ed EF EM Eq Et Ex Ez Fa Fb Fc Fd Fi Fn FP FR Fw Fy Gb Gc Gd Gh GL Gn GP Gz Ha HB HC HF hG Hl Ho Hp Hq Hr Hu Hv Hw Hx iA Ib Ic Id IH Ii IJ Ik Il Im In IO IP Iq Ir Is It Iu Iv IZ Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp KQ KR KS Kx Ky Kz Ld Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv nW Nx NY Oa OE OF Og OH Oi OK Om ON Op Or Ou Ow Oy Oz Pa Pb Pc Pd Pe PF Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tr Tt Tv Tz Ua Ub Uc Ud Ue Uf Ug Uh Uk Ul Um Un Uo Up Ur Us Ut Uu Uv Uw Ux Uy Uz Va Vb Vc Vh Vi Vj Vo Vp Vq Vs Vt Vu Vv Vw Vz Wb Wc Wd Wc Wf Wg Wh Yd Yg Yh Yi Yj Yk Yl Zq Zw Zx Ye Tm Tl Xa Wm Tj Ti Th tF Yf) Vi(aA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR Du Ed EF EM Eq Et Ex Ez Fa Fb Fc Fd Fi Fn FP FR Fw Fy Gb Gc Gd Gh GL Gn GP Gz Ha HB HC HF hG Hl Ho Hp Hq Hr Hu Hv Hw Hx iA Ib Ic Id IH Ii IJ Ik Il Im In IO IP Iq Ir Is It Iu Iv IZ Jd Je Jf Jg Jh Ji Jj Jk Jl Jm Jn Jo Jp Jq Jr Js Jt Ju Jv Jy Kc Kd Ke Kf Kg Ki Kj Kk Kl Kn Ko Kp KQ KR KS Kx Ky Kz Ld Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv nW Nx NY Oa OE OF Og OH Oi OK Om ON Op Or Ou Ow Oy Oz Pa Pb Pc Pd Pe PF Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tt Tv Tz Ua Ub Uc Ud Ue Uf Ug Uh Uk Ul Um Un Uo Up Ur Us Ut Uu Uv Uw Ux Uy Uz Va Vb Vc Vh Vj Vo Vp Vq Vs Vt Vu Vw Vz Wb Wc Wd We Wf Wg Wh Yd Yg Yh Yi Yk Yl Zq Zw Zx Ye Tm Tl Xa Wm Tj Ti Th tF) Im(AA Aj Du Eq Et Fc Fd Fi Fp Fr Gb Gh Hl Ho Hp Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt kC Ke kF kN kO Lh Li Lj Lp Lt Lu Lv Lw LX Ly Lz Ma Mb Mc Md Me MF Mg Mh MI Mj Mk Ml Mm Mn Mp Mq Mr Ms Mt Mu Mv Mw Mx My MZ Na Nb NC Nd Ne Nf Ng NH NI Nj NK NL Nm Nn No Nq Nr Ns Nt Nu Nv Nx Ny Oe Of Og Oh Oi Ok Om On Op Oy Oz Pa Pb Pc Pd Pe Pf Pg Po Pz Qa Qb Qc Qd Qe Rt Ru Rv Rx Ry Rz Sf Sh Si Sj Uw Ux Uy Uz Va Vb Vc Vh Vj Vw Vz Wb Wc Wd We Wf Wg Wh Yd Yg Yh Yi Yj Yk Yl Zq Zw Zx Ye Tm Tl Xa Ti Th Yf) Ji(AA Af Aj Bg bN bO CH De Ed Ef Et eZ Fc Fp Fr Gl hB HC Hq Hr Hu Hv Hw Hx Ih Ii IJ Ik Il In IO Ip Iq Ir Is It Iu Iv IZ Jg Jh Jj JK Jl Jm Jn JO JP Jq Jr Js JT Kj Ld Lh Li Lj lN Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny OE OF Og OH Oi Ok Om ON Oy Oz Pa Pb Pc Pd Pe PF Pg Po Pz Qa Qb Qc Qd Qe Qg Qw Ri Ru Ua Ug Uh Up Ur Us Uv Vs Wf Yd Wm Th) Li(aA Aj Du Eq Et Fc Fd Fp Fr Gb Hp Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe rS Rt Ru Rv

Figure 30 Continued

Figure 30 Continued

Wm) Li(Aa Gh Ho Kc Lp Lt Op Rx Si Uz Yi Yl Zw Tm) Ih(Gb Gh Ho Lp Rv Rz Si Uy Vc Yd Yl Zx Tm) Js(Aa Lt nI Op Ru Ry Ur Vc Vh Vz Wd We Zx) Pf(Fd Hu It Lw My Nj Nx Pg Rv Wf Yl Zq Zx) Mt(Aa Fc Hp It Rz Vz Wd Wh Yd Zw Tm Tl) Fw(Du Gb Gh Hl Lp Op Rx Uy Vw We Yd) Im(cH Gc Gd Gn kE Kk Ko kP mE mM Ur) Ld(Ed Em Fc Hp Jp mZ Uw Vh Vt Wc Yl) Pe(Gd kC kO Lw Mc Md mF Mh mZ Ny Oy) Qb(Aa Jg Rv Ry Rz Uw Wb Yi Yj Ye) Jn(Aa Eq Hp Lp Si Sj Yh Yj Yk) Ko(bN Ch eZ hO In qZ uZ vS yD) Ny(aA Hu Ip Jk Lw Md nL Of Oy) Ow(Gn Ho Jp kN kO kP Rt Si Tl) Nb(Gh Hp Lt Op Ry Yi Yl Yf) Vj(aA aX Cq cT Ha Kq Pi St) Nn(Aa Aj Lp Sf Uz Vc Th) Wf(Cu Hx It Iv Nt Tn Un) Vt(Aj Ax dK Lt Of Ri Us) Dr(dR hB Kd Qh St Vq) Sh(Cu Ir Iz St Yi Zq) Rm(Eq Fc Yd Zw Zx Ye) aA(Ip Lh Mn Nj Uw Yi) Om(Gd Rt Ux Va Ye) Aj(Ba Fr Kf Vq) Ir(Fc Lt Rt Rv) It(Aa Lh Mn Vb) Zq(Ha Hx Jm Kq) Qa(Hc Jg Kk nI) St(Ho mZ Ru Si) Ur(Id Kf Kn Lp) iP(hO qA qZ tT) Ch(Jp Tn Uf) Cu(Rt Rx Vb) Ng(Fr Jg Kq) Ru(Fp Hx Po) Vi(Vv Yj Yf) aZ(Ho Vw Wd) wD(Bg Kc Ou) Aa(Hr Qc) Ar(Yi Ti) Eq(Pd Uf) Th(Fa Nt) Fd(Mx Ql) Mn(Ip Nh) Tz(Va Yd) Kq(Yj Yk) Vq(nI Ye) GcdX GdOa HaRt MqSi MxRv MyPg NljK IdbN IpJg IvUw KkiB KnrB KprW LhnL RiuT OurN UtVc cQwB

Unconstrained panels with 2 analytes, where 1.0E-6 >= 'AUC p-value' > 1.0E-7. Contains 2,132 panels of 182,582 total panels evaluated. : Ji(aC AD aE aF aG aH aI aJ aK AL AN aO AP AR AS aU aV Aw aX aY aZ Ba Bb BC bE bF bG bH bI bL bM Bo bQ bR bS bU bV bW bX cA cB cC cD cE cF cG cJ cK cL cM cN CO CP CQ cR CS cT CU CV CW CX cY dA DB DC Dd dE dF DG dH DI DK dN Dp eT FN Gp HA Hb Hf hO hP Ib JD jE JF jG jL jM JY Kd Kf Ki Kn Kp Kq Kr Kx Ky lK lL lO Lp Oa Ou Ow Pj Pk qD Qh Ql Qm Qn Qu Qx Qz Ra Rc Rf Rh Rj rS Rx Sh Sr Ss St tU Tz Ub Uc Ud Uf Ul Um Un Uy Va Vp Vv wB We Tj) Ke(aA Ad aE aF aJ Ao Ap aQ aR AW bA bI bJ bL Bn bP bS bV bX cA Co cP Cs cT Cu dC Di dJ Dl Dp Du Ed eF Fr Fw gL GP hF Hr Hw iA Ib Ih Ij Il iO iP Ir Is It Jd Je Jh Jk Jm jO Jp Jq Jv Kf Kg Kk Kl Ko Kr KS Kx Li lL Md Me Mh Mj Mk Mp Mr Mv Mw My Mz Nb Nc Nh Ni Nj Nk Nl Nn Nr nW Oe oF oK Om Oz Pa PF Pg Ph Pi Pk Pz Qb Qc Qd qO qQ Qu Qw Rb Rj rU Si Sr Tn Tr tT Tv tX Ub Ue UG uI Uk uN Uo uP UT UU Uv UX Vb vC vH VO Vs vV vW We wF wG yJ yL zH Zx tM xA Wm) Uh(aD Af aM aN Ao aP aQ aR Aw aZ Ba Bc bF bG bJ bL BO bR bS cA cD cI cJ cM cN Ct Cv Cx cY Db dF dG DL Dp eC eM Ez Fa Fn FR Fy Ha Hc Hp Hq Hu iA iH Ii Ik Il Im Io Ip Iq Iu Iz Jd JH jI JK Jp jT Ju Jv Kc Kj kQ Kz lW Ly Lz Ma Mc ME Mf Mg Mh Mk MM Mn MP Ms Mu Mv Mw Mx My Nc Nd NJ nK Nl Nq Nu Nv nY Oe Of Og Oi Or Oy Oz Pa Pc Pd Pf Pg Ph Pj Qb Qg Qh Ql Qm Qt Qu Qw Qy Qz Rf Rh Rm Ru To Tr Tz Ua Ub Uf Ug Uk Uw Vo Vs Vu Yi) No(AA Ch De Fp Fr Ha hG Hq Hr Hv Hw Hx Ii Il In IO Iq Ir Is Iu Iz Jg Jh JK Jl Jm Jn Jo Jp Jr Js JT Kf Kn Kp Lh Lu Lv Lw Lx Ly Lz Ma Mb Mc Me Mf Mg Mh Mi Mj Mk Ml Mm Mn Mp Mt Mu Mv Mw Mx Na Nc Nd Ne Nf Nh Ni Nk Nl Nm Nn Nq Nr Nu Nx Ny oE Of Oh Oi Om Ow Oy Pa Pc Pd Pe Pf Pg Ph Po Pz Qa Qb Qe Ri Tn Up Uv Wm) Mz(AA dR eF Fc Fp Fr gL gP hA hC hF hG HV iA iC IH iJ iO IP Iq Iu jD jE Jg jI jM jO jP jR Jt jV jY kQ kR kS Ld lK lL lM lN lO Lu Lv Ma Mj Mv Mx mZ Ng nI Nv nW nY OH Ow Pc Pd pF Po Pz Qc Qd Qe qH qO qP qQ qW qY rB rC rV sC uT uU vU vV vW Wf yJ yK zH yE tM) On(aA Ch Fr hB Ho Hp Hv Hw Hx Ik Il In Io Iq Ir Iu Iv Jg Jl Jm Jo Jp Jq Jr Js Jt Lh Lv Ly Ma Mb Mc Me Mf Mh Mi Mj Ml MM Mp Mq Mr Mt Mu Mx Na Nb Nd Ne Nf Ni Nk nL Nm Nn Nq Nr Nt Nu Nv Nx Oh Om oN Pa Pd Pe Pf Pg Po Pz Qa Qe Qw Ur Vj Yg Yk Yl) Lj(Du Eq Fp Hq Hr Hu Hv Hw Hx Ii Il In Io Ir Iu Iv Jh Jk Jm Jo Jr Kk Lp Lu Ly Mb Mc Md Me Mf Mh Mj Mk Ml Mq Mr Mv Mx Na Nd Ne Nf Ng Nh Ni Nk Nm Nr Nu Of Oh Oi Om Op Ow Oy Pa Pc Pd Pf Qb Qc Rv Sf Sh Ur Va Vc Yh Yf) Lx(aA Fp Fr Gd Hq Hu Ih Ik Il In Io Iq Iv Jg Jh Jk Jl Jm Jn Jp Jr Js Jt Lh Lu Lz Ma Md Mf Mi Mj Ml Mp Mr Ms Mt Mv Mw Mx Nb Nd Nh NK Nl Nm Nn Nv Nx Ow Pa Pd Pz Qa Qb Qc Qe Sf Si Ux Uz Wg Yi Tl Yf) Ij(Gd Hc Hq Hr Hw Ih Ii Il Iq Ir Iu Iv Jh Jk Jr Js Kc Lv Ly Mb Mc Md Mf Mg Mh Mj Mk Ml Mq Mu Mx Na Nb nC Nf Ng Nj Nk nL Nq Nr Nt Nu Of Oh Om Pc Pd Pf Pg Pz Qa Qb Qc Qe Ur Vt) Qd(aA Fi Fp Fr Hp Hu Ih Ik Ip Is Jg Jn Jp Js Kc Kk Kn Ld Lh Ma Mm Mn Ms Mt Mw My mZ Nc nI Nj NL Nm Ns Nv Ny Oe oH Op Oy rS Rv Rz Sf Si Ur Us Uw Uz Vh Vz Wb Wc Wd Yh Tm Yf) Ok(Aa Fr Hv Hw Ik Io Iq Ir Iu Jg Jl Jm Jp Jq Jr Jt Lv Ly Ma Mb Me Mf Mh Mi Mj Ml Mm Mp Mq Mr Mu Mv Na Nb Nd Ne Nf Ni Nk Nm Nn Nq Nt Nu Nx Oh Om Pa Pc Pe Pf Pg Pz Rt Rx Ur) Xa(aH aS Bg bJ bP Ct Cx dC Dg Du Gd Gl Hc Ib Il Ir Jh Jm Jo Kk Kl kR Kx Ky Lh Lz Mh Mr Mv Nr Nu Nx nY Oi Om Ou Pg Ph Pi Qm Qt Qw Qx Ul Ur Va Vb Vu Wf Zq Th) Et(Aa Af aM AO Ar bA Bb bN bO bU cB cP cQ dM Ed HB Ic Id Kc Ki Kj Kk Kn Ko Kx oF Qu Qw Ri rW Sr Tv Ug Ur Us uT Uu Uy wB wC wD Wf wL wQ YD) Pf(Aa Fc Gd Ho Hq Hr Ik Ip Ir Is Jj Jn Jr Lp Lu Mb Mc Md Mf Mi Ml Mn Mp Mw Nb Nd Ne Ng Nk Nl Ny Of Oi Oy Oz Pa Pd Pe Qe Ry Sf Ux Uy Uz Va Vb Vc Vw) Nv(Aa Aj Du Fc Fi Fr Hl Ho Hp Ih Ip Jk Jn Js Lt Lz mM Mn Ms Mx NL Of Oz Pb Qa Qb Qc Ru Rv Ry Sf Sj Ur Uw Uz Vw Vz Wc Wd We Wg Wh Zq Zw Ti) Ny(Fp Hq Hr Ib Ih Ik Il Ir jK Jr Lu Lz Mc mE Mf Mi Ml Mn Mp Mr Mt Mw My mZ Nb Nc Nd Ne Nj Nl Nr Oe Oh Oz Pa Pb Pd Pg Qe Wm) Vt(aQ Ar bA CH cI cT dM Id Im Is jT Kc Kk Kn Ky Ma Mh Mn Ms Mt Nd Nj Nl Nn Nr nW OH Ou Ow Qa Qe Qg Rh Sr We Zq) Aa(Aj Fp Fr Hx Ih Il Ip Iv Jg Jl Jo Jr Lh Lu Mb Md Mk Mp Mq Mr Ms Mv Mw Nb Ne Nh Ni Nl Ns Oe Oh Oy Oz Pc Pe Pg Po) Js(aA Aj Fp Fr Gb Gh Ho Ip It Jg Jp Kc kO Lp Mm Ms Oe Oz Pb Rz Sf Uw Ux Uy Uz Vb Vw Wg Wh Zq Tl Ti Yf) Pe(Hq Hx Ik It Jr kF kN kP Lz Me Mi Ml Mn Mr mY nC nH nK nL nU Oz Pa Pd Pg Tn Uk Wm) Is(Fp Fr Hr Ip It Jg jK Jt Kc kE Kk kN Ko kP Ld Ma mI Mk Mw Nm Nx Pb Qe Qg rB Ur) Rm(Du Fi Gb Gc Hl Ho Lp Lt Rt Ru Rv Ry Uw Uy Vb Vc Vw Vz Wb Wd We Wh Yl Tl) Im(Ch Dr iO kI kK Ld mH mP mS mU mW mY nA nB nD nF nJ nM nO nR nT nU oH) Qe(Gb Ho Hu Ik jT Kc Kk Mn Ms My Ng nI Nj Nl Ns Oe Oy Oz Pb Rv Ry Sf Yi) Mt(Ip jK jT Lp Lt Mn Oe Op Oz rS Rt Ru Sj Uy Uz Va Vc Vw We Yh Yi Ti) Sh(aH Ar Ax cE Cp Dk Fy Gc Hq It Ju Ko Ks Mv Mx Nt Pg Ph Qh Sf Tn Uf) Oh(Aj Gz Ho jT Kc kF Kk kN KO Ld Lp lX mE mW rS Rt Ur Vb Wc Yg) Nn(Ch Fi Gb Gd Gh Hl Ho Hp It Rt Ry Rz Si Uy Vz Wc Yd Yi Zx Tm) Qa(Aj Fp Fr Ik Ip It Jp kE Kn KO Ld Ms Mw Oe Oz Pb Qw Ur Us) Jj(Hb Ir Jl Jm Jp Kg Kp Ks Mm Mw Nm Nr Nx Ow Pg rS Sr St Un Yi) Nw(eT fR Gd Gz hL mZ nC qU qW qX qY rA rB rR rY uY wC wJ wP yH) Mn(Aj Ch Fp Ih Ir Jn Jq Lu Lz Ms My Nc Ne Nj Nl Ns Oy Oz) aA(Fr Gb Ho Jg Jn Jt Ma Mm Op Oz Pz Ru Rz Wd We Wf Tl Ti) Sr(Aj cH Du Fc Gb Gc Gh Hp Kk Ld Lp Op Ur Wc Tm Ti) Ko(Ed jT Kj Ld Ng Ow tU UR Uu wB wC wF wP yH xA) Fp(Fr Ih Ik Ip It Jg Jp Jt Lh Ma Mm Nx Og Oz Pb) Ir(Gb Hl Hp Og Oz Rx Ry Sf Ur Va Vw We Wh Yj) Fr(Hu Ih Ip Jn My Nj Nl Ns Oe Oy Oz Pb Qb) Yi(aP Iv Jl Jn Kk Or Ow Rh Rj Rx Un Ur Uu) St(Fd Gb Gc Gh Rx Sj Uz Vw Wg Zx Ye Ti Yf) Qb(Fc Fd Fi Hp Ma Rt Ru Rx Sf Si We Wf) Ld(cH Gd iB Id mI mU nI Rt Sf We Yg Tl) Ow(Ch fR Gh mE Ng nI nL oO oQ Qw Yg Yk) Ih(Hl Hp Jg Jp Lh Op Sj Yg Yj Ti Th) It(Fc Ip Jg Ma Mw Nr Oz Pg Po Ru Va) Ur(Ax Dd Fy Ip Jt Lh Li Oa Pi Un) Mq(Gb Ux Uz Va Wf Wh Yd Zw Ye) Jl(Eq Hl Lp Og Rv Ux Yg Yh Yk) Kn(Aj hB hR iB jK jQ jR oE wD) Kq(Bg De Hc Ik Iz mZ Oy Tl Yf) Ru(Cs Dr Hb Jd Mp Mv Om Tz Vq) Vj(Dc Fy Il Jm Lp Nr Nt Qh Vq) Pg(Hq Hu Lu Lw Lz Mr Nk Ns Wf) Kk(dJ Dr Ed Jp jT rB Wb Wf) Aj(Bb Dg Id Lh Om Uc Un) Ar(Fi Ho nI Uy Uz Wb Wc) Li(Fi Hl jT pS Yh Tl Yf) Ut(Lp Rt Va Wb Wh Yd Th) wD(Co Ef Jd jF Kr Or rS) Po(Du Lp Uy Wb Yd Yh) Mx(Hp Rt Rx Rz Vw Vz) Ip(Jp Ma Mw Nc Oz Pb) Zq(aH dR Gd Ki Nr Tz) aZ(Fi Gb Ry Vh Ti Yf) hB(bN cH cQ Si Uy Ti) Lh(jO Ms nC Oz Pb) Og(Hx Jp Jt Nr Om) Th(Ax Ha Id Iv) Si(Dr fR oE Uu) Kc(cH iB jK rW) Kr(rS tQ tS wB) Rx(Fy Om Tz Un) Rt(Fd Fy Pi Tv) Yl(Ha Il Nr Vq) Va(Dc Ha Hb Vu) nI(Oa oE Rj Tz) qZ(dJ eC Hc qA) jT(Fa Jq Jr Un) Ti(Ax Iv Un) Eq(Ez Jd Nt) Fc(Fa Hx Mj) Fw(Yh Yj Yk) Id(aF Ch xA) Wb(oE Om Tz) Jn(Jp Op Yg) wB(dJ Nm Ri) Bo(Uw Yg) Dr(oE Tn) Gc(eP Uu) Mw(Nl Ye) Nb(Yh Yj) Wf(Jh Vu) Jp(Hc Oz) Om(Vc Zx) Pj(eP uT) cH(iB nC) dM(pS rB) mZ(cL Pi) nW(tX uX) ChJd EdGd EmOa FbrS FdNu GbIv NtVw MrLt NgUf HoaH HxLp TrVi JgOy JrrB KfOf RyaP RirN UwOz cZrR eCoQ nNiH oNuT

Figure 30 Continued

Unconstrained panels with 2 analytes, where 1.0E-5 >= 'AUC p-value' > 1.0E-6. Contains 3,286 panels of 182,582 total panels evaluated. :
Vt(aA aD aE AF aJ aM Ao Ap aR As aZ Ba bB BC bF BG bJ bL Bn BO bQ bR bS bV bW bX bZ cA cB cC cD cE cJ cL cM cO cP CQ Cs Ct Cv CX cY DC Dd De dF DG dH dI dJ DI Dp dR Ed Em EZ Fa Fc Fn Fp Fr Fy Gc gL Gp Hb Hc Hf Hp Hq Hr Hu Hx iA Ic Ih Ii Ik II In Io Ip Iq Ir It Iu Iv Jd Je Jf Jg Jh jI Jk Jm Jn Jo Jp Jq Jt Ju Jv Kd Kf Ki Kl Kp Kq Kx Lh Li Lu Lx Ly Lz Md Me Mg Mi Mk Ml Mm Mr Mw Mx My Mz Na Nc Ne Nf Ng Nh Nl Nk Ns Nu Nv Nx Oa OE Og Oi Ok On Or Oy Oz Pa Pb Pe Pi Pj Pk Pz Qc Qd Qh Qm Qt Qu Qv Qw Qx Qy Qz Ra Rb Rc Rf Rg Rj Rm rS Rx Ry Sh Ss St Tn Tr Tt Tv Tz Ua Uc Ud Ue Uf Ug Uk Um Un Uo Up Ut Uu Uv Uw Ux Uy Vo Vq Vw Zx Tl xA Wm)
Ke(aC aD aG aH aI aK AL AN aO aP AS aU aV aX aY aZ Ba BB BC bE bF bG bH bM Bo bQ bR bU bZ cB cC cD cE cF cG cJ cK cL cM cN cO Cq cR cS cU CV CW cY DB Dc Dd dE dF DG dH dI dL dN eM Ez Fa Fn Fp Gc Gd Gn Ha Hb hG Hp Hu Hv Hx iB Ic Id iJ Io Ip Iu Iv JF Jg jH Jl Jn Jr Js Jt Ju Jy Kd Ki Kp Kq kR Ky Kz Lh Lp Lt Lu Lv Lw Lx Ly Lz Ma Mb Mc Mf Mg Mi Ml Mm Mn Mq Mt Mu Mx Ne Nf Nm Nq Ns Nt Nu Nv Nx NY Og Oi Ok On Or Ou Pc Pd Pe Pj Po qG QH qI Ql Qm Qn Qt Qv Qx Qy QZ Ra Rc Rf Rg Rh Rm Ss St To Tt tV Tz Ud Uf Ul Um Un Uy Vh Vp Vv Vz Wb Wh Yh Yi yK Zw Tl Tj)
Et(aC AD aE aF aG aH aI aJ aK AL AN AP aQ aR AS aU aV AW aX aY aZ Ba bB BC bE bF bG bH bI bJ bL bM Bn Bo bP bQ bR bS bV bW bX bZ cA cC cD cE cF cG cJ cK cL cM cN CO Cp Cq cR cS cT CU CV CW CX cY cZ dA DB DC DD dE dF DG dH DI dJ DK DL dN Dp DR eF Fa Fb Fw GL GP hC HF hG Hp iA Ib iH iO iP Jd Je Jf jO jT Jv Kd Kf Kg Kl Kp Kq KR KS Ky Kz Lt nW nY oE oH oK oN Or Ou Ow pF Ph Pi Pj Pk Qh Ql Qt Rf Rm rS Rt Ru Rx Ss St Tn tO tQ tR tS tU Tz Uk Um uN Up Uv Ux Uz Va Vc Vo Vs wE wF wG wH wJ wK wP yH zA Zx Ye Tl)
Uh(Aa aC aF aG aH aI aJ aK AL aO Ap aU aV aW aX aY BB bC bE bH bM bP bQ bU bW bX bZ cB cC cE cF cG cK cL CO cP cQ cR cS cU cV cW cX cZ dA dB dC dD dE Dg dH DI Dk Ef Em Fb Fd fP Gl Gp Hb Hf hW iC jD JF Jg JM jP Jy kE kG Kl Kl kN kO Ks Ky IL IM IO Lu IX IY mF mH mU Nk nO nR Ou Pz Qc Qn Qv Rc Rg Ry Ss St Ue Tj Ti tF)
Qd(Ar bN CH eZ Gb hB Hc Hf Hl Hq Hr Hv Hw Hx iH Il Il In IO Iq Ir Iu Iv iZ Jh Jk Jl Jm Jo Jq Jr Jt Kf Kj Ko Lu Lv Lw Ly Lz Mb Mc Md Me Mf Mg Mh Mi Mj Mk Ml Mp Mq Mr Mu Mv Mx Na Nb nC Nd Ne Nf Ng Nh Ni NK Nn Nq Nr Nt Nu Nx Of Oh Oi Om Ow Pa Pc Pd Pe Pf Pg Ph Po Pz Qa Qb Qc Qe Qg Qw Vj Yj Yk Wm)
Qe(aA De Fp Fr Gd Hc Hq Hr Hv Hw Hx Ih Il In Io Ip Iq Ir Iu Iv Jg Jh JK Jl Jm Jn Jp Jq Jr Js Jt Ko Ld Lh Lu Lv Lw Ly Lz Ma Mb Mc Md Me Mf Mg Mh Mi Mj Mk Ml Mm Mp Mq Mr Mt Mu Mv Mw Mx mZ Na Nb NC Nd Ne Nf Nh Nk nL Nm Nn Nq Nr Nt Nu Nv Nx Of Oh Oi Om Pa Pc Pd Pe Pg Po Pz Qa Qb Qc Sj Tv Us Wm Yf)
Nv(aA Hc Hq Hr Hv Hw Hx Ii Ik Il In Io Iq Ir Iv Iz Jg Jh Jl Jm Jo Jp Jq Jr JT Kk kO kP Lh Lu Lv Lw Ly Ma Mb Mc Md Me Mf Mg Mh Mi Mj Mk Ml Mm Mp Mq Mr Mt Mu Mv Mw Na Nb NC Nd Ne Nf NH Ni Nj Nk Nm Nn Nq Nr Nt Nu Nx Ny Oh Oi Om oN Pa Pc Pd Pe Pf Pg Po Pz Qw Vh Vj Yg Yh Yk Wm Yf)
Xa(Af aN As Ba bI bL bM bN bO bQ cA cH cO Cu Cv dE dK Dp Dr eF Em Ex Fn Gc gP Gz Hf Ic Id iH iJ In It iZ Jd Jk Jq Jr Jv Ki Kj kS Lp Lu Lv Mb Me Mf Mj Mk Ml Mp Mz Nc Nd Ng Ni Nt Og Oy Pa Pb Pj Pk Qc Qg Qu Qv Qy Rc Rf Sf Si Ss Ug Uk Uo Uv Uw Uy Vj Vo Vz Wb Yl Zx Ye Tl Ti)
Is(aA Ch eM hB hG Hu iB Ih Ii iJ Ik In iO Ir Iz Jm Jn jO Js jV kC KF kG Kj kO kS Ky Lv LW lX Mc Md mE mF Mj Ml MM mP Mr Mt mU My Na Nc NF Ng Ni Nj Nn Nr Ns Nt nU oE Of oN Pc Pe Pg Ph Po Pz Qa Qc Qw Ri Rj Tv Ug Us Uv)
Mn(Aa Ar Bg cH Fr Hq Hr Hu Hv Hw Hx Ik Il In Iq Iv Jg Jh Jp Jr Js Ld Lh Lv Lw Ly Ma Mb Mc Md Me Mf Mg Mi Mk Ml Mm Mp Mq Mr Mu Mw Mx Na Nb Nd Nf Ng Ni Nk Nm Nn Nq Nr Nt Nx Oe Of Oh Oi Om Pa Pb Pc Pd Pg Po Qa Qb Qc Sh Ur) Mz(Ar Ch Cv DE eD Ef Ib Ii Io jG Jh JK JI Jp Js Kc Kd Kl Ks Kx Lh Mg Mh Mk Mm Ms Ne Nh Ni Nn Nq Nx Oi Om Qa qT qU QX Ri Ru rY rZ Sh Tn Tr Tt tU Tv Ue uP Ur Us uV vO vP vQ vT wD wJ wK wP wQ Yd zA zG xA Wm)
Ny(Aa Aj bS De Fr Gc Gn Hc hG Hv Hw Hx iB Ic Ii In Io Iq Iu Iv jD Jg Jh Jl Jm Jn jO Jp Js jT kQ Ld Lh lO Lv Ly Mb Mh Mj Mm Mq Ms Mu Mx Na nC Nf Ng NH Ni Nk Nm Nn Nq Nt NU Nx Oi Ow Pc Po Pz Qa Qb Qc qW Ua) Ji(bB bJ bP cZ dD DL eD Eq Ez Fa Fb fP Fw fY gW hL hX iC Id jH iJ jU jV Kz lM Or Pi pY qA qB qU QV qW qX qY rA rN rR uM uR Ux Vb Vh Vu Wb wC wG WH wL wQ yD YH yL zA Ye tL xA Ti tF) Pf(Du Eq Fp Fr Hl Hv Hw Hx Ih Il In Iq Iv Js kE kN Lt Ly Lz Mq Mr Mt Mx NC Nf Nh nl nK nL Nm Nr Oe Oh Op Pb Pc Qa Qb Qc rS Rt Ru Rx Si Sj Uw Vh Vj Wc Wd We Wg Wh Yd Yh Yi Zw Ye Tm Tl Ti Th) Aa(aJ Hq Hu Hv Hw Ii Ik In Io Iq Ir Iu Jh Jk Jm Jp Jq Jt Lv Lw Ly Lz Ma Mc Me Mf Mg Mh Mi Mj Ml Mm Mu Mx My Na Nc Nd Nf Ng Nj Nk Nm Nq Nr Nt Nu Nx Of Og Oi Om On Pa Pb Pd Pz Ur) Ld(AJ aQ bB bR cG Ch dM Dr Ex fR Fw Gn HB Ij Jj Jr Js KF Kq Lj Lt Lx mE mS Mt mW Nh nK nL Nn Nr Oa Ok On Op Ow Pa Pe Pg Qh Ri Rz Sh St Ub Uf Un Uv Vq Vw Yk Zx Th) Fr(Hq Hv Hx Ik Il In Io Iq Ir Iv Jl Jp Jq Jr Lh Lu Lv Lw Ly Lz Mc Md Mf Mh Mi Mj Mk Mp Mq Mr Ms Mt Mu Mv Mw Mx mZ Na Nb Nd Nf Ng nl Ni Nr Nu Nx Of Oi Pa Pe Pg Po Qc) Pg(Fp Hr Ih Ik Il In Ip Ir Iv Jn Jr Mb Mc Md Mf Mi Ml Mq Mt Mw Mx mZ Na Nb Nd Nf Ng nl Nq Nr Nu Nx Of Oh oN Oy Oz Pa Pb Qc rB rS Rt Ru Tn To Tr Tt Tv Va Vj Wb Wm Ti) Id(aE Af aQ cH cJ cQ Cx De dJ dK dM eC Ed eZ Fw Gp Hb Hc hP iB Im In Jd Jj jK jO Jp Kc Kk Ko Lj IL nI No Nr oE Oh Oi Ph qB qC Ug uM Us Uu uV vB Wf wK Ti) Qa(aA De Dr Gc Gd Hb Hr Hu Ih In IO Jn Js JT Kf Kj kN Lh Lu Lz Ma Mm My mZ NC Nd Ng Ni Nj NK NL Nm Ns Nx oH Oi Oy Pd Po Pz Qt Tn Tv Vs) It(Fd Ih Ik Il Io Ir Jh Jm Jr Jt Lt Lv Lw Lz Mc Mi Ml Mm Mp Mr Mx My Nb Nc Nd Nj Nl Nm Nq Ns Nu Nx Of Oh Om Oy Pa Pb Pd Pz Qb Qc Rx Uy Yl Ye Th) No(Bb Bg bO cH dJ Dp eC Ef hB Ib Ic iJ Iv Jq Ju Jv Jy Kd Kl Kq Ks Kx Ky Mq Mr Nb nK Nt nW oF oK Ou Pi Pj Pk Ql Qt Qz Rj rS St To Tt Ug Uu Vs) Lx(aV bZ Ch dA Gh Ho Hw Hx Ii Iu JO Jq kN Ko Kx Lp Lv Ly Mg Mh ml Mm Mq Mu mZ Na nC Nf Ng nH Ni Nq Nt Nu Oi Om Pc Po Qm Qt Tr Ur Yk Tm Wm) Js(Eq Fi Hl Hr In Io JT Kk Ko Lh Lv Lw Ma ME ml Ml Mt Mw My mZ Nc Ng Nj nK NL Nm Ns Nt Nu Nx Oy Pd Po Pz Si Sj Us Yj Yk Tm Th) Ir(Du Eq Fd Fi Fp Ho Hq Hr Hu In Kk Lw Lz Mc Me Mt Nr Ns Of Op Oy Pa Pb Pe Po Si Sj Uw Vc Vh wB Wc Wd Wg Yd Yl Zx Ye Tm Tl Ti Th) Ko(aA aM dK dM eC Gd hB Ij Jo Jp Jv Kc Kk Kx Lj Ml Oa oE Oi Ph pS QB rB Ri rR Sr Ss tQ tS uO Us uT vl vQ vT wE wK yK zA tL) Nw(Dr Em Ex Gc Gn kP mE mF mY nH nN nT pS qP qV qZ rC rX rZ sC sO tO tR tS tV uO uX vA vH vP vS wE wF wG wL yD yL zA zI yE tL) aA(cH Fc Fd Fi Fp Gc Gh Hb Hp Ih Ii Io Jj Jp Lp Lw Me Mt Mw Nc nK Nl Nm Nn Nr Ns Nt Nx Og Qb Qc Rx Va Vc Vh Wb Wg Wh Yj Zx Ye) Jj(Ad Ap Co Dd Ed Fa Fw hB Il Io Jd JK Jo Kc Kd Kk Kr Kx Ky Lv Mx Nh Nj Nl Nt Om Oz Pe Pi Qc Qh Rf Ri Rm Tz Uc vI Wm) Qb(Du Eq Fp Hl Ip Jp Jt Kc Kf Lh Lp Mm nC nH nl nK nL Og Op Sj Ux Uy Uz Vb Vc Vh Vz Wc Wg Wh Yg Zw Zx Tm Tl Ti) Pe(Il Ip Jg kG IW lX mE Mf ml Mj mM mP Mq Mt mU Mw Mx NA nB nD NF nJ nN nO NR nT Nx Pb Po To Tr Tt Tv) Im(aE aQ Ax Bb Bg bL bN bS bX cl cQ Ct De dJ dM Hb iJ iP jK jT Kc kG Kn IW IY mT nN nW oE oF oN oP oQ Ou Qw) Fp(Hu Hx Ii Io Jl Jn Jq Lv Lw Me Ml Mp Ms Mt Mw Mx My Nc Nh Nj Nl Nm Nn Ns Oe Om Oy Po Pz Qc Uw Zq Th) Nn(Du Fc Hu Ih Ip Jn Jp Kk Lt Mt Ng Oe Op Oy Oz Pb Ru Rv Rx Sj Uw Va Vh Wd We Wg Wh Yg Yl Zq Zw Tl) Mt(Aj Du Fi Gb Gh Hl Ho Ih Jg Jn Jp Lh Ma Nc nl Nj Ns Nx Pb Ry Sf Si Uw Vh Wc Wg Yg Yl Zq) wD(Aj aN Ao Aw Bb Bc bL bS Ch Cs Ct De Dg Dk Fa Hb Hc Iz Kd Kk Kp Kx Kz nW oN rB rC Tn) rS(Ao Ax cD Hb Iu Jl Kn Kp lM Mh nW Of Ok Pa Pj Ri rT Uk uT uX vI vW wB wJ yL yE Wm) Zq(Af Aj aP Ar bM Cs Dg Dr II Kd Kl Lp Mh Mm oE On Oz Pk Rf Rx Ss St Vo Vq Wf Yd) Jp(Aj Ar Bg Fa Iv Iz Jl Kc Kn Kq Kx Lv Lz Mp Ms Ng Ns Nx Oa Oe Ou Pb Po Qc Ql Wm) Kk(Aj aQ Ar Ax bN CH eC eD Fa Fd Hb jF jK Kq Kx Li mU Oa On Ow Pj Ri Ub Un Vq) Yi(bM Cx Fn Gn lh Jd Jo Lz Ml Mv Mx Nq nY Of Oh On Pc Ql St Us Vb Wf Yh Tl) Lh(Hr Hu Ik Ip Jg jK Jn Jo jP Nc Ng nH nK Ns Oe Oy Po Qc Sh Wb Yd) Vq(aZ Ch Eq hC Hl Hp iB In Lt nC Ng nL Rv Ry Us We Wf Yh Ti Th) hB(aE aW bS Ch eC Gb Gc Ij lp jO Lj Lu nC nK nL Ow Pj rB Ry Th) Ar(aE Aj Bb cH cJ Dc Gb Hb Hp Kc Kn nK Ri Rt Ru Si Ur Uw We) Jg(Hu Jn Jq Lw Lz Mp Ms Mw Mx My Nj Nl Ns Oe Of Oz Pb Po Sh) St(Du Gn Hp Lp Lt nK nL Rt Ry Ur Uw Vc Wc Wd Wf Yd Tm Tl Th) Oh(Hb kC kG Kn lW mF mH mP nB nD nF nR Og Si Us Uw Ux Vw Yf) On(Bg cH De Ef iH iP jK jT Kc Kj kP nC nl oE oF Ow Us Wm Yf) wB(aN Hq Hu iP Iq Jh Jk Lj Ly Ma Me Nd oE Oy Ph Pj rB rW)

Rz Tn Tv Tz Ua Uc Uf Ut Vq Vu We Zq) Mq(aA Ad Al bA Bc Bg bM cE cL Cp cQ CT Cw Dd Et Fd Fi Fy Gp Ho Hq Ic Ih Ii Il Im Ir Iz Jg Jh Jk Jm Jn Jp Js Jt Ke Ko Ks Li Lp Mg Mn Mx Nb Nd Ni Nr Nt Nv Nw Ny Of Oh Ok On Pa Pd Pf Pg Pi Pz Qa Qc Qd Qe Qh Qu Ri Rm Ru Ry Rz Si Sr St Tn Tt Tz Ua Uc Uf Uh Ut Uw Uy Vq Vt Yi Zq) Om(AF aM aN aP AR aW bA bG bJ Bo bQ cO cS Cv Cx cZ dI dN Ed Ef Ez Fp Fy Gd hG Ih Ij iO iZ Jd Jj Jq Ju Jv Kx Kz Li Lj Lx Mg Mi Mu Nc Nf Ni Nr Nv Nw Nx Ny ON Op Oy Oz Pd Pf QI Qu Qw Qy Qz Ri Rj Rm Rt Rx Rz Sr Tn Uf Ur Uv Vj Vw We Yd Yi Zx Yf) Li(aA aH aO aZ BA bF Bg bQ bZ cD cE cL cN CT CU Dc dF Dk dM Du Ef Ez Fd fR Fw Fy hB Hq Ih Ij Im Is Iz Jl Jm Jn Js Kq Lv Ma Mj Mp Nb Nd Nw Oh On Ou Pa Pd Pf Pg Ph Qa Qd Qh Ql Qn Rc Ri Rm Sr St Tn Tr Tt Tv Ua Uc Ut Vp Vq Vs Wd) Im(aG al aK AO aQ aU aW aZ bA bB bC bM bP bW bX bZ cB cE cl cL CO cS cT cV Cw cY De dF dK DR Et Ez Gp Hb Hc Ho Hq Hv iJ Ik iP Jh Ji Kz Ld Lu Lv Ma Mm Mp Nd Nu oE oF Oi Or Ou Ow Oz Pg Qg Qh Qv Tz Uc Un Vj Vq Vt Vu) Qd(Af aH Ap Ar aW Ax aZ BA bF BN Bo bQ bZ cE cL CO cS cT Cu Cw Cx dF dK Ez Fw Fy Gp hB Il Is Iv Jm Jn Kd Kq Kx Ld Lz Ma Mf Mg Nb Nr Nt Oe Oh On Pd Pf Ph Qu Qv Qx Ra Rf Rh Rm Ru Rx Rz Sr St Tn Ur Us Vq Wm) Rz(aA aH aX BA Bg bQ cE cL cN Cu dF Dk Ed Et Fw hB Hq Ih Ij Is Jk Jl Jn Jq Js Ke Kq Ld Lx Mj Mp Mx Nb Nd No Nv Nw Oa Oh On Ou Pf Qb Qe Qh Rm Sr Tn Tz Ua Uc Ut) Kq(aD aF AN aO Ap aU Bb bG Bo Co cW Dk Ex Ez Ho Ic Jh Kc Kd Kg kQ Ky Ld Lj Lu Mg Mi Mp Mu Ni No Nt Oa Or Pd Qw Qz Rb Rg Sr Tn Uf Uh Ul Vj Wd Yd Zx Tm Th) Nv(AF aU AX Ba bC Bn bW CO cS De dK DR Et Ez Gp Ic Ih Ij Iv Jh Kc Kd Ke Kg Kz Ld Mg Mi Mm Mp Mu Nb Nq Nt Oe Oh Qw Qy Qz Sr Ur Vj Vq Wd) Qa(aC aD aG Ap aU aW aX Ba bE Bo bW cE cL CO cP cS Cw Cx Dd dI dK Ex Ez Gn Ij Jh Kc Kd Ke Kg Ld Mg Mi Mp Mu Mv Nq Nt Pd Qy Qz Rj Rx Uf Vj Wd) Ke(aP Ba bJ bN bQ bZ cD cE cL cO Cu dK Ez fR Fw hB Il Is It Iv Iz Jk Jl Ma Mg Nb Nt Nu On Pd Pf Ph Pi Ql Qy Ri Rj Ru Rx Tn Us Ut Va Wh Yd) Ez(aA aH Al aZ Bo Ed Ef Fw Hq Ih Ij Is Iv Iz Jg Jk Jl Jm Jn Jp Kd Lj Lp Mw Mx No Nr Nw Ny Oh On Pf Qb Qe Qh Rm Sr Tn Tz Ua Uh Ut) Nb(Aj Ap aU aW bQ bW cG cL CO cS Cu cZ De dK Dl Et Gb Ho Iu Jd Jh Kc Kd Kg Ma Mg Mi Mm Mu Nm Nq Nt Qy Qz Uc Ue Un Vj Vq Wd) Ld(aP Ba cE cL Co Cp Cw dF Ed Fb fR Fw Gp Hq Is IZ Jl Jn Jp Kf Kn Kp Mn Nt On Pd Pf Ph Pk Pz Qc Qu Ri Tr Ua Uc Ut Vv Zq) Pd(aH aX aZ Bo bR cE Cu Ed Fb Fw hB Ih Ij Is Iz Jd Jh Jk Jl Jn Jp Js Nd No Nq Nr Nw Oh On Pf Qb Qe Qm Rm Sr Tn Tz Uh Ut) Jh(aH BA bQ bZ cE cL cT Cu Dc dF Fw Fy hB Ih Ij Jk Jl Jn Js Lx Mp Nw Ny Oh Ok On Pa Pf Rm Sr Tn Tr Tt Tz Ut) On(aF Ap aU aW aX aY Ba Bb bG Bo bW cL CO cS De dK Fc Fw Hv Ih Jd Kc Kd Kg Mg Mi Mp Mu Qy Qz Rb Rt Uf Wd) Is(aF Ap aU aW aX bE bN Bo bW CO cS Cv cZ De dI fR Hf Hv Jd Jq Kc Kg Mg Mi Mp Nu Oi Qz Rv Uf Vj Wd) Ij(aK aU Ba bQ bW cL CO cY dR Fb Hf Jd Jk Kc Kg Mg Mi Mp Mu Nc Nq Nw Qc Qy Qz Ua Uf Wd Wh Yf) Ut(aF Ap aU aW Bb Bo bW cL CO Fc Ho Iu Iv Kc Kd Kg Mg Mi Mp Mu Nt Nw oE Qy Sr Uf Uh Vq Wd) Ny(Aj Ap aU aX Ba bC bW Ch cL CO cS De Dg dK iH Kc Kg Ma Mi Mp Mu Mv Nq Nt Qy Qz Uu Wd) Mp(aA aP bA bQ Ef fR Fw Fy Ih It IZ Jg Jl Jn Nr Nt Nu Oh Pf Qy Rm Ru Sr St Tn Tt) Jn(aU aW bN bQ bW cE cL CO De dK Ho Jd Kc Kd Kg Mg Mi Mu Nq Qy Qz Ri Uf Vq Wd) Pf(aW bJ bW CO cZ dI Hf Hv Iv Jd Kc Kg Kz Mg Mi Mu Nt Pi Qz Sr Uf Vj Vz Wd Zq) Ba(aW Bo Co Ct Fw Ih Jd Kc Kg Mg Mi Mu Nq Nw Oz Pe Qe Qy Qz St Uf Uh Vj) Oh(aC bE Bo bW CO cZ dI Ef Fc fR Kc Kg Mh Mi Mu Nq Qz Uf Ur Vj Wb) Jd(bA bQ cL cT Dc dF Fw Fy Ih Il Jk Jm Js Lx Nr Nw oF Pa Rm Ru Tn Vq) Mg(aA aH aX aZ Bg cL dF Ed Fw Hq Jk Jl No Nw Qb Qe Qh Rm St Tn Ua) Co(aA aZ bA bQ cE Cu dF Ed Ef Fw Ih Jk Jl Js No Nw Rm Sr Tn Tz) Qy(bA cT Cu dF Ed Fw Fy Ih Jl Js Lx No Nw oF Rm St Tn Tr Yi) Uf(aA aZ bQ cE Ed Fw hB Ih Iv Jk Jl Js Kk No Nw Rm St Tn) Zq(aA aZ bA bF cL cT Fw Hq Iv Jk Jl Jm Mm Nr Oa Pa) aW(aA aH cE Cu Dk Ef Et Jk Mv Nq Nw Qe Rm St Tn Ua) Fw(aU bQ cO cS Kz Mi Mr Mu Nf Ni Nq QI Qz Vj Vu) No(Aj Ap aZ Ch Hc Ib Kg Mi Mu Mv oE Ur Wd Ye) Nq(bA cH cT Ed hB Ih Jm Js Kd Nt oF oN Sr) St(aU aX cZ dK Hv Kc Kd Kg Mi Mu Wd) Ih(bQ cE Ch cL cO Hq Mu Ri Rj Vu) Sr(aQ aU bQ cO cY fR Hv Kk Qz Ri) Nw(cO Kg Mi Mu Mw Nt Ph Qu Vj) Ed(bZ cS KI Ma Mv Vu Wd) Nt(bA cL cT Dc Js Ow Qh) Qz(bA cT Cu Js Lx Rm Tn) Vj(cL Jk Pa Ph Pi Rm Vq) Mi(bZ hB Jl Js Rm Tn) Mu(bA cT Jl Js Rm Tn) bQ(Dl Hb Iu Un Vq Vt) cO(Et Iz Jg Jp Qe Vq) Cu(cD Jm Pa Rt Ru) Ow(aA bJ Hu Ua Uo) Pe(AJ Ch Hc Hq) hB(Ef Ho Lx Si Vq) Jk(cS Et Iv Ur) Jl(Ap Kc Kd Kg) Tn(Ap Kc Kg) Rm(aU Kc Kg) Bo(Uc Vu) Et(aA Iv) Wd(Gp Uh) Vq(aA Kk) CxTz DcNu NdKz IzaU SifR JiRi KdQl OaaZ aFdF cEcS} Ke{sK(An AO aP Ar BA Bb bF Bg bL bQ cE cG Ch cL Co CP Ct Cu cW De dF Dk Ef Fr Gl hA Hc Hq Hr Hu Hw Hx Ib Ii It Iz Jd Je Jh Jk Jv Kg Lh lM lO Ma Me Mj Mk Mu Mv Mw My Nb Nd Nf Ng Nn Nq Nu Nv nW Ny oE Of oK Om ON Oy Pa Pb Pd Pg QT Qx Qy Ri rS rW uR UT uX Vu wH wK wQ yD Tj) Rx(aA Af aH Aj aM aP Ar aV AX aZ BA bJ bM bW CH cO cT Di Dr Fb Fy Ha hB hG Hx Ih Ij Im Ir Is iZ Jj Jl Jn Js Kc Kg Kj Kp Kq Kz Ld Lj Lx Lz Mh Mq Mr Mx Nc Ne Nf Ni Nl No Nu Nw Ny Oa oE oF Oh Ow Oy Oz Pa Pe Pf Pi Pk Qa Ql Qx Ra Rf Rm Rt Sr Ub Uk Vt Vu Yd Yi Wm) wD(aL AO aS Aw BA bF Bg bI bL bQ cG Ch cL CO Cp Ct cW De dF Dk Ef Fr Gl Hq Hr Hu Hw Hx Ib Ii Iz Jh Jk Kg Lj Lu Ma Md Me Mj Mk Mu Mv Mw My Nb Nd Nf Ng Nn Nq Nv nW oE Of oK Om ON Oy Pa Pb Pg qG qU rB Ri rP rW sO uI uR UT wH wJ wK wQ yD) Ru(aE Af aG aH Aj aM Ar aX aZ bM bN bR Ch cM Di Ed fP fR Fw Gd Ha HC Hf hG Iv IZ Jj Jl Jo Jv Ko Kp Kq Kz Me Mm Mn Mq Mr Nb Nc Nd Ne Nf Ni Nk Nl No Nt Nu nW Ny oE Oy Oz Pe Pk Ql Qu Qw Rf St To Ub Uk Uu Uv Vb Vc Vh Vt Vu Wb We Wh Yd Yh Tm Tl) wC(aK AN Ap aV Ax aZ bI bL bW cD CH cP cQ Db Dg Dk DL eD fN fP Fw Gl Hq Hu Ib Id jD Je Jk Jn Jo jP Jr JV Kc Ko Kz Li Lj Md Me Mf Mh Mu Nb Nd Nv Oa oE Og oH Pk qA Qd qQ qU Qz Ra rB Ri rW tO uI Ut wK wQ Wm tF) Yd(Aj Ar AX bA Bc BG bN Ch cT Cu cV Dc dF Di dK Em Ez Fd Fw Fy Ij Ik Is Jl Jn Kq Ks Lv Lz Mh Mq Ms Mt Mx Nb Nc Nn Nv Nw Ny Oa oF On Oz Pa Pe Pf Pg Pi Qa Qe Qh Qw Qz Rf Rj Sr St Tn Tv Tz Uc Vq Vt We) qA(aK Al aN aQ bL bN cH cW Dc dR eZ hP Hq Hw Ic Ih Ii Ik Iv Jk Jq Jr Ju JV Kg Me Ms oE Ph Pk qP rB Rh Ri rP rS rT tQ tU Tz uM Ur Ut uW tM) fN(Aj aN aQ cP Cv Dk Ef Fw Fy Gl Hc hO Hq Hu iB Ic Ii Ik Ir Iv Jj Jk Jo jT Ks lL Mg Ng Nl Nv nW Of Oy Ph Qc Qu Rh Tv Ug Up Ur Ut) Th(aA Af Ar Ax bV Cs cT fR gL hB hC hG Ij Iv iZ Jl Ju Jv Kj Kq Kx Ld Li Mh Ml Ni Nn Nt oF Oh Ow Oy Oz Qx Ra Rf Rh Ub Wm) wK(aA aK Ap aU aV cD Cv cZ dC Dg dJ dR eD Fw Gp iJ iO Jn Jq Jr jT Ki Ko Ky Mm Oe Pk pS qO qP qU sC vQ vV zA zG tL) Yh(Ax bN bQ cT Cu Dr Ez Fy Ih Ij Is Jn Kq Ld Lx Lz Mh Mq No Nr Oa oE oF Oh On Ow Pf Qa Qx Ra Rf Rh Yi Zw Wm) We(aA aW bQ cD Ih Il Im Is Iv iZ Jk Jl Jm Jn Kq Li Mt Mx Nn No Nr Nt Nv Ny Om On Pf Qa Qb Ri Rm St Ut Va) Rt(bA bL cH cT Dc Di Ed Fd Fw Il Is Jl Jm Js Kq Ms Mx Nv Oa Oh Ok On Pa Pi Qb Qe Qh Rm Sr Tn Tv Tz Uu Vq) Dr(As aZ bA bQ Ch cT dE dK Ed Em Gl Ih Im Jd Jm Jy Kk kQ Lj Lp Mh Ms Mx Nb Nd Nx Ny Oa oE Oh Pf Uu) yD(Aj aQ Cv dJ eD Ef Fw hR iB Ic iJ iO Iq Iv Iz Jk Jq Ky lL nW Oe Ph Pk pS qU Rf Rh Tz vA vQ vT zA) rS(Af aK aV aW bI Ch CV dC dD dJ eD Fw Ic Id iP Iv Jj Ki Ko Md Mf Ph Pk qY Ri rR uV Vt Wm) rR(aK aN Ap aQ aV cD Dg Dl eD fY Hc Id jP jQ JR JU JV Kc Ko Me OE qP qQ sC Tz) vT(Af AN bI bM Bn cD De Dl dM Hw Jk Jn Jq Jr JV kQ Ma Md Me Nm Nv oE rB Ri uL uM vQ) uM(Aj aN aQ aV Bg CH cJ Cv dC Fw Fy Hc Ic Ii iO Iv Iz Jj Jo jU Ks Na Pk pS qY Rf) Fc(Ax bN Cs cT Ez Fy Gd Hx Ih Ij Jn Js Kq Ld Li Lz Ml Mq Nn oE Oh Pf Rf Uu Yi) Va(aD aE aG aH aX aZ bA bM cT Dc Di Fd Fw Is Jm Nb Oh Pa Pi Qm Rm St Tz Vq) jP(bX CH cJ cQ eC Ef Hc Hu Iq Ji Jk Kc Kn Nj Nl Of Oy Pk Qu Qv Qw Ua Uh) rW(aK aM aQ aR aV bC dD dR Fw Hq Iv jD jQ jT Kc Nu Oe Ph Pk qP rN Um Up Vt) hP(Aj aN Bg Ch Cv dC eT Fw Fy Hu Ic Ii iO Iv Iz Jj Jo Kj Ks Pk Ur Wm) pS(aI aW bI Bn cL cW dD De Dk Gl Hr Hw Jo Md Nb nW oK Ow Ri sO wQ Tj) vQ(Aj aN Bg bI bL cQ Ef Gl Hc Hq Hw Jj Kc Kg Mg Nb Ng Nu qG tN) Ch(bN dK dM Et gL Hp jO Jp jT Nd Ow Ri rP Rz Us vS Wd Yi Yf) wQ(aE Af aG aQ Cv dJ eZ Gp iJ Jq Jr Ju Ky Md Oe Pk Rh Tz zG) sO(aE aG aQ Cv cZ eZ iJ jD Jq JU Na Oe oF Pk qH Tz) rN(Af bI bL cL CP De Dk Hq Hu Jk Ma Nn Nv nW Ri Tn) zA(AO bL bQ cW dD Dk Fr Hq Jh Ng nW Om oN Oy uR) rP(bM cD cH Cv dC Fw iO Jk Jo Jq Jv Ki Mf Pk Vt) vS(Aj aO Bg Dk Ef Ii Iz Jj Jk Jo Mg Ng Of Oy Ua) Wb(aW bA bQ dK Em Il Lj Mh Mx Nr oE Oh Pa Pf) jT(bI cH cQ Ct eT Hc Jk Kn Of Oy qG Qu wJ wL) Ye(bN Ed Fw Ih Iv iZ Jm Ld Mq No Ny Rm Vq) eP(aE aH Al aM

Figure 30 Continued aQ bB bR cH Dg dI Et Ow Vq) Du(Ax Cs Ih Jn Li Lj Mx No Oa oF Oh) cQ(Jj jY oE qP qZ rC rY sC vP wF wP) uR(aE aK aQ aV bW cD dC
Gp Jn Ko Mf) Ow(Aj Bg Hc Ij Jo oE Of oN Oy Zw) Ux(Ba bQ Fw Im Iv Nb Nn Pe Pf Vq) eT(aE aK aM cJ dM dR jD jV Oe Ur) Yi(aA Af aX
bM Fw GI Ny Uv) oE(cH cP NI uI uL uO vA wG) Lp(Aj bN Gd Kj Oy Ur Uu) tS(cH Dk Ef Jn Jr qQ rB) vV(aE aK aQ aV dR Oe qP) Vb(Ba bQ
Iv Nn Nt Pf) dD(eZ rT uZ wB zG tL) Nb(H

Vw Yg Yh Yi) tS(eZ hP Qg Qm Qw Rj Rm) Yh(Bo Cu Om On Vq) Yj(Ba cL Mp Pi Vq) Vw(cL Lv Ou Tz Vt) wD(aG bX cJ Ha rB) Si(aA bQ
fR Jl) iB(eZ Kc oH wP) pS(cJ dJ rB wQ) Gn(Pi Tv Vu) Rv(aH Pg Rm) Vc(bQ cE cL) aA(Op Vh Yd) Al(qZ uV) Bo(Yg Yi) Hp(aG Mp) Sj(Jh
Qy) Zw(Cu On) Wh(aG Dd) Tl(Om Pi) Va(Dc Rm) wC(cZ qZ) AjwP GcRi YdQy WeOm JkLp Rjnl OpPi UyVt cJIL dJwB w

Figure 30 Continued

QxcL} Nv{Yd(bS dR Et Hb Lu Oz Pj Si) Zw(Hc Kx Lz Mh Ml oE Po Qx) Gb(Bg Lz Mh Ml oE Oy Qx) Si(Af Ar Gd Kj Mh oE Oy) We(Cp Hv Mi Mt Nr Pd Pi) Ye(aF eM Hx It Iv) mZ(eC Ib Ii Mp Qe) Ti(Aa Bg Gd Oy) Rv(Lz Mh Ml Qx) Lp(Hc Kd Lu) Yl(Hc Lu Vt) nI(Ib nK Qw) Po(Du Yh) Wd(Bg Mi) Jj(Fi nK) Uy(Lz Oy) cH(mI nK) oE(Sj Vc) GcKj GdIc ZxOz QuRz eCmM iPrN} hB{Ti(Ax Cp Cu Dc Dd Fb Ha Hv Iv Jl Jp Jr Kd Mr Ok Pi Qe Qh St Tv Tz Vp) Uy(Cu Hx Jl Pi Qe Si Un Vq) Vc(Fi Fy Il Kd Nr Pi Vq) Si(Gd Il Lp Mx Nr) Lp(dR Lu Oz Vq) Em(mE nU Vq) Fi(bR oH Pi) Gb(Il Kd Pa) Ho(fP Oz St) nK(eC Qb St) Du(Po Qe) Gp(dX eP) Lu(hP Ry) Il(Yd Yl) Vq(Yh Zw) mI(bI Rj) HlKd VzUn SfPi RvRm UmkE fRnJ wQiP} Vt{rB(eC eZ Iq Kk QC Ri rR uG Up Us wQ xA) eZ(bL qH qT uR uU vO vS) Uy(Il Kd Lp Mx Nr) It(Gc Lt Ry We) Yd(Cu Et Mt Ut) nI(Kn nL Pi Rj) Lt(Ax Nr Nt) bN(Ko Yj Tl) bQ(Hp mZ nK) cW(sO tS uT) Du(Ax Po) Gp(eM eP) Jk(qO qP) bL(sO uT) cL(nC nL) eC(vS xA) hX(sO uT) EteP MhnC MtZx HwrT SffR RzOz cZvS hAwP iJqH iPuP wBoE qPvV} Mt{Yd(aH cT Dc Jq Lu Mp Or Pg Qe Tz) We(Dc Ef Hc Ir Iz Qb Qe Qw Ss St) Ye(cH fP Hx It Kz Qb St Vq) aX(Gb Rz Wd Yh Yj Zw Zx) mZ(cL cV Dc jK Or Tz) Vz(bA cH Ir Mx Pa) Tl(aY bM fP Jm) Zx(aE aH Oz) Rz(aE bG It) Lp(aH Hc Oy) aV(rW vP vV) Zw(Ir Qb) Vw(bG It) cH(Du Yl) AaTi GhbM WdaE TmaY} St{We(Cp Cu Cw Iv Jr Mi Nr Pd Vu) mZ(aU cL cO dK Ez kG Mp) nI(cH Fb Ib nK oE oF Rj) Ho(Ar bG Ki Mi Qv Ug) Hl(Cu Hv Iv Kd Mi) nK(Ad bG kC nA oF) Fi(bG Jj Ki Qv) Gb(Ar bG Mh Qv) cH(kG nC nH nL) Gn(Hv Iv Mi) Ar(Lp Uz) Gc(Ki Qv) Yd(aU Et) Wd(Bg Qv) Ye(aW Uf) nL(kO Ph) PoZw TlKd UzbG} Qe{Hl(aD aW aY BA bQ cD Cq cT cU dK Ez Jm Kd Mi Nx Pa Pd Qn Qx Ra Us Vq) nI(cH Ib oE oF Rj) Yd(aG cE Et Mp) We(Cp Iv Mi Pd) Ye(aY It Nu Pd) bM(Lp nK Yl Ti) Du(Ar bG Jj) Gn(Qx Ra Yh) cH(nC nH nL) oH(nC nH nL) Ti(hG Jo) Wd(aX De) aY(Lp Yj) GbQv NtVw KdUy RzaX bQmZ} eP{Gp(Fy Ic Kn KR Pj Qh Qw Qy Ri Rm Ua Uo Ut Vq Vs Vu tF) Et(Hc Je Jf Kg Kn Ks Or Qn Qu Qy Ra Uk Vs) Pj(aL bA cT dD dF Jl Pg Tz Uc) Aa(Fy Qm Qx Rf Rh Tz Vq Wm) Mn(Fb Ib Ql Qn Um) Tz(Ap bB Dg Jt) Gc(dH Mr) Vq(Kk Pz) IcdD JjKs KyaG VsbB} iP{rN(Al aV Aw Bg bL cW Dk dM Ef Fn Hc hR Hu Hw Ik Iz jD Je Jj Jk Jm Jv Mk Mu Mv Ng Nk oE Ou Oy Qh qQ QT rB Ri rW wP Tj) vS(aJ hW iB Id jI Tv Ub Uc Ud Um Un Up Us) bA(qA uR) rW(jF jK) sC(jQ jR) UmwB hRtQ} Ye{Mw(Ax bA cT It Mx oE oF Og oH Pa Qb Qw Rf Rm Tz) Qb(Ez fR Jd Jh Mg Mi Mu Nt Pd Qy Uf Wd) Rm(aF aW bG Hv Mi Qy Uf) Jl(aY BG gL) Tz(aF Mi Qy) Vq(Fp Iv Ut) Mx(Nt Ql) It(dR Ry) aW(Hx Iv) ArJk NrRh MgaX MvoE NdKz TnfP} mZ{cL(Ar Ax Cs Cu Cx Fp hC Iv Jy Kj Kx Lz Ma Mh Ml Mr Ni Nr oE Oy Pi Rf Rh Rj Rm Tz Us Vu Wm) Mp(Ar bQ gL Iv Nr Pi Rm) Pi(Et In oP Rj) Tv(aW cO Iv) Or(aW cO kG) Nl(hA jK) Tz(cO Iv) BgbZ GpdI MaiJ NeiB KxnC UnbQ} Jj{Vq(Ko Lp Lt nC nL Ri Ry We) Et(It rR rT rW uY wC) Fi(It Jl Jm Pa Qb Rm) Ko(rO uR vS wP) Kr(pS rN vT wB) rB(Kn rN vI wP) Aa(pS vW) Wd(Jm Mx) Lh(jO jP) uM(Dg Uf) ApuY CuLp HoJm HpaW UcvS IprV KdUy NxjP} Tz{Yd(aU aW Co Cu Cw Et Ez iJ Jh Kd Kg Mg Mi Mp Ni Nt Oz Pd Pj Uf Vq) Nt(Du Uy Yh Zw) Wd(Af Oz Us Uv) Ho(Af bN Cx) Fi(Af Nu) Vw(Jm Oz) aW(Hp Vz) nI(Ib nK) CxGb TiiZ EzYh GcUv KdUy aFoQ eCmE} Ar{Lp(aE aG aQ aU Et Gp Jk Mp Oz Uc Vq) Jk(Gb Ho Uy Uz Wc Wh Yl Zw) Du(Cu Dc Fy Hv Qh) Gp(Ho Hp Uz Wc) Ho(aE aX Pa) Vq(nI Ry Uy) Gb(Jm Pa) nI(nK oE) TiFb EtYd GnPi HqVc ItUy WdaX KdLt UwbM} Qb{Gb(Ax bG bN bQ Lz Mh Ml Ni Nr Qv Qx Ra Ri Wm) Rv(Ba Cu Iv Nr) Vw(bM Oz Qv Ri) Cu(Yd Yh) Hl(Hw Mi) Yj(aW bN) Si(bQ fR) Pd(Vz We) EtYd EzZw GcRi GnPi NtSj WdOz KdUy UwbM fRnK} Jl{Ti(Aa aY Bg Oz Qw Uv) Hc(Fi Gc Gh Lp Sf Si) Si(Af Bg Qw Us Yd) Wd(Bg Mi My Ua) Gc(Us Uv Yd) Yd(Gp Pj) We(Cp Mi) Qw(Gh Lp) CxZx DeHo HlaW HqrT JkqB KdLp RzaX cHvO} nI{nK(cL Dc dF hA Ky Mp Or Pg Qh Rm) Vq(Ax cH hC Jo Ug Um) Rj(aH cJ Ir Ky Um) Um(Dc Et Kn) Us(cL Lh Pi) Kj(cL Pi) Vu(cH oF) oE(aS dI) QwJp KnUg PicH} Id{vS(Ct Cw Ef Ib In Mg Ng Of) bN(eZ hO qC tM) Iv(hP vH wP) Or(rN rW uG) Jh(qC uZ) wP(Ne Nl) qB(bL Ib) NuwF HqqC IcuI IqjK JkqH aGuM cJjP cWeZ sCrR uRuT} Lp{Et(Af bM Gd Pk) aH(bJ cZ Ez gL) Gp(Hx Nf) Hb(bQ fR) Or(aW Ez) Un(bQ oE) bM(Kx Po) bZ(bF fP) CsMp CuOf CvVq DcNu FaaG NdKz ItRj JdQw QvQm JkOz JyoE QlUg} Ko{uR(aE bA cE cG dF Kp uT wB) hO(dM fN Hc Jv Kc) Ng(qC rO vS) Kc(rR rW) bN(pS wB) vS(Ma Ua) GdcU MgqC IvvU KpwC OurN yHjV oNuT} Vq{Hl(Dc eM Hv Iv Kd Mx Oz Qx Vu) nL(Ax cH Cs Jo Ug) nC(Ad cH Cs Jo) Vw(Nt Nu) nH(cH Jo) GdKk MxVz TviB YdUt RimS cJqU} Nl{qW(kE kI mS mY nA nC) jQ(kI mM mU mY nL) jK(kF mE nH Nk) kI(hA lN qX) jF(nB nU) jR(mY nT) kF(iC jl) ExlK hAmS jYkO} We{Rm(Cp Hv Iv Mi Pi Vu) Nr(Mv Ql Un Ut) Ut(Dc Ir Kd) Cu(cD Oz) Nt(Jq Mj) Mv(Kd Pa) Jk(Ml Qx) DcQl MwUc TnfP IrIv} bM{Ho(Ax Kx Lz Mh Ml Mx Qx) Uw(Iv Mh Mx oF) nK(Kx Lh oP) oF(Gc Si Ti) Ax(Wd Ti) PoUy EtRy NrTl IrLt SiaP KxmI} Et{Yd(Dc Nd Pi Rm) Iv(rW uN Yh) Jk(rN tT tX) It(Ng Og) AdnU AfRy AxDu GlHp MgyH JhwB cQtT rBrR} aW{Vz(Cu Mj Mx Pg Rm) Yl(Ax Cu It Or) Tl(Un Vu) iH(kK oP) CsDu HpOr HxYj SfRm LtUn cZwC oQoH} Ri{rN(cW oH Ou Rc) uT(cO cS oK oN) qC(cH Mg vB) RcvW KkwC KnrB aEvI nNiH wPhR oHvA} Po{Du(Ax cD Dc Dd Jk Jm Mk Mx Ry Uv) Yh(Ba Dc Jk) Zw(Jm Rm) SfUv WdaX} aH{gL(Gb Ho Si Uw Uy) nK(iJ Mh Mr oP oQ) Mh(Ho nL) EmnU GnHa IvUw WdkR KdUy} Hl{Ir(bI bR fR Lt Us Vu) Jm(Cu Hv) Kd(It Vu) Pa(Iv Kz) CxDc MiMx RmbG UyVu} Kn{Hw(qA rN) Ic(jO rB) Iv(fN hP) cH(iB jO) cQ(jQ jR) JkjQ UprB bLhR bNeD cSqA iBoK} Oz{Mx(Rz Wd Wh) Yd(Cu Mp Pg) Lz(pS uT) GnPi NdHp IrWd IvUw SifR ZxUt JkTl RzaX} aX{Rz(Ax Cs gL Ir Nr oE Pk) Wd(Ax Cs gL) fR(mI nK Si) EzYj NtTl} Kr{Ph(rN uL uT vI vT) wB(eC Ik Iv rR vT) TotS HccZ cZwK rBrR} rW{aV(Fa Hb Kk Kp Lz Ou Vv) Ok(Hw Iv Ph) LubA KkaQ KprB OurN} bQ{Hb(eM Op Yd Yh Zx) Si(fP hC) cH(nC nL) GcSs IvVc UwfP} Lu{bA(pS rN rR) eZ(An dM tU) wB(bN oE) YdUt OurN jDuT} nL{oQ(bR eC fR) cH(Lh Vu) cL(Kj Us) oP(aF bI) DiEx MhaE} Pa{Gd(Ez Jd Uf) Iv(Gb Yj Yl) Yj(Kz Nf) CsWd GcUg} Gn{Ha(Hv Pi Uz Vu) DcQl NfKd HxVu TnfP TvIv} Yd{Cu(dR Hb Si) Ut(Hb Hc) CxPg GcLv NdKz RmbG} Kf{uM(cW Hw Jk Mg) xA(Cw Ou) CtjO HwuP hRyD} Lh{jO(mP nO nU) nC(Bg cH) jP(kF nU) HqsC UsnA} Ex{Nj(iB jF jQ lK lN) NcjF NhlK KciB} Mx{Nt(Vz Yl) Kk(Gb Rv) CuYh HcWh SifR WdOy} mI{Or(bI bR Iv mF Rj) DiUt NeiB UscL} oQ{nC(bR eC fR) nH(bR eC) kE(bN Gp) HfnK} uT{Jd(bL hA oE) Ic(Pj uI) oN(Mw uR) PhPj} Nm{Mg(vI xA) wB(Ct cW) IzvI JktN OfqC} Si{fR(Ir Mh) iZ(bF oE) AfdF CuGl KjUt} Uy{Nt(Jq Or) CwQm FpaG GpHx NdKz ItRj} Du{Ax(Hv Mp Nq Un) Ut(cH oE)} Gb{Jk(Lz Mh Ml) CuGl NrOr MhcE} Tl{Qx(Dd Jk) Vu(Gp Kd) CxDc JmUn} Rm{Bg(Rz Wd) bG(Yh Zw) HoKj SfaY} Nc{Nk(eZ rN yL) IrLt lXjQ} Yj{Jm(Hx Kz Nf) IrRj KdQl} rR{rB(Fy Kp) AaJo BbJv cZdM} Gc{Kd(hC Nf) cTdX iZoE} dI{nN(cH oF) mU(Gp oF)} wB{Ph(Aa Pj) aN(Ic Ir)} rN{Ou(cP Dg Dl) cWcZ} Nd{Kz(Ho Uz Yh)} Iv{AnyL OkqC UwaY} Vz{Nr(Hv Mp) CuJm} Kp{rB(cF Ph) cQvQ} Ry{Dd(Lz Qx) ItRj} Vu{cH(nC nH) HoKd} Aa{mU(Ib Qv)} Gp{HpoE KkdX} Nt{Vw(Hx It)} Un{JkqC LtNx} cZ{aNyH dMeT} dH{HqpS cLwL} nN{NeiB QziH} CswCjV TidRiZ FacJeT MhMpHp MwSjQw NgTrvQ UccWzA HwjYkF TnZwfP IrKkRv YhUtoE JqnUjO KxaEnC fRnKkC

Constrained panels with 2 analytes, where 1.0E-8 >= 'AUC p-value' > 0. Contains 1,078 panels of 182,582 total panels evaluated. : Ps(Aj Ar aW aY aZ BG Bn Bo Ch cU Cx Ed Ef Eq Fw Gh Gp hB Hc Ib Ij Im Iz Ji Jj Kd Ke Ki Kl Kx Ld Li Lj Lx Lz Mh Ml Mx No Nw Oa OE Oh Oi Ow Oy Oz Pe Pf Qb Qv Qw Qx Rc Rj Rt Ru Rx Sh Sr Ss Ua Uh Ur Us Uu Va Vo Vs Vt Wf Wh Yg Yk Ye) Vi(Aj Ar aW Ax aZ bF BG Bo bZ CH Dk Ed Eq Fn Fw Hc Hq Hv Ih Im Ir Iv Iz Ji Jj Jn Jp Js Jy Kd Ke Kx Kz Ld Li Lj Lu Lz Mh Ml Mp Mq Mx My Nf Nw Nx Oa oE Of Og Oh Ow Oz Pe Po Qb Qd Qw Qx Rb Sh Sr Ss Tn Tz Uh Un Ur Uu Vb Vt Wf Zx) Uh(aA Ar As bA bV CH Cq Cs cT Dc dJ dK dM Dr Ed eF eP Et hB Hv Hw iB Id Ij In iO Ir Is It Ji Jj Jn Jq Jr Kd Ke Kf Kk Kn Ko Ld Li Lj Lw Ml Mr Mt MZ Na nC Nf nH nI nL No Nr Nw Nx Ny Pb Pe Pi Qa Ra Ri Rj Sr Tv Up Ur Vp Xa) Nw(AA Aj Bg bN bO CH cI De dJ Ed Et Fp Hu Hx Ic Id Ih iJ Im Is It Iv Ji Jj jO jP jT Jv Ld Li Lj Md Ms Mv Mw My Ng nI Nl Ns Ny Oa OE Og oN Ow Oy Oz Pb Ri rS Ru rW Rx Sh Tv Us Vt Wf Yd Yh) Et(aA Aj Bg Ch De Fp Hc Hu Ih Ij Im Ip Ir Is It Iv iZ Ji Jj Jl Jn Jq Js Li Lj Lx Lz Mr Ms My Mz Nc Ng Nl Nn No Ns Oe Of Og Ok Oy Oz Pb Pe Qa Qb Qd Qe Ry Sh Xa Th) Ji(AA Af Aj Bg bN

Figure 30 Continued

CH Dc Ed Ef eZ Fc GI Hc Ik Im Is It iZ Jj JO jP Jq jT Kj Ld Li Lj IN Ms My Ng No Ns Oe Og Om Oy Pb Qw Ri Ru Ur Us Uv Vs Yd Wm Th)
Im(AA Aj Eq Fd Fp Hu Iq Ir Is It Iv Jj Jl Jn Jq Jr Js Jt kC kN kO Lh Li Lj Lu Lw Lz mF Mn Mr Ms Mz Ng nK No Ns Oe Og Ok On Oy Pb Pe
Qd Sh Ux Ye) Xa(Ar aW aX aY aZ bG Bo cU Ed Fc Fw hB Hv Hx Ih Ij Iv Jj Jl Kd Kq Ld Li Lj Mq Mt Mx Nn Nv Ny On Oz Pc Pf Qb Qd Qe
Ql Rj Rm Rx Sh Sr St Un Uu Vq Vt) Ke(Aj Bg bN CH De Dr eC eP fN Hc Ik Jj Jo jP Kj Ld Ms No Oa oE Of Ow Oy qA Ri rS Ru rW Rx Sh
uM Ur Us Va vT wC YD Th) Mz(cH eZ hB hP Hr Hx Ir Is It Jr jT Li Lj Lw Lx Lz Md Mi My Nj Nl Ns Ny Og Oy Oz Pa Pb Pe Pf qZ rS rW vl
wB yH) Lj(aA Fc Fd Fr Gb Ho Ij Is It Jg Jj Jp Js Lw Lx Ma Mm Mn Mp No Nv Og Ok On Qd rS Uw Vw Wd Yj Zq Ti) Li(aA Aj Du Eq Fd Hu
Ih Ik Ip Is It Iv Jj Jl Jq Lw My Ng No Ns Oe Og Oi Ok On Oy Oz Pb rS Wb Th) Sh(Fw Ih Ij Is Jk Jl Jn Js Jv Kq Mt Nb Nn No Nv Ny Oh Om
On Ow Pe Pf Qa Qd Rm Sr Ut Vq) Ij(aA Aj Fr Hl Ip Is It Jj Lx Nl No Nv Og Ok Oy Pb Rt Vb Vh Vz Wb We Yh Yj Th Yf) Jj(Aa Ih Ii Is It Jg
Jn Js JT Ko Kq Lh Lx Mn No Nv Ok On Qa Qd Qe Vq Vt) Wf(Ih Ir Is Jl Jn Ld Mr Mt Mw Nb Nn No Nv Ny Om On Pe Qa Qe Ut Vt) On(Aj Eq
Fp Hc Hu Ip It Ms My Ng Ns Oe Of Og Oy Oz Pb Yd Yh Th) Is(Gd jT nC nH nl nK nL Og Oz Rt Va Wb We Yd Yh Zx) No(Aj Hc Ip It Kc Kk
Ns Oe Og Oz Ur Us Vj Ti Th) Vj(bA Ed Fw Ir Js Kd Mx Nb Ny Oa Pa Qb Qe Rm) Fd(Ar Bo Cx hB Ld Lz Mq Mt Nn Ow Qx Ur Va) Lx(Fc Ir
It Ns Ny Og Ok Oy Pe rS Wb Yd Zw) Zq(aX aZ Ch Ed Eq Fw Iv Nb Oa Qb Rm Uu Ux) Kq(Aj Ch Dr Ef Eq Gd Of Rt Ru Ux Yd Zx Th) Yi(aZ
Bo Ed Fw hB Ld Mq Nv Oz Qd Rt Vt) Ow(Dr Em eP Eq Gd Hp Lp mZ Rz Ux Wb Zw) Ru(aZ Ed Fw Hv Iv Ld Mr Qd Qe Un Vt) Ok(Aj Fp Hr
It Ns Oe Og Oz Qb Qd) Ed(Dr Gb Gc Si Uw Wd Yg Zw Ti) Oh(Gb mZ nC nl nK nl. Wb Wd Ti) Ld(Fi Ho Lp nN Uy Uz Wb Ye) Ny(It nl nK
Ns Og Rx Rz Ye) Aj(Ad Ap Dc Jg Jt Ko Uf) Eq(Mq Mt Nn Nv Om Qd Ut) Fc(aZ Jn Jr Js Qa St Tz) Vt(bN Dr eC Ko rB Ur Va) Pe(Du Hr kE nl
Ns Vz Yl) wD(An Db iP Ko Nd Pj Ri) It(aA Fr Jp Nv Og Ry) Qa(Aa Hl Kc Wc Yh Ye) Qd(De jT Yd Ye Ti Th) Oa(Dr Gc Rx Si Yj Ti) Pf(Gb
Hp Ns Og Vz Wb) Va(Ih Rm Sr St Vq) rS(aW iP Ko Lu Mf) Th(Cs Cu Mt Un) Fw(nl Si Vz Yl) Qb(Gb Ho Vw Wd) Rx(Ih Jn Js Rm) Lp(Ar hB
Mq Ql) Rt(Dc Js Qe Tn) Dr(Rm Sr Ut) Nb(Hl Tl Ti) Wb(hB Mq Nn) Og(Fr Jn Nv) Ux(Mt Nn Vq) jT(Id Kn Lh) Qe(Aa Hl) Sr(Gd nl) Ye(Ih Jn)
Om(We Yd) Ur(Dc Vq) Uw(aZ Uu) Vb(Iv Nt) aA(Ry Si) rN(iP nW) TiJl MqUy HohB YhJs SfRm StnI KoqC NvmZ VqeP cQqZ wBnW Constrained panels with 2 analytes, where 1.0E-7 >= 'AUC p-value' > 1.0E-8. Contains 457 panels of 182,582 total panels evaluated. : Uh(Ad aE
Aj Ax BN Cp Cu Cw Dd Fw Ic Iv iZ Jl Jt Kg Kp Kq Kr Kx Lh Mj Nb Nm Nn Oa Oh Ok Om Ow Pk Qd Qe Uc Ud Un Us Uu Vt Wm) Ij(Aa Fp
Hu Ik Jg Jl Jn Jp Jq JT Kk Lh Lw Lz Ma Mi Mm Mn Mp Mr Ms Mt Mw My Mz Nn Ns Ny Oe Oz Po Qd) Lj(Aa Ih Ip Jl Jn Jq Jt Kc Lh Lv Mg
Mi Mt Mw Nb Nl Nn Nq Ns Nt Nx Ny Oz Pe Po Pz Qa Ri Vj Vt Yi) Ok(aA Ih Ip Is Jn Jo Mn Ms My Mz Ng Nl No Ny Of On Oy Pb Qa) Jj(Bb
Dc Fp Fr Ip Kf Kn Ma Mt Mz Nn Ny Oa Pj Po Pz Qb Uf) Ji(bA cl dJ dM eC Ic Ju Jv Kc Kk Ko Ph rW Uu Vt wD Xa) Og(Ih Ip Iv Jg Js Lh Mn
Mt Mw Nn Nx Pe Pg Po Qa Qd Qe) Lx(Aa Ip Is kE Lw Mn My Nj nL Oe Oz Pb Qd Qw) Et(Ax cH cI Cs Ct Ef Eq Iz Ld Lp Oa Vt Wb) No(Hb
Hu Ih Ko Ld Ms Ng Nj On Pb Qd Qw Vt) Mz(Iv Jn Ml Mn Mp Mr Mt Mw Nc Nm Nr Of) Is(Aa Aj Hc Jp Lh Mn mZ Nv Ny Oe On Oy) Xa(aA
Aj aM Ch Hb Kz Of Or Po Ru Tz) Nv(Fp Hu My Ng nl nK Ns Oe Oy Ux) Aa(It Jn Js Li Mt Nn Qb Qc Qd) Aj(Ba Fr Kf Nn Qd Qe Vq Vt) It(Lh
Mn Mt Pf Qd Qe Vb Wf) Ld(Ed Em Jp mZ Uw Vh Vt Wc) On(Ih Iz Jk Jn Lz Mv mZ Qd) Ke(Af aM cQ dK jT Ng Vt) Nw(eC ml nK nL wB
wD wQ) Ur(Id Im Js Kf Kn Lp Qe) Vj(aX Cq cT Ha Jl Pi St) Pe(Gd kC kO Lw mZ Ny Oy) aA(Ip Lh Mn Nj Ny Uw Yi) Dr(dR hB Kd Qh St
Vq) Sh(Cu Ir Iz St Yi Zq) Wf(Cu Hx Iv Nt Tn Un) Ko(bN Ch hO Im In qZ) Vt(Ax dK Lt Of Ri) Ch(Jp Sr Tn Uf) Im(cH Gd Kk kP) Qa(Hc Jg
Kk nl) Qb(Jg Wb Yi Yj) Ru(Fp Hx Po St) Ny(Ip Lw nL Oy) Om(Gd Rt Ux Ye) Pf(Fd Lw Nj Nx) Nn(Lp Uz Vc) Ng(Fr Jg Kq) Zq(Ha Hx Jm)
aZ(Ho Vw Wd) wD(Bg Kc Ou) Cu(Rt Vb) Eq(Pd Uf) Mn(Ip Nh) Yi(Ar Li) Qd(Oz Pb) St(Ho mZ) Ye(Rm Vq) Ow(Jp kP) nl(Js Vq) iP(qZ tT)
ThNt FcRm FdQl NljK TzVa IdbN IpJg IrLt IvUw KcLi KkiB KnrB KprW LhnL RiuT OurN cQwB Constrained panels with 2 analytes, where 1.0E-6 >= 'AUC p-value' > 1.0E-7. Contains 731 panels of 182,582 total panels evaluated. : Et(Aa Ao bA bN cP cQ dM Ed hB Ic Id Kc Kj Kk Kn Ko Kx Qw Ri rW Sr Tv Ug Ur Us Uu wB wD Wf Yd) Qd(aA Fp Ih Ip Is Jg Jn Jp Kc Kk Kn Ld Lh Ma Mm Mn Ms MZ nI nL Ns Nv Oe oH Oy rS Ur Us) Lx(aA Fp Hq Hu Ih Iq Iv Jg Jl Jn Jp Jr Js Jt Lh Lz Ma Mi Mp Mr Ms nK Nl Nn Nv Ow Qa) Vt(aQ Ar bA CH cI cT Id Ij Im Is jT Kc Kk Kn Mh Mn Mt Nn Nr nW OH Ow Qa Qe Sr) Fp(Aa Fr Ih Ik Ip Is It Jg Jp Js Jt Lh Ma Mm Mn Mz Nx Ny Og Oz Pb Qa) Ur(Ax Dd Fy Ij Ip Ir Is Jt Ko Lh Li Lj Nv Oa Oh Ok On Pi Qa Sr Un Yi) Mz(aA Fr Hv Ih Ip Iq Jg Jt Ld Lv Ma Mx mZ nI Nv Ow Po Pz Qe rB Wf) Sh(aH cE Cp Dk Fy Gc Hq It Ji Ju Ko Ks Mv Mx Nt Pg Ph Qh Sf Tn Uf) Jj(Hb Ir Jl Jm Jp Kg Kp Ks Mm Mw Nm Nr Nx Ow Pf Pg rS Sr St Un Yi) Mn(Aj Ch Ih Ir Jn Jq Lu Lz Ms Mt Ne Nl Ns Nv Ny Oy Oz Pe Pf Qe) Qa(Aj Fr Ij Ip It Jp kE Kn KO Ld Ms Mw Nv Oe On Oz Pb Qw Us) Ny(Ib Ih Ir jK Jr Lz Mi Mp Mr Mt Mw mZ Nj Nl Oe Oz Pb Qe Wm) Fr(AA Hu Ih Ip Is Jn Js My Nj Nl Ns Oe Oy Oz Pb Qb) Is(Ip It Jg jK Kc Kk Ko Ld Ma mI Mw Nm No Pb rB) Uh(aM eM Fa fR Fy Hp Im Kc Mh Ms nK Ru Uw Vs Yi) Pf(Gd Ho Ip Ir Jn Jr Mi Mp Mw Nl Oy Oz Pd Pe Ux) Js(aA Aj Ij Ip It Jg Jp Kc Mm Ms Nv Oe Oz Pb) Aa(Aj Jl Lu Mk Mq Ms Ne Nl No Ok Oy Oz Po) Qe(Ij jT Kc Kk Ms nI Nj Nl Ns Oe Oy Oz Pb) No(aA Ch De iO jK Jn JT oE Ow Oy Ph) Nv(Aj Ih Ip Jn Lz mM Ms Nl Of Oz Pb Ti) Ij(Gd Hc Ih Iq Ir Iv Kc nC Ng nL Of) Kk(dJ Dr Ed Jp Lj Oh rB Sr Wb Wf Yi) Ld(cH iB Id Im Ko mI mU nI Oh Sr We) aA(Ho Jg Jn Jt Ma Mm On Oz Pz Ru Ti) Aj(Bb Dg Id Kn Lh Oh Om Sr Uc Un) It(Ip Jg Ma Mw Nn Nr Oz Pe Po Va) Xa(Bg Lz Mh Nr Nx Oi Pi Qx Vu Wf) Ke(aF dJ Ed jO Jv lL Ph Uu Vs Wm) Yi(aP Iv Mt Nn Or Rh Rx Un Uu) Ko(Ed jT Kj Ng Oh Ow uR Uu wB) Lj(Ir Iv Jo Mr Oh Om Ow Pa Pc) Ru(Cs Dr Hb Jd Mp Mv Qb Tz Vq) Vj(Dc Fy Il Jm Lp Nr Qh Vq) Ip(Jp Ma Mt Mw Nc Oz Pb) Ji(cT jE Lp Ou rS Rx wB) Kq(Bg De Hc Ik Iz mZ Oy) Og(Hx Ir Jl Jp Jt Nr Om) jT(Fa Jq Jr Li Mt Oh Un) Ch(Id Im Jd Nn On Ow) Lh(Ih jO Ms nC Oz Pb) hB(bN cH cQ Si Uy Ti) Ar(Ho nI Uz Wb Wc) Ir(Oz Rx Ry Va We) Zq(aH dR Gd Ki Tz) Kc(cH iB jK Oh rW) Rt(Fd Fy Ok Pi Tv) On(Iv mM nL oN Qw) aZ(Fi Gb Ry Vh Ti) oE(Dr Kn nI Si Wb) Nn(Gb Gd Ok Wc) Mt(jK Oe Oz Ti) Wf(Jh Mq Pg Vu) Jp(Hc Ih Jn Oz) wB(dJ Kr Nm Ri) qZ(dJ eC Hc qA) Eq(Ez Jd Nt) Th(Ax Iv Ut) Fc(Fa Hx Qb) Im(Dr iO oH) Rx(Fy Ok Tz) Nw(mZ nC rB) Ow(mE Ng Qw) Va(Dc Hb Vu) cH(iB nC Sr) nI(Oa Rj Tz) Bo(Uw Yg) Po(Du Wb) Ti(Ax Iv) Fd(Nu St) Mw(Nl Ye) Ho(aH Oh) Si(fR Uu) Jg(Ih Oy) Oz(Pe Uw) Pg(Hq Ns) Pj(eP uT) dM(pS rB) mZ(cL Pi) wD(Ef Kn) rS(Fb Kr) nW(tX uX) DrTn EmOa GbSt GcUu MaQb MqYe NgUf IdaF IlYI YdUt WbOm JrrB KfOf LipS RirN UkPe cZrR nNiH oNuT Constrained panels with 2 analytes, where 1.0E-5 >= 'AUC p-value' > 1.0E-6. Contains 1,148 panels of 182,582 total panels evaluated. : Jj(aA Ad Ap Co Dd Ed Fa Fw hB Id Il Io Jd JK Jo Kc Kd Kk Kr Kx Ky Ld Lv Mx Nh Nj Nl Nt Om Oz Pe Pi Qc Qh Rf Ri Rm Tz Uc vI Wm) Qe(aA De Fp Fr Hc Ih Ip Ir Iv Jg jK Jl Jn Jp Jq Js Jt Ko Ld Lh Lw Lz Ma Mi Mm Mp Mr Mw mZ nC nL Nn Nt Nv Pe Po Tv Us) Ld(AJ aQ bB bR cG Ch dM Dr Fw HB Ij Jr Js Kf Kq Lj Lx Mn Mt Nh nK nL Nn Nr Ny Oa Ok On Ow Qh Ri Uf Un Vq Th) Mn(Ar Bg cH Fr Hv Hw Iq Iv Jg Jp Jr Js Lh Lv Lw Ma Mi Mm Mp Mr Mw Mx Nm Nn Nr Nt Pb Po Qa Qb Qc Sh Ur) Jp(aA Aj Ar Bg Fa Fr Id Iv Iz Jl Kc Kn Ko Kx Lv Lz Mp Ms Mt Mz Ng Nn Ns Ny Oa Oe Pb Po Qb Wm) Kk(Aj aQ Ar Ax bN CH eC Fd Hb Id Ir jK Js Ko Kq Kx Li mU Nn Nv Oa On Ow Pj Ri Ub Un Vq) Ny(Aj De Fr Gc Hc Hv iB Ic Iq Iv Jg Jl Jn Js jT Lh lO Lv Mm Ms Mx nC Ng Nn Nt Po Qa Qb Qc) aA(cH Fd Fp Gc Hb Ih Ii Io Is Ko Lw Mt Mw nK Nl Nm Nn Nr Ns Nt Nv Nx Og Qa Qb Qc Vh Vt) It(Ih Ir Jr Jt Lv Lw Lz Mi Mm Mp Mr Mx Nb Nl Nm Ns Nx Om Pa Pb Pz Qb Qc Rx Uy Ye Th) Ko(aM dK dM eC Gd hB Id Ij Jo Js Jv Kc Kx Lj Lx Ml Oa oE Oi Qb Qd rB Ri Sr Ss Us) Vt(bS cE Cs dJ Dp dR Ed Em eZ Fy Gp Jq Kf Kq Kx Li nI Oa oE On Qd rS Tv Tz Uf Tl) Id(aE aQ cH cJ cQ dJ dK eC Ed Fw Hb Im In Ji jK Kc Lj IL nI oE Oh qC Us Wf) Qa(De Dr Hb

Figure 30 Continued

Hu Ih Jn JT Kf kN Lh Ma Mm MZ Nj Nm Ns oH Oy Tv Vs) Zq(Af Aj Ar bM Dg Dr Fp Il Kd Kl Lp Mh Mm oE Oz Pk Rf Ss Vo Vq Wf) Jg(Hu Jn Jq Lh Lw Lz Mp Ms Mt Mw Mx My Nl Ns Oe Of Oz Pb Pe Po Sh) hB(aE aW bS Ch eC Gb Ij Ip Is jO Lj Lu nC nK nL Ow Pj Qd rB Ry Th) Mz(Ar Ch De Jl Js Kc Kx Lh Mm Ms Nn Nx Ri Ru Sh Tv Ur Us wD Wm) Fp(Io Ir Jl Jn Jq Lw Mp Ms Mt Mw Nc Nj Nl Nm Nn Ns Pz Uw Th) Aj(Ar Ax bA Co Cu Dl Fa Fy Ih Kc Kx Lj Ma Mt Oa Ow Pj wD) Og(Aa Ii Il Iq Lw Ma Mi Mp Mr Mv Mx Nm Nt Nu Oh Pa Qb Qc) Pf(Eq Hv Iq Iv kE kN Lz Mr Mx Nc nI nK Nm Nr Pb Qc Yi Ti) rS(Ax Et Jl Kn Kp Mh No nW Ok Pj Ri Uk uX vl wB yL yE Wm) Qd(bN CH eZ Hc Iv Jl Jq Jt Kf Kj Mr nK Nn Ow Qw Wm) Im(aQ Bg bS cl Ct De dJ Hb iP jK jT Kc Kn oF Ou Qw) Ip(Ih Jn Jt Lh Lz Mp Ms Mx Nl Nn Nr Nt Nx Pe Po Qb) Is(Ch eM Hu iO Jn Kf Kj Lw Mm Mt My Nj Nn Ns Qw Us) cH(Ar Ed Hb Ij jT Kx nL No nY Oa On Ow Tn Tv Un Ur) Kq(bL cQ Ct Jo Kc Kj Kn kQ Lj oE oH Oi oN Qw Ur) Nv(Hc Ir Iv Iz Jl Jq JT Lw Mr Nj Nn oN Qw Wm) Ar(aE Bb cJ Dc Gb Hb Kc Kn nK Ri Ru Ur Uw We) Fr(Hv Ir Iv Jl Jq Jr Lw Lz Mp Mr Ms Mx Nc Pe) Js(JT Lh Lw Ma Mt Mw mZ nK nL Ns Oy Us Th) Sh(Ba bQ Dc Dd Ef Ii Jh Jt Lh Ok Si Tz Uw) nI(Ij Jn Mt nC nK nL nU On Pg Pi Qb Qc Um) wB(aN Hq Hu iP Jk Lj Ma Me oE Oy Pj rB rW) Ch(Fa Hb Ij Kf Kx Lx Oa Ok Un Vj Vq wD) Yi(bM Jo Kc Lz Ml Mx Of St Vb Wf Yh Tl) Lh(Hr Hu Jn Jo jP Ng nK Ns Oe Oy Qb Wb) Ur(Aa Bb Cq dM Ih Lx Nr Qh St Uc Uf) Oz(Fd Gc Ih Iv Jl Jn Mw Nn Nr Pg Po) Et(cT Dc Dr jO jT Kd Kl Ph Tz Ux) Sr(aE dJ In Kc Oe Of oH Oi Ri Uu) Pg(Jr mZ Nj Oy Pb Rt Ru Tv Vj Ti) Po(Ih Ir Jn Ma Ns Oe Oy Pb Pe) No(Bg bO dJ eC Ic Iv nK Ou Vs) Lx(aV bZ dA Jq kN Mm mZ Nt Tr) Mt(Ih Ir Jn Ma Nj Nn Ns Pb Pe) Qb(Jt Kc Kf Mm nC nH nK nL Ti) Wf(aM Ax Cp Fy Hv Jd Ok Pi Uw) On(Bg De Ef jT Kc Kj oE Ow Us) aZ(Fd nK Rt Uz Vb Vj Vq We Wg) Dr(Fw Ha Nw oF Ou Tz Uc Xa) Kf(Ed Hc hX Lj Oy uM Uu xA) wD(aN bS Ct Hb nW rB rC Tn) Fd(aP Cs Mw Nq Nr Nt Uh) Nn(Hu Ih Jn Ng Oe Oy Pb) Kn(dJ Ed jO Lj mU Oa Oh) Vj(Ax Dd Eq Jk Ph Ru Uy) nL(cL Kx Mh Oa Qc St Vq) Ir(Lw Lz Nr Ns Pb Pe) Kc(Ax Cs hW Ih Jl Oa) Ke(bR eM Gd Ic iJ Yh) Un(bN eC Lj Lt Us Va) mZ(bQ bZ cO Cu Iv Mp) uT(bL Hq Jd Nq Oy rW) Lp(Bo bZ Jd Kx Qm) Ow(bX dM Fa Oa rN) Eq(Ba bQ Cu Rz) Ma(Ih Mx Pb Qc) Mw(Jn Nj Ns Pe) Wb(aP Ji Kx oF) Xa(Cu Ml Mp Pa) Lj(Hb Jd jT oF) Ru(Dk Ha Nq Ou) Ri(eZ Kx qC vl) Gb(aH Bo oE) Gd(Jn Li Mq) Jq(jO jP Va) Ry(cU Hx Uh) Rx(Dc Ha Mr) Nw(kP nN nT) Oa(In Oe Oi) Vu(Hl Vb Tl) Vq(iB In nC) iP(hL tQ uX) rN(Hw Lu Nk) Aa(aJ Nc) Ti(Fa Tz) Em(nU Uh) Th(Ok Uf) Mm(Ih Jn) Ho(Bo Rf) Uc(Of Va) Qw(Ij Li) Rt(bA Cp) Oh(Hb Us) Uw(Af oE) Ux(Cu Uf) Pe(Nr Pb) IX(jR qW) nC(Kx Qc) nK(aH St) rB(aJ Kp) jT(Nx Or) AxWd DeLi GpeM MhjK MpVa MqWc MrYc NgJt HpoE HcOk IvmI YgUu YkRm SiaP JiyL JnOe RzaX UhhW VbPd PjdM aEiZ bLqZ bNoQ cZrW eCnU Constrained panels with 2 analytes, where 1.0E-4 >= 'AUC p-value' > 1.0E-5. Contains 1,845 panels of 182,582 total panels evaluated. : Jj(Ar Ax Ba Bc cH cP cQ Cs Cu Dg Dl Em Ez Fb Fi Fy Ha Hv Hw Hx iB Ic Iq Iu Iv jF Jh Ju Lp Lz Mg Mi Mj Mp Mr My Nc Ng Nq Nu oF Og Oh Ou Pa Ql rN rP Si Tr Ua uT Uw uX wB Yg) Ld(aA aM aP Ar Ax bA bN bS bV cE cJ cQ Cs cT Cu Cw cZ Dc dF dJ eC Fa Fy Gp Hf Ic Ih It Jd Jl Jn Jq Jt Kc Kd Kn Kx Ky Lh Li Mw Mx Ne Nv Oi Pi Pj Qb Qc Rf Tz Vp Zq) Kk(aA aM Bg bR bS cA cQ Cs Cu Dc Fw Gb Ho Hv Ih Iq It Iu Iv Jl Jn Jq Jr Jt Kd Kn Ky Kz Lh Lp ml Mx Mz Na Nc Nh Nl Nm nN Nr oE Ok Pi Qb Qc Qh rN rS Tz Uf Ur Uz) Aj(Bc cG Cs Cw Dd dF Ez Fw hB Ii Ip It Iz Jd Jo Kd Kg Kl Kp Kr Lx Mm Mw Mz Nm Nq Nx Po Pz Qb Qc Qh qZ Rf Ri Rm rS St Tn Tr Tz uT Uw Wd Yi) cH(bA dM Fa Fb gL Is It iZ Jp Js Kf Kn Ko Kp Kq Ky Li Lx ml Mt nl nN nR nU Nv Ny oF Ok Pj Qa Qe Qh qX Rf Ri St Tz Uf Vj Zq) hB(aQ bB Bg bL cJ Cu Dc dJ Em Fw Hb Hc Ih Im It Jn Jp Jq Jr Js Kc Kd Li IL mF ml mZ nI Ny oH oN Pi Qe Ri Tz Ur Vc Vq) Ko(aJ Ax bA Bg bS cA Dc Fa Fw Hc iB Ih Ik Ir iZ Jl Jq Kl Kn Kq Li Mh Ne Nh Nn Nr Oe oF Or Qw Rf rN Tz Ug Un Va Th) Ch(Aa Ar Ba Bb bQ Co Ef Fr Gc Jh Jt Kc Kn Lh Li Ma Mt nU Nv Oh Pj Qa Qe Qy qZ Rf Ri Rm St Tz Ua UT Uw wB Wd) Jp(Ax bA bN bO cl Cs Dc De Ed Hb Ir jK Jq Kf Lh Lw Ma Mi Mr Mx Nj Nl Nr Nt oE Oy Pe Pj Qw Ri Sh Sr Tz Ur Vq) Ow(AA Ar Ax Bg bS Cs Hb Hc Id In Kc Kf Kn Kp Kx Li Mn Mr Mt Nr Nv Oe oF Oh Ok Oy Pe pS Qa Qe Ri Sr Ur) Kq(aA aM aQ bN bS cA cl dM eC Em Fr Hq Id Im Jk jT Kl Lu Mv My nl Oa Ph Qu Ri Ss Tn Tv Ua Us Uu Uv Vs) Ar(AA aQ Ax bA bN cT Cu De dJ Ed Ic Ik It Iv Jd jK Jn Jq Jr jT Kd Kf Lw mZ nC nL Pj Tz Un Vq Yg) Mt(De eC Hb Hu Id Iq Iv Jl jO Jq Jr Jt Kf Lv Lw Mi Mm Mp Mr Ms Mw mZ Ng NL Nm Po Qb qW wD Wm) Hb(aJ aM Ax bA bN dG dM Ed Fc Ih Is Jl Jv Kc Kf Kn Kx Li Nn Nr Nv Oa pS Qd Qe Ri rW Sr Uf Ur) Ri(Ax Cs dM Ed Fa Id Im Jq Js Lh Li Lx Mn Nv Ny Oa Oh On Pe Pj Qa Qb Qd Qe Un vB Vq wP Zq) Kf(aA aM Ax Bg bN cQ Ct dM eC Gp Ij Im In Jo Kj Kx Li Ml Ng Oa OE Oh Qe rB rS Sh Us) Ur(BA Cs cT Dl Fa Il Iq Iu Jl Jq Kd Kr Nh nl Nm Nn Nt Nx Ny Pe Pj Pz Qc Rf Rm Tv wB) Oa(aQ bN bR bS bX cJ Dp Ij jT kO Kp Lh mZ nC Nh nK Ny oF oH Ok On Pi Pj Qg Sr Un Us) nl(aJ aP Ax bN cL dF eC Ed Fa Fp Ih Ir Iv Ji Ky Lh Lx ml NH nN No oF Pa Ug Us Ut) Kc(aA aQ dF dM eC Ed Fa Fp Jq Kx Lx Mn Mx Nn Nv oE Ok Qc Qh rB Rf rS Tz Un vA wB) Mw(Hu Ih Ir Iv Jr Jt Lu Lv Lw Lz Mr Ms Mx My Ng Nm Nr Nt Nx Oe Oy Pb Po Qb Qc) Kx(aA Ax bN bS dM Fd Fw iB Ij Im Is Js jT Kn Mn mZ Ng Nr Nv Oe Oi Ok On Pj Th) Oz(Hp Iq Jq Jt Lv Lz Ma Mm Mp Mr Mx Nb Nl Nm Nt Nx Og Om Pa Qb Ry Si Vj Vq Wd) Nn(Bg Fr Hc Id Iz Jg Jq Js Jt Kn Lh Ms Mx My Nj nK Nl Ns oH Pe Po Qa Qb Qw) Dr(cU dX Fy Ih Is Js Ky Li Lx Nd Pf Pg Qc Qe Um Un Uw Vb Vu Wf Yi Tl) Ma(Hu Ir Iv Jl Jn Jq Lv Lw Lz Mi Mr Ms Nc Ng Nj Nl Ns Ny Oe Oy Pe uT) Id(aW bS cA dR Ic Ij Il Is jQ Kn Li Mn Nh OF oH On Qa Qd rB Ru Sh) Jt(Ct Fr Ih Jg Jl Jn Jo Jq Lh Lv Lz Mn Mp Ms Ns Ny Oe Oy Pb Po Vb Th) Pj(aA aE Ax bA Ed Fa hC hO iB Is iZ Jq jT Lj oE oF Qa Qb Qe Tv Ug vl) Sr(Aa aN aQ Ax Bg bN cJ cQ dR Hc Ic Jq jT Kn Lj mZ Ng Oh Oy Ph Qw) Lh(Hc Hx Ir Iv iZ Jl Jq Kj Lw Lz Md Mp My mZ Nm oN Qw Us Uu Va Wf) Ij(bA Bg bN cl Ct De dJ Ib Ic iO Iz Jv Kn mZ nK Tv Ug Uk Us Vs) Og(Hv Hw Iu Jh Jk Jq Jr Lv Lz Mj Mm Mq Mu My Nb Nc Nh Nl Nq Pz) Fd(aH aM aN bJ Et Fp gL Jd Jh Ml Mv oE Qy Rx Us Ut Vj Vq Vt) Ip(Ed Hv Iq Ir Iv iZ Jl Jq Jr Lv Lw Mi Mm Mr Nj Ns Om Pa Qc) Jn(Ih It Jl Js Lv Mp Ms mZ nC nK NL nN Ns Pb Pe Pz Qb Wm) jT(aA aD aM aP Fr hW Ih jl Jl Lw Lz Mh Mj Ml Mq Nh Ok Po Qb) Un(Ax Bg cQ dK Et Gp Hc In jO Li Ms oE Of oH Oi Qw rB Ug) Lj(aE aQ Bb bF cJ cL Hf iB Ic iO Kp oH pS Qy Tz Uc Us) Zq(aC aL bA bR hC It Kz Me Mj Mr oF Om Pa Po Qh Uh) On(bN bO bZ cl Ct Ed iZ jO Kl nK Ou Ss Tv Tz Uu Vs) Kn(aA AfaM aQ bN cQ eC In Jo Li Of Qb Sh Us Uv) Uh(Fc Gn Hl Ho Lp Rt Uz Vh Wc Wd We Wg Yl Zw Tl) Nr(Iv Jr Lv Lw Mi Mp Mr Mx Nj nL Ns Oe Pb Wf) Ih(Jq Js Ky Lv Lw Mp Ms Nj Nm Ns Nt Oe Pe Us) Vj(aE aH aL Hx It Iv Ks oF Ok Pk Ry Tv Tz Vt) Po(aA Hc Hu Io Jq Jr Lw Mm Ms My Ng Nl Pz) Gc(aZ bQ cU dR Hx Jl Kz Mr oE Qb Qv Rf Ry) Ir(Hv Io Iq Jg kP Mp Mr Mx nC Nj nL Us Wm) Pe(bS Ct De Fp Io Mm Mp My Nc Nj Nm Qc Qw) wB(An Bg bL cP Dg dM Hc Ic My Ng Nq oN Um) Lx(Bb bO bQ bS cG cK De jK Kp IX pF Uk) Yi(aH aS cU Fc Ji Kj Kz Om Qx Tz Uv Vu) Qb(iO ml Mp Ms Mz Nl Nm Ns Nt Nx Oe Pb) Qd(aQ bA Bb eC jK jO kE mF oE rB Ua Vs) Jg(Hv Iq Iv Jl Jr Lv Mi Mr Nt Oi Qc Uu) Oh(bO Fp Ic jK jO Jv Kd Nc oH oN Qw Vq) aA(Ap Bb bN cQ Jl Jm Jq Lv Lz Mp nL Pb) Fa(Bg bS dJ Dp eC In jO pS rS Ru Us) Is(Bb bN Ct Dc Dp Ic Ms Up Uu Vv Wm) Qa(Bb bN cP Ct Iv jK Jl Jq Mp Mr Ou) Nv(Bg bS De Dp Ic jO oE oF Ou Us Uu) nC(aP Ax bR Gp Iv Ji Js Ke Mh St Vt) rB(aP bA Im iZ Ji Jl Js Ke Ny rN uX) Aa(aM aP Ax dF dM eP oE oF Ug Vt) No(aQ bS Ct jO kE kP IX oH oN Uo) Sh(Co Cw Fr Ky Nq Ou Pz Ua Uc Yg) Qe(Bb bN iJ iO kE Kp nK oH Qw Vs) Li(bA Bb bO Dc Dp Ic jO nL oH Us) Ok(Bg bN cP De Gd jK jO Kj rW Us) Et(eC Fc Fy jK jP rN rR uY Vq) Fp(Iq Iv Jr Lp Mi Mr Nt Pc Uy) Wf(Bc Dc Dk Ii Jq Jr Mj Ql Uc) Ru(aH dR Ex Hq Jr Kz Or Pi Vu) Nx(eC jK Lz Mx Oe Oy Pb Qc wD) nK(aD bQ cL fR iH Iv Or Pg Qc) Ax(Bb cE Ed Ho Ic Jd Mn nL) It(Hv Iq Iv Jl Jq Ms Nt Pc) Lp(aH aZ Mr Mv Nq oE Rf Vq) Mm(Iv Jq Ms Oe Pb Qc wD) Wb(aH aJ bQ dF Ml Ql Qx) Si(bQ dF hC iZ Nu oF Va) Js(Hc jF Jl Mp Mr qW Ug) Uf(Bg In Kj oH Oi Us Uu) nL(aH aS Gp Ji Mr oP Vt) iP(rV rW tU tV tX uP yL) pS(bA bN cJ Fb Kp Ou qZ) Dc(Ct De In Mn Tv Us) Gb(bQ dR Lz Qx Rf Uu) Mz(bN Hc Jo Jq Kp Nt) Im(aN bA Hc Kj Ua Vs) Vq(Ik Ki Oi To Ug Uu) iZ(aQ cJ cQ dD Mn Ti) wD(bH bX cQ dE dl tF) oF(aE cE cQ Mn Ny Ti) Nl(iB

Nv Ok Qa Qd) nH(bl bR cL Ih Ir Ke Mh Vt) wB(aE Ao Ba Dl Iz qA rV uR) Ct(Ba cT Fy Jg Js Nv qZ) Ma(Hv Iq Jr Jt kN Mp Mw) Nj(Iv Mx Nb Nq Og Pa Ql) Hp(bB Bo bQ cU dF Mh Mp) Im(EM Ic Jv Qt Ug Uu) Si(aJ aM cE cN Nf Qv Ra) Jd(Mz Nh Oe Oi Uu Ux Ye) Jl(Ih jO Mw oH Oy Po rW) Jp(cT Cu dJ Hv Jt Vs Zx) Gb(aM cU Mh Ml Or Uh) Tn(bL Lu Ng Oy Uu Vs) Ii(Lh Ms Mx Ng Oy Rx) Ip(Hw jF jQ nC qC Wm) Ye(Co Hw Pd Ql Qy Wd) Pi(Dp Ko Mz Of Ry Ug) dM(Gp Js Kp Ny uR uW) nU(Ad bR Ji Mu oE oH) mU(cK Db Em Gp Js Nh) qZ(aN bS Id Iz oN rS) Bo(eM Rt Uz Vh Zw) Nr(bS Hv Iq kP Ms) Mn(aJ cT Jv Kj oE) Qe(cP cT dJ Ic jQ) Jr(bF Lw Mi Pa Wm) Vs(Fy Is Lh Nv Ok) Pe(lO Lv pF Rg Tj) cJ(Mz qX rV rW uP) nC(aS cL Fp Ih Jh) iP(jF sO uU vA vW) Dg(tQ tT tU uY) Fi(dR fR Nq Qx) Mw(Hv Iq Mi Mp) Uc(Ng oH Oy Rt) Ij(Ao Kj Ph Uu) Iv(Hr Ih Lw Po) Jt(eP My Rt Ug) Kp(lL Mq Ng Qd) Uh(Du uY Vb vW) Ux(Co Ez Jg Pd) aF(dF Is oP oQ) qC(bM Fb Ok qA) rS(eD Id jV qX) An(uX yL tM) Dp(cE Ok On) Em(aM Fw No) Fr(bO Iz oH) Lu(dF Fw gL) Qa(Ib kC mF) Jv(Ju Lh On) Ry(aM Mk Nu) Nv(Af dJ Kj) Of(Ad Ut Yg) Og(Jm Jo Mg) iH(aE kG mI) rW(aN cE Di) oE(bF gL wJ) oN(bQ cE kP) Cp(Vb We) Fc(Mv Qh) Fy(Jo Ko) No(Fw Tj) Mp(Po Yi) Hx(mE Yj) Ic(Js Ok) Id(lK vS) Ir(Lv mF) Is(cP dJ) Qd(cT jQ) Wd(hC Jm) Rx(Vp Vv) Qm(eP Uz) Ug(Dd Vh) Vc(aZ cU) Oy(Nb Pa) Pf(bS eM) bI(oP oQ) dF(bO jO) tX(dJ Nd) jY(mP nM) rV(rO yH) nW(tT yL) BcLt CuKo EteM ExlK NuUz LwPa MlRv HvYi IhkP YgKj RctQ JgSs JieP QhOi LhOu RtVv UtmE UuVh VtvS aEuP aMbF aNwJ aWhC bBoH bQbZ cLmI cZqX dIoQ eDwP fNhO jIkN

Figure 30 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.2E1 | 9.8E1 | 8.1E1 | 1.1E2 | 5.0E1 | 8.3E1 | 8.0E0 | 7.0E0 | 2.4E2 | 4.8E2 | 178 | 120 | 178 | 120 | 0.61 |
| Ad | ug/mL | 3.8E-2 | 5.3E-2 | 6.7E-2 | 1.9E-1 | 8.2E-2 | 9.3E-1 | 6.8E-4 | 7.8E-4 | 3.7E-1 | 8.5E0 | 91 | 83 | 91 | 83 | 0.59 |
| Af | ng/mL | 1.3E0 | 1.2E0 | 1.2E1 | 7.6E0 | 5.7E1 | 2.1E1 | 1.7E-3 | 1.7E-3 | 5.3E2 | 1.9E2 | 91 | 83 | 91 | 83 | 0.51 |
| Aj | ug/mL | 1.8E0 | 4.8E-1 | 2.6E0 | 2.0E0 | 2.5E0 | 2.4E0 | 1.5E-3 | 1.3E-3 | 6.1E0 | 6.1E0 | 91 | 83 | 91 | 83 | 0.42 |
| Al | mg/mL | 8.5E-5 | 8.8E-5 | 2.6E-4 | 2.9E-4 | 4.6E-4 | 4.3E-4 | 4.3E-6 | 6.6E-6 | 1.8E-3 | 1.8E-3 | 91 | 83 | 91 | 83 | 0.54 |
| An | U/mL | 5.0E1 | 7.8E1 | 1.9E2 | 3.3E2 | 6.2E2 | 9.2E2 | 2.8E-1 | 6.4E-1 | 5.5E3 | 7.8E3 | 91 | 83 | 91 | 83 | 0.60 |
| Ao | pg/mL | 8.7E1 | 1.0E2 | 8.3E2 | 2.4E2 | 4.8E3 | 5.3E2 | 1.5E0 | 4.1E0 | 3.9E4 | 4.5E3 | 91 | 83 | 91 | 83 | 0.58 |
| Ap | ng/mL | 3.2E1 | 3.8E1 | 4.8E1 | 5.3E1 | 5.8E1 | 5.5E1 | 2.0E0 | 2.4E0 | 3.3E2 | 2.9E2 | 91 | 83 | 91 | 83 | 0.55 |
| Ar | ng/mL | 4.9E-1 | 1.3E0 | 1.5E0 | 4.9E0 | 3.1E0 | 1.0E1 | 3.4E-3 | 3.4E-3 | 2.0E1 | 5.1E1 | 91 | 83 | 91 | 83 | 0.65 |
| As | ng/mL | 8.0E-3 | 1.0E-2 | 1.1E-2 | 2.8E-2 | 1.6E-2 | 1.4E-1 | 1.7E-3 | 1.7E-3 | 9.8E-2 | 1.2E0 | 91 | 83 | 91 | 83 | 0.54 |
| Aw | pg/mL | 1.6E1 | 1.7E1 | 1.7E1 | 1.8E1 | 5.5E0 | 6.9E0 | 6.8E0 | 2.9E-2 | 4.2E1 | 5.1E1 | 91 | 83 | 91 | 83 | 0.52 |
| Ax | ng/mL | 1.3E0 | 5.5E0 | 7.3E0 | 5.4E1 | 1.6E1 | 1.6E2 | 1.3E-2 | 1.0E-4 | 1.1E2 | 8.5E2 | 91 | 83 | 91 | 83 | 0.62 |
| Ba | ng/mL | 7.7E1 | 1.3E2 | 4.5E2 | 9.8E2 | 1.3E3 | 2.3E3 | 1.9E0 | 1.1E0 | 8.1E3 | 1.5E4 | 91 | 83 | 91 | 83 | 0.60 |
| Bb | ng/mL | 3.7E0 | 6.0E0 | 6.0E0 | 9.0E0 | 8.0E0 | 9.6E0 | 4.1E-3 | 4.1E-3 | 4.9E1 | 4.8E1 | 91 | 83 | 91 | 83 | 0.61 |
| Bc | ng/mL | 2.7E1 | 6.0E1 | 1.1E2 | 1.6E2 | 2.2E2 | 2.5E2 | 4.9E-1 | 1.0E0 | 1.0E3 | 1.2E3 | 91 | 83 | 91 | 83 | 0.61 |
| Bg | ng/mL | 1.0E-1 | 1.3E-1 | 2.9E0 | 9.8E0 | 1.0E1 | 4.8E1 | 5.3E-4 | 5.3E-4 | 7.7E1 | 4.0E2 | 91 | 83 | 91 | 83 | 0.54 |
| Bn | ng/mL | 5.6E-2 | 5.6E-2 | 1.0E0 | 1.9E0 | 1.9E0 | 6.6E0 | 5.6E-2 | 5.6E-2 | 7.5E0 | 5.8E1 | 91 | 83 | 91 | 83 | 0.55 |
| Bo | ng/mL | 1.3E1 | 1.4E1 | 1.4E1 | 1.7E1 | 1.0E1 | 1.2E1 | 1.6E-2 | 1.6E-2 | 4.8E1 | 5.3E1 | 91 | 83 | 91 | 83 | 0.56 |
| Ch | uIU/mL | 1.0E0 | 1.0E0 | 3.7E1 | 3.1E1 | 2.0E2 | 1.4E2 | 3.4E-3 | 3.4E-3 | 1.8E3 | 1.2E3 | 91 | 83 | 91 | 83 | 0.49 |
| Co | pg/mL | 4.6E1 | 5.3E1 | 1.4E2 | 3.2E2 | 4.5E2 | 1.8E3 | 1.5E-1 | 1.5E-1 | 3.7E3 | 1.7E4 | 91 | 83 | 91 | 83 | 0.54 |
| Cp | ng/mL | 2.1E1 | 2.2E1 | 2.6E1 | 4.6E1 | 2.0E1 | 1.4E2 | 6.0E-1 | 2.5E0 | 1.3E2 | 1.3E3 | 91 | 83 | 91 | 83 | 0.58 |
| Cq | ng/mL | 2.2E-2 | 3.4E-2 | 7.6E-2 | 7.6E-1 | 2.3E-1 | 5.4E0 | 8.0E-4 | 8.0E-4 | 2.0E0 | 4.9E1 | 91 | 83 | 91 | 83 | 0.58 |
| Cs | ng/mL | 3.8E1 | 1.3E2 | 2.0E2 | 8.1E2 | 3.9E2 | 2.4E3 | 1.0E0 | 8.3E-1 | 1.9E3 | 1.8E4 | 91 | 83 | 91 | 83 | 0.64 |
| Ct | ng/mL | 6.0E-1 | 2.3E-1 | 3.4E1 | 5.0E1 | 1.1E2 | 1.3E2 | 1.3E-2 | 1.1E-4 | 4.7E2 | 6.2E2 | 91 | 83 | 91 | 83 | 0.46 |
| Cu | ng/mL | 2.2E-1 | 3.2E-1 | 4.4E-1 | 1.7E0 | 9.6E-1 | 7.5E0 | 1.9E-2 | 1.7E-2 | 9.0E0 | 6.6E1 | 91 | 83 | 91 | 83 | 0.61 |
| Cv | ng/mL | 4.1E0 | 8.5E0 | 2.6E1 | 3.3E1 | 7.4E1 | 6.9E1 | 2.0E-2 | 2.4E-2 | 5.3E2 | 4.7E2 | 91 | 83 | 91 | 83 | 0.56 |
| Cw | mIU/mL | 2.8E-2 | 4.3E-2 | 4.1E-2 | 1.3E-1 | 3.3E-2 | 7.4E-1 | 8.9E-4 | 1.5E-1 | 6.0E-1 | 6.0E0 | 91 | 83 | 91 | 83 | 0.54 |
| Cx | ng/mL | 9.5E-1 | 6.5E-1 | 5.3E1 | 4.7E1 | 1.0E2 | 9.6E1 | 9.3E-5 | 9.3E-5 | 3.9E2 | 3.9E2 | 91 | 83 | 91 | 83 | 0.50 |
| Db | ug/mL | 7.5E0 | 7.3E0 | 9.0E0 | 8.5E0 | 7.1E0 | 8.1E0 | 4.5E-1 | 8.1E-1 | 4.3E1 | 5.9E1 | 91 | 83 | 91 | 83 | 0.47 |
| Dc | nmol/L | 1.9E-2 | 2.4E-2 | 4.1E-2 | 2.9E-1 | 6.9E-2 | 1.6E0 | 5.2E-6 | 1.1E-3 | 4.8E-1 | 1.4E1 | 91 | 83 | 91 | 83 | 0.59 |
| Dd | ug/mL | 6.2E-2 | 1.2E-1 | 1.5E-1 | 2.7E-1 | 2.5E-1 | 4.7E-1 | 4.8E-4 | 1.3E-3 | 1.6E0 | 3.6E0 | 91 | 83 | 91 | 83 | 0.59 |
| De | ng/mL | 3.4E-3 | 3.4E-3 | 6.4E-2 | 1.1E-1 | 1.4E-1 | 1.8E-1 | 3.4E-3 | 3.4E-3 | 9.2E-1 | 1.1E0 | 91 | 83 | 91 | 83 | 0.58 |
| Dg | ng/mL | 3.1E1 | 3.9E1 | 4.4E1 | 5.3E1 | 3.9E1 | 4.2E1 | 1.0E0 | 7.1E-1 | 1.8E2 | 1.9E2 | 91 | 83 | 91 | 83 | 0.57 |
| Di | pg/mL | 1.8E0 | 2.7E0 | 2.2E0 | 2.8E0 | 2.4E0 | 2.0E0 | 1.8E-1 | 1.8E-1 | 1.3E1 | 9.3E0 | 91 | 83 | 91 | 83 | 0.60 |
| Dk | uIU/mL | 1.2E-2 | 1.7E-2 | 6.1E-2 | 6.3E-2 | 2.0E-1 | 1.5E-1 | 1.1E-4 | 1.1E-4 | 1.6E0 | 9.8E-1 | 91 | 83 | 91 | 83 | 0.56 |
| Dl | ng/mL | 1.8E2 | 2.3E2 | 2.6E2 | 3.5E2 | 2.3E2 | 3.3E2 | 8.9E0 | 4.4E0 | 1.1E3 | 1.6E3 | 91 | 83 | 91 | 83 | 0.56 |
| Dp | ng/ml | 2.4E0 | 1.8E0 | 5.3E0 | 5.5E0 | 7.3E0 | 1.0E1 | 1.5E-2 | 3.7E-3 | 3.5E1 | 5.6E1 | 65 | 70 | 65 | 70 | 0.44 |
| Dr | pg/ml | 2.1E1 | 3.0E1 | 4.4E1 | 3.9E2 | 5.8E1 | 1.8E3 | 7.5E-1 | 7.5E-1 | 2.5E2 | 1.0E4 | 39 | 33 | 39 | 33 | 0.54 |
| Du | pg/ml | 7.9E1 | 2.2E2 | 5.7E2 | 2.0E3 | 1.1E3 | 5.5E3 | 1.2E0 | 1.2E0 | 5.4E3 | 2.4E4 | 28 | 29 | 28 | 29 | 0.58 |
| Dw | ng/ml | 9.2E-3 | 2.0E-2 | 4.4E-2 | 5.2E-2 | 6.5E-2 | 6.9E-2 | 9.2E-3 | 9.2E-3 | 1.9E-1 | 1.9E-1 | 8 | 10 | 8 | 10 | 0.56 |
| Ef | ng/ml | 8.7E-2 | 1.2E-1 | 7.9E-1 | 9.9E-1 | 1.7E0 | 2.3E0 | 1.6E-3 | 5.7E-4 | 1.0E1 | 9.9E0 | 72 | 75 | 72 | 75 | 0.52 |
| Wm | % | 8.5E-2 | 8.5E-2 | 4.1E0 | 4.1E1 | 2.2E1 | 1.8E2 | 5.4E-2 | 8.5E-2 | 2.0E2 | 1.0E3 | 83 | 76 | 83 | 76 | 0.52 |
| Ed | pg/ml | 5.2E-1 | 1.5E1 | 2.3E1 | 5.0E1 | 3.6E1 | 9.0E1 | 5.2E-1 | 5.2E-1 | 1.9E2 | 5.0E2 | 65 | 70 | 65 | 70 | 0.58 |
| Eo | ng/ml | 6.1E0 | 3.0E0 | 6.6E0 | 7.3E0 | 5.6E0 | 1.2E1 | 3.6E-1 | 3.6E-1 | 1.6E1 | 4.0E1 | 8 | 10 | 8 | 10 | 0.44 |
| Yf | ng/mL | 1.6E1 | 1.5E1 | 4.2E1 | 6.5E1 | 5.8E1 | 1.3E2 | 2.9E-1 | 2.9E-1 | 2.4E2 | 5.9E2 | 31 | 28 | 31 | 28 | 0.46 |
| Tj | pg/mL | 3.7E-1 | 3.7E-1 | 2.6E1 | 5.1E1 | 1.1E2 | 2.7E2 | 3.7E-1 | 3.7E-1 | 8.7E2 | 2.3E3 | 73 | 72 | 73 | 72 | 0.52 |
| Po | pg/ml | 5.7E-2 | 1.9E0 | 8.2E0 | 1.4E1 | 2.8E1 | 3.5E1 | 8.0E-3 | 2.6E-2 | 2.7E2 | 2.2E2 | 217 | 137 | 217 | 137 | 0.60 |
| Ti | ug/mL | 2.9E0 | 5.3E0 | 4.1E0 | 5.8E0 | 3.8E0 | 4.6E0 | 1.2E-1 | 4.0E-1 | 1.6E1 | 1.8E1 | 43 | 41 | 43 | 41 | 0.61 |
| Em | ng/ml | 2.9E-3 | 2.2E-2 | 4.4E-2 | 1.0E-1 | 8.7E-2 | 3.0E-1 | 8.4E-4 | 8.4E-4 | 5.0E-1 | 1.9E0 | 48 | 44 | 48 | 44 | 0.56 |
| Et | ng/ml | 1.1E3 | 2.1E3 | 1.4E3 | 2.2E3 | 1.1E3 | 1.2E3 | 7.5E1 | 7.9E1 | 4.8E3 | 5.0E3 | 216 | 137 | 216 | 137 | 0.70 |
| Eq | pg/ml | 2.4E2 | 1.4E2 | 3.5E2 | 3.4E2 | 4.0E2 | 4.0E2 | 1.0E0 | 1.0E0 | 1.5E3 | 1.4E3 | 28 | 29 | 28 | 29 | 0.47 |
| Ew | U/ml | 1.9E0 | 2.1E0 | 2.7E0 | 2.4E0 | 2.6E0 | 1.2E0 | 1.1E0 | 1.3E0 | 8.8E0 | 5.0E0 | 8 | 10 | 8 | 10 | 0.59 |
| Th | ug/mL | 1.2E0 | 1.3E0 | 1.6E0 | 1.9E0 | 1.3E0 | 1.8E0 | 1.3E-1 | 2.6E-3 | 5.4E0 | 7.5E0 | 43 | 41 | 43 | 41 | 0.52 |
| Fa | ng/ml | 4.0E1 | 5.7E1 | 5.2E1 | 1.8E2 | 5.3E1 | 5.3E2 | 2.6E-1 | 6.0E-1 | 2.5E2 | 3.7E3 | 63 | 68 | 63 | 68 | 0.60 |

Figure 31

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ez | ng/ml | 3.4E0 | 4.1E0 | 1.7E1 | 1.4E1 | 3.2E1 | 2.9E1 | 1.3E-2 | 1.3E-2 | 1.6E2 | 2.0E2 | 65 | 70 | 65 | 70 | 0.53 |
| Fb | ng/ml | 2.3E1 | 2.7E1 | 2.1E1 | 2.5E1 | 1.2E1 | 1.1E1 | 9.4E-1 | 6.6E-1 | 4.3E1 | 4.3E1 | 63 | 69 | 63 | 69 | 0.60 |
| Ex | ng/ml | 4.5E-2 | 1.1E-1 | 1.7E-1 | 2.8E-1 | 3.6E-1 | 6.1E-1 | 3.5E-5 | 1.7E-4 | 2.2E0 | 4.1E0 | 50 | 55 | 50 | 55 | 0.64 |
| Fc | pg/ml | 2.2E-1 | 2.2E-1 | 1.9E1 | 2.8E1 | 8.3E1 | 9.1E1 | 2.2E-1 | 2.2E-1 | 4.5E2 | 3.9E2 | 29 | 29 | 29 | 29 | 0.56 |
| Fd | pg/ml | 8.0E1 | 1.6E2 | 4.0E2 | 2.3E3 | 7.9E2 | 6.2E3 | 4.5E-1 | 9.8E-1 | 2.9E3 | 2.5E4 | 29 | 29 | 29 | 29 | 0.55 |
| Fi | pg/ml | 2.5E-1 | 2.5E-1 | 7.4E1 | 1.1E2 | 2.1E2 | 3.5E2 | 2.5E-1 | 2.5E-1 | 8.5E2 | 1.8E3 | 29 | 29 | 29 | 29 | 0.54 |
| Fn | ng/ml | 2.1E-1 | 2.1E-1 | 4.2E0 | 3.6E0 | 8.3E0 | 5.8E0 | 1.1E-14 | 1.1E-14 | 3.7E1 | 2.7E1 | 65 | 70 | 65 | 70 | 0.53 |
| Fp | ng/ml | 9.3E0 | 2.0E1 | 1.9E1 | 3.1E1 | 2.3E1 | 3.2E1 | 6.0E-3 | 2.8E-1 | 1.1E2 | 1.3E2 | 217 | 139 | 217 | 139 | 0.62 |
| Fr | ng/ml | 2.8E4 | 6.2E4 | 1.1E5 | 1.7E5 | 1.8E5 | 2.3E5 | 1.9E2 | 1.3E3 | 8.4E5 | 8.4E5 | 222 | 141 | 222 | 141 | 0.63 |
| Fw | pg/ml | 8.5E-1 | 5.1E0 | 5.2E1 | 4.2E1 | 3.5E2 | 1.2E2 | 1.2E-1 | 1.2E-1 | 3.0E3 | 9.1E2 | 74 | 75 | 74 | 75 | 0.60 |
| Fy | ng/ml | 2.9E1 | 4.9E1 | 4.7E1 | 9.5E1 | 4.9E1 | 1.3E2 | 1.2E-1 | 1.2E-1 | 2.2E2 | 6.5E2 | 65 | 67 | 65 | 67 | 0.60 |
| Gh | pg/ml | 5.8E-1 | 3.9E0 | 3.0E1 | 1.3E1 | 7.1E1 | 2.8E1 | 2.9E-2 | 2.9E-2 | 3.2E2 | 1.4E2 | 29 | 29 | 29 | 29 | 0.54 |
| Gb | % | 4.1E1 | 4.2E1 | 4.7E1 | 5.8E1 | 4.4E1 | 6.2E1 | 3.7E0 | 2.2E0 | 2.3E2 | 3.0E2 | 29 | 29 | 29 | 29 | 0.55 |
| Gc | pg/ml | 7.1E1 | 1.3E2 | 1.2E2 | 2.3E2 | 1.4E2 | 2.6E2 | 6.4E0 | 6.9E0 | 7.3E2 | 1.2E3 | 39 | 33 | 39 | 33 | 0.64 |
| Gd | ng/ml | 3.1E1 | 3.4E1 | 3.3E1 | 3.4E1 | 1.8E1 | 1.9E1 | 6.3E0 | 3.0E0 | 8.1E1 | 8.0E1 | 46 | 36 | 46 | 36 | 0.51 |
| Gn | U/ml | 2.1E-1 | 2.2E-1 | 1.6E0 | 4.0E0 | 5.0E0 | 2.0E1 | 5.6E-3 | 5.6E-3 | 3.0E1 | 1.1E2 | 38 | 33 | 38 | 33 | 0.51 |
| Gl | pg/ml | 8.5E3 | 1.1E4 | 1.1E4 | 1.4E4 | 9.0E3 | 1.0E4 | 9.1E1 | 4.0E2 | 3.2E4 | 3.2E4 | 74 | 75 | 74 | 75 | 0.58 |
| Gp | U/ml | 1.5E0 | 9.9E-1 | 2.8E0 | 2.0E0 | 3.7E0 | 3.1E0 | 1.5E-2 | 1.5E-2 | 2.0E1 | 1.8E1 | 74 | 74 | 74 | 74 | 0.43 |
| Gz | ug/ml | 1.0E0 | 9.9E-1 | 6.5E0 | 4.5E0 | 6.0E0 | 5.4E0 | 6.2E-2 | 4.2E-2 | 2.5E1 | 1.9E1 | 42 | 52 | 42 | 52 | 0.41 |
| Ha | ng/ml | 1.9E0 | 2.5E0 | 5.4E0 | 1.2E1 | 1.4E1 | 2.4E1 | 1.7E-2 | 1.7E-2 | 1.0E2 | 1.0E2 | 63 | 70 | 63 | 70 | 0.57 |
| Nm | pg/ml | 1.1E4 | 1.7E4 | 2.5E4 | 5.8E4 | 5.8E4 | 1.3E5 | 1.0E-9 | 1.0E-9 | 7.8E5 | 9.6E5 | 218 | 139 | 218 | 139 | 0.61 |
| Nn | pg/ml | 1.3E2 | 2.8E2 | 1.2E3 | 5.7E3 | 5.1E3 | 3.0E4 | 1.0E-9 | 1.0E-9 | 6.0E4 | 3.1E5 | 218 | 139 | 218 | 139 | 0.61 |
| No | pg/ml | 1.2E1 | 2.1E1 | 2.8E1 | 6.0E1 | 5.9E1 | 1.3E2 | 1.0E-9 | 1.0E-9 | 5.6E2 | 9.1E2 | 218 | 139 | 218 | 139 | 0.63 |
| Nq | pg/ml | 1.7E0 | 3.0E0 | 1.9E1 | 3.1E1 | 6.6E1 | 1.0E2 | 1.0E-9 | 1.0E-9 | 6.2E2 | 6.7E2 | 218 | 139 | 218 | 139 | 0.55 |
| Nr | pg/ml | 9.7E-1 | 3.2E0 | 2.1E1 | 3.8E1 | 8.4E1 | 1.4E2 | 1.0E-9 | 1.0E-9 | 9.8E2 | 1.4E3 | 218 | 139 | 218 | 139 | 0.60 |
| Ns | pg/ml | 1.0E-9 | 1.0E-9 | 4.7E0 | 1.2E1 | 2.3E1 | 9.7E1 | 1.0E-9 | 1.0E-9 | 1.7E2 | 1.1E3 | 218 | 139 | 218 | 139 | 0.50 |
| Nt | pg/ml | 8.3E1 | 1.4E2 | 1.1E2 | 1.9E2 | 9.0E1 | 2.0E2 | 9.8E-1 | 1.5E1 | 5.9E2 | 1.7E3 | 218 | 139 | 218 | 139 | 0.69 |
| Nu | pg/ml | 8.2E0 | 4.6E1 | 4.2E1 | 8.1E1 | 7.9E1 | 1.1E2 | 1.0E-9 | 1.0E-9 | 4.2E2 | 6.3E2 | 218 | 139 | 218 | 139 | 0.66 |
| Lu | pg/ml | 1.0E4 | 1.0E4 | 1.6E4 | 1.5E4 | 3.3E4 | 4.8E4 | 7.7E2 | 5.2E2 | 3.9E5 | 5.6E5 | 218 | 139 | 218 | 139 | 0.47 |
| Lv | pg/ml | 1.0E-9 | 1.4E0 | 1.2E1 | 2.3E1 | 2.5E1 | 4.1E1 | 1.0E-9 | 1.0E-9 | 2.4E2 | 2.6E2 | 218 | 139 | 218 | 139 | 0.59 |
| Lw | pg/ml | 1.0E-9 | 1.0E-9 | 1.6E-1 | 2.8E0 | 2.2E0 | 1.7E1 | 1.0E-9 | 1.0E-9 | 3.2E1 | 1.8E2 | 218 | 139 | 218 | 139 | 0.53 |
| Lx | pg/ml | 1.0E-9 | 5.5E1 | 1.3E2 | 4.7E2 | 5.0E2 | 2.0E3 | 1.0E-9 | 1.0E-9 | 6.2E3 | 2.2E4 | 218 | 139 | 218 | 139 | 0.65 |
| Ly | pg/ml | 1.0E-9 | 1.0E-9 | 8.4E0 | 1.0E1 | 1.8E1 | 1.8E1 | 1.0E-9 | 1.0E-9 | 1.1E2 | 9.6E1 | 218 | 139 | 218 | 139 | 0.53 |
| Lz | pg/ml | 1.0E-9 | 1.0E-9 | 3.4E0 | 3.6E0 | 3.0E1 | 1.6E1 | 1.0E-9 | 1.0E-9 | 4.3E2 | 1.3E2 | 218 | 139 | 218 | 139 | 0.52 |
| Ma | pg/ml | 3.5E2 | 7.0E2 | 2.0E3 | 3.2E3 | 5.9E3 | 6.9E3 | 1.0E-9 | 1.0E-9 | 6.5E4 | 5.2E4 | 218 | 139 | 218 | 139 | 0.60 |
| Mb | pg/ml | 2.4E1 | 2.8E1 | 3.0E1 | 3.5E1 | 1.4E1 | 2.2E1 | 9.2E0 | 4.1E0 | 7.2E1 | 2.1E2 | 218 | 139 | 218 | 139 | 0.57 |
| Mc | pg/ml | 1.0E-9 | 1.0E-9 | 2.0E-2 | 1.1E-1 | 2.7E-1 | 1.1E0 | 1.0E-9 | 1.0E-9 | 4.0E0 | 1.3E1 | 218 | 139 | 218 | 139 | 0.50 |
| Md | pg/ml | 1.0E-9 | 1.0E-9 | 7.0E-1 | 6.1E-1 | 6.4E0 | 3.2E0 | 1.0E-9 | 1.0E-9 | 6.8E1 | 2.9E1 | 218 | 139 | 218 | 139 | 0.52 |
| Me | pg/ml | 3.2E1 | 3.1E1 | 3.1E1 | 3.2E1 | 1.6E1 | 3.4E1 | 1.0E-9 | 1.0E-9 | 1.2E2 | 3.2E2 | 218 | 139 | 218 | 139 | 0.48 |
| Mf | pg/ml | 1.0E-9 | 1.0E-9 | 3.6E-1 | 1.1E0 | 1.7E0 | 5.8E0 | 1.0E-9 | 1.0E-9 | 2.0E1 | 5.6E1 | 218 | 139 | 218 | 139 | 0.53 |
| Mg | pg/ml | 8.5E-1 | 1.6E0 | 5.9E0 | 8.7E0 | 1.1E1 | 1.9E1 | 1.0E-9 | 1.0E-9 | 8.8E1 | 1.5E2 | 218 | 139 | 218 | 139 | 0.54 |
| Mh | pg/ml | 1.0E-9 | 1.0E-9 | 1.3E0 | 1.0E0 | 9.0E0 | 4.2E0 | 1.0E-9 | 1.0E-9 | 1.1E2 | 4.2E1 | 218 | 139 | 218 | 139 | 0.55 |
| Mi | pg/ml | 1.0E-9 | 1.0E-9 | 8.9E-1 | 8.4E0 | 8.7E0 | 5.3E1 | 1.0E-9 | 1.0E-9 | 1.2E2 | 5.2E2 | 218 | 139 | 218 | 139 | 0.53 |
| Mj | pg/ml | 1.0E-9 | 1.0E-9 | 6.3E0 | 8.5E0 | 3.7E1 | 2.8E1 | 1.0E-9 | 1.0E-9 | 4.6E2 | 2.1E2 | 218 | 139 | 218 | 139 | 0.54 |
| Mk | pg/ml | 2.3E0 | 9.1E-1 | 1.4E1 | 2.0E1 | 7.2E1 | 1.2E2 | 1.0E-9 | 1.0E-9 | 1.0E3 | 1.3E3 | 218 | 139 | 218 | 139 | 0.48 |
| Ml | pg/ml | 1.0E-9 | 1.0E-9 | 1.2E1 | 1.0E1 | 1.4E2 | 5.4E1 | 1.0E-9 | 1.0E-9 | 2.1E3 | 5.1E2 | 218 | 139 | 218 | 139 | 0.51 |
| Mm | pg/ml | 4.1E2 | 7.9E2 | 8.8E2 | 1.5E3 | 1.2E3 | 1.8E3 | 1.0E-9 | 1.0E-9 | 1.0E4 | 1.0E4 | 218 | 139 | 218 | 139 | 0.61 |
| Mn | pg/ml | 4.8E0 | 8.4E0 | 1.1E1 | 1.2E1 | 3.0E1 | 1.1E1 | 1.0E-9 | 1.0E-9 | 3.5E2 | 6.8E1 | 218 | 139 | 218 | 139 | 0.66 |
| Mp | pg/ml | 1.0E-9 | 8.6E0 | 4.1E1 | 2.2E1 | 2.1E2 | 1.0E-9 | 1.0E-9 | 1.8E2 | 2.4E3 | 218 | 139 | 218 | 139 | 0.56 |
| Mq | pg/ml | 1.0E-9 | 1.0E-9 | 1.8E0 | 4.3E0 | 1.3E1 | 1.6E1 | 1.0E-9 | 1.0E-9 | 1.8E2 | 1.0E2 | 218 | 139 | 218 | 139 | 0.53 |
| Mr | pg/ml | 1.0E-9 | 1.0E-9 | 1.7E1 | 8.4E1 | 1.0E2 | 3.9E2 | 1.0E-9 | 1.0E-9 | 1.4E3 | 3.4E3 | 218 | 139 | 218 | 139 | 0.58 |
| Ms | pg/ml | 3.4E2 | 3.2E2 | 5.0E2 | 4.4E2 | 5.7E2 | 5.8E2 | 1.0E-9 | 1.0E-9 | 3.2E3 | 4.7E3 | 218 | 139 | 218 | 139 | 0.46 |
| Mt | pg/ml | 1.0E-9 | 9.5E-1 | 7.8E0 | 3.8E1 | 5.1E1 | 2.8E2 | 1.0E-9 | 1.0E-9 | 7.1E2 | 3.2E3 | 218 | 139 | 218 | 139 | 0.62 |
| Mu | pg/ml | 1.0E-9 | 1.0E-9 | 9.2E-1 | 2.9E0 | 7.6E0 | 2.1E1 | 1.0E-9 | 1.0E-9 | 9.9E1 | 2.3E2 | 218 | 139 | 218 | 139 | 0.54 |
| Mv | pg/ml | 1.0E-9 | 1.0E-9 | 7.1E1 | 7.0E1 | 4.1E2 | 1.9E2 | 1.0E-9 | 1.0E-9 | 4.5E3 | 9.2E2 | 218 | 139 | 218 | 139 | 0.54 |
| Mw | pg/ml | 2.8E1 | 5.6E1 | 3.1E2 | 2.9E2 | 1.7E3 | 7.9E2 | 1.0E-9 | 1.0E-9 | 1.8E4 | 5.3E3 | 218 | 139 | 218 | 139 | 0.56 |
| Mx | pg/ml | 1.0E-9 | 1.0E-9 | 1.7E-1 | 8.4E-1 | 8.3E-1 | 3.3E0 | 1.0E-9 | 1.0E-9 | 9.2E0 | 3.2E1 | 218 | 139 | 218 | 139 | 0.59 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| My | pg/ml | 1.0E-9 | 1.0E-9 | 4.3E2 | 1.7E2 | 3.0E3 | 7.4E2 | 1.0E-9 | 1.0E-9 | 3.9E4 | 8.0E3 | 218 | 139 | 218 | 139 | 0.50 |
| Mz | pg/ml | 8.6E0 | 1.9E1 | 2.1E1 | 6.2E1 | 4.8E1 | 2.0E2 | 1.0E-9 | 1.0E-9 | 5.5E2 | 1.9E3 | 218 | 139 | 218 | 139 | 0.66 |
| Na | pg/ml | 1.0E-9 | 1.0E-9 | 7.5E-1 | 8.3E-1 | 2.1E0 | 3.9E0 | 1.0E-9 | 1.0E-9 | 7.8E0 | 4.2E1 | 218 | 139 | 218 | 139 | 0.51 |
| Nb | pg/ml | 1.9E0 | 2.4E0 | 3.9E0 | 6.0E0 | 1.2E1 | 2.0E1 | 1.0E-9 | 1.0E-9 | 1.5E2 | 2.1E2 | 218 | 139 | 218 | 139 | 0.56 |
| Nc | pg/ml | 4.1E2 | 1.8E2 | 5.9E2 | 3.8E2 | 8.4E2 | 4.9E2 | 1.0E-9 | 1.0E-9 | 9.2E3 | 3.2E3 | 218 | 139 | 218 | 139 | 0.41 |
| Nd | pg/ml | 3.1E1 | 1.4E1 | 2.6E2 | 4.6E1 | 1.7E1 | 2.1E2 | 1.0E-9 | 1.0E-9 | 7.8E1 | 2.1E3 | 218 | 139 | 218 | 139 | 0.43 |
| Ne | pg/ml | 4.7E2 | 3.4E2 | 5.9E2 | 4.1E2 | 6.2E2 | 4.3E2 | 1.0E-9 | 1.0E-9 | 7.0E3 | 3.6E3 | 218 | 139 | 218 | 139 | 0.39 |
| Nf | pg/ml | 1.0E-9 | 1.0E-9 | 3.0E0 | 3.0E0 | 1.0E1 | 1.6E1 | 1.0E-9 | 1.0E-9 | 8.2E1 | 1.3E2 | 218 | 139 | 218 | 139 | 0.45 |
| Ng | pg/ml | 1.0E1 | 1.7E1 | 8.9E1 | 9.2E1 | 1.9E2 | 1.6E2 | 1.0E-9 | 1.0E-9 | 1.6E3 | 8.9E2 | 218 | 139 | 218 | 139 | 0.54 |
| Nh | pg/ml | 6.8E1 | 5.0E1 | 9.0E1 | 6.3E1 | 8.1E1 | 6.3E1 | 1.0E-9 | 3.1E0 | 5.6E2 | 5.1E2 | 218 | 139 | 218 | 139 | 0.38 |
| Ni | pg/ml | 2.2E0 | 1.0E-9 | 7.4E1 | 1.0E2 | 1.2E2 | 1.6E2 | 1.0E-9 | 1.0E-9 | 6.3E2 | 1.1E3 | 218 | 139 | 218 | 139 | 0.52 |
| Nj | pg/ml | 1.0E1 | 4.4E0 | 1.3E1 | 7.7E0 | 1.2E1 | 9.2E0 | 1.0E-9 | 1.0E-9 | 6.9E1 | 5.8E1 | 218 | 139 | 218 | 139 | 0.35 |
| Nk | pg/ml | 2.1E1 | 1.4E1 | 3.4E1 | 3.0E1 | 3.8E1 | 4.0E1 | 1.0E-9 | 1.0E-9 | 2.0E2 | 2.0E2 | 218 | 139 | 218 | 139 | 0.46 |
| Nl | pg/ml | 4.8E1 | 3.2E1 | 6.6E1 | 4.0E1 | 8.9E1 | 4.0E1 | 1.0E-9 | 1.0E-9 | 1.1E3 | 2.3E2 | 218 | 139 | 218 | 139 | 0.38 |
| Hl | pg/ml | 4.6E0 | 8.6E0 | 3.7E1 | 1.5E2 | 6.5E1 | 6.7E2 | 1.0E-9 | 1.0E-9 | 3.0E2 | 3.6E3 | 29 | 29 | 29 | 29 | 0.47 |
| Ho | pg/ml | 1.5E1 | 1.9E1 | 2.1E1 | 4.4E1 | 2.2E1 | 7.6E1 | 1.0E-9 | 6.7E0 | 8.3E1 | 3.9E2 | 29 | 29 | 29 | 29 | 0.65 |
| Hp | ng/ml | 1.6E0 | 1.6E0 | 1.3E2 | 1.3E2 | 3.1E2 | 3.1E2 | 3.6E-1 | 1.0E-9 | 8.9E2 | 8.9E2 | 29 | 29 | 29 | 29 | 0.50 |
| Tz | pg/ml | 3.3E3 | 7.2E3 | 5.3E3 | 4.5E3 | 7.6E3 | 2.5E5 | 7.4E1 | 1.0E-9 | 5.3E4 | 2.1E6 | 65 | 70 | 65 | 70 | 0.65 |
| Ua | pg/ml | 3.1E3 | 3.7E3 | 4.6E4 | 1.5E4 | 2.6E5 | 2.9E4 | 2.3E2 | 1.0E-9 | 2.1E6 | 1.3E5 | 65 | 70 | 65 | 70 | 0.51 |
| Ub | pg/ml | 7.2E2 | 4.1E2 | 1.1E3 | 6.2E2 | 1.4E3 | 7.6E2 | 1.6E1 | 1.0E-9 | 9.8E3 | 4.4E3 | 65 | 70 | 65 | 70 | 0.35 |
| Ue | pg/ml | 3.2E1 | 2.4E1 | 3.7E1 | 3.6E1 | 2.3E1 | 4.0E1 | 5.3E0 | 9.8E-2 | 1.0E2 | 2.7E2 | 65 | 70 | 65 | 70 | 0.43 |
| Uc | pg/ml | 6.9E2 | 7.8E2 | 1.1E3 | 2.4E3 | 1.1E3 | 7.0E3 | 2.2E1 | 1.0E-9 | 5.5E3 | 5.7E4 | 65 | 70 | 65 | 70 | 0.54 |
| Ud | pg/ml | 1.0E-9 | 1.0E-9 | 6.0E0 | 7.6E-1 | 4.8E1 | 6.4E0 | 1.0E-9 | 1.0E-9 | 3.9E2 | 5.3E1 | 65 | 70 | 65 | 70 | 0.50 |
| Hq | pg/ml | 1.1E0 | 1.3E0 | 1.0E2 | 2.4E2 | 1.4E3 | 2.4E3 | 1.0E-9 | 1.0E-9 | 2.0E4 | 2.8E4 | 218 | 137 | 218 | 137 | 0.53 |
| Hr | pg/ml | 1.0E2 | 8.0E1 | 7.3E2 | 5.2E2 | 1.4E3 | 1.2E3 | 1.0E-9 | 1.0E-9 | 1.2E4 | 8.9E3 | 218 | 137 | 218 | 137 | 0.45 |
| Hu | pg/ml | 1.0E-9 | 2.0E1 | 5.7E3 | 2.5E3 | 4.6E4 | 2.2E4 | 1.0E-9 | 1.0E-9 | 6.3E5 | 2.6E5 | 218 | 137 | 218 | 137 | 0.55 |
| Hv | pg/ml | 1.4E0 | 1.6E0 | 2.6E0 | 1.0E1 | 6.7E0 | 7.7E1 | 1.0E-9 | 1.0E-9 | 6.9E1 | 8.9E2 | 218 | 137 | 218 | 137 | 0.54 |
| Hw | pg/ml | 6.6E0 | 5.7E0 | 1.7E1 | 8.5E1 | 5.5E1 | 8.0E2 | 1.0E-9 | 1.0E-9 | 6.4E2 | 9.4E3 | 218 | 137 | 218 | 137 | 0.47 |
| Hx | pg/ml | 8.2E0 | 1.2E1 | 6.6E1 | 4.4E1 | 6.3E2 | 1.4E2 | 1.0E-9 | 1.0E-9 | 9.3E3 | 1.3E3 | 218 | 137 | 218 | 137 | 0.57 |
| Ib | ng/ml | 5.6E-2 | 2.5E-2 | 9.9E-1 | 1.8E0 | 4.2E0 | 8.1E0 | 1.0E-9 | 1.0E-9 | 3.0E1 | 5.6E1 | 65 | 68 | 65 | 68 | 0.45 |
| Ic | U/ml | 2.2E2 | 2.2E2 | 2.8E2 | 1.4E3 | 5.6E2 | 8.0E3 | 2.4E0 | 6.6E0 | 4.1E3 | 6.5E4 | 65 | 68 | 65 | 68 | 0.56 |
| Id | U/ml | 5.5E-1 | 8.2E-1 | 9.1E-1 | 8.1E0 | 1.2E0 | 5.2E1 | 1.0E-9 | 1.0E-9 | 6.9E0 | 4.3E2 | 65 | 68 | 65 | 68 | 0.61 |
| Tt | pg/ml | 1.6E2 | 1.7E2 | 1.7E2 | 1.8E2 | 5.0E1 | 6.4E1 | 4.3E1 | 7.3E1 | 3.0E2 | 4.4E2 | 60 | 64 | 60 | 64 | 0.55 |
| To | pg/ml | 1.8E0 | 1.5E0 | 2.3E0 | 2.0E0 | 3.3E0 | 2.5E0 | 1.0E-9 | 1.0E-9 | 2.3E1 | 1.2E1 | 63 | 68 | 63 | 68 | 0.46 |
| Tr | pg/ml | 3.5E0 | 3.3E0 | 5.5E0 | 1.2E1 | 6.8E0 | 3.9E1 | 1.0E-9 | 1.0E-9 | 3.8E1 | 3.1E2 | 62 | 66 | 62 | 66 | 0.54 |
| Tn | pg/ml | 2.2E1 | 4.3E1 | 9.7E1 | 1.7E2 | 2.8E2 | 4.3E2 | 1.0E-9 | 2.4E0 | 1.7E3 | 2.3E3 | 63 | 68 | 63 | 68 | 0.62 |
| Tv | ng/ml | 1.2E1 | 1.2E1 | 1.7E1 | 1.4E2 | 1.9E1 | 8.6E2 | 1.0E-9 | 1.0E-9 | 1.1E2 | 7.1E3 | 63 | 68 | 63 | 68 | 0.52 |
| Ih | ng/ml | 4.8E1 | 1.1E2 | 2.0E2 | 3.6E2 | 3.7E2 | 5.8E2 | 1.0E-9 | 1.0E-9 | 2.5E3 | 3.6E3 | 218 | 138 | 218 | 138 | 0.61 |
| Ii | ng/ml | 6.2E1 | 1.2E2 | 2.2E2 | 2.4E2 | 5.6E2 | 5.3E2 | 1.6E0 | 7.3E-1 | 5.2E3 | 4.5E3 | 218 | 138 | 218 | 138 | 0.59 |
| Ij | ng/ml | 7.1E1 | 1.1E2 | 1.9E2 | 3.6E2 | 6.9E2 | 2.1E3 | 2.8E0 | 9.5E0 | 6.4E3 | 2.4E4 | 217 | 135 | 217 | 135 | 0.64 |
| Ik | ng/ml | 7.7E0 | 1.7E1 | 1.9E3 | 2.5E2 | 1.4E4 | 4.7E2 | 5.9E-1 | 6.2E-1 | 1.2E5 | 2.1E3 | 216 | 136 | 216 | 136 | 0.60 |
| Il | ng/ml | 3.6E2 | 4.1E2 | 1.4E3 | 1.4E3 | 3.0E3 | 2.8E3 | 1.0E-9 | 1.0E-9 | 1.2E4 | 1.2E4 | 215 | 135 | 215 | 135 | 0.53 |
| Im | ng/ml | 1.8E2 | 2.9E2 | 3.1E2 | 8.2E2 | 3.7E2 | 1.7E3 | 1.4E1 | 2.2E1 | 3.1E3 | 1.5E4 | 216 | 136 | 216 | 136 | 0.66 |
| In | ng/ml | 3.8E0 | 2.7E0 | 2.4E1 | 5.0E1 | 1.1E2 | 3.9E2 | 1.0E-9 | 1.0E-9 | 1.1E3 | 4.5E3 | 218 | 138 | 218 | 138 | 0.48 |
| Hb | ng/ml | 2.0E1 | 3.2E1 | 2.8E1 | 4.2E1 | 2.8E1 | 4.2E1 | 1.6E0 | 4.8E-1 | 1.4E2 | 2.0E2 | 64 | 72 | 64 | 72 | 0.61 |
| Hc | pg/ml | 7.0E2 | 6.4E2 | 4.1E3 | 2.3E3 | 1.4E4 | 6.5E3 | 1.0E-9 | 1.0E-9 | 1.0E5 | 5.0E4 | 64 | 72 | 64 | 72 | 0.48 |
| Hf | ng/ml | 1.5E2 | 2.3E2 | 3.9E2 | 4.0E2 | 5.5E2 | 5.4E2 | 1.0E-9 | 1.0E-9 | 2.5E3 | 3.2E3 | 64 | 72 | 64 | 72 | 0.55 |
| Io | ng/ml | 6.7E3 | 1.4E4 | 1.8E4 | 2.2E4 | 5.4E4 | 2.8E4 | 1.2E2 | 1.0E-9 | 7.1E5 | 2.0E5 | 217 | 139 | 217 | 139 | 0.62 |
| Ip | ng/ml | 7.9E0 | 2.7E1 | 1.8E1 | 2.7E1 | 2.5E1 | 2.7E1 | 1.0E-9 | 1.0E-9 | 2.3E2 | 1.6E2 | 217 | 139 | 217 | 139 | 0.60 |
| Iq | ug/ml | 9.8E-2 | 1.4E-1 | 6.3E1 | 2.8E0 | 9.2E2 | 1.9E1 | 1.0E-9 | 1.0E-9 | 1.4E4 | 2.2E2 | 217 | 139 | 217 | 139 | 0.54 |
| Ir | ug/ml | 3.2E-1 | 7.6E-1 | 4.7E0 | 8.8E0 | 3.8E1 | 3.8E1 | 1.0E-9 | 1.0E-9 | 5.1E2 | 3.7E2 | 216 | 139 | 216 | 139 | 0.65 |
| Is | ng/ml | 1.5E0 | 3.9E0 | 7.6E0 | 1.6E1 | 3.9E1 | 3.4E1 | 1.0E-9 | 1.0E-9 | 5.5E2 | 2.6E2 | 217 | 139 | 217 | 139 | 0.64 |
| It | ng/ml | 1.4E0 | 2.9E0 | 2.3E1 | 2.5E1 | 1.1E2 | 1.0E2 | 1.0E-9 | 1.0E-9 | 1.1E3 | 8.3E2 | 217 | 139 | 217 | 139 | 0.61 |
| Iu | ng/ml | 1.6E2 | 1.8E2 | 1.3E3 | 1.6E3 | 4.2E3 | 4.7E3 | 1.0E-9 | 1.0E-9 | 2.9E4 | 2.4E4 | 217 | 139 | 217 | 139 | 0.53 |
| Iv | ng/ml | 8.1E0 | 2.2E1 | 1.0E2 | 1.4E2 | 1.1E3 | 5.6E2 | 1.0E-9 | 1.0E-9 | 1.6E4 | 3.8E3 | 217 | 138 | 217 | 138 | 0.66 |
| Iz | ng/ml | 1.2E2 | 1.3E2 | 4.7E2 | 2.8E2 | 9.7E2 | 3.6E2 | 1.5E0 | 8.8E-1 | 6.1E3 | 1.7E3 | 64 | 72 | 64 | 72 | 0.51 |
| Yg | pg/ml | 2.5E2 | 2.7E2 | 5.3E2 | 2.8E3 | 7.8E2 | 9.4E3 | 8.9E0 | 1.0E-9 | 3.4E3 | 5.0E4 | 26 | 28 | 26 | 28 | 0.56 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yh | pg/ml | 2.1E2 | 2.3E2 | 3.5E2 | 5.4E2 | 4.2E2 | 7.2E2 | 1.0E-9 | 1.0E-9 | 1.8E3 | 3.0E3 | 26 | 28 | 26 | 28 | 0.54 |
| Yi | pg/ml | 2.3E2 | 4.8E2 | 4.6E2 | 1.9E3 | 5.0E2 | 5.1E3 | 1.0E-9 | 1.0E-9 | 2.0E3 | 2.6E4 | 26 | 28 | 26 | 28 | 0.59 |
| Yk | U/ml | 1.0E-9 | 1.0E-9 | 1.5E-1 | 2.9E-1 | 4.5E-1 | 7.3E-1 | 1.0E-9 | 1.0E-9 | 1.8E0 | 3.0E0 | 26 | 28 | 26 | 28 | 0.52 |
| Yj | pg/ml | 2.0E2 | 1.1E2 | 3.9E2 | 2.0E2 | 6.4E2 | 2.9E2 | 9.7E0 | 1.0E-9 | 3.2E3 | 1.5E3 | 26 | 28 | 26 | 28 | 0.37 |
| Yd | ng/ml | 1.8E-1 | 2.8E-1 | 3.8E-1 | 4.2E-1 | 4.9E-1 | 5.4E-1 | 6.6E-3 | 1.6E-2 | 1.8E0 | 2.3E0 | 29 | 29 | 29 | 29 | 0.54 |
| Wb | pg/ml | 2.6E4 | 3.5E4 | 2.9E4 | 6.2E4 | 1.7E4 | 1.1E5 | 4.9E3 | 7.5E3 | 8.4E4 | 6.4E5 | 29 | 29 | 29 | 29 | 0.66 |
| Vz | pg/ml | 3.8E0 | 2.9E0 | 4.8E0 | 4.6E0 | 3.9E0 | 5.3E0 | 1.0E-9 | 7.6E-2 | 1.6E1 | 2.2E1 | 29 | 29 | 29 | 29 | 0.45 |
| Si | ng/ml | 1.2E0 | 1.2E0 | 2.3E0 | 1.7E0 | 3.1E0 | 1.6E0 | 1.1E-1 | 8.6E-3 | 1.0E1 | 6.0E0 | 29 | 29 | 29 | 29 | 0.52 |
| Sf | mIU/mL | 1.5E1 | 1.9E1 | 7.2E1 | 2.0E1 | 1.4E2 | 1.9E1 | 6.2E-1 | 1.3E0 | 7.2E2 | 8.3E1 | 29 | 29 | 29 | 29 | 0.43 |
| Sh | mIU/mL | 1.2E1 | 1.3E1 | 5.7E1 | 2.4E1 | 1.2E2 | 3.4E1 | 1.8E-1 | 7.8E-2 | 5.7E2 | 1.8E2 | 29 | 29 | 29 | 29 | 0.49 |
| Sj | ng/ml | 3.8E-1 | 4.4E-1 | 4.0E-1 | 4.5E-1 | 8.7E-2 | 9.7E-2 | 2.5E-1 | 3.2E-1 | 5.7E-1 | 7.2E-1 | 29 | 29 | 29 | 29 | 0.65 |
| Rc | pg/ml | 6.6E3 | 6.9E3 | 7.6E3 | 7.8E3 | 5.4E3 | 6.3E3 | 3.9E2 | 5.5E2 | 2.8E4 | 3.9E4 | 65 | 70 | 65 | 70 | 0.50 |
| Rb | pg/ml | 7.6E-1 | 7.0E-1 | 2.8E0 | 3.2E0 | 4.1E0 | 7.5E0 | 1.0E-9 | 1.0E-9 | 1.6E1 | 5.6E1 | 65 | 70 | 65 | 70 | 0.51 |
| Zq | 2.6ng/ml | 1.7E2 | 3.4E2 | 2.7E2 | 3.4E2 | 2.3E2 | 2.0E2 | 1.4E1 | 1.7E1 | 9.7E2 | 9.7E2 | 28 | 28 | 28 | 28 | 0.62 |
| Zw | 2.5ng/ml | 4.8E0 | 5.3E0 | 9.6E0 | 1.1E1 | 1.2E1 | 1.6E1 | 1.4E-1 | 2.4E-1 | 5.9E1 | 6.3E1 | 29 | 29 | 29 | 29 | 0.47 |
| Zx | 2.3mU/ml | 8.1E-2 | 1.4E-1 | 1.9E-1 | 3.9E-1 | 2.0E-1 | 6.8E-1 | 4.2E-2 | 3.2E-2 | 8.4E-1 | 2.9E0 | 29 | 29 | 29 | 29 | 0.61 |
| Pz | ng/ml | 3.0E3 | 5.7E3 | 5.1E3 | 6.5E3 | 5.1E3 | 7.0E3 | 1.6E1 | 4.0E1 | 2.9E4 | 7.0E4 | 216 | 136 | 216 | 136 | 0.59 |
| Qa | ng/ml | 2.9E3 | 6.2E3 | 5.7E3 | 1.1E4 | 7.2E3 | 2.0E4 | 1.5E2 | 2.9E2 | 4.2E4 | 2.2E5 | 216 | 136 | 216 | 136 | 0.65 |
| Qb | ng/ml | 9.1E1 | 1.5E2 | 2.1E2 | 2.9E2 | 4.5E2 | 4.2E2 | 7.9E-1 | 6.7E0 | 5.3E3 | 4.1E3 | 216 | 136 | 216 | 136 | 0.62 |
| Qc | ng/ml | 1.6E2 | 3.6E2 | 3.9E2 | 5.6E2 | 5.7E2 | 6.3E2 | 1.0E-9 | 1.0E-9 | 3.8E3 | 4.3E3 | 216 | 136 | 216 | 136 | 0.61 |
| Qd | ng/ml | 7.1E3 | 1.4E4 | 2.2E4 | 3.6E4 | 1.4E5 | 5.9E4 | 1.5E2 | 1.2E3 | 2.0E6 | 4.3E5 | 216 | 136 | 216 | 136 | 0.68 |
| Qe | ng/ml | 6.4E2 | 1.7E3 | 1.9E3 | 2.5E3 | 6.9E3 | 2.7E3 | 1.0E-9 | 8.8E0 | 9.7E4 | 1.8E4 | 216 | 136 | 216 | 136 | 0.67 |
| Jd | ng/ml | 4.1E-1 | 1.2E0 | 5.4E0 | 2.8E0 | 2.0E1 | 4.1E0 | 1.0E-9 | 1.0E-9 | 1.2E2 | 2.3E1 | 65 | 70 | 65 | 70 | 0.61 |
| Je | ng/ml | 1.0E-9 | 1.0E-9 | 2.0E0 | 1.6E0 | 6.5E0 | 2.5E0 | 1.0E-9 | 1.0E-9 | 4.6E1 | 1.1E1 | 65 | 70 | 65 | 70 | 0.55 |
| Jf | ng/ml | 1.0E-9 | 1.0E-9 | 9.6E-1 | 1.4E0 | 2.2E0 | 2.3E0 | 1.0E-9 | 1.0E-9 | 1.2E1 | 9.1E0 | 65 | 70 | 65 | 70 | 0.54 |
| Jg | ng/ml | 3.3E2 | 7.8E2 | 6.6E2 | 1.1E3 | 9.6E2 | 1.0E3 | 5.8E0 | 1.3E1 | 1.0E4 | 7.1E3 | 218 | 137 | 218 | 137 | 0.66 |
| Jh | ng/ml | 2.0E0 | 4.9E0 | 2.3E1 | 2.4E1 | 9.9E1 | 6.0E1 | 1.0E-9 | 1.0E-9 | 1.2E3 | 4.9E2 | 218 | 137 | 218 | 137 | 0.61 |
| Ji | ng/ml | 4.5E1 | 8.5E1 | 6.5E1 | 1.5E2 | 7.1E1 | 1.7E2 | 1.1E0 | 8.9E0 | 5.3E2 | 1.3E3 | 218 | 137 | 218 | 137 | 0.71 |
| Sr | pg/mL | 3.0E2 | 5.7E2 | 6.3E2 | 1.5E3 | 9.2E2 | 2.8E3 | 1.0E-9 | 1.0E-9 | 4.3E3 | 2.1E4 | 65 | 69 | 65 | 69 | 0.64 |
| Ss | pg/mL | 7.9E4 | 9.2E4 | 1.4E5 | 1.5E5 | 1.7E5 | 1.9E5 | 9.1E3 | 2.7E3 | 7.1E5 | 1.3E6 | 65 | 69 | 65 | 69 | 0.51 |
| St | pg/mL | 1.9E7 | 4.2E7 | 4.0E7 | 1.0E8 | 6.1E7 | 2.4E8 | 7.8E5 | 1.0E-9 | 4.1E8 | 1.7E9 | 63 | 70 | 63 | 70 | 0.64 |
| Wc | ng/ml | 1.0E-9 | 4.1E-3 | 5.9E-2 | 1.3E-1 | 1.2E-1 | 3.4E-1 | 1.0E-9 | 1.0E-9 | 5.2E-1 | 1.8E0 | 29 | 29 | 29 | 29 | 0.56 |
| Wd | ng/ml | 9.3E0 | 9.7E0 | 2.2E1 | 5.6E1 | 4.7E1 | 1.1E2 | 1.0E0 | 1.5E0 | 2.4E2 | 4.1E2 | 29 | 29 | 29 | 29 | 0.56 |
| We | ng/ml | 2.5E-1 | 4.9E-1 | 9.5E-1 | 1.8E0 | 1.4E0 | 4.5E0 | 1.0E-9 | 1.0E-9 | 5.5E0 | 2.3E1 | 29 | 29 | 29 | 29 | 0.57 |
| Wg | ng/ml | 1.0E-9 | 1.0E-9 | 5.6E-4 | 1.8E-2 | 3.0E-3 | 9.9E-2 | 1.0E-9 | 1.0E-9 | 1.6E-2 | 5.3E-1 | 29 | 29 | 29 | 29 | 0.50 |
| Wh | ng/ml | 9.7E-3 | 1.1E-2 | 3.8E-2 | 5.5E-2 | 8.5E-2 | 1.1E-1 | 1.0E-9 | 1.0E-9 | 3.6E-1 | 4.2E-1 | 29 | 29 | 29 | 29 | 0.56 |
| Wf | ng/ml | 1.0E-9 | 1.0E-9 | 6.5E-2 | 1.9E-1 | 1.4E-1 | 4.8E-1 | 1.0E-9 | 1.0E-9 | 4.8E-1 | 2.3E0 | 29 | 29 | 29 | 29 | 0.56 |
| Ra | pg/ml | 1.0E-9 | 1.0E-9 | 5.4E-1 | 1.2E0 | 1.1E0 | 7.7E0 | 1.0E-9 | 1.0E-9 | 3.8E0 | 6.4E1 | 65 | 70 | 65 | 70 | 0.44 |
| Qz | pg/ml | 1.1E1 | 9.0E0 | 6.4E1 | 3.9E1 | 1.0E2 | 6.6E1 | 1.0E-9 | 1.0E-9 | 4.5E2 | 2.8E2 | 65 | 70 | 65 | 70 | 0.44 |
| Qy | pg/ml | 3.8E-1 | 4.6E-1 | 5.3E0 | 1.9E1 | 2.9E1 | 1.0E2 | 1.0E-9 | 1.0E-9 | 2.3E2 | 7.3E2 | 65 | 70 | 65 | 70 | 0.53 |
| Qx | pg/ml | 1.0E-9 | 1.0E-9 | 4.3E0 | 3.2E0 | 2.4E1 | 1.4E1 | 1.0E-9 | 1.0E-9 | 1.9E2 | 1.1E2 | 65 | 70 | 65 | 70 | 0.52 |
| Qw | pg/ml | 3.1E-1 | 1.0E-9 | 2.0E0 | 3.5E0 | 5.3E0 | 1.2E1 | 1.0E-9 | 1.0E-9 | 3.0E1 | 6.6E1 | 65 | 70 | 65 | 70 | 0.44 |
| Qv | pg/ml | 2.2E4 | 1.2E4 | 3.3E4 | 3.9E4 | 4.7E4 | 1.2E5 | 1.4E3 | 1.0E-9 | 3.7E5 | 9.4E5 | 65 | 70 | 65 | 70 | 0.39 |
| Qu | pg/ml | 6.2E0 | 8.0E0 | 9.5E1 | 8.9E1 | 1.9E2 | 1.8E2 | 1.0E-9 | 1.0E-9 | 7.1E2 | 9.8E2 | 65 | 70 | 65 | 70 | 0.50 |
| Qt | pg/ml | 1.1E1 | 1.6E1 | 5.0E1 | 4.0E1 | 1.2E2 | 6.9E1 | 1.0E-9 | 1.0E-9 | 7.1E2 | 3.3E2 | 65 | 70 | 65 | 70 | 0.54 |
| Qh | ng/ml | 1.7E1 | 2.3E1 | 3.2E1 | 6.7E1 | 4.5E1 | 1.2E2 | 2.5E-1 | 4.3E-1 | 2.4E2 | 8.0E2 | 65 | 70 | 65 | 70 | 0.60 |
| Qg | ng/ml | 8.6E0 | 6.5E0 | 1.7E1 | 1.0E1 | 3.5E1 | 1.2E1 | 1.5E-1 | 3.0E-1 | 2.7E2 | 8.1E1 | 65 | 70 | 65 | 70 | 0.43 |
| Jj | ng/ml | 5.6E2 | 4.0E2 | 2.6E3 | 7.3E2 | 2.3E4 | 1.2E3 | 2.3E0 | 8.7E0 | 3.4E5 | 1.1E4 | 218 | 137 | 218 | 137 | 0.42 |
| Jk | ng/ml | 2.6E0 | 2.9E0 | 1.9E1 | 2.7E1 | 4.5E1 | 5.6E1 | 1.0E-9 | 4.3E-2 | 2.8E2 | 3.9E2 | 218 | 137 | 218 | 137 | 0.55 |
| Jl | ng/ml | 3.9E-1 | 6.4E-1 | 1.5E0 | 7.6E1 | 3.4E0 | 8.5E2 | 1.2E-3 | 5.4E-3 | 2.0E1 | 9.9E3 | 218 | 137 | 218 | 137 | 0.61 |
| Jm | ng/ml | 1.6E1 | 2.8E1 | 6.1E1 | 7.7E1 | 1.5E2 | 1.9E2 | 1.0E-9 | 1.0E-9 | 1.4E3 | 2.1E3 | 218 | 137 | 218 | 137 | 0.58 |
| Jn | pg/ml | 2.3E-1 | 5.5E-1 | 4.1E0 | 1.4E1 | 4.2E1 | 8.4E1 | 1.0E-9 | 1.0E-9 | 6.2E2 | 7.3E2 | 218 | 137 | 218 | 137 | 0.64 |
| Jo | pg/ml | 3.4E3 | 4.6E3 | 4.5E3 | 6.3E3 | 3.8E3 | 9.7E3 | 2.0E1 | 2.4E1 | 2.4E4 | 1.0E5 | 218 | 137 | 218 | 137 | 0.56 |
| Jp | pg/ml | 6.5E4 | 8.4E4 | 6.7E4 | 8.8E4 | 3.7E4 | 4.1E4 | 5.8E2 | 4.6E3 | 1.9E5 | 3.8E5 | 218 | 137 | 218 | 137 | 0.67 |
| Jq | pg/ml | 8.6E1 | 1.4E2 | 1.5E2 | 3.0E2 | 2.0E2 | 8.2E2 | 1.0E0 | 5.6E0 | 2.0E3 | 8.7E3 | 218 | 137 | 218 | 137 | 0.60 |
| Jr | pg/ml | 2.6E0 | 8.3E0 | 7.2E1 | 1.3E2 | 7.3E2 | 7.9E2 | 1.0E-9 | 1.0E-9 | 1.0E4 | 7.4E3 | 218 | 137 | 218 | 137 | 0.62 |
| Js | pg/ml | 1.2E1 | 1.8E1 | 7.8E1 | 1.1E2 | 6.9E2 | 4.4E2 | 1.0E-9 | 1.9E1 | 1.0E4 | 3.0E3 | 218 | 137 | 218 | 137 | 0.64 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jt | pg/ml | 2.1E3 | 3.1E3 | 2.6E3 | 4.4E3 | 2.1E3 | 6.2E3 | 2.2E1 | 1.5E2 | 2.2E4 | 5.2E4 | 218 | 137 | 218 | 137 | 0.63 |
| Xa | pg/ml | 1.0E-9 | 5.2E0 | 5.8E0 | 7.5E1 | 1.0E1 | 2.4E2 | 1.0E-9 | 1.0E-9 | 4.1E1 | 1.2E3 | 29 | 29 | 29 | 29 | 0.66 |
| Ye | pg/ml | 1.0E-9 | 1.0E-9 | 4.8E0 | 3.4E0 | 1.5E1 | 1.1E1 | 1.0E-9 | 1.0E-9 | 6.9E1 | 6.1E1 | 29 | 29 | 29 | 29 | 0.47 |
| Tm | pg/ml | 1.0E-9 | 1.0E-9 | 2.8E0 | 2.3E0 | 5.0E0 | 3.8E0 | 1.0E-9 | 1.0E-9 | 1.8E1 | 8.4E0 | 29 | 29 | 29 | 29 | 0.49 |
| Tl | pg/ml | 1.1E-1 | 1.3E-1 | 2.3E-1 | 1.2E0 | 3.6E-1 | 4.5E0 | 1.0E-9 | 1.0E-9 | 1.2E0 | 2.5E1 | 29 | 29 | 29 | 29 | 0.63 |
| Ju | mIU/ml | 7.5E0 | 1.2E1 | 2.8E1 | 2.0E1 | 4.3E1 | 2.3E1 | 2.5E-1 | 1.7E-1 | 2.3E2 | 1.1E2 | 65 | 70 | 65 | 70 | 0.54 |
| Jv | mIU/ml | 1.4E1 | 1.6E1 | 4.7E1 | 3.1E1 | 8.0E1 | 3.8E1 | 2.4E-2 | 1.7E-2 | 4.4E2 | 1.8E2 | 65 | 70 | 65 | 70 | 0.53 |
| Jy | ng/ml | 1.8E-3 | 1.6E-3 | 2.0E-3 | 3.3E-3 | 1.0E-3 | 6.9E-3 | 1.0E-9 | 1.7E-4 | 4.7E-3 | 4.1E-2 | 65 | 70 | 65 | 70 | 0.48 |
| Kc | pg/ml | 2.0E1 | 2.6E1 | 3.3E1 | 5.6E1 | 3.9E1 | 6.6E1 | 1.0E-9 | 1.0E-9 | 1.7E2 | 3.2E2 | 64 | 72 | 64 | 72 | 0.62 |
| Kd | pg/ml | 1.0E-9 | 1.0E-9 | 1.4E2 | 9.0E2 | 6.3E2 | 4.6E3 | 1.0E-9 | 1.0E-9 | 4.8E3 | 3.8E4 | 64 | 72 | 64 | 72 | 0.52 |
| Ke | pg/ml | 1.1E4 | 1.4E4 | 1.3E4 | 2.4E4 | 8.8E3 | 4.0E4 | 1.0E3 | 6.7E2 | 4.6E4 | 3.2E5 | 64 | 72 | 64 | 72 | 0.62 |
| Kf | pg/mL | 4.9E0 | 8.1E0 | 5.4E0 | 9.5E0 | 4.4E0 | 1.1E1 | 1.0E-9 | 1.0E-9 | 1.8E1 | 7.8E1 | 64 | 72 | 64 | 72 | 0.65 |
| Kg | pg/mL | 8.5E2 | 1.1E3 | 1.8E3 | 2.5E3 | 3.0E3 | 5.4E3 | 7.7E1 | 1.3E2 | 2.2E4 | 3.6E4 | 64 | 72 | 64 | 72 | 0.55 |
| Ki | pg/ml | 6.2E1 | 6.2E1 | 6.9E1 | 7.3E1 | 5.3E1 | 5.3E1 | 1.0E-9 | 1.0E-9 | 2.9E2 | 2.5E2 | 64 | 72 | 64 | 72 | 0.53 |
| Kj | pg/ml | 7.9E2 | 8.5E2 | 1.3E3 | 1.5E3 | 1.5E3 | 2.1E3 | 6.6E1 | 3.3E1 | 8.8E3 | 1.5E4 | 64 | 72 | 64 | 72 | 0.51 |
| Kk | pg/ml | 6.8E0 | 8.7E0 | 1.1E1 | 1.7E1 | 1.4E1 | 1.7E1 | 1.0E-9 | 1.0E-9 | 8.1E1 | 6.1E1 | 64 | 72 | 64 | 72 | 0.61 |
| Kl | pg/ml | 1.8E4 | 1.8E4 | 2.6E4 | 2.8E4 | 2.4E4 | 2.7E4 | 4.1E2 | 2.3E2 | 1.1E5 | 1.3E5 | 64 | 72 | 64 | 72 | 0.53 |
| Kn | pg/ml | 1.5E1 | 5.2E1 | 4.4E1 | 1.6E2 | 6.3E1 | 5.8E2 | 1.0E-9 | 1.0E-9 | 3.4E2 | 4.9E3 | 64 | 72 | 64 | 72 | 0.60 |
| Ko | pg/ml | 3.0E2 | 4.4E2 | 3.8E2 | 6.4E2 | 4.1E2 | 7.5E2 | 1.0E-9 | 1.0E-9 | 1.8E3 | 4.1E3 | 64 | 72 | 64 | 72 | 0.63 |
| Kp | pg/ml | 2.9E2 | 4.1E2 | 3.0E2 | 6.0E2 | 2.3E2 | 1.5E3 | 1.0E-9 | 1.0E-9 | 8.6E2 | 1.3E4 | 64 | 72 | 64 | 72 | 0.63 |
| Kq | pg/ml | 2.8E2 | 3.9E2 | 3.5E2 | 3.0E3 | 3.6E2 | 1.9E4 | 5.1E0 | 1.6E0 | 2.1E3 | 1.6E5 | 61 | 70 | 61 | 70 | 0.65 |
| Kr | pg/ml | 1.0E-9 | 7.3E-1 | 1.4E0 | 8.5E0 | 2.6E0 | 5.0E1 | 1.0E-9 | 1.0E-9 | 1.2E1 | 4.2E2 | 61 | 70 | 61 | 70 | 0.58 |
| Ks | pg/ml | 1.3E4 | 1.8E4 | 1.9E4 | 2.2E4 | 1.7E4 | 1.9E4 | 4.5E2 | 5.1E1 | 7.9E4 | 6.3E4 | 61 | 70 | 61 | 70 | 0.54 |
| Ps | ng/ml | 1.3E2 | 2.9E2 | 5.0E2 | 1.2E3 | 1.7E3 | 2.6E3 | 1.6E0 | 5.5E0 | 9.0E3 | 1.2E4 | 29 | 29 | 29 | 29 | 0.66 |
| Kx | ng/ml | 1.0E-9 | 3.8E-3 | 4.2E-3 | 1.2E-2 | 8.6E-3 | 2.0E-2 | 1.0E-9 | 1.0E-9 | 5.1E-2 | 1.0E-1 | 63 | 72 | 63 | 72 | 0.60 |
| Ky | ng/ml | 8.7E-2 | 2.2E-1 | 3.3E-1 | 4.8E-1 | 7.4E-1 | 7.9E-1 | 1.0E-9 | 1.0E-9 | 5.1E0 | 4.4E0 | 63 | 72 | 63 | 72 | 0.62 |
| Kz | ng/ml | 1.0E-9 | 1.0E-9 | 4.3E-3 | 3.6E-3 | 6.2E-3 | 6.2E-3 | 1.0E-9 | 1.0E-9 | 1.6E-2 | 2.5E-2 | 63 | 72 | 63 | 72 | 0.46 |
| Rz | ng/ml | 3.6E-1 | 3.3E-1 | 9.5E-1 | 8.9E-1 | 1.5E0 | 1.5E0 | 1.1E-2 | 4.6E-3 | 6.7E0 | 7.5E0 | 29 | 29 | 29 | 29 | 0.53 |
| Ry | ng/ml | 1.6E-2 | 2.3E-2 | 1.9E-2 | 4.1E-2 | 1.4E-2 | 6.8E-2 | 1.0E-9 | 1.0E-9 | 5.0E-2 | 3.5E-1 | 29 | 29 | 29 | 29 | 0.56 |
| Rx | ng/ml | 1.0E-9 | 1.0E-9 | 1.3E-3 | 1.7E-3 | 2.1E-3 | 2.6E-3 | 1.0E-9 | 1.0E-9 | 8.6E-3 | 8.6E-3 | 29 | 29 | 29 | 29 | 0.54 |
| Ld | pg/ml | 1.0E-9 | 1.0E-9 | 2.9E0 | 4.8E0 | 9.2E0 | 8.4E0 | 1.0E-9 | 1.0E-9 | 6.9E1 | 5.0E1 | 64 | 72 | 64 | 72 | 0.59 |
| Lh | pg/ml | 9.3E3 | 1.9E4 | 1.8E4 | 3.7E4 | 2.6E4 | 6.6E4 | 1.0E-9 | 1.0E-9 | 2.6E5 | 4.8E5 | 218 | 138 | 218 | 138 | 0.65 |
| Li | pg/ml | 2.6E3 | 6.6E3 | 1.6E4 | 3.1E4 | 9.1E4 | 9.5E4 | 1.2E1 | 1.3E1 | 1.3E6 | 9.2E5 | 218 | 138 | 218 | 138 | 0.64 |
| Lj | pg/ml | 2.1E3 | 4.9E3 | 1.7E4 | 2.8E4 | 5.6E4 | 6.1E4 | 1.0E-9 | 1.0E-9 | 4.3E5 | 4.1E5 | 218 | 138 | 218 | 138 | 0.60 |
| Lp | pg/ml | 1.1E1 | 9.5E0 | 8.0E1 | 1.4E2 | 2.1E2 | 3.5E2 | 1.0E-9 | 1.0E-9 | 1.1E3 | 1.4E3 | 29 | 29 | 29 | 29 | 0.51 |
| Lt | pg/ml | 1.0E-9 | 1.0E-9 | 1.4E0 | 1.6E0 | 5.3E0 | 5.9E0 | 1.0E-9 | 1.0E-9 | 2.5E1 | 2.5E1 | 29 | 29 | 29 | 29 | 0.50 |
| Rv | ng/ml | 5.0E-4 | 5.0E-4 | 1.1E-3 | 1.9E-3 | 1.8E-3 | 3.8E-3 | 1.0E-9 | 1.0E-9 | 9.2E-3 | 1.6E-2 | 29 | 29 | 29 | 29 | 0.54 |
| Ru | ng/ml | 1.0E-9 | 1.0E-9 | 1.8E-2 | 2.6E-2 | 6.8E-2 | 8.9E-2 | 1.0E-9 | 1.0E-9 | 3.1E-1 | 3.5E-1 | 29 | 29 | 29 | 29 | 0.52 |
| Rt | ng/ml | 7.2E-2 | 7.5E-2 | 1.0E-1 | 3.9E-1 | 9.9E-2 | 1.4E0 | 6.5E-3 | 1.3E-3 | 3.8E-1 | 7.4E0 | 29 | 29 | 29 | 29 | 0.52 |
| Yl | pg/ml | 1.4E1 | 1.2E1 | 1.7E1 | 2.5E1 | 1.3E1 | 4.2E1 | 1.0E-9 | 1.0E-9 | 4.7E1 | 2.2E2 | 29 | 29 | 29 | 29 | 0.48 |
| Rm | ng/ml | 1.8E1 | 1.9E1 | 4.0E1 | 5.9E1 | 6.6E1 | 1.0E2 | 2.2E-1 | 2.3E-1 | 3.4E2 | 6.5E2 | 65 | 69 | 65 | 69 | 0.54 |
| Rh | ng/ml | 1.8E2 | 1.7E2 | 6.2E2 | 5.1E2 | 2.1E3 | 2.1E3 | 7.5E0 | 2.5E1 | 1.7E4 | 1.7E4 | 65 | 69 | 65 | 69 | 0.46 |
| Ri | ng/ml | 4.1E-1 | 1.0E-9 | 4.6E0 | 3.0E0 | 9.1E0 | 6.8E0 | 1.0E-9 | 1.0E-9 | 4.9E1 | 4.5E1 | 65 | 69 | 65 | 69 | 0.44 |
| Rg | ng/ml | 1.0E-9 | 1.0E-9 | 8.1E-3 | 1.5E-1 | 3.6E-2 | 5.8E-1 | 1.0E-9 | 1.0E-9 | 2.7E-1 | 3.3E0 | 65 | 69 | 65 | 69 | 0.54 |
| Rj | ng/ml | 1.0E-9 | 1.0E-9 | 9.3E-1 | 4.7E0 | 1.9E0 | 3.2E1 | 1.0E-9 | 1.0E-9 | 1.1E1 | 2.7E2 | 65 | 69 | 65 | 69 | 0.48 |
| Rf | ng/ml | 4.1E-1 | 3.5E-1 | 8.3E-1 | 1.2E0 | 1.1E0 | 2.8E0 | 2.1E-2 | 2.1E-2 | 6.2E0 | 1.7E1 | 65 | 69 | 65 | 69 | 0.49 |
| Ql | pg/ml | 1.7E0 | 5.5E0 | 8.5E0 | 1.6E1 | 1.4E1 | 2.9E1 | 1.0E-9 | 1.0E-9 | 7.5E1 | 1.8E2 | 65 | 70 | 65 | 70 | 0.57 |
| Qm | pg/ml | 1.0E-9 | 9.4E0 | 1.7E1 | 2.4E1 | 3.5E1 | 3.5E1 | 1.0E-9 | 1.0E-9 | 1.9E2 | 1.8E2 | 65 | 70 | 65 | 70 | 0.59 |
| Qn | pg/ml | 6.1E-1 | 6.1E-1 | 6.3E0 | 7.6E0 | 2.7E1 | 2.6E1 | 1.0E-9 | 1.0E-9 | 2.2E2 | 2.0E2 | 65 | 70 | 65 | 70 | 0.51 |
| Nv | pg/ml | 3.1E3 | 5.9E3 | 7.3E3 | 1.5E4 | 1.5E4 | 2.6E4 | 1.0E-9 | 1.9E1 | 1.3E5 | 1.6E5 | 218 | 139 | 218 | 139 | 0.64 |
| Nw | pg/ml | 7.7E3 | 1.3E4 | 1.1E4 | 2.0E4 | 1.7E4 | 2.7E4 | 2.0E2 | 1.9E2 | 2.1E5 | 2.2E5 | 218 | 139 | 218 | 139 | 0.68 |
| Nx | pg/ml | 1.6E2 | 2.4E2 | 3.5E2 | 6.0E2 | 5.7E2 | 7.1E2 | 1.0E-9 | 1.0E-9 | 3.5E3 | 4.1E3 | 218 | 139 | 218 | 139 | 0.63 |
| Ny | pg/ml | 4.9E0 | 1.2E1 | 1.3E2 | 6.7E1 | 1.7E3 | 2.7E2 | 1.0E-9 | 1.0E-9 | 2.5E4 | 2.8E3 | 218 | 139 | 218 | 139 | 0.65 |
| Oa | pg/ml | 1.3E2 | 2.5E2 | 2.8E2 | 6.7E2 | 4.8E2 | 9.1E2 | 1.0E-9 | 1.0E-9 | 3.0E3 | 4.5E3 | 65 | 70 | 65 | 70 | 0.63 |
| Op | pg/ml | 4.3E5 | 4.4E5 | 4.4E5 | 4.4E5 | 1.4E5 | 1.9E5 | 2.1E5 | 5.2E5 | 7.3E5 | 7.5E5 | 29 | 29 | 29 | 29 | 0.51 |
| Wn | ng/ml | 9.4E0 | 1.1E1 | 1.2E2 | 1.8E1 | 3.8E2 | 1.7E1 | 1.2E0 | 7.6E-1 | 1.8E3 | 5.6E1 | 23 | 17 | 23 | 17 | 0.49 |
| Tk | ng/ml | 1.1E2 | 1.3E2 | 3.3E2 | 3.3E2 | 8.4E2 | 5.8E2 | 3.0E0 | 4.0E0 | 4.2E3 | 2.3E3 | 24 | 20 | 24 | 20 | 0.55 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oe | pg/ml | 4.7E1 | 9.6E0 | 2.4E2 | 2.5E2 | 3.6E2 | 4.1E2 | 1.0E-9 | 1.0E-9 | 2.2E3 | 2.3E3 | 217 | 138 | 217 | 138 | 0.49 |
| Of | pg/ml | 1.5E2 | 1.3E2 | 4.6E3 | 5.7E3 | 2.0E4 | 2.1E4 | 1.0E-9 | 1.0E-9 | 1.9E5 | 1.7E5 | 218 | 139 | 218 | 139 | 0.49 |
| Og | pg/ml | 7.3E-2 | 6.2E-2 | 4.8E-1 | 1.4E-1 | 1.9E0 | 3.0E-1 | 1.0E-9 | 1.0E-9 | 1.9E1 | 2.5E0 | 218 | 139 | 218 | 139 | 0.43 |
| Oh | pg/ml | 2.2E0 | 4.5E0 | 1.6E1 | 1.4E2 | 1.1E2 | 1.3E3 | 1.0E-9 | 1.0E-9 | 1.4E3 | 1.6E4 | 218 | 139 | 218 | 139 | 0.61 |
| Oi | pg/ml | 1.3E0 | 2.6E0 | 4.6E0 | 5.6E0 | 8.1E0 | 7.4E0 | 1.0E-9 | 1.0E-9 | 6.7E1 | 4.2E1 | 218 | 139 | 218 | 139 | 0.56 |
| Ok | pg/ml | 3.2E2 | 5.8E2 | 4.2E2 | 8.7E2 | 4.1E2 | 1.1E3 | 2.9E1 | 1.5E1 | 2.8E3 | 7.8E3 | 218 | 139 | 218 | 139 | 0.70 |
| Om | pg/ml | 3.7E2 | 5.4E2 | 8.1E2 | 1.3E3 | 2.5E3 | 4.4E3 | 1.0E-9 | 1.0E-9 | 3.0E4 | 5.1E4 | 218 | 139 | 218 | 139 | 0.62 |
| On | pg/ml | 1.4E2 | 2.7E2 | 2.4E2 | 5.1E2 | 4.3E2 | 8.7E2 | 1.0E-9 | 1.0E1 | 4.5E3 | 8.5E3 | 218 | 139 | 218 | 139 | 0.68 |
| Or | pg/ml | 9.6E0 | 1.9E1 | 1.8E1 | 6.3E1 | 2.3E1 | 1.1E2 | 1.0E-9 | 1.0E-9 | 9.6E1 | 5.1E2 | 64 | 73 | 64 | 73 | 0.60 |
| Ow | pg/ml | 2.8E1 | 5.2E1 | 1.3E2 | 3.1E2 | 3.7E2 | 1.0E3 | 1.0E-9 | 1.0E-9 | 2.7E3 | 8.1E3 | 64 | 73 | 64 | 73 | 0.59 |
| Ou | pg/ml | 4.1E2 | 5.8E2 | 8.4E2 | 1.6E3 | 1.4E3 | 2.4E3 | 2.2E1 | 1.0E-9 | 9.8E3 | 1.1E4 | 64 | 73 | 64 | 73 | 0.59 |
| Ul | ng/ml | 1.0E-9 | 1.0E-9 | 1.4E0 | 1.5E0 | 5.4E0 | 7.4E0 | 1.0E-9 | 1.0E-9 | 2.9E1 | 5.6E1 | 66 | 70 | 66 | 70 | 0.49 |
| Uo | ng/ml | 1.0E-9 | 1.0E-9 | 1.0E-1 | 4.8E-2 | 2.6E-1 | 1.4E-1 | 1.0E-9 | 1.0E-9 | 1.3E0 | 6.9E-1 | 66 | 70 | 66 | 70 | 0.45 |
| Uk | ng/ml | 1.0E-9 | 1.0E-9 | 2.9E-3 | 8.9E-3 | 5.8E-3 | 4.2E-2 | 1.0E-9 | 1.0E-9 | 2.6E-2 | 3.2E-1 | 66 | 70 | 66 | 70 | 0.43 |
| Um | ng/ml | 1.0E-9 | 1.0E-9 | 2.9E-1 | 1.7E-1 | 7.1E-1 | 4.9E-1 | 1.0E-9 | 1.0E-9 | 3.6E0 | 2.3E0 | 66 | 70 | 66 | 70 | 0.42 |
| Uf | ng/ml | 5.1E-2 | 8.0E-2 | 1.0E-1 | 2.5E-1 | 1.4E-1 | 6.3E-1 | 2.7E-3 | 1.0E-3 | 7.0E-1 | 5.1E0 | 66 | 70 | 66 | 70 | 0.62 |
| Uh | ng/ml | 1.4E0 | 3.6E0 | 2.7E0 | 4.6E0 | 2.9E0 | 3.9E0 | 3.6E-2 | 4.7E-2 | 1.5E1 | 1.8E1 | 66 | 70 | 66 | 70 | 0.67 |
| Un | ng/ml | 1.5E0 | 2.1E0 | 1.7E0 | 2.7E0 | 1.0E0 | 3.1E0 | 3.5E-1 | 3.4E-1 | 4.9E0 | 2.5E1 | 66 | 70 | 66 | 70 | 0.64 |
| Ug | ng/ml | 1.3E1 | 8.8E0 | 2.1E1 | 2.3E1 | 1.9E1 | 3.2E1 | 1.5E0 | 1.0E0 | 8.5E1 | 1.6E2 | 66 | 70 | 66 | 70 | 0.44 |
| Ur | ng/ml | 1.5E-1 | 7.0E-2 | 2.9E-1 | 4.4E-1 | 4.5E-1 | 1.2E0 | 1.0E-9 | 1.0E-9 | 2.6E0 | 7.3E0 | 66 | 69 | 66 | 69 | 0.40 |
| Up | ng/ml | 1.0E-9 | 1.0E-9 | 2.3E-3 | 3.9E-2 | 8.0E-3 | 2.9E-1 | 1.0E-9 | 1.0E-9 | 5.3E-2 | 2.4E0 | 66 | 69 | 66 | 69 | 0.55 |
| Us | ng/ml | 1.9E-3 | 3.6E-3 | 8.0E-3 | 4.9E-2 | 1.2E-2 | 2.1E-1 | 1.0E-9 | 1.0E-9 | 6.1E-2 | 1.7E0 | 66 | 69 | 66 | 69 | 0.55 |
| Uv | ng/ml | 2.5E-3 | 3.0E-3 | 1.9E-2 | 1.4E-2 | 5.5E-2 | 5.2E-2 | 1.0E-9 | 1.0E-9 | 3.5E-1 | 4.1E-1 | 66 | 69 | 66 | 69 | 0.47 |
| Ut | ng/ml | 5.3E-1 | 9.1E-1 | 2.2E0 | 4.3E0 | 6.8E0 | 9.3E0 | 1.0E-9 | 1.0E-9 | 5.2E1 | 6.5E1 | 66 | 69 | 66 | 69 | 0.62 |
| Uu | ng/ml | 7.2E0 | 6.4E0 | 7.6E0 | 7.3E0 | 5.0E0 | 5.1E0 | 5.4E-1 | 5.7E-1 | 2.6E1 | 2.9E1 | 66 | 69 | 66 | 69 | 0.47 |
| Uw | ng/ml | 2.0E0 | 2.7E0 | 2.6E0 | 4.5E0 | 2.6E0 | 7.0E0 | 1.5E-1 | 1.0E-9 | 9.8E0 | 3.9E1 | 30 | 29 | 30 | 29 | 0.64 |
| Vb | ng/ml | 1.2E0 | 1.1E0 | 1.2E0 | 1.1E0 | 4.3E-1 | 1.1E0 | 4.7E-1 | 8.5E-2 | 2.0E0 | 6.4E0 | 30 | 29 | 30 | 29 | 0.36 |
| Vc | ng/ml | 1.0E-9 | 1.0E-9 | 6.7E-3 | 4.6E-4 | 2.4E-2 | 2.5E-3 | 1.0E-9 | 1.0E-9 | 1.1E-1 | 1.3E-2 | 30 | 29 | 30 | 29 | 0.47 |
| Uy | ng/ml | 1.3E0 | 1.4E0 | 4.4E0 | 1.1E1 | 1.1E1 | 2.4E1 | 8.7E-2 | 2.0E-2 | 5.1E1 | 9.9E1 | 30 | 29 | 30 | 29 | 0.55 |
| Uz | ng/ml | 1.0E-9 | 1.0E-9 | 1.5E-2 | 1.1E0 | 7.9E-2 | 6.1E0 | 1.0E-9 | 1.0E-9 | 4.4E-1 | 3.3E1 | 30 | 29 | 30 | 29 | 0.52 |
| Ux | ng/ml | 1.9E2 | 1.7E2 | 1.8E2 | 1.9E2 | 1.5E2 | 1.3E2 | 1.2E1 | 4.5E0 | 4.8E2 | 4.9E2 | 30 | 29 | 30 | 29 | 0.52 |
| Va | ng/ml | 1.4E1 | 5.7E0 | 2.5E1 | 2.0E1 | 3.1E1 | 2.4E1 | 3.1E-1 | 3.6E-1 | 1.2E2 | 9.6E1 | 30 | 29 | 30 | 29 | 0.44 |
| Vh | ng/ml | 1.1E-2 | 1.7E-2 | 1.9E-2 | 4.9E-2 | 2.5E-2 | 1.6E-1 | 3.9E-4 | 1.0E-3 | 1.2E-1 | 8.6E-1 | 30 | 29 | 30 | 29 | 0.59 |
| Vi | ng/ml | 4.0E-3 | 5.3E-3 | 6.7E-3 | 8.1E-2 | 7.3E-3 | 3.4E-1 | 1.0E-9 | 1.0E-9 | 3.3E-2 | 1.8E0 | 30 | 29 | 30 | 29 | 0.59 |
| Vj | ng/ml | 2.2E1 | 5.9E1 | 4.5E1 | 9.4E1 | 4.7E1 | 1.3E2 | 4.6E0 | 1.4E0 | 1.8E2 | 6.5E2 | 30 | 28 | 30 | 28 | 0.62 |
| Vp | ng/ml | 1.0E-9 | 1.0E-9 | 1.5E-1 | 8.6E-1 | 7.2E-1 | 5.9E0 | 1.0E-9 | 1.0E-9 | 3.9E0 | 4.9E1 | 66 | 70 | 66 | 70 | 0.57 |
| Vt | ng/ml | 4.9E0 | 7.9E0 | 6.3E0 | 1.2E1 | 5.1E0 | 1.9E1 | 9.6E-1 | 5.6E-1 | 3.2E1 | 1.6E2 | 66 | 70 | 66 | 70 | 0.66 |
| Vu | ng/ml | 1.0E-9 | 1.3E-1 | 9.8E-1 | 2.2E0 | 2.4E0 | 4.0E0 | 1.0E-9 | 1.0E-9 | 1.6E1 | 2.2E1 | 64 | 68 | 64 | 68 | 0.59 |
| Vq | ng/ml | 1.0E2 | 2.9E2 | 5.6E2 | 9.0E2 | 1.0E3 | 1.9E3 | 9.2E-1 | 6.5E-1 | 5.0E3 | 1.2E4 | 55 | 53 | 55 | 53 | 0.59 |
| Vo | ng/ml | 2.6E1 | 2.6E1 | 2.4E1 | 2.5E1 | 4.5E0 | 6.5E0 | 9.7E0 | 1.9E0 | 3.5E1 | 4.8E1 | 66 | 70 | 66 | 70 | 0.51 |
| Vs | ng/ml | 1.0E-9 | 1.0E-9 | 4.9E0 | 1.1E1 | 1.3E1 | 5.6E1 | 1.0E-9 | 1.0E-9 | 8.9E1 | 4.5E2 | 66 | 67 | 66 | 67 | 0.47 |
| Vv | ng/ml | 2.2E0 | 3.6E0 | 5.6E0 | 6.5E0 | 1.1E1 | 8.9E0 | 1.0E-9 | 1.0E-9 | 8.4E1 | 4.4E1 | 66 | 69 | 66 | 69 | 0.53 |
| Vw | ng/ml | 3.6E1 | 4.1E1 | 3.3E1 | 3.7E1 | 1.7E1 | 2.0E1 | 3.1E0 | 2.5E0 | 6.7E1 | 6.9E1 | 30 | 29 | 30 | 29 | 0.57 |
| Oy | pg/ml | 4.7E-1 | 4.7E-1 | 7.7E0 | 3.5E0 | 3.7E1 | 1.1E1 | 1.0E-9 | 1.0E-9 | 4.0E2 | 9.9E1 | 218 | 138 | 218 | 138 | 0.48 |
| Oz | pg/ml | 6.7E-3 | 1.0E-9 | 2.5E-1 | 6.2E-1 | 3.9E-1 | 3.4E0 | 1.0E-9 | 1.0E-9 | 2.1E0 | 2.9E1 | 218 | 138 | 218 | 138 | 0.48 |
| Pa | pg/ml | 3.7E-1 | 5.1E-1 | 1.5E0 | 3.8E0 | 6.8E0 | 2.1E1 | 1.0E-9 | 1.0E-9 | 8.6E1 | 2.3E2 | 218 | 138 | 218 | 138 | 0.57 |
| Pb | pg/ml | 1.0E-9 | 1.0E-9 | 2.4E0 | 5.9E-1 | 3.3E1 | 3.6E0 | 1.0E-9 | 1.0E-9 | 4.9E2 | 3.2E1 | 218 | 138 | 218 | 138 | 0.47 |
| Pc | pg/ml | 4.8E-2 | 9.8E-3 | 4.2E-1 | 3.0E0 | 1.1E0 | 2.8E1 | 1.0E-9 | 1.0E-9 | 1.4E1 | 3.3E2 | 218 | 138 | 218 | 138 | 0.49 |
| Pd | pg/ml | 1.4E0 | 2.1E0 | 3.7E0 | 1.2E1 | 9.0E0 | 7.3E1 | 1.0E-9 | 1.0E-9 | 9.4E1 | 8.4E2 | 218 | 138 | 218 | 138 | 0.57 |
| Pe | pg/ml | 1.8E1 | 3.9E1 | 8.9E1 | 3.5E2 | 3.9E2 | 1.5E3 | 1.0E-9 | 1.0E-9 | 4.7E3 | 1.5E4 | 218 | 138 | 218 | 138 | 0.63 |
| Pf | pg/ml | 1.2E0 | 2.8E0 | 1.1E1 | 2.6E1 | 4.8E1 | 1.3E2 | 1.0E-9 | 1.0E-9 | 4.8E2 | 1.5E3 | 218 | 138 | 218 | 138 | 0.60 |
| Pg | pg/ml | 3.3E0 | 6.6E0 | 5.2E1 | 1.3E2 | 3.6E2 | 7.0E2 | 1.0E-9 | 1.0E-9 | 4.2E3 | 7.7E3 | 218 | 138 | 218 | 138 | 0.62 |
| Ph | ng/ml | 1.4E-1 | 1.8E-1 | 2.7E-1 | 4.9E-1 | 3.5E-1 | 8.3E-1 | 1.0E-9 | 1.0E-9 | 1.5E0 | 5.4E0 | 64 | 73 | 64 | 73 | 0.57 |
| Pi | ng/ml | 1.9E-1 | 2.2E-1 | 2.5E-1 | 1.5E0 | 4.1E-1 | 9.6E0 | 1.0E-9 | 1.0E-9 | 3.2E0 | 8.2E1 | 64 | 73 | 64 | 73 | 0.60 |
| Pj | ng/mL | 4.6E0 | 6.1E0 | 5.2E0 | 7.2E0 | 3.3E0 | 5.3E0 | 4.9E-1 | 4.0E-1 | 1.6E1 | 3.1E1 | 64 | 73 | 64 | 73 | 0.62 |
| Pk | ng/ml | 6.9E-3 | 1.1E-2 | 9.5E-3 | 4.1E-2 | 1.0E-2 | 1.8E-1 | 1.0E-9 | 1.0E-9 | 5.4E-2 | 1.5E0 | 64 | 73 | 64 | 73 | 0.63 |
| aA | mg/dL | 8.6E-1 | 1.0E0 | 9.7E-1 | 1.2E0 | 4.6E-1 | 7.9E-1 | 3.0E-1 | 3.0E-1 | 4.1E0 | 4.7E0 | 361 | 178 | 361 | 178 | 0.59 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aC | mg/mL | 2.7E0 | 2.1E0 | 2.9E0 | 2.3E0 | 1.4E0 | 1.2E0 | 1.1E0 | 7.5E-1 | 7.4E0 | 6.7E0 | 93 | 83 | 93 | 83 | 0.35 |
| aD | ug/mL | 2.8E0 | 3.3E0 | 4.7E0 | 4.6E0 | 5.4E0 | 3.8E0 | 7.5E-1 | 7.5E-1 | 3.5E1 | 2.1E1 | 93 | 83 | 93 | 83 | 0.51 |
| aE | mg/mL | 5.8E-1 | 5.7E-1 | 5.9E-1 | 6.0E-1 | 1.6E-1 | 1.8E-1 | 2.8E-1 | 1.8E-1 | 1.1E0 | 1.2E0 | 93 | 83 | 93 | 83 | 0.51 |
| aF | ng/mL | 2.2E0 | 2.3E0 | 5.2E0 | 4.9E0 | 8.4E0 | 6.7E0 | 4.3E-3 | 4.3E-3 | 5.0E1 | 3.5E1 | 93 | 83 | 93 | 83 | 0.52 |
| aG | mg/mL | 1.4E-1 | 1.3E-1 | 1.6E-1 | 1.5E-1 | 9.2E-2 | 8.0E-2 | 3.2E-2 | 5.1E-2 | 4.6E-1 | 4.8E-1 | 93 | 83 | 93 | 83 | 0.50 |
| aH | ug/mL | 6.9E1 | 7.1E1 | 7.6E1 | 7.8E1 | 3.9E1 | 4.2E1 | 8.9E0 | 1.1E1 | 2.0E2 | 2.0E2 | 93 | 83 | 93 | 83 | 0.50 |
| aI | ug/mL | 1.8E2 | 1.6E2 | 1.8E2 | 1.7E2 | 6.0E1 | 6.2E1 | 3.2E1 | 4.7E1 | 3.3E2 | 3.4E2 | 93 | 83 | 93 | 83 | 0.43 |
| aJ | ug/mL | 2.2E0 | 2.5E0 | 3.0E0 | 3.7E0 | 2.1E0 | 3.2E0 | 9.5E-1 | 8.2E-1 | 1.2E1 | 2.3E1 | 93 | 83 | 93 | 83 | 0.58 |
| aK | ng/mL | 1.5E0 | 1.1E0 | 2.2E0 | 1.7E0 | 2.0E0 | 1.8E0 | 2.8E-2 | 2.9E-4 | 9.1E0 | 1.0E1 | 93 | 83 | 93 | 83 | 0.42 |
| aL | mg/mL | 7.4E-1 | 7.4E-1 | 7.7E-1 | 7.5E-1 | 2.5E-1 | 2.6E-1 | 2.2E-1 | 2.7E-1 | 1.4E0 | 1.7E0 | 93 | 83 | 93 | 83 | 0.48 |
| aM | U/mL | 1.4E1 | 2.4E1 | 3.2E1 | 5.9E1 | 5.4E1 | 1.2E2 | 4.2E-2 | 4.2E-2 | 3.5E2 | 8.2E2 | 93 | 83 | 93 | 83 | 0.63 |
| aN | U/mL | 1.0E1 | 2.0E1 | 1.6E1 | 3.6E1 | 1.9E1 | 5.6E1 | 2.5E-3 | 2.5E-3 | 9.7E1 | 3.8E2 | 93 | 83 | 93 | 83 | 0.68 |
| aO | pg/mL | 4.5E1 | 7.4E1 | 4.6E2 | 4.2E2 | 1.1E3 | 7.7E2 | 6.0E-2 | 6.0E-2 | 6.6E3 | 3.9E3 | 93 | 83 | 93 | 83 | 0.55 |
| aP | ng/mL | 1.5E0 | 1.7E0 | 2.2E0 | 2.6E0 | 3.0E0 | 3.2E0 | 4.5E-1 | 6.8E-1 | 2.8E1 | 2.8E1 | 93 | 83 | 93 | 83 | 0.58 |
| aQ | ng/mL | 2.5E-1 | 2.4E-1 | 3.7E-1 | 3.4E-1 | 2.9E-1 | 3.5E-1 | 2.0E-4 | 2.0E-4 | 1.1E0 | 2.0E0 | 93 | 83 | 93 | 83 | 0.47 |
| aR | ng/mL | 1.7E0 | 2.1E0 | 2.6E0 | 3.5E0 | 3.4E0 | 4.6E0 | 2.6E-1 | 5.6E-1 | 2.1E1 | 3.4E1 | 93 | 83 | 93 | 83 | 0.59 |
| aS | ng/mL | 3.1E-1 | 5.1E-1 | 1.0E0 | 9.7E-1 | 3.5E0 | 1.2E0 | 4.2E-3 | 4.2E-3 | 3.3E1 | 6.2E0 | 93 | 83 | 93 | 83 | 0.60 |
| aU | pg/mL | 7.6E1 | 5.8E1 | 1.1E2 | 8.9E1 | 1.0E2 | 1.1E2 | 7.4E-2 | 7.4E-2 | 5.1E2 | 7.0E2 | 93 | 83 | 93 | 83 | 0.42 |
| aV | ng/mL | 6.3E-1 | 4.3E-1 | 9.5E-1 | 1.1E0 | 9.6E-1 | 3.6E0 | 3.8E-2 | 7.6E-4 | 5.2E0 | 3.3E1 | 93 | 83 | 93 | 83 | 0.42 |
| aW | pg/mL | 1.9E1 | 2.1E1 | 2.1E1 | 2.4E1 | 1.9E1 | 4.5E1 | 7.2E-2 | 7.2E-2 | 1.7E2 | 4.2E2 | 93 | 83 | 93 | 83 | 0.51 |
| aX | ng/mL | 8.9E0 | 7.4E0 | 1.5E1 | 1.8E1 | 2.6E1 | 3.8E1 | 3.0E-1 | 6.2E-1 | 2.2E2 | 3.1E2 | 93 | 83 | 93 | 83 | 0.48 |
| aY | pg/mL | 5.1E1 | 5.4E1 | 6.8E1 | 8.4E1 | 5.8E1 | 1.4E2 | 4.1E-1 | 4.1E-1 | 3.1E2 | 1.2E3 | 93 | 83 | 93 | 83 | 0.52 |
| aZ | pg/mL | 2.2E2 | 2.6E2 | 4.5E2 | 9.3E2 | 6.2E2 | 1.9E3 | 1.7E0 | 1.7E0 | 2.9E3 | 1.2E4 | 93 | 83 | 93 | 83 | 0.54 |
| bA | ng/mL | 9.5E0 | 2.5E1 | 3.9E1 | 1.1E2 | 8.9E1 | 2.3E2 | 3.0E-2 | 3.0E-2 | 6.8E2 | 1.5E3 | 93 | 83 | 93 | 83 | 0.65 |
| bB | ng/mL | 2.9E2 | 2.4E2 | 3.3E2 | 2.8E2 | 1.8E2 | 1.7E2 | 2.1E0 | 1.2E1 | 9.5E2 | 8.1E2 | 93 | 83 | 93 | 83 | 0.42 |
| bC | ng/mL | 3.2E2 | 3.3E2 | 5.4E2 | 7.8E2 | 6.8E2 | 1.1E3 | 1.4E1 | 3.5E1 | 4.0E3 | 4.7E3 | 93 | 83 | 93 | 83 | 0.53 |
| bE | mg/mL | 5.3E0 | 4.8E0 | 5.7E0 | 5.2E0 | 2.1E0 | 2.2E0 | 1.8E0 | 1.3E0 | 1.2E1 | 1.2E1 | 93 | 83 | 93 | 83 | 0.42 |
| bF | pg/mL | 3.5E1 | 4.3E1 | 2.5E2 | 4.5E2 | 1.2E3 | 1.5E3 | 5.0E-2 | 2.5E0 | 1.1E4 | 1.0E4 | 93 | 83 | 93 | 83 | 0.56 |
| bG | ng/mL | 1.5E0 | 1.8E0 | 2.8E0 | 3.6E0 | 3.7E0 | 5.1E0 | 1.1E-1 | 1.1E-1 | 2.3E1 | 3.0E1 | 93 | 83 | 93 | 83 | 0.53 |
| bH | pg/mL | 5.7E-1 | 5.7E-1 | 6.7E0 | 5.8E0 | 2.9E1 | 1.5E1 | 5.7E-1 | 5.7E-1 | 2.8E2 | 1.2E2 | 93 | 83 | 93 | 83 | 0.50 |
| bI | ng/mL | 4.0E-3 | 4.0E-3 | 8.2E-2 | 1.0E-1 | 1.6E-1 | 2.3E-1 | 4.0E-3 | 4.0E-3 | 6.8E-1 | 9.8E-1 | 93 | 83 | 93 | 83 | 0.49 |
| bJ | mg/mL | 2.0E0 | 1.9E0 | 2.5E0 | 2.2E0 | 2.0E0 | 2.0E0 | 2.5E-4 | 2.5E-4 | 7.8E0 | 1.1E1 | 93 | 83 | 93 | 83 | 0.45 |
| bL | pg/mL | 4.3E0 | 3.2E0 | 1.0E1 | 8.0E0 | 1.3E1 | 9.7E0 | 4.6E-2 | 4.6E-2 | 6.0E1 | 3.5E1 | 93 | 83 | 93 | 83 | 0.44 |
| bM | mg/mL | 1.5E0 | 2.2E0 | 1.8E0 | 2.5E0 | 1.2E0 | 1.7E0 | 1.4E-1 | 1.6E-2 | 6.2E0 | 8.6E0 | 93 | 83 | 93 | 83 | 0.64 |
| bN | ng/mL | 3.5E1 | 3.1E1 | 1.4E2 | 1.0E2 | 3.1E2 | 2.6E2 | 1.4E-1 | 1.4E-1 | 1.9E3 | 1.9E3 | 93 | 83 | 93 | 83 | 0.48 |
| bO | ng/mL | 4.0E-2 | 4.0E-2 | 8.8E0 | 9.3E0 | 1.6E1 | 2.4E1 | 4.0E-2 | 4.0E-2 | 6.4E1 | 1.3E2 | 93 | 83 | 93 | 83 | 0.43 |
| bP | mg/mL | 5.2E-1 | 5.3E-1 | 7.4E-1 | 7.6E-1 | 6.2E-1 | 7.8E-1 | 4.9E-2 | 9.2E-2 | 3.7E0 | 4.8E0 | 93 | 83 | 93 | 83 | 0.49 |
| bQ | pg/mL | 2.1E1 | 2.3E1 | 4.3E1 | 2.4E2 | 6.8E1 | 1.5E3 | 1.5E-1 | 1.5E-1 | 4.8E2 | 1.3E4 | 93 | 83 | 93 | 83 | 0.54 |
| bR | ng/mL | 1.2E-2 | 1.2E-2 | 1.4E-1 | 1.8E-1 | 3.7E-1 | 9.5E-1 | 1.2E-2 | 1.2E-2 | 3.4E0 | 8.7E0 | 93 | 83 | 93 | 83 | 0.46 |
| bS | pg/mL | 9.4E-1 | 9.4E-1 | 9.2E0 | 9.9E0 | 3.7E1 | 4.4E1 | 9.4E-1 | 9.4E-1 | 3.4E2 | 3.9E2 | 93 | 83 | 93 | 83 | 0.48 |
| bU | ng/mL | 9.2E-2 | 1.3E-2 | 1.8E-1 | 2.0E-1 | 2.5E-1 | 7.3E-1 | 1.3E-2 | 1.3E-2 | 1.8E0 | 6.6E0 | 93 | 83 | 93 | 83 | 0.43 |
| bV | pg/mL | 4.4E2 | 5.3E2 | 6.4E2 | 6.3E2 | 1.2E3 | 3.8E2 | 1.6E2 | 2.3E2 | 1.2E4 | 2.2E3 | 93 | 83 | 93 | 83 | 0.59 |
| bW | pg/mL | 3.1E2 | 3.3E2 | 4.8E2 | 5.7E2 | 4.4E2 | 8.1E2 | 8.4E1 | 1.1E2 | 2.4E3 | 4.8E3 | 93 | 83 | 93 | 83 | 0.53 |
| bX | ng/mL | 1.8E-3 | 2.5E-5 | 3.0E-3 | 2.2E-3 | 3.5E-3 | 2.7E-3 | 2.5E-5 | 2.5E-5 | 1.3E-2 | 8.4E-3 | 93 | 83 | 93 | 83 | 0.45 |
| bZ | pg/mL | 2.7E2 | 3.1E2 | 1.6E3 | 2.5E3 | 5.4E3 | 8.5E3 | 1.5E-1 | 1.5E-1 | 4.4E4 | 5.8E4 | 93 | 83 | 93 | 83 | 0.51 |
| cA | pg/mL | 6.0E-1 | 6.0E-1 | 2.0E0 | 6.4E0 | 3.5E0 | 4.1E1 | 6.0E-1 | 6.0E-1 | 1.5E1 | 3.7E2 | 93 | 83 | 93 | 83 | 0.49 |
| cB | ng/mL | 5.7E-2 | 3.5E-2 | 8.1E-2 | 6.7E-2 | 8.4E-2 | 9.2E-2 | 1.7E-3 | 1.7E-3 | 3.8E-1 | 4.3E-1 | 93 | 83 | 93 | 83 | 0.41 |
| cC | pg/mL | 4.6E1 | 3.9E1 | 4.8E1 | 4.2E1 | 4.7E1 | 5.3E1 | 1.0E0 | 1.0E0 | 3.7E2 | 4.5E2 | 93 | 83 | 93 | 83 | 0.44 |
| cD | pg/mL | 6.1E0 | 3.8E0 | 1.4E1 | 1.2E1 | 5.2E1 | 3.7E1 | 3.3E-1 | 3.3E-1 | 4.8E2 | 2.9E2 | 93 | 83 | 93 | 83 | 0.37 |
| cE | pg/mL | 4.9E1 | 7.0E1 | 2.5E2 | 2.8E2 | 5.9E2 | 5.9E2 | 1.2E-1 | 1.2E-1 | 3.1E3 | 3.8E3 | 93 | 83 | 93 | 83 | 0.56 |
| cF | pg/mL | 9.4E0 | 5.3E-1 | 1.8E1 | 1.3E1 | 2.7E1 | 3.2E1 | 5.3E-1 | 5.3E-1 | 1.4E2 | 2.7E2 | 93 | 83 | 93 | 83 | 0.42 |
| cG | pg/mL | 5.0E1 | 6.4E1 | 9.7E1 | 2.6E2 | 1.6E2 | 1.1E3 | 1.1E1 | 7.8E0 | 1.1E3 | 1.0E4 | 93 | 83 | 93 | 83 | 0.60 |
| cH | uIU/mL | 3.5E0 | 3.1E0 | 7.2E0 | 8.1E0 | 1.8E1 | 1.6E1 | 8.6E-3 | 8.6E-3 | 1.6E2 | 1.2E2 | 93 | 83 | 93 | 83 | 0.49 |
| cI | ng/mL | 6.0E0 | 6.4E0 | 1.2E1 | 1.7E1 | 1.6E1 | 2.5E1 | 2.3E-1 | 3.2E-2 | 1.0E2 | 1.2E2 | 93 | 83 | 93 | 83 | 0.52 |
| cJ | ug/mL | 7.4E1 | 5.1E1 | 1.1E2 | 8.8E1 | 1.0E2 | 1.0E2 | 6.9E0 | 5.6E0 | 6.4E2 | 6.2E2 | 93 | 83 | 93 | 83 | 0.43 |
| cK | ng/mL | 3.8E-3 | 3.8E-3 | 1.9E-2 | 2.7E-2 | 4.6E-2 | 1.6E-1 | 3.8E-3 | 3.8E-3 | 3.4E-1 | 1.5E0 | 93 | 83 | 93 | 83 | 0.48 |
| cL | pg/mL | 2.2E2 | 2.1E2 | 3.6E2 | 7.4E2 | 8.0E2 | 2.8E3 | 4.0E1 | 3.1E1 | 7.1E3 | 2.4E4 | 93 | 83 | 93 | 83 | 0.54 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cM | pg/mL | 2.8E2 | 2.6E2 | 3.1E2 | 2.6E2 | 1.9E2 | 1.2E2 | 2.5E1 | 4.2E1 | 1.1E3 | 6.7E2 | 93 | 83 | 93 | 83 | 0.43 |
| cN | pg/mL | 1.2E2 | 1.2E2 | 1.2E2 | 1.4E2 | 4.9E1 | 1.1E2 | 3.8E1 | 6.3E1 | 3.2E2 | 1.1E3 | 93 | 83 | 93 | 83 | 0.56 |
| cO | pg/mL | 2.1E2 | 2.1E2 | 3.1E2 | 5.2E2 | 2.9E2 | 2.1E3 | 5.4E1 | 8.2E1 | 1.7E3 | 1.9E4 | 93 | 83 | 93 | 83 | 0.50 |
| cP | ng/mL | 2.3E3 | 2.4E3 | 2.5E3 | 2.6E3 | 1.0E3 | 9.0E2 | 6.2E2 | 1.0E3 | 5.6E3 | 4.7E3 | 93 | 83 | 93 | 83 | 0.53 |
| cQ | ng/mL | 4.9E-2 | 5.3E-2 | 1.2E-1 | 1.3E-1 | 2.0E-1 | 2.2E-1 | 2.0E-3 | 2.0E-3 | 1.2E0 | 1.3E0 | 93 | 83 | 93 | 83 | 0.53 |
| cR | ng/mL | 3.5E2 | 3.2E2 | 5.3E2 | 6.8E2 | 4.8E2 | 1.1E3 | 3.6E1 | 2.0E1 | 2.9E3 | 7.7E3 | 93 | 83 | 93 | 83 | 0.49 |
| cS | ng/mL | 2.7E2 | 3.1E2 | 4.5E2 | 5.2E2 | 5.1E2 | 8.7E2 | 4.1E1 | 9.1E1 | 2.5E3 | 7.1E3 | 93 | 83 | 93 | 83 | 0.54 |
| cT | ng/mL | 3.7E1 | 6.5E1 | 9.5E1 | 2.3E2 | 1.4E2 | 4.1E2 | 3.6E0 | 4.2E0 | 8.4E2 | 2.1E3 | 93 | 83 | 93 | 83 | 0.61 |
| cU | ng/mL | 5.6E1 | 7.5E1 | 7.7E1 | 1.2E2 | 8.8E1 | 1.9E2 | 6.2E0 | 9.0E0 | 7.7E2 | 1.6E3 | 93 | 83 | 93 | 83 | 0.59 |
| cV | ng/mL | 1.7E-1 | 2.2E-1 | 8.3E-1 | 6.0E-1 | 4.9E0 | 1.5E0 | 2.5E-2 | 3.0E-2 | 4.7E1 | 9.7E0 | 93 | 83 | 93 | 83 | 0.52 |
| cW | mIU/mL | 4.9E-2 | 4.5E-2 | 1.1E-1 | 6.9E-2 | 4.6E-1 | 6.4E-2 | 4.8E-3 | 4.8E-3 | 4.5E0 | 3.9E-1 | 93 | 83 | 93 | 83 | 0.51 |
| cX | ng/mL | 8.9E-2 | 2.0E-1 | 1.5E0 | 2.2E0 | 5.0E0 | 6.2E0 | 2.3E-4 | 2.3E-4 | 2.8E1 | 2.8E1 | 93 | 83 | 93 | 83 | 0.55 |
| cY | ng/mL | 7.6E0 | 6.7E0 | 1.1E1 | 1.0E1 | 9.8E0 | 1.2E1 | 2.2E-1 | 1.7E-1 | 4.1E1 | 6.1E1 | 93 | 83 | 93 | 83 | 0.45 |
| cZ | ug/mL | 1.3E1 | 1.2E1 | 1.5E1 | 1.4E1 | 7.0E0 | 6.5E0 | 2.3E0 | 2.8E0 | 4.6E1 | 3.0E1 | 93 | 83 | 93 | 83 | 0.46 |
| dA | pg/mL | 3.1E2 | 3.2E2 | 3.5E2 | 4.3E2 | 1.8E2 | 6.3E2 | 1.0E2 | 1.1E2 | 1.3E3 | 5.8E3 | 93 | 83 | 93 | 83 | 0.51 |
| dB | ug/mL | 1.7E1 | 2.0E1 | 1.9E1 | 1.7E1 | 2.6E1 | 1.0E1 | 2.1E0 | 2.1E0 | 2.5E2 | 4.0E1 | 93 | 83 | 93 | 83 | 0.54 |
| dC | nmol/L | 3.4E1 | 3.2E1 | 3.8E1 | 3.6E1 | 1.8E1 | 1.5E1 | 1.0E1 | 7.8E0 | 1.4E2 | 9.1E1 | 93 | 83 | 93 | 83 | 0.48 |
| dD | ug/mL | 3.5E1 | 3.2E1 | 3.7E1 | 3.3E1 | 1.1E1 | 1.1E1 | 1.4E1 | 1.4E1 | 7.4E1 | 6.0E1 | 93 | 83 | 93 | 83 | 0.40 |
| dE | ng/mL | 5.5E-1 | 3.9E-1 | 6.1E-1 | 5.4E-1 | 5.8E-1 | 6.3E-1 | 8.4E-3 | 8.4E-3 | 2.7E0 | 2.9E0 | 93 | 83 | 93 | 83 | 0.45 |
| dF | ng/mL | 2.3E2 | 3.0E2 | 2.9E2 | 4.1E2 | 2.0E2 | 2.9E2 | 7.5E1 | 7.5E1 | 1.2E3 | 1.3E3 | 93 | 83 | 93 | 83 | 0.63 |
| dG | ng/mL | 1.1E1 | 1.4E1 | 1.5E1 | 1.9E1 | 1.4E1 | 2.3E1 | 3.2E0 | 3.0E0 | 9.7E1 | 1.8E2 | 93 | 83 | 93 | 83 | 0.58 |
| dH | pg/mL | 7.7E0 | 8.5E0 | 1.8E1 | 2.3E1 | 4.5E1 | 7.6E1 | 4.0E-2 | 4.0E-2 | 3.1E2 | 6.7E2 | 93 | 83 | 93 | 83 | 0.55 |
| dI | pg/mL | 4.6E-1 | 4.6E-1 | 1.9E0 | 5.9E0 | 5.7E0 | 3.6E1 | 4.6E-1 | 4.6E-1 | 4.2E1 | 3.3E2 | 93 | 83 | 93 | 83 | 0.55 |
| dJ | ng/mL | 2.0E0 | 2.1E0 | 2.2E0 | 2.1E0 | 1.1E0 | 1.2E0 | 3.2E-2 | 3.2E-2 | 5.6E0 | 4.9E0 | 93 | 83 | 93 | 83 | 0.49 |
| dK | uIU/mL | 1.5E0 | 1.1E0 | 2.5E0 | 1.8E0 | 4.5E0 | 1.9E0 | 2.8E-4 | 1.4E-2 | 3.9E1 | 1.1E1 | 93 | 83 | 93 | 83 | 0.45 |
| dL | ng/mL | 8.2E2 | 9.5E2 | 9.6E2 | 1.2E3 | 5.2E2 | 7.1E2 | 3.4E2 | 2.8E2 | 3.4E3 | 4.8E3 | 93 | 83 | 93 | 83 | 0.61 |
| dM | pg/mL | 9.5E2 | 1.0E3 | 1.3E3 | 1.5E3 | 1.6E3 | 1.4E3 | 3.9E2 | 3.7E2 | 1.5E4 | 9.6E3 | 93 | 83 | 93 | 83 | 0.56 |
| dN | ug/mL | 9.6E1 | 1.0E2 | 1.0E2 | 1.1E2 | 4.2E1 | 4.5E1 | 2.5E1 | 2.4E1 | 2.8E2 | 3.3E2 | 93 | 83 | 93 | 83 | 0.56 |
| dR | pg/ml | 1.8E3 | 1.2E3 | 2.2E3 | 1.9E3 | 1.8E3 | 2.2E3 | 2.8E2 | 1.3E2 | 7.8E3 | 9.8E3 | 60 | 73 | 60 | 73 | 0.38 |
| dU | pg/ml | 7.4E3 | 1.4E4 | 1.0E4 | 1.8E4 | 8.7E3 | 1.9E4 | 3.4E3 | 6.9E2 | 3.5E4 | 8.1E4 | 12 | 21 | 12 | 21 | 0.65 |
| dX | ng/ml | 5.2E-2 | 8.2E-2 | 1.4E-1 | 1.2E-1 | 2.2E-1 | 1.5E-1 | 2.6E-3 | 2.6E-3 | 1.2E0 | 6.6E-1 | 35 | 26 | 35 | 26 | 0.50 |
| dW | ng/ml | 1.2E-1 | 1.7E-1 | 1.7E-1 | 2.7E-1 | 1.6E-1 | 2.5E-1 | 6.4E-2 | 6.8E-2 | 5.8E-1 | 8.0E-1 | 9 | 10 | 9 | 10 | 0.62 |
| eF | ng/ml | 4.2E0 | 4.1E0 | 5.6E0 | 5.2E0 | 5.8E0 | 3.6E0 | 2.0E0 | 2.0E0 | 4.6E1 | 2.9E1 | 60 | 73 | 60 | 73 | 0.50 |
| eC | pg/ml | 3.0E2 | 2.8E2 | 3.8E2 | 3.5E2 | 2.9E2 | 3.1E2 | 9.9E0 | 1.9E1 | 1.4E3 | 2.0E3 | 50 | 67 | 50 | 67 | 0.44 |
| eD | pg/ml | 2.3E2 | 1.8E2 | 7.6E2 | 6.4E2 | 1.8E3 | 1.3E3 | 5.2E-1 | 5.2E-1 | 8.3E3 | 7.0E3 | 46 | 51 | 46 | 51 | 0.44 |
| eO | ng/ml | 4.6E1 | 9.4E1 | 3.2E2 | 1.2E2 | 4.3E2 | 8.7E1 | 2.0E1 | 4.1E1 | 9.9E2 | 3.3E2 | 9 | 10 | 9 | 10 | 0.61 |
| eM | ng/ml | 2.8E0 | 2.8E0 | 4.2E0 | 5.8E0 | 4.5E0 | 8.1E0 | 7.6E-1 | 6.9E-1 | 2.7E1 | 3.9E1 | 42 | 37 | 42 | 37 | 0.51 |
| eP | ng/ml | 3.7E-3 | 3.7E-3 | 7.3E-1 | 1.8E0 | 1.7E0 | 5.7E0 | 3.7E-3 | 3.7E-3 | 8.6E0 | 2.8E1 | 35 | 26 | 35 | 26 | 0.49 |
| eT | ng/ml | 2.7E2 | 2.9E2 | 7.1E2 | 7.8E2 | 8.4E2 | 8.9E2 | 1.0E2 | 7.1E1 | 2.9E3 | 2.9E3 | 28 | 27 | 28 | 27 | 0.55 |
| eQ | pg/ml | 1.0E0 | 1.0E0 | 8.5E1 | 3.4E1 | 1.5E2 | 6.4E1 | 1.0E0 | 1.0E0 | 4.7E2 | 2.2E2 | 12 | 21 | 12 | 21 | 0.45 |
| eW | U/ml | 1.1E-2 | 6.7E-3 | 6.2E-2 | 2.0E-1 | 9.7E-2 | 4.9E-1 | 6.7E-3 | 6.7E-3 | 3.1E-1 | 1.6E0 | 9 | 10 | 9 | 10 | 0.43 |
| fA | ng/ml | 1.9E2 | 2.3E2 | 3.6E2 | 4.9E2 | 4.8E2 | 4.7E2 | 3.9E1 | 4.0E1 | 1.5E3 | 1.4E3 | 12 | 19 | 12 | 19 | 0.60 |
| eZ | ng/ml | 4.8E1 | 5.6E1 | 5.7E1 | 5.6E1 | 2.8E1 | 2.3E1 | 2.3E1 | 1.8E1 | 1.2E2 | 1.1E2 | 28 | 27 | 28 | 27 | 0.52 |
| fB | ng/ml | 5.6E2 | 6.1E2 | 6.6E2 | 6.6E2 | 2.7E2 | 2.7E2 | 3.1E2 | 2.6E2 | 1.3E3 | 1.3E3 | 12 | 19 | 12 | 19 | 0.51 |
| fN | ng/ml | 2.1E-1 | 2.1E-1 | 4.4E0 | 3.4E0 | 1.1E1 | 5.6E0 | 2.1E-1 | 2.1E-1 | 5.4E1 | 2.1E1 | 28 | 27 | 28 | 27 | 0.49 |
| fP | ng/ml | 2.6E2 | 2.8E2 | 3.2E2 | 3.3E2 | 2.0E2 | 1.7E2 | 8.9E1 | 1.8E0 | 1.0E3 | 9.5E2 | 57 | 70 | 57 | 70 | 0.54 |
| fR | ng/ml | 1.3E5 | 1.8E5 | 2.0E5 | 2.5E5 | 1.6E5 | 2.0E5 | 3.9E4 | 1.9E2 | 6.9E5 | 8.7E5 | 63 | 52 | 63 | 52 | 0.59 |
| fY | ng/ml | 2.6E2 | 2.5E2 | 2.4E2 | 2.6E2 | 9.9E1 | 1.1E2 | 6.5E1 | 3.6E1 | 3.9E2 | 4.8E2 | 28 | 27 | 28 | 27 | 0.52 |
| gC | ng/ml | 2.5E2 | 2.4E2 | 2.8E2 | 2.5E2 | 1.2E2 | 1.2E2 | 1.4E2 | 8.3E1 | 6.4E2 | 5.9E2 | 22 | 25 | 22 | 25 | 0.42 |
| gL | pg/ml | 6.7E4 | 6.6E4 | 7.4E4 | 7.6E4 | 3.6E4 | 3.9E4 | 1.4E4 | 1.1E4 | 1.9E5 | 2.2E5 | 60 | 73 | 60 | 73 | 0.50 |
| gP | U/ml | 2.7E2 | 2.8E2 | 2.9E2 | 3.0E2 | 1.1E2 | 1.3E2 | 1.3E2 | 1.2E1 | 8.0E2 | 1.1E3 | 60 | 72 | 60 | 72 | 0.53 |
| gW | ng/ml | 6.6E2 | 3.8E2 | 1.2E3 | 6.8E2 | 1.2E3 | 8.1E2 | 6.8E1 | 2.3E0 | 6.1E3 | 4.2E3 | 48 | 51 | 48 | 51 | 0.37 |
| gV | ng/ml | 2.1E1 | 2.2E1 | 2.1E1 | 2.2E1 | 6.9E0 | 8.3E0 | 1.0E1 | 8.1E-2 | 3.7E1 | 3.4E1 | 23 | 15 | 23 | 15 | 0.58 |
| tF | pg/mL | 9.5E2 | 1.3E3 | 1.3E4 | 1.1E4 | 4.4E4 | 3.5E4 | 1.8E1 | 1.2E1 | 2.8E5 | 2.5E5 | 50 | 69 | 50 | 69 | 0.53 |
| gZ | ug/ml | 5.2E-1 | 9.0E-1 | 3.5E1 | 4.4E1 | 1.2E2 | 1.0E2 | 8.7E-2 | 1.4E-1 | 4.1E2 | 4.0E2 | 12 | 21 | 12 | 21 | 0.68 |
| hA | ng/ml | 2.4E0 | 2.9E0 | 1.5E1 | 1.4E1 | 5.6E1 | 4.3E1 | 1.7E-2 | 1.7E-2 | 3.5E2 | 2.9E2 | 46 | 52 | 46 | 52 | 0.55 |
| nM | pg/ml | 1.0E-9 | 1.0E-9 | 1.0E-9 | 3.3E1 | 0.0E0 | 2.2E2 | 1.0E-9 | 1.0E-9 | 1.0E-9 | 1.5E3 | 30 | 46 | 30 | 46 | 0.51 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nN | pg/ml | 1.2E3 | 2.1E3 | 1.7E3 | 9.4E3 | 1.8E3 | 2.7E4 | 8.1E1 | 2.3E2 | 7.1E3 | 1.5E5 | 30 | 46 | 30 | 46 | 0.66 |
| nO | pg/ml | 2.2E1 | 2.6E1 | 2.8E1 | 4.5E1 | 1.9E1 | 5.6E1 | 8.8E0 | 4.0E0 | 9.5E1 | 3.1E2 | 30 | 46 | 30 | 46 | 0.59 |
| nR | pg/ml | 1.6E1 | 1.8E1 | 4.7E1 | 1.4E2 | 7.1E1 | 3.5E2 | 1.7E0 | 1.0E0 | 2.6E2 | 1.9E3 | 30 | 46 | 30 | 46 | 0.55 |
| nT | pg/ml | 6.5E1 | 7.9E1 | 9.1E1 | 1.3E2 | 7.3E1 | 1.7E2 | 1.0E-9 | 1.0E-9 | 2.5E2 | 9.2E2 | 30 | 46 | 30 | 46 | 0.54 |
| nU | pg/ml | 4.4E1 | 4.4E1 | 5.3E1 | 1.4E2 | 6.0E1 | 2.8E2 | 1.0E-9 | 1.0E-9 | 2.0E2 | 1.5E3 | 30 | 46 | 30 | 46 | 0.55 |
| lW | pg/ml | 1.0E-9 | 1.0E-9 | 6.0E0 | 1.4E1 | 1.4E1 | 3.6E1 | 1.0E-9 | 1.0E-9 | 5.5E1 | 1.7E2 | 30 | 46 | 30 | 46 | 0.54 |
| lX | pg/ml | 1.0E3 | 8.1E2 | 1.1E3 | 9.4E2 | 5.8E2 | 5.6E2 | 3.2E2 | 1.9E2 | 2.6E3 | 2.5E3 | 30 | 46 | 30 | 46 | 0.42 |
| lY | pg/ml | 1.8E1 | 2.0E1 | 1.9E1 | 2.1E1 | 1.2E1 | 2.0E1 | 1.0E-9 | 1.0E-9 | 4.8E1 | 1.2E2 | 30 | 46 | 30 | 46 | 0.51 |
| mE | pg/ml | 1.0E-9 | 1.0E-9 | 1.4E0 | 3.3E0 | 2.4E0 | 9.3E0 | 1.0E-9 | 1.0E-9 | 7.8E0 | 5.7E1 | 30 | 46 | 30 | 46 | 0.55 |
| mF | pg/ml | 1.0E-9 | 5.7E-1 | 1.4E0 | 9.9E0 | 2.4E0 | 3.9E1 | 1.0E-9 | 1.0E-9 | 9.5E0 | 2.5E2 | 30 | 46 | 30 | 46 | 0.60 |
| mH | pg/ml | 4.3E0 | 2.7E0 | 4.8E0 | 5.6E0 | 5.6E0 | 9.0E0 | 1.1E0 | 4.0E-1 | 3.2E1 | 5.3E1 | 30 | 46 | 30 | 46 | 0.48 |
| mI | pg/ml | 1.0E-9 | 3.0E0 | 6.0E0 | 2.7E1 | 1.1E1 | 7.3E1 | 1.0E-9 | 1.0E-9 | 3.7E1 | 4.6E2 | 30 | 46 | 30 | 46 | 0.60 |
| mM | pg/ml | 2.5E1 | 4.5E1 | 5.3E1 | 1.0E2 | 6.1E1 | 1.9E2 | 1.0E-9 | 1.0E-9 | 2.1E2 | 1.1E3 | 30 | 46 | 30 | 46 | 0.56 |
| mP | pg/ml | 1.6E1 | 1.5E1 | 1.6E1 | 3.8E1 | 1.1E1 | 1.2E2 | 1.0E-9 | 1.0E-9 | 5.8E1 | 8.1E2 | 29 | 46 | 29 | 46 | 0.52 |
| mS | pg/ml | 1.6E3 | 1.5E3 | 1.8E3 | 1.7E3 | 8.9E2 | 1.1E3 | 8.8E1 | 1.0E-9 | 3.7E3 | 5.1E3 | 30 | 46 | 30 | 46 | 0.44 |
| mT | pg/ml | 5.0E1 | 6.0E1 | 1.5E2 | 1.5E2 | 2.8E2 | 3.0E2 | 1.0E1 | 1.2E1 | 1.4E3 | 1.7E3 | 29 | 46 | 29 | 46 | 0.49 |
| mU | pg/ml | 2.3E0 | 2.1E0 | 2.8E0 | 8.4E0 | 1.8E0 | 3.3E1 | 1.0E-9 | 1.0E-9 | 8.6E0 | 2.2E2 | 29 | 46 | 29 | 46 | 0.50 |
| mW | pg/ml | 2.3E3 | 2.0E3 | 2.4E3 | 2.7E3 | 1.1E3 | 2.3E3 | 3.1E2 | 1.0E-9 | 4.9E3 | 1.1E4 | 29 | 46 | 29 | 46 | 0.46 |
| mY | pg/ml | 6.2E2 | 6.6E2 | 8.0E2 | 1.1E3 | 8.6E2 | 1.4E3 | 1.0E-9 | 1.0E-9 | 4.2E3 | 8.0E3 | 30 | 46 | 30 | 46 | 0.55 |
| mZ | pg/ml | 1.8E2 | 1.7E2 | 4.1E2 | 3.5E2 | 5.9E2 | 3.9E2 | 1.0E-9 | 1.1E1 | 3.1E3 | 1.5E3 | 29 | 46 | 29 | 46 | 0.46 |
| nA | pg/ml | 1.5E0 | 2.3E0 | 6.0E0 | 7.6E0 | 1.1E1 | 1.5E1 | 1.0E-9 | 1.0E-9 | 5.4E1 | 6.5E1 | 29 | 46 | 29 | 46 | 0.50 |
| nB | pg/ml | 2.7E2 | 3.0E2 | 2.9E2 | 3.3E2 | 1.3E2 | 2.0E2 | 3.0E1 | 3.8E1 | 5.9E2 | 9.6E2 | 30 | 46 | 30 | 46 | 0.53 |
| nC | pg/ml | 1.0E-9 | 8.3E1 | 6.3E2 | 1.4E4 | 2.1E3 | 6.4E4 | 1.0E-9 | 1.0E-9 | 1.1E4 | 3.8E5 | 30 | 46 | 30 | 46 | 0.60 |
| nD | pg/ml | 8.5E0 | 6.6E0 | 8.8E0 | 1.7E1 | 7.5E0 | 4.1E1 | 1.0E-9 | 1.0E-9 | 3.3E1 | 2.6E2 | 29 | 46 | 29 | 46 | 0.48 |
| nF | pg/ml | 1.0E-9 | 1.0E-9 | 3.5E0 | 2.8E0 | 1.7E1 | 9.5E0 | 1.0E-9 | 1.0E-9 | 9.3E1 | 4.7E1 | 30 | 46 | 30 | 46 | 0.51 |
| nH | pg/ml | 1.0E-9 | 2.8E0 | 3.2E0 | 2.9E2 | 5.4E0 | 1.5E3 | 1.0E-9 | 1.0E-9 | 1.7E1 | 1.0E4 | 29 | 46 | 29 | 46 | 0.61 |
| nI | pg/ml | 4.8E1 | 1.0E-9 | 6.8E1 | 6.8E1 | 7.0E1 | 1.9E2 | 1.0E-9 | 1.0E-9 | 2.0E2 | 1.2E3 | 30 | 46 | 30 | 46 | 0.39 |
| nJ | pg/ml | 2.5E-1 | 1.7E-1 | 8.1E-1 | 4.1E0 | 1.1E0 | 2.0E1 | 1.0E-9 | 1.0E-9 | 4.9E0 | 1.3E2 | 30 | 46 | 30 | 46 | 0.49 |
| nK | pg/ml | 1.0E-9 | 1.0E-9 | 9.9E0 | 2.0E1 | 2.1E1 | 3.9E1 | 1.0E-9 | 1.0E-9 | 7.5E1 | 2.2E2 | 29 | 46 | 29 | 46 | 0.60 |
| nL | pg/ml | 1.0E-9 | 4.3E0 | 8.2E0 | 4.4E2 | 1.8E1 | 2.1E3 | 1.0E-9 | 1.0E-9 | 8.1E1 | 1.4E4 | 30 | 46 | 30 | 46 | 0.63 |
| hL | pg/ml | 1.6E4 | 1.9E4 | 2.2E4 | 2.3E4 | 1.7E4 | 1.3E4 | 2.6E3 | 5.1E3 | 7.2E4 | 6.0E4 | 28 | 27 | 28 | 27 | 0.56 |
| hO | pg/ml | 1.6E4 | 1.6E4 | 1.6E4 | 1.6E4 | 2.8E3 | 2.3E3 | 1.3E4 | 1.1E4 | 2.4E4 | 2.1E4 | 28 | 27 | 28 | 27 | 0.41 |
| hP | ng/ml | 4.4E5 | 4.4E5 | 3.8E5 | 5.9E5 | 1.8E5 | 6.3E5 | 4.7E4 | 1.7E4 | 9.0E5 | 2.8E6 | 28 | 27 | 28 | 27 | 0.60 |
| wJ | pg/ml | 1.4E5 | 1.1E5 | 1.5E5 | 1.8E5 | 7.5E4 | 1.4E5 | 1.1E4 | 1.3E4 | 3.0E5 | 5.8E5 | 26 | 31 | 26 | 31 | 0.51 |
| wK | pg/ml | 3.2E4 | 3.6E4 | 4.1E4 | 5.6E4 | 3.1E4 | 8.7E4 | 3.7E3 | 7.5E3 | 1.3E5 | 5.0E5 | 26 | 31 | 26 | 31 | 0.52 |
| wL | pg/ml | 5.6E0 | 6.7E0 | 5.4E1 | 4.6E1 | 1.7E2 | 1.1E2 | 1.0E-9 | 1.0E-9 | 8.4E2 | 4.7E2 | 26 | 31 | 26 | 31 | 0.48 |
| wP | pg/ml | 2.3E4 | 2.8E4 | 3.4E4 | 6.0E4 | 3.2E4 | 7.0E4 | 1.1E3 | 1.3E3 | 1.6E5 | 3.0E5 | 26 | 31 | 26 | 31 | 0.58 |
| wQ | pg/ml | 2.5E1 | 3.9E1 | 5.6E1 | 6.4E1 | 8.4E1 | 9.9E1 | 1.0E-9 | 1.0E-9 | 3.7E2 | 5.1E2 | 26 | 31 | 26 | 31 | 0.57 |
| hR | pg/ml | 3.0E4 | 2.4E4 | 3.2E4 | 2.6E4 | 1.2E4 | 1.0E4 | 1.2E4 | 1.0E-9 | 5.8E4 | 4.9E4 | 43 | 48 | 43 | 48 | 0.35 |
| hV | pg/ml | 5.3E2 | 3.7E2 | 5.0E2 | 4.1E2 | 2.4E2 | 2.1E2 | 1.3E2 | 1.0E-9 | 1.2E3 | 9.6E2 | 43 | 48 | 43 | 48 | 0.39 |
| hW | pg/ml | 1.7E3 | 1.9E3 | 2.0E3 | 3.0E3 | 1.1E3 | 5.6E3 | 7.1E2 | 1.0E-9 | 7.3E3 | 4.0E4 | 43 | 48 | 43 | 48 | 0.58 |
| hX | pg/ml | 1.1E3 | 1.0E3 | 1.2E3 | 1.0E3 | 1.2E3 | 5.3E2 | 3.3E2 | 2.5E0 | 8.6E3 | 2.9E3 | 43 | 48 | 43 | 48 | 0.46 |
| iA | pg/ml | 1.8E2 | 1.5E2 | 2.8E2 | 2.4E2 | 3.3E2 | 2.2E2 | 1.6E1 | 1.5E1 | 1.8E3 | 8.7E2 | 50 | 69 | 50 | 69 | 0.47 |
| iB | ng/ml | 4.6E0 | 5.8E0 | 5.6E0 | 7.5E0 | 4.3E0 | 5.5E0 | 3.3E-2 | 8.3E-1 | 1.9E1 | 2.4E1 | 46 | 52 | 46 | 52 | 0.63 |
| iC | U/ml | 2.5E-1 | 4.5E-1 | 4.1E-1 | 1.9E0 | 4.9E-1 | 7.6E0 | 1.0E-9 | 3.7E-2 | 1.8E0 | 5.5E1 | 46 | 52 | 46 | 52 | 0.65 |
| tQ | pg/ml | 1.3E3 | 1.5E3 | 1.4E3 | 1.5E3 | 5.2E2 | 6.3E2 | 3.7E2 | 5.0E2 | 2.5E3 | 3.3E3 | 25 | 28 | 25 | 28 | 0.57 |
| tT | pg/ml | 1.4E1 | 2.1E1 | 1.7E1 | 2.6E1 | 7.2E0 | 1.7E1 | 7.4E0 | 5.4E0 | 3.0E1 | 9.3E1 | 25 | 29 | 25 | 29 | 0.68 |
| tS | pg/ml | 1.1E0 | 7.7E-1 | 1.6E0 | 1.3E0 | 1.9E0 | 2.0E0 | 1.0E-9 | 1.0E-9 | 8.5E0 | 1.0E1 | 25 | 30 | 25 | 30 | 0.44 |
| tX | pg/ml | 1.0E0 | 1.2E0 | 1.3E0 | 2.1E0 | 1.1E0 | 2.5E0 | 2.5E-2 | 2.8E-1 | 4.4E0 | 1.0E1 | 25 | 29 | 25 | 29 | 0.54 |
| tO | pg/ml | 4.4E0 | 3.9E0 | 4.9E0 | 5.5E0 | 3.5E0 | 3.8E0 | 1.0E-9 | 1.7E0 | 1.4E1 | 1.8E1 | 25 | 30 | 25 | 30 | 0.55 |
| tR | pg/ml | 2.0E-1 | 2.2E-1 | 3.2E-1 | 3.7E-1 | 3.8E-1 | 5.3E-1 | 1.0E-9 | 1.0E-9 | 1.5E0 | 2.5E0 | 25 | 29 | 25 | 29 | 0.51 |
| tU | pg/ml | 1.1E1 | 9.8E0 | 1.2E1 | 1.4E1 | 7.5E0 | 1.7E1 | 1.6E0 | 2.2E-1 | 3.1E1 | 8.0E1 | 25 | 31 | 25 | 31 | 0.45 |
| tN | pg/ml | 2.0E1 | 2.0E1 | 2.4E1 | 3.7E1 | 1.8E1 | 4.0E1 | 1.0E-9 | 1.0E-9 | 8.0E1 | 1.6E2 | 25 | 28 | 25 | 28 | 0.56 |
| tV | ng/ml | 4.2E2 | 1.0E3 | 6.1E2 | 9.5E2 | 5.8E2 | 6.2E2 | 1.9E2 | 5.3E1 | 2.9E3 | 3.1E3 | 26 | 30 | 26 | 30 | 0.70 |
| iH | ng/ml | 1.5E5 | 1.7E5 | 1.5E5 | 1.6E5 | 4.5E4 | 5.3E4 | 7.1E4 | 2.9E3 | 2.6E5 | 2.5E5 | 50 | 69 | 50 | 69 | 0.57 |
| iJ | ng/ml | 5.6E4 | 4.4E4 | 5.5E4 | 5.5E4 | 2.3E4 | 4.3E4 | 5.5E3 | 1.8E3 | 1.0E5 | 2.5E5 | 50 | 69 | 50 | 69 | 0.44 |
| hB | ng/ml | 4.6E-1 | 5.1E-1 | 5.6E-1 | 7.0E-1 | 3.9E-1 | 5.7E-1 | 1.4E-1 | 1.2E-1 | 1.7E0 | 3.2E0 | 50 | 69 | 50 | 69 | 0.57 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| hC | pg/ml | 3.5E3 | 7.5E3 | 5.9E3 | 9.9E3 | 7.1E3 | 1.5E4 | 6.0E1 | 4.1E1 | 3.6E4 | 1.1E5 | 50 | 69 | 50 | 69 | 0.61 |
| hF | ng/ml | 1.0E-9 | 1.0E-9 | 8.0E1 | 1.0E-9 | 5.7E2 | 0.0E0 | 1.0E-9 | 1.0E-9 | 4.0E3 | 1.0E-9 | 50 | 69 | 50 | 69 | 0.49 |
| hG | pg/ml | 6.8E3 | 6.7E3 | 7.2E3 | 7.8E3 | 3.0E3 | 3.7E3 | 1.8E3 | 2.3E3 | 1.8E4 | 2.0E4 | 50 | 69 | 50 | 69 | 0.52 |
| iO | ng/ml | 3.7E5 | 3.9E5 | 4.1E5 | 4.2E5 | 2.0E5 | 1.9E5 | 1.1E4 | 9.8E4 | 1.1E6 | 9.2E5 | 50 | 69 | 50 | 69 | 0.53 |
| iP | ng/ml | 5.0E4 | 5.3E4 | 5.2E4 | 6.1E4 | 2.4E4 | 5.7E4 | 1.0E-9 | 7.1E3 | 1.1E5 | 4.4E5 | 50 | 69 | 50 | 69 | 0.51 |
| iZ | ng/ml | 1.5E3 | 1.8E3 | 1.7E3 | 2.0E3 | 8.2E2 | 9.5E2 | 6.6E2 | 7.5E2 | 5.1E3 | 5.7E3 | 50 | 67 | 50 | 67 | 0.59 |
| yH | pg/ml | 1.2E3 | 9.1E2 | 1.8E3 | 2.8E3 | 2.9E3 | 6.2E3 | 1.0E-9 | 1.0E-9 | 1.5E4 | 2.5E4 | 26 | 29 | 26 | 29 | 0.45 |
| yK | U/ml | 2.2E1 | 1.8E1 | 5.3E1 | 2.9E1 | 9.4E1 | 3.3E1 | 1.0E-9 | 1.0E-9 | 3.8E2 | 1.4E2 | 26 | 29 | 26 | 29 | 0.44 |
| yJ | pg/ml | 4.5E4 | 3.0E4 | 4.7E4 | 3.5E4 | 2.6E4 | 2.8E4 | 9.2E3 | 1.9E3 | 1.0E5 | 1.4E5 | 26 | 29 | 26 | 29 | 0.36 |
| yD | ng/ml | 1.2E-2 | 1.4E-2 | 1.2E-2 | 1.4E-2 | 5.6E-3 | 5.8E-3 | 1.0E-9 | 1.0E-9 | 2.8E-2 | 2.4E-2 | 26 | 31 | 26 | 31 | 0.59 |
| jB | ng/ml | 2.8E5 | 2.3E5 | 2.7E5 | 2.2E5 | 7.3E4 | 7.1E4 | 1.5E5 | 9.9E4 | 3.6E5 | 3.5E5 | 12 | 21 | 12 | 21 | 0.32 |
| wB | pg/ml | 9.2E3 | 1.1E4 | 1.1E4 | 1.3E4 | 7.5E3 | 9.9E3 | 1.7E3 | 1.9E3 | 3.3E4 | 4.2E4 | 26 | 31 | 26 | 31 | 0.54 |
| pY | pg/ml | 5.1E0 | 6.4E0 | 1.2E1 | 7.0E0 | 3.6E1 | 3.7E0 | 2.3E0 | 1.6E0 | 2.0E2 | 1.8E1 | 28 | 27 | 28 | 27 | 0.62 |
| sI | ng/ml | 4.7E-2 | 6.2E-2 | 4.7E-2 | 6.3E-2 | 1.3E-2 | 3.5E-2 | 2.1E-2 | 1.0E-2 | 6.6E-2 | 1.5E-1 | 12 | 17 | 12 | 17 | 0.65 |
| sF | mIU/mL | 1.1E1 | 5.6E0 | 1.6E1 | 1.4E1 | 2.2E1 | 2.0E1 | 6.2E-1 | 1.2E0 | 8.1E1 | 7.5E1 | 12 | 17 | 12 | 17 | 0.39 |
| sH | mIU/mL | 5.0E0 | 1.7E0 | 6.1E0 | 4.5E0 | 6.6E0 | 5.7E0 | 1.0E-9 | 7.9E-2 | 2.5E1 | 2.1E1 | 12 | 17 | 12 | 17 | 0.38 |
| sJ | ng/ml | 1.5E-1 | 1.5E-1 | 5.0E-1 | 5.3E-1 | 9.3E-1 | 1.5E0 | 1.0E-9 | 1.0E-9 | 3.3E0 | 6.4E0 | 12 | 17 | 12 | 17 | 0.44 |
| rC | pg/ml | 2.1E3 | 1.2E3 | 2.6E3 | 1.7E3 | 2.6E3 | 1.9E3 | 1.1E2 | 1.0E-9 | 1.5E4 | 1.1E4 | 42 | 46 | 42 | 46 | 0.37 |
| rB | pg/ml | 3.4E1 | 2.9E1 | 5.0E1 | 5.6E1 | 7.0E1 | 6.8E1 | 1.0E-9 | 1.0E-9 | 3.9E2 | 3.2E2 | 42 | 46 | 42 | 46 | 0.49 |
| zG | 2.5ng/ml | 2.4E-1 | 2.2E-1 | 5.7E-1 | 5.7E-1 | 9.8E-1 | 1.1E0 | 1.0E-9 | 1.0E-9 | 4.4E0 | 4.8E0 | 26 | 29 | 26 | 29 | 0.50 |
| zH | 2.3mU/ml | 9.2E-2 | 8.8E-2 | 1.1E-1 | 9.0E-2 | 5.5E-2 | 3.6E-2 | 1.0E-2 | 2.1E-2 | 3.1E-1 | 1.8E-1 | 26 | 29 | 26 | 29 | 0.39 |
| zI | 2.6ng/ml | 2.4E0 | 1.9E0 | 3.7E0 | 5.2E0 | 4.0E0 | 7.0E0 | 6.3E-1 | 5.4E-1 | 1.6E1 | 2.7E1 | 26 | 29 | 26 | 29 | 0.52 |
| qA | ng/ml | 8.9E6 | 1.2E7 | 1.1E7 | 1.3E7 | 7.5E6 | 7.2E6 | 3.7E6 | 4.3E6 | 3.9E7 | 3.0E7 | 28 | 27 | 28 | 27 | 0.62 |
| qB | ng/ml | 6.5E5 | 6.3E5 | 7.6E5 | 9.5E5 | 3.7E5 | 8.7E5 | 2.7E5 | 1.9E5 | 1.6E6 | 3.8E6 | 28 | 27 | 28 | 27 | 0.49 |
| qC | ng/ml | 3.3E5 | 2.6E5 | 7.3E5 | 6.2E5 | 1.1E6 | 1.0E6 | 3.6E4 | 2.5E4 | 5.2E6 | 4.7E6 | 28 | 27 | 28 | 27 | 0.46 |
| qD | ng/ml | 1.5E7 | 1.5E7 | 1.8E7 | 1.7E7 | 9.2E6 | 7.8E6 | 1.2E6 | 7.0E6 | 4.5E7 | 3.7E7 | 28 | 27 | 28 | 27 | 0.50 |
| jD | ng/ml | 2.6E1 | 4.1E1 | 3.4E1 | 6.1E1 | 3.4E1 | 8.5E1 | 1.0E-9 | 1.0E-9 | 1.1E2 | 5.1E2 | 46 | 52 | 46 | 52 | 0.60 |
| jE | ng/ml | 1.0E-9 | 1.0E-9 | 6.3E0 | 5.2E0 | 1.4E1 | 1.0E1 | 1.0E-9 | 1.0E-9 | 6.2E1 | 3.5E1 | 46 | 52 | 46 | 52 | 0.51 |
| jF | ng/ml | 5.0E1 | 2.1E1 | 5.9E1 | 3.7E1 | 5.7E1 | 4.8E1 | 1.0E-9 | 1.0E-9 | 2.1E2 | 1.9E2 | 46 | 52 | 46 | 52 | 0.39 |
| jG | ng/ml | 4.2E3 | 4.4E3 | 4.6E3 | 4.5E3 | 1.8E3 | 2.1E3 | 1.9E3 | 6.7E2 | 8.9E3 | 9.6E3 | 46 | 52 | 46 | 52 | 0.49 |
| jH | ng/ml | 7.8E1 | 7.9E1 | 7.7E1 | 9.4E1 | 3.6E1 | 7.0E1 | 2.1E1 | 1.3E1 | 1.6E2 | 4.3E2 | 46 | 52 | 46 | 52 | 0.54 |
| jI | ng/ml | 7.3E1 | 8.1E1 | 7.0E1 | 9.8E1 | 2.4E1 | 6.9E1 | 1.9E1 | 3.8E1 | 1.5E2 | 4.4E2 | 46 | 52 | 46 | 52 | 0.61 |
| sK | pg/mL | 3.8E3 | 3.8E3 | 3.9E3 | 5.0E3 | 1.3E3 | 4.2E3 | 1.8E3 | 2.1E3 | 7.1E3 | 2.3E4 | 26 | 27 | 26 | 27 | 0.53 |
| sM | pg/mL | 7.3E4 | 7.4E4 | 7.6E4 | 8.5E4 | 2.2E4 | 3.9E4 | 4.8E4 | 3.9E4 | 1.5E5 | 2.0E5 | 26 | 27 | 26 | 27 | 0.53 |
| sO | pg/mL | 2.4E8 | 2.2E8 | 2.5E8 | 2.3E8 | 8.2E7 | 1.0E8 | 4.9E7 | 6.6E7 | 3.7E8 | 4.4E8 | 26 | 27 | 26 | 27 | 0.43 |
| wC | ng/ml | 1.6E0 | 1.5E0 | 2.1E0 | 1.7E0 | 1.6E0 | 1.1E0 | 3.6E-1 | 6.1E-2 | 6.5E0 | 4.8E0 | 26 | 31 | 26 | 31 | 0.43 |
| wD | ng/ml | 2.0E1 | 2.8E1 | 1.2E2 | 4.9E1 | 4.1E2 | 5.7E1 | 3.8E0 | 2.8E0 | 2.1E3 | 2.9E2 | 26 | 31 | 26 | 31 | 0.67 |
| wE | ng/ml | 4.7E1 | 5.6E1 | 4.6E1 | 5.4E1 | 2.0E1 | 2.0E1 | 8.1E0 | 2.0E1 | 9.4E1 | 8.9E1 | 26 | 31 | 26 | 31 | 0.59 |
| wG | ng/ml | 1.1E-1 | 9.9E-2 | 1.4E-1 | 1.3E-1 | 1.7E-1 | 1.5E-1 | 1.0E-9 | 1.0E-9 | 7.1E-1 | 6.8E-1 | 26 | 31 | 26 | 31 | 0.50 |
| wH | ng/ml | 1.9E-2 | 3.9E-2 | 3.0E-1 | 3.9E-1 | 8.7E-1 | 1.0E0 | 1.0E-9 | 1.0E-9 | 4.2E0 | 5.6E0 | 26 | 31 | 26 | 31 | 0.56 |
| wF | ng/ml | 9.5E-2 | 3.3E-1 | 3.3E0 | 1.5E0 | 1.2E1 | 3.5E0 | 1.0E-9 | 1.0E-9 | 5.7E1 | 1.9E1 | 26 | 31 | 26 | 31 | 0.66 |
| rA | pg/ml | 2.4E1 | 2.2E1 | 3.1E1 | 2.9E1 | 3.1E1 | 2.3E1 | 1.0E-9 | 1.0E-9 | 2.0E2 | 1.1E2 | 45 | 50 | 45 | 50 | 0.50 |
| qZ | pg/ml | 4.7E1 | 4.5E1 | 3.4E2 | 7.2E2 | 1.7E3 | 2.4E3 | 2.8E-4 | 5.9E-4 | 1.0E4 | 1.0E4 | 35 | 36 | 35 | 36 | 0.50 |
| qY | pg/ml | 1.8E1 | 1.5E1 | 3.9E1 | 3.8E1 | 5.2E1 | 5.9E1 | 8.7E-1 | 2.1E0 | 2.3E2 | 3.3E2 | 45 | 50 | 45 | 50 | 0.47 |
| qX | pg/ml | 5.5E1 | 6.4E1 | 6.5E1 | 7.8E1 | 4.5E1 | 5.2E1 | 1.0E-9 | 1.0E-9 | 2.3E2 | 2.1E2 | 45 | 50 | 45 | 50 | 0.56 |
| qW | pg/ml | 7.7E0 | 7.5E0 | 1.3E1 | 1.0E1 | 2.0E1 | 9.9E0 | 1.0E-9 | 1.0E-9 | 1.2E2 | 3.6E1 | 45 | 50 | 45 | 50 | 0.49 |
| qV | pg/ml | 1.5E3 | 2.2E3 | 2.4E3 | 2.5E3 | 1.8E3 | 2.2E3 | 2.7E2 | 1.0E2 | 7.5E3 | 1.1E4 | 45 | 50 | 45 | 50 | 0.51 |
| qU | pg/ml | 5.3E1 | 9.6E1 | 1.5E2 | 2.3E2 | 2.4E2 | 3.6E2 | 1.0E-9 | 1.0E-9 | 1.2E3 | 2.1E3 | 45 | 50 | 45 | 50 | 0.58 |
| qT | pg/ml | 3.5E1 | 4.2E1 | 6.2E1 | 6.8E1 | 7.9E1 | 6.2E1 | 1.0E-9 | 1.0E-9 | 4.9E2 | 3.1E2 | 45 | 50 | 45 | 50 | 0.57 |
| qI | ng/ml | 5.1E4 | 6.5E4 | 5.7E4 | 6.7E4 | 2.9E4 | 3.2E4 | 1.0E4 | 2.5E4 | 1.3E5 | 1.6E5 | 27 | 25 | 27 | 25 | 0.59 |
| qH | ng/ml | 6.8E4 | 5.6E4 | 7.1E4 | 6.9E4 | 4.2E4 | 3.7E4 | 1.5E4 | 2.3E4 | 1.8E5 | 1.8E5 | 27 | 25 | 27 | 25 | 0.49 |
| qG | ng/ml | 1.8E5 | 1.9E5 | 1.9E5 | 2.0E5 | 6.7E4 | 7.2E4 | 3.4E4 | 8.4E4 | 3.0E5 | 4.2E5 | 27 | 25 | 27 | 25 | 0.52 |
| jK | ng/ml | 1.5E3 | 1.5E3 | 1.6E3 | 1.7E3 | 5.0E2 | 7.2E2 | 2.8E2 | 7.0E2 | 2.8E3 | 4.1E3 | 46 | 52 | 46 | 52 | 0.49 |
| jL | ng/ml | 1.7E2 | 2.1E2 | 2.7E2 | 2.8E2 | 2.2E2 | 1.8E2 | 5.6E1 | 6.4E1 | 9.6E2 | 7.6E2 | 46 | 52 | 46 | 52 | 0.57 |
| jM | ng/ml | 6.6E4 | 6.8E4 | 7.3E4 | 7.6E4 | 3.8E4 | 4.2E4 | 2.1E4 | 4.6E3 | 1.8E5 | 1.7E5 | 46 | 52 | 46 | 52 | 0.52 |
| jO | pg/ml | 2.1E5 | 2.5E5 | 2.7E5 | 2.8E5 | 1.9E5 | 1.4E5 | 6.0E4 | 9.6E4 | 1.1E6 | 6.5E5 | 46 | 52 | 46 | 52 | 0.54 |
| jP | pg/ml | 2.3E5 | 2.6E5 | 2.6E5 | 3.1E5 | 1.5E5 | 1.5E5 | 3.6E4 | 1.3E5 | 7.1E5 | 7.0E5 | 46 | 52 | 46 | 52 | 0.59 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jQ | pg/ml | 2.7E3 | 2.1E3 | 3.4E3 | 2.9E3 | 3.0E3 | 2.8E3 | 7.3E1 | 5.0E0 | 1.3E4 | 1.3E4 | 46 | 52 | 46 | 52 | 0.44 |
| jR | pg/ml | 7.1E3 | 4.9E3 | 1.0E4 | 9.9E3 | 1.2E4 | 1.3E4 | 3.0E1 | 1.0E-9 | 6.8E4 | 5.6E4 | 46 | 52 | 46 | 52 | 0.46 |
| jT | pg/ml | 1.7E5 | 1.8E5 | 1.8E5 | 1.8E5 | 7.8E4 | 6.4E4 | 7.1E4 | 7.5E4 | 5.5E5 | 3.5E5 | 46 | 52 | 46 | 52 | 0.52 |
| xA | pg/ml | 5.6E0 | 4.7E0 | 1.3E1 | 1.5E1 | 1.7E1 | 3.4E1 | 1.0E-9 | 1.0E-9 | 6.1E1 | 1.6E2 | 26 | 29 | 26 | 29 | 0.46 |
| yE | pg/ml | 8.3E1 | 7.9E1 | 8.4E1 | 8.5E1 | 2.9E1 | 4.0E1 | 3.6E1 | 6.4E0 | 1.4E2 | 2.0E2 | 26 | 29 | 26 | 29 | 0.48 |
| tM | pg/ml | 4.3E1 | 3.9E1 | 4.1E1 | 4.0E1 | 1.7E1 | 2.0E1 | 1.0E-9 | 1.0E-9 | 6.3E1 | 9.9E1 | 26 | 29 | 26 | 29 | 0.44 |
| tL | pg/ml | 1.0E-9 | 1.0E-9 | 2.8E0 | 3.4E-1 | 1.3E1 | 8.4E-1 | 1.0E-9 | 1.0E-9 | 6.7E1 | 3.6E0 | 26 | 29 | 26 | 29 | 0.52 |
| jU | mIU/ml | 5.5E0 | 5.4E0 | 1.4E1 | 1.0E1 | 2.3E1 | 1.3E1 | 8.1E-2 | 3.9E-1 | 1.1E2 | 5.7E1 | 46 | 52 | 46 | 52 | 0.48 |
| jV | mIU/ml | 1.9E0 | 1.9E0 | 4.7E0 | 3.4E0 | 6.8E0 | 4.0E0 | 2.7E-3 | 2.1E-2 | 3.2E1 | 1.8E1 | 46 | 52 | 46 | 52 | 0.47 |
| jY | ng/ml | 7.3E-4 | 1.7E-3 | 8.7E-3 | 6.6E-3 | 4.4E-2 | 1.5E-2 | 1.0E-9 | 1.0E-9 | 3.0E-1 | 9.4E-2 | 46 | 52 | 46 | 52 | 0.57 |
| kC | pg/ml | 9.3E1 | 1.1E2 | 1.0E2 | 2.4E2 | 6.6E1 | 4.3E2 | 2.1E1 | 3.6E1 | 2.8E2 | 2.7E3 | 30 | 46 | 30 | 46 | 0.62 |
| kE | pg/ml | 1.4E5 | 1.4E5 | 1.3E5 | 1.4E5 | 3.8E4 | 4.2E4 | 4.1E4 | 3.8E4 | 2.3E5 | 2.7E5 | 30 | 46 | 30 | 46 | 0.54 |
| kF | pg/mL | 6.1E1 | 6.6E1 | 6.3E1 | 7.2E1 | 1.9E1 | 2.8E1 | 2.7E1 | 4.0E1 | 1.1E2 | 1.5E2 | 30 | 46 | 30 | 46 | 0.56 |
| kG | pg/mL | 7.5E3 | 9.0E3 | 1.0E4 | 1.6E4 | 8.9E3 | 2.5E4 | 1.3E3 | 1.1E3 | 4.1E4 | 1.6E5 | 30 | 46 | 30 | 46 | 0.59 |
| kI | pg/ml | 1.7E2 | 2.1E2 | 1.9E2 | 2.3E2 | 8.8E1 | 1.3E2 | 6.4E1 | 1.0E-9 | 4.2E2 | 6.7E2 | 30 | 46 | 30 | 46 | 0.58 |
| kK | pg/ml | 1.1E2 | 1.2E2 | 1.3E2 | 2.1E2 | 1.1E2 | 3.0E2 | 6.4E0 | 2.1E1 | 5.0E2 | 1.9E3 | 30 | 46 | 30 | 46 | 0.59 |
| kN | pg/ml | 8.6E2 | 1.2E3 | 1.1E3 | 1.8E3 | 6.8E2 | 2.1E3 | 2.1E2 | 7.3E1 | 2.6E3 | 1.0E4 | 30 | 46 | 30 | 46 | 0.56 |
| kO | pg/ml | 7.0E3 | 7.2E3 | 7.3E3 | 1.1E4 | 2.0E3 | 2.1E4 | 4.0E3 | 3.7E3 | 1.1E4 | 1.5E5 | 30 | 46 | 30 | 46 | 0.50 |
| kP | pg/ml | 6.7E3 | 5.1E3 | 7.7E3 | 6.0E3 | 4.7E3 | 3.8E3 | 3.1E3 | 9.6E2 | 2.7E4 | 1.6E4 | 30 | 46 | 30 | 46 | 0.37 |
| kQ | pg/ml | 4.2E3 | 4.5E3 | 4.9E3 | 5.7E3 | 3.7E3 | 4.3E3 | 5.6E2 | 1.1E3 | 2.5E4 | 2.5E4 | 50 | 69 | 50 | 69 | 0.56 |
| kR | pg/ml | 1.9E1 | 2.6E1 | 4.3E1 | 3.1E1 | 1.4E2 | 2.4E1 | 1.0E-9 | 2.9E0 | 1.0E3 | 1.1E2 | 50 | 69 | 50 | 69 | 0.59 |
| kS | pg/ml | 8.6E2 | 8.8E2 | 1.0E3 | 9.7E2 | 6.0E2 | 5.8E2 | 2.6E2 | 8.2E1 | 3.2E3 | 3.0E3 | 50 | 69 | 50 | 69 | 0.49 |
| pS | ng/ml | 1.7E5 | 1.4E5 | 1.9E5 | 1.7E5 | 8.6E4 | 1.1E5 | 9.7E4 | 6.8E4 | 5.0E5 | 5.7E5 | 26 | 27 | 26 | 27 | 0.38 |
| rZ | ng/ml | 1.0E-9 | 5.3E-3 | 4.6E-3 | 1.7E-2 | 1.5E-2 | 4.6E-2 | 1.0E-9 | 1.0E-9 | 9.4E-2 | 3.0E-1 | 41 | 48 | 41 | 48 | 0.67 |
| rY | ng/ml | 6.1E-2 | 6.4E-2 | 2.5E-1 | 8.7E-1 | 9.8E-1 | 3.8E0 | 2.4E-3 | 1.0E-9 | 6.3E0 | 2.0E1 | 41 | 48 | 41 | 48 | 0.53 |
| rX | ng/ml | 1.0E-9 | 1.0E-9 | 1.2E-1 | 1.3E-1 | 5.9E-1 | 5.6E-1 | 1.0E-9 | 1.0E-9 | 3.7E0 | 3.1E0 | 41 | 48 | 41 | 48 | 0.53 |
| lK | pg/ml | 6.5E1 | 5.9E1 | 1.6E2 | 1.3E2 | 1.9E2 | 1.6E2 | 1.0E-9 | 1.0E-9 | 7.4E2 | 6.9E2 | 46 | 51 | 46 | 51 | 0.42 |
| lL | pg/ml | 1.8E3 | 1.7E3 | 2.6E3 | 3.2E3 | 3.0E3 | 5.9E3 | 7.5E1 | 1.2E2 | 1.9E4 | 4.2E4 | 46 | 52 | 46 | 52 | 0.49 |
| lM | pg/ml | 1.6E3 | 1.1E3 | 4.2E3 | 5.2E3 | 7.4E3 | 1.1E4 | 2.7E2 | 9.5E0 | 4.2E4 | 6.7E4 | 46 | 52 | 46 | 52 | 0.44 |
| lN | pg/ml | 1.0E-9 | 1.0E-9 | 3.2E0 | 3.4E0 | 7.4E0 | 6.2E0 | 1.0E-9 | 1.0E-9 | 4.3E1 | 2.4E1 | 46 | 52 | 46 | 52 | 0.52 |
| lO | pg/ml | 1.0E-9 | 1.0E-9 | 7.4E-1 | 5.2E0 | 5.0E0 | 2.6E1 | 1.0E-9 | 1.0E-9 | 3.4E1 | 1.4E2 | 46 | 51 | 46 | 51 | 0.51 |
| zA | ng/ml | 2.2E7 | 2.1E7 | 2.2E7 | 2.1E7 | 7.0E6 | 6.0E6 | 9.1E6 | 1.0E7 | 3.4E7 | 3.6E7 | 25 | 31 | 25 | 31 | 0.46 |
| rW | ng/ml | 1.2E-2 | 1.2E-2 | 2.9E-2 | 3.5E-2 | 4.0E-2 | 7.1E-2 | 1.0E-9 | 1.0E-9 | 1.7E-1 | 3.2E-1 | 27 | 25 | 27 | 25 | 0.50 |
| rV | ng/ml | 1.0E-9 | 1.0E-9 | 1.6E-2 | 1.2E-2 | 5.8E-2 | 3.2E-2 | 1.0E-9 | 1.0E-9 | 2.8E-1 | 1.5E-1 | 27 | 25 | 27 | 25 | 0.54 |
| rU | ng/ml | 7.1E-2 | 9.5E-2 | 2.2E-1 | 1.1E-1 | 5.3E-1 | 1.1E-1 | 1.0E-9 | 1.0E-9 | 2.7E0 | 4.0E-1 | 27 | 25 | 27 | 25 | 0.50 |
| rT | ng/ml | 6.7E0 | 4.4E0 | 7.2E0 | 6.7E0 | 4.2E0 | 5.2E0 | 6.5E-1 | 1.0E0 | 2.1E1 | 2.0E1 | 27 | 25 | 27 | 25 | 0.42 |
| rS | ng/ml | 3.9E0 | 4.2E0 | 6.1E0 | 1.1E1 | 5.9E0 | 1.8E1 | 7.6E-1 | 1.1E0 | 2.5E1 | 7.0E1 | 27 | 25 | 27 | 25 | 0.54 |
| sC | pg/mL | 5.4E3 | 7.9E3 | 8.7E3 | 1.3E4 | 9.1E3 | 1.7E4 | 2.4E3 | 1.7E3 | 3.9E4 | 7.4E4 | 26 | 27 | 26 | 27 | 0.55 |
| yL | pg/ml | 3.1E1 | 2.8E1 | 3.7E1 | 8.3E1 | 3.1E1 | 2.6E2 | 5.6E0 | 9.1E0 | 1.8E2 | 1.4E3 | 26 | 29 | 26 | 29 | 0.47 |
| rP | ng/ml | 1.3E2 | 1.3E2 | 2.0E2 | 2.3E2 | 1.8E2 | 2.3E2 | 1.0E-9 | 1.2E1 | 5.0E2 | 8.0E2 | 27 | 25 | 27 | 25 | 0.51 |
| rQ | ng/ml | 1.0E-9 | 1.0E-9 | 1.0E-9 | 1.3E1 | 0.0E0 | 4.1E1 | 1.0E-9 | 1.0E-9 | 1.0E-9 | 1.7E2 | 27 | 25 | 27 | 25 | 0.56 |
| rO | ng/ml | 1.5E-2 | 2.5E-2 | 4.1E-2 | 3.8E-2 | 8.1E-2 | 4.5E-2 | 1.0E-9 | 1.0E-9 | 4.0E-1 | 1.9E-1 | 27 | 25 | 27 | 25 | 0.58 |
| rR | ng/ml | 1.0E-9 | 4.0E0 | 5.6E0 | 1.6E1 | 1.5E1 | 2.5E1 | 1.0E-9 | 1.0E-9 | 7.9E1 | 9.5E1 | 27 | 25 | 27 | 25 | 0.66 |
| rN | ng/ml | 8.1E-1 | 6.2E-1 | 9.4E-1 | 1.3E0 | 5.9E-1 | 2.6E0 | 5.1E-2 | 2.1E-1 | 2.3E0 | 1.3E1 | 27 | 25 | 27 | 25 | 0.42 |
| qO | pg/ml | 8.3E3 | 8.2E3 | 1.1E4 | 1.4E4 | 7.9E3 | 1.2E4 | 2.7E3 | 7.4E2 | 2.8E4 | 4.8E4 | 27 | 26 | 27 | 26 | 0.53 |
| qP | pg/ml | 3.6E2 | 3.2E2 | 3.9E2 | 4.4E2 | 2.1E2 | 3.4E2 | 7.0E1 | 1.1E2 | 8.3E2 | 1.5E3 | 27 | 26 | 27 | 26 | 0.50 |
| qQ | pg/ml | 1.5E1 | 1.5E1 | 2.3E1 | 2.3E1 | 5.3E1 | 5.1E1 | 1.0E-9 | 1.0E-9 | 2.8E2 | 2.8E2 | 27 | 26 | 27 | 26 | 0.47 |
| nW | pg/ml | 1.1E5 | 1.1E5 | 1.1E5 | 1.1E5 | 2.8E4 | 2.8E4 | 5.8E4 | 3.6E4 | 1.9E5 | 1.7E5 | 50 | 69 | 50 | 69 | 0.50 |
| nY | pg/ml | 2.1E3 | 2.5E3 | 2.3E3 | 2.9E3 | 1.2E3 | 1.8E3 | 5.1E2 | 6.3E2 | 4.7E3 | 1.0E4 | 50 | 69 | 50 | 69 | 0.58 |
| oO | pg/ml | 8.9E4 | 8.9E4 | 9.9E4 | 1.1E5 | 5.4E4 | 8.7E4 | 1.5E4 | 3.3E3 | 2.6E5 | 4.0E5 | 27 | 42 | 27 | 42 | 0.49 |
| oP | pg/ml | 1.2E5 | 1.3E5 | 1.4E5 | 1.6E5 | 7.4E4 | 1.2E5 | 2.4E4 | 2.4E4 | 3.1E5 | 5.7E5 | 27 | 42 | 27 | 42 | 0.51 |
| oQ | pg/ml | 3.0E3 | 3.0E3 | 3.2E3 | 4.9E3 | 2.1E3 | 5.8E3 | 9.3E2 | 7.7E2 | 1.1E4 | 3.2E4 | 27 | 42 | 27 | 42 | 0.57 |
| oE | pg/ml | 1.4E2 | 2.6E2 | 3.5E2 | 6.3E2 | 4.4E2 | 7.7E2 | 1.0E-9 | 1.0E-9 | 1.7E3 | 3.4E3 | 50 | 69 | 50 | 69 | 0.62 |
| oF | pg/ml | 9.6E3 | 1.8E4 | 2.3E4 | 3.3E4 | 3.5E4 | 4.3E4 | 4.3E2 | 3.5E2 | 1.7E5 | 2.5E5 | 50 | 69 | 50 | 69 | 0.60 |
| oH | pg/ml | 4.0E1 | 3.4E1 | 8.6E1 | 7.2E1 | 1.4E2 | 9.4E1 | 5.4E0 | 4.3E-1 | 8.6E2 | 4.8E2 | 50 | 69 | 50 | 69 | 0.46 |
| oK | pg/ml | 8.2E2 | 8.8E2 | 1.8E3 | 1.5E3 | 2.0E3 | 1.8E3 | 8.8E1 | 1.4E2 | 9.2E3 | 1.2E4 | 50 | 69 | 50 | 69 | 0.51 |
| oN | pg/ml | 5.2E2 | 5.6E2 | 1.1E3 | 8.2E2 | 2.7E3 | 8.8E2 | 1.6E2 | 1.1E2 | 1.8E4 | 5.3E3 | 50 | 69 | 50 | 69 | 0.56 |

Figure 31 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| oW | pg/ml | 2.1E2 | 3.1E2 | 2.8E2 | 8.4E2 | 2.0E2 | 1.7E3 | 7.7E1 | 2.9E1 | 7.3E2 | 7.6E3 | 12 | 21 | 12 | 21 | 0.59 |
| oT | pg/ml | 3.2E2 | 2.8E2 | 3.4E2 | 3.2E2 | 1.6E2 | 1.9E2 | 1.0E2 | 1.1E2 | 7.4E2 | 7.9E2 | 12 | 21 | 12 | 21 | 0.42 |
| oV | pg/ml | 2.3E2 | 8.9E1 | 3.3E2 | 2.4E2 | 4.0E2 | 4.9E2 | 2.1E1 | 1.0E-9 | 1.4E3 | 2.2E3 | 12 | 21 | 12 | 21 | 0.38 |
| oD | pg/ml | 1.7E4 | 1.3E4 | 1.7E4 | 1.5E4 | 4.8E3 | 6.5E3 | 9.3E3 | 6.6E3 | 2.5E4 | 3.2E4 | 12 | 21 | 12 | 21 | 0.34 |
| uL | ng/ml | 3.5E1 | 3.9E1 | 5.4E1 | 4.4E1 | 5.8E1 | 2.2E1 | 1.5E1 | 1.4E1 | 2.9E2 | 1.1E2 | 25 | 27 | 25 | 27 | 0.51 |
| uO | ng/ml | 4.8E-1 | 2.4E-1 | 1.0E0 | 6.4E-1 | 1.8E0 | 7.4E-1 | 1.0E-9 | 1.0E-9 | 9.3E0 | 2.1E0 | 25 | 27 | 25 | 27 | 0.43 |
| uM | ng/ml | 6.4E-1 | 5.0E-1 | 1.3E0 | 5.8E-1 | 2.5E0 | 5.7E-1 | 1.0E-9 | 1.0E-9 | 1.3E1 | 2.5E0 | 25 | 27 | 25 | 27 | 0.41 |
| uI | ng/ml | 8.7E-2 | 5.9E-2 | 1.2E-1 | 1.0E-1 | 1.1E-1 | 1.2E-1 | 1.6E-2 | 1.5E-2 | 5.8E-1 | 4.3E-1 | 25 | 26 | 25 | 26 | 0.39 |
| uN | ng/ml | 1.5E1 | 1.6E1 | 1.6E1 | 1.8E1 | 5.7E0 | 8.0E0 | 8.0E0 | 9.9E0 | 3.0E1 | 4.1E1 | 25 | 27 | 25 | 27 | 0.57 |
| uG | ng/ml | 1.8E1 | 1.9E1 | 2.2E1 | 2.6E1 | 1.6E1 | 2.5E1 | 6.1E0 | 1.2E0 | 7.9E1 | 1.3E2 | 25 | 27 | 25 | 27 | 0.55 |
| uR | ng/ml | 2.4E0 | 1.8E0 | 2.9E0 | 2.7E0 | 2.3E0 | 2.1E0 | 1.1E0 | 7.5E-1 | 1.3E1 | 8.3E0 | 26 | 29 | 26 | 29 | 0.37 |
| uP | ng/ml | 2.1E0 | 2.4E0 | 2.4E0 | 2.7E0 | 1.1E0 | 1.2E0 | 1.2E0 | 9.3E-1 | 6.0E0 | 6.1E0 | 26 | 29 | 26 | 29 | 0.59 |
| uV | ng/ml | 1.1E-4 | 2.3E-3 | 1.9E-2 | 9.6E-3 | 4.3E-2 | 1.2E-2 | 1.0E-9 | 1.0E-9 | 2.0E-1 | 4.3E-2 | 26 | 29 | 26 | 29 | 0.51 |
| uT | ng/ml | 6.6E1 | 7.8E1 | 1.0E2 | 9.9E1 | 1.0E2 | 8.2E1 | 1.4E1 | 1.3E1 | 4.5E2 | 4.1E2 | 26 | 29 | 26 | 29 | 0.55 |
| uU | ng/ml | 1.9E0 | 1.6E0 | 2.1E0 | 2.3E0 | 1.4E0 | 3.5E0 | 5.2E-1 | 5.4E-1 | 6.0E0 | 2.0E1 | 26 | 29 | 26 | 29 | 0.46 |
| uW | ng/ml | 7.3E0 | 7.9E0 | 7.7E0 | 8.1E0 | 2.1E0 | 2.4E0 | 4.4E0 | 5.1E0 | 1.3E1 | 1.6E1 | 25 | 27 | 25 | 27 | 0.55 |
| vB | ng/ml | 3.0E0 | 3.2E0 | 3.1E0 | 3.6E0 | 1.5E0 | 2.6E0 | 1.1E0 | 5.9E-1 | 8.3E0 | 1.0E1 | 25 | 27 | 25 | 27 | 0.52 |
| vC | ng/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 25 | 27 | 25 | 27 | 0.50 |
| uY | ng/ml | 5.9E-1 | 7.5E-1 | 7.4E-1 | 1.2E0 | 5.6E-1 | 1.2E0 | 6.8E-2 | 3.1E-1 | 2.3E0 | 4.4E0 | 25 | 27 | 25 | 27 | 0.65 |
| uZ | ng/ml | 5.8E-1 | 5.3E-1 | 7.0E-1 | 7.7E-1 | 6.0E-1 | 9.0E-1 | 1.0E-1 | 1.7E-1 | 3.0E0 | 4.9E0 | 25 | 27 | 25 | 27 | 0.49 |
| uX | ng/ml | 8.0E0 | 8.6E0 | 1.2E1 | 1.4E1 | 8.0E0 | 1.5E1 | 4.5E0 | 3.6E0 | 4.0E1 | 6.5E1 | 25 | 27 | 25 | 27 | 0.53 |
| vA | ng/ml | 6.9E-2 | 6.3E-2 | 7.5E-2 | 8.9E-2 | 4.0E-2 | 8.6E-2 | 2.4E-2 | 2.5E-2 | 1.9E-1 | 4.2E-1 | 25 | 27 | 25 | 27 | 0.49 |
| vH | ng/ml | 1.2E-1 | 1.1E-1 | 1.5E-1 | 2.0E-1 | 1.2E-1 | 3.6E-1 | 3.5E-2 | 2.0E-2 | 6.6E-1 | 1.9E0 | 26 | 27 | 26 | 27 | 0.42 |
| vI | ng/ml | 2.0E0 | 2.4E0 | 2.1E0 | 2.8E0 | 1.5E0 | 2.5E0 | 3.0E-2 | 6.3E-3 | 6.4E0 | 1.0E1 | 26 | 27 | 26 | 27 | 0.59 |
| vP | ng/ml | 3.7E2 | 3.2E2 | 4.1E2 | 5.2E2 | 3.1E2 | 4.9E2 | 7.0E1 | 6.7E1 | 1.1E3 | 2.4E3 | 26 | 29 | 26 | 29 | 0.56 |
| vT | ng/ml | 7.2E1 | 8.3E1 | 8.4E1 | 9.1E1 | 4.7E1 | 3.8E1 | 4.1E1 | 4.6E1 | 2.4E2 | 1.8E2 | 26 | 29 | 26 | 29 | 0.58 |
| vU | ng/ml | 3.0E0 | 1.0E-9 | 3.3E1 | 1.9E1 | 4.6E1 | 3.2E1 | 1.0E-9 | 1.0E-9 | 1.3E2 | 1.1E2 | 26 | 29 | 26 | 29 | 0.42 |
| vQ | ng/ml | 3.9E2 | 4.5E2 | 4.1E2 | 4.2E2 | 1.6E2 | 1.7E2 | 7.2E1 | 1.2E2 | 8.1E2 | 8.4E2 | 26 | 29 | 26 | 29 | 0.53 |
| vO | ng/ml | 1.8E3 | 1.7E3 | 1.8E3 | 1.8E3 | 4.0E2 | 5.1E2 | 1.1E3 | 1.0E3 | 2.6E3 | 3.2E3 | 26 | 29 | 26 | 29 | 0.44 |
| vS | ng/ml | 1.3E3 | 1.3E3 | 1.3E3 | 1.2E3 | 3.6E2 | 5.2E2 | 1.0E-9 | 1.0E-9 | 2.1E3 | 2.0E3 | 26 | 29 | 26 | 29 | 0.50 |
| vV | ng/ml | 8.3E2 | 9.0E2 | 8.9E2 | 1.2E3 | 6.9E2 | 1.1E3 | 1.1E2 | 1.0E2 | 2.9E3 | 4.6E3 | 26 | 29 | 26 | 29 | 0.55 |
| vW | ng/ml | 1.1E2 | 1.1E2 | 1.6E2 | 1.8E2 | 1.2E2 | 1.5E2 | 4.3E1 | 6.0E1 | 6.6E2 | 7.7E2 | 26 | 29 | 26 | 29 | 0.54 |
| pF | pg/ml | 7.6E-1 | 5.2E-1 | 1.0E0 | 2.0E0 | 1.4E0 | 1.0E1 | 1.0E-9 | 1.0E-9 | 9.4E0 | 8.7E1 | 50 | 69 | 50 | 69 | 0.42 |
| pH | ng/ml | 7.3E0 | 8.8E0 | 8.8E0 | 1.0E1 | 4.3E0 | 5.6E0 | 3.9E0 | 1.2E0 | 1.8E1 | 2.3E1 | 12 | 21 | 12 | 21 | 0.57 |
| pI | ng/ml | 7.7E1 | 6.7E1 | 7.3E1 | 7.3E1 | 3.4E1 | 4.8E1 | 2.6E1 | 2.3E1 | 1.5E2 | 2.0E2 | 12 | 21 | 12 | 21 | 0.46 |
| pK | ng/ml | 4.0E-1 | 4.6E-1 | 4.1E-1 | 4.9E-1 | 1.6E-1 | 2.1E-1 | 2.3E-1 | 1.7E-1 | 7.7E-1 | 8.6E-1 | 12 | 21 | 12 | 21 | 0.63 |

Analyte panel data:

Unconstrained panels with 3 analytes, where 1.0E-10 >= 'model p-value' > 0. Contains 12,499 panels of 37,933,414 total panels evaluated. :
Ji{Po(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Et(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Fp(aA Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Fr(aA Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Nm(aA Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Nn(aA Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) No(aA Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Nq(aA Hq Hr Hu Hv Hw Hx Ih Ii Ij Ik Il Im In Io Ip Iq Ir Is It Iu Iv Jg Jh Jj Jk Jl Jm Jn Jo Jp Jq Jr

Nh Ni Nl Nu Nx Ny Of Om Oy) Iv(Il In Jg Jj Jl Jt Lw Mk Mm Mt Mx My Mz Nf Nl Nu Nx Of Oy Qe) Jg(Jj Mx Ng Of) Jj(Nl Nu Nx) MtMy
MzNl} Nw{Nj(aA Fp Fr Hr Hu Hw Hx Ih Ii Ij Ik Il In Io Ip Iq Ir Is It Iu Iv Jg Jh Jj Jl Jn Jp Jr Jt Lh Li Lj Lu Lv Lw Lx Ly Lz Ma Mb Mc Md Me
Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nu
Nv Nx Ny Oe Of Og Oh Oi Om Oy Oz Pa Pb Pc Pd Pe Po Qa Qb Qc Qd Qe) Iv(aA Fp Hr Hx Ih Ii Ik Il In Io Is It Iu Jh Jj Lu Lv Lw Lx Lz Ma
Mb Mc Md Me Mf Mh Mi Mj Mk Ml Mm Mn Mp Mq Ms Mt Mv Mw Mx My Mz Nb Nc Nd Ne Nf Ng Nh Ni Nl Nm Nn Nq Ns Nu Nx Ny Oe
Of Og Oh Om Oy Pb Qa Qd Qe) Og(aA Fp Ij It Jg Mx Nl Nu Qa Qd) Nl(aA Fp My Ni Nu Of Oy Qd) Qd(aA Il Ms My Nu Of) Of(aA Jg Mx Nu
Nx) Mx(Mh Mj My) Nu(My Oy) FpNf MyaA} Qd{Nj(aA Hr Hw Ik Il In It Iu Iv Jg Jh Jj Jl Jn Jp Jt Lh Lw Lz Mh Mj Mk Mm Mp Ms Mt Mx
My Mz Nd Nf Ni Nk Nl Nm Nn Nu Nv Nx Oe Of Og Oy) Og(aA Fp Hw Ij Ik Il In Is Iv Jg Jh Jj Jl Jn Jp Jt Lh Lw Lz Mb Mj Mm Ms Mt Mx My
Mz Nc Ne Nf Nh Nl Nm Nu Nv Nx Of) Jg(aA Ik Il Iv Jj Ms My Of Oy Pz) Jp(aA Ik Il Iv Jj Ms My Nl Nu Of) Iv(aA Il In Jj Mk Nl Of) aA(Mj
My Mz Nl Of) Nl(Ik Il Jj) Jj(Nu Nx) MtMy MzIl liLh NxOf] Jp{Nj(aA Fp Ih Ik In Ir Is It Iv Jj Jl Jn Jr Js Jt Lh Lw Lx Mh Mi Mk Mp Mr Ms Mt
Mx My Mz Nd Ni Nk Nm Nn No Nu Nv Nx Of Og Oy Pb Qa Qb Qe) Iv(aA Jj Mx Nu Of Og Oy) Og(Fp Ij Is Mx Nu Qa) Nu(Is Ij Of Oy) Of(Jg
Mx Nx) KxeP} Jg{Of(aA Fp Is Iv Jj Jl Jn Jq Js Lh Lw Mp Mx My Mz Nj Nl Nu Nv Nx Og Oy Pa Qa Qb Qe) Og(aA Fp Ij Is Iv Jl Js Lw Mx Mz
Nj Nl Nu Nx Qa Qb Qe) Jj(Iv Mx Nj Qe) Mx(Nj Oy) NjaA} Og{Nj(Ij Iv Jt Nv Qa Qe) Iv(Ij Nv Nx) QaNx} Jj{Nx(Qa Qe) NjNv} MzNjaA

Unconstrained panels with 3 analytes, where 1.0E-9 >= 'model p-value' > 1.0E-10. Contains 10,198 panels of 37,933,414 total panels evaluated. :
Et{Lj(Fr Hq Hr Hu Hv Hw Hx Ih Ii Ik Il In Io Ip Iq Ir Is It Iu Jg Jh Jk Jl Jm Jn Jo Jp Jq Jr Js Jt Lh Li Lu Lv Lw Lx Ly Lz Ma Mc Md Me Mf Mg
Mh Mi Mj Mk Ml Mm Mn Mp Mq Mr Mt Mu Mv Mw My Mz Na Nb Nd Ng Nh Ni Nk Nm Nn No Nq Nr Ns Nv Nw Nx Ny Oe Oh Oi Om On
Oz Pa Pb Pc Pd Pe Pf Pg Po Pz Qa Qb Qc Qe) Qc(Fr Hq Hr Hu Hv Hw Hx Ih Ii Ij Ik In Io Ip Iq Ir Is Iu Jg Jh Jk Jl Jm Jn Jo Jp Jq Jr Js Jt Lh Li
Lu Lv Lw Lx Ly Lz Ma Mc Md Me Mf Mg Mh Mi Mj Mk Ml Mm Mn Mp Mq Mr Mt Mu Mv Mw Mz Na Nb Nd Ng Nh Ni Nk Nm Nn No Nq
Nr Ns Nv Nw Nx Ny Oe Oh Oi Om On Oz Pa Pb Pc Pd Pe Pf Pg Po Pz Qa Qb Qe) Jp(Fr Hq Hr Hu Hv Hw Hx Ih Ii Ij Ik Il In Io Ip Iq Ir Iu Jg Jh
Jk Jl Jm Jn Jo Jq Jr Js Jt Lh Li Lu Lv Lw Lx Ly Lz Ma Mc Md Me Mf Mg Mi Mj Mk Ml Mm Mn Mp Mq Mr Mt Mu Mv Mw Mz Na Nb Nc Nd
Ne Nf Ng Nh Ni Nk Nn No Nq Nr Ns Nv Nw Nx Ny Oe Oh Oi Om On Oz Pa Pb Pc Pd Pe Pf Pg Po Pz Qb) Jq(Fr Hq Hu Hv Hw Hx Ih Ii Ij Ik Il
In Io Ip Iq Ir Is Iu Jg Jh Jk Jl Jm Jn Jo Jr Js Jt Lh Li Lu Lv Lw Lx Ly Lz Ma Mc Md Me Mf Mg Mh Mi Mj Mk Ml Mm Mn Mp Mq Mr Mt Mu
Mv Mw Mz Na Nb Nd Ng Nh Ni Nk Nm Nn No Nq Nr Ns Nv Nw Nx Ny Oe Oh Oi Ok Om On Oz Pa Pb Pc Pd Pe Pf Pg Po Pz Qb) Ih(Fr Hq
Hr Hu Hv Hw Hx Ii Ij Ik Il Io Ip Iq Ir Is It Iu Jg Jh Jk Jl Jm Jn Jo Jr Js Jt Lh Li Lv Lw Lx Ly Lz Ma Mc Md Me Mf Mg Mh Mi Mj Mk Ml Mm
Mn Mp Mq Mr Mt Mu Mv Mw Na Nb Nd Ng Nh Ni Nk Nn No Nq Nr Ns Nv Nw Nx Ny Oe Oh Oi Om On Oz Pa Pb Pc Pd Pe Pf Pg Po Pz Qa
Qb Qe) Nw(Fr Hq Hr Hu Hv Hw Hx Ii Ij Ik Il In Io Ip Iq Ir Is Iu Jg Jh Jk Jl Jm Jn Jo Jr Js Jt Lh Li Lu Lv Lw Lx Ly Lz Ma Mc Md Me Mf Mg
Mh Mi Mj Mk Ml Mm Mn Mp Mq Mr Mt Mu Mv Mz Na Nb Nd Ng Nh Ni Nk Nn No Nq Nr Ns Nv Nx Ny Oe Oh Oi Ok Om On Oz Pa Pb Pc
Pd Pe Pf Pg Po Pz Qb) Lx(Fr Hq Hr Hu Hv Hw Hx Ii Ik Il In Io Ip Iq Ir Is Iu Jg Jh Jk Jl Jm Jn Jo Jr Js Jt Lh Li Lu Lv Ly Lz Ma Mc Md Me
Mf Mg Mi Mj Mk Ml Mm Mn Mp Mq Mr Mt Mu Mv Mz Na Nb Nd Ng Nh Ni Nk Nm Nn No Nq Nr Ns Nv Ny Oe Oh Oi Om On Oz Pa Pb
Pc Pd Pe Pf Pg Po Pz Qa Qb) Pa(Fr Hq Hr Hu Hv Hw Hx Ii Ij Ik Il In Io Ip Iq Ir Iu Jg Jh Jk Jl Jm Jn Jo Jr Js Jt Lh Li Lu Lv Lw Ly Lz Ma Mc Md
Me Mf Mg Mh Mi Mj Mk Ml Mm Mn Mp Mq Mr Mt Mu Mv Mw Mz Na Nb Nd Ng Nh Ni Nk Nm Nn No Nq Nr Ns Nv Nx Ny Oe Oh Oi Om
On Oz Pb Pc Pd Pe Pf Pg Po Pz Qb) Lv(Fr Hq Hr Hu Hv Hw Hx Ii Ik Il In Io Ip Iq Ir Iu Jg Jh Jk Jl Jm Jo Jr Js Jt Lh Li Lu Lw Ly Lz Ma Mc Md
Me Mf Mg Mh Mi Mj Mk Ml Mm Mn Mp Mq Mr Mt Mu Mv Mw Mz Na Nb Nd Ng Nh Ni Nk Nm Nn No Nq Nr Ns Nv Nx Ny Oe Oh Oi Om
On Oz Pb Pc Pd Pe Pf Pg Po Pz Qb) No(Fr Hq Hr Hu Hv Hw Hx Ii Ik Il In Ip Iq Ir Is It Iu Jg Jh Jk Jl Jm Jn Jo Jr Js Jt Lh Li Lu Lw Ly Lz Ma
Mc Me Mf Mg Mh Mi Mj Mk Ml Mp Mq Mr Mt Mv Mw My Mz Nb Nd Ne Ng Nh Ni Nk Nm Nn Nq Nr Ns Nv Nx Ny Oe Oh Ok Om On Oz
Pb Pc Pd Pe Po Pz Qa Qb Qe) Mf(Hq Hr Hu Hv Hw Hx Ii Ik Il In Io Ip Iq Ir Is Iu Jg Jh Jk Jl Jm Jn Jo Jr Js Jt Lh Li Lu Lw Ly Lz Ma Mc Md Me
Mg Mh Mi Mj Mk Ml Mn Mp Mq Mr Mt Mu Mv Mw Mz Na Nb Nd Ne Nf Ng Nh Ni Nk Nm Nn Nq Nr Ns Nv Nx Ny Oe Oh Om On Oz Pb Pc
Pd Pe Pf Pz Qb) Mr(Fr Hq Hu Hv Hw Hx Ik Il In Io Ip Iq Ir Is Iu Jg Jh Jk Jl Jm Jn Jo Jr Js Jt Lh Li Lu Lw Ly Lz Ma Mc Md Me Mg Mi Mj Mk
Ml Mm Mn Mp Mq Mt Mu Mv Mz Na Nb Nd Ne Ng Nh Ni Nk Nm Nn Nq Nr Ns Nv Nx Ny Oe Oh Oi Om On Oz Pb Pc Pd Pe Pf Pg Po Pz Qb)
Ni(Fr Hq Hr Hu Hv Hw Hx Ii Ij Ik Il In Io Ip Iq Ir Iu Jg Jh Jk Jl Jm Jo Jr Js Jt Lh Li Lu Lw Ly Lz Ma Mc Md Me Mg Mh Mi Mj Mk Ml Mm Mn
Mp Mq Mu Mv Mw Mz Na Nb Nd Ng Nh Nk Nm Nn Nq Nr Ns Nv Nx Ny Oe Oh Oi Om On Oz Pb Pc Pd Pe Pf Pg Po Pz) Nv(Fr Hq Hr Hu Hv
Hw Hx Ik Il In Io Ip Iq Ir Is Iu Jg Jk Jl Jm Jn Jo Jr Js Jt Lh Li Lu Lw Ly Lz Ma Mc Md Me Mg Mh Mi Mj Mk Ml Mm Mn Mp Mq Mt Mu Mz
Na Nb Nd Nh Nk Nm Nn Nq Nr Ns Nx Ny Oe Oh Oi Ok Om On Oz Pb Pc Pd Pe Pf Pg Po Pz Qa Qb) Pe(Fr Hq Hu Hv Hw Hx Ik Il In Io Ip Iq Ir
Is It Iu Jg Jh Jk Jl Jm Jn Jo Jr Js Jt Lh Li Lu Lw Ly Lz Ma Mc Md Me Mg Mh Mi Mj Mk Ml Mn Mp Mq Mt Mv Mw Mz Nb Nd Ne Ng Nh Nk
Nm Nn Nq Nr Ns Nx Ny Oe Oh Oi Ok Om On Oz Pb Pc Pd Po Pz Qa Qb) Mg(Fr Hq Hr Hu Hv Hw Hx Ii Ij Ik Il In Io Ip Iq Ir Iu Jg Jh Jk Jl Jm
Jo Jr Js Jt Lh Li Lu Lw Ly Lz Ma Mc Md Me Mh Mi Mj Mk Ml Mm Mn Mp Mq Mu Mv Mw My Mz Na Nb Nd Ng Nh Nk Nm Nn Nq Nr Ns
Ny Oe Oh Oi Om Oz Pb Pc Pd Pf Pg Po Qb) Hw(Fr Hq Hr Hu Hv Hx Ii Ij Ik Il In Io Ip Iq Ir Iu Jg Jh Jk Jl Jm Jo Jr Jt Lh Li Lu Lw Ly Lz Ma Mc
Md Me Mh Mi Mj Mk Ml Mm Mn Mp Mq Mu Mv Mw My Na Nb Nd Nf Ng Nh Nk Nm Nn Nq Nr Ns Nx Ny Oe Oh Oi Om Oz Pb Pc Pd Pf Pg
Po Pz) Jr(Fr Hq Hu Hv Hx Ii Ij Ik Il In Io Ip Iq Ir Is Iu Jg Jh Jk Jl Jm Jo Js Jt Lh Li Lw Ly Lz Ma Mc Md Me Mh Mi Mj Mk Ml Mm Mn Mp Mq
Mu Mv Mw Na Nb Nd Ng Nh Nk Nm Nn Nq Nr Ns Nx Ny Oe Oh Oi Om On Oz Pb Pc Pd Pf Pg Po Pz Qb) Jt(Fr Hq Hu Hv Hx Ij Ik Il In Io Ip
Iq Ir Is Iu Jg Jh Jk Jl Jm Jn Js Lh Li Lw Ly Lz Ma Mc Md Me Mh Mi Mj Mk Ml Mm Mn Mp Mq Mu Mv Mw Mz Na Nb Nd Nh Nk Nm Nn Nq
Nr Ns Nx Ny Oe Oh Oi Ok Om On Oz Pb Pc Pd Pf Pg Po Pz Qb) Ik(Fr Hq Hr Hu Hv Hx Ii Ij Il In Io Ip Iq Ir Iu Jg Jh Jk Jl Jm Jo Js Lh Li Lu Lw
Ly Lz Ma Mc Md Me Mi Mj Mk Ml Mm Mn Mp Mq Mu Mv Mw Na Nb Nd Ng Nh Nk Nm Nn Nq Nr Ns Nx Ny Oe Oh Oi Om On Oz Pb Pc
Pd Pf Pg Po Qb) Ir(Hq Hr Hu Hv Hx Ii Il In Io Ip Iq Is It Iu Jg Jh Jk Jl Jn Jo Js Lh Li Lu Lw Ly Lz Ma Mc Md Me Mh Mi Mj Mk Ml Mp Mq Mt
Mv Mw My Mz Nb Nd Ne Ng Nh Nk Nm Nn Nq Nr Ns Nx Ny Oe Oh Om On Oz Pb Pc Pd Pz Qa Qb Qe) Jl(Fr Hq Hu Hv Hx Ij Il In Io Ip Is
Iu Jg Jh Jk Jm Jo Js Lh Li Lu Lw Ly Lz Ma Mc Md Me Mi Mj Mk Ml Mm Mn Mp Mq Mu Mv Mz Na Nb Nd Ng Nh Nk Nm Nn Nq Nr Ns Nx
Ny Oe Oh Oi Om On Oz Pb Pc Pd Pf Pg Po Pz Qb) Jo(Fr Hq Hr Hu Hv Hx Ii Ij Il In Io Ip Iq Jg Jh Jk Jm Lh Li Lu Lw Ly Lz Ma Mc Md Me
Mi Mj Mk Ml Mm Mn Mp Mq Mu Mv Mw My Na Nb Nd Nf Ng Nh Nk Nm Nn Nq Nr Ns Ny Oe Oh Oi Om On Oz Pb Pc Pd Pf Pg Po Qb)
Oe(Fr Hq Hr Hu Hv Hx Ii Ij Il In Io Ip Iq Iu Jg Jh Jk Jm Js Lh Li Lu Lw Ly Lz Ma Mc Md Me Mh Mi Mj Mk Ml Mm Mn Mp Mq Mu Mv Mw
Mz Na Nb Nd Ng Nh Nk Nm Nn Nq Nr Ns Ny Oh Oi Om Oz Pb Pc Pd Pf Pg Po Pz) Mp(Fr Hq Hr Hu Hv Hx Ii Ij Il In Io Ip Iq Iu Jg Jh Jk Jm Js
Lh Li Lu Lw Ly Lz Ma Mc Md Mh Mi Mj Mk Ml Mm Mn Mq Mu Mv Mw Na Nb Nd Ng Nh Nk Nm Nn Nq Nr Ns Nx Ny Oh Oi Om Oz Pb Pc
Pd Pf Pg Po Pz) Lh(Fr Hq Hu Hv Hx Ij Il In Io Ip Iq Is Iu Jg Jk Jm Jn Js Li Lu Lw Ly Lz Ma Mc Md Me Mh Mi Mj Mk Ml Mm Mn Mq Mu Mz
Na Nb Nd Nh Nk Nm Nn Nq Nr Ns Nx Ny Oh Oi Om On Oz Pb Pc Pd Pf Pg Po Pz Qb) Oz(Hq Hr Hu Hv Hx Ii Il In Ip Iq Is Iu Jg Jh Jk Jm Jn Js
Li Lu Lw Ly Lz Ma Mc Me Mh Mi Mj Mk Ml Mn Mq Mt Mv Mw My Mz Nb Nd Ne Nf Ng Nh Nk Nm Nn Nq Nr Ns Nx Ny Oh Om On Pb Pc
Pd Po Pz Qb) Mw(Fr Hq Hr Hu Hv Hx Ii Ij Il In Io Ip Iq Iu Jg Jh Jk Jm Js Li Ly Lz Ma Mc Md Me Mi Mj Mk Ml Mm Mn Mq Mu Mv My Na

Figure 31 Continued

Nb Nd Nf Ng Nh Nk Nm Nq Nr Ns Nx Ny Oh Oi Om Pb Pc Pd Pf Pg Po Pz) Nn(Fr Hq Hr Hu Hv Hx Ii Il In Io Ip Iq Is Iu Jg Jh Jk Jm Jn Js Li Lu Lw Ly Lz Ma Mc Md Me Mh Mi Mj Mk Ml Mm Mn Mq Mt Mv Mz Nb Nd Ng Nh Nk Nm Nq Nr Ns Nx Ny Oi Om On Pb Pd Pz Qb) Hu(Hq Hr Hv Hx Ii Ij Il In Io Ip Iq Iu Jg Jh Jk Jm Js Li Lu Lw Ly Lz Ma Mc Md Me Mh Mi Mj Mk Ml Mq Mu Mv My Mz Nb Nd Nf Ng Nh Nk Nm Nq Nr Ns Nx Ny Oh Om On Pb Pc Pd Pf Pg Po) Jh(Fr Hq Hr Hv Hx Ii Ij Il In Io Ip Iq Iu Jg Jk Jm Js Li Ly Lz Ma Mc Md Mi Mj Mk Ml Mm Mn Mq Mu Mv My Na Nb Nd Nf Ng Nk Nm Nq Nr Ns Nx Ny Oh Oi Om Pb Pc Pd Pf Pg Po Pz) Js(Fr Hq Hv Hx Ij In Io Ip Iq Is Iu Jg Jk Jm Jn Li Ly Lz Ma Mc Md Me Mi Mj Mk Ml Mm Mn Mq Mu Mv Mz Na Nb Nd Nh Nk Nq Nr Ns Nx Ny Oh Oi Om On Pb Pc Pd Pf Pg Po Pz Qb) Ng(Fr Hq Hr Hv Hx Ii Ij Il In Io Ip Iq Iu Jk Jm Li Ly Lz Ma Mc Md Me Mh Mi Mj Mk Ml Mm Mn Mq Mu Mv My Na Nb Nd Nk Nm Nq Nr Ns Ny Oh Oi Om Pb Pc Pd Pf Pg Po Pz) On(Fr Hq Hv Hx Ij Il In Io Ip Iq Iu Jg Jk Jm Li Lu Lw Ly Lz Ma Mc Md Mi Mj Mk Ml Mm Mn Mq Mt Mu Mz Na Nb Nd Nk Nq Nr Ns Nx Ny Oh Oi Om Pb Pc Pd Pf Pg Po Pz Qb) Hr(Fr Hq Hv Hx Ii Ij Il In Io Ip Iq Iu Jg Jk Jm Li Ly Lz Ma Mc Md Mi Mj Mk Ml Mm Mn Mq Mu Mv Na Nb Nd Nf Nk Nm Nq Nr Ns Ny Oh Oi Om Pb Pc Pd Pf Pg Po Pz) Nx(Fr Hq Hv Hx Ij Il In Io Ip Iq Is Iu Jg Jk Jm Li Ly Lz Ma Mc Md Mi Mj Mk Ml Mm Mn Mq Mu Mv Na Nb Nd Nk Nq Nr Ns Ny Oh Oi Om Pb Pc Pd Pf Pg Po Pz) Nm(Fr Hq Hv Hx Ii Ij Il In Io Ip Iq Iu Jk Jm Li Lu Ly Lz Ma Mc Md Mi Mj Mk Ml Mm Mn Mq Mu Mv Na Nb Nd Nk Nq Nr Ns Ny Oh Oi Om Pb Pc Pd Pf Pg Po Pz) Lw(Fr Hq Hv Hx Ii Ij Il In Io Ip Iq Iu Jg Jk Jm Li Ly Lz Ma Mc Md Mi Mj Mk Ml Mm Mn Mq Mu Mv Na Nb Nd Nk Nq Nr Ns Ny Oh Oi Om Pb Pc Pd Pf Pg Po Pz) Nh(Fr Hq Hv Hx Ii Ij Il In Io Ip Iq Iu Jg Jk Jm Li Ly Lz Ma Mc Md Mi Mj Mk Ml Mm Mn Mq Mu Mv Na Nb Nd Nk Nq Nr Ns Ny Oh Oi Om Pb Pc Pd Pf Pg Po Pz) Nx(Fr Hq Hv Hx Ij Il In Io Ip Iq Is Iu Jg Jk Jm Li Ly Lz Ma Mc Md Mi Mj Mk Ml Mm Mn Mq Mu Mv Na Nb Nd Nk Nq Nr Ns Ny Oh Oi Om Pb Pc Pd Pf Pg Po Pz) Lu(Fr Hq Hv Hx Ii Ij Il In Io Ip Iq Iu Jg Jk Jm Li Ly Lz Ma Mc Md Mi Mj Mk Ml Mm Mn Mq Mu Na Nb Nd Nk Nq Nr Ns Ny Oh Oi Om Pb Pc Pd Pf Pg Po Pz) Mh(Fr Hv Hx Ii Ij In Io Ip Iq Iu Jg Jk Jm Li Ly Lz Ma Mc Md Mi Mj Ml Mm Mn Mq Mu Mv Na Nb Nd Nk Nq Nr Ns Ny Oh Oi Om Pb Pc Pd Pf Pg Po Pz) Nf(Fr Hq Hv Hx Ii Ij Il In Io Ip Iq Iu Jg Jk Jm Ly Lz Ma Mc Md Mj Mk Ml Mm Mn Mu Mv Na Nb Nd Nk Nq Nr Ns Ny Oh Oi Om Pb Pc Pd Pf Pg Po Pz) My(Fr Hq Hv Hx Ii Il In Io Ip Iq Iu Jk Jm Li Ly Lz Ma Mc Md Mj Mk Ml Mm Mn Mq Mv Na Nb Nd Nk Nq Nr Ns Ny Oh Oi Om Pb Pc Pd Pf Pg Po Pz) Ne(Fr Hq Hv Hx Ij Il Io Ip Iq Jg Jk Jm Li Ly Lz Ma Mc Md Mi Mj Ml Mm Mq Mu Na Nb Nc Nd Nk Nq Nr Ns Ny Oh Oi Om Pc Pd Pf Pg Po Pz) Jn(Fr Hv Hx Ij Io Ip Iq Is Iu Jg Jk Jm Li Ly Lz Ma Mc Md Mi Mj Ml Mm Mn Mq Mu Na Nb Nd Nk Nq Nr Ns Ny Oh Oi Pb Pc Pd Pf Pg Po Pz) Ms(Fr Hv Hx Ii Ij In Io Ip Iq Iu Jk Jm Li Ly Lz Ma Mc Md Mj Mk Ml Mm Mn Mu Mv Na Nb Nk Nq Ns Ny Oh Oi Om Pc Pd Pf Pg Po Pz) Is(Fr Hv Hx Ij Io Ip Iq Jg Jk Jm Li Ly Lz Ma Mc Md Mi Mj Ml Mm Mn Mq Mu Na Nb Nd Nk Nq Nr Ns Ny Oh Oi Pb Pc Pd Pf Pg Po Pz) Qb(Fr Hv Hx Ij Io Ip Iq Jg Jm Li Ly Lz Ma Mc Md Mi Mj Ml Mm Mn Mq Mu Na Nb Nd Nk Nr Ns Ny Oh Oi Pb Pc Pd Pf Pg Po Pz Qa Qe) In(Hq Hv Hx Ii Ij Il Ip Iq Iu Jg Jj Jm Li Ly Lz Ma Mc Md Mi Mj Mk Ml Mq Mu Mv Na Nb Nd Nk Nq Nr Ns Ny Oh Om Pb Pc Pd Po) Mv(Hq Hv Ij Il Io Ip Iq Iu Jg Jk Jm Li Ly Lz Ma Mc Md Mi Mj Mk Mq Mu Nb Nd Nk Nq Nr Ns Ny Oh Om Pb Pc Pd Pf Pg Po) Mt(Fr Hv Ij Io Ip Iq Jg Jm Li Ly Lz Ma Mc Md Mi Mj Ml Mm Mn Mq Mu Na Nb Nd Nk Nr Ns Ny Oh Oi Pc Pd Pf Pg Po Pz) It(Fr Hv Ij Io Ip Iq Jg Jk Jm Li Ly Lz Ma Mc Md Mi Ml Mm Mn Mq Mu Na Nb Nd Nk Nq Nr Ns Oh Oi Pc Pd Pf Pg Po Pz) Mz(Fr Hq Hv Io Ip Iq Iu Jg Jk Jm Li Ly Lz Ma Mc Mi Mm Mn Mq Mu Na Nb Nd Nk Nq Nr Ns Oh Oi Pc Pd Pf Pg Po Pz) Mk(Hq Hv Hx Ii Ij Il Ip Iq Iu Jg Jm Li Ly Lz Ma Mc Md Mi Mq Mu Na Nb Nd Nk Nq Nr Ny Oh Om Pb Pc Pd Pf Po) Nc(Fr Hv Ij Io Ip Iq Jg Jk Jm Li Ly Lz Ma Mc Md Me Mf Mg Mh Mi Mj Mk Ml Mm Mn Mp Mq Mr Ms Mu Mv Mw My Mz Na Nb Nd Ng Nh Ni Nk Nm Nn No Nq Nr Ns Nv Nw Ny Oe Oh Oi Om Oy Oz Pa Pb Pc Pd Pe Pf Pg Po Pz Qc) Pz) Hq(Hv Hx Ii Ij Il Io Ip Iq Jm Li Ly Lz Mc Mi Mq Mu Nb Nd Nk Nq Nr Ns Ny Oh Om Pb Pc Pd Po) Il(aA Hv Hx Ii Ij Ip Iq Iu Jg Jm Li Ly Lz Ma Mc Mi Mq Nb Nd Nk Nq Nr Ns Ny Oh Om Pc Pd Pf) Pb(Hv Hx Ii Ip Iq Iu Jg Jm Li Ly Mc Mi Mj Ml Mq Mu Nb Nd Nk Nq Nr Ns Ny Oh Om Pc Pd Pf Po) Mi(Hv Hx Ii Ip Iq Iu Jg Jm Li Ly Lz Ma Mc Md Mj Ml Mq Nb Nk Nq Nr Ns Ny Ok Om Pd Po) Ii(Hv Ij Ip Iq Jg Jm Li Ly Lz Mc Md Mq Mu Nb Nd Nk Nr Ny Oh Om Oy Pc Pd Pg Po) Jg(Hv Hx Io Ip Iu Jk Ly Ma Mc Mj Ml Mq Nd Nk Nq Ny Oh Ok Om Pc Pd Pz Qa) Mq(Hv Hx Iu Ly Ma Mc Mj Ml Nb Nd Nk Nq Nr Ns Oh Om Pc Pd Qa) Ok(Ij Jk Jm Li Mc Md Mm Mn Mu Nk Nr Ns Oh Oi Pc Pf Pg) Nk(Hv Hx Ip Iu Ly Mc Nb Nd Nq Ny Om Pc Pd Qa Qe) Li(Hx Iu Ly Lz Ma Mc Mj Nd Nq Ny Om Pd Pz Qa Qe) Om(Hv Hx Ij Ip Ly Mc Mu Nb Nd Nr Ny Pc Pd) Qa(Ij Ip Md Mm Mn Mu Nb Nr Oi Pc Pf Pg) Qe(Ij Jm Md Mm Mn Mu Na Nb Nr Oi Pf Pg) Ly(Hv Hx Ip Iq Iu Mc Nd Nr Ny Pc Pd) Mc(Hv Hx Ip Iu Nd Nq Nr Ny Pc Pd) Ny(Hv Ip Iu Ml Nb Nd Nr Pc Pd) Hx(Hv Ip Iu Nb Nd Nr Pc Pd) Nq(Hv Nb Nd Nr Pd) Mb(Fr Ij Jk Po Pz) Nd(Hv Iu Nr Pc) Pd(Iu Lz Pc Pg) Iu(Ip Nr) Pz(aA Jj) MjHv MnOy IjaA} Ok[Jj(aA Fr Hq Hr Hu Hv Hw Hx Ih Ii Ij Ik Il In Io Ip Iq Ir Iu Jg Jh Jk Jl Jm Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mu Mv Mw My Mz Na Nb Nd Ng Nh Ni Nk Nm Nn No Nq Nr Ns Nv Nw Ny Oe Oh Oi Om Oy Oz Pa Pb Pc Pd Pe Pf Pg Po Pz Qc) Fp(Fr Hq Hu Hv Hw Hx Ih Ij Ik Il In Io Ip Iq Ir Is Iu Jg Jh Jl Jn Jo Js Jt Lh Li Lj Lu Lv Lw Lx Ly Lz Ma Mb Mc Md Me Mf Mg Mi Mj Mk Ml Mm Mn Mp Mq Mr Mt Mu Mv Mw Mx Mz Na Nb Nc Nd Ne Ng Nh Ni Nk Nm Nn No Nq Nr Ns Nu Nv Nw Nx Ny Oe Oh Oi Om Oz Pa Pb Pc Pd Po Pz Qa Qb Qc Qe) Nl(Fr Hq Hu Hv Hw Hx Ih Ij Ik Il In Io Ip Iq Ir Iu Jg Jh Jk Jl Jm Jn Jo Jq Jr Js Jt Lh Li Lj Lu Lv Lw Lx Ly Lz Ma Mc Md Me Mf Mg Mh Mi Mj Mk Ml Mm Mn Mp Mq Mr Mt Mu Mv Mw Na Nb Nc Nd Ne Ng Nh Ni Nk Nm Nn Nx Ny Oe Oh Oi Om Oz Pa Pb Pc Pd Pe Pf Pg Po Pz Qa Qb Qc) Mx(Fr Hq Hu Hv Hx Ih Ij Io Ip Iq Ir Is Iu Jg Jh Jk Jl Jm Jn Jo Jq Jr Js Jt Lh Li Lj Lu Lv Lx Ly Lz Ma Mc Md Mc Mf Mg Mi Ml Mm Mn Mp Mq Mr Mt Mu Mv Mw Mz Na Nb Nc Nd Ne Ng Nh Ni Nk Nm Nn No Nq Nr Ns Nv Nw Nx Ny Oe Oh Oi Om On Oz Pa Pb Pc Pd Pe Pf Pg Po Pz Qa Qb Qc Qe) aA(Fr Hq Hu Hw Hx Ih Ii Ik In Io Ip Iq Ir Is Iu Jg Jh Jl Jo Jp Jr Js Jt Lh Li Lj Lu Lv Lw Lx Ly Lz Ma Mc Md Me Mf Mg Mh Mi Mj Mk Ml Mm Mn Mp Mq Mr Mt Mu Mv Mw Mz Na Nb Nd Ne Ng Nh Ni Nk Nm Nn No Nq Nr Ns Nv Nw Nx Ny Oe Oh Oi Om On Oz Pa Pb Pc Pd Pe Pf Pg Po Qa Qb Qc) Jp(Fr Hq Hu Hv Hw Hx Ih Ij Ik Il In Io Ip Iq Ir Is Iu Jg Jh Jk Jl Jn Jo Jr Js Jt Lh Li Lj Lu Lv Lw Lx Ly Lz Ma Mc Md Me Mf Mg Mh Mi Mj Mk Ml Mn Mp Mq Mr Mt Mu Mv Mw Mz Na Nb Nc Nd Ne Ng Nh Ni Nm Nn Nq Nr Ns Nv Nw Nx Ny Oe Om On Oz Pa Pb Pc Pd Po Pz Qa Qb Qc Qe) Nf(Hr Hw Ih Ii Ij Ik Il In Io Ip Iq Ir Iu Jg Jl Jn Jq Jr Js Jt Lh Li Lu Lv Lw Lx Ly Lz Ma Mc Md Me Mf Mg Mh Mi Mj Mk Ml Mm Mn Mp Mq Mr Mt Mu Mv Mw My Na Nb Nc Nd Ne Ng Nh Ni Nk Nm Nn No Nq Nr Ns Nv Ny Oe Oh Oi Om Oy Oz Pa Pb Pc Pd Pe Pg Pz Qb Qc) Nu(Hr Hw Hx Ih Ii Ik Il In Io Ip Iq Ir Iu Jg Jl Jn Jo Js Jt Lu Lv Lw Lx Lz Ma Mb Mc Md Me Mf Mg Mh Mi Mj Mk Ml Mm Mn Mp Mq Mr Ms Mt Mu Mv Mw Mz Na Nb Nc Nd Ne Ng Nh Ni Nm Nn Nq Nr Ns Nv Nw Nx Ny Oe Oh Oi Om On Oz Pa Pb Pc Pd Pz Qa Qb Qc Qe) It(Fr Hq Hr Hw Hx Ih Ij Ik Il In Io Ip Iq Is Iu Jg Jh Jo Lh Lu Lv Lw Lx Ly Lz Ma Mc Md Me Mf Mg Mh Mi Mj Mk Ml Mm Mn Mp Mq Mr Mt Mu Mv Mw Mz Na Nb Nc Nd Ne Ng Nh Ni Nk Nm Nn No Nq Nr Ns Nv Nw Nx Ny Oe Oh Oi Om On Oz Pa Pb Pc Pd Pz Qa Qb Qc Qe) Mb(Hr Ih Ii Ik Il In Io Ip Iq Ir Is Iu Jg Jl Jn Jo Js Jt Lu Lv Lw Lx Ly Lz Ma Md Me Mf Mg Mh Mi Mj Mk Ml Mm Mn Mp Mq Mr Ms Mt Mu Mv Mw My Mz Nc Nd Ne Ng Nh Ni Nm Nn No Nq Nr Ns Nv Nw Nx Ny Oe Oh Om Oy Oz Pa Pb Pd Qa Qb Qc Qe) Ms(Hr Hw Ih Ii Ik Il In Io Ip Iq Ir Is Iu Jg Jl Jn Jo Js Jt Lu Lv Lw Lx Ly Lz Ma Mc Me Mf Mg Mh Mi Mj Mk Mp Mq Mr Mt Mu Mv Mw My Mz Nc Nd Ne Ng Nh Ni Nm Nn Nq Nr Ns Nv Nw Nx Ny Oe Om Oy Oz Pa Pb Pd Pz Qa Qb Qc) Oy(Hq Hr Hw Ih Ii Ij Ik Il In Io Ip Iq Ir Is Iu Jg Jh Jk Jl Jn Js Jt Lh Lu Lv Lw Lx Ly Md Me Mf Mg Mh Mi Mk Mm Mp Mq Mr Mu My Mz Nc Nd Ne Nh Ni Nm Nn Nq Nr Ns Nw Nx Ny Oe Om Oz Pa Pb Pc Pd Pe Pf Pg Qb Qc Qe) Qe(Hq Hu Hv Hw Hx Ik In Io Ip Iq Ir Is Iu Jg Jh Jk Jn Jo Js Lh Lu Lv Lw Me Mf Mg Mh Mj Mk Mp Mt Mv Mw My Mz Na Nb Nc Ne Ng Nh Ni Nm Nn Nq Nr Nw Nx Ny Oe Oh Om On Pb Po Pz Qd) Qa(Hq Hr Hw Hx Ii Ik Il In Io Iq Ir Is Iu Jg Jh Jk Jn Jo Lh Lu Lv Lw Me Mg Mh Mj Mk Mp Mt Mv Mw Mz Na Nc Ne Ng Nh Ni Nm Nq Nw

Nv Nx Qa) Nl(Ij Jt Nv Qa) Ij(aA Mt Nx) Qa(aA Jt Nm) Nv(Mb Nm) MtNx} Iv{Jj(Jt Mm Nv Nx Qa Qe) aA(Jn Mt Mz Nx Qe) In(Jt Nx) Nv(Of Oy) IiLh} Jj{Nx(Fp Jt Mt Nu) NuQe} aC{Ji(aN bM) AjJt}

Unconstrained panels with 3 analytes, where 1.0E-8 >= 'model p-value' > 1.0E-9. Contains 18,183 panels of 37,933,414 total panels evaluated. :
Ok{Nn(Fr Hq Hr Hu Hv Hw Hx Ih Ii Ik Il In Io Ip Iq Ir Is Iu Jg Jh Jk Jl Jn Jo Jq Jr Js Jt Lh Li Lj Lu Lv Lw Lx Ly Lz Ma Mc Md Me Mf Mg Mh Mi Mj Mk Ml Mm Mn Mp Mq Mr Mt Mu Mz Na Nb Nd Ng Nh Ni Nk Nm No Nq Nr Ns Nv Nw Nx Ny Oe Oh Oi Om On Oz Pa Pb Pc Pd Pe Pf Pg Po Pz Qa Qb Qc) Hw(Hq Hr Hu Hv Hx Ih Ii Ik Il In Io Ip Iq Ir Iu Jg Jh Jk Jl Jm Jo Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw My Mz Na Nb Nd Ne Ng Nh Ni Nk Nm No Nq Nr Ns Nv Nw Nx Ny Oe Oh Oi Om Oz Pa Pb Pc Pd Pe Pf Pg Po Pz Qc) Lu(Fr Hq Hu Hv Hx Ih Ij Ik Il In Io Ip Iq Ir Iu Jg Jh Jk Jl Jm Jn Jo Jq Jr Js Jt Lh Li Lj Lv Lw Lx Ly Lz Ma Mc Md Me Mf Mg Mh Mi Mj Mk Ml Mm Mn Mp Mq Mr Mt Mu Mv Mw Mz Na Nb Nd Ng Nh Ni Nk Nm No Nq Nr Ns Nv Nx Ny Oe Oh Oi Om On Oz Pa Pb Pc Pd Pe Pf Pg Po Pz Qb Qc) Lx(Fr Hq Hu Hv Hx Ih Ij Ik Il In Io Ip Iq Ir Is Iu Jg Jh Jl Jn Jo Jr Js Jt Lh Lj Lv Lw Ly Lz Ma Mc Md Me Mf Mg Mi Mj Mk Ml Mm Mn Mp Mq Mr Mt Mu Mv Mw Mz Na Nb Nc Nd Ne Ng Nh Ni Nk Nm No Nq Nr Ns Nv Nw Nx Ny Oe Oh Oi Om On Oz Pa Pb Pc Pd Pe Pf Pg Pz Qa Qb Qc Qe) Ih(Fr Hq Hr Hu Hv Hx Ij Ik Il Io Ip Iq Ir Is Iu Jg Jh Jk Jl Jn Jo Jr Js Jt Lh Lj Lv Lw Ly Lz Ma Mc Md Me Mf Mg Mh Mi Mj Mk Ml Mm Mn Mp Mq Mr Mt Mu Mv Mw Mz Na Nb Nd Ne Ng Nh Ni Nk Nm No Nq Nr Ns Nv Nx Ny Oe Oh Oi Om Oz Pa Pb Pc Pd Pe Pf Pg Po Pz Qa Qb Qc Qe) Jo(Hq Hr Hu Hv Hx Ii Ik Il In Io Ip Iq Ir Is Iu Jg Jh Jl Jm Jn Jq Jr Js Jt Lh Li Lj Lv Lw Ly Lz Ma Mc Md Me Mf Mg Mh Mi Mj Mk Ml Mm Mn Mp Mq Mr Mt Mu Mv Mw My Mz Nd Ne Nf Ng Nh Ni Nk Nm No Nq Nr Ns Nv Nw Nx Ny Oe Oh Om On Oy Oz Pa Pb Pc Pd Pe Pg Pz Qb Qc) Lv(Fr Hq Hr Hu Hv Hx Ii Ik Il In Io Ip Iq Ir Iu Jg Jh Jk Jl Jn Jq Jr Js Jt Lh Li Lj Lw Ly Lz Ma Mc Md Me Mf Mg Mh Mi Mj Mk Ml Mm Mn Mp Mq Mr Mt Mu Mv Mw Mz Na Nb Nd Ng Nh Ni Nk Nm No Nq Nr Ns Nv Nx Ny Oe Oh Oi Om Oz Pa Pb Pc Pd Pe Pf Pg Po Pz Qb Qc) Mg(Fr Hq Hr Hu Hv Hx Ii Ij Ik Il In Io Ip Iq Ir Iu Jh Jk Jl Jm Jn Jq Jr Js Jt Lh Li Lj Lw Ly Lz Ma Mc Md Me Mf Mh Mi Mj Mk Ml Mm Mn Mp Mq Mr Mu Mv Mw Mz Na Nb Nd Ng Ni Nk Nm No Nq Nr Ns Nv Nw Nx Ny Oe Oh Oi Om Oz Pa Pb Pc Pd Pe Pf Pg Po Pz Qb Qc) Ir(Fr Hq Hu Hv Hx Ij Ik Il In Io Ip Iq Is It Iu Jg Jh Jk Jl Jn Jq Jr Js Jt Lh Li Lj Lw Ly Lz Ma Mc Md Me Mf Mh Mi Mj Mk Ml Mm Mn Mp Mq Mr Mt Mu Mv Mw Mz Na Nb Nd Ng Nh Ni Nk Nm No Nq Nr Ns Nv Ny Oe Oh Oi Om Oz Pa Pb Pc Pd Pe Pf Pg Po Pz Qb Qc) Qc(Hq Hr Hu Hv Hx Ii Ik Il In Io Ip Iq Is Iu Jg Jh Jk Jl Jn Jq Jr Js Jt Lh Li Lj Lw Ly Lz Ma Mc Md Me Mf Mh Mi Mj Mk Ml Mm Mn Mp Mq Mr Mt Mu Mv Mw My Mz Nc Nd Ne Ng Nh Ni Nm Nq Nr Ns Nv Nw Nx Ny Oe Oh Om On Oz Pa Pb Pc Pd Pe Po Pz Qa Qb Qe) Oe(Fr Hq Hu Hv Hx Ii Ij Ik Il In Io Ip Iq Iu Jg Jh Jk Jl Jm Jn Jq Jr Js Jt Lh Li Lj Lw Ly Lz Ma Mc Md Me Mf Mh Mi Mj Mk Ml Mm Mn Mp Mq Mr Mu Mv Mw Mz Na Nb Nd Ng Ni Nk Nm No Nq Nr Ns Nv Nw Nx Ny Oh Oi Om Oz Pa Pb Pc Pd Pe Pf Pg Po Pz) Me(Fr Hq Hu Hv Hx Ii Ij Ik Il In Io Ip Iq Iu Jg Jh Jl Jn Jr Js Jt Lh Li Lj Lw Ly Lz Ma Mc Md Mf Mh Mi Mj Mk Ml Mm Mn Mp Mq Mr Mu Mv Mw Mz Na Nb Nd Ne Ng Nh Ni Nk Nm No Nq Nr Ns Nv Nx Ny Oh Oi Om Oz Pa Pb Pc Pd Pe Pf Pg Po Pz Qb) Mf(Fr Hq Hr Hu Hx Ii Ik Il In Io Ip Iq Is Iu Jg Jh Jl Jn Jr Js Jt Lh Lj Lw Ly Lz Ma Mc Md Mh Mi Mj Mk Ml Mm Mn Mp Mq Mr Mt Mu Mv Mw Mz Na Nb Nd Ne Ng Nh Ni Nk Nm No Nq Nr Ns Nv Nx Ny Oh Oi Om Oz Pa Pb Pc Pd Pe Pf Pg Pz Qa Qb) Mq(Fr Hq Hr Hx Ii Ik Il In Io Ip Iq Is Iu Jg Jh Jl Jn Jr Js Jt Lh Lw Ly Lz Ma Mc Md Mh Mi Mj Mk Ml Mm Mn Mp Mr Mt Mu Mv Mw Mz Na Nb Nc Nd Ne Ng Nh Ni Nk Nm No Nq Nr Ns Nv Nw Nx Ny Oh Oi Om On Oz Pa Pb Pc Pd Pe Pz Qa Qb Qe) Mr(Fr Hq Hr Hu Hx Ik Il In Io Ip Iq Is Iu Jg Jh Jl Jn Jr Js Jt Lh Lj Lw Ly Lz Ma Mc Md Mi Mj Mk Ml Mm Mn Mp Mt Mu Mv Mw Mz Na Nb Nd Ne Ng Nh Ni Nk Nm No Nq Nr Ns Nv Nw Nx Ny Oh Oi Om On Oz Pa Pb Pc Pd Pe Po Pz Qa Qb Qe) Nd(Fr Hq Hr Hx Ii Ik Il In Io Ip Iq Is Iu Jg Jh Jl Jn Jr Js Jt Lw Ly Lz Ma Mc Md Mh Mi Mj Mk Ml Mm Mn Mp Mt Mu Mv Mw Mz Na Nb Nc Ne Ng Nh Ni Nk Nm No Nq Nr Ns Nv Nw Nx Ny Oh Oi Om On Oz Pa Pb Pc Pd Po Pz Qa Qb Qe) In(Fr Hq Hr Hu Hv Hx Ii Ij Ik Il Io Ip Iq Iu Jg Jh Jl Jm Jq Jr Js Jt Lh Li Lj Lw Ly Lz Ma Mc Md Mh Mi Mj Mk Ml Mm Mn Mp Mu Mv Mw Mz Na Nb Ng Nh Ni Nk Nm No Nq Nr Ns Nv Ny Oh Oi Om Oz Pa Pb Pc Pd Pe Pf Pg Po Pz) Qb(Fr Hq Hu Hv Hx Ij Ik Io Ip Is Jh Jk Jl Jm Jn Jq Jr Js Jt Lh Li Lj Lw Ly Lz Ma Mc Md Mi Mj Mk Ml Mm Mn Mp Mt Mu Mv Mw Mz Na Nb Ng Nh Nk Nm No Nq Nr Ns Nv Nw Nx Ny Oh Oi Om On Oz Pa Pc Pd Pe Pf Pg Po Pz Qa Qe) Jg(Fr Hq Hu Hv Hx Ij Ik Il Io Ip Iq Is Iu Jk Jl Jm Jq Jr Js Jt Lh Li Lj Lw Ly Lz Ma Mc Md Mi Mj Mk Ml Mm Mn Mp Mt Mu Mv Mz Na Nb Nh Ni Nk Nm No Nq Nr Ns Nv Nw Nx Ny Oh Oi Om On Oz Pa Pb Pc Pd Pe Pf Pg Po Pz) Pb(Fr Hq Hr Hu Hv Hx Ii Ij Ik Il Io Ip Iq Iu Jh Jk Jl Jm Jn Jq Jr Js Jt Lh Li Lj Lw Ly Lz Ma Mc Md Mh Mi Mj Mk Ml Mm Mn Mp Mu Mv Mw Na Nb Ng Ni Nk Nm No Nq Nr Ns Nv Ny Oh Oi Om Oz Pa Pc Pd Pe Pf Pg Po Pz) Ng(Fr Hq Hr Hv Hx Ii Ij Ik Il Io Ip Iq Iu Jh Jk Jl Jn Jq Jr Js Jt Lh Li Lj Ly Lz Ma Mc Md Mh Mi Mj Mk Ml Mm Mn Mu Mv Mw My Mz Na Nb Ni Nk Nm No Nq Nr Ns Nv Nx Ny Oh Oi Om Oy Oz Pa Pc Pd Pe Pf Pg Pz) Lw(Fr Hq Hu Hv Hx Ij Ik Il Io Ip Iq Iu Jh Jk Jl Jm Jn Jq Jr Js Jt Lh Li Lj Ly Lz Ma Mc Md Mh Mi Mj Mk Ml Mm Mn Mp Mu Mv Mw Na Nb Ni Nk Nm No Nq Nr Ns Nv Nx Ny Oh Oi Om Oz Pa Pc Pd Pe Pf Pg Po Pz) Mp(Fr Hq Hu Hv Hx Ij Ik Il Io Ip Iq Iu Jh Jk Jl Jm Jn Jq Jr Js Jt Lh Li Lj Ly Lz Ma Mc Md Mh Mi Mj Mk Ml Mm Mn Mu Mv Mw Mz Na Nb Nk Nm No Nq Nr Ns Nv Nx Ny Oh Oi Om Oz Pa Pc Pd Pe Pf Pg Po Pz) Ni(Fr Hq Hu Hv Hx Ii Ij Ik Il Io Ip Iq Iu Jh Jl Jn Jq Jr Js Jt Lh Li Lj Ly Lz Ma Mc Md Mh Mi Mj Mk Ml Mm Mn Mu Mv Mw Mz Na Nb Nh Nk Nm No Nq Nr Ns Nv Ny Oh Oi Om Oz Pa Pc Pd Pe Pf Pg Po Pz) Jn(Fr Hq Hu Hv Hx Ij Ik Io Ip Iq Is It Iu Jh Jk Jl Jm Jq Jr Js Jt Lh Li Lj Ly Lz Ma Mc Md Mi Mj Mk Ml Mm Mn Mu Mv Mw Mz Na Nb Nk No Nq Nr Ns Nv Nx Ny Oh Oi Om Oz Pa Pc Pd Pe Pf Pg Po Pz) Nm(Fr Hq Hu Hv Hx Ij Ik Il Io Ip Iq Iu Jh Jk Jl Jm Jq Jr Js Jt Lh Li Lj Ly Lz Ma Mc Md Mh Mi Mj Mk Ml Mm Mn Mu Mv Mw Na Nb Nk No Nq Nr Ns Nv Ny Oh Oi Om Oz Pa Pc Pd Pe Pf Pg Po Pz) Nh(Fr Hq Hu Hv Hx Ij Il Io Ip Iq Jh Jk Jl Jm Jq Jr Js Jt Lh Li Lj Ly Lz Ma Mc Md Mi Mj Mk Ml Mm Mn Mu Mv Mw Na Nb Nc Ne Nk No Nq Nr Ns Nv Ny Oh Oi Om Oz Pa Pc Pd Pe Pf Pg Po Pz) Ik(Fr Hq Hr Hu Hv Hx Ij Il Io Ip Iq Iu Jh Jl Jq Jr Js Jt Lh Li Lj Ly Lz Ma Mc Md Mh Mi Mj Mk Ml Mm Mn Mu Mv Mw Mz Na Nb Nk No Nq Nr Ns Nv Nx Ny Oh Oi Om Oz Pa Pc Pd Pe Pf Pg Pz) Iq(Fr Hq Hu Hx Ii Ij Il Io Ip Iu Jh Jl Jq Jr Js Jt Lh Li Lj Ly Lz Ma Mc Md Mh Mi Mj Mk Ml Mm Mn Mu Mv Mw Mz Na Nb Nk No Nq Nr Ns Nv Nx Ny Oh Oi Om Oz Pa Pc Pd Pe Pf Pg Pz) Iu(Fr Hq Hu Hv Hx Ii Ij Il Io Ip Is Jh Jl Jr Js Jt Lh Li Lj Ly Lz Ma Mc Md Mh Mi Mj Mk Ml Mm Mn Mu Mv Mw Mz Na Nb Nk No Nq Nr Ns Nv Ny Oh Oi Om Oz Pa Pc Pd Pe Pf Pg Pz) Js(Hq Hu Hv Hx Ij Io Ip Is It Jh Jk Jl Jr Jt Lh Li Lj Ly Lz Ma Mc Md Mi Mk Ml Mm Mn Mt Mu Mv Mw Mz Na Nb Nc Ne No Nq Nr Ns Nv Nw Nx Ny Oh Om On Oz Pa Pc Pd Po Pz Qa) Mh(Fr Hq Hu Hv Hx Ij Il Io Ip Jh Jk Jl Jq Jr Jt Lh Li Lj Ly Lz Ma Mc Md Mi Mj Mk Ml Mm Mn Mu Mv Mw Na Nb Nk No Nq Nr Ns Nv Ny Oh Oi Om Oz Pa Pc Pd Pe Pf Pg Po Pz) Nx(Fr Hq Hu Hv Hx Ij Io Ip Jh Jk Jl Jm Jq Jr Jt Lh Li Lj Ly Lz Ma Mc Md Mi Mj Mk Ml Mm Mn Mu Mv Mw Na Nb Nk No Nq Nr Ns Nv Ny Oh Oi Om Oz Pa Pc Pd Pe Pf Pg Po Pz) Il(aA Fr Hq Hr Hv Hx Ii Ij Io Ip Jh Jl Jr Jt Lh Li Lj Ly Lz Ma Mc Md Mi Mj Mk Ml Mm Mn Mu Mv Mw Na Nb Nk No Nq Nr Ns Nv Ny Oh Oi Om Oz Pa Pc Pd Pe Pf Pg Pz) Oz(Hq Hr Hx Ii Io Ip Is Jh Jr Jt Ly Lz Ma Mc Md Mi Mj Mk Ml Mm Mn Mt Mu Mv Mw My Mz Na Nb Nc Ne Nk No Nq Nr Ns Nv Nw Ny Oh Om On Pa Pc Pd Pf Po Pz Qa Qe) Ne(Fr Hq Hu Hv Hx Ij Jh Jk Jl Jm Jq Jr Jt Lh Li Lj Ly Lz Ma Mc Md Mi Mj Ml Mm Mn Mu Mv Na Nb Nc Nk No Nq Nr Ns Nv Ny Oh Oi Pa Pc Pd Pe Pf Pg Po Pz) Io(Fr Hq Hr Hu Hx Ii Ip Is Jh Jl Jr Jt Lh Lj Ly Lz Ma Mc Md Mi Mj Mk Ml Mm Mn Mu Mv Mw Mz Na Nb Nk No Nq Nr Ns Nv Ny Oh Oi Om Pa Pc Pd Pe Pf Pg Pz) Ip(Fr Hq Hu Hx Is Jh Jl Jr Jt Lh Lj Ly Lz Ma Mc Md Mi Mj Mk Ml Mm Mn Mt Mu Mv Mw Mz Na Nb Nk No Nq Nr Ns Nv Ny Oh Oi Om Pa Pc Pd Pe Pf Pg Pz Qa) Hr(Fr Hq Hu Hv Hx Ij Jh Jk Jm Jq Jr Jt Lh Li Lj Ly Lz Ma Mc Md Mi Mj Mk Ml Mn Mu

Figure 31 Continued

Mv Mw Na Nb Nk No Nq Ns Ny Oh Oi Om Pa Pc Pd Pe Pf Pg Po Pz) Is(Fr Hq Hu Hv Hx Ij Jh Jk Jl Jm Jq Jr Jt Lh Li Lj Ly Lz Ma Mc Md Mi
Mk Ml Mm Mn Mu Na Nb Nk No Nq Nr Ns Nv Ny Oh Oi Pa Pc Pd Pe Pf Pg Po Pz) Nc(Fr Hq Hu Hv Hx Ij Jh Jk Jl Jm Jq Jr Jt Lh Li Lj Ly Lz
Ma Mc Md Mi Mj Ml Mm Mn Mu Na Nb No Nq Nr Ns Nv Ny Oh Oi Pa Pc Pd Pe Pf Pg Po Pz) Mw(Fr Ii Ij Jh Jk Jl Jq Jr Jt Lh Li Lj Ly Lz Ma
Mc Md Mi Mj Mk Ml Mm Mn Mv My Na Nb Nk No Nq Nr Ns Ny Oh Oi Om Oy Pa Pc Pd Pe Pf Pg Pz) Mz(Fr Hq Hu Hv Ij Jh Jk Jl Jm Jq Jr Jt
Lh Li Lj Ly Lz Ma Mc Md Mi Mj Mk Mm Mn Mu Na Nb Nk No Nq Nr Ns Nv Oh Oi Pa Pc Pd Pe Pf Pg Po Pz) Mt(Fr Hq Hu Hv Hx Ij Jk Jl Jm
Jq Jr Jt Lh Li Lj Ly Lz Ma Mc Md Mi Ml Mm Mn Mu Nb Nk No Nr Ns Nv Ny Oh Oi Pa Pc Pd Pe Pf Pg Po Pz) Om(Fr Ii Ij Jh Jl Jq Jr Jt Lh Lj
Ly Lz Ma Mc Md Mi Mj Mk Ml Mm Mn Mu Mv My Na Nb Nk No Nq Nr Ns Nv Ny Oh Oi Pa Pc Pd Pe Pf Pg Pz) My(Fr Hq Hu Hv Hx Ij Jh Jk
Jl Jm Jq Jr Jt Li Lj Lz Ma Mc Md Mj Mk Ml Mm Mn Mv Na Nb Nk No Ns Ny Oh Oi Pa Pc Pd Pf Pg Po Pz) Ii(Fr Hq Hu Hv Hx Ij Jh Jk Jm Jq
Jr Li Lj Ly Lz Ma Mc Md Mj Mk Ml Mn Mu Mv Na Nb Nk No Nq Ns Oh Oi Pa Pc Pd Pf Pg Po Pz) Mv(Fr Ij Jh Jl Jr Jt Lh Ly Lz Ma Mc Md
Mi Mj Mk Ml Mm Mn Mu Na Nb Nk No Nq Nr Ns Nv Ny Oh Oi Oy Pa Pc Pd Pe Pg Pz) Nw(Fr Hq Hu Hv Hx Ij Jk Jl Jm Jq Jr Jt Lh Li Lj Ly
Lz Ma Mc Mi Mm Mn Mu Nk No Nr Ns Nv Oh Oi Pa Pc Pd Pe Pf Pg Pz) Qa(Fr Hu Hv Ij Jl Jm Jq Jr Jt Li Lj Ly Lz Ma Mc Md Mi Ml Mm Mn
Mu Nb Nk No Nr Ns Nv Oh Oi Pa Pc Pd Pe Pf Pg Qe) Nq(Fr Ij Jh Jl Jr Jt Lh Lj Ly Lz Ma Mc Md Mi Mj Mk Ml Mm Mn Mu Na Nb Nk No Nr
Ns Nv Ny Oh Oi Pa Pc Pd Pe Pz) Ny(Fr Jh Jl Jr Jt Lh Ly Lz Ma Mc Md Mi Mj Mk Ml Mm Mn Mu Na Nb Nk No Nr Ns Nv Oh Oi Oy Pa Pc Pd
Pe Pg Pz) Mk(Fr Jh Jl Jr Jt Lh Ly Lz Ma Mc Md Mi Mj Ml Mm Mn Mu Na Nb Nk No Nr Ns Nv Oh Oi Pa Pc Pd Pe Pf Pg) On(Hq Hu Hv Ij Jk
Jl Jm Jq Jr Jt Lh Li Lj Lz Ma Mc Mi Mm Mu Nk No Ns Nv Oh Oi Pa Pc Pd Pe Pf Pg Pz) Mj(Jh Jl Jr Jt Lh Li Ly Lz Ma Mc Md Mi Ml Mm Mn
Mu Na Nb Nk No Nr Ns Nv Oh Oy Pa Pc Pd Pe Pz) Qe(Fr Ij Jl Jm Jq Jr Jt Li Lj Ly Lz Ma Mc Md Mi Ml Mm Mn Mu Nk No Ns Nv Oi Pa Pc
Pd Pe Pf Pg) Ms(Fr Hq Hu Hv Hx Ij Jh Jk Jm Jq Jr Lh Li Lj Md Ml Mm Mn Na Nb Nk No Oh Oi Pc Pe Pf Pg Po) Nv(Fr Hq Hu Hx Jh Lh Ly Lz
Ma Mc Md Mi Ml Mm Mn Mu Na Nb Nk No Nr Ns Oh Oi Pa Pd Po Pz) Ly(Jh Jl Jt Lj Lz Ma Mc Md Mi Ml Mm Mn Mu Na Nb Nk No Nr Ns
Nu Oh Oi Pa Pc Pd) Mb(Fr Hq Hu Hv Hx Ij Jh Jk Jm Jq Jr Lh Li Lj Mc Na Nb Nk Oi Pc Pe Pf Pg Po Pz) Jl(Hq Hu Hv Hx It Jh Jk Jr Jt Lh Lj Lz
Ma Mc Md Ml Mn Nb Nr Ns Pa Pd Po Pz) Pd(Hq Hx Jh Jr Jt Lz Ma Mc Md Mi Ml Mm Mn Mu Nr Ns Oh Pa Pc Pf Pg Po Pz) Oy(Fr Hu Hv Hx
Jm Jq Jr Li Lj Lz Ma Mc Ml Mn Na Nb Nk No Oh Oi Po Pz) Mu(Hu Hx Jh Jr Lz Ma Mc Md Mi Ml Mm Mn Nb Nk No Nr Ns Oh Pa Pz) Jh(Hq
Hu Hx Jq Jr Jt Lh Li Md Mi Mm Nf No Nr Ns Pa Pc Pe Pz) Nu(Fr Hq Hu Hv Ij Jk Jm Jq Jr Lh Li Lj Nk No Pc Pe Pf Pg) Nr(Lh Lz Ma Mc Md
Mi Ml Mm Mn Na Nb Ns Oh Pe Po Pz) Mi(Hx Lz Ma Mc Md Ml Mn Na Nb No Ns Oh Pa Po) It(Hu Hv Jk Jm Jq Jr Jt Li Lj Pe Pf Pg Po) Pa(Hq
Jr Lz Ma Mc Md Ml Mm Mn Ns Oh Pe Pz) Nf(Fr Hq Hu Hv Hx Jk Jm Lj Pf Po) Jp(Jm Jq Mm Nk No Oh Oi Pe Pf Pg) Ma(Lz Mc Md Ml Mm
Mn Nb No Ns) Ml(Lh Mc Mm Mn No Ns Oh Pe) Pz(aA Hq Hv Hx Jr Jt Lh Lj) Fp(Jk Jm Jq Jr Pe Pf Pg) Jt(Hq Hu Hx Jr Na Nb Po) Ns(Lz Mc
Md Mm Mn Oh) Mm(Lz Md Na Nb No) Pe(Hx Lz Md Nb Po) aA(Hv Ij Jk Jm Jq) Jr(Hq Hv Hx Po) Lh(Hx Md Nb Po) Mc(Lz Mn Oh) No(Na
Oh) PoLi NaNb] Nt{Na(Fr Hq Hr Hu Hv Hw Hx Ih Ii Ij Il Io Ip Iq Ir It Iu Jg Jh Jk Jl Jm Jn Jo Jq Jr Js Jt Lh Li Lj Lu Lv Lw Lx Ly Lz Mb Mc
Md Me Mf Mg Mh Mi Mj Mk Ml Mm Mn Mp Mq Mr Ms Mt Mu Mv Mw Nb Nc Nd Ne Nf Ng Nh Ni Nl Nm Nn No Nq Nr Ns Nu Nv Nx Ny
Oe Oh Oi Om Oz Pa Pb Pc Pd Pe Pf Pg Po Pz Qb Qc) Lj(Fp Fr Hq Hr Hu Hv Hw Hx Ih Ii Ij Il Io Ip Iq Ir It Iu Jg Jh Jk Jl Jm Jn Jo Jq Jr Js Jt Lh
Li Lu Lv Lx Ly Lz Ma Mb Mc Md Me Mf Mg Mh Mi Mj Mk Ml Mm Mn Mp Mq Mr Ms Mt Mu Mv Mw My Nb Nc Nd Ne Ng Nh Ni Nk Nm
Nn No Nq Nr Ns Nu Nv Ny Oe Oh Oi Om Oz Pa Pb Pc Pd Pe Pf Pg Po Pz Qb Qc) Fr(Fp Hq Hr Hu Hv Hw Hx Ih Ii Ij Il Io Ip Iq Ir It Iu Jg Jh Jk Jl
Jm Jn Jo Jq Jr Js Jt Lh Li Lu Lv Lw Lx Ly Lz Ma Mb Mc Md Me Mf Mg Mh Mi Mj Ml Mm Mn Mp Mq Mr Ms Mt Mu Mv Mw Nb Nc Nd Ne
Nh Ni Nk Nm Nn No Nq Nr Ns Nu Nv Nx Ny Oe Oh Oi Om Oz Pa Pb Pc Pd Pe Pf Pg Po Pz Qb Qc) Nn(Fp Hq Hr Hu Hv Hw Hx Ih Ii Il Io Ip
Iq Ir It Iu Jg Jh Jk Jl Jm Jn Jo Jq Jr Js Jt Lh Li Lu Lv Lw Lx Ly Lz Ma Mb Mc Md Me Mf Mg Mh Mi Mj Ml Mm Mn Mp Mq Mr Ms Mt Mu Mv
Nb Nc Nd Ne Ng Nh Ni Nk Nm No Nq Nr Ns Nu Nv Nx Ny Oe Oh Oi Om Oz Pa Pb Pc Pd Pe Pf Pg Po Pz Qb Qc) Ih(Fp Hq Hr Hu Hv Hw Hx
Ii Ij Il Io Ip Iq Ir It Iu Jg Jh Jk Jl Jm Jn Jo Jq Jr Js Jt Lh Li Lu Lv Lx Ly Lz Ma Mb Mc Md Me Mf Mg Mh Mi Mj Ml Mm Mn Mp Mq Mr Mt Mu
Mv Mw Nb Nc Nd Ne Ng Nh Ni Nk Nm No Nq Nr Ns Nu Nv Nx Ny Oe Oh Oi Om Oz Pa Pb Pc Pd Pe Pf Pg Po Pz Qb Qc) Mp(Hq Hr Hu Hv
Hw Hx Ii Ij Il Io Ip Iq It Iu Jh Jk Jl Jm Jn Jo Jq Jr Js Jt Lh Li Lu Lv Lx Ly Lz Ma Mb Mc Md Me Mf Mg Mh Mi Mj Ml Mm Mn Mq Mr Ms
Mt Mu Mv Mw Nb Nc Nd Ne Ng Nh Ni Nk Nm No Nq Nr Ns Nu Nv Ny Oe Oh Oi Om Oz Pa Pb Pc Pd Pe Pf Pg Po Pz Qb Qc) Qc(Fp Hq Hr
Hu Hv Hw Hx Ii Ij Io Ip Iq Ir It Iu Jh Jk Jl Jm Jn Jo Jq Jr Js Jt Lh Li Lu Lv Lx Ly Lz Ma Mb Mc Md Me Mf Mg Mh Mi Mj Ml Mm Mn Mq Mr
Ms Mt Mu Mv Mw Nb Nc Nd Ne Ng Nh Ni Nk Nm No Nq Nr Ns Nu Nv Ny Oe Oh Oi Om Oz Pa Pb Pc Pd Pe Pf Pg Po Pz Qb) Jq(Hq Hr Hu
Hv Hw Hx Ij Il Io Ip Iq Ir It Iu Jg Jh Jk Jl Jm Jn Jr Js Jt Lh Li Lu Lv Lx Ly Lz Ma Mb Mc Md Me Mf Mg Mi Mj Mk Ml Mm Mn Mq Mr Mt
Mu Mv Mw Nb Nc Nd Ne Ng Nh Ni Nk Nm No Nq Nr Ns Nu Nx Ny Oe Oh Oi Om Oz Pa Pb Pc Pd Pe Pf Pg Po Pz Qb) Li(Fp Hq Hr Hu
Hv Hw Hx Ii Il Io Ip Iq Ir It Iu Jg Jh Jk Jl Jm Jn Jo Jr Js Jt Lh Lu Lv Lx Ly Lz Ma Mb Mc Md Me Mf Mg Mi Mj Ml Mm Mn Mq Mr Ms Mt Mu
Mv Mw Nb Nc Nd Ne Ng Nh Ni Nk Nm No Nq Nr Ns Nu Nv Ny Oe Oh Oi Om Oz Pa Pb Pc Pd Pe Pf Pg Po Pz Qb) Mm(Hq Hr Hu Hv Hw Hx
Ii Ij Il Io Ip Iq Ir It Iu Jg Jh Jk Jl Jm Jo Jr Js Jt Lh Lu Lv Lw Lx Ly Lz Ma Mb Mc Md Me Mf Mg Mh Mi Mj Ml Mn Mq Mr Ms Mt Mu Mv Mw
Nb Nc Nd Ne Nh Ni Nk Nm No Nq Nr Ns Nu Nv Ny Oe Oh Oi Om Oz Pa Pb Pc Pd Pe Pf Pg Po Pz) Nh(Hr Hu Hw Hx Ii Ij Il Io Ip Iq Ir It Iu Jg
Jh Jl Jm Jn Jo Jr Js Jt Lh Lu Lv Lw Lx Ly Lz Ma Mb Mc Md Me Mf Mg Mh Mi Mj Mk Ml Mn Mq Mr Ms Mt Mu Mv Mw Nb Nc Nd Ne Ng Ni
Nk Nm No Nq Nr Ns Nu Nv Nx Ny Oe Oh Oi Om Oz Pa Pb Pc Pe Po Pz Qb) Pb(Hq Hr Hu Hv Hw Hx Ii Ij Ik Il Io Ip Iq Ir It Iu Jh Jk Jl Jm
Jo Jr Js Jt Lu Lv Lw Lx Ly Lz Ma Mb Mc Md Me Mf Mg Mh Mi Mj Mk Ml Mn Mq Mr Ms Mt Mu Mv Mw My Nb Nc Nd Ne Nf Ng Ni Nm
No Nq Nr Ns Nu Nv Ny Oe Oh Oi Om Oz Pc Pd Pe Po Pz) Pa(Fp Hq Hr Hu Hv Hw Hx Ij Il Io Ip Iq It Iu Jh Jk Jl Jm Jn Jo Jr Js Jt Lh Lu Lv Lx
Ly Lz Ma Mb Mc Md Me Mf Mg Mh Mi Mj Ml Mn Mq Mr Ms Mt Mu Mv Mw Nb Nc Nd Ne Ng Ni Nk Nm No Nq Nr Ns Nu Nv Ny Oe Oh Oi
Om Oz Pc Pe Pf Pg Po Pz Qb) Ne(Hq Hr Hu Hv Hw Hx Ii Ij Il Io Ip Iq Iu Jh Jk Jl Jm Jo Jr Js Lh Lu Lv Lx Ly Lz Ma Mb Mc Md Me Mf Mg Mh
Mi Mj Ml Mn Mq Mr Ms Mt Mu Mv Mw Nb Nc Nd Ng Ni Nk Nl Nm No Nq Nr Ns Nu Nv Ny Oe Oh Oi Om Oz Pc Pd Pe Pf Pg Po Pz) Lh(Fp
Hq Hr Hu Hv Hw Ij Il Io Ip Iq Ir It Iu Jg Jh Jk Jl Jm Jn Jo Jr Js Jt Lu Lv Lw Lx Ly Lz Ma Mb Mc Md Me Mf Mg Mi Mj Ml Mn Mq Mr Ms Mt
Mu Nc Nd Ng Ni Nk Nm No Nq Nr Ns Nu Nv Nx Oe Oh Oi Om Oz Pc Pd Pe Pf Pg Pz Qb) Ny(Hq Hr Hu Hv Hw Hx Ij Io Ip Iq Ir It Iu Jg Jh Jk
Jl Jm Jn Jr Js Jt Lu Lv Lx Ly Lz Ma Mb Mc Md Me Mf Mg Mh Mi Mj Ml Mn Mq Mr Ms Mt Mu Mv Mw Nb Nc Nd Ni Nk Nm No Nq Nr Ns
Nu Nv Nx Oe Oh Oi Om Oz Pc Pd Pe Pf Pg Po Pz) Oe(Hq Hr Hu Hv Hw Hx Ii Ij Il Io Ip Iq It Iu Jh Jk Jl Jm Jo Jr Jt Lu Lv Ly Lz Ma Mb Mc
Md Me Mf Mg Mh Mi Mj Ml Mn Mq Mr Ms Mu Mv Mw Nb Nc Nd Nf Ng Ni Nk Nl Nm No Nq Nr Ns Nu Oh Oi Om Oz Pc Pd Pe Pf Pg Po
Pz) Ms(Hq Hr Hu Hv Hw Hx Ii Ij Il Io Ip Iq It Iu Jh Jk Jl Jm Jo Jr Lu Lv Lx Ly Lz Ma Mb Mc Md Me Mf Mg Mh Mi Mj Mk Ml Mn Mq Mr Mu
Mv Mw My Nb Nc Nd Ng Ni Nk Nm No Nq Nr Ns Nu Oh Oi Om Oz Pc Pd Pe Pf Pg Po Pz) Mt(Hq Hr Hu Hv Hw Hx Ij Il Io Ip Iq Ir Iu Jg Jh Jk
Jl Jm Jo Jr Js Jt Lu Lv Lx Ly Lz Ma Mb Mc Md Me Mf Mg Mi Mj Ml Mn Mq Mr Mu Mv Nb Nc Nd Ni Nk Nm No Nq Nr Ns Nu Nv Oi Om
Oz Pc Pd Pe Pf Pg Po Pz Qb) Nc(Hq Hr Hu Hv Hw Hx Ii Ij Il Io Iq It Iu Jh Jk Jl Jm Jo Jr Js Lu Lv Ly Lz Ma Mb Mc Md Me Mf Mg Mh Mi Mj
Ml Mn Mq Mr Mu Mv Mw Nb Nd Ng Ni Nk Nl Nm No Nq Nr Ns Nu Nv Oh Oi Om Oz Pc Pd Pe Pf Pg Po Pz) Ip(Hq Hr Hu Hv Hw Hx Ij Io Iq
Ir It Iu Jg Jh Jk Jl Jm Jn Jr Js Jt Lu Lv Lx Ly Lz Ma Mb Mc Md Me Mf Mg Mi Mj Ml Mn Mq Mr Mu Mv Mw Nb Nd Ng Ni Nk Nm No Nq Nr
Ns Nu Nv Oh Oi Om Oz Pc Pd Pe Pf Pg Po Pz) Ng(Hr Hu Hw Hx Ii Ij Il Io Iq It Iu Jh Jk Jl Jm Jo Jr Js Lu Lv Ly Lz Ma Mb Mc Md Me Mf Mg

Figure 31 Continued

Mh Mi Mj Mk Ml Mn Mq Mr Mu Mv Mw My Nb Nd Nf Ni Nk Nl Nm No Nq Nr Ns Nu Oh Oi Om Oy Oz Pc Pd Pe Po Pz) Mh(Hq Hr Hu Hv
Hw Hx Ii Ij Il Io Iq Iu Jh Jk Jm Jo Jr Lu Lv Ly Lz Ma Mb Mc Md Me Mf Mg Mi Mj Mk Ml Mn Mq Mr Mu Mv Mw My Nb Nd Nf Ni Nk Nm
No Nq Nr Ns Nu Oh Oi Om Oz Pc Pd Pe Pf Pg Po Pz) Nv(Hq Hr Hu Hv Hw Hx Ij Io Iq Ir Iu Jg Jk Jl Jm Jn Jr Js Jt Lu Lv Lx Ly Lz Ma Mb Mc
Md Me Mf Mg Mi Mj Ml Mn Mq Mr Mu Nb Nd Ni Nk Nm No Nq Nr Ns Nu Nx Oh Oi Om Oz Pc Pd Pe Pf Pg Po Pz Qb) Mv(Hr Hu Hw Hx Ii
Ij Ik Il Io Iq Ir It Iu Jh Jn Jo Jr Jt Lu Lv Lw Ly Lz Ma Mb Mc Md Me Mf Mg Mi Mj Mk Ml Mn Mq Mr Mu Mw My Nd Nf Ni Nl Nm No Nq Nr
Ns Nu Oh Oi Om Oy Pc Pd Pe Po Pz) Js(Hq Hr Hu Hv Hw Hx Ij Io Iq Ir Iu Jh Jk Jl Jm Jn Jr Jt Lu Lv Lx Ly Lz Ma Mb Mc Md Me Mf Mg Mi
Ml Mn Mq Mr Mu Nb Nd Ni Nk Nm No Nq Nr Ns Nu Nx Oh Oi Om Oz Pc Pd Pe Pf Pg Po Pz Qb) Mw(Hr Hu Hv Hw Hx Ii Ij Il Io Iq It Iu Jh
Jk Jm Jo Jr Lu Lv Ly Lz Ma Mb Mc Md Me Mf Mg Mi Mj Mk Ml Mn Mq Mr Mu My Nb Nd Nf Ni Nk Nl Nm No Nq Nr Ns Nu Oh Oi Om Oz
Pc Pd Pe Po Pz) Ii(Hq Hr Hu Hv Hw Hx Ij Il Io Iq Iu Jh Jk Jm Jo Jr Lu Lv Ly Lz Ma Mb Mc Md Me Mf Mg Mi Mj Mk Ml Mn Mq Mu My Nb
Nd Nf Ni Nk Nm No Nq Nr Ns Nu Oh Oi Om Oy Oz Pc Pd Pf Pg Po Pz) It(Hq Hr Hu Hv Hw Hx Ij Io Iq Ir Iu Jh Jk Jl Jm Jn Jo Jr Lu Lv Ly Lz
Ma Mb Mc Md Me Mf Mg Mi Mj Ml Mn Mq Mr Mu Nb Nd Ni Nk Nm No Nq Nr Ns Nu Oh Oi Om Oz Pc Pd Pe Pf Pg Po Pz) Lx(Hq Hr Hu
Hv Hw Hx Ij Io Iq Iu Jg Jk Jl Jm Jo Jr Jt Lu Lv Ly Lz Ma Mb Mc Md Me Mf Mg Mi Mj Ml Mn Mq Mr Mu Nb Nd Ni Nk Nm No Nq Nr Ns Nu
Oh Oi Om Oz Pc Pd Pe Pf Pg Pz Qb) Il(Hr Hu Hv Hw Hx Ij Io Iq Iu Jg Jh Jm Jo Jr Lu Lv Lw Ly Lz Ma Mb Mc Md Me Mf Mg Mi Mj Mk Ml
Mn Mq Mr Mu My Nb Nd Nf Ni Nk Nm No Nq Nr Ns Nu Oh Oi Om Oz Pc Pd Pe Pf Po Pz) Ir(Hq Hr Hu Hv Hw Hx Ij Io Iq Jh Jk Jl Jm Jn Jr Jt
Lu Lv Ly Lz Ma Mb Mc Md Me Mf Mg Mi Mj Ml Mn Mq Mr Mu Nb Nd Ni Nk Nm No Nq Nr Ns Nu Oh Oi Om Oz Pc Pd Pe Pf Pg Po Pz)
Mk(Hq Hr Hu Hv Hw Hx Ij Io Iq Iu Jh Jk Jm Jo Jr Lu Lv Ly Lz Ma Mb Mc Md Me Mf Mg Mi Mj Ml Mn Mq Mr Mu Nb Nd Ni Nk Nm No Nq
Nr Ns Nu Oh Oi Om Oz Pc Pd Pe Pf Pg Po Pz) Lw(Hq Hu Hv Hw Hx Ij Io Iq Iu Jk Jm Jo Jr Jt Lu Lv Ly Lz Ma Mb Mc Md Me Mf Mg Mi Mj
Ml Mn Mq Mr Mu Nb Nd Ni Nk Nm No Nq Nr Ns Nu Oh Oi Om Oz Pc Pd Pe Pf Pg Po Pz) Jn(Hq Hr Hu Hv Hw Hx Ij Io Iq Iu Jh Jk Jm Jr Lu
Lv Ly Lz Ma Mb Mc Md Me Mf Mg Mi Mj Ml Mn Mq Mr Mu Nb Nd Ni Nk Nm No Nq Nr Ns Nu Oh Oi Om Oz Pc Pd Pe Pf Pg Po Pz) Nx(Hq
Hr Hu Hv Hw Hx Ij Io Iq Iu Jh Jk Jm Jr Lu Lv Ly Lz Ma Mb Mc Md Me Mf Mg Mi Mj Ml Mn Mq Mr Mu Nb Nd Ni Nk Nm No Nq Nr Ns Nu
Oh Oi Om Oz Pc Pd Pe Pf Pg Po Pz) Jl(Hq Hu Hv Hw Ij Io Iq Iu Jh Jk Jm Jo Jr Jt Lu Lv Ly Lz Ma Mb Mc Md Me Mf Mg Mi Mj Ml Mn Mq
Mr Mu Nb Nd Ni Nk Nm No Nq Ns Nu Oh Oi Om Oz Pc Pd Pe Pf Pg Pz Qb) Nf(Hq Hr Hu Hv Hw Hx Io Iq Iu Jh Jk Jm Jo Jr Lu Lv Lz Ma Mb
Mc Md Me Mf Mg Mi Mj Ml Mn Mq Mu Nb Nd Ni Nk Nm No Nq Nr Ns Nu Oh Oi Om Oz Pc Pd Pe Pf Pg Po Pz) Nl(Hq Hr Hu Hv Hw Hx Ij
Io Iq Iu Jh Jk Jm Jo Jr Lu Lv Lz Ma Mb Mc Md Me Mf Mg Mi Mj Ml Mn Mq Mr Mu Nb Nd Ni Nm Nq Nr Ns Nu Oh Oi Om Oz Pc Pd Pe Pf
Pg Po Pz) Jg(Hq Hr Hu Hv Hw Hx Ij Io Iq Iu Jk Jm Jr Jt Lu Lv Ly Lz Ma Mb Mc Md Me Mf Mi Mj Ml Mn Mq Mr Mu Nb Nd Ni Nk Nm No
Nq Nr Ns Nu Oh Oi Om Oz Pc Pd Pe Pf Pg Po) Ik(Hq Hr Hu Hv Hw Hx Io Iq Jh Jk Jm Jo Jr Lu Lv Ly Lz Ma Md Me Mf Mg Mi Mj Ml Mn Mq
Mr Mu Nb Nd Ni Nk Nm No Nq Nr Ns Nu Oh Oi Om Oz Pc Pd Pe Pf Pg Po Pz) Qb(Hq Hu Hv Ij Io Iq Jk Jm Jo Jr Lu Lv Ly Lz Ma Mb Mc Md
Me Mf Mg Mi Ml Mn Mq Mr Mu Nb Nd Ni Nk Nm No Nq Nr Ns Nu Oh Oi Om Oz Pc Pd Pe Pf Pg Po Pz) Jt(Hq Hu Hv Hw Hx Ij Io Iq Jk Jm
Jr Lu Lv Ly Lz Ma Mb Mc Md Me Mf Mg Mi Ml Mn Mq Mr Mu Nb Nd Ni Nm No Nq Nr Ns Nu Oh Oi Om Oz Pc Pd Pe Pf Pg Po Pz) Fp(Hq
Hu Hv Hw Ij Io Iq Jk Jm Jo Jr Lu Lv Lz Ma Mb Md Me Mf Mg Mi Ml Mn Mq Mr Mu Nb Nd Ni Nk No Nq Nr Ns Nu Oh Oi Om Oz Pc Pd Pe
Pf Pg Po Pz) My(Hq Hr Hu Hv Hw Hx Io Iq Iu Jk Jm Jo Jr Lu Lv Ly Lz Ma Mb Mc Md Mg Mi Mj Ml Mn Mq Nb Nd Ni Nk Nq Nr Ns Nu Oh
Oi Om Oz Pc Pd Pe Pf Pg Po Pz) Jh(Hr Hu Hv Hw Hx Ij Io Iq Iu Jk Jo Jr Lu Lv Ly Mb Mc Md Me Mf Mg Mi Mj Ml Mn Mq Mr Mu Nb Nd
Nm No Nq Nr Nu Oi Pc Pd Pe Po Pz) Mc(Hr Hu Hw Hx Ij Io Iq Iu Jo Lu Lv Ly Lz Mb Md Me Mf Mg Mi Mj Ml Mn Mq Mx Nb Nd Ni Nm No
Nq Nr Nu Oi Om Pc Pd Po Pz) Mx(Hq Hv Ij Io Iq Jk Jm Lu Lv Lz Ma Mb Me Mf Mg Mi Mn Mq Mr Mu Nb Nd Ni Nk Nq Ns Nu Oh Oi Om
Oz Pc Pe Pf Pg Pz) No(Hr Hu Hw Hx Io Iq Iu Jo Jr Lu Lv Ly Lz Mb Md Me Mf Mg Mj Ml Mq Mz Nb Nd Ni Nm Nq Nr Nu Oi Om Pc Pd Po
Pz) Ly(Hr Hu Hv Hw Hx Io Iq Iu Jm Jo Jr Lu Lv Mb Md Me Mf Mg Mj Ml Mn Mq Nb Nd Ni Nm Nq Nr Nu Om Oz Pd Po Pz) Hr(Hu Hv Hw
Hx Ij Io Iq Iu Jm Jo Jr Lv Lz Mb Md Me Mf Mi Ml Mn Mq Mr Nd Nm Nr Nu Oi Oz Pc Pd Pe Po Pz) Hx(Hu Hw Ij Io Iq Iu Jo Jr Lu Lv Mb Me
Mf Mg Mi Ml Mn Mq Mr Mu Nd Nm Nr Nu Oi Oz Pc Pd Pe Po Pz) Nm(Hu Hw Io Iq Iu Jo Jr Lu Lv Mb Md Me Mg Mj Ml Mn Mq Nb Nd Ni
Nq Nr Nu Oi Om Pd Po Pz) Iu(Hu Hw Ij Jm Jo Lv Mb Md Me Mf Mg Mi Mj Ml Mn Mq Nb Nd Nr Nu Oh Oi Pc Pd Po Pz) Jo(Hu Hv Ij Io Iq
Jm Lv Mb Md Me Mf Mi Ml Mn Mq Nd Nr Nu Of Oz Pc Pd Pe Po Pz) Mz(Hq Hv Jk Jm Ma Mg Mi Mn Mq Mr Mu Nd Ni Nk Oh Oi Oz Pc Pe
Pf Pg) Is(Hq Hv Ij Iq Jm Jr Lu Ma Mi Mn Mq Mr Mu Nk Oh Oz Pc Pe Pf Pg) Iq(Hu Hw Lv Mb Md Me Mf Mg Mj Ml Mn Mq Nr Nu Oi
Pd Po Pz) Mh(Hu Ij Io Md Me Mf Mi Mj Ml Mn Nd Nu Oi Pd Po Pz) Io(Hu Lv Md Me Mf Mg Mj Ml Nd Nu Oi Pd Po) Oy(Hu Hv Hw Jr Lz
Ma Mg Nb Ni Nk Ns Oh Oi) Po(Lv Lz Mf Mi Mr Nd Oz Pe) Of(Hq Hw Mg Om Pe Pf Pg) Lv(Md Me Mj Ml Nu) Md(Ij Mi Mr Pe) Ml(Ij Mi Mr
Pe) Hu(Me Mf Mu) Nr(Mr Pe) Nb(Mr Pe) In(Pf Pg) NuPd IjQa] Qd{Mt(Fp Fr Hq Hr Hu Hv Hw Hx Ih Ii Ij In Io Ip Iq Ir Is It Iu Jh Jk Jl Jm Jn
Jo Jq Jr Js Jt Lh Li Lj Lu Lv Lw Lx Ly Lz Ma Mb Mc Md Me Mf Mg Mh Mi Ml Mm Mn Mp Mq Mr Mu Mv Mw Mx Mz Na Nb Nc Nd Ne Ng
Nh Ni Nk Nm Nn No Nq Nr Ns Nu Nv Ny Oe Oh Oi Om Oz Pa Pb Pc Pd Pe Pf Pg Po Pz Qa Qb Qc Qe) Mb(Fp Fr Hq Hr Hu Hv Hw Hx Ih Ii In
Io Ip Iq Ir Is It Iu Jh Jk Jl Jm Jn Jo Jq Jr Js Jt Lh Li Lj Lu Lv Lx Ly Lz Ma Mc Md Me Mf Mg Mh Mi Mj Ml Mn Mp Mq Mr Ms Mu Mv Mw
Mx My Na Nb Nc Nd Ne Ng Nh Ni Nk Nm Nn No Nq Nr Ns Nv Ny Oe Oh Oi Om Oy Oz Pa Pb Pc Pd Pe Pf Pg Po Pz Qa Qb Qc Qe) Lw(aC Fp
Fr Hq Hr Hu Hv Hw Hx Ih Ii In Io Ip Iq Ir Is It Iu Jh Jk Jl Jm Jn Jo Jq Jr Js Jt Lh Li Lj Lu Lv Lx Ly Lz Ma Mc Md Me Mf Mg Mh Mi Mk Ml
Mm Mn Mp Mq Mr Mu Mv Mw Na Nb Nc Nd Ng Nh Ni Nk Nm Nn No Nq Nr Ns Nv Ny Oe Oh Oi Om Oy Oz Pa Pb Pc Pd Pe Pf Pg Po Pz Qa
Qb Qc Qe) Mx(aC aN Fp Fr Hq Hr Hu Hv Hx Ih Ii Io Ip Iq Ir Is Iu Jh Jk Jl Jm Jn Jo Jq Jr Js Jt Lh Li Lj Lu Lv Lx Ly Lz Ma Mc Md Me Mf Mg
Mh Mi Ml Mm Mn Mp Mq Mr Mu Mv Mw Mz Na Nb Nc Nd Ne Ng Nh Ni Nk Nm Nn No Nq Nr Ns Nv Ny Oe Oh Oi Om Oy Oz Pa Pb Pc Pd
Pe Pf Pg Po Pz Qa Qb Qc Qe) Nh(Fp Fr Hq Hr Hu Hv Hw Hx Ih Ii In Io Ip Iq Ir Is Iu Jh Jk Jl Jm Jn Jo Jq Jr Js Jt Lh Li Lj Lu Lv Lx Ly Lz Ma
Mc Md Me Mf Mg Mh Mi Mk Ml Mm Mn Mp Mq Mr Mu Mv Mw Na Nb Nc Nd Ne Ng Nh Ni Nk Nm Nn No Nq Nr Ns Nv Ny Oe Oh Oi Om Oy
Oz Pa Pb Pc Pd Pe Pf Pg Po Pz Qa Qb Qc Qe) Ms(Fp Fr Hq Hr Hu Hv Hw Hx Ih Ii Ij In Io Ip Iq Ir Is It Iu Jh Jk Jl Jm Jo Jq Jr Js Lh Li Lj Lu Lv
Lx Ly Lz Ma Mc Md Me Mf Mg Mh Mi Mk Ml Mm Mn Mp Mq Mr Mu Mv Mw My Na Nb Nd Ng Ni Nk Nm Nn No Nq Nr Ns Nv Ny Oe Oh
Oi Om Oy Oz Pa Pb Pc Pd Pe Pf Pg Po Pz Qa Qb Qc Qe) Mz(aC Fp Fr Hq Hr Hu Hv Hx Ih Ii Ij Io Ip Iq Ir Is It Iu Jh Jk Jl Jm Jn Jo Jq Jr Js Jt Lh
Li Lj Lu Lv Lx Ly Lz Ma Mc Md Me Mf Mg Mh Mi Mk Ml Mm Mn Mp Mq Mr Mu Mv Mw Na Nb Nd Ng Ni Nk Nm Nn No Nq Nr Ns Nv Ny
Oe Oh Oi Om Oy Oz Pa Pb Pc Pd Pe Pf Pg Po Pz Qa Qb Qc Qe) In(Fp Fr Hq Hr Hu Hv Hw Hx Ih Ii Ij Io Ip Iq Ir Is It Iu Jh Jj Jk Jl Jm Jo Jq Jr Js
Jt Lh Li Lj Lu Lv Lx Ly Lz Ma Mc Md Me Mf Mg Mh Mi Mk Ml Mm Mp Mq Mr Mu Mv Mw Na Nb Nc Nd Nf Ng Ni Nk Nm Nn No Nq Ns Nv
Ny Oe Oh Oi Om Oy Oz Pa Pb Pc Pd Pe Pf Pg Po Pz Qa Qb Qc Qe) Mj(Fp Fr Hq Hr Hu Hv Hw Hx Ik Il Io Ip Iq Ir Is It Iu Jh Jk Jm Jn Jo Jq Jr
Js Li Lj Lu Lv Lx Ly Lz Ma Mc Md Me Mf Mg Mh Mi Mk Ml Mm Mn Mp Mq Mr Mu Mv Mw My Na Nb Nc Nd Ng Ni Nk Nm Nn No Nq Nr
Ns Nv Ny Oe Oh Oi Om Oy Oz Pa Pb Pc Pd Pf Pg Po Pz Qa Qb Qc Qe) Nc(Fp Fr Hq Hr Hu Hv Hw Hx Ih Ii Ij Io Ip Iq Ir Is Jh Jk Jl Jm Jn Jo Jq
Jr Js Jt Lh Li Lj Lu Lv Lx Ly Lz Ma Mc Md Me Mf Mg Mh Mi Ml Mm Mn Mp Mq Mr Mu Mv Mw Na Nb Nc Nd Ng Ni Nk Nn No Nq Nr Ns
Nv Ny Oe Oh Oi Om Oy Oz Pa Pb Pc Pd Pe Pf Pg Po Pz Qa Qb Qc Qe) Nf(aC Fr Hq Hr Hu Hv Hw Hx Ih Ii Ij Io Ip Iq Ir Is It Iu Jh Jk Jl Jm Jo
Jq Jr Js Jt Li Lj Lu Lv Lx Ly Lz Ma Mc Md Me Mf Mg Mh Mi Mk Ml Mm Mn Mq Mr Mu Mv Mw Na Nb Nc Nd Ng Nk Nn No Nq Nr Ns Ny

Mc Nb Nd Nk Nq Nr Ny Om Pc Pd) Nb(Hv Ip Iu Jg Li Ly Mc Nd Nr Pc Pd) Nq(Hx Ii Ip Iu Ly Ny Om Pc) Nr(Hv Ip Jg Li Nk Pc Pd) Ip(Hv Li Mq Nd Pc Pd) Pc(Hv Iu Li Mi Nn) Hv(Iu Li Pd) Hx(Ii Mv Ny) aC(Ji Lw Mz) Nd(Mi Pd) Ii(Iu Mv) Li(Jg Nk) IuOm} Jg{Iv(Fr Hq Hr Hu Hv Hw Hx Ih Ii Il Io Ip Iq Ir Is It Iu Jh Jk Jm Jn Jo Jq Jr Js Jt Lh Li Lj Lu Lv Lx Ly Lz Ma Mb Mc Md Me Mf Mh Mi Mj Ml Mm Mn Mp Mq Mr Mt Mu Mv Mw Na Nb Nc Nd Ne Nf Nh Ni Nk Nm Nn No Nq Nr Ns Nv Nx Ny Oe Oh Oi Om Oz Pa Pb Pc Pd Pe Pf Pg Po Pz Qb Qc) Mx(Fp Fr Hq Hr Hu Hv Hw Hx Ih Ii Il Io Ip Iq Ir Is It Iu Jh Jk Jl Jm Jn Jo Jq Jr Js Jt Lh Li Lj Lu Lv Lx Ly Lz Ma Mc Md Me Mf Mg Mi Ml Mm Mn Mp Mq Mr Mt Mu Mz Na Nb Nc Nd Ne Nh Ni Nk Nm Nn No Nq Nr Ns Nv Nx Ny Oe Oh Oi Om Oz Pa Pb Pc Pd Pe Pf Pg Po Pz Qa Qb Qc) Nj(Fr Hq Hr Hu Hv Hw Hx Ih Ii Io Ip Iq Ir Is It Iu Jh Jk Jn Jo Jq Jr Jt Lh Li Lj Lu Lv Lx Ly Lz Mb Mc Md Me Mf Mg Mh Mi Mk Ml Mm Mn Mq Mr Ms Mt Mu Mv Mw Nb Nc Nd Ne Nf Ng Nh Nk Nl Nm Nn No Nr Ns Nv Nx Ny Oe Oh Oi Om Oz Pa Pb Pc Pd Pe Pf Pg Po Pz Qc) aA(Hr Hu Hw Hx Ih Ii Ik In Io Ip Ir Is It Jj Jk Jl Jm Jo Jq Jr Js Jt Lh Li Lj Lu Lv Lw Lx Lz Ma Mc Me Mg Mh Mi Mj Mk Mm Mp Mq Mr Ms Mt Mv Mw Nb Nc Nd Ne Nf Nh Ni Nm Nn No Nq Nr Nv Nx Ny Oe Oi Oz Pa Pb Pd Pe Pf Po Pz Qc) Qe(Fp Hq Hr Hu Hw Hx Ii Ik Il In Io Iq Is It Iu Jh Jk Jl Jm Jn Jo Jq Jr Js Jt Lh Lv Lw Lx Ma Mb Mc Me Mg Mh Mi Mj Mk Mp Mr Mt Mv Mw Mz Nc Nd Ne Nf Nh Ni Nm Nn Nq Nu Nx Ny Oe Oh Om Oz Pa Pb Pd Pe Pz Qa) Jj(Hr Hu Hv Hx Ih Ij Ik Ip Ir Jh Jm Jo Jq Jr Jt Lh Li Lj Lu Lv Lw Lx Ly Ma Mb Me Mf Mh Mi Mk Ml Mm Mp Mq Mr Ms Mt Mv Mw My Mz Nc Nd Ne Nf Ng Nh Ni Nm Nn No Nq Nr Nv Ny Oe Oh Oy Oz Pa Pb Pd Pe Pg Po Qc) Qa(Fp Hq Hr Hu Hw Hx Ii Ik Il In Io Iq Is It Iu Jh Jk Jl Jn Jo Jq Lv Lw Mb Me Mg Mh Mj Mk Mp Ms Mt Mv Mw Mz Na Nc Ne Nf Nh Ni Nl Nq Nu Nx Ny Oe Om Pb Pz) Fp(Hr Hu Hw Ik In Is It Jh Jk Jl Jn Jq Js Jt Lw Lx Mb Mg Mh Mk Mm Mp Ms Mt Mv Mw Mz Nc Ne Nf Ng Nh Ni Nl Nm Nn Nu Nx Oe Pa Pb Pz Qb Qc) Oy(Ih Is It Jl Jn Jq Jr Js Jt Lh Lv Lw Mb Mh Mi Mk Mp Mq Mr Ms Mt Mu Nc Nd Ne Ng Nh Nl Nn Nx Oz Pa Pd Pe Pg Po Qc) My(Ih Is Jl Jn Jq Js Lh Lw Lx Mb Mi Mp Mr Mt Mu Ne Nl Nn Nu Nx Pe) Mz(Hr Ii In Jh Jn Lw Mb Md Mh Ml Ms Nc Ne Nf Ng Nh Nl Nu Nx Om Qb) Qb(In Iu Jh Jk Lw Mb Mk Mp Ms Mv Mw Ne Nf Ng Ni Nl Nu Nx Oe Pz) Og(Fr Hq Hu Hx Ii Iq Iu Jk Jo Md Mj Ml Mn Na Nb Ns Oi Om Pf Pg) Ng(Ik Is Jl Jn Js Jt Lh Lw Lx Mp Mt Nl Nu Nv Nx) Nl(Ik Is Jl Jn Js Lw Lx Mg Mp Ms Ni Nu) Nu(In Is It Jl Jn Js Lw Mb Ms) Ms(Is Jn Js Lw Mt Nx) Ii(Jl Lh Mr Of Pe) Lw(Jn Js Mb Ne) Mw(Jl Lh Lx Nv) Mb(Jl Js Mp) Aj(aC bM) Lx(Mh Mv) MvLh PzOf JiaC} Iv{Mz(Fp Fr Hx Ik Il In Is Jh Jj Jl Jn Jt Lh Li Lw Lx Mb Mh Mk Ml Mm Mp Ms Mt Mx My Nc Ne Nf Nh Nl Nm Nn Nu Nv Nx Ny Of Oy Pb Qa Qe) aA(Fp Fr Hr Ih In Ip Ir It Jh Jl Jq Js Jt Lh Li Lv Lw Lx Mb Mm Mp Mx My Nc Ne Nf Nh Nl Nm Nn No Nr Nu Nv Ny Oy Pa Qa Qb) Nj(Fp Ih Ij Ik Ip Ir Is Jh Jn Jq Js Li Lw Ma Me Mi Mk Mm Mn Mp Mq Mr Mx Nd Nf Nh Ni Nk Nm Nr Nu Nx Of Oy Pa Pe Qb Qc) Nv(Fp Hr Hw Ii Ik Il In It Jn Jt Lw Lx Mb Mh Mk Ms Mt Mv Mw Mx My Ne Nf Ng Nh Ni Nl Nm Nq Nu Nx Oe Qe) Nx(Fp Fr It Jh Jl Jt Lh Li Lw Lx Mk Mm Mp Ms Mt Mx Ne Nf Nh Nl Nm Nn No Nu Ny Of Oy Qa Qe) Jt(Fp Hr Ii It Jl Jn Js Lx Mb Mj Mk Mm Ms Mt Mx My Na Ne Nf Nh Nl Nu Ny Of Oy Qa Qe) Qe(Hr Il In Jh Jl Jn Jq Lh Lw Lx Mb Mk Mm Mp Ms Mt Mx Ne Nf Nh Nl Nm Nn Nu Oy) Mt(Fp Ik In Is Jj Jl Jn Lh Lw Mk Mm Ms Mx My Nf Nl Nm Nn Nu Ny Of Oy Qa) Lx(Fp Ik In Jj Jl Jn Lh Lw Mh Mk Mm Mx My Ne Nf Nh Ni Nl Nm Nu Of Oy) Og(Ih In Ip Ir It Jh Jq Lw Mp Mr Nc Ne Nf Nh Nl No Nr Po Pz Qb) Nu(Fp Fr In Is Jj Jl Jn Jq Js Lh Lw Mm Mx Nf Nl Nn Ny Oy Qa) In(Fp Ih Is Jn Jq Js Lh Li Mm Mx Nl Nm Nn Ny Qa) Qa(Hr Hw Il Lw Mb Mk Mm Ms My Nf Nl Nm Of Oy) Jj(Fp Fr Is Jl Jn Jq Js Lh Li Mx Nl Nn Ny) Lh(Hr Hx Jn Mh Mk Mm Mw My Nb Nf Nl Oy) Nl(Fp Fr Jn Li Lw Mm Nm Nn No Ny) Mx(Fr Jn Lw Mk Mm Nf Nm Nn Ny) Nf(Fp Fr Jl Jq Js Li Nn Ny) Lw(Fp Jn Li Mm Ny) Fr(Mk My Of Oy) Mm(Fp Jl Jn Of) Jl(Hr Jn) Of(Nn Ny) FpNm LiOy} Nj{Qa(Fp Fr Hr Hw Ik Il Ip Is It Iu Jh Jl Jn Jq Js Jt Lh Li Lw Lx Mh Mi Mk Mm Mp Mr Ms Mt Mx My Nd Nf Nh Nm Nn No Ns Nu Nv Nx Ny Oe Of Oy Pa Pb Qe) Qe(Fp Fr Hr Ik Il Ip Is It Iu Jh Jl Jn Jq Js Lh Li Lv Lx Mh Mi Mk Mm Mp Mr Ms Mt Mx My Mz Nc Ne Nf Nh Ni Nn Nv Ny Oi Qe) Qe(Fp Ij Il Is Jh Jj Jl Jn Jq Js Lh Li Lv Lw Mb Mm Mp Ms Mu Mx Mz Nc Ne Nf Nh Nn Nv Ny) Nv(aA Fp Ij Ip Is It Jj Jn Jt Lv Lw Ms Mt Mx My Mz Nc Ne Nf Nh Ni Nx Of Oy) Nu(aA Fp Is It Jl Jn Jq Js Lh Lw Mt Mx Mz Nl Nm Ny Qb) Jt(aA Fp Ij Is Jl Jn Lx Mb Mt Mx Mz Ne Nh Nx Qb) Ij(Fp Is Jl Lw Mm Mx Mz Nc Ne Nf Nh Nm) Nx(aA Fp Fr Jl Lh Li Lx Mx Mz Nl Nm Qb) Mt(aA Fp Is Jn Js Lw Mx Mz Nl Nm Ny) Nl(aA Is Jl Js Li Lx Mz Nm) Nm(Fp Is Jl Js Mx Qb) aA(Jl Jn Js Li Mz) MmMx JiaC} aA{Qe(Fp Hr In Jt Lv Lw Mb Mm Mt Mx My Mz Ne Nf Nh Ni Nl Nm Nu Nx Oy) Jn(Fp Li Lv Lx Mb Mm Ms Mt Mx Mz Ne Nf Nl Nu Nv Nx Qa) Mt(Fp Hr It Js Jt Mb Mx My Mz Nl Nu Nx Oy Qa) Qa(Hr Mb My Mz Nf Nl Nu Nx Oy) Mz(Fp Jt Mx Ne Nl Nu Nx) Nv(Mb My Nl Of Oy) Fp(Jt Nl Nx) Mx(Jt Nu Nx) My(Ij Lh) Nl(Jt Li) NuNx NfLi} aC{Ji(aL aM aR AX aZ bA bU bV cD cM cN cQ cT cX cZ dH dJ Fp Ii Ik Io Jj Jo Jq Jt Li Lj Lw Mf Mk Ml Mp Mt Mx Mz Nf Nh Ni Nk Ns Nu Of Pa Pz Qa Qc Qe) Jt(aN aZ bM cM cN cX Jj Jo Lj Lw Mz Nf Ni Of) Lw(aN Ar Ax Li Lj Mx Nf) Mz(aN bM Li Nf Nh) CuNf} Jj{Nx(Fr It Jl Jn Js Lh Li Lx Mm Mx Mz Nl Nr Nv Qb) Nv(Fp It Jn Jt Mb Mx Nf Nl Nu Oy Qa Qe) Qe(Jn Js Jt Mm Ml Nl Nm) Nu(Jl Jn Js Jt Mm Qa) Qa(Jn Jt Mm Mz Nl) Jt(Fp Mt Mx Nl) Mm(Jn Mx Nl) bM(Ji Kf Mx) MtJs} bU{kR(dU fA gC gZ oT oV oW pH pK) oW(eF iA In Jn Nk oK) dU(cC Hq Nb) oD(Mb Nd nN) GdkE NbOV aReQ fAnW} Nx{Qa(In Ms Nf Nu Of Oy) Qe(In Ms Mt Nl Nu Of) Mt(Ms My Of) Nf(Fp Mz) Of(Jt Nv)} Jt{Ii(Lh Lx Mt Mx Mz Nv Qe) Mt(Ms My Oy) Nl(Fp Mz Qe) PoLx FpNf MjMx NvOf} Nv{Oy(Fp Mb Mt Mx Nl Nu Of Qa Qe) Of(Mb Nl Nm Nu) Nf(Fp Mb)} Qe{Nl(Lw Mz Nk Nm Nu) Nu(In Lw) MtMy IiLh} Qa{Mz(Ms Nl) Nuln liLh} Ji{MxaN bMcM} MtIiLh Unconstrained panels with 3 analytes, where 2.4E-8 >= 'model p-value' > 1.0E-8. Contains 9,120 panels of 37,933,414 total panels evaluated. : Qd{Mp(Fr Hq Hu Hv Hx Ih Io Ip Iq Ir Jk Jl Jm Jo Jq Jr Js Li Lj Lu Lx Ly Ma Mc Md Mf Mg Mi Ml Mn Mq Mr Mu Mv Na Nb Nd Ng Nk Nn No Nr Nv Ny Oh Oi Om Oz Pa Pc Pd Pe Pf Pg Po Pz Qa Qb Qc Qe) Is(Fr Hq Hu Hv Hx Ih Ii Io Ip Iq Ir Jk Jm Jo Jq Jr Li Lj Lu Lx Ly Ma Mc Md Me Mf Mg Mi Ml Mn Mq Mr Mu Mv Mw Na Nb Nd Ng Nk Nn No Ny Oh Oi Om Oz Pa Pc Pd Pe Pf Pg Po Pz Qa Qb Qc Qe) Jl(Fr Hq Hu Hv Ih Io Ip Iq Jk Jm Jo Jq Jr Lh Li Lj Lu Lx Ly Ma Mc Md Me Mf Mg Mi Ml Mn Mq Mr Mu Mv Mw Nb Nd Ng Nk Nn No Nr Nv Ny Oh Oi Om Oz Pa Pc Pd Pe Pf Pg Po Pz Qa Qb Qc) Iu(Fr Hq Hu Hv Hx Ih Ii Io Ip Iq Jk Jm Jo Jq Jr Lj Lu Ly Ma Mc Md Me Mf Mg Mi Ml Mn Mq Mr Mu Mv Mw Na Nb Nd Ng Nk No Nr Ns Oh Oi Om Oz Pa Pe Pf Pg Po Pz Qa Qb Qc Qe) Oe(aC Fr Hq Hu Hv Hx Ih Ii Io Ip Iq Jk Jm Jo Li Lj Lu Ly Ma Mc Md Me Mg Mi Ml Mn Mq Mr Mu Mv Mw Na Nb Nd Ng Nk No Nr Oh Oi Om Oz Pa Pc Pd Pe Pf Pg Po Pz Qa Qb Qe) Lv(Fr Hq Hu Hx Ih Io Ip Iq Jk Jm Jo Jq Jr Li Lj Ly Ma Mc Md Me Mf Mg Mi Ml Mn Mq Mr Mu Mv Na Nb Ng Nk No Nr Oh Oi Om Oz Pa Pc Pd Pf Pg Po Pz Qa Qb Qe) Mh(Fr Hq Hu Hv Hx Ih Ii Io Ip Iq Ir Jk Jm Jo Lj Ly Mc Md Me Mf Mg Ml Mq Mu Mv Mw Na Nb Nd Ng No Nq Nr Ns Ny Oh Oi Om Oz Pa Pb Pc Pf Pg Po Qa Qb Qc Qe) Ni(aC Fr Hq Hu Hv Hx Ih Ii Io Ip Iq Jk Jm Jo Jq Jr Lj Ly Ma Mc Md Me Mg Ml Mn Mq Mr Mu Mv

Figure 31 Continued

Mw Nb Ng Nk No Nr Oh Oi Om Pa Pc Pe Pf Pg Po Pz Qa Qb Qc Qe) Nv(Fr Hv Ih Io Ip Iq Ir Jm Jo Jq Jr Lh Li Lj Lu Lx Ly Ma Mc Md Mf Mg
Mi Mn Mq Mr Mu Na Nd Nk Nn No Nr Oh Oi Om Oz Pa Pc Pd Pe Pf Pg Pz Qa Qb Qe) Jt(Fr Hu Hv Ih Ij Io Ip Jm Jo Jq Li Lj Ly Ma Mc Md
Me Mf Mg Mi Ml Mn Mq Mr Mu Mv Nd Nk Nn No Nr Ny Oh Oi Om Oz Pa Pc Pd Pe Pf Pg Po Pz Qa Qb) Ns(aC Fr Hq Hr Hu Hv Hx Ii Io Ip
Iq Ir Jk Jo Jq Jr Js Li Lu Lx Mc Me Mf Mi Mq Mr Mu Mv Mw Na Nd Ng Nn No Ny Om Oz Pa Pc Pd Pe Qb Qc Qe) Lx(Hq Hr Hu Hv Io Ip Iq
Ir Jk Jm Jo Jq Jr Js Lh Li Lu Ly Mc Me Mf Mi Ml Mm Mq Mr Mu Na Nd Ng Nn No Ny Om Oz Pc Pd Pe Pf Qb Qc Qe) Lz(Fr Hq Hu Hv Hx Ii
Io Ip Iq Jk Jm Jo Jq Lj Ly Ma Md Mg Ml Mn Mu Mv Mw Na Nb Ng Nk No Nr Ny Oh Oi Om Pa Pc Pg Po Pz Qa Qb Qe) Pb(Fr Hq Hr Hv Hx Ii
Io Ip Iq Ir Jk Jm Jo Jq Jr Js Li Lu Ly Mc Md Me Mf Mi Mq Mr Mu Nd Nn No Nq Ny Oi Om Oy Pc Pe Pg Qb Qc Qe) Nn(Fr Hq Hr Hv Hx Ii Io
Ip Iq Ir Jk Jm Jo Jq Jr Js Li Lu Ly Mc Me Mf Mi Ml Mq Mr Na Nd Ng No Ny Om Oz Pa Pd Pe Qb Qc Qe) Jh(Fr Hv Hx Ih Io Ip Jm Jo Jq Li Lj
Ly Ma Mc Md Mg Ml Mn Mq Mr Mu Na Nb Nd Nk No Nr Ny Oh Oi Pa Pc Pe Pf Pg Po Pz Qa Qb) Nq(Fr Hq Hr Hu Hv Hx Ii Ip Iq Ir Jm Jo Jq
Jr Js Lu Mc Md Me Mf Mi Mq Mr Mu Na Nd No Ny Oi Oz Pa Pc Pd Pe Pg Qb Qc Qe) Mm(aC Fr Ih Io Ip Jm Jo Li Lj Ly Ma Md Mf Mg Mi Ml
Mn Mu Na Nb Nd Nk No Nr Ny Oh Oi Oz Pa Pc Pd Pe Pf Pg Po Qa Qb) It(Fr Hu Hx Ih Ii Ij Io Iq Jk Jm Lj Ly Ma Mc Md Mg Ml Mn Mu Mv
Mw Na Nb Ng Nk No Nr Oh Oi Om Pa Pc Pf Pg Po Pz Qb) Hr(Fr Hq Hu Hv Hx Io Ip Iq Ir Jr Li Lu Ly Mc Md Me Mf Mi Mq Mu Mw Nd No
Ny Om Oy Oz Pa Pc Pf Pg Qa Qb Qc Qe) Js(Hq Hu Hv Hx Ii Ip Iq Ir Jk Jm Jo Jr Li Lu Me Mf Mi Ml Mq Mr Mv Mw Na Nd No Ny Om Oz Pc
Pd Pe Qb Qc Qe) Oy(Hu Hv Hx Ih Ii Io Iq Jk Jm Lj Ly Ma Mc Me Ml Mn Mv Mw Na Nb Ng Nk No Nr Oh Oi Om Pf Po Pz Qa Qb Qe) Lu(Hq
Hu Hv Hx Ii Ip Ir Jk Jq Jr Lh Li Mc Me Mf Mi Mq Mv Mw Na Nd No Ny Oz Pc Pd Pe Qb Qc Qe) Mk(aC Hq Hu Hv Hx Ih Ii Io Jk Jm Lj Ma
Mg Ml Mn Mv Mw Na Nb Ng Nk Nr Oh Oi Pa Pf Po Pz Qa Qb) Lh(Fr Ih Ij Io Ip Jo Jq Li Lj Ly Ma Mc Mg Mi Mn Mq Mr Mu Nd Nk No Oh
Oi Oz Pc Pf Pg Pz Qa) Pd(Hq Hu Hv Hx Ii Ip Iq Ir Jk Jm Jq Jr Li Mc Me Mf Mv Mw Na Ng No Ny Om Pc Pe Pf Qb Qc Qe) aC(Aj aZ Ba Bb
Bc cD cQ cT dJ Dk Dl Io Jn Li Lj Ml Mt Ne Nh Nj Nk Nl Nm Nu Nw Nx Og Ok) Ir(Hq Hu Hv Hx Ii Ip Jk Jm Jo Jr Li Mc Me Mf Mi Mq Mr
Mw Nd No Oz Pc Pe Qb Qc Qe) Fp(Fr Ih Ij Io Jo Li Ly Ma Mc Md Mg Mn Mq Mr Nb Ng Nk Nr Oh Oi Pf Pg Pz Qa) Nc(Ih Ij Jo Lj Ly Ma Md
Mg Ml Mn Mv Nb Ng Nr Oh Oi Om Pa Pf Pg Po Pz Qa) Jr(Fr Hq Hv Hx Ii Ip Iq Jk Li Me Mf Mi Mq Mr Mw Nb Oi Oz Pa Pd Pe Po Pz Qc Qe)
Hw(Hq Ii Ij Jk Jm Lj Ma Mg Ml Mn Mv Na Nb Ng Nk Nr Oh Oi Om Pf Po Pz) Li(Hq Hu Hv Hx Ii Iq Jk Jm Jq Lj Me Mf Mi Mv Mw Nd Ng
Om Oz Qb Qc Qe) Jn(aN Ih Ij Io Ip Jo Lj Ma Md Mg Mn Nb Nk Nr Oh Oi Pf Pg Po Pz Qa) Nm(Fr Ih Io Lj Ma Md Mg Mn Nb Nk Nr Oh Oi Pc
Pf Pg Po Qa Qb) Me(Fr Hq Hx Ii Ip Mc Mf Mi Mr Na Nd No Ny Oz Pc Pe Qc Qe) Qc(Hq Hv Ii Ip Jq Mc Mf Mi Mq Mr Nd No Ny Oz Pc Qb
Qe) Ny(Hq Hx Ii Iq Jk Jq Mf Mi Mr Mw Nd Ng Om Oz Pc Qe) Mf(Hq Hu Ii Ip Jk Jm Jq Mi Mq Mr Nd No Oz Qe) Ii(Fr Ip Jo Mj Mq Mu Nb
Nd No Oz Pa Pg) Mi(Hq Hv Ip Iq Jk Ml Mv Mw Nb Po Qe) Jq(Hq Hx Ip Iq Ml Mw Nd Om Oz) Mr(Ml Mv Mw Na Nb Pa Po Qe) Pe(Hx Ml
Mw Nb Pa Po) Ij(Lw Mb Mj Mx Nh) Hq(Ip Mq Nd Oz) Mw(Fr Mq Pc) Na(Hv Jo Qa) In(Ma Mn Nr) Ip(Jm Oz Qe) aN(cM Ji Nf) Qe(Mq Oz)
FrJk Mjlh MuMv HvOz bMcM} On{Is(Fr Hv Ih Io Ip Ir Jl Jm Jo Jq Jr Js Jt Lh Li Lu Lx Ly Lz Ma Mc Md Mf Mg Mi Ml Mm Mn Mq Mr Mu
Na Nb Nd Nk Nn No Nr Ns Nv Nx Oh Oi Oz Pa Pc Pd Pe Po Pz Qb Qc) Hu(Fr Hq Hv Il Io Iq Ir Iu Jl Jm Jo Jq Jr Lh Li Lj Lu Ly Lz Ma Mc Md
Mg Mi Mj Ml Mm Mn Mq Na Nb Nd Nk No Nr Ns Nv Oh Oi Oz Pa Pc Pd Pe Pf Pg Po Pz Qc) Mt(Fr Hq Hv Ih Io Ip Ir Jg Jl Jm Jo Jq Jr Js Lh
Li Lu Lx Ly Lz Ma Mc Md Mf Mg Mi Ml Mm Mn Mq Mr Mu Na Nb Nd Nn No Nr Ns Oh Oi Oz Pd Po Pz Qb Qc) Nq(Fr Hq Hv Io Iq Ir Iu Jk
Jl Jo Jq Jr Js Lh Lu Ly Lz Ma Mc Md Mf Mg Mi Mj Ml Mm Mn Mq Mu Na Nb Nd Nk No Nr Ns Nv Oh Oi Oz Pa Pd Pe Po Pz Qc) In(Fr Hq
Hv Il Io Iu Jl Jm Jo Jq Lh Lu Ly Lz Ma Mc Md Mf Mg Mi Mj Ml Mm Mn Mq Mr Mu Na Nb Nd Nk Nn No Nr Ns Nv Oh Oi Oz Pa Pc Pd Pe Po
Pz Qc) Lw(Fr Hv Io Jl Jm Jo Jq Jt Lh Lu Lx Ly Lz Ma Mc Md Mf Mg Mi Mj Mm Mq Mu Na Nb Nd Nk Nm Nn No Nr Ns Nv Oh Oi Oz Pa Pc
Pd Pe Pf Pg Po Pz Qc) Me(Fr Hv Io Ip Ir Iu Jl Jo Jr Js Jt Lh Li Lu Lx Ly Lz Ma Mc Md Mf Mg Mi Mj Ml Mm Mn Mq Mr Na Nb Nd Nn No Nr
Ns Oh Oi Oz Pa Pd Po Pz Qb Qc) Mz(Fr Hq Hv Ih Io Ip Ir Jl Jo Jq Js Lh Li Lj Lu Lx Ly Lz Ma Mc Mf Mg Mi Mj Mm Mn Mq Mr Mu Nd Nk
Nn No Nr Ns Nv Oh Oi Oz Pa Pc Pd Pe Pz Qc) Nx(Hq Hv Hx Ih Ik Io Ip Iq Ir Iu Jg Jk Jl Jr Js Jt Lh Li Lu Lx Ly Lz Ma Mc Md Mf Mg Mi Mj
Ml Mm Mn Mq Mr Nb Nd Nn No Ns Oh Pd Po Pz Qb Qc) Lv(Fr Hq Hv Il Io Iq Jg Jl Jq Jr Js Jt Lh Li Lu Lx Ly Lz Ma Mc Md Mf Mi Ml Mm
Mn Mq Mr Mu Na Nb Nd Nk Nn No Nr Ns Nv Oh Oi Pa Pd Pz Qc) Hw(Fr Hq Hv Il Iq Jm Jo Jq Lh Lu Ly Lz Ma Mc Md Mg Mi Mj Ml Mm
Mn Mq Mu Na Nb Nd Nk Nn No Nr Ns Nv Oh Oi Om Oz Pa Pc Pd Pe Pf Pg Po Pz) Qa(Fr Ih Ij Ip Ir Jl Jo Jq Js Lh Li Lj Lu Lx Ly Lz Ma Mc
Md Mg Mi Mm Mn Mq Mr Mu Nd Nk Nn No Nr Nv Oi Oz Pa Pc Pd Pe Pf Pg Pz Qb Qc) Om(Fr Hq Hv Hx Iu Jk Jl Jo Jr Js Lh Li Lj Lu Ly Lz
Ma Mc Md Mf Mj Mm Mn Mq Mu Na Nb Nd Nk Nn Nr Ns Nv Oh Oi Oz Pa Pc Pd Pe Pf Pg Qc) Hr(Fr Hq Il Iq Iu Jm Jo Lu Ly Lz Ma Mc Md
Mf Mg Mi Mj Ml Mm Mn Mu Na Nb Nd Nk Nn No Nr Ns Nv Oh Oi Oz Pa Pc Pd Pf Pg Po Pz Qc) Mk(Fr Hq Hv Hx Ik Il Io Ir Iu Jk Jl Jo Jq Lh
Lu Ly Lz Ma Mc Md Mf Mg Mi Mj Ml Mm Mn Mq Nb Nd Nn No Nr Ns Oh Pa Pc Pd Pe Qc) Ny(Hq Hv Ih Ik Il Io Ip Iq Ir Iu Jg Jk Jl Jo Jq Jr
Js Jt Li Lj Lu Lx Ly Mc Mf Mg Mi Mj Ml Mn Mq Nm Nn Ns Nv Oh Pb Pe Qb Qc) Pb(Hq Hv Hx Ih Ik Il Io Ip Iq Ir Iu Jk Jl Jo Jq Jr Js Jt Lh Li
Lj Lu Lx Mc Mf Mg Mi Ml Mq Mr Nm Ns Oh Oz Pa Pe Qb Qc) Oe(Fr Hv Ij Jl Jm Jo Jq Lh Lu Ly Lz Ma Mc Mi Mm Mq Mu Na Nd Nk Nn No
Nr Ns Nv Oh Oz Pa Pc Pd Pe Pf Pg Pz Qc) Nm(Hq Hx Ih Ik Il Io Ip Iq Ir Iu Jl Jo Jr Js Jt Li Lj Lu Lx Ly Mc Md Mg Mj Ml Mn Mr Na Nb Ns Oh
Po Qb Qc) Ih(Hv Hx Ik Il Io Ip Ir Iu Jg Jl Jo Jr Js Jt Lh Li Lj Lu Lx Ly Mc Md Mf Mg Mj Ml Mn Mr Nb Ns Oh Po Qc) Nc(Fr Hv Jm Jq Lh Lu
Ly Lz Ma Md Mi Mm Mq Mu Na Nb Nd Nn No Nr Ns Nv Oi Oz Pa Pc Pd Pe Pf Pg Pz Qc) Jg(Hq Hx Ik Il Io Ip Iq Ir Iu Jl Jo Jq Jr Js Jt Lh Lj Lu
Lx Ma Mc Mf Ml Mn Mq Mr Nn Oh Pa Po Qc) Hx(Hq Hv Ik Il Io Ip Iq Ir Iu Jk Jo Jq Li Lj Lu Ly Mc Mf Mg Mi Ml Mn Mq Ns Nv Oh Pa Qb
Qc) Lj(Hq Hv Ik Il Io Ip Ir Iu Jk Jr Js Jt Lh Lu Lx Ly Mc Mf Mg Mj Ml Mn Mr Ns Oh Po) Jp(Fr Ij Jm Lz Md Mi Mj Mm Mu Na Nd Nk No Nr
Ns Nv Oi Oz Pa Pc Pd Pe Pf Pg Po) Jr(Hq Hv Ik Il Io Ip Ir Iu Jo Js Jt Lx Md Mf Mg Mj Ml Mm Mr Nb Po Qb Qc) Jk(Ik Il Io Ip Iq Iu Jl Jq Lh
Li Lu Lx Mc Md Mf Ml Mn Mq Mr Nn Ns Po Qc) Jt(Hq Hv Ik Io Ip Iq Ir Iu Jl Js Lu Lx Mc Md Mf Ml Mn Mr Po Pz Qb Qc) Il(Hq Hv Ij Ik Io
Ip Iq Iu Jl Lh Li Lx Ly Lz Mf Mg Mr No Ns Oh Pe) Ni(Hv Ij Jm Jq Lh Ly Mr Mu Nv Nv Oz Pa Pc Pd Pe Pf Pg Po Pz) Js(Hq Hv Ik Io Ip Iq
Iu Jl Lu Md Mg Ml Mn Mr Nb Nw Oh Po Qb) Mh(Ij Jm Mi Mq Mu Na Nd Nk Nn No Nv Oi Oz Pa Pc Pd Pf Pg Pz) Jn(Fr Ij Ir Jq Lz Mu Na
Nd Nk No Nr Nv Oi Pc Pd Pe Pf Pg) Iq(Hq Ik Io Ip Li Lx Mc Md Mf Mg Ml Mn Mr Nb Qb) Mp(Ij Jm Mu Na Nk Nv Oi Oz Pc Pd Pe Pf Pg Pz)
Nw(Ij Jl Jm Jo Jq Li Pa Pc Pd Pe Pf Pg Pz Qc) Ik(Hq Hv Io Ip Ir Iu Jl Li Lx Mf Ml Mr Qc) It(Ij Jm Jq Nk Nv Oz Pc Pe Pf Pg) Qb(Hq Hv Io Ip Iu
Mf Mj Ml Mr Po) Hq(Io Ip Ir Iu Jl Li Lx Mr) Ip(Iu Jo Mg Mj Ml Mr Oh) Qc(Ij Mu Nk Nv Oi Pf Pg) Ir(Iu Ly Mg Mj Ml Ns) Mr(Fr Iu Mf Mj
Ml) Ij(aA Jh Mv Ne Nh) Lx(Hv Iu Mj Oh) Li(Iu Mg Mj Po) Mv(Jm Pf Pg) Jl(Mj Nb Po) aC(aN Ji Of) Nh(Jm Pf) MlLh PaPe} Nw{Lw(aC Fr
Hw Hx Ij In Io Ip Iq Ir Iu Jh Jl Jr Js Jt Lh Li Lx Ly Lz Ma Mc Md Mf Ml Mk Mm Mn Mq Mr Mu Na Nb Nd Ng Nk Nm Nn No Nq Nr Ns
Nv Oe Oh Oi Qb) Jg(Hv Hv Hw Ih In Io Ip Iq Ir Iu Jk Jo Jq Js Lh Lj Lv Lx Ly Lz Mc Md Mf Mg Mi Mj Mk Ml Mm Mn Mq Mr Nb Nd Nk Nn
No Nq Ns Nv Oh Oz Pa Pc Pd Pe Po Qc) Jp(Hu Hv Hw Ii In Io Ip Ir Jh Jo Jq Js Lh Li Lj Lx Ly Lz Ma Mc Md Mf Mi Mj Mk Ml Mm Mq Mr
Mz Nd Ng Nn No Nq Ns Nv Oe Oh Om Oz Pa Pc Pd Pe Po Qc) Is(Fr Hu Hw Ih Ij Io Ip Ir Iu Jh Jl Jn Lh Li Lx Ly Lz Ma Mc Md Mf Mg Mi Mm
Mn Mq Mr Mu Na Nb Nd Nk Nn No Nq Nr Nv Oh Oi Oz Pa Pd Po Qb Qc) Nx(Fr Hu Hw Hx Ih Ij Io Ip Iq Iu Jh Jl Jn Lh Li Lj Ly Lz Ma Mc
Md Mg Mi Mj Mk Mn Mq Mr Mu Na Nb Nd Nk No Nq Nr Ns Nv Oh Oi Oz Pa Pd Pe Qc) Mt(Fr Hq Hv Hw Ih Ij Jk Jl Jo Jq Jr Js Lh Li Lj Lx
Ly Ma Mg Mm Mn Mq Mr Mu Na Nb Nk No Nr Nv Oi Oz Pa Pc Pd Pe Pf Pg Po Pz Qb Qc) Mw(Fr Hr In Io Ip Iq Iu Jh Jk Jo Jr Js Li Ly Lz Ma
Mc Md Mg Mj Mk Ml Mn Mv Na Nb Nd Ng Nk No Nr Ns Ny Oe Oh Oi Om Oy Pb Pc Pd) Me(Hw Hx Ih Ij Ip Iq Ir Iu Jh Jt Lv Lx Ly Lz Ma

Figure 31 Continued

Mc Mf Mi Mj Mk Mn Mq Mr Mu Mz Nb Nd Ng Nk Nn No Nq Nr Ns Nv Oe Oh Oi Oz Pd Qb) Mh(Fr Hr Hx Ii In Io Ip Iq Iu Jh Jr Li Lz Ma Mc
Md Mg Mj Mk Ml Mm Mn Mu Na Nb Nd Ng Nk No Nq Nr Ns Oe Oh Oi Oz Pa Pb Pd Qc) Il(Ii Ij Ik In Ip Jj Jl Js Lh Lx Ly Mc Md Mf Mi Mk
Ml Mm Mq Mr Nd Ng Nk Nn No Nq Nr Ns Nv Oe Om Oz Pb Pd Pe Qc) Qe(Fr Ih Ij Io Ip Ir Jk Jm Jo Jq Li Lj Lx Ma Mg Mi Mn Mq Mr Mu Na
Nb Nk No Nr Nv Oi Pa Pc Pe Pf Pg Pz Qb Qc) Jj(Hr Hv Ip Jh Jm Jr Lh Li Lu Lx Ly Lz Md Mf Mj Ml Mm Mq Mr Mv Nd Ng Ni Nk Nn No Nr
Ns Nv Oi Oz Pa Pd Po Pz) Jt(aC Hq Hu Hv Ih Ik Ir Iu Jl Jo Lv Lx Ly Lz Ma Mc Md Mf Mk Ml Mr Mz Na Nd Nm Nn Nq Ns Oe Oz Pd Po Pz
Qc) Mp(Hr Hx Ih Ii Ij In Ir Jn Lu Lv Lx Ly Lz Mc Md Mf Mj Mk Ml Mm Mr Mz Ng Nm Nn Nq Ns Oe Oi Om Pb Po Qb) Qa(Fr Ih Ij Ip Ir Jm
Jo Jq Js Li Lj Lx Ma Mg Mi Mn Mq Mr Mu Nb Nd Nk No Nr Nv Oi Pa Pc Pf Pg Pz Qb Qc) Mv(Fr Hr Ih In Io Ip Ir Jh Jl Jr Js Ly Lz Mc Mf Mg
Mm Mq Nd Nk No Nq Nr Ns Ny Oe Oi Om Pb Pd Pe Qb) Nh(Fr Hu Hv Hw Jh Jl Jq Jr Js Li Lj Ly Ma Mg Mn Mu Na Nb Nk Nq Nr Oz Pa Pc
Pd Pe Pf Pg Po Pz Qc) Nm(Hw Hx Ih In Ir Jh Jl Jn Jr Lx Ly Lz Ma Mc Md Mf Mj Mk Ml Mq Mr Mz Nd Nk Nn Nq Ns Oe Pb Qb) Ni(Hr Ih Ii Ij
Ip Ir Lv Lz Mc Md Mf Mi Mj Mk Ml Mm Mq Mz Nd Ng Nn No Nr Ns Nv Om Oz Pb Qb) Jn(Hu Hv Hw Hx Ii Ik In It Jh Jl Jr Lh Lv Lx Mf Mj
Mk Ml Mm Mz Ng Nn Ny Oe Om Oz Pd Po Qb) Ny(Ih Ij Ip Ir Jl Js Lx Ly Lz Mc Mf Mk Ml Mm Mq Nd Nn Ns Nv Om Pb Pd Pe Qb) Lv(Hx Ii
In Ip Ir Lu Lx Lz Mc Md Mf Mj Mk Ml Mm Mz Nd Ng Nn Ns Om Pb Qb) Ik(aC Hr Ih Ii Ij Ip Ir Lx Mc Md Mf Mk Ml Mm Mq Mr Mz Ng Nk
Nn Ns Om Pb) Lu(Hr Hx Ip Ir Lx Ly Lz Mc Md Mf Mj Mk Mm Mq Mz Ng Nn Nq Ns Om Qb) Nc(Fr Hq Hu Hv Jo Jq Jr Js Li Lj Mg Na Nr Pa
Pc Pe Pf Pg Po Pz Qc) It(Hq Hu Hv Ij Jo Jq Jr Js Li Lj Pa Pc Pe Pf Pg Po Pz Qb Qc) Pb(Hr Ih Ij Ir Jl Js Lh Lx Mi Mq Mr Nv Om Oz Pa Pd Pe
Qb) Oy(Hu Hv Hw Hx Ii Iu Jm Jq Lj Mn Na Ng Pz) Mz(aC Hr Ih Ij In Ir Lx Mf Mj Nn Ns Qb) Ii(Ij Ir Jo Js Lx Mi Mq Nn No Nv Qb) Ms(Hq Hu
Hv Jk Jm Lj Pf Pg Pz) Ne(Hq Hv Jk Jm Jo Jq Pf Pg Pz Qc) Nf(Hq Hu Hw Jk Jm Lj Pf Pg Pz Qc) aC(aL Ao Ax aZ Cs Ji Li Mx Nu) Ml(Ih Ij Ir
Lh Lx Mi Mr Pe) Hr(Hv Ir Jo Jr Js Lh Pe Qb) Hx(Jl Js Mi Mr My Pe Qb) Fp(Jk Jm Jo Jq Pf Pg) Om(Ih Ij Ir Lx Mf Nn) Mb(Hq Jk Jm Pf Pg)
Lx(In Mk Oe Po) My(Hq Hu Jm) Nb(Lh Mr Pe) Ih(Iq Ly Mk) In(Ij Ir Qb) Po(Jl Mr) Nn(Jh Nq) Ir(Ly Ns) Of(Hq Qc) aN(Im Mx) MdLh Nglj
HwQb} Jp{It(Fr Hq Hu Hv Hx Ii Io Ip Iq Ir Iu Jh Jk Jm Jo Li Lj Ly Lz Ma Md Mf Mg Mj Ml Mm Mn Mu Mv Mw Na Nb Nc Nd Nk No Nq Nr
Ns Ny Oe Oh Oi Om Oz Pa Pc Pd Pe Pf Pg Po Pz Qb Qc) Is(Fr Hq Hv Hx Io Ip Iq Ir Iu Jn Jo Jq Js Li Lj Lu Ly Lz Ma Md Mf Mg Mi Mj Ml
Mm Mn Mq Mu Na Nb Nd No Nq Nr Ns Nv Ny Oh Oi Om Oz Pa Pc Pd Pe Pf Po Pz Qb Qc) Qe(Fr Hq Hx Ih Io Ip Iq Ir Jh Jm Jo Js Li Lj Lu Lx
Ly Lz Ma Md Mg Mj Ml Mn Mq Mu Na Nb Nd Nk No Nr Ns Ny Oe Oh Oi Om Oz Pa Pc Pd Pe Pf Pg Po Pz Qb Qc Vs) Mt(Hq Hr Hv Hw Hx
Ih Ii Ij In Io Ip Iq Iu Jo Li Lj Lu Lx Ly Lz Ma Mf Mg Mi Mj Ml Mm Mn Mq Mr Nc Nd Nn No Nv Ny Oh Om Oz Pa Pc Pd Pe Po Pz Qb Qc)
Ms(Fr Hq Hu Hv Hw Hx Ii In Io Iq Jk Jm Jo Lu Ly Lz Ma Md Mg Mj Mk Ml Mn Mu Mv Mw Na Nb Nd Ng Nk No Nq Nr Ns Oe Oh Oi Om
Oz Pc Pd Pf Pg Po) Nx(Hu Hv Hw Hx Ii Io Ip Iq Iu Jh Jk Jo Jq Jr Js Li Lj Ly Lz Ma Mc Mf Mg Mi Mk Ml Mm Mn Mq Mv Mw Nd No Nq Nr
Nv Ny Oh Om Oz Pa Pc Pd Po Qc) Qa(Fr Ih Ij Io Ip Iq Ir Jm Jo Js Li Lj Lx Ly Lz Ma Md Mg Ml Mm Mn Mq Mr Mu Nb Nd Nk No Nr Ns Nv
Oh Oi Oz Pa Pc Pd Pe Pf Pg Po Pz Qb Qc) Mb(Fr Hq Hr Hu Hx Ii In Io Iq Iu Jh Jk Jm Lj Ly Lz Ma Mc Md Mf Mg Mj Ml Mn Mu Mv Mw Na
Nb Ng Nk Nq Nr Ns Oe Oi Om Pa Pf Pg Po Pz) Lw(Hq Hu Hv Hw Hx Ii Ij Il In Ip Jh Jk Jq Lj Lu Ly Lz Mf Mi Mk Ml Mm Mn Mq Mv Nd Nm
Nn No Nq Nr Nv Ny Oi Om Oz Pa Pe Po Qc) Jn(Hq Hr Hu Hv Hw Hx Ih Ii In Ir Jh Jq Jr Js Li Lu Lx Ly Mc Mf Mh Mi Mk Mm Mq Mr Mv
Mw Nc Ng Nn No Nq Nv Ny Oe Om Pc Pe Qb) Jg(Hr Hu Ih Il Io Ir Jh Jk Jq Jr Js Jt Lh Lj Lu Lv Lx Ma Mc Me Mi Mk Mq Mr Mv Nc Nf Nh
Nm Nn Nq Nv Oe Om Pa Pb Pe Pz) Of(Hq Hr Hu Hw Hx Ii In Io Iq Iu Jk Jm Lj Lz Ma Md Mg Mj Ml Mn Mu Mv Mw Na Nb Ng Nk Nq Ns Oe
Oh Om Pf Pg Pz Qc) Jt(aC Hu Hx In Ir Jh Jk Jl Jo Jr Js Lh Lu Lv Lx Ly Mc Me Mf Mg Mj Mk Mp Mq Mr Mv Mw Na Nb Nc Nq Nv) Jj(Hr Hv
Hw Hx Il Ip Jh Lj Lu Ly Lz Mc Mg Mi Mk Mu Mv Mw Nd No Nq Oh Oi Oz Pa Pc Pd Pe Qc) Nm(Hc Hr Hw Ii Ik Il In Ir Iz Jh Js Lh Li Lu Lv
Lx Ly Mc Me Mk Mq Mw Nc Nn Nq Nv Pb) Mz(aC Hw Ih Ij Ir Jh Jl Jr Js Lh Li Lv Lx Mc Md Me Mf Mk Mm Mq Mr Na Nc Ni Nn Nq Qb)
Mp(Hw Ih Ik Il Ir Jl Jq Jr Js Lv Lx Mc Me Mf Mh Mk Mr Mv Mw Nc Ng Nq Ny Pb Qb) Oy(Fr Ip Jh Jk Jo Lu Ly Mc Md Me Mf Mg Mk My
Nc Nd Nf Ni No Nr Om Oz Pa Pb Pc) Nh(Hr Ih Ik Ir Jq Jr Js Lh Li Lv Lx Me Mh Mi Mk Mr Nf Ni Nn Nv Ny Pb Pe Qb) Jl(Hu Hw Hx Ih Ik Ir
Jr Js Li Lv Lx Mc Me Mf Mj Mk Mv Nc Ng Ni Nq Ny Qb) Ne(Hr Ir Jq Jr Js Lh Li Lv Lx Me Mh Mi Mk Mr My Nf Nn Nv Ny Pb Pe Qb)
Ih(Hw Ik In Ir Jq Jr Js Lh Lu Lx Me Mh Mk Mr Nc Nf Ni Nn Nv Pb Pe) Lv(Ik Il Ir Iz Jq Jr Js Lh Lx Mh Mk Mw Nc Nf Ni Pb Qb) Lx(Hx Ii Ik Il
Jr Me Mk Mv Nc Nf Ng Ni Ny Pb Po) Lh(Hr Hw Ik Il Jh Jr Mk Ml Nb Ng Ni Ny Po Qb) Pb(Ik Jq Jr Js Li Me Mq Mr My Ni Nv Pa Pe Qb)
Mh(Hr Il Ir Jq Jr Js Mk Mr Ni Nn Nv Pe Qb) Nl(Hq Jm Ma Md Ml Mn Na Nq Ns Pf Pg Pz) My(Ik Ip Jr Me Mf Mm Mq Ni No Ny Po) Nf(Ij Ik
Ir Li Mi Mq Ni Nn Ny Pe Po) Iz(aN Ax bM cX Ik Lj Mk Mq Or Pk) Qb(Hr Hw Il In Jq Me Mk Mw Nq) Ni(Ik Ir Jq Jr Js Li Nn Nv) aC(Ax Cs
Cu Hc Li Mx Ow Pk) Ik(Ir Jr Js Me Nc Ng Pe) Nv(Hu Hx Ii Il Jh Ng Ny) Jr(Hr Ir Mk Mm Nn) Js(Hr Hw Ii In Mk) Mr(Hx Mw Nc Ny) Il(aA Ir
Pe) dX(Kx Ky Pi) Nn(Hu Mv) Mx(aN Hc) Jq(Hr Ii) Lj(Ib Vs) Pe(Hx Mw) MuHu Nglj PzaA KfeP} Nt{Ns(Hr Hu Hw Hx Ij Io Iq Iu Jh Jm Jo Jr
Lu Lv Ly Lz Mb Mc Md Me Mf Mg Mi Mj Ml Mn Mq Mr Mu Nb Nd Ni Nm No Nq Nr Nu Oh Oi Om Oz Pc Pd Po Pz) Lu(Hr Hu Hv Hw Ij Io
Iq Iu Jk Jm Jo Jr Lv Lz Ma Mb Md Me Mf Mg Mi Mj Ml Mn Mq Mr Mu Nb Nd Ni Nk Nq Nr Nu Oh Oi Om Oz Pc Pd Pe Po Pz) Ni(Hr Hu Hw
Hx Ij Io Iq Iu Jh Jm Jo Jr Lv Lz Ma Mb Md Me Mf Mg Mi Mj Ml Mn Mq Mr Mu Nb Nd Nk Nq Nr Nu Oh Oi Om Oz Pc Pd Pe Po Pz) Hw(Hq
Hu Hv Ij Io Jk Jm Jo Jr Lv Lz Ma Mb Md Me Mf Mg Mi Mj Ml Mn Mq Mr Mu Nb Nd Nk Nq Nr Nu Oh Oi Om Oz Pc Pd Pe Pf Pg Po Pz)
Om(Hr Hu Hv Hx Ij Io Iq Iu Jh Jo Jr Lv Lz Ma Mb Md Me Mf Mg Mi Mj Ml Mn Mq Mr Mu Nb Nd Nk Nq Nr Nu Oh Oi Oz Pc Pd Pe Po Pz)
Oz(Hq Hu Hv Ij Io Iq Iu Jh Jk Jm Jr Lv Lz Mb Mc Md Me Mf Mg Mi Mj Ml Mn Mq Mu Mv Nb Nd Nm No Nq Nr Nu Oh Oi Pc Pd Pg Pz)
Mn(Hq Hu Hv Ij Io Jk Jm Jr Lv Lz Ma Md Me Mf Mg Mi Mj Ml Mq Mr Mu Nb Nd Nk No Nq Nr Nu Oh Oi Pc Pd Pe Pf Pg Po Pz) Mq(Hq Hu
Hv Ij Io Iq Jk Jm Jr Lv Lz Ma Mb Md Me Mf Mg Mi Mj Ml Mr Mu Nb Nd Nk Nq Nr Nu Oh Oi Pc Pd Pe Pg Po Pz) Ij(Fr Hu Hv Io Iq Jk Jr Li
Lv Ly Lz Ma Me Mf Mg Mi Mj Mr Mu Nb Nd Nk Nm Nn No Nq Nr Nu Oh Oi Pc Pd Pe Po Pz) Oh(Hr Hu Hv Hx Io Iq Jh Jo Jr Lv Ly Lz Mb
Mc Md Me Mf Mg Mi Mj Ml Mr Mu Nb Nd Nm No Nq Nr Nu Oi Pd Po Pz) Pc(Hq Hv Io Iq Jk Jm Jr Lv Ly Lz Ma Mb Md Me Mf Mg Mi
Mj Ml Mr Mu Nb Nd Nk Nm Nq Nr Nu Oi Pd Pe Po Pz) Nk(Hr Hu Hx Io Iq Iu Jh Jo Lv Ly Mb Mc Md Me Mf Mg Mi Mj Ml Mv Na Nb Nd
Nm No Nq Nr Nu Oi Pb Pd Po) Jk(Hr Hu Hx Il Io Iq Iu Jo Jr Lv Ly Mb Mc Md Me Mf Mg Mi Mj Ml Mu Mv Nd Nh Nm No Nr Nu Pd Pe Po
Pz) Lz(Hu Hv Hx Io Iq Iu Jh Jo Jr Lv Ly Mb Md Me Mf Mg Mi Mj Ml Mr Mu Nb Nd Nm Nq Nr Nu Oi Pd Pe Pz) Ma(Hr Hu Hx Io Iq Iu Jh Jo
Lv Ly Mb Mc Md Me Mf Mg Mi Mj Ml Na Nb Nd Nm No Nq Nr Nu Oi Pd Po Pz) Pg(Hr Hu Hx Il Io Iq Iu Jh Jo Lv Ly Mb Mc Md Me Mf Mi
Ml Mv Mw Nd Ng Nh Nm No Nu Pb Pd Pe Po Pz) Hq(Hr Hu Hx Il Io Iq Iu Jh Jo Lv Ly Mb Mc Md Me Mf Mg Mj Ml Mv Mw Nd Ng Nh Nm
No Nu Pd Po Pz) Pf(Hr Hu Hx Io Iq Iu Jh Jo Lv Ly Mb Mc Md Me Mf Mj Ml Mv Mw Nd Ng Nh Nm No Nr Nu Pb Pd Po Pz) Mu(Hr Io Iq Iu Jo
Jr Lv Ly Mb Mc Md Me Mf Mg Mi Mj Ml Mr Nb Nd Nm No Nq Nr Nu Oi Pd Po Pz) Hv(Hu Hx Io Iq Iu Jr Lv Mb Mc Md Me Mf Mg Mi Mj
Ml Mv Nb Nd Ng Nh Nm No Nr Nu Oi Pd Po Pz) Jm(Hu Hx Io Iq Jh Jr Lv Mb Mc Md Me Mf Mg Mi Mj Ml Mv Nb Nd Nm No Nq Nr Nu Oi
Pd Po Pz) Nq(Hr Hu Hx Io Iu Jo Jr Lv Mb Md Me Mf Mg Mi Mj Ml Mr Nb Nd Nf Nu Oi Pd Pe Po Pz) Jr(Hu Io Iq Iu Jo Lv Mb Mc Md Me Mf
Mg Mi Mj Ml Mr Nb Nd Nr Nu Oi Pd Pe Po Pz) Nb(Hr Hu Hx Io Iq Jo Lv Mb Md Me Mf Mg Mi Mj Ml Mv Nd Nr Nu Oi Pd Po Pz) Mr(Hu Io
Iq Iu Jo Lv Ly Mb Mc Me Mf Mg Mi Mj Nd Nm No Nu Oi Pd Pz) Pe(Hu Io Iq Iu Lv Ly Mb Mc Me Mf Mg Mi Mj Nd Nm No Nu Oi Pd Pz)
Mg(Hr Hu Jo Lv Mb Md Me Mf Mj Ml Nd Nr Nu Oi Pd Po Pz) Nr(Hu Io Lv Mb Md Me Mf Mi Mj Ml Nd Nu Oi Pd Po Pz) Mi(Hu Io Iq Lv
Ly Me Mf Mj Nd Nm No Nu Oi Pd Pz) Mj(Hr Hu Hx Jo Md Me Mf Ml Nd Nu Oi Pd Po Pz) Oi(Hu Jo Lv Ly Md Me Mf Ml Nd Nu Pd Po Pz)

Figure 31 Continued

Pz(Hu Io Lv Md Me Mf Ml Nd Nu Pd Po) Md(Hu Hx Me Mf Ml Nd Nu Pd Po) Mf(Lv Me Ml Nd Nm Nu Pd) Ml(Hu Me Nd Nu Pd Po) Nd(Hu Lv Me Nu Pd) Po(Hu Me Nu Pd) Lv(Hu Mb Pd) Nu(Hu Me) Io(Iq Iu) Pd(Hu Me) Iqlu JiaC} Ok{Jq(Hq Hu Hv Hx Ih Il Io Ip Iu Jk Jl Jr Js Jt Lh Li Lj Lx Ly Lz Ma Mc Md Me Mf Mi Mj Mk Ml Mm Mn Mq Mr Mu Mv Na Nb Nd Nk No Nq Nr Ns Nv Ny Oh Oz Pa Pc Pd Pe Po Pz) Hv(Hq Hu Hx Io Ip Iq Jh Jt Lh Li Lj Ly Lz Ma Mc Md Mf Mi Mj Mk Ml Mm Mn Mq Mr Mu Mv Mw Na Nb Nd Nk No Nq Nr Ns Nv Ny Oh Om Oz Pa Pc Pd Pe Pf Pg Po) Li(Hq Hu Hx Ih Io Ip Jk Jl Jr Jt Lh Lj Lx Ly Lz Ma Mc Md Mf Mi Mk Ml Mm Mn Mq Mr Mu Mv Na Nb Nd Nk No Nq Nr Ns Nv Ny Oh Oi Om Oz Pa Pc Pd Pe Pz) Hu(Fr Hq Hx Il Jk Jm Jr Lh Lj Ly Lz Ma Mc Md Mi Mj Mk Ml Mm Mn Mq Mv Mw Na Nb Nd Ng Nk No Nq Nr Ns Ny Oh Oi Om Oz Pa Pc Pd Pe Pf Pg Po Pz) Jm(Hq Hx Ih Ik Il Io Ip Iq Ir Iu Jh Jl Jr Js Jt Lh Lv Lx Me Mf Mh Mi Mj Mk Mq Mr Mu Mv Mw Nd Ng Ni Nn Nq Nr Ns Nv Ny Om Oz Pa Pd Pz Qc) Pf(Fr Hq Hx Jh Jl Jo Jr Js Jt Lh Lj Ly Lz Ma Mc Md Mi Mj Ml Mm Mn Mq Mr Mu Mv Na Nb Nd Nk No Nq Nr Ns Nv Ny Oh Oi Pa Pc Pe Pg Po Pz Qc) Jk(Hq Hx Ik Il In Io Ip Iq Iu Jh Jo Jr Jt Lh Lj Lx Ly Ma Md Me Mf Mi Mj Mk Mq Mr Mu Mv Nd Ni Nq Nr Ns Nv Ny Om Oz Pa Pc Pd Pe Pz) Ij(Hq Hw Hx Io Ip Jh Jl Jo Lh Lv Ly Lz Ma Mc Md Mf Mi Mj Mk Ml Mm Mn Mq Mr Mu Na Nb Nd Nn No Nr Ns Nv Ny Oh Oi Oz Pa Pd Pz Qc) Pg(Fr Hq Hx Jh Jl Jr Js Jt Lh Lj Ly Lz Ma Mc Md Mi Mj Ml Mm Mn Mq Mr Mu Na Nb Nd Nk No Nq Nr Ns Nv Oh Oi Oz Pa Pc Pe Po Pz Qc) Po(Hq Hx Ik Il Io Ip Iq Iu Jh Jo Lj Ly Lz Ma Mc Md Mf Mj Mk Ml Mm Mn Mq Mu Mv Mw Na Nb Ng Nk No Nq Ns Ny Oh Om Pa Pc Pz) Fr(Hq Hw Hx Jh Jl Jo Jr Js Jt Lh Lj Ly Lz Ma Mc Md Mi Mj Ml Mm Mn Mu Na Nb Nk No Nr Ns Oh Oi Oz Pa Pc Pd Pe Pz Qc) Lj(Hq Hx Jh Jr Jt Lh Lz Ma Mc Md Mi Mj Mk Ml Mm Mn Mq Mu Mv Na Nb Nd Nk No Nr Ns Nv Ny Oh Oi Oz Pa Pc Pd Pe) Oi(Hq Hx Jh Jl Jo Jr Js Jt Lh Lz Ma Mc Md Mi Mj Ml Mm Mn Mu Na Nb Nk No Nr Ns Oh Oz Pa Pc Pd Pe Pz Qc) Nk(Hq Hx Jh Jl Jr Js Jt Lh Lz Ma Mc Md Mi Ml Mm Mn Na Nb No Nr Ns Oh Pa Pc Pd Pe Pz Qc) Hq(Hx Lh Ly Lz Ma Mc Md Mi Mj Mk Ml Mm Mn Mu Mv Mw Na Nb No Nq Nr Ns Ny Oh Om Pc Pe) Pc(Hx Jl Jr Jt Lh Lz Ma Mc Md Mi Ml Mm Mn Mu Na Nb No Nr Ns Nv Oh Pa Pe Pz) Hx(Ly Lz Ma Mc Md Mj Mk Ml Mm Mn Mv Mw Na Nb No Nq Nr Ns Ny Oh Om Pa) Pe(Jl Jr Js Jt Lh Ly Ma Mc Mi Mm Mn Mu Na Nd No Ns Nv Oh Oz Pd Pz) Na(Jh Jl Jo Jr Lh Lz Ma Mc Md Ml Mn Mu Ns Oh Pa Pd Pz Qc) Lh(Jr Jt Ly Lz Ma Mc Mi Mm Mn Mu Nd No Ns Oh Oz Pa Pd) Nb(Jh Jo Jr Lz Mc Md Ml Mn No Ns Oh Pa Pd Pz Qc) Jt(Lz Ma Mc Md Mi Ml Mm Mn Mu No Nr Ns Nv Oh Pa) Jr(Ly Lz Ma Mc Md Mi Ml Mm Mn No Nr Ns Nv Oh) Pz(Ly Lz Ma Mc Md Mi Mk Ml Mm Mn No Ns Oh) No(Jl Lz Mc Md Mn Nr Ns Pa Pd Qc) Oh(Jh Jl Lz Ma Md Mm Mn) Jh(Lz Ma Mc Ml Mn) Jl(Mi Mm Mu Nv Oz) Md(Lz Mc Ml Mn) aC(aN bM Im Ji) Mm(Mc Mi Mn) Lz(Ml Mn) NrPa} Im{Jt(Fr Hu Hv Hx Ih Ij Ip Is Jk Jo Jq Li Lj Lz Mc Md Me Mf Mg Ml Mn Mp Mq Mu Mv Nb Nd Nk Nm No Nq Nr Ns Ny Oi Om Oz Pa Pc Pd Pe Pf Pg Po Pz) Qe(Fr Hx Ih Ij Io Ip Ir Jk Jo Lj Lu Lz Ma Mc Md Mg Mi Mj Ml Mm Mq Mr Mu Mv Na Nb Nd Nk Nq Nr Ny Oh Oi Om Pa Pf Pg Po Pz Qa Qb Qc) Nx(Hq Hv Hx Ih Ij Io Ip Is Iu Jk Jm Jo Jr Lj Ly Lz Ma Mc Md Me Mg Mj Ml Mn Mq Mu Mv Na Nb Nd Nk Nq Nr Ns Ny Oh Oi Om Pa Pf Pg Po) aA(Hq Hu Hx Ih Ii Ik Iq It Iu Jk Jq Jr Lh Li Lj Lu Lx Ly Me Mh Mk Mp Mr Mv Mw Nd Nm Nn No Nq Oe Om Oz Pa Pb Pd Pe Pf Qc) Mz(Fr Hq Hu Hv Ij Ik Ip Iq Ir Iu Jm Jo Lu Mc Me Mf Mi Mk Mq Mr Na Nd Ng Ni No Nr Oh Om Oz Pa Pc Pd Pe Pf) Js(Fr Hq Hx Ii Ik Iq Is Jh Jm Jr Li Lu Lx Me Mf Mk Mp Mv Mw Ng Nn No Ns Nv Ny Oe Oz Pb Pd Pe Qa Qc) Nv(Hq Hu Hx Ik Iq Is It Jh Jk Jl Jm Jr Lh Lx Ly Me Mf Mh Mj Mk Mm Mp Mr Mv Nq Ny Om Oz Pb Qa Qc) Nf(Hq Hr Hu Hw Ii Iu Jk Jm Lj Lz Ma Mc Md Mj Mk Ml Mn Mu Mw Nb Nd Nq Nr Ns Oe Oi Om Pa Pg Pz) Mx(Fr Hv Ih Ij Is Jo Lu Ly Me Mf Ml Mn Mp Mv Mw Na Nd Nq Ns Ny Oe Oz Pa Pc Pd Pe Po Pz Qb) Jn(Fr Hq Hw Ik Iq Jh Jm Jq Li Lu Me Mf Mh Mi Mk Mr Ng Nn No Oe Oz Pb Pc Pd Pe Qa Qc) In(Hq Hr Hu Hv Hw Ik Il Iq It Jh Jo Ly Me Mh Mi Mm Mq Mr Ng Nn Om Oz Pb Pd Qb Qc) Mt(Fr Ih Ij Io Lu Lz Ma Md Mg Ml Mn Mq Mu Na Nb Nd Nk Nr Oi Pa Pf Pg) Of(Fr Hq Hr Hw Ik Iq Is Jo Jr Lu Mf Mi Mk Mr Nn No Oy Oz Pb Pd Pe Qa) Mb(Fp Ik Il Iu Jq Li Mi Mk Ms My Nc Ne Ng Nh Ni Nn Oy Pb Pe Qc) Jl(Hq Hw Hx Ik Iq It Jh Li Lv Mk Mv Mw Ng Ni Nn No Pb Qa Qc) aC(aM aS Ax bA cN Cu dJ Ik Io Is Iv Li Mf Mi Mk Ni Nj Nm Nu) Ms(Hq Hw Is Jh Jq Jr Lv Lx My Ng Nm Nn Oz Pb Qc) Ne(Hw Ik Is Iu Jh Jq Li Mk Mp Ng Nn No Ny Pb Qc) Lh(Fp Hw Ik Is It Lv Lx Md Mk Ni Nm Nn Om Qa Qc) Nh(Hr Ik Is Iu Jq Li Mp Ng Ni Nm Nn Na Qa Qc) Il(Ij Lw Lx Ly Mh Mi Mm Mp Mr My Nc Ni Oz Qc) Oy(Li Lv Mi Mk Mr Nc Ni Nm Nn Oz Pd) Qa(Fp Hr Hw Jm Lv Mk Mm Nc Ni Nm) Lw(Hw Iq Li Lv Lx Ng Ni Nn Qc) Fp(Hw Ik Jq Lv Mk Mp Ni Qc) Lx(Hr Lv Mh Mk Mm Nc Ni Nm) Jj(Ij Io Jk Jm Ma Mj Nb Pz) Mm(Hr Jq Jr Ng Ni Nm Qc) My(Fr Iq Li Mr Nc Nn Pe) Nc(Hr Jq Mr Nk Nm No) Lv(Li Mk Nm Nn Qc) Pe(Hr Hx Mh) aN(cM Ji Og) Nm(Hr Ng) Ni(Li Mp) MrIi} Jg{Qa(Fr Hv Ih Ij Ip Ir Jm Jr Js Jt Lh Li Lj Lu Lx Ly Lz Ma Mc Md Mf Mi Ml Mm Mn Mq Mr Mu Nb Nd Nk Nm Nn No Nr Ns Nv Oh Oi Oz Pa Pc Pd Pe Pf Pg Po Qb Qc) Fp(Hq Hv Hx Ih Ii Il Io Ip Ir Iu Jo Jr Lh Lj Lu Lv Ly Lz Ma Mc Md Me Mf Mi Mj Ml Mm Mn Mq Mr Mu Na Nb Nd No Nq Nr Ns Nv Ny Oh Oi Om Oz Pc Pd Pe Pf Po) Nl(Hr Hu Ih In Ip Ir It Iu Jh Jq Jr Jt Lh Lj Lv Mb Me Mh Mi Mk Mr Mt Mv Mw Nf Nh Nk Nm Nn No Nv Nx Oe Pa Pb Pe Pz Qc) Qb(Hq Hr Hu Hw Hx Ii Ik Il Io Iq Is It Jl Jm Jn Jq Jr Js Jt Lh Lv Me Mg Mh Mr Mt Nc Nh Nm Nq Ny Om Pb Qc) Nu(Hr Ih Ik Ip Ir Iu Jh Jq Jr Jt Lh Lj Lv Lx Mg Mh Mk Mp Mt Mv Mw Nc Ne Nf Nh Nv Nx Ny Oe Pa Pb Qc) Mz(aC Hu Hw Ih Ij Ik Il Is It Jk Jl Jo Jr Js Lv Lx Me Mg Mj Mk Mp Mq Mt Na Nb Ni Nq Oe Po Pz Qc) Qe(Fr Hv Ih Ip Ir Li Lj Lu Ly Lz Md Mf Ml Mm Mn Mq Mu Na Nb Nk No Nr Ns Nv Oi Pc Pf Pg Po Qc) Oy(Fr Hq Hv Ij Ik In Ip Ir Jk Li Lu Ly Lz Md Me Mg Mm My Nf Ni Nm No Nq Nr Ny Oe Om Pc Pf Pz) Jj(Hr Hq Hw Ii Il In Io Iq Iu Jk Lz Mc Md Mg Mj Mn Mu Na Nb Nk Ns Oi Om Pc Pf Pz) Ng(Ih Ij It Jq Jr Mb Mh Mi Mr Ms My Nc Nd Ne Nh Nm Nn Pa Pe Qc) aA(Fr Hq Hv Iq Iu Ly Md Mf Ml Mn Mu Na Nk Ns Oh Om Pc Pg) Lw(aC Hr In Is It Jh Jl Lx Mg Mh Mr Mt Mw Nc Nf Nh Nx) My(Ij Ik It Jr Jt Lv Mf Mg Mh Ms Nc Nh Nm Pa Po Qc) Jn(In Jh Jl Lx Mb Mg Mp Mt Mw Nc Ne Nf Nh Ni) Js(Ii Ik In Jh Jo Mg Mh Mt Mv Mw Ne Nf Ni Pz) Ms(Ih Jl Jq Jt Lx Mp Nc Ne Nh Pa Qc) Mt(Ik Is Jh Mb Mg Mk Mv Mw Nx Oe) Mb(Ik Is Jq Jt Lh Lx Mg Nv) Jl(Hr Jh Mg Mh Mv Nc Ne Nf) Nj(Ij Il Jm Ma Mj Na Nq) Mp(Mg Mv Mw Ne Nf) Is(Jh Mg Nc Ne Nf) Lx(Jh Mk Nc) Mw(Mr Nn Pe) Lh(Jh Mh Nf) Mv(Nn Nv) Ij(Iv Mx) AjcM MgNx MhPe NcNi IhIn JhJq} Iv{Nv(Fr Hu Hx Ih Io Ip Is Jh Jl Lh Li Lv Mc Md Me Mf Mg Mi Mj Ml Mm Mn Mp Mq Mr Nc Nn No Ny Om Pa Pb Qa) Nj(Hr Hx Iq It Jr Lj Lv Mc Mf Mh Ml Ms Mu Mw My Ne Nl Ns Oe Oh Oi Oz Pb Pc Pd Po Pz) Lx(Hr Ih Is It Jh Jq Js Li Lv Mb Mi Mj Mp Mr Ms Mt Mv Mw Nc Ng Nn No Ny Oe Pb Qa) Qa(Fp Fr Ik Is It Jh Jl Jn Jq Js Lh Li Lv Mh Mj Mp Mx Ne Nh Ni Nn No Ny Pb Qe) Nx(Hr Ih Ik Ip Ir Is Jn Jq Js Lj Lv Mb Mh Mi Mr My Nc Ni Nr Oe Pa Pb Pe Qb Qc) Mz(aC Hr Ih Ii Ij Ip It Jq Jr Js Lv Mi Mr Mv Mw Na No Nr Ns Pa Pe Pz Qb Qc) Jt(Fr Hw Ih Ik Il Ir Is Jh Jr Lh Li Lw Mh Mp Mr Nc Ng Ni Nn No Qb) aA(Ij Ik Is Jj Lj Ma Mh Mk Mn Mq Mr Ms Nd Ni Of Oi Pd Pe Po Pz Qc) Og(Ii Il Jj Jk Lv Ma Mb Me Mf Mg Mi Mk Mn Mq Mu Oi Pa Pe Qc) Qe(Fp Fr Hw Ik Is It Js Li Lv Mh Mi My Nc Ni No Ny Of Pb) Ny(Fp Jh Jl Jn Lh Mb Mk Mm Mp Ms My Ne Nh Ni Nm Oy) Mt(Hr It Jq Js Li Lv Mb Mh Mp Ne Ng Nh Ni No Oe) Fp(Fr Jh Jl Jn Jq Js Lh Mk Mp Mx Ne Nh Nn Oy) Nm(Fr Is Jj Jl Jn Js Lh Li Mm Ne Nf Nh Nn Nu) Nu(It Jh Li Lv Mb Mk Mp My Nh No Of Pa) Jl(In Li Lw Mb Mh Mk Mx Nh Nl Nn Of Oy) Mm(Fr Is It Js Mb Mp Ms Ne Nf Nh Oy) Jn(Fr Jh Li Mk Mp Ms Ne Nf Nh Oy) Lh(Is Lw Ml Mv Mx Nh Nn Of Pb Po) Lw(Fr In Is Js Nf Nh Nn No) Mx(Ik Jh Jq Li Nh Nl No Oy) Js(Fr Jh Mk Ms Nl Of Oy) Jj(Ih Ij Jh No Nr Qb) Fr(In Is Mb Ne Nh) Nn(Mk Ms Ne Nh Oy) Nl(Is Jh Jq Mp Nk) Li(Mk Nh Ni Of) In(Ij Mp Qb) Nf(Is Mp) NoNh MsJq JiaC} Nj{Nv(Fr Hu Hw Hx Ij Io Iq Ir Iu Jh Jk Jo Jq Jr Js Li Lj Lu Lv Ly Lz Ma Mc Md Me Mf Mg Mi Mj Ml Mn Mq Mu Na Nb Nc Ne Nl Nq Nr Ns Ny Oh Oi Om Oz Pc Pd Pe Qb Qc) Qa(Hq Hu Hv Hx Ih Ii Io Iq Ir Jk Jm Jo Jr Lj Lu Lv Ly Lz Ma Mb Mc Md Me Mf Mg Mj Ml Mn Mq Mu Mv Mw Na Nb Nc Ne Ng Nl Oh Oi Om Oz Pc Pd Pe Pf Pg Pz Qb Qc) Qe(Hq Hu Hv Hw Hx Ih Ii Ij Io Iq Ir Jm Jo Jr Lu Lv Lz Ma Mb Mc Md Mc Mf Mg Mh Mj Ml Mn Mq Ms Mu Mw Nb Nc Ne Nr Ns Oh Oi Oz Pb Pc Pd Pe Pg Qb) Mz(Ip Ir It Jq Jr Lv Ma Mb Me Mi Mn Mq Ms Nd Ne Nh Nl Nr Ns Oe Of Oi Pe Pz Qc) Lh(Fp Fr Hx Ih Ik Is

Figure 31 Continued

Jl Jn Js Li Lw Mk Ml Mm Mv Mw Nb Nm Nn No Nx Ny Of Pb Qb) Mt(Fr Hr Ih Ij Ip Ir It Jq Li Lj Lx Mi Mq Mr Ms My Nd Nf Of Pa Pe Qb Qc) Jt(Ip Ir Iu Jh Jo Jr Li Lw Mb Mh Mi Mj Ms Nd Ne Nf Ng Nh Nl Oe Pa Qc) aA(Ii Ik Jm Jq Lj Lv Mi Mn Mq My Nd Ng Nh Nl Oe Oi Oy Pd Pe Po Pz) Lx(Fp Ih Ik Is It Jh Jn Js Mh Mm Mp Mr Nf Nh Nm Nn No Ny Oe Oy) Jl(Fr Ih Jn Js Li Mk Mm Mx Nf Nk Nm Nn No Nx Ny Of Oy) Fr(Fp Ih In Is Jn Lw Mk Mp Nf Nk Nm Of) Js(Fp Hr Ik Jh Mp Mx Nf Nk Nm No Of Oy) Nu(Fp Ih Ip It Jq Li Mm Mp Ni Ny Qb) Fp(Jj Lw Mp Nm Nx) Mx(Ih Is Jn Li Mp) In(Ij Jn Mp Nn Nx) No(Jj Lw Mp Nx) Og(Jq Mu Nr Pz) Lw(Li Nn Ny) Mm(Jn Mr) Ni(Is Qb) Jj(Ih Is) Li(Nf Nx) NnMr JiaC} Og{Qa(Hr Hu Hv Iq Ir It Iu Jo Jr Lx Ly Lz Mc Md Me Mf Mg Mh Mi Mj Mq Mr Mu My Na Ng No Nq Ns Oe Of Oy Oz Pa Pb Pc Pd Pe Pz Qb) Nv(Hv Hw Ih Ii Ik Il In Ir Jh Jl Js Lh Li Lx Ly Mc Me Mf Mh Mk Mm Mp Mq Mr Mw Nn Nq Oi Om Pb Qb) Qe(Fr Hv Ik In Ip Ir It Jo Lx Mf Mg Mi Mr Ni No Oi) Nx(Ir Is It Jh Jj Jn Js Lw Mm Ne Nh) Ij(In Jn Js Lh Li Lx Mb Mp Ms Nn) Mt(Ir It Jl Jq Lh Li Mm Nn Qb) Nl(Fp Fr Jn Lh Mm Mx Nn Ny) Jt(Fr Js Li Mm Ms Nc Nn Ny) Nu(Fr Ir Li Lx Mm Nn) Mx(aA Jl Jn Lw Nn Ny) aA(Fp Mm Nr Qb) Lw(Jl Js) FpMm NmJn MbJl} aC{Ji(aF aH aI AJ aK AO aP Ar aS aV aW Ba BC bE bH bL bO bQ bX bZ cA cB cC cF cH cI cL cO cR Cs CU cV cW dA dF dG dI DK dL dM Fr Hr Hu Hx Ih In Ip Iq Ir Is It Iu Jn Jr Lh Lu Lv Lx Lz Ma Mc Mh Mi Mj Mm Mq Mr Ms Mu My Na Nb Nc Nd Ne Ng Nl Nm Nq Ny Oe Oi Om Oy Oz Pe Pf Pg Po Qb) Jt(AR Ax bA cD Cs Cu Li Lx Mk Mt Mx) Mz(AR Ax cD cM In Lj Lw Nk) Et(bM cM Is Jj Lj Mt Of) aN(Is Li Mt) Lw(Cs Qe) Io(Ax Cu) BbbM IsJj} aA{Mt(Ih Jh Jj Jl Jq Lh Li Lw Mk Mm Ms Nf Nm Nv Ny Qb) Qe(Hw Jh Jj Jl Jq Js Lh Li Lx Mp Ms Nc No Nv Ny Of) Jn(Fr Hr Ih In Jh Jl Jt Lh Lw Mp My Nc Nh Nm Nr Oy) Qa(Fp Hw In Jj Jt Lv Mm Ms Mx Ne Nh Ni Nm Of) Mz(Js Li Lx Mb Ms Nc Nf Nv Qb) Nl(Ih Js Lx Mm Mx No Nu Nx) Fp(Hr Js Mm Nf Nu Nv) Nu(Jl Js Jt Li Nv) Mx(Li Mm Nv) Nf(Js Nv Nx) Jt(Mb Of) Nx(Li Lx) IiLh} Jj{Qa(Js Lh Lv Mb Mt Mx Ne Nf Nh Nm Nn) Qe(Jo Jq Lh Lw Mb Mx Mz Ne Nh Nn) Nv(Is Js Mm Mt My Mz Ne Nh Nm Of) Nx(Ir Jh Nc Ne Nh Nm Nn Ny Pz) Nu(Is It Mt Mx Mz Nl Nn Ny) Jt(Jl Jn Mm Mz Ne Qb) Nl(Jn Js Mz Nn) bM(Dc Is Jn) Mm(Js Mt) aN(Ji Mx) MtJn} Jt{Nu(Ii In Mx Mz Nl Nx Of Oy Qa Qe) Mt(Fp In Mb Mk Nl Nx Of Qe) Qa(Ii In Mb Ms My Nl Nx) Mx(In It Jr Js Nl Nx) Fp(Hr Ii In Mj Nx) Qe(In Mb Ms My Nx) Nl(Ii In Lx Of) Aj(aN bM) Mz(Ms Ne) Nv(Mb Oy) MmOf IiJl InNx} Nx{Qa(Fp Hr Il Iu Lw Mb Mt Mx My Mz Ni Nl Nm) Qe(Hr Il Lw Mm Mx Nf Nm Oy) Nu(Fp In Mx Mz Of) Mt(Fp In Mx Oy) Mx(In Lw Nf) Of(Fr Li Lx) Fp(Mm Nl) IiLh NvOy} Nu{Qe(Il Is Jq Mb Ms Mx My Mz Nf Nm Oy) Qa(Lw Mb Ms My Mz Nf Nl Oy) Lh(Ii My Oy) Mz(Nf Nl) Nv(My Nf) LwMx InJs} Nv{Of(Fp Mm Mx My Nf Nh Ni) Oy(Jn Lw Ne Nh Nm) Nl(Fp Mz Ni) My(Mb Mt) Nf(Mx Mz)} Mt{Qe(Lw Mk Ms Nl Nm Oy) My(Js Lh Mz Qa) Ms(Jn Js Mz) Oy(Jn Lh Qa) MzNl} Nl{Mz(Fp Lw Lx Mp Nm) Qe(Il In Mm Ni) Qa(In Nk) FpMm IiLh} Nf{Mz(Fp Lh Qa) bM(Cu Ji) FpMm QaLh} Mx{cM(Uh Vt) NmQe LwaN IiLh} Qe{Nm(In Mb) MbMm MsMz} Ji{aN(bM cD Lj) JobM} Lh{Ii(Jn Js) QaOy} bU{cOoW fBkR} cM{UhbM bOoD} WmJkwQ LwLjaN jFqUkK

Unconstrained panels with 2 analytes, where 1.0E-8 >= 'model p-value' > 0. Contains 720 panels of 199,260 total panels evaluated. : Ji(aA aC Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pc Pf Pg Po Pz Qa Qb Qc Qd Qe) Et(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nt(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nu Nv Nw Nx Ny Oe Of Og Oh Oi Ok Om On Oy Oz Pa Pb Pc Pd Pe Pf Pg Po Pz Qa Qb Qc Qd Qe) Ok(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nu Nv Nw Nx Ny Oe Of Og Oh Oi Om On Oy Oz Pa Pb Pc Pd Pe Pf Pg Po Pz Qa Qb Qc Qd Qe) Qd(aA Fp Hr Hv Hw Ii Ik Il Im In Ip Ir Is It Iu Iv Jg Jh Jj Jl Jn Jp Jq Jr Js Jt Lh Li Lu Lv Lw Lx Lz Mb Me Mf Mh Mi Mj Mk Mm Mp Mq Mr Ms Mt Mx My Mz Nc Nd Ne Nf Nh Ni Nj Nl Nm Nn No Nq Ns Nu Nv Nw Nx Ny Oe Of Og On Oy Oz Pb Pc Pd Qc Qe) On(aA Fp Hr Hu Hw Hx Ih Ii Ik Il Im In Ip Iq Ir Is It Iv Jg Jh Jj Jk Jn Jp Jr Js Jt Lj Lv Lw Lx Mb Me Mh Mk Mp Mr Ms Mt Mv Mw Mx My Mz Nc Ne Nf Ng Nh Ni Nj Nl Nm Nq Nu Nw Nx Ny Oe Of Og Om Oy Pb Qa Qb Qe) Nw(aA Fp Ik Il Im Is It Iv Jg Jj Jn Jp Jt Lu Lv Lw Mb Me Mh Mp Ms Mt Mv Mw Mx My Nc Ne Nf Nh Ni Nj Nl Nm Nu Nx Ny Of Og Oy Qa Qe) Jp(aA Fp Im Is It Iv Jj Jn Jt Lw Mb Ms Mt Mx Nj Nl Nu Nx Of Og Qa Qe) Im(aA Iv Jg Jj Js Jt Mt Mx Mz Nf Nj Nl Nu Nx Og Qe) Jg(aA Fp Iv Jj Mx Nj Of Og Oy Qa Qe) Nj(Iv Nv Qa Qe) Iv(aA Lx Nv) Og(Nv Qa)

Unconstrained panels with 2 analytes, where 1.0E-7 >= 'model p-value' > 1.0E-8. Contains 363 panels of 199,260 total panels evaluated. : Nw(aC Fr Hq Hr Hu Hv Hw Hx Ih Ii Ij In Io Ip Iq Ir Iu Jh Jk Jl Jm Jo Jq Jr Js Lh Li Lj Lx Ly Lz Ma Mc Md Mf Mg Mi Mj Mk Ml Mm Mn Mq Mr Mu Mz Na Nb Nd Ng Nk Nn No Nq Nr Ns Nv Oe Oh Oi Om Oz Pa Pb Pc Pd Pe Pf Pg Po Pz Qb Qc) Jp(Hr Hu Hv Hw Hx Ih Ii Ij Ik Il In Ip Ir Iz Jg Jh Jl Jo Jq Jr Js Lh Li Lj Lu Lv Lx Ly Lz Mc Mc Mf Mh Mi Mk Mm Mp Mq Mr Mv Mw My Mz Nc Nd Ne Nf Ng Nh Ni Nm Nn No Nq Nr Nv Ny Oe Oh Oy Oz Pa Pb Pc Pd Pe Po Qb Qc) On(Fr Hq Hv Ij Io Iu Jl Jm Jo Jq Lh Li Lu Ly Lz Ma Mc Md Mf Mg Mi Mj Ml Mm Mn Mq Mu Na Nb Nd Nk Nn No Nr Ns Nv Oh Oi Oz Pa Pc Pd Pe Pf Pg Po Pz Qc) Qd(aC aN Fr Hq Hu Hx Ih Ij Io Iq Jk Jm Jo Lj Ly Ma Mc Md Mg Ml Mn Mu Mv Mw Na Nb Ng Nk Nr Oh Oi Om Pa Pe Pf Pg Po Pz Qa Qb) Im(aC Fp Hr Hw Il In Iq Jl Jn Jq Jr Lh Li Lv Lw Lx Mb Mm Mp Ms My Nc Ne Ng Nh Ni Nm Nn Nv Of Oy Pe Qa Qc) Jg(Ih Is It Jl Jn Jq Jr Js Jt Lh Lv Lw Lx Mb Mg Mh Mp Mr Ms Mt Mw My Mz Nc Ne Nf Ng Nh Nl Nu Nx Pa Qb Qc) Iv(Fp Fr Is Jl Jn Jq Js Jt Lh Li Lw Mm Mp Mt Mx Mz Nl Nm Nn No Nu Nx Ny Og Qa Qe) Nj(aA Fr Jl Js Jt Lh Li Lx Mt Mx Mz Nu) Qe(aA Jj Mt Nl Nu Nx Og) Qa(aA Jj Nl Nu Nx) Nv(aA Jj Nl Of Oy) Mt(aA Jt Nx Og) Jt(aC Nl Og) MzaC IjOg JnaA Unconstrained panels with 2 analytes, where 1.0E-6 >= 'model p-value' > 1.0E-7. Contains 431 panels of 199,260 total panels evaluated. : Jg(aC Aj Fr Hq Hr Hu Hv Hw Hx Ii Ij Ik Il In Io Ip Iq Ir Iu Jh Jk Jm Jo Li Lj Lu Ly Lz Ma Mc Md Me Mf Mi Mj Mk Ml Mm Mn Mq Mu Mv Na Nb Nd Ni Nk Nm Nn No Nq Nr Ns Nv Ny Oe Oh Oi Om Oz Pb Pc Pd Pe Pf Pg Po Pz) Im(aN Fr Hq Hu Hv Hx Ih Ii Ij Ik Io Ip Ir Is It Iu Jh Jk Jm Jo Lj Lu Ly Lz Ma Mc Md Me Mf Mg Mh Mi Mj Mk Ml Mn Mq Mr Mu Mv Mw Na Nb Nd Nk No Nq Nr Ns Ny Oe Oh Oi Om Oz Pa Pb Pc Pd Pf Pg Po Pz Qb) Iv(Aa Hr Ih Ij Ik In Ip Ir It Jh Jj Jr Lj Lv Ma Mb Mi Mk Mn Mq Mr Ms My Nc Nd Ne Nf Nh Ni Nr Of Oy Pa Pd Pe Po Pz Qb Qc) Qa(Fp Hr Hw Il In Is Jh Jl Jn Jq Js Jt Lh Li Lv Lw Lx Mb Mk Mm Mp Ms Mt Mx My Mz Nc Ne Nf Nh Ni Nm Nn Nv Of Oy) Qe(Aa aC Fp Il In Is Jh Jl Jn Jq Js Jt Lh Li Lv Lw Lx Mb Mm Mp Ms Mx Mz Nc Ne Nf Nh Ni Nm Nv) Jp(aC Fr Hc Hq Ib Io Iq Iu Jd Jk Jm Ma Md Mg Mj Ml Mn Mu Na Nb Nk Ns Oi Om Or Pf Pg Pk Pz Vs) Mt(aC Fp Is It Jj Jl Jn Jq Js Lh Li Lw Mb Mk Mm Ms Mx My Mz Nl Nm Nn Nu Nv Ny Oy) Nj(Fp Ih Ij Ip Ir Is Jh Jn Lw Mm Mp Mr Ni Nm Nn No Nx Ny Og Qb) Nv(Fp In Is It Jn Jt Lw Mb Ms Mx My Mz Ne Nf Nh Ni Nm Nu Nx) Nu(aA Fp Is Jj Jl Jn Jq Js Jt Lh Lx Mx Mz Nl Nx Ny Og) aA(Fp Ih Jl Js Jt Lh Li Lx Mm Mx Mz Nl Nr Nx Qb) Nl(Fp Fr Jl Jn Js Lh Li Lx Mm

Figure 31 Continued

Mx Mz No Nx) Jt(Aj Fp Jj Jn Lx Mb Mx Mz Ne Nh Nx Qb) aC(Ar Et Is Li Lw Nm Ok On) Mx(Jn Lw Lx Mm Nm Nx Og) Nx(Fp Jj Li Lx Mz Og) Og(Is Jl Js Li Lx) Lx(Jn Mz Nh) Ji(Aa aN bM) Js(Jj Ms Nf) Lh(Ii My Nf) Nw(aN bM) FpMm QdbM Unconstrained panels with 2 analytes, where 1.0E-5 >= 'model p-value' > 1.0E-6. Contains 905 panels of 199,260 total panels evaluated. : Mt(Aa aN Fr Hq Hr Hu Hv Hw Hx Ih Ii Ij Ik Il In Io Ip Iq Ir Iu Jh Jk Jm Jo Jr Lj Lu Lv Lx Ly Lz Ma Mc Md Me Mf Mg Mh Mi Mj Ml Mn Mp Mq Mr Mu Mv Mw Na Nb Nc Nd Ne Nf Ng Nh Ni Nk No Nq Nr Ns Oe Of Oh Oi Om Oz Pa Pb Pc Pd Pe Pf Pg Po Pz Qb Qc) Nv(Fr Hq Hr Hu Hv Hw Hx Ih Ii Ij Ik Il Io Ip Iq Ir Iu Jh Jk Jl Jo Jq Jr Js Lh Li Lj Lu Lv Lx Ly Lz Ma Mc Md Me Mf Mg Mh Mi Mj Mk Ml Mm Mn Mp Mq Mr Mu Mv Mw Na Nb Nc Nd Ng Nk Nn No Nq Nr Ns Ny Oe Oh Oi Om Oz Pa Pb Pc Pd Pe Pf Pg Pz Qb Qc) Qe(aN Fr Hq Hr Hu Hv Hw Hx Ih Ii Ij Ik Io Ip Iq Ir It Iu Jk Jm Jo Jr Lj Lu Ly Lz Ma Mc Md Me Mf Mg Mh Mi Mj Mk Ml Mn Mq Mr Mu Mv Mw My Na Nb Nd Ng Nk Nn No Nq Nr Ns Ny Oe Of Oh Oi Om Oy Oz Pa Pb Pc Pd Pe Pf Pg Po Pz Qa Qb Qc Ub) Qa(Aa aC aN Fr Hq Hu Hv Hx Ih Ii Ij Ik Io Ip Iq Ir It Iu Jk Jm Jo Jr Lj Lu Ly Lz Ma Mc Md Me Mf Mg Mh Mi Mj Ml Mn Mq Mr Mu Mv Mw Na Nb Nd Ng Nk No Nq Nr Ns Ny Oe Oh Oi Om Oz Pa Pb Pc Pd Pe Pf Pg Po Pz Qb Qc) Iv(aC Hq Hu Hv Hw Hx Ii Il Io Iq Iu Jk Jm Jo Lu Ly Lz Mc Md Me Mf Mg Mh Mj Ml Mu Mv Mw Na Nb Ng Nk Nq Ns Oe Oh Oi Om Oz Pb Pc Pf Pg) Jt(aN Fr Hr Hw Ih Ii In Ip Ir Is It Jh Jl Jq Jr Js Lh Li Lu Lv Lw Mh Mj Mm Mp Mr Ms My Na Nc Nf Ng Ni Nn No Nr Ny Of Oy Po Qc) Lx(aC aN Dw Eo Ew Fp Hr Ih Ik In Ip Ir Is It Jh Jj Jl Jq Jr Js Lh Li Lv Lw Mb Mk Mm Mp Mr Ms My Nc Ne Nf Ni Nm Nn Ny Oy Qb) Mx(aC aN cM Fp Fr Ih Ij Ik In Is It Jd Jh Jj Jl Jq Js Lh Li Lv Mb Mp Mz Ne Nf Nh Nn No Ny Pz Qb Ur Vt) Jp(aN Ed Id Je Ju Jv Kc Kl Kx Oa Ou Ow Qt Qu Qw Ra Rc Rf Rg Rh Tz Ua Ub Uc Ue Uk Um Ur Us Uu Uv Vt Vu) Nx(aC Fr Ih In Ir Is It Jh Jl Jn Js Lh Lv Lw Mb Mi Mm Mp Mr Ms Nc Ne Nf Nh Nm Nn No Nr Ny Of Pe Qb Qc) Js(Fp Fr Hr Ih Ik Il In Is Jh Jl Jn Lh Li Lv Lw Mb Mh Mm Mp Mz Nc Ne Nh Ni Nm No Ny Of Oy Qb) aC(aN Ap Ax BA Bb Bc Cp Cs Cu Dc dF Dg Dl Fr Ih Ij Io Jj Jn Kf Lh Lj Mi Mm Nt Pe Pj Un Vt) Nj(Aa Ik In It Jj Jq Jr Lj Lv Ma Mi Mn Mq Mu Mw Nd Ne Nf Nh Nk Nl Nq Nr Pa Pd Pe Po Pz Qc) Mz(aN bM Fp Fr Hx Ij Is Jl Jn Lh Li Lw Mb Mm Mp Ms Nc Ne Nf Nh Nm Ny Og Pb Qb rC) Nu(Fr Ih Ij In Ip Ir It Jh Jr Li Lv Lw Mb Mm Mp Nc Ne Nf Nh Nm Nn No Oy Pe Qb) Qd(Aa Aj aK AR aS Ax bA bE bJ bL cD cM cN CS cT cX dD Dk Kp Or Ub Wm) aA(Fr Ij Ip Ir Is It Jh Jq Lv Lw Mb Mp Nc Ne Nf Nh Nm Nn No Ny Og Po Pz) Ji(Aj aS Ax bA cD cM cN Cs dD dR eF gL gP hC iP iZ kR kS nY oE Ub Wm) Jn(aN Fp Fr In Jh Jj Jl Lh Li Lv Lw Mb Mm Mp Ms Nc Ne Nh Nm No Ny Og) Lh(Fp Hr Hx Is It Jj Li Lw Mb Mh Mm Mw Nb Ne Nh Nm Nn Ny Og Oy Qb) Nl(Aa Ih Ij Ip Ir Is Jh Jj Jq Lv Lw Mp Mr Ni Nk Nm Nn Ny Og Qb) Fp(Is Jh Jl Jq Lw Mp Nc Ne Nf Nh Nm Nn Ny Og Pz) Li(aN Is Jj Jl Lv Lw Mb Mm Nc Ne Nf Nh Nm Qb) aN(Ar Ax bA cT Et Is Lj Lw Ok On Pe) Jl(Hr Jj Lw Mb Mm Ms Ne Nf Nh Nm) Jj(Dc Jd Kf Mm Nn Ny Qb) Og(Fr Mm Nm Nn Ny Qb) Is(Fr Mm Ne Nh Nm) Aa(Et Mb Ne Nt) bU(dU eQ oD oW) jD(Wf Yd Zx Tl) Nh(Fr No Ny) Jd(Lj Or Ub) Kf(Lj rR Uu) bM(bA Et Ok) cM(Lj Uh Vt) Ax(Lw Or) Mb(Fr Mm) Sf(Dk Nd) Qb(Mm Nm) AjOn CsLw CuNf WmwQ MkOr QgVt KxeP Unconstrained panels with 2 analytes, where 1.0E-4 >= 'model p-value' > 1.0E-5. Contains 2,012 panels of 199,260 total panels evaluated. : Ji(AD aE AF aG aH al aJ aK AL aM An AO AP aQ AR As aU aV AW aX aY aZ Ba BB BC bE bF BG bH bI bJ bL BN BO bP bQ bR bS bU bV bW bX bZ cA cB cC cE cF cG CH cI cJ cK cL CO CP CQ cR cS CT CU CV CW CX cY cZ dA DB DC Dd DE dF DG dH Dl dJ DK DL dM dN eC Ef fP gW hB hF hG iA iC iH iJ iO jD kQ lM nW oF oH oK oN Or pF Qg qT Qv Qw Qz Rf Rg Sr Tz Ua Uc Ud Ue Uf Ug Uh Uk Ul Um Un Uo Ur Us Ut Uu Uv Vo Vp Vs Vt Vu Vv tF) Qd(AD aE AF aG aH al aJ AL aM An AO AP aQ As aU aV AW aX aY aZ Ba BB BC bF BG bH bI BN BO bP bQ bR bS bU bV bW bX bZ cA cB cC cE cF cG CH cI cJ cK cL CO CP CQ cR Ct CU CV CW Cx cY cZ dA DB DC Dd DE dF DG dH Dl dJ dK DL dM dN Ef Fa Hc Hf Ib Ic Iz Jd Jv Kc Kf Kn Ko Kx Kz oE Ou Pj Pk Qg Qv Qw Qz Ra Rf Rg Sr Ua Uc Ue Uh Uo Ur Us Vt) aC(Ad AJ Al aM An Ao aP aR Aw aX aZ bC Bg bM Bn Bo cD cG cM cN Co Cq CT cU Cv Cw Dd De Di Dk dL Ex Fa Fp Fw Fy Gl Gp Hx Id Ik Ip Iq Ir It Jd Jh Jk Jl Jq Jr Js Kc Ke Kn Ko Kp Kq Kx Lv Lz Mc Mg Mh Mj Mk Ml Mn Mp Mq Mr Mu Mv Mw Nb Nd Ne Nf Ng Nh Ni Nj Nk NL Nn No Nr Ns Nu Nv Ny Oa Og Om Or Pa Pd Pf Pk Po Pz Qb Qc Sr Ub Uh Vq Wm) Li(Aa Aj bA bM cD cM Cs Fp Fr Hq Hr Hu Hv Hw Ih Ij Ik In Ip Ir It Jd Jh Jo Jq Jr Lj Lu Ly Lz Ma Mc Md Me Mf Mh Mi Mj Mk Mn Mp Mq Mr Ms Mu Mv Mw My Nb Nd Ng Ni Nn No Nr Ns Ny Oe Of Oh Oi Or Oy Oz Pa Pb Pc Pd Pe Pg Po Pz Qc Ub Ur Vt) Jp(Aa Aj Ar Ax bM Cs Dp Ez Fa Fb Fn Fy Gz Ha Hb Hf iA Ic Jf Jy Kd Ke Kf Kg Ki Kj Kk Kn Ko Kp Kq KR Ks Ky Kz Ld oE Ph Pi Pj Qg Qh Ql Qm Qn Qv Qx Qy Qz Rb Ri Rj Rm Sr Ss St Tn To Tr Tv Ud Uf Ug Uh Ul Un Uo Up Ut Vo Vp Vv Wm) Mx(Ax bA bM cD cT Hq Hr Hu Hv Hw Hx Ii Il Io Ip Iq Ir Jk Jm Jo Jr Kp Lj Lz Ma Md Me Mf Mg Mh Mi Mj Mk Ml Mn Mq Mr Ms Mu Mw My Na Nb Nc Nd Ng Ni Nn Ns Of Oh Oi Or Oy Oz Pa Pb Pc Pd Pe Pf Pg Po Qc Ub Uh Uk Un Wm) Mz(Aj AR aS Ax bA bE bL bU cD cF cM Cs cT dD dF dL Dp Hr iB iC Ih Ii Ik Il In Ip Ir It Jd Jh Jj Jo Jq Jr Kc Kf Kp Lv Md Mh Mi Ml Mq Mr My Nn No Nr Or Oy Pe Pk Po Pz Qc Qv Qw Qz Ra Rf Rg Sr Ub Uh Um Ur Vt Wm) Js(aN Hq Hu Hv Hw Hx Ii Ij Io Ip Iq Ir It Iu Jk Jm Jo Jq Jr Lj Lu Ly Lz Ma Mc Md Me Mf Mg Mi Mj Mk Ml Mn Mq Mr Mu Mv Mw My Na Nb Nd Ng Nk Nn Nq Nr Ns Oe Oh Oi Om Oz Pa Pb Pc Pd Pe Pf Pg Po Pz Qc) Nu(Aa Hq Hr Hu Hv Hw Hx Ii Ik Il Io Iq Iu Jk Jm Jo Lj Lu Ly Lz Ma Mc Md Me Mf Mg Mh Mi Mj Mk Ml Mn Mq Mr Ms Mu Mv Mw My Na Nb Nd Ng Ni Nk Nq Nr Ns Oe Of Oh Oi Om Oz Pa Pb Pc Pd Pf Pg Po Pz Qc) Nx(Aa aN Hr Hu Hv Hw Hx Ii Ij Ik Il Io Ip Iq Iu Jk Jm Jo Jq Jr Lj Lu Ly Lz Ma Mc Md Me Mf Mg Mh Mj Mk Ml Mn Mq Mr Mu Mv Mw My Na Nb Ng Ni Nk Nq Ns Oe Oh Oi Om Oy Oz Pa Pb Pc Pd Pf Pg Po Pz rR) Lx(Aa bM cD Fr Hq Hu Hv Hw Hx Ii Ij Il Io Iq Iu Jk Jm Jo Lj Lu Ly Lz Ma Mc Md Me Mf Mg Mh Mi Mj Ml Mn Mq Mu Mv Mw Na Nb Nd Ng Nk No Nq Nr Ns Oe Of Oh Oi Om Oz Pa Pb Pc Pd Pe Pf Pg Po Pz Qc) Jn(Aa bM Hq Hr Hu Hv Hw Ih Ij Ik Il Ip Ir Is It Jo Jq Jr Lj Lu Lz Ma Mc Md Me Mf Mg Mh Mi Mk Mn Mq Mr Mu Mv My Nb Nd Nf Ni Nn Nr Ns Oe Of Oh Oi Oy Oz Pa Pb Pc Pd Pe Pf Pg Po Pz Qb Qc Vb) Jt(Ar Ax bM cD Cs Hq Hu Hv Hx Ij Ik Il Io Iq Iu Jk Jm Jo Lj Ly Lz Ma Mc Md Me Mf Mg Mi Mk Ml Mn Mq Mu Mv Mw Nb Nd Nk Nm Nq Ns Oe Oh Oi Om Or Oz Pa Pb Pc Pd Pe Pf Pg Pz) aA(aN Hq Hr Hu Hv Hw Hx Ii Ik In Io Iq Iu Jj Jk Jm Jo Jr Lj Ly Lz Ma Mc Me Mf Mg Mh Mi Mj Ml Mn Mq Mr Ms Mu Mw My Nb Nd Ng Ni Of Oh Oi Oy Oz Pa Pb Pc Pd Pe Pf Pg Qc) Nl(Hr Hv Hw Ii Ik In Io It Jk Jm Jo Jr Lj Ma Mb Mc Me Mf Mg Mh Mi Mk Mn Mq Ms Mu Mw My Nb Nd Ne Nf Nh Nq Nr Of Oh Oi Om Oy Oz Pa Pb Pc Pd Pe Pf Pg Po Pz Qc) Jl(Fr Hu Hv Hw Hx Ih Ii Ij Ik Il In Ip Ir Is It Jh Jq Jr Lh Lj Lv Mc Me Mf Mh Mi Mk Mp Mq Mr Mv Mw My Nc Ni Nn No Nr Ns Ny Of Oi Oy Pa Pb Pe Pz Qb Qc) Nj(aN Hq Hr Hu Hv Hw Hx Ii Il Io Iq Iu Jk Jm Jo Lu Ly Lz Mb Mc Md Me Mf Mg Mh Mj Mk Ml Ms Mv My Na Nb Nc Ng Ns Oe Of Oh Oi Om Oy Oz Pb Pc Pf Pg) Or(aN bM cF cM Cs dJ Et Fy Gp Hb Hf Hu Ik Im Io Jj Kc Ke Kf Kn Ko Kp Kq Lj Lv Mm Nf Nw Oa Og Pa Pj Pk Qe Qg Sr Ub Uh Ur) Lh(aN Fr Hw Ih Ij Ik Il In Ip Ir Iz Jh Jq Jr Lj Lv Md Me Mf Mk Ml Mn Mp Mr Ms Mv Na Nc Ni No Nr Of Oi Om Pb Po Pz Qc) Is(Aa Aj Ax bM cD cM Hr Ih Ij In Ip Ir It Jh Jj Jq Lv Lw Mb Mp Mr Ms Nc Nf Ni Nn No Nr Ny Oy Pe Po Pz Qb Qc) Lj(aK aR aS aZ BA bC bM bU cB cD cN cT Cu dD dF dJ Id Kc Ko Kp Kq Pk Qg Qz Sr Tz Ub Uh Un Ur Us Vt Wm) aN(aZ Bb bF bM cB cD cF cM Cs Cu Dc dD dF dK Fp Ij Io Ir Iv Jg Jj Jq Kn Ko Kp Kq Ks Kx Nm No Nr Oa Ph Pk Pz Uh Vt) Fp(Aa cM Fr Hr Ih Ij Ik In Ip Ir It Jo Jr Lv Mb Mf Mg Mi Mr Ms Ni No Nr Oy Qb Qc) Nw(Aa Aj Ao Ar aS Ax bA bE bL bU bV cD cF cM Cs cT cU dD dJ dL kC Kx Pk Ub Us Wm) Fr(Aa Hr Ih Ir It Jh Jq Jr Lv Lw Me Mp Ms My Nc Ne Nf Nm Nn No Ny Of Oy Qb Qc) bM(Aa Ar Ax aZ Bb cM

Figure 31 Continued

Cs cT Dc dD dF Im Jd Jg Ke Kf Kp Lw Mt On Pe Uh Vt) Og(Aa Ax Dc Ih Ip Ir It Jd Jh Jk Jq Kf Lv Lw Mp Nc Ne Nh No Nr Po Pz) Nm(Ax bA Ih Ij Ir It Jh Jq Jr Lv Mb Mp Mr Nc Ne Nf Nh Nn No Ny) Im(Aa Aj aS Ax bA cD cM Cs Iz Jd Kp Pk Rg Ua Ub Uh Uk Ur Us Vt) Kf(Aj Ax Cs Ef Ik Iz Jo IM Mk Of Pk Qa Rg Tz Ub Uk Ur Us Vt) Ny(In It Jh Jq Jr Lv Lw Mb Mi Mp Mr Ms Nc Ne Nf Ni Nn No Qb) Nn(Ir It Jh Jq Lv Lw Mb Mp Mr Ms Nc Ne Nf Nh No Qb Qc) Jd(Aj Ax cM Cs Ib Ik Iz Kq Lz Mt Oa Of Oh On Qa Us Vt) Aa(Ih It Jg Lu Lv Lw Me Mp Nb Nc Nh Ok On Po Qb Qc) Lw(Ar bA cD cK cT Ij Ir Jh Mb Nc Ne Nh No Nr Qb) Ax(cD cM Et Io Jg Mt Nf Nt Ok Ub Uh Un Ur Vt) Hv(Hp Sf Sh Si Sj Vb Vc Vi Wb Zw Zx Ye Tl Xa) Qa(Aj cM Kp Qg Ua Ub Uh Uk Um Ur Us Vs Vt Tl) Qb(In Jh Jq Lv Mb Mp Ms Nc Ne Nf Nh Ni No Oy) Ij(In Lv Mb Mp Ms My Nc Ne Nf Nh Oy) Vt(Ar aS Cs Ir Ko Kp Nf Oh Pk Ub Ur) bU(fA fB gZ jB nN oT oV pH pI pK) cM(Ar Cs Et gZ Kp Kx nY Oa oE Un) No(Ib Ir Jh Jq Lv Mb Mp Nc Ne) Nh(Ih Ir It Jh Jq Lv Mp Po Pz) Aj(Ad Ba Dc Et Kq Mt Nt Ok) rR(Ap Jv Kc Pj Rb rC Uf Wm) Cs(cD Et Io Jg Ok Ub Uh) Mp(Ir Jh Jq Mb Nc Ne Nf) Et(aG Ba cD kR Pk Ub) Jq(Lv Mb Ms Nc Ne Nf) Oh(Ra Ub Uh Ur Us Wm) Ne(Ir It Jh Lv) Ub(Dc Ir Kn Kp) cD(Ar bA Mt Ok) Nf(Dc Kq Po) Sf(Jr Nb Ut) Jh(Ir It Nc) On(Ao Hc Iz) Ur(Dc Ir Us) Vb(Cu Jr Ut) Kq(Hc Iz) Nv(Jm Po) Uh(Pk Wn) Pj(jD oE) bA(Nt Ok) ArcT Culo FaMk FwVc GchC LvIh MrNc KxdX aMeW bReO fRgW rCrZ qUkK Unconstrained panels with 2 analytes, where 1.0E-3 >= 'model p-value' > 1.0E-4. Contains 6,049 panels of 199,260 total panels evaluated. :
Mz(Aa AD aE AF aG aH al aJ aK AL aM An AO AP aQ As aU aV AW aX aY aZ Ba BB BC bF BG bH bl bJ BN BO bP bQ bR bS bV bW bX bZ cA cB cC cE cG CH cI cJ cK cL cN CO CP CQ cR cS Ct CU CV CW CX cY cZ dA DB DC Dd DE DG dH DI dJ DK Dl dM dN ED Ez Fa Fb Fn Fw Fy Gp gW Gz hA Hb Hc Hf hP Hq hR Hu HV HW hX Ib Ic Id Io Iq Iu Iz jD JE JF jG jH jI JK jL JM jO jP jQ jR jT JU JV jY Ke Kk Kn Ko Kq KR Ks Kx Kz Ld Lj IK IL IM IN IO Lu Ly Lz Ma Mc Me Mf Mg Mj Mk Mn Mu Mv Mw Na Nb Nd Ng Ni Nk Nq Ns Oa Oe Of Oh Oi Om Ou Ow Oz Pa Pc Pd Pf Pg Ph Pi Pj QG Qh QI Qm QT QU qV qW QX QY qZ rA RB Rc Rh Ri Rj Rm rO rQ rR rU rV rX rY rZ Sf Ss St Tn To tR tT Tv Tz Ua Uc Ud Ue Uf Ug Uk Ul Un Uo Up Us Ut Uu Uv Vo Vp Vs Vu VV wE wF wG wP wQ yH yJ) Or(aA AD AF aH AJ aK Al aM An AO Ap aQ AR AS aU aV AW aX aY aZ BA BB BC bE bF Bg bH bl bJ bL BO bP bQ bR bU bV bX cB cC cD cE cG CH cI cJ cK cN CO CP Cq cR CT cU CV CW CX cY dA Db DC DD De dF Dg dH DI DK DL dM Dp Ed Ez Fa Fb Fn Fr Fw Gc GI Ha Hc Ho Hq Hr Hv Hw Hx Ib Ic Id Ih Ij Il In Ip Iq Ir Is It Iu Iv Iz Je Jf Jg Jh Jk JI Jm Jn Jo Jq Jr Js Ju Jv Jy Kd Kg Ki Kj Kk KI Kr Ks Kx Ky Kz Ld Lh Lu Lw Lx Ly Lz Ma Mb Mc Md Me Mf Mg Mh Mi Mj MI Mn Mp Mq Mr Ms Mt Mu Mv Na Nc Nd Ne Ng Nh Ni Nj Nk NI Nm Nn No Nq Nr Ns Nt Nu Nv Nx Ny Oe Of Oh Oi Ok Om On Ou Ow Oy Oz Pb Pc Pd Pe Pf Pg Ph Pi Po Pz Qa Qb Qc Qh QI Qm Qn Qv Qw Qx Qy Qz Ra Rf Rg Ri Rj rR Sf St Tn To Tr Tv Tz Ua Uc Ud Uf Uk Um Un Uo Us Ut Uv Vp Vs Vt Vu Xa Wm Ti Th) Vt(Aa aD aE aF aG aH al AJ aK aL aM AO aP aQ aR As aU aV aW aX aY aZ BA bB BC bE bF BG bH bI bJ bL BN bO bP bQ bR bS bU bV bW bX bZ cA cC cE cF cG cH cI cJ cK cL cN cO cP CQ cR cS cT CU cV cW cX cY cZ dA dB DC DD DE dF DG dH DI dJ DK DL dM dN Dp dR Ed Ef eP Et Fa Fb FP Fr Fw Fy Gc Gp Hb Hf Hr Hu Hx Ic Id Ij Ik Il In Io Iq Is Iz Jg JI Jn Jq Js Jt Kc Ke Kk Kn Kq KR Ks Kx Ld Lh Lu Lv Lw Lx Ly Lz Ma Mb Mc Me Mh Mj Mk MI Mm Mn Mp Mq Mr Mt Mu Mv Nc Nd Ne NI Nn No Nr Ns Nt Nu Nv Nw Nx Oa OE Og Oi Ok On Ou Oz Pa Pc Pd Pe Pf Ph Pi Pj Ps Pz Qb Qc Qh Qm Qv Qw Qz Ra Rg rR Sr St Tn Tv Tz Uc Ud Ue Uf Ug Uh Uk Um Un Uo Us Ut Uv Vb Vi Vp wF wQ Wm Ti Th) Lj(Aa Ad aE AF al AJ AL aM An Ao AP aQ Ar As aU aV AW AX aY BB Bc bE bF BG bH bI bJ bL Bn BO bQ bR bS bV bW bX bZ cA cC cE cF cG CH cI cJ cK cL CO Cp CQ cR CS Ct cU CV CW CX cY cZ dA DB DC Dd DE DG dH DI dK dM dN Dp dR Ed Ew Ex Ez Fa Fb Fn Fp FR Fw Fy Gl Gp Gz Ha Hb HC Hf Ho Ib Ic IJ Is Iz Je Jf Jh Jq Ju Jv Jy Kd Ke Kg Ki Kj Kk Kl Kn KR Kx Kz Ld Lv Lw Mm Mp Ne Nh Nm Nn No Ny Oa oE Og Ou Ow Ph Pi Pj Qb Qh Ql Qm Qn Qt Qu Qv Qw Qx Qy Ra Rb Rc Rf Rg Rh Ri Rj Rm Sf Sj Ss St Tn To Tr Tv Ua Uc Ud Ue Uf Ug Uk Ul Um Uo Up Ut Uu Uv Vi Vo Vp Vq Vs Vu Vv Wb Wf Wh Zx Tl) Ax(Ad Aj aK aM An Ao AR aS aU aV aZ BA BB BC bE bF Bg bJ bL Bn BO bU bX cB cF cG cJ cK cL cN Cp Cs cT CU cX Dc DD DE dF Di dJ DK DL Dp Ed Fb Fr Fy gW Hb Hf Hq Hr Hu Hx Ic Id Ih Ii Ij Ik Il In Iq Ir It Iv Iz Jh Jk JI Jn Jo Jq Jr Ju Jv Jy Kc Ke Kk Kn Ko Kp Kq Kx Lh Lx Lv Lx Ly Lz Ma Mb Me Mf Mg Mi Mj Mk Ml Mm Mn Mp Mq Mr Mu Mv My Na Nb Nc Nd Ne Ng Nh Ni Nj Nk Nl Nn No Nr Ns Nu Nv Nx Ny Oa Of Oh Oi Om On Ou Oz Pa Pb Pd Pe Pf Pg Pj Pk Pz Qa Qb Qc Qg Qh QI Qm Qv Qw Qx Qz Ra Rf Rg Rh Ri Rj rR Sr St Tn Tz Ua Uc Ud Ue Uf Uk Ul Um Uo Up Us Ut Uv Vp Vq Vu Wm) Nw(AD aE AF aG aH al aJ aK AL aM An aO AP aQ aR As aU aV AW aX aY aZ Ba BB BC bF BG bH bl bJ BN BO bP bQ bR bS bW bX bZ cA cB cC cE cG CH cI cJ cK cL cN CO CP CQ cR cS Ct Cu CV CW CX cY cZ dA DB DC Dd DE dF DG dH DI DK Dl dM dN dX Ed Eo eP Fa Fb fP gV Hb HC HF iA Ib IC Id iP IZ Jd Ju Jv Kc Kd Ke Kf Kk Kl KN Ko KP Kq KR Ky Kz mF ml mI nK nL nN nO nY Oa oE oN Ou Ow Ph Pi Pj Qg Qh Qt Qv Qw Qx Qy Qz Ra RC Rf Rg Rh Ri Rj Rm Sr Tz Ua Uc Ud Ue Uf Uh Uk Um Un Uo Up Ur Ut Uu Uv Vo Vp Vu) Qe(AD AF aG aH al aJ aK AL aM An AO AP aQ aR As aU aV AW aX aY aZ Ba BB BC bE bF BG bH bl bJ BN BO bQ bR bS bU bV bW bX bZ cA cB cC cE cF cG CH cI cJ cK cL cN CO CP CQ cR CS CT cU CV CW CX cY cZ dA DB Dc Dd DE dF DG dH dI dJ DK DL dM Dp dR dW dX cF eM Eo fP Fy gL gP gV gW hB hC HF hG iA Id iH iJ iO iP iZ Jd Jf Ju Jv Jy Kc Kd Ke Kf Kj Kk Kn Ko Kq kR kS Kx Kz Ld mW mV Ny Oa oE oF oH oK oN Ou Ow pF Ph Pi Pj Qg Qh Qt Qu Qv Qw Qx Qy Qz Ra Rb Rc Rf Rh Ri Rm Sf Sr Tn To Tv Tz Uc Ud Ue Uf Ug Ul Um Un Uo Up Ut Uu Uv Vo Vp Vs Vu Vv wQ Tl Wm tF) Qw Qz Rf Rg Rm Sr Tn To Tv Uf Ug Ul Up Ut Uu Uv Uw Vb Vc Vo Vp Vq Vu Vv Wb Wf Vj Zw Zx Ye Tm Tl Xa) aN(Aa AD aE AF aG aH al AJ aK AL aM AO AP aQ aR AS aU aV AW aX aY Ba bB BC bE BG bH bI bJ bL BN BO bP bQ bR bS bU bV bW bX bZ cA cC cE cG cH cI cJ cK cL cN CO CP CQ cR cS Ct cU CV CW CX cY cZ dA dB dC Dd DE DG dH DI dJ Dh DL dM dN Fa Fr Fw Fy Gp Hq Hv Hx Id Ih Ii Ik Il Ip Iq It Iu Jd Jh Jk JI Jm Jr Kc Ke Kf Kn Kp Kq Kx Lv Ly Lz Ma Mb Mc Mg Mj Mk Ml Mm Mn Mp Mq Mr Mu Mv Mw Nb Nc Nd Ne Nf Nh Ni Nk Nl Nn No Nr Ns Nu Ny Oa Oh Om Oy Oz Pa Pb Pd Pg Pj Po Pz Sr Tz Ub Un Vu) Im(aK aM An AR aU aV aZ BC bE bF bI bJ bL bO bQ bU bV bX cB cC cF cG cI cK cL cN cT CU cV cX Dc dD dE dF Di dJ DK dL Dp dR Ed EF Ez Fa Fb Fw Fy gL GP gW HB HC HF hG iA Ib Ic Id iH iJ iO iP iZ Je JF Ju Jv Jy Kc Kd Ke Kf Kj Kk Kn Ko KQ KR kS Kx Kz Ld mW mV Ny Oa oE oF oH oK oN Ou Ow pF Ph Pi Pj Qg Qh Qt Qu Qv Qw Qz Ra Rb Rc Rf Rh Ri Rm Sf Sr Tn To Tv Tz Uc Ud Ue Uf Ug Ul Um Un Uo Up Ut Uu Uv Vb Vo Vp Vs Vu Vv wQ Tl Wm tF) aC(AA AD aE AF aG aH al aK aL aO aQ AS aU aV aW aY bB bE bF bG bH bI bJ bL bN bO bP bQ bR bS bU bV bW bX bZ cA cB cC cE cF CH cI cJ cK cL cO cP cQ cR cS cV cW CX cY cZ dA DB dC dD dE dG dH dI dJ dK dM dN Ed Ef Fb fR Gc Gz Hb Hc Hf Hq Hr Hu Hv Hw Ic Ii II In Iu Iz Jm Jo Ju Jv Jy Kd Kg Kk Kl Kr Lu Ly Ma Mb Md Me Mf Ms My Na Nc nH Nq Oe Of Oh Oi Ou Ow Oy Oz Pb Pc Pg Ph Pi Qh QI Qm Qw Qz Ra Rg St Tn To Tv Ua Uc Uf Ur Us Vu Tj) Jd(Ao Ar Bg cD Ch Cq Ct Cu Dc De Dp Ed Ef Et Ez Fa Fp Fr Fw Fy Ha Hc hR Hu Hv Hx Ic Id Il In Io Iq Ir Is Iu Je Ji JI Jn Jo Jq Jr Js Jt Ju Jv Jy Kc Kd Ke Kf Kk Kl Kn Ko Kp Kx Lh Lv Lw Lx Ly Mb Me Mg Mh Mi Mj Mk Ml Mm Mp Mq Mr Ms Mu My Na Nc Nd Ne Nf Ng Nh Ni Nj Nl Nm Nn No Nr Ns Nu Oi Ok Ou Oy Oz Pa Pb Pd Pe Pf Pi Pk Po Qb Qh QI Qm Qt Qu Qv Qw Qz Ra Rc Rg rR Sr St To Tv Tz Ua Uc Ue Uf Uh Uk Um Un Uo Up Ur Uu Vo Vp Vs Vu Vv Wm) Mx(Aa AJ aK aM AR aS aU aV aX aZ Ba BB BC bE bF bJ bL BO bR bS bU bV bX cB cF cG cI cJ cN Cp cQ cR Cs CU cV cX cY Dc dD De dF Di dJ dK dL Dp dR Ed Fa Fy gW Hb hC iC Id Iu iZ Je JF Ju Jv Jy Kc Ke Kf Kk Kn Ko Kq kR Kx Ln Ly Mc Mv Nk Nq nY Oa OE Om oN Pj Pk Qg QI Qm Qt Qv Qw Qz Ra Rf Rg Ri Rj rX Sf Sr St Tn Tv Tz Ua Uc Ud Ue Uf Ug Ul Um Uo Up Us Vo Vp Vs Vu Vv Tl) Li(aK aM An Ao AR aS aU aV aX aZ Ba BB Bc bE bF Bg bJ bL Bn Bo bQ bR bS bU bV bX cB cF cG cL cN Cp CT CU CV cX Dc dD DE dF Di dJ DK dL Dp Ed Ez fR Fy gV hC Hx Ib Ic Id Ii Il Io Iq Iu Iz Jk Jm Ju Jv Jy KC Kf Kk Kn Ko KP Kq kR Mg Ml Na Nk Nq oE Om Pf Pk Qg Qh Qv Qw Qx Qz Ra Rf Rg Sf Sr Tn Tv

Figure 31 Continued kR kS Kx lM lN Mk Mq nY oF Pk Qv rC Rg rZ Us) Pk(Cu dR Fa Fy Hu Id Ik Io Kc Ke Kk Ko Kq Kx Mk Ml Mq Nd Nf oE On Ou Pa Rg Sr tT Uf Ur Us wF Wm) Jt(An Ao Ap aR aS aZ bE Bn BO bV cN CT CU cV cX dD De dF Di DL Rg Ue Uk Ur Vb) Wm(Cu Fy hP hV jD Jq Kc Ke Kq On Pe qI Qv rB rC rU tO Tz UR Us wB wC wF wJ wL yJ zG) Kx(Aj aS cD cV dJ Dp gV Hb Hu Id Ik Io Iq Jv Kq Lv Mk Ml Mq Nd Pa Qw Qz Sr Tz Uo Ur Us) Pe(Aj aR aS aV aZ cD cF dJ dR eM eP Hr Ih It Jh Jq Lv Mb Mp Nc Ne Nf oE oN Pz Ur) Fy(Aj cD dJ Dp dR hC Hu Ik Iz kR kS Lv Mk Mq oE Of oN Qv Ra Rg Sf Ur Uv) Ne(Hr Ih Ik In Ip Jk Jo Ma Mb Mi Mn Mq Mr Ms Mw Nf Ni Nr Pa Pd Po Pz Qc) Cu(Aj cD Hw Ik In Iv Jg Jo Lz Mk My Na Nb Nj Nt Nu Of Pg Qc Ur Vc Tl) Gc(cB De Ed hG iZ kS oE Sf Tz Ua Ue Uk Um Us Ut Uy Va Vb Vi Vp Vq Vu) Nf(Ad Cp Cq cT Cw Fa Id Ih Ip It Jh Jo Ke Lv Mb Mi Mq Mr Nr Pz Us Vu) Jq(Hr Ih Ik In Ip It Jh Lu Mh Mi Mq Mr My Ni Nr Of Oy Pd Po Pz Qc Rg) On(aS bE cD cT dD Dk Ef fR iC kC lM Rg Sf Ua Uc Ur Us Uu Vb Vc Vu Zw) Ut(Du Eq fR Ho Lt Ps Ry Sh Si Uw Ux Uy Uz Va Vc Vi Vw Wb Zw Zx Tl) Kq(Ao Dk Ef Hu Ib Ii Ik Io Lv Mk My mZ Nq Of Pa Rg Tn Ur Vs) Nl(Hq Hu Hx Il Iq Iu Lu Ly Lz Md Mj Ml Mv Na Nc Ng Ns Oe) Us(Dp Du Ho Kc Ke Ko Mk Mq Pa Ps Qv Sr Uk Vb Vi Vj Wb Zx) Jh(Ih In Ip Jo Lv Mb Mi Mq Mr Ms Nr Oy Pa Pd Po Pz Qc) Mp(Ih Ik In Ip It Jo Lv Mr Ms Ni Nr Oy Pa Po Pz Qc) Nc(Ih In Ip It Jo Lv Mb Mi Mn Mq Ni Nk Nr Po Pz Qc) Sf(bR cF Dc De Ed Fw Ho Jk Mw Nr Nt Pi Qh Tz Zx Xa) cT(Aj aM aR aZ cB cD cF cN cU dD dF dL Iv Kc Nj Nt) Vb(Dc Dk Fw Ho Jk Mw Nb Nv Pi Ps Qh Tz Uc Vi) Fa(aS cX dJ Hu Ik Io Kc Ko Lv Ml Nd Ra Ur) Mb(eO eW gC Ih Ip It Jo Mi Mr Nr Po Pz Qc) Ke(Aj aS Hu Ik Iz lM Lv Mk Mq oE Of Rg) Nx(Hq hR iC jI kC tT Ur wD wE wF wP wQ) Dc(cD Ik Io Jo Lz Of Rg Sr Ua Uk Um) Nt(aK aR aS aZ bE bO cD cU cV cX dD) Nb(Si Sj Vc Wb Wc Wd We Wf Wg Wh Zw) It(Ih In Ip kC Lv Mi Mr Nr Po Pz Qc) aA(Il Lu Md Mk Mv Na Nk Nq Ns Oe Om) lL(kC kF kI mF mI nC nH nK nL nN uY) Mq(Id Kc Ko Rg Sr Tz Uk Um Ur wQ) Nd(Du Eq Fd Ho Kc Kk Sh Si Vi Wb) Dk(Eq Ho Hp Sh Si Sj Uw Vc wF) Ih(In Ip Mi Mr Ms Ni Po Pz Qc) Tz(Du Ho iC Kc nL Wb Zx Tl) In(kC mF mI nL nN Nr Pi Po) Pz(Ip Lv Mh Mi Mr Ms Of Po) hR(cV dK iB iC jI Mk rB rC) Ko(Aj Ik Iq Kc Mk Sr Ur) Um(kP mF mS mZ nI nL nO) bU(gC Ho mT nL Vi Tl Xa) kC(aL bB iB iH jI kP Nv) Bo(DW EO EW) Lv(Ip Mn Mr Nr Po Qc) cB(Dr dW Em eO EW) dF(Aj aO bL bZ cD Nj) eP(Ho Iv Mn Yi Zx Xa) qU(kF kI kP nN nR nU) dX(Ho Iv Mn Yi Zx) Aj(Dg Io Iv Nv) Nr(Ip Mi Mr Ms) Jg(cD cU fR Uu) Xa(cF eM kS Rh) Tl(Ed Fw Ps Qh) Ur(Iq Js Qh Tv) Vu(Mk Pa Qv Sr) aD(Dw EO Ew) aM(dW eO Ew gV) bB(eO fB gZ oV) nL(dD Gl iB Qz) hC(Ns Wb Zq Zx) Po(Hr Ik Oy) Tn(Iz mZ Vc) Ip(Mr Qc wQ) Kc(aS dJ Sr) Rg(Id Pa Sr) Nv(lM mI nK) gW(kK kN mF) rC(tT uY yJ) wF(Ef Ri Ti) rZ(jY kN Ti) oE(cX Mk Ns) Ex(cJ Pi) Gz(Hf uY) Mn(eM gV) Nj(fR gV) Iv(dD fR) Wb(cF De) Qc(dD Ik) Vi(bO Rh) cD(aZ cG) mZ(Gl Uf) jD(Yh Zq) kK(lK lN) AfIo LutT MkiC IztV WcqV QhVc OuwQ aLmI cCdW cFjB mFjF rBwD kFlN kNkP Constrained panels with 3 analytes, where 1.0E-10 >= 'model p-value' > 0. Contains 2,072 panels of 37,933,414 total panels evaluated. :
Et{Oy(aA Fp Ih Im Is It Iv Jg Ji Jj Jl Jn Js Lh Lu Lw Lx Mb Mh Mp Mr Ms Mt Mx Mz Nc Ne Nh Nj Nl Nn Nt Nu Nv Nx Of Ok On Pe Pg Qa Qb Qd Qe) My(aA Fp Im Is It Iv Jg Ji Jl Jn Js Lh Lu Lw Lx Mb Mf Mh Mr Ms Mt Mu Mx Mz Nc Ne Nh Nj Nl Nn Nt Nu Nv Nw Nx Ok On Qa Qb Qd Qe) Nf(aA Fp Ih Im Is It Iv Ji Jj Jl Jn Jq Jr Js Lh Lu Lw Mb Me Mh Mp Ms Mt Mx Mz Ne Nt Nu Nv Nx Ok On Qa Qb Qd Qe) Of(aA Fp Im Is It Iv Jg Ji Jl Jn Js Jt Lu Mb Ms Mt Mx Mz Nc Ne Nh Nj Nl Nt Nu Nv Nx Og Ok On Qa Qb Qd Qe) Hr(aA Fp Im Is It Iv Ji Jl Jn Jq Jr Js Jt Lh Lw Me Mh Ms Mx Mz Nc Ne Nh Nl Nu Nx Ok Pe Qa Qb Qe) Og(aA Fp Im Is It Iv Ji Jn Js Lw Mb Ms Mt Mx Mz Nc Ne Nh Nj Nl Nt Nu Nx Ok On Qa Qb Qd Qe) Ms(aA Fp Ih Im Is It Iv Jj Jn Js Lw Mt Mx Mz Nc Ne Nh Nl Nt Nu Nx Ok On Qa Qb Qd Qe) Jj(Fp Ih Im Is It Iv Ji Jn Js Mb Mt Mx Mz Nc Ne Nj Nl Nt Nu Nx Ok On Qa Qb Qd Qe) Ji(aA Fp Hx Ii Jh Jo Lu Mb Mh Ml Mp Mv Mw Mx Nj Nl Nm Nt Nu Ny Om Pb) aA(Fp Ih It Iv Jn Mb Mh Mt Mx Mz Nc Ne Nj Nl Nt Nu Qa Qb Qd Qe) Mb(Ih Ik Im Is It Jn Lw Mt Mx Mz Nc Nu Ok On Qa Qb Qd Qe) Ii(Im Jl Js Jt Lh Mr Mx Mz Nt Nv Nx Ok On Pe Qa Qb Qd Qe) Mz(Hx Jh Mh Ml Mv Mw Nc Ne Nj Nl Nm Nu Ny Om Pb) Nt(Im In Iv Jh Jo Mg Mk Mw Mx Ng Nj Nl Nm Qd) Nm(Fp Im It Jn Js Mt Nj Nl Nw Nx On Qd) Nu(Im Is It Iv Mx Nc Nl Ok Qa Qd Qe) Fp(Im It Iv Lw Mk Nc Nj Nl Ok Qd) Mx(Hw Im Iv Lw Mh Mj Mk Nj Nl Qd) Mw(Jl Lh Lx Mr Nn Nv Nw On) Nj(Im In Iv Ni Ok Qa Qd Qe) Ng(Im Jt Mt Nv Nx On Qa) Qd(Hw Im Iv Mj Nl Nq Pz) Ok(It Iv Jh Nc Ne Nl Qe) Lu(Ih It Jn Lw Nx) Ne(Im Is It Jn Lw) In(Ih Im Iv Qa Qb) Jh(Lh Mt Nv On) Mh(Jl Lx Mr) Mv(Lh Nv On) Nl(Im Iv Qe) Qa(Hw Iu Mj) Jo(Js Jt Nx) Mk(Iv Mt) Nc(Im Ni) It(Me Mt) MpOn HwQb ImIv JnJr} Ji{Ii(aA Fp Ik Im Iv Jg Jl Jp Jt Lh Lu Lx Mr Ms Mt Mx My Mz Ne Nf Nj Nl Nt Nu Ok On Pe Qa Qb Qd Qe) Nt(aA Hx Ik Im In Iv Jh Jj Jo Jp Mh Ml Ms Mv Mw My Nb Nf Nj Nm Ny Of Og Om Oy Po) My(aA Ik Im In Iv Jg Jj Jp Jq Lu Ms Mt Mu Mx Nf Nj Nl Nn Nu Nv Of Ok On Qd Qe) Oy(aA Fp Ik Im In Iv Jp Jq Lu Ms Mt Mx Nj Nl Nn Nu Nv Ok On Qa Qd Qe) Nu(aA Ik Im In Iv Jh Jj Jo Jq Lu Mp Ms Mw Nf Nj Nm Of Og Om Qd) Lu(aA Hx Ik Im In Jh Jj Jq Mh Mp Mv Mw Nf Nj Ny Of Og Pb Qd) Mx(aA Hu Hw Hx Ik In Jj Jq Jr Js Mh Mj Mp Ms Nf Nj Of Og) Im(Hw Ik In Iv Jh Jj Jq Mp Ms Mw Nf Ni Nj Nl Of Og Om Qd) Qe(aA Hw In Jj Jq Mb Mh Mp Ms Mw Nf Ni Nj Of Og Om) Of(aA In Iv Jg Jp Ms Nf Ni Nj Nl Og Ok On Qa Qd) Nf(aA Fp Ik In Iv Jj Mb Ms Ni Nj Og Ok Qd) Nj(aA Ik In Iv Jj Jp Jq Ms Ni Og Ok Qd) Mp(aA Ik In Iv Jp Lx Mt Ok On Qa Qd) Mw(Fp Iv Jg Jp Mt Mu Nn Nv Ok On) Qd(aA Hw In Jj Jq Mh Ms Nl Og Om) Iv(aA Ik In Jj Jo Jq Mk Ms Og) Jg(Hx Jh Ml Mv Nm Ny Og Om) Jp(Hx Lh Mb Ml Mv Nm Ny Om) Ok(Hr Jh Jq Mh Ms Nm Og Om) Nl(aA Ik In Jj Jq Ni Og) In(aA Fp Jj Ms Og Qa) Qa(Hw Jj Mh Og Om) aA(Hr Jh Jq Ms Og) Fp(Hr Ik Jj Mh) Mz(Hx Ny Om Pb) Ms(Jj Ni Og) Nb(Jl Mr Pe) Ik(Jq Mb Ne) Po(Lx Pe) Nn(Jh Mv) Jl(Hr Mh) MtJh NcNi OmOn} Nt{Jj(aA Fp Ih Ik Im In Ir Is It Iv Jg Jl Jm Jn Jp Jq Js Jt Mk Mm Mx Mz Nj Nl Nn Nv Nw Nx Ny Og Ok On Oy Pa Qa Qb Qd Qe) Og(aA Fp Ih Ij Im In Ip Ir Is Iv Jg Jl Jn Jp Jq Js Jt Lw Mx Mz Nj Nl Nm Nv Nw Nx Ny Ok On Qa Qb Qd Qe) Of(aA Fr Im In Ir Is Iv Jg Jp Jq Js Jt Li Lx Mm Mx Mz Nj Nl Nn Nv Nw Nx Ny Ok On Qa Qb Qd Qe) Ok(aA Hr Ii Ik Im In Iv Jh Jo Jp Mg Mh Mk Ms Mx My Nf Ng Nj Nl Nm Nr Oy Po Qd Qe) In(aA Fp Ih Ik Im Ir Is Iv Jn Jp Js Jt Lw Mx Mz Nj Nw Nx On Oy Qa Qb Qd Qe) Oy(aA Fp Im Is Iv Jg Jl Jn Jp Lh Lw Lx Mx Mz Nj Nv Nw Nx On Qa Qb Qd Qe) On(aA Ii Ik Il Iv Jh Jo Mb Mh Mk Ms Mv Mw My Nf Ng Nj Nl Nq Oe) Nj(aA Fp Ik Im Is Iv Jp Lx Mk Mx My Mz Nw Nx Pa Qa Qd Qe) Nw(aA Hx Ii Ik Im Iv Jh Mh Mk Ms Mv Mw Mx My Nf Nl Ny) Mz(aA Hx Ii Im Is Iv Mh My Nf Nl Ny Pb Qa Qe) Qd(aA Ii Ik Il Im Jp Mh Mj Mk Ms My Nf Nl) aA(Ih Ii Iv Jn Jp Mx My Nf Nl Qa Qb Qe) Im(Ii Ik Il Iv Jh Jp Mk My Nf Ng Nl) Qe(Ii Il Iv Lw Mh Mk My Nf Nl) Jp(Ii Ik Iv Mk Ms Mw Mx My Ng) Qa(Ii Il Iv Mh Mk My Nf) My(Is Iv Jg Lh Nv) Iv(Ik Lw Mk Nf) Mx(Ik Mk) Nf(Fp Is) Ii(Jt Lh) IkIs} Ok{Im(Hr Hw Ii Il In Iv Jh Jj Jn Jp Mb Mh Ms Mt Mx My Mz Nc Ne Nf Ng Nj Nl Nu Nw Nx Of Og Oy Qd) Og(aA Fp Is It Iv Jg Jn Jp Lw Mb Ms Mt Mx Nc Ne Nf Nh Nj Nl Nu Nw Of On Qa Qb Qd Qe) Nj(aA Hr Ii Ik In Iv Jj Jn Jp Mt Mx My Mz Nf Ni Nm Nu Nw Of On Oy Qd Qe) Iv(aA Hr Ii In Jj Jp Mg Mh Ms Mx My Mz Nf Nl Nu Nw Nx Of On Oy Qd Qe) Qd(aA Hr Hw Ii Il In Jj Mb Mh Mj Ms Mx My Na Ne Nf Nl Nq Nu Of Oy) Nf(aA Fp Is It Jj Jp Mb Ms Mx Mz Nl Nu Nw Nx Of On Qa Qe) Of(aA Hr It Jg Mb Ms Mx Nc Ne Nh Nl Nu Nx On Qa Qe) Jj(Fp It Jn Mb Mt Mx Nc Ne Nl Nu Nx On Qa Qb Qe) Mx(aA Hr Hw Ii In Jp Mb Mh Mj Ms My Nl Oy) Nl(aA Fp Hr Ii Jp Ms My Mz Ni Nw On Oy) aA(Fp Hr It Jn Mb Ms My Nc Nu Oy Qe) Ii(Fp It Jp Lh Mr Mt Mz Nw On Qe) My(Fp It Jp Mt Mu Nu Nw On Qa) Oy(Fp It Jp Mt Nu Nv On Qa) Fp(Hr It Jp Mh Ms On) Jp(Hr It Mb Ms Nu) Ms(It On Qe) Qe(Hr Il) On(Mb Mw)} On{Oy(Fp Hx Ii Im Iv Jg Jj Jn Jp Li Mb Mh Mm Mp Ms Mt Mw Mx My Mz Nb Nc Ne Nf Nh Nj Nl Nu Nw Nx Ny Of Og Pb Qa Qb Qd Qe) My(Fp Ii Im Iv Jg Jj Jn Jp Lw Mb Mf Mh Ms Mt Mx Mz Ne Nf Nh Nj Nl Nm Nu Nw Nx Of Og Qd Qe) Og(Fp Im Is It Iv Jg Jj Jn Lw Mb Mp Ms Mx Nc Ne Nf Nh Nj Nl Nm Nu Nx Of Qa Qd Qe) Nj(aA Hr Ii Ik Im In Iv Jh Jj Jp Mk Ms Mv Mw Mx Mz Nf Ng Ni Nk Nu Nw Of Qd) Jj(Fp Im It Iv Jh Jn Mb Mp Ms Mv

Figure 31 Continued

Mw Mx Nc Ne Nf Nh Nl Nu Nx Of Qa Qd Qe) Of(Fp Ii Im It Iv Jg Jh Mb Mp Ms Mv Mw Mx Ne Nf Nh Ni Nl Nq Nu Nx Qd) Iv(aA Ii Il Im In Jh Mb Mk Mp Ms Mv Mw Nf Ng Ni Nl Nq Nu Qd) Mb(aA Ii Im Jh Mk Ms Mv Mw Mx Nf Ng Nl Nu Qd) Ms(Fp Ii Im Jn Mw Mx Nf Ng Nl Nu Qd) Im(Ii Il Jh Mw Nf Ng Nl Nu Qd) Qd(Hw Ii Il Mw Nf Nl Nq Nu) Mw(Fp Jg Jp Mu Nu Nw) Ii(Mr Mx Nl Nu) Fp(Nf Nl) NuNg MjMx NiNl} Im{Nj(aA Ik Il In Iu Iv Jg Jj Jl Jn Jp Js Jt Lh Lv Lw Lx Mk Mm Mr Mt Mx Mz Nf Ni Nk Nm Nn No Nu Nv Nw Nx Of Og Oy Qc Qd Qe) Og(aA Fp Ij In Is Iv Jg Jj Jl Jn Jp Js Jt Lh Lv Lw Ly Mb Mm Ms Mt Mx Mz Nc Ne Nf Nh Nl Nm Nu Nv Nw Nx Qa Qd Qe) Iv(Il In Jg Jj Jl Jp Jt Lw Mk Mm Mt Mx My Mz Nf Nl Nu Nw Nx Of Oy Qd Qe) Nw(Ii Il In Jj Mb Mh Ms Mv Mw Mx My Nc Ne Nf Ng Nh Nl Nu Of Oy Qd) Jp(Fp Il Jj Lw Mb Ms Mx My Ne Nf Ng Ni Nl Nu Nx Of Oy Pb Qd) Qd(Hw Il In It Jg Jj Mb Ms My Mz Ne Nf Nh Nl Nu Nx Of) Jg(Jj Mx Ng Of) Jj(Nl Nu Nx) MtMy MzNl} Qd{Og(aA Iv Jg Jh Jp Jt Lw Mj Ms Mt Mx Mz Nc Ne Nf Nh Nj Nl Nm Nu Nw Nx) Nj(aA Il In Iv Jg Jj Jp Lw Mk Mz Ni Nk Nu Nw Of) Iv(aA Il In Jg Jj Jp Mk Nl Nw Of) Jg(aA Il Jj Ms My Of Oy Pz) Jp(aA Il Jj Ms My Nl Nu Of) Nw(aA Il Ms My Nl Nu Of) aA(Mj My Mz Nl Of) Jj(Nl Nu Nx) Il(Mz Nl) MtMy IiLh NxOf} Nw{Iv(aA Ii In Jj Mh Mk Ms Mv Mw Mx My Nf Nj Nl Nu Of Og Oy) Nj(aA In Jj Jp Mh Mx My Nf Ni Nu Of Og Oy Qe) Og(aA Fp Ij It Jg Mx Nl Nu Qa) Nl(aA Fp My Ni Nu Of Oy) Of(aA Jg Mx Nu Nx) Mx(Mh Mj My) Nu(My Oy) FpNf MyaA} Jg{Of(aA Fp Is Iv Jj Jl Jn Jp Jq Js Lh Lw Mp Mx My Mz Nj Nl Nu Nv Nx Og Oy Pa Qa Qb Qe) Og(aA Fp Ij Is Iv Jl Js Lw Mx Mz Nj Nl Nu Nx Qa Qb Qe) Jj(Iv Mx Nj Qe) Mx(Nj Oy) NjaA} Jp{Nj(aA Fp Ih Ik Is Iv Jj Jl Jt Lw Mp Mr Mx Mz Ni Nk Nm Nu Of Og Oy Qa Qe) Iv(aA Jj Mx Nu Of Og Oy) Og(Fp Ij Is Mx Nu Qa) Nu(Is Jj Of Oy) Of(Mx Nx) KxeP} Og{Nj(Ij Iv Jt Nv Qa Qe) Iv(Ij Nv Nx) QaNx} Jj{Nx(Qa Qe) NjNv} MzNjaA

Constrained panels with 3 analytes, where 1.0E-9 >= 'model p-value' > 1.0E-10. Contains 1,716 panels of 37,933,414 total panels evaluated. : Ok{Ii(aA Ih Is Jg Jl Jn Js Jt Lu Lw Lx Mi Nc Ne Nf Nh Nr Nu Nv Nx Ny Pe Qa Qb) Hr(Is It Jg Jl Jn Js Lw Mb Ms Mt Mz Nc Ne Nh Nu Nw Nx On Qa Qb) Jg(aA Fp It Jh Jn Mb Mg Ms Mw Mx My Nc Ne Nf Ng Nl Nu Oy Qe) My(Jn Js Lh Lw Mb Mf Mp Mz Nc Ne Nf Nh Nn Nv Nx Qb Qe) On(Hw It Jh Jn Mh Mp Mv Mx Nc Ne Ng Nh Nm Nq Nu Om) Oy(Jn Lu Mb Mp Ms Mu Nc Ne Nh Nn Nw Nx Pa Pg Qb Qe) Ms(Ih Jj Jn Lw Mt Mz Nc Ne Nh Nu Nw Nx Qa Qb) Nu(In Jn Js Mb Ng Nm Nr Nw Nx Po Qe) Mh(Is It Jn Js Lx Mr Mt Mz Nw Qa Qe) Mz(aA Hx It Ml Mv Mw Nh Ny Om Pb) In(Ih Is It Jn Mt Nc Nx Qa Qb Qe) Nf(Jn Js Li Me Mp Mt Ne Ni Qb) Nw(aA Fp It Mb Mw Mx Nc Ne Nh) Nx(Fp It Mb Mt Nc Ne Nh Qa Qe) Mt(aA It Jh Jn Mk Ng) Qa(aA Hw Il Mb Mj Po) Fp(Hw Jn Mj Nc Po) It(Hw Jo Mg Na Nm) Qe(Hw Jp Mb Mj Nh) Mx(Hu Jr Js Na) Jn(Nc Ne Nh Nl) Mb(Ik Js Nc) Mw(Mu Nn Nv) Jp(aA Jj Pb) Ih(aA Jj) Qb(Hw Il) PoLx NnMv MjJs NcNi NeaA} Qd{Nf(aA Fp Iv Jg Jj Jp Lh Lw Mb Mj Mp Ms Mx My Mz Ne Nh Ni Nl Nu Nv Nw Nx Of) Mj(In Iv Jg Jj Jl Jp Jt Lh Lw Ms Mt Mx Mz Ne Nh Nl Nu Nw Of On Pe) My(In Iv Jh Jj Jn Jt Lh Lw Lx Mm Mx Mz Ne Nh Nl Nm Nu Nv Nx Of) Of(Il In Jh Jn Jt Lh Lw Mb Mm Ms Mt Mx Mz Ne Nh Nl Nm Nu Nv) Ne(aA Il In It Iv Jg Jj Jp Lw Mk Ms Mz Nm Nu Nw Nx On) Il(Fp Jl Jn Lh Lx Mb Mh Ms Mt Mx Nh Nu Nv Nx Pe) Jj(Fp Jn Jt Lz Mb Mm Ms Mt Mx Mz Nc Nh Nm Nv Nw) Jg(Fp Ii In Iu Jk Lw Mb Mw Mx Ng Nl Nq Nu) Nx(aA Fp Ii In Iv Jp Lw Ms Mx Mz Nl Nu Oy) Ms(aA Iv Jn Jt Lw Mt Mx Mz Nh Nl Nu) Nu(aA In Iv Lw Mb Mk Mz Nl Oy) Mx(aA Hw In It Jp Lw Mk Nw) Mz(Hw In Iv Lw Mb Nc Nh Nl) On(In Jh Jk Mk Mp Mv Nb Ng) Mb(aA Jp Lw Mk Mm Nw) Nl(In It Lw Mk Ni Nk) Jp(Fp Hw Lw Nq Oy) Nw(Hw Ii In Mh Oy) aA(Hr In Jn Mt) Im(Is Js Mm) Oy(Lh Mt Nv) It(Jt Nh) LwIv MhLh MkMt IiJt InJn} Nt{Mk(Fp Ih Ik In Ir Is Jg Jl Jn Js Jt Li Lw Lx Mt Mz Nc Nl Nv Nx Of Pa Qb) My(Fp Fr Ij Ik In Jl Jn Jq Js Jt Lw Lx Mm Mt Mu Mx Nl Nn Nx Ny Pa Qb) Nf(Ih Ik Ir Jl Jn Jq Js Jt Lh Li Lw Lx Mp Mx Nl Nv Nx Ny Of Qb) Ii(Fp Ir Is Jg Jl Jq Js Lw Lx Mr Mt Mx Nv Nx Ny Pa Pe Qb) Ik(aA Fp Ir Jg Jn Js Lw Lx Mt Mz Nc Nl Nx Of Oy Qa Qb Qe) Oy(Fr Ih Ij Jq Js Jt Li Mm Mp Mt Nl Nn Ny Of Pa) Mx(Hu It Iv Jg Jr Js Lw Mh Mj Mz Na Nx) Mz(Ij Jg Lw Md Ml Ms Mv Mw Nb Om Po) Mh(Is Jl Jq Js Jt Lh Li Lx Nv Qb) Of(Fp Ih Ij Jl Jn Lh Lw Mt Pa) Ms(Ih Jn Jq Js Jt Nx Qa Qb) Nl(Fp In Is Jg Jn Jt Lw Lx) Jg(Fp Jh Jo Lw Mg Mw Ng) Lh(Hx Mv Mw Nb Ny Pb Po) Nv(Il In Jo Mv Mw Ng Nj) Jl(Hr Il Mw Nj Po) Lw(Fp Jn Nj Nx) Ng(Fr Jt Mm Ny) In(Jq Lx Nc Ny) Jo(Jq Js Jt Nx) Il(Is Js Qb) Fp(Jt Nx) Pa(Pb Pd) PoLx NnMw MjJt NjIh IvNx} On{Ii(aA Fp Ih Is It Jh Jj Jl Jn Js Jt Lh Lw Me Mh Mp Mt Mv Mw Mz Nc Ne Nf Ng Nh Nm Nq Nw Nx Pe Qa Qe) Mx(aA Hr Hu Hw Hx Il Im In Jh Jp Lw Mh Mk Mp Mv Mw Nf Ng Ni Nl Nu Om) Fp(aA Hr Hw Il Im In Jh Jp Mh Mj Mk Mp Mv Ne Ng Nh Ni Nq Nu Om) Mw(aA Jn Li Lv Lw Mh Mp Mt My Mz Ne Nf Nh Ni Nl Nn Nx Qa Qe) aA(Hr Ih It Jh Jn Jp Mh Mp Mv Mz Ne Nf Ni Nl Nq Nu Qe) Ms(Hr Ih Il It Jh Jp Lw Mv Mz Ne Nh Ni Nw Nx Qe) Nf(It Jn Me Mh Mz Ne Ng Nh Ni Nl Nu Nw Qa Qe) Im(Hr Hw In Jk Mp Mv Nc Ne Nh Ni Nq Oe Om) Mv(It Jg Jp Mh Mp Mz Ne Nh Nl Nu Nw) Ng(Jg Jn Jt Lw Mt Ne Nh Ni Nl Nm Qe) Jh(Jg Jn Mh Mp Ne Nh Ni Nl Nu) Nu(In Jp Mk Mp Nl Nq Nw) My(Hr Lv Mm Mp Nc Ni Qa) Ne(Mk Mz Ni Nw) Nl(Mk Mz Nk Nw) Mb(Ik Lw) Mp(Jn Nw) Jj(Ih Mh) MzHx NcNi IkOy IlQe ItNw} Nw{My(Fp Is It Jg Jp Jt Lh Lu Lv Lw Mb Mf Ms Mt Mu Mz Nc Ne Nf Nh Nm Nn Nv Nx Of Qa Qe) Ms(aA Fp Is It Jn Lw Mh Mt Mx Nc Ne Nf Nh Nl Nu Nx Of Og Oy Qa Qe) Of(Fp Ik Is It Jp Jt Lw Mb Mh Mt Nc Ne Nf Nh Nm Og Oy Qa Qe) aA(Fp Hr Ih Ii It Jg Jn Mb Mt Mw Mx Nc Ne Nf Nu Oy Qa Qe) Mb(Ik It Jt Lw Mh Mp Mt Mx Nc Nf Nm Nu Og Oy Qa Qe) Mx(Hx Ii It Jg Jj Jp Lw Mv Mw Nf Nl Nu Ny Oy Pb) Og(Ik Is Jn Jp Jt Lw Mt Nc Ne Nf Nh Nm Nx Qb Qe) Nf(Is It Me Mp Mz Ne Nh Ni Nl Nu Nx Qa Qe) Oy(Fp Is It Jg Mt Nc Ne Nh Nn Nv Qa Qe) Fp(Hr It Jp Lw Mh Mw Nc Ne Nh Nx) Nu(Ii It Jj Jp Jt Mh Mw Pb Qa Qe) Jj(Jg Nl Nx Qa Qe) Mh(It Ne Nl) Ii(Jt Lh) EtMv NnMw NcNi NeIt HrIm IlQe} Jp{Og(aA Ih Ik Ir It Jg Jl Jn Js Jt Lh Lw Mb Mp Ms Mt Mz Ne Nh Nl Nm Nv Nx Qb Qe) Fp(aA Hr Is It Iv Jg Jj Jt Lw Mk Mp Ms My Nf Nl Nm Nu Nx Of Oy Pb) Mx(aA It Jg Jj Lw Mb Mh Mj Mk Ms My Nf Ni Nl Nm Nu Nx Oy Pb) aA(Ih It Jn Mb Mh Ms Mt My Mz Nl Nu Nx Of Oy Qa Qe) Ms(Ih Is It Iv Jn Jt Lw Mt Nl Nu Nx Of Qa Qe) Of(Is It Jl Js Jt Lh Lw Mb Mt Nl Nm Qa Qe) Nu(It Lw Mb My Mz Nl Nx Pb Qa Qe) Iv(Is Lw Mb Mk My Mz Nl Nx Qe) Jj(Is It Jg Jn Nl Nx Qa Qe) Mb(Is Jt Lw Qa Qe) Nl(Is Lw Ni Oy Qe) My(Jg Mt Nv Qa) Oy(Jg Mt Nv Qa) eP(Ez Kl) IiLh JfdX} Im{Nf(aA Fp Jg Jj Jl Jn Jq Js Jt Lh Li Lv Lw Lx Mb Mt Mx Mz Ni Nl Nu Nv Nx Qa Qe) Nl(aA Fp In Jg Jl Jn Js Jt Lh Lv Lw Mm Mt Mx Ni Nk Nm No Nu Nv Nx Of Oy Qe) Nu(aA Hr Il In Iu Jg Jl Jn Js Jt Mk Ms Mt Mx My Mz Ng Nv Nx Of Oy Qe) Jg(aA Fp Il In Jh Jl Jn Lw Mb Ms Mt My Mz Nc Ne Oy Qe) Jj(Fp Jl Jn Js Jt Mb Mm Ms Mt Mx Mz Nc Ne Nh Nv Qe) Jt(Ii Il In Mb Mt Mx My Mz Ne Nx Of) Nx(Il In Ms Mt Mx Mz Of Qe) Mt(In Jn Ms Mz Oy Qe) Iv(aA Jn Lh Ng Nh Nv) In(Jn Js Mx Qe) Mz(Ms Ne Qe) Lh(Ii My Oy) Il(Jl Qe) Nv(Of Oy) aA(Jn Of) aC(aN cM) MxMy NyOg} Jg{Iv(aA Fp Ik In Jl Lw Mg Mk Ms Mx My Mz Ng Nj Nl Nu Oy Qa Qe) Mx(aA Ik In Lw Mb Mh Mj Mk Ms Mv Mw My Nf Ng Nl Nu) Nj(Fp Ik In Jl Js Lw Mp My Mz Ni Nu Oy Qa Qb Qe) Og(Ih Ir It Jj Jn Lh Mb Mp Ms Mt Nc Ne Nm Pa) aA(Fp Jh Jn Mb My Mz Ng Nl Nu Oy Qa Qb Qe) Jj(Fp Is It Jl Jn Js Nl Nu Nx Qa Qb) Oy(Fp Lx Mz Nu Nv Qa Qb Qe) Of(Ih Jt Lx Ms Ne Nh Ni) My(Fp Mz Nv Qa Qb Qe) Mz(Hx Mv Mw Ny Pb) Qe(Ms Ng Nl) EtMw NgQa} Nj{Iv(aA Fr In Jj Jl Jt Lh Lx Mt Mz Nn No Nv Ny Qa Qe) aA(Fr Ih Jn Js Jt Li Lx Mt Mx No Nu Nv Og Qa Qe) Mz(Hx In Jt Mh Mt Nu Nv Ny Og Pb Qa Qe) Og(Fr Is Jl Js Lh Mt Mx Nn Nu Ny) Qe(In Jj Jt Ni Nk Nu) Nv(In Ni Nk Of Oy) Qa(In Jj Ni Nk) Jj(Jl Js Jt) In(Js Jt) NiJt IiLh} Og{Iv(aA Fp Fr Is Jl Jn Js Jt Lh Li Lx Mm Mt Mx Mz Nm Nn Nu Ny Qa Qe) Qc(aA Jt Mt Nl Nm Nu Nx) Nu(Ij Jt Nv Nx Qa) Nl(Ij Jt Nv Qa) Ij(aA Mt Nx) Qa(aA Jt Nm) Nv(Mb Nm) MtNx} Et{Lx(Ii Mv Po) Pe(Mh Mw Po) Mr(Hx Ny) Ii(Jq Mi) Jh(Jq Jt) NnMv MhLh MuHu NiNk} Iv{Jj(Jt Mm Nv Nx Qa Qe) aA(Jn Mt Mz Nx Qe) In(Jt Nx) Nv(Of Oy) IiLh} Jj{Nx(Fp Jt Mt Nu) NuQe} aC{Ji(aN bM) AjJt}

Constrained panels with 3 analytes, where 1.0E-8 >= 'model p-value' > 1.0E-9. Contains 2,420 panels of 37,933,414 total panels evaluated. : Im{Mz(aA aC Fp Hr Hx Ii Il In Jl Jn Js Lh Lv Lw Lx Mb Mh Ml Mm Mp Mv Mw Mx My Nc Nh Nm Nv Ny Of Oy Pb) Mx(aA Hr Hu Hw Ik Il

Figure 31 Continued

Iq It Jn Jr Js Lv Lw Mb Mh Mj Mk Mm Ms Mt Nc Ne Nh Ni Nm Nv Of Oy Qe) Lh(Hr Hx Il In Jh Jj Jn Lw Mb Mh Ml Mm Ms Mv Mw Nb Nc Ne Ng Nh Nu Nx Ny Of Pb Po) Nf(aC Ik Il In Is It Jr Me Mm Mp Mq Mr Ms My Nc Ne Nh Nm Nn No Ny Of Pe Po) Lw(aC Fp Hr In Jj Jl Jn Js Mb Mm Ms Mt My Nc Ne Nh Nu Nv Nx Of Oy Qa Qe) In(aA Fp Is Jj Jl Jr Li Lv Lx Mb Mp Ms My Nc Ne Nh Nm Nv Of Oy Pe Qa) Of(aC Fp Il Jl Jn Js Lv Lx Ly Mb Mm Mp Ms Mt My Nc Ne Nh Ni Nm Qe) aA(Fp Hr Il Js Jt Lv Mb Mm Ms My Nc Ne Ng Nh Ni Nv Nx Oy Qa Qe) Ms(Fp Hr Il Jl Jn Js Jt Mm Mp Nc Ne Nh Ni Nl Nv Oy Qa Qe) aC(Aj aR aX aZ bM cD cX Dk Et Ji Jj Jp Jt Ml Mt Nw Og Qd) My(Fp Jj Jl Js Lv Lx Mm Mp Ne Nh Ni Nl Nm Nv Nx Qa Qe) Jn(Fp Il Jl Jt Lv Lx Mb Mm Nc Ne Nh Ni Nm Nv Nx Oy Qe) Ne(Fp Hr Il Jl Js Lv Lx Mm Ni Nm Nv Nx Oy Qa Qe) Jl(Fp Hr Ii Js Lx Mb Mh Mm Nc Nh Nm Nx Oy) Jt(Fp Hr Hw It Iu Na Nc Ng Nh Ni Oy Qe) Nv(Fp Hr Hw Ii Il Mb Mw Nc Ng Nh Ni Oe) Js(Hr Hw Il Lv Mb Mm Mt Nc Nh Ni Oy) Nx(Fp Hr Lx Mb Mm Nc Nh Ni Nm Oy Qa) Nu(Fp Ik Lv Lx Mb Mm Nc Pb Qa Qc) Oy(Fp Lx Mm Mp Nh Pe Pg Qa Qe) Mb(Lx Mm Mp Mt Nm Qa Qe) Il(Fp Lv Mt Nh Nl Pe Qa) Qe(Hr Lv Nc Nh Ni Nm) Fp(Hr Mm Nc Nh Nm) Lv(Jj Mm Nc Nh) Lx(Nh Nl) Mm(Nc Nh) Mt(Mk Ng) NcNi NIIu liPe IzJp QaJj} Iv{Mz(Fp Fr Hx In Is Jh Jj Jl Jn Jt Lh Li Lw Lx Mh Mk Ml Mm Mp Ms Mt Mx My Nc Ne Nf Nh Nl Nm Nu Nv Nx Ny Oy Pb Qa Qe) aA(Fp Hr Ih In Jh Jl Jq Js Jt Lh Li Lw Lx Mm Mx My Ne Nf Nh Nl Nm Nn No Nr Nu Nv Ny Oy Pa Qa Qb) Jt(Fp Hr Ii It Jl Jn Js Lx Mb Mj Mk Mm Ms Mt Mx My Na Ne Nf Nh Nl Nu Nv Nx Ny Of Oy Qa Qe) Nj(Fp Ih Ik Ip Is Jh Jn Jq Js Li Lw Mi Mk Mm Mp Mr Mx Nd Ni Nk Nm Nu Nx Oy Pa Qb Qc) Nx(Fp Fr Jl Jl Lh Li Lw Lx Mm Mp Ms Mt Mx Ne Nf Nh Nl Nm Nn No Nu Nv Of Oy Qa Qe) Nu(Fp Fr In Is Jj Jl Jn Jq Js Lh Lw Lx Mm Mt Mx Nf Nl Nn Nv Ny Oy Qa Qe) In(Fp Ih Is Jn Jq Js Lh Li Lx Mm Mt Mx Nl Nm Nn Nv Ny Og Qa Qe) Qe(Hr Il Jh Jn Jq Lh Lw Lx Mk Mm Mp Ms Mt Mx Nf Nh Nl Nm Oy) Og(Ih Ip Ir It Jh Jq Lw Mp Mr Nc Ne Nf Nh Nl No Nr Po Pz Qb) Lx(Jj Jl Jn Lw Mh Mk Mm Mx My Ne Nf Nh Ni Nl Nm Of Oy) Mt(Ik Jj Jl Jn Lh Lw Mk Mm Ms Mx My Nf Nl Nm Nn Ny Oy) Nl(Fp Fr Jj Jn Lh Li Lw Mm Nm Nn No Nv Ny Qa) Nf(Fp Fr Jl Jq Js Lh Li Mx Nn Nv Ny Qa) Jj(Fp Fr Is Jl Jn Jq Js Lh Li Mx Nn Ny) Nv(Fp Hr Ii Il Lw Mb Mk Mx My Ni Nm) Qa(Hr Il Lw Mk Mm Ms My Nm Of Oy) Lh(Hr Hx Jn Mh Mk Mm Mw My Nb Oy) Mx(Fr Jn Lw Mk Mm Nm Nn Ny) Lw(Fp Jn Li Mm Ny) Fr(Mk My Of Oy) Mm(Fp Jl Jn Of) Jl(Hr Jn) Of(Nn Ny) FpNm LiOy} Jp{Oy(Ih Ij Ik Ir Is It Jl Jn Jq Jr Js Jt Lh Li Lv Lw Lx Mb Mh Mi Mp Mq Mr Ms Mu Mz Ne Nh Nm Nn Nw Nx Pd Pe Pg Qb Qe) My(Ih Ij Ir Is It Jl Jn Jq Js Jt Lh Li Lv Lw Lx Mh Mi Mp Mr Mu Mz Nh Nm Nn Nx Pe Qb Qe) Jj(Ih Ij Ik Ir Jl Jr Js Jt Lh Li Lv Lw Lx Mb Mp Ms Mt Mz Ne Nh Nm Nv Nw Ny Qb) Nf(aA Is It Jl Jq Jr Js Jt Lh Me Mh Mp Mr Mz Nv Nw Nx Qa Qb Qe) Mb(Ih Ik It Jg Jl Jn Jq Js Lh Mp Mt Mz Nl Nm Nv Nw Nx Pb Qb) Of(Ih Ij Ik Ir Jn Jq Jr Li Lv Lx Mp Mz Ne Nh Ni Nv Ny Og Qb) Mz(Hr Hx Ii Jg Mh Ml Ms Mv Mw Ne Nh Nl Nx Ny Pb) Lw(aC Is It Jg Jn Mh Mt Ne Nh Nw Nx On Qa Qe) Nm(Is Jl Jn Jr Mh Ms Ne Ng Nh Nl Nx Qb Qe) Ms(Ir Jg Jl Jq Jr Js Mp Ne Nh Ni Nw Qb) Ni(Is It Jn Jt Mp Nc Nv On Qa Qb Qe) Nx(It Jt Mh Mp Mt Ne Nl Pb Qa Qe) Ne(aA Ih Is Jg Jl Jn Jt Mp) Mh(Jg Jl Lh Lx Og On Pb) Mp(It Jg Jn Nh Nl On) Mw(Jg Jl Lh Lx Nn Nv) Qa(Hw Il Jg Jk Mk Nl) Nh(Jl Jn Jt Nw Qe) Og(Jq Jr Li Lx Ny) aA(Hr Jg Lv Nw Qb) Mx(Iz Js Ua Vs) Nl(It Jl Jn Jt) Ii(Jl Jt Mr Pe) aC(aN Iz Ji Qd) Mt(Is It Mk) Mv(Iz Lh Nv) On(It Jh Nb) Ng(Jg Jt) Is(Nw Qe) Jl(Hr Pb) Lh(Hx Pb) LvIh IIQe ItNw IzQd QbJg KieP QmdX} Nj{Mz(Fp Fr Hr Ih Ii Ij Is Jh Jj Jl Jn Js Lh Li Lw Lx Md Mk Ml Mm Mp Mr Mv Mw Mx My Nf Ni Nk Nm Nn No Nx Oy Pa Qb) Jt(Fp Fr Hr Ih Ii Ik It Jg Jl Jn Js Lh Lx Mk Mp Mr Mt Mx My Nk Nn No Nu Nv Nx Ny Of Oy Qa Qb) Mt(Ik In Is Jg Jj Jl Jn Js Lh Lw Mk Mm Mp Mx Ni Nk Nm Nn No Nu Nv Nx Ny Oy Qa Qe) aA(Fp Hr Ij In Ip Ir Is Jh Jl Lh Lw Ma Mm Mp Mr Nf Ni Nk Nm Nn Nr Nx Ny Pa Qb Qc) Mx(Fr Ik In Jh Jj Lh Lw Lx Mm Ni Nk Nm Nn No Nu Nv Nx Ny Qa Qe) Qe(Hr Il Jh Jl Js Lh Lw Mk Mm Mp Nf Nm Nn No Nv Nx Oy) Og(Fp Ih Ip Ir Jh Jn Li Lw Lx Mm Mp Mr Nm No Nx Qb) Nu(Fr In Is Jj Jl Jn Js Lh Lx Nn No Nv Nx Qa) Qa(Hr Il Jl Lh Lw Mk Mm Mp Nf Nm Nv Nx Oy) Ni(Fr Jl Js Lh Li Lx Mm Mp Nn No Ny) Jj(Fr Ij Jn Lh Li Lx Mm Nn Nx Ny Qb) Lh(Hr In Jg Lx Mh My Nf Nk Oy) Nv(Fp Hr Ik Lw Mk My Nf Nm) Lx(In Jg Jl Lw Mk Nk Nx) In(Ih Is Jl Li Ny Qb) Jg(Ih Is Jn Mr Ng Pa) Fr(Js Nx Oy) bU(oD oV oW) Lw(Jl Js) Mm(Fp Js) HrJl} Jg{Oy(Ih Is Jj Jl Jn Jq Js Jt Lh Lv Lw Mb Mh Mi Mp Mr Ms Mt Mu Nc Ne Ng Nh Nl Nn Nx Oz Pa Pd Pe Pg) My(Ih Is Jj Jl Jn Jq Js Lh Lw Lx Mb Mi Mp Mr Mt Mu Ne Nl Nn Nu Nx Pe) Mz(Fp Hr Ii In Jh Jj Jn Mb Md Mh Ml Ms Ne Nf Ng Nl Nu Om Qa Qe) Fp(Ik In Jh Lw Mk Mp Ms Mw Nc Ne Nf Ng Nh Nl Nu Nw Nx Qe) Qa(Ii Il In Iu Jh Jk Lw Mb Mh Ms Mv Mw Nf Ni Nl Nu Nw Nx Pz) Ng(Is Jl Jn Js Jt Lh Lw Lx Mp Mt Nl Nu Nv Nw Nx Qb) Qb(In Iu Jh Jk Lw Mb Ms Mv Mw Ne Nf Ni Nl Nu) Nw(It Jh Lw Mb Mh Ms Mv Mw Nc Ne Nf Nm Qe) Nl(Ik Is Jl Jn Js Lw Lx Mg Mp Ms Ni Nu) Jj(aA Ih Ir Lh Lw Mb Mp Mt Nc Ne Nv Pa) Qe(Il In Iu Jk Lw Mb Mw Ni Nu Pz) Nu(In Is Jl Jn Js Lw Mb Ms) aA(Ih Mh Ms Mt Mw Nc Ne Nf) Ms(Is Jn Js Lw Mt Nx) Ii(Jl Lh Mr Mx Pe) Lw(Jn Js Mb Ne) Mw(Jl Lh Lx Nv) Mb(Jl Js Mp) Mx(Hu Jr Js) Aj(aC bM) Lx(Mh Mv) On(Mg Nm) MvLh InOk QdaC} Nw{Mh(Is Jl Jn Jt Lh Lu Lx Mr Mt Mz Nc Nh Nx On Pe Qa Qe) Mw(Is Jl Jn Jt Lh Lu Lw Me Mp Mt Mu Mz Nh Nv Nx Qa Qe) Jj(Fp Ih Is It Jn Js Jt Mb Mt Nc Ne Nf Nh Nm Qb) Ii(Fp Ih Is Jl Me Mr Mt Mz Nm Nx Pe Qa Qe) Oy(Jk Jl Jn Jt Lh Lu Lw Mp Nf Nx Oz Pd) Jt(Fp Hr In Jh Mj Ms Nc Ne Nf Nh) Mv(Is Lh Lu Mp Mt Mz Nn Nv Qa) Mz(Hx Md Ml Ms Ny Om Pb) Hr(Is Jl Lw Me Nm Qa Qe) Nf(Ih Jn Lh Lw Mt Nc) Qa(Hw Il In Mj Nc Ne Nf Nh Nx) Qe(Lw Nc Ne Nh Nx) On(Nb Nc Nh Ni Om) It(Me Mt Nh Nx) Lu(Nm Ny Pb) Mx(Hu Jr Js) Jn(Mb My Of) Lh(Hx Ny Po) Ms(Ih Ni) In(Ih Nx) aC(aN bM) PoPe LwNe MbPb MrNy NiNk JoOf} Og{Qe(Fp Ij Is Jh Jj Jl Jn Jq Js Lh Li Lv Lw Mb Mm Mp Ms Mu Mx Mz Nc Ne Nf Nh Nn Nv Ny) Qa(In Is Jh Jj Jn Jq Js Lh Lv Lw Mb Mm Ms Mt Mx Mz Ne Nf Nh Nn Nv) Nv(aA Fp Ij Is It Jj Jn Jt Lw Mt Mx Mz Ne Nf Nh Nx Of Oy) Nu(aA Fp Is It Jl Jn Jq Js Lh Lw Mt Mx Mz Nl Nm Ny Qb) Jt(aA Fp Ij Is Jl Jn Lx Mb Mt Mx Mz Ne Nh Nx Qb) Ij(Fp Is Jl Lw Mm Mx Mz Nc Ne Nf Nh Nm) Nx(aA Fp Fr Jl Lh Li Lx Mx Mz Nl Nm Qb) Mt(aA Fp Is Jn Js Lw Mx Mz Nl Nm Ny) Nl(aA Is Jl Js Li Lx Mz Nm) Nm(Fp Is Jl Js Mx Qb) aA(Jl Jn Js Li Mz) MmMx} Qd{aC(aN AR aS Ax bA bM cM cN cX Et Ji Jj Jt Lw Mx Mz Nf) In(Fp Jt Lh Lw Mb Ms Mt Nc Nh Nm) Ii(Jl Jq Lx Mi Mr Mz Nm Nv Pe) Oy(Jh Jl Jt Lx Mm Mp Nn Pd Pg) Mj(Fp Jn Lv Mb Mh Mr Nm Nv) Mk(Fp Jn Lh Lv Mm Nc Nh) Mx(aN Jr Js Lz Mb Mh Nm) Hw(Fp Jn Jt Lh Lw Nm) Mh(Jl Lx Mr Mz Nv) Lh(Hr Hx Mw Nb Po) Fp(It Lw Mm Nm) Mb(Jt Mt Nm) Mz(Hx Na Ny) Jq(Jr Js Na) Lw(Mt Nh) Jt(Js Na) Nv(Mv Mw) PoLx MrHx MuHu NcNi HrJl JnJr} On{Mh(Hr Hw Hx Il In Mj Mk Mp Mz Ni Om Po) Hr(It Jn Jt Lw Mw Mz Ne Nh Ni Qa Qe) Qe(Hw In Jh Jk Mk Mp Mv Nh Ni Nq) Qa(Hw Il In Jh Jk Mk Mp Ni Nq) In(Hu Ih It Jn Me Nc Nx) Mt(aA Jh Mk Mp Nq Oe) Jn(Hw Il Mv Ne Nh Ni) It(Hw Il Mk Ni Om) Po(Lh Lx Mr Pe) Mz(Ml Ny Om Pb) Jh(Jt Lw Me Nm) Mk(Lv Nc Oz) Nb(Lh Mr Pe) Js(Il Mw Mx) Nn(Mv Nq) Lw(Hw Mp) Nh(aA Mp) Ni(Hw Mv) AoaC MmMw MuHu MxJr NcaA IiQb JqOm} aA{Qe(Fp Hr In Jn Jt Lv Lw Mb Mm Mt Mx My Mz Ne Nf Nh Ni Nl Nm Nu Nx Oy) Jn(Fp Li Lv Lx Mb Mm Ms Mt Mx Mz Ne Nf Nl Nu Nv Nx Qa) Mt(Fp Hr It Js Jt Mb Mx My Mz Nl Nu Nx Oy Qa) Qa(Hr Mb My Mz Nf Nl Nu Nx Oy) Mz(Fp Jt Mx Ne Nl Nu Nx) Nv(Mb My Nl Of Oy) Fp(Jt Nl Nx) Mx(Jt Nu Nx) My(Ij Lh) Nl(Jt Li) NuNx NfLi} Jj{Nx(Fr It Jl Jn Js Lh Li Lx Mm Mx Mz Nl Nr Nv Qb) Nv(Fp It Jn Jt Mb Mx Nf Nl Nu Oy Qa Qe) Jt(aC Fp Mt Mx Nl Nu Qa Qe) Mm(Jn Mx Nl Nu Qa Qe) Qe(Jn Js Mt Nl Nm) Nu(Jl Jn Js Qa) Qa(Jn Mz Nl) bM(Ji Kf Mx) MtJs JiaC} aC{Ji(aL aR Ax aZ bA cD cM cN cX cZ Ii Jo Jt Li Lj Lw Mk Ml Mp Mz Nf Ni Nu) Jt(aN aZ bM cM cN cX Jo Lj Lw Mz Nf Ni Of) Lw(aN Ar Ax Et Li Lj Mx Nf) Mz(aN bM Et Li Nf Nh) CuNf} bU{kR(dU fA gC gZ oT oV oW pH pK) oW(eF iA In Jn Nk oK) dU(cC Hq Nb) oD(Mb Nd nN) GdkE NboV aReQ fAnW} Nx{Qa(In Ms Nf Nu Of Oy) Qe(In Ms Mt Nl Nu Of) Mt(Ms My Of) Nf(Fp Mz) Of(Jt Nv) JoOk} Nv{Oy(Fp Mb Mt Mx Nl Nu Of Qa Qe) Of(Jt Mb Nl Nm Nu) Nf(Fp Mb) MvOk IiJt} Ok{Po(Lh Mp Nd Pd Pe) Js(In Jo Ne) Mu(Hu Mv) Ij(Ii Il) NnJh MhJl MzIn HwIh PdPf} Nt{Ii(Ih Ij Li Mm) Nn(Ms Mv Nq) Mw(Fr Mu) Lh(Jh Ml) PoPe MhMr MkOz MsPa IjIl} Jt{Ii(Lh Lx Mt Mx Mz Qe) Mt(Ms My Oy) Nl(Fp Mz Qe) PoLx FpNf MjMx} Qe{Nl(Lw Mz Nk Nm Nu) Nu(In Lw) MtMy IiLh} Qa{Mz(Ms Nl) NuIn IiLh} Ji{MxaN bMcM} MtIiLh

Figure 31 Continued

Constrained panels with 3 analytes, where 1.0E-7 >= 'model p-value' > 1.0E-8. Contains 3,704 panels of 37,933,414 total panels evaluated. :
Nj{Mm(Ih Ij In Ip Ir Is Jl Jn Jr Lh Li Lw Lx Mp Mr Nk Nm Nn No Nu Nx Ny Of Oy Pa Pe Qb Qc) Mp(Fp Fr Ih Ij Ik In Ir Is Jh Jj Jl Jn Js Li Lx
Mr Mx Nf Nk Nm Nn No Nu Nx Ny Qb Qc) Lh(Fp Fr Hx Ih Is Jh Jl Jn Js Li Lw Mk Ml Mr Mv Mw Nb Nm Nn No Nx Ny Of Pb Po Qb) Nn(Fp
Ih Ik In Ip Ir Is Jh Jl Jn Lw Lx Mi Mr Nf Nk Nm No Nx Ny Of Oy Pa) No(Fp Ih In Ip Ir Is Jh Jj Jl Jn Js Li Lw Mr Nf Nh Nk Nm Nx Ny Oy Qb)
Nu(Fp Ih Ij Ik Ip Ir It Jh Jq Li Mi Mr Ni Nk Nm Ny Oy Pa Pe Qb Qc) Og(Ii In It Jk Jq Ma Mg Mi Mn Mq Mu Nd Nh Ni Nr Oi Pa Pe Po Pz Qc)
Jl(Fp Fr Ih Ir Is Jh Jn Js Li Mh Mk Mx Nf Nk Nm Nx Ny Of Oy Qb) Li(Hr Ih Ik Is Jh Jn Js Lw Mk Mr Mx Nf Nk Nm Nx Ny Of Oy) Nx(Fp In
Ir Is Jh Jn Lw Mi Mr My Nf Ni Nm Ny Of Oy Qb) Fp(Ih Ik In Is Jh Jj Jn Jq Lw Mx Nf Ni Nk Nm Ny) Fr(Ih In Ir Is Jn Lw Mk Mr My Nf Nk
Nm Of) Ny(Is Jh Jn Lw Mi Mr Nf Nk Nm Of Oy Pa) Nm(Ih In Is Jj Jn Js Lx Mr Ni Qb) Mr(Ih In Is Jh Jj Jn Lw Lx Nf) Js(Hr Jh Lx Mk Mx Nf
Nk Of Oy) Ni(Ih Ij Ir Is Jn Lw Nd Qb) Jj(Ih Ip Ir Is Jh Jq Nr Pz) Lw(Ih Ij In Is Jn Qb) Mx(Ih Ip Is Jn Mk Nf) Lx(Jh Jn Mh Nf Oy) In(Ij Ip Ir Jn
Jq) Nk(Is Nc Nl Qb) Mz(Jr Mi Pe) Ij(Nf Of Oy) Is(Ik Jh Nf) Aa(Iv Qe) Jh(Jn Qb) bU(dU pI) ImaC PzaA QdaN} Jt{Mx(aC Aj aN Fp Hr Hw Ik
Il In Ir It Jn Jr Js Lw Lx Mb Mh Mk Mm Ms Mt My Mz Na Ne Nf Nh Ni Nl Nu Nv Nx Of Oy Qa Qe) Nu(aA Fp Hr Ii In Is Jl Jn Js Lx Mb Mh
Mj Mk Mm Ms Mt My Mz Nc Ne Nf Ng Nl Nv Nx Ny Of Oy Qa Qb Qe) Nl(Fr Hr Ii In Ir Is It Jl Jn Js Li Lx Mb Mj Mm Mp Mr Ms Mt My Na
Ni Nk Nn No Nv Nx Of Oy Qa Qb) Og(aC Fr Ih Ii In Ip Ir It Jh Jj Jq Jr Js Lh Li Lv Lw Mm Mp Mr Ms Na Nc Nn Nr Ny) Fp(Hr Hw Ii In It Jn
Js Mb Mh Mj Mk Mm Ms Mt My Mz Nc Ne Nh Ni Nv Nx Of Oy Qe) Qe(Hr Hw Il In It Jn Js Mb Mh Mj Ms Mt My Mz Na Nc Ne Nf Nh Ni
Nx Of Oy) aA(Hr Ih Ii In Jl Jn Jr Js Li Lv Lx Mb Mm Ms My Nc Ne Nf Nh Nv Nx Of Qb) Qa(Hr Hw Ii Il In It Js Mb Mh Mj Mk Ms My Mz Na
Ne Nf Nh Ni Nx Of Oy) Jj(bM Ih Is Jl Jn Js Li Lx Mb Mm Mz Nc Ne Nh Nn Ny Qb) aC(aM AR Ax bA cD Cs Ct Cu Et Jp Li Lx Mk Mt Nk
Nw) Mt(Hr In It Jh Jn Js Mb Mj Mk Mz Na Nf Ng Nx Of) Mz(In Lx Mb Ms My Nc Ne Nf Nh Nx Of Qb) Nx(Hr Ii In Lx Mb Ms Ne Nf Nh Oy
Qb) Lx(In Mb Mh My Ne Nf Nh Of Oy) Jg(Ii In Jh Mb Mg Ms Mw My Nf) Ii(Jl Jn Js Mr Ne Pe Qb) Aj(aN bM cD cM Nf Qd) Nv(In Mb Ms
My Nf Oy) Mb(Jl Jn Nf Qb) Ms(Jn Js Ne Qb) In(Ih Jn Ne Qb) Of(Jl Mm Ne Nh) aN(Lj Qd) MyLh NeJn IkIv] Iv{Nf(Ih Ij Ip Ir Is It Jh Jj Jn Lv
Lw Mi Mm Mp Mq Mr Ne Nh Ni Nl Nm No Nr Pe Po Qb) Nh(Fp Fr Ih Ik In Is Jh Jj Jl Jn Jq Js Lh Li Lv Lw Mk Mm Mp Mx Nm Nn No Ny
Oy) Jh(Fp Ik In Is It Jj Jl Jn Jq Js Lh Lw Mk Mp Mx Ne Nl Nm Nn No Nu Of Oy Qb) Nm(Fr Hr Is Jj Jl Jn Jq Js Lh Li Mb Mm Mp My Ne Nn
No Nu Ny Of Oy Qb) In(Fr Ij Ip Ir It Jj Jl Lv Lw Mi Mp Mq Mr Nc Ne No Nr Pe Po Qb) Jj(Ih Ii Ij Ip Ir It Jm Jo Lv Lw Mp Nc Ne No Nr Pa Po
Pz Qb) Jl(Fp Ii Is Js Li Lw Mb Mh Mk Ms Mx My Nl Nn No Ny Of Oy) Oy(Fp Ij Is Jn Jq Js Lw Mm Mp Mx Nl Nn No Ny Pe Qb) Mp(Fp Is Jn
Jq Mb Mk Mm Mx Ne Nl Nn No Nu Ny) Lw(Aa aC Fr Hr Is Jq Js Lh Mb Ne Nn No Qb) Fp(Hr Ik Is Jn Jq Lh Mk Mx Ne Nn No Ny) Js(Fr Hr
Lh Mk Mm Ms Mt Mx Mz Nl Nx Of) Is(Fr Ik Lh Mk Mm Ms Ne Nl Nm No) Jq(Hr Mm Ms Mx My Mz Ne Nl No Of) Nn(Ik Lh Mb Mk Mm Ms
Ne Qa) Jn(Fr Ik Li Mk Ms Ne Nx Ny) Nl(Ih Ik Lv Mk Mx Ni Nk) Lh(Ml Mv Mx My Of Pb Po) Li(Hr Ik Mk Mx Ni Nu Of) No(Mk Mx Nc Ne
Nu Of) Mm(Fr Mb Ms Ne Ny) Og(Aa Ii Lv Pe Qc) Mz(Hr Ii Mv Na) Ij(aA My Of) Ny(Mb Ms Ne) Nu(It Mk) Mx(Ik Jr) AaQc FrMb NrMk
MhMr NaQa ImaN} aC{Jp(Aj aL AO AR AX aZ bM cD cM cN Cs Cu cX Hc Ih Is Jd Je Jj Jv Li Lj Lx Mi Mt Mx Mz Ni Nk Nm Nw Ok Or Ow
Pk Qe Vs Vt) Lw(aR BA Bb Bc bM bV cD cM cN Cs cT Cu cX dF Dg Dl Ij Is Jg Jj Jn Lh Lx Mm Mq Mt Mz Ni Nt Nu Nw Ok On Pe Qa Qe)
Et(aH al Aj aL aN aR AX aZ bA bM cM cN Cs Cu cX cZ Ih Is Jj Jn Jo Lh Li Lj Lx Mi Mt Mx Nf Nw Of Qe) Mz(AR AX bA Bb Bc cD cM Dl
In Jg Jj Jn Lj Mk Mx Nk Nm Nw Qe) Nw(aL Ao aR AX aZ cM cN Cs cX Jg Li Lj Mt Mx Nf Nm Nu Qe) Ok(Aj aL aN aR Ax bM cD cM Cs cX
Im Li Lj Mt Mx Nf Of) Im(aM aS Ax bA cN Cu Io Is Jg Mk Ni Nm Qe) Jj(Ba Cu Dc Is Jg Kf Mx Nm On Qa Qe) aN(Bb Cu Is Jn Li Lx Mm Mt
Nm On Qe) Li(aZ Bb bM cM Cu Is Jg Nf Nm) Mt(aZ Bb Bc bM Dl Jg Mx Nm) Is(AR Ax Bb bM cM Nf) Cu(In Io Jg Lj Mk Of) On(Aj aZ bM
Dk Of Oy) Nm(Aj Ax bA Cs Lj) Jg(aZ bM Cs Lj) cM(Ar Cs Lj Qe) Io(Af Ar Ax) bM(Ba Bb Kf) Qd(Bb Bc) aZ(Ar Qe) AjBa AxMm NlPe}
aA{Mz(Fr Hr Ih Ij Is It Jh Jl Js Lh Li Lv Lw Lx Mb Mm Mp Ms My Nc Nf Nh Nm Nr Nv Ny Qb) Fp(Hr Ih It Jh Jl Jq Js Lh Lv Lw Lx Mm Mx
Nc Ne Nf Nh Nm No Nu Nv Ny Og Pz Qa Qb) Nx(Fr Hr Ih In It Jh Jj Jl Js Lh Li Lx Mb Ms My Nc Ne Nf Nh Nl Nm No Nr Nv Of Qb) Nu(Ih Ij
Ir Is It Jl Jq Js Lh Li Lv Lw Lx Mb Mm My Nc Nf Nl Nn No Nv Ny Oy Qb) Mx(Fr Hr Ih In It Jh Jl Js Lh Li Lw Lx Mb Mm Ms Mt Nl Nm Nn No
Nv Ny Og Pz Qa Qb) Nl(Fr Hr Ih Ij Jh Jl Jq Js Lh Lv Lw Lx Mm Mp Ni Nk Nm Nn No Nr Ny Qb) Js(Fr Hr Ih Ii In Jh Li Lv Lw Lx Mb Mm Ms
My Nc Ne Nf Nm Of Oy) Li(Hr Ih Im Jl Lv Mb My Nc Ne Nh Ni Of Oy Qb) Lx(Hr Ih Im It Jl Mb Mm My Ne Nf Nh Og Oy) Jn(Fr Hr In Jh Jl
Lh Lw My Nc Nh Nm Oy) Og(Fr Ih Is Jq Lh Mm Nm Nn Nr Ny Pz Qb) Nv(Hr Ih Ii It Lv Mw Ne Nf Nh Ni) Qa(Hw In Lv Ms Ne Ni Of) Lh(Hr
Ii Im Nf Oy) Mt(Ih Mm Ms Nf) Mb(Jl Mm) Nf(Ij Qb) FrMy LvIh MmOf MsQe HrJl IjOy} Og{Nx(Ih In Ip Ir Is It Jh Jj Jn Js Lw Mb Mi Mm
Mp Mr Ms Mu Nc Ne Nf Nh Nn No Nr Ny Pe Po Pz Qc) Js(Fp Fr Ij In Is Jh Jj Jl Jn Lh Li Lw Lx Mb Mm Ms Mx Mz Ne Nc Ne Nf Nh Ny Qb)
Nu(Fr Ih Ip Ir Jh Jj Jk Jr Li Lv Lx Mb Mm Mp Mu Nc Ne Nh Nn No Pe Po) Jl(Fp Is It Jh Jj Jn Li Lw Lx Mb Mm Ms Mt Mx Mz Nc Ne Nf Nh
Ny) Ij(Fr In Ip Jh Jj Jn Jq Lh Li Lx Mb Mp Ms Nn Ny Qb) Mt(Ip Ir It Jq Lh Li Mb Mm Mp Ms My Nh Nn No Qb) Mx(Fr Is Jh Jn Jq Lh Li Lw
Lx Mz Nl Nn Ny Pz Qb) Nl(Fp Fr Ir Jh Jn Jq Lh Lw Mm Mp Nn No Ny Qb) Is(aN Fp Fr Lh Li Lw Lx Mm Mz Nc Ne Nh Nn) Nm(Fr Jn Lh Li
Lx Mm Mz Ne Nh Nn Ny) Mz(Fp Jn Lh Li Lx Mm Ne Nh Qb) Lh(Fp Jn Lx Mm Nf Nh Ny Qb) Fp(Jn Lw Mm Nh Ny Pz) Lx(It Jn Lw Mm Ne
Nh) Li(Jn Lw Ne Nf Nh Qb) Qb(Jh Lw Mm Nh) Jn(Fr Lw Mm) aN(Im Ji Qd) Ny(Lw Nh) InQe JibM} Jg{Nf(Ih Is It Jl Jq Jr Js Lh Lv Lx Me
Mh Mp Mq Mr Ni Nv Nx Pe) Ik(Ih Is It Jn Jr Mb Mh Mp Mt My Nc Ne Nh Nu Oy Pa) Jh(Is Jl Jp Jq Lh Lv Lw Lx Me Mp Mr Mt Ni Nn Nv Pe)
Mg(Ih Is It Jl Jn Lh Mb Mh Mp Ms Mt Ne Nh Nu Nx) In(Ih Is It Jn Jq Jr Js Lh Lx Mh Mp Mt Nc Nl Nx) Mw(Is Jq Js Lv Lw Mi Mp Mr Mt Mu
Nn Nx Pa Pe) Ms(Ih It Jl Jq Lx Mp My Nc Ne Ng Nh Pa) Mb(Ih Is Jn Jq Lh Lx Mt Nc Ng Nv) Mv(Jl Jq Js Mi Mp Mr Mt Nn Nv Pe) Lx(Hx Ii
Mk Ne Nh Ny Pb Po) Nc(Is Jl Lw Mp My Ng Ni Nx) Aj(aN cD cM Cu Mt Mx Qd) Mh(Jl Js Lh Mr My Nx Pe) Ne(Is Jl Jn Js Mp Ng Nx) Pe(Hr
Hx Nb Ny Pb Po) Mt(Is Jn Lw Mk Nx) My(Ij Ng Nh Ni Pa) Lh(Hr Hx Nb Ny Pb) Ii(Jq Js Nv Qb) Jl(Hr Jn Lw Mz) Mr(Hx Ny Pb) Ng(Ih Nm
Pa) Hu(Mu Nn Nv) Mp(Jn Nx) Ij(Mz Oy) Pb(Mi Pa) LwIs NbOn NiIh IlQb ItNx JjbM JoJs JqOm} Qe{Nu(Fp Hr Il Is Jh Jl Jn Jq Js Mb Mk Mm Ms Mt Mx My Mz Nf Nh Nm Nv Ny Oy) Nm(Fp Hr Il In Jn Js Mb Ms Mt Mx My Mz Nc Ne Nf Nh Ni Nx Of Oy) Nl(Fp Hr Il In Jh Jn Jq Lh Li Mk Mm Mp Ms Mt Mx Nf Ni No Nv Oy) Jj(Aa Fp Is Jh Jl Jo Jq Lh Li Lv Lw Mb Mx Mz Nc Ne Nf Nh Nn Ny) Mz(Hr Hx Il In Lw Mb Mh Mm Ms Mt Mx My Ne Nf Nh Nx Ny Pb) Lw(Fp Hr In Jn Js Mb Mm Ms Mt Mx Ne Nf Nh Nx Oy) Nf(Fp Jq Js Lh Li Mb Mm Mp Mt Mx Ni Nv Nx) Nx(Fp Hr Il Jh Mb Mm Mx My Ne Nh Ni Oy) Mm(Fp Jn Mb Ms Mx My Nh Ni Of Oy) eP(Rt Rv Ux Uy Uz Va Vh Vi Ti) Mt(Il In Jn Mb Mk Ms Mx Oy) Mb(Jn Jq Js Mp Mx Nv) Il(Jl Jn Js Lh Mx Nv) Ms(Jn Jq Js Mx Nh) Lh(Hr Mh My Oy) In(Jn Js Mx) dX(Vh Vi Ti) Jp(Ua Vs) Nv(My Of) AaOf LxMh NhJn HrJl UhcM} Qa{Mz(Fp Hr Hw Hx Il In Lv Lw Mb Mh Mk Mm Mp Mt Mx My Nc Nf Nh Nm Nu Nx Ny Oy Pb) Nf(Fp In Jj Jl Jn Jq Js Lh Li Lv Lw Mb Mm Mp Ms Mt Mx Nh Ni Nl Nm Nu Nv) Nl(Fp Hr Il In Jn Lh Lw Mk Mm Mp Ms Mt Nh Ni Nk Nm Nu Nx Oy) Mb(In Jj Jn Lh Lw Mk Mm Mp Mt Mx Nm Nu Nv Nx Oy) In(Fp Jj Jn Js Lh Lv Lw Mm Ms Mt Mx Nh Nm Nv) Nm(Fp Hr Im Jj Ms Mt Mx My Ne Nu Nx Oy) Nu(Hr Il Lw Mk Mm Ms Mx My Nv Of Oy) Jj(Fp Js Lh Lv Ms Mt Mx Ne Nh Nn) Nx(Fp Hr Hw Ii Il Lw Mt Mx My Ni) Oy(Jh Jn Lh Lv Lw Lx Mm Mp Mt Mx) Ms(Jn Jq Js Lw Mm Mt Nh Ni) Im(Hr Hw Lv Mm Nc Nh Ni Of) Lh(Hr Hx Il Mh Mw My Po) Mt(Il Lw Mk My) Mx(Il It Lw Mj) Mm(Fp My Of) Nv(Hw My Of) Hr(Jl Lw) Jp(Ua Vs) LvMk WfeP} Jp{Iz(aN Ar Ax bL bM Bn bU cD cM cN Cs cX dJ fP Ik Jd Jh Kf Kx Li Lj Lv Mk Mq Mt Mu Mz Nm Oa OE Or Ow Pk To Ub Ur Us Wm) Lj(aN Hc Ib Jd Jv Or Ow Pk Qw Ra Rf Ua Ub Vs) Hc(aN Ax bM Ik Lv Mx Nm Or Ow Pa Pk Qd) Nf(Ih Ir Li Lv Lx Mi Mq Ni Nn Pe Pk) Jd(aN Ax Ik Im Kq Mx Nm Or Pa Pk Qd) Lx(Hx

Figure 31 Continued li Mk Mv Nh Ni Ny Pb Po) Mx(aN Ib Ow Qt Qw Rf Ub Uc Uu) Or(Ao bM cM Hu Ik Jj Lv Mk Ow) Vs(Ax Im Ir Li Oa Oh Pk Qd) Ni(Ih Js Li My Nv) Pe(Hr Hx Mh Mw Ny) Pk(Hu Ik Jj Lv Uv) Mr(Hx Mh Mw Ny) Qd(aN Ib Ua Uc) eP(Fa Kf Wd Wh) My(Jr Mf Ny) Nv(li Ng Pb) Ow(Ax bM Lv) Nn(Hu Mv) Mu(Hu Mw) Ua(Im Li) Ib(Ax No) Ih(Nh Pb) Ij(Il Ng) Kf(Ef Uu) Lh(Hr Ny) aN(Im Ji) NmOa LvQb MzJr liJq} Mt{Mz(Fp Hx Ii Is It Jj Jn Lw Mb Mh Mk Ms Mx My Nf Nl Nm Nu Nx Ny Oy Pb) Nl(Fp Is Jj Jl Jn Js Lh Lw Mk Mm Mx My Nm No Nu Nx Oy) Jn(Fp In Jj Jl Lh Lw Mb Mk Mm Ms Mx My Nm Nu Nx Oy) Oy(Fp Ij Is Jl Jq Js Lh Lw Lx Mm Mp Mx Nm Nu Nx) My(Fp Ij Is It Jl Js Lh Lw Mm Mx Nm Nu Nv Ny) Jj(Fp Is It Jl Jq Lh Mm Mx Nm Nn Nu Nv Ny Qb) Nx(Fp In It Jl Lw Mb Mk Mx Nf Nm Nu) Js(Il In Lw Mb Mk Ms Nf Nu Of) Fp(Lw Mk Mm Ms Nf Nm Nu Nv) Mx(aN Ik In Lw Mk Ms Nm Nu) eP(Rt Vh Vi Wc Wd We Wf Wh) Mb(Jl Lw Mk Mm Nm Nv) Nu(Is It Jl Jq Lw) Ms(Is Jq Lw Mm Nv) Lh(Mh Mk Mv Mw Nf) Nv(Nf Of) Mklt MmOf JiaN} Im{Oy(Fr Ij Jo Li Lu Lv Ly Mb Mi Mk Mr Nc Ni Nm Nn No Ny Oz Pd Qc) ll(Fr Ij In Li Lw Lx Ly Mb Mh Mm Mp Mr My Nc Ni Ny Oz Qb Qc) Ni(Fp Hr Li Lv Lw Lx Mm Mp Nn No Ny Qb Qc) aN(Aj cD cM Ji Jj Jn Lw Mx Mz Nf Nw Qd) Nn(Hu Lv Lw Mb Ms Mv Mw My Ne Nh) My(Fp Ij Li Mr Ms Mu Nc Ny Pe) Mb(Fr Ik Li Mk Ne No Ny Qc) Hr(Is Jo Jq Li Mr Nh Nm Pe) Lv(Fp Ik Lw Mk Ms Ng Nm) Pe(Hw Hx Mh Mw Ny Pb Po) Lw(Hw Iq Li Lx Ng Qc) Nc(Lx Mk Mr Nk Nm No) Mm(Jr Lx Ng Nm Nv) Fp(Hw Ik Lh Mk) Mr(Hx Ii Mh Mw) Iq(Jl Lh Mp Mz) Nm(Hw Ng Nh) In(Ij Ny Qb) cM(Aj bM kR) No(Ne Nh) Lx(Mh Mk) Mi(Hx Mw) Mp(Hw Ng) MuHu NeLi NgJh HwJl JjbM OzPb} Nv{Oy(Is It Jn Js Lh Li Lv Lw Lx Mm Mp Ms Mz Ne Nf Nh Ni Nm Nn Nx Qb) Mx(Hw Ii Il In Jn Lw Mb Mh Mj Mk Ms My Nf Ni Nl Nm Nu Nx Of) Of(Fp In Is It Jj Jn Js Lv Lw Mm Ms My Mz Ne Nf Nh Ni) Nu(Fp Hr Ii In It Jn Lw Mb Mk Mw My Mz Nf Ng Nl Nx) Fp(Hr In Lw Mj Mk Mm My Mz Ne Nh Ni Nl Nm Nx) My(Jj Jn Lh Lw Lx Mb Mz Nf Nh Nl Nm Nx) Nf(Is It Jn Lw Me Mz Nh Ni Nl Nm Nx) Mb(Ik In Jn Lw Mk Mm Mz Nl Nm Pb) Jj(Ih Is Js Mm Mz Nc Ne Nh Nm) Nl(In Jn Lw Mk Mz Ni Nk Nm) Ii(Lh Mr Mz Nw) Ms(Jn Mz) MzHx} Nx{Jj(Ih Ij Ir Is Jh Jk Jm Jo Lw Mp Mr Ms Nc Ne Nf Nh Nm Nn No Ny Pe Po Pz Qc) Fp(Hr In It Jh Lw Lx Mm Mp Ms Mx My Mz Nc Ne Nh Nl Nm Nu Of Oy) Nu(In It Jl Jn Js Lh Li Lw Lx Mp Ms Mx My Mz Nf Nl Of Oy Qb) Mx(Fr In It Jh Jn Li Lw Lx Mm Ms Mz Nf Nh Nl Nm No Of Oy) Lx(In It Ms My Mz Ne Nf Nh Nl Of Oy) Mz(Hx In Mh Ms My Nl Ny Of Pb) Of(Fr Jl Js Lh Li Mm Nl Nm) Nl(Fr In Li Lw Nm No) Lh(Ii My Nf Oy) In(Js Li Qb) Nf(Js Li) MsJs} Nl{Mz(Fp Fr Hr Hx In Is Jh Jj Jl Jn Js Lh Li Lv Lw Lx Mh Mm Mp Ms Mx My Nf Nm Nn No Nu Ny Pb Qb) Lx(Fp In Jj Jl Jn Js Lh Lw Mk Mm Mx Nf Ni Nk Nm Nu Oy) Jj(Fp Fr Ij Is Jl Jn Js Lh Li Nn No Nu Ny Qb) Jn(Fp Fr In Jl Lh Li Lw Mm Mp Mx Nm Nu) Nu(Fp Is Jl Jq Js Lh Li Lw Mx No) Fp(Js Lw Mm Mp Nf Nk Nm No) Mx(Fr Lw Mm Nm No) Js(In Lw Ms Nm) Lh(Ii My Nf Oy) Li(Lw Nf Ni) FrOy MmOf} Nu{Mz(Fp Hx Is It Jj Jl Jn Js Lw Lx Mb Mh Mm Ms Mx My Nf Ny Oy Pb) Mx(In Is It Jh Jj Jl Jn Jq Js Lw Mm Nf Nm Oy) Jj(Fp Ij Ir Is It Jq Lh Li Lx Nn Ny Qb) Nf(Fp Is Jl Jq Js Lh Li) Jn(In Jl Lh Lw Lx Mm Ms) Js(In Lw Mb Mm Ms Oy) Lh(Ii Mw My Oy) Fp(Jq Lw Mm) Is(In Lx Oy) Jl(Mb Oy) LxOy InQb} aN{Ji(Aj aK Ax aZ bA bM bU cD cM cT dJ Ii Ik Jj Jn Jo Li Lj Lw Mp Mz Nf Of Qd) Qd(Aj Ar aS Ax bA bM cD cM cT dD dK Jj Jn Li Lj Lw Mz Nf) Mx(cM Et Jj Jn Lw Mz Nw) Lw(Ax Li Lj) Mz(Jn Li Nf) Is(Aj cD Jj) Nw(bM cD Lj) Nf(Cu Pe) Jn(Jj Li) On(Aj Of) LjcM} Jj{Js(Fp Fr Jh Jn Lh Li Lx Mb Mm Ms Mx Mz Nc Ne Nf Nh Nm Ny) bM(Ba Bb Cu Dc Et Is Jn Kp Ks Mz On Qd) Mm(Fp Is It Jl Lh Lx Mz Nc Qb) Mx(cM Jd Jn Kf Kp Nn Ny) Jn(Fp Jl Lh Li Lx) Kf(Lj Uu) MbJl} bU{kE(Dr Fc Gb Gc Gn gZ Hl Lt oD Ry Rz Sf Sh Wb Yd Zw Tm Tl) oW(bN cF cO dJ Hq Hv Jr) Gn(kK kP mS nl nJ) dU(aR dB gL) fB(dJ kR) nC(Hl Ho) JneQ cCpK iHkC} Lh{li(Fp Is Jn Js Lw Lx Mm Mx Mz Nf Nh Nm Ny Qb) Nf(Fp Is Jn Js Li Lx Mx My Mz) My(Is Jn Lw Lx Mx Nm) Nw(Hr Ml Nb Pb) eP(Wd Wh) MmOf MzHx JnOy} cM{Mx(bM Jd nY Qd Uh Ur Vt) Gn(kC lY mE mF mH ml) Uh(Ax bM Cs iO Lj) Zw(kF kN nB) Qd(Aj bM) Ji(iO oE) Vt(Ax Cs) mS(Gc Op) JdLj NwbM bOoD} bM{Ji(Aj aK aS aU Ax aZ bA cD cT dD Ii Jo Lj Mp Mx Nf Of) Nf(Cu Mz Qd) Aj(Ba On) Qd(aS dD) MxNw} Nw{Hx(Jl Lu Mi Mr Pe) Po(Lx Mr) Nb(Mr Pe) Ii(Jo Js) In(Jn Qb) Jl(Mv Ny) NnJh MuHu MzHr NiQb JnJr PaPe aDgV mFjF} Nf{Fp(Jq Js Lw Mm Mp Mz Nm Ny) Mz(Jn Li Lx Mm) Js(Li Mb Ms) Mx(Li Lx)} Mm{Fp(Jn Js Mz Nh Oy) Mb(Jn Js Mx Mz) Mx(Jn Lw Of) Mz(Hx Pb)} eP{Wh(Hv Ji Un Vt) Wd(Ar Js Vt) Kx(Kp Or) MnKc NbVb StUy} Mz{Lx(Ne Nh) Ms(Jn Js) NqrC LwMx UydX} Mx{Jn(In Lw Nm) IkJd QgVt} dX{St(Uy Wf) HvWh WeUn} rR{Nq(Uf Wm) JvrC KfwF} On{AaOf HpmM HvOm} AjBaQd AxMkOr WmJkwQ NqPegW LwLjcD KfiAwF RyLikN WnUhUu jFqUkK Constrained panels with 3 analytes, where 1.0E-6 >= 'model p-value' > 1.0E-7. Contains 8,591 panels of 37,933,414 total panels evaluated. : aC{Ax(aN Ao Ap aR aX aZ BA Bb BC bM cD cM Cp Cu Dc De dF Dg dJ Dl Ih Jg Jj Jn Jq Kf Li Mi Mk Ml Mt Nf Ni Nk Nu On Pj Qe Vt) aN(Ao Ap Ar aZ BA Bc Cp Cs cT Cw Dc Dd dF Dg Dl Fr Ih Ij Io Ir Iv Jg Kf Lh Lj Mi Mq Mx Nf Nj Nt Nu Nv Nx Ny Pe Qa Qc) aZ(Ad Ao Ap Ba Bb Bc bM Cp Cs Cu Dc Dd Dg Dl Fr Ih Ij Io Is Iv Jn Lh Lj Lx Mm Mq Mx Nf Ni Nm Nt Nx Ok Pe Pj Qa Qc) Bb(aL aM Ao AR aX bA cD cM cN Cs cT Cu dF dL Hu Ih Io Jj Lj Lx Lz Mi Ml Mm Mq Mx Nf Ni Nm Og On Pe Qa Qe) Lj(Ap aR aX BA BC bM cD cN cX De dF Dg dJ Dl Io Is Jj Kf Mg Mi Mk Ml Mm Mt Mu Nf Ni Nk Nt Nx On Vt) Jj(Ad Ao Ap Ar bA Bc bM Cp Cs Cw Dd Dg Dl Fw Ih Ij Iv Jn Js Kp Lh Li Lx Mm Mt Nt Nx Ok Pj Qc Vq Vt) Lx(Ao aR aX BA BC bM cD cF cM Cs cX dJ Dl Ih Io Jg Jn Mi Mk Ml Mm Nf Ni Nk Nm Nu Pg Qe) Qe(AR aS aX BA Bc cD cN Cu cX Di Dl Is It Jg Jq Li Mi Mk Ml Mm Mt Nf Ni Nk Nm Ok On) Mt(AR aX BA bU cD cF cM cN Cs cX dJ Io Is Jn Li Mi Mk Mm Nf Ni Nk On Qa Qc) Jg(aL aM Ao AR aX bA cD cM cN cU cX Ih Is Jn Mi Mq Mx Ni Nm Nu Of Og Pa Pe Qa) Li(aR BA Bc cD cN Cs cX Ih Io Jn Jq Mi Mk Ml Mm Mx Ni Nu On Pa Qa Qc Vt) Ar(aX Ba Bc bM cD cT Cu dJ Dl Et Ih Mi Mk Ml Mm Mx Nf Nj Nm Og Ok Qa Vt) Kf(Aj aL aM cD cM cX Ef Ik Im Iz Jv Lv Mk Ni Of Og Oi Or Pk Qd Ub Uu Vt) Nm(aR aS Bc bM bV cD cM cN cT cX dF Ih Is Jn Lh Mx Nf Ni Og On Pe Qa) bM(Ap bA Bc Cs cT Cu Dc dF Dg Dl Gp Ih Io Jn Kp Lh Mi Mm Mx Pj Pk) cM(Ba Bc Cp Cu Dc dF Ih Ij Iv Jn Lh Mm Mx Nt On Pj Qa Qc Uh Un Vt) Is(Aj aM aS aX bA Bc cD cN cX dJ Dl Mk Ml Mm Nh Ni Nk Nu On) Im(Hf Ic Iz Jd Ju Jv Kc Kp Kz Or Pj Pk Qw Ub Ur Vt Wm) Bc(Aj aR cD Cs Ih Io Iv Lz Mi Mm Mx Nf Nj Nu Og On) Pj(bA cN cX Ik Kp Lv Mk Mq Mx Mz Nd Or Pa Pk Ub Vt) Ba(aL aM aR cD Cs Ct Ih Io Lz Mi Mx Nd Nf Of Og) Mm(Aj aR aX bA cD cN Cs cT cX Ih Jn Mx Nf Ni Pk) Nf(Ad aR Cp Cs Cw Dc Ih Ij Jq Lh On Qa Vt) Ih(aR aS aX bA cD cN cX dF dJ Mi Nh Ni) On(aO aR aX bA bF cD cN Cs cX Hu Mk Ni) Vt(aS Ir Ji Kp Lv Mk Mx Pa Qd Qg Ub Wm) Cs(aR bC cD Dg Io Mi Mk Ml Ni Og) Qa(aR aX bA cN cX Et Jp Mk Ml Nh) aX(Dl Ij Jn Lh Mx Ok Pe) bA(cD Dc Dl Io Jn Mi Mx) Cu(Aj aL aR cD Jo Ml) Ub(Ir Ji Jp Qd Un Vq) Jp(Et Lh Nx Oa Wm) aR(Dg Jn Lh Mx Nu) Aj(Ad Ap Dg Io) Dl(cD dF Io Og) Ok(cN cZ Jn Ni) Dc(cD Io Og) Wm(Ji Nw Qd) Et(AO) Mi(Lh Mx) Jn(cN Ml) Kp(Or Qd) bU(dU oW) nL(jO jP) ApOf LwQc MkOr KcPk LhcN VqcF mWqU nHjO} Mz{Mx(bM cD cM Fp Fr Hr Hx Ii In Is It Jh Jj Jl Jn Js Lh Li Lv Lx Mb Mh Ml Mm Mp Ms My Nc Ne Nf Nh Nm Nn Nv Ny Pb) Nh(aN bM Fp Fr Hr Hx Is It Jj Jl Jn Js Lh Li Lv Lw Mh Ml Mm Mp Ms Mt My Nf Nm Nn No Nu Nv Nx Ny Pb Qb) Jn(bM Fp Fr Hr Hx Ii Ij In Jh Jj Jl Jt Lh Li Lv Lw Lx Mb Mh Ml Mm Mp My Nc Ne Nm Nv Nx Ny Oy Pb Qe) aN(Aj Ar Ax bA bM bU cB cD cF cM Cs cT dJ dK Et Iv Jj Jp Jt Lj Lw Lz Mh Mt Nj Nt Nw Nx Og Pe Qc Qe) Nf(Ar bA cD Fr Hx Ih Ij Ir Is It Jh Jl Jq Js Lv Lw Mb Mp Mq Mr Ms Nc Ne Nm Nn No Ny Og Pb Pz Qb) Ne(Fp Fr Hr Hx Is It Jh Jj Jl Jq Js Lh Li Lv Lw Mh Mm Mp Ms Mt Nm Nn No Nu Nv Nx Ny Pb Qb) Li(bM Hr Hx Ii In Is Jj Jl Lv Lw Mb Mh Ml Mm Mp Ms Mv Mw My Nc Nm Nu Nx Ny Of Oy Pb Qe) Fp(Hr Hx In Is It Jh Jj Jl Jq Js Lh Lv Lw Lx Mb Mh Ml Mp Ms My Nc Nm Nn Ny Pb Pz Qe) Lx(Hr Hx Ii In Is It Jj Jl Js Lw Mb Mh Mk Ml Mm Mp Ms Mv Mw My Nc Nm Ny Oy Pb) Mm(Hr Ii In Is It Jr Js Lh Lv Md Mh Ml Ms Mt Mv Mw My Nc Nx Ny Of Oy Qb) Lh(Hr In Is It Jj Lw Mb Mh Ml Ms Mt Mw My Nb Nc Nu Nx Ny Oy Pb Qb Qe) Nx(Fr Hr

Figure 31 Continued

Figure 31 Continued aA(Na Nr) bM(cM Nw) FpIk FrNg MuMw NiLi mFjF} cM{oD(Dp Fb Fw Hb Ib Iz Jd Ju Jy Kc Kf Ki Kj Kk Kp Kq Kr Ks Ld Mb Nb Nd nN Oa Or Ou Ow Pk Qm Qt Qu Qv Qw Rb Rc Ri Rm Ss St Tr Tt Tv Ub Ue Ug Ul Un Up Ur Us Ut Uu Vp Vq Vv) gZ(Dp Em Gp Ha Hb Ju Jv Kg Ki Kj Kk Kp Kr Ks Kx Nb Oa Qm Qt Qv Qw Rb Tr Ub Ue Ug Ul Un Up Ur Us Uu Vq) Qd(Ar aS Ax bA bV cN Cs cT Et Fp Iv Ji Jn Kp Lj Lw Nb Nf Nj Ns Nt oE Or Ub Uh Vt Wm) Lj(bA bM bV cN dF Et Im Ji Kc Kf Kp kR Lw Nt oE Or Pj Qm Sr Ub Un Vt) bM(Ax bA Cs cT dF Et Is Jd Jg Jn Ke Kf Kp Li Oa Ok Or Pk Qe Vt) eQ(Ed Fw Fy Hf Ic Ke Kf Kp Or Ow Ph Pj Qg Qm Qu Qy Sr Ss Uh Uu) fA(bO Dp Fw Ju Kg Ki Kj Kp Ks Qm Qv Rb Rh Sr St Tr Ub Up Ur) Vt(Ar aS Fp Im iO Ir Ji Kf Kp Li Nf oE Qa Qe Qg Ub Uh) gC(Dp Fb Fn Hb Hf Ib Id Ki Kj Kk Kp Kr Oa Pj Ql Qm) Ji(Aj Ax bV Cs Fp Ii Im Jo Mp Qe Ub Wm) jB(cF Ef Fw Fy Kp Ph Qg Qu Qy Uk Un) Uh(aN Ar Fp Im Ir Li Oa Or Qa Ub) Kp(dU Im Or oT oV pH pK Qa Qe) aN(Cs Fp Is Jn Li Lx Nw Qa Qe) Ub(Cs Im Ir Jd oW pI Qa Qe) Aj(Et Kf Nt Ok On Qe) Or(Ax Cs Im Li Mk Pj) Un(Ax Cs fB oT oV pH) nK(Fi Gn Hl Ho Yj Zw) oE(Cs Fy Ir Kn Pj Pk) dU(aL Ed Fn Fw Ow) Et(Cs kR nY) Um(nO oT oW) Pj(Ax iO nY) Gn(lW nJ) Im(Hf Qe) Ir(kR nY) Yj(mE mI) Li(iO mF) Ur(oW pI) fB(Hb Qm) CsUo GchB LwQe XamI YemZ KfrR UgoW cFpK eMnN} Nf{Lx(aN Fp Ih Ij Ir Is It Jl Jn Jq Jr Js Li Lv Lw Mb Me Mi Mm Mp Mq Mr Mt Ne Nh Ni Nm Nn Nu Nv Ny Og Qe) Nx(Fr Ij Ir Is It Jh Jl Jn Jq Lv Lw Mb Mi Mm Mp Mq Mr Ms Ne Nh Ni Nl Nm Nn No Ny Of Pe Po Qb) Li(aN bM Fp Ih Ir Is It Jl Jn Jq Jr Lv Lw Mb Me Mm Mp Mq Mr Mt Ne Nh Ni Nm Nv Ny Qb) Js(Fr Ih In Is Jh Jl Jn Lv Lw Me Mm Mp Mq Mr Ne Nh Ni Nl Nm Nn Nv Ny Of) Fp(Fr Ih Ij Ip Ir Is It Jh Jl Jn Lv Mg Mi Nc Ne Nh Ni Nn No Og Pz Qb) aA(Fr Ih Ip Ir Is It Jl Jq Lv Mb Mm Mp Ne Nh Nl Nm Nn No Nr Ny Og Po) Mt(Ij Ir Is It Jl Jq Lv Lw Mb Mm Mp Mr Ni Nm Nn No Nu Ny Pe Qb) Qd(Ad Aj AR AS Ax bA bE Bn cD Cq Cs cT Cu Cw Dc dD) Qe(aN In Is Jh Jl Jn Jr Lv Mi Mq Mr Ms Ne Nh Nn Ny) Nu(Fr Ij Ir It Jn Jr Lv Lw Mm Mp Nn No Ny Pe Qb) Ji(Aj Ax bA cD Cs Cu hC iP kS nY oE Ub Us Vt Wm) Nj(Ih Ip Ir Jq Lw Mi Mq Ni Nm Pe Po Qb) Lw(aN Ar Ax bA bM Cs cT Jl Jn Ny) Nl(Fr Ij Is Jl Jq Mp Nn Ny Qb) Vt(aS Ax Im Kf Kq Oh Qa) bM(bA Dc Is Jq Nw Ok Pe) Jl(Jn Mb Mm Nm Nn Ny) Nv(Jr Lv Mp Mr Ms Ne) Og(Fr Is Jn Nn Ny Qb) Jn(Fr Mm Mp Nm) aN(Is Lj Nw Qa) Cu(Aj Ar Lj) Pe(iA kS oE) Nm(Is Qb) Mb(Mm Ny) Mp(Ij Ny) Im(Or Us) Iv(Ik Jr) Qa(Ne Nn) AjOn FrIs MmQb} Nl{Mm(Fr Ih Ij Ir Is It Jh Jl Jq Jr Js Lv Lw Mb Mi Mp Mr Ms Ni Nk Nm Nn No Nu Nx Ny Oy Pe Qb) Jl(Fp Fr Hr Ih Ij In Is Jh Js Li Lw Mb Mh Mp Ms Ni Nk Nm Nn No Nx Ny Of Oy Qb) Mp(Fr Ih Ij In Ir Is Jh Jq Js Li Lw Mr Mt Ni Nk Nm Nn No Nu Nx Ny Oy Qb) Nm(Fr Hr Ih Ij In Ir Is Jh Jq Li Lv Mb Mr Ni Nk Nn No Nu Ny Oy Qb) Og(Ih Ii Ip It Jk Jo Lv Ma Mg Mi Mn Mr Mu Ni Nj Nk Nr Oi Pe Po Pz) Nx(Ij Ir Is It Jh Jn Js Lv Mi Mr Ms My Ni Nj Nk Nn Ny Oy Pe Qb) Nn(Fp In Is Jh Jn Jq Lv Lw Mb Mr Ms Mt Ni Nk No Nu Of Oy) Fp(Fr Hr Ih Ik In Ir Is Jh Jq Lv Mk Ni Nj Ny Oy Pz) Lw(Fr Hr Ih Ij In Ir Is Jh Lv Mr Ni Nk No Ny Pz Qb) Is(aA Fr Hr Ik In Jh Li Lv Ms Ni Nk No Ny Oy) Nu(Fr Ih Ij In Ir It Jh Lv Ni Nk Ny Oy Qb) No(Ih Ir Jh Jn Jq Js Li Lv Ni Nk Oy Qb) Js(Fr Hr Jh Jn Li Mb Nh Ni Nk Of Oy) Ny(In Jh Jn Lv Mb Ms Mt Ni Nk Of Oy) Fr(It Jq Mb Mk My Ni Nk Of) Ij(Il In Ms My Ni Nk Of Oy) Qb(In Jh Jq Lv Ms Ni Nk Oy) Jn(Ik Jh Lv Ms Ni Nk Oy) Li(Hr In Jh Lv Nk Of Oy) Aa(Iv Nb Qd Qe) Mt(In Ms Ni Nk) aA(Ip Ir It Pz) Lx(Jh Mh My) Ih(In Lv) Jq(In Ms) NiNj} Qe{Oy(Fp Fr Is Jh Jl Jn Jo Jq Js Li Lv Lx Mg Mi Mp Mr Mu Nc Ne Nh Nn Ny Of Pd Pe Pg) Il(Fp Ij Is Jh Jq Li Lv Lw Lx Mb Mi Mm Mp Mr Ms Nc Ne Nh Ni No Ny Pe Qa) Ne(Aa Fp Hr In Is Jh Jn Jq Js Li Lx Mb Mk Mm Mp Ms Ni No Nv) In(Fp Is Jh Jl Jo Jq Li Lv Lx Mb Mm Mp Ms Nc Nh Nn Nv Ny) eP(Du Fd Fi Gb Gh Hl Ho Hp Lt Rx Sh Si Sj Vz Yd Zw Tm Xa) My(Fr Is Jh Jl Jq Js Li Lv Lw Lx Mi Mp Mr Mu Nn Ny Om) Ni(Fp Hr Is Jl Jn Jq Js Li Lw Lx Mp Ms Nc Nn Nv Ny) dX(Eq Fi Gh Ho Hp Lp Rx Rz Sh Sj Vz Wb Yd Yl Zw) Hr(Fp Is Jn Jo Jq Js Li Mr Ms Nc Nh Nv Pe Qa) Aa(Hw Ii Iu Lu Lw Ma Mb Me Mj Nb No Nq Og) Ms(Fp Is Jh Jl Li Lx Mp Nc Nn Nv Ny) Jq(Fp Hw Ii It Jh Jr Js Lv Mh Nh Of) aN(aS cD Et Im It Jn Li Lw Nw Og) Mb(Fr Is Jh Jl Li Lx Mk Nn Ny) Nh(Fp Jh Jl Js Li Lx Mp Nv) Nc(Fp Is Jl Lw Mk Mp Nk) Js(Hw It Jh Lv Mh Mm Of) Nv(Hw Hx Ii Jn Lw Mv Mw) Of(Fr Jh Li Nn Ny) Fp(Jh Jn Mk Mp) Lx(Hx Mk Mw Po) Qg(Ub Ur Vs Vt) Aj(Ba Jg Ji) Lv(Jn Mk Mm) Mh(Jl Mr Pe) Mp(Jh Jn Mm) Ii(Jl Mr Pe) Ns(kS pF) aS(Ji Vt) bU(lX nN) NnHw LwLi UbJd ItQa ZwJr JhJn KfUu} Nx{Nm(Fr Hr In Is It Jh Jl Jn Js Li Lx Mb Mp Mr Ms My Nc Ne Nh No Nu Nv Oy Qb) Jl(Fp Fr Hr Ii In It Jh Jn Js Li Lw Lx Mb Mh Mm Ms My Nc Ne Nh No Oy Qb) Of(Ij In Ir Is It Jh Jn Lw Mi Mp Mr Ms Nc Ne Nh Nn No Nr Ny Pe Pz Qb) Mm(aA In Ir It Jh Jn Js Lv Mb Mr Ms My Nc Ne Nh Ni Nu Oy Pe Qb) Ms(Fr Ih Ij Ir Is It Jh Jn Li Lw Mp Nc Ne Nh Nn No Nv Qb Qc) In(Fr Ih Ij Ir Is It Jh Jn Lw Mp Mr Nc Ne Nh No Nv Ny Pe) Lw(Fr Hr It Jh Jn Js Li Lx Mb Mr Nc Ne Nh No Nv Qb) Ne(Fr Ir Is It Jh Jn Js Li Mp Nn No Nu Nv Qb) Nh(Fr Ir Is It Jh Jn Js Li Mp Nn No Nu Nv Qb) Fr(Fp Hr It Jn Js Mb My Nc Ng Nu Oy) Nc(Jn Js Li Lx Mp Mr Ni No Nu Qb) Nj(Hr Ih Ij Ip It Nd Pa Pe Qc) Jh(It Jn Js Li Lx Mp Nu Oy Qb) Li(aN Hr It Jn Mb My Ni Oy) Nu(Ii Ir Is Jq Mb No Ny) Mp(Ir It Jn Js Mb Oy Qb) Lx(Hx Jn Mb Mh Mk Ni) Qb(Hr Mb My Ni No Oy) Nv(Hr Ii It Mw Ng Ni) Js(Fp Hr Mb Ni Oy) Jn(Fp Mb No Oy) aA(Ij Ir Lv Oy) Og(Jq Lv Oi) Pe(Hr Ii Oy) aN(Im Is Lj) Fp(Ii Ni) rR(Hu Ml) AjQd NoIt IjOy bUoW} Og{Qb(Fp Fr Hu Ik In Ip Is Jl Jn Jo Jq Lv Lx Mb Mg Mp Ms Mu Nc Ne Ng Ni Nn No Ny Oi Pz) Jn(aN Ih In Ip Ir Is Jh Jq Lv Mb Mi Mp Mr Ms Mu Nc Ne Nh Nn No Nr Ny Pe Po Pz) Mm(Fr Ih Ip Ir It Jh Jq Li Lv Lw Mb Mp Mr Mu Nc Ne Nh Nn No Nr Ny Pe Po) aA(Ii Ik Ip Ir It Jh Jk Jm Jo Lv Lw Mb Mg Mp Nc Ne Ng Nh No Oi Po Qc) Nn(Fp Fr Ih Ip Ir It Jh Jl Jq Li Lv Lw Lx Mb Ms Nc Ne Nh Ny Pz) Nm(Ih Ik Ip Ir It Jh Jk Jq Jr Lv Mb Mp Mr Mu Nc No Nr Po Pz) Ny(Fr Ih Ip Is It Jh Jq Li Lv Lx Ly Mb Mp Nc Ne Nr Pz) Fp(Fr Ih Ip Ir It Jh Jo Jq Lv Lx Mg Mp Nc Ne No) Li(aN Ih In Ip Ir It Jh Jq Lv Lx Mb Mp Nc) Is(In Ip Ir Jh Lv Mb Mp Ms No Nr Po Pz) Fr(Ih Ip Ir It Jq Jr Lw Mb Nc Ne Nh) Lx(Ih Ir Jh Jq Mb Mp Nc Pz) Nj(Aa Jm Jo Jr Lv Me Mw Pd) Nh(Ir Jh Jq Lw Mp No Pz) Aa(Im Mt Nt Qa Qd) Lw(aN Ir Ne Nr Pz) Nu(In Mr Nr Pz) Ne(Ir Jq No Pz) Qd(Ar Ax bM Wm) Js(Ip Lv Mp Pz) aN(Ax Lj Nw On) Jl(Ir Jq Lv) Jd(Lj Ub) Jh(Ir It) Jq(Ms Pz) WmJi KfLj bUnN} bU{oV(bE bO Dp Ex Fa Fy Gl Hc Id Iz Ju Jy Kf Kg Ki Kj Ko Kp Kq Kr Ks Kx Ky Ou Pj Qn Qz Rc Rf Rj Rm Tn Tr Tt Tv Ua Ub Uc Ue Up Uu Uv Vq Vs Vt) oT(Ef Fy Gl Gp Hc Iz Kf Ko Kq Kr Ks Ou Pj Qt Rc Rh Ri Rj Ss St Tn Tr Ua Ub Uc Ue Uf Ug Uo Up Us Vq Vs) dU(aG bE bN cF cO Gd hC Hf Jy Ki Kq Nk Pi Pk Qt Qy Rh Ri Tn Ub Uk Um Up Ur Us) pH(aG cF cO gL Hq Id Jy Kq Pk Ql Qm Qn Rh Ri Rm Tn To Ub Uk Um Ur Us Vq) jB(Ed Ex Fw Gp Id Jy Ki Kx Ph Ql Qt Rf Rh Sr St To Up Us) fA(dB Iz Jd Ko Kq Kx Ky Pk Qt Tn Ua Ub Uf Uh Um Ur) kE(Du Eq Ps Rt Rv Uw Ux Uy Va Vb Vh Vi Wc Wf Wh Yj) oW(aG aN bE cN cZ gL hC iH mH Nb Nd) pK(Kq Pk Rj Tn Tr Ub Um Ur Vs) eQ(cC dB gL Hq Qt Qz Rh) aN(Im Is Lj Mt Nw) mU(Du Eq Gc Vh Zw) Hl(mW mZ nD nH) fB(Ko Kq Kx Tn) iH(kO nC nJ nL) Aj(Jg Ji On) Du(kG mZ nH) Gn(mW mZ oO) Ye(mW mZ nC) Tl(Hv Oa oQ) Vh(kG mW nA) gZ(Rh Ub Up) oD(Me Oz Wm) Gc(hC nB) Ho(nA nK) Lj(Ji Lw) Vb(mT nD) gC(Kq Mb) pI(Nb Wm) NomT YjkK UmnO} Nu{Is(aN Fp Fr Hr Jh Jl Jq Js Li Lv Lw Mb Mm Ms My Nc Ne Nh Nm Nn No Ny Of) Jl(Fp Hr Ii Il In It Js Li Lw Lx Mh Mm Ms My Nc Ne Nh Nm Nn Ny Of Qb) Jq(Fr In It Jn Li Lv Lw Lx Mb Mm Mp Ms My Nc Ne Nh Nn Ny Of Oy Qb) Lw(Fr Ih In Ir It Li Lv Lx Mb Mm Ms Nc Ne Nh Nn No Ny Oy Qb) Fp(Hr In Ir It Jh Jn Js Lv Lx Mp Ms Nc Ne Nh Nm Nn Ny Oy) Mm(Ij Ir It Jr Li Lv Lx Mb Mp Ms Nc Ne Nh Ny Of Oy Qb) Li(Hr In It Jh Jn Js Lv Mb My Nc Ne Nh Nm Of Oy Qb) Ny(In Jh Jn Js Lv Lx Mb Mt Nc Ne Nh Nm Of Oy) It(Fr In Jh Lv Lx Mb Mp Ne Nh Nm Nn No Oy) Nn(In Ip Lv Lx Mb Ms Ne Nh Of Oy Qb) Jn(Fr Jh Js Lv Mb Mp Nc Ne Nh Nm Oy) Lx(In Jh Js Mb Mh Mk My Ne Nh Nm) Qb(Fr Jh Lv Mb Mp Ms Ne Nh Nm Oy) In(aA Ih Ij Ir Jr Mp Mt Nc Nm) Fr(aA Ir Jr Js Mb My Of Oy) Js(Hr Jh Mh My Ne Nm Of) Mb(Ir Mp Mt Nm No) Nh(aA Lv Mp Nm No) Oy(Ij Ir Lv Mp Pe) Mt(Mk Ms Nm) Ne(aA Nm No) Ir(Lv Mp) aA(Nr Pz) AaNj AjJg MyIj NiNv NwaN} Nj{In(Ii It Jh Jo Jr Lj Lv Ma Mi Mn Mq Mu Nb Nd Ni Nr Pa Pd Pe Po Pz Qc) Pa(Fp Ih Ij Ik Ip Ir Is Jh Jn Jq Lw Mi Mp Mq Mr Nh Ni Nk Nm Pb Qc) Jh(Ih Ij Ik Ip Ir It Jq Jr Lj Lw Mi Mm Nd Ni Nm Nr Oy Pe Qc) Mr(Aa Fp Hx Ii Ij Ip Ir Jq Mh Mk Mn Nd Ni Oy Pz Qb Qc) Nk(Ih Ij Ip Ir It Jq Lw Mi Nd Ne Nh Nm Nr Pe Po Qc) Aa(Ih Im Is Lw Lx Mt Nb Ni Nt Nw Of Ok Qa Qc Qd) Ni(Ip It Jq Lj Ma Me Mi Mn Nq Nr Pe Po Pz Qc) Mi(Fp Ih Ij Ip Ir Jn Mm Nr

Figure 31 Continued

Figure 31 Continued cUqV} Mm{Mb(Ih Ij Ir Is Jq Li Nn Ny Qb) Of(Fr Ij Is Li Nm) Qb(In Ni Oy) Is(Ms Ne) DkSf IjOy} Nd{Sf(bB bR Cs Dk Ed Gc Ho Hv Jr Li Lj Mw Qh) Du(Up Us) Ti(hL qB) Gc(hC Va) Si(Hv Lj)} mF{jQ(bA cR cT Cx dM Kd Kn) qV(Pj Tz Ua Uc Ue) jR(bA cT) VqcY aSjY aViB bJiC} Or{Mk(Cs Im Ko Kp Li Lj Nw Pa Pj) Im(Hu Ik Mj) Ax(Lv Mj)} Is{Li(In Mb Ne Nh Oy) Fr(Mb My Oy) Nm(Mb Ne Nh) NoNh SfTl} kK{qU(jQ Ny qW) lM(aD Kp Pi) cP(jY lN) jE(Cw Kp) AfjD AnjQ aRjY} Vb{mZ(Ao Ef Fy Gp Iz Tn Uf) Qy(Du Hv Jr) GcHv PzmS} Vt{Qg(Ax Cs Im Lj Oh Pa Qb Ub) AxaS NoIb} rR{Et(Hc Jv Kp Wm) ApwF MlUf KcrC KxlL UkjV rBwD} Aa{Of(Im Jg Nt Ok) Et(Mb Me) MbIh NbNe} Hv{Gc(hC oE Uk Us Va) bR(Sf Si) XaeM} kN{qV(Ad Cp De Ef Hc) qW(An Ld) dLjU} Ti{rZ(aV Mg Nc Ng Qv Ue) QljD} jl{cP(kF nH nK) dI(mU nD) AnnT PjmM} lL{nK(aW bA dF dI) CpkF CtnL sHqC} Nm{Qb(In Mb Ne Nh) NeLi LjcD} Jg{Mi(Hx Ii Ny) Ir(In Iu) CscD} Dk{Sf(bR Kk Ma Nh Om)} jY{aS(mI mW) aRmZ cPkF dInD} Wm{wQ(jV Nq) iAuR yJrC} Pj{Ns(hC oE) qU(kP lX)} iB{AnnT aJmZ aSkI qUkP} Im{rC(Ef Iz) NspF} Pk{wD(rB wQ) GcVa} eQ{Uu(Ng Of) KlOk} wF{iA(Ap Uf) RijM} An{lY(jM rA)} Mk{GziC PeoE} Ni{NcLi sIuR} To{bBoV cRoD} Yi{Rh(mS nL)} cX{jQ(nH nL)} eC{pH(Kl Tv)} mZ{CqSh UfUx} jU{kF(Cp Kj)} lM{bAmW bFnB} CsNwcD FwbBoV GchCkS MpIjOy IdWnUh InQbLi ItrBwD cPnDiC Constrained panels with 2 analytes, where 1.0E-8 >= 'model p-value' > 0. Contains 275 panels of 199,260 total panels evaluated. : Nt(aA Et Fp Ik Im In Is Iv Jg Ji Jj Jn Jp Js Jt Lw Lx Mk Mx My Mz Nf Nj Nl Nv Nw Nx Of Og Ok On Oy Qa Qb Qd Qe) Nw(aA Fp Im Is It Iv Jg Jj Jn Jp Jt Lw Mb Mh Ms Mt Mw Mx My Nc Ne Nf Nh Nj Nl Nu Nx Of Og Ok On Oy Qa Qd Qe) Et(aA Fp Im Is It Iv Ji Jj Jn Lu Lw Mb Mh Ms Mt Mx My Mz Nc Ne Nf Nh Nj Nl Nu Of Og Ok Oy Qa Qb Qd Qe) On(aA Fp Ii Im It Iv Jh Jj Jn Jp Mb Mh Mp Ms Mv Mw Mx My Nc Ne Nf Ng Nh Ni Nj Nl Nu Of Og Ok Oy Qd Qe) Ok(aA Fp Hr Im It Iv Jg Ji Jj Jn Jp Mb Ms Mt Mx My Nc Ne Nf Nh Nj Nl Nu Nx Of Og Oy Qa Qd Qe) Qd(aA Fp Il Im In Iv Jg Ji Jj Jn Jp Lw Mb Mj Ms Mt Mx My Mz Ne Nf Nh Nj Nl Nu Nx Of Og) Ji(aA aC Ii Ik Im In Iv Jj Jq Lu Mp Ms Mx My Nf Nj Nl Nu Of Og Oy Qe) Jp(aA Fp Im Is It Iv Jj Jn Jt Lw Mb Ms Mt Mx Nj Nl Nu Nx Of Og Qa Qe) Im(aA Iv Jg Jj Js Jt Mt Mx Mz Nf Nj Nl Nu Nx Og Qe) Jg(aA Fp Iv Jj Mx Nj Of Og Oy Qa Qe) Nj(Iv Nv Qa Qe) Iv(aA Lx Nv) Og(Nv Qa)

Constrained panels with 2 analytes, where 1.0E-7 >= 'model p-value' > 1.0E-8. Contains 141 panels of 199,260 total panels evaluated. : Im(aC Fp Il In Iq Jl Jn Jq Lh Li Lv Lw Lx Mb Mm Mp Ms My Nc Ne Nh Ni Nm Nn Nv Of Oy Qa Qc) Iv(Fp Fr Is Jl Jn Jq Js Jt Lh Li Lw Mm Mp Mt Mx Mz Nl Nm Nn No Nu Nx Ny Og Qa Qe) Jg(Ih Is It Jl Jn Jp Js Lh Lw Lx Mb Mg Mh Mp Ms Mt My Mz Nc Ne Ng Nh Nl Nu Nx Qb) Jp(Ih Ir Iz Jl Jr Js Lh Lv Lx Mh Mp My Mz Ne Nh Nm Oy Qb) Nj(aA Fr Jl Js Jt Lh Li Lx Mt Mx Mz Nu) Qe(aA Jj Mt Nl Nu Nx Og) Qa(aA Jj Nl Nu Nx) Nv(aA Jj Nl Of Oy) Mt(aA Jt Nx Og) aC(Jt Mz Nw Qd) Jt(Nl Og) IjOg QdaN JnaA Constrained panels with 2 analytes, where 1.0E-6 >= 'model p-value' > 1.0E-7. Contains 250 panels of 199,260 total panels evaluated. : Qe(Aa aC Fp Il In Is Jh Jl Jn Jq Js Jt Lh Li Lv Lw Lx Mb Mm Mp Ms Mx Mz Nc Ne Nf Nh Ni Nm Nv) Mt(aC Fp Is It Jj Jl Jn Jq Js Lh Li Lw Mb Mk Mm Ms Mx My Mz Nl Nm Nn Nu Nv Ny Oy Qa) Qa(Fp Hr Hw Il In Jh Jn Js Jt Lh Lv Lw Mb Mm Mp Ms Mx My Mz Ne Nf Nh Ni Nm Nv Oy) Nj(Fp Ih Ij Ip Ir Is Jh Jn Lw Mm Mp Mr Ni Nm Nn No Nx Ny Og Qb) Nv(Fp In Is It Jn Jt Lw Mb Ms Mx My Mz Ne Nf Nh Ni Nm Nu Nx) Nu(aA Fp Is Jj Jl Jn Jq Js Jt Lh Lx Mx Mz Nl Nx Ny Og) Iv(Aa Ih Ij In Ip Ir It Jh Jj Lv Nc Ne Nf Nh Nr Pe Qb) aA(Fp Ih Jl Js Jt Lh Li Lx Mm Mx Mz Nl Nr Nx Qb) Nl(Fp Fr Jl Jn Js Lh Li Lx Mm Mx Mz No Nx) Jt(Aj Fp Jj Jn Lx Mb Mx Mz Ne Nh Nx Qb) aC(Ar Et Is Jg Jp Li Lw Nm Ok On) Mx(Jn Lw Lx Mm Nm Nx Og) Jp(Hc Ib Jd Or Pk Vs) Nx(Fp Jj Li Lx Mz Og) Og(Is Jl Js Li Lx) Lx(Jn Mz Nh) Im(aN Is No) Js(Jj Ms Nf) Lh(Ii My Nf) bM(Ji Nw Qd) Jg(Aj Ik) aN(Ji Nw) FpMm Constrained panels with 2 analytes, where 1.0E-5 >= 'model p-value' > 1.0E-6. Contains 496 panels of 199,260 total panels evaluated. : aC(aN Ap Ax BA Bb Bc Cp Cs Cu Dc dF Dg Dl Fr Ih Ij Io Iv Jj Jn Kf Lh Lj Lx Mi Mm Mx Nt Nx Pe Pj Qa Un Vt) Nx(Fr Ih In Ir Is It Jh Jl Jn Js Lh Lv Lw Mb Mi Mm Mp Mr Ms Nc Ne Nf Nh Nm Nn No Nr Ny Of Pe Qb Qc) Mx(aN cM Fp Fr Ih Ij In Is It Jd Jh Jj Jl Jq Js Lh Li Lv Mb Mp Mz Ne Nf Nh Nn No Ny Pz Qb Ur Vt) Lx(aN Dw Eo Ew Fp In Is It Jh Jj Jl Jq Js Lh Lw Mb Mk Mm Mp Mt My Nc Ne Nf Ni Nm Nn Nv Ny Oy) Mz(aN bM Fp Fr Hx Ij Is Jl Jn Js Lh Li Lw Mb Mm Mp Ms Nc Ne Nf Nh Nm Ny Og Pb Qb rC) Nu(Fr Ih Ij In Ip Ir It Jh Jr Li Lv Lw Mb Mm Mp Nc Ne Nf Nh Nm Nn No Oy Pe Qb) Js(Fp Fr Hr In Is Jh Jl Jn Jt Lh Li Lv Lw Mb Mm Mp Nc Ne Nh Nm No Nv Ny Of Oy) Jt(aN Fr Hr Ih Ii In Ir Is Jl Lh Li Lv Mm Mp Mr Ms My Na Nc Nf Nn Ny Of Oy) Nj(Aa In It Jj Jq Jr Lj Lv Ma Mi Mn Mq Mu Nd Nh Nk Nl Nr Pa Pe Po Pz Qc) aA(Fr Ij Ip Ir Is It Jh Jq Lv Lw Mb Mp Nc Ne Nf Nh Nm Nn No Ny Og Po Pz) Jn(aN Fp Fr In Jh Jj Jl Lh Li Lv Lw Mb Mm Mp Ms Nc Ne Nh Nm No Ny Og) Lh(Fp Hr Hx Is It Jj Li Lw Mb Mh Mm Mw Nb Ne Nh Nm Nn Ny Og Oy Qb) Nl(Aa Ih Ij Ip Ir Is Jh Jj Jq Lv Lw Mp Mr Ni Nk Nm Nn Ny Og Qb) Qd(Aa Aj Ar aS Ax bA bE cD cM Cs cT dD Kp Or Ub Wm) aN(Ar Ax bA cT Et Is Jp Li Lj Lw Mt Ok On Pe Qa Qe) Fp(Is Jh Jl Jq Lw Mp Nc Ne Nf Nh Nm Nn Ny Og Pz) Li(Is Jj Jl Lv Lw Mb Mm Nc Ne Nf Nh Nm Qb) Jp(Je Jv Kx Oa Ow Qu Rg Ua Ub Uu Vt) Ji(Aj aS Ax bA cD cM cN Cs dD Ub) Jl(Hr Jj Lw Mb Mm Ms Ne Nf Nh Nm) Mt(Aa In Ir Mp Nf Nh No) Jj(Dc Jd Kf Mm Nn Ny Qb) Og(Fr Mm Nm Nn Ny Qb) Is(Fr Mm Ne Nh Nm) Aa(Mb Ne Nt Qa) jD(Wf Yd Zx Tl) Nh(Fr No Ny) Qe(Hr Oy Ub) Jd(Lj Or Ub) Kf(Lj rR Uu) bM(bA Et Ok) cM(Lj Uh Vt) Ax(Lw Or) Mb(Fr Mm) Sf(Dk Nd) Qb(Mm Nm) Nv(Hw Lv) AjOn CsLw CuNf WmwQ MkOr QgVt Constrained panels with 2 analytes, where 1.0E-4 >= 'model p-value' > 1.0E-5. Contains 899 panels of 199,260 total panels evaluated. : Mz(Aj AR aS Ax bA bU cD cF cM Cs cT dD Dp Hr iB iC Ih In Ip Ir It Jd Jh Jj Jo Jq Jr Kc Kf Kp Lv Md Mh Mi Ml Mr My Nn No Nr Or Oy Pe Pk Po Pz Qv Qw Qz Ra Rg Ub Uh Um Ur Vt) aC(Ad aJ aM Ao aP aR aX aZ bC bM cD cG cM cN cT cU Cw Dd De dL Fa Fy Id Jd Jq Js Kc Ke Kn Ko Kp Kq Kx Mp Mq Nf Ni Nj nL Nu Nv Ny Oa Or Pa Pd Pf Pk Po Pz Qb Qc Sr Ub Uh Vq Wm) Or(aN bM cF cM Cs dJ Et Fy Gp Hb Hf Hu Ik Im Io Ji Jj Jt Kc Ke Kf Kn Ko Kp Kq Li Lj Lv Mm Mx Nf Nw Oa Og Pa Pj Pk Qe Qg Sr Ub Uh Ur) aN(aZ Bb bF bM cB cD cF cM Cs Cu Dc dD dF dK Fp Ij Io Ir Iv Jg Jj Jq Js Lh Mh Mi Nj Nm Nt Nv Nx Og Pf Qb Qc Uh Vt) Lj(aA aK aR aS aZ BA bC bM bU cB cD cN cT Cu dD dF dJ Kc Ko Kp Kq Nl Nx Pk Qg Qz Sr Ub Uh Un Ur Us Vt) Mm(Fr Ih Ij Ip Ir It Jh Jq Jr Lv Lw Me Mi Mp Mr Ms Nc Ne Nf Nh Ni Nm Nn No Nr Ny Of Oy Pe Po Qc) bM(Ar Ax aZ Bb cM Cs cT Dc dD dF Im Is Jd Jg Jj Jn Jp Jt Ke Kf Kp Li Lw Lx Mt Mx On Pe Qe Uh Vt) Aa(Fp Fr Ih Im Is It Jg Jj Jn Jp Li Lu Lv Lw Lx Me Mp Nb Nc Nh Nu Nw Nx Og Ok On Po Qb Qc) Jj(Ar Ax bA Cp Cs Cu Fp Fr Fy Ij Is Jq Kn Ko Kp Kq Ks Kx Nm No Nr Oa Ph Pk Pz Uh Vt) Ax(cD cM Et Im Io Is Jd Jg Jp Jt Kf Mt Mx Nf Nm Nt Nw Og Ok Qe Ub Uh Un Ur Vt) Ny(Fr In Is It Jh Jl Jq Jr Li Lv Lw Mb Mi Mp Mr Ms Nc Ne Nf Ni Nm Nn No Qb) Is(Aj cD cM Ij In Jh Jl Jn Lv Lw Mb Mp Mr Ms Nc Nf Ni Nn No Nr Oy Qb) Kf(Aj Cs Ef Ik Iz Jo lM Mk Of Og Pk Qa Qd Qe Rg Tz Ub Uk Ur Us Vt) Qb(Fp Fr In Jh Jl Jn Jq Lv Lw Mb Mp Ms Nc Ne Nf Nh Ni Nn No Oy) Jd(Aj cM Cs Ib Ik Im Iz Kq Li Lz Mt Oa Of Og Oh On Qa Qd Us Vt) Nm(bA Fr Ih Ij Ir It Jh Jq Jr Lv Mb Mp Mr Nc Ne Nf Nh Nn No) Li(Aj bA cD cM Cs Hr In Ir It Jh Jq Mp Ni Of Oy Ub Ur Vt) Og(Dc Ih Ip Ir It Jh Jk Jq Lv Lw Mp Nc Ne Nh No Nr Po Pz) Fr(Fp Ih Ir It Jl Jq Jr Lh Lv Lw Mp My Nc Ne Nf Of Oy) Nn(Ir It Jh Jl Jn Jq Lv Lw Mb Mp Mr Ms Nc Ne Nf Nh No) Nw(Aj Ao Ar aS bA bE bL cD cM Cs cT dL kC Kx Pk Ub Us) Ij(Fp In Jl Lv Lw Mb Mp Ms My Nc Ne Nf Nh Nx Oy) Im(Aj aS bA cD cM Cs Iz Kp Pk Rg Ub Uh Ur Us Vt) Qe(Aj Ar aS bA cD cM Cu dD Di Kp Uh Ur Vs Vt) Lh(Ih In Ir Iz Jh Jl Lv Ml Mp Mv Nc No Pb Po) Lw(Ar bA cD cK cT Ir Jh Mb Nc Ne Nh No Nr) Ji(Ar

Figure 31 Continued cT iC jD lM Qg Qv Qz Rf Rg Us Uv Vs) Vt(Ar aS Cs Ir Ko Kp Nf Oh Pk Qa Qd Ub Ur) cM(Ar Cs Et Fp gZ Kp Kx nY Oa oE Qa Un) Mx(bA cD cT Ip Ir Kp Nc Ub Uh Uk Un) Qd(Iz Kx Pk Qg Qv Qw Qz Rg Uh Ur Us) Jq(Jn Lv Mb Mp Ms Nc Ne Nf Nh No Nx) Aj(Ad Ba Dc Et Jp Kq Mt Nt Ok Qa) Fp(Hr Ih In Ip Ir It Lv Mi Ms No) Jl(Ih In It Jh Lv Mp Nc Of Oy Pz) Cs(cD Et Io Jg Jp Jt Ok Ub Uh) rR(Ap Jv Kc Nx Pj Rb rC Uf Wm) No(Ib Ir Jh Lv Mb Mp Nc Ne) Nh(Ih Ir It Jh Lv Mp Po Pz) Nl(In It Mi Mn Nr Pe Po Pz) Ub(Dc Et Ir Kn Kp Oh Qa) Jn(Ir Mi Mr Nf Pe Pz Vb) cD(Ar bA Et Jt Lx Mt Ok) Mp(Ir Jh Mb Nc Ne Nf) Qa(Kp Qg Uh Ur Vs Tl) Et(aG bA kR Pk) Ne(Ir It Jh Lv) Hv(Sf Si Sj Vc) Oh(Ra Uh Ur Us) aA(Hr Jm Jo Qc) Ar(cT Jp Jt) Nf(Dc Kq Po) Sf(Jr Nb Ut) Jh(Ir It Nc) Nx(Ip Ni Oy) On(Ao Hc Iz) Ur(Dc Ir Us) Vb(Cu Jr Ut) Fa(Jp Mk) Nu(Mi Mr) Kq(Hc Iz) Uh(Pk Wn) Pj(jD oE) bA(Nt Ok) CuIo FwVc GchC Lvlh MrNc JpkR aMeW bReO bUnN fRgW rCrZ qUkK Constrained panels with 2 analytes, where 1.0E-3 >= 'model p-value' > 1.0E-4. Contains 2,030 panels of 199,260 total panels evaluated. : Jj(Ad Al aR aZ Ba BB Bc cB cD cM cN Cq cT cU DD De dF Dk dL Ed Ex Fa Fb Fw Ha Hb Hf Ho IC Id Ih Ii Ip Ir It Jh Jk Jm Jo Kc Ke Kg Kk Kr Lv Lw ml Mp Nc Ne NH nL Ou Pi Pj Po Qh Ql Qm Sr St Tz Ub Uc Uf Un Us Vp Vu) bM(aA Ad Aj aK aS Ba Bc bE bF cB cD cG Cp CU Dd Di Dk Fa Fy Gc Gp gW Hb Id Ij Io Iv Jq Jr Js Kc Kk Kn Ko Kq Kx Lh Mi Mr Nf Nj Nm Nt Nv Nx Oa Og Ou Pd Pf Pi Pj Pk Qa Qb Qc Qg Qh Rg Sr St Tn Tz Ub Uf Un Vi Vu Xa) Ub(aK aN Ar Bc cD cM Cu Cv dD Fa Fb Fr Fy Gc Hb Hf Id Iq Is Jl Jn Js Jt Kc Ke Kk Ko Kq Kr Kx Lh Lx Mq Mt Nx Oa oE Og Ok On Pj Pk Qb Qh Rg rR Sr St Tz Uf Uh Un Ur Us Vu Wm) Cs(aK aR aZ bA Bb bC bU bX cB cT Dc dD dF dJ gW Id Ik Is Jq Ju Jv Kc Ke Ko Kp Kq Kx Lx Mi Mk Ml Mm Mt Mx Nf Ni Nj Nl Nm Nt Og On Pe Pj Pk Qc Qe Qg Qw Qz Ra Sr Un Us) Pk(Ar Ax cM Cu Fa Fr Fy Hu Id Ik Io Jd Ji Kc Ke Kk Kn Ko Kp Kq Kx Lh Li Lw Lx Mk Ml Mm Mq Mt Mx Nd Nf No Oa oE Og Oh On Ou Pa Pj Qa Qe Rg Sr tT Uf Un Ur Us wF Wm) Ar(Aj aK Ax aZ bA bE bL bU cB Cp Dc dF dJ Et gW Hu Ik Im Io Is Iv Jd Jg Jn Jq Kf Kp Kq Li Mi Mq Mt Mx Nf Nj Nm Nt Og Ok On Pe Qa Qc Qg Qz Tz Uh Us Vu) Kp(Aj aM aN aS Ax bL cD cV dH dJ dL Ed Fa Hb Hu Ik Iz Jd Ji Jl Jv Kq Kx Li Lv Lx Lz Mk Mq Nd Nf Oa oE Of Og Oh Pj Qc Ra Rg Sr Tz Uh Un Ur Us Vu Wm) Uh(Ao Cu Dc Dd dL Fa Fy Hu iC Id Ik Ir Is JD jl Jl Jt Kf Kn Ko Kq Kx Lh Li lM Lv Lx Lz Mq Mt Nd Oa Pa Pe Qh Qv Rg rR Sr Tz Un Ur Us Vt Wm) Vt(bL Cu Dc Dp Et Fa Fy Gp Io Jt Kn Kx Lh Lv Lx Lz Mk Mq Mt No Ns Nw Oa oE Og On Or Pa Pj Ps Qh Qv Rg rR Sr Tn Tz Uf Um Us Vb Vi wF wQ Wm) Mx(Aj aK aR aS aV aZ Ba Bb Bc Bo cB cN Cu cX Dc dD dF Di dJ Fa gW Hb iC Id jF Kc Ke Kf Kk Kn Ko Kq Kx nY Oa Pj Qg Qv Qw Ra Rg Sf Sr Tl) Jd(aN Ao cD Cu Ed Ef Fa Fy hR Hu Id Ji Jl Jv Kc Kf Kn Kx Lh Lv Lx Mh Mk Mq Nd Nm Nw Pa Pe Qe Qu Qv Qz Rg Sr Tz Ua Ue Un Uu Vs Vu Wm) cM(bA cT dF Ed Ex FA Fy hR Id Ij Iv Jg Jn Jp Jt KC Ke Kf Kn Ko Kq kR Lw Lx Mt nN Nt oD Ok On Pe Pj Qb Qc Qh Rg Sr St Us Vu Wm) Og(BA Cp Cu Fa Fy Hu Id Ii Ik Jm Jo Jr kC Ke Kn Ko Kq Kx Lj Mb Mg Mi Mn Mq Mr MU Mv Ng nN Oa Oh Oi Pd Pc Qc Un Us Vu Wm) Lj(Aa Bc bX cG cJ Cp cX De Di dL Ho Jh Jy Ke Kk Kn kR Lv Lw Mm Mp Ne Nh Nm Ou Pj Qm Qw Sf Sj Tn Vi Vu Wb Zx Tl) aN(Ba cG Cp cU Dd Dl Fa Fy Id Ih Jr Kc Ke Kf Kn Kq Kx Lz Ml Mm Mq Mr Mu Nf No Nu Ny Oa Pa Pd Pj Po Sr Tz Um Vu) Lw(Aj aS bE bV cF Cp Cu Dc dD dF Hr th Ik In Ip It Jq Jr Lv Mp Mr Ms Nm Po Pz Qc) Sf(bR cF Dc De Ed Fw Fy Gc Ho Im Is Jk Jl Li Mt Mw Mz Nr Nt On Or Pi Qh Tz Zx Xa) Kn(Aj aS dJ Ed Hu iC Ik lM Lv Mk Mq Nd oE Qa Qe Qv Ra rC Rg rR Sr Ur wF wQ Wm) bA(bL bV cB cF Dc dL Hu Io Is Iv Jg Jn Jt Kc Lx Mm Mt Nj Nu Nx On Or Pj Qa Qc) cT(Aj aR cB cD cF cU dF dL Im Is Iv Jn Jt Kc Li Lx Mt Nj Nm Nt Ok On Or Qa Qe) Ax(aZ bU cB Dc De dJ gW Hb Iv Jn Jq Kc Ke Ko Kq Li Mk On Pj Qa Qc Qz Ra Sr) Vb(Dc Dk Gc Ho Im Is Jk Jl Jt Lh Li Mw Nb Nv On Pi Ps Qa Qd Qe Qh Uc Vi) Mt(aS aV aZ bE bL bU cB cF Dc dJ Dp Ed Ko Or Qv Ra Rg Sr Tz Uk Un Ur) Ji(Fa hP hR hV Ib Iz Ju Jv kC kl mF ml nH nK nL nN Ow rR tT wE wF wQ) Im(aK bE bJ Cu dD dE dF Dk dL Fa gW Hf Kk Ko Kz Qg Qv Qw Vs wQ Tl) Ip(Ih Ir It Jh Jq Jr Lv Mb Mp Mr Nc Ne Nh Nm Nn No Nr Ny Pz Qc wQ) Kq(Ao Dk Ef Hu Ib Ii Ik Io Lv Mk My mZ Nm Nq Of Pa Rg Tn Ur Vs Wm) Or(aS aV cD cX Dl Fa Gc Ho Id Iq Iz Jg Mq Nd No Oh Qa Rg rR Xa Wm) Lx(Aj Ao aS aV bL bU cC cF cK dJ Hc Iz kC Ko oE oN Pj Ra Sr Ur) Un(aS Dc Dp Hu Ik Iz Ko Lv Mk Mq oE Pa Qg Qv Rg Sr Um Uo Ur Wm) Fy(Aj cD dJ Dp Hu Ik Iz kS Lv Mk Mq oE Of Qv Ra Rg Ur Uv Wm) Ih(In Ir It Jh Jq Mb Mi Mp Mr Ms Nc Ne Ni Nn No Ny Po Pz Qc) Li(aR aS aZ cN Cu cD dF KC Kk Ko kP Qg Qv Qw Rg Rm Yj Zw Tl) Nw(Eo Hc iC Iz Jv kN kP mF ml nH nK nL nN nO Ra rC Rf Rg) Jt(Aa aR aS aZ bV cN Ct CU cX dD dF dL Rg Ue Uk Ur) Lh(Aj cD Hc jD kC lM mF ml nK nL oN Qg Rg Ur Uv Vc Vs) Nr(In Ir It Jh Jq Jr Lv Mb Mi Mp Mr Ms Nc Ne Nh Nm) On(aS bE cD dD Dk Ef iC kC lM Rg Ua Uc Ur Uu Vc Zw) Pj(cN Fa hC hR hV iC Ik jl lM Mk Mq Mz Oh Qv Rg rZ) aC(aA Fb fR Gc Hb Ic nH Ql Qm Rg St Tz Uc Uf Ur Vu) In(Cu Ir It Jq kC mF ml Mp Nc nL Nm NN Pi Po) Jr(Aa Ij Ir Jh Lv Mp Nc Ne Nh Nn No Sh Si Sj Zw) Wm(Cu hP jD Jq Kc Ke Qv rB Tz UR wF yJ zG) Fa(aS dJ Hu Ik Io Kc Ko Lv Ml Mz Nd Ra Ur) Ir(gW It Jq Ko Lv Mb Mi Mr Ms Nc Ny Po Uk) Qa(aS cD dD Di Iz Kc Kk Ko Qv Qw Rg Rm Zw) Ke(Aj aS Hu Ik Iz IM Lv Mk Mq oE Of Rg rR) Cu(Aj cD Ik Iv Jn Jo Lz Nj Of Qc Ur Tl) Gc(De Ed hG iZ kS oE Qd Tz Uk Ut Va Vi) kC(aL bB iB iH It jI kP IL No Nv Nx Qd) Po(Hr It Jh Jq Lv Mb Mp Nc Ne Nm Oy) Mq(Id Kc Ko Nc Rg Sr Tz Uk Um Ur wQ) Mz(Ed gW hP Kk Ko kR rR rU rV tT yH) Qc(dD Ik It Jh Lv Mb Mp Nc Ne Nh Nm) Jn(Aj aR aZ cD cN dD dF dJ dL nN Tl) hR(cV dK iB iC jl Mk Nx Qd rB rC rR) Dc(cD Ik Io Jo Lz Of Rg Sr Uk Um) Ij(Aj cD Fr Il Jh Jq Nn No Ny Of) IL(kF kl mF ml nC nH nK nL nN nY) Mr(It Jh Jq Lv Mb Mp Ne Nh No) Is(aR aS bE bU dD dF dJ dL Ur) Nc(It Jo Lv Mb Mi Mn Ni Nk) Tl(bU Ed Jl Ny Ps Qd Qh Tz) Ko(Aj Ik Iq Kc Mk Oh Sr Ur) rR(Dg Dl Mm Ou Rg Ri Uk Vu) Nt(aR aS aZ bE cD cX dD) Nd(Ho Kc Kk Sh Si Vi Wb) Jh(Jq Lv Mb Mi Ms Oy Pa) Um(kP mF mS mZ nI nL nO) Aj(dF Dg Io Iv Nm Nv) Tz(Du Ho iC Kc nL Wb) It(Jq Lv Mb Mi Mp No) Qd(gW iC jD jU IK Vs) Xa(bU cF eM eP kS Rh) Nx(iC jl tT Ur wD wP) cD(aZ cG dF Fp Jg Nm) qU(kF kl kP nN nR nU) Nn(Me Mi Ni Of Oy) Ne(Jo Ma Mb Mi Mn) Wb(cF De hC Nb Ut) Ur(Iq Jl Js Qh Tv) nL(bU dD Gl iB Qz) Dk(Hp Sh Si wF) Mp(Lv Ms Ni Oy) Nh(Mi Mn Ms Pa) Kc(aS dJ Oh Sr) Rg(Id Jq Pa Sr) Ut(Ho Sh Si Vc) dF(aO bL bZ Nj) rZ(jY kN Mm Ti) No(Eo Ms nK) Mb(gC Jo Mi) Mk(iC oE Vu) Tn(Iz mZ Vc) Jl(Hp Sj wQ) Nv(lM ml nK) Ny(Ao Of Oy) Vi(bO bU Rh) gW(kK kN mF) tT(Lu Oh rC) hC(Ns Zq Zx) wF(Ef Ri Ti) Ex(cJ Pi) Nm(aS Hr) Nb(Si Sj) Ho(bU cP) lz(Fr tV) Jg(cU Uu) Jq(Hr Oy) Ok(aS bL) Vu(Qv Sr) dD(Iv Qb) dW(aM cC) eO(aD bB) mZ(Gl Uf) wQ(Oh Ou) rC(uY yJ) jD(Yh Zq) kK(IK IN) oE(cX Ns) AfIo GzuY LvMn MhMm WcqV QhVc aLmI cFjB mFjF rBwD kFlN kNkP Unconstrained panels with 3 analytes, where 0.0E0 >= 'AUC p-value' > 0. Contains 50,000 panels of 37,933,414 total panels evaluated. :
bU{eQ(AA aC AD aE AF aG aH aI AJ aK AL aM AN AO AP aQ Ar AS aU aV AW AX aY aZ BA BB BC bE bF BG bH bI bJ bL bM BN BO bP bQ bR bS bV bW bX bZ cA cB cC cD cE cF cG CH cI cJ cK cL cM cN CO CP CQ cR CS CT CU CV CW CX cY cZ dA DB DC DD DE dF DG dH dI dJ DK DL dM dN Dp DR DU eC Ed EF EM Et Ex Ez FA FB Fc Fd Fi Fn FP FR Fw Fy Gb GC Gd GL Gn Gp GZ HB HC HF hG Hp Hq Hr Hu Hv Hw Hx iA Ib Ic Id IH Ii IJ Ik Il Im In IO IP Iq Ir Is It Iu Iv IZ jB Jd Je Jf Jg Jh Ji Jj Jk Jl Jm Jn Jo Jp Jq Jr Js Jt Ju Jv Jy KC Kd KE

Figure 31 Continued

KF KG KI Kj KK Kl KN KO KP KQ KR KS Kz Ld Lh Li Lj Lp Lt Lu Lv LW LX LY Lz Ma Mb Mc Md ME MF Mg MH MI Mj Mk Ml MM
Mn MP Mq Mr MS MT mU Mv MW Mx MY MZ NA NB NC ND Ne NF Ng NH NI NJ NK NL NM NN NO Nq NR Ns NT NU Nv NW Nx
NY Oa oD OE OF Og OH Oi OK Om ON oO OP oQ Or oT Ou oV OW Oy Oz Pa Pb Pc Pd Pe PF Pg pH PI Pj PK Po Ps Pz Qa Qb Qc Qd Qe
Qg Qh Ql Qm Qn Qu Qw Qx Qy Ra Rb Rc Rf Rg Rh Ri Rj Rm Rt Ru Rv Rx Ry Rz Sf Sh Si Sj Sr Ss St Tn To Tr Tt Tv Tz Ua Ub Uc Ud Ue Uf
Ug Uh Uk Ul Um Un Uo Up Ur Uu Uv Ux Uy Uz Va Vb Vc Vh Vi Vj Vo Vp Vq Vt Vu Vv Vw Vz Wb Wc Wd We Wg Wh Yd Yl Zw Zx
Ye Tm Tl Xa Wm Tj Ti Th tF Yf) gZ(aA aC AD aE AF aG al AJ aK AL aM AN AO AP aQ AR AS aU aV AW AX aY aZ BA BB BC bE bF
BG bH bI bJ bL bM BN BO bP bR bS bV bW bX bZ cA cB cC cD cE cF cG CH cl cJ cK cL cM cN CO CP CQ cR CS CT CU CV CW CX cY
cZ dA DB DC DD DE dF DG dH DI dJ DK DL dM dN Dp DR DU eC Ed EF EM Et Ex Ez Fa FB Fc Fd Fi Fn FP FR Fw Fy Gb GC Gd GL Gn
Gp Gz HB HC HF hG Hp Hq Hr Hu Hv Hw Hx iA Ib Ic Id IH Ii IJ Ik Il Im In IO IP Iq Ir Is It Iu Iv IZ jB Jd Je Jf Jg Jh Ji Jj Jk Jl Jm Jn Jo Jp Jq
Jr Js Jt Ju Jv Jy KC Kd KE KF KG KI Kj KK Kl KN KO KP KQ Kr KS Kx Ky Kz Ld Lh Li Lj Lp Lt Lu Lv LW LX LY Lz Ma Mb Mc Md ME
MF Mg MH MI Mj Mk Ml MM Mn MP Mq Mr MS MT MU Mv MW Mx MY MZ NA NB NC ND Ne NF Ng NH NI NJ NK Nl NM NN NO
Nq NR NT NU Nv NW Nx NY Oa oD OE OF Og OH Oi OK Om ON oO OP oQ Or oT Ou oV OW Oy Oz Pa Pb Pc Pd Pe PF Pg PH PI Pj PK
Po Ps Pz Qa Qb Qc Qd Qe Qg Qh Ql Qm Qn Qt Qu Qw Qx Qy Qz Ra Rb Rc Rf Rg Ri Rj Rm Rt Ru Rv Ry Rz Sf Sh Si Sj Sr Ss St Tn To Tr Tt
Tv Tz Ua Ub Uc Ud Ue Uf Ug Uh Uk Ul Um Un Uo Ur Us Ut Uu Uv Uw Ux Uy Uz Va Vb Vc Vi Vj Vo Vp Vq Vt Vu Vv Vw Vz Wb Wc Wd
We Wg Wh Yd Yl Zw Ye Tl Xa Wm Tj Ti Th tF Yf) pK(aA aC AD aE AF aG aH aI AJ aK AL aM AN AO AP aQ AR AS aU aV Aw AX aY
aZ BA BB BC bE bF BG bH bI bJ bL bM bN BO bP bQ bR bS bV bW bX bZ cA cB cC cD cE cF cG CH cl cJ cK cL cM cN CO CP CQ cR CS
CT CU cV CW CX cY cZ dA DB DC DD DE dF DG dH DI dJ DK dL dM dN Dp DR dU eC Ed EF EM Et Ex Ez FA Fb Fc Fd Fi Fn FP FR Fw
Fy Gb GC Gd GL Gz Ha HB HC HF hG HI Hp Hq Hr Hu Hv Hx iA Ib Ic Id IH Ii IJ Ik Il Im In IO IP Iq Ir Is It Iu Iv IZ jB Jd Je Jf Jg Jh Ji Jj Jk
Jl Jm Jn Jo Jp Jq Jr Js Jt Ju Jv Jy KC KE KF KG KI Kj KK Kl KN KO KP kQ Kr KS Kx Ky Kz Ld Lh Li Lj Lp Lt Lu Lv LW LX lY Lz Ma Mb
Mc Md ME MF Mg MH MI Mj Mk Ml Mm Mn MP Mq Mr MS MT mU Mv MW Mx MY MZ NA NB NC ND Ne NF Ng nH NI NJ NK NL
NM NN NO Nq NR Ns NT NU Nv NW Nx NY Oa oD OE OF Og OH Oi OK Om ON oO OP oQ Or oT Ou oV OW Oy Oz Pa Pb Pc Pd PF Pg
PH PI Pj Pk Po Ps Pz Qa Qb Qc Qd Qe Qg Qh Ql Qm Qn Qt Qu Qw Qx Qy Qz Ra Rb Rc Rf Rg Rh Ri Rm Ru Rv Ry Rz Sf Sh Si Sj Sr Ss St To
Tt Tv Tz Ua Uc Ud Ue Uf Ug Uh Uk Ul Un Uo Up Us Uu Uv Uw Ux Uy Uz Va Vb Vc Vi Vj Vo Vp Vq Vt Vu Vv Vw Vz Wb Wc Wd We Wg
Wh Yd Yl Zw Ye Tm Tl Xa Wm Th tF Yf) pH(aA aC AD aE AF aG aH aI AJ aK AL aM AN AO AP aQ AR AS aU aV AW AX aY aZ BA BB
BC bE bF BG bH bI bJ bL bM BN BO bP bQ bR bS bV bW bX bZ cA cB cC cD cE cF cG CH cl cJ cK cL cM cN CO CP CQ cR CS CT CU
CV CW CX cY cZ dA DB DC DD DE dF DG dH DI dJ DK DL dN Dp DR DU eC Ed EF eM Et Ex Ez FA Fb Fc Fd Fi Fn FP FR Fw Fy Gb GC
Gd GL GP Gz HB HC HF hG Ho Hp Hq Hr Hu Hv Hw Hx iA Ib Ic IH Ii IJ Ik Il Im In IO IP Iq Ir Is It Iu Iv IZ jB Jd Je Jf Jg Jh Ji Jj Jk Jl Jm Jn
Jo Jp Jq Jr Js Jt Ju Jv Jy KC Kd KE KF KG KI Kj KK Kl KN KO KP kQ kR KS Kx Ky Kz Ld Lh Li Lj Lp Lt Lu Lv LW LX lY Lz Ma Mb Mc Md
ME MF Mg MH MI Mj Mk Ml MM Mn MP Mq Mr MS MT mU Mv MW Mx MY MZ NA NB NC ND Ne NF Ng NH NI NJ NK NL NM NN
NO Nq NR Ns NT NU Nv NW Nx NY Oa oD OE OF Og OH Oi OK Om ON oO OP oQ Or oT Ou oV OW Oy Oz Pa Pb Pc Pd Pe PF Pg Ph PI
Pj Pk Po Pz Qa Qb Qc Qd Qe Qg Qh Qt Qu Qw Qx Qy Qz Ra Rb Rc Rf Rg Rj Rt Ru Rv Ry Rz Sf Sh Si Sj Sr Ss St Tr Tt Tv Tz Ua Uc Ue Uf
Ug Uh Ul Um Un Uo Up Uu Uv Uw Ux Uy Uz Vc Vh Vi Vj Vo Vp Vt Vu Vv Vz Wd We Wg Wh Yd Yl Zw Ye Tm Xa Wm Tj Th tF Yf)
dU(AA aC AD aE AF aG aH aI AJ aK AL aM AN AO AP aQ AR AS aU aV AW AX aY aZ BA BB BC bE bF BG bH bI bJ bL bM BN BO bP
bQ bR bS bV bW bX bZ cA cB cD cE cF cG CH cl cJ cK cL cM cN CO CP CQ cR CS CT CU CV CW CX cY cZ dA DB DC DD DE dF DG
dH DI dJ DK DL dM dN Dp DR Du eC Ed EF eM Et Ex Ez FA FB Fc Fd Fi Fn FP FR Fw Fy Gb GC GL gP Gz HB HC hF hG Hr Hu Hv Hw
Hx iA Ib Ic Id IH Ii IJ Ik Il Im In IO IP Iq Ir Is It Iu Iv IZ jB Jd Je Jf Jg Jh Ji Jj Jk Jl Jm Jn Jo Jp Jq Jr Js Jt Ju Jv KC Kd KE KF KG kI Kj KK Kl
KN KO KP KQ KS Kx Ky Kz Ld Lh Li Lj Lp Lt Lu Lv LW LX LY Lz Ma Mb Mc Md ME MF Mg MH MI Mj Mk Ml MM Mn MP Mq Mr
MS MT mU Mv MW Mx MY MZ NA nB NC ND Ne NF Ng NH NI NJ NK NL NM NN NO Nq NR Ns NT NU Nv NW Nx NY Oa oD OE OF
Og OH Oi OK Om ON oO OP oQ Or oT Ou oV OW Oy Oz Pa Pb Pc Pd Pe PF Pg Ph pI Pj Po Ps Pz Qa Qb Qc Qd Qe Qg Qh Ql Qm Qn Qu
Qw Qx Qz Ra Rb Rc Rf Rg Rj Rm Rt Ru Rv Ry Rz Sf Sh Si Sj Sr Ss St To Tr Tt Tv Tz Ua Ub Uc Ue Uf Ug Uh Ul Un Uo Uu Uv Uw Uy Uz
Va Vc Vh Vi Vj Vo Vp Vq Vt Vu Vv Vz Wb Wc Wd We Wg Wh Yd Yl Zw Tm Tl Xa Wm Th tF) oT(AA aC AD aE AF aG aH aI AJ aK AL
aM AN AO AP aQ AR AS aU aV AW AX aY aZ BA BB BC bE bF BG bH bJ bL bM BN BO bP bQ bR bS bV bW bX bZ cA cB cC cD cE
cF cG CH cl cJ cK cM cN CO CP CQ cR CS CT CU CV CW CX cY cZ dA DB DC DD DE dF DG dH DI dJ DK DL dM dN Dp DR Du eC Ed
eF EM Eq Et Ex Ez FA Fb Fc Fd Fi Fn FP FR Fw Gb gC Gd gL Gn gP Gz HB hC HF hG Hp Hq Hr Hu Hv Hw Hx iA Ib Ic Id IH Ii IJ Ik Il Im
In IO IP Iq Ir Is It Iu Iv iZ jB Jd Je Jf Jg Jh Ji Jj Jk Jl Jm Jn Jo Jp Jq Jr Js Jt Ju Jv Jy KC Kd KE kF KG KI Kj KK Kl KN kO KP kQ kS Kx Ky
Kz Ld Lh Li Lj Lt Lu Lv LW LX LY Lz Ma Mb Mc Md ME MF Mg MH MI Mj Mk Ml MM Mn MP Mq Mr MS MT mU Mv MW Mx MY
MZ NA NB NC ND Ne NF Ng NH NI NJ NK NL NM NN NO Nq NR Ns NT NU Nv NW Nx NY Oa oD OE OF Og OH Oi OK Om ON oO
OP oQ Or oV OW Oy Oz Pa Pb Pc Pd Pe PF Pg PI Pk Po Ps Pz Qa Qb Qc Qd Qe Qg Qh Ql Qm Qn Qu Qw Qx Qy Ra Rb Rf Rg Rj Rm Ru
Rv Rx Ry Sf Sh Si Sj Sr St To Tt Tv Tz Uc Ud Uh Uk Ul Um Un Ur Ut Uu Uv Uw Ux Uy Uz Va Vb Vc Vi Vj Vo Vp Vt Vu Vv Vw Vz Wb
Wd We Wg Wh Yd Yl Zw Zx Ye Tm Tl Xa Wm Tj Ti tF Yf) fA(aA aC AD aE Af aG aH aI aJ aK AL aM aN aO aP aQ aR AS aU aV AW AX
aY aZ BA BB BC bE bF BG bH bJ bM BN BO bP bR bV bW bX bZ cC cD cE cF cG CH cJ cK cM cN CO CP CQ cR CS CT cU CV CW CX
cY cZ dA DB DC DD DE dF dG dH Di dJ DK DL dN Dp DR Du eC Ed EF EM Et Ex Ez Fa Fc Fi Fn FP Fr Fw Fy Gb GC Gd GL gP Gz HB
HC HfhG Hl Hp Hq Hr Hu Hw Hx Ib Ic Id IH Ii IJ Ik Il Im In IO IP Iq Ir Is It Iu Iv iZ jB Je Jf Jg Ji Jj Jk Jl Jm Jn Jo Jq Jr Js Jt Ju Jv Jy KC Kd KE
KF KG KI Kj KK Kl KN kO KP KQ KS Kz Ld Lh Li Lj Lp Lt Lu Lv LW LX lY Ma Mb Mc Md ME MF Mg MH MI Ml Mm Mn MP Mq mS
MT MU MW Mx mY Mz NA NB NC ND Ne Nf Ng NH NI NJ NK nL NN NO Nq NR Ns NT nU Nv Nw Nx NY Oa oD OE OF Og OH Oi OK
Om ON oO Op oQ Or Ou oV OW Oy Oz Pa Pb Pc Pd Pe PF Pg PI Pj Po Ps Qa Qb Qc Qd Qe Qg Qh Ql Qm Qn Qu Qw Qx Qy Qz Ra Rb Rc Rf
Rg Rh Ri Rj Rm Rt Ru Rv Ry Sf Sh Si Sj Sr Ss St To Tr Tt Tv Tz Ub Uc Ue Ug Uk Ul Un Uo Us Uu Uv Uw Ux Uy Uz Va Vb Vc Vh Vi Vj Vo
Vp Vq Vt Vu Vv Vw Vz Wb Wc Wd We Wg Wh Yd Yl Zw Tm Tl Xa Wm Ti Th tF Yf) oV(aC AD aE aG al aJ aK AL aM AN AO AP aQ aR
AS aU aV AW AX aY aZ BA BB BC bE bF BG bJ bL BN BO bP bR bS bV bW bX bZ cA cB cC cD cE cF cG CH cl cJ cK cM cN CO CP CQ
cR CS CT cU CV CW CX cY cZ dA DB DC DD DE dF Dg dH DI dJ DK DL dM dN DR Du Ed eF EM Eq Et Ez Fb Fd Fi Fn FP FR Fw gC Gd
gL Gn Gp Gz HB hC HF Hp Hq Hr Hu Hv iA Ib Ic IH Ii IJ Ik Il Im In IO Ip Iq Ir Is It Iu Iv iZ Jd Je Jf Jg Jh Ji Jj Jk Jl Jm Jn Jo Jp Jq Jr Js Jt Ju Jv
Kc Kd Ke kF kG kI KK Kl KN kO kP kQ kS Kx Kz Ld Lh Li Lj Lp Lt Lu Lv LW LX lY Lz Ma Mb Mc Md ME MF Mg MH MI Mj Mk Ml
MM Mn Mp Mq Mr mS MT mU mW Mx MY NA nB NC ND Ne NF Ng NH NI nJ NK NL NM NN NO Nq NR Ns Nt NU Nv nW Nx NY Oa
oD OF Og OH Oi OK Om ON oO oP oQ Or OW Oy Oz Pa Pc Pd Pe PF Pg Ph PI Pk Po Ps Qa Qb Qc Qe Qg Qh Ql Qm Qt Qu Qw Qx Qy
Ra Rb Rg Rh Ri Ru Ry Rz Sh Si Sj Sr Ss St To Tt Tz Ud Uf Ug Uh Uk Ul Um Un Uo Ur Us Ut Uw Uz Va Vc Vi Vj Vo Vp Vu Vv Vw Wb Wc
Wd We Wg Wh Ye Tm Xa Wm Tj Ti Th tF Yf) fB(aC AD aE aG al AJ aK AL aM aN AP AR AS aU aV AW AX aY BA BB BC bE bF Bg bJ

Du EM Fc Fd Gb Gc Gd Gh Gn Gz Hl Ho Hp Lp Lt Rv Rx Sh Si Uw Ux Uy Uz Vb Vc Wb Wf Wg Yd Yl Zq Zw Zx Ye Tm Tl Yf) mY(Du EM Fc Fd Fi Gc Gd Gn Gz Hl Ho Hp Op Rt Rv Rx Rz Sf Si Uw Va Vb Vh Vi Vj Vz Wb Yd Yi Yj Yl Zq Zw Zx Ye Xa) oQ(Dr Du EM Eq Fc Fd Fi Gc Gd Gn Hl Hp Lp Lt Op Rt Rz Sf Sh Si Sj Uw Vb Vh Vi Wb We Wh Yd Yj Zw Zx Tm Tl Xa) Gc(hB hC hG iH iZ kC kF kl kN kO kP kQ kR lW lX lY mE mF mH ml nF nI nJ nL nM nO nR nT nU nW nY oF oP) Xa(fP gP hB hC hG iA iH iO iP iZ kC kF kI kN kO kQ kS lW lX lY mF ml nJ nL nO nR nT nW oF oH oK oP pF) kN(Dr Du EM Fc Fd Gd Gn Gz Hl iH Lt Rv Rx Ry Rz Sf Sj Uy Vb Vh Vi Vj Wf Yd Yj Yl Zw Tl) lY(Dr Du EM Fc Fd Fi Gb Gd Gn Gz Hp iH Lp Op Rt Rx Rz Sf Uw Vb Vh Vj Vz Wb Yd Yj Zq) kl(Dr Du EM Eq Fd Fi Gd Gn Gz Hp Lp Lt Ru Rv Ry Rz Sf Sj Vh Vz Wb Yd Yj Zw Tm Yf) nO(Du EM Ex Fd Gd Gn Gz iH Lp Op Ps Qe Rv Sh Um Vb Vh Vi Vj Wb Yd Yj) nJ(EM Fc Fd Fi Gz Hl iH Lp Ps Rz Sf Sj Va Vb Vh Vi Vj Wb Yi Yj Zq Tl) lX(Du EM Fc Fd Gd Gh Gl Gn Gz lr Lh Li Lj No Qe Rv Rz Vh Vi Yj Zq) iZ(Du Em Gd Gh Gn Hl Ho Hp Lp Rt Rv Ry Uw Vh Vi Vz Wg Yd Yg Yh Zq) kC(Du EM Fd Gd Gn Gz iH jF Kx Lh Qe Rv Rz Vb Vh Wb Yd Zq Tl) nL(Dr Du EM Fd Gd Gn hV iH Ji Lh Lp Rv Sf Sj Vh Yj Yl Tl) kF(Du EM Fc Fd Gd Gn Gz iH Rv Sh Vb Vh Vi Vj Yl Zw Tl) kO(Dr Du EM Fc Fd Gd Gn iH Rz Vb Vh Vi Wb Wf Yd Tl) hC(Em Gb Gd Gn Ho Rz Uw Ux Vh Wg Yd Yl Zq Zx Tl) nU(Dr Du EM Gd Gn Hp Lp Rv Sf Vb Vh Vi Zw) lW(Du EM Fd Gd Gn Gz Hp Lt Vb Vi Wb Yl Tl) Eo(aC cB Cs Fp Hv Hx Li Lx Mb Ml Nw Po Qe) dW(aC aW Bo cB cC Fp Lj Lx Mb Nj No Qe) nR(Dr Du EM Gd Gn Lp Rv Vb Vh Wb Tl) mE(Du EM Gd Gn Gz Hp iH Vb Vh Vi Yj) mF(Du EM Gd Gn Gz Hl jF Rv Vh Vi Yj) ml(Du EM Gd Gn Gz iH Rv Vb Vh Vi Vj) nT(Du EM Fd Gd Gn Gz Vb Vh Wb Yl) Zq(fP gP hG iH iO kP kR nY oF oK) eO(aC aD aM Bo bR cB dC Fp Mb) kP(EM Gz Qe Sf Um Uw Vh Yj) oP(Du EM Fd Gd Gn Tt Um Tl) Ew(aC aM aN Bo cB Lx Mb Nj) Dw(aC aM aW cB Fp Lx Mb) eW(aC aM aW cB Fp Mb) nM(Du EM Gn Gz Vh) mH(Du eM Gn Gz Rv Vh) nF(Du EM Gn Gz Vh) nI(EM Gz Lh Um Vh) hB(Fd Gd Ho Wg Tl) nW(Gn Ho Rv Vz Wg) Tl(Oa On Qa) Wn(rR uO wE) hG(Du Gd Vh) Kx(eP gV) Rv(kQ oF) Tht(T GdkQ HoeP KrsI RziH dRgV) cM{gZ(aC aE al AL aM An aO aP aR Aw Ax aY BA bB Bc bE bG BN bO bQ bZ cE cF cG cH cN cO cR CS cT CU cV Cw cX dB Dc dD De dF dG dH dJ dK dL dN Dr DU Ed Ef Eq Ex Ez Fa Fb Fc Fd Fn Fp Fw Fy Gb Gc Gd Gh Gl Gz hB HC Hf Hl Hp Hq Hv Hw Hx Ib Ic Id Ih Im In Ip Iq Ir Is It Iv IZ jB Jd Je Jf Ji Jk Jn Jr Jy Kc Kd KE Kf kl kK Kl Kn Ko KQ kR Ky Kz Ld Li Lj Lp Lt Lu Lv lW Lx Lz Ma Mb ME Mf ml Ml MP Mq Mr Ms mW Mx MY Na NB Nd Nf Ng nH nI Nj nK nL NN NO nT Nv nW Ny oD oF Og Oh oK ON Op Or Ou OW Oy Oz Pa Pb Pe Pf Pg PH PI Pj Pk Ps Qa Qb Qc Qd Qe Qg Qh Ql Qn Qu Qy Qz Ra Rc Rf Rg Rh Ri Rj Rm Ru Rv Rx Ry Rz Sh Sr Ss St Tn To Tr Tt Tv Tz Ua Uc Ud Uf Uh Uk Um Uo Ut Uv Uw Ux Uy Uz Vb Vc Vi Vj Vo Vp Vs Vt Vu Vv Vw Vz Wb Wd Wf Wg Yd Yl Zw Zx Ye Tm Tl Wm Tj Ti Th Yf) dU(aC aL Aw Ax bA bB bE bJ bN bO bZ cE cF cK cO Cp Cs cT cV cX cZ dD dJ dK Dp Dr Du Ef Em Eq Ex Ez FA Fb Fc Fd Fi Fp Fy Gb Gd Gh Gl Gp Gz Ha Hb HC Hf Hl Ho Hp Ib Ic Id Ih Im Is Iv Iz Jd Je Jf Ji Jn Ju Jv Jy Kc Kd Ke Kf Kg Ki Kj Kk Kl Kn Ko Kq KR Ks Kx Ky Kz Ld Lh Li Lj Lp Lt Lx Ma Mb Mh Mn MP Ms Mx mY Mz Nb NC Nd Nf nH Nj NK NN Nr NT Nv Oa oD oF Oh Ok Om oN Op Or Ou oW Pe Pf Pg Ph Pi Pj Pk Ps Qa Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sr Ss St Tn To Tr Tt Tv Tz Ua Ub Uc Ud Ue Uf Ug Uh Uk Ul Un Uo Up Ur Us Ut Uu Uv Ux Uy Va Vh Vi Vj Vo Vp Vq Vs Vt Vu Vv Vw Vz Wb We Wf Wh Yd Yl Zx Tm Tl Xa Wm Tj Ti Th tF Yf) oD(Aa aC al aL aM Ar Aw AX bA bB bC bN BO bQ bV bZ cF cG cR CS cT cU dD dF dK dN Dr Ed Ef EM Eq Ex Ez FA Fc Fd Fi Fn Fp Fy Gb Gd Gh Gl Gn GP Gz Ha HC Hf Hl Ho Hp Ic Id Ih Ik Im Is Iv jB Je Jf Jh Ju Jv kC Kd Ke Kg Ki Kl Kn Ko Kp kQ Ks Kx Ky Kz Ld Li Lj Lp Lt Lu Lv Lx Ma Mb Me Mh ml Ml Mn mP Mq Ms Mt Mx mY NB Nc Nd Ne Nf nH Nj nK nL NN NO Nr NT Nu nW oF oH oN Op oW Oy Oz Pb Pe Pf PH PI Pj pK Po Ps Qa Qc Qe Qg Qh Ql Qm Qn Qv Qw Qx Qy Qz Ra Rb Rf Rg Rh Ri Rj Rv Rx Ry Sf Sj Sr Tn To Tr Tz Ua Ub Uc Ud Uf Ug Uh Uk Um Un Uo Up Ur Us Ut Uv Uw Ux Uy Uz Va Vb Vc Vo Vs Vt Vu Vw Vz Wf Wg Zw Ye Tm Tl Xa Wm Tj Ti Th tF Yf) jB(aC al aL Ax bA bH bN bO cF cG cN cO cU dJ dK Dp Dr Du Ed EM Eq Ex Ez fA Fc Fd Fi Fn Fw Gb Gc Gd Gh Gl Gp Gz Ha Hb HC Hf Hl Ho Hp Ib Ic Id Ih Iz Jd Je Jf Jn Ju Jv Jy Kc Kd Ke Kf Kg Ki Kj Kk Kl Kn Ko Kq KR Ks Kx Ky Kz Ld Li Lp Lt Lx Mn Ms Mx Nb Nd Nf nH Nj NK NN nO Ns Nt Nv Oa Op Or Ou Ow Pi Pj Pk Ps Qa Qg Qh Ql Qm Qn Qt Qu Qv Qw Qx Qz Ra Rb Rc Rf Rg Rh Ri Rj Rm Rt Ru Rv Rx Ry Rz Sf Sh Si Sj Sr Ss St Tn To Tr Tt Tv Tz Ua Ub Uc Ud Ue Uf Ug Uh Uk Ul Um Uo Up Ur Us Ut Uu Uv Uw Uy Uz Vb Vc Vh Vi Vj Vo Vp Vq Vs Vt Vu Vv Vw Wc Wd We Wf Wg Wh Yd Yl Zx Ye Tm Tl Xa Wm Tj Ti Th tF Yf) fA(aC al aL Aw Ax bB bE bJ bN bO cF cH cO cV DB dD dJ dK Dr Ed Ef Em Eq Ex Ez Fa Fb Fc Fd Fi Fn Fy Gb Gc Gd Gh Gl Gz Hb HC Hf Hl Hp Ib Ic Id Ih Iv Iz Jd Je Jf Jn Jv Jy Kc Ke Kf Kl Kk Kl Kn Ko Kq KR Kx Ky Kz Ld Li Lj Lp Lt Lv Mb Ml mP Mx mY Nb Nd Nf Nj nN nO Nq nT Oa oF Or Ou Ow Oy Pf Ph Pi Pj Pk Ps Qb Qe Qg Qh Ql Qn Qt Qu Qv Qw Qx Qy Qz Ra Rc Rf Rg Ri Rj Rm Rt Ru Rv Rx Ry Rz Si Ss Tn To Tt Tv Tz Ua Uc Ud Ue Uf Ug Uh Uk Ul Um Un Uo Up Us Ut Uu Uv Uy Va Vh Vi Vj Vo Vp Vq Vs Vt Vu Vv Vz Wb Wc We Wf Yd Yl Zw Zx Tm Tl Xa Wm Ti Th Yf) eQ(aC aI aL Ax bB bN bO cF Dp Dr Du Ef Em Eq Ex Ez Fc Fd Fi Fn Fy Gb Gd Gl Gp Gz Ha Hb Hc Hl Hp Ib Id Is Iz Jd Je Jf Jn Ju Jv Jy Kc Kd Ke Kg Ki Kj Kk Kl Kn Ko Kq Kr Ks Kx Ky Kz Ld Li Lp Lt Lx Mb Mn Mx Nb Nd Nj nK NN NO Nt Oa Ou Pe Pi Pk Qb Qc Qe Qg Qh Ql Qn Qt Qu Qv Qw Qx Qz Ra Rb Rc Rf Rg Rh Ri Rj Rm Rt Ru Rv Ry Rz Sf Sh Si Sj Sr St Tn To Tr Tt Tv Tz Ua Ub Uc Ud Ue Uf Ug Uk Ul Um Un Uo Up Ur Us Ut Uv Uw Uy Uz Va Vc Vh Vi Vj Vo Vp Vq Vs Vt Vu Vv Vw Vz Wb Wc Wd We Wf Wg Wh Yd Zw Zx Ye Tm Tl Xa Wm Tj Ti Th tF Yf) oW(aC Aj aL Aw Ax bA bB bE BN bO bV bZ cF cO cR Cs cT cX dD dJ Dp Dr Du Ed Ef Em Eq Ex Ez Fa Fb Fi Fn Fw Fy Gd Gh Gl Gz Ha Hb HC Hf Ho Hv Ib Ic Id Iz Jd Je Jf Jn Ju Jv Jy Kc Kd Ke Kf Kg Ki Kj Kk Kl Kn Ko Kp Kq KR Ks Kx Ky Kz Ld Li Lu Lv Mp Mx Nb Nd Nf Nj Nq Oa Or Ou Ow Ph Pi Pj Pk Qg Qh Ql Qm Qn Qt Qu Qv Qw Qx Qy Qz Ra Rb Rc Rf Rg Rh Ri Rj Rm Rt Ru Rx Rz Sf Si Sj Sr Ss St Tn To Tr Tt Tv Tz Ua Uc Ud Ue Uf Uh Uk Ul Un Uo Up Ur Us Ut Uu Uv Ux Uy Va Vb Vj Vo Vp Vq Vs Vt Vu Vv Vz Wc Wd Yl Zx Tm Tl Wm Tj Ti Th Yf) oT(aL bB bN bO cF dJ Dp Dr Du Ed Ef Em Eq Ex Ez Fa Fb Fc Fi Fn Fw Fy Gb Gc Gd Gh Gl Gz Ha Hb Hc Hf Hl Ho Ib Ic Id Iz Jd Je Jf Ju Jv Jy Kc Kd Ke Kf Kg Ki Kj Kk Kl Kn Ko Kq Kr Ks Kx Ky Kz Ld Li Lj Lp Lt Mb Mx Nb Nd nK nN Oa Op Or Ou Ow Ph Pi Pj Pk Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sr Ss St Tn To Tr Tt Tv Tz Ua Ub Uc Ud Ue Uf Ug Uh Uk Ul Uo Ur Us Ut Uu Uv Uy Va Vb Vi Vo Vp Vq Vs Vt Vu Vv Vz Wb Wc We Yd Yl Zw Zx Tm Tl Xa Wm Tj Ti Th Yf) pI(aC aL Aw Ax bN bO cF Cs dJ dK Dp Du Ed Ef Em Eq Ex Ez Fa Fb Fc Fi Fn Fw Fy Gd Gl Gz Ha Hb Hc Hf Hl Ho Ib Ic Id Iz Jd Je Jf Jn Ju Jv Jy Kc Kd Ke Kf Kg Ki Kj Kk Kl Kn Ko Kp Kq Kr Ks Kx Ky Kz Ld Li Lp lX mE mI Mx Nb nC Nf nH Nj nK nL NN Oa Or Ou Ow Pf Ph Pi Pj Pk Qg Qh Ql Qm Qn Qt Qu Qv Qw Qx Qy Qz Ra Rb Rc Rf Rg Rh Ri Rj Rm Rt Ru Rx Rz Sf Si Sr Ss St Tn To Tr Tt Tv Tz Ua Uc Ud Ue Uf Ug Uh Uk Ul Um Un Uo Up Us Ut Uu Uv Va Vb Vh Vo Vp Vq Vs Vt Vu Vv Vz Wc Yl Zw Tm Tl Xa Wm Tj Th) pH(Ax bB bN bO cF cO Cs dD dJ Dp Dr Ed Ef Em Eq Ex Ez Fa Fb Fc Fd Fi Fn Fw Fy Gc Gd Gh Gl Gz Ha Hb Hc Hf Hl Ho Ib Ic Id Iz Jd Je Jf Ju Jv Jy Kc Ke Kf Kg Ki Kj Kk Kl Kn Ko Kq Kr Ks Kx Ky Kz Ld Li Lp Lx Mp Mx Nb nK Nn Oa Op Or Ou Ow Ph Pi Pj Pk Qg Qh Ql Qm Qn Qt Qu Qv Qw Qx Qy Qz Ra Rb Rc Rf Rg Rh Ri Rj Rm Rt Ru Rx Ry Rz Sh Si Sr Ss St Tn To Tr Tt Tv Tz Ua Ub Uc Ud Ue Uf Ug Uh Uk Ul Um Uo Up Ur Us Ut Uu Uv Uy Vb Vh Vi Vj Vo Vp Vq Vs Vt Vu Vv Vz Wc Wh Yl Zw Zx Tm Tl Xa Wm Tj Ti Th) fB(aL bB bN bO cF Dp Dr Du Ed Ef Em Eq Ex Ez Fa Fb Fc Fd Fi Fn Fw Fy Gb Gc Gd Gh Gl Gp Gz Ha Hc Hf Hl Ho Ib Ic Id Iz Jd Je Jf Ju Jv Jy Kc Kd Ke Kf Kg Ki Kj Kk Kl Kn Ko Kp Kq Kr Ks Kx Ky Kz Ld Li Lp Lt Nb Nj nN Oa Op Or Ou Ow Pf Ph Pi Pj Pk Qg Qh Ql Qn Qt Qu Qw Qx Qy Qz Ra Rb Rc Rf Rg Rh Ri Rj Rm Rt Ru Rx Ry Rz Sf Si Sr Ss St Tn To Tr Tt Tv Tz Ua Ub Uc Ud Ue Uf Ug Uh Uk Ul Uo Up Ur Us Ut Uu Uv Uy Vb Vi Vo Vp Vq Vs Vt Vu Vv Wb Wc Wd We Wh Yd Zx Tm Tl Xa Wm Tj Th Yf) pK(aI aL Aw Ax bA bN bO cF dD dJ Dp Dr Du Ed

Figure 31 Continued

Um Un Uv Uw Uy Vi Vp Vq Vt Vv Vw Wd Wf Wh Yi Zx tF) Yi(AA AD AF aG aI Aj aK aL Ao aP AS aU aW aX aZ bB bF BG bI bJ bL bM Bn Bo bQ cA cC cD cJ cK cQ CS Ct CV cW Cx cY Db dC Dd dF Dg dH dK dL Dp Dr Du Ed Ef Eq Et Ex Ez Fa Fp FR Fw Ha Hf Ho Hq Hx Ih Ij Iq Ir Is It Jh Ji Jn Jp Ke Kg Ki Kk Kl Kr Ky Lh Lj Lt Mf Mh Ml Mn Mr Ms Mt Mv Mw Mx Nf Ni Nj No Nq Nr Nu Oa Oh Oi Oz Pa Pb Pc Pe Pg Ph Pi Po Ps Qa Qb Qd Qg Ql Qm Qx Rf Ri Rm Ry Si St To Tz Ub Uc Un Uo Up Ur Uv Uw Vh Vq Vs Vt Vu Vv We Wf Yj Tl Tj) Jp(Dp eC Ed Eq Ez Fa Fb Fc Fi Fn Fy Gh Gz Ha HB HC HF Ho Hp iA Ib Ic Id iH iJ iO iP IZ Jd Je Jr Ju Jv Jy Kc Kd Ke Kf Kg Ki Kj Kk Kl Kn Ko Kp Kq Kr Ks Ky Kz Ld Lt nW nY Oa oE oF oK oN Op Or Ou Ow pF Ph Pi Pj Pk Qg Qh Ql Qm Qn Qt Qu Qv Qw Qx Qy Qz Ra Rb Rc Rf Rg Rh Ri Rj Rm Ru Rx Ry Rz Sf Sh Si Sj Sr Ss St Tn To Tt Tv Tz Ua Ub Uc Ud Ue Uf Ug Uh Uk Ul Um Un Uo Up Ur Us Ut Uu Uv Vo Vp Vs Vt Vu Vv Vz Wb We Yd Yg Yh Yj Yk Yl Ye Tm Tl Xa tF) Zx(aC Aj Al Ar Ax bL bM bN cB Dc dD dI Dk Dr Du Ed Ex Fd Fp Fy Gd Gp Hl Hr Hu Hv Ih Ik In Is Iv Ji Jk Jl Jn Js Jv Ke Ki Kp Ks Li Mf Mh Ml Mr Mt Mz Nb Nn Nq Nr Ny Oa Oe Oh On Op Or Ow Pf Pg Pi Pk Po Qa Qe Qh Rf Rm Ry Sh St Tn Ua Un Us Vb Vo Vt Vz Wh Yg Yj Yl Zw Tl Xa) Ho(Aj aM aN Ar aX bF bG bL bM bN cB cE cF Db dH DK Em Eq Fy Hq Hv Hx Im Ir Is Jj Jq Js Jy Kc Kd Ki Kn Ko Kp Kq Ky Lh Lj Lt Lv Lx Lz Mf Mh Ml Mr Ms Mt Mx Nb Nd Ni No Nt Nu Or Pe Pi Pj Pk Po Pz Qa Qb Qg Qh Qn Rf Rx Sr St Tv Vq Vt Yd Tl Ti) Mn(Fc Fi Gz Hl Hp iA Id iP Kc Kk Kp kS Ky Ld oH oK oN Op pF Ps Qn Rt Ru Rv Rx Ry Sh Sj Ux Uy Uz Va Vb Vc Vh Vi Vj Vw Wc Wd We Wf Wg Wh Yg Yh Yj Yk Zq Zw Ye Tm Tl tF Yf) St(Dr Du eC Eq Fc Fd Fi Gb Gc Gh Gn Hl Hp Lp Op Ps Rt Ru Rv Rx Ry Rz Sf Sh Si Uw Ux Uz Va Vb Vc Vh Vi Vj Vw Vz Wb Wc Wd We Wg Wh Yd Yh Yk Yl Zq Zw Ye Tm Tl Xa Yf) Mz(Du Fc Fi Gb Gh Hl Hp Lt Op Ps Rt Ru Rv Ry Rz Sf Sh Si Sj Uw Ux Uz Va Vb Vc Vh Vi Vj Vw Vz Wc Wd We Wf Wg Wh Yd Yl Zq Ye Tm Tl Xa Yf) Un(aC DR Du Eq Ex Fc Fd Fi Gc Gh Gn Hl Hp Kc Kp Lp Lt oH Op Ps Rt Rx Sf Sh Si Vi Vz Wb Wd Wf Wh Yd Yh Yj Yk Yl Zq Zw Ye Tm) Tl(Cs Dk Ed Ef Fy Hp Id Ih Im Ir Jl Jn Jt Ke Kq Lx Mt Mv Nb No Nq Nt Nw Ok Om On Po Ps Qa Qb Qd Rm Tn Uc Ut Vi Vu We Yg Xa) Fd(Ao Ar Cs Dk Hf Hx Ij Im Iq Ir Ji Jn Js Ke Kq Lh Li Lx Ml Mr Mt Mw Nb No Nq Nu Nw Pe Pf Po Ps Pz Qa Qd Qe Ql Uh) No(Du Eq Fc Fi Gh Hl Hp Kc Kk Kp Ld Lt Op Qw Rv Rx Rz Sf Sh Si Sj Uy Vz Wb Wc Wd We Wf Wh Yg Yh Yk Zw Ye Tm Xa) Po(Eq Fc Fi Gb Gh Hl Kc Kp Lt Op Ps Ru Rx Ry Rz Sh Ux Uy Vb Vh Vi Vw Vz Wb Wc Wd Wf Wg Wh Yd Yg Yh Xa Th) Qa(Du Eq Fc Fi Gh Hl Hp Kc Lt Op Ru Rv Ry Sf Si Sj Uw Uy Uz Vb Vh Vz Wb Wc We Wf Wh Yd Yh Yl Zw Tm Ti) Qe(Du dW Eq Fc Gb Hl Kc Kp Ld Lt Ps Ru Rv Rx Sf Si Uw Ux Uy Uz Va Vb Vc Vj Vw Wf Wg Ye Tm Th Yf) Ke(Gn Hl Hp Lp Op Ps Ru Rx Ry Rz Sf Sj Ux Vj Vw Vz Wc Wd Wf Wh Yd Yg Yk Yl Zq Zw Ye Tm Xa Yf) Nw(Du eC Ed Fy hC iA iH iJ iO iP Kc Kp kQ kS Ky nY oH oK oN Or pF Ri Rx To Tv Uv Vv Vz Zw tF) Nb(Du Eq Op Ps Rv Ry Si Uw Ux Uy Vb Vc Vi Vw Vz Wc Wd We Wf Wh Yd Yg Yh Yl Tm Xa Ti Yf) Qb(Du Fc Gb Gh Hl Lt Op Rv Rx Rz Sf Sj Uw Ux Uy Vc Vw Vz Wc Wd We Wf Yd Yh Yl Zq Tm Ti) oH(aQ bB Ez Fy Iq Jf Ju Kk Ko Kp Lx Ow Pj Ql Qm Qn Qt Qw Qy Ss To Ua Ub Uc Uf Ut Vt) Hx(Fi gW Id iJ Kc Kk Ko Kp Ld Qn Qw Rx Sf Tn Uw Va Vt Wb Wc Wd We Wh Yd Yh Zw Xa) Hv(Eq gW Gz Lp Op Qx Rh Ru Rx Ry Rz Sj Uw Ux Uy Vb Vh Vj Wb Wd We Yl Zq Wm) Ry(Ao Cs Fp Gc Ha Ih Iq Jl Js Kq Lh Lx Lz Mt Mw Na Nr Nt Nu Rf Rm Ut) Yg(Aj aM Ar bF Bg dK Eq Fa Jn Ki Lh Lj Mh Ml Mr Mt Mw Mx Nm Vt) pF(aH aQ bB cG dD Ex Fr hC Iq Ko Kp Lh Ou Ow Qn Qt Qw Rg Ub Uf) Lx(eC eO Ew iH iJ iP Kc Kp Lt Ps Rx Tv Uv Vz Wb Wd We Wf Wh) Mt(Eq Gb Gh Hl Hp Ps Rv Sf Si Sj Vz Wb Yd Yh Yj Yk Zq Zw) Kp(Ar Cs eC Ed Ex Fp Im Iq Ir Jn kS Lj Mh oN Or Pe Qn) Vb(Ef Fy Ij Im Is Iv Jn Kq Mw Nt Pe Pi Ps Tn Ut Vu) aQ(hC hF hG iA iH iJ iO iP iZ kR nW nY oE oK tF) Ar(Hp Kc Lp Ps Rb Si Uz Vc Vi Vp Wb Wd Xa Yf) Du(Ao Cp Dk Im Is Js Kq Nd On Pa Pe Pi Ps Ut) Ir(iJ Kc Rx Vz Wc Wd We Wf Wh Yd Yh Yl Xa Ti) Iq(eC hC iA iO iZ Kc kQ kS nY oE oF oN Si) Or(Gc Kc Rz Si Uw Vh Vi Vw Wb Wd Yd Zq Xa) Ps(bM Fa Fy Ha Iv Ki Lh Lj Mh Mw Mx Vt) oN(aH aI bB dD Ex Lh Nq Ow Qn Tn Ub Uf) Yh(Fa Is Jn Li Lj Ml Mw Oa Of Vo Vt) Wb(As bL Im Lj Mh Mx Nd Oa Pk Qd Vu) Xa(aA Ao bM dH Hb Mh Mw Nd Pi Tv Vt) Eq(Co Dk Im Jd Kq Nq Nt Ok Tn) eC(Ib Kk Qn Tv Ua Uv Vp Vs Tj) tF(eM Ex Fr Ow Qm Qn Qu Tn Uf) Mx(Gb Si Uw Vj We Wh Yd Zq) Im(Fi Kk Rv Rx Rz Sf Sh Yl) Vz(Ao Jl Jn Js Nd Nt Pe Ut) Vu(Gh Hl Lt Rx Uy We Yd Zq) Bo(DW EO EW) Fa(Gb Gc Si Vh Vj Yd) Zw(Fb Is Ji Jn Mr Vt) Kq(Aj Jj Rz Vj Vw Zq) Ji(Hp iP Wd Wf Wh) Jl(Gh Lp Lt Rx Si) Jn(We Wh Yj Yl Yf) Lh(Hp Lp Wd We Wf) Vt(dR Ex Vi Wd Wh) Pe(Hl Uy Yj Yl Th) iA(bB Ed Ow Qn Qt) Cs(Lt Uw Wd Yd) Ew(aD aM bR cB) Lj(Wc Wd We Wh) dR(Id Qn Qw Uw) eO(aD aM cB cC) gW(aJ aN Lw Qd) kS(Id Ko Qn Qw) Nq(Gh Op Yd) Nt(Vj Vw Yl) Mr(Kc Rt Yk) Rx(Is Li Ow) Pi(Ex Wh Yf) hC(Di Et Ub) Ao(Sh Yl) Dk(Sf Sh) Dw(aD aM) Ed(Kc Ti) Fy(Gc Rz) Mw(Yd Yk) Jr(Kc Ub) Ok(kQ Yf) Ut(Jj Th) dW(cB cC) nY(bR Hb) CoRz EoaM FbSi MbeW IdYj IvYd OwoK UwgP} eO{bR(AA aC Ad aE AF aG aH aI AJ aK AL aM AN AO AP aQ AR AS aU aV AW AX aY aZ BB Bc bE BG bH bI bJ bM BN BO bP bS bX bZ cA cC cE cF cG CH cJ cK cL cN CO CP CQ CS Ct CU CV CW CX cY cZ dA DB DC DD De dF DG dH DI dJ Dk DL dM dN DW EM Eo Et EW FP FR Gd Hq Hr Hu Hw Hx Ih Ii Ij Ik Im In Io Ip Iq Ir Is It Jg Jh Ji Jk Jn Jo Jp Js Jt Lh Li Lj Lu Lv Lx Ly Lz Mb Mc Md Mf Mh Mi Mk Ml Mn Mp Mr Mt Mu Mv Mw Mx My Mz Nb Nc Ne Nh Nl Nm No Nq Ns Nt Nu Nv Nw Ny Oe Oh Oi Om On Oy Oz Pa Pc Pd Pf Pg Po Qc Qd) Mb(aA aC aD aF aG aH aI aJ AL aM aN AO AP aQ aR AS aV aW AX aY aZ bA Bb BC bF Bg bH bI bJ bL bM bN BO bP bV bX cA cB cC cD cE cF cG Ch cI cJ cK cL cN CO Cp cS Cu Cv CW CX cZ DB Dc dD dE dF DG DI dJ Dk DL dM dN DW EM Eo Et EW FP FR Gd Hq Hr Hu Hv Hw Hx Ih Ii Ij Il Im In Io Ip Iq Ir Is It Iu Iv Jg Ji Jj Jk Jl Jn Jq Jr Js Lh Li Lj Lv Lw Ly Lz Ma Mc Md Mf Mg Mh Mi Mj Mk Ml Mm Mn Mp Mq Mr Mt Mv Mw Mx My Mz Na Nb Nd Ne Ng Nh Ni Nj Nk Nl Nm Nn No Nq Nu Nv Nw Oe Of Oi Om On Oy Oz Pa Pb Pc Pd Pf Pg Po Pz Qa Qb Qc Qe) Lx(aA AD AF aG aH aI AJ aK AL aM AN AO AP aQ Ar AS aU aV aW aX aY aZ Ba Bb BC bE bF BG bH bI bJ bL bM BN BO bQ bS bV bW bX bZ cA cD cF cG Ch cJ cL cN CO cP cR CS Ct cU cV CW CX cY dA DB DC DD De DG Di dJ dK DL EM Et eW Fp FR Hq Hu Hv Hw Ih Ii Ik Im Io Ip Ir Is It Jg Jh Ji Jk Jl Jm Jn Jo Jp Js Jt Li Lv Ly Ma Me Mf Mh Mj Mk Ml Mn Mp Mq Mt Mu Mv Mw Mx My Mz Nb Nd Ne Nf Ng Nh Nk Nm No Nq Nt Nu Nv Nw Nx Oe Og Oh Oi Ok Om On Oy Oz Pa Pb Pc Pd Pz Qa Qc Qd) Bo(AA aC Ad aE AF aG aI AJ aK AL aM An AO aP aQ aR As aU aV Aw AX aZ BA Bb BC bE bF BG bH bJ bL bM bO bP bQ bS bX bZ cA cD cE cG CH cI cK cL cN CO CP CQ CS CT CU CV CW CX cY cZ dA Db DC Dd DE dF dG dH DI dJ DL dM dN dW eM Eo Et Ew fP FR Gd Hq Hr Hw Hx Ij Il Im Ip Iq It Iv Jg Jh Jl Jn Jp Jt Li Lj Lu Ma Mf Mh Mj Ml Mm Mn Mq Mx Nb Nd Nm No Nr Nt Nu Nw Ny Og Oh Om Oy Oz Pa Pd Pe Pf Pg Po Qd Qe) cB(aA aC AD aE AF aG aH aI AJ aK AL AN AO AP aQ AR AS aU aV AW Ax aY aZ BA bB BC bE bF BG bH bI bL bM BN bO bP bQ bS bV bX bZ cC cE cF CH cI cJ cK cL cN CO CQ cR CS cT CU CV CW Cx cY cZ dA DB DC dD DE dF Dg DI dJ DK DL dM DW EM Eo eW fP FR Gd Hw Ij Il Im In Io It Iv Jl Jo Jr Lu Lv Ly Lz Mg Mh Mj Mk Ml Mn Mq Mr Na Nd Nn Nt Nw Of Oh Oi Oy Oz Pc Pe Pf Po Qe) aD(aC Ad aE AF aG aH AI aM AN AO Ap Ar AS aU Aw Ax aY aZ BA BB Bc bE Bg bH bJ bN bO bP bV cC cD cE cF Ch cJ Co CP CQ CS CT Cu Cv Cx cY Db Dc Dd dE dF Di dJ dK Dl Dw Eo Et Fr Hq Hr Hv Hw Hx Ii Il Im In Io Ip Iq Ir Is Jg Jh Jj Jl Jn Jo Jr Js Jt Lh Li Lj Lu Ly Ma Mg Mi Mj Ml Mq Mr Mt Mv Mw Mx Mz Na Nb Nc Nh Ni Nk Nn No Nq Nr Nt Nu Nv Nw Ny Oe Of Og Oh Ok Om On Oz Pa Pb Pc Pf Pg Qa Qc Qd Qe) Of(aA aC Ad aF aI Aj An AO BB BC bF bG bO cC cD cE Ch cI cL CO cP Cu Cv cW dB Dc Dd dH Dk Dl dW Et Gd Hu Hv Hx Ih Ii Ij Im Io Iv Jh Jp Jq Jr Lh Lj Me Mf Mg Mm Mt Mv My Mz Nc Ne Ng Nk Nl Nn Nr Nt Nv Nw Nx Oe Og Oh Oi Om On Oy Po Pz Qa Qc Qe) aC(aM An Ao bB bE bI bN bP cF cP Cv cW dB dG Di dL dN Et Fr Ii Ik Im Is Jg Jh Ji Jk Jn Jo Jr Jt Lh Lv Lw Ly Ma Mm Ms Mt Mu My Mz Nb Nc Ni Nn Nq Nr Nt Nu Nv Ny Oe Og Ok On Pa Pe Po Pz Qa Qd Qe) bB(Aa aE aG aH aJ AL aN aO aR As aV aW Ax aY Ba bG bI bJ bM Bn bP bQ cD cF cG cH cI cN cQ cV cW cX cY DB dC DE DG Di dJ dL dN eM Hv Hx Il Ml Mm Ms Nd Ne Nk No Po) bM(aF Aj aM aO aS AW aZ cC cS dB Dg dJ DK Fp Gd Hv Hx Il Is Iv Ji Jj

IY(An nD Oh qU) Xa(dJ Gz pF) Tl(Ed Po Qm) Rv(Af Oz Qm) Rh(Ux Vh Yh) nN(cZ dA Nk) lW(dI qU Uo) kG(Ir rZ Sr) kI(kE Nw Pj) Fd(Dc Gp) Kr(sH sI) Um(kO nO) mH(qU Uk) AfHl ArkO BcRx DkSf GdKp GzuY MemW MhVw NdSj HcmU YdaJ VzJp KfoO PsRm RzbA QmOp WnvV OkVi UsnD UxcC eDoQ mEqU nChV} Wn{rR(aW Ax aZ Bc bL cC cD Ch cW DB dE Di fN Hf hL hO Hq Hu iH In Iq It Jd Je Jf jM jO jU jV Ke Kg Kp Ks Ky Li lN Mk Mz Na Nc Ng Ni No Nq Oa On pF qB QU qY rA Rb rU tN tO tQ tR tS TT tU tV tX Ug uI uO uP UR Us UU vH vP vT vV wC wD wE wF wG wH wL wQ yD yH yJ yK zA zH yE tM tF) bL(eT fN hO hP pS pY qB qC qD qO qP qQ qZ rQ rS rT rU rV rW sC sO tN tQ tS tT tV uI uL uM uO uP uT uU uV uX uY vA vB vC vH vI vP vQ vS vU vW wB wC wD wH wJ wP yD yH yK yL zA zG zI tM tL) cW(eT eZ fN fY hL hO hP oE pS qB qC qD qH qI qO qP qZ rN rO rP rQ rT rU rV rW sC sM tO tR tT tU tV tX uG Uh uI uL uM uN uO uT uw uX uY vB vI vT vU vV vW wC wE wF wK wL yD yJ yK zA tM) uO(aH AJ An Ap Ar aU BG bV cD cE cF cQ Ct cU Cw cY dL eT Fn fY hV It Kf Kn kQ Lx Lz Mg Mh Ml Mz Ng Nr Ow Oz Pa Pc Pe Po Qd qH Qt Qu Qx Qz rA Rg rW Ss Tz Uc Ur Uu Vs zA) sO(al bG Ch li lv Jh jK jV Kg Ky Ld Na Oz qU rN tN tQ TR tS tT tU tV tX uR uU uV vO vT vU vW wB wC wD wE wJ wK wP wQ yD yH yL zA zG zH zI yE tM xA) rN(aL aM BA bG bJ cD dD dJ Fb Fn jP jU Ko kR Ky My Mz Nx Ph Pz Qg ql Qu qY Rb Ss Tv uL Um Uu vT wH wK yJ) Uu(eZ fN hO hP pS qC qQ rO rU sM tN tO tQ tR Uh uL uR uU uX vA vI vO wE wG wH wJ wQ yH yK yL zH tM xA) bG(eZ fN fY hP pS qG qH rP rV rW sM tN tO tR tS tT tX uG uI uR uT uV uY vH vO vP vQ vV wJ wQ yJ yL) tV(aH aV BB Ct cU dA Dc fY gL Hf hV Ij iP It jH Ji jL Jn Jr Js Lu Mz Na nW Or Pj Qd qH Ql qQ uG) vV(bP cl Db dJ iA jV Kc Kd kQ Ky Mn Nx Og Oi Pd Ph Pz ql qV QW qZ rA rC sK St To Us uV vO wG) uL(aJ Aw cD cI cJ Ct Cw dB dK dL iP lt Ji Js Kf Kn kQ Kr Lu Oe qH qW Rf Tz uG Ur uV Vv) uG(aL cD Cu Cw Hw jO jV Ky Mx Mz Nd Nj Nx Qa Qe qG Qu tQ Ur vT wF wK yD yJ tM tF) wE(Ap aQ cF cI cU Dk gL iA lm iP It jH Jr Lu Oe Or qH Ql Qz Rc St) uR(Ap aV cU Dg DI iA jV Kc Kp Kx Mx Mz On rX sK TO uV wF) cD(hL qA qQ qZ rV sC Uh uI uM uW uX uY vB vC zG zH zI tM) tO(aA aH bJ eC eF Fn Jy Ky Mw Mz nW Or Pg ql qU Wm Tj) Cw(qG qZ rO rP rW tT uY vA wH wL wQ yJ zG yE tM xA) ql(Aw Ba Ch eC Ef Hu Jh Nq On Qu Tr tX Uc Uf uM) tM(aJ bP cH hG iZ Kd Kk qW St Tr Uk Ur uU vO wG) wH(aH Ap cU cY iA lt Ky Ly Oe Pc Qd Ur vQ wG) tT(aY bJ bW iA Js Lv Na nW Pz qU Ri uV zH) Ap(fN pS tN tS uT uU vT wC wF yL zG xA) Uh(aL Bn bZ Db Ib Id Mx Ok Rg To Ur) yD(aH bW dG eC kQ Lu nW rW Tn Tr wG) wG(aL Bo cZ DI Hu iA Il Jo Mz Ra) wF(aH aJ cU cV cY dG dN iA Uk Ur) uY(aJ aZ cR dB lt Ny Tz Uk uV vQ) vP(aK As Db jV Kc Ky Na Og qV sK) Ur(rC rO uV uZ wB wQ zH zl) Qu(uT uU uV uW vA zH) cU(fN tQ vO wC wP yJ) iA(wD wK yJ yK yE) qD(aJ Na Qz uV zH) vO(Dg DI Hu qA Uc) Mz(uT uV vQ wP) aH(fN tU wC tL) tQ(bW cY Js Qd) jV(eT qG qP uX) DI(uT uU yK) Ex(eC oE Ow) Mx(eD eT qQ) Kc(wP wQ yL) Ky(eT qO qP) Pc(uT uV zI) dB(fY rS rW) tN(JH nW) Na(fY rW) Pz(eZ yE) Uk(uT wQ) aL(rP uW) bJ(qG vU) yK(aQ cY) yJ(uV zH) qA(aJ iZ) sK(It yL) uU(Nk Ow) BowD DbrW DkfN WmyH NmwQ NqhP TosC TrhO JheZ SszH OezG bWqG dJfY qUuV lKuM} Dw{aD(aA aC Ad Af aH AJ aL AN AO aP aQ AR AS aU aV aW AX aZ bA BB BC bF BG bH bI bJ bL bM Bn bO bS bV bX bZ cA cB cC cD cE cF cG cH cI cJ cK cL CO CP CQ cR CS cT CU CV CW CX dA Db DC DD DE dF dG dH DI dJ dK DL dN Em Et fP Fr Hq Hr Hu Hw lh li Ij Ik Im In Io Iq It Jg Jh Ji Jj Jo Jt Lh Li Lj Lu Lx Ma Mb Me Mg Mh Mj Ml Mm Mn Mp Mq Mr Ms Mt Mu Mv Mw Mx Mz Nd Ne Nf Nh Ni Nk Nn Nq Nr Nv Nw Nx Oe Of Og Oh Oi Om On Oy Oz Pb Pd Pf Po Qa Qe) Bo(aC Ad aE Af aG Aj Al AN AO Ap Ar aS aU aV aW AX aY aZ bA bB bG bH bI bL bM bN bP bV bW cB cD cF Ch cI Cp Cq cR Cs CT Cu Cw CX dA DB DC DD dL EM Et FP Gd Hq Hx In Is It Jj Jl Jm Jr Lj Lx Mb Me Mh Mm Mr Mx Nd Nh Nj No Nr Nx Ny On Oy Pa Pe Pg Po Qa Qe) Lx(aC aE Af aG aH al aJ An Ap Ar As aV AW aX aZ Ba bB Bg bL Bn bQ bR bV bW cB cC cF Ch cJ cK cO cP Ct cU Cw cZ dA dC DG dH Dk DL dN EM fP Fr Gd Hr Ih Il Ji Jj Jk Jl Jo Lj Ma Mb Mg Mj Ms Nb Nh Nk Nm Nn No Nu Oe Of Og On Oy Oz Pb Pz Qb) Mb(Ad Af Aj aM AO aS aV aY Ba bG bl Bn bP bQ bR bW cB cC cD cE cF cG cO cP CQ CT cU Cx Dd DE dF Di dK dN Et fP Hq Hv Ik Io Ji Jj Jk Jl Jn Jp Jq Jt Lj Ly Ma Mg Ml Mn Mt Mu Nf Nq Ns Nt Nu Nw Of Og Oz Pd Qe) cB(aF aG al Aj aL An aO Ar aW Ax bA Bb Bc bF Bg bM bN bW bZ cA cC cD cE cG cH cI cK cL cO cP CT Cv cW Db dC Dd dH Di dM Fp Hx Im It Jn Jo Li Lv Lz Mg Mh Ml Mn Mr Nr Of Og Oh Pe Po Qa Qe) bM(aC Aj aO Ar aS AW aZ bB bI bR cC cF Cq Ct Cu DK Fp Hw Hx Ij Iv Ji Jl Jo Jq Jt Lj Mh Mi Mj Mn Mr Mt Mv Ne Ng Nr Nw Oe Oi Oy Pa Pg Po Qb) bR(aC aJ aM aP Ar bB cQ cW dB dC dG dJ dN Et Hv Hw li Il Im Iv Jm Jn Jq Jr Js Lh Li Lj Lv Mf Ml Na Nd Ne Nj Nk Nr Nv Nw Ny Qa Qb Qc Qe) aM(aC aG Aj aK aO Ar Aw Ax bB bG bQ cF Co cP CS Cv dB De Di dJ eM Fp Ih Jj Jo Lj Ly Ma Mn Nd Nj Of) Lj(Af al aN aQ aV aX bB bP cC cF Ct cW Dd dE Di dL eM Jj Ly Mn Mp My Nj Nm No Nt Nx Pa Pc Qa Qb) Qe(aC aH Aj aN Ar AS dC Fp Fr Ip Jj Jl Jo Js Ly Ma Mz Nd Of Qb) aC(aF aL bP cL Ct Di Et Hq Jh Ji Jn Jo Lu Ma Nc Nw Of Ok Pa) Of(Ad Al aN Ap aW bB DI Hq Io Jh Jq Nw Oh Pa Pe Po Qc) Nj(Ax cP Cs Db Et Lz Mh Ml Mn Mr Mt Nr Nw Oh Pe Po) Pe(aG Aj aN Bn cD Ct cX dC Dg Jo Ma Mg Pg) Po(Aj aN aO aW cO cP Di Ly Mg Oi Pa) aW(bI cC cP Et Lv Mt Nq Og On Qa) Mn(aG aJ aN As Ax cW Nd Ne No) Ji(aF aG aH aN cN cW Di Fp Mg) Nw(aG Ao Ap Ar cI Lv Ml My Oe) bB(aF aG aH cI cL Cs Di Mg No) dB(aF aO bF bZ cG Ct dH Hx) Ct(aN Dk Im Iv Nt Pa) Di(Iv Nd Og Ok Qb) No(aO cS Ne Nh Nl) Jn(aN aO Dg Js Nd) Et(aG Ao Cs Mm) Nn(Aj bW cS Jo) Jq(cX Jo Lv) aG(Hx Qa Qb) aN(aS Hx It) cC(Ar Ax Li) Aj(Cq Ny) Cs(Mz Qd) Fp(Ok Pa) Nt(aV dC) Ne(aO bW) AraF AxOk DeLv LyQb MzNd IpJj JrcS OhcO aOaP cFdC dGdL] Vb{mZ(Aj Ba bB bF Bg bZ cE cG Ch Co cR cS Dg Di Ef Eq Ez Fw HC Hq Hu U Im iO Is Iz Jd Jg Jh Ji Jk Jl Jn Jo Jp Jq Kf Kg Kq Ma Mg Mn Mu Mv Mw My Na Ng Nn Nq Nw Nx Ok Om On Op Ou Pf Ph Pi Pz Qd Qu Qz Rz Tz Ua Uc Uw Vi Vv Vw Wd Yg Xa) nK(aE An Ao Ba bI Co Cq Cu Ef Fy Hc Hq Hu iO Is It Iz Jd Jg Jk Jn Jq Jr Mh Mu Mv My Ng nI Nv Nx Of Om On oV Pz Qu Qz Rc Rj Rz Tn Tz Ua Uf Us Ux Vu Vv Wb Wd Wf Wh Xa) Iz(dU eQ fB gZ jB kE kF kG kI kK kN kO kP lW IX IY mE mH ml mM mP mS mT mU mW mY nA nB nC nD nF nH nI nJ nL nM nN nO nR nT nU oD oO oP oQ oT oV oW pH pl pK) Ao(eQ fB gZ jB kE kF kG kI kK kN kO kP IW IX IY mE mH ml mM mP mS mT mU mW mY nA nB nC nD nF nH nI nJ nL nM nN nO nR nT nU oD oO oP oQ oT oV oW pH pl pK) Ng(eQ fA fB gC gZ iJ jB kE kF kG kI kK kN kO kP lW IX IY mE mH ml mM mP mS mT mU mW mY nA nB nC nD nF nH nI nJ nL nM nN nO nR nT nU oD oO oT oV oW pH) Cu(dU fA fB gL iJ iZ jB kF kG kI kK kN kO kP IW IX IY mE mH ml mM mP mS mT mU mW mY nA nB nC nD nF nH nI nJ nL nM nN nO nR nT nU oD oP Qy) Fy(dR eQ fA fB hC iJ iZ jB kF kI kK kN kO kS lW IX IY mE mH ml mS mT mU mW mY nA nB nC nF nI nJ nL nM nN nO nR nT nU oD oV pF) Ba(eQ fA gC jB kE kF kG kI kK kN kO kP IW IX IY mE mH ml mM mS mT mU mW mY nB nC nD nF nI nJ nL nM nN nO nR nT nU oD oV oW pK) Pz(eQ fB kE kF kG kI kK kN kO kP IW IX IY mE ml mM mP mT mU mW mY nA nB nC nD nF nH nI nJ nL nM nN nO nR nT nU oO) Uf(dU fA fB kF kK kO IW IX IY mE ml mM mS mT mU nA nD nI nJ nL nN nO nR nT nU oO oP oV) Rz(eQ fA fB kE kF kK kO IW IY mE mH ml mM mS mT mU nA nD nI nJ nL nN nO nR nU oD oO) mE(Aj bl bR Co Ef Gc Hq Is It Jk Jn Jp Lh Mg Nv Ok On Ou Qu Tn Ux Vv Vw Xa) dU(bB bl cH Co Cq Ct Ef Hw lj II Is Jo Kf Li Nv On Qh Qu Tv Xa) nl(bB Co Dg Dk Ef Ez Fw Gc Ji Jo Jp Kf Lh Mg Ok On Ou Uw Vv Vw) mS(Fw Gc lh lj lm Is It Jo Js Of Ok On Qc Qu Ux Vq) oD(aW bB bJ Co cR Gc iJ lm iO Kq Li Mv Qz Tn Wd Xa) Hq(fA gZ jB kG IY ml mT mU nA nD nH nI nL nO nT) nO(aE Ef Fw iO Is Jp Nv Om Qu Tz) mM(Dg Ez Gc Is Jp Nv On Vv Vw Zq) ml(bI Co Cq Ef Jk Jn Ko Nx Qu) Gc(cF eQ gL hC kN IX IY oQ) Vv(kF kP IY mT nD nJ nL oP) nR(cG Co Kq Mg Nv Ok On Qu) nA(iJ iO Jp Mg Nx Op oV Vo) Fw(gZ kI IY mT nC nD oV) eQ(Hc Jn Mg Mn Ok On) nL(Cv ll Iq Is Nx Vq) oV(Cq Jo Li Qu Uk Xa) eM(Ef Is Jn Mv Om) fA(bI cH cI Cw Qz) iO(gZ Jp mT mW nH) jB(bI Cq Hw Nx Of) gL(Ji Jp Kf Ok) IY(bJ On Ux Vq) lW(bB Co Qu) kG(Ih Is Ux) Ef(IX mH) Qy(Du Jr) Jn(fR mW) fB(bB Xa) gZ(bI Me) mT(Hw Il) nH(Ip Iq) kN(Dd Mg) oW(Cq Nx) Mxpl lsnT WbpH QzmH QunC JooQ JpiJ OnmY UxnJ VqkF cRmW} Jp{eM(Dp Ez Fn Gz Ha Hc Hf Ib Ic Id Iz Je Jf Ju Jv Jy Kc Kd Ke Kf Kg Ki Kj Kk

Figure 31 Continued qQ rU rW sM uO vB vH vW wD wL wQ yH xA) rR(Ap Dg Fn Ji Jt Kf Kn Ok Pj Qd Vq Vt wJ) Ji(qH qQ qT qV qW qX qY rA uL vB) uR(Cv hW iC Kd Mz oF Pk uG vA Vt) Fn(rN rO rQ rS rU rV rW sM) Mz(qH qO qQ tX uU uV wB wH) wD(bQ bZ cO rB sC wH wQ) vB(Ap Dd Ic Kr Lu) vA(aV aW jO Kn Mf) Vt(qG ql uL yE) wH(Jl Ou rN wF) Kn(qU qV qW) tS(jO kR Vq) sC(jO jT Kk) Lu(uN vW) Kf(qH rO) eC(pH Tk) wP(cD dJ) qZ(Ic Iv) uL(jG Vq) uX(nW Qb) BbqX GchC MbrQ MkiC HveM TnuG HfxA KruI NxqH UmrN PjqU bQvW cJmZ fRlM} Ji{Nt(aA Et Fp Hr Hu Hv Hw Hx Ii Ij Ik Il Im In Io Ip Iq Is It Iu Iv Jh Jj Jo Jq Js Lh Lu Mh Mj Mk Ml Mp Ms Mu Mv Mw Mx My Mz Na Nb Ne Nf Ng Nh Nj Nm Nr Nu Ny Oe Of Og Oh Ok Om Oy Pa Pb Pd Po Pz Qa Qb Qc Qd Qe) Ms(aA Et Fp Hr Hw Hx Ii Ik Il Im In Is Iu Iv Jj Jl Jn Jo Jq Lu Mh Ml Mt Mu Mv Mw Mx My Mz Nc Ne Nf Nh Ni Nj Nl Nm Nu Ny Of Og Oi Ok On Oy Pa Po Pz Qa Qb Qc Qd Qe) Et(Fp Hr Hx Ii Im It Iu Iv Jh Jj Jo Lu Mb Mh Mj Mk Ml Mp Mv Mw Mx My Na Nc Nf Nj Nl Nm Nu Nx Of Og Om Oy Qa Qd Qe) Nj(aA Fp Hr Ii Ik Im In Iu Iv Jj Jl Jo Jq Lu Mk Mt Mx My Nf Ni Nu Of Og Ok Oy Pa Qa Qd Qe) Of(aA Fp Ik Im In Iv Jg Jq Lu Mt Mx My Nf Nl Nu Og Ok On Qa Qd Qe) Iv(Hw Ii Ik In Jj Jo Lu Mp My Nf Nu Og Oy Qd Qe sF) Nf(Fp Ik Im Jj Lu Mb Mx Nu Og Qa Qb Qd Qe) Qe(Ii Il In Iu Jj Jq Lu Mp Mw My Nu Og) sI(cS Nq Om Pf rU tV uM uO uW vB vV) Qa(Ii In Iu Jj Jq Lu Mp My Og) Nu(Ii In Jj Lu Mp My Og Oy) mZ(Gb Hl Hp Sf Si Um Va Vh) Qd(Ii In Jj Jq Lu Mp Og) Og(Fp Im Jg Mt Mx Qb) rR(Jv Kc Kd Kp Nq Ra) Vz(jQ jR qW qX rA) Jj(Fp Im It Lu Mx) Yk(lY mM mS nL) Im(Ii In Jq) fR(iC jK rA) wE(bI iA Tk) Nq(sF sJ) Lu(Jq My) Wc(jU qV) Wd(qT qX) Wf(nL rA) mM(Sf Si) nl(Gn Ye) WbjU ZwqX WhlM QysF XakS TleQ iAwD qUkI kNIN} Um{iC(kE kG kl kN kO kP lW lX lY mE mH ml mM mS mT mU mY mZ nA nB nD nF nH nI nJ nK nL nM nO nR nT nU oO oP) rC(kE kG kI kN kO kP lW lX lY mE mH ml mM mS mY nB nC nF nl nJ nL nM nN nO nR nT nU oO oP oQ) oO(eD hR hX iB jG jI jK jL jM jO jR jT jV jY lK lM lN lO qT qU qV qW qX qY rA rB rX rY) oP(eD hW hX iB jE jH jI jK jL jO jQ jR jT jU jY lK lM lN lO qT qV qY rX rY rZ) oQ(hA jG jH jK jL jO jP jQ jR jT jV jY lK lM qT qU qV qW qX qY rA rB rY rZ) hW(kE kG kI kN kO kP lX lY mE mH ml mM mS nB nC nF nI nJ nL nO nR nT nU) rZ(kE kG kl kN kO kP lY mE mH ml mM mS mY nB nF nJ nL nM nO nR nT nU) rB(kE kG kI kN kO kP lW lX ml mM mS mY nB nF nl nJ nL nM nO) hR(kE kG kN kP lX lY mE mH ml mS nB nI nJ nO nR nU) kl(bB hA hX iB jE jl jQ jU jV jY lK qU qV qW qX rA) nO(bB bX hX jQ jR jV Lh lK mZ qU qV qW qY rA) rY(kE kN kP lW lX lY mE ml mM mS mY nB nJ) rX(kE kN kP lW lX lY ml mM mS mY nC nJ nT) mZ(bB dD Gl Hq iB Jq Kq Lh Tn Uf) hX(kE kP lW ml mM mS mY nC nJ) iB(kO mE mW nF nJ nK nN) ml(jE jQ jV qV qY) nL(jl jP jU jY qY) nN(jH jY lM lO) jV(kN mW nH nR) lK(kN lW lY nB) jE(lY mM mP) qV(kN kO lW) nI(Gl Ks) qU(kP mW) kE(jl jY) kO(jU qW) XafB bBmH eCpH sFrR} Gc{hC(Aa aE AF Aj aK aL aM AN aO aP aQ aR AS aV AW aY aZ BA bB bC bF Bg bL BN bO bP bR bW bX bZ cB cD cF cG cH cJ cK cL cN CO cP CQ cS CT cU cV CX Db dC dD De dF dH dI dJ DK Dl dM Dr Du eF eM Et Fi FR Fw Fy Gb gC Gh gL Gn Gp Hb hG Hl Ho Hp Hr Hu Hv Hx Ib Ih Ik Il Im Io IP Iu Iv iZ jB Je Jg Jh Jj Jk Jl Jm Jn Jo Jq Jr Jt Kd kE KG kI Kj KN kO KP Kr kS Kx Ky Kz Lh Li Lj Lp Lv lW Lx LY Ma Md ME MH ml Mj Mk Ml MM Mn Mr MS MU Mv Mw MY MZ NB NC Nd Ne NF Ng NH nI nJ nK nL NM NN NO NR Ns NT NU Nv Nw Nx NY OE Og Oh Oi OK ON oO OP oQ Or Ow pF Pi Pj pK Pz Qb Qt Qv Qw Qy Rf Rh Ri Rj Sf Si Ub Ug Uh Uk Un Up Uw Uy Va Vh Vq Vw Wc Wg Yg Yj Zw Zx Tl Xa Tj Yf) kS(bA bQ cF cG cT dD dF dM Du Fy Ky Lx No nY Oa Po Tz Xa) eC(gC kI kN kO nL nT oO oP oT Rh) Hv(iZ jB kG nH nL nN oE oW pl) bB(lY mM mS mZ nL nR) nL(aV dD Qh Ug Us) oE(cQ cX Fy Mz Pi) aL(fB lW mZ) gC(nB nO Rg) oO(Jl nB Xa) Li(kG mW) Vq(Ed Nb) dD(lW mZ) eQ(Gd Jr) iZ(cF dJ) MxpI NdSf RgnH UgnA VaPk bAiA bXIY} bB{dU(Aa An cF dB eC Em Fc Fd fP fR Fw Gb Gd Gn hC Hl Ho Hp Hv Jn Jr Kk kR Lp Mx Nb Ns Ny Oa Qz Ru Ry Sh Si Tn To Uw Uy Vy Vj Vw Zw Zx Ye Tl Xa) fB(aL bC cF cL dJ Dr Em Fc fR Fw Gb Gd Gn Hl Ho Kk Nb Ny Ph Qd Ru Rv Ry Sf Sh Sj To Ux Uy Va Vh Vi Vv Wb Wc Wd We Wh Yd Zw Zx Ye Tm Tl Xa Yf) lW(Dr Em Fc Fd Fi Gd Gn Hl Ry Rz Sf Si Sj Uy Vh Vi Vz Wb Wh Yd Yk Yl Zw Tl Xa) Em(eQ fA gZ jB mE mH ml nI mM mS mZ nl nK nL nR oT oW pH pl pK) gC(Du Fc Fd Ho Kk Lp Ps Qz Rx Ry Sf Tn Uw Uy Vz Yd Yl Tl Xa) pl(bC Du Fw Gd Jn Kc Kk Ns Qz Sf Sh Tn To Uy Vv Vz Wd Yl) mZ(eM Gd Gh Gn Hl Hp Lt Op Ry Rz Sj Vi Wb Wf Ye Tl Xa) Gd(eQ fA gZ jB kN mE mH ml nI nK nL nR oT oW pK) Tl(eQ fA gZ jB kN mE ml nl oO oP oQ oT oW pH) nR(Eq Fd Gn Lt Op Ry Uw Vi Vw Wb Wf Zq Xa) pK(Du Gh Jn Kk Og Ry To Uy Vz Wh Yl Xa) Xa(eQ fA kN mE ml nB nK pH) oW(aL cF iA Ns Og oO Rf To) To(eQ fA gZ jB oT pH) Yk(kN lY mE mY nB nL) Wf(mE mM mY nB nL) Wb(mE ml nB nK) Ry(mE mH ml nK) eQ(aC Fw Jn Tn) gZ(An Fw Ny Og) Nq(sF sI sJ) Sf(kN ml nK) Wh(mE mH mY) fR(nI nL nT) Mk(nI nL) Uy(nL oT) Vi(mH ml) fA(Fw Nb) mM(Rx Zq) kN(Fc YI) KkoT RznB eDoQ eMnI} qU{Kf(kE kG kl kN kO kP lW lX lY mE mH ml mM mP mS mT mU mW mY mZ nA nC nD nF nI nJ nM nN nO nR nU oQ) Uh(kE kG kl kN kO lW lY mE ml mM mS mT mU mZ nA nB nC nH nJ nL nM nN nO nR nT nU oO) mM(aC aJ aK aU aW Ax Bc bJ Dp dR eF Fa Fw Ju Kc Kq Ld lN Oa Ql Rb Sr St Ub Un Ur) Gp(kl kP lX lY mE ml mT mW mY mZ nC nD nF nl nJ nK nL nN nU oQ) Kq(kN kP lW lX mE mH ml mS mW mY nC nD nJ nK nL nN nO nT nU) Un(kG kl kP lY mE ml mW mY mZ nC nD nF nl nJ nK nN) Yd(lr Jj Jk Mg Mh Mn Nc Nk Nl Nw Po Uc Vz Tm) mZ(Bb cP Fy Jd Jy Qh Qt Rc Tz Uc Uf Uu Uv) nN(aD Bb cJ cP Gl Jd Ql Tn Tz Up Uu Vp) kl(aC cJ Cw Fa Hb Jd Nw Ou Pj Qt Tz Ur) kP(cJ Cv Dl Gl iB Kn Ql Rc Up Ur Us) lX(An cJ Cw dM Gl Kn rZ Sr Ur) mE(aQ Cw cY dR Hb Jd oH Ql Vq) lY(aJ aQ bA dR Ko Ld oH) ml(aQ aU cJ dR Jd Ko Tn) Nx(mW mY nD oO oP oQ) Zx(jU jY Lu Ma Pz) cP(mP mW nD nH oQ) Gl(mY nD nF nK) Tl(Jj Lj Lx Nw) Ur(nJ nL nR nU) mW(cH cJ iB Ql) kN(aC dR Ld Nw) lM(Vz Wh Zq Xa) Kn(mP mY nD) Vq(mH mS nO) lW(aQ dR oH) nF(cJ Cw Ql) oP(aC KI lN) oQ(aR dG lN) Nw(nL nT) fR(lK Or) mH(aQ dR) mT(Aa Tn) nD(iB rZ) DpnJ PoYe NnZq JdnK WcqV WdJq aCnH aWmU nRrX nUqZ} sl{Kr(aA aC aE aH aK aN As aU aZ bA bF Bg bH bI bJ Bo bW cD cG Ch cR cS Cw cX dH Dk Ef Fa Fb fP Fw Ha Hq Ib Ih IJ Im iO Ip Iv jH jR jV Kc Kl kR lK Mr Mt Mu Mv Ne Ni Nm Nn No Nt Nu nW Nx nY Og Oi Ok Om Ou Oz Pb Pf Pg Qc Qd ql qO qP qT Ra Rg Rh rR tT vV wE wH Wm) Nq(al bA bF cE Ed Et Ez fY hL hO hR hW hX jG jK Jl jM jO jR Js Ju jV JY Ko lM Mp Mz Nv Nx Ny On pS qA Qg Ql Qm Qy qZ Ra rC Rf Ri sO Sr Ss St Tn To Tt TV Tz Ua Ub Uc Uf Uh vI VO Vu zH) lp(aD cD cE Fy Ha hG Hr hW Ib jG jK jL JY Lw Mf Mz Pg pS Pz Qc qW qX rA rC Rm tV Ub Uk uO Uu) Nx(aW BC dJ Hq Iq Iv Jh Jk Jq Jr Mf Om PF tQ uR vB yJ) wE(aR Ed hG Ju Ou Pg Qm Qv Rb Vu Wm Tj) tV(Cq Fa Hx Js Lu Pg Qm zG) Ib(Js Kg Ks rC Ua uO yH) tT(hG iA Ks Qg Ri wK tF) Wm(bC iA Je Nk wD) Ra(aY cY Nn uO wG) Pf(Aa cY dR Ny vO) Pg(iH pF uO uR yJ) Fa(tQ tR vP wD) Uh(Cw Hq Kp Uu) uR(Mr Nk Up Uu) vO(Bc Ef Jh Om) Js(Hf Hq Jk) dR(aK dJ hW) uO(Dk Ef Vs) An(bC jM) Ch(rC Ua) Cq(hW vI) Dg(KI Uu) Fn(Mx Na) Mz(Dk Iv) Rb(tQ wD) Rm(vP vV) iA(hW wB) iJ(bC jM) uM(Iv Ne) AsvP CsvV EfrC NaUp HqPj HfQy JlcW KswF RgaR QmtQ OarR} sF{Qy(aA aC Af aH Aw Ba bM Bn Ch Ct Cw CX DB De Dk dL dN Ef Hc Hf Hq hW Hx Ib iH iO Iu Jh Jk Jr Kf Ky Kz lN Mf Mk Mx Nc Ng Nk Nu Oe Of Og Oy Pa Pg pS Qe Ra rR Sr Ua uN uY Vs vI Vu Wm) rR(An Ar Bc bS cC Cp Cq Dk Dp Fn Gp Ha Ib Ic Id Jd Jf Ju Jv Ke Kf Kq Nx Oa Qg Qh Ql Qn Qt Qu Qv Qw Qx Qz Ra Rb Rc Rf Rg Rh Rj Sr Ss To Tv Tz Ue Uf Ug Uh Un Uu Vo Vs Vu Wm) Nq(al aR cE cY dF Et hO hR hW hX jE jG jK Jl jM jR Js jV Jy Ke Mz Nv Ny On pS Qg qZ rC Ss St tV Ua Ub Uc Uf vI Vo) lp(aD aR Bc cY Fy hG JY Mf Mx pS qV qW qX rA Ub Uk Uu) jM(An bJ cS cW Fw iA iJ nW Or Qg rC Rg Rm St Up) bJ(aR hW iC jE jL jR lK Ny Qd tT vP) cY(cS Dk Ef Hf Kr pF Ra rZ wD wE yK) Fa(Kr pS tN tO tR tS tX wD wH yL) Iv(jR Js Mz Nw Nx pS uY vP Vu) iA(hW Kr tS tT Uh wH yL) Wm(Je sK vA wD wK) pF(eT jR Lh uR vV) It(hW Qe tV uM) Qg(aR Ch Ef Ua) Bc(Is vV yH) Dk(Mz rW Vu) Ib(Ma Mg rC) Ir(hG uM) Ra(aY Nn) Kq(Kr pS) Rm(vP vV) Pg(tO wE) aR(Rg rV) cW(hO qC) dJ(jR vP) gL(vI Vu) Balo ChMa CqvI FyJk MxhW UbwE IuJs JevV KraH OutO PfdR cDjU hGyH jKjR} Kf{rR(aU aV bM Bn bQ bR bS cA cF cK cL cN CO CQ cS Cw dA dD dI Et Fp Hc hG hR Hu Ib Il jR Jt JU JV Kd Kp Li Lj Lx Lz Mb Mf Mi Mj Mk Ml Mp Mz Nd Ng Nq Ns Og Oi Or

Tz Up) Vz(Is Lx MI Mw Nw Qd Tz) ml(aJ Ax bA Cs cT dG iZ) kO(An dJ Kn Kp Pj Vq) lW(An bA cT iZ Qz) An(mU nD oO) Id(nC nH nJ) cX(IX mM nO) dM(kG nI nK) Sr(kG nJ) Qz(mU nD) iZ(mH nO) MpYd NfYg TzYe ZxWf UrnD PifR PjnA aJmE aRoQ nKrZ} qW{Vz(jK Jm jP Jq Lh Lv Lx Mk Ml Ng Nw Og Oi On Pf Po) Yd(It IN Nd Ne Ni Nk Nl Nn Oh) Wf(Mh My Og Po We Ye) Yc(Mh Mr Nd Og Oi) fR(Hr IK lN Or) Wc(Og Oi Pd) kO(dI gL Kn) Me(YI Tm) Id(kG nJ) bA(lW ml) WbOi ZwJr UhnA aJmW aRoQ cTlW} Zw{Jn(kE kG kP lW IX mE mH mP mS mU mW mY nA nB nC nD nF nI nK nM nO nR nU oO oP oQ) Lh(ml mM mS nD nH nI nR) Fy(dU fA hC mU oE) Tz(Ho jG nK) Mx(dU pI) Jq(kG nK) On(mM nR) jP(Mk Nn) lhkG JrnK NvnR dDlW} jH{Zx(lh li lo lt Jn Mk Mm Mz Ng Ni Nn Nr Oh Oz Pe Qa Wf Yg) Uh(kO mH mP mW nA nC nD nF nH nl nJ nK nN nU) nN(cP Dg Gp iO Kq Up) Wf(ln Jq Qd) PoYj MhYh NdYd JhWh SrlX aJmW aRoQ dFoP dRnO iHkO} jP{Yh(hA Hq lj In Jo Js Mj Mm Mw Mx Nf Oh Om Vz Wc) Uh(kE kG kO lW ml mU mW nA nD nH nN nU) Mk(Wb Wc We Wf Yd Ye) Wf(Nf Nn Oe Oi Oz) Mm(Yi Zx) Vz(Jh Tz) Wc(li Qd) nN(Up Vq) llYd YiOh WdJo UrnR aRoQ} pl{Mx(Dr Du Fc Fd Gb Gh Gn Hl Ho Ps Ru Rv Rx Ry Rz Uw Ux Uy Uz Va Vc Vh Vi Vj Vw Wd We Wf Wg Wh Yd Yl Yf) Fy(aL bX Ju Vh) Du(nO Uk) Ju(bX Cq) cR(To Uk) AnKx AoVh GnHw HacC LxRf RyLi RgbX UodD} mS{Yi(cD Fy Gp Ij Js Ko Lh Nn On Rf To Uf Us) Fy(Hl Ry Uw We Yg Yj) On(Hp Uw Vi Wc Yg) Eq(Ef Ij Qu Ua) Hq(Gh We Yj Ye) Yg(Gp Lh Uf) Yk(Gp Lh Tz) Wc(Lh Qm) HlVq Hplm ljRy JdhW JnTm NvVi OphC dllN} nK{Yk(aK aQ bQ dJ dR Nx) We(Hq Hu Mv Nv Nx Tn) Rh(Rz Vi Yd Yg Yi) iB(cP Dp iP No Nw) Jn(Hl Hp Si) qY(aJ ld Tz) Cq(Eq Sh) Ye(Hq nI) Nv(Vi Yg) hC(Op Wf) GdGl HlcR TzSi UbjV TnOg InrZ JlRy NxVa UhjM dMjR eMnl iPlK} jV{mW(aJ Dd Jv Kp Tt Ub Uk Up) Po(Vz Wb Wc Yj Zx) Tm(Ly Me Nj Og Tz) Uk(lW mE mH ml) Ub(mT nA nD) Zx(Jm Nb Ni) Kp(nH oP oQ) Mr(Vz Ye) We(Jh Nb) nH(cP iH) oP(Dg Kl) MeVz MpWb TtnC UpnR aRoQ aSml dlnN iHkO} Li{Ry(gC hC kE kG kO lW mE ml mW mY nR nU oE oW pH pK) mW(Gn Hp Vi We Wf Wh Yg Yi Yj Yk Ye Yf) We(mE nR nU) Uw(dU gZ mE) Vi(gC gZ pH) GbfA YimE YjmM WcgC WfnJ VjoT eMnl} ml{qY(aE Aj aM aN aV bJ Cs Ct DL hC Id Oa Qv Qz Ub Ue Ug Uk Vs) hC(Nk Op Yg Zx) aS(hR rB rY) Hq(We Ye) Nx(Va Wc) aQ(rZ Yk) bA(jR rA) qZ(It Lj) rY(cT Qv) RhrX NvVi UgrC iHlN} iA{Wm(rO rS tS tU uP uT uV vS vT wD wF wG wH wL wP yD yH yL zG zH yE tM tL) wF(Ap Dg Dl Kc Pj Ri Uf Vq Vt) Ou(wB wD wQ zA zH) Uf(tT uY) wD(Ap Ri) VqtQ} rZ{nT(aN bA bM Cp cT dB Dl Kp Qt) IX(bA dI iZ Kn Qz) Ub(kG mU mW nJ) nU(aQ aR bA iH) nN(Af Bn qZ) kG(aG aU cY) oP(Aa bA) oQ(Af aR) DpnJ QhnC UsnO VquX PjmE aQkO cTmH nRoH} On{Of(aA li Is It Iv Jg Jn Mb Mp Ms Mw Mx My Nh Nj NI Nq Nt Nu Nx Og Oy) mM(Gn Hp Yg Yj Ye) Nj(li My Og Oy) Yj(nR oP) GnnO HpmE VzrA WcjM VigP} gC{nO(Fd Fi Ps Ry Rz Wd Wh) nl(Fa Fb Fy Kq Kx Ow Vt) Kq(Kn Ny Vj) Ao(Sh Sj) Du(Pz Vq) Fy(Rv Wh) Ng(We Wh) Hq(Gh We) Qz(Eq Ye) AnKx MxVw NkHo IzRv YdOu QucR RzbL RuNx OwbX} iB{Qz(IX mW mY nF) cX(IX mU nT nU) An(kP IX nU) Zx(Me Mm Oz) Dp(kO nJ) Wc(Mr Oe) aJ(mW nU) aS(nA nJ) fR(cO Pi) nF(cQ dl) iZ(kP IX) oP(Dl Kl) YhOy VzOe JhWh UhnA UpnN aRoQ} jB{bl(Ps Rf Rv Uw Ux Vj Vo Vw Wc Wf) To(aW cA cQ cR Fd Fy) Rf(bN cA Fy Lh No) hC(Og Or Sh) Ao(Uu Ux) Gh(dB Hq) dD(Nb Uo) FyUw Mulb IdcA QgbJ LhNy NvVi} lN{Zx(hA Ma Me Ni Oh Pa Yd) Pj(lW mY nA oP oQ) nN(aC al cP dl Up) oO(aQ aS dl oH Rh) mW(aC cJ Cs) Tz(Wb Wh) iH(lW mE) oQ(dI Rh) GpfR lnoP UhnA aCmM cPnH} Vi{Nv(fA kE kG kO kP lW IX mE mH mM mT mY nB nD nJ nN nO nR nT nU) Fw(fA gZ kE kP IX mT nB nT) FyhC LhnH cGnR} mE{cT(hR hW hX rB rC rX rY) Yk(aQ bA bF bQ) We(Hq Tn Yg) rY(aS Qv Rh) Yi(dD Rh) jM(bA Uh) AoGd HqYe YgbQ SiJn WfhC PjrB aJlK dlhW} nl{Lh(Dp eM Gn Hl Lp Wd We Yg Yj Zx Ye) Gn(bM Fy Gl Js Nx) Fy(Hl We Yj) Hp(Jn Js Mw) rB(Jd Rh) DprC TjpK GlYe HqWe OphC} dU{Hq(Gb Gh Hl Lt Wf) Hl(Fy Mx Qb) Wf(bl Ip Nd) hC(Lp Sh Vz) Cq(Gd Si) Ny(Fy Ow) cR(Qu To) dD(bN Uo) DdGb GhdB MeHf NdLt IqUx aLcl} Eq{Ng(hB hC iH kR kS IX mY oE oF oH) Cq(mP mT nB nH oW) mY(Co Iz Nv Rz Ua) nO(Mv Qu Ua) Fy(kS oE) RjoW nRhC} nN{jT(aD Ao Bb Ct Dp Gp Jf Uh Vq) jR(An cP cZ dA) Up(hA jO rA) Nx(Rt We) qY(bM Tz) DprC GphA MwHp OphC UnjO dlrA} kG{Jd(hR hW rB rC rX rY) Uh(hR hW rC rX rY) Hq(We Yj Ye) Yk(Cq Hv Nx) rX(dC Pj Vv) Yj(Hv ll) Hllp OphC aGrC} oQ{aR(hA hR hW hX jG jK jM jO jR jT IK lO qY rA rX rY) cQ(hA jT qY rB rC) CqYg QzjL hXhB} oP{Gn(Ao Jn Lh Nx) Yj(Fy Jn Js Lh) rC(Gl Gp Kq) Dg(jT IK) rY(Kl Kn) AahA GphR JdlK KpjL KqhX iZqY} Yk{Cq(mT mW nA nD nH) IX(Fy Jq Lh Nx Tz) Tz(jL jT kP) Nx(nB nH nU) Jn(kP mY) QhnH aKnA} We{nA(Hq Mv Nv Nx Qu) Tn(mM mT nJ nR) nH(bl Hq ll Nx) Hq(mP nD) ConJ FwgZ JhjG JqrA NxnD} fR{hA(bN iH Kq Lh Nn Vq) rA(Db IK Nj Ow) IK(aG bl Gp) qY(Db Ql) jR(Nj tF) KxkS aEjL aZjO} nR{cG(Gd Gn Hl Ps Rv Vj Wc Wd Wf Yh Yj Yf) Up(rX rY) pH(Qu Uf) FyYj} nJ{rY(aS cK Ow Qv Vv) Dp(Lh rC) Du(Cq Nd) FwYl FyHl GlhW TnOg aSrX nUqZ iHrA} wF{nW(Ic Kn Pk Tz) Bb(Dk Nq rB) jM(Fw Kn Ri) Vt(Qm uR) NqKn TrVq KebQ RioK} jR{Vz(Jr Lx Nw Po) An(kE oO) Pj(kO nA) lW(bA cT) TzWh YgJr QznD UhnA cPnH iZoO} Ye{Hq(fA mT mU nA nB nD nH) Nx(nA nH) mU(Mv Mw) mY(Ao Jn) PojK NvmM} nO{Wc(Jn Lh Qm) Dp(Lh rC) Gn(Hq Tz) Hl(cR Jn) Hp(lm Mw) AnrY IjVh YiRh SrlK} rC{Dp(lW IX mY) yJ(Mz Qd Vt) Ch(tT uY) Hu(tT uY) lW(aC bJ) lmIz RhnB} Fy{Hl(mU nD) Yj(kP mM) Ry(hC oE) kS(Rv Sh) NqwQ RxoE RthC UwfA gZiO} Vz{rA(Jq Nw Oi Qd) Jh(hA jG jT) Tz(hA IK) JqIK cRmW} Zx{Me(jL jM rA) Oh(hA jT) hC(Gp pF) ltjT YdhA JmjM LhmM} gZ{bl(Rv Ux Vo Wc) AnKx GliO MeHf MnVh HlJn TocR UodD} Du{Nd(gL Qd Up Us) Jn(mM pK) CqnB FwmU HqoT RjnH} Nq{Wm(ql rU sK uY) Mz(rU rV) Un(uU wQ) VquY dFwQ} rY{lW(An cT Qv) aR(mY nC) dA(nC nT) aSnB cKkO cTnT} Hp{Mw(lW nD) Jn(kP nU) HqmT ImkP YiiZ NvmM cRmW} Uh{jT(kO lW mU nA nD) nA(jL jO IK) mlhR} oW{aL(aO bN bR dH) MeHf TocR ShhC NxVa UodD} Tz{Wh(hA jM jO lO) Wc(hA jL) YdhA TmjM} Nw{Nj(aA Im Mk My Nt Og) Nt(Of Og)} Vq{pF(hO tT uY) yJ(St Tv) TruO JkuY UuwH} mW{cR(Hl Yg Yj) Jn(Hl Wc) IK(iP Sr) DpLh} wQ{wD(Ef Pk Ql) Mz(lp Iq) EfPd WmJk Frlz} Wf{rA(Is Jo Mh) PojG MhqY OilK hCkP} Rh{Yi(gL hC iP) nB(hR hW rX) kOrX} pK{Tj(aW bJ) CqYd TocR UodD aEcF aLbN} eM{Hv(Ho Sh Wh Yg Yi) MvHo} nC{Up(hR hX) aR(hR hW) DpLh PjhX} rB{wD(It Js Mx Pk) aRmY bGnT} Hl{mU(Qa Qe) JnkE LhmM cHfA} Wc{Po(jK jM qY) qY(ln jK)} Vt{Pc(tN tO tR tT) QgyJ} dD{Uo(fA oT pH) lW(Dr Wb)} oO{Pi(jM jO) GdhC aRjM iZqY} Nt{lm(Of Og) Qd(Of Og)} Yj{NijO JroE LhmM RgnA} Yd{PojG MerA MkhA PblO} Nx{Va(lW mH nB) LytT} IK{YhJo JhWh UrnD nAqZ} oT{Mx(Rz Wd) AnKx TocR} Fw{Yl(lW mU) GbmU} Wb{GphC NdbM cXoE} Pj{hX(kO nF) IXrX} fA{UbIp QunH RzhC} mT{Hq(Fi Gn) KqRf} Wm{uR(Jk uY)} Yh{NfhA lnjM} Yi{NoiJ RfnB} Pk{MzwE dJtT} nU{MyqZ KphR} IX{AnhW hXiZ} jL{GpnA QzmU} pH{MeHf TocR} BcEfuO CqShnB DpLhkP NjlmOg JhWhjT WdJqqY JkRyoE RgOpnH aRhWkE Unconstrained panels with 2 analytes, where 1.0E-8 >= 'AUC p-value' > 0. Contains 1,351 panels of 199,260 total panels evaluated. : Jp(aA aC Et Fp Fr Hc Hr Hu Hv Hw Hx Ib Id Ih Ii Ij Ik Il Im In Ip Ir Is It Iu Iv Iz Jd Je Jg Jh Ji Jj Jk JI Jm Jn Jq Jr Js Jt Kk Kq Kx Ky Lh Li Lj Lu Lv Lw Lx Ly Lz Mb Mc Md Me Mf Mg Mh Mi Mj Mk Ml Mm Mn Mp Mq Mr Ms Mt Mu Mv Mw Mx My Mz Nb Nc Nd Ne Nf Ng Nh Ni Nj Nk Nl Nm Nn No Nq Nr Nt Nu Nv Nw Nx Ny Oa Of Og Oh Oi Ok On Or Ou Ow Oy Pa Pb Pc Pd Pe Pg Pi Pj Pk Po Qa Qb Qc Qd Qe Qm Qw Ra Rg To Tz Ub Ud Uf Ug Ul Um Un Uo Ut Uv Vs Vt Vu) Ji(aA aC aN Et Fp Fr Hq Hr Hu Hv Hw Hx Ih li Ij Ik Il Im In Io Ip Iq Ir Is It Iu Iv Jg Jh Ji Jk Jl Jm Jn Jo Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe rR wE) Nw(aA aC aN Eo Et Fp Fr Hq Hr Hu Hv Hw Hx Ih li Ij Ik Il Im In Io Ip Iq Ir Is It Iu Iv Jg Jh Jj Jk Jl Jm Jn Jo Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na

Figure 31 Continued

Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz
Qa Qb Qc Qd Qe) Ok(aA aC aN Et Fp Fr Hq Hr Hu Hv Hw Hx Ih Ii Ij Ik Il Im In Io Ip Iq Ir Is It Iu Iv Jg Jh Jj Jk Jl Jm Jn Jo Jq Jr Js Jt Lh Li Lj
Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng
Nh Ni Nj Nk Nl Nm Nn No Nq Nr Ns Nt Nu Nv Nx Ny Oe Of Og Oh Oi Om On Oy Oz Pa Pb Pc Pd Pe Pf Pg Po Pz Qa Qb Qc Qd Qe) Et(aA
aC Fp Fr Hq Hr Hu Hv Hw Hx Ih Ii Ij Ik Il Im In Io Ip Iq Ir Is It Iu Iv Jg Jh Jj Jk Jl Jm Jn Jo Jq Jr Js Jt Lh Li Lj Lu Lv Lw Lx Ly Lz Ma Mb Mc
Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq
Nr Ns Nt Nu Nv Nx Ny Oe Of Og Oh Oi Om On Oy Oz Pa Pb Pc Pd Pe Pf Pg Po Pz Qa Qb Qc Qd Qe) Qd(aA aC Fp Fr Hq Hr Hu Hv Hw Hx Ih
Ii Ij Ik Il Im In Io Ip Iq Ir Is It Iu Iv Jg Jh Jj Jk Jl Jm Jn Jo Jq Jr Js Jt Lh Li Lj Lu Lv Lw Lx Ly Lz Ma Mb Mc Md Me Mf Mg Mh Mi Mj Mk Ml
Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og
Oh Oi Om On Oy Oz Pa Pb Pc Pd Pe Pf Pg Po Pz Qa Qb Qc Qe) On(aA aC aN Fp Fr Hq Hr Hu Hv Hw Hx Ih Ii Ij Ik Il Im In Io Ip Iq Ir Is It Iu
Iv Jg Jh Jj Jk Jm Jn Jo Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv
Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Om Oy Oz Pa Pb Pc Pd Pe Pf
Pg Po Pz Qa Qb Qc Qe) Nt(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jq Jr Js Jt Lh Li Lj Lu
Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh
Ni Nj Nk Nl Nm Nn No Nq Nr Ns Nu Nv Nx Ny Oe Of Og Oh Oi Om Oy Oz Pa Pb Pc Pd Pe Pf Pg Po Pz Qa Qb Qc Qe) Jg(aA Aj Fp Ih Im Ip
Is It Iv Jj Jn Jq Jr Js Lh Lj Lu Lx Mb Mh Mq Mr Ms Mt Mx My Mz Nc Ne Ng Nh Nj Nl Nu Nv Nx Of Og Oy Pa Po Qa Qb Qc Qe) Iv(aA Fp Fr
Hr Ij Il Im In Io Ip Ir Is Jj Jl Jn Js Jt Lh Li Lj Lx Ma Mm Mn Ms Mt Mx Mz Nh Nj Nm No Nu Nv Nx Ny Of Og Oy Pa Qa Qe) Qe(AA aN dW
EO eW Hr Hw Il Im In Is Iu Jj Jn Jq Jt Lh Lw Mb Mh Mt Mx Mz Nc Ne Nf Nh Ni Nj Nl Nm Nu Nx Of Og Oy) Nj(aA Ew Fp Fr Ij Im Ip Ir Is Jl
Jn Js Jt Lh Li Lx Mr Mt Mx Mz Ni Nm Nn No Nr Nu Nv Nx Ny Og Pa Qa Qb Qc) Nu(Fp Ij Im Ir Is Jl Jn Js Jt Lh Lx Mn Mx Mz Nv Nx Ny Og
Pe Pg Qa) Mz(aC Hr Ih Im Ir It Jn Lx Mn Ms Mx Nf Nx Og Qa) bU(dU eQ fA fB gZ jB nN oD oT oV oW pH pl pK) jD(Vz Wb Wd Wg Yd Yg
Yh Yi Yj Zq Zx Ye Tm Xa) Im(aC aN In Jj Jn Lh Mt Mx Ne Nf Nh Nl Og) eO(aD aM bB bM Bo bR cB cC dB Lx Mb Of Po) dW(aM bM Bo
cB cC Lj Lx Mb No Qb) Jt(aC Fp Jj Mt Mx Ne Nl Og Qa) Eo(aD Bo cB Jn Mb No Po) cM(dU fA gZ jB oD oW Uh) eW(aD aM Bo cB Lj Lx
Mb) Ew(aD aM Bo cB Lj Mb) Zx(dX eP gW jU IN qU) Dw(aD aM Bo cB Mb) Mx(Ir Jn Lh Nv Ny) Og(Ir Is Jn Nv Qa) gW(fR kF kK kN mF)
Jj(Jn Kf Nv Nx) gV(Ko Kq Kx Ow) Ti(rT rZ wF) Th(tT yJ zA) Mt(aA Is Qa) Ir(Il Lh Mn) Xa(Nd oD oV) eP(Ho Kx Yi) Lx(Jn Mn) Sf(Dk Nd)
Zq(jY lM) Qa(Nl Nx) Wc(jl qV) Ut(dU Vb) aC(Ar nL) bB(dU oD) dX(Kx Yi) rR(Kc Kf) FpNv GchC GlmZ NmLh UbJd HrPe Ydjl ZwJr
WflM QysF YeqT KrsI WnUh Umnl mFjF qUkK Unconstrained panels with 2 analytes, where 1.0E-7 >= 'AUC p-value' > 1.0E-8. Contains 655 panels of 199,260 total panels evaluated. : Qe(aC
Fp Fr Hq Hu Hv Hx Ih Ii Ij Ik Io Ip Iq Ir It Jh Jk Jl Jm Jo Jr Js Li Lj Lu Lv Lx Ly Lz Ma Mc Md Me Mf Mg Mi Mj Mk Ml Mm Mn Mp Mq Mr
Ms Mu Mv Mw My Na Nb Nd Ng Nk Nn No Nq Nr Ns Nv Ny Oe Oh Oi Om Oz Pa Pb Pc Pd Pe Pf Pg Po Pz Qb Qc Tl) Jp(Cs Dp Ed Ez Fa Fn
Fy Gz Ha Hb hF Hq iA Ic Io Iq Jf Jo Jv Jy Kc Kd Ke Kf Kg Ki Kj Kl Kn Ko Kp KR Ks Kz Ld Ma Na Ni Ns OE Om Oz Pf Ph Pz Qh Ql Qn Qt
Qu Qv Qx Qy Qz Rb Rf Rh Ri Rj Rm Sr St Ua Uc Ue Uh Uk Up Ur Us Uu Vo Vp Vv) Jg(aC Fr Hq Hr Hu Hv Hw Hx Ii Ij Ik In Io Iq Ir Iu Jh Jk
Jl Jm Jo Jt Li Lv Lw Ly Lz Ma Mc Md Me Mf Mg Mi Mj Mk Ml Mm Mn Mp Mu Mv Mw Na Nb Nd Nf Ni Nk Nm Nn No Nq Nr Ns Ny Oe Oh
Oi Om Oz Pb Pc Pd Pe Pf Pg Pz) Mz(aA aN Fp Hq Hv Hw Hx Ij In Io Iq Is Jl Lh Lj Lv Lw Mb Mc Mf Mi Mm Mq Mt My Ne Nl Nm No Ny Of
Oh Oi Pb Pe Qb Qc Um yJ) Im(aA Fp Hw Il Ip Iq Ir Is Jl Jm Jr Js Jt Lv Lx Ly Mb Mk Mm Ms My Nc Ng Ni Nm Nv Nx Ny Of Oy Pb Qa)
Qa(aA Hr Hw Il In Is It Jh Jj Jn Js Lh Li Lv Lx Mb Mk Mm Ms Mx My Nc Ne Nf Nh Ni Nm Nv Of Oy Pb) Iv(Hu Ih Ik It Jh Jq Lu Lv Lw Ly
Lz Me Mf Mi Mj Mk Mr My Nc Ne Nf Nk Nl Nn Nr Om Pe Po Qb Qc) Lh(aA Fp Hr Hw Ih Ij Ik In Ip Is It Jj Jn Lw Lx Mi Mm Mn Mr Mt My
Ne Nf Nh No Nx Ny Of Og) Nu(aA Fr Hr Hv Ih Io Ip Iq It Jh Jj Jq Jr Lv Lw Mh Ms Mt Nl Oh Om Oy Pa Pf Qc) Lx(aA aN Hr Hw Io Iq Ir Is It
Jh Js Jt Mk Nc Ne Nf Nh Nl Nv Nx Ny Og Oy) Nj(Ih In It Jh Jj Jq Jr Lj Ma Mi Mm Mn Mp Mu Nb Nf Nk Pe Po) Nv(aA aN Is It Jn Jt Mb Mt
My Ne Nf Nh Nl Nm Of Oy) Nx(aA Fp Fr Ir Is It Jt Li Ms Mt Mx Nc Nh Nl Ny Og) aC(Ba Bb Cu dF Ih Io Is Kf Kp Li Mm Mt Nm Pj) Jn(aA
aN Fp Fr Hr Hw Jl Li Ms Mt Ny Of) Mx(aN Fr Ij Io Is Js Li Mm Mn Nm Qc) Mt(Fp Ij It Jj Js Mk My Nl Og Qc) Jt(aA Aj aN In Is Mb Nh Of
Qb) Js(Fp In Jj Ms Ne Nf Nl Og) Mn(It Lw Mi My Nh Ny Og) Ir(Hr In Jh Mm Nm Ny Oy) Is(aN Jj Mb Ne Nh Nl Nm) Ji(Aa bM hC iZ jD oE
wQ) Li(aA aN gV Jj Ne Nl Og) Ny(Hr Hu Io Jj Og) bM(bA eW Jd Nw Qd) cM(nN oT pH pl pK) aN(Ar Et Io Qc) bB(gZ oV oW pl) Gc(hG kS
oE) Nl(aA Fr No) oV(Qu Ub Ut) Ti(rC vB) Et(bA Pk) Fp(Nf Nm) Hv(Sj Tl) Ij(In Og) Ip(sF sI) Kf(lM Uu) dW(aD aF) gV(Nw Vt) qU(kF kP)
oD(Ut Tl) uY(Ex Gz) AjKq ArcD CsUb CuVb DuNd WmuR GlnL NoNh MmaA TnmZ SfJr QysH JlOn WnrN TktT aLfB nNIL Unconstrained panels with 2 analytes, where 1.0E-6 >= 'AUC p-value' > 1.0E-7. Contains 1,073 panels of 199,260 total panels evaluated. :
Qa(Aa aC aN Fp Fr Hq Hu Hv Hx Ih Ii Ij Ik Io Ip Iq Ir Iu Jk Jl Jm Jo Jq Jr Lj Lu Lw Ly Lz Ma Mc Md Me Mf Mg Mh Mi Mj Ml Mn Mq Mr Mu
Mv Mw Na Nb Nd Ng Nk Nn No Nq Nr Ns Ny Oe Oh Oi Om Oz Pa Pc Pd Pe Pf Pg Po Pz Qb Qc Qe Uh Tl) Im(bM Fr Hq Hr Hu Hv Hx Ih Ii Ij
Ik Io It Iu Jh Jk Jo Jq Li Lj Lu Lw Lz Ma Mc Md Me Mf Mg Mh Mi Mj Ml Mn Mp Mq Mr Mu Mv Mw Na Nb Nd Nk Nn No Nq Nr Ns Oe Oh
Oi Om Oz Pa Pc Pd Pe Pf Pg Po Pz Qb Qc) Lh(aC aN Fr hC Hq Hu Hx Io Iq Iu Jh Jo Jr Js Jt kC kR Li Lj Lu Lv Lz Ma Mb Mc Me Mf Mg Mh
Mj Mk Ml Mp Mq Ms Mu Na Nb Nc Nd Ni NL Nn Ns Nv OE Oh Oy Pb Pc Pd Pe Pf Pz Qb Qc) Mz(bM cD Hu iC Ik Il Ip Iu Jh Jj Jm Jr Js Jt Li
Ly Lz Ma Md Mh Mj Mr Mu Na Nb Nc Ng Nh Ni Nq Nr Ns Nv Oy Pa Pc Pd Pf Pg Po Qv rC rR rU Sr Uh Uk Uo Ur Vt) Nj(Aa aN Hr Hv Hw
Hx Ii Ik Il Io Iq Iu Lv Lw Ly Lz Mc Md Mf Mh Mj Mk Ml Mq Mv Mw My Na Nc Nd Ne Ng Nh Nl Nq Ns Oe Of Oh Oi Om Oy Oz Pb Pc Pd
Pf Pg Pz) Lx(aC Fp Fr Hq Hx Ih Ij Ip Iu Jj Jl Jm Jq Jr Li Lj Ma Mb Mg Mj Mm Mr Mt Mx My Na Nm No Ns Oe Of Oh Pb Pd Pe pF Pg Po Qb
Qc Ur) Ir(aA aN Fp Hq Hv Hx Ik Io Iq Is Iu Jj Jm Jn Js Jt Li Lw Ma Mc Mi Mk Ml Ms Mt Mu My Na Nf Ni Nn No Ns Nv Of Om Pe Pf Pg Qc
Ub) Jp(aN Ar Ax bM eC Ef Fb fP hB hC Hf hG iH iJ iO iP iZ Ju kC kQ kS nC nL nW nY oF oH oK oN pF Qg Rc Sf Ss Tn Tr Tv Vc Vq Wm
tF) Nu(aC aN Hq Hu Hw In Iu Jm Li Lj Ly Lz Ma Mb Mc Md Mf Mi Mk Mm Mq Mr My Na Nb Nc Ne Nf Nh Nm Nn No Nq Nr Of Pb Pc Pd
Qb) Ny(aA Fp Hv Hw Hx Ii Is It Iu Jh Jr Js Jt Li Lj Lv Lw Mc Md Mf Mi Mq Mr Ms Mt Mw My Nf Nh Nl Nm No Ns Of Oh Oy Pe Pg Qc)
Nv(aC Fr Hq Hr Hw Ih Ii Ij Ik Il In Ip Jh Jr Js Li Lj Lv Ly Mh Mk Mm Mr Ms Mv Mw Nc Ng Ni No Nq Nr Nx Oe Oi Pb Qb Qc) Iv(Aa Hq Hx
Ii Iq Iu Jm Jr Mb Mc Md Mh Ml Mp Mq Mu Mv Mw Na Nb Nd Ng Ni Nq Ns Oe Oh Oi Oz Pb Pc Pd Pf Pg Pz) Mn(aN gV Hq Hr Hv Hw Hx Il
Io Iq Is Jh Jn Lv Ma Mc Md Mf Mq Mr Ms Mt Mu Ne Nl Nm No Nq Ns Nx Of Om Oy Pe) Jn(aC cD gV Hu Ij Il In Io Is Jh Jt Lj Lv Lw Lz Mm
Mr Ne Nf Nh Nl Nm No Nx Oy Pa Pe Pg Po Qb Qc) Is(aA bM Fp Fr Hr Hw Ij Il In Jh Js Li Lj Lv Mh Mm Ms Mw My Nc Nf Ni Nn No Of Oi
Om Oy Qc) aC(Ad aN Ao Ap Ax bA Bc Bo Cp Cs Dg Dl eO Fr Id Ij Kc Mx Nt Pk Qc Ub Uh Un Vq Vt) aN(bA Bb bM cB cD cM Cs cT dD dF
dK Ij It Jr Lj Lw Mq Nf No Nt Nx Og Pc Qd Uh) Ji(Aj Ar aS Ax bA bL bO bV cD cM cQ CS dR iO iP lM nY oF pF Ub wF Wm) Li(Hr In Ip Jh
Js Jt Lv Lw Mb Mk Mm Mt My Nc Nf Nh Ni Nm Nn Of Pa Pz Qb) Jt(Fr Hr Ih Ip It Jl Jo Jr Js Lj Lu Mr Ms My Nc Ng Ni No Qc Vb) Mt(Aa Ip
Jl Jq Jr Lj Lv Mb Mm Mx Nc Ne Nh Nm No Of Oy Qb) Nx(Ih Ij In Jh Js Lj Mr Ne Nf Nm No Of Pe Qb Qc rR sI) Mx(aA bA Fp Jh Jr Kp Ma

Figure 31 Continued

Nl Nn No Pe Pg Qv Uh Ur) Js(aA Hr Hw Il Jh Lv Mb Mm Nc Nh Nm No Of) Og(Fp Fr Ik It Jh Jl Mm Nh Nl No Qb) aA(Fp Fr Ih Ij Lv Ne Nh Nm Nn No Nr) Fp(Ij Jh Jj Mm Ne Nh Nl Pz) qX(Vz Wd Wh Yd Zw Zx Ye Tm) Nm(Jr Lj Ne Nh Nl No Qb) Ij(Jj Mb Nc Ne Nh Nl Of) Xa(eM eP fB Hv kS pF pH) Uh(Ax bM Cs hC iA jD Pk) Aj(Ba Et Kf Nt Ok On) Ub(Ax Lj Oa Oh Qd Qe) Jj(Dc Fr Jd Mm Nn Pz) Vb(Gc Hv Jr Kf Nb On) cM(Ar Cs eQ fB Oa Qe) Et(Aa aG bM Cs hC) No(Ew Hr Ib It Ne) Nl(Jh Jl Nk Pa Qb) Zx(hC jF jH qT rA) bB(eQ jB oT pH pK) rR(Ap Jv rC Uf Wn) Ar(bA bJ cJ Qd) Vt(bM Kf Qg wF) jD(Pj Wc We Yk) qU(nN nR nU Yd) Aa(Mb Nt Qd) Eo(aM Qb Qd) Fr(It Ne Nh) Nd(Eq Gh Sh) Ip(Nh sH wQ) Qe(aS Ur Zw) Ut(nL Sf Si) kC(iB iH rZ) IL(kF kl nK) oD(cR Du Rz) Cs(cD Ml) Fw(oV Vc) Gc(iZ nY) Ik(Jd Kf) Yd(jH qT) Wb(Hv jU) Tl(jl Qh) Kq(Ef mZ) Lj(Dw Kf) Nw(cD eP) Um(mZ nO) Pj(hC oE) aL(nL oW) bM(Kp Ok) eW(cC Qb) wF(Ri Th) TitT GzvT Mmlt NbSf NfJr NhPa HodX TzZw IlJg IzOn YhjP ZqhC QcdW SroE Yejl KrsH WnsO UfnL UneP PepF aMgV cFjB fRIM tVsl kKlK Unconstrained panels with 2 analytes, where 1.0E-5 >= 'AUC p-value' > 1.0E-6. Contains 1,866 panels of 199,260 total panels evaluated. : Ji(aE aG aH aJ aK aM AO aQ aR aU aV aW aX aZ Bc bE bH bl bJ bN bR bS bU bZ cA cC cF cI cK cL cN cO CP cT cU CV cX cY dB dD DE dF dH dJ DK dL dM EF eP fP gL gP gW hB hF hG iA iC iH iJ kC kQ kR kS nL nW oH oK oN Qg Qv Qw Ra Rg sI tT tV Tz Ue Uh Uk Um Uo Ur Us Uv Vo Vp Vs Vt Vu Vv wD wG wJ) aN(AA AD aK aM Ao aQ aS aU aW Ax Ba bB bC bE bF bG bH bl bJ bL Bn bO bQ bR bS bU bV cA cC cF cI cK cL cP CU cV cW cY cZ Dd Di dJ Dk eO Ew Fp Fr Gl Hr Hx Ih Ii Ip Iq Iu Jg Jm Jq Js Kx Lz Mh Mi Mr Mt My Nc Ne Nl Nm Ny Oa Oh Om Pa Pc Pf Qb St Tz Vt) aC(AJ aM An aO aP aR Aw aX aZ bC Bg bM bV cF cG cN Co cT cU Cv Cw Dc Dd De dG dH Di Dk dL dN Ew Ex Fp fR Fw Fy Gp Ip Iv Jd Jh Jj Jq Js Ke Kn Ko Kx Lj Mg Mi Mk Mn Mq Mu Mw Nb Ne Nf Ng NH Ni Nj Nk Nr Nx Ny Pa Pd Pe Po Qb Sr) Mz(aS Cs Fr Hb Hc hP hR hV hX iB Ii JD jF jl jK jM jP JQ jR jY Kc Kf IK IL IM IO Me Mg Mk Ml Mv Mw Nk Nn OE Oz Pk Pz qB qQ qT QU QW qX qY Qz rA rB Rg Rj Rm rV Ss To tT Tz Ua Ub Uc Ue Ul Uu Uv wC wE wF wQ yE Wm) Li(cD Fp Fr Hq Hu Hv Hw Hx Ih Ii Ij Ik Il Io Iq It Iu Jk Jl Jm Jq Jr Lj Lu Ly Lz Ma Mc Md Me Mf Mg Mh Mi Mj Ml Mn Mp Mq Mr Ms Mu Mv Mw Na Nb Nd Ng Nk No Nq Nr Ns Oe Oh Oi Om Oy Oz Pb Pc Pd Pe Pf Pg Po Qc Ub Uh) Is(Aa Hq Hu Hv Hx Ih Ii Ik Io Ip Iq It Iu Jk Jl Jm Jo Jq Jr Lu Lw Ly Lz Ma Mc Md Me Mf Mg Mh Mi Mj Mk Ml Mn Mq Mr Mu Mv Na Nb Nd Ng Nk Nq Nr Ns Oe Oh Oz Pa Pb Pc Pd Pe Pf Pg Po Pz Qb Ub Ur Vb) Js(Fr Hq Hv Hx Ih Ii Ij Ik Io Ip Iq It Jk Jl Jm Jn Jo Jq Jr Lj Lu Lw Lz Ma Mc Md Me Mf Mh Mi Mk Ml Mn Mp Mq Mr Mu Mv Mw My Na Ng Ni Nk Nn Ns Oe Oh Oi Om Oy Pa Pb Pd Pe Pf Pg Po Pz Qb Qc) Jn(Ar bA bM Cs dD dW Hv Hx Ih Ii Ik Ip Iq It Iu Jm Jq Jr Kx Lu Ly Ma Mb Mc Md Mf Mh Mi Mk Mq Mu Mw My Na Nb Nc Ng Ni Nk Nn Nq Nr Ns Oe Oh Oi Om Oz Pb Pc Pd Pf Pz Ub Ur Vt Zw Tl Wm) Ij(Fr Hq Hr Hu Hw Ih Ik Il Ip Iq Ir It Iu Jh Jl Jq Jt Lj Lu Lv Lw Ly Ma Mh Mi Mj Ml Mm Mn Mp Mr Ms Mu My Na Nb Nf Ni Nk Nm Nn No Nq Ns Ny Oi Om Oy Pa Pe Pg Qc) Uh(Ar bA bL Dc dL dR eC eF fP Fy gP gW hG Hu Hx Id iH iJ Im iP Ir Jd Jj Kf KQ kR kS Kx Lh Lj Lx nY Oa oE oF Oh oN Pa Pe pF Qd Qe rR Ub Vp Vu Wm) Qe(Aj aK AR aU bA BB Bc bE bJ bM Bn bS bU cD cL cN CT dD dF Di dL Dw Ef Ew iJ Jd Kc Kf Ko Kp Qg Qw Ua Uc Uk Uv Vb Vs Vt Wc WF Zx Tm) Lx(Aa bJ bM bR bU cD cF gV Hu Hv Il In Jk Jo Lu Lv Lw Ly Lz Mc Md Me Mf Mh Mi Ml Mq Ms Mu Mv Mw Nb Ng Ni Nk Nn Nq Nr Oi Oz Pa Pc Pf Pz Rm) Nv(Hu Hv Hx Io Iq Iu Jk Jl Jm Jo Jq Lu Lw Lz Ma Mc Md Me Mf Mg Mi Mj Ml Mn Mp Mq Mu Na Nb Nd Nk Nn Ns Ny Oh Om Oz Pa Pc Pd Pe Pf Pg Po Pz) Jp(Aa Ao Aw bA Bb bL Bn bS cD Ch cK cM cU De eF Fw Gl Gp kG kI kO kP lX mE mF ml mS nH nl nJ nK nN Si Sj Tt Uw Vb Wb Yd Tm Tj) Ny(Fr Hq Ih Ik Il In Ip Jl Jm Jq Ly Lz Ma Mb Mh Ml Mm Mu Mv Na Nb Nc Ne Ng Nk Nn Nq Nr Oe Om Pa Pb Pc Pd Pf Po Qb) Ir(Fr Hw Ih Ip It Jr kR Lj Lu Lv Lz Mb Md Me Mf Mh Mj Mp Mq Mr Mw Nc Nd Nh Nk Nl Nq Nr Oe Oh Oz Pb Pc Pd pF Ur) Nx(Cs Hr Hu Hv Ii Il Io Ip Jr Lv Lw Lz Mb Md Mf Mh Mi Mm Mq Mu My Nb Ni Nn Nr Oe Oh Om Oy Pa Pb Pf Pg Po Pz wD) Mx(aV bM bV cD cM Cs Cu dF Di Hr Ih Ii Ip It Jj Jl Jq Kc Kf kR Mb Nc Ne Nf Nh Nr Oh Om Pf Pz Qb Ub Uf Vt Tl) No(Dw eO eW Fp Fr Hx Ih Ik In Ip Jh Jj Jo Jr Lj Lv Ma Mb Mf Mk Mm Ms Mw My Nc Ni nK Of Oi Oy Pd Pe Qb Qc) Lh(Hv Ii iJ Il iZ jD Jl Jm lX Ly Md mF Mv Mw mZ Ng nH nl NK Nq Nr nU Oi Om Oz Pa pF Pg Po Ub Uo Vs Vt) Jt(bM Hq Hu Hw Ii Ik Jh Jq Lv Lw Ly Lz Md Me Mf Mg Mk Mm Mn Mp Mq Mu Na Nf Nn Nr Oh Oi Oy Pa Pe Po Pz) Mt(Fr Hr Ih In Io Jh Jm Jo Ma Mh Mj Ms Nf Ng Ni Nn Nq Nr Oe Oi Pa Pb Pe Pg Po Pz Ub Vb) Mn(aA Cs eP Ew Fp Ip Jr Lj Lz Mb Me Ml Mm Nf Ni nL Nr Oe Oh Oz Pa Pc Pd Pf Pg Qc) Et(aH aR aS bE bL bV cD cI cK cM cU cX dD dI iO kR Kx IM nY oE oK Or rR Ub Vt) Fr(Fp Hr Hu Hw Ii Il Io Ip Jh Jq Jr Lj Lv Mb Mm Mr Ms My Nc Nf Ng Nm Of Oy Qb Qc) Nu(bA Hx Ii Ik Il Lu Me Mg Mj Ml Mp Mu Mv Nd Ng Ni Nk Ns Oe Oi Oz Po Pz) Ar(aK aM aS aZ bE bL bM bU bX cB cT cU dD dF gW Jd Lw Nw Og Qc Ub Vt) Fp(cM Hr Hw In Io Ip It Jm Jq Lv Lw Ma Mb Mf Mg Ms Nc Ni Nn Qb Qc) Nl(Aa Ih In Ip It Jj Jq Jr Lj Lv Ma Mm Mp Mr Mu Ni Nn Nr Po Pz Qc) Kf(aS Ax bM Cs Ed hC hR Iz jD Jo oE Of Or Pk Qa Qd Rg Ss Ub Uk Ur) Jj(Ad Bc bM Cs Fb Fy Ih Ii Io Jl Jm Kp Ks Kx Ne Nh Nm Pi Qb Uf) Vt(aS Ax bL cM Cs dL Im Kc Kk Ko Kp Kq Nf Og Oh On Pa rR Tz Ub) Mm(Ih Ip Jl Jq Jr Lj Mb Me Mr Ms Nc Ne Nh Pe Qb Qc rR) bM(aZ Bb dF Dw Eo Ew Gp lo Jg Jq Kc Oa On Or Qa Vi Xa) Ub(Cv Dc Fa Hb Id Kk Kn Ko Kp Kq Kx Nw oE Qa Sr Tz) aA(Hr Ik Io Ip It Jh Jl Lj Ma Mb Nc Nf Ni Pz Qb) Nm(Ih Ip Jl Jq Mb Mr Nc Nf Nn Og Pa Pe Po Qc) nL(bB bU dD iB IL Nw On Ou qU Rv rZ Tn Tz Um) Ne(Aa Ip It Jh Jl Jq Lj Ma Nn Og Pa Qb Qc) Nh(Aa In Io It Jh Jq Lj Lv Ma Ms Nn Qb Qc) Hv(Du Eq Hl Hp Iv Ry Sf Si Yi Yj Zq Zx) Og(Cs Io Ip Jd Kq Nn Nr Oa Po Pz Qc Tz) Nj(bA Hq Hu Jk Jm Jo Lu Mb Me Mg Ms) Qd(Aj aS bA bS bU cD Cs iJ Kc Kp Tl) Nw(aS aU bA bL bU cM Cs dL kC Qz Rf) Jr(bS Fc Gz Hp Hr Io Jh Si Ye Tl) Ur(Cq Dc Im Oh On Pa Pe Qa St Tz) Vb(Dc De Fw Fy nK Ok Pz Qa Qy Tz) Pj(dR gW hG hV iC jI kS nY Or rR) cM(Im Jd kC Kp Kx Lj nY oE oV Qa) Nd(Fd Ho Pe Ry Rz Sj Uw Uy Wb) Jh(It Jl Jq Lj Nc Pg Qb Qc) Ut(Gc pl Rt Sh Uy Va Vc Tl) kC(aL bB bU gW jF jI IL qU) Th(rR vP vT vU vV wQ zG) Xa(bU eQ gC iP iZ kG pl) Lj(bA bU cD EO Kp Nn) rZ(kN IX IY nI nT oP rC) Aa(Ih Im Me Nb Ok Qc) Tz(Gc Ho Kc Ko kP Tl) Iv(bA Cs Hw Jk Jo Mg) Qa(dD Kc Kp Mp Qw Rm) Qb(Jq Lv Mb Nc Ni Nn) Pe(cD Io Lw Lz Nf Pg) Gz(nl qT qV qW qX) Im(Aj aS cD hC Sf) Jl(Hp It Ms Nc wQ) Tl(bU Cs jB On Ps) nH(aL cY Gl jF lL) IM(Id Ke Kn Yj Yk) Ax(Kc Nb Uu Vo) Dk(On SH Si) Wm(rB rR vO wF) Ti(iC rO sK uW) Nn(Ip It Of Qc) Mk(Fa iC Ke Kq) Zq(gW kS IN oE) bB(dW fA fB nl) rC(Kn tT uY yJ) qU(kl ml nD oQ) IL(mF ml sH uY) oV(dD Ko Kx Pk) Aj(Ad bA Jd) Cs(Jg Nb Qw) Du(gL oT Qy) Po(dW eW Nf) Gc(iH oD Us) Zx(bO jQ jR) Kq(Iz Of Pa) cD(bA Jg Ok) eP(Ow Wh Yg) fR(eD jE Kx) hC(nl Uw Wb) jD(Wh Yl Zw) jI(nT Wf Yl) rR(jV Kn Ri) Di(dW eO) Ew(aW bR) Mb(gC Ip) Ho(bO bU) Ih(In Qc) Io(It Ms) Kc(Oa Pa) Kp(dX Ed) Ld(IX oD) On(aS Hc) Vc(cG dF) dD(eQ fB) gV(aD Tn) nN(IN Nk) uR(Or sl) DpnO DwcC EoHx ExcJ FyQv GdaM GlnC NfJq NibA TojB ItQc YimS YdjE WbUs JdOf JgUu WcjY WfjP RaOh YeiC KnoE KoPk WnuO OkcU UmkI UfmZ UwgP VuPa aWeW bRdW bUmT dXgW mliH nJiB kNkP Unconstrained panels with 2 analytes, where 1.0E-4 >= 'AUC p-value' > 1.0E-5. Contains 4,319 panels of 199,260 total panels evaluated. : Qe(AD aE AF aG aH al aJ AL aM An AO AP aQ As aV AW AX aZ Ba bC bF BG bH bl bL bN BO bP bQ bR bV bW bX bZ cA cB cC cE cF cG CH cl cJ cK CO CP CQ cR CS CU CV CW CX cY cZ dA DB DC Dd DE DG dH dl dJ DK Dl dM dN Dp dR eP fP Fw Gc gP gV gW HB hC Hf Hp iA Ib Ic iH iI iP Iz Jf Ju Jv kC Kk Kn kR kS Kx Ld nW oE oH oK oN Or Ou Ow pF Pi Pj Pk Ql Qm Qv Qy Qz Ra Rb Rf Rm Sf Sr St Tn To Tv Tz Ud Ue Uf Ug Ul Um Un Uo Uu Vc Vo Vp Vv Wb Yj Xa Wm) Uh(AD aF aG aH aJ aK aM An AO aP aR AS Aw Bc bE Bn bO bU bV bX cD cE CH cN Cp Cq cT Cu Cv cX dA DD De dF dl dJ Dk Dp dX Ed Et Fa Fp Fr Fw gL Ha HB Hc hF Hw IB IC Ih Ik Il iO Is IZ Je Jf jH jI Jl Jn Jr Js Jt Kc Kd Kk Kn Kp Kr Ld IM Lv Lw Lz Mb Mj Mk Ml Mq Mr Ms Mt Mu Mv Mw mZ Nd Nf nH Ni nL No Nr Ns Nv NW Nx Ny Og oH OK On Or Ou Pb Pd Pi Pj Po Qb Qg Qh Ql Qv Qw Ra Rg Rh Ri Rj Rm Sr St Tn Tv Tz Uc Ue Uf Uk Um Un Ur Us Ut Vt Vv Tk

Io It Jf Jh Mr Ms Ne Nm Of Og Pk Qc Qg Qv Qw Rf Rh Sr St tT Ua Uk Ul Um Un Vs) nL(aK aQ aU aV bC bE bF cG cJ cM cX cY dF Dp eM Fy Gc Gp iH Is jI Kc Op Qv Ug Un Ur We Ti) Gc(bR cB eC Ed gP hB iP kQ Nb nW oF Pk Qh Qt Qv Sf St Ua Ue Uk Um Un Uy Va Vi Vp Vq) Ir(eC hC Hu iA iH Ii iJ Jo Jq Ko kS Ly Mg Mv Nb Ne Ng oE Oi oK Pa Po Pz Rm tT Tz Um) Nm(Aj Hr Hu Ik In Io It Jh Ko Lu Lv Ma Me Mf Mh Mj Mm Mp Mu My Ng Ni Nr Of Oy Pg) cD(aJ aR Ax aZ Bb bV cG cT cU Dd dF Io Is Iv Ko Kp Lw Lz Mq Nj Nt Oa Pa Po Qc Xa) Mm(Hr Hu Ik Jh Lu Lv Mh Mi Mj Mq Mu My Nf Ng Ni Nn Nr Of Oy Pa Pb Pf Pg Po Pz) Im(aK aR aU bJ bL cT cX dD dL Hf iA Ib iJ Jd Kc Kk Kp kR oE oF oH pF Qg Qw Tl) Ax(aU cU Hb Iv kG Ko Kp kR lX Nt Nu oE Og Ou pF Pk Rf Rh Sr Tz Uf Un Ur tF) Io(In Ip Jh Kx Lv Lw Ma Mb Me Mi Mq Mr Mu Nc Ne Ni Nn Nr Of Om Pa Pd Pf Po) Jd(Bg Ch CX Ef Ib Iz Kn Kp Nd Ng Oa Oi Or Pa Pk Qv Qw Qz Tz Ue Un Uu Vb) Vb(aM Ba Cq dF gL iJ Iz Jg Jk Jq Kp mE mF Nt Nv Ps Qh Tn Uc Ux Vi Vu Xa) Un(aS cM dD dX Gp gV Ib iC Ik jD Kc Kp lM Lv Mk oE Pa Qw rR Sr Uk Uo) bB(Dw eW gV kN kO lW lY mE mF mH mI mZ nB nC nD nF nH nJ nK nR nT) Xa(aM bO cF De dR dU dX eC gL hC jB kQ Nb nW oE oF oH oK Rh tF) jI(kF kI kK kN lY mF mY mZ nD nJ nN Vz Wb We Wg Wh Yh Yi Zw Tm) It(Aa Hr Ih Ii In Ip Jq Lv Ma Mp Mr Mu Nc Nf Nr Om Pa Po Pz) Nb(eP Hp Js Ry Si Sj Vc Vh Vw Wb Wc We Wf Wg Wh Yj Zw Tl) Tz(Du Ib iC Kp lX mZ Nf oE Of Qg Qv rB Sf Si Sr Ua Um Wb) bU(Ex Fd gC Gz kF kK kN Kx lX mF mS nH nR Oa Vh Wb Zq Zx) Lv(Aa Ih Ip Jh Jq Ke Ko Kp Ma Mr Ne Nf Nn Nr Om Pz Qc) Ur(aM Fw Js Ko Kp Li Mq Nr Oa Or Po Qh Sr Us uY Vp Vu) cM(bV dF Ex Fa Fy hB hR Iv iZ Ke kF Ko kQ Li Nt Or Sr) oE(Bb Cu cX Fy Hb Id Ke Ko Kp Mk Oa Ou Pk Qm Uf Uw Tl) Qc(Aj dD Ii Ik Il Ip Jm kC Ma Mi Mp Mu Nc Nr Pd Pg) Jh(Aa Hr Ih Ip Jm Ma Md Mr My Nn Nr Of Oy Pa Po Pz) qU(Gz kN lX mH mW mY nC nF nH nJ nM nO oO oP Wf Zq) Nd(Fc Js Kc Kk Kx Lp Lt Ru Rx Uz Vi Zq Tm Tl Ti) Ny(Aa Eo Iq Jk Jo Lu Me Mg Mj Mk Mp Ni Oi Oz Pz) Nn(Hr Hw Ih In Jq Mb Mr Ms My Nc Nf Ni Oy Pb) Ne(Hr Ih In Jo Lw Mp Mr Ms Mu Nf Nr Oi Po Pz) Og(Aa Id Ih Ii Jm Jq Ko Ma Nc Om Pg Pk Sr St) Kp(Aj aS dJ eP hC Kx Li Oa Or Pk rR Sr Us) Wm(Hb hP hV rC tO uI uY wB wD wJ wQ yJ) Kx(aV dF gZ Hb Ik kS lX Mb Mf Mk mZ uR) dD(dU gZ jB kC mI nK oD oT oW pH pI pK) hC(Aa Bb dU Fy Gb Ho Kc Li mI Yd Yi Yj) rR(Bb Cv Dg Gl hR Ke Kk Kr lL Or Qw Qz) Js(Hu Iu Ly Mg Mj Nq Nr Oz Pc Qv Um) Ko(Aj Ex Hx Ik Mk Oa Of Pa Qv Uu Vu) rZ(Bb kG kI kK Kn mZ nD nN nO qW Th) Ip(Jq Lu Ma Nc Nf Pz sJ tT tV yJ) Sr(aS iC jV lM Mk Nf oH Pk Qw Uk) Li(Aa aS bL Di dL dW Jo kP Qw Tl) Aj(Ap Bc Cu Dc dF Dg Is Iv Nv) Fw(Ho lX mZ Rv Sf Wc We Zx Tl) Mr(Hr Ih Jq Ma Nc Nf Om Pg Pz) aM(Ho Kc Nj Vi Yg Yi Yj Zw Ti) mF(aK aQ cY Gl iB Qv Tn Ug Um) Po(Aa Dw Ih Jq Nc Om Oy Pz) Oa(cX gV Ik Kz Mk Ml Nf Rf) tT(Ap Dl Lu Ly Nq nW Pk Wn) wD(iA Lu Pk rB uT vP Vs wQ) Is(aS dL gV Mp Sf Um Zw) Iv(aK aR aU aV bO Di dW) Wb(bO cB cC De Ed gL qT) Kc(aS gV Hx oD Pk Qh St) Pg(Lw Mi Mq Nf Of Om Pd) eP(dB dR gW Ke Ld Ps Wd) mZ(bF Ex Fa gW Ke Nv Pi) kC(Bo eC Gl iC jQ jY Nv) lL(kG kK kO mM nC nO rQ) Aa(Jg Lu Mq Nc Ni Nu) Nr(Hr In Jq Nc Nf Sf) Ih(Hr Jq Ma Mb Ms Mu) Kn(aS hV iC wE wF wQ) Um(Hx iC kP nC oO Pa) nN(aL cX iH jV jY qT) oV(aL bO Fy Hl Ld Ow) Gz(Ex rA rN vA vW) Nt(aR aS cI cX Sf) Mk(Ex hR Or Ou Pk) Om(Hq Lw Nf Oy Pf) cB(Dr Em Wf Wh Tl) eM(gW nH nI nK Ps) fR(hA iC jF lK Nj) iH(mE nC nI nJ nK) De(Eq Gd Ps Yj) Fy(dL kR kS Vc) Nc(Jq Ma Pa Pz) Sf(Cq Dc Qh Zx) St(Hu Ib Ik Of) Qv(Iq kI Ks Pi) Nv(Hc jD lM lX) Uw(gW iZ kS Rh) dF(aR bL Iz Rz) dX(Fd Ky Ow Tn) tV(Iz Lu Ly wQ) Cu(Nf Nj Zw) Dk(Sj Vc Zw) Ti(fY wH Tk) Th(uM wK wL) Gl(lX mW nK) Nu(Jk Jo Mw) Hx(dW Qg rC) In(Cq Ik mI) Zx(jV lM Us) Wf(jE jO qX) Tl(Ed eQ Rh) Kk(aS cF Qm) Wn(tO uG uY) Uf(lX nC nH) Pi(Ex Hu Sj) Pk(Ik wE wF) aL(lY mI nI) gV(cP dR Nj) jF(kN mI nK) qW(Vz Wc Ye) oD(Hl Lt Wd) Nq(sI sJ) Ms(Jq Pz) Id(aK aV) Zq(mM mS) Or(aS Gp) Us(Du Ps) aR(sF uY) cC(Eo Ew) cF(nO oQ) cT(gW Nf) dL(aS Bb) eO(aW cW) nH(aK aU) iB(kK kO) jB(cA eC) sH(iA jM) jD(Ql Qm) jY(kF kN) BaCt CvrC ExHc FdgL MaMb HpJk HrPd TnVs YhjE YiiZ YjkG VzqV PzJq WglM QhVc QgPa YejP RhVi TkwE OuuR UgnO VqyJ PheQ aFeW bLdU cRgZ cXlX dJfA tXnW sIuO sFjM jHkK jKuY rQpF

Unconstrained panels with 2 analytes, where 1.0E-3 >= 'AUC p-value' > 1.0E-4. Contains 10,135 panels of 199,260 total panels evaluated. : Vt(AA AD aE Af aG aH aI Aj AL An AO AP aQ As AW aY aZ Ba Bb Bc bE BG bH bI bJ BN Bo bR bS bU bW cB cC cE CH cJ CO Cp cQ cR cS Ct Cv CW Cx cY cZ dA DB dC DI Dk dM dN dR eC Ed Ef eP Ez Fa Fb fR GL gP gW Ha HB HC hF hG Ho hP Hq HR Hv Hw Hx Ic IH Ii IJ Il IO IP Is It Iu Iv Iz Je Jf Jg Jh Jk Jm Jr Jt Ju Jv Jy Kd Ke Kg Ki Kj Kl Kn kQ kS Kx Ky Kz lM Lu Lw Ly Lz Ma Mb Mc Md Mf Mg Mh Mi Mj Mn Mp Mq Mr Ms Mu Mv Mw My Na Nb Nc Ne Ng Nh Ni Nj Nk NL Nm Nn Nq Nt nW nY Oa oE Of oH Oi oK Om oN Or Ou Ow Oy Oz Pb Pc Pd Pe PF Ph Po Pz Qh qI Ql Qm Qu Qx Qy Qz Ra RB RC Rf Rg Ri Rj Rm Sj sK Ss To tT Tv Ua Uc Ud Ug Uk Ul Um Un UO Up uR Ut Uu UV Vb Vi Vj Vo Vs Vu WB wJ yE tM Tl Xa Tj tF) Cs(AD aE AF aG aH aI AJ AL An aO AP aQ AR As aV AW AX aY aZ bB Bc bE bF BG bI bJ bL BN Bo bQ bR bS bV bW bZ cA cB cC cE cF cG CH cI cJ cK cN CO cP CQ cR cS CT CV CW CX cY cZ dA DB DC Dd dE DG dH dI dJ DK DL dM dR Ed Fb Fp Fr Fw Fy Ha Hb HC Hf Hq Hr Hu Hv Hw Hx iA Ib Ic Ih Ii IJ Ik Il Im In Ip Iq Ir Is It Iu Iz Jd Jf Jh Jk Jl Jm Jo Jr Js Jv Kd Ke Kg Kj Kl Kn Kq kR kS Kx Kz Ld Lj Lu Lv LX Ly Lz Ma Mb Mc Md Me Mf Mg Mh Mm Mq Mr Ms Mu Mv Mw My Nc Nd Ne Ng Nk Nl Nm Nn No Nq Nr Ny Oa OE Oh Oi oK Om oN Or Ow Oz Pa Pb Pc Pd Pe Pf Ph Pi Pj Po Qb Qh Ql Qt Qu Qv Qx Qy Qz Ra Rb Rc Rg Rh Ri Rm Sj Sr Ss St To Tr Tt Tv Ua Ud Ue Uf Ug Uk Ul Un Uo Up Uu Uv Ux Vo Vq Vs Vu Vv Wb Wm tF) On(aD aE AF aG aH aI AL aM An aO aQ aU AW aX aZ bA BB BC bF Bg bH bI bJ BN BO bP bR bS bU bV bW bX cA cB cF cG Ch cI cJ cL cN Co CP cQ cS CT cU CV cW cX cY cZ DB dC Dd De dH DI dJ dK DL dN Dp eC ED eF Ex Ez Fn fP fR Fy gL gP Gz HA hB hF hG Ho Hp hR iA iB Ic Id iJ iO iP iZ jD jE Jf jG jI jK jL jM jO jP jQ jR JU jV jY Kc kE KF kG Kl Kj kK Kl kN KO Kp KQ KR kS Ky lK lL lN lO Lp lW lY mH mM mP mT mU mW mY nA nB nD nF nJ nM nO nT nU nW nY Oa oF oH oK oO oQ Ou Ow pF Pi Pj Qg Qh Ql Qm QT QU qV qW QX QY RA RB RC Rh Ri Rj Rm Rt Rx Ry Sf Si Sj Sr St Tn To Tr Tv Tz Uc Ud Ue Uf Ug Ul Un Up Us Ut Uv Uy Uz Va Vh Vi Vp Vu Vv Wb Wd We Wf WG Wh Yd Yh Ye Xa Ti tF) Kf(Ad AF aK Al aM An Ao Ap aR As aV Aw aX aZ bA Bb Bc bE Bg bH bJ bL Bn Ch cI cN Co Cp Cq CT CU CV Cw CX Dc dD De dF Dg dH Di Dk Dl Dp dR eC eD eF Ez Fb fP Fr Fw Fy Gl gP gW Gz HA HB Hc HF hG Hr HV Hw Hx iA iB Ic Id iH Ii IJ Il In IO iP Iq Ir Is Iu Je jF jG JH jI jK JL Jm Jn jO jP jQ JR Js JU JV jY Kc Kd Ke KG Ki Kj Kk Kl Kn Ko Kp Kq KR KS Ky Kz Ld Lh lL lN lO Lv Mb Md Me Mf Mg Mh Mi Mj Ml Mm Mn Mp Mq Mr Ms Mt Mu Mw My Na Nc Nd Ne Nf Ng NH Nl Nj NL Nn No Nq Nr Ns Nu nW NY Oe oF oH OK Om oN Ou Ow Oy Oz Pa Pb Pc Pd Pe PF Pg Ph Pj Po Pz Qg Qh Qm Qt QW Qx QY RB rC Rf Rh Ri Rj Rm rZ Sf St Tn To Tv Ud Uf Ul Um Uo Up Ut Uv uY Vp Vs Vv wF wQ Tj) Ub(AD aE AF aG aH aI aJ AL AN AO aP aQ aR AS aU AW aX aY aZ bA bB BC bE bG bH bI bJ bL bN BO bP bQ bR bS bV bW bZ cA cB cE cH cI cJ cK cL cN cO cP CQ cR cS CT CU cV cX cY cZ dA dB dC Dd dF dG dH dI dJ DK dM dN Dp dR Du eC Ed eF Ex Ez Fn FP fR Fw gL GP Ha hB hC Ho Hq Hr Hu Hv Hx iA Ib Ic Ih IJ Ik In Io IP It Iu Iv Iz Jf Jg Jh Jj Jl Jm Jq Jt Ju Jv Jy KG kI Kj Kl kQ Ky Lu Lv Ma Mb Me Mf Mh mI Mj Ml Mm Mn MP Mq Mr mS mT mU nA nB nD Ne Nf nH nI Nj NK NN Nr Ns Nt NU Nv NY Oe OF Og oH Oi oK oN Op Ou Ow Oy Oz Pe Ph Po Pz Qc Qg Qh Ql Qm Qn Qu Qw Qz Ra Rb Rc Rf Rh Ri Rj Rm rZ Ss Tn To Tv Uf Uk Ul Up Ut Uu Uv Vp Vq Vs Vu Wb Xa Wm Ti tF) Uh(aA aE Af aI Aj AL Ap aQ aU aV aW aX aY aZ Ba BB bC bF BG bH bI bJ bN Bo bP bQ bR bS bW bZ cA cB cC cF cG cI cJ cK cL CO cP cQ cR cS Ct cU cV CW Cx cY cZ DB dC dE DG dH Di dK Dl dM dN Ef eP Ex Ez Fb Fn Gc Gl Gp gV hA Hf Hq HR HV hW Ii Ij In Io Ip Iq It Iu Iv jE jF JG Jh Jk Jm JO jP Jq jT Ju JV JY Ke KG Ki Kj Kl Ko Ks Ky Kz lK lL lN lO Lu Ly Ma Mc Md Me MF Mg Mh Mi Mm Mn Mp My NA Nb Nc Ne Ng Nh NJ NK Nl Nm Nn Nq Nt Nu Oe Of Oi Om Ow Oy Oz Pc Pf Pg Ph Pz Qc Qm Qn QT Qu QX QY Qz Rb Rc Rf rZ Ss To Tr Tt Ua Ud Ug Ul Uo Up Uu Uv Vo Vs wF Tj) Ar(Ad Af aG aH aJ Al An

Figure 31 Continued

AO Ap As AW Ax BN Bo bW cE Ch cN Co Cp cS Ct Cu Cv Cw Cx dA Db Dc DG dM Dp dR eC Ed eO eP Fn FP Fr Fw Fy Gp gV Hb HC Hf
Hq Hr Hu Hv Hw Hx Ib Ic Id Ih Ii iJ Il In IP Iq Ir It Iu Iz Je Jm Jo Js Jt Ju Jv Jy Kc Kc Kk Kn Ko KR KS Li Lj Lu Lv Ly Lz Ma Mb Mc Md Me
Mf Mg Mh Mj Ml Mp Mq Mr Ms Mt Mu Mv Mw My Na Nb Ng Nh Nk Nn Nq Nr Nv Ny OE oF Oh Oi oK Om oN Ou Oy Oz Pb Pc Pf Pg Pi
Pk Po Ql Qm Qn Qt Qu Qx Qy Rb Rc Rg Rh Rj Rm Ss Tr Tt Tv Ua Ud Ue Uf Ug Ul Un Up uR Ut Uu Uv Vo Vs Vv wF wQ Th tF) Nw(AD aE
AF aH al aJ AL An AP aQ As aV AW aY Ba Bb bF BG bH bN Bo bP bQ bW cE CH cl CO CP Cq cR Ct Cu Cv CW Cx cY cZ dA Db DC Dd
DG DI Dk Dl dM dN Dp Dw Ed Ef EW Fb fP fR Fy Gp gW HB HF hG hV iA Ib IC Id iH iJ iO iP IZ Jd JF jG jH jQ jR Ju Kc Kd Ke KG Ki Kj
Kk Kl KN Ko KQ KR Ks Ky Kz Ld IK IL IM IO mS nH nJ nN nO nT nW nY oF oH oK oN Ou Ow pF Ph Pj Pj Qh Qt Qu qV qW QX Qy RA
RB Rh Rj Rm rX rZ Sr Ss St Tn To Tv Ua Uc Ud Uf Ug Uk Ul Um Up Ut Uu Uo Vp Vs Vv Th tF) Qa(AD aE Af aG aH al AL aM An AO Ap
aQ aR As aU aV AW AX aZ BB BC bE bF BG bH bI bJ BN BO bP bR bV bW bX bZ cA cB cC cF cG CH cI cJ cK cL cN CO CP CQ cS CT
CV CW CX cY cZ DB DC Dd DE dF DG dH dI dJ DK DL dM dN Dp Ez Fb Gc gV HC HF HI Hp iA Ic iH iJ Je Jf Ju Jv Kd Ke Kn kP kR kS
Kx Ky Kz Ld nL nW oE oH oK oN Ow pF Pi Pj Pk Qm Qu Qx Qy Qz Rg Rh Sj Sr St Tn To tV Tz Ud Uf Ug Uk Ul Un Uo Up Us Uu Uz Vc Vi
Vo Vp Vu Vv Wb Wc WE wQ Yd Yj Tm Xa Wm Ti) Qd(AD aE AF aG aH al aJ aK AL An Ao AP aQ aR As aV AW aX aY aZ Ba Bb bF BG
bH bI bL bN BO bP bQ bW bZ cA cB cC cE cF cG cH cI cJ CO CP Cq cR Ct CU CV CW Cx cY cZ Db dC DG dH dI dJ dK Dl dM dN eC Ed
Fa Fb fP Fy GP gW Gz Ha hB HF hG Hp hV iA IC Id iH iO iP IZ jD Jf Ju kC Kd Ke Kg Ki Kl kP KQ Kr kS Ld nK nW Oa oF oH oK oN Ou
Ow pF Ph Pi Ql Qm Qn Qt Qu Qw Qx Qz Ra Rf Rg Rh rR Ry rZ Sr Tn tT Tv Ud Uf Uk Ul Uo Up Us Vp Vs Vu Vv Wb wE wG yJ tF) Mz(AD
aE Af aG aH al aJ aL An AO Ap aQ aU Aw aX aY bB BC bF BG bH BN Bo bP bQ bV bW bZ cE cG CH cL Co cP CQ cR cS Ct CU Cv CW
Cx cY cZ dA DB DC DD DE DG dH DI dJ DK Dl dM Ef eP eT Ex Fa Fb fN Fw FY Gl Gp Ha hC HF hL hO iA Id iH iO iZ Je Jf Jk Ju Jv Jy Ke
Kg Ki Kl kQ Kr kS Ld Oa oH oK oN Ou Ow Ph Pi pS pY qC qD Qm Qn qO qP rO rP rW RY rZ sF sH sO Tn tO tS tX uG ul uN Us uT uV uY
uZ Vb vH vI vO vP Vq VS vW wD wH yL zA zH tL Tj Ti) Lh(Aa al Ao aP aR aX Bb Bc bI bJ bL bO bS bU bX cC cD cG cL cM Cp cS cT cU
dD dE dF dG dH Di dL dM Dp eD Ez Fn fP Fy gL gP HA Hf hR hV IC Id Jd jE JF jG jH jI jK jL jM jO jP jQ jR jT jU jV jY Kd KE kF KG Ki
Kj Kl Kn Ko Kq Kr Ky Kz IL IN lW mE mH mM mP mT mU mW mY nA nB nD nM nR Oa oP Or Ou Ow Ph Pi Pj Qh Qm Qn QT QU qV qW
QX Qy RA RB RC Rf Rg Rh Ri rY rZ Sf St Tn To tT tV Ud Uf Ug Up Ut Va Vp Vu Wb wD wG wP Yd Yi Zw Th tF) bM(aA AD Af aG aJ
aK AL aM An AO aP aQ aR aV bB bC bE bF bG bI bJ bL BN BO bP bQ bV cA cB cC cE cF cG cI cK cM Cp Cq CV Cw CX cZ DB DE Dg
dH Dl DK dL dM dR dX Ed Ef eP Fa Fd Fn Fp Fr Gc Gn Ha Hc Hf Ho Hq Hr Hv Hw Ih Ip Iq Ir It Iu Jk Jl Jm Ju Jv Kr Ks Ky Kz Ld Lv Lz Ma
Mc Mh Mj Mm Mp Mq Mr Mt Mv Nd Ne Ni Nl Nm No Nr Ns Nu Ny Oe Oi Om Ow Pb Pc Pf Po Ps Ql Qm Qv Qw Ra Rb Rg Rh Ri Rj Rm Ry
Sj To Tv Uc Ue Uk Um Ur Us Vq Vs Vv Tj Ti) bA(AD aE AF aH al aL aQ AS AW Ax BB BC bE bG bH bL BN bO bP bQ bR bS bV bW bX
cA cE cI cJ cN cO CP CT Cu CV cW CX cY cZ dA DB DC DD DE dF dG dH DI dJ dK dM eC Ex Fp FR Gc Gd gL Gz Hb hC Hq HR Hu Hw
Hx Ih Ii Ik Il In Io Ip Iq Ir Iu Jd Jh Jl Jm Jq Jr Js KC Ko Kp kR Kx IX Lz Ma Mc Md MF Mg Mi Mj Mk Mm Mt Mu Mv Na Nc Ne Nl Nm Nn
No Nq Nr Nv Nx OE Oh Om Or Oz Pa Pb Pc Pd pF Pi Qb Qc Qv Qz Un Vb) Kq(aA AF aM Ao aR As aV Aw Ax Bc bI bL Bn cC cM Co Cp
Cq cU CV Cw CX De dH dJ dL eF eP Ex GP Gz Hb Hf Hp Hu Hv Hw Hx Ib Ic Id Ij Im In Iq Ir It Jf Jh Ji Jn Jo Ju KC Kd kG kl Kj Kk Kl Ko
Ks Kz Lj LX Ma Md Me Mf Mg Mh Mj Ml Mn Mr MT Mv Mw My Ns Nc Nd Ng nl NJ NK Nl Nn NO nR Ns Ny oD OE OH Oi Ok Om oP
oV Ow Oy Pe Pi Pk Pz Qb Qe Qh Qu Qv Qz Ra Rg Rh Ri Rj Rm Ry Sr Ss St To Tv Tz Uc Ul Un Uo Us Ut Uu Uv Vb Vc Vo Vs Wm) Un(aF
AJ aK aM aO aQ aR As aU aV aZ bB Bc bE bH bJ bL bN bO bR bU bV bW bX cA cB cD cF cG cH cI cL cN cP cT CV cX Dc dF dH dJ DK
dL Dp dR eC Ed eF Ex Fb fP Fr Fw Fy gL gW Gz Hb hC Ho Hu Hx iB Ic Id iH lJ Im In IO iP Ir iZ Jf Jg jI Jj Jo Jt Kk Ko KR kS Kx Ky Ld Li
Lj Lx Ly Ml Mn Mw Nf nH Nr Ns Oe Of Og oH OK oN Pc pF Pi Pj Pk Pz Qc Qg Qh Qm QV qW Qz Ra rB rC Rf rZ St Tn To Tz Ue Uf Um
UR Us Uv Vb Vp Vs wF yJ Xa Wm) Ji(Dp Dw EO eT Ez Fa Fb FN Fy Gl Gp gV Gz HA Hb Hc hL hP hR iB Ic Id JE jF jG jK jL jM jO jP jQ
jR jT jU jV jY Kc Kd Ke Kg Kl Kj KN KO Kr Ks Ky Ld IL IN IO IX mF ml mE mF ml mT mW nC Nd nH nl nK nN nO nU Or Ou Ph Pi Pj pS qG qH ql Ql Qm Qn qO qP
qQ Qu qV qW qX rA rB rP rQ rS rT rW rX rZ sC SF sK sM sO Tr tX uG uL uN uO uP uR uT uU uV UW Uy uZ VA VC vH vl Vq vS vT vV
vW Wd Wf Wg Wh yH yK yL zI yE tM Tl xA Wn Tj) Ok(AD aE AF aG aJ An Ap aQ As aV Aw Ax aY aZ Ba Bb BC bE bF BG bH bJ Bn BO
bV bW cB cE cF CH cO CP Cq cR Ct CV Cx cY Db DC De dF DG Di dJ Dk dR dX eC Ed EF Ex fP gL gP Gz HB Hc hF hG Hp iA Ib iH iJ iP
IZ Jf KC Kj Kk kP kQ kR KS Kx mF ml nC nl nJ nK nU nY oE oH oK oN Or pF Pi Pk Qv Qy Ra Rg Rh rR Sf Sr St Tz Ua Uc Uk Ul Um Uo
Uu Uv Uz Vh Vo Vp Vs Vu Wc Wd We Wf Wg Yd yJ Zw Wm) Et(Ad Af Al An As Aw Ba Bc Bg Bo Ch Cq Ct Cu Cv Cw Cx Db Dg dW eO
eT eW Ex Fb Fn Fw Gl Gp gV Gz hA Hb Hc Hf hP hR hV hX iB JE JF jG jH jl jK jL jM jO jP jQ jR JU JV JY KC Kd Ke Kg Ki Kj Kl Kn Ko
kP Kr Ks Ky Kz Ld IK IL IN IO nL Ow Ph Pj qA qD QG Ql Qm Qn qO Qt QU qV qW QX QY rA RB RC Rf Rh Rj Rm rO rQ rT rU rZ sI Ss St
Tn TO tT Tv Uc Ud Uf Ul uM Uo Up Ut Uv uY Vs wE wQ yJ Tj) Jn(aD aE Af aH aI aJ aK AL An AO aP aR As aU aV AW aY Ba Bb Bc bE
bF bI BN Bo bP bR bV bW bX bZ cA cB cG Ch cI cJ cK cN CO cP Cq cS Ct cU CV cW CX dA DC Dd dG dH dl dJ dK Du dX Ed eM eP eW Fc
Gc Gd gW Hb Hc hF Ib Ic jB Jf Kc kF Kn Ko Kp Ky Ld ml nC Oa oE Ou Pk Qg Qh Qv Qw Qx Qy Ri Rj Rt Ru Rv Ry rZ Sh Sj Sr Ss St To tV
Ua Ud Uf Ug Ul Up Ut Uu Uw Vc Vh Vj Vo Vv Wc We Wd Yh Yj Yl Zx Tm Xa) Mx(Ad aE al aJ aL An AP aQ aR aZ bC bE bF Bg bJ bN BO
bQ bU bW bX cC cE cG cJ cK cL cN Cp Ct CV Dc Dd De DG dH dI dJ dK Dl dN Ed Fa Fw Fy Gl Gp hB hC Hf hP hV Ib IC Id iH iJ Il iP iZ Je
JF Jk Jo Kn kQ Kr kS Ky Kz Ld Lw Mg Mp Mr Ms Mw My Na Nb Ng Nq nY Of Ou oV Pb Pd Pi Pj Ql Qm Qy Ra Rb Rf Rh Rj Rm rR rS
rY rZ sH Sj sO St Tr Tt TV Ua Ug Up uR Uu Uv uY Vp Vs Vu Wb wF Yj Zx Ti Th) Jr(Aj Ao aR aS AW BB bI bJ bN bO bP bU bZ cA cB Ch
cK cL cM Co cP Cq CU cW dC dD De dF Di dL Du Em Eo Eq eW Ex Fi Gh hF HI Ho Hq Hu Hv Hw Hx Ih li iJ Il In Ip Iu Jj Jq Ko Ky Lj Lp Lt
Lu Ly Lz Mc Md Mf Mg Mh Mi Mk Ml Mp Mq Ms Mv Mw My Na Nb Ng Nk Nq Ns Oe Of Oi Op Ow Oy Oz Pa Pc Pd Pf Ps Qc Ra rB Ru Rv
Rz Sr tV Tz Uk Um Uo UR uU Uw Uy Va Vc Vi vO Vp Vw Vz Wd Wh Yd YJ Zq Zx Tm Wm Yf) Lx(Ad aE Af aH AJ aL An Ao Ap aQ aR
aW Ax aY Ba bC bE bF BG bI BN BO bQ bX cA cG cJ Co CP Cq cS Ct cU CV Cw Cx cY cZ dA DB DD DE dG dH dl dJ DK DL dM Dp eC
Fb fR Gp gZ Ha hF hG iA Ib Ic iH iO iP jD Jf Kc Ke Kg Kk kN Ky Lp IX mE mF ml mT mW nC Nd nH nl nK nN oD oK oT Pi Pj Qg Ql Qm
Qv Qw Qx Qy Qz Ra Rf Ri Ss St Tn To Tv Tz Ud Uf Ul Um Uo Uu Uv Vb Wb Tl tF) Im(aE al aM An aO aQ aV aW Ax BB BC bE bl bO
bS bU bV bW bZ cA cB cC cE cF cG cK cL cN cP cS Ct cU CV cY cZ dB Dc DE dF dG dH Di Dp eC eF Ex Fb gV HB Hc hF hG Hp iH iO iP
iZ Ju kC Ke Ki Kn Ko kQ Kr kS Kx Ky Kz nK nW nY oK oN Ou Ow Pi Pj Pk Qt Qv Qz Ra rC Rf Rh Rm Ry Si Sj SrtN tT tU TV Tz Ua Ue
Uf Ug Uk Um Uo uR uU uV Vb vO Vp Vs vU Wc wE wG wQ Yi yJ Zw yE tM) Ax(aD aK Ao AS aV Bb Bc bJ bL bO bU bX cE cG cJ cL cM
cP cT Cu cW dE dF Di dK eC Ed Fb Fn Fy gW hC Hq Hr Ic IJ Ik Il IO Ip Ir Is Iu Jd Jg Jj Js Jt JV kC Ke Kg Ki Kk kP Ky Li Ma Mb Mk Ml
Mm Ms Mt MW Nc Ne Ni Nj Nk NL No Ns Nv nW Ny OF oK oN Oz Pa Pb Pd Ph Pi Pj Qb Qc Qg Ql Qm Qu Qv Qz Ra Rc Ri Rj Rm Ss St Tn
To Tv Ua Ud Uc Ug Um Uo Up Us Uv Vq Vu Wm) Lj(Aa al Aj aK aM An aR aS aU aV Bb bC bF bJ bL Bn bO bV bX cC cF cG cJ cL cN Cp
cQ cU Cv cY Dc DD DE Dg dH dK dL Dp dR eM Ex Fb fP Gl Gp gW Hb hC Hu Hv li iJ Ik In iP Iu Jk Jm Jo Kk Kn Ko kS Kz Lu Lz Mb Md
Mf Mg Mh Mi Mp Mr Ms Mu Mw Nb Nd Nf Ng Ni Nq Ns nW oE Of Oi Om Or Pa Pb Pd Pe Pf Pg Pj Pk Po Qm Qv Rh Rj Sr St Tn Uf Ur
Us Ut Vo Vp Vu Wb Wf Yj Tl Wm) aC(aD aE aH al aL aQ aU aW aY bG bH bI bJ bL bN bP bQ bS cA cH cI cJ cK cO cP cQ cV cW cY cZ

Vu(Du Hb Hu Lu Qg rB sF Uv) aK(Ij iZ nA nC nI nK nO nY) yJ(aF Cv Dl iJ iP Ri rP wE) kF(Dp jF jQ jU jV kP lK lN) Dc(Hb Nf Ni Ra Tv Uk Vc) Yd(gL hA iZ jP qV qW rA) Jg(bV cN CT cU dE fR) Wf(hA jH jU qV qW qY rA) Ow(dU eM fR lW mY nM nR) aV(Ky Lz mP nH nI nO nY) eC(dU fA gC gZ pH pI pK) sI(bC cT cW pS qH uM wE) sH(bJ cY hW jK jR Nq uM) uY(Iz jV Ly Ri Vs Vv wE) Fa(cX dJ lX Ml Qw Rf) Sj(Ao aP bR cN gL Mw) Pf(Hq Hr Lw Ms Nf Pd) mI(aQ bF Bo cY Hr jY) nI(aQ bF bN Db Gn tF) iZ(Gb Gp Hl Qm Vq Yg) jB(bN bR dJ fB Gh nU) kP(Dp My nK Qz Vv Yj) Cq(Qw Sh Uk uR Vs) Ps(As Du gP Rm Up) Rh(Rt Ry Uy Yg Yi) Wn(uL uR uT wE tM) aI(dU eQ fA fB gZ) cU(An bE Ij wE wQ) cX(dR Ic nC nY Yj) fR(dR jQ qT qV qW) nH(aQ Bo cJ Cw Op) hV(Cv Dl iA Ni Qz) jY(lY mM mW nD oQ) Ba(Iz lX Of oP) Lu(tN wB wE wQ) Mb(Jm Jo Mi Mp) Nf(Di Jm Jo Pd) Wc(jP lM qT qX) Vi(eM eP Gp Ry) Vp(Hu Ij Qm rB) Pi(Gn In Of Uk) cT(Ct dR Mq Ni) dJ(dU gZ oW pK) mS(Vq Yg Yh Yj) nK(bE bQ cY Hl) iA(rQ sF wP zH) jF(Iq LY Qz) Ew(aF cP dB) Hr(dU Jo Mp) Qu(eQ lX pI) Ld(gZ mW pI) Tk(tO vO tM) bV(An Hb Ni) eP(Fd Ky Yh) wQ(iJ Iq Jv) lM(Cw Yg Yl) lN(lY oO oQ) Bn(dW uR) Du(kS Up) Ha(kS Yj) Nq(sF vI) Ns(Ky Nl) Ue(Mq Vq) Yi(eM nW) We(qT qX) Jm(In Mu) Ri(wE tM) Qm(hB oF) Of(Ad Fb) Us(Fc Wh) aU(dU gC) bR(Dw gZ) cY(nA nY) dB(Em eW) gL(Op Vc) mE(bQ Yj) rB(Tv Vq) qV(Ql Wg) kI(Dp Ug) CvVj FdHf GphB MwHp TodU IjQw HbcN IqUo YgjP ShJk QysJ YenA TmqT YlqX UueQ aFuO bJsF cRlX dEoW eMgZ fYjV lYlK

Constrained panels with 3 analytes, where 1.0E-10 >= 'AUC p-value' > 0. Contains 43,069 panels of 37,933,414 total panels evaluated. :
Jp{Mx(aA aC aN cM Ef Eo Hc iA Ib Im It Iv Iz Jd Je Jg Jj Js Jv Lw Mb Mh Mj Mk Ms My Nf Ni Nj Nl Nm Nt Nu Nw Nx Of Og Ok ON Or Ou Ow Oy Pb Pk Qd Qt Qu Qw Ra Rf Rg Ua Ub Uc Uu Uv Vs Vv) Jd(aC aN AR Ax bL bM cD cM Cs cX Ef fP Hu Ib Ik Im Iz jD Jj kC Kq Kx Lh Li Lj Lv Lx Lz mF Mk Mq Mt Mu Mw Mz nC nH nI nJ nL Nm Oa oE Of Oh On Or Ow Pa Pk Qa Qd Qy Rg To Ub Vs Wm) Oy(aA Fp Ih Ij Im Ir Is It Iv Jg Ji Jl Jn Jq Jr Js Jt Kx Lh Li Lv Lw Lx Mh Mp Mq Mr Ms Mt Mz Ne Nh Nj Nl Nm Nn Nt Nu Nv Nw Nx Oa Ok On Or Ow Pd Pe Pg Pk Qa Qb Qd Qe Rg Ub Vs) aC(Aj aL aN AO AR AX aZ bM cD cM cN Cs Cu cX Et Hc Ih Im Is Iz Je Ji Jj Jt Jv kC Lh Li Lj Lw Ml Mt Mz nA Ni nJ NK nL Nm Nw Oa Ok Or Ow Pk Qd Qe Sf Ub Vs Vt Wm) Pk(Aj aN Ao Aw Ax Bg bL bM cD Ch cM Co Cp Cs Cw cX dJ EF fP Hc Hu Ib Ii Ik Iz Je Jj Jo Jv Kx Lh Lj Lv Mk Ml Nf Nm Oa oE Of oN Or Ow Qd Qt Rg Tn To Ua Uv Vc Vs Vt Wm) Iz(aN Ar Ax bL bM Bn bU cD cM cN Cs cX dJ Fa fP hR Ik Im Jh kC Kf Kx Li Lj Lv Mk Mq Mt Mu Mv Mz nH nI nJ nL Nm Oa OE Or Ow Qd rC rR To Ub Ur Us Wm) Jj(Fp Hc Ih Ij Ik Im Ir Is It Iv Jg Jl Jn Jr Js Jt kC Kf Kx Lh Li Lv Lw Lx Mb ml Mp Ms Mt Mz Ne Nh Nj Nl Nm Nt Nu Nv Nw Nx Ny Oa Ok Or Qa Qb Qd Qe To) Of(aA Fp Hc Ih Ij Im Ir Is It Iv Jg Ji Jl Jn Jq Jr Js Jt Kf Kx Lh Li Lv Lw Lx Mp Ms Mt Mz Ne Nh Nj Nl Nm Nt Nu Nv Nw Nx Ny Oa Og Or Ow Qa Qb Qd Qe) Hc(aN AR Ax bL bM cD cM Cs cX dJ fP Hu Ib Ik Im kC Kx Lh Li Lj Lv mF Mk Mq Mz nC Nd nH nI nJ nL Nm Oa oE Or Ow Pa Qd Rg rR To Ub Us Vs Wm) My(aA Fp Ib Ih Ij Im Is It Iv Jg Ji Jl Jn Jq Jr Js Jt Lh Li Lx Mf Mi Mt Mu Mz Nh Nm Nt Nu Nv Nw Nx Ny Oa Ok On Pe Qa Qb Qd Qe Qy Rg Ub Vs) Og(aA Fp Ih Ij Ik Im Ir Is It Iv Jg Jl Jn Jq Jr Js Jt kC Lh Li Lw Lx Mb Mh Mp Ms Mt Mz Ne Nh Nj Nl Nm Nt Nu Nv Nw Nx Ny Ok Qa Qb Qd Qe) Kx(aN Ao Aw Bg bL bQ cD cE Ch cM Co Cw cX dJ EF fP Fr Hu Ib Ik Je Jo kC Lh Lv Mf Mg Mk Mm mZ Nd Nm Nq oE oN Ow Qt Qw Uv) Ib(aN Ao Ar Ax bL Ch cM Cs Ed fP Hu Ik Im kC kI Li Lj Lv Lz mF Mk Mq Mt Mz Nm No Oa Oe Or Pi Qa Qd Ra Rg Ub Wm) Ms(aA Fp Ih Im Ir Is It Iv Jg Jl Jn Jq Jr Js Jt Lw Mp Mt Mz Ne Nh Ni Nl Nm Nt Nu Nw Nx Ok On Qa Qb Qd Qe) Ow(aN Ao Ax bM Ch cM Cs eF fP Hu Ik Im kC kI Lj Lv mF Mk mM Mz nA nL Oa oE Oh Or Qe Ra Sj Ub Vc) Vs(aN Ax Cs Im Ir Is Je Ji Kf Kr Li Lj Lv Mk Mq Mt Mz nJ Oa Oh Qa Qd Qe Tz Um Vu Wm) aA(Fp Hr Ih It Iv Jg Jn Lv Mb Mh Mt Mz Ne Nf Nj Nl Nt Nu Nw Nx Ok On Qa Qb Qd Qe) Ub(aN AO bL Cs eF fP Hu Ik Ir Je Li Lj Lv Lz Mk Mt Mz Oa Oh oN Ou Qd Qe Qw) Im(aN Ez Fp iA Il Iv Je Lw Mb Ne Nf Ng Ni Nj Nl Nt Nu Nx Ok Pb Qd Qt Qw Ua Uc) mF(cM Ef gW Hp It JE jF jM jQ jR lL Qv Qw Rb rC rZ Si To Tr Ug Um Ur Uw) Mb(eW Is It Iv Jg Ji Jl Jn Js Jt Mt Mz Nl Nm Nu Nv Nw Ok Pb Qa Qb Qd Qe) Nj(Fp Ih Ik Is Iv Ji Jl Jt Lw Mp Mr Mz Ni Nk Nm Nt Nu Nw Ok On Qa Qd Qe) Oa(aH aN Ao Aw bL bM bZ cD Ch cM Co Ef fP Hu iA Ik Lv Mj Mk Nm oN Rf To) Je(aN Ax bL bM cD cM Cs fP Ik kC Li Lv Mq Mz nC nH nJ nL Nm Qd To Wm) Or(aH aN Ao Aw Ax bL bM cD cM Cs cX Hu Ik Lh Lj Lv Mk Nm Nq Ou To) Nf(Fp Id Is It Jq Jr Js Kq Lh Li Lx Mq Mz Nw Ok Qa Qb Qd Qe Vt) kC(bR cM Dp eC Ef hC Hf iB It jF lL qU Qw Rb Tr Uk Ur Uu Wm Tj) nJ(bE Dp Ef Hf Kl lL Qx Qz Rb Ri Ry Sf To Uk Vb Vi Vj Yk Tj) Fp(Hr Is It Iv Jg Jt Lw Mk Mp Nl Nm Nu Nw Nx Ok On Pb Qd) Mz(Hr Hx Ii Iv Jg Jr Mw Ne Nh Nl Nu Nx Ny Pb Qw Qz Rf Uv) oE(cM cX Gb Gd Hp Kn Qx Rg Ry Sf Si To Uw Vi Vj Yg Yi Yk) Qd(Eo Hw Il Iv Lw Mj Ne Nl Nq Nt Nu Nx Qt Qw Ua Uc Uv) nL(Ao bR cX Dp lL Qx Qz Rb Rv Ry To Um Ur Vi Vj Yk Tj) Nm(Is Ji Jl Jn Jr Kf Ne Ng Nh Nl Nx Pj Qb Qe Rg Vt) nI(Ao Gd Hp Kk Qx Qz Ry Um Uw Ux Vb Vi Vj Yg Yi Ye) Ua(aN bL fP Ir Kf Li Lj Lv Mk Oe Qa Qe Tz Vu Wm) Si(bL bM bU eF eM fP iA mE mM mZ nA Nd nK oK Ut) mZ(Gb Gd Hl Hp Qy Ug Um Uw Ux Vb Vw Yg Yi Ye) Mk(Fa Iv Kl Lx ml Mt nK Nt Qa Qu Rg To Vt) Nl(Is It Iv Jl Jn Jt Lw Ni Nu Nx Ok Qa Qe) nA(Fy Gd Hp Kr Ks Qy Rx Ug Ur Uw Vb Vw Ye) nH(Dp Eq Hf lL Qx Qy Qz Ry To Um Vi Vj Tj) kI(cM Ef jY Kk qU Qv Rb To Tr Ug Um Ur Tj) Eo(cF dB Jn Li Lj Mj Nr Nw Ny Po Qb Qc) Ji(aN Hx Ii Lh Ml Mp Mv Mw Nt Ny Om Uv) nK(bE cX Gb Gd It jF lL Qy rZ Uw Vb Vj) Nu(Is It Iv Lw Nw Nx Ok On Pb Qa Qe) Rg(aH aN Ao bL cM eF fP Hu Lv oN Um) Cs(bL cD cM iA Qw Ra Rf To Uu Vt) Sf(bL bM bR cK fP Gc iA mM Nd pI) Qa(Hw Il Jg Jk Ni Nx Qw Uc Uu Uv) Qe(Il Is Iv Lw Nh Ni Nx Ok Uc Uu) Lx(Hx Mh Mv Mw Nh Ni Ny Pb Po) Kf(Aj Aw Bg Ch Ef eM eP Ik Uu) nO(bU cF Dp Fy Ks Ug Um Vh Tj) nC(bR lL Qx Qz Ry To Ur Vi Vj) Ne(eO Ih Is Jg Jl Jn Jt Nx) Hp(bM bU Ed Hv iZ mE mM Nd) It(Lw Mp Mt Ni Nw Nx Ok On) Yg(Bn bU De Hv iJ mM mY Nd) Jv(aN Ax bL eF fP Lj Lv rR) eP(Fa iJ Ki oH oK Ru Tn We) kP(cX Dp Hb Ju Kc kN Yi Yk) Nt(Ii Ik In Iv Mw Ng Ok) Lh(Hr Hx Ii Mh Mw Pb Uv) Lj(iA Ju Qg Qw Qz Ra Rf) On(Jh Mh Mp Mv Mw Nb Ni) Vt(aN Ax bL cM Hu Lv Uv) fP(Ef Kn Ra To Vi Yk Wm) Uu(Ar Ax bL Lv Oe Wm) Vb(bU Gc iJ Jn Nd Pi) eM(Hb Tn Wh Zq Tl Xa) mM(Gb Ry Sh Uw Vi Yi) Ef(aN Kq Ug Vu Wm) Nh(Ih Jl Jn Jt Nw) Jg(Jh Mh Mw Ng Qb) Li(Ez Ni Qt Qu Qw) Vc(aO Fw hC Kk Ry) Vj(kG ml mT nN oT) Pb(Ih Jl Nv Nx Ok) Pe(Hr iA Ii oN Uv) eF(Fy Ju Ra To Um) eO(aO aW cS dK Mv) lM(Id Kn Sr Yk Ye) Th(tO tR wJ yJ) Fa(Ao bL Hu Lv) Lw(Is Iv Jn Nw) Nd(Rx Ry Sh Uw) Ax(Ra Rh Uv) Wm(Qt Qw Rh) Lv(kR Qb Qu) Hu(Ed Mu Um) Ir(iA Uc Uv) Is(Iv Mt Nw) Yi(iJ mS mY) Nv(Mv Mw Ng) Ok(Hr Ii Iv) Uw(Fw mE mY) bL(Ar Id Kc) dX(eC Jf Qm) eQ(Id Lt Tl) Ao(jD kR) Ew(aN aY) Gc(kS Uh) Gd(iJ mE) Gz(bU vT) Mq(Qw Uv) Ni(Jn Qb) To(Ik jB) Vz(gW rA) Sj(Ik Ma) Wc(iC jQ) Wh(jL qT) Jl(Hr Mw) Jt(Ii Ng) Kq(Dk Nq) Ry(hC mY) Nx(Iv Mt) Oe(Uc Ur) Um(bM nD) Vi(hC iZ) cM(Kl kR) cX(lX ml) kK(lK qU) ArRf DukQ TivB FbjB HaoN MpJn InPi YkiA ShkS RbkG ZwqT ZxjH TlbU JugC KeoV KkoP LtlW RhOh UgmI UrmU dRgV sJpF kNlK kOlL} Th{yJ(aA AD Af aG aH aM An Ar AS BB Bn cE cG cH cM Cp Cq CT CV cW Cx cZ dA Dc dD De dF Di dJ Dl dM eC Ed Et Fa Fb Fn Fw Gl hC hG HV Hw Ib Id Ih Ii Ik In Iu Iv Jd jE jF Jg JH jK jM Jn JO jP Jq Jr Js Jy Kc Kg Kj Ko Kp kQ Kr Kx Ky Kz Ld Li lN Lw Mb Md Me Mf Mi Mj Ml Mn Mq Mr Mt Mu Mv Mw Mx Na Nb Nf Nm Nn Nt Nv Nw Nx Ny oE OF Ok Om ON Pb Pf Ph Pk pY Qc Qd Qe Qh Ql Qn Qt qV QX qZ Ra Rb Rj Rm rN rO rP rR rZ sK Sr Tn TT tU Tv Tz Ub Ud Uf UG UM uN Uo Up Us Ut uU UV uX uY vA vH vI Vp Vs wB wF wH wP wQ yD zG zI tL Tj) tO(Ad Af aM AS Ax BA bB bE bJ Bn bV cE Cp CQ Cs CT CV CW Cx cZ Dc DD De dF Dl Fa Fn Fw Fy Gl HA hL hW IB IC Im Jd JE jF jH jI Jj Kd Ke Kf Kg Kj Kk Ko Kp KQ Kr Kx Ld lO Mn Ms Mz Nw Oa oE Oh oN Or Ou Ow Pe Pi Pk qI Ql QX qZ Ri rP rR rS rV rZ tS UN Up uT uU uW Vt Vv wF wG wP zI tL Tj) wJ(AF AS bA Bc Bn cG CQ Ct Cu cW Cx dD De dF Fn Fy Ha hO Hv hW Ib Id Ii Im Iq Ir Is Jl Jj jO jP Jt Kd Ke Kg Kn Kp kQ Kx Ld lO Lw Lx Mb Md Mi Ml Mq Mr Mt Mv Mx Nn Nr Nv Nw OF Oh Om On Ow Pa Pd Pe Pf Pi Pk Po Qb Qh qT Qv Qx qZ rS

In iZ Jd Ji Jj Jn Ke kF kG kK kN kQ Lh Li Lj lY mM nB Nf Nu Nv NW Oa Og oK On oP Ou Ow Pf Po Qx Qz Rj Sr Tz Ue Ug Uk Um Uo Ur Us) jF(aA aD aE aF aG aR aS aW aZ bF bH bL bP bQ bS bU cE cF cG cJ cL cR cT cV cW dA dE dG dM Dp In It Jl Jj Jt kK lL lN Lx Ma Mn Mp No Nv Nw Oh On Qc qT qU rZ) qW(aJ aP Ar aW Ax aZ bA bL Bo bQ cJ cR Cs cT CW cX dE dF dG dI dM Fa GL hC Id iO Jj Kn Kx Ld Mr No Oa Or Pj qU Qz Rj rZ Sr St Tv Tz Ue Uk Un Uo) lL(aQ aS aV aW aZ Bc bH bJ Bo bQ bS cA cI cJ cR cS cV cY dE dI Ez Fa Gl Hv iC In It Jm Kd kF Ki Ko kQ Lh Li lK No Nw Og Pj Pz Ql Qt Rb Rj Ue) jR(aJ aP Ar Ax Bc cR Cs Cu CX dF dG dM Fa GL Gp hC Id iP Jj Kd Kk Kn Kx Ld Oa Ow pF Pj Ql Qn qU Qz Rj Sr To Tv Ua Ue Ug Uh Uk Un) jE(aJ Ao Ap Ar As aW aZ bA bF Bo bQ cE cF Cs cT cV Cw dF dG dM Hb hG iH Ji Js Ke Ky Lh Lx Ma No Nv Nw oE oF ON Or Ou Ow Pj Uo) cY(Ar Ax bN Fa Fw Fy Gl iB Im Ir Is Ji Jn jY Kd Kn Kq Kx Ld Lh Li Lj Mx No Nr Oa Oh Or Pe Qa Qd Qe Ql qU rZ Sr St Tz Vq Vu) qV(Ad AJ aM aW aZ bA Bg Bo bQ bS bX cJ cK Cp cR CT cU cV Dc De dF dI dM Ef Ez hC iH iO lZ Jj kQ Ky Nw Ph Rj Tz Uo) jU(aJ Ar aS aV aW bA BC Bo bS cA cV cX dE dF dG dI dL Fa Fn hC hG Kp kQ Qv Qw Qz Rj Tt Ub Ue Un Uo Up Ur Ut) cM(Ax bQ cF cG Cs dF Ex Gl Gn Gp Hl Hp Ke Ko Kx Lh Li Lx nN No Nq Qe Qm Rb Rx Sj Ub Uf Uh Um Vb Vz Yj Ye Xa) aK(Ax Fa Gl Gp hC Hq iB iH Im jI jY Kd Ko Kq Kx Ld Li Mh No Oa Or Pe Pj Qe qU Rb rZ Sr St Uf Vq Vu) qY(Aj AN Ar bH bN Bo cJ Cs Ct DL Ed Ef Ez HC Id Ks Oa qU Qz Rb Rj Ub Ue Ug Uk Ur) qU(aQ aU aV bA cH cJ Cs cV Cw Hb Id Jv Ko kP KQ Ld nN Nw oH Ou Ql Qn Qt Sr St Tn) Ug(bB Cw Fy Gc Hq Im Ir jD Ji Jn Kf Kg Kq Kx Lh nI No Nr Nw Oh Ok On Pz Tn Uf) aV(Fa Fw Fy Gl Im jY Kc Kf Kn Kq Kx Ld Lh No Pj Qm Rm rZ St Tz Uf Vq Vu) Vb(Ba bI Cw Gc iJ Jk Kf Ko Ld Li Mg Nq Nv Nx Op Ow Qz Rz Vu Wd Yg Xa) rA(aJ Ar Ax bA bL Bo cR Cs cT cX dI gL Id iH Kd Kn Kp Kx Ld Oa Ue) iB(aC aQ aS aU bJ bS cA cF cP cV Dp It Jj Jm My Og Qv Qy Ur) Um(bB bN Cw eC Et Im Ir Ji jV kP Kq Kx Lh nI nO Nw Ok On) eD(Ar Ax Ba Bc bS Cs Hb Kk kQ Ld Ou Ql Qn Qy Qz Rj Un Ur) Ub(Ax bI Cs eC Fa Ji Jn jV jY Lh Li Lj nI Nw Oh Qd) Jj(bB Fy hV iC jM Kf Kq Ks Kx lN On Ph Qu Tn Tz Uf) Ur(bB Cq Cu Cw Gl Ji Kf Lh Li Lx Nn Nv Oh On Tn Ut) aQ(Ax Fw iC jI jK jY Kd Ld Li lN Oa Qe Qz Vq Vt Yk) lX(Fa Fw Fy Gl Ke Kq Kx Ld Oa Ql rZ Tn Tv Tz Uf Vu) aU(Fa Gl jY Kd Ko Kq Kx Ld Oa Pj Qe Ql Qz Vq Vu) eC(Gc Gl Hl Ke Ld Pj Qv Qz Rv Ry Sr Tn Tz Uf Uh) jV(aS aW bQ dB dE iH Kp oE oH Ri Ue Uk Up Vv) Qv(bI bR Im Ir jD Ji Lh Lv Mx Ns Nw Oh On) hV(aF bA bS cG cK cX dC Hv Jd Jt Kq Nw Us) nI(Dp Ex Fa Fw Gz Ha Kf Kq Kx Oa Rb Tz) rZ(aS cI Hb Ih Jm Ke oE Og Ow Qa Qb) Dp(bA bB Fy Gl hR hW iC Li lY rC) Zw(Jl Jn Js Lh Li Lx Oh Ok Tz Yi) rY(aJ bA bG bS cP dC dD dE dI dM) Og(bB Gp Ke Kf lN Qu Tn Uf Tl) kS(Fw Fy Ke Kq Kx Ld Tn Tz Uf) Rb(bI bR bU dD Lh Li Nw On) cF(Fa iC Kf Kq Lh Or Ql Rg) jD(Hb hG Jd oE oN Ou Ow Up) jY(bJ cT cV dR Hb In Nw oH) lK(aJ Cs cT cV Ld Nv Qz Uo) We(Hq Mv Nv Nx Tn Yg Xa) Li(aC iH Qw Qz Rv Ry Yi) hX(Al cJ Cu cV cX iZ Ko) Lh(aC aL Qw Qx Qz Rx) hW(aR aS bJ Bo cI Jd) jL(bA cT cV Gp Pj To) bB(Gp Oy Qg Tn Tl) dR(Fw Kp Kx Ld Tn) hR(aJ bG Hf iZ Ks) jM(bA cT Hv My Uh) aC(Ba Cu Gl Uf) iC(aS cP oH Ri) jO(dF Qn To Uh) jT(dL oH Ue Uk) oV(Fw Gp Qu To) Gc(Gd Hv lY) Xa(bN Rh Ye) Rf(Kx No Oh) Ow(Mk Oy Qx) aL(Fa Kc Kx) rC(Aj Al Rm) jH(aZ Nw Pj) qX(Ar cT iH) kP(Fy Tz Uf) lM(bF bQ cE) lN(Hw In oH) Cw(Rg Uu) Tl(Et Gp) WmjI GlnL NnRy MvYe HlbR YiRh YjbL SiJn SrdD QzOn KphC RvbN RmOh NwrX NxVa UfiH UhjP bQbU} oD{cM(aM aR Aw AX bA bB bC BO bQ bZ cG Cp cR Cs cT cU dD dF dK dU Em fA Fd Fp Fw gP Hb hC Hl Hp Ih Im Is Iv jB Jh Ju Ki Kp Ks Ld Li Lj Lu Lv Lx Ma Mb Me Mh mI Ml mP Mq Ms Mt mY NB nC Nd Nf nH nK nL NN NO Nr NT Nu oF oH oN Or oW Oz Pb Pe Pf Po Qa Qc Qe Qm Qv Qw Rb Ri Ru Rx Sf Tr Ub Ug Un Up Ur Us Ut Va Vh Vj Vz Wc Tl Xa) Tl(Ao Ap aX bC bE bG bZ cE cG Ch cL CO cR cS Cu Cw cZ Dd De Di dK Ef Ez Fw Gc gL Hq Hu Hv IH iJ Im iO Iu Iv Iz jB Jd Jh Ji Jk Jo Jy Kc Kd Ke kF KG Kq Kz Ld Li Ma mE Mg Ml MP Mq MT Mu Mw My Na Ng nH nK nL NN Nq nU Nv oH Om Ou oV OW Pd Pe Pf Ph Pi Ps Qa Qd Qt Qu Qy Qz Tn Ua Uf Vj Vu Wd Wh Xa) Du(aK Ao aU aW aX bB bC bE bJ bR bW bZ cA cE cG Ch cL Co cS Cu cZ Dd De Ef Ez Fi Fw Gc gL Gp Hq Hu Hv Im iO Iu Iv Iz Jd Jh Jk Kc Kd KG Kq kS Ld Ma mE Mg Ml MP Mq MT Mu Mv Mw My Na nC Ng nH nJ nK NN Nq Nv Om Ou oV OW Pd Pe Ph Pi Qd Qt Qu Qy Qz Rz Tn Ua Uf Vj Vu Wd) Ut(Al Bb cA cF Co Cu Db Ef Eq Gb Hf Hv Ib Ih Ii Ij Io Is Jh Jj Jn Jr Js Ju Jv Kn Ma Mf Mj Mm Ms Mx Mz Na Ne Nh Nl Nl Nn nR Nv Ny Oi Pe Pf Ph Pi Qh Qw Qz Rc Rf Rm To Ub Uk Up Uu Uv Uw Ux Vb Vh Vo Vp Vs Vv We Wh) Gc(Ad aH aM BG bN Ch cL Dg Dl Eq Gd hC Io Jd Jg Jr Jt Kl kS Lj Mh mM Ms Mx nA NB Nh Nl Op Pg Qu Sf To Uc Uh Uu Vh Wc) Sf(aF Ao aR aS bB bI bN cD Co Dd Et Fd Fy Hq Hv Ij Im Ip Iu Iv Jh Ji Jk Jo Kg kP Kq Ks Lh Lu Mn Mw Na Ow Ph Pj Qa Tn Vu) Rz(aG aH aM aO Bg bL bN Ch Dg Dl Eq Gd Jd Jg kF Kl kS Lj mM Ms Mx nA NB Nh Nl nR Op Pd Pe Pf Pg Qu To Uc Uo Us Uu Vb) Vb(Ap bC cG Co cR Cu cZ Ez Fy Im iO Iz Jh Ji Jo Kq Ld Ma Mg mI mP Mv Na Ng nK Nq Nv Om OW Pe Ph Qt Qz Tn Ua Vw Wd) Xa(aM aO aW bB bH bJ bM bN bX cI dM eC Eq Hv iP Jd Jn kF lW Mx nA nK Nl nO nT Nx nY Oi Pi Qu Ry Tz Ua Uc Uo Us Vi) Ld(aM An aO aW bC bF bJ bN bP bX bZ cA cD cI cU dM Hu kF Mj mM Mt Mz Nh nI Nk nR Ny Og Pe Rf To Vi Vj Vs) Eq(cG Co Cu eC hC Iz Jh kG Kq Li Mg mT Mw Mx Ng NN Nq Om oV OW Ph Qd Qz Tn Ua Uf) cR(bC bH bR bU cI eC Hp In Mb Nd Ne Nh nI nK Nl Ny Oa Og oO Or Qz Rf Ry Sj Uw Vj tF) bB(Aa aH aR bC bW cD Gd Kc Kk mH Ni Ns Ny Og Op Qz Sh Uy Yd Yl) Wd(aG aM aO bM bN hC Jd Kx Lj Ms Mx nA Nb Nh Nl nR Qu To Uo) bJ(bO Gh Ju Kx Nd Qg Qh Qv Rf Rm Ub Uk Up Ur Vo Vp Vv Yl Tj) bU(aD aM dL Ih Iv kE kP kQ Me My Nd Nj nN nO oK oW Oz Po Qc) Wh(aO bG bN bX cK cL De Ji kG Kl kP Lt mE mM nA Nh To Uo) Kq(Gd Kl Mm Ms Nh nI Nn nR Nv Ny Op Ps Rf Uu Vi Vj Vw) Fy(Hl iO Ju nH Op Qh Rf Rt Rx Ry Si Uw Vh Yd Zw) bC(bO Fd hC Kl kP Kx Lt Lu Nd Nf Nj Qu Ub Wc) Fw(cA Jj Jn Jr Js Mj Mz Nh Nl Vi Vj) Iz(Bb Bg cD Gd Kl nR Ny Op Uc Ux Wc) Lt(bE Db dU Ih Mr Nc Ni Nk Nl Nq Us) Gn(Fd Hw In Iv Js Ks Mw On Pi Vu) Kx(An cZ eQ gL iO Kc Ky nI Ny Rf) We(Ao Hq Na Ng Ph Pi Qz Tn Ua) Vi(cZ Im Iv Mv Mw Nn Nq Pi Qa) Vj(Cu Im Mx nA Nh Nn Nq Ow To) Kc(aM bM hC Mv nH nK nL nR) Op(Ao Cu Ji mI Mv Na nK Pe) iO(Ed Ef Fd Fn Jd Kl To Uo) Wf(dU Ih Ip Nc Ni Nk Nl) aW(Hf Ju Pi Ra Uk Vp Yd) Ao(Si Ux Va Vh Vw Wc) Li(Nn Ny Og Ry Sj Uw) nL(Id Kk Lp Qw Uy Vz) Fi(bN Mw Mx Nl nR) Ho(bN hC Mx Nl nR) Hp(Iv Jk Mw Pi Qa) Si(Ji Mw Na nK Pj) Wc(De dU oV Qz) Pi(cA Nh Ry Zw) cD(Ju Kd Ow Qu) eC(Kk Nd Ry Tt) nI(Fa Fd Gl Pk) Lx(Ny Og Rf) Yd(Gl Hv Ji) Vz(mI nK Pe) Ye(Dd Qz Vu) bN(Fc Uw Ux) bX(Ju Kn Ow) mT(Jd Kn Vv) Yf(Iv Qa) Gh(Jf oH) Ms(nK Tn) Ps(Im mM) Rf(No Po) nH(Kk Lp) iJ(aG Kl) CwGd DrcL FcnA FdJu NsnK MeHf MvUy TnnR IoKo QaRy QuPe LhNy RvbI YlaR} eP{Wh(Al aM An Ao aP Ar Ax aZ bB bM bO cG cJ cO Cq Cs CU Dd dF Dk Du Ed Et Ex Fa Fb Fd Fr Fw Fy Gl Ha Hq Hw Ib Id Ih Ii Ij Il Im In Ip Iq Ir Iv Jh Jk Jl Jn Jq Kd Ke Kn Kp Kr Ks Ky Li Lv Lx Lz Me Mj Mm Mr Mv Mw Mx Na No Nq Nr Nt Nu Nv Nw Ny Oh Ok Om On Ow Pe Pf Pg Pj Po Ps Qa Qd Qh Rm Si Sr Tz Uf Uh Up Ut Uw Uy Vi Vq Vu Vv Wb Yi Zq Tm) Ho(aM aN bB cG Co Cs CU Dc dK Du Ed Et Ex Fp Fr Fy Gd Hc Hf Hr Hx Ib Ij Im Iq Is Iv Iz Jd Jh Jj Jl Jq Js Jv Jy Ki Kk Kn Kq Ks Lh Lv Lx Lz Mf Mj Ml Mm Mp Mr Mw Mx Na Nb Nd Ne Ni Nl Nq Nt Nu Nv Nw Ny Om On Op Pk Ps Pz Qg Qm Qt Qz To Tv Tz Ue Uf Up Ur Ut Uw Vi Vz We Yg Yh Yi Tm Xa) Wd(Al aM aP Ax bB bM bO cG cJ cO Cq Cs cU dD De dF dG Dk dL Du Ed Et Ex Fa Fb Fd Fp Fr Fw Fy Hb Hx Ih Ip Iq Iv Ji Jj Jk Jl Ke Kp Kq Kx Li Lx Mf Mj Mp Mr Mt Mx Ni Nn No Nq Nr Nu Nw Ok Ow Po Qa Qb Qg Qh Rg Uf Uh Un Uw Vb Vq Vu Yi Ye Tm) Xa(aA Af aM aR aW aX bJ bM Bn cG cJ cO Cp cU cV Cx De Ed Fc Fw Fy Hb Hw Hx Id Ij Il Im Iq Iv Jd Ji Jn Js Jy Kc Ke Kq Lh Li Lz Mi Mp Mq Mr Ms Mu Mv Mw Na Nb Ni Nt Of Om Or Ou Pe Pj Po Ps Qa Qd Qe Qg Qm Qy Si Sr Tr Uf Ur Ut Vq Vt) Yg(Al aM aP Ar Ax aY bB cG cJ dD dF dL Du Ed Fr Fw Fy Gd Iq Iv Jl Js Kj Lh Li Lx Mj Mp Mt Mx Ni Nk Nn Nq Nu Ok Ou Ow Po Qa Rg Tt Ur Uy Vq Vt Vz Yi Yl) Yi(Ao aX bC bF Bg bQ Ch Co cV eM Fb Hc Hq Hu Ib Iz Jd Jk Kq Kz Ld Lh Me Mj Mv My Na Nb Nf Ng Nq Nt Nv Om On Oz Pa Pb Pc Ph Qa Qn Ry Ua Up Ut Vp Vs) Yh(Al aQ aV Ax bB cG cJ cN dD Du Ed Fa Fb Fr Iq Iv Jd Ji Js Kr Li Lx Ml Mr Mt Mx Ni Nq Nu Of Ou Po Qa Qg Qh Qv Rg Uf Uh Ur Va Vq Vt Vv) Kx(aV Aw cD cU Cw Db Fc Hf iH In iP Jo Jr Kc Kk Kp kR Kz Lt Me Mu Nb Nw Nx OF Or Pa

Figure 31 Continued

Pb Pc Qy Rb Tr Tv Ur Uy Vt) Ry(Ao Ar cG Co CU Ex Fr Fw Ij Jd Jk Js Kq Lh Li Lx Mk Mp Nn Nq Nr Nt Nw Oh Om Ou Ow Pj Tn Uf Ut)
Du(Ao Ex Hu Iz Jd Jk Ld Mn Mt My Na Nt Nv Nw Om On Uf Un Ut Vi) Uw(Ar Bg Cp De Ed Ex Fb Hu Jh Jk Ld Mj Mu Mw My Nq Qz Ua
Vs Vu) Wb(Cs Ed Ex Jd Js Ks Ld Mw Mx Nn Nq Oh Om On Qa Qz Ut Vu) Kc(Ar bV cG Co dD dF Ex Fr hC Lh Mn Mt Nv Nw Oe Ok Om
Tn) Vz(Co Cp Cu Fw Iz Jk Js Ke Lh Lx Nd No Nt Nw On Uf Ut) Zx(Ar cG dD De dF Ex Fb Fr Gl Nn Nq Nv Qv Sj Tn Uf) Rt(Ao Ar Ed Fw Im
Iv Li Mq Mr Mw Nn Nq Nu Po Qa Un) We(Ar bB Ed Fa Fb Fr Jk Js Li Lx Mp Mt Qa Tn Vt) Vb(Ao Bg Co Cu Ih Iz Jd Jk My Ng Om Qz Tn Ua
Vs) Uy(Ao Bg Co Ef Iz Ld Lh Mv Nn Nt Nw Om On Tn Ut) Or(Ad Ao Dg Eq Et Ir Jg Ji Jt Kf Ko Nw On) Ps(aO Ar De dF Ed eF Gd Js Lh Mt
Mx Ok) Vi(aM Ar bB cJ De Ed Li Nu Qg Sf Vq Yl) Nw(Fc hG Kk Lt Qv Rz Tr Tv Ur Uv Ux) Mt(Gh Rx Sf Si Sj Vh Yk Zq Tm Tl) Tl(cG Co
Cu Fr Fw Jd Jn Nq Om) Ex(aN Fc Fi kS Ld Rz Sf Vw) Yk(Ar Ed Fr Iv Mr Ni Qa Vq) Lh(iJ Kk Lt Sf Ux Vw Wc Wf) Yl(Cu Fw Iz Na Nt On Uf
Ut) Un(bL Gh Ow Pf Ra Rx Va Wc) Fc(Co Cq Jq Nv Ny Ok Tn) Fd(Co Cu Fw Iz Kq Om Uf) dW(aD bP Lv Lx Mb Nc No) hC(bB cF De Dg
eM Ld) Tn(In Kk Tv Wf Ye) Sh(Ao Fw Ke Om Rf) Kq(bL In Pf Qv Vw) Ow(bQ cG cO dH tF) gW(aN Im It Mr Qd) Ok(Fi hB Rz Si) Ao(Kk
oF Yj) Co(Lt Vj Wf) Gh(Jd Nq Om) Mx(Rz Vj Vw) Nb(Ko Ub Uh) Qe(eW Hl Rx) Wc(Ar Mw Qb) Ke(Mm Nx Sf) Va(Ks Nt Om) eO(Ij Jj Mb)
eM(hB iJ pF) Fb(Op Vh) Fi(Jl Mz) Fw(aN Wg) Fy(Yj Zq) Gb(Fa Lj) Ir(Rx Uh) Zw(bO Uf) Kk(Na Ut) Ld(bB Jj) Rf(Sf Vc) eW(Lv Qb) oF(De
Mv) ArVw CuHl EoLx PoUh EwaN FriJ NqOp MnSi MwSj TvUt IqeC JdYe JiVv StVh WfLi JkTm RxLj VccG VtbL} Vb{nK(aE Aj An Ao Ba Bg bl cE cG Ch cM Co Cq cR Ct Cu Cv Dc Dk Ef Eq Ez Hc Hq Hu Hw Ib iO Iq Is It Iz Jd Jg Jh Jk Jl Jm Jq Kf Ko Kq Ks Lh lY MH mT Mu Mv Mw My Nd nI Nq Nv Nx Of Ok Om On Op Ou Qt Qy Qz Rc Rj Rz Ss Tn Tv Tz Ua Uc Ue Us Ux Va Vo Vs Vu Wb Wd Wf Wh Yg Tl Xa Tj) dU(Aj An Ao bI bL cH cI cK Co Cq Ct Cu Dd Ef Ez Fw Hc Hu Hw Hx Id Ij Il Im Is It Jd Jf Jg Jj Jk Jo Js Jt Kf Kg Kj Lh Lt Mg Mw nA Ng Nn Nv Nx Ok Om On Ow Pg Ph Qc Qh Qt Qu Rt Tv Ua Uf Vq Wd We Wh Xa) Qy(As Ax Cq Cs Cu Dc De Du Em Ex Fd Fy Gc Ha Hv Ib Id Ir Is Iv Ji Jn Jq Jr Js Jt Kd Ke Kf Kn Kp Kq Kr Lh Li Mx Mz Nb nO Ny Oa On Or Pi Pk Qa Qe Rj Rt Tv Uc Us Ut Vi Vv Tl Xa) Ut(aE aM aO bU cB CH cM Cs Dc Dd De eM Fw Gc gL Ho Hv iJ jB Jl Jn Jr Jt kF kK lY mM mS mT mU Mz Nb ND nl Pb Pz Qh Rj Up Ur Us Uz Vi Vt Wb) Gc(aM aN BA cF cN Cu dF dM eF eQ Fb Fw Fy gL hG Hv Is iZ Jh Jk Jn Jr Kp Lh mS Mt Nb Nd On Pi Pk Pz Qa Qh Qt Ry Ss Tn Tz Us Vu) jB(Aj An Ao bI Co Cq Dc Ex Ez Fy Gl Hq Hu Hw Hx Il Iz Jk Kf Kg Kq Lh Na Ng nO Nv Nx Of Ok Om On Ph Rj Tv Uk Up Us Vu) gV(aH aI AL bB bM bO bR bV cB cE cF cH cK dD dI Et Ih Ik Ir Mf Mn Mt Nh Nu Pd Pf Qc Qt Qw Rh Rm Sr Ub Uf Vs) mE(Ba bI bR cA cI Cu Gl Hc It Jg Jk Kf Ks Lh Li Mg Mh nI Nm Nq Nv Nx Of On Op Qz Rc Rj Ss Vu Wd Wh Yg Xa) gL(Ad bR bU Cu Cv Cw Dc De Dk Ij Ji Jl Jq Jt Ke Kf Kp Kq Lh Lx Ng NO Nx Ok On Ou Pi Pz Qe Uw Vq Zq) nI(cG Ch Dg Dk Ef eM Fy Gl Iz Ji Jo Jq Js Kg Kr Lh Mg Mn Ng Nx Ok Op Ou Qc Qd Qe Tz Uf Us Uw Vv Vw Zq) mS(Ad Ao bI bU Dc Dg Fy Hq Ih Ii Ij Il Im Iq Is It Jo Js Jt Kg Lh Of Ok On Ps Qc St Tz Uf Vq) Cu(aD aO bL bM bQ cW Dc De Dk fA Hf Hv lZ Jg Jk Kz Lv mM Nd oP Pz Qh Qm Rh Ry Us Tl) eQ(Ao cG Fy Hc Jo Jq Js Kf Kg Kq Ld Lh Me Mg Mn Na Ng Nv Oh Ok Om On Pz Tn Tt Tz Ua) nO(aE bU Cq Hc Hu Im iO Is Jd Jh Jk Jl Mu Mv Mw Nd Nk Nq Nv Om pI Qw Tz Ua Wd Xa) mI(An Ba bI cM Cq Hq Hu Jd Jk Kf Ko Mh Mu My Nd Nq Nx Of Op Ou Qz Rc Ss Ua Yg) Pz(aA bA De dM Du Ex Fy hC Hv Id iJ iZ Ji Jn Jr kG mM Nv On Or) iJ(Dk dM Fy Im iZ Jk Kf Kq Lh lX nA Ng Nv On Vw Zq) Nd(Fy Ho Iz Jk Ke Kf Kp Kq On Pi Qh Tn Vz Xa) nA(cE iO Iz Mg Nx Op Ou oV Uw Ux Vo Wb Wd Wf) Jr(Dc De Iz Jg Jk Jt Kc Nb Ps Qh Qm Ss Vq) oV(Co Cq Fw Fy Il Jo Me Ok Qu Rc Uf Uk Xa) mT(aE Cq Hq Il Ip Mx Op Rj To Tv Vo Vv) nL(An Cv Hq Hw Il Iq Jq Ng Nx Op Ux Wf) kG(aS Cq Cv Hw Ih Ip Iq Rj Ue Us Ux Wf) gZ(bI Fw Hq Hw Il iO Iz Me Mg Ng) mM(Dg Ez Ji Kl Ng Ok On Uf Vv Zq) Ba(Em Hv Ir Jq lW mH Up Us Vt) eM(Co Jk My Ng Om Ua Vs Wd Xa) nR(Ao cG Co Dg Fy Kq Ok Tn Uf) fA(bI cH cI Cw Dc Fw Rz Ux) lY(bJ Dg Iu Jo Of oH Ux Vq) nH(aS Dc Il iO Ip Iq It Vq) Ef(Dr Ir Js Rj Up Us Vt) On(aE bU dM Hv Rf Rh Tl) Jk(Fw Jn Jt kF mH Tz) Nx(kN mH nB nN oQ oW) bU(kF kK mY nC nJ pH) Ao(hC iZ kF kN mH) Fy(aD cN cQ mU pF) Hv(Iz Jg Jn Nt Tl) Sf(Dc Dk Im Jt Kf) Is(De Oe Rm Up) Iz(Jn nJ oO Us) Kf(aD iZ Ju Us) Rj(kE mP nU oW) cM(kF kN lW mH) mY(bI Ih iO Of) hC(Ap Bc Jg Vq) oQ(Cq Jo Kg Kj) Fw(Dc nC Tz) Nb(cX Mg Tz) Jn(Kp mW Ng) Jt(cF Mt Nh) Rz(eC fB mU) nJ(An Kq Rc) kN(cE Dd Mh) De(Ir Mr) Qz(lW mH) Tl(Ps Qa) Ux(bA nC) bI(kF nB) dX(Iv Mz) mW(cR iO) oW(Cq Mh) pH(Vo Wb) AsJg DccX MalW MgJl NgfB HoTz ImKp ItmP WfnU KskF OpnN OfnB OkiZ VvoP aEpK cGpF cQgW nCiO} Wn{uO(aH aJ An aO Ar aS aU bF BG bU bV bZ cE cF cJ cO cQ cU cW cX cY dL dR eT Fa Fn fY hL Hu hV iA iP Is It jF Kn kQ Lu Lz Mf Mg Mh Ml Mp Mr Mt Mv Mz Nk Nl Nq Nr nW Ny Ow Oz Pa Pb Pc Pe Po Qd qH Qt Qw Qx Qz rA Rg rW sK Ss tR tX Tz Uc Uh Up Us Uu uV vP vV wL zA) uG(aL aM AP bM Bo cH Cu cW eD Fn HR Hw Ih In jE Jl jO jP Ju JV Kk Ko kR Ky Ld My Mz Nc Nd Ni Nj Nk Nx Pc Qa Qe qG qH qI Qu rZ sK tN tQ tV uL uP Ut uX vT wE wF wH wK wL yD yJ tM tF) vV(aN bG bJ Bo bP cI Db dJ Et Fb gW hG Ih In iZ Ji jV Jy Kc Kd Ko kQ kS Kx Ky Kz Lu Mn Mz Nd Nj Nu Nx Ny Og Oi Om Ou Pd qH qI qO qU qV QW qZ rA rC rN sK St To tV Us Ut uV vO vQ yK) rN(aL aM bA bJ bM cD dD dJ Fa Fb Fn Ih In Ir Iv Jl jP Jr jU Ko kQ kR Ky My Mz Ne No Nx Ph Qa Qe Qg qI qU Rb sO Ss Tv uL Um uR vA vT wH wK yD yJ yE) qI(Aj Aw Ba bM Ch cW cX cY dR eC Ef hA Hu iA Iz Jd jF Jh Jk jV Mp Mv Nn Nq On Oy Qw Qx Qy Ss tO tV tX Ua Uc Uf uM Vs wE wG) tV(aH aU aV Bb cI cW Dc fY Hf hV Ih Ij iP jH Ji Jm Jn Jr Js Kn Lh Lu Mz nW Or Pj Qd qG qH Ql rW sO Tz UV uX zG zH) Uh(aL Ap Ar bA bG bL bU bZ cH cU cW DB eC Fn Fw iA Ib Id Is Kc Kp Ky Mx Mz Nq oE Ok Qn Rc Rg To Uu Wm) yD(aH bL bW cW cY dG dK eT It jF Ji kQ Ld Lu nW Oe Pc pY Qy Rf rO rW Tn Tr uX wG yL zA) uY(aJ aR Aw Bc bG Bo bW cR cW Dd Et It JF Ji Js Kg Kn Ks Lu Ny Ql qW Qx Rf Tz uV vQ) vP(aK As bG bL cI Db Fn gW Hc iH Ik jV Kc Ki Ky Mb Mz Na Oe Og qV qW rC sK Ut uV vO wC) uL(aJ Aw cI dK dL iP It jH Ji Js Kn kQ Ks Lj Lu Mn Mz Nw Oa Oe oH qH Ql qW Rf Tz uV) sO(bG bL Ch cX Dc Ii Iv jF Jh JV Kg Kr Ks Ky Ld Na Oz qB qU rA Rf To Tr) uV(Ba bG cT cX Fb fP jF jY Ky Mz Nq Pc Pi qD Qe QU Qx tT uR uT Vs yJ yL) wE(Ap aQ Ax cI cW dK Ih Im iP It Jr Ke Lu Mk Oe Or Pj qH Ql Qz St Tz) wH(aH bC cH cU Cw cY iA It jF kQ Ky Ly Ny Oe Pc Qd rO rW Ur Uu vQ wG) tM(aJ bL bP cD cH CW dB hG iZ jF Kd Kk kQ nW qW St Tr uU uX vO wG) bG(eZ fN iB qG qH rV rW tN tO tR tS tT uI uT vO wJ wQ yJ tL) cW(eT hL oE qB qC qD rU tX uN uW uX vB vT wF wL yK) tT(bJ bL bP bW dL Dp iZ jF Js Lv Mz nW Oe qU Ri zH) wG(aL Bo bP cZ dB Dl Fb Hu Il Jo Mz Na Nt Ra Ug) jV(eT fY qG qP qQ rR rW sC tO uM uR uU uX vS yL) bL(hO qO qP qQ rR rW sC tN tS uP vQ vW wC yH) uU(aL Ap aV Aw bM Mp Ni Nk Ow Pc Qb Qu tO) uT(Ap aV aY Fn jH Kc Mz Or Pc Qu Rj Uk) tO(eF Fb Fn Mw My Mz nW Or qU Wm Tj) wF(aH aJ Ap cV cY dN Oe Uk) yL(Ap Aw DB Kc Mz Na sK) uR(Ap aV Ld My Mz Oe qW To) zH(bM cD jD qD Ss Ur yJ) rR(Ch Di jO Ks Ni pF uI) vO(cU Hu Kj Ld Mz qA Uc) fN(aH aW Dk qQ qU Uu) fY(DB dJ Ks Na To) tQ(bW cY dK jH Oe pY) jF(hP sM wK wL yJ yK) Wm(tS uP wB yH yJ) cD(qA rV sC uM uW) wQ(Nm Pc Uk Ur Uu) tN(cU cX eT jH Or) wC(aH cU eC jH jR) Mx(bV eC hL oE) To(qO qP sC vT) aJ(qA qC qD sK) dB(qD qZ rS rW) qG(bW cY rA uW) yE(Cw iA Kc Pz) Ch(qC tX vH) Mz(tS vQ wP) Ky(eT qO qP) aL(rP uW uX) yK(aQ cY dR) yJ(bW nW Oe) qU(eZ sK vB) rW(Db Na uI) Bg(pY vB) Bo(wD yH) Cw(zG xA) Ex(cP nW) Lu(oE tS) It(sK vI) Qv(Kg Ks) Ld(hL qQ) Rf(qZ uI) Uu(Kg rC) wJ(Fn Jh) wB(Dp Ur) qA(iZ Ks) AppS CtjL MyvW NaqD IcuI TrhO InrO IrtS PzeZ QbuW KcwP KkqO OezG PczI aQvT bJvU cUrU cYwL iHqZ lKuM} Nj{Mz(aA Et Fp Fr Hr Hx Ih Ii Ij Im In Is Iv Jg Jh Jj Jl Jn Js Jt Lh Li Lw Lx Md Mh Mi Mk Ml Mm Mr Mt Mv Mw Mx My Nf Ni Nk Nm Nn No Nt Nu Nv Nx Ny Og Ok On Oy Pa Pb Pe Qa Qb Qd Qe) aA(Et Fp Fr Hr Ih Ij Im In Ip Ir Is Iv Jg Jh Ji Jl Jn Js Jt Lh Li Lw Lx Ma Mm Mp Mr Mt Mx Nf Ni Nk Nm Nn No Nr Nt Nu Nv Nw Nx Ny Og Ok On Pa Pz Qa Qb Qd Qe) Nu(Fp Fr Ih Ij Ik Im In Ip Ir Is It Iv Jg Jh Ji Jj Jl Jn Jq Js Jt Lh Li Lw Lx Mi Mp Mr Mt Mx Ni Nm Nn No Nv Nw Nx Ny Og Ok On Oy Pa Pe Qa Qb Qc Qd Qc) Og(Et Fp Fr Ih Ii Ij Im Ip Ir Is Iv Jg Jh Ji Jl Jn Js Jt Lh Li Lx Mm Mn Mr Mt Mu Mx Nm

Figure 31 Continued

Uv Uw Vi Wm) Ph(Du Eq Fi Ho Hp In Nh Sf Vh) Gp(bJ bX cR Du iA kG) Uk(bO cF cT dD eC Wf) hC(Kp Lp Mr Sh Vz Tl) Fn(bA bX cT cX Mv) Tv(cF eC nC nH nL) Ks(Fi Ho Hp In nR) dD(Hf Mb To Tz Ua) mE(Ld Pk Ri Tn Tl) Ng(Eq Hp Kj Tj) Kk(bX cT dK Mv) Ow(Bn Mk Mr nR) Uf(bX Ms nR Vj) aW(Hf Sj Ur Tj) bL(bO Ho Hp Ye) Du(aP gC tF) Fc(bW cK Nx) Nn(bO Qy Vi) Mj(Kq Tn Tz) Mw(Hp Ki Ur) Ok(Kl Uc Vh) cF(Hf nO Uo) nL(Id Ql We) Mv(bO Zw) Sj(bN cI) Wf(aE iJ) Ye(Hq mM) Kr(cG tF) bA(Or Sh) AoUx BaKl DrQl EqcT HaIn LxMk MeHf MnVh MsPk TnVi IlVq KcbW} Ji{Ii(aA aC bM Et Fp Ik Im Iv Jg Jl Jt Lh Lu Lx Mr Ms Mt Mx My Mz Ne Nf Nl Nt Nu Ok Pe Qa Qb Qd Qe) aC(aL aN aR Ax aZ bA bM cD cN cX cZ Im Jj Jo Jt kI Li Lj Mk Ml Mp Mz nC Nf Ni nL Nu Qd Ub) aN(Aj aK Ar Ax aZ bA bM bU cD Cs cT dJ Dw Ew Ik Im Jj Jn Jo Li Lj Mp Mx Mz Nf Of Og Qd) Et(aA Fp Hr Hx Jh Jj Jo Lu Mb Mh Ml Mp Mv Mw Mx My Nf Nl Nm Nt Nu Ny Of Og Om Oy Pb) sI(aW aY bU cS dI Dk Hq Im Ip Iq Iv Jh oE Om Pa Pb Pf Rg rU rV tV uM uO uR vB vV) Nt(aA Aj Hx Ik Im In Iv Jh Jj Jo Mh Ml Ms Mv Mw My Nb Nf Nm Ny Of Og Om Oy Po) wE(bI Ef Gz Hu iA Ik Iz jD Jh Jk Li lM Lu Ly Mk Mz Nc Ph Qy rO Uu uY wF wQ Tk) My(aA Ik Im In Iv Jg Jj Jq Lu Ms Mt Mu Mx Nf Nl Nn Nu Nv Of Ok Qd Qe) Nf(aA bM Fp hC Ik Im In Iv Jj Lu Mb Ms Mx Ni Nu oE Of Og Ok Qd Qe) Nu(aA Ik Im In Iv Jh Jj Jo Jq Lu Mp Ms Mw Nm Of Og Om Oy Qd) Lu(aA Hx Ik Im In Jh Jj Jq Mh Mp Mv Mw Ny Of Og Oy Pb Qd) Mx(aA Hu Hw Hx Ik In Jj Jq Jr Js lM Mh Mj Mp Ms Of Og Oy) wF(Dk Ef Hu iA Ib Iz Jh Jk Kp Nq Qu Qx Ra rB Uv Vs Vt Vv) Im(Hw Ik In Iv Jh Jj Jq Mp Ms Mw Ni Nl Of Og Om Oy Qd) wQ(aY cL Ef iA Il Ip Iq Ir Kp Mh Nb Nk Nq rO Uu wD) Iv(aA Ik In Jj Jo Jq Mk Mp Ms Mw Of Og Oy sF sH) Qe(aA Hw In Jj Jq Mb Mh Mp Ms Mw Ni Of Og Om Oy) bM(Aj aK aS aU aZ bA cT DW gW Hr Jj Jo Mp Of) jD(AO aZ bN cX Iz Jd Qx Qz Ra sK Vu Wc Xa Wm) Qd(aA Hw In Jj Jq Mh Mp Ms Nl Of Og Om Oy) Ok(Hr Jh Jq Mh Mp Ms Mw Nm Of Og Om Oy sF) Gz(eC kS oE qH qQ rB vB vH vT wC wH) Oy(aA Fp Ik In Jq Ms Mt Nl Nn Nv Qa) Jg(Hx Jh Ml Mv Mw Nm Ny Of Og Om) nI(eM Gn Hp Sf Si Um Yj Ye Tl Xa) In(aA Fp Jj Mp Ms Nl Of Og Qa) Si(gL iZ jB kS mM Nd nJ Tl) aA(Hr Jh Jq Mp Ms Nl Of Og) sF(bJ Il Iq Kq Qy rU rV St) Yk(kG lX lY mM mS nH nL) Qa(Hw Jj Mh Mp Of Og Om) Wc(jH jK jU lY qV qW qY) Tl(bU dX eQ iZ Ju Rh Sf) tT(Hu Ly Mh Mk Nq Pc rC) Nl(Ik Jj Jq Ni Of Og) bU(kI lX mT nJ nL nN) eW(As bN Cs cV Di Ly) sH(cS Dk Io Kq Qh uY) kS(Du fR Gc Gn Sf Xa) oE(cX Iz Lv Mk Ra Rf) Dw(cN cW Di Ew Nk) Fp(Hr Ik Jj Mh Mw) Vz(jQ jR qW qX rA) nL(dD Dp Qx Qz Um) Wm(jH Mk rC wJ) Mp(dW Ik Lx Mt) Ms(Jj Ni Of Og) Mw(Mt Mu Nn Nv) Mz(Hx Ny Om Pb) eO(Ar dB De dJ) kI(lL lN qU Ug) kN(jY kP lK lN) Ew(cF Cw Mn) Nq(uM wD wP) Nb(Jl Mr Pe) Ik(Jq Mb Ne) Sf(mM Nd nK) We(iB jQ lM) Wh(jL lM qX) Wf(jH jU rA) iA(rU uO wD) uY(Iz lL Ly) Po(Lx Pe) Gn(hC iZ) Nn(Jh Mv) Ni(Nc Of) Hp(gL iZ) Wb(jU jV) Wd(qT qX) Jl(Hr Mh) Ye(iC jQ) mM(Va Yj) nJ(Ub Ug) CpsJ ExyH LyuM MarQ MmeM MtJh IztV YimS YdrA ZwqX YliC NydU OfOg UolM UwgL VhnO aFdW bOeQ cDdR cQgZ fRgW nKlL yJrC rBwD} nL{lL(An AO aQ aS aU aW bA Bc bE Bo Ch cJ Co CP cQ Cv De Dp dR Ef Ez gW Hc Hv IB iC iH iO Iz Jd Je jF Jj jQ kN kQ Kx Ld lK My nN Nw Og Pj Qm qU Qw Qx Ra Rb St Uh Uk Um Un Vs Tj tF) aC(aM Ba bB bC Bo bR bU cF cG Cu Cw cX Db Dg Di Dl Et Gl Gp Hq Hr Im In Ir jD Jn jO jP jY Ke Kq Lh Li lN Lx Ly Nk No Nq Nr Nu Nv Nw Oh Ok Pe Pj Pz Qd Qe Ra Tn Tz Ub Uf Uh Un Vq) Gl(aK Ao aU aV bU cJ Co Ct dD Dp eQ Gc hC Hr Ij In Iz Jd Jh Jj lM Mk Nf nI Ns Of Og Om Oy Qd Qz Rg Rv Um Ur Yk Tj) Uf(Ao bE cE Co dD Dp Du eC Iz Jd Jh Jj kP lM Mg Mk mS My nI Ns Of Og Om Oy Qx Qz Rg Rv rZ Uk Um Vs Yl) Qz(bB bU cG cJ Cq Cu Cw Di Fy hA Hq Is Jq jU jY Kf Kq Lh Lx No Nq Nw Ok Ou rZ Tn Tz Ut) Jj(bU Cq Fy iB Is Jn Kg Ko Ks Kx Lh Ng Ou Ph Qc Qh Qu Tn Tv Tz Ua Uc Uh Un Us Ut Uv Tl) Lh(aL Ao bU cE cO Ct cX dD dE Dp Iz Jd Mk qU Qx Rv Ry Sf Si Um Ur Vi Yk Zw) rZ(Af aS aU bW cJ cP cY dH Dp Hw In Jd Je Jf Qb Qt Qx Qy Ub Uk Vo Vs Tj) Rv(aE An Cq cR Cv dB Du Fy Il Iq Li Ng Nk Ok Pe To Ud Us Vq) Gc(aL An aV bB cB cD cQ dD Hq Hv Hx Jl kS oE Qh Qv Ug Us) jF(Ap bC cO Cv Cw dA Dg Id Jd Ke Kl KN Sr Tz Vq Vv) Ut(Ao bI Ch Co Hc Jd Jh Mk My Of Og Oy Qx Ra Rg Ur) bU(aZ bF DU iH Ir Mh Mk mT Mx Oh Ou Qc Qd Qe) Tz(Hp Hr jD jE jQ kP Mk Og qY Si Ug Ur Yk Zw) Um(eC Fy Hq iH Im Iq Ir Jq jY nD nI nO Ou Un) iB(aS aV Hr Jh Jm Ma Mk My No Nw Oy qU Ur Vq) jU(Ao Ar aV Bc bM Co Ct cX dK dL iZ Ri Un) jY(bA cC cJ cP Cv Dg Gp iP Kn Kq Uh Un) Dp(Fy Hq iC jE jI Jq nO Nx Ou Tn Us) aL(Ax bC Fa fB Fy iH Kx Li lW Lx Qe) We(An bI Hq Il Jq Ng Nx Ok Om Tn) Vi(Cu Fy Jl Jn Mw Nv Ou Qh Rh Tn) jD(aJ Ap Bb dM Gp Kf Kq Uh Vq) qU(cP Ma nR Nw Nx oQ qW qZ Un) lM(cE Cw dF Gp Id Kn Pj Sr Vq) Yk(Cq Jn Ke Nv Nx Ou Qh Sj) Og(EM Gp Tn Us Vp Vq Vt) Rg(aD cP Cw Fy Gd Mk Ok) Ou(Ao Gn Mk nI Of Oy Qx) Ur(Cq Hq Im Iq No Nv Tn) dD(fB Hq Ir Qe Ry Vq Wf) Op(Du hC Hv Lj Pe Us) jV(aS cJ dF iH iZ Kq) Sf(Cq Et Hq Is Qh) Ry(hC Iq Jl Ow Qh) bB(cF Gp Mk Oy Uy) Du(Cq Nd Qt Rj) Nx(Gn Rt Ru Ye) Ug(Iq Ir Is Pz) cM(bR dM nI Nk) gW(bM Id kF kN) hR(Jy Kq Tn Vp) rY(An dA dI Rh) lN(cJ cP Id Sr) Ao(Gd Hp Zw) Mk(Jd Ow Uh) Hw(Gn Hp Yj) In(Fy Is Qc) Tl(cQ Gp gZ) Rf(Im No Oh) eD(aV dR iP) jE(iJ Jy Vq) jI(cB cP Jv) jT(Gp Jv Uh) Hq(Hp Ye) Hv(Uw Zq) Sr(jQ jR) Wf(hC Li) Qv(Fy Im) Yl(Rj Vq) Rh(Rz Xa) Oy(bC Ow) Pj(hV hX) bM(qY rA) nI(kQ Us) iC(aQ cP) qW(cS iO) BaCt CqUk CuPs CvVj EtQx GdPz MyNw HriH IdjR TvdU IrbE SjfA ZwJq KnhV RteQ hXkS} sH{Dk(Ar Ax Cs cY Dc eT Hx Im Io Is jE jM jQ jR Js Kd Ke Ky Lh Lj lK Lx Lz Mh Ml Mp Mr Nw Ny Oa oF Or Pe Po pS QD Qe Qv Qy Rf rU rW sC Sr St Tv uR vI VP vQ vS Vt Vu vV yH zG) Kr(aD aH aL aN Ba bF Bg cE Ch cQ Ct cU cX dD dJ Ef Fy gW hC Hu hW iA IB Ic Jh Jk Jy Kl Kq Ne Ng Of Po qD Qh qO qZ Ra sI Ua Ub Uk Uu VT wD wF yH) lL(An Ao aW Ba bJ bM Ch Cp cU dR Ef Ez gL hO Hx iA Ib Ip Iu Iv Je JR lM Mh Nq OH Pf Pg Pk qD Qx Ra Rg rP rQ sC sI Sr Ua uY uZ vI Vs Vu Wm Tj) Qy(aD Af aH Ba Ch Ct CX De Ef Fr Hq Hr hW Ib Iu Jh Jk jM Ky lN Mf Mg Nb Ng Oe Of Oy Ra Ua uR Wm) jM(Ar Bg bJ cS cW eC Fb Fw hL iA Ic iZ jH Kf kQ Kx Nq nW Nx Pg Qg Qx Qz Rg Rm rU St Wm) Kq(aR Ba Bg hW Im Kc kR lN Lx Nq Nw Ny Oa Og Pf Qd Qe rS Un uR Vu wD wH yL tL Wm) hW(Bg bJ Cp Cq cW cY Di dR Fa fY gL gW Hx It jR Ko oK Ql qO qW Rb Rg vP Wm) Ra(aQ aU aV Aw cW cY dK dN eT iA Ip jF jO jV Lj rO rU rV vP vQ vV wE yH) Wm(Ax Cv hA hP iB Ip Ir jF jV Lj Mh Mr Qv Rf rU tO uZ Vu wE wH yL) Ib(aR Dc iH IO Ip Iu Jo Ju Kg Ky Ma Mw Nr Pj Qg qY Vo vV) Ef(cY Dc eT Io jF Js jV Kc Nr Qg rO rU rV rW vP vV yH) Io(Ba Bc Bg Ch Ct Ez Fy Hf iA Kl Ky lN Qe Ua Uu) Jh(Cv Dc Fy Ir Is It Ke Oa Or Pk Qg Sr Vp Vt Vu) Ip(aD Aj Bg bJ Ct Ez Fy hC Ic lN rO Ua Uk Uu) cS(aR bM cY hO hV jD jQ jR Ub uP vP Vu vV yJ) Pf(Bc eT hV Is jF jR jU jV St Tv uM Uo Vu) vV(Ba Bc Ch Ct Cw Dp Ed Hf Je Ph Qh Ua Vs) iA(aD Iu jV Po tO tR tS tX Vo vP wH yL) Jk(Cs Dc Fy Js Jv Oa Qg Rf Sr Tv Vu) Ky(bC cD dK Fa Iu Nq Ok pF qT Qx Rg) aR(bJ dE Fn hG Hq iH rV uL uM uO Uu) Ch(cY Dc Iu jF Js jV Ma Qg rU) Pk(dJ dK Iq Ir Is Iu Iv Je wD) Bc(Iq Is Iu rU sC Uf uX Vt) Ct(cY eT Iq Ir Is Iu rO vP) Uu(Dl Iq Ir Is Iu jV Ke yH) Ua(cY jF Js jV Nq Qg rO) Rg(jE Nw pS qD rU uY yJ) It(Hu jK jU Jy tV yJ) cW(aP hO Po qC qD vW) yH(Aj Cq hG Kp Tr Uf) vP(As jK Ks pF Ph Qh) Nq(fN Ju Jv Ow Ub) Ir(dR Fy gW hG Ub) Pg(jV uZ wE yJ xA) uM(hC iJ iO Kx Ne) pF(eT iO Mz uR Vu) Ba(cY Iu jV Ke) Vs(rO rU rW uL) bJ(bA nY tT Uh) jK(aV cY jR qO) uZ(cD Cq Ql Qm) Ed(rU rV uL) Hf(eT Iu jV) Qh(jR Mx Nx) dR(Mh rT yK) iH(eT Ic Qt) sC(Cq Je St) Bo(wD wF) Cp(fN vQ) Fa(vS tL) Fy(Iq Is) Mz(Il Kz) Ub(rU rV) Hu(Js Mx) Iu(Aw Rf) Qz(jE tO) Qx(qD uY) Qg(Iz yJ) Ke(bQ Kl) Vu(cG wE) tT(gL kS) hG(Iq Is) AjrU CoJu DcOf DiuR DpeT TzHq HxjG IlpS IvhL JfuY StLj QwaH JsJv KpjI KsvS RfOh OutR VtdK cYyK dNuP iJyJ jVkQ} dW{aF(aC aI aJ aP aQ Ar aU AW bB bM bR bZ cC cF cG cU cW dD dF dG dL dN eO Et Iv Jj Jq Jr Js Lh Lj Mb Mr Nb Nc Nh Nl Nq Nw Qa Qc Qe) Jn(aD aG An aO aR aV bF bG Bn bQ bR bS bW bZ cD cG cL cO cP cS Ct cX dH Dl eO Hq Iu Jg Jj Jt Lj Mh Ml Mm Mn Oi Oy Pz Qb) eO(dL Et Hx Ij Im Is Iv Jm Jq Jr Lh Li Lj Mb Mh Ml Mq Mr Mt Mx Nn No Nq Nr Nw Ny Oe Oh Ok Pe Po Qa Qc Qd) bR(aM Aw bZ Dk Ew Fr gV Hw Hx Ip Is Iv Jl Jr Lh Li Lj Me Mj Mq Mw Mz Nb Ng Nq Nv Om Pf Qa Qb Qc Qe) Qc(aG Aj An bM bQ bW bZ cD cG cO cP Ct cU dF Di fP Hq Hx Ik Ma Mg Mj No Of Oi Oy) Of(aA Ap cC Ch Fr Ii Io Jk Jq Lh Mt Mv Nc Ng Nn Nq Nr Nv Oe Om Pd Pz Qa Qb Qe) Di(aC aD bF Bn cD Dc Fr Hr Ip Jm Jq Li Lj Me Mf Mx Nm Nr Og Ok Po Qa Qd Qe) aO(dF Fp Ij Is Iv Li Lj Mb Mh Mj Ml Mq Mr Mv Mx Nd

Ax cR Cs dU Fw Fy Gc Gl Im Ir Is Jn Jq Ke Kn Kq Kx Ld Lh Li Lj Mh Mk Mx No Nv Nw Ny Oa Oh Or Ou Pe Pi Pj Po Qa Qb Qc Qd Qe Sr St Tz Vt Vu) mT(Ar Ax bB Bo bQ bZ cG cR Cs Cw dU Fp Gl Ij Im Ir Is Kq Kx Ld Li Lj Lx Mp Mq Mt Nf No Nv Ny oE Oh oW Pe Pj Qa Qe Sr Wb Yl) oW(aC aG aL aN bE bJ bN bW cF cN cO cX cZ Dg dJ gL hC Hq Hv iH In Is Jn Jr kG mH mS Mx Nb Nd nH Nx) dU(aC aG aN aR bE bN cF cO dB eF fP gL hC Hf Hv Iv Jr Jy Kq Mm nC nH Nk oK Pi Ub Ux) nO(bF cF Dp dR Ed Gd Gz hC Im Ir Lh Li Lj Nw Ny Oa Oh Or Qa Qe Sr St Ug Um Vi Xa) mS(Ax bF Ex Fd fR Gn Gz hC Hq Im Ir Lj Mk Nv Ny Oa Pi Qa Qe St Ub Um) iH(Du Gc Gn Ho kF kO mI nA nC nD nF nH nJ Rz Uw Ux Vh Zq) Gc(hC hG iZ kG kN kQ lY mY nB nC nW oE oF Vu) Ho(Dk hB hC iZ nA Nd nW oE oF Or pH Ut Vt) eQ(aR aX cC dB eF fP gL Hq Ih Jn kO Rh) kE(Dr Du gZ Hl Lt Rt Ry Rz Uw Uy Wb Tm) Rv(hC hG iZ kF kG kQ mM mY nW oE oF) Vh(gL hB hC hG iZ lY nB nD nW oE oF) pH(aG cF cO gL Hp Hq kR Pk Qm Um Tm) kP(Hq Ir Mk Oa Qd Qe Qz St Um Zq) Du(gL hG lY mM nB nC nH nW oT) hC(Em Gn nI Uw Ux Wf Wg Zq Zx) kG(Gp Gz Ir Kf Op Rb Rx Uh Zw) Gn(iZ kQ nC nI nW oF oO) Xa(gL hB iZ lW Nd nW oE) Em(hB hG iO iZ nY oE) Zx(aC Mx oE oF St Ut) fA(dB Hl Iq Kq kR Ub) nD(Li Lj Mh Pi Qa Um) nI(Ax eM Ir Li Lj Um) jB(Ex Gp Jy Qz To Up) kF(Dp eM Hf Kx Or Qz) Dk(Hp Sf Sh Si Yg) Zq(fP gP iZ mY oE) Wg(hB iZ kQ nW oF) aC(fB Gz mM Mt Vq) oQ(Dr Fc Hf Hp Tm) oT(kR Pj Rj St Uc) Zw(kN mM mU nC) gC(Lp Mb Qe Rx) gP(Rz Uw Vi Vj) oP(Jd Kq No Tt) Ew(Ba cX Of) Hl(hB nW pK) Hp(Mt nB oO) Vz(iZ nW oF) Ut(Lt Sh Si) oE(Rz Vw Wd) Im(aN nJ) Ye(mY nC) bQ(mE mI) fB(bO dJ) kI(Or Tz) pK(cC Pk) AjJg MbnH MtRy MymU NbpI UbgZ YhiZ YjnB RbkN QznR KxmW NwaN VchB dCeO nTjY} eO{Of(aA aC aF aI Aj An Ao Bb BC bG bO cC cD Ch Co Cu Cv cW Dc Dd Dl Et Gd Hu Hv Ih Ii Io Jh Jq Jr Lh Mf Mg Mt Mv My Nc Ng Nk Nn Nr Nt Nv Nx Oe Og Oi Om Oy Pz Qc Qe) dB(aC aI Aj aK aM An aQ Ar aV Ax Ba bB bM Bn cB cH cJ Cs CT cX cY cZ dA dC Fp fR Hv Ip Jn Jq Js Lh Lj Lv Lx Lz Mb Mj Ml Mp Mq Mt Nn Nq Nr Nw Ny Oh Oy Pe Po Qb) Ar(Ad aS bR cB cO Cq cW cZ Dc eM Et Ii Ij Ik Io Ip Is Jh Jm Jn Jq Lv Mf Mm Mp My Mz Nm Nn Nq Nw Nx Ny Oh Om Pa Pe Pg Po Qb Qe) Mb(aA aF AO aV bL bM Bo bP bX cB cF cG cL Cp cS Cu Cv dI eW Hu Jn Ly Mf Mt Nb Ni Nu Oe Pd) bB(Aa aC aH aN aR As aV aW Ax Ba cD cG cN cQ cV cW Db dC dL dN eM Hx Il Ml Ms Nd Ne Nk Po) aW(aS bI bN bR cF Cx Di dL dN Ew Hx Ij Js Mm Mw Nb Nq Nr Nv Oe Og Po) aC(aD An bE bI Bo cF cP Di dL dN Fr Ik Jh Jn Lh Mt Nr Oe Og Po) Oh(aA aG aN aO aR aY Dg DK Fp Lx Mm Mt Mv Nb Nc Ne Nl Nn) bR(Aa aF aM aN aP As cE cL cQ cW Dd dG Et Fp Hx Ip Li Lj Lu) cB(An aO aR Ax bF bN bZ cE cF cL Cv cW cY fP Io Mk Mn Pc) dC(bN cF cW Hx Ij Ip Iv Jn Jq Mj Mn Mr Mw Mx Nq Og Pa Pg) Mv(Cu Iv Jn Lh Mg Mt Nn Nr Nt Nv Ny Pe Po Qa) Ij(aR Ax Ba cH Cs eM Fp Ih Ik Iu Lv Ly Ml Ny) aO(aP Di dL Et Iv Jj Lu Nb Ne Nk Nw Og Po) cF(aD Ax cQ dL Fp Hq Li Lx Nd Ne Nk Po) Jj(AF aG bH bW cL cO cS Db De Hx) aN(aS bN cA Cu Di Mj Mt Nq Nr Og Po) Iv(aA aF bW bZ cG cL cO dH Hq Ly) Ax(bI In Mp Nc Ne Nh Ni Nl Pa) Di(Bb bE cX dD dX Fp Jo Ni Nx) aF(aD Ct Fp Io Jr Mt Nc Nd Og) cO(Fp Jr Li Lu Mk Ml Mq Mr Mx) eM(Jq Li Lj Mh Mj Ml Mq Nd Pe) Po(aY cQ dK Ma Mn Nv Oi Qa) aR(Jq Mn Mt Nq Nr Ny Pe Qd) Bo(Ao aX dJ Ip Jg Mx Nd) Et(aY cS Dk Mt Ne Nh) Nn(aG aY Mt Ne Nh Oi) Jo(Ad bM Cq Jr Lv Nk) Jq(aE aY bN Hx Iu Om) Aj(bM cC Hq Ih Mw) Nd(aK bZ cL dH Nq) Jr(bW bZ cG dH Hq) Pe(aE bC Ct De Ml) aD(aE aS aZ bA Oe) Fp(bZ cC cL Oe) Ma(aM cW Lz Mh) dL(dG Dk Ne Nh) No(cS Ct Dk) Lu(cL dH Nw) Lx(aA Oe Qa) bM(Gd Ms Oi) dJ(Jn Mn Nw) Bg(cC Qc) Ly(Ip Jm) Ne(aA bI) Hx(aA An) Il(Aw Pa) Qe(My Om) Lj(aQ bF) Og(bZ cL) bS(aM Bn) AdBb CsNx CtIh DkcW LvMp MncL NhNw NkbW JhcC LhcS PbaQ} Nw{My(aA Et Fp Im Is It Iv Jg Jn Jt Lh Lu Lv Lw Mb Mf Ms Mt Mu Mx Mz Nc Ne Nf Nh Nl Nm Nn Nt Nu Nv Nx Of Qa Qd Qe) Nf(aA aC Fp Ih Im Is It Iv Jg Jj Jn Jt Lh Lw Mb Me Mp Ms Mt Mx Mz Nc Ne Nh Ni Nl Nt Nu Nx Of Og Oy Qa Qd Qe) Oy(aA Fp Im Is It Iv Jg Jk Jn Jt Lh Lu Lw Mb Ms Mt Mx Nc Ne Nh Nl Nn Nt Nu Nv Nx Of Oz Pd Qa Qd Qe) Mh(Fp Im Is It Iv Jg Jl Jn Jt Lh Lu Lx Mb Mr Ms Mt Mx Mz Nc Nc Nh Nl Nt Nu Nx Of Pe Qa Qd Qe) Og(aA Fp Ij Ik Im Is It Iv Jg Jn Jt Lw Mb Ms Mt Mx Nc Ne Nh Nl Nm Nt Nu Nx Of Qa Qb Qd Qc) Mw(aA Et eW Fp Im Is Iv Jg Jl Jn Jt Lh Lu Lw Me Mt Mu Mx Mz Nh Nn Nt Nu Nv Nx Qa Qe) Of(aA Fp Ik Im Is It Iv Jg Jn Jo Jt Lw Mb Ms Mt Mx Nc Ne Nh Nl Nm Nt Nu Nx Qa Qd Qe) Ms(aA Fp Ih Im Is It Iv Jg Jn Jt Lw Mt Mx Mz Nc Ne Nh Ni Nl Nt Nu Nx Qa Qd Qe) Jj(Fp Ih Im Is It Iv Jg Jn Js Jt Mb Mt Mx Nc Ne Nh Nl Nm Nt Nu Nx Qa Qb Qd Qe) Mx(aA aC aN Hu Hx Ii Im It Iv Jg Jr Js Lw Mb Mj Mv Nl Nt Nu Ny Pb Qd) Ii(aA Fp Ih Im Is Iv Jt Lh Me Mr Mt Nm Nt Nu Pe Qa Qd Qe) Mb(aA Ik Im It Jg Jn Jt Lw Mp Mt Nc Nm Nu Pb Qa Qd Qe) aC(aL aN Ao aR bM cN cX Et Im Jt mI nJ nK Nm Nu Qe Ub) aA(Fp Hr Ih It Iv Jg Jn Mt Nc Ne Nl Nt Nu Qa Qd Qe) Im(aN Hr Il In Iv Mv Nc Ne Ng Nh Nl Nt Nu Qd) Mv(Et Is Iv Jg Lh Lu Mt Nn Nt Nv Qa) Hr(Fp Is Jl Jt Lh Lw Me Mz Nm Qa Qe) Jg(Fp It Jh Lw Nc Ne Ng Nm Qa Qe) Nt(aN Hx Ik In Iv Jh Mk Nl Ny) Nu(aN It Iv Jt Nl Pb Qa Qd Qe) eW(aF As bN Bo Ch cV dC Fr Pz) qU(kI kN nC nH nK nT nU Yd Tl) Fp(It Jt Lw Nc Ne Nh Nl Nx) Ew(aO aY Mn Nc Ne Nh Nl) In(Ih Iv Jn Jt Qa Qb Qd) nK(iB jL jU jV jY lL rZ) kN(gW jH jY kP lK lN rZ) Ne(It Jt Lw Qa Qd Qe) Vz(jQ jR qT qW qX rA) Lh(Hx Ml Nb Ny Pb Po) Qd(Hw Il Iv Mj Nl) Qe(Il Lw Nc Nh Nx) Ni(Nc Nk Nl Qb) It(Me Mt Nh Nx) Qa(Hw Il Mj Nx) Jt(Jh Mj Nc Nh) aN(bA cD cF dJ) sI(Pb Pf Ra Rg) kI(jY lN qT rY) Lu(Nm Ny Pb) Iv(Mk Nl sF) Wf(jE jH jU) Pe(Hx Nb Po) lK(kF lY mT) Ub(kG nJ) Wc(iC jU) Um(nI nO) sJ(Cp pF) qT(Ye Xa) DwLv PoMr EtNm MuHu MzNy HfnJ YdrA ZqqX TkwE UgmI aSbM bJsF nNlL jLkF} kF{gW(Ad aJ An bA Bg bH bM bN cD Ch cJ cK Cp cQ cT cY dA dI Ed Ef gL hC iH Ii Ik Io lZ Jj Jm Kj KN Kr Ky Lv mI Ms Ne Ng nH Ns nY Of Og Or Ow Oy Qt qU Qv Qz Rg rY Ss Tr Uc Uk Uo Up Us Vs) jQ(aA Ad aJ aK An aP aW Ax bA bG bH bN bS cK Cp cR Cs cT cY dA dI dJ dM gL Id iH IZ Kn Kr Ky Ld lL nY Or Qn QU Qv Qz Ue Uk Uo Vq) qW(Ad aJ aK An aS bA bH bI bN bS cB cK cP Cs cT cY dI dJ dM Ed gL hC Id iH iZ Jf Kn Kr Ky lL nY Or Pj QU Qv Qz Tz Ue Uk Uo tF) jU(Ad AJ Aw bA bH bN cD Ch Ct dB dI dL Fb hC iH Iz Ju Kc Kr Ky Qt Qu Qw Qz Rj Ss Tt Ue Uk Uo Ur Us Vp Vs) lL(aC aQ aW bJ cH cJ cQ cW dB Dl Fb iH Kc Kj Kn Kr lK lN My nK Og oH Pj Qz Uh Ur Us tF) qV(Ad aJ Al bA bH bN bS cK Cp cT Ed hC IZ Kj Kr Ky nY Or Qu Qz Ss Ue Uk Uo Up Vs) qU(aC aK aL aQ aU bA bE bJ cH cJ cP cQ cY dR Is jV jY Kn kP Ld lN nD Ns Nx oH Tv Ur) jR(Ad aJ An aQ Ax bA bG bH cK Cs cT dM Ed Iz Kn Kr Ld nY Pj Qt Qu Qv Qz Ue Uk Uo) jE(Ao As aW bA bF bN cK cT Cw Gp Kf Kn Ky nY oE oH oN Or Ow Pj Uh Uk Uo Up) lK(aJ Ax bA Cs cT iP Ld Ny Pb Qt Qz Rf Rj Sr Tv Ua Ub Ue Ug Uk Um Uo Ur Vs) iB(aC aK aQ aS aU aV bJ cP cQ cY dI dN iP Jj Jm My Og Qz Up Vs Vu) jY(aC aK aQ aS bA bJ bW cH cI cJ cT cY iP Jj Kn nW oH Ow Pj Qv Up) jL(aG aJ Ax bA cH Cs Gl Gp Kx Ld Ow Pj Qz St To Tv Uk Vt) rY(bE bI cK cP cT dI dK Dp dR Kn kR nW Ow Pj Qv Rh Ug tF) hV(aG aK aS aW bH bS bW cK cS cT dA dM Kn Qv Rh Up tF) jO(AJ bA dF Ed Pj Qn Qu Qz Ss To Uh Uk Ur Vp Vt) lN(aC aS bW cI cJ cP cQ dI Ed Jj Og Pj Qu) eD(bA Cp Cv Fb Kr Ld Ql Qn Qz Rj) Ut(Lp Ps Rt Rx Sh Si Wd Yj Ye) qY(bH bI bN Cp dB hC Qu Us) jM(bA cT Fb hC iH Kj Qu) lM(bF cE cT Cw oN Ow Uh) iC(aQ bW cJ cP Ju oH) gC(Kq Ld Rz Tn Uf) jT(hC Qu Ss Ue Uk) rX(aS cP nW Rh tF) rA(cK Cp cT Kr) qX(An cT Qu Uo) iH(jH jV qT) jI(aC aQ cQ) Dp(eC rC) bB(eM Yk) cP(hA jG) dR(jH rB) jD(Al Up) CqEq DlhW QujG LdeC LieM RhhX UkjV UmhR UhjP aLoW bGrB cQjH cTrC dDdU rZoH} Et{aC(aH aI Aj aL aN AO AR AX aZ bA bM cN Cs Cu cX cZ Ih Im Is Jj Jn Jo Jt Lh Li Lj Lw Lx Mi Mt Mx Mz Nf Of Qa Qd Qe Ub) Oy(aA Fp Ih Im Is It Iv Jg Jj Jl Jn Js Lh Lu Lw Lx Mb Mh Mp Mr Ms Mt Mx Mz Nc Ne Nh Nl Nn Nt Nu Nv Nx Of Pe Pg Qa Qb Qd Qe) My(aA Fp Im Is It Iv Jg Jl Jn Js Lh Lu Lw Lx Mb Mf Mh Mr Ms Mt Mu Mx Mz Nc Ne Nh Nl Nn Nt Nu Nv Nx Qa Qb Qd Qe) Nf(aA Fp Ih Im Is It Iv Jj Jl Jn Jq Jr Js Lh Lu Lw Mb Me Mh Mp Ms Mt Mx Mz Ne Nt Nu Nv Nx Pk Qa Qb Qd Qe) Of(aA bM Fp Im Is It Iv Jg Jl Jn Js Jt Lu Mb Ms Mt Mx Mz Nc Ne Nh Nl Nt Nu Nv Nx Og Qa Qb Qd Qe) Hr(aA Fp Im Is It Iv Jl Jn Jq Jr Js Jt Lh Lw Me Mh Ms Mx Mz Nc Ne Nh Nl Nu Nx Pe Qa Qb Qe) Jj(aG bM eW Fp Ih Im Is It Iv Jn Js Mb Ms Mt Mx Mz Nc Ne Nl Nt Nu Nx Pk Qa Qb Qd Qe) Ms(aA Fp Ih Im Is It Iv Jn Js Lw Mt Mx Mz Nc Ne Nh Nl Nt Nu Nx Og Qa Qb Qd Qe) Og(aA Fp Im Is It Iv Jn Js Lw Mb Mt Mx Mz Nc Ne Nh Nl Nt Nu Nx Qa Qb Qd Qe) Ii(eW Im Jl Jq Js Jt Lh Lx Mi Mr Mx Mz Nt Nv Nx Pe Qa

Un Up Ur Uu) Wf(Ir jY Li Lx Me Mr Nb Nc Ne Nk Ny Oe Qa Qd Qe) Yd(lM Me Mq Mr Nc Nd Ne Ni Nk Nl Nu Pe Tm Xa) Uh(kl kO mM nA
nD nJ nN nO nR nT nU oQ) mT(aJ Al AP bA cD Dg gL Gp iZ Kq) kl(dF Dp iZ Jd Ke oN Ou Pj Sr Uk Uo) lW(Ao bA cT Kf Kp Ky oE oN Ou
Ow) mM(aC aN bN cQ cX dJ Dp Ri Sr Vq) nK(cP Gl Gp Jd Ju Jv Jy Kq nW) Zx(Il lu Jm Mm Ni Oh qT) lX(An Ar dM gL Id Sr Tz) We(Jh Jq
Me Po Tz) nJ(Dp iO Ri Sr Uo) Wh(Jh Jq Me Pz) Xa(lt Ng Oh Oi) nN(An Up Uu Vv) nR(Ri Up Us Uu) sF(As Dk gL Je) Vz(iB Mr qV) mU(aJ
Cs iZ) mW(As bA Cu) kO(Cw Kp Pj) oP(Ba Dg Kl) Po(Wc Ye) Nf(Wb Tm) Yg(Jj Jm) Yi(lu jD) Sr(kP nC) Wd(jD Me) Ur(nD uY) sJ(Dd iJ)
oO(Dg Kf) DlGz ldnC IrYk WcaA YeiC YlqT UpnU nTiZ nBiO} sI{Kr(aC aH aN aU aZ bF Bg bH bl bJ Bo cD cG cX eD Fb fP Fw Ha Hq hV Ib Ih iO jH jR jT jV lK Mr Ni Nn No Nq Nu nW Nx nY Pb Pg Qc qO qP qT Ra Rg Rh rV tT uU vT vV wE wF wH yH xA Wm) Nx(aR aW aY BC dI dJ Dk hA Hq Hu hW iH Iq Jh Jk Jq Jr Mf Na Ng Om Oy PF pS rA uM uR vB vH yJ) Ip(aI bB cZ Ha hG Hr iO Je Jj jK jL Jm jY Kk Lw Mf Mh Pg pS Pz qX rC Rm Ub Uk uO) uR(Ad aE Aw Bc Bo cD Cp DC Ef Mr Mv Ng Nk Nq Ou Pg uM Up Uu zH xA) wE(cY dR eD hA hG iO Ju Ko Mz Ou Pg Qm Qv Rb vS Vu zG Wm Tj) tT(Ar bJ Cq cW Db eC hA hG iA iZ KS nW Qg rC Ri wK tF) Js(Cp Dk Fn Hf Hq Ib Iq Jk Pf qG Qh tQ tV) uO(Aj cI Cq Ct Dp eC Hf iP Pf Pg Qm Ra Vs) bC(aG An Hf iJ iO jH Lh lN Ou Qz Uh Wm) tV(cW cY Hf Hx Lu Mf Mx Pg Qm uM wF zG) vO(Bc Ef Fr Jh Mv Mw Ni Nq Om Pf Vs) Uh(bJ Cw dB Hf Hq iH Kp Mt uM Uu) Pf(Aa Ny Pg Pj Ql Ri zH) iH(dR jH Ke Pg Ql Qw Wm) rC(Ch Ef Ib Iz Jh Ua uM) pS(dR eC hA hC Nq rU Ug) Hq(Is Jl Pj Qz Vo Wm) Rb(hW Lu nW tQ Up Uu) Ks(Aj cD IB Pg wF) Pj(Cw Jk Jt Qh Uu) cW(dL hR Jl jU lN) Wm(cD Fn Nk tQ) Pg(Db Qh uM vV) dR(aK dB kS rT) Dg(Ba Kl Uu) Ib(Kg Ua yE) Ql(hW Qh tQ) Fn(Mx Na) Lu(Qh Ra) Hr(Bg Cp) Ny(Rh uM) Up(Mx Na) cD(Bn jH) dB(jH Qw) hW(Db iO) zH(Dk yJ) vV(Dd Kk) AsvP BcLh ChUa CqzG NqRf MfeC JhKg RawG KeuM QmtQ aVcY hAiJ iAwB} aC{Ar(aN aX aZ Ba Bb Bc bM cD cT Cu dJ Dl Io Is Jj Jt Lw Mi Mk Ml Mm Mt Mz Nf Nm Pz Qd Qe Ub Vt) Jt(Aj aM aN aR Ax aZ bA bM cD cN Cs Ct Cu cX Im Jj Jo Li Lj Lx Mk Mt Mx Mz Nf Ni Nk Of Qd) Im(Aj aM aN aR aS aX aZ bA bM cD cN cX Dk Io Jj Kp Mk Ml Mt Mz Nf Ni nK Nm Of Pj Ub) aN(Ba Bb Cu Dl Ih Io Ir Is Jn Kf Lh Li Lx Mm Mt Mx Mz Nm Pj Qa Qd Qe) Ub(Cs dX Id Ir Is Jd Kc Kf Kn Kp Li nJ Pj Qa Qd Qe Uh Un Vq Vt) Bb(aM aR AX bA bM cT dF dL Ih Io Li Mt Mx Mz Ni) Kf(Aj aL aM bM cX Ef Gz Jj Jv Lj Lv Mk Of Pk Uu Vt) Pj(Aa bM cN cX dH Kc Kp Lv Mk Ml Nd Of Or Pa Pk) nH(Ba bC Bo Cw Db Di Gl jD jO Lh No Nv Qc Uf Un) Mz(aR aX bA Bc bM cD Jn Li Mk Mx Nf Nh Nk Qe) Io(Af Aj Ax Ba Bc bM Cs Cu Kc Li Lx Mt) nK(Ba Cu Cw Db Dg Gl Ir Lh No Nv Ps) Nm(Aj aR Ax bV Cs cX Li Lj Mx Qe) Qd(aR aS bA bM cX Jj Mx Nf) Ba(Aj aL bM Jj ml nJ Of) Ew(aR bQ cU Hq Ma Nc) bM(Gp Is Kc Kp Mt Uh) kI(iB jI jY Lh lN rZ) Cu(Aj mU Nf nI Of) eW(aA aF bJ cH Hx) Mk(Ex Or Vq Vt) Mx(aX Kp Uh Vt) Nd(Kc Sf Wb Zq) Lh(aR ml nC nJ) Li(aR lW Nf nI) mM(jI jR lN rX) Ir(kG nC nI) Qe(aZ Jj nJ) Kc(aS Lv Pk) eQ(bB Jh Qu) mI(Bo Cw No) mW(jI jY lN) Dw(Ct Hq) Gz(uY vT) Nu(Is Lw) Mt(aX cF) Ih(aS aX) Jj(Bc Vq) dX(Qm Tv) lW(qY rC) nC(Uf Un) nJ(Cw Gl) oQ(eD rY) CsMl DkSf MmaR QysF QgVt UwgW VqcF PenI nOjI nFhV} dX{pF(aH aI aL aQ bB bC Bg Bo cB cG Ch dD dF Dg eM hC iJ Ke Kk Ko Kp Kq Mn Mp Mt Nq Ou Ow Qm Qn Qt Qw Rg Tn Ub Uf Uh) eC(Cp hC Ib Id Im Kc Ke Kf Kk Ko Kp Kq Kr Lx Mt Nc No Nx NY Or Pz Qd Ql Qm Qn Qw Rc St Tn Tv Ua Uv Vp Vs Tj) oH(aH bB Ez Fy Jf Kc Ke Kf Kk Ko Kp Kr Mn Mp Ow Pj Qm Qn Qt Qw Qy Ss To Ua Ub Uf Un Uv Vq Vt) oN(aH aI bB cG Ch dD Ex hC Ke Kf Ko Kp Mn Nn Nq Ow Pj Pz Qm Qn Qt Qu Qw Tn Ub Uf Uh) Ho(aX bF bG bN Bo bW cB cE cF cG dH Em Fi Gb Hq Kd Kp Lt Ms Pi Pk Qn Rx Vc) tF(aH aQ bB dD eM Ib Kg Ko Kx Mn Qm Qn Qu Tn Ua Ub Uf Vs) iA(aQ bB dD Ed Qm Qn Qt Tn Ub Uf Vs) Fd(Ar Lh Li Lx Lz Ml Mw Nq Ow Pe) hC(aI bR bZ cC cL cU dH Di Jf Ub) kS(Fy Ke Ko Kp Qm Qn Qw Tn Ub Vs) Zx(bL bM cB dI Ik Jv Sh Vo) gW(aN bM cT dL fR Il Jj Lw) Mw(Ps Rt Yd Yg Yh Yk Xa) iJ(Cp Hx Jf nY Or Qn Uv) Po(Fc Lt Rx Ry Wd Wf) Mz(Fi Hl Sf Vi Vj Yl) Lh(Hp Lp Ry Yg Ye Xa) Wb(As bL Nd Pk Qn) Un(Fi Lp Rt Yh Yk) Du(Ao Cp Im Kq) Fa(Sh Si Vj Yd) Mn(Fc Fi Sj Zq) dR(Qm Qn Qw Uv) nY(aE bR Hb Pj) oK(aQ bB Ow Qm) Eq(Jd Ng Qe) Yj(Id Jn Pe) Kp(aQ As Qn) Ry(bL bM Ms) Lx(Hp Lp) Nd(Sf Sh) Tn(cD Vv) Yi(bJ Fw) Vz(No Qb) Si(Fb Or) Zw(Ke Li) Wh(fP gP) Yl(Ao Qb) ArYg YfPi EwbR MlWe MxVj HxWc YhLi QeRx WfKx JrUv JtVo KokQ UwgP VceF} Jj{Qe(Aa eW Im Is Jh Jn Jq Js Jt Kf Kp Lh Lv Lw Mb Mm Mt Mx Mz Nc Ne Nf Nh Nl Nm Nn Nu Nv Nx Ny) Jt(bM Fp Ih Im Is Jl Jn Js Lh Li Mb Mm Mt Mx Mz Nc Ne Nh Nl Nn No Nu Nv Nx Ny Qa Qb Qd) Nx(Fp Fr Im Ir Is It Jn Js Lh Li Lx Mt Mx Nc Ne Nh Nl Nm Nr Nu Nv Pz Qa Qb Qd) Jn(aN bM eM Fp Fr Im Lh Li Lx Mm Mt Mx Ng nH Nl Nm nN No Nu Nv Pz Qa Qd) Qd(Fp Im Kf Kp Lz Mb Mj Mm Ms Mt Mx My Mz Nc Ne Nf Nh Nl Nm Nu Nv) Im(Fp In Jl Lh Lv Mb Mm Ms Mt Mx My Mz Nc Ne Nf Nh Nl Nu) Kf(aN bM Cs Ik jV kP Lj lM Mx Oa Pk Qa Ra Rg Us Uu Vt) Mx(aN bM Hf Jd Kp Mm Nv oN pF Sr Uf Uh Vt) Nu(Is It Jl Js Lh Mm Mt Nl Nn Nv Ny Qa) nH(Fy Gl iB Jk Lh lN Ng Nv Qc Tt Tz Uf) bM(Ad Ba Bb Is Jd Kn Kp Ks Pi Uh) ml(Cu Fy gW Lh lN No Nv Ou Uf) kP(Fw Fy Kn Pi Qc Sr Tz Uf Vv) nK(Fy Gl Lh No Nv Wd Yg Xa) jV(Tz Vz Wd Yh Yi Yl Zw) Yd(jH jM jQ lM qT rA) Fy(kI kS nA nC nO) Vz(jQ jU qT qW rA) Ye(iB jI jP jT lM) Nl(Js Nv Ny Qa) Yg(jD jR mE Nd) Yi(jD jU mE mS) Zq(kS lM mM oK) Wf(jG jL jR rA) Lh(Ih nC nO oN) Mm(Is It Qa) Mt(Is Js Mz) Yh(jD jQ jU) Xa(mE mW Nd) Nv(It Ne Nf) eW(aF Bo Lx) nC(Gl iB Tt) Qa(Kp Mz) Wd(jD jU) We(jH jQ) Ks(aN eQ) Uh(Dc sJ) nO(Qu Um) mM(Kn Rz) AxEw WmsJ FwnI GzuY NdHo UbJd IsaN YkmE WbqT ZwlM ZxlN PzJs KqkI PhnU PjiC} Xa{kS(aM bG bM BN bO bX cD Cu cX Ha hC Ik Jq Jr Lh Lx No Nx Op Ou Pe Po Ql Qw Sf Ub) eM(Aj aM aZ bG cD Cx Ed Fc gL hC Hv Jn Kd Mh Ms Mv Mx Nb Nl Nq Pk Vt Vv Zx Tj) fB(aF aL aS bA bI bL cQ cT dJ Dr Nm Nn Ny Qu Rj Sr Uo Us) eQ(bL cP Dd Gh Hu iH Ik Jy kP lY mH mS mT nH nW Up tF) nO(aE bO cA cQ cR dD gC Gp Gz hC Kn pH pI pK Rf To Tj) dU(aG Bc bH Ch dG hC Hq Hv iA Kl Oi Qn Tz Ua Vj Wd) pF(aM bB bN bO gW It Lx oE Oi Sf Ua Ub Uk We) nK(bB bN cD cR Iu kG nI Pd pI Rf Rg Rh Uk) pI(bM bX Hv Lz Ms Nh Ss Tz Ua Ub Uc Ue) lW(aW bN bO cQ cR dD Gp Ry To Ye) gC(Ao bX Lp Pz Ri Rj To Uo Vq) Nd(bM cD cQ Ik Ju Rh Sf Uk) qT(Im Jq Lh Lx Mt Oy Qa Qd) kG(An aS bI cA Ip Nk To Yk) lM(hA Ik It Jm Ms Pc Yk Ye) oE(bG cQ CX Mz nR Rf Ry) To(kE kP mI mS mT pK) Rh(bM eC gL hC mE nH) We(gZ mE mW nR nU) aM(hC iA mU nJ oQ) jU(Lu Me Oy Pg Ye) Oi(gL jH jI jQ) Vi(fA hC iZ oW) bN(mE mI nJ oN) mS(bL bX Rf Us) Nf(iC jP oP) Vs(mE mT mW) bO(De iZ oN) eC(Bn mI pK) gL(Bg bR Pi) gZ(Fn Hq tF) qV(Mh Oz Po) nW(nR oO Rf) oQ(bC nB Vv) Nn(jY oW) It(jP jT) Qe(Rf Rm) Wc(iC jY) Ye(mU nI) bB(mH pK) bM(dE Vt) cD(iZ oN) dJ(dR gW) hA(Lu Me) iA(cQ cX) hC(Db Ry) jV(Nb Oy) pH(bX Uo) GlnI MajI HvmU QuoW UkmE PaeD bGmT cIfA cRmW} gW{Uw(An aO aW Ax aY bF bQ bS bW bZ cC cE Co cR cS cU dH dJ Ez fP Hq Jo Ki Ma Mj Mx Nd Nn oH Om oN Pi Pk Tn Uf Um Vc Vi) Zx(aO aV bF bG Bn bS bZ cC cE cL cO cQ cU dH dJ Gd Gh Hp Kk Ma Mm Nd Ni Oh oN Pa Pi Qn Qt Qz Rc Rf Vc) mI(aJ Ax bA cT cX dG dI dL hC iC iZ kO Li Lj nA nH nN Pe Pf Ug Uk Uo) Vj(aO bF bZ cE cG cL cS cU dH dJ Ez Hq kS Ma Mm oN Pa Pi Vc) lY(aJ An Ax bH bM cX dL gL hC Id iZ jl Lv nA nD nN Oe Pe rC) nK(aJ aP bM Cu cX dM Id Im iP jl Jn jY lW Mr No Nv Ny Pe) fR(aN bH bI bO cA cH cT Fp gL jD Kx Mr Nn Ns oH Ow) nA(aL bM cJ Cu Hc Io Ir lW Oi Pj Uh Up Ur Us) cB(Eq Gh Hl Rt Sf Sh Sj Uy Vc Yd Yj) kO(aL Ar bM dB Id Ir Kn Kp Um Us) lW(cT dI hC iZ nH nN Uk Uo) Zq(bF bQ cU De dJ Mg Mw) Vc(aO bA Fr hB hG Ky oF) kG(bM cX Id Ir rZ Sr) De(Fd Hl Lp Rt Sj) Gh(cQ CT Qd Vt) cC(Fd Ho Ux Uy Wd) eM(Is Jt Mr Qd Qe) nN(An cZ dA Id Mk) Eq(Fr Fy Ho Tn) Vz(Ke Ky Mt Qd) bM(mE nB nH nJ) mU(An Hc Qz Us) mW(Cu cX iZ jI) Rh(Vh Yh Yi) dJ(Hl Uy Yj) nJ(dM hX Id) iZ(Em mH oO) kI(cX kE rC) An(kE oQ) Yl(Ky Qd) Ql(Va Vi) nH(Cu Id) FdGp FidM NqPe NdSj HoPh InYi YjcS ShKo RvOz RtcQ UkmH UmnO UnmP UsnD eDoQ nTrX} hV{oQ(Ad aF aK An Ao As aV Aw bF bM bP bQ bZ cE Ch Co Ct cX cY dA Dc De dF Dk Dp EF Fn hB Hc Ib Iz Jd Jf Ke Oa oE oF Ou Qu Qv Qw Qx Qy Ra Rm Us Vs Tj) kI(Af aG aP aW Ba bL bO bS cG cQ cT Cu Cw cX dF dM Fa Fb Ic Id Jd Je Ju Jv Kj Kl Ko Qu Qv Qx Ss Tn To Tv Uf Uk Un Up Vs Vt) mS(aF aK AP aV bN bZ cK cL Cw Db dF Dg dM Gp Jd Kd Kg Kn Kp Kq Ow Pj Pk Qm Qv Rh Tv Ug

Figure 31 Continued

Figure 31 Continued dA Dp iA iJ kR Qv) jl(aI aK An aQ bJ cK dR Kf Ld oH Pk) qV(aJ AN bH dA gL iZ kQ nY Tz Uk) Fy(Dp Hp Rt Ry We Yg Yj Yk) rC(Af bJ
Bn dN kS oK Qn Up) IN(aQ aW cP iH Kq Ld oH Ow) rZ(cK dA Kn Ld Ow Pk Qv) jR(An Ax cK Cs cX dA) Hp(bJ Hq Js Qa Qe) Yk(Cq Ij Jn
Pg Tz) jL(aJ Ax bA cN Cs) Vq(cF jH jK Wc) jU(aJ Ax cX Uk) Zq(Ko mM To) bJ(Gn Hl iC) qY(aN bH bM) jO(bB dF iA) An(iB qX) Du(Dd
mE) Hq(We Ye) Rv(eC nK) dI(hW hX) iC(aQ aS) jT(hC Kf) DpLx GnIl MwWe IjRy KlhR OrjH UkjV UmbX aJjG hWkS} Sf{Nd(Ad Al aM
aN Ax bB bL bM bR cD cF cG cK Cs Dc Dd De Dk Du Ed Ex Fp Fw Fy Gp Ha Ho Hv Ij Io Iq Ir Is Iu Jd Jk Jl Jn Jr Js Ju Ke Kk Kp Kq Kx Li
Lj Md Mn Mq Mr Mt Mw Mx Na Nb Nm No Nq Nr Nu Ny Oa Or Pi Pj Qa Qb Qc Qd Qe Qh Rh Sr St Tz Ub Un Up Us Vh Vi Vt Vz Wb)
Dk(aN Ap aW bL bM bR bW cF cK De Ed Gl Hf Ho Hp Hv Jm Kk kP Lh Lj Ma Mm Nb Nh Nn Ny Om Ow Ry Tr Uw Vc Yg) pl(aW bB bL
bM bR bX cA Cq Fd Hv Ij Js Ks Kx Lh Mn nK nO Nr Pj) mM(Cu Gp Ij Jn Js Ke Kq Lh No Nv Tn Uf Zq) nK(al aK Cu dA dJ Jn kP Kq Lh mH
nT Nv) Fy(eF gC Hv iA kP kS nJ nT oE oH Rh) kP(aS Cu Dd Ih Ij Ip Jn Js Tz Zq) Hv(cF Fw Gp Hf mT Nb Nf Qy) lj(gC iA kS mY oN oQ pF)
oE(cF Cu Ke Kp Uw Zq) Nb(bR cX Kk Tz Wb) Qh(gC Ju nH nJ Tz) Jr(bM bR cF Dd De) iA(aM cF No Qt Zq) kS(Ke Ng No Zq) Cq(fB nJ pK)
gC(Fd Hq Tn) Dd(nT oT) Jn(aN mE) Kq(mP oQ) cF(fP Nu) fB(aL dD) mY(aW Hq) DcUb EdKp FwnJ MnnR MxmT ZxbL PzhC JunB bRhB}
jU{nH(aF Al An Ao Ar aS aV Bc bM bS cD cE cJ Co Cp cQ Ct dA Dc dL Dp Id Iz Jd Ju Qn Qx Ra Ri Uk Up Vp Vt Tj) nK(aJ aP Ar aS Ax bA
Bc bM bS bX cJ cR Cu cV Cx dG dM Ed Fa GP iP iZ Kp Kq Oa Qn Ra Un) nA(Al aS bO Cu Ju Jv Qn Qt Qz Ra Ub Ue Uk Un Ur Vs Vt)
oQ(aF Ao Co Ct dH Dp hB Jd Je Jf Qx Qy Qz Vs Tj) Wf(eD In Jo Js jY Lh Lj Lx Lz Ml Mp Mq Qb We) Zx(eD Me Mh Mm Mv Nb Ne Nf Ni
Oy Pc Wc Ye) nN(AN aY cP cX cZ dA dJ Fn iZ Uo Up) Wb(Is jP Js Lx Lz Mh Mp Mq Pf Qb Qd) We(Iq Is Jh Jl Mt Mw Nb Qa Uc Yh Yi)
Yh(jI jY Lz Mh Ml Mp Mq Of Oy) Uk(kI lW mE mH mI mU nD nJ nO) nD(Dc Ju Qn Qz Up Ur Vs) Vz(jY Mc Mj No Qa Tz) Yi(Jk jP Mh Of
Oy) Yj(jD Nc Ne Nk Nl) Wh(Lv Mj Mt Nb Qa) Tm(iC jI Mc Nb Tz) mI(bA cX dG Ub tF) Ye(jD jI Jl qW) Up(mE nR nT nU) nC(cX dK Tt Uo)
Wc(Jq Lh Qa) dL(mM mW oP) mU(Qt Ur Vs) kI(dF dG Uo) kO(aJ dB Kc) Mh(Wd Zq) mW(aJ dG) nJ(Ri Uo) BckG TzZw YgQa dJoO}
kI{jQ(aJ An aP Ax bA Bc bL Cs Cu CX dF dG dM gL iZ Jd Ke Kn kS oN Or Ou Pj Ql Qz Sr St Uf Un Uo Vq Vt) iB(aK aQ aV Ax bA bJ Bo
cF Cs cT cV cX dI Dp Ic iP iZ Jd Pj Rj Sr Ug Uk Um Uo Up Ur) rY(aJ AP Ba bG bL bP bQ bS cK cW dA dD dE dF dG dM In iO iZ Ke Kf oH
Ow Qw Qz Us) rC(Af Ax Ba bE bG bW Cs Dp Fa hC iP Kn kR Rh Uk tF) qV(bH Cu hC iO iZ KQ nY Or Rg Uk Un Uo Vt) qW(aJ aP bA bL
cW dF gL hC iZ Kn oN Or Uo) jY(aK aS aV bJ cF Fn Jd oE Qv Rj Uo Vv) jI(aK aS aV aZ bA bJ cF Fn iO Pj Wm) iC(aR aS aZ Dp Ri St Ug
Um Uo) jR(bA Bc Fa Ql Qz Sr Uf Uo) rZ(aV cT Ic Jq Pj Ue Uk Up) hR(aS bA cT Qv Uh) Kq(hX Qv Rf Ug) Lh(Qv Ug Um Tj) Uo(lK qX qY
rA) Pj(hA jL lN rB) bB(gZ oW Um Tj) eD(Fa kQ Ql Tn) Jd(jD jL lK) eC(Ld Tz Um) hW(cF Cu Dp) jT(Cw Jv Uh) hA(aR Dp) hX(Cu iZ)
jD(oE Ou) jL(Ke Un) jV(dF Uk) lN(Hw Rj) SrlK RyLi OrcF UrqY iOjH iZrA} Ew{Nd(Ad aF Ao aQ aX Bb Bc bV cO cR cZ Dc Dd dH Dl fP
Ik Io Is Jh Jt Lu Mf My Nm Pb Pd Pe Qc) aN(Ax aZ bG cL dl Ih Ij Il Jq Li Lv Lz Mh Mk Ml Mr Ms Mv No Nr Oh Oi Oy Pe Qa Qb Qd) aW(aA
bS bW cT Dl Dw Ih Ij Jq Js Li Lv Lz Mh Mk Ml Mr Mv Nc Ne Nk Nr Oh Oi Oy Pb) bR(aH aI aM aY Bb bM bZ cC cG cW dF dG Jr Nh Nx Pd
Qb Qe) Mb(aO aY bF bG bM bQ bZ cG cL cU Cx Dd dI Ml Ms Pc) Mn(Ad bP Cq Hx Jl Jn Jq Jr Mt Ni Qa Qb) Hx(aO aY bB cF dK Nc Ne Nh
Nl) aD(aZ cP Cu Dc Il Jr Lx No Qc) Cs(Hv Lw Me Mf Mg My Nq Oy) Fp(Io Jh Jn Jq Ma Mf Qc) bM(Aj aS bI cF It Of Oi) aO(dF dN Mt Ne
Nk Qb) Lj(aX Jt Nq Ny Pd) Nc(aV bE cS Mv) Of(aY cC cW Nx) Ne(bW cS dK) Qe(Cv Ly Mv) aM(bS cF Cv) bB(aG bP Jo) Di(Hq Me) Po(cQ
Mw) Nk(cS Jq) Qb(cQ Mg) Pa(cY Oy) Pe(aH Jh) cB(aH bW) AsQc CtCu NoNb HqcO IndC aJcS cCcX} Qd{Of(aA Il In Jh Jn Jt Lh Lw Mb
Mm Ms Mt Mx My Ne Nf Nh Nl Nm Nu Nv Nx) Mx(aA aN Hw Il In It Jr Js Lw Lz Mb Mh Mj Mk Ms My Nf Nm Nx) My(aA In Jh Jn Jt Lw
Lx Mm Mt Ne Nf Nh Nl Nm Nu Nv Nx) In(aA Fp Jn Jt Lh Mb Ms Mt Nc Ne Nh Nl Nm Nu Nx) Nf(aA Fp Lh Lw Mb Mp Ms Ne Nh Ni Nl Nu
Nv Nx) Il(Fp Jn Lh Mb Mh Ms Mt Ne Nh Nl Nu Nv Nx) Mk(Fp Lh Lv Mb Mm Mt Nc Ne Nh Nl Nu oE) aA(Hr Jn Mb Mj Ms Mt Ne Nl Nu
Nx) Jt(Hw Ii It Js Mb Mj Ms Na Oy) Nu(Lw Mb Mj Ms Ne Nl Nx Oy) Lh(Hw Hx Ii Mh Mj Mw Nb Po) Nl(It Lw Mj Ms Ni Nk Nx) Nm(Fp Hw
Ii Mb Mj Ne) Ms(Jn Mt Ne Nh Nx) Ub(cD kG kP nJ oE) Oy(Jh Mm Mt Nv Nx) Fp(Hw It Mm Nx) Vz(jQ jR lK rA) Mt(Lw Mb Mj) Nd(Du Hp
Si) Wc(jK jP lK) Nv(Ii Mj Mw) Ne(It Nx) Yg(jH jM) Zw(jQ qX) Wd(qT rA) Wf(jH jR) Ye(jP qT) DwaG NqwP MbMm NhIt HpmS HwJn IiNx
YdjP WblN KfUu KpbM aLfB yJrC rBwD} hC{Zq(aE Bn bW cK cQ cS cT cU Cx dC dJ Hv iA kS Kx Kz Ma Mj MM Nd Nf nR Oh Oi oK oN
Or Ow pF Qu Rf Rh Ry Vi) Zx(An bG bO bX dB dJ Gn Gp Hv jB Lu mE mI Mj Mk Nd Nk oE pF Pi Rh Um) Ry(Ba cB cF Co Cu Dk Fb Fr Fy
Gp Ha Ij Jh Jk Ke Lh Li Lx Mw My Uw Yi) dU(Gd Lp Lt nI Oa Or Ow Rz Sh To Vz Wd) Wb(cB cF Gp Hv Kp Mj mS Nd Nf Or) nI(eM Ic jB
Kc Kf Kq nK Ns Op) Wf(Fy Gp kP Li mE nK nN Vt) fB(aL Aw cR dD dJ dK iJ jB) Rh(Ps Rz Uw Vw Vz Yg Yi) Vi(Cu Fy Ke Li Nv Pz Uw)
jB(bR Gh Oa Op oQ Or Sh) Gn(Hw Ii mT Pz Vq Vt) Vc(cF cL Fy gL Kp Vq) Op(mM mS nH nK nN) Uw(cK Mj Or pF Rf) mI(In jT Nk qV
qY) Eq(Fy Ng nR Qt) Gd(Ao nR oO pI) Fy(We Yj Zw) Gb(aM cF Nd) Rz(bR gC nR) nK(cP Cw Gl) Du(Nd pI) Ho(Lu Nd) Yi(cX Rf) Yj(Dc
Or) Pz(Hp We) Pj(Lv Ns) sJ(Ip Kr) oW(aL Sh) CuRt IzKf ZwVq LpoT OrUy dKpH eDoQ nUrZ} jD{Zq(Fr Hu Il In It jH Li Lv Ly My Ni Nq
Oh Oy Oz Qc Vz Wc Yg Yh Yi) Vz(aA Ii Is JH jI Jl Lh Mm Nm Nv Oi Om Pe Po qW Wh) Yj(Ij jL Jq jR jV Mk Mn Mp Ne Nk Nu Nv Pa Qe
Wb Yd) We(Hr Io Jl Ly Mb Me Mv My Nb Nd Ne Nq Oy Yi Ye) nN(aD Ap Bb Dg dM Gp Jd Jy Kf Kq Qg Tn Vp Vq) Zw(Jo jP Mk Mx Nc Ne
Nk Oc Oi Oy Oz Wc Wh) Wd(hA Ih Ir It jL Ma Mh Mk Mx Oi Oy) Wh(Hr Ih jT Ly Mb Me Nb Nc Nd Oi Ye) Pj(aZ cA cX iC jY Kx Ly Mk Mt
Or Wm) Wb(Jh jT Mf Mg Mn Nc Nu Pd Pg qT) Yi(Hx Io jL jM jQ Nl Nm Pb Pz) Wm(Gp Ly Mk rC Uh uR Ye) oQ(aD cK cP cQ Jd Ju Uh)
Ye(Jh Jk Ml Pz qW) nH(Al Ap Gp Kf Kq) Yd(Ik jO Nq Yl) Wc(Ii Jl Lh Po) Uh(mU Mx nA Qa) Yg(Mx Nl Pb) Yh(eD Jm Pc) Jd(mI nC nK)
Kf(Iz oO Ra) Up(mI nA nO) aJ(mW nC nT) Al(mW nA) Yl(jM Pc) Tk(rN zH) DdmW ExtQ GpnK LusK KxuR UokP PkwE dMlX dRfR nIqZ}
Tk{vV(aV bH bQ cF cG cL Co Cq dH Kr lO Mk Mn Mp Mt Mx Nd Oz Pd Pe PF Rg Tr Us Wm) wE(aH aJ Ap aQ aW cW Gp Hf iP Ju Ke kQ
Kr Ks Lu Mn Oi oK Pg qI Rf vO zA) Ap(fN hO pS qC qZ rN rQ rV tU tX uG uO vB vI wF wG wJ yH yL zH xA) Fn(qI rN tO tS uL uO uT uV
vO vP wG yL tM) tT(aV Co cU Fy Jo Js Mn Mw Nr qC rP uG) vO(aV bM bP Jq Kj Kx oF qA tV tX Ub tM) aH(tN tV tX wD wJ wP yH zH zI
tL) Mn(fN qZ sK tN tQ tV wQ yD yJ) cU(fN tN uU wF wL wP zA) tL(bL cD cW iA qG sO Uu) Uu(hO rV tO wF xA) tN(aW bG cW eC eT)
tM(hG Kk uU uX wG) Pz(hO rN uO vI) qD(dB Kr Na zH) qI(sK tX wB wG) Wm(uP wB yH) Mx(qQ rC tV) aV(tQ uO vT) rN(Ba Kl Qu)
Cw(rV zG) cB(uL vT) cW(rQ yH) tO(dJ pF) tV(dA Jr) rC(sO vP) sK(aA jI) wG(Jq Mb) yL(aN rY) uY(aJ dB) ExnW IbzI TrvP TvyE IrIu
KxwB cDrQ cOuO} nK{Zw(Jn Jq Jr Js Nv Nx Qa Qb Qm Tn Tz Yi) Rh(Eq Hl Op Rt Rz Vi Wd Wh Yd Yg Yi Zx) Si(Cq Dk Ij Is Jn Ke Lh Mn
Nq nT Tz) cD(bA Cu dF Dg Gl Gp iO Kq Ou rZ Tn) jY(aG aS cP Dg Gl Gp iP Jd Ju Kq Uh) Yk(aK aL aQ bQ cY dJ dR nT Nx oH) rZ(Ih In It
Jm jQ lX Ma Qb qW) Cu(Gd iC jQ Ps qV qW rA Vw) We(Hq Hu Jq Mv My Nv Nx Tn) nI(dF eM Gh Gl Gn Kq Um Ye) No(aK aL iB jL jV lN
Rf) Wb(aK aQ aU dA dJ Gp) Nv(Hp Ps Ry Vi Vw Yg) iB(aS cP Dp Gp iP Jd) qV(aJ iP iZ Kq nY Tz) Gl(aK cJ Gd lK Om) Hl(cR Cv dD Ip Iq)
Nx(Rt Va Wc Yg Ye) cP(iC jI jO jP) eM(bR cX Nk pF) qY(aJ bM Id Tz) jQ(aJ dM Sr Tz) Jl(Hp Ry Vi) Lh(Mk Nc Yi) Cq(Eq Sh) Ua(Eq Ye)
Hq(dD Fi) Rv(cY eC) Yl(dJ Tj) Uh(jM qT) aL(fB Ir) qW(aJ Tz) AoGd DraV DuoH FdRf GbcR GnHx GpjV HoJn IuYi YjPd WhgC WfmH
JkYe PsbE LdpI aDjI aKdU bArA dMjR iPlK} wF{Vt(aJ aY bQ dG Dk hP iA Jk Jl Lu Ly Mj Nq nW Pc Qm QW Qy rC Rg Ri uR uU uX vW
wQ) iA(Ad Ap Bb Bc Dg Dl Fb Ic Jd Kc Ke Kf Kl Kn Mm Pj Ri Uf Ug Uh Vq tL Wm) Bb(bF Bg bQ Dk Ef Hu Iz Jd Je Jk Mu Mv Mw Nq Oa
Oy Qy rB Ri vA wQ) Ri(aQ aR bQ Cv Il jI Jk jM Lu Mv Nq nW Of oK oN qT Tz vH tL tF) Nq(Ap Dc Dl Fy Hb Id Ke Kg Kn Ko Oh Pj rC Tz
Uf Un) Kn(aH bQ cS dJ Dk eT Ib jM nW oK Ra rB Vs wE tF) nW(Ap Ar Cv Ic Jy Oa Pk To Tz Un Wm) uR(Ar Cv Dk Ef Id Ki Oa Pk To Tz

Figure 31 Continued

Figure 31 Continued

Ye) bL(Hf Hl Kn Lh Lx oN Ow To) Wc(Is Lh Nv Nx Tn Up) eC(dJ Id Mn Nc Rt Tv) Cq(Gd Hp Op Si To) Hl(Hq Iq Mx Qa Qb) Ow(cl cK Nn
oK Vq) dD(aG cI fP nR) Tn(bW Uc Uw) aL(aO cI To) Gh(dB Hq) Gb(Dd Hq) Tv(Hp nH) Hf(cF Me) Nx(Ru Uy) Uw(Ng Qh) Ux(bI Iq) bH(dJ
lX) cR(Qu Uf) FdQv MvcF MxZw HodB ToaQ JfaK} qW{Vz(Fp jK JM jP Jq Lh Lv Lx Lz Mk Ml My Ng Nh Oi Oy Pf Po) Yd(hA It lN Ma Mg Mn Nd Ne Ni Nk Nl Nn Oh) kO(aY bF cI cJ cT dI dJ gL iO Kn Um Vq) Wc(Fr iC Ip Ng No Nq Nv Oi Oy Pd) Ye(It Mh Mr Nd Nn Ny Oh Oi qT Wf) nA(bA Cu gL Gp Kn Pj Qn Un) lW(An bA cT dI gL Kn Uk) Wf(Hv My Oi Oy We) mW(Cs Cu Id iZ Tz) An(kE mU nD nN) cX(mM nN nO nR) nJ(Ha Id Sr Tz) bA(mE mI nT) gL(mI mT nT) kG(dM Id Tz) We(Nb Nx) Qz(mU nD) nN(dA Tz) CumI FnoQ LvYl MmZx WbOi ZwJr UomU UmnO bMmM fRlN nHiO} iC{Wc(Hx Io Iu Jl Jr Ni Pa Po Qa Qc Uc) Ye(Hx Io Iq Ir It Iu Mk Oe qY Zx) lX(An Ar bA cT dA Id Kn St Tz Vq) Tz(kP Mk mT nT Vz We Yg Zw) Vz(Jh jL Jq Mj Mx Pa Wd) Yh(Fp jG Mh Mj Mx Nf) nT(An Ar Kn St Um Vq) Zx(Ij It lN Mh Nf) Mx(Mk Wf Yi Yl) mT(dI Gp Kn Kq) Dp(mW nC nJ) Mj(Wf Yi Yl) Yg(Jn Jr Mh) Yd(jM Nd Nh) Pz(We Wh Yl) Pa(Wd We Wh) cP(mU nB nH) mE(aW bJ dR) iA(wQ yJ zG) oO(aR Kp Um) Mk(Sr Wm) Ra(Kf Kn) Ri(kG yJ) Vq(mH nU) nN(Kq Un) oQ(Qz Vo) CumI HanJ NfTm HwYj JhWd JqYl KnmH UmkE aRfR bJlW} qT{Yd(hA Hu Jk jL Jm jP Lh Ma Mu Nd Ng Nu Oy Ua Wh Ye) Wb(Hx In Ip Is jK lK Lv Mh Mp Mq Ng Nq Oi Oy Pc Tz) Zx(Hx Jm lN Ma Md Mh Mj Mv Mx My Ni Nq Ye) kP(Fa Jd Ql Qz Sr St Tz Ub Uf Uh Un Vq Vt) Ye(Hr Iq Ir Is jL jO Jq Mf Ms Qa Qc Tz) Wc(Ip Jo jP Mb Oy Pc Pd) Wd(Ir Jh Jq Lv Mw Nx) We(Hv Iq Is jK Lv Qa) Wh(Ir Is Nx Oi Qa Zw) nN(cP Kq qZ Tn) Vz(Lx Mk Ml) Yl(Md Mx Oe) Oy(Wf Wg Zw) oP(Gl Gp Kq) Tm(Lv Nl) Uh(mH nB) Vo(oO oQ) CunU ExuY KqmW UmR} jP{Yh(hA Hq Ij In It Jn Jo Js Lh Md Mf Mg Mh Mj Mm Mw Mx Nf Ng Ns Oh Om Vz Wc) Wf(hA Hq Ii It jO Ma Mj Ml Mx Nd Nf Nn Oe Oh Oi Oz Pa Pc Yd Zx) Yd(Il jH Jl Jn Me Mk Ml My Nb Nd Ny Oe Pc Pe Vz Ye) Wc(aA Fr Hu Ii Jl Jq Mk My No Ny Oe Pe Qa) Vz(Jh Jl Jq Pa Pd Qa Tz Wd Yi Zw) Uh(kE kO lW mI mU nA nD nH nN) Yi(Jo Mm Nf Oh Oz) Wd(Jo Ma Mm Nn Oh) Yg(Ij Jo Js Ng) Ye(Me Nb Zx) Yj(Hw Oh) CumW CwoO NnZw MmZx JqYl UrnR VvoQ} sJ{Nq(Hr Mm pS rP tR tT tV tX uO vW wC yL zH) Qy(aW bM Db dH dM Hq Ib Kp Ky Mx Nb Pa Ra) Uh(Ad Bc Ch cV Cw Ib Kd Kj Li Mf Tr) wD(aQ cY dR Jn JR Js Pg Ql qP) Mf(Cu Fb Ha Jr Ke Lh Pg Ql Tj) Fa(jK Kr Lx Ny pS vP vV) aR(aY bP Iu Kr Pg wE) Cq(hW rP rW vU yH) pF(aZ Lx Pg rW tT) Wm(aI cI In Kz) Ib(Kf Kl Ql Qm) iA(dH Kr tX yL) jM(iJ iP Lz St) Ch(Dg Kl Qg) Hf(cB cD Ed) Pg(Bc iH Jl) Dg(Ef Ua) Qg(Ef Ua) Ql(cV Kz) BcyH IpJy StM KqKy aJcW cDkR hWiH} Dw{bM(Ar cF Ct Ij Jo Mi Mr Mt Mv Ne Nr Oe Oi Pg) Mb(aO Ba bP bQ cF cG cP Ct cU fP Jn) bR(dE Hw Jn Jr Lj Mf Ml Na Nk Nr Qc) Jn(aG aO cS Dg Js Mt Ne Nh Nl) Ct(aN aY cC dB Dk Jh Jm Qc) aD(Aj aO aS aU cF cP lj Nr) Jo(aM Cq eM Jh Jm Jq Nq) aG(aS bB Hx Lh Mn Mp) aN(aS It Lj Nr Pe) aW(bI cF It Nq Of) No(aQ aU bJ Bo) Nd(aS Di Is Jt) Of(Io Oh Po) bW(cB Ne Oh) Aj(Jh Oy) Bo(Hx Jl) Di(Nm Qb) cC(Ax Mg) dC(aS cF) HxcB IpLj OhcO aEaF} wQ{Nq(aP CU dF dG Fa hB Iq Jl Ke Kf Kn Kx Oa Oh Ou Qa qZ St Uc Un Vt Wm Tj) wD(Aw Dk Ef Iz Kn Nx Pk Ql Qm Ri To Ua Ul Vs) Wm(Ef iA Ib Jd Jk JV Mb Nr Pc pF rB) Cu(Aw aY Dk Ef Ib Jh Jk Vs) Ip(Fr hB Jl Lh nY Ur vI zI) Ou(Aw aY bC Ef iA Iz Jk) Vq(iJ Mb Tn Tr Tt uY) Ef(dG Jl Lh oF Pd) Lh(Ch Hc Ib Iz) Vt(Jk Pc Uu uY) iA(dH Kf Lx) tV(Bb Lu Pk) Jl(Jk Lu) Kn(hW wE) uY(Ar Kf) DgUu FrIz UadH TnPd SrVs JvOa KdhB VujV} mI{qY(aE Aj aM aN Ar aS aV bE bH bJ bN Bo cJ Cs Ct Cu dI DL dR Ed Fa Id IZ Oa Or Qv Qz Rg Rj Ub Ue Ug Uk Um Uo Ur Vs) qZ(Ih Ip Iq Ir It Lj Qa) Rh(hW rB rX Vi) bA(jL jM jR rA) iH(aL In Li lN) jV(aS In Uk Up) rY(cT Cx kS Qv) Cu(hX jM rA) Zw(Nx Rg Tz) aQ(hW rX Yk) iB(aS In My) Cq(Eq Uk) Qg(bB hW) Rg(Vi Yg) Nx(Va Wc) Ug(jT Kq) eC(Lt Rv) jR(aJ cT) AoGd EqUa NojL LxMk UbLi HqWe HvYj YkbQ StjM KfjT OrcF UhlN bJhW dBeM rXoH} jB{To(aW bI bL bM bR cA cD cF cQ dJ Fd Gh Hx Ik nU Ow Qw Sr Vv) Rf(aW bI bN bR cA Fa Fd Jn Lh Nb No) cF(An bH bR cX Ex Fr Mx nO Sr) bI(Gb Qz Rm Uc Ux Vo Vv Wf) bN(cQ dE Mk Ns Ny Wd Wh) Gh(An dB Ex Hq Id Qz) cA(cX dB Ex Id Mx) Jn(Mk Ne Nh Nl) Ny(Lh Mn Nn Pk) Us(Fd Lt Ux Zw) Ao(Kl Ux Vw) Gb(aW Dd Fd) bR(cX Ex Hf) eC(Qw Rt Up) Vi(Jk Nv) bJ(Gp Qg) FdNn GlSi MuIb MvQw MxZw HpbL WhaW WfaS LhUw VscG PkkS aLaO} Nd{Sh(aN bB bM bR cK Cs Dd Dk Hv Jr Kk Li Lj Mn Mt Mx Nq Qh) Du(Ed mE mT nJ Nu oN oT pF Qy Rh Up Us Vc) Wb(aM aN aP bM bO cD De dF jT Rh Uk Us) Si(Dk Hv Ke Li Lj Mn Mr Pj Qa Un Uw) Ho(aM bM cD Ik Rh Tz Ub Uk Us) Ry(bB dF Oa Qh Tn) Hp(Ed Jk Jl Qa) Vz(bM cB cD cK) Eq(cG Jd mT) Yj(bB De Hv) Vc(cG dF Kx) nN(iB lN qZ) Yd(jH qY) Tm(aN cK) Vi(aM bM) HlbM HvLp YiRh ZxjV WcPi WfbB KqRz NxUy eCpH} nO{Um(aE bB bX Db dD In Iq JR Js Lh Lv Nh Nk Nx oO qY Qz Tz Ub Up) Dp(Cq Cu eC Jn Jq Lv Mu Nv Nx Qu Tz) Eq(Co Ef Hq Hu Jh Mv Om Qu Ua) Gn(cR dD Hq Mw Nv Nx Qm Tz) Tz(Hl Hp Ug Va Wc Zw) Ug(bX gL Lv Pz Qu) Hl(cR Hq Ip Qa) Jn(Si Vh Wc Zw) Yj(cR dD Rg) Vh(Ij Lh pI) rY(An Dc dI) rX(An aS Dd) Hp(Mw Nv) Wc(Lh Qm) Rh(Vi Yi) pI(Du Ry) TjbB GpWb NqYe UbbX InSt YgUu WeNv QuUr JmqZ OrcF VidD aSiB dRjH} mS{Yi(aF bX cD cQ Cu Fp Hv Ij Is Js Kk Ko Lh mE Ng Nm Nn Nv Qh Rf To Yg Zw Ye) Eq(Co Ef Hu Ij Iz Om Qu Rz Ua) Yg(Ij Js Lh Nv Qc Qh Uf Uu) Uw(bL Ij Js Lh To Uf) Hp(Ao Ij Js Qa Vq) Hq(Gh Hl We Yc) Wc(Lh Nx Qm Tz) lN(cI cJ cT dI) Ij(Ry Si Vi) Zw(Is Jn Tz) Ao(Ux Ye) Hl(Js Vq) Yk(Jn Tz) Yj(An Tv) Qu(Hc Ur) Ps(cD Us) Um(eC Lh) Vi(Cu Jn) hR(aS Rh) hX(kS Pj) YfUs GpWb IsYe JdhW RzbL VqcF dIrY} Nx{Of(Fr Ir Is Jt Lh Lx Mt Nm Nu Nv Qa) Mx(aA Fr Hr In Jt Nf Nm Nu Nv) We(kO mE mU nA nB nD nH nN nU) Yk(kG lX mE nB nH nU oE) Ye(mU nA nB nD nH nU oW) Ly(tT uM uY wD wE wP) Mt(aA Fp It Jt My Qa) oW(bB Rm Ur Va Wc Zw) Nu(In Ir Jl Lx Ms) Qa(In Ms Nf Nl Oy) Va(lW mE mH nB) wD(Jk Mk Nq) Fp(Nf Nl) Gn(oE oP) Yj(nB oE) Wc(nB nH) Rt(nN nU) DunJ MktT NlaA InIt YdjH ZwoQ} iB{nF(aS cP cQ dI iP Jd Kf Pj Qz Uh Um Up) fR(aE aO cG cO cS dH dN hA) lX(AN cX dM iZ Qz Vq) Dp(kO mP nA nC nH nJ) nU(aJ An Cs cX iZ My) Ur(kO mP nA nD nJ) My(kP mW nC nR) Vz(Jq Oe Wb Yd) Zx(Me Mh Mm Oy) We(Jl Jq Qa Yh) aS(nA nH nJ) nT(aJ cX iZ) mW(iZ Um Up) Ye(Mk Oe) Oy(Yh Yi) nN(cZ Up) mU(aJ cX) nJ(cI nD) kG(Cu iP) kP(An iZ) oP(Dl Kl) MhWb JhWh WcOe QzmY TmOz UmoO aVnH dImT} iA{wD(Ap cU Dg dH Dl Ip Jd Je Jv Kc Kd Kf Kn Kr Kz Oa OH Or Pj Qa Qx rB Ri Uf Uh Un Vt Vu tL) Kf(rQ tX uN uP uW uY wE zH) Vq(tQ tT uR vW wG Yj) zH(dL Ip Ou qZ Un) Wm(rB rS uR yJ) Yj(aM Ha Lh Lx) Ou(uR wB yL) Uf(tQ tT uY) Gp(Du fR) Uh(dL Ub) dH(uR wP) tT(Ap bW) wE(Un Vt) oW(aL bB) CuRt MmqZ HpJl IpvS SiKe QvUw KcuY KnuO VccG VuzA dGuR mWjH} kG{rY(Bb Bn Dg Id In iP It Kc Ow Pk Pz Rb Rg Tz) Yj(An Hq Hv Il Iq Ir Js Mt Mx Qa Qb) Yk(Cq Cu Jn Lh Ng Nv Om Qh Rj Tz) Hl(aS bI bJ Ip Jn Vq) Zw(Ao Ih Jn Jq Js Tz) Hq(Dp Gh Gn We Ye) rX(dC Pj Uf Vv) Dp(Ir Lh rB) Jd(hR hW rB) Wc(Cu Jn Us) Rh(Fd Op Yi) Ho(Ip Jn) Ih(Hp Yi) Yg(Nv Om) Wb(Hv Iq) bI(Gn We) hX(aJ lN) CqEq NoRf IraL NvVi OaOp dMjR} jV{Zx(Jm jT Ly Ms Nb Ne Ni Nu Po Wb) mW(aJ aW bA Dd iZ Jv Kp Uk Um Up) nH(aS cP cQ dR iH Kp Ra Rb Um Vv) We(Jh Jl Jq Mt Nb Qa Wf Yh Yi) Wb(Ml Mp Mq Pf) Tm(Ly Me Nl Tz) fR(dR iO Kx Or) nC(aJ iZ Jd Up) Vz(Me Mr No) Uk(lW mE mH) oP(Ba Dg Kl) Mh(Wf Yh) Yi(Jk Of) Yj(Nc Nl) Wh(Jq Mt) Kp(nN oQ) iH(nD nF) oO(dJ Um) WmhP PoWc MrYe UbnA YhOy UpnR PkwE} Mx{Nv(aA Hr Hw Ii In Mk My Nf Nl Nm Of Oy) Jt(aA Aj aN Fp In Mb Ms Ne Nf Nl Oy) Lh(Hr Hu Ii In Lw Mh Mj Mm My Nf Nm) Nu(aA In Jl Jn Mk Ny Oy) Nf(aN Ir Jn Li Mm Nm Ny) In(Ij Ir Jn Pi) aA(Jn Li Mm Mt) aN(cD Jn Qc Uh) Kp(bM dJ Ur) pI(Ry Wc Yl) Ik(Jd Kf) eM(Wd Wh) mT(Hp Si) wD(Ef rB) AjBa NqrQ MkoE QgVt KfUu UhoN aLoW} Du{kS(aE aZ bR De Gp Io Ir Jq Ke Ld Ny Pi Qm Tz Up Us) oT(Al Dd Fw Hq Hu Jk Jm Qu Ru To) pI(aM bL De Fw Jn Pi Qu To Uf Uk) pF(aD aM cF cG Fw) gL(aE bR dH Pi) To(mE mT pH) Uf(mM mP nH) nJ(Cq Nv Op) Hq(gZ lX) Jn(mM pK) Us(Nb Qy) cF(oH oN) nH(Op Rj) DdoO FwmU GpmM HvmT aDoN bBpK bJlX} Kf{Uu(aS Ax Cs Jd Ko Lj Lz Mk Nh Oa Or Pk Ra Rg Ub Vt Wm) hR(Ef Iz Mk Mv Nq nT oO Ra) Ex(eZ qZ sC sM vB) bM(Aj aS Jo Of Vt) Cs(Ik Of Rf Ub) Lj(Ik Of Rf Ub) jT(nN oO oP oQ) Aj(Mk Us Vt) Ef(Jd uO vB) Vv(uY vB yJ) fR(hA kS lN) rB(tO tT yJ) Ib(rQ uO) EqoE NquO NgrQ IzKq JkvB VtaS cBuY} Lh{mM(Gn Hl Hp Si Yg Yi Yj Yk Zw Zx Ye) nC(Ao cO Dp Qx Qz Ry Vi) nH(Ao Dp Qx Ry Vi Zw) mE(Ry Vi Yg Yi Yk) Zw(gL nA nR pF)

Figure 31 Continued

Figure 31 Continued

Mt{aA(Js My Nl Oy) LyuM MsJs MyIs QaOy} jG{Po(Wf Yd) Me(Wh Yd) LxWf TzmW InYh JhWe} Qa{Nl(aA Ms) Rm(Vc Zx) NfaA IkJd
WdeM} Lj{Yj(Dc mW mY) cX(Ho Yg Zx) IkJd} Vt{Pc(tO tR yJ) HpPs QgyJ cLuR wLnW} wE{Kn(Ef Ib Iz Uu) Pk(dJ Qm) TzPc} cF{pK(aE aL) TopH ShJr VciZ kErX} eM{Nb(Wd Wh) CqFc MvUy UaYe bRnC} Fp{Nf(Jq Js Mm Nm) NmNl} Tz{Ho(bO Si) WelO JkwP nUhW} Yg{CqoQ UukE aMcX bOiZ cRmW} nD{Um(bX Db Hq) InPi QuUr} pH{cA(Sr To) DdFi WcRj RmbR} Ed{Hp(Iz Kp Pz) KpVc} Gn{nU(bL Gl) UwgP cRmW} Vi{Cu(iZ nB) KeiZ cGpF} nC{Gl(Dp Mk Oy) CuhW} rX{HfoO KnnT RhkO dGoQ} Aj{Kq(Lv Ml) BacD} Cq{nB(Sh Yk) AapK} Ha{InmW YjpF RyiJ} Hl{cR(mW nB) PekS} Oa{IkJd ZxRf RyiJ} mY{Ye(Ao Is) RvbN} oT{AnKx QtaW cRdJ} Yj{JloQ bLnU} We{HqkE JhlO} Pe{UhoN UvuR} Pj{NsdR MkOr} jO{NnWf PioO} nW{VvwL PktN} pK{TjaW aEbN} ArLwcD ChUftO CvRiyJ GhaMiJ MynUqZ NbSicX NgShkS HpOuiZ ToVchB YkbQoQ ZxVubO JkUnuU JrRhUy aRhWkE

Constrained panels with 3 analytes, where 4.3E-10 >= 'AUC p-value' > 1.0E-10. Contains 6,931 panels of 37,933,414 total panels evaluated. : Jp{Ub(Aw cD Ch cM Cv Dc Im Ji Or Qa Qu Rg To Vt Wm) Vb(As bM Fw Ho Hv Jt Li Nb Ps Qe Sf Uh Us Vt) Nf(Ih Jt Lv Me Mh Mr Nv Nx Oa Pe Pi Us) Vs(Ao bM Cq cX Dc fP Kx Lz Mh Or Ql Rg) Uv(Fw Fy Id Kf Kn Kp Ml Mt Nx Pi Sr) Je(aG AR cX Lz Or Ow Pa Rg Us) Rf(Ax Fp Im Ji Kx Lz Nw Qa Qb Qd) Uu(Dc fP Im Ir Ko Li Mk Mz Qd Ra) Lw(Jg Mb Mh Mt My Ne Nh On Qa) Uc(Ji Kf Li Mk Mq Mz Oa Tz Wm) Qu(aN Ar Ax bL Im Kf Pk Qd Um) Ow(bL cX Ed Li Mh Mq Qa Qd Wm) Fa(aH cM eF Jd Nm Of Oy To) Mb(Ih Ik Jq Lh Mp Nx Of Oy) Ra(Ik Li Lz Mz Nm Oa oE Oh) Mh(Ib My Mz Nm Pb Pe Rh) Ua(Cs Ji Mq Mz Oa Oh Um) Jj(bM Cs kI kR nH Rg Us) Or(dJ Ef Im Mj Qd Rg Wm) kC(bE bN cF In Ji kR Lu) My(Ir Lv Mp Mr Nn Us) Ni(Ih Is Js Nc Nv Nx) Oa(Al Bg Cw dJ Lh Nd) Uw(aO bM bU Gc Hv Vc) Ik(Of Oy Rg Vc Yg) Sf(gC Hv Kk Ut Vc) Kf(Ap Co Jo Kl lM) Vt(aG aS Oh Qg Um) mI(bE hC In jV Nk) iA(Ax Li Lx Qd Yj) Cs(Jv Mx oN Qz) Ef(bL bM Fb Im) Mp(Jg Nh Nl Nx) Mq(Ez Qt Rg To) Ii(Jq Lx Mr Nv) Oy(kR Mi Mu nL) aC(kI Lx Nx Qa) aN(Ar cD cM Lj) Mk(Jv nL oE) Mv(Lh Mz Nn) Mw(Kq Nn Pe) Nd(Kc Kk Qw) Ib(cX Oh Us) Sj(bM bP Mm) Rg(aO bM Im) cM(lW nN nO) oN(Ax Kn Lx) Ar(cD Qt) Mz(Ml oE) Ne(Ry Yi) Hv(Si Zw) Id(Ad gC) To(aO Ed) Ij(Il Ng) Kl(aW cX) Kq(Fr Ut) Kx(Aj Ap) Rh(Um Yi) Ny(Lh Pe) Vj(iJ pI) nU(lM qU) nK(Nc Nk) kR(Ch Lj) AxQw WmjD FyfP GcUf NqQy MmVc MxbM NhPi HuUs HxPe IzrZ SicE RcPk QaQt WdeM WheP JoKr RzbU UnoV UmH bHnL cOkG mFlN nIhC jMkN kIlL} aC{Kf(Ar Ax cD Ch cZ Ik Im Iz Kj mF MZ Ni nL Og Oi Pj Un Ur) Bb(aL Ao cD cM cN Cs Cu fR Is Lx Lz Ml Mq Og On Pe Qd Qe) Qe(Aj aS aX bA Cu Im It Jg mF Mi Ml Mm Nf Ni Nk Ok On) Jj(Ad Cs Cu Dc Fw Is Jg Jn Kp Mx Mz Nm Nt Ok On Pj Qa) Mt(aR Ba cN cX Lw Mk Mx mZ Nf Nk Nm Nw On Ub) Li(aZ Ba bM cM cN Cu cX Ih Is Mk Nw Ok On) Nm(aS bA bM cD cN dF Ih Jn Lh Mz Nf On) Io(aR bV cN cU Dc dF Dl Ni Pa Pk) On(Ax Bc bF cD cN cX Ef Is Mk Oy) nH(bB bU Cu Ir jK jL lN Lx Nk Pe) Ih(AR aZ bA bM cT dF Mm Nf) Cs(cM Mi Mk Mm Nf Nw Ok Vt) Mx(Ar Ba BC cX dF Kc Pj) Jg(aL aN cD cN Im Mz Nu Of) Is(aR aS cM cX Im Mm Nf) Pj(Ax aZ bA Ik Mq Un Vt) aN(Ao Ap dF Dg Nt Nu Qc) bM(Aa bA Cu Jd Ke Ko Pk) nK(Di eM Hq nl Nq Ok Pz) Kp(Ar cM dJ Lv Mk Of) Ax(Im Mm Mz Nw Qd) Cu(aR Im In Lj Mk) aX(Lh Lx Nu Nw Ok) Ba(aR Ct Lj Nd) Mz(Dl In Qd Ub) Nk(kC kF mI nC) cM(Ij Iv Ok Un) Aj(Ap Dg Dl) Ar(Nj Og Uh) Mm(bA cX Pa) Ub(Ke Lj Oa) Qd(Bc cN Im) Vt(Et Im Pa) aR(dF Nt Nu) mZ(Fb Kg No) nI(bB Nr Um) nL(dF Mu Qc) kC(bU Gl iH) Di(kI mI) Nd(Ho Sh) Nf(Cp Pe) Nw(aZ kI) Ok(cD cN) Vq(bE Ur) Pk(cX Et) mF(Ji Qu) nA(Cw Db) nJ(Bo Qm) AdOf TirC GcHv MkUn HobU InmI JncN TloD UteQ} Vb{Gc(aP aR As Cs De Dk Ed Ho Im Iz Jg Kd Mu Mw Nv Qe Si Uc Vi Xa) Qy(bA cB hC Ho Ij In Iq Mq Mr Nx Of Ok Om Pb Ra Tn Up Vp Vt) Ut(cI Cq Cu Is Iv Ju Kf Lj Ml Om Ow Ps Qa Qe Ra Sf Tv Uc Vp) De(aD Ba Bc Dc Im jB Jg Jl Jt mZ Pi Ps Qa Qt Tz Vt) Ef(Cq Du Hw Id Ij In Jj Kd Kr Ml Ny oD Pk Ra Tv) jB(cG Jh Jq Ks MW My Pi To Ua Vs Vv Wd Wh) Pz(Cs cT Em Is Jl Jt Lh Nb Nd Qa Sf Us Vt) dU(Bg Cw Fd Jh Kq Ma Mu Na nI Oh Op Tz) gL(cB Cq iJ Jo Nv oD Po Uc Vt Wb Xa) mZ(cL Dk eM Et Lx Ow pH Qh Tn Uf Yd) mI(Bg Dd It Ks Qh Vu Wh Tl) Nb(bM cF Jt Qm Qw Ss) Us(Is Jg nA On Ss Ux) eQ(Bg Ji Jt Nx Qm Vs) nO(Ch It My oV pK Ue) iJ(aM Ba Is Jg Tz Vq) Nd(mF Ok Pj Qa Wb) Kp(Cu Ed Ho Ps Qa) Fy(Mb Oe Ow Sf) Hv(Dc Hf Jd Kz) Jk(Dl Ir kN Vt) Jr(Dk Ho Im Vt) kC(cl Kf Nq Qz) kG(Aj Al It Op) oD(bZ Jd Ou Vu) Ba(eC hC Qc) mF(An Cq Na) nK(aL Hx Tt) Cu(aU Zx) Dk(aM Ju) Nt(bO cF) Ho(bU Jn) Im(cQ Tl) Iz(Na Up) Jt(Qv Vu) Ux(eC nH) cX(Is Qe) lY(Ih Zq) mE(Ib Ii) mS(Ip Kj) oW(Op Va) AdSf AsnJ DdJn TzQh TtoV IloP IqmT WbbA JhcB SsVu LigZ OkaD OnaO VqoT VonB aEhB bUdF dCfB} Th{wJ(aA Ad Ax Ba Cp Cs cT Cv Cw cZ Dc Dd Hw Hx Ij In It Iv Je Jh Jn Jq Jr Js Kf Kr Lh Me Mj Mu Mw Na Nb Nf Nm No Ny Ok Or Ph Qa Qd Qn Ra Ri Rj St Tv Uc Ud Uv uY Vs) wL(Ad As Bc bN Cp cT Dd Fy Im Ir It Ke Kf Kn Kr Me Mj Na Oa Of Qa Qb Ql Rm Ss Tn Um Uo Ur Us uU vH Vs wD zG) vP(Af Bn CQ Cu Cw cZ Fw Gl Ii Iu Ks Ld Lw Mi Ml Mq Mt Mx No Pi Ri uN wG) vV(Ap Ax cZ Fy Kd Kn Lx Mx Nl Pg Qe Sr Tr wG) tR(cW Fn Fw Gl Ke Kg Ky Nw Ou Qh wG) wG(aU cB cl cY dK Nr Pc Ur wF) wH(bC bR Kf Kl Mg Qw Uk vU vW) vO(cH Iq Ne Nl Oz Up wK) tO(An cH Ji Md Ph Qb) tN(cU Ik Na Nu Ou Ri) wF(aL aP Bg Jy Nr vS) vW(dD Kg Md Mt Pb Pd) mZ(bF Cu Ou Tz Us) Li(sK uV uX zG) tL(Co cY Mg Nr) zG(cI cU Hu) sK(eD qI qU) wD(aK bI Nt) uM(Cx jG rW) vT(bZ Rc uY) vU(bZ cH My) Ir(rC wB) Ur(sM uN) wK(aS Ky) tM(Gl uV) pS(Mj qD) AfyE ApyH BnuP TiuN NquT NdOr HuuG IbrN TnnR IkuV IqlY StyD LhmM PdwB PkwP aJsM bIvH bJfY bRuW wQsC rCjP qHrZ} Mz{rC(Bg cA cD fP iA Jv Ma Mk Nf Ng Nk Pj Pk Qu uY) Mx(In Is Jl Jt Lx Mt My Na Nv Nx Pb Qa Qe Qw) Ms(aA Fp Hr Jj Jr Jt Lw Lx Mt Nl Nm No Nx) Nf(aA Ip It Mb Mi Mm Mr Mt Ne Nx Ny On) Im(Jn Js Jt Lh Lw Lx Mh Mm My Nh Nm Of) Qe(Hr Jq Lh Mb Mh Mm My Nc Nh Ny Pb wE) Og(aA iC Ik Ip Jh Lh Li Mm Ne Nh Nr Nx) Nu(Fp Jj Jq Lh Li Lv Mv Nl Nv Nx Ny) Qa(aA Hr In Mk Mt My Na Ne Nm Nx Oy) Nm(Fp Lh Ne Nl Nx Ny Pb Qb) Hr(Hx Ip Is It Mb Nl No Pb) Jn(aA Ij In Lx Mm Ny Oy Pb) wQ(aF cY Ef Ib Kn Lh Lu Ua) Jj(bM Is Kf Mm Nl Nx Pz) Mt(Fp Is Jt Mk Nl Nx) Jg(Aj Ii Ij Mh Om Pb) Nw(Hx Ii Ml Mv Om Pb) aN(bU dJ Et Ic Uh Ur) Of(Jd Jt Kf Mm Nv) Lx(aA It Mk My) Nh(My Nx Ny Pb) Nl(Fp Hx In Jt) hP(Ez hR Mk Qg) Mh(Ir Qd tT) Uh(bM cM Hu) aA(Li Ne On) yH(Dk Ef Ly) Fp(Jt Lw) Mm(Hx Mb) Mp(Iv Nj) My(hR Jt) Qd(Ii Ny) Jd(bM Hu) Ra(jD wG) yJ(Uk Wm) sI(bC IL) sH(iH Iu) rR(iA zH) AjKf EfhV TiuY NtuM MwOn NeIs NjJr IhPb ZqoE JijD QywE KdrU KkeP PktQ bIuO qUkC jYkN lLrQ} Jj{Nv(Fp Im Is kC kI kP Mb Mm Mt Nc Nh Nm Of Og Oy Qa) Mx(bA Bc cM Kc Kk Ko Kq Lh Nj Nm Nu Pk Pz Us) Nx(Ih Jh Jl Jm Ms Nf Nn No Ny Og Pe Po Qc) Nu(Fp Fr Ih Ij Ip Ir Li Lx No Pz Qb) Jn(cD Is It Jh Jl Js Ne Nh Nn Ny Og) Mt(Fp It Mm Nl Nm Nn Ny Pz Qa) Iv(Ih Ii In Ir Jh Jm Nh Nl Nr) Kf(Ax cM Fy Mk Of Or Rc Ub Wm) bM(Dc Ij Ke Ko Kr Ok On Or Pk) Jt(aN Cs Ij Ir It Lv Lx My) Lh(Ir Is Js mF Mm Nm Ny Pz) nL(Ax Ba Cw Fw iH Jg Ke Tt) Tl(bU cF Nb Qb Qt Tn Tz) Nl(Fr Is Li Mm Nn Pz) nO(Im Is lL No Pz Tz) Nj(Fp Ii Jm Ma Mn) Qc(aN Fp Jl Jo Li) Js(Fp Li Mm Ms Ne) Qa(Aa Nf Nm Og) mF(Fw Ke Kg Ou) mI(Lx Nk Nw Tn) Cs(cD cM Kp) Is(kN nH Nm) Uh(aN cM Pk) Ut(kP mW Vc) mZ(Kg Ua Vv) nK(Ou Tt Wh) Ti(uY vB) Mm(Ih Li) Jd(Lj Oa) Kp(Ed Or) nC(lL Un) nH(qU rZ) iC(kK Tz) hC(Et Pj) kC(jQ kP) AaQd FpNm FwfA NtaN LwIm HobU IzkP PzLi JibL XaeM iBkN} cM{Mx(Cs dF hP Ji Ko Lj mF mI nN Or Pj Qd Qe Qw Un Wm) Uh(aG cN Dc eQ Fa Id Iq jD Ji Kn Kp Lz Nd Sr) kC(bA bO bV bZ cE cJ dF Dp In Ke Kf nN Nw Qa) nN(cX fR Hr Ld lW mE Mh mI Nf Ns Sr) Ji(aS Ax bV Cs Fp lW Mp Qe Ub wJ) oE(Ax Jd Kn Kp No Oa Pe Qd Qm) Lj(bM Kc Ko mI mM Nt Qm Vt) mI(aL Bo Ex Gp Im Ny Qa) iO(Fy Ke Kf Kn Oa Sr Un) Et(aN bA Fp kR lM qG) Vt(bM bV Im Ko Kp Mk) kF(Ax Gp iH Ke Kf Rb) Cs(bM Kx Pj Pk Uo) Ub(Ar gZ kN Li Qd) aN(Fp Jt Nt Ok Qd) lW(bQ cF Gl iH Ko) Aj(Jt Ko On Qd) Ax(kK Kp Or Un) bM(Im Kf Nw Qd) mF(Cw Ed Nw Ug) wQ(dH Fy Il Kn) Nq(lY nL tX) Zx(iZ oF oK) Lh(jM kI nY) Oa(Ko Kp Mk) gZ(Qt Rb Up) nO(Bo Ny Sr) iH(mE nD nH) Ar(cD Qd) Tz(Ho wF) Qe(Kp Vs) Kf(lM Uu) Or(Ex kI) lX(Fw Sr) nL(Mh Qc) rR(Kn Kr) TimU GpnK GzgL UeoD IpuP SjiZ QaTl QyeQ KewJ UmoT PktT bQlY

Figure 31 Continued

Figure 31 Continued

Figure 31 Continued jF(cO dF jD) Ow(eC oH) iB(jM oN) jE(cL cU) IK(cA gP) IM(iC oK) JqqV KpeC KqkS QlqU OuoH dReD} nH{jF(aR bC cX lr kN) cF(aL bB
bE) Gl(aK Om) Mk(Ou Uf) Rg(Cw Va) cP(jE jY) qU(Ma Ni) CuPs FwYg TzeC KxaV RvaE OwoW Umnl Ufbl aLbC aQjV aUcR iClL qZoQ}
eP{Wd(aY Jm Jq Lz Mq) Wh(Cp Mi Nn) Kc(De eM Jd) lr(Ke Pj) Yh(Mf Mp) Jh(oF Uy) Nw(Aa cl) Or(Dl Kq) Uw(bC Oe) ExiP FrVi NnWe
MunY JfVt KcbL KxkQ} jB{To(bN dN Hu Mw Oy Pf) bN(Qu Rt We) Fd(kS Ma) Qz(fB We) Rf(aS Mw) aO(Wd Wh) AfDe DuaJ FaLj FbLv
FyNn GbaS MsdJ Uebl WfUs RtkS OuUw UfVs aLfB} gC{Rz(Eq kS Qb) nl(Gh Tn Un) Du(gL Vt) Nk(Ju Ou) Wh(mT pH) Qu(Lp Vz) Kx(Ky
Ny) CoWe CuYd FnRx MbHw WbbA JfbC WdLj WfVt QzUy QwLi JuKq PsmS LpkG} dX{tF(Ao bV cG Hc lz Mv Pk) oH(al aM bC Ch lu
Mm) pF(aE aM Ao aV Or Oz) oN(eM Jf Ou) BbYf BgTn StWf QtoK KpdR aEoE} qU{kP(An Ap Bc Uc) nD(aY dl rX) kl(Dg nU Po) IX(Bc
Db) mM(Ou Pi) tT(Kd Pk) qX(nJ nR) kK(Bb Kl) kN(Jq Ko) ArmE CvnF ManU IsnN nAlK qVkF} Gz{vA(Id Je jl pF qZ) jF(Dg qW uL) lc(uL
wP) iB(Dg Dl) tB(Ok uX) wH(oF qZ) AdqB UevT UmqZ aDrQ aWrS aZrU bXlY iJyL yHrP wDqT qXjT} Pj{jD(Bn cN Cx lr Kn Lv sK) rZ(lz
Nt Of Uk) Lv(kR oF Or) IM(dF kl nN) Ly(hR hV) nF(lL qT) Umnl cNjL hVlN jFkG qWkO qTkP} Hv{Si(Gn Hf lo Kp Nf) Yj(Hu iJ Lj) Zw(Dc
Jk Yi) Dk(Ry Rz) Fy(Hp Sh) Yg(Ok Vs) GnJv GpVc HoTz HpHf YiRh SjLj RyOa nNIL mSIN} kN{Ny(jQ kP qW) qX(Kn Ld Or) jY(ln ls Ni)
Ar(jU rA) No(jF jL) Lx(lN qW) Jq(lK Zw) AnqY WmhV MyjM UejU IskP JllL KejE OrrA VugW} Zq{mS(aF cK cQ Ko Nm Nn Uw) oK(aM
Ch Jv Sh Si) mM(Bb Mh Na nW) kS(cK Du Lj Oa) FwgP MhiJ TooE Jml VjlY} eO{Ar(bC Bg bN Ch) aS(Ax dJ Fp) aF(Bc dC) aY(cQ dL)
bN(cV dW) cF(aP cZ) cO(Bb bZ) AfbS AwcW CtDi FpeM aHdC aWdG bQdD dKdL} nO{Dp(Ba bB Bg Fw gL Kq Li Tn Uf) Yf(Mw pl)
Gn(Jq To) Tz(iC Vh) ln(Cu Ha) Ug(Nk Tn) TjYi MpNw HpcR Ylpl UmaK aEcF} wD{rB(Cv ll Mh Po Sr Tz vQ) iA(hF Jr Mm Mp Qm Vq)
jM(Fw Kd Kn) Ri(Uu vH) bQ(Cq Rg) LuyJ IbKn ToPk IzqP OrnW} nl{Um(bN Cq Dd lh Jn Ou Qz) Ye(Cq Jn mT Ng Om Vu) Nf(Ax Db oE
pK) bB(bC Ns Tj) No(Gn Hp) AxtF NgeM} Kn{IM(Al iC Jd nJ Uo) Mk(hV oE rZ tT) wE(dJ Ra Vs) jM(IY tU) JhrZ RawG UruO UwoE cXIX
mSIN jEkG rAkF} Wm{uR(Bn bS Of sK Ua Uu) rB(Ct oE Ur) iA(pS Uh) uY(jD Ur) vO(lb IM) CvyJ Jkql UurS nFhV jVrU ILuN} Nw{Jl(Hx
li Mv Ny Oy) Mp(Mv Mw Oy) Mr(Hx Nb Ny) Hx(Lu Mi) li(Jo Js) DukS PoLx MynU JnJr nNjL kFlN} Vc{Fw(Ax Cs dF Dk Du Gp lo Nb Pg
Qh) gL(Du Li Ou Rg) gW(cQ Vt) hB(Cu Ou) GpiZ NbcG HqoE} Fp{Nf(lp lr ls lt Jh Lv Ne Nl Ny) dW(aR bZ cL cU) Nm(Hr Ne Nh) Hr(Jn
Js)} Et{Aj(bA bL cD cL Nt) Pk(Ax lk Mk Nm Of) bA(bL cD Mp) EfrZ LylM OftR gWkO} Uh{jD(Bn iC lr Jn Kx) Ax(iA Mk Pk Ra) iA(Mq
Pe) DukS MloE NfOa HuPk IdIM TtsJ} IY{aL(Ax fB Li No) gW(Ed Sr) jY(bS cA) AnjU Dplr GnaW HfjM YjJs WcUf UkjE jFlN kKlK}
kl{jQ(Ar Dk Gp Tz) My(iB IN) eC(Qv Uf) qW(Ar Ou) AxjR BojE TzUg KxaL UogW nJjl} Du{kS(cX Dk ls Jn) gL(bZ oN) nJ(Qu Vi) oT(Lp
Uy) GhpK NbRf Hopl TzQy dCoN} Mk{Cs(cD Or) Lx(Nl Pk) Oa(oE tT) FrNl FwlX KelM KitT OrPa UoiC PeoN nNlL mErZ} kF{Kj(jL jO)
aA(lK lN) jU(Ld Ua) ApjE CvlK DpbB EfiB TzjL UeqY OwjR OulM cReM} Hp{Dk(aM cX Jv) De(Jl Jr) AonB CuiZ EdFy NomM NbcX
IsmS JlgP PskP OkgL} kG{lr(aK cY Kq) Gp(jF jV) Yj(Lj Ng) lqZw YgUu YkJk LjOp PbrX PijE aLfB} kK{IM(Bo Cq Ko) Qu(Yg Yk) jL(Cs
No) jQ(Nn Tz) ColL MajT UejU LdlK nNlN} uY{Vt(Ly Ur vT) Qy(jK sJ) IL(cA Ql) ApLy TzJk IzaF RiwG OajK VqjF} Lx{Jn(aA ln Mh Ms)
Ry(gL oE) AngZ NfJq NlaA Inlt YjiJ JhOy} Cu{Eo(Ba Em Gd) oP(Dp Yj) GniA ShkS RyLj RxnR RtgP VwmY} dW{Aw(aO bF bZ cG cO
dH) bG(aW dD) BnbS bWdN cGcL} nN{jY(Ni Nk) AnqV ArjU CoiB InJn JrRy KglM KljD Upbl bGeD} lX{Gl(Li Ns) Pe(bC Uf) gL(Kx Qz)
Fwlq NrcX HqLd YkJr PijI} mS{Ng(We Yg) Tn(Eq Vi) ls(Uw Yg) lqYj ZwJl KlUw RzcD UmbX} nJ{Tz(jF jQ kP) iH(bC Gl ln) Cw(lM Rg)
Fy(Rt Yl) KkjF} uO{aF(Dk Ph Ur) Bc(Ua Vs) ChKq MjVt MnTk UaVq HwUr SrVs} tT{Dl(Ef Ly Pk) Hu(Bc Kg) Pk(Kd Pc) ApMh FbnW
JkKg} oE{Lv(Fy Sr) Ho(aE cX) FdGp GnHw WbbC ZxbB WfLi RyOa} Eq{gL(Co Dk Ou) pl(Ok Tn) EfmY FyoT UaoF cGpF} aL{fB(Co Ij lu
Po tF) IW(Ax cR) HqpK bHoW} eC{mW(Ld Tz Uf) pK(Aw cT oK) WeRh RykO UfnF} sJ{rZ(Fa Ql Qm) Hx(jG vW) Pg(aY Mv) MlVu QlrO}
jE{mE(As Ke Kl Ou) AplW BamH YhjY QzmM aDmT} kP{Um(Fw Qz Tz) FwUp GhaE Tzjl SrRf KkjF VqcF} IL{Kc(nT sK) nC(Ar Iz)
AxnT CvkO QmuN aQnD aVnA} iZ{Gp(Gh Ho Wb) Ry(bR cB) FyYg YicD YdaM} uR{cL(ld Or Un) Ef(oF Ou) JliA KzoF OraF} De{Zw(Jr
Lj Oa) Wb(Lj Mh) DkSh nFiB} Yj{Ha(gP iJ) oP(cL ls) FriA FykS OaiJ} Jn{Nl(aA Fr Nm) MsJh YiiJ VimM bAcD} Li{aA(Hr My Ne Nf)
YfmU RygZ LtlW} mT{Us(Hl Ho) FiTo MjKq YgcL YkcT JfeM} nA{cP(iB jP) UngW UraQ cDjU dFqW mYqZ} nD{iC(aR cJ) FwNk Haln
UmUf aSjU dlIN} tV{Iz(aF Ij Kg kR) BcJk HuKq QybR} Jd{Ik(ld Or) Qw(Cs Lj) EdKp TzOf} Tk{qD(Db Hf) uG(Dg iC) MnuL aVfN}
Ok{kS(Hl Yk) AaOf AjNt ShnR VheM} nC{Cw(jF IM) Gl(Ns Om) GpjD KelM} kO{qW(An Ar Kp) WcbR KljF OrqV} Dk{Ry(lk Lj) NhSh
YgJu SiaM} Eo{Cq(Aw Cs) AxdL CpcW bAcT} Kx{pl(bC bX gL Rf) bXpK} Uw{gW(cG cL) QvgP RzfB OugL} Vt{Qg(Pa Qb) LvKo IbuU
yJnW} Vq{pF(iC jP yH) RtgW iAwE} nR{CoYe MyjY HlKq ZwJl bBoW} IW{GnMn UeqY QzgW LtcR bSjF} jl{nT(Bc Cs) mW(cJ cX)
OrnU} Aj{Nt(Ad Bc Io) KqPa} Ar{cD(bA Bg cT) mEjU} Ef{DgrZ UnuU nFiB hRqZ} Nm{In(Ih Js) ls(Ne Nl)} Ke{SioN ShkS iClM tOrB}
bO{Zx(Na Us) HoaM dDeW} fA{FwUr ZwPi KoRg bJdD} Gn{HagP NokS OuoN} Nf{MbJs MqNy PeiA} Yi{RhcF RfkE OaiJ} Wb{Lj(bA
gL) NbRh} Pk{wE(Ml Ri) rBwH} aF{eW(cE Ct dA)} fB{AxUa MmRz dJmP} mE{NnVi NylK OrcF} rZ{ApNg Bblz LutL} nW{NbtX TzwL
jMzA} Dw{AxaS CqCt} Tj{RipK mHjF} Ex{JrrU hAuL} Fc{MveM JrmY} Fr{Nl(aA Oy)} Fw{bCpl iAzH} Fy{ZwpF RtmU} ln{MsJs ltNy}
Jk{YemU UnvB} Op{mM(cW Lj)} bl{RmpH RggZ} nU{KpiB qZqT} mW{FaUm bSqV} iJ{AoGd NoZw} rB{TvuP oFvQ} CsLwcD DdHlgZ
DgnTjF EwcPdK NsYhjY MvLpoT TzSiQh HrIrPe KqUolM RzbLpK UxdJgW Constrained panels with 2 analytes, where 1.0E-8 >= 'AUC p-value' > 0. Contains 555 panels of 199,260 total panels evaluated. : Jp(aA aC Fp
Hc Ib Ih Im Ir Is It Iv Iz Jd Je Jg Jj Jl Jn Jr Js Jt Kx Lh Lv Lw Lx Mb Mh Mp Ms Mt Mx My Mz Ne Nh Nj Nl Nm Nt Nu Nw Nx Oa Of Og Ok
On Or Ow Oy Pk Qa Qb Qd Qe Rg Ub Vs Vt) Nj(aA Et Ew Fp Fr Ij Im Ip Ir Is Iv Jg Ji Jl Jn Js Jt Lh Li Lx Mr Mt Mx Mz Ni Nm Nn No Nr Nt
Nu Nv Nw Nx Ny Og Ok On Pa Qa Qb Qc Qd Qe) Iv(aA Et Fp Fr Ij Im In Ip Ir Is Jg Ji Jj Jl Jn Js Jt Lh Li Lx Mm Mt Mx Mz Nh Nm No Nr Nu
Nv Nw Nx Ny Og Ok On Qa Qd Qe) Qe(AA aN dW Eo Et Hr Il Im In Is Jg Ji Jj Jn Jq Jt Lh Lw Mb Mt Mx Mz Nc Ne Nf Nh Ni Nl Nm Nt Nu
Nw Nx Og Ok On Oy) Jg(aA Aj Fp Ih Im Is It Jj Jn Js Lh Lx Mb Mh Ms Mt Mx My Mz Nc Ne Ng Nh Nl Nt Nu Nw Nx Of Og Ok Oy Qa Qb
Qd) Nw(aA aC aN Eo Fp Im Is It Jj Jn Jt Lw Mb Mh Ms Mt Mw Mx My Nc Ne Nf Nh Nl Nt Nu Nx Of Og Ok On Oy Qa Qd) Et(aA aC Fp Im
Is It Ji Jj Jn Lu Lw Mb Mh Ms Mt Mx My Mz Nc Ne Nf Nh Nl Nt Nu Of Og Ok Oy Qa Qb Qd) On(aA aC aN Fp Ii Im It Jh Jj Jn Mb Mh Mp
Ms Mv Mw Mx My Nc Ne Nf Ng Nh Ni Nl Nt Nu Of Og Ok Oy Qd) Nt(aA Fp Ik Im In Is Ji Jj Jn Js Jt Lw Lx Mk Mx My Mz Nf Nl Nv Nx Of
Og Ok Oy Qa Qb Qd) Ok(aA aC aN Fp Hr Im It Ji Jj Jn Mb Ms Mt Mx My Nc Ne Nf Nh Nl Nu Nx Of Og Oy Qa Qd) Qd(aA aC Fp Il Im In Ji
Jj Jn Lw Mb Mj Ms Mt Mx My Mz Ne Nf Nh Nl Nu Nx Of Og) Ji(aA aC aN Ii Ik Im In Jj Jq Lu Mp Ms Mx My Nf Nl Nu Of Og Oy rR wE)
Nu(Fp Ij Im Ir Is Jl Jn Js Jt Lh Lx Mx Mz Nv Nx Ny Og Pe Qa) Mz(aC Hr Ih Im Ir It Jn Lx Ms Mx Nf Nx Og Qa) Im(aC aN In Jj Jn Lh Mt Mx
Ne Nf Nh Nl Og) Jt(aC Fp Jj Mt Mx Ne Nl Og Qa) jD(Wd Yd Yg Yh Yi Zq Zx) Mx(Ir Jn Lh Nv Ny) Og(Ir Is Jn Nv Qa) eO(aD bB bR dB Of)
gW(fR kF kK kN mF) Jj(Jn Kf Nv Nx) cM(fA gZ oD Uh) Ti(rT rZ wF) Mt(aA Is Qa) Zx(jU IN qU) Xa(Nd oD oV) Eo(Jn No) Th(yJ zA) Sf(Dk
Nd) Qa(Nl Nx) Lh(Ir Nm) Ut(dU Vb) aC(Ar nL) aM(dW eW) rR(Kc Kf) FpNv GchC GlmZ LxJn HoeP UbJd HrPe ZqlM ZwJr WcqV QysF
YeqT Krsl WnUh Umnl bUnN cCdW mFjF qUkK Constrained panels with 2 analytes, where 1.0E-7 >= 'AUC p-value' > 1.0E-8. Contains 340 panels of 199,260 total panels evaluated. : Mz(aA
aN Fp Hx Ij In Is Jl Lh Lv Lw Mb Mi Mm Mt My Nc Nl Nm No Ny Pb Pe Qb Um) Qa(aA Hr Hw Il Im In Jh Jj Jn Js Lh Lv Mb Mm Ms Mx My

Figure 31 Continued

Ne Nf Nh Ni Nm Nv Oy) Lx(aA aN Im Is It Jh Js Jt Lh Mk Nc Ne Nf Nh Nl Nv Nx Ny Og Oy Qe) Im(aA Fp Il Iq Is Jl Js Jt Lv Mb Mm Ms My Nc Ni Nm Nv Nx Of Oy) Lh(aA Fp Hr Ih In Is It Jj Jn Lw Mm Mt My Ne Nf Nh No Nx Ny Og) Nj(Ih In It Jh Jj Jq Jr Lj Ma Mi Mm Mn Mp Mu Nk Pe Po) Nv(aA aN Is It Jn Jt Mb Mt My Ne Nf Nh Nl Nm Of Oy Qe) Nx(aA Fp Fr Ir Is It Jt Li Ms Mt Mx Nc Nh Nl Ny Og) aC(Ba Bb Cu dF Ih Io Is Jg Kf Kp Li Mm Mt Nm Pj Qe) Nu(aA Fr Ih Ip It Jh Jj Jq Jr Lv Lw Mt Nl Oy) Iv(Ih It Jh Jq Lv Lw Nc Ne Nf Nl Nn Nr Pe Qb) Js(Fp In Jj Ms Mt Mx Ne Nf Nl Og Qe) Is(aN Jj Jt Mb Mx Ne Nh Nl Nm) Qe(Fp Jh Jl Li Lv Mm Mp Ms Tl) Jn(aA aN Fp Fr Jl Li Ms Mt Ny) Jt(aA Aj aN In Mb Nh Of Qb) Mt(Fp It Jj Mk My Nl Og) Jp(Cs Fa Jv kR Qu Ua Uu) Li(aA aN Jj Mx Ne Nl Og) Mx(aN Fr Ij Mm Nm) Ir(In Jh Mm Nm Ny) Jg(Ik Jl Lw Mg Mp) bM(bA Jd Ji Nw Qd) aN(Ar Et Io Qc) Gc(hG kS oE) Nl(aA Fr No) Og(Ij Mn Ny) oV(Qu Ub Ut) Ti(rC vB) Et(bA Pk) Fp(Nf Nm) Nh(Mn No) Ji(jD wQ) Kf(lM Uu) nN(cM lL) qU(kF kP) AjKq ArcD CsUb CuVb WmuR GlnL GzuY MmaA HvSj TnmZ IjIn SfJr QysH JjNy WnrN aFdW aLfB

Constrained panels with 2 analytes, where 1.0E-6 >= 'AUC p-value' > 1.0E-7. Contains 512 panels of 199,260 total panels evaluated. : aC(Ad aN Ao Ap Ax bA Bc Cp Cs Dg Dl eO Fr Id Ij Jn Kc Lh Lx Mx Nt Nu Nv Pk Qa Qc Ub Uh Un Vq Vt) aN(bA Bb bM cB cD cM Cs cT dD dF dK Ij Ir Jp Jr Lh Lj Lw Mq Nf Nj No Nt Nu Nx Og Pe Qa Qd Uh) Mz(bM cD iC Ip Jh Jj Jr Js Jt Li Md Mh Mr Nc Nh Nr Nv Oy Po Qv rC rR rU Uh Ur Vt) Li(Hr Im In Ir Is Jh Js Jt Lh Lv Lw Mb Mm Mt Nc Nf Nh Ni Nm Nu Ny Of Qb) Ny(aA Fp Is It Jh Jr Js Jt Lv Lw Mi Mr Ms Mt Nf Nh Nl Nm No Of Oy Pe) Nx(Ih Ij In Jh Jl Jn Js Lj Mr Ne Nf Nm No Nv Of Pe Qb Qc rR sI) Lh(Fr Hx Jh Js Jt kC Lv Mb Mh Ml Mp Nb Nc NL Nn Oy Pb Qb) Is(aA bM Fp Fr Ij In Jh Jn Js Lv Mm Ms Nc Nf Ni Nn No Oy) Jn(cD In Ir Jh Jt Lv Lw Mm Mr Ne Nf Nh Nl Nm No Pe Qb) Fp(aA Ij Ir Jh Jj Lx Mm Mx Ne Nh Nl Og Pz Qa) Nu(In Mb Mi Mm Mr Nc Ne Nf Nh Nm Nn No Qb) Js(aA Hr Jh Jt Lv Mb Mm Nc Nh Nm No Nv Of) Mt(Aa Ir Jl Jq Lx Mb Mm Mx Nh Nm No Oy) aA(Fr Ih Ij Ir Lv Mx Ne Nh Nm Nn No Nr) Ji(Aj Ar aS Ax bA cD cM Cs lM Ub wF) Mx(bA Jh Kp Lx Nl Nn No Qv Uh Ur) Ir(Jj Jt Lw Mi Ms Nf Nn No Pe Ub) Og(Fr Ik It Jh Jl Mm Nh Nl No Qb) Jt(Fr Hr Ih Jl Mr Ms My Nc Vb) Nm(Jr Lj Lx Ne Nh Nl No Qb) Nj(Aa Lv Lw Mq Nd Nh Nl Pz) Jj(Dc Fr Ij Jd Lx Mm Nn Pz) Jp(Ar Ax bM Ef kC nL Sf Vc) Im(bM Jq Lw Mp Nn No Qc) Aj(Ba Et Kf Nt Ok On) Lx(Jl Jq Mb Mm My Ur) Mn(Lv Mq Mr Ms Ne Nl) Ub(Ax Lj Oa Oh Qd Qe) Ij(Mb Nc Ne Nh Nl Of) Uh(Ax bM Cs jD Pk Qa) Aa(Iv Mb Nt Qa Qd) Nv(Hw In Lv Ms Ni) Vb(Gc Jr Kf Nb On) Cs(cD cM Et Ml) Nl(Jh Jl Nk Qb) Qe(aS cM Ur Zw) Vt(bM Kf Qg wF) hC(Et Pj Zq Zx) qU(nN nR nU Yd) rR(Ap Jv rC Uf) Ar(bA cM Qd) Fr(It Ne Nh) No(Ib It Ne) Xa(eM cP kS) Ut(nL Sf Si) bM(Et Kp Ok) lL(kF kI nK) Fw(oV Vc) Nh(Ip Pa) Ik(Jd Kf) Yd(jH qT) Zx(jH rA) Qa(Lw Tl) Kq(Ef mZ) Um(mZ nO) Pj(jD oE) aL(nL oW) wF(Ri Th) qX(Wd Wh) kC(iB iH) oD(cR Rz) EoQd TitT EtaG GciZ GzvT MmIt MpIv NbSf NdSh NfJr IpwQ IzOn YhjP SroE QhTl YejI KfLj KrsH NwcD OacM WnsO UfnL cFjB fRIM kKIK Constrained panels with 2 analytes, where 1.0E-5 >= 'AUC p-value' > 1.0E-6. Contains 812 panels of 199,260 total panels evaluated. : aC(aJ aM aP aR aX aZ bC bM cG cN cT cU Cw Dc Dd De dL fR Fy Iv Jd Jj Jq Js Ke Kn Ko Kx Lj Mi Mq Nf nH Ni Nj Nx Ny Pa Pd Pe Po Qb Sr) aN(Ax Ba bF cF CU Dd Ew Fp Ih Iv Jg Jq Js Kx Lz Mh Mi Mr Mt Nm Ny Oa Pa Pf Qb St Tz Vt) Ub(Ar Cv Dc Et Fa Hb Id Is Jn Kf Kk Kn Ko Kp Kq Kx Lh Li Mt Mx Mz Nw oE Qa Sr Tz Uh Vt) Mx(aV bM cD cM Cs Cu dF Di Ih Ip It Jj Jl Jq Kc Kf Mb Nc Ne Nf Nh Pz Qb Vt Tl) Uh(Ar Dc dL Fy Hu Id Im Ir Jd Jj Kf Kq Kx Lh Li Lj Lx Oa Oh Pa Pe Qd Qe rR Wm) Mm(Fr Ih Ij Ip Jl Jq Jr Jt Lj Mb Me Mr Ms Nc Ne Nh Nl No Nx Ny Pe Qb Qc rR) Jj(Ad Bc bM Cs Fb Fy Ih Ii Jl Jm Kp Ks Kx Ne Nh Nl Nm No Pi Qb Uf) Kf(aS Ax bM Cs Ed hC hR Iz jD Jo Mz oE Of Or Pk Qa Qd Qe Rg Uk Ur) Qe(Aj Ar bA bE bM cD cT dD dF Di Jd Kc Ko Kp Qg Qw Vb Vs Vt) Fr(Fp Ih Ij Ir Jq Jr Js Lv Mb My Mz Nc Nf Nm Ny Of Oy Qb) Nn(Fp Ij Ip It Jn Jt Lx Mt Mz Ne Nh Nl Nm Nx Ny Of Og Qb) Vt(Ar aS Ax bL cM Cs Et Im Ko Kp Lh Nf Og Oh On Pa rR Tz) bM(Ar aZ Bb dF Gp Io Jg Jn Jq Jt Kc Lx Oa On Or Qa Vi Xa) Ar(aK aZ bE bL bU cB cT dF gW Jd Jn Lw Nw Og Qc) Mz(aS Cs hP iB Jd Jq Kc Ml Pk Pz Qw Qz Rg rV tT) Nl(Aa Ih In Ip Ir It Jq Lj Lv Mp Mr Ni Nr Po Pz) Jl(aA Hp Ij Is It Jh Js Lh Li Ms Nc Ne Nm Ny wQ) Jp(Aa Ao bA bL cD cM cU ml nH nK nN Si Sj Uw Vb) Ji(cN cT dD iC kC nL Qg Qv Rg sI tT Us Uv Vs) Ij(Il Jh Jq Lv Lw Mp Ms My Nf Nm No Ny Oy) Qb(aA Fp Is Jh Jq Lv Mb Nc Ne Nh Ni No Ny) Ur(Cq Dc Im Ir Is Jn Oh On Pa Pe Qa St Tz) nL(bB bU dD iB lL Nw On Ou qU Rv Tn Tz Um) Og(Cs Ip Jd Kq Ne Nm Nr Oa Po Pz Qc Tz) cM(Et Fp Im Jd kC Kp Kx Lj Nw nY oE Qa) Ir(Ih Ip It Jr Lv Mb Mp Mr Nc Nh Nr) Aa(Ih Im Is Lx Mc Nb Ne Nh Ok Qc) Fp(Hr In Ip It Jq Lv Lw Ms Nc No) Nm(Ih Ip Jq Mb Mr Nc Nf Pe Po Qc) Jh(aA It Jq Jr Lj Nc Ne Nh No Qc) Jn(bA dD Jq Js Mb Mi Nc Pz Tl Wm) Vb(Dc De Fy Is Mt nK Ok Pz Qa Qy) cD(bA Et Im Jg Li Lj Lx Ok Pe Qd) Lh(Ii jD mF Mv Mw nH nK Po Vs) Nx(Ip Lv Lw Mb Mi Ni Nr Oy wD) kC(aL bB bU gW jF jI lL Nw qU) No(Ih Ip Jr Lv Mb Ms Nc nK) aA(Hr Ip It Lj Mb Nc Nf Pz) Et(aS cU kR Kx lM Or rR) Ne(Ip It Jq Lj Ma Ny Qc) bA(Aj Iv Lj Nj Nu Nw Qd) Nh(It Jq Lj Lv Ms Qc) Tz(Gc Ho Kc Ko kP Tl) Qa(dD Kc Kp Mp Qw Rm) Jt(Ii Lv Mp Na Nf Oy) Ny(Ih In Ip Jq Mb Nc) Cs(Jg Nw Qd Qw Tl) Lw(Is Js Lx Nv Pe) Pj(hV iC jI Or rR) bU(Ho Lj Lx Tl Xa) nH(aL cY Gl jF lL) rC(Kn rZ tT uY yJ) Aj(Ad Im Jd Qd) Ti(iC rO sK uW) Mk(Fa iC Ke Kq) Mn(Jr Mb Me Ni) Nf(Jq Mt Pe Po) Li(It Jq Mp Oy) Nw(aS bL dL Rf) lL(mF mI sH uY) lM(Id Ke Kn Yj) Dk(On Sh Si) Wm(rB rR wF) Gc(oD Us Ut) Lx(cF In Ni) Nd(Ho Uw Wb) Qd(aS Kp Tl) Kc(Ax Oa Pa) Kq(Iz Of Pa) Vc(cG dF Ut) nI(bB Gz hC) Mb(gC Ip) Mp(Js Nu) Mt(In Ms) Hv(Sf Si) Ih(In Qc) Im(aS Sf) Is(Mr Nr) Wb(hC Us) Zq(kS oE) Wh(eP jD) Tl(jB Ps) Kn(oE rR) Ko(oV Pk) Kp(Ed Lj) Ld(lX oD) On(aS Hc) bO(Ho Zx) fR(eD jE) nN(lN Nk) kN(kP rZ) uR(Or sI) DieO DpnO DuQy EoHx ThwQ ExcJ FyQv GlnC TojB ItQc YimS YdjE SiJr ShUt JdOf JgUu WcjY WfjP RaOh JsOy XakG RirR WnuO UfmZ UwhC mIiH qUkI Constrained panels with 2 analytes, where 1.0E-4 >= 'AUC p-value' > 1.0E-5. Contains 1,423 panels of 199,260 total panels evaluated. : bM(Aj aS Ax Ba Bc cD Cs cT CU Dc DD Fy gW Hb Id Ij Iv Jr Js Kd Ke Kk Kn Ko Kq Kx Lh Li Lj Mi Mn Nf Nj Nt Nv Nx Og Ou Pe Ph Pi Pj Pk Qb Qc Qg Qh Sr St Tn Tz Ub Uf Un Vp Vu Wb) Jj(Aa aN Ar BA Bb Cp CU Dd De dF Ex Fw iC Ip It Jh Jk Kg Kn Ko Kq Lj ml Mn Nc Ng nH nL nN Nr Or Ou Ph Pk Qh Sr Tz Vq Vt Tl) Ub(aK cD cM dD Fb Fr Fy Gc Hf Im Iq Js Kc Ke kP Kr Lx Lz mF Mk nL No Nx Ok On Or Pa Pi Pj Pk Qb Rg rR St Um Un Uo Ur Us) cD(aC aJ aR Ax aZ Bb bV cG cT cU Dd dF Fp Ij Is Iv Jr Jt Kf Ko Kp Kq Lw Lz Mn Mq Nj Nt Nx Oa On Pa Po Qa Qc Xa) Uh(Ao Cu Dd Fa iC Ik Is jI Jl Jt Kn Kp lM Lv Lz Mk Mq Mt mZ Nd nH nL Nx Or Qh Qv Rg Sr Tz Un Ur Us Vt) Vt(Cu Dc Dp Fy Gp Ir Jd Li Lj Lv Lx Mk Mt No Ns Nw Pj Pk Ps Qa Qd Qv rZ Sr Tn Uf Ur Us uY wQ yJ Wm) Cs(aK bA Bb bC bU bX dD dF gW Io Jt Ju Kc Ko Kp Li Lw Mi Mk Mt Nf Ni Nj Nt Ok On Pk Qc Qe Qg Us) Mx(Aj aK Ar aS Ax Ba Bb Bc cB cT cX dD gW Hb In Jd Ke Kk Ko Kq Lv Oa Og Pk Qg Qw Sr Uk uM Un) On(Aa Ao Ar Ax bE bL cM dD Ef iC Jd kC Kk lM mF mI nH nK Pk Qv Rg Ua Um Uu Uw Vc Vs Yg Zw) Ur(aC aN Ax bA Fw Jl Js Jt Ko Kp Kq Lh Li Mq Mt No Nr Oa Ok Or Po Qd Qh Sr Us Ut uY Vp Vu) Jd(aN cX Ef Ib Im Iz Ji Kf Kn Kp Kq Lj Lx Nd Oa Or Pa Pk Qa Qd Qv Qz Tz Ue Un Uu Vb) Ar(Aj dJ Et Ik Im Io Is Iv Jg Jq Kf Kp Kq Mi Mz Nf Nj Nt Ok Pe Qa Qg Qz Tz Us Vu) aN(aZ cG Cp Dc Dl Ex Gc gW Id Kc Kf Ko Kq Ml Mm Mu Or Pd Pj Po Ql Sr Uf Un Vu Wb) cM(aC bA bV dF Ex Fa Fy hR Iv Jn Ke KF Ko Li Lx Mz nL Nt Ok Or Pj Qb Qd Sr Un) Lv(Aa Ih Ip It Jh Jl Jq Jr Ke Ko Kp Kq Lj Mm Mr Ne Nf Nm Nn Nr Pe Pz Qc Un) Et(Ao Ap Ax cN cT Dc Ed Ef Fa Ib iC Id Iz Oa qT Qv Rg Sr Tz Um Us Vu) Kp(Aj aS Ax dJ Im Ji Kq Kx Lh Li Lx Mz Oa oE Or Pj Pk Sr Tz Un Us Vb) bA(An cB cF dL gW Im Is Jg Jt Li Lw Lx Mz Nf nL Nt Og Ok Pe Pj Qa Wb) Jn(Aa Aj aM aS Ax bU cT De dF Di dL Gz hC Id kC kP Mp nN Rg Sf Vb) Kf(dL Ef Fa

Figure 31 Continued

Hu iC Im Kx Li Lz Mk Nm Oa Og Oh Oi Qv Ra Tz Us yJ Wm) aC(aA Fa Fb Gc Hb Ic Kq ml Mp nC nK Oa Or Pf Pz Ql Qm St Uf Vu Wm)
Vb(Ba Cq Fr gL iJ Iz Jg Ji Jk Jq Lh Nt Nv Ps Qh Tn Uc Vi Vu Xa) nL(aA aK aU aV bC bE cG cJ cX cY Dp Gc Gp iH Is Kq Lx Nx Ok Qd)
Aj(Ap Bc Cu Dc dF Dg Fr Ij Is Iv Jp Ko Lh Mz Nm Nv Nw Qa Qc) Pe(aS aV bL cB Ip It Jh Jr Kc Mh Mr Nh Nl Nn Nr Og Oy Pb Qc) Pk(Ax
Gc Ik Ji Kc Lh Lx Mk Nw oE Og Oh Qd Qe Sr tT wD wE wF) Mz(aR Ax bU cF cT Dp Ed gW Jo Kk Ko kR Kx Mp Or Pj Ra yH) Nf(cT Cu Ip
It Jl Kq Mm Mr Ne Nh Nn No Nr Oa Qb Sr Tz) Nw(Aa Ao Ax bE cT Hc jD kl kP Kx mF ml nK Or rC Rg Us) Lh(aS He Iz Kc kP IK IM ml nJ
nN oN Qg Us Uv Vc wQ) Lj(Ba Bc cB cT Cu cX dF Di Kc kR Lw Nc Og Ou Qg Qw) oE(Cu cX Fy Hb Id Ke Ko Lx Mk Oa Qm Uf Un Uw Tl
Xa) Qe(Ax aZ Cu gW Hp Iz kC Kk Kn Kx Or Qv Rm Sf Yj) Jq(aA Ih Ip Ir It Mr Ms Nc Nn No Nr Nx Og Po Pz) Jr(Aa Ij It Lw Mr Nc Ne Nh
Nn Nr Og Pz rZ Sh Sj) Mp(aA Fp Fr Is It Lx Mt Ne Nh Nm No Nx Ny Qc) Jl(Eo Fp Fr Hr Ih In Kc Lw Mb Nh Of Oy Qb Tl) aS(dL Is Kc Kk
Kn Kq Li Lx Nt Ok Or Qa Sr Un) Aa(Fp Fr hC It Jg Li Lu Nc Nu Nx Og Po Qb) Ko(Ax Ex Ik Ir Lx Mk Oa Of Og Pa Qa Qv Vu) Ji(hV Ib Iz Ju
kP Kx nH Oa Ow Qz Rf uY) Po(aA Ih Ir It Jh Mm Nc Ne Nh Oy Pz) Nn(Ih In Jh Mb Mm Mr Ms Nc Ni No Oy) Tz(Du iC IX mZ No Qg Qv rB
Sf Sr Wb) Jp(aG aR cX dE dL Hp jD rB Rz Sh Yg) Og(aA Ax Id Ih Ii Jm Ma Nc Oh Sr St) kC(Bo dD eC Gl iC jQ jY Lx No Nv Qc) Im(aK bJ
cT dD dL Hf Kk Qg Qw Tl) Sf(Cq Dc Fw Gc Is Mt Nr Nt Qh Zx) Qd(Ax bE cT dD hR Kx Or Qg Qv Wm) Kq(Dk Ez Hc Ik Io mF Nm Nq Pj
Tl) Mk(Ex hR Kx Oa Or Ou Pj Sr Un) Pz(Ip Ir It Jh Mr Ms Nc Ne Nh) mF(aK aQ cY Gl iB Qv Tn Ug Um) tT(Dl Ip Ir Lu Ly Nq nW Nx Oh)
Nr(In It Jh Mb Nc Ne Nh Nm) Lw(aA Fr Mt Ne Nh Nl No Qb) Ih(Fp It Jh Mb Mr Ms Ne Nh) Ik(In Kx Mn Oa Pj Qc St Un) Wb(bO cB De Ed
Nb Qb qT Ut) mZ(Ex Fa Fw gW Ke Kx Pi Ut) Mm(Jh Mh Mi Ni Nm Of Oy) Qa(Di Lz Kk Qg Qv Vs Zw) hC(Bb dU Ho Jt Kc ml Xa) Wm(Hb
hP uI uY wQ yJ) Gc(bR Ed Qv Uk Va Vi) Mr(Hr It Jh Nc Ne No) Qc(aA dD Ip Mi Nc Pd) Sr(Ax iC jV IM Uk Un) Kn(hV iC rZ wE wF wQ)
Pj(dD hR IM rZ Uk wF) IX(cX Fw Gl Kx Uf Ut) nK(aA dD eM Gl iH jF) Lx(aV bL cC cK cT) Nd(Kc Kk Kx Vi Zq) Iv(aK aR Ax bO Di) Qv(Iq
Js kI Ks Pi) Xa(aM bO cF De Rh) Tl(cB Ed cQ Li Rh) Ok(bL cT nH Uw Vc) Um(Hx iC Js kP Pa) dL(Bb Fy Is Jt Nx) ml(aL dD In jF No) tV(Ij
Iz Lu Ly wQ) wD(iA Lu rB vP Vs) rR(Dg hR Ke IL Or) Nm(Hr In It Jh) Ip(It Jh Nc yJ) Qb(dD In Ms Oy) Kc(Hx No oD Qh) Un(Ax iC Pa Uo)
bU(Ex Gz Mt Vh) Fy(kS oV Vc) Nt(aR Ax cX) Mi(Fp Nh Nl) Mn(Ao Mh Nc) Nb(Hp Si Sj) Io(Kx Mb Ni) Nv(Hc jD IM) Us(Du Ps Zx) Pi(Ex
Hu Sj) aM(Ho Nj Vi) nN(cX iH jY) nH(aK aU qU) qW(Vz Wc Ye) Ti(fY wH) Th(uM wK) Gz(rN vA) Ne(Ir Jo) Hx(Qg rC) Hb(Ax Kx) It(In
Nc) Iz(dF Fr) Jh(Oy Pa) Wd(eP oD) Kk(No Qm) Li(kP Qw) Rh(Uw Vi) Ny(Eo Ni) Oh(eO Ms) Ut(eQ Ho) Vc(Hv Qh) aA(Jm Jo) bL(dF dU)
gV(bB dR) nO(cF Ug) nC(iH IL) jD(Ql Qm) jE(Wf Yh) jF(fR kN) jM(sF sH) jY(kF kN) kK(iB jH) rQ(IL pF) uR(Kx Ou) uY(aR jK) BaCt CuNj
CvrC DeYj ExHc GpOr MaMb MlOa MtRa HpJk HrPd HuSt IdaK TnVs YiiZ ZqmM QgPa JtdD WnuG OmOy aLlY bOoV cAjB cTgW eMnI nJiH tXnW sIuO

Constrained panels with 2 analytes, where 1.0E-3 >= 'AUC p-value' > 1.0E-4. Contains 2,205 panels of 199,260 total panels evaluated. : Jj(Al Ax bB cB cD cG cN Cq cT dD Dk dL Ed Fa Gc Ha Hf Ho Id Ik Jo Jq Jr KC Ke kI Kk kN kP Kr Lv Ma mF Mg nK nO nU Oa Oh Pd Pe Pg Pj Po Qc Qm St Ub Uc Un Us Vu Wb Yg Yi Xa) cM(An Ax Bb bM cF Cp cT cU dL Ed Gz Hf Ho hP Id Ij Is Jg jI jP Jr Jt Kc Kk KN Kq kR Lh mF mI Nj nO Nu Nv Nx Pe Pk Po Qc Qm Qv rR Sj St Tn Tz Uf uP Ur uY Vq wQ yJ) cD(Ad Aj An aS Ba BC bF Bg bQ cN Cp Cq Cu Dc dD De Dl Dk dL dR Fr Fy Hb Hq Id Ih Jd Jl Jq Js Kc Ke Kx Lh Mh Mi Mm Mp Mr Mt Mu Nb Nm No Nu Nv Or Pd Pf Qb) Og(Ad An Ba Bb Bc Cu Dc Dd De dF Dk dL Fa Fb Fw Fy Hb Hu Jk kC Ke kK Kn Kp Kx mF mI Mp Mr Mu Mw Ng nL nN oE Oi Or Ou Pd Pi Pj Qh Qm Tn tT Ub Uc Un Vq Vu Wm) Pk(Aj aN Ar aS Bc cV cX Dc dD dF dH dJ dL Ex Fb Fr Hb Hu Im Io Jn Ke Kk Kn Kq Kx Lj Lv Ml Mm Mt Nd No Nu Oa Or Ou Pa Pe Pj Qa Qv tQ Uf Un Ur uY wQ) Vb(Ad Ao bA Bc bV Cp cT Cw Dd Dk Ef gV Hc Ho Ij Im Ir Iv Jh Jl Kc Kj Kq Li Mr Mu Mv Mw Mz Om Ou Pi Qc Ss St Tt Uf Un Us Vh Vt Vv Vw Wb Yg) Lj(Aa aK aR aS bC bX cG cJ cN Cp dD De dL eM gW Ik In Jo Kk Kn Ko Kq Mb Mg Mi Mp Ms Mu Nf Or Pd Pj Qm Sj Sr Tn Un Ur Us Vu Wb Yj Tl) Aj(Ao Bb bC Bg cG cT Dd De Dk dL Fb Fw Fy Ih Io Jk Jr Js Kg Kl Kn Kx Li Lx Mg Mm Mn Mq Mt Nf Nj No Nu Nx Ny Pa Pd Pe Pi Pz Uf) Qv(aN bM Dk Ed Fw Hb Hx Id Ij Il Im Io Ir Jn Jq Jt Kg Kn Lv Mq Mt Nd NO Nx Oa Oe Ok Ou Pa Pe Pj Qh Ql Qm Sr St Uf Un Vu Wm) Ur(aS Bc bM cT Cu Cv Dd De dL Ed Fr Fy Ha Hx Id Ij Il Iq Jg Jq Jr Kn Kx Mp Mu Nv Nx Ou Pd Pi Qb Tn Tv Uc Uf Un Vq Wm) kC(aA aC aK aQ aU aV Ax bA bF bQ cF Cw cY dR Et Fy hA hC In Ir Is It Jq kP Li Mh Mp Nk Nx Ny Ok Or Ou Pe Pg Qd Ug) Kc(Ar bA cX dF dH dJ dL Ed Fa Hb Ij Io Iq Ir Is Jd Jn Js Ko Li Lv Mk Nr Nu oE Oh Ok On Or Qb Qc Sr Us uY Wm) aS(aR Bc Cu Dc Dd Ed Fa Fp hR Id Ih Ij Iv Jg Jq Jr Js Jt Kd Ke Kx Lw Mh Mt Nj Nm Nu Nv Oa Pj Qb Qc Qz St Vu) bM(aA Ad aK bE bF cB cG Cp Di Dk dR Ed Fa Fd Fp Gc Ho Kr Lv Mq Mr Mt Ni Nm No Pf Ps Rg Ry Sj Tv Uc Um Us) Sf(Al aM bB cB cF Cu Dd De dF Ed Fb Fy Gp Ho Ij Jd Jg Ji Jk Js Ke Kf Kp Lh Mn No Nq Nu Ok On Wb Tl Xa) Pj(aJ aK Ax cN Cs cT cX Dc dF dH dL Ed Fa Kk Kx Lv Lx Mq Mx Nd Ns Oa Of Oh Ou Pa Rg Tz Ue Vp Vu Wm) Qc(aK An aR Ax bA BC bE bV cN Cp cT CU dF dL Jo Jr kI Kk Kp Lw Mb mF Mq Mr Ms Nf nL Wb Zx) hR(aF bA Bb cA cT cV dK Et hW iB iC JD Ji Jp Jt Kn Kp Lh Ly Nx Ny On rB rC rS rZ Uh Um Vt wE) Ub(aN Bc Cu Dd Dk Du Ex Fp Ho Ip Jl Jq Jt mI Mj Mq Nr Pe Qh Tn Tv Uf Vp Vq Vu Wb Xa Wm Ti) Cs(AR aZ cB cT Dc dJ dR Ik Im Is Jd Jv Ke Kq Kx Lx Mm Nl Nm Or Pe Qz Ra Sj Sr Un Wb) Mk(Ax dR Fb Fy Hb hV iB Id Jd jF jI Kk Kn Kp Kr mI nN oF Ph Pi Qh rZ St Tn Tz Uf Us Vu) oE(Ar Ba Gl Gp Ho Jd Jg Jn Jq Jt Kq Kx Mt nI Nx Or Pd Pe Qz Ra rC Uk Vq Vt Vu Wb Zx Wm) mF(aL aU aV Bo bQ cF Dp dR eC Fa Gp iC iH In Ji jQ Ke Ko Li Lx nN Ok Qe Rb Tz Uf Uh) Kp(aM aN bL cV dH dL Fa Hb Hu Ik Iz jD Jl Jv Ko lM Mq Nd Nf Of Oh Ra Rg Sh Vu Wm) Or(aV bA cF cX dJ Dl Fy Gc Hb Ho Hu Ik Io Jg Ji Jt Ke Ko Li Lv Mm Nd Pa rC Sr Vt) Sr(Dc Ed Gp Ir Iz JD Kn Ko kP Kq Kx Lv LX mZ Ns Oa Pa Ra rB Rg Um Vp) Mx(aR aZ Bo cN Dc dJ Fa Gp hP hV iC Id jF Kn Lw Mp nY oV Ra tV Wb Yj Zx) Jd(Ax Ed Fa Fy Hu hV iC Id Jv Kx Lh Li Lv Mt Nw Oh Pe Qu Ua Vc Vs Vu) aR(bF cB cT dD Fp Ij Is Jn Jq Jr Jt Lh Li Nj Nu Pe Qb tT Tz wE wQ yJ) Ko(Ar bA cX Ed Fa Gz Im Iq Kq Kx Lh Lz Nd Oh Pe Qz Ra Rg Uh Un Vp) Vt(Fa Ho hP Io Jt Kn Kx Lz Mq Oa Qh qI rC Rg sK tT Um uO Vi Tl Xa) dD(An Bb cF cU dL Id Ih Io Is Iv Jg Jr Js Lh Li Lw Mz nH Nm Nt Nx) kP(aA Bc Dp Et Fy Ir Jq Jt nK nN Nv Ny Oa Ok Pe Qa Qd Qe Qz Uf Yj) nL(Ax Bo cF Cu Cw Et In Ir jF Jq Kf kQ Kx Ma Nq Nv Qe Qz Ra Rg) Wb(aC aM As aZ bL cF cN cT dF Hf Ir Is Lh Mh Nq Nu Oa Rh Sj) Kq(Ao Ax Hu Ib Jo kG lX Mw My oD Oy Rg Uo Us Uu Uv Vc Vs Wm) Pa(aV bU Ed Hc Id Ik Ke Kx Nf Ou Ra Rg rZ St Tn Tz Uf Uk Us) yJ(aF Bc Cv Dl Et iC iJ Im Is Jl Jp Jr Ke Kn Kx Un wD wE Ti) Cu(bE bL Et Hb In Io Jn Jp Li lM lX mZ nI Of Ra uR Vs Tl) dL(Aa An cF cT Dd Fp gW Hb Io Jg Jq Jr Ke Kn Lh Nj St Tn) Ar(Ax Cp Dc dR eO Fy Hu Jt Kk Kn kR Li Mq Mt oN uR wQ) Tz(aC Fr hP jD Kk Kx Li Lx Lz nC nH Nx Ok Pe wE wF Wm) Fy(aN cN cX dJ Dp Hu lM Lv lX mZ Of Ra Si Sj Uk Un) Mt(aV Ax bA bE cB cF Hb Id Kf Kk lM Sh Uk Um Vc Vu) Jn(bE bV bX cG cN cU Dc dJ Ed gW mI Qg Sj St tV Uf) nK(aK aL bE bQ cY dF Im Is Ji Lx Nv Nx Ny Ok oV Qd) iC(Gz Id jD Jp kK Lh Ly Ni Nk Nw Nx Ny Qd Ra rR Uo) Lv(Fa Hb Kf Kk Kn Kx Nc Oa Ou Po Qh St Uf Vp Vu) Jt(Aa Ax bV cN CT cU cX dF jD Kk nY Ue Uk Um) Pe(cF cK Hb Hx Ih Jq lX Mb My Nc Ne oN Pz Qg Uv) aN(dR Ed Fa Ic Ke Kk Kn Kr Ou Ps Qh Rg Vp Vq Wm) nH(aQ aV Bo cF cJ Cw iB iH Ke Lx No Nw Ou Un Ut) Gc(bA bU cF cK cT De Hv Ik Ju kG Mm Ni Pi Qy) Lw(aC Ih Ik Ip It Jh Jq Mm Nc Nm Nn Nr Po Pz) Nf(Dc Di Ih Ii Ik Jh Jo Ke Ma nN Oh Pd Pz Un) Ra(Ax Dc iB Id Is Js Ke Kn Li Lx Nw Nx Tn wD) wQ(cU Et Fr Im Iq Js Jv Kf Lu Nv Ou Po Qa Qe) Mp(Aa Ih Ip Jh Jl Jq Jr Mb Mm Nc Nn Nr Qb) Tl(aP cC cG dF Ex Is Lx Mq Ny Oa Qb Qy Tn) bA(bL bV Dc Ex Gz Hb Hu Io Kx Mm Nm Nx On) cT(Ct Is Iv Jg Jp Lh Li Nj Nt Nu On Qa Qb) rC(Dc Dd Dl Ez hV iB Id Im jD Jv qA Un Vu) Ax(bU gW Im Io Is Jg Ke Li Ok Qa Qz Us) Bc(cK Di Fp gW Iv kR Lz Nj Qb Qg Um

Figure 31 Continued uR) Sj(aP bO bR Fr Im Jl Li Mr Mw Nu Oa On) dF(aH An aO bZ cF Im Li lM nl Nj Nx Vs) Mb(Ii It Jh Jo Jq Mi Nc Ne Nr Po Pz) Tn(Ch Hu Ib Iz ml Nd Nu Ua Uk Um Vc) Hb(aM bV cN Ed Fw hC Jl Kk Nd Uf Vu) Jr(Bb cB cU Ih In Ip Mi Ms rB tV Wm) Kf(aM Ao dH Ju Jv kG Kj Mq Nd uY Vs) jD(Gl Js Ke Mm Nx Ny Qd Qe St Uf Wm) Iz(Ba Jl No Nv Nw Ok Qd Uf uY wD) Kk(cX dJ Ed Ex Fw Io Js Li Nr Us) Kx(cV dJ eQ Hu Im Ke Ml Qa rR Un) nN(aC bX Dp iB In Ji Jm Nd Nw Nx) ml(aA aQ bF cF cY gW Ji Lx Nv Ok) Pz(Du Ih In Jl Mh Nm No Nr Of) Kn(dH Ed Et Ik lX Nd Of Qa uO) On(aZ Ct Ed Hp Id Si Uc Ue Us) Uk(Cq Dc Ir Js Ou Pi Qh rZ Uf) Un(Dc Dp Hu Qg Um uR Us Uv Wm) mZ(Gp Ha Hf Hl Ld Ou Qu Vi Vv) tT(Et iA Ij Il Im Js Mh Mm Ri) rR(Dl hX jK Jl Ou Rb Vu wD zH) Qd(gW hV Qw Qz Rg rZ Us Vs) Vc(Fr gL Ji No Nt Om Ou Xa) hC(Ba cP Dl dX jB Jg Mm Ny) Nr(Id Ih Ip Mi Mr Ms Oy) Nu(aK bE bO bV cU Di eM) Nc(Ih In Jo Mi Mq Ni Nk) Ik(Fa Fb Id Ke Oy Pi Vu) Io(bO bV Cp cU Di Fw Mh) Zx(aC Ed Ha jE Ju Qb Rh) Rg(Fr Js Lh No Ok Qa Qe) gW(An dH Ex Ir nA Nw Po) jF(Gz Ir Js kF kK LY) uY(Et Id Ly Ri Vs Vv wE) Nj(aK Bb bV cU dU oV) Ho(aC As bR cX Us Zw) Im(bE dE Hp Kz Si Vs) In(Ii Ip Jm Jq Pi Po) Qz(Dk Fr iB Li Lx St) Xa(bR cN dE Ju mS Us) Ke(Hu nC Nm Of Si Wm) Ok(Ed Ef Hc Um Uu Uv) Uf(Gz Jo lM mS Of Vs) rZ(Dl Et Js Mm Nk Uh) Ti(lM Rh tN tX wJ) Fa(dJ Ji lX Ml Mz) Ex(aV bR cB nI Us) Mi(Ih It Jh Ne Nn) Oa(Dp Hf Ns Qg Ry) Vu(Du Qg rB sF Uv) bU(Bb Is nO Ry Vi) sI(bC Et lL pS wE) wF(Lu Qm Qw Ua Vs) kF(Dp iB jQ lK lN) kN(aL Ji Li Lx Nw) Ba(Fp lX Of Qb) Wm(Gp Pi St uO) Gz(cK Nt qZ vB) Nd(Ld Si Vh Yj) Hr(Ii Jo Jq Po) Id(dJ Ed hV Hx) Ih(bE Ip Mq Ni) Iv(aM bE cG cX) Lh(Ao bL Dp Zw) aK(Ij Nb nO nY) cB(cU Lz Nx Vi) wD(cY Dk Mm Qy) Bb(aM cU Mh) Cq(Qw uR Vs) Dc(Ni Nt Um) Mr(Ip Jo Nh) Hp(Dk Mw Qa) Is(bE Qg Vs) Sh(Jk Mn Nb) Qb(Di Qg Um) Ji(hP kI Wn) Ps(aC bO Rm) Rh(Ry Yg Yi) Nw(hV lM nO) Ny(iB jB jI) Vq(cF iZ Ue) bL(cG Nv Zq) cN(Jg Jp Li) nI(cG Fw tF) wP(iA Jq Nx) kK(jV jY lN) Cv(hV Vj) Du(kS Up) Ed(Nx wE) Fp(bV cG) Nn(Jl Mc) No(Kd Vp) Nt(aZ bE) Lx(Ao dJ) Ms(Jh Ma) Ij(cU Qw) Hc(Fr Ut) Yj(Ha Ne) Yd(lL qW) Qu(eQ lX) Of(Ad Fb) Uh(Iq nJ) Us(Li Oh) Oy(Ii Jq) aC(Uc Vj) aV(Lz nO) cX(dR Ic) nA(cY iH) iA(rQ zH) iB(lK nC) tV(Js nW) jB(bN Nb) rB(Tv Vp) kG(Hq Nk) lM(Cw Gl) BnuR DeVi DkQw PobS EtrQ ThwG GpiZ NqvI LutN MmrX MneQ MyOm NibV ItJo YgbO QewE JgcU JlUm JphP LtoV OutO UgkI UwcK VagV aFuO aLlW aMdK bBnY bCoD bQmE cRlX dXpF lYlK iHkO sHjR sKlL

Figure 31 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 8.4E1 | 6.0E1 | 9.5E1 | 8.1E1 | 6.6E1 | 7.3E1 | 8.0E0 | 7.0E0 | 4.8E2 | 4.0E2 | 261 | 34 | 261 | 34 | 0.41 |
| Ad | ug/mL | 4.7E-2 | 5.4E-2 | 1.3E-1 | 7.5E-2 | 7.0E-1 | 7.7E-2 | 6.8E-4 | 7.8E-4 | 8.5E0 | 3.5E-1 | 147 | 26 | 147 | 26 | 0.52 |
| Af | ng/mL | 1.2E0 | 1.8E0 | 1.1E1 | 6.2E0 | 4.8E1 | 7.4E0 | 1.7E-3 | 1.7E-3 | 5.3E2 | 2.1E1 | 147 | 26 | 147 | 26 | 0.54 |
| Aj | ug/mL | 1.1E0 | 6.6E-1 | 2.4E0 | 2.0E0 | 2.5E0 | 2.4E0 | 1.5E-3 | 1.3E-3 | 6.1E0 | 5.8E0 | 147 | 26 | 147 | 26 | 0.47 |
| Al | mg/mL | 8.8E-5 | 7.9E-5 | 2.7E-4 | 3.3E-4 | 4.5E-4 | 4.6E-4 | 4.3E-6 | 6.6E-6 | 1.8E-3 | 1.5E-3 | 147 | 26 | 147 | 26 | 0.51 |
| An | U/mL | 5.8E1 | 8.7E1 | 2.4E2 | 3.4E2 | 8.1E2 | 6.3E2 | 2.8E-1 | 1.1E0 | 7.8E3 | 2.5E3 | 147 | 26 | 147 | 26 | 0.59 |
| Ao | pg/mL | 9.1E1 | 1.4E2 | 5.7E2 | 4.2E2 | 3.8E3 | 9.0E2 | 1.5E0 | 4.1E0 | 3.9E4 | 4.5E3 | 147 | 26 | 147 | 26 | 0.60 |
| Ap | ng/mL | 3.3E1 | 3.5E1 | 4.8E1 | 6.1E1 | 5.4E1 | 7.0E1 | 2.0E0 | 2.7E0 | 3.3E2 | 2.4E2 | 147 | 26 | 147 | 26 | 0.52 |
| Ar | ng/mL | 6.8E-1 | 1.1E0 | 2.5E0 | 6.6E0 | 5.6E0 | 1.4E1 | 3.4E-3 | 4.1E-2 | 4.7E1 | 5.1E1 | 147 | 26 | 147 | 26 | 0.56 |
| As | ng/mL | 8.7E-3 | 8.2E-3 | 2.1E-2 | 9.0E-3 | 1.0E-1 | 8.3E-3 | 1.7E-3 | 1.7E-3 | 1.2E0 | 3.3E-2 | 147 | 26 | 147 | 26 | 0.47 |
| Aw | pg/mL | 1.6E1 | 2.0E1 | 1.7E1 | 2.0E1 | 6.3E0 | 5.7E0 | 2.9E-2 | 8.2E0 | 5.1E1 | 3.2E1 | 147 | 26 | 147 | 26 | 0.68 |
| Ax | ng/mL | 2.0E0 | 2.6E0 | 2.3E1 | 6.7E1 | 9.1E1 | 1.9E2 | 1.2E-2 | 1.0E-4 | 7.7E2 | 8.5E2 | 147 | 26 | 147 | 26 | 0.51 |
| Ba | ng/mL | 8.3E1 | 4.4E2 | 5.2E2 | 1.8E3 | 1.4E3 | 3.3E3 | 1.9E0 | 1.1E0 | 8.1E3 | 1.5E4 | 147 | 26 | 147 | 26 | 0.64 |
| Bb | ng/mL | 4.1E0 | 5.9E0 | 7.1E0 | 9.4E0 | 8.4E0 | 1.2E1 | 4.1E-3 | 4.1E-3 | 4.9E1 | 4.8E1 | 147 | 26 | 147 | 26 | 0.52 |
| Bc | ng/mL | 3.5E1 | 7.6E1 | 1.3E2 | 1.6E2 | 2.4E2 | 2.4E2 | 4.9E-1 | 1.0E0 | 1.2E3 | 9.9E2 | 147 | 26 | 147 | 26 | 0.56 |
| Bg | ng/mL | 1.1E-1 | 2.6E-1 | 3.4E0 | 2.2E1 | 1.3E1 | 8.2E1 | 5.3E-4 | 5.3E-4 | 1.0E2 | 4.0E2 | 147 | 26 | 147 | 26 | 0.59 |
| Bn | ng/mL | 5.6E-2 | 4.4E-1 | 1.5E0 | 1.4E0 | 5.1E0 | 2.0E0 | 5.6E-2 | 5.6E-2 | 5.8E1 | 7.4E0 | 147 | 26 | 147 | 26 | 0.62 |
| Bo | ng/mL | 1.3E1 | 2.0E1 | 1.4E1 | 2.0E1 | 1.1E1 | 1.2E1 | 1.6E-2 | 2.2E0 | 5.0E1 | 5.3E1 | 147 | 26 | 147 | 26 | 0.65 |
| Ch | uIU/mL | 1.0E0 | 1.1E0 | 3.0E1 | 6.1E1 | 1.7E2 | 2.3E2 | 3.4E-3 | 1.5E-1 | 1.8E3 | 1.2E3 | 147 | 26 | 147 | 26 | 0.54 |
| Co | pg/mL | 4.7E1 | 5.9E1 | 2.4E2 | 1.9E2 | 1.4E3 | 4.1E2 | 1.5E-1 | 3.6E0 | 1.7E4 | 2.1E3 | 147 | 26 | 147 | 26 | 0.54 |
| Cp | ng/mL | 2.2E1 | 2.7E1 | 3.5E1 | 4.0E1 | 1.1E2 | 3.1E1 | 6.0E-1 | 4.7E0 | 1.3E3 | 1.4E2 | 147 | 26 | 147 | 26 | 0.62 |
| Cq | ng/mL | 2.8E-2 | 4.2E-2 | 4.4E-1 | 1.9E-1 | 4.1E0 | 4.7E-1 | 8.0E-4 | 8.0E-4 | 4.9E1 | 2.3E0 | 147 | 26 | 147 | 26 | 0.60 |
| Cs | ng/mL | 5.9E1 | 1.1E2 | 4.7E2 | 6.1E2 | 1.8E3 | 1.3E3 | 8.3E-1 | 8.9E-1 | 1.8E4 | 5.1E3 | 147 | 26 | 147 | 26 | 0.55 |
| Ct | ng/mL | 3.1E-1 | 8.7E-1 | 4.0E1 | 4.9E1 | 1.2E2 | 1.2E2 | 8.9E-3 | 1.1E-4 | 6.2E2 | 4.4E2 | 147 | 26 | 147 | 26 | 0.56 |
| Cu | ng/mL | 2.5E-1 | 7.9E-1 | 9.0E-1 | 1.9E0 | 5.5E0 | 4.1E0 | 1.9E-2 | 1.7E-2 | 6.6E1 | 2.1E1 | 147 | 26 | 147 | 26 | 0.69 |
| Cv | ng/mL | 6.1E0 | 5.1E0 | 2.8E1 | 3.7E1 | 6.7E1 | 9.4E1 | 2.0E-2 | 7.5E-2 | 5.3E2 | 4.7E2 | 147 | 26 | 147 | 26 | 0.48 |
| Cw | mIU/mL | 3.3E-2 | 4.9E-2 | 8.8E-2 | 5.5E-2 | 5.6E-1 | 3.8E-2 | 8.9E-4 | 2.8E-3 | 6.8E0 | 1.5E-1 | 147 | 26 | 147 | 26 | 0.60 |
| Cx | ng/mL | 6.9E-1 | 7.2E-1 | 4.9E1 | 5.6E1 | 9.7E1 | 1.1E2 | 9.3E-5 | 9.3E-5 | 3.9E2 | 2.8E2 | 147 | 26 | 147 | 26 | 0.47 |
| Db | ug/mL | 7.5E0 | 8.1E0 | 8.7E0 | 9.3E0 | 7.9E0 | 5.7E0 | 4.5E-1 | 8.1E-1 | 5.9E1 | 2.3E1 | 147 | 26 | 147 | 26 | 0.56 |
| Dc | nmol/L | 2.1E-2 | 2.3E-2 | 1.4E-1 | 2.7E-1 | 1.2E0 | 5.6E-1 | 5.2E-6 | 1.1E-3 | 1.4E1 | 2.2E0 | 147 | 26 | 147 | 26 | 0.56 |
| Dd | ug/mL | 7.7E-2 | 6.8E-2 | 2.0E-1 | 2.3E-1 | 3.8E-1 | 3.5E-1 | 4.8E-1 | 1.3E-3 | 3.6E0 | 1.5E0 | 147 | 26 | 147 | 26 | 0.51 |
| De | ng/mL | 3.4E-3 | 1.7E-1 | 7.0E-2 | 1.7E-1 | 1.4E-1 | 2.3E-1 | 3.4E-3 | 3.4E-3 | 9.2E-1 | 1.1E0 | 147 | 26 | 147 | 26 | 0.69 |
| Dg | ng/mL | 3.6E1 | 4.0E1 | 4.8E1 | 4.7E1 | 4.0E1 | 3.9E1 | 7.1E-1 | 7.8E-1 | 1.9E2 | 1.2E2 | 147 | 26 | 147 | 26 | 0.50 |
| Di | pg/mL | 2.0E0 | 3.3E0 | 2.3E0 | 3.3E0 | 2.2E0 | 1.9E0 | 1.8E-1 | 1.8E-1 | 1.3E1 | 9.3E0 | 147 | 26 | 147 | 26 | 0.67 |
| Dk | uIU/mL | 1.4E-2 | 3.0E-2 | 5.2E-2 | 1.2E-1 | 1.7E-1 | 2.3E-1 | 1.1E-4 | 1.1E-4 | 1.6E0 | 9.8E-1 | 147 | 26 | 147 | 26 | 0.61 |
| Dl | ng/mL | 2.1E2 | 2.0E2 | 3.0E2 | 2.9E2 | 2.8E2 | 2.8E2 | 5.5E0 | 4.4E0 | 1.6E3 | 1.1E3 | 147 | 26 | 147 | 26 | 0.49 |
| Dp | ng/ml | 2.4E0 | 1.2E0 | 5.9E0 | 3.1E0 | 9.4E0 | 5.0E0 | 3.7E-3 | 3.7E-3 | 5.6E1 | 1.8E1 | 111 | 23 | 111 | 23 | 0.37 |
| Dr | pg/ml | 2.9E1 | 2.2E1 | 2.4E2 | 6.1E1 | 1.4E3 | 1.1E2 | 7.5E-1 | 7.5E-1 | 1.0E4 | 3.6E2 | 57 | 15 | 57 | 15 | 0.44 |
| Du | pg/ml | 1.6E2 | 2.2E2 | 1.6E3 | 5.2E2 | 4.6E3 | 6.4E2 | 1.2E0 | 1.2E0 | 2.4E4 | 1.8E3 | 43 | 14 | 43 | 14 | 0.48 |
| Ef | ng/ml | 9.3E-2 | 2.0E-1 | 7.5E-1 | 1.8E0 | 1.8E0 | 3.0E0 | 5.7E-4 | 5.7E-4 | 1.0E1 | 9.9E0 | 124 | 22 | 124 | 22 | 0.59 |
| Wm | % | 8.5E-2 | 8.5E-2 | 9.8E0 | 4.8E1 | 7.0E1 | 2.0E2 | 5.4E-2 | 8.5E-2 | 7.7E2 | 1.0E3 | 130 | 28 | 130 | 28 | 0.47 |
| Ed | pg/ml | 4.4E0 | 3.1E1 | 3.1E1 | 7.0E1 | 5.9E1 | 1.1E2 | 5.2E-1 | 5.2E-1 | 5.0E2 | 4.8E2 | 111 | 23 | 111 | 23 | 0.63 |
| Yf | ng/mL | 1.5E1 | 1.7E1 | 3.8E1 | 9.9E1 | 5.5E1 | 1.8E2 | 2.9E-1 | 2.9E-1 | 2.4E2 | 5.9E2 | 45 | 14 | 45 | 14 | 0.54 |
| Tj | pg/mL | 3.7E-1 | 3.7E-1 | 4.1E1 | 2.5E1 | 2.3E2 | 6.7E1 | 3.7E-1 | 3.7E-1 | 2.3E3 | 2.5E2 | 121 | 23 | 121 | 23 | 0.46 |
| Po | pg/ml | 1.4E-1 | 7.4E0 | 9.2E0 | 1.9E1 | 3.0E1 | 3.8E1 | 8.0E-3 | 2.6E-2 | 2.7E2 | 2.2E2 | 307 | 44 | 307 | 44 | 0.69 |
| Ti | ug/mL | 3.2E0 | 3.9E0 | 5.0E0 | 4.7E0 | 4.4E0 | 3.8E0 | 1.2E-1 | 4.0E-1 | 1.8E1 | 1.1E1 | 66 | 17 | 66 | 17 | 0.49 |
| Em | ng/ml | 2.9E-3 | 2.6E-2 | 7.7E-2 | 4.8E-2 | 2.4E-1 | 6.7E-2 | 8.4E-4 | 8.4E-4 | 1.9E0 | 2.4E-1 | 74 | 18 | 74 | 18 | 0.54 |
| Et | ng/ml | 1.4E3 | 2.6E3 | 1.6E3 | 2.3E3 | 1.2E3 | 1.3E3 | 7.5E1 | 7.9E1 | 4.8E3 | 5.0E3 | 306 | 44 | 306 | 44 | 0.65 |
| Eq | pg/ml | 1.3E2 | 3.0E2 | 3.1E2 | 4.6E2 | 3.8E2 | 4.6E2 | 1.0E0 | 1.0E0 | 1.5E3 | 1.4E3 | 43 | 14 | 43 | 14 | 0.59 |
| Th | ug/mL | 1.2E0 | 1.5E0 | 1.7E0 | 2.1E0 | 1.5E0 | 1.7E0 | 2.6E-3 | 2.6E-1 | 7.5E0 | 5.9E0 | 66 | 17 | 66 | 17 | 0.56 |
| Fa | ng/ml | 4.2E1 | 5.8E1 | 1.3E2 | 9.7E1 | 4.2E2 | 1.1E2 | 2.6E-1 | 1.6E0 | 3.7E3 | 4.3E2 | 110 | 20 | 110 | 20 | 0.55 |
| Ez | ng/ml | 3.7E0 | 5.3E0 | 1.4E1 | 2.2E1 | 2.7E1 | 4.5E1 | 1.3E-2 | 1.3E-2 | 1.6E2 | 2.0E2 | 111 | 23 | 111 | 23 | 0.52 |
| Fb | ng/ml | 2.5E1 | 2.7E1 | 2.2E1 | 2.6E1 | 1.1E1 | 1.3E1 | 6.6E-1 | 8.9E-1 | 4.3E1 | 4.3E1 | 111 | 20 | 111 | 20 | 0.58 |
| Ex | ng/ml | 6.0E-2 | 1.6E-1 | 1.7E-1 | 5.0E-1 | 3.1E-1 | 9.7E-1 | 3.5E-5 | 1.7E-4 | 2.2E0 | 4.1E0 | 86 | 19 | 86 | 19 | 0.65 |

Figure 32

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fc | pg/ml | 2.2E-1 | 2.2E-1 | 2.1E1 | 3.2E1 | 8.0E1 | 1.0E2 | 2.2E-1 | 2.2E-1 | 4.5E2 | 3.9E2 | 44 | 14 | 44 | 14 | 0.53 |
| Fd | pg/ml | 8.2E1 | 1.1E2 | 9.6E2 | 2.6E3 | 3.8E3 | 6.2E3 | 4.5E-1 | 9.8E-1 | 2.5E4 | 2.2E4 | 44 | 14 | 44 | 14 | 0.55 |
| Fi | pg/ml | 2.5E-1 | 2.5E-1 | 5.9E1 | 2.0E2 | 1.7E2 | 5.0E2 | 2.5E-1 | 2.5E-1 | 8.5E2 | 1.8E3 | 44 | 14 | 44 | 14 | 0.57 |
| Fn | ng/ml | 2.1E-1 | 2.8E-1 | 4.3E0 | 2.3E0 | 7.6E0 | 3.7E0 | 1.1E-14 | 2.1E-1 | 3.7E1 | 1.6E1 | 111 | 23 | 111 | 23 | 0.51 |
| Fp | ng/ml | 1.3E1 | 1.5E1 | 2.3E1 | 3.1E1 | 2.6E1 | 3.6E1 | 6.0E-3 | 3.0E-1 | 1.3E2 | 1.3E2 | 309 | 44 | 309 | 44 | 0.56 |
| Fr | ng/ml | 3.3E4 | 1.1E5 | 1.1E5 | 2.7E5 | 1.7E5 | 2.9E5 | 1.9E2 | 1.3E3 | 8.4E5 | 8.4E5 | 314 | 46 | 314 | 46 | 0.67 |
| Fw | pg/ml | 1.1E0 | 1.4E1 | 4.9E1 | 3.7E1 | 2.8E2 | 6.1E1 | 1.2E-1 | 1.2E-1 | 3.0E3 | 2.5E2 | 125 | 23 | 125 | 23 | 0.69 |
| Fy | ng/ml | 3.4E1 | 4.4E1 | 6.3E1 | 1.2E2 | 8.9E1 | 1.5E2 | 1.2E-1 | 1.2E-1 | 6.5E2 | 5.3E2 | 110 | 21 | 110 | 21 | 0.60 |
| Gh | pg/ml | 1.3E0 | 5.0E0 | 2.5E1 | 9.5E0 | 6.1E1 | 1.2E1 | 2.9E-2 | 2.9E-2 | 3.2E2 | 4.6E1 | 44 | 14 | 44 | 14 | 0.59 |
| Gb | % | 4.4E1 | 2.7E1 | 5.6E1 | 4.2E1 | 5.6E1 | 4.4E1 | 3.7E0 | 2.2E0 | 3.0E2 | 1.5E2 | 44 | 14 | 44 | 14 | 0.39 |
| Gc | ng/ml | 9.9E1 | 1.2E2 | 1.7E2 | 1.5E2 | 2.2E2 | 1.5E2 | 6.4E0 | 2.7E1 | 1.2E3 | 5.1E2 | 57 | 15 | 57 | 15 | 0.52 |
| Gd | ng/ml | 3.3E1 | 2.9E1 | 3.4E1 | 2.9E1 | 1.9E1 | 1.6E1 | 3.7E0 | 3.0E0 | 8.1E1 | 5.6E1 | 66 | 16 | 66 | 16 | 0.43 |
| Gn | U/ml | 2.2E-1 | 1.3E-1 | 3.3E0 | 5.1E-1 | 1.6E1 | 6.7E-1 | 5.6E-3 | 5.6E-3 | 1.1E2 | 2.2E0 | 56 | 15 | 56 | 15 | 0.44 |
| Gl | pg/ml | 8.6E3 | 2.3E4 | 1.2E4 | 1.8E4 | 9.1E3 | 1.1E4 | 9.1E1 | 5.3E2 | 3.2E4 | 3.2E4 | 125 | 23 | 125 | 23 | 0.68 |
| Gp | U/ml | 1.2E0 | 1.5E-1 | 2.6E0 | 9.2E-1 | 3.6E0 | 1.3E0 | 1.5E-2 | 1.5E-2 | 2.0E1 | 4.2E0 | 125 | 22 | 125 | 22 | 0.33 |
| Gz | ug/ml | 1.5E0 | 8.1E-1 | 6.0E0 | 3.2E0 | 5.9E0 | 4.4E0 | 6.2E-2 | 4.2E-2 | 2.5E1 | 1.1E1 | 75 | 19 | 75 | 19 | 0.36 |
| Ha | ng/ml | 2.0E0 | 2.6E0 | 8.4E0 | 9.8E0 | 2.0E1 | 2.0E1 | 1.7E-2 | 1.7E-2 | 1.0E2 | 9.2E1 | 109 | 23 | 109 | 23 | 0.57 |
| Nm | pg/ml | 1.3E4 | 1.4E4 | 3.6E4 | 5.0E4 | 9.3E4 | 9.4E4 | 1.0E-9 | 1.0E-9 | 9.6E5 | 4.4E5 | 310 | 44 | 310 | 44 | 0.53 |
| Nn | pg/ml | 1.4E2 | 7.5E2 | 1.1E3 | 1.6E4 | 4.5E3 | 5.1E4 | 1.0E-9 | 1.0E-9 | 6.0E4 | 3.1E5 | 310 | 44 | 310 | 44 | 0.69 |
| No | pg/ml | 1.5E1 | 2.5E1 | 3.5E1 | 8.5E1 | 7.9E1 | 1.7E2 | 1.0E-9 | 3.3E-1 | 9.1E2 | 7.7E2 | 310 | 44 | 310 | 44 | 0.62 |
| Nq | pg/ml | 1.6E0 | 1.1E1 | 1.8E1 | 6.4E1 | 6.7E1 | 1.4E2 | 1.0E-9 | 1.0E-9 | 6.3E2 | 6.7E2 | 310 | 44 | 310 | 44 | 0.65 |
| Nr | pg/ml | 1.3E0 | 7.1E0 | 2.3E1 | 5.7E1 | 8.6E1 | 2.1E2 | 1.0E-9 | 1.0E-9 | 9.8E2 | 1.4E3 | 310 | 44 | 310 | 44 | 0.61 |
| Ns | pg/ml | 1.0E-9 | 1.0E-9 | 4.9E0 | 2.7E1 | 2.5E1 | 1.7E2 | 1.0E-9 | 1.0E-9 | 2.4E2 | 1.1E3 | 310 | 44 | 310 | 44 | 0.51 |
| Nt | pg/ml | 1.0E2 | 1.5E2 | 1.3E2 | 2.2E2 | 1.3E2 | 2.3E2 | 9.8E-1 | 3.5E1 | 1.7E3 | 1.2E3 | 310 | 44 | 310 | 44 | 0.67 |
| Nu | pg/ml | 1.7E1 | 5.0E1 | 5.3E1 | 9.0E1 | 8.8E1 | 1.2E2 | 1.0E-9 | 1.0E-9 | 6.3E2 | 6.3E2 | 310 | 44 | 310 | 44 | 0.64 |
| Lu | pg/ml | 1.0E4 | 9.0E3 | 1.4E4 | 2.1E4 | 2.8E4 | 8.3E4 | 5.2E2 | 1.3E3 | 3.9E5 | 5.6E5 | 310 | 44 | 310 | 44 | 0.42 |
| Lv | pg/ml | 1.0E-9 | 1.6E1 | 1.4E1 | 3.6E1 | 2.8E1 | 5.3E1 | 1.0E-9 | 1.0E-9 | 2.4E2 | 2.6E2 | 310 | 44 | 310 | 44 | 0.63 |
| Lw | pg/ml | 1.0E-9 | 1.0E-9 | 5.2E-1 | 5.9E0 | 5.4E0 | 2.7E1 | 1.0E-9 | 1.0E-9 | 8.0E1 | 1.8E2 | 310 | 44 | 310 | 44 | 0.55 |
| Lx | pg/ml | 1.0E-9 | 1.8E2 | 2.3E2 | 5.0E2 | 1.4E3 | 7.2E2 | 1.0E-9 | 1.0E-9 | 2.2E4 | 2.8E3 | 310 | 44 | 310 | 44 | 0.71 |
| Ly | pg/ml | 1.0E-9 | 1.0E-9 | 9.6E0 | 5.3E0 | 1.8E1 | 1.1E1 | 1.0E-9 | 1.0E-9 | 1.1E2 | 4.8E1 | 310 | 44 | 310 | 44 | 0.45 |
| Lz | pg/ml | 1.0E-9 | 1.0E-9 | 3.3E0 | 4.7E0 | 2.7E1 | 1.5E1 | 1.0E-9 | 1.0E-9 | 4.3E2 | 6.2E1 | 310 | 44 | 310 | 44 | 0.53 |
| Ma | pg/ml | 3.9E2 | 8.0E2 | 2.0E3 | 5.9E3 | 5.3E3 | 1.1E4 | 1.0E-9 | 1.0E-9 | 6.5E4 | 5.2E4 | 310 | 44 | 310 | 44 | 0.59 |
| Mb | pg/ml | 2.5E1 | 3.0E1 | 3.1E1 | 3.7E1 | 1.7E1 | 2.0E1 | 4.1E0 | 1.5E1 | 2.1E2 | 1.1E2 | 310 | 44 | 310 | 44 | 0.58 |
| Mc | pg/ml | 1.0E-9 | 1.0E-9 | 5.6E-2 | 3.8E-2 | 7.8E-1 | 2.5E-1 | 1.0E-9 | 1.0E-9 | 1.3E1 | 1.7E0 | 310 | 44 | 310 | 44 | 0.51 |
| Md | pg/ml | 1.0E-9 | 1.0E-9 | 6.8E-1 | 6.1E-1 | 5.7E0 | 1.9E0 | 1.0E-9 | 1.0E-9 | 6.8E1 | 9.8E0 | 310 | 44 | 310 | 44 | 0.55 |
| Me | pg/ml | 3.2E1 | 2.4E1 | 3.2E1 | 2.8E1 | 2.3E1 | 3.5E1 | 1.0E-9 | 1.0E-9 | 3.2E2 | 1.8E2 | 310 | 44 | 310 | 44 | 0.38 |
| Mf | pg/ml | 1.0E-9 | 1.0E-9 | 5.1E-1 | 1.3E0 | 3.5E0 | 5.6E0 | 1.0E-9 | 1.0E-9 | 5.6E1 | 3.7E1 | 310 | 44 | 310 | 44 | 0.55 |
| Mg | pg/ml | 1.1E0 | 2.7E-1 | 6.4E0 | 1.1E1 | 1.2E1 | 2.7E1 | 1.0E-9 | 1.0E-9 | 9.2E1 | 1.5E2 | 310 | 44 | 310 | 44 | 0.50 |
| Mh | pg/ml | 1.0E-9 | 1.0E-9 | 1.2E0 | 1.3E0 | 8.0E0 | 3.7E0 | 1.0E-9 | 1.0E-9 | 1.1E2 | 1.8E1 | 310 | 44 | 310 | 44 | 0.57 |
| Mi | pg/ml | 1.0E-9 | 1.0E-9 | 2.0E0 | 1.7E1 | 2.0E1 | 8.0E1 | 1.0E-9 | 1.0E-9 | 3.2E2 | 5.2E2 | 310 | 44 | 310 | 44 | 0.56 |
| Mj | pg/ml | 1.0E-9 | 1.0E-9 | 5.9E0 | 1.6E1 | 3.3E1 | 3.8E1 | 1.0E-9 | 1.0E-9 | 4.6E2 | 2.1E2 | 310 | 44 | 310 | 44 | 0.61 |
| Mk | pg/ml | 1.5E0 | 5.4E0 | 1.6E1 | 2.0E1 | 9.7E1 | 7.6E1 | 1.0E-9 | 1.0E-9 | 1.3E3 | 5.0E2 | 310 | 44 | 310 | 44 | 0.56 |
| Ml | pg/ml | 1.0E-9 | 1.0E-9 | 1.1E1 | 1.2E1 | 1.2E2 | 5.4E1 | 1.0E-9 | 1.0E-9 | 2.1E3 | 3.4E2 | 310 | 44 | 310 | 44 | 0.48 |
| Mm | pg/ml | 5.5E2 | 8.3E2 | 1.0E3 | 1.7E3 | 1.3E3 | 2.2E3 | 1.0E-9 | 1.0E-9 | 1.0E4 | 1.0E4 | 310 | 44 | 310 | 44 | 0.57 |
| Mn | pg/ml | 5.7E0 | 1.0E1 | 1.1E1 | 1.1E1 | 2.6E1 | 9.8E0 | 1.0E-9 | 1.0E-9 | 3.5E2 | 5.1E1 | 310 | 44 | 310 | 44 | 0.61 |
| Mp | pg/ml | 1.0E-9 | 1.0E1 | 1.3E1 | 8.4E1 | 5.1E1 | 3.6E2 | 1.0E-9 | 1.0E-9 | 6.3E2 | 2.4E3 | 310 | 44 | 310 | 44 | 0.66 |
| Mq | pg/ml | 1.0E-9 | 1.0E-9 | 2.3E0 | 6.2E0 | 1.4E1 | 1.6E1 | 1.0E-9 | 1.0E-9 | 1.8E2 | 7.4E1 | 310 | 44 | 310 | 44 | 0.57 |
| Mr | pg/ml | 1.0E-9 | 1.0E-9 | 3.3E1 | 1.2E2 | 1.9E2 | 5.3E2 | 1.0E-9 | 1.0E-9 | 2.2E3 | 3.4E3 | 310 | 44 | 310 | 44 | 0.59 |
| Ms | pg/ml | 3.2E2 | 3.5E2 | 4.6E2 | 5.4E2 | 5.2E2 | 8.7E2 | 1.0E-9 | 1.0E-9 | 3.2E3 | 4.7E3 | 310 | 44 | 310 | 44 | 0.49 |
| Mt | pg/ml | 1.7E-1 | 2.3E0 | 8.9E0 | 9.4E1 | 4.6E1 | 4.9E2 | 1.0E-9 | 1.0E-9 | 7.1E2 | 3.2E3 | 310 | 44 | 310 | 44 | 0.67 |
| Mu | pg/ml | 1.0E-9 | 1.0E-9 | 7.5E-1 | 8.5E0 | 6.4E0 | 3.6E1 | 1.0E-9 | 1.0E-9 | 9.9E1 | 2.3E2 | 310 | 44 | 310 | 44 | 0.61 |
| Mv | pg/ml | 1.0E-9 | 1.0E-9 | 6.0E1 | 1.5E2 | 3.5E2 | 2.8E2 | 1.0E-9 | 1.0E-9 | 4.5E3 | 9.2E2 | 310 | 44 | 310 | 44 | 0.61 |
| Mw | pg/ml | 3.6E1 | 7.7E1 | 2.7E2 | 5.7E2 | 1.4E3 | 1.2E3 | 1.0E-9 | 1.0E-9 | 1.8E4 | 5.3E3 | 310 | 44 | 310 | 44 | 0.61 |
| Mx | pg/ml | 1.0E-9 | 1.0E-9 | 2.3E-1 | 1.9E0 | 8.9E-1 | 5.6E0 | 1.0E-9 | 1.0E-9 | 9.2E0 | 3.2E1 | 310 | 44 | 310 | 44 | 0.64 |
| My | pg/ml | 1.0E-9 | 1.0E-9 | 3.4E2 | 2.4E2 | 2.6E3 | 5.2E2 | 1.0E-9 | 1.0E-9 | 3.9E4 | 2.1E3 | 310 | 44 | 310 | 44 | 0.57 |
| Mz | pg/ml | 1.1E1 | 2.9E1 | 2.7E1 | 1.1E2 | 8.6E1 | 2.9E2 | 1.0E-9 | 1.0E-9 | 1.3E3 | 1.9E3 | 310 | 44 | 310 | 44 | 0.72 |
| Na | pg/ml | 1.0E-9 | 1.0E-9 | 7.7E-1 | 9.3E-1 | 3.0E0 | 2.2E0 | 1.0E-9 | 1.0E-9 | 4.2E1 | 9.6E0 | 310 | 44 | 310 | 44 | 0.52 |

Figure 32 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nb | pg/ml | 2.1E0 | 3.3E0 | 3.9E0 | 1.0E1 | 1.2E1 | 3.2E1 | 1.0E-9 | 1.0E-9 | 1.5E2 | 2.1E2 | 310 | 44 | 310 | 44 | 0.61 |
| Nc | pg/ml | 3.2E2 | 1.6E2 | 5.3E2 | 3.3E2 | 7.6E2 | 4.1E2 | 1.0E-9 | 1.0E-9 | 9.2E3 | 1.6E3 | 310 | 44 | 310 | 44 | 0.42 |
| Nd | pg/ml | 2.8E1 | 1.7E1 | 3.5E1 | 2.6E1 | 1.4E2 | 2.8E1 | 1.0E-9 | 7.2E-1 | 2.1E3 | 1.5E2 | 310 | 44 | 310 | 44 | 0.50 |
| Ne | pg/ml | 4.3E2 | 3.2E2 | 5.3E2 | 4.0E2 | 5.6E2 | 5.6E2 | 1.0E-9 | 1.0E-9 | 7.0E3 | 3.6E3 | 310 | 44 | 310 | 44 | 0.38 |
| Nf | pg/ml | 1.0E-9 | 1.0E-9 | 3.0E0 | 3.4E0 | 1.2E1 | 1.6E1 | 1.0E-9 | 1.0E-9 | 1.3E2 | 1.1E2 | 310 | 44 | 310 | 44 | 0.49 |
| Ng | pg/ml | 1.3E1 | 9.4E0 | 9.1E1 | 7.7E1 | 1.9E2 | 1.2E2 | 1.0E-9 | 1.0E-9 | 1.6E3 | 5.9E2 | 310 | 44 | 310 | 44 | 0.49 |
| Nh | pg/ml | 6.3E1 | 4.1E1 | 8.2E1 | 5.9E1 | 7.4E1 | 7.6E1 | 1.0E-9 | 4.5E0 | 5.6E2 | 5.1E2 | 310 | 44 | 310 | 44 | 0.38 |
| Ni | pg/ml | 1.0E-9 | 3.1E1 | 8.1E1 | 1.1E2 | 1.3E2 | 1.7E2 | 1.0E-9 | 1.0E-9 | 1.1E3 | 7.1E2 | 310 | 44 | 310 | 44 | 0.55 |
| Nj | pg/ml | 7.2E0 | 6.3E0 | 1.1E1 | 7.5E0 | 1.2E1 | 6.4E0 | 1.0E-9 | 1.0E-9 | 6.9E1 | 2.2E1 | 310 | 44 | 310 | 44 | 0.43 |
| Nk | pg/ml | 1.8E1 | 1.2E1 | 3.3E1 | 2.3E1 | 4.0E1 | 2.8E1 | 1.0E-9 | 1.0E-9 | 2.0E2 | 8.8E1 | 310 | 44 | 310 | 44 | 0.44 |
| Nl | pg/ml | 4.3E1 | 3.1E1 | 5.9E1 | 3.5E1 | 7.8E1 | 3.6E1 | 1.0E-9 | 1.0E-9 | 1.1E3 | 1.8E2 | 310 | 44 | 310 | 44 | 0.37 |
| Hl | pg/ml | 1.1E1 | 2.3E0 | 1.2E2 | 1.6E1 | 5.4E2 | 2.2E1 | 1.0E-9 | 1.0E-9 | 3.6E3 | 6.1E1 | 44 | 14 | 44 | 14 | 0.40 |
| Ho | pg/ml | 1.6E1 | 2.3E1 | 2.9E1 | 4.4E1 | 5.9E1 | 5.0E1 | 1.0E-9 | 7.6E0 | 3.9E2 | 1.7E2 | 44 | 14 | 44 | 14 | 0.66 |
| Hp | ng/ml | 1.6E0 | 2.6E0 | 1.2E2 | 1.3E2 | 3.1E2 | 3.2E2 | 3.6E-1 | 1.0E-9 | 8.9E2 | 8.9E2 | 44 | 14 | 44 | 14 | 0.57 |
| Tz | pg/ml | 3.9E3 | 9.8E3 | 5.9E3 | 1.2E5 | 6.7E3 | 4.3E5 | 1.0E-9 | 9.8E1 | 5.3E4 | 2.1E6 | 111 | 23 | 111 | 23 | 0.69 |
| Ua | pg/ml | 3.3E3 | 6.3E3 | 3.1E4 | 2.8E4 | 2.0E5 | 4.1E4 | 1.0E-9 | 2.7E2 | 2.1E6 | 1.3E5 | 111 | 23 | 111 | 23 | 0.57 |
| Ub | pg/ml | 5.8E2 | 4.2E2 | 9.3E2 | 5.0E2 | 1.2E3 | 4.4E2 | 1.0E-9 | 2.3E0 | 9.8E3 | 1.4E3 | 111 | 23 | 111 | 23 | 0.38 |
| Ue | pg/ml | 3.1E1 | 1.9E1 | 3.9E1 | 2.6E1 | 3.4E1 | 2.3E1 | 9.8E-2 | 4.5E0 | 2.7E2 | 1.1E2 | 111 | 23 | 111 | 23 | 0.35 |
| Uc | pg/ml | 6.8E2 | 9.4E2 | 1.7E3 | 1.8E3 | 5.5E3 | 2.4E3 | 1.0E-9 | 1.5E1 | 5.7E4 | 9.4E3 | 111 | 23 | 111 | 23 | 0.57 |
| Ud | pg/ml | 1.0E-9 | 1.0E-9 | 4.0E0 | 1.0E-9 | 3.7E1 | 0.0E0 | 1.0E-9 | 1.0E-9 | 3.9E2 | 1.0E-9 | 111 | 23 | 111 | 23 | 0.49 |
| Hq | pg/ml | 1.1E0 | 2.4E0 | 1.8E2 | 1.9E1 | 2.0E3 | 5.7E1 | 1.0E-9 | 1.0E-9 | 2.8E4 | 3.4E2 | 308 | 44 | 308 | 44 | 0.62 |
| Hr | pg/ml | 9.1E1 | 9.3E1 | 6.9E2 | 4.0E2 | 1.4E3 | 8.3E2 | 1.0E-9 | 1.0E-9 | 1.2E4 | 3.8E3 | 308 | 44 | 308 | 44 | 0.49 |
| Hu | pg/ml | 5.4E0 | 2.4E1 | 4.1E3 | 7.1E3 | 3.9E4 | 4.0E4 | 1.0E-9 | 1.0E-9 | 6.3E5 | 2.6E5 | 308 | 44 | 308 | 44 | 0.56 |
| Hv | pg/ml | 1.3E0 | 2.6E0 | 5.3E0 | 7.8E0 | 5.1E1 | 2.5E1 | 1.0E-9 | 1.0E-9 | 8.9E2 | 1.6E2 | 308 | 44 | 308 | 44 | 0.66 |
| Hw | pg/ml | 6.4E0 | 6.5E0 | 4.6E1 | 2.6E1 | 5.3E2 | 7.8E1 | 1.0E-9 | 1.0E-9 | 9.4E3 | 5.0E2 | 308 | 44 | 308 | 44 | 0.54 |
| Hx | pg/ml | 8.4E0 | 1.8E1 | 5.6E1 | 7.4E1 | 5.3E2 | 2.0E2 | 1.0E-9 | 1.0E-9 | 9.3E3 | 1.3E3 | 308 | 44 | 308 | 44 | 0.63 |
| Ib | ng/ml | 3.6E-2 | 2.6E-2 | 1.2E0 | 2.5E0 | 6.2E0 | 8.0E0 | 1.0E-9 | 1.0E-9 | 5.6E1 | 3.6E1 | 110 | 22 | 110 | 22 | 0.48 |
| Ic | U/ml | 2.2E2 | 2.2E2 | 9.6E2 | 2.1E2 | 6.3E2 | 1.5E2 | 2.4E0 | 1.6E1 | 6.5E4 | 4.2E2 | 110 | 22 | 110 | 22 | 0.52 |
| Id | U/ml | 6.3E-1 | 8.2E-1 | 5.1E0 | 1.6E0 | 4.1E1 | 2.2E0 | 1.0E-9 | 1.0E-9 | 4.3E2 | 9.4E0 | 110 | 22 | 110 | 22 | 0.53 |
| Tt | pg/ml | 1.7E2 | 1.9E2 | 1.7E2 | 1.8E2 | 5.9E1 | 5.0E1 | 4.3E1 | 1.0E2 | 4.4E2 | 2.8E2 | 103 | 20 | 103 | 20 | 0.57 |
| To | pg/ml | 1.6E0 | 1.4E0 | 2.3E0 | 1.8E0 | 3.0E0 | 1.9E0 | 1.0E-9 | 1.0E-9 | 2.3E1 | 6.4E0 | 107 | 23 | 107 | 23 | 0.46 |
| Tr | pg/ml | 3.4E0 | 3.0E0 | 9.0E0 | 7.8E0 | 3.1E1 | 1.3E1 | 1.0E-9 | 1.0E-9 | 3.1E2 | 5.4E1 | 106 | 21 | 106 | 21 | 0.50 |
| Tn | pg/ml | 3.0E1 | 7.2E1 | 1.1E2 | 2.5E2 | 3.5E2 | 4.4E2 | 1.0E-9 | 9.0E0 | 2.3E3 | 2.0E3 | 107 | 23 | 107 | 23 | 0.68 |
| Tv | ng/ml | 1.2E1 | 1.2E1 | 9.2E1 | 4.1E1 | 6.9E2 | 9.1E1 | 1.0E-9 | 1.0E-9 | 7.1E3 | 4.3E2 | 107 | 23 | 107 | 23 | 0.52 |
| Ih | ng/ml | 6.3E1 | 8.4E1 | 2.5E2 | 4.0E2 | 4.4E2 | 6.2E2 | 1.0E-9 | 1.4E0 | 3.6E3 | 2.8E3 | 309 | 44 | 309 | 44 | 0.57 |
| Ii | ng/ml | 7.9E1 | 1.2E2 | 2.2E2 | 2.8E2 | 5.3E2 | 6.8E2 | 7.3E-1 | 7.5E-1 | 5.2E3 | 4.5E3 | 309 | 44 | 309 | 44 | 0.56 |
| Ij | ng/ml | 7.8E1 | 1.2E2 | 2.5E2 | 2.8E2 | 1.5E3 | 4.7E2 | 2.8E0 | 9.5E0 | 2.4E4 | 2.0E3 | 305 | 44 | 305 | 44 | 0.61 |
| Ik | ng/ml | 1.1E1 | 5.1E1 | 1.4E3 | 2.7E2 | 1.2E4 | 4.1E2 | 5.9E-1 | 6.2E-1 | 1.2E5 | 1.5E3 | 305 | 44 | 305 | 44 | 0.61 |
| Il | ng/ml | 3.6E2 | 2.8E2 | 1.3E3 | 1.9E3 | 2.8E3 | 3.6E3 | 1.0E-9 | 1.0E-9 | 1.2E4 | 1.2E4 | 304 | 43 | 304 | 43 | 0.50 |
| Im | ng/ml | 2.0E2 | 6.3E2 | 4.0E2 | 1.2E3 | 6.5E2 | 2.5E3 | 1.4E1 | 2.2E1 | 5.8E3 | 1.5E4 | 305 | 44 | 305 | 44 | 0.66 |
| In | ng/ml | 3.7E0 | 2.2E0 | 3.5E1 | 3.2E1 | 2.7E2 | 1.0E2 | 1.0E-9 | 1.0E-9 | 4.5E3 | 5.9E2 | 309 | 44 | 309 | 44 | 0.44 |
| Hb | ng/ml | 2.6E1 | 1.9E1 | 3.6E1 | 3.5E1 | 3.5E1 | 4.5E1 | 1.6E0 | 4.8E-1 | 2.0E2 | 1.9E2 | 113 | 22 | 113 | 22 | 0.42 |
| Hc | pg/ml | 6.7E2 | 5.9E2 | 2.9E3 | 4.8E3 | 1.0E4 | 1.1E4 | 1.0E-9 | 1.4E2 | 1.0E5 | 5.0E4 | 113 | 22 | 113 | 22 | 0.54 |
| Hf | pg/ml | 2.0E2 | 1.2E2 | 4.3E2 | 2.2E2 | 5.8E2 | 2.5E2 | 1.0E-9 | 1.0E-9 | 3.2E3 | 8.8E2 | 113 | 22 | 113 | 22 | 0.41 |
| Io | ng/ml | 8.4E3 | 1.2E4 | 1.9E4 | 2.1E4 | 4.7E4 | 3.3E4 | 1.0E-9 | 2.4E2 | 7.1E5 | 2.0E5 | 309 | 44 | 309 | 44 | 0.56 |
| Ip | ng/ml | 8.9E0 | 3.0E1 | 2.0E1 | 3.2E1 | 2.5E1 | 3.2E1 | 1.0E-9 | 5.0E-3 | 2.3E2 | 1.6E2 | 309 | 44 | 309 | 44 | 0.61 |
| Iq | ug/ml | 1.0E-1 | 1.8E-1 | 4.5E1 | 6.6E0 | 7.7E2 | 3.3E1 | 1.0E-9 | 1.0E-9 | 1.4E4 | 2.2E2 | 309 | 44 | 309 | 44 | 0.55 |
| Ir | ug/ml | 3.6E-1 | 7.7E-1 | 5.6E0 | 1.1E1 | 3.9E1 | 3.1E1 | 1.0E-9 | 1.0E-9 | 5.1E2 | 1.3E2 | 308 | 44 | 308 | 44 | 0.61 |
| Is | ng/ml | 1.7E0 | 9.4E0 | 8.3E0 | 3.0E1 | 3.4E1 | 4.9E1 | 1.0E-9 | 1.4E-1 | 5.5E2 | 2.6E2 | 309 | 44 | 309 | 44 | 0.71 |
| It | ng/ml | 2.1E0 | 2.3E0 | 2.1E1 | 4.3E1 | 9.9E1 | 1.5E2 | 1.0E-9 | 1.0E-9 | 1.1E3 | 8.3E2 | 309 | 44 | 309 | 44 | 0.55 |
| Iu | ng/ml | 1.8E2 | 1.1E2 | 1.4E3 | 1.9E3 | 4.3E3 | 5.4E3 | 1.0E-9 | 1.0E-9 | 2.9E4 | 2.4E4 | 309 | 44 | 309 | 44 | 0.47 |
| Iv | ng/ml | 1.1E1 | 2.4E1 | 9.8E1 | 2.6E2 | 9.3E2 | 8.1E2 | 1.0E-9 | 1.0E-9 | 1.6E4 | 3.8E3 | 308 | 44 | 308 | 44 | 0.67 |
| Iz | ng/ml | 1.2E2 | 2.2E2 | 3.6E2 | 4.0E2 | 7.6E2 | 5.1E2 | 1.5E0 | 8.8E-1 | 6.1E3 | 1.7E3 | 113 | 22 | 113 | 22 | 0.54 |
| Yg | pg/ml | 2.5E2 | 1.7E3 | 4.5E2 | 5.3E3 | 6.5E2 | 1.3E4 | 1.0E-9 | 1.0E-9 | 3.4E3 | 5.0E4 | 40 | 14 | 40 | 14 | 0.64 |
| Yh | pg/ml | 2.1E2 | 5.7E2 | 3.4E2 | 7.6E2 | 4.7E2 | 8.1E2 | 1.0E-9 | 1.0E-9 | 2.1E3 | 3.0E3 | 40 | 14 | 40 | 14 | 0.69 |
| Yi | pg/ml | 2.6E2 | 8.4E2 | 4.6E2 | 3.2E3 | 4.5E2 | 7.1E3 | 1.0E-9 | 1.0E-9 | 2.0E3 | 2.6E4 | 40 | 14 | 40 | 14 | 0.63 |
| Yk | U/ml | 1.0E-9 | 1.0E-9 | 1.1E-1 | 5.5E-1 | 3.7E-1 | 9.7E-1 | 1.0E-9 | 1.0E-9 | 1.8E0 | 3.0E0 | 40 | 14 | 40 | 14 | 0.61 |

Figure 32 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yj | pg/ml | 1.6E2 | 1.0E2 | 3.5E2 | 1.3E2 | 5.6E2 | 1.2E2 | 9.7E0 | 1.0E-9 | 3.2E3 | 4.7E2 | 40 | 14 | 40 | 14 | 0.35 |
| Yd | ng/ml | 1.9E-1 | 3.3E-1 | 3.5E-1 | 5.7E-1 | 4.2E-1 | 7.3E-1 | 6.6E-3 | 1.6E-2 | 1.8E0 | 2.3E0 | 44 | 14 | 44 | 14 | 0.56 |
| Wb | pg/ml | 2.7E4 | 3.3E4 | 3.4E4 | 8.1E4 | 2.4E4 | 1.6E5 | 4.9E3 | 7.5E3 | 1.5E5 | 6.4E5 | 44 | 14 | 44 | 14 | 0.60 |
| Vz | pg/ml | 3.9E0 | 2.4E0 | 5.2E0 | 3.0E0 | 5.0E0 | 2.6E0 | 1.0E-9 | 3.0E-1 | 2.2E1 | 9.6E0 | 44 | 14 | 44 | 14 | 0.36 |
| Si | ng/ml | 1.3E0 | 9.3E-1 | 2.1E0 | 1.6E0 | 2.6E0 | 1.7E0 | 1.1E-1 | 8.6E-3 | 1.0E1 | 6.0E0 | 44 | 14 | 44 | 14 | 0.47 |
| Sf | mIU/mL | 1.7E1 | 1.6E1 | 5.6E1 | 1.7E1 | 1.2E2 | 1.3E1 | 6.2E-1 | 1.3E0 | 7.2E2 | 4.3E1 | 44 | 14 | 44 | 14 | 0.42 |
| Sh | mIU/mL | 1.5E1 | 1.2E1 | 4.5E1 | 2.6E1 | 9.7E1 | 4.6E1 | 7.8E-2 | 1.4E-1 | 5.7E2 | 1.8E2 | 44 | 14 | 44 | 14 | 0.44 |
| Sj | ng/ml | 4.2E-1 | 4.5E-1 | 4.2E-1 | 4.6E-1 | 8.0E-2 | 1.3E-1 | 2.5E-1 | 3.2E-1 | 5.7E-1 | 7.2E-1 | 44 | 14 | 44 | 14 | 0.59 |
| Rc | pg/ml | 6.9E3 | 5.5E3 | 7.6E3 | 8.3E3 | 5.3E3 | 8.2E3 | 3.9E2 | 5.5E2 | 2.8E4 | 3.9E4 | 111 | 23 | 111 | 23 | 0.48 |
| Rb | pg/ml | 8.8E-1 | 1.0E-9 | 3.1E0 | 2.5E0 | 6.4E0 | 4.2E0 | 1.0E-9 | 1.0E-9 | 5.6E1 | 1.3E1 | 111 | 23 | 111 | 23 | 0.44 |
| Zq | 2.6ng/ml | 3.0E2 | 3.4E2 | 3.0E2 | 3.0E2 | 2.3E2 | 1.7E2 | 1.4E1 | 1.7E1 | 9.7E2 | 5.0E2 | 43 | 13 | 43 | 13 | 0.53 |
| Zw | 2.5ng/ml | 5.2E0 | 5.0E0 | 1.0E1 | 1.2E1 | 1.4E1 | 1.7E1 | 1.4E-1 | 2.4E-1 | 5.9E1 | 6.3E1 | 44 | 14 | 44 | 14 | 0.50 |
| Zx | 2.3mU/ml | 1.3E-1 | 1.5E-1 | 2.3E-1 | 4.9E-1 | 3.4E-1 | 8.4E-1 | 3.2E-2 | 6.1E-2 | 2.1E0 | 2.9E0 | 44 | 14 | 44 | 14 | 0.60 |
| Pz | ng/ml | 3.4E3 | 5.9E3 | 5.4E3 | 7.5E3 | 4.9E3 | 1.1E4 | 1.6E1 | 4.0E1 | 2.9E4 | 7.0E4 | 306 | 43 | 306 | 43 | 0.58 |
| Qa | ng/ml | 3.5E3 | 9.0E3 | 7.0E3 | 1.4E4 | 1.4E4 | 1.2E4 | 1.5E2 | 2.9E2 | 2.2E5 | 3.6E4 | 306 | 43 | 306 | 43 | 0.68 |
| Qb | ng/ml | 1.0E2 | 2.1E2 | 2.2E2 | 3.8E2 | 4.0E2 | 6.5E2 | 7.9E-1 | 8.7E0 | 5.3E3 | 4.1E3 | 306 | 43 | 306 | 43 | 0.63 |
| Qc | ng/ml | 2.0E2 | 3.5E2 | 4.4E2 | 5.9E2 | 6.0E2 | 6.0E2 | 1.0E-9 | 5.8E0 | 4.3E3 | 2.8E3 | 306 | 43 | 306 | 43 | 0.60 |
| Qd | ng/ml | 8.6E3 | 1.4E4 | 2.3E4 | 6.4E4 | 1.2E5 | 8.7E4 | 1.5E2 | 1.2E3 | 2.0E6 | 4.3E5 | 306 | 43 | 306 | 43 | 0.68 |
| Qe | ng/ml | 8.4E2 | 1.9E3 | 2.0E3 | 3.1E3 | 5.9E3 | 3.6E3 | 1.0E-9 | 5.7E1 | 9.7E4 | 1.8E4 | 306 | 43 | 306 | 43 | 0.62 |
| Jd | ng/ml | 7.8E-1 | 1.5E0 | 4.0E0 | 4.3E0 | 1.6E1 | 5.3E0 | 1.0E-9 | 1.0E-9 | 1.2E2 | 1.8E1 | 111 | 23 | 111 | 23 | 0.61 |
| Je | ng/ml | 1.0E-9 | 1.0E-9 | 1.8E0 | 1.5E0 | 5.2E0 | 2.9E0 | 1.0E-9 | 1.0E-9 | 4.6E1 | 1.1E1 | 111 | 23 | 111 | 23 | 0.48 |
| Jf | ng/ml | 1.0E-9 | 1.0E-9 | 1.3E0 | 5.7E-1 | 2.4E0 | 1.2E0 | 1.0E-9 | 1.0E-9 | 1.2E1 | 4.1E0 | 111 | 23 | 111 | 23 | 0.42 |
| Jg | ng/ml | 4.3E2 | 8.6E2 | 7.7E2 | 1.2E3 | 9.6E2 | 1.3E3 | 5.8E0 | 2.4E1 | 1.0E4 | 7.1E3 | 308 | 44 | 308 | 44 | 0.62 |
| Jh | ng/ml | 2.6E0 | 7.0E0 | 2.1E1 | 3.6E1 | 8.9E1 | 5.9E1 | 1.0E-9 | 1.0E-9 | 1.2E3 | 2.9E2 | 308 | 44 | 308 | 44 | 0.69 |
| Ji | ng/ml | 5.5E1 | 1.0E2 | 8.5E1 | 1.9E2 | 1.1E2 | 1.9E2 | 1.1E0 | 8.9E0 | 1.3E3 | 6.9E2 | 308 | 44 | 308 | 44 | 0.68 |
| Sr | pg/mL | 3.8E2 | 6.7E2 | 9.8E2 | 1.5E3 | 2.2E3 | 1.6E3 | 1.0E-9 | 1.0E-9 | 2.1E4 | 5.4E3 | 110 | 23 | 110 | 23 | 0.61 |
| Ss | pg/mL | 7.9E4 | 1.2E5 | 1.5E5 | 1.3E5 | 1.9E5 | 8.2E4 | 2.7E3 | 7.6E3 | 1.3E6 | 2.4E5 | 110 | 23 | 110 | 23 | 0.56 |
| St | pg/mL | 2.4E7 | 5.3E7 | 5.3E7 | 1.7E8 | 8.2E7 | 4.0E8 | 1.0E-9 | 9.9E5 | 5.4E8 | 1.7E9 | 109 | 23 | 109 | 23 | 0.58 |
| Wc | ng/ml | 1.0E-9 | 3.2E-2 | 9.5E-2 | 8.7E-2 | 2.8E-1 | 1.6E-1 | 1.0E-9 | 1.0E-9 | 1.8E0 | 6.3E-1 | 44 | 14 | 44 | 14 | 0.59 |
| Wd | ng/ml | 9.3E0 | 1.3E1 | 2.6E1 | 7.8E1 | 6.7E1 | 1.3E2 | 1.0E0 | 2.3E0 | 3.8E2 | 4.1E2 | 44 | 14 | 44 | 14 | 0.65 |
| We | ng/ml | 2.6E-1 | 5.9E-1 | 1.3E0 | 1.7E0 | 3.5E0 | 2.6E0 | 1.0E-9 | 1.0E-9 | 2.3E1 | 9.7E0 | 44 | 14 | 44 | 14 | 0.66 |
| Wg | ng/ml | 1.0E-9 | 1.0E-9 | 1.3E-2 | 1.0E-9 | 8.1E-2 | 0.0E0 | 1.0E-9 | 1.0E-9 | 5.3E-1 | 1.0E-9 | 44 | 14 | 44 | 14 | 0.48 |
| Wh | ng/ml | 9.2E-3 | 3.1E-2 | 3.6E-2 | 8.2E-2 | 8.4E-2 | 1.3E-1 | 1.0E-9 | 1.0E-9 | 3.6E-1 | 4.2E-1 | 44 | 14 | 44 | 14 | 0.68 |
| Wf | ng/ml | 1.0E-9 | 1.0E-9 | 1.2E-1 | 1.5E-1 | 3.6E-1 | 3.4E-1 | 1.0E-9 | 1.0E-9 | 2.3E0 | 1.2E0 | 44 | 14 | 44 | 14 | 0.54 |
| Ra | pg/ml | 1.0E-9 | 1.0E-9 | 1.0E0 | 3.3E-1 | 6.1E0 | 1.4E0 | 1.0E-9 | 1.0E-9 | 6.4E1 | 6.5E0 | 111 | 23 | 111 | 23 | 0.45 |
| Qz | pg/ml | 9.0E0 | 1.2E1 | 5.1E1 | 4.5E1 | 8.9E1 | 6.3E1 | 1.0E-9 | 1.0E-9 | 4.5E2 | 1.8E2 | 111 | 23 | 111 | 23 | 0.57 |
| Qy | pg/ml | 3.9E-1 | 5.4E-1 | 3.8E0 | 5.4E1 | 2.3E1 | 1.7E2 | 1.0E-9 | 1.0E-9 | 2.3E2 | 7.3E2 | 111 | 23 | 111 | 23 | 0.57 |
| Qx | pg/ml | 1.0E-9 | 1.0E-9 | 3.8E0 | 3.2E0 | 2.1E1 | 8.0E0 | 1.0E-9 | 1.0E-9 | 1.9E2 | 3.1E1 | 111 | 23 | 111 | 23 | 0.55 |
| Qw | pg/ml | 1.0E-9 | 4.5E-1 | 2.5E0 | 4.3E0 | 9.0E0 | 1.1E1 | 1.0E-9 | 1.0E-9 | 6.6E1 | 5.1E1 | 111 | 23 | 111 | 23 | 0.55 |
| Qv | pg/ml | 2.0E4 | 1.2E4 | 4.1E4 | 1.5E4 | 9.9E4 | 1.3E4 | 4.0E2 | 1.0E-9 | 9.4E5 | 5.1E4 | 111 | 23 | 111 | 23 | 0.33 |
| Qu | pg/ml | 6.2E0 | 2.4E1 | 8.4E1 | 1.3E2 | 1.8E2 | 2.1E2 | 1.0E-9 | 1.0E-9 | 9.8E2 | 7.3E2 | 111 | 23 | 111 | 23 | 0.55 |
| Qt | pg/ml | 1.1E1 | 2.1E1 | 4.1E1 | 6.2E1 | 9.9E1 | 9.0E1 | 1.0E-9 | 1.0E-9 | 7.1E2 | 3.3E2 | 111 | 23 | 111 | 23 | 0.64 |
| Qh | ng/ml | 1.8E1 | 3.0E1 | 4.2E1 | 9.2E1 | 6.8E1 | 1.7E2 | 2.5E-1 | 1.6E0 | 4.6E2 | 8.0E2 | 111 | 23 | 111 | 23 | 0.60 |
| Qg | ng/ml | 7.9E0 | 5.3E0 | 1.4E1 | 1.0E1 | 2.7E1 | 1.7E1 | 1.5E-1 | 1.0E0 | 2.7E2 | 8.1E1 | 111 | 23 | 111 | 23 | 0.40 |
| Jj | ng/ml | 5.4E2 | 2.1E2 | 2.1E3 | 4.5E2 | 1.9E4 | 4.6E2 | 2.3E0 | 8.7E0 | 3.4E5 | 2.0E3 | 308 | 44 | 308 | 44 | 0.34 |
| Jk | ng/ml | 2.6E0 | 4.4E0 | 1.8E1 | 4.7E1 | 4.3E1 | 8.1E1 | 1.0E-9 | 4.3E-2 | 2.8E2 | 3.9E2 | 308 | 44 | 308 | 44 | 0.59 |
| Jl | ng/ml | 4.3E-1 | 1.3E0 | 1.8E0 | 2.3E2 | 4.5E0 | 1.5E3 | 1.2E-3 | 5.4E-3 | 4.0E1 | 9.9E3 | 308 | 44 | 308 | 44 | 0.69 |
| Jm | ng/ml | 2.0E1 | 2.0E1 | 7.1E1 | 4.7E1 | 1.8E2 | 6.6E1 | 1.0E-9 | 1.0E-9 | 2.1E3 | 2.9E2 | 308 | 44 | 308 | 44 | 0.50 |
| Jn | pg/ml | 3.2E-1 | 1.0E0 | 5.4E0 | 2.4E1 | 5.0E1 | 1.1E2 | 1.0E-9 | 1.0E-9 | 6.2E2 | 7.3E2 | 308 | 44 | 308 | 44 | 0.64 |
| Jo | pg/ml | 3.8E3 | 3.9E3 | 5.2E3 | 5.5E3 | 6.8E3 | 6.4E3 | 2.0E1 | 2.4E1 | 1.0E5 | 3.6E4 | 308 | 44 | 308 | 44 | 0.49 |
| Jp | pg/ml | 7.0E4 | 9.8E4 | 7.2E4 | 9.6E4 | 3.9E4 | 4.1E4 | 5.8E2 | 4.6E3 | 3.8E5 | 2.1E5 | 308 | 44 | 308 | 44 | 0.69 |
| Jq | pg/ml | 9.3E1 | 1.8E2 | 1.8E2 | 4.0E2 | 5.2E2 | 6.4E2 | 1.0E0 | 7.4E0 | 8.7E3 | 3.3E3 | 308 | 44 | 308 | 44 | 0.66 |
| Jr | pg/ml | 4.1E0 | 1.5E1 | 7.3E0 | 2.5E2 | 6.8E2 | 1.2E3 | 1.0E-9 | 1.0E-9 | 1.1E4 | 7.4E3 | 308 | 44 | 308 | 44 | 0.65 |
| Js | pg/ml | 1.4E1 | 1.9E1 | 7.8E1 | 1.8E2 | 6.0E2 | 6.2E2 | 1.0E-9 | 2.1E0 | 1.0E4 | 3.0E3 | 308 | 44 | 308 | 44 | 0.63 |
| Jt | pg/ml | 2.4E3 | 2.9E3 | 3.1E3 | 5.0E3 | 3.6E3 | 7.4E3 | 2.2E1 | 1.5E2 | 5.2E4 | 4.1E4 | 308 | 44 | 308 | 44 | 0.56 |
| Xa | pg/ml | 3.1E-1 | 1.4E1 | 3.3E1 | 6.3E1 | 1.8E2 | 1.5E2 | 1.0E-9 | 1.0E-9 | 1.2E3 | 5.6E2 | 44 | 14 | 44 | 14 | 0.69 |
| Ye | pg/ml | 1.0E-9 | 1.0E-9 | 3.6E0 | 5.6E0 | 1.2E1 | 1.6E1 | 1.0E-9 | 1.0E-9 | 6.9E1 | 6.1E1 | 44 | 14 | 44 | 14 | 0.55 |

Figure 32 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Tm | pg/ml | 1.0E-9 | 1.0E-9 | 2.6E0 | 2.4E0 | 4.6E0 | 3.9E0 | 1.0E-9 | 1.0E-9 | 1.8E1 | 8.4E0 | 44 | 14 | 44 | 14 | 0.50 |
| Tl | pg/ml | 1.3E-1 | 1.1E-1 | 8.6E-1 | 2.5E-1 | 3.7E0 | 3.2E-1 | 1.0E-9 | 1.0E-9 | 2.5E1 | 8.2E-1 | 44 | 14 | 44 | 14 | 0.45 |
| Ju | mIU/ml | 1.1E1 | 6.4E0 | 2.6E1 | 1.4E1 | 3.7E1 | 1.5E1 | 1.7E-1 | 6.0E-1 | 2.3E2 | 6.2E1 | 111 | 23 | 111 | 23 | 0.44 |
| Jv | mIU/ml | 1.6E1 | 1.1E1 | 4.1E1 | 3.1E1 | 6.5E1 | 4.6E1 | 1.7E-2 | 7.9E-2 | 4.4E2 | 1.4E2 | 111 | 23 | 111 | 23 | 0.43 |
| Jy | ng/ml | 1.6E-3 | 1.6E-3 | 2.3E-3 | 4.6E-3 | 3.7E-3 | 9.1E-3 | 1.0E-9 | 4.5E-4 | 3.9E-2 | 4.1E-2 | 111 | 23 | 111 | 23 | 0.53 |
| Kc | pg/ml | 2.2E1 | 2.8E1 | 4.2E1 | 6.4E1 | 5.0E1 | 7.9E1 | 1.0E-9 | 6.2E0 | 2.7E2 | 3.2E2 | 113 | 22 | 113 | 22 | 0.59 |
| Kd | pg/ml | 1.0E-9 | 1.0E-9 | 5.2E2 | 6.6E2 | 3.6E3 | 1.6E3 | 1.0E-9 | 1.0E-9 | 3.8E4 | 5.2E3 | 113 | 22 | 113 | 22 | 0.52 |
| Ke | pg/ml | 1.3E4 | 1.6E4 | 1.7E4 | 2.5E4 | 3.1E4 | 2.6E4 | 1.0E3 | 6.7E2 | 3.2E5 | 1.1E5 | 113 | 22 | 113 | 22 | 0.59 |
| Kf | pg/mL | 5.9E0 | 8.5E0 | 7.3E0 | 8.5E0 | 9.0E0 | 6.0E0 | 1.0E-9 | 1.0E-9 | 7.8E1 | 2.2E1 | 113 | 22 | 113 | 22 | 0.59 |
| Kg | pg/mL | 9.9E2 | 7.8E2 | 2.0E3 | 3.3E3 | 3.4E3 | 7.9E3 | 7.7E1 | 1.6E2 | 2.7E4 | 3.6E4 | 113 | 22 | 113 | 22 | 0.43 |
| Ki | pg/ml | 6.1E1 | 6.7E1 | 7.1E1 | 7.3E1 | 5.7E1 | 2.6E1 | 1.0E-9 | 6.0E0 | 2.9E2 | 1.1E2 | 113 | 22 | 113 | 22 | 0.59 |
| Kj | pg/ml | 8.3E2 | 7.3E2 | 1.4E3 | 1.4E3 | 1.9E3 | 1.8E3 | 6.6E1 | 3.3E1 | 1.5E4 | 7.7E3 | 113 | 22 | 113 | 22 | 0.46 |
| Kk | pg/ml | 7.1E0 | 9.2E0 | 1.4E1 | 1.4E1 | 1.6E1 | 1.5E1 | 1.0E-9 | 1.0E-9 | 8.1E1 | 5.8E1 | 113 | 22 | 113 | 22 | 0.55 |
| Kl | pg/ml | 1.8E4 | 1.8E4 | 2.8E4 | 2.6E4 | 2.7E4 | 2.0E4 | 2.3E2 | 2.4E2 | 1.3E5 | 5.0E4 | 113 | 22 | 113 | 22 | 0.51 |
| Kn | pg/ml | 2.9E1 | 3.0E1 | 1.1E2 | 9.1E1 | 4.6E2 | 1.4E2 | 1.0E-9 | 1.0E-9 | 4.9E3 | 4.7E2 | 113 | 22 | 113 | 22 | 0.56 |
| Ko | pg/ml | 3.5E2 | 2.0E2 | 5.1E2 | 4.2E2 | 5.9E2 | 4.1E2 | 1.0E-9 | 1.0E-9 | 4.1E3 | 1.5E3 | 113 | 22 | 113 | 22 | 0.48 |
| Kp | pg/ml | 3.6E2 | 3.9E2 | 4.7E2 | 4.0E2 | 1.3E3 | 2.5E2 | 1.0E-9 | 1.0E-9 | 1.3E4 | 8.0E2 | 113 | 22 | 113 | 22 | 0.54 |
| Kq | pg/ml | 3.2E2 | 6.1E2 | 1.9E3 | 1.4E3 | 1.5E4 | 2.6E3 | 5.1E0 | 1.6E0 | 1.6E5 | 1.2E4 | 108 | 22 | 108 | 22 | 0.61 |
| Kr | pg/ml | 3.7E-1 | 2.3E-1 | 6.0E0 | 1.5E0 | 4.0E1 | 2.1E0 | 1.0E-9 | 1.0E-9 | 4.2E2 | 6.0E0 | 108 | 22 | 108 | 22 | 0.48 |
| Ks | pg/ml | 1.6E4 | 1.1E4 | 2.1E4 | 1.8E4 | 1.8E4 | 1.8E4 | 4.5E2 | 5.1E1 | 7.9E4 | 5.0E4 | 108 | 22 | 108 | 22 | 0.44 |
| Ps | ng/ml | 1.4E2 | 5.0E2 | 5.0E2 | 1.9E3 | 1.4E3 | 3.5E3 | 1.6E0 | 5.5E0 | 9.0E3 | 1.2E4 | 44 | 14 | 44 | 14 | 0.68 |
| Kx | ng/ml | 5.5E-4 | 4.6E-3 | 7.5E-3 | 1.3E-2 | 1.6E-2 | 2.1E-2 | 1.0E-9 | 1.0E-9 | 1.0E-1 | 7.9E-2 | 112 | 22 | 112 | 22 | 0.58 |
| Ky | ng/ml | 1.1E-1 | 4.8E-1 | 3.3E-1 | 7.9E-1 | 6.9E-1 | 1.0E0 | 1.0E-9 | 1.0E-9 | 5.1E0 | 4.4E0 | 112 | 22 | 112 | 22 | 0.70 |
| Kz | ng/ml | 1.0E-9 | 1.0E-9 | 3.8E-3 | 4.6E-3 | 5.9E-3 | 7.6E-3 | 1.0E-9 | 1.0E-9 | 1.8E-2 | 2.5E-2 | 112 | 22 | 112 | 22 | 0.51 |
| Rz | ng/ml | 3.0E-1 | 9.5E-1 | 7.7E-1 | 1.4E0 | 1.3E0 | 1.9E0 | 1.1E-2 | 4.6E-3 | 6.7E0 | 7.5E0 | 44 | 14 | 44 | 14 | 0.61 |
| Ry | ng/ml | 1.6E-2 | 2.0E-2 | 3.1E-2 | 2.7E-2 | 5.5E-2 | 2.6E-2 | 1.0E-9 | 1.0E-9 | 3.5E-1 | 7.5E-2 | 44 | 14 | 44 | 14 | 0.51 |
| Rx | ng/ml | 1.0E-9 | 1.7E-3 | 1.1E-3 | 2.6E-3 | 2.0E-3 | 3.0E-3 | 1.0E-9 | 1.0E-9 | 8.6E-3 | 8.6E-3 | 44 | 14 | 44 | 14 | 0.63 |
| Ld | pg/ml | 1.0E-9 | 1.0E-9 | 3.9E0 | 4.0E0 | 9.0E0 | 7.4E0 | 1.0E-9 | 1.0E-9 | 6.9E1 | 2.9E1 | 114 | 21 | 114 | 21 | 0.51 |
| Lh | pg/ml | 1.3E4 | 3.0E4 | 2.2E4 | 4.5E4 | 4.2E4 | 6.8E4 | 1.0E-9 | 1.0E-9 | 4.8E5 | 4.1E5 | 309 | 44 | 309 | 44 | 0.64 |
| Li | pg/ml | 3.5E3 | 6.6E3 | 2.0E4 | 3.9E4 | 9.4E4 | 8.6E4 | 1.2E1 | 1.3E1 | 1.3E6 | 4.1E5 | 309 | 44 | 309 | 44 | 0.56 |
| Lj | pg/ml | 3.0E3 | 2.9E3 | 2.0E4 | 2.8E4 | 5.7E4 | 6.7E4 | 1.0E-9 | 1.0E-9 | 4.3E5 | 3.9E5 | 309 | 44 | 309 | 44 | 0.50 |
| Lp | pg/ml | 1.2E1 | 4.8E0 | 9.8E1 | 1.6E2 | 2.5E2 | 4.0E2 | 1.0E-9 | 1.0E-9 | 1.1E3 | 1.4E3 | 44 | 14 | 44 | 14 | 0.43 |
| Lt | pg/ml | 1.0E-9 | 1.0E-9 | 1.9E0 | 1.0E-9 | 6.3E0 | 0.0E0 | 1.0E-9 | 1.0E-9 | 2.5E1 | 1.0E-9 | 44 | 14 | 44 | 14 | 0.45 |
| Rv | ng/ml | 5.0E-4 | 5.0E-4 | 1.5E-3 | 1.4E-3 | 3.2E-3 | 2.4E-3 | 1.0E-9 | 1.0E-9 | 1.6E-2 | 9.2E-3 | 44 | 14 | 44 | 14 | 0.56 |
| Ru | ng/ml | 1.0E-9 | 1.0E-9 | 2.7E-2 | 5.0E-3 | 8.9E-2 | 1.9E-2 | 1.0E-9 | 1.0E-9 | 3.5E-1 | 7.1E-2 | 44 | 14 | 44 | 14 | 0.49 |
| Rt | ng/ml | 7.8E-2 | 5.8E-2 | 2.7E-1 | 2.0E-1 | 1.1E0 | 2.5E-1 | 6.5E-3 | 1.3E-3 | 7.4E0 | 6.3E-1 | 44 | 14 | 44 | 14 | 0.49 |
| Yl | pg/ml | 1.3E1 | 6.9E0 | 2.4E1 | 1.3E1 | 3.5E1 | 1.5E1 | 1.0E-9 | 1.0E-9 | 2.2E2 | 4.9E1 | 44 | 14 | 44 | 14 | 0.35 |
| Rm | ng/ml | 1.8E1 | 2.6E1 | 4.9E1 | 5.6E1 | 8.9E1 | 6.7E1 | 2.2E-1 | 2.3E-1 | 6.5E2 | 2.5E2 | 110 | 23 | 110 | 23 | 0.55 |
| Rh | ng/ml | 1.8E2 | 1.6E2 | 4.9E2 | 9.2E2 | 1.7E3 | 3.5E3 | 7.5E0 | 2.5E1 | 1.7E4 | 1.7E4 | 110 | 23 | 110 | 23 | 0.42 |
| Ri | ng/ml | 4.4E-2 | 1.0E-9 | 3.9E0 | 3.6E0 | 7.8E0 | 9.4E0 | 1.0E-9 | 1.0E-9 | 4.9E1 | 4.5E1 | 110 | 23 | 110 | 23 | 0.47 |
| Rg | ng/ml | 1.0E-9 | 1.0E-9 | 9.7E-2 | 1.4E-2 | 4.7E-1 | 4.4E-2 | 1.0E-9 | 1.0E-9 | 3.3E0 | 2.1E-1 | 110 | 23 | 110 | 23 | 0.51 |
| Rj | ng/ml | 1.0E-9 | 1.0E-9 | 3.4E0 | 5.2E-1 | 2.6E1 | 1.0E0 | 1.0E-9 | 1.0E-9 | 2.7E2 | 3.2E0 | 110 | 23 | 110 | 23 | 0.48 |
| Rf | ng/ml | 3.9E-1 | 3.3E-1 | 7.6E-1 | 2.3E0 | 9.9E-1 | 4.6E0 | 2.1E-2 | 2.1E-2 | 6.2E0 | 1.7E1 | 110 | 23 | 110 | 23 | 0.52 |
| Ql | pg/ml | 1.7E0 | 1.1E1 | 1.1E1 | 1.6E1 | 2.4E1 | 2.0E1 | 1.0E-9 | 1.0E-9 | 1.8E2 | 5.6E1 | 111 | 23 | 111 | 23 | 0.60 |
| Qm | pg/ml | 1.7E0 | 1.0E1 | 2.0E1 | 2.4E1 | 3.7E1 | 2.9E1 | 1.0E-9 | 1.0E-9 | 1.9E2 | 8.6E1 | 111 | 23 | 111 | 23 | 0.58 |
| Qn | pg/ml | 6.1E-1 | 1.3E0 | 5.3E0 | 1.5E1 | 2.2E1 | 4.3E1 | 1.0E-9 | 1.0E-9 | 2.2E2 | 2.0E2 | 111 | 23 | 111 | 23 | 0.57 |
| Nv | pg/ml | 3.8E3 | 1.0E4 | 8.3E3 | 2.5E4 | 1.6E4 | 3.9E4 | 1.0E-9 | 1.9E1 | 1.3E5 | 1.6E5 | 310 | 44 | 310 | 44 | 0.69 |
| Nw | pg/ml | 9.3E3 | 1.7E4 | 1.3E4 | 3.1E4 | 1.6E4 | 4.5E4 | 2.0E2 | 1.9E2 | 2.1E5 | 2.2E5 | 310 | 44 | 310 | 44 | 0.68 |
| Nx | pg/ml | 2.2E2 | 2.4E2 | 4.3E2 | 5.9E2 | 6.4E2 | 6.3E2 | 1.0E-9 | 1.0E-9 | 4.1E3 | 2.3E3 | 310 | 44 | 310 | 44 | 0.60 |
| Ny | pg/ml | 6.4E0 | 1.8E1 | 1.1E2 | 1.1E2 | 1.4E3 | 2.2E2 | 1.0E-9 | 1.0E-9 | 2.5E4 | 1.2E3 | 310 | 44 | 310 | 44 | 0.64 |
| Oa | pg/ml | 1.6E2 | 2.2E2 | 4.4E2 | 6.9E2 | 7.2E2 | 9.2E2 | 1.0E-9 | 1.0E-9 | 4.5E3 | 3.4E3 | 111 | 23 | 111 | 23 | 0.56 |
| Op | pg/ml | 4.4E5 | 4.5E5 | 4.4E5 | 4.5E5 | 1.5E5 | 2.1E5 | 5.2E4 | 1.4E5 | 7.3E5 | 7.5E5 | 44 | 14 | 44 | 14 | 0.51 |
| Oe | pg/ml | 2.5E1 | 1.0E-9 | 2.4E2 | 2.6E2 | 3.8E2 | 3.9E2 | 1.0E-9 | 1.0E-9 | 2.3E3 | 1.4E3 | 308 | 44 | 308 | 44 | 0.49 |
| Of | pg/ml | 1.3E2 | 1.7E2 | 5.0E3 | 5.1E3 | 2.1E4 | 1.9E4 | 1.0E-9 | 1.0E-9 | 1.9E5 | 1.2E5 | 310 | 44 | 310 | 44 | 0.50 |
| Og | pg/ml | 6.3E-2 | 7.7E-2 | 3.8E-1 | 1.2E-1 | 1.6E0 | 1.8E-1 | 1.0E-9 | 1.0E-9 | 1.9E1 | 9.4E-1 | 310 | 44 | 310 | 44 | 0.49 |
| Oh | pg/ml | 2.3E0 | 6.9E0 | 1.3E1 | 4.1E2 | 9.1E1 | 2.4E3 | 1.0E-9 | 1.0E-9 | 1.4E3 | 1.6E4 | 310 | 44 | 310 | 44 | 0.69 |
| Oi | pg/ml | 1.9E0 | 2.2E0 | 4.9E0 | 5.4E0 | 7.9E0 | 7.6E0 | 1.0E-9 | 1.0E-9 | 6.7E1 | 3.1E1 | 310 | 44 | 310 | 44 | 0.50 |

Figure 32 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ok | pg/ml | 3.8E2 | 5.6E2 | 5.2E2 | 1.1E3 | 6.1E2 | 1.4E3 | 2.9E1 | 1.5E1 | 7.8E3 | 7.0E3 | 310 | 44 | 310 | 44 | 0.63 |
| Om | pg/ml | 4.1E2 | 8.7E2 | 9.3E2 | 1.5E3 | 3.6E3 | 1.7E3 | 1.0E-9 | 1.0E-9 | 5.1E4 | 6.9E3 | 310 | 44 | 310 | 44 | 0.67 |
| On | pg/ml | 1.7E2 | 4.3E2 | 2.8E2 | 8.2E2 | 4.2E2 | 1.4E3 | 1.0E-9 | 1.0E1 | 4.5E3 | 8.5E3 | 310 | 44 | 310 | 44 | 0.71 |
| Or | pg/ml | 9.6E0 | 3.5E1 | 3.3E1 | 9.1E1 | 7.2E1 | 1.3E2 | 1.0E-9 | 1.0E-9 | 5.1E2 | 4.5E2 | 114 | 22 | 114 | 22 | 0.64 |
| Ow | pg/ml | 3.7E1 | 5.4E1 | 1.9E2 | 3.8E2 | 8.1E2 | 7.6E2 | 1.0E-9 | 1.0E-9 | 8.1E3 | 3.0E3 | 114 | 22 | 114 | 22 | 0.60 |
| Ou | pg/ml | 5.2E2 | 6.7E2 | 1.0E3 | 2.4E3 | 1.7E3 | 3.0E3 | 1.0E-9 | 2.0E1 | 9.8E3 | 1.1E4 | 114 | 22 | 114 | 22 | 0.60 |
| Ul | ng/ml | 1.0E-9 | 1.0E-9 | 1.7E0 | 1.8E-1 | 7.1E0 | 8.8E-1 | 1.0E-9 | 1.0E-9 | 5.6E1 | 4.2E0 | 112 | 23 | 112 | 23 | 0.48 |
| Uo | ng/ml | 1.0E-9 | 1.0E-9 | 8.8E-2 | 1.1E-2 | 2.3E-1 | 5.0E-2 | 1.0E-9 | 1.0E-9 | 1.3E0 | 2.4E-1 | 112 | 23 | 112 | 23 | 0.39 |
| Uk | ng/ml | 1.0E-9 | 1.0E-9 | 7.1E-3 | 8.3E-4 | 3.4E-2 | 2.3E-3 | 1.0E-9 | 1.0E-9 | 3.2E-1 | 1.1E-2 | 112 | 23 | 112 | 23 | 0.43 |
| Um | ng/ml | 1.0E-9 | 1.0E-9 | 2.8E-1 | 1.0E-9 | 6.6E-1 | 0.0E0 | 1.0E-9 | 1.0E-9 | 3.6E0 | 1.0E-9 | 112 | 23 | 112 | 23 | 0.35 |
| Uf | ng/ml | 5.8E-2 | 1.5E-1 | 1.2E-1 | 4.1E-1 | 1.8E-1 | 1.0E0 | 2.7E-3 | 1.0E-3 | 1.1E0 | 5.1E0 | 112 | 23 | 112 | 23 | 0.62 |
| Uh | ng/ml | 2.2E0 | 3.4E0 | 3.4E0 | 5.0E0 | 3.2E0 | 4.9E0 | 3.6E-2 | 4.7E-2 | 1.5E1 | 1.8E1 | 112 | 23 | 112 | 23 | 0.59 |
| Un | ng/ml | 1.7E0 | 1.7E0 | 2.1E0 | 2.7E0 | 2.5E0 | 2.0E0 | 3.5E-1 | 3.4E-1 | 2.5E1 | 8.0E0 | 112 | 23 | 112 | 23 | 0.60 |
| Ug | ng/ml | 1.1E1 | 8.8E0 | 2.3E1 | 1.4E1 | 2.8E1 | 1.5E1 | 1.5E0 | 1.0E0 | 1.6E2 | 6.9E1 | 112 | 23 | 112 | 23 | 0.41 |
| Ur | ng/ml | 1.1E-1 | 7.5E-2 | 3.7E-1 | 3.1E-1 | 9.7E-1 | 5.4E-1 | 1.0E-9 | 1.0E-9 | 7.3E0 | 2.3E0 | 111 | 23 | 111 | 23 | 0.45 |
| Up | ng/ml | 1.0E-9 | 1.0E-9 | 2.4E-2 | 5.4E-3 | 2.3E-1 | 1.6E-2 | 1.0E-9 | 1.0E-9 | 2.4E0 | 7.4E-2 | 111 | 23 | 111 | 23 | 0.58 |
| Us | ng/ml | 2.1E-3 | 6.4E-3 | 3.2E-2 | 1.6E-2 | 1.6E-1 | 2.0E-2 | 1.0E-9 | 1.0E-9 | 1.7E0 | 6.4E-2 | 111 | 23 | 111 | 23 | 0.56 |
| Uv | ng/ml | 2.3E-3 | 4.9E-3 | 1.7E-2 | 1.3E-2 | 5.7E-2 | 3.2E-2 | 1.0E-9 | 1.0E-9 | 4.1E-1 | 1.5E-1 | 111 | 23 | 111 | 23 | 0.56 |
| Ut | ng/ml | 6.7E-1 | 1.9E0 | 2.7E0 | 6.1E0 | 8.1E0 | 8.3E0 | 1.0E-9 | 9.2E-2 | 6.5E1 | 3.0E1 | 111 | 23 | 111 | 23 | 0.68 |
| Uu | ng/ml | 6.9E0 | 6.4E0 | 7.4E0 | 7.3E0 | 4.9E0 | 5.3E0 | 5.4E-1 | 8.1E-1 | 2.9E1 | 2.3E1 | 111 | 23 | 111 | 23 | 0.49 |
| Uw | ng/ml | 2.1E0 | 4.4E0 | 3.4E0 | 4.1E0 | 6.0E0 | 2.4E0 | 1.5E-1 | 1.0E-9 | 3.9E1 | 7.1E0 | 45 | 14 | 45 | 14 | 0.68 |
| Vb | ng/ml | 1.1E0 | 1.1E0 | 1.2E0 | 9.3E-1 | 9.0E-1 | 4.7E-1 | 2.8E-1 | 8.5E-2 | 6.4E0 | 1.4E0 | 45 | 14 | 45 | 14 | 0.43 |
| Vc | ng/ml | 1.0E-9 | 1.0E-9 | 4.5E-3 | 9.5E-4 | 2.0E-2 | 3.6E-3 | 1.0E-9 | 1.0E-9 | 1.1E-1 | 1.3E-2 | 45 | 14 | 45 | 14 | 0.50 |
| Uy | ng/ml | 1.4E0 | 9.3E-1 | 9.2E0 | 3.5E0 | 2.0E1 | 1.0E1 | 8.7E-2 | 2.0E-2 | 9.9E1 | 3.8E1 | 45 | 14 | 45 | 14 | 0.36 |
| Uz | ng/ml | 1.0E-9 | 1.0E-9 | 7.4E-1 | 2.2E-2 | 4.9E0 | 8.3E-2 | 1.0E-9 | 1.0E-9 | 3.3E1 | 3.1E-1 | 45 | 14 | 45 | 14 | 0.51 |
| Ux | ng/ml | 1.7E2 | 1.8E2 | 1.9E2 | 1.9E2 | 1.3E2 | 1.5E2 | 1.2E1 | 4.5E0 | 4.8E2 | 4.9E2 | 45 | 14 | 45 | 14 | 0.48 |
| Va | ng/ml | 1.4E1 | 3.6E0 | 2.5E1 | 1.5E1 | 2.9E1 | 2.2E1 | 3.1E-1 | 3.6E-1 | 1.2E2 | 6.2E1 | 45 | 14 | 45 | 14 | 0.36 |
| Vh | ng/ml | 1.2E-2 | 1.9E-2 | 3.8E-2 | 1.9E-2 | 1.3E-1 | 1.6E-2 | 3.9E-4 | 1.0E-9 | 8.6E-1 | 5.8E-2 | 45 | 14 | 45 | 14 | 0.54 |
| Vi | ng/ml | 3.4E-3 | 1.9E-2 | 4.7E-2 | 3.1E-2 | 2.7E-1 | 3.7E-2 | 1.0E-9 | 1.5E-4 | 1.8E0 | 1.2E-1 | 45 | 14 | 45 | 14 | 0.71 |
| Vj | ng/ml | 2.5E1 | 7.5E1 | 4.9E1 | 1.4E2 | 5.4E1 | 1.8E2 | 4.6E0 | 1.4E0 | 2.5E2 | 6.5E2 | 45 | 13 | 45 | 13 | 0.69 |
| Vp | ng/ml | 1.0E-9 | 1.0E-9 | 5.6E-1 | 3.6E-1 | 4.7E0 | 1.2E0 | 1.0E-9 | 1.0E-9 | 4.9E1 | 5.6E0 | 112 | 23 | 112 | 23 | 0.61 |
| Vt | ng/ml | 6.2E0 | 6.0E0 | 9.3E0 | 1.0E1 | 1.5E1 | 1.0E1 | 9.6E-1 | 5.6E-1 | 1.6E2 | 3.8E1 | 112 | 23 | 112 | 23 | 0.52 |
| Vu | ng/ml | 1.0E-9 | 1.5E0 | 1.2E0 | 3.4E0 | 3.0E0 | 4.5E0 | 1.0E-9 | 1.0E-9 | 2.2E1 | 1.3E1 | 109 | 22 | 109 | 22 | 0.66 |
| Vq | ng/ml | 1.6E2 | 2.1E2 | 6.9E2 | 8.7E2 | 1.6E3 | 1.4E3 | 9.2E-1 | 6.5E-1 | 1.2E4 | 4.9E3 | 88 | 20 | 88 | 20 | 0.57 |
| Vo | ng/ml | 2.6E1 | 2.5E1 | 2.5E1 | 2.4E1 | 5.3E0 | 6.9E0 | 4.9E0 | 1.9E0 | 4.8E1 | 3.4E1 | 112 | 23 | 112 | 23 | 0.50 |
| Vs | ng/ml | 1.0E-9 | 6.3E-1 | 7.8E0 | 8.8E0 | 4.4E1 | 1.4E1 | 1.0E-9 | 1.0E-9 | 4.5E2 | 4.9E1 | 110 | 22 | 110 | 22 | 0.61 |
| Vv | ng/ml | 2.6E0 | 5.1E0 | 5.2E0 | 1.0E1 | 9.5E0 | 1.2E1 | 1.0E-9 | 1.0E-9 | 8.4E1 | 4.4E1 | 111 | 23 | 111 | 23 | 0.61 |
| Vw | ng/ml | 3.6E1 | 4.4E1 | 3.4E1 | 3.9E1 | 1.7E1 | 2.3E1 | 3.1E0 | 2.5E0 | 6.7E1 | 6.9E1 | 45 | 14 | 45 | 14 | 0.59 |
| Oy | pg/ml | 4.8E-1 | 3.9E-1 | 6.4E0 | 3.5E0 | 3.2E1 | 8.4E0 | 1.0E-9 | 1.0E-9 | 4.0E2 | 4.0E1 | 309 | 44 | 309 | 44 | 0.51 |
| Oz | pg/ml | 1.0E-9 | 5.4E-2 | 3.2E-1 | 9.2E-1 | 1.7E0 | 4.2E0 | 1.0E-9 | 1.0E-9 | 2.9E1 | 2.8E1 | 309 | 44 | 309 | 44 | 0.56 |
| Pa | pg/ml | 3.9E-1 | 4.3E-1 | 1.7E0 | 7.1E0 | 8.3E0 | 3.4E1 | 1.0E-9 | 1.0E-9 | 1.0E2 | 2.3E2 | 309 | 44 | 309 | 44 | 0.57 |
| Pb | pg/ml | 1.0E-9 | 1.0E-9 | 1.8E0 | 7.5E-1 | 2.8E1 | 4.2E0 | 1.0E-9 | 1.0E-9 | 4.9E2 | 2.8E1 | 309 | 44 | 309 | 44 | 0.52 |
| Pc | pg/ml | 2.0E-2 | 2.6E-1 | 3.7E-1 | 8.8E0 | 9.2E-1 | 5.0E1 | 1.0E-9 | 1.0E-9 | 1.4E1 | 3.3E2 | 309 | 44 | 309 | 44 | 0.57 |
| Pd | pg/ml | 1.6E0 | 1.7E0 | 7.0E0 | 6.3E0 | 4.9E1 | 1.2E1 | 1.0E-9 | 1.0E-9 | 8.4E2 | 5.5E1 | 309 | 44 | 309 | 44 | 0.53 |
| Pe | pg/ml | 2.1E1 | 4.4E1 | 1.5E2 | 5.2E2 | 6.5E2 | 2.3E3 | 1.0E-9 | 1.0E-9 | 6.7E3 | 1.5E4 | 309 | 44 | 309 | 44 | 0.62 |
| Pf | pg/ml | 1.6E0 | 5.0E0 | 1.6E1 | 2.6E1 | 9.4E1 | 6.9E1 | 1.0E-9 | 1.0E-9 | 1.5E3 | 4.3E2 | 309 | 44 | 309 | 44 | 0.61 |
| Pg | pg/ml | 3.7E0 | 1.3E1 | 7.5E1 | 1.4E2 | 5.5E2 | 3.2E2 | 1.0E-9 | 1.2E-1 | 7.7E3 | 1.3E3 | 309 | 44 | 309 | 44 | 0.68 |
| Ph | ng/ml | 1.4E-1 | 2.3E-1 | 3.6E-1 | 5.2E-1 | 6.5E-1 | 7.1E-1 | 1.0E-9 | 1.0E-9 | 5.4E0 | 2.8E0 | 114 | 22 | 114 | 22 | 0.57 |
| Pi | ng/ml | 2.0E-1 | 3.0E-1 | 1.0E0 | 5.7E-1 | 7.7E0 | 9.9E-1 | 1.0E-9 | 1.0E-9 | 8.2E1 | 4.8E0 | 114 | 22 | 114 | 22 | 0.63 |
| Pj | ng/mL | 5.6E0 | 4.8E0 | 6.2E0 | 6.0E0 | 4.3E0 | 5.5E0 | 4.9E-1 | 4.0E-1 | 3.1E1 | 2.3E1 | 114 | 22 | 114 | 22 | 0.44 |
| Pk | ng/ml | 8.8E-3 | 1.3E-2 | 2.8E-2 | 1.9E-2 | 1.4E-1 | 2.4E-2 | 1.0E-9 | 1.0E-9 | 1.5E0 | 1.1E-1 | 114 | 22 | 114 | 22 | 0.60 |
| aA | mg/dL | 8.8E-1 | 1.2E0 | 9.8E-1 | 1.6E0 | 4.8E-1 | 1.0E0 | 3.0E-1 | 4.0E-1 | 4.1E0 | 4.7E0 | 474 | 63 | 474 | 63 | 0.73 |
| aC | mg/mL | 2.3E0 | 1.9E0 | 2.7E0 | 2.4E0 | 1.3E0 | 1.5E0 | 7.5E-1 | 9.7E-1 | 7.4E0 | 6.7E0 | 149 | 26 | 149 | 26 | 0.40 |
| aD | ug/mL | 2.9E0 | 3.5E0 | 4.7E0 | 4.2E0 | 5.0E0 | 2.8E0 | 7.5E-1 | 1.1E0 | 3.5E1 | 1.1E1 | 149 | 26 | 149 | 26 | 0.52 |
| aE | mg/mL | 5.8E-1 | 5.7E-1 | 5.9E-1 | 5.9E-1 | 1.8E-1 | 1.4E-1 | 1.8E-1 | 3.4E-1 | 1.2E0 | 1.0E0 | 149 | 26 | 149 | 26 | 0.49 |
| aF | ng/mL | 2.2E0 | 2.7E0 | 4.6E0 | 8.1E0 | 7.1E0 | 1.0E1 | 4.3E-3 | 4.3E-3 | 5.0E1 | 3.5E1 | 149 | 26 | 149 | 26 | 0.58 |
| aG | mg/mL | 1.4E-1 | 1.1E-1 | 1.6E-1 | 1.4E-1 | 8.9E-2 | 6.9E-2 | 3.2E-2 | 6.9E-2 | 4.8E-1 | 3.5E-1 | 149 | 26 | 149 | 26 | 0.43 |

Figure 32 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aH | ug/mL | 7.4E1 | 6.1E1 | 7.8E1 | 7.3E1 | 4.0E1 | 3.9E1 | 8.9E0 | 2.3E1 | 2.0E2 | 2.0E2 | 149 | 26 | 149 | 26 | 0.46 |
| aI | ug/mL | 1.7E2 | 1.5E2 | 1.8E2 | 1.6E2 | 6.3E1 | 5.1E1 | 3.2E1 | 7.5E1 | 3.4E2 | 2.9E2 | 149 | 26 | 149 | 26 | 0.39 |
| aJ | ug/mL | 2.2E0 | 4.2E0 | 3.0E0 | 5.4E0 | 2.1E0 | 4.6E0 | 8.2E-1 | 1.5E0 | 1.2E1 | 2.3E1 | 149 | 26 | 149 | 26 | 0.71 |
| aK | ng/mL | 1.3E0 | 1.3E0 | 2.0E0 | 1.5E0 | 2.0E0 | 1.4E0 | 2.9E-4 | 1.3E-1 | 1.0E1 | 6.5E0 | 149 | 26 | 149 | 26 | 0.45 |
| aL | mg/mL | 7.4E-1 | 7.2E-1 | 7.8E-1 | 6.9E-1 | 2.6E-1 | 2.0E-1 | 2.2E-1 | 3.2E-1 | 1.7E0 | 1.2E0 | 149 | 26 | 149 | 26 | 0.41 |
| aM | U/mL | 1.7E1 | 2.6E1 | 4.0E1 | 7.5E1 | 8.1E1 | 1.4E2 | 4.2E-2 | 4.2E-2 | 8.2E2 | 6.8E2 | 149 | 26 | 149 | 26 | 0.64 |
| aN | U/mL | 1.4E1 | 2.3E1 | 2.5E1 | 2.8E1 | 4.4E1 | 2.8E1 | 2.5E-3 | 4.8E0 | 3.8E2 | 1.3E2 | 149 | 26 | 149 | 26 | 0.61 |
| aO | pg/mL | 3.7E1 | 1.8E2 | 3.8E2 | 7.9E2 | 9.5E2 | 1.1E3 | 6.0E-2 | 2.1E0 | 6.6E3 | 3.9E3 | 149 | 26 | 149 | 26 | 0.70 |
| aP | ng/mL | 1.6E0 | 2.9E0 | 2.1E0 | 4.0E0 | 2.5E0 | 5.2E0 | 4.5E-1 | 1.1E0 | 2.8E1 | 2.8E1 | 149 | 26 | 149 | 26 | 0.73 |
| aQ | ng/mL | 2.5E-1 | 2.4E-1 | 3.6E-1 | 3.1E-1 | 3.3E-1 | 2.3E-1 | 2.0E-4 | 5.2E-2 | 2.0E0 | 9.2E-1 | 149 | 26 | 149 | 26 | 0.48 |
| aR | ng/mL | 1.7E0 | 2.8E0 | 2.8E0 | 4.1E0 | 4.0E0 | 3.8E0 | 2.6E-1 | 5.6E-1 | 3.4E1 | 1.5E1 | 149 | 26 | 149 | 26 | 0.65 |
| aS | ng/mL | 3.7E-1 | 6.0E-1 | 1.0E0 | 9.9E-1 | 2.8E0 | 1.1E0 | 4.2E-3 | 2.8E-2 | 3.3E1 | 4.9E0 | 149 | 26 | 149 | 26 | 0.58 |
| aU | pg/mL | 6.8E1 | 4.7E1 | 1.0E2 | 7.9E1 | 1.1E2 | 1.0E2 | 7.4E-2 | 7.4E-2 | 7.0E2 | 5.1E2 | 149 | 26 | 149 | 26 | 0.41 |
| aV | ng/mL | 6.1E-1 | 4.7E-1 | 1.1E0 | 6.5E-1 | 2.8E0 | 5.4E-1 | 7.6E-4 | 1.2E-1 | 3.3E1 | 2.4E0 | 149 | 26 | 149 | 26 | 0.46 |
| aW | pg/mL | 1.9E1 | 2.2E1 | 2.3E1 | 2.2E1 | 3.6E1 | 1.2E1 | 7.2E-2 | 7.2E-2 | 4.2E2 | 4.7E1 | 149 | 26 | 149 | 26 | 0.58 |
| aX | ng/mL | 7.6E0 | 1.3E1 | 1.3E1 | 3.3E1 | 2.1E1 | 6.5E1 | 3.0E-1 | 1.7E0 | 2.2E2 | 3.1E2 | 149 | 26 | 149 | 26 | 0.57 |
| aY | pg/mL | 5.3E1 | 5.9E1 | 7.5E1 | 8.2E1 | 1.1E2 | 7.6E1 | 4.1E-1 | 1.2E1 | 1.2E3 | 3.9E2 | 149 | 26 | 149 | 26 | 0.57 |
| aZ | pg/mL | 2.2E2 | 3.8E2 | 5.0E2 | 1.7E3 | 1.1E3 | 2.4E3 | 1.7E0 | 1.5E1 | 1.2E4 | 7.9E3 | 149 | 26 | 149 | 26 | 0.65 |
| bA | ng/mL | 1.2E1 | 1.0E2 | 6.0E1 | 1.6E2 | 1.5E2 | 2.9E2 | 3.0E-2 | 3.0E-2 | 9.4E2 | 1.5E3 | 149 | 26 | 149 | 26 | 0.72 |
| bB | ng/mL | 2.8E2 | 2.1E2 | 3.1E2 | 2.7E2 | 1.8E2 | 1.8E2 | 2.1E0 | 6.5E1 | 9.5E2 | 7.4E2 | 149 | 26 | 149 | 26 | 0.41 |
| bC | ng/mL | 3.2E2 | 3.3E2 | 5.9E2 | 9.8E2 | 7.8E2 | 1.3E3 | 1.4E1 | 4.6E1 | 4.7E3 | 4.0E3 | 149 | 26 | 149 | 26 | 0.55 |
| bE | mg/mL | 5.2E0 | 5.1E0 | 5.5E0 | 5.6E0 | 2.1E0 | 2.5E0 | 1.3E0 | 2.6E0 | 1.2E1 | 1.2E1 | 149 | 26 | 149 | 26 | 0.49 |
| bF | pg/mL | 3.3E1 | 6.6E1 | 3.0E2 | 6.0E2 | 1.3E3 | 1.5E3 | 5.0E-2 | 1.1E1 | 1.1E4 | 6.3E3 | 149 | 26 | 149 | 26 | 0.63 |
| bG | ng/mL | 1.5E0 | 1.8E0 | 2.8E0 | 5.0E0 | 3.5E0 | 7.7E0 | 1.1E-1 | 1.6E-1 | 2.3E1 | 3.0E1 | 149 | 26 | 149 | 26 | 0.56 |
| bH | pg/mL | 5.7E-1 | 5.7E-1 | 6.5E0 | 5.0E0 | 2.5E1 | 6.3E0 | 5.7E-1 | 5.7E-1 | 2.8E2 | 2.3E1 | 149 | 26 | 149 | 26 | 0.55 |
| bI | ng/mL | 4.0E-3 | 4.0E-3 | 9.3E-2 | 9.4E-2 | 1.9E-1 | 2.5E-1 | 4.0E-3 | 4.0E-3 | 8.8E-1 | 9.8E-1 | 149 | 26 | 149 | 26 | 0.47 |
| bJ | mg/mL | 1.9E0 | 2.2E0 | 2.4E0 | 2.5E0 | 2.0E0 | 2.0E0 | 2.5E-4 | 2.5E-4 | 1.1E1 | 8.9E0 | 149 | 26 | 149 | 26 | 0.53 |
| bL | pg/mL | 3.7E0 | 5.8E0 | 9.5E0 | 7.9E0 | 1.2E1 | 6.7E0 | 4.6E-2 | 4.6E-2 | 6.0E1 | 2.4E1 | 149 | 26 | 149 | 26 | 0.55 |
| bM | mg/mL | 1.8E0 | 1.9E0 | 2.1E0 | 2.3E0 | 1.4E0 | 1.8E0 | 1.8E-2 | 1.6E-2 | 7.9E0 | 8.6E0 | 149 | 26 | 149 | 26 | 0.51 |
| bN | ng/mL | 3.5E1 | 2.5E1 | 1.3E2 | 5.2E1 | 3.0E2 | 6.9E1 | 1.4E-1 | 1.4E-1 | 1.9E3 | 2.7E2 | 149 | 26 | 149 | 26 | 0.43 |
| bO | ng/mL | 4.0E-2 | 4.0E-2 | 9.8E0 | 5.3E0 | 1.9E1 | 2.3E1 | 4.0E-2 | 4.0E-2 | 1.3E2 | 1.2E2 | 149 | 26 | 149 | 26 | 0.37 |
| bP | mg/mL | 5.2E-1 | 5.7E-1 | 7.4E-1 | 8.1E-1 | 7.1E-1 | 7.0E-1 | 4.9E-2 | 9.2E-2 | 4.8E0 | 2.7E0 | 149 | 26 | 149 | 26 | 0.54 |
| bQ | pg/mL | 2.1E1 | 3.4E1 | 1.5E2 | 7.0E1 | 1.1E3 | 7.4E1 | 1.5E-1 | 8.1E0 | 1.3E4 | 3.2E2 | 149 | 26 | 149 | 26 | 0.65 |
| bR | ng/mL | 1.2E-2 | 1.2E-2 | 1.8E-1 | 7.0E-2 | 7.6E-1 | 1.1E-1 | 1.2E-2 | 1.2E-2 | 8.7E0 | 3.8E-1 | 149 | 26 | 149 | 26 | 0.44 |
| bS | pg/mL | 9.4E-1 | 9.4E-1 | 9.8E0 | 7.9E0 | 4.4E1 | 1.9E1 | 9.4E-1 | 9.4E-1 | 3.9E2 | 7.2E1 | 149 | 26 | 149 | 26 | 0.51 |
| bU | ng/mL | 8.7E-2 | 8.3E-2 | 2.0E-1 | 1.1E-1 | 5.7E-1 | 1.2E-1 | 1.3E-2 | 1.3E-2 | 6.6E0 | 4.1E-1 | 149 | 26 | 149 | 26 | 0.46 |
| bV | pg/mL | 4.6E2 | 6.5E2 | 6.1E2 | 7.7E2 | 9.4E2 | 4.5E2 | 1.6E2 | 3.4E2 | 1.2E4 | 2.2E3 | 149 | 26 | 149 | 26 | 0.70 |
| bW | pg/mL | 3.2E2 | 3.3E2 | 4.8E2 | 6.7E2 | 5.2E2 | 9.9E2 | 8.4E1 | 1.1E2 | 4.8E3 | 3.9E3 | 149 | 26 | 149 | 26 | 0.51 |
| bX | ng/mL | 2.5E-5 | 2.5E-5 | 2.6E-3 | 2.4E-3 | 3.2E-3 | 2.8E-3 | 2.5E-5 | 2.5E-5 | 1.3E-2 | 7.2E-3 | 149 | 26 | 149 | 26 | 0.49 |
| bZ | pg/mL | 2.7E2 | 7.2E2 | 1.8E3 | 3.4E3 | 6.8E3 | 8.4E3 | 1.5E-1 | 1.5E-1 | 5.8E4 | 4.3E4 | 149 | 26 | 149 | 26 | 0.64 |
| cA | pg/mL | 6.0E-1 | 6.0E-1 | 4.5E0 | 1.7E0 | 3.1E1 | 4.2E0 | 6.0E-1 | 6.0E-1 | 3.7E2 | 2.1E1 | 149 | 26 | 149 | 26 | 0.47 |
| cB | ng/mL | 5.3E-2 | 2.9E-2 | 8.0E-2 | 4.3E-2 | 9.1E-2 | 6.1E-2 | 1.7E-3 | 1.7E-3 | 4.3E-1 | 2.6E-1 | 149 | 26 | 149 | 26 | 0.35 |
| cC | pg/mL | 4.4E1 | 3.9E1 | 4.7E1 | 3.6E1 | 5.3E1 | 2.5E1 | 1.0E0 | 1.0E0 | 4.5E2 | 7.7E1 | 149 | 26 | 149 | 26 | 0.45 |
| cD | pg/mL | 4.9E0 | 4.5E0 | 1.3E1 | 8.0E0 | 4.9E1 | 1.4E1 | 3.3E-1 | 3.3E-1 | 4.8E2 | 6.9E1 | 149 | 26 | 149 | 26 | 0.48 |
| cE | pg/mL | 5.5E1 | 8.3E1 | 2.6E2 | 2.8E2 | 6.1E2 | 4.6E2 | 1.2E-1 | 6.1E0 | 3.8E3 | 1.7E3 | 149 | 26 | 149 | 26 | 0.60 |
| cF | pg/mL | 9.4E0 | 5.3E-1 | 1.8E1 | 5.1E0 | 3.1E1 | 9.7E0 | 5.3E-1 | 5.3E-1 | 2.7E2 | 3.8E1 | 149 | 26 | 149 | 26 | 0.33 |
| cG | pg/mL | 5.3E1 | 1.3E2 | 1.7E2 | 1.9E2 | 8.6E2 | 2.2E2 | 7.8E0 | 2.4E1 | 1.0E4 | 1.1E3 | 149 | 26 | 149 | 26 | 0.70 |
| cH | uIU/mL | 3.2E0 | 3.9E0 | 6.6E0 | 1.3E1 | 1.5E1 | 2.6E1 | 8.6E-3 | 8.6E-3 | 1.6E2 | 1.2E2 | 149 | 26 | 149 | 26 | 0.53 |
| cI | pg/mL | 6.0E0 | 8.2E0 | 1.5E1 | 1.0E1 | 2.3E1 | 1.1E1 | 3.2E-2 | 2.3E-1 | 1.2E2 | 4.1E1 | 149 | 26 | 149 | 26 | 0.49 |
| cJ | ug/mL | 6.7E1 | 4.7E1 | 1.0E2 | 8.1E1 | 1.0E2 | 8.5E1 | 6.9E0 | 5.6E0 | 6.4E2 | 3.4E2 | 149 | 26 | 149 | 26 | 0.45 |
| cK | ng/mL | 3.8E-3 | 3.8E-3 | 2.4E-2 | 1.6E-2 | 1.2E-1 | 4.2E-2 | 3.8E-3 | 3.8E-3 | 1.5E0 | 2.1E-1 | 149 | 26 | 149 | 26 | 0.50 |
| cL | pg/mL | 2.1E2 | 2.3E2 | 5.0E2 | 7.7E2 | 2.1E3 | 1.5E3 | 3.1E1 | 6.7E1 | 2.4E4 | 7.4E3 | 149 | 26 | 149 | 26 | 0.60 |
| cM | pg/mL | 2.7E2 | 2.8E2 | 2.9E2 | 2.7E2 | 1.7E2 | 8.6E1 | 2.5E1 | 1.2E2 | 1.1E3 | 4.4E2 | 149 | 26 | 149 | 26 | 0.50 |
| cN | pg/mL | 1.2E2 | 1.4E2 | 1.3E2 | 1.4E2 | 9.0E1 | 3.6E1 | 3.8E1 | 8.6E1 | 1.1E3 | 2.2E2 | 149 | 26 | 149 | 26 | 0.65 |
| cO | pg/mL | 2.1E2 | 2.5E2 | 4.2E2 | 3.5E2 | 1.6E3 | 3.1E2 | 5.4E1 | 8.2E1 | 1.9E4 | 1.5E3 | 149 | 26 | 149 | 26 | 0.58 |
| cP | ng/mL | 2.4E3 | 2.8E3 | 2.5E3 | 2.7E3 | 9.5E2 | 9.6E2 | 6.2E2 | 1.4E3 | 5.6E3 | 4.7E3 | 149 | 26 | 149 | 26 | 0.57 |
| cQ | ng/mL | 5.3E-2 | 5.9E-2 | 1.3E-1 | 1.3E-1 | 2.2E-1 | 1.4E-1 | 2.0E-3 | 2.0E-3 | 1.3E0 | 4.8E-1 | 149 | 26 | 149 | 26 | 0.57 |

Figure 32 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cR | ng/mL | 3.4E2 | 3.8E2 | 6.1E2 | 5.6E2 | 8.7E2 | 5.5E2 | 2.0E1 | 8.9E1 | 7.7E3 | 2.2E3 | 149 | 26 | 149 | 26 | 0.51 |
| cS | ng/mL | 2.7E2 | 3.6E2 | 4.0E2 | 9.1E2 | 4.3E2 | 1.5E3 | 4.1E1 | 1.2E2 | 2.5E3 | 7.1E3 | 149 | 26 | 149 | 26 | 0.67 |
| cT | ng/mL | 4.9E1 | 1.2E2 | 1.3E2 | 3.2E2 | 2.7E2 | 4.4E2 | 3.6E0 | 1.4E1 | 2.1E3 | 1.5E3 | 149 | 26 | 149 | 26 | 0.65 |
| cU | ng/mL | 5.6E1 | 1.4E2 | 9.1E1 | 1.5E2 | 1.5E2 | 9.2E1 | 6.2E0 | 1.7E1 | 1.6E3 | 3.9E2 | 149 | 26 | 149 | 26 | 0.74 |
| cV | ng/mL | 2.1E-1 | 1.9E-1 | 7.3E-1 | 7.1E-1 | 3.9E0 | 1.9E0 | 2.5E-2 | 3.4E-2 | 4.7E1 | 9.7E0 | 149 | 26 | 149 | 26 | 0.49 |
| cW | mIU/mL | 4.8E-2 | 6.2E-2 | 9.1E-2 | 7.7E-2 | 3.7E-1 | 6.0E-2 | 4.8E-3 | 1.6E-2 | 4.5E0 | 2.9E-1 | 149 | 26 | 149 | 26 | 0.59 |
| cX | ng/mL | 1.1E-1 | 1.8E-1 | 1.7E0 | 2.6E0 | 5.2E0 | 7.5E0 | 2.3E-4 | 9.1E-3 | 2.8E1 | 2.8E1 | 149 | 26 | 149 | 26 | 0.54 |
| cY | ng/mL | 7.5E0 | 6.5E0 | 1.1E1 | 8.5E0 | 1.1E1 | 7.8E0 | 1.7E-1 | 6.0E-1 | 6.1E1 | 3.6E1 | 149 | 26 | 149 | 26 | 0.45 |
| cZ | ug/mL | 1.3E1 | 1.2E1 | 1.5E1 | 1.4E1 | 6.9E0 | 6.4E0 | 2.3E0 | 6.2E0 | 4.6E1 | 3.0E1 | 149 | 26 | 149 | 26 | 0.47 |
| dA | pg/mL | 3.2E2 | 3.1E2 | 3.9E2 | 3.8E2 | 4.8E2 | 1.8E2 | 1.0E2 | 1.7E2 | 5.8E3 | 8.8E2 | 149 | 26 | 149 | 26 | 0.53 |
| dB | ug/mL | 1.8E1 | 2.2E1 | 1.8E1 | 2.0E1 | 2.1E1 | 8.0E0 | 2.1E0 | 2.9E0 | 2.5E2 | 3.7E1 | 149 | 26 | 149 | 26 | 0.63 |
| dC | nmol/L | 3.5E1 | 3.0E1 | 3.7E1 | 3.5E1 | 1.7E1 | 1.6E1 | 7.8E0 | 1.5E1 | 1.4E2 | 9.1E1 | 149 | 26 | 149 | 26 | 0.43 |
| dD | ug/mL | 3.4E1 | 2.9E1 | 3.6E1 | 3.2E1 | 1.1E1 | 8.2E0 | 1.4E1 | 2.0E1 | 7.4E1 | 5.2E1 | 149 | 26 | 149 | 26 | 0.38 |
| dE | ng/mL | 4.6E-1 | 4.7E-1 | 5.5E-1 | 7.5E-1 | 5.5E-1 | 8.3E-1 | 8.4E-3 | 8.4E-3 | 2.7E0 | 2.9E0 | 149 | 26 | 149 | 26 | 0.54 |
| dF | ng/mL | 2.4E2 | 3.8E2 | 3.2E2 | 5.0E2 | 2.4E2 | 3.0E2 | 7.5E1 | 1.3E2 | 1.3E3 | 1.2E3 | 149 | 26 | 149 | 26 | 0.70 |
| dG | ng/mL | 1.1E1 | 1.5E1 | 1.7E1 | 2.0E1 | 2.0E1 | 1.3E1 | 3.0E0 | 6.7E0 | 1.8E2 | 6.5E1 | 149 | 26 | 149 | 26 | 0.66 |
| dH | pg/mL | 8.0E0 | 9.6E0 | 2.1E1 | 1.6E1 | 6.6E1 | 2.2E1 | 4.0E-2 | 8.3E-1 | 6.7E2 | 9.7E1 | 149 | 26 | 149 | 26 | 0.56 |
| dI | pg/mL | 4.6E-1 | 4.6E-1 | 4.0E0 | 2.4E0 | 2.7E1 | 4.3E0 | 4.6E-1 | 4.6E-1 | 3.3E2 | 1.9E1 | 149 | 26 | 149 | 26 | 0.52 |
| dJ | ng/mL | 2.1E0 | 1.8E0 | 2.2E0 | 2.0E0 | 1.1E0 | 1.0E0 | 3.2E-2 | 3.7E-1 | 5.6E0 | 4.5E0 | 149 | 26 | 149 | 26 | 0.45 |
| dK | uIU/mL | 1.4E0 | 1.0E0 | 2.2E0 | 1.6E0 | 3.8E0 | 1.8E0 | 2.8E-4 | 1.4E-2 | 3.9E1 | 7.3E0 | 149 | 26 | 149 | 26 | 0.43 |
| dL | ng/mL | 8.7E2 | 1.2E3 | 1.0E3 | 1.2E3 | 6.5E2 | 4.3E2 | 2.8E2 | 5.8E2 | 4.8E3 | 2.3E3 | 149 | 26 | 149 | 26 | 0.64 |
| dM | pg/mL | 9.5E2 | 1.3E3 | 1.3E3 | 1.8E3 | 1.5E3 | 1.3E3 | 3.7E2 | 5.2E2 | 1.5E4 | 5.8E3 | 149 | 26 | 149 | 26 | 0.65 |
| dN | ug/mL | 9.8E1 | 1.1E2 | 1.0E2 | 1.2E2 | 4.5E1 | 3.9E1 | 2.4E1 | 6.4E1 | 3.3E2 | 2.2E2 | 149 | 26 | 149 | 26 | 0.61 |
| dR | pg/ml | 1.5E3 | 9.3E2 | 2.2E3 | 1.4E3 | 2.1E3 | 1.3E3 | 1.4E2 | 1.3E2 | 9.8E3 | 5.5E3 | 111 | 21 | 111 | 21 | 0.38 |
| dU | pg/ml | 9.7E3 | 1.1E4 | 1.6E4 | 1.3E4 | 1.8E4 | 1.1E4 | 6.9E2 | 1.7E3 | 8.1E4 | 3.5E4 | 24 | 9 | 24 | 9 | 0.48 |
| dX | ng/ml | 6.6E-2 | 8.2E-2 | 1.4E-1 | 1.2E-1 | 2.0E-1 | 1.3E-1 | 2.6E-3 | 2.6E-3 | 1.2E0 | 4.2E-1 | 50 | 11 | 50 | 11 | 0.55 |
| eF | ng/ml | 4.1E0 | 5.5E0 | 5.1E0 | 6.7E0 | 4.6E0 | 5.5E0 | 2.0E0 | 2.0E0 | 4.6E1 | 2.9E1 | 111 | 21 | 111 | 21 | 0.65 |
| eC | pg/ml | 3.0E2 | 2.7E2 | 3.7E2 | 3.1E2 | 3.2E2 | 1.8E2 | 9.9E0 | 1.1E2 | 2.0E3 | 7.3E2 | 98 | 18 | 98 | 18 | 0.45 |
| eD | pg/ml | 2.2E2 | 2.6E2 | 6.0E2 | 1.3E3 | 1.4E3 | 2.1E3 | 5.2E-1 | 5.9E1 | 8.3E3 | 7.0E3 | 81 | 15 | 81 | 15 | 0.58 |
| eM | ng/ml | 2.7E0 | 3.2E0 | 4.8E0 | 5.7E0 | 5.6E0 | 9.4E0 | 6.9E-1 | 7.6E-1 | 2.7E1 | 3.9E1 | 64 | 15 | 64 | 15 | 0.54 |
| eP | ng/ml | 3.7E-3 | 3.7E-3 | 1.2E0 | 1.4E0 | 4.1E0 | 3.0E0 | 3.7E-3 | 3.7E-3 | 2.8E1 | 1.0E1 | 50 | 11 | 50 | 11 | 0.50 |
| eQ | pg/ml | 1.0E0 | 1.0E0 | 5.7E1 | 4.2E1 | 1.2E2 | 8.4E1 | 1.0E0 | 1.0E0 | 4.7E2 | 2.2E2 | 24 | 9 | 24 | 9 | 0.45 |
| fA | ng/ml | 1.8E2 | 3.0E2 | 4.0E2 | 5.3E2 | 4.8E2 | 4.7E2 | 3.9E1 | 7.5E1 | 1.5E3 | 1.3E3 | 23 | 8 | 23 | 8 | 0.65 |
| fB | ng/ml | 5.9E2 | 6.0E2 | 6.7E2 | 6.3E2 | 2.9E2 | 2.1E2 | 2.6E2 | 3.5E2 | 1.3E3 | 9.2E2 | 22 | 9 | 22 | 9 | 0.46 |
| fP | ng/ml | 2.6E2 | 2.8E2 | 3.2E2 | 3.3E2 | 1.8E2 | 2.0E2 | 3.7E1 | 1.8E0 | 1.0E3 | 9.5E2 | 106 | 20 | 106 | 20 | 0.53 |
| fR | ng/ml | 1.3E5 | 2.2E5 | 2.1E5 | 2.9E5 | 1.7E5 | 2.1E5 | 3.6E4 | 1.9E2 | 6.9E5 | 8.7E5 | 95 | 20 | 95 | 20 | 0.63 |
| gC | ng/ml | 2.4E2 | 2.7E2 | 2.6E2 | 2.8E2 | 1.1E2 | 1.6E2 | 8.3E1 | 9.7E1 | 6.4E2 | 5.9E2 | 37 | 10 | 37 | 10 | 0.52 |
| gL | pg/ml | 6.5E4 | 7.7E4 | 7.1E4 | 9.5E4 | 3.3E4 | 5.1E4 | 1.1E4 | 2.7E4 | 1.9E5 | 2.2E5 | 111 | 21 | 111 | 21 | 0.62 |
| gP | U/ml | 2.7E2 | 2.8E2 | 2.8E2 | 3.3E2 | 1.0E2 | 2.0E2 | 1.2E1 | 6.5E1 | 8.0E2 | 1.1E3 | 110 | 21 | 110 | 21 | 0.58 |
| gW | ng/ml | 5.4E2 | 5.2E2 | 9.6E2 | 6.3E2 | 1.1E3 | 4.6E2 | 2.3E0 | 2.0E2 | 6.1E3 | 1.8E3 | 87 | 11 | 87 | 11 | 0.49 |
| gV | ng/ml | 1.9E1 | 2.3E1 | 2.0E1 | 2.6E1 | 7.5E0 | 5.1E0 | 8.1E-2 | 2.1E1 | 3.7E1 | 3.4E1 | 30 | 8 | 30 | 8 | 0.73 |
| tF | pg/mL | 9.0E2 | 4.8E3 | 9.7E3 | 2.4E4 | 3.4E4 | 5.8E4 | 1.2E1 | 1.8E1 | 2.8E5 | 2.5E5 | 99 | 19 | 99 | 19 | 0.66 |
| gZ | ug/ml | 6.8E-1 | 1.2E0 | 4.3E1 | 3.4E1 | 1.2E2 | 7.8E1 | 8.7E-2 | 1.4E-1 | 4.1E2 | 2.4E2 | 24 | 9 | 24 | 9 | 0.63 |
| hA | ng/ml | 2.3E0 | 5.2E0 | 1.4E1 | 1.5E1 | 5.3E1 | 3.0E1 | 1.7E-2 | 7.4E-1 | 3.5E2 | 1.1E2 | 81 | 16 | 81 | 16 | 0.68 |
| nM | pg/ml | 1.0E-9 | 1.0E-9 | 1.0E-9 | 8.0E1 | 0.0E0 | 3.5E2 | 1.0E-9 | 1.0E-9 | 1.0E-9 | 1.5E3 | 57 | 19 | 57 | 19 | 0.53 |
| nN | pg/ml | 1.3E3 | 2.4E3 | 2.5E3 | 1.8E4 | 3.3E3 | 4.1E4 | 8.1E1 | 2.3E2 | 2.1E4 | 1.5E5 | 57 | 19 | 57 | 19 | 0.63 |
| nO | pg/ml | 2.4E1 | 4.1E1 | 3.6E1 | 4.5E1 | 4.8E1 | 3.9E1 | 4.0E0 | 9.7E0 | 3.1E2 | 1.5E2 | 57 | 19 | 57 | 19 | 0.65 |
| nR | pg/ml | 1.5E1 | 4.8E1 | 3.8E1 | 2.9E2 | 5.9E1 | 5.0E2 | 1.0E0 | 3.5E0 | 2.6E2 | 1.9E3 | 57 | 19 | 57 | 19 | 0.75 |
| nT | pg/ml | 7.3E1 | 8.8E1 | 9.3E1 | 1.9E2 | 7.6E1 | 2.4E2 | 1.0E-9 | 1.0E-9 | 3.3E2 | 9.2E2 | 57 | 19 | 57 | 19 | 0.59 |
| nU | pg/ml | 3.1E1 | 1.2E2 | 4.8E1 | 2.8E2 | 5.5E1 | 3.9E2 | 1.0E-9 | 1.0E-9 | 2.0E2 | 1.5E3 | 57 | 19 | 57 | 19 | 0.70 |
| lW | pg/ml | 1.0E-9 | 1.0E-9 | 1.0E1 | 1.2E1 | 3.2E1 | 2.1E1 | 1.0E-9 | 1.0E-9 | 1.7E2 | 7.0E1 | 57 | 19 | 57 | 19 | 0.57 |
| lX | pg/ml | 9.0E2 | 9.1E2 | 1.0E3 | 9.9E2 | 5.9E2 | 5.0E2 | 1.9E2 | 4.8E2 | 2.6E3 | 2.5E3 | 57 | 19 | 57 | 19 | 0.52 |
| lY | pg/ml | 2.0E1 | 1.2E1 | 2.1E1 | 1.7E1 | 1.8E1 | 1.3E1 | 1.0E-9 | 1.0E-9 | 1.2E2 | 4.5E1 | 57 | 19 | 57 | 19 | 0.41 |
| mE | pg/ml | 1.0E-9 | 1.0E-9 | 3.0E0 | 1.2E0 | 8.4E0 | 2.6E0 | 1.0E-9 | 1.0E-9 | 5.7E1 | 9.2E0 | 57 | 19 | 57 | 19 | 0.43 |
| mF | pg/ml | 2.7E-1 | 7.1E-1 | 3.5E0 | 1.6E1 | 1.4E1 | 5.6E1 | 1.0E-9 | 1.0E-9 | 1.1E2 | 2.5E2 | 57 | 19 | 57 | 19 | 0.58 |
| mH | pg/ml | 3.3E0 | 2.6E0 | 5.3E0 | 5.5E0 | 7.9E0 | 7.8E0 | 4.0E-1 | 5.4E-1 | 5.3E1 | 3.2E1 | 57 | 19 | 57 | 19 | 0.45 |
| mI | pg/ml | 1.0E-9 | 2.6E0 | 1.2E1 | 3.8E1 | 2.7E1 | 1.0E2 | 1.0E-9 | 1.0E-9 | 1.8E2 | 4.6E2 | 57 | 19 | 57 | 19 | 0.55 |

Figure 32 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| mM | pg/ml | 2.8E1 | 5.1E1 | 6.4E1 | 1.3E2 | 8.9E1 | 2.6E2 | 1.0E-9 | 1.0E-9 | 4.0E2 | 1.1E3 | 57 | 19 | 57 | 19 | 0.57 |
| mP | pg/ml | 1.5E1 | 1.6E1 | 1.5E1 | 7.2E1 | 9.9E0 | 1.8E2 | 1.0E-9 | 8.2E0 | 5.8E1 | 8.1E2 | 56 | 19 | 56 | 19 | 0.63 |
| mS | pg/ml | 1.6E3 | 1.6E3 | 1.8E3 | 1.8E3 | 9.9E2 | 1.1E3 | 1.0E-9 | 1.0E-9 | 5.1E3 | 4.2E3 | 57 | 19 | 57 | 19 | 0.49 |
| mT | pg/ml | 5.7E1 | 5.6E1 | 1.2E2 | 2.4E2 | 2.1E2 | 4.5E2 | 1.0E1 | 1.6E1 | 1.4E3 | 1.7E3 | 56 | 19 | 56 | 19 | 0.52 |
| mU | pg/ml | 2.0E0 | 3.5E0 | 2.7E0 | 1.7E1 | 2.0E0 | 5.0E1 | 1.0E-9 | 6.1E-1 | 1.0E1 | 2.2E2 | 56 | 19 | 56 | 19 | 0.68 |
| mW | pg/ml | 2.1E3 | 1.9E3 | 2.3E3 | 3.4E3 | 1.1E3 | 3.2E3 | 1.0E-9 | 2.0E2 | 6.2E3 | 1.1E4 | 56 | 19 | 56 | 19 | 0.54 |
| mY | pg/ml | 6.5E2 | 6.7E2 | 8.7E2 | 1.2E3 | 9.9E2 | 1.8E3 | 1.0E-9 | 6.1E1 | 5.6E3 | 8.0E3 | 57 | 19 | 57 | 19 | 0.56 |
| mZ | pg/ml | 1.5E2 | 3.0E2 | 3.3E2 | 4.9E2 | 4.9E2 | 4.2E2 | 1.0E-9 | 3.9E1 | 3.1E3 | 1.4E3 | 56 | 19 | 56 | 19 | 0.67 |
| nA | pg/ml | 1.5E0 | 2.7E0 | 5.9E0 | 1.0E1 | 1.2E1 | 1.9E1 | 1.0E-9 | 1.0E-9 | 6.5E1 | 5.7E1 | 56 | 19 | 56 | 19 | 0.52 |
| nB | pg/ml | 2.8E1 | 3.0E2 | 3.0E2 | 3.7E2 | 1.6E2 | 2.1E2 | 3.0E1 | 1.3E2 | 6.9E2 | 9.6E2 | 57 | 19 | 57 | 19 | 0.58 |
| nC | pg/ml | 1.0E-9 | 8.3E1 | 1.1E4 | 1.8E3 | 5.8E4 | 4.7E3 | 1.0E-9 | 1.0E-9 | 3.8E5 | 2.0E4 | 57 | 19 | 57 | 19 | 0.60 |
| nD | pg/ml | 6.6E0 | 9.2E0 | 1.2E1 | 1.8E1 | 3.4E1 | 2.7E1 | 1.0E-9 | 1.0E-9 | 2.6E2 | 1.2E2 | 56 | 19 | 56 | 19 | 0.59 |
| nF | pg/ml | 1.0E-9 | 1.0E-9 | 3.0E0 | 3.2E0 | 1.3E1 | 1.1E1 | 1.0E-9 | 1.0E-9 | 9.3E1 | 4.7E1 | 57 | 19 | 57 | 19 | 0.50 |
| nH | pg/ml | 5.6E-1 | 4.2E0 | 2.3E2 | 2.7E1 | 1.4E3 | 7.5E1 | 1.0E-9 | 1.0E-9 | 1.0E4 | 3.3E2 | 56 | 19 | 56 | 19 | 0.60 |
| nI | pg/ml | 3.0E1 | 1.0E-9 | 6.1E1 | 8.7E1 | 8.0E1 | 2.7E2 | 1.0E-9 | 1.0E-9 | 3.5E2 | 1.2E3 | 57 | 19 | 57 | 19 | 0.40 |
| nJ | pg/ml | 1.7E-1 | 6.1E-1 | 3.1E0 | 1.9E0 | 1.7E1 | 3.7E0 | 1.0E-9 | 1.0E-9 | 1.3E2 | 1.5E1 | 57 | 19 | 57 | 19 | 0.53 |
| nK | pg/ml | 1.0E-9 | 1.0E-9 | 1.4E1 | 2.1E1 | 2.4E1 | 5.2E1 | 1.0E-9 | 1.0E-9 | 1.0E2 | 2.2E2 | 56 | 19 | 56 | 19 | 0.48 |
| nL | pg/ml | 1.0E-9 | 2.5E0 | 3.4E2 | 7.5E1 | 1.9E3 | 2.1E2 | 1.0E-9 | 1.0E-9 | 1.4E4 | 9.0E2 | 57 | 19 | 57 | 19 | 0.56 |
| wJ | pg/ml | 1.3E5 | 2.5E5 | 1.5E5 | 2.9E5 | 9.4E4 | 1.7E5 | 1.1E4 | 1.1E5 | 4.3E5 | 5.8E5 | 49 | 7 | 49 | 7 | 0.78 |
| wK | pg/ml | 3.2E4 | 6.6E4 | 3.9E4 | 1.2E5 | 2.8E4 | 1.7E5 | 3.7E3 | 2.5E4 | 1.3E5 | 5.0E5 | 49 | 7 | 49 | 7 | 0.79 |
| wL | pg/ml | 3.9E0 | 2.9E1 | 3.8E1 | 1.4E2 | 1.3E2 | 1.8E2 | 1.0E-9 | 6.7E0 | 8.4E2 | 4.7E2 | 49 | 7 | 49 | 7 | 0.83 |
| wP | pg/ml | 2.4E4 | 4.3E4 | 4.8E4 | 5.7E4 | 5.8E4 | 5.8E4 | 1.1E3 | 4.5E3 | 3.0E5 | 1.7E5 | 49 | 7 | 49 | 7 | 0.57 |
| wQ | pg/ml | 3.1E1 | 7.6E1 | 5.5E1 | 9.7E1 | 9.2E1 | 9.4E1 | 1.0E-9 | 1.1E1 | 5.1E2 | 2.4E2 | 49 | 7 | 49 | 7 | 0.70 |
| hR | pg/ml | 2.9E4 | 2.0E4 | 3.0E4 | 2.0E4 | 1.2E4 | 4.0E3 | 1.0E-9 | 1.4E4 | 5.8E4 | 2.7E4 | 76 | 14 | 76 | 14 | 0.20 |
| hV | pg/ml | 4.7E2 | 3.5E2 | 4.6E2 | 3.9E2 | 2.3E2 | 2.1E2 | 1.0E-9 | 1.3E2 | 1.2E3 | 8.8E2 | 76 | 14 | 76 | 14 | 0.40 |
| hW | pg/ml | 1.7E3 | 1.9E3 | 2.6E3 | 2.3E3 | 4.5E3 | 1.3E3 | 1.0E-9 | 7.1E2 | 4.0E4 | 4.7E3 | 76 | 14 | 76 | 14 | 0.53 |
| hX | pg/ml | 1.1E3 | 9.6E2 | 1.1E3 | 1.1E3 | 9.5E2 | 6.4E2 | 2.5E0 | 5.2E2 | 8.6E3 | 2.9E3 | 76 | 14 | 76 | 14 | 0.47 |
| iA | pg/ml | 1.6E2 | 1.8E2 | 2.6E2 | 2.5E2 | 2.9E2 | 2.0E2 | 1.5E1 | 2.3E1 | 1.8E3 | 6.8E2 | 98 | 20 | 98 | 20 | 0.51 |
| iB | ng/ml | 4.8E0 | 6.8E0 | 6.2E0 | 8.6E0 | 5.1E0 | 4.8E0 | 3.3E-2 | 2.5E0 | 2.4E1 | 1.9E1 | 81 | 16 | 81 | 16 | 0.69 |
| iC | U/ml | 2.8E-1 | 5.3E-1 | 1.3E0 | 5.3E-1 | 6.2E0 | 2.5E-1 | 1.0E-9 | 1.4E-1 | 5.5E1 | 1.1E0 | 81 | 16 | 81 | 16 | 0.67 |
| tQ | pg/ml | 1.4E3 | 1.3E3 | 1.5E3 | 1.5E3 | 6.0E2 | 4.9E2 | 3.7E2 | 9.5E2 | 3.3E3 | 2.2E3 | 45 | 7 | 45 | 7 | 0.50 |
| tT | pg/ml | 2.0E1 | 1.8E1 | 2.2E1 | 2.0E1 | 1.5E1 | 9.3E0 | 5.4E0 | 1.0E1 | 9.3E1 | 3.4E1 | 46 | 7 | 46 | 7 | 0.51 |
| tS | pg/ml | 7.7E-1 | 1.3E0 | 1.5E0 | 1.0E0 | 2.1E0 | 7.6E-1 | 1.0E-9 | 1.0E-9 | 1.0E1 | 2.0E0 | 47 | 7 | 47 | 7 | 0.52 |
| tX | pg/ml | 1.1E0 | 1.3E0 | 1.8E0 | 1.4E0 | 2.1E0 | 1.1E0 | 2.5E-2 | 4.0E-1 | 1.0E1 | 3.3E0 | 46 | 7 | 46 | 7 | 0.50 |
| tO | pg/ml | 3.9E0 | 5.9E0 | 5.2E0 | 5.6E0 | 3.9E0 | 2.0E0 | 1.0E-9 | 2.9E0 | 1.8E1 | 8.9E0 | 47 | 7 | 47 | 7 | 0.62 |
| tR | pg/ml | 1.9E-1 | 3.4E-1 | 3.5E-1 | 3.3E-1 | 4.9E-1 | 2.7E-1 | 1.0E-9 | 9.8E-3 | 2.5E0 | 8.7E-1 | 46 | 7 | 46 | 7 | 0.58 |
| tU | pg/ml | 1.1E1 | 5.5E0 | 1.3E1 | 1.3E1 | 1.3E1 | 1.9E1 | 2.2E-1 | 1.5E0 | 8.0E1 | 5.5E1 | 48 | 7 | 48 | 7 | 0.36 |
| tN | pg/ml | 2.0E1 | 2.5E1 | 3.2E1 | 2.6E1 | 3.4E1 | 1.9E1 | 1.0E-9 | 1.0E-9 | 1.6E2 | 5.3E1 | 45 | 7 | 45 | 7 | 0.52 |
| tV | pg/ml | 5.3E2 | 1.1E3 | 7.7E2 | 8.8E2 | 6.5E2 | 4.5E2 | 5.3E1 | 2.1E2 | 3.1E3 | 1.2E3 | 48 | 7 | 48 | 7 | 0.57 |
| iH | ng/ml | 1.6E5 | 1.8E5 | 1.6E5 | 1.7E5 | 5.1E4 | 4.3E4 | 2.9E3 | 8.1E4 | 2.6E5 | 2.5E5 | 98 | 20 | 98 | 20 | 0.58 |
| iJ | ng/ml | 4.8E4 | 5.1E4 | 5.3E4 | 6.5E4 | 3.2E4 | 5.0E4 | 1.8E3 | 1.5E4 | 2.5E5 | 2.5E5 | 98 | 20 | 98 | 20 | 0.58 |
| hB | ng/ml | 4.8E-1 | 6.4E-1 | 6.2E-1 | 7.2E-1 | 5.2E-1 | 4.3E-1 | 1.2E-1 | 2.3E-1 | 3.2E0 | 1.9E0 | 98 | 20 | 98 | 20 | 0.59 |
| hC | pg/ml | 4.0E3 | 1.0E4 | 7.9E3 | 1.0E4 | 1.3E4 | 8.0E3 | 4.1E1 | 2.3E2 | 1.1E5 | 2.6E4 | 98 | 20 | 98 | 20 | 0.63 |
| hF | ng/ml | 1.0E-9 | 1.0E-9 | 4.1E1 | 1.0E-9 | 4.0E2 | 0.0E0 | 1.0E-9 | 1.0E-9 | 4.0E3 | 1.0E-9 | 98 | 20 | 98 | 20 | 0.49 |
| hG | pg/ml | 6.7E3 | 7.7E3 | 7.2E3 | 9.5E3 | 3.1E3 | 4.1E3 | 1.8E3 | 4.5E3 | 2.0E4 | 1.8E4 | 98 | 20 | 98 | 20 | 0.68 |
| iO | ng/ml | 3.7E5 | 4.6E5 | 4.1E5 | 4.5E5 | 2.0E5 | 1.7E5 | 1.1E4 | 1.0E5 | 1.1E6 | 7.7E5 | 98 | 20 | 98 | 20 | 0.60 |
| iP | ng/ml | 5.2E4 | 6.2E4 | 5.4E4 | 7.4E4 | 3.1E4 | 8.9E4 | 1.0E-9 | 2.5E4 | 2.2E5 | 4.4E5 | 98 | 20 | 98 | 20 | 0.55 |
| iZ | ng/ml | 1.6E3 | 2.1E3 | 1.8E3 | 2.3E3 | 8.0E2 | 1.2E3 | 6.6E2 | 8.4E2 | 5.1E3 | 5.7E3 | 95 | 21 | 95 | 21 | 0.63 |
| yD | ng/ml | 1.2E-2 | 1.8E-2 | 1.3E-2 | 1.7E-2 | 5.8E-3 | 4.0E-3 | 1.0E-9 | 1.0E-9 | 2.8E-2 | 2.2E-2 | 49 | 7 | 49 | 7 | 0.76 |
| jB | ng/ml | 2.3E5 | 2.3E5 | 2.4E5 | 2.4E5 | 7.4E4 | 8.0E4 | 9.9E4 | 1.3E5 | 3.6E5 | 3.5E5 | 24 | 9 | 24 | 9 | 0.50 |
| wB | pg/ml | 8.9E3 | 1.1E4 | 1.2E4 | 9.4E3 | 9.3E3 | 5.6E3 | 1.7E3 | 1.9E3 | 4.2E4 | 1.6E4 | 49 | 7 | 49 | 7 | 0.45 |
| rC | pg/ml | 1.6E3 | 1.2E3 | 2.1E3 | 2.5E3 | 2.1E3 | 3.2E3 | 1.0E-9 | 6.0E2 | 1.5E4 | 1.1E4 | 74 | 13 | 74 | 13 | 0.47 |
| rB | pg/ml | 3.0E1 | 6.9E1 | 4.8E1 | 8.7E1 | 6.4E1 | 8.4E1 | 1.0E-9 | 4.0E0 | 3.9E2 | 3.2E2 | 74 | 13 | 74 | 13 | 0.67 |
| jD | ng/ml | 2.7E1 | 5.5E1 | 3.9E1 | 9.8E1 | 4.1E1 | 1.3E2 | 1.0E-9 | 1.0E-9 | 1.9E2 | 5.1E2 | 81 | 16 | 81 | 16 | 0.68 |
| jE | ng/ml | 1.0E-9 | 1.0E-9 | 5.3E0 | 7.3E0 | 1.3E1 | 1.1E1 | 1.0E-9 | 1.0E-9 | 6.2E1 | 2.9E1 | 81 | 16 | 81 | 16 | 0.58 |
| jF | ng/ml | 4.2E1 | 1.4E1 | 4.9E1 | 4.0E1 | 5.3E1 | 5.2E1 | 1.0E-9 | 1.0E-9 | 2.1E2 | 1.5E2 | 81 | 16 | 81 | 16 | 0.45 |
| jG | ng/ml | 4.0E3 | 5.3E3 | 4.4E3 | 5.3E3 | 2.0E3 | 1.5E3 | 6.7E2 | 3.6E3 | 9.6E3 | 9.5E3 | 81 | 16 | 81 | 16 | 0.66 |

Figure 32 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jH | ng/ml | 7.6E1 | 1.2E2 | 8.0E1 | 1.2E2 | 5.1E1 | 7.6E1 | 1.3E1 | 1.5E1 | 4.3E2 | 2.4E2 | 81 | 16 | 81 | 16 | 0.66 |
| jI | ng/ml | 6.8E1 | 1.3E2 | 7.6E1 | 1.3E2 | 4.9E1 | 6.3E1 | 1.9E1 | 5.2E1 | 4.4E2 | 2.6E2 | 81 | 16 | 81 | 16 | 0.81 |
| wC | ng/ml | 1.6E0 | 1.3E0 | 2.0E0 | 1.2E0 | 1.4E0 | 4.0E-1 | 6.1E-2 | 5.7E-1 | 6.5E0 | 1.7E0 | 49 | 7 | 49 | 7 | 0.29 |
| wD | ng/ml | 2.2E1 | 2.6E1 | 8.8E1 | 3.1E1 | 3.0E2 | 1.3E1 | 2.8E0 | 1.6E1 | 2.1E3 | 5.4E1 | 49 | 7 | 49 | 7 | 0.58 |
| wE | ng/ml | 4.9E1 | 4.3E1 | 5.1E1 | 4.6E1 | 2.1E1 | 1.5E1 | 8.1E0 | 2.6E1 | 9.4E1 | 6.5E1 | 49 | 7 | 49 | 7 | 0.43 |
| wG | ng/ml | 9.9E-2 | 1.1E-1 | 1.4E-1 | 1.5E-1 | 1.7E-1 | 1.3E-1 | 1.0E-9 | 1.0E-9 | 7.1E-1 | 3.3E-1 | 49 | 7 | 49 | 7 | 0.56 |
| wH | ng/ml | 3.2E-2 | 1.2E-1 | 3.7E-1 | 2.4E-1 | 1.0E0 | 2.3E-1 | 1.0E-9 | 1.3E-2 | 5.6E0 | 5.7E-1 | 49 | 7 | 49 | 7 | 0.70 |
| wF | ng/ml | 1.5E-1 | 8.6E-1 | 2.5E0 | 9.6E-1 | 9.1E0 | 6.0E-1 | 1.0E-9 | 2.7E-1 | 5.7E1 | 2.1E0 | 49 | 7 | 49 | 7 | 0.80 |
| rA | pg/ml | 2.4E1 | 2.7E1 | 3.0E1 | 3.0E1 | 2.8E1 | 2.0E1 | 1.0E-9 | 9.2E0 | 2.0E2 | 7.1E1 | 79 | 15 | 79 | 15 | 0.54 |
| qZ | pg/ml | 5.4E1 | 1.3E1 | 4.7E2 | 9.3E2 | 1.9E3 | 3.0E3 | 2.8E-4 | 6.5E-4 | 1.0E4 | 1.0E4 | 59 | 11 | 59 | 11 | 0.30 |
| qY | pg/ml | 1.5E1 | 2.2E1 | 3.8E1 | 4.6E1 | 5.7E1 | 5.3E1 | 8.7E-1 | 5.6E0 | 3.3E2 | 1.8E2 | 79 | 15 | 79 | 15 | 0.60 |
| qX | pg/ml | 6.0E1 | 7.3E1 | 7.0E1 | 8.4E1 | 4.9E1 | 5.1E1 | 1.0E-9 | 2.3E1 | 2.3E2 | 2.1E2 | 79 | 15 | 79 | 15 | 0.59 |
| qW | pg/ml | 7.7E0 | 7.6E0 | 1.2E1 | 1.0E1 | 1.7E1 | 9.3E0 | 1.0E-9 | 1.0E-9 | 1.2E2 | 3.6E1 | 79 | 15 | 79 | 15 | 0.49 |
| qV | pg/ml | 1.7E3 | 2.2E3 | 2.4E3 | 3.1E3 | 1.8E3 | 2.7E3 | 1.7E2 | 1.0E2 | 9.6E3 | 1.1E4 | 79 | 15 | 79 | 15 | 0.58 |
| qU | pg/ml | 7.3E1 | 1.1E2 | 1.9E2 | 2.2E2 | 3.2E2 | 2.8E2 | 1.0E-9 | 1.0E-9 | 2.1E3 | 1.1E3 | 79 | 15 | 79 | 15 | 0.57 |
| qT | pg/ml | 3.9E1 | 4.6E1 | 6.2E1 | 8.7E1 | 6.7E1 | 8.9E1 | 1.0E-9 | 2.2E1 | 4.9E2 | 3.1E2 | 79 | 15 | 79 | 15 | 0.59 |
| jK | ng/ml | 1.5E3 | 1.5E3 | 1.6E3 | 1.8E3 | 5.7E2 | 8.9E2 | 2.8E2 | 7.0E2 | 3.6E3 | 4.1E3 | 81 | 16 | 81 | 16 | 0.54 |
| jL | ng/ml | 2.0E2 | 2.6E2 | 2.6E2 | 3.2E2 | 2.1E2 | 1.8E2 | 5.6E1 | 1.3E2 | 9.6E2 | 7.0E2 | 81 | 16 | 81 | 16 | 0.63 |
| jM | ng/ml | 6.8E4 | 6.7E4 | 7.5E4 | 7.2E4 | 4.0E4 | 4.1E4 | 4.6E3 | 1.1E4 | 1.8E5 | 1.4E5 | 81 | 16 | 81 | 16 | 0.48 |
| jO | pg/ml | 2.1E5 | 3.2E5 | 2.7E5 | 3.3E5 | 1.7E5 | 1.4E5 | 6.0E4 | 1.3E5 | 1.1E6 | 6.5E5 | 81 | 16 | 81 | 16 | 0.66 |
| jP | pg/ml | 2.5E5 | 3.2E5 | 2.8E5 | 3.6E5 | 1.4E5 | 1.6E5 | 3.6E4 | 1.4E5 | 7.1E5 | 5.8E5 | 81 | 16 | 81 | 16 | 0.65 |
| jQ | pg/ml | 2.3E3 | 2.3E3 | 3.1E3 | 3.3E3 | 2.9E3 | 2.6E3 | 5.0E0 | 6.4E2 | 1.3E4 | 9.2E3 | 81 | 16 | 81 | 16 | 0.55 |
| jR | pg/ml | 5.6E3 | 6.0E3 | 1.0E4 | 1.0E4 | 1.3E4 | 1.1E4 | 1.0E-9 | 1.6E3 | 6.8E4 | 4.6E4 | 81 | 16 | 81 | 16 | 0.56 |
| jT | pg/ml | 1.7E5 | 1.9E5 | 1.7E5 | 1.9E5 | 7.1E4 | 7.0E4 | 7.1E4 | 1.0E5 | 5.5E5 | 3.5E5 | 81 | 16 | 81 | 16 | 0.59 |
| jU | mIU/ml | 5.5E0 | 5.1E0 | 1.2E1 | 1.0E1 | 1.9E1 | 1.4E1 | 8.1E-2 | 3.9E-1 | 1.1E2 | 5.3E1 | 81 | 16 | 81 | 16 | 0.45 |
| jV | mIU/ml | 2.0E0 | 1.2E0 | 4.2E0 | 3.1E0 | 5.9E0 | 3.5E0 | 2.7E-3 | 2.1E-2 | 3.2E1 | 1.0E1 | 81 | 16 | 81 | 16 | 0.45 |
| jY | ng/ml | 7.4E-4 | 2.6E-3 | 8.1E-3 | 4.9E-3 | 3.5E-2 | 7.3E-3 | 1.0E-9 | 1.0E-9 | 3.0E-1 | 2.6E-2 | 81 | 16 | 81 | 16 | 0.59 |
| kC | pg/ml | 9.6E1 | 1.1E2 | 1.7E2 | 2.2E2 | 3.7E2 | 2.6E2 | 2.1E1 | 3.6E1 | 2.7E3 | 1.1E3 | 57 | 19 | 57 | 19 | 0.57 |
| kE | pg/ml | 1.4E5 | 1.4E5 | 1.3E5 | 1.5E5 | 3.8E4 | 4.5E4 | 3.8E4 | 5.1E4 | 2.3E5 | 2.7E5 | 57 | 19 | 57 | 19 | 0.56 |
| kF | pg/mL | 6.0E1 | 7.0E1 | 6.5E1 | 7.9E1 | 2.3E1 | 2.8E1 | 2.7E1 | 5.2E1 | 1.5E2 | 1.4E2 | 57 | 19 | 57 | 19 | 0.67 |
| kG | pg/mL | 8.2E3 | 1.1E4 | 1.1E4 | 2.3E4 | 1.0E4 | 3.6E4 | 1.1E3 | 3.3E3 | 5.8E4 | 1.6E5 | 57 | 19 | 57 | 19 | 0.63 |
| kI | pg/ml | 1.9E2 | 2.1E2 | 2.1E2 | 2.4E2 | 9.9E1 | 1.5E2 | 4.4E1 | 1.0E-9 | 5.5E2 | 6.7E2 | 57 | 19 | 57 | 19 | 0.55 |
| kK | pg/ml | 1.2E2 | 1.5E2 | 1.5E2 | 2.8E2 | 1.5E2 | 4.2E2 | 6.4E0 | 3.4E1 | 9.1E2 | 1.9E3 | 57 | 19 | 57 | 19 | 0.62 |
| kN | pg/ml | 1.0E3 | 1.1E3 | 1.3E3 | 2.3E3 | 9.7E2 | 3.0E3 | 2.1E2 | 7.3E1 | 4.9E3 | 1.0E4 | 57 | 19 | 57 | 19 | 0.55 |
| kO | pg/ml | 7.1E3 | 7.6E3 | 1.0E4 | 7.9E3 | 1.9E4 | 3.6E3 | 3.8E3 | 3.7E3 | 1.5E5 | 1.9E4 | 57 | 19 | 57 | 19 | 0.51 |
| kP | pg/ml | 6.3E3 | 4.9E3 | 7.0E3 | 5.8E3 | 4.3E3 | 4.1E3 | 1.5E3 | 9.6E2 | 2.7E4 | 1.6E4 | 57 | 19 | 57 | 19 | 0.40 |
| kQ | pg/ml | 4.2E3 | 5.3E3 | 5.3E3 | 5.5E3 | 4.3E3 | 2.5E3 | 5.6E2 | 1.5E3 | 2.5E4 | 1.2E4 | 98 | 20 | 98 | 20 | 0.60 |
| kR | pg/ml | 2.2E1 | 2.6E1 | 3.8E1 | 3.0E1 | 1.0E2 | 2.1E1 | 1.0E-9 | 2.9E0 | 1.0E3 | 7.5E1 | 98 | 20 | 98 | 20 | 0.53 |
| kS | pg/ml | 8.7E2 | 9.2E2 | 1.0E3 | 9.6E2 | 5.9E2 | 5.9E2 | 2.5E2 | 8.2E1 | 3.2E3 | 2.5E3 | 98 | 20 | 98 | 20 | 0.49 |
| rZ | ng/ml | 1.0E-3 | 1.4E-2 | 5.7E-3 | 4.6E-2 | 1.3E-2 | 8.3E-2 | 1.0E-9 | 1.0E-9 | 9.4E-2 | 3.0E-1 | 75 | 13 | 75 | 13 | 0.82 |
| rY | ng/ml | 6.2E-2 | 4.7E-2 | 1.8E-1 | 3.0E0 | 7.3E-1 | 7.1E0 | 1.0E-9 | 1.2E-2 | 6.3E0 | 2.0E1 | 75 | 13 | 75 | 13 | 0.53 |
| rX | ng/ml | 1.0E-9 | 1.0E-9 | 7.1E-2 | 4.3E-1 | 4.4E-1 | 1.0E0 | 1.0E-9 | 1.0E-9 | 3.7E0 | 3.1E0 | 75 | 13 | 75 | 13 | 0.53 |
| lK | pg/ml | 5.8E1 | 7.4E1 | 1.4E2 | 1.5E2 | 1.7E2 | 1.9E2 | 1.0E-9 | 1.0E-9 | 7.4E2 | 5.1E2 | 80 | 16 | 80 | 16 | 0.47 |
| lL | pg/ml | 1.6E3 | 3.8E3 | 2.2E3 | 6.3E3 | 2.6E3 | 9.8E3 | 7.5E1 | 6.9E2 | 1.9E4 | 4.2E4 | 81 | 16 | 81 | 16 | 0.77 |
| lM | pg/ml | 1.2E3 | 1.2E3 | 3.7E3 | 1.0E4 | 6.1E3 | 1.9E4 | 2.1E2 | 9.5E0 | 4.2E4 | 6.7E4 | 81 | 16 | 81 | 16 | 0.48 |
| lN | pg/ml | 1.0E-9 | 3.4E0 | 2.8E0 | 6.3E0 | 6.5E0 | 7.6E0 | 1.0E-9 | 1.0E-9 | 4.3E1 | 2.4E1 | 81 | 16 | 81 | 16 | 0.66 |
| lO | pg/ml | 1.0E-9 | 1.0E-9 | 3.7E0 | 1.0E-9 | 2.1E1 | 0.0E0 | 1.0E-9 | 1.0E-9 | 1.4E2 | 1.0E-9 | 80 | 16 | 80 | 16 | 0.48 |
| zA | ng/ml | 2.1E7 | 2.5E7 | 2.1E7 | 2.5E7 | 6.1E6 | 7.1E6 | 9.1E6 | 1.7E7 | 3.4E7 | 3.6E7 | 48 | 7 | 48 | 7 | 0.67 |
| nW | pg/ml | 1.1E5 | 1.2E5 | 1.1E5 | 1.2E5 | 2.9E4 | 2.3E4 | 3.6E4 | 8.4E4 | 1.9E5 | 1.6E5 | 98 | 20 | 98 | 20 | 0.62 |
| nY | pg/ml | 2.2E3 | 3.8E3 | 2.5E3 | 3.7E3 | 1.3E3 | 2.3E3 | 5.1E2 | 1.2E3 | 8.1E3 | 1.0E4 | 98 | 20 | 98 | 20 | 0.67 |
| oO | pg/ml | 9.0E4 | 8.1E4 | 1.0E5 | 1.2E5 | 6.3E4 | 1.1E5 | 3.3E3 | 3.1E4 | 3.0E5 | 4.0E5 | 52 | 17 | 52 | 17 | 0.47 |
| oP | pg/ml | 1.2E5 | 2.0E5 | 1.3E5 | 2.3E5 | 6.5E4 | 1.5E5 | 2.4E4 | 5.0E4 | 3.1E5 | 5.7E5 | 52 | 17 | 52 | 17 | 0.71 |
| oQ | pg/ml | 2.9E3 | 3.8E3 | 3.2E3 | 7.4E3 | 1.9E3 | 8.3E3 | 7.7E2 | 1.4E3 | 1.1E4 | 3.2E4 | 52 | 17 | 52 | 17 | 0.65 |
| oE | pg/ml | 1.6E2 | 5.8E2 | 4.4E2 | 8.9E2 | 5.9E2 | 9.1E2 | 1.0E-9 | 1.0E-9 | 2.8E3 | 3.4E3 | 98 | 20 | 98 | 20 | 0.68 |
| oF | pg/ml | 1.2E4 | 2.8E4 | 2.5E4 | 4.4E4 | 3.5E4 | 5.9E4 | 4.3E2 | 3.5E2 | 1.7E5 | 2.5E5 | 98 | 20 | 98 | 20 | 0.63 |
| oH | pg/ml | 3.6E1 | 3.4E1 | 7.9E1 | 7.1E1 | 1.2E2 | 9.1E1 | 4.3E-1 | 6.3E0 | 8.6E2 | 3.2E2 | 98 | 20 | 98 | 20 | 0.50 |
| oK | pg/ml | 8.4E2 | 1.3E3 | 1.6E3 | 1.7E3 | 2.0E3 | 1.4E3 | 8.8E1 | 2.1E2 | 1.2E4 | 5.9E3 | 98 | 20 | 98 | 20 | 0.56 |

Figure 32 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| oN | pg/ml | 5.4E2 | 5.8E2 | 9.7E2 | 8.7E2 | 2.0E3 | 7.5E2 | 1.1E2 | 2.8E2 | 1.8E4 | 3.6E3 | 98 | 20 | 98 | 20 | 0.59 |
| oW | pg/ml | 2.2E2 | 2.7E2 | 4.0E2 | 1.3E3 | 5.3E2 | 2.4E3 | 2.9E1 | 9.3E1 | 2.7E3 | 7.6E3 | 24 | 9 | 24 | 9 | 0.57 |
| oT | pg/ml | 3.0E2 | 2.5E2 | 3.6E2 | 2.3E2 | 1.9E2 | 7.2E1 | 1.0E2 | 1.1E2 | 7.9E2 | 3.2E2 | 24 | 9 | 24 | 9 | 0.27 |
| oV | pg/ml | 1.4E2 | 7.0E1 | 3.4E2 | 1.0E2 | 5.2E2 | 1.0E2 | 1.1E1 | 1.0E-9 | 2.2E3 | 3.3E2 | 24 | 9 | 24 | 9 | 0.36 |
| oD | pg/ml | 1.5E4 | 1.7E4 | 1.5E4 | 1.6E4 | 5.3E3 | 7.7E3 | 6.6E3 | 8.7E3 | 2.5E4 | 3.2E4 | 24 | 9 | 24 | 9 | 0.49 |
| pF | pg/ml | 5.6E-1 | 6.0E-1 | 1.8E0 | 7.0E-1 | 8.8E0 | 4.6E-1 | 1.0E-9 | 4.3E-2 | 8.7E1 | 1.6E0 | 98 | 20 | 98 | 20 | 0.49 |
| pH | ng/ml | 7.9E0 | 9.9E0 | 8.8E0 | 1.2E1 | 4.0E0 | 7.3E0 | 1.2E0 | 3.0E0 | 1.8E1 | 2.3E1 | 24 | 9 | 24 | 9 | 0.59 |
| pI | ng/ml | 6.9E1 | 7.1E1 | 7.5E1 | 6.7E1 | 4.8E1 | 2.6E1 | 2.3E1 | 3.5E1 | 2.0E2 | 1.1E2 | 24 | 9 | 24 | 9 | 0.52 |
| pK | ng/ml | 4.9E-1 | 4.0E-1 | 4.9E-1 | 3.7E-1 | 2.0E-1 | 1.4E-1 | 2.3E-1 | 1.7E-1 | 8.6E-1 | 6.2E-1 | 24 | 9 | 24 | 9 | 0.34 |

Analyte panel data:

Unconstrained panels with 3 analytes, where 1.0E-10 >= 'model p-value' > 0. Contains 4 panels of 25,049,241 total panels evaluated. : NnIsJj MzNfaA TzHbYg QdJocF Unconstrained panels with 3 analytes, where 1.0E-9 >= 'model p-value' > 1.0E-10. Contains 94 panels of 25,049,241 total panels evaluated. : Is{Jj(Fr Ik Iq Iu Iv Jk Lj Mu Nt Nv On Pc Pg) Nn(aA Ii Iq Iu Jm Jo Oy) Ii(cF Nv On Pg) cF(Dd Jo Jt) NtJo HraA JmNv} Qd{cF(Ad Ax Dd Hr Ii Jt Li Me) Im(aA Iu Jj Lj Nn Pc) Li(Ba cB cT dF) Nn(Il Jj) MmeM NdUm} Nn{Jj(Iv Jl Jq Me Mx Nt Nv Nx On Pg) Oy(Nw On) MzNf} nU{jI(jG jL kF kO IL nC nH nL) IKIL} IL{IK(IX mT mU nT) aAmY mUjD} hR{rZ(jY IO rC)} Tz{Si(Mv Ua)} Jj{IiOn IvPg} Nw{MecF JkOy} PoHraA MuOnOy NdHIJI QaLiUm nTjIkO Unconstrained panels with 3 analytes, where 1.0E-8 >= 'model p-value' > 1.0E-9. Contains 932 panels of 25,049,241 total panels evaluated. : Qd{Im(Ax cF Fp Fr Hq Hr Hv Hw Ih Ii Il In Ip Iq Ir Is It Iv Jh Ji Jk Jl Jm Jn Jo Jp Jr Js Jt Lh Li Lu Lv Lw Lx Ly Ma Mb Mf Mh Ml Mm Mp Mq Mt Mu Mv Mx Mz Na Nc Nd Nf Ni Nj Nl Nq Ns Nt Nu Nv Nw Nx Og Oh Ok On Oz Pa Pd Pf Pg Po Qc) cF(Aa AS aZ Ba Bb bN Bo cB cL Cp Cq Cs CU Cw Dc Dl Hb Hv Hw Ij In Iq Ir It Iu Iv Jh Ji Jm Jn Jr Js Ko Lh Lj Lu Lv Mj Mm Mr Mt Mw Na Nb Nd Nf Ng Nm Nn Nr Ns Nx Ny Of Oh Om Oy Oz Pb Pc Pd Pe Pj Po Qa Qe Um Uo) Li(aA aF aK aL aO aP aS aU aZ bA bF bL bN BO bQ bS bV cG eK cL cN cQ cU cY Dd De dJ Gl Gp Nn Tz Um Wm) Ax(aK aP aS aU aZ BA bL bN bO bV cB cK cL cT cU cY De dF Hr Iv Lu Ma Me Nd Nf Ns Tr Tt) cB(bN Dd Hr Hw Ii Iu Jm Jo Jt Lh Lu Mm Ns Pd) Jj(aA Ik Il Is Jk Lj Mu Nt Nv Nx On Pc Pg) Nn(aA Ii Ik Is Iu Iv Jm Jo Jt Lj Me Oy) Il(aA Fr Is Iv Jk Lj Ma Nv On Pc) Lu(Ad As aU aZ bL Cq Cs Dd Ha) Ik(aA Fr Is Iu Iv Jo Ma Nv Pc) Ii(aU Ba cL dF Is Nv On) Jo(aU Ba Bg cL De Nv) Nd(Ha Hb Hl Rm Wm) aA(Hr Iu Lj Ma Pc) Ba(Ad Hb Jt Mm) Um(Hb Lj Mv Nj) Bg(Ad Mm Oy) Hr(Bb De Hb) Is(Dd Iu Jm) Lh(aO cL dF) cT(dX eM eP) Mm(Bo Dd) GpHb NsbN MrdF UyeM} Is{Jj(aA Et Fp Hq Hr Hu Hv Hw Hx Ih Ii Ij Il Im In Io Ip Ir It Jg Jh Ji Jl Jm Jn Jo Jp Jq Jr Js Jt Lh Li Lu Lv Lw Lx Ly Lz Ma Mb Mc Md Me Mf Mg Mh Mi Mj Ml Mm Mn Mp Mq Ms Mt Mv Mw Mx My Mz Na Nb Nc Nd Ne Nf Ng Nh Ni Nj Nk Nl Nm No Nq Nr Ns Nu Nw Nx Ny Oe Of Og Oh Oi Ok Om Oy Oz Pa Pb Pd Pe Pf Po Pz Qa Qb Qc Qe) Jm(aA Fr Hr Ii Im In Iq Iu Iv Jk Jl Jo Jt Lj Lx Ma Mb Ml MU Mx Nc Nd Nj Nk Nl Nq Ns Nt NU Nw Of On Pa Pc Pg Po Pz Qa Qe Yi) aA(Hw Ih Ii Ij Ik Im In Iq Iu Iv Jo Jt Li Lj Lv Ly Ma Mb Mu Mx Nd Nf Nj Nl Nt Nv Nw Of Og Oz Pc Pg Po) Nn(Hr Ih Il Im In Iv Jt Lh Li Lj Mb Me Mg Mw My Ng Ni Nj Ns Nt Of Og Oi Oz Pz Qb) Iu(Fr Ii Il Im In Iq Iv Ma Mb Mx Nl Nt Nu Nv Og On Pc Pg) Jo(De Fr Iq Iv Jl Lj Ma Nv Ok On Pc Pg Po) Ii(De Fr Iv Ji Jk Jl Nt Nw Pc Po) cF(Aa Ad Cq Fr In Ir Um Uo) Um(Hb Lj Mv Nd) Dd(De Lu Me) In(Iq Iv Nt) On(Jt Of Oy) Ad(De Lu) Mu(My Oy) Iq(Fr Ly) Yi(Ju Sf) Yl(Ju Sf) AaMe AwdX CqLu DeHr NtJt MzNf NvNx} Jj{On(aA Hq Hr Ik Im Iq Iu Iv Jk Jl Jo Jt Lh Li Lj Lv Mb Mm Mr Mu Mx Nb Nf Nj Nl Nm Ns Nt Nv Nx Of Oy Oz Pc Pe Pg Po) JI(aA Hr Ii Ik Im Iv Jk Jq Lj Ma Mb Mu Mx Nj Nl Ns Nt Nu Nv Nx Pc Pg) Nn(aA Ik Im Jh Ji Jk Jp Lv Lx Nj Nl Nu Nw Ok Po Qa) Pg(aA Hq Ik Im Jk Jq Mu Mx Nj Nt Nu Nv Nx Pe Pf Po) Nt(aA Im Iv Jk Jq Ly Mu Mx Nd Nv Nx Po) Nv(aA Hq Ik Im Iv Lh Mb Mx Nj Nu Nx) Iv(aA Fr Jk Jq Mu Nx Po) Mu(kK mE nO nR) Jk(aA Ji Nx Oy) Mx(aA Nx) Ut(dX eP) PoaA UaeP HunR} aA{Nn(Hr Ik Im Iv Jh Ji Jl Jq Lv Lx Ma Mb Me Mj Mx Mz Nf Nj Nl Nt Nv Nw Nx Ok On Oy Oz Pg Po) Hr(Iv Ji Jl Jq Lv Mx Mz Nv Nw Ok On Pg) Mb(Ji Jl Jq Mx Nd Nv On Pc Pg) Iv(Ma Mx Nv Pc Pg) Nj(Ma Mx Nd Nv) Jo(Nt On Pg Po) Ma(Mx Nv) Mu(My Oy) Ii(On Pg) PoLi NtLy MxPc NfNw HqNv OfOn PePg eDnU mUIL} On{Ii(eP Iv Jl Mx Nn Oy Pg Po) Jo(Iv Mb Mx Nn Nt Oy) Oy(Iv Jk Lj Mb Mx) Nn(Mw My Ng) Mu(Mw My) Iz(dX eP) YjOk KsdX RmeP} Jo{Nn(Iv Ji Jl Jq Nt) Cu(cF Me Yg) Nt(Jl Jq) Ma(kl mU) UteP} eP{Ut(aO bA Jp Ug Ur) Kq(aO Ax Ii Ik) ImVo HcKx} Um{Nd(Jq Mz Oh Qa Tn Tz) Qa(Ax Lj) MvMz} Tz{Si(Co Hu Uf Yg) AaIN HbYh} Nn{Nw(Mw My) Oy(Jl Nv) ImIv} Mz{Nf(Im Mu Nq Nv) AdcF} Cu{nI(Dg Jt Nm) NbYi} dX{Im(Qz Vo) IiKq OuPe} eM{Uy(Hv Ut) UaLp TvXa} hR{rZ(hA hX jG qW)} Mu{Nw(My Oy) NvOy} Yl{Or(Hu Mv) HbNw} Nd{HIPe OaUy} Ji{IiJl NvNx} oO{TncT bAfR} BoGzgW GdHqkN RgeDnY nBIKIL Unconstrained panels with 3 analytes, where 1.0E-7 >= 'model p-value' > 1.0E-8. Contains 7,173 panels of 25,049,241 total panels evaluated. : Qd{Ax(aA aC AD aE AF aG aH al aJ AL aM AN AO Ap aQ AR As aV AW aX aY BB BC bE bF BG bH bl bJ bM Bn Bo bP bQ bR bS bU bW bX bZ cA cC cD cE cG CH cl cJ cM cN CO CP CQ cR CS Ct Cu CV CW CX cZ dA DB DC DD dE DG dH Dl dJ DK DL dM dN Et Fp Fr Gp Hb Hq Hu Hv Hw Hx Ih Ii Ij Ik Il In Io Ip Iq Ir Is It Iu Jg Jh Ji Jj Jk Jl Jm Jn Jo Jp Jq Jr Js Jt Lh Li Lj Lv Lw Lx Ly Lz Mb Mc Md Mf Mg Mh Mi Mj Mk Ml Mm Mn Mp Mq Mr Ms Mt Mu Mv Mw Mx My Mz Na Nb Nc Ne Ng Nh Ni Nj Nk Nl Nm Nn No Nq Nr Nt Nu Nv Nw Nx Ny OE Of Og Oh Oi Ok Om On Oy Oz Pa Pb Pc Pd Pe Pf Pg Po Pz Qa Qb Qc Qe Qv Rf Ue Um Wm) cF(aA aC aD aE AF aG aH al AJ aK AL aM AN AO AP aQ AR aS aV AW aX aY bA bB BC bE bE bF BG bH bl bJ bM Bn BO bP bQ bR bS bU bV bW bX bZ cA cC cD cE cG CH cl cJ cK cM cN CO cP cQ cR cS CT CV cW CX cY cZ dA DB dC dD DE dF DG dH Dl dJ DK dL dM dN Ef Et Fp Fr Gp Ha Hq Hu Hx Id Ih Ik Il Io Ip Is Je Jg Ji Jk Jl Jp Jq Jv Kd Ke Kf Kj Kn Kq Kr Lw Lx Ly Lz Ma Mb Mc Md Mf Mg Mh Mi Mk Ml Mn Mp Mq Ms Mu Mv Mx My Mz Nc Ne Nh Ni Nj Nk Nl No Nq Nt Nu Nv Nw Oe Og Oi Ok On Pa Pf Pg Pz Qb Qc Rj Tv Tz Uc Ud Ue Ul Up Ur Us Vp Vt Vv) Lu(aA aC aD aE AF aG aH al AJ aK AL aM AN AO AP aQ AR aS aV AW aX aY BA BB BC bE bF BG bH bl bJ bM BN BO bP bQ bR bS bU bV bW bX bZ cA cC cD cE cG CH cl cJ cK cL cM cN CO CP cQ cR cS CT CU CV CW CX cY cZ dA DB DC dD DE dF DG dH Dl dJ DK DL dM dN Fn Gp Hb Id Ik Il Je Ju Kn Ko Kr Nn Tj) cB(Aa aC AD aH aK Al aN aO Ap aR AS aU aX aZ BA BB Bc bF BG bL Bn BO bP bV bW cH cK cL Co Cp Cq cR Cs cT CU Cw cZ Dc De DG dJ Dl Et Fp Hb Hv Hx Ij Im In Iq Ir It Iv Jh Jj Jn Jp Jq Jr Js Lj Lv Ly Ma Mb Me Mj Ml Mn Mp Mr Mt Mv Mw Mx Mz Na Nb Nd Ne Nf Ng Nh Nk Nm Nn No Nr Nv Nw Nx Ny Oe Of Og Oh Oi Ok Om Oy Oz Pa Pb Pc Pe Pg Po Pz Qa Qe) Li(aC

Mf Mq Mt Mu Na Nd Nf Nj Nl Nu Oz Pc) Im(Fr Hq Hr Hw In Iq Iu Jh Jj Jk Jm Li Lj Lw Lx Mf Mu Nd Nf Nj Nl Nu Nx Oz Pa Pc) Nj(Fr Hr In Ip Jh Jj Jk Jp Lx Ly Mf Mj Mp Mt Mu Mz Ni Nq Nu Oz Pa Pc) Hr(Et Fr Ij Ik Ip Jh Jk Lw Lx Mf Mj Mq Mt Mu Nl Nu Nx Pa Pc Qa) Pc(Ij Ik Jh Jj Jk Jp Lx Mj Mq Mt Mz Nl Nu Nx Ok Oz) Lx(Ik In Iu Jh Jj Jk Jo Li Lj Mf Mu Nd Nl Oz) lL(hR kK kP lY mE mP mS nA nI nN nO nT nU) Jj(Fr Ij Ik Jh Mf Mj Mt Mu Nl Nu Nx) nU(hR hV hW hX rB rC rX rY rZ) Jk(Hq Ii Jm Nd Ng Nl Og Oy) Nl(Fr Jh Ly Mu Mz Nd) Hw(Ij Lw Mz Ok Qa) nR(hW rX rY rZ) Mu(Jh Mw Ng) hR(eD lN rZ) Mz(Ij In) Nd(Ik Mp) Nf(Mt Ok) JoOk mWrZ} Is{Iu(Et Fp Hq Hr Hu Hv Hw Hx Ih Ij Ik Io Ip Ir It Jg Jh Ji Jk Jl Jn Jo Jp Jq Jr Js Jt Lh Li Lj Lu Lv Lw Lx Ly Lz Mc Md Me Mf Mg Mh Mi Mj Mk Ml Mm Mn Mp Mq Mr Ms Mt Mu Mv Mw My Mz Na Nb Nc Nd Ne Nf Ng Nh Ni Nj Nk Nm No Nq Nr Ns Nw Nx Ny Oe Of Oh Oi Ok Om Oy Oz Pa Pb Pd Pe Pf Po Pz Qa Qb Qc Qe Um) Jm(Aa Ad As Cq Cu Cw Dd Et Fp Hq Hu Hv Hw Hx Ih Ij Ik Il Io Ip Ir It Jg Jh Ji Jn Jp Jq Jr Js Kr Lh Li Lu Lv Lw Ly Lz Mc Md Me Mf Mg Mh Mi Mj Mk Mm Mn Mp Mq Mr Ms Mt Mv Mw My Mz Na Nb Ne Nf Ng Nh Ni Nm nN No NR Nx Ny Oe Og Oh Oi Ok Om Oy Oz Pb Pd Pe Pf Qb Qc Um Uy Uz Vi Wg Yl) Jo(Ad aF Al aO As Aw Ax Ba bR bU bV cA cB cL Cq cS cU Dd dF Di dJ Et Hr Hw Ih Ii Ik Il Im In Ip It Jg Jh Ji Jk Jp Jq Jt Lh Li Lu Lv Lw Lx Ly Mb Md Me Mg Mh Mi Ml Mm Mp Mq Ms Mt Mu Mv Mx Mz Nc Nd Ne Nh Ni Nj Nk Nl No Nq Ns Nu Nw Nx Oe Og Oh Oi Oz Pa Pz Qa Qb Qc Qe Um) Nn(Dd Et Fp Fr Hq Hu Hv Hw Hx Ij Ik Io Ip Ir It Jg Jh Ji Jk Jl Jn Jp Jq Jr Js Lu Lv Lw Lx Ly Lz Ma Mc Md Mf Mh Mi Mj Mk Ml Mm Mn Mp Mq Mr Ms Mt Mu Mv Mx Mz Na Nb Nc Nd Ne Nf Nh Nk Nl Nm No Nq Nr Nu Nv Nw Nx Ny Oe Oh Ok Om On Pa Pb Pc Pd Pe Pf Pg Po Qa Qc Qe Um) Ii(Aa aO aR Ax bR bU bV cB Dd dX eP Et fR Hr Hw Ih Ik Il Im In Ip Iq It Jh Jp Jq Lh Lj Lu Lv Lw Lx Ly Ma Mb Md Me Mg Mh Mi Mj Ml Mm Mp Mq Ms Mt Mu Mv Mx Mz Nc Nd Ne Ni Nj Nk Nl No Nq Ns Nu Nx Oe Of Og Oh Oi Ok Oz Pa Pb Pz Qa Qb Qc Qe) Iq(Aa Et Hr Hw Ih Il Im It Iv Jh Ji Jk Jl Jp Jq Jt Lh Lj Lu Lv Lw Lx Ma Mb Mg Ml Mp Mq Mt Mu Mx Mz Nd Nh Ni Nm Nq Ns Nt Nu Nv Nw Oe Of Og Oh Oi Ok On Oy Oz Pa Pc Pg Po Pz Qb Qe) In(Ad Al Ax bU cB Dd De Fr Hb Hr Ik Il Im It Jh Ji Jl Jt Lh Lj Lv Lw Ly Ma Mb Mg Mp Mq Mu Mx Mz Nd Nj Nl Nm Ns Nu Nv Nw Of Og Oh Ok On Oz Pc Pg Po Pz Qa Qb Qc Qe) Hr(aC Ad Al aR Ax Bb bR bU bV cA cB cU Dd Fr Hb Im Iv Ji Jl Lj Mu Mx Mz Nt Nv Nw Ok On Pc Pg Po Pz Wm) Og(Fr Ih Ik Im It Iv Jh Jk Jl Jt Lj Ly Ma Mb Mu Mx Nd Nj Nq Ns Nt Nu Nv Nw Oh On Oz Pc Pg Po Pz Qb) Dd(aC aR Ax Bo bU bV cA cB cH Di Im Iv Js Lh Li Lj Ly Mb Mm Mu Mv Nb Nd Nh Nm Ns Oz Pb) cF(As Bo Cp Cw Hv Hw Ij It Jn Jr Js Kr Mc Mr Na Nf Pb Uc Ud Ul Up Us Vp Vv) Fr(Hq Il Im Iv Jt Lh Li Lj Ly Mb Mg Mx My Ng Nm Ns Nx Ny Of Oy Pz Qb) Iv(Ih Il Im It Jt Lj Ly Ma Mg Mu Mx Nd Ns Nv Nw Of Oi On Pc Pz Qb) Nv(Hq Hw Il Im Jt Lh Li Ly Mb Mg Mx My Ng Ni Ns Of Oy Pz) Aa(Al aO aS Ax aZ bA bR bU bV cA cB cC De dJ Gp Ih) Nt(Il Im It Lh Li Lj Ly Mg Mx Nd Ng Nm Of Oi Pc Pz) Ax(Ad As Cq Cw Hv Hw Ij Ir Jn Jr Me Nf Pb Um) Pc(Im Jt Li Lj Mb Mg Mx My Ng Ni Of Oy Pz) On(Lh Li Mb Mg My Nb Ng Nm Nx Ny Po Pz) Mx(Ih Im Ir Jr Js Jt Lj Ma Mb Ns) Nw(Im Jt Lj Mh My Nf Nx Ny Oy Pb) Um(aR Ju Li Ly Ml Mu Nj Qy Rm Ub) Pg(Il Im Jt Lh Ly Mg Of Oy Pe Pf) Ad(bU cB Me Mm Mu Mv Uy Wd Wh) Lj(Il Im Ly Mb Nd Of Oy rY) nU(jH jI lL qT qU qV qW qY) Hb(Up Vp Yg Yh Yi Yj Yl) Jt(cB De Et Jh Ji Jp Ok) Mb(Im It Ly Ml Nd Ok) Cq(De Me Mm Mu Ns) Gb(Dc Hu mY Yg Yl) Lu(As Cp Cu Cw Yl) Ir(Al bU cB De Mz) Mm(Bo dX eM eP) Nd(Hl Rm Up) Yj(Et Ju Sf) Ok(Hw Ij Nx) Uy(bO Ju Sf) De(Hw Nf) Ma(Mg Of) Me(As Cw) Ng(Jk Mu) Yi(Bn Si) Jj(Mk Mr) Oy(Jk Nq) lL(mU nA) AweP DrdX PoLi EtYl NsIm NuLy MzIj NiNk HlIW SiUo PzJp JiNx UweM nRqV} Jj{Pg(Et Fp Fr Hr Hu Hv Hw Hx Ih Ii Ij Il In Io Ip Iq Ir It Iu Jg Jh Ji Jm Jn Jo Jp Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mv Mw My Mz Na Nb Nc Nd Ne Nf Ng Nh Ni Nk Nl Nm No Nq Nr Ns Nw Ny Oe Of Og Oh Oi Ok Om Oy Oz Pa Pb Pc Pd Pz Qa) Jl(Et Fp Fr Hq Hu Hv Hw Hx Ih Ij Il In Io Ip Iq Ir It Iu Jg Jh Ji Jm Jn Jo Jp Jr Js Jt Lh Li Lu Lv Lw Lx Ly Lz Mc Md Me Mf Mg Mh Mi Mj Mk Ml Mm Mn Mp Mq Mr Ms Mt Mv Mw My Mz Na Nb Nc Nd Ne Nf Ng Nh Ni Nk Nm No Nq Nr Nw Ny Oe Of Og Oh Oi Ok Om Oy Oz Pa Pb Pd Pe Pf Po Pz Qa Qb Qc Qe) Nv(Et Fp Fr Hr Hv Hw Hx Ih Ii Ij Il In Io Ip Iq Iu Jh Ji Jk Jm Jn Jo Jp Jq Jr Js Jt Li Lj Lu Lv Lw Lx Ly Lz Ma Mc Md Me Mf Mg Mh Mj Ml Mm Mn Mp Mq Ms Mt Mu Mv My Mz Na Nb Nc Nd Ne Nf Ng Nh Ni Nk Nl Nm Nq Ns Nw Ny Oe Of Og Oh Oi Ok Om Oy Oz Pa Pb Pc Pd Pe Pf Po Qa Qb Qc) Nt(Fr Hq Hr Hu Hv Hw Hx Ih Ii Ij Ik Il In Io Ip Iq Ir It Iu Jh Ji Jm Jn Jo Jp Js Li Lj Lu Lv Lw Lx Lz Ma Mb Mc Md Mf Mh Mj Ml Mp Mq Ms Mt Mv My Mz Na Nc Nf Ni Nj Nk Nl Nm No Nq Nr Ns Nu Nw Ny Oe Og Oh Oi Ok Om Oy Oz Pa Pb Pc Pd Pe Qa Qb Qc) On(Et Fp Fr Hu Hv Hw Hx Ih Ij Il In Io Ip Ir It Jg Jh Ji Jm Jn Jp Jq Jr Js Lu Lw Lx Ly Lz Ma Mc Md Me Mf Mg Mh Mi Mj Mk Ml Mn Mp Mq Ms Mt Mv Mw My Mz Na Nc Nd Ne Ng Nh Ni Nk No Nq Nr Nu Nw Ny Oe Og Oh Oi Ok Om Pa Pb Pd Pf Pz Qa Qb Qc Qe) Nn(Et Fp Fr Hq Hr Ih Ij Il In Io Ip Iq Ir It Jg Jn Jo Jr Js Lh Lj Lu Lw Ly Ma Mb Md Mi Mj Ml Mp Mq Mr Ms Mt Mu Mv My Mz Nb Nc Nd Ne Nf Nh Ni Nk No Nq Nr Ns Ny Oh Oi Oy Oz Pa Pd Pe Pz Qb Qc Qe) Mu(Im Ji Jq kC kE kF kG kI kN kO kP lW lX lY mF mH mI mM mP mS mT mU mW Mx mY mZ nA nB nC nD nF nH nI nJ nK nL nM nN nT nU Nx Po) Jk(Ih Im Jq Js kF kG kK Lv Lx Ma Mb Mx Ng Nj Nl nO nR NU Nw Oh Ok Po Qa) Mx(Fr Ik Im Iv Jh Ji Jp Jq Lv Lx Ma Nj Nq Nu Nw Pc Po) Iv(Im Jh Ji Lv Lx Ma Mp Mt Nd Nq Nu Nw Oh Ok Pa Pc) Po(Hr Ih Ik Im Jh Ji Jq Lj Ml Nd Nl Ns Nu Nx Pc) Nx(Fr Il Im Jh Lv Lx Ma Nd Nq Nu Qa Qb) Im(Fr Jq Lj Lv Pc) Yg(kG kP mI mW nI) Fr(Ji Jq Nl) Tn(dX eM eP) lL(mT mU nU) Hu(kN nU) Ik(Jq Nw) NuJq MamU MecF MhNw MvkK MzNf} nU{eD(Fp Fr Hq Hr Hw Hx Ih Ii Im In It Jg Jk Jl Jn Js Li Lx Me Mj Mq Mu Mv Mw Mx Nf Ng Nn Nv Ny Oe Of On oP oQ Oy Oz Pb Pc Pe Pf Pg Po Pz Qa Qb Qc) oQ(hA hR hV hW hX iB iC jD jE jF jG jH jI jK jL jM jO jP jQ jR jT jU jV jY lK lL lM lN lO qT qU qV qW qX qY rA rB rC rX rY rZ) Mq(hA iB iC jD jE jF jG jH jI jK jL jM jO jP jQ jR jT jU jV jY lK lL lM lN lO qT qU qV qW qX qY rA) Mx(hA iB iC jD jE jF jG jH jI jK jL jM jO jP jQ jR jT jU jV jY lK lL lM lN lO qT qU qV qW qX qY rA) lL(Fp Hx Im In Ji Jo Jq Lh Li Lj Lx Lz Mj Ml Mp Mv MW Nf Nq Nw Ny Oh Pa Pe Pf Qa Qb) Pe(hA iB jD jF jG jK jL jM jO jP jQ jR jT jU jV jY lK lN qT qU qV qX qY rA) Fp(hA iB jD jE jF jG jI jK jM jO jP jQ jR jU jV lK lM lN qU qW qX qY rA) Qb(hA iB iC jD jG jH jI jL jM jO jP jQ jT jU jV jY lM qT qU qV qW qY Xa) jI(hR hX iC lm kG kI Lz Mb Me Mf mI Mj Ml mS nO Nw Oi Pf Qa rX) Qa(hA iB jD jG jK jL jM jQ jR jT jY lK lM lN qW qX rA) Me(hA iB jE jF jK jM jO jQ jR jU jV qT qW qX rA) Mj(jD jE jF jG jH jL jM jP jT jU lM qU qV qY) rZ(hR jD jH kC kF kK lK mW nT oP rY) oP(hR jD jH jK jR lN qU qW rB) Nw(jH jQ qT qU qV qW qX qY) hR(jD jH jT mW nT qY) lM(Ij Jq Lh Nq Ny Po) Nq(jE jF Mm qY) Lz(Oz Pb qU) Im(jK jP jV) Ny(jG lK qT) Pd(jF jM jV) Po(jE Wh) Mv(My Oy) Nf(jF jM) Wd(Jr Lx) Jo(Ma Vv) Jq(jP qY) Oh(Jm qV) rC(jD jH) AjYg CuGb MbjM MlqU MwjE NhiB NijU TzXa HqOy SfPg WhJr JsjD LijF PfjH mWhV} On{Oy(Fr Hq Hr Hu Hv Hw Ih Ij Ik Im In Ip Iq Ir Iu Jh Jl Jm Jt Lh Li Lv Lx Ly Ma Md Mf Mi Ml Mq Mr Mt Mv Na Nb Nc Nd Nf Nh Ni Nj Nl Nm No Nq Nr Ns Nt Nu Nv Nw Nx Of Om Oz Pa Pb Pc Pd Pe Pg Po Qa) Ii(Ih Ik Im Ip Ji Jk Jo Jq Jt Lh Lv Mb Me Mg Mh Mj Mm Mq Mu Mw My Nc Nd Ng Ni Nj Nk Nl Nm Nt Nu Nv Nw Nx Of Og Oh Oz Pa Pc Pe Qa Qb) Jo(Ik Im Ip Iq Iu Ji Jk Jl Jm Jq Js Lh Li Lj Lv Ma Me Mh Mm Mq Mu Mw My Nd Ng Ni Nj Nl Nm Ns Nu Nv Nx Oe Of Og Oh Ok Oz Pc Pg Po) Of(Hq Hr Im In Iq Iu Iv Jm Jt Lh Li Lv Ma Mb Mm Mn Mw Mx My Ng Ni Nj Nl Nm Nn Ns Nt Nx Og Oz Pg) Iv(Hr In Iu Jm Jt Lh Li Mg Mx My Nb Ng Nm Nn Og) Nn(Im Iu Jm Jt Lh Li Mb Me Mg Mx Nm Og) My(Hr Hw Lj Mb Mr Mv Mx Nf Nr Nw Nx Pe) Mb(Lh Ly Mg Mx Nd Ng Nm) Mm(dX EM eP fR Yj) Mx(Iu Jm Jt Li Nb Po) Nd(eP Hl Um Yi) Ng(Jk Lh Mu Nm) Fy(dX eP) Hr(Dg Wm) mU(jE lL) AaYi GbYj MzNf OwVh UtnI cUeP nNlL} Nn{Iv(Hr In Iu Jh Ji Jl Jm Jp Jq Lv Lx Ly Ma Mb Me Mg Mx My Mz Nd Ng Nj Nl Nt Nv Nw Og Oi Ok Oy Oz Pa Pg Po) Im(Iu Ji Jl Jm Jo Jp Jq Lv Lx Mb Me Mx Nj Nl Nt Nv Nw Oy Oz Pg) Mx(In Jh Ji Jl Jm Jo Jp Jq Lv Ly Mb Me Nt Nw Og Ok Oy Pg) Jl(Hr Ii Iq Iu Jm Lh Li Mb Me Mg My Ng Nj Og) Ji(Ii Iu Jm Lh Li Mb Me My Nf Ng Oy Oz Pd) Nv(Hq Ii Jo Lh Mb Me Mw My Ng Of) Ok(Hr Hw Jo Mb Me Nf Nm Om Oy Pd) Nt(In Jm Ly Me Mg Nd Ng Oy) Oy(Jk Jq Lv Lx Me Pg Po) Me(Jp Jq Lx My

Jr Js Lj Lu Lw Lx Ly Lz Mc Md Me Mf Mg Mh Mi Mj Mk Ml Mp Mq Mr Ms Mt Mu Mv Mz Na Nb Nc Nd Ne Nf Nh Nk No Nq Nr Nu Nv Nw
Ny Oe Oh Oi Ok Om Pa Pb Pc Pd Pe Pf Po Pz Qa Qb Qc) Iv(Fp Fr Hq Hu Hv Hw Hx Ij Ik Il Im Io Ip Iq It Jg Jh Ji Jk Jl Jq Lj Lu Lv Lw Lx Ly
Ma Mb Md Me Mh Mk Ml Mm Mn Mp Mq Mr Ms Mt Mu Mv Mw Mz Nd Nf Ni Nj Nl Nr Ns Nt Nu Nv Nw Nx Ny Oe Oh Oi Ok Om Oz Pa
Pb Pc Pd Pe Pf Pg Po Pz Qb) Jo(cB cF Cu dX eP Et Fp Fr Hq Hr Hu Hv Hw Hx Ih Ij Il In Io Ir It Jg Jh Jn Jp Jr Jt Lu Lw Lx Ly Lz Mc Md Mf
Mg Mi Mj Mk Ml Mn Mp Mr Ms Mt Mv Mz Na Nb Nc Ne Nf Nh Nk No Nq Nr Nw Ny Oi Om Pa Pb Pd Pe Pf Pz Qa Qb Qc Qe Yl) Ii(dX Et
Fp Fr Hq Hr Hu Hv Hw Hx Ij Il In Io Iq Ir It Iu Jg Jh Jm Jn Jp Jr Js Li Lj Lu Lw Lx Ly Lz Ma Mc Md Mf Mi Mk Ml Mn Mp Mr Ms Mt Mv Mz
Na Nb Ne Nf Nh No Nq Nr Ns Ny Oe Oi Ok Om Pb Pd Pf Pz Qc Qe Vh Yg Yl Yf) Ng(Fr Hq Hr Hw Ik Im In Ip Iq Iu Jh Jl Jm Jt Li Lj Lu Lv
Lw Lx Ly Ma Me Mf Mg Mh Ml Mm Mn Mp Mq Mr Ms Mt Mv Mw Mx Nb Nc Nd Ne Nf Nh Ni Nj Nl Nq Ns Nt Nu Nv Nw Nx Ny Oe Og Oh
Oi Ok Oy Oz Pa Pc Pe Pg Po Pz Qa) Mx(Fp Fr Hq Hr Hu Hv Hw Ij Im In Ip Iq Ir Ji Jl Jn Jr Js Lh Lj Lv Lw Ly Ma Me Mg Mh Mk Ml Mm Mn
Mp Mq Mr Ms Mu Mw Na Nd Nf Ni Nj Nl Nm Ns Nt Nu Nv Nw Nx Ny Oe Og Oh Oi Om Oz Pc Pd Pe Pf Pg Pz) Nm(Hq Hr Hw Im In Ip Iq Iu
Jh Ji Jl Jm Jq Jt Lh Li Lu Lv Lx Ly Ma Me Mg Mk Mn Mq Ms MU Mw Nd Ni Nj Nl nR Ns Nt NU Nw Nx Oe Og Oh Oi Ok Om Oz Pc Pd Pg
Po) Jt(cP Hq Hr Im Ip Iq Iu Jh Ji Jl Jm Jq Js Lh Li Lv Lw Ly Ma Mb Me Mg Mm Mn Mp Mq Mw Mz Nd Ni Nj Nl Ns Nt Nu Nw Nx Oe Og Oh
Ok Oz Pc Pg Po Qa Yj Yl) Jm(eP Hq Hr Ih Im In Ip Iq Ir Jl Jq Lh Li Lv Lw Ly Ma Mb Md Mg Mm Mn Mq Mu Mw Nd Ni Nj Nl Nt Nu Nv Nw
Nx Og Oh Oi Oz Pc Pg Po Pz Qa Qb Wg) Mb(Fr gV Hq Hr Im In Ip Iq Iu Jg Jh Ji Jl Li Lj Lw Mc Mk Ml Mm Mn Mp Mu Mw Mz Nb Ni Ns Nv
Nx Ny Oe Og Oh Oi Ok Oz Pc Pg Po Pz) Oy(Et Fp Hx Il Io It Jg Ji Jn Jp Jq Jr Js Lu Lw Lz Mc Me Mg Mh Mj Mk Mm Mn Mp Ms Mw Mz Ne
Nk Ny Oe Og Oh Oi Ok Pf Pz Qb Qc Qe) Mg(Fr Hq Hr Ik Im In Ip Iq Iu Jl Lh Li Lj Lv Ly Ma Mm Mq Mu Mw Nd Ni Nj Nl Ns Nt Nu Nv Nx
Oe Og Oh Oz Pc Pg Po) Lh(Hq Hr Im In Ip Iq Iu Ji Jl Jq Lv Ly Ma Mn Mw Nd Ni Nj Nl Ns Nt Nv Nw Nx Oe Og Oh Oi Oz Pc Pg Po Pz Qa
Vh) Hr(aC Ad Ap Ax aZ Bb cB cF De gV Im Iu Ji Jl Jq Mm Mw Mz Nb Ni Nj Nl Nt Nv Ok Pg Po Pz Qa Tz Um) Im(gV Hq In Iq Iu Jl Li Lv Ly
Mm Mw Nb Nd Ni Nj Nl Ns Nv Nw Nx Og Oh Oz Pc Pg Po Pz) gV(aC bA bW cA cO dB dH dX eP Hq Hw Ik Iu Jj Mm Ms Nd No Ns Og Pe
Po Qe) Og(Hq Iq Iu Jk Jl Li Mm Mu Nb Nd Ni Nj Nl Ns Nt Nv Nw Oz Pc Pg Po) Iu(Hq Jl Lv Ma Mm Mn Ni Nj Nl Nt Nx Pg Po Qa) Vh(Gb
Hb Hp Ib Ih Kq Ks Ma Nd Ny Oh Si) Yj(Aa Bb Hb Jg Nd Oh Ow Pj Rc Uh Zq) eP(Ad Aw bO cD cl Jj Kf Mc Vo Ti Th) Nx(cF Ji Jl Jq Lv Mm
Nv Nw Ok Pg) Nd(Du dX Iq Nj Nl Nt Ru Ry) Mm(Bo Iq mU Nj Nl nU Um) Yi(Ad bU cF Hb Hv Ki Oh) dX(Ha Jj Kf Pe Vo Ti Th) Gb(Ad Gn
Hl Um Yg Yl) Nt(Hq In Li Ly Nb Po) Nb(Ji Me Mz Ni Qa) Ad(Ry Si Yg Yl) Ly(Iq Nj Nl Nu) Tn(fB oT oW pK) Po(Jl Li Pg) Ni(Nj Nk Nl)
Qa(Hw Ij In) Nw(Mh Ny Pb) nU(jE IL lM) mU(Uw Uy Zq) Mz(Ij In) Hq(Nv Pg) Li(Nl Pc) Um(Si Tz) Ut(lX lY) nT(jE IL) jG(Gz mH) AaZw
MecF MwPc HlOk NypK PfPg] Tn{fB(aF Al An Ap Ar aU Ax Bb bG cl cJ cM cN cQ Cs Ct cU dB Dc Dg Dk dN Ed Et Ez Fb Fp Fy Gl Hb Hc
Hq Hw Hx Id Ii Im In Ir Jh Ji Jl Jp Jq Js Jt Ju Jv Jy Ke Kf Kk Kn Ko Kq Ks Kx Ky Kz Lh Li Lj Lu Ma Mk Mm Mn Ms Mz Nd Nf Nk Nm No
Nr Nv Nw Ny Of Oh Ok Om Ow Oy Oz Pa Pb Pc Pj Pk Qa Qb Qc Qe Qm Rf Sr Tv Ug Uh Un Uu Vt) pK(Ad aF Aj Al aO Ax Bb bC Bn cC Co
Cs Dc Dg Dl eM Ez Fa Fb Fp Ha Hb Hq Ih Ii Ij Ik Im In Io It Iu Iz Jj Jm Jo Jt Kc Kf kG Kj Kl Kq Ks Li Lj Lu mF Mm Nj Nm Ns Nv NY Oa Of
Oh Ok Ou Pf Ph Pj Pz Qa Qe Qh Qv Qz Rc Rf Rm St Ue Uf Ug Uu Vo Vq Vv) eP(Ad Al aO Aw cC CO cR Cx dA Dd Dg Dl Dp Ed Gd hB Ii Ik
Jt Kk Kl Lv Ma Nj Nm Nq Nx nY Og Oh Oi Ok Ow Pz Rc Rm Uf Uh Ur Uu Vo Ti Th) Mm(dU eQ gC gZ jB kC kE kF kG kl kK kN kP lW lX
mE mF ml mM mP mS mW mY nB nF nl nN nO nR nT nU oD oO oP oQ oT oV oW pH pl Um) Hp(kC kE kF kG kl kK kN kO kP lW lX lY
mE mF mH ml mM mP mS mT mU mW mY mZ nA nB nC nD nF nH nl nJ nK nL nM nN nO nR nT nU) Rt(kC kE kF kG kl kK kN kO kP lW
lX lY mE mF mH ml mM mP mS mT mU mW mY mZ nA nB nC nD nF nH nl nJ nK nL nM nN nO nR nT nU) Vb(kC kE kF kG kl kK kN kO
kP lW lX lY mE mF mH ml mM mP mS mT mU mW mY mZ nA nB nC nD nF nH nl nJ nK nL nM nN nO nR nT nU) eM(Aw Ax Bb Bg bW
DG dH Dl Fy Ha Hl Hu Ii Jt Kf Kl Ks Lh Lj Lv Mu Mv Nk Nm Nq Nv Oh Oi Ok Rc Ss Vo) oT(Al Ax Cs Fp Ha Hb Ii Im Ji Jq Js Ke Kn Kq Ks
Lh Li Lj Mn Nv Ny Oh Ok Pj Qa Qe) oV(Al Ax Cs Dc Fp Hb Ji Jm Jq Js Ke Kf Kq Ks Lh Li Lj Nm Nv Oa Oh Ok Pj Qa Qe Rm) gC(Al Ax Bb
Cs Fa Fb Fp Fy Ha Ih Ii Ij Im Jo Js Kj Ks Li Lj Nv Ny Oa Oh Qe Rm) nl(Ad dH Gb Gn Hl Iz Jo Jt Kd Kj Kl Ks Ky Lp Mp mU Nm Ok Ph Pk
Rc Um Ux Uy Vw) eQ(Al Ap Ax Cs Dc Dg Fb Fp Hb Jt Kf Ks Li Lj Nm Nv Oh Ok Pj Qa Qe Rc) Gb(kC kF kl kK kN kP lW mF mH ml mS
mU mZ nA nJ nN nO nR nT) Jo(cF dU fR kl lW lX ml mM mP mU nN nO nR nT nU Oh pH Tz Um) Al(dU gZ jB kl lW mH mS mT mU nB
nD nF nH oD oO oW pH pl) oO(Ad Ao Ap aS bA Bb bX cF Cv Dd Hb Kj Nm Pj Ug Um Ti) Nd(Gn Gz Hr kl kK mS Pa Pb Ry Uk Uz Wg Yg
Yi Yj Yf) mU(Ii Jt Mb mE Nm Nv Oh Ok Rb Ss Uw Ux Uy Yg Yi) pH(Ax Cs Fp Ha Ii Im Jj Kn Kq Ks Lj Oh Qe Rm Ug) dU(Ax Cs Fp Ha Ii
Im Jq Kn Ks Lj Nv Oh Qe Ug) oW(Ax Cs Fp Ha Hb Kf Kn Ks Lj Nm Nv Ok Qa Qe) pl(Ax Cs Fp Ha Ii Ij Im Jj Jq Ks Lj Oh Qa Qe) Cv(kl lW
lY mE mH mM mS mT nC nF nH nK nL) jB(Ax Cs Fp Ha Ii Im Ir Kq Ks Lj Oh Qa Qe) gZ(Ax Cs Fp Im Ks Li Lj Nv Oh Ok Qa Qe) oD(Ax Cs
Fb Fp Js Ks Li Lj Nv Oh Qe) Yi(kC kF kl kP mH mP mS mZ nA nJ) Uy(kC kE kF kl lX mH mS mZ nT) Ux(kK kN lW mH mP mY nA nN nO)
nJ(Fd Gn Hl Ho Uw Vj Vw Yj Zx) Yg(kC mF mH ml mS mW nA nU) Um(Bb Li mE Mz Oh Rc Rh Tz) dX(Ba dG nY Of Ou Vo Ti Th) Nm(kl
lW lX mE mS nN) Hl(lW mE mT nH nT nU) mH(Rz Sf Si Uw Va Vw) Ok(kl mS nA nF oQ) Uw(kC kl mS nA) nN(Lp Rz Va Vw) lW(Lp Ph
Vw Wb) nH(Fd Gn Yj Zx) Bb(kG lX nB) Dg(lX nA nD) Oh(kl Li lX) nU(Mb Rb Yj) Si(kE kl) Zq(kl mS) Ug(oP oQ) mT(bX Yj) GnnC LykG
TzcF HuOy LpnR VwnB] Jj[Jk(Et Fp Fr Hq Hr Hw Hx Ii Ij Ik In Io Ip Iq Ir Jg Jm Jn Jo Jp Jr Jt kC kE kl kN kO kP Lj Lu Lw lX LY Md ME
MF MH Ml Mj Mk Ml MM MP Mq Mr MS MT MU Mv MW MY MZ nA NB NC ND Ne NF NH Nl nJ NK nL NM nN No Nq Nr Ns nT Ny
Of Og Oz Pa Pb Pc Pd Pe Pz Qb Qc Qe) Po(cF Et Fp Fr Hq Hu Hv Hw Hx Ii Ij Il In Io Ip Iq Ir It Iu Jg Jm Jn Jo Jp Jr Js Jt Lh Li Lu Lv Lw Lx Ly
Lz Ma Mb Mc Md Me Mf Mg Mh Mi Mj Mk Mm Mn Mp Mq Mr Ms Mt Mv Mw My Mz Na Nb Nc Ne Nf Ng Nh Ni Nj Nk Nm No Nq Nr Nw
Ny Oe Of Og Oh Oi Ok Om Oy Oz Pa Pb Pd Pe Pf Pz Qa Qb Qc Qe) Iv(Et Fp Hq Hr Hu Hv Hw Hx Ih Ii Ij Ik Il In Io Ip Iq Ir It Iu Jg Jm Jn Jo Jp
Jr Js Jt Lh Li Lj Lu Lw Ly Lz Mb Mc Md Me Mf Mg Mh Mi Mj Mk Ml Mm Mn Mq Mr Ms Mv Mw My Mz Na Nb Nc Ne Nf Ng Nh Ni Nj Nk
Nl Nm No Nr Ns Ny Oe Of Og Oi Om Oy Oz Pb Pd Pe Pf Pz Qa Qb Qc Qe) Mx(Et Hq Hr Hu Hv Hw Hx Ih Ii Ij In Io Ip Ir Jg Jm Jn Jr Js Jt Lh
Lj Lu Lw Ly Lz Mb Mc Md Mf Mg Mh Mi Mj Ml Mm Mp Mq Ms Mt Mv Mw Mz Na Nb Nc Nd Ne Nf Ng Nh Ni Nk Nl Nm No Nr Ns Ny Og
Oh Oi Ok Oy Oz Pa Pb Pd Pe Pz Qa Qb Qc Qe) Im(cF Et Hr Hu Ih Ij Ik In Ip Iq Iu Jh Ji Jm Jp Jr Js Jt Lh Li Lu Lw Lx Ma Mb Md Me Mf Mg
Mh Mi Mj Ml Mp Mq Ms Mt Mv Mz Nb Nc Nd Ne Nh Ni Nj Nk Nl No Nq Nr Ns Nu Nw Og Oh Ok Oy Oz Pa Pe Qa) Ji(Hr Hu Hw Ih Ii Ij Ik Il
In Ip Iq Iu Jh Jo Jp Jq Jr Js Lh Li Lj Lu Lv Lx Ly Ma Mb Mj Ml Mp Mq Mt Mv Nb Nc Nd Ne Ni Nj Nk Nl Nq Nr Ns Nu Nw Nx Oh Ok Oy Oz
Pa Pc Pe Pz Qa Qb Qe) Nx(Et Fp Hr Hu Hx Ih Ij Ik In Ip Ir It Jg Jp Jq Js Jt Lh Lj Lu Lw Ly Mb Md Mf Mg Mh Mi Mj Ml Mm Mp Mq Mr Mt
Mv Mz Nb Nc Ne Nh Nj Nk Nl No Nr Ns Nw Oh Ok Oz Pa Pc Pe Pz Qc Qe) Jq(Hr Ih Ij Il In Ip Jg Jh Jp Lj Lu Lv Lx Ma Mb Mj Mp Mq Mt Mv
Mz Nc Nd Ne Nh Nj Nk Nl No Nq Nr Ns Nw Oh Ok Oz Pa Pc Pz Qa Qb Qc Qe) Fr(Hq Hr Ih Ij Ik Jh Jn Jp Jr Js Lv Lx Mb Mj Mp Mq Mt Mu
Mz Nc Nd Nh Nj Nk Ns Nu Nw Oh Ok Oy Pa Pc Qa Qb Qc) Qa(Hr Hw Ij Ik Il In Iu Jh Jm Lj Lv Ma Mb Ml Mp Mq Mt Mu Mz Nd Nj Nl Nq
Ns Nu Nw Oh Ok Pc) Hu(kE kF kG kl kK kP lW lY mE mF ml mM mP mS mT mU mY mZ nB nM nN nO nT nV) Nw(cF Hx Ih Jh Lj Lv Lx
Ma Md Ml Mq Mt Mu Mv My Nf Nj Nl Nq NU Ny Pb Pc) Nt(Et Fp Jg Jr Jt Lh Me Mg Mi Mk Mm Mn Mr Mw Nb Ne Ng Nh Of Pf Pz Qe)
Mu(Ih Ik Jh Jp Js Lv Ma Mj Mt Nj Nl Nu Ok oO oP oQ Qb) Lx(Ih Ik Jh Lj Lv Ma Mq Nj Nl Nq Nu Oh Ok Pc) Ik(Et Jp Js Lv Mj Mp Mt Nd
Nq Nu Ok Pa Qb) Nv(Ir It Jg Mi Mk Mr Mw No Nr nU Pz Qe) Lv(Ih Jh Jp Js Mt Nl Nq Nu Oh Pc) nU(iB jl Ma Mj Mv Ny Oz Pb Pg Pz) Ok(Hr

Lv) Mj(kF kG nO) Hr(Lx Po Qa) Aa(Dc Qa) Bo(Lv Mi) Hv(Yh Yj) HwQa YdnI aJcU} Pg{Im(Hr Ii In Iu Lv Ly Og Pc Pe Pf) li{Jh Jq Nt Ok Po)
Ok(Hr Hw Pc Pf) nl(Gd Hl Ju Si) oP(Hp Op Si) HI(kC pF) Pf(Fr Lx) oQ(Hp Si) DeHr NtLy} Oh{Wm(Fr Hr Im Jp Li Lj Ly Mc Ml Mm Mv My
Nq Ns Pz) wJ(Hu Iu Jt Lj Pf) Ua(Gd Hp Si) Hv(Du Yj Yl) Hu(Gd Yf) Li(Qy Ra) eM(Aw Wd) AxGp} Qa{Hw(Im Jm Jq Nt) In(Im Jq Nt Ok)
Li(Ud Up Vv) eM(Mm Wd Wh) Ax{mE nl) Hr(cB De) Hb(Yh Yj) Ok(Hv Ij) AacB HapK NtIu liJq YkSi LjVu} Ua{Sh(Gh Gp Ib Lp Lz Mb Mk
Pc Rt Rv Ry Tr) Mh(Du Eq Gd Sf Si) Si(Ed Lz Ow) Yl(Gd Or) JmoW LplW Ugnl PcfB dUkG} Ps{Hp(eM kG kP IW mH ml mM mS nT)
Uo(Hb Hv Ih Ny Ow Si) nJ(aV bO Gp Lh) Gp(lW mE) Rc(eM Vv) HbkI WbeM PbkE} nl{Kq(Ap Cv Dg Dl Hb Mm Nk Pj) Va(Jq Ou Vs Yd)
Yh(Gn oE Ug) Ky(kF Vv tF) AwGd CoUx C

Pf Po) Nt(aA Im Iv Jk Jq Ly Mu Mx Nd Nv Nx Po) Nv(aA Hq Ik Im Iv Lh Mb Mx Nj Nu Nx) Iv(aA Fr Jk Jq Mu Nx Po) Mu(kK mE nO nR)
Jk(aA Ji Nx Oy) Mx(aA Nx) PoaA UaeP HunR UtdX} aA{Nn(Hr Im Iv Jh Ji Jl Jq Lv Lx Ma Mb Me Mx Nf Nj Nl Nt Nv Nw On Oy Oz Pg Po)
Hr(Iv Ji Jl Jq Lv Mx Mz Nv Nw Ok On Pg) Mb(Ji Jl Jq Mx Nd Nv On Pc Pg) Iv(Ma Mx Nv Pc Pg) Nj(Ma Mx Nd Nv) Jo(Nt On Pg Po) Ma(Mx
Nv) Mu(My Oy) Ii(On Pg) PoLi NtLy MxPc NfNw HqNv OfOn PePg mUlL} On{Ii(eP Iv Jl Mx Nn Oy Pg Po) Jo(Iv Mb Mx Nn Nt Oy) Oy(Iv
Jk Lj Mb Mx) Nn(Mw My Ng) Mu(Mw My) Iz(dX eP) YjOk KsdX RmeP} Jo{Nn(Iv Ji Jl Jq Nt) Cu(cF Me Yg) Nt(Jl Jq) Ma(kl mU) UteP}
eP{Ut(aO bA Jp Ug Ur) Kq(aO Ax Ik) ImVo HcKx} Um{Nd(Jq Mz Oh Qa Tn Tz) Qa(Ax Lj) MvMz} Tz{Si(Co Hu Uf Yg) AaIN HbYh}
Nn{Nw(Mw My) Oy(Jl Nv) ImIv} Mz{Nf(Im Mu Nq Nv) AdcF} Cu{nI(Dg Jt Nm) NbYi} hR{rZ(hA hX jG qW)} Mu{Nw(My Oy) NvOy}
YI{Or(Hu Mv) HbNw} dX{Im(Qz Vo) OuPe} eM{UaLp HvUy TvXa} Nd{HlPe OaUy} Ji{IiJl NvNx} oO{TncT bAfR} BoGzgW GdHqkN RgeDnY nBlKlL

Constrained panels with 3 analytes, where 1.0E-7 >= 'model p-value' > 1.0E-8. Contains 3,193 panels of 25,049,241 total panels evaluated. : Qd{Hb(Ad aM aO As aU Ax Bg Bo cB Ch Cq Cu Cw cY dA Dc Dd Fn Gl Ha Hc Hf Hv Hw Id Ii Ij In Ir It Je Jn Jo Jp Jr Js Kd Kn Ko Kr Li Lj Lu Lw Ly Mi Mj Ml Mr Mt Mv Nf Nj Nm Ns Oh Oy Oz Pb Pd Pe Pi Pz Qa Ra Rj Tv Tz Ud Ue Uh Ul Uo Up Us Vp Vt Vv Yg) cL(Ad As Bb bL bN Bo bR bS bU cA cB cK Cq Dd dI Hr Hw Iu Jm Js Jt Me Mm Mr Mt Nd Nf Nm Nn Oh Oy Pa Pb Pd Pe Po Qe Um) Nd(Ad Al Bb bN Bo cB cK Cq Cs Dd Fn Gb Gp Hf Id Ke Kn Ko Kr Lp Pj Qv Rg Tr Tv Uc Ue Uk Ul Uo Up Us Uy Vp Vt) aU(Ad aK As Bb bN Bo Cq Cw Dd Dl Hr Hv Hw In Iq Ir Iu Jm Js Jt Lh Me Mm Mr Mt Nf Nn Ns Oh Oy Pa Pb Pd Pe Po) cF(Ef Gp Ha Id Je Jv Kd Ke Kf Kj Kn Kq Kr Rj Tv Tz Uc Ud Ue Ul Up Ur Us Vp Vt) Ba(Al Bb cB Dd Hr Hw Ij Iq Jm Js Lh Me Mr Mt Nf Nm Nn Ns Ny Oy Pa Pd Pj Qe) cT(Aa Ad As bA Cq Cs Dd Ha Hr Hv Hw In Js Lh Mr Nf oO Pa Pd Pe Po Um Uo Vt) Bg(Al Bb bN Co Dd Hr Hw Ii Ij Iq Iu Jm Jt Lh Me Mr Nf Nn Ns Pd Qe Um) Ad(aO bN cB cK cY De dF Is Iv Jq Lj Lv Ma Me Mv Mz Nb Nf Ns On Pz) dF(Cs dG Hr Hw Ij Jo Js Jt Mm Nm Nn Nr Nv Oh Oy Pa Pd Pe Po) nU(Hu Iu Jk Jm lL lN lY Ma mE Mm Mu Ns Nv Oz Pb Pc Pz Qe Xa) cB(Aa Bb Cs Cw Dl Ij In Ir Js Lj Me Mr Nf Nm Nn Oy Pe Qe) Dd(Ax Bb BN bV cK De Iu Lh Lj Lv Me Mv Mz Ne Nl Ns) Jm(aA As Bb bN Fr Iv Jk Jl Lj Ma Mu Mx Nq Nv On Pc Pg) aO(Aa Bb bN Cs Hw Ii Jo Js Jt Ke Mm Mr Nn Oy Pd Pe Po) De(As Bb bN Cq Hw Ii In Jt Lh Mm Mr Nf Oy Pd Pe) Iu(bN Fr Jj Jk Jl Lj Ma Mu Mx Nt Nv On Pc Pg Um) Um(Ax Bb Ju Ly Ml Mm Mu Nn Oh Pj Qv Tz Ub Ue) Nn(aZ bN Bo cY Iq Lh Mx Ng Ns Nv Og Pz) Bb(aZ Gp Hw Im In Lj Mr Nf Ns Oy Pz) Lu(bN Cp Cw Dc dG dJ Gp Id Kn Ko Kr) Jo(Aj bF Ct cY Jk Jl Lj Ma Nt Nx On) Li(Fr Is Nv On Pc Qv Qy Rf Ue Uo Ut) Ax(Bo Gp Is Lh Nb oE Qv Rf Ue Wm) Bn(As Cq Hr Hw Ii In Mr Nf Oy Pd) Jj(Fr Iv Jl Jq Lv Ma Mx Nq Ns Po) Nv(aA eM Hq In Iq Jt Lh Lj Ng Oy) bN(Al Cs Hr Hw In Me Mm Mr Oh Pd) Me(As aZ cK Cp Cq Cs Cw Dc) Mr(Al aS bA bO bV cK cU Di) Jt(aZ cK Cu cY Is On Tt) Lj(Ao As Bo Co Is Pc Wm) bV(Cs Hr Hw In Lh Pd Pe) Ii(aK cY Gl Jk Jl Wm) Aa(aS aZ bA bW Gp) Cs(aS bA cK Nf Ns) aA(Iv Lv Mb Mu Mx) Ns(As bS cK Cq) Is(Cq Ih It Lh) On(Lh My Nb Pz) Pj(Gp Hr Oh Pz) Gz(jG lL lN) Mm(aZ bS Gp) Mu(kK My Oy) Nf(Al dJ Mz) cK(Hr In Js) Aw(dX Oy) Wm(Fp Ml) Fy(dX eP) Lh(bF Bo) Pd(Al cY) aZ(cA Nb) nR(lK Nm) CuHw MvUe IdlL JsbF RmOh PaaS PebA aCaX} Is{Jo(Ad aF Al aO As Aw Ax Ba bR bU bV cA cB cL Cq cS cU Dd dF Di dJ Et Iu Jh Ji Jk Lv Mb Mu Mx Nj Nl Ns Nu Nx Og Oh Um) Hr(aC Ad Al aR Ax Bb bR bU bV cA cB cU Dd Fr Hb Iq Iu Iv Ji Jl Lj Mu Mx Mz Nt Nv Nw Ok On Pc Pg Po) Dd(aC aR Ax Bo bU bV cA cB Di Ii Im Jm Js Lh Li Lj Ly Mb Mm Mu Mv Nb Nd Nm Ns Oz Pb) Ii(Aa aO aR Ax bR bU bV cB Iq Jh Jp Lj Lv Lw Lx Ma Mb Mu Mx Nj Nl Ns Nu Og Oh Ok) cF(As Bo Cp Cw Hv Hw Ij It Jn Jr Js Kr Me Mr Na Nf Pb Uc Ud Ul Up Us Vp) Aa(aA Al aO aS Ax aZ bA bR bU bV cA cB cC De dJ Gp Ih Iq Jm) In(Ad Al Ax bU cB De Hb Lj Mb Mx Mz Ns Nu Nv Of Og On Pc Pg) Nv(Hq Hw Il Im Iq Iv Jt Lh Li Ly Mb Mg My Ng Ni Of Og Oy) Og(Fr Iq Iv Jk Jl Jm Lj Mb Mu Mx Ns Nt Nu Nw On Pc Pg) Pc(Im Iq Iv Jt Li Lj Mb Mg Mx My Ng Ni Nt Of Oy) Ax(Ad As Cq Cw Hv Hw Ij Ir Jn Jr Me Nf Pb Um) Fr(Hq Iv Jt Lh Li Ly Mb Mg Ng Nm Ns Nx Of Oy) Jm(Ad As Cq Cu Cw Kr nN nR Um Uy Uz Vi Wg Yl) Nt(It Lh Li Lj Ly Mg Mx Nd Ng Nm Of Oi Pz) Iq(Im Jl Jp Ma Mu Mx Nd Ns Nw Of Oh On Pg) On(Lh Li Mb Mg My Nb Ng Nm Nx Ny Po Pz) Um(aR Iu Ju Li Ly Ml Mu Nj Nn Qy Rm Ub) Mx(Ih Im Ir Iv Jr Js Jt Lj Ma Mb Ns) Nw(Iu Iv Jt Lj Mh My Nf Nx Ny Oy Pb) Ad(bU cB Me Mm Mu Mv Uy Wd Wh) Jt(cB De Et Iv Jh Ji Jp Ok Pg) Lj(Im Iu Iv Ly Mb Nd Of Oy rY) nU(jH jI lL qT qU qV qW qY) Hb(Up Vp Yg Yh Yi Yj Yl) Pg(Lh Ly Mg Of Oy Pe Pf) Ir(Al bU cB De Mz Nn) Cq(De Me Mm Mu Ns) Gb(Dc Hu mY Yg Yl) Lu(As Cp Cu Cw Yl) Mb(It Ly Ml Nd Ok) *Iv(Ly Mg Mu Nd Of) Iu(Jl Mu Ni Po) Nd(Hl Rm* Up) Yj(Et Ju Sf) Ok(Hw Ij Nx) Uy(bO Ju Sf) De(Hw Nf) Ma(Mg Of) Me(As Cw) Mm(Bo eM) Ng(Jk Mu) Yi(Bn Si) Oy(Jk Nq) lL(mU nA) DrdX PoLi EtYl NsIm NuLy MzIj NiNk HllW SiUo JiNx UweM nRqV} nU{eD(Fp Fr Hq Hr Hw Ih Ii In It Jg Jk Jl Jn Js Li Lx Me Mj Mq Mu Mv Mw Mx Nf Ng Nn Nv Oe Of On oP Oy Oz Pb Pc Pf Pg Po Pz Qb Qc) lL(aA Fp Hx Im In Ji Jj Jo Jq Lh Li Lj Lx Lz Mj Ml Mp Mq Mv MW Mx Nf Nq Nw Ny Oh Pa Pe Pf Qa Qb) Mq(hA iB iC jE jF jG jH jI jK jL jM jO jQ jR jT jU jV jY lK lN qT qU qV qW qX rA) Mx(hA iB iC jE jF jG jH jI jK jL jM jO jQ jR jT jU jV jY lK lN qT qU qV qW qX rA) Pe(hA iB jD jF jG jK jL jM jO jP jQ jR jT jU jV jY lK lN qT qU qV qX qY rA) Qb(hA iB iC jD jG jH jI jL jM jO jP jQ jT jU jV jY lM qT qU qV qW qY Xa) Fp(hA iB jD jE jF jG jI jK jM jO jP jQ jR jU jV lK lM lN qU qX qY rA) jI(hR hX iC Im kG kI Lz Mb Me *Mf mI Mj Ml mS nO Nw Oi Pf Qa rX)* Qa(hA iB jD jG jK jL jM jQ jR jT jY lK lM lN qW qX rA) Me(hA iB jE jF jK jM jO jQ jR jU jV qW qX rA) Mj(jD jE jF jG jH jL jM jP jT jU lM qV qY) rZ(hR jD jH kC kF kK lK mW nT oP rY) oP(hR jD jH jK jR lN qU qW rB) Nw(jH jQ qT qU qV qW qX qY) hR(jD jH jT mW nT qY) lM(Ij Jq Lh Nq Ny Po) Nq(jE jF Mm qY) Lz(Oz Pb qU) Im(jK jP jV) Jj(Hu Jk Mu) Ny(jG lK qT) Pd(jF jM jV) Po(jE Wh) Mv(My Oy) Nf(jF jM) Wd(Jr Lx) Jo(Ma Vv) Jq(jP qY) Oh(Jm qV) rC(jD jH) AjYg MbjM MlqU MwjE NhiB NijU TzXa HqOy SfPg WhJr JsjD LijF PfjH mWhV} aA{Mb(Fr Hr Im Ip Iv Jh Jj Jk Jp Lv Lw Lx Ly Ma Mj Mp Mt Mu Mz Nt Nu Nw Ok Pa Po) Hr(Et Fr Ij Ik Im Ip Jh Jk Lw Lx Ma Mf Mj Mq Mt Mu Nj Nl Nt Nu Nx Pa Pc Qa) Nw(Hx Ii Iv Jh Jj Jk Lh Li Lj Lv Ma Md Mf Mh Mx My Nj Nl Nt Nu Ny Oy Pb Pc) Pc(Ik Im Jh Ji Jj Jk Jl Jq Lv Lx Ma Mj Mt Nj Nl Nt Nv Nx On Pg Po) *Mx(Fr Hw In Ir Jh Ji Jn Jq Jr Js Lv Lw Mu Nf Nt Nv On Pg Po)* Nj(Fr Im In Jh Jj Jk Jl Jq Lv Lx Ly Mj Mp Mu Mz On Pa Pg Po) Ji(Hv Hw Ii Ij In Iu Iv Jj Jk Jo Lj Ma Mu Nd Nf Nv Oz) Jj(Fr Ij Ik Im Jh Jq Lv Lx Ma Mf Mj Mt Mu Nl Nu Nx) Nv(Hw Ii Im In Jo Lh Li Lv Mr Nd Nf Nl Of Oy) Ma(Jk Jl Jo Jq Lv Mu Nd Nl Nt On Pa Pg Po) Jq(Hw In Iv Jh Jk Jo Lv Mu Nf Nl Nt Oz) lL(hR kK kP mE mP mS nA nI nN nO nT) Hw(Ij Jl Lv Lw Mz Nt Ok Pg Po Qa) Iv(Fr In Jh Jl Lv Lx Mu Nd On Po) Jk(Hq Ii Im Jm Nd Ng Nl Og Oy) On(Iu Jt Lh Li My Nb Nm Oy Oz) Pg(Hq In Iu Jh Jm Lh Nd Nf Pf) Lv(Im Jh Jo Mu Nd Nl Nt) Nl(Fr Jh Ly Mu Mz Nd) Jl(Ii Iu Jo Lh Mr Pe) Po(Ii In Iu Lj Nf) Im(In Iu Lj Nx Oz) Nt(Hq Ii In Nd) nR(hW rX rY rZ) Mu(Jh Mw Ng) Lx(Li Lj) Mz(Ij In) Nd(Ik Mp) Nf(Mt Ok) hR(eD lN) JoOk mWrZ} Nn{Mx(Im In Iv Jh Ji Jl Jm Jo Jp Jq Lv Ly Mb Me Nt Nw Og Ok On Oy Pg) Im(Iu Ji Jl Jm Jo Jp Jq Lv Lx Mb Me Nj Nl Nt Nv Nw On Oy Oz Pg) Iv(In Jh Ji Jl Jm Jq Lv Ly Me My Nd Ng Nv Nw Og Oi Ok On Oy Pg) Jj(Et Fr Ih Ij Js Mb Mj Mq Mt Mz Oh Oy Pa Qb Qc) Jl(Hr Ii Iq Iu Jm Lh Li Mb Me Mg My Ng Nj Og) Ji(Ii Iu Jm Lh Li Mb Me My Nf Ng Oy Oz Pd) On(Iu Jm Jt Lh Li Mb Me Mg Nm Of Og) Nv(Hq Ii Jo Lh Mb Me Mw My Ng Of) Ok(Hr Hw Jo Mb Me Nf Nm Om Oy Pd) Nt(In Jm Ly Me Mg Nd Ng Oy) Oy(Jk Jq Lv Lx Me Pg Po) Me(Jp Jq Lx My Nw) Pg(Ii Jm Jo Ng Pf) kK(jE jF lL lM Mu) Nw(Li Mv Nf Ng) Mz(Ij In Um) Tz(Li Si Um) Jo(Lv Nx Po) Jq(Ii Mb) oV(Ba cT) NdUm HllW TneP YgJr} Jj{Jk(Ih Im Jq Js kF kG kK Lv Lx Ma Mb Mx Ng Nj Nl nO nR Nu Nv Nw Oh Ok Po Qa) Nv(Hr Hx Ih Ii Jh Ji Jp Jq Li Lj Lx Md Mt Mu My Nl Of Oy Pb Po Qa Qb) Mx(Fr Ik Im Iv Jh Ji Jp Jq Lv Lx Ma Mu Nj Nq Nu Nw Pc Po) Iv(Im Jh Ji Lv Lx Ma Mp Mt Nd Nq Nu Nw Oh Ok Pa Pc) Po(Hr Ih Im Jh Ji

Figure 32 Continued

Uo) Qa(eM mY) NbUo UaSh JdlW PsbO PgnI} eP{Ld(Dk Ed Fw Ib Im It Kq Mr Mv No Nr Ny Pg Qa Qb Qe Ua Vu) Ny(cC cO De Mi Mp Mt) nY(Iz Mv Na Nt Uc Uf) Ti(Ed Fw Ir Nq Qe) Th(No Om Pe Qa Qe) Kq(Iu Jp Nm Ou) Ua(hB Jp Ur) Aw(bA bO) DeMj EfUg MpcT MvhB UeJd} jI{jG(kP IN mM mP mT mZ nN nT) IL(hR kP IO mM mP mT nB oO) Me(An Ax bA Bc CT Gz) nC(IK mP nD Ne nO nT) Gz(Ax Dk In Lv Mb) nL(IK mU nD nO) hR(eD Lj IN rY) kO(IK mU nD) Id(Na Qm) AreD NcnN nKIK lNlO} Jr{Hb(Dr Du Gn nl Rt Uz Vh Vi Wg Yl Tl) Yj(Aa Oh Ow Ua Uh Wd Zq) Si(Cv Du Hl Uo Us Yl) Yl(De Ou Rh Uo Va) nl(cL Wb Zq tF) Em(Aw cF De) Hr(De Gz) Vu(Dr Zw) AaDu SfoP PsnJ NyUz} lL{nN(hR iC jD Jp Mp mW nF) Nq(kK mE mF nA nO nT) mY(Fr iC jH My oQ) Mp(kN mT nA nC) mU(iC jH Js mW) oP(lY nC rX rY) hR(eD jD lM) oQ(nA nK nO) Mj(nI nO) nT(Lx Mt) kP(mW qV) nBiC} cF{Me(aJ aO aP bA cL cU De Fr Lv Lx Mi Mp Ok) Qa(Aa dX Hr Hw Uo) aP(bR cB cU dG Lv) Im(aN cU Jm Lv) Uo(Dc Jq Kq Or) Mj(kF kG nO) Bo(Lv Mi) Hr(Lx Po) AaDc YdnI aJcU} Uf{oV(Ad Al Fb Jt Kf Li Lj Nm Oh Pj Pz Uu) pK(Bb Ha Io Jt Ny Pj Qz) dU(aO Ha kG Ns Og Vo) gZ(Al Li Lj Ny) Jt(eQ fB kN) Li(jB Oh) Pj(fB oT) NmkN OzpH dXnY} Pg{Im(Hr li In Iu Lv Ly Og Oy Pc Pe Pf) li(Jh Jq Nt Ok Po) Ok(Hr Hw Pe Pf) nI(Gd Hl Ju Si) oP(Hp Op Si) Fr(Oy Pf) Hl(kC pF) oQ(Hp Si) DeHr NtLy LxPf JkOy} mU{Ma(Fr Ih Ii Ip It Iu jQ kP Lh Li lM mE Mm Mn Ns Of Og Ok Pd) jF(It Pe) NqMm HuOy TrYd YhQv ZqcS SsRz RvcM NyVi UgVv PdhA} Ua{Sh(Gh Gp Ib Lp Lz Mb Mk Pc Rt Rv Ry Tr) Si(Ed Lz Mh Oh Ow Oy) Gd(Oh Yl) Hp(Oh Oy) MhSf JmoW LplW YlOr UgnI UrdX PcfB dUkG} Qa{dX(dL Qz Rm Ti Th) Hw(Im Jm Jq Nt) In(Im Jq Nt Ok) Ax(mE nI) Hr(cB De) Hb(Yh Yj) Li(Ud Up) Ok(Hv Ij) AacB HapK NtIu MmeM IiJq YkSi} Ps{Hp(eM kG kP lW mH mI mM mS nT) Uo(Hb Hv Ih Ny Ow Si) nJ(aV bO Gp Lh) Gp(lW mE) Rc(eM Vv) HbkI WbeM PbkE} nI{Kq(Ap Cv Dg Dl Hb Mm Nk Pj) Va(Jq Ou Vs Yd) Yh(Gn oE Ug) Ky(kF Vv tF) AwGd CoUx CvmZ MjqY MwjF HpeM JqRt XaOi} Me{jV(aJ aP Ba bC bL CT cX dK iJ Kg Ki Kj Or) Im(aN aO cB) jU(Bc CT) De(Hr Nf) KylN cBcU} Nt{Ly(Fr Im In Iu Jq Lv Mg Ng Oi Pc) Im(In Iu Jm Pc) Fr(Mg Ng Oy) PoIi NmoP NgJk InJq dXnY} oV{cT(Fa Ha Hb Im Mm Ny Oa Om Rm) Fa(bQ bZ) Mm(Ba Hc) Hb(aO Ma) bF(Dp Ju) FyPb HcaF OabQ VtaO} Yl{Or(Aw De Ef Hc Jh Mw Nb Ng Wd) Ou(cE Hb Ju Mm Nb Op Sf) Hv(Oh Ow) GdHu MvOw} oP{lN(hW lY mE qV) Rz(aF Nm Ny) cM(Gh Vz Ti) Yh(aF Nm) Sf(aQ bU) DubB GpHl HvSi mErX} Oh{wJ(Hu Iu Jt Lj Pf) Wm(Fr Mv Nq Pz) Hv(Du Yj) Li(Qy Ra) AxGp GdHu WdeM} Vi{Aa(cC De Gc kO mH mS Ql Qx Yj) Uo(Hv nJ Ny) nJ(Jq Lx) AdHc PbkE} fB{Ez(Cs Ny Qb Qv Rf Sr To Un Vt) Qt(cL Pb) bZ(Ny St) BaRc FyLj LvTo} Gz{lM(Dk Lx No Rf) Ky(jL jR jT) jP(bN Ed St) Dk(jD jK) Nq(jV lN) LyiB} mE{Qu(Hr Mm Qz Rb Ug Ur) Nm(Kq Ma) Mv(Co Hl) EfHl MpjF JdUx OmVa} kK{Mv(Jh Mk Om qV) Nq(jE lM Mm) Mj(iC jO) Mw(jT qV) jF(Fr Jk) ZqPf} kN{Mp(jE jG Nm) Hl(Pf Qt Qz) Ke(Nm Pj) Ou(Ux Zq) GpWd MwjT XaRt OmUx} Oy{Jk(Fr Jq Lx Ma Ok Pc Po) DcNq PoLj FrJq MvcB MwVv MyrY} Hr{De(cB cU Hx Mj Ny Po) Ok(Fr Jk Po) PocB NycU} Im{cB(aN bV Jm Li Lv Mm) Lv(Ax Pc) PoJm FrNl GcdX} Va{Ou(kI kO lX nA) lX(aQ Om Vs) Yh(mH nO) OmnJ VseM} kG{dU(Hc Ib Iz Jd Vs) Mj(Jm Nm) GnHv ZqOm XaOi} dX{Th(Jt Ny Pe) nY(Mv Na Pz) EdTi GnPe JfbV} lN{Ky(bC Gp Ko Kr) mS(Mj oQ) hR(dE Lj) AaQl} Ma{Nm(kI mF) pK(Ny Qz) NgJk JtnA LioQ LjjB} eM{Lx(Wd Wh) Vs(Lp Rt) MjWh MmQe ZqJn} kE{Cp(Hp Si) MyHl YhQv WhbF XaOi RzUx} Hv{Gn(mP nC) AaXa LuYk HbYj VzUo} fA{Ke(Lj Mm) Ou(Ar Ny) AxFw LxLj} Rt{Om(mY nJ) AaQl ComT YhnO} aJ{cU(cB dG dH) IdlM dFdG} Fr{jG(eD Ly) NgJk IiJq} Rv{nL(Jd Lv Uv) JdnC} Ow{Sr(gC pK) QegC VtpK} Ux{Rz(kI mS) EfnN OunD} lW{AlKq CoHl GpWd XaOi} hR{iB(rX rY) MdLj jDrY} kO{GpWd SsRz RxVs VjbF} oT{iO(Qg Rf Rm) NicT} Ly{wL(Mm Nx) wDwF} Mw{nD(jT qV) nLlK} Hu{EdHp IhwJ RyOa} Yj{Mv(Ch Sh) dRlX} Ny{bZpK cToW nKlK} aP{dG(cB dF) cUdH} eD{Rg(gL iZ) iZjY} Aa{VjPi dRlX} Nm{LwOk KqmM} Ii{PoJq VvpI} Hc{AloD DeGd} Lj{oW(cT Vv)} bZ{AxpH RfpK} mT{EfHl ShJh} TilMoE LvTopH NgJkOk YhUgnO ZqJnmY WcOmnJ LdaUjB VjbFnA cUdHfR

Constrained panels with 2 analytes, where 1.0E-8 >= 'model p-value' > 0. Contains 9 panels of 149,894 total panels evaluated. : Is(aA Jj Jm Nn) Qd(cF Im) Jj(Jl On) NnaA Constrained panels with 2 analytes, where 1.0E-7 >= 'model p-value' > 1.0E-8. Contains 42 panels of 149,894 total panels evaluated. : aA(Fr Im Iv Ji Jl Jq Lv Lx Ma Mb Mx Nj Nt Nv Nw On Pg Po Qd) Is(Fr Ii In Iq Iu Jo Og) Qd(Ax bN cB Dd Jj Nn) Jj(Nn Nt Nv Pg) On(Ii Jo Of Oy) NnIv hRrZ Constrained panels with 2 analytes, where 1.0E-6 >= 'model p-value' > 1.0E-7. Contains 129 panels of 149,894 total panels evaluated. : Qd(Ad Al As aU Ba Bb Bg Bo cL Cs Fr Gp Hb Iu Iv Jm Jo Lj Mu Mx nU Nv Nw On Pc Pj Um) Is(Aa Ad Dd Hr Iv Lj Ly Ma Mb Mu Mx Ns Nt Nv Nw Of On Pc Pg Um) aA(HR Jh Jj Jk Jp Mj Mt Mu Mz Nl Nu Nx Ok Pc Qa) Nn(Im Ji Jl Jq Lv Lx Me Mx Nt Nv Nw Ok On Pg) On(Im Iv Jm Jt Lh Mb Mg Mx My Ng Nm Og) Jj(Fr Im Iv Ji Jk Jq Mx Nx Po Qa) Jl(Hr Ii Im Iv Jo) Um(Mv Mz Nd Qa Tz) rZ(jD nR nU oP) Iv(Fr Nv Nw) Jo(Cu Nt Nv) Vi(dX eP) FrMx MukK MzNf TzcF ImNv nUjI lLoQ lNoP Constrained panels with 2 analytes, where 1.0E-5 >= 'model p-value' > 1.0E-6. Contains 342 panels of 149,894 total panels evaluated. : nU(aA hR Hu Is jD jH Jj Jk Jm Jo Jq lL Lv Lx Lz Ma mE Mj Ml Mp Mq Mu Mv Mx Nd Nm Nq Ns Nu Nv Nw Ny Oh Oz Pb Pc Pe Pf Pz Qa) Qd(Ha Hf Id Ji Jk Jl Jq Ju Ke Kn Ko Kr Ks Lv Ma Nd Nq nR Ns Nt Ok Pg Qv Rm Tz Ue Uo Vt) Ji(Fr Hr Hv Hw Ii Ij Im In Iv Jk Jl Jo Lu Lx Ma Mb Mu Mx Nd Nf Nt Nv Nw Pc Pg Po Um) Nn(Et Fr Ip Jh Jo Jp Ma Mb Mj Mq Mt My Mz Ng Nj Nl Nu Nx Og Oy Po Qa Tz Um) Nw(cB cF Hx Im Jj Jl Lv Ma Md Mh Ml Mx My Nf Nt Nu Ny Oy Pb Pg Po Qa) Jl(Iu Jh Jm Jq Lh Ma Mb Mx Nj Ns Nt Nv Og Oh Ok Pc Pg Um) Iv(Et Im Jh Jp Jq Lv Lx Ma Mu Mx Nd Nt Ok Pc Pg Po) Nv(Hq Hr Ii Lh Lx Mb Mx My Ng Nt Nu Of Og Ok Oy Qa) Um(Hx Jh Jp Jq Kq Mp Mu Nb Nq Oh Or Ou Tn Ut) Mx(Im Jh Jp Jq Lv Lw Lx Ma Nt Ok Pc Pg Po) Jj(Ih Ij Ik Js Lv Lx Mj Mt Mu Nq Nu Ok) Is(As Bo cF Cp Cq Cu Cw Kr Uy Yi Yl) rZ(iC jG jI jY kC kO lL mT nC nH qZ) Nt(Fr Im In Jp Jq Ly Nd Pg) On(eP Hr Iu Jh Lx Mm Mw Nb) lL(aA hR jD jI MU mW nN) Tz(Fr Mu Mv Nd Oh Qv Uy) Im(cB cF Fr Lv Pg Po) Yg(dX Gb Hv Jo Rc) jI(jG lN lO nC nR) Ok(Hr Hw Jo Pg) cF(aJ aP cU Me) Cu(gV Yi Yj) Mu(kG lY nR) aA(hW lN lO) Fr(Jq Nl) Tn(eP mU) Yi(Hv Jr) Qa(Hw In) Jo(Pg Po) Ut(eP lW) aZ(Aa Nb) gV(Li Qe) AdMz MamU MjkG NdQv UaSh QumE YlOu OhwJ aPcB rYoP Constrained panels with 2 analytes, where 1.0E-4 >= 'model p-value' > 1.0E-5. Contains 850 panels of 149,894 total panels evaluated. : Tz(Aa aJ aO aP Bg bN Bo bV cB cS De Eq Fn Gb Gp Hb Hc hG Hr Im Jo Jp Kc kG Li lN Ly Ma Ml Mm Nb nI Nq nU Nw Qy Rf Rx Si St Ub Uf Uk Uo Uw Va Vz Wh Yg Yl) Um(aA aJ aO aP bV cF cT Cu Dc De Fr Fw Gl Hc hG Ij Im Iv jI Jy Ke Lv Ly Ma Mj Mq Mw Mx My Na Nj Nv Nw Om On Pg Po Ps Qb Qe Qh Qt Qv Qy Rf Ub Uf Un Vp Vu) Im(aC aF aN aO aU aZ bV cU De Et gV In Iq Iu Jh Jk Jm Jo Jp Jq Js Lj Lu Lw Lx Ma Mi Mj Mp Mq Mt Mu Mv Mz Nc Nj Nl Nq nR Nu Nx Og Oh Ok Pc Qa) nR(aA HR Hu Is jD jH Jj Jk Jm Jo Jr jY Lh Li lK lL Lx Lz Mb Mj Ml Mm Mn Mp Mq mU Mv Mw Nd Nm Nn Nq Nv Ny Oh Pb Pc Pe Pf Qa qV rX rY) Nd(cB cF De Dp Gp Gz Hf Hl jI Ky lL Lp Lx Mx Ok Pg Po Qn Qt Qy Rf Rx Rz Sf St Tn Ub Ue Uf Uh Uk Uo Ut Vp Vu yD Yg Yi Yf) Is(Al aO aP Ax aZ Bn bU bV cB cS cU Dc De Em Gb Gp mU Qv Rj Rm Tv Uc Ud Ul Uo Up Us Uz Vh Vp Wg Yg Yj) Jj(cB cF Et Ip Ir Jg Jh Jn Jp Lh Ma Mi Mm Mp Mq Mv Mz Nj Nl No Nr Oh Pa Pc Qb Qc Qe Yg) Nw(aZ cU De Fr Gb Hb Hq Hr Jh Jk Jq Lh lL Lx Mp Mq Mt Mu Nj Nl Nm Nv Og Ok Pc Uy Yl) Pg(cB cF Fr Gb Hq Hr Ii In Iu Jh Jm Jp Jq

Figure 32 Continued

Lv Lx Ly mU Nl Nu Nv Og Oy Pc Pe Pf Po Qa) Ok(Fr Hv Ij In Jh jI Jk Jp Jq Lv Lx Ma Mb Mp Mt Mu Na Nl Nm Nq Nt Nu Pc Po Qa) Nv(Et Fr In Iu Jh Jm Jp Jq Lv Ly Ma Mg Mt mU Nj Nl Pc Po rY rZ Yi Yj Yl) Yg(Ad aZ Bb bO cF Ed Hb Jl Jr Ju Ko Ks Mh Or Ow Qa Qd Qx Sf Sh Si Va) jI(An cT Gz hR hW iC Id Ij In Ir Iv Jo kG Ko Ly mP Mr mU Na nH nL nT) Jq(Et Hr In Jh Jk Jo Jp Lu Lv Lx Ma Mb Mt Mu Nl Nq Nu Og Pc Po Qa) Lx(cB Fr Iu Jh Jk Jm Jo Lv Ma Mi Mp Mq MU Mz Nl Nt Oh Pc) Mx(cB Et In Jk Jm Jo Jr Ly Mm Mp Mq Mt Mu Nl Nq Nu Nx Oh Qa) Po(cB cF Fr Hr Ii In Iu Jh Jm Jp Lv Ma Nl Nt Og Oh Oy Pc) Iv(aZ cB In Jk Jo Lw Ly Mi Mm Mp Mq Mt Mz Nq Og Oh Pa Qa) Me(aJ aO aP aU aX aZ bA bV cB cS CU De dF gL Hc nY) Qa(Et Fr Hv Ij Iu Jh Jm Jo Jp Lv Ma Mu Ns Nt Nx Pc Yj) aZ(aA aJ aO aP cF cS cU De dF Fr Hr Lu Lv Mu Nt Yh) cF(aA aO BA cG cS dF Fr Jo Lv Mi Mu On Or Yi) mU(AA Hu Jm Lu Lv Mj Mv Nq Ny Pf Qd Vv) lL(Fr lK Ly mM mP mT nB Nn Nq nT oO oP Qd) Nt(Jh Jm Lv Ma Mg Mp Mu Mz Ng Oh Pa Pc) Jr(cB Dr Du Em Gb Gz Hl Uz Wg Yj Yl Tl) Fr(Hq Hr jG Jo lN Lv Mb Mq Ng Nj Oy) cU(aA aJ aP aV bA Bo bR cB De dH Hr) Cu(Aa Ad Hr Mm nI Nm oO Pb Uz Wg) aP(aC bL bN bR bW dA De dG dH) oO(aJ Aw bQ cT dF Kq oQ Ps Vi) Mz(As Cq Cw Hr Hw Ij In Rj) kK(Hu Jk Mj Mv Mw Nn Nq Qd) Lv(Bo cB Jh Ji Jp Mt Mu) Ua(eP Gd Lp Sf Si Va Vb) aJ(bN bR cB De dG iC lM) Mu(cB lN lO My Oy Ue) Qd(Gb mP mZ Si Uy tF) Ji(Iu Jh Jp Nl Nu Om) Jo(Ba cB De Et Tn Ut) nI(Kq Ky Qu Tn Ut Uw) Hu(Gb Gd kG Vb Yi) Jl(Hl Uy Yi Yj Yl) Oh(Qv Qz Ra Rg Uo) On(cB gV Vh Yi Yj) nU(Jn lK oP oQ Vv) gV(bA Mn Pf Qb) oP(lK qV rB rX) Aa(aA bA Ed) De(Bo cS Hr) Qu(kI lW lY) Jk(kG Ng Oy) Ut(Hr Mm Qv) Vb(Hc Mv Vv) hR(lN rX rY) oQ(jL lN rY) Ly(wL yD) Mj(kF mP) Mp(kN wJ) Nb(cB Yj) Ps(Uo Uy) Pc(Jp Mt) aA(cB lM) cP(Jd Uf) AwkN GzjP MvUe HrVu HvYj TnpK XadX KylN YlOr NymP UoVi UwnH VaVv jDrY

Constrained panels with 2 analytes, where 1.0E-3 >= 'model p-value' > 1.0E-4. Contains 1,952 panels of 149,894 total panels evaluated. : Yg(AA AJ Al aM AP aR aV bI cA cB cC cK cN cU Cv De dJ dL dM Ex Fn Gd Gz HC Hp Ib Ii Iz Jn Js Jt Jv kE KG kI Kj Ld Lz Ma Mj Ml Mm Mq Mz Nb nH nI Nm Nn Nw oE oF Oh Oi Om oO Ou Oy Pf Pj Qb Rh Rt Rx Tr Um Uo Uu Vb Wh Yi Yj) cF(aN aR aX BO bQ bV cL cT Cu De dG Di dM ED Fw Gl Gp Hf HR Iv Jf Jl Jl Jp Jq Jr Jy kF Ky Lu Lx Ly Ma Mb Mj Mp Mq Mt Mv Mx Nb nI nO Nq nR Nt nU Nv nY Ok oO oP Ou Pe Qa Qb Qe Qh Qv Rf Sf St Tn Ub Uf Uo Ut Vp Vu Yh tF) jI(Ad aK As Ax bA Bc Bo Cp Cq Cs Ct Cu CW Dc Dd Gp Hr Hv Hw Ii It Jn Jr Js Kd Kj Kn Kp Kq Kr Ld Li Mf Mu Mz Nf Ni Nj Nn Nq Nr Om Pc Pe Pi Pk Ra Rj rY Tv Uc Ud Ul Uo Up Us Vp) Is(An Bb bN Dg Di Dr Du Fn Gn Hb Hl Id Ju kC Kd kF kG kK Kn Ko Kp Kq Ks IL mP nN nT nY oP Pi Pj Pk Qy Ra Rb Rt rY rZ Si Ub Ue Ug Uk Ur Uu Uw Va Vb Vi Vo Vs Vt Wc wJ Tl) Mu(aJ aO aP As bA Bo bV cK cT cU dF ED Et Gp HR jG Jh Jo Jp Js Lw Ly Ma Mb Mi Mj Mp Mt Mz Nd Ng Nj Nl No Nu Nx nY Og Oh Pc Qb Qv Qz Rf rY Ub Uk Uo Ut Yi Yj Yf) aZ(aN AR Aw BA BG Bn BO bV cA cC cG cT Cu Di Dk dM Eq gV Ih Ji Jj Jl Jo Jr kN Lx Ly Ma Mb Mj Mq Mt Mv Mx Nd Ni Nn Nq nU Nv nY Og On Pg Po Uy Wd Wh Yi) Yi(Aa aV Aw cN Dc Dk dM Dr Gb Hb Hc Hq Jh Jn Jo Js Ju Kq Ks Lu Mj Mq Mv Mw Nb Nq Nw Oh oO Ou Ow Qa Qd Qw Qy Rh Sf Ua Ub Um Uo Ut Uy Vp Wh Yj Xa) Ut(aJ As Bb bN Bo cB Dp Gb Gd Gp Gz Hb Ii Im Iu Jj Jp Ju Kj Ks Lh Li Ly Ml Nb Nf Nm Nn Nw Of oO Rf Si Tr Ub Ue Ug Uk Ul Uo Uu Vb Vh Yj Tl) Nd(aJ aO aP bA Bo bV CU dF Di Et Fw Gb Gl Hc hG Jh Jj Jq Kc kG Lv Ma Mb Mj MP Mt Nj Nl Nu nY oE Ou Ow Ru rZ Uy Vj Wb wJ Yj Tl) Bo(aA aJ aN aO aP aR aX BA bO bV cG cS cT Cu dF Fr Im Iv Ji Jl Jq Jr Mc Mi Mj Mm Mx Mz Nb Nt Nw nY Ok On Or Qe Tn tF) De(aA aO Ar As BA bO bV cT Cu dF Di Fr Gd Gp Iv Jj Jr Lu Lv Ly Ma Mb Mm Mx Nb Ne Nf Of Og Oy Oz Qb Qe Yj) mU(Cu Cv Di Ez Fy hA Hq iB Ii jD Jj Jk Jl Jn lK Lz Me Mp mZ Ne Nm Nn Ns Nw Og Ou Pb Pc Rz Tr Uf Um Uy Vi Vu) Lv(aJ aP aR As aX bN bU bV cS cU dB Et Gp Ih Ip Jk Jo Js Ly Ma Mi Mj Mm MP Mq Mz Nl nN No Nq Nu Oh Pc) Mv(aJ aP cU Dp Ed Gb Gd Hl Iz Jd Jf kG kN lL Qv Rf Rt Ru rY rZ Sf Sh Si St Uk Uo Uy Vh Wc Yj Yl Tl Yf) Um(aR bA Bg bN bP cB cL Cp cS cU dF Dk Ef Ex Fy gL Gp jH Kd Ky lL nI nR nU nY oE Qn St Vi Yh Xa tF) Mz(Et Hv Id Jh Jk Jp Kr Ma Mb Mi Mm Mp Mq Mt Nj Nl Nq Nu Nx Oh Om Pc Qa Ra Tv Ud Ul Up Us Wg wL) Oh(Et Gp Hb Hf Jh Jk Jp Ju kF kG kK kN Kr lL Ma Mp Mt mZ Nl Nu Nx nY Qa Ru rY rZ Uy wK Yj Yl) Cu(aN As bN Cq cU Dg Dl Gb Hl Hw Ii Im In Jj Jt Lh Li Lu Mb Nf Ng Of Oy Uy Vb Vh Vi Wc Yl) Gp(Aa aC aJ cA cB cU Fw hG Im Jl Jo Jr Ju Lu Me Mm Mq Mx Nb Nw nY Or Ou Oz Pg Po Qv Rf) Ma(cB Et Ih Jh Jk Jo Jp Js Lw Mi Mj Mp Mq Mt Nc Nj Nl No Nu Nx Pa Pc pK Qb Qe rY rZ) Im(aK aP aY bA bF Bg Bn bO bS cG cL cS cT dF Di Dl Gb Gl hG Ju lL Ou Qe Qv Ue Ul Uo) Nw(aC aP aU Ax Bb Bg bU bV cK cL cS Di Ju mP nT Pj Qt Qv Qy Rg Rx Sf Si Uo Uw Vz Yj) cU(aO As Aw Ba bU cA cS cT cY dB Di dJ Fr gV Iv Ji Jj Jo Jr Lh Ly Mb Nb nI Nt Oy Pz) Qa(Aa Ad As cB Cq Cw Du Hl Hr kK Kr Lj mP mZ Nq Og Ra Rj Tv Ud Ul Up Us Uz Vp Wg) Jk(Et In Ip Jh Jm Jo Jp Js kF Lw Ly Mb Mi Mj MP Mq Nj Nl No nT Nu Nx Og Pc rY) lL(aD aM bC bO Gz iB In Jl Jq Ky lM Lw lY Mf Mm Mw Mx mY Ni NO Nv On Pc Po Tz) nI(aF aO Aw bQ bZ cG cS Cv dF Di Dk Fw Fy iB Jl nY Ou Pi Ua Uf Vu Vv Yd Yj tF) Ly(aJ aP cB hA Hc hG hR jG jO lM mP Mt Nl nY oE oF Qv rZ St Tn Uo Vp Vu wK) Jh(Et gV Ip Jp Js Lw Mi Mj Mp Mq Mt Nj Nl No Nq Nu Nx Og Pa Pc Qb Yj) Jl(cB Dp Du Fd Gb Hp Jf jG Ks mP nC Qv Ry Uo Uz Vb Vh Vi Vj Wc Wg Tl) Jo(aJ aO aP Aw bA Bg cG cL Cp cS cT dF Dk Fw Gl Jp Js Mt Nx Ou Uf Vu) Tn(Ad aJ As Bb cA cB Dp Gb Gz Hr Ib Kj Li Mm Nm Of Qv Ue Uk Uy Vb) oO(aF aO aP bA bV bZ cL Cv dG Di fR Hc hG lN oE oF oP pH Rz Wh Xa) Jj(aP Bg Ii Il Io Jr Jt Lw Mb Md Mf Mg mP Mr Nc Nh Ny oP Pe Pz) Jp(Gb Hb Lh Lw Mb Mi Mj Mp Mq Mt Nj Nl Nq Nu Nx Qv Qy Rf Tr Uo) cB(bA bV cS Fr Hr Ji Lu Mi Mj Mm Mq Ns Nt nY Qb Qe Rf Uo Vu Yh) kG(Aw Di Dk Fw Ib Mw Nq Nv Ny oP Ou Pb Pc Pg Ps Ua Vv Wh Yj Xa) Nv(eD Hl jG jT lN lO mP rX Ry Uy Uz Vb Vh Vi Wc Wg wJ Tl) Uo(aA aJ aO aP bA bV cT dF Ex Fr hG Nb Nn nY Qv Rf Xa tF) Ps(Gb Hb nU Ud Ul Up Us Uz Vb Vh Vp Wc Wg Yj Yl Tl Xa) mP(aA Hu Jn Jq Lx Lz Ml Mq Nm Nq On Pc Pf Pg Pz Tz Vv) Nn(hR jG lN nK Qv Ra Rf Ru rX rY rZ St Ub Ue Uk Ul) Me(aK aR aV Ba bF bO bU cG cL cN cT cY Di Dk Fw tF) aJ(Aw Ba Bg dF Di Gl gW HR Iv Jf Jr Mi Nb Oi On) gV(aL Ao Ba bO Cp cT dB Dc dD gP It Iv Mt Nt Ok Po) Fr(aC aR aU bA bL cT Dg Di Dp eD hR kK lO Qv rY) Gb(Co Dk Fw Hc Hq Lx Nt On oP Ou Ow Pf Ua Vu Vv) Yj(Dk Hu Jn Js Mj Mq Mw Ny Ou Ow Pg Qd Ua Vi Xa) Pc(Et Js kK Mb Mi Mj Mp Mq Nj Nl No nT Nu Nx Qb) aA(aC aN aR Ba Bg bO dB dF Di Dk kN mZ oP rY rZ) aP(Bg Di Hr iC Iv Jf Jr Lh lM lN Mb Mm Nb Nm Oi) Nq(jG lN Nj Nl nN Nu Oy Qv Rf rY rZ Sf Ue Yl) Hl(Dk Hc Ho kN Mw Nb On Ou oW Qd Vi Vu Xa) Hr(Aw bA bV cT Dc dF Ed Fw hG nY Or Ou Vp) hR(eD hX iB In jD jH jO Ld Lj lM mM nN oQ) Mp(Hq Jq lY Mb Mi Mj Mq Mt Nj Nl Nu Qv) Hu(kF nN nT oP Rx Sf Sh Ux Va wJ Yl Yf) On(Ad As Du Em jG Rt Uz Vb Vi Wg Yl Tl) aO(aN aR aX bA bN bO cS Iv Jf Jr lW Mi) Aa(cT Dc Iv Ji Ke nU Pi Qd Vi Vj Xa) Pg(kF kK nN nT nY Qv Sf Si Uy Vb wJ) Tz(eD cF gL jD jV kN nR nY Vj tF) Ua(Gz Hp kN mE nN nR Rt Ux Uy Yl) Ou(Gn kF kI kN Qv Rf Uy Uz Vh Wg) cS(aC aN bA bN bO cT dF Di Dk Iv) wJ(Hv Ih Il Ip Ir It Iu Iv Mx wL) Mi(bV In Mb Mq Mt Nj Nl Nu Nx) Mj(Et In Lw Mm Nj Nl Nu Og rY) Nb(Du Gz kK Qv Ue Vh Wg Yl Tl) Qd(Hp jG lN Lp oP Rv Vb Yk Yl) Aw(bA Em Gd kE lW oV Oy Yf) Di(aR bA cT dF Iv kN nR nU) Jq(Ad As Cq Cw Hw Ii Mq Wg) Jr(bA bO dF Gn Rx Ry Si Xa) Fw(aF cA cT hG Mm nK Qv) Hc(eQ Gd Gz Sf Ux Va Tl) Wd(dX kE kN nC nH nU Vb) nY(cI Gl hG Jf oE Oz tF) Nl(Et Lw Mm Mq No Nu) Wh(dX Ed nC nH nL nU) Qv(Gl Ml Mx Ns Po Vu) Xa(Dr kE nH nU Rj Vu) Vv(nN nR Ux Uy Vj Vw) cT(Dr Em eQ Gn oT oV) jG(bO Gz hA jD Ky Po) rZ(Il Mf Mx Nj Qc Wm) Hq(Sf Uy Vb Vj Yl) Iv(aU aX Bg bO bV) Ji(Ad As Cq Cw Dd) Kq(Hw lW lY mE Ud) dF(aR aX Dg dH Lh) nR(Cv Ju kN mW Rb) wL(Ih Ip Nu Og tN) iB(Gz mW mY nA nT) oP(Lx Mb Mm mZ Nm) Ba(Dg Mm oT oV) Et(Mb Mq Mt Pa) Gl(cA Hb Lu Mm) Ny(kF lO nN nT) Ow(Si Vz Yk Yl) Vi(Ad Dr nH nJ) Pf(kK mZ nN nT) kN(aF Cv Ke Uf) Mq(Mt Nu Yk) Hv(Uy Uz Wg) Uw(mH nC nJ) Vu(Dp Lp Si) bV(Jf nU Po) As(Dc Or) Dk(mE Yl) Ef(Oy Uk) Ed(Lu Yh) Gz(lN Pz) Lw(Mt Nu) Lx(kK mZ) Mx(aX rY) My(rY Vb) Qy(Oy Ue) Jn(Uz Wg) Js(In Uy) Ky(eD lM)

Figure 32 Continued

Rz(kE kI) Uf(nK pK) gL(aC tF) nU(Cv Qn) mW(hA jF) nH(Rv Zx) jD(IN rX) lO(Md Mw) oQ(mZ rX) oV(bA bF) AdDc PoaU ExMm LuaX HodX YhaV YkbO QbJm JfhG LdeP RftF OaUy VjPa bCoT bRkF cGdH eDiZ

Unconstrained panels with 3 analytes. where 0.0E0 >= 'AUC p-value' > 0. Contains 50,000 panels of 25,049,241 total panels evaluated. : eP{Ut(AA aC aD aE AF aG aH aI AJ AL aM AN AO AP aQ Ar AS aU aV AW AX aY aZ Ba BB BC bE bF BG bH bI bJ bL bM BN BO bP bQ bR bS bU bV bW bX bZ cA cB cC cD cF cG CH cI cJ cK cL cM cN CO Cp CQ cR CS CT CU CV cW CX cZ dA DB DC DD DE dF DG dH DI dJ dK DI dM dN Dp DR dX Ed eF EM Eq Ex Ez Fa Fb Fd Fi Fn FP FR Fw Fy Gb Gc Gd Gh GL Gn gP Gz Ha HB HC HF hG Hq Hr Hu Hv Hw Hx iA Ib Ic IH Ii Ij Ik Il In IO Ip Iq Is It Iu Iv IZ Jd Je Jf Jg Jh Jj Jk Jl Jm Jn Jo Jp Jq Jr Js Jt Ju Jv Jy Kc Kd Kf KG Ki Kj Kk Kl Kn Ko Kp kQ KR kS Kx Ky Kz Li Lj Lp Lu Lv Lw Lx Ly Lz Ma Mb Mc Md Me Mf Mg Mh Mi Mj Mk Mm Mn Mp Mq Mr Ms Mt Mv Mw Mx My Mz Na Nb Nc Nd Ne Nf Ng Nh NI Nj Nk Nl Nm Nn No Nq Nr Ns Nt Nu Nv Nw Nx Ny Oa OE OF Og Oh Oi oN Op Or Ou Ow Oy Pa Pc Pd Pe Pf Pg Ph Pi Pj Pk Po Ps Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sh Si Ss St Tn To Tt Tz Ua Ub Uc Ud Ue Uf Ug Uh Uk Ul Um Un Uo Up Us Uu Uv Uw Ux Uy Va Vb Vh Vi Vo Vp Vq Vs Vu Vv Vw Wd Wh Yd Yg Yh Yi Yj Zw Zx Tl Xa Wm Tj Ti Th Yf) Ps(AA Ad aE AF aG aH aJ aK AL aM AN AO aP aQ aR AS aU aV aW Ax aY aZ BA Bb BC bF BG bH bI bJ bM BN BO bP bQ bR bS bU bV bW bZ cA cB cC cD cG Ch cI cK cL cM cN cO cP CQ cR cS CT CU CV Cw cX cY DB dC DD De dF dG dH DI dJ dK DL dM dN DR Du Ed eF EM Eq Et Ez Fc Fd Fi FR Fy Gb Gc Gd GL GP Gz hC Hf HI Hr Hu Hv Hw Hx iA Ic Id iH Ii IJ Ik Il IO iP Iq Ir Is Iu IZ Je Jf Jg Jj Jk Jm Jo Jp Jq Jr Ju Jv Jy Kc Kd Ke Kf Kg Ki Kp KQ KR KS Kx Ky Kz Lh Li Lp Lt Lu Lv Lw Lx Ly Lz Ma Mb Mc Md Me Mg Mh Mi Mj Mk Ml Mm Mn Mr Mu Mw Mx Na Nb Nc Nd Ne Nf Ng Nh Ni Nk Nl Nm No Nq Ns Nu Nw Nx NY Oa Oe Of Og Oh Oi Ok Om ON Or Ou Pa Pc Pd Pe Pg Ph Pi Pj Pk Po Pz Qa Qb Qc Qd Qe Qh Ql Qm Qt Qu Qv Qw Qz Ra Rb Rc Rf Rj Rt Ru Rv Ry Rz Sf Sh Sj Ss St To Tv Tz Ua Ub Uc Ud Ue Uf Uh Uk Ul Um Un Up Ur Us Uu Uv Uw Uy Uz Va Vc Vh Vi Vo Vp Vq Vs Vt Vv Wb Wc We Wf Wg Yd Yg Yj Yl Zw Ye Tm Tl Xa Tj Ti Th Yf) Tn(AA aC AD AF aG aH aI AL AN AO AP aR AS aV AW aX aY BA bB BC bF BG bI bL BN BO bP bR bS bU bV bW bX cA cB cC cD cE cF cG CH cI cJ cK cL cM cN CO CP CQ cR CS CT CU Cv CW Cx cZ dA dB Dc DD DE dF DG dH DI dK DL dM dN Dp dR dX Ed EF EM Ex Ez Fa Fb Fp FR Gc Gn gP Gz Hc HF hG Hr Hu Hv Hw Hx Ic Id Ih Ii Ik Il In Io Ip Iq It Iv Jd Je Jf Jg Jh Jj Jk Jm Jn Jr Js Jt Jv Jy Kd Kg Kk Kl Ko Kp Kq kR Kx Ky Kz Li Lj Lp Lu Lv Lw Lx Ly Ma Mb Mc Md Me Mf Mg Mh Mi Mn Mp Mq Mr Ms Mt Mv Mw Mx My Mz Na Nb Nc Nd Ne Nf Ng Nh Ni Nj Nk Nl Nm Nq Nr Nt Nu Nv Nx Oe OF Og OH Oi oK Ou Ow Oy Oz Pa Pb Pc Pg Pi Pj Pk Po Pz Qe Qg Qh Ql Qn Qt Qu Qv Qw Qy Ra Rb Rc Rf Rg Ri Rj Rm Rt Rx Sf Si St To Tr Tt Tv Ua Ub Uc Ud Ue Uf Uh Uk Ul Um Uo Up Ur Us Uu Uv Uw Ux Va Vb Vi Vo Vp Vq Vs Vt Vv Vw Wd Yj Zw Wm Tj Ti) Xa(AA AD AF aG aI aJ aL AO aV aW aY aZ bA BB BC bE BG bH bJ bL Bn Bo bQ bV bW bX cB cC cE cF cG Ch cI cJ cL cM cN cO cP CS CT CV Cx cY cZ dA DC dD De dG dH Dk dL dN Dp Dr Du dX Ed eF Eq Et Fc Fd Fi Fn Fp fR Fy Gc Gd Gh Gn Gz HB Hc Hl Ho Hp Hq Hr Hu Hw Hx iA Ib Ih Ii Ik Il Im Ip Iq Is Iu Iv Iz Jd Je Jf Jg Jj Jk Jl Jo Jp Jq Jr Jt Ju Kd Kf Kg Kj Kn Ko Kp Kq kS Kx Ky Kz Lj Lp Lu Lv Lx Mg Mk Ms My Mz Na Nb Nd Ng Nh Nk Nm No Nq Nr Nt Nu Nv Nw Nx Oa Oe Og Ok Om On Op Ou Oy Pb Pd Pg Pi Pk Pz Qc Qd Qm Qt Qu Qv Qw Qz Rf Rg Rh Ri Sf Si St To Ua Uc Ue Uf Uk Us Uu Uv Uw Vh Vo Vp Vq Vs Vu Vv Vz Wb Wd Wh Yg Yh Yj Zx Tl Tj Yf) Yg(aA aH aI aJ aM Ao aQ AS aU AX aZ bC bL bX bZ cC cE cH cJ cN cQ Cs cU Cv cW Cx cZ dD dE Dg dH dJ DK DL dN Du dX Ed Eq Fd Fn Fr Fw Gb Gc Gd Gl Gn Gp Gz HB Hc Hf Hl Hq Hv Hx iA Ic Id Ih Ij Im In Io Iq Is Jd Jf Jh Jj Jl Jo Jp Jq Jv Jy Kc Ke Ki Kk Kr Ky Lh Li Lj Lp Lx Lz Mb Mf Mg Mk Ml Mm Mr Ms Mt Mv Mx Mz Nb Nd Nf Nh Ni Nj Nm Nn Nq Nr Nu Nv Nw Ny Oa Oe Oi On Or Ou Ow Pe Pf Ph Po Pz Qa Qb Qd Qh Ql Qm Qn Qu Qx Qy Qz Rc Rf Rg Ri Rm Rt Rv Si Sj Sr Ss St Tv Tz Ub Uc Uf Un Up Ur Uu Uv Uw Ux Vb Vi Vt Vu Vw Wb Yh Yi Yj Yl Zx Tl Tj) Vi(aA aE aH aJ aM An Ao aR aY aZ bJ bN bW bZ cD cF cI cM CO cR Cs Ct Db dD Dg Di DK Dl dN Du dX Ed Fd Fn Fp Fr Fw Gc Gd GL gP Gz HC Hf Hl Ho Hw iA Ih Im Iv Iz Jd Jj Jq Jr Ju Jv Ke Ki Kl Kq Kr kS Ky Li Lj Lp Lv Lz Mj Ml Ms Mw Nb Ne Ni Nn Nq Nr Nu Nw nY Oa Oe Oh Om ON Or Pe Pf Ph Po Qa Qb Qc Qd Qe Qg Ql Qm Qx Rg Ri Rt Rz Sf Si Sj St Tv Ub Ue Un Up Ur Uu Uw Va Vo Vt Vw Vz Yi Tj Ti Yf) Yi(aD Ao Ar Aw aY aZ Bb bC Bg bH bL bQ bV cE Ch CP Cs cU cV De DK dN Dr dX Ed eF Fd Fn Fp Fw Fy Gc Gn Gz Hb Hu Hv Hx iA Ib Id Ih In Is Iv Iz Jf Jg Ji Jk Jm Jq Jt Ju Jv Kj kQ Ky Lh Lx Lz Me Mf Mk Ml Mt My Mz Nb Ng Nk Nl Nr Nt Nv Oh Oi Om On Or Ow Pb Qa Qc Qd Ql Qm Qw Qx Qy Qz Rf Rh Ri Rm Sf Sh St To Tv Tz Ua Uc Ue Uh Un Ur Us Uv Vs Vu Wd Zx Wm Tj) On(Ad Aj Aw Ax bI bO cI cU Cv dB Dl Dr Du Ed Eq Ez Fa Fc Fd Fi Fy Gb Gc Gd Gh Gn gV Ha Hl Ho Hp Ii Io Iu Jf Jj Jo Jt Kc Kf Kj Kk Kl Kn Ks Ky Ld Lp Lt Mm Nd Nm Nn nY Oa Of Oh Ok Op Ou Ph Pz Qv Qz Rc Rf Rm Rt Ru Rv Rx Ry Rz Sf Sh Si Sj Ss Ug Ur Uu Uv Uw Ux Uy Uz Va Vb Vc Vh Vo Vv Vw Vz Wb Wc Wd We Wf Wg Wh Yd Yh Yj Yk Yl Zw Zx Ye Tm Tl Ti Th Yf) Uw(Aa Ao Aw Ax cG Ch cM cQ Cs cU cW Dc dG Di dL dR Ed eF FP fR Fw Gc gL GP Gz hB HC hF hG iA Ib Ic Id IH IJ Im iO iP Iv iZ Jf Jg Jl Jn Jq Jr Jt Ke KQ kR KS Ky Lj Mj Mn Ms Mw Mx My Mz Nb Nn Nq Nv NW NY Oa oE oF oH oK Om oN PF Pi Pk Po Qa Qb Qc Qd Qe Ql Qm Rf Sf Sh St Up Vp Vu Vv Wd) Ld(aA aJ aP Ax bA Bg bO Cp Cq Cs Ct CU dB dF dG Dk dM Ed Ef Ex Fb Fp FR Fy Ha Hq Hu Hv Hw Hx Ij Ik Im In Ip Iq Ir Is It Iv IZ Jd Jh Jk Jl Jn Jp Jq Jr Js Jt Ke Kj Kq Kr Ky Li Lx Me Mj Mt Mv Mw Mx My Mz Nn No Nq Nu NY Oa Oh Ok Om Pf Pg Pi Po Qa Qc Qd Qe Qh Qu Qy Rm Sr St Tv Ua Uc Un Ur Vs Vv) Kq(aC Ad aF Aj Ap aR Aw bA bF bI bV cI cO cT CU Cw Dg dH dK Dl Dr Ed EF Ex Fa Fi Fp Gh Gn Hb Hc Hq Iu Iz Jj Jo Jp Jt Kf Kl Kn kR Ks Li Lj Lu Me Mm Nj Nk Nm Nn Ns Nx nY Oa Og OH Ou Pf Ph Pj Po Pz Qz Rm Ry Rz Sf Sj Ss Ue Ug Uu Ux Uy Va Vb Vh Vo Vq Vv Wb Wc We Wh Yj Zx Tm Ti) Is(aO Aw Ax bA bO bV cD cF cH cI cT cU Cv dB Dr Du Ed Eq Fc Fd Fi Fy Gb Gc Gd Gh Gn gV Hl Ho Hp Hu Ii Iu Jf Jj Jm Jo Kf Lp Lt Lu Mm Nm Nn Ns nY Oa Oh Op Rm Rt Ru Rv Rx Ry Rz Sf Sh Si Sj Ub Ux Uy Uz Va Vc Vh Vo Vw Vz Wc Wd We Wf Wg Wh Yd Yh Yj Yk Yl Zw Zx Ye Tm Tl Ti Th Yf) Wd(aG aH aI Ao aP Ar aU AX bO bZ cE cO Cq Cs dG Dk dL dX Fr Fw Gp Hb Hf Hq Hx Ih Ii Im Iq Ir It Jd Jj Jl Jp Jq Js Lh Li Lj Lp Lv Lx Lz Mb Mj Ml Mm Mp Mq Mr Mv Mz Nb Nh Nq Nr Oa Oe Ok Or Ow Pf Qa Qb Qc Qh Qx Rf Rm Si St Uc Uf Un Up Vb Vq Vt Vu Wf Yd) Jd(aA aC aH aI Aj aL aO aS Aw bF bI bU bV cF cO Cq cT cU dB dF dK dR Ed Eq Ex Fa Fb Fc Fd Fi Fy Ho Hp Jf Jj Jo Jp Jr kG Kl Kp kR Kx Ky Lp Lt Mm Nj Nm Nx nY Og Ou Ow Pa Pz Rt Ss Ue Ug Uh Uu Ux Uz Vh Vo Vz Wb Wc Wf Yh Yk Yl Zx Ye Th Yf) Qa(aC aO Aw bA bV cT cU dB dH Du Eq Fa Fc Fd Fy Gb Gd Gh Ha Hc Hl Ho Hp iA Iu Jf Kf kR Lp Lt Mm Ns nY Oa Op Ou Rt Rv Rx Ry Rz Sf Sh Si Sj Ub Ux Uy Uz Va Vb Vc Vh Vo Vq Vw Vz Wb Wc We Wh Yd Yh Yj Yk Yl Ye Tm Tl Ti Th Yf) Pe(aL aO Aw Ax bA Bn bV cI cT cU dA dK DR Eq Fc Fi Fy Gb Gc Gd Gh Gn gV Hl Hw Ii Ik Jf Jj Lj Lp Lt Mm Nk Nl Nn Ns nY Oa oH Op Ou Pf Qw Ru Rx Rz Sf Si Sj Uz Va Vc Vh Vo Vw Vz Wb We Wf Wg Yd Yh Yj Yl Zw Zx Ye Tm Ti Th) Qd(aC aO aS Aw bA bF bV cT cU dB dK Dr Du Em Ex Fc Fd Fi Fy Gb Gh Hc hG Hl Ho Hp Jr kR Lt Lu Ns nY Op Rt Ru Rv Rx Ry Sf Sh Si Sj Ub Ux Uy Uz Va Vb Vc Vh Vw Vz Wc We Wf Wg Wh Yd Yh Yj Yk Yl Zw Zx Ye Tm) St(aO Aw cU dK Dr Du Ed Eq Fc Fd Fi Fy Gb Gc Gd Gh Gn Hl Ho Jj Jp Kc Lp Lt Mm nY Ou Ow Rt Ru Rv Rx Rz Sf Sh Si Sj Ux Uy Uz Va Vb Vc Vh Vw Vz Wb We Wf Wg Wh Yd Yh Yj Yk Yl Zw Zx Ye Tm Tl Ti Yf) Jr(Aw aX Ba bO bW cF Co cS CU dB De Du Em Eq Fd Fi Gh Gp Gz Ho Hp Ii Im Jj Jm Jp Kj Kx Li Lp Lt Lv Mi Mk Mu Mv Mw Nh Nn Nq nY Om Ow Qy Rb Rj Rx Rz Si Ua Ub Uc Uf Ur Vc Vu Vz Wb Yk Yl Ye Tm) Im(Aw bA Ed Ef Ez Fc Fy Gb Gc Gd gV Ha Hb Hc hG Ho iA Je Jy Kf kG Mm Nj Nk nY Oa oH Ou Ph Pj Qw Qz Rm Rt Rv Si Sj Ss Ub Uc Ug Uh Uu Uy Uz Va Vb Vc Vh Wc Wf Wh Yd Yh Yk Zw Ye Wm Ti Th) Wh(Aa Ax cG Cp Cq cU Et Fw Gc Hq

Figure 32 Continued

Fr Hu Hv Hx Ih Ij Ik Io Iq Is Ji Jl Jo Js Lh Li Lj Lx Ly Lz Mb Me Ml Mp Mq Ms Mt Mv MW Mz Nc Nd Nf Ni Nj Nl Nn No Nq Nv Nw Ny Oh oO oP Pd Pf Po Qa Qc rZ) hA(aA Fr Hv Hx Ih Ij Ik Im Is Ji Jl Jn Jo Jq Js Lh Li Lj Lx Ly Lz Mb Mj Ml Mp Mr Mt Mv MW Nc Nf Ni Nl Nn No Nq Nr Nw Nx Ny Oh On oO oP Pd Pf Po Qc Qd Qe rZ) jQ(aA Fr Hx Ij Im Io Iq Is Jh Ji Jn Jo Jq Js Lh Li Lj Lx Ly Lz Mb Mj Ml Mp Mt Mu Mv MW Na Nc Nf Nh Ni Nn No Nq Nu Nv Nx Ny Oh On oO oP Pd Pf Po Qc Qe rZ) jH(aA Fp Fr hV hW HX Ij Im In Ji Jj Jo Jq Js kE kl Lh Li Lj Lx Ly Lz Mb Me Ml Mp mS Mt Mv Mw mY Nf Ni Nn Nq Nr Nv Nw Ny Oh On oO Pe Po Qa Qc rB rX rY) lO(aA Fp Fr Hx Ih Ij Im Is Jh Ji Jn Jo Jq Js Lh Li Lx Ly Lz Me Mj Ml Mq Mt Mv MW Mx Nc Nf Ni Nn No Nq Nr Nv Nw Ny Oh On oO oP Pd Pe Pf Po Qa Qb Qc rZ) Hl(Aw bA cT Cu dG dI Dk Ef Gl Hc Hq Hu Jh Jk Jl Jn Jr Js Kq Mj Mu Mv My Nn Nv Oh Om oN Pb Pf Pg Ps Pz Qa Qt Qu Qw Qz Tv Tz Ua Uc Ur Vp Vs Vu Vv Wf Yg) qX(aA Fr Hx Im Is Jh Ji Jn Jo Jq Js Lh Li Lj Lx Ly Lz Mb Mj Ml Mp Mq Mu Mv MW Nc Nf Nh Ni Nn No Nq Nr Nu Nv Ny Oh On oO oP Pd Pf Po Qb Qc Qe rZ) Tn(Al Bb Cv Dr Eq fB Fc Fd Fi Gd Gn Ho Jo Jt Lp Mb Mm nI Nm Oh Oi oO Op Ph pK Rb Ru Rz Sf Si Ug Ux Uy Va Vh Vj Vw Wb Wc Yh Yi Yk Zw Zx Ye Th Yf) jL(aA Fp Fr Ij Ik Im Io Is Ji Jj Jn Jo Jq Js Lh Li Lj Lx Ly Lz Me Ml Mt Mv Mw Nc Nf Ni Nn No Nq Nr Nv Nw Ny Oh On oO oP oQ Pd Pf Po Qc Qe rZ) rZ(hV hW hX jO kE kG kI kN kO kP lW IX lY mE mF mH ml mM mP mS mT mU mY mZ nA nB nC nD nF nH nI nJ nK nL nM nN nO nR oO qT qW rB rC rX) qT(aA Fp Fr Hx Ih Ij Im In Io Ji Jo Jq Js Lh Li Lx Ly Lz Me Mj Ml Mp Mt Mv MW Nc Nf Ni Nn Nq Nr Nv Oh On oO oP Pd Pf Po Qa Qc) jO(aA Fr Hx Ij Im Io Is Jh Ji Jn Jo Jq Js Lh Li Lx Ly Lz Mj Ml Mt Mv Mw Nc Nf Ni Nn No Nq Nr Nv Nw Ny Oh On oO oP Pd Pf Po Qa Qc) Yg(Ad aF aZ Bb dH Gb Gd Hv Iz Jj Jo Kg Kj Nm Pf Qa Qb Qd Qu Qv Qx Rc Rg Rt Ss Tz Ug Uk Ul Uu Ux Vj Vo Vt Vw We Yj) qW(aA Fp Hq Hx Im In Io Ji Jo Jq Js Lh Li Lj Lx Ly Lz Mj Ml Mp Mt Mv Mw Nf Ni Nn Nq Nv Ny Oh On oO Pd Pe Pf Po Qc) Jr(Dr Du Eq Gb Gn Ps Rt Ru Rv Ux Uy Uz Va Vb Vc Vh Vi Vj Vw Vz Wc We Wf Wg Yi Yj Yl Zw Yf) Hq(Du Fd Fi Gb Gn Lp Ps Rt Rv Rz Sf Sh Va Vi Vw Wc We Yi Zw Yf) Ps(aQ Aw bF bO Co Dd Di Gb Gp Hp Jh Jm Jq Ld Lp Mv Nc Pb Tz) Uy(aV Aw Co Cu Jq Kq Lh Mj mU Nd Nn Nv Nw Om oP Ou Pg Qa Tz) Vi(Aa aV Aw bO DD Dl Dr Fc Hc Jm Lh oP Po Tz Uo Yh) Om(Gb Rt Ru Rv Ux Va Vb Vh Vj Vw Wc Yi Ti Th) Rz(aZ Hv Jj Nm Qa Qb Qd Qx Rg Ss Tz Ux Vj) Vj(Aw Ba bF Co CT Cu Hu Ib Mv My Vv) Yj(aQ Aw bA bQ cT Hc Lh Mv On Pg Yh) Cu(Dr Rt Rv Va Vh Vw Wc Yi Zq Yf) oP(Gb hV hW hX rC Rv rX rY Ti Th) Vb(Ba Co cT Ef Jd Jh Nv On Pf) Aw(Al Kd mE Nd oV Sf Sh) Gn(Hv Pg Qa Qd Tv Uv Vp) Yi(aF Co Is Kq Nv On Pf) Tz(Aa Eq Vz Yh Yl Zx) mW(hW hX rB rC rX rY) Ua(Du Eq Hp Lp Ye) Rv(Ba Ez Jd Nv Ou) rB(kO mM nN nT rX) oO(bV hW rC rX Tr) Co(Ux Vw We Yf) Gb(Dk Kq Nv Pf) Ou(Sf Vw Wf Yl) Th(Di Lh On) Yh(Qv Ug Um) Kq(Nm Nn Zq) Vs(Du Rt Va) Pf(Gd Ru Ux) Pg(Fd Fi Si) aQ(Gh Sf Wf) hV(aA lX mM) rX(mH mZ nN) Hu(Jj Qd) Is(Jm Sf) Zx(Vp Vv) Wc(Nv On) Lh(Vh Ti) cT(Fi Qd) EqUg NmUf NnRu LxWf MjVz MvWe ZqJn PzJj JoVv RtNv OnVh aArC} oO{Ps(aC aE Af aH Aj aK aL AN aO aQ aR AS aV aW aX aZ bB bC BG bH bI bJ bL bM BN bO bP bQ bR bS bV bW bX bZ cA cB cC cD cE cG Ch cJ cK cM CO Cp cS CT cU Cw cX cY cZ dA DB DE dF dH Di dJ Dk dM Dp Du Ed Em Eq Ez Fa Fc Fd Fi FR Fw Gd Gh Gz Hc Hf Ho Hv Ib Ih Ij Il Ip Iq Ir Iu Jd Je Jf Jh Jj Jn Jr Jy KC Kd kF kG kI kK KN kP Kr Kx Ky Kz Lt Lw LX IY Lz Mc Md mE Mf Mg mH Ml Mj Ml mM Mn Mp Mq Mr mS Mt Mu Mv Mw Mx MY MZ NA Nc Nd Ne NF nI nK Nl nM nN NO Nq NR Ns NT Nx Oa Og Oi Or Pe Pf Pg Ph Pi Pk Qa Qc Ql Qt Qu Qx Qy Qz Ra Rb Ru Rv Rx Ry Sr To Tz Ua Uc Ud Ue Uk Uo Ur Us Ut Uz Vc Vh Vp Vq Vs Vu Vv Vz Wd We Wf Wg Wh Yh Yk Yl Zw Zx Tl Xa Wm Tj Th Yf) Tn(aC Ad aE Af aG aH AJ aK AL AN Ao AP aQ AR aS aU aV AW AX aY aZ BA BB BC bE bF Bg bH bI bL bM Bn BO bQ bR bS bV bW bX bZ cA cB cC cE cF cG CH cK cL cM Co Cq cS Cu CV CW CX cY dA DB Dc DD DE dF DG dH DI Dl dM dN Dp dR DU eC eF eF EM EQ FA Fb Fc Fd Fi Fp Fw Fy Gh Gp GZ Hb Hc Hf hG Hr Hu Hw Ic Id Ii Ij Im Ir Iz jB Je Jg Jj Jk Jl Jo Jt Kc Kd Ke Kf Kg Ki Kj Kl Kn Ko Kp KQ Kr KS Kz Ld Lh Lt Lu mE MM Mn MU Mx Nb Nd Nf Nk Nm NN nO nR Ny oD oE oF Og OH Ok oQ oT Ou oV OW Pa PH pI Pj PK Qc Qd Qv Qy Rc Ru Rv Ry Si Ug Uk Um Uz Vc Vh Vo Vq Vt Wd We Wg Wh Yh Yi Yk Yl Zx Ye Tl Xa Th Yf) Vi(Aa aE Aj aK AN aO aQ aR aW AX BB bG bl bJ bM BN bO bP bR bS bV bW bX bZ cA cB cC cD cG cK CO cS Ct cU cV Cw CX cY cZ dA DB De dF dG dH dJ dL dM Dp Dr Du Ed Em Eq Fa Fc Fd Fi Fn fR Fw Gd Gh Hf Ho Hu Hv Id Ih Ik Il Io Ip Iq Ir Iu Je Jf Jn Jp Jr Js Ju Jy Kc Kd kF kG KN kO Kr Kx Ky Kz Lt Lw lX lY Lz Mc Md mE mH Mi Mj Ml MM Mp Mq Mr mS Mt Mu Mv MW Mx MY MZ Na Nc Nd Ne NF nI nK Nl nM nN NO Nq NR Ns Nt Oa Oi oQ Or Pb Pe Pf Pg Ph Pk Po Qc Qn Qt Qu Qx Qz Ra Rb Ru Rv Rx Sf Sh Sr To Tz Ua Uc Ud Ue Uk Uo Up Us Ut Uz Vb Vc Vh Vp Vs Vv Vz Wd We Wg Wh Yd Yh Yk Yl Tl Xa Wm Tj Th Yf) Wh(aH aJ aK Al aN aO aP AS aV Ax aY BB Bn BO cC cF cG cH cI cK cP cQ cR Ct Cu CV cW CX cY Db Dc dF dG dH DI Dk dL dN Ez fB Fc Fd Fn Fy Gb Gc Gn Hb Hc Hp Hr Hv Hw Ib Ij Is Iz Je Jf Jl Jn Jq Jr Js Jt Jv Kc kE Kf Ki Ko Kp Kq Kx Ky Lh Lp Lt Lv lW Lx Ly Ma Mb mF Mh Mj Mm Mn MP Mq mT mU mW Mx MZ nA Nc nH Ni NJ nL Nm Nn No Nq nR Nu Nv Nw Ny Oa Oh Ok Om On oP oQ Or Ou Ow Oy Pa Pc Pd Pe Pg Pj Pk Po Qa Qb Qd Qe Qg Qh Qn Rh Rj Si Sj Ss Tv Tz Ua Ub Uc Ue Ug Ul Um Ur Ut Uw Va Vp Vs Vt Vv Vw Wb Wf Yd Yg Yh Yi Yj Yk Zx Ye Tm Xa) Yg(Aj aO aP aQ aS Aw Ax aY aZ Ba BC bE bF bH bI BO bQ cF cJ cP cQ Cv CW cX cY Dd dF Dg dH dI DL dM dN Fr Fy Gn Gp Hb Hc hG Hl Hq Hr Hu Hv ti iJ Il In Is Iu Je Jg Ji Jj Jk Jn Jq Jt Jy Kc kE kG Kp kR KS Kx Ky Kz Li Lj lW Lx LY Mb ME Mj mP mT mU MW Mz nB Nd Nf nI Nk Nu Nx Oe Ok oN Oy Oz Pa Pb Pf Pg Pk Qc Qm Qn Qt Qu Qw Qx Qz Ra Rb Ru Rv Rx Ry Sr To Tz Ua Uc Ud Ue Uk Uo Ur Us Ut Uz Vc Vh Vp Vq Vs Vu Vv Wb Wd We Wg Yh Yl Zw Zx Ye Wm Th Yf) cT(Aa aJ aM aP Aw bQ Cu Cv Cx Dd Di dN Dp dU eC Ed eF cM eQ Et Ex Ez Fa FB Fd Fn FR Fw Fy gC gL Gn GZ Ha Hl Ho Hq Hr Hu Hv Hx Id jB Jd Je Jf Jg Jh Ji Jj Jk Jl Jm Jo Jp Jq Jr Jt Ju Jv Jy Kq Ks Lp Lx Ma Mb Mt Mu Nb Ni Nn Nq nR Nt Nu oE oF oH oK oQ oT oV oW Oy Oz Pa Pb Pc Pd Pe Pf Pg pI pK Po Qa Qb Qd Qe Qg Qh Ql Qm Qt Qu Qv Ra Rf Rg Rh Ri Rj Rm Rx Sf Ss Tr Ua Uc Uf Ug Uk Um Un Uo Ut Uv Uw Ux Uy Va Vs Vu Vv We Yd Yh Yi Yj Zx Tl Xa Tj tF) Tr(Aa aC Ad aE aF aG aI AJ aK AN Ao AP aQ Ar AS aU aV AW AX aY bA BB BC bE bF bG bL bM BN BO bP bQ bR bV bW bX bZ cB cD cE cF cG Ch cI cJ cL cM cN Co Cp CQ cR CS Ct Cu CV Cw Cx cY dA DB DC Dd dF DG dH DI dJ DK DL dM dN dU eC EF EM FA FB fP Gl Hb hG Ic iP Iz jB Jl Kc Kd Ke Kf Kg Ki Kj Kl Kn Ko Kp kQ Kr Ks Kz Ld MU nR oD Oh oQ Ow pF PH Pi Pj Pk Ua) Xa(aO aP aQ aS aV aY aZ bA bF bQ cE cL cN cP Ct cU cW cY DR Du eF Gb Gn HC hG Hq iJ In Io Is Jl Jo Ju Jv kE kN kR kS Kx Kz Li Lj Lu Lv Ma Mb Me Mh Mj Ml mP MU mW nA nB Ng Nm Nn Nq Nu nW OE oF Oi ON oP oQ oV Pa Pf Pg Qa Qd Qe Qg Qh Qn Qt Qu Qv Qw Qy Qz Rb Rf Rg Rh Ri Rj Rv Sf Ua Uc Ue Ug Uh Uk Ul Um Ur Us Ut Uv Uw Va Vb Vp Vs Vu Vv Wd We Wf Yi Yj Tl Wm Tj Ti Th Yf) Yi(aA aF aO aP aQ aV Ax aZ BA bF bZ cE cL cY dF dG dH Dr Ez Gb Gn Hq Hv Is Je Jv kR IW Lx Ma Mm mP mU NB Ng Nm Nn Nq Nv Ny Of Oh ON oP oQ Oy Oz Pb Pd Pf Pg Pz Qb Qc Qt Qv Qz Rt Sh St Tv Ua Uc Ug Uh Ul Um Un Ut Uw Uy Vb Vp Vs Vt Vv Wd Zq) bA(Aa aJ aR bR Cv dU eC cM Eq Et Ez fA FB Fy gC Gn gZ Hq Hr Hu Hv Hx Jd Jk Jl Jm Jn Jp Jr Ju Jv Jy Kq Nu oD oT oV oW Oy Pa Pb Pd Pe Pf Pg pH Po Pz Qa Qb Qd Qt Qu Qv Rf Rg Rh Ri Rj Tt Ua Uc Uf Um Ut Uw Vs Vu Vv Vw Yh Yj Zw) Kq(aA Ad aJ Al aS aU bV cF cQ Cv Dc Dd Dg Dl Dr fA fB Fy Gc Gd Gn Hb Hl Hu Ii Jj Jo Jt Ju Jv KG Kj Ks Lu lY Mb Mm nA Nb Ng nI Nm Nn Ny Of Ok oQ oV Pj Pz Qe Qv Rc Rh Rm Rt Sf Ub Ug Uk Um Uv Va Vb Vo Vw Wb Yj Zq Ti) dF(AA Af aJ aM aP Ax Ba cF Cs Dd Dp eC Ez fA Fy Hb Hc Hr Io Is Iz Jd Je Jj Ju Jv Kd Lh Lx Lz Ma Mb Mh Ml Mm Mn My Nb Nl Nn No Nv Nx Ny Oe Oh Pc Pe Qt Qv Qz Rc Rf Rh Rj Rt Rz Ug Uk Um Ur Uy Vu Wd Yj Yk Zq Yf) Cu(AA Ad aJ Al aS Aw bV cF Cv Dd Dg Dl fB Gc Gn hG Hl Ii Jj Jo Jt Ju Kg Ks Lu Mb Mm Nb Nm Nn Ny Oe Of Ok Op Pj Qe Qg Qv Rh Rj Rm Ru Rv Rx Sh Ug Uk Um Uv Uy Uz Vc Vh Vj Vo Vz Wb Wc Wd We Wf Wg Yj Zw Tl Ti Yf) fA(aD aF aJ aO Aw bF bM bV cE cL dM Ez Fn Fw Fy Gz Hc Hf hG Ic Iz Je Jl Kc Kf Kg Kk Kn Kp Kr Lv Lx Ma ME ml nA Nb nO nR oF Oh Ou oV Pg pH Qh Ql Qm Qn Rb Rg Ri Rj Rm Tv Tz Ua Uc Ut Vp

Ip Iq Ir It Iu Iv Jg Jh Ji Jj Jk Jl Jm Jn Jo Jp Jq Jt Lh Lj Lu Lv Lx Ly Lz Mb Mf Mg Mh Mj Mk Ml Mm Mn Mq Mr Ms Mt Mu Mv Mx My Na Nc Nd Ne Nf Ng Nh Ni Nj Nl Nm Nn No Nq Nr Ns Nu Nv Nw Nx Ny Oe Of Oh Oi Om Oy Oz Pa Pb Pc Pd Pg Po Pz Qa Qc Qd Qe) Qe(AA AD Af aG AJ aK aM AN AO AP AR aS aV Ax aY aZ Ba BC bE bG bH bI bJ bL bM BN Bo bP bQ bR bS bU bV bW bZ cA cB cC cD cE cF cH cI cJ cK cM cN cO CP CQ cR CS CT cU CW cX cZ Db DC dD dF DG dH dI DK DL dM dN EM Et Fp FR Gd Hq Hv Hw Hx Ih Ii Il In Io Iq Ir It Ji Jj Jk Jl Jm Jn Jo Jp Jr Js Jt Lh Lv Lw Lz Ma Mb Mc Md Me Mf Mh Mi Mk Ml Mm Mp Mq Mr Mt Mu Mw My Mz Nb Ne Nh Ni Nk Nl Nm Nn No Nq Ns Nt Nu Nv Nx Og Oh Oy Oz Pa Pb Pc Pg Po Qa Qc Qd) Mj(aC AD aE AF aG aH AJ aK Al aM AN AP aQ AR AS aU aV AW AX aY aZ Ba BB BC bF Bg bH bI bJ bL bM BN BO bP bQ bR bS bU bV bW bX bZ cA cB cC cD cE cF cG CH cI cJ cK cL cM cN cO CP CQ cR CS CT CV CW CX cY cZ DB DC DD DE dF Dg dH DI DK DL dM dN EM Et FR Hr Hu Hw Ih Ip Iq Ir It Iv Ji Jj Jn Jp Jq Jr Jt Lj Lv Lx Lz Mb Me Mg Mi Mm Mn Mp Mq Ms Mt Mv Mw Mx Mz Nb Nd Ni Nj Nn Nt Nw Ny Oh Oi Om Oy Oz Pf Po Pz Qa Qc Qd) Ny(aC AD AF aH al AJ aK AL aM aN aO aP aQ AR As aU AW AX aY aZ bA BB Bc bE Bg bI bL bM bN BO bQ bR bS bU bV bW bZ cA cD cE cF cG CH cI cK cL cM Co Cq cS Ct CV CW Cx cY cZ DB DD De dF dG dH DI dJ dL eM Et Fp FR Hq Hr Hu Hv Hw Ih Ii Io Ip Iq Ir Iu Jg Jh Ji Jj Jk Jm Jn Jo Jq Jr Js Lh Lj Lu Lx Lz Ma Mb Mf Mg Mh Mk Ml Mm Mn Mq Mr Ms Mt Mu Mv Mx My Nb Nc Nd Nh Nj Nk Nn No Nq Nr Ns Nt Nv Nw Nx Oe Of Og Oh Oi Ok Om Oy Pa Pb Pc Pf Pg Po Pz Qa Qc) Mn(AA aC AF aJ aL aN aP aQ AR As AW Ax bA Bb BC bJ bM BN BO bS bU bX cD cE cF cJ cK cL Co CP Cq cS cT cV cX dD De dG dL dN eM FR Gd Hu Ih Ij Ik Ip Iq Ir Iu Jh Jk Jl Jn Jr Jt Lj Lu Lv Lx Lz Mb Me Mh Mm Mq Ms Mt Mu Mv Mw Mx My Nb Nd Ne Nf Nh Ni Nl No Nr Nt Nu Nv Oe Of Og Oh Pf Pg Po Pz Qa Qd) Pf(aC AF Aj aK AL An AO aU Aw aZ Bb bE Bn bS bW bZ cD cE Co CP Cq CV cY dA dB Dc dD De dF dG DI Dk dN Et Gd Hq Hv Hw Hx Ih Ik Iq Ir It Iv Jg Jh Ji Jj Jk Jl Jm Jn Jq Jr Jt Lv Ma Mb Me Mi Mm Mr Ms Mx Mz Nc Nd Nf Ni Nk Nl No Nt Nw Oe Of Oh Oi Ok Om Oy Pa Po Pz Qa Qc Qd) Qd(aC aK aL aO aQ AR AS aU Aw Ax BA bN bO bU bV bW bZ cF cG cP CS cT cU cV cY Db dC dD dF Dg dK Em Hr Ih Ij Il Ip Ir It Iv Jg Jh Ji Jn Jt Lj Lv Lx Ly Ma Mf Mg Mh Mk Ml Mq Mr Ms Mt Mv Mx Na Nd Ni Nn No Nr Oe Oh Ok Om Oy Pc Pd Po Pz Qa) bA(aD aE aH al aJ aL aM Ao aP aV aW aX Ba bB Bg bI bL BO cB cC cD cF CH cJ cK Co Cp Cq cR cS cT cU cV CW Db dD De Di Dk dM dN dR Et Fr Fw Gd GL Ih Ij Ik Iq Ir Iu Iv Jk Jq Lx Lz Mq Ms Mt Mv Mw Nb No Nq Nu Nw Ok Om Po Pz Qa Qc) Qa(Af aK aL AO aR aU aV AW aX Ba bB bI bJ Bn bR bS bV bW cA cB cF cO cT cU cV Cx cY dB dD dG Dk Em Hq Hr Hw Ii Ik It Iu Jg Ji Jj Jo Jt Lv Lz Mb Me Mi Mm Ms Mx Nd Nh Nj Nx Oh Ok Om Oy Oz Pa Pb) Aw(aC aF aJ AL An Ao aP Ar Ax bG BO bX cH Cp Cs cT Cw dB Dc DD dJ Dk Et Fp Fr Hx Ih Ij Iq Ir It Ji Jm Jn Jp Jr Lj Lv Lx Mb Mf Mk Ml Mr Mt Mx Mz Ne Nj Nl Nw Oh Ok Po) Ij(aD Af aJ aN Ao AR bO bP bV cD cE cH CP Cq cV dB De dH Fr Gd Hq Hr Hu Hv Hw Il In Iq Ir It Jg Jh Ji Jj Jm Jq Jr Lv Mp Ms Mu Mw Mz Nj Nk Nr Nt Nw Ok Om) Ok(Aa aC Ad aJ aP aR As Bb BC bH bP cK Cs dB dD Fp Hu Hx Ih Ik Ir Iv Jl Jn Jr Lj Lu Lv Lx Lz Mb Mh Mq Mt Mu Mx Nb Nc Ne Nh Nj Nl Nr Nt Of Po) It(aL aN Ao aZ bC bO Cp cT cU dB De dl dK Fr Hr Iv Jg Jh Jj Jq Lh Lv Lx Mp Ms Mt Mw Mz Nc Ne Nh Nk Nl Nr Nv Po) Mt(aC aG Aj aR Bn bW CT dB dD Dg Fp Ik Iv Jo Jq Lv Mb Me Mm Ms Mx My Nd Nj Nt Nx Oe Oh Om Oy Qc) Jq(aJ aP aR Ax bO bV Cs cT dD Fp FR Hx Ih Ik Iv Jh Lv Lx Mb Mh Mk Ml Mq Mr Nr Oh Po) jB(aL Ao aU aZ Ba bB bO cC Cp Cw Dc Et Fw gP Ih Ir Iv Jh Ji Jp Lh Lv Lx Ms Nh No Oh Po) dD(Ad Al Ao aP aR Ba bO cG Cp Cq cT CW De dI gP Ih Io Ir Jh Jt Lv Mp Mw Mz Nj Om) Oh(Ao aX Bn bR cC cD cI Cp dC Ih Ik Jh Jk Jn Jt Ms Mu Mv Mw Nj No Nt Nv Om Po Pz) Lx(Af aL Ao aR Ba Bn bX cD Ct cV De Hu Ik Iv Jg Jh Ms Mu Mw Nj Nt Om Oy Pz) Ms(aJ aP Ax Cp Cq Cs cU Fp Hx Ih Ik Iv Jl Lj Nb Nd Ne Nj Nl No Nr Nt Po) Ji(AA aJ aP aR Cv Fp Hu Iv Jn Jr Lu Me Mq Mr Mu Mx Nd Nr Nu Po) Om(aA cP Cs cT Fp Hx Ik Jl Jr Lj Lu Lv Lz Me Mh Mk Ml Mr Nb Nd Nt) Mx(aM Ao Ap aU aX aZ Ba bC bO Cw De Jt Lv Mi Mp Nb Nj Nw) Ik(Ao bO cD Cw Dc Io Iq Ir Jk Jp Jt Lh Lv Mp Mz Nc Nj Nw) Cp(aL aM AR Ax Ba bQ bZ cT cU Em Iv Lv Mk Ml Mq Oy) Po(Af Ao aX Ba bS bX cB cT dH Em Hq Hr Hw Mi Nw Pz) Ao(Ax bO bW Cs cT cU dJ Fp Hx Lj Me Mh Mr Nd) Ba(aC bC bG Cs Dc Dk Fp Hx Lj Lv Lz Mb Mr Qc) Jn(Ar bO cT De Hr In Iq Jj Jm Lv Ma Mf Nh Nw) Lv(bO Dk DI Hu Iv Jh Jl Jt Mv Nr Nt Pz) cU(aA Bn Bo bX cE cO Dc Dd De Hx Nw Qc) Fp(aU aX aZ bC bO cV Cw De Jt Nw Pz) Iv(Ar bO bX De Dk Fr Hx Iq Lh Mp Pa) Nt(dI In Iq Ir Jj Lh Mb Mk Mz Nw) Nj(bO Fr Iq Ir Jh Ma Mq No Nr Pz) cT(aP aR bO De Dk Fr Ir Iu Jh Mw) gP(aO aW Ax aY bE bP bW Dc dG dN) Dk(aU eF Fw Gl Ir Nb Oy) Jh(Aj bN Lz Mb Mh Mk Oy) Nw(Jl Lu Mq Mr Nb Nr Nu) aL(aJ aP aR bO Ih Nu Qc) bO(Al aN bR bX dR Fw) Mr(aU bC De Jt Mp) Nd(Ir Mp Mz Nb Nm) Mb(dC Jt Nb Pz) dH(aP Ir Nh Nr) Dc(aR bB cS) Dc(Ax Cs Lj) Lz(bB Ct Mi) Me(Jt Nx Pz) Jr(Hr In Nh) aC(aX Fw gL) bW(eF Ih Nh) Ar(dC Gl) Mq(Jt Mz) Lj(aX Pz) dR(aR dM) CqJj FraU FwcA NocO MkHu MlJt MzbB NbaW NhIh HrHx aPdG} Tn{pK(aA aC aD aE Af aG aH aI aJ aK AM AN Ao AP aQ AR AS aU aV AW aX aY aZ BA bB Bc bE bF BG bH bI bJ bL bM bN BO bP bQ bR bS bU bV bW bX bZ cA cB cD cE cF cG CH cI cJ cK cL cM cN cO CP CQ cR cS CT CU CV CW CX cY cZ dA DB dC DD DE dF dG dH DI dJ DK dL dM dN Dp dR dU eC Ed EF Em eQ Et Ex fA Fn fP FR Fw Fy gC GL GP GZ hB HC HF hG Hr Hu Hv Hw Hx iA Ib Ic Id iH iJ Il iO IP Iq Ir Iv iZ jB Jd Je Jf Jg Jh Ji Jj Jk Jl Jn Jp Jq Jr Js Ju Jv Jy kC Kd KE kF Kg KI KK KN KO KP kQ KR KS Kx Ky Kz Ld Lh Lv LW LX LY Lz Ma Mb Mc Md ME Mf Mg MH MI Mj Mk Ml mM Mn MP Mq Mr MS MT MU Mv MW Mx MY MZ NA NB NC ND Ne NF Ng NH NI nJ NK NL nM NN NO Nq NR NT Nu NW Nx Ny oD OE oF Og oH Oi oK Om oN oP oQ Or oT oV OW Oy Pa Pc Pd Pe pF Pg pH Pl Pk Po Qb Qc Qg Ql Qm Qn Qt Qu Qw Qx Qy Ra Rb Rg Rh Ri Rj Sr Ss To Tt Tv Tz Ua Ub Uc Ud Uh Uk Ul Um Un Uo Up Ur Us Ut Uv Vp Vs Vt Vu Wm Tj tF) fB(aA aC AD aE Af aG aH aI AJ aK aL aM aN AO aP aQ aR AS aV AW aX aY aZ Ba bB BC bE bF Bg bH bI bJ bL bM BN BO bP bQ bR bS bU bV bW bX bZ cA cB cC cD cE cF cG CH cK cL CO CP Cq cR cS cT Cu CV CW CX cY cZ dA Db dC DD DE dF dG dH DI dJ dK DL dM Dp dR dU Ef EM eQ Fa Fi Fn fP Fr Fw Gh Gn Gp Gz HB Hf Hl Hr Hu Hv Ic Ih Ij Ik Il IO IP Iq Is It Iu Iv Iz Jd Je Jf Jg Jj Jk Jm Jn Jo Jr Kc Kd kE kF KG Kl Kj kK kN kO KP KR kS Ld Lv Lw LX LY Lz Mb Mc Md ME MF Mg Mh Ml Mj Ml MM MP Mq Mr mS MT Mu Mv mW Mx MY mZ NA NB Nc nD Ne nF Nh Nl Nj nK NL nM nN NO Nq nR Ns NT Nu Nx nY Oa oD OE Og oH Oi OK oN oP oQ Or oT Ou oV Pd Pe PF Pg Ph Pl Pj Po Pz Qg Qh Ql Qn Qt Qu Qv Qw Qx Qy Qz Ra Rb Rc Rg Rh Ri Rj Rm Rv Ry Rz Sh Si Ss St To Tt Tz Ua Ub Uc Ud Ue Uf Uk Ul Um Uo Up Ur Us Ut Uv Va Vh Vo Vp Vq Vs Vt Vu Vv Wd Wh Yj Zx Xa Wm Tj Ti Th tF) nI(Aa Ad aF aG Aj Al Ao Ap aQ aR As aU aV Aw Ax bA BB Bc Bn bW bX cF cN cS cT Cv Cw Cx dA dC Dd Dg dH DI dJ Dl DR dU eM Eq Fb Fc Fd Fi fR Fy gC Gh Hb Hl Ho Hp It Iz jB Jg Jl Jo Jt Kd Kf Kj Kk Kl Kn Ko Kp Ks Ky Lh Lp Lu Mm Mn Mp mU Nb Nd Nk Nm Oi Ok Op oT Pc Ph Pi Pj Pk Rc Ru Rv Rx Ry Sf Sh Si Sj Uc Ug Um Uo Uu Uw Va Vh Vi Vj Vo Vu Vw Vz Wb Wc We Wf Yd Yg Yh Yi Yj Yl Zq Zw Zx Ye Tm Tl Xa Ti Th Yf) cQ(Ad aF Ao Ar Bb Bc bF cM Cu Cw Dl Et Ez Fa Ha Hw Id Ih Ii Ij Im IO Ir Is It Jg Ji Jj Jm Jo Jq Js Jy Ke Kf Kj Kl Kn Kq Kz Lh Lu Ma Mm Mn Ms Ng Nk Nm Nn No Nr Nw Ny Oa Of Om On Pc Pz Qb Qh Qm Qn Rf Rm Ss St Uf Ug Uu Vo Vt) gC(Aa Ad AO Ar bF bI cS Cu Cx Dc Dg Dl eF Ez Hb iO Ir It Iu Iz Jd Jh Ji Jj Jm Jq Jt Ju Kc Ke Kf kG Kl Kn Kq Kz Lh Lu Ma Mm Mn mT Mw nD Nj Nk Nm No Ns Ok Om On Ou Ph Pj Qa Qb Qh Qm Qn Qz Rc Rf St Uf Ug Uu Vo) nH(Al Bb Cv Dg Dr Du Eq Fc Fi Fy Gb Gc Gd Gh Jo Jt Ks Lt Mm Mn Nm Ok Op Ps Ru Rv Rx Ry Rz Sf Sh Si Sj Ug Uw Uy Uz Va Vc Vh Vi Vj Vw Vz Wb Wc Wd We Wf Wg Wh Yd Yg Yh Yi Yl Zw Ye Tm Tl Xa Yf) oV(Aa aF Ao Ap Ar Bb Bc bF Cu Cv Dg Dl Et Ez Fa Fb Ha Ih Ii Ij Im iO Ir Is It Jd Jg Jj Jo Jt Jy Kl Mn Ms MT Nk No Nr Nw Oe Of Oi Om On Pc Qb Qc Qm Qn Rc Rf St Ub Uf Ug Un Uu Vq Vt) dU(Aa Ad aO Ap Ar Bb bF bU cM cQ cS Dc eF Fa Fb Fy Hb Ih Ij iO Ir Ji Jj Jm Js Jt Kc Ke Kf kG Kl Kq Lh Li Lu Ma Mm Mn Nj Nm Nn No Nr Ny Oa Og Ok On Ou Pj Qa Qb Qc Rm St Vo) oP(Aa Al Ax Dr Du Eq Fc Fy Gb Gc Gh Gn Hb Hl Hp Ii Jo Js Jt Li Lp Lt Mm Nk Nm Nn Nv Ny Of Oh Ok On Qe Rv Rx Ry Sf Sh Si Sj Ug Ux

Figure 32 Continued

Figure 32 Continued kI kO kP IX IY mF mH mI mM mS mT mY mZ nK nN nO nT oF) aV(kE kG kI kO kP IW IX IY mF mM mP mZ nB nD nF nM nN nO nT)
Qv(kC kI kO mF mM mZ nA nD nO) Ug(kC kE kI kO mF mH mS nK nT) aU(eQ gC kC kO mF nA nD pH pI) Hb(aZ Jr kI oD Qa Qd) Va(kI
mH mI mS nA nT) Nm(kF kG mP nN pH) cF(aZ eQ Hv kE kI) kE(bF cY Pb Ri) Gp(IW mM nN) Rt(mI nO nT) Aa(aA aZ) Ri(kI mS) LuHv
NbNe HwkG JrKs JupI bFgZ} wJ{Oh(Fp Hu Ii It Iu Jg Ji Jk Jm Js Jt Li Lj Ma Mg Mr Ng Nk Nm Nr Ny Of Og Ok On Pc Pd Pf Pz wH wL wQ yD) Mz(Hv Hw Ii Ij In Ir Jh Jn Jq Jr Jt Lw Mi Ml Mq Mr Mu Mv Nf Nm Nr Ny Of Om Pb Pd Pe Po wL) Mp(Fp Li Lj Mm Ng Nm Of Pf wL) Ih(Hu Ii Jm Jt Nr Ny Pd wH wL) Hu(Il Ir It Iv Mx Nt Nv) Iu(Hx Ir It Mx Nt Qb) Nv(Ii Jt Nm Ny) wL(Hx Iv Pg) Ii(Ij Pg) Pa(Ma Pd) NmJI MmJp HxJt IlwH ItPc wDwF} Uf{gZ(Ax Bb cM Cs Dg Fa Fp Fr Fy Ii Io Jm Jt Kf Kl Kn Lh Mm Nm Oh Pc Pj Qe) eQ(Aa Ad Al Ap Cw Dg Dl Fb Hb Kf Li Lj Nm Nn Oh Pc Pj Qe) pH(Aa Bb cM Cs FP iO Jt Li Lj Ma Mm Nn Ny Oh Pc Pj Qe) pI(Aa aO Jj Jo Jt Li Lj Mm Nm Nn Ny Oh Pc Pj) gC(Aa Al eF iO Jt Li Lj Nn Ny Oh Pc Pj) oD(Aa Ap Bb bF Jt Li Lj Nm Nn Ny Pj) jB(Bb iO Jt Nm Nn Ny Pc Pj) Nm(mF nK) AakI KylN eDiZ} Mj{mP(hA iC jE jF jG jH jK jL jM jO jQ jR jY lK lO qU qX rA Vz) lK(kE kG kO kP mF mH mM mS mW mZ nA nB nD nF nK nO) nT(iB jD jE jG jK jM jO jR jU jV jY qY Wh) kP(iB iC jE jK jP lN qT qV qW qY) nO(cF iC jE jG jM jR jY lM qY) jG(lX mH mS mZ nB nD nN) mS(jD jE lN qY) mZ(hA jE jL jO) Wd(eM kC mT) nK(jM jU qY) kG(Dr Vz Zx) nA(jM jU) qV(kE nD) VzmT WheM RtmY cFlY lXqY kOlN} Va{Om(eM kC kE kF kG kI kO kP lW lY mF mH mI mM mP mS mT mW mY mZ nA nB nD nF nK nM nN nO nT) Vs(eM kC kE kG kI kO kP lY mF mH mM mP mS mT mY mZ nB nD nF nM nN nO nT) Ou(kC kE kF kP lW mF mH mI mP mT mY mZ nD nN Vv) Nv(kC kI lW lX mS nN) Jr(Du Kd Vu Yk Yl) nN(Kq Ld Ma On) lX(aQ bF cL dR) lW(Co Jd Kq) Ua(eM kO) Hc(kI mI) mY(Jn Jq) ComT VvmH PbkE} Wd{Gp(eM kC kE kG kI lX mF mH mI mM mP mS mT mZ nA nB nD nF nK nM nN nO nT) Jj(eM kC kE kF kG kI kO kP lW lX lY mF mM mP mS mT mY nB nK nN nT) eM(aU aZ bW Jn Jr Js Lx Nb Nw Oh Ow Po Qa Qd) kE(aF bF bO bW Fb hC Hp mT Pa) Jr(kO lW mF mI mT nT) bO(kO mT mY nO) lW(hC Lp Lx Pf) hC(kI lX mS) kO(bF In Ug) MhmF MvmT JnmH YlOr RhkG OukC UglX} On{jG(kC kE kF kG kI kO kP lW lX lY mF mH mI mP mS mW mY nA nB nD nF nK nM nN nO nT) Vh(Hb Hp Ib Ih Ii Kq Ks lW Ma Ny Oh Ow Rc Si) lK(kC kG kI lW mF mH mS nK nM nO) nT(iC jE jF lM qV qY) Rt(kE mM mY nN) Ad(Ry Si Yl) lW(qV Rx Wc) Aa(Ry Zw) Mm(eM eQ) Zq(mM nA) Yl(Jt Rh) mH(qV qW) mP(jE lM) mY(lM qY) DrKs YfIi MzTl HbeQ YkOk SiUm nNjE mSjT nAjF qVkP} Wh{Gp(eM kC kE kG kI kO kP lW mF mH mM mT mW mY mZ nA nB nD nK nN nT) bO(kC kE kI kO lW lX lY mH mI mT mY nD nK nO) eM(aZ Dk Hv Jn Jq Jr Js Lx Oh Po Qa Qd Up) Lp(kF kO lW lY mF mP mZ nB) bF(kO lX lY mS nD nO) aF(kE kI nD nK) mH(Et Jj Uk Uo) bB(kC kP nO) kE(Cv Jj Pb) Hp(kO nD) kI(Jj Ou) AaaZ MvmT InmF HbQd QalW JrnT UmnB aUkC dAkO} Pg{Si(gZ kC kE kF kG kI kO kP lW lX mF mH mI mM mP mS mT mW mY mZ nA nB nD nF nK nM nN nO) Sf(kC kE kF kG kI kO kP lW lX lY mF mH mI mM mP mS mW mY mZ nA nB nD nF nK nM nN nO nT) Hp(kC kF kG kO lY mF mW mY nB nD nN nO) Gd(kC kG mY nD) Zq(kC kF kG nD) kG(Dr Tm) lK(mS nK) FdkO FinD LywL RtmY cFhR qVkP} Ux{Co(eM kE kG kI kO lW mF mH mM mS mT mY nB nD nO) Om(eM kC kE kF kG kI kO mH mP mZ nA nD nK nT) Ef(kC kE kF kG kI kO lW mH mM mS nK nO nT) Pf(kC kF kG lX mI mY nB) Hc(kF kG mP mT nK nN) kO(Hu Jh Mu Mv My Ou) Nv(kG lX nD nK nT) Kq(lW mY nN) Ou(kC kI nA) Mv(lW mW) kE(Cp Pb) DkkG NnnK JhlW} eQ{Hc(aF Al Ap Bb Fb Jg kG Li Mm Nm Nn Ny Of Oz Pb Pc Qg Rc Ss Ug Um Uu) cT(Al Io Jm Lp Ni Rx tF) Ax(bZ Fy Lx Ma Oh Tr) Lj(bZ Fy Lx Ma Ow Tr) Pc(Aw Eq Ou Ua Vs) Ow(Oz Pb Qe Vt) Al(bA Tt Vv) Ba(Fa Fb Nn) Fp(bZ Ez) Fy(Oz Pb) Mm(Ma Mv) Ny(bF bZ) Vs(kC kG) GlLp HaLd LvTo MgUg NbaO TreM JubF OabQ} Ua{Sh(cF eM Gh Gp Hf Lp lX Mh Mz Pc Rt Rv Ry Tr) Si(aZ Ed kE Lx Lz Mh Nw Oh Ow Vj) Hp(Ed kE kG kI kO nD nK oF) Mh(Du Lp Ry Sf Yl Ye) Lp(Ch fR kO mI nD) Pc(gZ jB oD pH pI) Gd(kO oF Yl) Rt(bH eM kG) jB(Al Em iO) kE(Sf We) kG(Eq pI) kO(Rx Ye) AloD GhoF JjfR YlOr cFgC} pH{Lj(bZ Ez Fy Hc Lx Ma Nb Ow Pf Po Qt Qu Rf Tr) Cs(Qt Qx Ra Rf Rh Tr Tt) Hc(aF Al Gc Mm Nm Nn Ny) Ax(bZ Fy Kx Lx Ma Oh) Ny(Ba bF bZ cT Ma Mv) Fp(Ez Qt Rf Tr) Mm(Kq Mg Mv Pz) To(Ba iO Mv Ng) Al(Ow Vv) Ba(Fa Nn) Fy(Pb Qe) Ma(Ha Zw) Vs(iO Pc) QeOw QuPb JubF UkiO} Ou{Yl(Aa bP cN Hb hC Hu Iv Ju kC kI kO Lu Mm mP Mv Nb Op Pa Pb pF Pj Sf Si) kC(Dr Gc Op Rt Rv Rx Sf Sh Uz Vc Vh Vw Wf Wg Yd Zq) nD(Du Rt Sf Vj Vw Yd Zq) Pc(gZ jB oD pI) kO(Rt Sf Vz Wc) Rt(kI mY) jB(gL kG) TrgZ SikG SfkI OpVv VtoD cSpI eDiZ} Ly{wL(Hv Hx Ih Ij Il Im In Io Ip Ir It Iv Ji Jl Jn Jq Js Mc Mm Mx Mz Nc Ne Nf Nh Nj Nl Nv Nx Ny Og Oh Qa Qb Qc Qd Qe tV wC wD wF yD) yD(Hw Ih Il It Mb Mm Mx Nm Nv Of Oh tS wF wG) Ky(eD jD lN) FpwC cFhR nTjE nBjF wDwF} pI{Vv(Aa Al aO Fy Ha Jo Kf kG mF Mm Nn Oa Oh Rm Ug Vo) Lj(bZ Ez Fy Lx Ma Pf Qa Tr) Hc(aF aO Bb Jg Nm Ug) Ax(bZ Fy Lx Ma Tr) Ny(Ba bF bZ Ma) Ow(Cs Fp Qe Vt) Aw(Ju Jv Pc) Fy(Oz Pb Qe) Kq(Nn Qe) Vs(iO kG) cT(Kc Rx) ArMa BaFa CpSf EqPc LvTo NbaO ShJv JubF} Zq{Jn(kC kF kG kI kO kP lW lY mH mI mM mP mS mT mZ nA nB nD nK nN nO nT) Jr(kE kF lW mM mT mW mY mZ nA nK nN nO) Nv(kC kE kF kG mM nD nK) Kq(kF kG lW mM nA nN) Pf(kF kO mZ nK nN) kE(bF dF Om Oz Vs) aZ(Hb Hc) DkkG JlmM} lK{nK(aA Fr Hx Jk Jl Jn Jq Js Lu Lx Mu Mv Mz Nn Nq Nr Nv Ny Oh) mS(Jk Jl Jq Ma Mu My Mz Nn Nq Nv Ny Oh) Nv(kE kI lX lY mF mM mY nD nO) Ny(kC kI kO kP mH mI mM nD) Mu(kC mH mW) Mz(mF mZ nO) Ma(kE mF) NqlY MqmZ JknD NwmF cFhR} Rt{Om(eM kC kE kF kG kI kO kP lW lX lY mF mH mI mM mP mS mT mW mZ nA nB nD nF nK nM nN nO nT) Nv(kF kG kI kP mM mS mT mY nB nD nK nN) bF(kC kI kO mF nA nD) Co(lW mZ) eM(Cp Vs) lX(aQ dR) mY(Jn Kq) AaQI HbJr VvmH} jB{Ow(aD Al Cs Fa Fp Ha Ir Jm Kz Nf Ny Qa Qb Qe Sr Vt Tj) Ma(Ax bU Dr Ha Kz Lj Nf) Lj(bZ Ez Fy Nb Rf Tr) iO(Qg Ub Uh Vp Vs Vv) Ax(bZ Fy Lx Tr) Fy(aU Pb Qe) cT(aU Kc Ni) Fp(Ez Ri) Ny(bF bZ) bU(bF bZ) AlVs AwPc BaFa MmVv ZwaU KcbA} hR{cF(aA aM aQ bO Ct cY eD hV hW hX Ib Jv Ld Li lN Og Oy Um) aA(eD kP lN lX mP mS mZ nO nT) lN(Aa aJ Bo Cv dE Ky Mu) Bo(Id JV Ld Li) jF(mM mW nN nT) Ld(aO Md Oz) iB(mY nA nT) mZ(jD nT) MdLj LiaO VqOz nNrY mMjR} kG{Hp(Co Ef Hc Jd Jl Jn Jr Pf) Rv(cN Dk Nb Oi Oz Pb Ri) Si(Jn Jq Ke Nv Om Pf) Dk(Gd Vz Wb Zw) Jr(Dr Gc Yl Zw) Nv(Dr Wb We Zw) Hc(Gd Lp Vw) Zx(cN Pb Pc) Wb(Jd Jl) AaoD NmKq NqjG MuJj IbaU YdcN QdVs LtlW OmVj VvgC} eD{iZ(Ar Ax Bc Cq Cs Fw Gp hA iC Id Jd jY Ko Ld Li Oa Ow pF Qh Ra Rg Tr Um Tj) Ky(Bo Ic Iu Ko Kr Oh) aJ(Ar cF Ld pF) gL(hA pF Rg) Mu(Ic mP) cF(qT qV) dI(qV qX) ArQd MakI IuVu RanY LdaA aPpF} oD{Ax(bZ Fy Lx Ma Oh Tr) Lj(bZ Ez Fy Ma Ow Tr) Ny(bF bZ cT Ez kF Ma) Wb(Ez Ma Mg Mv) Kq(Li Mm Nn Qe) cT(Fa mM Yl Zw) Pc(Aw Eq Kc) Al(bC Vv) Cs(Ow Tr) Fy(Pb Qe) Ma(Ha Oa) BaFa EzGd GcMv LvTo IiVv QeOw UkbF UrVs} kE{Pb(Dr Du Fc Fd Fi Fy Gc Gd Ho Hp Lp Lt Op Ru Ry Sf Si Vh Vj Vw Yd Zx) bF(Ho Rx Sf Vh Wc We Wf Yk Yl) Nv(jG We Yl) Om(Hp Ry Si) Cp(Hp Si) Eq(Oz Pc) Mz(iC jG) Sf(Jk Vs) YfMv NmKq VjOz} lN{Ky(aK Ax bC Cs Gp Hf hV Im Iq Ir Iu jG Jo Kd Kn Ko Kr Ld lM Mk Mr Oh Pe pF Ra Um Us Vq) mS(aA Hu Jk Mf Mp Mu Mx My Nn Nq Nv) Aa(Ed Ql) Qd(Ax Ko) iZ(BC) MuhX JqnN} lW{Lp(Hu Jh Mv Nn Nq Nv Om Pf Qu Uv Vu) Lt(cS cU gL Mv Pf Qa) Rx(Co Ef Jr Nv Om) Vj(aO bF bQ Qu) Wb(Co Jd Nv) Kq(Jo Nm Vw) Sh(Jh Mv) Qu(Jj Jo) aA(hV jR) GhdR NqjF LxqV MuJj WfaQ RvRi RuPf} nT{Nw(jE jF jG qT qU qV qW qX) jE(Fr Jq Mz Nn Nq Nv Om) jF(Lx Ma Mp Nq Nv Om) jM(Jq Mb Mu Nq Om Qd) Pf(Hp Op Sf) Nv(jG qY) hA(Mq Mx) iB(Jj Mt) FrjG NmKq NqqY LxqV MziC NijR LpVv NyjO} Yl{Jr(Aa cF Ii lX mP Nn oE oF Pj Rh Si) Or(Aw De Ef Hu Jh Mu Mv Ng) Nw(Aa cF De Hb kS Pj Si) Lx(Hb Hv Mv) Ld(eF kS) Nv(Jo kI) LuOw HvOh JlkI aQgZ} gC{iO(Rb Rg Ri Rj Rm Ue Uk Um Vq Vs Vt Vv) Ax(cT Ez Fy Ma Ow Tr) Qz(bZ Ef Ez Ma Ow) Al(cT Tr Vv) Lj(Fy Ow Tr) eF(Qu Ri) AwPc CvaU FyPb YkaQ QeKq NyOw} gZ{Ax(bZ Fy Lx Ma Oh Ow) Lj(bZ Fy Lx Ma Ow) Ow(Ha Nn Qe Sr) bF(Ju Ny Rx Yk) Al(Fw Hc Tr) Ez(Fp Nn) Ma(Nn Ny) Pc(Aw Eq) FyPb LvTo UeiO RxcT LpaQ NybZ} Kq{Nm(eM kC kF kI kO kP lX lY mF mI mM mS mT mW mY mZ nA nB nD nF nK nM nN nO) Cv(lY nK) Nn(eM lX) MmeM HbnA QemT VwnN} kP{qV(aA iB Lx Ma Mp Mv

Figure 32 Continued

Mz Nq Nv Nw Ny Oh) jG(Jl Mu Nv Ny Qd) aA(hV jD lM) Mu(Jj qY) qW(Nv Ny) GhdR NqqY MqiB HcSh YkaQ VjbF} jF{Nq(lX mF mI mP mS mY nA nB nD nK) Om(mH mP nB nN nO) Jq(mM mP nB) Ma(mW nA) lX(Mp Mz) MmnA QdnB aAmS} mT{Mv(Du Eq Gd Sh We Ye) Jh(Hp Lp Sf Sh Ye) Nn(Ru Th) Qd(bA cT) Jd(Rv Yf) Lp(Hu Qu) CoRv GdHc RuPf PdiB aAhV} Hb{Jr(Dr Du Ru Uz Vh Wc Wg Yk Tl Yf) Nw(Vh Vw Vz Yk Yf) Yk(cU Qa Qd) Qd(cF Gl) VjVv} aA{mZ(hV hW rB rC rX rY) hV(lX lY mY nD) jR(mF mS nA nF) Aa(Vj Yd) mW(rX rY) mSlM mYiB kOrY} mP{Qd(hA jE jM jQ jR rA) Mq(hA iB jR) jE(Jq Nq Om) Nw(qV qW) DuJr NqqY LxqV MuJj JqlM RvRi} jG{mS(Jl Mu Mz Nn Nv Ny) mY(Fr Mz Nq Nv) kI(Fr Mz Nv) mZ(Mq Qd) oE(Ti Th) NqnB MzkC KybO} kO{Mv(Vh Vw We Yf) Co(Vh Vw Yf) Lp(Tr Uv) Ri(Rv Zx) Om(Vh Vw) AwGd EqUg NqqV MyVh WcbF} Si{aZ(Co Ef Hc Hu Im Mv Ng) Vv(Mq Nq Ow Vj) NgQd YkQa QyNw JnmY JrVu aQlX} mH{Sf(Hc Js Mv Nn Qu) Vz(Jl Qa) Wf(Ma Ow) Vv(Lp Wc) Pf(Op Ru) YfNn NqqY LxqV MvSh} Aa{Vj(Fy Jr nA Pi Tv) Vz(Hv Jr Nw) Jr(Du Zw) rY(Hx Mx) EdjV YkQa aZkF dRlX} Hp{mY(Jn Nw Pf Qa Qd) eM(Jn Qa Rm) Jl(mM nB) aQ(mF nD) mI(gL Jh) VsnD} wL{Nu(Nh Nx Og wC wD) Ma(Ih Oh Pa) Nj(Ir Nl Nx) MzLi HuIt OhtN} lM{Ex(Ky No Nw Qd St Uo) Jq(mM nB nN) Ky(Ko Oz) ThoE MpmS IdaJ} nA{iB(Ji Jj Jq Lv Nq Nw Pd Qc) Jq(jM rA) LxqV MziC RuPf} lX{dR(Gh Rv Ry Sf) aQ(Gd Rx Wc) cY(Gh Sf) EqHc VjVv} eM{Vs(Lp Vj Wc) Mm(Ke Qa) Lj(Pe Qa) EfVw WeOm} lY{Qd(cF cS Hc Qu Vz) Qa(Ax Cs Oa) JjiB} mS{Nn(jE qY) Mu(jD qU) NqqV MvSh MziC NchA LpVv} mY{Nv(jE jY qV qY) FcQu MqhA ZwJr QdLp} Vj{bF(kC mF nD) OmnD OwVv VucF OzoE} nN{jE(Jq Mz Om) DrLd MziC JoVv NwqV} nK{Nn(We Th) AlQa LxqV MpjT LpVv NyqY} Jj{Mu(kC kF mW mZ nB) JknO} Hc{Sf(aZ mI) DeGd ShaZ VwkF} Rv{Ri(kC kF mF) nO(Ld Ma)} cF{Lx(Cs Du) YkaM JrTl JvhX} kI{Pc(Eq Qu) VzJl WfbF LpVv} Nj{yD(Il It Mx Nv)} mF{GhaQ LxLj MpjR MziC} mZ{MqjE MziC WbNv OpPf} nD{EqVs NqqV VzJl OmVw} Ti{QcqU hAoE iOjV} Gd{kF(Mv Pf) HuoF} Yk{LuHv JrRf aQkC} Li{aO(hV hW hX)} mM{ZwJr QdcT JqjE} Md{hV(Ld Lj)} Mv{Sh(mW nB)} Hu{oF(fR Gh)} Id{QdjH iZjP} Ko{Ky(jL jV)} Lp{Vv(mI nO)} Oh{DuHv OkwK} iO{ThjV GljD} wC{MmJp tXwF} kC{ZxaU RuPf} CoVwkF YfJrNy EqPcmI NuwDwF MzmWiC bCtFqT

Unconstrained panels with 2 analytes, where 1.0E-8 >= 'AUC p-value' > 0. Contains 249 panels of 149,894 total panels evaluated. : rZ(hR hW iC jD jE jF jG jI jO jV jY kC kE kF kG kI kK kN kO kP lK lL lN lO lW lX lY mE mF mH mI mM mP mS mT mU mW Mx mY mZ nA nB nC nD nF nH nI nJ nK nL nM nN nO nR nT nU Nv oO oP oQ qZ) gV(bA cT CU dB dR gP Ij Im Is Ji Jn Li Mj Mn Mt Nw Ny Ok On Pe Pf Po Qa Qb Qd Qe) jI(Gz jG kC kG kK kN kO kP lN mE mH mM mP mS mU mZ nB nC nH nI nJ nL nN nO nR nT nU) oP(Gb lK lL lN qV rB rX rY Sf Vj Vw Wd Wh Ti) dX(Ho Is Jn Jr Ps Tn Ut Vi Wd We Yg Yi Xa) oO(aJ bV dF lL oE Ps Tn Ut Vi Wh Yg Yi Xa) lL(aA mP mT mU mW nB nN nR nT nU oQ) eP(Aw Jn Jr Kq Ps Tn Ut Yg Yi Xa) Yg(Ad Gb Hv Ks Mh Nd Rc Rx) Is(aA Iq Jj Jm Uy Yi Yl) nU(hR iB jD jH lK rB Vi) Yi(Cu Hv Jl Jr On) aA(hR Iv Ji Lv On) Jj(Jk Nt Nv Pg) Ut(lW lX lY nI) Uw(nC nH nI nJ) nR(hR jY Nm rB) Nd(Lp Sf yD) Tn(fB nI pK) Yl(Jr Lx Ou) hR(cF nN rY) oQ(jL lM lN) Gz(iB jP) Ly(wL yD) AwnI GbJr NuwL TzUy OhwJ VinH Unconstrained panels with 2 analytes, where 1.0E-7 >= 'AUC p-value' > 1.0E-8. Contains 168 panels of 149,894 total panels evaluated. : aA(eD Fr Jh Jk Jl Jp Jq lN Lx Mt Mu Mz Nj Nl Nn Nt Nv Nw Nx Pg Po) rZ(eD hA hV iB Il jH jL jM jP jQ jR jT jU lM qT qW qY rC) jI(eD hR kE kF kI Ko lL lW LY mT mW mY nA ND) On(eP Ii Iu Iv Jj Jo Jt Of Vh) Is(eP Gb Ii Iu Iv Jo Jt Lj) Nd(Hl Ru Rx Tn Um wJ Yf) gV(aL Ao Aw bO Cp dD Lx) lL(hR kP Ky mM Mu nC nO) nU(Aw hV Ps Tn Uw Wd) hR(lN Ly nO oQ rX) Gb(mU Nw Pg Ua) Tz(dX lN Si Va) Ut(kC kF kG mE) Uw(dX eP nL oP) Vi(mU nI nJ oP) Tn(kG mE mT) eD(aJ iZ Ky) eP(Jd Kx Ua) kK(iB Mu Mv) oO(Aw bQ dG) Mz(Jh Me) Yg(Gd Jo) Yi(Lx Nv) Jj(Iv Jl) Jr(Du Si) cF(aP nR) dX(Fy Qa) oP(Ps Uy) AamU FwnI GzjG NnNf NuNv UaSh IhwL HbQd HceQ WhnH KylN VaVv qVoQ Unconstrained panels with 2 analytes, where 1.0E-6 >= 'AUC p-value' > 1.0E-7. Contains 388 panels of 149,894 total panels evaluated. : Is(Ad Ax cF Hr Hw Ih Ij Il It Jh Jp Lh Li Ly Mb Mg Ml Ms Mu Nd Ni Nj Nl Nm Nn Ns Nt Nu Ny Of Og On Oz Pf Pg Pz Qa Qb Qc Qd Qe Rm Yj) aA(Aa cF Et Hr Ih Ij Ik Im Ip Ir Jg Jj Js lM Lw Ma Mb Mf Mj Mq Mv Mx Nc Ne Nh Nk Nq NR NU Ok Pc Qa Qd) Ut(eM Gb kE kI kN mF mI mS mT mU mW nC ND nF nK nL nM nR Si) lL(Fr Gz jD kG lM LY mE mI Mx mY mZ nA Nd nH Ni nL) gV(Cq Dc Hx Ih Ir It Iv Jh Jq Jr No Nr Nt Oh) Nd(Du Eq Ho Lt On Qv Ry Rz Tz Va Vu Yi Tl) jI(Id jD jO lK lX mF mI nF Ni nK nM oP oQ) oO(aO aP bZ cF cT Cu fA Kq lN oF Uf Yj) oP(Hl Ho hR jF jV jY lM Lt Rt Rx Va Th) rZ(hX jK Ly Nn On qU qV qX rA rB Wm) Lx(cF Iu Jj Lj Me Mp Mz Ns Pf) Jl(Hr Ii Iq Iu Iv Jm Um Uy Yl) On(Gb Hr Iq Jm Lj Ng Nm Ny Oz) Cu(Aa Dg Gb Jo Mm Nm Ux Va) Mz(Hw Iq Mq Mx Nn Ns Oh Po) Jr(cU Dr Em Hl nR Rx Sf Yj) Tz(cF eP Gb Hp Qv Rx Um) Jj(Ik Im Mx Nn Nx Po Qd) Nv(Jo Jp Me Mx Ne Of Va) nR(Aw jF lM Mq Mu rX rY) oQ(hA hV jF jH rB rX rY) eP(Fy Ky Ld Pe Vu Wd) nU(Hu iC jY Pz qU rX) Aw(Gd kE kN lW mE) Gb(Hq Im Ps Qd Vu) Iv(In Jp Nw wJ wL) hR(hA jH jL jO Lj) Me(bV cB cF gW) Yg(Bb cN Hb Rt) Wh(dX kE nC nL) Vi(nC nL nT Yi) Pg(Jo Pf Uy Yi) mU(Hl iB Lu Uy) nI(cG iB Kq Yj) Hv(Nn Yh Yf) Tn(gC kK nA) Qd(cF dX Iu) Jp(Mx Nn Um) Uw(kP mH mM) Nb(Um Yj) Hl(oV oW) Ua(Lp Va) Hq(nD Uy) Xa(kG pK) Oh(Hb wK) aP(cB eD) cF(bA cU) dX(Pe Pi) iB(mY nT) lN(aJ Fr) DeGd PoLj GzjO NtJo MpwJ NeNw QumE PsnC KyUm OpnH OuVa UfpK cUfR dDlW eDnY Unconstrained panels with 2 analytes, where 1.0E-5 >= 'AUC p-value' > 1.0E-6. Contains 1,156 panels of 149,894 total panels evaluated. : On(Ad dX Et Fp Fr Hq Hu Hv Hw Hx Ih Ij Ik Il Im In Io Ip Ir It Jg Ji Jk Jl Jn Jp Jq Js Lh Li Lu Lv Lw Lx Ly Lz Mb Mc Md Me Mf Mg Mh Mi Mk Ml Mm Mn Mp Mq Mr Ms Mt Mu Mv Mx My Mz Na Nb Nc Ne Nf Nh Ni Nj Nk Nl Nn No Nq Nr Ns Nt Nu Nv Nw Nx Oe Og Oh Oi Om Oy Pa Pb Pc Pd Pe Pf Pg Po Pz Qa Qb Qc Qe Um Yj Yl) Is(Aa aC aO bU bV cB cN Co cQ Cv dJ Et Fp Fr Hb Hq Hu Hv Hx Ik Im In Io Ip Ir Jg Jl Jk Jl Jn Jq Jr Js Lu Lv Lw Lx Lz Ma Mc Md Me Mf Mh Mi Mj Mk Mm Mn Mp Mq Mr Mt Mv Mw Mx My Mz Na Nb Nc Ne Nf Ng Nh Nk No Nq Nr Nv Nw Nx Oe Oh Oi Ok Om Oy Pa Pb Pc Pd Pe Po Um Uw Va Vb Vh) aA(aU bO cB cU Fp Hu Hw Hx Ii Il In Io Iq It Iu jH jl Jm Jn Jo Jr Jt kF kP Lh Li Lj Ly Lz Mc Md Me Mg Mh Mi Mk Ml Mm Mn Mp Mr Ms mU Mw My mZ Na Nb Nd Nf Ng Ni Nm No Ns Ny Oe Of Og Oh Oi Oy Oz Pa Pb Pd Pe Pf Pz Qb Qc Qc) Lx(cB Cs eP Fp Hq Hr Hu Hv Hx In Iq Iv Jh Ji Jl Jm Jp Lu Lv Ly Mc Md Mi Mq Mt Mu Mx My Na Nb Nm Nn Nt Nu Nv Nw Ny Of Oh Oy Oz Pc Pd Pg) Mz(Hq Ii It Iu Iv Jl Jm Jp Lh Li Lj Lv Lw Ly Mc Mh Mi Ml Mn Mp Ms Mt Mu Nf Ni Nm Nq Nu Nv Nw Ny Oy Pc Pf Qa Qd Um wL) Nd(cU Ed Fd Fi Gh Gp Gz Hp Iv Ji Jl Ky Nt Oa Op Ps Qd Ra rZ Sh Si Uf Uo Uw Uy Uz Vb Vi Vj Vp Vv Wb Wd wK wL Yl) cU(Aa aJ aN aO aP aR aV Aw bA BG BN BO bU bV cA cB cI cM cT dB dD De dF Di Dk dL dX eP lW Me nI Yg) Jl(Gb Hq Im Jh Ji Jo Jp Jq kK Lh Lj Lv Mb Md Mg Mi Mx Ng Nj Nl Nm Nn Ns Nt Nu Nv Nw Og Oy Pf Pg Yj) Nw(cF Hb Hr Ik Iq Jh Jj Jk Jp Lj lL Mb Me Mx Nf Nh Ni Nn Nt Nu Oz Pg Po Si Uy Yi Yl) Nv(Hq Hr Hv Ii Ik Iq Iu Iv Jh Ji Jm Lh lL Lv Mb My Ng Nh Nn Nt Og Oh Oy Pf Po Yl) aP(aC aF aK aL aO aU aV Aw aZ bA bF bN bO bR bU cT dA De dG dH Di dJ gV lN Me Um) jI(Bc Bo cB cF cH Ex hA iB iC jF jH jK jP jQ jR jT jU jV jY Li lM lO Nc Nj Nk Nu) Po(cB cF Hr Ii Iu Iv Jh Ji Jm Jo Jp lL Mp Nn Ns Nt Nu Of Og Oh Oy Pf Pg Um) nU(eD hA jE jG jL jM jT Lu Mb mE Mu Mv Nq Ns Nt Pb Pc Pg Qd qV rY Ut Wh Xa) Jj(Et Fr Ij Jg Jh Ji Jp Jq Js Lv Mj Mt MU Mv Nh Nl Nq Nu Qa Yg) Jp(Hr Ik Im Jh Ji Jk Lj Lv Ma Mp Mq Nq Nt Nu Oh Pg Qb wJ) Ut(Jo kK kO kP mH mM mP mY mZ nA nB nH nJ nN nO nT Qv Um) Me(aJ aO aR aU aZ bA cG cL Cu De dF dR eF gL Hc Jh Nn) Iv(Et Fr Im Jh Ji Jk Jm Jq Lv Ly Ma Mp Nn Pg Qa Qd Yg) lL(aD bO jL kE kK lK lX mF

Figure 32 Continued mH mS Mw nF nM Nq Qd) oO(bA dD eC eF fB fR Hc oQ Ou pH Qt Qu Ua Vu Wd) oP(cF eD Gh jG jU Nm rC Ru Rv Rz Vb We Yh Zq Yf) Nn(Ji Jq kK Lh Lv Ml Mx Ne Ns Nu Om Oy Pd Pf) Tn(dU eM Gb Hb kI kP lW lY mU nD nF nJ nK Um) Yg(aJ Ed Jt Ju kE KG Kj Ko Ma Nb oF Uu Va) Pg(Et Ii Im Iu Jh Ji Jm Mb Nu Um Va Vb wJ Yj) nI(bF bQ bZ Cu Cv dF Di eM Pi Qu Tz Ua Vu Yd) wL(Hx Il Ir It Jg Mm Nj Nm Og Oh Pd tN wC wQ) dX(Aw kF Kq Ky Nt NY Pf Qc St Ua Vu Vw) iB(hR kP lY ml mP mW mZ nA nD nK nN nR oQ) Tz(Eq Hl Ho jV kG Lj Rt Ry Uw Vz Wh Yl) Jr(BO cF dB De eM fR Gn Gz Jh Zw Tl) Qd(aO Ax bV cB cT dF Jh Jm Uy tF) Ji(cF Hb Iu Jh Jk Jo Lj Lu Oz Pa) Vi(cM kG kK kN kO mH mZ nD Ny Ow) hR(aO Bo eD hW iC In jP Ld lK lM) Hv(Lv Lw Oh Um Uz We Wg Yj Yk) Ps(eM Hb kG mH nD nH nJ Uy Yi) cF(aJ aZ cG cS dF Ky Lv Or Yi) mU(jD Ly Nm Nq Ns Pc Rv Uw Vv) Aw(eM kF lY mF nF nT oV pK) Cu(Ad eP Jt Uw Uy Vh Vw Yj) Mx(cB Jh Jq Mp Ne Nx Oh Om) gV(aR aZ Ba Dk Fw Gl Lv Nb) nR(Hu lK Mj Mm Mn Mv qV Rb) kG(Dk Fw Hu Mj Nq Ua Uw Yj) Ly(hA jO Nt nY wC wF wK) Hq(mF oT Um Va Yi Yl Tl) Oh(Jh Md Ns Nu Om Rf Um) rZ(It Lj Ma Mj My Nj Nq) Nb(Du Hl Lp Uo Yi Tl) Xa(dU eM kE mH nA oV) Vv(Gb Ky Lp Rt Rx Si) De(aC bA bO bV Oy) Nt(aZ In Mg Mp Ng) Mv(lY mE mY Sh Ue) aJ(aO cB Di jV lM) kK(Hu Jk Mw Nq Uw) oV(aO bA bF cT Lp) Ua(Rt Rx Ry Uy) Yi(Dk Gb Hb Jn) Qa(Iq Iu Jh Jm) Ky(jF jG lM Uo) eP(Cq Qb Qe Uf) oQ(eD jG lK mZ) Fr(Dg jG Nl) Gz(jD jV lN) Im(cB Si Ue) Hc(Gb Va Vb) Jh(Hx Jq Mp) Ou(kC kN Op) aZ(Aa aO Lu) bA(Aa fR Nq) lY(Kq Mu Mw) nH(Rv Wd Zx) wJ(Ih Nm Qb) Fw(nK Um) Nu(wF yD) Mj(mZ nO) Wh(Ed nJ) dF(aR Zq) dU(cS Rz) fB(Tr Uf) oT(eF iO) DkGb NqmP MqmZ NjyD HlkN ltwK QumT aUgC bOjG bUpK tFnY iZlN wDwF Unconstrained panels with 2 analytes, where 1.0E-4 >= 'AUC p-value' > 1.0E-5. Contains 2,970 panels of 149,894 total panels evaluated. : cU(aC aD aE AF aG aH aI aK aL aM An Ao aQ Ar aS aU aW aX aY aZ Ba bB bC bE bF bH bI bJ bL bM bP bQ bR bS bW bX cC cD cE cG CH cJ cK cN cO CP cQ cR cS Cu CV CW CX cY cZ dA Db DC dE dH dI dJ dK dM dN Fr Fw Gd Hr Hw Im Is Iv Jh Ji Jj Jk Jl Jo Lh Lu Lx Ly Mb Mm Mq Mu Mv Mx Mz Nb Ne Nf Ni Nl Nt On Oy Oz Pc Pg pK Po Pz Qd Si Um Yk) Jp(Et Fr Gb Hb Hq Hu Hv Hw Hx Ih Ii Ij Il In Io Ip Iq Ir It Iu Jg Jm Jn Jo Jq Jr Js Lh Li Lu Lw Ly Lz Mb Mc Md Me Mf Mg Mi Mj Mk Ml Mn Mr Ms Mt MU Mv Mw My Na Nb Nc Nd Ne Nf Ng Nh Ni Nj Nk Nl Nm No Nr Ns nU Nx Ny Oe Of Og Oi Ok Om Oy Oz Pa Pb Pc Pd Pe Pf Pz Qa Qc Qd Tz Uo Ut Wm) Jl(cF De Dp Et Fp Fr gV Hl Hp Hu Hv Hw Hx Ih Ij Ik Il In Io Ip Ir It Jf JG Jk Jn Jr Js Jt kG kP Li lL Lp Lu Lw Ly Lz Ma Mc Me Mf Mh Mj Mk Ml Mm Mn Mp Mq Mr Ms Mt Mu Mv Mw My Na Nb Nc Ne Nf Nh Ni Nk No Nq Nr Nx Ny Oc Of Oh Oi Ok Om Oz Pa Pb Pc Pd Pe Po Pz Qa Qb Qc Qd Qe Qv Vz) Po(aZ bA bV De Et Fp Fr Hq hR Hu Hv Hw Hx Ij Ik Il Im In Io Ip Iq JG jI Jn Jq Js Lh Li Lu Lv Lw Lx Ly Lz Ma Mb Mc Md Me Mg Mh Mi Mj Mk Ml Mm Mq Ms Mt Mu Mw Mx My Na Nc Nd Ne Nf Ng Nh Ni Nj Nk Nl Nm No Nq nU Nx Ny Oe Oi Ok Oz Pa Pb Pc Pd Qa Qb Qc Qd Qv wL) Qd(aC Ad AI aS aU bA Bb BN bO bU cL cQ De dJ eP Et Fr hG Hr Hw Ii Ik Il Im Ip Iq It Jg Ji Jk Jo Jq Jt Lh Li Lj lN Lu Lv Lx Ly Ma Md Ml Mm Mq Mu Mv Mx mZ Nc Ni Nl Nn Nq Ns Nt Nu Nv Nw Nx Og Oh Ok On Oz Pa Pc Pf Pg Pj Pz Qc Qv Ue Vz wJ Yl) Pg(Aa cB cF Fr Hb Hl Hp Hq HR Hw Ij Ik Il In Ip Iq Jq Ju kK Lh Lj Lp Lu Lv Lw Ly Ma Mc Mg Mi Mm Mp Mr Mt MU Mw Mx My Mz Nc Nd Ne Ng Nh Nj Nk Nl Nm Nn Nq Ns Nt Nv Nx OE Of Og Oh Oi Ok Oy Pc Pe Qa Qv Rt Sf Sh Si Ux wL Yg Yl) Lx(bU cK De dI Dr Et Fr Gb Hw Ii Ik Il Im Io Ip It Jg jI Jn Jo Jq Jr Js kK Lh lL Lw Lz Mb MF Mg Mh Mj Mk Ml Mn Mr Mv Mw mY mZ Nc Ne Nf Ng Nh Ni Nk Nl NO Nq Nr nU Nx Oe Og Oi Om Pa Pb Pe Qa Qc Um Uy wF wL Yj) Ji(aC aO Bb bU bV De Et Fp Fr Hq Hr Hu Hw Hx Ih Ii Ik Il Im Ip Iq Jm Jt Lh Li Lv Ly Mb Me Mf Mg Mj Mk Mm Mn Mq Ms Mt Mu Mv Mx My Mz Nc Ne Nf Ng Nh Ni Nj Nk Nl Nm Nq Ns Nt Nu Nw Ny Of Og Oh Oy Pc Pe Pz Qa Qb Qc Qe) Nv(cB eD Et Fp Fr hR Hu Ih Im Ip Ir It jI Jn Jq Jr Js Jt kG kK Lj lN Lu Lw Ly Lz Mc Mg Mi Mk Mp Mq Mr Ms Mt Mu Na Nc Ni Nj Nl Nm No Nq Ns nU Nw Nx Ny OE Oi Ok Oz Pa Pb Pc Qa Qb Ry Ux Uy Vb Vh Vz wJ wK wL Yj) Nd(aO aP bA Bo bV cB dF Dp Et Fc Fw Fy Gb Gl Hf hR Im Je Jf Jq Ju Kc kG Kx nR Or Ou Ow Qa Qh Ql Qm Qn Qt Qy Qz Rf Rj Rt Rv Sj St To Ub Ue Ug Uh Uk Un Up Ur Ux Vc Vh Vs Vw wC wD We Wg Wh Yh Yj Yk Zq Tm Xa Wm) aP(AA aD aE aI aN Ap aQ aS aW AX Ba bB Bc bE BG bI bJ bL Bn Bo bS cA cC cD cG cH cI cJ cK cL cM cO cR cS Cu cW cX cY cZ dB dD dF Dg dI dK DL dM Hr Is Jr jV lM Lu Lv Mb Mm Mv Nb Yg) Jr(AD aE Af aJ AI aO AW bA Bc bE bJ bN bR bS bV cA cB cG cL cN cO Cq Cw dC dF DI dL Eq Ex Gc Gd Gh Gp Iv Lp Lt Mp Mt Mz Nn Nu oE Oh Om On Ry Rz Sh Sj Um Vz Yg Yh Yk Zq Ye) Jh(Et Fr Hq Hr Hu Hv Im In Ip Iq Ir Iu Jm Jn Js Lh Lv Lw Ly Lz Ma Mc Md Mg Mi Mj Mq Mt Mu Mw My Nb Ne Nf Ng Nh Nl Nm Nn Nq Nr Ns Nt NU Nx Of Og On Oy Oz Pa Pc Pd Pe Qb Um wL) jI(aK aO aW bC bO cC cI dJ Fr hV hW Ij Il In Io Ip Iq Ir It Iu jE Jg jL jM Jn Jo Jt Mf Mm Mp Mr Ms Mu Mw Mx Na Nh Nl Nn Nx Ny Ok Om oO Oy Oz Pc Pe Pf qT qU qW qX qY rA rX rY Um) Nw(cB eP Et Fr Hu Hv Hx Ih Ii Il Im Ip Ir It Iu Jm Jo Jq Js Lh Li Lu Lv Ly Lz Mc Mj Mk Mn Mp Mq Ms Mt Mu Nc Nk Nl Nm Nq Nr Ns nU Nx Ny Oe Oh Oi Pa Pb Pc Pf Pz Qa Qb Qe rZ Va) Is(aF aH aJ AI aN aR AS aU aV Aw bA Bb bC bL bN bR cC cD cG cL cR cS cT cV Cw cX dB Dd De dF Dg Di dL dN fR kC kF lL lN mU mZ nO nU oE Qv Rt rZ Sf Si Uc Ux Vi Vt wJ wL) aA(aC aK aN aO aX aZ bA bC bG bN bR cG cH cS cY dB dD De dF Di Dk fR hA Hq HV iB jG jR kG kI kK kN kO Lu lX lY mE mP nA nC nH nI nK nL nN nT Om oO oP Um tF) hR(aJ bQ cB cE Fr hV hX jD jE jF jG jK jM jQ jR jT jU jV jY kP lO Lu Md Mf Mh Ml mM MP Mt MU Mx nB Nn Nq nT Nx Og Oh Oz Pc qT qU qV qW qX qY rA rB rC Um) lL(Aa aJ bC bI Bo cH Et Ex hA Hu iB iC In jG jH Jk jM jO jP JQ jR jU Jy kC kF kI kN kO LW Mf Mj Mm Mv nD Ne nI nJ nK Nn No Og Oh On qT qU qV qW qX qY rA) Fr(aC Ad aF aO Ap aZ bA Bb bV cB cR cT DI eD gV Hr Hv Ik Iq Iu Jq Jv kG kK Lj Lv Mb Me Mh Mx Mz Nc Ne Ng Nh Nj Nk Nn Nt Nu oE Oi Oy Oz Pd Pf rZ Um Ux Wm) Tz(Aa bN Bo cL Dp Du eF Fd Fp Gd Gn Hr Ib Jm Jt jU kF Li Lp Lu Mm Nb Ni Nm Of oO Rc Ru Rv Rz Sf Sh Uk Uo Uz Vb Vh Vi Vw Wc Wd We Wf Wg Yj Zq Zw Tl) Me(Aa aC aK aL aN aQ aV aX Ba bF bL BO bQ bU cC cN cS cT cY dD dG Di dJ Dk dL Ex Fw GP hB hG iZ Mp Mt Mu Mx Nq nR nU nY oE oF Oh pF tF) Aw(aC aJ aN aZ bA bO bV cH Em fR gC Gn kC kG kI kK kO kP lX mH mI mM mP mS mT mU mW mY mZ nA nB nC nD nH nJ nK nL nM nN nO oP oQ oT Sh Yf) nR(Di Hl Hq Hr HV hW hX iC Il Ip Iu jG jH Jj Jo Ju kP Lh lW Lz Mb mE mF Mh Mw Mx nA Nb Nl Nq nU oO oP Oz Pb Pc Qu rC Tn Um Uw Vi) Nt(Bo cB cF De eP Et Gb Hr Hv Hx Ii Ik Im Ip Iu Iv Jk Jm Jq Jt Lv Ma Mb Mc Mj Ml Mx Mz Nm Nn Nq Nu Oe Of Og Oh Oi Ok Oz Pa Qa Qb wJ) De(aJ aL aO aU aZ bF Bo cF cG cP cS cT Cu dD dF Di dL Em Fw Gp gV Hx Iv Jj Jn Jo Lv Mb Mj Mm Mt Mx Nb Ni Nu Of Og Oi Um Yi Yj) bA(aD aJ aN aO aU aW aX aY aZ bI bL BN BO bR bU cB cC cG cI cN cS dF dH Di dJ dL dX Em Fw Hr Im Jf Lv Ly Mq Mu Mv Oi oT) Qa(eP Et Fp Hr Hw Ii Ij In Ip It Jg Jq Lh Lj Lu Lv Ly Ma Md Ml Mt Mu Mx Nc Ni Nl Nn Ns NU Nx Og Ok Oy Oz Pa Pf Pz Um wL) Tn(Ad Bb cF eQ Ez Gd Gz Ib Jo kE kF kN kO Ks lX mH mM mS mW mY mZ nB nC nH nL nM nN nO nT oT oV Qv Rc Rt Rx Si Uy Vb) Iv(aO bO bV cB cF Hr Ii Ip Iu Jg Jo Lh Lj Lu Mb Mg Mj Ml Mm Mt Mu Mx Ne Ng Nh Ni Nl Nq Nu Nx Og Oh Ok Oz Pa Pb wK Yj) nU(bQ bV Di Hq hX Ip jF Jj jK Jn Jo jP jQ jU jV kG Lh lM LY Mj Mq Mx mZ Nb Ng nI Nm Nu Oz Pf Qc qT qW qY rC Vv) oP(bF Eq Fd Fi Gc Gd hA Hp hV hW hX iB iC jK jL jM jP jQ jT kG lO Lp mZ oO qT qU qW qX qY rA Si Ux Uz Vc Vh Xa) wL(Hu Ij In Io Ip Iu Jn Jq Js Li Lu Ma Mc Mg Mv Mx Ne Nf Ng Nx Of Oi Oy Pa Pc Pf Qe tT tU tX wF wJ wK yD) Mz(dX gV Hr Hx Ik Im In Ip Jj Jn Jq Lu Lz Md Mf Mj Mk Mv My Ne Nh Nx Of Oi Oz Pb Pd Qb rZ wJ Yg Yi) Oh(dX Im Iu Jj Jn Lh Lv Lw Mc Mi Mj Ml Mn Mp Mq Mt Mw mZ Nn Nq Oe oO Pe Pf Qv Ra rZ Ub Uy yD Yl tF) cF(aM aO bV cN cT Cu dG Ed Fw Gp Jj Jo Ju kF Mi Mj Mx Nb nI nO nT nY Ps Qv Sf Ub Vu Wb Wc Wh Yh tF) mU(aF bF Cv Eq hA Hp Hu Ii Ip Jm Jn Lp Lv Ma Mj Mm Mu Mv mZ Ne Nn Og On Ry Rz Si Va Wd Wh Yj) Im(aC aO aU Ax bV cL dF DI dX eP Iq Iu Jm Jq Lj Lu Mp Mt Mx Nc Nl Nn Nu Nx oE Oz Qv rZ Yi) Uw(kC kE kF kI kN kO lW lX lY mE mF mI mP mS mT mW mY

Figure 32 Continued mZ nA nB nD nF nK nM nN nO nT On oO) Yg(Aj aM aO Ap aZ cC Dg dH dJ dL dM dU Fn hC Ii Ij Jv mH Mm Oi On Pj pK Qv Sf Sh Si Uy Vo) Nn(Hq Hx In Ip Iu Jn IN Lw Ly Mc Md Mh Mi Mj Mk Mp MT My Nh Nl Nm Oz Pb Pe Ue wJ) aJ(aC aF aI aK aL aN aU aZ bF bL bN bO bQ bR bU bV cG cH cS cT dB dD dF dG gV jK Um) rZ(Ij Ip Iq Jk Jm Lz Mf Ml Mn Mp Mu Mv Mw Ni Nl No Ns Nx Ny Of Pa Pd Pf Pz Qc rX rY) Vi(Aa Ad Cu Ib kC kE kF kI kP lW IX mE ml mM mP mT mW nA nB nF nK nM nO Um Uo Yj) gV(Ad aU Ax bB bV bX cG CS CW Dd Fp Ik Jg Jk Js Jt Lh Lj Mw Mx Nj Nl Om Qc] Nq(bV Jq kC kF kN lN lX Md mF mH mS Mx mZ nC nD Ne nF nL nO Nu Om Ue Um Yl) Jj(cB Cu Fw Ih Il Ir Jn Lh Ma Mp My Nc Ne Nj No Nr Ok Pa Pe Pz Qb Qc Qe Ut) Hq(Fd Fi Gd Hl Ho Hp Lp mE nF nM Rt Rv Rx Ry Sf Sh Si Sj Vh Vj Vz Yj Yf) Um(aO bV Cu dF Gl Hx jO Mj Mp Mt Mv Mx My nl oE Om oO Qt Qv Ue Vu Yh tF) Hv(Dr Du Hl Lp Lt Md Mi Mj Mt Mu Om Ru Rx Ry Sh Uy Vh Vz Wh wJ Yl Zw) Mx(dX eP Et Gp In Ip Iu Lh Lj Lv Lw Ly Mb Mt Mu Nh Nu Ok Qc wJ wK) oO(aF aL Ax Ba bF cE cG Cs Ct Cv Dd Di Ez hC hG iB Ld Ma oV Tt Uy) Cu(aN Ap aR Ax aZ Bb bL Bn bV Dl Dr Hl Ne Of Rt Rv Uz Wc Wg Wh) On(aC Al Ap Ax Bb cB Cv Du Hl jG kK Ko lW Ma mE Mj nO Ok Si Vb) Nb(aZ cB eM fB Gb kK oT Ou Rv Rx Sf Uy Uz Vb Wg Yh Yk Yl Tm) Mt(Hl Hx Ik In Iu Jq lN Lv Ly Mp My Na Ne Ng Nu Pc Pd Pf) Mu(jG Jq kF kG lN Lv Mp mT mY mZ Ne Nl nO Nu oE Qv Ue Yl) eP(Ao Ba Cp Ex Hc Ho Js Ke Mj nY Om Pi St Vs Yh) Mv(Gb kE kF kG lW mM mT mZ nO nT Qv wF Yj Yl) aO(aM aN aR bN bO cB cL cS Ed Fw Mb Mi nl Yi) dF(aZ Bo bR cB cC cE cH Dg dH Di Gb Jo Mb Mm) iB(kC kF Ly mE mF mH mM mS nB nC nF nH nL nM) Ky(jD jL jO jR jT lK Lu nl Nm oE Rg Ue tF) Ut(Dr fB fR Gd Gz Ks Mm oQ pl Ue Uo Vb Yj) wJ(Hu Hw Il Ir It Iu Ly Mb Mg Ng Of Oy wF) pK(aU Ba bC cS Ez Hc kG Ld Ma nO Ow Qu Vv) Fw(aF bV cT Gb Gp hG Jo Mm Qv Uo Uy Yj) Ly(cB hG jG jL jP jQ jT lN oF Qv tU) dX(Cq cT Jf Jq Js Ke Mj Qb Uf Vh Vs) oT(aU bC bF bU cT Hc nl Ow Pb Vv Xa) Vu(Du eD Gh Hl Iu Lp Qv Rv Va Vb) cB(bV Jo Lu Lv Lz Mj Ml Ng Ns Oi) Mp(Iu kF lN Lv Mj Mq Nu Om wF) Hc(Gd oE oV Ps Rt Sf Ux Uy Tl) cG(Aa aC Bo Dg Di Gb Mb Mm Ng) oQ(bF bQ hW hX jD jP jU jY Wh) Ua(Gd Gh Gn Hp kE Sf Si Ux) Vv(fB Hl nl oE Qv Ux Uy Vb) Aa(bV cT Ed Gl Gp Ke Vj) Wh(fB kG kI kK mF mH mS) nl(cS Gn Uf Vp Yh Xa tF) wK(Hw Ih Il Ir Iu Mm Nu) wF(Mm Mq Og tN tX wC yD) Gz(gW hA jM jR jT lM) Lv(bV Et Iu Jq Lu Nu) Mj(kF kK kP lY mP Yl) Yi(Ex Jo kG Kq Rx Uy) Ou(kF kl Qv Sf Si Vz) oE(Lu No qT qV qX rA) oV(aF cS Cv Ld Pc Yh) Wd(kE kN nC nL oF) Jq(Ik Ip Iq Jk Nu) Yl(Dk Ex Lh Or Pf) aZ(cS Di fR Ni Yh) Bo(bV jV lM tF) Ed(bV Gn hG Uy) Et(Jk Lu Mb Nl) Gb(dM My nH Pf) Ma(kC IY Ne Nl) Hu(Gd kF IY mY) Qu(dU kK lW lY) Ps(kE kN kO Uo) Pe(Dr Lj mZ Om) bF(cQ gZ oD oW) cT(aR oD oW Rx) eD(dM gL iH rB) kG(Ib Jk Kq Mw) Cv(kF kN lW) Di(aN bV nT) Gp(Ne Oz tF) Yh(oF Qv Rc) Xa(jB kN Rj) Ok(Ik Jt Mb) Uy(Fy Qe Vp) fA(aU Ax Lj) hA(mF mW Ni) nH(Gn Hl Vj) yD(Hw Il It) lN(aM Mw nY) Ba(Dg Jo) Gl(Hb Jo) Nu(Lh Om) Sf(Ct Dk) Jn(bO eM) Kq(lW mE) Rx(dM Fy) Rv(nC nL) Uo(bV Ex) mZ(Mw Pf) hG(Jf tF) kF(bR Dd) EzfB MbcL MiaC HlHo UbOr HxOm YjhC RzmH LdpH UfdU VbVs VjPa bCjO nNqV mWjF iZjV rBkK jDrY

Unconstrained panels with 2 analytes, where 1.0E-3 >= 'AUC p-value' > 1.0E-4. Contains 7,626 panels of 149,894 total panels evaluated. : bA(aC Ad aE AF aG aH aI Aj aK AL aM An Ao Ap aQ AR AS aV Ax Ba BB BC bE bF BG bH bJ bM bP bQ bS bV bW bX bZ cA cD cE CH cJ cK cL cM CO CP CQ cR Cs CT Cu CV CW CX cY cZ dA DB DC DD dE DG dI DK Dl dM dN dR Ed eP Et Gb Gd Gl Gn Gp Gz Hf Ho Hq Hu Hv Hw Ii IJ In Iv Jh Jl Jj Jl Jm Jo Jp Jq Jt Ky Lh Li Lj Lu Lw Lx Lz Ma Mb Mg Mh Mi Mj Ml Mm Mp Mr Mw Mx Mz Na Nb Ne Nf Ng Nl Nk Nm Nn No Nr Nt NU Nv oD Oe Of Og Oh On Or Ou oW Oy Oz Pb Pd Pe Pf Pg pK Qb Qc Qe Rx Ub Um Uo Yg Yh Yj Yl) bV(aC Ad aE AF aG aH aI Aj aK aL aM AN aO AP aQ AR AS aU aV aW AX aY aZ Ba bB Bc bF BG bH bI bJ BN bO bP bQ bR bS bU bW bX bZ cA cC cD cE cG CH cI cJ cL cM cN CO CP Cq CS CT Cv CW CX cY cZ DB dC DD dF DG dH dJ DK DL dM dN dR eF Et Fp Gp HR Hv Hw Ip Ir Je Jf Jh jI Jj Jl Jn Jo Jp Jq Js Ky Lh Li Lj Lu Lx Ly Lz Ma Mb Mi Mj Ml Mm Mp Mq Mt Mu Mv Mw Mx Nb Ne Ng Nh Ni Nm Nn nR Nt Nu Nv Nw Nx OE Og Oi Ok On Or Ou oV Oz Pb Pe Pg Pj pK Qa Qb Qc Qe Qv Tz Ut tF) jI(aC aD aE aF aG aI aL AN AP aQ aR aS aU aV AX aY Ba BB bE bF bG bI bL bM bP bQ bR bS bU bW bZ cA cD cE cG cJ cK cL cM cN CP cR cS CT cU cV cW cX cY dA DB dC DD De dF Dg dH dI dK dM dN Ed Ef Et Fp Fw Gl Gp Hb Hq Hr Hu Hv Hw HX Ih Ii Ik Im Iv Je Jh Ji Jj Jk Jl Jm Jp Jq Jr Js Jv Kk Kl Kn Kq Kr Ky Lh Lj Lu Lv Lw Lz Ma Mc Md Me Mg Mh Mi Mj Mk Ml Mn Mq Mt Mv My Mz Nb Ne Nf Ng Nm No Nq Nr Ns Nt Nw Oe Of Og Oh Oi On Ow Pa Pb Pd pF Pg Pz Qa Qb Qc Qe Qn Qt qV Qz Ra RB Rj Tz Uc Ue Uo Ut) aO(Aa aC aD aE aF aG aH aK aQ Ar AS aU aV AW AX aY Ba bB bC bE bF bG bH bI bJ bL bM Bo bP bQ bR bS bU bW bX bZ cA cC cD cE cG cH cI cJ cK cN cO CP CQ cR cT Cu cV cW cX cY cZ dA dB dC dD dF DG dH DI dJ DK dL dM Dp eD fB Fp Gb Gh Gl Gp Gz Hb Hf Ho Hr Je Jf jG Jj Jo Jq Ju kE Ki Kl Ko Ks Ky Lh lL lM Lv lW Lx Ly Mj Mm Mq MU Mv Mx Nb Ne Nl Nq nR Nt nU Nw Oa oE Of On Or Ou Oy Pe Pg Pi Pj Po Qa Qb Qe Qz Rb Rx Sf Tn Tz Ub Uo Ut Vu Vv Yh Yl Zq Ye tF) Fw(aA aC Ad aJ aK aN aP aQ aR AS aU aV aX aY aZ bC bF bI BN BO bQ bR bU bX cA cB cE cG cH cL cQ cS cV Cw cX cY dB dE dF dH DI dK Dl dN Dp DR dX eF eM eP gL Gn Hf Hl Hp Hr Hw iJ In Ir Is Iu Jf Jm Jr Ju kC kE kF kK kN Kr Ks Ky Lj lL lN Lu lW lX LY Mb mE mF mS mW mZ nA NB nD nF nJ nL Nm NN nO nR Ns nT nU nY oE OF oO Or oT Oz Pj Ra Rt Ru Rv Rx Sf Si To Tv Ub Ue Ug Uk Ul Ut Uv Uw Uz Va Vb Vh Vi Wd Wg Yg Yl Ye) dF(Aa aC AD aF aG aH aI Aj aK aL aM aN Ao Ap aQ Ar AS aU aV AW AX aY Ba BB BC bE bF bG bH bI bJ bL bM BN bO bP bQ bS bU bX bZ cA cD cG cI cJ cK cL cM cN cO CP cQ cR cS cT Cu CV CW CX cY cZ dA DB dC dD dG dI dJ DK DL dM dN Ed Fp Fr Gh gV Hb HR Iv Jf Ji Jj Ky Lh Lj Lv Ly Mh Mi Mj Mu Mx Nb Ne Ng Nj Nk Nl Nm Nn Nq Nt Oe Of Og Oi On Oy Oz Pg Pj Po Qa Qb Qe Qv Rx Ry Si Uo Ut Ux Uy Yg Yi Yl) aJ(AA aD aE aG aH aM AP aQ aR AS aV aW AX aY Ba bB BC bE BG bH bI bJ bM Bn Bo bP bS bW bX bZ cA cC cD cE Ch cI cJ cK cL cM cN cO CP CQ cR Cu cV cW CX cY cZ dA Db dC dE Dg dH dI dJ DK DL dM dN dR Fr Gb Gl Gp gW Hf Hr iB iC Iv jD Jf jG jH Ji Jj jM jO jP JQ jT Lu Lv Lx Ly Ma Mb Mj Mm Mv Mx Nb Nd Ng Nn Ns Nt Nu Nv OE Oi Ok On Ou Oz Pg Po Qv Rx Sj Tn Tz Ub Uo Ut Uy Vv Yd Yh Yi Yk Zq tF) Fr(aK AL aN aP aR AS aU Aw bF bL Bn BO bR cC cF cG cH cJ cK cL cN Cv cX De Di dJ dL dN Dp Ed Et Ez Gb Gd Gp Hb Hq Hu Hw Hx Ih Ii Ij Im In Io Ip Ir It Jg Jk Jm Jn Jo Jr Js kF Ko kP Lh Li lM Lu Lw LY Lz Ma Mc Mg Mi Mj Mk Ml Mn Mp Mq Ms MT mU Mv Mw My mZ Nb Nd Nf Ni Nm NO Nq NR Ns Nx Ny Oe Of Og Oh Ok Om Pa Pb Pc Pj Pz Qa Qb Qc Qe qT Qv Qz Rb Rc Rm rY Tz Ub Ue Ul Uo Uu Uw Uy Vb Vo wF wL Yj Yl tF) Jr(aC aF aG aH aK aL aM aN Ao Ap aQ aR AS aU aV AX aY aZ Ba bB bC bF Bg bH bI bL bM Bn bP bQ bU bW bX bZ cC cD cE CH cJ cK cM Co CP cQ cR CS CT Cu CV cW Cx cZ dA Db dD DG dH dJ dK Dl dM dN Et Fd Fi Hp Hr Hv Ib Im Jf Ji Jj Jq Kd Ke Kk Kn Ko Ky Lh Li lL Lu Lw Mc Md Me Mi Mn MU Mw Nq Nt nU Nw nY Op Ow Pc Pe Pg Pi Pk Po Qa Qd rZ Uo Uz Vc Vh Vj Wb We Wg wL Yd Zx Tm Xa Yf) aP(Ad Af aG aH Aj Al aM An Ao AR As aY Bb bC bH bM bP bQ bW bX bZ cE Ch cN Co CP CQ Cs Ct CV Cw Cx Db DC Dd dE Dk dN fR Gl Gp gW hR Hv Hw iC Ii Im Iq Iu Iv Jf jG Ji Jj Jk Jl Jm Jo jP Jt Lh Li Lj lL lO Lx Ly Ma Mh Mj Ml Mq Mu Mx Ne Nf Ng Ni Nk Nl Nm Nn Nq nR Ns Nt Nu Nv Nw Ny OE Of Og Oh Oi Ok Om On Ou Oy Oz Pg Po Pz Qc Qd Qe Qv Sj Tn Tz Ub Uo Up Ut Vv Vz Wd Wh Yh Yi Yk tF) De(Aa AF aG aI Aj aK aM AN AR AS aV Aw Ax aY Bb bC bG bJ bM bN bQ bR bU bZ cA cB cI cK cL cN Cq cR Cs Cv cW Cx cY dA dB DG dH dI dJ Dk dM dN Dp eD eP Et fR Gb Gh Gl Gn hG Hl HR Hv Hw Im Ip It Iu Jh Jm Jp Ky lN Lu Ly Lz Mh Mi Ml Mp Mq Mr Mv Mz Nd Ne Nf Ng Nh Nj Nk Nl Nm No Nq Nr Ns Nw OE Oh On oO Or Ow Oz Pc Pg Ps Qa Qb Qc Qv Rx Sh Tr Uy Va Vi Vz Yg Yh Yl Xa Yf) Pg(aR aU Aw aZ Bb bL BO bU cL cN Di dJ dL Dp Du Ez Fd Fp Gd Gp Gz hG Ho Hu Hv Hx Ih Io Ir It JG Jk Jn Js Jt Jv kC kF kG Ki Ko kP Kr Ks Ky Li lL Lt Lz Md ME Mf Mh Mj Mk Ml Mn mP Mq Ms Mv mZ Na Nb nD Nf Nl NO NR nT NY Om Op oT Oz Pa Pb Pd pF Pj Pz Qb Qc Qe Qt Rc Rv Rx Ry RZ Sj Tz Ue Ug Uo

Figure 32 Continued

Uu Uw Uz Vc Vh Vj Vw Vz Wb Wc Wg Wh wK Yd Yh Yk Zq Zw Zx Ye Tm Tl Xa) IL(aF aH al aM Bc bP bR cA cB cF cK cN cR cW cY cZ
dE Dp eD Fp Hq Hr HV Hw Hx Id Ih Ij Ik Il Im Io Ip Iq Ir It Iu Iv jE jF Jg Jh Ji Jj jK Jm Jn Jo Jp Js JT jV jY Kj Lh Lj lN lO Lu Lv Lz Ma Mb
Mc Md Me Mg Mh Mi Mk Ml Mn Mp Mq Mr Ms Mt My Mz Na Nb Nc Nf Ng Nh Nj Nk Nl Nm Nr Ns Nt Nu Nx Ny Oe Of Oi Ok Om Oy Oz
Pa Pb Pc Pd Pe Pf Pz Qa Qb Qc Qe Qt rB rC Rf rX Tz Ue Um Vp Vu) cU(Ad Aj Al Ap As Ax Bb Bc bZ cL Co Cq Cs Ct Dd DG Dl Em Et Ex
Fp Gb Gc Gl Gp Hf Ho Hp Hq Hu Hv Hx Id Ih Ii Ij Ik Il In Io Ip Iq Ir It Iu Jf Jg Jm Jn Jp Jq Js Jt Ky Li Lj Lt Lv Lw Lz Ma Mc Md mE Mf Mg
Mh Mi Mj Mk Ml Mn Mp Mr Ms Mt Mw My Na Nc Ng Nh Nj Nk Nm Nn No Nq Nr Ns Nu Nv Nw Nx Ny Oe Of Og Oh Oi Ok Om oO oV Pa
Pb Pd Pe Pf Qa Qb Qc Qe Sf Ub Uo Ut Vz Wd Yi Yj Zx Ye) Nb(aC Al aN aR aU Aw Ax BN BO bR cA cG cL cN cR Cu dB dD Di dL Dp Dr
dX Ed eP Et Ex Fd Fi fR Fy Gd Gh Gn Gp Gz Hb Hf Ho Hp hR Im Iv Jf Ji Jj Jq Ju kG Kr Kx Ky Lt Mp Mt mU Mx Mz Nn Nt Nu Nv Nw oE
Oh oO Or Pj pK Po Ps Qa Qd Ql Qn Qt Qv Qz Ra Rb Rj Rm Rt Ru Ry rZ Sh Si Sj Ub Ud Ue Uf Ug Uk Ul Us Ut Uu Ux Va Vc Vh Vi Vj Vo
Vp Vu Vv Vw Vz Wb Wc Wd Wh wK wL Yd Zw Ye Yf) nR(Aa aE aF aY Bb bP bR bU cA cM Cv DD dl Dk Dp Ed Ez Fn Fy Gn Hb Hc Hw
Hx Ib Ij Im Is It Iv jD Jh jK Jl Jm Jn Jq JT jV kC kE kF kK kN Ko lN lO Lu Lw LX LY Mc Md Mf Mg mH Mk Ml Mp mS Mt mU mW My MZ
Na nC nD Ne Ng nH NK nL nM NN nO Nr Ns NT Nu Nv Nx Ny Of Oh Om On oQ Ou Oy Pa Pf Pj pK Po Ps Pz Qd Qn Qt QW rA Ri To Tz
Ua Uf Ug Vs Wh) cF(Aa aL aN aR Aw aX Ba bF BO bQ bZ cB cH cL DB dC dD Di dL dM dN Dp Du eD eF Fy Gb Gl gV Gz Hb Hc Hf hG Hl
Hq Hu Hv iB Im Io Iu Jf JH jO Jp Jq Jv Kc kE Ki Kj Ko Kr Lj Lu LW LY Mb Mh mP Mq Mt MU Mv My MZ Nd Ne Ni Nl Nq Nr Nu oE Og
Oi Ok On oQ oT oV Oz Pb Pe Pj Qa Qb Qe Qh Ql Qt Qz Rx Si To Ue Uf Uh Um Uo Ut Vi Vp Vv Wd Yd Yg Yk Yl Ti) aA(aD aE AF aG aH al
aL aM Ao aQ aR aS aV AW aY Ba bB bE bF Bg bH bI bJ bL Bo bP bQ bS bU bZ cC cD cE Ch cI cJ cK cL cN cO CP cQ cR cT Cu cV cW CX
cZ Db DC dE dG dH dJ dK dL dM dN dR dX fP hW jD jE jF jK jL jM jO jP jT jV jY kC kE lK lO lW mF mH ml mM mS mT mW mY nB nD
nF nJ nM nO oE oQ Ou Ps qU Qv Tn Uf Uo Ut Uy Yg Yh Yi Yj) Tz(aK aR Ax bF cB cM CS dB dG dL dN Dr eD Em Fc Fi fR Gc Gh Gp Gz
Ha Hb hG In Iq Is It Iu Iv JD Jf Jh Jj jM JO Js jT Ju Jv Kc Ks Lh Lt Lv lX Ly Mb Me mF Ml Mr Mt Mu mZ Ne Ng Nj Nt nU Ny Oa OE Og Oh
Oi Ok Om Oz Pa Pc Ps Qb Qd Qg Qt Qz Ri Rj Rm Sj To Tv Ub Ue Ug Ul Ur Ut Uu Uv Ux Vc Vj Vt Wb Yd Yg Yh Yi Yk Zx Ye Tm Xa tF Yf)
hR(Aa aF aM aV bC bF bJ bO bW cI cK cL cQ dG dK dM Et Fp Hq Hr Hu Hw Hx Ih Ij Il Im Io Ip Iq Ir Is It Iu Iv Jh Ji Jj Jk Jl Jm Jn Jp Jq Js Jv
Lv Lw Lx Lz Ma Mb Mc Me Mg Mi Mj Mk Mm Mn Mr Ms Mv MW MY MZ Na NC Ne Nf Nh Ni Nj Nk Nm No Nr Ns Nt Nu Nw Ny Oe Of
Oi Ok Om On oO Oy Pa Pc Pe Pf Pz Qb Qc Qd Qe Qt Qv qZ Ss Ue Uv Vq) Me(aD aE aF aG aH al Aj aM An Ao Ap Ar AS AW aY BB bC bE
bG bH bI bJ bM BN bP bR bS bW bX bZ cA cD cE CH cI cJ cK cM Co CP cQ cR CV cW CX cZ dA dB DC dE dH dI dK dM dN Ef Et fP Gl
hC hF Hv iA iH iJ Im iO iP Iv Jj Jn Jq Kc kQ kR kS Ky Ld Lh Lw Ma mU Mw Nt Nu nW oH oK Om oN Or Pc Qa Qd rZ Um wK wL) Im(aF
aK aN aS aV bF BN BO cG cN cT dD Di dJ Dp Et Ez Gp hG Hq Hr Hu Hv Hw Hx Ii Ik Il In Io Ip Ir It jG Jn Jo Js Jv Lh Li lN Lv Lw Ly Lz Ma
Mb Mc Md Mf Mg Mh Mi Mj Mk Ml Mn Mq Ms MU Mw My Na Ne Nf Ng Nh Ni Nk Nm No Nq Nr Ns nU Ny Oe Of Og Oi Ok Om Oy Pa
Pb Pc Pd Pe Pf Pj Qa Qb Qc Qe Sf Ub Um Vb Vz wJ wL Yj tF) Nd(aC aR Aw cG cN cS Cu dB dD Di Ez Fa Fb Fn HA Hb Hc hG Ib Ic Id Ik Jd
jG Jh Jj jO jP jT Jv Jy Ke KF Kg Ki Kj Kk Kn Kp Kq Kr Ks Kz lN Lx Mb Mp Mt mU Ne Nh Nl nU Nv Nw nY oE oF Ph Pi Pj Qg Qu Qw Qx
Rb Rc Rg Rh Ri Rm rX rY Sr Ss tO Tt TV Ua Uc Ud Ul Us Uu Uv Vo Vq Vt Vz Wc WF wQ Yd Zw Zx Ye Ti Th tF) Is(aD aG al aK aL Ap aQ
aW aX aY aZ bB Bc bF bH bJ bM BO bP bQ bW bX cA cE cH cI cJ cK cM cO Cs Cu cW cY cZ dA Db dC dD dH dI dK Dr Du eD eF Gn Gp
Hf hG Hl jG jH jT Ju Jv kE kG kl kK Kn Ko Kr Ks Ky lW lY mE mP nT oO Pj qT qY Ra Rc Ru Rv Rx To Tv Ub Ue Uk Ul Un Uo Ut Uu Uz
Vc Vo Vw Vz Wg Wh wK yD Zq Wm tF) Ky(AD aF aG Al Ar aV bC bF bJ bU cA cB cG cH cK cL cN cP cS cT Cv cW cY dB dC Di dJ dK
dL dR Ed eF Fa Gp gW Hb Hc hG Hv Hx iB iC Id Jd jE jH JM jP jQ Ju jV kF kG Kk Kq kS Lj lO lW Ly Mf Ml Mm Mt Mu Mv Nj nO Nu Ny
Om Pb Pc Pz Qg Qt Qu Qv Qx Qy Qz RA Rb Sr To Tr Tt Tv Ub Ud Uf Uk Ul Us Vt Vu We Wm) Mt(aZ BO cB Cw Di eP Et Fp Gb Gp Hq Hr
Hu Hw Ih Ii Ij Io Ip Iq Ir It Jf JG Jm Jn Jo Js kK Lh Li Lj Lu Lw Lz Ma Mb Mc Md Mf Mg Mh Mi Mj Mk Ml Mn Mq Mr Ms Mu Mv Mw Nc
Nf Nh Ni Nj Nk Nl Nm No Nq Nr Ns nU Nx Ny Oe Of Og Oi Ok Om oO Oy Oz Pa Pb Pc Pj Qb Qc Qd Qe rZ Ul Uo Uz Wg wJ wL Yj Yk
Yl) Jq(Aa Bo cB Et Fp Hq Hr Hu Hv Hx Ih Ij Il In Io Ir It Iu JG Ji Jm Jn Jo Js Jt Lh Li Lj lN Lu Lw Ly Lz Ma Mb Mc Md Mf Mg Mh Mi Mj
Mk Ml Mm Mn Mp Mq Mr Ms Mv Mw My mZ Na Nc Ne Nf Ng Nh Ni Nj Nk Nl Nm No Nr Ns nU Nx Ny Oe Of Og Oh Ok Om Oy Oz Pa Pb
Pc Pd Pe Pf Pz Qb Qc Qe Qv rZ Um Uy Va Yi) mU(Ax bQ DD Di dR Du Fp Fy Gn Hb Hc Hq Hr Ih Ik In Io It Iu Iv Jh Jk Jl Jo Js Jt Ju kG Lh
Lj Lw Lx Lz Mb Mf Mg Mh Ml Mn Mp Mw Mz Na Nc Nf Ng Nh Ni Nj Nl Nr Nt NU Nv Nw Ny Oe Of Oh Oi Ok Ou Oz Pb Pf Pj Po Ps Pz Qd
Qe Qu Qv Rt Ru Rx Sf To Ub Uf Ug Um Uo Vb Vj Vt Vw Wf Yg Ye Ti Th tF Yf) Ut(Aa aC aN aR aS aU aV Bb bl bL BN Bo bU cA cB cL cR
cT DB Dl dL Dp Du Em Ex Ez Gn Gp Hb hG Hl Ho Hp Ib Ii Iq Iu Je Jf jG Jl Jm JT Ju Jv Kj Lh Li Lp Ly Ml Mn Mp Nf Ng nW Oh Ok oP oV
Oz Pa Pc Pj pK Rc Rt Ru Rv Rx Ry Sf Sh Ub Ug Uk Ul Ur Uu Uw Ux Uy Va Vh Vo Vw Vz Wc Yl Ye tF) Qd(Aa aF aK Ap aQ aR bF bL bR
cG cN cR CS cY Dd Di eM Fp Gp Hq Hu Hv Hx Ih Ij In Io Ir jG Jn Js Ju Jv Kj kK Ko kP Ks Lw Lz Mb Mc Mf Mg Mh Mi Mj Mk Mn MP Mr
Ms Mw My Na Ne Nf Ng Nh Nj Nk Nm NO Nr Ny OE Of Oi Om Oy Pb Pd Pe Qa Qb Qe Rc Rm rZ Si Ub Um Va Wh wK wL) Aw(aF aK aL
AR As aU aV Ax bC bF bG bL bN Bo bQ bS bU bZ cA cB cC cD cE cG cI cK cL cN cO cP cQ cR cS cT Cu dB dD dG dH Dl dJ dL dM Dr
dU eQ Ex Gb Gc Gh gZ Ho Hr Iv Ji Lj Ly Mb Mm Mx Nf oE Of Og Or Oy Pe pl Po Ps Rv Rx Sf Um Uy Va Vb Wg Yi Yj Yk Yl Tl) Cu(aC aF
aH Aj An AS aU aV aW aY bB Bc bM bN BO bP bQ bU cA cB cC cI cK cL cM cN cO cR cT Cv cW cX Dd dH Di dJ Dk dL dM Du dX Gd
Gn Hb Hp Ii In Iq Iv Jm kG Ks Lh Lj Lt Lu lW Mb mE mM Mx Ng Nl Nn Ok Oz Pj Ps Ru Rx Sf Si Uo Vb Vc Vj Wd Yh Yl Zw Tl Yf) Po(Aa
aC aF aK aL aN aR aS aU aV Ax bC bF bL BN BO bR bS bU cA cC cD cG cH cJ cK cL cN cO cS cT dB dC dD Dl dJ dL dN Dp dX eP Gb Gp
hG Ih Ir It Jk Jt Ju kG kK lN lY Mf Mn Mr Mv mZ nO Nr nY oE Om Pe pF Pz Qe qY rZ Ub Ue Uo wF wJ Yi Yj tF) Nq(aR Bn cB cN Co cT
Du Et Fc Gb Gh Gp Gz Ho Hv Hx Ik Ip Iq Iu JD jG Jn Js Jv kE kl kO kP Lh Lv LW LY Mc mE Ml Ml mM Mp mW mY nA nB NH nl nJ nK
Nl nM NN Ns nT Nx Ny oE Of Ok oO oP Oy Oz Pa Pd Pe Qa Qb Qv Rx Si Ub Uo Vz wF wL Tm) Lx(aE aU aV aZ bl BO bR bS cA cC cN cO
Cw dA dB dC Di Dp Du dX Fa fR Gd Gp Gz Ha Hl Ih Ij Ir Jf jG Jk Jt kC kE kF kG kO Li lN Lt lW lY Ma mE ml Mm mP MS nB nC nF nH Nj
nK nL Oa Ok oO Op oT Pz Qb Qe Qv Rv Rx Ry rZ Sh Uo Vi Vz Wb Wf Wh Yk Ye) Iv(aK Al aR aU aZ Bn Bo bR cG cL cN cS Di dX eM eP
Fp Gn Gp hG Hq Hu Hv Hw Hx Ih Ij Ik Il Io Iq Ir It Jn Js Li Lw Lz Mc Md Mf Mh Mi Mk Mn Mq Mr Ms Mv Mw My Na Nc Nf Nj Nk Nm No
Nr Ns nU Ny Oe Of Oi Om Oy Pc Pd Pe Pf Pz Qb Qc Qe Qv rZ wQ yD Yh Yk) Um(aC Ao aR Bg Bn bP cG cL cN cS Ct dB dG Di Dk dL Ed
eF Et Ex Fy Gb Hw iB iC Jd Ji Jn Js jT Kc kF KQ Lh Ly Mk Ml Mn Mq Mu Mw Nj Nn No Nr Nt nU Nv Nw Nx nY oP Or Ou Ow Oz Pe Pi Pk
Ps Qb Qc Qe Qh Ql Rh Sr Ub Uf Un Up Uw Vp Vs Vv Wd Wh Zx Xa) cG(Ad aF aH Aj aL aM aN Ap AR AS aV aY aZ Bb Bc bG bJ bL BN
bO bP bQ bR bU bW cA cB cC cH cI cM cO cP cQ cR cS cT CV cW cX DB dD dH dI Dk DL dM eP Fp Jj Jo Jt Lh Lu Ly Lz Mh Mj Mx Ne
Nm Nn OE Oh Oi Oy Oz Rx Si Uy Yl) Nt(Ad aF Aj aN aY bO cN Dg Dl Fp Gz hG Hq Hu Hw Ih Ij Il Io Iq Ir It Jg Jn Js Lh Li Lj Lu Lw Lz Md
Mf Mh Mi Mk Mm Mn Mq Mr Ms Mu Mv Mw My Na Nc Nc Nf Nh Ni Nj Nk Nl No Nr Ns Nx Ny Om Or Oy Pb Pc Pd Pe Pf Pz Qc Qe Qv Rx
Vb wK wL) kF(Aa aE aF Bb Bc bG bQ cA cM dD Dg Di Dk Dl Dp Ed eP Fa Fn Hc Hq Hv Ii It Jj Jk Jl Jn Jo Ju Lu Ly Lz Ma Mb Mq Mw Mz
Ne Nm nU Nv Nw Ny On oP Or oV Oz Pb Pc Pf Pj Ps Qu Qw Ri To Ua Ug Uk Uo Up Us Uu Uv Vs Vt Vv Wh Zx Tj) oO(aE aM aQ aS aW aY
aZ bC BG bM Bo bR bX cB Ch cL cN Cp Cq cS cV Cx Dc Dk Dl dM dR dU eD eM Fy GL Gn Gp hA HB Hf iA Jl Kd Ke Kf Kl Kn Kp kQ Kx

Figure 32 Continued

Figure 32 Continued hG JU Ml Mq Oz Pz Uc tF) pK(aQ bZ cT Cv Fy Ju Kq Kx mP oF Rz) Ed(bG Eq Hl Hp jD Sf Sj Vz Yk Zx) Hu(kE IW mE mP mZ nB nO nT Va
Yl) Uy(cL dM Js kN My nH Oa Qh Uo Wb) Pf(Du Gd kC kK mP nO Rx Sf Si Wc) bO(aR Bg cN Cp Cq cT Dk dM Ny Pe) Mq(Du hG kP mP
Ne Nl nO Ue tF) aM(eD jG jH jM jO jP lO Vz Yk) oV(eM Ez fA Gn Hb Rz Sj Vz tF) Dk(aR dK Hb Hl Jv nO Rx Si) Mm(Ex Mb Ne Nl oW wC
wH yD) Nh(Hx ln Ip Jg No Pa Pc Qc) Qu(fB kl mF mY mZ nD nJ nK) Va(Bn cL cT Ng Nx Pz Vp Yk) jD(iJ iO iZ jG Ni Qn qZ rX) Nl(ln Ip Mr
Ni No Pa Qc) Rx(Bn dG My Ow Qn Vp Yk) Yl(Bg cL Ef Ld My Ow Vp) Pc(kK kP mP mZ Ne nT oW) eD(Bn hG Ic qV qZ Uv Vs) kN(aE Al
Ax bM Gn Vs Zx) Qt(fB jG jO jP jT Uo) Rz(Ap fB kE IW nH oF) Vb(Fy Iz Ng Pz Qy Vw) aF(aR dG dL fA oW tF) hA(jG jH Li nA nN rY)
hV(jR Lj Md mP mY nT) Ex(Du Hl lM Qw Vh) Mb(aU cN eF gL Ip) Qb(Jg Jm Md Ni Nx) Jf(aC cN dG oF tF) aR(aI aL bG Cp dD) cT(dL eQ
fR Jo Kc) hG(Bn Hb Rb Ub Uo) kK(Cv dD iC Pb Pz) Ef(aC Oy Sh Ue) Gn(mM nC pH Vp) Qe(cL Iu Jm Nx) Js(In Jm Nx Of) Lj(Ip Oa oW pH)
mE(bZ dD Pi Qw) mZ(Li Lz Ny rB) jG(cW jL jO nN) Bn(aX Mi Yf) Cp(eM fR Jo) Nm(Ho mP oW) My(rX rY Sh) Hl(nD oF pH) Ub(eF Ho
Uo) Vz(nH Oa Ow) Zx(Ju nL Sf) Kq(nJ nK nL) Ld(dU eQ jB) aC(aX dM Lw) tF(gL Jo Uo) kE(Eq Pi Vs) kP(Ny qV rB) Dr(Fy nC) Ne(In Ip)
Nj(wC wQ) Hr(Hx No) Ir(Iu Jm) Ke(Hb Pj) Ow(jB Si) Vp(Dp Rt) Pe(Ax Iu) aU(jB pI) bC(dU oD) dD(mP nT) dG(bR Yk) eF(gC Hf) nN(jP lM)
IW(bZ Pi) jO(bW Ni) CvnO FyRv GhkR MdHx NglY NkfR UeUo HwwD IhyD IjJm IzSh YdnH JdnF JgPa WeQx LpbU VhnC VsfB PbpH dBdM dRlX mMiC mPrB mWjM nKlK iOjV iZjK

Constrained panels with 3 analytes, where 1.0E-10 >= 'AUC p-value' > 0. Contains 44,065 panels of 25,049,241 total panels evaluated.: oO{cT(AA aJ aM aO aP aR Aw AX aY bC Bg Bo bQ bR bV bW bZ cF cG cL cR CS CU Cv Cx Dd dF dG Di Dk dL dN EF FR Gn Hc Hr Hu iA Is Jl Ju Jy kE Kq Kx Lu Lv Lx Lz Ma Mb Me Mh Mj Ml mP Mq Mr Mt Mu MZ Nb Ni Nn NO Nq NR NT NU OE oF OH oK oP oQ Ou oW Pf Pg Pi Qa Qd Qg Qu Qv Tr Ua Uc Uf Ug Um Ut Uw Va Vv We Yd Yi Yj Zx Xa tF) aJ(Aa aF aL aO aQ aU aV Aw AX aZ BA bF Bo bQ bR bU bV bZ cB cE cF cG cL CS CU Cv cY dA DD dF Dl dK dN eC Ez Fy Gb Gh Gn Ho Hr Is Jl Jr kE kG kN Kq Kx Ld Lv Lx Lz Ma Mb Mh Ml Mq mY MZ nA Nb nC Ne nH Nl nL Nn NO Nq nR oE oF Og Oh oT Ou oV Pa Pc Pe Pf pH Qg Qt Qv Rf Rh Rv Rz Tr Tt Ug Um Ut Vv Yd Yh Yj Yl Zw Yf) Kq(AA Ad aF Aj Al Ap aQ aS aU Aw bA Bb Bo bQ bV cF Cv Dc Dd Dg dl Dl Dr dU eF Gc Gd Gn Hb hG Hl Hr Hu Hw Ii Iz Jg Ji Jj Jo Jq Jt Ju Jv Kf KG Kj Kl KS Li Lu lW lY Mb mE Mh Mm Mn mT mU Nb Ng nl Nk Nm Nn Nv Nx Ny oE OF Oh Ok oQ oV Pa Pc Pj Qe Qv Rc Rm Rt Sf Sh Ub Ug Uk Um Uu Uv Vb Vo Vq Vt Vw Wb Wh Yd Yj Zq Ti) Yi(aA aF aM aO aP aQ aV aY aZ BA Bb bC bl cE cF cL cP Cv cY dF dG dH Dk dL dM dN DR dU eM Gb Gc Gd Gn Hb hC hG Hl Hr Hu Hv In Is Je Jn Jo Jv kE kG kR KS Lu lW Lx Ly Mh Ml Mm mP mU NB Ng Nk Nm Nn Nq nW Ny oE Of Oh ON oP oQ Ou Ow Oy Oz Pb Pd Pf Pg Pj Po Qv Sh Tv Ug Ul Um Uw Uy Vb Vs Vt Wb Zq) Wh(aN aO aP aY BB Bo cF cG cH cP CV CX Db Dc dF dH Dl Dk dL fB Fd Gb Gn Hr Hv Is Iz Jn Js Kc kE Ki Ky Lv Lx Ly Ma Mb mF Mh Mj MP Mq mT mU mW MZ nA Nc nH nJ nL No Nq NU Nv Ny Oh On oP Or Ow Pa Pc Pd Pe Pg Pk Po Qa Qd Qg Qh Qn Tv Tz Ub Uc Ue Ug Um Ur Ut Vi Vp Vs Wb Wf Yh Yj Yk Ye Xa) Cu(AA Ad aF Al Ap aS aU Aw AX bA Bb bl bV cF Cv Dc Dd Dg dl Dl dN Gc Gd Gn Hb hG Hr Hw Ii Ij Ip Jj Jm Jo Js Jt Ju Jv Kf KG Kj KS Li Lu lY Mb ME Mf Mh Mm Mq mU Nb nl Nm Nn nO Ns Nv Nx Ny Oe Of Ok Op Pb Pc Pj Qe Qg Qv Rm Rx Sh Si Ub Ug Uk Um Ur Uv Vo Vz Wb Yj Zw) Xa(Aa aM aO aP aQ aS aV aY aZ bA Bb bF bQ cE cL cN cP Ct cU cY Dd dH DR DU Gb Gc Gd Gn HC hG Hv iJ In Is Jo Ju Jv kE kR kS Lu Lv lW Mb Me Mj Mm mP mU mW Mz nA Nm Nu Nv nW oE oF oN oP oQ Or Ou oV Pb Pc Pg Pj Po Qa Qd Qt Qv Qz Rg Sf Uc Ur Vi Vp Vs Vv Wd Yj Tj) Um(aO aP As aU Aw Ax BA bF bQ bV bX bZ cE cL Co CS Ct DD dF dG Dk eC EF Ex Ez Fy Gl hB Hc hG Jd Jh Jk Jl Kx Ky Ld Lx Ma Mj Mk Mt mU Mv Mw Nb Nd Ng Nj Nn nO Nq nR Nv oE OF Oh ON oP oQ Ou oV Pk Po Qa Qt Qu Tn Ua Uf Ut Uw Vs Vu Wd Zw) bV(AA aM An aO aP Aw bJ cE cF cG cl cL Ct Cv cW dG Dl dN eC eF Ez fP Fy gZ Hr iO Is Iv Jl Ju Ld Lv lW Lx Lz Ma Mb Me mF Mh MP Mq Mr mU Mz Nb Nl Nn nR NU oE Oh oP oQ Ou oV Pe Pf Pg pH Pi Qa Qd Qt Rf Rh Rm Uc Uf Vs Vv Yh) cF(aA aE aO aP Aw bQ Ct cU CV Dc DD dF dG dH dM Ez fR Fy Hc Is Jl Jr Ju kF Ld Lv Lx Lz Ma Me Mh Mj Ml Mp Mq Mr Mz nO nR nT oE oF Oh oP oQ Or Ow Pe Pf Pg pH Po Qa Qd Qh Ql Qn Qt Rf Rh Rm Tn Tr Tv Tz Ua Uc Ut Vs Vu Vv Zw Wm) Aw(aC Ao Ap aQ aU Ax aZ bA Bb Co Cs DD dF dL Dp Ez fR Fy Hb hC Hr Is Iz Je Jh Jj Jl Ju Jv Kd kF kG kN Kx Ld Lv Lx lY Lz Ma Mb Mh Mk Ml Mq Mw My Nd Ni oE OF Oh oV Oy Pe Pf Qa Rf Rh Rz Tr Ug Uk Ur Uw Vv Yg Zw Wm Yf) Ju(aK aL aO aQ aU Ax aZ BA bF Bg bQ bZ cE cG cL Cp Cq Ct cY Dc dF dG Di Dk dR eC Fw Fy Gl Hc hG Is Jk Jl Kx Ky Lx Mj Mt MU Mv Nb Nd Ng Nn nR Nv oE oF Oh oN oP oQ Or Ou oW Pg Ph Pi Qh Qu Rz Tn Tr Ua Uf Ut Vi Yh) Rf(Aa aE aL aO aQ aU aV aX aZ bC bF Bg bL bQ bR bX bZ cB cE cG cL cN Cq cV cY Dc dD dF dG Di Dk eF eM Eq Fd fR Gz hB Hc hG iJ Jk Jl Kd Kl Kp kQ Mj Mp MU Nd nR oE OP Or Ou oV pH Sj Ua Ux Vu Vw We Wf Yh Yk Zx) Rz(aO aQ aV aY bF bQ cE cL cP cR cX cY dF dH dL dR Gc Gd Gn Hl Is Iv Jo Js Jv Kc Kg kR Ld Lv lW lY Mb Me Mj Mp mT mU NB Nk oE Oh oN oP Or oV Ow Oy Pa Pb Pc Pg Qa Qd Qg Sf Sh Tv Tz Ua Uc Up Uu Vp Vs Wb Yj) bA(Aa aP aR aY bR cU Cv dG Di eC Eq Ez fA Fy Gn Hr Jl Jv Jy Lx Ma Mb Mq Nb Ni Nq nR Nu oD oE oF Oh oQ oV Pb Pf Pg pH Po Qa Qd Qg Qt Qu Qv Rh Tn Tr Ua Uc Uf Ug Ut Uv Uw Ux Uy Vs Vu Vv Vw We Yd Yh Yj Yl Zw Wm) dF(AA Af aM aP Ax Bb Cs Cv Cx Dd dN Dp fR Gn Hb Hr Ii Io Jj Jo Jq Jv Ld Lh lW Lz Mb Mh Ml Mm Mn My Nb Nl Nm Nn nO Nu Nv Nx Ny OE Of Oh oQ oV Oy Pc Pe Qd Qm Qv Rh Rt Rx Ug Uk Up Ur Uy Vz Wc Yk Yf) Tn(Ad Af Al Ao Ap aS aU aX Bb bX Ch Cv Dc Dd Dg dH Dl dR eC Hb Hr Hu Ij Iz Ji Jk Jl Jo Jt Kd Ke Kf Kg Kj Kl Ko Kr Ks Lu Me mM MP Mt MU Mx Nd Nj NN nO nR nT nU Of Oh Ok oQ Ph Pj Qv Rc Ug Uk Vu) Uy(Aj aM aO aP As Ba bZ cE cL Ct Dc dG Eq Ez Fd Fw Ih Im Ip Iq Is Jm Jr Js Kf Lv Mf Mj mU Mz Nb Nd nR Nv Ny Oa oQ Or Ow Oy Pa Pd Ph Pi Po Qa Qd Qe Qh Ql Qt Qz Rg St Tv Vp Vq Vu Wd Yd) Oh(aF Al aO aQ aS aU aV AX aZ BC bF bl bQ cB cE cG cL cN cS cU Cv Dd De Di Dl dN Dr eF Eq fR Gb Gn Hb Hc hG Hl Jv Kd Ks Lp oE Ou pH Pj Qg Qv Rm Ru Sf Ua Ub Ug Vo Wd We tF) Tr(AA Ad Ap aU aV AX BC Bo bP cN Cs Cv Dc Dd Dg Di Dl dN dU EF eM Hb Hr Hu Iz Jk Kf Kj Ks Lu Me Mj mM MP Mt MU Mw Mx Nh NN nO Nq nU oD oQ Pc PH Pj Qy) Ut(Aa Ao aQ Ax Bb bC bX cS Dd dG dL Dp dU eF Em Gh Hb Hr Hv Iz Jd Je Ji Jo Jq Jt Jv Kd Ke KF KG Kj lY Mn Ms mU Nj Nk Nx Ok oQ oV Pa Pc Pj Qv Rc Si Ug Uk Ur Uu Va Yj) Rh(Aa aE aL aO aQ aU aV aZ bC bF bQ bR bX cB cE cG cL cN cV cY Dc dD dG Dk dR eF Fd Hc hG Hu Jk Jl Kl kQ Mj Mp MU Nd nR oE oQ Or Ou oV pH pK Sj Ua Uw Vu Yd Yh Yj Yk) Fy(aK Al aM aQ Ar aS aU aV Ax aZ bC Bo cE cL cN cR cX cY Dd dG Di dJ dL Dr dU eF Gb Gc Gd Gn Hb hC Hl Hu Jk KS Mj MU Nd Nj nO nR oQ oV Pj Sf Ux Wb Yj Zq Ti) Ba(AA aF aY Bb bR Cv Dd fB Gd Gh Hl Hp Hr Jj Jl Jo Jt Jv kF kG Ks Mb Mm Nm Nn nR oE OF oV Oy pH Qa Qd Qg Qv Rg Sh Si Uc Ug Uk Ur Uw Ux Va Vb Vv Yg Ye Tj) Uw(aO AP aQ aS aU bQ cN cP dL Gb Gc Gn Hl Is Iv Jg Jl Jn Jt Kf Ki Kl Kp Ly Mh mP Mq mU NB Nk nL nU On Oz Pc Pd Pj Po Qv Rc Rm Ub Uc Ux Vb Vw Wb Wf Tm) oE(Aa aQ aU AX bC bP cE cL cS Cv Dd Di dL dN dU eF Ez Gb Hc Hr Iu Iv Jr kF kG kK Ld lY Mm mP Mq mU mZ Nb nl Nk Nm Nn nO nR Ns pH Pj Rx Vv Yd Yh Yj) bQ(Aa aP Ax Bb bR cA Cv Dd dl dL dN Dp Em fR Hb Hr Jd Je Jo Kd Lv lW Lx Lz Mb Mh Ml Mm mP Mq Mw My Nb Nn nO Nx Ny oF Pc Pe Qz Rv Ug Uk Ur Vv Wd Yl) Yj(Aa aO Ax bZ cL cM cO gL Hc Ij It Iv Jk Jn Js kG Ld Lx Lz Mg Mh Mj Ml Mq Mv Nb nl Nn Nq Nr Nv Nw Oa oF ON Ow Pe Po Qa Ql Qt Qx Ra Vu Zw Wm) Yg(aM aO aP aQ aS aY aZ bH bl cP cR Dg dH dl dL dN dU Gn hG Hq Hu iJ Je kE kR Li Lu lW Ly Mb Me mP mT mU nB Nu Nx oN Oy Oz Pa Pb Qn Rx Wb Ye) oF(AA Ao bC cE Ch cL cN Cv Db Dd Di Dr dU eF hG Hl Hr kF kG lW Mk Mm mP Mq mU My mZ Nb Nd Nm nO nR Ns Op oQ Oy pH Rb Ry Sh Ua Ug Vv Yh Yk) dG(AA aL aO Ap aQ aS AX bR cU DD Di fB fR Gb Gc Hb hG Hl Hr Kd kP Lz Mb Mh Ml Mm mY nl Nm nO oT pH Qv Ru Rx Ug Vi Vz Wc Zw Ti Yf)

Figure 32 Continued oQ(aC aL Ap aQ aX aZ bF cE cS cU DD Di Dp Fc fR Gc Hb HI Jd Je Kd Lt nR nU oT pH Qg Qv Qx Qz Rg Ry Ua Ug Uk Ur Vi Vv Wc Yd Yh
Yl Yf) aP(aF aL aO Ap aQ aS aU aV aZ bF cG cL cV cY dA DD Di dR fR hG Hr Jl kG Lv lY Mq mZ Nd nR oT oV pH Qg Qh Rt Sj Ua Uc Ug
Wd Yd) pH(aR Ax cJ cP CS Ct Dd dl dL Ez Hc hG It Iv Lx Lz Mb ME Mh Mk Ml Mq Nb nl Nr nW oP Oz Pc Pe Pf Qt Qx Ra Ri Uf Vv Yl
Wm) bZ(AA Ao Co Cv Dd dl Gb GC Gn gZ Hl Hr Ij Jo Kd IW Mm Mn Nd nl Nm Nn nO Ny oV Oy Pj Qv Qx Qz Rb Sf Ug Uk Ur Vi Wb Wd)
Hc(Ao aQ aU aZ Bo cG Cv cX Dd Dp dU Fd Gb Gn Hr Jj Kd kG lY Mb Me Mh Mq mU My Nd nO Of oV Oy Ps Qd Qz Sj Tz Ug Uk Ur Yh)
fR(Aa aF aZ bF cP cU dI dL dN eC Gb Gn Hr Iv Jo kE kF kK Lv lW Mb Mh Mj Mm Mq mT mU NB nR nW Ou Pa Pc Pe Po Rg Rv) Dd(aA aU
Ax cE cG cL Ct cU Ez Fw Is Jl kG Ld Lv Lx Ma Mq mU Nb Nn Nq nR Nt oW Pf Pg Ph Qa Qd Qu Tt Ua Uc Uf Vu Vv) Ld(AA aU aY aZ cB
cL Dr dU eF Eq Gb Gn gZ hG Hr jB Jl lW Mb Me Nb Nd nR oV Qd Qg Qh Qv Ua Uc Ug Vv Vz Zx) Lx(AI Ao aQ aS aU aV AX aZ bC Bo cE
cL cN Cv Db Di dJ Dr Gb Gc Gn Hb hG Hl Kd Pj Sf Vz Wb Wd We Ti) oV(bO cG Ct cU Cv Ez fB Fw Hb Hl Iv kK Lp Lu mP Nb nL nO nR
oN Pc Pf Pg Qg Qu Qv Qx Ra Ri Rj Ub Uf) Ma(Ad Al Ap aQ aS aU aV AX aZ Ch cN Cv Db Dg Dl Gc Gn Hb hG Kd Kg Kj KS Kz Pj Wb Wd
Zw Ti) Ua(Aa Ax Cs Dp eC Em Hr Jv kF kG kN Kx lY Lz Mb mF Mh Ml Nb Ni Nn Nx Pa Pe Qv Ue Ug Uk Ur Wm Yf) Ez(Aa Ao aQ aU aV
aY aZ bC Bo cE cN Cv Db Dl Dr dU eM Gb Gc Gn Hb Hr Kd Kg KS mU Nd Pj) Nb(aE aO aQ Ax bX cL CS Cv dD Dr gL hC hG Hl Kd Kx
Lp Ru Sf Uf Ug Vs Vu Vw Yh Zw Tm Tl) Vv(Aa aQ aS aU Ax bF bX Cs Cv Cx Di dR eC eF Eq Gb Gc Gd Gn Hb Kf Lp Lt mU Nn Pj Va Wb
Yf) Qv(aE Ax cG cL Cq Ct Dc Dk eC Gl Jl Kx Mp Mv Nd Ng Nn nR OP pF Tz Uf Vu Vw Wd Yd Zw) Aa(aH aO aQ aU Ax bB cG Ct dH dJ
dM dR Fw hC Kx Ow Qu Ri St Tt Tz Uc Uf Vi Vj Vs Vu) Mq(aF aL aO aS aX bC bF bR cS cU Cv dl dN eF Eq fB Gb gL Gn hC hG iZ Sf Vi
Wd We Ti) Hl(aM aO Ct gC gL hB Jn Js kG kN Mj nU NW ON oP Ow Po Pz Qa Ql Qt Qz Rm Uc Vq) eC(aA aL aW bM cV cX dJ dM Je Kd
kF kK Mf Nq Pj Qg Qh Qn Qu Ra Tv Tz Uf Ug Uk Vs Vu) Sf(cE Co Cq Dk dR Ef Fw Jk Js Ng Nn Nq nR Nv Om ON oP Ou Ow Pf Ph Ri Rm
Uf Vi) aQ(aA Bb Cv eF Jv Lu Lv Lz Mb Mh Mj Ml Mm Nn Ou Pe Pf Pj Qa Uf Wd Yh Wm Yf) aU(aA Ax Cs Cv hC Is It Jl Jr Kx Lu Lz Mh Mj
Ml Pe Pf Qa Uc Uf Vw Yl Wm Yf) aA(aE aK a V hC bF bR cL cS cW cY dD Dk eF Kx IN nR oP Ou Qt Yh Zw) IL(eD iC jD kP IN lW lY mF
mM mT mU mY nA nC nH nL nT nU rB rC rZ) Ax(aF aO aV bF cE cG cL dD hG Is Jl Lv nA nR Ou Qa Qd Tt Uc Vs) Cv(cS Ct dD Dk eF Is Jl
kF kN kQ Lv Mz Nv oW Pg Qa Qd Tt Uc Vu) Gb(Ct Dg Dk hB Is Js Kf Kl mU Nq Nw On oP Ow Pd Pf Pg Ql Uc Vs) Yf(aO aZ bF cE cY Dk
Jr Lv Mj Nv Om oP Ou Oy Po Rm Uc Vs Yd) Wd(aY cL cP dL dN Gn Iv Js kE Kj Mj mU nB nU Ow Pd Po Qa Rm) Jl(Al aX bR CS Dc Dp Hb
Jv Ks Qg Rb Ub Uf Ug Up Ur Us) aO(bC cL dL Eq Gn Hp Hr IW Lz Mb Mh nB nI nO oW Pb Vz Yl) hG(cG dL hC Hr Is kF Lv Lz Mb Mh mP
NO nR oW Pe Qa Ur) Qt(Al dU eM Fd Gn Hr Kd Mj mU Nd Pa Qg Sj Vb Wb Yd Yk) bF(Cs Dp Hr Jd Je Kx Lz Mb Mh nO Pe Qa Qz Ug Uk
Ur Wm) Uf(gZ Hr Hw Is Jj Jo Jv Kj lY mE mZ Ue Ug Uk Vo) Ur(Bg cL Ct Dk EF Iz Jk Mv Mw Nn Nq oP Ou Vs) nR(Ap Cs eD Hb Ko Kr Ks
Kx IN Mh Nm Rb Ug Uk Wm) Tt(Al aY Bb cN dC dL dN Hb Kf Ks Mm Nm Pj Rc) Zw(aV cE cN dR Gn Hq Is kR mU On Qg Qy Ri Rm)
cL(fB Lp Lu Lz Mh Ml Nr Pf Ub Uk Vw Yl Wm Th) Ct(fB Gh Hr Jj kG Lp Og oT Rv Ug Vb Vz Ye) Nn(aF cV Fd Kd Pj Qg Ra Sj Tz Uc Ug
Uk Yk) Vi(Bb dL Em Gd Jp Kn kO Mm Pb Po Sh Up Vb) eF(aZ Ed fB hC Kd Lt nO oT Qa Rb Tz Ub Ug) Eq(Bb dL Iv Jn Js kG nW Ny oN
Ow Pc Qa) Gn(Dp hB Is Js Ow Pe Po Qa Ql Rm Uc Wm) Mh(aF aV cE cG cV dD De Dk Ou Sj Vu Yd) Pf(aF Al aV aZ cN Fi Gc Gd Lp Ru
Wb Zq) Hr(cS dD Fa hB Ou Ow Qu Qy Tz Vs Vu) Is(Al aX cS Di Dr Gc Hb Rm Sh Ux Wb) cG(Bb Dl Jo Jr Kr Lz Mb nl Nm Pj Uk) Wm(aV
dD dU eM Fd Ou Sj Yd Yh Yk) Vu(kF kG Lp lY Lz mE nl Pc Qx Rm) IN(jH IK mH mM mT mU nN nU oP rX) Nq(Bb Fb Kd Kf Ks nU Pj Wb
Zq) Sh(cE Ef Jh Mv Ng Nv On Ou Pg) Zx(dL Ef hC Iv Js nW oN Ow Qa) Ug(Aj bC cS Kx Ng ON oP Qu) fA(Fw Hf Kn Me ml Ql Rb Ri Rj)
Uc(Al aX Di Hb Kx Lp Va Yh) Yk(cS hB Iv kG oN Qa Qx Ra) Ps(aS aV aZ cE Gd Ib Mn Pi) kF(bR dR hC iH Lt Ou pF Qg) Qa(Al aS aX cS Di
Dr Qg) Lv(aX bC CS Hb Qu) Lz(aF aV cE cV dD Ou) Rm(Hp Lp Rt Va Vw Yl) On(Rx Si Vh Wb Yl Ti) Pe(aF aL aV cE dD Ou) fB(aM aR Ik
Mg NI) Ow(Dr Gc jB Nd We) Uk(Ef mU Ng Qu Yh) Vs(dN Dp Em Pc Tm) Pg(Al cS Fd Fi oT) nO(Bg cE dD dR Qg) nU(eD hR jK jT qU)
hC(bC Cx Di nl Ye) kG(Dk Fd Kd Or Ou) Tz(Cx Di Mb Yh) Jv(Bg Jk Nd Ng) aF(Cs Cx Li Nt) cS(dU Mz Qg Qh) oW(Kd Lp mE Pc) Dk(Hb
Ru Va) Nm(Kl oP Qu) Mj(Wb Wc Wf) Yd(Ou Qx Ra) Sj(cP Iv Mb) We(cP dL Js) Ye(Ef nW oN) Kx(nA Qg Qh) Ri(dD gZ Yh) dU(Ql Qx Ra)
oT(Iv Mb mP) Cs(cE nA) Nt(Ap Pj) Rb(hB oN) Zq(Jn Js) Kl(Gd Vb) Lh(Rt Va) Rv(Pd Po) Ru(Im oP) Nv(Rt Va) bC(Qg Ub) CxcX DiOa DrJs
EfWb FdMg GhoN MukK NdKk NgUe NiaL YhUo SiJn QdaS QzLp QxeM QumZ KynI YldR OuPc VjPa VwmU dDlW lKoP} nI{ Yj(aF AO Aw aZ Ba bF Bg bQ cF Ch Co Cp Cq cS CT CU dA DD De Di Dk Ef Eq Ex Ez Fr Fw Fy Gp Hc Hu Is Iz Jd Jh Jk Jl Jq Jr Js kG Kj kN Kq Ky Lh Lx Ma Mg Mj Mt Mu Mv My Mz nC Nd Nk Nn Nq Nr Nv Nw Nx Oh Ok Om ON Ou Pf Pg Ph Pi Po Qn Qu Ri Rz Tn Tz Ua Uo Uv Uw Vi Vs Vu Vv Vz Wd We Wh Yd Yg Yi Zw Xa) Ut(Aa Ad Al Ao Ap aV bA Bb bX cF Ch Co cT Cv Dd Dg dH DI Dl Dp Fb fP fR gC Hb Hc Hr Ij Is It Iz jB Jd Je Jg Jh Jm Jo Jt Ju Jv kC Kd KF kG KK Kl KN Ko Ks Ky Lh Li lW Ma Mb Mk Mn Mq My Nd Nh Nk Nm Nn Nv Nx Ny Of Oh Ok Om On Op Ow Oy Pc Pj Pk Pz Qx Qz Rc Ss Tr Tz Ug Uk Um Uu Uw We Yi) Kq(Aa Ad aF Al Ap Ar aU aV Aw Ax bA Bb Bc bV cF cO cR cT Cv dA Dd Dg DI Dl eM Et Fa Fb Fp Gb Gc Gn Hb Hp Hw Ii It Iz Jg Jj Jm Jo Jr Jt kF kG Kl kN Ko Ks Lh Li Lp lW lY Mm Mn mT Nd Ng Nk Nm Nn Nv Ny Of Oi Ok On Oz Pb Pj Qe Rb Rc Rm Rx Ss Tr Tz Ug Um Un Uo Vo Vq Vt Vv Vw Vz Wb) Yd(aF Al Aw aX aZ bA bO bQ bV cF cN cS cU Cv cW Dc Dd Di dM Ex Fw Gb Gd gL Gn Gp Hb HC Hl Hr Hu Iv Jh Jj Jm Jo Ju kC kE kF kG kN Lp Lu Lx Mh mU Mv NB ND nH Nk nL Nm Nn Nw oN Oz Pb Pc Pi Po Ps Qa Qu Qx Rt Sf Tr Tv Tz Ub Um Uo Uy Vs Vv Vz Wd We Wh Yh Xa) Uw(Ad aF aG Al Ap aV bF cF Co Cv cW dA dC Dg Dl eM Et Fb Fr Gb Gd GL Gn Gp Hb hC Hl Hp Hw Ib Ii In It Iz Jg Jq Jr Jt Jv Kf kN Ks Lh Li Lp Mm Mn MZ nC nH nJ nL Nm Nn Ny Of Oh Om Ow Oz Pb Pc Pg Pj Pz Rc Rf Tn Tr Ug Um Un Ux Va Vb Vo Vq Vt Wb Yg Yi) Tn(Aa Ad Al Ao Ap aR aU aV Bb Bc bF bQ bR bX Cv Dd Dg dH Di Dl dR fB fP fR Fy gC Hu It Iz Jg Jk Jl Jt Ju kC Kd kF Kj Kl Kn Ko Ks Ky Lp Ly MF Mj MP MU Mx Nb Nd Nk NN nT nU Nx Oh Ok Pc Ph Pj Pk Rc Ss Tz Ua Ug Um Uo Uu Vu Vw Wb We Yg Yi) Cu(Aa Ad aF Al Ao Ap Ax Bb Bc cF cO Cv Cw Dd Dg dI Dl Fy Gc Gd Hb Hl Hp Ii It Iz Jg Jj Jm Jo Jr Jt Ju Kd kF Kg Kj Kl Ko Ks Lh Lp Lu lW Ma Mb Mm Nb Nd Nk Nm Nn Nv Nx Ny Of Oh Ok On Pj Pz Rc Rt Rx Ss Tr Uc Uf Ug Um Uo Uu Va Vo Vq Wb Yg Yi) Aw(Aa Ad Al Ao Ap Bb cU Cv Cw DD dU fP Fw Gb gC Gd Gn hC Hl Hp Hr Is Jj Jl Jo Jr Jt Ju Jv Kd kF kG kN Ko Ky Lp Lu Lv Lz Ma Mb mF Mj Mk Mm Mn MZ Nd Ni Nm nT Of Oh Oy Pi Pj pK Qz Sf Sh Tz Ug Um Uo Ux Va Vb Vi Vp Vu Yh) Gn(Aa aF aO bO cU Cx Dd De Dk Ez Fd fP Fr Fy Hc Hu Hv Is Jd Jl Jm Jr Js Jy kN Kr Ky Lv Lx Ma Mj Mu Mv Mz nR Nv nY Om Ou Pb Pg Po Ps Qd Qh Qn Qt Qu Qw Tr Tv Tz Ua Uc Uo Uv Vu Vv Wf Yg Yh Yi Zw Xa) Um(AO bF cG Ch Co cS dF Di Dk Ef Eq Ez Fr Fw Fy Gl Hc Hq Hu Jd Jh Jk Jl kF Ky Lv Lx Ma Mj Mk Mu Mv Mw My MZ Nb Nd Nj Nn Nq nR Nv Of Om On oP Ou Pg Pi Pk Po Qa Qu Rz Tz Ua Vs Vu Vv Yg Yh Zw) Cv(aL bA bF Bg bQ cG Ch cS cU dD dF Di Dk Ef eM Eq Ez Fr Fw Fy Hc Is Jk Jl Jq Jr kF kN Ky Lu Lv Lx Ma Mj MU Mv MZ Nb Nd Nn nR Nv Ny Ou Pf Pg Pi Pk Po Qd Qu Rz Uc Vi Vu Vv Yg Yh Xa tF) Yg(aF Al aO Ap aQ aU aV aY aZ bB bO Co cU cY dA Dg Dl dR eM Gd Gp hC Hl Hp Hv In Jg Jm Jt Kf kG Kl kN Lh Lp Lx Mb Mh mZ Nd Ng oE oF Og Om Oy Pg Pz Rj Rx Rz Sh Ss Tt Tv Ug Ux Vw Wd Ye) Fw(Aa aF Ap aV Ax aY bA Bb Bc cF cS dA Dd Di Dl Gb Hb Hp Hr It Jj Jl Jm Jo Jr Jt Ju Jv Kd kF kG kN Ky Lh Li Lp Lu Lv Mm Mn Mu mZ Nd NK Nm Nn Of Oi oT Ou Pj Ru Sf Ug Uy Yh) Yh(aF aO aV aZ bQ cB cF cS cU cV cY dA Di Dp dR eM Gb Gp hC Hl Hr In Is Jl Jn Lv Lx Ma Mj Mz Nb Nd Nf Nm oF oN oP Ou Pf Pg Qa Qd Qh Qv Qw Qx Rg Rt Tv Tz Ub Uy Va Vb Vi Wc) Lp(aO bF cE cF Cp De dF Dk eF eM Ez fP Fr Fy Gl Hc Hq Is Jh Jk Jl Jn Jp Jq Jr Lh Lv Lx Ma Mj Mu Mv My Mz Nq Nv oE Om ON Ou Pf Qa Qd Qw Tr Tv Ua Uc Uv Vi Vu Vv Yi) Vv(Aa Ad Ap aQ aV BB Bc bX cF cS Cx dA Dg Di Dk Dl dR Gb gC Gd Hb Hl Jl

Figure 32 Continued

Figure 32 Continued

Uo Vt Yj) aZ(Aa aM bO cF Et Hc Ib Ii Iv Jh Jp Jt Ju Ke Lu Mv nC nH Ni NJ Nn nU Nv Ny Oh Ok On Ow Pj Rx Si Va) Gd(Al bI bO cA cF cU
Cv De dM eQ Fn Gp Gz Ha Hc Hl Ii Jh Jm Kx mW Mz NB Nq nR Ns oD Oi Ry Yi Yj) aJ(Ap Bc Dg Gz Hu Ib Jg Jt KI Ko Li Ma Mm Mv Mz
Ng Nm Nn Ny Oh Oi Ok Ow Rx Ry Rz Ua Uu Ux Yi Zq) cU(Aa Ap cB Dg dJ Hp Hu Ib Jt Jv Kq Ma Mm Mv Mz nH nJ Nm Nn Ny Oh Ok Om
Ow Pj pK Sh Si Ua Yi Xa) nU(aO Ap Cv cX dH hC Hl Jg Jt Kg Kj Kq Og Pf Qa Qb Qd Qv Qx Rg Ss Tt Ug Uk Ul Uu Ux Vo Vw We Xa)
dM(Aw Bc Co Dg dR Ef Hu Ib Jg Jh Jt Kl Kq Ma Mu Mv Mw Nm Nn Nq Nv Ny Oi On Ou Ow Rx Ua Ut Ux) nH(aF Aj aO aU bB Dd dH gL
Gp hC In Jn Jp Kg Lx nJ Oi Or Pg Qb Qe Qg Rg Rv Ss Uh Uk Vt Vw) Ou(eP gL Ii Ji Ju Jv Kg kN Ko Kq kS Mm Mz nD Nn Ok Om Op Pj Rt
Sf Sh Si Tr Uh Uu Va Yi) Mz(aM aP bO cH cN Ex Fw hC Jl Jn Js Lh Lv Lx Mt Nb nN Nv Nw oE oP Or Ow Pg Qa Sh) Rx(Al aP bO cA cK dG
dL dU eQ GZ Kg kK kN KO lW mE mM Ns pK Qt Sh Yj) Or(cF Ib Ju Kq Lh Ma Mm Nn Nw Oh Ok Om Op Ow Pj Qb Qe Rm Si Uh Va Yi
Yl) Gz(aP aU bA Hc Hp Ib Jj Jt Kj Ko Kq Ma Mm Nb Om Pc Pj Si Tr Uo Uy Vb) oP(Ax Bc bH cM Cw Di GL Jp Kp Oi Op Pg Ql Qt Qu Qz Tn
To Ut Vu Wd) pK(aQ aU aY bA bH bL cY dH dJ dR fB gL hC II lW Ng oE Pa Pg Sf) Kg(bO Co De dX Ez Fi Ho Kq Mi mP MT Mu Mv nK
NN Nq Nv) nJ(Aj dH Et Hq Jg Jn Kf Lx Pf Pg Qb Qd Qe Qx Rg Uh Uk Vt We) mH(Al Cv Dd eM Jm Ju kN Nu Rj Sf Sh Tt Uk Uo Uw Va We
Wh) aP(Ap Bc Ib Jg Jt Ma Mm Nm Nn Ny Oh Oi Ow Ua Uy Yi) kN(aQ Aw Cp Dg eM Hl Iv Jg Kn Nb Oi Om Pg Rh Ss Xa) fB(Aw Cs Fr Hu
Jh Ke Kq Lh Li Mu My Nr Ow Rz Ua) nR(Bg Dg Jg Jt Kf Kj Kl Ko Mm Nm Oi Rt Ux Vw Xa) kO(aU Aw eM Gp Jt Oi Qv Ri Ug Um Ur Uu
Va Vh Vw) Nn(dF eP Ex Fw hB hC iA iZ Lh mS Ne nK nY Ow) cF(aM In Jj Jq Ju Jv Ko Mm Nb Nw On Pg Sf Sh) Qa(Aa Ih Ii Kq Nw Oh Pb
Pj Qb Qe Rf Rm Si) oD(bA cS cT Dk Et Ez Jh Ji Mg Ng Op Pb Rz) Yi(aM dJ dL Ex Fw hC Iv JI kK Lv Nb Po) mE(Co Dr gL Gp Hl Jd Jh Ko
Mv Nv Rf Ut) Si(Aj dX Jn Ke Lx Nw Ow Qb Qd Qe Qx) Oi(aA dG dH dL hC iZ kF kK kR nY Sh) mS(aF Gc Iz Jg Mm Nm Pj Pz Ug Uu Ux)
nC(Aj Qb Qd Qg Qu Qx Rg Rv Tt Vt Wb) Ko(Bo cB dJ Gp Hl Jj On Pg Rh Rj) dX(cW dB Dg dN Dp Hf Mx Nf Ue Zx) Aa(aA Aj cC Jj Qb Qd
Qx Uh Vt) Nm(aM dH dL iZ kK mM Mt nN Uo) Ow(aA Ex hC Jj Li Lu nY Pj Rf) eM(aF Ih Jn kC kF nD On Ps Ut) eP(bZ cC Fw hB iA Lp Mt
Nv Uw) eQ(Ax Cw Dc Kl Li oE Op Pa Rz) dU(bU cQ cY fP gL Jv Sh Tj) lW(Aj Dp dR Gp Hl Kj Lp Mk) hC(Aw Ib Ii In Kx Ny Oh Ry) iZ(Aw
Ch Hp Ib Mm Ny Oh Xa) Ma(aO BO dF dH Lx Pg) Nb(Jm Ju Md Ne Ry Sf Uo) Hc(Aj Jt Kj Oy Sh Uu Va) nL(Qb Qd Qx Rg Rv Vj Vt) De(Dg
Jj Jl Jn Kj Vi) Jv(iJ Lz Mj Nq Qx Ry) Rf(Ex Jn Js Lx Mq Oa) Pf(kK mY mZ nB nT oT) Pg(gL hG kF Mm nD oQ) oE(Ne Oz Pb Pc pF Ry)
Md(Jj Jt Kj Rt Va) Oh(aA Ex Jj Lx nY) On(cB Ii nA Ok Om) bA(Mv Mw oT oW pH) bO(cN iJ Iv Ps Uy) dF(Dg Jh Mv Ok Ua) ml·(aQ bQ Qb
Qx Vj) kF(Dg Jt Kj Lx Vj) kK(Of Qu Rt Tr Tv) Lh(Ii Mm Om Pj) Nv(Rt Ry Tr Va) Uo(iJ Ua Uy Vi) aO(Dg JI Kl Ps) dG(Ap Dg Kl Uy) nN(aF
Ap Qu Vj) nA(Hq Jg Kp Xa) oT(Ba Ct Ju Sf) Yj(Iv Jg Jt) Sh(iJ oW Ry) Uw(kP ml mM) cT(Jh pH Ua) dJ(iJ Jl Vi) gL(Aw ml Xa) nT(Aj bZ Rg)
mY(Jn Lx Nw) nD(aQ bQ Rh) oQ(Aw Cp Fr) Lu(Lx Qd) Mm(cC Qx) Ib(aA nY) li(Jn Qb) Rt(mW tF) Va(Lv Vv) Pc(Qd Rh) cN(cS Ry) gC(Pk
Sf) gZ(bQ Dr) nO(Rj We) mM(Jg Jj) jB(cY Hr) pH(Ba Mv) ApdL BnQv GhnW MjJu MqLi TrdH TnmZ KjmW NynY UtbH UyaM VimP OzpI PjcC aQlX} Gb{Jr(AD aJ aM An Ao Ap As AW aX Ba Bb Bc bE Bg BN Bo bW cF cL Co Cp Cq cS Cu Cv CW cZ Dc Dd De Dg Dk Dr Du Ef Em Eq Ez Fw Gn Gp Hb Hc Hl Hq Hr Hu Hv Hw Hx Id Ii Ij Im In Ir Iv Iz Jd Jg Jh Jn Jo Jq Js Jt Kc Kd Ke kG Kk Kl Kn Ko Kp Kq Kr Ld Li Lw Mb Md Me Mg Mi Mj Ml MP Mr mT MU Mv Mw MY Mz Na Nb Nd Nf Ng nH nK nL Nm NN Nq NR Nt nU Nw Ny Om oP oV OW Oy Pb Pd Pe Pf Pg Ph Pi Pk Ps Pz Qd Qt Qy Ra Rb Rj Rt Ru Rx Ry Rz Sr Tv Ua Ub Ud Uf Ul Um Un Uo Up Us Uy Uz Vh Vi Vj Vp Vt Vu Vz Wc Wd Wg Yj Yl Ye Tl Xa) oP(aK Ao Ap aU aV AW aX Ba bB bC bR bU bW bZ cC cF cI cL cM Co Cp cR cS Ct cY dA De Di dJ DK Eq Ez Fd Fi Fw Fy Gh GL Ho Hu Hv Hw iJ Im iO Is It Iv Iz Jd Jf Ji Jk Jn Jo Jp Js Jt Kc Kd Ke Kf Ko kP Ks Ld Lh Li Lx Ma Mg Mh Mi Mm MP Mq MT MU Mv Mw My Na Nb Ng nH nK nL NN Nq Nt nU Nv Nw Om On oV OW Pd Pe Pf Ph Pi Pj Po Ps Pz Qd Ql Qu Qy Rz Si Tn Ua Ue Uf Uk Ut Uv Vj Vq Vw Wd Wh Yh Ye Xa Wm Ti) mU(aI Ao aQ Aw Ba bB Bg bR bU bZ cA cE cF cG Ch cI cM Cp cS Ct Cu cY De Dg Dl Dk Ef Eq Et Ez Gc Gl Gn Hu Ij iO Is It Iz Jd Jh Jl Jn Jp Js Jt Jy Kf Kg Kl kN Ko Kp Ld Lh Lv Lx Ma Mg Mj Mk MT Mu Mv Mw My Mz Nd Ng Nn Nq Nr Nt Nw Nx Of Oh Ok On Op Ou oV Ow Ps Pz Ql Qy Ri Rz Ua Uc Uf Uv Uw Vi Vu Vv Vw Wd Wh Yd Yh Yi Zx) Tz(aF aJ aM Ao Ap Aw aX Ba bC bN bW cB cF cG cL CO cS Ct Cu cX De Dg Ef Eq Ez Fr gL Hc Ho Hq Hu Im Is Iz Jd Jg Jh Jk Jp Kc Ld Li Lx Ma Mg Mi Mk Mp MT Mu Mv Mw My Nd Ng Nj Nn Nq Nt Nu Ou Ow Pd Pf Pg Pz Qd Ql Qt Qw Qy Rz Ss Tn Ua Uf Ut Ux Vj Vq Vs Vu Vv Vw Wd Wh Yh Yi Wm) Cu(Ad aJ An Ao As aZ Bc cF Co Cp Cv CW Dc Dd Dr Du Em Gn Gp Hc Hl Hq Hr Hu Hv Hw Id Ii Ij Im Ir Jh Jn Jo Jq Jt Kd Kk Kn Ko Kp Kq Kr Lw Mv Mz Na Nd Nf Ng Nm Nq Nt Ny oV Pb Pe PH Pi Pk Ql Qw Qy Rt Ru Ua Ud Ul Um Uo Up Us Uy Uz Vb Vh Vu Wg Yi Yj Yk Yl Zx Tl Tj) Ua(aA aJ aM aP Ar Ax aZ bA bH bN bO cH Cs cT cU dF dI Dk dM Ed Fw Fy Gh Gp Hc Im Is Ji Jj Jl Jp Js kE kG Kj kN kO Lx Lz mE Mx Nb Nd nH nL No Nu Nw Oa oE oF Oh On Ou Ow Oy Pe Pf Pg Po Ps Qd Qe Qx Qz Sh Tn Ub Uh Uk Un Uo Vv Yi Yj Yl Wm) Is(aE aJ Ao aX aZ cF Co Cv cZ Dc Dd De Ef Gz Hc Hl Hq Hu Im Ir Jd Je Jh Jj Jm Jo Ju kG Mf Ml Mu Mv My Nd Ng nH nL Nq Ns Nt Nu oV Pb Pd Pf Pg pK Qb Qd Qw Qy Rm Rz Sf Ub Ud Ul Um Uo Up Us Uy Uz Vh Vj Vp Vv Vw Vz Wd Wg Yj Yl Zw Tl) nH(AO Aw Ba bB Bg bZ cE cG cI Co Cp Cq Ct Dl Dk Ef Fw Fy Gl Hc It Iz Jd Jk Jl Jn Jp Jq Js Kl Lh Lv Ma ml Mj Nd Ng Nq Nw Nx Of Oh On Op oV Pf Pg Ps Pz Qh Rm Uc Ue Uf Uw Vi Vj Vs Wd Wh Yd Yh Yi Yj Yk Xa) Qd(Ao aS Aw BA Bg cF Co cR CT De Dg dI Dk dM Fr Fy Gn Hc Hf Hq Hu Ib Iz Jd Je Jg Jh Jp Kf Kl Lh Mv MY Nd Ng Nt Of On Ou Pa Pb Pc Pd Pg Ps Pz Ql Rz Tn Ub Uy Vj Vu Vv Vw Vz Wd Wh Yh Yi Yk Yl) Ps(Ao aP aX aZ bC bR cF cG Co De Fr gL Gp Hq Hu Jm Jp Kc kF kN Li ml Ml Mu Mv ND nJ nN Nq Ns NT nU Nw Po Qy Rx Ud Uf Ul Um Uo Up Us Uy Uz Vh Vj Vp Vs Vu Vv Vw Vz Wc Wd Wg Wh Yj Yl Tl Xa) On(Ad An As aZ Cq Cv Cw Dc Dr Du eQ Gn Hc Hl Hq Hr Hu Hw Id Ii Ij In Jo Jq Kd Kn Kp Kq Kr Lw MM Na Nd Nf nU Om oV Pb Ph Pi Pk Ra Rb Rj Rt Ru Tv Ud Ul Um Uo Up Us Uz Vh Vi Wg Yi Yj Yl Tl) Nd(aJ Ao aP Aw Co De Ed Ef Et Ez Fa Fd Fp Gz Hc Hq Hu Im Iv Jd Jh Jl Jp Js kG Kz Lx Mi Mq mT Mv Mw Mx My nD Nq Nt nU Nw Oa oV Ow Pe Pf Pg pH Po Ql Qy Tn Uf Ut Vu Vv Wb Yi Zq Tl Xa) Yi(aA aJ AO aP Aw aZ cF Co De Dk dM Ef Fw gL Gz Hc Hu Hv Im Jd Jh Kc Ke kG Kq Ld mP Mq mS mT Mu Mv Mw My nL Nq Nv Nw Om Ou oV Pe Pf Pg pH pK Ql Qm Ut Uy Yj) Nw(aD aJ Ao aZ Ba bE bN bU cF Ct cZ Dk Dl Ef Fw gL Hc Hq Hu Im Iz Jd Jg Jh Jp Kc Ml mT Mu Mv MY Ng Ns Nt Oy Oz Pb Pc Pf Qy Rz Ub Vu Vv Vw Vz Yj Yl Ye) Pg(aJ aX Ba bU cF Co Cv cZ Ef eQ gL Hc Hu Im Jd Jh Jj Jm Jn Jp kG Li Mi Mt Mu Mv Nb Ng nL Nn Nq Ns Nt oT oV Ow Pc Ql Qy Ub Ul Um Uy Vj Vu Vv Yj Zx Xa) Jl(Ao Ap aX aZ bC cF Co Cv Dc Dr Ef Ez Hc Hf Hl Hq Hu Im Jd Jh Kc Kg Li Mg Mp mT Mu Mv nB Nf Ng nL Nn Nq Ow Qy Rz Uf Uy Vj Vu Vv Wd Yj Yk) Vu(Ao aP Aw aZ bA cF cT Dk dM Ex Fw Hc Hl Hr Hu Hv Ib Im Jn Jp Jq Js Ki Kp Kq Lx Mj Nt Nv Oh Pe Pf Pz Ub Um Uo Ut Vi Vj Vv Yj Xa) Hq(aJ Ax bR cE Cs Dk dM Ed Fw gL Gz Hc Im Iv Jh Js kC kE kK kN kO Lx Lz mE mP Ms mT mW Nb Nq Oa oF Oh oN Ow Pe pF Qy) Hc(aA aJ aM aP aZ cG De dX Ed eQ Ez Fd Fy Hv jB Jp kG Ld Lx Mi MP Mq mT nC nL Nq Oa Oh Ou oV Ow Pe Po Tn Wb Xa) Vv(aJ Aw aZ cF Co dX Ed Hu Hv Im Jd Jh Kc Ke kI Kq Li Mq MT Mv Mw Nq Nv Om Ou Ow Pf Qa Ql Qy Tn Um Vj Wd) oV(Aw bA bQ bV bW cG cL Co Cp Cq dF dK Fw Fy Gn KF Kl Lh Mg Mv Ng Nv Om oN Op Pf Yd Yh Yk) aZ(Co Ct Dk Ef Fr Fw Hu Im Iz Jd Jh Mg Mu Mv Mw My Ng Nn Nt Pf Pz Ql Qy Wd Yh) Im(aN aS bA Bn cB cG cT De dI dM Fy Jp Ml My Ns Tn Ub Vs Vz Yj Yk Yl) pK(Ao bB bZ Dg Iu KF kG Lx Ma Mg Ng Nn Ow Pd Pe Po Ql Rz Yh) Hu(aJ cT cU dM Ed Fd Fy Jp Js kE kN Lx Mx Oa oF Oh Pe Tn) kN(aQ Aw cL Cp Ke Lh Mp Mu Mv Mw My Nq Nv Om Ow Wd Xa) oD(bZ cS cZ Ez iH Jh kG Kq Ma Mg Mt Mv Ng Nn Nq Ow Rz) Ed(Ao Aw Ba Co Ef Jg Mu Mv My Ng Pf Pz Tn Vs Wd) Yj(Hv Jn Jq Js Ke kG Kq mP nU Nv Qa Ut Vi Xa) Oh(Co Ef Hv Iz Ml Mu Mv MY Ng Nt Qy Rz Wd) Dk(Gp Hl kG mP mT Mv nC nK nL nN nU Ow Ub) Lx(cF De Ef eP kF Ml Mu Mv MY Ng Qy) Ou(kC kI kO mF mY nA nD nL oQ

Figure 32 Continued

Mw Oy Pd Pf) Ps(Hb Kr Uc Ud Ul Un Uo Up Us Uw Vp Vs) Sh(Bg Co Hq Hu Is Iz Mv Ng Nq Pg Ua) jI(Bc Ct Gz Id jG Ko IL Ni Nk Ul Us)
Hp(Cu dX Ed Im Jl mU Mv Pg Ua Uo) Uw(dX Id Is Kp Kr Lx Nw Pg Pk Qn) Gz(iB Jr lL Pz Ua Ub Ut Yh Th) Ho(Cv dX Hr Jo Kp Nm Ug Ul
Uo) Fi(dB Gd iJ Jo kE Ug Ul Uo) lL(aA Ky lM Mu nA nN Nq rZ) Dr(Ed Ez Fy Oa Ow Ql Ut) Eq(aZ dl Gd kE Mh Qb Tz) Fd(Cv Is Jl Kp Pg Ul
Uo) Yh(aA aZ Ed fB Gd Ju Ne) Wd(dX kE Kp Mv Oy Pk Uo) We(dX Mv My Nv Pg Uo) Gh(Hq Mv Nq Ua Vs) Me(aO aP bV cB cF) mE(Jd
Qu Qy Ua Ut) kN(Aw Cv Jd Ju Ou) wF(Li Ma Mm Pf) Gd(Ez Jd Ua) Tz(Aa cF Qv) lm(Qv Ue Uo) Hb(Gl Ji Oh) Rv(mP nH nL) hR(cF Lj rZ)
wD(Ma Mm Pf) Nt(aA Jj) Ua(Ux Ye) Is(Iq Rm) Wh(dX Uo) Ju(nR oT) Ky(cF jG) Ur(mF oD) Ut(lW Mm) fB(Qt Uf) nU(Cv jU) mU(Kk Ye)
rZ(jY lO) AwkE NsVu LvaA LxZw MukK MvUe NeVz HcnO SjVv ZqaP RaOh LdjB RjoT OgwK OukI UkkF VwdX aQpK nRlM nBjF}
gV{bA(aE aH aL aM Ao aW aZ bB bI bL bO cC cD cH cK Co Cp Cq CU cV dD De Dk dM dN Et Fr Fw Gl Hu Ih Ii Ij Ik Io Ip Iq Ir Iu Iv Jg Ji
Jk Jl Jq Jr Jt Lh Lv Lx Ly Lz Me Ml Mp Mq Ms Mt Mu Mv Mw Mx Mz Nb Ng Nm No Nq Nt Nu Nv Nw Ny Oh Ok Om Po Pz Qa Qc Qd)
dB(aH aK aL aM Ao Ap aQ aU Aw aX aZ Ba bB bO cC cG cH Cp Cq Cw Dc De dR Et Fw gP Hx Ih Ii Ij Im Io Iq Ir Is It Iu Iv Jh Ji Jk Jl Jp Jt
Lh Lv Lx Mi Mj Mp Ms Mt Mv Mz Nb Nc Ne Nf Nh Nj Nl No Nr Ny Ok On Oy Oz Pf Po Pz Qa Qc) Nj(Ad Ax Ba bI bO cF cK Cq cT CU Cw
dD dF Dk Et Fp FR Hx Ih Ii Ij Ik Iq Ir Iv Jg Jh Jk Jl Jm Jq Jt Li Lu Ma Me Mh Mj Ml Mq Mr Ms Mt Mw Mx Mz Nb Ni Nn Nq Nr Nu Nv Nw
Oh Ok Om On Pc Pe Po Pz) dD(Ad Af Al Ao Ap AR Aw aX aZ Ba bC Bn bO bX cM Cp Cq cT CU CW Dd De dI Fr gP Hx Ih Ij Io Iq Ir Is It Jh
Jk Jm Jn Jq Jt Lh Lv Lx Lz Mi Mp Mt Mw Mz Nb Nm Ny Oh Ok Om Po Qa Qb Qc Qd Qe) Mn(Aa aC aJ aP aR As Aw bC BN bO bX cE cK
CP Cq Cu cV De dG dX eP fR Hu Ih Ij Ik Im Ir Iv Jl Jn Jr Lj Lu Lx Mb Me Mh Mm Mq Mt Mu Mx Nb Nf Nt Nu Oh On Pe Pf Po Qa Qb Qd)
cU(aA Ad aF Ao Aw bF Bn BO bX bZ cD cE cL cO CP cT Dc Dd De dH Di Dk Et Fp Hx Ih Im Iq Ir It Iv Jg Jh Ji Jk Jl Jp Jt Lj Lv Lx Mb Ms
Mz Nr Nt Ok Po Pz Qa Qb Qc Qd Qe) Im(aK aM aN Ao aU aX BC bQ bR bX cB cC cF cG cJ cK cN Cp cT Cu cV cW cY dA DC De dI dK Ij
Ir Iv Jn Jt Lw Lx Me Mi Mp Ms Mw Ne Nl Nt Nw Oi Oy Qa Qe) Ok(Aa aC Ad aF aJ aP As Aw Bb Bc bH bP cI cK cM CP Cs dX Hx Ih Ik Ir Is
Iv Jl Jn Jr Lj Lu Lx Mb Mf Mh Mm Mt Mx Nb Ne Nf Nh Nk Nl Nr Nt Nu Of Pf Po) Ms(aJ aP Ax bO Cp Cq Cs cT Cu dG dJ dM Fp Hu Hx Ih Ij
Ik Il Ir It Iv Jh Jk Jl Li Lj Lx Me Mt Mv Mx Nb Nc Ne Nh Nk Nl Nr Nt On Pf Po Qa) It(aL aN Ao aU aZ Ba bC bO bQ bV cG Cp cT cV Cw Dc
dH dI dK Et Hr Io Is Iv Jg Jh Lx Ma Mp Mt Mw Mz Nc Ne Nk Nl Nr Nx On Pf Po Qa Qb) Ik(aL Ao aU aX aZ Ba bO cD Cp cT Cu Cw Dc Fr
Hx Ih Io Iq Ir Is Jg Jk Jp Jt Lh Lv Lx Mi Mp Mt Mz Nb Nc Nk Nl Nw Nx Oh Om Pa Qb) Qb(Al aO aQ aR Aw Ax Ba bB bO bU bW bZ cG CT
cW Dd Dg Dl Et Hr Hv Ip Jg Jh Lx Lz Mg Mh Ml Mq Mt Ni Nn Oh Oy Pd Pz) aL(aJ Ao aP AR AW Ax Ba Cp Cs cW De Di Dk Fp Fr Hu Hx
Ih Ir Jh Lv Lx Lz Mb Mk Mq Mr Mx Nr Nt Nu Pf Po Pz Qc) cT(aM Ao aP aR aS Aw aX aZ bI bO cC cD Cp cV Dc De Dk Fr Gl Hx Ih Ir Iu Jh
Jk Mq Mt Nb Nq Nu Om On Pf Po Qd Qe) Cu(aC aG AN AR As bF bG Bn Bo bW bX cE cH cL cP Dc Dk Fp Hr Hv Hw In Jm Lv Mb Me Mr
Mx Oh Om Oz Pf Po) Ba(aC aF Aj An bC bG bO Cp Cq Cs Dc De Dg Dk Fp Hx Ih Ir Li Lj Lv Lz Mb Mc Mk Ml Mr Mx Nh Nk Nl Oh Qe)
Ir(aR aZ BN bV Dc dH Dk Fp Iq Iu Iv Jg Jh Ji Lv Lz Mb Ml Mq Mw Mx Nk Nl Nm Nr Nt Om Pa Pc Pd Pz) Iv(AR Bn bO bX cH Cp Dc De Dk
Fr Hx Iq Jh Ji Jq Jt Lh Lj Lv Lx Ma Mj Mp Mt Mz Oh Om Pa Pb Pf) Pf(aC Aj aZ Bn bZ cE cV Dc Dd eP Iq Ji Jk Jn Jq Jr Lv Ma Mi Mj Mm Mz
Nk Nl Oe Oh Oy Pc Qc Qd) bO(aC aF Al AN Ax aZ bN bX cB CP Dc Dd dR Fp Ih Ji Jm Jq Lv Mb Me Mi Mk Mx Mz Nt Oh Oy) Pe(aM Ao
aR aV aX aZ bX cB cD CS cW De dI dJ Hr Io Ji Jp Lj Lw Mi Mp Mt Nx Oi Oy Qe) Lv(aE bB bU cF cG Ct De dI Dk Dl Ih Ij Jh Jl Jt Ly Mr Mt
Mv Mx Ng Nq Nt Pd Po Pz) Li(aC aE aV Bc Bo bS bW bX cB cO Ct cX dC dH dX Hq Hr Hw Ii Il Jh Lx Mj Mv No Pz) Fp(aK aM aU aX aZ
bC bQ cC cG Cp CW cY De Jg Ji Jt Lw Mi Mp Mz Nm Nx) Mr(aM Ao aU Aw aX aZ bC CW cY De Jg Jh Ji Jp Jt Lw Mi Mp Mz Nb Nw Om)
Mt(aC aG Aj aO aR aW bE bG bI bN Dk eP Jq Mb Me Mm Nh Nx Oe Oh Oy Qc Qe) Mx(Ad aM Ap aR aU Aw aX aZ bC cH cS Cw cY Dc De
Ih Jt Lw Mi Mp Mz Nb) Qe(Af aK aO bC bJ Bn bQ bV Ct dF DK dX EM Ma Mu Nq Nt Nu Oz Pb) Ao(aC aF AR aW Ax bI bN bW Cs Dc dJ
Hx Ij Lj Mb Mh Mm Nh Nr Nt) Is(aG Ar aX bI bN bW cF cJ cQ Db Dk Gd Jh Jo Js Nf Nh Ni On Pa) aR(aZ cK Cp Cq Dc Dd dR Gl Hx Ij Ji Jl
Jn Lj Lx Mz Nr Nt Po Qa) Dc(aM aP bB bQ cC cH CS cW De dF gP Ih Jh Ni Nn Nt Pz) Mb(aZ cG Cp dC De Jg Jh Jk Jt Mi Mz Nb Nt Nv Nw
Om On Pz) Lj(Af aM aU Aw aX aZ cC cG cS cW dC De Ih Jt Mi Nb Pz) Po(aU aX aZ bS bX cB cY De dH Em Hq Hr Hw Ji Jj Mi) Jh(aC Aj
Ar Ax bN cK dI Hx Jq Mi Mk Mm Mz Oe Oh Oy) Aw(aC aF Al An bE bG bX Cp Cs Dd dJ Ih Iq Mf Nt) Hx(aM aU bC bQ cG cV De Hr Hw Ji
Mi Om Oy Pz) On(aF aN bS cA cB eP Hq Hw Il Mm Ns Nv Og Om) aC(aM Ap aX CW De eF Fr Fw gL Jt Mi Mp Mz) Nt(An Ar Bo De dI Et
Hr Iq Jj Jo Mz Na Oe) Me(Cw De Jg Ji Jp Jt Lx Mg Mz Nx Oh Om Pz) Cs(aU aX aZ bC cG Cp Cq cW De Dk dR Gl) Nr(bI bX cV Dc dH Hq
Hr Hw Iq Ji Mz Om) Mj(Ap aQ aU Bc bS bX cB cS CW cY Oy) Ih(aW bI bW cF De dH Jq Mm Nh Nx Om) Ij(aD aN cD cO cW Hr Hw Jj Jo
Mz Qd) Cp(aM Ar Ax aZ bB Em Et Hr Jj Oy) Qd(bW dF Em Ma Mg Mq Ni Oh Oy Pd) Ji(Aa aJ aP Cv De fR Lu Mq Ni Nu) dR(aJ aK aU Ax
bG cY dM Fr gL gP) Lx(aU bI bX cD cK Hr Jq Oh Oy) gP(aO aW Ax aY bE bP bW dG dN) Oh(aM aX cC cD dC Jt Mi Om) bB(Ar bX cD cH
Lz Mz Nw Ny) Dk(aU cP cS Nb Ne Nl Oy) Gl(aF Aj Ar bN bW dJ eP) Om(aP cP Mh Ne Nh Nu) Fr(aK aU aZ Jm Oy) Fw(cA cO Cq dX eP)
Pz(Aj Mh Mk Mz Nl) Qa(bI Mm Nh Nx Pa) Jn(Hr In Iq Ma Mp) aP(aU bI bW cV Jq) Ar(aZ Cq dC Jk) Ax(aU aX De Jq) Ct(cD Lz Mk Ml)
Jt(bW Jo Lu Mh) aF(bQ cG De dF) gL(bE bW cO dH) Et(bV De Nl) Nw(cP Ni Nu) cF(Ne Nh Nl) Mq(Dd Mp) Mz(aM Nn) Jl(cW Hr) Oy(Jg Jk)
AnNo CqJj CwLu DeJs LzcB MhMi NbaW NhdH QcbV JpbI JqaJ aMbG bWcF cGeP} mU{Uw(Aa AO Ap aU Ba BB Bg bW bZ Ch cM Cp cS
Cu Cw dF Di Dk Ef Eq Et Ez Fb fP Fr Fy gL Hb Hc Hp Hu Ib Is Iz Jd Jh Jl Jn Jp Jq Jr Ke KN Kq Lh Li Lj Lv Lx Ma Mg Mj Mm Mn Mu Mv
Mw My Mz nJ Nn Nq nR Nw Nx Ny Oh Ok Om oN OP Ou Ow Oz Pb Pg Pz Qc Ql Qu Qw Ry Rz Si Tr Ua Uf Uv Vb Vi Vp Vt Vv Wd Wh Yd
Zx) Uy(aK aO aU aV Bg bI bZ cE cM cS dA dI Dk eC Ef eM Eq Ez Fy Gp Hu iA Il In Iq Is Iz Jd Jh Jk Jl Jp Jq Jy Kg Kj kN Kq Kx Lh Lj Lv Lx
Ma Mg mH Mj Mn Mu MW Mz Ni Nn Nq NR nU Nv Nw Of Ok Op Pz Qu Qw Rb Rg Rz Tr Tz Uc Uf Ur Us Uv Vi Vp Vu Vv Wh Yd Yh Zx)
Hp(aO aQ Ba bQ bZ Co cS Cu cY Di Ef Eq Ez fP GL Hc hG Hu Is Jh Jl Jn Jp Jr kG kS Ma Mg mI Mu Mv My Nb Ng Nq Nx On Pf Pg Ps Pz
Qh Qt Qu Qw Qy Qz Rb Rm Rz St Tr Tz Ua Uc Uf Uv Vi Vj Vp Vs Vu Vv Vw Wd Wf Wh Wm) Hl(AO bF bZ cE cF cS Cu cW dI eF Eq Ez
Fy gL Gp iH In iO Is Iz Jf Jl Jy kE kG kN Lh Lv Lx Ma Mg Mj Mk mW Mz Ni Nq NR nU oE oF Ok ON Ou Pa Pf Pg Qt Qu Rv Rz Tr Uc Uf
Uv Vp Vu Vv Wf Yd Zx Wm) Ry(aO bF Bg bZ Ch Co cS Cu dD Di dR Ef Eq Ez Gn HC Hq Hu Is Jd Jh Jl Jp Jr kN Kq Lh Ma Mg Mj Mu Mv
My Mz Nn Nv Nx Ok Om On Ou Pf Pg Qu Rz Tn Vi Yd Xa) Vb(AO Ba bF Bg bZ Ch Co cS Ct dF Di Eq Ez gL iJ iO Is Iz Jh Jl Kl kN Ma Mj
Mu Mv My Mz Nx Ok ON Op Ou Pg Pz Qu Tr Tt Uc Uf Vi Vs Vv Vw Wh Yh) Tn(Aa aU Ax Bc cM Cx dH Dl Fa Fb Fp Fy Ii Jg Jj Jm Jo Jt kG
Kl Lh Li Ma Mb mE Mm Mn mT Nk Nm Nn Ns Nv Ny Of Oh Oi Qe Rb Rc Si Ss Uf Ug Uu Vo Zq) Yj(Aa aF aK aO aQ Ar aS bA Bo bQ bW
bZ cF Ch cM Co cQ CT Dd dI dR Fy Gp Hb Hc Id Jf kG Lh Lu Ma Mg mW Nm Nr Oi Pf Qt Qu Rv Rz Vp Vt Vu) Rz(aU Bb Bc Bg cM Cu Cw
Dd Dg Dl Fb Fy Gd Ib Iz Jg Jj Jt Kl Ks Lj Ma Mm Mn Mz Ng Nn Ny Of Oi Om Rc Rt Rx Tr Tt Tv Ug Uu Ux Vj Vw We Zq) Aa(aA aF aO aU
Aw aZ bA cU Cv dR Hc Hf hG Is Jn Jr Ly Me Mj Nq Nw Ou Pf Pg Ps Qa Qd Qu Rg Ri St Tz Uf Up Ut Vh Vv Vw Wh Ti) Vi(aA aQ aU Bb cI
cJ cM dC Dd dI Fb fP Gn Ib Iq iZ Jl Jm Kk Kn Kq Ks Lh Ma mE Mk Mm Mn Mz nJ Nn Oh Om Ow Pb Si Tr Wb Zq) Wh(aF Al aV BB bF bN
bZ cD cI cM cO cQ cW Dd Fb fP Gp hC Ib Kf kG Kn Lp Lu Mb Og Oi Ow Qv Rx Si Tr Ug Uk Uo Va Ye) Si(Ao Cu GL Hc Jh Jn Jp Jr Lh Lx
Mv Nq On Pg Ps Pz Qu Qw Rb Rm Rt Tr Tz Ua Uf Uv Vh Vj Vu Vv Wd Wf) jI(hR hW iC Ih Il Is It jG jL kC kF kG kO Lj lL Na NC Ne nH Ni
Nj Nk nL Pd Pf rX rY) Gn(BO Cv Dd Ez Hc Id Ii Jf kG Lt Lu Lw mY Nm Qu Qw Rb Rg Ri Tr Tv Up Uv Vp Vu Wm) Vv(aU Ax bX Dg Dl Gd
Ii Jj Jo Jt kG Lp Mb Mm Nm Nn Nv Of Oh pK Rc Ss Ug Ux Vo Zq) jF(aA Is jD Ji Jl Jp Jq Lx Ly Mm Mn Mp Mu Mw Mz Nm Nn Nq Nv Ny

Figure 32 Continued

Om On Pd Pe Pf Pg) Eq(Bb bW cJ cQ Fb Hc Jj Mh Mz nJ Nm Nn Ny Oi Oz Pc Qx Rc Ri Rt Tr Ug Um Zq) Wd(BB bO bW cl cM cW Dd Fb
Gp hC Ib Kn Lp Mb Mk Og Sh Tr Ug Uk Uo Va Ye) jE(Fr Hq Hu Il Is Ji Jl Jq Lv Lx Mn Mp Mv My Mz Nn Nq Nv Nx Om On Pg Po) jL(aA Et
Fr Jh Ji Jl Jq Lh Ly Mm Mn Mt Mw Mz Ne No Nq Nv Nw Nx Of Ok On) Ut(Ax dH Fa Fb Fp Ha Ij Jm kG Kn Lh Li Ma mE Mm Nk Nn Nv Ny
Oh Qe Rm) hA(aA Hr Ii In Is jG Ji Jp lK Ly Me Mq Na Nc Ni Nj Nk Og Pa Pd Pf Qd) IL(aA Hu iC jH Ji Jp Js kP IW Lx mH Mn Mt MW Nv
Nw Nx Pb Pd) Rv(bB bN bU cl cY Ez Fr iO Jm kG Lp Ma Mk nC Po Qy Ri Uf Yh) Ma(Ax Fr Ii Ip Jj Jm Jo jQ Jt jU IM Mm Nm Nn Ns Of Ok)
Zq(bQ bZ Co cU dF gL HC Jd Jl Lh oF oN Ou Pf Pg Uf) Lp(cF dl Hc Hu kS Kx Qt Qu Qw Qz Ri Tr Ua Uc Uv Vs Vu) Ax(Cu Ez Fy Jr Kq Kx
Lx Ml Oh Pf Rh Tr Tt Uf Xa) jR(aA Ii Il Io Is It Jj Lu Lx Me Mu Nn Og Pd Pf) jM(Il Is Jp Li Lv Me Mf Mu Nn Oi Om Pd Pf Qd) IM(aA Ji Jq
Js Lx Mn Mp Nv Nw Nx Ny Om On Pd) jG(Fr Jl Jp Lh Lv Lx Mn Mz Nv Nw Nx On Pf) Nm(Aw Cu Hc Is Ji Mg nR Nw On Op Tt Yh) jQ(aA
Il Is It Jj Jk Lx Me Nn Og Pd Pe) Hc(Ad Dl Gd Of Rt Sf Sh Ux Va Vw We) Yh(aU Gp Ha kS Qu Ri Ss Ug Uk Uo Va) Wf(Bb bN cl cM cW fP
Gp hC Ib kG Tr) Sf(cF dl dR Hf Jh kQ Mg Mv Pz Vu) iB(Hr Io It Jj Nc Ni Nk Og Pa Pd) Mm(Aw Di Nq nR Nw On Tt Uf) Zx(cQ Dd Gp hC Ju
Jv kG Tr) Rt(bF Co Ef Mg Mk Mv My Nx) Va(iO Iz Ng Nx Of Ou Ua Yk) Cu(Ad Gd Jo Jt Of Vw Wb) We(Bb Co Ef Mb Mv My On) Op(Mz
Nn Ny Ri Tr Ug Vt) iC(Is Jl Mz Nc Nj Nx On) rA(aA Jj Lu Me Og Pd Pf) nR(Ip jD jH Jj Jt lK) Di(Bb Fb Hb Pj Rc) Xa(cM Gp hC Kx Up)
Ou(mE Pc To Vz Yl) Ux(Ao Co Jh Mg On) Pd(jH jP jY qW qX) Al(Aw Is Tr Vu) Du(bB cl Jr Lx) Gd(Hf Pg Qu Uf) Hq(lK Oy Um Yf) Yk(aQ
bO cY Vs) Yd(Bb cQ Mz Tr) Rx(Mg On Us Vs) Lj(Lz Vj Vu Ti) Vw(Bb fP Li Mg) dX(aO dK Ic kF) mE(Jy oT Qu tF) jP(Nc Ni Nj Pf) rZ(hR
kC kF kI) Gh(cY dR kS) Is(Jm qV Vz) Sh(Bg Co Jh) Jr(Fa Id Zw) Ps(fP Om Ow) Uf(Dg Jo Jt) Vj(fP Li oP) bF(Cv Dd Kd) IN(Ji Jq Ne) Fc(Qu
Qy) Fd(Pg Vp) Fi(Pg Qu) Fy(aU Qe) Vz(cM hC) eP(hB Je) nU(jD Ns) ArLx AwJu ChFb DdcF TicM Nnlu MvJj MzqT UbQd HuOf TrJp QeKq
JhlK QtYe JtOn KzoT LtcS YlhC NwqV OgqX aAhV bUpK mZhR} oP{Uw(aG aK Ao aQ As AW Ba BC bQ bU cG Ch cK cL CO Cp cS Ct Cu dD De Dg DK Eq Ez Fd Fi Fw Gd Gl Hc Ho Hu Hv Hx Ii Il Im Iz Jd Jg Ji Jk Jl Jn Jo Jq Kd Ke Kf kG Kj Kl Kn Ko Kp Ks Kz Lh Li Lp Lx Mh Mi mM MP Mq Ms MT Mu My Mz Ng Nk NN Nq Nt Nw Nx Of Oh Ok On Ou Ow Pd Pe Pf Ps Pz Qa Qd Qh Ql Qt Qu Qy Qz Rz Sj Sr Tv Tz Ua Ub Uh Ul Un Up Ut Vi Vj Vt Vu Vw Yh Ye Wm Ti) Vj(aF aK bH Bo bZ Ch Cp cQ Cu Di Et Fb Fi Hb Hp Hu Hv Hw Ic Ij Jd Ji Ke Kf KG Kj Kn Kp Kq Lh Li Lj Mm Mn Mq Ms Mu Mw My Mz Ng Nm NN Nv Ny Oh Oi Om Ow Pd Pg Qa Ql Qm Qu Rz Si Sr To Ua Uf Uh Ul Un Up Vt Vu Wd Wh Yh Xa) Vb(Aj Ao As Aw bC Bg bQ bZ cG Ch Co cS Ct Cu Di Eq Fi Gl Hu Hw Ij Il Im Is Iz Jd Jg Ji Jo Ke Kf Kg Kj Ma Mm Mu Mw My Na Ng Nn Nv Nw Of Om On Ou Pf Pg Ph Pi Pz Qh Qt Qz Tv Ua Vu Vv Vw We Wh Yh Xa) Uy(Aj An Ao aV Bb bC bG cG Ch cL Co cS Cu dA Dc De Eq Fd Fi Gp Ho Hu Il Ip Iq Iz Jd Ji Jo Jq Js Ju KF Kg Kj Kl Kq Lh Mg Ml Mm Mu mW My Ng nR Nx Oh Ok On Ph Pi Qc Qd Qz Rz Sf Tv Us Vu Wd We Wh) Zq(AO BA bG bH bQ bU cG cI cM Co cQ CT cX Ez Fy Gl Hc Hr Hw Hx Id Ij Im It Iv Jf Jl Jn Jp Js Kf Kq Lh Lx Ly Ma Mg mW Mx Mz Na Nb Nn Nr Nw Nx Oh Ok On Ow Pf Pg Rz Sj Yh Ye) Sf(aK aN aU Aw Ax bB Bc Bg cF Ch cK cM Co Cp Cq cY dA Dc Di dJ dR Gh Gl Hl Hq Hu Hv iA Id Iz Jf Kg kP Kr Lj Lt mM Mu MY Nc Ng Nk Nl Nn oK On Oy Pb Qn Qz Ri Tv Ut Uv Wc Yd Yh) Vw(Aa aG Bb Bc Dg Et Fb Gd Hb Hp Ib Ii Ij Is Jd Jp Js Jt Kf Kn Kp Lh Ma Mm Ms Mz Na nJ Nm Nn No Nr Ny Oh Oi On Ow Pj Rc Si Uh Ul Un Up Ux Vt Wb Wh Xa) Ux(Aj Ao bC Ch Co cS Ct Cu Eq Fy Gl Hw Ij Il Iz Jd Jg Jh Ji Jo Js Kf Kg Kj Kq Lh Ma Mm Of Om On Ou Pf Pz Qc Qt Tn Ua Ut Vu Wd We Yh) Yh(Ar aZ Bb Bc cQ cX dJ Du Gd Hb Hl Ju kG Mz Nn Pk Ps Pz Qb Qc Qe Qh Ql Qn Rc Rm Rx Sr Ss Uh Ul Un Uu Vh Vo Vq Vt We) Wd(Aa aF aG Ap Bc bH cI cQ Gd Gl Gp Hb Hp Ic Iz Jg Jh Jp Kq Lh Mn Ms mT nC nJ Nm Nn Oi Om Ow Pj Po Ql Qn Qy Si Sr) Ho(aF Ap Bb Bc bW cI cQ cT Du Fr Gd Gh Hb hC Hl Hp Hq Id Lh Mm Mn Mz Nm Nn Ny Oe Om Qg Ql Qn Sr Uh Ul Un Up Vt) Rx(An BA Bg cI cL CQ CT cX Dk Fy Gh Gl Hq Hr Id Jq Lh Na Nc Ng nU Of Ok On Ou Qt Rt Tv Vv Wh Yk Xa) Rz(Ad Bb Bc bH Co cQ cR Cw Dg Dl Fr Gc Jg Jt Kl Kp Nm Nn No Oe Oi Pz Ql Qn Qy Rc Sr To Uh Ul Un Up Uu Vt) Gh(aK aQ aU aV bB bQ bR cY dA De dJ dR eM Fn hC Jn Ju kR kS LX Mz Nb Nm Nq Oi Qd Qt Qw Qy Qz Vu Wm) Wh(aG aN cF cM Cs Cw fR Gl Hb Hf Hp Ib Jd Je Jf Jg Jh Ke Kf Oe Oi Op Ow Ql Qm Qn Si Sr Uh Ul Un Vt) Ps(aG Bo Cs Fa Fb fR Jf Kn Kp Lh Lj Mm Mn Ms Mz No Ny Oh oQ Ow Oy Qm Sr To Ul Un Up Ut Vt Xa) Hl(An Ao bB bC bU cM cS Ct cU GL iH Il Jf Js Ju Kg Kx Ml mS mW Mz nU Oe Ph Pk Qc Qt Us) We(aG Bg bN Dk dM Gd Gl Gp Iv Kk Ks Lv Ly Mb Me Ms Nb nJ nL nU Og Op Si Uh Un Uu Vt) Xa(aF Ap aZ Bb Bc cM cQ Cw Fb Gp Hv Jf Mz Oe Pk Ql Qn Qy Rf Sr To Ug Uh Ul Up Va) Du(aQ bB bU bZ Ct Ez gL Hc Iv kG Li Lx Ma Mg Na Ng Nn Ow Po Qt Uf Wm) Fi(aF aZ Bb bH cQ hC kS Mz Nm Nn Ny Oi Pc Pk Rc Sr To Uh Ul Un Up Vt) Hp(Di Fw GL Hv Jp kG Mg Pz Qa Qd Qh Qt Qu Qy Qz Tv Tz Uf Ut Vu Wm) Va(Ba bC bU cL Cq Ct Dk Fy Is Jk Jq Kf Kj Lh mW Nv Nx Om On Qz Tv Uf) Vi(Al Bo Fb Hb Ib Jp kI Kn Lh Ms Mz nJ No Oe Oh Om Qm Uh Ul Up) Gd(Aw bU Ct De Eq Ez Gl Hu Mv Om Pg Pz Qu Qz Ua Vs Vv Ti) lL(cD iC kP lK lW lY mF mW nA nC nH nK nL nT rB rC rX rY) Si(aQ GL kG Qa Qd Qt Qy Qz Sr Tv Uk Un Ut Vs Vt Vu) Nm(Eq Fd Is Jg Ji Jn kF kG Ma Mg Mv Nt On Qd Vv Ti) Ti(Aa aF cM Et Hb Kn Kp Lh Mm Mn Ms Sr Ul Vt) Eq(Ap Bb bH Cw Mz Nn Ny Oi Pg Qz Rc Sr Uh Ul) Lp(Ba Bg bU Ct Gl Hv Ng Pg Pz Qd Qh Qt Qz Vu) Lt(bC bU cC cS Ju Ky Ml mS Nn Pb Qt To Uf Uo) qV(hV jI lK lN lW mF mY nC nK rC rX rZ) Fd(Mz Nn Ny Oi Rc Sr Uh Ul Un Up Vt) Rt(Aa bN Ct dE Kp Mk Ms nJ Oe Pg Rc) Wc(An bI cG Gp Ju Kf Qz Ri Up Us) Wf(Aj Bo cS Hc Iz nH nL Ri Us Vv) Ye(aF hC Hq Hv To Uh Ul Un Up Vt) rX(aA hR hX jI kN mE mF nR qU rB) Zx(Bg Ef Gp Hu Jv Mu Mv My Ou) lK(aA eD hR jP jU kN lN mF rB) Gc(aU bU Hq Jf Mg Mv nK Ut) Sh(bU Cp Ct Di Gl Ng Pg Ua) rZ(hX iC kN lM lN nA nL nR) rY(aA hR hX jI kN mF qU rB) Yf(Ax Cs dA Hf Hv Ml Rf) Sj(cI cM Ib Mz Nn nU Ny) jV(eD hR jI lM mF nC nK) Wb(bU Jd Pg Uf Ut Vu) Vv(Ii Jj kG Mm Op Ug) Yk(Jv kG Kp Oe Rc) Vz(cL Ct Hv Ju Pi) lM(aA jU mW mY nT) Ax(fA Pe Ru Zw) Rv(Iv Mt Mw nH) Op(bU Pz Ua Vs) lN(hW lY mE nD) Vh(cL Jf Qz) jF(aA nH qW) kG(cF Qg Th) Al(Qh Vu) Fy(Rf To) Mm(Qu Tt) Tn(Ii Ug) Zw(Ez Rf) Ru(Hv Ml) nT(hR jI) mY(hR iB) nA(iB jU) nK(hX jU) jG(jI jY) jL(nC nH) ThbB NnfA UaPc TtOh IiUf IsJm YddA NyoT cFnO nUjQ} eP{Ld(aA aJ aP Ax aZ bA bO bU cG Cp Cq Cs CU dB Dc dG Dk dM dX Ed Ef Ex Fp FR Fy gP Ha Hc Hq Hu Hv Hw Hx Ih Ij Ik Im Ip Iq Ir Is It Iv IZ Jd Jf Jk Jl Jn Jp Jr Js Jt Kd Ke Kj Kq Kr Ky Li Lx Mi Mj Mp Mt Mu Mv Mw Mx My Mz Na No Nq Nu NY Oa Oh Ok Om On Ow Pa Pd Pf Pg Ph Pi Po Qa Qc Qd Qe Qh Qt Qu Qw Qy Sr St Tv Ua Uc Uf Un Up Ur Us Vp Vs Vv) Jd(aC Aj aL aO Aw bF bH bO bR bU bV cF Cq cT cU dB dD dF dI dK Ed Ex Fb Fy Ho Hp Ik Jj kG kR Kx Lp Mm Mv Na Nj Nm Ns Nw Nx nY Og Ok Ou Ow Pa Rt Ss Ua Ub Ue Ug Uh Uu Uz Vh Vo Vs Vv Vz Wb Wd Yh Xa) Ua(Aj AO aP Ar Ax bA BO bV bZ Cq Cs cT cU dF Dk Dp Et Ex Fw gP Hf hG Ic In Jo Jp kG Kj Kk kR Lh Lp Lz Mb Mj Mk Mp Mt Mw Nn Nq nY oF Ou Pc Pf Ph Ql Qv Qx Rt Rv Sr Ue Ug Uh Un Ur) Ut(AA Aj aL aO bI BO bV CO cQ dB dD Ha hB Hc hG Hq Hw Il Iz Jo Jp Kc Kf KG Kj Kk Kp Lu Lv Me Mm Nj Nm Nn Nx OF Ou Pa Pc Pj Qv Qw Qz Ss Ug Uk Uu Vo Vv) Wd(aG aH aI AO aP Ar aU bQ bZ cB cC cE cO dD dG Dk dL dX fP Fr Fw Hq Ii In Iv Jp Lh Lp Ma Mj Mm Mp Mq Nq Nr Oe Pf Uf Uw Vb Vq Wf) Kq(Aw bA bF Bg bI bV Ch cI cT eM Fb Fp Hc Hu Ib Iu Jp Kn Li Lj Lu Me mT Mv Na Nm Ns Nv Nx NY Ou Ph Qz Rm) On(Ad Aj Al aO Ap Aw Ax Bc bO cD cI cS cU Cv dD Dg Dl Ii Io Iu Jm Jo Jt Kc Kn Lu Nl Nm Nn Nt Nx Of Og Oh Rm) Uf(aO Aw bA bV Co Cq Cw Dd Dk Dp Ex gP Hc Hp Jj Jo Jp kR Kx Lp Lu Mm Mv Nb Nm Nv Ou Ph Ri Tn Vo Wf Wh Yh Ye) Ex(aU Aw bW cC CO cU De Ed Ez Hc Iz Kc Kd Kg Kj Li Mi Mp Mt Mu Nn Nq Nt Ou Ow Qu Qy Uc Vq Vu) Tn(Ad Al cC cO Cx Dd Dl Dp Ed Fb Ii Jt Kk Kl kR Lv Ma Nj Nm Nq Nx Og Ou Ow Pz Rc Rm Ur Uu Vo Vq) Uw(Aa Ao Aw bC bF cG Ch Cs dA Dc dG Di dL Fp fR Gp Ib Id Jg Jr Ke Lj My Ns Nw Oa Qb Qe Rf Uk We) cU(AO Aw Cp Cq De Ef Fr Hc Ho Ib Jg Jh Jk Jp Jt Lh Mu Mv Mw Nt Nv Nw Ny Ok Om Pz Vs We Wh) Mv(hG Kc Kk Kr oF oH Or Ou Ow Qh Qv Qw Rg Tv Ue Ug Uh Un Up Ur Vs Vt Vu Th) Ef(bO Gz hB Iz Jj Kj Kk nY oF Ou Ql Qv Qz Rg Ss Ue Uh Um Un Ur Vo Vt Vv) Hc(aC

Figure 32 Continued

Ao Aw bO Cp dR Et Fi Gh Gz Ke Mi Mp Mt NA nU Nw oF Ou Ow Sf Uh) Om(aA bA bO bV Dp Ed Fy Iz Kf Kj Kn Nl nY Ou Qz Sj Ue Uu Uy Vo Zw Yf) Bg(Fy Gh Ho Ic Kk Lp Op Qv Qx Ss Uh Um Un Uo Up Ur Uu Va Wh Ye) Fw(Aw Cq Hl Ho Jj kG Kx Lp lW nY Ou Vh Vw Wh Yh Tl Ti) Si(aJ aP Cs dG dL Hx Ih It Kf Mq Nu Qa Qe Qt Rf Rm Sr) Lp(Cp Ho Hp Ih Iz Jk Jt Kj Kr Ky My Nn Nt Qm Rf) Oa(Du Gd Gh Gn Hl Jf Qa Uy Vc Wc Wf Yj Yl Tm Ti) Aw(BA bO cG Cu iZ Kr Mj nC nH Ok Ph Vp Vq) Yh(aU aV bO dA gL Kr oH Pf Pz Qz Sr Ss Um Uo) Wh(aG bB cE cG Et Fr Hq Ii Jh Ke Mt Nn Nq Vq) nY(cG Co Cp Gp Hu Kg Kj Mg Na nC nL Ph Qu tF) Cu(hG Ii Jj Jm Kx Lu Nl Ra Rb Sf Ub Uy) Nv(Eq Fc Kc kG Ou Ow Ur Ux Vb Yj Ti Th) Qe(Du Fy Gn Hl kG Sh Uy Vw Vz Yj Yf) Nw(cS Du Eq Hb Qu Rz Vb Vh Vz Tl Xa) cG(cE dH Ho Im Jf kK Vc Vh We Yd Xa) nU(bV dE Hu Ib mI Na Qn Qu To Uk tF) Zw(Ed Kr Li Qb Qc Qd Tz Un Up Yj) Pe(Ax Fi Gh nD Sj Vz Yd Yj Yl Th) Hu(Ed hB iZ Kx oF Ow Sr Un Ur) Rt(bZ Ij Iv Jl Jy Mt Pf Qz Vu) Hx(Hl kG kR Op Uy Uz Yd Zx) Yk(bZ CO cS Nn Nq Pf Qz) We(bZ Et fP Fr Ih Jp Nn Vq) Ny(bW cC kG Mi Mp Mt Uy Yf) Vs(aP bO cC cS Gn Mb Rv Va) aO(Ho Iz Ke Kj mI mT Vu Yj) bV(Ed Ji Ke Mi Mp Mt Ow Uc) Ao(aA Ed Fy Jf Uh Uo Vo) Nt(Gz hB hG Ou Ug Ur Wm) Qa(cl Fy mF nD Sh Uz Th) Vc(Ax Mx Nq Po Rm Sr St) kF(aH bB bP eM Kx Ri Tj) Ho(dF Hq Jv Mm Qz Sf) Yj(Jl Ky Nb Qz Rf St) Yd(Fp iZ Lj Mj Nb Sr) hB(Ib Kg Kj kO Na Xa) Co(Kk Ko Ug Ur Wc) Fd(Lx Lz Qd Qz Vu) No(Du Fi Ux Vz Tl) Mt(bA cT Ib Vh Yf) Ih(Fc Op Vb Wf Zx) Iz(bA Fi Jp Kx Op) Qb(Dr Gh kG Yl Ti) Ky(dR Ry Um Uo Wb) Un(bF Gh Hp Lt Tl) nC(Dd dF kR Ph Ql) Cq(Fi Kc Qu Qy) De(aA bA cT Mj) Eq(aZ Gc Jq Mn) Hl(fP It Nb Nq) Jh(Kk Qw Ue Ug) St(Du Gh Ux Vz) Wc(Lj Mz Nn Qz) Kj(Jj Jp Kx Ow) Vu(Ch eM Lu Ry) kG(It Mr Qm Qn) kK(cS gL Kc Nu) Fc(Nq Nr Sr) Mp(bA cT Di) Hp(Hb Lx Ql) Xa(Gc iA Iv) Ke(hG Lu Ns) Kr(Gh Rv Zx) Ow(cT eM Wf) Ou(kN nD Tt) Vq(Ch kR mF) Du(Lj Po) Ed(Ch Ph) Mr(kI kR) Nb(Op Rv) It(Vb Th) Qd(Fy Uy) Qz(Dr Sf) Qm(dB oF) Ur(Cp Vv) Vw(Lh Rm) Pf(mF Vh) YfHv FrSh GcKf NnWf NqTm LxYe MibA MjbC MyRv NaKk UcOp IboF IrUy ZxVv SreM QycT QumY JlRx JqRz KcOk KggP UhdB aAdR aUlX dEmI dFnH nRmZ} nU{Wh(aC Ad Aj Al aM aO aP Ar aU aV aZ bA bB bE Bn bO bW bZ cD cG Cs Cv dA DD dF dG Di dL Du Em Eq Ex Fn Gd hB hC Hl Ho Hv Ik In Is Ji Jj Jl Jm Jn Jo Jq Js KE kG kI Kj kK Kx Ld Lh Li Lp Lv Lx Lz Me Mh Mj Mk Ml Mp Mq mS Mv Ne Ni Nm Nq Nw Oa oF Og Oh Oi oN Or Ou Ow Pe Pf Ps Qa Qb Qd Ql Qn Qx Rg Sh Tz Ug Uk Ul Uo Ux Vb Vp We Yd Yj Tl) Hl(Af aJ AO aP aQ As Aw bA bO Cp Cq cS cT DD dF dG dH Dl Dk dM Eq Fy Gl Hc Hu Hv Ib Ii Im Iz Je Jh Jl Jn Jq Js Ke Kf kN Ld Lh lW Lx Mj Mw Ng Nw oD Oe Oh Om ON Ow Oz Pb Pc Pe Pg Po Ps Pz Ql Qn Qt Qu Qw Qy Qz Rj Rm Rv Rz Tr Tv Tz Ua Uc Ur Us Ut Uu Uv Vi Vp Vs Vu Vv Wd We Wf Ye Xa) Wd(Ad aJ aK Al aM aO aP Ar aU aV aZ bA bB bO bW bZ Cs Cv DD dF dG dL Dp Du Em Ez Fn hB Ho Hv Ij In Is Ji Jj Jm Jn Jq Jr Js Kc KE kI kK Kx Ky Lh Li Lp Lv Lz Ma Mh Mk Ml Mp Mq Mr Ni Nm No Nq Nw Oa oF Og Oh oN Or Ou Ow Oy Pe Po Ps Qb Qd Qn Qx Rg Sh Tz Ug Ul Uo Vb Vv Yj Ye Tl) Xa(Ad aF Aj Ap aU aV aZ Bb bO cC cU Cv cX Dd Dg dJ Gd Hq Hv iJ Il In Jg Jj Jn Jo Jr Jt kE KG Kj Ko Ks Mh Mz nA Ng nJ Nm Nn Ph Pk Qa Rt Rz Ss Tt Tv Tz Uh Uk Ux Vt Yj Tj) Uw(Ad aF aK AL aO aQ aU aV Aw Cv cY dA dD Dg Di dJ Dl Fc Fi Gd Gn Hv Jm Jq Jt Ld Lp mH ml mS Nc Nm oH Oz Qn Qv Tz Ug Vq Yj) Ps(aK Al aQ aU bE Cv cY dA Dd Di Em Ex Fc Gn Ib Jm Jq Jr Lp Lz mE Na Nc Ng nJ Ns Pb Qn Qx Rv Tz) Vi(Al aN aQ aU aV Aw Bn Cv dA DD Dl Dr Fc Jm Jq Lv mE Mj Nf Nx Ou Oz Rv Sf Wb Yd Yh Yj) lL(aA Fp iC Is Iv jD jH Jo Jq Js kI Li Lv Lz Mk Ml Mq mS Mt MW Pd Pe Pf Qb Qd) Tn(Dp Fd Fi Gn Ho Ii Jj Jm Jo Jr Jt Kd Mb mT Of Oi Ph Rb Ss Ug Uk Uu Zx) jE(Et Fr Hq Hx Ij Jh Ji Jo Jq Lh Lv Lz Mj Ml Mp Mq Mv Nf Om On Pa Pd Pf) jI(hR iC In Is Jj Jo jU jV kG kI ml mS Nc Ni NK nO Nw Pa Pd rC rX) Yj(aO aQ Aw BA bQ bW Cp cT Gl Jq Lh Nc On Tz Ua Ut Uv Vs Vu We) Uy(aV Aw bA Cu dM Fw Hv Jn Jq Js Lh Mj Nw Ny Oh Om Ry Tz Vp Vs Vv) jF(Et Fr Hx Ik Ji Jo Jq Lh Lj Lv Lz Ml Mp Mq Mw Nw Om Pa Pf Po) Jo(Aw Hu iB iC jM jU jV lK Lx Ma Mu Mv Nq Nt Nw Pb Pz Vv) lM(Fr Hq Hu Im Jh Ji Li Lx Mw Nf Nn No Nr Nv Oh Om On) Aw(Ad Al Ap Cv Dd dI Gd Jm Kd Lp mE Oy Qz Sf Sh) qV(Is jD Ji Js Lh lK Lx mH Ml Mp nJ nN Nw Pf Qc) Pb(Cv Hr Jj Jm kG Li Lx lY Lz Ml Mq Nq Pf Vj) qY(In Io jD Ji Lh Li Lx Lz Ml Mv Mw Ny On Po) Qd(Hu Iu Jk Jm Lu lY mE Mu Ns Pc Pz Rz Ub) Gn(Fn Hv Jr Js Mj Pg Qb Qn Tv Ua Uv Vp) Jr(Al cF Cv Dr Eq Um Vv Vz Wf Zw Zx) Rz(Aj aU aV aZ Hv Qx Rg Rh Ss Tz Ug) jM(Ik In Jq Mb Me mW Nc Ni Nq Pa Pf) Hu(Jj Jt kG lY Mb mE Nm Of Pc Qa) Rv(aO Ba Cv Di Fw Jd Nq Oi Po Yh) Vv(aQ bX Cv Dd Jj Jt Kj mE Ug Zx) hR(iB iC jK lK mH mM mW mZ nC nN) jG(Fp iC Im In Lh Li Lj Lx Oh Pf) jH(hA iB Ji jP kI Lx mM mS Nw Oh) Tz(Aa Al cF Em lY Si Vz Yl Zx) Pz(Gd Jj kK mE Mj Mx Ns Nw Pc) Jm(iB Is Jn jU jV jY Lx Pg Qa) Nm(Is Mv Nq Nt Nw On Vh Yh) qU(Ji Jq kI lK Lz Ml mM mS) jV(lK Ly Mp MW Nc Ni Nl) Nq(Gh Jj mE Mm Ns Oz Pc) Mv(Jj JT kG Mm Oy We) Ua(Al Du Ho Hp Lp Ye Tl) Yh(aZ Qv Qx Rb Ug Ul Vq) Sf(aQ Fw Jn Ke Om Ou Vs) jU(Hv Ly Nc Nj Nl Nx Pd) Mq(jK lK lN Ns qX rA) We(Ef Fi Lv My Po Ug) Vj(As Bn Cx eM Oz Qn) Vs(Du Ho Lp Rt Sh Tl) mE(aA Di Fw Mb Mu Um) Cv(aC aL bA cT Yk) Lx(Al Jj Mm Oz Wf) Hq(eD Lp Mm Oy Yf) Vb(Ba CT Ib Kf) iB(Is Jj lK Mb Pd) jY(Im Nc Ni Pd rX) Fi(cT Pg Uf Ut) Mu(kG lY Of Pc) Vz(Jq Js Mj Nw) Zx(aF aO hC Vp) Wf(aQ Ld Oh Ow) Oz(kG Lz Pe Pf) iC(Nc Ni Pa Pd) jD(kE kI Mh mS) rZ(kO mH nR qT) lK(kI Li mM mS) Di(Qz Rb Uk) Yf(Ba Co Js) Eq(Hv Ug Ul) Fd(Om Ut Vp) Jj(Jk Ng Nv) On(Jt Mm Vh) Vw(aV Co Cu) Pc(Ji Jk Lh) eD(It Jk Oe) lY(Mj Nv Ny) hV(jK jR lX) rA(Fp Mb Me) jT(Is Mw rB) Al(Jn Vu) Dd(Fw Pg) Dr(Js Ld) Gh(aQ eM) Ns(Qa Rb) Yk(Qx Ul) Op(Ul Vq) Ou(dX Si) Ut(Kd Rb) Vh(Ao Lh) Pf(Gd Ru) jK(aA Nu) AaPg AxQa CuRx DpcT NtJt LuIs MbNv MjkG MmNw IbUr YdQx ZqKq JslN OwpK hAmW nNrX} dX{We(Ax aZ BA bL bX cB cF cM cN Cs cT cU Cv cW cZ Dc Dl dR eF fP Fy gL GP hB Hc Hf Hp Hw iA Ic lH Il Io iP Iq Iu Jf Jl Kn Ko Ks Lj Mb Mh Ml Ms Na Nf Nu nW Oa oE oF Pa Pc Pd Qh Qm Qt Qv Qx Qy Ra Rg Rh Ru Si To Uc Ue Uf Un Up Ur Uv Uw Uy Vq Vv Yj Yk Wm Th Yf) Ho(Aa aE aG aH Ap BA cD Db Di dN Dr Du Et Ez Fy Gh Hc Hr Id Ih Ii Ip Iu Iz Jl Jy Kf Kk Kp Lv Mn Mr Na Ng Nm Nu Ok Op Pa Pi Qn Qt Qy Ra Rc Rf Rg Ru Rv Si Uh Us Vo Vp Vv Vw Vz Wh Yd Yj Zw Tl Wm Ti) Wd(Aa aE Aj Ao aQ aX bA bL cB CQ Cu cV cX dE dl Dk Dl DR EM Fd Fy Ha HC Hv Hx Ic Ih Io Jf Jl Jp Kn Ko Mf Mr Ms Mv Nc Nr Oe Ok Pa Pc Pd Pg Qn Rc To Tv Uc Um Ur Uw Vh Vp Vv Yk Ti) Wh(aD aE Aj Bb cB CQ cW Dd Dl dM dN dR Fy Ha Hc Hp Hw Hx Ih Il In Io Iu Jf Jk Jm Kd Kj Ko Lp Mi Ms My Na Nc Nf Nk oH Ok Pd Pi Qa Qc Rb Rf Rt To Tv Uf Un Vq Vu Wb Wc Yj Tj Yf) Yk(Ad aF Ap Ba bJ bU cZ Db Dg Dl gL Hw Hx Ih Iq lZ Jf Jg Jy Kl Mg Na Ni Nj Nt Pc Pd Pz Qc Qn Qt Rf Rt Ue Uf Un Ur Uy Vw Wm Th Yf) Jf(aA aO BA bF Bg bO bQ bV cG Ch Co cT dD dE Eq Gn Hc Je Kj Kl Ks Ma Mg My Mz Na Ng nY Oi Pa Pd Qu Rt Ry Rz Tt Ua Vw) Vw(Aa aC bA bL Cp Cq cT cV cW cX Dc dE dR Fd Gp Hv Hx Iq Ko Kr Ks Ms Oe oH oK Or Pa Pb Pg Qh Qm Qn Rc Rf Si Tv Yd) Uw(Aa aD aM aY Ba BB Ch cM CT cW Di dL fR Hu Io Jg Ks My Nc Nf Nk Ns Pb Pi Qy Rc Rf Rg Rv Tn Tz Ub Uv) Vh(aD aE bA Bc cN Ct cW Dl Hc Hu Ib iO Iq Na nW Oa Oe oH Oy Pb Pc Pi Qc Qm Qn Qy Rc Ry Tn Ua Uc Yj) Yj(Ad Ba Ch CT Dc hC Hu Ib Jk Jr Kf Kj Mu Mz Na Ng Nt Nx Oe Ok Pi Pz Qn Rc St Ug) nY(Aa aE aQ Ba Bb cT Di Dk Gp Hu Jg Ji Jt Kj Mn Ms Mu mW Mz Ok Pa Pd Pi Pk Ub) Yf(Ao Bb Bg Ch De Hu Ib Kf Kj Kl Mu My Nt Ny Om Pb Pe Qa Ql Qm Qn Rc Ua Vp) Hp(Ba Bb Ch Dr Hu Ib Kc Kf Kj Kp kQ Kz Mu Na Ng No Ns Nx Pz Uk Yh Ti) Rt(Ap Db Dg Dl dR Hx Jp Mg Ng Nu Ny Pd Pi Qc Qt Qy Ua Un Vp Vu Vv Wm) Uy(Bb Bc Cp Cq Dc Fd Fy Ii Jk Jp Kj Ko Ks My Pz St Tv Ua Up Vp Wb) Xa(aA aD aI bB bL dG Dr hG Kr Nf Nn oE Oy Rg Sr Tn Uc Vu) Fd(Ba Iz Jg Me Mw My Na Ng Nq Nt Ow Pe Pf Pz Ql Qm Vs) Yh(aD aY Bb cT dR Hc Hx Iq Jg Nc Nl Oa oH Qb Qc Tn) Zw(Cp Cu Dk Ij Iz Jg Jk Kj Ko My Nq Pz Sr Ua Uf Vs) nR(aO Aw cF Ez Gz Hu kC Ma Mu Mv Na Pk Rb To) kF(aH cA cZ In kQ Lz Mv mW mY nF Ph Qg Qx Rb) Wb(Aa BA bL cT Dc dR Gp Hc iH kQ Ks Ng) Dr(Hc iP Kj Kl Qd Qm Qn Qu Rc Ub Vv) Yd(aD Ba Ct Fw Iz Na Nb Nr Nt Pe Qa) Si(bA bV cT dM dR Jg Js Ng Of Qm Qu) Ou(Fr kI ml nA Nb nC nD nH nL Rm Uc) Vb(dR Hx Jl Jq Ke Mz Nt Nw Pi Qh) Vc(Ba Bg bV Ct fP Hc Kr Of Qz Tn) Ti(Cq Ib Jk Mj Ny Pa Qa Tz Vp) Fy(aN Bb Dp Kr Mw Nf Pb Qd Qy) Hl(dR iO iZ kS Nb oH pF Rm St) Wc(Hc Hx Ih iP Kl Ng Qc Qm Qt) aO(kO mI mM mP nA nC nD nJ Pi) Eq(Bg dR Hc Iz Jg Ng Pi Qz) Sj(Ad Dl Jl Mr Nq

Figure 32 Continued

Figure 32 Continued

Figure 32 Continued jM(It Ms) DuNq FimH GhdR NmJd MaJt NbYd HvYk HcdA YhQv SfOh LtPf RvRi VsfB} kG{Dk(Aa Ad Al aU Bb cR Cv Dd Dg Dr Fb Fw Gn Hb Hl Hr Ic Jm Jt Ju Jv Kl Ks Lh mE Mn Nb Nm Of Oz Pb Pj Rb Sf Ug Uw Ux Uy Vb Vv Yj Zq) Yj(Aa As cL cM cN Cp Cq dM dU Ef Fd Hu Hv Ib Iq Jh Jk Jl Jq Js Mq Mu Mw My Nm Nq Om Oy Oz Pb Po Ql Qn Qt Rv Ua Vp Wh Yh Th) Xa(aF Bb bW Dd dK dU eQ Hc Hp Hu Hv iJ In Jf Jj Jn Jr kl Ks Lh Ma Mb Mj Mk Mm Mn Mq Nb Nm Nn Nq Oh Om Or Ow Pf Rv Tj) Ps(Aa aF Bb bW Dd dI Dr Fb Fc Gh Hc Hu Ib Iq Ks Lh Ma Mm Mn Nf Nm Nn Ny Oh Om Ow Oz Pb Rv Tr Uw Vb Vj Wb Zq) dU(cT Ed Eq Ez Fw Hl Je Kf Kl Kp Kz Nb Op Ou Qg Qn Qt Qu Qw Qy Rc Rj Sh Sj Tn Tt Ut Vo Vv Yk Zx Tj) Vb(Aj Aw Bg Ch Cp Cq Ct Ef Eq Hu Ib Iz Jd Jk Kf Kl Mu My Nv Pg Pz Qt Ua Uu Vi Vs Vv Wd We Wh) Hl(Cq dG dM Hc Hu Iq Jk Jl Jq Js kO Mj Mw My Nv Om oN Oy Pg Qd Ql Qn Qt Qw Tv Vv Wf) Uw(aF bW fP Gl Jl Jn Jp Jq Jr Ko Ks Ma Mm Mn Nn Nq Nv Oz Pb Pc Pg Rh Rm Rv Tr Uf) Rv(Ba bF cF cN Cp Fw Hv Ib Jk Jl Nb nL Nq Oi Oz Pb Po Qd Qw Ri Ua Um Vi Wh) Tn(aZ bG dl dK dR eQ Fb gC Hv Kd Kg Kj Kn Ly Mv Mw Nb Oz Pb Pc Ph pI Qw) Hp(Co Cp Ef Ib Jd Jh Jk Jl Jn Js Kq Mj Mv Mw Nq oD Ql Ua) Gn(aJ Cx Fd Ha Hv Ib Jl Jn Js Mj Mq Ny Qd Ql Qn Vp Yh) Wh(aF Al Bb Bn bW Hr Hv Jm Jn Mj Mm Mq Nk Nm Pb Rh Um) jl(iB It kK lK Mm Mp Mz Nc Ne Nk Nl nR nT Pf qV) Zx(cN Cx hC Hv Jn Jr kO Mj Ny Oz Pb Pc Qn Vp) Ut(bG cR dI fP Hw Kn lW Ly Mb Mu Oz
Pb pI Rb) Pg(Al cF Dd Dr Fi Gd Ho Ib Pj Si Ux Zq Yf) Vi(cN Dd dI Fc lW Ma Mm Nn Ow Oz Si) Dr(Jq Jr Js Kq Mj Nv Nw Om On Ql) Nb(aE
Al Aw Cv dA Dd dI gC Qn Yh) Qd(aU Aw Ba Ct Hb Ib Ua Uf Vs Vt) Ou(fB Gc jB lW Oz Pb Pc pI Si Ye) Fw(Aa Aw Dd lW Mm Mn nK Nm
Nq) Yh(Hw Nf Nm Nq Oz Pb Pf Rh Ti) Mj(cF Ju Nm Rz Uy Vz Wd Zq) Hc(EQ Gd lW pI Rb Ux Vw) Si(Cu Jn Jq Jr Ke Nq Om Pf) Kq(cR dI
lW nK Oz Pb Rb) fB(Ez Fn Hq Sj Tr Tv Vs) Ua(aU cR eQ mE pI Rt) cN(Eq Op Rz Vz Wd Yd) Nm(Eq Hq Jd Nq Yk) Ib(aQ aU aV aZ eQ)
gC(cL Fd lW Mm Vv) pI(Qn Tv Uf Vs Vv) Yk(eQ Jn Mq Rh) Wd(bW In Jj Rh) Ux(Ef Iz Om Qt) aU(Mu Qu Qw Wf) lW(Gp Lt oT Qu) jB(bA
cE cT Ow) oD(Aa Gc Pb Wb) Nq(Gc jG Pj) Hu(aZ Fd Jj) Yd(dK Mq Mw) Zq(Jd Jq Nv) Jl(Al Rb Vz) Jr(Al Aw Zw) Rz(bW Ef Rh) eQ(cT Uf
Vs) Hq(Kd Um) Wb(Jd Nv) Uy(Hv Vp) Vv(Dd dK) CqGd DiFn EdPb EqbW FcPf MbQu MuaZ VzJs SjVs WfcL QwcR JjJk YeaV OmVj
rZrX} Jr{Yl(Aa aJ aM aP aV Aw aZ bP cA cB cF cG cL cN De dI dJ dL DR Ed Gz Hb Hl Hq Hv Ii Iv Jo Jt Ju kE Kn kR Ks Lh Ml Mm Mp Mq
Mz Nb Nm Nn Nq Nw oE oF Om Op Or Ou OW pH Pj Ps Qd Qt Qy Rc Rf Rh Sf Si Ua Ud Ug Um Uo Uw Uy Uz Va Wg Zq) Si(Ad An Co cU
Cv Dd De Dr Du Gn Hl Hr Hu Ii In Ir Jo Jt Kd Kn Ko Mu Mv Nf Nm Nq nR Ow Ph Pk Qa Qy Ra Rb Rj Rt Sr Tv Ua Uc Uf Ul Um Un Uo Up
Us Uy Vh Vi Vj Vp Vu Wc Yj Tl) Du(Aa aJ aR Aw bE cB cF cH cN Cv De dG dL Hb Hc Hq Ib Ii Iv Ju kE kR Ks Lh Lu Ml Mm mP Mz Nb
Nm Nn Ny oE oF Oh Op OW Pj Rc Sf Ub Uh Uy Va Wh Zq) Uy(Ad aJ An As aZ bO bP cF cL cO Cp Cq cV Cw Dc Dd Dr Gn Gz Hb Ib Id Ju
Kd Ke Kn Kp Ks Lw mP Ow Pj Qm Sf Ud Um Uo Uz Wg Zq Zw Tl) Hl(Aa cB cF cN De Gz Hb Hc Hq Ib Ii Ji Ju Ke KS Lu Ml Mm mP Mz
Nn Oh Op Ow Pj Rc Rx Ry Sf Sr Ua Uh Un Va Wh Zq Ye) Yj(Aa bU cN dJ Gz Hb Hq Hv Ib Iv Jv kS Lh Lj Mm mY Nb Nm Nn oE Oh Ok Ow
Pj Rc Rx Sr Uh Un Uw Zq Ye) Va(Ad aM An As Cp Cq Cu Cv CW Dc Dr Em Gn Hc Id Kd Kn Kp Kq Kr Lw Ph Pi Pk Ud Uo Uz Wg Yk Ye
Tl) Rx(Ad An Cv Cw Dd De Gn Hr Hu Ii Ji Jo Jt Kd Ko lW Ml Nf Nm Ns Qt) Gn(cF De Ed Gz Hb Ks Mm mY nL Nn Ow Pj Sr Ub Uh Un Zq)
Hb(Dr Em Ps Rt Ru Ry Uz Vb Vh Vi Vj Wc Wf Wg Tl Xa) Wg(Ax cF cL cV De Ib Ii Jm Ju Ks Ny Ow Rc Zq Zw) Dr(cF De Ez Gp Ju mP mT
nC nK nL Ow Pj Ub Vu) Tl(cF De Ii Ju Ks Ml Mz Nb Nn Ow Pj Zq) nR(Al cF Hp Hr Jj Jm jV Mm Nm Rb Um Uw) Em(Aw cF De Ii Mm Mz
Nm Nn Oh Pj Ub) Ry(Aa cF De Hq Hu Ju Ml Ua Ub Um Vu) Uz(aR Ax cF cL cV De Ii Ju Ks Ny Ow) Vz(Aa Jo Kn mP mT nC nL pH Pj Vu)
Zq(An aO Cv dF Hr In Jq lW Nf Uo) Gz(Aa Hr iC jI jV lN lO Uo) Rz(Aa dU kE Ko lW mE nJ Pj) Uw(An mP mT nC nJ nL nN oQ) Wh(Aa Ad
Cv nC nJ nL nT) Zw(Aa mM mP mY nC Vu) Vh(cF De Hc Ju Ow Pj) Vi(cF cL De nJ Ow Pj) lW(cS Fc Fi Ho Lt Vj) Wc(cF De Hc Ib Ow)
Rt(An cF Eq Ow Pj) kE(Al bF cL Fa Xa) rZ(Aa Il jI lN qZ) Hp(De oQ Ua Vu) Vj(Aa Ke Ow Pj) nJ(Fc Ux Vw Wd) kF(aQ aV bR dA) oW(Al
Ax Fa Lj) Hc(Sf Sh Vb) Rv(bE Cv nL) Op(Hr Us Vv) cS(dU lX nK) Ho(Aa Jm) Yh(Jo Ks) Wd(Ib Ko) Vb(bE cF) fB(Tr Uf) wJ(Mz Of) DeGd
EqNn FdMl UaLp HuSh IdjI YkJv aUmF nKlK} Gz{jI(Ad aM An aO Ap As Ax bA Bc bF Bg Bn Bo bP bZ cM Cp Cq Cs cT Cu CW Dc Dd De
dF dG Dk Dl Ed Gp Ha Hr Hv Hw Hx Ib Id Ii Ij In Io Iq Ir It Iv Je Jf jG jH Jn JO jP Js Jv Jy Kd Ke Kf Kg Ki Kj Kn Ko Kp Kq Kr Kz Ld Li lN
lO Lv Lw Ly Ma Mb Me Mf Mh Mi Mq Mr Mu Mw Mx Mz Na Nb Nc Nf Nh Nj Nm Nr Nu Nx Ny Of Og Oi Ok Om Ow Oy Pb Pd Pe Pf Pg
Ph Pi Pk Qa Qw Qx Ra Rb Rg Rj Sr To Tv Uc Ud Ue Ul Um Un Up Ur Us Vp Vt) jG(aD aH aI aM aN aO Aw bB BC bF BG bN bS bW bZ cA
cG Cu cZ DD dF dJ Ed Ef Fr Gl Hq Hu iB Il Im In Jh Ji JK Jl Jo Jp Jq Kq Ky lK Lu Lx Ma Mf Mj Mn Mu Mv Mw Nb No Nr Nv Nw Oh Oi
Om On Or Ou Pf Po Qc Qw Rf St Tn Tt Ua Uh Up Ut Uv Vp) lN(aJ Ao aP Aw bC bZ Cu Ef Et Fr Gp Hq lB Ih Im Jh Ji Jk Jl Jq Jy Kq Ky Lx
Mn Mp Mr Mt Mu Mw Nb No Nq Nr Nt Nv Nw Oh Om On Or Pe Pf Pg Po Qa Qc Qh Qm Qt Qy Rf St Tn Ua Ut Tj) jO(aD BC bS bW dJ Et Fr
Fw Gl Gp Hr Hu Ih Im In jD Ji Jj Jo Jq Jy Kq Lv Lx Mn Mt Mw Nb No Nq Nr Nv Nw Og On Or Pe Po Qa Qc Qd Qh Qm Qt Qv Rf St Tv Ug
Uh Uk Un Up Ut) jD(aO aP Aw aZ bF bQ bZ cE cG dF Dk dM Ef Gl Gp Hq iB Jh Jk Jl jP Jy Ko Kq Lx Ma Mf Mh Mj Mn Mu Mv Mw Nn Nv
Oh On Or Pf Qc Qh St Tn Ua Up Ut Uv) iB(aJ aQ Bb BC Bo bS cA Dd dJ Ed Gp Hr Hx iC Ik In Jo jR Jv Kg Kj Ko Kz Ld Lu Ly Mb Me Mh
Nf Nh No Nt Og Oz Qm Qt Qz Ra Rb Uh Um Uo Vv) jP(aD aJ aP BC Bg bI BN Bo bR bS cA cI cN cR DD Ed Fr Gp In Jh Jk Jl Kg Kj Kr Lu
Lv Lx Ly Mn Mu Nq Ny Om Pg Qd Qt Qv Ss St Ub) lM(aA aM aO aP Cv Dk Ed Ex Jl Jy Lw Lx Me Mu No Nv Nw Pa Pg Qd Qw Qz Rf Rg
St) jV(aJ aP Im Jo Lx Mq Mr Nq Oh Or Pe Pf Qb Qc Qd Ql Tn) lO(Cu Jh Ji Jn Jq Kq Mw Mz Om Pg Po Qa Un) Hc(dU gC Gd Lp Sf Ux Uy Va
Vb Yk) jH(aA aJ Gp Nq) jM(BC Nb Qw) jR(In Ky Nb Nq) jU(Jv Or Ou Qc) Dk(jF jK jY) Ky(jL jT) bA(Yh Yj) gW(aJ iZ) jK(Lv Pg) jY(Lx Pf)
AwiC GpjT MejF MmTn UaLp HqUy YkoF JpjL UoVi UmpH aQjQ} nR{qV(Fp Hq Hv Hx jD Jl Jq Js jY kI kP Lh Li lK Lx Ly Lz mH Mj Ml
Mp mS Mv Mw Mx Mz Nf NN Nq Nv Nw Ny Oe Oh On oQ Pa Pd Pe Pf Po Qa Qb Qc) lM(aA Fp Fr Hq Hu Im Jl jY Lh Li Lj Lx Lz Mb Me
mF Mj Ml Mq Mt Mu MW Mx Nc Nf Ni Nk Nn No Nq Nv Nw Ny Om On Pe Pf Po Qa Qb Qd) Nm(Ez Hc Hq Hu Im Iq jI Jk Jn Jq Lh Li Lx Lz
Ma Mj Mq Mu Mv Mw Mx Nb Ng Nn No Nq Nt Nv Nw Ny On Pb Pe Pf Pg Po Qu Wh Yh Xa) lK(aA Fr Hq hR Hu Hx Ik JH jI Jk Jl Jq Js jY
kE Li Lx mF Mj Mv MW Nf Nn Nq Nv oQ Pe Pf Po Qa Qb qT qU qW rZ) Hl(aJ aP bS dG dM Hc Hq Hu Ib Im It Jn kO mF Mj Mq Mr Mw Pb
Pc Pe Ql Qt Qw Qy Qz Ur Vp Wf Ye Xa) Xa(Ad Bb Dg Fy Gd Hv Jj Jo Ko Ks Mz Nn Ok Qu Rh Rt Tr Tv Uf Uw Ux Va Vb) jI(hX iC jG Jj jL
Jm Jo Jt jU jV mW Nb NC Ni Nk Ok Pa Pd Pf Pz rX rY) jF(aA Fr Hu Hx Jl Jo Ly Mp Mu Mv MW Mx Mz Nf Nn Nq Om Pa Po) jY(hR Hv hW
Iu jG jH Jm Ly Ms Mx Nc Nf Ni Nj Nl Nx Og Ok Pa rY) jT(Hq Hv Ly Ma Mv Mz Nf Ni Nj Nk Nn Nq Ny Oe Og Oh On) cF(aE Dd Dg dI dK
Kd Ko Ly mE Mm Mq Nb Pj Qb Rv Wh) Jj(Hq Hu iB Jk Mu Ng Nt Nv Oz Pb Pz Ua Vv Wd Wh) jG(Fp iC Li Lj Lx Mj No oQ Pe Pf Po Qa Qb
Qd rB) jV(hR Hv Jl Jm mF MW Mz Nc Nf Ni Nl Nx Og oQ) Vb(Ba Ct Hu Ib Iz Mu Ps Pz Qu Ua Vv Wd Wh Yh) Jo(Hq Hu iB Jk kC Ma Mu
Mv Nt Pb qT qW Vv) Mm(Di Hq Mj Mq Mu Mv Ne Nq On Ua Vi Wh) jE(Mp Mw Mz Nn Nq Om On Pa Po rX rY) Wh(Ad Al Bb Cv Jm Kf
Lp Tr Ux Va) hR(jK mF mY nC nK nL qY rX rY) Al(Fw Jn Lx Nb Ps Qa Ua Vu) Mu(Bb Jk Jm Jt Nn Of Ok) jH(kE kI mS mY nT Pa) rZ(aA jD
kF kO mW oQ) lN(Jq Mq Mw Mx oQ Qd) Mv(Hp Jt Oy Rt We) Hq(Fd Fi Oy Rt Sf) Hu(Jt Lh Mb Of Rt) Rb(cM Di Hc Nb Tn) rX(aA jD jK
mM qU) Jm(Jn Mq Ps Qa) Pa(iB jM qT qY) qW(Lz Ml Mp Nw) Bb(Di Ef Wd) Dg(Di Ps Rz) Nb(Cv Dd Um) Hv(jD qY Uy) Hc(Ad Rt Vw)
Jt(Mw On Qu) iB(Iu nA Pd) Fw(Dd Ks) Gn(bS Tn) Mb(Iu Tn) Ng(Ad Rt) Yh(Vh Vw) Zq(On Ut) Ps(Lp Pb) Rz(Pg Ss) Pc(Ua Tj) aA(hX rY)
mW(jM jU) hW(mF mM) DrLd MjjP MwjD UbQd HbVj IzUx JdUw RvRi NwqY UyPg mIrB} Uw{nJ(aC aF aK aL aO Ap As aU aV Aw aZ
bA Bb Bc bE bF bQ bW cK cL cT cY dD Dg dJ Dl dN dR eM Ex Fc Gd Gp hC Hl Hv In Jd Jf Ji Jn Jq Js Jt Ke kI Kr Kx Ky Ld Lh Li Lt Lx Lz
mF mH Mj Ml Mq mS Mv Mz Nb Nk Nm Nq nT Nv Nx NY Oh oK Om ON Or Ow Pe Pf Po Qa Qb Qd Qn Qv Qx Rg Ri Rv Uh Ut Uv Vi Vp

Figure 32 Continued

Figure 32 Continued

Figure 32 Continued kI(aA jH lK mP nN oQ rX) nL(hA jK jR kP rB rC) jV(Ly Mf Mu Mv Nj Nk) kF(mP mS mY nN nT rB) nO(hA kP mZ rC) hV(jQ jR mS nJ) rX(jT kP lY mZ) Li(Js lM Nn) hW(aA Fr Mj) oQ(jH lM nK) Aa(It Jn) Ma(hA qY) Ip(jT qY) mI(lK nN) mW(jH lK) nD(kK rB) jE(Ly Qc) qW(jQ jR) jU(Mf Mv) MjPe MyOy MzHw NijO NjqU IlPf OmOn mZqT} nJ{Wd(aJ aP aQ Ar aV aZ bA bB bO cU dD Et Ex Fw hB Hv Ij In Ji Jl Jn Jq Js KE kI Kk Kq Kx Ky Ld Lh Li Lv Lz Mj Ml Mp Mq Mx Mz Nw Oa oF Oh ON Or Ou Ow Pe Pf Pg Po Qa Qb Qd Qe Qx Rg Uh Ut) Vi(Af aJ aN aP As aU aV Aw Ba bB bF bM Bn bO bP bZ cG Co cS DD dG dI dL Dr Ex Ez Fn Hc hG Hu Hv Iq Jf Ji Jn Js Ke Ld Lh Lv Ma Mj My Nw Oh Ou Pe Pf Pg Po Qa Qd Qn Uo Uv Vp Vv Yd Yh) Ps(Aa aC AO As Aw bQ Co DD Eq Ex Ez fP Hb Hq Ib Jd Jh Jq Lx Mj Mn Nw Nx Ny Ok oN Ou) Rz(aZ Fn Hq Hv Jn Mj Pg Qa Qb Qd Qe Qx Rg Uh Vt) Eq(aZ Hv Jn Qa Qb Qd Qe Qx Rg Ut Vu) Xa(cU Hq Kk Lx oF Pf Pg Qa Qb Qd Qe) We(aP Jn Lx Mq Oh Om Ow Pf Po Qa) Wf(aQ dR Js Ld Lh Lx Oh Ou Ow Qa) Qa(Gn Op Sj Yd Yh Yk Zx) Rv(Co eM Ez Jd Lx Nv Ut) Vj(As Ct Ez Mj Pg Vp Yh) Dr(Cu Jl Kq Tn Ut) Va(Cu Jq Ou Tn Ua) Vz(Jl Kq Nv Nw) Qd(Op Sj Yh Yk) Vw(Jq Lx Mj Ou) Pf(Rt Ru Sf Yh) Ua(Hp Lp Tl) Tn(Lp Wc Zw) Zx(aO Ut Vv) Om(Sf Sh Wc) On(Vh Wc Yf) Pg(Aa Fi Gn) lN(aA Mj oQ) Aw(Sf Sh) Mw(jM qY) Hq(Lp Zw) Yd(gL Qu) Ut(Gn Yk) CuRx YfJs EzVb FdNv NnRu LxjG HbKq SjgC JqjM RtoQ aAhV} oW{cT(Al Ar As Ax Bc cM Cs dM Fa Fp FR Gn Ha Hp Ii Ij Im Jk Jm Jq Js Jt Li Lj Ma MM Mw Nm NN Nv Ny Oa Oh Om oQ Qa Qc Rm Ry Si Vt Zw) Lj(aF aO BA bV Fw Fy hC Iv Jn Kq Kx Ld Lv Mj Mx Oa oE oF Oh Ou Pg Qh Qn Rf Ri Tr Tv Ua Ut Vs) Nn(BA bF Cp dF eM Ez Hq Hu Ib Jd Ke Lh Mu Mv Om On Ou Pb Sj Ua Ut Vs Vv Yk) Vs(Aa Al Bb Fb Ha Ii Jj Jk Jm Jq Kn Li Mm Ny Oa Oh Om Pc Qb Qc Qe Rm) Mm(Ao BA bF bV Ct Cu dF Hc Kf Lh Ok On Oz Pb Pg Sj Tt Ua Vv) bA(Al Ar Ax cM Cs dM Fp Gn Ha Hp Im Jm Lh Li Ma mE Ny Oa Pc) Pc(Aw Ba bF Gn Ha Hq Hr Ib Ou Sh Sj Yd Yk Zx) Yk(Ad aF Bb bF cQ Gc Jj Ju Ko Nm Ny Sf) Ou(Al Jm Oz Pb Qb Qc Qe Qh Rm Uh Vt) Vv(Ax Fp Ha Kn Ks Nm Nv Oa Oh Qd Qe) Pb(aO Cv Ha Kn Lp Oa Sf Ug Tm) aF(cF Ed Gn Hc Ib mE nN Sh Zx) Ua(Al Fb Jk Kn Li Nv Oh Rm) Oz(aO bF Fy Ha Kn Oa Sf) aO(Ed Gn Ha nN Ny Oa) Al(Gl Hq Jk Pg Qh) Fp(Rf Rh Ri Tr) Hq(Jk Om Sf Zx) Sj(Bb cJ Mn Ny) bF(Bb nN Qc Uk) Ha(Jl Lx Pg) Hc(Ap Jg Li) Gn(dH Hv) Nm(cG Yh) Tr(cL Qe) Sh(hC Jv) Xa(Ap Iz) Ny(dF Nv) AxPo BaMw LxQe ToOw TnJy TvJm SiPg ZxhC KnUt} eQ{Hc(Ad aF Al aO Ap aQ Ar aU Bb bF bR bV cA cD cF cM cQ cS Ct cU Cw dA Dg Dl dN eM Fb Fp Fr Gd Iz Jg Jo Jt Kf Kl Ko Kx Li Lj Lp lY Mf Mm Nm Nn Of Og Oh oN Oz Pb Pc Pj Pz Qg Rc Ss Ug Um Ur Uu) Xa(aF Al Ap Bg bO cF Cw Dc Dg Dl Fa Gc Gd HB Ih Il Iz jB Jk Jt Ke Kf Kl Kp Kq Lp Mh Mv Nf Nt Nv Op Oz Pa Pc Pj Rx Wb) Tn(Ad aF Ao Ar bF cQ Cw Dl Hw Hx Ih It Iu Jg Kf Kl Ko Kz Lu Ma Ne Nk Nm Nn Pa Pc Pz Qh Qm Rf Ss St Uf Uu Vo) cT(Al aR aU aX bC cL cM cS Cx dM Gh Io Jm KC Ld Lp mZ Nb Ni Oa Rf Rx tF) Uf(Aa Ad bF Cw Dg Dl Hb Io It Jg Kf Kl Nm Pc Pj Qh Qm Rc) Pc(bF bQ Ef Eq Jd Kg Kj Qu Sj Ua Ut Vs Vv) Cu(Dg Gc Hb Jt Nm Pj Rm Ry St Vt Wb) Lp(aU Aw BA bQ bV dR Gl On Pg) bF(aX fA Ju kC nD Qx Ra Rh Sh Wm) Ld(aU bA Ha Ip Mm Ny Un Vt tF) Mg(Hb Jy Kf Qg Ss Ug) kC(bA Ou Pb Pg Ua Vs) Hb(bV bZ Kq On Ut) bQ(Hp Kz Oa Ry Sf) Al(bA Qu Rm Tt) Nm(Nt On Rz) Yh(aQ dR Gp) bA(cS Jm tF) Ba(cD Fa) Ct(Fa Gh) Mv(Jy Qw) Rz(Iz Ko) Ow(Ih Iu) aO(Gh Nb) bZ(Qe Tl) DcVv EzcF NtaF MaJy HpbV HqSf TtJm TreM RbiO LjfA RhPb} mE{Qu(Ad Al Ap aU Bb Cv Dg Dp eC Gn Hp Hr Hw Ii Iz Jj Jo Jt Kg Kj Lp Lv Lz Mb Mm Mp mT Nm Nn Of Pk Qd Qz Rb Ss Uc Ug Um Ur Ux Vb Wb Yf) Qd(aL aO aQ aS Aw bA bF bV bW cF cS dF Di eC Gn Hb Hc Ub Un Vi Vt Vz tF) Ut(Ao Dp Gc Hr Ii Jd Je Jj Lp Ly Mk My Nx Om Oy Qx Qz Rx Uk Um We Tj) Mu(aC Aj Al Bb cU Cv Ed Fw Gd hC Iz Kg Kj Ue Ug Um Vb Vi) Kq(Ad Ap Bb cF Cv Dc Hb Jj Jo Nm Nn Ny Ok Pj Un Vh Ti) Mv(Ao cF Co Hp jM Ju Kd Ps Um Vb Wb Ye Yf) Nv(Gn Hp Lp Rt Rx Si Ux Vz Wb We Zq) Um(Hq Jd Jh Mw My Nn Nq Om On Tn Yh) Ua(cS Jj Lp Mb Og Rt Rx Ug Va Vi) Mw(Gn hA jF jM Lp qY Sf Ur Vi) Ef(Ad Bb Eq Iz Lp Ux Vb) Qa(Ax cF Cs Fa Gn Oa Vz) Jd(Gn Hp Rx Ry Ux Vz Wb) Co(Hp Rt Rx Ux Vb We) Nq(Du Gc Gh hA jM rA) Rz(Ed Fw hC Hv Nb Nm) gL(Gn Hp Rb Ux Vb Xa) Tn(Dp Ly Rx Va Wb) Jh(Ps Sf Ux Wb Ye) oQ(hA hR hV iB jH) Nn(Ap jM Tj Yf) Hq(Ru Vj Vz Ye) Hu(Gd Gn Lp Ye) Mp(iB lM qV) Om(Rx Vz Yd) Vi(Hv My Qy) Pg(cF Vh Wc) Fw(Mm Nm) Mj(jM rA) Jk(Lp Rt) Ps(dA My) Vu(Cv Jm) Vv(Vb Wc) AwmF DrbZ NmMa MxjM WfcL QyLp NylK UfgC VaVs cFpH nNhR} kE{Wd(Aa aF Al aO aZ bA Bb bF bW bZ cL cM cT cV dF Fb Gp hC Hp Hw Ib iO Iz Jl Kn Lh Lp Lv Ma Mm Mn Mp mT Mz nC Ni nL Oh Om Ow Pa Pg Pi Ps Qn Ri Si Ss Tn Ux Vb Vp Vv We) Xa(Aa aF aQ Ar aU Bb bF cF cM Cs cY dR Du Fb Fy Gn Hb Hc Hp Ib Ks Kx Lh Li Lj Mm Mn Mz Nb Ng Nm Nn Ny Oh Oi Ow Oy Oz Pb Pc Rx Ry To Tr Vu We Zq Tj Yf) Rz(aF aK Ap aU bA Bb bF bW cM Cw cX Fb Fy Hp Hv Iz Jg Li Lj Mm mT Mz Nk Nm Nn Ny Pc Pj Ri Ug Uu Vp Vs Vw) Ps(bF cF cL Cs cY Fp Hb Hu Jh Lj Mv My Ng Oy Oz) Aw(aE Al Fb Hp Ju Lh Mm Mn Nm Nn Pb Pc Vb) Ua(Al Em Gn Hp Lp Pc Sf Si Ux Vb We Ye) Cp(Gd Hp Mm Sf Si Ux Vb We Zq) Om(Gc Hp Rx Ry Si Ux Vb Vz Zq) Vs(Hp Rt Rx Sf Sh Si Va We Yk) Yh(aK cF cY Gn Pb Ri Um) Zq(Ba bQ dF Jh Nv Tn Vv) Pb(Fy Ou Vj Yd Zx Ye) Gn(Ct Hu Mu Oz Pi) Eq(cF Oz Pc Ri) Hp(Hu Jk Mv My) Vz(Cu Ez Hq Ma) Uf(Aa Jt Nm Pj) Vb(Ct Ef Hu Ng) Ux(Ef Mv Ng Vv) bF(Ho Rx Wf Ye) Dr(Cu Ez Ma) jG(Mz Nv On) We(Co Ef) Vi(iO Oy) Oz(Fy Vj) BaGh YfNg MwjT MziC HqYe SfJk WcRi WfcL aEcF} Vb{Hc(aA aJ aM aP aZ cF Cu De dG dM Ed Fy Ho Hq Hv Iv Jl Js Ju kF Ml Ml mT nC nL nT Nw Oa Pg Ps Qd Qe Qn Sf Ub Va Vs Vu Vw Wb Xa) kF(Ao Aw Ba Bg Cp Dk Ef Eq Hu Iz Jk Kf Kl Lx Mu Mw My Nq Om Pf Pg Pz Qt Qw Qz Ua Vi Vs Vu Wd) oQ(Aw Co Cp Di Eq Hu Iz Kf Kg Kj Mg Mu My Ou Pg Ua We Yh) Cu(Aa cF Dr Hb Kq Ks Lh Mm Mz Ny Oh Ok Ow Pj Uh) nD(Aw Ba bF Bg Eq Hu Kf Mg Nv Om Ps Ua Uf Vs Wd) kO(Aw bZ Cp Hu Iz Mg Mu My Nq Om Ou Ua Uf Wd) kC(Aw Bg Cp Ef Iz Mg Nq Om Ou Pf Pg Uv) nC(Ao Aw Bg Ez Iz Kf Kl Pz Uc Yh) eM(Ih Ij Im It Jn Nq Pc Ps Rm) mT(bF CT Ez Kf Vi Vs Vv Xa) nK(Bg Cp Ef Eq Om Ua Ut Wd) Ef(kI mI mM mP nO nT) Ua(aJ aP mM oF Pc) Vv(kI kP lX mH Qy) nN(Ez Kq Ma Nn Qu) mY(Nw Oh Pf Ps Qa) On(Aa cF Mz Pb) mF(Aw Ma Mg Ng) mM(Co Mu Qt Wd) mZ(Ng Pf Ps Pz) nB(Ba Jl Ps Xa) kK(Iz Mv Qt Qu) Vw(mH mI nA) nT(cS Ut Wd) mP(Bg Pz Vi) mW(Nq Ps Xa) kI(Ct Eq Ou) oF(Hq Hu Wd) Mg(kP nA) Vs(Jh Qy) cF(Lx Pg) gL(mH mI) nO(Ao Yh) lX(aQ cY) nL(Bg Uc) DkHb NnmH OunA} hR{cF(aJ aK aM aO aP aQ aV bO cE cN Cq Ct cY dM ED Hr hV hW HX Ib Iu Jf Jm JO jR Jt JV Kc Kj Ld Li Lj lN Lu Ly Me Mq Ms Ng Oe Of Og Oy Oz Pg Qv Ra Rj Tv Ue Uk Um Uu) lN(aA aF aJ aO aP Bo bV Cv dE dK Fr iB In jD jH jO Ky Ld Lj lM Ly Mf mM Mu Mw Mx Nn Nq rY Vq) Ld(aA aJ aO bA Bo dF dG Gp JV Kc Ki Ly Md Me No Oz Qt Uv) Me(aJ aV aW Ax BC bW Cq Ct Ib Id Kc Kj Ky Kz Pk) rY(aA eD iB jD jH jO Lj lM Ly MM Mv nN Nx oQ qW) nT(aA hA hV iB iC jD jF jQ jR kP mH mM mZ oQ qW) Lj(aA Ly Md Mh Mu No Nv Qd Qe qW rX) mZ(aA jD jH lM mP mW mY nB nN oQ) rX(aA iB jD jO lM Mu Mx Nn Oh oQ) Bo(aW Bc eD Hq Id JV Li Oy) Ly(aW eD jO Ju lM Ml Nx Vq) iB(kP mY nA nB nC nK nN oQ) aA(eD kK kP Li lO lX Ni) mM(iC jF jQ jR lK mY rA) aO(Dg Ib Jv Ko Oy) jF(mP mW nN nO oQ) eD(aJ Gp In qW) kP(mW mY qV rB) Vq(jO Oz Qt) kK(nN oQ rB) lK(nA nK oQ) Gl(Hb Js) hA(mY nO) mW(jR mH) AajG HfJv aJjV nOjR mPiC mSrB jUoQ} wJ{Mz(Hv Hw Ii Ij In Ir Jh Jn Jo Jq Jt Lw Mi Mj Ml Mq Mr Mu Mv Mw Nb Nf Nm Nr Ny Of Om Oy Pb Pd Pe Po wL) Oh(Fp Hq Hu Ii Ip Iu Jg Jt Li Lj Ma Nm Ny Ok On Pc Pd Pe Pf Qd wH wL wQ) Iv(Hu Ii Ik Iu Jg Jm Jo Lj Lv Ly Mg Ng Nj Nm Nr Of Pd tS wH wL wP) Ih(Hu Ii Iu Jg Jm Jo Jt Ma Mp Ng Nm Nr Ny Pc Pd Pz wF wH wL wP) Mp(Hu Il Ir It Jg Li Lj Ma Mg Mm Mx Ne Ng Nm Of Pf wF wL) Iu(Hx Il Io Ir It Ly Mx Ne Nh Nl Nt Nv On Pg Qa Qb Qd) Nm(Et Hv Hx Im In Ir It Jl Jn Jp Nv Nx Og On Pg Qb) wL(Hx Il Io Ip It Jl Jp Js Mj Mx Nt Nv On Pg Qd Qe) Hu(Ij Il Ir It Mj Mx Nn Nt Nv On Pg Qd Qe) Hx(Ii In Jo Jq Jt Na Ny Of Pd Pe) Of(Fr Hv Hw Ir Nn Nv Oe Oy Pa) Mx(Jg Jt Mr Nj Ny Pc wH wP) Ii(Ij Il Ir Nv On Pg Qa Qb) Mg(Ir Jl Nn Oe Og) Il(Jo Nr Ny Pc wH) It(Jg Jt Ny Pc wH) wF(Mm Nx Og Pg wD) Jt(Ij Js Nv Pg) Ng(Oe Og Oy) Ir(Jo Nr wH) Nv(Jg Ny Pc) Pa(Ma Mv Pd) Nj(Nh Nl) Qd(Ny Pc) Jp(Mm Og) Pd(Hv No) Pg(Jg Ny) NqMv NtwH LyJl HwPc} nC{Rv(aQ aU aV Aw Ba bB Co Cp cS Ct Cu Cv Di Ef Gl Hc Hu Hv Jh Jp Ke Li Lv Lx Mg Mk Mq Mt Mu Mv Mw My Ng Nq Nw Nx Om Ou Ow Pg Po Ps Qd Ql Qy Rz Tr Ua Uf Uv Vj Vu Wd Yd Yh Zx Xa)

Figure 32 Continued

Wd(aM aP bB bW cH Dp Fc Hb Hf Hp Ij In Iq Ji Jq Js Ke kI Kx Ld Lh Li Lv Lx Lz Mb Mh Mj Mk Ml Mp Mq Nq Nw Oh Or Ow Pe Pf Po Qa
Qb Qd Qe Ql Qx Rg Vt) Ps(Aa aQ aV Dd dI Dr Fc Hf Hq Iq Ji Jq kI Lz Mj Mk Ml Qx Rg Uo Yh Zx) Zx(aF Hv Qa Qd Qe Qt Tr Uc Uo Vh Vp
Vs Vu Vv) Yh(aZ Nm Qa Qb Qd Qv Qx Rg Rt Tv Uk Vi) lK(Fr iB Jl Js Lx Mu Mw Mz Nr Nv Ny) Wf(bB Lx Mq Nq Oh Ow Po) Vj(Aa Bo Ed
Fc Iq Ur Us) Gn(Hv Qa Qd Qe Qt Vu) Mz(iB jF jM jT jV qV) Fc(Pz Qd Qy Uf Ut) Gh(aQ cE Ou Ua Vs) Qx(Eq Rz Yd Yk Xa) lN(aA Fr Mj Nq
oQ) We(bB Lv Mk Po) Xa(Qb Qd Qg Rg) iB(Jj kK Ny Pd) Yk(Qa Qd Ut) Rz(Qb Rg Vt) Ru(Oh Ow Pf) Eq(Qb Qd) Hp(Rm Vu) Wb(Qy Vu)
Sf(Ou Pf) Vi(cI Uo) Pg(Fd Fi) EfVw YfOh TrOp HcTm YdQa OnlM} kK{jF(aA Fr Hq Hu Jk Jl Lh Ly Mf Mg Mj Mm Mp Mv mW Mx My Nb
Ng Nn Nv Om On oQ Po Qa) Mu(Fr Hr Ii Jj Jk Jm JO Jt Lh lY Mb Mm Mn Nm Nn Nu Ny Of Qd qT) Mv(jE Jj Jm Jo jT jY lK lN Mb Mm My
Nm Nn Nu Og Oy Pc Qd qV Rx) Mw(iC jE jG JT jV lK lN Mm Nm Of qV) Nn(iC Iu jD jG Jm Jt jU jV Mm Nm qV) Hc(Ad Of Rt Rx Ug Um
Ux Va Vh Vw) iC(Fr iB Jl Mj Mz Nq Nv Ny On Pg) jE(aA Fr Jl Mj Mp Nb Nq Nv Ny On) lK(Hq Im Jh Ma Mt Nb Ny Pf Pg Po) jG(Fr Jl Lx Nq
Nv Ny On Pg Qa) Jk(Jj Jm jT jV Nm Of Qd Rt) lM(aA Mj Mp Mx Nq Nv Ny oQ) Wd(Bb bW Gp Hp Ib Mb Mk) qV(Hq Nq Nv Ny Oh Pg Po)
jV(Fr Jl Mj Mz Nq Nv On) hA(Hu Im Mf Nc Ni Qa) Nm(Nq Pg Qu Uf Yh) Rx(Hq Jh Qt Rz Ua) iB(Jj jY Mf mW Nj) Hu(Jj lN Pc Qd) Qu(aU
Hp Mm Ny) jT(Hq Nv Ny Pg) Yh(Qv Qw Ug) Ut(Fp Nv Ny) jU(Fr Jl oQ) lN(Mf Mx oQ) Nq(jP Mm) Mj(jD jO) Nb(jY Vz) Hq(jH Ru) Zx(Qt
Ri) Pf(Gd Ux) iO(Rb Rv) jL(aA oQ) CuZq WmGn EmQw FaTn MfjM HpQt UaRt TvRz QarA WfaU} nL{Rv(AO aQ aU aV Aw aX Ba bB bF
Bg bH bZ cE Ch cL CO Cp cS cT Cu cY dA dF Di Dk dR Ef eM Eq Ex Ez Fr Fw Fy Gl Hc Hu Iz Jd Jh Jk Jl Jn Jp Jq Jy Kq Ky Lh Li Lx Ma
Mg Mk Mq MT Mu Mv Mw My Nb Ng Nn Nq Nv Nw Nx oE Oh Om On Ou Ow Pf Pg Po Ps Pz Qa Qd Qh Ql Qu Qw Qy Ri Rz Tr Ua Uf Vi
Vj Vs Vu Wd Yd Yh Zx Xa) Wd(aV bB Dd Dp Hf Hp In Ji Jq kI Lh Lv Lz Mb Mh Mj Mk Ml Mp Nq Nw Or Pf Qb Qd Qx Rg Uo) Zx(aF aQ
bA hC Hv Ju Ps Qa Qd Qt Qx Uc Uo Us Vp Vs Vu Vv) Wf(aQ aU dR Js Lh Lv Lx Mq Nq Oh Ow Pf) lK(Fr iB Jh Jl Js Lx Mw Mz Nr Nv Ny
On) lN(aA Fr Mj Mz Nq Nv Om On oQ) Gn(Mj Qt Tv Ut Vp Vu) Ps(dI Fc Hc In Lv Mj) Mz(jF jT jV qV) Yh(aZ Nm Uk Vi) Rz(Qb Qx Rg Vt)
Eq(Qb Qd Qx) Fc(Qa Qd Vi) Nq(Gc Hp Sf) Vw(Cu Ef On) Pg(Fd Fi Gd) Cv(Kq Mu) Hc(Ux Tm) Yd(Qt Qx) Wb(Jh Jl) Sf(Dk Ou) iB(Jj Pd)
AaVj AlQu DrJl LvWe MjVz SiJn ZqOn XaaF KqKs RuPf OmUx OuVa VidI} wL{Ih(Hq Hu Iu Jg Jk Jl Jt Li Lx Ly Lz Ma Mj Mm Mq Mr Mt
Nj Nl No Nq Nr Nu Nw Ny Og Ok Oy Pc Pd Pe Pf Po Qa Qd wH wK wQ yD) Og(Hw Hx Il Ip Ir It Jg Js Ly Mg Mm Mx Mz Ng Nj Nm Nu Nv
Of Oh Oi Oy Pa Qb tU wF) Mz(Jg Jt Li Ly-Ma Mj Mq Mr Mv Mw Nj Nm No Nr Nu Of Pd Pe Pf Qa tN wD wF) Nj(Hv Hx Il Io Ir It Iv Js Mm
Mx Ne Nh Nl Nt Nx Oh Qd Qe wC wD wF yD) Ly(Hw Ip Iv Ji Mm Ne Nh Nl Nq Nx Oh Pg tS wC wD wF yD) Nu(Hw Il It Iv Mm Mx Ne Nh
Nx Of wC wD wF yD) Hx(Hq Jg Ma Mm Mr Mt Ny Pc Pd tN wK yD) Oh(Hu Iu Ma Mr Mt Nr Nw Pd Pf tN wK wQ) Il(Hq Jg Jk Ma Mr Nm
On Oy Pd wK yD) It(Hu Ip Jg Ma Mr Ny Pc tN wK wQ) Iv(Hu Jg Ma Nm Of Pd tN wK wQ yD) Ip(Mm Mu Nm Of Oy Pd Pf) Ma(Io Mj Nn Nv
Pa Pg) Pa(Hq Lx Mv Oy Pf) Pd(Im Ir Nx Pg wC) Mx(Na Pc tN wK) Js(Jg Pc tN wK) Nm(Im Pc wF) Nv(Hu Jg wK) Ir(Iu tN) MmPc HwwD
IoJg LjtN OytS} eD{iZ(Ar Ax Bc bG bH bQ cF Co Cq Cs Ef Fw Gp HA Hw IC Id Iq Iu Jd Je jF Jm JU Jv jY Kj Ko Kr Kz Ld Li Lj Me Mk Ns
Oa Ok Ou pF Qh Ra Rg Rh Rm Sr Tr Tv Uc Uf Um Un Uo Uv Vt Tj) Ky(aK aU Bo cF cT dI Gp hA Hb Hf Ic iJ iO Iu jG Jo Kd Kg Kn Ko Kr
Ld lM Lu Ly Me Nm Ns Nw nY Oh Ok Qx Ra Um Us) aJ(Ar Ax bA Bg bW Cs cT dG dH Gp Iu Ld pF Ra Um Uv) aA(Bg cF Gp Ic Id kQ kS
Ld Ly Ni Nj pF Um Uv Tj) nY(bH cF Cs Fp Jo JU Jv Kj Li Oy Ra Uv) Ic(cF Fr gL hG Jy Mu No Nw Qd Rf St Vs) gL(hA Hb Ko Ld pF Ra Rg
Uf) Uv(bC Bo Im Jo Kg Mu Ow) aP(Ar dH Gp pF Ra Um) cF(Bn qT qV qW qX rA) qZ(Mf Mu Mv Mx Nn Nq) dI(qT qU qV qX Vu) Ld(Md
Mt No Qd) Ar(Dk Fr Qd) Bg(Jo Kg) De(Ra Tj) Fr(jG Jm) Nq(Ra Tj) Ma(kI rY) Me(bW pF) Mu(jG Jm) Rg(hG iH) Vu(Iu Qh) EfJo LymT QdpF
bCqT dHqV hAhG} Ua{Sh(aZ Bb bH cF cU Gh Gp Hc Hf Hp Ib iJ Jk Jo Kj Kn Ks Lp Lz Mb Mh Mk Mu Mz Nq Ns Of Oh Om Ow Oy Pc Rj
Rt Rv Rx Ry Si Tr Uo) Si(aJ aP Ar aZ bH Cs cU Ed Im In Ji Jj kI kO Lx Lz Mh Mk No Nq Nw Oa oF Oh On oQ Or Ou Ow Oy Pe Pf Qb Qd Ql
Qx Uh) Lp(aX bH bO Ch dI Eq Gd Hc Hv Ib kO nD oF Ow Qz Rc Uo Tl) Hp(aJ aP Ch CU Ed Iv kI kO Lz Mh nD oF oQ) Va(bH dI eM Hc Ib
kO Mu Oh Ou Ph Uo) Rt(bH bO cH Cu eM Fi Ib Jv kO Tj) Gd(aZ bO Gp Hc kO nK oF Oh Vz) Gh(aM Bb Jj Kj oE oF Oy) Ry(aM Ed Jv Lx
Mh Oh Ow) Vj(Mh Mm Nn Om Ow Rc) Sf(bH Gp Jo kI Mh) Jj(nF nN nO nT Yf) Ye(Ch Kj kO Mh Tr) Pc(Eq kI pH pI) kO(Gn Rx Ux Vh)
Al(fA jB kI) oQ(cT eC We) Yf(Kg Kj) Em(jB kI) Rx(aZ Oy) Ux(aP Uo) AapI AdVi ChRv FiKj LzmZ HoIb TofA YhkI UgmH UroD aUlX
eFgC iOjB} On{Vh(Aa Bb cF cV De Et Fb Gl Hb Hc Hp Ib Ih Ii Jl Jm Ke Kq Ks Kx Lh Li Ma Mm Mz Ng Nn Nr Nv Ny Oh Ok Om Ow Pj Qa
Qe Rc Rh Rm Ry Si St Tr Uh Um Un Uo Va) Si(Ad aZ Jo nA Rj Ul Um Uo Up Us) Hb(Dr Gn Rt Ru Uz Vi Wg Tl) Ks(Dr Du Gn Rt Uz Vi Wg
Tl) Aa(Du Gh Rx Ry Ux Vj Zw) Ad(Hp Rx Ry Va Vz Ye Xa) Ii(Iv Pg Uz Vi Vz Wg Tl) Pj(Dr Rx Uz Vi Vj Wg Tl) nT(iC jE jF jG lM Mm qY)
Jo(aA Iv Rx Ry Vz Wd) mH(iC jE jG qV qW qY) mP(jE jF Jt lM Mm Nm) mY(jE jF lM qV qY Rt) aA(Iv Jj Jt Of Oy) Du(cF Mm Ok Rc)
Gn(Kq mM Rc Uh) Zq(aZ Nf Um Uo) Ut(kF lX lY pI) Wg(Jm Kq Rc) Jt(Iv My Oy) Tl(cF Mz Ok) Ny(fA Uz Vi) Um(Hp Ry Ux) mM(Hp Sf
Wb) mS(jG lK lN) jE(mW nN nO) Nm(Ho Rx) Jj(Iv Mb) Kq(Uz Vi) nA(iB jF) CvRy DrUh NnfA MecF NfVa SfpI NvwK OpUs UfgZ nNlM
nOiC nBjF nFqY nKlK qVkP} Ps{eM(Bb Bc cH Dg Fb fP Gl hG Hp Hw Ib Io Jg Jp Kl Kn Ks Lh Ma Mb Mh Mk Mm Nn Nv Ny Oi Om Ow
Qu Rc Rt Rz Ss Tr Tv Ux Va Vw Wb) mH(Aa Al aN aP bO cS cW Dd Ez Gh Ib Jj Jm Ju Jv kC Ms nD Nn Pe Po Sf Si Uo Va Vz) Uo(Ap Gd
Hb Hv Ib Ih Ii Jo Nb Nh Ny Ow Pj Rc Rm Si Va) kI(Aa aF bF cF Hb Hq Ju Lj Lu Ny Oh Ow Pb Qb Si Vt Zq) Hb(aZ Dp Gp Lx Lz mS Nq Nw
Ou Qd Qy Uh Um) nD(aK Dd Dl Et Gd Ih Kn Lj Nk Si) Aa(aA aZ Dp iJ Ke kP mS Ql Vj) mW(Bb Dg Gd Jm Ny Ux Vw Wb) oQ(An cL Gn Ju
Lu Pj Sf Si) mS(cF Hq Lh Mn Ny Om Ow) lX(aK aU cY Qv Ug Va) Hc(Ad Jo Va Vo) nB(Gd Tr Va Wb) kC(aU In Nq Oi) Rc(Hu Mv Vv)
mY(Hp In Tv) kO(aK aU dR) Oi(kF lY) Um(Hv Si) Vv(Jo Ks) mM(cS Hq) nK(bO Gp) CunO IncF OwVu aFmT aUmF bWmP} Tn{gC(Ad Af
aO cS Cu Cx Dl eC eF Ez Hb Hu Ir Iu Iz Jd Jh Jt Kc Ke Kf Kz Lu Lv mM mT Mw Nj Nk Ou Ph Pj Pk Qc Qm Qz Sr St Ug Uu Vo) kI(Aa Al Ap
Ax cF dH Fa Fb Hb Ii It Ji Jo Jq Ks Lh Mm Mn Nk Nm Nn Nv Nw Oh Ok Pc Pj Vt) mT(Al bH bX Cv Cx dH Kd Kn Kq Mb Mp Mu NN Ok
Ph) pI(Aa Ad aO Ap Dl It Jt Kc mF Nn Ns Oh Ph Vo) nN(Jj Jo Mb Nk Nn Oi Rb Rx Ss) mS(Aa cF Hb Jq Nk Ok Pj Si Vh) oD(Ap Jt Kl Mn Oh
Pj Qh Uf) nA(Ap Dg fP Hb Ko Ok Wb) oQ(Aa bA cT Jm Nv Ti) nT(Ii Jo Nn Ss Vo) Gn(eM kF mH mM) Um(Hb Li Ny Rc) Vj(Aa Kq Mm
Ow) mP(Jo Mb Nk Ss) nF(Jm Ks Ny Ok) jB(aD In iO Kc) lX(Ap Nn Oh) mH(Lp Zq Zw) eM(Ou Zx) fR(Ks Nm) gZ(Hw Jy) nO(Ry Zw)
mM(Mb Rb) AaGc BbnB CvnK DcfA DgnD LvmF MaTl WbmZ RcVh WemI OikF} Ut{lY(Ao cF Co Dp Fa Fb Hr Ii Jd Je Jh Jk Jm Jq Ks Mb
Mk Mt My Nv Nx Ny Oe Oi Ok Om Oy Qd Qz Rc Rz Tv Uk Um Ux Vj Zq) kF(aV Ax Cs dA Dg Dp Fb Fp Ha Hw Ii Jg Jm Jt Kl Kn Ks Li Ma
Mb Mz Nn Nv Ny Oi Ok Om Pb Ss Tv) pI(Ad aO Ax Bb Fb Hb Jj Jt Ju Ke Kn Kq Li Mm Nj Nm Nn Oa Of Oh Ok Ou Ph Pj Qe Vo Vq) lX(Bb
Dd Hb Hp Io Jj Jt Kf Li Ma Mm Mn Nm Nn Nv Of Oh Ok Ow Pj Tr Uk) Si(aZ nA Nf Nw Ow Ul Um Uo Vu) mT(bP cS iO Ju Ni Nj Uk Xa)
mM(Aa Bb Dd dI Em Kd Pk) kC(aU Ha Kn Mb Oi Ou Ss) Lp(mH mI mP nK nN nO) nD(Aa Hb Nv Tr Ux) Wb(mI nA nK) We(mS nK nO)
eM(Wd Zx Xa) mF(aQ aU cY) Aa(Gc Yk) dI(Dr Vh) nO(Em Ry) kI(Jo Ti) DdmW YfOw YkRc JjfR RzmP OmnT VanN aUkP bOjG cToQ
eFgC iOjB} Qd{cF(Aa Ad Ax Bb bN cL Cs cU Dd Gp Hb Hr Ii Ij Iu Jj Jm Jo Jt Jv Ke kF Kj Ko Ks Lh Li Lj Lu lY Me Mm mY Ng nO Pj Qe
Ue Yh tF) Hb(aO Ba cB cY Em Gl Gn Gp Hc hG Hr Jp lN Lu LY Mv Oz Um Vj Yh Yk Yf) lY(aS Aw Bb bF bU cS Dd dF Di Hc Ou Qu Uf Uo
Vt Vz Yh) lN(Ap Ax Cs Dg Id Ke Kk Kn Ko Kr Ld pF Ph) dF(Dg Jt Ke Kq Lh Li Mm Nn Nw Oh) Lu(aU Ax aZ bN cB dJ Ha) Si(Ba Hc Hu Ng
Vu Vv Yk) Aa(aO aS bA cT Yk Xa) kF(aU bW eC Pj Un Vt) Gn(kI kP mM mY) Li(aO Ba cB cT) Ax(bA cB cL) Ub(fR mP nN) cT(mM mT
oQ) gC(bA Fy Hc) mY(Hp Lp Va) jG(bO kP mZ) jM(mP nA nT) jV(Bo iO Ko) kC(Aw bF Zx) Ba(Ad mT) Mm(aO eM) Id(jH lM) aU(lX Me)

Vs) Ny(Ba bF cE CT dF Dk Ez Gl Lv Om Pg Tr Vs) Lj(Dc eC Jl Jn Ke Mf Mj Mz Nw oF Oh Pg Tr) Ax(cV Dc Jl Jq Lv Mj Mz Nw oF Oh Oy Pg) Mm(aQ dJ Pg Tr Uc Uv Vs) Uf(Ad Fr Jt No) bF(cD cM Mw No) Tr(Ha Oh Qe) Ou(Li Ma To) cM(aF bA cT) Al(Fw Qu) Fp(Pg Uv) Pb(Qy tF) QwiO RmOm QmVs PePg} kI{Rz(aF Ap Bb Cw Gc hC Iz Jg Mm Nm Nn Ny Oz Pb Pc Pj Pz Ug Uu Vw) Ou(cF Gc Gd Gn Ju Rt Sf Sh To Ux Vz Zq Zx) Wd(bA bF cW hC Jv Mm nW Pc Pi) Qu(Al Em Hp lY Mm Pc) Ct(Gh Hp Sf Va) Eq(hC Oz Pc Ri) jG(Fr Jl Mz Nv) Sf(Cp Cq Vs) Rt(bF Lh Om) Dr(Ez Ma) Lx(Ax Gn) Hq(Gd Yf) Uf(Pc Pj) bF(Wf Ye) lK(Jk Mu) DuQt FyPb LvWe MaJo ShVs ZqJl RvRi NvqV VuPc} cF{Lx(Cs Du Em Li Pe Ru Sf Vh Tl Ti) Nw(cU Du Hb Jt Lu Sf Si Vz Tl) nO(Dk Lv Mj Mv Or Ou Pf) Tl(Hq Hv Jl Jq Nb Pg) aZ(aJ aP Lu Lv Po Ye) lY(Kq Ky Mj Mq Pg Qa) Yk(aM aP Ju Sf) Du(Dk Jl Oa) Jo(Ji Pg Po) Mz(Ad Um) Hv(Uz Wg) Sf(Ou Vu) Jq(Uz Wg) Ky(jG tF) Or(kF tF) aP(dG dH) mM(Ez Mv) DlIm PoJj FwnK LuJi MjkF MqmW HbOh JvhX RvVu OukC PgmS aMlO} nA{iB(It jD Ji Jj Jq kC Lx Ly Lz Ma Mq Mw Mx Nh Nq Nw Ny Pd Pe Qc) hA(Jq Ly Lz Ml Mq Nc Ni Nx Om Pa) jF(Fr Hq Ma Mg Mm Mz Om) jM(Hq Jp Jq Lv Ma Om Pf) Gn(aU dR Hv Lx Ou) jR(Jq Ma Mj Nv Oh) Hq(Gd Lp Zw) Ou(Sh Ux Yd) bF(Rt Rx Zx) dR(Gh Hp Ry) Zq(Js Lh) Kq(Hb Si) AlQa MaJt HpaQ JqrA LpUv RvRi RuPf RtOm VjaF} nK{lK(aA Fr Hq Hw Hx Im Iq Jh Jk Jl Jn Js Lu Lx Ly Ma Mp Mt Mu Mv Mz Nf Nn Nq Nr Nv Nw Ny Oh Pb Pe Pg Po Qa Qc) Nn(Ap Cv Hp Ry Vz Tj) cS(Cv Fw Lx Nm Ou) Qu(eC Jj Ur) Kq(Bb Cv Ny) iB(Lx Mt Nt) Fi(Hq Pg) Fw(Mm Nm) Mj(Dr qY) Mp(jT qV) Vz(bZ Ow) Om(jM Ux) AlQa AxPc FrjG FyaV GdHq GnVp MwqY MxhA ZqPf JoUf JuPg aArY} Si{aZ(Ao Co cS Dk Ef Fr Fw Hu Im Iz Mg Mu Mv My Ng Nq Nt Nw Ql Wd) Nw(De Hu Jh Ng Pz Qw Qy Ub Vu Vz Wd Th) Vu(Ex Jq Ke Lh Oh Ou Pg Ub Vj) Ou(kC nD Qy Ub Um) Ed(Hu Mv Ng Pz) Yk(cU Hv Nq Qa) Vj(Pa Pg Vp) Nq(bA cT) Lx(Hu Mv) Qy(Oh Ow) Jn(mP mT) Pf(kF mZ) Pg(Cv kF) cU(Fw Hu) MlOw ImUm KqnN aQlX} Ly{yD(Fp Hw Ih Il It Iv Li Lj Mb Mg Mm Mv Mx Ng Nm Nt Nv Oh wF) jV(aJ aP BO Ct Fw iJ iO iZ Kg Kj Ky nY Or Ue) wC(Fp Iu Li Lj Ma Mm Mv) Ky(iC jF jG jM lO) wF(Li Nf Nq Pf wD) wK(Iu Lj Nx Oh) jF(lX mP mT nB) Id(iB jD) Li(wD wQ) jG(bO hA) ExlM MvwQ OrjU UmjO mFjM} Hb{Nw(Dr Du Gn pl Rt Ru Rv Ry Rz Um Uz Vh Vw Vz Wb Wc Wg Yk Tl Th) Yk(cU Ji Lx Nq Ou Ow Pf Qa Vj) aZ(Eq Gc Rz Vw Wb Wd Yd Zq) Vj(Jl Oh Pg Qh Vp Vu Wb) Um(Ji Jq Kq Mz Oh Qa) Gn(Dk Lx Oh Qa) Lx(Dr Em Ru) Wg(Jn Js Qa) Oh(Ru Vw Wd) Yf(Jq Ou) Ji(Hr Ul) Uz(Jn Js) ImRu} Hq{oF(Dr Gd Gn Ru Ry Uz Vh Wg Tl) Yf(Jo mW oH oN pF Tj) nD(Gd Lp qV Rx Ux Ye) mW(Gn Rv Va Ye Ti) kC(Gd Rx Sh Va Vj) pF(Gd Lp Ry Wg Tl) Mh(Sf Wc Ye) Tl(lY NB) mM(Rx Va We) qV(kP mH nB) kF(Gd Rx Va) Ed(Fd Vz) Ex(Ry Vh) Gn(nO pl) qY(kP mH) FinN Gdml HoJo SfbL WdeM RyhC LplY UmmP} pl{Pc(Aw Eq Gl Iz Kc Ou Rz Sj Vs) Sf(Aw bA Cp Fw Oz Pa Pb Yk) cT(cS dN Io Ju Kc Lp Rf Rx) Ju(Aw bA Cq Ou Pa Pg) Ld(Nn Oz Pb Qe Sr Vt) Uf(aO Dl It Jj Ou Vo) Fy(Oz Pb Qb Vt) Lp(bA Gl Pg) aO(Kc Kf Nb) Aw(bU Jv) Rz(Hv Jg) NmKq NsTr UbbC ShJv ZwPb KcbA NyaQ OuOz aUbU} mH{Sf(Fw Ih Jn Js Mv Nn Pf Qt Qu Rm) Rz(Cv hC Rj Ug Uo Ux Va) Wf(bZ Ez Ma Ow Pf) Om(jF jM lK qV qY) Gn(aJ Mq Pe Qa) Wd(aP Mv oN) Jn(Rx Vj Zq) Dr(Js Pe) Mw(lK qY) Hp(gL Qa) Vz(Mq Qa) Sh(Ef Ng) Jl(Gh Rx) Pf(Gc Op) qV(Mp Oh) PoVw FdcS MuqY JhlK QuLp NvjG} lX{aQ(Dr Gc Gd Gn Hp Rt Rx Sf Va Wc Wf Yk) aU(Cv Gc Ib Ju Qw Sf Um Va Vz Wf) dR(Cv Dr Gh Gn Rt Rv Ry Sf Um Wf) cY(Gd Gh Gn Rt Rv Sf Va) Wd(bF hC Ug) Va(bF cE cL) jF(Mm Mp Mz) Rz(Ug Ux) Uv(Gn Lp) qY(Mj Nn) MmKq ZqbQ RtbF} jG{bO(aM bl Gl Jy Kf Ky Ne Oi Or Qc Ra Uk Um Up Uv) Ky(An bM Bo Ed Ld Lu pF Pj Rb Um) mS(Jl Ma Mj Mp Mu Mz Nn Nv) kP(Fr Jl Mq Mu Mw Nv Ny Pf) nN(Fr Jq Pf) hA(mF mW) mP(Lx Nw) oE(Vu Ti) BciZ PoUc FrnO MamW MjnD} gC{eF(Jf Qg Qt Qu Qy Ri Uc Uf Vq Vs Vu) Qz(bZ Ef Ez Ma Mg Mv Ng Nn Ow Pd) Ow(Dr Ny Qc Qh) cS(aU Tr Tv Uc) Qt(Kc Ny Oa) Qa(Ha Oa) Sr(Ld Ma) iO(Rb Um) CtRx DrEz FyLj MwRz HobA TrbC YkaQ SfPf KqNy UfPj OzbF} mP{jF(Fp Ji Jq Lx Mq Mt Mv Mw Nc Ng Ni Nl Om Pf) Gn(Hv Hx Mj Vp) Nw(jT lM qV qW) Nm(Mv Nq Nv) Om(jE jM lM) jR(Fp Im Qa) Lx(lM qV) Jj(Hu Jk) jE(Mw Mz) AlVu FiPg NqMm MaJo MjVz MqhA ZxhC JhlK WdbW JqlM RvRi PdiB} mF{Wd(Gp Lh Lx Mh Mk Nw Oh Ow) Ma(jF Jo Jt lK Nm) aU(Cv Ez Fy Gh Rz) Gn(aQ dR Lx) Mp(jF jR lM) Uf(Dg Jt Nm) lK(Mz Nw Oh) Gh(aQ dR) Lx(Ax Lj) bF(Rt Rx) MvUr HpaQ ItiB ZqdF JqjM LpUv RvRi OmjF OuVa aAjQ hAmS} mT{Jh(Hp Lp Rt Rx Sf Sh Ye Tl) Mv(Hp Sh Va Wd We Ye) Kq(Ax Jt Nn Pj Qe Vt) Rz(Jo Nc Nm Uk Uu) Ef(Eq Sh We) Nn(Ru Tj Th) Qu(Lp Nm Uk) Eq(Qa Qx) Gn(Mj Vp) Vz(Jd Mj) YfJd NqSf MpjF HuLp WdbO RvRi PdiB} kP{qV(aA hA Hx iB Jk Jq Js Ma Mj Mm Mp Mq Mv Mw Mz Nn Nq Nv Nw Nx Ny Oh Pf Pg) qW(Ma Mj Nv Nw Ny Pg) qY(Jq Mj Mu Mv) Gn(Jl Mj Vp) Mq(hA iB) GhdR MwlM ImhA YkaQ JliC NyjT aAjD} Hv{Yk(Ax bO cS Lu Lx Mh Mt Ni oF Pf Va) Vz(Kd Lw Oh Ow Ud Um Uo Wg) Rv(Kd Lw Ud Um Uo) Oh(Du Ru Rx Uz Wg) Du(Lx Ow) Eq(Mh Tr) Gn(Kd nD) Mv(Uz Wg) Pf(Uz Wg) NnRu ZxkC KdLp VaVu VjPa} nD{Ou(Du Gc Sf Sh Va Yd Zq) Mw(jF jT lK qV qY) Pg(Fd Fi Hp Zq Zx) lK(Jk Mj Nv Ny) Om(Gd Ux Vw) Eq(aQ aZ) Hp(aQ Vs) Zq(Nv Nw) Wd(aF In) aU(Gh Rv) qV(Mv Nq) GnaO ShVs ZxaF JjiB RzRh RtbF} nN{Kq(Gd Hp Lp Ux Va Vw) Va(bZ Ez Ld Ma Nv) Om(jE jF lM qV) Ma(Dr qV Rt) Jq(jE jF lM) Ez(Gd Ux) Gn(Pe Vp) Mz(jE jF) Ld(Dr Vz) Nw(qV qW) bZ(Gc Lt) BbWd FiPg GpRz NnSf NchA ZqPf ZxPc PdiB} kC{Ou(aQ bR Gc Op Rb Rx Sf Sh Ux Va Vz Yd Zq) Zq(Lv Mj Pf Pg) Zx(aQ aU bF Ug) Hp(aQ Pg Vu) Gd(Pf Pg) Wd(Lv Or) Ux(Nq Om) aU(Wf Yd) bF(Rt Rx) AxLx GhdR MaJt JjiB LpUv RvRi} kF{Mb(aL aQ aV bR cY) Zq(Lx Mj Nv Pf Pg) Hp(Lx Pg Vu) Ou(Gc Oz Pb) Pf(Gd Lt Ux) Al(Dk Vu) Dd(Fw Nb) Nm(Lx Wd) Nq(Mm Ux) Yk(aQ dR) AwMm BcKq GdPg MwUr NbLp JjJk JmVu RvRi RgPb UvVj} lM{Ex(As cW Gp Iq Jo Mb Nx Of Ra Rb Tr Tv Um Uo) Ky(cH Id Ko Ld Ok Oz Um) Id(aA aJ aP Bo Vu) mS(aA Mp Nn) nB(aA Jq Js) Mx(Bo Vs) TicH ThUr MamW TriZ JqmM} Jj{Pg(aA Ik Iv Jh Nt Nx Pe Pf) Jk(aA Iv mZ Nn nO Nt Oy) Nv(aA Ik Iv Mb Nt Nu) nO(Hu iB Mu Mv) aA(Lv Nt Nx) Yf(Hu Mv) mM(iB Rz) Eqml NtJl MxNx PzmZ lYiB} lY{Kq(Al Ax Bb Bc Cv Dd Ks Ny Ok Vz) Qa(Cs Fa Oa Vz) Qu(Al Lz Pb Qb) Pg(Op Rt Va Wc) Gh(Co Nq Om) Mu(Cv Dp) NnJm NqUm MjcS MvlK WbJd RziJ RvbF} mM{Kq(Ad aF bA cT Gn Jt Nm Nn Pj Qe) Gn(aJ Js Mq Nv Qa) Aw(Al Lz Oh) Jq(jE jF qV) Di(Mb Oh) Zq(Jl Nv) lK(aA Js) FdcS MqaF InRz SfJn NwqV} mS{lK(aA Jk Jl Ma Mj Mp Mt Mu My Mz Nn Nr Nv Oh Pe Pf Pg) Nn(jE qY) Rz(Ap Ug) Uf(Gc Pj) hA(aA Nc) iC(Jl Mz) qV(Nv Oh) NqjE WdhC} wK{Oh(Et Iu Ji Jt Li Mm Mr Nw Ok Qa) It(Iu Mr Ny Ok Pc) Iu(Il Ir Mx Nv) Ok(Hx Mx Mz Nv) Mm(Iv Mp) Nv(Jt Pc) NuLj HwJo IiPg wDwF} eM{Hp(Ih Jn Pe Qa Rm) Wd(aU aZ Lx Mj Oh) Vs(Lp Rt Rx Va) Mm(Ih Pe Qa) Jl(Rt Rx Zq) Ux(Ih Nq Om) Qa(Fa Zq) Jn(Rx Ry) Va(Om Rm) GpYe} Yk{Qa(Ih Lu Mz Oh Qb Qc Rc Rm) Mt(Jo Ma Mm Nn Oh Om Ow) Mh(Jh Mu) Mz(Jl Jn) Rc(Jl Jn) Va(Nv Ou) aJ(Oi Rx) NqJv LuOw NbJu} yD{Nu(Hw Hx Ih Il It Mx Nm Nv Oh) Nj(Hw Ih Il It Mx Nl Nv Oh) Nt(Il It Nv) Mm(Jp Oh) It(Jg Mr) LvIv IlIu LiOh} wF{wD(Lx Mc Mm Mp Nu Og tN tX) Hw(Jg Jl Mq Nr Pe Po) wC(Mp Nu tN tX) Og(Mm Mv Of) Mr(Il It) Ih(Lx Mp) NuPf MmNx} Hu{oF(Du fR Gd Gh Gn Hp Ry Vh We Tl) Ry(Ed Jl Lx Oa) Gd(cU Gp Oh) Ed(Hp Sf) Sh(cU Gp) Rx(aZ Fy) nMlK} mZ{Mz(jF jT jV lK qV) Pf(Op Ry Ux Zq) Mu(Lz Ml) Mx(iC jF) Va(Ou Vs) lK(Jh Mq) FwRv GdPg MwUr RzaF RtbF} aA{Lv(Hr Iv Jh Nl Nn Nt Nv) Hr(Jl Nv Po) Lj(Ji Nw Po) Jk(Ji Oy) mW(rX rY) MzNf IvJh PfPg mIrY} De{Gd(cA cT Oh Ow Pf) Lx(Dr Du Zq) Ky(hA iC jR) Ed(Gn Hp) AxDr YfNm MhWb NbTl ZwOh RaiB} Mv{Sh(Gp Mb Nf Rj Ry) Ed(Hp Ry Sf) Yf(Jo Kg Nm) Jo(Fd Ho) oF(Vh Tl) GhcN nBjF jUrY} Sf{Dk(Ad Id In Kd Kn Kr Pk Rj Um Uo Us) Pg(Cv iJ kQ) BgEd FwnO NbNl} Ou{Ub(Gn Rt Uz Vh Wg Ye) Va(An Cv Pa Ul Vt) Vw(Lh Mm Pj) Gcml UmaR} Nb{Tl(Md Nc Ne Nl Ns) Lp(Cv Du Ul Um) Yf(Bn Jm) Ry(Nv Uo) DdnB RvUm} Jl{Vz(Ad Cv Dr Kn) Ad(Eq Rz) Dr(Ib Rf) Hp(Kn nB) CvRy NfZq IvJm OhVj VanB} oE{Oz(Gh Rz Vj) qV(Ez iJ Je) rA(bC iJ) qT(aN Je) MyRy UmqX VsjH} Ky{Bo(jR jU jV) jD(iJ iO) jT(Oz Rb) ExjR IdjH KojP KrjL bPlK} nB{jF(Fr Iq Jq Mz Nq Om) Pf(Ux Vw Zq) qV(Jq Ny) LhVa} Hp{mI(gL Jn Nn Qu) Pg(Cv gL mW) Ed(Ng Pz) FbaZ VudM} Nv{Va(Kk Ul Uo Vh) Vz(Ad Jo) Lj(rX rY) NtJo MzTl LirY} nO{jE(Jq Mj Nq Ny) Dk(Al Cv) lK(iB Mz) NqUm LdRv OmjF} jV{Bo(aM Ed hX Im iZ) iO(aJ iZ nY Qt) JeiZ} Um{Li(Kq Oh Qa) Lj(Hx Oh Qa) CsLx WdoF JqVa} mW{Ma(jE jF jM Rv) DdFw MqlK MzjE

Figure 32 Continued

RvbF PdiB} Ow{Vj(Fy Pa Vu) Vw(Nw Pj) LuVz MlRx} ml{jF(Ma Om) YfNn EqPc ZqJn QuLp RvRi} oF{My(Du Ry Tl) Wd(Jo Uo) GhNg}
Hw{wD(Iu Jg Jo) wQ(Jt Nm)} Pg{Lp(aH kS pF) GnpF WdJo} cB{Im(Ax Dl Li) PoJo LuJi} Yf{BnNq JqVa KsOm NwUh} Mm{wC(Jp Nu)
RzNw VjPa} Mw{nF(jE qY) GdGp nMjE} Lj{Oa(Gn Vj) rY(jD Mx)} aZ{Ye(cS Lu) FrZq NgRx} Md{hV(Bc Ib Ld)} Vu{Rv(Ad Aw) DcjD} Pj{ImVz NwVw VjPa} Du{AwhC PokR} Ti{QcqU KcjT} Gh{MlPf NwkS} Mz{wH(Mr Pe)} Ho{NmLx InJn} Id{aJ(hX jP)} iO{PojU GljD} BoJvhX CoFdKo CtNqjD DkDrJu EdIbWd NnnFlK MlRxOh MyRyhC NjNlwQ TrhGjL ZqbWdF JqUoVa bCtFqT

Constrained panels with 3 analytes, where 4.3E-10 >= 'AUC p-value' > 1.0E-10. Contains 5,935 panels of 25,049,241 total panels evaluated. : oO{Ju(aP aV Ch cS eF fR hB Hr Ma On Qa Qt Tt Vs Vu Yj) Dd(bF fR Gn kF kN Lz mP Mx Nv Ou Pe Pi Qe Rm) Um(Fr Hu Iz Jy mM Mp Mu My nU Oy Pc Pd Tt Tz) Qv(Bg cD cS Ez Hc Jk nO Nv Ou Pg Qa Qu) Hc(aV cY Di hC Iz Kx lW lX Mk Uf) eF(aJ Al bA Is Kx Me Mh Pb Qg Uc) Cv(aL bC cG fR nA Nd nR oQ Ou) Ba(Al aP aX Dp fR Gz Kq mZ) Di(aA kF kG Lv Mh Pg Rh Wm) Nn(aV cL cN dG Fy Gc oF Qn) Ug(cL Co Fw hB Jk Nd Pi Qt) Aa(aZ cE cU dL gL Rm Wm) Ax(aA aQ cF cV mZ Pf Pg) aP(Hb Is kF Ms nD Oy Yk) bQ(Ap bV Ld Me Ni Nu Qa) bZ(cF Ch Hb Jj Jt Mk My) nR(Gn hC Hr Lz Ma Oh Pj) hG(aJ cF cL Cs Gn Ni Pf) Aw(Jd Jo Jr Nc Om Uc) aO(aM bN bR Pe Pf Ur) cE(Gn Jo Kx Ml Ur Yj) cG(Cs Jt Ko Ml Pc Pe) fR(bH Ct Hb hC nI Nm) Cu(aZ Jq Lh oE Pa) Ld(aV kE Pz Tt Uk) Rh(aF Bg Cq Gl oP) Ut(Ap Mk Om Oy Qx) bF(My Ni Nu Nx Oy) kG(cL Cp Dc dM hC) Cs(aV Ou Qa Uc) Ez(dJ Hu Mj Vu) Fy(Mp nU Qg Qy) Nq(Ad Ap Hb Rf) Lv(dG gL Vu Vz) Lz(aZ bA oE Yd) Kq(cN dR hC mP) Pg(aJ aU aX Hb) cF(aZ bA gL Lu) cT(dD Io Kj kN) eC(aD aS Jd mE) kF(aF Cx dM Gc) Bb(aU Jl Ua) Mj(aX Dr Gn) Ml(aF dD Ou) Tr(mT Nj nT) Yj(As Ef hB) Qa(cL Ha Ua) Qu(gZ lW Mp) Qt(bC Db Mp) Kd(Im Mv oF) cS(Qd Tv Uc) Ma(Ao Vu) Mq(Bo bU) Nb(Qz Tz) Nd(oE Ur) Hr(aF Ri) Is(bC dN) Rf(Mv Nv) Pf(aS dJ) aA(Bg Gl) aQ(Jl Mr) dD(Me Po) dG(Jo Jr) oQ(aS mZ) CtNm WmcB EmRg ExHb GcJs GnHx NraU MhOr MuJv NioF UcPc YknW WbNw KpoE UloW UfbR UroN UuUw VumU VsoV PiaJ aLdN aYbV bAcL bCfB nOiP hRiB} Yg{Ks(aP cF cX dJ Jn Jq Js Ld Lz Ml Mp Mq Nb nY Ps Ql) oF(An Aw bE Cp Ed eQ Fb Ii iJ Kn Ko Kx Li Ml Uf) Jr(Aa cG cS Hu Ih Jh Jt Kq Lu Om Pg Ry Un Zq) Gz(Aa aM dF Iz Ju Nm On Sf Va Yj) Or(Ii Ji Ke kG nI Ny Rf Rx Ry Sf) Kg(cA cK Hu Jh Mg Mp Mw Ow Rj) Ou(Ap Jt Kj Lh Mh nI Nm Nw Uf) aP(Dg dJ Kq Li Ng Ok Pj Uf Um) Rx(aN aR Cu Jl Nb Nm Ow Oy) Oh(Aj dF Ii Jn Ma mY Rf Ut) nI(dF kE Ko Lv Mj Rg Ur Yd) kG(Cv kE Ld Mu nH Nw Ok Pj) Ad(cA Gh Jh Ko Ql Tn Vv) Bb(Im Jj Jp Nv oE Rh Um) Nn(aA dL Jj Lx Mk Nv Ql) Mh(Bn cB Dk Mp Qd Ut Vp) Mm(aZ dF dH dM Lx Nq Qa) Tz(bQ dF Jt Ju Ke Ni Tr) aO(Bg Jh Mw Nm Oi Tr Xa) Ed(Al cF Dd Sr Tr Uy) Gd(cB cK Mp Ny Uy Tj) Mz(dJ dL iZ Jj kN Ko) Ii(bO Js Lx Nb Ow Pg) Is(cT Ih Jq Jt Ry Tr) Sh(De Hb Mb Pg Uy Yj) aZ(Cp Hv Ko Ma Sf Uy) dM(bO dA Mt My Ok Rz) hC(Fd Gh Lp mP Ne Rt) Cu(aS Dg Nb Om Ua) Qa(Li Lj Lu Ow Qd) On(bI cN De Dr St) aJ(Hp Jf Kq Uw Uy) kI(cY Ib Rj Uo Xa) Yi(cC dG Ko Lh) Oi(iJ oE oN Yj) Va(Bn Jq Mp Vu) dF(Hu Kl My Tr) iZ(bO Jt Ma Ow) Sf(cR Hc iJ) Jl(Ma nB Ok) Jo(cS Mp Mv) Lh(cU Ok Op) Uo(cN mS Uu) Oy(cF Hb Pb) mU(Jk Ur Vp) kN(Fy Kl Ld) Dl(kO nR) Mq(Pj Si) Nb(cX Yj) Hv(Jn Ld) Jt(Fw Pg) Jv(mH Ml) Ko(aV oE) Om(Lx Pg) Ow(Fn Pe) bA(Jh Nv) bO(Ap dJ) cC(Hp Ib) cF(dL Ph) dG(Nm Ry) lW(Kf Ur) mS(Ri Rj) nY(Si Xa) DckE ExNy GhoE GbUu LvTr MwcT UaaM InIv HbdJ HcKl JuiJ KknJ RfQl PenH cNcU cWmH} Nd{Tl(cN Cq cS dF Em Fd Fi hC Me Mh Mu No Og Ow Qe Ql Rb Rz Yj) Ru(Fr Il Mp Nl Nt Nu Pz Qb Qx Ra Ub Vi Wm) Yl(Aw bP Cu De dG Hu Iv Jr Mj Mv Ow Po Rh) Du(cG cN Co dM Ef Hc Ho Ih Jh Mu Ne Tj) Ry(Aw Ax cG dF Ef Ex Mi Mx Nw Ps Ql Tj) Gb(Ax aZ Dk Fr Fw Fy Ha mP Mu nL Nn) Yi(Fr hC Hr Ic Jm Ld Ly nI Nk Nt Nw) Si(Aw Ax Gp Iv Li Mi Mj Mq No Po Pz) Uy(aZ Ez Im Jp Mt Nb Nv Or Qb Qt Uf) Lp(Ao bU bX Ez Gl Is Kz Mu nD Vs) Vb(Aw Im Ld Nq Nv Nx Qe Ql Rz Vw) Yj(cF Dk Fi Fp Jf Ld Lt Mq Vu) Qd(Fn Hf Kn Ko Ks lL Ul Us) Um(Fd Fw Gz Kc Ou Qy Rf Yf) Vi(Cq Cu Dr Fy Jd Mw Pk Vp) Xa(Ad Cq Cw Kr Pi Us Vp) Uo(Ex Gz Ly Po Qa Tn Yh) Uz(Ha Ij Li Nb No Oh Ou) Fd(Dd Ii Kn Rj Up Wc) Hl(aO De Ld Lu oF Qt) Qv(Is Ly oD Po Ut Vu) Uw(Fr Jd Kq My On Ql) Va(Gl Jk Lx Mp Of Wd) lL(aD Dp Fr Nv Nw qU) Hc(Gd nI nR Rx Sh) Wg(Ho Ld Mj Nb Vs) Rz(Bb Dp Gz Oi Ug) Vh(Cu Fi Jh Li Mw) jl(Bo Ir Mr Na Ra) Yh(aV Dp Ub Ug) Wb(Bb Bo Gz Ug) Wd(Gn Id Kq Kr) Ps(Kp Mk nY Vt) Rx(dI Iv Po Qt) Yf(iP Lv To) Ho(Aa Bo Rj) Tn(Dp Ii Of) Jo(Cu Eq Nt) mU(jP Vv Th) wL(Mu Of wH) Fi(Gp Kp) Gh(cG Jl) Mb(nU Tz) Me(cG De) Nj(aA gV) Hb(nR Nw) Is(cF Kr) Sf(bF Qw) Jf(aP dX) We(Ut Vp) Lt(kC kN) Rt(No Ou) wC(Li Pe) DrVp EzGz FrjG GcOw LxRv TzjV HuYe IrwJ ZqaJ PzgV JiaA StpH WcQl JuPg KmR KyiC OunO aOnI cSnK nUkG} Gb{Cu(aM Bn Dk dN Gz In Kc Ks Ml My Nb Ns Ps Rb Tv Vi Vj Vz Wc Ye Xa) Vu(aJ aO Ba Cp dI Fy Jg Jh Mq Mx Ny Ou Rv Tn Ua Vs Vw Yi) On(Bb Cp Ed Ml Mp Mv My Mz Nb Nm Nq Tz Ub Vp) Vv(Ao De gL Ji Ld Lh Mu Nb Qe Ut Uw Vi Wh Zx) Pg(aH aY aZ Gp Jo Ks Ld Lh Mw My Nw pF Wd Yl) Yi(Bb cB cS cU Ed iZ Ms Ng Nt Ow Sf) Nw(Co Hr Nq Pd Pz Qt Qw Tn Tz Uy Zx) Hq(aZ cN Fy Li Nt Pi Qn Ua Ut Yl) Im(aE dF Hc Hv Lx Oh Ou Ru Ul Um) Ps(aJ aM Aw cS Hv Nn Nu Rz Ub Vi) Tz(Bg Dk Fw Nb Rx Ub Vz Yl Zx) Is(Al bC Fw Jr Kc Mw Pz Uf) aZ(Bg Jg Jr Nq Nv Po Vw Wm) Ua(Ch Eq Lv Mp Mu Qb Ul) Hc(cB Fw Gz Ml Mv My Qh) Hu(bA dF Gp Ow Qe Yl) Jl(Gn Iz Ld Mi Nt Pb) nH(Ib Kf Ql Uv Vo Zx) Dk(Gn Mi Nn Yj Yl) Lx(Ao Hv Iz Je Kc) Mv(aA Ax dM Fw Tn) Jp(Co Mp Pd Ql Qy) mU(Ad Aj dA Hf Nb) Nq(Mx Oh Pa Vp) Yk(aJ Jn Pe Pf) Yj(Mw Nb nR Om) Jr(Gz Qa Qm Uc) nD(cL Ke Ld Lh) De(Ed Fy Oh) Ef(aJ mP Mx) Ml(Nb Pe Pf) My(cU nL Oa) Yh(dM Ed Vi) Qd(Ns Ok Zx) Js(Jd mT mY) Ba(kE nU) Nn(dM lW) Mu(Fd nL) Tn(bQ Ph) Kc(cT Oa) Kq(Um Uo) Oh(Ao Vw) Uf(aJ nA) mP(Mj Vi) nC(Aw Gl) kO(cL Ma) EdIz HaoP NtOu MiNv HvOw IbnU IvJd WbPf QaUo JhQh WdOa JknI NykG VjPa} nI{cU(Aa aL cF cN dD Di Fw Fy Jk kF Pg Ua) Vu(bC cF Hr Iu Ju kN Lu Mz Ok Pb tF) Aw(aC Dg Hb Iz Jd Jh kC Qa Qn Uk) Cv(aF aM bZ cT kK Lh nU Ok Qa Qh) Di(bZ cG dD Dg kG kN Mm nU Oh tF) Um(Ba De mU Oi pI Uf Wf Yi tF) Yh(aU bO dF Dk Jp kG mZ Nq) Yj(aV bO Ho Hw Lv mU nU Qw) Ky(bC bV dJ eM Nk Pg Rz Sj) Pi(dI Dr Gn Jl Lv Rg Rx Wb) Is(aF cF Dc Qu Rz Vt Yl) Yd(cT Hv kO Na Ng Pf Yi) tF(cN Dd dF Dk Lx nY Oa) Gn(aX Bn Eq Fn Lu nC) Tz(Cu Fr kN Mb Nm Qd) Ua(mF mZ nR Of Uk Ur) Vv(bG Dd Jo mU Nn Rc) aF(Ez kF kN Mv Qd Ql) bZ(Dd Dg Jo kF Nm Pj) Fw(aN Cu Mz Rz Th) Ju(Cq Jl Mu Ou Po) Kq(Kd Ma mE Pc Qn) Uf(kN MZ Nb Ug) cG(Bb cF Dg Jo Jt) dA(aA Cu Ez Jl Pe) Fy(aU Bb Lu Oz) Mv(Ap Kd Rc Uo) Lp(aV Co mU Rz) dF(cF Dd Qd Ug) nR(Hb Hl jH Nm) iB(nC Nh Nw Qa) Al(Jk Ma Ou) Dk(Rb Uo Vz) Nb(aO dD Qz) Qu(Bb Dg Dl) Xa(Hp Li Po) Vi(Ex Fb Us) bF(Jo kF Pc) cS(aO Ly Ou) eM(cV Mp Qa) Aa(Kc Qh) Bg(Sh Ug) Cu(Ng Ns) Dd(bQ Nq) Gd(Iz On) Ma(Fi Hb) Mu(aZ Ye) Mz(aX Yk) Vz(Oh Qn) Rz(bB bO) Yl(aV Jd) Pg(nU Vq) aU(nY Qn) bV(Jl Mj) cF(Lv Ql) kF(Dg Pj) BbNq CoNm DuEx EdHc PoaL EqUx FrUg GpWf LuQh LxHp TvoT IljI HbmU YikN YkoK SfJq SjnU WeoE QgpI JplL LddU LhqY NwjH OuPb VpPk cLnY} Yi{Nv(Cs Ed Em Fy It Jl Js Ld Li Mk Na Qx Rh) Mv(aP aX cN Cs dG dI dL Fd kG Mj Mx Qa) cF(Ad Ax dE Gd Hb In Kq nJ Nm Oi Rv Tr) Nb(Af bF cG Co dF Hu Jh Kq Mq Ng Vi) Ou(Ad bA Fy Hv Ih kG Lu Qa Rh Vv) Jh(cT Ed Fw Iv Oa oE Oh Ow Pg) Dk(Aa dJ Iv Lx Mz Nn oP Qx) Ua(aP cU Js Kj Ml On Pe Rh) Hu(aJ cU Iv mH Oh Pe Po Qa) Hc(aP Dg Gz Jj Ju Nw Oh Xa) Pg(aP cT Jo Lz Ml Mt Mw Mz) De(Aa Bb cN Hl Hq Ow Qa) Hb(bI Ed Jl Jo Oh Uh Uy) Tz(cB cS Js Mw Nw Qb) Vi(aV bU cB cC cN Dr) mU(Fr kN mH Mu Vw Yd) aO(Js Ks Lx Nm Ps) Bn(aP Mt Ow Qv) Jl(Na Nw Ql Wd) Jn(dJ My Of Wh) Jo(Hq Lu Mu nH) Kq(cN dM Fw Iv) kE(Ba Pc Qh To) Aa(cC Uh Uy) Po(eM nC nR) Gz(aV Hq Ks) Lv(nA nH Ny) Mt(cT Mj Yk) Mz(Ex Lh Nw) Ng(Lx Mj oF) Rc(Ef Om Ut) Jq(aM gL Ps) Js(dJ Mw My) Oh(Ml nU Ut) kG(Cq Dd Mq) kN(Al Nq Yd) oP(Ap aZ kS) Ad(Ef Wh) Lu(aZ Ks) Yh(Im oF) Qa(dJ Wc) Xa(Fw Lh) Lj(kI Qd) Rh(My Oz) Oi(nH Pb) Pj(cU Ke) cT(Fr Nq) mH(Cv Tr) mS(Pb Up) kC(bF Ug) oE(Om Ut) AwGd AxaJ BanU CphC DinR ExNn FykI GloQ LxYe MaHq MwbA TnKs TvnL IiLh PzNw PsOn RxdM RfVu QnoF VbnC UybO ValX dAlW} mU{Aa(aH cG cS cT Cu Dk Hx Jp Lx Lz Ma Ml Og Oh) Hp(Ao Aw Bg bU cE dI Dk iO Jk Lh Lx Nn

Figure 32 Continued

Qu(bP Cv) EfUk MwLp ZxhC WhbW JqUw} kO{Wd(Rg Rj) Rx(Jh My) Ri(Eq Rz) AwZq EfVw VzOw WhoE RvUv} Dk{Sf(Cv Dc Dr Mm Nf Pi Tv Wg) UgnO VjnJ} Hp{Ed(Aw Bg Iz My) mI(Im Js Pe) IteM JnmH bZnT} Gz{jO(bG cA Ex Oi) jD(cJ cU Il) bFhA cGjV} Nb{Du(aZ Bn cX Md) Lp(Ml Yf) BnRy RvVu NvVh} Im{cB(bV Jo Lu Ns) nT(jE jR) BnUw LuaZ PfPg} eQ{Ha(bQ cT) Uu(Ef Mg) NkUf TrbV TvkC QhbQ UriO} mH{Dr(Ez Ow) Gh(bZ dG) SfPe JsVj JuRz OmqT UwhC} nL{Cv(Ma Nn Qu) Zx(aU cY Jv) AlFw RviO rXoQ} wF{Og(Jg Mp Mw Nu Oy tX) NqIh NuNx ItyD} oD{Gd(cS Kq Ma) bC(Tr Uu) bF(To Ub) GcNn HabA} Jo{Nt(cB Pg) jO(Jy Uv) AwmF YfOm PocL MunO} Nv{Vh(cV Ny Rc) Wg(Ib Rc) AsVa RyoE UoUx} fA{Ar(bF dD) Ax(Ct Ip) Ny(Jq Mz) CtNn LjbR} nA{jR(Mp Ny) LxLj MnjF ZqdF JihA WhUg PfiB} oF{My(Gh Vb Vh We) Wd(An Of) IbTl TrjH} nN{jF(Ma Nc) DrOw EqGp NihA ZxPb qVkP} nD{Rv(aV cY) GhaQ IzVb WdOr WhUg JqUw} kI{AxPf CtRx EqaF MaJt QuPb JubF RzOf} Mm{FwhG NuyD QeeM JpwK OgwH VjPg} Uf{gZ(Iz Pz) mF(aU Uu) DdmM EmgC} nC{Vj(dI Wf) iB(It Iu) RzRh RveM} nJ{Lx(Eq Rz) AwTl RzOr VheM VuPc} kC{ThbB GcNq LxZw ZqdF ZxcY RtUv} nT{jE(My Nf) jM(In Jp) MuPc} lX{aU(Dd Uo) JpjF PjaQ dRfR} mS{lK(Mg Ng) EqRi MaqV hAmW} Bo{jV(aJ Mq Ql) KyjH} Ko{iZ(jQ qV) KyjH aOhA} Ow{BnYf UbRv SfgC VwaZ} Vu{JmmP JqVa LpcN UoUx} mF{jM(Mn Om) MplK PahA} nB{jF(Lx Ma Mn) EqbW} yD{Hx(Of Qa) LwMz NjIo} oE{Gh(Ng Pb) MfqV iCiZ} pI{Fy(aF Qh) QuaO QhcT} Aw{GdgL MamM TliZ} Dr{JnmM JskS PekR} Ml{EqMh GhaM RxPf} Tr{NygC bCoQ iOjB} Vb{NsPg MreM QlmW} Vj{UePa NyVp PcPg} aZ{LuMb NgVa NiNk} gZ{EmdR FwHa GciO} wK{MrMx IhIt NyPg} Cv{FyRx TojB} Po{JeqT mPjE} Hw{NjwD OmwQ} Vz{AxOa NwPj} Zq{dF(aJ dI)} Ky{BniC aNqT} Li{NuwC WdoQ} Pf{AlnF RygC} mW{QuUk hArY} mY{NgjF ItiB} wH{MqMz JgOg} kP{ZxaQ PeqV} rX{MxLj mIoQ} DgFrcB DpWhmZ EdPzUw GpUbYc NcmPiB RaiJjD QtPcjB KqUgmM LteFgC

Constrained panels with 2 analytes, where 1.0E-8 >= 'AUC p-value' > 0. Contains 151 panels of 149,894 total panels evaluated. : rZ(hR iC jD jG jI jY kC kO lL mT Mx nC nH nR nU Nv oP qZ) gV(bA cT CU dB gP Im Li Mn Mt Ok On Pf Po Qb Qe) lL(aA mP mT mU mW nB nN nR nT nU oO oP oQ) jI(Gz jG kG lN mP mU nC nH nL nR nT nU) oO(aJ bV dF oE Ps Ut Vi Wh Yg Yi Xa) Yg(Ad dX Gb Hv Ks Mh Nd Rc Rx) oP(Gb lK lN qV rB rX rY Sf) Is(aA Iq Jj Jm Uy Yi Yl) hR(aA cF nN nR nU rY) Yi(Cu Hv Jl Jr On) dX(Ho Vi Wd We Xa) Jj(Jk Nt Nv Pg) Uw(nC nH nI nJ) aA(Iv Ji Lv On) Nd(Lp Sf yD) Tn(eP nI pK) Yl(Jr Lx Ou) Ut(eP lW nI) nU(jD jH lK) Gz(iB jP) Ly(wL yD) nR(jY Nm) oQ(jL lN) AwnI GbJr NuwL TzUy OhwJ VinH Constrained panels with 2 analytes, where 1.0E-7 >= 'AUC p-value' > 1.0E-8. Contains 105 panels of 149,894 total panels evaluated. : aA(Fr Jh Jk Jl Jp Jq lN Lx Mt Mu Mz Nj Nl Nn Nt Nv Nw Nx Pg Po) On(eP Ii Iu Iv Jj Jo Jt Of Vh) Nd(Hl jI Ru Rx Tn Um wJ Yf) hR(jI lL lN Ly nO oQ rX) Is(Gb Ii Iu Iv Jo Lj) gV(aL Ao bO Cp dD) lL(jI Ky mM Mu nO) Gb(mU Nw Pg Ua) Tz(lN Si Va) oO(Aw bQ dG) Ua(eP Sh) Yg(Gd Jo) Yi(Lx Nv) Jj(Iv Jl) Jr(Du Si) Ky(eD lN) Vi(mU nJ) cF(aP nR) nU(Ps Wd) jI(Ko Ly) kK(Mu Mv) AamU FwnI GzjG NuNv MzJh IhwL IlrZ HbQd HceQ JdeP WhnH VaVv eDiZ Constrained panels with 2 analytes, where 1.0E-6 >= 'AUC p-value' > 1.0E-7. Contains 208 panels of 149,894 total panels evaluated. : aA(Aa cF Hr Im Jj lM Ma Mb Mj Mx nR NU Ok Pc Qa Qd) Is(Ad Ax cF Hr Ly Mb Mu Nn Ns Nt Of Og On Pg Rm Yj) gV(Cq Dc Hx Ih Ir It Iv Jh Nr Nt) lL(Fr Gz jD lM LY Mx mY Nd Ni) oO(aO aP bZ cF cT Cu Kq lN oF Yj) Gb(Cu Hq Im On Ps Qd Tz Ut Vu) Jj(Ik Im Lx Mx Nn Nx Po Qd) Jl(Hr Ii Iu Iv Jm Um Uy Yl) Nd(Qv Rz Tz Ut Vu Yi Tl) Jr(cU Dr Em Hl nR Rx Yj) Mz(Hw Lx Mq Nn Ns Oh) cF(bA cU Lx Me Qd Tz) Cu(Aa Dg Jo Mm Nm) Jp(Iv Mx Nn Nv Um) On(Hr Jm Ng Nm rZ) Aw(Gd kE kN lW) Hl(mU oP oV oW) Yg(Bb cN Hb Rt) nR(Mq Mu rX rY) nI(cG iB Kq Yj) Tz(Qv Rx Um) Iv(In Nw wJ) Wh(dX nC nL) Jo(Nt Nv Pg) Uy(Hq mU Pg) hR(jH jO Lj) iB(mU mY nT) rZ(Ly Nn Wm) Lx(Iu Mp) Me(bV cB) Nb(Um Yj) Ua(Lp Va) Nv(Mx Of) Oh(Hb wK) nU(Hu Pz) jI(Id Ni) oQ(rX rY) DeGd FrlN LumU MpwJ IuQd SiUt QumE XakG KyUm LdcP OpnH UfpK UwmH PfPg aPcB dDlW eDnY Constrained panels with 2 analytes, where 1.0E-5 >= 'AUC p-value' > 1.0E-6. Contains 549 panels of 149,894 total panels evaluated. : Nv(Hq Hr Ii Is Iu Iv Jh Ji Jl Jm Lh lL Lv Lx Mb My Ng Nn Nt Og Oy Po Yl) Jj(Et Fr Ij Jg Jh Ji Jp Jq Js Lv Mj Mt MU Mv Nh Nl Nq Nu Nw Qa Yg) Po(cB cF Hr Ii Iu Iv Jh Ji Jm Jo Jp lL Nn Nt Nw Og Oh Oy Pg Um) Nw(cF Hb Hr Is Jh Jk Jl lL Lx Mx Nf Nn Nt Nu Pg Si Uy Yi Yl) cU(aA aJ aO aP aV Aw bA Bo bU cA cB cT dB De Di Me Nd nI Yg) Iv(Et Fr Im Jh Ji Jk Jq Lv Lx Ly Ma Mp Mz Nd Nn Pg Qa Qd) Is(Aa aO bU bV cB Fr Hb In Ma Mx Pc Um Uw Va Vb Vh) Jl(Gb Im Jh Ji Jo Jq Lh Mb Mx Nj Nn Ns Nt Og Pg Yj) On(Ad Im Lh Lx Mb Mg Mm Mx My Nb Nn Og Oy Um Yj Yl) Me(aJ aO aP aR aU aZ bA cG cL Cu De dF gL Hc Nn) Lx(cB Jh Ji Jm Lv Mi Mq Mu Mx Nn Nt Oh Pc Pg) Mz(Jp Lv Lw Mi Mp Mt Mu Nf Nq Nu Pc Qa Um wL) Nd(Gp Gz Ji Ky Nt Qd rZ Uf Uo Uy Vj Vp Wb wK) Yg(aJ Ed Jt Ju kE KG Kj Ko Ma Nb oF Uu Va) nI(bF bQ bZ Cu Cv dF Di eM Pi Qu Tz Ua Vu Yd) Jp(Im Jh Ji Jk Lv Ma Mp Mq Nq Nt Nu Oh Pg) cF(aJ aZ cG cS dF Jl Jr Ky Lv oP Or Yi) aP(aC aZ bN bR dA De dG dH Di gV lN Um) Pg(Ii Im Iu Jh Ji Jm Nu Um Vb wJ Yj) nU(mE Mu Mv Nq Ns Pb Pc Qd Wh Xa) oO(bA dD eF fR Hc oQ Ou pH Qt Vu) kG(Dk Fw Hu Mj Nq Ps Tz Ua Yj) nR(Hu lK Mj Mm Mn Mv qV Rb) mU(aA jD Nm Nq Ns Pc Tn Vv) Nn(Ji Jq kK Lv Mx Nu Oy) hR(aO Bo eD iB In Ld lM) Cu(Ad Jt Uw Uy Vh Yj) Nt(aZ In Ly Mg Mp Ng) Mx(cB Jh Jq Mp Nx Oh) Nb(Du Hl Lp Uo Yi Tl) Tz(Eq jV Uw Vz Wh Yl) Qd(Ax cB Jm lL Uy tF) Ji(Hb Iu Jh Jk Jo Lu) Jr(BO De Gn Gz Tl) wL(Hx Il It Nj Og tN) jI(Bc Bo iC Li lO Nj) oV(aO Aw bA bF cT Lp) Gb(Dk Hc Tn Vv Yi) Nq(bA kK lL mP rZ) Ly(hA jO nY wC wK) De(bA bO bV Oy) Yi(Dk Hb Hq Jn) Jh(Jq Mp Oh Qa) Um(Fw Oh Tn Ut) aZ(Aa aO gV Lu) nH(Ps Rv Wd Zx) rZ(Ma Mj My Nj) lL(aD bO lK Mw) Fr(Dg jG Nl) Nu(Oh wF yD) Hv(Uz Wg Yj) Im(cB Si Ue) Ky(jG lM Uo) aA(bO cB mZ) aJ(cB Di lM) gV(aR Ba Dk) kK(Hu Jk Mw) oP(Nm Yh Zq) Mv(Sh Ue) Ua(Rt Uy) Hb(Ps Tn) Hc(Va Vb) Qa(Iu Jm) Ou(kC kN) Ut(Jo Qv) Vi(Ny Ow) dF(aR Zq) dU(cS Rz) lY(Kq Mu) iB(mW nA) oT(eF iO) AabA EdWh FwnK GzlN NjyD HlkN HqYl TrfB IhwJ XakE PsUy UfcP VwdX bOjG bUpK tFnY mZoQ wDwF Constrained panels with 2 analytes, where 1.0E-4 >= 'AUC p-value' > 1.0E-5. Contains 1,162 panels of 149,894 total panels evaluated. : Im(aC aO aU bA bV cL cU dF Dl Iq Iu Jh Ji Jm Jq Lj Lu Lx Mp Mt Mx Mz Nc Nl Nn Nt Nu Nv Nw Nx oE Oh Po Qd Qv Yi) Pg(cB cF Fr Hb Hl Hp Hq Hr In Jq Ju kK Lv Ly mU Mx Nd Nl Nn Nt Nv oE Og Ok Oy Pc Pe Qa Qd Qv Rt Sf Si Ux Yl) Um(aA aJ aO bV CU De dF Fr Gl hR Hx Jh jI jO Mj Mp Mv Mx My nI Nq nR oE Om oO Qa Qt Qv Vi Vu Yh tF) Nd(aO aP bA Bo bV cB dF Dp Et Fw Gb Gl Hf hR Jq Kc kG nR Ou Ow Po Qn Qt Qy Rf St Ub Ue Uh Uk wC Yj) Qd(Ad Al aU Bb bN cL Fr Ji Jk Jl Jo Jq Lj lN Lv Ma Mu Mx mZ Nn Nq Ns Nt Nv Nw Ok On Pc Pj Qv Ue Yl) cF(aO bV cN cT Cu De dG Ed Fw Gp Iv Jj Jl Jo kF Mi Mj Mx Nb nI nO NT nY Qv Sf Tn Ub Vu Yh tF) Is(Al aP As Bb bN cS cU Cw Dd Dc Dg Di kC kF lL lN mU nU oE Qv Rt rZ Sf Si Uc Vi Vt wJ) Jj(cB CU De Fw Ih Il Ir Jn Lh Ma Mp Mz Nc Nj No NR nU Oh Ok Pa Pe Pz Qb Qc Qe Ut) Fr(aC aZ bA cB cT cU eD gV HR Ji Jq kK Lv Lx Mb Mx Ng Nj Nn Nt Nv Nw Oy Po rZ Ux) De(aA aJ aO aZ Bo cS cT Cu dF Di Fw Gp gV Iv Jo Lv Mb Mm Mx Nb Of Og Yi Yj) Mu(bA cU hR Iv jG Jh Jl Jp Jq kG lN Lv Mp Mx Nl Nu Nw oE Qa Qv rZ Ue Yl) Nv(eD Et hR Jq kG lN Ly Mg Mt Nj Nl nU Nw Ok Pc Qa Ry Uy Vb Vh Vz wJ wK Yj) cU(aZ Ba bR cS Cu cY dH dJ Hr Iv Ji Jo Lh Ly Mb Mv Nb Nt Oy pK Pz Yk) Yg(Aj aM AP aZ cC dJ dL dM Fn hC Ii Jr Jv Mm Mz Oi Pj Sf Sh Si) Jh(Et Ip Js Lv Lw Ma Mi Mj Mq Mt Nl Nn Nq Nt Nu Nx

Figure 32 Continued

Og On Pa Pc Qb) Oh(hR Iv Jl IL Lv Lw Mj Mp Mq Mt mZ Nq Nt Qv Ra rZ Uy yD Yl tF) Me(aK aV aX Ba bF BO bU cN cS cT cY Di Dk Ex Fw Gp nY tF) Qa(Et Hr Hw Ij In Jp Jq Lj Lv Ma Mx Nn Ns Nt nU Nw Nx Og Ok) mU(aF bF Cv hA hR Hu Ii Jm Jn Lv Ma Mj Mv mZ Ne Nn Og Rz Yj) Jp(Gb Hb Jo Jq Lh Lw Mb Mi Mj Mt Nj Nl Nx Ok Pc Tz Uo Ut) jI(aK hW Ij In Ir It Jn Jo Mf Mr Na Nn Ok Om Pc Pe rX rY) oO(aF aL Ax Ba cE cG Cs Ct Cv Dd Di hC hG Ld oP oV Tt Uy) Mx(Et Gp In Iv Ji Lv Lw Ly Mt Nq Nt NU Ok Po wJ) bA(aO Aw aZ Bo cB cS Di Fw Hr Jf Jr Ly Mv Oi oT Po) gV(Ad aU Ax bB cG Cs Cw Dd Fp Ik Jg Jk Jt Lj Nj Nl) hR(aJ cB hX jD kP Lu Md Mf Ml mM mP nB Nn Nq nT Pc) Nw(cB Hx Ji Jq Lh Lv Mp Mq Mt Nl Nm nU Ny Pb Pc) IL(bC bI Bo iB In Jl Jq Jy Lw Mf Mm Mv Nn No On) Nb(aP aZ cB Gb kK oT Rx Sf Tz Uy Uz Vb Wg Yl) Iv(aO bO bV cB Jo Mm Mt Nq Nt Og Ok Pa wK Yj) Ji(aC aO bV Hr Hw Ii Lv Mb Nf Nl Nt Nu Pc) Jr(aJ aO aP bR bV cB cG cL dF Di Gp oE Ry) nR(Di Hl Hr jH Jo Ju Lh Lz Mb Mw Nq Pb Pc) Fw(aF aO cT Gb Gp hG Jo Mm Qv Uo Uy Yj) Tn(Ad Bb Ez Gz Ib Jo Ks Qv Rt Si Uy Vb) nU(bV Di Jn Jo Lx Mj Mq Nm Nu Oz Pf Vv) Cu(aN aZ Dl Dr Hl Of Rt Uz Vi Wc Wg) Po(aZ bV In jG Jq Lv Ma Nl Ok Pc Qv) Nt(Bo cB Gb Jm Jq Lv Ma Mz Nn Ok Pa) Jl(Dp Hl Hp Jf jG Lp Ma Ok Pc Qv Vz) aA(aC aN aZ dB dF Di Dk kN mP oP tF) Aa(bV cG cT Ed Gl Gp Ke Tz Vi Vj) Lx(bU cK Gb Jo Jq kK mZ Nl Uy Yj) Ut(Dr Gd Gz Ks Mm pl Ue Uo Vb Yj) aO(aN aR bN bO cS Ed Mb Mi nl Yi) dF(aJ aZ Bo Dg dH Di Gb Jo Mb Mm) pK(aU bC cS Ez kG Ma nO Ow Qu Vv) Aw(aJ aN aZ bO bV Em Gn kG Yf) Mv(aP Gb kG Mz Qv rZ wF Yj Yl) On(Bb cB Du Hl jG Ko Si Uw Vb) nl(cS Gn Ky oT Uf Vp Vv Yh tF) Lv(aP bV cB Et Jq Mp Mt Nu) Mj(cB kF kK MP Mz Nn Yl) Tz(bN Bo eF Hr Li Mm Uk Uo) wJ(Hu Hv Il Ir It Iu wF wL) Mt(Hl Jq lN Ly Mp Nn Pc) Mz(Hr In Ip Jn Nx Qb Yi) Hc(Gd oE oT oV Sf Ux Tl) Yl(Dk Ex Hv Lh Nq Or Pf) Uy(Ed Fy Hv Qe Vp Vv Yi) Vu(Hl Iu Lp Qv Rv Va Vb) aP(Bg bL Bo Hr lM Mb Mm) Ou(kF kl Qv Sf Si Vz) kG(Ib Jk Mw oP Wh Yi) rZ(Jk Mf Ni Nx Pf Qc) lN(aM Mp Mw Nn Nq nY) Bo(bV cG jV lM tF) Gb(cG dM My nH Pf) Ly(cB hG jG oF Qv) Ua(Gd Hp Sf Si Ux) Rx(cT dM Fy Hv Yi) aZ(aJ cS Di Ni Yh) wK(Ih Il Iu Mm wL) yD(Hw Il It wF wL) oT(bC bU cT Ow Vv) oV(aF Cv Ld Pc Yh) Nn(Ip My Nl Ue) Nq(bV Jq Nu Ue) Mb(cG cL Et Ok) Wd(kE kN nC nL) Jo(Ba cB Gl Yi) Uo(bV Ex Ps Vi) wF(Mm Og tN wC) kF(bR Cv Dd Hu) Di(aN bV cG) Gp(Ne Oz tF) Lu(cB Ky oE) Hl(Ho Hv nH) Sf(Ct Dk Hq) Kq(lW mE Yi) aJ(bN bR dG) hA(mF mW Ni) mZ(oP Pc Pf) Et(Jk Nl) Ex(eP Yi) Gn(Ed nH) Nu(Jq Mp) Hv(Lp Vz) Yh(oF Qv) Yj(hC Vi) Qu(lW lY) Ky(oE tF) Rv(nC nL) Vb(Vs Vv) Vj(Hq Pa) cB(bV Ns) wL(Ip Pc) hG(Jf tF) AdVi BaDg CvkN DrPe GdHu GlHb MaNl MpMq NgcG UbOr JkJq XaRj UfdU UxVv aRcT bCjO eDgL nNqV mWjF rBkK jDrY

Constrained panels with 2 analytes, where 1.0E-3 >= 'AUC p-value' > 1.0E-4. Contains 2,094 panels of 149,894 total panels evaluated. : cF(Aa aN aR Aw aX Ba BO bQ cL Di dL dM eD Fr Fy Gl Gz Hf hG Im Jf Jp Jq Lu lW Ly Mb mP Mq Mt MU Mv Nd Nq oE Ok On oV Pe Qa Qb Qe Qh Uf Uh Um Uo Ut Vp Vv Yg) Gp(aC aJ aO aU Bn bP bU cA cB cU Dk Fr Hb hG Im Is Iv jl Jl Jo Ju Ky lN Lu Lx Nb Nu nY oE Oh Or Ou Pg Pj Po Qd Qv Sf Tz Ub Um Uo Ut Vi Vu Wd) Bo(aA aJ aN aO aR aX aZ Ba bO cL Cp cS cT Cu Fr Fw Gl Im Is Iv jG Jl Jq lN Lu Lx Mj Mt Mv Mx Mz Nb Nu Nv oE Ok On oO Pg Po Qa Tn Uo Ut Vv) Um(aR bA Bg bP cL cS Dk Ex Fy hG iB Im Ji Jq jT kF Kq lL Ly Mq MU Mw Nj Nn nU Nv Nw nY oP Or Ou Ps Qb Qd Qe Qh Ub Uf Un Vp Wd Xa) aJ(Ba Bg Fw Gb Gl gW Hf Hr iC Iv Jf Ji Jj Lv Ly Ma Mb Mm Mv Mx Nb Nd Nt oE Oi On Ou Po Qv Rx Tn Tz Ub Uo Ut Uy Vv Yd Yh Yi Yk tF) Yi(aA Ad aP aV Aw aZ Bn cB cC cN cU dF dJ dM Dr Ed Fy Gz Hc Jq Js Ju Ks Lu Mw nH Nm Nn Pb Pf pK Po Qa Rh Sf Ub Va Wh Yg Xa) Im(aF aK aN aP bF Bn bO cG cT De Di Et Fr hG In jG Jo Js lL lN Lv Lw Ma Mi Mj Mq Mu Nq nR Og Ok Pc Pj Qa Qe Sf Vb Yj tF) aO(Aa aX Ba Di Dp Gz Hb Hf Hr Jf jG Jj Jo Ks Lh lM lW Ly Mj Mm MU Mx Nb Nt nU oE Po Qa Qb Qe Sf Tz Ub Uo Vu Yl tF) Fw(aA aU aZ cA cB cS Di dR eF eP gL Hf Hl Hr Jf Jr Ju kN Ks Lu Ly Mb mE Nm Nn nR Ns nY oE Or Oz Pj Sf Ue Uk Ut Yl) Nd(aC aR Aw cG cS Cu dB dD De Di Hc hG Ik jG Jh Jj jO jP jT kF lN Lx Mb Mp Mt Ne Nh Nl nU nY oE rY wF wQ tF) Is(aZ Cu Dr Du Gn hG Hl jG Ju Jv kG kK Kn Ko Kr Ks mP nR nT Pj Ra Rx Tv Ub Ue Uk Ul Uo Uu Uz Vo Vz Wg Zq tF) Uo(aA aP bA Cu dF Di Fr Gl Gz hG jI Jl Ly Mv Mx Mz Nq Oh On Pg Po Qa Qt Qv Tn Ub Ue Uy Vj Vu Wd Yh Xa tF) Ut(Bb bN cB Dp Gn Hb hG Hl Ib Ii Iu jG jT Ju Kj Lh Li Ly Ml Nb Nf Pj pK Rt Ru Ub Ug Uk Ul Uu Uy Vh Yl tF) Gb(Aw Ba Bg Co Ed Ef Fr Fy Hu Iz Jd Jk Js Mj Mt Mu Mw Ng Nq Nv Oa Oh Ok Ou Ow Pe Po Ql Uf Wd Yh Xa) Nb(aR aU bA bO bV cG cL Cu dF Di Dp Dr Gn Gz Hf Ju kG Ky oE Qv Ra Rt Ru Ry Ue Uf Uk Ul Vh Vi Vj Vz) Nw(aP Bb bU bV cU De Di Hq hR kF lN Ma Md Mh Ml mP mU My Nj oE Og Ok Oy Pj Qv Rx Sf Uw Vz Yj tF) Ly(aP Aw cG cS De dF Hc Ik iZ kF kG kK Ky lM Lv Mj mP Ne Nh Nl Nq Nu oE Or Qh St Tn Tz Vu tF) Tn(aA As cA cB Dg Dp Gn Hl Hr Ii Iu Jj Jt Ju Kj Kl Li Mm Nf Ng Ue Ug Uk Uu Uw Ux Vo Yl) Yj(Bn bU cU Dk dX Ex Fr Gd Jh Jn Js Lh Mj Mt nH nU Ny oF Ou Pe Po Ps Ql Ua Vu Yg Yh) Qv(aA aP cL De dF Dk Fr Fy Gl hR Iv Jp Ky Mj Ml Mp Mx Nn Nq nY oO Or Qe Qh Qn Qt Vp) Jj(aP BA cG cL Cp dF Di Ii Io Ip Jr Jt kF Lw Mb Md Mf Mg Mi Mm Mq Mr mZ Ny oP Pc) jI(An Ax bA Cp CT cW Dd Hr Hv Hw Ii Iv Jr Js Kn Kq Kr Mz Nf Nq Nr Qt Ra Rj Uc Ue) Pg(aU aZ bL bO bU bV Di Dp Gz hG jG kF kG Kr Ks mP nT nY oT pF Pj Ue Uw Vh Vj Zq) nR(Aa bU cM Cv DD dI Gn jD Jm kN Lx Ml Mp mU mW Nn Nv Ny Oh Pf pK Qd Qn Tz Ua) Cu(As bN Du Gn Hb Hp Ii In Iv Jm Jr Ks Lh Lu Mb Ng Nn Pj Ru Rx Sf Si Vb Yl Tl) Aa(Ba bZ Cp Cq Dc De dF Dk Fy jG Ji Jq Js kF kK lN Mx oT Pi Ps Qa Qd Ql Yg) Di(aR aX bO cL cS cT Fr Iv iZ Ji Jl kG Lu Lx Mj Mt mU Mx Ne Nu nY oE Po Qb) On(As bV Dg Dp Gn Hb Hp Kr lN mP Mw Pj Rt Rx Ry Sf Ux Uy Uz Va Vi Wg Zq) Po(aC aU aV Ax bL bO bR bU cS cT Dp hG Ju kG kK lN mZ oE rZ Ub Ue tF) Nq(Co cT Gz Ip Jd jG Js Lv Lw Mp Nh Nl nN Nx Ok Oy Qa Qb Si Ub Vz wF) Mx(aU aX aZ bA bV cS dF Gl hG Jm Jo lN Ma Mm mZ Nl Pc rY Ub Ue Uy tF) mU(Ax bQ DD Fy Gn Hc Hq Jk Jl Lx Lz Me Mp Nv Ny Ou Pb Pf Qd Uf Ye) kF(bG cM dD Dk Fn Hc Hq Jk Jn Ky Lu Lz Mq Ne Nm Ny Or Pb Pc Qw Ri Vs) Aw(AR As aU aV cS cT Dr Hr Mb Mm Nf Of Og Oy Sf Uy Vb Wg Yl Tl) Tz(aP bV cB cS eD Fr Hb hG jD Jo Kc lL Ml Mu nU Oh Qd Ub Vj Yg tF) aZ(aR Bn bO bV cG cT Eq Iv Jl Jr Lv Lx Mb Mt Mu nI nY oO Uy Wd Wh) cB(aR Ba cG dM Hr Ji Jl Ky Ma Mm Mq Mu nY Qa Qb Qe Vu Wd Yg Yh) nI(aF aM bB Ch DD Dk Fy Gl HC Hl Jl nY oE Ou Pk Qh Vs Yg) oO(aM aY bC bR cL cS cU Dk dM Fy gL hR Kx Qg Rf Rh Rz Tr Vs tF) De(Ar As Dp Fr Gh Gl Hl Hr lN Lu Ne Nf Or Oz Qb Uy Yg Yl Yf) Vb(Ba Fr Fy Hq Iz Jh Jk Jp Mv Ng Nt Ps Pz Qy Ua Vi Vw Wd Yg) Pc(Et Iv Jq kG kK kP lL Lv Me MP mZ Nh NT Nu oW Qa Vj) bV(aR Ba Bg bO Hr Jf Jo Mb Mi Mu Mv Nt Oi Ou oV Qb Qc Qe tF) dF(aX cS gV Hr Iv Jf Lh Mi Mu Ng Nm Nn Oi Oy Qb Qe Rx Uy Yl) Lx(aU aV bO bR bS cA cC dA Dp Du Hl Jf jG Jk Ma mP Ok oT) aP(bW gW hR iC Iv Jf jG Jo Lh Mu Nm oE Oi Sj Ub Vz Yk tF) kG(Cp Dd dI Hc Hl Hq Ke Lu Ng Ny Ou Oz Pb Rv Vs Wd Yd Zx) lN(aD bC Bn iB jD jH Jl Jq Jy Mj Mv No Oh Or Qb Qt qZ Vu) Mb(aU bA cN cS eF gL gV Ip Jk Jq Mm Mp Mu Mz Nn oP oT) Mt(Et Jf jG Jo kK Lw Ma Mi Mq Mu Nf Ok rZ Uz Wg Yk Yl) nU(aL cT Cv dD Hl Jk Jm Jq Lv Lz Ma Ny Oh oP oQ Pe Rb) oE(aA aF Ed Gh GL Jf Ns nY Oz Pb Qt Ub Uf Vu Yg tF) Fr(aR aU bL Dp Ed Hb Hq Jo Mq Ok Qa rY Ue Uw Uy tF) Yh(aA aV cN Ed Gd Iv Jo Ju Ks Mh Ne oT Qx Sf Ub Va) bO(aR Ba Bg cG cS cT Dk dM hR Jl Mv Nt Qa Vi Vu Wd) Nl(Ip Jk Jq Lv Mj Mm Mp Mq Mr Mv Mz No Nu Ok Pa) bA(Bg Gz Hf Iv Ji Jo Ma Mi Mj Nn Nt Qb Qe Rx Yl) cS(aC aN bN cT Dk dM gC Iv Jo Jr lW Or Ps Yk) kN(Al bF bM bQ Gn Hq Mp Mv Ua Uf Uy Vj Vs Zx) Gl(Bb bP cA cR Dg Hr Lu Mm Nm Nn nY Or Pj) Jq(Et Hr In jG Jo Lu Ma Mp Mq Og Ok Uy Va) hR(dM Hr Jl Jm Ma Mv mW mY mZ Na Ni Qd Ue) Gz(Ba cT Dk Hc Jn Jp Nt Oh Pz Ua Vv Yg) Nu(In Ip Jk Lw Mj Mv No Og Ok Pa Qb wC) Mu(aC cT eD Et Js Nj Nt Nx Oh Ok Oy Qb) Vu(aC aU Dp Hb kK Lj mE Mm Qz Rm Si Xa) cG(As bR bU cC cH dH eP Iv Jo Oi Oy Uy) Ky(Ed Hc Ju Me Ml Mm Mv Pz Qt Ub Uf) gV(aM Ar aX bQ Jm Mi Mr Ms Ne Nh Pz) jG(cW hA iB jD jL jO Mv Mw Nv Qd Qt) oV(Ba bQ cU eM Ez fA Hb Sj Uf Vz tF) Lv(aR bU cU Js kC Mi Mj Mm Ok tF) Ji(aF aU Ax cT Hv Ij In Ma Om Pj) Jl(aU Hb Kr Ks Pj Rx Si Ue Uk

Figure 32 Continued

Tl) Jr(aF aR aU aX bU cT Uz Vj Wg Xa) Oh(Et Ip Ju Nx Pj Qa Qz Rx Vz Yg) kK(dD Hc Hq Lh Lu Pb Pf Pz Qa Qd) Mp(Js jT Lw lY Mi Nh Nj Og Ok) Mz(Ad Et Hv Ij Jg Jk Ma Nj No) Hl(Dk Ex Hc Jh Mj nD Nv oF Vi) Uy(aA dM Jp Js My Oa Ou Qh Wb) Va(Hu Jk Ng Nx Ps Pz Vp Wd Yk) Vj(Bn Hb Hv Mm Ow Oz Pj Ub Vv) mP(Hq Hu Lu Mq Nm oT Pf pK Qd) nY(aK cI Hf Id Jf Ju jV Qt Ub) Iv(aU Gn Lw Mi Mq wQ yD Yk) Yg(aA Hc Iz Nm Nn Om Rh Tr) Yl(Ef Hu Jh Ld Mw Ow Ua Vp) Or(Ju Lu Me Ml Mv Oz Pz Ue) lL(aM bR Dp Id Kj Qt Rf Vp) Ed(bF Hp Lu Sf Wd Yk Zx) Qd(Cs Dd Ju Ko Ks Rm Si) Jm(Ij Ir Jk Js Mj Qb Qe) Jo(Cp cT Et Ok Qa Uf tF) Nv(Dp In jT Ma Rx rY yD) Vi(An Cq Cv Dr Gn Id Si) aR(aA aL Ba bF bG bQ Dk) pK(aQ bZ Fy Ju Kq Kx oF) Nn(Et Mq Ng Nj Nx Ok) Ue(Ef Jk Ma Mq Ou Uf) Jh(Jk Nj No Ok Rx Uk) Jp(Ju Pj Qy Si Tr Uw) Ps(Hp Iu Ny Ow Rc Si) cU(As Hf Jf Qe Wd Zx) eD(aM Bn Ic Mw qZ Uv) jD(iB iJ iO Ni Qn rX) oT(Ba cL eM Ez Ju oN) Ex(Du lM Mm Qw Vh) aA(Ba Bg hW lO Uf) lW(bF bQ bZ Hc Ou) mZ(Jn Li Lz Qa rB) Dk(dK Hb Rx Si) Et(Ma Mj Mq Pa) Mm(Ba oP oW wC) Yk(aM dG dX Rx) Qt(fB iB jP jT) Xa(Ad Cv Dr Nf) aC(aX Ba Ef Jf) tF(aF gL Jf Mq) wF(Ma Mc Pd Pf) Dp(Mw Vp Vv) Nm(Ho oW Uf) Lu(nT Ou rZ) My(RX rY) Ub(Hc hG Ou) ln(Jn Js Mj) Vz(aM Oa Ow) Sf(bF Pf Zx) Qb(Jg Ma Nx) Jk(Nh No Oy) iB(Ni Ra rY) Bn(aX Yf) Mv(Gd Ng) Nj(wC wQ) Ua(mE nN) Hr(Lh Ok) Zx(Ju nL) Wd(dI Mh) Jn(Uz Wg) Kc(cT Me) Ke(Hb Pj) Rz(kE nH) Rt(dX Vp) Ow(jB Si) Pa(Jg Nh) aF(Nt oW) bQ(cC mF) cL(Qa Qe) nK(lK Uf) wJ(Ip wH) hV(jR mY) jO(bW Ni) AxPe DrFy DuMq EfOy GhkR GnVp MaNc MjaU HunT HwwD IhyD HclY HfeF IrIu IzSh YdnH RbhG QukI RxQn LddU LirZ LjoW OuOz UgoP VvVw PikE bRdG cTeQ dBdM dRlX hArY mWjM iOjV qVkP

Figure 32 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.0E1 | 1.0E2 | 8.0E1 | 1.2E2 | 5.6E1 | 8.1E1 | 7.0E0 | 1.2E1 | 4.0E2 | 4.8E2 | 171 | 101 | 171 | 101 | 0.65 |
| Ad | ug/mL | 3.8E-2 | 5.8E-2 | 6.1E-2 | 2.2E-1 | 7.5E-2 | 1.0E0 | 6.8E-4 | 9.4E-4 | 3.7E-1 | 8.5E0 | 75 | 67 | 75 | 67 | 0.64 |
| Af | ng/mL | 1.3E0 | 1.1E0 | 1.2E1 | 7.8E0 | 6.1E1 | 2.4E1 | 1.7E-3 | 1.7E-3 | 5.3E2 | 1.9E2 | 75 | 67 | 75 | 67 | 0.50 |
| Aj | ug/mL | 1.6E0 | 3.6E-1 | 2.5E0 | 2.0E0 | 2.5E0 | 2.4E0 | 1.5E-3 | 2.1E-3 | 6.1E0 | 6.1E0 | 75 | 67 | 75 | 67 | 0.41 |
| Al | mg/mL | 8.3E-5 | 9.6E-5 | 2.3E-4 | 3.1E-4 | 4.2E-4 | 4.5E-4 | 4.6E-6 | 7.6E-6 | 1.8E-3 | 1.8E-3 | 75 | 67 | 75 | 67 | 0.58 |
| An | U/mL | 6.1E1 | 7.8E1 | 2.4E2 | 3.5E2 | 7.3E2 | 9.9E2 | 6.1E-1 | 6.4E-1 | 5.5E3 | 7.8E3 | 75 | 67 | 75 | 67 | 0.58 |
| Ao | pg/mL | 9.2E1 | 9.9E1 | 9.7E2 | 1.7E2 | 5.3E3 | 1.8E2 | 2.8E0 | 5.4E0 | 3.9E4 | 8.3E2 | 75 | 67 | 75 | 67 | 0.58 |
| Ap | ng/mL | 3.1E1 | 3.8E1 | 3.9E1 | 5.1E1 | 4.1E1 | 4.8E1 | 2.0E0 | 2.4E0 | 2.8E2 | 2.9E2 | 75 | 67 | 75 | 67 | 0.60 |
| Ar | ng/mL | 4.1E-1 | 1.7E0 | 1.6E0 | 5.6E0 | 3.6E0 | 1.1E1 | 4.1E-2 | 3.4E-1 | 2.0E1 | 5.1E1 | 75 | 67 | 75 | 67 | 0.71 |
| As | ng/mL | 8.0E-3 | 1.1E-2 | 1.1E-2 | 3.2E-2 | 1.6E-2 | 1.5E-1 | 1.7E-3 | 1.7E-3 | 9.8E-2 | 1.2E0 | 75 | 67 | 75 | 67 | 0.57 |
| Aw | pg/mL | 1.6E1 | 1.6E1 | 1.7E1 | 1.7E1 | 5.9E0 | 7.0E0 | 6.8E0 | 2.9E-2 | 4.2E1 | 5.1E1 | 75 | 67 | 75 | 67 | 0.52 |
| Ax | ng/mL | 1.3E0 | 6.6E0 | 8.1E0 | 6.5E1 | 1.8E1 | 1.7E2 | 1.3E-2 | 1.2E-2 | 1.1E2 | 8.5E2 | 75 | 67 | 75 | 67 | 0.66 |
| Ba | ng/mL | 7.7E1 | 1.3E2 | 6.1E2 | 6.6E2 | 1.6E3 | 1.5E3 | 1.1E0 | 3.1E0 | 8.1E3 | 8.1E3 | 75 | 67 | 75 | 67 | 0.58 |
| Bb | ng/mL | 3.6E0 | 6.0E0 | 5.8E0 | 8.9E0 | 8.2E0 | 8.4E0 | 4.1E-3 | 6.8E-3 | 4.9E1 | 3.7E1 | 75 | 67 | 75 | 67 | 0.65 |
| Bc | ng/mL | 2.6E1 | 6.0E1 | 1.0E2 | 1.6E2 | 2.1E2 | 2.6E2 | 4.9E-1 | 3.4E0 | 1.0E3 | 1.2E3 | 75 | 67 | 75 | 67 | 0.64 |
| Bg | ng/mL | 1.0E-1 | 1.3E-1 | 5.1E0 | 9.6E0 | 2.1E1 | 5.0E1 | 5.3E-4 | 1.1E-2 | 1.5E2 | 4.0E2 | 75 | 67 | 75 | 67 | 0.53 |
| Bn | ng/mL | 5.6E-2 | 5.6E-2 | 9.7E-1 | 2.1E0 | 1.8E0 | 7.3E0 | 5.6E-2 | 5.6E-2 | 7.4E0 | 5.8E1 | 75 | 67 | 75 | 67 | 0.52 |
| Bo | ng/mL | 1.3E1 | 1.4E1 | 1.4E1 | 1.7E1 | 9.8E0 | 1.3E1 | 1.6E-2 | 1.6E-2 | 3.8E1 | 5.3E1 | 75 | 67 | 75 | 67 | 0.55 |
| Ch | uIU/mL | 1.2E0 | 1.0E0 | 4.7E1 | 3.3E1 | 2.3E2 | 1.6E2 | 3.4E-3 | 3.4E-3 | 1.8E3 | 1.2E3 | 75 | 67 | 75 | 67 | 0.44 |
| Co | pg/mL | 4.4E1 | 5.4E1 | 1.5E2 | 3.7E2 | 5.0E2 | 2.0E3 | 1.5E-1 | 1.5E-1 | 3.7E3 | 1.7E4 | 75 | 67 | 75 | 67 | 0.57 |
| Cp | ng/mL | 2.1E1 | 2.2E1 | 2.7E1 | 5.0E1 | 2.2E1 | 1.5E2 | 6.0E-1 | 2.5E0 | 1.3E2 | 1.3E3 | 75 | 67 | 75 | 67 | 0.57 |
| Cq | ng/mL | 2.8E-2 | 4.1E-2 | 7.9E-2 | 9.1E-1 | 2.5E-1 | 6.0E0 | 8.0E-4 | 8.0E-4 | 2.0E0 | 4.9E1 | 75 | 67 | 75 | 67 | 0.60 |
| Cs | ng/mL | 4.6E1 | 2.1E2 | 2.1E2 | 9.8E2 | 4.1E2 | 2.6E3 | 1.0E0 | 8.3E1 | 1.9E3 | 1.8E4 | 75 | 67 | 75 | 67 | 0.66 |
| Ct | ng/mL | 5.7E-1 | 1.8E-1 | 4.6E1 | 4.5E1 | 1.3E2 | 1.3E2 | 2.2E-2 | 1.1E-4 | 4.7E2 | 6.2E2 | 75 | 67 | 75 | 67 | 0.43 |
| Cu | ng/mL | 2.1E-1 | 3.3E-1 | 3.4E-1 | 1.9E0 | 3.6E-1 | 8.4E0 | 2.8E-2 | 3.5E-2 | 1.7E0 | 6.6E1 | 75 | 67 | 75 | 67 | 0.63 |
| Cv | ng/mL | 2.8E0 | 9.1E0 | 2.0E1 | 3.6E1 | 6.5E1 | 7.4E1 | 2.0E-2 | 2.4E-2 | 5.3E2 | 4.7E2 | 75 | 67 | 75 | 67 | 0.61 |
| Cw | mIU/mL | 2.8E-2 | 4.3E-2 | 3.8E-2 | 1.5E-1 | 3.0E-2 | 8.2E-1 | 8.9E-4 | 4.1E-3 | 1.5E-1 | 6.8E0 | 75 | 67 | 75 | 67 | 0.58 |
| Cx | ng/mL | 8.5E-1 | 4.6E-1 | 4.8E1 | 4.5E1 | 9.4E1 | 9.5E1 | 9.3E-5 | 9.3E-5 | 3.9E2 | 3.9E2 | 75 | 67 | 75 | 67 | 0.51 |
| Db | ug/mL | 7.5E0 | 7.3E0 | 8.6E0 | 8.5E0 | 6.9E0 | 8.6E0 | 4.5E-1 | 8.2E-1 | 4.3E1 | 5.9E1 | 75 | 67 | 75 | 67 | 0.48 |
| Dc | nmol/L | 1.5E-2 | 2.9E-2 | 3.4E-2 | 3.5E-1 | 5.2E-2 | 1.7E0 | 5.2E-6 | 1.3E-3 | 3.0E-1 | 1.4E1 | 75 | 67 | 75 | 67 | 0.65 |
| Dd | ug/mL | 4.7E-2 | 1.6E-1 | 1.3E-1 | 3.0E-1 | 2.4E-1 | 5.0E-1 | 4.8E-4 | 3.4E-3 | 1.6E0 | 3.6E0 | 75 | 67 | 75 | 67 | 0.65 |
| De | ng/mL | 3.4E-3 | 3.4E-3 | 7.5E-2 | 9.8E-2 | 1.5E-1 | 1.9E-1 | 3.4E-3 | 3.4E-3 | 9.2E-1 | 1.1E0 | 75 | 67 | 75 | 67 | 0.52 |
| Dg | ng/mL | 2.9E1 | 4.2E1 | 4.0E1 | 5.5E1 | 3.5E1 | 4.2E1 | 7.8E-1 | 7.1E-1 | 1.2E2 | 1.9E2 | 75 | 67 | 75 | 67 | 0.61 |
| Di | pg/mL | 2.0E0 | 2.7E0 | 2.4E0 | 2.6E0 | 2.4E0 | 1.9E0 | 1.8E-1 | 1.8E-1 | 1.3E1 | 9.0E0 | 75 | 67 | 75 | 67 | 0.57 |
| Dk | uIU/mL | 1.2E-2 | 1.8E-2 | 6.9E-2 | 6.9E-2 | 2.2E-1 | 1.6E-1 | 1.1E-4 | 1.1E-4 | 1.6E0 | 9.8E-1 | 75 | 67 | 75 | 67 | 0.57 |
| Dl | ng/mL | 1.8E2 | 2.5E2 | 2.6E2 | 3.7E2 | 2.3E2 | 3.4E2 | 8.9E0 | 5.5E0 | 1.1E3 | 1.6E3 | 75 | 67 | 75 | 67 | 0.59 |
| Dp | ng/ml | 2.1E0 | 2.1E0 | 4.9E0 | 5.8E0 | 7.1E0 | 1.1E1 | 1.5E-2 | 3.7E-3 | 3.5E1 | 5.6E1 | 57 | 57 | 57 | 57 | 0.48 |
| Dr | pg/mL | 9.6E0 | 3.2E1 | 3.6E1 | 5.1E2 | 5.7E1 | 2.1E3 | 7.5E-1 | 7.5E-1 | 2.5E2 | 1.0E4 | 33 | 25 | 33 | 25 | 0.70 |
| Du | pg/ml | 4.8E1 | 5.4E2 | 5.3E2 | 2.6E3 | 1.1E3 | 6.2E3 | 1.2E0 | 1.2E0 | 5.4E3 | 2.4E4 | 26 | 22 | 26 | 22 | 0.68 |
| Dw | ng/mL | 9.2E-3 | 3.0E-2 | 4.4E-2 | 5.7E-2 | 6.5E-2 | 7.1E-2 | 9.2E-3 | 9.2E-3 | 1.9E-1 | 1.9E-1 | 8 | 9 | 8 | 9 | 0.59 |
| Ef | ng/mL | 8.4E-2 | 1.3E-1 | 7.5E-1 | 9.6E-1 | 1.4E0 | 2.4E0 | 5.7E-4 | 5.7E-4 | 4.7E0 | 9.9E0 | 62 | 62 | 62 | 62 | 0.56 |
| Wm | % | 8.5E-2 | 4.5E-1 | 4.2E0 | 5.1E1 | 2.3E1 | 2.0E2 | 5.4E-2 | 8.5E-2 | 2.0E2 | 1.0E3 | 70 | 61 | 70 | 61 | 0.57 |
| Ed | pg/mL | 5.2E-1 | 1.5E1 | 2.4E1 | 5.4E1 | 3.5E1 | 9.7E1 | 5.2E-1 | 5.2E-1 | 1.3E2 | 5.0E2 | 57 | 57 | 57 | 57 | 0.58 |
| Eo | ng/mL | 7.0E0 | 1.8E0 | 7.5E0 | 7.1E0 | 5.2E0 | 1.3E1 | 3.6E-1 | 3.6E-1 | 1.6E1 | 4.0E1 | 8 | 9 | 8 | 9 | 0.33 |
| Yf | ng/mL | 1.5E1 | 1.5E1 | 3.4E1 | 8.1E1 | 5.0E1 | 1.5E2 | 2.9E-1 | 2.9E-1 | 2.4E2 | 5.9E2 | 28 | 21 | 28 | 21 | 0.47 |
| Tj | pg/ml | 3.7E-1 | 3.7E-1 | 2.8E1 | 6.2E1 | 1.2E2 | 3.0E2 | 3.7E-1 | 3.7E-1 | 8.7E2 | 2.3E3 | 61 | 59 | 61 | 59 | 0.56 |
| Po | pg/ml | 1.1E-1 | 2.5E0 | 7.9E0 | 1.6E1 | 2.7E1 | 3.8E1 | 8.0E-3 | 2.6E-2 | 2.7E2 | 2.2E2 | 155 | 114 | 155 | 114 | 0.61 |
| Ti | ug/mL | 2.2E0 | 5.8E0 | 3.4E0 | 6.5E0 | 3.3E0 | 4.7E0 | 1.2E-1 | 6.0E-1 | 1.4E1 | 1.8E1 | 38 | 31 | 38 | 31 | 0.72 |
| Em | ng/mL | 1.3E-2 | 2.2E-2 | 5.9E-2 | 1.2E-1 | 9.6E-2 | 3.4E-1 | 8.4E-4 | 8.4E-4 | 5.0E-1 | 1.9E0 | 39 | 34 | 39 | 34 | 0.49 |
| Et | ng/mL | 1.3E3 | 2.2E3 | 1.5E3 | 2.3E3 | 1.1E3 | 1.2E3 | 7.9E1 | 3.1E2 | 4.3E3 | 5.0E3 | 154 | 114 | 154 | 114 | 0.70 |
| Eq | pg/mL | 2.6E2 | 6.6E1 | 3.9E2 | 3.0E2 | 4.2E2 | 4.1E2 | 1.0E0 | 1.0E0 | 1.5E3 | 1.4E3 | 26 | 22 | 26 | 22 | 0.40 |
| Ew | U/ml | 1.9E0 | 2.2E0 | 2.8E0 | 2.5E0 | 2.5E0 | 1.2E0 | 1.1E0 | 1.3E0 | 8.8E0 | 5.0E0 | 8 | 9 | 8 | 9 | 0.58 |
| Th | ug/mL | 1.2E0 | 1.6E0 | 1.8E0 | 2.0E0 | 1.4E0 | 1.9E0 | 2.4E-1 | 2.6E-3 | 5.4E0 | 7.5E0 | 38 | 31 | 38 | 31 | 0.50 |
| Fa | ng/ml | 3.3E1 | 6.5E1 | 4.5E1 | 2.2E2 | 4.5E1 | 5.9E2 | 2.6E-1 | 6.0E-1 | 2.2E2 | 3.7E3 | 56 | 55 | 56 | 55 | 0.66 |

Figure 33

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ez | ng/ml | 5.0E0 | 4.1E0 | 1.6E1 | 1.5E1 | 2.9E1 | 3.2E1 | 1.3E-2 | 1.3E-2 | 1.6E2 | 2.0E2 | 57 | 57 | 57 | 57 | 0.53 |
| Fb | ng/ml | 2.3E1 | 2.7E1 | 2.1E1 | 2.5E1 | 1.3E1 | 9.6E0 | 8.9E-1 | 6.6E-1 | 4.3E1 | 4.1E1 | 56 | 56 | 56 | 56 | 0.57 |
| Ex | ng/ml | 5.5E-2 | 1.4E-1 | 1.5E-1 | 2.2E-1 | 2.4E-1 | 3.1E-1 | 3.5E-5 | 1.7E-4 | 1.0E0 | 1.5E0 | 43 | 45 | 43 | 45 | 0.64 |
| Fc | pg/ml | 2.2E-1 | 2.2E-1 | 4.1E0 | 3.6E1 | 9.9E0 | 1.0E2 | 2.2E-1 | 2.2E-1 | 4.4E1 | 3.9E2 | 27 | 22 | 27 | 22 | 0.57 |
| Fd | pg/ml | 2.3E1 | 2.1E2 | 2.9E2 | 2.9E3 | 6.2E2 | 7.0E3 | 4.5E-1 | 9.8E-1 | 2.7E3 | 2.5E4 | 27 | 22 | 27 | 22 | 0.62 |
| Fi | pg/ml | 2.5E-1 | 2.5E-1 | 2.1E1 | 1.4E2 | 6.1E1 | 4.0E2 | 2.5E-1 | 2.5E-1 | 2.5E2 | 1.8E3 | 27 | 22 | 27 | 22 | 0.61 |
| Fn | ng/ml | 2.1E-1 | 2.1E-1 | 4.8E0 | 4.1E0 | 8.6E0 | 6.3E0 | 1.1E-14 | 1.1E-14 | 3.7E1 | 2.7E1 | 57 | 57 | 57 | 57 | 0.50 |
| Fp | ng/ml | 9.3E0 | 2.3E1 | 1.9E1 | 3.4E1 | 2.4E1 | 3.2E1 | 6.0E-3 | 2.8E-1 | 1.2E2 | 1.3E2 | 156 | 116 | 156 | 116 | 0.66 |
| Fr | ng/ml | 3.0E4 | 6.5E4 | 1.2E5 | 1.7E5 | 1.9E5 | 2.3E5 | 1.9E2 | 1.8E3 | 8.4E5 | 8.4E5 | 159 | 117 | 159 | 117 | 0.63 |
| Fw | pg/ml | 8.5E-1 | 5.1E0 | 5.5E1 | 4.8E1 | 3.7E2 | 1.4E2 | 1.2E-1 | 1.2E-1 | 3.0E3 | 9.1E2 | 63 | 61 | 63 | 61 | 0.62 |
| Fy | ng/ml | 3.2E1 | 5.4E1 | 4.7E1 | 1.0E2 | 4.9E1 | 1.4E2 | 1.2E-1 | 1.2E-1 | 2.2E2 | 6.5E2 | 57 | 55 | 57 | 55 | 0.63 |
| Gh | pg/ml | 2.0E0 | 2.8E0 | 2.4E1 | 1.4E1 | 6.8E1 | 3.1E1 | 2.9E-2 | 2.9E-2 | 3.2E2 | 1.4E2 | 27 | 22 | 27 | 22 | 0.52 |
| Gb | % | 4.3E1 | 5.2E1 | 3.9E1 | 6.9E1 | 2.6E1 | 6.6E1 | 2.2E0 | 1.3E1 | 1.0E2 | 3.0E2 | 27 | 22 | 27 | 22 | 0.65 |
| Gc | ng/ml | 6.2E1 | 1.6E2 | 1.0E2 | 2.8E2 | 1.3E2 | 2.7E2 | 6.4E0 | 6.9E0 | 7.3E2 | 1.2E3 | 33 | 25 | 33 | 25 | 0.77 |
| Gd | ng/ml | 3.3E1 | 3.7E1 | 3.4E1 | 3.6E1 | 1.7E1 | 2.0E1 | 3.0E0 | 3.7E0 | 6.9E1 | 8.0E1 | 40 | 27 | 40 | 27 | 0.51 |
| Gn | U/ml | 2.3E-1 | 2.7E-1 | 1.7E0 | 5.2E0 | 5.4E0 | 2.3E1 | 5.6E-3 | 1.2E-2 | 3.0E1 | 1.1E2 | 32 | 25 | 32 | 25 | 0.55 |
| Gl | pg/ml | 8.9E3 | 1.1E4 | 1.2E4 | 1.4E4 | 9.4E3 | 9.9E3 | 9.1E1 | 4.0E2 | 3.1E4 | 3.1E4 | 63 | 61 | 63 | 61 | 0.56 |
| Gp | U/ml | 1.3E0 | 1.0E0 | 2.2E0 | 2.2E0 | 2.8E0 | 3.3E0 | 1.5E-2 | 1.5E-2 | 1.6E1 | 1.8E1 | 63 | 61 | 63 | 61 | 0.46 |
| Gz | ug/ml | 1.1E1 | 1.1E0 | 6.5E0 | 4.6E0 | 6.2E0 | 5.5E0 | 4.2E-2 | 1.0E-1 | 2.5E1 | 1.9E1 | 38 | 42 | 38 | 42 | 0.46 |
| Ha | ng/ml | 1.6E0 | 3.3E0 | 5.5E0 | 1.3E1 | 1.5E1 | 2.6E1 | 1.7E-2 | 1.7E-2 | 1.0E2 | 1.0E2 | 55 | 57 | 55 | 57 | 0.63 |
| Nm | pg/ml | 1.3E4 | 2.0E4 | 2.7E4 | 6.1E4 | 6.6E4 | 1.3E5 | 1.0E-9 | 1.0E-9 | 7.8E5 | 9.6E5 | 156 | 116 | 156 | 116 | 0.61 |
| Nn | pg/ml | 1.4E2 | 2.9E2 | 1.6E3 | 6.6E3 | 6.0E3 | 3.2E4 | 1.0E-9 | 1.0E-9 | 6.0E4 | 3.1E5 | 156 | 116 | 156 | 116 | 0.60 |
| No | pg/ml | 1.3E1 | 2.5E1 | 2.9E1 | 6.7E1 | 5.6E1 | 1.4E2 | 1.0E-9 | 1.0E-9 | 5.6E2 | 9.1E2 | 156 | 116 | 156 | 116 | 0.63 |
| Nq | pg/ml | 2.0E0 | 2.9E0 | 2.5E1 | 3.5E1 | 7.8E1 | 1.1E2 | 1.0E-9 | 1.0E-9 | 6.2E2 | 6.7E2 | 156 | 116 | 156 | 116 | 0.52 |
| Nr | pg/ml | 1.3E0 | 4.2E0 | 2.1E1 | 4.5E1 | 9.2E1 | 1.5E2 | 1.0E-9 | 1.0E-9 | 9.8E2 | 1.4E3 | 156 | 116 | 156 | 116 | 0.61 |
| Ns | pg/ml | 1.0E-9 | 1.0E-9 | 1.3E1 | 4.2E0 | 9.3E1 | 2.6E1 | 1.0E-9 | 1.0E-9 | 1.1E3 | 2.4E2 | 156 | 116 | 156 | 116 | 0.49 |
| Nt | pg/ml | 9.8E1 | 1.4E2 | 1.3E2 | 1.9E2 | 1.1E2 | 2.0E2 | 1.5E1 | 1.5E1 | 8.8E2 | 1.7E3 | 156 | 116 | 156 | 116 | 0.64 |
| Nu | pg/ml | 1.9E1 | 4.7E1 | 5.2E1 | 7.7E1 | 8.2E1 | 9.9E1 | 1.0E-9 | 1.0E-9 | 3.7E2 | 6.3E2 | 156 | 116 | 156 | 116 | 0.61 |
| Lu | pg/ml | 1.0E4 | 1.0E4 | 2.0E4 | 1.1E4 | 5.8E4 | 1.0E4 | 9.4E2 | 5.2E2 | 5.6E5 | 5.9E4 | 156 | 116 | 156 | 116 | 0.48 |
| Lv | pg/ml | 1.0E-9 | 1.4E0 | 1.3E1 | 2.5E1 | 2.6E1 | 4.3E1 | 1.0E-9 | 1.0E-9 | 2.4E2 | 2.6E2 | 156 | 116 | 156 | 116 | 0.58 |
| Lw | pg/ml | 1.0E-9 | 1.0E-9 | 2.0E-1 | 3.0E0 | 2.6E0 | 1.8E1 | 1.0E-9 | 1.0E-9 | 3.2E1 | 1.8E2 | 156 | 116 | 156 | 116 | 0.53 |
| Lx | pg/ml | 1.0E-9 | 6.0E1 | 1.5E2 | 5.4E2 | 5.6E2 | 2.2E3 | 1.0E-9 | 1.0E-9 | 6.2E3 | 2.2E4 | 156 | 116 | 156 | 116 | 0.65 |
| Ly | pg/ml | 1.0E-9 | 1.0E-9 | 8.5E0 | 1.1E1 | 1.7E1 | 1.9E1 | 1.0E-9 | 1.0E-9 | 1.1E2 | 9.6E1 | 156 | 116 | 156 | 116 | 0.54 |
| Lz | pg/ml | 1.0E-9 | 1.0E-9 | 3.0E0 | 4.3E0 | 3.4E1 | 1.8E1 | 1.0E-9 | 1.0E-9 | 4.3E2 | 1.3E2 | 156 | 116 | 156 | 116 | 0.55 |
| Ma | pg/ml | 4.3E2 | 8.2E2 | 2.2E3 | 3.3E3 | 6.4E3 | 7.4E3 | 1.0E-9 | 1.0E-9 | 6.5E4 | 5.2E4 | 156 | 116 | 156 | 116 | 0.60 |
| Mb | pg/ml | 2.5E1 | 2.8E1 | 3.1E1 | 3.5E1 | 1.4E1 | 2.3E1 | 9.2E0 | 4.1E0 | 6.9E1 | 2.1E2 | 156 | 116 | 156 | 116 | 0.54 |
| Mc | pg/ml | 1.0E-9 | 1.0E-9 | 3.8E-2 | 1.1E-1 | 3.5E-1 | 1.2E0 | 1.0E-9 | 1.0E-9 | 4.0E0 | 1.3E1 | 156 | 116 | 156 | 116 | 0.49 |
| Md | pg/ml | 1.0E-9 | 1.0E-9 | 5.5E-1 | 7.1E-1 | 5.2E0 | 3.5E0 | 1.0E-9 | 1.0E-9 | 6.5E1 | 2.9E1 | 156 | 116 | 156 | 116 | 0.52 |
| Me | pg/ml | 3.1E1 | 3.3E1 | 2.9E1 | 3.4E1 | 1.7E1 | 3.6E1 | 1.1E-1 | 1.0E-9 | 1.2E2 | 3.2E2 | 156 | 116 | 156 | 116 | 0.52 |
| Mf | pg/ml | 1.0E-9 | 1.0E-9 | 3.9E-1 | 1.3E0 | 1.9E0 | 6.3E0 | 1.0E-9 | 1.0E-9 | 2.0E1 | 5.6E1 | 156 | 116 | 156 | 116 | 0.54 |
| Mg | pg/ml | 1.0E0 | 1.8E0 | 6.7E0 | 9.6E0 | 1.2E1 | 2.0E1 | 1.0E-9 | 1.0E-9 | 8.8E1 | 1.5E2 | 156 | 116 | 156 | 116 | 0.54 |
| Mh | pg/ml | 1.0E-9 | 1.0E-9 | 1.1E0 | 1.2E0 | 8.9E0 | 4.6E0 | 1.0E-9 | 1.0E-9 | 1.1E2 | 4.2E1 | 156 | 116 | 156 | 116 | 0.57 |
| Mi | pg/ml | 1.0E-9 | 1.0E-9 | 1.2E0 | 9.5E0 | 1.0E1 | 5.8E1 | 1.0E-9 | 1.0E-9 | 1.2E2 | 5.2E2 | 156 | 116 | 156 | 116 | 0.53 |
| Mj | pg/ml | 1.0E-9 | 1.0E-9 | 6.1E0 | 9.8E0 | 3.8E1 | 3.0E1 | 1.0E-9 | 1.0E-9 | 4.6E2 | 2.1E2 | 156 | 116 | 156 | 116 | 0.53 |
| Mk | pg/ml | 3.7E0 | 2.2E0 | 1.6E1 | 2.3E1 | 8.4E1 | 1.3E2 | 1.0E-9 | 1.0E-9 | 1.0E3 | 1.3E3 | 156 | 116 | 156 | 116 | 0.48 |
| Ml | pg/ml | 1.0E-9 | 1.0E-9 | 1.5E1 | 1.2E1 | 1.7E2 | 5.9E1 | 1.0E-9 | 1.0E-9 | 2.1E3 | 5.1E2 | 156 | 116 | 156 | 116 | 0.54 |
| Mm | pg/ml | 4.0E2 | 8.7E2 | 9.0E2 | 1.5E3 | 1.1E3 | 1.8E3 | 1.0E-9 | 1.9E1 | 6.0E3 | 1.0E4 | 156 | 116 | 156 | 116 | 0.63 |
| Mn | pg/ml | 5.2E0 | 9.3E0 | 1.2E1 | 1.3E1 | 3.5E1 | 1.2E1 | 1.0E-9 | 1.0E-9 | 3.5E2 | 6.8E1 | 156 | 116 | 156 | 116 | 0.66 |
| Mp | pg/ml | 1.0E-9 | 1.0E-9 | 1.0E1 | 4.7E1 | 2.5E1 | 2.3E2 | 1.0E-9 | 1.0E-9 | 1.8E2 | 2.4E3 | 156 | 116 | 156 | 116 | 0.55 |
| Mq | pg/ml | 1.0E-9 | 1.0E-9 | 2.1E0 | 4.6E0 | 1.5E1 | 1.7E1 | 1.0E-9 | 1.0E-9 | 1.8E2 | 1.0E2 | 156 | 116 | 156 | 116 | 0.53 |
| Mr | pg/ml | 1.0E-9 | 1.0E-9 | 2.2E1 | 9.9E1 | 1.2E2 | 4.2E2 | 1.0E-9 | 1.0E-9 | 1.4E3 | 3.4E3 | 156 | 116 | 156 | 116 | 0.57 |
| Ms | pg/ml | 3.9E2 | 2.9E2 | 5.1E2 | 3.7E2 | 5.8E2 | 3.7E2 | 1.0E-9 | 1.0E-9 | 3.3E3 | 1.5E3 | 156 | 116 | 156 | 116 | 0.43 |
| Mt | pg/ml | 1.0E-9 | 1.0E0 | 1.0E1 | 4.4E1 | 6.0E1 | 3.0E2 | 1.0E-9 | 1.0E-9 | 7.1E2 | 3.2E3 | 156 | 116 | 156 | 116 | 0.61 |
| Mu | pg/ml | 1.0E-9 | 1.0E-9 | 1.3E0 | 3.4E0 | 9.0E0 | 2.2E1 | 1.0E-9 | 1.0E-9 | 9.9E1 | 2.3E2 | 156 | 116 | 156 | 116 | 0.54 |
| Mv | pg/ml | 1.0E-9 | 1.0E-9 | 9.8E1 | 7.4E1 | 4.8E2 | 2.0E2 | 1.0E-9 | 1.0E-9 | 4.5E3 | 9.2E2 | 156 | 116 | 156 | 116 | 0.54 |
| Mw | pg/ml | 2.3E1 | 5.8E1 | 4.0E2 | 3.2E2 | 2.0E3 | 8.5E2 | 1.0E-9 | 1.0E-9 | 1.8E4 | 5.3E3 | 156 | 116 | 156 | 116 | 0.59 |
| Mx | pg/ml | 1.0E-9 | 1.0E-9 | 2.4E-1 | 8.8E-1 | 9.0E-1 | 3.5E0 | 1.0E-9 | 1.0E-9 | 7.4E0 | 3.2E1 | 156 | 116 | 156 | 116 | 0.58 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| My | pg/ml | 1.0E-9 | 1.0E-9 | 5.7E2 | 1.9E2 | 3.5E3 | 8.1E2 | 1.0E-9 | 1.0E-9 | 3.9E4 | 8.0E3 | 156 | 116 | 156 | 116 | 0.50 |
| Mz | pg/ml | 9.6E0 | 1.8E1 | 2.0E1 | 6.6E1 | 5.0E1 | 2.2E2 | 1.0E-9 | 1.0E-9 | 5.5E2 | 1.9E3 | 156 | 116 | 156 | 116 | 0.67 |
| Na | pg/ml | 1.0E-9 | 1.0E-9 | 5.9E-1 | 8.6E-1 | 1.9E0 | 4.1E0 | 1.0E-9 | 1.0E-9 | 9.6E0 | 4.2E1 | 156 | 116 | 156 | 116 | 0.52 |
| Nb | pg/ml | 1.8E0 | 2.5E0 | 4.2E0 | 6.5E0 | 1.4E1 | 2.2E1 | 1.0E-9 | 1.0E-9 | 1.5E2 | 2.1E2 | 156 | 116 | 156 | 116 | 0.57 |
| Nc | pg/ml | 4.1E2 | 1.7E2 | 6.0E2 | 3.7E2 | 9.0E2 | 4.9E2 | 1.0E-9 | 1.0E-9 | 9.2E3 | 3.2E3 | 156 | 116 | 156 | 116 | 0.39 |
| Nd | pg/ml | 2.8E1 | 1.3E1 | 2.4E1 | 5.1E1 | 1.8E1 | 2.3E2 | 1.0E-9 | 1.0E-9 | 7.8E1 | 2.1E3 | 156 | 116 | 156 | 116 | 0.46 |
| Ne | pg/ml | 4.6E2 | 3.5E2 | 5.8E2 | 4.3E2 | 6.7E2 | 4.4E2 | 1.0E-9 | 1.0E-9 | 7.0E3 | 3.6E3 | 156 | 116 | 156 | 116 | 0.41 |
| Nf | pg/ml | 1.0E-9 | 1.0E-9 | 2.9E0 | 3.4E0 | 1.1E1 | 1.7E1 | 1.0E-9 | 1.0E-9 | 8.2E1 | 1.3E2 | 156 | 116 | 156 | 116 | 0.47 |
| Ng | pg/ml | 1.7E1 | 1.9E1 | 1.1E2 | 9.7E1 | 2.2E2 | 1.7E2 | 1.0E-9 | 1.0E-9 | 1.6E3 | 8.9E2 | 156 | 116 | 156 | 116 | 0.52 |
| Nh | pg/ml | 6.4E1 | 5.3E1 | 8.9E1 | 6.6E1 | 8.3E1 | 6.7E1 | 1.0E-9 | 3.1E0 | 5.6E2 | 5.1E2 | 156 | 116 | 156 | 116 | 0.40 |
| Ni | pg/ml | 2.2E0 | 1.0E-9 | 8.2E1 | 9.8E1 | 1.3E2 | 1.6E2 | 1.0E-9 | 1.0E-9 | 7.1E2 | 1.1E3 | 156 | 116 | 156 | 116 | 0.50 |
| Nj | pg/ml | 7.4E0 | 4.5E0 | 1.1E1 | 7.9E0 | 1.1E1 | 9.7E0 | 1.0E-9 | 1.0E-9 | 6.8E1 | 5.8E1 | 156 | 116 | 156 | 116 | 0.38 |
| Nk | pg/ml | 2.0E1 | 1.4E1 | 3.2E1 | 3.0E1 | 3.8E1 | 4.1E1 | 1.0E-9 | 1.0E-9 | 2.0E2 | 2.0E2 | 156 | 116 | 156 | 116 | 0.48 |
| Nl | pg/ml | 4.6E1 | 3.3E1 | 6.4E1 | 4.2E1 | 9.6E1 | 4.2E1 | 1.0E-9 | 1.0E-9 | 1.1E3 | 2.3E2 | 156 | 116 | 156 | 116 | 0.40 |
| Hl | pg/ml | 2.2E1 | 1.2E1 | 4.0E1 | 1.9E2 | 6.7E1 | 7.6E2 | 1.0E-9 | 1.0E-9 | 3.0E2 | 3.6E3 | 27 | 22 | 27 | 22 | 0.51 |
| Ho | pg/ml | 1.7E1 | 2.0E1 | 2.3E1 | 5.2E1 | 2.0E1 | 8.6E1 | 1.1E0 | 6.7E0 | 8.3E1 | 3.9E2 | 27 | 22 | 27 | 22 | 0.61 |
| Hp | ng/ml | 1.8E0 | 1.6E0 | 1.4E2 | 1.2E2 | 3.2E2 | 3.1E2 | 1.0E-9 | 5.3E-1 | 8.9E2 | 8.9E2 | 27 | 22 | 27 | 22 | 0.47 |
| Tz | pg/ml | 3.2E3 | 7.3E3 | 4.9E3 | 5.3E4 | 5.7E3 | 2.8E5 | 7.4E1 | 1.0E-9 | 3.2E4 | 2.1E6 | 58 | 57 | 58 | 57 | 0.67 |
| Ua | pg/ml | 2.1E3 | 4.1E3 | 1.6E4 | 1.3E4 | 3.2E4 | 2.3E4 | 2.3E2 | 1.0E-9 | 1.4E5 | 1.2E5 | 58 | 57 | 58 | 57 | 0.58 |
| Ub | pg/ml | 6.6E2 | 4.1E2 | 9.6E2 | 6.5E2 | 1.4E3 | 8.1E2 | 5.4E0 | 1.0E-9 | 9.8E3 | 4.4E3 | 58 | 57 | 58 | 57 | 0.42 |
| Ue | pg/ml | 3.1E1 | 2.6E1 | 3.4E1 | 3.9E1 | 2.1E1 | 4.3E1 | 6.6E0 | 9.8E-2 | 9.5E1 | 2.7E2 | 58 | 57 | 58 | 57 | 0.48 |
| Uc | pg/ml | 6.6E2 | 9.4E2 | 1.1E3 | 2.7E3 | 1.1E3 | 7.7E3 | 1.5E1 | 1.0E-9 | 5.5E3 | 5.7E4 | 58 | 57 | 58 | 57 | 0.57 |
| Ud | pg/ml | 1.0E-9 | 1.0E-9 | 6.7E0 | 9.4E-1 | 5.1E1 | 7.1E0 | 1.0E-9 | 1.0E-9 | 3.9E2 | 5.3E1 | 58 | 57 | 58 | 57 | 0.50 |
| Hq | pg/ml | 1.1E0 | 1.3E0 | 1.4E2 | 2.8E2 | 1.6E3 | 2.7E3 | 1.0E-9 | 1.0E-9 | 2.0E4 | 2.8E4 | 156 | 114 | 156 | 114 | 0.52 |
| Hr | pg/ml | 8.8E1 | 8.0E1 | 5.6E2 | 5.6E2 | 1.1E3 | 1.3E3 | 1.0E-9 | 1.0E-9 | 8.4E3 | 8.9E3 | 156 | 114 | 156 | 114 | 0.49 |
| Hu | pg/ml | 7.7E0 | 2.1E1 | 7.9E3 | 2.8E3 | 5.5E4 | 2.5E4 | 1.0E-9 | 1.0E-9 | 6.3E5 | 2.6E5 | 156 | 114 | 156 | 114 | 0.54 |
| Hv | pg/ml | 1.5E0 | 1.4E0 | 2.7E0 | 1.2E1 | 6.5E0 | 8.5E1 | 1.0E-9 | 1.0E-9 | 6.9E1 | 8.9E2 | 156 | 114 | 156 | 114 | 0.51 |
| Hw | pg/ml | 5.5E0 | 5.6E0 | 1.8E1 | 1.0E2 | 6.3E1 | 8.8E2 | 1.0E-9 | 1.0E-9 | 6.4E2 | 9.4E3 | 156 | 114 | 156 | 114 | 0.49 |
| Hx | pg/ml | 8.4E0 | 1.2E1 | 8.4E1 | 4.8E1 | 7.4E2 | 1.5E2 | 1.0E-9 | 1.0E-9 | 9.3E3 | 1.3E3 | 156 | 114 | 156 | 114 | 0.57 |
| Ib | ng/ml | 4.1E-2 | 3.3E-2 | 1.8E0 | 1.2E0 | 6.6E0 | 7.6E0 | 1.0E-9 | 1.0E-9 | 3.6E1 | 5.6E1 | 57 | 55 | 57 | 55 | 0.49 |
| Ic | U/ml | 2.2E2 | 2.2E2 | 3.0E2 | 1.6E3 | 5.9E2 | 8.8E3 | 2.4E0 | 6.6E0 | 4.1E3 | 6.5E4 | 57 | 55 | 57 | 55 | 0.58 |
| Id | U/ml | 4.8E-1 | 9.9E-1 | 7.9E-1 | 9.8E0 | 1.0E0 | 5.8E1 | 1.0E-9 | 5.1E-2 | 6.4E0 | 4.3E2 | 57 | 55 | 57 | 55 | 0.70 |
| Tt | pg/ml | 1.7E2 | 1.8E2 | 1.7E2 | 1.8E2 | 5.1E1 | 6.5E1 | 4.3E1 | 7.3E1 | 3.0E2 | 4.4E2 | 51 | 53 | 51 | 53 | 0.53 |
| To | pg/ml | 1.8E0 | 1.6E0 | 1.9E0 | 2.2E0 | 1.9E0 | 2.6E0 | 1.0E-9 | 1.0E-9 | 7.6E0 | 1.2E1 | 55 | 55 | 55 | 55 | 0.50 |
| Tr | pg/ml | 2.9E0 | 3.8E0 | 5.3E0 | 1.4E1 | 6.5E0 | 4.3E1 | 1.0E-9 | 2.4E-1 | 3.8E1 | 3.1E2 | 53 | 54 | 53 | 54 | 0.58 |
| Tn | pg/ml | 2.6E1 | 4.4E1 | 8.2E1 | 1.8E2 | 2.3E2 | 4.6E2 | 3.5E0 | 2.4E0 | 1.7E3 | 2.3E3 | 55 | 55 | 55 | 55 | 0.62 |
| Tv | ng/ml | 1.2E1 | 1.5E1 | 1.5E1 | 1.7E2 | 1.6E1 | 9.6E2 | 1.0E-9 | 1.0E-9 | 7.5E1 | 7.1E3 | 55 | 55 | 55 | 55 | 0.57 |
| Ih | ng/ml | 5.3E1 | 1.3E2 | 1.8E2 | 3.8E2 | 3.2E2 | 5.9E2 | 1.0E-9 | 1.0E-9 | 1.8E3 | 3.6E3 | 156 | 115 | 156 | 115 | 0.63 |
| Ii | ng/ml | 6.3E1 | 1.2E2 | 2.2E2 | 2.7E2 | 5.4E2 | 5.8E2 | 1.6E0 | 7.3E-1 | 5.2E3 | 4.5E3 | 156 | 115 | 156 | 115 | 0.61 |
| Ij | ng/ml | 7.3E1 | 1.2E2 | 2.1E2 | 3.9E2 | 7.5E2 | 2.3E3 | 2.8E0 | 2.1E1 | 6.4E3 | 2.4E4 | 156 | 112 | 156 | 112 | 0.64 |
| Ik | ng/ml | 1.0E1 | 1.5E1 | 2.6E3 | 2.6E3 | 1.7E4 | 4.9E2 | 5.9E-1 | 2.1E0 | 1.2E5 | 2.1E3 | 155 | 113 | 155 | 113 | 0.56 |
| Il | ng/ml | 3.4E2 | 4.4E2 | 1.3E3 | 1.5E3 | 2.9E3 | 2.9E3 | 1.0E-9 | 1.0E-9 | 1.2E4 | 1.2E4 | 154 | 112 | 154 | 112 | 0.55 |
| Im | ng/ml | 1.8E2 | 3.1E2 | 3.4E2 | 7.5E2 | 5.9E2 | 1.1E3 | 1.4E1 | 4.5E1 | 6.0E3 | 6.2E3 | 155 | 113 | 155 | 113 | 0.68 |
| In | ng/ml | 3.5E0 | 2.7E0 | 2.0E1 | 5.6E1 | 9.2E1 | 4.2E2 | 1.0E-9 | 1.0E-9 | 1.1E3 | 4.5E3 | 156 | 115 | 156 | 115 | 0.49 |
| Hb | ng/ml | 1.8E1 | 3.7E1 | 2.5E1 | 4.8E1 | 2.8E1 | 4.3E1 | 4.8E-1 | 2.6E0 | 1.4E2 | 2.0E2 | 57 | 59 | 57 | 59 | 0.71 |
| Hc | pg/ml | 7.3E2 | 6.4E2 | 4.2E3 | 2.1E3 | 1.4E4 | 6.8E3 | 1.0E-9 | 1.0E-9 | 1.0E5 | 5.0E4 | 57 | 59 | 57 | 59 | 0.45 |
| Hf | ng/ml | 1.5E2 | 2.6E2 | 3.9E2 | 4.3E2 | 5.7E2 | 5.8E2 | 1.0E-9 | 1.0E-9 | 2.5E3 | 3.2E3 | 57 | 59 | 57 | 59 | 0.56 |
| Io | ng/ml | 9.5E3 | 1.4E4 | 2.1E4 | 2.2E4 | 6.3E4 | 2.4E4 | 1.2E2 | 1.0E-9 | 7.1E5 | 1.1E5 | 155 | 116 | 155 | 116 | 0.60 |
| Ip | ng/ml | 8.7E0 | 2.7E1 | 2.0E1 | 2.7E1 | 2.7E1 | 2.6E1 | 1.0E-9 | 1.0E-9 | 2.3E2 | 1.6E2 | 155 | 116 | 155 | 116 | 0.59 |
| Iq | ug/ml | 1.1E-1 | 1.5E-1 | 6.5E-1 | 3.3E0 | 2.8E0 | 2.1E1 | 1.0E-9 | 1.0E-9 | 3.4E1 | 2.2E2 | 155 | 116 | 155 | 116 | 0.57 |
| Ir | ug/ml | 3.3E-1 | 9.4E-1 | 1.2E0 | 1.0E1 | 3.3E0 | 4.1E1 | 1.0E-9 | 1.0E-9 | 2.6E1 | 3.7E2 | 154 | 116 | 154 | 116 | 0.68 |
| Is | ng/ml | 1.5E0 | 3.8E0 | 6.0E0 | 1.7E1 | 1.2E1 | 3.5E1 | 1.0E-9 | 1.0E-9 | 8.8E1 | 2.6E2 | 155 | 116 | 155 | 116 | 0.63 |
| It | ng/ml | 1.3E0 | 3.2E0 | 1.5E1 | 2.0E1 | 7.5E1 | 8.3E1 | 1.0E-9 | 1.0E-9 | 8.3E2 | 6.8E2 | 155 | 116 | 155 | 116 | 0.63 |
| Iu | ng/ml | 1.5E2 | 2.0E2 | 9.6E2 | 1.9E3 | 3.2E3 | 5.0E3 | 1.0E-9 | 1.0E-9 | 2.9E4 | 2.4E4 | 155 | 116 | 155 | 116 | 0.57 |
| Iv | ng/ml | 1.1E1 | 2.2E1 | 3.7E1 | 1.5E2 | 9.1E1 | 6.0E2 | 1.0E-9 | 1.0E-9 | 7.7E2 | 3.8E3 | 155 | 115 | 155 | 115 | 0.62 |
| Iz | ng/ml | 1.1E2 | 1.3E2 | 4.2E2 | 2.7E2 | 9.3E2 | 3.2E2 | 1.5E0 | 4.9E0 | 6.1E3 | 1.7E3 | 57 | 59 | 57 | 59 | 0.54 |
| Yg | pg/ml | 2.4E2 | 2.8E2 | 2.3E3 | 8.0E2 | 9.5E3 | 1.0E3 | 1.0E-9 | 1.0E-9 | 5.0E4 | 3.9E3 | 27 | 21 | 27 | 21 | 0.58 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yh | pg/ml | 2.1E2 | 2.6E2 | 3.3E2 | 4.7E2 | 4.4E2 | 5.8E2 | 1.0E-9 | 1.0E-9 | 1.8E3 | 2.1E3 | 27 | 21 | 27 | 21 | 0.56 |
| Yi | pg/ml | 2.2E2 | 5.1E2 | 4.4E2 | 2.3E3 | 5.4E2 | 5.9E3 | 1.0E-9 | 1.0E-9 | 2.0E3 | 2.6E4 | 27 | 21 | 27 | 21 | 0.68 |
| Yk | U/ml | 1.0E-9 | 1.0E-9 | 2.5E-1 | 1.5E-1 | 7.0E-1 | 4.0E-1 | 1.0E-9 | 1.0E-9 | 3.0E0 | 1.4E0 | 27 | 21 | 27 | 21 | 0.46 |
| Yj | pg/ml | 1.5E2 | 1.1E2 | 3.6E2 | 2.2E2 | 6.4E2 | 3.2E2 | 1.0E-9 | 5.2E1 | 3.2E3 | 1.5E3 | 27 | 21 | 27 | 21 | 0.45 |
| Yd | ng/ml | 1.6E-1 | 2.8E-1 | 3.6E-1 | 4.5E-1 | 5.0E-1 | 5.9E-1 | 6.6E-3 | 1.7E-2 | 1.8E0 | 2.3E0 | 28 | 22 | 28 | 22 | 0.59 |
| Wb | pg/ml | 2.6E4 | 4.3E4 | 3.0E4 | 7.1E4 | 1.8E4 | 1.3E5 | 6.3E3 | 1.0E4 | 8.4E4 | 6.4E5 | 28 | 22 | 28 | 22 | 0.69 |
| Vz | pg/ml | 3.7E0 | 3.9E0 | 4.6E0 | 5.4E0 | 4.0E0 | 5.7E0 | 1.0E-9 | 7.6E-2 | 1.6E1 | 2.2E1 | 28 | 22 | 28 | 22 | 0.54 |
| Si | ng/ml | 1.0E0 | 1.4E0 | 2.1E0 | 1.9E0 | 3.1E0 | 1.7E0 | 8.6E-3 | 3.3E-1 | 1.0E1 | 6.0E0 | 27 | 22 | 27 | 22 | 0.61 |
| Sf | mIU/mL | 2.0E1 | 2.0E1 | 7.4E1 | 2.3E1 | 1.5E2 | 2.0E1 | 7.8E-1 | 1.7E0 | 7.2E2 | 8.3E1 | 27 | 22 | 27 | 22 | 0.47 |
| Sh | mIU/mL | 1.8E1 | 1.2E1 | 6.4E1 | 2.1E1 | 1.2E2 | 1.8E1 | 1.4E-1 | 7.8E-2 | 5.7E2 | 6.1E1 | 27 | 22 | 27 | 22 | 0.47 |
| Sj | ng/ml | 4.4E-1 | 4.5E-1 | 4.2E-1 | 4.5E-1 | 9.2E-2 | 8.6E-2 | 2.5E-1 | 3.2E-1 | 6.1E-1 | 7.2E-1 | 27 | 22 | 27 | 22 | 0.59 |
| Rc | pg/ml | 6.5E3 | 7.4E3 | 7.5E3 | 7.6E3 | 5.3E3 | 5.0E3 | 5.5E2 | 6.7E2 | 2.2E4 | 2.7E4 | 57 | 57 | 57 | 57 | 0.53 |
| Rb | pg/ml | 7.5E-1 | 8.8E-1 | 2.7E0 | 3.3E0 | 4.1E0 | 8.0E0 | 1.0E-9 | 1.0E-9 | 1.6E1 | 5.6E1 | 57 | 57 | 57 | 57 | 0.53 |
| Zq | 2.6ng/ml | 1.8E2 | 3.6E2 | 2.3E2 | 3.8E2 | 1.5E2 | 1.9E2 | 1.7E1 | 4.8E1 | 5.2E2 | 9.7E2 | 27 | 21 | 27 | 21 | 0.72 |
| Zw | 2.5ng/ml | 5.3E0 | 6.5E0 | 9.4E0 | 1.3E1 | 1.2E1 | 1.8E1 | 2.4E-1 | 2.4E-1 | 5.9E1 | 6.3E1 | 28 | 22 | 28 | 22 | 0.52 |
| Zx | 2.3mU/ml | 1.2E-1 | 1.4E-1 | 2.9E-1 | 3.5E-1 | 5.4E-1 | 5.6E-1 | 4.2E-2 | 3.2E-2 | 2.9E0 | 2.1E0 | 28 | 22 | 28 | 22 | 0.56 |
| Pz | ng/ml | 3.2E3 | 5.7E3 | 5.8E3 | 6.1E3 | 7.2E3 | 4.4E3 | 1.6E1 | 1.9E2 | 7.0E4 | 2.5E4 | 153 | 114 | 153 | 114 | 0.57 |
| Qa | ng/ml | 2.8E3 | 6.5E3 | 5.8E3 | 1.2E4 | 7.5E3 | 2.2E4 | 1.5E2 | 4.1E2 | 4.2E4 | 2.2E5 | 153 | 114 | 153 | 114 | 0.67 |
| Qb | ng/ml | 1.0E2 | 1.5E2 | 2.0E2 | 3.1E2 | 3.1E2 | 4.5E2 | 7.9E-1 | 6.7E0 | 2.8E3 | 4.1E3 | 153 | 114 | 153 | 114 | 0.61 |
| Qc | ng/ml | 1.7E2 | 3.8E2 | 3.9E2 | 5.8E2 | 5.3E2 | 6.5E2 | 1.0E0 | 1.0E-9 | 3.8E3 | 4.3E3 | 153 | 114 | 153 | 114 | 0.61 |
| Qd | ng/ml | 7.2E3 | 1.4E4 | 2.8E4 | 3.7E4 | 1.7E5 | 6.2E4 | 2.4E2 | 1.7E3 | 2.0E6 | 4.3E5 | 153 | 114 | 153 | 114 | 0.68 |
| Qe | ng/ml | 6.5E2 | 1.8E3 | 2.0E3 | 2.6E3 | 8.0E3 | 2.7E3 | 7.6E0 | 8.8E0 | 9.7E4 | 1.8E4 | 153 | 114 | 153 | 114 | 0.70 |
| Jd | ng/ml | 4.1E-1 | 1.4E0 | 5.4E0 | 2.9E0 | 2.1E1 | 4.3E0 | 1.0E-9 | 1.0E-9 | 1.2E2 | 2.1E1 | 57 | 57 | 57 | 57 | 0.65 |
| Je | ng/ml | 1.0E-9 | 1.0E-9 | 2.3E0 | 1.6E0 | 7.0E0 | 2.6E0 | 1.0E-9 | 1.0E-9 | 4.6E1 | 1.1E1 | 57 | 57 | 57 | 57 | 0.54 |
| Jf | ng/ml | 1.0E-9 | 1.0E-9 | 1.0E0 | 1.5E0 | 2.2E0 | 2.4E0 | 1.0E-9 | 1.0E-9 | 1.2E1 | 9.1E0 | 57 | 57 | 57 | 57 | 0.54 |
| Jg | ng/ml | 3.7E2 | 8.2E2 | 7.2E2 | 1.2E3 | 1.0E3 | 1.1E3 | 5.8E0 | 1.3E1 | 1.0E4 | 7.1E3 | 156 | 114 | 156 | 114 | 0.66 |
| Jh | ng/ml | 2.9E0 | 4.8E0 | 2.9E1 | 2.6E1 | 1.2E2 | 6.4E1 | 1.0E-9 | 1.0E-9 | 1.2E3 | 4.9E2 | 156 | 114 | 156 | 114 | 0.59 |
| Ji | ng/ml | 4.6E1 | 8.5E1 | 6.9E1 | 1.5E2 | 7.4E1 | 1.7E2 | 1.1E0 | 1.4E1 | 5.3E2 | 1.3E3 | 156 | 114 | 156 | 114 | 0.70 |
| Sr | pg/mL | 2.5E2 | 7.4E2 | 6.5E2 | 1.6E3 | 1.0E3 | 3.0E3 | 1.0E-9 | 1.0E-9 | 4.3E3 | 2.1E4 | 57 | 56 | 57 | 56 | 0.70 |
| Ss | pg/mL | 1.0E5 | 8.8E4 | 1.4E5 | 1.6E5 | 1.5E5 | 2.1E5 | 7.6E3 | 2.7E3 | 7.0E5 | 1.3E6 | 57 | 56 | 57 | 56 | 0.50 |
| St | pg/mL | 2.1E7 | 5.3E7 | 4.0E7 | 1.2E8 | 6.4E7 | 2.7E8 | 7.8E5 | 1.0E-9 | 4.1E8 | 1.7E9 | 55 | 57 | 55 | 57 | 0.69 |
| Wc | ng/ml | 1.0E-9 | 1.0E-9 | 3.5E-2 | 1.5E-1 | 7.2E-2 | 3.9E-1 | 1.0E-9 | 1.0E-9 | 3.0E-1 | 1.8E0 | 28 | 22 | 28 | 22 | 0.55 |
| Wd | ng/ml | 9.7E0 | 9.7E0 | 2.7E1 | 4.8E1 | 5.7E1 | 1.1E2 | 1.0E0 | 1.5E0 | 2.9E2 | 4.1E2 | 28 | 22 | 28 | 22 | 0.52 |
| We | ng/ml | 2.8E-1 | 4.9E-1 | 1.1E0 | 1.7E0 | 1.5E0 | 4.8E0 | 1.0E-9 | 1.0E-9 | 5.5E0 | 2.3E1 | 28 | 22 | 28 | 22 | 0.52 |
| Wg | ng/ml | 1.0E-9 | 1.0E-9 | 1.0E-9 | 2.4E-2 | 0.0E0 | 1.1E-1 | 1.0E-9 | 1.0E-9 | 1.0E-9 | 5.3E-1 | 28 | 22 | 28 | 22 | 0.52 |
| Wh | ng/ml | 1.2E-2 | 1.0E-2 | 4.2E-2 | 3.2E-2 | 8.5E-2 | 7.1E-2 | 1.0E-9 | 1.0E-9 | 3.5E-1 | 3.4E-1 | 28 | 22 | 28 | 22 | 0.49 |
| Wf | ng/ml | 1.0E-9 | 1.0E-9 | 1.2E-1 | 1.8E-1 | 2.6E-1 | 4.9E-1 | 1.0E-9 | 1.0E-9 | 1.2E0 | 2.3E0 | 28 | 22 | 28 | 22 | 0.48 |
| Ra | pg/ml | 1.0E-9 | 1.0E-9 | 4.9E-1 | 1.5E0 | 1.1E0 | 8.5E0 | 1.0E-9 | 1.0E-9 | 3.8E0 | 6.4E1 | 57 | 57 | 57 | 57 | 0.47 |
| Qz | pg/ml | 1.1E1 | 9.0E0 | 6.5E1 | 3.6E1 | 1.0E2 | 6.5E1 | 1.0E-9 | 1.0E-9 | 4.5E2 | 2.8E2 | 57 | 57 | 57 | 57 | 0.41 |
| Qy | pg/ml | 3.9E-1 | 4.6E-1 | 6.7E0 | 2.2E1 | 3.2E1 | 1.1E2 | 1.0E-9 | 1.0E-9 | 2.3E2 | 7.3E2 | 57 | 57 | 57 | 57 | 0.52 |
| Qx | pg/ml | 1.0E-9 | 1.0E-9 | 4.7E0 | 3.7E0 | 2.5E1 | 1.5E1 | 1.0E-9 | 1.0E-9 | 1.9E2 | 1.1E2 | 57 | 57 | 57 | 57 | 0.50 |
| Qw | pg/ml | 6.4E-1 | 1.0E-9 | 3.0E0 | 3.1E0 | 8.6E0 | 1.2E1 | 1.0E-9 | 1.0E-9 | 5.1E1 | 6.6E1 | 57 | 57 | 57 | 57 | 0.41 |
| Qv | pg/ml | 1.9E4 | 1.2E4 | 2.8E4 | 4.4E4 | 4.9E4 | 1.3E5 | 1.4E3 | 1.0E-9 | 3.7E5 | 9.4E5 | 57 | 57 | 57 | 57 | 0.46 |
| Qu | pg/ml | 6.2E0 | 8.3E0 | 1.0E2 | 9.4E1 | 1.9E2 | 2.0E2 | 1.0E-9 | 1.0E-9 | 7.1E2 | 9.8E2 | 57 | 57 | 57 | 57 | 0.50 |
| Qt | pg/ml | 1.4E1 | 1.5E1 | 5.5E1 | 3.9E1 | 1.3E2 | 6.5E1 | 1.0E-9 | 1.0E-9 | 7.1E2 | 2.2E2 | 57 | 57 | 57 | 57 | 0.49 |
| Qh | ng/ml | 1.7E1 | 2.6E1 | 3.1E1 | 7.7E1 | 4.0E1 | 1.3E2 | 4.6E-1 | 4.3E-1 | 1.8E2 | 8.0E2 | 57 | 57 | 57 | 57 | 0.64 |
| Qg | ng/ml | 7.6E0 | 7.3E0 | 1.3E1 | 1.1E1 | 1.5E1 | 1.3E1 | 1.5E-1 | 3.0E-1 | 7.5E1 | 8.1E1 | 57 | 57 | 57 | 57 | 0.48 |
| Jj | ng/ml | 6.0E2 | 4.3E2 | 3.2E3 | 7.8E2 | 2.7E4 | 1.3E3 | 2.0E1 | 1.2E1 | 3.4E5 | 1.1E4 | 156 | 114 | 156 | 114 | 0.43 |
| Jk | ng/ml | 3.0E0 | 3.0E0 | 2.2E1 | 2.7E1 | 5.2E1 | 5.6E1 | 1.0E-9 | 2.4E-1 | 2.8E2 | 3.9E2 | 156 | 114 | 156 | 114 | 0.55 |
| Jl | ng/ml | 4.6E-1 | 6.4E-1 | 1.5E0 | 9.1E1 | 3.1E0 | 9.3E2 | 1.2E-3 | 2.0E-2 | 2.0E1 | 9.9E3 | 156 | 114 | 156 | 114 | 0.59 |
| Jm | ng/ml | 1.6E1 | 3.2E1 | 5.4E1 | 8.6E1 | 1.3E2 | 2.1E2 | 1.0E-9 | 1.9E-1 | 1.0E3 | 2.1E3 | 156 | 114 | 156 | 114 | 0.61 |
| Jn | pg/ml | 2.8E-1 | 5.5E-1 | 1.8E0 | 1.6E1 | 6.5E0 | 9.2E1 | 1.0E-9 | 1.0E-9 | 5.8E1 | 7.3E2 | 156 | 114 | 156 | 114 | 0.63 |
| Jo | pg/ml | 4.1E3 | 4.9E3 | 4.9E3 | 6.7E3 | 3.9E3 | 1.0E4 | 2.6E2 | 2.3E2 | 2.4E4 | 1.0E5 | 156 | 114 | 156 | 114 | 0.55 |
| Jp | pg/ml | 6.8E4 | 8.3E4 | 7.1E4 | 9.0E4 | 3.7E4 | 4.2E4 | 2.1E3 | 2.8E4 | 1.9E5 | 3.8E5 | 156 | 114 | 156 | 114 | 0.65 |
| Jq | pg/ml | 9.1E1 | 1.4E2 | 1.4E2 | 3.2E2 | 1.8E2 | 9.0E2 | 5.6E0 | 5.6E0 | 1.1E3 | 8.7E3 | 156 | 114 | 156 | 114 | 0.60 |
| Jr | pg/ml | 2.5E0 | 8.6E0 | 3.0E1 | 1.5E2 | 1.7E2 | 8.7E2 | 1.0E-9 | 1.0E-9 | 1.9E3 | 7.4E3 | 156 | 114 | 156 | 114 | 0.63 |
| Js | pg/ml | 1.3E1 | 1.9E1 | 4.3E1 | 1.2E2 | 1.6E2 | 4.8E2 | 1.0E-9 | 1.9E0 | 1.6E3 | 3.0E3 | 156 | 114 | 156 | 114 | 0.63 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jt | pg/ml | 2.2E3 | 3.3E3 | 2.7E3 | 4.7E3 | 1.8E3 | 6.6E3 | 1.5E2 | 3.8E2 | 9.2E3 | 5.2E4 | 156 | 114 | 156 | 114 | 0.64 |
| Xa | pg/ml | 1.0E-9 | 6.9E0 | 9.1E0 | 9.1E1 | 2.0E1 | 2.8E2 | 1.0E-9 | 1.0E-9 | 9.6E1 | 1.2E3 | 28 | 22 | 28 | 22 | 0.64 |
| Ye | pg/ml | 1.0E-9 | 1.0E-9 | 7.3E0 | 1.3E0 | 1.8E1 | 3.4E0 | 1.0E-9 | 1.0E-9 | 6.9E1 | 1.4E1 | 28 | 22 | 28 | 22 | 0.40 |
| Tm | pg/ml | 1.0E-9 | 1.0E-9 | 3.5E0 | 1.9E0 | 5.1E0 | 3.6E0 | 1.0E-9 | 1.0E-9 | 1.8E1 | 8.4E0 | 28 | 22 | 28 | 22 | 0.43 |
| Tl | pg/ml | 1.2E-1 | 1.3E-1 | 3.0E-1 | 1.5E0 | 3.6E-1 | 5.2E0 | 1.0E-9 | 1.0E-9 | 1.2E0 | 2.5E1 | 28 | 22 | 28 | 22 | 0.55 |
| Ju | mIU/ml | 1.0E1 | 1.4E1 | 2.9E1 | 2.3E1 | 4.5E1 | 2.4E1 | 2.5E-1 | 1.7E-1 | 2.3E2 | 1.1E2 | 57 | 57 | 57 | 57 | 0.57 |
| Jv | mIU/ml | 1.4E1 | 1.8E1 | 5.1E1 | 3.3E1 | 8.3E1 | 3.6E1 | 2.4E-2 | 1.7E-2 | 4.4E2 | 1.8E2 | 57 | 57 | 57 | 57 | 0.54 |
| Jy | ng/ml | 1.6E-3 | 1.6E-3 | 1.9E-3 | 3.6E-3 | 1.0E-3 | 7.6E-3 | 5.3E-4 | 1.7E-4 | 4.4E-3 | 4.1E-2 | 57 | 57 | 57 | 57 | 0.51 |
| Kc | pg/ml | 2.1E1 | 2.6E1 | 2.9E1 | 5.8E1 | 3.1E1 | 6.8E1 | 1.0E-9 | 1.0E-9 | 1.4E2 | 3.2E2 | 57 | 59 | 57 | 59 | 0.63 |
| Kd | pg/ml | 1.0E-9 | 1.0E-9 | 1.8E2 | 1.1E3 | 7.3E2 | 5.1E3 | 1.0E-9 | 1.0E-9 | 4.8E3 | 3.8E4 | 57 | 59 | 57 | 59 | 0.55 |
| Ke | pg/ml | 1.1E4 | 1.5E4 | 1.2E4 | 2.6E4 | 7.8E3 | 4.3E4 | 6.7E2 | 4.2E3 | 3.1E4 | 3.2E5 | 57 | 59 | 57 | 59 | 0.66 |
| Kf | pg/mL | 5.4E0 | 8.1E0 | 5.3E0 | 1.0E1 | 4.4E0 | 1.1E1 | 1.0E-9 | 1.0E-9 | 1.8E1 | 7.8E1 | 57 | 59 | 57 | 59 | 0.67 |
| Kg | pg/mL | 7.6E2 | 1.2E3 | 1.5E3 | 2.7E3 | 1.7E3 | 5.7E3 | 7.7E1 | 1.3E2 | 8.1E3 | 3.6E4 | 57 | 59 | 57 | 59 | 0.60 |
| Ki | pg/ml | 5.9E1 | 6.1E1 | 6.7E1 | 7.4E1 | 5.5E1 | 5.7E1 | 1.0E-9 | 1.0E-9 | 2.9E2 | 2.5E2 | 57 | 59 | 57 | 59 | 0.54 |
| Kj | pg/ml | 7.0E2 | 9.3E2 | 1.3E3 | 1.6E3 | 1.5E3 | 2.3E3 | 6.6E1 | 3.3E1 | 8.8E3 | 1.5E4 | 57 | 59 | 57 | 59 | 0.56 |
| Kk | pg/ml | 6.8E0 | 1.0E1 | 9.7E0 | 1.8E1 | 1.4E1 | 1.8E1 | 1.0E-9 | 1.0E-9 | 8.1E1 | 6.1E1 | 57 | 59 | 57 | 59 | 0.66 |
| Kl | pg/ml | 1.8E4 | 1.9E4 | 2.6E4 | 3.0E4 | 2.4E4 | 2.8E4 | 2.4E2 | 2.3E2 | 1.1E5 | 1.3E5 | 57 | 59 | 57 | 59 | 0.55 |
| Kn | pg/ml | 1.5E1 | 5.7E1 | 4.1E1 | 1.8E2 | 6.3E1 | 6.4E2 | 1.0E-9 | 1.0E-9 | 3.4E2 | 4.9E3 | 57 | 59 | 57 | 59 | 0.65 |
| Ko | pg/ml | 2.2E2 | 5.0E2 | 3.6E2 | 7.2E2 | 4.2E2 | 7.9E2 | 1.0E-9 | 1.0E-9 | 1.8E3 | 4.1E3 | 57 | 59 | 57 | 59 | 0.68 |
| Kp | pg/ml | 3.0E2 | 4.0E2 | 3.1E2 | 6.5E2 | 2.4E2 | 1.7E3 | 1.0E-9 | 1.0E-9 | 8.0E2 | 1.3E4 | 57 | 59 | 57 | 59 | 0.63 |
| Kq | pg/ml | 2.8E2 | 4.2E2 | 3.3E2 | 3.6E3 | 3.2E2 | 2.1E4 | 1.6E0 | 6.1E1 | 2.1E3 | 1.6E5 | 54 | 57 | 54 | 57 | 0.70 |
| Kr | pg/ml | 1.0E-9 | 9.9E-1 | 1.4E0 | 1.0E1 | 2.4E0 | 5.5E1 | 1.0E-9 | 1.0E-9 | 1.2E1 | 4.2E2 | 54 | 57 | 54 | 57 | 0.61 |
| Ks | pg/ml | 1.2E4 | 2.0E4 | 1.9E4 | 2.4E4 | 1.9E4 | 1.8E4 | 5.1E1 | 9.9E2 | 7.9E4 | 6.3E4 | 54 | 57 | 54 | 57 | 0.60 |
| Ps | ng/ml | 1.3E2 | 3.2E2 | 2.9E2 | 1.4E3 | 4.0E2 | 3.0E3 | 5.5E0 | 1.6E1 | 1.5E3 | 1.2E4 | 27 | 22 | 27 | 22 | 0.69 |
| Kx | ng/ml | 1.0E-9 | 4.8E-3 | 4.4E-3 | 1.4E-2 | 9.9E-3 | 2.2E-2 | 1.0E-9 | 1.0E-9 | 5.1E-2 | 1.0E-1 | 56 | 59 | 56 | 59 | 0.65 |
| Ky | ng/ml | 1.1E-1 | 2.0E-1 | 3.7E-1 | 5.1E-1 | 7.6E-1 | 8.6E-1 | 1.0E-9 | 1.0E-9 | 5.1E0 | 4.4E0 | 56 | 59 | 56 | 59 | 0.57 |
| Kz | ng/ml | 1.0E-9 | 1.0E-9 | 3.7E-3 | 4.0E-3 | 5.6E-3 | 6.5E-3 | 1.0E-9 | 1.0E-9 | 1.4E-2 | 2.5E-2 | 56 | 59 | 56 | 59 | 0.49 |
| Rz | ng/ml | 3.6E-1 | 3.2E-1 | 7.2E-1 | 8.6E-1 | 9.5E-1 | 1.6E0 | 4.6E-3 | 1.7E-2 | 3.4E0 | 7.5E0 | 27 | 22 | 27 | 22 | 0.54 |
| Ry | ng/ml | 1.6E-2 | 2.4E-2 | 1.9E-2 | 4.5E-2 | 1.9E-2 | 7.5E-2 | 1.0E-9 | 1.0E-9 | 6.5E-2 | 3.5E-1 | 27 | 22 | 27 | 22 | 0.61 |
| Rx | ng/ml | 1.0E-9 | 1.8E-5 | 1.7E-3 | 1.4E-3 | 2.7E-3 | 2.3E-3 | 1.0E-9 | 1.0E-9 | 8.6E-3 | 7.6E-3 | 27 | 22 | 27 | 22 | 0.52 |
| Ld | pg/ml | 1.0E-9 | 7.5E-1 | 2.9E0 | 5.5E0 | 9.6E0 | 8.9E0 | 1.0E-9 | 1.0E-9 | 6.9E1 | 5.0E1 | 57 | 60 | 57 | 60 | 0.63 |
| Lh | pg/ml | 1.1E4 | 2.1E4 | 2.0E4 | 4.0E4 | 2.9E4 | 7.1E4 | 1.0E-9 | 1.0E3 | 2.6E5 | 4.8E5 | 156 | 115 | 156 | 115 | 0.65 |
| Li | pg/ml | 2.8E3 | 7.7E3 | 8.5E3 | 3.6E4 | 2.6E4 | 1.0E5 | 1.3E1 | 3.7E1 | 2.9E5 | 9.2E5 | 156 | 115 | 156 | 115 | 0.69 |
| Lj | pg/ml | 1.9E3 | 6.1E3 | 1.1E4 | 3.3E4 | 4.3E4 | 6.6E4 | 1.0E-9 | 3.4E1 | 4.3E5 | 4.1E5 | 156 | 115 | 156 | 115 | 0.67 |
| Lp | pg/ml | 6.4E0 | 1.5E1 | 5.6E1 | 1.6E2 | 1.3E2 | 3.8E2 | 1.0E-9 | 1.0E-9 | 5.8E2 | 1.4E3 | 27 | 22 | 27 | 22 | 0.56 |
| Lt | pg/ml | 1.0E-9 | 1.0E-9 | 1.5E0 | 2.1E0 | 5.5E0 | 6.7E0 | 1.0E-9 | 1.0E-9 | 2.5E1 | 2.5E1 | 27 | 22 | 27 | 22 | 0.51 |
| Rv | ng/ml | 5.0E-4 | 5.0E-4 | 8.8E-4 | 2.2E-3 | 8.6E-4 | 4.4E-3 | 1.0E-9 | 1.0E-9 | 2.6E-3 | 1.6E-2 | 27 | 22 | 27 | 22 | 0.46 |
| Ru | ng/ml | 1.0E-9 | 1.0E-9 | 1.9E-2 | 3.4E-2 | 7.1E-2 | 1.0E-1 | 1.0E-9 | 1.0E-9 | 3.1E-1 | 3.5E-1 | 27 | 22 | 27 | 22 | 0.53 |
| Rt | ng/ml | 6.5E-2 | 8.1E-2 | 9.0E-2 | 4.8E-1 | 9.5E-2 | 1.6E0 | 2.2E-3 | 1.3E-3 | 3.8E-1 | 7.4E0 | 27 | 22 | 27 | 22 | 0.61 |
| Yl | pg/ml | 1.1E1 | 1.3E1 | 1.4E1 | 3.1E1 | 1.3E1 | 4.7E1 | 1.0E-9 | 1.0E-9 | 4.7E1 | 2.2E2 | 28 | 22 | 28 | 22 | 0.60 |
| Rm | ng/ml | 1.5E1 | 2.0E1 | 3.7E1 | 6.7E1 | 6.4E1 | 1.1E2 | 2.2E-1 | 3.9E-1 | 3.4E2 | 6.5E2 | 57 | 56 | 57 | 56 | 0.61 |
| Rh | ng/ml | 1.4E2 | 1.8E2 | 2.9E2 | 5.9E2 | 5.1E2 | 2.3E3 | 7.5E0 | 2.5E1 | 3.8E3 | 1.7E4 | 57 | 56 | 57 | 56 | 0.52 |
| Ri | ng/ml | 2.0E-1 | 1.0E-9 | 4.1E0 | 2.3E0 | 7.9E0 | 4.8E0 | 1.0E-9 | 1.0E-9 | 4.5E1 | 2.5E1 | 57 | 56 | 57 | 56 | 0.42 |
| Rg | ng/ml | 1.0E-9 | 1.0E-9 | 4.8E-3 | 1.9E-1 | 1.7E-2 | 6.4E-1 | 1.0E-9 | 1.0E-9 | 8.4E-2 | 3.3E0 | 57 | 56 | 57 | 56 | 0.57 |
| Rj | ng/ml | 1.0E-9 | 1.0E-9 | 9.1E-1 | 5.6E0 | 1.9E0 | 3.6E1 | 1.0E-9 | 1.0E-9 | 1.1E1 | 2.7E2 | 57 | 56 | 57 | 56 | 0.47 |
| Rf | ng/ml | 3.5E-1 | 3.9E-1 | 6.7E-1 | 1.4E0 | 8.1E-1 | 3.1E0 | 2.1E-2 | 3.2E-2 | 3.6E0 | 1.7E1 | 57 | 56 | 57 | 56 | 0.56 |
| Ql | pg/ml | 1.7E0 | 5.5E0 | 9.9E0 | 1.7E1 | 1.6E1 | 3.1E1 | 1.0E-9 | 1.0E-9 | 7.5E1 | 1.8E2 | 57 | 57 | 57 | 57 | 0.56 |
| Qm | pg/ml | 4.7E-1 | 1.2E1 | 1.6E1 | 2.6E1 | 3.5E1 | 3.7E1 | 1.0E-9 | 1.0E-9 | 1.9E2 | 1.8E2 | 57 | 57 | 57 | 57 | 0.59 |
| Qn | pg/ml | 5.6E-1 | 6.1E-1 | 6.1E0 | 4.9E0 | 2.9E1 | 1.3E1 | 1.0E-9 | 1.0E-9 | 2.2E2 | 7.5E1 | 57 | 57 | 57 | 57 | 0.56 |
| Nv | pg/ml | 3.1E3 | 6.2E3 | 9.5E3 | 1.5E4 | 2.1E4 | 2.5E4 | 1.0E-9 | 2.9E2 | 1.5E5 | 1.6E5 | 156 | 116 | 156 | 116 | 0.64 |
| Nw | pg/ml | 8.3E3 | 1.4E4 | 1.2E4 | 2.1E4 | 1.9E4 | 2.9E4 | 1.9E2 | 1.3E3 | 2.1E5 | 2.2E5 | 156 | 116 | 156 | 116 | 0.69 |
| Nx | pg/ml | 1.8E2 | 2.6E2 | 3.9E2 | 6.1E2 | 6.1E2 | 7.4E2 | 1.0E-9 | 1.0E-9 | 3.5E3 | 4.1E3 | 156 | 116 | 156 | 116 | 0.62 |
| Ny | pg/ml | 4.3E0 | 1.4E1 | 1.8E2 | 7.4E1 | 2.0E3 | 2.9E2 | 1.0E-9 | 1.0E-9 | 2.5E4 | 2.8E3 | 156 | 116 | 156 | 116 | 0.67 |
| Oa | pg/ml | 1.0E2 | 3.7E2 | 2.8E2 | 7.6E2 | 5.3E2 | 9.6E2 | 1.0E-9 | 1.0E-9 | 3.0E3 | 4.5E3 | 57 | 57 | 57 | 57 | 0.70 |
| Op | pg/ml | 4.0E5 | 4.5E5 | 4.0E5 | 4.6E5 | 1.5E5 | 1.7E5 | 1.4E5 | 5.2E4 | 7.3E5 | 7.5E5 | 27 | 22 | 27 | 22 | 0.64 |
| Wn | ng/ml | 9.4E0 | 1.4E1 | 1.4E2 | 2.2E1 | 4.2E2 | 1.8E1 | 1.2E0 | 3.8E0 | 1.8E3 | 5.6E1 | 19 | 12 | 19 | 12 | 0.59 |
| Tk | ng/ml | 1.2E2 | 1.3E2 | 3.6E2 | 4.0E2 | 9.1E2 | 6.5E2 | 3.0E0 | 1.4E1 | 4.2E3 | 2.3E3 | 20 | 15 | 20 | 15 | 0.56 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oe | pg/ml | 9.3E1 | 1.0E1 | 2.7E2 | 2.5E2 | 3.9E2 | 4.1E2 | 1.0E-9 | 1.0E-9 | 2.2E3 | 2.3E3 | 155 | 115 | 155 | 115 | 0.48 |
| Of | pg/ml | 2.0E2 | 1.3E2 | 6.2E3 | 6.4E3 | 2.3E4 | 2.3E4 | 1.0E-9 | 1.0E-9 | 1.9E5 | 1.7E5 | 156 | 116 | 156 | 116 | 0.47 |
| Og | pg/ml | 8.2E-2 | 5.8E-2 | 5.6E-1 | 1.4E-1 | 2.1E0 | 3.1E-1 | 1.0E-9 | 1.0E-9 | 1.9E1 | 2.5E0 | 156 | 116 | 156 | 116 | 0.41 |
| Oh | pg/ml | 2.6E0 | 4.5E0 | 2.0E1 | 1.6E2 | 1.3E2 | 1.5E3 | 1.0E-9 | 1.0E-9 | 1.4E3 | 1.6E4 | 156 | 116 | 156 | 116 | 0.58 |
| Oi | pg/ml | 2.3E0 | 2.8E0 | 5.0E0 | 5.8E0 | 7.2E0 | 7.4E0 | 1.0E-9 | 1.0E-9 | 3.6E1 | 4.2E1 | 156 | 116 | 156 | 116 | 0.55 |
| Ok | pg/ml | 3.5E2 | 6.1E2 | 4.3E2 | 8.4E2 | 3.5E2 | 9.6E2 | 1.5E1 | 6.4E1 | 2.0E3 | 7.8E3 | 156 | 116 | 156 | 116 | 0.70 |
| Om | pg/ml | 3.8E2 | 5.4E2 | 9.4E2 | 1.4E3 | 2.9E3 | 4.8E3 | 1.0E-9 | 1.0E-9 | 3.0E4 | 5.1E4 | 156 | 116 | 156 | 116 | 0.61 |
| On | pg/ml | 1.6E2 | 2.7E2 | 2.9E2 | 5.2E2 | 5.0E2 | 9.3E2 | 8.4E-1 | 2.2E1 | 4.5E3 | 8.5E3 | 156 | 116 | 156 | 116 | 0.65 |
| Or | pg/ml | 9.7E0 | 2.2E1 | 2.1E1 | 7.1E1 | 2.8E1 | 1.2E2 | 1.0E-9 | 1.0E-9 | 1.5E2 | 5.1E2 | 57 | 60 | 57 | 60 | 0.59 |
| Ow | pg/ml | 2.8E1 | 5.3E1 | 1.3E2 | 3.6E2 | 3.9E2 | 1.1E3 | 1.0E-9 | 1.0E-9 | 2.7E3 | 8.1E3 | 57 | 60 | 57 | 60 | 0.61 |
| Ou | pg/ml | 3.8E2 | 6.6E2 | 8.6E2 | 1.6E3 | 1.5E3 | 2.5E3 | 2.0E1 | 1.0E-9 | 9.8E3 | 1.1E4 | 57 | 60 | 57 | 60 | 0.62 |
| Ul | ng/ml | 1.0E-9 | 1.0E-9 | 1.2E0 | 1.8E0 | 4.5E0 | 8.1E0 | 1.0E-9 | 1.0E-9 | 2.3E1 | 5.6E1 | 58 | 57 | 58 | 57 | 0.48 |
| Uo | ng/ml | 1.0E-9 | 1.0E-9 | 9.3E-2 | 5.5E-2 | 2.4E-1 | 1.5E-1 | 1.0E-9 | 1.0E-9 | 1.3E0 | 6.9E-1 | 58 | 57 | 58 | 57 | 0.47 |
| Uk | ng/ml | 1.0E-9 | 1.0E-9 | 2.8E-3 | 1.1E-2 | 6.1E-3 | 4.7E-2 | 1.0E-9 | 1.0E-9 | 2.6E-2 | 3.2E-1 | 58 | 57 | 58 | 57 | 0.45 |
| Um | ng/ml | 1.0E-9 | 1.0E-9 | 2.6E-1 | 2.1E-1 | 6.9E-1 | 5.4E-1 | 1.0E-9 | 1.0E-9 | 3.6E0 | 2.3E0 | 58 | 57 | 58 | 57 | 0.46 |
| Uf | ng/ml | 5.2E-2 | 9.5E-2 | 8.8E-2 | 2.8E-1 | 1.0E-1 | 7.0E-1 | 1.0E-3 | 6.8E-3 | 4.3E-1 | 5.1E0 | 58 | 57 | 58 | 57 | 0.66 |
| Uh | ng/ml | 1.5E0 | 4.2E0 | 2.6E0 | 5.0E0 | 2.5E0 | 4.1E0 | 3.6E-2 | 2.5E-1 | 9.6E0 | 1.8E1 | 58 | 57 | 58 | 57 | 0.71 |
| Un | ng/ml | 1.5E0 | 2.3E0 | 1.6E0 | 3.0E0 | 9.6E-1 | 3.4E0 | 3.4E-1 | 4.6E-1 | 4.4E0 | 2.5E1 | 58 | 57 | 58 | 57 | 0.70 |
| Ug | ng/ml | 1.1E1 | 8.9E0 | 2.0E1 | 2.5E1 | 2.0E1 | 3.5E1 | 1.5E0 | 1.2E0 | 8.5E1 | 1.6E2 | 58 | 57 | 58 | 57 | 0.47 |
| Ur | ng/ml | 1.4E-1 | 6.0E-2 | 3.5E-1 | 4.5E-1 | 5.5E-1 | 1.3E0 | 1.0E-9 | 1.0E-9 | 2.6E0 | 7.3E0 | 58 | 56 | 58 | 56 | 0.39 |
| Up | ng/ml | 1.0E-9 | 1.0E-9 | 2.5E-3 | 4.7E-2 | 8.7E-3 | 3.2E-1 | 1.0E-9 | 1.0E-9 | 5.3E-2 | 2.4E0 | 58 | 56 | 58 | 56 | 0.58 |
| Us | ng/ml | 3.9E-3 | 2.6E-3 | 8.5E-3 | 5.7E-2 | 1.2E-2 | 2.3E-1 | 1.0E-9 | 1.0E-9 | 6.0E-2 | 1.7E0 | 58 | 56 | 58 | 56 | 0.52 |
| Uv | ng/ml | 3.2E-3 | 2.8E-3 | 1.6E-2 | 1.4E-2 | 4.2E-2 | 5.5E-2 | 1.0E-9 | 1.0E-9 | 2.3E-1 | 4.1E-1 | 58 | 56 | 58 | 56 | 0.45 |
| Ut | ng/ml | 5.8E-1 | 1.2E0 | 2.4E0 | 4.7E0 | 7.3E0 | 1.0E1 | 1.0E-9 | 1.0E-9 | 5.2E1 | 6.5E1 | 58 | 56 | 58 | 56 | 0.63 |
| Uu | ng/ml | 7.3E0 | 6.5E0 | 7.6E0 | 7.3E0 | 5.1E0 | 4.7E0 | 8.3E-1 | 5.7E-1 | 2.6E1 | 2.9E1 | 58 | 56 | 58 | 56 | 0.48 |
| Uw | ng/ml | 2.0E0 | 2.8E0 | 2.6E0 | 4.9E0 | 2.3E0 | 7.9E0 | 1.0E-9 | 3.7E-1 | 7.1E0 | 3.9E1 | 28 | 22 | 28 | 22 | 0.64 |
| Vb | ng/ml | 1.2E0 | 9.7E-1 | 1.1E0 | 1.2E0 | 4.4E-1 | 1.2E0 | 8.5E-2 | 2.6E-1 | 2.0E0 | 6.4E0 | 28 | 22 | 28 | 22 | 0.36 |
| Vc | ng/ml | 1.0E-9 | 1.0E-9 | 4.9E-3 | 1.0E-9 | 2.1E-2 | 0.0E0 | 1.0E-9 | 1.0E-9 | 1.1E-1 | 1.0E-9 | 28 | 22 | 28 | 22 | 0.45 |
| Uy | ng/ml | 8.2E-1 | 1.6E0 | 2.7E0 | 1.5E1 | 6.8E0 | 2.7E1 | 8.7E-2 | 2.0E-2 | 3.5E1 | 9.9E1 | 28 | 22 | 28 | 22 | 0.67 |
| Uz | ng/ml | 1.0E-9 | 1.0E-9 | 1.6E-2 | 1.5E0 | 8.2E-2 | 7.0E0 | 1.0E-9 | 1.0E-9 | 4.4E-1 | 3.3E1 | 28 | 22 | 28 | 22 | 0.53 |
| Ux | ng/ml | 2.0E2 | 1.7E2 | 1.8E2 | 2.1E2 | 1.3E2 | 1.3E2 | 4.5E0 | 2.0E1 | 4.6E2 | 4.9E2 | 28 | 22 | 28 | 22 | 0.55 |
| Va | ng/ml | 1.2E1 | 7.9E0 | 2.4E1 | 2.3E1 | 3.2E1 | 2.6E1 | 3.1E-1 | 1.2E0 | 1.2E2 | 9.6E1 | 28 | 22 | 28 | 22 | 0.53 |
| Vh | ng/ml | 7.9E-3 | 2.0E-2 | 1.7E-2 | 6.1E-2 | 2.6E-2 | 1.8E-1 | 1.0E-3 | 3.0E-3 | 1.2E-1 | 8.6E-1 | 28 | 22 | 28 | 22 | 0.72 |
| Vi | ng/ml | 4.0E-3 | 1.0E-2 | 7.1E-3 | 1.0E-1 | 7.2E-3 | 3.9E-1 | 1.0E-9 | 1.0E-9 | 2.7E-2 | 1.8E0 | 28 | 22 | 28 | 22 | 0.60 |
| Vj | ng/ml | 3.2E1 | 5.7E1 | 6.2E1 | 9.0E1 | 7.6E1 | 1.4E2 | 1.4E0 | 8.3E0 | 3.4E2 | 6.5E2 | 28 | 21 | 28 | 21 | 0.58 |
| Vp | ng/ml | 1.0E-9 | 1.0E-9 | 1.2E-1 | 1.0E0 | 5.9E-1 | 6.5E0 | 1.0E-9 | 1.0E-9 | 3.9E0 | 4.9E1 | 58 | 57 | 58 | 57 | 0.58 |
| Vt | ng/ml | 5.0E0 | 9.0E0 | 6.0E0 | 1.4E1 | 5.0E0 | 2.1E1 | 5.6E-1 | 1.2E0 | 3.2E1 | 1.6E2 | 58 | 57 | 58 | 57 | 0.72 |
| Vu | ng/ml | 1.0E-9 | 4.5E-1 | 1.0E0 | 2.5E0 | 2.5E0 | 4.4E0 | 1.0E-9 | 1.0E-9 | 1.6E1 | 2.2E1 | 56 | 55 | 56 | 55 | 0.61 |
| Vq | ng/ml | 7.2E1 | 3.5E2 | 4.7E2 | 1.1E3 | 9.1E2 | 2.1E3 | 9.2E-1 | 3.6E0 | 5.0E3 | 1.2E4 | 50 | 41 | 50 | 41 | 0.66 |
| Vo | ng/ml | 2.5E1 | 2.6E1 | 2.4E1 | 2.5E1 | 5.2E0 | 6.0E0 | 9.7E0 | 4.9E0 | 3.5E1 | 4.8E1 | 58 | 57 | 58 | 57 | 0.54 |
| Vs | ng/ml | 1.4E-1 | 1.0E-9 | 4.9E0 | 1.2E1 | 1.4E1 | 6.2E1 | 1.0E-9 | 1.0E-9 | 8.9E1 | 4.5E2 | 58 | 54 | 58 | 54 | 0.47 |
| Vv | ng/ml | 2.6E0 | 3.7E0 | 6.0E0 | 6.2E0 | 1.2E1 | 8.4E0 | 1.0E-9 | 1.0E-9 | 8.4E1 | 4.4E1 | 58 | 56 | 58 | 56 | 0.51 |
| Vw | ng/ml | 3.7E1 | 4.2E1 | 3.2E1 | 3.9E1 | 1.8E1 | 1.9E1 | 2.5E0 | 4.4E0 | 6.7E1 | 6.9E1 | 28 | 22 | 28 | 22 | 0.62 |
| Oy | pg/ml | 4.9E-1 | 5.0E-1 | 9.5E0 | 4.0E1 | 4.4E1 | 1.2E1 | 1.0E-9 | 1.0E-9 | 4.0E2 | 9.9E1 | 156 | 115 | 156 | 115 | 0.48 |
| Oz | pg/ml | 4.9E-2 | 1.0E-9 | 2.8E-1 | 6.8E-1 | 4.0E-1 | 3.7E0 | 1.0E-9 | 1.0E-9 | 2.1E0 | 2.9E1 | 156 | 115 | 156 | 115 | 0.43 |
| Pa | pg/ml | 3.7E-1 | 5.4E-1 | 1.6E0 | 4.4E0 | 7.7E0 | 2.3E1 | 1.0E-9 | 1.0E-9 | 8.6E1 | 2.3E2 | 156 | 115 | 156 | 115 | 0.59 |
| Pb | pg/ml | 2.9E-3 | 1.0E-9 | 3.2E0 | 6.9E-1 | 3.9E1 | 4.0E0 | 1.0E-9 | 1.0E-9 | 4.9E2 | 3.2E1 | 156 | 115 | 156 | 115 | 0.44 |
| Pc | pg/ml | 1.7E-1 | 1.0E-9 | 4.9E-1 | 3.5E0 | 1.2E0 | 3.1E1 | 1.0E-9 | 1.0E-9 | 1.4E1 | 3.3E2 | 156 | 115 | 156 | 115 | 0.45 |
| Pd | pg/ml | 1.6E0 | 2.4E0 | 3.7E0 | 1.4E1 | 8.9E0 | 7.9E1 | 1.0E-9 | 1.0E-9 | 9.4E1 | 8.4E2 | 156 | 115 | 156 | 115 | 0.58 |
| Pe | pg/ml | 1.9E1 | 4.4E1 | 9.2E1 | 4.1E2 | 4.4E2 | 1.7E3 | 1.0E-9 | 1.0E-9 | 4.7E3 | 1.5E4 | 156 | 115 | 156 | 115 | 0.66 |
| Pf | pg/ml | 1.2E0 | 3.1E0 | 8.6E0 | 3.0E1 | 3.4E1 | 1.5E2 | 1.0E-9 | 1.0E-9 | 3.3E2 | 1.5E3 | 156 | 115 | 156 | 115 | 0.63 |
| Pg | pg/ml | 3.8E0 | 7.3E0 | 7.2E1 | 1.5E2 | 4.3E2 | 7.7E2 | 1.0E-9 | 1.0E-9 | 4.2E3 | 7.7E3 | 156 | 115 | 156 | 115 | 0.60 |
| Ph | ng/ml | 1.3E-1 | 2.2E-1 | 2.7E-1 | 5.1E-1 | 4.0E-1 | 8.7E-1 | 1.0E-9 | 1.0E-9 | 2.2E0 | 5.4E0 | 57 | 60 | 57 | 60 | 0.60 |
| Pi | ng/ml | 1.8E-1 | 2.2E-1 | 2.4E-1 | 1.8E0 | 4.3E-1 | 1.1E1 | 1.0E-9 | 1.0E-9 | 3.2E0 | 8.2E1 | 57 | 60 | 57 | 60 | 0.62 |
| Pj | ng/mL | 3.8E0 | 7.3E0 | 4.6E0 | 8.0E0 | 3.3E0 | 5.4E0 | 4.0E-1 | 1.5E0 | 1.6E1 | 3.1E1 | 57 | 60 | 57 | 60 | 0.72 |
| Pk | ng/ml | 7.1E-3 | 1.1E-2 | 8.2E-3 | 4.6E-3 | 7.9E-3 | 2.0E-1 | 1.0E-9 | 1.0E-9 | 3.9E-2 | 1.5E0 | 57 | 60 | 57 | 60 | 0.67 |
| aA | mg/dL | 8.6E-1 | 9.6E-1 | 9.9E-1 | 1.1E0 | 4.9E-1 | 7.3E-1 | 3.0E-1 | 3.0E-1 | 4.2E0 | 4.7E0 | 265 | 142 | 265 | 142 | 0.55 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aC | mg/mL | 2.4E0 | 2.1E0 | 2.7E0 | 2.2E0 | 1.3E0 | 1.0E0 | 1.1E0 | 7.5E-1 | 7.2E0 | 5.5E0 | 75 | 68 | 75 | 68 | 0.38 |
| aD | ug/mL | 2.8E0 | 3.6E0 | 4.3E0 | 4.9E0 | 4.2E0 | 4.0E0 | 8.5E-1 | 7.5E-1 | 3.1E1 | 2.1E1 | 75 | 68 | 75 | 68 | 0.54 |
| aE | mg/mL | 5.6E-1 | 5.9E-1 | 5.9E-1 | 6.0E-1 | 1.6E-1 | 1.9E-1 | 2.8E-1 | 1.8E-1 | 1.1E0 | 1.2E0 | 75 | 68 | 75 | 68 | 0.52 |
| aF | ng/mL | 2.2E0 | 2.2E0 | 6.2E0 | 4.0E0 | 9.9E0 | 4.9E0 | 4.3E-3 | 4.3E-3 | 5.0E1 | 2.9E1 | 75 | 68 | 75 | 68 | 0.47 |
| aG | mg/mL | 1.3E-1 | 1.4E-1 | 1.6E-1 | 1.6E-1 | 8.1E-2 | 8.1E-2 | 5.0E-2 | 5.1E-2 | 4.2E-1 | 4.8E-1 | 75 | 68 | 75 | 68 | 0.49 |
| aH | ug/mL | 6.4E1 | 7.2E1 | 7.3E1 | 7.8E1 | 3.5E1 | 4.2E1 | 1.5E1 | 1.1E1 | 2.0E2 | 1.8E2 | 75 | 68 | 75 | 68 | 0.51 |
| aI | ug/mL | 1.8E2 | 1.6E2 | 1.7E2 | 1.7E2 | 5.7E1 | 6.4E1 | 6.1E1 | 4.7E1 | 3.3E2 | 3.4E2 | 75 | 68 | 75 | 68 | 0.46 |
| aJ | ug/mL | 2.2E0 | 2.5E0 | 3.1E0 | 3.4E0 | 2.4E0 | 2.3E0 | 9.5E-1 | 8.2E-1 | 1.4E1 | 1.1E1 | 75 | 68 | 75 | 68 | 0.57 |
| aK | ng/mL | 1.6E0 | 1.1E0 | 2.2E0 | 1.8E0 | 1.9E0 | 1.9E0 | 6.9E-2 | 2.9E-4 | 7.5E0 | 1.0E1 | 75 | 68 | 75 | 68 | 0.41 |
| aL | mg/mL | 7.1E-1 | 7.4E-1 | 7.4E-1 | 7.6E-1 | 2.1E-1 | 2.7E-1 | 2.2E-1 | 2.7E-1 | 1.3E0 | 1.7E0 | 75 | 68 | 75 | 68 | 0.52 |
| aM | U/mL | 1.3E1 | 2.3E1 | 2.7E1 | 5.7E1 | 5.0E1 | 1.1E2 | 4.2E-2 | 4.2E-2 | 3.5E2 | 8.2E2 | 75 | 68 | 75 | 68 | 0.65 |
| aN | U/mL | 1.1E1 | 2.0E1 | 1.9E1 | 3.7E1 | 2.3E1 | 6.1E1 | 2.5E-3 | 2.5E-3 | 1.3E2 | 3.8E2 | 75 | 68 | 75 | 68 | 0.65 |
| aO | pg/mL | 7.4E1 | 4.8E1 | 5.5E2 | 3.3E2 | 1.3E3 | 6.1E2 | 6.0E-2 | 6.0E-2 | 6.6E3 | 2.4E3 | 75 | 68 | 75 | 68 | 0.50 |
| aP | ng/mL | 1.5E0 | 1.7E0 | 2.0E0 | 2.2E0 | 1.3E0 | 1.3E0 | 5.4E-1 | 6.8E-1 | 6.5E0 | 6.6E0 | 75 | 68 | 75 | 68 | 0.58 |
| aQ | ng/mL | 2.3E-1 | 2.5E-1 | 3.2E-1 | 3.6E-1 | 2.6E-1 | 3.8E-1 | 2.0E-4 | 2.0E-4 | 1.1E0 | 2.0E0 | 75 | 68 | 75 | 68 | 0.51 |
| aR | ng/mL | 1.8E0 | 1.9E0 | 3.0E0 | 3.2E0 | 3.8E0 | 4.5E0 | 2.6E-1 | 5.6E-1 | 2.1E1 | 3.4E1 | 75 | 68 | 75 | 68 | 0.55 |
| aS | ng/mL | 3.7E-1 | 4.6E-1 | 1.3E0 | 9.2E-1 | 3.9E0 | 1.1E0 | 4.2E-3 | 4.2E-3 | 3.3E1 | 6.2E0 | 75 | 68 | 75 | 68 | 0.53 |
| aU | pg/mL | 7.1E1 | 6.1E1 | 1.0E2 | 9.7E1 | 1.0E2 | 1.2E2 | 7.4E0 | 7.4E-2 | 5.1E2 | 7.0E2 | 75 | 68 | 75 | 68 | 0.45 |
| aV | ng/mL | 6.3E-1 | 4.4E-1 | 8.6E-1 | 1.3E0 | 7.4E-1 | 4.0E0 | 5.9E-2 | 7.6E-4 | 4.0E0 | 3.3E1 | 75 | 68 | 75 | 68 | 0.44 |
| aW | pg/mL | 2.0E1 | 2.0E1 | 2.2E1 | 2.5E1 | 2.0E1 | 4.9E1 | 7.2E-2 | 7.2E-2 | 1.7E2 | 4.2E2 | 75 | 68 | 75 | 68 | 0.48 |
| aX | ng/mL | 8.0E0 | 7.0E0 | 1.1E1 | 1.2E1 | 9.6E0 | 1.6E1 | 3.0E-1 | 6.2E-1 | 5.4E1 | 1.1E2 | 75 | 68 | 75 | 68 | 0.46 |
| aY | pg/mL | 5.3E1 | 5.4E1 | 6.9E1 | 8.3E1 | 5.9E1 | 1.5E2 | 4.1E1 | 4.1E-1 | 3.1E2 | 1.2E3 | 75 | 68 | 75 | 68 | 0.50 |
| aZ | pg/mL | 2.2E2 | 2.4E2 | 5.5E2 | 7.2E2 | 9.0E2 | 1.6E3 | 1.7E0 | 1.7E0 | 5.4E3 | 1.2E4 | 75 | 68 | 75 | 68 | 0.50 |
| bA | ng/mL | 1.3E1 | 2.2E1 | 4.2E1 | 1.0E2 | 6.8E1 | 2.0E2 | 3.0E-2 | 3.0E-2 | 4.1E2 | 9.4E2 | 75 | 68 | 75 | 68 | 0.59 |
| bB | ng/mL | 2.8E2 | 2.5E2 | 3.0E2 | 2.7E2 | 1.5E2 | 1.7E2 | 5.7E1 | 1.2E1 | 7.4E2 | 8.1E2 | 75 | 68 | 75 | 68 | 0.43 |
| bC | ng/mL | 3.2E2 | 3.2E2 | 4.9E2 | 7.3E2 | 5.0E2 | 1.0E3 | 2.7E1 | 3.5E1 | 3.0E3 | 4.7E3 | 75 | 68 | 75 | 68 | 0.52 |
| bE | mg/mL | 5.2E0 | 4.6E0 | 5.4E0 | 5.1E0 | 1.7E0 | 2.2E0 | 2.5E0 | 1.3E0 | 9.5E0 | 1.2E1 | 75 | 68 | 75 | 68 | 0.43 |
| bF | pg/mL | 3.7E1 | 3.8E1 | 3.6E2 | 4.5E2 | 1.5E3 | 1.5E3 | 5.0E-2 | 2.5E0 | 1.1E4 | 1.0E4 | 75 | 68 | 75 | 68 | 0.51 |
| bG | ng/mL | 1.7E0 | 2.2E0 | 3.2E0 | 3.6E0 | 4.7E0 | 4.8E0 | 1.1E-1 | 1.1E-1 | 2.6E1 | 3.0E1 | 75 | 68 | 75 | 68 | 0.51 |
| bH | pg/mL | 5.7E-1 | 5.7E-1 | 7.6E0 | 6.2E0 | 3.2E1 | 1.6E1 | 5.7E-1 | 5.7E-1 | 2.8E2 | 1.2E2 | 75 | 68 | 75 | 68 | 0.50 |
| bI | ng/mL | 4.0E-3 | 4.0E-3 | 1.0E-1 | 9.2E-2 | 2.1E-1 | 2.1E-1 | 4.0E-3 | 4.0E-3 | 9.8E-1 | 8.8E-1 | 75 | 68 | 75 | 68 | 0.46 |
| bJ | mg/mL | 1.7E0 | 1.8E0 | 2.1E0 | 2.2E0 | 1.6E0 | 2.1E0 | 2.5E-4 | 2.5E-4 | 6.6E0 | 1.1E1 | 75 | 68 | 75 | 68 | 0.49 |
| bL | pg/mL | 4.3E0 | 3.0E0 | 9.4E0 | 8.3E0 | 1.1E1 | 1.0E1 | 4.6E-2 | 1.6E-2 | 4.9E1 | 3.5E1 | 75 | 68 | 75 | 68 | 0.45 |
| bM | mg/mL | 1.6E0 | 2.2E0 | 1.9E0 | 2.6E0 | 1.3E0 | 1.6E0 | 2.4E-1 | 1.8E-2 | 8.6E0 | 7.9E0 | 75 | 68 | 75 | 68 | 0.63 |
| bN | ng/mL | 3.7E1 | 3.5E1 | 1.3E2 | 1.1E2 | 2.7E2 | 2.8E2 | 1.4E-1 | 5.9E-1 | 1.9E3 | 1.9E3 | 75 | 68 | 75 | 68 | 0.48 |
| bO | ng/mL | 4.0E-2 | 4.0E-2 | 8.1E0 | 9.3E0 | 1.5E1 | 2.2E1 | 4.0E-2 | 4.0E-2 | 6.4E1 | 1.3E2 | 75 | 68 | 75 | 68 | 0.45 |
| bP | mg/mL | 4.9E-1 | 5.1E-1 | 7.0E-1 | 7.1E-1 | 5.5E-1 | 7.7E-1 | 8.2E-2 | 9.2E-2 | 2.5E0 | 4.8E0 | 75 | 68 | 75 | 68 | 0.48 |
| bQ | pg/mL | 2.1E1 | 2.3E1 | 4.2E1 | 2.7E2 | 5.6E1 | 1.6E3 | 3.5E0 | 1.5E-1 | 3.2E2 | 1.3E4 | 75 | 68 | 75 | 68 | 0.51 |
| bR | ng/mL | 1.2E-2 | 1.2E-2 | 1.3E-1 | 2.0E-1 | 4.0E-1 | 1.0E0 | 1.2E-2 | 1.2E-2 | 3.4E0 | 8.7E0 | 75 | 68 | 75 | 68 | 0.50 |
| bS | pg/mL | 9.4E-1 | 9.4E-1 | 9.1E0 | 1.1E1 | 4.1E1 | 4.9E1 | 9.4E-1 | 9.4E-1 | 3.4E2 | 3.9E2 | 75 | 68 | 75 | 68 | 0.49 |
| bU | ng/mL | 8.7E-2 | 1.3E-2 | 1.7E-1 | 2.2E-1 | 2.6E-1 | 8.0E-1 | 1.3E-2 | 1.3E-2 | 1.8E0 | 6.6E0 | 75 | 68 | 75 | 68 | 0.46 |
| bV | pg/mL | 4.3E2 | 5.2E2 | 5.4E2 | 6.0E2 | 2.9E2 | 3.7E2 | 1.8E2 | 2.3E2 | 1.6E3 | 2.2E3 | 75 | 68 | 75 | 68 | 0.56 |
| bW | pg/mL | 3.1E2 | 3.3E2 | 4.2E2 | 5.5E2 | 3.6E2 | 7.8E2 | 8.4E1 | 1.3E2 | 2.2E3 | 4.8E3 | 75 | 68 | 75 | 68 | 0.55 |
| bX | ng/mL | 1.8E-3 | 2.5E-5 | 2.7E-3 | 2.2E-3 | 3.0E-3 | 2.8E-3 | 2.5E-5 | 2.5E-5 | 1.2E-2 | 8.4E-3 | 75 | 68 | 75 | 68 | 0.45 |
| bZ | pg/mL | 2.9E2 | 2.9E2 | 1.5E3 | 2.7E3 | 5.4E3 | 9.3E3 | 1.5E-1 | 3.5E1 | 4.4E4 | 5.8E4 | 75 | 68 | 75 | 68 | 0.51 |
| cA | pg/mL | 6.0E-1 | 6.0E-1 | 1.5E0 | 7.5E0 | 2.8E0 | 4.5E1 | 6.0E-1 | 6.0E-1 | 1.2E1 | 3.7E2 | 75 | 68 | 75 | 68 | 0.52 |
| cB | ng/mL | 4.2E-2 | 4.1E-2 | 6.1E-2 | 7.3E-2 | 6.2E-2 | 9.8E-2 | 1.7E-3 | 1.7E-3 | 3.1E-1 | 4.3E-1 | 75 | 68 | 75 | 68 | 0.48 |
| cC | pg/mL | 4.6E1 | 4.0E1 | 4.9E1 | 4.4E1 | 4.9E1 | 5.7E1 | 1.0E0 | 1.0E0 | 3.7E2 | 4.5E2 | 75 | 68 | 75 | 68 | 0.45 |
| cD | pg/mL | 6.3E0 | 3.9E0 | 1.6E1 | 1.2E1 | 5.9E1 | 4.0E1 | 3.3E-1 | 3.3E-1 | 4.8E2 | 2.9E2 | 75 | 68 | 75 | 68 | 0.37 |
| cE | pg/mL | 6.5E1 | 6.7E1 | 2.7E2 | 2.8E2 | 6.5E2 | 6.1E2 | 1.8E0 | 1.2E-1 | 3.1E3 | 3.8E3 | 75 | 68 | 75 | 68 | 0.54 |
| cF | pg/mL | 5.3E-1 | 5.3E-1 | 1.6E1 | 1.5E1 | 2.8E1 | 3.5E1 | 5.3E-1 | 5.3E-1 | 1.4E2 | 2.7E2 | 75 | 68 | 75 | 68 | 0.49 |
| cG | pg/mL | 5.2E1 | 6.3E1 | 9.8E1 | 2.7E2 | 1.7E2 | 1.3E3 | 1.5E1 | 7.8E0 | 1.1E3 | 1.0E4 | 75 | 68 | 75 | 68 | 0.56 |
| cH | uIU/mL | 3.4E0 | 2.8E0 | 8.1E0 | 8.0E0 | 2.0E1 | 1.7E1 | 8.6E-3 | 8.6E-3 | 1.6E2 | 1.2E2 | 75 | 68 | 75 | 68 | 0.47 |
| cI | ng/mL | 5.9E0 | 6.0E0 | 9.8E0 | 1.8E1 | 1.2E1 | 2.7E1 | 2.3E-1 | 3.2E-2 | 5.9E1 | 1.2E2 | 75 | 68 | 75 | 68 | 0.54 |
| cJ | ug/mL | 6.7E1 | 5.1E1 | 9.6E1 | 9.2E1 | 1.0E2 | 1.1E2 | 6.9E0 | 7.2E0 | 6.4E2 | 6.2E2 | 75 | 68 | 75 | 68 | 0.47 |
| cK | ng/mL | 3.8E-3 | 3.8E-3 | 1.2E-2 | 3.2E-2 | 2.7E-2 | 1.8E-1 | 3.8E-3 | 3.8E-3 | 1.3E-1 | 1.5E0 | 75 | 68 | 75 | 68 | 0.50 |
| cL | pg/mL | 2.2E2 | 2.0E2 | 5.0E2 | 6.8E2 | 1.2E3 | 2.9E3 | 5.0E1 | 3.1E1 | 7.4E3 | 2.4E4 | 75 | 68 | 75 | 68 | 0.50 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cM | pg/mL | 2.7E2 | 2.6E2 | 3.2E2 | 2.6E2 | 1.9E2 | 1.3E2 | 6.0E1 | 4.2E1 | 1.1E3 | 6.7E2 | 75 | 68 | 75 | 68 | 0.43 |
| cN | pg/mL | 1.2E2 | 1.2E2 | 1.3E2 | 1.4E2 | 5.3E1 | 1.2E2 | 3.8E1 | 6.3E1 | 3.2E2 | 1.1E3 | 75 | 68 | 75 | 68 | 0.53 |
| cO | pg/mL | 2.0E2 | 2.1E2 | 3.2E2 | 5.7E2 | 3.2E2 | 2.3E3 | 5.4E1 | 8.2E1 | 1.7E3 | 1.9E4 | 75 | 68 | 75 | 68 | 0.51 |
| cP | ng/mL | 2.4E3 | 2.4E3 | 2.6E3 | 2.6E3 | 1.1E3 | 9.0E2 | 6.2E2 | 1.0E3 | 5.6E3 | 4.7E3 | 75 | 68 | 75 | 68 | 0.50 |
| cQ | ng/mL | 4.9E-2 | 5.3E-2 | 1.2E-1 | 1.3E-1 | 2.0E-1 | 2.3E-1 | 2.0E-3 | 2.0E-3 | 1.2E0 | 1.3E0 | 75 | 68 | 75 | 68 | 0.49 |
| cR | ng/mL | 3.0E2 | 3.1E2 | 4.4E2 | 7.1E2 | 3.5E2 | 1.2E3 | 3.6E1 | 2.0E1 | 1.4E3 | 7.7E3 | 75 | 68 | 75 | 68 | 0.53 |
| cS | ng/mL | 2.4E2 | 2.8E2 | 4.0E2 | 4.0E2 | 4.5E2 | 3.8E2 | 8.0E1 | 9.1E1 | 2.5E3 | 2.4E3 | 75 | 68 | 75 | 68 | 0.54 |
| cT | ng/mL | 5.3E1 | 6.2E1 | 1.2E2 | 2.2E2 | 1.7E2 | 4.1E2 | 5.1E0 | 4.2E0 | 8.4E2 | 2.1E3 | 75 | 68 | 75 | 68 | 0.55 |
| cU | ng/mL | 5.7E1 | 6.6E1 | 8.2E1 | 1.2E2 | 9.4E1 | 2.1E2 | 6.2E0 | 9.0E0 | 7.7E2 | 1.6E3 | 75 | 68 | 75 | 68 | 0.56 |
| cV | ng/mL | 1.9E-1 | 2.2E-1 | 9.9E-1 | 6.7E-1 | 5.4E0 | 1.6E0 | 3.4E-2 | 3.0E-2 | 4.7E1 | 9.7E0 | 75 | 68 | 75 | 68 | 0.51 |
| cW | mIU/mL | 4.8E-2 | 4.5E-2 | 1.1E-1 | 6.7E-2 | 5.1E-1 | 6.2E-2 | 4.8E-3 | 4.8E-3 | 4.5E0 | 3.9E-1 | 75 | 68 | 75 | 68 | 0.51 |
| cX | ng/mL | 1.1E-1 | 1.6E-1 | 2.1E0 | 2.1E0 | 6.3E0 | 6.0E0 | 2.3E-4 | 2.3E-4 | 2.8E1 | 2.8E1 | 75 | 68 | 75 | 68 | 0.53 |
| cY | ng/mL | 7.6E0 | 7.1E0 | 1.1E1 | 1.1E1 | 9.4E0 | 1.3E1 | 2.2E-1 | 1.7E-1 | 4.1E1 | 6.1E1 | 75 | 68 | 75 | 68 | 0.47 |
| cZ | ug/mL | 1.2E1 | 1.2E1 | 1.4E1 | 1.4E1 | 5.2E0 | 6.7E0 | 6.0E0 | 2.8E0 | 2.9E1 | 3.0E1 | 75 | 68 | 75 | 68 | 0.49 |
| dA | pg/mL | 3.0E2 | 3.2E2 | 3.3E2 | 4.4E2 | 1.3E2 | 6.9E2 | 1.0E2 | 1.1E2 | 9.4E2 | 5.8E3 | 75 | 68 | 75 | 68 | 0.53 |
| dB | ug/mL | 1.9E1 | 2.0E1 | 2.1E1 | 1.7E1 | 2.8E1 | 1.0E1 | 2.1E0 | 2.1E0 | 2.5E2 | 4.0E1 | 75 | 68 | 75 | 68 | 0.48 |
| dC | nmol/L | 3.4E1 | 3.6E1 | 3.9E1 | 3.7E1 | 2.0E1 | 1.4E1 | 1.0E1 | 7.8E0 | 1.4E2 | 7.0E1 | 75 | 68 | 75 | 68 | 0.52 |
| dD | ug/mL | 3.4E1 | 3.2E1 | 3.6E1 | 3.3E1 | 1.0E1 | 1.1E1 | 1.4E1 | 1.4E1 | 7.4E1 | 6.0E1 | 75 | 68 | 75 | 68 | 0.42 |
| dE | ng/mL | 5.0E-1 | 3.8E-1 | 5.7E-1 | 5.0E-1 | 5.7E-1 | 5.4E-1 | 8.4E-3 | 8.4E-3 | 2.7E0 | 2.4E0 | 75 | 68 | 75 | 68 | 0.46 |
| dF | ng/mL | 2.4E2 | 2.8E2 | 3.1E2 | 4.0E2 | 2.1E2 | 2.9E2 | 7.5E1 | 7.5E1 | 1.2E3 | 1.3E3 | 75 | 68 | 75 | 68 | 0.59 |
| dG | ng/mL | 1.1E1 | 1.3E1 | 1.6E1 | 1.9E1 | 1.4E1 | 2.4E1 | 3.2E1 | 3.0E0 | 9.7E1 | 1.8E2 | 75 | 68 | 75 | 68 | 0.55 |
| dH | pg/mL | 7.1E0 | 8.8E0 | 1.6E1 | 2.4E1 | 3.8E1 | 8.3E1 | 4.0E-2 | 4.0E-2 | 3.1E2 | 6.7E2 | 75 | 68 | 75 | 68 | 0.59 |
| dI | pg/mL | 4.6E-1 | 4.6E-1 | 1.4E0 | 6.7E0 | 4.1E0 | 4.0E1 | 4.6E-1 | 4.6E-1 | 3.4E1 | 3.3E2 | 75 | 68 | 75 | 68 | 0.58 |
| dJ | ng/mL | 1.9E0 | 2.2E0 | 2.1E0 | 2.2E0 | 1.0E0 | 1.2E0 | 3.2E-2 | 3.2E-2 | 5.1E0 | 4.9E0 | 75 | 68 | 75 | 68 | 0.54 |
| dK | uIU/mL | 1.5E0 | 1.2E0 | 2.6E0 | 1.9E0 | 5.0E0 | 2.0E0 | 2.8E-4 | 2.9E-2 | 3.9E1 | 1.1E1 | 75 | 68 | 75 | 68 | 0.46 |
| dL | ng/mL | 8.2E2 | 9.3E2 | 9.5E2 | 1.2E3 | 5.0E2 | 7.5E2 | 3.4E2 | 2.8E2 | 3.4E3 | 4.8E3 | 75 | 68 | 75 | 68 | 0.59 |
| dM | pg/mL | 9.6E2 | 9.9E2 | 1.3E3 | 1.4E3 | 1.8E3 | 1.4E3 | 3.9E2 | 3.7E2 | 1.5E4 | 9.6E3 | 75 | 68 | 75 | 68 | 0.53 |
| dN | ug/mL | 9.6E1 | 1.0E2 | 1.0E2 | 1.1E2 | 3.7E1 | 4.7E1 | 2.5E1 | 2.4E1 | 2.2E2 | 3.3E2 | 75 | 68 | 75 | 68 | 0.55 |
| dR | pg/ml | 1.7E3 | 1.2E3 | 2.1E3 | 2.0E3 | 1.8E3 | 2.3E3 | 2.8E2 | 1.3E2 | 7.8E3 | 9.8E3 | 53 | 60 | 53 | 60 | 0.41 |
| dU | pg/ml | 7.4E3 | 1.8E4 | 9.1E3 | 2.2E4 | 8.2E3 | 2.1E4 | 1.7E3 | 6.9E2 | 3.5E4 | 8.1E4 | 14 | 15 | 14 | 15 | 0.70 |
| dX | ng/ml | 4.3E-2 | 8.2E-2 | 1.4E-1 | 1.3E-1 | 2.5E-1 | 1.6E-1 | 2.6E-3 | 2.6E-3 | 1.2E0 | 6.6E-1 | 24 | 21 | 24 | 21 | 0.55 |
| dW | ng/ml | 9.9E-2 | 2.1E-1 | 1.7E-1 | 2.9E-1 | 1.8E-1 | 2.5E-1 | 6.4E-2 | 6.8E-2 | 5.8E-1 | 8.0E-1 | 8 | 9 | 8 | 9 | 0.72 |
| eF | ng/ml | 4.4E0 | 4.0E0 | 5.1E0 | 4.7E0 | 2.4E0 | 2.2E0 | 2.0E0 | 2.0E0 | 1.2E1 | 1.5E1 | 53 | 60 | 53 | 60 | 0.45 |
| eC | pg/ml | 3.1E2 | 2.8E2 | 3.9E2 | 3.5E2 | 2.6E2 | 3.3E2 | 1.1E2 | 1.9E1 | 1.4E3 | 2.0E3 | 47 | 55 | 47 | 55 | 0.41 |
| eD | pg/ml | 2.3E2 | 1.8E2 | 8.5E2 | 5.1E2 | 1.6E3 | 1.2E3 | 5.2E-1 | 5.2E-1 | 6.8E3 | 7.0E3 | 40 | 43 | 40 | 43 | 0.42 |
| eO | ng/ml | 4.5E1 | 9.8E1 | 2.4E2 | 1.3E2 | 3.7E2 | 8.7E1 | 2.0E1 | 4.3E1 | 9.6E2 | 3.3E2 | 8 | 9 | 8 | 9 | 0.72 |
| eM | ng/ml | 3.0E0 | 2.7E0 | 3.8E0 | 5.3E0 | 2.8E0 | 6.6E0 | 7.6E-1 | 6.9E-1 | 1.2E1 | 2.6E1 | 34 | 28 | 34 | 28 | 0.50 |
| eP | ng/ml | 1.7E-2 | 3.7E-3 | 8.6E-1 | 1.6E0 | 1.9E0 | 6.0E0 | 3.7E-3 | 3.7E-3 | 8.6E0 | 2.8E1 | 24 | 21 | 24 | 21 | 0.42 |
| eT | ng/ml | 2.8E2 | 2.8E2 | 7.4E2 | 7.3E2 | 8.1E2 | 9.2E2 | 1.0E2 | 7.1E1 | 2.9E3 | 2.9E3 | 26 | 23 | 26 | 23 | 0.48 |
| eQ | pg/ml | 1.0E0 | 1.0E0 | 7.3E1 | 3.2E1 | 1.5E2 | 5.4E1 | 1.0E0 | 1.0E0 | 4.7E2 | 1.5E2 | 14 | 15 | 14 | 15 | 0.50 |
| eW | U/ml | 8.8E-3 | 6.7E-3 | 6.1E-2 | 2.2E-1 | 1.0E-1 | 5.1E-1 | 6.7E-3 | 6.7E-3 | 3.1E-1 | 1.6E0 | 8 | 9 | 8 | 9 | 0.47 |
| fA | ng/ml | 2.3E2 | 1.6E2 | 3.6E2 | 5.0E2 | 4.4E2 | 5.2E2 | 3.9E1 | 4.0E1 | 1.5E3 | 1.4E3 | 14 | 13 | 14 | 13 | 0.51 |
| eZ | ng/ml | 4.5E1 | 5.6E1 | 5.7E1 | 5.8E1 | 2.8E1 | 2.4E1 | 2.3E1 | 1.8E1 | 1.2E2 | 1.1E2 | 26 | 23 | 26 | 23 | 0.54 |
| fB | ng/ml | 5.6E2 | 6.6E2 | 6.6E2 | 7.0E2 | 2.7E2 | 2.8E2 | 3.1E2 | 2.6E2 | 1.3E3 | 1.3E3 | 14 | 14 | 14 | 14 | 0.57 |
| fN | ng/ml | 2.1E-1 | 2.1E-1 | 2.0E0 | 3.5E0 | 3.9E0 | 5.8E0 | 2.1E-1 | 2.1E-1 | 1.4E1 | 2.1E1 | 26 | 23 | 26 | 23 | 0.54 |
| fP | ng/ml | 2.8E2 | 2.7E2 | 3.5E2 | 3.2E2 | 2.3E2 | 1.5E2 | 1.8E0 | 3.7E1 | 1.0E3 | 7.7E2 | 52 | 58 | 52 | 58 | 0.50 |
| fR | ng/ml | 1.5E5 | 1.7E5 | 1.9E5 | 2.4E5 | 1.5E5 | 1.9E5 | 3.9E4 | 1.9E2 | 6.3E5 | 6.8E5 | 50 | 42 | 50 | 42 | 0.58 |
| fY | ng/ml | 2.5E2 | 2.6E2 | 2.4E2 | 2.5E2 | 1.0E2 | 1.1E2 | 6.5E1 | 3.6E1 | 4.2E2 | 4.8E2 | 26 | 23 | 26 | 23 | 0.53 |
| gC | ng/ml | 2.4E2 | 2.2E2 | 2.6E2 | 2.5E2 | 1.3E2 | 1.0E2 | 9.7E1 | 8.3E1 | 6.4E2 | 4.8E2 | 20 | 18 | 20 | 18 | 0.49 |
| gL | pg/ml | 6.5E4 | 6.5E4 | 7.3E4 | 7.2E4 | 3.2E4 | 3.4E4 | 2.3E4 | 1.1E4 | 1.6E5 | 1.7E5 | 53 | 60 | 53 | 60 | 0.47 |
| gP | U/ml | 2.6E2 | 2.9E2 | 2.8E2 | 2.9E2 | 1.4E2 | 9.4E1 | 6.5E1 | 1.2E1 | 1.1E3 | 5.2E2 | 53 | 59 | 53 | 59 | 0.59 |
| gW | ng/ml | 5.4E2 | 3.7E2 | 1.0E3 | 6.9E2 | 1.1E3 | 8.4E2 | 6.8E1 | 2.3E0 | 6.1E3 | 4.2E3 | 39 | 44 | 39 | 44 | 0.39 |
| gV | ng/ml | 1.7E1 | 2.2E1 | 1.9E1 | 1.9E1 | 5.7E0 | 8.3E0 | 1.0E1 | 8.1E-2 | 2.7E1 | 3.0E1 | 18 | 11 | 18 | 11 | 0.56 |
| tF | pg/mL | 1.6E3 | 9.0E2 | 1.5E4 | 1.1E4 | 4.6E4 | 3.7E4 | 1.8E1 | 1.2E1 | 2.8E5 | 2.5E5 | 47 | 57 | 47 | 57 | 0.43 |
| gZ | ug/ml | 6.7E-1 | 7.8E-1 | 3.0E1 | 4.1E1 | 1.1E2 | 1.1E2 | 8.7E-2 | 1.7E-2 | 4.1E2 | 4.0E2 | 14 | 15 | 14 | 15 | 0.60 |
| hA | ng/ml | 2.6E0 | 2.9E0 | 1.7E1 | 1.5E1 | 6.0E1 | 4.6E1 | 1.7E-2 | 1.7E-2 | 3.5E2 | 2.9E2 | 40 | 44 | 40 | 44 | 0.53 |
| nM | pg/ml | 1.0E-9 | 1.0E-9 | 1.0E-9 | 4.2E1 | 0.0E0 | 2.5E2 | 1.0E-9 | 1.0E-9 | 1.0E-9 | 1.5E3 | 28 | 36 | 28 | 36 | 0.51 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nN | pg/ml | 1.1E3 | 2.2E3 | 1.8E3 | 1.2E4 | 1.8E3 | 3.0E4 | 1.1E2 | 3.5E2 | 7.1E3 | 1.5E5 | 28 | 36 | 28 | 36 | 0.69 |
| nO | pg/ml | 2.0E1 | 2.5E1 | 2.6E1 | 4.6E1 | 1.5E1 | 6.0E1 | 8.8E0 | 4.0E0 | 6.2E1 | 3.1E2 | 28 | 36 | 28 | 36 | 0.57 |
| nR | pg/ml | 2.0E1 | 1.8E1 | 5.1E1 | 1.4E2 | 7.2E1 | 3.6E2 | 1.8E0 | 1.0E0 | 2.6E2 | 1.9E3 | 28 | 36 | 28 | 36 | 0.51 |
| nT | pg/ml | 6.7E1 | 9.2E1 | 9.0E1 | 1.4E2 | 6.8E1 | 1.8E2 | 1.0E-9 | 1.0E-9 | 2.4E2 | 9.2E2 | 28 | 36 | 28 | 36 | 0.55 |
| nU | pg/ml | 4.4E1 | 4.5E1 | 5.6E1 | 1.4E2 | 6.4E1 | 2.9E2 | 1.0E-9 | 1.0E-9 | 2.1E2 | 1.5E3 | 28 | 36 | 28 | 36 | 0.56 |
| lW | pg/ml | 1.0E-9 | 1.0E-9 | 9.3E0 | 1.4E1 | 1.6E1 | 4.0E1 | 1.0E-9 | 1.0E-9 | 5.5E1 | 1.7E2 | 28 | 36 | 28 | 36 | 0.46 |
| lX | pg/ml | 9.1E2 | 8.8E2 | 9.4E2 | 9.7E2 | 4.7E2 | 6.2E2 | 3.2E2 | 1.9E2 | 1.9E3 | 2.5E3 | 28 | 36 | 28 | 36 | 0.49 |
| lY | pg/ml | 1.6E1 | 2.3E1 | 1.6E1 | 2.4E1 | 1.2E1 | 2.1E1 | 1.0E-9 | 1.0E-9 | 4.8E1 | 1.2E2 | 28 | 36 | 28 | 36 | 0.62 |
| mE | pg/ml | 1.0E-9 | 1.0E-9 | 9.0E-1 | 4.1E0 | 1.8E0 | 1.0E1 | 1.0E-9 | 1.0E-9 | 7.6E0 | 5.7E1 | 28 | 36 | 28 | 36 | 0.61 |
| mF | pg/ml | 1.0E-9 | 5.5E-1 | 1.0E1 | 5.1E1 | 4.6E1 | 1.8E1 | 1.0E-9 | 1.0E-9 | 2.5E2 | 1.1E2 | 28 | 36 | 28 | 36 | 0.59 |
| mH | pg/ml | 4.0E0 | 2.9E0 | 5.1E0 | 5.5E0 | 5.9E0 | 8.9E0 | 1.1E0 | 4.0E-1 | 3.2E1 | 5.3E1 | 28 | 36 | 28 | 36 | 0.48 |
| mI | pg/ml | 1.0E-9 | 3.6E0 | 5.6E0 | 3.2E1 | 1.1E1 | 8.1E1 | 1.0E-9 | 1.0E-9 | 3.7E1 | 4.6E2 | 28 | 36 | 28 | 36 | 0.63 |
| mM | pg/ml | 3.3E1 | 5.7E1 | 5.9E1 | 1.2E2 | 6.0E1 | 2.1E2 | 1.0E-9 | 1.0E-9 | 2.1E2 | 1.1E3 | 28 | 36 | 28 | 36 | 0.54 |
| mP | pg/ml | 1.3E1 | 1.6E1 | 1.6E1 | 4.4E1 | 1.1E1 | 1.3E2 | 1.0E-9 | 1.0E-9 | 5.8E1 | 8.1E2 | 27 | 36 | 27 | 36 | 0.56 |
| mS | pg/ml | 1.6E3 | 1.6E3 | 1.7E3 | 1.7E3 | 8.2E2 | 1.1E3 | 8.8E1 | 1.0E-9 | 3.7E3 | 5.1E3 | 28 | 36 | 28 | 36 | 0.50 |
| mT | pg/ml | 5.0E1 | 6.6E1 | 1.5E2 | 1.7E2 | 2.9E2 | 3.4E2 | 1.0E1 | 1.2E1 | 1.4E3 | 1.7E3 | 27 | 36 | 27 | 36 | 0.51 |
| mU | pg/ml | 2.5E0 | 1.9E0 | 3.4E0 | 9.6E0 | 2.9E0 | 3.7E1 | 1.0E-9 | 1.0E-9 | 1.6E1 | 2.2E2 | 27 | 36 | 27 | 36 | 0.44 |
| mW | pg/ml | 2.3E3 | 2.1E3 | 2.5E3 | 2.6E3 | 1.1E3 | 2.0E3 | 4.3E2 | 1.0E-9 | 4.9E3 | 1.1E4 | 27 | 36 | 27 | 36 | 0.45 |
| mY | pg/ml | 5.7E2 | 7.5E2 | 7.8E2 | 1.2E3 | 9.0E2 | 1.6E3 | 1.0E-9 | 1.0E-9 | 4.2E3 | 8.0E3 | 28 | 36 | 28 | 36 | 0.59 |
| mZ | pg/ml | 2.5E2 | 1.5E2 | 4.3E2 | 3.1E2 | 6.0E2 | 3.8E2 | 4.7E1 | 1.1E1 | 3.1E3 | 1.5E3 | 27 | 36 | 27 | 36 | 0.38 |
| nA | pg/ml | 1.5E0 | 1.8E0 | 6.7E0 | 6.3E0 | 1.4E1 | 1.3E1 | 1.0E-9 | 1.0E-9 | 5.4E1 | 6.5E1 | 27 | 36 | 27 | 36 | 0.52 |
| nB | pg/ml | 2.6E2 | 3.0E2 | 2.9E2 | 3.5E2 | 1.2E2 | 2.1E2 | 3.0E1 | 3.8E1 | 5.9E2 | 9.6E2 | 28 | 36 | 28 | 36 | 0.55 |
| nC | pg/ml | 1.0E-9 | 8.3E1 | 7.0E2 | 1.8E4 | 2.1E3 | 7.3E4 | 1.0E-9 | 1.0E-9 | 1.1E4 | 3.8E5 | 28 | 36 | 28 | 36 | 0.57 |
| nD | pg/ml | 6.2E0 | 7.3E0 | 8.2E0 | 1.6E1 | 8.2E0 | 4.3E1 | 1.0E-9 | 1.0E-9 | 3.7E1 | 2.6E2 | 27 | 36 | 27 | 36 | 0.52 |
| nF | pg/ml | 1.0E-9 | 1.0E-9 | 3.7E0 | 2.2E0 | 1.8E1 | 7.6E0 | 1.0E-9 | 1.0E-9 | 9.3E1 | 3.5E1 | 28 | 36 | 28 | 36 | 0.52 |
| nH | pg/ml | 1.0E-9 | 2.8E0 | 3.9E0 | 3.6E2 | 6.0E0 | 1.7E3 | 1.0E-9 | 1.0E-9 | 1.8E1 | 1.0E4 | 27 | 36 | 27 | 36 | 0.60 |
| nI | pg/ml | 2.5E1 | 1.3E-1 | 5.6E1 | 4.9E1 | 6.7E1 | 8.1E1 | 1.0E-9 | 1.0E-9 | 2.0E2 | 3.5E2 | 28 | 36 | 28 | 36 | 0.45 |
| nJ | pg/ml | 6.1E-1 | 2.9E-1 | 1.0E0 | 4.6E0 | 1.6E0 | 2.2E1 | 1.0E-9 | 1.0E-9 | 7.0E0 | 1.3E2 | 28 | 36 | 28 | 36 | 0.48 |
| nK | pg/ml | 1.0E-9 | 1.2E1 | 5.4E0 | 1.9E1 | 1.6E1 | 2.6E1 | 1.0E-9 | 1.0E-9 | 5.7E1 | 1.0E2 | 27 | 36 | 27 | 36 | 0.69 |
| nL | pg/ml | 1.0E-9 | 4.3E0 | 6.1E0 | 5.4E2 | 1.2E1 | 2.3E3 | 1.0E-9 | 1.0E-9 | 4.9E1 | 1.4E4 | 28 | 36 | 28 | 36 | 0.64 |
| hL | pg/ml | 1.6E4 | 2.4E4 | 2.0E4 | 2.4E4 | 1.5E4 | 1.4E4 | 2.6E3 | 5.1E3 | 7.2E4 | 6.0E4 | 26 | 23 | 26 | 23 | 0.60 |
| hO | pg/ml | 1.6E4 | 1.5E4 | 1.6E4 | 1.5E4 | 2.7E3 | 2.2E3 | 1.3E4 | 1.1E4 | 2.4E4 | 2.1E4 | 26 | 23 | 26 | 23 | 0.40 |
| hP | ng/ml | 4.4E5 | 4.4E5 | 3.8E5 | 6.3E5 | 1.9E5 | 6.8E5 | 4.7E4 | 1.7E4 | 9.0E5 | 2.8E6 | 26 | 23 | 26 | 23 | 0.62 |
| wJ | pg/ml | 1.5E5 | 1.0E5 | 1.6E5 | 1.6E5 | 9.5E4 | 1.4E5 | 1.1E4 | 1.3E4 | 4.0E5 | 5.8E5 | 25 | 26 | 25 | 26 | 0.44 |
| wK | pg/ml | 3.2E4 | 3.4E4 | 6.0E4 | 4.0E4 | 9.7E4 | 3.0E4 | 3.7E3 | 7.5E3 | 5.0E5 | 1.2E5 | 25 | 26 | 25 | 26 | 0.46 |
| wL | pg/ml | 9.5E0 | 3.1E0 | 7.8E1 | 3.1E1 | 1.9E2 | 9.0E1 | 1.0E-9 | 1.0E-9 | 8.4E2 | 3.5E2 | 25 | 26 | 25 | 26 | 0.36 |
| wP | pg/ml | 3.0E4 | 2.8E4 | 3.9E4 | 6.4E4 | 3.4E4 | 7.5E4 | 4.5E3 | 1.3E3 | 1.6E5 | 3.0E5 | 25 | 26 | 25 | 26 | 0.56 |
| wQ | pg/ml | 3.1E1 | 4.1E1 | 6.0E1 | 6.3E1 | 8.6E1 | 1.0E2 | 1.0E-9 | 1.0E-9 | 3.7E2 | 5.1E2 | 25 | 26 | 25 | 26 | 0.53 |
| hR | pg/ml | 2.8E4 | 2.6E4 | 3.2E4 | 2.7E4 | 1.1E4 | 1.1E4 | 1.8E4 | 1.0E-9 | 5.8E4 | 4.9E4 | 36 | 41 | 36 | 41 | 0.40 |
| hV | pg/ml | 4.7E2 | 4.4E2 | 4.5E2 | 4.2E2 | 2.1E2 | 2.2E2 | 1.3E2 | 1.0E-9 | 9.3E2 | 9.6E2 | 36 | 41 | 36 | 41 | 0.45 |
| hW | pg/ml | 1.7E3 | 2.4E3 | 2.0E3 | 3.3E3 | 1.2E3 | 6.0E3 | 9.0E2 | 1.0E-9 | 7.3E3 | 4.0E4 | 36 | 41 | 36 | 41 | 0.62 |
| hX | pg/ml | 1.1E3 | 1.1E3 | 1.3E3 | 1.1E3 | 1.3E3 | 5.5E2 | 3.3E2 | 2.5E0 | 8.6E3 | 2.9E3 | 36 | 41 | 36 | 41 | 0.49 |
| iA | pg/ml | 1.9E2 | 1.7E2 | 3.0E2 | 2.4E2 | 3.3E2 | 2.3E2 | 3.0E1 | 1.5E1 | 1.8E3 | 8.7E2 | 47 | 57 | 47 | 57 | 0.44 |
| iB | ng/ml | 4.8E0 | 5.7E0 | 5.8E0 | 7.8E0 | 4.0E0 | 5.9E0 | 3.3E-2 | 8.3E-1 | 1.9E1 | 2.4E1 | 40 | 44 | 40 | 44 | 0.59 |
| iC | U/ml | 2.6E-1 | 4.5E-1 | 4.2E-1 | 2.1E0 | 4.8E-1 | 8.3E0 | 1.0E-9 | 3.7E-2 | 1.8E0 | 5.5E1 | 40 | 44 | 40 | 44 | 0.63 |
| tQ | pg/ml | 1.3E3 | 1.6E3 | 1.4E3 | 1.6E3 | 5.1E2 | 6.6E2 | 3.7E2 | 5.0E2 | 2.5E3 | 3.3E3 | 24 | 23 | 24 | 23 | 0.55 |
| tT | pg/ml | 1.4E1 | 2.3E1 | 1.7E1 | 2.7E1 | 7.4E0 | 1.8E1 | 7.4E0 | 5.4E0 | 3.2E1 | 9.3E1 | 24 | 24 | 24 | 24 | 0.71 |
| tS | pg/ml | 8.9E-1 | 7.7E-1 | 9.7E-1 | 1.4E0 | 9.5E-1 | 2.2E0 | 1.0E-9 | 1.0E-9 | 4.0E0 | 1.0E1 | 24 | 25 | 24 | 25 | 0.53 |
| tX | pg/ml | 8.7E-1 | 1.2E0 | 1.1E0 | 2.3E0 | 8.9E-1 | 2.5E0 | 2.5E-2 | 2.8E-1 | 3.3E0 | 1.0E1 | 24 | 24 | 24 | 24 | 0.64 |
| tO | pg/ml | 4.4E0 | 3.9E0 | 4.4E0 | 5.5E0 | 2.6E0 | 4.0E0 | 1.0E-9 | 1.7E0 | 9.9E0 | 1.8E1 | 24 | 25 | 24 | 25 | 0.56 |
| tR | pg/ml | 1.7E-1 | 2.2E-1 | 2.5E-1 | 3.7E-1 | 2.6E-1 | 5.7E-1 | 1.0E-9 | 1.0E-9 | 9.1E-1 | 2.5E0 | 24 | 24 | 24 | 24 | 0.54 |
| tU | pg/ml | 9.0E0 | 9.9E0 | 1.2E1 | 1.4E1 | 1.1E1 | 1.6E1 | 1.6E0 | 2.2E-1 | 5.5E1 | 8.0E1 | 24 | 26 | 24 | 26 | 0.53 |
| tN | pg/ml | 1.9E1 | 2.0E1 | 2.0E1 | 4.1E1 | 1.4E1 | 4.3E1 | 1.0E-9 | 9.5E0 | 5.4E1 | 1.6E2 | 24 | 23 | 24 | 23 | 0.63 |
| tV | ng/ml | 3.9E2 | 9.8E2 | 5.6E2 | 9.9E2 | 4.1E2 | 6.5E2 | 1.9E2 | 5.3E1 | 1.8E3 | 3.1E3 | 25 | 25 | 25 | 25 | 0.73 |
| iH | ng/ml | 1.6E5 | 1.7E5 | 1.6E5 | 1.6E5 | 4.4E4 | 5.6E4 | 7.1E4 | 2.9E3 | 2.6E5 | 2.5E5 | 47 | 57 | 47 | 57 | 0.54 |
| iJ | ng/ml | 5.6E4 | 4.3E4 | 5.7E4 | 5.5E4 | 2.2E4 | 4.6E4 | 2.1E4 | 1.8E3 | 1.2E5 | 2.5E5 | 47 | 57 | 47 | 57 | 0.39 |
| hB | ng/ml | 4.6E-1 | 5.1E-1 | 6.0E-1 | 7.0E-1 | 4.3E-1 | 5.9E-1 | 1.4E-1 | 1.2E-1 | 1.9E0 | 3.2E0 | 47 | 57 | 47 | 57 | 0.55 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| hC | pg/ml | 3.7E3 | 7.7E3 | 6.1E3 | 1.0E4 | 6.4E3 | 1.6E4 | 6.0E1 | 4.1E1 | 3.3E4 | 1.1E5 | 47 | 57 | 47 | 57 | 0.60 |
| hF | ng/ml | 1.0E-9 | 1.0E-9 | 8.5E1 | 1.0E-9 | 5.8E2 | 0.0E0 | 1.0E-9 | 1.0E-9 | 4.0E3 | 1.0E-9 | 47 | 57 | 47 | 57 | 0.49 |
| hG | pg/ml | 7.0E3 | 6.6E3 | 8.2E3 | 7.5E3 | 3.4E3 | 3.5E3 | 1.8E3 | 2.3E3 | 1.8E4 | 2.0E4 | 47 | 57 | 47 | 57 | 0.41 |
| iO | ng/ml | 4.1E5 | 3.8E5 | 4.6E5 | 4.1E5 | 2.0E5 | 2.0E5 | 1.9E5 | 9.8E4 | 1.1E6 | 9.2E5 | 47 | 57 | 47 | 57 | 0.43 |
| iP | ng/ml | 6.0E4 | 5.1E4 | 6.2E4 | 5.5E4 | 6.1E4 | 3.4E4 | 8.3E3 | 7.1E3 | 4.4E5 | 2.2E5 | 47 | 57 | 47 | 57 | 0.46 |
| iZ | ng/ml | 1.5E3 | 1.8E3 | 1.8E3 | 2.0E3 | 9.1E2 | 8.4E2 | 8.2E2 | 7.5E2 | 5.7E3 | 4.6E3 | 47 | 55 | 47 | 55 | 0.59 |
| yH | pg/ml | 1.0E3 | 1.1E3 | 1.7E3 | 3.2E3 | 3.1E3 | 6.6E3 | 1.0E-9 | 1.0E-9 | 1.5E4 | 2.5E4 | 24 | 25 | 24 | 25 | 0.54 |
| yK | U/ml | 1.9E1 | 2.1E1 | 5.1E1 | 3.2E1 | 9.8E1 | 3.4E1 | 1.0E-9 | 1.0E-9 | 3.8E2 | 1.4E2 | 24 | 25 | 24 | 25 | 0.55 |
| yJ | pg/ml | 3.8E4 | 3.6E4 | 4.5E4 | 3.8E4 | 2.6E4 | 2.9E4 | 9.2E3 | 1.9E3 | 1.0E5 | 1.4E5 | 24 | 25 | 24 | 25 | 0.41 |
| yD | ng/ml | 1.2E-2 | 1.3E-2 | 1.3E-2 | 1.3E-2 | 5.9E-3 | 6.1E-3 | 1.0E-9 | 1.0E-9 | 2.8E-2 | 2.4E-2 | 25 | 26 | 25 | 26 | 0.52 |
| jB | ng/ml | 2.8E5 | 2.0E5 | 2.7E5 | 2.0E5 | 7.0E4 | 6.1E4 | 1.5E5 | 9.9E4 | 3.6E5 | 3.3E5 | 14 | 15 | 14 | 15 | 0.21 |
| wB | pg/ml | 9.5E3 | 9.8E3 | 1.1E4 | 1.3E4 | 7.6E3 | 1.0E4 | 1.9E3 | 2.3E3 | 3.3E4 | 4.2E4 | 25 | 26 | 25 | 26 | 0.55 |
| pY | pg/ml | 5.3E0 | 6.4E0 | 1.3E1 | 7.3E0 | 3.8E1 | 3.8E0 | 1.6E0 | 3.0E0 | 2.0E2 | 1.8E1 | 26 | 23 | 26 | 23 | 0.64 |
| sI | ng/ml | 4.8E-2 | 6.2E-2 | 5.3E-2 | 6.1E-2 | 2.3E-2 | 3.7E-2 | 2.1E-2 | 1.0E-2 | 1.1E-1 | 1.5E-1 | 13 | 13 | 13 | 13 | 0.57 |
| sF | mIU/mL | 6.7E0 | 5.6E0 | 1.2E1 | 1.1E1 | 2.0E1 | 1.4E1 | 6.2E-1 | 1.5E0 | 7.5E1 | 5.2E1 | 13 | 13 | 13 | 13 | 0.51 |
| sH | mIU/mL | 4.6E0 | 3.5E0 | 5.1E0 | 4.1E0 | 5.7E0 | 4.0E0 | 1.0E-9 | 3.9E-1 | 2.1E1 | 1.5E1 | 13 | 13 | 13 | 13 | 0.49 |
| sJ | ng/ml | 1.5E-1 | 1.5E-1 | 8.8E-1 | 1.9E-1 | 1.9E0 | 1.8E-1 | 1.0E-9 | 1.0E-9 | 6.4E0 | 6.1E-1 | 13 | 13 | 13 | 13 | 0.44 |
| rC | pg/ml | 1.9E3 | 1.4E3 | 2.5E3 | 1.9E3 | 2.8E3 | 2.0E3 | 1.1E2 | 1.0E-9 | 1.5E4 | 1.1E4 | 34 | 40 | 34 | 40 | 0.42 |
| rB | pg/ml | 3.1E1 | 2.9E1 | 5.2E1 | 5.6E1 | 7.8E1 | 7.0E1 | 1.0E-9 | 1.0E-9 | 3.9E2 | 3.2E2 | 34 | 40 | 34 | 40 | 0.52 |
| zG | 2.5ng/ml | 2.4E-1 | 1.9E-1 | 5.6E-1 | 6.3E-1 | 1.0E0 | 1.1E0 | 1.0E-9 | 1.0E-9 | 4.4E0 | 4.8E0 | 24 | 25 | 24 | 25 | 0.51 |
| zH | 2.3mU/ml | 9.2E-2 | 8.7E-2 | 1.0E-1 | 8.9E-2 | 5.4E-2 | 3.9E-2 | 1.0E-2 | 2.1E-2 | 3.1E-1 | 1.8E-1 | 24 | 25 | 24 | 25 | 0.41 |
| zI | 2.6ng/ml | 2.1E0 | 2.3E0 | 3.2E0 | 5.7E0 | 3.3E0 | 7.4E0 | 6.1E-1 | 5.4E-1 | 1.5E1 | 2.7E1 | 24 | 25 | 24 | 25 | 0.57 |
| qA | ng/ml | 8.0E6 | 1.3E7 | 1.0E7 | 1.3E7 | 7.7E6 | 6.7E6 | 3.7E6 | 4.3E6 | 3.9E7 | 3.0E7 | 26 | 23 | 26 | 23 | 0.69 |
| qB | ng/ml | 7.2E5 | 5.7E5 | 8.5E5 | 8.7E5 | 5.0E5 | 8.7E5 | 2.7E5 | 1.9E5 | 2.4E6 | 3.8E6 | 26 | 23 | 26 | 23 | 0.42 |
| qC | ng/ml | 3.6E5 | 2.6E5 | 6.6E5 | 5.2E5 | 7.9E5 | 9.5E5 | 3.6E4 | 2.5E4 | 3.1E6 | 4.7E6 | 26 | 23 | 26 | 23 | 0.41 |
| qD | ng/ml | 1.5E7 | 1.5E7 | 1.7E7 | 1.6E7 | 7.8E6 | 7.0E6 | 7.0E6 | 7.0E6 | 3.7E7 | 3.4E7 | 26 | 23 | 26 | 23 | 0.47 |
| jD | ng/ml | 4.0E1 | 3.2E1 | 4.1E1 | 5.3E1 | 3.4E1 | 6.1E1 | 1.0E-9 | 1.0E-9 | 1.1E2 | 2.9E2 | 40 | 44 | 40 | 44 | 0.52 |
| jE | ng/ml | 1.0E-9 | 1.0E-9 | 5.0E0 | 5.2E0 | 1.3E1 | 1.0E1 | 1.0E-9 | 1.0E-9 | 6.2E1 | 3.5E1 | 40 | 44 | 40 | 44 | 0.53 |
| jF | ng/ml | 5.0E1 | 2.1E1 | 5.2E1 | 3.7E1 | 5.3E1 | 4.8E1 | 1.0E-9 | 1.0E-9 | 1.9E2 | 1.9E2 | 40 | 44 | 40 | 44 | 0.42 |
| jG | ng/ml | 4.4E3 | 4.0E3 | 4.7E3 | 4.2E3 | 1.9E3 | 2.0E3 | 1.9E3 | 6.7E2 | 9.5E3 | 9.6E3 | 40 | 44 | 40 | 44 | 0.43 |
| jH | ng/ml | 8.0E1 | 7.5E1 | 8.2E1 | 8.9E1 | 4.3E1 | 6.9E1 | 2.1E1 | 1.3E1 | 2.1E2 | 4.3E2 | 40 | 44 | 40 | 44 | 0.49 |
| jI | ng/ml | 7.4E1 | 7.7E1 | 8.0E1 | 9.4E1 | 3.3E1 | 7.0E1 | 3.8E1 | 3.8E1 | 1.9E2 | 4.4E2 | 40 | 44 | 40 | 44 | 0.53 |
| sK | pg/mL | 4.3E3 | 3.6E3 | 4.1E3 | 5.0E3 | 1.7E3 | 4.5E3 | 1.8E3 | 2.1E3 | 8.8E3 | 2.3E4 | 24 | 23 | 24 | 23 | 0.50 |
| sM | pg/mL | 7.4E4 | 7.4E4 | 7.9E4 | 8.5E4 | 2.9E4 | 3.9E4 | 4.8E4 | 3.9E4 | 1.6E5 | 2.0E5 | 24 | 23 | 24 | 23 | 0.54 |
| sO | pg/mL | 2.3E8 | 2.3E8 | 2.4E8 | 2.4E8 | 8.2E7 | 1.1E8 | 4.9E7 | 6.6E7 | 3.7E8 | 4.4E8 | 24 | 23 | 24 | 23 | 0.48 |
| wC | ng/ml | 1.6E0 | 1.5E0 | 2.0E0 | 1.8E0 | 1.4E0 | 1.1E0 | 3.6E-1 | 6.1E-2 | 6.5E0 | 4.8E0 | 25 | 26 | 25 | 26 | 0.47 |
| wD | ng/ml | 2.1E1 | 2.8E1 | 1.2E2 | 5.3E1 | 4.2E2 | 6.1E1 | 3.8E0 | 2.8E0 | 2.1E3 | 2.9E2 | 25 | 26 | 25 | 26 | 0.63 |
| wE | ng/ml | 4.6E1 | 5.7E1 | 4.6E1 | 5.6E1 | 1.8E1 | 2.0E1 | 8.1E0 | 2.0E1 | 7.6E1 | 8.9E1 | 25 | 26 | 25 | 26 | 0.62 |
| wG | ng/ml | 1.2E-1 | 8.1E-2 | 1.5E-1 | 1.3E-1 | 1.4E-1 | 1.5E-1 | 1.0E-9 | 1.0E-9 | 4.8E-1 | 6.8E-1 | 25 | 26 | 25 | 26 | 0.45 |
| wH | ng/ml | 4.7E-2 | 3.3E-2 | 3.2E-1 | 4.4E-1 | 8.8E-1 | 1.1E0 | 1.0E-9 | 1.0E-9 | 4.2E0 | 5.6E0 | 25 | 26 | 25 | 26 | 0.51 |
| wF | ng/ml | 2.7E-1 | 2.7E-1 | 3.5E0 | 1.6E0 | 1.2E1 | 3.8E0 | 1.0E-9 | 1.0E-9 | 5.7E1 | 1.9E1 | 25 | 26 | 25 | 26 | 0.55 |
| rA | pg/ml | 2.4E1 | 2.2E1 | 2.6E1 | 2.9E1 | 1.6E1 | 2.4E1 | 1.0E-9 | 1.0E-9 | 5.9E1 | 1.1E2 | 38 | 43 | 38 | 43 | 0.50 |
| qZ | pg/ml | 4.7E1 | 5.4E1 | 3.9E2 | 8.6E2 | 1.8E3 | 2.6E3 | 2.8E-4 | 5.9E-4 | 1.0E4 | 1.0E4 | 30 | 30 | 30 | 30 | 0.55 |
| qY | pg/ml | 1.7E1 | 1.4E1 | 4.1E1 | 3.3E1 | 5.2E1 | 5.7E1 | 8.7E-1 | 2.1E0 | 1.8E2 | 3.3E2 | 38 | 43 | 38 | 43 | 0.46 |
| qX | pg/ml | 5.5E1 | 6.8E1 | 6.2E1 | 7.8E1 | 3.9E1 | 5.4E1 | 1.0E-9 | 1.0E-9 | 1.6E2 | 2.1E2 | 38 | 43 | 38 | 43 | 0.56 |
| qW | pg/ml | 7.1E0 | 7.6E0 | 8.6E0 | 1.0E1 | 8.0E0 | 9.7E0 | 1.0E-9 | 1.0E-9 | 3.6E1 | 3.6E1 | 38 | 43 | 38 | 43 | 0.52 |
| qV | pg/ml | 1.5E3 | 2.2E3 | 2.3E3 | 2.4E3 | 2.1E3 | 1.8E3 | 2.7E2 | 1.0E2 | 1.1E4 | 9.6E3 | 38 | 43 | 38 | 43 | 0.53 |
| qU | pg/ml | 4.7E1 | 9.5E1 | 1.4E2 | 2.4E2 | 2.4E2 | 3.8E2 | 1.0E-9 | 1.0E-9 | 1.2E3 | 2.1E3 | 38 | 43 | 38 | 43 | 0.61 |
| qT | pg/ml | 3.7E1 | 4.1E1 | 7.3E1 | 6.1E1 | 9.6E1 | 4.6E1 | 1.0E-9 | 1.0E-9 | 4.9E2 | 1.8E2 | 38 | 43 | 38 | 43 | 0.54 |
| qI | ng/ml | 6.0E4 | 6.4E4 | 6.0E4 | 6.7E4 | 2.8E4 | 3.4E4 | 1.0E4 | 2.5E4 | 1.3E5 | 1.6E5 | 24 | 22 | 24 | 22 | 0.55 |
| qH | ng/ml | 6.3E4 | 5.7E4 | 7.1E4 | 7.1E4 | 4.2E4 | 3.9E4 | 1.5E4 | 2.3E4 | 1.8E5 | 1.8E5 | 24 | 22 | 24 | 22 | 0.52 |
| qG | ng/ml | 1.8E5 | 1.9E5 | 1.8E5 | 2.0E5 | 6.3E4 | 7.6E4 | 3.4E4 | 8.4E4 | 3.0E5 | 4.2E5 | 24 | 22 | 24 | 22 | 0.55 |
| jK | ng/ml | 1.5E3 | 1.4E3 | 1.6E3 | 1.6E3 | 6.3E2 | 6.5E2 | 2.8E2 | 7.5E2 | 4.1E3 | 3.6E3 | 40 | 44 | 40 | 44 | 0.46 |
| jL | ng/ml | 1.7E2 | 2.1E2 | 2.7E2 | 2.8E2 | 2.1E2 | 1.8E2 | 5.9E1 | 6.4E1 | 8.1E2 | 7.6E2 | 40 | 44 | 40 | 44 | 0.55 |
| jM | ng/ml | 6.3E4 | 6.8E4 | 6.6E4 | 7.8E4 | 3.2E4 | 4.5E4 | 2.1E4 | 4.6E3 | 1.5E5 | 1.7E5 | 40 | 44 | 40 | 44 | 0.57 |
| jO | pg/ml | 2.2E5 | 2.5E5 | 2.7E5 | 2.7E5 | 1.5E5 | 1.5E5 | 7.6E4 | 9.6E4 | 7.7E5 | 6.5E5 | 40 | 44 | 40 | 44 | 0.50 |
| jP | pg/ml | 2.6E5 | 2.7E5 | 2.9E5 | 3.2E5 | 1.5E5 | 1.5E5 | 6.1E4 | 1.3E5 | 7.1E5 | 7.0E5 | 40 | 44 | 40 | 44 | 0.55 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jQ | pg/ml | 2.5E3 | 2.1E3 | 3.1E3 | 2.9E3 | 2.5E3 | 2.9E3 | 2.5E2 | 5.0E0 | 1.0E4 | 1.3E4 | 40 | 44 | 40 | 44 | 0.45 |
| jR | pg/ml | 5.9E3 | 4.3E3 | 8.7E3 | 1.0E4 | 8.4E3 | 1.3E4 | 3.0E1 | 1.0E-9 | 3.5E4 | 5.6E4 | 40 | 44 | 40 | 44 | 0.47 |
| jT | pg/ml | 1.7E5 | 1.7E5 | 1.7E5 | 1.7E5 | 6.1E4 | 6.0E4 | 7.1E4 | 7.5E4 | 3.5E5 | 3.5E5 | 40 | 44 | 40 | 44 | 0.51 |
| xA | pg/ml | 9.0E0 | 3.9E0 | 1.4E1 | 1.5E1 | 1.7E1 | 3.7E1 | 1.0E-9 | 1.0E-9 | 6.1E1 | 1.6E2 | 24 | 25 | 24 | 25 | 0.37 |
| yE | pg/ml | 8.1E1 | 8.6E1 | 8.0E1 | 8.7E1 | 3.2E1 | 3.8E1 | 6.4E0 | 3.5E1 | 1.4E2 | 2.0E2 | 24 | 25 | 24 | 25 | 0.53 |
| tM | pg/ml | 4.3E1 | 3.9E1 | 4.0E1 | 4.1E1 | 1.7E1 | 2.0E1 | 1.0E-9 | 1.1E1 | 6.1E1 | 9.9E1 | 24 | 25 | 24 | 25 | 0.46 |
| tL | pg/ml | 1.0E-9 | 1.0E-9 | 3.0E0 | 3.4E-1 | 1.4E1 | 8.8E-1 | 1.0E-9 | 1.0E-9 | 6.7E1 | 3.6E0 | 24 | 25 | 24 | 25 | 0.49 |
| jU | mIU/ml | 5.4E0 | 6.4E0 | 1.4E1 | 1.1E1 | 2.4E1 | 1.3E1 | 8.1E-2 | 7.1E-1 | 1.1E2 | 5.7E1 | 40 | 44 | 40 | 44 | 0.53 |
| jV | mIU/ml | 1.8E0 | 2.1E0 | 4.5E0 | 3.6E0 | 6.7E0 | 4.2E0 | 2.7E-3 | 4.9E-2 | 3.2E1 | 1.8E1 | 40 | 44 | 40 | 44 | 0.49 |
| jY | ng/ml | 5.8E-4 | 1.7E-3 | 1.0E-2 | 7.2E-3 | 4.7E-2 | 1.6E-2 | 1.0E-9 | 1.0E-9 | 3.0E-1 | 9.4E-2 | 40 | 44 | 40 | 44 | 0.57 |
| kC | pg/ml | 9.7E1 | 1.1E2 | 1.4E2 | 2.3E2 | 1.9E2 | 4.7E2 | 2.1E1 | 3.6E1 | 1.1E3 | 2.7E3 | 28 | 36 | 28 | 36 | 0.56 |
| kE | pg/ml | 1.5E5 | 1.4E5 | 1.4E5 | 1.4E5 | 3.8E4 | 4.3E4 | 4.1E4 | 3.8E4 | 2.3E5 | 2.7E5 | 28 | 36 | 28 | 36 | 0.50 |
| kF | pg/mL | 6.8E1 | 6.5E1 | 6.8E1 | 7.3E1 | 1.7E1 | 3.1E1 | 3.5E1 | 4.0E1 | 1.1E2 | 1.5E2 | 28 | 36 | 28 | 36 | 0.47 |
| kG | pg/mL | 8.0E3 | 8.9E3 | 1.1E4 | 1.7E4 | 9.2E3 | 2.8E4 | 1.9E3 | 1.1E3 | 4.1E4 | 1.6E5 | 28 | 36 | 28 | 36 | 0.55 |
| kI | pg/ml | 2.2E2 | 2.0E2 | 2.3E2 | 2.2E2 | 1.2E2 | 1.2E2 | 6.4E1 | 1.0E-9 | 6.7E2 | 5.5E2 | 28 | 36 | 28 | 36 | 0.47 |
| kK | pg/ml | 1.2E2 | 1.2E2 | 1.4E2 | 1.7E2 | 1.1E2 | 1.7E2 | 2.2E1 | 2.1E1 | 5.0E2 | 9.1E2 | 28 | 36 | 28 | 36 | 0.52 |
| kN | pg/ml | 1.0E3 | 1.2E3 | 1.5E3 | 1.8E3 | 1.9E3 | 1.9E3 | 2.1E2 | 3.8E2 | 1.0E4 | 8.7E3 | 28 | 36 | 28 | 36 | 0.53 |
| kO | pg/ml | 7.0E3 | 7.4E3 | 7.6E3 | 1.2E4 | 2.9E3 | 2.3E4 | 4.0E3 | 3.8E3 | 1.9E4 | 1.5E5 | 28 | 36 | 28 | 36 | 0.52 |
| kP | pg/ml | 5.6E3 | 5.3E3 | 7.3E3 | 6.1E3 | 4.8E3 | 3.8E3 | 3.1E3 | 9.6E2 | 2.7E4 | 1.5E4 | 28 | 36 | 28 | 36 | 0.42 |
| kQ | pg/ml | 4.4E3 | 4.5E3 | 5.3E3 | 5.9E3 | 3.7E3 | 4.6E3 | 5.6E2 | 1.1E3 | 2.5E4 | 2.5E4 | 47 | 57 | 47 | 57 | 0.52 |
| kR | pg/ml | 2.2E1 | 2.6E1 | 4.8E1 | 3.2E1 | 1.5E2 | 2.4E1 | 1.0E-9 | 3.4E0 | 1.0E3 | 1.1E2 | 47 | 57 | 47 | 57 | 0.54 |
| kS | pg/ml | 8.1E2 | 9.3E2 | 9.4E2 | 1.0E3 | 5.9E2 | 6.0E2 | 8.2E1 | 2.5E2 | 3.2E3 | 3.0E3 | 47 | 57 | 47 | 57 | 0.56 |
| pS | ng/ml | 1.8E5 | 1.4E5 | 2.0E5 | 1.7E5 | 9.2E4 | 1.1E5 | 7.5E4 | 6.8E4 | 5.0E5 | 5.7E5 | 24 | 23 | 24 | 23 | 0.36 |
| rZ | ng/ml | 1.4E-3 | 2.2E-3 | 5.7E-3 | 1.2E-2 | 1.6E-2 | 2.2E-2 | 1.0E-9 | 1.0E-9 | 9.4E-2 | 1.1E-1 | 34 | 41 | 34 | 41 | 0.60 |
| rY | ng/ml | 6.4E-2 | 6.7E-2 | 3.1E-1 | 5.7E-1 | 1.1E0 | 3.1E0 | 1.6E-2 | 1.0E-9 | 6.3E0 | 2.0E1 | 34 | 41 | 34 | 41 | 0.51 |
| rX | ng/ml | 1.0E-9 | 1.0E-9 | 1.4E-1 | 8.9E-2 | 6.4E-1 | 4.8E-1 | 1.0E-9 | 1.0E-9 | 3.7E0 | 3.1E0 | 34 | 41 | 34 | 41 | 0.50 |
| lK | pg/ml | 7.2E1 | 4.4E1 | 1.5E2 | 1.3E2 | 1.8E2 | 1.6E2 | 7.6E0 | 1.0E-9 | 7.0E2 | 6.9E2 | 40 | 43 | 40 | 43 | 0.41 |
| lL | pg/ml | 2.0E3 | 1.4E3 | 3.7E3 | 2.3E3 | 7.0E3 | 2.1E3 | 7.5E1 | 1.2E2 | 4.2E4 | 7.7E3 | 40 | 44 | 40 | 44 | 0.42 |
| lM | pg/ml | 1.6E3 | 1.2E3 | 4.6E3 | 5.4E3 | 8.2E3 | 1.2E4 | 2.2E2 | 9.5E0 | 4.2E4 | 6.7E4 | 40 | 44 | 40 | 44 | 0.48 |
| lN | pg/ml | 1.0E-9 | 1.0E-9 | 3.7E0 | 3.0E0 | 8.0E0 | 6.2E0 | 1.0E-9 | 1.0E-9 | 4.3E1 | 2.4E1 | 40 | 44 | 40 | 44 | 0.49 |
| lO | pg/ml | 1.0E-9 | 1.0E-9 | 8.5E-1 | 6.1E0 | 5.4E0 | 2.8E1 | 1.0E-9 | 1.0E-9 | 3.4E1 | 1.4E2 | 40 | 43 | 40 | 43 | 0.51 |
| zA | ng/ml | 2.2E7 | 2.0E7 | 2.3E7 | 2.0E7 | 7.1E6 | 5.2E6 | 1.0E7 | 1.0E7 | 3.6E7 | 3.1E7 | 24 | 26 | 24 | 26 | 0.39 |
| rW | ng/ml | 8.5E-3 | 1.4E-2 | 2.4E-2 | 4.1E-2 | 3.9E-2 | 7.6E-2 | 1.0E-9 | 1.0E-9 | 1.7E-1 | 3.2E-1 | 25 | 21 | 25 | 21 | 0.60 |
| rV | ng/ml | 1.0E-9 | 1.0E-9 | 1.3E-2 | 1.4E-2 | 5.6E-2 | 3.5E-2 | 1.0E-9 | 1.0E-9 | 2.8E-1 | 1.5E-1 | 25 | 21 | 25 | 21 | 0.58 |
| rU | ng/ml | 4.2E-2 | 9.7E-2 | 1.9E-1 | 1.2E-1 | 5.3E-1 | 1.1E-1 | 1.0E-9 | 1.0E-9 | 2.7E0 | 4.0E-1 | 25 | 21 | 25 | 21 | 0.60 |
| rT | ng/ml | 6.3E0 | 4.4E0 | 6.7E0 | 7.2E0 | 4.3E0 | 5.5E0 | 6.5E-1 | 1.0E0 | 2.1E1 | 2.0E1 | 25 | 21 | 25 | 21 | 0.50 |
| rS | ng/ml | 3.6E0 | 5.8E0 | 5.5E0 | 1.3E1 | 5.7E0 | 1.9E1 | 1.8E0 | 1.1E0 | 2.5E1 | 7.0E1 | 25 | 21 | 25 | 21 | 0.63 |
| sC | pg/mL | 4.9E3 | 9.6E3 | 7.1E3 | 1.4E4 | 7.7E3 | 1.8E4 | 2.4E3 | 1.7E3 | 3.9E4 | 7.4E4 | 24 | 23 | 24 | 23 | 0.65 |
| yL | pg/ml | 3.2E1 | 2.8E1 | 3.9E1 | 9.0E1 | 3.3E1 | 2.8E2 | 5.6E0 | 9.1E0 | 1.8E2 | 1.4E3 | 24 | 25 | 24 | 25 | 0.44 |
| rP | ng/ml | 1.2E2 | 2.0E2 | 1.9E2 | 2.6E2 | 1.9E2 | 2.4E2 | 1.0E-9 | 1.2E1 | 5.0E2 | 8.0E2 | 25 | 21 | 25 | 21 | 0.56 |
| rQ | ng/ml | 1.0E-9 | 1.0E-9 | 1.0E-9 | 1.5E1 | 0.0E0 | 4.4E1 | 1.0E-9 | 1.0E-9 | 1.0E-9 | 1.7E2 | 25 | 21 | 25 | 21 | 0.57 |
| rO | ng/ml | 1.5E-2 | 2.5E-2 | 3.7E-2 | 4.1E-2 | 8.1E-2 | 4.8E-2 | 1.0E-9 | 1.0E-9 | 4.0E-1 | 1.9E-1 | 25 | 21 | 25 | 21 | 0.61 |
| rR | ng/ml | 1.0E-9 | 4.0E0 | 6.4E0 | 1.8E1 | 1.7E1 | 2.6E1 | 1.0E-9 | 1.0E-9 | 7.9E1 | 9.5E1 | 25 | 21 | 25 | 21 | 0.68 |
| rN | ng/ml | 7.0E-1 | 6.2E-1 | 8.6E-1 | 1.5E0 | 5.7E-1 | 2.8E0 | 5.1E-2 | 2.1E-1 | 2.3E0 | 1.3E1 | 25 | 21 | 25 | 21 | 0.47 |
| qO | pg/ml | 7.4E3 | 1.0E4 | 9.9E3 | 1.4E4 | 6.9E3 | 1.3E4 | 2.7E3 | 7.4E2 | 2.8E4 | 4.8E4 | 24 | 23 | 24 | 23 | 0.58 |
| qP | pg/ml | 3.3E2 | 3.4E2 | 3.6E2 | 4.7E2 | 2.0E2 | 3.5E2 | 7.0E1 | 1.1E2 | 8.3E2 | 1.5E3 | 24 | 23 | 24 | 23 | 0.55 |
| qQ | pg/ml | 1.5E1 | 1.5E1 | 2.3E1 | 2.5E1 | 5.6E1 | 5.4E1 | 1.0E-9 | 1.0E-9 | 2.8E2 | 2.6E2 | 24 | 23 | 24 | 23 | 0.50 |
| nW | pg/ml | 1.1E5 | 1.1E5 | 1.1E5 | 1.1E5 | 2.7E4 | 2.9E4 | 5.8E4 | 3.6E4 | 1.8E5 | 1.7E5 | 47 | 57 | 47 | 57 | 0.47 |
| nY | pg/ml | 2.2E3 | 2.5E3 | 2.6E3 | 2.8E3 | 1.7E3 | 1.5E3 | 5.1E2 | 6.3E2 | 1.0E4 | 8.1E3 | 47 | 57 | 47 | 57 | 0.56 |
| oO | pg/ml | 9.1E4 | 9.3E4 | 1.0E5 | 1.1E5 | 5.4E4 | 8.3E4 | 3.2E4 | 3.3E3 | 2.6E5 | 4.0E5 | 24 | 33 | 24 | 33 | 0.50 |
| oP | pg/ml | 1.4E5 | 1.3E5 | 1.6E5 | 1.6E5 | 6.9E4 | 1.1E5 | 4.9E4 | 2.4E4 | 3.1E5 | 5.7E5 | 24 | 33 | 24 | 33 | 0.46 |
| oQ | pg/ml | 3.4E3 | 3.1E3 | 3.5E3 | 5.0E3 | 2.1E3 | 6.0E3 | 1.1E3 | 7.7E2 | 1.1E4 | 3.2E4 | 24 | 33 | 24 | 33 | 0.53 |
| oE | pg/ml | 2.0E2 | 2.3E2 | 4.7E2 | 6.3E2 | 5.2E2 | 8.0E2 | 1.0E-9 | 1.0E-9 | 1.9E3 | 3.4E3 | 47 | 57 | 47 | 57 | 0.54 |
| oF | pg/ml | 1.1E4 | 1.9E4 | 2.3E4 | 3.6E4 | 2.9E4 | 4.7E4 | 4.3E2 | 5.1E2 | 1.5E5 | 2.5E5 | 47 | 57 | 47 | 57 | 0.58 |
| oH | pg/ml | 3.6E1 | 3.4E1 | 8.5E1 | 7.6E1 | 1.5E2 | 1.0E2 | 5.4E0 | 4.3E-1 | 8.6E2 | 4.8E2 | 47 | 57 | 47 | 57 | 0.47 |
| oK | pg/ml | 9.1E2 | 8.8E2 | 1.7E3 | 1.5E3 | 1.8E3 | 1.9E3 | 8.8E1 | 1.4E2 | 7.8E3 | 1.2E4 | 47 | 57 | 47 | 57 | 0.49 |
| oN | pg/ml | 5.5E2 | 5.7E2 | 1.2E3 | 8.2E2 | 2.8E3 | 8.9E2 | 1.6E2 | 1.1E2 | 1.8E4 | 5.3E3 | 47 | 57 | 47 | 57 | 0.54 |

Figure 33 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| oW | pg/ml | 2.0E2 | 3.7E2 | 2.6E2 | 1.1E3 | 1.9E2 | 2.0E3 | 7.7E1 | 2.9E1 | 7.3E2 | 7.6E3 | 14 | 15 | 14 | 15 | 0.66 |
| oT | pg/ml | 2.8E2 | 3.0E2 | 3.2E2 | 3.5E2 | 1.5E2 | 2.1E2 | 1.0E2 | 1.3E2 | 7.4E2 | 7.9E2 | 14 | 15 | 14 | 15 | 0.53 |
| oV | pg/ml | 1.1E2 | 8.9E1 | 2.7E2 | 2.9E2 | 3.9E2 | 5.7E2 | 2.1E1 | 1.0E-9 | 1.4E3 | 2.2E3 | 14 | 15 | 14 | 15 | 0.47 |
| oD | pg/ml | 1.7E4 | 1.3E4 | 1.7E4 | 1.5E4 | 4.8E3 | 6.9E3 | 8.7E3 | 6.6E3 | 2.5E4 | 3.2E4 | 14 | 15 | 14 | 15 | 0.36 |
| uL | ng/ml | 3.4E1 | 3.7E1 | 5.2E1 | 4.1E1 | 5.9E1 | 1.9E1 | 1.5E1 | 1.4E1 | 2.9E2 | 8.0E1 | 24 | 23 | 24 | 23 | 0.51 |
| uO | ng/ml | 4.6E-1 | 3.4E-1 | 9.9E-1 | 7.3E-1 | 1.9E0 | 7.7E-1 | 1.0E-9 | 1.0E-9 | 9.3E0 | 2.1E0 | 24 | 23 | 24 | 23 | 0.49 |
| uM | ng/ml | 6.1E-1 | 5.0E-1 | 1.3E0 | 6.2E-1 | 2.6E0 | 6.1E-1 | 1.0E-9 | 1.0E-9 | 1.3E1 | 2.5E0 | 24 | 23 | 24 | 23 | 0.41 |
| uI | ng/ml | 7.4E-2 | 5.9E-2 | 1.0E-1 | 1.1E-1 | 1.1E-1 | 1.2E-1 | 1.6E-2 | 1.5E-2 | 5.8E-1 | 4.3E-1 | 24 | 22 | 24 | 22 | 0.46 |
| uN | ng/ml | 1.5E1 | 1.6E1 | 1.7E1 | 1.8E1 | 6.2E0 | 8.3E0 | 8.0E0 | 9.9E0 | 3.0E1 | 4.1E1 | 24 | 23 | 24 | 23 | 0.53 |
| uG | ng/ml | 1.8E1 | 1.9E1 | 2.2E1 | 2.6E1 | 1.6E1 | 2.7E1 | 6.1E0 | 1.2E0 | 7.9E1 | 1.3E2 | 24 | 23 | 24 | 23 | 0.53 |
| uR | ng/ml | 2.5E0 | 1.7E0 | 3.2E0 | 2.5E0 | 2.6E0 | 2.0E0 | 1.1E0 | 7.5E-1 | 1.3E1 | 8.3E0 | 24 | 25 | 24 | 25 | 0.35 |
| uP | ng/ml | 2.0E0 | 2.4E0 | 2.3E0 | 2.7E0 | 1.0E0 | 1.2E0 | 1.2E0 | 9.3E-1 | 6.0E0 | 6.1E0 | 24 | 25 | 24 | 25 | 0.64 |
| uV | ng/ml | 1.1E-4 | 2.3E-3 | 2.0E-2 | 8.9E-3 | 4.5E-2 | 1.2E-2 | 1.0E-9 | 1.0E-9 | 2.0E-1 | 4.3E-2 | 24 | 25 | 24 | 25 | 0.49 |
| uT | ng/ml | 6.6E1 | 8.4E1 | 1.0E2 | 1.0E2 | 1.0E2 | 8.7E1 | 3.4E1 | 1.3E1 | 4.5E2 | 4.1E2 | 24 | 25 | 24 | 25 | 0.54 |
| uU | ng/ml | 1.6E0 | 1.7E0 | 1.9E0 | 2.4E0 | 1.3E0 | 3.7E0 | 6.0E-1 | 5.4E-1 | 6.0E0 | 2.0E1 | 24 | 25 | 24 | 25 | 0.52 |
| uW | ng/ml | 7.7E0 | 7.9E0 | 7.9E0 | 8.2E0 | 2.1E0 | 2.5E0 | 4.4E0 | 5.1E0 | 1.3E1 | 1.6E1 | 24 | 23 | 24 | 23 | 0.53 |
| vB | ng/ml | 3.0E0 | 3.2E0 | 3.4E0 | 3.4E0 | 2.3E0 | 2.2E0 | 5.9E-1 | 8.3E-1 | 1.0E1 | 1.0E1 | 24 | 23 | 24 | 23 | 0.51 |
| vC | ng/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 24 | 23 | 24 | 23 | 0.50 |
| uY | ng/ml | 5.7E-1 | 7.5E-1 | 8.7E-1 | 1.1E0 | 9.0E-1 | 1.0E0 | 6.8E-2 | 3.1E-1 | 3.8E0 | 4.4E0 | 24 | 23 | 24 | 23 | 0.66 |
| uZ | ng/ml | 5.8E-1 | 5.3E-1 | 6.8E-1 | 8.0E-1 | 5.9E-1 | 9.7E-1 | 1.0E-1 | 1.7E-1 | 3.0E0 | 4.9E0 | 24 | 23 | 24 | 23 | 0.52 |
| uX | ng/ml | 7.8E0 | 9.1E0 | 1.1E1 | 1.5E1 | 7.8E0 | 1.6E1 | 3.6E0 | 4.2E0 | 4.0E1 | 6.5E1 | 24 | 23 | 24 | 23 | 0.59 |
| vA | ng/ml | 6.2E-2 | 6.6E-2 | 7.0E-2 | 9.4E-2 | 3.1E-2 | 9.3E-2 | 3.2E-2 | 2.5E-2 | 1.5E-1 | 4.2E-1 | 24 | 23 | 24 | 23 | 0.52 |
| vH | ng/ml | 1.3E-1 | 8.5E-2 | 1.8E-1 | 1.9E-1 | 1.6E-1 | 3.8E-1 | 4.6E-2 | 2.0E-2 | 6.6E-1 | 1.9E0 | 24 | 23 | 24 | 23 | 0.34 |
| vI | ng/ml | 2.2E0 | 2.9E0 | 2.3E0 | 3.0E0 | 1.4E0 | 2.7E0 | 4.4E-1 | 6.3E-3 | 6.4E0 | 1.0E1 | 24 | 23 | 24 | 23 | 0.57 |
| vP | ng/ml | 3.4E2 | 3.1E2 | 3.7E2 | 5.5E2 | 2.6E2 | 5.2E2 | 7.0E1 | 6.7E1 | 1.0E3 | 2.4E3 | 24 | 25 | 24 | 25 | 0.60 |
| vT | ng/ml | 7.1E1 | 8.2E1 | 8.1E1 | 8.8E1 | 4.2E1 | 3.8E1 | 4.1E1 | 4.6E1 | 2.4E2 | 1.8E2 | 24 | 25 | 24 | 25 | 0.58 |
| vU | ng/ml | 1.0E-9 | 1.0E-9 | 2.3E1 | 2.1E1 | 3.7E1 | 3.4E1 | 1.0E-9 | 1.0E-9 | 1.2E2 | 1.1E2 | 24 | 25 | 24 | 25 | 0.48 |
| vQ | ng/ml | 3.9E2 | 4.5E2 | 3.9E2 | 4.2E2 | 1.4E2 | 1.8E2 | 7.2E1 | 1.2E2 | 7.0E2 | 8.4E2 | 24 | 25 | 24 | 25 | 0.54 |
| vO | ng/ml | 1.8E3 | 1.7E3 | 1.8E3 | 1.8E3 | 4.5E2 | 4.9E2 | 1.1E3 | 1.0E3 | 2.9E3 | 3.2E3 | 24 | 25 | 24 | 25 | 0.48 |
| vS | ng/ml | 1.3E3 | 1.3E3 | 1.3E3 | 1.2E3 | 3.7E2 | 5.6E2 | 1.0E-9 | 1.0E-9 | 2.1E3 | 2.0E3 | 24 | 25 | 24 | 25 | 0.50 |
| vV | ng/ml | 7.4E2 | 9.0E2 | 8.0E2 | 1.2E3 | 5.5E2 | 1.1E3 | 1.1E2 | 1.0E2 | 1.9E3 | 4.6E3 | 24 | 25 | 24 | 25 | 0.58 |
| vW | ng/ml | 1.1E2 | 1.1E2 | 1.4E2 | 1.9E2 | 7.6E1 | 1.6E2 | 4.3E1 | 6.0E1 | 2.9E2 | 7.7E2 | 24 | 25 | 24 | 25 | 0.56 |
| pF | pg/ml | 7.9E-1 | 5.2E-1 | 1.0E0 | 2.2E0 | 1.4E0 | 1.1E1 | 2.3E-2 | 1.0E-9 | 9.4E0 | 8.7E1 | 47 | 57 | 47 | 57 | 0.43 |
| pH | ng/ml | 6.6E0 | 8.9E0 | 8.2E0 | 1.1E1 | 4.4E0 | 5.7E0 | 3.0E0 | 1.2E0 | 1.8E1 | 2.3E1 | 14 | 15 | 14 | 15 | 0.66 |
| pI | ng/ml | 7.4E1 | 6.7E1 | 6.9E1 | 7.6E1 | 3.4E1 | 5.5E1 | 2.6E1 | 2.3E1 | 1.5E2 | 2.0E2 | 14 | 15 | 14 | 15 | 0.48 |
| pK | ng/ml | 3.6E-1 | 5.5E-1 | 3.8E-1 | 5.6E-1 | 1.7E-1 | 2.0E-1 | 1.7E-1 | 2.7E-1 | 7.7E-1 | 8.6E-1 | 14 | 15 | 14 | 15 | 0.77 |

Analyte panel data:

Unconstrained panels with 3 analytes, where 1.0E-10 >= 'model p-value' > 0. Contains 876 panels of 38,188,712 total panels evaluated. :
Ji{Ms(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Lj(aA Et Fp Hq Hu Hv Hx Ii Ik Il Im In Io Ir It Iu Iv Jg Jh Jj Jl Jo Jp Jq Js Jt Li Lu Lv Lw Ly Lz Mb Me Mf Mh Mj Mk Ml Mm Mn Mp Mu Mv Mw Mx My Nb Nc Nd Ne Nf Ng Nh Ni Nj Nl Nm Nn Nq Ns Nt Nu Nx Ny Oe Of Og Oh Ok Oy Oz Pb Pc Pd Pg Po Pz Qa Qb Qc Qd Qe) Og(aA Et Fp Hv Hx Ij Ik Il Im In Ir Is It Iu Iv Jg Jh Jj Jl Jm Jp Jq Jt Li Lu Lw Lx Ly Lz Me Mf Mh Mm Mn Mp Mt Mv Mw Mx My Mz Nc Ne Nf Nj Nl Nm Nn Ns Nu Ny Of Oi Ok Oy Oz Pb Pc Po Pz Qa Qb Qc Qd Qe) Li(Et Fp Hq Hu Hv Hx Ii Ik Im In Io It Jh Jj Jk Jo Jq Lu Lz Mj Mp Mv Mw My Nf Ng Nj Nm Nq Nx Ny Of Oh Ok Om Oy Pb Po Pz Qa Qc Qd Qe) Qe(Et Fp Hv Hx Ii Ik Il In Io It Iu Jh Jj Jk Jo Jq Lu Lz Mh Mj Ml Mp Mv Mw My Nf Ng Nj Nq Ny Oe Of Oh Ok Om Oy Pb Pg Pz Qc) Et(Fp Hx Ii Im It Jh Jj Jo Lu Lz Mh Ml Mp Mv Mw My Nf Ng Nm Ny Of Om Oy Pb Pz) My(Fp Ik Im Jg Jl Jp Jt Lu Lz Mm Mp Mu Nn Nw Ok Pb Qa Qd) Fp(Hv Hx Ik Jh Jj Lu Mj Mp Mv Mw Nf Of Ok Oy Pb) Lu(Ik Im Jh Lz Mp Mv Mw Of Ok Oy Pb Qa Qd) Pb(Im It Jj Jl Jp Lz Mp Of Ok Qa Qd) Mp(Ik Im Lx Lz Nn Ok Qa Qd) Qa(Jh Jj Jk Mv Mw Of Oy) Ok(Ii It Jh Of Om Oy) Lz(Ik Il Im Oy Po) Im(Ng Of Oy) Qd(Of Oy) wE(Gp jD) IiJl YkeF JgOy} Et{Lj(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Fp(Im It Jh Lw Mp Ms Mv Mw My Nc Nf Ng Nj Of Og Oy Pb Qe) Li(Im It Jh Mp Ms Mv Mw My Ng Nj Of Og Oy Pb) Ms(Im It Lz Mz Nj Of Og Ok Qa Qe) Qe(Mp My Ng Nj Of Og Oy Pb) Of(Im It Lz Nj Ok Qa Qd) Im(Lz Ng Oe Og Oy) Og(It Jm Lz Qa) Lz(It Oy) QaOy} Ok{Of(Fp Hv Ik Il Im Io Ip Iq Ir Is It Iu Iv Jm Li Lj Lu Lv Ly Lz Me Mf Mm Mp Ms Mu Mv Mw Mx My Mz Nc Nd Ne Nj Nl Nn Nq Nw Ny Oe Og Oy Oz Pb Pc Pd Qa Qd Qe) Lj(Hv Hx Ik Il Im Io Ip Iq Ir Is It Iu Jj Jp Li Lu Lw Ly Lz Mh Mj Mm Mp Ms My Na Nc Ne Nf Nj Nl Nn Nq Nr Nw Ny Oe Og Pb) Ms(Fp Ih Im Io Ir Is It Jm Jn Li Lu Lw Lz Mf Mh Mp Mt Mx My Mz Nc Ng Nj Nn Nw Og Oy Oz Pb Qa Qe) Og(Fp Ij Il Im Io Ir Is It Jm Li Lu Lw Ly Lz Me Mh Mp Mx Nc Nj Nn Ny Pb Qa Qe) Li(Ii It Jh Mp Mv

Figure 33 Continued

Mw My Ng Nq Oy Pb) It(Fp Jj Lz My Pb) Im(Lz My Ng Pb)} Og{Im(Fp Iq Ir It Jg Jl Jp Jt Lh Li Lj Lw Ly Lz Me Mm Mz Nj Nm Nn Nt Nw Pb Qd Qe) Li(aA Ir It Jt Lw Me Nj Nm Nw Pb Qa Qd Qe) Lj(Jg Jt Nw On) QeJt} cM{Vt(Ax Cs Lj) Uh(Cs Lj)} Gc{hC(bG Hp)} Nj{Lj(Jp Nw)} MwImLi MzPkwE

Unconstrained panels with 3 analytes, where 1.0E-9 >= 'model p-value' > 1.0E-10. Contains 3,580 panels of 38,188,712 total panels evaluated. :
Ji{Lz(aA Fp Fr Hq Hr Hu Hv Hw Hx Ih Ii Ij In Io Ip Iq Ir Is It Iu Iv Jg Jh Jj Jk Jl Jm Jn Jo Jp Jq Jr Js Jt Lh Lv Lw Lx Ly Ma Mb Mc Md Me Mf Mg Mh Mi Mj Mk Ml Mm Mn Mq Mr Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oz Pa Pc Pd Pe Pf Pg Pz Qa Qb Qc Qd) Qa(aA Et Fp Fr Hq Hr Hu Hv Hw Hx Ii Ij Ik Il Im In Io Ip Iq Ir Is It Iu Iv Jg Jl Jm Jn Jo Jp Jq Jr Js Jt Lh Lv Lw Lx Ly Ma Mb Mc Md Me Mf Mg Mh Mi Mj Mk Ml Mm Mn Mq Mr Mt Mu Mx Mz Na Nb Nc Nd Ne Nf Ng Nh Ni Nj Nk Nl Nm Nn No Nq Nr Ns Nt Nu Nv Nw Nx Ny Oe Oh Oi Ok Om On Oz Pa Pc Pd Pe Pf Pg Po Pz Qb Qc Qd Qe) Oy(aA Fr Hq Hr Hu Hv Hw Hx Ih Ii Ik Il In Io Ip Iq Ir Is It Iu Iv Jh Jj Jk Jl Jm Jn Jo Jp Jq Jr Js Jt Lh Lv Lw Lx Ly Ma Mb Mc Md Me Mf Mg Mh Mi Mj Mk Ml Mm Mn Mp Mq Mr Mt Mu Mv Mw Mx My Mz Nb Nc Nd Ne Nf Nh Ni Nj Nk Nl Nm Nn No Nq Nr Ns Nt Nu Nv Nw Nx Ny Oe Of Oh Oi On Oz Pa Pb Pc Pd Pe Pf Pg Po Pz Qb Qc) Lu(aA Fr Hq Hr Hu Hv Hw Hx Ih Ii Ij Il In Io Ip Iq Ir Is It Iu Iv Jg Jj Jk Jl Jm Jn Jo Jp Jq Jr Js Jt Lh Lv Lw Lx Ly Ma Mb Mc Md Me Mf Mg Mh Mi Mj Mk Ml Mm Mn Mq Mr Mt Mu Mx Mz Na Nb Nc Nd Ne Nf Ng Nh Ni Nj Nk Nl Nm Nn No Nq Nr Ns Nt Nu Nv Nw Nx Ny Oe Oh Oi Om On Oz Pa Pc Pd Pe Pf Pg Po Pz Qb Qc) Pb(aA Fr Hq Hr Hu Hv Hw Hx Ih Ii Ij Ik Il In Io Ip Iq Ir Is Iu Iv Jg Jh Jk Jm Jn Jo Jq Jr Js Jt Lh Lv Lw Lx Ly Ma Mb Mc Md Me Mf Mg Mh Mi Mj Mk Ml Mm Mn Mq Mr Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Oh Oi Om On Oz Pa Pc Pd Pe Pf Pg Po Pz Qb Qc) Fp(aA Fr Hq Hr Hu Hw Ih Ii Ij Il Im In Io Ip Iq Ir Is It Iu Iv Jg Jk Jl Jm Jn Jo Jp Jq Jr Js Jt Lh Lv Lw Lx Ly Ma Mb Mc Md Me Mf Mg Mh Mi Mk Ml Mm Mn Mq Mr Mt Mu Mx Mz Na Nb Nc Nd Ne Ng Nh Ni Nj Nk Nl Nm Nn No Nq Nr Ns Nt Nu Nv Nw Nx Ny Oe Oh Oi Om On Oz Pa Pc Pd Pe Pf Pg Po Pz Qb Qc Qd) My(aA Fr Hq Hr Hu Hv Hw Hx Ih Ii Ij Il In Io Ip Iq Ir Is It Iu Iv Jh Jj Jk Jm Jn Jo Jq Jr Js Lh Lv Lw Lx Ly Ma Mb Mc Md Me Mf Mg Mh Mi Mj Mk Ml Mn Mq Mr Mt Mv Mw Mx Mz Na Nb Nc Nd Ne Nf Ng Nh Ni Nj Nk Nl Nm No Nq Nr Ns Nt Nu Nv Nx Ny Oe Of Oh Oi Om On Oz Pa Pc Pd Pe Pf Pg Po Pz Qb Qc) Et(aA Fr Hq Hr Hu Hv Hw Ih Ij Ik Il In Io Ip Iq Ir Is Iu Iv Jg Jk Jl Jm Jn Jp Jq Jr Js Jt Lh Lv Lw Lx Ly Ma Mb Mc Md Me Mf Mg Mi Mj Mk Mm Mn Mq Mr Mt Mu Mx Mz Na Nb Nc Nd Ne Nh Ni Nj Nk Nl Nn No Nq Nr Ns Nt Nu Nv Nw Nx Oe Oh Oi Ok On Oz Pa Pc Pd Pe Pf Pg Po Qb Qc Qd) Mp(aA Fr Hu Hv Hx Ih Ii Ij Il In Io Ip Iq Ir Is It Iu Iv Jg Jh Jj Jl Jm Jn Jo Jp Jq Jr Jt Lh Lv Lw Ly Mb Mc Md Me Mf Mh Mi Mk Ml Mm Mn Mr Mt Mu Mv Mw Mx Mz Nb Nc Nd Ne Nf Ng Nh Nj Nl Nm No Ns Nt Nu Nv Nw Nx Ny Oe Of Oh Oi Om On Oz Pc Pd Pe Pf Pg Po Pz Qb Qc) Qd(Fr Hq Hu Hv Hw Hx Ii Ik Il Im In Io Ip Ir Is It Iu Iv Jh Jj Jk Jl Jo Jp Jq Jr Js Jt Lw Lx Ly Mb Md Me Mf Mh Mi Mj Mk Ml Mm Mn Mv Mw Mx Mz Nb Nc Nd Ne Nf Ng Nh Nj Nl Nm Nn Nq Ns Nu Nv Nw Nx Ny Oe Oh Ok Om Oz Pc Pd Pe Pg Po Pz Qc Qe) Qe(aA Fr Hq Hr Hu Hw Ih Ij Im Ip Iq Ir Is Iv Jg Jl Jm Jn Jp Jr Js Jt Lh Lv Lw Lx Ly Ma Mb Mc Md Me Mf Mg Mi Mk Mm Mn Mq Mr Mt Mu Mx Mz Na Nb Nc Nd Ne Nh Ni Nk Nl Nm Nn No Nr Ns Nt Nu Nv Nw Nx Oi On Oz Pa Pc Pd Pe Pf Po Qb) Li(aA Fr Hr Hw Ih Ij Il Ip Iq Ir Is Iu Iv Jg Jl Jm Jn Jp Jr Js Jt Lh Lv Lw Lx Ly Ma Mb Mc Md Me Mf Mg Mh Mi Mk Ml Mm Mn Mq Mr Mt Mu Mx Mz Na Nb Nc Nd Ne Nh Ni Nk Nl Nn No Nr Ns Nt Nu Nv Nw Oe Oi On Oz Pa Pc Pd Pe Pf Pg Qb) Ok(Fr Hq Hr Hu Hv Hx Ij Ik Il Im In Io Ip Iq Ir Is Iu Iv Jj Jk Jm Jo Jp Jq Lw Lx Ly Mb Mc Md Me Mf Mg Mh Mi Mj Mk Ml Mm Mn Mv Mw Mx Mz Na Nb Nc Nd Ne Nf Ng Nh Nj Nl Nm Nn Nq Ns Nu Nv Nx Ny Oe Oh On Oz Pc Pd Pg Po Pz Qb Qc) Im(Hq Hu Hv Hx Ii Ij Ik Il In Io Iq Ir It Iu Iv Jh Jj Jk Jl Jo Jp Jq Jt Lw Me Mh Mj Ml Mm Mn Mv Mw Mx Mz Nc Ne Nf Nj Nl Nm Nn Nq Ns Nu Nx Ny Oe Oh Om Pc Pd Pg Po Pz Qc) Of(Fr Hv Hx Ik Il In Ir Is It Iv Jg Jh Jj Jl Jm Jp Jq Jt Lh Lw Lx Ly Me Mf Mh Ml Mm Mt Mv Mw Mx Mz Nc Nd Ne Nf Nj Nl Nm Nn Ns Nt Nu Nw Ny Oi On Oz Pc Po Pz Qb Qc) Jj(aF aO bM Hv Hx Ik Il Io Ir Is It Iv Jg Jh Jl Jm Jp Jq Jt Lh Lw Lx Ly Md Me Mf Mh Ml Mm Mv Mw Mx Mz Nc Nd Ne Nf Nj Nl Nn Ns Nt Nu Ny Om Oz Pc Po Pz Qb Qc) Og(Hq Hr Hu Hw Ih Ii Io Ip Iq Jk Jn Jo Jr Js Lh Lv Ma Mb Mc Md Mg Mi Mj Mk Ml Mq Mr Mu Na Nb Nd Ng Nh Ni Nk No Nq Nr Nt Nv Nw Nx Oe Oh Om On Pa Pd Pe Pf Pg) Mv(Fr Hv Ik In Io Ir Is It Iv Jg Jl Jo Jp Jq Jt Lx Ly Me Mh Mm Mt Mu Mx Mz Nc Nd Nf Nj Nl Nn Nt Nu Nw Ny Oz Pc Pe Po Pz Qb Qc) Ik(Hv Hx Ii In Io Iq Ir It Iv Jh Jl Jo Jp Jq Jt Lx Ly Mb Mh Ml Mm Mw Mx Mz Nc Ne Nf Ng Nj Nl Nn Nu Nx Ny Oe Om Pc Po Pz Qc) Jh(aA Fr Hv Hx In Io Ir Is It Iv Jg Jl Jp Jq Jt Lw Lx Ly Me Mh Mm Mt Mu Mx Nc Ne Nf Nj Nl Nn Nt Nu Nw Ny Pc Po Pz Qb Qc) Mw(Fr Hv In Ir Is It Iv Jg Jl Jp Jq Jt Lw Lx Ly Me Mh Mm Mr Mt Mu Mx Mz Nc Nf Nj Nn Nu Nw Ny On Pc Pe Po Pz Qb Qc) Lj(Fr Hr Hw Ih Ij Ip Iq Is Jk Jm Jn Jr Lh Lx Ma Mc Md Mg Mi Mq Mr Mt Mz Na Nk No Nr Nv Nw Oi Om On Pa Pe Pf) It(Hq Hv Hx Ii In Ir Jl Jo Jp Jq Lx Ly Me Mh Ml Mm Mz Nf Ng Nj Nn Ns Nu Nx Ny Pc Pg Po Pz Qb Qc) Ir(Hv Hx Ii Ij Il In Jo Jp Jq Js Ly Me Mm Nb Nf Nn Ny Om Po Pz) Pz(Hv Hx In Iv Jg Jl Jp Jq Jt Lx Ml Mm Nc Nf Nn Nu Ny Pc) Hx(Jl Jp Jq Jt Lx Ly Mh Mm Mr Mz Pc Pe Qb Qc) Jl(Hv Jo Jq Mh Ml Nb Nf Nx Ny On Po) Nf(Hv Mh Mz Nn Nu Pc Po Qb Qc) In(Hv Iv Jm Jt Mh Nj Nu Pc Qb) Ny(Jp Jq Mh Mm Mz Pc Pe Qb Qc) Jq(Is Jm Jt Nn Pc Qb Qc) Om(Jg Jp Jt Mm Mz Nn Nw) Ng(Jg Jp Jt Mm Nn Nu) Ii(Jm Jp Jt Lh Mr Pe) Hv(Jp Lx Qb Qc) Mh(Jp Me Mm) Jo(Jt Mm) Pe(Nb Po) AaMs NnOh NcNk NjJp IlIq YkiA SfaW VtcM PfPg aOdH} Et{Fp(aA Fr Hq Hr Hu Hv Hw Hx Ih Ii Ij Ik Il In Io Ip Iq Ir Is Iu Iv Jg Jj Jk Jl Jm Jn Jo Jp Jq Jr Js Jt Lh Li Lu Lv Lx Ly Lz Ma Mb Mc Md Me Mf Mg Mh Mi Mj Mk Ml Mm Mn Mq Mr Mt Mu Mx Mz Na Nb Nd Ne Nh Ni Nk Nl Nm Nn No Nq Nr Ns Nt Nu Nv Nw Nx Ny Oe Oh Oi Ok Om On Oz Pa Pc Pd Pe Pf Pg Po Pz Qa Qb Qc Qd) Li(aA Fr Hq Hr Hu Hv Hx Ih Ii Ik Il In Io Ir Is Iv Jg Jj Jk Jl Jm Jn Jo Jq Jr Jt Lh Lu Lv Lw Lx Ly Lz Ma Mb Mc Md Me Mf Mg Mh Mi Mj Mk Ml Mn Mt Mx Mz Nb Nc Nd Ne Nf Nh Ni Nl Nm Nn No Nq Ns Nt Nu Nv Nw Nx Ny Oe Oh Oi Ok Om Oz Pc Pd Pe Pf Pg Po Pz Qa Qb Qd Qe) Ms(Hq Hu Hv Hx Ih Ik Io Iq Ir Is Iv Jh Jj Jl Jm Jn Jo Jp Jq Jr Js Jt Lh Lu Lv Lw Lx Ly Mb Me Mf Mh Mi Ml Mm Mn Mp Mr Mt Mv Mx My Nb Nc Nd Ne Ng Nh Nl Nm Nn No Nq Nr Ns Nt Nu Nw Nx Ny Oe On Oy Oz Pb Pc Pd Pe Po Pz Qb Qc Qd) Of(Hu Hv Hx Ih Ij Ik Il Ir Is Iv Jg Jh Jj Jl Jm Jn Jp Jq Jr Js Jt Lh Lu Lv Lw Lx Ly Mb Me Mf Mh Ml Mm Mp Mr Mt Mv Mw Mx My Mz Nb Nc Nd Ne Ng Nh Nl Nm Nn No Nq Ns Nt Nu Nv Nw Nx Ny Oe Og On Oy Oz Pb Pc Pd Pe Pf Pz Qb Qc) Og(aA Hr Hv Hx Ih Ij Ik Il Io Ir Is Iv Jg Jh Jj Jl Jn Jq Jr Js Jt Lh Lu Lv Lw Lx Ly Mb Me Mf Mh Ml Mp Mr Mt Mv Mx My Mz Nb Nc Nd Ne Ng Nj Nl Nm Nn No Nq Ns Nt Nu Nw Nx Ny Oe Oi Ok On Oy Oz Pb Pc Pd Pe Po Pz Qb Qc Qd) Qe(aA Aj Fr Hq Hu Hv Hx Ii Ik Il Im Io Ip Ir Is It Iu Jh Jj Jk Jl Jn Jo Jq Jr Jt Lu Lw Ly Lz Mb Me Mf Mg Mh Mj Mk Ml Mv Mw Mx Mz Nb Nc Nd Ne Nf Nh Nl Nm Nn Nq Ns Nu Ny Oe Oh Ok Oz Pc Pd Pg Pz Qc Qd) It(Hq Hu Hx Ik Im Io Ir Is Jh Jj Jl Jm Jo Lu Lv Lw Lx Mb Me Mg Mh Mk Ml Mp Mt Mv Mw Mx My Mz Nb Nc Ne Nf Ng Nj Nl Nm Nn Nq Ns Nu Nw Ny Oe Ok Oy Oz Pb Pc Pd Pz Qa Qb Qd) Lz(Hu Hv Hx Ih Ik Il Ir Is Jh Jj Jl Jm Jn Jo Jq Jr Jt Lu Lw Mh Mj Mk Mp Mt Mv Mw Mx My Mz Nb Nc Ne Nf Ng Nj Nl Nn Nq Ns Nw Nx Ny Oe Ok Oz Pb Pc Pz Qa Qd) Im(Hq Hu Hx Ii In Io Iq Ir Jh Jj Jk Jl Jo Jr Lu Lw Ly Mb Mh Ml Mp Mv Mw Mx My Mz Nc Nf Nj Nl Nm Nq Ok Pb Pz Qd) Oy(Ih Ir Is Jg Jl Jm Jn Jt Lh Lu Lw Lx Mh Mt Mx Mz Nc Nj Nl Nn Nw Ok On Pd Pe Po Qb Qd) My(Ih Ir Is Jg Jl Jm Jt Lh Lu Lw Lx Mf Mh Mt Mx Mz Nc Nj Nn Nw Ok On Qa Qb Qd) Qa(Hq Hx Jh Jj Jk Jo Lu Mb Mh Mp Mv Mw Nc Ng Nj Nq Oe Pb Pz) Nj(Ih Ir Jh Jj Lu Mh Mx Mz Ng Ok Pb Qd) Pb(Ir Jl Lu Lx Mh Mx Mz Nc Nw Ok Qd) Mh(Jh Lu Mv Mw Mz Nc Ng Qd) Pk(Ch Hu Ib Ik Jj Lj) Mz(Hx Mv Mw Nc Ny) Qd(Mp Ng Nq Oe Pz) Ng(Jm Jt Ok) Jh(Is Ok) MpOk JjJm} Ok{Og(aA Fr Hq Hr Hu Hv Hw Hx Ih Ii Ik In Ip Iq Iu Iv Jg Jh Jj Jk Jl Jn Jo Jp Jq Jr Js Jt Lh Lv Lx Ma Mb Mc Md Mf Mg Mi Mj Mk Ml Mm Mn Mq Mr Mt Mu Mv

Figure 33 Continued

Mw My Mz Na Nb Nd Ne Nf Ng Nh Ni Nk Nl Nm No Nq Nr Ns Nt Nu Nv Nw Nx Oe Oh Oi Om On Oy Oz Pa Pc Pd Pe Pf Pg Po Pz Qb Qc Qd) Ms(AA Fr Hq Hr Hu Hv Hw Hx Ii Ij Ik Il In Ip Iq Iu Iv Jg Jh Jj Jk Jl Jo Jp Jq Jr Js Jt Lh Lv Lx Ly Ma Mb Mc Md Me Mg Mi Mj Mk Ml Mm Mn Mq Mr Mu Mv Mw Na Nb Nd Ne Nf Nh Ni Nk Nl Nm No Nq Nr Ns Nt Nu Nv Nx Ny Oe Oh Oi Om On Pa Pc Pd Pe Pf Pg Po Pz Qb Qc Qd) Li(Fp Fr Hq Hr Hu Hv Hx Ij Ik Il Im In Io Ip Iq Ir Is Iu Iv Jj Jk Jl Jm Jn Jo Jp Jr Lh Lu Lv Lw Ly Lz Ma Mb Mc Md Me Mf Mg Mh Mi Mj Mk Ml Mm Mn Mr Mu Mx Mz Na Nb Nc Nd Ne Nf Nh Ni Nj Nk Nl Nm Nn No Nr Ns Nu Nv Nw Nx Ny Oe Oh Oi Om On Oz Pc Pd Po Pz Qa Qc Qd Qe) Lj(aA Fp Fr Hq Hr Hu Hw Ih Ii Ij In Jg Jh Jk Jl Jm Jn Jo Jq Jr Js Jt Lh Lv Lx Ma Mb Mc Md Me Mf Mg Mi Mk Ml Mn Mq Mr Mt Mu Mv Mw Mx Mz Nb Nd Ng Nh Ni Nk Nm No Ns Nt Nu Nv Nx Oh Oi Om On Oy Oz Pa Pc Pd Pe Pf Pg Po Pz Qa Qb Qc Qd Qe) Of(AA Fr Hq Hr Hu Hw Hx Ih Ii Ij In Jg Jh Jj Jk Jl Jn Jo Jp Jq Jr Js Jt Lh Lv Lx Ma Mb Mc Md Mg Mh Mi Mj Mk Ml Mn Mq Mr Mt Na Nb Nf Ng Nh Ni Nk Nm No Nr Ns Nt Nu Nv Nx Oh Oi Om On Pa Pe Pf Pg Po Pz Qb Qc) It(Hx Ii Ij Ik Il Im In Io Ir Iu Jh Jo Jp Lu Lv Lw Lx Ly Ma Mb Mc Md Me Mf Mg Mh Mj Mk Ml Mm Mp Mt Mu Mv Mw Mx Mz Na Nb Nc Nd Ne Nf Ng Nh Nj Nl Nm Nn Nq Nr Ns Nu Nw Ny Oe Oh Om On Oy Oz Pc Pd Pz Qa Qe) Fp(Hv Ii Ik Im Io Ir Is Jh Jj Lu Lw Lz Me Mh Mj Mk Mm Mp Mv Mw My Nb Nc Nf Ng Nj Nl Nn Nq Nw Ny Oe Om Oy Pb) Im(Ii Il In Io Ir Iu Jh Jj Jk Lu Ly Mj Mp Mv Mw Mz Nb Nc Nf Nj Nq Oe Om Oy Pz) Lz(Ii Ik Il Io Ir Is Jj Lu Mh Mj Mp Mv Mw My Nc Nf Ng Nj Nq Oy Oz Pb Qe) Pb(Io Ir Is Jj Lu Lw Mh Mm Mp Mx My Nc Nj Nn Nw Oe Oy Qa Qe) My(Ir Is Lu Lw Lx Mf Mh Mm Mu Mz Nc Nj Nn Nw Ny Qa Qe) Qe(Ii Jh Jj Mp Mw Ng Nj Nq Oe Oy Pz Qc) Oy(Ir Is Lu Nc Nj Nn Nw Qa) Mp(Ir Is Nj Nn Nw Qa) Nj(Ir Jj Lu Nw) Nw(Ii Mv Mw) Lu(Ir Ng) Qa(Jj Nq) MuMw JjJm} Og{Li(Fp Fr Hq Hr Hu Hv Hx Ih Ij Ik Il In Io Ip Iq Is Iu Iv Jg Jh Jj Jl Jm Jn Jp Jq Jr Js Lh Lj Lu Lv Lx Ly Lz Ma Mb Mc Md Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nn No Nq Nr Ns Nt Nu Nv Nx Ny Oe Of Oh Oi Om On Oy Oz Pa Pc Pd Pe Po Pz Qb Qc) Im(aA Fr Hq Hr Hu Hv Hw Hx Ih Ii Ij Ik Il In Io Ip Is Iu Iv Jh Jj Jk Jm Jn Jo Jq Jr Js Lu Lv Lx Ma Mb Mc Md Mf Mg Mh Mi Mj Mk Ml Mn Mp Mq Mr Ms Mt Mu Mv Mw Mx Ms My Na Nb Nc Nd Ne Nf Ng Nh Ni Nk Nl No Nq Nr Ns Nu Nv Nx Ny Oe Of Oh Oi Om On Oy Oz Pa Pc Pd Pe Pf Pg Po Pz Qa Qb Qc) Qe(AA It Jg Jp Lh Lj Lw Me Mm Nj Nm Nn Nw Ny) Nw(Fp Ij Il It Jt Lw Lz Ms Nj Nm Pb Qa) Lj(Ij Jp Lh Lw Mg Mm Nm Nn Ny Qa) Fp(Jg Jt Mm) Qa(Jg Jt)] Li{Im(In Jh Jj Jk Jp Lj Lz Ms Mv My Nf Ng Nj Nw Of Oy Pb) Pb(Ir It Jj Jl Jp Lh Lw Ms Mz Nc Nf Nj Nw Of Qa Qe) Nw(It Jh Lj Lu Mp Ms Mv Mw My Ng Nj Of Oy) Qe(Jj Mj Mp Ms Mv Mw My Ng Nj Nq Of Oy) Oy(Jg Jl Jp Lw Nj On Qa) My(aA Jg Jp Lw Mz) Of(Jp Lh Mm On Qd) Jj(It Jm Lh Nj) Mz(Hx Mv Mw) Jp(It Lj Ms) Ng(Jt Lw) Jl(Mv Mw) NjLj VtcM} Lj{Jp(Hv Hx Ik Im Ir It Jj Jl Jt Lu Lw Ly Lz Mh Mm Mp Ms Nc Nl Nm Nq Nt Of Pb Qe) Nw(Ik Im Ir It Iv Jt Lu Lw Ly Lz Mj Mm Mp Ms My Nc Ne Nl Of Pb) Im(In Jj Jl Jt Lu Lw Lz Mm Ms Nj Pb) Mm(Jj Lu Ms Nj) On(Mp Ms Nj Of) Jg(My Nj Of) Ms(Jt Lh) NjJt PjcM} Nw{Ms(Fp Im Ir Is It Iv Jt Lu Lw Lz Mm My Nc Nj Nl Ny Of Pb Qa Qe) My(Fp Im It Jg Lu Lw Lz Mf Nj Pb Qe) Fp(It Mj Mv Mw Nj Oy Pb) Im(Lz Ng Of Pb) It(Mv Pb) QePb} Qe{Aa(Jj Lu Ms Nj No Oe) Ms(Jp Jt Mm) Jg(Mw My Oy) cM(Uh Vt) DdJj LzIm} cM{Uh(Ar Ax bM Dd Id Jj Rg Vt) Vt(Ar Dd Fp Ir Pj) PjdH} Im{Lz(Jj Jp Jt Ms Nf Ng Nj Oy Pb) Ng(Jg Jt) MsJp} Jp{Ms(It Lz) ChPk FpPb} Gc{hC(eC Mj Yk)} AadLiA FpMyJg MsOfOn IddHuR Unconstrained panels with 3 analytes, where 1.0E-8 >= 'model p-value' > 1.0E-9. Contains 12,438 panels of 38,188,712 total panels evaluated. : Ji{Hu(aA bM Fr Gl hC Hq Hr Hv Hw Hx Id Ih Ii iJ Ik Il In Io Ip Iq Ir Is It Iu Iv iZ Jg Jh Jj Jk Jl Jm Jn Jo Jp Jq Jr Js Jt Lh Lv Lw Lx Ly Ma Mb Mc Md Me Mf Mg Mh Mi Mj Mk Ml Mm Mn Mq Mr Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Oh Oi Om On Oz Pa Pc Pd Pe PF Pg Pk Po Pz Qb Qc) Nh(aA bM Fr Gl Hq Hr Hv Hw Hx Ih Ii Ij Ik Il Im In Io Ip Iq Ir Is It Iu Iv Jg Jh Jj Jk Jl Jm Jn Jo Jp Jq Jr Js Jt Lh Lv Lw Lx Ly Ma Mb Mc Md Me Mf Mg Mh Mi Mj Mk Ml Mm Mn Mq Mr Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Oh Oi Om On Oz Pa Pc Pd Pe Pf Pg Po Pz Qb Qc) Mb(aA Fr Hq Hr Hv Hw Hx Ih Ii Ij Il Im In Io Ip Iq Ir Is It Iu Iv Jg Jh Jj Jk Jl Jm Jn Jo Jp Jq Jr Js Jt Lh Lv Lw Lx Ly Ma Mc Md Me Mf Mg Mh Mi Mj Mk Ml Mm Mn Mq Mr Mt Mu Mv Mw Mx Mz Na Nb Nc Nd Ne Nf Ng Ni Nj Nk Nl Nm Nn No Nq Nr Ns Nt Nu Nv Nw Nx Ny Oe Of Oh Oi Om On Oz Pa Pc Pd Pe Pf Pg Po Pz Qb Qc) Mn(aA Fr Hq Hr Hv Hw Hx Ih Ii Ij Ik Il In Io Ip Iq Ir Is It Iu Iv Jg Jh Jj Jk Jl Jm Jn Jo Jp Jq Jr Js Jt Lh Lv Lw Lx Ly Ma Mc Md Me Mf Mg Mh Mi Mj Mk Ml Mm Mq Mr Mt Mu Mv Mw Mx Mz Na Nb Nc Nd Ne Nf Ng Ni Nj Nk Nl Nm Nn No Nq Nr Ns Nt Nu Nv Nw Nx Ny Oe Of Oh Oi Om On Oz Pa Pc Pd Pe Pf Pg Po Pz Qb Qc) Hq(aA Fr Hr Hv Hw Hx Ih Ii Ij Ik Il In Io Ip Iq Ir Is Iu Iv Jg Jh Jj Jk Jl Jm Jn Jo Jp Jq Jr Js Jt Lh Lv Lw Lx Ly Ma Mc Md Me Mf Mg Mh Mi Mj Mk Ml Mm Mp Mq Mr Mt Mu Mv Mw Mx Mz Na Nb Nc Nd Ne Nf Ng Ni Nj Nk Nl Nm Nn No Nq Nr Ns Nt Nu Nv Nw Nx Ny Oe Of Oh Oi Om On Oz Pa Pc Pd Pe Pf Pg Po Pz Qb Qc) Iq(aA aM Fr Hr Hv Hw Hx Ih Ii Ij In Io Ip Ir Is It Iu Iv Jg Jh Jj Jk Jl Jm Jn Jo Jp Jq Jr Js Jt Lh Lv Lw Lx Ly Ma Mc Md Me Mf Mg Mh Mi Mj Mk Ml Mm Mq Mr Mt Mu Mv Mw Mx Mz Na Nb Nc Nd Ne Nf Ng Ni Nj Nk Nl Nm Nn No Nq Nr Ns Nt Nu Nv Nw Nx Ny Oe Of Oh Oi Om On Oz Pa Pc Pd Pe Pf Pg Po Pz Qb Qc Qd) Nt(aA Fr Hr Hv Hw Hx Ih Ii Ij Ik Il Im In Io Ip Ir Is It Iu Iv Jg Jk Jl Jm Jn Jo Jp Jq Jr Js Jt Lh Lv Lw Lx Ly Ma Mc Md Me Mf Mg Mh Mi Mj Mk Ml Mm Mq Mr Mt Mu Mv Mw Mx Mz Na Nb Nc Nd Ne Nf Ng Ni Nj Nk Nl Nm Nn No Nq Nr Ns Nu Nv Nw Nx Ny Oe Oh Ok Om On Oz Pa Pc Pd Pe Pf Pg Po Pz Qb Qc Qd) Jj(aA aC aE aG aH aK aL aM aN Ar aU aV aW AX bC bI bL bO bQ bW bX bZ cA cC cD cI cM cR cS cZ dB Dc dD dE dH dI dK dL EF Fr GL hG Hr Hw iA Jh Ii Ij Il In Ip Iu Jk Jn Jo Jr Js Lv Ma Mc Mg Mi Mj Mk Mq Mr Mt Mu Na Nb Ng Ni Nk Nm No Nq Nr Nv Nw Nx Oe Oh Oi On Pa Pd Pe PF Pg Pk Wm) Md(aA Fr Hr Hv Hw Hx Ih Ii Ik Il Im In Io Ip Ir Is It Iu Iv Jg Jh Jk Jl Jm Jn Jo Jp Jq Jr Js Jt Lh Lv Lw Lx Ly Ma Mc Me Mf Mg Mh Mi Mj Mk Ml Mm Mq Mr Mt Mu Mv Mw Mx Mz Na Nb Nc Nd Ne Nf Ng Ni Nj Nk Nl Nm Nn No Nq Nr Ns Nu Nv Nw Nx Ny Oe Of Oh Oi Om On Oz Pa Pc Pd Pe Pf Pg Po Pz Qb Qc) Mf(aA Fr Hr Hv Hw Hx Ih Ii Ij Ik Il Im In Io Ip Ir Is It Iu Iv Jg Jh Jk Jl Jm Jn Jo Jp Jq Jr Js Jt Lh Lv Lw Lx Ly Ma Mc Me Mg Mh Mi Mj Mk Ml Mm Mq Mr Mt Mu Mv Mw Mx Mz Na Nb Nc Nd Ne Nf Ng Ni Nj Nk Nl Nm Nn No Nq Nr Ns Nu Nv Nw Nx Ny Oe Oh Oi Om On Oz Pa Pc Pd Pe Pf Pg Po Pz Qb Qc) Oz(aA bM Fr Hr Hv Hw Hx Ih Ii Ij Ik Il Im In Io Ip Ir Is It Iu Iv Jg Jh Jk Jl Jm Jn Jo Jp Jq Jr Js Jt Lh Lv Lw Lx Ly Ma Mc Me Mg Mh Mi Mj Mk Ml Mm Mq Mr Mt Mu Mv Mw Mx Mz Na Nb Nc Nd Ne Nf Ng Ni Nj Nk Nl Nm Nn No Nq Nr Ns Nu Nv Nw Nx Ny Oe Oh Oi Om On Pa Pc Pd Pe Pf Pg Po Pz Qb Qc) Mt(aA Fr Hr Hv Hw Hx Ih Ii Ij Ik Il Im In Io Ip Ir Is It Iu Iv Jg Jk Jl Jm Jn Jo Jp Jq Jr Js Jt Lh Lv Lw Lx Ly Ma Mc Me Mg Mh Mi Mj Mk Ml Mm Mq Mr Mu Mx Mz Na Nb Nc Nd Ne Nf Ng Ni Nj Nk Nl Nm Nn No Nq Nr Ns Nu Nv Nw Nx Ny Oe Oh Oi Ok Om On Pa Pc Pd Pe Pf Pg Po Pz Qb Qc Qd) Nd(aA Fr Hr Hv Hw Hx Ih Ii Ij Ik Il Im In Io Ip Ir Is It Iu Iv Jg Jh Jk Jl Jm Jn Jo Jp Jq Jr Js Jt Lh Lv Lw Lx Ly Ma Mc Me Mg Mh Mi Mj Mk Ml Mm Mq Mr Mu Mw Mx Mz Na Nb Nc Ne Nf Ng Ni Nj Nk Nl Nm Nn No Nq Nr Ns Nu Nv Nw Nx Ny Oe Oh Oi Om On Pa Pc Pd Pe Pf Pg Po Pz Qb Qc) Oe(aA Fr Hr Hv Hw Hx Ih Ii Ij Il In Io Ip Ir Is It Iu Iv Jg Jh Jk Jl Jm Jn Jo Jp Jq Jr Js Jt Lh Lv Lw Lx Ly Ma Mc Me Mg Mh Mi Mj Mk Ml Mm Mq Mr Mu Mv Mw Mx Mz Na Nb Nc Ne Nf Ng Ni Nj Nk Nl Nm Nn No Nq Nr Ns Nu Nv Nw Nx Ny Of Oh Oi Om On Pa Pc Pd Pe Pf Pg Po Pz Qb Qc) Pg(aA bM Fr Hr Hv Hw Hx Ih Ii Ij Ik Il In Io Ip Ir Is Iu Iv Jg Jh Jk Jl Jm Jn Jo Jp Jq Jr Js Jt Lh Lv Lw Lx Ly Ma Mc Me Mg Mh Mi Mj Mk Ml Mm Mq Mr Mu Mv Mw Mx Mz Na Nb Nc Ne Nf Ng Ni Nj Nk Nl Nm Nn No Nq Nr Ns Nu Nv Nw Nx Ny Of Oh Oi Om On Pa Pc Pd Pe Po Pz Qb Qc) aA(Fr Hr Hv Hw Hx Ih Ii Ik Im In Io Ip Ir Is It Iu Iv Jg Jk Jl Jm Jn Jo Jp Jq Jr Js Jt Lh Lv Lw Lx Ly Ma Mc Me Mg Mh Mi Mj Mk Ml Mm Mq Mr Mu Mv Mw Mx Mz Na Nb Nc Ne Nf Ng Ni Nj Nk Nl Nm Nn Nq Nr Ns Nu Nv Nw Nx Ny Of Oh Oi Ok Om On Pa Pc Pd Pe Pf Po Pz Qb Qc Qd) Ns(Fr Hr Hv Hw Hx Ih Ii

Figure 33 Continued

Figure 33 Continued aN bM cI dR EF GL hC hG iH iJ iZ kS Li Lj Mp oE oN pF Qe Rg Uh Uv Wm) Ir(Aj aM aN bM Hr Hw Ip Jk Jl Lv Ma Mc Mg Mi Mq Mu Na Nq Nr Nv Oi On Pa Pc Pe Qc) Nf(bM Hr Hw Hx Ij Ip Jk Jq Js Lv Ma Mc Mg Mi Mq Mu Na Nq Nr Nv Ny Oi On Pa Pe) Hv(Hr Hw Hx Ij Ip Jk Jq Js Lv Ma Mc Mg Mi Mq Mu Na Nq Nr Nv Ny Oi On Pa Pc Pe) Ik(aN bM Gl Hr Hw Ij Ip Jk Js Lv Ma Mc Mg Mi Mq Mu Na Nq Nr Nv Oi On Pa Pe Pk) Pz(aN bM Hr Hw Ij Ip Jk Js Lv Ma Mc Mg Mi Mq Mu Na Nq Nr Nv Oi On Pa Pe Qc) Hx(Hr Hw Ij Ip Jk Js Lv Ma Mc Mg Mi Mq Mu Mv Mw Na Nq Nr Nv Ny Oi On Pa) Qc(Hr Hw Ij Ip Jk Jl Js Lv Ma Mc Mg Mi Mq Mu Na Nq Nr Nv Oi On Pa Pc Pe) Jh(Hr Hw Ij Ip Jk Js Lv Ma Mc Mg Mi Mq Mv Mw Na Nq Nr Nv Oi On Pa Pe) Jl(Hr Hw Ij Ip Jk Js Lv Ma Mc Mg Mi Mq Mu Na Nq Nr Nv Oi Ok Pa Pc Pe) Jq(Aa Hr Hw Ij Ip Jk Js Lv Ma Mc Mg Mi Mq Mu Na Nq Nr Nv Oi On Pa Pe) It(Hr Hw Ij Ip Jk Js Lv Ma Mc Mg Mi Mq Mu Na Nq Nr Nv Oi On Pa Pe) Pc(Hr Hw Ij Ip Jk Js Lv Ma Mc Mg Mi Mq Mu Na Nq Nr Nv Oi On Pa Pe) Mv(Hr Hw Ij Ip Jk Js Lv Ma Mc Mg Mi Mq Mw Na Nq Nr Nv Oi On Pa) Ny(Hr Hw Ij Ip Jk Js Lv Ma Mc Mg Mi Mq Mu Na Nq Nr Nv Oi On Pa) Of(Hr Hw Ij Ip Jk Js Lv Ma Mc Mg Mi Mq Mu Na Nq Nr Nv Pa Pe) Mw(Hr Hw Ij Ip Jk Js Lv Ma Mc Mg Mi Mq Na Nq Nr Nv Oi Pa) Im(Hr Hw Ip Js Lv Ma Mc Mg Mi Mq Mu Na Nr Nv Oi On Pa Pe) Mp(Aa aN Ar Ax bM dH Hr Hw Jk Js Ma Mg Mq Na Nq Nr Pa) bM(Aa aC Aj aK aN aO Ch cI dI EF Gl Li Lj Lz Ms Vv) Gl(aC aK Ar dH Ef Et Ju Jv Li Lj Ms Qe Qw Vt) Qd(Hr Ij Lv Ma Mc Mg Mq Mu Na Nr Oi On Pa) Pe(Hr Ij Jk Mi Mu Nq Nv Oi Ok On Pa) Li(aC Aj aN aO bQ cD Ch Co Ef Qw) Ok(Hw Js Lv Ma Mq Mu Nr Oi Pa) aN(aC aF aO cD Ch Lj Lz Ms Qe) Ch(dH Et iJ Qe Rg Uk Wm) Qw(aO Ar Ax Cs Id Lj Wm) Lj(aC Aj aK bQ cD iJ) Vt(aF aK aO Ax bL Pk) Nq(iJ Lv Mi Mu Oi) Qe(Aa Aj aO cD Co) Jv(Ar As Ax Id Jd) Wm(Iz Ms Qz) Lv(Jk Nv Oi) Mu(Jk Mg Nv) Vv(Ax Jd Kp) aC(aL aO cZ) bQ(dH Lz Rg) Aa(Lu Lz) Aj(Ad Ms) Et(aO Pk) Ij(Hw Oy) Yk(fP gP) aM(dK Ip) ArRf CoRg EfJd FwSf NaOy IziJ JkOi YemM aFdH aKaQ} Et{Ir(Aj Fr Hq Hr Hu Hv Hw Hx Ih Ii Ij Ik Il In Io Ip Iq Is Iu Iv Jg Jh Jj Jk Jl Jm Jn Jo Jp Jq Jr Js Jt Lh Lu Lv Lw Lx Ly Ma Mb Mc Md Me Mf Mg Mh Mi Mj Mk Ml Mm Mn Mp Mq Mr Mt Mu Mv Mw Mx Mz Na Nb Nc Nd Ne Nf Ng Nh Ni Nk Nl Nm Nn No Nq Nr Ns Nt Nu Nv Nw Nx Ny Oe Oh Oi Ok Om On Oz Pa Pc Pd Pe Pf Pg Pk Po Pz Qa Qb Qc Qd) Ok(Fr Hq Hr Hu Hv Hw Hx Ih Ii Ij Ik Il In Io Ip Iq Is Iu Iv Jg Jj Jk Jl Jm Jn Jo Jp Jq Jr Js Jt Lh Lu Lv Lw Lx Ly Ma Mb Mc Md Me Mf Mg Mh Mi Mj Mk Ml Mm Mn Mq Mr Mt Mu Mv Mw Mx Mz Na Nb Nc Nd Ne Nf Nh Ni Nk Nl Nm Nn No Nq Nr Ns Nt Nu Nv Nw Nx Ny Oe Oh Oi Om On Oz Pa Pc Pd Pe Pf Pg Po Pz Qa Qb Qc Qd) Qd(aA Fr Hq Hr Hu Hv Hw Hx Ih Ii Ik Il In Io Ip Iq Is Iu Iv Jg Jh Jj Jk Jl Jm Jn Jo Jp Jq Jr Js Jt Lh Lu Lv Lw Lx Ly Ma Mb Mc Md Me Mf Mg Mi Mj Mk Ml Mm Mn Mq Mr Mt Mu Mv Mw Mx Mz Na Nb Nc Nd Ne Nf Nh Ni Nk Nl Nm Nn No Nr Ns Nt Nu Nv Nw Nx Ny Oh Oi Om On Oz Pa Pc Pd Pe Pf Pg Po Qa Qb Qc) Pb(aA Fr Hq Hr Hu Hv Hw Hx Ih Ii Ij Ik Il In Io Ip Iq Is Iu Iv Jg Jh Jj Jk Jm Jn Jo Jp Jq Jr Js Jt Lh Lv Lw Ly Ma Mb Mc Md Me Mf Mg Mi Mj Mk Ml Mm Mn Mp Mq Mr Mt Mu Mv Mw My Na Nb Nd Ne Nf Ng Nh Ni Nk Nl Nm Nn No Nq Nr Ns Nt Nu Nv Nx Ny Oe Oh Oi Om On Oy Oz Pa Pc Pd Pe Pf Pg Po Pz Qb Qc) Mh(aA Fr Hq Hr Hu Hv Hw Hx Ih Ii Ij Ik Il In Io Ip Iq Is Iu Iv Jg Jj Jk Jl Jm Jn Jo Jp Jq Jr Js Jt Lh Lv Lw Lx Ly Ma Mb Mc Md Me Mf Mg Mi Mj Mk Ml Mm Mn Mp Mq Mr Mt Mu Mx Na Nb Nd Ne Nf Nh Ni Nk Nl Nm Nn No Nq Nr Ns Nt Nu Nv Nw Nx Ny Oe Oh Oi Om On Oz Pa Pc Pd Pe Pf Pg Po Pz Qb Qc) Nj(aA Fr Hq Hr Hu Hv Hw Hx Ii Ij Ik Il In Io Ip Iq Is Iu Iv Jg Jk Jl Jm Jn Jo Jp Jq Jr Js Jt Lh Lv Lw Lx Ly Ma Mb Mc Md Me Mf Mg Mi Mj Mk Ml Mm Mn Mp Mq Mr Mt Mu Mv Mw Na Nb Nc Nd Ne Nf Nh Ni Nk Nl Nm Nn No Nq Nr Ns Nt Nu Nv Nw Nx Ny Oe Oh Oi Om On Oz Pa Pc Pd Pe Pf Pg Po Pz Qb Qc) Ng(aA Fr Hr Hu Hv Hw Hx Ih Ij Ik Il Io Iq Is Iu Iv Jg Jh Jj Jk Jl Jn Jo Jp Jq Jr Js Lh Lu Lv Lw Lx Ly Mb Mc Md Me Mf Mi Ml Mm Mn Mp Mq Mr Mt Mu Mv Mw Mx My Mz Nb Nc Nd Ne Nf Nh Nl Nm Nn No Nq Nr Ns Nt Nu Nv Nw Nx Ny Oe Oh Oi On Oy Oz Pa Pc Pd Pe Pf Pg Po Pz Qb Qc) Qa(aA Fr Hr Hu Hv Hw Ih Ii Ij Ik Il Im In Io Ip Iq Is Iu Iv Jg Jl Jm Jn Jp Jq Jr Js Jt Lh Lv Lw Lx Ly Ma Mc Md Me Mf Mg Mi Mj Mk Ml Mm Mn Mq Mr Mt Mu Mx Mz Na Nb Nd Ne Nf Nh Ni Nk Nl Nm Nn No Nr Ns Nt Nu Nv Nw Nx Ny Oh Oi Om On Oz Pa Pc Pd Pe Pf Pg Po Qb Qc Qe) Nc(Fr Hq Hr Hu Hv Hw Hx Ih Ii Ik In Io Iq Is Iu Iv Jh Jj Jk Jl Jm Jn Jo Jq Jr Js Jt Lh Lu Lv Lw Lx Ly Ma Mb Mc Me Mf Mg Mi Mk Ml Mm Mn Mp Mq Mr Mt Mv Mw Mx Nb Nd Ne Nf Nh Ni Nk Nm Nn No Nq Nr Ns Nt Nu Nw Nx Ny Oe Oh Oz Pa Pc Pd Pe Pf Pg Po Pz Qb Qc) My(aA Fr Hq Hr Hu Hv Hw Hx Ij Ik Il In Io Ip Iq Iu Iv Jh Jj Jk Jn Jo Jp Jq Jr Js Lv Ly Ma Mb Mc Md Me Mg Mi Mj Mk Ml Mm Mn Mp Mq Mr Mu Mv Mw Na Nb Nd Ne Nf Nh Ni Nk Nl Nm No Nq Nr Ns Nt Nu Nv Nx Ny Oe Oh Oi Om Oy Oz Pa Pc Pd Pe Pf Pg Pk Po Pz Qc) Mz(aA Fr Hq Hu Hv Hw Ih Ii Ij Ik Il Io Iq Is Iu Iv Jh Jj Jk Jl Jm Jn Jo Jp Jq Jr Js Jt Lh Lu Lv Lw Lx Ly Ma Mb Mc Md Me Mf Mg Mi Mj Mk Ml Mm Mn Mp Mr Mt Mx Nb Nd Ne Nf Nh Ni Nk Nl Nm Nn No Nq Ns Nt Nu Nw Nx Oe Oh Om Oz Pc Pd Pe Pf Pz Qb) Oy(aA Fr Hq Hr Hu Hv Hw Hx Ii Ij Ik Il In Io Ip Iq Iu Iv Jh Jj Jk Jo Jp Jq Jr Js Lv Ly Ma Mb Mc Md Me Mf Mg Mi Mj Mk Ml Mm Mn Mp Mq Mr Mu Mv Mw Na Nb Nd Ne Nf Nh Ni Nk Nm No Nq Nr Ns Nt Nu Nv Nx Ny Oe Oh Oi Om Oz Pa Pc Pf Pg Pk Pz Qc) Mx(Fr Hq Hr Hu Hv Hx Ih Ii Ik Il In Io Is Iv Jh Jj Jk Jl Jm Jn Jo Jp Jq Jr Jt Lh Lu Lv Lw Lx Ly Ma Mb Mc Md Me Mf Mg Mj Mk Ml Mm Mp Mt Mv Mw Nb Nd Ne Nf Nh Nl Nm Nn No Nq Ns Nt Nu Nv Nw Nx Ny Oe Om Oz Pc Pd Pg Pz Qb Qc) Lu(aA Fr Hq Hu Hv Hx Ih Ik Io Iq Is Iu Iv Jh Jj Jk Jl Jm Jn Jo Jp Jq Jr Js Jt Lh Lv Lw Lx Ly Mb Me Mf Mg Mi Mk Ml Mm Mp Mr Mt Mv Mw Nb Nd Ne Nf Nh Nl Nm Nn No Nq Nr Ns Nt Nu Nw Nx Ny Oe Oz Pc Pd Pe Pf Pz Qb Qc) Im(aA Fr Hr Hv Hw Ih Ij Ik Il Ip Is Iu Iv Jg Jm Jn Jp Jq Js Jt Lh Lv Lx Ma Mc Md Me Mf Mg Mi Mj Mk Mm Mn Mq Mr Mt Mu Na Nb Nd Ne Nh Ni Nk Nn No Nr Ns Nt Nu Nv Nw Nx Ny Oh Oi Om On Oz Pa Pc Pd Pe Pf Pg Po Qb Qc) Ih(Fr Hq Hu Hv Hx Ii Ik Il In Io Is It Iv Jh Jj Jk Jl Jm Jn Jo Jq Jr Jt Lh Lv Lw Lx Ly Mb Me Mf Mg Mj Mk Ml Mm Mp Mt Mv Mw Nb Nd Ne Nf Nh Nl Nm Nn Nq Ns Nt Nu Nw Nx Ny Oe Oz Pc Pd Pe Pf Pg Pz Qe) Lz(AA Fr Hq Hr Hw Ii Ij In Io Ip Iq Iu Iv Jg Jk Jp Js Lh Lv Lx Ly Ma Mb Mc Md Me Mf Mg Mi Ml Mm Mn Mq Mr Mu Na Nd Nh Ni Nk Nm No Nr Nt Nu Nv Oh Oi Om On Pa Pd Pe Pf Pg Pk Po Qb Qc) Jj(aO bM Dc Hu Hv Hx Ik Il Io Iq Is Iv Jh Jl Jn Jq Jr Js Jt Lh Lv Lw Lx Ly Mb Me Mf Ml Mm Mp Mr Mt Mv Mw Nb Nd Ne Nl Nm Nn No Nq Ns Nt Nu Nw Nx Ny Oe On Oz Pc Pd Pe Pf Po Pz Qb Qc) It(aA Fr Hr Hv Hw Ii Ij Il In Ip Iq Iu Iv Jg Jk Jn Jp Jq Jr Js Jt Lh Ly Ma Mc Md Mf Mi Mj Mm Mn Mq Mr Mu Na Nd Nh Ni Nk No Nr Nt Nv Nx Oh Oi Om On Pa Pe Pf Pg Po Qc) Is(Hq Hu Hv Hx Ii Ik Io Iv Jk Jl Jm Jn Jo Jr Jt Lh Lw Lx Ly Mb Me Mf Mg Mj Mk Ml Mp Mt Mv Mw Nb Ne Nf Nl Nm Nn No Nq Ns Nt Nu Nw Ny Oe Om Oz Pc Pd Pz Qb) Jh(aA Hv Hw Hx Ij Ik Io Iv Jg Jl Jm Jn Jq Jr Js Jt Lh Lv Lw Lx Ly Mb Me Mf Ml Mp Mr Mt Nb Ne Nl Nm Nn No Ns Nt Nu Nw Nx Ny Oe On Oz Pc Pd Pe Pk Po Pz Qb) Qe(Aa aO cM Hr Hw Ij In Iq Iv Jg Jm Jp Js Lh Lv Lx Ma Mc Md Mi Mm Mn Mq Mr Mt Mu Na Ni Nk No Nr Nt Nv Nw Nx Oi Om On Pa Pe Pf Pk Po Qb) Jn(Hq Hu Hv Hx Ik Il Io Jk Jl Jm Jo Jr Jt Lv Lw Lx Ly Mb Me Mf Mg Ml Mp Mt Mv Mw Nb Ne Nf Nl Nm Nn No Nq Ns Nu Nw Ny Oe Oz Pc Pz Qb) Jl(Fr Hq Hu Hv Hx Ii Ik Iv Jk Jm Jo Jr Jt Lw Lx Mb Me Mf Ml Mp Mt Mv Mw Nb Ne Nf Nl Nn Nq Ns Nu Nv Nw Ny Oe Oz Pc Pd Pz Qb) Jm(aA Hq Hu Hx Ii In Io Jk Jo Jq Jr Jt Lv Lw Lx Mb Me Mg Ml Mp Mt Mv Mw Nb Ne Nf Nl Nm Nn No Nq Nu Nw Ny Oe Oz Pc Pz) Pk(Aj Ao Ar Aw Ax Ba Bg cM Cs Dk Ef Gl Gp Hc Ic Id In Iz Jd Je Kc Kk Ld Li Lv Ly Me Mw Nb Nf Nk Ny Og Or Ph Pj Rg Vt) Mv(Hx Iv Jg Jq Jr Js Jt Lh Lv Lw Lx Mb Me Mf Mi Ml Mp Mr Mt Mu Nb Ne Nl Nn No Nt Nu Nw Ny Oe On Oz Pc Pe Po Qb) Og(Fr Hq Hu Hw Ii In Ip Iq Iu Jk Jo Jp Ma Mc Md Mg Mi Mj Mk Mm Mn Mq Mu Mw Na Nf Nh Ni Nk Nr Nv Oh Om Pa Pf Pg) Nn(Hu Hx Ik Io Iv Jk Jo Jq Jr Jt Lv Lw Lx Ly Ma Mb Me Mf Ml Mp Mt Mw Ne Nf Nl Nm Nq Ns Nu Nw Oe Oz Pc Pz) Of(aA Fr Hq Hr Hw Ii In Io Ip Iq Iu Jk Jo Ma Mc Md Mg Mi Mj Mk Mn Mq Mu Na Nf Ni Nk Nr Oh Oi Om Pa Pg Po) Ms(AA Fr Hr Hw Ii Ij Il In Ip Iu Jg Jk Ma Mc Md Mg Mj Mk Mq Mu Mw Na Nf Ni Nk Nv Oh Oi Om Pa Pf Pg) Oe(aA Hx Ij Ik Il Iv Jq Jr Js Jt Lh Lw Lx Ly Mb Me Mf Ml Mp Mt Mw Ne Nl No Ns Nt Nu Nw Nx Ny Oz Pc Qb) Mw(Hx Iv Jg Jq Jr Js Jt Lh Lv Lw Lx Mb Me Ml Mp Mr Mt Mu Nb Nl No Nt Nu Nw Ny On Oz Pe Po Pz Qb) Nl(Hu Hv Hx Ik Io Iv Jo Jq Jr Jt Lv Lw Lx Mb Me Mf Ml Mp Mt Nb Nd Nh No Ns Nw Ny Oz Pc Pz Qb) Qb(Hq Hu Hv Hx Io Jk Jo Jr Jt Lw Mb Me

Figure 33 Continued

Mk Ml Mp Nb Ne Nf Nm Nq Ns Nu Ny Oz Pc Pz) Nw(Hu Hv Hx Io Iv Jr Jt Lw Mb Me Mf Ml Mp Ne Nm Nq Ns Nu Ny Oz Pc Pz) Hx(aA Jq Jr Js Jt Lh Lw Lx Mb Me Ml Mp Mr Mt No Ny Oz Pc Pe Pz) Li(Aj aO Hw Ij Ip Iq Iu Jp Js Mm Mq Mr Mu Na Nk Nr On Pa Qc) Lw(Hu Iv Jo Jr Lh Lx Mb Me Ml Mp Mt Ne Nq Ns Ny Oz Pc Pz) Jr(Hv Ik Io Jo Jt Lx Mb Mf Ml Mp Mt Nf Nq Ns Ny Oz Pz) Mb(Aa Ik Jq Jt Lx Mp Mt Nd No Ns Nu Ny Oz Pc Pz) Lx(Hu Hv Jo Jt Mk Ml Mp Nq Ns Ny Oz Pc Pz) Mt(Hu Hv Io Jk Jt Mk Ml Mp Nq Ns Oz Pc Pz) Mp(Iv Jq Js Jt Lh No Nq Ny On Pe Pz) Pz(Iv Jt Lh Ml Nb Ns Nt Nu Ny Qc) Jt(Hu Ii Jo Mg Ml Ne Nq Ns Om) Aj(aH bM cM Dc Dd Lj) Jo(Js Lh Ml Nt Nu Ny) Lj(aC aO cM Jd Or) Nq(Iv No Ny) Nu(Ns Oz Pc) Ml(Ny Oz Pc) Ii(Lh Mr Pe) Hu(Mf Mu) Iq(Ik Il) Pe(Nb Ny) AaFp NeOz JqOm VtcM} Ok{Qe(AA Fp Fr Hq Hr Hu Hv Hw Hx Ih Ij Ik Il Im In Io Ip Iq Ir Is Iu Iv Jg Jk Jl Jm Jn Jo Jp Jq Jr Js Jt Lh Lu Lv Lw Lx Ly Ma Mb Mc Md Me Mf Mg Mh Mi Mj Mk Ml Mm Mn Mq Mr Mt Mu Mv Mx Mz Na Nb Nc Nd Ne Nf Nh Ni Nk Nl Nm Nn No Nr Ns Nt Nu Nv Nw Nx Ny Oh Oi Om On Oz Pa Pc Pd Pe Pf Pg Po Qa Qb Qd) Oy(aA Fr Hq Hv Hx Ih Ii Ik Il In Io Ip Iq Iu Iv Jg Jh Jj Jk Jl Jm Jn Jo Jp Jq Jr Jt Lh Lv Lw Lx Ly Ma Mb Mc Md Me Mf Mg Mh Mi Mj Mk Ml Mm Mn Mp Mq Mr Mt Mu Mv Mw Mx Mz Na Nb Nc Nd Ne Nf Ng Nh Ni Nk Nl Nm No Nq Nr Ns Nt Nu Nv Nx Ny Oe Oh Oi Om On Oz Pa Pc Pd Pe Pf Pg Po Pz Qb Qd) Nj(Aa Fr Hq Hu Hv Hx Ih Ii Ik Il In Io Ip Iq Is Iu Iv Jh Jk Jl Jm Jn Jo Jp Jr Jt Lh Lv Lw Lx Ly Ma Mb Mc Md Me Mf Mg Mh Mi Mj Mk Ml Mm Mn Mq Mr Mt Mu Mv Mw Mx Mz Na Nb Nc Nd Ne Nf Ng Nh Ni Nk Nl Nm Nn No Nq Nr Ns Nt Nu Nv Nx Ny Oe Oh Oi Om On Oz Pa Pc Pd Pe Pf Pg Pz Qa Qb Qd) Lu(AA Fr Hu Hv Hx Ih Ii Ik Il In Io Ip Iq Is Iu Iv Jh Jj Jl Jm Jn Jo Jp Jt Lh Lv Lw Lx Ly Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nk Nl Nm Nn No Nq Nr Ns Nt Nu Nv Nw Nx Ny Oe Oh Oi Om On Oz Pc Pd Pe Pf Pg Pz Qa Qb Qd) Pb(aA Fr Hq Hr Hu Hv Hw Hx Ih Ii Ik Il In Ip Iq Iu Iv Jg Jh Jk Jl Jm Jn Jo Jp Jq Jr Js Jt Lh Lv Lx Ly Ma Mb Mc Md Me Mf Mg Mi Mj Mk Ml Mn Mq Mr Mt Mu Mv Mw Mz Na Nb Nd Ne Nf Ng Nh Ni Nk Nl Nm No Nq Nr Ns Nt Nu Nv Nx Ny Oh Oi Om On Oz Pa Pc Pd Pe Pf Pg Po Pz Qb Qc Qd) Lz(AA Fr Hq Hr Hu Hv Hw Hx Ih Ij In Ip Iq Iu Iv Jg Jh Jk Jl Jm Jn Jo Jp Jq Jr Js Jt Lh Lv Lw Lx Ly Ma Mb Mc Md Me Mf Mg Mi Mk Ml Mm Mn Mq Mr Mt Mu Mx Mz Na Nb Nd Ne Nh Ni Nk Nl Nm Nn No Nr Ns Nt Nu Nv Nw Nx Ny Oe Oh Oi Om On Pa Pc Pd Pe Pf Pg Po Pz Qa Qb Qc Qd) Ir(Fr Hq Hu Hv Hx Ih Ii Ij Ik Il In Io Ip Iq Is Iu Iv Jh Jj Jk Jo Jp Jr Js Lv Lw Lx Ly Ma Mb Mc Md Me Mf Mg Mh Mi Mj Mk Ml Mm Mn Mq Mr Mt Mu Mv Mw Mx Mz Na Nb Nc Nd Ne Nf Ng Nh Ni Nk Nl Nm Nn No Nq Nr Ns Nt Nu Nv Nw Nx Ny Oe Oh Oi Om On Oz Pc Pd Pf Pz Qa Qd) My(AA Fr Hv Hx Ih Ii Ij Ik Il In Io Ip Iq Iu Iv Jg Jh Jj Jl Jm Jn Jo Jp Jq Jr Js Jt Lh Lv Ly Ma Mb Mc Md Me Mg Mi Mj Mk Ml Mn Mp Mq Mr Mt Mv Mw Mx Na Nb Nd Ne Nf Ng Nh Ni Nk Nl Nm No Nq Nr Ns Nt Nu Nv Nx Oe Oh Oi Om On Oz Pa Pc Pd Pe Pf Pg Po Pz Qb Qd) Mp(aA Fr Ih Ii Ik Il In Io Ip Iq Iu Iv Jh Jj Jl Jm Jn Jo Jp Js Jt Lh Lv Lw Lx Ly Ma Mb Mc Md Me Mf Mg Mh Mi Mj Mk Ml Mm Mn Mq Mr Mt Mu Mv Mw Mx Mz Na Nb Nc Nd Ne Nf Ng Nh Ni Nk Nl Nm Nq Nr Ns Nt Nu Nv Nx Ny Oe Oh Oi Om On Oz Pc Pd Pe Pf Pz Qb Qd) Im(Fr Hq Hr Hu Hv Hw Hx Ih Ij Ik Ip Iq Is Iv Jg Jl Jm Jn Jo Jp Jq Jr Js Jt Lh Lv Lw Lx Ma Mb Mc Md Me Mf Mg Mh Mi Mk Ml Mm Mn Mq Mr Mt Mu Mx Na Nd Ne Nh Ni Nk Nl Nm Nn No Nr Ns Nt Nu Nv Nw Nx Ny Oh Oi On Oz Pa Pc Pd Pe Pf Pg Po Qa Qb Qc Qd) Ng(aA Fr Hv Hx Ih Ij Ik Il Io Ip Iq Is Iu Iv Jg Jj Jl Jm Jn Jp Jt Lh Lv Lw Lx Ly Ma Mb Mc Md Me Mf Mg Mh Mi Mj Ml Mm Mn Mq Mr Mt Mu Mv Mw Mx Mz Na Nb Nc Nd Ne Nf Nh Nl Nm Nn No Nq Nr Ns Nt Nu Nv Nw Nx Ny Oe Oh On Oz Pc Pd Pe Pf Qa Qb Qd) Jj(Hu Hv Hx Ih Ii Ik Il Io Ip Iq Is Iu Iv Jg Jh Jl Jn Jo Jp Jq Jr Js Jt Lh Lv Lw Lx Ly Ma Mb Mc Md Me Mf Mh Mi Mj Mk Ml Mm Mn Mt Mu Mv Mw Mx Mz Nb Nc Nd Ne Nf Nh Nl Nm Nn No Nq Nr Ns Nt Nu Nv Nw Nx Ny Oe Om Oz Pc Pd Pe Pf Po Pz Qb Qd) Fp(AA Fr Hq Hr Hu Hv Hw Hx Ih Ij Il In Ip Iq Iu Iv Jg Jk Jl Jm Jn Jo Jp Jq Jr Js Jt Lh Lv Lx Ly Ma Mb Mc Md Mf Mg Mi Ml Mn Mq Mr Mt Mu Mx Mz Na Nd Ne Nh Ni Nk Nm No Nr Ns Nt Nu Nv Nx Oh Oi On Oz Pa Pc Pd Pe Pf Pg Po Pz Qb Qc Qd) Nc(Hv Hx Ih Ii Ik In Io Ip Iq Is Iu Iv Jh Jl Jn Jo Lv Lw Lx Ly Ma Mb Mc Md Me Mf Mg Mh Mj Mk Ml Mm Mn Mr Mt Mu Mv Mw Mx Mz Nb Nd Ne Nf Nh Ni Nk Nm Nn No Nq Ns Nu Nw Ny Oe Oh Om Oz Pc Pd Pf Pz Qa Qd) Qa(Fr Hq Hu Hv Hw Hx Ii Ik Il In Io Ip Iq Is Iu Iv Jh Jk Jl Jo Jp Lw Ly Mb Mf Mg Mh Mj Mk Ml Mm Mv Mw Mz Nb Ne Nf Nh Nl Nm Ns Nv Nw Ny Oe Oh Om On Oz Pc Pd Pg Pz Qc Qd) Nw(Fr Hv Hx Ij Ik Il Io Ip Iq Is Iu Iv Jh Lw Lx Ly Ma Mb Md Me Mf Mh Mj Mk Ml Mm Mn Mt Mu Mv Mz Na Nb Nd Ne Nf Nh Nl Nm Nn Nq Ns Nu Nv Nx Ny Oe Oh Om On Oz Pc Pd) Mh(Hx Ih Ii Ik Il In Io Ip Iq Is Iu Iv Jh Jo Jp Lw Lx Ly Md Me Mf Mg Mj Mk Ml Mm Mt Mv Mw Mx Mz Nb Nd Ne Nf Nl Nm Nn Nq Ns Ny Oe Oh Om Oz Pc Pz Qd) Nn(Fr Hx Ii Ik Il In Io Ip Iq Is Iu Iv Jh Jo Lw Lx Ly Ma Mb Mf Mj Mk Ml Mm Mt Mv Mw Mx Mz Na Nb Ne Nf Nh Nl Nm Nq Ns Ny Oe Oh Om On Oz Pc) It(aA Fr Hq Hr Hu Hv Hw Ih Ip Iq Is Iv Jg Jk Jl Jm Jn Jq Jr Js Jt Lh Mi Mn Mq Mr Ni Nk No Nt Nv Nx Oi Pa Pe Pf Pg Po Qb Qc Qd) Mx(Hu Hv Hx Ii Ik Il In Io Ip Iq Is Iu Iv Jh Jo Lw Mb Mg Mj Mk Ml Mm Mv Mw Mz Nf Nl Nm Nq Ns Ny Oe Om Oz Pc Pd Pz) Io(Aa Ih Ii Ik Is Iv Jh Jo Jp Lw Lx Ly Mb Me Mf Mg Mm Mt Mv Mw Mz Nb Nd Ne Nf Nl Nm Nq Ns Nu Ny Oe Oz Pc Pz Qd) Is(Hx Ii Ik Jh Jo Jp Lw Ly Ma Mb Mf Mg Mj Mm Mt Mv Mw Mz Nb Ne Nf Nl Nm Nq Ns Nu Ny Oe Om On Oz Pc Pz Qd) Oe(Aa Ih Ik Il Ip Iq Iu Iv Jm Lw Lx Ly Mf Mg Mm Mt Mv Mw Mz Ne Nf Nl Nm Nq Ns Ny Oz Pc Qb Qd) Mv(Ih Ip Iq Iu Iv Jl Jp Lh Lw Lx Ly Mf Mi Mm Mt Mu Mz Nb Nd Ne Nl Nm Nq Ny Oz Pd Pe Qd) Mm(Ih Ip Iq Iu Iv Jh Jn Jo Lw Lx Mb Mw Mz Nb Nf Nl Nm Nq Ny Om Oz Pc Qd) Mw(Iq Iu Iv Jg Jl Jp Lh Lw Lx Ly Mf Mt Mz Nd Ne Nl Nm Ny Oz Pc Qd) Ii(Ih Il Ip Iq Iu Iv Jl Jm Jp Lh Lw Lx Mr Mt Mz Nl Nv Ny Pe Qd) Jh(Iv Jg Jl Jn Jp Jt Lh Lw Lx Mt Mu Mz Nl Ny Oz Pz Qd) Li(aA Hw Ih Jg Jq Js Jt Lx Mq Mt No Nt Pa Pe Pf Pg Qb) Nq(Ih Iq Iv Jo Jp Lw Lx Mf Mt Mz Nd Nf Nm Ny Qd) Mz(Hx Ik Il Iq Iv Lw Ml Nb Ne Nf Nl Nm Ny Om) Qd(Hv Hx Ik Il Jk Jo Mj Nb Ne Nl Nm Pz Qc) Nl(Ik Iq Iu Iv Jo Lw Mg Ns Ny Oz Pc) Lw(Iq Iv Jo Mb Mg Ne Nf Om Pc) Ny(Il Iv Jo Lx Ly Mj Nb Nf Om) Iv(Jo Mg Nb Nf Om Oz Pz) Nb(Ip Iq Iu Jp Lh) Iq(Ik Il Mj Nf) Jo(Jm Jn Jt) Aj(bM cM Dc) Aa(Mb Og) Hx(Jl Jp) Mjlh MkPd MuHu PzJt JpOm} Li{Qe(AA Fp Fr Hq Hr Hu Hv Hw Hx Ii Ik Il Im In Io Ip Iq Ir Is It Iu Iv Jg Jh Jk Jl Jm Jn Jo Jp Jq Jr Js Jt Lh Lj Lu Lv Lw Lx Ly Lz Ma Mb Mc Md Me Mf Mg Mh Mi Mk Ml Mm Mn Mq Mr Mt Mu Mx Mz Na Nb Nc Nd Ne Nf Nh Ni Nk Nl Nm Nn No Nr Ns Nt Nu Nv Nw Nx Ny Oe Oh Oi Om On Oz Pa Pc Pd Pe Pf Pg Po Pz Qa Qb Qc Qd) Pb(aA Fp Fr Hq Hr Hu Hv Hw Hx Ik Il In Io Ip Iq Is Iu Iv Jg Jh Jk Jm Jn Jo Jq Jr Js Jt Lj Lu Lv Lx Ly Lz Ma Mb Mc Md Me Mf Mg Mh Mi Mj Mk Ml Mm Mn Mp Mq Mr Mt Mu Mv Mw Mx My Na Nb Nd Ne Ng Nh Ni Nk Nl Nm Nn No Nq Nr Ns Nt Nu Nv Nx Ny Oe Oh Oi Om On Oy Oz Pa Pc Pd Pe Pf Pg Po Pz Qb Qc Qd) Nw(aA Fp Fr Hq Hu Hv Hx Ih Ii Ik Il In Io Ir Is Iu Iv Jj Jk Jl Jm Jn Jo Jp Jr Jt Lh Lv Lw Lx Ly Lz Ma Mb Mc Md Me Mf Mg Mh Mi Mj Mk Ml Mm Mn Mq Mr Mt Mu Mx Mz Na Nb Nc Nd Ne Nf Nh Ni Nk Nl Nm Nn No Nq Nr Ns Nt Nu Nv Nx Ny Oe Oh Oi Om On Oz Pc Pd Pg Po Pz Qa Qc Qd) Im(Fp Fr Hq Hr Hu Hv Hw Hx Ii Ij Ik Il Io Iq Ir Is It Iu Iv Jg Jl Jm Jo Jq Jr Jt Lh Lu Lv Lw Lx Ly Ma Mb Mc Me Mf Mg Mh Mj Mk Ml Mm Mp Mt Mu Mx Mz Nb Nc Nd Ne Nh Ni Nl Nm Nn Nq Ns Nt Nu Nv Nx Ny Oe Oh Oi Om On Oz Pc Pd Pe Pf Pg Po Pz Qa Qc Qd) Oy(aA Fp Hq Hv Hx Ih Ik In Io Ir Is It Iv Jh Jj Jm Jn Jq Jr Js Jt Lh Lj Lu Lv Lx Ly Lz Md Me Mf Mh Mi Mj Mk Mm Mn Mp Mr Ms Mt Mu Mx Mz Nb Nc Nd Ne Nf Nh Ni Nl Nm Nn Nq Ns Nt Nu Nv Nx Ny Of Oz Pc Pd Pe Pf Pg Po Pz Qb Qc Qd) Nj(aA Fp Hq Hu Hx Ih Ik In Io Ir Is It Iv Jh Jl Jm Jn Jo Jp Jq Jr Jt Lh Lu Lv Lw Lx Lz Me Mh Mj Mk Mm Mp Ms Mt Mv Mw Mx My Mz Nc Nd Ne Nf Ng Ni Nk Nl Nm Nn Nq Ns Nt Nu Nx Ny Oe Of On Oz Pc Pd Pz Qa Qb Qd) Jj(Dc Fp Hu Hv Hx Ih Ik Il Ir Is Iv Jg Jh Jl Jn Jp Jq Jr Js Jt Lj Lu Lv Lw Ly Lz Me Mf Mh Mj Mk Mm Mp Ms Mv Mw Mx My Mz Nc Nd Ne Nf Ng Nh Nl Nm Nn Nq Ns Nt Nu Nv Nx Ny Of On Oz Pc Pd Po Qa Qb Qd) Jp(Fp Fr Hq Hu Hv Hx Ib Ih Ik Il Io Ir Is Iz Jh Jk Jl Jm Jn Jq Jr Jt Lu Lv Lw Ly Lz Ma Mb Me Mf Mh Mj Mk Mp Mv Mw Mx Mz Nc Ne Nf Ng Nl Nm Nq Ns Nu Ny Oe Oz Pc Pz Qa Qd Qw) Ir(aA Fp Hq Hu Hv Hx Ii Ij Ik Il In Is It Iv Jh Jk Jl Js Lh Lj Lu Lv Lw Ly Lz Me Mf Mj Mk Mm Mp Ms Mv Mw My Mz Nb Nc Ne Nf Ng Nl Nn Nq Nr Ny Oe Of Om Oz Po Pz Qa Qd) Ms(aA Fp Hu Hx Ih Ik Is It Iv Jg Jl Jm

Pb) Lh(Fp Ih Is It Jj Jt Lz Pb Qa Qd) Jt(Fp Mm Mz Nn Qa) Mm(Fp Qa Qd) Qa(Aa Jg) LzJg} Gc{hC(As bO bU cP Dl Em Gn Nh Nk Nl Ql Qv Rb Vp Wc Wc Wm) eC(Aj Cs Fp Pa Uu) SfPk} Jj{Dc(bM Jv Pk Sr Uh Ur Vt) Lh(It Jm Jt Pb Pk Qa) Mm(Fp It Pk Qa) Pk(Kf Kg Uh) AabM FpJt} Jg{My(Lh Lx Lz Mx Mz Qa Qb Qd) Qa(Jh Mw Ng Of Oy) Fp(Jh Mw Oy) Lh(Of Oy) LzOy QdOf} Vt{Ar(aK aP bL bX Nf) Cs(aK aU bB bL bX) bL(Ax bB) AabM DcUr ThgW IbJd} Fp{Jt(Jh Mm My Nc Ng Nj Oy Pb) Mm(It Of Oy Pb) On(My Oy)} Aj{Ad(Ar bC bM dl Ir Lz Mt) JtbM} Qd{Of(Lh Mm On) Lz(Ik Il)} uR{Wm(iA jD tX) Or(Id Mz)} bB{oW(cR dU kl) OzdU} bU{Ax(dU oV) pH(aO Oz)} Nk{DdpK NxgZ bNjB} Ib{Jd(Cq Fa lr)} Kq{ArFr EfKf HuPa} On{Of(My Oy) LzOy} Aa{LuQa IsbM} Ye{IsmS NxnN} cR{NooD NjoW} MIKfrR NgQaJt HumEjB RgUhPk

Unconstrained panels with 3 analytes, where 1.0E-7 >= 'model p-value' > 1.0E-8. Contains 26,971 panels of 38,188,712 total panels evaluated. : Et{Pk(aA aC Ad AF aH aK Al AN aO Ap As Bb Bc bL bM Bn Bo cl Co Cp Cq cR Ct Cu Cv Cw Cx DB Dc Dd De Dg Di DL Dp Ed Ez Fa Fn Fp Fr Fw Fy Hb Hf Hq Hr Hv Hw Hx Ih Ii Ij Il Im Io Ip Iq Is It Iu Iv Jf Jg Jk Jl Jm Jn Jo Jp Jq Jr Js Jt Ju Jv Jy Kd Ke Kf Kg Ki Kj Kl Kn Ko Kp Kq Kr Ks Kx Ky Kz Lh Lu Lw Lx Ma Mb Mc Md Mf Mg Mh Mi Mj Mk Ml Mm Mn Mp Mq Mr Ms Mt Mu Mv Mx Mz Na Nc Nd Ne Ng Nh Ni Nj Nl Nm Nn No Nq Nr Ns Nt Nu Nv Nw Nx Oa Oe Of Oh Oi Ok Om On Ou Ow Oz Pa Pb Pc Pd Pe Pf Pg Pi Po Pz Qa Qb Qc Qd Qm Qn Qt Qu Qv Qw Qx Qz Ra Rb Rc Rf Sr Ss Ua Ub Uc Uh Uk Un Ur Us Ut Uu Uv Vp Vs Vu Vv Wm) Ma(AA Fr Hq Hr Hu Hv Hw Hx Ih Ii Ij Ik Il In Io Ip Iq Is Iu Iv Jg Jh Jj Jk Jl Jm Jn Jo Jp Jq Jr Js Jt Lh Lu Lv Lw Lx Ly Mb Mc Md Me Mf Mg Mi Mj Mk Ml Mm Mn Mp Mq Mr Mt Mu Mv Mw Mx Mz Na Nb Nd Ne Nf Ng Nh Ni Nk Nl Nm No Nq Ns Nt Nu Nv Nw Nx Ny Oe Oh Oi Om On Oz Pa Pc Pd Pe Pf Pg Po Pz Qb Qc) Nr(aA Fr Hq Hr Hu Hv Hw Hx Ih Ii Ik Il In Io Ip Iq Is Iu Iv Jg Jh Jj Jk Jl Jm Jn Jo Jp Jq Jr Js Jt Lh Lv Lw Lx Ly Mb Mc Md Me Mf Mg Mi Mj Mk Ml Mm Mn Mp Mq Mr Mt Mu Mv Mw Mx Mz Na Nb Nd Ne Nf Nh Ni Nk Nl Nm Nn No Nq Ns Nt Nu Nv Nw Nx Ny Oe Oh Oi Om On Oz Pa Pc Pd Pe Pf Pg Po Pz Qb Qc) Hr(aA Fr Hq Hu Hv Hw Hx Ih Ii Ik Il In Io Ip Iq Is Iu Iv Jg Jh Jj Jk Jl Jm Jn Jo Jp Jq Jr Js Jt Lh Lu Lv Lw Lx Ly Mb Mc Md Me Mf Mg Mi Mj Mk Ml Mm Mn Mp Mq Mr Mt Mu Mv Mw Mz Na Nb Nd Ne Nf Nh Ni Nk Nl Nm Nn No Nq Ns Nt Nu Nv Nw Nx Ny Oe Oh Oi Om On Oz Pa Pc Pd Pe Pf Pg Po Pz Qb Qc) Hw(aA Fr Hq Hu Hv Hx Ih Ii Ij Ik Il In Io Ip Iq Is Iu Iv Jg Jj Jk Jl Jm Jn Jo Jp Jq Jr Js Jt Lh Lu Lv Lw Lx Ly Mb Mc Md Me Mf Mg Mi Mj Mk Ml Mm Mn Mp Mq Mr Mt Mu Mv Mw Mx Na Nb Nd Ne Nf Nh Ni Nk Nl Nm Nn No Nq Ns Nt Nu Nv Nw Nx Ny Oe Oh Oi Om On Oz Pa Pc Pd Pe Pf Pg Po Pz Qb Qc) Qc(AA Aj Fr Hq Hu Hv Hx Ih Ii Ij Ik Il In Io Ip Iq Is Iu Iv Jg Jh Jk Jl Jm Jn Jo Jp Jq Jr Js Jt Lh Lv Lw Lx Ly Mb Mc Md Me Mf Mg Mi Mj Mk Ml Mm Mn Mp Mq Mr Mt Mu Mv Mw Mz Na Nb Nd Ne Nf Nh Ni Nk Nl Nm Nn No Nq Ns Nt Nu Nv Nw Nx Ny Oe Oh Oi Om On Oz Pa Pc Pd Pe Pf Pg Po Qb) Jp(aA Fr Hq Hu Hv Hx Ih Ii Ik Il In Io Ip Iq Is Iu Iv Iz Jg Jh Jj Jk Jl Jm Jn Jo Jq Jr Js Jt Lh Lv Lw Lx Ly Mb Mc Md Me Mf Mg Mi Mj Mk Ml Mm Mn Mp Mq Mr Mt Mu Mv Mw Na Nb Nc Nd Ne Nf Nh Ni Nk Nl Nm Nn No Nq Ns Nt Nu Nv Nw Nx Ny Oe Oh Oi Om On Oz Pa Pc Pd Pe Pf Pg Po Pz Qb) Oh(aA Fr Hq Hu Hv Hx Ih Ii Ik Il In Io Ip Iq Is Iu Iv Jg Jh Jj Jk Jl Jm Jn Jo Jq Jr Js Jt Lh Lu Lv Lw Lx Ly Mb Mc Md Me Mf Mg Mi Mj Mk Ml Mm Mn Mp Mq Mr Mt Mu Mv Mw Mx Na Nb Nd Ne Nf Nh Ni Nk Nl Nm Nn No Nq Ns Nt Nu Nv Nw Nx Ny Oe Oi Om On Oz Pa Pc Pd Pe Pf Pg Po Pz Qb) Mc(aA Fr Hq Hu Hv Hx Ih Ii Ik Il In Io Ip Iq Is Iu Iv Jg Jh Jj Jk Jl Jm Jn Jo Jq Jr Js Jt Lh Lu Lv Lw Lx Ly Mb Md Me Mf Mg Mi Mj Mk Ml Mm Mn Mp Mq Mr Mt Mu Mv Mw Na Nb Nd Ne Nf Nh Ni Nk Nl Nm Nn No Nq Ns Nt Nu Nv Nw Nx Ny Oe Oi Om On Oz Pa Pc Pd Pe Pf Pg Po Pz Qb) Mq(aA Fr Hq Hu Hv Hx Ih Ii Ik Il In Io Iq Is Iu Iv Jg Jh Jj Jk Jl Jm Jn Jo Jq Jr Js Jt Lh Lu Lv Lw Lx Ly Mb Md Me Mf Mg Mi Mj Mk Ml Mm Mn Mp Mr Mt Mv Mw Mx Mz Na Nb Nd Ne Nf Nh Ni Nk Nl Nm Nn No Nq Ns Nt Nu Nv Nw Nx Ny Oe Oi Om On Oz Pa Pc Pd Pe Pf Pg Po Pz Qb) Ni(aA Fr Hq Hu Hv Hx Ih Ik Il In Io Iq Is Iu Iv Jg Jh Jj Jk Jl Jm Jn Jo Jq Jr Js Jt Lh Lu Lv Lw Lx Ly Mb Md Me Mf Mg Mi Mj Mk Ml Mm Mn Mp Mr Mt Mu Mv Mw Mx Na Nb Nd Ne Nf Ng Nh Nk Nl Nm Nn No Nq Ns Nt Nu Nv Nw Nx Ny Oe Oi Om On Oz Pa Pc Pd Pe Pf Pg Po Pz Qb) Iu(aA Fr Hq Hu Hv Hx Ih Ii Ik Il In Io Ip Iq Is Iv Jg Jh Jj Jk Jl Jm Jn Jo Jq Jr Js Jt Lh Lv Lw Lx Ly Mb Md Me Mf Mg Mi Mj Mk Ml Mm Mn Mp Mr Mt Mu Mv Mw Mx Na Nb Nd Ne Nf Nh Nk Nl Nm Nn No Nq Ns Nt Nu Nv Nw Nx Ny Oe Oi Om On Oz Pa Pc Pd Pe Pf Pg Po Pz Qb) Pf(aA aO Fr Hq Hu Hv Hx Ii Ij Ik Il In Io Ip Iq Is Iv Jg Jh Jk Jl Jm Jn Jo Jq Jr Js Jt Lh Lv Lw Lx Ly Mb Md Me Mf Mg Mi Mj Mk Ml Mm Mn Mp Mr Mt Mu Mv Mw Mx Na Nb Nd Ne Nf Nh Nk Nl Nm Nn No Nq Ns Nt Nu Nv Nw Nx Ny Oe Oi Om On Oz Pa Pc Pd Pe Pg Po Pz Qb) Mi(aA Fr Hq Hu Hv Hx Ih Ii Ik Il In Io Ip Iq Is Iv Jg Jh Jj Jk Jl Jm Jn Jo Jq Jr Js Jt Lh Lv Lw Lx Ly Mb Md Me Mf Mg Mj Mk Ml Mm Mn Mp Mr Mt Mu Mw Mx Na Nb Nd Ne Nf Nh Nk Nl Nm Nn No Nq Ns Nt Nu Nv Nw Nx Ny Oe Oi Om On Oz Pa Pc Pd Pe Pg Po Pz Qb) Na(aA Fr Hq Hu Hv Hx Ih Ii Ik Il In Io Iq Is Iv Jg Jh Jj Jk Jl Jm Jn Jo Jq Jr Js Jt Lh Lu Lv Lw Lx Ly Mb Md Me Mf Mg Mj Mk Ml Mm Mn Mp Mr Mt Mv Mw Mx Mz Nb Nc Nd Ne Nf Ng Nh Nk Nl Nm Nn No Nq Ns Nt Nu Nv Ny Oe Om On Oz Pa Pc Pd Pe Pg Po Pz Qb) Iq(aA Aj Fr Hq Hu Hv Hx Ih Ii Ij In Io Ip Is Iv Jg Jh Jk Jl Jm Jn Jo Jq Jr Js Jt Lh Lv Lw Lx Ly Mb Md Me Mf Mg Mj Mk Ml Mm Mn Mp Mr Mt Mu Mv Mw Mx Nb Nd Ne Nf Nh Nk Nl Nm Nn No Nq Ns Nt Nu Nv Nw Nx Ny Oe Oi Om On Oz Pa Pc Pd Pe Pg Po Pz Qb) Po(aA Fr Hq Hu Hv Hx Ih Ii Ik Il In Io Ip Is Iv Jg Jk Jl Jm Jn Jo Jq Jr Js Jt Lh Lu Lv Lw Lx Ly Mb Md Me Mf Mg Mj Mk Ml Mm Mn Mp Mr Mt Mu Mx Mz Nb Nd Ne Nf Nh Nk Nl Nm Nn No Nq Ns Nt Nu Nv Nw Nx Ny Oe Oi Om On Oz Pa Pc Pd Pe Pg Pz Qb) Nh(aA Fr Hq Hu Hv Hx Ii Ij Ik Il In Io Ip Is Iv Jg Jh Jj Jk Jl Jm Jn Jo Jq Jr Js Jt Lh Lv Lw Lx Ly Mb Md Me Mf Mg Mj Mk Ml Mm Mn Mp Mr Mt Mu Mv Mw Nb Nd Ne Nf Nk Nm Nn No Nq Ns Nt Nu Nv Nw Nx Ny Oe Oi Om On Oz Pa Pc Pd Pe Pg Pz Qb) Il(Aj Fr Hq Hu Hv Hx Ii Ij Ik In Io Ip Is Iv Jg Jh Jk Jl Jm Jo Jq Jr Js Jt Lh Lu Lv Lw Lx Ly Mb Md Me Mf Mg Mj Mk Ml Mm Mn Mp Mr Mt Mu Mv Mw Nb Nc Nd Ne Nf Nk Nl Nm Nn No Nq Ns Nt Nu Nv Nw Nx Ny Oi Om On Oz Pa Pc Pd Pe Pg Pz Qb) aA(Fr Hq Hu Hv Ih Ii Ik In Io Ip Ir Is Iv Jg Jj Jk Jl Jn Jo Jq Jr Js Jt Lh Lv Lw Lx Ly Mb Md Me Mf Mg Mj Mk Ml Mm Mn Mp Mr Mt Mu Mv Mw Mx Nb Nc Nd Ne Nf Nk Nl Nm Nn No Nq Ns Nt Nu Nv Nw Nx Ny Oi Ok Om On Oz Pa Pc Pd Pe Pg Pz Qb) On(Fr Hq Hu Hv Hx Ih Ii Ik In Io Ip Is Iv Jg Jk Jl Jm Jn Jo Jq Jr Js Jt Lh Lu Lv Lw Lx Ly Mb Md Me Mf Mg Mj Mk Ml Mm Mn Mr Mt Mu Mx Mz Nb Nc Nd Ne Nf Nk Nl Nm Nn No Nq Ns Nt Nu Nv Nw Nx Ny Oe Oi Om Oz Pa Pc Pd Pe Pg Pz Qb) Pa(Fr Hq Hu Hv Hx Ih Ii Ik In Io Is Iv Jg Jh Jj Jk Jl Jm Jn Jo Jq Jr Js Jt Lh Lu Lv Lw Lx Ly Mb Md Me Mf Mg Mj Mk Ml Mm Mn Mp Mr Mt Mv Mw Mx Mz Nb Nd Ne Nf Nk Nl Nm Nn No Nq Ns Nt Nu Nw Nx Ny Oe Om Oz Pc Pd Pe Pg Pz Qb) Mm(Fr Hq Hu Hv Hx Ii Ik In Io Ip Is Iv Jg Jh Jk Jl Jm Jn Jo Jq Jr Js Jt Lh Lv Lw Lx Ly Mb Md Me Mf Mg Mj Mk Ml Mn Mp Mr Mt Mu Mv Mw Nb Nd Ne Nf Nk Nl Nm Nn No Nq Ns Nt Nu Nv Nw Nx Ny Oe Oi Om Oz Pc Pd Pe Pg Pz Qb) Nk(Fr Hq Hu Hv Hx Ih Ii Ik In Io Is Iv Jg Jh Jj Jk Jl Jm Jn Jo Jq Jr Js Jt Lh Lu Lv Lw Lx Ly Mb Me Mf Mg Mj Mk Ml Mn Mp Mr Mt Mv Mw Mx Nb Nd Ne Nf Ng Nl Nm Nn No Nq Ns Nt Nu Nw Nx Ny Oe Om Oz Pc Pd Pe Pg Pz Qb) In(Fr Hq Hu Hv Hx Ii Ij Ik Io Is Iv Jg Jh Jj Jk Jl Jn Jo Jq Jr Js Jt Lh Lu Lv Lw Lx Ly Mb Md Me Mf Mg Mj Mk Ml Mn Mp Mr Mt Mv Mw Mz Nb Nd Ne Nf Ng Nl Nm Nn No Nq Ns Nt Nu Nv Nw Nx Ny Oe Om Oz Pc Pd Pe Pz Qb) Mg(Fr Hq Hu Hv Hx Ii Ij Ik Io Ip Iv Jg Jh Jj Jk Jl Jo Jq Jr Js Lh Lv Lw Lx Ly Mb Md Me Mf Mj Mk Ml Mn Mp Mr Mt Mu Mv Mw Nb Nd Ne Nf Ng Nl Nm Nn No Nq Ns Nt Nu Nv Nw Nx Ny Oe Oi Om Oz Pc Pd Pe Pg Pz Qb) Mk(Fr Hq Hu Hv Hx Ii Ij Ik Io Ip Iv Jg Jh Jj Jk Jl Jm Jn Jo Jq Jr Js Jt Lh Lv Lw Ly Mb Md Me Mf Mj Ml Mn Mp Mr Mu Mv Mw Nb Nd Ne Nf Ng Nl Nm Nn No Nq Ns Nt Nu Nv Nw Nx Ny Oe Oi Om Oz Pc Pd Pe Pg Pz) Mn(Fr Hq Hu Hv Hx Ih Ik Io Is Iv Jg Jh Jj Jk Jl Jm Jn Jo Jq Jr Js Jt Lh Lu Lv Lw Lx Ly Mb Md Me Mf Mj Ml Mp Mr Mt Mv Mw Mx Nb Nd Ne Nf Nl Nm Nn No Nq Ns Nt Nu Nv Nw Nx Ny Oe Oz Pc Pd Pe Pg Pz Qb) Mr(aO Fr Hq Hu Hv Ih Ij Ik Io Ip Is Iv Jg Jk Jl Jm Jn Jo Jq Jr Js Jt Lh Lv Lw Lx Ly Mb Md Me

Figure 33 Continued

Mf Mj Ml Mp Mt Mu Mx Nb Nd Ne Nf Nl Nm Nn No Nq Ns Nt Nu Nv Nw Nx Ny Oe Oi Om Oz Pc Pd Pe Pg Pz Qb) Nd(Fr Hq Hu Hv Hx Ii Ij
Ik Io Ip Is Iv Jg Jh Jk Jl Jm Jn Jo Jq Jr Js Jt Lh Lv Lw Lx Ly Md Me Mf Mj Ml Mp Mt Mu Mv Mw Nb Ne Nf Nm Nn No Nq Ns Nt Nu Nv Nw
Nx Ny Oe Oi Om Oz Pc Pd Pe Pg Pz Qb) Jg(Fr Hq Hu Hv Hx Ih Ii Ik Io Is Iv Jj Jk Jl Jm Jn Jo Jq Jr Js Jt Lh Lu Lv Lw Lx Ly Mb Md Me Mf Mj
Ml Mp Mt Mx Mz Nb Nc Ne Nf Nl Nm Nn No Nq Ns Nt Nu Nw Nx Ny Oe Om Oz Pc Pd Pe Pg Pz Qb) Ip(Fr Hq Hu Hv Hx Ih Ik Io Is Iv Jh Jj
Jk Jl Jm Jn Jo Jq Jr Js Jt Lh Lu Lv Lw Lx Ly Mb Me Mf Ml Mp Mt Mv Mw Mx Mz Nb Nc Ne Nf Ng Nl Nm Nn No Nq Ns Nt Nu Nw Nx Ny
Oe Oz Pc Pd Pe Pz Qb) Md(Fr Hq Hu Hv Hx Ih Ii Ik Io Is Iv Jh Jj Jk Jl Jm Jn Jo Jq Jr Js Jt Lh Lu Lv Lw Lx Ly Mb Me Mf Ml Mp Mt Mv Mw
Nb Nc Ne Nf Nl Nm Nn No Nq Ns Nt Nu Nw Nx Ny Oe Om Oz Pc Pd Pe Pz Qb) Nv(Fr Hq Hu Hv Hx Ih Ii Ik Io Is Iv Jh Jj Jk Jm Jn Jo Jq Jr Js
Jt Lh Lu Lv Lw Lx Ly Mb Me Mf Ml Mp Mt Mv Mw Mz Nb Nc Ne Nf Nl Nm Nn No Nq Ns Nt Nu Nw Nx Ny Oe Oz Pc Pd Pe Pg Pz Qb)
Oi(Hq Hu Hv Hx Ih Ik Io Is Iv Jh Jj Jk Jl Jm Jn Jo Jq Jr Js Jt Lh Lu Lv Lw Lx Ly Mb Me Mf Ml Mp Mt Mv Mw Mx Mz Nb Nc Ne Nf Nl Nm
Nn No Nq Ns Nt Nu Nw Nx Ny Oe Oz Pc Pd Pe Pz Qb) Mu(Fr Hq Hv Hx Ih Ii Ik Io Is Iv Jh Jj Jk Jl Jm Jn Jo Jq Jr Js Jt Lh Lu Lv Lw Lx Ly Mb
Me Mf Ml Mp Mt Mx Mz Nb Nc Ne Nf Nl Nm Nn No Nq Ns Nt Nu Nw Nx Ny Oe Oz Pc Pd Pe Pz Qb) Ij(Fr Hq Hu Hv Hx Ih Ii Ik Io Is Iv Jj Jk
Jl Jm Jn Jo Jq Jr Js Jt Lh Lu Lv Lw Lx Ly Mb Me Mf Ml Mp Mt Mv Mw Mx Nb Nc Ne Nf Nl Nm Nn No Nq Ns Nt Nu Nw Ny Oz Pc Pd Pe Pz
Qb Qd) Lj(Aa aF aH aK aM aN Ao aP aU aW bL bM bO bQ bZ cA cB cD Ch cI Co cR cX cZ dA dB DD dI eC Ef Gl Hb Hc hG iA Ib Ic Id iJ
iO Iz Jv Kc Kk Kl Ou pF Ph Pj Qw Qz Rf Rg Vt Vv Wm) Pg(Fr Hq Hu Hv Hx Ii Ik Io Is Iv Jh Jj Jk Jl Jm Jn Jo Jq Jr Js Jt Lh Lu Lv Lw Lx Ly
Mb Me Mf Ml Mp Mt Mv Mw Mz Nb Ne Nf Nl Nm Nn No Nq Ns Nt Nu Nw Nx Ny Oe Oz Pc Pd Pe Pz Qb) Mj(Hq Hu Hv Hx Ik Io Iv Jh Jj Jk
Jl Jm Jn Jo Jq Jr Js Jt Lh Lu Lv Lw Lx Ly Mb Me Mf Ml Mp Mt Mv Mw Nb Nc Ne Nf Ng Nl Nm Nn No Nq Ns Nt Nu Nw Nx Ny Oe Oz Pc Pd
Pe Pz Qb) Om(Hq Hu Hv Hx Ib Ih Ik Io Iv Jh Jj Jk Jl Jm Jn Jo Jr Js Lh Lu Lv Lw Lx Ly Mb Me Mf Ml Mp Mt Mv Mw Nb Nc Ne Nf Ng Nl Nm
Nn No Nq Ns Nt Nu Nw Nx Ny Oe Oz Pc Pd Pe Pz Qb) Fr(Hq Hu Hv Hx Ik Io Is Iv Jh Jj Jk Jm Jn Jo Jq Jr Js Jt Lh Lv Lw Lx Ly Mb Me Mf Ml
Mp Mt Mv Mw Nb Ne Nf Nl Nm Nn No Nq Ns Nt Nu Nw Nx Ny Oe Oz Pc Pd Pe Pz Qb) Nx(Hq Hu Hv Hx Ii Ik Io Is Iv Jk Jl Jm Jn Jo Jq Jr Js
Jt Lh Lv Lw Lx Ly Mb Me Mf Ml Mp Mt Mv Mw Nb Ne Nf Nl Nm Nn No Nq Ns Nt Nu Nw Ny Oz Pc Pd Pe Pz Qb) Hq(Hu Hv Hx Ii Ik Io Iv
Jh Jj Jk Jo Jq Jr Js Jt Lh Lv Lw Lx Ly Mb Me Mf Ml Mp Mt Mv Mw Nb Ne Nf Ng Nl Nm Nn No Nq Ns Nt Nu Nw Ny Oe Oz Pc Pd Pe Pz)
Ii(Hu Hv Hx Ik Io Iv Jh Jj Jn Jo Jq Jr Js Lu Lv Lw Lx Ly Mb Me Mf Ml Mp Mt Mv Mw My Nb Ne Nf Ng Nl Nm Nn No Nq Ns Nt Nu Nw Ny
Oe Oz Pc Pd Pz Qb) Pd(Hu Hv Hx Ik Io Iv Jk Jm Jn Jo Jq Jr Js Jt Lh Lv Lw Lx Ly Mb Me Mf Ml Mp Mt Mv Mw Nb Ne Nf Nl Nm Nn No Nq
Ns Nt Nu Nw Ny Oe Oz Pc Pe Pz Qb) Pe(Aj aO Hu Hv Ib Ik Io Is Iv Jk Jl Jm Jn Jo Jq Jr Js Jt Lh Lv Lw Lx Ly Mb Me Mf Ml Mt Mx Ne Nf Nl
Nm Nn No Nq Ns Nt Nu Nw Oe Oz Pc Pz Qb) Aj(aC Ad aF aG aI aK aL aM aN AO aQ Ar Ax bC bW cA cB cD cI cR Cs Cu Cv cX cZ dA dB
dI dK Hx Im Is Ji Jm Jt Lw Lz Mt Mz Nm Qa Qd) Ly(Hu Hv Hx Ik Io Iv Jl Jm Jn Jo Jq Jr Js Jt Lh Lv Lw Lx Mb Me Mf Ml Mp Mt Mv Mw Nb
Ne Nf Nl Nm No Nq Ns Nt Nu Nw Ny Oz Pc Pz Qb) Nf(Hu Hv Hx Ik Io Iv Jh Jj Jk Jo Jq Js Jt Lh Lv Lw Lx Mb Me Mf Ml Mp Mt Mv Mw Nb
Ne Nl Nm No Nq Ns Nt Nu Nw Ny Oe Oz Pc Pz Vt) Js(Hu Hv Ih Ik Io Is Iv Jk Jl Jm Jn Jq Jr Jt Lh Lv Lw Lx Mb Me Mf Ml Mt Mx Nb Ne Nl
Nm Nn No Nq Ns Nt Nu Nw Ny Oz Pc Pz Qb) Aa(Hu Hx Im Io It Iv Ji Jj Jr Li Lu Lw Lx Me Mf Mh Ml Mp Mt My Mz Nb Nc Ne Nj Nl Nn No
Nq Oe Of Og Ok Oy Oz Pc Pz Qa Qb) Jk(Hu Hv Hx Ik Io Iv Jh Jj Jo Jq Jr Jt Lh Lv Lw Lx Mb Me Mf Ml Mp Mv Mw Nb Ne Nl Nm No Nq Ns
Nt Nu Nw Ny Oe Oz Pz) Nm(Hu Hv Hx Ik Io Iv Jl Jo Jq Jr Jt Lh Lv Lw Lx Mb Me Mf Ml Mp Mt Mv Mw Nb Ne Nl No Nq Ns Nt Nu Ny
Oe Oz Pc Pz) Nt(Hu Hv Hx Ik Io Iv Jl Jm Jn Jq Jr Jt Lh Lv Lw Lx Mb Me Mf Ml Mp Mt Nb Ne Nl Nn No Nq Ns Nu Nw Ny Oz Pc Qb) Lv(Hu
Hv Hx Ik Io Is Iv Jl Jo Jq Jr Jt Lh Lw Lx Mb Me Mf Ml Mp Mt Nb Ne No Nq Ns Nu Nw Ny Oe Oz Pc Pz Qb) Ik(Hu Hv Hx Io Iv Jm Jo Jq Jt Lh
Lw Lx Me Mf Ml Mp Mt Mv Mw Nb Ne No Nq Ns Nu Nw Ny Oz Pc Pz Qb) Lh(Hu Hv Ib Io Iv Jl Jm Jn Jq Jr Jt Lx Mb Me Mf Ml Mt Nb Ne
Nl Nn No Nq Ns Nu Nw Ny Oz Pc Qb) Nb(Hu Hv Hx Io Iv Jo Jq Jr Jt Lw Lx Mb Me Mf Ml Mp Mt Ne Nn No Nq Ns Nu Nw Ny Oe Oz Pc)
Hv(Hu Hx Io Iv Jm Jo Jq Jt Lw Mb Me Mf Ml Mp Mv Mw Ne Nn No Nq Ns Nu Ny Oe Oz Pc Pz) Qe(aC aF aH aK aN Ao Ap bL bM bQ cA
cD Ch cI Co cS Ct dB Dg dI Dk dN Ef Gl Ib Qw Vt) Io(Hu Hx Iv Jl Jo Jq Jt Lw Lx Mb Me Mf Ml Mp Mv Mw Ne No Nq Ns Nu Ny Oe Oz Pc
Pz) Jq(Hu Is Iv Jl Jn Jo Jr Jt Lw Lx Me Mf Ml Mt Ne No Nq Ns Nu Nw Ny Oz Pc Pz Qb) No(Hu Ih Iv Jl Jo Jr Jt Lw Lx Me Mf Ml Mt Ne Nn
Ns Nu Nw Ny Oz Pc Pz Qb) Li(aC aF aH aM aN Ao bL bM bQ cA cD Ch cI cM Co Ct dB Dd dI Ef Ib Qw Vt) Mf(Hx Iv Jm Jo Jt Lw Lx Mb
Me Ml Mp Mt Mw Ne Nq Ns Nu Ny Oz Pc Qb) Hu(Hx Id Iv Jh Jo Jr Mb Me Ml Mp Mv Mw Ne Nq Ns Nu Ny Oe Oz Pc Pz) Ji(aC aF aH aN
Ao Ax bL bM bQ cD cI cM Co Cs dB dI Dk Ef Ib Iz Wm) aO(aC Ar Ax bM cI Cs dH dI Ir Is Lw Lx Lz Mt Mz Nw Og Or Vt) Ne(Hx Iv Jo Jr
Lx Mb Me Ml Mp Mt Mw Nl Nq Ns Nu Ny Pc Pz) Iv(Hx Jm Jn Jo Jr Jt Lx Mb Me Ml Mt Ns Nu Ny Oz Pc Qb) Nq(Cs Hx Jh Jo Mb Me Ml Mv
Mw Nl Ns Nu Oe Oz Pc Pz) Jo(Hx Jh Jj Mb Me Mp Mt Mv Mw Ns Nw Oe Oz Pc Pz) Ch(aC aH bM cA cI cM Cs Dc Dd dI Id Ir Jd Or) Me(Jr Jt
Lx Mb Ml Mp Mt Ns Nu Ny Oz Pc Pz) Ib(Ax Cq Cs Dc Dd Fa Id Ir Kn Kq Qa Us Vt) Jj(aC aF aG aH Ax cA cI cM Cs dB Dd dI Or) Nu(Hx Jr
Jt Lw Lx Ml Mp Mt Nl Ny) aC(aF aH aI aL cM Cs cZ Ir Lz Vt) Ns(Hx Jm Ml Mp Mv Mw Ny Oz Pc) cM(Ax bM cI Cs Ef Id Iz Or) Pc(Jr Jt Mp
Mw Ny Oz Pz) Dc(Ct Ef Iz Uc Uu Vv) Qb(Ih Jm Lx Mt Nn Nw) Cs(Ic Qw Vt Vv) Ny(Jt Mt Nn Oz) Lz(bQ cI Dd) Mv(Jh Mw Pz) Or(aF bQ Iz)
Vt(Ax bL cI) Oz(Jt Mp Pz) Lx(Mt Nw) Ml(Mb Mp) aM(dK Ir) Axlc LwJt MtNw MwJh NcNl ldRg IzKq PzOe} Ok{Hu(AA Fr Hq Hr Hv Hw
Hx Ih Ii Ik Il In Io Ip Iq Is Iu Iv Jg Jh Jk Jl Jm Jn Jo Jp Jq Jr Js Jt Lh Lv Lw Lx Ly Ma Mb Mc Md Me Mf Mg Mh Mi Mj Mk Ml Mm Mn Mp
Mq Mr Mt Mv Mw My Mz Na Nb Nc Nd Ne Nf Ng Nh Ni Nk Nl Nm Nn No Nq Nr Ns Nt Nu Nv Nw Nx Ny Oe Oh Oi Om On Oy Oz Pa Pc Pd
Pe Pf Pg Po Pz Qb Qc Qd) Qb(aA Fr Hq Hr Hv Hw Hx Ih Ii Ij Ik Il In Io Ip Iq Ir Is Iu Iv Jg Jh Jk Jl Jm Jn Jo Jp Jq Jr Js Jt Lh Lv Lw Lx Ly Ma
Mb Mc Md Me Mf Mg Mh Mi Mj Mk Ml Mm Mn Mq Mr Mt Mu Mv Mw Mx Mz Na Nb Nc Nd Ne Nf Nh Ni Nk Nl Nm Nn No Nq Nr Ns Nt
Nu Nv Nw Nx Ny Oh Oi Om On Oz Pa Pc Pd Pe Pf Pg Po Pz Qa Qc Qd) Jr(Fr Hq Hr Hv Hw Hx Ih Ii Ik Il In Io Ip Iq Is Iu Iv Jg Jh Jk Jl Jm Jn
Jo Jp Jq Js Jt Lh Lu Lv Lw Lx Ly Ma Mb Mc Md Me Mf Mg Mh Mi Mj Mk Ml Mm Mn Mp Mq Mr Mt Mu Mv Mw Mx Mz Na Nb Nc Nd Ne
Nf Ng Nh Ni Nk Nl Nm Nn No Nq Nr Ns Nt Nu Nv Nw Nx Ny Oe Oh Oi Om On Oz Pc Pd Pe Pf Pg Po Pz Qa Qc Qd) Jm(aA Fr Hq Hr Hv Hw
Hx Ih Ij Ik Il In Io Ip Iq Ir Is Iu Iv Jg Jh Jk Jl Jn Jp Jq Js Jt Lh Lv Lw Lx Ly Ma Mb Mc Md Me Mf Mg Mh Mi Mj Mk Ml Mm Mn Mq Mr Mt
Mu Mv Mw Mx Mz Na Nb Nc Nd Ne Nf Nh Ni Nk Nl Nm Nn No Nq Nr Ns Nt Nu Nv Nw Nx Ny Oh Oi Om On Oz Pa Pc Pd Pe Pf Pg Po Pz
Qa Qc Qd) Lv(AA Fr Hq Hr Hv Hw Hx Ih Ii Ik Il In Io Ip Iq Is Iu Iv Jh Jk Jl Jn Jo Jp Jq Js Jt Lh Lw Lx Ly Ma Mb Mc Md Me Mf Mg Mh Mi Mj
Mk Ml Mm Mn Mq Mr Mt Mu Mv Mw Mx Mz Na Nb Nd Ne Nf Nh Ni Nk Nl Nm Nn No Nq Nr Ns Nt Nu Nv Nw Nx Ny Oe Oh Oi Om On
Oz Pa Pc Pd Pe Pf Pg Po Pz Qa Qc Qd) Me(AA Fr Hq Hr Hv Hw Hx Ih Ii Ij Ik Il In Ip Iq Is Iu Iv Jg Jh Jk Jl Jn Jo Jp Jq Js Jt Lh Lv Lw Lx Ly Ma
Mb Mc Md Mf Mg Mi Mj Mk Ml Mm Mn Mq Mr Mt Mu Mv Mw Mx Mz Na Nb Nc Nd Ne Nf Nh Ni Nk Nl Nm Nn No Nq Nr Ns Nt Nu Nv Nx
Ny Oe Oh Oi Om On Oz Pa Pc Pd Pe Pf Pg Po Pz Qa Qc Qd) Jn(aA Fr Hq Hr Hv Hw Hx Ih Ii Ij Ik Il In Io Ip Iq Ir Is Iu Iv Jg Jk Jl Jp Jq Js Jt Lh
Lw Lx Ly Ma Mb Mc Md Mf Mg Mh Mi Mj Mk Ml Mn Mq Mr Mt Mu Mv Mw Mx Mz Na Nb Nd Ne Nf Nh Ni Nk Nl Nm Nn No Nq Nr Ns
Nt Nu Nv Nw Nx Ny Oe Oh Oi Om On Oz Pa Pc Pd Pe Pf Pg Po Qa Qc Qd) Jt(Aj Fr Hq Hr Hv Hw Hx Ih Ii Ik Il In Io Ip Iq Ir Is Iu Iv Jg Jk
Jl Jp Jq Js Lh Lw Lx Ly Ma Mb Mc Md Mf Mg Mh Mi Mj Mk Ml Mm Mn Mq Mr Mt Mu Mv Mw Mx Mz Na Nb Nc Nd Ne Nf Nh Ni Nk Nl
Nm Nn No Nq Nr Ns Nt Nu Nv Nw Nx Ny Oe Oh Oi Om On Oz Pa Pc Pd Pe Pf Pg Po Qa Qc Qd) Lh(aA Fr Hq Hr Hv Hw Hx Ih Ij Ik Il In Io Ip
Iq Ir Is Iu Iv Jg Jk Jl Jo Jp Jq Js Lw Lx Ly Ma Mb Mc Md Mf Mg Mh Mi Mj Mk Ml Mm Mn Mq Mr Mt Mu Mv Mz Na Nc Nd Ne Nf Nh Ni Nk

Pz Qb Qc) Mw(Fr Hq Hr Hv Hw Hx Ii Ij Il In Io Ip Iq Iu Iv Jk Jm Jo Jr Js Ly Ma Mb Mc Md Me Mf Mg Mh Mi Mj Mk Ml Mn Mq Mr Mt Mv My Na Nb Nd Nh Ni Nk No Nr Ns Nt Nu Nv Nx Oe Oh Oi Om Oy Oz Pa Pc Pd Pe Pf Pg Po Pz Qb Qc) Ik(Aa Fr Hq Hr Hv Hw Hx Ii Ij Il Io Ip Iu Jg Jk Jm Jo Jq Jr Js Lx Ly Ma Mc Md Me Mf Mg Mi Mj Mk Ml Mn Mq Mr Mt Mu Na Nb Nd Nh Ni Nk No Nr Ns Nu Nv Nx Oe Oh Oi Om On Oz Pa Pc Pd Pe Pf Pg Pj Pk Po Pz Qb Qc) Qa(Fr Hr Hv Hw Ii Ij Il Io Ip Iq Iu Iv Jg Jl Jm Jo Jq Jr Js Lx Ly Ma Mb Mc Md Me Mf Mg Mh Mi Ml Mn Mq Mr Mt Mu Mz Na Nb Nd Nh Ni Nk No Nr Ns Nt Nu Nv Nx Oh Oi Om On Oz Pa Pc Pd Pe Pf Pg Po Pz Qb Qc Qd Qw) Mv(Fr Hq Hr Hv Hw Hx Ii Ij Il In Io Ip Iq Iu Iv Jk Jm Jo Jr Js Ly Ma Mb Mc Md Me Mf Mg Mh Mi Mj Mk Ml Mn Mq Mr My Na Nb Nd Nh Ni Nk No Nr Ns Nu Nv Nx Oe Oh Oi Om Oy Oz Pa Pc Pd Pe Pf Pg Po Pz Qb Qc) Lw(Aa aC Aj aN bQ cD CO Fr Hr Hv Hw Ii Ij Il Io Ip Iq Iu Jg Jm Jo Jq Jr Js Lx Ly Ma Mc Md Me Mf Mg Mi Ml Mn Mq Mr Mt Mu Na Nb Nd Nh Ni Nk No Nr Nt Nu Nv Nx Oe Oh Oi On Pa Pd Pe Pf Pg Po Qb Qc) Jp(aC Aj aN aO bM bQ Hc Hr Hw Id Ii Ij In Ip Iq Iu Iv Jd Jg Jo Js Jv Lx Mc Md Mg Mi Ml Mn Mq Mr Mt Mu Na Nb Nd Nh Ni Nk No Nr Nt Nv Nx Oh Oi Om On Pa Pd Pe Pf Pg Pj Pk Po Qb Qc Qt Qu Ua Vs Vt Vv) Mz(Fr Hq Hr Hv Hw In Io Ip Iq Iu Iv Jg Jk Jm Jo Jq Jr Js Lx Ly Ma Mb Mc Md Me Mf Mg Mi Mk Mn Mq Mr Mt Mu Na Nb Nd Nh Ni Nk No Nr Ns Nt Nu Nv Nx Oe Oh Oi On Oz Pa Pc Pd Pe Pf Pg Po Pz Qb Qc Qw) Qd(Fr Hq Hr Hv Hw Ii Ij In Io Ip Iq Iu Iv Jg Jm Jo Jq Jr Js Lx Ly Ma Mb Mc Md Me Mf Mg Mi Ml Mn Mq Mr Mt Mu Na Nb Nd Nh Ni Nk No Nr Ns Nt Nu Nv Nx Oh Oi Om On Oz Pa Pc Pd Pe Pf Pg Po Qb Qc) Mh(Aa Fr Hq Hv Hx Il In Io Ir It Iv Jg Jk Jm Jo Jq Jr Js Lj Lx Ly Mb Mc Md Me Mf Mi Mj Mk Ml Mn Mr Ms Mt Nb Nd Nh Ni Nk No Nr Ns Nt Nu Nv Nx Oe Of Oh Om On Oz Pc Pd Pe Po Pz Qb Qc) My(Fr Hq Hr Hv Hw Hx Ii Ij Il In Io Ip Iq Iu Jk Jm Jo Jr Js Ly Ma Mb Mc Md Mg Mi Mj Mk Ml Mn Mq Mr Na Nb Nd Nh Ni Nk No Nr Ns Nu Nv Oe Oh Oi Om Oy Oz Pa Pc Pd Pe Pf Pg Po Pz Qc) On(Fr Hq Hv Hx Ii Il In Io Ir Iu Iv Jk Jl Jm Jo Jq Jr Lx Ly Ma Mb Mc Md Me Mf Mg Mi Mj Mk Ml Mn Mr Mt Mu Nb Nd Nh Ni Nk No Nr Ns Nt Nu Nv Nx Oe Oh Oi Om Oz Pc Pd Pg Po Pz Qb Qc) It(Fr Hr Hv Hw Ii Ij Il Ip Iq Iu Iv Jg Jk Jm Jo Jq Jr Js Ly Ma Mb Mc Md Mf Mg Mi Ml Mn Mq Mr Mt Mu Na Nb Nd Nh Nk No Nr Nt Nu Nv Oe Oh Oi Om Oz Pa Pc Pd Pe Pf Pg Po Qb Qc) Jl(Hr Hw Ij In Io Ip Iq Iu Iv Jg Jm Jo Jq Jr Js Lx Ly Ma Mb Mc Md Me Mf Mg Mi Ml Mn Mq Mr Mt Mu Na Nd Nh Ni Nk No Ns Nt Nu Nx Oe Oh Oi Om Pa Pc Pd Pe Pf Pg Pz Qb Qc Qw) Of(Aa Fr Hq Hr Hv Hw Hx Ii Ij Il Io Ip Iq Iu Jk Jo Jr Js Lx Ma Mb Mc Md Mg Mi Mj Mk Ml Mn Mq Mr Mt Mu Na Nb Nd Ni Nk No Nr Ns Nu Oe Oh Oi Om Oz Pa Pc Pd Pe Pf Pg Po Qc) Ms(Aa Fr Hq Hr Hv Hw Ii Ij Il In Io Ip Iq Iu Jk Jo Ly Ma Mb Mc Md Mg Mi Mj Mk Ml Mn Mq Mr Mu Na Nb Nd Nh Ni Nk No Nr Ns Nu Nv Oe Oh Oi Om Pa Pc Pd Pe Pf Pg Po Pz Qc) Jj(Aa aN bM Cv Fr Hb Hq Hr Hw Ii Ij In Io Ip Iq Iu Jd Jk Jo Kf Lx Ma Mb Mc Md Mg Mi Ml Mn Mq Mr Mt Mu Na Nb Ni Nk No Nr Oe Oh Oi Om Pa Pe Pf Pg Pj Pz Qc Uh Vt) Jq(Fr Hq Hr Hv Hx Ii Ij Il In Io Ir Iv Jg Jk Jm Jo Jr Lx Ly Ma Mb Mc Md Me Mf Mg Mj Mk Ml Mn Mt Na Nb Nd Nh Ni Nk Ns Nt Nu Nv Nw Nx Oe Oh Om Oz Pc Pd Pg Po Pz Qb Qc) Lj(Fr Hq Hr Hv Hw Hx Ii Ij Io Ip Iq Iu Jd Jk Jm Jo Jr Js Lx Ma Mb Mc Md Mg Mi Mk Ml Mn Mq Mr Mu Na Nb Nk No Nr Ns Nv Oe Oh Oi Om Oz Pa Pc Pe Pf Pg Po Pz Qb Qc) Nt(Fr Hq Hv Hx Ii Il In Io Ir Iv Jk Jm Jo Jr Lx Ly Ma Mb Md Me Mf Mg Mj Mk Ml Mn Mt Nb Nd Nh Ni Nk Nr Ns Nv Nx Oe Oh Oi Om Oz Pc Pd Pg Po Pz Qb Qc) Vt(aC aF AJ aK aN aO aP Ar aS aU aV Ba bB bH bM bQ bU bX cA cC cD cl cV cX cY dB Dc DD dE dI dJ dK dL dN eF Hb Ib In Jd Pj Pk Qg Qw Qz Ti) In(Fr Hq Hv Hx Ii Il Io Ip Iv Jg Jk Jm Jr Js Lx Ly Ma Mb Me Mf Mi Mj Mk Ml Mn Mr Mt Nb Nd Nh Ni No Ns Nu Nv Nx Oe Oh Oz Pc Pd Pe Po Pz Qb) Ir(Fr Hr Hw Io Ip Iq Iu Jg Jm Jo Jr Lx Ma Mb Mc Md Mg Mi Ml Mn Mq Mr Mt Mu Na Nd Nh Ni Nk No Ns Nu Nv Nx Oh Oi Om Pa Pc Pd Pe Pf Pg Qb Qc) Iv(Fr Hq Hv Hx Il Io Ip Iq Iu Jg Jk Jm Jo Jr Lx Ly Mb Me Mf Mg Mi Mj Mk Ml Mn Mt Nd Nh Ni Nk No Ns Nu Nx Oe Oh Oi Oz Pc Pd Po Pz Qb Qc) Me(Fr Hq Hv Hx Il Io Jg Jk Jm Jo Jr Lx Ly Ma Mb Mf Mg Mi Mj Mk Ml Mn Mr Mt Nb Nd Nh Ni Nk No Ns Nu Nv Nx Oe Oi Oz Pc Pd Pe Pz Qb) Nj(Aa Fr Hr Hv Hw Ii Ij Il Ip Iq Iu Jg Jk Js Ly Ma Mb Mc Md Mf Mg Mi Ml Mn Mq Mr Mu Na Nb Nh No Nr Nv Oh Oi Om Pa Pe Pf Pg Po Qc) Mk(Hq Hv Hx Il Io Jg Jk Jm Jr Js Lx Ly Ma Mb Mf Mi Mj Mn Mr Mt Nb Nd Nh Ni No Ns Nu Nv Nx Oe Oz Pc Pd Pe Pf Po Pz Qb Qc) Oz(Hq Hv Hx Io Ip Jg Jk Jm Jo Jr Js Lx Ly Mb Mf Mj Ml Mn Mt Nd Nh Ni No Ns Nu Nv Nx Oe Pa Pc Pd Pe Pf Po Pz Qb) Mf(Fr Hq Hv Hx Il Io Jg Jk Jm Jo Jr Lx Ly Mb Mg Mi Mj Ml Mt Nd Nh Ni No Ns Nu Nx Oe Pc Pd Po Pz Qb Qc) Hx(Hv Jg Jk Jm Jo Jr Js Lx Ly Mb Mi Mj Mn Mr Mt Nd Nh Ni No Ns Nu Nv Nx Oe Pc Pd Pe Po Pz Qb Qc) Nx(Fr Hq Hv Io Jk Jm Jo Jr Lx Ly Mb Mj Ml Mn Mt Nd Nh Ni Nk No Ns Nu Oe Oh Pc Pd Po Pz) Oy(Fr Hr Hv Ii Ij Il Ip Iq Iu Jk Jo Ma Mb Mc Mg Ml Mq Na Nk No Nr Oe Oh Oi Om Pa) Mj(Aa Iq Jg Jm Jr Js Lx Ly Mb Mr Mt Nd Nh Ni No Ns Nu Nv Oe Pc Pd Pe Pz Qb Qc) Nh(Fr Hq Hv Io Jg Jk Jm Jr Lx Ly Mb Mn Mt Nd Ni Nk Ns Nu Oe Pc Pd Po Pz Qb) Pc(Hq Hv Il Io Jg Jk Jm Jo Jr Js Lx Ly Mb Mt Nd Ni Ns Nu Oe Pa Pd Pz Qb) Jg(Aj Fr Hq Hv Io Jk Jm Jo Jr Ma Mb Mg Nd Ni Ns Nw Oe Pd Po Pz Qb) Jk(Hv Jm Jr Js Lx Ly Mi Mr Mt Mu Nd No Ns Nu Oe Pd Pe Pz Qb Qc) Nw(aC Aj aN aO bM bQ cD Hr Hw Ij Ip Iq Js Pa Pe Pf Pk Qb) Nd(Fr Hq Hv Il Jm Jr Lx Ly Mb Mt Ni Ns Nu Oe Po Pz Qb) Jd(Aj Ba Ch Ef Ib Id Iz Jv Or Qt Qu Qw Qz Ua Uc Vs Vv) Ns(Hq Hv Jr Lx Ly Mb Mn Mt Ni No Nu Oe Pd Pz Qb) Jr(Hq Hv Jm Lx Ly Ni Nk Nu Oe Pd Po Pz Qb Qc) Im(Aa Ip Jm Js Md Mi Mn Mq Mr Na No Pa Qb) Mb(Aa Jm Lx Ly Mt Ni Nu Oe Pd Pz Qb Qc) Qw(Dc fP Hb Il Or Pj Qe Sr Uh Un Vu) Lx(Fr Hq Hv Io Ly Ml Ni Oe Po Pz) Pj(Aj cM fP hC iJ Jv Or Pk Qz Rg) Qb(Hq Hv Il Io Ni Nu Oe Pd Pz) Jm(Hq Hv Il Jo Ni Nu Oe Pd Pz) Mt(Fr Hq Hv Io Ni Oe Pz) Aj(Ap Bb Cv Dc Dg Qe) Nu(Hv Jo Ni Oe Pd Pz) Pd(Hq Hv Jo Po Pz) Il(Aa Oe Pe Qc) Or(bQ cM Hb Ti) Uh(aN iA Pk Rg) Ly(Hv Ni Oe) Mr(Ii Nb Po) Nk(aC aN bM) Pz(Hq Hv Ni) Qe(aN cM Ij) Pe(li Nb Po) Aa(Nb Og) Oc(Ni Nv) Pb(Ii Ij) cM(aN bM) DcUr TiPk GchC HvJs] Ji{bM(aA aD aE aF aG aH al aJ aL aM Ao aP aQ AR aS aU aV aW AX aY aZ bA bB bC bE bF bG bH bI bJ bL BN bO bP bQ bR bS bU bV bW bX bZ cA cB cC cD cE cF cG cH cI cK cL cN CO cQ cR cS Ct cU cV cW cX cY cZ dA dB dD dE dH dI dJ DK dL dN Ef Fp Fr Hq Hr Hv Hw Hx Ih Ii IJ Il Im In Io Ip Iq Is It Iu Iv Jg Jh Jk Jl Jm Jn Jp Jq Jr Js Jt Jv Ld Lh Lu Lv Lw Lx Ly Ma Mb Mc Md Me Mf Mg Mh Mi Mj Mk Ml Mm Mn Mq Mr Mt Mu Mv Mw Mx My Mz Na Nb Nc Nd Ne Ng Ni Nj Nl Nm Nn No Nq Nr Ns Nt Nu Nv Nw Nx Ny OE Of Og Oh Oi Om On Or Oy Oz Pa Pb Pc Pd Pe Pf Pk Qa Qb Qc Qd Qe Qt Qw Rg Uk Vs Vt Wm) aN(aD aE aG aH aI Aj aK aL aM Ao aP aQ Ar aS aU aV aW AX aZ bA bB bC bF bH bI bJ bL BN bO bQ bR bS bU bW bX bZ cA cB cC cE cF cG cH cI cJ cK cL cN CO cP cQ cR CS Ct cU cV cW cX cY cZ dA dB dD dE dH dI dJ DK dL dN Ef Fp Fr Gl Hq Hr Hu Hw Hx Ih Ii Ij Il Im In Io Ip Iq Is It Iu Iv Jh Jk Jl Jm Jn Jo Jp Jq Jr Jt Jv Lh Lu Lv Lw Lx Ly Ma Mc Md Me Mf Mg Mh Mi Mj Mk Ml Mm Mn Mq Mr Mt Mv Mw Mx My Mz Na Nb Nc Nd Ne Nf Ng Nh Ni Nj Nl Nm Nn No Nq Ns Nt Nu Nv Nw Nx Ny Of Og Oh Om On Oy Oz Pa Pb Pc Pd Pe Pf Pk Qa Qb Qc Qd Qw Rg Vs Vt Vv Wm) Gl(Ad AF AJ Al aM An AO Ap As aU aV AW Ax BA bB BC Bg bH bI Bn Bo bQ bU bW cA cC cD cG Ch cI cN Co CQ cR Cs Ct CU CV Cw CX cY Db Dc dD Dg Dl dJ DK DL dR Ed Fa Fp Fr Fw Hq Hv Hx Id Ih Ii IJ Il Im In Io Ip Iq Ir Is It Iu Jd Jh Jl Jm Jn Jo Jq Js Jt Lh Lu Lv Lw Lx Lz Ma Mc Md Me Mf Mh Mi Mj Mk Ml Mm Mp Mq Mt Mv Mw My Mz Na Nb Nc Nd Ne Nf Ng Ni Nj Nl Nm Nn No Nq Ns Nt Nv Nw Nx Ny Oe Of Og Oh Oi Om Or Oy Oz Pa Pb Pc Pd Pe Pf Pg Pk Po Pz Qa Qb Qc Qd Qt Qx Qz Ra Rf Rg Sf Ub Uh Uo Us Vv Wm Tj) Ch(aC Ad aE aF Aj aK aL aM AO Ar As aU aV aW Ax bB bC bL Bn Bo bW cA cC cD cl cM cN Cp cQ Cs Cu cV cX cZ dB Dc dD Dl dK dL dR Ed EF FP gL gP hB hC hF hG iA Id iH Ik In IO IP Iq Ir Is Iu iZ Jd Jg Jj Jp Jt Ju Jv KQ kR kS Lj Lw Lx Lz Mg Mp Ms Mt Nf Nh Nk Nm Nn nW nY oE oF oH oK oN Pc PF Pg Pk Po Pz Qa Qb Qc Qd Qg Qh Qw Qx Qz Ra Rc Rf Ri Sr Ss Ub Uc Ue Uf Ug Uh Un Uo Up Ur Us Uv Vs Vt Vv tF) Lj(aa AD aE aF aG aH AL aM AO aP aQ AR As aU aV AW AX aY aZ BA bB bC bE bF bG bH bI bJ bL BN bO bP bR bS bU bW bX bZ cA cB cC cE cF cG cH cI cK cL cN CO cQ cR cS Ct cU cV cW CX cY cZ dA dB dC dD dE dG dH dI dJ DK dL dN dR EF fP gL gP hB hC hG iA Ib Ic Id iH iO iP IZ Jd Ju Jv Kc kQ Ld nW nY oE oF oN Or Ou pF Pj Pk Qt Qz Rf Rg Rm Sf Sr Ub Uh Uk Ur Uv Vs Vt Vv Wm) Jj(Aa AD Af aJ Al An Ao AP aQ aR AS Aw aY aZ BA BB

Figure 33 Continued

Bc bE bF BG bH bJ BN Bo bP bR bS bU bV cB cE cF cG cH cJ cK cL cN CO CP CQ Cs CT CU CV CW CX cY dA Db dC Dd De dF DG Di
dJ Dk Dl dM dN dR eC Ex fP Fw GP hB hC hF Ib Id iH iO iP IZ Jd Ju Jv Kc Kf Kk kQ kR KS Kx Kz Ld nW nY oE oF oH oK oN Or Ou Pj
Qw Qz Rg Sr Uf Uh Uk Vt tF) aC(aE aF aH aI Aj aK aM Ao aQ Ar aV aW AX aZ BC bE bF bH bI bJ bL bO bQ bW bX bZ cA cB cC cD cE
cH cI cJ cN Co cR cX dA dB dE dH dI dJ DK dL Ef Fp Fr Hr Hu Hw Ii Ij Ik Il Im In Io Ip Iq Ir Is It Iu Jk Jo Jp Jq Jt Jv Lv Lw Lx Ly Lz Md Me
Mf Mj Mk Ml Mm Mp Mr Ms Mt Mv Mw My Mz Na Nb Nc Ne Nf Nh Ni Nj Nl Nm Nq Nu Nv Nw Of Og Oy Oz Pb Pd Pe Pf Pg Po Pz Qa Qc
Qd Qe Qw Vt) Vt(aD aE aG aH aI AJ aL aM An Ao aP aQ AR AS aU aV AW aX aY aZ BA bB BC bE bF BG bH bI bJ BN bO bP bQ bR bS
bU bV bW bX bZ cA cB cC cD cE cF cG cH cI cJ cK cL cN CO cP cQ cR CS cT cU cV cW cX cY cZ dA dB DC DD dE dF dG dH dI dJ DK
dL dM dN EF Fw Gp Hu Ib Ic Id In Iz Jd Jv Lz Mp Ms Nf Ou Qg Qw Qz Rg Wm Ti Th) cM(aE aF aH aL aM AO Ar aW Ax bL bQ bW cC cD
cN Co Cs Ct dB dE dH dI Dk dL Ed Ex FP gP hB hF Hu iA Id Ii Ik IO IP Iq Ir Iu Iz Jo Jq Ju Jv kQ kR Ld Ly Lz Ml Ms Mt My Nh Nk nW nY
oF oH oK Or Oy Oz Pb Pg Pk Po Pz Qa Qb Qc Qd Qt Qu Qw Qx Qz Rc Sr Ss Tn Tt Ua Uc Uk Uo Ur Us Ut Uu Vs Vv tF) Aj(aF aH aK aL aM
AO Ar As aU aV Ax BC bL Bn bQ bU bW bX cA cB cC cD cI cN cR Cs Cu Cv cZ dB Dc DD dE Dg dH dI DK dL Fp Hu Hx iJ Ik Il Im Io Ip
Iq Is Jg Jm Jp Jt Lw Ly Lz Mg Mp Mt Ne Nf Nh Nk Nm Oi Pd Pe Pf Pg Po Pz Qa Qb Qc Qd Qw Rg Vv Wm) Aa(Fp Hu Hv Hw Hx Ii Ij Ik Im
In Io It Iv Jg Jh Jk Jo Jp Jr Js Lh Lw Lx Ma Mb Mc Mh Mj Ml Mm Mn Mr Mt Mu Mv Mw Mx My Mz Na Nb Nc Ne Nf Ng Nh Ni Nj Nl Nm
Nn No Nq Ns Nu Nx Ny Oe Of Og Oh Om Oy Oz Pa Pb Pc Pd Pf Pg Po Pz Qa Qb Qc Qd) aO(aJ aK aM Ar As aU Ax bW bX cD cI cN Cs dB
dD dF dG dI dL dR EF Ex Fp gL gP hC Hu iJ Ik In IO Ip Ir Iu iZ Jo Jp Ju Jv Lw Lx Ly Lz Mp Mr Ms Mt Mz Nf Nh Ni Nk Nw oF Og Pe PF Po
Pz Qa Qb Qc Qd Qz Rg Uh Vs Vv Wm) Ax(aF aK aM Ao As Ba bL Bn bQ cC cD Co Ct dB Dk Ef Fp Fr Hu Hx Ib Ii IJ Ik Ip It Jo Js Ju Lw Lz
Mj Mk Ms Mv My Ne Nf Nh Nv Of Og Ou Oz Pb Pd Pe Pg Pk Po Pz Qe Qt Qx Qz Rc Rf Rg Sr Ss Ua Uh Uk Uo Ur Uu Uv Vs Wm) Nk(aE aF
aH aK aM Ao Ar aU aW bL cC cD cN Cs dB dH dI dL Ef gP hB hC hG Hr Hw iA iH IJ iO IP Iu Jk Jn Js kS Lh Lv Ma Mc Mg Mi Mk Mq Mr
Mu Na Ni Nq Nr Nv nW oE oF Oi oK ON Pa Pe PF Pk Rg Sf Wm) Wm(aF aK Ao Ar As aV Ba Bg cD Co Ct Dk Ef Fw Gp Hb Hc Hu Ib Ic Id
Ik Io Ir Jh Jp Jv Kc Kk Lz Mj Mk Mp Mt Mu Mx My Ne Nf Ng Nh Nq Og Ou Ow Pc Pg Pk Qe Qt Qx Rf Rg Sr Ss Ua Uc Uh Ur Uu Uv Vv)
Qw(aF aK aM Ao AS aU aW Ba Bg bL Bn bQ bV bW cA cB cC cD cI cN Co Cq Cv dB Dc Dd dE dH dI Dk dL Ed fP fR Fw Gp Ib Ic Il In Ir Iz
Jd Jp Kx Kz Lv Lz Ms Mt Mu Mx Nn Ou Pk Qa Qc Rg Sr Vu Vv) iJ(aF Ao Ar Ba Bg bL cD cI Co cR Cs dI Dk dL EF fP Fr Hc iA Ib Ii Ik Io Ir
iZ Jd Jh Jk Jo Lv Lz Mj Mk Mp Ms Mv Mw My Nb Nf Ng Nh Nv oE Of Og On Oy Oz pF Pg Pk Pz Qe Vv Yk) cD(aF aK aM Ao Ar aU aW
bW cA cB cI cN dB dD dH dI dL dR EF Fp gL Hu Ii Ik In Ip Ir Iu Jo Jp Jq Jv Lw Lx Lz Mp Ms Mt Nf Nh Nm Oy Oz Pb Pe Pf Po Pz Qa Qb Qc
Qd Rg Vv) Qe(aE aF aH aK AL aM Ao aP Ar AS aU aV aW aZ bC Bg bL Bn bO bQ bW bX bZ cA cB cC cE cF cI cO CS Ct cX cY cZ dB DD
dE dH dI dJ DK dL Ef Iz Jv Vs) Ef(Ad aF aK Ao Ar As aU aV BC bL Bn bW cA cC Cs Cv dB Dc Dd Dg dH dI Dl Hu Ik Im In Io Iq Ir Is Iu Jp
Jt Kq Lw Lz Ms Mt Nf Nh Nm Nn Oe Pa Pf Pk Qa Qd) Hu(aK aM Ar As aU Bn cI Cs dB dD dH dI dR eF Fa Fw gL GP hB hF hG iA iH Ij iO
iP Iz Jd Ju Jv Kk KQ kR kS Kx Kz Ld nW nY oE oF oH oK oN Or Ou Rg) Mp(aE aF aJ aK aM Ao As aU aV aW aX bA bC bL Bn bQ bW bX
cA cB cC cG cI cN cR Cs CU Cv dA dB Dc dD dE dG dI DK dL dR eF gL hC iZ Rg Sf) Vv(aF aK An Ao Ar As aW Ba Bc Bg bL Bo bQ bX
cC Co Cq Cs Cu Cv Dc Dd dH Di Dk DL Ed Fw Gp hC Ib Ic Id IZ Jp Jv Kc Kf Ld Pj Pk Rg) Rg(aF aK Ao Ar As aV Ba bF Bg bL Bn bX cC cE
Cs Cv Dc Dk dL Fw Gp Hc Ib Ic Id Ik In Ir Iz Jp Jv Mk Ou Pj Pk Qz Sr Uh) Pa(Ao Dk Fr Hr Hw Ih Ij Ip Iu Jk Jn Jr Js Lh Lv Ma Mc Mg Mi Mk
Mq Mr Mu Na Ni Nm No Nq Nr Nv oE Oi On Pf Sf Vu) Ar(aF aK Ao bQ Co Dk fP Fr hG Ib Ic Ik Iz Jd Ju Lw Ms Nf Nv oN pF Pg Pk Po Qg
Qt Qx Qz Rc Ss Ua Uk Uu Vs) Yk(dR gL hB hC hF hG iH iO iP iZ kF kN kO kP kQ kR kS lW lX mM mP mZ nA nR nT nW nY oE oF oH oK
oN pF Uu) Mq(Fr Hr Hw Ih Ij Ip Iu Jk Jn Jr Js Lh Lv Ma Mc Mg Mi Mk Mr Mu Na Nb Ni Nm No Nq Nr Nv Oi On Pd Pe Pf) dH(aG aH aK aM
Ao bL bZ cE cI CO dB Dk Fr iA Ik Iz Jo Lz Ms My Nh Nq Nv Of Og oN Oy Oz Pb pF Pg Vs) Na(Fr Hr Hw Ih Ij Ip Iu Jk Jn Jr Js Lh Lv Ma Mc
Mg Mi Mj Mk Mr Mu Nb Ni No Nq Nr Nv Oi On Pd Pe Pf) Nr(Fr Hr Hw Ih Ij Ip Iu Jk Jn Jr Js Lh Lv Ma Mc Mg Mi Mk Mr Mu Ni Nm No Nq
Nv Oi On Pd Pe Pf) Ik(aF aH aK aM Ao aU bL bQ bW cC cI cN Co Cs dB dI Dk dL Ex Fa Id Iz Jd Jv Kx Kz Ld Or pF Pj) Jv(aF aK Ao cI Cs
Cv dB Dc Fw Gp iA Ib Ic In Ir Jp Kc Kk Ko Kp Kx Ld Mc Ms Nh Ou Pj Pk) aK(aF aH aL aM cI Cs cY cZ dI dR eF Id Io Ir Iu iZ Jo kS Ly Lz
Ms oE Oz Pz Uv Vs) Js(Hr Hw Ij Ip Iu Jk Lh Lv Ma Mc Mg Mi Mj Mk Mu Nb Ni Nm No Nq Nv Oi On Pe Pf) Ij(aA Fr Hr Ip Iu Jk Lv Ma Mc
Md Mg Mi Mj Mk Mr Mu No Nq Nv Oh Oi On Pf) Nq(dR eF gL gP hC hG Hr Hw iH iO Ip iZ Jk Kq Ma Mc Mg Nv oF On pF) Ms(aF aM Ao
aU aV bL bQ bX cC cI Co dB dE Dk hG Ju nK oE pF Pk Qz) Ma(Hr Hw Ih Ip Jk Jn Lv Mc Mg Mi Mj Mr Mu Ni No Nv Oi On Pe Pf) aF(aM cI
dI dL eF Ex Fp hC Ir iZ Ju Ly Lz Nh Og Or Po Pz Qd Uh) Iz(As hC iA iH iO iZ Jd Jp Ju Kk Kq oN pF Qa Qz Sr Uc Uk Us) On(Hr Hw Ih Ip Jk
Jn Jr Lh Lv Mc Mg Mi Mk Mr Mu Ni Nv Oi Pf) Sf(Al aQ aY bO Cv dB Dc Dd Il Jm Kd Mj Mx Nh Nl Pi Pk Ql) iZ(aJ Ao aP bN bQ Dk fP Fr
Hc hG iA Io Is It Mj Nf Nt Pb) Pk(Ao Ba Ib Id In Ir Jp Ju Kc Kk Ld Ly Nb Nf Qz Uv Vs) Lz(aM Ao aU aV bL bU bZ cC cI CO dB eF oE oN
pF) Mc(Hr Hw Ip Jk Jn Lh Lv Mg Mi Mu Nv Oi Pe Pf) cI(aM bQ bW bX cC dL Ju Ly Nh Oz Pb Pg Po Pz) Mi(Hr Hw Ip Jk Jn Lh Lv Mg Mu
Ni Nv Oi) hC(Ao Dk fP Fr Hc hG Ib Mj Mw Nf oN pF) Ip(Hr Hw Iu Jk Jn Lv Mg Mu Nv Oi Pe) Co(As Cs dI Lx Mt Pe Pf Qa Qd Uk) Ao(As
dR eF gL Ju oF pF Pz Qz) Hw(Hr Jk Lv Mg Mu Ni Nv Oi Pe) Vs(aM As Cq Cs cX Dc dL Fw Id) dI(aM bQ cC dB Mk Nh oE Oz Pg) Ib(As Cq
Jd Jp Ju Qa Sr Us) pF(dL Io Ir Is Jp Lv Mj Oz) Cs(Fp Ju Nh Po Pz Qz Rf) Mg(Hr Jk Lv Mk Nv Oi Pe) bQ(cN Lw Lx Mt Pe Pf Pz) Nh(bW dL
dR eF gL gP) Io(dR eF gL gP hG iH) Hr(Jk Lv Mu Nv Oi) Ju(Ba Fw Id Ir Jd) aM(It Iv Ly Nf Pz) Mj(dR eF gL iH) Nv(Jk Mk Ni Oi) Lv(hG Mu
Pe) Nf(Bn iA oE) Id(As Qt Qz) Ih(fR No Oi) Ir(aU dB hG) Pz(bL cC dB) aA(Il nK No) dL(iA oE oN) rR(aZ cA iC) Bg(Jd Uk) Dc(Ur Uu)
Dk(Bn Qd) Gp(Qz Uv) Ni(Jk Mr) Is(eF hG) Oi(Lh Mu) Uy(bU cC) oN(Lx Pe) DdSh EmeF FrdR MkJk HcJp SimZ QdbL JdUu SrRf QzKk
JodB aDgV aLdD aQaU bIwE} Nw{Qa(aA Fr Hq Hr Hu Hv Hw Hx Ii Ik Il Im In Io Ip Iq Ir Is Iu Iv Jg Jj Jl Jm Jn Jo Jp Jq Jr Js Jt Lh Lv Lw Lx
Ly Ma Mb Mc Md Me Mf Mg Mh Mi Mk Ml Mm Mn Mq Mr Mt Mu Mx Mz Na Nb Nc Nd Ne Nf Ng Nh Ni Nk Nl Nm Nn No Nr Ns Nt Nu
Nv Nx Ny Oe Oh Oi Om On Oz Pa Pc Pd Pe Pf Pg Po Pz Qb Qc Qd Qe) Lu(AA Fr Hu Hv Hw Hx Ih Ii Ij Ik Il In Io Ip Iq Is Iu Iv Jg Jh Jj Jk Jl
Jm Jn Jo Jp Jq Jr Lh Lv Lx Ly Ma Mb Mc Md Me Mf Mg Mi Mj Mk Ml Mn Mq Mr Mt Mu Mx Mz Na Nb Nd Ne Nf Ng Nh Ni Nk Nl Nm Nn
No Nq Nr Ns Nt Nu Nv Nx Oe Oh Oi Om On Oz Pa Pc Pd Pe Pf Pg Po Pz Qb Qc Qd) Ir(aA aC aM aN bM Fr Hq Hu Hv Hw Hx Ih In Io Ip Iq Is
Iu Iv Jg Jh Jj Jk Jl Jm Jn Jp Jr Js Jt Lh Lv Lw Lx Ly Ma Mb Mc Md Me Mf Mg Mh Mi Mk Ml Mm Mn Mq Mr Mt Mu Mx Mz Na Nc Nd Ne Ng
Nh Ni Nk Nl Nm Nn No Nq Nr Ns Nt Nu Nv Nx Oe Oh Oi On Oz Pa Pc Pd Pe Pf Pg Pk Po Pz Qb Qd) Lz(AA aC aN aO bM cD Fr Hq Hr Hu
Hv Hw Hx Ih Ii Ij In Io Ip Iq Is Iu Jg Jh Jj Jk Jl Jm Jn Jo Jp Jq Jr Js Lh Lv Lx Ly Ma Mb Mc Md Me Mf Mg Mi Mk Ml Mn Mq Mr Mt Mu Mx
Mz Na Nb Nd Ne Nh Ni Nk Nn No Nq Nr Ns Nt Nu Nv Nx Oe Oh Oi Om On Pa Pd Pe Pf Pg Pk Po Pz Qb Qc Qd) Nc(aA Fr Hu Hv Hx Ih Ii Ij
Ik Il In Io Ip Iq Is Iu Iv Jg Jh Jj Jl Jm Jn Jp Jr Jt Lh Lv Lw Lx Ly Ma Mb Mc Md Me Mf Mg Mh Mi Mj Mk Ml Mm Mn Mq Mr Mt Mu Mx Mz
Na Nb Nd Nc Nf Ng Nh Ni Nj Nk Nl Nm Nn No Nq Nr Ns Nt Nu Nv Nx Ny Oe Oh Oi Om On Oz Pc Pd Pe Pf Pg Pz Qc Qd) Oy(aA Fr Hq Hr
Hu Hv Hw Hx Ih Ii Ij Ik Il In Io Ip Iq Iu Jh Jj Jk Jl Jm Jn Jo Jp Jq Jr Js Lh Lv Lx Ly Ma Mb Mc Md Me Mf Mg Mi Mj Mk Ml Mn Mq Mr Mt
Mu Mv Mw Mz Na Nb Nd Ne Nf Ng Nh Ni Nk Nm Nn No Nq Nr Ns Nv Nx Oe Oh Oi Om On Oz Pa Pc Pe Pf Pg Po Pz Qb Qc Qd) Of(aA bM
Fr Hu Hv Hx Ih Ii Ij Ik Il In Io Ip Iq Is Iu Jh Jj Jl Jm Jn Jo Jp Jr Lh Lv Lx Ly Ma Mb Mc Md Me Mf Mg Mh Mi Mj Mk Ml Mn Mp Mq Mr Mt
Mu Mx Mz Na Nb Nd Ne Nf Ng Nh Ni Nk Nm Nn No Nq Nr Ns Nt Nu Nv Nx Oe Oh Oi Om On Oz Pc Pd Pe Pf Pg Po Pz Qb Qc) Mw(aA Fr

Nb Nf Oe Or Pe Pf Pk) Lu(Iv Lw Lx Mb Mm Mt Mz Nn) Mb(Lw Mm Mt Mz Nn Qc) Nn(Mh Ne Nj) Mt(My Nj) DdpK MzNj} Kq{Ar(Bg Ch Dk Hc Hu Ib Iz Mw Nb Nf Nq) Hb(Ch Dk Ef Hu Ib Iz Nq) Cq(Dk Hu Ib Iz) Pa(Dk Hc Ib My) Pk(Ch Ib Ik Iz) Hu(Id Ir Kf) Ef(aA Oe) Nq(Lx Or) Iz(Id Kf) BgKf EqmS} On{Of(Ir It Jh Jt Lu Mb Mm Mp Mv Mw Ng Nj Nn Nq Ny Pb) Oy(Ir It Jn Jt Lu Lw Mh Mm Mp Nj Nn Ny) My(aA It Jt Mf Mh Mm Mp Mz Nj) Ng(It Jt) Pk(Ch Ib)} Mm{Ir(Ik It Lu Lx Nj Of Oy Pb) Pk(Ax Ch Ik Ln Ld Or) Mz(Hx Mv My Ny Pb) Of(Is It Jl Jt) It(Jl Lx) NgJt IsOy JlPb} uR{Wm(bS gP Id Mz Ne oH oN tN Ur) Id(cA cG dG Oz Pa uI wF Tj) Ar(dA Or wF) Or(Fb iP) MzbE JliA KfcF} Hb{Wm(Ao Ed Fw Id Iz Mk My Pk Qz) Or(Ax Ch Id Iz My Pk) Ao(Lx Pa) Jv(Ax Dc) Falb LxMy HuPa IdRg} Jt{Ng(Fr Jl Lu Lx Mt Mz Nc Nn Nv Ny Qb) Nn(My Nj Of Oy Pb) Mz(My Nc Nj) LxMy NyOy} nK{Nx(aA Ct Ed My Nc Nk Ye) Nk(aC bN cJ Ir Oh) aA(Mz Nn No) IrbE IsWe VzcZ} Kf{cF(rR rW sO) rR(hG qV) Falb IkPk VqyJ} Dc{Ur(Jv Lv Rg Wm) ArJv SrRg} Pk{Ik(Dg Ke) EqUc HuKe SrRg bUpK} Ax{fA(cl Nk) LuOr eCpH} Dd{Mz(Sf We) DunA MnSh} Eq{iJ(Ng Ut) MniO IjmS} Nk{KxgZ aCnL bNoO} Sr{Rg(Kn oN) MlrR} cR{mW(Ry Xa) OwpK} gV{AdMb HucP aDaK} Ar{CqIb LuOr} Bb{tV(Ba Hu)} Cs{Qw(aK Il)} Du{FwmU aWkI} Kx{Anpl blgZ} Ut{TiaM ShiJ} eC{NjdU bEpH} rR{WmrB UrVq} CuGnoP FyYgmT MzHxNy NcKkrW RzUumS bBfBnN Unconstrained panels with 2 analytes, where 1.0E-8 >= 'model p-value' > 0. Contains 300 panels of 199,783 total panels evaluated. : Ji(aA Et Fp Fr Hq Hr Hu Hv Hw Hx Ih Ii Ij Ik Il Im In Io Ip Iq Is Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Et(Fp Hu Hx Ih Im Ir Is It Iv Jh Jj Jl Jm Jn Jo Jq Jr Jt Lh Li Lj Lu Lv Lw Lx Lz Mb Me Mf Mh Ml Mp Ms Mt Mv Mw Mx My Mz Nb Nc Ne Ng Nj Nl Nn No Nq Ns Nt Nu Nw Ny Oe Of Og Ok Oy Oz Pb Pc Pk Pz Qa Qb Qd Qe) Ok(Fp Hx Ih Ii Ik Im Io Ip Iq Ir Is It Iu Iv Jh Jj Jo Li Lj Lu Lw Lx Ly Lz Mb Mf Mg Mh Mm Mp Ms Mt Mv Mw Mx My Mz Nc Nd Ne Nf Ng Nj Nl Nm Nn Nq Ns Nw Ny Oe Of Og Oy Oz Pb Pc Pz Qa Qd Qe) Li(aA Ik Im Ir It Jj Jl Jp Lj Lu Lw Ms Mv Mw My Mz Nc Nf Ng Nj Nw Of Og Oy Pb Qa Qd Qe) Nw(Fp Im It Lj Lz Ms Mv Mw My Nj Og Pb Qe) Lj(Im Jg Jp Jt Lh Mm On) Im(Lz Og) Qe(Aa Og)

Unconstrained panels with 2 analytes, where 1.0E-7 >= 'model p-value' > 1.0E-8. Contains 365 panels of 199,783 total panels evaluated. : Li(Fp Fr Hq Hr Hu Hv Hw Hx Ih Ii Ij Ik Il In Io Ip Iq Is Iu Iv Jg Jh Jk Jm Jn Jo Jq Jr Js Jt Lh Lv Lx Ly Lz Ma Mb Mc Md Me Mf Mg Mh Mi Mj Mk Ml Mm Mn Mp Mq Mr Mt Mu Mx Na Nb Nd Ne Nh Ni Nk Nl Nm Nn No Nq Nr Ns Nt Nu Nv Nx Ny Oe Oh Oi Om On Oz Pa Pc Pd Pe Pf Pg Po Pz Qb Qc) Nw(aA bM Hv Hx Ih Ik Il Io Ir Is Iv Jh Jj Jl Jn Jt Lh Lu Lv Lw Lx Ly Mb Md Me Mf Mh Mj Ml Mm Mp Mt Mx Mz Nb Nc Nd Ne Nf Ng Nh Nl Nm Nn Nq Ns Nt Nu Nx Ny Of Oy Oz Pc Pd Pk Qa Qd) Ok(AA Fr Hq Hr Hu Hv Hw Ij Il In Jg Jk Jl Jm Jn Jp Jq Jr Js Jt Lh Lv Ma Mc Md Me Mi Mj Mk Ml Mn Mq Mr Mu Na Nb Nh Ni Nk No Nr Nt Nu Nv Nx Oh Oi Om On Pa Pd Pe Pf Pg Po Qb Qc) Et(AA Fr Hq Hr Hv Hw Ii Ij Ik Il In Io Ip Iq Iu Jg Jk Jp Js Ly Ma Mc Md Mg Mi Mj Mk Mm Mn Mq Mr Mu Na Nd Nf Nh Ni Nk Nm Nr Nv Nx Oh Oi Om On Pa Pd Pe Pf Pg Po Qc) Lj(aA Ir Is It Iv Jd Jl Lu Lv Lw Lz Mg Mp Mt Mz Nc Nj Nl Nm Nn Nt Nv Nx Ny Og Pj Qa Qd Qe) Qe(aA Fp Im Ir It Jg Jj Jp Jt Lh Lz Mm Ms Nj Nl Nm Nn Pb) Im(Fp Ir Jj Jl Jp Jt Lh Lu Mm Ms Mz Ng Nj Pb Qd) Ji(Aa aC Aj aN aO Ax bM cD Ch cM Ef Gl iJ Wm) Jp(Fp It Lz Ms Og Pk Qa Qd) Og(Jg Jt Lh On Qa Qd) Fp(Jt Mm Qd) Ms(Lh On Qd) Nj(Qa Qd) Jj(Dc Lh) Pj(Or Pk) cM(Uh Vt) AaQa AdAj GchC Unconstrained panels with 2 analytes, where 1.0E-6 >= 'model p-value' > 1.0E-7. Contains 717 panels of 199,783 total panels evaluated. : Ji(aD aE aF aG aH aJ aK aL aM Ao aQ Ar As aU aV aW aX aZ bA bB bC bE bF Bg bH bI bL BN bO bQ bR bU bV bW bX bZ cA cB cC cE cG cH cI cJ cL cN CO cR CS Ct cU cV cW cX cY cZ dA dB Dc dD dE dH dI dJ DK dL dR eF fP gL gP hB hC hG iA Id iH iO iP IZ Ju Jv kR kS Ld nW nY oE oF oH oK oN Or pF Pk Qw Qz Rg Sf Sr Uh Uv Vs Vt Vv) Qe(Aj aN cM Fr Hq Hr Hu Hv Hw Hx Ih Ii Ik Il In Io Ip Iq Is Iu Iv Jd Jh Jk Jl Jm Jn Jo Jq Jr Js Lu Lv Lw Lx Ly Mb Me Mf Mh Mi Mj Mk Ml Mn Mp Mq Mr Mt Mu Mv Mw Mx My Nb Nc Nd Ne Nf Ng Nh Ni Nk No Nq Nr Ns Nt Nu Nv Nx Ny Oe Of Oh Oi Om On Oy Oz Pa Pc Pd Pe Pf Pg Pj Po Pz Qa Qb Qc Qd Qw Uh Vt) Im(AA Fr Hq Hu Hv Hw Hx Ih Ik Il In Iq Is It Iu Iv Jg Jh Jk Jm Jn Jo Jq Jr Js Lv Lw Lx Ly Mb Me Mf Mh Mi Mj Mk Ml Mn Mp Mr Mt Mv Mw Mx My Nb Nc Nd Ne Nf Nh Ni Nl Nm Nn No Nq Ns Nt Nu Nv Nx Ny Oe Of Oh Om On Oy Oz Pa Pc Pd Pe Pf Pg Po Pz Qa Qc) Lj(Aa Fp Fr Hb Hq Hu Hv Id Ih Ii Ij Ik Il In iO Ip Iq Iu Jh Jj Jk Jm Jn Jo Jq Jr Js Kf Kq Lx Ly Ma Mb Mc Md Me Mf Mh Mi Mj Mk Mn Mq Mr Ms Mu Mv Mw Mx Nb Nd Ne Nf Ng Nh Ni Nk No Nq Nr Ns Nu Oe Of Oh Om Oz Pa Pb Pc Pd Pe Pf Pg Po Pz Qb Qc Uh Un Vt) Nw(Aa aC aN aO Fr Hq Hr Hu Hv Ii Ij In Ip Iq Iu Jg Jk Jm Jo Jp Jq Jr Js Ma Mc Mg Mi Mk Mn Mq Mr Mu Na Ni Nk No Nr Nv Oe Oh Oi Om On Pa Pe Pf Pg Po Pz Qb Qc) Qd(AA Hv Ik Il Ir Is It Jg Jj Jl Jn Jr Jt Lh Lu Lw Lx Lz Mh Mj Mk Mm Mp Mt My Mz Nc Ne Nh Nl Nm Nn Nq Nt Nu Ny Oe Of On Oy Oz Pb Pd Pz Qa Qc) Jp(Hc Id Ih Ir Is Iz Jj Jl Jm Jn Jr Jt Jv Lh Lu Lv Lw Lx Mh Mm Mp Mt Mx My Mz Nj Nl Nm Nn Nt Nu Ny Of Oy Oz Pb Pj Qb Vt) Qa(aA Fp Ik Ir It Jg Jj Jn Jt Lh Lu Lw Lz Mm Ms My Mz Nc Nf Nl Nm Nn Nq Nt Nu Ny Oe Of On Oy Pb Vt) Vt(aC aK Ar aU aV Ax bB bL bM bX Cs cV cX Dc dD dl dL Et Ir Jd Kn Kq Li Pj Pk Ti Th) Aa(bM Fp Iv Jg Li Lu Lw Lx Lz Mb Mm Ms Mt Nb Ne Nj Nl Nn Og Qc) Lh(Fp Ih Ik Ir Is It Jt Lz Mm My Nj Ny Of Oy Pb) Pj(aC Ar Ax cM dH dL Fa hC iJ Ir Jj Li Lx Lz Rg) Mm(Ir Is It Jj Jl Jt Lx Lz Ms Og Pk) Jt(Aj Jj Lx Lz Ms Mz Ng Nj Nn Ny) Et(aC Aj aO bM Ch cl Cs Id Or) Jg(Fp Ir Jj Lz Ms My Ng Of Oy) On(Fp It Jj Lz My Ng Of Oy) Uh(Ar Ax Cs Dc Id Li Pk Rg) Nn(Fp Ir It Jj Lz Ms Og) Kq(Aj Bg Ch Ef Hu Iz Jj) Jd(Ar Fa Id Ir Li Lz) Og(Fp Ij Nv Ny) Ok(aC Aj Pk We) Hb(Ax Or Wm) Li(aN Ij Qw) Dc(Aj Ur) Fp(It Ny) GceC LzNy SrRg NxnK Unconstrained panels with 2 analytes, where 1.0E-5 >= 'model p-value' > 1.0E-6. Contains 1,623 panels of 199,783 total panels evaluated. : Vt(AD aE aF aG aH aI AJ aL aM aN AO aP aQ aR AS aW aX aY aZ BA bC bE bF bG bH bI bJ bN bO bP bQ bR bS bU bV bW bZ cA cB cC cD cE cF cG cH cI cJ cK cL cN cO cP CQ cR cS cT CU cW cY cZ dA dB dC Dd dE dF DG dH dJ dK Dl dM dN Ed eF Fa Fp Fw Hb Id Il Im Iq Jj Jl Jt Kc Ke Kf Kk Ko Kp Kr Ks Kx Lh Lx Lz Me Mh Mm Mt Mx Mz Nf Nn No Nr Nw Oh Ok On Or Ou Pd Pe Qd Qg Qz Rg Sr Tz Uf Uh Ur Wm) Ji(Ad Af al Al An AP aR aS Aw aY Ba Bb Bc bG bJ Bo bP bS cF cK CP CQ cT Cu Cv Cw Cx Db dC Dd De dF DG Di Dl dM dN eC Ed Ex Fa fR Fw Gp Hb Hc HF Ib Ic Jd Kc Kf Ki Kj Kk Kl Kn Ko Kp KQ Kx Ky Kz nK Oa Ou Ow Ph Pi Pj Qg Qh Qt Qu Qv Qx Qy Ra Rb Rc Rf Rh Ri Rj Rm Sh Si Ss St Tn To Tr Tt Tv Tz Ua Ub Uc Ud Ue Uf Ug Uk Ul Um Un Uo Up Ur Us Ut Uu Uy Vj Vo Vp Vu We Wh Tj Ti Th tF) Jp(AA aC aN aO Ar Ax bM Ch Cs Ed Fa Fr Hb Hq Hr Hu Hv Hw Hx Ib Ic Ii Ij Ik Il In Io Ip Iq Iu Iv Jd Je Jg Jh Jk Jo Jq Js Kc Ke Kf Kk Kl Kn Ko Kq Kr Ks Kx Ld Ly Ma Mb Mc Md Me Mf Mg Mi Mj Mk Ml Mn Mq Mr Mu Mv Mw Na Nb Nc Nd Ne Nf Ng Nh Ni Nk No Nq Nr Ns Nv Nx Oa Oe Oh Oi Om On Or Ou Ow Pa Pc Pd Pe Pf Pg Pi Po Pz Qc Qt Qw Rg Tz Ua Uh Un Us Vs Vu Vv Wm) Qe(aC Ad AF aK Al An AO AP Ar AS aU aV AW Ax aZ BA BB BC bE Bg bJ bL bM Bn Bo bQ bS bU bW bX cA cB cC cD cF cG Ch cl Co Cp Cq cR CS Ct Cu CV Cw CX cY DB Dc DD DE Dg dH Dl dJ DK Dl Gc Hb Ib Id IJ Jv Kc Kf Kk Kn Kp Or Pk Qg Qt Qz Rb Rg Sr Tn To Tr Tv Ua Ub Uf Uk Un Ur Vs Vv Wm Ti) Lh(AA aC Aj aN Fr hG Hu Hv Hx iA Ib Id Ii Ij Il In Io Ip Iq Iu Iv Iz Jd Jg Jh Jk Jl Jm Jn Jo Jq Jr Js Lu Lv Lw Lx Ly Mb Mc Md Me

Bb Cu Dg Nm) Ms(Ih Ij Jm Jq Qb) Sh(Dd Dk Mn Qh Ut) rR(Ap Dg Nx Tk Wm) Nk(gZ mI nN pK) Cu(Rg Vv Wh) Wm(hP wE wH) Ih(aA Lv Nu) Zq(aM bU cM) Bb(aN bM) Dr(Mn Ut) Ib(Cq Pe) Sf(Dk Mn) Qb(aA Nm) Rg(Dd Jq) Oa(cM Kc) bB(dU fB) AdCh BogV FycM IcOh ljO

Mc Mf Mg Mh Mi Mn Mq Mr Mu Mw Nb Nd Ng nK Nr Nx nY Oa Oh Oi Om oN Op Or Ou Ow Oy Oz Pa Pc Pd Pe PF Po pY Pz qA qB QC
qD qG qH ql qO qP qQ qT qU qV QW qX qY QZ rA rB rC Sf Sh Si Tr Tz Uf Ur Us Uv Vu Wb Yd Yg Yk Yl Zq Ye Wm Ti) Pk(AA Af aI Aj
Al aM AN Ao As aU aV Aw Ba bB bC Bg bL Bn BO bQ bU bW bX cC cD cG Ch cl cN Co Cp Cq cR Ct cV Cw Cx cY DB DD DE dG dH DI
dJ Dk dL Dp DR eC Ed EF Ex Ez Fb Fp Fy Gl Gp HC Hf hG Hq Hv Hw Hx Ib Ic Ih Ij IO Ip Iq It Iv Iz Je Jk Jm Jn Jq Jr Ju Jv Jy Kd Kg Ki Kj
Kl Kr Ks Ky Kz Lv Ly Ma Mb Mc Md Mf Mg Mh Mi Mj Mk Ml Mq Mr Ms Mu Mv Mw Mx My Na Nb Nc Nd Ne Ng Nh Ni Nj Nl Nq Ns Nt
Nu Oe Of Oi Om oN Ow Oy Oz Pa Pb Pc Pd Pg Ph Pi Po Pz Qb Qc Qh Ql Qm Qn Qw Qz Rb Rm St Tn Tr Tv Tz Ub Uc Uk Uo Up UR Us Uv
Vp Vq Vu Wb wE Yi) Ax(Aa Ad aF Aj aK aM AO Ap AS aU bB BC Bn Bo bU bW cA cC cl Cp Cq cR Cs Ct Cu Cv dB DD Dg dH DI DL Dp
dU eC Ez fA Fb Fn Fy Gc Ha HC Hf hG Hu iA Ib Ih Ii IJ Ik Il Im In IO iP Iq Is It IZ jB Je Jf Jg Jl Jm Jn Jq Jr Js Kd Kg Ki Kj Kl Kp Kr Ks Kx
Ky Ld Lu Lv Lx IY Md ME Mg Ml Mj Mk Ml Mn Mp Mq Mt Mu Mx My Nd Ne Nf Nh Ni Nj Nn Nt Nv nW Nx Ny Oa oE oF Og OH ON Ou
Ow Oz Pa Pb Pd Pe PF Ph Pi Po Qb Qc Qg Qh Ql Qm Qn Qt Qu Qv Qx Qy Rb Rc Rf Rh Rm Ss St Tn To Tr Tt Tv Ua Uc Ud Ue Ug Ul Um Ut
Uu Uv Vo Vp Vq Vs Vu Th tF) Kf(aF aK Al aM aN AO As aV Aw Ba Bb Bc Bg bL cB cC cD cl Cq Ct Cu CV dB dD dH dl Dk dL eC eD EF
Ex FP FR Fw Fy Gp Gz Ha HC hG hO hP hR iA IC IJ Im In Iq Is iZ jD Je jG Jh Jk Jl JM JO JQ jR Js Ju Jv jY Kc Ki Kk Kn Ko Kr Kx Ky Ld IL
Lu Lv Lw Lx Mf Mh Mi Mk Ml Mm Mp Mr Ms Mt Mw Mx My mZ Na Nb Ne Nf Ng NH NK Nm Nn No Ns Ny oE Of Oh Ok ON Ou Oy Oz
Pa Pb Pd Pe PF Pg Po Pz qA Qb Qc Qh QT QU Qv Qw Qx Qz Ra rB Rc Rh rO rW St Tv Tz Ua Ub Uc Ud Ue Uf Ug Uk Up uR Ut Uv Vb vH
Vo Vs Vu wE wQ yJ Tj) Kn(aC aF Aj aM aN AO Ap As aU aV BB BC bH bL bW cA cC cD Ch cl cN cR Ct Cu cV cY dB Dg dl dJ DI Dp dR
eC eD EF Ex FP Fr Fw gL gP Ha hB HC hF hG Hu iA Ib IC iH Ij Ik Il Im In IO iP Iq Is IZ Jl jQ Js Jt Ju Jv Kc Kk Ko Kp kQ kR kS Kx Ky Ld
IK IM Lu Lv Lw Lx Mk Ml Mm Mp Mt Mx My Nb Ne Nf Nk Nm Nn No nW NY Oa oE oF Og OH oK ON Ou Oz Pe PF Po Pz Qb Qc Qg Qh
QT QU Qv Qw Qx Qy Ra Rb Rc Rf Rh Ri Rj Rm rR Ss St Tn To Tr Tt Tv Tz Ua Ub Uc Ud Ue Ug Uk Ul Um Uo Up uR Ut Uu Uv Vo Vp Vs
Vu Vv wE wQ Tj) Sr(Ad Aj aK Al aM aN AO As aU aV Aw Ba BB Bc bM Bn bX cD Ch Cq cR Cu cV Cw cX dD Dg dl dJ dK DL Dp Dr eD
eF FP Fw Fy Gc gW HA Hc hP Hq Hr Hu Hw Hx iA Ib IC Ih Ii Ij Ik In Io IP Iq Is Iu Iz jD Je jF JG jl Jl JM Jn jO JQ JR Js Jt jU JV Jy Kd Kg
Kk Ko Kp Kr Ks Kx Ld IL IM Lv Lw Md Me Mh Mi Mj Mk Ml Mm Mp Mq Mr Ms Mu Mx My Nb Nc Ne Ng Nj Nk Nl Nm Nn No Nr Ns Nv
Nx Ny oE Og Oh ON Ou Ow Oz Pa Pb Pd PF Ph Pi Po Qb Qh Qm Qn QT Qw Qz rR St Tn Tr Tv Tz Ua Ub Uc Uk Uo Up UR Us Vp Vv Tj Ti)
Or(Aa aC AD aE aF aG aH al aJ AL aM aN AO aP aQ aR aS aU aW aX aY aZ bA bB BC bE bF bG bH bI bJ bL bN bO bP bQ bR bS bU bV
bW bX bZ cA cB cC cD cE cF cG cH cl cJ cK cL cN cO cP cQ cR cS cT CU cV CW cX cY cZ dA dB dC DD dE dF dG dH dI dJ dK dL dM
dN Dr Ed Ex Fp Fr Fw Fy Gb Hc Hf Hu Ib Ic Ih Ii IJ Ik Il Io Iq Is Iu Iz Jg Jl Jm Jn Jq Js Jv Kg Kk Kr Ks Kx Ld Lv Lw Lx Me Mh Mk Ml Mn
Mt Na Ne NK No Nr Nv Nx Ny Of Og Oh Oi On Ou Oz Pd Pe Pf Pi Qc Qg Qh Qm Qw Qz Rg rR St Tr Tt Tv Tz Uc Us Uv Wb Zq Wm)
Gc(al Aj aK aN AS aV aW aY bA bB bE bG bI bM bN bO bP bQ bR bU cB cC cD cF cG cJ cM cQ cT CU cV cW cX cZ dC dF dH Dk Dr Ed
Ef EM eP Et Ex Fw gW Ha Ij Ik Im Is jE jH jK Jl jM jO Jp jQ jR Ju Jv Kd kG kl kP Kx Ky Li IK IO Lv Lx IY Lz ME Ml Mn Mr mS Mt Mw
Mx nB Nc Ne nH nK nL nN Ns Oa Og Oh On Oy Oz Pe Pf Pg Po Ps Qg Qt Qu Qv Qw Qx Qy Ra Rb Rc Rf Rh Ri Rj Rt Ru Rv Ry Sh Ss St Tn
To Tr Tt Tv Tz Ua Ub Uc Ud Ue Uf Ug Uh Ul Um Uo Up Ur Ut Uv Uw Ux Vc Vh Vo Vp Vq Vs Vu Vv Vw Wc Wd We Wf Wg Wh
Wm Tj Ti Th Yf) Qa(Ad AF aJ aK Al aM An AO AP AS aU aV AW aZ BA bB BC bE Bg bH bJ bL bM Bn BO bQ bR bS bU bX cA cC cF cG
Ch cl cN Co Cp Cq cR CS cT Cu CV CW CX cY DB dD DE Dg Dl dJ DK Dl Dr Du eC Ed Ef Eq Ez Fb Fc Fn Fw Fy Gb Gl Gp Ha hC hF hG
Hp iA iH iJ iO iP Jf Ju Jy Kd Kg Ki Kj Kl kQ KR Ks Ky Kz Lt nK nW nY Oa oE oF oH oK oN Op Ow pF Ph Pi Ps Qh Ql Qm Qn Qv Qy Ra
Rc Rt Ru Rv Sf Sh Ue Ug Up Ut Uw Ux Uy Uz Va Vb Vc Vh Vi Vo Vp Vq Vu Vw Wb Wc Wd We Wf Wg Yd Yg Yl Zw Tl Tj tF Yf) Cs(aF
Aj aM aN AO Ap AS aU aV bA bB BC bE bM Bn Bo bU bW bX cA cC cl Cp Cq cR Ct Cu Cv cY dB DD Dg dH DI Dp eC Ed Ez Fb
Fn Fy Ha HC Hf hG Hq Hu iA Ib IJ Ik Il Im In IO Iq Is Iz Je Jf Jl Jm Jn Jq Jr Js Ju Jy Kd Kg Ki Kj Kk Kl Kr Kx Ky Ld Lu Lv Lx Md Me Mg
Mi Mk Ml Mn Mt Mu Nc Ne Nf Nh Ni Nj Nk Nl Nn Nv Nx Ny Oa oF Og ON Ou Ow Pa Pb Pd Pe PF Ph Pi Po Pz Qb Qc Qg Ql Qm Qn Qt Qu
Qv Qx Qy Rb Rc Rf Rh Ri Rj Rm Ss To Tt Ua Ud Ue Ug Ul Um Ut Uu Uv Uy Vo Vp Vu Th) Lx(aC Ad aF Aj aK aN AO aU aV Bb Bc bL bM
bQ cC cD cl cM Cv dB Dd Dk Dl Dp Du Dw Ed eO Eq EW Fc Fd Fi Gb Gh hG Hl Ho Hp Hq Hr iA Ib Ic Ii iJ Il Io Je Jf Jk Jv Kc Kg Kk Ko Kp
Kr Kx Ld Lp Lt Ma Mc Md Mg Mj Mq Mu Na Nb Nk Nr Oa oE Oh Om oN Op Ou Pa PF Pg Ps Qg Qh Qt Qv Qw Qx Qz Ra Rb Rg Ri Rt Ru
Rv Rx Ry Rz Sf Sh Si Sj Tr Tz Ua Ub Uc Ud Ue Uf Ug Uk Ul Uo Up Ur Us Ut Uv Uw Ux Uy Uz Va Vb Vc Vh Vi Vs Vv Vw Vz Wc Wd We
Wf Wg Yd Yg Yk Yl Zq Zw Zx Ye Tm Tl Xa Yf) Jp(Ad aE Af al aJ AL An AP aQ aR aS aV AW aY aZ BA BB BC bF BG bH bl bJ bN BO
bP bR bS bU bV bW bX bZ cA cB cE cF cG cH cJ cK cL cN cO CP CQ cS CT cU cV CW Cx cY cZ dA Db dC dD De dF DG dH Di dJ DK
DL dM dN DR Eq Ex Fd fP fR gL Gp Gz hA hB hC hF hP hR iB iC iH iJ iO iZ jD jF jK jM jO jR jU jV kP kQ kR kS IL IM mE mF ml nL nN
nO nW nY oF oH oK oN qT qU qV qW qX qY rB Rz Sf Vc Vh Vq Wb Yg Yl Ye Tj Th tF) Jd(aA AD AF aK aM AN aO Ap aU aV BB bI bL
BO bQ bX cC cD cE cH cl cN Co CP cR cV CW cX dA DB dD De Dg dH Dl DK DL Ed eD Fb Fn Fn fP Gl gW hA Hf hP Hq HR hV hW hX iB
iC It Iv jD jE JF JG JH jl JK jL jM JO jP jQ jR jT jU jV jY Kg Ki Kj Ks Ky Kz IM IN IO Ly Ma Mf Mn Mv Mw Nb Nf Nh Ni Nt Nu Oe Oi Om
Ow Pc pY qA Qc Qg Qm qT Qx Qy rB rC Rf Rh Ri Rj rR rW rX rY rZ Tn To Tr Ud Ug Ul Um Ut Vq wE Tj Ti) Lz(aF Aj Al aM AO Ap As aU
aV BA bB bC bE bL bM Bn bR bU bW bX cC cl cM cO Cp Cq cR Ct Cu cV Cw cX cY dB dD dE Dg dH dJ DK DL Ed Fb Fw Fy Hq Hr Hu
Hv Hw Hx Ic iJ In Io Ip Iq Iu Jj Jk Jo Jr Jv Jy Kd Kg Kk Kp Kr Ks Kx Ld Lu Ly Ma Mb Mc Md Me Mf Mg Mh Mi Mj Mk Ml Mp Mq Mr Mu
Mv Mw My Na Nb Nd Ne Nf Ng Ni NK No Nq Nr Ns Oc Of Oh Oi Om Oy Pa Pc Pd Pe PF Pg Pi Po Qc Qg Qh Qw Qz Rb Rg Ri Rm St Tr Tv
Ub Uc Up Ur Vp Vu Wm Ti) Vt(Du EM Ex Fc Fd Fi Gb Gd Gh Gn gW Gz Hl Ho HP iZ IK Lp Lt nK Op PS qG qH ql qO qP qQ qT qU qV qX
qY qZ rA rB rC rN rO rP rQ rS RT RU RV rW RX RY RZ sC Sf Sh Si Sj sM sO TO tR tT tV uG ul uL uM uN uO uT uU uV UW UX UY UZ
VA VB VC vH vl Vj vO vP vQ Vs vU vV VW Vz Wb Wc Wd We Wf Wg WH wQ Yd yH Yi yK Yl zH zl Zq Zw Zx YE TM TL XA Yf)
Ok(Ad Af Al An Ap Ba Bb Cp Cq Cw Cx Db De Di Dp dR DU eC Ed Em Ez Fb Fd fP Fy Gd Gh gP hB hC HF hG Ho iH iJ iO iP iZ Je Jf Ju Jv
Jy Kd Kg Ki Kj Kl Ko Kp kQ kR KS Ky Kz IK Lp Lt ml nL nN nW nY Oa oE oF oH oK oN Ow pF Ph Pi Qg Qh Qt Qu Qv Qw Qx Qy Qz Ra
Rb Rc Rf Rh Ri Rj Rm Ry Ss St Tn To Tr TT Tv Tz Ua Ub Uc Ud Ue Uf Uk Um Uo Up Ur Us Uu Uv Vp Vs Vu Vv Yh Yi Zq Tj Th tF Yf)
Uf(aC aN AO As Aw Ba bL bM cD Ct Cu Cv Dd eC Ed EF Ez FP Fw Fy Gp Hc Hu Hx iA Ib Ic Ii Ik Il Im In Iq Is Je Jl Jm Jn Jq Jr Js Jt Jv Kc
Kk Kl Ko Kp Kx Ld Lv Lw Md Mh Mk Ml Mm Mq Mt Mx My Nc Ne Nj NK Nl Nn No Nq Nr Ns Nx Ny Oa Of Og Oh ON Oy Oz Pa Pb Pe Pf
Pg Po Pz Qb Qc Qh Qt Qu Qw Qz Rb Rc Rf Ri Rj Rm rR Ss St Tn To Tr TT Tv Tz Ua Ub Uc Uk Ur Us Uu Uv Vp Vu Vv Wm Ti) Mt(Ad aF Aj aK aM aN
aO Ap aV BB Bc bL bM bQ cC cD cM Cu CV Dd Dl Dr Ed Fr Hq Hr Hu Hv Hw Hx Ib Ii Ij Ik Il In Io Ip Iq Iu Jv Jj Jk Jo Jr Jv Kc Kk Ko Lu
Lv Ly Ma Mb Mc Md Me Mf Mg Mh Mi Mj Mk Ml Mn Mp Mq Mr Mu Mv Mw Mx Na Nb Nc Nd Ne Nf Ng Nh Ni NK Nl No Nq Nr Ns Nu
Oa Oe Of Oh Oi Om Oz Pa Pc Pd Pe Pf Pg Po Pz Qb Qc Qh Qw Qz Rg Sh Tz Ua Ur Us Uv) Is(aA aC Ad aF Aj aK aM aO Ap aU aV BB Bc cC
cD Ch cl cR Ct Cv dB Dd Dg dl dL Dr Du Hq Hr Hu Hv Hw Hx Ib Ih Ii Ij Ik Il In Io Ip Iq Iu Jh Jj Jk Jo Jq Jr Js Jv Kc Kk Ko Kx Lu Lv Ly Ma
Mb Mc Md Me Mf Mg Mh Mi Mj Mk Ml Mn Mp Mq Mr Mu Mv Mw Mx Na Nb Nd Ne Nf Ng Nh Ni Nk No Nq Nr Ns Oe Of Oh Oi Om Oz
Pa Pc Pd Pe Pf Pg Po Pz Qc Qw Qz Rg Sf Sh Ur Us Wh Ye Ti) Lj(aD aE AF aG aH al aJ AL An aP aQ aR aS AW aX aY aZ bE bF bG bH bI bJ

Figure 33 Continued bN BO bP bR bV bZ cB cE cF CH cK cL CO cP cQ cS Ct cU cW Cx cZ Db dC DE dG Dk dM dN DR EF Ex Fc Fd Fi fR Gb GL GP gW Ho iZ Ky Kz lK mE ml nK nN Op Ps Rt Ry Rz Sf Sh Sj TT tV Uw Ux Uy Va Vc Vh Vi Vw Vz Wc Wd Wg Wh Yd Yj Yl Zq Zx Ye Tm Tl Xa Tj Th) Ji(DU dX eD Em Eo eP Eq eZ Fc Fd Fi fN fY Gd Gh Gn hA HL HO Hp hR iB jB jE jF jG jH jI jK jL jM jO jP jQ jR jT jU jV jY lL lN lO Lp Lt ml mZ nL nN Op qB qC qD qG qH ql qO qP qQ qT qU qV qW qX qY rA rO rQ rS rU Rx Ry Rz sC Sj tN tO tR tS tV tX uM vH vV Vz wC wD wF wG wH wK wL wP wQ Yd Yg YH Yi Yj Yk Yl zA Zq Zw Zx Yc Tm Tl XA) Js(aC Aj aN bM cM Hq Hr Hu Hv Hw Hx IC Ih Ii IJ Ik Il In Io Ip Iq Iu Iv jD Jh Jk JM Jn Jo Jq Jr jU Jv Kk Ko Kx Ld lK Lv Ly Ma Mb Mc Md Me Mf Mg Mh Mi Mj Mk Ml Mn Mp Mq Mr Mu Mv Mw Mx My Na Nb Nd Ne Nf Ng Nh Ni NK No Nq Nr Ns Nu Nv Nx Oe Of Oh Oi Om Oy Oz Pa Pc Pd Pe Pf Pg Po Pz Qb Qc Qw Qz Rg Sf Sh Ub Ur Us Wm Ti) Oa(aC Ad Aj aK aN Ao Ap As aU aV Ba BB Bc bM bW bX cD Ch Cq Ct Cu CV Dd Dg dH dI dJ DL Dp Dr Ex Fr Fw Fy Hf Hu Ib Ic iJ Ik Il Im In Iq Iu Jg Jl Jq Jt Jv Jy Kg Kk Ko Kp Kx Ld Lu Lw Mb Mc Mj Mk Mp Mu Mx Nc Nf Nh NK Nm Nn No Nr Nx Ny Og Oh On Ou Ow Pa Pd Pe Qw Qz Rg Ur Us Wm) Jl(bM Hc Hq HR Hu Hv Hw Hx Ii Ik Il In Io Ip Iq Iu Jh Jk jM Jo Jq Jr Kc Kk Ko Kx lK Lu Lv Ly Ma Mc Md Me Mf Mg Mh Mi Mj Mk Ml Mn Mp Mq Mr Mu Mv Mw Na Nb Nd Ne Nf Ng Nh Ni NK No Nq Nr Ns Oe Of Oh Oi Om Pa Pc Pd Pe Pf Pg Po Pz Qc Qw rB Rg Ur wH wQ Ye Wm Ti) Ti(aC Al aN aP As bA bB Bc bO cG cM cN Cq cU CV cX dB Dd dF dH Dk dL Du Et Fb Fp Fy Ha Ii IJ Il Im Iq Iu Iv iZ Jj Jk Jm Jq Jr Jt Kd Ko Ks Kx Me Mi Mp Mq Mr Mx Nb Nk Nm Nt Nv Nw Nx Ny Oe Om Ou Ow Pf Pg Pi Pj Qb Qc qU Rg rU Sf St Tn Tv Tz Uc Uh Wm Tj) Nw(Dp eP Ex Ez Fb Fn fR Fy gW Gz HA hR iB iC jD JF jG jH jM jO jQ jR jT jU jV Jy lL lM mI nL nN nO qA Qg Ql Qm Qn qT QU QV qW QX QY RA Rb Rc Rh Ri Rj Rm Sf Ss St Tn To Tr TT Tv Ua Uc Ud Ue Ug Ul Um Ur Ut Uu Vo Vp Vq Vs Tj Th) Uh(aA Af An Ap Bb Bo Co Ct Db De Dg Di Dk Dp Dr eD Ef Ez Fb Fn hA Hf iB Ip jE JF jG JH jI jK jL jM jO jP jQ jR jT JU jV jY Ki Kj Kl Ks Ky Kz lL lM lN lO Ma Mg Mn Mv Mw mZ nL Ow Ql Qm Qn qT qU qV qW QX qY rA To Tt Ug Ul Um Uo Ut Vo Wn Tj) Im(aM aO aU aV bE bL bX cC cD Ch cI Ct Cu Cv dB DD dE Dk dL Dp Dr EF gL HC Hf hG iA Ib Ic iJ iO iP Iz Jf Ju Jv Jy Kc Ko Kp Kr Kx Ld nK oN Ou pF Pi pK Qg Qh Qt Qu Qv Qz Rb Sf Ss To Tr Tv Tz Ua Ub Uc Uk Up Ur Us Uu Uv Vp Vs Vv Ye Wm) Wm(BB cD cM Cu Dd Ed Fp Fw Fy hO Jj Jq Jt Kc Kk Ko Kp lK Mx No Nv Nx On Pe Po pY qA qG QH qI Qw QZ rB Rg rO rP rQ rS rT rU rV rW sC St tN tO tQ tR tS tT tU TV tX Tz Ur Us uV uW vO vU wB wC wD wF wG wJ wK wL wP yD yJ zA) Nt(Dr Hq Hr Hu Hv Hw Hx Ii Ij Il Io Ip Iu Iv Jh Jk Jo Jr Lu Lv Ly Ma Mb Mc Md Me Mf Mg Mh Mi Mj Mk Ml Mn Mp Mq Mr Mu Mv Mw Na Nb Nd Ne Nf Ng Nh Ni Nk Nl Nm No Nq Nr Ns Nu Nx Oe Of Oh Oi Om Oz Pa Pc Pd Pe Pf Pg Po Pz Sf Sh Uy) Qe(dU Eq Ex Fb Fc Fd Fi fR Gb gC Gd Gh gL Gn gP Gz hB Hl Ho iH iP iZ jB kP kQ kR kS Ky Lp Lt mE mI mZ nL nN nY oF oH oK Op Ps Rt Ru Rv Rx Ry Rz Si Sj Uw Ux Uz Va Vh Vj Vw Vz Wb Wg Yd Yg Yh Yi Yj Yk Yl Zq Zx Tm Tl Xa tF) nK(aH aI aK aL Bc bE bI bN Bo cJ cM cR Cu Cv Cw DD dU Et Fp Fy Gl Gz Hq Hw Hx iH Ii Ij In Ip Iq It jB Jg Jm Jn Jt Lv Lw Md Mf Mh Mj Mm Mq Mr Ms Mx mY Nb Ng Nj Nm nN Nr Ny Og Ou Ow Oz Pa Pc Pe Pg Pj Po Qb Qc Qn Vz Yl) Jn(aC aN bM cM Hu Hv Hw Hx Ii Ij Ik Il In Ip Iq Iu jB Jh Jm Jo Jq Jr Kc Lu Ly Ma Mb Mc Md Me Mf Mg Mh Mi Mk Mn Mq Mr Mu Mv Mw My Na Nb Nd Ne Nf Ng Nh Ni Nk Nr Ns Nx Oe Of Oh Oi Om Oy Oz Pa Pc Pd Pe Pf Pg Po Pz Qc) Ih(aC Hq Hu Hv Hw Hx Ii Ij Ik In Ip Iq Iv Jh Jj Jk Jm Jo Jq Jr Lu Lw Ly Ma Mb Me Mf Mg Mh Mi Mk Mn Mp Mq Mr Mu Mw Mx My Nb Nc Nd Ne Nf Ng Nh Ni Nk Nl Nm No Nr Ns Nx Oe Oy Oz Pb Pc Pd Pe Pf Pg Po Pz Qb Qc) On(aF aH aK aM Ao bE bL bQ cC cD cM Ct Cv dB Dd dI Dk Dr Ed EF Eq fR HC hG iA Ib Je jM Jv Kc Kk Ko Kx Ld lK oE oN Ou pF Qt Qw Qz Sf Sh Ss Tz Ua Ur Us Uu Uv Uy Vb Vc Vs Vu Vv Wb We Wh Ye Th) Cu(Ad aF aN aO Bb bM cD Ch cI Ct Dd Dr Du eF Eq Gb Hu iA Ib Io Iz Jg Jt Kc Kk Ko Kx Ld Lw Mm mZ Nf Nk Nm Nn oN Oz Qw Rv Ry Rz Sf Sh Ua UR Us Uv Uy Vc Vh Vs Wb Wd We Wf Yd Yg Yl Zw Ye Tl Xa) Li(DR Ex Fb Fn fR Gb GL gP Gz hB hF iH iP iZ Kd Kg Ki Kj Kl kQ KR KS Kx Ky Kz mE mI nW nY oE oF oH oK Ow Ph Pi pK Ql Rt Sf Sh TT tV Uy Va Vb Vc Vh Vi Wb Wc Wd We Wh Th tF) Fr(aC Aj Dr Hu Hv Hw Hx Ij Ik Ip Iq Iu Iz Jh Jj Jk Jm Jo Jq Jr Lu Lv Ly Mb Me Mf Mh Mi Mk Ml Mn Mp Mq Mr Mv Mw My Nb Nd Ne Nf Ng Nh Nm No Nq Ns Nu Nv Nx Oe Of Oz Pc Pd Pe Pf Po Qb Qc) Mm(aH aK aM aO bA bE bL bM cD Ch cI cM cR cT dB Dd dI dL Ed Fy Gz HC iA Iz Jv Kc Kk Ko Kp Kr Kx Ld Ou Pi Qh Qw Sf Sh St tN tO tR tS TV tX Tz Us Vu Vv wD wE wF wP wQ yJ) Jt(aD aK aM AO As aU aW BB Bc Bg bL Bn Bo bQ bX cC cI cM cN cR cU cV dA dB dD dE dH dI Dk dL EF hC hP Ib Jv Kc Kk Kx Ld lK Qw Qz Sf Sh tT Tz Uk Ur Us Uu Vb Vv Th) Nv(aC Aj aN aO bM Hq Hr Hv Hw Hx Ii Ij Il Io Ip Iu Iz Jk Jm Jo Jq lK Ly Ma Mc Md Mf Mg Mi Mj Mk Mn Mq Mr Mu Na Nb Nd Ni Nk Nr Nx Oh Oi Om Pa Pd Pe Pf Pg Po Pz Qb Qc Qw Rg) Qb(cM Dd Hu Hv Ik In Ip Iq Iu Iv Jh Jo Jq Jr Kc Kp Lu Lv Lw Ma Mb Me Mf Mh Mi Mk Mn Mp Mr Mx My Nb Nc Ne Nf Nh Nl No Nr Nu Nx Oe Of Oy Oz Pb Pc Pd Pe Pf Po Pz Qc Rg) It(Hv Ii Ij Ik In Ip Iq Iu Jh Jm Jo Jr Lu Ly Ma Mb Md Me Mf Mg Mh Mi Ml Mn Mq Mr Mu Mv Mw My Nb Nc Nd Ne Nf Ng Nh Ni Nl Nr Ns Oh Oi Oy Oz Pa Pb Pc Pd Pe Pf Pz Qc) Pj(aA Dp Dr eD eM eP Ez Fn fR Gd Gz hO hP HR hV hW hX Je Jf Jg Jh Jk mE nC nH nL nN Ps pY qA Ql Qm Qn qT qU qV qW qX qY rA rB rC Ry rZ Si Tt Vb Vc Vi Vq Th) Pe(aC Ad aF Aj aK aN AO aV Bb Bc bM bQ cD cI cM cR Ct Cv dB Dd Dk Dr Hc Iv Iz Jm Jq Kc Kk Ko Kp Kx Nc Nj Nl Nu Nx oE Og oN Qw Rg Tz Ur Us Uv Vp Vu Ye Th) Kx(Aa Aj aK Ap Bb Bc Dg DL Ed eM eQ Fw Gb Gd gV Gz Hu Ic Ij Ik Il Iq Jg Jq Jv Kc Kk Ko Lu Lw mZ Nk Nm Nn Ny Og Qw Qz Rg Ri Sf Sh Tz Ur Us Uy Vc Wb) Rg(Aa Ad aK Bb Bc bX cM Cv Dg Dl Dr Ed Fp Fw Fy Ic Ii Ij Il Iq Jg Jj Jm Kc Kg Kk Ko Kp Mx Nk Nm Nn No Nr Ny Oh Pa Pd Qh Tz Uc Ur Us Vh Vq Vu Zq) Jj(aC aK aN Ap bB Bc bM Cp Cq Cv Cw Dg dI Dl Dr Fw Ha Ic Ij Iv Jq Kc Kj Kk Ko Kr Mx Nj nL Nm Nu Nx Ou Ph Pi Po Pz Qh Rm St Tz Uc Us Vh Vu) Ko(aC Aj aK Ao Bc bM cD Ch cM dH dI dL Ed eM Ex Fp fR Fw Ik Il Iq Iz Jv Kc Ld Ml My Ne Nn No Ny Og Oh Pa Pf Po Qz rR Sf Sh Tz Ur Us Th) No(aA Hp Ib Ic Ij Iv jB Jh Jm Jq Jr Jv Kc Kk Kp Lv Lw Mn Ms Mx Nc Ne Nh Nl Nm Nu Nx Oz Pb Qw Qz Sf Tz Ur Us Uy Yl Ye Th) Kc(aC Bb Bc cM Cq dL Ed Ex Fb Fp fR Fw Fy Ij Il Iq Jm Jq Kr Ks Lu Ml Mx Nk Nm Nn Nr Ny Oh Oz Pa Pf Po Qh rR Tz Us) Og(Ad Bb Bc Dd Il Ip Iq Iu Jh Jk Jo Jr Lv Ma Me Mf Mg Mn Mp Mr Mu Mv Mw Nc Ne Ng Nh Nj Nl nN Nr Oi Pd Pf Qc Vu) Ij(aA aC Aj aN bM cM Dr In Iv Iz Jr Kk Lu Lv Lw Mp Mv Mx My Nc Ne Ng Nh Nl Nm Nu Of Pb Qw Sf Sh Vc We Wh) Dr(Aa aC aM bB bU cB cG Co dC dD dF Dk Ed Fw iJ Kd Ky Ne Nk Nm Om Ou Ow Pf Pi Qc Qh Sf Tn Uk Us Uy) cM(Bb bM cI Dd Ed Ex Fp iZ jB jM Kk Kp Kr kS Ld Ml Nn Nx NY oF Qh Rm St Tv Tz Up Ur Us Vh Vq Vu) Zq(aE aN aO aS aW bB bE bM bO bR bS bW cB cC cD cV dD Fw hC iJ iP Jv kP Ne Ns Pi Po Qw Sf Sh Us) Nm(aA aN bA bM cD cI cR dI Iv Jm Jq Jr Kk Lu Lv Mp Ms Mx Nc Ne Nh Nj Nl Nu Nx Po Sf tT Tz Vb) Dd(aC Aj aN Bc bM cD dI Ef Ex Fp Lw Ml Nn Ny Pf Po Qc Qw Qz Sf Tz Uk Ur Us Uy Vb Vc We Wh) aA(Aa Ii Ip Iv Jh Jq Lu Lv Lw Mb Mh Mn Mp Ms Mw Mx My Nc Ne Nh Nl Nr Nu Nx Pb Pd Po Pz Qc) Et(Du Ex Gz hB hF iH kQ lK nY oF oH qA qO rR rW Sf Sh Tn TO Tr tS Tt Ut Vc Vq Th tF) Fy(aC Aj aK Ao aV Ba bM cD Ch Ct dL Dp Hu Ib Ic iJ Ik In Iz Jv Ld Nn Oh Qw Sf Sh Ur Uv) Nj(aC Bc dU Ii Ip Iq Iv Jh Jq Jr Lv Lw Mi Mn Mp Mr Ms Mw Nc Nh Nl Nr Nx Pd Pf Po Pz Qc) bB(Bb eQ fA Gb gZ jB lY mE mI mZ nB nH nL nN oD oT oV oW pH pI pK Sh Uy Vc Vh Vi Wb) Jq(Aj aN bM Iv Jm Jv Ld Lu Lv Lw Mh Mp Mx My Nc Ne Nh Nl Nu Oy Pb Po Pz Qw Ur) Kk(aK Ao Ed Ex fR Fw Il Iq Jv Lu Mx Nc Ne Nl Nn Ny Oh Qh Qz rR Tz Ub Us Vq Vu) Nk(aC cI dU eQ fA fB Fd gC jB Nc nH nL oD oT oV oW pH pI Qh St Vh Vi Vu) Mx(Bb Ii Ik Iv Jh Jm Jr Lv Lw Mn Mp Ms Nc Nh Nl Nu Nx Oz Pb Po Pz Qc) Bb(aK aM Ao cD Ch cI Ct dI dL Ed Fp hC Hu Ik Lw Mh Ml Pf rR Ur) aC(aN Ao Ba Cp cR Cv Cw Ic Ii Io Iq Kp Lw nL Nn Nx Ny Oh Pd Pf) Po(Ib Ik Iv Iz Jm Lw Mn Ms My Nc Nl Op Oy Pb Uy Vh Vu Wb Wh) Nn(Aj aN bM cD Ch Il Iz Jv Kp Ld lK mE mI Qw Tz Us Vq Vu) Jm(Aj aN In Iv Jr Lu Lv Lw Mh Mp Nc Ne Nh Nl Nu Oy Pb Ur) Mn(dU eM Eq Ex fR Gn Ic Iv mI Ms Nc Ne Nl Nu Uy Vc Wb) Ur(Ad Cq Cv Fd Fw Ii Il Iq Kg Ks nL Qh Tv Tz Uc Us Vq) Lw(Ad aK aN Bc bM cD cI Iv Ms Nc Ne Nl Nu Nx Pb Qc) Nx(aN bM Ed Iv mI Mp Ms My Nc Nl Nu Oy Pb rW

Figure 33 Continued

Vu) Ny(Aj aN bM Ib Ic Ii Io Jv Ld IK pF Pg qA Qw tT) Us(Du Fp Fw Gb Ic Il Kp Oh Op Ps uR Uy Vh Vi Wb) Ad(aN bM cl Ct dI Eq Fp Ik Iz
Jv Ml Of Sf Sh) jB(aW bl bM bN bU cF cR Fd Hu mE Oy Oz Pd pK) uR(An aP Bc Bn cN Cq dF dG dH Dl Jy Ou sH) Fw(Kp Ld Lu Qw Rv Sf
Uy Vb Vc Vh Wh Yl) Iv(Ii Iq Jh Lv Mh Mp Ms Nc Nl Nr Nu Qc) Vu(Fp Il Oh Qw rB rR tV Uv wE wG wH wL) Aj(Aa Ba Bc Dl Ii Kg Kp Ks
Pd Vq) aM(Aa dK Fd Gb Io Si Vh Wb Yi Xa) Nu(Jr Lu Lv Mp Ms Nc Nl Pb Qc) Qh(bM Du Eq Qw Sf Vc Wh Yk Th) Ut(dU Eq Sf Vc Wb Wc
Wh Ye Th) Il(Hc Kp Ld IK Qw St Tz Ul) Bc(aN bM cD cl dl kP Ml) Jr(Gb Uy Vc Vh We Wf Wh) Kp(bM Ed Fp Hu Ib Jv Tz) Oh(Ib Jv mE ml
nL oN Tz) bU(dU nN oW pH pK Vh Yi) rR(Dl Ou Ql Qm Rb Ri Uk) Bo(DW EO EW) Nc(Lv Mp Mr Ms Pz Qc) Sf(Al Ii Ks Om Ou Pi) Jg(aN
cD Ch cl Eq tT) Vq(cD Ct cV Ed In oE) Fp(aK bM Qw Qz Tz) Sh(Al Iz Om Ou Pi) Vh(bO Ed jY Ne Uu) Pf(aN aO bM cD mI) Du(iJ Pi Ps Up)
Ex(Hf Ld Lu Pi) Mp(mE mZ Nl Qc) Yi(aW bO cC iP) Qw(Iq Nr Ps Tz) Cv(dl Ed Ml) Dk(Eq Uy Ye) Ms(Ii Nr Pz) Ib(Om Tv Uc) Ic(hO hP hR)
Pa(hA Hc Je) aN(Aa bA Mr) bM(bA Ld Pd) bO(Gb Vi Wb) cR(oT oW pK) mE(Ld nN Ow) Ap(qA tT) Th(rU rW) Mb(eW gV) Nl(Lv Qc)
Yd(hA jY) Ye(iJ Tz) Ri(rW wE) Vb(Cw Pi) Vc(jP Tn) dD(dU pK) cC(pH pK) hC(Aa Gb) DltT EqiJ NrUy MhPz Uclz Hxml IkIq InPi IptN
ZxjD WhOm XacD TljY KrtO QmqA VaiC PbPd aDgV aFdF Constrained panels with 3 analytes, where 1.0E-10 >= 'model p-value' > 0. Contains 362 panels of 38,188,712 total panels evaluated. : Ji{Et(Fp Hx Ii It Jh Jo Lj Lu Lz Ml Mp Ms Mv Mw My Nf Ng Ny Of Og Om Oy Pb) Li(Ii Ik In Jh Jj Jo Lu Mp Ms Mv Mw My Nf Ng Of Og Om Oy Pb Po) Qe(Hv Ii Jh Jj Lu Mj Mp Ms Mv Mw My Of Og Oh Om Oy Pb Qc) My(Fp Ik Im Jg Jl Jp Lu Lz Mm Mp Mu Nn Nw Ok Pb Qa) Og(Fp Im It Jm Jt Lj Lu Lz Me Mp Ms Ok Pb Qa Qd) Lu(Ik Im Jh Lj Lz Mp Ms Mv Mw Of Ok Oy Pb) Fp(Ik Jh Jj Mj Mp Mv Mw Nf Of Oy Pb) Mp(Ik Im Lj Lx Lz Nn Ok Pb Qa Qd) Ok(Ii It Jh Lj Ms Of Om Oy Pb) Qa(Jh Jj Jk Mv Mw Of Oy Pb) Pb(Im Jj Jl Lj Lz Ms) Lz(Ik Im Ms Oy) Lj(Ik In Ms Nj) Im(Ng Of Oy) wE(Gp jD) MeMs IiJl YkeF QdOf JgOy} Ok{Of(Et Fp Im It Li Lj Lu Ly Lz Ms My Nc Nj Og Pb Qa Qd Qe) Og(Fp Im It Jm Li Lj Lu Lw Lz Mp Ms Nj Nn Pb Qa Qe) Ms(Et Fp Im It Li Lj Lu Lz Nj Pb Qa Qe) Li(Ii It Jh Mp Mv Mw My Ng Nq Oy Pb) Lj(It Jj Lu Mj Mm Mp Nc Nj Pb) It(Fp Jj Lz My Pb) Im(Lz My Ng Pb)} Et{Li(It Jh Mp Ms Mv Mw My Ng Nj Of Og Oy Pb) Ms(Fp Im It Lj Lz Mz Nj Of Og Qa Qe) Fp(It Jh My Nc Nj Of Og Oy Pb) Qe(Mp My Ng Nj Of Og Oy Pb) Lj(It Lu Mp Nc Nj Of Og Pb) Im(Lz Ng Oe Of Og Oy) Of(It Lz Nj Qa Qd) Og(It Jm Lz Qa) Lz(It Oy) QaOy} Og{Im(Fp Iq Ir It Jg Jl Jp Jt Lh Li Lj Lw Ly Lz Me Mm Mz Nj Nm Nn Nt Nw Pb Qd Qe) Li(Ir It Jt Lw Me Nj Nm Nw Pb Qa Qd Qe) Lj(Jg Jt Nw On) QeJt} cM{Vt(Ax Cs Lj) Uh(Cs Lj)} Gc{hC(bG Hp)} Nj{Lj(Jp Nw)} MwImLi MzPkwE Constrained panels with 3 analytes, where 1.0E-9 >= 'model p-value' > 1.0E-10. Contains 751 panels of 38,188,712 total panels evaluated. : Et{My(Ih Im Ir Is It Jg Jl Jm Jt Lh Lu Lw Lx Lz Mf Mh Mt Mx Mz Nc Nj Nn Nw Of Ok On Qa Qb Qd) Oy(Ih Ir Is It Jg Jl Jm Jn Jt Lu Lw Lx Mh Mt Mx Mz Nc Nj Nn Nw Of Ok On Qb Qd) Of(Ih Ir Is Jl Jm Jn Jt Lh Lu Ly Mx Mz Nc Nl Nn Nx Og On Pb Qb) Pb(Im Ir It Jl Lu Lx Lz Mh Ms Mx Mz Nc Nj Nw Og Ok Qa Qd) Nj(Ih Im Ir It Jh Jj Lu Lz Mh Mx Mz Ng Og Ok Qa Qd) Ms(Ih Ir Is Jm Jn Jq Jt Lu Mh Nc Nn Nw Qb Qd) Im(Hx Ir Jh Jj Jk Lu Mh Mp Mv Mw Mz Nm Nq Pz) Qa(Hx Jh Jj Jk Lu Lz Mh Mp Mv Mw Ng Nq Oe Pz) Og(Ih Ir Is Jt Lu Lw Mh Mx Mz Nc Nn Ok Qb Qd) Qe(Aj Hx It Jh Jj Li Lz Mh Mv Mw Nq Pz) It(Hx Jj Lu Mh Mz Ng Ok Pz) Li(Hx Jj Lu Mj Nq Pz) Pk(Ch Hu Ib Ik Jj Lj) Mz(Hx Mv Mw Nc Ny) Ng(Jm Jt Lz Ok Qd) Qd(Mh Mp Nq Pz) Lz(Lu Nc) Mh(Mv Nc) Jh(Is Ok) MpOk JjJm} Ok{My(Fp Lu Lw Lx Lz Mf Mh Mm Mu Mz Nc Nj Nn Nw Ny Qa Qe) Im(Fp Ii In Jh Jj Jk Lu Mp Mv Mw Nf Nj Nq Oe Om Oy Pz) It(Ii Ij Jh Jo Jp Lu Mm Mp Mv Ng Nj Nn Nw Oy Pz Qe) Fp(Ii Jh Jj Mj Mm Mp Nb Nc Nf Nj Nq Nw Oy Pb) Qe(Ii Jh Jj Lz Mp Mw Ng Nj Nq Oy Pb Pz Qc) Ji(Hx Jj Jo Ml Mv Mw Nb Nf Nx Ny) Pb(Jj Lu Lz Mh Mm Nc Nj Nn Nw Qa) Li(Fr Jj Lu Mj Nb Nf Nj Om Pz) Lz(Jj Lu Mj Mp Ng Nj Oy) Nw(Ii Mp Mv Mw Nj Oy) Oy(Lu Nc Nj Nn Qa) Mp(Nj Nn Qa) Jj(Jm Nj Qa) Aa(Ms Of) Lu(Ng Nj) Og(Mm Qd) NqQa MuMw} Ji{Im(Ii Ik In Jh Jj Jk Jq Mv Mw Nf Oe Om) Om(Fp Ir Jg Jp Jt Mm Mz Nn Nw Qa Qd) Ik(Hv Ir It Jh Jq Mv Mw Ng Of Oy) Jj(aF aO bM It Jm Lu Lz Mm Mp) Mv(Jg Jl Jp Lz Mm Mu Nn Nw) Mw(Jg Jl Jp Lz Mm Mu Nn Nw) Ir(Hx Ii Ij In It Jq Nb Nf) Mp(aA In Jl Jp Jt Mm) Ii(Jm Jp Jt Mr Pe Qa) Of(Jg Jp Jt Mm Nn) aA(Jh Lu My Oy Pb) Ng(Jg Jp Jt Qa) Hx(Jl Jp Mm Mz) Ny(Jl Jp Mm Mz) Nf(Lz Mz Qa) In(Fp It Qa) Nb(Jl Pe) Jh(Jg Jt) AaMs MjQa YkiA SfaW JlOy JoJt VtcM PfPg aOdH} Li{Pb(Im Ir It Jj Jl Jp Lh Lw Ms Mz Nc Nf Nj Nw Of Qa Qe) Im(In Jh Jj Jk Lj Lz Ms Mv My Nf Ng Nj Of Oy) Qe(Jj Mj Mp Ms Mv Mw My Ng Nj Nq Of Oy) Nw(It Jh Lu Mp Ms Mv Mw My Ng Nj Of Oy) Og(Ih Is Jl Jm Jp Lh Lj Mm Mz Ny) Oy(Jg Jl Jp Lw Nj On Qa) My(aA Jg Jp Lw Mz) Of(Jp Lh Mm On Qd) Jj(It Jm Lh Nj) Mz(Hx Mv Mw) Ng(Jt Lw) Jl(Mv Mw) Jp(It Ms) NjLj VtcM} Nw{Ms(Fp Im Ir It Iv Jt Lj Lu Lw Lz My Nc Nj Og Pb Qa Qe) My(Fp Im It Jg Lu Lw Lz Mf Nj Pb Qe) Og(Fp It Jt Lw Lz Nj Nm Pb Qa Qe) Fp(It Mj Mv Mw Nj Oy Pb) Lj(It Jt Lu Lw Mp Nc Pb) Im(Lz Ng Of Pb) It(Mv Pb) QePb} Lj{Jp(Ir It Jl Jt Lu Lw Ly Lz Ms Of Og Pb) Im(In Jj Jl Jt Lu Lw Lz Mm Ms Nj Pb) Og(Ij Lh Lw Mg Mm Nm Nn Ny Qa Qe) Mm(Jj Lu Ms Nj) On(Mp Ms Nj Of) Jg(My Nj Of) Ms(Jt Lh) NjJt PjcM} Qe{Og(Aa It Jg Jp Lh Lw Me Mm Nj Nm Nn Ny) Aa(Jj Lu Ms Nj No Oe) Ms(Jp Jt Mm) Jg(Mw My Oy) cM(Uh Vt) DdJj LzIm} Im{Lz(Jj Jp Jt Ms Nf Ng Nj Oy Pb) Ng(Jg Jt) Og(Lu Qa) MsJp} cM{Uh(Ar Ax bM Dd Id Jj Rg Vt) Vt(Ar Dd Fp Ir Pj) PjdH} Fp{Og(Jg Jt Mm) MyJg JpPb} Gc{hC(eC Mj Yk)} Ms{Jp(It Lz) OfOn} Qa{Og(Jg Jt)} AadLiA ChJpPk IddHuR Constrained panels with 3 analytes, where 1.0E-8 >= 'model p-value' > 1.0E-9. Contains 1,926 panels of 38,188,712 total panels evaluated. : Li{Mz(aA Ii Ij Im Ir It Jh Jj Lu Lw Mh Mj Ml Mp Ms Nc Nf Nj Nl Ny Of Om Oy) Ms(Ih Ir Is It Iv Jl Jn Jq Jt Lh Lj Lw Mm Nc Nj Nn Ny On Qa Qd) Mw(aA Ir Is Jg Jp Jt Lh Lu Lv Lw Lx Mm Mu Nj On Qa Qd) Jl(Fr Hu Ii It Jh Jj Jk Lj Mj Mp My Nf Ng Nj Nq Of Po) Mv(aA Ir Is It Jg Jp Jt Lh Lu Lw Lx Mm Nj On Qa Qd) My(Ir Is It Jt Lh Lu Mf Mm Nj Nm Ny Of On Qa Qd) Jj(Dc Ir Jp Jt Lj Lw Mm Nc Nw Nx Ny Of Oy Qa Qd) Jh(aA Ir Is Jg Jp Jq Jt Lh Lw Mm Nj On Qa Qe) Mp(aA Im Is Jp Jt Lh Lw Mm Nn Ny On Qa Qd) Ng(aA Is Jg Jp Lh Lu Me Mm Nm Ny On Qa Qd) Ji(aC Aj aN aO bM bQ cD Ch cM Co Ef Gl Qw) Ir(Ij In It Jp Lj Lw Mj Nf Nj Nw Of Oy) Nq(aA Im Jp Jt Lw Nn Nw Ny On Qa Qd) Lu(aA Im Jp Jt Lj Lw Mm Oy Pb Qa) Nf(Ik Is It Lh Lw Lz Nw Qa Qd Qe) Of(It Jg Jt Lw Nj Nn Nx Ny Qa) Oy(Is It Jt Lh Mm Nc Ny Pb Pd) Jp(Hx Ib Iz Lw Lz Mj Nj Qw) Im(Fp Hu Il Lw Mm Oe) It(Ik In Lj Lw Nj Qe) Qa(Hu In Jk Mj Nj) Jt(Aj In Jo Lj Nc) Ik(Jd Mx Nc Nl) Et(Aj aO Pk) Lw(Lj Nj Qe) Qd(Jk Nj Pb) Mx(Hu Mj) Qe(Il Jk) Lj(Mm Nc) aA(Nj Pb) AabM AdAj MuHu IhIn UhcM VtbL} Lj{Og(aA Fr Ir Is It Iv Jd Jh Jl Jm Jq Lu Lv Lx Ly Lz Mi Mp Mt Mu Mz Nc Ne Nh Nj Nl Nt Nu Nv Nx Of Pd Qd) Nj(aA Fr Ir Is Iv Jl Lh Lu Lw Lx Lz Mi Mp Mt Mu Mz Nm Nn Nt Nu Nv Ny Pd Qa Qd Qe) Jd(Ba Ch cM Et Hu Ib Ik In Iz Jj Jp Jv Kc Lz Mj Nq Or Pj Pk Qu Qw Qz Ua Ub Vt Vv) Jl(It Jg Jt Lh Lu Lw Mj Mm Ms Nc Nl Nm Nn Nu Ny Pb Qe) Jg(aA Ir Jh Jj Lu Lw Lz Mp Ms Mv Mw Nc Oy Pb Qe) Mm(aA Ir Is It Jt Lh Lw Lz Nc Of Pb Qe) Ji(aC Aj aK aN bM bQ cD cM Gl iJ Qw) Ny(aA Jj Lu Lw Ly Lz Mp Ms Nc Nl Nt) Qe(Jj Jt Lw Lz Ms Nc Nc Nl Nm Pb) Jt(In Jj Lu Ly Lz Nc Ne Nl Pb) Lh(aA Ir It Jj Lu Lw Of Pb) On(Jj Lu Lw Mj Mw My Nq Pb) Jp(Hc Ib Iz Jv Pj Pk Qw) cM(Et Hb Id Kc Or Ou Qw) Nn(Ir Jj Lu Lw Ms) Pj(aK iJ Jj Or Pk) Et(aC Aj aO Or) Im(Ir Ly Oe) Vt(aK bB bL) AabM GchC LuLw MsQd JjKf bBdU} Nw{Mw(Et Im Ir Is It Iv Jg Jt Lu Lw Lz Mh Mu Mx Nc Nj Nn Of Qa Qe) Mp(Et Fp Im Ir Is It Iv Jt Lw Lz Mm Mv Mx My Nc Nj Qa Qd Qe) Of(Fp Ir It Iv Jg Jt Lu Lw Mm Mv My Nc Nj Nl Ny Pb Qa Qd Qe) Oy(Im Ir It Iv Jg Jt Lu Lw Lz Mh Mm Nc Nj Nl Pb Pd Qa Qe) Mv(Et Im Ir Iv Jg Jt Lu Lz Mh Mu Mx Nc Nj Nn Pb Qa Qe) Lu(Fp Im Ir It Jt Lz Nj Ny Og Ok Pb Qa) Ir(Ii Ij Mj My Nb Nf Nj Ny Og Om Pb) Qe(Hv Hx It Jh Jj Lz Mj Ng Nj Nq) Pb(Jt Lw Lz Mh Nc Nj Nl Pd Qa Qd) Im(Jh Jj Jk Mh Nc Nf Nj Nl Oe) Ok(Hx Jh Lz Nb Nc Nf Ng Ny Om) Fp(Hv Hx Jh Jt Mh Nc Nf Ny) My(Iv Jt Mh Mu

Figure 33 Continued

Nc Nm Og Qa) Og(Is Jg Jm Nc Nl Ny Qd) Lz(It Jt Mh Nc Nj Qa) Qa(Jh Jk Mj Nj Nq) It(Hx Jj Nj Ny) Ji(Hx Ii Ml Ny) Ms(Jm Jn Qd) Jt(Jh Ng Nj) Pk(Hu Ik Nb) Ny(Mh Mz) nK(aC bE) AabM EtJh MjMx NjQd} Et{Pk(Aj Ao Ax Ba Bg cM Cs Dk Ef Gl Gp Hc Ic Id In Ir Iz Jd Je Kc Kk Ld Me Mw My Nb Nf Or Ph Qe Rg Vt) Ng(aA Ih Ir Is Iv Jg Jl Jn Lu Lw Lx Mt Mx Mz Nc Nn Ny Qb) Jh(aA Ir Jg Jl Jm Jn Jq Jr Jt Lu Lw Lx Mt Mz Nn Qb) Mw(Is Jg Jl Jm Jt Lh Lx Mr Mt Mx Nn Ok On Pe Po Qb) Jj(aO bM Dc Is Jn Jt Lh Mz Nc Nn Pb Qb) Mv(Is Jl Jm Jt Lh Lx Mt Nn Ok Pe Qb) Lu(aA Ih Ir Jm Jn Mz Nn Ok Qb Qd) Mp(Ih Is Jl Js Jt Lx Mt Mx Nn Qb) Hx(aA Ih Is Jl Jm Jn Mr Pe Qb) Mz(aA Ii Ir Jr Ml Nf Nl Om) Pb(aA Ih Is Jm Jn Lw Nn Qb) Aj(aH bM cM Dc Dd Ir) My(aA Jn Jq Mr Pe Po) Pz(Ih Iv Jm Jt Ok Qb) Ii(Jl Lh Mr Ok Pe) Aa(Fp Lz Mb Ms) Jm(aA Jo Mb Oe) Hu(Mf Mu Mx) Nn(Nm Nq) Mh(aA Ih) Nj(aA Jl) Qe(aO cM) Ji(aO Gl) Jo(Jt Lh) Ny(Lx Pe) NqQb MbJl NbPe NcOk IvOy JqOm VtcM} Ji{bM(aC Aj aK aN aO Ch cI cM dI Ef Gl Hu Ik Jo Lz Mp Ms Nf Nh Nk Oz Pg Vv) Gl(aC aK Ar cM dH Hu Ik Jj Jp Ju Jv Ms Nh Nk Qe Qw Vt) Jj(aC aK aN Ar Ax bL cD cM dB Dc hG iJ pF Pk Wm) cM(aC Aj aN cI Ef Mp oE oN Qe Rg Uh Uv Wm) aN(aC aF aO cD Ch Ik Lz Mp Ms Nk Qe) Ax(Jv Mp Nk Qw Vt Vv) Ch(dH iJ Qe Rg Uk Wm) Om(Fr Lh Lx Nt Nu Ny) Wm(In Iz Ms Qw Qz) Hu(hC Id iJ pF Pk) Qe(Aa Aj aO cD Co) Vt(aF aK aO bL Pk) Ar(Jv Mp Qw Rf) aA(Ii Mv Mw Of) aC(aL aO cZ Nk) Aa(Jq Lu Lz) Aj(Ad Ir Ms) Jd(Ef Jv Vv) Qw(aO Cs Id) bQ(dH Lz Rg) Ml(Jp Mm) Yk(fP gP) Jv(As Id) dH(aF Mp) iJ(Iz Nq) CoRg FwSf MrNb NkcI IkPk YemM KpVv aKaQ aMdK} Ok{Ii(Ir Jl Jm Jp Lh Lx Mm Mr Mt Mz Nc Nn Ny Pe Qa Qd) Mp(aA Jj Jp Lh Lu Lw Lx Mm Mt Mx Nc Qb Qd) Mv(Jl Jp Lh Lu Lx Mm Mu Mz Nn Ny Qa Qe) Ng(Jg Jp Jt Lh Lw Mm Nc Nj Nn Qa Qd) Mw(Jg Jl Jp Lh Lx Mm Mz Nn Ny Qa) Jh(Jg Jn Jp Lh Lu Mm Nj Nn Ny Qa) Aa(Fp Io Lu Lz Mb My Nj Oe Og) Qd(Jj Lu Mh Mj My Nj Nq Pb Pz) Qa(Hx Jk Lu Mj Nb Nj Oe Pz) Jp(Fp Lu Lz My Nj Nq Oy Pb) Mm(Jj Lu Lz Nc Nj Oy) Ny(Mz Nc Nq Om Oy Pb) Nn(Lu Nb Nj Nq Om) My(Jg Jj Jm Jn Lh) Jo(Ir Jm Jt Mx Nj) Mz(Hx Ml Nf Om) Oy(Lh Mh Mu Pd) Aj(bM cM Dc) Hx(Im Jl Qe) Mj(Mx Qe) Nb(Lh Qe) Hu(Mu Mx) Pz(Ir Pb) Jj(Lu Nc) FpIj NmIm MkPd LhPb} Jp{Ms(Fp Ih Ir Is Jm Jn Jq Jt Lh Lw Mh Mz Nj Ny Pb Qa Qd) Fp(Ik Im Ir It Jt Lw Lz Mm My Nj Nm Of Og Oy Qe) Lz(It Jt Lu Lw My Nj Ny Og Oy Oz Pb Qa Qd Qe) Im(Ir It Jj Jk Lu Mh My Ng Nj Of Oy Pb) Qe(It Iz Jj Mp My Nj Nq Of Oy Pb) Pk(Ba Hc Hu Ib Ik Iz Jj Nb Pj Vv) Og(Ij Ir Is It Jm Jt Ny Qa Qd) Qa(Ib Iz Nj Of Pb) Qw(kP mM nK nL nO) Ch(Jd Kq Ks Pj) It(Jj Nj Of Pb) Iz(Ar Dc Kq) Vv(Ax Dc Pj) Ib(Ir Kq) Vt(bL cM) ArHc MhPb MyJg HuKq QdOf JjJm KxcP} Og{Jg(Ih Ij Ir Is It Jl Jm Jt Lh Lw Lz Mx My Mz Nn Ny Of Qb Qd) Qd(Fp It Jm Jt Lh Lw Lz Me Mm Nc Nj Nm Nn Ny On) Qa(Fp It Lh Lw Lz Me Mm Nj Nm Nn Nu Ny On Pb) Jt(Jl Jm Lh Lz Mm Mt Mz Nc Nj Nn Ny On Qb) Lh(Fp Ih Ir Is It Lw Lz Ms Nm Ny Pb) Qe(Fp Hv Jq Lz Ms Nc On Pb) On(Fp It Lw Lz Ms Nm Of) Mm(Ij Ir Is It Lz Ny) Fp(Nm Nn Ny) Nn(Ir It) FanK} cM{Vt(aC Aj bB bL bM cI cV cX Dc dH dI Ed eF Fw Hu Id Il Jd Jj Js Kf Kn Kr Lh Lx Lz Mh Ml Mt Mx Nf No Nr Oh Pk Qa Rg Sr Ur Wm) Uh(aH Aj aN AO Ba Ch Dc FP Fw Gp Hu Ir Kx Lz Oa oE oN Or Pj Pk Qa Wm) Pj(Aj Ar Ax Cs dL Fa hC Ir iZ Jj Or Qe Rg) Ax(dU gZ jB oW pI pK Ur) Qe(Aj Jj oN)} Im{Fp(Ik In Jj Jt Lw Lz Mj Mm Ms My Nf Ng Nj Oy Pb) Ms(Jj Jl Jt Lh Mm Mz Nj Nn On Pb Qd Qe) Qe(Il Jj Jk My Ng Nj Oe Of Oy Pb) Jj(Jt Lh Mm Mz Nj Nn Pb Qd) Lz(Il In Lu Mm My Mz Qd) Ng(Lh Lw Mm Nj Nt On) Nj(Jt Mz Oy Pb Qd) Of(Jg Jt Lh Mm Qd) My(Jg Jt Mz Qd) Pb(Ir Jl Jt Lh) Oy(Jg Jl Jt) MzHx IrIt QdOe} Qe{Ms(Fp It Jg Jn Jq Lh Lz Nj Nl Nm Nn Ny On Pb) Aa(Ij In Jk Lw Lz Mb Mx My Nq Of Pz) Jt(Aj Fp Jj Lz My Ng Nj Of Oy Pb) Jg(Aj Jh Jj Lz Mv Ng Nj Of Pb) Mm(Fp Jj Lz My Nj Of Oy Pb) Jj(Dc It Kf Lh Nj Nn) Nj(Lz My Oy Pb) Aj(Ad Dc) Lh(Of Pb) LzIl MyaA OfOn} Pj{Or(aC aK aN aV Ax bM dH iA Ik Jj pF Pk) Jj(aK bM Dc dH Fa Pk Qa) Pk(aC Ik Kk Rg Vt) dH(Aj iA Ik Vt) Kq(Aj Ef) Vt(aC aK) HchC} Ms{On(Fp It Jj Jn Jt Lz Mm My Nj Oy Pb) Lh(Fp Ih Is It Jj Jt Lz Pb Qa Qd) Jt(Fp Mm Mz Nn Qa) Mm(Fp Qa Qd) Qa(Aa Jg) LzJg} Gc{hC(As bO bU cP Dl Em Gn Nh Nk Nl Ql Qv Rb Vp Wc We Wm) eC(Aj Cs Fp Pa Uu) SfPk} Jj{Dc(bM Jv Pk Sr Uh Ur Vt) Lh(It Jm Jt Pb Pk Qa) Mm(Fp It Pk Qa) Pk(Kf Kg Uh) AabM FpJt} Jg{My(Lh Lx Lz Mx Mz Qa Qb Qd) Qa(Jh Mw Ng Of Oy) Fp(Jh Mw Oy) Lh(Of Oy) LzOy QdOf} Vt{Ar(aK aP bL bX Nf) Cs(aK aU bB bL bX) bL(Ax bB) AabM DcUr ThgW IbJd} Fp{Jt(Jh Mm My Nc Ng Nj Oy Pb) Mm(It Of Oy Pb) On(My Oy)} Aj{Ad(Ar bC bM dI Ir Lz Mt) JtbM} Of{Qd(Lh Mm On) On(My Oy)} uR{Wm(iA jD tX) Or(Id Mz)} bB{oW(cR dU kI) OzdU} bU{Ax(dU oV) pH(aO Oz)} Nk{DdpK NxgZ bNjB} Ib{Jd(Cq Fa Ir)} Kq{ArFr EfKf HuPa} Aa{LuQa IsbM} Ye{IsmS NxnN} cR{NooD NjoW} LzOnOy MlKfrR NgQaJt HumEjB RgUhPk

Constrained panels with 3 analytes, where 1.0E-7 >= 'model p-value' > 1.0E-8. Contains 5,355 panels of 38,188,712 total panels evaluated. : Ji{iJ(aF Aj AO Ar Ax Ba Bg bL bM cD cI Co Cs Dk EF fP Fr Gl Hc iA Ib Ii Ik Io Ir iZ Jd Jh Jk Li Lz Mj Mp Ms Mv Mw My Nb Nf Ng Nh Of Oy pF Pk Pz Qe Vv) Wm(aF Aj aK aN AO Ar As aV Ba Bg bM cD Co Ct Ef Gl Hb Hc Ib Id Ik Jh Jv Kc Mj Mk Mp Nf Ng Nk Og Ou Pk Qt Rg Uh Uu Uv Vt Vv) Ar(aC aF Aj aK aN AO bM bQ cD Ch cM Co Dk Ef fP hG Hu Ib Ic Ik Iz Jd Ju Ms Nf Nk oN pF Pg Pk Po Qt Qz Rg Uu Vs Vt Vv) Rg(aF aK aN AO aV Ba bF bL bM bX cD dL Fw Gl Hu Id Ik In Ir Iz Jj Jp Jv Li Mk Nk Ou Pj Pk Qw Qz Sr Uh Vt Vv) aK(aF Aj aL aN aO Ax cD Ch cI Cs cY cZ dH dI Ef Hu Id Ik Ir iZ Jo Jv kS Li Ly Lz Mp Ms Nk oE Oz Qe Qw Uv Vs) Qw(aF aM Ao As Ba bM Ch cM dB Ed fP Fw Gp Il In Ir Iz Jd Jj Jp Lv Lz Ms Mt Mu Mx Nn Pk Qa Qe Vt Vu Vv) Jv(aC aF Ao bM cD Ch cI cM Cs Cv Dc Fw Hu Ik In Ir Jj Jp Kc Kk Ko Kp Kx Ld Li Lj Me Ms Nh Pk Qe Vt Vv) Ax(aC aF Aj aN AO bM bQ cD Ch cM Co dB Ef Gl Hu Ib Ik Ju Lz Mj Nh Ou Pg Pk Qt Qx Qz Rf Uk Uu Vs) aO(Aj aM As bW cD cI cM Cs dI dL hC Ik Ir Jp Ju Lj Lx Ly Lz Ms Mt Nk oF Og Pe Pf Qz Uh Vs Vv) cM(aE aF aL Ao cD Ch Co Cs Ct dH dI Dk Hu Id Ik Ir Iz Ju Ld Lz Ms Nk Or Pk Qt Ss Ua Vs Vv) dH(aC Aj aN Ao bL bZ cD cE Co Dk Ef Fr Hu iA Ik Iz Jo Ms My Nh Nk Nq oN Oz Pb pF Pg Vs) Vt(aC Aj An Ao aU aV Ba bM Ch Cs eF Hu Ib In Iz Jd Jj Li Lj Lz Mp Ms Nf Ou Qg Qz) Pk(Ao Ba bM Ch Gl Ib Id In Ir Jp Ju Kc Kk Ld Lj Ly Ms Nb Nf Nk Qz Sf Uv Vs Vv) Sf(Al aY bO Cv dB Dc Dd Gl Il Jm Kd Lj Mj Mp Mx Nh Nk Nl Pa Pi Ql) Vv(aF aN Ao As bL bX Ch Cs Dc dL Ed Fw Gl Ib Ic Id Iz Jp Li Lj Pj) Aj(aC aF aM aN As bW cC cD Cv dB Dc Et Ik Jt Lz Mp Nh Nk Nm) Ch(aC As bW cI dI Id Ir Jd Jp Ju Kq Lj Lz Mp Ms Mt Nh Us) aF(aC aM cD cI dI Ef Et hC Ju Ly Lz Ms Nh Nk Og Or Qe Uh) Ao(aC aN As bM cD Et Gl hC Ik Ju Li Lz Ms Nk Pa Qe Qz) Hu(aC aM aN As Bn cD cI Cs dI Fa Jd Ju Kq Ld Or) Ik(aC aM cD cI Co Cs dB Dk Fa Id Iz Jd Kx Kz pF) Ef(Ad aN As Cs dB Dc Et In Jp Kq Lz Ms Nk Qe) Gl(aM aN aV cD dD Ed Fa Id Jd Lz Qz Ra Rf Uh) Yk(kF kN kO kP lW lX mM mP mZ nA nR nT oK Uu) Vs(aM aN As bM Cq Cs cX Dc dL Fw Id Li Lj Qe) Ms(aM bL bQ cC cD Co dB Dk Ju nK oE pF Qz) hC(Dk fP Fr Hc hG Ib Mj Mp Mw Nf Nq oN pF) Lj(Co Ic Id iO Iz Ju Kc pF Qz Rf Uh Uk) dI(aM bQ cC cD Co dB Mk Nh Nk oE Oz Pg) Ju(Ba cI Cs Fw Ib Id Ir Iz Jd Jj) Co(aC As Cs Lx Lz Mt Pe Pf Uk) Li(bL Ct fP hG iA oN pF Qt Qz) Lz(aC aV cC cD cI oE oN pF) Mp(aC aM As bW cI Cs dB dL) Ib(As Cq Et Jd Jp Qa Sr Us) bQ(aC cN Lw Lx Mt Pe Pf Qe) Iz(As Jd Jp Kk Kq Uk Us) cD(aC cI Lw Mt Nh Nk) Cs(aN Nh Nk Qz Rf) Jj(Aa Id Jd Qz Uk) dL(iA Nh oE oN pF) Dk(Bn Et Pa Qe) Nf(aC aM Bn iA) bM(Ld Or Qt Uk) cI(aM aN Oz Pg) iZ(aJ aP hG Nt) Aa(Mb Of Og) Nk(aM dB hG) Id(As Qt Qz) rR(aZ cA iC) Bg(Jd Uk) Dc(Ur Uu) Gp(Qz Uv) Nq(iO Kq) Nh(aC bW) Ir(aC aU) Qe(bL Ct) Jp(Hc pF) Uy(bU cC) Oz(aN pF) oN(Lx Pe) DdSh EmeF LvhG LyaM SimZ JdUu SrRf QzKk JodB PaoE aDgV aLdD aQaU bIwE} Jp{Iz(As Ax bL bM Bn cC cM Cq Cs Cv dB Et Fa fP Fw Gp Hb Id Ik Il Im Iq Ir Iu Jd Jm Jq Kf Kk Ko Ks Kx Ld Lx Lz Mm Mt Mx Mz Nk Nm Nn Ns Ny Oa Oe Om Or Pj Po Qb Qd Rg Rm Uc Ue Ug Un Us Vt Vv Wm) Pk(aC Ao Ar Aw Ax Bg bL bM cM Cs Cv dB Dk Fr Gp Id Ir Jd Je Jv Kc Kk Kx Ld Li Lu Lz Me Mm Ms Mw Nf Nk Nq Nw Oa Or Oz Pb Qe Qt Qu Qw Rg Uh Uv Vs Vt Wm) Hc(Ax Bn cD Ch cM Cs Cv dB Dc Fa Fw Gp Hb Id Ik Il Ir Jd Jm Kq Ks Li Lx Lz Mz Nk Ns Or Pa Pj Po Qa Qb Qd Qe Rg Vt Vv Wm) Pb(Ih Ir Is Jj Jl Jm Jn Jt Lh Lu Lv Lw Lx Mb Mp Mt Mx Mz Nj Nl Nm Nn Nt Nu Ny Of Og Pd Pe Po Qb Qd) Vv(aN AO Ar Ba bL bM bQ cC Ch cM Cs dB Dd Ed eF fP Fw Ib Id Jd Je Jv Kf Kn Li Lj Oa Qe) Nj(Ih Ik Ir Is Jj Jl

Figure 33 Continued

Jm Jn Jt Lu Lw Lx Mh Mp Mx My Mz Nt Ny Of Og Oy Qb Qd) Ib(Ar Ax Bn Cq Cs Dc Fa Fw Id Kn Kr Ml Mz nK nL Ny Om Pe Qe Tv Uc Un Us Vt) Og(Ih Jg Jl Jn Jq Lh Lu Lw Lx Mh Mm Ms Mt Mx Mz Nm Nn Nt Nu Oz Po Qb) Ch(Fa Hb Id Kf Kj Kx Oa Qe Qh Rg Tz Uc Ue Ug Uk Un Up Us Vt Vu Wm) My(Hb Id Ir Is It Jl Jt Kq Lh Lw Lx Mh Mz Nt Ny On Qa Qd) Pj(aC Ar Ax Ba cM Ef fP Hu Ik Jj Jv Li Lz Or Qe Rg Uu Vt) Ms(Aa Iv Jl Js Lu Lx Mm Mt Mx Nm Nn Nt Nu Nx Of On Qb) Lj(aC aN bM bQ cD cM Hb hG iA iJ iO Je Kc pF Qz Vs Vt) Oy(Ir Is It Jg Jl Jm Jt Lu Lw Lx Mh Mx Nt Ny On Qa Qd) Qe(Aj aN aO bL cM Hx Jk Jv Mh Mv Mw Ng Qt Qw Ua Vs) Lu(Fp Id Ih Ir Is It Jm Jt Lw Mh Ny Qa Qd) Li(aC Aj aN aO bM bQ Jd Jv Qt Qu Ua Vs V

Constrained panels with 2 analytes, where 1.0E-8 >= 'model p-value' > 0. Contains 127 panels of 199,783 total panels evaluated. : Li(aA Et lm Ir
It Ji Jj Jl Jp Lj Lu Lw Ms Mv Mw My Mz Nc Nf Ng Nj Nw Of Og Ok Oy Pb Qa Qd Qe) Et(Fp Ih Im Ir Is It Ji Jj Lj Lu Lz Mh Ms Mx My Mz
Nc Ng Nj Of Og Ok Oy Pb Pk Qa Qd Qe) Ok(Fp Im It Ji Jj Lj Lu Lz Mm Mp Ms My Nc Ng Nj Nn Nw Ny Of Og Oy Pb Qa Qd Qe) Ji(aA Fp Ik
Im Jh Jj Lj Lu Lz Mp Ms Mv Mw My Of Og Oy Pb Qa Qe) Nw(Fp Im It Lj Lz Ms Mv Mw My Nj Og Pb Qe) Lj(Im Jg Jp Jt Lh Mm On) Im(Lz
Og) Qe(Aa Og)

Constrained panels with 2 analytes, where 1.0E-7 >= 'model p-value' > 1.0E-8. Contains 126 panels of 199,783 total panels evaluated. : Lj(aA Ir
Is It Iv Jd Jl Lu Lv Lw Lz Mg Mp Mt Mz Nc Nj Nl Nm Nn Nt Nv Nx Ny Og Pj Qa Qd Qe) Qe(aA Fp Im It Jg Jj Jp Jt Lh Lz Mm Ms Nj Nl Nm
Nn Pb) Im(Fp Ir Jj Jl Jp Jt Lh Lu Mm Ms Mz Ng Nj Pb Qd) Ji(Aa aC Aj aN aO Ax bM cD Ch cM Ef Gl iJ Wm) Nw(bM Ir Jt Lu Mh Mp Nc Nl
Ny Of Oy Pk Qa Qd) Jp(Fp It Lz Ms Og Ok Pk Qa Qd) Og(Jg Jt Lh On Qa Qd) Aa(Et Ok Qa) Fp(Jt Mm Qd) Ms(Lh On Qd) Nj(Qa Qd) Jj(Dc
Lh) Pj(Or Pk) cM(Uh Vt) AdAj EtaA GchC JtLi LhOk Constrained panels with 2 analytes, where 1.0E-6 >= 'model p-value' > 1.0E-7. Contains 313 panels of 199,783 total panels evaluated. : Jp(Hc Id
Ih Ir Is Iz Jj Jl Jm Jn Jt Jv Lh Lu Lw Lx Mh Mp Mx My Mz Nj Nl Nm Nn Nt Nu Ny Of Oy Oz Pb Pj Qb Vt) Ji(aF aK aM Ao Ar cI Cs dB dH Id
Iz Ju Jv Ld Or pF Pk Qw Qz Rg Sf Uh Uv Vs Vt Vv) Aa(bM Fp Im Iv Jg Li Lj Lu Lw Lx Lz Mb Mm Ms Mt Nb Ne Nj Nl Nn Nw Og Qc Qd)
Vt(aC aK Ar Ax bB bL Cs cV Dc dI Et Ir Jd Kn Kq Li Lj Pj Pk Qa Qe) Lj(Fr Hb Id iO Jh Jn Jq Kf Kq Lx Mi Ms Ne Nh Nu Pb Pd Uh Un) Qd(It
Jg Jj Jn Jt Lh Lu Lz Mh Mm Nc Ne Nl Nn Ny Of Pb) Qa(Fp It Jg Jj Jt Lh Lu Lz Mm Ms My Nn Nt Ny Oy Pb) Im(In Iq It Lv Lw Ly Mx My Nc
Nl Nn Nt Oe Of Oy) Pj(aC Ar Ax cM dH dL Fa hC Ir Jj Li Lx Lz Qe Rg) Lh(Fp Ih Ir Is It Jt Lz Mm My Nj Ny Of Oy Pb) Qe(Aj aN cM Jd Jn
Lw My Nc Ny Oy Qw Uh) Mm(Ir Is It Jj Jl Jt Lx Lz Ms Og Pk) Jt(Aj Jj Lx Lz Ms Mz Ng Nj Nn Ny) Et(aC Aj aO bM Ch cI Cs Id Or) Jg(Fp Ir
Jj Lz Ms My Ng Of Oy) On(Fp It Jj Lz My Ng Of Oy) Uh(Ar Ax Cs Dc Id Li Pk Rg) Nn(Fp Ir It Jj Lz Ms Og) Kq(Aj Bg Ch Ef Hu Iz Jj) Jd(Ar
Fa Id Ir Li Lz) Og(Fp Ij Nv Ny) Ok(aC Aj Pk We) Hb(Ax Or Wm) Nw(aC aN aO) Dc(Aj Ur) Fp(It Ny) Li(aN Qw) GceC LzNy SrRg NxnK Constrained panels with 2 analytes, where 1.0E-5 >= 'model p-value' > 1.0E-6. Contains 788 panels of 199,783 total panels evaluated. : Pj(AJ aK
aM aN As Bc bM Bn Ch cN Cq Cs Cu Dc dD dG dI Ed Et Fp Fw Id Ik Il Is iZ Jd Jl Ju Jv Kc Kk Kn Kq Kx Ld Lh lK Lw Ms Mt Mz No Nw Oa
Oh Ok Pa Pe Pf Po Qa Qd Qv Sf Uh Uk Un Us Vv Wm) Vt(Cu Dd Ed eF Fa Fp Fw Hb Id Il Im Iq Jj Jl Jt Kc Kf Ko Kp Kr Kx Lh Lx Lz Me Mh
Mm Mt Mx Nf Nn No Nr Nw Oh Ok On Or Pd Pe Qd Qg Qz Rg Sr Tz Uf Uh Ur Wm) Jd(Aj Ax Ch Cs Dc Et Fw Hu Ik Il Im Iz Ji Jj Jp Jv Kc
Kn Kx Lh Lx Mh Mt Mx Mz No Nw Oa Oh Or Pe Pk Qa Qd Qu Rg Sr Uh Un Us Vv) Uh(aC aM aN aO bM Cv Dd dL Fa Fw hC iA Ir Jj Jl Jp
Kn Kq Kx Lh Lx Lz Mt Mz Oa Or Pe pF Qa Qd Un Us Vv Wm) Mm(aA aC Fa Id Ih Iv Jg Jn Jq Jr Js Lu Lv Lw Mb Mh Mt Mx Mz Nc Ng Nj
Nl Nn No Nt Ny Of On Oy Pb Pe Qb) Fp(aA Ih Ik Ir Is Jj Jl Jm Jn Jq Js Lw Lx Lz Me Mp Ms Mt Mz Nc Nf Nh Nj Nl Nm Nt Nu Nv Nx Pb Pz
Qb) Jt(aA aC Ar Ih In Ir Is It Iv Jg Jh Jl Jn Lu Lv Mh Mt Mx My Nc Ne Nh Nl Nt Nv Of On Oy Pb Qb) Nn(aA Ih Is Iv Jg Jl Jn Jr Lu Lv Lw Lx
Mh Mt Mx Mz Nc Ne Nj nK Nl Nm No Nt Nu Ny On Oy Pb) Lj(aC aK aN BB Bc bM cD cM Dc iJ Jy Kc Ke Kk Kn Ko Kp Or Ou Ow Pk Qw
Qz Sr Uc Uf Ur Ti) Qe(aC aK Ax cD Dc Dd Gc Hb Ib Id iJ Jv Kc Kf Kk Kn Kp Or Pk Qg Qz Rg Sr Uk Ur Vs Vv) Lh(AA aC Aj aN hG iA Ib Id
Iv Iz Jg Jl Jn Lw Lx Mx Ng nK oN pF Pk Qw Rg Ur Uv Vv) Et(aF aH aM aN Ao Ar Ax cM Dc Dd dI Ed Ef Fa Hc Iz Jv Kc Kn Kx Oa Rg Un
Us Vu Vv) Jp(AA aC aN aO Ar Ax bM Ch Cs Fa Hb Je Kc Kx Ld Oa Or Qt Qw Rg Un Us Vs Vv Wm) Jg(aA Aj Ih Ik Is It Jh Jl Jn Js Lw Lx
Mh Mp Mv Mw Mx Mz Nc Nj No Ny Pb Qb) Kq(aM Ar Ax Ba Ct Dk Fr Hb Hc Ib Id Ik Ir Jv Li Lz Mw My Ng Nq Or Pk Ua) Ny(AA Ih Ir Is It
Iv Jj Jl Jn Lu Lv Lw Lx Ms Mt Mx Mz Nc Nj Nl Nt On) Li(aC Aj aK Bb Bc bM cD cM Cv Dc Hb Ib Id Kc Or Pk Qz Rg Sr Un Ur Ti) Id(aK Ar
cM Dc Fa Hb Il Ir Lz Mn Nw Oh Ok Or Pk Qa Qd Rg Un Us) Nw(aF Aj aK Ao Ar Ax bL bM cD Ch cl cM Cs Dc dI Hc iA Iz Kx nK Or Rg) Pk(Ar Ax Cs
Dc Dg Gc Hb Ir Kc Ke Kf Kk Ko Ld On Or Qa Qd Un) Ok(aH aN aO Ar Ax bL bM cD Ch cl cM Cs dB dI Ef Or Sf Yk) Aa(Fr It Jj Jl Jr Lv Me
Mh Mp Mz Nc Nh Nt On Po Qb) Hb(Ar Cs Dc dL Fa Fw Il Ir Jj Kx Lx Lz Mt Mz Oa Qa) On(Aj Ir Iz Jh Jn Lu Mb Mh Mp Mv Mw Mz Nj Pb)
Og(Dc Fr Ih Ir Is It Jl Jm Js Lx Mt Nt Qb) Lx(Ir Is It Jl Jn Lz Ms Mz Nj Pb Ti) Ar(aC cM Dc Jv Ke Lw Qh Qz Un Us) Dc(aC Ct Jv Lz Rg Sf Sr
Tv Un) Ji(Fa Kc Kk nK Oa Sh Si Uy Vj) Nv(Ir It Jj Lz Ms My Nj Oy Pb) Ke(Ax bM Ch cM Hu Ik Jj Rg) Lz(It Jn Kf Mt Mz Nt Nx) Mz(aA Hx
Ir It Nt Pb) Qa(Ib Kc Kn Qw Rg Ti) Jj(Ad Jm Kf Kg Ks Uf) Ir(aC Mt Or Rg Sr) Un(Ax cM Cs Ib Rg) Fa(cM Ib Lu) It(Fr Jl Mt) Wm(uR wQ)
Gc(oE Sf) Kf(Rg rR) Kn(Rg Sr) aC(Bb Im) AjQd AxUr CsQw CuVb NtNj MsJs IsnK OruR Constrained panels with 2 analytes, where 1.0E-4 >= 'model p-value' > 1.0E-5. Contains 1,381 panels of 199,783 total panels evaluated. : Hb(aC
aM Ao As Bc bM Ch cM Cq Cu dH Ed Fp fR Fy Hu Ik Im Is Iz Jd Jl Js Jv Kc Ke Kf Kk Kn Ko Kp Ld Lh Lw Mh Ml Mm Ms Mx My Nn No
Nw Oh Ok Pa Pd Pe Pf Pj Po Qd Qh Qz Rg Sf Sr Uf Uh Un Us Vu) Pk(aC Ad aK Ap Bb Bc bM cM Cu Cv Dl Fa Fr Fw Hu Ii iJ Ik Il Im In Is Iu
Jg Jj Jl Js Jt Kn Kp Kx Lu Lw Lx Lz Me Mn Mp Mt Mz Nf Nk Nm Nn No Nr Nv Ny Oa Og Oh Ou Pe Pf Rg Sr Uf Zq Wm Ti) Id(aC As aU Ax
bB bM bX cD Cs Cu dD dH dL Fw Fy hR Hu hV Im Is Jj Jl Jm jQ Js Kc Ke Kf Kk Kn Ks Kx lK Lu Lx Mt Mx Mz Nn No Nr Ny Oa On Pa Pe
Pf Qh Qz rR Sr Uf Ur Wm Ti) Lz(aA aC Ad aK aN Ar Ax Bb Bc cD Cs Cv Dd Fa Fr Ih Ii iJ Ir Is Iv Jh Jl Jm Jq Js Kc Ke Kn Ko Lv Lw Mn Ms
Mx Nc Nh Nj Nl Nm Nu Oa Og Or Oz Pb Pz Qb Sr Tz Uf Un Us) Ke(aC Aj aK aM aN AO cD cI Cs Dc dH dL eF Fa fP Fw Gp iA Ib Il Ir Iz Jd
Jv Kc Kx Li My Nb Nf Ng Nn Oa Or pF Qa Qd Qe Qt Qw rR Sf Sh Sr Ur Us Uu Vs Vv Wm) Ir(Aj aK aM aN Ar aU Bb bM cD cM Cs Dc Fa Fr
hG Ib Ih iJ Is It Iv Jl Jm Jn Js Jv Kc Kf Kk Ko Lv Lw Mn Ms Nc Nj nK Nl Nm Nt Nu Nx Pb Qb Qw Uf Un Ur Ti) Kq(aN Ao bM cD cl cM Cs
dL eF Eq Fa Fw Gp Jd Je Kc Kl Kx Lu Lv Nb Nf Ny Of Og Ql Qu Qw Rg Sf Sh Sr Ss Tn Uc Uo Ur Ut Uu Vb Vs Vv Wm Ti) Mz(aC Ar Ax bM
Dc Fa Fr hP Ih Ij Is Iv Jj Jl Jm Jn Jr Js Kc lK Lv Lw Ml Mp Ms Mt Mv Mx My Nc Ne Nf Nh Nj Nl Nm No Nu Nv Og Qb Rg Sr) Dc(aN Ax bM
cD Ch cI cM Cs dI Fa Hu Ik In Iz Jp Ju Kc Kk Ko Kx Ld Lw Mt Nk Oa Ok Or Qd Qt Qw Sh Ua Ub Uk Uu Vb Vs Vv Wh Wm Ti) Ar(Ad aF Aj
aK aN aO Ax Bb Bc bE bM cD Cu Dd fP Fy Hu Ik Iq Is Jg Jj Kc Kf Kk Kn Lh Lj Mm Mt Nj Nk Nm oN Or Qa Qd Up Ti) Lh(aF aK aM aO Ax
bL bM cD Ch cI cM Cs dB eF Fa fP Gl hA HC jD jM Jv Kc Kk Kx lK IM Oa Or Ou Sf Sh Uu Vc Vs Wh Ti) Uh(Ao As Bn cD cE Ch Cq Cu dB
Ed Et Fy Gp iC Il Iq Is jD Jt Kc Kf Kk Ko Kp lK Lw Ml Mx nK No Oh Ok Pd rR Sr Tv Uf Vs) Gc(aC aM dD hA iB iC jD jF jG jI Jj jL jP jT jU
jV jY Lj lL lM lN Ni Nk Or Pi Qh Qz Rg Uk Un Us Uu Uy Vb Vi Vt) Fa(Aa aK Bb bQ Dg Dl Hu Ik Il Jj Jt Kc Kf Ko Li Lj Mj Mk Nf Nk Nm
Nw Ok Or Oz Qa Qd Qe Qw Qz Sr Uf Un Wm) Jd(aC Ao Ba Bg bM cM Cu Ed Fp Fy Ha Iq Is Je Jl Kf Ld lK lL Ml Mm Ng Og Qt Qz Tz Ua
Ub Uu Vs Vu Wm) Ax(aC aN Bb bM cD cM Ic Jj Jt Jv Kc Kf Kk Kn Ko Lj Lw Mm NK Nm Or Qa Qd Qw Qz Sr Uf Us Vv Ti) Un(aC Aj aK
aN aO bL Ch Dd eC Ed eF Fw hG Hu iJ Il lh Iz Jj Kc Kf Kn Nw Qa Qw Sr Uf Ur Uv Wm Ti) Cs(aC Ad aK Bb cD cM Ic Jg Jj Jt Jv Kc Kf Kn
Ko Kp Lw Mm nK Nm Or Qd Qz Sr Ub Uf Us Vq Ti) Jl(aA Fr Ih Ij Is Iv Jj Jm Jn Js Lw Mb Ms Mt Mx My Nc Nj Nl Nm Nt Nu Nv Nx Oy Oz
Pb Qb) Kf(aC Aj bM Ch cM Ed Hu Ib Ik Il Iz Li lK lM mE Oa Og Or Qa Qd Sr Ss Ur Us Uu Vv Wm) Or(aK Ap aV Bb bM cM Dg Dl Im Jj Jt
Kc Kn Ko Kp Lu Mm Nm Nn Oa Qa Qd Sr Uf Ur Ti) Is(aN bM cM Fr It Iv Jm Jn Lw Ms Mt My Nc Nj Nl Nm Nt Nu Nv Nx Oy Pb Qb We)
Qd(aC aK aN bM cD Ch cM Dd iJ Iz Jv Kc Kk Kn Kp Kx Qw Qz Rg Sr Uf Us Wm Ti) Jn(aA Fr Ih It Iv Jj Lv Lw Mp Ms Mt Mx Nc Nj Nl Nm

Mn Mw Mz NC Ng Nj NN No Nt Nv nW Nx Oa Oh Ok Om On Ou Ow Oz PH Pj Pk Po Ps Qa Qb Qc Qd Qe Qg Qh Qm Qn Qt Qu Qv Qw Qx
Qy Qz Ra Rb Rc Rf Rg Rh Ri Rj Rm Rv Rx Sj Sr St Tn To Tr Tt Tv Tz Ua Ub Uc Ud Ue Uf Ug Uh Uk Ul Um Un Uo Up Ur Us Uu Uv Uw Ux
Vb Vi Vo Vp Vq Vs Vt Vu Vv Vz Wd Wf Wh Yi Yl Xa Wm Yf) gZ(aF aK Al An aO AR Ax bB bl bM BN cJ Cp Cq cR Cs DD Dp Fa Fc Fd
Fp Fy Ha Hb Hc Hf Hw Hx iA IH Ii Ij Il Im Ip Iq Ir Is Iu Iv Je Jk Jm Jn Jq Jr Js Ju Ke Kg Ki Kl Kq KS Ky Kz Lh Li Lj Lt Lx mE Mf Mn Mp
Mq Mt Mw Mx Mz nA Nf Ng nH Nj nL Nn No Nv nW Ny Oa Oh Ok Om On Ou Ow Oz Pa Pe PH Pi Pj Pk Po Pz Qa Qb Qc Qd Qe Qg Qh Qm
Qt Qu Qv Qz Rb Rc Rf Rj Rm Rt Rv Sf Sr Ss Tn To Tv Tz Ua Ub Uc Ue Uf Ug Uh Uk Um Uo Up Ur Us Ut Uu Uv Uw Ux Vb Vi Vo Vp Vq
Vs Vu Vv Wc Wf Yg Yi Xa Wm Yf) fB(Al Ar Ax bB bN Cq Cv Dd Dp Fa Fb Fd Fi FP Fy Gn Ha Hf Hw Ib Ij Im Ir Is Iv Iz Je Jk Jo Jq Jr Ju Jv
Kg Kj Ko Kq KS Kx Ky Kz Li Lj Lt Lx mE Mf Mn Mw nC Ng nH NJ nL NN No Nt Nx Oh Ok Om On Ow Oz Pe Ph Pi Pj Pk Ps Qa Qb Qc Qe
Qg Qh Qm Qn Qt Qu Qv Qw Qx Qy Qz Ra Rb Rc Rf Rg Rh Ri Rj Rm Rt Ru Rv Sh Sr Ss St Tn To Tr Tz Ua Uc Ud Ue Uf Ug Uh Uk Ul Um
Un Up Ur Us Uu Uv Uw Ux Uy Uz Va Vc Vi Vj Vo Vp Vq Vs Vt Vu Vv Vw Wd We Wg Wh Yi Yj Yl Xa Wm Yf) pH(aC Al aO Ar aW Ax
bB bE bN cF cM cN cO Cq Cs DD dH dM Dr eC Ed Eq Ez Fa Fd Fn Fw Fy Gn Gp Ha Hb Hw iA Id IH iP Ir Is Jd Je Jf Jk Jn Jq Jr Ju Jy kF Kg
Kl Kn Kp Kx Ky Li Lj Lt Lx mE Mf Ml Mn Mx Nj nL Nn No NR Nx Oh Ok oP Or Ow Pe Ph Pi Pj Pk Qa Qb Qc Qe Qh Ql Qm Qn Qu Qw Rc
Rf Rg Ri Rj Rm Ss To Tv Tz Ua Ub Uc Ue Uk Un Uo Up Ut Uv Ux Vb Vi Vo Vs Vu Vv Wb Wd Yj Zx Xa) oD(Ar Ax bB BN cJ cR De Fa Fd
Fp Fw Fy Hw Il Ir Is Iv Jk Js Kg Ks Kx Ky Lh Li Lj Lx mE He Mn Mt Mw nC Ng nH nJ nK nL Nn No Nv Nx Oh On On Pe Ph Po Qa Qb Qe
Qu Qz Tz Uk Uu Vb Vq Vu Wf Yi) nK(aC aH aK AL aQ Ar Ax bB bE BN cJ Cs cZ Dd dI dR eF Eq Fa Fc Gd hC iH Ir Is Je Jp Kf Kl Kx Ld Lh
Lp Lt Lx Mn Nn Nv Nx Ny Or Ou Pe pF Pi Qe Qv Rg Ss Uh Uu Uw Ux Vb Vw Yi Yl Ye) eQ(aO Ax bB bN bU cJ Cs Dd Fa Fd Gn Ha Hb Hv
Ih Ij Im Iq Ir Is Jk Jq Jr Kl Ks Kx Ky Li Lj Lx mE Mf Mn Mx nC nL Nn No Nr Nt Nx Oh Ow Pe Ph Pi Pj Qa Qb Qe Qm Rc Ss Tz Ut Vb)
oW(Ax bB bE BN bW cJ cK Cq cR CS DD De Dr Fa Gn Ha Hb Hu Hw iH Ir Is Jk Jr Kl Ks Kx Ky Li Lt mE Mn Mx nC Nj nL Nn oK Ph Po Qa
Qb Qe Qm Ss Up Ut Uu Ux Vb Yi) bN(kC kE kF kG kl kK kN kO kP lW lX lY mE mF mH ml mM mP mS mT mU mW mY mZ nA nB nC nD
nF nH nl nJ nL nM nN nO nR nT nU oO oP oQ oT oV pI) oT(Al Ax bB Fa Fy Ha Ir Is Jk Ks Kx Li Lj Lx Mn Mx nL Nn No Nx Oa Pe Ph Po
Qa Qb Qe Qn Qu Rm Ss Tn Tt Tv Tz Uc Ue Uk Ut Uu Vb Xa) oV(Ax bB Dd Fa Fd Fy Ir Is Jn Kg Ks Kx Ky Li Lj Mn Mx nL Nn No Pe Ph Qa
Qb Qe Qu Ss Tn Tt Tv Uk Ut Uu Ux Vb Wf Yi) pl(Ax bB Cs Dd Fa Fd Fy Ha Ir Is Jk Ks Kx Li mE Mn nH nL Nn No Pe Ph Qa Qb Qc Qe Ss
Uu) mW(aC Ax cJ Dr Du Fa Kx Ld Or Pi Ru Rv Uu Ux Uy Vb Vh Vi Vj Vq Vw Vz Wc Wg Yi Yl Yf) gC(Cq Fa Fd Fy Ha Ho Ih Ir Is Ks Kx
nC nH nL Nx Ow Ph Pi Pj Qa Qb Qe Qn Ut Vb Yi) nL(aC Al AR Ax bB cJ Cs cZ Dd Hp iO Je Kx Lx Or Pj Rg Ss Uh Ur Vq Ye) kG(Ow Rt Ru
Rv Uh Ur Uw Uy Uz Vb Vc Vw Wc Wd We Wf Wg Wh Yf) nH(Ar Ax cJ Eq Hp Je Pi Pj Rz Ss Uh Uu Uw Vb Vw We Ye) bB(Fd mE mH mZ
nB nC nN Ps Rt Uy Vc Vi Wb Wc Yf) Vb(mE mP mT mU mY nA nJ nN nO nR nT nU Pi) mE(aC Ar Ax bE cJ Cs Kf Kx Lp Qv We Ye) Vh(jI
jK jL jO jP jT jU jV jY lL) nO(Qw Rg Ss Ug Um Uo Ur Uu Vq) aC(ml mP nC nJ nN nT nU Zq) oP(Ax Fa Fd Kf Ow Sr Tz Um) nN(An Ar aY
cJ Dd dI Pj) kP(Ar Bc Kf Oa Vq Vu Zq) Ye(mT nA nJ Qa Qd Qe) lX(Ar cJ Fw Pj Sr Vq) ml(Ar Ax cJ Dd iH Vq) Eq(dX Jp nA nJ Ok) Yd(iC jE
jH jP lM) Sf(Hb Mn Ok Pj Qh) oO(Ax Dd Fd Kf Yi) nC(Ar cJ Kx Pj) Si(hA jP jT) Ok(Sh We Yg) nD(Pi Pj Vq) oQ(Ax Fw hC) Wm(sF sH)
Yi(gP iP) Zq(cM Vt) Tl(jP Qh) cJ(mZ nF) dX(Kx Vt) AjeO ArmZ GnjE MbgV MnSh VzjY KfyJ OpiB TkrR VchA VqmS bEnJ sHpS}
nK{Lh(aA aC AD AF aG aH al AJ aK aL aM aN AO AP aQ aR aU aV Aw AX aY aZ Ba BB bE BG bI bJ bM bN BO bU bW bZ cA cE cG Ch
cI cJ cK cL cM cN CO CP cQ cR CS Ct cU CV Cw CX cY cZ dA DB dC DD DE DG dH DI Dk DL dM dN Dp dR eC EF Ez gL gW Gz HC Hf
hG Hu Ib Ic iH iJ Is Iz Jd Je Jf Jj Ju Ke Kg Ki Kj Kl kR Kx Lj IL Mk MS My Nc nD Nl Nx Om Or Ou Pz Qn QU Qv Qw Qx Qy Qz Rf Rg Rm
Ss Tn Ua Ug Uk Ur Uu Uw Vs Vz We Wh Yg Yk Yl Wm Tj) Jp(aC aO Ax bB bE Bg Cp Cs Cv cX Dp Ed EF Eq Ez Fa Fb Fn Fw Fy Gl Gz Ha
Hb Hc Hf IB Ic Id Is Iz Jd Je Jf Ju Jy Kc Kd Kf Kk Kl Kr Kx Ky Ld Nx Oa Or Ow Pi Pj Qg Qh Ql Qn Qt Qu Qv Qw Qx Qy Qz Ra Rb Rc Rf Rg
Rh Ri Rj Rm Sr Ss St Tn To Tr Tv Tz Ua Ub Uc Ud Ue Uf Ug Uh Uk Ul Um Un Uo Up Ur Us Ut Uu Uv Uw Vb Vo Vp Vq Vs Vt Vu Vv Vz
Wd We Wh Yg Yl Wm Tj) Yl(AA aC aH al aK aL Ao AW aZ bB bE bl bN bO bR bU bX cA cD cM cN cQ cR Ct Cu cY cZ Db DD dE Dg dK
dM Et fA Fi Gb HB Hu Hx iJ Ik iP Iu Jj Jn Jt kC kG kl KO KP Kq KR Ks lX lY mH mM Mn mP mS mU nA nB Nc nD Nf nJ Nl Nm nO nT Nx
oD Og oH Ok On Op oT Ou oV Pb Pd pl Pj Qm Rf Rg Rh Ri Rj Wb We Yd Yg Yh Yk Zq Tj Yf) Nx(aA aC aH al Aj aK aL Ar aU Ax bB bE bJ
Bo Cs Ct Dp dR Du Ed Fi Fp Gd Gn gW Gz hC Ho Is Je Jj Jo Kj Kx Lj lL Mh Mr My Nc nN Oa Or pK Qz Rz Sh Ur Va Vb Vs Vz Wd We Wh
Yg Yh Yk Zw Zx Xa) Og(aH aK Al Ax bB Bc bE Bo cJ CS Cv Cw Dc DD Dr Du Ed Eq Fa Fb Fy Ha Is Ke Kf Ki Kn Ko Kq Ks Kx Nw Oa Ow
Pk Qh Qn Rm Rt Sr Tr Tz Uc Ue Uf Uh Un Us Ut Va Vq Vt Vu Vz Yi Yj Yk Xa) Vz(aC aH al aK aL aQ aU aV bB bE bU cD cJ Cq cR Ct Cu
cV cY dA dD dE dR eC eF Et fP hB hG iJ iP kI kP mH Mn mP nA Nf nT oD oF oH Oi Ok Op oT Ou oV pI Yd Ye) jU(aG aH al aO bB bC bF
bG bH bN bQ cD cE cJ cR Cu cV dF dJ Fw gL Gp gW iA Ib iH iJ iO iP Ju Ki NW nY oH oN PF Pi Ql Qn Qz Ua Uh Ur Vp Wm tF) aC(AA
aG Ao Ba bB Bc Bo cR Cu Cw Dg Dr Et Fy Hb Ip Ir Is Jq Kc Ke Kf Ko Kq Kx Ma Mg Mm Mp Nm Nn No Nv Nw Ok On oQ Ou Ow Qe Uf
Uh Un Vi Zq) Nw(aA Aj aL Ax bB bE bJ bN cJ cM Cs dD EF gW hC Hf IB Ic iH Iz jE jL kP IL Ms My Or Qv Qy Rg Ri Ug Ur) jF(aD An aR
bA Bn cE cT Cv Dp Fa fP Gl Ha Hf Ic Ld Oa Ow Pj Qn Qt Qw Qy Rf Sr To Ud Uh Un Up Us Vp Vt Wm) qY(aE Aj aM Ar aV Bb bC bH bI bJ
bN cI cJ cP Cs Ct CU DL Dp Ed iH iO nY Or qU Rg Ri Tz Ue Ur tF) bE(AA bU bX cF cR Cw Dr Et Gl Ir Kf Kq Kx Ma Mm Nm Nn Wo Nv
Ok On oO oQ oV Ow Un Vi Wb Yi Zq Xa) cR(bB Du Eq Fc Fd Gb Hl Hp Lp Lt oD Op Rt Rv Rx Sj Uh Ux Va Vb Vh Vw Wd Wf Wh Yd Yi
Zx Ye Tm Xa) al(Dr Du Eq fB Fc Fi Gd Gn Lp Lt Op Ps Rv Rx Sf Si Uw Ux Vb Vh Vi Vw Wc Wd We Wh Ye Tl Xa Yf) gW(aL cJ cP cQ CU
Hc iO lr jE Jk Js jV kK kS IL lY Mr nF No Ou Pe Qz Uh Un Vt) Ok(aA Ad Aj aL Ax Bo cJ Cs dD EF Eq Ez Gd hC Ib Iz Kx Or Rg Rx Rz We
Yg) aA(aM Ax cJ Cs Fa Fp Ip Is Kx Lj Lx Mn Mz Nn No Oa Oh On Qc Qe Qv Un) cP(eD hA iB iC jD jH jl jL jO jQ jR jT IK IL IM IN IO qT
qU qW qX rA) Kx(aG aK aL aR cM Cv Dd eC eQ fA gC Hw iJ Jj mH nW oH oV Rf Rg) Uh(aL cM eC hC jD jE Jj jM jP jQ jR jT IK mH Nh
oV qU qW Rf Rg) oV(Ax Dr Du Fa Fc Pk Qn Qv Qw Qy Rv Us Uu Uw Wd We Wf Wh) Ye(Dd Is Jk Jm kI Ks Mn Ng Oh On Qz Rm Tz Ua
Yi) Vb(Ao cM Cv Dc Et Hb Hw iJ Jm kl Kq Ks Oz Pb Pc) bB(Ax Bc cl dI Dr fB Gh Gz Qe Uy Vs Wb We Yx Wm) cM(Ar Ax Cs Dr Ir No oO
pH Pj pK Qe Rv Vj Zq) We(Fy Jl Jm kI Kq Ks Mn Ng oD oH Rg Tn tF) qV(bH cJ cU Ed eF gP hC iH iO Ki Or Qz Rg) Ou(Ct Hu jD jE Jj lM
Mv Of Uw Yg Yk) iB(aK aS bJ Hc My Pf Pj Qc qU Qy Qz) Du(aH aL Cu Dd Et kI oD oH Op oT) jE(Bo bQ bZ cE eF Gp nW Or Ow Pj) Et(Ax
Cs Eq Gd Or Qv Sf Vh Vw) aK(Ax Cs Dr lr No oO Qe Qn Wb) Jj(Al Fy Kf Kq Ks Ow Pj Uf) Rg(Aa Hl No Sr Vj Yh Zq Zx) cJ(Dr Gz Kf Kq
Nn Ow qW Yk) jD(Ad Aj eF Gp Ib Ld Ow Pj) Ur(Al Jm Kf Ks No Nv On) jQ(Ar Cu Cx dM Fy Gp Sr) jV(aG aR aS cQ dR iO oH) IL(aG dI Hc
Ju Pj Rj rZ) Dr(aL aU aV cY dD Qv) Mn(Eq Gd Sf Si Wb Yk) Yg(Cu Nv Qh Tn Ut Yi) Kq(Aj Ct Ef fB My oP) Or(Aa Cw Gl Mm Wc Yf)
Fa(aG fA Op oT pI) Gz(Dd Kk Ks mH Mm) Pj(hC jT jY lM qU) aL(fB lr oO Qe Zq) qW(bA Cu Gp kS Qz) kl(Gh pK Rv Wd Wh) On(Aj Ef Eq
Vw) aH(fB Uy Vi Tl) dD(Dd Ir oO pK) jY(aR aS Ju nW) Gp(eD jO jR) Is(In It My) Yi(Ct Oy Oz) Wh(Jl Jn Nq) kP(Bc Tz Yf) Yh(Fy Jq) Zq(Dl
mH) Qe(bU cY) Qz(jL jR) Ow(Ct Oi) Vt(eF mH) bA(jR rA) iC(aR nW) hB(Wd Tl) pK(gC Mk) AxeC CwhC DdEq YfaM GlmM NoRf MyUt
NgUf HbSi IrQv YkoH ZwKs JmLp KfUu KofB RxoT NvoP dRIK iOqT} eP{Kx(Aa aC Ad aE aG aH al Aj aK aL aM aN AO aP aQ aU aV
Aw aY bA BB Bc bE bF Bg bH bJ bL bN Bo bS bW bZ cB Ch cI cL cM cN cO cS Ct cU Cv Cw cY cZ dA Db dD Dg dH dN DR eF Et Fb FP
Gb Gd Gh Gn gP HB HC Hf hG Hu Hv Hx iA Ib IH iJ Ik In iO It Iu iZ Jj Jr Jt Kc Ke Kk Kn Ko Kp kR kS Kz Ld Li Lj Lu Lv Ly Me Mf Mq Mv

Mw Mx Mz Nb Nc Nf Nl Nr NW Nx nY OE OF Og Oi OK Om oN Op Or Oy Pa PF Pi Pj Pk Po Pz Qb Qg Qt Qu Qv Qw Qy Ra Rb Rv Ry Rz
Sh Sj Tv Ug Uh Um Un Ur Uy Va Vb Vh Vq Vt Vv Vw Wb Wf Yj Zw Ye Tm Tl tF) Jp(Dp Du eC Ez Fa Fb Fc Fd Fi Fn Fy Gh Gz Ha HB HC
HF hG Hl Ho Hp iA Ib Ic Id iH iJ iO IZ Jd Je Jf Ju Jv Jy Kc Ke Kf Kg Ki Kj Kk Kl Kn Ko Kp KQ KR KS Ky Kz Ld Lp Lt nW nY Oa oE oF oH
oK Op Ou Ow Ph Pi Pj Pk Qh Ql Qm Qn Qu Qv Rg Ri Ru Rx Ry Sh Si Sj To Ub Ug Uh Uu Vt Vv Vw Vz Wb Wd We Yd Yg Yh Yi Yj Yk Zw
Zx Ye Tm Tl Xa tF) Vt(aA Ad Aj aN Ao aQ Ar aS bG bH bL cC cM Cp Cs cY Dd dJ Dp DR Eq Et Fc Fd Fi Gh Gn Hb Hl Ho Hp Ib Ih In Ip Iu
Jf Jj Jm Jt Kc Kf Kk Kn Kp kS Ld Lp Lt Lx Ly Mn Nt Nw Og Oi Om Op Ow Pj Pk Qb Qc Qg Qv Qw Ra Rb Rc Rj Rm Rv Rx Ry Rz Si Sj Tt
Tv Ub Ue Ur Ut Uv Ux Uy Uz Va Vb Vc Vh Vi Vj Vw Wb Wc We Wf Wg Yi Yj Yk Yl Zw Zx Ye Tm Tl Xa Yf) Nw(aN Eq Ex Fc gP Gz HB
HC HF hG Hp iA Id iH iJ iO iP IZ Kc Ki Kl kQ kR kS Ky Lp Lt nW oE oF oH oK oN Or pF Ph Pi Pj Pk Qn Qu Qx Rg Ri Rm Rv Sf Tn To Tr
Tt Tv Tz Ua Ub Uc Ue Un Ur Uv Uy Vb Vi Vv Zx Ye Tl tF) Un(Aj dR Eq Fc Fd Fi Gd Gh Gn Hl Ho Hp Kc Ld Lp Lt Op Ow Pj Ps Qv Qw Ra
Rt Ru Rv Rx Ry Rz Si Sj Ur Uw Ux Uy Uz Va Vb Vc Vh Vi Vj Vw Vz Wb Wc Wd We Wf Wg Wh Yh Yi Yj Yl Zw Ye Tm Tl Xa Yf) Mn(Dr
Du Eq Fc Fi Gb Gh Gz Hc Hl Ho Hp Kc Kk Ld Lt Op pF Ps Qw Rt Ru Rv Rx Ry Rz Sf Sh Si Sj Uw Ux Uy Uz Va Vb Vc Vh Vj Vw Vz Wb
Wc Wd We Wf Wg Wh Yd Yh Yi Yj Yk Yl Zq Zw Zx Tm Tl Yf) Lx(Du dW Eo Eq Fd Gh Ha Hb Hl Ho Hp Ib iJ Kc Kk Kp Ks Ld Lp oH Op Pj
Qw Rm Rt Ru Rv Rx Ry Rz Sf Sh Si Sj Tv Ur Ux Uz Va Vb Vc Vh Vi Vj Vw Vz Wb Wd We Wg Wh Yh Yl Zw Ye Tm Tl Xa Yf) Hb(aC aK
aM aQ Ar aS aV Ax bM cM Cs Db dD dL dM eC Fa Fp Fy Gd hC Hl Hr kS Lh Lj Nf Or Ow Po Qn Qv Ry Vz Wh Yj Tl Xa) Vq(bL Fc Fi Gb
Gn Hl Hp Jj Kc Kn Lp Lt Ru Ry Rz Sf Sh Si Uw Uz Va Vb Vc Vh Vw Vz Wd We Wg Wh Yd Yg Yh Yj Yk Zq Ye Tl) Ou(Dr Eq Fc Fd Gh Gn
Hl Ho Hp Jj Lp Lt Op Rt Ru Rx Ry Rz Sf Si Uy Vb Vh Vz Wc Wd We Wh Yi Yk Yl Ye Tm Tl Xa Yf) Pj(aM aN Ar Ax Bc bH Bn Cv dD De
dG dL Du Ex Gd hC Ho Hx Ir Jq Jr Ki Mp nW Oa Ok Or Po Qn Ry Sf Sh Uy Vz Yl) Ar(Eq Fc Fd Gb Ho Kc Ps Rt Ru Rv Rx Sf Sh Uh Ux Uy
Uz Va Vc Vi Vj Vw Wb Wc Wd Wf Wg Wh Yi Yk Ye Xa Yf) cG(Dr Du Eq Fc Gb Hl Ho Hp Lp Lt Op Ps Rv Ry Rz Sf Sh Si Uw Ux Vb Vi Vj
Vw Vz Wc Wd We Yg Yl Zx Ye) Yi(Aj aM aW bB Bn bS cJ Ct Cx Hc Hp Hu Ih Io It Jk Lp Lv Ml Nv Ny Qn Qw Rg Tv Ua Vp Vv Yg Ye Tl)
Lh(Du Eq Fc Ho Kc Lt oH oN pF Rv Ry Sf Sh Tv Uv Uw Uy Vj Vz Wb Wc Wd We Yd Yl Zw Zx Ye Tm Tl Xa) Mt(Fc Fi Hl Lp Op Rv Rx Sf
Sh Si Sj Uw Uy Va Vb Vh Vi Vj Vw Wc Wh Yl Zq Tl) Eq(Ao Bc CO Cu Dk Gl Is Ke Ld Li Mr Nb Ni Nn Nq Om Ow Pi Po Rz Uf Zq) Vb(bB
Fy Hw Ij Il Is Iu Iv Jr Li Mg Mk Na Nb Nm Nt Nu Ow Pd Po Qe Uf) Ok(dR Du eF Gb Hp Kc Lp Op Qn Rv Rx Rz Sf Uw We Wf Wh Zx Ye Tl
Yf) Fy(Dr Hp In Jj Kc Ld Lp Op Rv Rx Vw Wf Yl Zw Zx Ye Tl Yf) Ye(aM Fa Fr Fw Hv Iv Jl Js Ni Nq Nu Om Po Qa Qe Tn) aM(Du Fi Ho Kc
Kf Ko Kp Ld Ps Rt Vh Wf Yd Yk Tm) Po(Fc Kc Kp Lt Qw Ry Sf Sh Tv Uy Wc Zw Zx Tl) Dr(Du Ke Ky Mr Pi Qe Qg Qh Sr St To Ul Tm)
Ow(bQ cM Fc iA Jj Kc Lt oK oN Vj Zx Tl tF) Fa(Aa Fc Fi Hl Hp Ih In Jj Kc Op Si Wf) Uy(bB bZ cO Cu Ij Is Jr Ld Li Lj Mk Mz) bB(Fc Ho Ld
oF Ry Vz Wc Wd Wh Yl Yf) Du(aK Jj Ke Lv Mp Nd Uf Uh Ur Wc) Qe(Hp Ps Rv Sh Uw Vw Wf Wh Yg Tl) Or(Ad Et Ho Jt Kc Ko Ld Vw Wd
Zq) Mp(gW Ho kS Ld oH Rt Tv Va Yf) Sh(Ao Fw Hv Id Jr Ke No Sr) Tl(cU Et Ij Is Jr Ke Kq Uf) Fc(Cs dF Iq Ir Jr Lj Mx) Ho(Dc dF Gd Jj Mf
Qh Ur) Jj(Fi iJ Kc Kg Ld Yg) Bo(DW eO EW) Mr(gW Lp Rv Si Wf) Kc(dL Gd Iq oE oF) Ke(Gb Qc Sf Vz Yl) Ur(Fd Jq Lp Wb Zx) Mz(Fi gW
Wf Yj) Wc(cO Li Lj Mf) cB(Dw eO EW) Et(Aj hC Qn) Hp(Jl Js Qa) Si(dD Gd Ml) Jr(Rv Vi Wf) Ld(aN Gd Qh) Yl(Cu Na Uf) dW(aD dC Lv)
gW(Aa aN Hv) Mk(Ry Vz) Hc(Fr Xa) Sf(Ij Sr) Zq(Di Mh) Zx(Hu Mf) We(Om Tn) Uu(Fi Gb) Uw(gP Io) bC(gC oF) cM(oE oF) dR(Gn gV)
eW(Lv Mb) AjKq GlRv NoQw NiWf HvLp IceC IqiZ RxdF UfVj aQiA cCiP} dX{Vt(aA aC Ad AF Aj aK Al aM aN aO Ap aQ Ar aU aV Aw
AX aZ BA BB BC bF BG bH bL bM bN Bo bP bQ bR bS bU bV bW bZ cA cB cC cD cE cF cG Ch cI cJ cL cM cP cR CS CT Cu cV cW cY
dA DB Dc dD dE Dg dH Di dJ DK dL Dp DR eC eF Et Fa Fb Fc Fi Fn Fp FR Fw Fy Gb Gd Gh gL Gp gV Hb Hc Hf Hl Ho Hp Hq Hu Hw Hx
Ib Id Ih Il In Ip Iq Ir Iu Iv Jj Jk Jm Jo Jp Jq Jr Js Jt Kc Kk Kn Kp kQ kS Kx Ky Ld Lh Li Lj Lp Lt Lu Lv Lx Ly Lz Mb Me Mf Mg Mh Mj Mk
Ml Mm Mn Mq Mt Mu Mw Mx My Na Nb Nc Ne Nf Ng Nh Nj Nl Nn No Nr Ns Nt Nu Nv Nw Ny Oa Oe Of Og OH Oi Ok Om On Op Ow Oy
Pa Pc Pd Pe Pf Pg Pi Pj Pk Po Ps Pz Qb Qc Qd Qe Qg Ql Qm Qu Qv Qw Qx Qy Qz Ra Rb Rf Rh Rj Rm Rv Rx Ry Rz Sh Sj Sr Tn Tr Tt Tz Ua
Ub Uc Uf Ug Uh Uk Up Ur Ut Uu Uv Uy Uz Vb Vc Vh Vi Vp Vw Wb Wc We Wf Wg Wh Yh Yi Yj Yk Yl Zw Zx Ye Tm Tl Xa Wm Tj Yf)
Kx(AA Ad aE Aj aK aM aN AO aQ aR aU aV AW aX aY Ba Bb Bc bE bF bG bH bJ bL bN Bo bQ bS bW bZ cB cG Ch cL cM cN cS CU Cv
Cw cY dA Db dF DG dH Dk Dl dM dN Dr Du eF Et Fb Fc fP Gb Gd Gh Gn gV Hb Hc Hf hG Hl Ho Hq Hv Hx iA Ih iJ Ik In It Jg Jj Jo Jp Jr Jt
Jv Kc Ke Kf Kl Kn Ko Kp kQ KR kS Kz Ld Lu Lv Ly Ma Me Mf Mn Mq Mv Mw Nc Nf Ng Nl Nw Nx Oe Of Oi OK Om oN Op Or Ou Ow
Oy Oz Pa Pf Pi Pj Pk Pz Qb Qg Qu Qw Qy Rv Rx Rz Sh Tv Uh Um Un Uy Va Vb Vh Vq Vv Wd We Wf Yd Yh Yj Zw Ye Tm Tl tF) Jp(Dp eC
Eq Ez Fa Fb Fc Fd Fi Fn Fy Gh Gz Ha HB HC HF hG Ho iA Ib Ic Id iH iJ iO iP IZ Jd Je Jf Ju Jv Jy Kc Ke Kf Kg Ki Kj Kk Kl Kn Ko Kp KQ
KR KS Ky Kz Ld Lt nW nY Oa oE oF oH oK oN Ou Ow pF Ph Pi Pj Pk Qg Qh Ql Qm Qn Qu Qv Qw Qy Rg Rm Ru Rv Rx Sh Ss To Ua Uc
Ue Ug Uh Ur Uu Vs Vv Vz We Yd Yi Yj Yk Zx Tm Tl tF) Mn(Dr Du eC Eq Fc Fd Fi Gb Gh Gz Hc Hl Ho Hp Kc Kk Ld Lp Lt Op pF Ps Qw Rt
Ru Rv Rx Ry Rz Sf Sh Si Sj Uw Ux Uy Uz Va Vb Vc Vh Vi Vj Vw Vz Wb Wc Wd We Wf Wg Wh Yd Yg Yh Yi Yj Yk Yl Zq Zw Zx Ye Tm
Tl Yf) Lx(Du eC Eq Fd Fi Gb Gh Ha Hb Hl Ho Hp iJ Kc Kk Kp Ks Ld Lp Lt oH Op Pj Ps Qw Rm Rt Ru Rv Rx Rz Sf Si Sj Tv Uh Ur Uw Ux
Uz Va Vc Vh Vi Vw Vz Wd We Wf Wg Wh Yg Yh Yi Yj Yk Yl Zw Ye Tm Xa Yf) eC(Aj Bo bS dE Ed Hb Hc Hq Hx Ic Id Ik In Iq Iv Jj Kc Ke
Kf Kk Ko Kp Ly Me Nr Nw Ok Or pF Pj Qg Ql Qt Qu Qv Qw Qx Rb Rf Ss St Tv Ug Un Up Ur Ut Uv Vp Vq Vs Vu Vv Tj tF) Un(Aj DR Fc
Fd Fi Gb Gd Gn Hl Ho Jj Kc Ld Lt Op Rt Ru Rv Rx Rz Sf Sh Sj Uw Uy Vb Vh Vw Wc We Wf Yg Yh Yk Yl Zq Zw Tm Tl Xa Yf) Nw(Fy gW
HB HC hF hG iA iH iJ iO iP IZ Ki Kl kQ kR kS nW nY oE oF oH oK oN Or pF Pj Pk Ri Rv Sf Tr Tv Ua Uc Ur Uv) Po(Du Eq Fc Fd Fi Gh Hl
Hp Kc Kp Lt Op Ps Qw Rt Ru Rv Rx Ry Rz Uy Uz Va Vc Vw Vz Wb We Wg Yd Yg Yi Yl Zw Zx Ye Tm Xa) Yi(Aj aM Bn bS Cx fR Hc Hp
Hu Ic Ih Jk Kl Lh Lv Lz Mh Ml Mt Mw My Ny Oi Oy Pk Qn Rg Tt Vp Vv Zx Ye Tl) aM(Eq Fd Hb Ho Kc Ko Kp Ld Op Pj Ps Qg Rt Rv Si Ux
Uy Va Vb Vh Vi Wb Wd Wf Wh Yd Yk Xa Yf) Hb(aC aN Ar Ax dL DR Eq Gb Gd hC kQ kR kS oE oH pF Qv Ry Sf Wh Yd Yj Yl Tl Yf)
Eq(Ao Ap Ar aW aX Bc Co Dl Kd Ke Kr Ld Li Nd Ni Om Ou Pi Pj Pz Qe Uf Ur Vq) Vb(Hw Ij Il Is Iu Jr Js Jt Ks Lv Mk Mz Na Nm Nt Nu Ok
Ow Pd Pe Qe Uf Vq) Sh(Ao Fy Id Js Ke Kn Lh Mt Mz No Ok Op Ou Pi Qe Rf Sr Vq) Pj(aN Ax Cv dL Fa gP hC hG iJ iP Ki nW oE oH oK Vz
Yl Tl) Lh(Du Fd Ho Hp oN pF Rx Ry Sj Uv Uy Wb Wc We Zx Xa) Mz(Du Hp Lp Ps Rv Uy Va Vw Wf Yj Yl Ye Yf) Fy(Dr Hl Hp In Jj Op Rt
Rz Sf Si Yh Yl) Qe(Hp Lp Rv Sf Uw Vw We Wf Wh Yg Tl) Jj(eO Fa gW iJ Kg Ou Uh Vq Yg Xa Yf) Ok(dR eF hG kQ Op Rv Rz Sf Uw Zx
Yf) Dr(Du Kc Ky Ou Qg Qh Sr To Ul Uv) Fa(Hl Ib In Kc Ld Op Si Yd) Ke(Gb Ho Vh Vz Wh Yj Yl Tl) gW(Aj cT dR Hv Hx Lw Mp Nx) Sf(Ij
Jr Js Mp Qh Sr Uh) Vq(Aj Fi Ld Rv Uz Tl Yf) Zx(Aj bS Dc Hu Ks Uu) Wc(Ar Du Ki Lj Mf Ml) Ow(iA Ik oN pF Qu tF) Mt(Rv Si Yd Yj Tl)
Jr(Du Rv Uy We Wf) Ar(Qw Rb Uy Vc) Tl(bB Cu Et Iq) Ur(oH oN pF tF) aQ(iA iP oN pF) Aj(Ho Kq Rz) Bo(dW EO) Hv(Gz Lp Ye) Or(iJ Kc
Yg) Uh(aN Du Ki) bS(hC iO kR) cM(kR oE oF) Mh(Kp Zq) Mp(oH pF) Mr(Hp Si) Iq(hG iZ) Lj(Lt Uy) ChKo DpYf DuNd EwbR FrHc NoQw
MfUy IbtF QbRv NxoE UwgP bBoH cCiP dRgV} jD{Op(aD aI aK aM An aQ As Aw Ax bA Bb Bc BN Bo cC cD cM Cp Ct Cu Cw Dd De Di
Dk DL dM Ef Eq Et Ex Fc Fd Fn Fy Gb Gn Gp Ha Hf Hl Hr Hv Hw iB IC Id Ii Ij Il In Ir Is Iv Jd jE Jg JH jI Jl jM Jn Jo Jp JR Js Jt Kc Kd Ke Kg
Kj Kk Kn Ko Kp Kx Ky Ld Lh Li lO Lp Lv Lw Lx Mb Me Mf Mi Mj Ml Mm Mn Mr Mv Mw Mx Mz Na Nb Nf Nh Ni Nr Nv Nw Nx Of Ok
Om On Or Ou Oy Oz Pa Pc Pe Pg Pi Pj Pk Ps Qc Qe Qh Ql Qx Ra Rb Rj Rm Ru Ry Si Sr Tn To Tr Tv Uc Ud Ue Ug Um Uo Uw Uy Uz Vb Vh
Vq Wc Wd We Wf Wg Wh Yl Zq Zw Wm Tj) Zx(aJ aO aP aQ aS Ba bJ bM bW cC cJ cO Cu Cv DB DE Dg Dr Ed Eq Et Fp Fr hA Hb Hf Hu

Ri sI uV) Wm(cX hP Kc Kn Ko IL Lu nW pF Pg rB Ri rS) Vq(Aa bP cM Ke Kk Kn Ko Mb Tt vO wE wH) Et(Gp Ib Iz Jv Or qV Sr Ub Vu Vv)
Ke(cA cM cN Hu IL Nb Or qA sH tF) Uh(bC cM iC Jv IL Or sH sI sJ tF) Bb(hP Jd Je Qy Ri Sr tV Vu Vv) Sr(dR jR Jv Lu sF sI uV) Kc(Ex Nx
tN tV Un uV wE) Ex(aV Kk OK vT) Uf(Jk Nq Qw rB wE) sJ(Js Lx Nx Ql tT) Kn(Gz iC Uk wE) Ko(Bc cN dI sH) sF(Nw Nx Ql Rf) Dl(Gz Pk wE) Kr(Iv tQ wE) Ri(Cv iC qC) Un(Qc uV tF) sH(Nw Nx Ql) lL(Jd Kx Nx) Mm(tN tT) Jv(Jp Nw) Qm(iC sI) Vu(rB wH) GzHb NcKk UcwE IccM KdiC OrrB} cR{oD(aC aG aJ aK aL aO aQ Ar AS aU aV AW AX bB bG bH bI bM Bo bR bU bV bX Ch cJ cM Cp CQ Cs Ct cW cY cZ DE dG Di DK dM dN Dp dR Du eC Ed Ef Em Eq Fd FP FR Fw Fy Gh Gn Gz Ha Hb HC Hf hG Hl Hq Hr Hu Hw Hx iA Ib Ic IH Ij Im In iP Iq Ir It Iu Iz Je Jf Jj Jk Ju Ke Kg Kl KN Ko Kq kR KS Kx Ky Kz Lh Li Lj LX LY Lz ME MF mH Mk Mn Mp Ms mU Mv mW Mx mY MZ NA Nc nD Ne Ng NH Ni Nj NL NN Nr nT nU NY Oa Oe Of oH Oi OK oN Op oT oV OW Oy Oz Pa Pb Pc Pe Pf Ph Pl Pj PK Po Pz Qb Qc Qd Qe Qg Ql Qm Qt Qu Qv Qw Qx Qy Qz Ra Ri Ru Ry Sh Si Sr Ss St Tn Tt Tv Tz Ua Ub Uc Ud Ue Ug Uk Um Un Uo Up Ut Uv Uy Vb Vj Vo Vp Vq Vs Vt Vu Vv Vw Wd We Wf Wh Yi Yj Zx Ye) oW(Aa AX bH Bo bU Ch cM Cw cZ Dp Du Ed Ef Eq Ez Fa Fb Fc Fd Fi Fn Fy Gb Gh Gp Gz Ha Hb Hc Hf hG Hl Ho Hp Ib Ic Id Io Iz Jd Je Jq Ju Jv Jy Kd Ke Kf Kg Ki Kj Kk Kl Kn Ko Kp Kq Kr Ks Kx Kz Lp Lt Lw Mf Mk Mn Mv My Nm Nx Oa Ok Op Ow Ps Qe Qg Qh Ql Qm Qn Qt Qu Qv Qw Qx Qz Ra Rb Rc Rf Rg Rh Ri Rj Rm Ru Rv Rx Rz Sh Si Sj Sr Ss St To Tr Tt Tz Ua Ub Uc Ud Ue Uf Ug Uh Uk Ul Um Un Uo Up Ur Us Uu Uv Ux Uy Va Vb Vh Vo Vp Vq Vs Vt Vu Vv Vz Wb Wc Wd We Wf Wh Yd Yh Yj Yl Ye Tm Tl Xa Tj Yf) eQ(Ax bB bH cZ Ed Ez Fa Fd Fn Fw Fy Gp Ha Hb Hc Hf Ib Ic Id Ir Iz Jd Je Jf Ju Jv Jy Kc Kd Ke Kj Kk Kl Ko Kp Kq Kx Ky Lp Lt mE Mn Nj No Oa Ow Pj Pk Qc Qe Qg Qh Ql Qm Qn Qt Qu Qv Qw Qy Qz Rb Rc Rj Rt Ru Rv Ry Sf Sj Sr Ss Tn To Tr Tt Tv Tz Ua Ub Uc Ud Ue Uf Ug Uh Uk Ul Un Up Ur Ut Uu Ux Uy Vb Vo Vp Vs Vt Vw Wd Wf Wh Yi Yl Zx Ye Tm Xa Tj) pK(Aa aK AX bB bH Bo cZ Dc Dd eC Ed Fa Fb Fw Fy Gp Hr Ih Im Io Ip Ir Is Je Jf Jg Jk Jm Jq Ju Ke Kk Ko Kp Kq Ks Li Lp Lx Mk mU mY Nj NN No Nv Ny Oa Oh Om oN Pf Ph Qc Qd Qe Qh Qm Qn Qt Qu Qy Ru Ry Sr Tn To Tr Tv Tz Ul Um Ut Uy Vb Yi Xa) mW(Du Eq Fc Fd Fi Gb Gh Hl Ho Hp Lp Lt Op Ps Rt Ru Rv Rx Rz Sf Sh Si Sj Uw Ux Uy Uz Va Vb Vc Vh Vi Vj Vw Vz Wb Wc Wd We Wf Wg Wh Yd Yg Yh Yi Yj Yk Yl Zq Zw Zx Ye Tm Tl Yf) oT(aC aH aI aL AX bB bH bL Bo cF Cq cZ dD dJ Ed Fa Fn Fy Gp Ir Je Jf Jy Kd Li Lj Lp LX Mk Mn Nj Nr Oa oH Ow Qe Qh Qm Qu Ru Sr Ss Tn Tz Ul Um Ut Uu Uy Vb Wd Yi Ye) pH(bB Eq Fa Fi Fy Gz Ha Hc Ic Jd Je Jf Ko Kq Lp Nj Nn Ow Qe Ql Qm Qt Qu Ru Sf Tn Uy Vb Vs Vz Yg Yh Yj Yk) gZ(bB bH Ed Fd Fy Gp Ha Hb Ir Je Jq Kd Ke Kq Lp Nj Nn Oa Ow Qe Qh Qt Qu Rg Rt Ru Tn To Ul Ut Uy We) pI(Ax bB bH cZ Fa Fy Gp Ha Hb Jd Je Jf Kd Ko Kx Lp Nj Nn No Oa Ow Qe Qt Qu Tn Tv Ua Uk Ul Uo Ut) oV(bB bH bU Fa Fd Fn Fy Ir Je Jf Kd Ko Lp Nj Oa Ow Qe Qh Ru Tn Ul Uy Yi) fA(bB bH Fy Kd Ke Lp Nj Ow Qe Qh Ru Tn Tv Ul) Ye(kE mE mF mI mP mT mU mY mZ nA nB nC nD) fB(aL Ax bB dD Fy Tn) Wf(mI mU mZ nB nC) Ru(mU nD oO oP) eO(Aj Bo bR Of) gC(Fy Kd Uy Vt) Ex(qZ rO rV) Ok(Eq Sh We) dW(Bo Lj Lx) oP(Fd Sj Xa) Yd(hA jI) bB(mE mZ) EoLx EwcB FdmU WhnB XaoQ KfmE OpnN VcjP PjhC} jP{Vc(aA Ad aE aF aG aH Aj aN Ao Ap Ar As aV AX aY BA bB BC Bg bH bJ bL BO bP bQ bR bS bV bW cB cE cF cG Ch cI cM cN cO cP cQ cS CT CU CV cW CX dA dB dC dD De dF Dg dH Di Dk dM Dp Du Ef Em Eq Et Ex Fc Fn Fr Fw Gb Gh Gl Gp HA Hb Hc Hf Hu Hx Ic Ik In Ip Iq Ir It Iv JG jH Jj Jk jM Jp Js jT JU jV Kc Ke Kf Ki Kj Kl Kr Ks Ky Kz Lh Li lK lM Lv Lx Ma Mb Me Mg Mk Ml Mm Mn Mr Ms Nc Nd Ne Nf Ng Nh Ni Nm Nq Nr Ns Nt Nv Oa Oe Of Og Oh Oi Ok Or Ou Oy Oz Pc Pe Pg Pj Po Ps Pz Qa Qc Qd Qe Qg Qh Ql Qt Qu Qy Rf Rg Rj Rm Rt Rx Ry Rz Sf Sj Sr Ss St Tn Tr Tt Ua Uc Uf Ug Uk Um Uo Uw Ux Uy Vi Vo Vq Vw Vz Wd We Yd Yl Zq Tm Xa) Yd(aC aF aG aH An aS aU aY BA Bb Bc bL Bo bP bR bU bW bZ cB cC cD Ch cI cM Co cP cQ CS CT cU CX dA Db dC dD dE Dg Dl dJ DK Dl dN Ef Em Et Ez Fd Fp Fw Gb Gz hA Hb Hc Ii jF JG jH Jj Jm jO jT JV Kd Kj Kr Ks lL Mb Me Mj Mk Mn Mv Mx Nc Nd Ne Nh Nj Nl Nm Nn Nt Nu Nw Oe Or Oz Pb Pe Pj Ps Pz Qc Qd Qh Qm Qv Qw Rg Ru Rv Ry Sh Sj St Ug Uh Uk Ul Ux Uy Va Vt Vw Wb Wh Zx) Dr(Af Aj Ap Aw aY bC bO cF cQ Dg Ef Ez Fn Hc Hf Hu Ic Ii Iz Jg Jt jU jV Kf Kl Kp Kz lL Mg Nf Ng Nu Oi Oy Oz Pc Pf Qm Qu Qy Rj Sr Tt Ua Uc Ug Uk Um Uo Ux Vs Vw Zq Tl) Pj(Du Em Eq Fc Fd Fi Gb Gd Gh Gn Ho Hp Lp Lt nN Op Ps Rt Ru Rv Rx Ry Rz Sf Sh Si Sj Uw Ux Uy Uz Va Vb Vh Vi Vw Vz Wb Wc Wd We Wf Wg Wh Yl Zq Zw Zx Ye Tm Tl Xa) bR(Em Eq Fc Fi Gb Gd Gh Gn Hl Hp Lt Ru Rv Rx Ry Rz Sf Sj Uw Ux Uz Va Vi Vw Vz Wb Wc Wd We Wf Wg Yl Zq Zw Zx Ye Tm Xa) Vh(aG aY Ba bU cC cH cM cS Ct cU Di dJ Em Ez Gz Ic Jf jO jU jV lL Mk Mw Nc Ng Nh Or Oz Pe Po Qm Qv Rx Ug Va Vz Zx) Ic(Fc Fi Gb Gh Hp Lt Ps Ru Rv Rx Ry Rz Uw Ux Uz Va Vw Wb Wc Wf Wg Wh Yl Zx Ye Tm Xa) Va(aE aI aK aV bB cB cZ Dk Et Hf Jl jM jR Ky Lh Li lL Pe Ps Qd Qm St Vt) lL(Du Eq Fd Fi Gb Ho Op Ps Rx Rz Sj Ux Vw We Wf Wg Wh Zq Zw Ye Tm Xa) Si(Aj bU cI Ct Du Fn Gl Io Mg Nc Ne Ni Nl Nv Oe Po Qa Ry Sr Ug) Mz(Em Fc Fi Gn Op Sh Sj Uw Uy Uz Vi Vw Wc Wf Wg Yl Zx Ye Tm) Qm(Fd Hl Ho Lp Rt Ry Sh Sj Ux Uy Vb Vi Vw Yl Tm) Uh(Du kC kF kG kN mE mF mP mZ nD nH nI nN nR nU) Ps(aP bS cM cU Em Fn Hf Kz Mq Nf Oz Ri Tl) aE(Du Fc Op Rv Rx Sf Ux Vi Vw Wd Zq Zw Ye) Du(cU Ii Jf jO Jp Kc Nf Oi Qc Ri Um) Nm(Vz Wb Wc Wd We Wf Wh Ye Tm Tl Xa) Zw(cB jU Mj Mx Nn Oi Ok Oz Qc Ql Vz) Tl(aS Ih Ii Jm Nc Ni Nl Ou Sr) Ry(bZ Hf Hq Ii Ok Pa Ql Qy Vq) Yl(cO cU CX Hf jU jV Ok Ql) jO(Sj Uw Ux Vi Vw Wd Zx Tm Xa) Ri(Fc Gb Sf Uw Ux Vw Zq Xa) Jf(Eq Gb Ux Vw We Zq Xa) Rz(Bc Dg Gl Ne Qu Ug Ux) Ii(Eq Gn Hp Op Sj Vb) Qc(Gh Rx Vz Wd Zq Xa) Eq(Dg Mg Ng Qu) Hf(Em Lp Sf Ye) Zq(cD cL jK Nc) Op(cM cQ Ct Id) Ux(aR bN cL cU) Ho(aJ aP bH) Lp(Hb Ql Um) Ug(Sh Sj Uw) Vq(Gb Ru Vz) Po(Vz Zx) Em(Ld Pz) Wd(Ez Ok) Rv(aR Ke) Rt(aG Hb) Vi(aP dF) cL(Vw Xa) nN(Qz Ur) AjZx AnlX FiOu FnGb HpOk HxUw ToUy WhKj YeVt KfyJ cMfR} Ok{We(aC AD aE aF aG aJ aM aN aO aQ AR AS aU aV aY bA bB bC bF bG bH bJ bL bM bO bQ bR bS bU bV bX cA cC cD cE cF cJ cK cM cO cQ Cs cT cW cX cZ dB DC DD dG dH dI Dk dL dM dN DR eC EF eM eQ FP Fw gL Gn gP hA HB hC hF hG Hv iA iH iJ iO iP Is Iu Iv IZ jE jF jH jI JK jO jQ JR Jt jU JY KC KE kF KG KI Kj kK kN KO kP kQ kR KS Kx Lh lK lL lM lN lW lX lY mE MF mH mI mM Mn mP mS MT mU Mv MW mY mZ nA nB nC nD nF nH NI nJ nL nM nN NO nR NT nU nW nY oE oF oH oK Om oN oO OP oQ Or Ou Pe pF Pi Pj Pk Po Qa Qb Qe Qh Qm Qw Rh Ut Vh Vt Vz Wb Yl Ye Tl tF) Eq(aC aD aE aF aG aI aJ aK aL aM aN aO aQ aR aS aU aV aW aX aY aZ bA bB bC bE bF bG bH bJ bL bM bN bO bP bQ bR bS bU bW bZ cA cB cC cD cE cF cH cJ cK cL cM cO cP cQ cS cT cV cW cX cY cZ dA dB dC dD dE dF dH dI dJ dK dL dM dN dR eC eF eM eQ fA fP fR gL gP hB hC hF hG iA iH iJ iO iP iZ kC kE kF kG kI kK kN kO kP kR kS lW lX lY mE mF mH mI mM mP mT mU mW mY mZ nA nB nC nD nF nH nI nJ nL nM nN nO nR nT nU nW nY oE oF oH oK oN oO oQ oV oW pF pH Pl Pk tF) Yk(aC aE aG aM aO aS bB bF bR bS bU bX cE cM dI dK dM dR eC eF eM fA fB fP gC gL gP HB hC hF hG iA iH iJ iO iP iZ kC kF kG kI kK kN kO kP kQ kR kS lW lX lY mE mF mH mM mS mU mW nA nD nJ nO nR nW nY oD oE oF oH oK oN oO oP oQ oT oV oW pF pI Pk Qw Uu Vt tF) mS(Dr Em Fc Fd Gd Gh Gn Hl Hp Op Ps Rx Ry Sh Uw Vi Vz Wb Wc Wd Wf Wh Yd Yg Yh Yj Yl Zq Zw Zx Ye Tm Tl Xa) iP(Dr Du Fc Fd Gd Gh Gn Hl Hp Lt Rt Rx Ry Rz Sf Sh Sj Uy Vb Vc Vh Vz Wb Wc Wh Yd Yg Yh Yj Zq Zw Zx Ye Xa) Sf(aE aG aJ aM aO aS aW aY bA bB bF bG bJ bL bO dB Dd dG dM eF Hb Ju kP Mf Pj Pk) Sh(aG aJ aS bB bF bG bJ bL bU cM cQ cW Dd dG dI dM Hb iJ Mf nY Pk Tl) Vb(aD aE aG aQ aS bC bF bG bJ bU cC cM cQ cX eM iJ iO Qw) Rx(aM aQ bF bG bJ eF eQ fP gZ Hb iJ kI kR mE mI mW nR) Em(eF hA iB iC jE jF jM jO jV jY lL lM lN lO qU) Hp(bF bU hA hC iJ jE jG jH jK jR jU lK lM lO) Wh(aC bO bU cM DD dI eC Fw hC iJ Jr Mf oK) Wd(hA iC iJ iO jF jH jO jQ jT jU jV lK lM) eQ(Gd Gn Hc Kl Kn Kx Nd Or Tr Uw Vo Vv Wb) Ye(hC iJ jI jM kP mE mM mU mZ nI Qw) Gd(iA iC iJ jI jL jY kR lK nR qW) Rv(aJ aW bG bJ bO bU cM cQ dI nR) Uu(fA fB gC gZ oD Op oT oV oW pK) Yg(bJ cM iJ Ki mE nI nL oK Vt) Eo(Bo Cs dC Dl Lj Lv No Oi) fA(Ax Du Fp Ic kP Oy) Gn(eF hC mW Ni oP) Uw(aG bU cM jF Vt) dW(aD Bo Dg Mb Ml) fB(bB Hc Hf Kz Uo) Du(aS eF jI kQ) Ew(Aj Bo Ct Oi) Wb(bG bO cC kI) Lp(jE jG jK lM)

Figure 33 Continued fR(jE jF jL Kx) hC(Dr Vi Wc Zw) eW(cX Lv Pz) Dr(aC Vt) Hl(bF cM) Yj(kP oP) Wf(iC Qw) Rt(eM oP) Yl(bG mE) Op(iB jY) Va(bO iC)
eC(pH Zw) sH(Bc cW) oV(Ef Kl) BoeO DwPz ExaO GzyH IbnC YdhA WcoO LjOg RmpH RgnL NwsJ UzcM VheM VibG VjiJ PagZ}
pK{bU(aC Al aR aS Ax bN cC Cs Cv Dc Dd Em Fd Fw Fy Gb Ha Hf Ii Im Ip Iq Is Jk Jm Jn Jq kI kK Ko Kq kR Ks Kx Ky Kz Ld Li Lj Lx Mf
Mx Mz nC Ng nH nL NN No nU Ny Oa Oh Or Ow Oz Pa Ph Pi Pz Qa Qb Qd Qe Qg Qh Qt Qv Qw Qx Qy Qz Ra Rb Rc Rf Rg Rh Ri Rj Rm
Rv Rx Sr Ss St Tn To Tr Tt Tv Tz Ua Ub Uc Ud Ue Uf Ug Uh Uk Ul Um Un Uo Up Ur Us Ut Uu Uv Ux Uy Vb Vo Vp Vs Vt Vu Vv Vz Wc
We Wh Wm) eC(Aa Af aI aL aR Ax bB bM Bn Bo cF cK cP Cs cT Cw cX Dc Dd Di dJ Dr eF Fa Fp Fw Fy Gn Hc Hf Hl Hq Hv Id Ih Ii Im Io
Ip Is It IZ Jd Je Jk Jm Jq Jy Kf KI KN Ko Kp Kq KR Ks Kx Ky Kz Ld Li Lj lW Ly Md mE Mk Mn Mq MW Na Nb nC Ng nH Nj nL NN No Ns
Nv Nx Ny Oa Of Oh Oi Oz Pa pH Pk Qa Qc Qe Qg Qv Qz Rf Rj To Tv Tz Ub Ug Ul Um Uo Up Us Uu Vj Vq Vz Wb Wc Yl Xa Wm) Li(AA
aE aK aL aX aY bB Bc bG Bo cM cQ dB dD dL Dp Dr EQ Ez FB Fi Fn Fr Gb gC Gp Gz Hb Hf Ic IO Je Jf Jj Jq Ju Jy kF Kg kI Kj Kn Ko Kq
Lp Lt LW ME Mk mP mU mY Ne Ng Nh nI Nj nN nR Nv Nx oD oN pI Qd Qm Qn Qt Qw Rf Rg Ri Rj Rm Rx Ry Sf To Tz Uo Up Ut Uu Uv
Vi Vj Vs Vz Wb We Wh Yl Zx Wm Tj Yf) Ut(AA Ad aE Aj aL aY Bc bF BG bP cM cQ Ct dD eQ Fn hB iJ In IP Iv Jj Kn Ky lX mM mS MZ
Nc Nh nI Nl nR Of Og Oy Pg pI Qv Rb Rf Rg Rh Ri Rm To Up Uu Vp Vs Wb We Yg Yk Tj) Aa(Cq dD Dr Em Fa Fw Ha Ii Il Im Iq Ir Is Iz Jk
Jm Jq Kg Kq Lh Mf Mn Ng Nn Nx Oa Oh Ph Pk Qa Qc Qe Qg Qm Qu Rb Rg Rh Rm Tn To Tv Ud Uy Vq) Dd(Ax bG bO bR dD Dr Du Em Ex
Ho In Ju Ki Kj Ko Kr Kx Ld Lu Ne Nl Of Og Ow Oy Ph Pi Qt Qv Si Ug Ul Ur Uu Va Vh We Yj Xa) cM(Ar Fb Fw Fy Ih Im Is Ko Kp Ky Lj
Mx nC nH nL NN No Oa Oh Ow Qa Qe Qv Sr Tr Ug Um Up Ur Uu Xa) dD(aF Al aO aW bN cF Dr Fw Ih Im Ip Je Jn Ko Kq Ld Lj mE mZ Ng
nI nL Nm NN No Ny Oh Pe Pf Pk Vi) Im(aA aC aL Aw bE bG cQ eQ fA gC Hu In iP Iv Ki mU nR Og Pa Qv Ul Uu Vq) Uu(Ao Ba bI Dc Et Fy
Jg Jk Jp Jt Ke Kf Ko Kq Of On Pz Rz Zq) aL(aF aS aW bI bN Ip Jk Kq NN No Qa Qd Qe Qy Vq Vt Vu) Xa(aA aE bG cQ fB iP Iv Ly Nc Og Rf
Ri To Wb) nR(aI bB bZ cG Cu Et Fw Kq Ld Mp Nv Ow Qd Uf) bB(Ax aY Bc kI mZ nN Oy Oz Pa Qe Vt) Ks(aE Dp eQ Hl Jj Ki Qv Up Ur
We) aE(Ax bN Fy Ha Kq Ky Lj Oa Pk) Ng(Ax bN Eq Gn Ip Ki We Yj) eQ(Ha No Ph Pk Qg Ud) Is(Gn In Nh Nl Yk) Kq(Bg dC kE Ki Kn)
nL(fB Mk Oz Rg Rj) Ax(aA bJ iP Mu) Fw(iO kI pI Rm) No(aA Ip Nx Rf) Ri(bX Jp mE Um) aW(bP kI Uk Tj) Ha(Dp In Nh) Nn(bP gC kI)
Ip(aA Ph Pk) Wb(Cq dK Mx) Rm(Oa Qa Um) Bo(Mx To) Mn(bG Yk) Ij(Ki We) Jk(Jj Pa) Ld(Mk pI) Qm(Ki Qv) bI(Fn Tj) iP(Nv Ny) AoVb
EtVh GnpI MfIn TohB YiYk ZqmM QecQ QukI JnPa JraI LjaA OnmS OznH PhkO PkiJ bNdB} jY{Vh(Ad aF aH aL aO aR Ax BA bH bL bN
cD cH cI cQ Cs CT Cu Cv cX Dc dD DE dF dI Dk Dp Ed Em Fd Fn Fw Fy Gh Gl Gp Ha Hf Ho iC Ih Il In Ip Is It Iv jG jH Jk jM jR jT JU JV
Kc Ki Kj Kl Kx Li Lj Mb Me Mh Mj Ml Mm Ms Mt Mu My Nc Nh Nl Nq Ns Nu Nv Nw Oa Of On Op Or Ou Pf Po Pz Qd Qg Qt Qu Qz Rm
Rt Rv Ry Rz Sf Sh Ss St To Ue Un Vi Vq Vs Vz We Yl Zq) Yd(aA Ad aE Al aM aO aY Ba bB bI bS cG cI cL Co Dc dG dH Dk dL dM Dp Fy
hA Hf Hq iC Id Ij Il Ir It Iu jH jI jK Js Jy Kc Ki Kx Li lO Lw Lx Ma Mb Me Mg Mi Mj Ml Mp Mq Mr Mu Mv Mx My Na Nf Nh Nn No Nr Ns
Nw Nx Ny Og Pb Pe Pf Pg Pj Qa Rv Tz Ua Ud Ug Vq Wf Wg Zq Zx Tl Xa) Tl(aM Ap Ar bS Dg Dk Fn Gh Hf Hq Ij Ik Im In Ip Iq It Jh Jk Jl Jm
Jo jR Ld Li lK Lx Lz Ma Mj Ml Mm Mp Mq Mr Ms Mu Mv Mx My Ne Nf Nn No Nq Nu Nw Ny Ou Oy Pf Pj Po Qc Qh Qm Qt Qx Rh Ua Vq
Wf Yl Zq Xa) Zq(aP aW bP cI cN Cx dB Dc Dd dM Dp Fn Fp Ha Hp Hu Ib Ih Im It Je jL jV Kz Lj Lp Mf Mg Mh Mq Mw Mx Nf Nm Nu Oi
Op Ou Pj Ps Qd Qn Qt Qy Qz Rf Rj Ua Uh Wf Ye) aR(Du Gh Ho kC kE kF kG kI kO kP lW lX lY mE mF mH mI mM mP mS mW mY nA nB
nC nD nF nH nI nJ nL nM nO nR nT nU Sj Ux Vw Vz We Zw) Va(aD aH aI bB Co cV cZ dD Et iB Is Jp Jy Kc Kq Ks Ky Lv Lx Mg Mj Mz Nd
On Or Ou Pj Qh Rm Tr Vq Yl Zx) Fn(Du Em Eq Fc Fd Gb Gn Hl Ho Lp Op Ps Rt Rv Ry Rz Si Uw Uy Uz Vb Vi Wc Wd We Wg Wh Zw Xa)
Hf(Dr Eq Fd Fi Gd Gh Gn Hl Hp Lp Lt Rt Ru Rv Rx Rz Sf Sh Si Vb Vc Vw Wc We Wf Wh Zw Ye) Pj(Dr Eq Gb Gd kP mH mW mY nF nI Op
Ps Rt Rv Ry Rz Si Ux Vi Vz Wd We Wf Wh Yl Zx Tm Xa) Dc(Gb Hl Ho Hp Lt mU Op Ps Ru Rz Si Sj Ux Uy Uz Vb Vi Wc Wf Wg Zx Tm)
bS(Du Eq Fc Fd Fi Gb Gn Hp Lt Op Ps Ru Sf Uy Uz Vc Vw Vz Wc Wg Ye) Vq(Dr Eq Fc Fi Gb Gh Ho Lt Op Rx Uw Vb We Wh Ye) mU(AN
aZ bB bN bO bU cB cP Cu dD dI eC Kf Pi) Dr(Ap aY Ez Hc Jd Jh Jp Mg Ou Pd Po Uo) Hp(Ad aE Ef Iq Jp Kc Pa Ql Vw Zw) Ye(Ad aE Ef Jh
Jp Jr Kc Ng Qm Tz) Kg(Fc Fi Lp Ru Uz Vb Vc Wc Wg Zx) Op(Bc cM cQ Ct Dp Id Kc Kj Po) mW(aC aK cH cJ De dI Hc Iz Qz) Si(Al Cv Dd
Lh Mg Ou Uf Ux) Nd(Fd Gh Lt Rx Vz Zx Tm) Zw(aG Ha Ib Im Mx Oi Qn) Jp(Fd Ry Rz Vi We Wf Yl) Vc(cL Et hA Mg Mm Ou Uf) Wb(aE
bU Iq Jt Kc Pa) Qm(Rv Sj Uy Uz Vi Wg) Zx(Mg Nn Oz Qw Ug) Wf(Ad Jn Jr Jt Uc) Kc(Em Fd fR Ps Uw) Yl(Ic Kz Mx Nf Nx) Gh(Ic Kz Mg
Nx) aS(mI nI nJ nO) Vz(Iq Kz Mq) Ux(dB Ic Oi) Vw(aG aJ Nu) Dg(Eq Sh) Mg(Rz Sj) Wd(Mx Uh) Lp(aE Jn) Rv(Kz Nf) DpLt DuQc PoFd
FiHb NmWe MfUy NeWc NjSh PsaE RxOu RtaG WnnW UwaW dInD fRoH} bB{fB(Aa aF aI AL aM AN aO aQ Ar aW aX aY Bb Bc bG bI
bM bN Bo bX cC cF Ch cJ CS Cv Cw Dc Dd dH DI dK Dr Em Fb Fc Fd Fp FR Fw Fy Gb Gl Ha HB Hf Ih Il Im Io Ip Ir Is It IZ Je Jf Jg Jk Jm
Jn Jy Kd kF kI Kk kN Ko kP Kq Ky Ld Li Lp mE Mf mI Mk Mr Mt mU Mw Mx mY MZ nA NB nC nH nL Nn No Nr Nu Nv Nw Ny Oh Om
On oO oQ Ou OW Oy Oz Pa Pb Pe Pf PH Pi Pk Po Pz Qa Qb Qc Qd Qe Qy Rc Ru St Tt Ua Uh Ul Uo Ut Uv Uy Vo Vs Vt Vz Wb We Yd Yh
Yl Zq Zx Ye Xa Wm) oW(aA aC aO Ap aS AW aY Bc bE bF bG bP bU cE cG cM cQ Cs Cv dD dI dL Dr eC fA Fp Gz HC Hu Hv iP Is Jr kC
kF Li lW Ly Mk mU mZ Nc Nd Nl nR Nx Of Og Oy Oz Pa Pb Pd pF Pg Pk Pz Qe Rf Rg Rh Ri Rj Rm Ul Uu Vt Wb) Vt(Ar bL Dr Du EQ Fc Fi
Gb gC Gh Gn gZ Hl Hp kP Lp Lt mE mH mM mZ nL nT oD Op oT oV pH pI Pj Ps Rt Ru Rv Rx Rz Sh Sj Uw Ux Uy Uz Va Vb Vc Vh Vi Vj
Vw Vz Wb Wc Wd We Wf Wg Wh Yi Yj Yk Yl Zw Tm Tl Xa Yf) mZ(Ax Dr EM eQ gC Gd gZ Hu Ib Ld Lh Lj Lt Oa oD Og oV pH pI Pz Qc
Qe Qw Qx Qz Sr Ua Uh Um Un Ur Uu Uy Vs Vz We Wh Yl Tj) eO(aC aD aE aG aH aM Ap aV aW Ba bM Bo cB cE Ch Ct cV cW dC dW Em
Ik It Iu Jh Lj Lx Mb Mv Nd Ng Nu Of Pz) fA(Al aM aO Ax Bc bI Cs dN Du Ip iZ Li Lj mE Mk Mx mY nB NN No Oa Oh oO Oz Pb Ph Pk Qa
Qc Qd Qe Uy Vz) oV(Ax cC Fw Ha Li Lj Mx NN Oa Oy Oz Pb Pk Pz Qe Qw Ru Ua Uu Uy Vs Wd We Wm) Eo(aD aH aN Ao Ap Ax bM cB
Ch Cq Ct Cu dC Gd In Ir It Jn Lx Ma Mr No Nu) pI(aM Ax Bc Cs Du Fa Ha Li Lj Mx nN Oa Oy Oz Pb Pd Qe Rg Uy Vv Vz Yl) Ew(aD aG aH
aN AO Ap bG bR cP Cs Ct dC It Mg Nu Of Om) mE(Dr Hu Ib Lh Lj Oa Og Qe Qw Rg Uk Uy Vs Vu Vz We Yg Yk) pH(aO Ax Bc Di eC iA
kF nR Oz Pd Qd Qe Rg Rh Ri Rj Rm) Dw(aD aG aH Aj bG bM Cs Ct dC Dg It Jo Lx Mg Nu Of) eQ(aC Ax Bc Ha kI Ks Lh Li Lj nN Oy Oz Pb
Pk Qe) eW(aD aF Aj aN bG Cs Ct Dg Dl It Lx Mb Nu Of) dW(aD aH Aj aN Ao Ax Bo bR bS Ct dC Dl It) gZ(aS Ax bG bI Cs kI Li Lj Mk nN
Oz Pb Qd) Qw(kC kE kF kP lY mF mY nB nC nL nN) oD(aO Ax Bc Li Lj nN Oy Oz Pz Qe Vs) nB(Gb Og Vi Wb Wd We Wh Yk Zq) oT(aC
Ax Bc kI Lj nN Oz Uy) Og(mF mI nH nL nN nR) Uy(Db Dr gC kI kK nL) Eq(Bc Kq lK Ut Zq) nR(gC Op Qe Uh Zq) Sh(Bc Dd jM Ut) We(kI
lW mI) Vc(jM jR lK) Va(hA iC jQ) Vs(kE mM nT) Bc(Wd Wh) Dr(lK nN) Gb(jM jR) gC(nN Rg) mH(Up Ut) MhZq YkkK VzjM SfPj RyeM
LtlW OznT mUjV} hA{Yd(aA aC aF aG AL aO aQ As aW AX BA Bb bI bJ bL bN Bo bU bZ cA cC cJ cM cN cP Cq Ct cZ Db Dc Di dK Du
Em Gb Gh Hc Hl Hq Hr Hv Hx iC Id Ii Ik Il Im Iq Ir Is It Iu Iv JE jF JG Jh JL jM Jn JO Jp JQ jR Js JT Kj Lh Lj lL lO Lw Lx Ly Lz Ma Mb Mc
Md Me Mg Mi Ml Mp Mq Ms Mv Mw My Na Ng Nh Nr Ns Nx Ny Oe Of Og Oh Oi Om On Oy Pf Pi Pj Pk Po Qa Qb Qd Ql Qm Qv Qw Qy
Rx Si Sr Tz Uc Ud Ue Ug Va Wb Wc Wd We Wf Zq Zx Tl Wm) Vc(Ad aF aI AL aM Ao aU Aw AX aY aZ Ba Bc bI bJ Bn bR bV bW cB cG
cI Co Cu Cw cZ Db dC Dg dH Di dJ Du Ed Em Et Fy Gz Hf Hu Hx Ip Is Iu Iz Jg jH jK JM Jp Jq jR jT Ju Kc Kf Kl Kq Ma Mf Mg Mm Ms Mz
Nb Oe Om Op Oy Pg Pi Pj Po Qc Qm Qy Rf Rt Rz Sf Si Sj Sr Tn Ua Ub Uf Ug Uh Un Vo Vp Wc Zw Zx Tm) Pj(Dr Du Em Eq Fc Fd Fi fR Gb
Gd Gh Gn Hl Ho Hp kC Lp Lt Op Ps Rt Ru Rv Rx Ry Rz Sf Sh Si Sj Uw Ux Uy Uz Va Vb Vh Vi Vw Vz Wc Wd We Wf Wg Wh Yl Zq Zw Zx
Ye Tm Tl Xa) Qm(Du Eq Fc Fd Fi Gb Gh Gn Ho Hp Lp Lt Op Ps Rt Ru Rv Rx Ry Rz Sf Sh Si Sj Uw Ux Uy Uz Va Vh Vi Vw Vz Wb Wc Wd

Figure 33 Continued

Nv Oh On Ow Qa Qd Qe Tz Uf) mZ(Fa Ks Nv On Or Qa Rt) On(nA nC nH nO) nN(jG jO lO) nH(Mn Qa Qe) Yi(iP iZ) YfQe MnnC QaVa
KsnA cDkF} Sf{Dc(Ar bO Db Hb Id Jj Ju Ke Kx Lj Mn Nd No Of Qe Uh) Mn(Dr eM fR kI lY mH ml mW nB Ne Up) Hb(Al Cu Fw Fy Or)
Ij(kO kP mU) Qe(aJ bS) aW(kl Yi) AaAI DkQw NobS LuhC KsoW} jO{Hp(Fw Jn Jq Nu Ps Sr) Vh(Nc Nl Nu Po Qm) Dr(Nu Po Qm Uo)
Yd(cC Kn Nw Ql) Qz(kF mY mZ nA) Tl(Po Ql Qm) Sh(Mg Uf) Sj(Ql Qm) Zx(Qw Un) Uh(kF nl) Ux(Mk Or) GztS NiSi HfWb QeLp QwVi
LtdF UwaW VccG} Gz{Dl(ul uL vB vT yH) Jr(qH rU rV rW sM) wH(Jl Oa rZ Vu Wm) Hb(rW vT wF yH) Kr(tR tS uL yH) vB(Ap Ax Oi Uf)
Lu(rU uX yH) aV(rU rW yH) Oa(qQ yD) rN(lv Ml) MmrW lcrU KewB KlqA cJmZ} jG{Vh(Kd Kn Nc Nl Ql Ru Ul Vc) Dr(Nu Sr Uo) Hp(Dk
Iq Jn) Tl(Qm Tz Un) Va(aD aM Or) Em(aE Nw) Iq(Sh Uy) Yd(Kn Ql) Zx(cC Oz) Qw(Uw Vi) Rz(Gl Ux) Yl(Db Un) Vc(cG Mf) CumW MgSh
QukF XacC UnUx aRnN} oW{aL(aO aW Dr Fd Fy Ha No) Ax(al cQ iP Mk Ng Wb) Aa(Fa Fd Gn Nx) Kx(eC Me Mh) bX(Rg Rh Ri) Cq(Dr
Vz) Cs(Mk Ng) No(dD Rf) Xa(aJ iP) Oy(Jq Tt) ApKo DrQl YfMx FiKs InNx YgYi LjcQ aInR blcX} hC{Lu(Hp Ps Rt Ru Rv Uw Ux Uy Vc Vi
Vw Wd Wf Wg Wh Yf) Aa(Uy Vc Vi Wh Yi) Gb(aW bG dB kQ Oi) Nm(Gn Hp Rz) Hb(Hp Uy Wh) Si(Qw Rf Wh) Vi(Ke Qa Uh) UhmZ
VabO} Id{dH(sO uO uT uW vI wB wJ wQ yK zG) Ri(uV vI wD wG wQ yK) Kd(hR hV rQ ul wF) Wm(hP uW) Il(uW uY) Pc(tN wQ) rQ(bQ
nW) qQ(cF Jd) ul(bJ iA) LuzA IchF ItwD VuwQ bPwF tVnW} jH{Yd(aG Kn Nc Ni Nl Ql Qm Zx) Qm(Fc Fi Ho Vh Tl) Po(Dr Va Vh Tl)
Hp(Dk Ii Ne) Zx(Hx Mg Qw) Dr(Lp Nu) Uw(Hx Qw) Va(In Ql) Vh(aG Nu) AdSh DcWh EmNw GlRz XacC UmnN} gZ{Oz(bR Fa Kx Ld Mq
Yg Yh Yj Xa) bG(Ko Kx Mn On Tn Uf Un Yi) No(dD Rf Vi) Mn(Gn Rt Vh) Qe(aL cX nR) Kx(An Hx Ip) Ax(Ng Wb) AaFa DpHa GnKs
MxKo Kzbl} mZ{Ib(Cq Cu Fa Jq Lx Mn Nn Nv On Ow Qa Uf) Uf(Ap Bb Ng Wd Wh Yg) Cu(aC Qy Uw Wd) Dr(cJ dD) Wd(bZ Nq) Qw(Nn
Nv) Jj(Ks Ow) Yl(aW Mn) BoQe CtYi OrUh} oT{Mx(Dr Gb Gh Ko Lp Ps Rt Rx Rz Sh Sj Uw Ux Uy Va Vh Vz Wb Wc Wd Wf Yl) Ha(Dp Gn
In) No(dD eC) Qe(aL nR) AaFa AnKx AxNg NeXa VzaW KoLj} Wh{mS(Fy Ij Is On Uf Yi) Cu(Hb Lj Mx nB Qh) Dc(Kx Lx Qa) Qe(Aa Hb
Pk) Jn(gP iP nY) lO(Ad Ef Jr) Qa(Hb iP) kl(Fy Js) AaeC NoiO IhkG XanY KxkR UfnR} tV{Bb(Ao Ba Ch Dk Hc Hu Iz Jd Je My Oa Qt Qy Vu
wH) Kn(fP oK qT vH) Pk(nW oK vH) It(hG Kc) Kr(Oa vH) Vu(cQ tF) AxNb ChtF LudH IcfP} oD{Ha(Dp Gn In Jj Nh Rm Yj) Kx(An aW bG
eC hB) No(dD eC Rf) Nc(Wf Yi Xa) Vz(ml Pe) Qa(Nl Yf) Qe(aL nH) aW(Qn Yl) Arbl AxNg GnKs TnbF YibG XaOz} Wm{hP(dE Dg Hb lc
Jq Ke Kn Nw Qd Qm rA Ri rW sC) Kn(rT tQ wF) sC(rB Tv uW) qA(Jd rB) pF(rS vW) KcyJ RitO WnUh PktQ cFwH tSnW} lO{Vh(Jj Kn Ne
Ni Nu Po Ql Qm) Dr(bO Nu Po Uo) Dk(Hp Wd) Yd(Kn Qm) PoTl EmaG GdHb GlRz HpJn InVa IqLp SjQm QwVi UwaW VccG} Wn{Uh(aL
aM aW cF cH cW iA lc Tv Vv tF) eD(aL Ba bP Il Jm Ma Md Nx Qu Ss) Dk(rB rC) TnJd LjeC aJrB} Yg{mS(Cu Ij Is On Uf Yi) Fy(kl IX lY
mU nH) kG(Qa Qh Tn) mT(cL Tn) CuoP YimW QakI QhnH Rgml NxnN} mF{hV(Hx Jj Js Jt Oy Qc) Jl(hW hX rB rY) rY(Jk Mg Oy) hW(Hw
Qd) rA(Fn rX) rZ(Jo Jq) IbOw JrhX JsrC} Yl{aW(lY mP mS mT mU mW mY nA nC nD nH nJ) Mn(eM mH ml) Fw(mU nO) mS(lj Il) NomU
QweC} Aa{eC(Dr Fd Gn Wb Yf) nW(Dr Gn Vc Yi Yj) Ni(Dr Gn) FaeM FdiP HpQe WdiO RtaM UhbM dLiA} nL{Ib(Fy Jq Mn On Qe Uf)
Uf(Ng Oi Rg Vs) Fy(Ct Oi) Hp(Hw Jm) CwaC MmRg MnQz QeRf} wD{Kn(cT hB Nb oF oK uT wQ) Pk(Ml Nb nW rB wQ) sC(Tn To Tt)
Ql(Of pF) JsrB} Hb{Cu(Sh Si Uy) Gd(aM As Lx) eM(Ax Lj Qv) Lx(fR Si) aM(Fc Fi) MtSh YdOn QwVi KxfR} tT{Ap(cF eC nW Pk Uh)
Dl(cC cF Vv) Dg(cF Vv) Fb(eD tF) BbJe MkMm ItrB RiwG PkdJ} qT{Gd(Ir Nt Nu) Uh(Em mH nl) nN(Ib Qw Um) Qz(kP nC) CtmW CumU
QukF JloP KkfR UvkP} Dr{mS(Gp Iq Lj Mn Us) bO(Kx Ru Sr Un) Qw(Lj Mt) Rg(Fw ml) MneM HpQe dDnO} Xa{nO(aW Ct iP kR Oy Rg
Ri) aW(mS oO) cD(iP kI) mU(Mp No) IlkG KxkR OymS} Sh{Mn(aS Dc iO Qw Up) Qh(bJ Db Tl) Jn(iP nY) DcKx Fykl NgnY QaiP KeUp}
oP{Yj(Cu Js Ks Ph Qa Qe) Gn(Js On Ph) rZ(In kN Mg) Cu(Ho Rt) TlhB} kC{hX(In Iq Jm Mw Pb Qb) rY(Lu Mr Ms Mw Ns) LurB JlrZ}
tN{Lu(CH Pk) lc(fP Kr oK) Bb(Hu Je) Ke(Ch Hu) JdJk PknW} sC{Kk(cN rB zA) Tr(Uv Vs) dH(Co Tn) AlJl BbJe KdqZ RmVu VviO}
No{Hp(gP iA iO iP oF oN) Vi(iO iP kl mW nY)} Lj{Wb(bO bS cX mW Pi) Gb(Cu mW) Qw(Vi Yd) UhiO VimW} kN{rY(Iv Js Lu Ms Nl Pa
Pg) rX(In Jl Js Pb)} rA{fR(Kc Kk Nj) An(kG nJ) Em(Nw Uh) FnnJ GdNu aRnN} qX{Em(Hf In Uh) An(kG lY) nN(aR Ib) GdHf KcfR}
Qa{Vi(gC gP iP) Yj(mU oQ) GnoQ HlmU WdiO} Pk{tQ(Ap Dg Ml Nm Ql) JdvH JjUh dHwH} eD{cP(nD nH) nN(iP nY) FbwF Qznl VuwH
aSnO} Qe{Qw(Hp Yj) AdAj HlmU IkJd ZwkG gCnR} Wd{iO(Ke On) kG(Ao Ih) CumM QdiP UfmS} rW{Kk(Nc Ne Nl) Vv(On Un) cF(Ap
Dl)} Mn{eM(Uy Vz Yd) Vzml SinB TmnR} Jj{Dc(Jv Sr Uh) kP(Fy Kg) YimW} Kx{fR(aK Ik oH Rf) WbUs VckR} wQ{It(cF iO) Kn(eC Jh)
ArEd JlnW} Un{Nq(uU tM) IchF JkuU KdvP} yJ{Ke(fN Nb) Vv(Ap Dg) LuSr} Yi{Ct(mS mT) UveC cDiP} rZ{oO(In My) LuwL JdJk}
Fw{mU(Rx Vz) LuzA} Gb{CsmW JniP cDeC} Wb{iP(Jn Oa) Rgml} Qw{EmLx MtVh IjVc} Js{Hp(iA kl) HlmU} Uh{Ar(aO oN) dLiA}
aW{Vz(mT nA) Lpkl} gC{MxVw OwbF UodD} nH{Uf(Ng Oi) CtFy} tQ{Ql(Jk pF) DgqP} wH{Jl(dN Mk) RiVu} Jd{TvqA JkxA} Kd{rO(Ke
Kn)} Rg{Wfml bXnN} Vh{IjnO aMbP} wG{TzJv RaKn} BbIchP DcVcbO HaYjkR MsmIrC TlhBoQ VuiApS VvrQnW Unconstrained panels with 2 analytes, where 1.0E-8 >= 'AUC p-value' > 0. Contains 1,385 panels of 199,783 total panels evaluated. : Ji(AA aC
aD aF aG aH Aj aK aM aN AO aQ Ar As aU aV aW AX bA Bc bH bL bM Bn bQ bU bW bX bZ cA cB cC cD CH cl cM cN Co cR CS Ct Cv
cX cY cZ dB dD dE dH dI dJ DK dL DR EF Eo ET Ex FP FR GL GP hB hC hF hG hP Hq Hr Hu Hv Hw Hx iA lb ld lH li lJ lk Il lm In lO IP
lq lr ls lt lu lv lZ jB Jg Jh Jj Jk Jl Jm Jn Jo Jp Jq Jr Js Jt Ju Jv kQ kR kS Kx Ld Lh Li Lj Lu Lv Lw Lx Ly Lz Ma Mb Mc Md Me Mf Mg Mh Mi
Mj Mk Ml Mm Mn Mp Mq Mr Ms Mt Mu Mv Mw Mx My Mz Na Nb Nc Nd Ne Nf Ng Nh Ni Nj NK Nl Nm Nn No Nq Nr Ns Nt Nu Nv NW
Nx NY OE OF Og OH Oi OK Om ON Ou Oy Oz Pa Pb Pc Pd Pe PF Pg Pj Pk Po Pz Qa Qb Qc Qd Qe Qt Qw Qx Qz Rb Rg rR Rv rW Sf Sh Si
tS Uh Uk Uo Uv Uy Va Vb Vc Vj Vs Vt Vu Vv Wb Wc Wd WE Wh Yk Wm Th) Qe(AA aC Aj aK Al aN aO Ar cA cD Ch cM Dd Dr Et Fp Fr
Gc Hb Hp Hq Hr Hu Hv Hw Hx Ih Ii Ij Ik Il Im In lo Ip Iq Ir Is It Iu Iv jB Jd Jg Jh Jj Jk Jl Jm Jn Jo Jp Jq Jr Js Jt Kc Lh Li Lj Lu Lv Lw Lx Ly Lz
Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj NK Nl
Nm Nn No Nq Nr Ns Nt Nu Nv Nw Nx Ny Oc Of Og Oh Oi Ok Om On Oy Oz Pa Pb Pc Pd Pe Pf Pg Pj Pk Po Pz Qa Qb Qc Qd Qw Qz Sf Tn
To Tv Uh Ur Vi Vt Wh Zw Ye Wm Ti Th) Ok(AA aC Aj aN Ar bM Ch dl Dr Eq Et Fp FR Hq Hr Hu Hv Hw Hx lh li Ij Ik Il Im In lo Ip Iq Ir Is
It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms
Mt Mu Mv Mw Mx My Mz Na Nb Nc Nd Ne Nf Ng Nh Ni Nj NK Nl Nm Nn No Nq Nr Ns Nt Nu Nv Nw Nx Ny Oe Of Og Oh Oi Om On Oy
Oz Pa Pb Pc Pd Pe Pf Pg Po Pz Qa Qb Qc Qd Rx Sf Sh Vb Wb Wc Wh Yk) Et(AA aC Aj aO Ar Ch Cs Fa Fp Fr Hq Hr Hu Hv Hw Hx Id Ih Ii Ij
Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml
Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oa Oe
Of Og Oh Oi Om On Or Oy Oz Pa Pb Pc Pd Pe Pf Pg Pk Po Pz Qa Qb Qc Qd Vt) Li(aA Fp Fr Hb Hq Hr Hu Hv Hw Hx Ih Ii Ij Ik Il Im In Io Ip
Iq Ir Is It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr
Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Om On
Oy Oz Pa Pb Pc Pd Pe Pf Pg pK Po Pz Qa Qb Qc Qd Qw Uh Ti) Nw(aC aN Ar bM Fp Fr Hv Im Io Iq Ir Is It Iv Jg Jj Jm Jn Jr Jt Lh Lj Lu Lv Lw
Lx Ly Lz Mb Me Mf Mh Mj Mk Mm Mp Mq Ms Mt Mu Mv Mw Mx My Mz Nb Nc Ne Nf Nh Nj nK Nl Nm Nq Nr Nt Nu Nx Ny Of Og On
Oy Oz Pb Pc Pe Pk Qa Qd) Pj(aC aM Ar Ax Bc bM cM Cs Dc dD dH dL dR eC eF Fa FP gL gP gW hB hC hF hG iA iC Id iH iJ Ik iO iP Ir iZ
jB jD jG Jj Jp jQ Kk KQ kR kS Kx Lj lK Mz nW nY Oa oE oF oH oK oN Or Pa pF Pk Qa Rg Sf Un Vt Vv) Gc(aC eC eF eP fP gP gW hB hC

Figure 33 Continued hF hG iA iH iJ iO iP iZ jE jH jK jM jO jQ jR jV kQ kR kS IK IO nB nH Ni Nk nN nW nY oE oF oH oK oN pF Pk Qw Rg Sf Uk Un Us Uy Vb Vt tF) Vt(aC aK aM Ar aU aV Ax bB bH bL bM bQ bX cA cI cM cR Cs Cu cV cX dB Dc Dd Dg dH dI dL dX eF eP Jp Kf Kp Kq Kr Ks Lh Lj Mm Pk Qa rO Tz uR uU uY Vh wE yJ Ti Th) Lj(aA cM dW Fr Hb iJ Im iO Iv Jg Jl Jn Jp Jt Kf Kk Lh Lv Lw Lz Mm Mt Mu Mz Nh Nj Nm Nt Nu Nv Ny Og On Pb Qa Qd Qw Uh Wb) Jp(Ar Eq Fa Fp Hb Hc Ib Id Im It Iz Jd Je Jr Jv Kc Kk Kr Kx Ms Oa Pk Rg Vv) Im(Fp In It Jg Jj Jn Jr Lh Lz Ms Mt Nc Ng Nj Og Oy Pb pK) Hb(Ar Ax dL eP Ex Il Ir jB Kk Kx Lx Oa Or Sf Wm) Uh(Ar Ax bM cM Cs Dc fP hC iA Id Ir Jj Pk Qa rR) jB(aO Ax bB bl bN cM Fd Hu Kx Kz mE Oy pK Qw) Ti(Ax Ed Lx Pk Qa qU rU rW tN tO tV wE) Fp(Jg Jt Mm Mz Nj Nm Nx Ny Og On Qd) Qd(Hv Jg Jj Lz Ms Nj Nm Of Og Pb) Ar(aC aK cD cM Jd Kq Kr Qz Ri) Lh(hG iA Ib It Jj Ms nK oN Pk) Og(Ih Ir It Jg Jt Mz Ny On Qa) nK(aC bB bE dD Is Nn Nx Yl) rR(Ap Dg Kc Kf Ko Uf Tk Wm) Bo(DW EO EW gV) Ir(Hw Iq Ko Lx Mz Nf Ny) Kq(Aj Bg Ch Ef Iz Jj Nq) Qa(Aa Jg Ms Pb Qw Ye) Kx(dX eP eQ fR gV mE) eO(bB bR cB Lx Mb Of) Jg(Jj Lz Ms Ng Of) jP(Dr Vc Vh Yl Zw) uR(Kf Or Ou sH Wm) pK(Ax bU dD eC Nk) Dw(aD cB Lx Mb) Mn(Dr Ew Sf Sh) Mz(hP It Iv Nj) Zq(aC aM cM kP) Jj(Dc Kf Kg Ny) bB(dU dW fB oW) Eo(aD cB Lx) Th(rU rW sC) Yd(hA jD jY) dU(Ax Nj Ut) dW(aD aM cB) eW(aM Lx Mb) Aj(Ad Jt) Dc(Sf Ur) Ew(cB Lx) Si(hA jD) Jd(Ax Ch) On(Ms Of) cM(Id Oa) jY(Vh Tl) pH(bU eC) AaNj CuVb DrUt MmtT HuNy ShQh ZxjD QwUn KfyJ KnwE VaiC aDgV cRoD Unconstrained panels with 2 analytes, where 1.0E-7 >= 'AUC p-value' > 1.0E-8. Contains 1,189 panels of 199,783 total panels evaluated. : Ji(Ad aE Af aI aJ AL An AP aR aS Aw aY aZ Ba BB bC bE bF BG bI bJ bN BO bP bR bS bV cE cF cG cJ cK cL cO CP CQ cT CU cV CW Cx dA Db DC Dd De dF DG Di DI dM dN dU eC Ed eM eP Fa Fc Fw Gb Gn Gz Hb Hc Ic Jd Kc Kf Kk Ko Ky Kz Oa Or Ow Ph Pi Ps pY Qg Qu Qv Qy Ra Rc Rf Ri Rj Rt Sr Ss To Tt Tv Tz Ua Ub Uc Ud Ue Uf Ug Um Un Ur Us Ut Uw Ux Uz VH Vi Vo Vp Vw Wf Wg Ti tF Yf) Vt(AD aE aF aG aH aI AJ AL aN aO aP aQ aR AS aW aX aY aZ BA bC bF bG bI bJ bN bO bP bR bS bU bV bW bZ cB cC cD cE cF cG cH cJ cK cL cN cO cP CQ cS cT cU cW cY cZ dA dC dD dE dF dG dJ dK DI dM dN Dr eC Fa fP Fw Hb hG Id Il Im Iq Ir Jd Jj Jt Kc Kk Kn Ko Ld Li Lx Me Mh Mt Mx Nf Nm Nw Oh On pF Qd Qg qH Qw Qz rR tT Uh Ur uV uX vA vH Zq) Qe(Ad AF An Ao AP AS aU aV AW Ax Ba BB Bc BG bL bM Bn bQ bW bX bZ cB cC Cp Cq CS Ct Cu Cv CX cY DB Dc De Dg dH DI DK DI dM Dp DU eQ iA Ib Ic Id iJ Jv Kf Kk Kn Ld Ou pF Ps Qg Qt Qu Rb Rf Rg Ri Rj Rm Sh Si Sr Ss St Tr Tt Tz Ua Ub Uc Ud Uk Um Un Ux Vb Vc Vs Vv Wd We Wf Tl Yf) Pj(AJ aK aN As aV aW aX aY aZ bB bE Bn bO bQ bR bS bW cA cD cF cG Ch cl cN Cq cR CU CV cX dA dF dG dI Ed eM eP Et Ex Hb Hu Il Im Jd jF jR Jv jY Kn Ld Li IM IO Lx Mq Ms Mt Nk Nm Nw Ny Oh Ok Ou Pe Po Qb Qd Qz rR Uh Uk Us Vp Wm tF) Lj(bM cD Fp hG Hv Hx Ij Ik In Ip Iq Ir Is It Iu Jd Jh Jj Jk Jm Jo Jq Jr Js Kc Kq Lu Lx Ly Ma Md Me Mf Mg Mi Mk Mn Mp Ms Mv Mw Mx Nb Nc Nd Ne Nf Ng Ni Nk Nl Nn No Nq Nx Oe Of Oh Or Ou Pd Pe PF Pg Po Pz Qc Tz Un Ti) Qd(Aa Fr Hu Hx Ik Il Im In Io Ip Iq Ir Is It Iu Iv Jl Jm Jn Jp Jr Jt Lh Lu Lv Lw Lx Mb Me Mf Mh Mk Ml Mm Mn Mt Mv Mw Mx My Mz Nc Ne Nf Ng Nh Nk Nl Nq Ns Nt Nu Ny Oe Oi Oy Oz Pc Pe Pg Qa Qc Uh) Nw(aA aM aO bL cD Hq Hr Hu Hw Hx Ih Ii Ij Ik Il In Ip Iu Jh Jk Jl Jo Jp Jq Js Ma Mc Md Mg Mi Ml Mn Mr Na Nd Ng Ni Nk Nn No Ns Nv Oe Oh Oi Om Pa Pd Pf Pg Po Pz Qb Qc) Ar(aU bA BB Bc bE bU Dc Dd Hc Ic Id iJ Je Jg Jj Jt Ju Jv Kc Ke Kn Ks Lw Mz oN Pk Qg Qh Qw Ra Rb Rf Rg Rj Rm Sr St Tn To Tr Tv Tz Uc Uf Ug Un Uo Up uR Us Vp Vu) Im(Aa aC Fr Hu Hx Ik Il Ir Iv Jh Jk Jl Jq Jt Lu Lv Lw Lx Ly Mh Mk Mm Mn Mv Mw Mx My Mz Ne Nf Nh Ni Nl Nm Nn Nq Ns Nt Nu Nv Nx Ny Of Om On Pe Pz Qa Sf) Jp(aC aO Ch Dp Ed Ez Fn Fy Ha Ic Ir Jj Kd Kf Kg Kl Kn Ko Kp Kq Ks Ky Kz Ld Lx Lz nK Ny Og Or Ou Ow Oz Pb Pi Qa Qm Qn Qt Qw Sh Ua Ub Uf Uh Un Uu Uv Vs) Qa(Fp Gc Hb Hv Ib Ir It Iv Jh Jj Jk Jn Jt Kc Kk Lh Lu Lx Lz Mj Mk Mm Mv Mw My Mz Nc Ne Nf Ng Nj Nl Nm Nq Nt Nu Ny Oe Of Oy Sh Tv Vh Wh) Et(aG aH aM aN Ao Ax bM cl cM Dc Dd dI EF GI Ha Hc Iz Jd Jv Kk Kl Kx Ld Rg Wm) Uh(aC aM aN Ch Cv Dd dL eF iJ iP Iq iZ Jd Kn Kq Kx Lh Lx Mz nK Oa Pa pF Rg Wm) Lh(aC aN FP Hb hC hP iJ IZ Jg jM IM nL Og Pb pF Qw Sf Sh Uy Wh Wm) Gc(aM bU cB cM DI dR eM gL Ik Jj kP Mz Nc nL Ok Or Qb Qh Qz St Vq Wh) Hb(As bM Cs Dc dH Ed Fa fR Fw Id Kq Mm Mt Mz No Oh Pa Pk Po Sh Yf) Ir(aN bM Hu Hx Ik Il In Kq Lw Lz Mc Mj Mn Mu Mx Nj nK Om Oy Pe pF) Ny(Hr It Iv Jg Jr Lw Lx Ly Lz Mx Ms Mx My Mz Nj nK Ns Nu Of Pb Pe) Fp(Aa It Jm Jn Js Lw Lx Me Mn Ms Nc Nf Nt Nv Pb Qc) Ok(aH aO cD cl dB dU EF Ex Gz Id Pk Rv Uw Yg Ye) Mz(Ax eZ fN Hc Ij Jg Lx Lz Mn Mx Nc Of Pb qA) nK(aK Ax cJ Cs jB Jq Kx Mn No Nv On Ou Ow Qc) Jg(Aj Ih It Jr Lx Mh Mx My Nj Qb) Kq(Dk Hc Hu Ib Id Ik mZ Sf Sh Vb) Aa(bM Iv Li Lx Lz Mb Ms Mt Nb) jB(aW bU cF Dr Fa fB Ip Oz Uu) Ti(Dc hC Id No Oa Or Qb Sr) Un(aC Ax cM Cs Dc Li uR) Id(aK aV dL Jd rR wQ) Ax(fA Ic Pk Sr Ur) Zq(bU dD iJ jY mM) Jd(bM Cs Jj IL qA) Kf(aC Li IM mE Pk) Og(Ij Is Jn Lx Mn) On(It Iz Jj Oy Pk) Lx(It Nj Ur) Mm(aC Pk rR) Nk(gZ nN oW) Sr(Ib oN uR) Jj(Ad Jt Uf) Ke(Ch cM rR) Kn(rR tV wQ) Ut(pK Sh Uy) Cs(cM Qw) Fa(cM mZ) Mn(It Nj) Sf(Dd Dk) Zx(jY IN) Jt(aC Ng) Va(iB jY) dX(eC Yi) qU(oO oQ) uR(Bc Cq) BbtV DcSh DrhA WmhP EqiJ FwYl FyfB NmVb NoUy NjJn HuPe YdjE WfdU TljP KrwE KxgZ LiaN OabM OpiB bRdW cRoT Unconstrained panels with 2 analytes, where 1.0E-6 >= 'AUC p-value' > 1.0E-7. Contains 2,213 panels of 199,783 total panels evaluated. : Pj(aD aE AF aG al AL AO AP aQ aR aS aU Aw bA Bb bC bF BG bH bl bJ bL bN bP bU bV bX bZ cB cC cH cJ cK cL CO cQ cS CT cW Cx cY cZ dB dC Dd dE dJ dK dM dN Ef Fr Fw Gp HA hV Hx iB Ic Ih Ii In Ip Iq Is Iz jE jH jl jK JL jM jO jP Jq jT JU Kc Kf Ki Kp Kr Ks Lh IL IN Lu Lv Md mE Mg Mh Mi Mj Mk Ml Mm Mp Mr Mu Mv Mx Na Nb nC Nd Ne Ng Ni Nj NL Nn No Nq Nr Ns Nt Nu Nv Nx Of Og On Oz Pb Pd Pf Pg Pi Pz Qc Qh QT qU Qv Qw qX Qy rA Rc Ri Sh Sr Ss Tn Tr Tv Tz Ua Ub Uc Uf Ug Um Uo Ur Uu Uv Uy Vb Vo Vu Tj) Qe(aD aE aG aH aI aJ aL aM aQ aR aX aY aZ bA bC bE bF bH bI bJ bN BO bP bR bS bU bV cE cG cH cJ cK cL cN cO cP cQ cR cT cU cV CW cZ dA dC dD dE dF dG dJ dL dN dR eC Ed EF Eq Ez Fa Fd Fi Fn fP Fw gC Gh GI Gp Ha Hc Hf hG HI iO iP Iz Je Jf Ju Ke Ki Kj Kl Ko Kp Kq Kr Kx Ky nL nW Oa oH oK oN Op Or Ow Ph Pi Qh Ql Qm Qn Qv Qx Qy Ra Rc Rh Rt Ru Rv Rx Ry Ue Uf Ug Ul Uo Up Ut Uu Uv Uw Uy Uz Va Vh Vj Vo Vp Vw Wb Wc Wg Yg Yh Yj Yk Yl Tj) Ar(aA Ad aE aF aG al AJ aM aN AO Ap aV Aw aX aZ bC Bg bL bM bX cB cC cG Ch cI cJ Cp CQ cR cT CU CV cY dB dC dD dE dF Dg dH dI dJ DK DL dM Dp eC Ed Ez Fb Fn fP Fy Gp Ha Hf Hu Hv Hx Ib Ii Ij Ik Io Iq Ir Is Iz jB Jk JI Jm Jn Jq Jr Js Jy Kf Kk Ko Kp Lh Lx Me Mf Mm Mt Mx Nf Nj Nk Nm Nx Ny Oa Og On Pa Pd Pe Pf Pi Qa Qc Qd QI Qm Qn Qt Qu Qv Qx Qy Rc Rh Ss Tt Ua Ub Ud Ue Uk Ul Um Ur Ut Uu Uv Vo Vs Vv Wm Ti) Vt(Af An Ao Ap Aw Bc bE Bg Bn Bo Ch Co Ct Cv Cw Db De Dk Dp dR Ed Ef Fp Fr Fy gL Gp gV HC Hf hP Hu Hx Ib Ic Ih Ij In Io iP Is Iz Je Jg Jl Jm Jn Jq Js Jv Kd Ke Kg Kl Kx Kz Lv Mc Mf Mj Mk Ml Mr Mu Nj NK Nn No Nr Nu Nv nW Nx Oa OE Oi Ok Or Ou Ow Pa Pd Pe Pf Pg Ph Pi Po Qb Qc qG Qh qI Qm qQ Qt Qv qZ RB Rg Rj rQ rW sC sK Sr St tO Ub Uc Ud Uf uM uO Uv vV zl yE tM Wm tF) Qa(aA Aj aN Du Eq Fr Hq Hr Hu Hw Hx Ic Id Ih Ii Ij Ik Il In Io Ip Iq Is Iu Iz Jd Jl Jm Jo Jq Jr Js Jv Ke Kf Kn Kp Lv Lw Ly Ma Mb Mc Md Me Mf Mg Mh Mi Ml Mn Mp Mq Mr Mt Mu Mx Na Nb Nd Nh Ni Nk Nn No Nr Ns Nv Nx Oh Oi Om On Ou Oz Pa Pc Pd Pe Pf Pg Pk Po Pz Qb Qc Qg Qt Qz Rg Rm Sf Tn To Un Ur Vc Vs Wc Wd We Th) Uh(aD aF AO As Ba bB Bc bL Bn bO cD cE cF dA dB dR eC Et Fa Fp Fw gL Gp gW hG Hu Hx iC iH Il Im iO Is jD JI Js Jt Kf Kk Ko Kp Kr Ld IM Mk Ml Mq Ms Mt Mx Nk Nm No Nw Nx oE oF Oh OK ON Or Pd Pe Po Qb Qw Rj Rm sH Sr tT Ub Uc Uf Un Vu Vv Wn) Lh(Aa aO Ax eF hA hB Hc hO Id IH Ii Ik iO iP Ir Is Iv JD Jn jO Jp jQ Jr Jt jU JV Kk kQ kR Kx IK IL Lx Mh Mt Mx My Nc Nj Nl Nm Nt nW NY Oa oE Of oH oK On Or Ou Oy Oz Qb Qz Rg Ss TT Ua Ub Un Uo Ur Uu Uv Vc Vs Vv We Ti) Et(aE aF aK Al Ap As aU aW aX Bc bE bl bL BN cA cB cD cF cG cH cN Co cP cR Ct Cv cX dB dD dE Dg dJ DK DL dN Dp Dr Ez fP Fw Gp Hb hC iA Ib Ic iP Je Kc Kf Kn Kq Ou Pi Qh Qt Qu Qv Qw Qz Sr tT Un Up Ur Us Uu

Figure 33 Continued

Uv Vs Vu Vv) Jp(Aa aM aN Ax bM Cs Ef Fb fP Hf hP Ih Is Jf Jg Jm Jn Js Jt Ju Jy Ke Ki Kj Lu Lv Mh Mt Mx My Mz Ng Nj Nm Nt Of Pc Ph Po Qb Qg Qh Ql qT Qu Qv Qx Qy Qz Ra Rb Rh Rj Rm Sf Sr Ss St Tv Tz Uc Ud Ue Ug Uk Ul Um Uo Ur Ut Vo Vp Vu Wm) Lj(Aa aK aN bU bX Cu Dc Dd Dg dl eC fP hB hC hF Hq Hr Hu Hw iA Ic Id Ih Ii Il Io iP Kn Ko Kp kQ kR kS Kx Mb Mc Mh Mj Ml Mq Mr My Na Nr Ns nW nY oF Oi oK Om oN Ow Oy Oz Pa Pc Ph Pi Pk Qb Qm Qz Ri Sr St tV Vp Vu Zq Wm tF) Ji(Dp Du dW dX Em Eq eZ Fb fN fY Gc gW Ha Hf hL hO Hp jD Je Jf Kd Ke Kg Ki Kj Kl Kn Kp Kq Kr Ks lM qA qB qD qG QH ql Ql Qm Qn qO qP qQ qU Rh Rm rO Ru Rx Ry Sj St Tn Tr tT tV Ul Up Uu Vz Yd Yg Yl Zw Zx Ye Tl Xa Tj) Hb(aC aM Ao Bc Ch cM Cq Cu Dg Du eM Fc Fi Fp Fr Fy Gd Gp Gz hC lj lm lp Is Iz Jd Jj Jv Kc Kf Kn Ko Ky Ld Lw Lz Mh Mk Mq Ms Mx My Nm Nn Nr Nv Nw Ny oE oF Og Ok On Ou Pd Pe Pf Qd Qz Rg Uf Un Us Uy Vu) Ok(aG aK aL aM Ao aP aU aV aW AX aY bB bE BG bL bQ bX cB cC cM Co cP Cs cX dA Dc dD dE DK dL dN Du Gh Gl Gn HC Hl Hp Iz KK Kx Ld Op Or Rg Rz Sj Uy Uz Va Vc Vi Vj Wc Wf Yd Yl Tl Ti) Qd(aA Aj aM bM Cs Du Gc Hq Hr Hw Id Ih Ii Ij Jd Jh Jk Jo Jq Js Jv Kc Kk Kn Ly Ma Mc Md Mg Mi Mj Mp Mq Mr Mu Na Nb Nd Ni nK Nn No Nr Nv Nx Oa Oh Om On Pa Pd Pf Pk Po Pz Qb Ub) Fp(aA Fr Hu Hv Hx Ih Ii Ij Ik In Ip Iq Ir Is Iv Jh Jj Jl Jq Jr Lu Lv Ly Lz Ma Mc Mf Mg Mh Mi Mk Ml Mt Mu Mv Mw Mx My Nb Ne Nh Ni Nk Nl Nn No Ns Nu Oe Of Oi Oy Oz Pz Qb) Mz(Aa aN bM dl eT hC hL Hq Hr Hu Hx Ib Ik Il Io Is Iu Jj Jn Jr Jt Kc Kk lK Lw Mc Mh Mj Ms Mt My Nb Ne Nm No Ns Nt Oa Oh oK Pe Pf Pk pY qB qD qO qP qQ Sr Ur Yk) Im(aA aN bM dU Hq Hr Hv Hw Ih Ii Ij Io Ip Iq Is Iu Jm Jo Js Ma Mb Mc Md Me Mf Mg Mi Mj Ml Mp Mq Mr Mu Na Nb Nd Nk No Nr Oe Oh Oi Oz Pa Pc Pd Pf Pg Po Qb Qc) Ny(Aa Hq Hv Hx Id Ih Ii Is Jh Jk Jn Jq Jt Lu Lv Ma Mc Mf Mh Mi Mj Ml Mr Mt Mu Mw Nb Nc Ne Nf Ng Nh Nl Nm No Nr Nt Nx Oe Oh Om On Oy Pa Pc Pd Pf Pg PK) Jg(Aa bM Hr Hu Ik Ip Ir Is Iv Jh Jm Jn Jq Js Lu Lv Lw Mb Ml Mm Mn Mp Mq Mr Mt Mv Mw Nc Ne Nh Nl Nm Nq Ns Nu Nv Nx Oe On Oy Oz Pa Pb Pc Pe Po Pz Qc) Id(aC aF aM aU Ax bB bM bX cD Cv Dc dD dH dJ hO hR Hu hV Il jQ Ko lM Mm Mn No Nr Nw Oh On rC Rg Sr Un uO uR uV vI yK) Nw(Aa aF aG aH aK bB bE bX cC cl cM Cs dB Dc dH dl dK dL eC eP fP hC iA iJ iP JD Kq Kx oE Or pF sF sJ Un) Gc(al AJ aS aX bB bM bN bR cV dC dD dH Ed jB kE kG lY mF Mr mS Ne nK Ns oO Pi Pz Qc Qv Uu Vv Wd) lr(cM hG Hq Hr It Iv Jn Jr Jt Kc Kf Ma Mf Mi My Na Nm No Nq Ns Nu Nx Pb Pd Pg Pk Qw Sr Un Ur Ti) Lx(Hq Hu Hv Ij Ip Is Iv Jj Jm Jn Jr Jt Ma Mk Mm Mn Ms My Nc Nh nK Nl Nm Nx Om On Oy Oz Pb Pe) On(Aa aC Aj aN cl Jh Jn Jr Lu Lz Mb Mh Mp Mv Mw My Nc Ng Nj Nl Nq Nt Oz Pb Rg Sh Wh Ti) Un(bM Cv Dd eC Ed eF Fw hG Hu Ib Ic iJ Ik Jd Jj Kc Kf Ko Mk nK Pa Pk Qg Qz Sr Ti) Kq(aM Aw Ax Ba bM cD Cs Ct eF Eq Fr Jv Li Lu Lv mE Mw Ng nK Pk Qw Ua Vs Wh) jB(al aS bG bM cA cR dM Du Gh Hc Jn kF Kp Nk Pk Qc Vb Vs Vz Yl Zq Tl) Ax(cM Jv Jy Kf Kk Ko lY Nk Or oV oW Qw Qz Ra Rg Rj Tz Uf Up Us Vv) Aa(Fr Ih Is Jl Lu Lv Ma Me Mf Mh Ml Mp Mr Ne Nl Nt Og Po Qc) Pk(aV cM Cs Dc Dg Jj Kc Ke Kk Ko Ld Lu Nv Sr uR wE Zq) nK(aA al aL Bo cM Cu Dd Fa Gl iH Js Li Nk Oa Oh Or Vz) Og(Fr Ii Iv Jd Jm Mm Mt Nm No Nt Nu Nv Nx Oa Pf Vq) Jt(aN In Is It Kk Lz Mr Ms Mt Mx Ne Nj Of Qb Vb) Li(bM cD cM Dc hG Kc Kk Kp oD Qz Sr tT tV Tz Vp) Ti(aM cM Cs Fw Fy lq Jm Mr Mt Nr Pe Po) Mn(dU Dw eW Hu Is Iv Lz My Ne Nh Ns Nu) Jd(Aj Bg Fa Hu Ik Kn Ld Ng Oa Qu Qw Uu) Jj(Dd dW eO Fy Jm Jn Ke Ko Ks Mm Vq) Oa(aN bX dH dI Js Kc Kf Mm Sr Wb wE) bB(eQ Ew fA gZ mE mZ oD oV pK Sh Uy) Sr(aN Ch Dc eF Hc lK lM Rg rR) dU(bU cR eC Fd Fy Jq Nn Qc) Dc(Aj Ct Jv Tv Ub Uk Wh) Js(hC Ib Kk Ms Qw Rg Ur) Kf(Cs Fa lK qA tT Uu wE) Kx(cM Dr Ex mZ Nk pl Wb) Pe(Hq Hr Lw Lz Mx Ns Pg) No(Eo Nj pK Qw Sf Wb) Mm(Fa It Jn Ms tO tV) Ke(dL eF Hu Sf Sh yJ) aC(Ad Ap Bb Cu nL Vq) Wm(rT sC tR vW wH) Nj(Ew Is Ma Nm Nt) Nv(It Ms Mx Pb pK) Vh(bU Fw iB jE lM) Bb(aM bM hP rR) Dd(Kk pK Sh Vb) Eo(Is Jn Mb Oh) Zq(bO Mh mS Or) uR(aP Cu Dl Vv) Dr(Ky Qh Sf) Du(iJ mE Up) Nk(Fa oD pH) Nx(aM aN rR) Uf(Ch Cs nL) dW(aF Lv Mb) Ew(aM Mb) Nm(Is tT) Nt(Is It) Lu(Fa hC) Yi(bO cD) Sh(Ad Fy) Wh(Cu Ut) Qh(Sf Yk) Kk(rR sC) Ko(fB Or) gV(cP dR) jD(Op Tk) qU(nA oP) pK(bN Nn) AjAp BckP CsiO CtDw ThrR Frlt GbhC LvcO WbaM SijP QwVi JnaN QmqA OwmE OunL UtVc cBeW cMnN cRoW dXgW mUrZ Unconstrained panels with 2 analytes, where 1.0E-5 >= 'AUC p-value' > 1.0E-6. Contains 3,998 panels of 199,783 total panels evaluated. : Uh(aA Ad aG aH aI AJ aK Al AP aQ aR aS aU aV AW aY aZ bA bC bE bF BG bH bI bP bQ bR bU bV bW bX bZ cA cB cC cG cH cI cN cO Cp CQ cT CU cV Cw CX cY dD DE dF DG dH Dl dJ dK Dl dM Dp Dr Ed Ef Fr Fy Gc Gl gP Ha HB Hc hF Hq Hr Hv Hw IB Ic Ih Ii Ij Ik In Io Ip It Iu Iv Iz Je JF Jg jH Jk Jm Jn Jo Jq Jr Ju Jv Kc Kd Ke Kg Ki kQ kR kS Kz lK lO Lv Lw Ly Ma Mb Mc Md Me Mf Mh Mi Mj Mm Mn Mp Mr Mu Mv Mw My mZ Na Nb Nc Nd Ne Nf Ng NH Ni Nj NL Nn Nq Nr Ns Nt Nu Nv nW NY Oe Of Og oH Oi Om Ow Oy Oz Pb Pc Pf Pg Ph Pi Pz Qc Qg Qh Ql Qm Qt Qv QX Qz Ra Rb Rc Rf Rh Ri Ss St Tn Tr Tv Tz Ua Ud Ue Ug Uk Up Ur Us Ut Uu Uv Vo Vp Vs Ti tF) Lh(aA aF Aj aK aM aX bH bL bM cD Ch cM CS dB dE dH dU eC ED Ef Fa Fr gP hF Hq Hr Hu Hv Hx iB IC Ij Il In Io Ip Iq Iu jB JE jF jG JH jI JK JL Jm Jo jP Jq jR Js jT Ju jY Kc Ke Kn Ko Kp Kr kS Ld lN lO Lu Lv Lw Ly Lz Ma Mb Mc Md Me MF Mg MI Mj Mk Ml Mm Mn Mp Mq Mr Mu Mv Mw MZ Na Nb nC Nd Ne Nf Ng Nh Ni Nk Nn No Nq Nr Ns Nu Nv Nx Oe oF Oh Oi Om Ow Pa Pc Pd Pe Pg Ph Pi pK Po Pz qA Qc Qg Qh QT QU Qv qW QX QY RA RB Rc Rf Rh Ri Rj Rm Sr St TN TO Tr tS TV Tz Uc Ud Ue Uf Ug Uk Ul Um Up Us Ut Uw Vb vH Vo Vp Vu Wb Wc Wd wE wK wP wQ zA Th tF) Vt(aA Bb Cp Cx Di Du Ex Ez Fb Fn Gl gP Ha hB hF Hl Hq Hr Hv Hw iA iH Ii iJ Ik iO Ip It Iu Iv iZ Jf Jh Jk Jo Jr Ju Jy Ki Kj kQ kR kS Ky lK Lu Lw Ly Lz Ma Mb Md Mg Mi Mn Mp Mq Ms Mv Mw My Mz Na Nb Nc Nd Ne Ng NH Ni NL Nq Ns Nt NY OF Og oH oK Om oN Op Oy Oz Pb Pc pS Pz Ql Qn qO qP Qu Qx Qy Ra RC Rf Rh Ri Rm rN rP rS RT rU rV Sj sM Ss Tn To TR Tt TV Ua Ue UG uI Uk UL Um UN Uo UP Us uT Uu uW uZ vB vC vI VO VP VS vT VU Vv vW wB wQ yH yK yL zG zH tL xA Tj) Hb(Ad Af AJ aK Al aN AP aU aV Aw aY Ba Bb bC Bg Bn bQ bW bZ cD cG cI cN Co Cp Ct Cv Cw CX dA DD De dF dG dI Dk Dl DR dX EF Fb fP Gb Ha Hc Hq Hu Hx iA Ic Ih Ii iJ Ik In Io Iq It Iu Iv iZ Je Jg Jl Js Jt Ju Jy Kd Ke Kg Ki Kj Kp Kr Ks Lv Ly Ma Mc Md ME Mf Mi Mj Ml Mn Mp Mr Mu Mw Na Nb Nc Nd Ne Ng Nh Ni Nj Nk NL Nq Ns Nt Nu Nx Oe Of Oi Om Ow Oy Oz Pb Pc pF Pg Ph Pi Ps Qb Qc Qg Qh Qv Qw Ra Rc Rt Ru Rv Ry Si Sj Sr Tn Tr Tv Ub Uc Uk Uo Ur Va Vi Vp Vv Yl Xa Tj Ti) Ar(Aa aD Af aH AL An aP aQ aR AS aW Ax aY Ba bF bG bH bI bJ BN BO bP bQ bR bS bV bW bZ cA cE cF cH cK cL cN CO cP CS Ct CW CX cZ dA Db De dG Di dN Fa Fp Fr Fw Gc Gl hC hG Hq Hr Hw iA Ih Il Im In iO lP It Iu Iv Jf Jh Jo Kd Kg Ki Kj Kl Kx Ky Li Lj Lu Lv Ly Lz Ma Mb Mc Md mE Mg Mh Mi Mj Mk Ml Mn Mp Mq Mr Ms Mu Mv Mw My Na Nb Nc Nd Ne Ng Nh Ni Nl Nn No Nq Nr Ns Nt Nu Nv nW nY Oc OF OH Oi oK Om Or Ou Ow Oy Oz Pb Pc pF Pg Ph Po Pz Qb rR wQ Tj tF) Gc(aD aF aG aH aK aL aN aO aP aQ aR As aU aV aW aY aZ BA bC bE bF bG bH bI bJ bL bO bP bQ bS bV bW bX bZ cA cD cE cF cG cH cI cJ cN cO cP cQ cR CS cT cU cW cX dA dB Dc dE dF DG dI dJ DK dM dN Dr Du Ef Em Et Fp Fw Gd Ha Hu Ip Is Jl Jm Ju kI kK kN Kx Ky Kz Li Lj LX Lz Ma ME Mf Mh Ml Mn Mp Mt Mx mY nC Nd Nf Nh Nl Oa Og Oh Oi Oy Oz Pa Pb Pd Pf Pg pH Po Ps Qg Qt Qx Qy Ra Rb Rt Rv Sh Si Sr Tn Tz Ud Ue Ug Ul Um Uo Up Ur Ut Ux Vc Vi Vo Vs Wc We Wf Wm Th) Et(AD Af aI aJ aL An aP aQ aR aS aV Aw aY aZ BA BB bC bF BG bH bJ BO bP bQ bR bS bU bV bW bX bZ cC cE cJ cK cL cO Cp CQ cS cT CU cV CW Cx cY cZ dA Db dC De dF dG dH Di dM dR Ed Eq Fb Fn fR Fy gL gP Hf hG iJ iO iZ jB Jf Ju Jy Kd Ke Kg Ki Kj Ko Kp KR KS Ky Kz nK nY oE oF oK oN Ow pF Ph pK Qg Ql Qm Qn Qx Qy Ra Rb Rc Rf Rh Ri Rj Rm rW Ry Sf Sh Ss St tO tS Tv Tz Ua Ub Uc Ud Ue Uf Ug Uk Ul Um Uo Ut Vo Vp vV Tj) Ok(AD aE AF aI aJ Al An Ap aQ aR AS Aw aZ BA Bb BC bF bH bI bJ BN BO bP bR bS bU bV bW bZ cA cE cF cG cH cJ cK cL cN cO Cp CQ cR cS CT CU CV CW Cx cY cZ Db dC Dd De dF DG dH Di dJ Dl dM dR Em eP FA Fc Fd Fi Fw Gb Gd Gp hG Ho iA Ib Ic iP Je Kc Kf Kl Kq Kr Ks Lp Lt Ou Ow pF Ph Ps Qw Rt Ru Ry Si Sr Un Ur Uu Uv Ux Vh Vu Vw Vz Wd Wg Yj Zw Zx Tm Xa Wm Th Yf) Id(aE aI Aj

Figure 33 Continued

Figure 33 Continued

Unconstrained panels with 2 analytes, where 1.0E-4 >= 'AUC p-value' > 1.0E-5. Contains 6,741 panels of 199,783 total panels evaluated. :
Un(aA aD aE Af aG aH al aJ AL An AP aQ aR aS aU aW aX aY aZ BA BB bC bE bF BG bH bI bJ BN BO bP bQ bR bS bU bV bW bX bZ cA cB cC cE cF cG cH cJ cK cL cN CO CP CQ cR cS CT CU CW CX cY cZ dA Db dC DE dF dG DI Dk Dl dM dN Du dX Ef Ez Fa Fb Fn fP Fr Fy GL GP gW Gz HA hB HF hG HO HP Hq Hr Hv Hw Hx iB iC IH Ii Ij IO Ip Is It Iu Iv iZ jD JF jG Jh Jk Jl jM Jo Jr Jy Kd Kg Ki Kj Kl kQ kR KS Ky lK lM Lu Lw Lz Ma Mb Mc Md Mf Mg Mh Mi Mj Ml Mn Mq Mr Mt Mu Mv Mw My Na Nb Nc Nd Ng Nh Ni Nj NL Nn Nq Nt Nu Nv nW nY OF OH Oi oK Om ON Op Or Ow Oy Pb Pc Pd Pf Pg Ph Pi Po Pz qA Qb Ql Qn qT Qu QV Qx Qy Ra rB Rc Rf Rh Rm Sf Sh Si Sj Tn To Tt Tv Tz Ub Uc Ud Ue Ug Uk Ul Um Up Us Ut UU uV Uy Vb vH Vo Vp Vu Wb Wh Yd Ye Tl Xa Tj Th tF) Id(aA AD Af aG aH aJ AL Ao AP aQ aR aS AW aX aZ BA Bb bF BG bJ Bn BO bV cB cC cE cH Co cP CQ cR cS CT CW cX cZ dC Dd De dF Di DK Dl dM dN Dp dR eC Ed eF eT EZ FN FP FY Gp Ha HC Hf hG hL Hq Hr Hv Hw HW HX iA Ih It Ii Ij Ik IO Iq Is It Iv Iz jD Jf Jh jI JK jL jM jO Jq JR jT JU JY Kd Ke Kg Ki Kj Kl Kn Kx Ld Lv Lw Ly Ma Mb Mc Md Mf Mh Mi Mj Mk Ml Mp Mq Mr Ms Mu Mv Mw My Na Nb Nc Nd Ne Nf Nh Ni Nl Nm Nq Ns Nt Nu Nx oE Om oN Ou Ow Oy Pc Pd Pe Pg Ph Po pY Pz qA Qb QC qD QG QH Ql Qm Qn qO qP Qt QU Qv Qw Qx QY RB Rc Rf Rh Ri Rj Rm rX sC sH sI sJ sM sO Ss Tn TO Tr tS tT tU Tv Tz Ua Ub Uc Ud Ue UG Uk UL UM Up Ut Uu Uv uY uZ vA vB vC vH Vo Vp Vq Vs VU VV wB wG wH wJ wK wL yH zA zG yE tM tL Tj Th) Mz(aA AD Af aG aH al AJ aK AL aM Ao AP aQ aR aX aY aZ Bb Bc bE Bg bH bL bN Bo bP bQ bU bV bW bX cB cC cG Ch cI cJ cM cN CO cP cR cS CU Cv CW CX cZ dA Db DC Dd De dF Dg dK Dl dN Dr DU eC Ed Eq Fa Fi Fr Fw Gb GL Gz Ha HF hG Ho iA iB Ic iH iO iZ JE JF jG JH jI jK JL jO jP Jq jR Js jT JU jV jY Kg Ki Kj Kl Kp kQ kR KS Ky Kz IN IO Ly Mb Me Mg Mk Ml Mp Mu Mw Nd nK Nq oE oH oN Op Ou Ow Ph Pz Qb Qg Ql Qn QT QU Qv QX Qy QZ rA RC Rf Rh Ri Rj rQ rW Sh Si To Ud Uf Ug Uk Up Ut Uv Vh Vp Vv Vz Wb Wf Wh Yd Yg Yi Yj Yl Zq Tl Tj tF) Kq(aA AD aE Af aH AL An aO Ap As aU aW Bb Bc bE bF bG bH bL Bn BO bP bQ bX bZ cB cE cF cH cN CP CQ cR cV Cw cX cY DB Dc Dd De Dg dl dJ Dl dM Dp Dr Du Fb Fc Fi Fn Fp fR Fw Gc Gl Gn gZ Hf hG Ho Hq Hr Hv Hw Hx iA Ic Ih Ii IJ Il Im IP Iq It Iu Iv jB Je Jg Jl Jm Jn Jo Jq Jr Js Jy Kd Ke Kf Kg Ki Kj Kn Kr Ks Ky Kz Lh Lx Ly Ma Mb Mc Md Mf Mi Ml Mn Mp Mq Mr Ms Mt Mu Na Nc Nd Ne Nf Nh Ni Nj NL Nm No Nr Ns Nt Nx Ny OE OH Oi Om ON Ou Ow Oy Ph Pc Pd Pe Pf Ph Pi Po Qb Qd Qm Qn Qu Ra Rc Rf Rg Rx Si Sr Tt Ub Uc Uk Uo Up uR Us Ut Uv Uy Vc Vv Wb Yd Yg Yk Yl Wm) Hb(aA aD aE aF aG al aL An aO aR aS aW aX aZ bA bB bE bF bG bH bI bJ bL bN BO bP bR bS bU bV bX cA cB cC cE cF cH cI cK cL cO cP cQ cR cS cT cU cV cW cY cZ DB dC Di dJ dK dM dN Dp dU eC Em Ez Fd Fn Gc Gh GL Gn gP gV hB HF hG Hl Ho Hp Hr Hv Hw Ib iH iO iP Jf Jh Jk Jm Jn Jo Jq Jr Kl kQ kR kS Kz Lp Lu Mb Mg Mv nC Nf nK nW nY oH oK oN Op oW pK Pz Ql Qm Qn Qt Qu Qx Qy Rb Rf Rh Ri Rj Rm rR rW Rx Ss St To Tt Tz Ua Ud Ue Ug Ul Um Up Ut Uu Uv Uw Ux Uz Vb Vc Vh Vj Vo Vq Vw Vz Wb Wc Wd We Wf Wg Wh Yd Yi Yj Yk Zq Ye Tm Tl tF) Jp(aA AD Af aG aH al aJ aK AL An aQ aR AS aU aV AW aX aY bA BB BC bE bF bJ bN BO bP bQ bR bS bU bV bW bX bZ cA cB cC cE cF cG cH cI cK cL cN CO CP CQ cR cS CT CU cV CW CX cY cZ dA dB dC dD DE dF dG dH Di dJ Dk Dl dM dN Dr eC eT Ex Fc fN Gc gL Gz hA hB Hq Hw iB iC iH IO iZ jD jE jF jG jI jK jL jM jO jP jQ jR jT jU jV jY kS IL IM IN IO Mc mF Mg ml Mj Mn Na Nd Nf nL nN nW nY oF OH Oi oK Om pK Pz qO qQ qU qV qW qX qY rW Rx Vc VH Vq Vz Wb Wh Yd Yg Yj Yl Th tF) Lh(AD aG aH al Ao aP aQ aR AS aU aV aW aY aZ bA BB BC bE bF bG bI bJ BN bP bQ bR bS bU bW bX bZ cA cB cC cE cF cG cH cI cJ cK cL CO cP cQ cR cT cU CV cW CX cY cZ DC DD dF dG dl dJ DK dL dM dN Dp DR Eq eT Ex Ez FN fR Fw Fy Gb Gc GL Gp Gz Ha Hf hL hR hV HW hX Jf Jy kC Kd Kf Kg Ki Kj Kl kN kP Ks Ky Kz lW IY mE mH mM mS nB nH nN nO nR Pf Ps pY qB qD Ql Qm Qn qO qQ qV Rt Ru Rv rW Si tR tU Ux uY Uz Va Vh Vi Vj Vq Vw Vz wC wD WF WG wH wL Yd Yg Zw Ye Tm Xa Tj) Oa(aA aC aE Af aH Aj aL aM An aX bH bN bO cA cB cE cI cK cP Cq cR Cs CT cU Cv Cw CX cY cZ Db dC dD dE Di DK dL dM dN Dp dU eC Ed eF Ex Fb fP Fr Fw Gb Ha HC Hr Hv Hw iA Ib Ii Ij Ik Im iO Iq Ir Is It Jf Jj Jm Jn Jo Jq Jr Ju Jy Kd Ke Kg Kj Kk Kl kQ Ks Ky Kz Ld Lv Lw Ma Mc mE Mf Ml Mj Ml Mr Mt Nb Nc Ne Ni Nj Nl Nm No Nr Ns Nu nY Oe Of Oh OK Om oN Op Ow Pc Pd Pe Ph PK Pz qA Qc Qg Ql Qm Qv Qx Qz Ra Rb Rc Rf Rg Rj Rm rR To Tv Ud Ue Uf Ug Ul Uo Up uR Ut Uu Uv Vh Vo Vp Vs wB Wm Th tF) Qd(aD AF aG aH al Al An Ao AP aR As aU aV aW aY Ba BB Bc bE Bg bJ bL Bn Bo bS bU bX cA cB cC cG cH cI Co Cp CQ cR cS Ct Cu Cv Cw CX dA DB dD DE Dg dH Dl dJ DK DL dM dN Dp Dr Ed EF Ex Ez Fb Fn Fw Gl Gz Ha hB Hc HF hR Ib iH iO iP Iz Jf Ju Jy Kd Ke Kg Ki Kj Kl KR Ks Ky Kz nY oE oF oH oN pF Ph Pi pK Qg Qh Ql Qm Qn Qt Qu Qv Qx Qy Ra Rb Rc Rf Rh Ri Rj Rm Si Ss St Tn To Tr Tt Tv Tz Uc Ud Ue Uf Ug Ul Um Uo Up Us Ut Uu Uv Vo Vp Vu Vv Wd Wh Tl Tj Th) Gc(aE Af Al An Ao Ap Aw Ax Bg Bn Bo cC Ch cK cL Co Cp Cq Ct Cu Cv Cw cY cZ Dd De Di dL Ex Fa fB Fd FR Fy Gl Gn Gp Hc Hq Hr Hv Hw Hx Ih Ii Ij Il Im In Io Iq Ir It Iu Iv Jg Jh Jn Jo Jq Jr Js Jt Jv kC Kd kF Lu Lv LW Ly Mb Mc Md Mg mH Ml Mj Mk MM Mq Ms mT Mu Mv MW My NA Nb nF Ng nI NJ NM NO Nq Nr NT NU Nv Nw Nx Ny Oe Of Om On oP Ou Ow Pc Pe Qu Rc Rf Rh Rj Rm Ru Ry Sj Ss To Tr Tt Tv Ua Ub Uc Uf Uv Uw Uz Va Vh Vj Vp Vu Vw Wg Yl Zx Ye Tj Ti Yf) Sr(aA aD aG aH Aj An Ao Ap aR AS aU Ba bF BG bJ bL bS cA cD cH cM Cq cS Ct cU Cv cX dC Dd Di dL dM Du Fa Fp Fw gL gP HA hB hF hG Hq Hu Hx Ic Ik Il Im In Io Iz jD jG Jh jI jK jM Jn jO JQ jR jV Kc Kf Ki kQ kR Kx Ld IL Lw Ly Mc Mh Mi Ml Mm Mn Mq Mr Mt Mw Mx My Nb Nf Ng Nh Nk nL No Nr Nt Nv nW Nx nY OE OF OH oK Om Or Oy Po Qh Qm Qu Qv Qx Rb Rc Rf Rh Rj Rm Tn To Tt Tv Tz Ub Ud Ue Uf Ug Ul Um Uo Uu UV Vc vH Vo Vp Vs Vv wE Th tF) Js(aC aM Ax dL Ef Ez Fa Fn Fr Ha hB Hc hF hG HP Hu Hv Hx iA Ih Ij In IP Is Iz Je Jh Jj Jl JM Jn Jr JU jV Kd Kf Kj Kl Kn Ko Kp kQ kR kS Kx Ld Lu Lv Lw Lz Mb Mf Mh Mk Mv Mw Mx My Ng Nh Nm No Nq Ns Nv OE oF oK On Or Ou Oy Pc Pe PF Pg Ph Pi Po Qb Qc Qm Qn Qt Qu Qv Qy Qz Ra RB Rc Rf Rh Ri Rj Rm sJ Ss St Tn To Tt TV Tz Ua Ub Ud Ue Ug Uk Ul Um Up Ut Uu Vb Vc Vp Vs Vu Vv Wb Wh Ye Wm Ti Th) Ti(Ad Af aH aJ aK Al aN aP aQ aR As aU aV aY bB Bc bF bH bI bJ bM bQ bR bS bW bX bZ cA cB cD cG cK cL CO cT cV cZ dA dC dE dG dI Dk dM Em Et Fb Gp gW Hq Hv Ib Ic iH lj Il Im Io Is Iu Iv iZ jB Jh Jj Jk Jn Jr Jt Ju Jv Kd Kk Kn Ko Kx Ld Lv Lz Me Mh Mi Mj Mk Mn Mq Nd Ne Ng Ni Nk Nm Nt Nu Nv Nw Ny Og Oh Om Ou Ow Oz Pf Pi Pj Qc Qm Qn qV Rg rQ rX Tn Tv Ub Uc Ud Uf ul Up Vi Vp Wb wH) Qa(Ad AF aK Al aM An Ao Ap As aU aV Aw Ax Ba Bc bE Bg bH bL Bn Bo bS bU bX cA cC cF cI Co Cp Cq cS Ct Cu Cv Cw Cx DB dD DE Dg DI dJ DK DL Dr eC Ef Ez Fb Fc Fd Fi Fn Fw Fy Gb Gh Gl Gp Ha hB hC hF Ho iH iJ iO iP Jf Jy Kd Kg Ki Kj Kl KR KS Ky Lp nW nY oE oH oK oN pK Qh Ql Qm Rt Rv Rx Ry Rz Sj Us Uu Ux Vj Vu Vw Vz Yg Yi Yj Yl Zq Zx Tm Xa Tj tF Yf) Li(aE al AJ aL Ao Ap aR aU aV aW aX bC bE Bg bl bL Bn bU bW bX cA cC cG Ch cI cJ Co Cq Ct cU Cw CX DB dE dF dH dl DK dL Dr dW eF eQ Fa Fy Ha Hc hF Ic iH iO jB Kd Kg Kl kQ Kr Kx Ld mE ml nW Or oT oV OW pH Pi qA Ql Qn Qv Qx Qy Ra Rc Rf Rg Rh Rj Rm Ss St Tn tO Tv Ua Ud Ue Uk Ul Um Uo Us Ut Uv Uy Vc Vh Vq Vs Wb WE Wh wQ yD yJ) Cs(Ad aM aN Ap As aU bB BC bE bU bX cC Cp Cv dB Dc DD Dg dH dI Dl Dp eC Ed Ez Fa Fb Fy Ha hC Hf hG iA Ib Im In iP Is Je Jf Jm Jn Jy Kj Kl Kx Ld Lj Mg Mk Mn Mt Ne Nh Ni Nj Nm nW Nx Ny Og Oh ON Or Ou OW pF Ph Pi pK Qc Ql Qm Qn Qt Qu Qv Qx Qy Rc Rf Rg Rh Ri Rj Rm Ss Tn To Tr Tt Tv Tz Ua Ud Ul Um Ut Uu Uy Vo Vs Vu Vv Wb Zq Wm Th) Nw(Ad Af Al An Ap Aw Ba Bb bF Bg Bo Co CP Cq CT Cu Cw Cx Db dC De Dg Di Dl dR dU dX Ed Ex Fb Fn fR Fw Fy GP gV HA HfhP hR Ib iC jB Je JF jG jM jO jQ jR jT Ju jV Kd Ke Kg Kj Kl kS Kz IL IM nL nN qA Qg Qh Ql Qn QT qU QV qW QX qY rA RC Rf Rj Rm rR Sf sH St tT tV Ua Uc Ue Uf Ug Uk Uo Up Ur Us Uu Vq Vs Vu wE Wm) Lj(aE Af aG al aJ AL aO aP aQ Aw Ax BA bC bF BG bH bJ bN bQ bR bS bZ cB cF cG cl cJ cL Co CP Cq cR cS cU Cw Cx cZ DB dE dF Di DK dL dM dN DR Ed eF eQ Ex Ez fA Fb Fy gL gP gW Ha Ib Jc Jf Ju Jv Ki Ks Ky ml nN Op oW pH pK Ps qA Qg Qh Qt Qu Qx Qy Ra Rc Rf Rh Ss TN Tr tT Tv Ua Ue Uk Um Us Uv Uw Ux Vq

Pe Qc Ql Sr Ug Va) kG(Fy Il Is Mf Ng Nm Nx Pz Rj Rm Tz Va Vq) lM(Fw Gl Ib Jr Ke Nm Nv Oy Po Qa Sr Uc) Qw(Dk Kq Li Nt Om On Qa Ut) jO(Al Dk Fr Fw Jg Jl Nt Nu) kI(Dd Fy Jo Js Kg Li Ph Qa) Rm(jU mI mP nA nH nL nN) Nx(mI mP nA nL nU oW) mM(Ez Ii Ij Mm Nm On) Ne(jE jH Qa Qd Ut) Is(fA mY nH nL nO) Qm(jE jH jK jL jR) bU(Kq Mz nN On Vq) jM(Db Jl Kq On Qd) kP(Iz Nm Tz Uw Vq) Ut(aM bR lY Vc) cR(mW nA nB nC) mI(dD Jk Ks Yi) iP(Ih Jn nN Qa) Db(jI Qd Qh) Ha(aG kR pF) Js(kO oN pF) Li(eM iA kN) bR(jF jR lK) nL(Ii Jq Ng) jT(Hf Ii Ug) lL(dK Nt Nu) oV(Jo Ng Tv) Qa(Nd Pk) Kg(lY nD) Ks(nB nC) fA(Fy On) nO(Tz Xa) nR(Kq Mn) nA(Ou Rg) iC(dB Dl) jV(Mr Ni) AlnN AokO DdnC NoiO MzdX HwpI QcjR JqlK QljG UgjI VajK VuoD aWnD} lK{Vc(aC aH aI aL Ar aV bB bE bJ bZ cE cI cJ cU cZ dD iB Is Jj jK Jq Kq Kx Ky Ld Li Ml Mn Mp Mt Nw Oh Ow Pg Qh Qx Rv Vi) Dr(aD aP aV BB Fr In jI jK Ky Lp Lv Lz Mk Ml Or Ow Pe Pg Ph Qb Qd Qg Qm Qx Rg Tv Tz Uk Vb Yd Yl) Yd(aD aH Ar cC cH Cs cZ dD Ed Fw Hf iC Is Kr Ky Ld Mp Mq No Nw Ny On Or Ou Ow Pg Ps Ql Rv Sr) mW(Ad Ao bA Bc Bg Ch Co Cp Ct Cu Cv Cx De Ef Fn Hc Iz Jd Kn Qg Qt Qw Ra Sr Ua Un Uv Vs) mU(Cs Ct cU Cx cY dA dJ dK dM Id iO kS Oa Pi Qg Qy Ri Sr Uf Un) kF(cT Fb Je Qt Qz Rb Rj Uc Ug Uk Uo Ur) Qc(Fc Fd Gb Gn Rt Ru Uz Vb Wc Wg Xa) lY(An Ar aS bC cA cV Fn Kz Qz Rb Uk) Zx(aZ bR cL dB Hf Ii Ke Mz Oi) Vh(aM bR cB dI In Jq Ky Oi Or) nD(An Ar cU Cv dJ Id Ms Sr Uv) nA(Cp Ct Dc Hc Id lL qU Ri) Vi(bV dB Hf Ke lL Nf Ph) Id(Jd Kd Lp Nf Uo) Oi(Ps Ry Wd Yl Zw) Va(iC Ky Nw Or Ou) mT(cD Rf Uk Uo Vs) Rz(bB cV On Qu) Fn(kC kK mM) Mz(Hp Qw Ua) Hf(Lp Yl Zw) Sr(Jj Nf oN) Jq(Hp Lp Tl) Ps(cN Hp Ih) Uw(aR Hx Mf) Dc(Vb Wd) Si(On Or) Jd(cP nW) Qz(kK mY) Tl(Lx Nu) Nw(Em sI) Ur(fR mM) Uy(Mf Or) MkRx UaUx HxVw JekK JjKg RvaP YlcD UoUn UpnR aGfR} Vb{Dc(aM As bJ bO bU cD Cu Cw cX Db dC Dd fA Fw Hv Ij Iv Jo Jr Js Jt kG Kq Kx Li Lx Md Ml Ml Mt Mz Na Ni Nm NO Nr On Pd Pe Po Qx Ra Sf Sr Un Yk) Cu(Aa Ad aJ Al aM As Aw Bb bF bG bS Cv Dd dG Dr Ef Fr Hq Hu Ib iC Ir Jt Kr Ks Lu Mf Mg Mm Mn mU Nm nO oP Pi Pk Qh Qw Rj Ua Us Ux Uy Va Yk Tl) Nm(aE aM Ao bB bQ bU cQ dC dD dF Dr gL hC hG iB iO iP jL Jm Jr kG kI Kp Kq oV Pk Qa Us) Jt(aM As cD cR hC iP jL Mf Or Pi Pk Qw Sf Us Yk) Kq(aD aG cC Db fB Hu iP mU Qw Ug Up Us) Dd(Db Mz Ni On oQ oW Po Ux Vw) Ao(kI kO mU nB nN Pi Pk Us) eP(cG cO Jo Ma Mg Rz Uf Vq) On(bF dC Dr iP Pk Qw Yk) Cw(Db Dr fA iA Qw) cR(eQ mW nC oT oW) Qw(Ij Li Om Vi) Ux(kG nO Pi Qa) Db(Aa Li Om) Dr(As dF Om) Jo(jV kI mS) Ke(bU Us Yk) Uf(eM mS mU) Va(iC oW Qa) Vq(jH lO lW) mW(Fr Jn Ng) kG(Al Hw Ng) Bc(bB Ut) Fy(cD mU) Ii(Pi Pk) Il(jU jV) Ks(eQ kF) Ou(bG bU) Us(Ap Ko) aG(Ha Kx) aM(Kg Ut) aW(nC nH) mI(kI Oz) jM(Of Uy) lO(Fn Mg) AaiO DgPk DkYk FwUn LvdX MmmS MxoT NejE HwbB IrjV IsnO YicX WboW JniP QljI QmiC OmbG VwkI nCnL} Sf{Dd(Al aM Ar bB bR Cs Dc Dk Dr Fa Fy Hf Ii Ij Il Im Iq Ir Is Jm Jq Jr Js Ke kI Ko kP Kq Kx Ky Li Lj Lx Lz Mf Ml Mm Mn Mr mS Mt Mw Mx Mz Ne Nl No Nr Nw Oa Oh Om On oO Or Ou OW Pe Pf Po Qa Qb Qh Rg Sr St Un) Dc(Aa Ar aW bB bJ bO bR cD Db Dk dX Ed Fw Ij Jj Ju Ke Kq Ks Kx Ky Ld Li Lj Lx Lz Mn Mw Mz Nd Ng No Pe Pi Pk Po Qm Sr Ur Ut Uu) Mn(aS bR Cv DB Dr eM eQ Fw Im Ir Jm Ju lY Mf mH mI mW Mz nB Nc Ne Ni Nl Nm Ns Or Pk Qw Up Vc) Dr(bO Cu Dk Fw iB Ij Kc Kx Ng On Qh Ut) Kc(Al aW bS Cv dB eF Il Nm Qw Up) Ij(eF kO kP mS mU mW oQ Qw) aW(Dk kI Kq Ny On Qh Un Yi) No(Ad aJ bS Cv mW nY pI) jV(Fw Jj Nu Po Qg Ql Sr) Dk(aJ cD Hu Lj Oi Qw) Kq(eF Fw Hu kO oQ Up) Lj(Ad Jt Kg Ou Up) dX(Cu Fy Js Mp Qh) Aa(Al hG Mf Ni) Im(aJ bS Hu) Qh(cD Db Sr) On(aJ bS Qw) Up(Ko Sr Un) Ut(mU Qa Qw) Pk(Al Ii Mm) iB(Il Un Vq) jK(Ug Va Zx) Fy(bR kI) Ha(kR pI) Nm(aM eF) Mz(jF jM) AdAj ArbR PojM LuhC LxjU MfKo MmkP HfiC IqjL YicD QaiP JqjI JsbS NybB VqlM aImI} sJ{vV(Ax bA Bb cV dA Db gW Hr Hw Hx Ip Jg Kc Kq Kr Ld Nm Oi Pa Qg Qm Qv qZ Ue Ur) tT(As bJ cV Fa hF Hq kR Ks Ld No Nq Pc Qg Ss Tr Uc Ue Ur Vo) Ib(As Dc Io Jg Ju Li Ma Oi Qg Qz rT Tr Uf vS) Nw(Io Is jE Nq Of Oh Qn tO tR tS wE wG yH) vP(bA Dg Dl Hr Hx iA Ks Nd Pa Qg Qm Uc Ur) rS(aQ Bg cV cY eC iA Ks Nq Qx Qy Rg Uv) Id(aR bL Ip jl Nn Nu Ny Oi qT Qx Ug) cV(dF Jl Jr Lx Nx rW tV uO vI) Qg(Ef Jh Lj Nn Nq Qu Ua Wm) Dk(An eD Lj Mz Oi rT rV) wE(Kc Ki Ko Kr Ky pS Ub) jM(As Fb Or Qx Qz tV Up) Ic(Ax Ip Nn vS vT vW) Ke(Aw dN qY Tn tR tX) wD(hV Js Ki Lj Rb Tz) Mz(Cp Je Qx Qy To) lo(Ad Ba iA Ph Tv) tM(Bc hG Kd Kk To) vO(Ch Ef Qt Qw Vs) Nn(Rf Sr Uf Un) Nq(tS tV vI zI) yH(Aw Je pS To) Aj(Aa Ks Oi) Ub(Iq Ir tL) Qz(Aw Lj Uk) Jk(Js Jt Jv) Kr(tO tS tV) cY(aK Ax Kd) iA(Bn Jl Ny) qT(Lj Pk yJ) Bg(Jg Uc) Ef(Oi rT) Ip(Fy rU) Iu(Aw Fn) Je(sC yL) Qy(cQ Hr) Js(Jh wG) Or(tO tS) Ou(tR tX) eC(vQ wG) tV(Fa Hx) rW(Kp Nd) uO(cU rU) CoDg CpvQ WmsK HaeT InLj IzOi JdcW JgUu QwxA KqrV LdaY QlwL NyyJ UkUg VulL PgiH cDtS hXpS jErT} oW{bU(aC aL aN AR bE cR CS Cv Dc Dr eF Fa Fc Fp Fr gL Gn Ha Hf Hu Hx iA Ib iH Is Je Jq kI KS Kx Kz Li Lt Mf Mk Mv Mx My Nd Nf Nj nW Nx Ny Oa oK Pa Pz Qa Qb Qn Qu Tv Ua Ut Uu Vs Vz Yl) cR(Aa aJ bH bM Ch cJ cS cX cZ dD Fa Fc fR Fy hC hG Hl Ic Io Je Jq Kx Ky Kz Lt LW Me Mk Mv My Na Nm Nx oD ON Pk Qh Tz Va Wf Yl) bB(aC aS Aw aY bE bF bG bP cE cG cQ Cs Cv dD dL Dr Fp Gb Gz Hu iP kF Ki kQ Ly Mk mU nR Nx Oy Pa Pd pF Pg Pz Vz Wb) aL(aO Ar aS aW Ax bM Dr Fd Fy Ha Ks Li Mx No nR Pk Ut) Nx(Aa Ax bR bX Dr Fc Fp In Nd Of Vs Yj Yk Zx) dD(aW bM Dd Dr Jn Jy nL No Pk Ut) Dr(bE cJ cK Gn Kx mS Ql Vq) Ax(cQ cX iP Mk nR Oy) Yk(cJ Dd Hu Jr No Ow) Ko(Ap Bb Dl Jg Kl mS) Wb(aC bE cJ Kx Nj) Mk(Cs eC Kx Li) Fd(Aa Mb Rj) Fi(Dd Ha Ks) Xa(aJ iP kR) Kx(Mb Me Mh) Cs(iO Ng) Fa(Gb Hu) Yg(Ow Yi) Wc(Dd Hu) Li(eC iP) Oy(Jq Tt) bX(Rh Ri) kF(Fw hB) AaGn CtYi YfMx NobE YjUr VzoD LjcQ RvRj UuVa aInR bIcX} eW{Mb(Aa aF aK AR aX bF bG bJ bR bS bZ cF cL cO cP Cs cV cZ dF Dg dH dI dN Dw eP Gd Hq Jo Lu Mn Nx Of Oy Oz Pc Qb) aM(aC Aj aN aP aW Ax aY bA bO bR bW cS cT DG eM Fr Gd Mk Mq Mu Mv Nf Ni Oe Oi) Mn(aG Ao Ax bM cE cW cX dL dN Em Hx It Jh Li Lj Mh Ml Ms) aF(aC aI bB bE bS cX dF Gd Lv Lx Mh Mk Mp Mu Nw) Lv(aC aG aO bE bN dA Dg eP fR Hr Mh Pe Pf) Nj(aS bR cD CX dD Ew Jg Mh Ml Mr Ni Qb) aC(aL aX bO bS cR Ct CX fR Ik) Ml(Al Dc Ii Iq Jm Jt Mz On) Nx(cB Cs Ct dA Fp Lj Lx Oy) Of(Al Cv Ii Io Iq Jm Mp Pd) aW(Af aV bR Ct CX cY cZ) cB(AD Ap Bb Jo Oz Pb) Aj(Bg Ch Co Ih Nn Qc) cX(Aa aO bR Dd Dk Iq) Bb(Aa Dd Ii Jm Jq) aY(bS cL fP Ir Lx) Nm(Bg Dl Gd Ng) Lj(As bO cW eM) Oi(Al bC Em Qb) Fr(Hx Po Qb) Nd(aV fR Ik) Jj(Al DC) Jo(aI Dd Jm) Jr(fR Mv Nb) aD(bH dD Mh) Gd(bM Pa) Lx(bG Po) Mu(Jn Qa) Jq(Ao Dl) bE(aL cP) bO(dD Mh) bR(cZ dE) BgJm BoDg CtJn CwJg LyIr MkbM IvfR OycW cPcS} wE{Pk(Ap bG cF Dg dH dJ DL Ez fN Fw hP Im iP It Jd jI Jl jT jV Kc Kc Kk Ko Kr Ky Ml Mm Mt Mw Mz Nm Nw Nx Ny Oa Oi On Ou Qd Ql Qm Ri rS rV Ss St tT tV Uc Ur wD) Kn(bQ cF dH dJ Dk DL Ed Ef fN Fw hG hP Hx Ib Ic Im Jd Jh jM Kc Ml Mz Nb Oa oH Ou Ql Qm RA rO rS Ug uM uO Ur uV Vu wK wQ yH) Mz(aQ aU Bb bJ bP bQ cF cQ Cw cY Dd eC fY gL hP Ic Jd jH jM Kc Ki Ky oH pF Ql qO qP tF) Ic(Bb cF dB Dl Id Im iP It Jd Js Nw Oa Ql Tz Un uV) Im(cF Ch cQ dB Ef Hf hG iA iO Iz lL nW pF Ph tF) Kr(bJ hC Mt Nl Oa oH Om rZ sC sI tO Tz uV yH) lL(Fa Fw Fy Js Ny Oa Om Ou Ql Tz) Jd(Ch Id jE Jk Jr Jv qA) Tz(dJ Dl hP Hx Jv nW) Ri(Bb cF Cv Hx Id jM) Oa(Bb Hx jK pF rS rW) It(hG jK jV pF rB) tF(Ed Fw Ou Un Vu) cF(Ap Dl Ou Ql) Bb(Ed Je Vu) Ke(pF tO uV) Ap(Ed jE) Dl(cU qO) Js(jK Ra) Un(Hx nW) Vu(Ao cQ) sC(Kk Wm) DkOn PohG FwnW LudL MtQm IddJ TrVq QvsI QtPd JlbQ QlcQ OupF} pH{eC(aC aE aI aO bB bH bN bR bU cF cL cN cO Cs cX cZ Dd dH dJ Fp iA In Io Ir Jn Ko kR kS Li Lj mI Mk Ml Mn Na Nb Nd Nj NN No Nr Oh Or Oz Qc Rj Uw Vs Wm) bU(aC aG aM bE bN cC cL cN cO Cv cZ dH Dr eF Gb gL Hl Hu Ib iH iP Iq Je Jn kF Ko kR Ks Mf My Nj Oy Pa Pb Qw Ua Uw Uy Vi Vs Vz Yj Zx) Rm(Al Ax bH bI bJ bR Dd Fb Fy Ha Ir Iu Jn Lj Lx Mn Mx Nm No Nr Qa Sr Yi) Yk(aC Aw bL Dd dG Hu Ii Jr Kg Ks Li Me Mn Mw Nx oQ Pk Rj Wd) Ko(aC aL aO Bg dD Dl Fn iP Kl Nh nR Pd Pg) Li(Gb Hf kF Kn Qh Rj Ry Up Vj Vp Wb Xa) Vi(Ax Fb Ih Ij Jn Mn Mx No Nr Oa Sr Xa) Yi(BG Dk Ef Fn Jj Nh Nl Ql Uu Yg) iP(Ax cF Gp Ir Nn Xa) Mn(nR Si Up Vh Wc) Lj(Gb Kn To Wb Tl) bB(aO kF nR Qd Rg) cA(bE dD Hf Mf Uu) cR(Kd Lp Ru Vs Vz) Me(Fd Hf Wc) Nh(bE Is Jn) Yj(aL Ks Mf) Wb(aC bX dD) Fn(bI Rx) Nl(dD Jn) Yg(Cq Rh) Wc(Jn Rj) Rg(bX nL) Rf(Kx Nr) nR(aI Uf) AxfB DdFi YfMx JjKs XadM} iC{Va(aD aG aH Aj As aX aZ BA bB Bn Bo Ct cW cZ dA dC Dl dM dN Ed Hl Ho Ic Is Jg jH jK Jt Ju Jv Ki Ky Ld Lv Mb Me Mf Mk Mm Mn Mp Ms Ng Nr Nt Nu Nv Oi Or Ou Ow Pa Pb Pc Pf Qc Qx Rx Ry Si Ss Tv Vq

Figure 33 Continued

Vw Wd Wf Zx) Dr(Al Ap aQ Ar aY bC bE bR cP Ex Ez Hc Ik Jd Jh Kc Nd Ng Nr Pd Qc Qw Sr Um Un Ux Vq) Yd(cH dK Hx jM Kd Mn Nc Nd Ne Ni Nl Nn Ph Ru Ul Vc) Si(Al Cv Db Fn Hf Io Iq Nc Nd Ne Nl Sj Ux Vo) Ux(aG aR aX bN dB Ki Mf Ph Tt Tv Ue) Fn(Em Gd kP mY Rt Ru Vc Wd Zx) Vc(bS bW Cw Dd Kg Mf Vq) Mz(Ez hP Ib Sj Wf Tl) Ri(sC sK tO tR vV yJ) Em(aE Hf Ko Lt Zx) Tl(dK Jq Js Nl Nw) Ps(Hu Im On Qn Qy) mT(Af An As Dc Ib) Mf(Gb Rx Uy Vw) aR(kG nH Sj Zx) Ex(uT wB wQ) Ne(Ho Rt Vh) Wf(Iq Jn Qm) Kd(sC vP vV) aG(Fd Ho Rt) cP(mP nD nH) Cu(Gh Rt) Dd(lX lY) Hp(Dl On) Vz(Dc Qc) Zx(Hx Mg) Ke(Sj yJ) Lp(Db On) Um(kE kP) Vi(Nu Qm) fR(Kk Ko) AdWd AnlX DgRz FdIi GbbS NmHl NhVh IqWb JemP RuVq WnnW UmL bCnN bJnJ} eQ{Kx(aD aH aL AO aW Ax bI bL bU bX cR Dd Di dK Dr eC gZ Ho Hu Ik Im Jn kE kF kN Ko Ks Ly Me mI Mn mS mT nH Oz Pa Ph pI Po Qc Qm Qy Rf Tz Wb) Ha(aH aI Al bB cR Db Dp Ex Ho Hu Hv Jj Jn Jr Js Ko mI Mn mT Mx Ne Nh Nl Oi Pi Qm Rm Rv Up Uv Vp) cR(aC Ax Ed Fd iH Ir Je Jy Ky Mn No Oa Ph Pk Qc Sr Tt Ul Ut Uu Wf Tm) Mn(Cs Dr Fa Fp KQ Ld nW Oy Qn Qw Si Sj Uu Vz Wb Yd Yk Yl) Ks(Ax bB cA Ex Gh Jj mI nH nW Rv Va Wd Yg Zx) Yi(Ba Bg Ct Hu Ng Oz Pz Qw Uo Uw Vs Yg Zx) No(aO bE cQ cU Gn Hu iP kF nI Qn Qw Tl) Hu(Fa Kq Lx Nn Ow Qu Sr Ut Xa) Uu(Ba bX Ma mT Ng Nn Om Ow) Dr(Ax cJ Cq Dd Jn Nr Ph) Ut(bF cC Ho Hq nW Qw) On(aC aO Ax Ef Hc) Fa(Aa Dd mT Ng) Kq(aC bF oP Qw) Ph(cA Ex Wd Yl) nW(Kg Ko Ky Li) Ax(Db Gl Qm) Gn(Fb Ij Jn) Ho(Ng Oz Pk) Js(Uw Vi Yg) bU(aS Ip Rh) Wf(Jn Rm) Qw(Li Mt) Kz(dK mT) CweC DdEx EdVi FymT JnUw RtnH} eP{Fc(Ar bB cG Cs dD dF Fa Gd Iq Ir Js Lj Mx Nw Oh Or Ow Po Qa Qb Qh Uu Yi) Ho(Aj Ar bB bS cO dF Gd Jj Lp Mf Mh Or Ou Qh Ur) Kc(aN Ar bB dL Ed Gd Iq Jj oE oF Ou Ow Qv Vq) Uy(Ar bZ cO Cu Ij Kq Ld Li Mk Nn Nq Om Pf Tn) Ur(Dr Fd Gn Hp Kx Lp Mp Rt Uw Wb Yg Zx) Ar(Gb Ps Rv Rz Uz Wc Yi Xa Yf) bB(kR Ld oE oF Ry Vz Yi Yl Yf) Fi(aM dF Fa Gd Jj Mz Or Uu) Kx(aL Ib Jj kR kS Kz oF Tv) Ow(Kk Lt Un Vj Wc Yl Zx tF) Ld(dL Ed Gd Jj Mp Qv Rg) Nw(aN Ih Io iP Or Pk Tv) cG(Dr Lp Lt Rv Vc Wc Yg) Wf(aM Fa fP Id Mr Ni) Or(Ad Ao Cw Dg Jt Ko) Fy(Hp In Lp Rx Zw) Mp(dR Kk kS Ry Tv) Uu(Gb Rz Si Yh Tm) gW(Aa Jt Mr Mz Oy) Tl(cU Jr Rm Uf) Ou(In oE Yi Yk) Dr(Co Mr Uf) Si(dD dF Gd) Un(Dc Qw Va) Vq(bL Kk Kn) hB(aK cB cY) Mk(Ry Vz) Mn(pF tF) Mr(Lp Rv) Mt(Uw Vw) Ni(Wc Yf) Hp(Js Qa) Tm(aU Mb) Ke(bH Db) Rz(Gd Jj) Yl(Fw Uf) Vj(aM Uf) bC(oF oH) GlRv MmQn HvLp HcXa IoUw YhQv YicJ VzbO WccO KobL RxdF NxoF aKhC} fB{Uo(Ad aI An Ao Ap aW bI bJ bU bX cA cF cG cI Co Cq Cw Dc Dg Dl Fw Fy Gd Gp Hq Il Im Ip Iq Ir Is It Iz Jd Jf Jo Jt Ko Kq Li Ma Mg Mm Mn Ng Nm Nn Of On Qa Qc Qd Qu Rz Tr Tv Uf Ut Vo) Fy(aA Bo cR Ct Dd Dp hB Hf Hr In Jj Jy Ld Lx mF Mk Nc Ne Nh Nl No Oy Pa Pg Qh Rm Up Ur Vs Wm) Ax(aL Ao bB bU cJ cR dD De gL hB iZ mF mT Ng Nn Qu Xa) Dd(Hr Jf Jy Kq Kz Ne Nl Qm Qn Qt Rx Ss Ub Up Ut Yk) Kq(Ii kR Mj Mk Ne Ng Nh No nR Rm Vp Vs Wm) aL(cR Ld Li Ma mI mP nN Nu Pe Qa) Hf(bI Cw Dg Jg Jt Ko Nm Of) Aa(Il Iq Qt Ss Tn Vq Vu) Ut(aM cT cW Mk Nh Nl) Pk(Ao bI Cw Dg Jg Rz) dD(cR mI nL nO Nu oO) Ne(Ko Qz Tt Tv) Nh(Ij Jg On Qc) Xa(cD Hu Ib Jk) bI(Ed Kx Rv Ur) bX(Ps Qy Vi Vq) Hr(Hw Jo Ks) Jy(Ao Cq Ng) Rz(nA nL No) bB(Fc Ny Yh) Rc(Kz mF) Jg(Ua Ub) aW(Qt Rx) AoUu BaVs GpNo NgKp NlQc HwUr IjYk IzZx YgdC YicJ KobJ LioF} gW{kK(Af An As Aw Bg Bn cB Co CT dA De Dl Ez Fn Fr gP Hq Hv Ib Ii Ik In Iz Jd Jh jR kG Kj Kz Mb mP mS Mu Mv Mw My Ne Nf Ng nH nL Nn Nq Nt Of Om Oy Oz Pb Po Qt Qu Qw Qy Qz Rc Ua Up Vs) kF(Ad Bg bN Bo Ch cJ cK cQ cT cY De dI Ef Fb Hu Ii Ik In It Iz Jk kG Kj Kn Kr Ld Mu Mv Nb Nf nH Nl Ns Nt Of Ow Oy Qt Qu Qv Qw Qz Rj Ss Tr Uc Uk Uo Us Vs) mW(Bg CH Cu cX dL Ef Hu Hw Ib Jk Mu Mv mY nJ Qg qU Ua) dX(bB bP bV cT dE dR Jj Lw Mp Nx) nN(aL Ch cY Dk Jh Jl Oy Ql Us) lY(An Ar dA In Lv Mb mP Nf Oh) mI(bA dL hC mP Ne qU Tt Uk) mP(bM cC cY Ni Sr Un Ur) nJ(cU Fw Ri Sr Uo Ur Us) eM(Aa Aj Jt Mr Mz Oy) kG(An Ar Ir nT Sr Uv) nH(Cu Io Iq Ir Uu) kC(Ch Ef In Tt Ur) nA(Jk Ua Up Uu) kN(Ch Ef Hc Mu) Nf(mH nO) fR(bH oK) mF(Nw Un) nB(An Hc) NimT UkmH UmnO UpnR UsnD dlnT} iB{Ux(Bg bS bV cC cF Dg Dl Ez Hf It Iz Ld Lx Lz Mk Ml Mp Oi Ou Oy Ph Qb Qm Qx Qz Rg Rx Rz Ss Tn Tz Vw Zx) Va(aI Aw Bb BG bN cC Hf Ik In It Jj Ju Jv Ms Oi Oy Ph Po Qm Qn Qt Qz Rc Rj Tt Wd) mW(Af Bb Bg Ch Cp Ct Dk Ef fP Ib Iz Qt qU Qw Uk) Yd(cC CH dI Ez Hx Mn Qc Ru Ul Vc) Qz(Fd Hl lX nF nI nJ nL nT nU Ps Zw) Lp(bU cD Ii Iq Jn Nm Nw Oe Qm Sr) nF(Cp Ct De Dk Ef Ib Qt Qw Ur) Hp(aS bR Ii Ir Nw Ps Qc Sr) mU(AN Bg Cs cX Ef Iz) Em(aG Fn Lt Ur Ut Uv) Zx(cH Hx Il Mb Rc Rt) Bc(Fc Fi Ho Rt Rx) Wf(cD Db Nt Qm Sr) Vc(bC bW dH Fn Uf) kF(Dk Ib Qt Qw Ur) Uw(Hu Jh Mu Qy) qU(kP mF mY nD) Fn(kP Ru Vz) My(mI nC nU) Vh(Ef Ru Ul) kC(Ct Ha It) An(lX nT) De(mY nD) Mh(Uy Vw) Ho(Aw Ph) Qy(mP nH) Qw(lX nC) Tl(Ar aS) Rv(Un Vq) Ri(lW mF) Ur(mP nC) aE(Fc Fi) DcWd DrbC GzrP IiLt IlUy WbbU VzSr SjcC ZwVq QtmY JqPs TmaS OiVw aNlW} lL{wQ(Ar Ed Fa Fw Im Jl Ke Kp Kx Nw Ny Oa Ou Vu Wm Tj) rQ(Cv Cx Id Jd Js Ke Ko Kx Mz Ny Vv) Ou(Gd Gh Rz tN tO Uw Uy Vi Vw wG) Jd(Ed fN Id Jj Lj nN Of Or sK) Mz(hP sC sI vQ vV Wf zG Zw) Qw(kI mI nC nH nI nJ nL nN) Ke(qG rO sC sI tO vV wJ yJ) Rj(kC mF mI mP mS nA nI Zx) Ib(mF mI nA nC nJ nL nO) Ny(vV wJ wK yD yH yJ zG) Fw(Hp Lp uV Wf zG Tl) nJ(Ez Ha Qt Qu Ug Vv) sI(Bo NW Nx Qm tV) Fb(qZ rS sK tQ zG) Hp(aP Ex Nu Po Sr) Id(fN hP Nf uO yK) Kx(hP rW vV wJ yH) nN(dI gP Qt Qz Ua) Ct(Dr mW nL Vc) Kk(sC wJ wK yH) Un(rW Vi vV Yd) Fa(hP uU uV) Sj(Nu Po Ql) Lp(Po Sr Vw) Oa(tQ wF wP) Ur(mI nA nO) Vv(qZ rW yH) mW(bJ cH Cp) Wm(hP rS) Zx(jE Oz) Qz(nH nI) Qt(mI nO) Lt(dF Or) Ql(tQ wF) Nw(Vh wJ) Uk(qZ sC) mF(bN qU) nA(Ha Hc) hW(kC kN) tV(It jM) rW(Ip Nx) AnnD BaVc CpkF CwTm DrdF TjqH NiSi UamI VzcU SrRx JjUx JstQ TlPh KcyH KnwJ KofN RisK QnkI UgtT VhcH VuyD aKfY dInI dLmU wDjM} jL{Dr(Af Ap aR DK Ex Fr Hc Hu Ik Jd Jh Jr Nr Pd Pf Qy Tz Um) Ux(aM Is Jq Ke Ky Ld Lx Ml Nw Or Pe Po Qa Qx Rz) nJ(aR aS Ax Dp Gp Id Ju Jv Ke Qz Ri Sr St Un) Zx(Ad Aj Cu Dl Ic Is Jt Mf Mg On Ug Zw Wm) Vc(Ad Ar aY cP Cw Ex Fw Jd Jh Mm Pd Uc) Va(Jn Ke Kk Kq Lx Mj Nw Ny Pe Ql Uw) Qz(mP mT mU mY nA nB nN nR nT nU) Vw(aM Ke Ld Lz Ml Nw Or Qx Rv Rz) Hl(aG aR Hr Is Lx Mf Or Po) kF(Ax bA cT Ki Ld oH Qw) Qc(Gh Gn Vz Wd Yl Zw) Ps(bS cC Dc jE jF Mg) Un(mP Vz Wd Yl Zw Tl) Vh(cC Iq Nh Oe Rh Tz) Ho(aG dK Ne Tt Tz) Uw(DB Io Nm Ug) lY(An Ax Cs Kz Ld) Rz(cP Ql Sr Uc) Yl(bR cB Nt Ug) mT(Bc bN dI Ki) Em(aR bR Kc) Gb(Lv Mf Or) Hp(Dk Po Qm) Yd(cP Ex Fw) Kz(kE kK nN) Lp(aE Jq Ke) Vi(bF Ko Ug) Gn(aR Qm) Wb(bU Ke) Wf(aE Jn) Ra(mP mU) Tl(dK Id) Rv(Jt Ug) mH(Bc Uu) AxmU CvnN FwSi ZwSr RxaE LdkC LtOn UydK aRnO cPnD} jV{Zx(aD aH Ar aX aZ Bc BO Cu Cv cW dE Dk Gb Gl Gp Io Iq Ir Jn Js Jy Ke Kn Kx Mr Mz Qa Rm Ry) mW(Ad Af Aw bA Bb Bg bN Ch Cq cT Dk Ha Qm Qu Rb Rf Rj Uc Ue Uk Up tF) mU(aN Ax bB bG bH bP bU cB cF eC Fw Kn oH Or) Rv(aQ bJ cC DB Dg Fn Hx Iq Jo jR Mg Qw) Rz(Iq Jd Jn Kn Kq Mg Mm Nu Ql Sr) Sr(Fd Gn Hl Ho Hp Ps Rt Vw) Iq(Gd Gh Hl Hp Rt Rx Ux) Dr(aD dF Jr Js Ql Qm) Gb(aI Ar Lv Or Qm Tz) Si(Fw Ni Nu Ql Tz Tm) Ux(Ij Lx Ml Nw Ou Ow) Va(aD Jq Lx Mj Or Pf) Lt(aD aH Is Lx Pe) Yl(cD dK Ql Qm Tz) Un(Fd Uy Wd Zw Tm) Rj(kC lY mF mI) Ar(Vc Vh Wb) Cu(Hl Lp Vw) Fd(Fw Mz Po) Qg(Vw Zw Xa) Tm(Ke Ny Ow) Rx(Id Mk Mr) mI(In It qU) nH(cN cQ gP) Em(aI Ur) Tz(Vh Tl) Hf(nC nL) Wc(cC Mr) Wf(Nw Ou) Uw(aG cF) Vc(cU Mm) Vi(Jk Tt) aR(nL nN) nA(Cp Hc) FbkF HlQm IlLp VzQl WdKq JsTl PscF RycC RtPh NwVw UydK VhcQ VuwL rZoP} Lj{Qw(aK aU bC bW bX cD CQ Cu cY Dg Dr Il iO Jd Jt Kq Mm Mt Mu Mz Nn On Or Pd Qa Tz Uc Uf Un Vi Vu Wb Yd Tl) Wb(Af As bB bC bO bS cV cX iP kI mS mW nA Pi Pk Qm Up Us Ut) iO(aK bB bM bX cX hP Hu Ik Ir Jj Mj Mk Nj Nw Qz yJ) Jd(Ba Bg bM cD Ch Cx Hu Ib Ik Ju Jv Kc Nq Qu Rf) Gb(cD Cu cV cX Fw hC mW Or oV Pi Up Us) tV(Ap cH jM Kc Kr Mk nW Vu Wm) Nw(bM Lu Lw Mp Ms Nj Pb) Ew(aN Dd Fr Mu Mx Nj) Vi(cX Db mW nO oV pI) bB(iA lY mI oV pF pI) Dr(mS nO Ou Pi Ut) Jg(Jj Ms My Of) Qz(Cu Kc Pk Un) On(Mp Ms Nj Of) Uy(Dd jM Up Ut) Im(In Ms Nj) Kq(Hu Nb Nq) Li(Jj Lw Nj) Or(aK aV bM) oV(Lt Qn Ry) oD(cR Db mT) pF(Mm Nx Ow) Dc(Jv Ur) Dw(eM Mn) Ut(Vc Wc) Va(bO Fw) Vh(bU cX) Vw(eF Up) bX(eC Rg) pI(Qn Ry) AabM AdAj CuYg DbkI InsI YicX JjKg KkPk WneC UxbO aKiA bUnN cIfA rBwD} jM{Uy(bB cZ dD In Is Ke Ld Lv Lz Ml On Ow Pe Pg Ph Qa Qb Qg Qx Rx Tv Tz) Yd(aL aM cG dD Fw Hf Id Ij Ir Jq Ky Lx Ml Mp Nb Nw Ny Pe Pf Qa) Uw(aI aV aX cI Em Hp Hu Ic Il It Jg jK Rg) Ri(rW tN tT tV tX wD wF wG wJ wK wP yD) Rv(aH

Ao Cs Cu Cv Dc Fa Fy Gl hB Hw Hx Ii Ij Im Is Jl Jm Ke Kk Ks Mm Mn Nn Nr Nv Ny Oh On Or Ou Ow Oz Qa Qb Qd Qh Tz Uf Un Vq) Ib(Ao Cu Fy Gl Im Jq Mn Nr Nv Nx On Oz Sr Uf) Uf(Bg Ct Iz Je Jh Ng Of Oi Om Qu Qz Rg Vs) Rg(Aa Cw Dg Fy Ir Mm Nm No Qc Sr) aC(Ar bB Bo Cw Dg Jg Jt No Nw Vq) Ct(Ba Fy Ks Nx On Ou Vq) Mn(Iz Je Qw Qz Vs) Ou(Cp Hq Hu Iz Je) Jj(Al bB Dc On) Cw(Bg Oy Uu) Fy(Oi Qv Yg) bB(cI Cv Wm) Hp(Hw Jm) On(Iz Qw) Ow(bE fA) Oz(aK bC) cJ(jR rA) FnrA MmQz MyNw TnYg TvoV HchB IrdM KogZ KxaR UojU} Dr{Mn(bU cC dC Ik Jj Ju Jv Mr mS Ne Ni Qw Si Uk Uu Uy) jU(Ar Hf Is jT Ld Lv Lz Ml Mp Or Ow Ph Qb Qg Qx) Ut(aM bB bO dF eC Hp Jj Ju Mt Qw Uk Uv Uy) bO(eC Fy Kd Ke Kx Ky Qh Ru Sr Un Us Yl) mS(bU cJ DD Fy Gp Il Iq Ir Us) Kx(As aW bU cD CX dF Fw) jI(bP Fr Gl Lp Mg Sr Tt) jT(aG bL cV Fn jG Ki Yd) As(Kd Ke Ou Sr) jG(Mf Sr Tz Vq) lN(Ql Qm Sr Zx) Aa(eC hC nW) Rg(dF Fw mI) On(eC Uu Uy) bB(Kd nN Uy) jH(Lp Yd Zx) jK(Ap Bc Fn) Qw(Li Mt) Qh(cD Jj) Uk(Dd Nm) jR(aG Gp) CweC DkUu FrKd FwRj HpmT QaUr aLmI dDnO dFjO} tV{Bb(Ao Ba Ch cQ Dk Ed Hc Hu Iz Je lM My Nq Oa Of Ph Qt Qy wH wQ) Kn(Ba cT Dk Ef fP Hc Hu It Jh Mj My Nb Oa oK Ou qT Qx vH Vu) Kr(bI Ch Ef Hc Hu Iz Kc Mj Mv My Nb Oa Qt tO vH Vu) It(CH cR cT Ef Hc hG Id Iz Kc nW rB Wm tF) Pk(Ap Dg dJ Hc Hu Lu Mj nW Oa oK Qm vH) Vu(An Ao cQ dH Hu Ic Id jK wH tF) Js(cQ Dk Ef Iz oK pF rB) nW(Cv dH Id Oa Om Ou Sr) Ch(Ap Im Kg tF) Iz(Dc Jg Kg Om) Ef(Dc Ij Pd) Lu(dH fP Or) Ql(cQ Hu tF) Hx(Oa Ri) sC(Kk Uk) AxNb GzwH IcfP lptF SroK JkUf} Id{wQ(Af cE dH Hr Jl Lx Mt Pa Pc Pd Pe Po) rQ(bQ dJ eD iA Kd Lu Ma nW oK tF) dH(uO uT uV uW uY wB yK tM) wF(bJ bP bQ It Kd nW uU tF) hP(cA Ic iO jI Lu Mm Wm) hV(eC iA Ic Kd Mp Nf Nq) tN(Ic Kd Lu nW Pc Ri) uO(Ap Ic Il Ra Ri wD) uV(bJ cF Il Ph Ra Ri) hO(dJ Fb Kd Tt Vo) hR(iA Ic Kd Mp Nq) rC(bQ iA lM oN uY) uW(bR cA Il Pd Wm) Yd(jK jR lM lN) cF(qQ uU wH) yK(Il Kn Ri) wD(aH It uT) Gz(tX wB) Lu(hC zA) aK(Ar qO) yJ(cA Uk) jI(uM wP) wG(Qm Ri) lN(mU Zx) uY(Il Jg) vI(Bb Ic) WmvO EmjH HrqI TrtL IttS UnuU bJtU} Ew{Nj(aK Ar Ax Ch Cs DC dM Hu Hv Ij Lv Lz Mk Mw My Na Nm Nr Oz Pb) bB(aG aL aO bG bR cD cP Ct dC It Jg Mg Mn Nu Of Om) Mn(Ad aI aM aY bM bP Cw Dc dL Nd Ne Oi) bR(aI aM cG Cp Cx dF dN Mp Nm) cB(Bg cP cR Cv Ik Mw Nq Nv) aN(Ij Il Ir Oi Oy Pb Pe) Fr(cP Iv Nc Ne Nl On) Lx(An Ct cY dC fP) Mb(Aa aS Ct Mq Pb) Nd(Aa aX Dc Ik Pb) dC(cR In Iv Nc) Hu(cP Hx Nc) aM(aV Ly Ns) aW(Oi Oz Pb) Aj(bM Mp) Nw(Co Nh) aC(Ip Mj) bU(cX Ml) DcJj LvcQ MwQc NcbE aVcW cCcX} jR{kF(bA Cp Fb Ib Kn Qt Qu Qv Qw Qz Ss Ua Ue Uk Ur) Vh(aG cB dI Kj Oi Qz Ru Uk Zx) Yd(aH Jj Ky Ml Mp Oh Ow Pf) nO(aS Fn Ib Qz Um Ur Vs) nJ(Fn Kr Qt Qz Rf Uo Ur) Zx(Hx Ic jG Kg Nx Vo) aG(Fc Rt Rv Ry Uw Yl) fR(Nb Nj oK Ow Qv) Qz(kK mF nI nT) Xa(aV cC Oi Qw) Ur(mP nA nD nT) Va(Ky Ni Nu Ql) cT(kK lW lY mI) Hp(On Ps Sr) Ib(mF mW nN) Vc(aH bB bQ) mU(Ar cB dR) Db(Ry Vz) Gd(Bc Ni) Tl(Lx Pf) Ux(cC Ni) bB(Gb Vz) nN(An Je) lY(cK dA) mW(cH Ct) CuLt EmVi FnnT GnGp HxYl TmaV KzkK RzcV UnmP} Li{Qw(aK Ar Cv Dc fP Il Mm Mt Nn Nw Oe Or Pd Pk Qa Qh Qz Tz Uk Un Vi Vu Wb Tl Wm) Nw(bM Jj Lu Ms Mv Mw My Nj Of Oy Pb) Lw(Jh Jj Mv Mw My Ng Of Oy Pb) Jj(Im It Jt Kg Nj Ny Pb) oV(Jf Yg Zx Xa Wm) My(Ir Lu Nj Nm) Wd(Cu gZ iO kI) Of(Jt Nj Pb Qd) mW(Gb Ib Vi Yf) tT(Mk Ml Nq Pc) Pb(Jl Nf Nj) gZ(Yg Xa Wm) mU(Fd Yd Yf) oT(cR Hu Vj) Ng(Im Jt) Wn(Bg Tv) Uy(Dd eM) Pk(Ik Wb) bB(lY mI) cF(Un Va) hC(Gb Vc) AabM AdAj CuRz MmwQ NjOy YdlM JktN KxpI RykI UrnH VinO} lN{nN(aI Cp De dI Dk Ef Ez Hc Qt Qu Ua Ut) Zx(Bc cT Hv Jf Mr Ni Nj Po Ri Sr Wf) Yd(dD Jn Jr Js Mr Nw Oa Ps Sr Xa) mW(aC bA bN cH cJ Cs Cu Ef Kd qU) mU(Ar aZ bH Cs Cu iO Or Pi) Uy(Ke Lx Po Qa Qm Tz) bN(mP mT nD nJ nT) dI(kI mP mT nA nJ) Si(Hf Mr Ou Ql) Vh(cC Fw Mr Sr) lY(aQ Kc oH Ow) Vc(cG Fw Mm) cP(kK mM nH) Fi(aG Qw) Ou(Rz Va) Vi(cC Ph) Vw(aG Lz) mM(My oP) nD(cI cT) nJ(jT qU) ArnT DgRv DkHp GhQm UbUw WcVq XaOi PscN YlcX aCnO nAqU kCrX kKnW} jK{Zx(Db Hp Hu Jv Kr Me Mu Mv My Ni Nq Nu Pc Qh Qt Rf St Ua Uk Uo) Ux(bI cA Cq Db Gh Hl Hx Jj Mr Nb Ni Ua Ub) Va(bN bO cC Fr Ik Jj Me Mr Nu Po Ql Rf Uk) Vw(aG bV In Rz Tt) Pa(Lt Ru Vc Wd Tm) Db(Rv Ry Uw Uy) Gb(Fn Nu Ph Sr) Hx(Rv Uw Vi Wb) Vz(Ap bC cD Iq) Bc(Ru Vc Zw) Wm(vP vV wQ) Wb(bI cZ Qw) Em(aE Lt) Hp(Ql Tz) Qw(Gh Xa) Tl(Jj Mr) Rz(Dg Sr) Rx(Cu Qz) Vc(Ap dH) Uy(bI Nd) AnlY DlLp DpLt FdQl GdVq NmTm NuSi ZwJt WcUg RubC VuwH cHmW} oV{Ax(aL bB Hc Hf Hv iP Jf Mk Ml nA Ne Nh Oy Pc Ra Rf Vi Wd Wm) Mx(bB Dp Ko Kx Pi Qh Qn Ub Up Vp Vz Yl Yf) bB(Fw Hl Kd Lp nN Oa Qw Ru Ua Uy Vs Wd) Fy(bF Bg cE Ef Hq Pz Uu Uw Wd Zx) Ha(Dp Fi Gn In Nh Rm Si Ur Yj) Kx(An aW Dd Fw kK mF Mk Po) Ks(Bg Fi Ho Hp Zx) Yi(Bg Ct Ql Yg) aW(Kz Qn Vz Yl) Uk(aL iZ Zx) bX(Qw Tv Uu) Cq(Vs Wd) Qu(bG Ef) aL(Oz Qw) DdWc PoFa FiPh FwbM MkPe TtOy WdbU JoUu UvUt} jU{Zx(AR aX aZ dB Io Kg Mf Qv Ri Vq) kF(Aw Fb Kj Qt Qu Qw Qz Rb Rj Uk Ur) mW(Bc Cp Ct dL Ib Iz Kj Uk Up tF) nH(aV Ct Hc Iz Ju Qz Uk) Uk(mI nD nI nJ nT) mU(Ax cB dL Ur Vs) nA(Ib Iz Qz Ua Ur) Or(Gb Lt Si Va) Uo(mS nC nI nJ) Vc(cU Lv Mf Yl) mP(Qy Tt Ua Vs) Qz(kK mY nI) Va(aI Lx Pf) Qc(Vz Yl) Tl(Nw Ql) Vh(Mx Ul) kC(bC Rb) kK(Ct Ib) AnlY PoHp FnmI GhIq LvXa TtnJ SjUn QwnU QtnD QgRt KnYl RjmF OwUx UmnC UpnR} jI{Yd(bR cH cR Hx Mn Mu Nc Nd Ne Nl Nn Va) Vc(bS cG Cx dF Fn Hp Hu Hx Im Qy) Ql(Fi Hl Rt Rv Sj Uw Vi Wd Yl) Va(aG aH aJ Hp Ik It Lp Ou Rj) Hp(bJ bR Db Ii Ne) Zx(Hx Jr On Ou Sr) Fn(Gd Hl Rt Rz) Vw(Jq Lx Mk Or) aG(Em Fd Fi Ho) Po(Hl Uw Vi) Nu(Hl Rv Vi) Ux(aD Ky Rv) nN(Qt Qw Um) mU(As dI dL) Qz(mW nJ) Lp(Qm Ug) Uw(Fw Qm) Vh(Qw Ua) CuRt DemW EmUr FdIi HxSi SrJj WfJn YlOi bNmT cImF dInD} lM{Yd(aA Ba Bc cE cH cQ Ct Cw dF Fd Fw Fy Ij Iq Jr Js Ke Nc Ne Ni Nl Nm Om Ou Pa Pe Ry Uw) nN(aG bF bP cE Cw Dd Kg Kn Kp Kz Qw) Vh(aE cP Hf Hu Ip Iz Nx Rv) Ou(Fc Fi mW Rv Ux Vw Zx) Hp(Ke Nv Om Po Sr Tr) bF(kF nB nJ nO nT) mW(Cu dF dR Kn Ow) Sr(Lp Ps Tv Va) Uy(cE Hf Mg) Po(Va Wf) Wc(Cw Hf) Vc(cU jT) FiaG FnRv GlYl MgUw HxZx WdVq TldD KnnJ OrmU OwlY cEkF nRoE} hC{Gb(aJ aW bB bG bO bU cD cN Cx dB Hc Hp Il kQ kR Lu Oi Or Qu Ur Uu) Lu(Gz Kn Or Rg tN tR tT tX Un Ux Uy Vq Vu Wb Yi Yj) Yi(Aa bG bU cN Db Hp Iv Mj Ur) Vi(Cw Fy Ke Nm Nw On Qa Qd Si) Vc(Aa Il Jt Kg Mm Mn Ut Vq) Si(bO Qu Qw Rf Rm) Uy(Aa bU Nx Or) Hp(Nm Qd Vq) Uw(cN Oi Or) Aa(bM Wb) bO(Ux Va) bU(Vh Wf) HcOn XacN RivH cRoT mIqY} tT{Ap(bU cB cF Ch eC Ed hO Jk nW Of oK Pk Tv Vv wG) Dl(bU cC cF cJ dE hO Kk Kp Nb Oz Pk Ri Vv wG) Vq(dA dM Kk Ri Tn Tr Tv tM) tF(Fb Fw Md Mf Mm Ou rP Un) Bb(Ao Ba Hu Je My Oa) Mm(Hx Jk Mh Mk Of Oz) Dg(bU cF Of Pk Vv) Ri(Oi oK uV wG) eC(It Js Oh qZ) Ar(nW oK) Lu(Pk rQ) It(iO rB) Ra(Ke Kr) Jk(Jg Ny) eD(Fb Vu) AxNb MkPd IcuV PkdJ zHoH} bB{mI(Ax cR Hu Jh Nw Oa Oz Qt Ua Uk Uy Vz Yl) Uy(bR Db eM mH nB Nc oE pI Ul Un Ut) pI(Ax Cs Fa Fp Ha Oa Yl) Vc(Bc Db Dc kR Us Ut) lY(Ax Dd dI Hq Hu Nw) nT(Ax Bc Ld Oa Oz) Wb(Db nB Nc nN) Lt(kP lW nN nR) Wm(kC nD nH) Qw(mF mY nN) nR(Nw Sr Uf) mH(Ir Vz Yl) Db(Lp Vi) Gb(nB Nl) mU(qU Xa) BcWd IbmF WfmY RyeM OakE VinB aSgZ} Jj{Kg(Ar Ax Cs Dc dH dL Ed Fa Fp Ir kP Kx lY nN Oa Pk Qa Rg Wm) Dc(Aj Ar bM dI Fa Ju Jv Kc Nx Pk Rg Sr Un Ur Vv) Dd(mI Qa Sr Uf Un Uy) Yi(aW bU cD cX iP mW) kP(Al Fy Kn Sr Uf Vq) Qa(Kc Kp Pk Tl) Ks(mI mW pF) Vq(aC bL Cs) Pk(Mm Qd Uf) Fy(nC nH) Ux(jG jO) hP(Ic Wm) AabM AdAj ApyJ MmOa QhTl JmKc JtaC UfnH VhbU} Ur{nH(Al Ao Im Is Jm Mn No Nv On Qa) qU(kF kK lW lX mF mW nR) Dc(Ar bM Jv Lv Rg Wm) Vq(aC kP mI nN nR nU) nC(Al Ao Fy Ii Mn On) Yi(iP iZ mW nO pF) Lp(aC bO eM iP nW) Wm(hP uU uV zI) Qa(mI nT Va Tl) On(kK mM nA nO) nA(Ii Jq Mn) Fd(kR Qd) Uy(No Ut) nN(Ao Nx) qT(kP lW) LxmI MnnJ IlvH ImnO IpuV KkmW eDkF} cR{oT(aC aH aI aK aL Ax bE bI bL bN Bo bR bW cA cF Cq Ct cZ dA dD dJ Hu Io Ip Jn lX Mk Mn No Nr Ny oH Qb) mW(Fi Hp Ow Qz Ru Si Uy Wd Wf Yi Tm) Wf(mF mH mI nB nC nN) Ru(mU nA nC nD nO) Uy(mU nA nD) Wd(nB nC) Yl(nN nO) gZ(Qt Tv) mU(Fd Ps) pI(Pk Uk) AdAj ZxjG SroP QhfA XanO VqlX bUnN} Ut{Uy(aG aH aM bR bS bU cI Cs Jk mU mW Ne Nl No Qw Rg Ul) Vc(aM Bc bS eC gP Hu iP Ml Or Qw Rg Ua) Wd(aM iP kG kI lX lY mF mT) mU(Fc Ru Rx Wf Yg Yh Xa) nO(Uw Yg Yh Yl Yf) oP(Fi Gn Yh Yj) Yg(lX lY mF) Yd(oQ oT) Wb(aM bS) Qw(lX Rv) Vi(lX oO) bR(Fc Lt) gZ(Oz Pb) lY(Hp Zx) GbaM IpfA RvkG bFpI} jT{aG(Fc Gb Gn Ho nN Ry Rz Si Uw Uy Vc Vi Vw Wd Yd Zw) Ct(Hp Lp Ps Ry Zx) mW(dR Gp Ib Iz Jv) Va(aV cV Hf Ou) Yd(Nc Ne Nl) Vz(Mg Vq Yl) Si(bA Ki Ou) Zx(Ba cT Io) Hp(aE Ug) Ii(Fd

Figure 33 Continued

Zw) Hf(Vc Tm) Tl(Mr Ni) Rz(cV Ou) Ry(bS Oi) Ow(mT mU) aR(nO nR) nN(aD Kz) DkWn UaPs UcWd TmUn LpaE NvoP OiUx VcbC UycB PimU aUnO kFoH} qY{mI(aC aE Aj aV bE bJ bN cJ Ct Cu DL eF Fn Ib Iz Kr Qz Ub Ue Ug Uk) mW(Ad Ao Aw Bg Ch Co Cp De) An(kE kG kK lX lY nD nN) aN(kN mM mY nF nI nU) kK(Ap Ct eF Ib Iz) Fn(kP nO nT) eF(kN mF nJ) fR(cF Db Hr) kF(Cp Fb Uk) kC(Rg Rj) CpnN EzmF HcnA SrkG UonI UmnO bNlY cYlX} bU{Vh(Aj Ar Cs eC Ed iP kG kI nN Oa oE Or Pk Rg Uu Uy Vo) nN(Ar Fc Hu Ib Ir Kx Lp Rv Wd Yl) Uy(Ar Cs Kx Mf Nr Nt On Or Ou) Gb(gP iP Kx Oa oO) oP(Nw Sr Tr Tt) Wd(Ke mT oQ) oO(Fd Gz Hl) Ar(lX Wc) Ax(mS mW) Wf(kE nC) Yl(nT Vq) iP(Yi Xa) pI(Hl Kx) QamU VjgP PkgC} Nw{Fp(It Mj Mp Ms Mv Mw My Nc Nf Nj Of Pb) aC(aN aO Ar bM cZ mI nJ) Ms(Im It Lz Nc Pb Qa) It(Lz My Of Pb) Pk(bM Hu Ik Nb) Nj(Im Lz Pb) bM(Aa aK aO) wQ(bJ cO dH) oP(Gn Ki Yj) Ar(fP oN) nN(aN cF) WmhP MymI HpoK IbnH QaPb WdiO TljH VajG PagZ aMdK aOdH dLiA qAqB kNrX} Vq{Tv(qA qG qI qO qP qU qX sC sO tO uN uO uT uV vH yL) yJ(bP iO Ri rT To Tr) Kk(qG vH vP vV) Tt(sC vP vV) cD(Cs hP lX) tO(bP pS To) jG(Ru Vc Vz) kP(Ii In Qz) Aj(qX tM) Yl(bO nH) Of(rT tM) mS(Qz Wd) iA(pS rS) rW(cF pF) sC(Al St) CtqX ZwjH TllO KoUu aCnH bPvV bXlX} Wm{hP(cX dE Dg Ez Fb hO Ic Jq Jr Ke Kn Ko Lu Mk Pk Qd Qm Ri rW sC Sr Un uV) Kn(rB tQ uO wB wF yJ) sC(aK bP Kk Tv uW) Pk(qB rS tQ uW) hO(Qm rC rS) iA(pY rB vO) yJ(bP Kc tF) pF(rS rT rW) Ri(tO uV) rB(Vp tM) qA(Ke Qm) LupY QwUn PhrS cFwH nWvQ} Xa{nO(AW cD Ct eF Gp iP kR Oi Oy pI Rg Vs) cD(Dc eC iP kI kR mU nY) mU(aM hB Mp No Ow Oz) mS(aW Il mW Oy Oz) iP(Bg mI On Qc Qd) cC(eC jG jH) mW(Hu Kx Oy) Qw(jG Mn) bG(mT tF) kR(Kx Ou) CuoP NeoT IlkG JnlO JqjO UnbO OzmI aWoO hBoQ} wD{Kn(aH aL Ba cT Dk hB Nb oF oK rB uT wQ) Pk(Kr Ml Nb nW Nx oN qT rB wQ) Ri(cY iA oN qO qP vH vP vV) Ql(Of pF qA rB Vv wQ) rB(It Js Mt Qd qP) sC(Je Kk Kr Tn To) Tn(qO qP) It(hG Tt) ArwQ AxNb CsbQ MmbJ TzIz JeqP KgiA OmW} fA{Ax(An Ao aS Ba bG bI cH Cw Ez gZ Hq Hw Hx Il iO Iq Ng Of On Oz Qt Rz Tv) bI(aC bE dD Qv Vz Yl) Yl(bR cA cH Cw) Fa(aI bX cH) Fy(Qv Uw Yg) nH(Ow Tv Yi) Ip(aI Kx) Yg(Ng Qh) Oa(bX Vi) DpHa FcKx NmUu YiRh VzbX JqaI} Wb{Kx(aW bS cD cV nC Pk Qw Us) Lx(bS cD cX Pk Qw Us) aM(Aa Ax bP Dc Ng Nm) bO(Dc Ii Ir No On Po) bS(Ax No Oa On Po) iP(Jn No Oa On Qc) Us(Lz Mf Mh Pe) Mn(kI nB Qw) dD(nO oO) AaeC GpnO MfgC MxoT HfjO YlnH OaPk OzgZ} jH{Yd(aG Ch dK Ez In Mh Ms Nc Nd Ni Nl Nn Qc Qm Ua Vc Zx) Zx(Db Hx Mf Mg Nx Ub) aG(Em Fi Vh Yl Zw) Hp(Dk Ii Ne Qa) Nu(Fd Ho Wc) Qm(Fc Fi Ho) Va(In Po Ql) nN(nY Um) AnlY BcFc PoVc FdNt FiOu GlRz UamW HxUw IiPs ZwJr} Uu{Vh(Dk Iz Jk Om On Pi Qa Qd Qh) Ko(Fd Gd gZ oT Ry Uy Vc Yl) Yi(bR iP kG mS mW nO) Cw(kC nC nD nH nJ) Rz(kE kG kI nC) Uw(kI kP mS mW) Jt(gZ oT Yl) Ad(oT Vc) Gb(Mn On) Va(Dk mT) DgoP NmoT YgmW OnmH UxkE VinO} Gz{vB(Ad Ap Ax Dd Ik Jr Kl Kn Ko Kr Nm Oi Uf) Kr(tR tS uI uL vT yH yK) Jr(qH rU rW uO uZ) Lu(rU uX vA yH) wB(Fa Ke rV) jO(tR tS yD) Dl(wC yH) Ic(qZ rU) bC(rU rW) wH(dH Jl) vA(Ax Oi) DdmI MmrW IvrN JnuY cDwP} qU{mU(aC aK Ar Ax cP Cu dR Fw nT Or) mW(aC aK Bc cQ dR Mp mY nR Ua tF) nN(gP Ha Ib Qt Qw Ua) nA(kF Nn rX rY) Gd(cP Nu Ou) hX(kN lY nH) kP(aR bC Cv) Cu(kN mF) hW(mT nH) IsnD QznI RilW RjmI PgoP rZoO} jG{Va(aD aM Jq Lv Or Ou) Zx(cC Ho Mh Oz) Vc(Ar cU Mf Uf) Ux(aX Ky Rz Un) Db(Si Vi Yl) Iq(Hp Uy Vh) Tl(dK Nu Tz) aE(Em Fc Fi) Rz(dF Nu) CumW HxPs VzQc SiOu SrfP WdJq QzmT QukF LtOr YlUn UwcC VwPh mFrZ} tN{Ic(Ch dN eT fP Jk Kr Lu Mv Ne Nq nW oK qZ Ua uV) Lu(bP CH dL Ed Jv Ks Ou Pk yH) Ch(Ap Bb Ij Im Ke Ri) Jk(Im Jg Jt Ny) Bb(Bg Hu Je) Ke(Hu Nq) Pk(dJ nW) AjDl BgJg} wQ{Kn(Ap cF dH dJ eC Hf hP hW Ic Jh Jl Nb Nq Ou Ph rO) Ar(cF Ed It Js Kr) Jl(aY Hx Jk nW) Js(eC Ef Qw) cF(Dg Dl It) Bb(Ed Je) Mt(aY Ef) Ke(cO Ra) dH(iO Lu) MmbJ ItiO QwPd OuaY} Aj{Ad(aC aK Ar As BC bM bW cD cI CU dA dB dI Ik Il Im Ir Lw Lx Md Mq Nm Qd) Jt(aC Ar As bM cD dB dH dI) Dc(Ap Jg Un) Pk(Ap Dg Mm) bM(Bb Jg) ImrC} jO{Zx(aQ bW dF Fw Md Un) Vc(bI bX cA cQ dI Jf) Qz(kF nA nI nR nU) Ux(Mk Mp Or Ou Pf) Hp(Fw Jq Nu Sr) Sr(Fi Rx) Rz(Ct Un) Ql(Sj Tl) kP(Fn Um) CumU NtLp MkVw NiSi YdcC LtdF VhbR bCnN} gZ{Oz(bR Fa Kx Ld Lx Mq Mt Nx) bG(Fb Fy Ko Kx On Tn Uf Un) bI(Ar Cs Fp Hf Ky Kz Zx) Mn(Gn Rt Si Vh) Kx(An Hw Hx Ip) On(iP Oy Pa) AxFn CsNg DpHa MmHf IpKz} Yg{Fy(kG kI lX lY oT pI) mS(Cu Ij Is On Uf Yi) kG(Ng Qa Qh Tn) eC(On Qc Qd) nN(Is Jr Nx) mT(cL Ow Tn) Yi(mW pF) Qa(kI mU) Qh(mI nH) kP(Uf Uw) CuoP NoiO JskI RgmI cGnR} Aa{bM(aC eC Fa Is Jg Oa Or Pk Uk Vp) Gn(aM eC Mr Ni nW) eC(Fc Fd Fi Yf) nW(Vc Yh Yi Yj) Fd(aM iP) Ni(Ho Si) Vi(nO Qw) qA(bJ Kk) CuVj YiiP WdiO RtaM UykG dLiA} Pk{tQ(Ap bW cD Dg dJ Dl Kr Ml Mm Nm Ou Ql Ss) Ik(Dg Ir Mm) On(Hp Ib Iz) Lu(tX Wn) Jl(hP wH) Kk(Nm Oz) dH(uW wH) ApyJ ChMm CvVj DgtO IraV RivH dJwF} sC{Kk(cN Hf Ne Nh Nl rB wP zA) Al(Ar cF dH Jl Js Kn Lx) dH(Co Nq St Vs) Tr(rB Uv Vs) Ap(cF Tv) Mj(Jl Vu) Kd(Ou qZ) Vv(Dg iO) BbJe DlcF RmVu UkrB} pI{Kx(Af aG Ax bG bX dC dR gL hB Hw mF Mk) Fa(aW dR mF nA Uk) Ha(Gn Hl In Nh Yj) Mx(Qn Vz Yl) eC(Dd Io Mn) AxGl FybF QdaL YlnO QnbX OabM} Wd{iO(Jl Jn Ke On Qa Un Yi) Cu(bF mM mS nR Qh) Uf(kI mM mS nR) kG(Ao Dd Ih Iz) mS(Ij Is On) iP(On Qa Qd) lO(Ad Dc Dk) DcFw FymT NxnN cGnR} Ar{Dc(Jv Qw Qz Rf Uk Vc) aC(Bb Bc cD Dg Ic Ir) Qw(aK Il Qh Vi) oN(Kn Pd Rg Tj) aK(aQ Ic Qt) Up(Uy Vc) Us(Gb Vc) ChKe CqIb KryJ mFrA qXkG} Yl{aW(lY mS mT mY nC nO) mU(Fw Fy Ij Js No) bO(Gb No Nu Un) mS(Ij Il Mm Nm) Fw(Db nO Qw) Mn(mH mI mW) CueF QweC PheM mIiP} Yi{Ct(mI mP mS mT nN) cD(Gn iP Mk Mx Uv) mS(Gp Ib Oy) iP(BG Jv) iZ(Hc Hp Ib) Uv(bO eC) cX(aM Lx) UnbO OzmI aWnW bGoE cCeC} Ke{yJ(Ap fN Nb nW Or qQ rO Uk) tO(Ch Ef Nq nW oH) qA(Ap dJ Kd Ml) Ch(Il vI) bQ(rQ wF) hP(Ic vH) HpeF TnWn KdrO cFvH dLiA} Uy{Dd(Cs Jr Kx Lx Lz Mh Ml Ni No Oa Pe Po) eF(Cu Kx On Ow) Cs(Up Us) Kx(aG Us) PoUp HaaG NobS MnNi QmaM NxoE OnaJ hBoQ} Un{Qw(Ax Cs Gn Il Qa) Nq(qC uU vH tM) Tv(rO rW vH) Kd(vH vP vV) Ic(hP vA) Pa(Hc Ib) rW(cF Vv) nW(tS wG) uU(Jk Mp) TnuI ZweC} oP{Cu(Fi Ho In Rt Up Yj Tl) Yj(Jn Js Ks On Ph Qa) rZ(In kN mF Mg rC) Gn(Jn Js On Ph) Tl(hB Ld) TjTr InOn JlqT} Vi{No(iO iP kI kO mW nY) Qa(gC gP iP kI kP oE) On(kP lX mS nB) Mn(nB oQ Qw) mW(Fb Ow) CunN IhkG IjmS QwKx aInB} nH{Ib(Fy Im Mn No On) Uf(Ng Oi Rg Vs) Cw(aC Bg Iz) Ct(Fy On) Cu(aC qT) Mm(aC Rg) FyOi GdRg LuOr QwOn cPeD} hP{Ic(Bb Il Jl Js Mb Mt Oa Sr) Nq(Jl Om On Pa Pe Po) Bb(cN Oa rW) Sr(Lu Ml) Pa(Hu Pg) vH(Kn Om)} wH{Vu(cF cQ eD Jk Mt qA Ri tF) Jl(Bb bQ dN Mk Nb nW) Kk(Nc Ne Nl) Ou(cF Vv) NedH ItrB JsJv QlbJ} rW{cF(Ad Ap Bb Cv Dl Kg Kj Oa) Kk(Nc Ne Nh Nl yK) Vv(Bb Ii Mm On) aK(Ic Tz) BbMl CvRi KrtQ} Gb{cD(Dc eC iP Kx Lx Oa Qh) Us(Ed Fw Kx Or) Ni(Dd Mn) aM(Fw Jn) CsmW LxbG KxkR OaiP OrbO cCeC} qT{nN(cP Ib Qt Qw Um) kP(Qg Qz Ra Uv) Gd(Ir Nt Nu) nA(De Qz) iH(kC nJ) CumU NjfR QdoO KnrO RilW} Hp{No(iO iP kI mU mW nY oK Qw Us) Js(iA kI oN pF) DdoO NemT IjmS QdiP JnfP KsnB} rA{Fn(kC kI mF mI nJ nO) fR(cK Kc Kn Nj) nJ(An eF Uo) Gd(Cu Nt) mF(rX rY) AnkG cTkF} Vh{Fw(aM Pg Rg) aM(aA bP) lO(Kd Ph) AwLx DdoO MnmW MtQw NebO UaQa IjnO RgbS OraW bGoE cCeC} Vc{Dd(Cs Hv Ml Mr Mx Rg) iP(Fy Jn Js On Qa) bO(Dc Nm) FwRg MnbG HuOm KxkR} yJ{Ap(An Is Js Kn Mt Vv) Lu(dH Or Sr) Bb(Je Oa) Ny(cH tF) DgVv SrnW KrRi} kN{rY(lv Js Lu Ms Mx Nl Pa Pf Pg Qa) rX(In Jk Jl Js Pb) InhX} eD{Wn(Ba bP Dk Jm Ma Md Nx) nN(Fw Ha iP nY) Fb(tX wF) QznI cPnD} Qa{Jg(Mw My Ng Of) Yj(Hu mU oQ) Hl(Hu mU) Jt(Ms Ng) MkRg IbKc hXkC} Vz{aW(kE mS mT nC nJ) Mn(mH mI mW) mI(aI iP) FwmU MxoT IlmS} Qw{On(Gn nC Yj Zw) Cs(aK Il) Gn(Ij No) Mn(nC Ps) YfeC LxYj NbHl} lO{Lp(Dk Iq Ps) Yd(Ph Qm) Ux(Ph Tt) DgGd EmaG InVa ItPs WfQm} Vu{wG(cQ dJ Ip) iA(pS rS) BbwP MbwL HuvO bLrU cQuV tSnW} Kn{tQ(fP oK rO) wF(Dk oK) IcwB RawG KcuV KdrO OutO} qA{Ny(Ic nW qB Tv) Tv(Fb Iq) Kk(Ap Qm) QltM QmcF} Js{kI(Gn Rt Si) Zw(iP mU) DltQ HlmU TvWn SibS} mI{Dd(aC Or) Rg(No Wf) Ow(Hu Ib) AxiH EfOn MsrC} tX{Mm(bJ Of) nW(Ap Ou) BbdJ LubJ HuKg IptF ItrB} tO{Kr(aX rS uL) Ch(Kg Uf) Lu(Or Ou) DlcF MkMm} kC{hX(Ih Iq Jm Mw Qb) rY(Lu Ns) NdrZ LdeC} qX{An(kG lY) Fn(mM nJ) EmIn RikP cTkF mFrX} oT{Mx(Ko Lp Rx Rz Ux) AoWc FyYd TvbX} Mn{Si(nB Ne) mW(Gn Rt) nC(Ib Iz) TmnR} Im{Ng(Jg Jt) wG(Iz nW) LzMs PhuV wLnW} Vv{Ap(qI uY vH) Ri(uY vH) DgvV rQnW} aW{mS(Fd Ps Sj) Fc(kI lY) SjoO LpkI} cF{Dl(tR tS vH vV)

Figure 33 Continued

AppY IttR KcyH} Bb{Ed(uV vH) Je(vV yH) NfhW wLrZ} Sr{Rg(nJ oN) Rf(kG kP) NfhW IbnC} oO{Dd(Fi Gn Wc) rZ(In Jq My)} Fy{IbnC IneM YhmU RzmT RxkI} Ic{DlhO IpuV aKfY dBzA tSqZ} Jl{yK(Mj Nq) TnwF JkwK tSnW} Jt{Fp(Ms Ng) Gd(iP kR) mFhV} Rv{eC(cD Nm) DcbO DdkG JnmW} nN{Cu(aC Ps) EfOn RgbX UpbI} Fw{LuzA TlOz RxmU wLnW} Yj{Ha(gP iP kR) gChB} Ri{vH(Dl sK) cHuV rQoN} Wn{Tv(cO Pf) KkPi aJrB} cD{Ps(eC iP) DcRt UweC} No{IbmF WfiO VabO} Lu{OutR dHsM wLrZ} Il{Yh(kG mS) GnlY} Jv{Qh(Si Tl) TzwG} On{nC(Ct Ib) MsOf} Us{FcKx FimS GdKo} nR{Uf(aC Ng) WfhB} mU{MxrX WccG mFrZ} wF{FbtF MmbJ ItrB} Ap{EdtS aKqO} Dc{DbVa PoZw} Jg{FpMy QdOf} Jn{WcmW WfaM} Kd{rN(Cs Oa)} Kk{rO(Nc Nl)} gC{FdhB MxVw} nO{Yflj GnRg} tQ{DgqP QlpF} tR{MkPd ItrB} AxdIlY CuRyeF MaKorQ MmiAqZ MsnUrC NdnThV IbOwmF IrRfkP YhQceC TlhBoQ OutSnW VabOoE OzbCnC dHrSvH Constrained panels with 2 analytes, where 1.0E-8 >= 'AUC p-value' > 0. Contains 636 panels of 199,783 total panels evaluated. : Ji(AA aC aF Aj aK aM aN AO Ar Ax bM cD Ch cI cM Cs dB dH Ef Eo Et Fp Gl hP Id iJ Ik Im Iz jB Jh Jj Ju Jv Ld Li Lj Lu Lz Mp Ms Mv Mw My nK Of Og Ok Oy Pb pF Pk Qa Qe Qw Qz Rg rR rW Sf Sh Si tS Uh Uv Uy Vj Vs Vt Vv Wb wE Yk Wm) Qe(AA aC Aj aK aN cD cM Dd Et Fp Gc Hb Hp Im It jB Jd Jg Jj Jn Jp Jt Kc Lh Li Lj Lw Lz Mm Ms My Nc Nj nK Nl Nm Nn Nw Ny Og Ok Oy Pb Pj Pk Qw Qz Sf Uh Ur Vt Ye) Lj(aA cM dW Et Fr Hb iJ Im iO Iv Jg Jl Jn Jp Jt Kf Kk Lh Li Lv Lw Lz Mm Mt Mz Nh Nj Nm Nt Nu Nv Nw Ny Og Ok On Pb Pj Qa Qd Qw Uh Vt Wb) Ok(Aa aC Aj aN Ar bM Ch dI Eq Et Fp Im It Jj Jp Lh Li Lu Lz Mm Mp Ms My Nc Ng Nj nK Nn Nw Ny Of Og Oy Pb Qa Qd Rx Sf Sh We Yk) Pj(aC aM Ar Ax Bc bM cM Cs Dc dD dH dL Fa Fp hC iC Id Ik Ir iZ jD jG Jj Jp Kk Kq Kx lK Mz Oa Or Pa Pk Qa Rg Sf Un Vt Vv) Et(AA aC Aj aO Ar Ch Cs Fa Fp Id Ih Im Ir Is It Jj Li Lu Lz Mh Ms Mx My Mz Nc Ng Nj Oa Of Og Or Oy Pb Pk Qa Qd Vt) Li(aA Hb Im Ir It Jj Jl Jp Jt Lu Lw Ms Mv Mw My Mz Nc Nf Ng Nj Nw Of Og Oy Pb pK Qa Qd Qw Uh Ti) Nw(aC aN Ar bM Fp Im Ir It Jt Lu Lz Mh Mp Ms Mv Mw My Nc Nj nK Nl Ny Of Og Oy Pb Pk Qa Qd) Vt(aC aK Ar Ax bB bL cM Cs Cu cV Dc Dd dI eF Gc Jp Kf Kp Kq Kr Lh Mm Pk Qa Tz uR wE yJ) Jp(Ar Eq Fa Fp Hb Hc Id Im It Iz Jd Je Jv Kc Kx Ms Oa Pk Rg Vv) Gc(aC eC eP hC jV nB Ni Nk nN oE Pk Rg Sf Uk Un Us Uy Vb) Im(Fp In It Jj Lh Lz Ms Nc Ng Nj Og Oy Pb pK) Uh(Ar Ax bM cM Cs Dc hC iA Id Ir Jj Pk Qa rR) jB(aO Ax bI bN cM Fd Hb Hu Kx Kz mE Oy pK Qw) Ti(Ax Ed Lx Pk Qa qU rU rW tN tO tV wE) Hb(Ar Ax dL Il Ir Kk Kx Lx Oa Or Sf Wm) Fp(Jg Jt Mm Mz Nj Nm Nx Ny Og On Qd) Og(Ih Ir It Jg Jt Mz Ny On Qa Qd) Lh(hG iA Ib It Jj Ms nK oN Pk) Kq(Aj Ar Bg Ch Ef Iz Jj Nq) nK(aC bB bE dD Is Nn Nx Yl) Qd(Jg Jj Lz Ms Nj Of Pb) rR(Ap Dg Kc Kf Ko Uf Wm) Ar(aC aK cD cM Jd Qz) Qa(Aa Jg Ms Pb Qw Ye) Mz(hP Ir It Iv Nj) Jg(Jj Lz Ms Ng Of) uR(Kf Or Ou sH Wm) Zq(aC aM cM kP) Jj(Dc Kf Kg Ny) dU(Ax bB Nj Ut) jP(Dr Vc Vh Zw) pK(bU dD eC Nk) Mn(Dr Sf Sh) Ir(Ko Lx Ny) Yd(hA jD jY) Aj(Ad Jt) Dc(Sf Ur) Th(rU sC) Si(hA jD) Jd(Ax Ch) Kx(eQ mE) Of(eO On) cM(Id Oa) dW(aD aM) jY(Vh Tl) AaNj CuVb DrUt EoLx MbeW MmtT MsOn ShQh ZxjD QwUn KfyJ KnwE VaiC bBoW bReO cRoD eCpH Constrained panels with 2 analytes, where 1.0E-7 >= 'AUC p-value' > 1.0E-8. Contains 514 panels of 199,783 total panels evaluated. : Pj(AJ aK aN As Bn Ch cN Cq Cu dG dI Ed eM Et Ex Hb Hu Il Jd Jv Kn Ld Li Lx Ms Mt Nw Ny Oh Ok Pe Po Qd Qz rR Uh Uk Us Wm) Vt(Fa Fw Hb Id Il Im Iq Ir Jd Jj Jt Kc Kn Ko Li Lx Me Mh Mt Mx Nf Nw Oh On pF Qd Qg Qz rR tT Uh Ur) Lj(bM cD Ir Is It Jd Jh Jq Kc Kq Lu Lx Mg Mi Mp Ms Nc Ne Nl Nn Nx Or Ou Pd Un Ti) Ar(Bb Bc bE Dc Dd Id iJ Jg Jj Jt Jv Kc Ke Kn Lw Mz oN Pk Qh Un Up uR Us) Lh(aC aN FP Hb hC hP Iz Jg jM lM nL Og Pb pF Qa Qd Qw Sf Sh Uh Uy Wh) Jp(aC aO Ch Ir Jj Ld Lx Lz nK Ny Og Or Oz Pb Qa Qd Qt Qw Sh Uh Un Vs) Hb(As bM Cs Dc dH Ed Fa fR Fw Id Kq Mm Mt Mz No Oh Pa Pk Po Qa Sh) Uh(aC aM aN Ch Cv Dd dL Iq Jd Kn Kq Kx Lx Mz nK Oa pF Qd Rg Wm) Im(Aa aC Ir Jl Jt Lu Lv Lw Ly Mm Mx My Mz Nl Nn Nt Of Qd Sf) Et(aH aM aN Ao Ax bM cI cM Dc Dd dI Ef Hc Iz Jd Jv Kx Rg) Qa(Fp Ib It Jj Jt Kc Kk Lu Lz Mm My Nj Nt Ny Oy Sh Wh) Qe(Ax Dc dU Ib Id iJ Jv Kf Kk Kn Qg Rg Sr Uk Vs Vv) nK(aK Ax cJ Cs Ir jB Jq Kx Mn No Nv Ny On Ou Ow Qc) Fp(Aa It Jm Jn Js Lw Lx Me Ms Nc Nf Nt Nv Pb) Ny(It Iv Jg Lw Lx Ly Lz Ms Mx My Mz Nj Pb Qd) Kq(Dk Hc Hu Ib Id Ik Ir mZ Sf Sh Vb) Ok(aH aO cD cI dB dU EF Id Pk Yg) Aa(bM Iv Li Lx Lz Mb Ms Mt Nb Qd) Mz(Ax Gc Ij Jg Lx Lz Mn Mx Nc Pb) Qd(It Jn Jt Lu Mh Mm Nc Ne Nl) Jg(Aj Ih It Lx Mh Mx My Nj Qb) Ti(Dc hC Id No Oa Or Qh Sr) Gc(aM bU cM Ik Jj Or Qh Qz) Ji(dU Fa Jd Kc Kk Oa Or vH) Un(aC Ax cM Cs Dc Li uR) jB(aW cF Dr Fa Ip Oz Uu) Ir(aN bM Lw Lz Mn Nj) Jd(bM Cs Id Jj lL qA) Zq(bU dD iJ jY mM) Kf(aC Li lM mE Pk) Og(Ij Is Jn Lx Mn) On(It Iz Jj Oy Pk) Ax(Ic Pk Sr Ur) rR(Id Ke Kn Mm) Nj(Jn Lx Mn) Jj(Ad Jt Uf) Ut(pK Sh Uy) cM(Cs Fa Ke) uR(Bc Cq Sr) Mm(aC Pk) Nk(gZ nN) Id(aK dL) It(Lx Mn) Sf(Dd Dk) Zx(jY lN) Jt(aC Ng) Kn(tV wQ) Nw(aO cD) Va(iB jY) BbtV ChKe CsQw DcSh DrhA WmhP FamZ FwYl FyfB NmVb NoUy IbSr YdjE WfdU KrwE LiaN OabM OpiB bRdW dXeC Constrained panels with 2 analytes, where 1.0E-6 >= 'AUC p-value' > 1.0E-7. Contains 836 panels of 199,783 total panels evaluated. : Hb(aC aM Ao Bc Ch cM Cq Cu Du Fc Fi Fp Fy hC Im Is Iz Jd Jj Jv Kc Kf Kn Ko Ld Lw Lz Mh Ms Mx My Nn Nw Ok Pd Pe Pf Qd Qz Rg Uf Un Us Uy Vu) Lh(Aa aO Ar Ax eF hA Hc Id Ih Ir Is Iv JD Jn Jp Jt Jv Kk Kx lK Lx Mx My Nj Ny Oa Of Or Ou Oy Pj Rg tT Ur Uu Uv Vc Vs Vv We Ti) Uh(AO As Bn cD cE dB Et Fa Fw Gp iC Il Is jD Jl Jt Kf Kk Ko Kp Ml Mt Mx No Oh Ok Or Pd Pe Sr tT Uf Un Vv Wn) Id(aC aU Ax bB bM bX cD Dc dD dH hR Hu hV Il jQ Lj Mm Mn No Nr Nw Ny Oh On Qa Qd Rg Sr Un uR vI) Mz(Aa aN bM Hx Ib Is Jj Jn Jp Jr Jt Kc Kk lK Lw Ms Mt My Ne Nm No Nt Oa Pe Pk Sr Ur Yk) Ar(Ad aF Aj aN aO bM Cu fP Fy Hu Ik Iq Ir Is Kf Kk Mm Mt Nj Nk Nm Qa Qd Ti) Jp(Aa aM aN Ax bM Cs fP hP Ih Is Jm Jn Jt Lu Mh Mx My Nj Nm Nt Of Qb Sf Wm) Pk(aV cM Cs Dc Dg Ir Jj Kc Ke Kk Ko Kq Ld Lj Lu Nv Ny Qa Qd Sr Un uR wE Zq) On(Aa aC Aj aN cI Jh Jn Lu Lz Mb Mh Mp Mv Mw My Ng Nj Ny Pb Rg Sh Wh Ti) Vt(Dp Ed Fp Fy hP Jl Kx nK Nn No Nr Oa Ok Or Pd Pe qZ Rg sK Sr St Uf Wm) Kq(aM Ax Ba bM cD Cs Ct eF Eq Fr Jv Li Lu Lv mE Mw Ng nK Qw Ua Vs Wh) Un(Dd eC Ed eF Et Fw hG Hu Ib iJ Ir Jd Jj Kc Kf nK Nw Qa Sr Ti) Pj(Fw Is Jl Ju Kc Kp mE nC nL No Pd Pf Qv Sh Sr Tz Ur Uu Uy Vu) Fp(aA Fr Ih Ik Ir Is Iv Jh Jj Jl Jq Lz Mt Nh Nl Nn Nu Pz Qb) nK(aI aL Bo cM Cu Dd Fa Gc Gl iH Js Li Lx Nk Oa Oh Or Qd Vz) Lj(Aa aK aN bX Cu Dc Dd Dg Kn Ko Kp Kx Ow Qz Sr tV Vu Zq) Ir(cM hG It Iv Jg Jn Jt Kc Kf Nm Nu Nx Pb Qw Sr Ur Ti) Qa(Aj aN Iz Jd Jv Ke Kf Kn Kp Nn Qg Qt Qz Rg Sf Ur Vs) Og(Aa Fr Ii Iv Jd Jm Mm Mt Nm No Nt Nu Nv Nx Oa Pf Vq) Jt(aN In Is It Kk Lx Lz Ms Mt Mx Ne Nj Ny Of Qb Vb) Aa(Fr Jg Jl Lu Lv Me Mh Mp Ne Nl Nt Nw Ny Po Qc) Ax(cM Jv Kf Kk Ko lY Nk Ok Or Qw Qz Uf Us Vv) Jg(bM Ik Is Jh Jn Js Lw Mm Mp Mv Mw Nc Oy Pb) Jd(Aj Bg Fa Hu Ik Kn Ld Ng Nw Oa Qd Qu Uu) Ny(Ih Is Jn Lu Lv Mt Nc Ne Nl No Nt Oy pK) Ti(aM cM Cs Fw Fy Iq Jm Mr Mt Nr Pe Po) Lx(Is Iv Jn Mm Ms My Nc Nh Nl Nm Oy Pb) Nw(aF aK cI cM Cs Dc dI iA Kx Or sF sJ) Et(aF Dr iA Kc Kn Sr tT Us Vs Vu Vv) Li(bM cD cM Dc hG Kc Kk Qz Sr tT tV) jB(aS bG bM cA cR Du Hc Jn kF Qc Vb) Gc(aS bB dD Ed Mr mS Ne Ns Pi Uu) Jj(Dd eO Fy Jm Jn Ke Ko Ks Mm Vq) Ok(Ao bL cM Cs Dc Hc Iz Kx Or Rg) Qd(Aj bM Cs Du Jv Kc Kk Kn Nn) dU(bU eC Fd Fy Im Jq Mn Nn Qc) Dc(Aj Ct Jv Sr Tv Ub Uk Wh) Kf(Cs Fa lK Oa qA tT Uu wE) Qe(eC Fa Ke Kp Kx nL Or) Mm(Fa It Jn Ms Oa tO) Sr(Ch lK lM Oa Rg rR) Ke(dL eF Hu Sf Sh yJ) aC(Ad Ap Bb Cu nL Vq) No(Eo Nj pK Qw Sf) Mn(Iv Lz Ne Nh Nu) Js(Kk Ms Qw Rg Ur) Kx(cM Dr mZ Nk Wb) Nv(It Ms Mx Pb pK) Bb(aM bM hP rR) Dd(Kk pK Sh Vb) Nj(Ew Is Nm Nt) Im(aN bM Iq Oe) Zq(bO Mh mS Or) Oa(bX Kc Wb wE) bB(mE mZ Sh Uy) Dr(Ky Qh Sf) Du(iJ mE Up) Eo(Is Jn Oh) Ji(jD lM tT) Nx(aM aN rR) Uf(Ch Cs nL) uR(aP Cu Dl) Fa(Lu Nk) Nm(Is tT) Nt(Is It) Yi(bO cD) Sh(Ad Fy) Wh(Cu Ut)

Figure 33 Continued

Qh(Sf Yk) Kk(rR sC) Vh(bU Fw) hC(Gb Lu) pK(bN Nn) AjAp BckP CsiO CtDw WmwH Frlt LwPe WbaM S Nc Ne Nh Nl Ny Pb) Mn(Ao EQ Jh Jq Mh ml Mp Mr mZ Pb Pd Po Uy Wb) Jd(Ba dL Fw Jv IK Mx No Oh Or Qt Qz Tz Ua Vs Vu) Du(Al aW bU Et iA mW Pi Ps Qc Qy St Tz Us Vq) Nu(aA Iv Jq Jr Lv Lz Mh Mx Nc No Pb Po Qb Qc) Ih(aA aN Fr Iv Jl Jn Lv Lw Lz Ms Mx Nc Nl Pb) Wb(Ar Cs dD dF Ex Li Ml Nk Oh Pj Po Qb Tz Up) Zq(Al iA Ik Ja kl Ml Ni Nk Ns Oi Qz Rg Rz Vc) Nv(Aj aM aO hA Hc iA Iz Jl IL Lw Mw mZ pF Rg) Ny(Aj Ax cD Ch Dd hC Ic Iz IK IL Mp Qz Rg tN) Kc(Bc cD cM Ex Jl Kr Mx No Oh Qb tV wE Wm) nL(bB Bc cJ Cv dD Fy Gl Ji Jp jQ Ki Nw Un) rR(dH Et Hb IC iO Kl Kp lL Nw Qm tV Uc) Fr(aA Iz Jq Lw Mh Nc Nl Oz Pb Qb Sh tT) Iv(Jn Lz Mh Ms Mx Nc Nr Oz Pb Po Qb Qc) Pj(Fd Gd Lw rQ Ry rZ Si tN tT tV tX wD) aM(Ax cl Dd Fd Gb It Jn Oh Op Ps Si Xa) cM(Dd Ex Fp Fy hP jM Kp Ld oW Qh St Tz) wE(dH Dl Ed Et Fw Ic Nw Ou Ql Rm sC St) Cs(aN aU BC Cv Dd Dg dl Or oW Uy) li(Aj Iz Ms Mx Pb qA Qc Rg rW Sh Vb) Vq(Ar Ax bB bL cD In kP Lj lX Nw oE) nN(bl Ji Jn Jp Lh Lj mE mZ Nw Op Qe) It(Ik Jh Jl Jn Jq Lw Mr Ms Pd Qb) Li(Aj mE ml Or qA Rg tO Vc Wh yJ) Oa(eC Ex Ik mE ml Oh Op Qz Rg Wm) aN(Ap Ax Dd dl Jg Lz Nk Oh Oz St) No(eQ Ic Kp Lw Mx Pb Qz Rg Ye) Sf(Al Ar Cq Fw Fy Nt Nw Om Qc) Jl(hP Ib Jn Ms Oz rW sC vH wQ) Or(aK aV Bc Dl Gb iJ Jg Kg mZ) Vc(Ar Dd dF Et Fy Jp Om Ou Qh) Lh(Ao cI Ct Gb Gl mE rW Yg) Lj(Ax gW mI Op tN tT Ux Vw) qA(Aa Ap Cv Et Jg Jq Nw Uh) Aj(Aa Ax Ba Fy Kg Ks Qc) Sh(Co Iz Jk Kg Ks Nt Ou) Jn(aA cD Lv Lw Mx Qb Rg) Jp(aA dB dE mI rW vH Yg) Un(hP lK Lz uU uV Vb vH) tV(Ap aQ dB Jg Nw Qm tF) Wm(Jr rB rS Tz vO wQ) Nc(Jh Jq Jr Mx Po Qb) Qc(Eq Lz Ms Ne Nl Ye) Ps(bO cD iP Mf Nk Rg) hC(Aa Ap Kg Op Yd Yi) Ax(aU bB dI mI Qa) Dd(Lz mE mI Ml Qz) Gc(Jv Kd Ow Ry Yl) Nt(aA Ik In Lw Oy) Tz(As Fp Fw St Yk) Uy(aG Ar Et Jr St) tT(Dg Mh NW wL) jB(aD bF nW Oh Us) Id(eC Fy Qh Vu) Qa(aK Ct eC iJ) Qb(Lv Ne Nl Pb) Ld(lX mW mZ St) Pi(dL Hu Rv Vb) cD(Fp Jg Lz Vi) hP(Jq Jr lL Nw) vH(Dl Et Om rS) Bc(eF mE sH) Dg(Eq hO lK) Po(Ms Oy Pb) Lu(Fw iZ rS) Ib(Cq Fy Hx) Yi(cC eC Nk) Qd(hR Iz Us) Ji(mI mZ tX) Qh(Nk Wh Yg) Uh(Lz tN tO) Ux(iB jD jK) lL(fN Ou sC) rW(Hb iO Nh) Ar(gW Vi) Et(qO qP) Eq(Dk Qu) Ex(dI mZ) Gb(bO Ni) Nr(Jr Qz) Ne(Jq Ma) Jg(Ss Uu) St(Iq rB) Xa(kR mU) Ye(mE mT) Op(iC jH) Om(Wd Wh) Vt(kP nC) Pa(hA Rg) Pb(Pd Pf) aK(Lz Mr) mI(Hx Qc) AaGn ApyJ ChTn EdKp FpQz FyeF MsJq HuoW IctN HbnC WemE KrtO RybU YlbO RiwG QlwD NwUs OhUp OwmZ OuVb UksC VuwL PdwQ dHwH tFjF nDqU iOsH

Constrained panels with 2 analytes, where 1.0E-3 >= 'AUC p-value' > 1.0E-4. Contains 2,389 panels of 199,783 total panels evaluated. : cM(Aa aC Ad Aj aN Bc bM dU Ed Ha hR Ic Is Jg Jn Jq Js Jt Kr kS Lx lY mE mI Mm Mr Mx Nn Nt Nv Nx Ny Oh Ou Pe pH Pi Ps qA Qb Qc qG qO Rg Rm rR sC Tr Tv Up UR Us Uw Vi Vj Xa Wm) cD(Aa aC Ad bA Bc cA cG Cq CU Dd dF Dg dH dI Fy Gb Ih Ij Io Jl Js Kp Kr Lw Mm Mq Mr Mt Mx Nm Nr Nv Oh Ou Oz Pa Pd Pf Po Qb Qc Qh Rg Tz Uf Uw Vu Wb Wm) Jj(aC aK aN bB Cp Cv Cw dI Dk Dl Du Ez Fb IC Ip Iq Iv Jk Jo Jq Jr Ju Kc Kj Kk Ld Ma Mx Nc Ne Nh Nj NL nO Nr Om Op Or Ou Po Qc St Tr Uc Wb Yi Wm) Kc(Ad aK Bb bM Cq Cu Cv dB Dd dH dL Ed Fp Fw Fy Il Iq Jn Jq Jt Ks Kx Lu Ml Mm Mr Mt mZ Na Nk Nm Nn Nr Nv Ny Og Or Oz Pi Po Qz Rm tT Uf Up Us Vu) Ld(aC Ad aK Al Ap BB Cu Cv Dd Dg dH dL Ed Ex Fw Fy Ha Ih Ii Ij Il Iq Jg Jm Jn Jq Kf Kn Kr Lu Mt Mx Nm Nn Nr oD Pa Pi Qc Qh Qz Tz Ub Ur Uy Vq) uR(aR bA Bb bV bW bZ cA cE cF cK Cs cU dA dL dM Ed fN Fy IC Jv Kr Kx Li lO Lx Mq Mt Nk Ns Nx Of Pb Pd Pe Po qZ rQ rS Tn Tr Tv tX vW wD) Jq(aC Aj aN Ax Cs Ib iJ iO Iv Iz Jh Jl Jm Jn Jv Kr Lu Lv Lz Mh Mx Nh Nl Nn No Nx Or oW Oy Pb Pe Po Qb Rg rW Sf Sh Uf Ur Uy Vs Wb We Wm) aC(aM aN Ax Cp cR dI Du Fp Fy Ic Iq Jl Jm Jn Kg Kn Lu Lx lY mE Mg mI mM Mr Mw nH Nj Nt Nx Oh oW Oz Pd Pf Qb Qc Ql Qw Ur Uw Ux Vw Xa) aK(Aj aQ Bb bM dA Dc Dd dI Ex Fp FY Ha Ih Ij Jn Js Kp kS lY mE Mm Mt Mx Nj Nk Nn Nt Nv Nx Ny Oh Oz Pe Qb Qc Qh qO Qw Rg Rm St Tz) Ur(Bb Bc bM Cp Dg dL Fd Hx iC Ih Ij Iu Jg Jk Jr Ke Kj kP Kr Mm Mp nK Nm Nx Pd Ph Pi Qb Rg Rm Tn Tv Uc Up Us Vp Yi) mZ(Bo cJ Cq cR Cs Cw DD Fy Gl Gz Ha Ib Jl Ke Ks Ky Lj Lx Mp Mr Mz Nn Nw Nx On Ou Pi Qa Qh Sr Tz Vt Vu Th) Rg(Aa Ap Bc bM bX Cv Dd Dg Dl Gb Ij jB Jd Jg Jm Ke Kp mE mI Mm Mt nL Nr Oh Pe Pi Pk Qz rR sC St Tz Vq Vw) Nx(aA Aj Ao Dg dL Ed Fw Hc iJ Iq Jh Jl lK Lu Lv Lw mE mI Mr Nl Nu Oy Pd Pf Po Qz tT tV Uy Vu Wm Ti) Vq(As Ba bX cC cE Ct cV Dp Ed Fp Hq Ic Iz Ko Lx Mk mS Ne Ng nL Nn pF Pk qX Sh Sr Uk Uu wE yJ Yl Ye) aN(aF Aj bA Bc cI Cq Cu Cv Dg Dl Ed Fp Ha Ic Ii Iq Ks Lw Mh Ml Mr Mx Nm Nt Ou Pd Pf Po Qb Uf Vu Wm) Bb(Ao cI Ct Cu Ed Ex Fw Hu iC Ik Iz Jv Kx lK Mh Mt Og Pf Qb Qw Qz rQ rZ Sf tS vV wE wF yJ Wm) Tz(Ad bB Bc bX Ch Cv Dd Dg DL IC Il Jt KP lL Lz mE Ml Mm Mt Nm Nn Oh Pk rW Uf Vh Ye) Cu(Aa aO bM Ch cI Cs Ct Cv dB dI Eo Hu iA Io Jd Kx mE mI Nj Nk Or Oz Qc Sh Sr Us Uv Vc Wm) Kp(Aj Ch dL Fp Fw Hu Ib Ij Il Is Jm Jv lL Lu Mm Mx Nk Nn Ny Oh Or Oz Pe qA Qb Qh Uf Us Wm) nL(aL bE Bo cR Cs Ct Cw Dc Dd dU Et Fa Ib iH Is Ke Kn lL Lx Ma Mm nN No Nv Oh Or Oz Qc Qv) Bc(Aa Ax cI Ct Dd dI Dp Fp Ij Is Js Kr Lv Ml Mm Mt Mx Nj Nn Og Qb Qc rR sC Sh St Up yJ) Nm(aA aM Ax bM Ch hP Jh Jl Kx Lu Lv Lw Mh Mp Ms Nn Nu Pb qO Sf St Uk Uy vH Vi Vp WE) Aj(Al bC bM Cq Cv dI Dk Dl Fr Ih Iz Jk Jm Jn Js Kl Kn Ko Lx Mn Mt Ng Nt Oi Pd Tr Uc) Uf(AO bL Du Ed eF Eq Fw hC Il Is Jv Kx Ml Mt Nk No Oh ON Or Pe Qu sC Us wE Wm) Fy(aO aV Ba bM Ch Ct dL Dp Hu Ic iJ In Iz Jd Kf Lu Mm nC nH Pk Qw Sr Vs Wb Wh Wm) Uy(aI bR cC cR Dk Fp Fr hC Ii Ij Is Js Jt Mf Ni Nr Nw Om Op Ou Ps Qc Uh Vh Zq Ti) mE(bI bN bO Cs Cw Dc dD Dr Et Is Ji Ke Lj Lx Mn Mp Nn Nv Nw Ou rZ Sr Uh Un Yl Ti) Cv(Ax dH dI dL ED Ex Fp Ic Ij Jn lK Ml Mm Mt Mx Ny Og Or Pf Qc Vb Vj Zq Wm) Nl(aA Ii Ip Iq Iv Jh Jl Kk Lv Lz Me Ms Mw Mx Nj Nk No Nr Nu Og Oz Pb Po Pz rW) Qw(aU bB Dd Du Ed Ex Fr Fw Jl Jn Mx nN Or Pd Pf Pi Qh Rm Si Tn Tr Uc Us Uw Vj) Wb(Ax bS Du Ed hC Hf Is Lv Lz Mf Mh Mx Ni Om Or Ou Ow Oz Qc Qx Sr Vh Yl Ye) Sh(Al cG Cw Fb Ir Jg Jm Jr Kf Kx Ma Mt Nr Nw Oh Op Pi Ps Qc Sr Tn Up Vh Ti) bM(cT dD dF Ed Ha Ic Ii Ks Lv Lw Lz Ml Mt Nt Ou Pd Pf Ph Ps Rm Ry Uc Vi Vp) Sf(Aa Ax Fb Gb Id Ih Ir Jg Jm Jr Kg Kx Li Mf Mt Nr Oh Op Ps Qb Sr Uh Up) hP(Ic Ih Ii Im iO Iq Jg Kn Li Lx Mm Mt Nv Ny Oa Om Ou Pa Pd Pk Po Qa Qd) Nn(aA aM Ax Cs Is Iz Jv Ke Kn Kx Lv Lz mI Mm Mt My Mz No Nu Oa Oy St) qA(Dg Dl Fb Hb iJ Im Ir Iu Kl Lu Mm Mu Nv Om On Ql qZ Tr Ug Uk wE tM) tV(An Ao Ch Cs Dl Hc Hu Iz jM Kk lM Mk Ne nW oK Ou qT Qy rS rW sC) Nc(aA Ii Ip Iq Jl Kk Lv Lw Lz Mh Mp Mr Ms Nj No Oz Pb Pd Pz Qc) Qb(aA Dg Dl dU In iO Is Jh Jl Ko Lu Lw Lz Mp Mx Nh No Oy Qg Ye) Vb(As Ax Cq Dk Gb Ho Id Ij Jo Kf Kg Kn Kr Mt Tn Uc Up Vi Yi Zq) Dd(Ax dD dH dI dL Ik Im Lw Mt Nf Nk nN Or Pf Ry Vv We Wh Wm) Jm(aM Ax Dp Du hC Ik Jl Jr Lu Lv Lw Mb Mp Oy Pb Pe Po Sr Ub) Og(aA Al Dg Ha Jk Kr Lw Lz Mf Mg Mh mI Mp Mv Ne Ng Oi Pz Uc) Pk(bW cR Dr dU Eq Fa Fw Ho Ib Kr Mp Pf Qh tN Tr tT Uc Us Vu) Is(aF aO Dr dU hC hG Ib Iz Jd Jl Kk Kx mI Ms Qz Sr Vs Ye) wE(aP Ar Cs cU dL Fa lL Mt Mw Nv Po Qa Qd Qe Qm qX qZ Rf) Du(aG bR bS Cq Gb Il kI Ni Nu Op Pz Uc Uh Vc Vh Vi Vu) Ne(Dr Ii Ip Iv Jh Jr Ko Lv Lz Me Mw No Nr Oz Pb Pz rW) Nh(Ih Ii Iv Jh Jr Lv Lz Me Mh Ms Nj No Nr Pb pH Po Qc) Ke(eP Fw hR Jd lK My Nb nC Nf nH Qt rO Sr Us Uu Vv Yk) Kx(Ap cV dH DL eC Ed iJ Il Iq Jl Jv Kk mW Vc Vi Wm) Or(Aa Fa Fw Hu Ic Il Io Kk Kr lL Me mI Mz No Ny Oa sC) dU(bI bL Ij Ip Jf Lt Mf mI Nr Ny Oh On Pe Ph Qa Qd Tn) Ad(aM hC Hu Ik Iz Lw Lz Ml Mt Nf Of Pf Qt Qz Vs Vv) Gb(As bU dD dF Ed Mf Ml Mr Mt Mx Op Up Us Uu Yl Ye) Mm(aO bA cI dI Eq Fd iA Iz Lw pY Qh St Tv Vu VV) Ko(cI dI dL eC Ed fP Gc hO Iq Jl Lz nK Ra rW Tv Vu) Nk(cI Cp dF Fd Fw Ha Ho nH nO nT Ph Pi Vi Vu Ye) Jg(aM Ao Ax Ch cI Ct dI dL hC Iz Jv lK tN tX Vs) Jt(cI eC Ed Ib iC Iz Jv lK rR Sr Uk Uu Vc Vu Yl) Eq(Ao bB Fb Fr Iz Jk Kf Ng Om Pz Tn Tr Uc Ux) Fa(Dr eC Hu iJ Mj mW Nf nW oN Op pF vH Zq Wm) Jl(Fr Iv Iz Jd jM Kk Mx My Nu Pb rB rR Sr Ye) iC(Dg Dl Dr Gc Hb Hv Ic Il Im Js Qd Qe Uo yJ) Aa(aD aJ Ax bE bO Cs dA dD dH dI iA iZ Kk) Ii(Ch Ed In Iv Lu Lv Lz Mh My Oy Uv Vv Ye) Nv(aA aF Ao Ch cI Je lK mI oE oN oP Vs Vv) Vc(Ax Cs Fp Fr gL hC Ij Jn Mn Mt Nr Tn Vh) lY(aH aL bE bN bU Cs dD eC gW hW Lj lK Zq) Ap(aM Ch Ct Fp hO lK Pi qO qP rS rW sC) Jd(eC Ed Iq Je Mh Ml rR rW Us Vv xA Wm) Ye(Dk Fr Ha Mr nN Nr Om Pe Pz St Zq Ti) mI(Bo cR Cs dD Hb In oD Ou Oz Pf Vt Yl) Dg(Ch Fp hC iA Iz Jr Kl Mx Pi pY Vv) Lx(aF Ao bQ Cs dI Dk gW hA iA lK Oa) Lz(aA aV Cs Id Jh Kf

Figure 33 Continued

Kq Mt nK Oz Pc) Ms(Ip Jh Ma Mw Mx No Nr Nu Pd Pf Pz) Ij(aA Ao Ch Ct dI Eo Hc iA Ib Jv Mv) Qc(aA dI dW Jh Jr kP Lv Lw Mh Mp Pd)
Kn(Ib Ik II kP IK nK oN Qz Us Vs Vv) Op(Ax Ed jI Jv Kd kG IO nB Po Tv Wc) tT(Ic Ip Mf Mg Mk Mw Om Pd qT rP Un) Yi(aW kG mS mW
Ni Oz Pi Vs We Wh) Kk(Ao Cq dH dL Ed Oh Ra Uc Vu yJ) nN(bX cR Hb In Ip Ir On Qz Sr Ti) rR(aP bB cN Kr Ok Om QI Rb r Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ad | ug/mL | 4.8E-2 | 9.7E-2 | 7.5E-2 | 1.2E0 | 8.8E-2 | 3.0E0 | 6.8E-4 | 7.8E-4 | 5.4E-1 | 8.5E0 | 166 | 8 | 166 | 8 | 0.66 |
| Af | ng/mL | 1.2E0 | 2.7E0 | 1.0E1 | 6.9E0 | 4.5E1 | 8.6E0 | 1.7E-3 | 1.5E-1 | 5.3E2 | 2.3E1 | 166 | 8 | 166 | 8 | 0.55 |
| Aj | ug/mL | 1.0E0 | 5.7E0 | 2.2E0 | 3.7E0 | 2.4E0 | 2.9E0 | 1.5E-3 | 1.3E-1 | 6.1E0 | 5.8E0 | 166 | 8 | 166 | 8 | 0.62 |
| Al | mg/mL | 8.3E-5 | 3.2E-4 | 2.6E-4 | 5.2E-4 | 4.4E-4 | 5.4E-4 | 4.3E-6 | 7.8E-6 | 1.8E-3 | 1.5E-3 | 166 | 8 | 166 | 8 | 0.67 |
| An | U/mL | 6.0E1 | 2.5E2 | 2.0E2 | 1.3E3 | 5.4E2 | 2.6E3 | 2.8E-1 | 2.7E1 | 5.5E3 | 7.8E3 | 166 | 8 | 166 | 8 | 0.75 |
| Ao | pg/mL | 9.4E1 | 3.7E2 | 5.3E2 | 8.4E2 | 3.6E3 | 1.5E3 | 1.5E0 | 4.1E0 | 3.9E4 | 4.5E3 | 166 | 8 | 166 | 8 | 0.67 |
| Ap | ng/mL | 3.3E1 | 5.1E1 | 4.9E1 | 8.2E1 | 5.4E1 | 9.3E1 | 2.0E0 | 4.4E0 | 3.3E2 | 2.4E2 | 166 | 8 | 166 | 8 | 0.58 |
| Ar | ng/mL | 6.8E-1 | 2.4E0 | 2.9E0 | 8.6E0 | 6.7E0 | 1.7E1 | 3.4E-3 | 2.2E-1 | 5.1E1 | 5.0E1 | 166 | 8 | 166 | 8 | 0.67 |
| As | ng/mL | 8.6E-3 | 1.1E-2 | 1.2E-2 | 1.6E-1 | 1.7E-2 | 4.4E-1 | 1.7E-3 | 1.7E-3 | 1.3E-1 | 1.2E0 | 166 | 8 | 166 | 8 | 0.53 |
| Aw | pg/mL | 1.6E1 | 2.5E1 | 1.7E1 | 2.6E1 | 5.6E0 | 1.2E1 | 2.9E-2 | 1.3E1 | 4.2E1 | 5.1E1 | 166 | 8 | 166 | 8 | 0.77 |
| Ax | ng/mL | 2.1E0 | 4.4E0 | 2.5E1 | 1.4E2 | 9.2E1 | 3.0E2 | 1.2E-2 | 1.0E-4 | 7.7E2 | 8.5E2 | 166 | 8 | 166 | 8 | 0.58 |
| Ba | ng/mL | 8.3E1 | 7.5E2 | 6.2E2 | 2.4E3 | 1.5E3 | 5.0E3 | 1.1E0 | 4.1E0 | 8.1E3 | 1.5E4 | 166 | 8 | 166 | 8 | 0.76 |
| Bb | ng/mL | 4.1E0 | 1.0E1 | 7.2E0 | 1.2E1 | 8.9E0 | 8.6E0 | 4.1E-3 | 3.5E-1 | 4.9E1 | 2.5E1 | 166 | 8 | 166 | 8 | 0.68 |
| Bc | ng/mL | 3.7E1 | 7.6E1 | 1.2E2 | 3.2E2 | 2.2E2 | 4.3E2 | 4.9E-1 | 2.9E0 | 1.2E3 | 1.0E3 | 166 | 8 | 166 | 8 | 0.62 |
| Bg | ng/mL | 1.1E-1 | 2.4E0 | 4.0E0 | 5.1E1 | 1.7E1 | 1.4E2 | 5.3E-4 | 3.1E-2 | 1.5E2 | 4.0E2 | 166 | 8 | 166 | 8 | 0.75 |
| Bn | ng/mL | 5.6E-2 | 8.0E-1 | 1.2E0 | 8.0E0 | 2.0E0 | 2.0E1 | 5.6E-2 | 5.6E-2 | 8.6E0 | 5.8E1 | 166 | 8 | 166 | 8 | 0.61 |
| Bo | ng/mL | 1.3E1 | 1.5E1 | 1.5E1 | 1.7E1 | 1.1E1 | 1.7E1 | 1.6E-2 | 1.6E-2 | 5.0E1 | 5.3E1 | 166 | 8 | 166 | 8 | 0.50 |
| Ch | uIU/mL | 9.8E-1 | 1.6E0 | 2.8E1 | 1.5E2 | 1.6E2 | 4.2E2 | 3.4E-3 | 9.2E-1 | 1.8E3 | 1.2E3 | 166 | 8 | 166 | 8 | 0.67 |
| Co | pg/mL | 4.6E1 | 1.5E2 | 2.2E2 | 4.4E2 | 1.3E3 | 6.9E2 | 1.5E-1 | 8.8E0 | 1.7E4 | 2.1E3 | 166 | 8 | 166 | 8 | 0.72 |
| Cp | ng/mL | 2.2E1 | 6.0E1 | 2.8E1 | 2.0E2 | 2.2E1 | 4.4E2 | 6.0E-1 | 1.1E1 | 1.4E2 | 1.3E3 | 166 | 8 | 166 | 8 | 0.68 |
| Cq | ng/mL | 2.9E-2 | 1.1E-1 | 1.2E-1 | 6.3E0 | 4.7E-1 | 1.7E1 | 8.0E-4 | 3.0E-2 | 5.1E0 | 4.9E1 | 166 | 8 | 166 | 8 | 0.77 |
| Cs | ng/mL | 6.2E1 | 1.3E2 | 4.5E2 | 1.3E3 | 1.7E3 | 2.3E3 | 8.3E-1 | 5.7E0 | 1.8E4 | 5.1E3 | 166 | 8 | 166 | 8 | 0.59 |
| Ct | ng/mL | 3.2E-1 | 7.6E0 | 3.8E1 | 1.1E2 | 1.2E2 | 2.0E2 | 1.1E-4 | 4.4E-2 | 6.2E2 | 4.7E2 | 166 | 8 | 166 | 8 | 0.65 |
| Cu | ng/mL | 2.6E-1 | 2.0E0 | 6.3E-1 | 9.6E0 | 1.9E0 | 2.3E1 | 1.9E-2 | 1.7E-2 | 2.1E1 | 6.6E1 | 166 | 8 | 166 | 8 | 0.74 |
| Cv | ng/mL | 5.1E0 | 1.0E1 | 2.6E1 | 9.9E1 | 6.2E1 | 1.8E2 | 2.0E-2 | 1.0E-1 | 5.3E2 | 4.7E2 | 166 | 8 | 166 | 8 | 0.57 |
| Cw | mIU/mL | 3.5E-2 | 7.4E-2 | 4.3E-2 | 9.1E-1 | 3.5E-2 | 2.4E0 | 8.9E-4 | 1.1E-2 | 2.3E-1 | 6.8E0 | 166 | 8 | 166 | 8 | 0.74 |
| Cx | ng/mL | 7.3E-1 | 7.6E-3 | 5.0E1 | 5.7E1 | 9.8E1 | 1.1E2 | 9.3E-5 | 9.3E-5 | 3.9E2 | 2.8E2 | 166 | 8 | 166 | 8 | 0.42 |
| Db | ug/mL | 7.5E0 | 1.1E1 | 8.6E0 | 1.2E1 | 7.5E0 | 8.8E0 | 4.5E-1 | 4.0E0 | 5.9E1 | 3.1E1 | 166 | 8 | 166 | 8 | 0.62 |
| Dc | nmol/L | 2.1E-2 | 1.7E-1 | 6.6E-2 | 2.1E0 | 1.8E-1 | 4.9E0 | 5.2E-6 | 2.1E-3 | 1.6E0 | 1.4E1 | 166 | 8 | 166 | 8 | 0.78 |
| Dd | ug/mL | 7.0E-2 | 4.3E-1 | 1.8E-1 | 7.8E-1 | 2.7E-1 | 1.2E0 | 4.8E-4 | 6.4E-3 | 1.6E0 | 3.6E0 | 166 | 8 | 166 | 8 | 0.76 |
| De | ng/mL | 3.4E-3 | 2.2E-1 | 7.3E-2 | 3.4E-1 | 1.3E-1 | 4.1E-1 | 3.4E-3 | 3.4E-3 | 9.2E-1 | 1.1E0 | 166 | 8 | 166 | 8 | 0.72 |
| Dg | ng/mL | 3.6E1 | 5.2E1 | 4.8E1 | 5.8E1 | 4.1E1 | 3.9E1 | 7.1E-1 | 1.9E0 | 1.9E2 | 1.2E2 | 166 | 8 | 166 | 8 | 0.60 |
| Di | pg/mL | 2.0E0 | 4.4E0 | 2.4E0 | 4.2E0 | 2.1E0 | 2.5E0 | 1.8E-1 | 1.8E-1 | 1.3E1 | 9.0E0 | 166 | 8 | 166 | 8 | 0.74 |
| Dk | uIU/mL | 1.4E-2 | 1.8E-1 | 4.9E-2 | 3.2E-1 | 1.5E-1 | 3.8E-1 | 1.1E-4 | 1.1E-4 | 1.6E0 | 9.8E-1 | 166 | 8 | 166 | 8 | 0.65 |
| Dl | ng/mL | 2.0E2 | 3.5E2 | 2.9E2 | 4.9E2 | 2.7E2 | 5.2E2 | 5.5E0 | 4.4E0 | 1.3E3 | 1.6E3 | 166 | 8 | 166 | 8 | 0.60 |
| Ef | ng/ml | 9.4E-2 | 6.4E0 | 6.9E-1 | 5.0E0 | 1.6E0 | 4.2E0 | 5.7E-4 | 4.6E-3 | 1.0E1 | 9.9E0 | 140 | 7 | 140 | 7 | 0.78 |
| Wm | % | 8.5E-2 | 2.5E0 | 2.1E1 | 3.1E1 | 1.3E2 | 6.4E1 | 5.4E-2 | 8.5E-2 | 1.0E3 | 1.9E2 | 149 | 10 | 149 | 10 | 0.68 |
| Po | pg/ml | 2.6E-1 | 2.8E1 | 8.3E0 | 5.9E1 | 2.6E1 | 7.3E1 | 8.0E-3 | 2.6E-2 | 2.7E2 | 2.2E2 | 339 | 15 | 339 | 15 | 0.79 |
| Et | ng/ml | 1.4E3 | 4.0E3 | 1.6E3 | 3.5E3 | 1.1E3 | 1.4E3 | 7.5E1 | 5.9E2 | 4.8E3 | 5.0E3 | 338 | 15 | 338 | 15 | 0.84 |
| Ex | ng/ml | 7.6E-2 | 1.6E-1 | 1.8E-1 | 9.6E-1 | 3.1E-1 | 1.5E0 | 3.5E-5 | 5.8E-2 | 2.2E0 | 4.1E0 | 98 | 7 | 98 | 7 | 0.73 |
| Fp | ng/ml | 1.3E1 | 3.1E1 | 2.3E1 | 3.8E1 | 2.7E1 | 3.2E1 | 6.0E-3 | 2.3E0 | 1.3E2 | 1.3E2 | 341 | 15 | 341 | 15 | 0.68 |
| Fr | ng/ml | 3.5E4 | 6.0E5 | 1.1E5 | 5.1E5 | 1.7E5 | 3.1E5 | 1.9E2 | 7.0E3 | 8.4E5 | 8.4E5 | 346 | 17 | 346 | 17 | 0.84 |
| Fw | pg/ml | 2.7E0 | 9.4E0 | 4.6E1 | 5.9E1 | 2.6E2 | 1.2E2 | 1.2E-1 | 1.2E-1 | 3.0E3 | 3.3E2 | 142 | 7 | 142 | 7 | 0.67 |
| Gl | pg/ml | 8.9E3 | 2.5E4 | 1.2E4 | 2.3E4 | 9.5E3 | 1.0E4 | 9.1E1 | 8.7E3 | 3.2E4 | 3.2E4 | 142 | 7 | 142 | 7 | 0.80 |
| Nm | pg/ml | 1.3E4 | 4.5E4 | 3.4E4 | 1.3E5 | 8.2E4 | 2.2E5 | 1.0E-9 | 1.0E-9 | 9.6E5 | 8.2E5 | 342 | 15 | 342 | 15 | 0.70 |
| Nn | pg/ml | 1.5E2 | 5.3E3 | 1.4E3 | 4.0E4 | 6.6E3 | 8.1E4 | 1.0E-9 | 1.0E-9 | 9.5E4 | 3.1E5 | 342 | 15 | 342 | 15 | 0.81 |
| No | pg/ml | 1.5E1 | 5.1E1 | 3.2E1 | 2.5E2 | 5.7E1 | 3.2E2 | 1.0E-9 | 1.6E0 | 5.6E2 | 9.1E2 | 342 | 15 | 342 | 15 | 0.71 |
| Nq | pg/ml | 1.9E0 | 5.5E1 | 1.8E1 | 1.6E2 | 6.5E1 | 2.1E2 | 1.0E-9 | 1.0E-9 | 6.7E2 | 6.3E2 | 342 | 15 | 342 | 15 | 0.78 |
| Nr | pg/ml | 1.5E0 | 1.5E1 | 2.1E1 | 1.8E2 | 7.5E1 | 3.7E2 | 1.0E-9 | 1.0E-9 | 9.8E2 | 1.4E3 | 342 | 15 | 342 | 15 | 0.73 |
| Ns | pg/ml | 1.0E-9 | 1.0E-9 | 7.8E0 | 4.8E-1 | 6.5E1 | 1.3E0 | 1.0E-9 | 1.0E-9 | 1.1E3 | 3.6E0 | 342 | 15 | 342 | 15 | 0.53 |
| Nt | pg/ml | 1.0E2 | 2.2E2 | 1.3E2 | 4.1E2 | 9.9E1 | 4.8E2 | 9.8E-1 | 7.5E1 | 8.8E2 | 1.7E3 | 342 | 15 | 342 | 15 | 0.74 |
| Nu | pg/ml | 1.7E1 | 1.0E2 | 5.5E1 | 1.2E2 | 9.1E1 | 1.0E2 | 1.0E-9 | 1.0E-9 | 6.3E2 | 3.7E2 | 342 | 15 | 342 | 15 | 0.74 |
| Lu | pg/ml | 1.0E4 | 6.2E3 | 1.6E4 | 7.0E3 | 4.0E4 | 4.6E3 | 7.7E2 | 5.2E2 | 5.6E5 | 1.7E4 | 342 | 15 | 342 | 15 | 0.36 |
| Lv | pg/ml | 1.0E-9 | 6.7E1 | 1.4E1 | 7.2E1 | 2.8E1 | 6.4E1 | 1.0E-9 | 1.0E-9 | 2.6E2 | 1.9E2 | 342 | 15 | 342 | 15 | 0.78 |

Figure 34

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Lw | pg/ml | 1.0E-9 | 1.0E-9 | 4.7E-1 | 1.7E1 | 5.0E0 | 4.6E1 | 1.0E-9 | 1.0E-9 | 8.0E1 | 1.8E2 | 342 | 15 | 342 | 15 | 0.62 |
| Lx | pg/ml | 1.0E-9 | 8.7E2 | 1.7E2 | 2.4E3 | 5.5E2 | 5.6E3 | 1.0E-9 | 1.0E-9 | 6.2E3 | 2.2E4 | 342 | 15 | 342 | 15 | 0.81 |
| Ly | pg/ml | 1.0E-9 | 1.0E-9 | 9.2E0 | 7.5E0 | 1.8E1 | 1.6E1 | 1.0E-9 | 1.0E-9 | 1.1E2 | 6.0E1 | 342 | 15 | 342 | 15 | 0.51 |
| Lz | pg/ml | 1.0E-9 | 1.0E-9 | 3.2E0 | 8.7E0 | 2.6E1 | 2.0E1 | 1.0E-9 | 1.0E-9 | 4.3E2 | 6.2E1 | 342 | 15 | 342 | 15 | 0.60 |
| Ma | pg/ml | 3.9E2 | 3.8E3 | 2.1E3 | 1.0E4 | 5.4E3 | 1.5E4 | 1.0E-9 | 2.4E1 | 6.5E4 | 5.2E4 | 342 | 15 | 342 | 15 | 0.76 |
| Mb | pg/ml | 2.5E1 | 2.2E1 | 3.2E1 | 2.8E1 | 1.8E1 | 1.7E1 | 9.2E0 | 4.1E0 | 2.1E2 | 5.8E1 | 342 | 15 | 342 | 15 | 0.38 |
| Mc | pg/ml | 1.0E-9 | 1.0E-9 | 5.6E-2 | 1.0E-9 | 7.4E-1 | 0.0E0 | 1.0E-9 | 1.0E-9 | 1.3E1 | 1.0E-9 | 342 | 15 | 342 | 15 | 0.49 |
| Md | pg/ml | 1.0E-9 | 1.0E-9 | 5.7E-1 | 2.7E0 | 5.2E0 | 7.6E0 | 1.0E-9 | 1.0E-9 | 6.8E1 | 2.9E1 | 342 | 15 | 342 | 15 | 0.63 |
| Me | pg/ml | 3.2E1 | 2.9E1 | 3.1E1 | 3.4E1 | 2.4E1 | 4.4E1 | 1.0E-9 | 1.0E-9 | 3.2E2 | 1.8E2 | 342 | 15 | 342 | 15 | 0.44 |
| Mf | pg/ml | 1.0E-9 | 1.0E-9 | 6.3E-1 | 7.4E-1 | 3.9E0 | 1.7E0 | 1.0E-9 | 1.0E-9 | 5.6E1 | 5.0E0 | 342 | 15 | 342 | 15 | 0.59 |
| Mg | pg/ml | 9.4E-1 | 1.4E1 | 6.1E0 | 2.6E1 | 1.2E1 | 4.2E1 | 1.0E-9 | 1.0E-9 | 9.2E1 | 1.5E2 | 342 | 15 | 342 | 15 | 0.64 |
| Mh | pg/ml | 1.0E-9 | 4.0E-2 | 1.1E0 | 2.5E0 | 7.6E0 | 5.5E0 | 1.0E-9 | 1.0E-9 | 1.1E2 | 1.8E1 | 342 | 15 | 342 | 15 | 0.65 |
| Mi | pg/ml | 1.0E-9 | 1.0E-9 | 1.0E0 | 6.7E1 | 8.4E0 | 1.5E2 | 1.0E-9 | 1.0E-9 | 1.2E2 | 5.2E2 | 342 | 15 | 342 | 15 | 0.69 |
| Mj | pg/ml | 1.0E-9 | 1.0E-9 | 5.6E0 | 4.2E1 | 3.1E1 | 6.8E1 | 1.0E-9 | 1.0E-9 | 4.6E2 | 2.1E2 | 342 | 15 | 342 | 15 | 0.67 |
| Mk | pg/ml | 1.8E0 | 5.3E0 | 1.5E1 | 4.9E1 | 9.2E1 | 1.3E2 | 1.0E-9 | 1.0E-9 | 1.3E3 | 5.0E2 | 342 | 15 | 342 | 15 | 0.61 |
| Ml | pg/ml | 1.0E-9 | 1.0E-9 | 1.0E1 | 3.5E1 | 1.2E2 | 1.3E2 | 1.0E-9 | 1.0E-9 | 2.1E3 | 5.1E2 | 342 | 15 | 342 | 15 | 0.50 |
| Mm | pg/ml | 5.4E2 | 2.6E3 | 1.0E3 | 3.1E3 | 1.3E3 | 2.8E3 | 1.0E-9 | 1.0E-9 | 1.0E4 | 1.0E4 | 342 | 15 | 342 | 15 | 0.74 |
| Mn | pg/ml | 5.7E0 | 1.5E1 | 1.1E1 | 1.7E1 | 2.5E1 | 1.2E1 | 1.0E-9 | 1.1E0 | 3.5E2 | 5.1E1 | 342 | 15 | 342 | 15 | 0.75 |
| Mp | pg/ml | 1.0E-9 | 3.0E1 | 1.2E2 | 2.4E2 | 4.3E1 | 6.0E2 | 1.0E-9 | 1.0E-9 | 6.3E2 | 2.4E3 | 342 | 15 | 342 | 15 | 0.80 |
| Mq | pg/ml | 1.0E-9 | 1.0E-9 | 2.1E0 | 1.8E1 | 1.3E1 | 3.3E1 | 1.0E-9 | 1.0E-9 | 1.8E2 | 1.0E2 | 342 | 15 | 342 | 15 | 0.60 |
| Mr | pg/ml | 1.0E-9 | 1.5E1 | 2.3E1 | 5.1E2 | 1.3E2 | 1.0E3 | 1.0E-9 | 1.0E-9 | 1.5E3 | 3.4E3 | 342 | 15 | 342 | 15 | 0.68 |
| Ms | pg/ml | 3.3E2 | 1.9E2 | 4.8E2 | 2.8E2 | 5.8E2 | 3.2E2 | 1.0E-9 | 1.0E-9 | 4.7E3 | 9.8E2 | 342 | 15 | 342 | 15 | 0.39 |
| Mt | pg/ml | 2.2E-1 | 7.3E1 | 8.0E0 | 2.8E2 | 4.3E1 | 8.2E2 | 1.0E-9 | 1.0E-9 | 7.1E2 | 3.2E3 | 342 | 15 | 342 | 15 | 0.85 |
| Mu | pg/ml | 1.0E-9 | 4.4E0 | 1.4E0 | 9.1E0 | 1.4E1 | 1.4E1 | 1.0E-9 | 1.0E-9 | 2.3E2 | 4.8E1 | 342 | 15 | 342 | 15 | 0.80 |
| Mv | pg/ml | 1.0E-9 | 1.4E2 | 5.9E1 | 3.4E2 | 3.3E2 | 3.8E2 | 1.0E-9 | 1.0E-9 | 4.5E3 | 9.2E2 | 342 | 15 | 342 | 15 | 0.73 |
| Mw | pg/ml | 3.5E1 | 1.0E3 | 2.5E2 | 1.6E3 | 1.3E3 | 1.8E3 | 1.0E-9 | 1.0E-9 | 1.8E4 | 5.3E3 | 342 | 15 | 342 | 15 | 0.83 |
| Mx | pg/ml | 1.0E-9 | 6.0E-2 | 3.5E-1 | 2.1E0 | 1.9E0 | 5.1E0 | 1.0E-9 | 1.0E-9 | 3.2E1 | 2.0E1 | 342 | 15 | 342 | 15 | 0.69 |
| My | pg/ml | 1.0E-9 | 2.3E2 | 3.2E2 | 4.9E2 | 2.4E3 | 6.5E2 | 1.0E-9 | 1.0E-9 | 3.9E4 | 1.9E3 | 342 | 15 | 342 | 15 | 0.76 |
| Mz | pg/ml | 1.1E1 | 7.7E1 | 2.6E1 | 2.8E2 | 5.0E1 | 5.6E2 | 1.0E-9 | 1.0E-9 | 5.5E2 | 1.9E3 | 342 | 15 | 342 | 15 | 0.76 |
| Na | pg/ml | 1.0E-9 | 1.0E-9 | 6.4E-1 | 4.0E0 | 1.9E0 | 1.1E1 | 1.0E-9 | 1.0E-9 | 9.6E0 | 4.2E1 | 342 | 15 | 342 | 15 | 0.60 |
| Nb | pg/ml | 2.1E0 | 8.1E0 | 3.5E0 | 3.1E1 | 9.9E0 | 5.7E1 | 1.0E-9 | 1.0E-9 | 1.5E2 | 2.1E2 | 342 | 15 | 342 | 15 | 0.73 |
| Nc | pg/ml | 3.4E2 | 2.3E1 | 5.2E2 | 2.5E2 | 7.4E2 | 4.1E2 | 1.0E-9 | 1.0E-9 | 9.2E3 | 1.3E3 | 342 | 15 | 342 | 15 | 0.36 |
| Nd | pg/ml | 2.7E1 | 3.9E1 | 2.7E1 | 1.8E2 | 6.8E1 | 5.4E2 | 1.0E-9 | 1.0E-9 | 1.2E3 | 2.1E3 | 342 | 15 | 342 | 15 | 0.61 |
| Ne | pg/ml | 4.2E2 | 3.2E2 | 5.2E2 | 4.9E2 | 5.4E2 | 8.9E2 | 1.0E-9 | 1.0E-9 | 7.0E3 | 3.6E3 | 342 | 15 | 342 | 15 | 0.38 |
| Nf | pg/ml | 1.0E-9 | 1.0E-9 | 2.3E0 | 2.0E1 | 8.6E0 | 4.3E1 | 1.0E-9 | 1.0E-9 | 8.2E1 | 1.3E2 | 342 | 15 | 342 | 15 | 0.58 |
| Ng | pg/ml | 1.1E1 | 5.3E1 | 9.0E1 | 9.7E1 | 1.8E2 | 1.2E2 | 1.0E-9 | 1.0E-9 | 1.6E3 | 4.2E2 | 342 | 15 | 342 | 15 | 0.56 |
| Nh | pg/ml | 6.2E1 | 3.2E1 | 8.0E1 | 6.8E1 | 7.3E1 | 1.2E2 | 1.0E-9 | 4.1E0 | 5.6E2 | 5.1E2 | 342 | 15 | 342 | 15 | 0.33 |
| Ni | pg/ml | 1.0E-9 | 1.0E-9 | 8.1E1 | 1.7E2 | 1.3E2 | 2.9E2 | 1.0E-9 | 1.0E-9 | 7.1E2 | 1.1E3 | 342 | 15 | 342 | 15 | 0.52 |
| Nj | pg/ml | 7.2E0 | 4.4E0 | 1.1E1 | 7.2E0 | 1.2E1 | 7.4E0 | 1.0E-9 | 1.0E-9 | 6.9E1 | 2.2E1 | 342 | 15 | 342 | 15 | 0.40 |
| Nk | pg/ml | 1.8E1 | 4.6E0 | 3.3E1 | 1.7E1 | 3.9E1 | 2.4E1 | 1.0E-9 | 1.0E-9 | 2.0E2 | 6.9E1 | 342 | 15 | 342 | 15 | 0.39 |
| Nl | pg/ml | 4.3E1 | 1.5E1 | 5.7E1 | 3.7E1 | 7.5E1 | 5.4E1 | 1.0E-9 | 1.0E-9 | 1.1E3 | 1.8E2 | 342 | 15 | 342 | 15 | 0.34 |
| Hq | pg/ml | 1.2E0 | 1.5E1 | 1.5E2 | 2.1E2 | 1.9E3 | 7.1E2 | 1.0E-9 | 1.0E-9 | 2.8E4 | 2.8E3 | 340 | 15 | 340 | 15 | 0.74 |
| Hr | pg/ml | 8.9E2 | 2.8E2 | 6.2E2 | 1.4E3 | 1.3E3 | 2.4E3 | 1.0E-9 | 1.0E-9 | 1.2E4 | 8.9E3 | 340 | 15 | 340 | 15 | 0.62 |
| Hu | pg/ml | 5.4E0 | 4.5E2 | 4.6E3 | 1.4E3 | 4.0E4 | 2.1E3 | 1.0E-9 | 1.0E-9 | 6.3E5 | 6.5E3 | 340 | 15 | 340 | 15 | 0.70 |
| Hv | pg/ml | 1.4E0 | 3.0E0 | 2.9E0 | 6.7E1 | 1.0E1 | 2.3E2 | 1.0E-9 | 1.0E-9 | 1.6E2 | 8.9E2 | 340 | 15 | 340 | 15 | 0.70 |
| Hw | pg/ml | 6.1E0 | 1.5E1 | 1.5E1 | 6.9E2 | 4.5E1 | 2.4E3 | 1.0E-9 | 4.6E-1 | 6.4E2 | 9.4E3 | 340 | 15 | 340 | 15 | 0.65 |
| Hx | pg/ml | 8.6E0 | 3.8E1 | 5.2E1 | 1.8E2 | 5.0E2 | 3.7E2 | 1.0E-9 | 3.9E0 | 9.3E3 | 1.3E3 | 340 | 15 | 340 | 15 | 0.77 |
| Ih | ng/ml | 6.3E1 | 3.3E2 | 2.5E2 | 6.9E2 | 4.4E2 | 7.9E2 | 1.0E-9 | 2.4E0 | 3.6E3 | 2.8E3 | 341 | 15 | 341 | 15 | 0.70 |
| Ii | ng/ml | 7.9E1 | 2.9E2 | 2.0E2 | 9.0E2 | 4.6E2 | 1.4E3 | 7.3E-1 | 7.5E-1 | 5.2E3 | 4.5E3 | 341 | 15 | 341 | 15 | 0.68 |
| Ij | ng/ml | 7.8E1 | 1.7E2 | 1.8E2 | 1.9E3 | 5.7E2 | 6.2E3 | 2.8E0 | 9.5E0 | 6.4E3 | 2.4E4 | 337 | 15 | 337 | 15 | 0.75 |
| Ik | ng/ml | 1.1E1 | 2.0E1 | 1.3E2 | 1.8E2 | 1.2E4 | 3.8E2 | 5.9E-1 | 6.2E-1 | 1.2E5 | 1.5E3 | 337 | 15 | 337 | 15 | 0.59 |
| Il | ng/ml | 3.3E2 | 8.0E2 | 1.3E3 | 3.9E3 | 2.8E3 | 5.1E3 | 1.0E-9 | 1.9E-1 | 1.2E4 | 1.2E4 | 335 | 15 | 335 | 15 | 0.68 |
| Im | ng/ml | 2.1E2 | 7.0E2 | 4.6E2 | 1.5E3 | 1.0E3 | 2.0E3 | 1.4E1 | 2.2E1 | 1.5E4 | 6.2E3 | 337 | 15 | 337 | 15 | 0.76 |
| In | ng/ml | 3.5E0 | 2.2E0 | 2.0E1 | 3.6E2 | 8.9E1 | 1.2E3 | 1.0E-9 | 1.0E-9 | 1.1E3 | 4.5E3 | 341 | 15 | 341 | 15 | 0.49 |
| Io | ng/ml | 9.5E3 | 1.0E4 | 2.0E4 | 1.2E4 | 4.7E4 | 1.1E4 | 1.0E-9 | 1.0E3 | 7.1E5 | 3.3E4 | 341 | 15 | 341 | 15 | 0.49 |
| Ip | ng/ml | 1.0E1 | 4.3E1 | 2.1E1 | 4.2E1 | 2.6E1 | 1.7E1 | 1.0E-9 | 9.8E0 | 2.3E2 | 7.1E1 | 341 | 15 | 341 | 15 | 0.80 |
| Iq | ug/ml | 1.0E-1 | 3.2E-1 | 4.1E1 | 1.9E1 | 7.4E2 | 5.6E1 | 1.0E-9 | 1.0E-9 | 1.4E4 | 2.2E2 | 341 | 15 | 341 | 15 | 0.71 |

Figure 34 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ir | ug/ml | 3.7E-1 | 1.2E0 | 4.5E0 | 4.7E1 | 3.2E1 | 9.9E1 | 1.0E-9 | 3.5E-2 | 5.1E2 | 3.7E2 | 340 | 15 | 340 | 15 | 0.77 |
| Is | ng/ml | 2.0E0 | 3.5E1 | 9.0E0 | 5.4E1 | 3.4E1 | 6.9E1 | 1.0E-9 | 4.3E-1 | 5.5E2 | 2.6E2 | 341 | 15 | 341 | 15 | 0.83 |
| It | ng/ml | 2.1E0 | 6.2E0 | 2.2E1 | 5.5E1 | 1.0E2 | 1.7E2 | 1.0E-9 | 1.0E-9 | 1.1E3 | 6.8E2 | 341 | 15 | 341 | 15 | 0.64 |
| Iu | ng/ml | 1.6E2 | 1.0E3 | 1.2E3 | 6.0E3 | 3.9E3 | 9.8E3 | 1.0E-9 | 1.0E-9 | 2.9E4 | 2.4E4 | 341 | 15 | 341 | 15 | 0.64 |
| Iv | ng/ml | 1.3E1 | 6.1E1 | 9.4E1 | 6.3E2 | 8.9E2 | 1.3E3 | 1.0E-9 | 1.0E0 | 1.6E4 | 3.8E3 | 340 | 15 | 340 | 15 | 0.71 |
| Pz | ng/ml | 3.5E3 | 1.0E4 | 5.6E3 | 6.7E3 | 6.0E3 | 4.3E3 | 1.6E1 | 4.0E1 | 7.0E4 | 1.3E4 | 337 | 15 | 337 | 15 | 0.60 |
| Qa | ng/ml | 3.6E3 | 1.9E4 | 6.8E3 | 3.0E4 | 7.9E3 | 5.4E4 | 1.5E2 | 9.4E2 | 4.2E4 | 2.2E5 | 337 | 15 | 337 | 15 | 0.79 |
| Qb | ng/ml | 1.1E2 | 2.8E2 | 2.3E2 | 4.0E2 | 4.4E2 | 3.8E2 | 7.9E-1 | 3.2E1 | 5.3E3 | 1.6E3 | 337 | 15 | 337 | 15 | 0.72 |
| Qc | ng/ml | 2.1E2 | 5.0E2 | 4.5E2 | 6.4E2 | 5.9E2 | 7.8E2 | 1.0E-9 | 1.3E1 | 4.3E3 | 2.8E3 | 337 | 15 | 337 | 15 | 0.56 |
| Qd | ng/ml | 8.8E3 | 6.0E4 | 2.5E4 | 8.8E4 | 1.2E5 | 8.4E4 | 1.5E2 | 1.9E3 | 2.0E6 | 2.3E5 | 337 | 15 | 337 | 15 | 0.75 |
| Qe | ng/ml | 8.6E2 | 4.1E3 | 2.0E3 | 5.0E3 | 5.6E3 | 4.6E3 | 1.0E-9 | 1.2E2 | 9.7E4 | 1.8E4 | 337 | 15 | 337 | 15 | 0.78 |
| Jg | ng/ml | 4.6E2 | 2.0E3 | 7.7E2 | 2.1E3 | 9.4E2 | 1.7E3 | 5.8E0 | 8.4E1 | 1.0E4 | 7.1E3 | 340 | 15 | 340 | 15 | 0.78 |
| Jh | ng/ml | 2.9E0 | 6.0E1 | 2.0E1 | 1.0E2 | 8.2E1 | 1.4E2 | 1.0E-9 | 1.0E-9 | 1.2E3 | 4.9E2 | 340 | 15 | 340 | 15 | 0.80 |
| Ji | ng/ml | 5.6E1 | 3.2E2 | 8.6E1 | 3.6E2 | 9.6E1 | 3.2E2 | 1.1E0 | 2.3E1 | 6.9E2 | 1.3E3 | 340 | 15 | 340 | 15 | 0.84 |
| Jj | ng/ml | 5.3E2 | 1.1E2 | 1.9E3 | 4.7E2 | 1.8E4 | 5.2E2 | 2.3E0 | 8.7E0 | 3.4E5 | 1.4E3 | 340 | 15 | 340 | 15 | 0.34 |
| Jk | ng/ml | 2.6E0 | 6.5E1 | 1.9E1 | 8.1E1 | 4.6E1 | 7.8E1 | 1.0E-9 | 1.2E-1 | 3.9E2 | 2.4E2 | 340 | 15 | 340 | 15 | 0.77 |
| Jl | ng/ml | 4.8E-1 | 2.0E1 | 1.8E0 | 6.7E2 | 4.4E0 | 2.6E3 | 1.2E-3 | 1.1E-1 | 4.0E1 | 9.9E3 | 340 | 15 | 340 | 15 | 0.84 |
| Jm | ng/ml | 2.0E1 | 4.9E1 | 6.7E1 | 7.3E1 | 1.7E2 | 9.7E1 | 1.0E-9 | 4.0E-1 | 2.1E3 | 3.6E2 | 340 | 15 | 340 | 15 | 0.59 |
| Jn | pg/ml | 3.3E-1 | 1.5E0 | 4.0E0 | 9.2E1 | 3.6E1 | 2.4E2 | 1.0E-9 | 2.4E-1 | 6.2E2 | 7.3E2 | 340 | 15 | 340 | 15 | 0.80 |
| Jo | pg/ml | 3.8E3 | 5.5E3 | 4.7E3 | 1.6E4 | 3.9E3 | 2.6E4 | 2.0E1 | 2.4E1 | 2.4E4 | 1.0E5 | 340 | 15 | 340 | 15 | 0.64 |
| Jp | pg/ml | 7.0E4 | 1.0E5 | 7.4E4 | 1.2E5 | 3.9E4 | 4.4E4 | 5.8E2 | 6.5E4 | 3.8E5 | 2.1E5 | 340 | 15 | 340 | 15 | 0.79 |
| Jq | pg/ml | 9.5E1 | 3.3E2 | 1.6E2 | 1.2E3 | 2.0E2 | 2.3E3 | 1.0E0 | 1.3E1 | 2.0E3 | 8.7E3 | 340 | 15 | 340 | 15 | 0.76 |
| Jr | pg/ml | 4.0E0 | 4.0E1 | 5.9E1 | 8.8E2 | 6.0E2 | 2.2E3 | 1.0E-9 | 6.7E0 | 1.1E4 | 7.4E3 | 340 | 15 | 340 | 15 | 0.87 |
| Js | pg/ml | 1.5E1 | 2.7E1 | 7.4E1 | 4.6E2 | 5.7E2 | 1.0E3 | 1.0E-9 | 2.7E0 | 1.0E4 | 3.0E3 | 340 | 15 | 340 | 15 | 0.69 |
| Jt | pg/ml | 2.4E3 | 4.3E3 | 3.0E3 | 1.1E4 | 2.4E3 | 1.6E4 | 2.2E1 | 1.5E2 | 2.2E4 | 5.2E4 | 340 | 15 | 340 | 15 | 0.66 |
| Lh | pg/ml | 1.3E4 | 3.8E4 | 2.1E4 | 1.3E5 | 2.7E4 | 1.6E5 | 1.0E-9 | 1.8E3 | 2.6E5 | 4.8E5 | 341 | 15 | 341 | 15 | 0.80 |
| Li | pg/ml | 3.5E3 | 1.5E4 | 1.9E4 | 1.0E5 | 9.0E4 | 1.3E5 | 1.2E1 | 3.7E1 | 1.3E6 | 4.1E5 | 341 | 15 | 341 | 15 | 0.67 |
| Lj | pg/ml | 2.9E3 | 3.8E3 | 2.0E4 | 3.9E4 | 5.6E4 | 1.0E5 | 1.0E-9 | 8.9E1 | 4.3E5 | 3.9E5 | 341 | 15 | 341 | 15 | 0.58 |
| Nv | pg/ml | 3.9E3 | 2.5E4 | 8.9E3 | 4.3E4 | 1.8E4 | 4.2E4 | 1.0E-9 | 1.6E2 | 1.6E5 | 1.2E5 | 342 | 15 | 342 | 15 | 0.80 |
| Nw | pg/ml | 9.5E3 | 2.4E4 | 1.3E4 | 5.1E4 | 1.6E4 | 6.9E4 | 1.9E2 | 4.5E3 | 2.1E5 | 2.2E5 | 342 | 15 | 342 | 15 | 0.79 |
| Nx | pg/ml | 2.2E2 | 1.1E3 | 4.2E2 | 1.2E3 | 6.0E2 | 1.1E3 | 1.0E-9 | 1.0E-9 | 3.5E3 | 4.1E3 | 342 | 15 | 342 | 15 | 0.74 |
| Ny | pg/ml | 6.4E0 | 4.6E1 | 9.7E1 | 3.3E2 | 1.3E3 | 7.0E2 | 1.0E-9 | 1.0E-9 | 2.5E4 | 2.8E3 | 342 | 15 | 342 | 15 | 0.81 |
| Oe | pg/ml | 2.9E1 | 1.0E-9 | 2.4E2 | 2.4E2 | 3.8E2 | 4.2E2 | 1.0E-9 | 1.0E-9 | 2.3E3 | 1.1E3 | 340 | 15 | 340 | 15 | 0.45 |
| Of | pg/ml | 1.3E2 | 1.4E2 | 4.8E3 | 1.1E4 | 2.0E4 | 1.9E4 | 1.0E-9 | 1.0E-9 | 1.9E5 | 6.6E4 | 342 | 15 | 342 | 15 | 0.60 |
| Og | pg/ml | 6.9E-2 | 1.7E-2 | 3.6E-1 | 7.4E-2 | 1.5E0 | 1.1E-1 | 1.0E-9 | 1.0E-9 | 1.9E1 | 3.2E-1 | 342 | 15 | 342 | 15 | 0.39 |
| Oh | pg/ml | 2.5E0 | 2.5E1 | 1.4E1 | 1.2E3 | 8.8E1 | 4.1E3 | 1.0E-9 | 1.0E-9 | 1.4E3 | 1.6E4 | 342 | 15 | 342 | 15 | 0.76 |
| Oi | pg/ml | 2.0E0 | 1.0E-9 | 4.9E0 | 6.1E0 | 7.8E0 | 8.8E0 | 1.0E-9 | 1.0E-9 | 6.7E1 | 3.1E1 | 342 | 15 | 342 | 15 | 0.49 |
| Ok | pg/ml | 3.9E2 | 1.5E3 | 5.3E2 | 2.0E3 | 6.2E2 | 2.1E3 | 1.5E1 | 5.3E1 | 7.0E3 | 7.8E3 | 342 | 15 | 342 | 15 | 0.78 |
| Om | pg/ml | 4.1E2 | 1.9E3 | 7.9E2 | 5.7E3 | 2.0E3 | 1.3E4 | 1.0E-9 | 7.0E1 | 3.0E4 | 5.1E4 | 342 | 15 | 342 | 15 | 0.80 |
| On | pg/ml | 1.8E2 | 1.2E3 | 2.8E2 | 1.8E3 | 4.0E2 | 2.1E3 | 1.0E-9 | 1.6E1 | 4.5E3 | 8.5E3 | 342 | 15 | 342 | 15 | 0.88 |
| Oy | pg/ml | 4.6E-1 | 3.3E0 | 6.0E0 | 7.2E0 | 3.1E1 | 9.3E0 | 1.0E-9 | 1.0E-9 | 4.0E2 | 3.3E1 | 341 | 15 | 341 | 15 | 0.69 |
| Oz | pg/ml | 6.3E-3 | 1.0E-9 | 3.3E-1 | 2.0E0 | 1.6E0 | 7.2E0 | 1.0E-9 | 1.0E-9 | 2.9E1 | 2.8E1 | 341 | 15 | 341 | 15 | 0.42 |
| Pa | pg/ml | 3.9E-1 | 9.2E-1 | 1.3E0 | 2.6E1 | 5.7E0 | 6.1E1 | 1.0E-9 | 1.0E-9 | 8.6E1 | 2.3E2 | 341 | 15 | 341 | 15 | 0.70 |
| Pb | pg/ml | 1.0E-9 | 1.0E-9 | 1.6E0 | 2.2E0 | 2.6E1 | 8.1E0 | 1.0E-9 | 1.0E-9 | 4.9E2 | 3.2E1 | 341 | 15 | 341 | 15 | 0.43 |
| Pc | pg/ml | 4.8E-2 | 1.0E-9 | 3.8E-1 | 2.5E1 | 8.8E-1 | 8.5E1 | 1.0E-9 | 1.0E-9 | 1.4E1 | 3.3E2 | 341 | 15 | 341 | 15 | 0.50 |
| Pd | pg/ml | 1.6E0 | 5.4E0 | 6.2E0 | 2.2E1 | 4.6E1 | 3.3E1 | 1.0E-9 | 7.3E-2 | 8.4E2 | 1.2E2 | 341 | 15 | 341 | 15 | 0.67 |
| Pe | pg/ml | 2.1E1 | 2.2E2 | 1.1E2 | 2.0E3 | 4.4E2 | 4.1E3 | 1.0E-9 | 3.3E0 | 4.7E3 | 1.5E4 | 341 | 15 | 341 | 15 | 0.77 |
| Pf | pg/ml | 1.6E0 | 1.8E1 | 1.5E1 | 6.2E1 | 9.0E1 | 1.1E2 | 1.0E-9 | 1.0E-9 | 1.5E3 | 4.3E2 | 341 | 15 | 341 | 15 | 0.80 |
| Pg | pg/ml | 3.8E0 | 7.8E1 | 6.7E1 | 4.4E2 | 5.1E2 | 6.5E2 | 1.0E-9 | 4.6E-1 | 7.7E3 | 2.2E3 | 341 | 15 | 341 | 15 | 0.83 |
| aA | mg/dL | 9.0E-1 | 1.5E0 | 1.0E0 | 2.1E0 | 5.0E-1 | 1.3E0 | 3.0E-1 | 5.5E-1 | 4.2E0 | 4.7E0 | 516 | 23 | 516 | 23 | 0.78 |
| aC | mg/mL | 2.2E0 | 2.4E0 | 2.6E0 | 2.9E0 | 1.3E0 | 1.7E0 | 7.5E-1 | 1.1E0 | 7.4E0 | 5.5E0 | 167 | 9 | 167 | 9 | 0.51 |
| aD | ug/mL | 2.9E0 | 3.7E0 | 4.6E0 | 5.9E0 | 4.7E0 | 5.3E0 | 7.5E-1 | 1.8E0 | 3.5E1 | 1.8E1 | 167 | 9 | 167 | 9 | 0.57 |
| aE | mg/mL | 5.7E-1 | 5.7E-1 | 5.9E-1 | 5.7E-1 | 1.7E-1 | 1.2E-1 | 1.8E-1 | 3.9E-1 | 1.2E0 | 7.2E-1 | 167 | 9 | 167 | 9 | 0.47 |
| aF | ng/mL | 2.2E0 | 9.1E0 | 4.9E0 | 8.0E0 | 7.7E0 | 5.4E0 | 4.3E-3 | 4.3E-3 | 5.0E1 | 1.5E1 | 167 | 9 | 167 | 9 | 0.68 |
| aG | mg/mL | 1.4E-1 | 9.5E-2 | 1.6E-1 | 1.1E-1 | 8.7E-2 | 3.8E-2 | 3.2E-2 | 6.9E-2 | 4.8E-1 | 1.7E-1 | 167 | 9 | 167 | 9 | 0.37 |
| aH | ug/mL | 7.1E1 | 5.6E1 | 7.8E1 | 5.9E1 | 4.1E1 | 2.7E1 | 8.9E0 | 1.1E1 | 2.0E2 | 1.0E2 | 167 | 9 | 167 | 9 | 0.39 |
| aI | ug/mL | 1.7E2 | 1.4E2 | 1.8E2 | 1.3E2 | 6.1E1 | 5.7E1 | 3.2E1 | 7.5E1 | 3.4E2 | 2.6E2 | 167 | 9 | 167 | 9 | 0.28 |

Figure 34 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aJ | ug/mL | 2.4E0 | 6.8E0 | 3.1E0 | 7.6E0 | 2.2E0 | 6.5E0 | 8.2E-1 | 2.2E0 | 1.4E1 | 2.3E1 | 167 | 9 | 167 | 9 | 0.79 |
| aK | ng/mL | 1.3E0 | 1.6E0 | 1.9E0 | 2.3E0 | 1.9E0 | 2.3E0 | 2.9E-4 | 1.3E-1 | 1.0E1 | 6.5E0 | 167 | 9 | 167 | 9 | 0.52 |
| aL | mg/mL | 7.4E-1 | 7.3E-1 | 7.7E-1 | 7.2E-1 | 2.5E-1 | 3.5E-1 | 2.2E-1 | 2.7E-1 | 1.7E0 | 1.4E0 | 167 | 9 | 167 | 9 | 0.44 |
| aM | U/mL | 1.9E1 | 4.7E1 | 3.9E1 | 1.6E2 | 7.0E1 | 2.7E2 | 4.2E-2 | 4.2E-2 | 6.8E2 | 8.2E2 | 167 | 9 | 167 | 9 | 0.69 |
| aN | U/mL | 1.4E1 | 2.6E1 | 2.5E1 | 3.3E1 | 4.3E1 | 2.6E1 | 2.5E-3 | 7.4E0 | 3.8E2 | 8.8E1 | 167 | 9 | 167 | 9 | 0.68 |
| aO | pg/mL | 4.9E1 | 1.3E3 | 4.0E2 | 1.1E3 | 9.7E2 | 9.8E2 | 6.0E-2 | 1.3E1 | 6.6E3 | 2.4E3 | 167 | 9 | 167 | 9 | 0.77 |
| aP | ng/mL | 1.6E0 | 4.9E0 | 2.2E0 | 6.4E0 | 2.4E0 | 8.3E0 | 4.5E-1 | 1.6E0 | 2.8E1 | 2.8E1 | 167 | 9 | 167 | 9 | 0.80 |
| aQ | ng/mL | 2.4E-1 | 4.1E-1 | 3.5E-1 | 3.8E-1 | 3.2E-1 | 2.6E-1 | 2.0E-4 | 5.1E-2 | 2.0E0 | 9.0E-1 | 167 | 9 | 167 | 9 | 0.56 |
| aR | ng/mL | 1.7E0 | 3.8E0 | 3.0E0 | 3.3E0 | 4.1E0 | 1.9E0 | 2.6E-1 | 5.6E-1 | 3.4E1 | 5.5E0 | 167 | 9 | 167 | 9 | 0.63 |
| aS | ng/mL | 3.7E-1 | 5.4E-1 | 9.9E-1 | 1.0E0 | 2.7E0 | 1.1E0 | 4.2E-3 | 7.2E-2 | 3.3E1 | 2.8E0 | 167 | 9 | 167 | 9 | 0.54 |
| aU | pg/mL | 6.6E1 | 7.8E1 | 9.8E1 | 1.4E2 | 1.0E2 | 1.7E2 | 7.4E-2 | 7.4E-2 | 7.0E2 | 5.1E2 | 167 | 9 | 167 | 9 | 0.51 |
| aV | ng/mL | 5.8E-1 | 5.8E-1 | 1.0E0 | 1.3E0 | 2.6E0 | 1.9E0 | 7.6E-4 | 1.0E-1 | 3.3E1 | 6.0E0 | 167 | 9 | 167 | 9 | 0.50 |
| aW | pg/mL | 1.9E1 | 2.1E1 | 2.2E1 | 2.4E1 | 3.4E1 | 1.3E1 | 7.2E-2 | 7.2E-2 | 4.2E2 | 4.7E1 | 167 | 9 | 167 | 9 | 0.63 |
| aX | ng/mL | 8.0E0 | 1.8E1 | 1.5E1 | 3.7E1 | 3.1E1 | 4.9E1 | 3.0E-1 | 2.6E0 | 3.1E2 | 1.3E2 | 167 | 9 | 167 | 9 | 0.64 |
| aY | pg/mL | 5.3E1 | 6.0E1 | 7.5E1 | 8.4E1 | 1.1E2 | 6.8E1 | 4.1E-1 | 2.7E1 | 1.2E3 | 2.0E2 | 167 | 9 | 167 | 9 | 0.56 |
| aZ | pg/mL | 2.2E2 | 3.0E2 | 6.8E2 | 5.0E2 | 1.5E3 | 6.1E2 | 1.7E0 | 7.5E1 | 1.2E4 | 2.1E3 | 167 | 9 | 167 | 9 | 0.59 |
| bA | ng/mL | 1.3E1 | 1.2E2 | 6.0E1 | 3.3E2 | 1.3E2 | 5.2E2 | 3.0E-2 | 4.7E0 | 9.4E2 | 1.5E3 | 167 | 9 | 167 | 9 | 0.76 |
| bB | ng/mL | 2.8E2 | 1.9E2 | 3.1E2 | 1.9E2 | 1.8E2 | 1.1E2 | 2.1E0 | 3.3E1 | 9.5E2 | 3.8E2 | 167 | 9 | 167 | 9 | 0.31 |
| bC | ng/mL | 3.2E2 | 4.7E2 | 6.1E2 | 1.5E3 | 8.1E2 | 1.6E3 | 1.4E1 | 1.4E2 | 4.7E3 | 4.0E3 | 167 | 9 | 167 | 9 | 0.69 |
| bE | mg/mL | 5.1E0 | 5.5E0 | 5.4E0 | 6.8E0 | 2.1E0 | 3.8E0 | 1.8E0 | 1.3E0 | 1.2E1 | 1.1E1 | 167 | 9 | 167 | 9 | 0.57 |
| bF | pg/mL | 3.5E1 | 6.8E1 | 3.1E2 | 9.6E2 | 1.3E3 | 2.1E3 | 5.0E-2 | 2.0E1 | 1.1E4 | 6.3E3 | 167 | 9 | 167 | 9 | 0.74 |
| bG | ng/mL | 1.6E0 | 4.6E0 | 2.9E0 | 8.0E0 | 3.8E0 | 9.5E0 | 1.1E-1 | 2.4E-1 | 2.6E1 | 3.0E1 | 167 | 9 | 167 | 9 | 0.70 |
| bH | pg/mL | 5.7E-1 | 9.2E0 | 6.1E0 | 9.3E0 | 2.4E1 | 7.9E0 | 5.7E-1 | 5.7E-1 | 2.8E2 | 2.3E1 | 167 | 9 | 167 | 9 | 0.71 |
| bI | ng/mL | 4.0E-3 | 4.0E-3 | 9.1E-2 | 1.2E-1 | 2.0E-1 | 2.0E-1 | 4.0E-3 | 4.0E-3 | 9.8E-1 | 5.1E-1 | 167 | 9 | 167 | 9 | 0.56 |
| bJ | mg/mL | 1.9E0 | 2.3E0 | 2.3E0 | 3.3E0 | 1.9E0 | 3.3E0 | 2.5E-4 | 2.5E-4 | 1.1E1 | 9.0E0 | 167 | 9 | 167 | 9 | 0.57 |
| bL | pg/mL | 3.7E0 | 1.1E1 | 9.1E0 | 1.2E1 | 1.2E1 | 7.6E0 | 4.6E-2 | 3.0E0 | 6.0E1 | 2.4E1 | 167 | 9 | 167 | 9 | 0.69 |
| bM | mg/mL | 1.8E0 | 2.2E0 | 2.2E0 | 2.0E0 | 1.5E0 | 1.0E0 | 1.6E-2 | 5.5E-1 | 8.6E0 | 3.8E0 | 167 | 9 | 167 | 9 | 0.52 |
| bN | ng/mL | 3.3E1 | 5.9E1 | 1.2E2 | 7.8E1 | 2.9E2 | 8.5E1 | 1.4E-1 | 6.7E0 | 1.9E3 | 2.5E2 | 167 | 9 | 167 | 9 | 0.53 |
| bO | ng/mL | 4.0E-2 | 4.0E-2 | 9.3E0 | 4.2E0 | 2.0E1 | 1.2E1 | 4.0E-2 | 4.0E-2 | 1.3E2 | 3.8E1 | 167 | 9 | 167 | 9 | 0.39 |
| bP | mg/mL | 5.3E-1 | 4.9E-1 | 7.5E-1 | 7.1E-1 | 7.1E-1 | 4.9E-1 | 4.9E-2 | 9.2E-2 | 4.8E0 | 1.6E0 | 167 | 9 | 167 | 9 | 0.52 |
| bQ | pg/mL | 2.1E1 | 9.3E1 | 1.4E2 | 1.0E2 | 1.1E3 | 6.6E1 | 1.5E-1 | 1.3E1 | 1.3E4 | 2.2E2 | 167 | 9 | 167 | 9 | 0.80 |
| bR | ng/mL | 1.2E-2 | 1.2E-2 | 1.6E-1 | 8.3E-2 | 7.2E-1 | 1.4E-1 | 1.2E-2 | 1.2E-2 | 8.7E0 | 3.8E-1 | 167 | 9 | 167 | 9 | 0.46 |
| bS | pg/mL | 9.4E-1 | 9.4E-1 | 9.0E0 | 1.9E1 | 4.1E1 | 3.0E1 | 9.4E-1 | 9.4E-1 | 3.9E2 | 7.2E1 | 167 | 9 | 167 | 9 | 0.61 |
| bU | ng/mL | 8.7E-2 | 1.3E-2 | 1.9E-1 | 1.3E-1 | 5.4E-1 | 1.5E-1 | 1.3E-2 | 1.3E-2 | 6.6E0 | 4.1E-1 | 167 | 9 | 167 | 9 | 0.48 |
| bV | pg/mL | 4.9E2 | 6.8E2 | 6.2E2 | 1.0E3 | 8.9E2 | 6.8E2 | 1.6E2 | 3.4E2 | 1.2E4 | 2.2E3 | 167 | 9 | 167 | 9 | 0.74 |
| bW | pg/mL | 3.2E2 | 5.6E2 | 4.9E2 | 1.2E3 | 5.4E2 | 1.5E3 | 8.4E1 | 1.8E2 | 4.8E3 | 3.9E3 | 167 | 9 | 167 | 9 | 0.67 |
| bX | ng/mL | 2.5E-5 | 2.5E-5 | 2.6E-3 | 2.4E-3 | 3.2E-3 | 3.0E-3 | 2.5E-5 | 2.5E-5 | 1.3E-2 | 7.2E-3 | 167 | 9 | 167 | 9 | 0.49 |
| bZ | pg/mL | 2.7E2 | 1.8E3 | 1.8E3 | 6.8E3 | 6.5E3 | 1.4E4 | 1.5E-1 | 1.8E2 | 5.8E4 | 4.3E4 | 167 | 9 | 167 | 9 | 0.72 |
| cA | pg/mL | 6.0E-1 | 6.0E-1 | 4.1E0 | 2.9E0 | 2.9E1 | 6.8E0 | 6.0E-1 | 6.0E-1 | 3.7E2 | 2.1E1 | 167 | 9 | 167 | 9 | 0.50 |
| cB | ng/mL | 4.9E-2 | 4.6E-2 | 7.4E-2 | 8.3E-2 | 8.7E-2 | 9.8E-2 | 1.7E-3 | 1.7E-3 | 4.3E-1 | 2.6E-1 | 167 | 9 | 167 | 9 | 0.49 |
| cC | pg/mL | 4.1E1 | 3.7E1 | 4.6E1 | 3.4E1 | 5.1E1 | 2.7E1 | 1.0E0 | 1.0E0 | 4.5E2 | 6.7E1 | 167 | 9 | 167 | 9 | 0.43 |
| cD | pg/mL | 4.9E0 | 2.9E0 | 1.3E1 | 4.2E0 | 4.7E1 | 3.9E0 | 3.3E-1 | 3.3E-1 | 4.8E2 | 9.6E0 | 167 | 9 | 167 | 9 | 0.40 |
| cE | pg/mL | 5.9E1 | 2.6E2 | 2.6E2 | 3.2E2 | 6.0E2 | 3.7E2 | 1.2E-1 | 3.4E1 | 3.8E3 | 1.3E3 | 167 | 9 | 167 | 9 | 0.71 |
| cF | pg/mL | 4.5E0 | 5.3E-1 | 1.6E1 | 8.6E0 | 3.0E1 | 1.6E1 | 5.3E-1 | 5.3E-1 | 2.7E2 | 3.8E1 | 167 | 9 | 167 | 9 | 0.39 |
| cG | pg/mL | 5.4E1 | 2.3E2 | 1.7E2 | 2.4E2 | 8.2E2 | 1.7E2 | 7.8E0 | 3.6E1 | 1.0E4 | 4.9E2 | 167 | 9 | 167 | 9 | 0.75 |
| cH | uIU/mL | 3.2E0 | 3.1E0 | 7.3E0 | 1.2E1 | 1.7E1 | 1.9E1 | 8.6E-3 | 8.6E-3 | 1.6E2 | 5.3E1 | 167 | 9 | 167 | 9 | 0.51 |
| cI | ng/mL | 6.1E0 | 9.1E0 | 1.4E1 | 1.2E1 | 2.2E1 | 1.4E1 | 3.2E-2 | 1.1E0 | 1.2E2 | 4.1E1 | 167 | 9 | 167 | 9 | 0.50 |
| cJ | ug/mL | 6.7E1 | 3.6E1 | 1.0E2 | 4.7E1 | 1.0E2 | 5.0E1 | 6.9E0 | 5.6E0 | 6.4E2 | 1.7E2 | 167 | 9 | 167 | 9 | 0.31 |
| cK | ng/mL | 3.8E-3 | 3.8E-3 | 2.2E-2 | 4.7E-2 | 1.2E-1 | 6.8E-2 | 3.8E-3 | 3.8E-3 | 1.5E0 | 2.1E-1 | 167 | 9 | 167 | 9 | 0.67 |
| cL | pg/mL | 2.1E2 | 2.3E2 | 5.5E2 | 3.6E2 | 2.0E3 | 3.9E2 | 3.1E1 | 6.7E1 | 2.4E4 | 1.3E3 | 167 | 9 | 167 | 9 | 0.56 |
| cM | pg/mL | 2.7E2 | 2.2E2 | 2.9E2 | 2.2E2 | 1.7E2 | 7.6E1 | 2.5E1 | 5.7E1 | 1.1E3 | 3.1E2 | 167 | 9 | 167 | 9 | 0.37 |
| cN | pg/mL | 1.2E2 | 1.2E2 | 1.3E2 | 1.3E2 | 8.6E1 | 4.0E1 | 3.8E1 | 8.6E1 | 1.1E3 | 2.0E2 | 167 | 9 | 167 | 9 | 0.55 |
| cO | pg/mL | 2.1E2 | 3.2E2 | 4.0E2 | 4.9E2 | 1.5E3 | 4.4E2 | 5.4E1 | 9.6E1 | 1.9E4 | 1.5E3 | 167 | 9 | 167 | 9 | 0.68 |
| cP | ng/mL | 2.4E3 | 2.3E3 | 2.5E3 | 2.8E3 | 9.4E2 | 1.2E3 | 6.2E2 | 1.4E3 | 5.6E3 | 4.7E3 | 167 | 9 | 167 | 9 | 0.56 |
| cQ | ng/mL | 4.9E-2 | 9.1E-2 | 1.2E-1 | 2.2E-1 | 2.1E-1 | 2.9E-1 | 2.0E-3 | 2.0E-3 | 1.3E0 | 8.7E-1 | 167 | 9 | 167 | 9 | 0.59 |
| cR | ng/mL | 3.0E2 | 5.7E2 | 5.9E2 | 7.7E2 | 8.3E2 | 6.1E2 | 2.0E1 | 3.2E2 | 7.7E3 | 2.2E3 | 167 | 9 | 167 | 9 | 0.69 |
| cS | ng/mL | 2.8E2 | 6.6E2 | 4.2E2 | 1.6E3 | 4.7E2 | 2.2E3 | 4.1E1 | 1.4E2 | 3.3E3 | 7.1E3 | 167 | 9 | 167 | 9 | 0.76 |

Figure 34 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cT | ng/mL | 4.9E1 | 1.2E2 | 1.5E2 | 4.0E2 | 2.8E2 | 5.9E2 | 3.6E0 | 1.9E1 | 2.1E3 | 1.5E3 | 167 | 9 | 167 | 9 | 0.70 |
| cU | ng/mL | 5.8E1 | 1.3E2 | 9.6E1 | 1.6E2 | 1.5E2 | 8.6E1 | 6.2E0 | 7.8E1 | 1.6E3 | 3.3E2 | 167 | 9 | 167 | 9 | 0.80 |
| cV | ng/mL | 1.9E-1 | 3.5E-1 | 7.3E-1 | 5.7E-1 | 3.8E0 | 7.8E-1 | 2.5E-2 | 3.0E-2 | 4.7E1 | 2.5E0 | 167 | 9 | 167 | 9 | 0.56 |
| cW | mIU/mL | 4.8E-2 | 9.4E-2 | 8.7E-2 | 1.2E-1 | 3.5E-1 | 1.1E-1 | 4.8E-3 | 2.7E-2 | 4.5E0 | 3.9E-1 | 167 | 9 | 167 | 9 | 0.68 |
| cX | ng/mL | 1.2E-1 | 3.3E-2 | 1.9E0 | 3.6E-1 | 5.7E0 | 8.1E-1 | 2.3E-4 | 1.1E-2 | 2.8E1 | 2.5E0 | 167 | 9 | 167 | 9 | 0.42 |
| cY | ng/mL | 7.4E0 | 8.9E0 | 1.1E1 | 1.4E1 | 1.1E1 | 1.5E1 | 1.7E-1 | 6.0E-1 | 6.1E1 | 3.7E1 | 167 | 9 | 167 | 9 | 0.50 |
| cZ | ug/mL | 1.3E1 | 1.1E1 | 1.5E1 | 1.4E1 | 6.7E0 | 8.2E0 | 2.3E0 | 3.3E0 | 4.6E1 | 3.0E1 | 167 | 9 | 167 | 9 | 0.45 |
| dA | pg/mL | 3.1E2 | 6.3E2 | 3.8E2 | 5.6E2 | 4.6E2 | 3.0E2 | 1.0E2 | 1.7E2 | 5.8E3 | 9.3E2 | 167 | 9 | 167 | 9 | 0.68 |
| dB | ug/mL | 1.8E1 | 2.2E1 | 1.8E1 | 2.1E1 | 2.0E1 | 8.2E0 | 2.1E0 | 4.5E0 | 2.5E2 | 3.0E1 | 167 | 9 | 167 | 9 | 0.63 |
| dC | nmol/L | 3.4E1 | 3.0E1 | 3.7E1 | 3.2E1 | 1.7E1 | 6.5E0 | 7.8E0 | 2.5E1 | 1.4E2 | 4.1E1 | 167 | 9 | 167 | 9 | 0.42 |
| dD | ug/mL | 3.4E1 | 2.8E1 | 3.5E1 | 3.0E1 | 1.1E1 | 9.7E0 | 1.4E1 | 2.1E1 | 7.4E1 | 5.0E1 | 167 | 9 | 167 | 9 | 0.32 |
| dE | ng/mL | 4.1E-1 | 8.6E-1 | 5.6E-1 | 1.0E0 | 5.8E-1 | 8.8E-1 | 8.4E-3 | 8.4E-3 | 2.9E0 | 2.4E0 | 167 | 9 | 167 | 9 | 0.67 |
| dF | ng/mL | 2.5E2 | 7.7E2 | 3.3E2 | 6.3E2 | 2.4E2 | 3.5E2 | 7.5E1 | 2.3E2 | 1.3E3 | 1.2E3 | 167 | 9 | 167 | 9 | 0.78 |
| dG | ng/mL | 1.2E1 | 2.4E1 | 1.6E1 | 3.1E1 | 1.8E1 | 2.8E1 | 3.0E0 | 6.7E0 | 1.8E2 | 8.7E1 | 167 | 9 | 167 | 9 | 0.69 |
| dH | pg/mL | 8.0E0 | 1.4E1 | 2.1E1 | 1.8E1 | 6.3E1 | 2.3E1 | 4.0E-2 | 8.3E-1 | 6.7E2 | 7.6E1 | 167 | 9 | 167 | 9 | 0.60 |
| dI | pg/mL | 4.6E-1 | 2.9E0 | 3.7E0 | 5.0E0 | 2.6E1 | 6.1E0 | 4.6E-1 | 4.6E-1 | 3.3E2 | 1.9E1 | 167 | 9 | 167 | 9 | 0.69 |
| dJ | ng/mL | 2.0E0 | 2.5E0 | 2.1E0 | 2.4E0 | 1.1E0 | 1.3E0 | 3.2E-2 | 4.9E-1 | 5.6E0 | 4.4E0 | 167 | 9 | 167 | 9 | 0.57 |
| dK | uIU/mL | 1.4E0 | 6.4E-1 | 2.2E0 | 1.1E0 | 3.6E0 | 1.9E0 | 2.8E-4 | 1.4E-2 | 3.9E1 | 6.1E0 | 167 | 9 | 167 | 9 | 0.27 |
| dL | ng/mL | 8.7E2 | 1.2E3 | 1.0E3 | 1.5E3 | 5.6E2 | 1.3E3 | 2.8E2 | 5.8E2 | 3.8E3 | 4.8E3 | 167 | 9 | 167 | 9 | 0.58 |
| dM | pg/mL | 9.7E2 | 2.5E3 | 1.3E3 | 2.9E3 | 1.4E3 | 2.1E3 | 3.7E2 | 7.1E2 | 1.5E4 | 5.8E3 | 167 | 9 | 167 | 9 | 0.70 |
| dN | ug/mL | 9.8E1 | 1.4E2 | 1.0E2 | 1.6E2 | 4.0E1 | 6.9E1 | 2.4E1 | 9.4E1 | 2.8E2 | 3.3E2 | 167 | 9 | 167 | 9 | 0.81 |
| eD | pg/ml | 2.2E2 | 2.1E2 | 7.3E2 | 2.5E2 | 1.6E3 | 1.6E2 | 5.2E-1 | 5.9E1 | 8.3E3 | 4.9E2 | 90 | 7 | 90 | 7 | 0.50 |
| fR | ng/ml | 1.5E5 | 3.4E5 | 2.1E5 | 3.7E5 | 1.7E5 | 2.8E5 | 3.6E4 | 1.9E2 | 6.9E5 | 8.7E5 | 106 | 9 | 106 | 9 | 0.68 |
| hA | ng/ml | 2.5E0 | 5.4E0 | 1.4E1 | 2.3E1 | 5.0E1 | 4.1E1 | 1.7E-2 | 1.7E-2 | 3.5E2 | 1.1E2 | 91 | 7 | 91 | 7 | 0.65 |
| nM | pg/ml | 1.0E-9 | 1.0E-9 | 1.0E-9 | 2.2E0 | 0.0E0 | 5.8E2 | 1.0E-9 | 1.0E-9 | 1.0E-9 | 1.5E3 | 69 | 7 | 69 | 7 | 0.57 |
| nN | pg/ml | 1.4E3 | 2.4E3 | 4.1E3 | 2.9E4 | 1.3E4 | 5.7E4 | 8.1E1 | 4.1E2 | 1.0E5 | 1.5E5 | 69 | 7 | 69 | 7 | 0.61 |
| nO | pg/ml | 2.4E1 | 4.1E1 | 3.9E1 | 3.4E1 | 4.8E1 | 1.5E1 | 4.0E0 | 9.7E0 | 3.1E2 | 5.2E1 | 69 | 7 | 69 | 7 | 0.59 |
| nR | pg/ml | 1.6E1 | 7.1E1 | 6.8E1 | 4.3E2 | 1.7E2 | 7.0E2 | 1.0E0 | 1.1E1 | 1.1E3 | 1.9E3 | 69 | 7 | 69 | 7 | 0.77 |
| nT | pg/ml | 7.3E1 | 5.7E1 | 1.1E2 | 2.2E2 | 1.1E2 | 3.3E2 | 1.0E-9 | 1.0E-9 | 6.4E2 | 9.2E2 | 69 | 7 | 69 | 7 | 0.51 |
| nU | pg/ml | 4.4E1 | 1.2E2 | 8.7E1 | 2.9E2 | 2.0E2 | 3.4E2 | 1.0E-9 | 1.0E-9 | 1.5E3 | 9.2E2 | 69 | 7 | 69 | 7 | 0.69 |
| lW | pg/ml | 1.0E-9 | 1.0E-9 | 1.1E1 | 6.4E0 | 3.0E1 | 1.4E1 | 1.0E-9 | 1.0E-9 | 1.7E2 | 3.9E1 | 69 | 7 | 69 | 7 | 0.48 |
| lX | pg/ml | 9.0E2 | 9.2E2 | 9.6E2 | 1.3E3 | 5.5E2 | 7.4E2 | 1.9E2 | 4.8E2 | 2.6E3 | 2.5E3 | 69 | 7 | 69 | 7 | 0.64 |
| lY | pg/ml | 1.9E1 | 1.4E1 | 2.0E1 | 2.1E1 | 1.7E1 | 1.5E1 | 1.0E-9 | 3.1E0 | 1.2E2 | 4.5E1 | 69 | 7 | 69 | 7 | 0.52 |
| mE | pg/ml | 1.0E-9 | 1.0E-9 | 2.5E0 | 2.6E0 | 7.7E0 | 3.9E0 | 1.0E-9 | 1.0E-9 | 5.7E1 | 9.2E0 | 69 | 7 | 69 | 7 | 0.55 |
| mF | pg/ml | 2.7E-1 | 6.3E0 | 6.6E0 | 5.6E0 | 3.2E1 | 5.2E0 | 1.0E-9 | 1.0E-9 | 2.5E2 | 1.3E1 | 69 | 7 | 69 | 7 | 0.75 |
| mH | pg/ml | 3.0E0 | 5.3E0 | 5.4E0 | 4.7E0 | 8.1E0 | 3.3E0 | 4.0E-1 | 5.4E-1 | 5.3E1 | 1.0E1 | 69 | 7 | 69 | 7 | 0.57 |
| mI | pg/ml | 1.0E-9 | 3.4E0 | 1.2E1 | 8.4E1 | 2.6E1 | 1.7E2 | 1.0E-9 | 1.0E-9 | 1.8E2 | 4.6E2 | 69 | 7 | 69 | 7 | 0.65 |
| mM | pg/ml | 3.3E1 | 5.1E1 | 7.9E1 | 1.0E2 | 1.5E2 | 1.7E2 | 1.0E-9 | 1.0E-9 | 1.1E3 | 4.7E2 | 69 | 7 | 69 | 7 | 0.56 |
| mP | pg/ml | 1.5E1 | 1.6E1 | 1.7E1 | 1.5E2 | 1.6E1 | 2.9E2 | 1.0E-9 | 1.4E1 | 1.2E2 | 8.1E2 | 69 | 7 | 69 | 7 | 0.65 |
| mS | pg/ml | 1.6E3 | 2.0E3 | 1.7E3 | 2.1E3 | 1.0E3 | 1.0E3 | 1.0E-9 | 6.7E2 | 5.1E3 | 3.5E3 | 69 | 7 | 69 | 7 | 0.62 |
| mT | pg/ml | 5.3E1 | 1.4E2 | 1.2E2 | 4.6E2 | 2.2E2 | 6.4E2 | 1.0E1 | 1.6E1 | 1.4E3 | 1.7E3 | 68 | 7 | 68 | 7 | 0.67 |
| mU | pg/ml | 2.4E0 | 1.8E0 | 6.3E0 | 5.6E0 | 2.7E1 | 8.2E0 | 1.0E-9 | 6.1E-1 | 2.2E2 | 2.3E1 | 68 | 7 | 68 | 7 | 0.45 |
| mW | pg/ml | 2.1E3 | 1.9E3 | 2.4E3 | 4.8E3 | 1.2E3 | 4.8E3 | 1.0E-9 | 3.7E2 | 6.2E3 | 1.1E4 | 68 | 7 | 68 | 7 | 0.53 |
| mY | pg/ml | 6.5E2 | 6.5E2 | 8.8E2 | 1.7E3 | 9.6E2 | 2.8E3 | 1.0E-9 | 1.9E2 | 5.6E3 | 8.0E3 | 69 | 7 | 69 | 7 | 0.59 |
| mZ | pg/ml | 1.8E2 | 3.0E2 | 3.6E2 | 5.2E2 | 4.7E2 | 5.4E2 | 1.0E-9 | 6.6E1 | 3.1E3 | 1.4E3 | 68 | 7 | 68 | 7 | 0.59 |
| nA | pg/ml | 1.5E0 | 3.4E0 | 7.1E0 | 5.5E0 | 1.4E1 | 6.5E0 | 1.0E-9 | 1.0E-9 | 6.5E1 | 1.9E1 | 68 | 7 | 68 | 7 | 0.56 |
| nB | pg/ml | 3.0E2 | 2.8E2 | 3.1E2 | 3.5E2 | 1.6E2 | 3.0E2 | 3.0E1 | 1.3E2 | 8.2E2 | 9.6E2 | 69 | 7 | 69 | 7 | 0.44 |
| nC | pg/ml | 1.0E-9 | 7.0E2 | 9.6E3 | 2.2E3 | 5.3E4 | 3.1E3 | 1.0E-9 | 1.0E-9 | 3.8E5 | 7.2E3 | 69 | 7 | 69 | 7 | 0.71 |
| nD | pg/ml | 6.4E0 | 1.6E1 | 1.4E1 | 1.4E1 | 3.4E1 | 7.6E0 | 1.0E-9 | 1.0E-9 | 2.6E2 | 2.2E1 | 68 | 7 | 68 | 7 | 0.68 |
| nF | pg/ml | 1.0E-9 | 1.0E-9 | 3.2E0 | 1.9E0 | 1.3E1 | 5.1E0 | 1.0E-9 | 1.0E-9 | 9.3E1 | 1.3E1 | 69 | 7 | 69 | 7 | 0.52 |
| nH | pg/ml | 5.6E-1 | 1.1E1 | 2.0E2 | 3.2E1 | 1.2E3 | 4.4E1 | 1.0E-9 | 1.0E-9 | 1.0E4 | 1.2E2 | 68 | 7 | 68 | 7 | 0.70 |
| nI | pg/ml | 3.0E1 | 1.0E-9 | 7.2E1 | 2.3E1 | 1.6E2 | 3.9E1 | 1.0E-9 | 1.0E-9 | 1.2E3 | 8.0E1 | 69 | 7 | 69 | 7 | 0.40 |
| nJ | pg/ml | 1.7E-1 | 1.1E0 | 3.0E0 | 1.2E0 | 1.6E1 | 1.1E0 | 1.0E-9 | 1.0E-9 | 1.3E2 | 3.0E0 | 69 | 7 | 69 | 7 | 0.61 |
| nK | pg/ml | 1.0E-9 | 1.0E1 | 1.5E1 | 2.3E1 | 3.4E1 | 2.7E1 | 1.0E-9 | 1.0E-9 | 2.2E2 | 6.2E1 | 68 | 7 | 68 | 7 | 0.63 |
| nL | pg/ml | 1.0E-9 | 1.5E1 | 2.9E2 | 7.0E1 | 1.7E3 | 9.0E1 | 1.0E-9 | 1.0E-9 | 1.4E4 | 2.3E2 | 69 | 7 | 69 | 7 | 0.64 |
| hR | pg/ml | 2.8E4 | 1.8E4 | 3.0E4 | 2.0E4 | 1.2E4 | 6.0E3 | 1.0E-9 | 1.6E4 | 5.8E4 | 3.2E4 | 84 | 7 | 84 | 7 | 0.21 |
| hV | pg/ml | 4.4E2 | 4.3E2 | 4.5E2 | 4.0E2 | 2.3E2 | 2.3E2 | 1.0E-9 | 9.5E1 | 1.2E3 | 6.7E2 | 84 | 7 | 84 | 7 | 0.44 |

Figure 34 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| hW | pg/ml | 1.7E3 | 3.7E3 | 2.0E3 | 8.4E3 | 1.1E3 | 1.4E4 | 1.0E-9 | 1.5E3 | 7.3E3 | 4.0E4 | 84 | 7 | 84 | 7 | 0.79 |
| hX | pg/ml | 1.1E3 | 1.3E3 | 1.1E3 | 1.4E3 | 9.2E2 | 7.8E2 | 2.5E0 | 7.0E2 | 8.6E3 | 2.9E3 | 84 | 7 | 84 | 7 | 0.61 |
| iB | ng/ml | 4.9E0 | 1.4E1 | 6.2E0 | 1.2E1 | 4.7E0 | 6.4E0 | 3.3E-2 | 4.2E0 | 2.4E1 | 2.2E1 | 91 | 7 | 91 | 7 | 0.78 |
| iC | U/ml | 3.1E-1 | 7.0E-1 | 1.2E0 | 9.3E-1 | 5.8E0 | 8.6E-1 | 1.0E-9 | 1.5E-1 | 5.5E1 | 2.8E0 | 91 | 7 | 91 | 7 | 0.73 |
| jD | ng/ml | 3.1E1 | 5.3E1 | 4.0E1 | 1.6E2 | 4.0E1 | 1.9E2 | 1.0E-9 | 8.8E-1 | 1.9E2 | 5.1E2 | 91 | 7 | 91 | 7 | 0.72 |
| jE | ng/ml | 1.0E-9 | 1.8E1 | 5.0E0 | 1.5E1 | 1.2E1 | 1.5E1 | 1.0E-9 | 1.0E-9 | 6.2E1 | 3.5E1 | 91 | 7 | 91 | 7 | 0.69 |
| jF | ng/ml | 3.5E1 | 1.2E1 | 4.9E1 | 2.9E1 | 5.3E1 | 4.4E1 | 1.0E-9 | 1.0E-9 | 2.1E2 | 1.2E2 | 91 | 7 | 91 | 7 | 0.40 |
| jG | ng/ml | 4.4E3 | 4.2E3 | 4.5E3 | 4.8E3 | 2.0E3 | 1.4E3 | 6.7E2 | 3.6E3 | 9.6E3 | 7.3E3 | 91 | 7 | 91 | 7 | 0.57 |
| jH | ng/ml | 7.6E1 | 1.3E2 | 8.0E1 | 1.7E2 | 4.2E1 | 1.3E2 | 1.3E1 | 1.5E1 | 2.4E2 | 4.3E2 | 91 | 7 | 91 | 7 | 0.75 |
| jI | ng/ml | 7.3E1 | 2.1E2 | 7.6E1 | 2.1E2 | 3.1E1 | 1.2E2 | 1.9E1 | 5.8E1 | 1.9E2 | 4.4E2 | 91 | 7 | 91 | 7 | 0.89 |
| jK | ng/ml | 1.5E3 | 1.3E3 | 1.6E3 | 1.6E3 | 6.2E2 | 7.7E2 | 2.8E2 | 7.5E2 | 4.1E3 | 2.9E3 | 91 | 7 | 91 | 7 | 0.46 |
| jL | ng/ml | 2.0E2 | 4.0E2 | 2.7E2 | 3.7E2 | 2.0E2 | 2.0E2 | 5.6E1 | 1.2E2 | 9.6E2 | 6.3E2 | 91 | 7 | 91 | 7 | 0.66 |
| jM | ng/ml | 6.8E4 | 6.5E4 | 7.5E4 | 7.3E4 | 3.9E4 | 5.2E4 | 4.6E3 | 1.3E4 | 1.8E5 | 1.4E5 | 91 | 7 | 91 | 7 | 0.49 |
| jO | pg/ml | 2.2E5 | 2.7E5 | 2.7E5 | 3.3E5 | 1.7E5 | 1.6E5 | 6.0E4 | 1.8E5 | 1.1E6 | 6.5E5 | 91 | 7 | 91 | 7 | 0.64 |
| jP | pg/ml | 2.5E5 | 5.0E5 | 2.8E5 | 4.4E5 | 1.4E5 | 1.7E5 | 3.6E4 | 1.6E5 | 7.1E5 | 5.8E5 | 91 | 7 | 91 | 7 | 0.77 |
| jQ | pg/ml | 2.2E3 | 2.9E3 | 3.1E3 | 3.6E3 | 2.9E3 | 2.9E3 | 5.0E0 | 9.2E2 | 1.3E4 | 9.2E3 | 91 | 7 | 91 | 7 | 0.58 |
| jR | pg/ml | 5.6E3 | 8.9E3 | 9.8E3 | 1.5E4 | 1.2E4 | 1.6E4 | 1.0E-9 | 1.0E3 | 6.8E4 | 4.6E4 | 91 | 7 | 91 | 7 | 0.60 |
| jT | pg/ml | 1.7E5 | 1.6E5 | 1.8E5 | 1.7E5 | 7.2E4 | 5.0E4 | 7.1E4 | 1.1E5 | 5.5E5 | 2.5E5 | 91 | 7 | 91 | 7 | 0.50 |
| jU | mIU/ml | 5.4E0 | 6.7E0 | 1.2E1 | 8.0E0 | 1.9E1 | 7.3E0 | 8.1E-2 | 1.2E0 | 1.1E2 | 1.8E1 | 91 | 7 | 91 | 7 | 0.49 |
| jV | mIU/ml | 1.9E0 | 1.1E0 | 4.1E0 | 2.0E0 | 5.7E0 | 2.3E0 | 2.7E-3 | 3.0E-1 | 3.2E1 | 6.6E0 | 91 | 7 | 91 | 7 | 0.40 |
| jY | ng/ml | 9.7E-4 | 3.1E-3 | 7.7E-3 | 6.2E-3 | 3.3E-2 | 9.4E-3 | 1.0E-9 | 1.0E-9 | 3.0E-1 | 2.6E-2 | 91 | 7 | 91 | 7 | 0.60 |
| kC | pg/ml | 9.6E1 | 1.1E2 | 1.9E2 | 1.1E2 | 3.6E2 | 3.8E1 | 2.1E1 | 5.9E1 | 2.7E3 | 1.6E2 | 69 | 7 | 69 | 7 | 0.50 |
| kE | pg/ml | 1.4E5 | 1.2E5 | 1.4E5 | 1.2E5 | 4.0E4 | 4.5E4 | 4.1E4 | 3.8E4 | 2.7E5 | 1.9E5 | 69 | 7 | 69 | 7 | 0.42 |
| kF | pg/mL | 6.4E1 | 7.6E1 | 6.7E1 | 8.5E1 | 2.3E1 | 3.9E1 | 2.7E1 | 5.1E1 | 1.5E2 | 1.4E2 | 69 | 7 | 69 | 7 | 0.61 |
| kG | pg/mL | 8.2E3 | 1.6E4 | 1.1E4 | 4.5E4 | 9.6E3 | 5.5E4 | 1.1E3 | 3.3E3 | 5.8E4 | 1.6E5 | 69 | 7 | 69 | 7 | 0.78 |
| kI | pg/ml | 2.0E2 | 1.5E2 | 2.1E2 | 2.2E2 | 1.1E2 | 1.6E2 | 1.0E-9 | 7.2E1 | 6.7E2 | 5.5E2 | 69 | 7 | 69 | 7 | 0.45 |
| kK | pg/ml | 1.2E2 | 1.1E2 | 1.9E2 | 1.2E2 | 2.6E2 | 5.6E1 | 6.4E0 | 3.4E1 | 1.9E3 | 2.1E2 | 69 | 7 | 69 | 7 | 0.46 |
| kN | pg/ml | 1.1E3 | 1.1E3 | 1.5E3 | 2.1E3 | 1.6E3 | 2.9E3 | 7.3E1 | 7.0E2 | 1.0E4 | 8.7E3 | 69 | 7 | 69 | 7 | 0.55 |
| kO | pg/ml | 7.2E3 | 6.2E3 | 9.7E3 | 7.0E3 | 1.7E4 | 2.3E3 | 3.7E3 | 5.0E3 | 1.5E5 | 1.2E4 | 69 | 7 | 69 | 7 | 0.44 |
| kP | pg/ml | 5.6E3 | 5.4E3 | 6.7E3 | 6.8E3 | 4.3E3 | 4.6E3 | 9.6E2 | 1.6E3 | 2.7E4 | 1.5E4 | 69 | 7 | 69 | 7 | 0.51 |
| lK | pg/ml | 6.6E1 | 3.2E1 | 1.4E2 | 9.5E1 | 1.7E2 | 1.7E2 | 1.0E-9 | 7.4E2 | 4.8E2 | | 90 | 7 | 90 | 7 | 0.32 |
| lL | pg/ml | 1.7E3 | 2.7E3 | 2.9E3 | 3.1E3 | 4.9E3 | 2.5E3 | 7.5E1 | 5.3E2 | 4.2E4 | 6.8E3 | 91 | 7 | 91 | 7 | 0.59 |
| lM | pg/ml | 1.2E3 | 3.1E3 | 3.8E3 | 1.7E4 | 6.3E3 | 2.6E4 | 2.1E2 | 9.5E0 | 4.2E4 | 6.7E4 | 91 | 7 | 91 | 7 | 0.68 |
| lN | pg/ml | 1.0E-9 | 1.0E-9 | 3.3E0 | 3.6E0 | 6.8E0 | 7.1E0 | 1.0E-9 | 1.0E-9 | 4.3E1 | 1.9E1 | 91 | 7 | 91 | 7 | 0.52 |
| lO | pg/ml | 1.0E-9 | 1.0E-9 | 1.8E0 | 2.0E1 | 1.4E1 | 5.2E1 | 1.0E-9 | 1.0E-9 | 1.3E2 | 1.4E2 | 90 | 7 | 90 | 7 | 0.56 |
| oO | pg/ml | 9.0E4 | 5.4E4 | 1.0E5 | 1.5E5 | 6.2E4 | 1.5E5 | 3.3E3 | 3.8E4 | 3.0E5 | 4.0E5 | 62 | 7 | 62 | 7 | 0.44 |
| oP | pg/ml | 1.3E5 | 2.0E5 | 1.4E5 | 2.4E5 | 8.8E4 | 1.7E5 | 2.4E4 | 5.0E4 | 4.2E5 | 5.7E5 | 62 | 7 | 62 | 7 | 0.72 |
| oQ | pg/ml | 3.0E3 | 4.0E3 | 3.6E3 | 9.7E3 | 3.0E3 | 1.1E4 | 7.7E2 | 1.9E3 | 2.1E4 | 3.2E4 | 62 | 7 | 62 | 7 | 0.64 |

Analyte panel data:

Unconstrained panels with 3 analytes, where 1.0E-8 >= 'model p-value' > 0. Contains 13,657 panels of 645,860 total panels evaluated. :
Fr{Et(aA Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) No(aA Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nt(aA Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nu Nv Nw Nx Ny Oe Of Og Oh Oi Ok Om On Oy Oz Pa Pb Pc Pd Pe Pf Pg Po Pz Qa Qb Qc Qd Qe) Lv(aA Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nu Nv Nw Nx Ny Oe Of Og Oh Oi Ok Om On Oy Oz Pa Pb Pc Pd Pe Pf Pg Po Pz Qa Qb Qc Qd Qe) Mz(aA Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Na Nb Nc Nd Ne Nf Ng Nh Ni Nj Nk Nl Nm Nn Nq Nr Ns Nu Nv Nw Nx Ny Oe Of Og Oh Oi Ok Om On Oy Oz Pa Pb Pc Pd Pe Pf Pg Po Pz Qa Qb Qc Qd Qe) Na(aA Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Nb Nc Nd Ne Nf Ng Nh Ni Nj Nk Nl Nm Nn Nq Nr Ns Nu Nv Nw Nx Ny Oe Of Og Oh Oi Ok Om On Oy Oz Pa Pb Pc Pd Pe Pf Pg Po Pz Qa Qb Qc Qd Qe) Hw(aA Fp Hq Hr Hu Hv Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt

Oy Oz Pa Pb Pc Pd Pe Pf Pg Po Pz Qa Qb Qc Qd Qe) Jr(Fp Hq Hr Hu Hv Hw Hx Ih Ii Ij Ik Il Im In Io Ip Iq Ir Is It Iu Iv Jg Jh Jj Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Lv(Fp Hq Hr Hu Hv Hw Hx Ih Ii Ij Il Im In Io Ip Ir Is It Iu Iv Jg Jh Jj Jk Jn Jo Jp Jq Js Jt Lh Li Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Nf Ng Ni Nj Nk Nl Nm Nr Ns Nt Nu Nv Nw Nx Ny Oe Of Og Oh Oi Ok Om Oy Oz Pa Pb Pc Pd Pe Pg Po Pz Qa Qb Qc Qd Qe) Lh(Hq Hu Hv Hw Hx Ih Ii Ik Il Im In Io Ip Ir Is Iv Jg Jh Jj Jk Jm Jn Jo Jp Jq Jt Li Lj Lu Lw Ly Lz Ma Md Me Mf Mg Mh Mi Mj Mk Ml Mm Mn Mp Ms Mt Mu Mv Mw Mx My Mz Na Nb Nc Nd Ne Nf Ng Nh Ni Nj Nk Nq Ns Nt Nu Nv Nw Ny Oe Of Og Oi Ok Om Oy Oz Pa Pb Pc Pe Pg Po Pz Qa Qb Qc Qd Qe) Pe(Hu Hw Im In Io Ip Ir Is Iv Jh Jj Jn Jo Jp Jq Li Lw Ma Mc Mf Mh Mk Ml Mm Ms Mt Mu Mx My Mz Ng Ni Nj Nt Nw Og Oi Ok Oy Pb Pc Pg Qa Qd) Is(Hu Hw In Io Ip Jj Jo Jp Jq Lu Lx Ma Mf Ms Mt Mu Mz Ne Ng Ni Nj Nw Og Oi Ok Om Pa Pc Pg Pz Qc) Nt(Hu Hv Hw Hx In Io Ip Ir Jj Jn Jo Jp Jq Lw Ma Mf Ms Mt Mu Mz Ne Ng Ni Nj Nw Og Oi Ok Om Pb Pc Pg Qa Qd) Jq(Hu Hw Hx Il Im Ip Iu Iv Jj Jn Jo Jp Lx Ma Mi Mm Mp Mr Ms Mt Mu Mx Nd Nj Nr Og Oi Ok Oz Pa Pg Po) Hu(Hw Hx Ii In Ip Ir Jh Jk Jn Jo Jp Jt Lu Lx Mr Mt Mu Mz Nb Nq Nv Nw Nx Oi Ok Om Pa Pg Po Qa) Pg(Hv Hw Im In Io Ip Ir Jj Jn Jo Jt Mr Ms Mu My Mz Na Ng Ni Ns Og Oi Ok Oy Pa Pb Pc Qa) Jn(Hw Io Ip Jj Jo Js Lu Lx Ma Mi Mp Mr Ms Mu Nd Og Oi Ok Pa) Ok(Hw Hx Il Ip Jp Lx Ma Mi Mp Mr Ms Mt Mu Nd Og Oi Pa) Mr(Ip Jj Jp Lw Ma Ms Mt Ni Nj Og Oi Pc Qa Qd) Ip(Hw Hx Jj Jo Lx Mi Mz Nb Nr Oi Pa Po Qa) Pa(Hv Hw Jo Mk Ms Mt Mz Na Ni Nj Oi Qa) Jo(Jj Jp Ms Mt Nw Og Oi Pb) Hw(Jp Lx Mt Nj Nw Oi) Oy(Jh Mw Nb Om Po) Og(Hx Nb Om) Ms(Nb Om) Qa(Lx Mi) Jj(Il Jk) Oi(Ir Mt) MwMy} Jr{Mm(Fp Hq Hr Hu Hv Hw Hx Ih Ii Ij Ik Il Im In Io Ip Iq Ir Is It Iu Iv Jg Jh Jj Jk Jm Jn Jo Jp Jq Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nw Ny Oe Of Og Oh Oi Ok Om Oy Oz Pa Pb Pc Pd Pe Pf Pg Po Pz Qa Qb Qc Qd Qe) Nq(Hr Hu Hv Hw Hx Ii Ij Ik Im In Io Ip Ir Is It Iv Jg Jh Jj Jk Jm Jn Jo Jp Jq Js Jt Lh Li Lu Lv Lw Ly Ma Mb Me Mg Mh Mi Mj Mk Ml Mp Mr Ms Mt Mu Mv Mw My Mz Na Nb Nc Ne Nf Ng Nh Ni Nj Nk Nm No Nr Ns Nt Nu Nw Ny Oe Of Og Oh Oi Ok Om Oy Oz Pa Pb Pc Pe Pg Pz Qa Qc Qd) Lh(Fp Hr Hx Ii Ik Im In Io Ip Is It Jg Jh Jj Jo Jp Jq Lj Lv Lw Ly Ma Md Mg Mh Mi Mj Ml Mp Ms Mt Mu My Ne Ng Ni Nj No Ns Nw Ny Oe Of Og Oh Oi Om Oy Pb Pc Pg Po Qc) Mu(Hr Hw Hx Ik Im In Io Ip Is It Iu Jj Jo Jp Jq Js Jt Lu Lv Lw Lx Ma Mg Mh Mi Ml Mp Mr Ms Mt Mz Nd Ng Nj No Nr Ns Nt Nu Nw Og Oh Oi Ok Pa Pb Pc Pe Pg Qc) No(Hr Ii Im In Io Ip Is Jg Jh Jj Jk Jo Jp Jq Jt Lj Lu Lv Lw Ma Mb Mf Mg Mh Mi Mj Ml Mn Mp Mt My Nj Nm Ns Nt Nu Og Oh Ok Om Oz Pb Pc Pg Qc) Pc(Hw Im Io Ip Is Jj Jk Jo Jp Jq Lu Lv Lx Ma Mg Mi Mp Mr Ms Mt Mz Nd Ns Nt Og Ok Om Pa Pe Pg) Ip(Hw Io Jg Jj Jk Jo Jp Jq Lu Lv Lw Lx Ma Mg Mi Mp Mr Mt Nb Nt Nv Og Ok Om Pa Pe Pg Qc) Mp(Hq In Io Jg Jh Jj Jk Jp Jq Lv Ma Mg Mr Mt Mz Ni Nj Ns Nt Nw Ok Om Pa Pd Pe Pg) Mi(In Io Jg Jh Jj Jp Jq Lv Lw Ma Mg Mh Ml Ms Mt Ni Nj Og Ok Om Pg) Nt(In Io It Jj Jp Jq Lv Lw Ma Mg Ml Mt Ne Nj Nw Og Om) Lv(Io Jj Jk Lu Lx Ma Mg Mr Mt Oh Ok Om Pa Pe Pg) Mg(In Jj Lu Mr Ms Ng Og Ok Pa Pc Pg) Ma(Jj Jk Jq Lx Mb Mr Pa Pe Pg) Pg(Ii Io Jj Jq Lw Og Ok Pb) Jj(Jk Jo Lx Nv Om) Og(Jg Jk Mw Nb Om) Lw(Lu Pa) Ms(Jg Om) Mw(My Oy) JhOy JqPa} Lv{No(Fp Hq Hr Hu Hv Hw Hx Ih Ii Ij Ik Il Im In Io Ip Iq Ir Is It Iu Iv Jg Jh Jj Jk Jm Jn Jo Jp Jq Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Mu(Fp Hq Hr Hu Hv Hw Hx Ih Ii Ij Ik Il Im In Io Ip Ir Is It Iu Iv Jg Jh Jj Jm Jn Jo Jp Jq Js Jt Lh Li Lj Lu Lw Lx Ly Lz Ma Mb Md Me Mf Mg Mh Mi Mj Mk Ml Mm Mn Mp Mq Mr Ms Mt Mw Mx My Mz Na Nb Nc Nd Ne Nf Ng Nh Ni Nj Nk Nl Nm Nq Nr Ns Nt Nu Nv Nw Nx Ny Oe Of Og Oh Oi Ok Om Oy Oz Pa Pb Pc Pd Pe Pg Po Pz Qa Qb Qc Qd Qe) Mm(Hw Hx Io Ip Ir Is Jn Jq Lh Lu Lx Mi Mr Mt Mz Nb Nf Nr Nt Nw Ok Om Pa Pe Pg Po Qa) Mt(Hw Io Ip Is Iu Jj Jo Lh Mi Mr My Nq Nt Ny Og Pa Pb Pe) Lh(Io Ip Is Jj Jn Jo Jp Jq Lw Mg Mz Nj Nw Og Oh Pb Pc) Nt(Io Ip Jj Jn Jp Jq Mz Nf Nj Nw Oh Pc) Mi(Io Ip Is Jj Jn Jp Jq Mz Nj Om) Jj(Ip Jk Jo Mr Nq Om Pa Pg) Jq(Ip Lx Mp Mr Nq Pa Pc Pe) Mz(Ip Mg Mp Nq Pa Pc Pg) Mr(Ip Lw Mg Oh Pc) Pa(Io Ip Jn Oh Pc) Og(Jg Mw Nb Om) Nq(Hu Jn Ok) Io(Is Jn Nw) Pe(Ip Oh Pc) Mw(My Oy) HwIp JnPc} Jq{Lh(Hx Ii Io Ip Is Jj Jn Jp Ma Md Mh Ml Mm Mp Ms Mt Mu My Nj Ny Og Oy Pb Pc) Mp(Hq Ip Is Jg Jp Ma Mm Mr Mt Mu Nj No Ns Nt Pa Pc Pd Pe) Pa(Hx Ii Ip Ma Md Mh Mk Ml Mm Mt Mu Nj Nq Ny Og Pb Pc) Nt(Ii Io Ip It Jj Jp Ma Ml Mm Mt Mu Nj Nq Og Pc) Mm(Il Ip Is Lx Ma Mi Mr Mt Mu No Nq Pe Pg) Ip(Hw Jk Lx Mi Mr Mt Mu No Nq Pc Pe Pg) Nq(Hu Jj Ms My Nj No Og Oy Pe) Mi(Jp Ma Ml Mt Mu Nj Pc) Pc(Lx Mr Mt No Pe Pg) No(Ma Mg Mu Nj) Mw(My Og Oy) Pg(Ii Jj Pb) Ma(Mr Pe) Mu(Nj Og) MlPe JgOg} No{Pc(Hv Hw Hx Ij Im In Io Ip Is Iv Jj Jn Jo Jp Lh Ma Mg Mi Mm Mt Mu Mz Na Nf Ni Nj Oi Ok Om Pe Pg Qa) Ip(Is Jg Jj Jk Jn Jt Lw Ma Mb Mg Mi Mm Mp Mt Mu Mz Nj Nq Oh Ok Om Oz Pb Pg Qa) Mm(Hv Hw Ij In Io Is Jn Jo Lh Ma Mt Mu Mz Ni Nj Om Pe Pg Qa) Is(Ii Io Jj Lw Ma Mg Mp Mu Nj Nq Og) Mu(Jj Jn Lw Ma Mp Nj Ok Pb) Jj(Jk Jn Mg Nq Pg) Jn(Ma Mg Mp Nq) Mw(My Og Oy) Nj(Mg Mp Nq) Om(Mp Og Pb) Ng(Jg Mg) NqHu JgOg} Lh{Ip(Ii Is Jj Jn Jo Mm Ms Mt Mu Og Pb Pc) Mu(Is Jj Jn Mm Ms Ng Nj Og Oy Pb) Pb(Is Jn Ma Mm Mp Mt Om Pc Pg) Jj(Is Jk Jn Ma Mt Nq Pc Pg) Og(Is Jg Jh Jn Mm Mw Om Pc) Is(Ii Io Mm Ms Pc) My(Jh Mv Mw Om) Oy(Jh Mw Nq Om) Mm(Io Jn Ng) Pc(Jn Ms Mt) Ng(Jg Mg) MaJn IiPg} Pg{Jj(Hq Hw Ik Im Io Ip Ir Is Iu Iv Jg Jh Jk Jn Jo Jp Jt Lw Ma Mb Mg Mi Mm Mp Mt Mu My Mz Nf Nj Nq Nt Nu Og Oh Ok Om Oy Oz Pb Pc Qa Qe) Mm(Io Is Jn Mz Ng Oy) Oy(Jg Jh Mu Mw Om) Mu(Ng Og Pb) My(Mv Mw) Mz(Pb Pc) Jg(Ng Og) IoIs OkPb} Mu{Is(Ik Io Ip Jj Mi Mm Mp Ms Ng Nj Nt Og Oi Pb Pc Pz) Ip(Jj Mi Mz Nj Nt Og Ok Pb) Og(Hx Mi Nb Nt Ok Om) Nj(Jn Mi Mz Nt Ok) Jj(Jn Jo Nt Pe) Pb(Mi Nt Ok Pe) Ng(Mi Nt Pa) Mm(Jn Mz) NqHu MkPa MwOy} Og{Om(Hx Ip Is Mi Mt Nb Nq Nt Nv Pa Pc) Mw(Ip Ir Is Jn Mz Ok Qd) Is(Jg Mg Nq Pc) Jg(Hx Ip Nb) NqJn NbIp} Nq{Hu(Ip Ir Is Jn Mz Ok Om Qa) Jn(Jj Ms Ng Oy) Ip(Jj Mz Ok) Oy(Nb Om Po) Is(Jj Ms) MyOm NgJg} Mw{My(Ip Ir Is Jn Lx Mt Mz Nw Pe) Oy(Ip Is Jk Lx Nv Pb Pe) MsIs HuPb} Nt{Ip(Jj Mt Mz Pc) Jj(Is Jk Jn) Mm(Jn Mz) Io(Is Jp) Pc(Jn Mz)} Is{Io(Lw Mi Mm Mp Pc) Ms(Jg Pc) LuLw MmMz OiPc} Mm{Jn(Io Ip Mr Pe) MzIp IoPe} Oy{Jh(Lx Mi Pa Po) MiOm MtJk} My{Mi(Jh Om) MtJg MvNb} Jj{Jk(Ip Jo Ma)} MiNgOm MpMzIp MtHwPb

Unconstrained panels with 3 analytes, where 1.0E-7 >= 'model p-value' > 1.0E-8. Contains 29,252 panels of 645,860 total panels evaluated. :
On{Qb(Et Fp Hq Hr Hv Hw Hx Ih Ii Ij Ik Il Im In Iq Ir Is It Iu Iv Jg Jh Jk Jm Jn Jo Jp Js Jt Lh Li Lj Lu Lw Lx Ly Lz Ma Mb Mc Md Me Mf Mg Mh Mi Mj Mk Ml Mn Mp Mq Mr Mt Mu Mv Mw Mx Mz Na Nb Nc Nd Ne Nf Nh Ni Nj Nk Nl Nm Nq Nr Ns Nt Nu Nv Nw Nx Ny Oe Oh Oi Ok Om Oz Pa Pb Pc Pd Pe Pf Pg Po Qa Qc Qd Qe) Jp(Et Fp Hq Hr Hv Hw Hx Ih Ii Ij Ik Il Im In Iq Ir Is It Iu Iv Jg Jh Ji Jk Jm Jn Jo Js Jt Lh Li Lj Lu Lw Lx Ly Lz Ma Mb Mc Md Me Mf Mg Mh Mi Mj Mk Ml Mn Mp Mq Mr Mt Mu Mv Mw Mx Mz Na Nb Nc Nd Ne Nf Nh Ni Nj Nk Nl Nm Nq Nr Nt Nu Nv Nw Nx Ny Oe Oh Oi Ok Om Oz Pa Pb Pc Pd Pe Pf Pg Po Qa Qc Qd Qe) It(Et Fp Hq Hr Hv Hw Hx Ih Ii Ij Ik Il Im In Iq Ir Is Iu Iv Jg Jh Jk Jm Jn Jo Js Jt Lh Li Lj Lu Lw Lx Ly Lz Ma Mb Mc Md Me Mf Mg Mh Mi Mj Mk Ml Mn Mp Mq Mr Mt Mu Mv Mw Mx Mz Na Nb Nc Nd Ne Nf Nh Ni Nj Nk Nl Nm Nq Nr Nt Nu Nv Nw Nx Ny Oe Oh Oi Ok Om Oz Pa Pb Pc Pd Pe Pf Pg Po Qa Qc Qd Qe) Jh(Fp Hq Hr Hv Hw Hx Ih Ii Ij Ik Il Im In Iq Ir Is Iu Iv Jg Ji Jk Jm Jn Jo Js Jt Lh Li Lj Lu Lv Lw Lx Ly Lz Ma Mb Mc Md Me Mf Mg Mh Mi Mj Mk Ml Mn Mp Mq Mr Mt Mu Mv Mw Mx Mz Na Nb Nc Nd Ne Nf Nh Ni Nj Nk Nl Nm Nq Nr Nt Nu Nv Nw Nx Ny Oe Oh Oi Ok Om Oz Pa Pb Pc Pd Pe

Mu Mv Mw Mz Na Nd Ni Nk Nm Nq Nt Nx Ny Oe Oh Ok Pa Pd Pe Pg Qa Qc Qd) Nk(Hq Hv Hw Hx Ik In Ir Is Iu Iv Jn Jo Jt Lh Lu Lw Lx Ly Ma Mg Mh Mi Mk Ml Mp Mr Mt Mu Mv Mw Mz Na Nd Nj Nm Nq Nt Nx Ny Oe Oh Ok Pa Pc Pd Pe Pg Qa Qc Qd) Qd(Hq Hv Hw Hx Ii In Ir Is Iu Iv Ji Jn Jo Jt Lh Lu Lw Lx Ly Ma Mg Mh Mi Mk Ml Mp Mr Mt Mv Mw Mz Na Nd Ni Nj Nm Nq Nt Nx Ny Oe Oh Ok Pa Pc Pd Pe Pg Qa) Ok(Hq Hv Hw Hx Ii Ik In Ir Is Iu Iv Jn Jo Lh Lu Lw Lx Ly Ma Mg Mh Mi Mk Ml Mp Mr Mt Mv Mw Mz Na Nd Ni Nj Nm Nq Nt Nx Ny Oe Oh Pa Pc Pd Pe Pg Qa Qc) Pd(Hq Hv Hw Hx Ik In Ir Is Iu Iv Jn Jo Jt Lh Lu Lw Lx Ly Ma Mg Mh Mi Mk Ml Mr Mt Mu Mv Mw Mz Na Nd Ni Nj Nm Nq Nt Nx Ny Oe Oh Pa Pc Pe Pg Qa Qc) Nd(Hv Hw Hx Ii Ik In Ir Is Iu Iv Jn Jo Jt Lh Lu Lw Lx Ly Ma Mg Mh Mi Ml Mp Mr Mt Mu Mv Mw Mz Na Nj Nm Nq Nt Nx Ny Oe Oh Pa Pc Pe Pg Qa Qc) Iv(Hq Hv Hw Hx Ik In Ir Is Iu Jn Jo Jt Lh Lu Lw Lx Ly Ma Mg Mh Mi Mk Ml Mp Mr Mt Mv Mw Mz Na Ni Nj Nm Nq Nt Nx Ny Oe Oh Pa Pe Pg Qa Qc) Ny(Hq Hv Hw Hx Ii Ik Ir Is Iu Jn Jo Jt Lu Lw Lx Ly Ma Mg Mh Mi Mk Ml Mp Mr Mt Mv Mw Mw Na Ni Nj Nm Nq Nt Nx Ny Oe Oh Pa Pb Pc Pe Pg Qa Qc) Nq(Hq Hv Hw Hx Ii Ik In Ir Is Iu Jo Jt Lh Lu Lw Lx Ly Ma Mg Mh Mi Mk Ml Mp Mr Mt Mv Mw Na Ni Nj Nm Nt Nx Oe Oh Pa Pc Pe Pg Qa Qc) Lu(Hq Hv Hw Hx Ii Ik In Ir Is Iu Jn Jo Jt Lh Lx Ly Ma Mg Mh Mi Mk Ml Mp Mr Mt Mv Na Ni Nj Nm Nt Nx Oh Pa Pe Pg Qa Qc) Ly(Hq Hv Hw Hx Ii Ik In Ir Is Iu Jn Jo Jt Lw Ma Mg Mh Mk Ml Mp Mr Mt Mu Mv Mw Mz Na Ni Nj Nm Nx Oe Oh Pa Pc Pe Pg Qa Qc) Ml(Hq Hv Hx Ii Ik Ir Is Iu Jo Jt Lw Lx Ma Mg Mh Mi Mk Mp Mr Mt Mu Mv Mw Na Ni Nj Nm Nt Nx Oe Oh Pa Pb Pc Pe Pg Qa Qc) Mr(Hq Hv Hw Hx Ik In Ir Is Iu Jn Jo Jt Lh Lw Lx Mg Mi Mk Mp Mt Mu Mv Mw Mz Na Ni Nj Nm Nt Nx Oe Oh Pa Pe Pg Qa Qc) Mv(Hq Hv Hw Hx Ii Ik In Ir Is Iu Jn Jo Jt Lh Lw Lx Mh Mi Mk Mp Mt Mw Mz Na Ni Nm Nt Nx Oe Oh Pa Pc Pe Pg Qa Qc) Hq(Hv Hw Hx Ii Ik In Ir Is Iu Jn Jo Jt Lh Lw Ma Mg Mh Mi Mk Mt Mw Mz Na Ni Nj Nm Nt Nx Oh Pa Pc Pe Pg Qa Qc) Hx(Hv Hw Ii Ik In Ir Is Iu Jn Jo Jt Lw Lx Ma Mg Mh Mi Mk Mp Mt Mw Na Ni Nj Nm Nt Nx Oe Oh Pc Pe Pg Qa Qc) Pg(Hv Hw In Ir Is Iu Jn Jo Jt Lh Lw Lx Ma Mg Mh Mi Mk Mt Mu Mz Na Ni Nj Nm Nt Nx Oe Oh Pa Pc Pe Qa Qc) Iu(Hv Hw Ik In Ir Is Jn Jo Lh Lw Lx Ma Mg Mh Mi Mk Mp Mt Mw Na Nj Nm Nt Nx Oe Oh Pa Pc Pe Qa Qc) Ir(Hv Hw Ik In Is Ji Jn Jo Lh Lw Lx Mg Mh Mi Mk Mt Mw Mz Na Ni Nm Nt Nx Oe Oh Pa Pe Qa Qc) Qc(Hv Hw Ii Ik In Jo Jt Lh Lw Lx Ma Mg Mh Mi Mk Mp Mu Na Ni Nj Nm Nt Nx Oe Pa Pc Pe Qa) Mt(Hv Hw Ii Ik In Is Jn Jo Jt Lh Lw Lx Ma Mg Mi Mk Mp Mu Mz Na Nx Oe Oh Pa Pe Qa) Pa(Hv Hw Ik In Is Jn Jo Jt Lh Lw Lx Ma Mg Mi Mp Mu Mw Mz Na Nm Nt Nx Oe Oh Pe Qa) Mk(Hv Hw Ii Ik In Is Jn Jo Jt Lw Ma Mg Mh Mi Mw Mz Na Ni Nm Nx Oe Oh Pb Pc Qa) Pe(Hv Hw In Is Jn Jo Jt Lh Lw Lx Mg Mi Mp Mu Mw Mz Na Ni Nj Nm Nt Nx Oe Oh Qa) Lx(Hv Hw Ik In Is Jo Jt Lh Mg Mh Mi Mp Mu Mw Mz Na Nm Nt Nx Oe Oh Qa) Mh(Hv Hw Ik In Is Jo Jt Lw Ma Mg Mp Mw Na Nj Nt Nx Oe Oh Pc Qa) Na(Hv Hw Ik In Is Jn Jo Lh Lw Mg Mi Mw Mz Ni Nt Nx Oe Oh Qa) Nx(Hv Hw Ii Ik In Jo Jt Lh Lw Mg Mi Mp Mw Mz Nm Oh Pc Qa) Hv(Hw Ik In Is Ji Jn Lh Lw Mg Mw Mz Ni Nt Oe Oh Qa) Mw(Hw Ii Ik Jo Jt Lw Mi Mp Mz Nm Nt Oe Oh Qa) In(Ik Is Jo Lw Mg Mi Mu Mz Ni Nm Oe Oh Qa) Ik(Hw Ii Jt Lw Mi Mz Nm Oe Oh Pc Qa) Qa(Hw Is Ji Jn Lh Lw Mg Mz Ni Nt) Lw(Hw Jo Mg Mi Mp Nj Oh Pc) Mz(Hw Is Ji Jn Jo Lh Ni Oh) Mi(Jo Lh Mg Mp Nt Oe Oh) Mg(Hw Is Jt Oe Oh) Mp(Jo Nt Oe Oh Pc) Jo(Is Jn Oe Oh) Hw(Lh Ni Nt) NtLh MaJt IsJn OhPc} Jl{Lx(Fp Hq Hr Hu Hv Hw Hx Ih Ii Ij Ik Il Im In Ip Iq Ir Is It Iu Iv Jg Jh Jk Jm Jn Jo Jp Js Jt Lh Li Lj Lu Ly Lz Ma Mb Mc Md Me Mf Mg Mh Mi Mj Mk Ml Mn Mp Mq Mr Ms Mt Mv Mw Mx My Mz Na Nb Nc Nd Ne Nf Ng Nh Ni Nj Nk Nl Nm No Nq Nr Ns Nt Nu Nv Nw Nx Ny Oe Of Oh Oi Ok Om Oy Oz Pa Pb Pd Pe Pf Pg Po Pz Qa Qc Qd Qe) Oe(Fp Hq Hr Hu Hv Hw Hx Ih Ii Ij Ik Il Im In Io Ip Iq Ir Is It Iu Iv Jg Jh Jk Jm Jn Jo Jp Js Jt Lh Li Lj Lu Ly Lz Ma Mb Mc Md Me Mf Mh Mi Mj Mk Ml Mn Mp Mq Mr Ms Mt Mv Mw Mx My Mz Na Nb Nc Nd Ne Nf Ng Nh Ni Nj Nk Nl Nm Nq Nr Ns Nt Nu Nv Nw Nx Ny Of Oh Oi Ok Om Oy Oz Pa Pb Pd Pe Pf Pg Po Pz Qa Qb Qc Qd Qe) Lu(Fp Hq Hr Hu Hv Hw Hx Ih Ii Ij Ik Il Im In Iq Ir Is It Iu Iv Jg Jh Jk Jm Jo Jp Js Jt Lh Li Lj Ly Lz Ma Mb Mc Md Me Mf Mh Mi Mj Mk Ml Mn Mp Mq Mr Ms Mt Mv Mw Mx My Mz Na Nb Nc Nd Ne Nf Ng Nh Ni Nj Nk Nl Nm No Nq Nr Ns Nt Nu Nv Nw Nx Ny Of Oh Oi Ok Om Oy Oz Pa Pd Pe Pf Pg Po Pz Qa Qb Qc Qd Qe) Md(Fp Hq Hr Hu Hv Hw Hx Ih Ij Ik Il Im In Iq Ir Is It Iu Iv Jg Jh Jk Jm Jn Jo Jp Js Jt Lh Li Lj Ly Lz Ma Mb Mc Me Mf Mh Mi Mj Mk Ml Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Of Oh Oi Ok Om Oy Pa Pd Pe Pf Pg Po Pz Qa Qb Qc Qd Qe) Pg(Fp Hq Hr Hu Hv Hw Hx Ih Ij Ik Il Im In Iq Ir Is It Iu Iv Jg Jh Jk Jm Jn Jo Jp Js Jt Lh Li Lj Lv Ly Lz Ma Mb Mc Me Mf Mg Mh Mi Mj Mk Ml Mn Mq Mr Ms Mt Mv Mw Mx My Mz Na Nb Nc Nd Ne Nf Ng Nh Ni Nj Nk Nl Nm No Nq Nr Ns Nt Nu Nv Nw Nx Ny Of Oh Oi Ok Om Oy Pa Pd Pe Pf Po Pz Qa Qb Qc Qd Qe) Nm(Fp Hq Hr Hu Hv Hw Hx Ih Ij Ik Il Im In Iq Ir Is It Iu Iv Jg Jh Jk Jm Jn Jp Js Jt Lh Li Lj Lv Ly Lz Mb Mc Me Mf Mh Mi Mj Mk Ml Mn Mp Mq Mr Ms Mt Mv Mw Mx My Mz Na Nb Nc Nd Ne Nf Ng Nh Ni Nj Nk Nl Nq Nr Ns Nt Nu Nv Nw Nx Ny Of Oh Oi Ok Om Oy Oz Pa Pd Pe Pf Po Pz Qa Qb Qc Qd Qe) Ni(Fp Hq Hr Hu Hv Hw Hx Ih Ii Ij Ik Il Im In Io Iq Ir Is It Iu Iv Jg Jh Jk Jm Jn Jo Jp Js Jt Lh Li Lj Lv Ly Lz Ma Mb Mc Me Mf Mh Mj Mk Ml Mn Mq Mr Ms Mt Mv Mw Mx My Mz Na Nb Nc Nd Ne Nf Ng Nh Nj Nk Nl Nr Ns Nt Nu Nv Nw Nx Ny Of Oi Ok Om Oy Oz Pa Pd Pe Pf Po Pz Qa Qb Qc Qd Qe) Jt(Fp Hq Hr Hu Hv Hw Hx Ih Ij Ik Il Im In Iq Ir Is It Iu Iv Jg Jh Jk Jm Jn Jp Js Lh Li Lj Lv Ly Lz Mb Mc Me Mf Mh Mi Mj Mk Ml Mn Mp Mq Mr Ms Mt Mv Mw Mx My Mz Na Nb Nc Nd Ne Nf Ng Nh Nj Nk Nl Nq Nr Ns Nt Nu Nv Nw Nx Ny Of Oh Oi Ok Om Oy Oz Pa Pd Pe Pf Po Pz Qa Qb Qc Qd Qe) Hw(Fp Hq Hr Hu Hv Hx Ih Ii Ij Ik Il Im In Iq Ir Is It Iu Iv Jg Jh Jk Jm Jn Jo Jp Js Lh Li Lj Lv Ly Lz Mb Mc Me Mf Mh Mj Mk Ml Mn Mq Mr Ms Mt Mv Mw Mx My Mz Na Nb Nc Nd Ne Nf Ng Nh Nj Nk Nl No Nr Ns Nt Nu Nv Nw Nx Ny Of Oi Ok Om Oy Oz Pa Pd Pe Pf Po Pz Qa Qb Qc Qd Qe) Qa(Fp Hq Hr Hu Hv Hx Ih Ii Ij Ik Il Im In Iq Ir Is It Iu Iv Jg Jh Jk Jm Jn Jo Jp Js Lh Li Lj Lv Ly Lz Mb Mc Me Mf Mh Mj Mk Ml Mn Mq Mr Ms Mt Mv Mw Mx My Mz Na Nb Nc Nd Ne Nf Ng Nh Nj Nk Nl No Nr Ns Nt Nu Nv Nw Nx Ny Of Oi Ok Om Oy Pa Pd Pe Pf Po Pz Qb Qc Qd Qe) Jp(Fp Hq Hr Hu Hv Hx Ih Ii Ij Ik Il Im In Iq Ir Is It Iu Iv Jg Jh Jk Jm Jn Jo Js Lh Li Lj Ly Lz Ma Mb Mc Me Mf Mh Mj Mk Ml Mn Mq Mr Ms Mt Mv Mw Mx My Mz Na Nb Nc Nd Ne Nf Ng Nh Nj Nk Nl Nq Nr Ns Nu Nv Nw Nx Ny Of Oh Oi Ok Om Oy Pa Pb Pd Pe Pf Po Pz Qc Qd Qe) Jg(Fp Hq Hr Hu Hv Hx Ih Ii Ij Ik Il Im In Iq Ir Is It Iu Iv Jh Jk Jm Jn Jo Js Lh Li Lj Ly Lz Ma Mb Mc Me Mf Mg Mi Mj Mk Ml Mn Mp Mq Mr Mt Mu Mv Mw Mx Mz Na Nb Nc Nd Ne Nf Nh Nj Nk Nl Nq Nr Ns Nt Nu Nv Nw Nx Ny Of Oh Ok Om Pa Pc Pd Pe Pf Po Qb Qc Qd Qe) Na(Fp Hq Hr Hu Hx Ih Ii Ij Ik Im In Iq Ir Is It Iu Iv Jh Jk Jm Jn Jo Js Lh Li Lj Lv Lw Ly Lz Mc Me Mf Mh Mi Mj Mk Ml Mn Mq Mr Ms Mt Mv Mw My Mz Nb Nc Nd Ne Nf Ng Nh Nj Nk Nl No Nr Ns Nt Nu Nv Nw Nx Ny Of Oh Oi Ok Om Oy Oz Pa Pd Pe Pf Po Pz Qc Qd) Nf(Fp Hq Hr Hu Hv Hx Ih Ij Ik Il Im In Iq Ir Is It Iu Iv Jh Jk Jm Jn Jo Js Lh Li Lj Ly Lz Mb Mc Me Mf Mi Mj Mk Ml Mn Mq Mr Mt Mv Mw Mx My Mz Nb Nc Nd Ne Ng Nh Nk Nl No Nr Ns Nt Nu Nv Nw Nx Ny Of Oh Oi Ok Om Oy Oz Pa Pd Pe Pf Po Pz Qb Qc Qd Qe) Im(Fp Hq Hr Hu Hv Hx Ih Ii Ij Ik Il In Iq Ir Is It Iu Iv Jh Jk Jm Jo Js Lh Li Lj Ly Lz Mb Mc Me Mf Mi Mj Mk Ml Mn Mq Mr Ms Mt Mv Mw Mx My Nb Nc Nd Ne Ng Nh Nj Nk Nl Nq Nr Ns Nt Nu Nv Nw Nx Ny Of Oi Ok Om Oy Pa Pd Pe Pf Po Pz Qb Qc Qd Qe) Nw(Hq Hr Hu Hv Hx Ih Ii Ij Ik Il In Iq Ir Is Iu Iv Jh Jk Jm Jn Jo Lh Li Lj Ly Lz Ma Mb Mc Me Mf Mi Mj Mk Ml Mn Mq Mr Ms Mt Mv Mw Mx My Mz Nb Nc Nd Ne Ng Nh Nj Nk Nl No Nq Nr Ns Nt Nu Nv Nx Ny Of Oh Oi Ok Om Oy Pa Pb Pd Pe Pf Pz Qc Qd) Oi(Fp Hq Hr Hu Hv Hx Ih Ii Ij Ik Il In Io Iq Ir It Iu Iv Jh Jk Jm Jo Js Li Lj Ly Lz Mb Mc Me Mf Mh Mj Mk Ml Mn Mq Mr Ms Mv Mw Mx My Nb Nc Nd Ne Ng Nh Nj Nk Nl Nr Ns Nt Nu Nv Nx Ny Of Ok Om Oy Oz Pa Pb Pd Pe Pf Po Pz Qb Qc Qd Qe) Is(Fp Hq Hr Hu Hv Hx Ih Ij Ik Il In Iq Ir It Iu Iv Jh Jk Jm Jn Jo Js Lh Li Lj Ly Lz Mb Mc Me Mf Mj Mk Ml Mn Mq Mr Ms Mt Mv Mw Mx My Mz Nb Nc Nd Ne Ng Nh Nj Nk Nl Nr Ns Nt Nu Nv Nx Ny Of Oh Ok Om Oy Pa Pd Pe Pf Po Qb Qc Qd Qe) Mh(Fp Hq Hr Hu Hv Hx Ih Ii Ij Ik Il In Io Iq Ir It Iu Iv Jh Jk Jm Jo Js Li Lj Lv Ly Lz Ma Mb Mc Me Mf Mi Mj Mk Ml Mn Mp Mq Mr Ms Mv Mw Mx My Nc Nd Ne Ng Nh Nj Nk Nl Nr Ns Nu Nv Nx Ny Of Oy Oz Pa Pb Pd Pf Po Pz Qb Qc Qd Qe) Lh(Fp Hq Hr

Figure 34 Continued

Hu Hv Hx Ih Ij Ik Il In Iq Ir It Iu Iv Jh Jk Jm Js Li Lj Lz Mb Mc Me Mf Mi Mj Mk Ml Mn Mq Mr Mt Mv Mw Mx My Mz Nb Nc Nd Ne Nh Nk Nl No Nq Nr Ns Nt Nu Nv Nx Ny Of Ok Om Oz Pa Pd Pe Pf Po Pz Qb Qc Qd Qe) Ok(Fp Hq Hr Hu Hv Hx Ih Ij Ik Il In Iq Ir It Iu Iv Jh Jk Jm Jn Js Li Lj Ly Lz Mb Mc Me Mf Mj Mk Ml Mn Mq Mr Mt Mv Mw Mx My Mz Nb Nc Nd Ne Ng Nh Nj Nk Nl Nr Ns Nt Nu Nv Nx Ny Of Om Oy Pa Pd Pe Pf Po Qb Qc Qd Qe) Lv(Fp Hq Hr Hu Hv Hx Ih Ii Ij Ik Il In Iq Ir It Iu Iv Jh Jk Jm Jo Js Li Lj Ly Lz Mb Mc Me Mf Mj Mk Ml Mn Mq Mr Ms Mv Mw Mx My Nb Nc Nd Ne Ng Nh Nk Nl Nr Ns Nu Nv Nx Ny Of Oy Oz Pa Pd Pe Pf Po Pz Qb Qc Qd Qe) Mi(Fp Hq Hr Hu Hv Hx Ih Ij Ik Il In Iq Ir It Iu Iv Jh Jk Jm Js Li Lj Ly Lz Mb Mc Me Mf Mg Mj Mk Ml Mn Mp Mq Mr Mv Mw Mx My Nb Nc Nd Ne Nh Nk Nl Nq Nr Ns Nt Nu Nv Nx Ny Of Oh Pa Pd Pe Pf Po Pz Qb Qc Qd Qe) Ms(Fp Hq Hr Hu Hv Hx Ih Ii Ij Ik Il In Iq Ir It Iu Iv Jk Jm Jo Js Li Lj Ly Lz Ma Mb Mc Me Mf Mj Mk Ml Mn Mq Mr Mv Mx My Nb Nc Nd Ne Ng Nh Nj Nk Nl No Nr Ns Nu Nv Nx Ny Of Oy Pa Pd Pe Pf Po Pz Qb Qc Qd Qe) Om(Fp Hq Hr Hu Hv Hx Ih Ij Il In Iq Ir It Iu Iv Jh Jk Jm Jn Js Li Lj Ly Lz Ma Mb Mc Me Mf Mg Mj Mk Ml Mn Mq Mr Mt Mu Mv Mw Mx Mz Nb Nc Nd Ne Nh Nj Nk Nl Nq Nr Ns Nt Nu Nv Nx Ny Pa Pd Pe Pf Po Qb Qc Qd Qe) Oh(Fp Hq Hr Hu Hv Hx Ih Ii Ij Ik Il Iq Ir It Iu Iv Jh Jk Jm Jo Js Li Lj Ly Lz Mb Mc Me Mf Mj Mk Ml Mn Mp Mq Mr Mt Mv Mw Mx My Nb Nc Nd Ne Ng Nh Nk Nl Nr Ns Nu Nv Nx Ny Of Oy Pa Pd Pe Pf Po Qb Qc Qd Qe) Jn(Fp Hq Hr Hu Hv Hx Ih Ij Ik Il In Iq Ir It Iu Iv Jh Jk Jm Js Li Ly Lz Mb Mc Me Mf Mj Mk Ml Mn Mq Mr Mv Mw Mx My Mz Nb Nc Nd Ne Ng Nh Nj Nk Nl Nr Ns Nu Nv Nx Ny Of Oy Pa Pd Pe Pf Po Qb Qc Qd Qe) Jo(Fp Hq Hr Hu Hv Hx Ih Ii Ij Ik In Io Ir It Iu Iv Jh Jk Jm Li Lj Ly Mb Mc Me Mf Mj Mk Ml Mn Mq Mr Mt Mv Mw Mx My Nb Nc Nd Ne Ng Nh Nj Nk Nl No Nr Ns Nu Nv Nx Ny Of Oy Oz Pa Pd Pe Po Pz Qc Qd) Nt(Fp Hq Hr Hu Hv Hx Ih Ij Il In Iq Ir It Iu Iv Jh Jk Js Li Lj Lz Mb Mc Me Mf Mj Mk Ml Mn Mp Mq Mr Mv Mw Mx My Nb Nc Nd Nh Nk Nl No Nq Nr Ns Nu Nv Nx Ny Of Oy Pa Pd Pe Pf Po Pz Qb Qc Qd Qe) Mz(Fp Hq Hr Hu Hv Hx Ih Ij Ik Il In Iq Ir It Iu Iv Jh Jk Jm Js Li Ly Lz Mb Mc Me Mf Mj Mk Mn Mq Mr Mv Mw Mx My Nb Nc Nd Ne Ng Nh Nk Nl Nr Ns Nu Nv Nx Ny Of Oy Oz Pa Pd Pe Pf Po Pz Qb Qd Qe) Ma(Fp Hq Hr Hu Hx Ih Ii Ij Il Iq Ir It Iu Iv Jh Jk Jm Js Li Lj Ly Lz Mc Me Mf Mg Mj Mk Ml Mn Mq Mr Mv Mw Mx My Nb Nc Nd Ne Nh Nk Nl Nq Nr Ns Nu Nv Nx Ny Of Oy Pa Pd Pe Pf Po Qb Qc Qd Qe) Oz(Fp Hq Hr Hu Hv Hx Ih Ii Ij Ik Il In Iq Ir It Iu Jk Jm Js Li Lj Ly Lz Mb Mc Me Mf Mj Mk Ml Mn Mq Mr Mv Mw Mx My Nb Nc Ne Ng Nh Nk Nl Nr Ns Nu Nv Nx Ny Of Oy Pa Pb Pf Po Pz Qb Qc Qd Qe) Io(Fp Hq Hr Hu Hv Hx Ih Ii Ij Ik Il In Iq It Jk Jm Js Li Lj Ly Lz Mb Mc Me Mf Mj Mk Ml Mn Mq Mr Mv Mw Mx My Nb Nc Nd Ne Ng Nh Nk Nl Nr Ns Nu Nv Nx Ny Of Oy Pa Pd Pe Pf Po Pz Qb Qc Qe) Pb(Fp Hq Hr Hu Hx Ih Ii Ik Il Iq Ir It Iu Iv Jk Jm Js Li Lj Ly Lz Mb Mc Me Mf Mj Mk Ml Mn Mq Mr Mv Mw Mx My Nc Nd Ne Ng Nh Nj Nk Nl Nr Ns Nu Nv Nx Ny Of Oy Pa Pd Pf Po Pz Qb Qc Qd Qe) No(Fp Hq Hu Hv Hx Ih Ij Ik Il In Iq Ir It Iu Iv Jh Jk Jm Js Li Lj Ly Lz Mb Mc Me Mk Ml Mn Mq Mr Mv Mw Mx My Nb Nc Nd Ng Nh Nk Nl Nr Nu Nv Nx Ny Of Oy Pa Pd Pe Pf Po Pz Qb Qc Qd Qe) Mt(Fp Hq Hr Hu Hv Ih Ii Ij Il In Iq Ir It Iu Iv Jh Jk Jm Js Li Lj Ly Lz Mb Mc Me Mf Mj Mk Mn Mq Mr Mv Mw Mx Nb Nc Nd Ne Ng Nh Nj Nk Nl Nr Ns Nu Nv Nx Of Pa Pd Pe Pf Po Qb Qc Qd Qe) Nq(Fp Hq Hr Hx Ih Ij Ik Il In Iq Ir It Iu Iv Jh Jk Js Li Lj Ly Lz Mb Mc Me Mf Mg Mj Ml Mn Mp Mq Mr Mv Mw Mx Nb Nc Nd Ne Nh Nk Nl Nr Ns Nu Nv Nx Ny Of Pa Pd Pe Pf Po Qb Qc Qd Qe) Nj(Fp Hq Hr Hu Hv Hx Ih Ii Ij Ik In Ir Iu Iv Jh Jk Jm Js Lj Ly Lz Mb Mc Mf Mj Mk Ml Mn Mq Mr Mv Mw Mx My Nb Nd Ne Ng Nh Nk Nr Ns Nu Nv Nx Ny Of Oy Pa Pd Pe Pf Po Pz Qc Qd Qe) Ip(Fp Hq Hr Hu Hv Hx Ih Ij Il Iq Ir It Iu Jk Js Li Lj Ly Lz Mc Me Mf Mj Mk Ml Mn Mq Mr Mw Mx Nb Nc Nd Ne Ng Nh Nk Nl Nr Ns Nu Nv Nx Ny Of Oy Pa Pd Pe Pf Po Qb Qc Qd Qe) Mp(Fp Hr Hu Hx Ih Ik Il Iq Ir It Iu Iv Jh Jk Jm Js Li Lj Ly Lz Mb Mc Me Mf Mj Ml Mn Mq Mr Mv Mw Mx My Nb Nc Nd Ne Nh Nk Nl Nr Nu Nv Nx Ny Of Pa Pe Po Pz Qb Qc Qd Qe) Pc(Fp Hq Hr Hx Ih Ik Il Iq It Iu Jk Jm Js Li Lj Ly Lz Mb Mc Me Mf Mj Mk Ml Mn Mq Mv Mw Mx My Nb Nc Ne Nh Nk Nl Nr Nu Nv Nx Ny Of Oy Pd Pf Po Qb Qc Qe) In(Fp Hq Hr Hu Hv Hx Ii Ij Ik Ir It Iu Iv Jh Jk Jm Li Ly Me Mf Mj Mk Ml Mn Mr Mv Mw My Nb Nc Nd Ne Ng Nh Nk Nl Ns Nu Nv Nx Ny Of Oy Pa Pe Pz Qc Qd) Mg(Fp Hq Ih Ij Il Iq Ir It Iv Jh Jk Js Li Lj Ly Lz Mb Mc Me Mf Mj Mn Mq Mr Mv Mw Mx Nb Nc Nd Ne Nh Nk Nl Nr Nu Nv Nx Pa Pd Pe Pf Po Qb Qc Qd Qe) Pz(Hr Hu Hv Hx Ih Ii Ij Ik Ir Iu Iv Jh Jk Jm Li Ly Mb Mf Mj Mn Mr Mv Mw Mx My Nb Nc Nd Ne Ng Nk Nl Ns Nu Nv Nx Ny Of Oy Pa Pd Pe Po Qd Qe) Mu(Fp Hx Ih Il Iq It Iu Jh Jk Js Li Lj Lz Mb Mc Me Mf Ml Mn Mq Mr Mv Mw Mx Nb Nc Nd Nk Nl Nr Nu Nv Nx Ny Pa Pd Pe Pf Po Qb Qc Qe) Ii(Hr Hu Hv Hx Ih Ij Ik Il Ir Iu Iv Jh Jk Js Mb Mf Mn Mq Mr Mv Mw Mx My Nb Nc Nd Ne Ng Nk Nl Nr Ns Nu Nv Nx Ny Pa Pd Pe Po Qd) Lw(Fp Hv Hx Ih Ij Il Iq Ir It Js Li Lj Ly Lz Mb Mc Me Ml Mn Mq Mv Mw Mx Nb Nc Nk Nl Nr Nu Nv Nx Ny Pf Po Qb Qd Qe) Mm(Fp Hr Ih Il Iq It Iu Jk Jm Js Li Lj Ly Mb Mc Mf Mj Ml Mn Mq Mw Mx Nb Nc Nd Nh Nk Nl Nr Nu Nv Nx Ny Po Qb Qc Qe) Hv(Fp Hr Hu Hx Ik Ir It Iu Iv Jh Jk Jm Me Mf Mj Mk Ml Mn Mv My Nd Ne Ng Nh Nk Ns Nu Nv Of Oy Pa Pe Qc Qd) Ij(Hr Hu Hx Ik Ir It Iu Iv Jh Jm Ly Mf Mj Mk Ml Mn Mv My Nd Ne Ng Nk Nl Ns Nu Nv Ny Of Oy Pa Pe Qc Qd) Iv(Hr Hu Ik Ir Iu Jh Jk Jm Lj Ly Mb Mf Mj Mk Ml Mr Mv My Nb Nd Ne Ng Nh Ns Nv Nx Of Oy Pa Pe Qc) Jh(Hq Hr Hu Hx Ik Ir Iu Jm Li Ly Mb Mf Mj Mk Ml Mn Mr Nb Nd Ne Ng Nk Nl Ns Nv Of Pa Pe Qc Qd) Pe(Fp Hq Hr Hu Hx Ik Iu Jm Lj Ly Lz Mb Mf Mj Mk Ml My Nd Ne Ng Nr Ns Nv Of Oy Pf Qc) Ng(Hr Hu Ir Iu Jk Mb Mf Mn Mr Mv Mw My Nb Nd Ne Ns Nu Nv Nx Pa Po Qd) Ns(Hr Ik Ir Jk Jm Mb Mn Mq Mr Mv My Nb Nd Ne Nu Nv Of Pa Po Qd) Ir(Hr Ik Iq It Iu Jm Jr Lj Mb Mj Ml Mv My Nd Ne Nv Of Pa Qc) Ik(Hr Hu Jk Mf Mn Mr Mv My Nb Nd Nu Nv Pa Po Qd) Of(Hr Jk Mb Mf Mn Mr Mv My Nb Nd Ne Nv Nx Pa Qd) Qd(Hr Il Jm Jr Lj Mb Mj My Nd Nv Og Pa Qc) Jm(Hr Iu Jk Mf Mn Mr Mv Nd Ne Nv Pa) Og(Fp Iq It Js Li Mc Mx Nc Nr Qb) Jr(Hu Ih Il Mq Mx Nc Nl Po Qe) Oy(Jk Mn Mr My Nb Nd Nv Pa Po) Ne(Hr Mf Mr Mv Nc Nd Nl Nv) Pa(Hr Hx Ly Mf Mj Ml My Ny) Nb(Hr Hx Mk Ml My Ny) Mf(Mb Mj Mr Nd Nv) Mv(Hr Hu Hx Mj Ny) Mr(Hr Ly Mj Mk) Nd(Hq Hr Ly Mk) Nv(Hr Hu Mj My) PoMk MjMx MyHr HuJk LiLj} Fr{Fp(Hq Hr Hu Hv Hx Ih Ii Ij Ik Il Im In Io Iq It Iu Iv Jg Jh Jj Jk Jm Jo Jp Js Li Lj Lu Lx Ly Lz Ma Mb Mc Md Me Mf Mg Mh Mi Mj Mk Ml Mm Mn Mp Mq Mr Ms Mt Mu Mv Mw Mx My Nb Nc Nd Ne Nf Ng Nh Ni Nj Nk Nl Nm Nn Nq Nr Ns Nu Nv Nw Nx Ny Oe Of Og Oh Oi Ok Om Oy Oz Pa Pc Pd Pe Pf Pg Po Pz Qb Qc Qd Qe) Nu(Hq Hr Hu Hv Hx Ih Ii Ij Ik Il Im In Io Iq It Iu Iv Jg Jh Jk Jm Jo Jp Js Li Lj Lu Lx Ly Lz Ma Mb Mc Md Me Mf Mg Mh Mi Mj Mk Ml Mm Mn Mp Mq Mr Ms Mt Mu Mv Mw Mx My Nb Nc Nd Ne Nf Nh Ni Nk Nl Nm Nn Nq Nr Ns Nv Nw Nx Ny Oe Of Og Oh Oi Ok Om Oz Pa Pc Pd Pe Pf Pg Po Pz Qb Qc Qd Qe) Hr(Hq Hu Hv Hx Ih Ii Ij Ik Il Im In Io It Iu Iv Jg Jh Jj Jk Jm Jo Jp Js Li Lj Lu Lx Ly Lz Ma Mb Mc Md Me Mf Mg Mh Mi Mj Mk Ml Mm Mn Mp Mq Mr Ms Mt Mu Mv Mw Mx My Nb Nc Nd Ne Nf Ng Nh Ni Nj Nk Nl Nm Nn Nq Nr Ns Nv Nw Nx Ny Oe Of Og Oh Oi Ok Om Oz Pa Pc Pd Pe Pg Po Pz Qb Qd Qe) Mf(Hq Hu Hx Ih Ii Ij Ik Il Im In Io Iq It Iu Iv Jg Jh Jj Jk Jm Jp Js Li Lj Lu Lx Ly Lz Ma Mb Mc Md Me Mg Mh Mi Mj Mk Ml Mm Mn Mp Mq Mr Ms Mt Mu Mv Mw My Nb Nc Nd Ne Nf Nh Ni Nj Nk Nl Nm Nq Nr Ns Nv Nw Nx Ny Oe Of Og Oh Oi Om Oy Oz Pa Pb Pc Pd Pe Pf Pg Po Pz Qb Qc Qd Qe) Oe(Hq Hu Ih Ii Ij Ik Il Im In Io Iq It Iu Jg Jh Jj Jk Jm Jp Js Li Lj Lu Lx Ly Lz Ma Mb Mc Md Me Mg Mh Mi Mj Mk Ml Mm Mn Mp Mq Mr Ms Mt Mu Mv Mw Mx My Nb Nc Nd Ne Nf Ng Nh Ni Nk Nl Nm Nn Nq Nr Ns Nv Nw Nx Ny Of Og Oh Oi Om Oy Oz Pa Pb Pc Pd Pe Pf Pg Po Pz Qb Qc Qd Qe) Nd(Hu Hx Ih Ii Ij Ik Il Im In Io Iq It Iu Iv Jg Jh Jk Jm Jp Js Li Lj Lu Lx Ly Lz Ma Mb Mc Md Me Mg Mh Mi Mj Mk Ml Mm Mn Mp Mq Mr Ms Mt Mu Mv Mw Mx My Nb Nc Ne Nf Nh Ni Nj Nk Nl Nm Nn Nq Nr Ns Nv Nw Nx Ny Of Og Oh Oi Om Oy Oz Pa Pb Pc Pd Pe Pf Pg Po Pz Qb Qd Qe) Nx(Hq Hv Hx Ih Ii Ij Ik Il Im In Io Iq It Iu Iv Jg Jh Jk Jm Jo Jp Js Li Lj Lu Lw Lx Ly Lz Ma Mb Mc Md Me Mg Mh Mi Mj Mk Ml Mm Mn Mp Mq Mr Mt Mu Mv Mw Mx Nb Nc Ne Nf Nh Ni Nj Nk Nl Nm Nn Nq Nr Ns Nv Nw Ny Of Oh Oi Ok Om Oz Pa Pc Pd Pe Pf Pg Po Pz Qb Qc Qd Qe) Ma(Hq Hu Hx Ih Ii Ij Ik Il Im Io Iq It Iu Jg Jh Jk Jm Jp Js Li Lj Lu Lx Ly Lz Mb Mc Md Me Mg Mh Mi Mj Mk Ml Mm Mn Mp Mq Mr Ms Mt Mu Mv Mw Mx My Nb Nc Ne Nf Nh Ni Nj Nk Nl Nm Nn Nq Nr Ns Nv Nw Ny Of Og Oh Oi Om Oy Oz Pa Pb Pc Pd Pf Pg Po Pz Qb Qc Qd Qe) It(Hq Hx

Lz Ma Mb Mf Mg Ml Mv Mx Na Nc Nd Ng Ni Nj Nk Nl Nm Ns Ny Oe Of Ok Oy Oz Pb Pd Pg Qb Qd) Iu(Fp Hr Hu Hv Ij Ik Im In Iv Jh Jj Jo
Jp Jt Lh Li Ma Mb Mg Ms Mv Mw Mx My Na Nc Nd Ne Ng Ni Nj Nk Nm Ns Nu Oe Of Og Ok Oz Pb Pd Qb Qd) Nd(Fp Hq Hr Hv Ih Ij Ik Im
In Iv Jj Jo Jt Lh Li Ma Mb Mf Mg Ms Mv Mx My Na Nc Ng Ni Nj Nk Nl Nm Ns Oe Of Og Ok Pb Pg Qb Qd) Jj(Fp Hr Hu Hv Ih Ii Ij Im In Iv
Jg Jh Jm Jo Jt Li Ly Ma Mb Mg Ms Mv Mw Mx My Na Nc Nj Nk Nl Nu Nx Oe Og Ok Oy Pd Qb Qd) Lh(Fp Hq Hv Ih Ij Im Iq It Jg Jh Jm Jp Js
Lj Lz Mb Mc Me Mf Mj Mk Mn Mq Mv Mw Mx Na Nc Nl Nu Nx Ny Ok Oz Pd Pf Qb Qc) Ma(Fp Hr Hv Ih Ii Ij Ik Im In Iv Jo Jt Li Ly Lz Mb
Mg Ms Mx My Na Nc Ng Nj Nk Nl Nm Nx Oe Of Og Ok Pb Qb Qd) Nj(Fp Hr Hu Hv Ih Ii Ij Ik Im In Iv Jo Jt Mb Mg Ms Mv Mx My Na Ng Ni
Nl Nm Nu Oe Of Og Ok Pb Pd Qb Qd) Pg(Fp Hr Ih Ij Iq It Jg Jh Jm Jp Js Li Lj Ly Lz Mc Me Mf Mj Mk Ml Mn Mq Mv Mw Mx Nc Nl Nu Ny
Pd Qb Qd) Nk(Fp Hr Hu Hv Ij Ik Im In Iv Jh Jo Jt Mb Mg Mq Ms Mv Mw Mx My Na Ne Ng Ni Nm Nu Oe Of Og Ok Pb Qb Qd) Qd(Hr Hu Hv Ih
Ij Ik Im In Is Iv Jo Jt Ly Mb Mg Ml Ms Mv My Na Nl Nm Oe Of Og Ok Oz Pb Qc) Ms(Fp Hr Hv Ih Ii Ij Im In Iv Jg Jh Jo Jt Mb Mg Mv Mw
Mx My Na Nl Nu Nx Oe Ok Qb) Og(Fp Hr Hu Hv Ih Ii Ij Im In Iv Jg Jh Jo Jt Mb Mg Mx My Na Nc Nl Nx Ok Pd Qb) In(Fp Ik Im It Iv Jo Jt Li
Lz Mg Ml Mv Mx My Nc Ng Nl Nm Oe Of Ok Pb Qb) Jt(Fp Hu Ik Im Iv Jo Li Ly Mg Mv Mx My Nc Ng Nl Nm Ns Oe Of Pb Pd Qb) Nm(Fp
Hv Ih Ij Im Iv Jo Li Mv Mw Mx My Na Nc Nl Oe Ok Pd Qb) Iv(Hv Ij Ik Im Jo Mb Mg Mv My Na Ng Ni Nl Ns Oe Of Ok Pb) Oe(Fp Ih Ij Ik Im
Jo Mb Mg Mv Mx My Na Nc Nl Ok Pd Qb) Mv(Hv Ik Im Jo Mb Mg Mx Na Nc Ng Nl Of Ok Oy Pb) My(Ik Im Jg Jh Jo Mg Mx Na Nc Ng Nl
Of Ok Pb) Pb(Fp Hr Hv Ii Ij Jo Li Mx Na Nu Ny Ok Pd) Nl(Hv Ij Ik Mb Mg Na Ne Ng Ni Of Ok Qb) Mb(Fp Hu Im Li Lz Mf Mg Mx Nc Qb)
Ok(Hu Ih Ik Ly Mg Mx Nc Of Pd Qb) Na(Im Li Lz Mg Nc Of Qb) Jo(Ik Im Mg Mx Ng Of Qb) Mx(Hu Ik Jg Mg Of) Ik(Fp Ij Li Mj) Of(Hu Hv
Ij Pd) Ns(Mq Mw) Mg(Ng Qb) Nc(Ne Ni) Mjlm MwHu NgJg HvIt} Ji[Nd(Fp Hq Hr Hu Hv Hw Hx Ih Ii Ij Ik Il Im In Iq Ir Is It Iu Iv Jg Jh Jj Jk
Jm Jn Jo Jp Jq Js Jt Lh Li Lj Lu Lw Lx Ly Lz Mb Mc Md Me Mf Mg Mh Mi Mj Mk Ml Mm Mn Mp Mq Mr Mv Mw Mx My Mz Na Nb Nc Ne
Nf Ng Nh Ni Nj Nk Nl Nm Nq Nr Ns Nt Nu Nv Nw Nx Ny Oe Of Og Oh Oi Ok Om Oy Oz Pa Pb Pd Pe Pf Po Pz Qa Qb Qc Qd Qe) Iu(Fp Hq
Hr Hu Hv Hw Hx Ih Ii Ij Ik Il Im In Iq Ir Is It Iv Jg Jh Jj Jk Jm Jn Jo Jp Jq Js Jt Lh Li Lj Lw Lx Ly Lz Mb Mc Md Me Mf Mg Mh Mi Mj Mk Ml
Mm Mn Mp Mq Mr Mt Mv Mw Mx My Mz Na Nb Nc Ne Nf Ng Nh Ni Nj Nk Nl Nm Nr Ns Nt Nu Nv Nw Nx Ny Oe Of Og Oh Oi Ok Om Oy
Oz Pa Pb Pd Pe Pf Po Pz Qa Qb Qc Qd Qe) Nv(Fp Hq Hr Hu Hv Hw Hx Ih Ii Ij Ik Il Im In Iq Ir Is It Iv Jg Jh Jj Jk Jm Jn Jo Jp Jq Js Jt Lh Li Lj
Lu Lw Lx Ly Lz Mb Mc Md Me Mf Mg Mh Mi Mj Mk Mn Mp Mq Mr Mt Mv Mw Mx My Mz Na Nb Nc Ne Nf Ng Nh Ni Nj Nk Nl Nm Nq
Nr Ns Nt Nu Nw Nx Ny Oe Of Oh Oi Ok Om Oy Oz Pa Pc Pd Pe Pf Pg Po Pz Qa Qb Qc Qd Qe) Jo(Fp Hq Hr Hu Hv Hw Hx Ih Ii Ij Ik Il Im In
Iq Ir Is It Iv Jg Jh Jj Jk Jm Jn Jp Jq Js Jt Li Lj Lu Lw Lx Ly Lz Ma Mb Mc Md Me Mf Mg Mh Mi Mj Mk Ml Mm Mn Mp Mq Mr Mt Mv Mw
Mx My Mz Na Nb Nc Ne Nf Ng Nh Ni Nj Nk Nl Nm Nq Nr Ns Nu Nw Nx Ny Oe Of Oh Oi Ok Om Oy Oz Pa Pd Pe Pf Po Pz Qa Qb Qc Qd
Qe) Mr(Fp Hq Hr Hu Hv Hw Hx Ih Ii Ij Ik Il Im In Iq Ir Is It Iv Jg Jh Jj Jk Jm Jn Jp Jq Js Jt Li Lj Lu Lw Lx Ly Lz Mb Mc Md Me Mf Mg
Mh Mi Mj Mk Mn Mp Mq Mt Mv Mw Mx My Mz Na Nb Nc Ne Nf Ng Nh Ni Nj Nk Nl Nm Nr Ns Nt Nu Nw Nx Ny Oe Of Oh Oi Ok Om Oy
Oz Pa Pd Pe Pf Pg Po Pz Qa Qb Qc Qd Qe) Jp(Fp Hq Hr Hu Hv Hw Hx Ih Ii Ij Ik Il Im In Iq Ir Is It Iv Jg Jh Jj Jk Jm Jn Jq Js Jt Lh Li Lj Lu Lw
Lx Ly Lz Ma Mb Mc Md Me Mf Mg Mh Mj Mk Ml Mm Mn Mq Mt Mv Mw Mx My Na Nb Nc Ne Ng Nh Ni Nj Nk Nl Nm Nr Ns Nu Nw Nx
Ny Oe Of Og Oh Oi Ok Om Oy Oz Pa Pb Pd Pe Pf Po Pz Qa Qb Qc Qd Qe) Pe(Fp Hq Hr Hu Hv Hw Hx Ih Ii Ij Ik Il Im In Iq Ir Is It Iv Jg Jh Jj
Jk Jm Jn Jq Js Jt Lh Li Lj Lu Lw Lx Ly Lz Mb Mc Md Me Mf Mg Mi Mj Mk Mn Mp Mq Mt Mv Mw Mx My Mz Na Nb Nc Ne Nf Ng Nh Ni
Nj Nk Nl Nm Nr Ns Nt Nu Nw Nx Ny Oe Of Oh Oi Ok Om Oy Oz Pa Pd Pf Pg Po Pz Qa Qb Qc Qd Qe) Is(Fp Hq Hr Hu Hv Hw Hx Ih Ii Ij Ik Il
Im In Iq Ir It Iv Jg Jh Jj Jk Jm Jn Jq Js Jt Lh Li Lj Lw Lx Ly Lz Mb Mc Md Me Mf Mg Mh Mi Mj Mk Ml Mn Mq Mt Mv Mw Mx My Mz Na
Nb Nc Ne Nf Ng Nh Ni Nj Nk Nl Nm Nr Ns Nu Nw Nx Ny Oe Of Oh Oi Ok Om Oy Oz Pa Pb Pd Pf Po Pz Qa Qb Qc Qd Qe) Lx(Fp Hq Hr Hu
Hv Hw Hx Ih Ii Ij Ik Il Im In Iq Ir It Iv Jg Jh Jj Jm Jn Jq Js Jt Lh Li Lj Lu Lw Ly Lz Mb Mc Md Me Mf Mg Mi Mj Mk Mn Mp Mq Mv Mw Mx
My Mz Na Nb Nc Ne Nf Ng Nh Ni Nj Nk Nl Nm Nq Nr Ns Nt Nu Nw Nx Ny Oe Of Oh Oi Ok Om Oy Oz Pa Pd Pf Po Pz Qa Qb Qc Qd Qe)
Mi(Fp Hq Hr Hu Hv Hw Hx Ih Ii Ij Ik Il Im In Iq Ir It Iv Jg Jh Jj Jm Jn Js Jt Lh Li Lj Lw Ly Lz Mb Mc Md Me Mf Mg Mh Mj Mk Mn Mp Mq
Mv Mw Mx My Mz Na Nb Nc Ne Nf Ng Nh Ni Nk Nl Nm Nq Nr Ns Nt Nu Nw Nx Ny Oe Of Oh Oi Ok Om Oy Oz Pa Pb Pd Pf Po Pz Qa Qb
Qc Qd Qe) Il(Fp Hq Hr Hu Hv Hw Hx Ih Ii Ij Ik Im In Iq Ir It Iv Jg Jh Jk Jm Jn Jq Js Jt Lh Li Lj Lw Ly Lz Mb Mc Md Me Mf Mg Mh Mj Mk
Mn Mq Mv Mw Mx My Mz Na Nb Nc Ne Nf Ng Nh Ni Nj Nk Nl Nm Nq Nr Ns Nt Nu Nw Nx Ny Oe Of Oh Oi Ok Om Oy Oz Pa Pd Pf Pg Po
Pz Qa Qb Qd Qe) Mm(Fp Hq Hr Hu Hv Hx Ih Ii Ij Ik Im In Iq Ir It Iv Jg Jh Jj Jm Js Jt Li Lj Lw Ly Lz Mb Mc Md Me Mf Mg Mh Mj Mk Ml
Mn Mq Mv Mw Mx My Mz Na Nb Nc Ne Nf Ng Nh Ni Nj Nk Nl Nm Nr Ns Nu Nw Nx Ny Oe Of Oh Oi Ok Om Oy Oz Pb Pd Pf Po Pz Qa Qb
Qc Qd Qe) Pc(Fp Hq Hr Hv Hx Ih Ii Ij Ik Im In Iq Ir It Iv Jg Jh Jj Jm Jn Jq Js Jt Li Lj Lw Ly Lz Mb Mc Md Me Mf Mg Mh Mj Mk Ml Mn Mq
Mv Mw Mx My Mz Na Nb Nc Ne Nf Ng Nh Ni Nj Nk Nl Nm Nr Ns Nu Nw Nx Ny Oe Of Oh Ok Om Oy Oz Pb Pd Pf Po Pz Qa Qb Qc Qd Qe)
Hw(Fp Hq Hr Hu Hv Hx Ih Ij Ik Im In Iq Ir It Iv Jg Jh Jm Jn Jq Js Jt Lh Li Lj Lw Ly Lz Mb Mc Md Me Mf Mg Mh Mj Mk Mn Mq Mv Mw Mx
My Mz Na Nb Nc Ne Nf Ng Nh Ni Nj Nk Nl Nm Nr Ns Nt Nu Nw Ny Oe Of Oi Ok Om Oy Oz Pa Pd Pf Po Pz Qa Qb Qc Qd Qe) Ma(Fp Hq Hr
Hu Hv Hx Ih Ii Ij Ik Im In Iq Ir It Iv Jg Jh Jj Jm Jn Jq Js Jt Li Lj Lw Ly Lz Mc Md Me Mf Mg Mh Mj Mk Mn Mq Mv Mw Mx My Mz Na Nb
Nc Ne Nf Ng Nh Ni Nk Nl Nm Nr Ns Nu Nw Nx Ny Oe Of Oh Oi Ok Om Oy Oz Pd Pf Po Pz Qa Qb Qc Qd Qe) Mp(Fp Hr Hu Hv Hx Ih Ii Ij Ik
Im In Iq Ir It Iv Jg Jh Jj Jm Js Jt Li Lj Lw Ly Lz Mb Mc Md Me Mf Mg Mh Mj Mk Ml Mn Mq Mv Mw Mx My Mz Na Nb Nc Ne Nf Ng Nh Ni
Nk Nl Nm Nr Nu Nw Nx Ny Oe Of Oh Oi Ok Om Oy Oz Pb Pd Pf Po Pz Qa Qb Qc Qd Qe) Mt(Fp Hq Hr Hu Hv Hx Ih Ii Ij Ik Im In Iq Ir It Iv
Jg Jh Jj Jm Jn Jq Js Jt Li Lj Lw Ly Lz Mb Mc Md Me Mf Mg Mh Mj Mk Mn Mq Mv Mw Mx My Mz Na Nb Nc Ne Nf Ng Nh Ni Nj Nk Nl Nm Nr
Ns Nu Nw Nx Ny Oe Of Oh Oi Ok Om Oy Oz Pd Pf Po Pz Qa Qb Qd Qe) My(Fp Hq Hr Hu Hv Hx Ih Ii Ij Ik Im In Ir It Iv Jg Jh Jj Jn Jq Js Jt Li Lw
Ly Lz Mb Md Me Mf Mg Mh Mj Ml Mn Mq Mx Mz Na Nb Nc Ne Ng Nh Ni Nj Nk Nl Nm Nr Ns Nu Nw Nx Ny Oe Of Og Oh Oi Ok Om Oy
Oz Pb Pd Po Pz Qa Qb Qc Qd Qe) Lh(Fp Hq Hr Hu Hv Ih Ij Ik Im In Iq Ir It Iv Jg Jh Jm Jn Js Jt Li Lj Lw Ly Lz Mb Mc Md Me Mf Mg Mj Mk
Mn Mq Mv Mw Mx Mz Na Nb Nc Ne Nf Ng Nh Ni Nk Nl Nm Nq Nr Ns Nt Nu Nw Oe Of Oh Oi Ok Om Oy Oz Pa Pd Pf Po Pz Qa Qb Qd Qe)
Lu(Fp Hq Hr Hu Hv Hx Ih Ii Ij Ik Im In Iq Ir It Iv Jg Jh Jj Jm Jn Jq Js Jt Li Lj Ly Lz Mb Mc Md Me Mf Mg Mh Mj Mk Mn Mq Mv Mw Mx Mz Na
Nb Nc Ne Nf Ng Nh Ni Nk Nl Nm Nr Ns Nu Nw Ny Oe Of Ok Om Oy Oz Pd Pf Po Pz Qa Qb Qd Qe) Og(Fp Hq Hr Hu Hv Ih Ii Ij Ik Im In Iq Ir
It Iv Jj Jm Jn Jq Js Jt Li Lj Lw Ly Lz Mb Mc Md Me Mf Mh Mj Mk Ml Mn Mq Mx Mz Na Nc Ne Nf Ng Nh Ni Nj Nk Nl Nm Nr Ns Nu Nw Nx
Ny Oe Of Oh Oi Ok Oy Oz Pb Pd Pf Pz Qa Qb Qc Qd Qe) Pa(Fp Hq Hr Hu Hv Ih Ij Ik Im In Iq Ir It Iv Jg Jh Jj Jm Jn Js Jt Li Lj Lw Ly Lz Mb
Mc Me Mf Mg Mj Mn Mq Mv Mw Mx Mz Na Nb Nc Ne Nf Ng Nh Ni Nk Nl Nm Nr Ns Nt Nu Nw Nx Oe Oh Oi Ok Om Oz Pd Pf Po Pz Qa
Qb Qd Qe) Ip(Fp Hq Hr Hv Ih Ii Ij Ik Im Iq Ir It Iv Jh Jj Jm Js Jt Li Lj Lw Ly Lz Mb Mc Md Me Mf Mh Mj Mk Mn Mq Mw Mx Mz Na Nc Ne
Nf Ng Ni Nl Nu Nw Nx Ny Oe Of Ok Om Oy Oz Pd Pf Qa Qb Qd Qe) Ml(Fp Hq Hr Hu Hv Hx Ih Ij Io Ir Iv Jg Jh Jj Jn Jq Li Ly Lz Mb Md Mg
Mh Mj Mn Mq Mv Mw Mx Mz Na Nb Nc Nf Nh Ni Nj Nk Nl Nm Nr Ns Nu Nw Nx Ny Oh Oi Om Oy Oz Pb Pd Pz Qa Qc Qd Qe) Nq(Fp Hq
Hr Hv Ih Ii Ij Ik Im In Iq Ir It Iv Jg Jh Jm Js Jt Li Lj Lw Ly Lz Mb Mc Me Mf Mg Mh Mj Mk Mn Mq Mw Mx Nb Nc Ne Nh Ni Nl Nm Nu Nw
Oe Oh Ok Om Oz Pd Pf Po Qa Qb Qd Qe) Io(Fp Hq Hr Hu Hv Ih Ii Ij Ik Im In Iq It Jh Jj Jm Jq Js Li Lj Ly Lz Mc Md Me Mf Mh Mj Mk Mn
Mq Mw Mx Mz Nc Ne Nf Ng Nh Ni Nm Ns Nw Nx Ny Oe Of Oi Ok Om Oy Oz Pd Pf Pz Qb Qc) Jq(Hu Hv Hx Ii In It Iv Jg Jh Jj Jn Jt Li Lv

Figure 34 Continued

Lw Ly Lz Mb Md Mg Mh Mj Mq Mv Mx Na Nb Ne Nh Ni Nj Nk Nl Nm Nr Ns Nu Nx Ny Oe Oh Oi Ok Oy Oz Pb Pd Pg Po Pz Qa Qc Qe)
Jk(Fp Hq Hr Hv Ih Ij Im Iq Ir It Iv Jg Jh Jm Js Li Lj Lw Ly Lz Mb Mc Me Mf Mg Mj Mk Mn Mq Mx Mz Na Nb Nc Ne Nf Nh Nk Nl Nr Nu Nw Ok Oz Pd Pf Po Qa Qb Qd Qe) Hx(Hu Ii Ik In It Iv Jg Jh Jj Jn Jt Li Lw Mb Md Mg Mh Mj Mv Mz Na Nb Ne Ng Nh Ni Nj Nk Nl Nm Nr Ns Nu Nx Ny Oe Of Oh Oi Ok Om Oy Pb Pd Po Pz Qa Qb Qc Qe) Pg(Hq Hr Hu Hv Ih Im Iq Ir Iv Jg Jh Jm Js Li Lj Lw Ly Lz Mc Me Mf Mj Mk Mn Mq Mv Mw Mx Mz Na Nb Nc Nf Nk Nl Nm Nr Nu Nw Oe Ok Om Oz Pd Pf Po Qa Qd Qe) Nt(Fp Hq Hr Hu Hv Ih Ij Im Iq Ir Iv Jm Js Li Lj Lw Lz Mc Me Mf Mg Mj Mk Mn Mq Mv Mw Mx Na Nb Nc Nf Nk Nl Nr Nu Nw Oe Of Ok Om Oz Pd Pf Po Qa Qb Qd) Oh(Hr Hu Hv Ii Ik In Ir Iv Jh Jj Jn Jt Li Ly Mb Mg Mh Mj Mq Mv Mz Na Nb Ne Nf Nh Ni Nj Nl Nm Nr Ns Nu Nx Oe Oi Ok Om Oy Oz Pb Pd Po Pz Qa Qc Qe) Lv(Fp Hq Hv Ih Ii Ij Ik Im In Iq Ir It Jm Js Jt Lj Lw Lz Mc Md Mf Mh Mj Mk Mn Mq Mw Mx Nc Ne Ng Nh Ni Nk Nm Nu Nw Ny Oe Of Ok Oy Pf Qa Qd Qe) Nr(Fp Hu Ii Ik In It Iv Jg Jh Jj Jn Jt Li Lw Mb Md Mg Mh Mv Mz Ne Nf Nh Ni Nj Nk Nm Ns Nu Nw Nx Ny Oe Of Oi Om Oy Oz Pb Pd Po Pz Qa Qc Qe) Po(Fp Hu Ii Ik In Iv Jg Jh Jj Jn Jt Li Lw Ly Mb Md Mg Mh Mq Mv Na Ne Ng Nh Ni Nj Nl Nm Ns Nx Ny Oe Of Oi Om Oy Pb Pd Pz Qa Qb Qc Qe) Qc(Hu Ii Ir Iv Jg Jh Jj Jn Jt Li Lz Mb Mg Mh Mj Mn Mq Mv Mx Mz Na Nb Nc Nf Nj Nk Nl Nm Ns Nu Nw Nx Oi Om Oy Oz Pb Pd Qa Qd Qe) Ms(Hq Hv Ih Ij Ik Im Iq Ir Iv Jm Js Li Ly Lz Mc Md Me Mf Mh Mk Mq Mx Nc Ng Ni Nk Nl Nu Nw Ny Oe Of Ok Oy Pf Qa Qb Qd) Jn(Hu In It Iv Jg Jh Jj Jr Js Jt Li Lw Ly Mb Mg Mh Mv Na Nb Nh Ni Nj Nk Nl Nm Ns Nu Nx Ny Oi Om Oy Oz Pb Pd Pz Qb Qe) Qe(Hu Ih Ii In It Iv Jg Jh Jj Jt Li Ly Mb Mg Mh Mv Na Ne Nh Ni Nj Nl Nm Ns Nu Nx Ny Oe Oi Om Oy Oz Pb Pd Pz Qb) Nx(Hr Hu Ir Iv Jg Jh Jt Li Lw Ly Mb Md Mg Mh Mq Mv Mz Na Nb Ne Nf Nh Ni Nl Ns Nu Oi Ok Om Oy Oz Pb Pd Pz Qa) Jr(Hq Hv Ij Im Iq Ir Iv Jm Lz Mc Md Mf Mj Mk Mn Mq Mw Mx Mz Na Nc Nf Ng Nk Nl Nw Ny Of Ok Pf Qa Qd) Mv(Ii Ik In Iv Jh Jj Jt Li Ly Mb Md Mg Mh Mz Ne Ng Nh Ni Nj Nk Nl Nm Ns Ny Of Oi Oy Oz Pb Pd Pz) Pb(Hq Hu Ii In Iv Jg Jh Jt Li Ly Mb Md Mg Mj Mq Mz Na Nb Nf Ni Nj Ns Nu Ny Ok Om Oy Oz Pd Qa) Mg(Hu Ik In Ir Iv Jh Jj Ly Mb Md Mh Mx Mz Na Nc Ng Nj Nk Nl Nm Ns Ny Oi Ok Oy Oz Pz Qa) Jj(Hr Hu Ii Iv Jg Jh Jt Li Mb Md Mq Mz Na Nb Nf Nh Nj Nl Ns Oi Om Oy Pd Qa) Mb(Hu In Iv Jh Li Ly Lz Mf Mh Mz Ni Nj Nl Nm Nw Oi Pd Qa Qd) Jg(Hu In Iv Jt Ly Md Na Ng Ni Nj Nk Nl Nm Ns Ny Oi Oy Pd Pz) Nj(Hu Iv Jh Ly Md Mj Mq Na Nb Ni Ns Nu Om Oy Oz Pb Pd Pz Qb) Oi(Hu Ir Iv Jh Jt Li Lw Mh Mz Nb Om Oy Pd Qa) No(Hq Im Mc Mk Mx Nc Nf Nw Pf Qd) Om(Iv Md Mh Ng Nl Nm Ny Of Oy Pz) Nb(Ii In Md Mh Ny Of Oy Pz) Pd(Hu In Jh Nl Nm Ns Pz) Jh(Iv Nk Nl Nm Pz) Ne(Nc Nk Nl) Hu(Ik Ns Ny) Ii(Md Mh Ny) In(Iv Jt Mh) Pz(Iv Jt Qa) Nm(Jt Qa) Mz(Lj Lw) Nh(Nl Qa) Ni(Nk Nl) Ik(Li Mj) Nslv LiLj} aA{Pe(Fp Hq Hr Hu Hv Hw Hx Ih Ii Ij Ik Il Im In Io Ir Is It Iu Iv Jg Jh Jj Jk Jm Jn Jo Jp Jq Js Jt Lh Li Lj Lu Lx Ly Lz Mb Mc Md Me Mf Mh Mi Mj Mk Ml Mn Mp Mq Mr Ms Mt Mv Mw Mx My Mz Na Nb Nc Nd Ne Nf Ng Nh Ni Nk Nl Nm No Nq Nr Ns Nt Nu Nv Nw Nx Ny Oe Of Og Oh Oi Ok Om Oy Oz Pa Pb Pd Pf Po Pz Qa Qc Qd Qe) Jk(Fp Hq Hr Hv Hw Hx Ih Ii Ij Ik Il Im In Iq Ir Is It Iu Iv Jg Jh Jm Jo Jp Jq Js Jt Lh Li Lj Lu Lx Ly Lz Mb Mc Md Me Mf Mh Mi Mj Mk Ml Mn Mp Mq Mr Mt Mv Mw Mx My Mz Na Nb Nc Nd Ne Nf Ng Nh Ni Nk Nl Nm No Nq Nr Ns Nt Nu Nv Nw Nx Ny Oe Of Og Oh Oi Ok Oy Oz Pa Pb Pd Pf Po Pz Qa Qb Qc Qd Qe) Is(Fp Hq Hr Hu Hv Hw Hx Ih Ii Ij Ik Il Im In Iq Ir It Iu Iv Jg Jh Jj Jm Jn Jo Jp Jq Js Jt Li Lj Lu Lx Ly Lz Mb Mc Md Me Mf Mh Mi Mj Mk Ml Mn Mq Mr Mt Mv Mw Mx My Mz Na Nb Nc Nd Ne Nf Ng Nh Ni Nk Nl Nm No Nr Ns Nt Nu Nv Nw Nx Ny Oe Of Og Oh Oi Ok Om Oy Oz Pa Pb Pd Pf Po Pz Qa Qb Qc Qd Qe) Nq(Fp Hq Hr Hv Hw Hx Ih Ii Ij Ik Il Im In Io Iq Ir It Iu Iv Jg Jh Jj Jm Jo Jp Js Jt Lh Li Lj Lu Lx Ly Lz Mb Mc Md Me Mf Mh Mi Mj Mk Ml Mm Mn Mp Mq Mr Mu Mv Mw Mx My Mz Na Nb Nc Nd Ne Nf Ng Nh Ni Nk Nl Nm Nn No Nr Ns Nt Nu Nv Nw Nx Ny Oe Of Og Oh Oi Ok Oy Oz Pa Pb Pd Pf Po Qa Qb Qd Qe) Jg(Fp Hq Hr Hu Hv Hw Hx Ih Ii Ij Ik Il Im In Io Iq Ir It Iu Iv Jh Jj Jm Jo Jp Js Jt Lh Li Lj Lu Lx Ly Lz Mb Mc Md Me Mf Mh Mi Mj Mk Ml Mm Mn Mq Mr Mt Mv Mw Mx My Mz Na Nb Nc Nd Ne Nf Nh Ni Nk Nl Nm No Nr Nt Nu Nv Nw Nx Ny Oe Of Oh Oi Ok Om Oy Oz Pa Pb Pc Pd Pf Po Pz Qa Qb Qc Qd Qe) Mp(Fp Hq Hr Hu Hv Hw Hx Ih Ii Ik Il Im In Iq Ir It Iu Iv Jh Jj Jm Jo Jp Js Jt Li Lj Lu Lx Ly Lz Mb Mc Md Me Mf Mh Mi Mj Mk Ml Mm Mn Mq Mr Ms Mv Mw Mx My Mz Na Nb Nc Nd Ne Nf Ng Nh Ni Nk Nl Nm No Nr Ns Nt Nu Nv Nw Nx Ny Oe Of Og Oh Oi Ok Oy Oz Pa Pb Pd Pf Po Pz Qa Qb Qc Qd Qe) Jn(Fp Hq Hr Hu Hv Hw Hx Ih Ii Ij Ik Il Im In Iq Ir It Iu Iv Jh Jj Jm Jo Jp Jq Js Jt Li Lj Lu Ly Lz Mb Mc Md Me Mf Mh Mi Mj Mk Ml Mn Mq Mr Mt Mv Mw Mx My Mz Na Nb Nc Nd Ne Nf Ng Nh Ni Nk Nl Nm No Nr Ns Nt Nu Nv Nw Nx Ny Oe Of Og Oh Oi Ok Oy Oz Pa Pb Pd Pf Po Pz Qa Qb Qc Qd Qe) Jq(Fp Hq Hr Hu Hv Hw Hx Ih Ii Ij Ik Im In Io Ir It Iu Iv Jh Jj Jm Jo Jp Js Jt Li Lj Lu Lw Lx Ly Lz Mb Mc Md Me Mf Mh Mi Mj Mk Ml Mn Mq Mr Ms Mv Mw Mx My Mz Na Nb Nc Nd Ne Nf Ng Nh Ni Nk Nl Nm No Nr Ns Nu Nv Nw Nx Ny Oe Of Og Oh Oi Ok Om Oy Oz Pa Pb Pd Pf Po Qa Qb Qc Qd Qe) Mt(Fp Hq Hr Hu Hv Hw Hx Ih Ii Ij Ik Im In Iq Ir It Iu Iv Jh Jj Jm Jo Jp Js Jt Li Lj Lu Lx Ly Lz Mb Mc Md Me Mf Mh Mi Mj Mk Ml Mn Mq Mr Mv Mw Mx My Mz Na Nb Nc Nd Ne Nf Ng Nh Ni Nk Nl Nm No Nr Ns Nt Nu Nv Nw Nx Ny Oe Of Og Oh Ok Oy Oz Pa Pb Pd Pf Po Pz Qa Qb Qc Qd Qe) Lh(Fp Hq Hr Hu Hv Hw Hx Ih Ii Ij Ik Im In Iq Ir It Iu Iv Jh Jm Jo Jp Js Jt Li Lj Lu Lx Ly Lz Mb Mc Md Me Mf Mh Mi Mj Mk Ml Mn Mq Mr Mv Mw Mx My Mz Na Nb Nc Nd Ne Nf Ng Nh Ni Nk Nl Nm No Nr Ns Nt Nu Nv Nw Nx Ny Oe Of Og Oh Ok Oy Oz Pa Pd Pf Po Pz Qa Qb Qc Qd Qe) Om(Fp Hq Hr Hu Hv Hw Hx Ih Ii Ij Ik Im In Iq Ir It Iu Iv Jh Jj Jm Jo Jp Js Jt Li Lj Lu Lx Ly Lz Mb Mc Md Me Mf Mh Mj Mk Ml Mn Mq Mr Mv Mw Mx My Mz Na Nb Nc Nd Ne Nf Ng Nh Ni Nk Nl Nm No Nr Ns Nt Nu Nv Nw Nx Ny Oe Of Oh Oi Ok Oy Oz Pa Pd Pf Po Pz Qa Qb Qc Qd Qe) Lw(Fp Hq Hr Hu Hv Hw Ih Ii Ij Ik Im In Iq Ir It Iu Iv Jh Jj Jm Jo Jp Js Jt Li Lj Lu Ly Lz Mb Mc Md Me Mf Mh Mi Mj Mk Ml Mn Mq Mr Mv Mw Mx My Mz Na Nb Nc Nd Ne Nf Ng Nh Ni Nk Nl Nm Nr Ns Nu Nw Nx Ny Oe Of Og Oh Oi Ok Oy Oz Pb Pd Pf Po Pz Qa Qb Qc Qd Qe) Mm(Fp Hq Hr Hu Hv Hw Ih Ii Ik Im Io Iq Ir It Iu Iv Jh Jj Jm Jo Jp Js Jt Li Lj Lu Lx Ly Lz Mb Mc Md Me Mf Mh Mi Mj Mk Ml Mn Mq Mr Ms Mv Mw Mx My Mz Na Nb Nc Nd Ne Nf Ng Nh Ni Nk Nl Nm Nr Ns Nu Nv Nw Ny Oe Of Og Oh Oi Ok Oy Oz Pa Pb Pf Po Pz Qb Qc Qd Qe) Il(Fp Hq Hr Hu Hv Hw Hx Ih Ii Ij Ik Im In Io Ir Iu Iv Jh Jj Jm Jo Jp Jt Li Lu Lx Ly Mb Md Me Mf Mh Mi Mj Ml Mn Mq Mr Ms Mv Mw Mx My Mz Na Nb Nc Nd Ne Nf Nh Ni Nk Nm No Nr Ns Nt Nu Nv Nw Nx Ny Oe Og Oh Oi Ok Oy Oz Pa Pd Po Qa Qb Qd Qe) Mu(Fp Hq Hr Hv Hw Ih Ii Ik Im In Iq Ir It Iu Iv Jh Jj Jm Jp Js Jt Li Lj Lu Ly Lz Mb Mc Md Me Mj Mk Ml Mq Mr Mv Mw Mx My Na Nb Nc Nd Ne Nf Ng Nh Ni Nk Nl Nm Nr Ns Nu Nv Ny Oe Of Oh Oy Oz Pd Pf Po Pz Qa Qb Qc Qd) Nv(Fp Hr Hu Hv Hw Hx Ih Ij Ik Im In Ir Iv Jh Jj Jo Jp Jt Li Lx Mb Me Mf Mh Mi Mn Mq Mr Ms Mv Mw Mx My Mz Na Ne Nf Ng Nh Ni Nk Nm No Ns Nt Nu Nw Nx Ny Oe Og Oh Oi Ok Oz Pa Pb Pd Po Qa Qb Qd Qe) Nx(Fp Hq Hr Hu Hv Hx Ij Ik Im In Io Ir Iu Iv Jh Jj Jo Jp Li Lu Lx Me Mf Mh Mi Ml Mn Mr Ms Mv Mw Mx My Mz Nc Nd Ne Nf Nh Ni Nk No Ns Nt Nu Nv Ny Oe Og Oh Oi Ok Oz Pa Pb Pd Po Qa Qb Qd Qe) Nt(Hq Hr Hx Ij Ik Im In Io Ir It Iv Jh Jj Jo Jp Jt Li Lu Lx Ly Mb Me Mf Mh Mi Ml Mn Mq Ms Mv Mw Mx My Mz Nb Ne Nf Nh Ni Nk No Ns Nw Ny Oe Og Oh Oi Ok Oz Pa Pb Pd Po Qa Qb Qd Qe) Po(Fp Hr Hv Hw Hx Ij Im In Io Ir Iu Iv Jh Jj Jo Jp Jt Li Lj Lx Mb Me Mf Mi Ml Mn Mq Ms Mv Mw My Mz Nb Nd Ne Nf Nh Ni Nm No Ns Nw Oe Og Oh Oi Ok Oz Pa Pb Pd Qa Qd Qe) Jo(Hr Hx Ij Ik Im In Io Ir It Iv Jh Jj Jp Jt Li Lu Lx Ly Me Mf Mh Mi Ml Mn Ms Mv Mw Mx My Mz Ne Nf Ng Nh Ni Nk No Ns Nw Ny Oe Og Oh Oi Ok Oz Pa Pb Pd Qa Qb Qd Qe) Pc(Fp Hq Hv Ih Ik Iq It Iu Jh Jj Jm Js Jt Li Lj Lu Ly Lz Mb Mc Md Me Mf Mh Mj Mk Ml Mq Mv Mw Na Nb Nc Nd Ne Ng Nh Nk Nl Nm Nr Ns Nu Oe Of Oh Oy Oz Pb Pf Pz Qb Qc) Nw(Hr Hv Hw Hx Ii Ij In Io Ir Iu Iv Jh Jt Lu Lx Mb Me Mf Mh Mi Mn Mq Mr Ms Mv Mx My Mz Na Nb Nd Nf Ni Nk Nm No Nu Oe Og Oh Oi Oz Pa Pb Pd Qa Qe) No(Hv Hx Ij Im In Io Ir Iv Jh Jj Jp Jt Lx Mb Me Mf Mi Mn Mq Ms Mv Mw Mx My Mz Nb Ne Ni Nm Ns Nu Ny Og Oh Oi Ok Oz Pa Pb Pd Qa Qb Qd Qe) Ij(Hr Hx Ik In Io Ir It Iu Iv Jh Jj Jp Li Lu Lx Mb Me Mf Mh Mi Ml Mn Ms Mv Mw My Mz Nd Nk Ns Nu Oe Og Oh Oi Ok Oz Pa Pb Pd Qa Qd Qe) Lx(Hv Hw Hx Im In Io Ir Iv Jh Jp Jt Ly Mb Me Mf Mh Mn

Figure 34 Continued

Mq Ms Mv My Mz Na Ne Ni Nm Ns Nu Ny Og Oh Oi Ok Oz Pb Pd Qa Qd Qe) Hx(Hr Im In Io Ir Iv Jh Jj Jp Li Lu Me Mf Mh Mi Ml Mn Ms My Mz Ne Ni Ns Nu Ny Oe Og Oh Oi Ok Oz Pa Pb Pd Qa Qd Qe) Ma(Fp Hq Hu Ih Iq It Iu Jj Jm Js Lj Lu Ly Lz Mc Md Mf Mh Mj Mk Mx Nc Ne Ng Ni Nl Nm Nr Nu Oe Of Oh Oy Pf Pz Qc) Jr(Fp Hq Hu Hv Ii Iq Ir Iv Jm Jt Ly Lz Mc Md Mj Mk Mq Mx Na Nc Ng Nk Nl Nr Ny Of Pf Pz Qa Qb Qd) Nj(Fp Hu Hv Iq It Jj Js Lh Lj Lu Ly Lz Mc Mk Ml Mr Nc Ng Nk Nl Nr Oe Of Oz Pb Pf Pz Qc) Mn(Hw Im In Io Ir Lu Mf Mh Mi Mq Ms My Mz Nb Nf Ni Og Oh Oi Pa Pd Qa Qd Qe) Io(Im In Ir Iv Jh Jp Jt Mf Mi Mv My Mz Nb Nr Ny Ok Pa Qa Qd Qe) Mg(Hq Ii Iq It Iu Js Lj Lz Mc Md Mi Mk Mv Nb Nm Pf Pz Qc) Qa(Jh Jp Me Mf Mi Ml Ms Mv Mw Mz Oe Og Oh Oi Pa Pb) Ms(In Jh Jp Mi Mv My Mz Nb Ny Ok Pa Qd Qe) Nn(Iq Jm Ly Lz Mc Mk Mv Of Oh Pf Pz Qc) Mz(Im Jh Jp Me Mf Mi Ml My Og Oi Pb Qe) Qe(In Jh Jp Mf Mi Mv Oe Og Oi Ok Pa) Mf(In Jp Mi My Og Oi Ok Pa Qd) Jp(Hw In Ir Mi Oi Pa Pd) My(Im Jh Mi Mv Oi Ok) Og(In Jh Mv Nb Ok Pa) Qd(Mi Mw Oi Pa) Jh(Hu Mi Ns Oy) Ok(Mi Pa) MwNg NbPb} Jr{Pg(Fp Hq Hr Hu Hv Hw Hx Ih Ij Ik Il Im In Iq Ir Is It Iu Iv Jg Jh Jk Jm Jn Jo Jp Js Jt Li Lj Lu Lx Ly Lz Mb Mc Md Me Mf Mh Mj Mk Ml Mn Mq Mr Ms Mt Mv Mw Mx My Mz Na Nb Nc Nd Ne Nf Ng Nh Ni Nj Nk Nl Nm Nr Ns Nt Nu Nv Nw Nx Ny Oe Of Oh Oi Om Oy Oz Pa Pd Pe Pf Po Pz Qa Qb Qc Qd Qe) Ma(Fp Hq Hr Hu Hv Hw Hx Ih Ii Ij Ik Il Im In Io Iq Ir Is It Iu Iv Jg Jh Jm Jn Jo Jp Js Jt Li Lj Lu Lw Ly Lz Mc Md Me Mf Mg Mh Mj Mk Ml Mn Mq Ms Mt Mv Mw Mx My Mz Na Nb Nc Nd Ne Nf Ng Nh Ni Nj Nk Nl Nm Nr Ns Nu Nv Nw Nx Ny Oe Of Og Oh Oi Ok Om Oy Oz Pb Pd Pf Po Pz Qa Qc Qd Qe) Mg(Fp Hq Hr Hu Hv Hw Hx Ih Ii Ij Ik Il Im Io Iq Ir Is It Iu Iv Jg Jh Jk Jm Jn Jo Jp Jq Js Jt Li Lj Lw Lx Ly Lz Mb Mc Md Me Mf Mh Mj Mk Ml Mn Mq Mt Mv Mw Mx My Mz Na Nb Nc Nd Ne Nf Nh Ni Nj Nk Nl Nm Nr Ns Nu Nv Nw Nx Ny Oe Of Oh Oi Om Oy Oz Pb Pd Pf Po Pz Qa Qb Qc Qd Qe) Nt(Fp Hq Hr Hu Hv Hw Hx Ih Ii Ij Ik Il Im Iq Ir Is It Iu Iv Jg Jh Jk Jm Jn Jo Js Jt Lh Li Lj Lu Lx Ly Lz Mb Mc Md Me Mf Mh Mi Mj Mk Mn Mq Mr Ms Mv Mw Mx My Mz Na Nb Nc Nd Nf Ng Nh Ni Nk Nl Nm Nr Ns Nu Nv Nw Nx Ny Oe Of Oh Oi Ok Oy Oz Pa Pb Pd Pe Pf Po Pz Qa Qb Qc Qd Qe) Lv(Fp Hq Hr Hu Hv Hw Hx Ih Ii Ij Ik Il Im In Iq Ir Is It Iu Iv Jg Jh Jm Jn Jo Jp Jq Js Jt Li Lj Lw Ly Lz Mb Mc Md Me Mf Mh Mj Mk Ml Mn Mq Ms Mv Mw Mx My Mz Na Nb Nc Nd Ne Nf Ng Nh Ni Nj Nk Nl Nm Nr Ns Nu Nv Nw Nx Ny Oe Of Og Oi Oy Oz Pb Pd Pf Po Pz Qa Qb Qc Qd Qe) Mi(Fp Hq Hr Hu Hv Hw Hx Ih Ii Ij Ik Il Im Iq Ir Is It Iu Iv Jk Jm Jn Jo Js Jt Li Lj Lu Lx Ly Lz Mb Mc Md Me Mf Mj Mk Mn Mp Mq Mr Mv Mw Mx My Mz Na Nb Nc Nd Ne Nf Ng Nh Nk Nl Nm Nr Ns Nu Nv Nw Nx Ny Oe Of Oh Oi Oy Oz Pa Pb Pd Pe Pf Po Pz Qa Qb Qc Qd Qe) Mp(Fp Hr Hu Hv Hw Hx Ih Ii Ij Ik Il Im Iq Ir Is It Iu Iv Jm Jn Jo Js Jt Li Lj Lu Lw Lx Ly Lz Mb Mc Md Me Mf Mh Mj Mk Ml Mn Mq Ms Mv Mw Mx My Na Nb Nc Nd Ne Nf Ng Nh Nk Nl Nm Nr Nu Nv Nx Ny Oe Of Og Oh Oi Oy Oz Pb Pf Po Pz Qa Qb Qc Qd Qe) Ip(Fp Hq Hr Hu Hv Hx Ih Ii Ij Ik Il Im In Iq Ir Is It Iu Iv Jh Jm Jn Js Jt Li Lj Ly Lz Mb Mc Md Me Mf Mh Mj Mk Ml Mn Mq Ms Mv Mw Mx My Mz Na Nc Nd Ne Nf Ng Nh Ni Nj Nk Nl Nm Nr Ns Nu Nw Nx Ny Oe Of Oh Oi Oy Oz Pb Pd Pf Po Pz Qa Qb Qd Qe) Pc(Fp Hq Hr Hu Hv Hx Ih Ii Ij Ik Il In Iq Ir It Iu Iv Jg Jh Jm Jn Js Jt Li Lj Lw Ly Lz Mb Mc Md Me Mf Mh Mj Mk Ml Mn Mq My Mw Mx My Na Nb Nc Ne Nf Ng Nh Ni Nj Nk Nl Nm Nr Nu Nv Nw Nx Ny Oe Of Oh Oi Oy Oz Pb Pd Pf Po Pz Qa Qb Qc Qd Qe) No(Fp Hq Hu Hv Hw Hx Ih Ij Ik Il Iq Ir It Iu Iv Jm Jn Js Li Lx Ly Lz Mc Md Me Mk Mq Mr Ms Mv Mw Mx Mz Na Nb Nc Nd Ne Nf Ng Nh Ni Nk Nl Nr Nv Nw Nx Ny Oe Of Oi Oy Pa Pd Pe Pf Po Pz Qa Qb Qd Qe) Lx(Fp Hq Hr Hw Hx Ik Im In Io Is Iv Jg Jh Jk Jm Jn Jo Jp Jq Js Jt Lh Lj Lu Lw Ly Lz Mb Mf Mh Mj Ml Ms Mt Mv My Mz Na Nb Ne Ng Ni Nj Nm Nq Nr Ns Nu Nv Nw Ny Og Oh Ok Om Oy Pa Pb Pe Qa Qc) Mu(Fp Hq Hu Hv Ih Ii Ij Il Iq Ir Iv Jg Jh Jk Jm Jn Li Lj Ly Lz Mb Mc Md Me Mf Mj Mk Mn Mq Mv Mw Mx My Na Nb Nc Ne Nf Nh Ni Nk Nl Nm Nv Nx Ny Oe Of Om Oy Oz Pd Pf Po Pz Qa Qb Qd Qe Wm) Mt(Fp Hr Hw Hx Ik Il Im In Io Is It Iu Jg Jh Jj Jk Jo Jp Jq Js Jt Lj Lu Lw Mb Mh Ml Mr Ms My Mz Nb Nd Ne Nf Ni Nj Nm Nr Ns Nv Nw Ny Oe Og Oh Oi Ok Om Oz Pa Pb Pe Po Pz Qc) Lh(Hq Hu Hv Hw Ih Ij Il Iq Ir Iu Iv Jk Jm Jn Js Jt Li Lu Lz Mb Mc Me Mf Mk Mn Mq Mr Mv Mw Mx Mz Na Nb Nc Nd Nf Nh Nk Nl Nm Nr Nu Nv Nx Ok Oz Pa Pd Pe Pf Pz Qb Qd Qe) Jk(Hr Hu Hw Ii Ik Im In Io Is It Iv Jg Jh Jm Jo Jp Jq Js Jt Lu Lw Mh Ml Mr Ms My Mz Ng Ni Nj Nm Ns Nw Oe Oh Oi Ok Om Oy Pa Pb Pe Qa Qc) Om(Hu Hw Ii Ik Im In Io Is It Iu Jh Jo Jp Jq Js Jt Lu Lw Mb Mh Ml Mr My Nd Ng Nj Ns Nv Nw Ny Oe Of Oh Oi Ok Oy Pa Pb Pe Pz Qc) Jj(Hw Hx Ij Il Im Is Iu Jg Jh Jp Jq Jt Lu Lw Ml Mn Mr Mv Mw My Nb Nd Nj Nr Nu Nw Nx Oh Ok Pa Pd Pe Po Qe) Pa(Hr Hw Ik Im In Io Is Jg Jh Jo Jp Jt Lj Lu Lz Mh Mk Ml Ms Mz Ni Nj Nm Nv Nw Og Oh Ok Pb Qa Qc) Jq(Hw Hx Im Is It Iu Jg Jh Jo Jp Js Lu Lw Ml Mr Mv My Nb Nd Nj Nr Nu Nv Nw Og Oh Ok Pe Po) Lw(Hw Hx Il Im In Io Is Iu Jg Jh Jo Jp Mr Ms Mv Mz Nb Nd Nj Nr Nv Nw Og Ok Pe Po) Nq(Fp Hq Ih Il Iq Iu Lj Lz Mc Md Mf Mn Mq Mx Nd Nl Nv Nx Pd Pf Po Qb Qe) Jo(Hr Ik Im In Io Is It Iv Jg Jh Jp Js Lu Ml Ms Mz Nj Nv Nw Og Oh Ok Pb) Nw(Hw Io Is Iu Jh Jt Lj Lu Mb Mh Ml Mr Ms Nd Nj Ns Og Oh Ok Pe Qc) Ok(In Io Is It Iu Jg Jh Jp Lu Ml Mr Ms Nd Nj Nv Og Oh Pb Pe Qc) Nv(Hw Im In Io Is Jh Jp Mr Ms Mz Ni Nj Ns Oe Og Oi Pb Pe) Pe(Hr Ik Im In Io Is Jg Jh Jp Lu Mh Ml Ms Nj Og Oh Pb) Mr(Hr Im In Io Is Jg Jh Jp Lu Mh Ml Ms Nj Og Oh Pb) Jp(Hw Im Io Is Iu Jt Lu Mb Ms Nd Nj Nr Oh Qc) Jg(Hu Hw Io Lu Ml My Nd Ng Ns Oh Oi Oy Pz) Is(Hw In Io It Lu Ml Ms Mz Nj Og Oh Qc) Lu(Im Jt Me Nj Oh) Jh(Io Ms My Og Oh) Nb(Mh Ml Ms Nj) Hw(It Ml Nj Oh) Io(Im Iu Jt) Wm(Js Nn) Mv(My Og) Mz(Lj Ml) Nj(Nd Oh) MsMw HxOg ImOh ItJt} Nn{Mr(Fp Hq Hr Hv Hw Hx Ih Ii Ij Ik Il Im In Io Iq Ir It Iu Iv Jg Jh Jk Jm Jo Js Jt Lh Li Lj Lu Lx Ly Lz Mb Mc Md Me Mf Mg Mh Mi Mj Mk Ml Mm Mn Mp Mq Mu Mv Mw Mx My Mz Na Nb Nc Nd Ne Nf Ng Nh Nk Nl Nm Nq Nr Ns Nt Nu Nv Nw Nx Ny Oe Of Oh Om Oy Oz Pa Pb Pd Pe Pf Po Pz Qb Qc Qe) Jn(Fp Hq Hr Hv Hx Ih Ii Ij Ik Il Im In Iq Ir Is It Iu Iv Jg Jh Jk Jm Jp Jt Li Lj Lw Ly Lz Mb Mc Md Me Mf Mg Mh Mj Mk Ml Mm Mn Mq Mt Mv Mw Mx My Mz Na Nb Nc Ne Nf Ng Nh Ni Nj Nk Nl Nm Nq Nr Ns Nu Nv Nw Nx Ny Oe Of Oh Om Oy Oz Pb Pc Pd Pf Po Pz Qa Qb Qc Qd Qe) Ok(Fp Hq Hr Hv Ih Ii Ij Ik Im In Io Iq Ir It Iu Iv Jg Jh Jj Jk Jm Jo Js Jt Li Lj Lu Lw Ly Lz Mb Mc Md Me Mf Mg Mh Mj Mk Ml Mm Mn Mq Mv Mw Mx My Mz Na Nb Nc Ne Nf Ng Nh Ni Nj Nk Nl Nm Nq Nr Ns Nu Nv Nw Nx Ny Oe Of Oh Om Oy Oz Pb Pc Pd Pf Po Pz Qa Qb Qc Qd Qe) Pg(Fp Hq Hr Hx Ih Ii Ij Ik Il Iq It Iu Iv Jg Jh Jk Jm Jp Js Li Lj Lu Lw Lx Ly Lz Ma Mb Mc Md Me Mf Mg Mh Mi Mj Mk Ml Mm Mn Mp Mq Mt Mv Mw Mx Nb Nc Nd Ne Nf Nh Nj Nk Nl Nm Nq Nr Nu Nv Nw Nx Ny Oe Of Oh Om Oz Pd Pf Po Pz Qb Qc Qd Qe) Jq(Fp Hq Hr Hv Ih Ii Ij Ik In Io Iq Ir It Jg Jh Jk Jm Js Jt Li Lj Lu Lw Ly Lz Mb Mc Md Me Mf Mg Mh Mj Mk Ml Mn Mq Mv Mw My Mz Na Nb Nc Ne Nf Ng Nh Ni Nk Nl Nm Nq Ns Nu Nv Nw Nx Ny Oe Of Oh Om Oy Pb Pc Pd Pf Pz Qa Qb Qc Qd Qe) Nt(Fp Hq Hr Ih Ii Ij Ik Il Im Iq It Iu Iv Jg Jh Jk Jm Js Jt Li Lj Lu Lx Ly Lz Mb Mc Md Me Mg Mh Mi Mj Mk Ml Mm Mn Mp Mq Mv Mw Mx My Na Nb Nc Nd Nf Nh Nk Nl Nm Nq Nr Ns Nu Nv Nx Ny Oe Of Oh Oy Oz Pa Pd Pf Po Pz Qb Qc Qe) Is(Fp Hq Hr Hv Hx Ih Ii Ij Ik Il Im Iq Ir It Iu Iv Jg Jh Jk Jm Js Jt Li Lj Lw Ly Lz Mb Mc Md Me Mg Mh Mj Mk Ml Mm Mn Mq Mt Mv Mw Mx Na Nb Nc Ne Nh Nk Nl Nm Nq Nu Nv Nw Nx Ny Oe Of Oh Om Oz Pb Pd Pf Po Qa Qb Qd Qe) Pe(Fp Hq Hr Hv Hx Ih Ii Ij Ik Il Iq It Iu Jg Jk Jm Js Jt Lj Lu Lx Ly Lz Mb Mc Md Mg Mi Mj Mn Mp Mq Mv Mw Na Nb Nc Nd Ne Nf Nh Nk Nl Nm Nq Nr Ns Nu Nv Nx Ny Oe Of Oh Om Oz Pa Pd Pf Po Pz Qb Qc Qe) Jo(Fp Hw Hx Ih Ii Ik Il Im In Io Ir Iu Iv Jg Jh Jk Jt Lu Lw Lx Lz Ma Md Me Mf Mg Mh Mi Ml Mm Mn Mp Mu Mx My Mz Nb Nd Nf Ng Ni Nj Nk Nl Nr Ns Nv Ny Oe Of Om Oy Oz Pc Po Pz Qa Qb Qd Qe) Ip(Hr Hv Ii Ij Il Im In Io Ir Iu Iv Jg Jh Jk Jp Jt Lu Lw Lz Ma Mb Md Me Mf Mh Mj Mm Mn Mp Mq Ms Mt Mu Mx Na Nd Nf Ni Nj Nk Nl Nu Nv Nw Nx Ny Og Om Oz Pb Pc Qd Qe) Mz(Hw Hx Il Im Io Ir Iu Iv Jg Jh Jj Jk Jp Lu Lx Ma Md Me Mf Mg Mh Mi Ml Mm Mp Ms Mt Mu Mv Mx My Nd Ng Nj Nk Nl Nr Nv Nw Ny Of Og Oi Om Oy Oz Pb Pc Po Qa Qd Qe) Qa(Hw Hx Ii Il Im Io Ir It Iu Iv Jg Jh Jj Jk Jp Lu Ly Ma Me Mf Mg Ml Mm Mn Mp Ms Mt Mu Mx Nb Nd Ni Nj Nl Nr Ns Nv Nw Nx Og Oi Om Oz Pb Pc Po Qc Qd) Pa(Fp Hr Hx Ih Ij Im In Io Ir Iv Jg Jh Jj Jk Jp Jt Lu Lw Lx Ma Mb Me Mf Mh Mi Mm Mn Mp Mq Mu My Nf Ng Nm Ns Nv Nw Nx Ny Og Om Oy Pb Pc Po Qd Qe) Hw(Hx Ih Ii Il Im In Io Ir Iu Iv Jg Jh Jj Jk Lu Lw Ma Mc Mf Mg Mi Mm Mn Mp Ms Mu Mx Nb Nd Ni Nl Ns Nv Nx

Figure 34 Continued

Om Oy Pa Pe Po Pz Qa) Mi(Hv Hw Ii In Ip It Jj Jm Jo Jp Lu Lw Ly Ma Mg Mh Ms Mt Mz Ne Nf Ng Ni Nj Nw Og Oi Ok Om Qa) Mp(Hq Hw Ij In Ip Jj Jm Jo Jp Lu Ma Mr Ms Mt Mz Nb Nf Ni Nj Ns Nt Nw Og Oi Ok Om Pa Pe) Nt(Ii Ik In Ip It Jm Jp Lu Lw Ly Ma Mg Ms Mt Mz Ne Nf Nj Nq Nw Og Oh Oi Ok Om) Ip(Hw Jj Jp Lu Lw Lx Ma Mg Mr Ms Mt Mz Nf Nq Nv Nw Og Oh Oi Ok Om Pa Pe Po) Ms(Jh Jj Jk Jo Jp Lw Lx Mg Mr Mt Mv Mz Nb Nv Nw Oh Ok Om Pa Pe Po) Nq(Hw Jm Jp Lw Ma Mt My Mz Nf Ng Ni Nj Ns Oi Ok Oy Pe) Og(Hw Hx Jh Jk Jo Lw Lx Mr Mt Mv Mz Nb Nv Nw Pa Pe Po) Jj(Hw Jg Jk Jo Lu Lx Ma Mg Mr Mt Nv Om Pa Pe Po) Ma(Hw Lw Lx Mb Mr Mt Mz Nf Nw Oi Ok Pa Pe) Mg(Hw Ik In Jp Lu Lx Mr Mz Ng Oi Ok Pe Pz) Lx(Jm Jp Lw Ly Mh Mz Ni Oh Ok) Mt(Lw Mh My Ny Oi Pb Qc) Pa(Lw Mh Mk Ni Nj Oh) Oh(Mr Oi Om Pe) Lw(Jp Mr Pe) My(Jg Mv Om) Mz(Ml Qc) Hw(It Nw) Jo(It Nw) Om(Oy Pb) LuNj NgJg JhOy NvOi PbPe} Pg{Jj(Fp Hr Hu Hv Hx Ih Ii Ij Il In Iq It Jm Js Li Lj Lu Lx Ly Lz Mc Md Me Mf Mh Mj Mk Ml Mn Mq Mr Ms Mv Mw Mx Na Nb Nc Nd Ne Ng Nh Ni Nk Nl Nm Nr Ns Nv Nw Nx Ny Oe Of Oi Pa Pd Pe Pf Po Pz Qb Qc Qd) Mm(Hq Hu Hv Hw Hx Ii Ij Ik Im In Ip Ir Iv Jm Jo Jp Jt Lu Mg Mi Mk Mr Ms Mt My Na Nb Nf Ni Nj Ns Nt Nw Of Og Oi Ok Om Oz Pa Pb Pd Pe Pf Pz Qa Qd) Ip(Hq Hw Ii Ik Im Io Ir Jm Jn Jo Jp Jt Lu Lw Mb Mg Mi Mp Mr Ms Mt Mz Na Nb Nf Ng Ni Nj Nm Nq Ns Nt Nw Og Oh Ok Om Oy Oz Pa Pb Pc Pe Qa) Mz(Hq Hu Hx Ii Ik Im In Io Iu Jh Jn Jo Jp Jt Lw Ma Md Mg Mh Mi Ml Mp Ms Mt My Ng Ni Nj Nq Ns Nt Ny Of Og Oh Oi Ok Oy Pa Qc) Ok(Hq Hu Ii Ik In Io Iu Jh Jn Jo Jp Lu Lw Ma Mg Mi Ml Mp Ms Mt My Ng Nj Nq Ns Nw Of Og Oh Oi Oy Oz Pc Pz) Pb(Hv Hw Ij In Io Jh Jn Jo Jp Jt Lw Ma Mb Mg Mi Mq Mr Mt Na Nb Nf Ni Nr Nt Nw Om Pa Pc Pe Qa) Pc(Hw Im Io Ir Jn Jo Jp Mi Mr Ms Mt My Nf Ng Ni Ns Nt Og Oy Pe Qa) Oy(Io Jk Jn Jp Lw Mg Mi Mt Mv Nb Nf Nq Nw Pa Pe Po) Mt(Hw Ik Io Jt Lw Mh My Ng Ni Nt Ny Of Og Qa) Jn(Ii Ik In Io Jm Js Lw Ma Mg Mi Mp Nq Nt Og) Og(Jh Jt Lw Mg Mv Mw Nb Nw Om) Io(Ir Jp Jt Lw Mi Nt Qa) My(Jg Jh Nb Nq Nw Om) Lw(Hq Jp Lu Ns) Ng(Mg Mi Nq Om) Ms(Jg Nb Om) Mi(Hq Qa) Mp(Hq Ns) Jt(Ii Jo) Of(Nb Om) NqHu} Ip{Nt(Hw Hx Ii Ik In Io Jg Jh Jk Jm Jn Jo Jp Jt Lu Lw Ly Ma Mb Md Mg Mi Mm Mn Mp Ms Mv Ne Nf Ng Nj Nm Nq Ns Nw Og Oh Oi Ok Om Oz Pb Pe Qa Qd) Mt(Hw Jj Jn Jo Jt Mh Mi Mm Mp Mr My Mz Nb Ny Og Ok Pa Pb Pc Pe Qa) Mm(Hw Hx In Ir Jo Lu Lx Mr Nb Nf Nr Nv Nw Ok Om Pa Pe Po Qa) Mz(Hw Iu Jj Jk Jo Lx Ma Mg Mi Ml Mr Nj Nv Og Ok Pa Pb Pc Pe) Jj(Hw Hx Il Jn Jo Jt Lx Md Mg Mi Mp Mr Nb Nv Om Pa Pe Po) Ok(Jk Jn Jp Lu Lx Mg Mi Mp Nv Nw Og Oh Pa Pb Pc) Pe(Jn Jp Lw Ma Mg Mi Mp Nq Nw Og Oh Pb Pc) Om(Hw Jn Lu Mi Mp Ms Ng Oh Oy Pa Pb Pc) Og(Hw Hx Jh Jk Mi Mr Mv Nq Nv Pa Po) Jn(Jk Lx Ma Mi Mp Mr Nq Nv Pa Pc) Hw(Jp Mi Mp Nq Nv Nw Oh Pb Pc) Qa(Lx Mi Mp Nq Nv Nw Pa Pc) Mr(Lw Ma Mp Nq Oh Pb Pc) Mi(Io Jp Ms Nj Nw Pc) Nb(Mp Ms My Pb) Jt(Lx Nq Nw Pa) Pa(Lw Oh Pc) Po(Pb Pc) Nq(Ir Ms) Lx(Ly Pc) Mp(Jp Nw) MsJg MvMy HuJk JhOy JoNw} Jn{Mm(Hw Hx Il In Ij Jk Jo Jp Lu Lx Ma Mi Mp Ms Mt Mz Nb Nd Nf Ni Nq Nr Nv Nw Og Oi Ok Om Pa Pc Pd Po Pz Qa) Nq(Hw Ik In Io Jm Jo Jp Js Lw Ma Mp Mr Mt My Mz Ni Nj Nr Ns Nt Nw Oi Ok Pa Pb Pc Pe Qa) Mp(Hq Hw In Io Jg Jj Jp Js Lu Ma Mr Mt Mz Nb Ni Nj Ns Nt Nw Ok Om Pa Pc Pe) Pc(Hw Io Jj Jo Jp Lu Lx Ma Mi Mr Ms Mt Mz Nd Oi Ok Pa Pe Po) Mi(In Io Jj Jp Js Lw Ma Mh Ms Mt Mz Ni Nj Og Ok Om) Nt(In Io It Jp Js Lw Ma Mt Mz Ne Nj Nw Og Om) Jj(Jk Jo Lx Ma Mg Mr Nv Om) Og(Jg Jk Mg Mt Nb Om) Lw(Io Lu Lx Mr Pa) Ma(Lx Mr Pa Pe) Lx(Js Mh) Ms(Jg Om) MtPb MwOy IoNv} Jj{Jk(Fp Hr Hu Hv Hw Hx Ij Il Im In Io Ir Iu Iv Jg Jh Jp Jt Li Lu Lw Lx Md Mg Mh Mi Mm Mn Mp Mq Mr Ms Mt Mv Mx My Mz Na Nb Nd Nf Ng Ni Nj Nm Nq Nr Ns Nu Nv Nw Nx Oc Og Oh Oi Ok Om Oy Oz Pa Pb Pc Pd Pe Po Qa Qd Qe) Nt(Io Jg Jo Jp Ma Mg Mm Mp Mt Mz Nj Nq Nv Nw Ny Oh Om Pc Pe Po Qa Qe) Nq(Hu Hw Ir Iv Jo Jt Mt Mz Nv Ok Om Pe Qa Qd Qe) Mt(Hw Il Jo Lx Mi Mp Mr Nv Pe) Om(Hw Iu Jo Lx Mi Mp Nv Og Oh) Jo(Mz Nv Nw Pe) Pe(Mg Mm Pc) Nv(Io Pc) MiQa MpMz} Og{Om(Hq Hw Ik Il Im Io Ir Iu Iv Jg Jk Jo Jp Jt Lu Lw Lx Ma Mg Mh Mm Mr Ms Mv Mw Mx Mz Nj Nl Nr Ns Nw Oh Ok Oz Pb Pe Po Qa Qe) Mw(Hu Hx Ih Ij Il Im Iv Jk Jo Jp Jt Lx Ma Mg Mi Mt Mx My Nb Nt Nv Nw Oh Oy Pe Po Qa Qe) Jg(Hw Il Ir Jk Lx Mi Mr Mt Mx Mz Nq Nt Nv Nw Pa Pe Po Qa Qe) Nb(Im Jh Jk Ma Mg Mm Mt Mv Nq Nv Nw Pc) Nq(Hx Ir Mz Nw Ok Pe) Nt(Jh Mt Mv Mz Nw Pc) Mt(Hx Jh Jk Jo Mi) Mz(Jk Mg Mm Pc) Hx(Jh Mm Pc) Jh(Mi Pa) Jk(Nw Ok) Pe(Mm Pc) LwPa MvOk JoNw} Mm{Pe(Hq Hv Hw Hx Ij Ik In Ir Iv Jh Jo Jp Jt Li Lu Lz Ma Mg Mk Mr Ms Mt Mz Na Nf Ng Ni Nj Ns Nt Nw Oi Ok Om Oy Oz Pb Pc Pd Pf Pz Qa) Mz(Hw Hx Il Im Io Ir Iu Iv Jk Jo Lu Lx Ma Mi Ml Mp Mr Ms Mt Mz Nq Nr Nv Nw Om Pa Pb Pc Pd Qa Qd Qe) Qa(Il Io Lu Lx Ma Mi Mr Mt Nq Nt Nv Nw Om Pa Pz) Nt(Io Ir Jp Mt Nf Nw Om) Mr(Io Ma Mt Ni Om Qd) Nw(Hv Hw Jo Na) Om(Ir Ms Ng Oy) Ir(Io Lu) PoOy MtHw MwMy NgJk NiPa} Nq{Mz(Ir Jp Lw Ma Md Mh Ml Mp Ms Mt Mv My Nf Ng Nj Nt Ny Of Ok Oy Pb Pc Qd) Hu(Hv Hw Hx Ij In Iv Jh Jk Jo Jp Jt Mr Mt Mx Na Nf Nt Nv Nw Pc Qd Qe) Ok(Ir Jp Mp Ms Mt My Ng Nj Nk Ns Nw Oy Pb Pc Pe Qa Qd Qe) Ms(Ir Jt Mt Nb Nw Om Pe) Oy(Hx Jh Mr Mw Nw Pa Pe) My(Jg Mt Mw Nb Nw) Ng(Nb Nw Om Pe) Nw(Hw Jo Qa) Mk(Pa Pe) NjQa PbPe} Pc{Pe(Hw Im Io Jp Li Lu Ma Ms Mt Mz Ni Nt Nw Oi Ok Pb Qa Qd) Nt(Io Ir Jp Ma Ms Mt Nf Nj Nw Oi Ok Om Qa Qd) Mz(Im Iu Jo Jp Lx Ma Mi Mp Mr Ms Mt Nd Pa Qd) Mt(Hw Jo Mi Mr Ms My Oi Ok Pa Qa) Qa(Io Jp Lx Mi Mr Nw Pa) Mr(Jp Ma Nw Om Qd) Ok(Jp Lx Mi Mp Pa) Hw(Jp Nw) Om(Ms Oy) MiJp MwMy JhOy JoNw} Mp{Mz(Hq Im Jg Jk Jp Ma Mt Nj Ns Nt Nw Ok Om Pa Pb Pd Pf) Nw(Hv Hw In Io Jo Jt Na Ni Nt Ok Qa) Om(Hq Ir Ms Ng Nj Ns Of Oy Pb Pd) Ok(Hq Io Jk Jp Mt Nj Ns Qe) Jp(Hq Hw Io Ns Nt Qa) Mw(My Oy) Io(Nt Qa) MkPe MtHw NgJg JhOy NyPb} Nt{Mt(Hx Ik Io Lw Ma Mh My Mz Nj Nw Ny Oi Pb) Mz(In Io Jp Lw Ma Mg Ml Nj Nw Pb) Nw(Io Lw Ma Mh Ms Nj Pb Qa) Om(Ms Ng Nj Of Oh Oy Pb) Io(Lw Nj Nv Qa) Jp(Lw Ne Nj Oh) Mw(My Oy) Jg(Ms Ng) MvMy NjOh ItQa JhOy} Mw{My(Hx Il Iv Jg Jp Lu Lw Ma Mg Mi Mr Ms Mv Mx Nb Nf Ng Nj Nv Nx Oh Ok Om Oy Pa Pb Po Qa Qd Qe) Oy(Hx Ir Jo Mi Ml Mt Mz Nd Nw Ny Oh Ok Om Pa Po Qa Qd) Hu(Hx Ny)} Mi{Om(Hx Io Jp Ml Ms Mt Mz Nj Ny Of Pb Qa) Mt(Hw Io Ms Mz Ng Nj Ok Qa) Mz(Jp Ma Ml Nj Pb) Qa(Io Jp Ma Nj Nw) Jp(Io Ni Ok) Ms(Jg Jh) Ng(Jg Jk) Nw(Hw Io) NiNj} Mt{My(Hx Jh Jk Nb Om Pa) Pb(Jo Mz Ns Oy Pe Qa) Mh(Ii Mr Pa Pe) Ml(Hw In Mz Qa) Lw(Io Mr Pa) Ms(Nb Om) Oy(Jh Om) IoJt JoNw OhPe} Om{Ms(Iu Jt Lw Oh Pa) Oy(Jk Lx Nv Pa Po) Ng(Jk Lx Nv Pa) My(Nb Nv Pa) Pb(Hw Mr Pc) LxOf MkPa} Nw{Jo(Io Ma Mh Ml Ms Pb) Io(Hw Jt Lw Qa) Jk(Ms My Ng Oy) Hw(Ma Pb) MhPe JhOy} Jh{Oy(Hx Jk Mr Nb Nv Pe) My(Nb Pa)} Ng{Jg(Jk Lx Nv Pa Pe) Mg(Jk Lx)} Lw{Io(Jp Pa) WmJp MaMr} Ml{Mz(Mg Nb Pa)} Lx{Mh(Hq Ns)} Io{QaNv JpJt} Pe{MaPb MvMy} PoJgOy

Unconstrained panels with 3 analytes, where 1.6E-7 >= 'model p-value' > 1.0E-7. Contains 7,091 panels of 645,860 total panels evaluated. :
Ji{Hu(Fp Hq Hr Hv In Ir It Iv Jh Jt Li Lw Ly Lz Md Me Mh Mj Mn Mq Mv Mw Mx Mz Na Nb Nc Ne Ng Nh Ni Nk Nl Nm Nu Oe Of Ok Om Oy Oz Pz Qa Qb Qd) Mv(Fp Hq Hr Hv Ih Ij Im Iq Ir It Jg Jm Js Lj Lw Lz Mc Me Mf Mj Mk Mn Mq Mw Mx Na Nb Nc Nf Nu Nw Oe Ok Om Pf Qa Qb Qd) Qe(Fp Hq Hr Hv Ij Ik Im Iq Ir Jm Js Lj Lw Lz Mc Md Me Mf Mj Mk Mn Mq Mw Mx Mz Nb Nc Nf Ng Nk Nw Of Ok Pf Qa Qd) Jn(Fp Hq Hr Hv Ih Ii Ij Ik Im Iq Ir Jm Lj Lz Mc Md Me Mf Mj Mk Mn Mq Mw Mx Mz Nc Ne Nf Ng Nw Oe Of Ok Pf Qa Qd) Mz(In Iv Jg Jh Jp Jq Jt Li Ly Md Mh Mj Mq Na Nb Ne Nh Ni Nj Nk Nl Nm Ns Nu Ny Ok Om Oy Oz Pd Po Pz Qa) Iv(Fp Hq Ik It Jt Li Lw Ly Md Me Mh Mj Mn Mq Mw Na Nb Ne Nf Nh Ni Nk Nl Nm Nu Nw Ny Oy Oz Pd Qa Qb) Po(Hq Hr Hv Ih Ij Im Iq Ir It Jm Js Lj Lz Mc Me Mf Mj Mk Mn Mw Mx Nb Nc Nf Nk Nu Nw Ok Oz Pf Qd) Nr(Hq Hr Hv Ih Ij Im Iq Ir Jm Js Lj Ly Lz Mc Me Mf Mj Mk Mn Mq Mw Mx Na Nb Nc Ng Nl Ok Pf Qb Qd) Nj(Fp Hq Hr Hv Ii In Ir It Jt Li Lw Lz Mf Mh Mn Mw Mx Ne Nf Nh Nk Nl Nm Nw Nx Ny Oi Ok Pz Qb Qd) Jh(Hr Hv Ik In Ir Jg Jt Li Ly Lz Md Mh Mj Mn Mq Mx Na Nb Nc Ne Nh Ni Ns Nu Ny Om Oz Qa Qb Qd) Mb(Fp Hq Hr Ii Ir Jg Jt Lw Md Mj Mq Mx Na Nb Ne Nf Nh Nk Ns Nu Ny Oe Of Ok Om Oy Oz Pf Pz) Oh(Fp Hq Ih Ij Im Iq It Jm Js Lj Lw Lz Mc Md Me Mf Mk Mn Mw Mx Nc Ng Nk Nw Ny Of Pf Qb Qd) Hx(Fp Hq Hr Hv Ih Ij Im Iq Ir Jm Js Lj Ly Lz Mc Me Mf Mk Mn Mq Mw Mx Nc Nf Nw Oz Pf Qd) Pd(Ii Ik Ir It Jt Li Lw Ly Md Mg Mh

Po(Mh Pb) Hw(Ml Oh) Ik(Om Pe) Pa(Jm Ok) NgOm InPe JgOy} Jq{Lx(Hv li Im In Io Ir Iu Js Jt Li Lu Lw Mb Mf Mn Mq Mr Mw Ng Nv Nw Om Oz Po) Mr(Hv Hx In Iv Js Lu Md Mn Mw Nd Ns Nv Nw Oi Ok Oy Oz Pa Pe Po Qc Qd Qe) Mt(Hv Ii Ik Im Jn Js Li Lw Mb Mh Mn Mv My Ne Nh Nl Ns Nu Oe Oh Oz Qa Qc) Ip(Fp Hq Ih Ij Iq Ir Jm Lj Ly Mc Md Mj Mq Nf Ng Ni Nx Oe Of Oy Pf Pz Qb) Pa(Hq Hu Hw Ih Ik Il Iq Jm Jt Lj Lz Mb Mc Mz Na Ne Nh Nm Nr Nx Pf Pz) Pe(Hv Hw In It Iu Iv Jo Js Lu Mf Nv Of Oi Ok Oy Po Qe) Mm(Ik Iq Jm Lj Lw Lz Mb Mc Md Me Mk Nh Nx Of Oh) Nq(Hq Iq Ly Mc Me Mj Mk Ne Nh Nm Nx Pf Pz) Ma(Hv Il Io Ir Iv Mg Mv Nl Nu Og Oz Pb) Nd(Hq Hx Jj Jn Jo Mi Mv Nr Nu Nw Qa Qe) Pc(Fp Hv Io Jg Jj Ml Mz Nl Ny Oi Om Qb) Mi(Ik Iq Lj Lz Mj Mk Na Nm Nx Pz) Pg(Ih Il Iq Lj Mc Mj Mk Nc Nf Nv) Mg(Jk Jn Lu Ml Ms Ng Nj Ok Qe) Jo(Im Io It Ml Ms Nj Nw) Ml(Hw Hx Jk Jp Nb) Nj(Lu Mv My Nb Nr) Jk(Ms Ok Oy Pb) Jp(Iu Lu Ms Nu) Jg(Hw Jj Ns) Il(It Og) WmFr MsNb MvJj ItQa NvPb} Pg{Ok(Fp Hr Hw Hx Ih Im Ir It Iv Jg Jk Jm Jt Lx Ly Mb Mc Me Mh Mj Mk Mx Nd Ne Nf Nh Ni Nk Nm Nt Nx Ny Oe Om Pa Pd Pf Qa Qc Qd Qe) Mz(Hr Hw Ir It Iv Jg Jk Jm Js Lj Lu Lx Ly Mb Me Mf Mk Mq Mr Nf Nl Nm Nr Nw Oe Oz Pd Pe Pf Pz Qa Qd Qe) Mm(Hr Ih Iu Jh Js Lw Lx Ly Ma Mb Me Mj Mq Mx Ne Nm Nr Oe Oh Pc Qe) Ip(Hu Hv Hx Ij In Iu Iv Jg Jh Lx Ly Ma My Nr Of Oi Pz Qd) Jn(Hw Im It Jp Jt Lu Mb Ms Mt Ni Ns Oh Oi Pa Pe) Qa(Ii It Jo Lw Ma Mg Mp Nq Og Oh Oy) Pc(Hu Hv In Iv Jt Lu Na Nw Oi Pa Qd) Pb(Hx Im Ir Jg Jk Jm Lu Nm Nq Po) Io(Ik Iu Iv Nm Nw Og Oh Oz Qd) Nt(Jm Jp Lw Ly Ne Nj Og Oy) Mt(Hx Ii Im Jo Mi Nj Ns) Jt(Im In Jp Ma Ms Ng Oy) Hw(Ii Jo Jp Ns Nw) Og(Hq Mi Nf Nm Nq) Oy(Jo Mb Mp Mr Ni) Lw(Ii Im Mr Ng) Mi(Jp Ni Nj) Ng(Jk Jp Mw) Ns(Jg Mq) NqMs LxHq MgMy MkPa MpOm HuJg JoNw JpOh} Fr{Iq(Hr Ii Jg Jh Jm Li Lj Lu Ly Lz Mc Mj Mk Ml Mn Mv Mw Ne Nh Nq Ny Pd Pf Po) Qc(Hr Ii Jg Jh Jm Li Lj Lu Ly Lz Mc Mk Ml Mn Mv Mw Nd Ne Nh Nq Ny Of Pd Po) Pf(Hr Ii Jg Jh Jm Li Lj Lu Ly Lz Mc Mj Mk Ml Mn Mv Mw Ne Nh Nq Ny) Mc(Ii Jg Jm Li Lj Lu Ly Lz Mj Mk Ml Mn Mv Mw Ne Nh Nq Ny Po) Nh(Ii Jg Jm Li Lj Lu Ly Lz Mj Mk Ml Mn Mv Mw Ne Nq Ny Po) Jg(Ii Jh Jm Li Lj Lu Ly Lz Mj Mk Ml Mn Ne Nq Ny Po) Jm(Ii Li Lj Lu Ly Lz Mj Mk Ml Mn Mv Mw Ne Nq Ny) Ne(Li Lj Lu Ly Lz Mj Mk Ml Mn Mv Mw Nq Ny) Mw(Li Lj Ly Lz Mj Mk Ml Mn Mv Nq Ny) Mk(Li Lj Lu Ly Ml Mn Mv Nq Ny) Mv(Li Lj Ly Lz Mj Ml Mn Ny) Nq(Li Lu Ly Lz Mj Ml Ny) Li(Ly Mj Ml Mn Ny Po) Ly(Lz Mj Ml Mn) Ml(Lj Lz Mn) WmMz MjLj} Ip{Nt(Hr Hv Ij Im Ir It Iv Li Lx Mf Ml Mw Mx My Na Nb Nh Ni Nk Nv Nx Ny Oe Of Pa Po Pz) Mi(Hq Hv Jg Jk Jo Jt Lw Mm Na Nf Ni Nq Nv Pb Qd) Om(Iu Jt Lw Lx Mr Mt Mz Nj Nm Nq Nv Ok Pe Qa) Ok(Hw Hx Jj Ma Md Mr Mv Nd Nj Nk Pe Po) Nq(Jo Jp Mt Na Ng Nj Nr Nw Pa Qd) Mz(Jg Jp Jt Lu Lw Nb Nr Oh) Jn(Hw Jp Lu Mg Nb Nw Og Po) Mt(Hx Io Lx Nv Oh Oi Po) Pc(Ir Jo Jp Lu Nb Nf Nw) Jj(Iu Jg Mv Nf Nr Qa) Jt(Io Lu Mm Mp Nv Og) Nj(Hw Nb Nv Pa Pe) Jp(Jo Mm Mr Nv Pa) Oh(Jk Lx Nb Po Qa) Mg(Hw Mr Og Qa) Mm(Hv Ij Jk) Hw(Jg Lx Ma) Io(Nv Nw Qa) Pe(Ms Nv Oz) Po(Lw Oy) Mp(Nf Pa) Jo(Og Pb) Nw(Mr Og) LuLw MaQa NbOy NgJg JkJm PaPb} Mm{Pe(Hu Ii Im Iu Jg Jk Jm Lw Lx Ly Mb Me Mh Mi My Nb Ne Nm Nq Nr Nv Oe Of Oh Pa Qd Qe) Jn(Hr Hu Hv Ii Ij Ik Im Jg Jh Js Jt Lw Ly Mb Md Mh Mv My Na Ng Ns Oe Pf Qc Qe) Mz(Fp Hu In Jh Jp Md Mh Mv Mx My Nb Nd Ni Nj Nl Ny Oi Po Pz Qb) Nt(Hv Hw Hx In Ms Ng Ni Nj Og Ok Pc Qd) Qa(Hx Jk Jp Mp Nb Nf Og Pc Po) Mt(Hx Io Ma Nf Ok Om Pa) Mr(Ir Jp Nw Og Pc) Nq(Ir Ok) Mw(Og Oy) Hw(Jp Om) Pa(Hv Mk) LxIr MiOm MsNb JtNw} Om{Og(Hu Ih Ii Ij In Jh Lz Mb My Na Nd Nf Nk Nu Nx Oy Pd Qb Qd) Ms(Hw Hx Ir Jj Lx Mr Nb Nv Nw Pb Pe Qa Qe) Mp(Hw Ik Io Jp Mk Mr Mt My Nt Nw Ok Qa) Mi(In Ir Iv Jo Ly Md Mg Mh Pc Qd Qe) Nt(Ik In Io Jo Jp Lw Ly Mt My Mz) Pc(Jj Jn Lx My Ng Pa Pe Qa) Oy(Hx Lu Mr Nb Oh Pe Wm) Jj(Il Mt Nd Pe Qe) Pb(Mt Nr Nv Pa) Lx(My Oh) Of(Nv Pa) NqJn MtNg} Nt{Jj(Hx Ij Il Im Ir Jh Lw Mb Mn Mv Mw My Nf Nx Ok Qb Qd) Nw(Hv Hw Hx Jo Jp Jt Ly Mb My Ne Ng Ny Oh Oi Ok) Mt(Jp Ly Ms Ne Oh Ok Oy Qa) Mz(Im It Jg Ly Ms Ne Oh Oi) Jn(Ik Jg Jm Mg Ms Oh Oi Ok) Jp(Ma Ms Ng Nq Ok Pb) Pc(Hx Im Mi Mp Ni Qe) Nj(Lw Ma Nf Nq) Io(Jk Pb Qd) Og(Jk Lw Nb) Nq(Ms Ok) Ma(Ik Lw)} Pc{Pe(Hu Ik In Ir Iv Jh Jo Mi Mr Nf Nj Ns Nv Oy Oz Pf Qe) Mz(Hw Il Ir Iv Jk Ml Nv Nw Oi Ok Qa Qe) Ok(Hx Jk Lu Mr Nd Nw Og Qa Qd Qe) Lx(Hw Ir Jp Jt Mt Qd) Jn(Jk Mg Nr Nv Nw Og) Mr(Im Ir Jj Ms Og) Mt(Hx Jj Nf) Jp(Io Jo Pa) Mi(Io Qd) MaQa MsNb NiPa JjJo} Nq{Jn(Ii Im Jt Lu Lx Mb Mh Mi Mv Na Oe Oz Pz) Mz(Hw Hx Im Iu Iv Jo Nr Nw Pa Pe Qa) Ok(Hx Ih Io Iv Ma Nc Oh Oi Pa) Hu(Im Jg Nb Ni Nj Nr Nx) Qa(Jp Ms Ng Og Oy Pb) Jj(Hx Ih Ij Jp Nw) Ng(Hx Ir Jp Mt) Hw(Jp Mt Nj) Oy(Ir Jg Mt) Ms(Jp Mr) MyPe NaNw JtOg} Mp{Mz(Hw Hx Il In Io Ir Iv Jh Jo Lz Ml Mr Ms Nv Og Oy Pe Qa Qd Qe) Jn(Hx Jh Jk Jo Ms Nr Oi Pd Qa) Nw(Hq Ij Ir Ms Mt Nj Ns Pe) Ok(Hx Jg Ma Ms Pb Pd) Mt(Mr Ns Pe Qa) Jp(Ir Mr Ni Pe) Jj(Ij Nv Pe) Mw(Ng Og) Jg(Ns Og) MkPa NbOy NgJk NjQa HqPe} Jj{Jk(Ih Ii Ik Js Lz Mb Mc Me Mf Mj Ml Mw Nc Nk Nl Ny Of Pf Pz Qb) Nv(Hw Il Ma Mg Mi Mr Pe Qa) Mt(Hx Jt Mg Pa Pb) Jn(Il Jg Pa) Pe(Jg Mi Ml) Jo(Qa Qe) LxJt MwMy} Mi{Jn(Jg Jh Jm Lu Ly Ml Ng Nw Oi Oy Pb Qa) Mt(Hv Jo Jp Lw Ly Na Ni Oi) Nw(Hv Jo Mh Ms Na Og) Mz(Mh Og Qa) Io(Nv Ok Qd) Nj(Jp Ok) Jg(My Qa) NgJh HwJp JkOg} Og{Mw(Hq Hw Iu Jg Js Lw Mr Ms Nx Pa) Nb(Jp Nj Ok Pe Po Qa) Pe(Jh Mg Mt Mv) Hx(Ma Mg Nw) Jn(Lx Nv Pa) Mt(Ok Pb) Jh(Nv Nw) MgNw MvJo} Mt{My(Il Jn Mv Nv Nw Pe) Pb(Hu Hx In Mr Ok) Ny(Jn Mz Ok) Lx(Jt Ok) Ms(Pa Pe) NrMh LwPe MdMz MrOh HwNw OkPa} Nw{Ma(Jt Mb Na Pe Qa) Jo(Ii Md My Ny Oy) Hw(Mg Ml Nj) LuLw MhMr MlQa MsNb HuJk PbPe} Mw{My(Ih Im Iu Js Jt Mn) Oy(Iv Jp Mh Mx Pf) MlHu} Pe{Jg(Ms My Oy Pb) Lw(Io Jn) MaIk MgNg MlMz JpOh OkPb} Lx{Mz(Mh Ml Pb) Jg(My Oy) MaJt JnOk JoPb} Lw{Io(Nv Qa) Jp(Lu Mr) MzPa} Mg{Ng(Jg Mr Nv Pa) MzPb} My{Mv(Ir Ok) NbJg} Jh{Oy(Ir Jn Oh)} Nv{Io(Jt Qd) MzPb} Wm{LyOn MkJp} Jk{Ok(Ng Pb)} MaMzPa MsHxJg

Unconstrained panels with 2 analytes, where 1.0E-7 >= 'model p-value' > 0. Contains 750 panels of 16,788 total panels evaluated. : Fr(aA Et Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jl(aA Et Fp Hq Hr Hu Hv Hw Hx Ih Ii Ij Ik Il Im In Io Ip Iq Ir Is It Iu Iv Jg Jh Ji Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) On(aA Et Fp Hq Hr Hu Hv Hw Hx Ih Ii Ij Ik Il Im In Io Ip Iq Ir Is It Iu Iv Jg Jh Ji Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Ji(aA Et Hq Hr Hu Hv Hw Hx Ii Ik Il In Io Ip Ir Is Iu Iv Jg Jh Jj Jk Jn Jo Jp Jq Jr Jt Lh Li Lu Lv Lw Lx Ly Lz Ma Mb Md Mg Mh Mi Mj Ml Mm Mn Mp Mq Mr Ms Mt Mu Mv Mw Mx My Mz Na Nb Nc Nd Ne Nf Nh Ni Nj Nk Nl Nm Nn No Nq Nr Ns Nt Nu Nv Nw Nx Ny Oe Og Oh Oi Ok Om Oy Oz Pa Pb Pc Pd Pe Pg Po Pz Qa Qb Qc Qd Qe) Et(aA Fp Hr Hu Hv Hw Hx Ih Ii Ij Ik Il Im In Io Ip Ir Is Iu Iv Jh Jj Jk Jn Jo Jq Jr Js Jt Lh Li Lu Lv Lw Lx Lz Ma Mb Md Mg Mh Mi Mm Mp Mr Ms Mt Mu Mv Mw Mx My Mz Na Nb Nc Nd Nf Ni Nj Nk Nl Nm Nn No Nq Nr Nt Nu Nv Nw Oe Of Og Oh Oi Ok Om Pa Pb Pc Pd Pe Pg Po Pz Qa Qb Qd Qe) aA(Hx Ij Il In Ip Ir Is Jg Jk Jn Jo Jp Jq Jr Lh Lv Lw Lx Ma Mf Mg Mi Mm Mn Mp Mt Mu My Mz Nj Nn No Nq Nt Nv Nw Nx Ok Om Pa Pc Pe Pg Po Qa Qd Qe) Jr(Ip Is Jg Jj Jk Jo Jp Jq Lh Lv Lw Lx Ma Mg Mi Mm Mp Mr Mt Mu Nn No Nq Nt Nv Nw Ok Om Pa Pc Pe Pg) Nn(Hu Hw Hx Ip Ir Is Jn Jo Jq Lh Lv Lx Mi Mr Mt Mz No Nt Nw Ok Om Pa Pe Pg Qa) No(Ip Is Jg Jn Jp Jq Jt Lv Lw Ma Mg Mm Mp Mt Mu Nj Nq Ok Om Pc Pg Qa) Jq(Ip Is Lh Lv Lx Mi Mm Mp Mr Mt Mu Nq Nt Pa Pc Pe Pg) Lh(Ip Is Jj Jn Jp Lv Lw Ma Mm Mt Mu Og Pb Pc Pg) Lv(Is Mi Mm Mr Mt

Figure 34 Continued

Mu Mz Nq Nt Pa Pe Pg) Mu(Ip Is Jj Jn Mi Nt Nw Ok Pe Pg) Is(Io Mi Mm Mp Nq Nt Pc Pg) Pg(Ip Jj Mm Mz Ok) Mm(Jn Mz Pe) Nq(Jn Ok) NtIp JjJk OgOm PcPe

Unconstrained panels with 2 analytes, where 1.0E-6 >= 'model p-value' > 1.0E-7. Contains 659 panels of 16,788 total panels evaluated. : aA(Fp Hq Hr Hu Hv Hw Ih Ii Ik Im Io Iq It Iu Iv Jh Jj Jm Js Jt Li Lj Lu Ly Lz Mb Mc Md Me Mh Mj Mk Ml Mq Mr Ms Mv Mw Mx Na Nb Nc Nd Ne Nf Ng Nh Ni Nk Nl Nm Nr Ns Nu Ny Oe Of Og Oh Oi Oy Oz Pb Pd Pf Pz Qb Qc) No(Fp Hr Hv Hw Hx Ih Ii Ij Ik Il Im In Io Ir Iu Iv Jh Jj Jk Jo Js Lh Lu Lx Ly Mb Md Me Mf Mh Mi Mj Ml Mn Mq Ms Mv Mw Mx My Mz Na Nb Ne Nf Ni Nm Ns Nt Nu Nv Nw Nx Ny Oe Og Oh Oi Oz Pa Pb Pd Pe Po Qb Qd Qe) Lh(Hq Hr Hx Ih Ii Ik Im In Io Ir Iv Jg Jh Jk Jo Jt Lu Lx Ly Md Mf Mg Mh Mi Mk Ml Mn Mp Mr Ms Mv Mw Mx My Mz Nc Ne Ng Ni Nj Nk Nq Ns Nt Nu Nv Nw Ny Oe Of Oh Oi Ok Om Oy Oz Pa Pd Pe Po Qa Qb Qd Qe) Pg(Hq Hu Hv Hw Ih Ii Ik Im In Io Ir Iu Iv Jg Jh Jm Jn Jo Jp Jt Lu Lw Ly Ma Mb Mg Mi Mp Mq Mr Ms Mt My Na Nb Nf Ng Ni Nj Nm Nq Ns Nt Nw Of Og Oh Om Oy Oz Pa Pb Pc Pe Qa Qd Qe) Jr(Hr Hw Hx Ij Ik Il Im In Io Ir It Iu Iv Jh Jn Js Jt Lj Lu Mb Md Mh Ml Mn Mq Ms Mv Mw My Mz Nb Nd Nf Ni Nj Nm Nr Ns Nu Nx Ny Oe Og Oh Oz Pd Po Qa Qc Qd Qe) Is(Hw Hx Ij Ik In Ip It Jg Jh Jj Jk Jm Jo Jp Jt Li Lu Lw Lx Ma Mb Md Mg Mq Mr Ms Mt Mv Mz Nb Nd Nf Ni Nj Nr Nu Nv Nw Oe Og Oh Oi Ok Om Pa Pe Po Qa) Mu(Hw Hx Ih Im Ir Iu Iv Jo Jp Jt Lw Lx Ma Mm Mp Mr Ms Mt Mz Nb Ng Nj Nn Nr Nv Og Oh Om Pa Pc Po Qa Qd Qe) Lv(Hw Hx Im Ip Ir Iu Iv Jg Jh Jj Jk Jn Jo Jp Jt Lu Lw Lx Ma Mg Mp Nb Nf Nr Nv Nw Oh Ok Om Pc Po Qa Qd) Jq(Hw Hx Il Im Iu Iv Jg Jh Jk Jn Jo Jp Lu Ma Mg Mv My Nb Nd Nj Nr Nu Nv Nw Ok Om Po Qa Qe) Et(Hq Iq It Jg Jm Jp Lj Ly Mc Me Mf Mj Mk Ml Mn Mq Ne Ng Nh Ns Nx Ny Oy Oz Pf Qc) Ip(Hw Jj Jk Jn Jp Jt Lx Mi Mm Mp Mr Mt Mz Nb Nq Nv Nw Ok Om Pa Pe Po Qa) Nn(Hv Ii Ij Il Im In Iv Jk Jp Jt Ma Mp Na Nb Nf Nr Nv Nx Oi Po Qd Qe) Nt(Io Ij Jn Jp Lw Ma Mm Mp Mt Mz Nj Nq Nw Oh Ok Om Pc Qa Qd) Mt(Hw Jj Jn Jo Jt Mi Mm Mp Mr My Mz Ok Om Pa Pb Pc Pe) Ji(Fp Ih Ij Im Iq It Jm Js Lj Mc Me Mf Mk Ng Of Pf) Nw(Hw Jk Jn Jo Jt Ma Mi Mm Mp Nq Pc Pe Qa) Jn(Lx Ma Mi Mp Mr Nv Ok Om Pa Pc Pe) Om(Ir Jj Mi Mm Mp Ms Oh Oy Pc Qa) Pe(Jj Jp Lw Mi Mp Nq Oh Ok Pb) Qa(Lx Ma Mi Mm Mp Nq Pc) Ok(Jk Lx Mi Mm Mp Nv Pc) Mz(Ma Mi Mp Nq Pc) Mm(Hw Hx Ir Mr) Nq(Hu Ir Qd) Mi(Jp Pc Qd) Mp(Ir Jp) Mr(Lw Pc) Mw(My Og) Jj(Jo Nv) WmJp LxJt NbOg IrPc hRjI Unconstrained panels with 2 analytes, where 1.0E-5 >= 'model p-value' > 1.0E-6. Contains 1,159 panels of 16,788 total panels evaluated. : Nt(Fp Hq Hr Hv Hw Hx Ih Ij Ik Im In Iq Ir It Iu Iv Jg Jh Jk Jm Jo Js Jt Li Lj Lu Lx Ly Lz Mb Md Me Mf Mg Mh Mi Mj Mk Ml Mn Mq Mr Ms Mv Mw Mx My Na Nb Nc Ne Nf Ng Ni Nk Nm Ns Nu Nv Nx Ny Oe Og Oi Oz Pa Pb Pd Pe Pf Po Qb Qe) Jq(Fp Hq Hr Hu Hv Ih Ii Ij Ik In Io Iq Ir It Jj Jm Js Jt Li Lj Lw Ly Lz Mb Mc Md Me Mf Mh Mj Mk Ml Mn Mq Ms Mw Mx Mz Na Nc Ne Nf Ng Nh Ni Nk Nl Nm Ns Nx Ny Oe Of Og Oh Oi Oy Oz Pb Pd Pf Pz Qb Qc Qd Wm) Mu(Fp Hq Hr Hu Hv Ii Ij Ik Il In Io Iq It Jg Jh Jk Jm Js Li Lj Lu Ly Lz Mb Mc Md Me Mf Mg Mh Mj Mk Ml Mn Mq Mv Mw Mx My Na Nc Nd Ne Nf Nh Ni Nk Nl Nm Nq Ns Nu Nx Ny Oe Of Oi Oy Oz Pb Pd Pf Pz Qb Qc) Pe(Fp Hr Hv Hw Hx Ik Im In Io Ir Iu Iv Jg Jh Jk Jo Jt Lj Lu Lx Ly Lz Ma Mb Md Mg Mh Ml Mn Mq Mr Ms Mv Mx My Mz Na Nb Nf Ni Nj Nm Ns Nv Nx Ny Oe Og Oi Om Oy Oz Pa Pf Po Qa Qd Qe) Nw(Hv Hx Ij Il Im In Io Ir Iu Iv Jg Jh Jj Jp Lu Lw Lx Mb Me Mg Mh Mq Mr Ms Mt Mv Mx My Mz Na Nb Nd Nf Ni Nj Nk Nl Nm Nr Nu Nv Oe Og Oh Oi Ok Om Pa Pb Pd Po Qd Qe) Is(Fp Hq Hr Hu Hv Ih Ii Il Im Iq Ir Iu Iv Jn Js Lj Ly Lz Mc Me Mf Mh Mj Mk Ml Mn Mw Mx My Na Nc Ne Ng Nh Nk Nl Nm Ns Nx Ny Of Oy Oz Pb Pd Pf Pz Qb Qc Qd Qe) Nn(Fp Hq Hr Ih Io It Iu Jg Jh Jj Js Li Lu Lw Lz Mb Md Me Mf Mg Mh Mj Mm Mn Mq Ms Mv Mw Mx My Nc Nd Ni Nj Nk Nl Nm Nq Ns Nu Ny Og Oy Oz Pb Pc Pd Pf Qb) Mt(Hv Hx Ii Ij Ik Il Im In Io Ir Iu Iv Jg Jk Jp Lu Lw Lx Ma Mb Md Mg Mh Ml Mn Mq Ms Mx Na Nb Nd Nf Ni Nj Nm Nq Nr Nv Nx Ny Oe Og Oh Oi Po Qa Qd Qe) Om(Hu Hw Hx Ih Ik Im In Io Iu Iv Jk Jo Jp Jt Lu Lw Lx Lz Ma Mg Mh Ml Mr Mx My Mz Na Nb Nc Nd Ng Nj Nk Nl Nq Nr Ns Nv Ny Oe Of Oi Ok Pa Pb Po Qd Qe) Ok(Hw Hx Ih Il Im Io Ir Iu Iv Jg Jh Jj Jo Jp Jt Lu Lw Ma Md Mg Mn Mr Ms Mv Mx My Mz Nb Nc Nd Nf Nj Nk Ny Og Oh Pa Pb Pd Po Qa Qb Qd Qe) Pg(Fp Hr Hx Ij Il Iq It Jk Js Li Lj Lx Lz Mc Md Me Mf Mh Mj Mk Ml Mn Mv Mw Mx Nc Nd Ne Nh Nk Nl Nr Nu Nv Nx Ny Oe Oi Pd Pf Po Pz Qb Qc) Lv(Fp Hq Hr Hu Hv Ih Ii Ij Il In Io Js Li Lz Mb Md Mh Mj Mn Mq Ms Mv Mw Mx My Na Nc Nd Nj Nk Nl Nm Nu Nx Ny Oe Og Oi Oz Pb Pd Qb Qe) Mi(Hv Hw Hx Ih Ij Il Im In Io Ir Iu Iv Jg Jh Jj Jk Jo Jt Lu Lw Lx Ma Mm Mp Mr Ms Mv My Na Nb Nf Ni Nj Nq Nv Nx Ny Og Oh Po Qe) Nv(Hv Hw Im Io Ir Iu Iv Jo Jp Jt Lw Lx Ma Mg Mm Mp Mr Ms Mz Na Nb Nf Ni Nj Nq Nr Oe Og Oh Oi Pa Pb Pc Qa Qd Qe) Jr(Fp Hq Hu Hv Ih Ii Iq Jm Li Ly Lz Mc Me Mf Mj Mk Mx Na Nc Ne Ng Nh Nk Nl Of Oi Oy Pb Pf Pz Qb Wm) Lh(Fp Hu Hv Hw Ij Il Iq It Iu Jm Js Li Lj Lz Mb Mc Me Mj Mq Na Nb Nd Nf Nh Nl Nm Nr Nx Pf Pz Qc) aA(eD Ef hA hR hV hW hX iB iC jD jE jF jG jH jI jK jL jM jO jP jQ jR jT jU jV jY lK lL lM lN lO) Mp(Hq Hv Hw Hx Ii Ij Im In Iv Jg Jh Jj Jk Jo Jt Ma Mr Na Nb Nf Nj Nr Ns Nx Pa Po Qd Qe) jI(eD hA hV hW hX iB iC jD jE jF jG jH jK jL jM jO jP jQ jR jT jU jV jY lK lL lM lN lO) Mz(Hw Im Ir Iu Iv Jg Jh Jk Jn Jo Jp Jt Lw Lx Mg Ml Mr Mv Nd Nj Og Oh Pa Po Qa Qd Qe) Ip(Hv Hx Ii In Ir Iv Jg Jh Jo Lu Lw Lz Ma Md Mg Mn Mv Mx Na Nf Nr Nx Og Oh Pc Qd) No(Hq Hu Iq It Jm Li Lj Lz Mc Mk Mr Nc Nd Ng Nh Nk Nl Nr Of Oy Pf Pz Qc) Jn(Hw Hx Io Jg Jh Jj Jk Jo Jp Jt Lu Lw Md Mg Ms Mv Nb Nd Nr Og Oh Po Qa) Mm(Hv Ii Ij Il In Iv Jk Jo Jp Jt Lu Lx Mx Na Nb Nf Nq Nr Pa Po Qd Qe) Qa(Hx Io Jg Jh Jj Jk Jo Jp Jt Lu Lw Md Mg Mn Mr Nb Nd Nj Oh Pa Po) Nq(Hv Hw Hx Im Iv Jj Jo Jp Jt Lw Mr Ms Na Nf Nr Pa Po Qe) Lx(Hq Hw Ir Iv Jg Jj Jk Jo Jp Lw Ly Ma Mh Na Oh Pc Qd Qe) Jp(Hw Hx Ir Iv Jk Jo Jt Lw Mg Mr Nb Nr Oh Pa Pc Po) Pc(Hw Hx Im Iv Jk Jo Jt Nb Nf Nr Pa Po Qd Qe) Ma(Hw Hx Ir Iv Jk Jo Jt Mr Nb Nf Pa Po Qe) Mr(Im Ir Jg Jj Jk Jt Mg Oh Po Qd Qe) Qd(Hw Hx Jg Jk Jo Jt Nb Pa Po) Jt(Hx Im Jj Jk Lu Nd Pa Po) Ir(Jg Jj Jk Lw Mg Pa Po) Lw(Hx Jk Nb Pa Po) Jo(Im Jk Oh Po Qe) Wm(Et Fr Ji On) Nb(Im Ms My) Jg(Hw Ng Og) Dc(cS Fr) Po(Jj Pb) Hx(Jj Og) Jk(Og Oh) Oy(Jh Mw) DdFr EfdK MgHw OhPa Unconstrained panels with 2 analytes, where 1.0E-4 >= 'model p-value' > 1.0E-5. Contains 1,459 panels of 16,788 total panels evaluated. : Qa(Fp Hq Hr Hu Hv Hw Ih Ii Ij Ik Il Im In Iq Ir It Iu Iv Jm Js Li Lj Ly Lz Mb Mc Me Mf Mh Mj Mk Ml Mq Ms Mv Mw Mx My Na Nc Ne Nf Ng Nh Ni Nk Nl Nm Nr Ns Nu Nx Ny Oe Of Og Oi Oy Oz Pb Pd Pf Pz Qb Qc Qd Qe) Fr(aC Ad aF aJ aL aM AN Ao AP Ar As Aw Ax aZ bA BB bC bE bF bH bJ bL bM Bn Bo bR bU bV bW cC cD cE cF cJ cL cM Cp Cq CS cT CU CV Cw cY Db dC De dF Dg dH DI DK DL dM dN Ef) Mz(Fp Hq Hr Hu Hv Hx Ih Ii Ij Ik Il In Io Iq It Jj Jm Js Li Lj Lu Ly Lz Mb Mc Md Me Mf Mh Mj Mk Mn Mq Ms Mw Mx My Na Nb Nc Ne Nf Ng Nh Ni Nk Nl Nm Nr Ns Nu Nx Ny Oe Of Oi Oy Oz Pb Pd Pf Pz Qb Qc Wm) Jn(Fp Hq Hr Hu Hv Ih Ii Ij Ik Il Im In Iq Ir It Iu Iv Jm Js Li Lj Ly Lz Mb Mc Me Mf Mh Mj Mk Ml Mn Mq Mw Mx My Na Nc Ne Nf Ng Nh Ni Nj Nk Nl Nm Ns Nu Nx Ny Oe Of Oi Oy Oz Pb Pd Pf Pz Qb Qc Qd Qe) Nv(Fp Hq Hr Hu Hx Ih Ii Ij Ik Il In Iq It Jg Jh Jk Jm Js Li Lj Lu Ly Lz Mb Mc Md Me Mf Mh Mj Mk Ml Mn Mq Mv Mw Mx My Nc Nd Ne Ng Nh Nk Nl Nm Ns Nu Nx Ny Of Oy Oz Pd Pf Po Pz Qb Qc Wm) Jt(Fp Hq Hu Hv Hw Ih Ij Il In Io Ir It Iu Iv Jg Jh Jo Li Lw Lz Md Mg Mh Mj Ml Mn Ms Mv Mw Mx My Nb Nc Nf Ng Ni Nj Nk Nr Ns Nu Nx Ny Og Oh Oi Oz Pb Pd Pf Qb Qe) Nq(Fp Hr Ih Ii Ij Il In Iu Jg Jh Jk Js Li Lj Lx Lz Ma Mb Md Me Mg Mh Mj Mn Mp Mq Mv Mw Mx My Nb Nc Ng Ni Nj Nk Nl Nm Ns Nu Nx Ny Og Oh Oi Oy Oz Pb Pc Pd Qb) Mi(Fp Hq Hr Hu Ii Ik Iq It Jm Js Li Lj Ly Lz Mb Mc Md Me Mf Mg Mh Mj Mk Ml Mn Mq Mw Mx Nc Nd Ne Ng Nh Nk Nl Nm Nr Ns Nu Oe Of Oi Oy Oz Pa Pb Pd Pf Pz Qb Qc) Po(Hr Hv Hw Hx Ih Ii Ij Ik Im In Io Iu Iv Jg Jh Jk Lu Lx Mb Md Mf Mg Mh Mn Mq Ms Mv Mx My Na Nb Nd Nf Ni Nj Nl Nm Nr Ns Nx Ny Oe Og Oh Oi Oy Oz Pa Qb Qe) Lx(Hv Hx Ih Ij Ik Im In Iu Jh Js Li Lu Mb Md Me Mf Mg Mj Ml

Figure 34 Continued

Mn Mp Mq Mr Ms Mv Mw Mx My Nb Nc Nf Ng Ni Nj Nm Nr Ns Nu Nx Ny Of Og Oy Oz Pa Pb Pd Qb) Ip(Fp Hq Hr Hu Ih Ij Ik Il Im Io Iq Iu Jm Js Li Ly Mb Me Mf Mh Mj Mk Mq Ms Mw My Nc Nd Ni Nj Nk Nl Nm Ns Nu Ny Oe Of Oi Oy Oz Pb Pd Pf Qb Qe) Ir(Hu Hv Hw Hx Ii Ij Ik Im In Io It Iv Jh Jo Li Lu Mb Md Ml Mn Mq Ms Mv Mw Mx My Nb Nd Nf Ni Nj Nm Nr Nu Nx Ny Oe Og Oh Oi Oz Pb Pd Pf Qd Qe) Ok(Fp Hq Hr Hu Hv Ii Ij Ik In Iq It Jm Js Li Lj Ly Lz Mb Mc Me Mf Mh Mj Mk Ml Mq Mw Na Ne Ng Nh Ni Nl Nm Nr Ns Nu Nx Oe Of Oi Oy Oz Pf Pz Qc) Qd(Hr Hv Ih Ii Ij Ik Il Im In Io Iu Iv Jh Jj Jp Lu Lw Ma Mb Md Mg Mh Mn Mq Ms Mv Mw Mx My Na Nd Nf Ni Nj Nm Nr Nu Nx Ny Og Oh Oi Oz Pd Qc) Mr(Fp Hv Hw Hx Ih Ij In Iu Iv Jh Jo Js Lu Ly Mb Md Mf Mh Mn Mq Ms Mv Mw Mx My Na Nc Nf Ni Nj Nk Nm Nu Nx Ny Og Oi Oz Pa Pb Pd Qb) Jk(Fp Hu Hv Hw Hx Ih Ij Im In Io Iu Iv Jg Jm Js Li Lu Lz Md Mg Mh Mj Mn Mq Ms Mx Na Nb Nf Ng Ni Nj Nm Nr Nu Nx Oe Oi Oy Pa Pb Qe) Jp(Fp Hr Hv Ih Ii Ij Il Im In Io Iu Jg Jh Jj Js Li Lu Lz Ma Mb Md Mf Mh Mj Mq Ms Mv Mx My Na Nd Nf Ni Nj Nm Nu Nx Ny Oi Pd Qb Qe) Om(Fp Hq Hr Hv Ii Ij Il Iq It Jg Jh Jm Js Li Lj Ly Mb Mc Md Me Mf Mj Mk Mn Mq Mv Mw Ne Nf Nh Ni Nm Nu Nx Oz Pd Pf Pz Qb Qc Wm) Mm(Fp Hr Hu Ih Im Io Iu Jg Jh Jj Js Li Lw Ma Md Me Mg Mh Mj Mn Mp Mq Ms Mv Mw My Nc Nd Ni Nl Nu Nx Ny Og Oh Pc Pd Pf Qb) Mt(Fp Hq Hr Hu Ih Iq It Jh Jm Js Li Lj Ly Lz Mc Me Mf Mj Mk Mv Mw Nc Ne Ng Nh Nk Nl Ns Nu Of Oy Oz Pd Pf Pz Qb Qc Wm) Nw(Fp Hq Hr Hu Ih Ii Ik Iq It Jm Js Li Lj Ly Lz Mc Md Mf Mj Mk Ml Mn Mw Nc Ne Ng Nh Ns Nx Ny Of Oy Oz Pf Pz Qb Qc Wm) Mp(Fp Hr Hu Ih Il Io Iu Js Li Lu Lw Mb Md Me Mf Mg Mh Mj Mk Mn Mq Ms Mv Mw Mx My Nc Ni Nm Nu Ny Og Oh Pc Pd Pf Qb) Jo(Hx Ih Ik Il In Io Iu Iv Jg Jh Li Lu Lw Lz Md Mg Mh Mn Ms Mv Mw Mx My Nb Nd Nf Nj Nx Ny Og Oz Pa Pb Qb) Pe(Hq Hu Ih Ii Ij Il Iq It Jm Js Li Mc Me Mf Mj Mk Mw Nc Nd Ne Ng Nh Nk Nl Nr Nu Of Pd Pz Qb Qc) Pa(Hv Hw Hx Ij Im In Iv Jg Jh Jj Js Md Mg Mk Mn Mq Ms Mv Mx My Na Nf Ni Nj Nm Nx Ny Og Qe) Jg(Hu Hv Hx Im In Io Iu Iv Jj Lu Lw Ma Mq Ms Mx My Na Nb Nf Nr Ns Oh Oi Oy Pc Qe Wm) Ma(Hr Hv Ih Ii Ij Il Im In Iu Jj Js Lu Lw Mb Md Mh Mq Mx Na Nl Nr Nx Oh Pc Qb) Pc(Hu Hv Ih Ii Ij Il In Iu Jh Js Lu Md Mg Mj Mv Mx Na Nd Ni Nx Ny Pd Qb) Lv(Ik Iq It Jm Lj Ly Mc Me Mf Mk Ml Ne Ng Nh Ni Ns Of Oy Pf Pz Qc) Lw(Hw Ii Ij Il Im Iu Iv Jh Js Lu Mg Mv Mx Nf Nr Ny Oh Qe) Nb(Hx Iv Jh Jj Md Mg Mh Ml Mv Mx Nd Nj Ny Of Oh Oy Pb Qe) Nn(Ik Iq Jm Lj Ly Mc Mk Ml Ne Ng Nh Oe Of Oh Pz Qc) Im(Hw Hx Ii Iv Jj Lu Md Mg Mj Mq Mv Nf Nr Nx Oh Qe) Ef(aJ An aO aP bA cD cJ cS cT Cv Db Dc dF dN Gl) Hx(Hw Iu Iv Jh Lu Md Mg Mn Ms Mv Nj Nx Oh Qe) Qe(Hw Iv Jh Jj Lu Md Mg Mv Nf Nr Nx Og Oh) Nt(Hu Ii Il Mc Nd Nh Nl Nr Of Oy Pz Qc) Hw(Iv Jh Jj Md Mn Mv Nj Nx Ny Oh) cS(Ad An As Aw Cp Cq Cu Cw Dd Dk) Mg(Hv Iv Jj Mx Na Nf Nr Og Qb) Iv(Jh Jj Md Mv My Nf Nx Oh) Jj(Ih Ii Ij Il Mv Nx Ny) Oh(Ii Ij In Jh Nr Nx) Dc(aX bW cJ) Wm(Jl Mw No) Mv(My Nx Og) Jh(Nf Nr Og) aA(cJ kG) hW(hR jD) NfIu IjOg NyPb aPdH bGdN jDjP

Unconstrained panels with 2 analytes, where 1.0E-3 >= 'model p-value' > 1.0E-4. Contains 1,769 panels of 16,788 total panels evaluated. : Ef(aC AD aE AF aG aH aI Aj aK AL aM aN Ao Ap aQ AR AS aU aV AW AX aY aZ Ba BB BC bE bF BG bH bI bJ bL bM BN BO bP bQ bR bS bU bV bW bX bZ cA cB cC cE cF cG CH cI cK cL cM cN CO CP CQ cR Cs Ct CU cV CW CX cY cZ dA dB dC DD DE DG dH DI dJ Dk DL dM Ex Fw) aA(aC aG aH aI aJ aM aN aO aP aU Aw aX aZ bA bB bC bE bF BG bH bJ bL bM bO bQ bR bS bU bV bW bX bZ cB cC cD cE cF cG cH cK cM cN CO Cq cR cS cT cU cX cY dB DC DD DE dF dH dI dJ DK dM dN mP nR Wm) Hx(Fp Hq Hr Hu Hv Ih Ii Ij Ik Il In Io Iq It Jm Js Li Lj Ly Lz Mb Mc Me Mf Mh Mj Mk Ml Mq Mw Mx My Na Nc Nd Ne Nf Ng Nh Ni Nk Nl Nm Nr Ns Nu Ny Oe Of Oi Oy Oz Pb Pd Pf Pz Qb Qc Wm) Qe(Fp Hq Hr Hu Hv Ih Ii Ij Ik Il In Io It Iu Jm Js Li Lj Ly Lz Mb Mc Me Mf Mh Mj Mk Ml Mn Mq Ms Mw Mx My Na Nc Nd Ne Ng Ni Nj Nk Nl Nm Ns Nu Ny Oe Of Oi Oy Oz Pb Pd Pf Pz Qb Qc Qd) Fr(aD aE Af aG aH aI Aj aK Al aO aQ aR aS aU aV aW aX aY Ba Bc BG bI bN bO bP bQ bS bX bZ cA cB cG CH cI cK cN CO cP cQ cR Ct cW CX cZ dA dB dD dE dG dJ Ex fR Fw Gl) Iv(Fp Hq Hr Hu Hv Ih Ii Ij Ik Il In Io Iq It Iu Jm Js Li Lu Ly Lz Mb Mc Me Mf Mh Mj Mk Ml Mn Mq Ms Mw Mx Na Nc Nd Ne Ni Nj Nk Nl Nm Nr Ns Nu Ny Oe Of Og Oi Oy Oz Pb Pd Pf Qb Qc) Nb(Fp Hq Hr Hu Hv Hw Ih Ii Ij Ik Il In Io Iq It Iu Jm Js Li Lj Lu Ly Lz Mb Mc Me Mf Mj Mk Mn Mq Mr Mw Na Nc Ne Nf Ng Nh Ni Nk Nl Nm Nr Ns Nu Nx Oe Oi Oz Pa Pd Pf Pz Qb Qc Wm) Nx(Fp Hq Hu Hv Ih Ii Ij Il In Io Iu Jg Jh Js Li Lu Lw Lz Mb Md Mg Mh Mj Mn Mq Ms Mw Mx My Na Nc Nd Nf Ni Nj Nk Nl Nr Ns Nu Ny Oe Og Oi Oz Pb Pd Pf Qb) Ma(Fp Hq Hu Ik Io Iq It Jh Jm Li Lj Ly Lz Mc Me Mf Mg Mj Mk Ml Mn Ms Mv Mw My Nc Nd Ne Ng Nh Ni Nj Nk Nm Ns Nu Ny Oe Of Og Oi Oy Oz Pb Pd Pf Pz Qc) Pa(Fp Hq Hr Hu Ih Ii Ik Il Io Iq It Iu Jm Li Lj Lu Ly Lz Mb Mc Me Mf Mh Mj Ml Mw Nc Nd Ne Ng Nh Nk Nl Nr Ns Nu Oe Of Oi Oy Oz Pb Pd Pf Pz Qb Qc) Jg(Fp Hq Hr Ih Ii Ij Ik Il Iq It Jh Jm Js Li Lj Ly Lz Mb Mc Md Me Mf Mg Mh Mj Mk Mn Mv Mw Nc Nd Ni Nj Nk Nl Nm Nu Ny Oe Of Oz Pb Pd Pf Pz Qb) aJ(Ad aH aI aM AN aO As Aw bA bB bC bF BG bH bJ bM bP bQ bR bZ cD cE cF cG cJ cK cM cN Cp Cq cS CU Cw Dc DD De dF dH dI DK dN) Hw(Fp Hq Hu Hv Ih Ii Ij Il In Io Iq Iu Jo Js Li Lu Lz Mf Mh Mj Mq Ms Mw Mx My Nc Nd Nf Ni Nk Nl Nm Nr Ns Nu Oe Og Oi Oy Oz Pb Pd Pf Qb) Im(Fp Hq Hr Hu Hv Ih Ij Il In Io Iu Jh Js Li Lz Mb Me Mf Mh Mk Mn Ms Mw Mx My Na Nc Nd Ni Nj Nk Nl Nm Nu Ny Oe Og Oi Oy Oz Pb Pd Pf Qb) Dc(aG Aj An aO AP Aw Ax BA bB bC bE bF BG bH bJ bL bQ bS bV bZ cD cG Ch CO Cq cU Cx DB DE dF dI DK dN Gl) Jo(Fp Hq Hr Hu Hv Ii Ij Iq It Jm Js Lj Ly Mb Mc Me Mf Mj Mk Ml Mq Na Nc Ne Ng Nh Ni Nk Nl Nm Nr Ns Nu Oe Of Oi Oy Pd Pf Pz Qc) Mg(Fp Hr Ih Ii Ij Ik Il In Io Iu Jh Js Li Lu Lz Mb Md Me Mh Mj Mn Mq Ms Mv Mw My Nc Nd Ng Ni Nj Nk Nl Nu Ny Oh Oi Oz Pb Pd) Lw(Fp Hq Hu Hv Ih In Io Jj Li Lj Lz Mb Md Mf Mh Mj Mn Mq Ms Mw My Na Nc Nd Ni Nj Nk Nl Ns Nu Og Oy Oz Pb Pc Pd Pf Qb Wm) Pc(Fp Hq Hr Io Iq It Jj Li Lj Ly Lz Mb Me Mf Mh Mk Mn Mq Ms Mw My Nc Nj Nk Nl Nm Ns Nu Of Og Oh Oi Oy Oz Pb Pf Qc) Mv(Hv Ih Ii Ij Il In Iu Jh Jk Js Li Lu Mb Md Mh Mj Mn Mq Ms Mx Na Nd Nf Ni Nj Nl Nm Nr Nu Ny Oh Oi Pd Qb Wm) dN(aG aI AN aO aP Aw bA bB bF Bg bH bL bS bW bZ cJ cK cM cN Cp Cq cS cT cU dC Dd DE dF dH DK dM) Jk(Hq Hr Ii Ik Il Iq It Jh Lj Ly Mb Mc Me Mf Mk Ml Mw My Nc Nd Ne Nh Nk Nl Ns Ny Of Oz Pd Pf Pz Qb Qc) Ir(Fp Hq Hr Ih Il Iq Iu Jm Js Lj Ly Lz Mc Me Mf Mh Mj Mk Na Nc Ne Ng Nh Nk Nl Ns Of Oy Pz Qb Qc Wm) Qd(Fp Hq Hu Iq It Jm Js Li Lj Ly Lz Mc Me Mf Mj Mk Ml Nc Ne Ng Nh Nk Nl Ns Oe Of Oy Pb Pf Pz Qb Wm) Mr(Hq Hr Hu Ii Ik Il Io Iq It Jm Li Lj Lz Mc Me Mj Mk Ml Nd Ne Ng Nh Nl Nr Ns Oe Of Oy Pf Pz Qc) Nf(Ih Ii Ij Il Jj Li Lu Lz Md Mh Mj Mn Mq Ms Mw Mx My Nc Nd Nj Nl Nr Nu Ny Og Oh Oz Pb Pd Qb Wm) Jh(Fp Hu Hv Ih Ii Ij Il In Iu Jj Js Li Lu Lz Mb Md Mh Mj Mn Mq Ms Mx My Na Nd Nj Nl Nm Ny Pd Qb) Jp(Hq Hu Ik Iq It Jm Lj Ly Mc Me Mk Ml Mn Mw Nc Ne Ng Nh Nk Nl Ns Oe Of Og Oy Oz Pb Pf Pz Qc) Po(Fp Hq Hu Il Iq It Jm Js Li Lj Ly Lz Mc Me Mj Mk Ml Mw Nc Ne Ng Nh Nk Nu Of Pd Pf Pz Qc) cS(Aj Al aN aO Ap Ar Ax BA Bc BG bH Bn Bo Ch Co Cs Ct cU Cv Db De dF Dg Di Dl dM Gl) Mm(Hq Ik Iq It Jm Lj Ly Lz Mb Mc Mf Mk Ml Nc Ng Nh Nj Nk Nm Ns Oe Of Oi Oy Oz Pb Pz Qc) Oh(Fp Hu Hv Ih Il Iu Jj Js Li Lu Md Mh Mj Mn Mq Mw Mx My Na Nd Ni Nj Nm Nu Ny Oe Pd Qb) Nr(Ih Ii Ij Il In Iu Jj Js Lu Md Mf Mn Mq Ms Mw Mx My Nd Nj Nm Nu Ny Og Oz Pb Pd Qb) Jt(Hr Ii Ik Iq Jm Js Lj Ly Mb Mc Me Mf Mk Mq Na Ne Nh Nl Nm Oe Of Oy Pz Qc Wm) Lx(Fp Hr Hu Ii Il Io Iq It Jm Lj Lz Mc Mk Nd Ne Nh Nk Nl Oe Oi Pf Pz Qc) Mp(Ik Iq It Jm Lj Ly Lz Mc Ml Nd Ne Ng Nh Nk Nl Oe Of Oi Oy Oz Pb Pz Qc) Nq(Hq Ik Io Iq It Jm Lu Ly Mc Mf Mk Ml Nd Ne Nh Oe Of Pf Pz Qc) Mx(Hv Ii Ij Il In Iu Jj Lu Mb Md Mn Mw My Na Nd Nj Nm Ny Og Pd) aP(Ad aM An aO Aw bB BG bH bR cF cJ Cp Cq Cw Dd De dF Dk) Ij(Iu Li Lu Lz Md Mh Mj Mn Mq Ms My Nd Nj Ny Pb Pd) Ny(Hv Ii In Iu Lu Md Mh Mq My Na Nd Nj Nu Og Wm) Wm(Ip Iq Is Jn Lh Lv Mi Mu My Nn Ok Pg Qa) Jj(In Iu Jm Js Li Md Mj Mn Mw My Nd Pd Qb) Dd(aO aX bE bF Bg bW bZ cU De dF dI Dk) De(An Ax bA bV cJ Cq dF dI dM Ex Gl) Md(Ih Ii Il Iu Js Mj Mn Mw My Nj Qb) Mn(Hv Ii In Iu Lu Mq Ms My Na Ni) bA(An aO Aw bE BG bJ bZ cU Dk) Ip(It Lj Mc Ml Ne Ng Nh Pz

Figure 34 Continued

Qc) Iu(Hv In Js Lu Mq Mw My Na Pd) Cp(aX bE bH bZ cJ dE dI) Cw(aX bE bH bW bZ cU dI) My(Hv Ii In Js Mh Mq Nj) Aw(An AX cJ dI Gl) Ii(Ih Mh Ms Mw Nj Og) jH(hR hW iB jD jP IM) dK(bG Dk Ex Fw Gl) Ad(aX bZ cU dI) Cq(aX cJ Db dE) Lu(Ih Js Nm Qb) Mq(Il Js Mw Ns) An(aX bC cJ) Ex(bR cD cJ) Nj(In Js Na) iB(hR hW jD) Mj(Ih Il) aO(aM dM) bE(dF Gl) fR(Co cX) kG(IX mW) CubZ DkcJ MsMw NaNd bHdF mFmP hWjR jDIO Unconstrained panels with 2 analytes, where 1.0E-2 >= 'model p-value' > 1.0E-3. Contains 3,097 panels of 16,788 total panels evaluated. :
Cq(aC AD aE AF aG aH al Aj aK AL aM AN AO Ap aQ AR AS aU aV AW Ax aY aZ BA BB BC bE bF BG bH bI bJ bL bM BN BO bP bQ bR bS bU bV bW bX bZ cA cB cC cD cE cF cG CH cI cK cL cM cN CO CP cQ cR Cs CT CU CV CW CX cY cZ dA dB dC DD dF DG dH DI dJ DK DL dM Ex fR Fw Gl) dF(aC AD aE AF aG aH al Aj aK AL aM AN AO Ap aQ AR AS aU aV AW AX aY aZ BA BB BC bF BG bI bJ bL bM BN BO bP bQ bR bS bU bV bW bX bZ cA cB cC cD cE cF cG CH cl cJ cK cL cM cN CO CP cQ cR Cs CT CU CV CW CX cY cZ dA DB dC dD dE DG dH DI dJ DK DL dM Ex Gl) Aw(aC AD aE AF aG aH al Aj aK AL aM aN AO Ap aQ AR AS aU aV aW aY aZ Ba BB BC bE bF BG bH bI bJ bL bM BN BO bP bQ bR bS bU bV bW bX bZ cA cB cC cD cE cF cG CH cI cK cL cM cN CO CP cQ cR Cs CT CU CV CW CX cY cZ dA DB dC DD DE DG dH Di dJ DK DL dM Ex fR Fw) De(aC AD aE AF aG aH al Aj aK AL aM aN AO Ap aQ AR AS aU aV aW aX aY aZ Ba BB BC bE bF BG bH bI bJ bL bM BN BO bP bQ bR bS bU bW bX bZ cA cB cC cD cE cF cG CH cI cK cL cM cN CO CP cQ cR Cs CT CU CV CW CX cY cZ dA DB dC dD dE DG dH Di dJ DK DL fR Fw) bA(aC AD aE AF aG aH al Aj aK AL aM aN Ao AP aQ AR AS aU aV aW AX aY aZ Ba BB BC bF bH bI bL bM BN BO bP bQ bR bS bU bV bW bX cA cB cC cD cE cF cG CH cI cJ cK cL cM cN CO CP cQ cR Cs CT Cu CV CW CX cY cZ dA DB dC DD dE dG dH DI dJ dK DL dM Ex fR Fw Gl) Cp(aA AD aE AF aG aH al Aj aK AL aM AN AO Ap aQ AR As aU aW Ax aY aZ Ba BB BC bF BG bI bJ bL bM BN BO bP bQ bR bS bU bV bW cA cB cC cD cE cF cG CH cI cK cL cM cN CO cQ cR Cs CT CU Cv CW CX cY cZ dA DB DC DD dG dH Di dJ DK DL dM Ex fR Fw Gl) aP(aC aD aE AF aG aH aI AJ aK AL aN Ao Ap aQ AR AS aU aV aW AX aY aZ Ba Bb BC bE bF bI bJ bL bM BN BO bP bQ bS bU bV bW bX bZ cA cB cC cD cE cG CH cI cK cL cM cN CO cP cQ cR CS CT CU CV cW CX cY cZ dA DB dC dD dE DG DI dJ dK DL dM Gl) Cw(aA Ad aE Af aG aH aI Aj AL AN AO Ap aQ Ar As aU aV aW Ax aY aZ Ba BB BC bF BG bI bJ bL bM BN BO bP bQ bS bU bV cB cD cE cF cG CH cI cJ cK cM CO cR Cs CT Cu CV CX cY cZ dA DB DC DD dE DG Di dJ DK Dl dM dN Ex fR Fw Gl) aA(AD aE aF Aj aK AL An Ao aQ AR AS aV aW Ax aY Ba bI BN Bo bP cA Ch cI cL cP cQ Ct Cu CV cW Cx cZ dA Db dG Di DL fR Gl kC kE kF kI kK kN kO kP lW lX lY mE mF mH mI mM mS mT mU mW mY mZ nA nB nC nD nF nH nI nJ nK nL nM nN nO nT nU oO oP oQ) dN(aC AD aE AF aH Aj aK AL aM Ao Ap aQ AR AS aU aV aW AX aY aZ Ba Bb BC bE bI bJ bM BN BO bP bQ bR bU bV bX cA cB cC cD cE cF cG CH cI cL CO cP cQ cR Cs Ct Cu CV cW CX cY cZ dA DB dD DG DI dJ DL Ex fR Fw Gl) Cu(AD aE Af aG aH aI Aj AL AN AO Ap Ar As aU AX aY aZ Ba BB BC bE bF BG bH bI bJ bL bM Bn Bo bQ bR bS bU bV bW cD cF cG CH cI cJ cK cL cM cN Co cR Cs CT cU Cv CX cY DB Dc Dd dE Dg dH DI DK Dl dM Ex fR Gl) cS(aC aD aE AF aG aH aI aK aL aM Ao aQ aR aS aU aV aW aX aY aZ BB bC bE bF bI bJ bL bM bN bO bP bQ bR bS bU bV bW bX bZ cA cB cC cD cE cF cG cH cI cJ cK cL cM cN cO cP cQ cR cT cV cW CX cY cZ dA dB dC dD dE dG dH dI dJ dK dL Ex fR Fw) Dc(aC AD aE AF aH aI aK AL aM aN Ao aQ AR AS aU aV aW aY aZ Bb Bc bI bM BN BO bP bR bU bX cA cB cC cE cF cH cI cK cL cM cN cP cQ cR Cs CT CV cW cX cY cZ dA dC DD DG dH Di dJ DL dM Ex fR Fw) aJ(aC aD aE AF aG Aj aK AL Ao Ap aQ AR aS aU aV aW AX aY aZ Ba Bb Bc bE bI bL BN BO bS bU bV bW bX cA cB cC CH cI cL CO cP cQ cR Cs CT CV cW CX cY cZ dA DB dC dE DG Di dJ DL dM Gl) Dd(Ad aF aG aH aI Aj Al AN Ao Ap Ar As aU Ax Ba BB BC bG bH bJ bL Bn bO bQ bS bU bV cB cD cE cF cG CH cI cJ cK cM CO cR CT Cv cW Cx dA DB dC dD dE dG dH Di dK DL dM Ex fR Gl) aO(AD aF aG aI aK AN aR As aU aX aY bB BC bE BG bH bJ bL Bn bO bQ bR bS bU bV bW bZ cB cC cD cE cF cG cJ cK cL cM cN cP cQ cR cT cU CV cW cX cY dA dB dE dG dH dI DK DL Ex Gl) An(Ad aG aH aI Aj Al aM Ao Ap As aU Ax Ba BB Bc bE bF BG bH bJ bL Bn bQ bS bV bW bZ cD cE cF cG Ch cK cM CO cR CT cU Cv cW cX Db dC dD dE dG DI DK DL dM Ex fR Gl) Js(Fp Hq Hr Hu Hv Ih Ii Ij Ik Il In Io Iq It Jm Li Lj Ly Lz Mb Mc Me Mf Mh Mj Mk Ml Mn Ms Mw Mx Na Nc Nd Ne Nf Ng Nh Ni Nk Nl Nm Ns Nu Ny Oe Of Og Oi Oy Oz Pb Pd Pf Pz Qb Qc Wm) Ii(Fp Hq Hr Hu Hv Ij Ik Il In Io Iq It Iu Jm Li Lj Lu Ly Lz Mb Mc Me Mf Mj Mk Ml Mq Na Nc Nd Ne Ng Nh Ni Nk Nl Nm Ns Nu Oe Of Oi Oy Oz Pb Pd Pf Pz Qb Qc Wm) dM(Ad aG aH aI aM aN aU aW aX aZ bB bC bE bF BG bH bJ bL bO bQ bS bV bW bZ cC cD cE cF cG cJ cK cM cN cO cR cT cU cW cX dA dB dD dE dI DK dL fR) Ny(Fp Hq Hr Hu Ih Ik Il Io Iq It Jm Li Lj Ly Lz Mb Mc Me Mf Mj Mk Ml Mn Ms Mw Nc Ne Ng Nh Ni Nk Nl Nm Ns Oe Of Oi Oy Oz Pd Pf Pz Qb Qc) Md(Fp Hq Hr Hu Hv Ik In Io Iq It Jm Li Lj Lu Ly Lz Mb Mc Me Mf Mh Mq Ms Na Nc Nd Ng Ni Nk Nl Nm Ns Nu Oe Og Oi Oy Oz Pb Pd Pf Pz Qc) Ij(Fp Hq Hr Hu Hv Ih Ik Il In Io Iq It Jm Lj Ly Mb Mc Me Mf Mk Ml Mw Na Nc Ne Ng Nh Ni Nk Nl Nm Ns Nu Oe Of Oi Oy Oz Pf Pz Qb Qc Wm) Mx(Fp Hq Hr Hu Ih Ik Io Iq It Jm Li Lj Ly Lz Mc Me Mf Mh Mj Mk Ml Mq Ms Nc Ne Ng Nh Ni Nk Nl Ns Nu Oe Of Oi Oy Oz Pb Pf Pz Qb Qc) kG(kC kE kF kI kK kN kO kP lW lY mE mF mH mI mM mP mS mT mU mY mZ nA nB nC nD nF nH nI nJ nK nL nM nN nO nR nT nU oO oP oQ) Nr(Fp Hq Hr Hu Hv Ik Io Iq It Jm Li Lj Ly Lz Mb Mc Me Mh Mj Mk Ml Na Nc Ne Ng Nh Ni Nk Nl Ns Oe Of Oi Oy Pf Pz Qc Wm) Dk(Ad aI aM aN Ap As aU aX Ba bB bC bE bF BG bH Bn bQ bV bW bZ cD cF cG cM Co cT cU Cv Db dG DI dL Ex fR Gl) Qb(Fp Hq Hr Hu Hv Ih Il In Io Iu Li Lz Mb Me Mf Mh Mj Mn Mq Ms Mw My Na Nc Nd Ni Nj Nl Nm Nu Oe Og Oi Oz Pb Pd Pf) cU(aG aH aI aM As aX aY Ba bB bC bE BG bH bL Bn bR bU bV cC cD cF cJ cK cL cM cN cT Cv cW dE dH dK Dl Ex fR) Mw(Fp Hq Hr Hu Hv Ih Il In Io Jh Li Lu Lz Mb Mf Mh Mj Mn Mv Na Nc Nd Ng Ni Nj Nk Nl Nm Ns Nu Oe Oi Oz Pd Pf) My(Fp Hq Hr Hu Ih Ik Il Io Iq Li Lj Lu Lz Mb Me Mf Mj Ms Na Nc Nd Ng Ni Nk Nl Nm Ns Nu Oe Og Oi Oz Pb Pd Pf) Iu(Fp Hq Hr Hu Ih Ik Il Io Jm Li Lz Mb Me Mf Mh Mj Mk Ms Nc Nd Ni Nj Nk Nl Nm Ns Nu Oe Of Og Oi Oy Oz Pb Pf) Nf(Fp Hq Hr Hu Hv Ik In Io Iq It Jm Lj Ly Mb Mc Me Mf Mk Ml Na Ne Ng Nh Ni Nk Nm Ns Oe Of Oi Oy Pf Pz Qc) Oh(Hq Hr Ik Io Iq It Jm Lj Ly Lz Mb Mc Me Mf Mk Ml Ms Nc Ne Ng Nh Nk Nl Ns Of Og Oi Oy Oz Pb Pf Pz Qc Wm) Ad(aG Al Ao Ar Ax Ba bB bC bE bF BG bH bJ bL bQ bS bV bW cD cG cJ cK CO cT DB dE dK Ex fR Gl) Hv(Fp Hq Hu Ih Il In Iq It Jj Li Lu Lz Me Mf Mh Mj Mq Ms Nc Nd Nj Nk Nl Nm Nu Og Oy Oz Pb Pd Pf Wm) Ex(aH aI Aj aM Ar As aU Ax aZ bB bE bF Bg bJ Bn Bo bS bU bW bX bZ cA cC cG Ch cI Co Cv dH DI Gl) Mn(Fp Hq Hr Hu Ih Il Io Iq Li Lz Mb Me Mf Mh Mj Nc Nd Nj Nk Nl Nm Ns Nu Oe Og Oi Oz Pb Pd Pf Wm) Mv(Fp Hq Hr Hu Ik Io Iq It Jm Lj Ly Lz Mc Me Mf Mk Ml Nc Ne Ng Nh Nk Ns Oe Of Oy Oz Pb Pf Pz Qc) Jh(Hq Hr Ik Io Iq It Jm Lj Ly Mc Me Mf Mk Ml Nc Ne Ng Nh Ni Nk Ns Nu Oe Of Oi Oz Pb Pf Pz Qc Wm) Ih(Fp Hq Hr Hu Il In Io Li Lz Mb Me Mf Mh Mq Ms Na Nd Ni Nj Nl Nm Nu Oe Og Oi Oz Pd Pf Wm) In(Fp Hq Hu Il Iq It Li Lu Lz Mf Mh Mj Ml Mq Ms Na Nc Nd Nk Nl Nm Nu Og Oy Oz Pb Pd Pf) Pd(Fp Hu Ik Il Li Lu Lz Mb Mh Mj Mq Ms Na Nc Nd Ni Nj Nk Nl Nm Ns Nu Og Oi Oz Pb Wm) Jj(Fp Hq Hr Hu Iq Lu Lz Mb Mf Mh Mq Na Nc Ng Ni Nj Nk Nl Nm Nu Of Oy Oz Pf Pz Wm) Nm(Fp Hq Il Io Li Lw Lz Mg Mh Mj Mq Ms Na Nc Nd Nj Nk Nl Nu Nx Og Oz Pf Wm) bG(aM aN As aX bB bC bE bJ Bn bQ bV bW cD cJ cK cM cR cT cW dE dG dI dL fR) hW(eD hA hV hX iC jE jF jG jK jL jM jO jP jQ jT jU jV jY lK lL lM lN lO) jD(eD hA hR hV hX iC jE jF jG jK jL jM jO jQ jR jT jU jV jY lK lL lM lN) Gl(Aj aM As aX aZ bB Bg bJ Bn Bo bP bW bX cA cD cJ cT Cv cX Db DL) Na(Fp Hq Hu Hw Il Li Lu Lz Mf Mh Mj Mq Ms Nc Nk Nl Nu Og Oz Pb Pf Wm) fR(aM aN bC bF Bg bH bJ Bo bS bU bW cC cD cF CH cK cM cN Cx dA dH) jH(eD hA hV hX iC jE jF jG jK jL jM jO jQ jR jT jU jV jY lK lL lN lO) Mg(Hq

Figure 34 Continued

Hu Iq It Jm Lj Ly Mc Mf Mk Ml Ne Nh Ns Oe Of Oy Pf Pz Qc Wm) Li(Hq Il Io Lu Mb Mh Mj Mq Ms Nc Nd Ni Nj Nk Nl Nu Og Oi Oz Pb) Nx(Hr Ik Iq It Jm Lj Ly Mc Me Mf Mk Ml Ne Ng Nh Of Oy Pz Qc Wm) aM(bC bF Bg bH bJ bL bQ bS bV bW bZ cE cG cJ cK cT dE dG dI dK) Bg(Ar As AX bC bE Bn bV bW cD cJ cT Cv dE dG dI dK dL) Lw(Hr Ik Iq It Jm Ly Mc Me Mk Ml Ne Ng Nh Oe Of Oi Pz Qc) Mq(Fp Hq Hu Lu Lz Mb Mf Mh Mj Nc Nd Nj Nk Nl Nu Og Pb Pf) Hw(Hr Ik It Jm Lj Ly Mb Mc Me Mk Ml Ne Ng Nh Of Pz Qc Wm) mP(kC kE kN lW lX mM mU mW mZ nB nC nF nH nI nN nO nR nT) As(aX Ba bC bE bF bH bV bW bZ cJ Co DB dE dI dK) Wm(Iv Jk Jo Lx Ly Ma Mj Mp Mr Nq Nt Pa Pc Pe Po Qe) Mj(Fp Hq Hu Ik Lu Lz Mb Ms Nc Nd Ni Nj Nl Nu Og) Il(Fp Lu Lz Mb Mf Mh Ms Nc Nd Ni Nj Nu Og Pb Pf) Im(Ik Iq It Jm Lj Ly Mc Ml Ne Ng Nh Ns Of Pz Qc) cJ(Al Ar Ax Ba Bc bH Bn bV bZ cK Co Cv Db Di Fw) bQ(aN aX bE bJ bR cC cD cE cL cN dE dH dK) Bn(aX Ba bC bE bF bH bW bZ dE dI dK) Lu(Fp Hq Iq Lz Mb Mh Nd Nj Nl Nu Pf) nR(kK lX mF mI mW nC nH nI nK nT) Nj(Fp Hq Lz Mb Mh Nd Ni Nu Pf) Pc(Ik Jm Mc Ml Ne Ng Nh Oe Pz) bV(Ao bB bE bH bW cK Co dK) mF(mI mT mW nM nN oP oQ) Nu(Hq Lz Mb Mh Nd Og) bW(Ax cD cT Cv Db dE) bZ(aN bC bH cT Cv dK) iB(jE jP jR lK lM lO) Nd(Fp Hq Mf Mh Ni) cK(aI bB cF cT dK) Mb(Fp Lz Mf Mh) Ni(Lz Nc Nk Nl) Iv(Lj Ng Nh Pz) Jg(Ml Ne Nh Qc) lM(hR jE jP lO) bB(bC bH dK) cD(Ba cG dA) cT(bC bE bH) dI(cC Cv DI) Qe(Iq Nh) aI(bE dE) mW(kE nC) hR(hX jP) oQ(nB nO) AxdK CvbH MhNl bRdA cGcL nNmU jEjF jPlO

Constrained panels with 3 analytes, where 1.0E-8 >= 'model p-value' > 0. Contains 3,259 panels of 645,860 total panels evaluated. : Nn{Lv(aA Et Fr Hu Hw Hx Ii Il Im Io Ip Ir Is Iu Iv Ji Jj Jl Jn Jo Jp Jq Jr Lh Lu Lx Mi Mr Ms Mt Mu Mz Na Nb Nj No Nr Nt Og Oi Ok On Pa Pc Pe Pg Po) Hu(aA Et Fr Hw Hx Ii In Ip Ir Is Jh Ji Jk Jl Jn Jo Jp Jq Jr Jt Lh Lu Lx Mr Mt Mu Mz Nb No Nq Nt Nv Nw Nx Oi Ok Om On Pa Pe Pg Po Qa) Jq(aA Et Hw Hx Il Im Ip Is Jl Jn Jo Jp Jr Lh Lx Ma Mi Mm Mp Mr Ms Mt Mu Nd Nj No Nr Nt Og Ok On Pa Pe Pg) Jr(aA Et Fr Hw Ip Ji Jj Jl Jo Lh Lj Lu Lx Mi Mm Mr Ms Mu My Ng No Ns Nt Og Oi Ok On Oy Pa Pe Pg Qc) Et(aA Hw Hx Il Io Ip Is Ji Jl Jn Lh Lu Lx Mi Mm Mr Ms Mz No Nr Nt Oi On Pa Pe Pg Pz Qa) aA(Hx Il In Io Ip Is Ji Jl Jn Jo Lh Ma Mf Mg Ms Mt Mu Mx Mz Nj Nt Oi Om On Pc Pe Pg) Ip(Hw Hx Is Ji Jj Jl Jn Jo Lh Lx Mi Mr Mz Nb No Nr Nt Oi Ok On Pa Pe Pg Po Qa) Jn(Hw Io Jj Jl Jo Js Lh Lu Lx Ma Mi Mp Mr Ms Mu Nd No Nt Og Oi Ok Pa Pe Pg) Ok(Fr Hw Hx Il Is Jl Jp Lx Ma Mi Mp Mr Ms Mt Mu Nd No Nt Og Oi Pa Pe Pg) Pg(Hw Io Is Ji Jj Jo Mr Ms Mu My Mz Ng Ni Ns Og Oi Oy Pb Pc Qa) Jl(Im Io Is Ji Jj Mf Mh Ms Mu Ni No Nt Og Oi On Oz Pb Pc Pz) Fr(Hv Hw Ij In Jo Lh Mf Mr Ms Mu Ng Ni Nj No Oi Oy Pe) Is(Hw Io Jj Jo Lh Lx Mi Mr Ms Ni No Nt Og Oi Pa Pc Pz) Ji(Hw Io Lh Lu Lx Ma Mm Mr Ms No Nt Og Oi On Pa Pe Qc) On(Io Jj Mm Ms Mu Mw My Ng Ni No Ns Of Og Oi Oy Pz) Mr(Jj Jp Lw Ma Ms Mt Ni Nj Og Oi Pc Qa Qd) Pa(Hv Hw Jo Mk Ms Mt Mz Na Ni Nj Oi Qa) Pe(Jj Jp Li Ma Ms Mt Nj Og Oi Oy Pb Pc) Nt(Io Jj Jp Ms Mt Mz Nj Nw Og Oi Qa) Lh(Io Jj Ma Ms Ng Nj Og Oi Oy Pb Pc) Jo(Jj Jp Ms Mt Nw Og Oi Pb) Hw(Jp Lx Mt Nj Nw Oi) No(In Jj Nj Oi Pc) Oy(Jh Mw Nb Om Po) Og(Hx Nb Om) Ms(Nb Om) Qa(Lx Mi) Jj(Il Jk) Oi(Ir Mt) MwMy} Et{Io(aA Hw Hx Ih Il Ip Ir Is Iu Iv Ji Jk Jl Jn Jq Jr Jt Lh Lu Lv Lw Lx Mh Mi Mp Mr Mt Mx Mz Nb Nc Nk Nl No Nq Nr Nt Nv Nw Oh On Pa Pc Pe Pg Po Qa Qb Qd Qe) Pz(Fr Hw Hx Il Ip Ir Is Ji Jk Jl Jn Jq Jr Lh Lu Lv Lx Mi Mp Mr Mt Mu My Mz Nk Nq Nt Nv Nw On Pa Pc Pe Pg Po Qa Qd Qe) Mm(Fr Hx Il Ip Is Ji Jk Jl Jn Jq Jr Lh Lv Lw Lx Md Mi Mp Mr Mt Mu Mz Nf No Nq Nt Nv Nw Om On Pa Pc Pe Pg Qa Qe) Ip(aA Fr Hw Hx Il Is Ji Jk Jl Jn Jq Jr Lh Lu Lv Lx Mi Mp Mr Mt Mu Mz Nf Nm No Nq Nt Nv Oh On Pa Pc Pe Pg Qa) Pc(aA Hw Hx Il Is Ji Jl Jn Jq Jr Lh Lu Lv Lx Mi Mr Ms Mt Mz Nf No Nr Nt Nw Og Oi Pa Pe Pg Qa) Lv(aA Hw Hx Ji Jj Jk Jn Lh Lu Lx Mi Mp Mr Mt Mu Mz Nf No Nq Nt Nw Oh Oi On Pa Pe) Og(Hx Il Is Ji Jk Jl Jr Lh Mt Mu Mv Mw Nb Nq Nv Om On Pa Po) Jq(Il Jl Lh Lu Lx Mi Mp Mr Mu Nd Nj No Nq Nt Pa Pg) Mu(aA Is Ji Jj Jl Jn Jr Ms Ng Nj No Of Oy Pb) Mp(Hw Hx Ji Jn Jr Lu Mt Mz Nf Nj No Nw Qa) Jk(Hu Ji Jj Lw Mg Ms My Ng Nm Of Oi Oy) Nq(Hu Hw Jj Jn Jr Ms My Mz Ng Oy Qa) Mt(Hw Lw Mh Ms My Nj Nt Ny Oi Pb) Jn(aA Fr Lh Lu Lx Mi No Nt Oi Pg) On(Hu Jj Jr Ng Nj Nm Ns Of Oi Pb) Il(aA Ji Jj Lw Ms Ng Of Oh Oi) Pb(Hw Hx Lh Mr Om Pe Pg Po) Lu(Hx Is Ji Jr Lw Nj Qa) Pg(aA Ii Ji Jj Mz Of Oy) Fr(Hw Jl Mz Ng No Qa) Nj(aA Mi No Nt Nv Pa) Jr(aA Jl Lh Mi No Nt) Ms(Hx Is Nb Om Pa) Lw(aA Lx Mr Pa) Mz(Mi Ml Nt Oi) Jj(Jl Lh Nt Nv) Oh(Mr Oi Pa Pe) Mw(My Ng Oy) Is(Nm No Oi) aA(Jl Ma Mg) My(Mv Nb) Ng(Nv Pa) Ji(Nm No) Lh(Ii Jo) Nw(Hw Nt) Oy(Jh Om) MaMr MiQa MkPa JlOz NvOi} Jl{Pb(Fr Hw Ij In Ip Is Jg Jh Ji Jn Jo Jq Jr Jt Lh Lw Ma Md Mg Mp Mt Mu Mz Na Nf Ni Nm No Nq Nt Ok Om On Pe Pg Qa) Io(aA Fr Ip Is Ji Jj Jn Jp Jq Jr Jt Lh Lv Lw Ma Mg Mi Mm Mp Mt Mu Mz Nm No Nq Nt Og Oh Ok On Oz Pc Pg Qa) Mh(Fr Im Ip Is Jg Ji Jj Jn Jq Jr Lh Lw Mg Mt Mu Mz Nb Nf No Nq Nt Nw Oh Ok Om On Pc Pe) Oz(aA Fr Im Ip Is Jj Jn Jq Jr Lw Ma Mg Mm Mp Mt Mu Nd No Nq Nt Og Om On Pc Pd Pe Pg) Og(Fr Ip Jg Jh Ji Jn Jq Jr Lh Lw Mg Mi Mm Mt Mu Mv Mw Mz Nb Nf Nm Nq Om On Pc) Mm(aA Fr In Ip Is Ji Jj Jn Jq Jr Lh Lv Mg Mt Mu Mz Nf Ni No On Pz Qa) Pc(aA Ip Is Jn Jp Jq Jr Lh Lv Mg Ms Mt Mz Nf Ni No Nt Oi Ok Om Qa) Mg(aA Ii Ip Is Jj Jn Jo Jq Jr Lv Lw Ms Mz Ng No Oi Oy Pz) Jj(Fr Ip Is Jn Jo Jq Jr Lh Lv Lw Ma Mt Mu Nq Nt On Pg) Ii(Ji Jn Jq Jt Lh Lw Md Mi Nf Nm No Nt Om On Pg) Nq(Hu Ip Is Jn Jq Jr Lv Mk Ms My Mz Ng Ok Oy) Ip(aA Fr Ji Jn Jq Jr Lh Ma Mt Mu Mz No Oh) Mp(Hq Jn Jq Jr Lv Mk Mz Ni Ns Ok Oy) Ms(Fr Jg Jh Ji Lw Mt Mu Mw Nf Om) Lv(Jn Lh Mi Mt Mu Mz Nf Nt Oh) Lw(aA Fr Is Jn Jr Lu Mu No) Ma(aA Jn Jq Jr Lh Mz Nf No) Mt(Hx Jq Ml My Ny Oi Oy Pz) Mu(Is Ji Jn Jr Ng Nj Oy) On(aA Hu Ng Ns Of Oi Pz) Mi(Jn Jq Jr Mz Ni Nj) Jg(aA My Ng Oi Oy Pz) Ji(aA Ml Nx Pz Qc) Oy(Fr Jh Mv Mw Om) My(Jh Mv Mw Om) Jo(Jt Lh Nm Nt) Fr(aA Ng Pz) Ml(Jq Mz) Nj(aA Nf) Pz(Is Jn) Jr(aA No) Om(Ng Of) MkPa OhOi} Fr{Ng(Hv Hw Hx Ih Ij In Ip Is Iu Iv Jg Jh Ji Jk Jn Jo Jr Jt Lh Lv Lw Lx Md Mg Mi Mp Mq Mr Mt Mu Mx Mz Nb Nf Nt Nv Nx Om On Pa Pe Pg) Oy(Hv Hw Hx Ii Ij In Is Iv Jh Jn Jo Jq Jr Jt Lh Lx Md Mi Mp Mq Mr Mt Mu Mw Mx Mz Nb Nf Nt Nv Nx Om On Pa Pe Pg Po) Pb(Hv Hw Hx Ij In Ip Iv Ji Jo Jq Jt Lh Mp Mq Mr Mt Mu Mx Mz Na Nb Nf Ni No Nr Nt Nu Ny Ok Om On Pe Pg Qa) Og(Hx Ij In Ip Is Jg Jh Ji Jn Jo Jr Jt Lh Lw Mi Mr Mt Mu Mw Mx Mz Nb Nf Nm Nt Nv Nx Om Pe Pg Qe) Nj(aA Hv Hw In Ip Ir Is Jj Jo Jq Jr Jt Lh Mi Mp Mq Mu Mx Mz Na Nf Ni No Nt Oh On Pe Pg Pz Qa) My(Hx Ii Ij In Jg Jh Lh Md Mi Mr Mt Mu Mv Mw Nb Nf Nt Nv Nw Nx Om On Pe Pg) Ms(Hx Ij In Is Jg Jh Ji Jn Jo Jt Lh Lw Mi Mr Mu Mx Nb Nm Nt Om Pc Pe Pg) Ip(aA Hv Hw Io Ir Jj Jn Jq Jr Jt Lh Lv Mm Mz Na No Nt On Pz Qa) Jj(Hw Hx Ih Ij In Jk Jo Lh Lv Mp Mt Mu Nl Nt On Pe Pg) Hu(Hv Hx In Is Jh Jk Jo Lh Mu Mx Nq Om On Pg) Lv(aA Hw Io Is Ji Jn Jq Mt Mz Na No Nt Oh) Mp(Hq Hv Ij In Io Jq Mz Ni Ns Ok) Io(Is Iu Ji Jt Lw Mi Mx Nl) Pz(Hw Ir Is Ji Jn On Qd Qe) Of(Hx Ij In Lh Nb Om On) Mh(In Mr Mt Nb) Ni(Mi Nk Nl Oh) On(Mm Mv Mw Ns) In(Ml Ny Oh) Pc(Mk Oh Pc) aA(Ji Jn Lw) Mm(Ji Mt) Nb(Hx Ny) Hq(Lx Nd) NoLw NsMq NtMz MgJo MkPa MtNy NlIj IiLh QcJr} Ji{Io(aA Hw Hx Il Ip Is Iu Jg Jk Jo Jp Jr Jt Lh Lu Lv Lw Lx Mi Mm Mp Mr Ms Mt Mu My Nj Nl No Nq Nt Nv Oh On Pa Pc Pe Pg Qe) Ms(aA Hw Hx Il Ip Is Iu Jg Jh Jk Jo Jp Jr Lh Lu Lv Ma Mb Mi Mm Mp Mr Mt Mu Mv Mw My Nb No Nq Nt Nv On Pa Pc Pe Pg) Og(Hx Il Ip Is Jg Jh Jk Jo Lh Lv Mg Mi Mr Mt Mu Mv Mw Nb Nq Nv Om Pa Pc Pc Pg Po) Mm(Hw Il Ip Is Jk Jq Jr Lh Lu Lv Lx Ma Mi Mp Mr Mt Mu No Nq On Pa Pc Pe Pg) Pc(aA Hu Hw Il Ip Is Iu Jo Jr Lh Lu Lv Lx Ma Mi Mr Mt Nd No Nt Oi Pa Pe) Lv(aA Hw Il Ip Jk Jr Lh Lu Lx Mi Mp Mr Mu No Nq Nt Oh On Pa Pe) Ml(Il In Jk Jr Lh Lu Lx Ma Mr Mt Mu No Nq Nv On Pa Pe Pg Po) Ip(aA Hw Il Jk Jr Lh Lu Lx Mi Mp Mu Nm No Nq Nt Pa Pg) Jk(aA Hu Ii Jj Jr Jt Lu Ma My Ng Nm Nx Oy Pb Pz Qc) Jr(aA Lh Lu Lx Ma Mi Mp Mu No Nq Nt Pa Pg Qc) Pb(Hw Jo Lh Lu Mr Mt Mu Nq Nv On Pa Pe Pg) Ma(aA Hw Lh Lx Mb Mi Mr Nd No Nt Pa Pe) Pa(Hx Jq Md Mh Mk Mt My Nj Ny Oy) Nq(aA Hu Hw Jj Jq My Ng Oy) Mu(aA Jj Ng Nj Oi Pz) Nj(aA Lu Mi No Nt) Ii(Lh No Nt Pg) Jj(Il Lh Nt Pg) My(Mt Mv Mw) aA(Il Mg Pg) Mh(Lx Pe) Qc(Il On) Oy(Jh Mw) LuLw MpJq JtOn NxPg} Jr{Ip(aA Hw Io Jg Jj Jk Jo Jp Jq Lh Lu Lv Lw Lx Ma Mg Mi Mm Mp Mr Mt Mu Nb No Nq Nt Nv Og Ok Om On Pa Pc Pe Pg Qc) Pc(aA Hw Io Jj Jk Jo Jp Jq Lh Lu Lv Lx Ma Mg Mi Mp Mr Ms Mt Mu

Figure 34 Continued

Figure 34 Continued

Qd) Nt(Ik Io Jp Lw Ly Mt Nw Oh Ok Oy Pc) Pg(Hq Hu Ii Ik Ir Jq My Ns Of Ok Qa) Oy(Jh Lx Mi Mt Nb Nw Om Pa Pe Po) Pc(Ir Jq Lh Mi Mr Ok Pa Pe Qa Qd) Qa(Io Lx Ma Mi Nw Oh Oi Pa) Lh(Jo Lw Ly Ma Mh My Of Qd) Jq(Lx Ma Mr Mt Ok Pe) Nw(Hw Jo Jt Ma My Oi) Lw(Ir Mr Pa Pe) Lx(Hq Jt Ly Qd) Mi(Ik Ok Om Qd) Ma(Ir Jt Mr) Mt(Jt My Pe) My(Mw Nb) Ik(Pe Qd) Ir(Io Oi) Oh(Mr Pe) Ok(Pz Qe) NoHu QdOi} Is{Ip(Hw Io Jj Jp Lu Lw Lx Ma Mg Mi Mm Mp Mr Ms Mt Mz Nf Nq Nt Nv Nw Og Oh Ok Om Pa Pc Pe Pg Po) Ms(Io Jh Jj Jk Jo Jp Lw Lx Mg Mi Mm Mp Mr Mt Mv Mz Nb Nt Nv Nw Oh Ok Om Pa Pe Po) Og(Hw Hx Io Jh Jk Jo Jq Jr Lw Lx Mi Mm Mr Mt Mv Mz Nb Nt Nv Nw Pa Pe Pg Po) Io(Hw Jj Jo Jp Jq Jr Jt Lx Ma Mg Mr Mt Mz Nj Nq Nv Nw Oh Ok Pa Pe) Ma(Hw Jj Jq Lh Lw Lx Mb Mi Mr Mt Mz Nf Nt Nw Oi Ok Pa Pc Pe) Jj(Hw Jg Jk Jo Jr Lu Lx Mg Mi Mp Mr Mt Nv Om Pa Pc Pe Po) Pc(Hw Jo Jp Jq Lu Lx Mi Mr Mz Nf Ni Nt Ok Pa Pe Pg) Jq(Jt Jp Jr Js Lu Lx Mg Mi Mr Nd Nj Nq Pa Pe) Nq(Hw Jm Lw My Mz Ng Ni Nj Oi Ok Oy Pe) Mm(Hw Lu Lx Mr Nf Ni Nt Oi Pa Pe Pz) Mg(Hw Ik Jp Lu Mz Ng Oi Ok Pe Pz) Lw(Jp Jr Lh Lx Mr Mt Nt Pa Pe) Mp(Hw Jp Mz Nf Ni Nj Nw Ok Om) Nt(Jm Jp Mt Mz Ne Nj Oh) Mt(Mh My Ny Oi Pb
Qc) Oh(Lx Mr Oi Om Pa Pe) Mi(Jp Mz Ni Nj Om) Pg(Ii Ik Jm Mz Pb) Pa(Mh Mk Ni Nj) Lx(Jm Ly Mh) My(Jg Mv Om) It(Hw Jo Jr) Lu(Jr Nj)
Mz(Ml Qc) Nw(Hw Jo) Om(Oy Pb) NgJg QcJi JhOy NvOi PbPe} Ip{Mm(Hw Hx In Ir Jo Lu Lx Mr Mt Nb Nf Nr Nt Nv Nw Ok Om Pa Pe Pg
Po Qa) Mt(Hw Jj Jn Jo Jt Mh Mi Mp Mr My Mz Nb Ny Og Ok Pa Pb Pc Pe Pg Qa) Mz(Hw Iu Jj Jk Jo Lx Ma Mg Mi Ml Mr Nj Nv Og Ok Pa
Pb Pc Pe Pg) Jj(Hw Hx Il Jn Jo Jq Jt Lx Md Mg Mi Mp Mr Nb Nv Om Pa Pe Po) Ok(Jk Jn Jp Lu Lx Mg Mi Mp Nt Nv Nw Og Oh Pa Pb Pc Pg)
Og(Hw Hx Jh Jk Jq Mi Mr Mv Nq Nt Nv Pa Pe Pg Po) Jn(Jk Lx Ma Mi Mp Mr Nq Nt Nv Om Pa Pc Pe Pg) Jq(Jg Jo Jp Lu Ma Mg Mv Nd Nj Nr
Nv Po) Om(Hw Lu Mi Mp Ms Ng Nt Oh Oy Pa Pb Pc) Pe(Jp Lw Ma Mg Mi Mp Nq Nw Oh Pb Pc) Hw(Jp Mi Mp Nq Nv Nw Oh Pb Pc Pg)
Nt(Ik Io Jo Jp Lw Nj Nw Oh Pb) Qa(Lx Mi Mp Nq Nv Nw Pa Pc Pg) Mr(Lw Ma Mp Nq Oh Pb Pc) Pg(Io Jt Oh Oy Oz Pb Pc) Mi(Io Jp Ms Nj
Nw Pc) Nb(Mp Ms My Pb) Jt(Lx Nq Nw Pa) Lh(Io Lw Ly Oh) Pa(Lw Oh Pc) Po(Pb Pc) Nq(Ir Ms) Lx(Ly Pc) Mp(Jp Nw) MsJg MvMy HuJk
JhOy JoNw} Mt{Nt(Hx Ik Io Jj Jn Lw Ma Mh Mm My Mz Nj Nw Ny Og Oi Pb Pc Pg) Jr(Hx Io Jj Jo Jq Lw Lx Ma Mh Ml Mr My Ny Og Ok
Pa Pb Pe) Pg(Hw Ik Io Jt Lw Mh Mm My Ng Ni Ny Of Og Oy Pb Pc Qa) Jq(Io Jo Lx Ma Md Ml Mr Nd Nj No Nq Ny Pb Pe) Mi(Hw Io Jj Jn
Ms Mz Ng Nj Og Ok Om Pc Qa) Lh(Ii Io Lw Ly Ma Mh Mm Ms My Ng Ny Og Oi) Pc(Hw Jn Jo Mr Ms My Mz Oi Ok Pa Pe Qa) No(Jj Jt Lw
Ma Mg Mh Mp My Nj Nq Ny) Jj(Hw Il Jk Jo Lx Mp Mr Nq Nv Pe) Og(aA Hx Jg Jh Jk Jn Jo Mw Nb) My(aA Hx Jh Jk Nb Nq Om Pa) Pb(aA Jn
Jo Mz Ns Oy Pe Qa) Mh(aA Ii Ji Mr Pa Pe) Mm(Hw Jn Mr Mz Pe Qa) Nq(Hu Ms Mz Ok) Ml(Hw In Mz Qa) Mp(Hw Jn Mz Ok) Lw(Io Mr Pa)
Oy(Jh Mw Om) Ms(Nb Om) Ji(Md Ny) EtNm IoJt JlLj JoNw NyaA OhPe} Og{Mw(Hu Hx Ih Ij Il Im Iv Jk Jo Jp Jt Lx Ma Mg Mi Mx My Nb
Nt Nv Nw Oh Om Oy Pe Pg Po Qa Qe) Jg(Et Hw Il Ir Jk Jn Lx Mi Mr Mx Mz Nq Nt Nv Nw Om Pa Pe Po Qa Qe) Om(Hw Il Ir Iu Jk Jn Jt Lw
Lx Mg Mm Mp Mr Mz Oh Pe Pg Qe) Nb(aA Im Jh Jk Jn Jq Lh Ma Mg Mm Mv No Nq Nv Nw Pc Pg) Jq(aA Hx Ji Jk Jo Lx Mg Mi Mr Mv Nv
Pc Pe Pg Po) Pg(Jh Jn Jt Lh Lw Mg Mm Mv Mz Nw Ok Pc) Lh(Jk Jp Lw Ma Mg Mp Mv Mz Nq Nw) Jr(Hx Jh Jo Lw Mr Mv Nv Pa Pe) Jh(aA
Et Hx Mi No Nt Pa) Jk(aA Jj Jn Mz No Nw Ok) Nq(Hx Ir Mz Nw Ok Pe) Nt(Jn Mv Mz Nw Pc) Et(Lw My Nw Qe) Mg(Jn Mz No) Mv(aA No
Ok) Ji(Ii My Nr) Pc(Hx Mz Pe) Mm(Hx Pe) LwPa MiJn JoNw} Jr{Jj(Hw Hx Il Iu Jg Jh Jp Jq Lu Lw Ml Mn Mr Mv My Nb Nd Nj Ok Pa Pe Po)
Jp(Hw Io Jo Jq Lu Lw Lx Ma Mg Mr Nj Nv Oh Ok Pa Pe) Jq(It Jg Jk Jo Js Lu Lx Mg Ml Mr Mv Nd Nj Nv Pe) Io(Im Iu Jg Jh Jk Jo Jt Lw Ma
Nv Nw Ok Pa) Nj(Hw Jk Lu Lx Ma Nb Nd Nv Oh Pa Pe) Lw(Jk Jo Lx Ma Mr Nd Nv Nw Om Pe) Jg(Hu Lu Ma My Ng Ns Oh Oi Oy Pz)
Ml(Hw Jo Ma Mr Mz Nb Om Pa Pe) Oh(Hw Im Jh Jk Lu Mr Om Pa Pe) Jk(In Mh Ms Ng Ns Ok Oy) Ma(Hw Nv Nw Ok Om) Lx(Mg Mh Ok
Om) Ms(Jh Jo Mw Nb) It(Hw Jo Jt) Nw(Hw Jo Qc) Ok(Nd Nv Pa) Lu(Jt Me) Mh(Nb Pa) My(Jh Mv) In(Jo Mr) Om(Oy Pb) WmJs MkPa MzLj
PbPe} Lh{Ms(Jg Jh Jk Jn Jp Lw Ma Mg Mh Mm Mp My Nq Nw Oh Om Pb Pg) Jj(Il Io Jg Jp Lw Mg Mh Ml Mm Mp Nj No Nt Nv Om Pb Qa)
Ma(Io Jo Jp Lw Mg Mh Ml Mm Mz Ng Nj No Nw Pc Qd) Mp(Hq Io Jn Jo Jp Ly Mk Mz Nj Ns Nw Ok Oy) Io(Jg Jn Jp Lw Mh Mi Nw Pb Pc Pg
Qa Qd) Nw(Hx Ii Md Mh Ml My Nj Ny Oy Pb) Om(Hx Ii Jo Mh Ml Ng Ny Of Oh) Pg(Jo Ly Mh Mm My Ng Of Oy) Nj(Ly Mh Mz No Nq Oh
Pb) Pb(Jk Jp Lw Mg No Nq) Mh(Jn Jp Lx Mz No) Ii(Jk Jn No Nv Qa) Oy(Jg Jk Mg Mv) Pc(Jp Mz Oi Qd) Nq(Hu My Ng) Jn(Js Lw Ml) My(Jg
Mg) Mz(Ml Mm) Ng(Jh Jk) Jp(Lw Oh) JkJo} Nq{Mz(aA Ir Jj Jn Jp Lw Ma Md Mh Ml Mm Ms Mv My Nf Ng Nj No Nt Ny Of Ok Oy Pb Pc
Qd) Hu(Hv Hw Hx Ij In Iv Jh Jj Jk Jo Jp Jt Mr Mx Na Nf Nt Nv Nw Pe Pg Qd Qe) Jj(Hw Ir Iv Jk Jo Jt Nt Nv Ok Om Pe Qa Qd Qe) Ok(Et Jn Jp
Jq Ms My Ng Nj No Oy Pb Qd Qe) Jn(Io Jm Jq Js Lw Mm My Nj Nt Oi Pe) Oy(Hx Jh Mr Mw Nw Pa Pe Pg) Ms(Ir Jt Nb Nw Om Pe) Ng(Jq Nb
Nw Om Pe Pg) My(Jg Mw Nb Nw Pg) Qa(aA Mm Nj No Nw) Jq(Jp Ma Mr Nr Pb) Et(Ir Lw Oi) No(Jp Lw Pb) Pe(aA Mk Pb) Nw(Hw Jo)
MkPa} Pg{Pb(Hv Hw Ij In Io Jn Jo Jp Jt Lw Ma Mg Mi Mm Mq Mr Na Nb Nf Ni No Nr Nt Nw Om Pa Pc Pe Qa) Pc(Hw Im Io Ir Jn Jo Jp Mi
Mr Ms My Nf Ng Ni Ns Nt Ok Oy Pe Qa) Oy(Io Jk Jl Jp Lw Mg Mi Mv Mz Nb Nf Nw Pa Pe Po) Mm(Hq Hv Hw In Ir Mr Na Nf Ni Ns Ok Qa)
Io(Ir Jn Jp Jq Jt Lw Mi Mz Nt Ok Qa) Lw(Hq Jp Lu No Ns) Mi(Hq Jn Jq Ng Qa) My(Jg Jh Nb Nw Om) Mz(Ii Ml Mp Nj Of) Ii(Jn Jt No Ok)
Mp(Hq Jn Ns) Ms(Jg Nb Om) Jq(Nj No Pa) Ng(Mg Om) Of(Nb Om) NoNj MhJl MkOn JnJs JoJt} Jq{Pc(Hw Hx Il Im Jk Jn Jo Jp Lu Ma Mg
Ms Nd Nj Nr Nv Ok Po Qa Qe) Ma(Hw Hx Jg Ji Jj Jk Jn Jp Lx Nd Nj Nr Nv Nw Po Qa Qe) Jp(Hw Io Jk Jo Lx Mg Mr Nd Nj Nr Nv Pa Pe)
Lx(aA Jj Md Mg Mh Ml Ms Nj Pb) Mm(Hw Hx Jk Jn Lu Nd Nr Nv Qa) Mg(Hw Jj Mr Nd Nr Pa Pe Qa) Nj(Hw Jk Mr Nd Nv Pe Po) Jj(Il Jk Jo
No Nv Pe) Ms(aA Jg Mi Pa Pe) Mh(Mi Mr Pe Po) Ml(Mr Nr Po Qa) Jg(My Nd Ng Oy) Pb(Mi Mr Pe Po) Pa(aA My Oy) Nd(Ji Ok) Jk(aA Hu)
NoIo MiaA MvMy} No{Jj(Hx Ij Jg Jh Jo Jt Ma Mn Mp Mv My Nj Nt Nv Nx Ok Om Pe Qa Qe) Nj(Jg Jk Jn Jp Jt Lw Ma Mb Mi My Mz Nb Ni
Nv Oh Ok Om Qa) Ma(Hx Jg Jk Jp Jt Lw Mb Mz Nw Nx Ok Om Pb Qa) Jg(aA Hu Io Mp Ms My Ns Oh Oy Pb Qa) Jp(Io Jt Lw Mf Mg Mi Mp
Oh) Pb(Jk Jo Mg Mz Nb Nx Ok Qa) Io(Jk Jn Jt Lw Mi Nw) Mp(Hq Mz Ns Ok Qa) Oh(Jk Mz Om Qa) Mi(Jn Mz Qa) Lw(Jn Om) Mf(aA Mb)
Mg(Ok Qa) MlMz MvMy MwNg IiJk JhOy JoNw} Jn{Pc(Hw Io Jj Jo Jp Lu Lx Ma Mi Mp Mr Ms Mz Nd Oi Ok Pa Pe Po) Mp(Hq Io Jg Jj Jp Js
Ma Mr Mz Nj Ns Nt Nw Ok Om Pa Pe) Mm(Hw Jk Lu Lx Ma Mi Ms Mz Ni Nv Oi Pa Pz Qa) Nt(In Io It Jp Js Lw Ma Ne Nj Nw Om) Mi(In Io
Jj Jp Js Lw Ma Ms Nj Ok Om) Jj(Jk Jo Lx Ma Mg Mr Nv Om) Lw(Io Lu Lx Mr Pa) Ma(Lx Mr Pa Pe) Lx(Js Mh) Ms(Jg Om) Ji(Ml Qc) MwOy
IoNv} Nt{Jj(Io Jg Jo Jp Ma Mg Mm Mp Mz Nj Nv Nw Ny Oh Om Pc Pe Po Qa Qe) Pc(Io Ir Jp Ma Ms Nf Nj Nw Oi Ok Om Pe Qa Qd) Io(aA
Lw Mm Mp Mz Nj Nv Nw Qa) Jp(aA Lw Mm Mp Mz Ne Nj Oh) Om(Mm Ms Ng Nj Of Oh Oy Pb) Mz(Lw Ma Mg Ml Mp Nj) Nw(Ma Mh
Mm Ms Nj) Mm(Ir Nf Qa) Mw(My Oy) Jg(Ms Ng) MvMy NjOh ItQa JhOy} Et{Pz(Iu Iv Jt Lw Mv Nb Nf Nj Nl Nr Oh Om) Oi(Ir Iu Jt Lw My
Nb Nw Qe) Ng(Jg Mg Mv My Nb Om Po) Jj(Iu Jo Mv My Nd Pd) Mm(Ir Iu Oh Po Qd) Ms(Jg Jh Mv Mw My) Pb(Jo Nb Nr Ny) My(Jg Jh Om)
Nf(Io Lw Nj) Oy(Mv Nb Po) Mg(Jo Mv) Ne(Nc Nl) Nj(Jk Nb) Om(Of Oh) PoLw NsMq MaMb MlIn MwHu NiNk} Om{Mp(Hq Ir Jj Ms Mz
Ng Nj Ns Of Oy Pb Pd) Mi(Hx Io Jj Jp Ms Nj Ny Of Pb Qa) Oy(Jk Lx Mm Mw Nv Pa Pc Po) Ms(Iu Jt Lw Mm Oh Pa Pc) Jj(Hw Iu Jo Lx Nv
Oh) Ng(Jk Lx Mm Nv Pa) My(Mw Nb Nv Pa) Pb(Hw Ji Mr Pe) Mm(Ir Mr Qa) LxOf MkPa MrPc} Mm{Mz(Il Io Jk Lx Ma Mi Mp Mr Nv Pa
Pe Qa) Qa(Io Lu Lx Ma Mi Mr Nv Nw Pa Pe) Pe(Ik Jj Lu Ma Ng Oy Pb) Mr(Io Ma Ni Qd) Ji(Iu Jo Jp My) Nw(Hv Hw Jo Na) aA(Io Jo Nv Qe)
Ir(Io Lu) PoOy FrPz MwMy NgJk NiPa} Mw{My(Hx Il Iv Jg Jp Lu Lw Ma Mg Mi Mp Mr Ms Mv Mx Nb Nf Ng Nj Nv Nx Oh Ok Oy Pa Pb Pc
Po Qa Qd Qe) Oy(Hx Ir Jo Mi Ml Mp Mz Nd Nw Ny Oh Ok Pa Po Qa Qd) Ng(aA Jl) Hu(Hx Ny)} Ji{Ml(Hu Hx Ii Mh Mv Mz Nb Nr Qe)
Po(Hx Md Mh My Ny Oy Pb Qc) Qc(Iv Jp Mj Mz Pe Qe) Pb(Hx Ii Nb Nr Ny Pd) My(Jg Jh Jj Nb Pz) Mh(Ii In Mr) Jj(Jo Mg Nv) Jg(Ng Pz)
MrIi NcNe NiNk NjNv IlOh} Pc{Mz(Im Iu Jo Jp Lx Ma Mi Mp Mr Ms Nd Pa Pe Qd) Pe(Im Jj Jp Ma Ms Nw Oi Ok Pb Qa Qd) Qa(Io Jp Lx Mi
Mr Nw Pa) Ok(Jp Lx Mi Mp Pa) Mr(Jp Ma Nw Qd) Hw(Jp Nw) MiJp JhOy JjNv JoNw} Mp{Mz(aA Hq Im Jg Jp Ma Nj Ns Nw Ok Pd Pf)

Figure 34 Continued

Nw(Hv Hw In Io Jo Jt Na Ni Ok Qa) Ok(Hq Io Jk Jp Nj Ns Qe) Jp(Hq Hw Io Ns Qa) Jk(aA Jj) MkPe NgJg HxaA IoQa JhOy NyPb} aA{Io(Hx Ij Ir Jg Jh Jo Jp Jt Mi Mn Mv My Nw Nx Ny Ok Qa Qd Qe) Ms(Ij Jh Mn Mv My Nb Nx) Mf(Il Jp My Pa) Jg(Hu My Oy Pe) My(Jh Mv) MiJp JhOy JoNw} Jl{Mh(In Ir Jp Lx Ma Mi Mv Nj Pa Qa) Nb(Hx Ml My Ny Of Oy) li(Ij In Jo) Jk(Hu Oy Pb) Ng(Jh Mv) Pz(Im Jp) Jo(Hw In) LxLy NdHq NiNj HuJh NyPb OyPa} Mi{Qa(Io Jj Jp Ma Nj Nw) Mz(Jp Ma Ml Nj Pb) Jp(Io Ni Ok) Ms(Jg Jh) Ng(Jg Jk) Nw(Hw Io) NiNj JjJk} Nw{Jo(Io Jj Ma Mh Ml Ms Pb) Io(Hw Jt Lw Qa) Jk(Ms My Ng Oy) Hw(Ma Pb) MhPe JhOy} Jj{Jk(Io Lx Mr Oh Pe) Jo(Mz Nv Pe) MgPe IoNv} Nb{On(Hv Hw Ij Jo Mz Qa) Jh(My Oy) MlMz} Ng{Jg(Jk Lx Nv Pa Pc) Mg(Jk Lx)} Jh{Oy(Hx Jk Mr Nv Pe) MyPa} Io{Lw(Jp Pa) QaNv JpJt} Lx{Mh(Hq Ns)} Ma{LwMr PbPe} Ml{Mz(Mg Pa)} PoJgOy MkOnPd MvMyPe

Constrained panels with 3 analytes, where 1.0E-6 >= 'model p-value' > 1.0E-7. Contains 5,375 panels of 645,860 total panels evaluated. :
Mt{Ny(Hu Hw Hx Ii Ij Im In Ir Iv Jj Jn Jo Jp Jt Ma Mr Ms Mu Mz Na Nb Ng Ni Nj Nr Ns Nv Nw Og Ok Om Oy Pa Pb Pe Qa Qd) Mm(Hv Hx Ij In Io Ir Iv Jj Jk Jo Jp Jt Lu Lx Ma Ms Mu My Na Nb Nf Ni Nr Nv Nw Og Oi Ok Om Pa Pb Po Qd) Og(Hw Ii Ij Il Im Ir Iv Jp Jt Lw Lx Ma Mg Mh Mr Mv Mz Nj Nq Nr Nv Nw Nx Ok Pa Pb Pc Pe Po Qa Qd Qe) Pb(Hu Hv Hx Ii Ij Im In Ir Iv Jj Jk Jp Lx Ma Mr Ms My Na Nb Ng Ni Nj Nq Nr Nw Ok Om Pa Po Qd Qe) Mh(Hu Hw Hx Im Ir Iv Jj Jk Jn Jo Jp Lx Ma Ms Mu Nb Ng Nj Nr Ns Nv Nw Ok Om Oy Qa Qd Qe) Jo(Hx Ik Im Io Is Jn Lx Md Mg Mi Ml Mp Ms Mu My Mz Ng Nq Of Oh Oi Oy Pg Qa Qd Qe) Pa(Hv Hw Hx Io Jj Jn Jt Ma Mk Mp Ms Mu Mz Na Ng Ni Nj Nq Oh Oi Ok Om Oy Qa) Lw(Hw Hx Ip Jj Jn Jp Lu Lx Ma Ms Mu Mz Nb Nf Nq Nr Nv Nw Oi Om Pe Po Qa) Mp(Hq Hv Hx Ij In Io Ir Jp Jt Mr Ms Na Nb Nf Ni Nj Ns Nw Om Oy Pe Qa) Nq(Hv Hw Hx In Ip Ir Jp Jt Mr Mv Na Nf Ng Ni Nj Nr Oi Oy Pe Qa) My(Hw Ii Ij Il Im Iv Jn Jp Ma Mg Mr Mv Nj Nr Nv Nw Ok Pe Qa Qe) Jj(Hx Io Iu Jg Jn Jt Ma Mg Mz Nb Nd Nf Nj Nr Nx Oh Om Pc Po Qa) Lx(Hq Hv Hw Ip Jn Jt Ly Ms Mz Na Ng Ni Nj Oh Ok Om Oy Pc Qa) Ms(Hx Ip Jg Jh Jn Jt Mg Mr Mw Mz Nf Nr Nt Nv Nw Ok Pe Po) Pc(Hv Hx In Io Ir Jp Jt Lu Mu Na Nb Nf Ni Nr Nw Om Po Qd) Hw(Hx Io Is Jn Jp Ma Md Mg Mu Mz Nj Ns Nw Oh Oi Om) Ip(Hx Io Jk Lu Ml Nf Nj Nr Nv Nw Oh Oi Om Oy Po Qd) Hx(Li Io Jn Ma Ml Mr Nb Nr Oe Oh Oi Om Pe Qa) Oi(Ir Jn Jt Mg Mi Mr Mu Mz Nb Nv Nw Oh Om) Ml(Hv Ij Jn Jt Mu Na Nb Ni Ok Om Oy Pe) Io(Ir Iu Jn Jp Mr Nb Nv Nw Oh Pe Qa) Ma(Ir Jn Jt Mb Mr Mz Nb Nf Pe Qa) Nj(Is Mz Nb Nf Nv Oh Pe Pg Qa) Nt(Jp Ly Ne Oh Ok Om Oy Qa) Mr(Is Jn Jt Ly Mu Mz Oh) Ng(Jg Jk Mg Mw Nb Nv Om) Qa(Lj Md Mg Nv Nw Oh Qc) Md(Hv Ij In Mz Om) Mi(Hv Jp Ly Na Ni) Nw(Hv Iu Jt Mb Na) Oh(In Mu Nb Om Po) Oy(Jg Jr Nb Pe Po) Mg(Ir Jn Mz Ok) Mu(Hu Ik Of) Nv(Hv Jn Oe) Pe(Jn Lj Mz) Nb(Oe Of) Om(Ik Of) NsMq MzIu HuJk QcQd} Ip{Oh(Hv Hx Ii Ij Im In Ir Iv Jg Jh Jj Jk Jn Jo Jp Lu Lw Lx Ma Mg Mn Mv Mz Na Nb Nf Nj Nq Nr Nv Nw Og Oi Po Qa Qd) Jj(Hv Ii Ij In Ir Iu Iv Jg Jh Jp Lu Lw Lz Ma Mm Mn Mv Mw Mx My Na Nd Nf Nj Nk Nr Nu Nw Nx Pc Pd Qa Qd Qe) Pc(Hu Hv Hx Ii Ij Il Im In Ir Iv Jh Jk Jo Jp Jt Lu Ma Md Ms Mv Mx Na Nb Nd Nf Ni Nr Nv Nw Og Oi Qd Qe) Jk(Hw Io Ir Iv Jm Jo Jp Jt Lu Lw Ma Mg Mi Mm Mp Ms Na Nf Ng Ni Nj Nr Nw Oi Oy Pa Pb Qa Qd) Jp(Hx In Io Ir Iu Iv Jn Jo Jt Lu Lw Lx Ma Md Mg Mm Mr Na Nb Nf Nj Nq Nr Nv Nw Pa Po Qa) Mp(Hq Hv Hx Ii Ij In Io Ir Iv Jg Jh Jo Jt Lu Na Nf Ni Nj Nr Ns Nv Pa Po Qd) Nq(Hv Hx Ij In Iv Jo Lw Mi Mm Na Nb Nf Ng Nj Nr Nw Om Oy Pa Pb Po Qd) Jg(Hw Hx Io Ir Jn Jo Lu Mi Mx My Mz Nf Ng Nr Ns Oi Oy Pz Qa Qd) Ma(Hv Hw Hx In Ir Iv Jo Jt Lu Lx Na Nb Nf Nr Nw Pa Po Qa) Lw(Hw Hx Io Ir Iv Jn Lu Lx Mx Mz Nb Nf Nr Nv Nw Og Po) Nw(Hv Io Ir Iu Jn Lu Lx Mb Mg Mr Ms Na Nj Nr Og Pa) Mm(Hv Ii Ij Il Io Iv Jt Md Mi Ms Na Ni Og Qd Qe) Lu(Hw Hx Ir Jn Jo Jt Mg Mn Mv Nf Nj Nr Qa Qd) Pa(Hv Hw Io Jo Mg Mk Ms Na Nf Ni Nj Nv Pb Qd) Og(Ii Il Ir Jn Jo Jt Lx Md Mg Nf Nr Nx Qa) Lx(Hq Hv Hw Ir Jo Mh Na Nb Om Pb Qd) Nb(Hx Jn Mh Ml Nj Ny Of Oy Qa Qd) Jo(Hx Jn Jt Mg Mi Ms Nj Nv Pb Qd) Nv(Hv Io Jt Mi Mr Nj Pb Pc Qd) Po(Jn Jt Mh Ms Nj Oy Qa Qd) Mg(Hw Ir Jn Mr Ms Nf Nr Qa) Pb(Hx Jt Mi Nf Nr Ny Qa) Md(Hw Ir Nj Nr Ok Qd) Om(Mr Mz Nj Nm Pe Qa) Mi(Hv Jt Na Ni Qd) Hw(Jn Mn Nj Pe) Io(Jn Jt Qa Qd) Ms(Jh Jt Mw) Nf(Iu Nj Qd) Nr(Oz Qd) Mr(Jt Qa) Mv(Ir Jn) Hx(Jh Qd) Pe(Nj Oz) MyJh NdJt ItQa} Ma{Mz(Hw Hx Im Ir Iu Iv Jg Jj Jk Jn Jo Jp Jt Lw Lx Ml Mr Nd Nj Nl Nr Nv Nw Og Ok Om Pa Pb Pe Qa Qd Qe) Mu(Hu Hv Hw Hx Ih Ik Iu Iv Jo Jp Lw Lx Mb Mg Ms Na Nb Nf Nr Og Oh Oy Pa Pb Pc Pe Po Qb Qe) Qa(Hx Io Jg Jj Jk Jp Lv Lw Lx Mb Ml Mp Mr Nb Nj Nq Nt Nv Nw Oh Ok Pa Pb Pc Pe Po) Nw(Hv Hx Ij In Ir Iu Iv Jk Jn Jt Lw Lx Mb Mi Mm Mr Na Nd Nr Og Ok Pa Pb Pc Pe) Pe(Hw Ik Ir Jg Jj Jk Jp Jt Lw Mb Ml Mp Ms Ng Nj Nq Nv Og Oh Ok Om Pg Qd Qe) Mr(Ik Io Ir Jj Jk Jp Jt Mb Mh Mp Ms Ng Nj Nq Nv Og Oh Ok Om Pb Pg Qd Qe) Nn(Hr Hv Ij Il Iu Jj Jk Lw Mb Ms Nd Nf Ni Nj Nl Nv Nx Po Qb Qe) Nt(Hx Ik Io Ir Jg Jk Jt Lw Mb Mp Nf Ng Nj Og Oh Oi Ok Pb Qd Qe) Jn(Hw Hx Ik Io Jg Jk Jo Jp Jt Lu Lw Mb Nb Nd Nr Nv Oi Ok Om Po) Ir(Jg Jj Jk Jp Lv Lw Lx Mb Mi Mm Mp Nq Nv Oi Ok Om Pa Pc) Lv(Hx Ih Io Iu Iv Jk Jt Lu Lw Mb Na Nb Ng Nr Oh Pc) Hw(Jj Jk Jp Lx Mi Mm Mp Nq Nv Ok Om Pa Pb Pc Pg) Mi(Hv Hx Io Jj Jk Jt Lw Na Ng Nj Ok Qd Qe) Jj(Hx Il Iv Jo Jt Lx Nq Nv Om Pa Po Qe) Jt(Hx Io Jk Jp Lx Mm Mp Nq Nv Pa Pc) Ok(Hx Jk Jp Lx Mm Nd Nv Pa Pb Pc Qe) Mm(Hv Hx In Nb Nf Nv Pa Po Qd) Pc(Hx Jo Jp Lx Nf Pa Po Qd) Lw(Hx Io Jp Lu Lx Pa) Pb(Hx Jo Nb Ny Om Po) Jp(Hx Is Lx Nv Pa) Og(Hx Is Jg Jk) Pg(Ik Mb Na Ng) Lx(Hq Na Qd) Nb(Ms My Oy) Po(Is Oy) Mp(Hx Nf) Om(Ik Pa) MbQd MkPa MsIs MwOy NgJk} Pc{Jp(Hr Hv Hx Ii Ij Il Im In Io Ir Iv Jk Jo Jt Lu Lx Mp Ms Mu Mx Na Nb Nd Nf Ni Nr Nv Nw Oi Om Pa Po Qd Qe) Lx(Hq Hv Hw Hx Ij Im In Ir Iv Jh Jj Jk Jo Jt Ly Mh Ms Mu Na Nf Ng Ni Nv Nw Og Om Oy Qd Qe) Pa(Hu Hv Hw Ij Im In Ir Iv Jh Jj Jo Jt Lw Mk Mm Ms Na Nf Ni Nj Nv Nw Og Om Po Qd Qe) Qd(Hu Hw Hx Ij Im In Io Jk Jo Lu Mi Mm Mp Ms Nb Nd Nf Ni Nq Nr Nv Nw Oi Ok Om Po) Ok(Hu Hw Hx Il Io Ir Iv Jk Lu Mg Mm Mr Ms Mx Mz Nd Nv Nw Og Oi Om Po Qa Qe) Ir(Hw Hx Io Jj Jo Lu Mg Mi Mp Mr Ms Mz Nd Nf Nq Nv Nw Og Oi Om Pe Po) Nw(Hv Hx Ij Im In Io Iv Jk Jn Jt Lu Mi Ms Mz Na Nd Ni Nr Og Oi) Nv(Hv Hw In Io Iv Jn Jo Jt Ms Mz Nf Ng Ni Nr Ns Og Oi Qa) Jo(Hx Im Iv Jj Jk Lu Mi Mp Ms Mu Mx Nf Og Pb Po Qe) Om(Hu Hw Iv Jj Jn Lu Mu Mx My Nd Ng Ns Oi Pb Qa Qe) Po(Hw Im Iv Jj Ms Mu My Ni Nn Ns Og Oy Pb Qa) Nn(Iu Jh Lu Me Mf Mp Mq Mx Ni Nj Nu Nx Oz) Mi(Hu Hv Hw Hx Io Iv Jk Jt Ms Ni Nt Qe) Mu(Hv Hw Hx Im In Iv Nf Ng Nj Nr Oi Qe) Hw(Im Iv Jh Jj Jk Mp Mz Nq Qa Qe) Lv(Ih Il Jh Jt Mp Mx Ns Oh Oi) Qa(Jj Lu Mg Mp Mz Nd Nq Og Oi) Mr(Im Iv Jj Mm Ms Ni Og Qe) Mz(Il Iv Jk Ml Oi Qe) Jk(Ms Nf Ng Ni Og) Hx(Iv Jj Mp Ms) Im(Lu Nb Nf Nr) Og(Ij Jh Jn Qe) Jj(Ij Il Qe) My(Jh Nb) Nf(Iv Qe) NrJn MpJt MsNb MwOy} Og{Jg(Hr Hv Ih Ii Ij In Io Iu Iv Jh Jo Js Jt Lu Lw Md Mg Mj Mp Mq Mv Mw Na Nf Nr Nx Oh Ok Pd Qb Qd) Jk(Hw Hx Io Ir Iv Jh Jo Jp Jt Lw Lx Mg Mi Mm Mp Mr Mu Mv Nf Nm Nq Nr Nt Nv Nx Oh Pa Pe Pg Po Qa) Nw(Hw Hx Ii Ij Il In Jh Jn Jt Lw Lx Mg Mi Mm Mr Mv Mz Nr Nv Ok Pa Pe Po Qa) Nq(Hw Ij In Iv Jo Jp Jt Lw Mi Mr Mu Nf Nr Nt Nv Nx Pa Pg Po Qa Qd Qe) Nt(Hx Im Io Ir Jt Lw Mg Mi Mp Nb Ne Nf Nj Nv Nx Ok Pe Pg Po Qa Qe) Nv(Hx Io Ir Jh Jn Jo Jp Jt Lw Mg Mi Mm Mr Mv Mz Ok Pa Pe Qa Qe) Jh(Ir Jn Jq Jt Lx Mm Mp Mr Mu Mx Mz Ok Pe Po Qa Qe) Mw(Hq Hw Iu Js Lw Mm Mn Mp Mr Ms Nf Nr Nx Ny Pa) Nb(Hx Iv Jp Lw Lx Mp Mz Nj Ny Ok Pe Po Qa Qd Qe) Mv(Hx Ir Jn Jo Jt Lw Mr Mu Mz Nr Pa Pe Qa Qe) Hx(Jn Jo Jp Lv Lw Lx Mg Mi Mp Mz No Ok Pg) Pg(Hq Io Ir Jo Jp Mi Mr Nf Nm Ns Pa Pe) Nn(Hv Im In Iu Lw Me Mf Nf Nm Ny Qe) Mi(Ij Im Ir Mz Nx Ok Pe Po Qa Qe) Pa(Ij Im Jn Jt Mg Mm Mz Nx Ok Qa) Lv(Li Im Iv Jo Jt Lw My Nr Oh) Jq(Il Im Iu Iv Jn My Nr Ok Qe) Mu(Ih Im In Iu Jp Nf Oh Qb) Mg(Ir Lx Mr Ok Pc Po Qa) Mz(Iu Jo Lx Mr Pe Po) Is(Jp Lu Nf Nr Oh Ok) Jn(Jo Lw Lx Mr Pe Po) Lw(Lx Mr Pe Po) Ij(Lx Mm Mp No) Jr(Iu Nm Nr Po) Jt(Lx Pe) PoMm QeOk OhPe} Jj{Nq(Fp Hr Hv Hx Ih Ii Ij Il Im In Iu Jg Jh Jp Js Lw Lx Mi Mn Mp Mq Mr Mx Na Nb Nf Ni Nj Nr Nw Nx Ny Oh Pa Pd Po Qb) Nn(Fp Hr Hv Ih Im Iu Jg Jh Js Md Me Mf Mg Mn Mp Mq Mv Mw Mx My Na Nd Nf Ni Nj Nl Nu Ny Oi Pd Qb) Jo(Hx Ih Il Im Ir Iv Jg Jh Jp Lv Lw Lx Mg Mi Mm Mn Mp Mv Mw Nf Ny Oh Ok Pa Pb Po Qa Qb Qd Qe) Lv(Hu Ih Ii Ij Io Iv Jh Jm Li Lu Lw Mb Md Mn Mv Nd Nl Nx Ny Pd Qa Qd Qe) Mp(Hw Ij Il Ir Iv Jg Jh Jp Jt Mr Nb Nf Nv Nx Ny Pe Po Qa Qd Qe) Jn(Hw Hx Il Iu Jg Jh Jq Jt Lu

Ij(Jk Mm Oy Pd Qd Qe) Jk(Hu Iv Jo Pd Qd) Nr(Nf Oy Pd Qd) Ii(Mk Mm Oy Pd) Jo(Iv Mk Nv Qe) Nv(Nf Qd Qe) Nb(Iv Qe) Hw(Hx Mi) NqOy LzMj MkOz MvMy NfPd HxIv} Nq{Ng(Fp Hv Ih Ii Ij Il Im In Jh Js Mb Md Mf Mg Mm Mn Mq Mv Mx My Na Ni Nm Nn Nr Ny Qb) Oy(Fp Hr Hv Ih Il Im Jk Js Md Mf Mi Mm Mn Mq Mx Na Ni Nm Nn Ny Oz Qb Qe) My(Hv Ij Il In Iv Jk Js Mf Na Nf Nm Nr Nv Ny Qe) Ni(Hx Ih Im Jk Mm Mr Mx Nc Nk Nl Nv Pa Po Qb Qe) Im(Hv Ij In Jo Mj Mm Mq Mr Na Nb Nf Nr Pa) Mm(Fp Hr Ih Ii Ij Js Me Mh Mx Qb Qe) Qe(Hv In Jm Jo Mi Mr Na Nf Nr Oi) Na(Ih Iv Jh Mi Nv Pa Po) Nb(Hx Mv Mw Ns Ny Of) Pa(Hv Ij In Jp Nf Nm) Ih(Hv Ij In Mq Oi) Iv(Ik Jo Mi Mr Oi) Ns(Mq Nv Nx Po) Hv(Hx Nv Po) Mi(Hq Jo) Mr(Ly Mh) Jp(Hx Ij) WmJq PoOf NfIu} Mg{Pa(Hv Hw Hx Im In Ir Iv Jo Jp Mh Mk My Na Nf Ni Ny Oy Qd Qe) Jp(Hv Hx In Iv Lu Mb Mt Mx Na Nb Nf Nr Oi Qd Qe) Qd(Hw Hx Ik Ip Jk Lu Mb Mr Nf Ng Nr Oi Pe) Ip(Hv Hx In Iv Lz Mb Md Mx Na Ng Oi) Qe(Hw Jo Jt Lu Mr Nf Ng Nr Oi Pe Po) Ng(Hw Hx Ii Ir Mw Nb Nn Nr) Nv(Hw Ir My Na Nr Of Oi Oy) Pe(Hx Ir Mh Mk Ml Ny Of) Mr(Hx Ir Iv Mh My Oy) Mt(Hv Ik Mb Na Nf Nr) Nb(Hx Mh Ml Ny Of Oy) Hw(Im Iv Jk Mx Po Qb) Nw(In Iv Lu Mh Ny Oy) Po(Mh My Ny Of) Nr(Im Jk Mx Oi) Ir(In Lu Oi) Iv(Ik Mb Oi) Jk(Hu Jo Oy) Mi(My Oy) Om(Ik My) WmJq NtIn LuJt MjIm MuOi PzOk JhOy} Jk{Ng(Hu Hw Hx Im Jh Jo Jt Md Mr Mv Nd Nf Ni Nm Nr Nv Nx Oi) Hu(Hw Im Ir Jh Jo Jp Jt Mi Nf Ni Nv Nx Pe Po Qa Qd) Jp(Hw Ir Jt Mm Ni Nr Oi Oy Pa Pz Qa Qd) Mt(Hx Ik Iv Ml Ni Ny Oe Of Oi Qd) Pa(Hv Hw Jo Mk My Na Nf Ni Oe Oy) Nb(Hx Mh Ml Mm My Ny Oe Of Oi) Oy(Hx Jn Jo Jt Mm Nf Nv Nx) Mz(Hx Im Jn Mh My Ny Of) Ni(Ir Iv Lz Mh Mr Nv Po) Qd(Hw Ik Jt Nf Oz Pz) Mi(Hq Hv Jm Jo Ly) Oi(Ir Iv Jn Jt Nv) Po(Mh My Ns Of) Mm(Ij Iv Lu Pz) Ik(Iv Jo Om) Mr(Jt Ly) NsMq MvMy InIv IrJm ItQa JoJt NvOe} Jh{Oy(Hw Ih Ii Ij Im Js Lu Md Mj Mk Mn Nc Nf Nk Nl Ny Oz Pf Qb Qd) My(Hx Ir Jn Jp Jt Mm Mr Mu Mv Mz Po Qa Qd Qe) Hu(Ip Ir Jn Mm Mt Mu Nt Nv Nw Pe Qa Qd) Ip(In Iu Iv Lu Lz Mx Na Nf Ng Nr Ns) Pa(Hv Hw Ir Iv Jo Mz Na Nf Ng Qe) Ns(Hw Jn Lv Mi Mt Nw Pe Qa Qd) Mi(Hv Hw Iv Jo Na Nf Ni Of) Ng(Mm Mt Nt Nv Nw Pe Po) Mz(Hw Iu Iv Ml Mr Nd) Hx(Ir Iv Jn Jo Jt Qd) Ir(Lu Mr Oi Pe Po) Mt(Iv Mh Ml Ny) Po(Iv Mh Of) Hw(Jn Qd Qe) Mr(Iv Qe) Nf(Jt Qd) Jn(Nd Oi) WmNw MbQd MmQb} Mm{Lu(Fp Ih Ii Il Im Iv Jp Js Mv Mx My Na Ni Nm Nx Ny Pd Qb Qe) Ni(Fp Ih Ii Im Iu Js Md Mh Mj Mn Mv Mx Nc Nk Nl Nr Nx Pd) Im(Hv Ii Ij In Jt Md Mh Mj Mt Na Nx Pd) Jp(Fp Hr Ii Il Jt Mh Mx Na Pd Pz Qb Qe) Na(Fp Ih Il Mh Mv Mx Pd Qb Qe) Ij(Ih Il Iu Iv Nr Qb Qe) Fp(Ii My Nn Nx Pd) In(Il Iv Nr Pd Qb) Ng(Mi Mv Mw Pd) Hv(Iv Pd Qb Qe) Mx(Il Nf Nx) Nb(Hx Ny Qe) Jo(Iv Nf Qb) Nr(Iv Qe) Mv(Ih My) Jt(Il Qe) WmNw NnHr NsMq MhMy MjIh MtNy NfIu} Nb{Ml(Hu Hx Im Ir Jp Mi My Ns Nt Nv Nw Ok Om Oy Pa Pe Po Qa Qd) Mh(Hu Im Ir Jp Mi My Ns Nv Om Oy Pa Pe Po Qa Qd) Hx(Im Jn Jp Mi My Mz Ns Nt Nv Om Oy Pa Pe Po) My(It Jn Mi Mz Nt Ny Ok Pa Po Qa Qd Qe) Oy(Im Jp Mi Mz Nd Nt Ok Pa Po Qa Qe) Ny(Im Jp Mi Mz Ns Nv Om Pa Pe Po) Of(Im Jp Mv Mz Nv Nw Pe Po) Nd(Hq Jn Jp Qd) Md(Mz Om Pe) Ng(Jp Mv Nv) Im(Jp Qd Qe) Oi(Nv Nw) MkPa InIr QcQd} Pa{Mk(Hv Hw Hx Ij Im Ir Iv Jp Mi Mv Mz Na Ni Nm Nt Nx Pd Pe Po Qe) Im(Hv Hw Hx In Jo Mh Mq Na Nf Ni Oy) Jp(Hv Hw In Ir Iv Jo Mf Na Ni Nm Om) Qd(Hw Jo Mz Nf Ni Nx Qc) Ml(Hv Hw In Jo Mt Nx) Nv(Hv My Ng Ni Oe Oy) Mz(Jt Md My Of Om) Nw(Hx In My Ny Oy) Nx(Hx Mh My Ny Oy) Po(Hv Hw Na Ni) Qe(Hv Hw Jo Ni) Ni(Mn Nk) Ij(My Oy) NmNg NtLy HwIv JoOy} Mt{Ml(Hu Ii Im Ir Iv Jp Mx Nf Ng Nr Ns Nv Nw Nx Qd Qe) Oy(Hw Ii Ij Il Im Iv Jn Jp Mk Mv Nr Nv Oz Qa Qe) Hx(Ij Im Ir Iv Ns Nv Qd Qe) Mh(In Iu Jt Mb Mx Po) Im(Iu Iv Mq Ni Nr Qe) Oi(Iu Iv Jp Nr Qd Qe) Ni(Iu Nk Qe) Ir(It Iv Js) Wm(Ik Lz) Mb(Iv Qd) Mv(Ng Om) Nd(Hq Ns) Hv(Iu Ny) Qe(Ny Qc) Lj(Li Qd) PoNg NmLu NrJp MdNa MwHu NfIu HwOf IkIv} Nw{Wm(Hv Ij Ik In Ip Ir Jn Jr Ly Mi Mu Mz Na Ns Nv Nx Ny) My(Hx Ii Il Nv Nx Oi Po) Mh(Hx Ir Jn Nx Po Qe) Iu(Ij Im In Jp Lu Oi) Ny(Hx Ii In Na Om) Oi(Ir Iv Mv Mx Qe) Oy(Hx Il Nv Po) Nr(Im Jp Lu) Mq(Im Lu Ns) Nd(Ij In Ni) Nm(Jp Lu) Md(In Om) Ml(Ij Om) Ni(Nl Nv) MbIv MjIm MwNg HxIi QcQd} Mz{Ml(Hx Ii Il Im In Ir Iv Jp Jt Lz Mf Mh Mj Mv Mw Mx Nl Po Qd Qe Wm) Nd(Hq Iv Jn Jp Jt Ok Qd Qe) Mh(Ii Il Mr Mv Nr Po) Ny(Hx Il Mr Mv Mw Po) Wm(Ik Ip Lj Lv Ne) Mr(Hx Im Jp Qd) Im(Hw Jt Qe) Qa(Lj Pe Qc) Po(Hx Oy) Mw(Md Of) Iu(Jn Ok) Qd(Lj Pe) NsMq HwJp QcQe} Lu{Ip(Hv Ij Im In Iu Iv Lz Mb Mw Mx My Na Nm Nx) Qd(Hx Im Jo Jp Jt Mb Nf Nm Nr Nx Ok) Jp(Hx Ij Im Ir Iu Jo Nf Nm Nx Qe) Ok(Hx Ih Ir Iu Jt Mn Qa) Nn(Ih Mn Mq Qb) Im(Jo Jt Mj Nr) Ir(Hx Jo Mn Oi) Qa(Iu Jt Mn) Jt(Hx Mn) NmNv HuOm} Mi{Ng(Hu Ij Mv Mw My Nm Nx Ny Po) Oy(Hu Hx Ij In Mv Nf Nv Nx Po) Ni(Hx Im Iv Mn Nc Nk Ny Qb) Im(Hv Hw Jo Jt Na Nf Pe) Nf(Hx Mh Ml My Ny) Hw(Iv Nv Po Qe) In(Ih Mh Ml Ny) My(Hx Ij Nx) Hv(Nv Po Qe) Mh(Ii Mr) Hq(Mv Pd) Ij(Hx Ny) LyHu QeJo} Nv{Im(Hv Hw Jo Jt Mj Mr Ni Nr Pe Qe) Of(Hv Ij In Jo Nf Pe Po) Ng(Jo Mv Mw My Nm Po) Ni(Iu Mn Nk Po Qe) Ns(Hw Mq Om Po) Qe(Hw Jo Oe Oi) Nf(Iu My Ny) Oi(Ir Iu Iv) Oy(Jp Mv Pe) Wm(Ik Qd) Hv(It Jp) Jo(In Jt) PoMy HwQd NyOm} Ip{Lz(Hv Ij In Mb Mn My Na Ni Oz) Mn(Hv In Ir Iu Md Na Ni) Mv(Iv Md Na Nf Oy) Nd(Hq Hv Ij Na) Iu(Hv Ij In Na) Mb(Iv Mh Qd) Nf(Ir Iv Nr) Wm(Ji Jq) Md(Iv Mx) Ir(Hx It) NrIm NsMq MwNg NiNk HvIt IlJm} Po{Oy(Hx Ij Im Jn Jo Jt Lj Md Mn Mv My Nt Nx Qa Qe) Mh(Ir Jn Jp Mr Ns Om) Ml(Jn Om Qa) Ns(Hw Mq) My(Jp Lz) Ng(Jp Mv) Om(Ik Ny) ImJt InJo} Ef{cD(aA An cK cS dE dI dK dN Ex) Dc(Ad Ax cI cJ cS Db Dk Dl) aA(Ax bR cI cJ) bA(bE cY Db) dK(An bE bG) cJ(Db dN) AnAx bRdI} Jp{Iu(Hv Ij In Md Mx Na Nf Ni) Qd(Jo Mb Md Nd Nf Qc) Qe(Im Nf Ni) Nd(Ij Na) Ng(Jo Mw) Qa(Mr Pz) Jn(Jt Nr) NsMq MbMf MvMy NfIm NiNk} Wm{Jr(Ik In Ji Jm Jq Mj Mx) Ji(Fp Jq Ly Nm Ns) Lv(Jn Nf Qd) Ly(Jq No Ny) Ik(Mu No Qd) Jq(Mu Mv)} Fr{bE(aC Ad As Bn Cp Cq Cu Cw Dc Dd) Dc(bH bJ cJ) Dd(Ad bJ) cS(Ap Dg) dH(aP dN) CqcE cJdN} Mv{My(Ii Ij Im Iv Mx Na Nn Qd Qe) Oy(Jo Jt Lv Mr Mu Ok) Ng(Jo Mr) MlQa IrOi} Om{Ik(Jo Mh Mx Nl) Of(Jo Mh Mx) Ml(Hx In) My(Il Iv) Ny(Hx Oy) NsMq MkPe NdOk NiNk IvOi} Lv{Ns(Mq Mw Pd Pf) Mb(Il Mx Nl) Nd(Hq Ij Na) Hq(Pd Pf) MeHv MwHu NaLi} Jn{It(Hw In Jt Na Qa) Ml(Hw Nr) Nd(Hq Jt) NsMq MhIi MwNg IuOi LiLj} Mu{Hu(Ij Il Md) Ik(Fp Mx Nu) Oi(Js Mn Nl) Oy(Ii Mn) NsNd NiNk} Nt{Ik(Ir Iv Mj My) It(Hv Js Na) Hq(Nd Pd) LyMr InNx NyOi} Qd{Nd(Jt Nx Ok) Nr(Im Md) Mb(Im Md) Nf(Iu Qc) MlHw MwNg PzOk} cS{Dc(Ax Bg bH cH cJ) An(bR cJ dH Dk) Dk(cD cJ Dd)} Qa{Ml(Lz Md Nf Ny Pe) It(Hx Ir Iu Iv) MwNg NdJt} Ok{My(Md Pz) Ng(Jo Mw) MbMh MlIn NcNe NdJt NiNk IuOi} Nn{Mf(My Nm Oy) Mb(Fp Mh) NsPd MjIh MwNg} Im{Qe(Hw Jo Jt) Mj(Iv Mh) NrMd MrJt NfIu} Jo{In(Hx Ih Ir Pe Qe) HwLh IrIt} Mw{Ng(Ir Nd Pe) MdJq HuIs} cJ{Dc(aX bH) aA(bG bH) DkbE} dH{aP(aO bG bQ) aJ(bQ cU)} Pe{NsMq NdHq IkIv LjOy} Dc{GlbE aXbH} aA{nBkG hWlM} hR{hWjR hXjH} AdGlbE NdHxJt NlJqJs

Constrained panels with 2 analytes, where 1.0E-7 >= 'model p-value' > 0. Contains 373 panels of 16,788 total panels evaluated. : aA(Et Fr Hx Ij Il Ip Ir Is Jg Ji Jk Jl Jn Jo Jp Jq Jr Lh Lv Lw Lx Ma Mg Mi Mm Mn Mp Mt Mu My Mz Nj Nn No Nq Nt Nv Nw Nx Ok Om On Pc Pe Pg Po Qa Qd Qe) Et(Fr Hw Hx Il Io Ip Ir Is Ji Jk Jl Jn Jq Jr Lh Lu Lv Lw Lx Md Mi Mm Mp Mr Mt Mu Mz Nb Nf Nn No Nq Nr Nt Nv Nw Oh Om On Pa Pc Pe Pg Po Pz Qa Qe) Fr(Hu Hv Hw Hx In Ip Ir Is Iv Ji Jj Jl Jn Jo Jq Jr Jt Lh Lv Lw Mp Mq Mx Mz Na Ng Nj No Nt Oh Ok On Oy Pb Pe Qa) Jr(Ip Is Jg Ji Jj Jk Jl Jo Jp Jq Lh Lv Lw Lx Ma Mg Mi Mm Mp Mr Mt Mu Nn No Nq Nt Nv Nw Ok Om On Pa Pc Pe Pg) Ji(Hw Il Io Ip Is Iu Jk Jl Jo Lh Lu Lv Lx Ma Mi Mm Mp Mr Ms Mt Mu Nd Nn No Nq Nt Nv Og On Pa Pc Pe Pg) Jl(Io Ip Is Jj Jn Jq Lh Lv Lw Ma Mg Mh Mi Mm Mp Mt Mu Mz Nn No Nq Nt Og Oh Ok Om On Oz Pb Pc) Nn(Hu Hw Hx Ip Ir Is Jn Jo Jq Lh Lv Lx Mi Mr Mt Mz No Nt Nw Ok Om On Pa Pc Pg Qa) No(Ip Is Jg Jn Jp Jq Jt Lv Lw Ma Mg Mm Mp Mt Mu Nj Nq Ok Om On Pc Pg Qa) Jq(Ip Is Lh Lv Lx Mi Mm Mp Mr Mt Mu Nq Nt On Pa Pc Pe Pg) On(Hu Io Ip Jj Lv Mm Ms Mw My Ng Ns Of Og Oi Oy Pb Pz) Lh(Ip Is Jj Jn Jp Lv Lw Ma Mm Mt Mu Og Pb Pc Pg) Lv(Is Mi Mm Mr Mt Mu Mz Nq Nt Pa Pe Pg) Mu(Ip Is Jj Jn Mi Nt Nw Ok Pe Pg) Is(Io Mi Mm Mp Nq Nt Pc Pg) Pg(Ip Jj Mm Mz Ok) Mm(Jn Mz Pe) Nq(Jn Ok) NtIp JjJk OgOm PcPe

Figure 34 Continued

Constrained panels with 2 analytes, where 1.0E-6 >= 'model p-value' > 1.0E-7. Contains 336 panels of 16,788 total panels evaluated. : Mu(Hw Hx Ih Im Ir Iu Iv Jo Jp Jt Lw Lx Ma Mm Mp Mr Ms Mt Mz Nb Ng Nj Nn Nr Nv Og Oh Om Pa Pc Po Qa Qd Qe) Lv(Hw Hx Im Ip Ir Iu Iv Jg Jh Jj Jk Jn Jo Jp Jt Lu Lw Lx Ma Mg Mp Nb Nf Nr Nv Nw Oh Ok Om Pc Po Qa Qd) Jq(Hw Hx Il Im Iu Iv Jg Jh Jk Jn Jo Jp Lu Ma Mg Mv My Nb Nd Nj Nr Nu Nv Nw Ok Om Po Qa Qe) Is(Hw Ip Jj Jo Jp Lu Lw Lx Ma Mg Mr Ms Mt Mz Nf Nv Nw Og Oh Oi Ok Om Pa Pe Po) Ip(Hw Jj Jk Jn Jp Jt Lx Mi Mm Mp Mr Mt Mz Nb Nq Nv Nw Ok Om Pa Pe Po Qa) Nn(Hv Ii Ij Il Im In Iv Jk Jp Jt Ma Mp Na Nb Nf Nr Nv Nx Oi Po Qd Qe) Nt(Io Jj Jn Jp Lw Ma Mm Mp Mt Mz Nj Nq Nw Oh Ok Om Pc Pg Qa Qd) Mt(Hw Jj Jn Jo Jt Mi Mm Mp Mr My Mz Ok Om Pa Pb Pc Pe Pg) Nw(Hw Jk Jn Jo Jt Lh Ma Mi Mm Mp No Nq Pc Pe Pg Qa) Pg(Hw Io Ir Jn Jp Jt Lw Mi Og Oh Oy Pb Pc Qa) Jr(Hw Hx Im Jh Jt Lu Mv Mz Nb Nd Nj Oh Po) Om(Ir Jj Jn Lh Mi Mm Mp Ms Oh Oy Pc Qa) No(Hx Jj Jk Jo Lh Mf Mi Mz Nx Oh) Jn(Lx Ma Mi Mp Mr Nv Ok Pa Pc Pe) Pe(Jj Jp Lw Mi Mp Nq Oh Ok Pb) Qa(Lh Lx Ma Mi Mm Mp Nq Pc) Ok(Jk Lx Mi Mm Mp Nv Pc) Lh(Mh Mp Ms Nj Oh Qd) Mz(Ma Mi Mp Nq Pc) Mm(Hw Hx Ir Mr) Nq(Hu Ir Qd) Mi(Jp Pc Qd) Mp(Ir Jp) Mr(Lw Pc) Mw(My Og) Jj(Jo Nv) LxJt NbOg IrPc hRjI Constrained panels with 2 analytes, where 1.0E-5 >= 'model p-value' > 1.0E-6. Contains 521 panels of 16,788 total panels evaluated. : Nv(Hv Hw Im Io Ir Iv Jo Jp Jt Lw Lx Ma Mi Mm Mp Mr Mt Mz Nf Ni Nj Nq Nr Nt Oe Og Oh Om Pa Pb Pc Pe Qa Qd Qe) Mz(Hw Im Ir Iu Iv Jg Jh Jk Jn Jo Jp Jt Lw Lx Mg Ml Mr Mv Nd Nj Nw Og Oh Ok Om Pa Pe Po Qa Qd Qe) Ok(Hw Hx Il Io Ir Iu Iv Jg Jh Jj Jp Lu Ma Md Mg Mr Mv Mx My Nb Nd Nw Oh Om Pa Pb Po Qa Qd Qe) Mp(Hq Hv Hw Hx Ii Ij Im In Iv Jg Jh Jj Jk Jo Jt Ma Mi Mr Na Nb Nf Nj Nr Ns Nx Pa Po Qd Qe) Mi(Hv Hw Hx Ij In Io Ir Iv Jg Jh Jj Jk Jo Jt Lw Ma Mm Na Nf Ni Nj Nq Nt Nx Og Po Qe) Mt(Hv Hx Ir Iu Jp Lw Lx Ma Mb Mg Mh Ml Ms Na Nb Nf Nj Nq Nr Nw Ny Og Oh Oi Po Qa Qd) Ip(Hv Hx Ii In Ir Iv Jg Jh Jo Lu Lw Lz Ma Md Mg Mn Mv Mx Na Nf Nr Nx Og Oh Pc Qd) Mm(Hv Ii Ij Il In Iv Jk Jo Jp Jt Lu Lx Mx Na Nb Nf Nn Nq Nr Pa Po Qd Qe) Qa(Hx Io Jg Jh Jj Jk Jn Jo Jp Jt Lu Lw Md Mg Mn Mr Nb Nd Nj Oh Pa Pe Po) Nw(Hv Hx In Io Ir Iu Iv Lu Lw Lx Mb Mg Mr Ms Mv Na Nd Nr Oh Om Pa) Jp(Hw Hx Ir Iv Jk Jn Jo Jt Lw Lx Mg Mr Nb Nq Nr Oh Om Pa Pc Po) Om(Hw Iu Iv Jt Lw Lx Ma Mr Mx My Ng Nl Nq Of Pa Pb Pe Qd Qe) Jn(Hw Hx Io Jg Jh Jj Jk Jo Jt Lu Lw Mg Mv Nb Nd Nr Oh Po) Nn(Iu Jg Jh Jj Lu Lw Me Mf Mq Ms Mx Nd Ni Nj Ny Pc Qb) Nq(Hv Hw Hx Im Iv Jj Jo Jt Lw Mr Ms Na Nf Nr Pa Po Qe) Lx(Hq Hw Ir Iv Jg Jj Jk Jo Lw Ly Ma Mh Na Oh Pc Qd Qe) Lv(Ih Ii Ij Il Io Li Mb Md Mv Mw Mx My Na Nj Ny Qe) Nt(Hx Im Ir Jg Jh Jk Jt Mg Ne Nf Og Pe Po Qe) Ma(Hw Hx Ir Iv Jk Jo Jt Mr Nb Nf Pa Pe Po Qe) Pc(Hw Hx Im Iv Jk Jo Jt Nb Nf Nr Pa Po Qd Qe) Mr(Im Ir Jg Jj Jk Jt Mg Oh Po Qd Qe) Qd(Hw Hx Jg Jk Jo Jt Nb Pa Pe Po) Jt(Hx Im Jj Jk Lu Nd Pa Pe Po) Pe(Im Jg Jh Jk Mg Og Po Qe) Ir(Jg Jj Jk Lw Mg Pa Po) Lw(Hx Jk Nb Pa Po) Mu(Hv Mh Nf Pb Qb) Jo(Im Jk Oh Po Qe) Nb(Im Ms My) Jg(Hw Ng Og) Dc(cS Fr) Ef(aA dK) Wm(Ji Jq) Po(Jj Pb) Hx(Jj Og) Jk(Og Oh) Oy(Jh Mw) DdFr MgHw OhPa Constrained panels with 2 analytes, where 1.0E-4 >= 'model p-value' > 1.0E-5. Contains 508 panels of 16,788 total panels evaluated. : Pa(Hv Hw Hx Ij Im In Iv Jg Jh Jj Jk Jo Js Lx Md Mg Mk Mn Mq Ms Mv Mx My Na Nf Ni Nj Nm Nx Ny Og Po Qe) Jg(Hu Hv Hx Im In Io Iu Iv Jj Jo Jt Lu Lw Ma Mm Mq Ms Mx My Na Nb Nf Nq Nr Ns Oh Oi Oy Pc Po Qe) Ma(Hr Hv Ih Ii Ij Im In Iu Jj Jp Js Lu Lw Mb Md Mh Mm Mq Mx Na Nl Nq Nr Nx Oh Pc Qb Qd) Pc(Hu Hv Ih Ii Ij Il In Iu Jh Js Lu Md Mg Mj Mm Mp Mv Mx Na Nd Ni Nq Nx Ny Pd Qb) Nq(Ih Ii Ij In Jh Jk Js Lx Mh Mp Mq Mx My Nb Ng Ni Nj Nm Nx Ny Og Oh Oy Qb) Im(Hw Hx Ii Ip Iv Jj Jk Jp Lu Lw Lx Md Mg Mj Mm Mq Mv Nf Nr Nx Oh Po Qd Qe) Nb(Hx Ir Iv Jh Jj Jk Lx Md Mg Mh Ml Mv Mx Nd Nj Ny Of Oh Oy Pb Po Qe) Jp(Hv Ii Ij In Io Jj Lu Md Mh Mq Mv Mw My Nf Nj Nx Og Pb Qb) Dd(aA aJ aO aP aX bE bF Bg bW bZ cU De dF dI Dk dN) Mn(Hv Ii In Jj Lu Md Mq Ms Mv My Na Nb Nf Ni Pc) aJ(Ad aM An As Aw BG Cp Cq CU Cw De Dk dN) My(Hv Hw Ii Im In Jj Js Md Mh Mq Nf Nj Nx Pc) De(aA An aP Ax bA bV cJ cS dF dI dM dN Ex) Nf(Hw Ih Ij Il Jj Lu Mv Mw Nd Nj Nl Qb Wm) Md(Ih Ii Ij Il Jg Jj Js Mj Mv Mw Nj Qb) aA(Aw bB bF BG bH Co Cq cU Dk mP nR) bA(An aO Aw bE BG bJ bZ cS cU Dk) Mv(Hv Ih Ii Ij In Js Mq Ms Na Nj) Jg(Ih Ii Ij Js Lz Mh Nd Ni Nx Qb) Jj(In Jm Js Li Mj Mw Nd Pc Pd Qb) aP(Ad An Aw BG cJ Cp Cq Cw Dk) Im(Hv Ij In Mb Mh Na Nj Og Pd) dN(An Aw Bg bH cJ Cp Cq cS Dk) Mw(Hw Ii Iv Mq Ms Nx Pa Pc) Cp(aX bE bH bZ cJ dE dI) Cw(aX bE bH bW bZ cU dI) Lu(Ih Ij Iv Js Nm Nx Qb) cS(aO bG Bn cU Cv dF dM) Nj(Ii Ij In Js Na Pc) Qe(Hv Ii In Na Nd Ni) jH(hR hW iB jD jP lM) Aw(An AX cJ dI) Ex(bR cD cJ dK Ef) Nx(Lz Mh Ms Nd Og) Ad(aX bZ cU dI) Cq(aX cJ Db dE) Mq(Il Js Ns Pc) Hw(Ih Js Pb Qb) Ii(Ih Mh Ms Og) An(aX bC cJ) Wm(Ip Iq Qd) Pc(Fp Ms Og) dK(bG Dk Gl) Ef(aN dE) Nd(Ij Na) Ih(Mj Nb) Iv(Mb Og) aO(aM dM) bE(dF Gl) fR(Co cX) iB(hR jD) kG(IX mW) CubZ DkcJ MfPa MsIj bHdF mFmP hWjR jDIO Constrained panels with 2 analytes, where 1.0E-3 >= 'model p-value' > 1.0E-4. Contains 505 panels of 16,788 total panels evaluated. : Jh(Hu Hv Ih Ii Ij Il Im In Iu Jg Jj Js Li Lu Lz Md Mg Mh Mj Mn Mq Ms Mx My Na Nd Nj Nx Ny Pd Qb) Oh(Fp Hu Hv Ih Il Iu Jj Js Li Lu Md Mg Mj Mn Mq Mv Mw Mx My Na Nd Nf Ni Nj Nm Ny Pd Qb) Mg(Fp Ih Ii Ij Il In Iu Jg Js Lu Lz Mb Md Mh Mj Mn Mq Ms Mv Nd Ng Nx Ny) Ny(Hv Ii In Iu Iv Jg Lu Ma Md Mh Mq Mv Mx My Na Nd Nf Nj Nr Nu Nx Og) Lw(Fp Hu Ih In Io Jj Li Lz Md Mf Mh Mj Mn Ms My Nd Nx Og Pc Qb) Mx(Hv Hw Ii Ij Im In Iu Jj Mb Md Mn Mv Mw My Na Nf Nj Nm Nr Nx) Dc(aJ aP Ax BA bC bE BG bH bJ bZ cU DE dF dI dK dN) Iu(Hv Hw Ij Im In Iv Jj Js Lu Md Mn Mq Mv Mw My Na Nr Nx Pd) Nr(Ih Ij Iv Jj Js Lu Md Mn Mv Mw My Nf Nj Nx Og Pb Qb) Dd(aA aJ aO aP aX bE bF Bg bW bZ cU De dF dI Dk dN) Mn(Hv Ii In Jj Lu Md Mq Ms Mv My Na Nb Nf Ni Pc) aJ(Ad aM An As Aw BG Cp Cq CU Cw De Dk dN) My(Hv Hw Ii Im In Jj Js Md Mh Mq Nf Nj Nx Pc) De(aA An aP Ax bA bV cJ cS dF dI dM dN Ex) Nf(Hw Ih Ij Il Jj Lu Mv Mw Nd Nj Nl Qb Wm) Md(Ih Ii Ij Il Jg Jj Js Mj Mv Mw Nj Qb) aA(Aw bB bF BG bH Co Cq cU Dk mP nR) bA(An aO Aw bE BG bJ bZ cS cU Dk) Mv(Hv Ih Ii Ij In Js Mq Ms Na Nj) Jg(Ih Ii Ij Js Lz Mh Nd Ni Nx Qb) Jj(In Jm Js Li Mj Mw Nd Pc Pd Qb) aP(Ad An Aw BG cJ Cp Cq Cw Dk) Im(Hv Ij In Mb Mh Na Nj Og Pd) dN(An Aw Bg bH cJ Cp Cq cS Dk) Mw(Hw Ii Iv Mq Ms Nx Pa Pc) Cp(aX bE bH bZ cJ dE dI) Cw(aX bE bH bW bZ cU dI) Lu(Ih Ij Iv Js Nm Nx Qb) cS(aO bG Bn cU Cv dF dM) Nj(Ii Ij In Js Na Pc) Qe(Hv Ii In Na Nd Ni) jH(hR hW iB jD jP lM) Aw(An AX cJ dI) Ex(bR cD cJ dK Ef) Nx(Lz Mh Ms Nd Og) Ad(aX bZ cU dI) Cq(aX cJ Db dE) Mq(Il Js Ns Pc) Hw(Ih Js Pb Qb) Ii(Ih Mh Ms Og) An(aX bC cJ) Wm(Ip Iq Qd) Pc(Fp Ms Og) dK(bG Dk Gl) Ef(aN dE) Nd(Ij Na) Ih(Mj Nb) Iv(Mb Og) aO(aM dM) bE(dF Gl) fR(Co cX) iB(hR jD) kG(IX mW) CubZ DkcJ MfPa MsIj bHdF mFmP hWjR jDIO Constrained panels with 2 analytes, where 1.0E-2 >= 'model p-value' > 1.0E-3. Contains 459 panels of 16,788 total panels evaluated. : Bg(Ad An Ar As aX bC bE Bn bV cD cJ cT cU Cw dE dG dI dK dL dM Ex fR) Nj(Fp Hv Ih Il Iu Jj Lu Lz Mb Mh Mj Mn Mq Mw Nd Ni Nm Nu Pd Pf Qb) An(aA aO Ba bE bV bW bZ Co Cq CU Cw Dd dF DK fR Gl) Nu(Hq Hv Ih In Iu Jj Lu Lz Mb Md Mh Mj Mn Mq Mw My Na Nd) Pd(Hv Ih Il In Lu Md Mn Mq Mw My Na Nl Ns Ny Og Pb Qb) Nm(Fp Hv Ih Il Iu Jj Lz Md Mh Mj Mn Mw Nd Nl Og Qb) As(aO aX Ba bC bE bF bG bH bW bZ cJ cU dE dI Gl) Bn(aJ aO aX Ba bC bE bF bG bH bW bZ cU dE dI dK) Lu(Fp Hv Il In Jj Li Lz Mh Mj Mq Mw My Na Nd Nl) Ad(aA aO bC bE bF bH bV bW cJ dE DK Ex Gl) Nd(Fp Hq Hv Ih In Js Li Mh Mj Mq Mw My Ni Qb) Jj(Fp Hq Hu Hv Iq Lz Mh Mq Na Nc Nl Oy Pf Wm) Ih(Hv Il In Iu Mh Mn Mq Ms Mw My Na Ni Og) Dd(aJ Aw bA bC bG bH bL bV cJ dE fR Gl) Dk(aO aX bC bV bW bZ cD cU dF DI fR) aM(bF bG bH bL bQ bW bZ cK cU dF dI Gl) Cu(aO aX bC bE bF bW cJ cU dE dI Gl) Na(Fp Il Li Lz Md Mh Mj Mw My Nl Qb)

Figure 34 Continued bG(bC bE bW cD cJ cR Cw dE dM fR) Mq(Li Lz Mb Md Mh Mj Nk Nl Qb) Mw(Hu Hv Il In Mh Mj Ng Nl Ns) bH(aO Aw bA bB bV cJ cT Cv fR) Ni(Il Iu Li Lz Nc Nk Nl Qb) In(Il Li Lz Md Mh Nl Og Qb) Ex(aU Ax bB bE Bo bU Cp) My(Fp Li Lz Ms Nl Og Qb) Hv(Il Li Lz Md Mh Nl Qb) bW(Ax cD Cp cT Cv Db dE) cK(aI aO bB cF cJ cT dK) mF(mI mT nM nN nR oP oQ) Cq(bE bV bZ cD dB Gl) Cw(aO bF cJ dE dF Gl) Mj(Hu Iu Lz Mb Mn Og) dK(Ax bB bQ bZ cU dF) Mn(Il Lz Mh Nl Qb) Mb(Fp Lz Mf Mh) Iu(Fp Li Og Qb) bC(aO bB cT fR) bQ(bE cC cD dH) bV(Ao bB cJ Co) Cv(bZ cJ cU) Wm(Js Ly Oh) Gl(aA cD cJ) Md(Li Mh Nl) al(bE dE dM) fR(Bo Ch cU) Ii(Li Qb) Il(Ij Og) cD(cG dA) nR(mW nC) mP(mU nT) hR(hX lM) iB(jP lM) AwdE CpcU NsJh QbOg bAbB bEcT bRdA cCdI cGcL nNmU nBoQ jEjF Unconstrained panels with 3 analytes, where 1.0E-8 >= 'AUC p-value' > 0. Contains 37,732 panels of 645,860 total panels evaluated. :
On{Nm(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Mm(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nj Nk Nl Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Nj(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Ip(aA Et Fp Fr Hq Hr Hu Hv Hw Hx Ih Ii Ij Ik Il Im In Io Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Jr(aA Et Fp Fr Hq Hr Hu Hv Hw Hx Ih Ii Ij Ik Il Im In Io Iq Ir Is It Iu Iv Jg Jh Ji Jj Jk Jl Jm Jn Jo Jp Jq Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Og(aA Et Fp Fr Hq Hr Hu Hv Hw Hx Ih Ii Ij Ik Il Im In Io Iq Ir Is It Iu Iv Jg Jh Ji Jj Jk Jl Jm Jn Jo Jp Jq Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Ns Nt Nu Nv Nw Nx Ny Oe Of Oh Oi Ok Om Oy Oz Pa Pb Pc Pd Pe Pf Pg Po Pz Qa Qb Qc Qd Qe Wm) Ns(aA Et Fp Hq Hr Hu Hv Hw Hx Ih Ii Ij Ik Il Im In Io Iq Ir Is It Iu Iv Jg Jh Ji Jj Jk Jl Jm Jn Jo Jp Jq Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Pz Qa Qb Qc Qd Qe Wm) Ly(aA Et Fp Fr Hq Hr Hu Hv Hw Hx Ih Ii Ij Ik Il Im In Io Iq Ir Is It Iu Iv Jg Jh Ji Jj Jk Jm Jn Jo Jp Jq Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Pz Qa Qb Qc Qd Qe Wm) Ii(aA Et Fp Fr Hq Hr Hu Hv Hw Hx Ih Ij Ik Il Im In Io Iq Ir Is It Iu Iv Jg Jh Ji Jj Jk Jm Jn Jo Jp Jq Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Pz Qa Qb Qc Qd Qe Wm) Is(aA Et Fp Fr Hq Hr Hu Hv Hw Hx Ih Ij Ik Il Im In Io Iq Ir It Iu Iv Jg Jh Ji Jj Jk Jl Jm Jn Jo Jp Jq Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Pz Qa Qb Qc Qd Qe) Iu(aA Et Fp Fr Hq Hr Hu Hv Hw Hx Ih Ij Ik Il Im In Io Iq Ir It Iv Jg Jh Ji Jj Jk Jm Jn Jo Jp Jq Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Pz Qa Qb Qc Qd Qe Wm) Pz(aA Et Fp Fr Hq Hr Hu Hv Hw Hx Ih Ij Ik Il Im In Io Iq Ir It Iv Jg Jh Ji Jj Jk Jm Jn Jo Jp Jq Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Qa Qb Qc Qd Qe Wm) Ji(aA Et Fp Fr Hq Hr Hu Hv Hw Hx Ih Ij Ik Il Im In Io Iq Ir It Iv Jg Jh Jj Jk Jl Jm Jn Jo Jp Jq Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Qa Qb Qc Qd Qe) Jj(aA Et Fp Fr Hq Hr Hu Hv Hw Hx Ih Ij Ik Il Im In Io Iq Ir It Iv Jg Jh Jk Jm Jn Jo Jp Jq Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Qa Qb Qc Qd Qe Wm) Jo(aA Et Fp Fr Hq Hr Hu Hv Hw Hx Ih Ij Ik Il Im In Io Iq Ir It Iv Jg Jh Jk Jm Jn Jp Jq Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Qa Qb Qc Qd Qe Wm) Jq(aA Et Fp Fr Hq Hr Hu Hv Hw Hx Ih Ij Ik Il Im In Io Iq Ir It Iv Jg Jh Jk Jl Jm Jn Jp Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Qa Qb Qc Qd Qe) Nv(aA Et Fp Fr Hq Hr Hu Hv Hw Hx Ih Ij Ik Il Im In Io Iq Ir It Iv Jg Jh Jk Jl Jm Jn Jp Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nv Nw Nx Ny Oe Of Oh Oi Ok Om Oy Oz Pa Pb Pc Pd Pe Pf Pg Po Qa Qb Qc Qd Qe) Nx(aA Et Fp Fr Hq Hr Hu Hv Hw Hx Ih Ij Ik Il Im In Io Iq Ir It Iv Jg Jh Jk Jm Jn Jp Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nw Ny Oe Of Oh Oi Ok Om Oy Oz Pa Pb Pc Pd Pe Pf Pg Po Qa Qb Qc Qd Qe Wm) Oe(aA Et Fp Fr Hq Hr Hu Hv Hw Hx Ih Ij Ik Il Im In Io Iq Ir It Iv Jg Jh Jk Jl Jm Jn Jp Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nw Ny Of Oh Oi Ok Om Oy Oz Pa Pb Pc Pd Pe Pf Pg Po Qa Qb Qc Qd Qe) Of(aA Et Fp Fr Hq Hr Hu Hv Hw Hx Ih Ij Ik Il Im In Io Iq Ir It Iv Jg Jh Jk Jm Jn Jp Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nw Ny Oh Oi Ok Om Oy Oz Pa Pb Pc Pd Pe Pf Pg Po Qa Qb Qc Qd Qe Wm) Oh(aA Et Fp Fr Hq Hr Hu Hv Hw Hx Ih Ij Ik Il Im In Io Iq Ir It Iv Jg Jh Jk Jm Jn Jp Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nw Ny Oi Ok Om Oy Oz Pa Pb Pc Pd Pe Pf Pg Po Qa Qb Qc Qd Qe Wm) Ok(aA Et Fp Fr Hq Hr Hu Hv Hw Hx Ih Ij Ik Il Im In Io Iq Ir It Iv Jg Jh Jk Jm Jn Jp Js Jt Lh Li Lj Lu Lv Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nn No Nq Nr Nt Nu Nw Ny Oi Om Oy Oz Pa Pb Pc Pd Pe Pf Pg Po Qa Qb Qc Qd Qe Wm) Oy(aA Et Fp Fr Hq Hr Hu Hv Hw Hx Ih Ij Ik Il Im In Io Iq Ir It Iv Jg Jh Jk Jl Jm Jn Jp Js Jt Lh Li Lj Lu

Mj Mk Mq Mz Na Ne Nf Ng Nh Ni No Nr Of Oy Oz Pd Pf Qd Qe) No(Fp Hq Hu Hv Ih Ir Jl Jo Lu Ly Md Mk Mq Mz Na Ne Nf Ng Ni Of Oy Oz Pd Pf Pz Qd Qe) Nr(Fp Hq Hu Hv Ih Ir Jo Jt Lu Ly Mb Md Mj Mk Mq Mz Na Nf Ng Nh Ni Of Pd Pf Pz Qd Qe) Mj(Fp Hq Hu Hv Ir Jo Lu Ly Mb Md Mk Mq Mz Na Ne Nf Ng Nh Ni Of Oy Oz Pf Pz Qd Qe) Ng(Fp Hq Hu Hv Ih Jo Ly Mb Mk Mq Mz Na Ne Nf Nh Ni Of Oy Oz Pd Pf Pz Qd Qe) Ni(aA Fp Hq Hu Hv Ih Lu Ly Mb Md Mk Mq Mz Na Ne Nf Nh Of Oy Oz Pf Pz Qe) Qe(aA Fp Hq Hu Hv Ih Ir Jo Lu Ly Mb Mk Mq Na Ne Nh Of Oz Pd Pf Pz Qd) Oz(aA Fp Hq Hu Hv Ih Lu Ly Mb Md Mq Mz Na Nf Nh Of Oy Pd Pf Pz Qd) Jo(aA Fp Hq Hu Hv Ih Ir Jt Lu Ly Mb Mk Mq Ne Nh Of Oy Pd Pf Pz) Hu(aA Fp Hv Ih Lu Mb Mk Mq Mz Na Ne Nf Nh Of Pd Pf Pz Qd) Hv(Fp Ih Ly Mb Md Mk Mq Mz Na Ne Nf Nh Of Pd Pf Pz Qd) Pz(Fp Ih Ir Jl Ly Mb Mk Mq Mz Na Ne Nf Nh Of Pd Qd) Of(Fp Ih Jl Jt Lu Ly Mb Md Mk Mq Mz Na Nf Nh Qd) Lu(aA Fp Hq Mb Mq Na Ne Nf Nh Oy Pd Pf Qd) Mk(Fp Ih Ly Mb Md Mq Mz Na Nf Nh Pd Qd) Mq(Fp Hq Ih Ly Md Mz Na Ne Nf Nh Pf) Qd(aA Fp Hq Ir Ly Mb Na Ne Nh Pd Pf) Mz(Fp Ih Jl Ly Mb Md Na Nf Nh Pd) Nh(Fp Ih Mb Na Ne Nf Pd Pf) Ih(aA Fp Ly Mb Na Pd Pf) Fp(aA Ir Na Ne Nf) Na(Ly Ne Nf Pd) Ne(Jl Ly Oy) Pf(Hq Mb Pd) LyMd MbHq NfJl PdaA} Ji{Lv(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Ms(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Js Jt Lh Li Lj Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Jp(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jq Js Jt Lh Li Lj Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Io(aA Et Fp Fr Hq Hr Hu Hv Hw Hx Ih Ii Ij Ik Il Im In Ip Iq Ir Is It Iu Iv Jg Jh Jj Jk Jl Jm Jn Jo Jq Js Jt Lh Li Lj Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Ip(aA Et Fp Fr Hq Hr Hu Hv Hw Hx Ih Ii Ij Ik Il Im In Iq Ir Is It Iu Iv Jg Jh Jj Jk Jm Jn Jo Jq Js Jt Lh Li Lj Lu Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Lu(aA Et Fp Fr Hq Hr Hu Hv Hw Hx Ih Ii Ij Ik Il Im In Iq Ir Is It Iu Iv Jg Jh Jj Jk Jl Jm Jn Jq Js Lh Li Lj Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Mt(aA Et Fp Fr Hq Hr Hu Hv Hw Hx Ih Ii Ij Ik Il Im In Iq Ir Is It Iu Iv Jg Jh Jj Jk Jl Jm Jn Jo Jq Js Jt Lh Li Lj Lw Lx Ly Lz Ma Mb Mc Md Me Mf Mg Mh Mi Mj Mk Ml Mm Mn Mp Mq Mr Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Oi(aA Et Fp Fr Hq Hr Hu Hv Hw Hx Ih Ii Ij Ik Il Im In Iq Ir Is It Iu Iv Jg Jh Jj Jk Jl Jm Jn Jo Jq Js Jt Lh Li Lj Lw Lx Ly Lz Ma Mb Mc Me Mf Mg Mh Mi Mj Mk Ml Mm Mn Mp Mq Mr Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Ok Om Oy Oz Pa Pb Pc Pd Pe Pf Pg Po Pz Qa Qb Qc Qd Qe) Pg(aA Et Fp Fr Hq Hr Hu Hv Hw Hx Ih Ii Ij Ik Il Im In Iq Ir Is It Iv Jg Jh Jj Jk Jl Jm Jn Jo Jq Js Jt Lh Li Lj Lw Lx Ly Lz Ma Mb Mc Md Me Mf Mg Mh Mi Mj Mk Ml Mm Mn Mp Mq Mr Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Ok Om Oy Oz Pa Pb Pc Pd Pe Pf Po Pz Qa Qb Qc Qd Qe) Nm(aA Et Fp Fr Hq Hr Hu Hv Hw Hx Ih Ii Ij Ik Il Im In Iq Ir Is It Iu Iv Jg Jh Jj Jk Jl Jm Jn Jo Jq Js Lh Li Lj Lw Lx Ly Lz Ma Mb Mc Md Me Mf Mg Mh Mi Mj Mk Ml Mn Mp Mq Mr Mu Mv Mw Mx My Mz Na Nb Nc Nd Ne Nf Ng Nh Ni Nj Nk Nl Nn No Nq Nr Ns Nt Nu Nv Nw Nx Ny Oe Of Og Oh Ok Om Oy Oz Pa Pb Pc Pd Pe Po Pz Qa Qb Qc Qd Qe Wm) Nj(aA Et Fp Fr Hq Hr Hu Hv Hw Hx Ih Ii Ij Ik Il Im In Iq Ir Is It Iu Iv Jg Jh Jj Jk Jl Jm Jn Jo Jq Js Jt Lh Li Lj Lw Lx Ly Lz Ma Mb Mc Md Me Mf Mg Mh Mi Mj Mk Ml Mm Mn Mp Mq Mr Mu Mv Mw Mx My Mz Na Nb Nd Ne Nf Ng Nh Ni Nl Nn No Nq Nr Ns Nt Nu Nv Nw Nx Ny Oe Of Og Oh Ok Om Oy Oz Pa Pb Pc Pe Pf Po Pz Qa Qb Qc Qd Qe Wm) Jj(aA Et Fp Fr Hq Hr Hu Hv Hw Hx Ih Ii Ij Ik Il Im In Iq Ir Is It Iu Iv Jg Jh Jk Jl Jm Jn Jo Jq Js Jt Lh Li Lj Lw Lx Ly Lz Ma Mb Mc Md Me Mf Mg Mh Mi Mj Mk Ml Mm Mn Mp Mq Mr Mu Mv Mw Mx My Mz Na Nb Nc Nd Ne Nf Ng Nh Ni Nk Nl Nn No Nq Nr Ns Nt Nu Nv Nw Nx Ny Oe Of Og Oh Ok Oy Oz Pa Pb Pc Pd Pe Po Pz Qa Qb Qc Qd Qe) Jk(aA Et Fp Fr Hq Hr Hu Hv Hw Hx Ih Ii Ij Ik Il Im In Iq Ir Is It Iu Iv Jg Jh Jl Jm Jn Jo Jq Js Jt Lh Li Lj Lw Lx Ly Lz Ma Mb Mc Md Me Mf Mg Mh Mi Mj Mk Ml Mm Mn Mp Mq Mr Mu Mv Mw Mx My Mz Na Nb Nc Nd Ne Nf Ng Nh Ni Nk Nl Nn No Nq Ns Nu Nv Nw Nx Ny Oe Of Og Oh Ok Om Oy Oz Pa Pb Pc Pd Pe Pf Po Pz Qa Qb Qc Qd Qe) Jl(aA Et Fp Fr Hq Hr Hu Hv Hw Hx Ih Ii Ij Ik Il Im In Iq Ir Is It Iu Iv Jg Jh Jm Jn Jo Jq Js Jt Lh Li Lj Lw Lx Ly Lz Ma Mb Mc Md Me Mf Mg Mi Mj Mk Ml Mm Mn Mp Mq Mr Mu Mv Mw Mx My Mz Na Nb Nc Nd Ne Nf Ng Nh Ni Nk Nl No Nq Nr Ns Nt Nu Nv Nw Nx Ny Oe Of Og Oh Ok Om Oy Pa Pb Pc Pd Pe Pf Po Pz Qa Qb Qc Qd Qe) Ne(aA Et Fp Fr Hq Hr Hu Hv Hw Hx Ih Ii Ij Ik Il Im In Iq Ir Is It Iu Iv Jg Jh Jm Jn Jq Js Jt Lh Li Lj Lw Lx Ly Lz Ma Mb Mc Md Me Mf Mg Mh Mi Mj Mk Ml Mm Mn Mp Mq Mr Mu Mv Mw Mx My Mz Na Nb Nd Nf Ng Nh Ni Nl Nn No Nq Nr Ns Nu Nv Nw Nx Ny Oe Of Og Oh Ok Om Oy Oz Pa Pb Pc Pd Pe Pf Po Pz Qa Qb Qc Qd Qe) Nh(aA Et Fp Fr Hq Hr Hv Hw Hx Ih Ii Ij Ik Il Im In Iq Ir Is It Iu Iv Jg Jh Jm Jn Jq Js Jt Lh Li Lj Lw Lx Ly Lz Ma Mb Mc Md Me Mf Mg Mh Mi Mj Mk Ml Mm Mn Mp Mq Mr Mu Mv Mw Mx My Mz Na Nb Nd Nf Ng Ni Nl Nn No Nq Nr Ns Nt Nu Nv Nw Nx Ny Oe Of Og Oh Ok Om Oy Oz Pa Pb Pc Pd Pe Pf Po Pz Qa Qb Qc Qd Qe) Il(aA Et Fp Fr Hq Hr Hu Hv Hw Hx Ih Ii Ij Ik Im In Iq Ir Is It Iu Iv Jg Jh Jm Jn Jq Js Jt Lh Li Lj Lw Lx Ly Lz Ma Mb Mc Md Me Mf Mg Mh Mi Mj Mk Ml Mm Mn Mp Mq Mr Mu Mv Mw Mx My Mz Na Nb Nd Nf Ng Ni Nl Nn No Nq Nr Ns Nt Nu Nv Nw Nx Ny Oe Og Oh Ok Om Oy Oz Pa Pb Pc Pd Pe Pf Po Pz Qa Qb Qc Qd Qe) Qe(aA Et Fp Fr Hq Hr Hu Hv Hw Hx Ih Ii Ik Im In Iq Ir Is It Iu Iv Jg Jh Jm Jn Jq Js Jt Lh Li Lj Lw Lx Ly Lz Ma Mb Mc Md Me Mf Mg Mh Mi Mj Mk Ml Mm Mn Mp Mq Mr Mu Mw Mx My Mz Na Nb Nc Nd Nf Ng Ni Nk Nl Nn No Nq Nr Ns Nt Nu Nv Nw Nx Ny Oe Of Og Oh Ok Om Oy Oz Pa Pb Pc Pd Pe Pf Po Pz Qa Qc Qd) Jn(aA Et Fp Fr Hq Hr Hu Hv Hw Hx Ih Ii Ij Ik Im In Iq Ir Is It Iu Iv Jg Jh Jm Jq Js Jt Lh Li Lj Lw Lx Ly Lz Ma Mb Mc Md Me Mf Mg Mh Mi Mj Mk Ml Mm Mn Mp Mq Mr Mu Mv Mw Mx My Mz Na Nb Nd Nf Ng Ni Nl Nn No Nq Nr Ns Nt Nu Nv Nw Nx Ny Oe Of Og Oh Ok Om Oy Oz Pa Pb Pc Pe Pf Po Pz Qa Qb Qc Qd) Et(aA Fp Fr Hq Hr Hu Hv Hw Hx Ih Ii Ij Ik Im In Iq Ir Is It Iu Iv Jg Jh Jm Jo Jq Js Jt Lh Li Lj Lw Lx Ly Lz Ma Mc Md Me Mf Mg Mh Mi Mj Mk Ml Mm Mn Mp Mq Mr Mu Mv Mw Mx My Mz Nb Nc Nd Nf Ng Nk Nl Nn Nq Nr Ns Nt Nu Nv Nw Nx Ny Oe Of Og Oh Ok Om Oy Oz Pa Pb Pc Pd Pe Pf Po Pz Qa Qc Qd) Fr(aA Fp Hq Hr Hu Hv Hw Hx Ih Ii Ij Ik Im In Iq Ir Is It Iu Iv Jg Jh Jm Jo Jq Js Jt Lh Li Lj Lw Lx Ly Lz Ma Mb Mc Md Me Mf Mg Mh Mi Mk Ml Mm Mn Mp Mq Mr Mv Mw Mx My Mz Na Nb Nc Nd Nf Ng Ni Nk Nl Nn Nq Nr Ns Nt Nu Nv Nw Nx Ny Oe Of Og Oh Ok Om Oz Pa Pb Pc Pd Pe Pf Pz Qa Qb Qc Qd) Is(aA Fp Hq Hr Hu Hv Hw Hx Ih Ii Ij Ik Im In Iq Ir It Iu Iv Jg Jh Jm Jq Js Jt Lh Li Lj Lw Lx Ly Lz Ma Mb Mc Md Me Mf Mg Mh Mi Mj Mk Ml Mm Mn Mp Mq Mr Mv Mw Mx My Mz Nb Nd Nf Ng Ni Nk Nl Nn Nq Nr Ns Nt Nu Nv Nw Nx Ny Oe Of Og Oh Ok Om Oy Oz Pa Pb Pc Pd Pe Pf Po Pz Qa Qc Qd) Og(aA Fp Hq Hr Hu Hv Hw Hx Ih Ii Ij Ik Im In Iq Ir It Iu Iv Jg Jh Jm Jq Js Jt Lh Li Lj Lw Lx Ly Lz Ma Mb Mc Me Mf Mh Mi Mj Mk Ml Mm Mn Mp Mq Mr Mu Mv Mw Mx My

Figure 34 Continued

Mz Na Nb Nc Nd Ng Ni Nk Nl Nn Nq Nr Ns Nt Nu Nv Nw Nx Ny Oe Of Oh Ok Oy Oz Pa Pb Pc Pd Pe Pf Po Pz Qa Qb Qc Qd) Pa(aA Fp Hq Hr Hu Hv Hw Hx Ih Ii Ij Ik Im In Iq Ir It Iu Iv Jg Jh Jm Jq Js Lh Li Lj Lw Lx Ly Lz Ma Mb Mc Md Me Mf Mg Mh Mj Mk Ml Mm Mn Mp Mq Mr Mu Mv Mw Mx My Mz Na Nb Nd Nf Ng Ni Nl Nn No Nq Nr Ns Nt Nu Nv Nw Nx Ny Oe Oh Ok Om Oy Oz Pb Pc Pd Pe Pf Po Pz Qa Qb Qc Qd) aA(Fp Hq Hr Hu Hv Hw Hx Ih Ii Ij Ik Im In Iq Ir It Iu Iv Jg Jh Jm Js Jt Lh Li Lj Lw Lx Ly Lz Ma Mb Mc Mf Mg Mh Mi Mj Mk Ml Mm Mn Mp Mq Mr Mu Mv Mw Mx My Mz Nb Nc Nd Ni Nk Nl Nn Nq Nr Ns Nt Nu Nv Nw Nx Ny Oe Of Oh Ok Oy Oz Pb Pc Pd Pe Pf Po Pz Qa Qb Qc Qd) Nu(Fp Hq Hr Hu Hv Hw Hx Ih Ii Ij Im In Iq Ir It Iu Iv Jg Jh Jm Jq Js Lh Li Lj Lw Lx Ly Lz Ma Mb Mc Md Me Mf Mg Mh Mi Mj Mk Ml Mm Mn Mp Mq Mr Mu Mx My Mz Na Nb Nd Nf Ng Ni Nk Nl No Nq Nr Ns Nt Nv Nx Ny Oe Of Ok Om Oy Oz Pb Pc Pe Pf Po Pz Qa Qb Qc Qd) Ml(Fp Hq Hr Hu Hv Hw Hx Ih Ii Ij Ik Im In Iq Ir It Iu Iv Jh Jm Jq Js Jt Lh Li Lj Lw Lx Ly Lz Ma Mc Me Mf Mh Mi Mj Mk Mn Mp Mq Mr Mu Mv Mw Mx My Mz Na Nb Nd Nf Ng Nk Nl Nn No Nq Nr Ns Nt Nv Nw Nx Ny Oe Oh Ok Oy Oz Pb Pc Pe Pf Po Pz Qa Qb Qc Qd Wm) Hx(Fp Hq Hr Hu Hv Hw Ih Ii Ij Ik Im In Iq Ir It Iu Iv Jg Jh Jm Jq Js Jt Li Lj Lw Lx Ly Lz Ma Mb Mc Md Me Mf Mg Mh Mj Mk Mm Mn Mp Mq Mv Mw Mx My Mz Na Nd Nf Ng Ni Nk Nl Nn No Nr Ns Nv Nw Nx Ny Oe Of Oh Ok Oy Oz Pb Pc Pd Pe Pf Po Pz Qa Qb Qc Qd) Pb(Fp Hr Hu Hv Hw Ih Ii Ij Ik Im In Iq Ir It Iu Iv Jg Jh Jm Jq Js Lh Li Lj Lw Lx Lv Lz Ma Mb Mc Me Mf Mg Mh Mj Mk Mm Mn Mp Mq Mr Mu Mv Mw Mx My Mz Na Nb Nd Nf Ng Nl Nn No Nq Nr Ns Nt Nv Nw Nx Ny Oe Of Oh Ok Om Oy Oz Pc Pe Po Pz Qa Qb Qc Qd) Qa(Fp Hq Hr Hu Hv Hw Ih Ii Ij Ik Im In Iq Ir It Iv Jg Jh Jm Jq Js Jt Lh Li Lj Lw Lx Ly Ma Mb Mc Md Me Mf Mg Mi Mj Mk Mm Mn Mp Mq Mr Mu Mw Mx My Mz Nb Nd Nf Ng Ni Nn Nq Nr Ns Nv Nw Nx Ny Oe Of Oh Ok Om Oy Oz Pc Pd Pe Pf Po Pz Qc Qd) Ns(Fp Hq Hr Hu Hv Ih Ii Ij Ik Im In Iq Ir It Iu Iv Jh Jm Js Lh Li Lj Lx Ly Lz Ma Mc Me Mf Mg Mh Mi Mj Mk Mm Mn Mp Mr Mu Mv Mw Mx My Mz Na Nd Ng Ni Nl Nn No Nq Nr Nt Nv Nw Nx Ny Oe Of Ok Oy Oz Pe Pf Po Pz Qb Qc Qd Wm) Mp(Fp Hq Hu Hw Ih Ii Ij Ik Im Iq Ir It Iu Iv Jh Jm Js Jt Lh Li Lj Lw Lx Ly Lz Ma Mb Mc Md Me Mg Mh Mi Mj Mk Mm Mn Mq Mr Mv Mw Mx My Mz Nb Nd Ng Nk Nl Nn Nq Nr Nv Nw Nx Ny Oe Oh Ok Oz Pc Pd Pe Pf Po Pz Qc Qd) Ly(Fp Hu Hv Hw Ih Ii Ij Ik Im In Iq Ir It Iu Iv Jg Jh Jm Js Li Lj Lz Ma Mb Mc Me Mf Mg Mh Mj Mk Mm Mn Mv Mw Mx My Mz Ng Ni Nl Nn Nq Nr Nv Nw Nx Ny Oe Of Oh Ok Om Oy Oz Pc Pf Po Pz Qb Qc Qd Wm) Qc(Fp Hq Hu Hv Hw Ii Ij Ik Im In Iq Ir It Iu Iv Jg Jh Jm Jq Jh Lx Ma Mc Mf Mg Mh Mi Mj Mk Mm Mn Mu Mv Mw Mx My Mz Nb Nd Nf Ng Ni Nl Nn Nq Nr Nt Nv Nw Nx Ny Of Oh Ok Om Oy Pe Po Pz Qb Qd) It(Fp Hu Hw Ih Ii Ij Ik Im In Iq Iu Iv Jh Jm Lh Li Lj Lw Lx Ma Mc Me Mf Mg Mh Mi Mj Mk Mm Mn Mr Mx My Mz Nb Nd Ng Nk Nl Nn Nq Nr Nt Nv Nx Ny Oe Of Ok Oy Oz Pc Pe Po Pz Qb Qd Wm) Lx(Hq Hr Hu Hv Ih Ii Ik Im Iq Ir Iu Iv Jh Js Li Lj Lw Lz Ma Mb Mc Md Me Mg Mh Mj Mk Mn Mq Mr Mw Mx My Mz Nb Nd Nf Ng Nl Nn Nq Nr Nv Nw Nx Ny Oe Ok Oz Pc Pe Po Pz Qd) Nd(Fp Hq Hu Hv Ih Ii Ij Ik In Iq Ir Iv Jg Jh Js Lh Lj Lw Lz Ma Mb Mc Md Me Mh Mj Mk Mn Mq Mr Mv Mw Mx My Nb Nf Ng Nn Nq Nr Nv Nw Nx Ny Oe Oy Oz Pc Pe Pf Po Pz Qd) Nx(Fp Hu Hv Hw Ii Ik In Iq Iv Jg Jh Lh Lj Lw Ma Me Mg Mh Mi Mj Mk Mm Mn Mr Mu Mv Mw Mx My Mz Nb Nk Nl Nn Nq Nr Nt Nv Ny Oe Of Ok Oy Pd Pe Po Pz Qd) Pe(Fp Hu Hv Hw Ih Ii Ik Im In Iu Iv Jg Jh Jo Jt Lh Li Lj Ma Mb Md Me Mh Mj Mk Mm Mn Mr Mw My Nb Ng Nl Nn No Nq Nr Nv Ny Om Oy Pf Po Pz Qb Qd) Mx(Fp Hq Hu Ih Ij Ik Im In Iq Ir Iv Jg Jh Jm Js Li Lj Lw Lz Ma Mc Me Mf Mg Mh Mk Mn Mv Mw My Ng Nl Nn Nq Nv Ny Oe Of Ok Oy Oz Pc Pf Pz Qd) Po(Fp Hu Hw Ih Ii Ik Im In Iq Ir Iu Iv Jg Jh Li Lj Ma Mb Md Me Mg Mh Mi Mn Mr My Nb Nf Ng Nk Nl Nn Nq Nr Nv Nw Ny Oe Ok Om Oz Pz Qd) Hv(Fp Hq Hu Hw Ih Ii Ik Im Iq Ir Iv Jg Jh Jm Jq Js Lj Lw Ma Mc Mf Mg Mk Mn Mr Mu Mw My Mz Nb Ng Nl No Nq Nw Ny Oe Of Ok Oy Oz Pz Qd) Qd(Hq Ih Ii Ik Im In Iq Ir Iv Jg Jh Jm Js Lh Li Lj Lz Ma Mb Mc Me Mf Mh Mk Mn Mr Mw My Ng Nn Nq Nv Ny Of Ok Oy Oz Pc Pf Pz) Pz(Fp Hu Hw Ii Ij Ik Im In Ir Iv Jg Jh Lh Ma Mc Mg Mi Mj Mm Mn Mu Mv My Mz Nb Ng Nk Nn Nq Ny Of Ok Oy Pc Pd Wm) Nv(Fp Hq Hu Hw Ii Ik Im In Iq Iv Jh Js Jt Ma Mb Mc Md Me Mh Mk Mm Mn My Nf Ng Ni Nk Nn Nq Nw Ny Oe Of Ok Om Oz Pf) My(Fp Hu Hw Ih Ii Ik Im In Iq Ir Iv Jq Js Jt Lj Lw Ma Mb Md Me Mm Mw Mz Nf Ng Nn Nq Nw Ny Oe Of Oh Ok Oy) Nn(Fp Hu Hw Ij Ik Im In Ir Iv Jh Js Jt Lh Li Lj Mb Mc Me Mg Mk Mm Mu Mz Nb Ng Nq Of Oh Ok Oy Pc Pd) Jh(Fp Hq Hu Hw Ii Ik Im Ir Iv Js Lh Lj Lw Mb Mc Md Me Mi Mj Mn Mw Mz Nb Nf Ng Nr Ny Oe Oh Ok) Nq(Hw Ii Ik Iq Ir Iv Jm Jq Js Jt Mb Md Me Mf Mg Mh Mj Mk Mm Mz Na Nf Ng Nr Nw Oe Ok) Ir(Hq Hu Ih Ii Ik Im In Iq Iv Jg Jt Lj Ma Mb Mc Me Mk Mn Mw Ng Ny Of Ok Oy Pc Pf) Jt(Hw Iu Jg Jo Jq Lh Lw Ma Mg Mi Mj Mm Mr Mu Mv Na Nb Nl No Nr Nt Oh Ok Pc Wm) Ii(Hu Hw Iu Jg Lh Ma Md Me Mg Mh Mi Mr Mu Mw Nb No Nr Nt Ny Ok Pd Wm) Mb(Fp Hq Hu Hw Im In Iv Lh Ma Mm Mu Mw Ni Oe Ok Om Oy Pf Qb) Hu(Hr Hw Ik Im In Iq Lh Lj Ma Me Mm Mn Mr Ng Nl No Nw Oe) Mm(Hw Iu Jg Jo Ma Mg Mi Mu Mv Oh Ok Pc Qb Wm) Ng(Hq Hw In Lh Lj Ma Mg Mn Mu Mv Mw Ny Ok) Ik(Fp Hw In Iv Li Mg Mu Mv Ny Oe Ok Oy Wm) Iv(Hw Jq Lh Ma Mi Mu Mz Nb Oe Ok Oy) Mw(Iq Lh Lj Md Mh Mj Ny Oy) Hw(In Jg Jo Js Li Ma Mu Of) Oy(Fp Im Lj Md Mn Of Ok) Wm(Fp Iu Li Mk Of Oh) Lh(Im Jo Li Mh Nf Nr) Ny(Ij In Js Mc Me Oe) Ma(Me Ni Oe Of Qb) Mu(Jg Jo Mg Nf Pf) Fp(Jm Lj Me Mn) In(Ij Md Mh Oh) Mn(Hq Im Pf) Nr(Me Mh) Jo(Mr Nt) Of(Mi Ok) MeMj MgQb MhNb MzLj HqIm JgOe} Et{Mm(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Nj(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Pz(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Qa Qb Qc Qd Qe Wm) Lv(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Qa Qb Qc Qd Qe) Ip(aA Fp Fr Hq Hr Hu Hv Hw Hx Ih Ii Ij Ik Il Im In Io Iq Ir Is It Iu Iv Jg Jh Jj Jk Jm Jn Jo Jp Jq Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Qa Qb Qc Qd Qe Wm) Jn(aA Fp Fr Hq Hr Hu Hv Hw Hx Ih Ii Ij Ik Il Im In Io Iq Ir Is It Iu Iv Jg Jh Jj Jk Jm Jo Jp Jq Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Qa Qb Qc Qd Qe Wm) Of(aA Fp Fr Hq Hr Hu Hv Hw Hx Ih Ii Ij Ik Il Im In Io Iq Ir Is It Iu Iv Jg Jh Jj Jk Jm Jo Jp Jq Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Og Oh Oi Ok Om Oy Oz Pa Pb Pc Pd Pe Pf Pg Po Qa Qb Qc Qd Qe Wm) Og(aA Fp Fr Hq Hr Hu Hv Hw Hx Ih Ii Ij Ik Il Im In Io Iq Ir Is It Iu Iv Jg Jh Jj Jk Jl Jm Jo Jp Jq Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Oh Oi Ok Om Oy Oz Pa Pb Pc Pd Pe Pg Po Qa Qb Qc Qd Qe Wm) Pg(aA Fp Fr Hq Hr Hu Hv Hw Hx Ih Ii Ij Ik Il Im In Io Iq Ir Is It Iu Iv Jg Jh Jj Jk Jm Jo Jp Jq Js Jt Lh Li Lj Lu Lw Lx Ly Lz Ma

Figure 34 Continued

Mr Mv Mw My Nr Nx Ny Qe) Nt(Ii Ik Jo Ly My Ng Nm Ns Oh) Mw(Hu Mi Mr Mx My Ns Oh Oy Qe) Mi(Ik Il Ly Ne Ns Ny Pz) Mr(In Jl Jo Ly Ml Ns Qe) Mv(Ik Mx Ng Nm Ns Pz Wm) Jl(Jm Lw Nm Oe) Hw(In Jo Oh) Ir(In Jm Ml) Nx(Li Mx Ng) Lw(Mx Qe) My(Iv Ng) Il(Jm Oh) Ny(Li Oh) WmLy NsQe HuPc Hvlt Inlv} Nj{Fr(aA Fp Hq Hr Hu Hv Hw Hx Ih Ii Ij Ik Il Im In Io Iq Ir Is It Iu Iv Jg Jh Jj Jk Jl Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Is(aA Fp Hq Hr Hu Hv Hw Hx Ih Ii Ij Ik Il Im In Io Iq Ir It Iu Iv Jg Jh Jj Jk Jl Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Pg(aA Fp Hq Hr Hu Hv Hw Hx Ih Ii Ij Il Im In Io Iq Ir It Iu Iv Jg Jh Jj Jk Jl Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Po Pz Qb Qc Qd Qe Wm) Qa(aA Fp Hq Hr Hu Hv Hw Hx Ih Ii Ij Ik Il Im In Io Iq Ir It Iu Iv Jg Jh Jj Jk Jl Jm Jn Jo Jp Jq Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Po Pz Qb Qc Qd Qe) Jl(aA Fp Hq Hr Hu Hv Hw Hx Ih Ii Ij Ik Il Im In Io Iq Ir It Iu Iv Jg Jh Jj Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Pa Pb Pc Pd Pe Pf Po Pz Qb Qc Qd Qe) Mt(aA Fp Hq Hr Hu Hv Hw Hx Ih Ii Ij Ik Il Im In Io Iq Ir It Iu Iv Jg Jh Jj Jk Jm Jn Jo Jp Jq Js Jt Lh Li Lj Lu Lv Lw Lx Ly Lz Ma Mb Mc Md Me Mf Mg Mi Mj Mk Ml Mm Mn Mp Mq Mr Ms Mu Mv Mw Mx Mz Na Nb Nc Nd Ne Nf Ng Nh Ni Nk Nl Nm Nn No Nq Nr Ns Nt Nu Nv Nw Nx Ny Oe Of Og Oh Oi Ok Om Oz Pa Pb Pc Pd Pe Pf Po Pz Qb Qc Qd Qe Wm) aA(Fp Hq Hr Hu Hv Hw Hx Ih Ii Ij Il Im In Io Iq Ir It Iu Iv Jg Jh Jj Jk Jm Jn Jo Jp Jq Js Jt Lh Li Lj Lu Lv Lw Lx Ly Lz Ma Mc Md Mf Mg Mh Mi Mj Mk Ml Mm Mn Mp Mq Mr Ms Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Po Pz Qb Qc Qd Qe) Lx(Fp Hq Hr Hu Hv Hw Hx Ih Ii Ij Il Im In Io Iq Ir It Iu Iv Jg Jh Jk Jn Jo Jp Jq Js Jt Lh Li Lj Lu Lv Lw Ly Lz Ma Mc Md Me Mf Mg Mh Mi Mj Mk Ml Mm Mn Mp Mq Mr Ms Mu Mv Mw Mx My Mz Na Nb Nd Ne Nf Nh Ni Nk Nl Nm Nn No Nq Nr Ns Nt Nu Nv Nw Nx Ny Oe Of Og Oh Oi Ok Om Oy Oz Pa Pc Pd Pe Pf Po Pz Qb Qc Qd Qe) Ok(Fp Hq Hr Hu Hv Hx Ih Ii Ij Il Im Io Iq Ir It Iu Iv Jg Jh Jk Jm Jn Jo Jp Jq Js Jt Lh Li Lj Lu Lv Lw Ly Lz Ma Mc Md Me Mf Mg Mi Mj Mk Ml Mm Mn Mp Mq Mr Ms Mu Mv Mw Mx My Mz Na Nb Nd Ne Nf Ng Nh Ni Nk Nl Nm Nn No Nq Nr Ns Nt Nu Nv Nw Nx Ny Oe Of Og Oh Om Oy Oz Pa Pb Pc Pd Pe Pf Po Qb Qc Qd Qe) Pe(Fp Hq Hu Hv Hw Hx Ii Ij Il Im In Io Iq Ir It Iu Iv Jg Jh Jj Jk Jm Jn Jo Jp Jq Js Jt Lh Li Lu Lv Lw Ly Lz Ma Mc Md Me Mf Mg Mh Mi Mk Ml Mm Mn Mp Mq Mr Ms Mu Mv Mw Mx My Mz Na Nb Nd Ne Nf Ng Nh Ni Nk Nl Nm Nn No Nq Nr Ns Nt Nu Nv Nw Nx Oe Of Og Oh Oi Om Oy Oz Pa Pb Pd Pf Po Pz Qb Qc Qd Qe) Po(Fp Hq Hr Hu Hv Hw Hx Ih Ij Im Io Iq Ir It Iu Jg Jh Jk Jm Jn Jp Jq Jt Lh Li Lj Lu Lv Lw Ly Lz Ma Mc Me Mf Mg Mh Mi Mj Mk Ml Mm Mn Mp Mq Mr Ms Mu Mv Mw Mx My Mz Na Nb Ne Nf Nh Ni Nl Nm Nn No Nq Ns Nt Nu Nv Nw Nx Ny Oi Om Oy Pa Pb Pc Pf Pz Qb Qc Qd Qe) Nv(Fp Hq Hr Hu Hv Hw Ih Ii Ij Im In Io Iq Ir It Iu Iv Jg Jh Jj Jk Jn Jo Jp Jq Js Jt Lh Li Lj Lv Lw Ly Lz Ma Mc Md Me Mf Mg Mi Mj Mk Ml Mm Mn Mp Mq Ms Mu Mv Mw Mx My Mz Na Nd Ne Nf Nh Ni Nk Nl Nm Nn No Nq Nr Nt Nu Nw Ny Of Og Oh Om Oy Oz Pd Pf Qb Qd Qe Wm) Lv(Fp Hq Hr Hu Hv Hw Hx Ih Ii Ij Im Io Iq Ir Iv Jg Jh Jj Jk Jn Jp Jq Js Jt Lh Li Lj Lu Ly Lz Ma Mb Md Mh Mi Mj Mk Mm Mn Mp Mq Mr Ms Mu Mv Mw Mx My Mz Na Nb Nc Nd Nf Ng Nk Nl Nm Nn No Nq Nr Nt Nu Nw Nx Ny Og Oh Om Oy Pa Pb Pc Pd Pf Qb Qc Qd Qe) Jn(Fp Hu Hv Hw Hx Ii Ij Il Im In Io Iq Ir It Iu Iv Jg Jh Jk Jp Jq Lh Li Lj Lu Lw Ly Lz Ma Mc Md Mg Mi Mj Mk Ml Mm Mn Mp Mq Mr Ms Mu Mv Mw Mx My Mz Na Nb Nc Nd Ne Nf Nh Nl Nm Nn Nu Nw Nx Oe Of Og Oh Oi Om Oy Pa Pb Pc Qb Qc Qd Qe) Nn(Fp Hq Hr Hu Hv Hw Hx Ii Ij Ik Il Im In Iq Ir It Iu Jg Jk Jp Jq Lh Li Lj Lw Lz Ma Mc Md Me Mg Mi Mj Mk Ml Mn Mp Mq Mr Ms Mu Mv Mw Mx My Mz Nb Nd Ne Ng Nm No Nq Nr Ns Nt Nu Nw Nx Ny Of Og Oh Oi Om Oz Pa Pc Pf Qb Qc Qd Qe) Mu(Fp Hq Hr Hv Hw Hx Ih Ii Ij Il Im In Iq Ir Iu Iv Jg Jh Jk Jo Jp Jq Js Jt Lh Li Lj Lu Mb Md Mf Mg Mh Mi Mj Mm Mn Mp Mr Ms Mv Mw Mx Mz Nb Nd Ne Nf Ng Nh Nm No Nq Nr Ns Nt Nu Nw Nx Ny Oe Og Oh Oi Om Pa Pb Pf Qb Qd Qe) Nq(Fp Hq Hr Hu Hv Hw Hx Ih Ii Ij Ik Il Im In Io Iq Ir It Iu Jg Jk Jp Jq Jt Lh Li Lj Lw Ly Lz Mc Me Mf Mi Mj Mk Mn Mp Mq Mr Ms Mv Mw Mx My Mz Na Nb Nd Ne Ng Nm No Nr Ns Nu Nw Ny Og Oh Oi Om Oz Pa Pf Pz Qb Qd Qe) Lh(Hq Hu Hv Hw Hx Ij Il Im In Io Iq Ir It Iu Iv Jg Jh Jk Jo Jp Jq Lj Lu Lw Lz Ma Mc Mg Mh Mi Mj Mk Ml Mm Mn Mp Mq Mr Ms Mw Mz Na Nb Nd Ne Nh Ni Nl Nm No Nr Nw Nx Ny Og Oh Oi Om Pd Pf Pz Qb Qc Qd Qe) Mp(Fp Hq Hr Hu Hv Hw Hx Ii Ij Il Im In Iq Ir Jg Jk Jp Jq Jt Li Lu Lw Ma Mc Me Mf Mg Mi Mj Ml Mm Mr Ms Mv Mw Mx My Mz Nb Nd Ne Nm No Nr Ns Nw Nx Ny Og Oh Oi Om Pa Qb Qc Qd Qe) Jp(Fp Hq Hw Hx Ih Ii Ij Il Im In Io Ir Iu Iv Jg Jk Jo Jq Li Lw Ma Md Mg Mi Mj Mm Mq Mr Ms Mv Mw Mx My Mz Nb Nd Ne Nf No Nr Nt Nu Nw Nx Ny Oh Om Pa Pf Qb Qd Qe Wm) Qd(Hv Hw Hx Ii Ij Ik Im In Io It Iv Jh Jj Jk Jm Jq Jt Lu Ma Mb Mc Md Mh Mi Ml Mm Mq Mr Ms Mv Mw Mx My Mz Na Nb Nd Nf Ng No Nr Ns Nt Nw Nx Og Oh Oi Pa Pb Pz Qc) Qe(Hv Hw Hx Ii Ij Im In Io Iu Jg Jh Jj Jk Jq Jt Lu Mc Md Mi Mj Ml Mq Mr Ms Mw Mx Mz Na Nb Nd Nf No Nr Ns Nt Nw Ny Og Oh Oi Om Oz Pa Pb Pz Qc) Ir(Hu Hv Hw Hx Ii Ij Il Im In Io It Jg Jh Jj Jk Jm Jq Jt Li Lj Ma Mc Mi Mj Ml Mq Mr Ms Mw Mz Na Nb Nd Nf Ni Nr Nt Nw Og Oh Oi Om On Pa Pb Qc) Nw(Fp Hu Hv Hw Hx Ii Ij Il Im In Io Jg Jk Jq Lj Lu Ma Mg Mi Mj Mq Mr Ms Mv Mx My Mz Na Nb Nd Ne Nf Nh Ni No Nr Nt Nu Oe Oh Oi Pa Qb Wm) Jq(Fp Hq Hu Hv Hw Hx Ii Ij Il Im Iu Iv Jg Jk Jo Ma Mg Mi Mj Mm Mn Mr Ms Mv Mw Mx My Mz Nb Nd No Nr Nt Nu Ny Om Oy Pa Pf Qb) Mz(Fp Hq Hu Hv Hx Im Io Iq It Iv Jg Jk Li Ma Mg Mh Ml Mm Mn Ms Mv Mw My Nb Nm No Nt Nu Og Oh Om Oy Pf Qb Wm) Nb(Fp Hq Hu Hx Ij Il Im In Io Iq Jg Jh Jk Li Ma Mh Ml Mm Mn Ms Mw Mx Nm No Ns Ny Oh Om Pb Pf Qb Wm) Hx(Hu Il Im Io Jg Jh Jj Jk Li Lu Lw Ma Md Mg Mi Mm Mn Mr Ms Mv Mw Ni No Nt Nx Og Oh Om Pa) No(Fp Hq Ij Il Im Io Jg Jk Ma Mg Mm Mn Mv Mw My Nl Nu Nx Ny Om Oy Qb) Jk(Hw Im Io Iv Jj Jt Lu Lw Md Mi Mr Mx Na Nf Nt Og Oh Om Oy Pa) Mw(Hu Hv Ii Md Mi Mr Mx Nf Nr Ns Nt Ny Og Oh Oy Pa) Om(Hv Hw Il Io Lu Mi Mr Ms Mx Nd Nt Og Oi Pa Pb Qb) Nt(Im Io Jg Mm Mn Ms My Ne Og Pa Qb) Ma(Hw Ii Jg Lu Mi Mx Ny Pa) Mm(Hu Hw Ii Il In Ms Nr Pa) Mn(Hw Ii Md Mi Mr Nr Oh Pa) Mi(Im Jg Ms Ny Pf) Oh(Hu Il Iq Mv My) Pa(Im Jg Jh Mg Pf) Mx(Jg Mg Mv) Im(Jj Lu Mj) Pf(Mr Mv Nr) Ms(Jt Nr) Jg(Ny Og) NyPb} Lv{Jp(aA Fp Fr Hq Hr Hu Hv Hw Hx Ih Ii Ij Ik Il Im In Io Iq Ir Is It Iu Iv Jg Jh Jj Jk Jl Jm Jn Jo Jq Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Is(aA Fp Fr Hq Hr Hu Hv Hw Hx Ih Ii Ij Ik Il Im In Io Iq Ir It Iu Iv Jg Jh Jj Jk Jl Jm Jn Jo Jp Jq Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Mm(aA Fp Hq Hr Hu Hv Hw Hx Ih Ii Ij Ik Il Im In Io Iq Ir It Iu Iv Jg Jh Jj Jk Jl Jm Jn Jo Jq Js Jt Lh Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Jn(aA Fp Fr Hq Hr Hu Hv Hw Hx Ih Ii Ij Ik Il Im In Io Iq Ir It Iu Iv Jg

Figure 34 Continued

Jh Jj Jk Jm Jo Jq Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Jj(aA Fp Fr Hq Hr Hu Hv Hw Hx Ih Ii Ij Ik Il Im In Io Iq Ir It Iu Iv Jg Jh Jk Jl Jm Jo Jq Js Jt Lh Li Lj Lu Lw Lx Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oz Pa Pb Pc Pd Pe Pf Pg Po Pz Qa Qb Qc Qd Qe) Jq(aA Fp Fr Hq Hr Hu Hv Hw Hx Ih Ii Ij Ik Il Im In Io Iq Ir It Iu Iv Jg Jh Jk Jl Jm Jo Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Of Og Oh Oi Ok Om Oy Oz Pa Pb Pc Pd Pe Pf Pg Po Pz Qb Qc) Nw(aA Fp Fr Hq Hr Hu Hv Hw Hx Ii Ij Ik Il In Io Iq It Iu Iv Jh Jk Jl Jm Jo Js Lh Li Lj Lu Lw Lx Ly Lz Ma Mc Md Me Mf Mg Mh Mi Mj Mk Ml Mp Mq Mr Ms Mt Mu Mx Mz Na Nb Nc Nd Ne Nf Ng Nh Ni Nk Nl Nm Nn No Nq Nr Ns Nu Nv Nx Ny Oe Of Og Oh Oi Ok Om Oy Oz Pa Pb Pc Pd Pe Pf Po Pz Qb Qc) Fr(aA Fp Hq Hr Hu Hv Hw Hx Ii Ij Ik Il In Io Iq It Iu Iv Jg Jh Jl Jm Jo Js Lh Li Lu Lw Lx Ly Lz Ma Mb Mc Md Mf Mg Mh Mi Mj Mk Ml Mn Mp Mq Mr Mt Mu Mv Mw Mx My Mz Nb Nc Nd Ng Ni Nk Nl Nm Nn Nq Nr Ns Nu Nv Ny Of Og Oh Oi Ok Oy Oz Pa Pb Pc Pe Pf Pg Po Pz Qb Qc) Mt(aA Fp Hq Hr Hv Hw Hx Ih Ii Ij Ik Il In Io Iq It Iu Iv Jg Jh Jl Jm Jo Js Lh Li Lj Lw Lx Ly Lz Ma Mb Mc Md Me Mf Mg Mh Mi Mj Mk Ml Mn Mp Mq Mr Mu Mv Mx My Mz Na Nc Nd Nf Ng Ni Nk Nl Nm Nn Nr Ns Nu Nv Nx Ny Of Og Oh Oi Ok Om Oy Oz Pb Pc Pd Pe Pf Po Pz Qc) Mx(aA Fp Hr Hu Hv Hw Hx In Io Iq It Iu Jg Jh Jk Jm Lh Li Lj Lw Lx Ly Ma Mc Md Me Mf Mh Mi Mj Mk Ml Mn Mp Mq Mr Ms Mu Mz Na Nc Nd Ne Nf Ng Nh Ni Nl Nm Nn Nq Nr Ns Nx Ny Oe Of Og Oh Oi Ok Om Oy Oz Pa Pb Pc Pd Pe Pz Qb Qc) Lh(aA Fp Hq Hv Hx Ii Ik Im In Io Iq It Iv Jg Jh Jl Jm Jo Js Li Lw Lx Ly Lz Ma Mb Mc Me Mh Mi Mj Mk Ml Mp Mr Mu Mz Na Nb Nc Nd Ne Ng Ni Nk Nl Nm Nn No Nq Nr Ns Nu Nx Ny Of Og Oh Oi Ok Om Oy Oz Pa Pb Pc Pf Pz Qb Qc) Mu(aA Hq Hr Hu Hw Hx Ih Ii Ij Ik Il Im Io Ir Iu Iv Jg Jh Jl Jm Jo Js Lu Lw Ly Ma Mb Mc Md Me Mf Mg Mh Mi Mk Ml Mn Mp Mv Mw Nc Nd Ng Nk Nl Nm Nn Nr Nt Nu Nv Ny Og Oh Oi Ok Om Oy Oz Pa Pb Pc Pe Pg Pz Qb Qc) Ok(Hr Hu Hv Hw Hx Ih Ii Ik Il In Io It Iu Iv Jg Jh Jo Js Li Lj Lw Lx Lz Ma Mb Mc Me Mf Mg Mh Mi Mj Ml Mp Mq Mr Mz Nb Nc Nd Ng Nk Nl No Nq Nr Ns Nt Nu Nv Of Og Oh Oi Oz Pa Pb Pc Pf Pg Po Pz Qb Qc) Nn(aA Hr Hu Hw Hx Ih Ij Ik Il Im Io It Iu Iv Jg Jh Jm Jo Js Lu Lw Lx Ma Mb Mc Mf Mg Mh Mi Mj Ml Mn Mp Mq Mr My Na Nc Nd Ne Ng Nh Ni Nk Nl Nm Nr Ns Nt Nu Nv Nx Og Oh Oi Om Oy Pa Pb Pe Pf Pg Pz Qc) Oh(aA Hr Hw Hx Ik Il In Io It Iu Iv Jg Jh Jl Jo Js Li Lj Lw Lx Lz Ma Mb Mc Md Me Mf Mg Mh Mi Mj Ml Mp Mq Mr Na Nc Nd Nh Ni Nl Nm Nq Nr Ns Nu Nv Nx Of Og Om Oz Pa Pb Pc Pe Po Pz Qb Qc) aA(Hr Hu Hv Hx Ih Ij Im Io Ir Iu Iv Jg Jh Jk Jl Jo Li Lw Lx Ly Ma Mb Me Mf Mg Mh Mi Mk Ml Mn Mp Mq Mv My Nc Ni Nk Nl Nq Nr Ns Nt Nu Nx Ny Og Om Oz Pb Pc Pd Pe Pg Qa) Jl(Hu Hx Ii Im Io Iq It Iu Iv Jh Jm Jo Li Lu Lx Ly Ma Mc Mg Mi Mj Ml Mp Mr Ms Mz Nc Ng Ni Nk Nl No Nq Ns Nu Nx Of Og Oi Oy Pa Pb Pc Pg Po Pz Qb Qc) Lx(Hq Hr Hw Hx Ih Il Io It Iu Iv Jg Jh Jm Jo Js Ma Mb Me Ml Mn Mp Ms Nc Nd Ng Ni Nk Nl Nm Nr Nu Nv Nx Og Oi Om Oy Oz Pb Pc Pz) Og(Hr Hw Hx Ii Il Im Ir Iu Iv Jg Jh Jk Jo Ma Mb Mi Mn Mp Mq Mr Mw My Nb Nl No Nq Nr Nt Nu Nv Nx Om Pa Pc Pe Pg Po Qb) Mp(Hq Hr Hv Hx Ih Ik It Iv Jg Jh Jm Js Ly Lz Ma Md Me Mh Mi Mz Nc Nd Ng Nl No Nr Nu Nv Nx Om Oy Pb Pc Pe Qb) Hx(In Io Iv Jg Jh Jm Li Ly Ma Mh Mi Mr Ms Mz Nc Nf Ng Nk Nl No Nq Nu Nx Of Om Oy Pb Pc Pe Po) Pb(Fp Hv Ih Im Ir Iu Iv Jg Jh Js Li Lz Ma Mi Nh Nl No Nq Nt Nu Nv Ny Om Pa Pc Pe Pg Qa Qb) Ma(Hr Ik Io Iv Jh Lu Mb Mh Mi Mr Mz Nc Ng Nk Nl No Of Oi Pa Pc Pe Pz Qb) Jg(Hu Hv Io Iv Jm Lz Mf Mi Mj Mr Ms Mz Nc Nd Ng Nk Nl No Nu Oy Pa Pf) Om(Hr Ik Io Ir Iv Jh Lu Mb Mh Mi Nc Ng Nk Nl Nu Oi Pa Pz Qc) Jh(Hr Hu Ik Ir Iv Js Li Lz Mb Mi My Nc Ng Nl Nx Oy Qb) Iv(Ik Im In Io Ly Mb Ms Na Nc Ng No Ns Oi Po Qc) Po(Ii In Io Ly Mb Me Nl Nu Nx Oi Oy Qc) Io(Ir Js Mb Mi Mr Mz No Nv Pe Pg Qa) Nc(Im Js Li Ly Mi Mr Nu Nx Pc Pg) No(Ii Im Ly Mj Ml Nl Nu Nx Oi) Ns(Fp Hv Im Ir Js Mr Mz Qa) Nl(Fp Li Ly Mz Na Nq Qa Qb) Mr(Ii Ly Mb Ml Nu Oy Qc) Mi(Hq Jm Ly Mb Nu Oy) Im(Lu Mh Nk Pg Pz Qd) Pe(Ii Ly Mb Nu) Js(In Na Oi) Pg(Ii Jm Lu) Nq(Ng Nx) Mb(Li Nf) Me(Hv Qa) Mz(Ml Qc) LyPa JmNv LiNx} Jl{Io(aA Fp Fr Hq Hr Hu Hv Hw Hx Ih Ii Ij Ik Il Im In Iq Ir Is It Iu Iv Jg Jh Jj Jk Jm Jn Jo Jp Jq Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Pa Pb Pc Pd Pe Pf Pg Po Pz Qa Qb Qc Qd Qe) Pz(aA Fp Fr Hq Hr Hu Hv Hw Hx Ih Ii Ij Ik Il Im In Iq Ir Is It Iu Iv Jg Jh Jj Jk Jm Jn Jo Jp Jq Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Pa Pb Pc Pd Pe Pf Pg Po Qa Qb Qc Qd Qe) Og(aA Fp Fr Hq Hr Hu Hv Hw Hx Ih Ii Ij Ik Il Im In Iq Ir Is It Iu Iv Jg Jh Jj Jk Jm Jn Jo Jp Jq Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Oh Oi Ok Om Oy Pa Pb Pc Pd Pe Pf Pg Po Qa Qb Qc Qd Qe) Ii(aA Fp Fr Hq Hr Hu Hv Hw Hx Ih Ij Ik Il Im In Iq Ir Is It Iu Iv Jg Jh Jj Jk Jm Jn Jo Jp Jq Js Jt Lh Li Lj Lu Lw Lx Ly Lz Ma Mb Mc Md Me Mf Mg Mi Mj Mk Ml Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Oh Oi Ok Om Oy Pa Pb Pc Pd Pe Pf Pg Po Qa Qb Qc Qd Qe) Jj(aA Fp Hq Hr Hu Hv Hw Hx Ih Ij Ik Il Im In Iq Ir It Iu Iv Jg Jh Jk Jm Jo Jp Jq Js Jt Lh Li Lj Lu Lw Lx Ly Lz Ma Mb Mc Md Me Mf Mg Mi Mj Mk Ml Mn Mp Mq Mr Ms Mu Mv Mw Mx My Mz Na Nb Nc Nd Ne Nf Ng Nh Ni Nk Nl Nm Nn No Nq Nr Ns Nt Nu Nv Nw Nx Ny Oe Of Oh Oi Ok Om Oy Pa Pb Pc Pd Pe Pf Pg Po Qa Qb Qc Qd Qe) Of(aA Fp Fr Hq Hr Hu Hv Hw Hx Ih Ij Ik Il Im In Iq Ir It Iu Iv Jg Jh Jm Jo Jp Jq Js Jt Lh Li Lj Lu Lw Lx Ly Lz Ma Mb Mc Me Mf Mg Mi Mj Mk Ml Mm Mn Mp Mq Mr Ms Mt Mu Mv Mw Mx My Na Nc Nd Ne Ng Nh Ni Nk Nl Nm Nn No Nq Nr Ns Nt Nu Nw Nx Ny Oe Oh Oi Ok Oy Pa Pb Pc Pd Pe Pf Pg Qa Qb Qc Qd Qe) Lu(Fp Hq Hr Hu Hv Hw Hx Ih Ij Il Im In Iq It Iu Iv Jg Jh Jm Jo Jp Jq Js Lh Li Lj Lw Lx Ly Lz Ma Mb Mc Me Mf Mg Mi Mj Mk Ml Mm Mp Mq Mr Ms Mt Mu Mv Mx My Mz Na Nb Nc Nd Ng Nh Ni Nk Nl Nm Nn Nq Nr Ns Nt Nu Nv Nw Nx Ny Oe Oh Oi Ok Om Oy Pa Pb Pc Pd Pe Pf Pg Qa Qb Qc) Oi(aA Hq Hr Hu Hv Hw Hx Ij Il Im In Iq It Iu Iv Jg Jh Jm Jn Jo Jp Jq Js Jt Lh Li Lj Lw Lx Ly Lz Ma Mb Me Mf Mg Mh Mi Mj Mk Ml Mm Mp Mq Mr Ms Mu Mv Mw Mx My Mz Nb Nc Nd Nf Ng Ni Nk Nl Nm Nn No Nq Nr Ns Nt Nu Nv Nw Nx Oe Oh Ok Om Oy Pb Pc Pd Pe Pg Po Qa Qb Qc Qd) Mp(aA Fp Hq Hr Hu Hv Hw Hx Ih Ij Ik Il Im In Iq It Iu Iv Jh Jk Jm Jo Jp Jq Js Lh Li Lj Lw Ly Lz Ma Mb Mc Me Mg Mi Mj Mk Ml Mm Mq Mr Ms Mt Mw Mx My Mz Na Nb Nc Nd Nf Ng Ni Nn Nq Nr Ns Nu Nv Nw Nx Ny Oe Oh Oy Pa Pb Pc Pd Pe Pf Pg Po Qb Qc) Ms(aA Fp Fr Hu Hv Hx Ij Im In Iq Is It Iu Iv Jg Jh Jm Jn Jo Jp Jq Lh Li Lj Lw Lx Ly Lz Ma Mc Me Mf Mg Mh Mi Mj Mk Ml Mm Mq Mt Mu Mv Mw Mx My Na Nc Ni Nk Nl Nm Nn Nq Ns Nt Nu Nw Nx Oe Oh Ok Om Oy Pb Pc Pd Pe Pg Qa Qc) Nn(Fp Hq Hr Hu Hv Hw Ih Ij Ik Il In Iq It Iu Jk Jm Jo Js Lh Li Lw Lx Ly Ma Mc Me Mf Mi Mj Mk Ml Mm Mn Mq Mr Mu Mv Mw Mx My Mz Na Nb Nc Nd Ne Nf Ng Nh Ni Nk Nl Nq Nr Ns Nu Nv Nx Oe Oh Ok Oy Pa Pd Pe Po Qc) Iv(Fp Hq Hu Hv Ih Ij Ik Il Im In Iq It Iu Jh Jm Jo Js Lh Li Lw Lx Ly Lz Ma Mc Me Mf Mg Mi Mj Mk Ml Mu Mw Na Nb Ng Ni Nk Nq Nr Ns Nu Nx Oe Oh Oy Pb Pd Pe Pf Pg Qa Qc) Jo(Hv Hw Ij Ik In Ir Iu Jg Jh Jm Jp Jq Jt Lh Lw Lx Ma Mb Md Mf Mg Mi Ml Mm Mn Mr Mu Mv My Mz Na Nb Nd Nf Ng Ni Nm No Nq Nt Nu Nx Oe Ok Om Pb Pe Pg Po Qa) Nq(aA Hq Hu Hw Hx Ij Ik Il Im In Iq Iu Jh Jm Jq Lx Ly Lz Mb Mc Mf Mg Mi Mj Ml Mm My Nb Nc Nd Ng Nk Nl Nr Ns Nu Nv Nx Ny Oy Pa Pb Pd Pf Pg Po Qc) Im(Hq Hu Hv Hx Ij Iq It Iu Jg Jh Jm Jp Jq Lh Li Lw Ly Ma Mg Mk Ml Mt Mw Mx Nb Nc Nd Ng Nk Nl Ns Nu Nv Nw Nx Oe Oh Oy Pb Pc Pd Pe Pg Qc Qd) Mg(Hq Hu Ij Ik Il Iq It Iu Jh Jm Jp Jq Lh Li Lx Ly Lz Mb Mc Mj Mk Mm Mq Mt Mx My Nc Ng Nk Nl Nm Ns Nu Nw Nx Oy Pa Pb Pe Pg Qc) Jh(Hq Hu Hx Ij Ik Il In Iq Iu Jm Jp Jq Lh Li Lj Ly Mc

Figure 34 Continued

Mf Mj Mk Ml Mn My Nc Ng Nk Nl Ns Nu Nx Ny Oy Pa Pc Pe Pf Pg Qb Qc) Jp(Hu Ij Il In Iq Iu Jk Jm Jq Lh Li Lw Lx Ma Mi Mj Ml Mu Mx Nb Ng Ni Nk Nl Ns Nt Nu Nx Oe Oy Pa Pb Pd Pe Pg Qc Wm) Jm(Fr Hx Il Iq Ir Is Iu Jn Jq Lh Li Lw Lx Ma Mi Ml Mm Mt Mu Mx My Nc Nd Nk Nl Ns Nu Oe Pa Pb Pc Pe Pg Qc) Iu(aA Hw Hx Il In Jq Lh Li Lw Lx Ma Mf Mi Mx Nb Nc Nk Nl Nm Ns Nt Nu Oe Oy Pa Pb Pd Pe Pg Po Qa) Jq(Iq Is It Jn Jt Lh Li Lj Ma Mj Ml Mu My Nk Nl Nm Ns Nt Nu Oe Pb Pg Qc) Mm(Fr Lh Li Lw Lx Ma Mr Mt Ne Ng Nm No Nr Nt Nw Nx Oe Oh Ok Pc Po Qc) Pb(Hu Ij In Lh Li Ma Mf Mq Mt Mu Mw Mx Ng Ni Nm Ns Nt Nu Oe Pd Pe Pg) Ml(Hv Ij In Jg Li Ma Mt Mu Mx Mz Nf Ni Ns Nu Nw Oe Ok Pg Qa) Ma(aA Hx Ik Iq Is Lh Mb My Nc Ng Nk Nl Ns Nu Oy Pg Qc) Mu(Ik Iq Lh Mb Mj Mk My Ng Nk Nl Nv Nx Oe Oy Pe Pg Qc) Jn(Fr Ij Jt Lh Lx Mr Mz Ne Nf Nm No Oe Oh Ok) Pg(Ik Iq Jg Lh Ly Mj Ng Ni Nv Nx Ok Om Oy Qc) Is(Fr Ij Js Lh Lx Mi Mz Nm Oe Oh Ok Qb) Mt(Hx Lh Lx My Ng No Ny Oe Ok Oy Qc) Iq(Hx Ir Jg Lh Li Ly Mi Qa) Mj(Lh Li Mx Nu Oe Pe) Ik(Hu Ni Nt Pe Qd) Nm(Jt Lw Ok Om) aA(Jt Ns Oe Oh) Ly(Nl Oe Pa) Nd(Lh Lx Mi) Qc(Mz Oh Om) Mv(My Oy) Ng(Fr Oe) Ni(Nk Nl) It(Hv Hw) Jt(Lw Ok) MxOy} Pg{Mm(aA Fp Fr Hq Hr Hu Hv Hw Hx Ih Ii Ij Ik Il Im In Io Iq Ir Is It Iu Iv Jg Jh Jj Jk Jm Jn Jo Jp Jq Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Po Pz Qa Qb Qc Qd Qe Wm) Jj(aA Fp Fr Hq Hr Hu Hv Hw Hx Ih Ii Ij Ik Il Im In Io Iq Ir Is It Iu Iv Jg Jh Jk Jm Jn Jo Jp Jq Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Po Pz Qa Qb Qc Qd Qe Wm) Is(aA Fp Fr Hq Hr Hu Hv Hw Hx Ih Ii Ij Ik Il Im In Io Iq Ir It Iu Iv Jg Jh Jk Jm Jn Jo Jp Jq Js Jt Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Po Pz Qa Qb Qc Qd Qe) Ii(aA Fp Fr Hq Hr Hu Hv Hw Hx Ih Ij Ik Il Im In Io Iq Ir It Iu Iv Jg Jh Jk Jm Jn Jo Jp Jq Js Jt Lh Li Lj Lu Lw Lx Ly Lz Ma Mb Mc Md Me Mf Mg Mi Mj Mk Ml Mn Mp Mq Mr Mt Mu Mv Mw Mx Mz Na Nb Nc Nd Ne Nf Nh Ni Nk Nl Nm Nn No Nq Nr Ns Nt Nu Nv Nw Nx Ny Oe Oh Oi Ok Om Oz Pa Pb Pc Pd Pe Pf Po Pz Qa Qb Qc Qd Qe Wm) Jn(aA Fp Fr Hr Hu Hv Hw Hx Ih Ij Ik Il Im In Io Iq Ir Iu Iv Jg Jh Jk Jm Jo Jp Jq Js Lh Li Lj Lu Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nn Nq Nr Ns Nt Nu Nv Nw Nx Ny Oe Og Oh Oi Ok Om Oy Oz Pa Pb Pc Pd Pe Pf Po Pz Qa Qb Qc Qe) aA(Fp Fr Hq Hr Hu Hv Hw Hx Ih Ij Ik Il Im In Io Iq Ir It Iu Iv Jg Jh Jk Jm Jo Jp Jq Js Jt Lh Li Lj Lu Lw Lx Ly Lz Ma Mb Mc Md Me Mf Mg Mh Mi Mj Mk Ml Mp Mq Mr Ms Mt Mu Mv Mw Mx My Mz Na Nb Nc Nd Nf Ng Ni Nk Nm Nn No Nq Nr Ns Nt Nu Nv Nw Nx Ny Of Og Oh Oi Ok Om Oy Oz Pa Pb Pc Pd Pe Pf Pz Qa Qb Qc Qd) Im(Fp Fr Hq Hr Hu Hv Hw Hx Ij Ik Il In Io Iq Ir It Iu Iv Jg Jh Jm Jo Jp Jq Js Lh Li Lj Lu Lw Lx Ly Lz Ma Mb Mc Md Me Mf Mg Mh Mj Mk Ml Mn Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Of Og Oh Oi Ok Om Oy Oz Pa Pb Pc Pd Pe Pf Po Pz Qa Qb Qc Qd) Mu(Fp Fr Hq Hr Hu Hv Hw Hx Ij Ik Il In Io Iq Ir It Iu Iv Jg Jh Jk Jm Jo Jp Jq Js Lh Li Lu Lw Lx Ly Lz Ma Mb Mc Md Me Mf Mg Mh Mi Mj Mk Ml Mn Mp Mq Mr Ms Mt Mv Mw Mx My Mz Na Nb Nc Nd Ne Nf Ng Nh Ni Nk Nl Nm No Nq Nr Ns Nu Nv Nw Nx Ny Of Og Oh Oi Ok Om Oy Oz Pa Pb Pc Pd Pe Pf Po Pz Qa Qb Qc) Io(Fp Fr Hq Hr Hu Hv Hw Hx Ih Ij Il In Ir It Iu Iv Jg Jh Jm Jo Jp Jq Js Jt Lh Li Lu Lw Lx Ly Lz Ma Mb Mc Md Me Mf Mg Mh Mi Mj Mk Ml Mn Mp Mq Mr Ms Mt Mv Mx My Mz Na Nb Nc Nd Ne Nf Ng Nh Ni Nk Nl Nm Nn No Nq Nr Ns Nt Nu Nv Ny Oe Of Og Oh Oi Ok Om Oy Oz Pa Pb Pc Pd Pe Pf Pz Qa Qb Qc) Jp(Fp Fr Hq Hr Hu Hv Hw Hx Ij Il In Iq It Iu Iv Jg Jh Jm Jo Jq Js Lh Li Lu Lw Lx Ly Lz Ma Mb Mc Me Mf Mg Mh Mi Mj Mk Ml Mn Mp Mq Mr Ms Mt Mv Mw Mx My Mz Nb Nc Nd Nf Ng Ni Nk Nl Nm Nn No Nq Nr Ns Nt Nu Nv Nw Nx Ny Of Og Oh Oi Ok Om Oy Oz Pa Pb Pc Pd Pe Pf Po Pz Qa Qb Qc Wm) Pb(Fp Fr Hq Hr Hu Hv Hw Hx Ij Il In Ir It Iu Iv Jg Jh Jk Jm Jo Jq Js Jt Lh Li Lu Lw Lx Ly Ma Mc Md Mf Mg Mh Mi Mj Ml Mp Mq Mr Ms Mt Mv Mw Mx My Mz Na Nb Nc Nd Ne Nf Ng Ni Nk Nl Nm Nn No Nq Nr Ns Nt Nu Nv Nw Ny Oe Of Og Oh Oi Ok Om Oy Oz Pa Pc Pd Pe Pf Po Pz Qa Qb Qc Qd) Fr(Fp Hq Hr Hu Hv Hw Hx Ih Ij Ik Il In Iq It Iu Iv Jg Jh Jm Jo Jq Js Li Lu Lw Lx Ly Lz Ma Mb Mc Md Mf Mg Mh Mi Mj Mk Ml Mm Mq Mr Ms Mt Mv Mw Mx My Mz Nb Nc Nd Ne Nf Ng Ni Nk Nl Nm Nn Nq Nr Ns Nu Nv Nw Nx Ny Of Og Oh Oi Ok Om Oy Pa Pc Pd Pe Pf Po Pz Qa Qb Qc) Mt(Fp Hu Hx Ih Ik Il In Iq Ir It Jh Jm Jq Js Lh Li Lu Lx Ly Mb Mc Mh Mi Mp Mr Ms Mx My Mz Nb Nd Ne Nf Nh Nk Nn No Nr Ns Nv Nw Nx Ny Oe Og Oh Oi Ok Oy Oz Pa Pc Pe Pf Po Pz Qb Qc) Og(Hq Hr Hu Hv Hw Hx It Iv Jg Jh Jm Jo Jq Lh Li Lu Lw Lx Ly Ma Mb Mc Me Mg Mh Mi Mp Mq Mr Ms Mw Na Ne Nf Nk Nl Nm Nn Nq Nu Nv Nw Nx Ny Of Oh Ok Om Oz Pa Pe Po Pz Qc) Ok(Hv Hx Ij Ik In Iq It Iv Jg Jh Jm Jo Jq Jt Li Lj Lu Lx Ly Ma Mb Mi Mj Ml Mp Ms Na Nb Nc Ng Nk Nm Nn Nq Nu Nw Nx Oi Om Pf Pz Qc) Jh(Hu Hx In Iv Jm Jq Lh Lu Lx Ly Mb Mi Mp Mr Mx My Na Ng Nl Nn Nq Ns Nw Oh Oi Om Oy Oz Pf Pz Qc) Jo(Hv Hw Ij Ir Iu Jg Jq Jt Lh Lw Mb Mg Mq Mr Mz Na Nb Nf Ni Nm Nt Om Pe Qa Wm) Pz(Hx In Iv Jg Jm Jq Lh Li Lu Ly Ma Mg Mi Mp Nn Nq Ns Nu Nw Oh Om Oy Oz) Nn(Hu Hx Ik Jm Jq Li Lu Mb Mg Mx Na Ng Nw Nx Oh Oi Oy Pf) Om(Hu Ik In Jm Lu Ly Mb Mg Ms Mx Ng Ns Nw Nx Oi Oy Pf Qc) Jq(Hv In It Iv Jg Jt Lu Lx Ma Ms Nm Nq Nu Nx Oi Pf Qc) Jm(Hx Jg Lu Lx Mh Mi Mp Ms Mx Nk Nq Nu Nw Oi Oz Qc) Lu(Hu Ly Mp My Nq Nw Oy Oz Pc Pf) Jg(In Mg Ms Mx My Ng Oi Oy) Pf(Lh Ma Nf Nq Nw Oy Pc Wm) Mp(Hq Ly Na Ng Oi Oy Pd) Ma(Ik Mb Mg Ng Nw Oi) Oi(Iv Lh Nq Nu Nw) Wm(Ik Ly Of) Nq(Hu Mx Ng) In(Lh Mi Mx) Nw(Ms Nx Qc) Mg(Ik Ng) Iv(Ik Oz) LxHq MwOy MzQc} Mt{Jn(aA Fp Fr Hq Hr Hu Hv Hw Hx Ih Ii Ij Ik Il Im In Io Iq Ir Is It Iu Iv Jg Jh Jj Jk Jm Jp Jq Js Lh Li Lj Lw Lx Ly Lz Ma Mb Mc Me Mf Mg Mh Mi Mj Mk Ml Mm Mn Mp Mq Mr Ms Mu Mv Mw Mx Mz Na Nb Nc Nd Ne Nf Ng Nh Ni Nk Nl Nm Nn Nq Nr Ns Nu Nv Nw Nx Ny Oe Of Og Oh Oi Ok Om Oz Pa Pc Pd Pe Pf Po Pz Qa Qb Qc Qe) Io(aA Fr Hq Hr Hu Hv Hx Ii Ij Ik Il In Ir Is It Iu Iv Jg Jh Jj Jk Jm Jo Jp Jq Lh Li Lj Lw Lx Lz Mb Mc Me Mf Mg Mi Mj Mk Mm Mn Mp Mq Mr Ms Mu Mv Mw Mx Mz Na Nb Nc Nd Ne Ng Nh Nk Nl Nm Nn No Nq Nr Ns Nt Nu Nv Nw Nx Oe Og Oh Oi Ok Om Oy Oz Pa Pc Pd Pe Po Pz Qa Qb Qc Qe) Hx(Fp Fr Hq Hr Hu Hv Hx Il In Iq It Jg Jh Jj Jm Jp Jq Js Li Lj Lu Lw Lx Ly Ma Mc Md Me Mf Mg Mi Mj Mk Mm Mn Mp Mq Ms Mu Mv Mw Mx Mz Na Nb Nc Nd Ne Nf Ng Nh Ni Nk Nl Nm Nn Nq Nu Nw Nx Oe Og Oh Oi Ok Oy Oz Pc Pd Pf Po Pz Qb Qc) Qc(Fr Hq Hr Hu Hv Hw Ii Ij Ik Il In Is It Jg Jh Jm Jp Jq Lh Li Lj Lw Lx Ly Ma Mc Me Mf Mg Mi Mj Mk Mn Mp Mq Mr Ms Mu Mw Mz Nb Nc Nd Nf Ng Ni Nk Nl Nm Nn Nq Nr Ns Nu Nv Nx Ny Of Oh Oi Om Oy Oz Pa Pb Pc Pe Po Pz Qb) Ms(aA Fr Hr Hu Hv Hw Ii Ik Il Is Iu Iv Jg Jk Jm Jo Jp Jt Lh Li Lj Lu Lw Lx Ly Lz Mb Mc Mf Mg Mi Mj Mk Mm Mn Mp Mq Mr Mu Mv Mw Mx Mz Nb Nc Nk Nl Nn Nq Ns Nt Nu Nv Nw Nx Ok Om Oz Pa Pc Pe Po Qa Qe) Oi(Fr Hq Hr Hu Hv Hw Ik Ir Iv Jg Jh Jk Jm Jo Jp Jq Lh Li Lw Lx Ly Lz Mb Mc Me Mf Mg Mi Mj Mk Mm Mn Mp Mq Mu Mv Mw Na Nb Nc Ng Nk Nl Nn Nq Ns Nt Nu Nv Nw Nx Oe Og Ok Om Oy Oz Pa Pc Pd Po Pz Qa Qe) Nl(Fr Hu Hv Hw Ii Ij Ik Il In It Jh Jq Li Lj Lw Lx Ma Mc Mf Mh Mj Mk Mn Mp Mq Mu Mw Nb Nc Nd Nk Nm Nn Nq Nr Ns Nv Nx Of Oh Ok Oy Oz Pa Pb Pc Pe Po Qa) Lh(Fp Fr Hq Hu Ij Ik Im In Iq Is It Iu Jh Jj Jm Jp Jq Li Lj Lu Lw Lx Lz Ma Mb Me Mh Mj Mk Ml Mp Mu Nb Ng Nm Nn Nq Nw Nx Ny Og Oy Pb Pc Pf Pz) Ik(Fr Hr Hu Hv Hw Il In Is Iu Jg Jh Jm Jo Jq Li Lj Lw Lx Ma Mc Mg Mi Mp Mq Mu Mx Ng Nk Nm Nn Nq Nv Nx Oe Of Ok Pa Pb Pc Qa Qd Wm) Jq(Hq Hu Hv Hw Il Iq Is It Jh Jk Lj Lw Lx Mb Me Mg Mi Mn Mp Mu Mw Nb Nd Nk Nm Nn Nq Ns Nu Nv Og Oy Pa Pc Pe Po Qb) Is(Fr Hr Hv Ij Il Iu Jg Jj Jm Jp Lx Ly Mb Mi Mr Mz Nb Ne Nh Nn Nv Nw Nx Oe Og Oh Ok Om Oz Pa Pc Pe Po Pz) Nu(Hr Hu Hv Hw Ij Il In It Lj Lw Lx Mc Mi Mk Mp Mr Mu Nb Nd Ng Ni Nn Nq Ns Nv Nx Ny Of Pa Pb Pc Po) Jm(Hr Hu Hv Ij Il In Jh Li Lj Mc Mj Mk Mp Mq Mu Mw Nb Ng Nk Nn Nq Nx Of Oh Oy Oz Pa Pe Po) Nx(Hu Hw Ii Il It Jh Jj Lx Mh Mi Mk Ml Mp Mu Nd Ne Ng Nn Nq Ns Ny Of Oy Pa Pb Pc

Dc(Ax cJ Cx cY dB) Dd(Ax bF cD cJ dB) bA(aU Bo cK Db) bG(bR cD cU dK) dH(aJ aP cK) cD(Ex Gl) DbcJ FwdK aVcF} Mm{Hu(Hx Ik In Lu Ms Mz Ng Nx Oi Pa Pe) Oi(Hx Mz Nb Nv Nx Ny Ok Pa Pe Po) Ms(Hx Ii Mw Nb Nv Nx Pa Pe Po) Pe{Ik Iu Li Lu Pz) Nv(Mg Mh Ng Wm) Wm(Nw Om) Lu(Hx Nx) MpNw PzJk QaJt} Mu{Hx(Hu Ii Jh Lu Mh Ms Ng Nu Nx Oi Oy Pz) Qc(Mi Mj Nb Ny Oh) Nx(Ii Lu Ng Nk Pa) Nl(Ii Mp Nb Nv) Ny(Hq Mk Ml My) Wm(Ik Ns) Nu(Ij Nd) Mk(Pa Pe) Mp(Mx Nd) Nv(Ng Nk) MxIt} Nq{Hx(Ii Jh Lu Ms My Ng Oi Oy) Nl(Hw Ii Ij In Mj Ne Nr) Ng(Mb Mw Ns Nx Ny Qb) Mx(Ms Oi Oy) Mb(In Mz) Mk(Ij Pe) Jm(In Qb) Nw(Ms Oi) MzQc OiOk} cU{cK(al aL aM bA bU bV cD cF dD) Dc(Ax cJ cM cN Cq dB dI dK) aJ(bR bU cD dH) bE(Ad aM cZ) An(cJ cM) aMdI aPdH bAdE bGdK cXfR} Mp{Nx(Hq Hx Lu Mg Ms Mz Nb Ng Oi Pa) Ik(Ij Il Mj Mz Ny) Nl(Mj Ne Nr Ny) Nd(Mj Ny) Ok(Nk Oi) MsHr MzQc JkOy} Wm{Ly(Mz Nb No Nv Nw Nx Ny Om) Ns(Mw Mz Nb No Nw Ny Qd) Ik(Jg Jh Nv Om Qd) Ii(No Nv Ny) MwOy NvOf} mF{nR(kE kK mU mW nI oP oQ) oP(kG nB nI oO) oQ(kG mW nB oO) mP(kC mU nT) kC(mI mT) nNmU} dK{Ex(Aw bB BG bU bZ cD cJ De) Gl(bB BG cD cJ) bG(aX bC cR Dc) FwbB aPdH} Mw{Oy(Ik Il Jh Jk Mi Mx Nl Ns Pa Pc Pd) Hu(Mx Nl Oh) NsNl NuLw LuMy} cD{Cq(aX bZ dE dI) Ex(cJ Cx) aJ(bG dH) aP(bG dH) bH(aO dF) AwdI DdaX cXfR} Nw{Hx(Il Ma Ms Oi) Qa(Nm Pz Qc) Jk(Ms Ng Oy) Oi(Mg My) MaMb JoJt} Dc{Ax(aX bC bH dI Gl) cJ(aX bH cH Cx) CqCx bHdB} Ng{Jk(Jg Ma Mg Om) Nv(Jh Mg Om) MaHx HqJh} dH{aP(aO bB bF bU bZ cE cJ) aJ(bF bU)} Qa{Ns(Ik In It Lw Ml) NlIt IiNv} Po{Lj(Mk Ml Oh) Nl(Ma Mh) MlOy} dI{Aw(bU cJ) Cq(Ax bU) BnCx aMbF} Dd{bF(aX cE cJ) AxbZ} jD{jP(hA hW lK) hWjG} An{aO(aX cJ) aXcJ} Ex{AwBo AxCo bUcI} Pe{MaMb MlOh IiNx} bA{bJ(aI Bg) bEbG} Hu{LwMx JkOm} Hx{MsJg OiOm} Jh{LyPa JkOy} Ok{MgOi MlIj} DbbVcJ MaMbMz IkQdNx bUcXfR nTlXkG nBoOoQ hVhWjR

Unconstrained panels with 3 analytes, where 4.0E-8 >= 'AUC p-value' > 1.0E-8. Contains 12,268 panels of 645,860 total panels evaluated. : Et{Qe(Fp Fr Hq Hr Hv Hw Ih Ii Ij Ik Im In Iq Ir It Iu Jg Jm Jp Jq Js Lh Li Lj Lw Lx Ly Lz Ma Mb Mc Md Me Mf Mi Mj Mk Mn Mp Mq Mr Mt Mu Mw Mx My Mz Nb Nc Nd Nf Ni Nl Nq Nr Nt Nu Nv Nw Nx Ny Oh Om Oy Oz Pd Pe Pf Po Qb Qc Qd) Mu(aA Fp Hq Hr Hu Hv Ih Ik Im Iq Ir It Iu Jh Jk Jm Jp Jq Js Lh Li Lj Lw Lx Ma Mb Mc Md Me Mf Mi Mj Mk Mn Mp Mq Mr Mt Mv Mw My Mz Nb Nc Nd Nf Nl Nn Nq Nr Ns Nt Nu Nv Nw Nx Ny Oh Om Oy Pc Pd Pf Po Qd) Lh(aA Fp Fr Hq Hr Hu Hv Hw Ij Ik Im Iq Ir It Jg Jh Jp Jq Js Li Lj Lw Lx Lz Ma Mc Md Me Mf Mh Mi Mk Mn Mp Mq Mr Mt Mv Mw Mx Mz Nd Nl Nq Nr Ns Nt Nu Nv Nw Nx Ny Oh Ok Om Oy Oz Pd Pf Po Qc Qd) Lx(aA Fp Fr Hu Hv Hw Ih Ii Ij Ik Im Iq Ir It Iu Jg Jh Jq Js Lj Lw Lz Ma Mc Me Mf Mi Mj Mk Ml Mn Mp Mq Mt Mv Mw Mx Mz Nb Nc Nd Nl Nq Nr Ns Nt Nu Nv Nw Nx Ny Oh Oy Pc Pd Po Qc Qd Wm) Jh(aA Fp Fr Hq Hr Hv Hw Ih Ii Ij Ik Im Iq It Iu Jg Jj Jm Jo Jq Li Lj Lw Ly Lz Ma Mc Me Mf Mi Mj Mk Mn Mq Mr Mt Mw Nb Nd Nf Ni Nq Nr Ns Nt Nu Nv Nx Oh Ok Oz Pc Pd Pf Po Qc Qd Wm) Jp(aA Fp Fr Hq Hr Hv Ii Im Iq Ir Iu Jg Jm Jo Jq Js Li Lj Lz Ma Mb Mc Md Me Mf Mg Mj Mk Ml Mn Mq Mr Mt Mv Mw Mx My Nb Nf Ni Nl No Nr Nv Nw Nx Ny Oh Ok Om Oy Pd Po Qc Qd) Nq(Fp Fr Hq Hr Hu Hv Ih Ii Ik Ir Iu Jg Jm Js Li Lw Ma Mc Md Mf Mj Mk Ml Mn Mp Mq Mr Mt Mw Nb Nd Nf Nl Nn Nr Nt Nu Nv Nw Nx Ny Oh Om Oy Oz Pc Pd Pf Po Qc Qd Wm) Hw(aA Fr Hq Hr Hv Ih Ij Ik In Ir It Jg Jm Jq Li Lj Ly Ma Mc Me Mj Mk Mn Mp Mq Mt Mw Mx My Mz Nb Nc Nd Nr Ns Nt Nu Nv Nw Ny Oh Ok Om Oy Oz Pd Pf Po Qb Qc Qd) Mp(Fp Fr Hq Hv Ih Ii Ik Ir Iu Jg Jm Js Li Lj Lw Ma Mc Mj Mk Ml Mn Mq Mt Mw Mx My Nb Nl Nn Nr Ns Nt Nu Nv Nw Nx Ny Oh Ok Oy Oz Pc Pd Pf Po Qc Qd Wm) Mz(aA Fp Fr Ih Ii Ij Ik Iq Ir It Iu Jg Jm Jq Li Ma Mc Md Me Mf Mg Mi Mj Mk Mn Mq Mr Mv Mw Nb Nf Nl Nr Nt Nu Nv Nw Nx Ny Oh Ok Om Oy Oz Pd Po Qa Qd) Nc(Fp Hq Hr Ih Ii Ij Im Iq Ir It Iu Jg Jm Jo Jq Js Li Lj Lw Lz Mc Md Me Mg Mi Mj Mk Mn Mr Mv Mx Nb Nd Nf Nr Nt Nv Nw Nx Ny Oh Ok Om Oy Pf Po Qd Wm) My(Fp Fr Hq Hu Hv Ih Ii Ij Ik Im Ir It Jm Li Lj Ly Ma Mc Me Mj Mk Ml Mn Mq Mt Mv Mx Nb Nd No Nr Ns Nt Nu Nv Nx Ny Oh Ok Oy Oz Pd Pf Po Qc Qd Wm) Iv(aA Fp Hq Hr Hv Ii Im Iq It Iu Jg Jm Jo Js Jt Li Lj Lz Ma Mb Mc Md Me Mf Mi Mj Mk Mn Mq Mr Mv Na Nb Nf Ni Nl No Nt Nu Nw Nx Ny Oh Ok Oy Pd Pf) Nn(Fp Fr Hq Hr Hu Hv Ih Ik Im Iq It Iu Jm Jo Js Jt Lj Lw Lz Ma Mc Md Me Mf Mi Mj Mk Mn Mq Mr Mv Mw Nb Nf Ni Nl Nt Nw Nx Ny Ok Om Oy Oz Pf) Po(aA Fp Fr Hq Hr Hu Ih Ii Ij Ik Ir Jg Jq Js Lw Lz Ma Mc Me Mf Mh Mi Mj Mk Mq Mw Mx Nb Nd Nl Ns Nt Nu Nv Nw Nx Ny Oy Oz Pd Qc Qd) Ir(aA Fp Fr Hr Hv Ih Ii Ij Ik Im Iq It Iu Jq Li Lw Ma Mb Mc Me Mf Mn Mq Mt Mw Mx Nd Nr Nt Nu Nv Nx Ny Om Oy Oz Pc Pd Qb Qc Qd) Ly(aA Fp Hv Ii Im Iq It Jg Jm Js Li Lj Mc Me Mf Mg Mj Mk Ml Mn Mq Mt Mv Mw Nb Ni Nr Ns Nu Nv Nw Nx Ny Ok Om Oy Pd Pf Qc Qd) Jq(aA Fp Fr Ii Ij Im Iq It Iu Jg Jm Js Li Lj Lw Ma Md Me Mf Mg Mi Mj Ml Mn Mr Mv Mw Mx Nb Nd Ng Ni Nl Nr Ns Nt Nu Nv Pc Qd) Qd(Fp Hq Hr Ih Ii Ij Iq It Jg Jm Li Lj Lw Lz Ma Mb Mc Mf Mj Mn Mt Mw Mx Nd Ng Nr Ns Nu Nv Nx Ny Oh Om Oz Pc Pe Pf Qc) Pb(aA Fp Hq Hr Ih Ik Im It Iu Jg Jm Jo Js Jt Lj Mc Md Me Mf Mg Mj Mk Ml Mn Mt Mv Na Nd Nf Ng Ni No Nw Ny Oh Ok Oz Qc) Mx(aA Fp Hv Ih Ii Ik Jg Jm Li Lj Mc Me Mf Mg Mj Mk Mn Mq Mt Mw Nb Nd Ni Ns Nt Nu Nv Nw Nx Ny Ok Om Oy Pd Pf Qc) Lw(Fp Ih Ii Ik Im Iu Jg Jm Li Ma Mc Me Mf Mi Ml Mn Mt Mv Mw Nb Nd Nr Ns Nt Nu Nv Nw Nx Ny Oh Ok Pc Pd Qc) Qb(Fp Hr Hv Ii Im Iq It Iu Ji Jo Jt Lj Lz Mb Md Me Mf Mg Mj Mk Mr Mv Na Nf Ni Nl No Nr Nt Nv Nw Nx Ok Om) Ml(Fp Fr Ih Ii Jg Js Li Lj Ma Md Mi Mj Mn Mr Mt Mv Mw Nb Nd Nf Ng Ns Nu Nv Nw Nx Ny Oh Ok Om Oz Pc Pd) Pc(Fp Fr Hv Ih Ii Ik It Iu Jm Ma Mc Md Mi Mk Mn Mq Mt Mw Nb Nd Ng Nl Nr Ns Nt Nu Nv Nw Ny Pd Pf Qc) Ij(Fp Fr Hr Ih It Iu Jg Li Ma Mb Mc Md Me Mf Mi Mn Mt Mw Nb Ni No Nt Nu Nv Nw Nx Ny Oh Ok Pd Pf) Wm(aA Hr Ih Il In Io Jg Ji Jk Jm Lv Ma Mh Mk Mn Nb Nh Nk Nl No Nr Nv Ny Oh Om On Oz Pd Pe Qc) Nu(aA Fp Fr Ik It Jg Jm Lj Ma Mc Mj Mn Mt Mw Nb Nd Nr Ns Nv Nw Ny Oh Ok Oy Oz Pd Qc) Ng(aA Fp Hq Hr Hv Ih Ik Im It Jg Jm Js Lj Mc Md Me Mq Nf No Nw Nx Ny Oh Ok Om Qc) Ns(Fp Fr Ih Ii Im Jg Jm Li Lj Ma Mc Mi Mj Mn Mt Nb Nr Nt Nv Nw Oh Om Pd Qc) Nd(aA Fr Ih Ik Jg Li Ma Mc Mj Mk Mn Mq Mt Mw Nb Nr Nv Nw Ny Oh Om Oy Oz Pd) Nv(Hq Hu Ii Ik In Jg Jk Li Ma Mc Mk Mt Mw Nb Nr Nw Ny Oh Oy Oz Pd Qc) Lu(Hr Hv Im Iq Iu Jm Jo Jt Lz Mb Md Mv Na Nb Nf Ni Nl No Nr Ok Om) aA(Ih Ik Im It Jg Jj Jm Li Lj Mc Me Mf Mg Mj Mk Mn Mv Mw Nx Qc) Mh(Hr Ih Iq Iu Jo Js Jt Mb Mi Mv Na Nf Nr Nt Ny Oh Ok Om Pf) Mt(Fp Fr Hu Hx Ih Ii Jg Jm Lj Ma Mc Mj Mn Mw Nr Nt Nx Ny Pd) Fr(Fp Hu Ih Iu Jg Jj Jk Li Mb Mc Mf Nb Nl Nr Oz Pa Qc) Mw(Ih Ii Ik It Jg Lj Ma Mc Mj Mk Mn Nb Nr Nw Ny Pd Qc) Ny(Fp Ik It Jg Jm Lj Ma Mc Mj Mn Nb Oh Oy Oz Pd Qc) Oe(Hq Im Iq Js Jt Lz Mv Na Nf Ni No Ok Om Oy Pf) Oz(Ii It Jg Li Ma Mc Mj Nb No Nr Nt Nw Pd Qc) Ma(Fp Ii Ik Jg Jm Mc Mi Nb Nr Nw Pd Qc) Nm(Hq Hr Iq Lz Mb Me Mq Na Ni Nl Oy) In(Hq Im Iq Iu Lz Mb Md Mi Mv Nl Nw) Nt(Ii Iu Jg Jk Me Mk Mn Ne Nw Qc) Nh(Hq Ik Iq Jo Jt Lj Mk Mq Na Oy) Ih(Fp Ik Jg Mg Mj Mn Nr Pd Qc) Hx(Jt Lz Mb Mr Na Nf Ni No) Qc(Jg Li Mi Nb Nr Nw Oh Om) Hu(Ii Js Jt Lz Na Nb Ni) No(Hv Ii Ji Jk Pa Pe) Nr(Hr Hv Jg Nb Nw Pd) Ne(Iq Jt Mb Mq Na Oy) Pa(Mb Md Mr Nf Pf) Mg(Hq Hr It Ni) Jg(Ii Mc Mj Pd) Jj(Hq Jt Oy Pf) Jk(Md Mi Mr Nf) Fp(Ik Nw Pd) Ms(Hq Iq Pf) Na(Ji Jo Qa) Oy(Ii Mj Mv) Nb(Hr Mk) Hv(Mj Om) Io(Hq Iq) Ji(Mb Ni) Pd(Mn Nw) MiIu MrIi JoJt OgPf OhPe} Jl{Ma(Fp Hq Hr Hu Hv Hw Ih Ij Il In Ir It Jg Jh Jk Js Li Lj Lw Lx Ly Lz Mc Me Mf Mg Mi Mj Mk Mn Mq Mr Mt Mu Mv Mw Mx Mz Na Nb Nd Ne Nf Nh Ni Nm No Nq Nr Nt Nv Nw Nx Ny Oe Oh Ok Om Pa Pc Pd Pe Pf Po Qa Qb Qe) Mu(aA Fp Hq Hr Hu Hv Hw Hx Ih Ij Il Im In It Iu Jg Jh Jk Js Jt Li Lj Lw Lx Ly Lz Mc Md Me Mf Mg Mi Mn Mp Mq Mr Mv Mw Mx Mz Na Nb Nc Nd Ne Nf Nh Ni Nm Nq Nr Ns Nu Nw Ny Oh Om Pa Pc Pd Pf Po Qa Qb Qe) Nu(aA Hq Hu Hv Hw Hx Ij Il In Iq Ir It Jg Js Lh Li Lj Lw Lx Ly Lz Mb Mc Mf Mi Mk Mq Mr Mw Mx My Na Nb Nc Nd Ng Ni Nk Nl Nm No Nr Ns Nw Nx Ny Oe Oh Ok Om Oy Pa Pc Pd Pe Pf Pg Qa Qc Qe) Pg(Fp Hq Hr Hu Hv Hw Hx Ih Ij Il In Ir It Jk Js Jt Li Lj Lw Lx Lz Mb Mc Me Mf Mi Mk Mn Mq Mr Mt Mv Mx My Mz Na Nb Nc Nd Nf Nk Nl Nm No Nr Ns Nt Nw Ny Oh Pa Pc Pd Pe Pf Po Qa Qb Qe) Iq(aA Fp Hq Hu Hv Hw Ih Ij Il In Iu Jk Jo Js Jt Lj Lw Lx Lz Mc Mf Mj Mk Ml Mq Mr Mx My Mz Na Nb Nc Nd Nf Nk Nl Nm No Nr Ns Nt Nv Nw Nx

Figure 34 Continued

Ly Mg Mh Mj Ml My Nu Oh Oz Pc Pd) Og(Fp Hq Hr Ih In Lw Mb Ms Na Nc Nf Nm Ns Oh Oz Pd Pf Qb) Ma(Ih Iq It Iu Jo Js Me Mf Mg Mk Ml Na Ni Oe Oz) Mr(Ii Il Iv Jm Lw Mh My Mz Ne Nu Oh Oz Pf Po) Ms(Ih Ij Il Io Iu Jo Li Lz Mh Na Nk Ns Oh) Nj(Hq Ij Iu Js Me Mg Mk Oe Oy Oz Pc Pd Qb) Hx(Hw Ih Ii Iu Js Jt Lz Mj Mk Nl Nr Qb) My(Hw Ik Lw Md Mh Mj Na Nr Oh Pb Pz) Il(Io Iv Jt Li Lw Md Mj Na Nf Pb Pc) Mi(Fp Hu Hv Jm Lw Mg Nu Oh Pf Po) Nn(It Iv Md Mg Nc Nk Nm Oe Pd) Nq(Iu Js Jt Lj Nc Nl Nm Pb Pd) Jg(Hr Js Jt Md Mh Nc Of Qb Wm) Oh(Hu Ii Ij In Io Mj Na Nr Ns) Nv(Hr Ih Iu Jo Jt Lz Nl Wm) Po(Hr Hw Iu Jo Md Nf Nk) Mz(Hr Lz Md Nc Nk Of Pz) Nw(Jo Lw Lz Md Nr Pc) Ik(Hw Ij Li Mj Wm) Oi(Ih Lz Mj Nr Pf) Io(Ih Ii Ij Nu) Jq(Hr Jo Nc Pz) Nr(In Ml Oz) Hw(It Ly Ml) Qa(Jo Jt Oe) Jk(Fp Hr Oe) Li(Ij Mj Qb) Pb(Hv Jo Na) Wm(Mu Pg) Jt(Lh Nm) NsPf NuMd MjMl IhLh ItJj] Pg{Pz(Hq Hu Hv Hw Ij Il It Iu Jo Js Lv Lw Lx Mc Md Mh Mj Mk Ml Mq Mr Ms Mv Mx My Mz Na Nb Nc Nd Ne Nf Nh Ni Nk Nl Nm No Nr Nt Nx Ny Of Oi Pa Pc Pe Qa Qb Qc) Jh(Fp Hq Hr Hv Hw Ij Il Iq Ir It Jg Jo Js Li Lv Lw Lz Ma Mc Md Me Mh Mj Mk Ml Mn Mq Mw Mz Nb Nc Nd Ne Nf Nh Ni Nk No Nr Nu Nv Nx Ny Of Pa Pc Pd Pe Po Qb) Lu(Hq Hv Hw Hx Ij Il In It Jg Lh Li Lw Lx Ma Mc Md Me Mg Mh Mi Mk Ml Mq Mr Mz Na Nc Nd Ne Nf Ng Nk Nl Ns Nu Nx Ny Oe Of Oh Oi Pa Pd Pe Qc) Ok(Fp Hq Hu Hw Il Iu Jk Js Lh Lw Lz Mc Md Me Mf Mg Mh Mk Mn Mq Mr Mx My Nd Nf Ni Nl No Nr Ns Nt Nv Ny Of Oh Oy Oz Pa Pc Pe Po Qa Qb) Oz(Fr Hr Hu Hx In It Jq Lh Li Lv Lx Ly Ma Mc Mi Ml Mp Mr Ms My Nb Nc Ne Ng Nk Nl Nn Nq Ns Nu Nw Nx Ny Of Oh Oi Oy Pa Pc Qb Qc) Jm(Hq Hu Hw Ij Il In Iv Jq Lh Lw Ly Ma Mb Mc Me Mg Mk Mr My Na Nb Nc Nd Nf Ng Nl No Ns Nv Ny Oe Of Oh Oy Pa Pc Pe Qa Qb Wm) Og(Fp Ii Ij Il In Ir Iu Js Jt Lj Lz Md Mf Mj Mk Ml Mn Mv Mx My Mz Nc Nd Ng Nh Ni No Nr Ns Nt Oe Oi Oy Pc Pd Pf Qa Qb) Om(Fp Hx Il It Iv Jg Lh Li Lv Lx Ma Mc Md Mh Mi Mk Ml Mn Mr Mv Mw My Na Nd Nl Nn Nq Nu Nv Ny Of Oh Pa Pc Pd Po Qb) Nw(Hq Hu Hv Hw Ij Il In Iv Jq Lh Li Lj Lv Lx Ly Lz Mb Mc Mg Mi Mk Na Ni Nk Nl Nq Ns Nu Nv Pe) Nn(Hq Hr Iq Iv Lh Lx Ly Lz Mc Mf Mh Mk Mn Mp Ms Mu My Nc Nk Nl No Ns Nu Pc Pe Qb Qc Wm) Lv(Hr Hx In Iv Lh Lx Ly Mh Mp Mx Mz Na Ng Nk Nl No Nx Of Oh Oi Oy Pf Qb Qc) Jq(Hu Ik Iq Js Mb Md Mg Mh Mi Mj Ml Mx Na Ni Nt Oy) In(Hw Hx Iv Lx Ly Mr Mz Na Nf No Nt Nu Pe Po Qa) Pf(Hv Hw Iv Jg Ly Mg Mv Nb Ng Ni Nm No Nt Of Qa) Oi(Hx Li Lx Ly Mg Mi Mr Ms Mz No Oh Oy Pc Qa) Oy(Hx Iv Lh Lx Ma Mh Mi Mv Nq Nu Of Po) Pb(Ih Iq Lj Lz Mb Me Mk Mn Nh Nx Qe) Jp(Ih Ik Ir Lj Md Mz Ne Nh Oe Qe) Fr(Ir Jk Lj Me Na Nh No Oe) Ly(Hx Iv Lx Mi Mr Mx Nq Nu) Io(Ik Iq Lj Mw Nv Po Qe) Jg(Hu Hx Ik Mb Ns Nx Qc) Mp(Hx Im Mh Mk Ns Nu) Mu(Ih Jt Lj Nt Oe Qe) aA(Mn Ne Nl Po Qe) Na(It Lx Ma Nq) Ng(Hx Iv Mw Nu) Ik(Mi Nj Qa Qd) Im(Ih Jt Mi Qe) Ms(Iv Mh Of) Jn(Jt No Qd) Nq(Mg Mh) Mv(My On) Iv(Ns Qc) Lh(Mj Nx) WmIu MaHx MxPc HqOf} Fr{Mx(Fp Hq Hv Ih Ij Il In Ir It Iv Jg Js Lw Lx Mc Md Mi Mp Mq Mr Mu Mv Mw Nb Nd Nn Nr Ns Nv Ny Of Oh Ok Om Pa Pc Pd Pe Pf Qb) Mh(aA Hq Hr Hu Hv Hw Ij It Iu Jj Jo Li Lj Lu Lw Lz Ma Mc Mf Mj Mm Mp Mv Mw My Nd Ne Nh Nn Nq Nu Nv Nx Ny Of Oh Pd Pf) Hx(Hq Il Ir Iv Jg Jm Lh Ly Lz Ma Mb Mc Md Mf Mj Mk Mn Mp Mv Mw Nd Ne Nh Nn Ns Nu Nv Nw Nx Oe Oh Oz Pa Pc Pd Pf Po Qb) Mb(aA Hu Im In Ir It Iv Lh Li Lx Ly Ma Mf Mn Mp Ms My Nd Ne Nl Nn Nq Ns Nv Nx Of Oh Pa Pb Qc Wm) Nl(Fp Hr Hu Ih Ik Iq Ir It Iu Jh Ma Mc Md Mr Mu Mv Mw Na Nc Nf Nq Ns Nu Nv Ny Oh Oz Pf Qb) Lh(Fp Hq Ii Ij In Jh Jq Lz Ma Mc Md Mf Ml Mn Mp Ms Mv Nb Nd Ne Nn Nu Nw Nx Ny Pc Pe Qb) Mg(Hr Hv Jh Li Lx Ma Md Mj Mm Mr Mu Nb Nd Nf Nm Nn Nq Nv Oe Oh Pc Pd Po Qa) Nk(Fp Iq Ir It Iv Jg Li Lj Ly Md Me Mu Mw Na Nc Nf Nm No Nq Nt Oe Oy Pc) aA(Hr Hu Ij In Iv Jj Jo Jp Jq Lu Ma Ml Mm Nn Nu Nw Nx Of Pd Pe Pz Qb) Ng(Ih Ii Im Io Ir Jj Lx Md Mr Mu Mv Nd Nf Nn No Nq Om Oz Pc Po Qa) Nc(Hu Hw Jh Jm Jq Ly Mf Ml Mn Ms Mz Nu Nw Nx Oy Pa Qc Wm) Nu(Hq Ij In Io Jq Lu Mk Mm Mn Nq Ns Nx Of Pa Pd Qc) Jp(Hr Hw Ij Ik Ir Iv Lu Mp Ne Nh Nx Pa Pe Qa Qb Qc) Pb(Hr Hw In Io Ir Iv Jh Jj Lu Mm Nr Nw Of Om Pe Pz) Jq(Ik Im Io Ly Ml Mp Ms Nb Ne Nf Ni Of Pa Pe Qb) Lv(Ih Jk Me Ms Na Nf No Nt Nx Oe Om Pd Qa) Qb(Hu Iq Jh Jm Li Lu Ml Mm Ms My Nw Oy Qc) Jj(Hr Hw Io Lu Ly Ml Mn Nv Om Pd Pz Qc Qd) Oi(Fp Im Iq Jk Jt Me Na Ne Ns Oe Ok Qe) Og(Fp Jk Jt Me Mn Ms Nh Ni No Oy Qe) dB(Ad As bA bU cJ Cp cT Cu Cw Dc dK) Io(Hw Ii Ij In Jh Jo Ms Ny Pa Qa) Qc(Hu Ij Iv Js Lu Nw Nx Pa Pe Qa) Nq(Hw Ii Jh Lw Mp Mu Nd Nr) Ir(Ii Ik Iu Iv Jh Li Lx Ml) cD(An bA bE bH bI Bo cB cE) cJ(aL Ap aU bJ Bo cU cV dJ) In(Ik Jm Lu Ml Ni Nw Of) Pz(Ih Il It Jo Mw Nx Pa) On(Jt Mv Mw Ns Nt Qd) Ax(Ad bA Cu Cw Fw) Li(Iv Mp Mz Nr Nw) Oy(Hu Il Jk Ns Pa) Pe(Iq Lu Mk Mr Nd) bU(cY Dg dI dK dN) Mm(Jk Mn Mw Ok) Ij(Lu Ml Mv Mw) dK(bG Bo cT cY) dN(bE bJ Cx dG) Ms(Jo Nb Nx) Mz(Lj Ml Nb) Ik(Jo Nx Qa) Db(Ap Dg) Wm(Jn Nh) Hw(Iq Nb) Ii(Pa Qa) Of(Im Jk) bA(Bo dH) NmQa NrMl NxPa aKcT bFcE bIcY} Lv{Om(Hq Hu Hv Hw Ii Ij Il Im It Jg Jm Js Li Lw Ly Mc Md Me Mf Mj Mk Ml Mn Mq Mr Ms My Mz Nb Nd Ne Nf No Nq Nr Ns Nx Ny Of Ok Oy Oz Pc Pd Pe Pf Po Qb) Hx(Fp Hq Hv Hw Ih Ik Im Iq It Js Lj Lw Lz Mb Mc Md Me Mf Mj Mk Ml Mn Mq Na Nd Ne Nh Ni Nm Nr Ns Nv Ny Oi Oz Pa Pz Qa Qb Qc) aA(Fp Hq Hw Ii Ik Il In Iq Jm Js Jt Lj Lu Lz Mc Md Mj Mr Mw Mz Na Nb Nd Nf Nm No Nv Oe Of Oi Ok Pa Pf Po Pz Qb Qc Qd Qe) Ma(Hq Hv Hw Ih Im In Ir Jg Jm Js Li Lj Lz Mf Mj Ms Nb Nd Nf Nq Ns Nu Nv Nx Ny Oy Po Qa Qc) Mp(Hw Il Iu Jo Li Lj Lu Lw Mb Mc Mj Mk Ml Mn Mr Ne Nf Ni Nk Nm Ns Ny Oi Oz Pa Pd Po Qa) Jh(Fp Hv Ih Im Io Jg Lj Mf Mh Mj Mn Mr Ms Mz Na Nf Nk No Ny Oi Pa Pc Pe Po Qa) Nc(Fp Hv Ih Io Lj Lz Mn My Mz Na Nb Nf Nl No Nq Nv Ny Og Oz Pa Pb Pe Po Qb) Lx(Fp Hu Hv Ii Ij In Li Lu Lw Ly Lz Mc Mg Mh Mk Mu Ny Of Pe Qa Qb) Iv(Hr Jm Li Me Mh Mi Ml Mr Mx Mz Nd Ne Nk Nl Nq Nu Of Pa Pc Pe Pz) Mu(Fp Hv In Jk Li Lz Mj Mq Mr Ms My Mz Na Nf Ni No Oe Of Pd Pf) Ok(Fp Ij Im Iq Jk Jt Ly Md Mk Ms Mv My Na Ne Ng Nh Nx Ny Oe) Nn(Fp Hv Ii In Iq Li Lz Md Mk No Nq Ny Of Oz Po Qa Qb Wm) Lh(Hr Hw Ij Il Iu Lj Lu Md Mf Mn Mq Nf Nh Nv Pd Qe) Jg(Hw Ii Js Lj Lw Mn Mq Nr Ns Of Oi Oz Pz) Im(Ik Io Ir Mb Mi Mz Nl Nw Nx Of Oh Pa) Nu(Hr Hv Li Ly Lz Mx Nd Ng Nl Nv Pa) No(Hv Ih Iq Ir Jm Lj Me Ni Nk Qc) Nj(Ik Iu Jo Lw Mc Mf Ml Nh Oe Oz) Oh(Hv Ih Ii Mv My Nf Ng Nt Ny Oi) Mr(Hq In Jm Me Ng Nl Nx Oi Pb) Og(Fp Hv Ih Nm Ny Oi Pd Qa Qe) Po(Il Jo Js Mx Ng Nr Pb Pz) Nx(Hv In Ly Mi Mz Na Nk Qa) Nw(Ih Mb Mn My Nt Qa Wm) Pb(Hr Jk Jt Mj Mq Mz Nm) Nl(Io Jm Js Mi Ng Oz) Qb(Io Jm Li Ly Mh Nq) Mx(Ii Il Lz Mv Nv) Jq(Lu Oe Qa Qd Qe) Ns(Ih Lj Nf Qd) Ly(Jj Nd Nt Nv) Mb(Ir Js Mh Nv) Oi(Ih Ir Li Pe) Mz(Lj Mh Wm) Mi(Me Ng) Na(Ih Nv) Ik(Li Qd) Io(Mn Ny) Qc(Lz Nv) Js(Ml Nk) Oy(Jj Pa) Pe(In Of) WmPc MhNi HqPf PzQa} Jn{Jh(Fp Hq Hr Hv Ii Ij Ik Iq Ir It Iu Iv Lj Lz Mb Mc Mg Mi Mj Mr My Na Ne Nf Ng Nh Nl Nr Ns Nx Ny Oe Oi Qb Qe) Jg(Fp Hq Hr Hw Ij Ik It Iu Jj Jq Js Li Ly Ma Mc Me Mj Mn Mr Mz Nh Nk Nl Nn Ns Nw Nx Ny Oh Ok Qa Qb Qe) Jk(Hu Hv Hx Il It Iv Lj Lu Lw Lx Mc Me Mg Mh Mi Mj Mk Mq Mx My Na Ne Nl Nm Ns Nu Nv Nx Oh Oz Pc Pz Qb) Jp(aA Hw Ii Ik In Iq It Iu Iv Jj Lj Lu Mb Me Mh Mq Mr Mv My Nb Ne Ng Nh Nk Nl Ns Nt Nw Nx Oe Ok Om) Ok(Hv Hw Hx Io It Iu Li Lj Lw Mg Mi Mx Nd Ne Nk Nl Nv Nw Of Oi Om Pc Pe Qa Qb) Po(Hx In Jj Jm Lj Lw Lx Ly Lz Me Mk Mn Ms Mx My Ng Nv Nw Oh Oi Pc Qc) Ma(Hr Ij Il It Iv Li Lj Lu Mn Mr Mz Ne No Nr Ns Nu Nx Ny Oi Qa Qb) Ml(Hw Hx Ii Il Im Io Iu Li Lu Lw Mg Mj Mn Mv Mx Mz Nr Nu Og Pc Qa) Nw(Hx Ih Im Js Lu Mg Mh Mx My Nd Ne Nh Ns Nv Oe Og Om Pa Pb Pz Qe) Lx(Ik Ir Jm Jo Lu Ly Mi Mj Mk Mr Mv Nb Nc Ng Nh Of Pe Pz Qb Qe) Nj(Hq Hr Ih Ik Jj Jo Jt Me Mf Mh Ng Ni Nk Ny Oz Pd Pf Pz Wm) Io(Ii Il Im Iv Jj Jo Li Lw Lz Me Mr Ms Nd Nr Nu Nx Pb Pe Qe) Nv(Hr In Li Lw Ly Me Mg Mn Mz Ne Ng Ns Nu Nx Of Oy Pb Pc Qa) Om(aA Hw Il Im It Jj Mg Mi Nb Nd Ne Nh Nn Ns Pe Pz Qa Qe) Lw(Hv Hw Hx Im Lh Lu Mi Mx My Nu Oi Pa Pe Qa) Jj(aA Hq Ij Lu Mi Mn Ms Nd Nt Nx Ny Og Pe Qd) Im(Hx Il Li Mg Mn Mw My Nk Nx Ny Og Qa Qc) Lh(aA In Iu Jq Me Mh Ms Ne Oi Pb Pc) Og(aA Hw Il Mi Mn Nt Pc Qa Qe Wm) Mw(aA Hw Iq Li Mh Nq Ny Pz Wm) Pc(Hu Hx Il Lu Mx Pa Pe Qc) Pb(aA Hw Il Iu Nb Nt Pe) Mg(aA Ii Jq Mx Ng Qc) Nt(Ii Jo Mb Mp Oi) Nn(Iv Mv Oe Qd) Qa(Ik In Js Lj) Nq(Jo Oe Qb) Mp(Jt Mv No) Ms(Mn My Nx) Mu(Jt No Oe) Mz(Li Ns Qc) Pa(In It Ly) Hx(In Jq) Ii(Hw Pe) Li(Lj Oi) WmOf NsMi NuOi LuMe MmNa IlJm JsaA} Nj{Nw(Hq Hr Ih Iu Iv Jh Jj Jm Jo Js Li Lw Mc Md Me Mf Mh Mm Mn Mw Nm Ns Nx Of Og Om Pc Pd Pz Qc) Qd(Fp Hu Iq Ir Iu Jg Js Li Lw Ly Me Mg Mj Mk Ne Nh Ni Nl Nm Nu Ny Of Om Qb Qe) Ir(Fp Iu Lu Lw Ly Md Me Mf Mg Mh Mm Mv

Figure 34 Continued

Im Iu Jg Mg Mi Mm Mn Mv My Nb Nd Nj Nt Nu Ny Pa Pe Pf Qa Qb Qe) Ny(Hv Hw Ik Io Jg Lw Mc Ml Mm Mn Mq Mv Mx My Mz Nd Ne Nu Of Oh Ok Pc Pz Qa) Mp(aA Hx Ir Jm Lu Lw Mn Ms Mx My Mz Nr Nu Nv Of Oh Oi Ok Qa Qe) Mu(Hr Hv Ii Ir Iu Jk Mj Ml Mn Ms Mx Nc Nk Nr Pb Pe Pf Qa Qe) Nv(Fp Hu Hx Iv Jg Ma Mb Mm Mx My Na Ng Nq Ns Oi Oy Pf Qa) Nq(Hw Ij Il Io Ir Jm Mx Ng Nl Nr Nu Og Pa Pe Pf Qe) Ok(Hu Ih Im Io Ir Iv Jk Ml Mx Og Pa Pb Pe Po Qa Qe) Pg(Ih Ik Iq Ir Jk Jt Lj Mb Mn Mv Nt Po Qd Qe Wm) Mm(In Io Ir Jk Ms Mz Nj Nx Oi Pa Po Qa Qb Qd) Qa(aA Hx In It Jg Lu Ma Ml Nx Og Oi) jI(hX iB jE jF jH jK jM jT lK lM lN) Jg(aA Hx Io Ir Lu Ms Mx Nj Pe Qe) Po(Fp Hq Hx Jj Lj Ma Nl Nr Oh) Ma(Ir Iv Mx Nj Pa Pe Qb Qe) cU(aA aJ An bA cM Dc dK dN) Ef(aK Ax bA cP cT cY dN) Mt(Ih Jl Jo Js Jt No Wm) Nx(aA Hx lm Ms Og Pe) Ji(Jo Nc Nk Pd Wm) Pf(Hr Io Mx Nb Ng) aA(cJ Mf Mg Mv My) cS(bG Bo cK Cq Dd) Nj(lm Mn My Nt) Jj(Hx lm Ir Qd) Pe(In Io Mn Oh) Is(Jl Md No) Dk(bE cJ) Im(Jk Qe) Og(Jk Qe) bF(Dd dN) jD(hW iB) AnaX Awdl CqdN DcdB WmOn HxPb aPdH bGdK nRmF nCkG hRjH Unconstrained panels with 2 analytes, where 1.0E-4 >= 'AUC p-value' > 1.0E-5. Contains 1,520 panels of 16,788 total panels evaluated. : Nv(aA Hq Hr Hv Hw Ih Ii Ij Ik Il In Iq Ir It Iu Jk Jm Jo Js Jt Li Lj Lu Lw Ly Lz Mc Md Me Mf Mg Mh Mi Mj Mk Ml Mn Mq Mr Ms Mv Mw Mz Nb Nc Nd Ne Nf Nh Ni Nk Nl Nm No Nr Nt Nu Nx Ny Oe Of Oh Ok Oz Pa Pb Pc Pd Pe Po Pz Qb Qc Qd Qe Wm) Qa(Hq Hr Hu Hv Hw Ih Ii Ij Ik Il Im Iq Ir Iu Iv Jk Jm Jo Js Jt Li Lj Lu Lw Ly Lz Mb Mc Md Me Mf Mg Mh Mi Mj Mk Mn Mq Mr Ms Mv Mw Mx Mz Na Nb Nc Nd Ne Nf Ng Ni Nk Nm No Nq Nr Nt Nu Of Oh Oz Pa Pc Pe Pf Po Pz Qb Qc Qe) Po(aA Hr Hu Hv Hw Ih Ii Ij Ik Il Im In Io Ir It Iu Jg Jk Jm Js Lu Lw Lx Ly Lz Mb Mc Md Mg Mh Mi Mj Mk Ml Mn Mp Mq Mr Ms Mu Mx My Mz Na Nc Nd Ni Nk Nm Nn Nq Nt Nu Nx Oe Oi Oz Pa Pb Pc Pd Pe Pf Pz Qb Qc Qe) Ok(Fp Hq Hr Hv Hw Ii In It Iu Jg Jj Jm Jo Jq Js Li Lj Lw Ly Ma Mb Mc Me Mg Mh Mi Mk Mm Mn Mq Mr Ms Mu Mw My My Mz Nb Nc Nd Ne Nh Ni Nk Nl Nn Nq Nt Nu Nx Oe Of Oh Oi Oz Pd Pf Pz Qc Qd) Om(Hq Hr Hu Ih Ii In Iq It Iu Jg Jj Jm Js Jt Li Lj Lu Lw Ly Lz Ma Mc Md Me Mf Mg Mh Mj Mk Ml Mq Mr Mu Mv Mw My Na Nc Nf Ng Ni Nm No Nr Nt Ny Oe Of Oh Oy Oz Pc Pd Pz Wm) Qe(aA Hq Hr Hv Hw Hx Ik Io Iq Ir Iv Jk Jm Li Lj Lw Mb Mc Mg Mh Mi Mj Ml Mn Mr Ms Mw Mx My Mz Na Nb Nd Ne Ni Nk Nl Nm No Ns Nt Nx Ny Oh Oi Oy Pa Pb Pc Pe Pf Pz Qb Qc) Nw(aA Hv Ih Ii Ik Iq It Iu Jg Jm Js Jt Li Lj Lw Ly Lz Mb Mc Md Me Mf Mi Mj Mk Ml Mq Mr Na Nc Nd Ne Nf Ng Nh Nk Nl Nm No Nr Ns Nt Nu Ny Of Oh Oy Oz Pb Pc Pd Pf Pz Wm) Lh(Hq Hr Hu Hv Hw Hx Ii Il Iq Ir It Iu Iv Js Lj Lx Ly Lz Mc Md Me Mf Mg Mi Mj Ml Mq Mr Ms Mx My Nb Nd Nf Ng Nh Ni Nk Nl Nm Nr Ns Nt Nu Nx Ny Oy Pa Pc Pd Qd Wm) Pf(Hq Hv Hw Hx Ii Ij Ik Il In Iq Ir It Iu Jg Jk Jm Jp Lj Lv Lw Ly Lz Mc Md Me Mg Mi Mj Ml Mm Mn Mq Mr Mv My Nd Ne Nl Nm Nr Ns Nu Nx Of Og Oh Oy Pa Pc Pe Pz) Jk(aA Fp Hx Ik Io Ir Iv Jg Jm Js Li Lu Lv Lw Ly Ma Mb Mh Mi Mn Mp Ms Mw Mx Mz Na Nb Nc Ng Ni Nn No Nq Ns Nx Ny Of Oh Oi Oy Oz Pa Pb Pc Pd Pe Pz Qb) Jp(Fp Hq Hr Hu Hv Ih Ik Iq It Jh Jj Jm Js Jt Lj Lu Ly Lz Mb Mc Md Me Mf Mh Mk Ml Mn Mr Mw Na Nc Ne Nf Ng Nh Ni Nk Nm Ns Oe Of Oh Oi Oy Oz Pb Pz Qc) Jg(Fp Hr Hv Hw Ii Ij Ik Il Im In Iu Jj Li Lw Lx Ma Md Mi Mj Ml Mm Mn Mp Mr Mu Mw Mz Nb Nd Nf Ni Nl Nn Nq Nr Nt Nx Oh Oi Pa Pb Pd Pz Qb Qd) Mu(Fp Hq Ih Ik Im In Io Iq It Iv Jj Jm Jo Js Lu Lw Lz Ma Mc Md Me Mg Mh Mi Mm Mq Mv Mz Nb Nd Ne Ng Nh Nl Nm Nt Of Oh Oi Oy Oz Pz Qd Wm) Jh(aA Fp Hr Hv Ih Im Iq Iu Iv Jm Js Li Lw Ly Lz Ma Mc Md Me Mg Mh Mk Ml Mm Mq Mr Mv Nc Ne Nf Nh Nk Nl Nm Nt Nu Of Og Oh Oz Pb Pc Qd) Ny(aA Hq Hr Hu Hx Ij Il Im In Iq Ir It Iu Lj Lz Md Me Mf Mg Mh Mj Mr Na Nf Ng Nh Ni Nl Nm Nr Ns Nt Nx Og Oi Oy Oz Pa Pe Qb Qc Qd) Pe(aA Hr Hu Hx Il Im Ir It Iv Jm Jo Lu Lw Lx Ly Mb Me Mf Mg Mh Ml Mp Ms Mv Mw My Mz Ng Ni Nl No Ns Nt Nu Og Oi Oy Oz Pc Qc) Lx(aA Fp Hq Ih Ii In Iq Ir Iv Js Lu Ly Ma Mb Md Me Mf Mm Mr Mv Mz Na Nb Nc Ne Nf Ni Nk Nm Nq Ns Nt Pa Pd Qd Wm) Ma(Fp Hq Hr Hv Hw Ii Ij Il Im In Io Jj Jq Lu Mb Mi Mj Mn Mp Ms Mw My Mz Nb Nc Nk Nl Nn Nq Nr Nu Nx Og Pd Qd) dN(aG aI aJ AN aO aP aU bA bB Bg bJ bL bN bQ bZ cE Ch cJ cK cN cR cS Cx cY DB DD dE dF dI DK) Mp(Hq Hr Hu Hv Hw Ih Ik Im Iq It Lz Mc Md Me Mf Mg Mh Mi Ml Mq Mr Mv Nb Nc Ne Ng Nk Nq Nt Pa Pz Qb Qd) aA(bF bH bJ bZ cS Cx dB hA Hu hW HX iB Ij Il Im Io jH jI Jo jP jV kG Li Lw Mh Mn Nk Nt Nu Og Oz Pc) Nn(Hq Hr Hu Im Io Iq Li Lu Ly Lz Mb Md Me Mh Mk Ml Mn Mq Mr Ms Mv Mz Nb Nc Nq Nt Of Oh Oy Oz Pb Qd) Hx(Hr Hu Ij Il Im In Io Ir Lu Lw Ly Mf Mg Mh Mi Mn Ms Mv Mw Mz Ni Nm No Nt Nu Oh Oi Oy Oz Pc Qd) Jq(Fp Hu Ih Ii Ij Ir Iv Jm Jo Li Lw Ly Me Mh Mk Ml Mr Mx Mz Nf Nl No Nr Ns Nx Oe Og Oy Qd) Nq(Fp Hr Hv Ih Ii Ik Im In Iq Iu Iv Jj Lu Ly Mb Mf Mj Mn Mz Nb Nd Ne Nh Nx Oh Oi Qd) Lv(Hu Ii Ij Il Io Iq It Iu Jo Jt Mb Mc Me Mj Mk Ml Mq Ms Mv Na Ni Oi Qc Qd) Mw(Hq Hr Hw Ii Il Im Io Ir It Iu Jj Jm Lj Mf Mh Mm Mn Mv Na Nm Nu Pz Qd) Fr(aK An aO bA bB bE bl bJ Bo bU Cq cS cU Cx Db Dg Iq It Lj Ne Oy) Mm(Fp Hq Hw Ii Il Im Jj Jl Js Lu Mh Mj Mn Mx My Nb Nr Nt Nu Og) cS(aM aO AP As aU Aw bA Bn Cp CU Cv Cw cY Db Dc Dg Dk dM) Jn(Hr Ih Jm Jo Js Jt Ly Lz Mb Md Nc Ne Nf Ng Nh Of Oy Oz Pd) Ir(Hr Im In Io Li Lw Mc Mf Mg Ml Mn Mv My Ns Nx Og Pb Pc) cU(aO aP Aw aZ bB bF bV Cp Cq cW dA Dd dE dF dG Dk dM fR) Im(Hq Iv Lu Lw Mi Mj Mn Mv My Mz Nb No Nt Pa Pc Qd) Nx(Fp Ij Io Jj Mn Mx Mz Nj Nk No Nt Pa Qb Qd) Mn(Hw Ij Io Jj Lw Mi Mx Mz Nb No Pa Qd) Nj(Fp Hq Ij Iv Jt Mi Mj Mv Nr Oy Pa Qb) Ip(It Ly Mc Mf Ml Ne Ng Nh Ni Pz Qc Wm) Oh(Hu Hv Hw Il Mi Mj Mx My Nb Nr Ns Nu) Mz(Hv Li Mb Mg Ml My Ns Nu Qb Wm) Ij(Jj Mi Mr Mx Nb No Og Pa Pb) aP(bB bF bG bH bR bU cD cF cJ) Ef(An aO aV bF Cx Db dJ) Nt(Io Mx My Og Pa Pb Qb) Qd(Iv Mb Mh Mx My Pb Wm) aJ(bB bF bG bU cD cJ dH) Cq(aX bF cD dB dE dl) cK(al bQ bV cG dD dF) My(Jj Lw Md Og Pa) Nb(Io Mx Nl Nu Wm) aO(An bC bH bJ dI) mF(kG mP mT nM oP) Dc(aX bF cP cX) Jj(Il Jo Mv Qb) Nu(Lw Md Nr) Mx(Hq Hu Mv) Jl(Et Mh On) cD(bQ Dd Ex) dF(bH bJ dK) An(bZ cJ) Dk(Aw dB) Lw(Hu Hv) Mi(Og Pb) Mt(Ml Og) Pa(Oz Pb) bA(bF bJ) dI(De Di) dK(Ex Gl) hR(jP lO) kG(oP oQ) DbbV DddB HuPc Hwln bQcY cXfR jHjP Unconstrained panels with 2 analytes, where 1.0E-3 >= 'AUC p-value' > 1.0E-4. Contains 2,062 panels of 16,788 total panels evaluated. : aA(aG al aO aX bB bE bG bQ bU cD cH Cq cX Db dE dF dI dK dN eD Ef Fp Hq Hr HV Hw Ih In Ir Iu Iv jD jE jF Jj jK jL Jm Jq jR Js jT jU Lj lK Lu Mc Me mF Mi Mj Mk Ml Mq Mr Ms Mx Mz NB Nc Nd Ng Ni Nl Nm NR Ns Oe Of Oh Oi Ok Pa Pb Pd Pf Pz Qb Qc Qd Wm) Qd(Fp Hq Hr Hu Hv Hw Ih Ii Ij Ik Il In Io Iq Ir It Iu Jk Jm Jo Js Jt Li Lj Lu Lw Ly Lz Mc Md Me Mf Mg Mi Mj Mk Ml Mq Mr Ms Mv Mz Na Nb Nc Nd Ne Nf Ng Nh Ni Nk Nl Nm No Nr Ns Nt Nu Of Og Oh Oi Oy Oz Pa Pc Pd Pe Pf Po Pz Qa Qb Qc Qe) cU(aC Ad aE aF aG aH aI aJ aK aL aM aN Ao aQ AR aS aU aW Ba Bb BC bE BG bH bJ bL bM BN BO bQ bR bS bU bW bX bZ cA cC cD cI cJ cL cN CO cP cQ cR CT Cu CV Cw cX cY cZ DB dC dD De dH Di dL Ef Ex Gl) dN(aC AD aE aF aH Aj aK AL aM Ap aQ AR aS aV AW AX aY aZ Ba bC bE bl bM BO bP bR bS bU bV bW bX cA cB cC cD cF cG cH cl cL cM CO CP cQ CT cV CW cX cZ dA DC De dG dH Di dJ dL dM fR Gl) Im(Fp Hr Hu Hv Hw Ih Ii Ij Ik Il In Io Iq It Iu Jm Jo Js Jt Li Lj Ly Lz Mb Mc Md Me Mf Mg Mh Mk Ml Mq Mr Ms Mx Nb Nc Nl Nm Nr Ns Nu Oe Of Og Oh Oi Oy Oz Pb Pd Pf Pz Qb Qc) Ir(Fp Hq Hu Hv Hw Ih Ii Ij Ik Il Iq It Iu Iv Jm Jo Js Jt Lj Lu Ly Lz Mb Mc Md Mh Mi Mj Mk Mq Mr Ms Mx Mz Na Nb Nc Nd Ne Nf Ng Nh Ni Nk Nl Nm No Nr Nt Nu Oe Of Oh Oi Oy Oz Pa Pd Pz Qb Qc) Mn(Fp Hq Hr Hu Hv Ih Ii Ik Il In Iq It Iu Iv Jm Jo Js Jt Lu Ly Lz Mb Mc Md Me Mg Mh Mj Ml Mq Mr Ms Mv My Na Nc Nd Nf Ng Nh Ni Nk Nl Nm Nr Ns Nt Nu Of Og Oh Oi Oy Oz Pc Pd Pz Qb) Fr(aC Ad AF aG aH al AJ aL aN Ao AP aR Aw AX aY aZ Bb bC bH bL bM bN bO bQ bR bV cA cC cE cL cM cN Co cP cQ Ct Cu cV Cw cX cZ dA DC DD dF dH dI dJ Dl dM Jl) Ij(Fp Hq Hr Hu Hv Hw Ih Ii Ik In Io It Iu Iv Jk Js Li Lj Lu Lw Ly Lz Mb Mc Md Me Mg Mh Mj Mk Ml Ms Mv Mw My Mz Na Nc Nd Ne Nf Nh Nk Nl Nm Nr Nt Nu Oh Oy Pc Pd Pe Pz Qb Qe) aP(aC aE aG aH al aK aL aM aN aO aR aV Aw aZ bA bE Bg bl bJ bM bN bP bQ bZ cA cB cE cG CH cl cK cL cM cN cP Cq cR cT CX cY DB dC dD dE dF dG dJ dK dL) Ma(Hu

Figure 34 Continued

Ih Ik Iq It Iu Jm Jo Js Jt Li Lj Lw Ly Lz Mc Md Me Mf Mg Mh Mk Ml Mm Mq Mr Mv Na Nd Ne Nf Ng Nh Ni Nm No Ns Nt Oe Of Oh Oi Oy Oz Pb Pc Pf Pz Qc Wm) Mm(Hr Hv Ih Ik Iq It Iu Iv Jm Jo Jt Li Lw Ly Mb Mc Md Me Mf Mg Mi Mk Mp Mq Mr Mv Na Nc Nd Nf Ng Nh Nk Nl Nm Nn No Nq Ns Oe Of Oh Oy Oz Pb Pd Pz) bQ(aF aG al aJ aK aL AN aO aQ aU aX aY aZ bA bE bG bH bJ bL bN bO bR bU bV cA cC cE cF cG cJ cL cM cN cR cS cV cX dA DB dC DD dH dJ dK) Hx(Fp Hq Hv Hw Ih Ii Ik Iq It Iu Iv Jm Jo Js Jt Lj Lz Mc Md Me Mj Mk Ml Mq Mr Mx My Na Nc Nd Ne Nf Ng Nh Nk Nl Nr Ns Oe Of Pa Pd Pz Qb Qc Wm) dF(aJ aK aL An aO aU aV Aw AX aZ bB bC bE bG bL bR bU bW bZ cC cD cE cF cJ cM cN Cq cR cS cV CX cY cZ dA DB Dd DE dH dl dJ dM Ef) Mz(Fp Hq Hu Hw li Hw li Ik Il In Io It Iu Iv Jj Lw Mc Md Me Mf Mh Mi Mj Mk Mq Ms Mv Mx Nb Nc Nd Nf Nh Nk Nl Nm Nt Of Og Oh Oi Oy Pa Pb Pf Pz Qc) Nt(Fp Hq Hr Hu Hv Hw li Ik In It Iv Jj Jk Li Lj Lw Ly Mb Me Mh Mi Mj Mk Ml Mr Ms Mv Mw Nb Ng Nk No Nq Nr Ns Nu Oh Oi Oy Oz Pc Pf Pz) My(Fp Hq Hu Hv Ih Ik Iq Iv Jg Jk Lu Lz Mc Mf Mh Mi Mj Mq Mr Ms Mw Mx Nc Nd Ne Ng Nh Nk Nl Nm No Nq Nr Ns Nu Nx Oi Pb Pz Qa Qb Wm) Nx(Hq Hu Hv Hw Ih Il In Iq Iu Iv Js Li Lj Lu Lw Mf Mg Mi Mj Ml Mq Mr Mv Mw Na Nb Nc Nd Ne Ni Nm Nr Ns Oe Of Oh Oi Pb Pd Pz Qc) Pe(Fp Hq Hv Hw Ih li Ik Iq Iu Js Jt Li Lj Lz Mc Md Mi Mj Mk Mq Mr Mx Na Nb Nc Nd Ne Nf Nh Nk Nm Nr Oe Of Pa Pd Pz Qb Wm) Jk(Hq Hr Hv Hw Ih li Il In Iq It Iu Jo Jt Lj Lz Mc Md Me Mf Mg Mj Mk Ml Mq Mr Mv Nd Ne Nf Nh Nk Nl Nm Nr Nu Oe Qc Wm) Jg(Hu Ih Iq It Iv Jm Jo Js Lj Ly Lz Mb Mc Me Mf Mg Mh Mk Mq Mv Na Nc Ne Ng Nh Nk Nm No Ns Nu Oe Of Oy Oz Pc Qc Wm) Qb(Hq Hw Ih Il Io Iu Iv Jo Jt Li Lu Lw Md Mf Mg Mh Mi Mj Mq Ms Mv Mw Mx Nb Nl Nm No Nr Nu Og Oh Pa Pb Pc Pf) Nq(Hq Hu It Jo Js Li Lj Lw Lz Mc Md Me Mg Mh Mi Mk Mq Mr Ms Mu Mv Na Nc Nf Nk Nm No Ns Oe Oy Oz Pc Pz) cS(Ad Af AJ aK Al aN Ao Ar Ax Ba BB Bc bF Bg cD cF Ch Co cR Cs CT Cx dA De Di dJ Dl Ef Ex Gl) Mv(Il Io Iq It Iu Iv Js Lh Lu Lw Mb Md Ml Ms Nc Ng Nk Nl No Nr Nu Of Og Oh Oi Ok Oy Oz Pa Pb Po Qe) Jq(Hr Ik Iq It Js Jt Lj Lu Lz Mc Md Mf Mj Mq Ms Na Nc Ne Ng Nh Nk Nm Of Oh Oi Oz Pb Pc Pd Pz Qc Wm) Qe(Fp Hu Ih li Il In It Iu Jo Js Jt Lu Ly Lz Md Me Mf Mk Mq Nc Nf Ng Nh Nr Nu Oe Of Oz Pd Wm) aJ(aG aH al Aj aO aX aZ bC Bg bH bJ bN bR bZ cF CH cl cK cM cN cQ cR CX dB dD dG dI) Ef(aC AF aH Aj aN Ap aS aU Aw bB BG bl bN Bo bP bR bU cM cR dA dE Dg dl Dl Gl) Mp(Fp Ii In Io Iu Iv Jj Jo Js Jt Li Ly Mb Mk Na Nf Ni Nm No Ns Oe Oz Pb Pc Pd Qc) aO(aF aM aN aR Aw aX bA bE bG bV bW cE cG cJ cK cM Cq cR Cw cX dA Dd De DK dM) Aw(Al AN Ar AX BC bG bH bJ Bo bS bV bZ cB cJ cK Cq dA Db Dd Gl) No(Fp Hu Il Jh Jo Lx Mg Ml Ms Mu Mw Mx Nn Nu Ny Og Oi Ok Oz Pb Po Wm) An(aG al Ba bB bC bF Bg bH bL bV cG Co Cq Cu Cw dB Dc De Di dK) Mx(Fp Ih li Il Io Jj Lw Mf Mg Ms Nc Nj Nl Nm Nr Nu Og Oy Oz Pb) bA(aX bC bE BG bH bW bZ cD Ch cK cO cR dB Dc DE dl DK) Nb(Fp Hq Hr Hu Il In Li Lv Lw Ml Ms Na Ni Nm Og Oz Pb Po Pz) Nu(Hq Hr Hv Hw Ih Il Il Iu Mi Mj Mr Nd Nh Ns Of Oy Pa Pb) Oh(Hq Ii Ik In Iq It Iu Lw Mc Ml Mq Ne Nh Nj Of Oy Pa) dI(Ad aF al aM aS bB BG Bn bV Ch Cp Cu cV Dc dD Dk) Cq(bE bJ bL Bo cG cJ cK cM Cp cR Cx Db Dc De DK) Ny(Fp Ih li Iv Jj Js Lu Ly Mb Mk Ms Nc Nk Oe Pd Wm) Ok(Ik Iq Jt Lu Lz Md Mf Mj Na Nf Ng Nm Nr Ns Oy Pc) Pf(Ih Js Mb Mf Mk Ms Na Nc Nf Nh Ni Nk Oi Oz Pb Qc) Mw(Fp Ih Iv Js Lu Ly Mg Mk Nc Ni Oe Oi Pb Qc Wm) Jh(Io It Jo Jt Lj Lu Mb Mf Na Ns Oe Oi Pd Qc Wm) Lv(Hq Ik In Jm Lw Mf Mg Ne Oe Of Oy Oz Pz Wm) Dd(aH aX bB bZ cF cG Ch cl cJ Cu Db DK) Nn(Fp Ih Iv Jj Js Mf Mg Na Nf Ni Nm Qc Wm) Mu(Jt Li Lj Ly Mf Mr Na Nf Ni Ns Oe Pc Pd) bF(aM aN Ar Ax BC bV Cu Cw dA Dk dM Ex) Po(Iq Iv Jo Jt Li Me Mf Ne Nf Nh Ns Wm) Nr(Hv Ik Io Lw Ly Mi Nh Nl Nm Og Pa Pb) Hq(Hv Iv Jj Lw Na Ng Nl Og Oy Pa Pc Pz) Dk(aX Ba bB bC bH cK Co Cx Db dK Gl) Nj(Hu Hw Ih li Il Js Li Mg Mr Nm Pd) Jj(Fp Ih li Iv Jm Js Lx Mg Mj Pa Pd) Dc(Af Ax bC bH bN cD cJ Cv Cx Gl) bV(Aj bB bE bG bH bJ bL cR De dK) Gl(Ad bB Bg Bo cD cJ cX De) Il(li Iv Lw Ly Mh Nm Og Pd) Lx(Ik Jm Jt Lj Ng Pb Qc) Lh(Ih Ik Jt Nc Oe Of Oz) cJ(Ba BG cK Cu dM Ex) dK(aN Ax Bg bZ dA dM Fw) Nm(Hu Ik Iq Ns Og Pa) Qa(Fp Nh Oe Oy Pd Wm) cG(aK aU bG bH cY dA) hW(eD jG jH jR jV 1K) Mi(Hu Lw Mb Ms Pa) li(In Ly Nl Og Pb) Iv(Io Ms Og Oi Pb) bB(bH bS cK dA dM) bZ(Bo cK cT dA dM) fR(bH bU cD Cx dH) Wm(Ih Is Ly Og) Hu(Md Mh Mj Nl) nR(kE nC nK oQ) mF(ml nN nU oQ) hR(iC jE jL IM) iB(jE jG jH jR) kG(kK IX mS nK) Cu(aX bJ Db) Lw(Fp Hw Iq) cK(aL bC Di) Ex(bU Cx) Mg(Ng Pa) Ml(Hv Mr) Jt(Og Oi) aM(aX dE) bG(bC bW) cD(Ba Bg) dA(al De) AdaX MdHv MfPa MhMt MrPb HwOg JlOz aLbE bHdM mPmU jFjR

Unconstrained panels with 2 analytes, where 1.0E-2 >= 'AUC p-value' > 1.0E-3. Contains 3,089 panels of 16,788 total panels evaluated. : Gl(aA aD aE AF aG aH al aJ aK AL aM AN AO AP aQ AR AS aU aV aW AX aY aZ BA Bb BC bE bF bG bH bl bJ bL bM BN bO bP bQ bR bS bU bV bW bX bZ cA cB cC cE cF cG CH cl cK cL cM cN CO CP CQ cR cT cV CW cY DC DD De dH Di dJ Dk fR iC li Ik Iq It jG jM jO jQ Jt jY kE kF kN kO IL IN IO Ly Lz Mb Md mT Na nC Ne NfNH No oO Oy) Cq(AD aE aF aG aH al Aj aK AL aN Ao Ap aQ AR AS aU aW Ax aY aZ BA BB BC BG bH bl bM BN bO bP bQ bR bS bU bV bW bX bZ cA cB cC cE cF CH cl cL cN Co cQ Cs CT Cu CV Cw cX cY cZ dA dC DD DG dH Di dJ DL dM Ef Ex fR Fw) aO(aC AD aE aG aH al Aj aK AL Ao Ap aQ Ar AS aU aV aW Ax aY aZ Ba BB Bc bF bl bL bM bN BO bP bR bS bU bX bZ cA cB cC cD cF cH cl cL cN CO CP cQ Cs CT Cu CV cW Cx cY cZ DB DC dD dE dF Dg dH DI dJ DL dM Fr) Aw(aC Ad aE Af aG aH al AJ aK aL Ao aQ aR AS aY aZ BA bB bE bF Bg bL BN bO bQ bR bU bW cC cD cE cF CH cl cL cM cN CO Cp cR Cs cT CV CW CX cY cZ dB DC dD dE DG dH Di dJ dK Dl dM Ex Fw) Dc(AD aF aG aH al AJ aK aL aM Ao AP AR AS aV aW aZ Ba BB Bg bl bJ bL bM Bn BO bQ bR bU bV bW bX bZ cC CH cl cK cL cM cN CO Cp cQ cR Cs cT cV Cw Db dC DD DE dF Di dJ DK DL Ef) bA(aC AD aE Af aG al aJ aK aL aM An Ao Ap aQ aR aS aU aV aW aZ bB bl bL bM bN bO bP bR bS bU bV bX cA cC cE cF cH cl cJ cL cM cN Co CP cQ cT cV CW CX cY cZ dA Db dC DD dF dG dH Di dJ fR) dF(aC AD aE AF aG aH al Aj Al aM aN Ao Ap aQ AR AS aW aY Ba Bb Bc bF Bg bl bM BN BO bP bQ bS bV bX cA cB CH cl cL CO CP cQ Cs CT Cu Cv Cw dC dD DG Di Dk DL fR) Iv(Fp Hr Hu Hv Hw Ih li Ik In Iq It Iu Jm Jo Js Jt Li Lj Lu Lw Ly Mb Mc Md Me Mf Mg Mh Mi Mj Mk Ml Mq Mr Mx Na Nb Nc Nd Ne Ng Nh Ni Nk Nl Nm No Nr Ns Nu Oe Of Oh Oy Oz Pa Pc Pd Pf Pz Qc) fR(aC aE aF aG aH al AJ aK aM AN aP aQ aR aU aV aW aY aZ bB bC bE bF bG bl bJ bL bM bN Bo bQ bR bW bZ cC cE cF cH cJ cK cL cM cN cR cS cV cY cZ dA Db dC DD dl dJ dK dL dM Fr) bV(aC Ad aE aF aG al aJ aK aM aN Ao AP aU aV aX aY aZ Ba bC Bg bN BO bR bU bW bZ cA cB cC cD cE cF CH cJ cM cN CO Cp cS CT Cw CX cY dB dC DD dE Dg Di dJ Dk Ef) An(Ad aF aH AJ AL aM aN Ao AP aQ Ar aU aV aW aY aZ Bb Bc bE bG bl bJ bM bO bR bS bU bW cE cF CH cl cK cM cN cO Cp cR CT cW CX cY Db dC DD dE DG dH dI Dk) cS(aE aF aG aH al aL aQ aR aS aV aW aX aY aZ bC bE bH bl bJ bL bM bN bO bP bR bS bU bW bX bZ cA cB cC cE cH cl cJ cL cM cN cO cP cQ cV cW cX cZ dB dC dD dE dG dH dl dK dL Fw) Ba(aC aD aE aH al aJ aM aN Ao AP As AX aZ bB Bc bF BG bH bL bM bQ bR bU cF CH cl cK cL cM Co Cp cR Cs Cu Cv Cw CX cY dA DB Dd De Dg dH DI dK Ef Fr) Dd(AD AF aG al aJ aK Al aM Ao aP aZ Bb bC bE BG bH bl bL bM bN BO bR bU bW bX cA cC cE cH cK cM CO Cp cQ cR CW CX cY dD DE dG DI dJ DI Ef) Ih(Fp Hq Hu Hv Hw Ih li Ik Il In Io Iq It Jm Jo Js Jt Lj Lu Lw Mb Mc Mf Mg Mh Mi Mj Ml Mq Mr Ms Mv Mz Na Nb Nc Nd Ne Nh Nl Nm No Nr Ns Nt Oe Of Og Oh Oi Oy Pa Pb Pz) bQ(aC aD aE aH Aj aM AR AS aV aW Ax BB bC bF Bg bl bM Bn Bo bP bS bW bX cB CH cl CO CP cQ CT Cu CW Cx cZ DE DG Dl Dk DL dM Ef) aJ(aC AD aE aF aK aL aM aN Ao aP aQ aR aS aU aV aW aY bE bl bL bO bP bS bW bX cA cB cC cE cL CO cP CT Cu cV cW cY cZ Db dC DE Di dJ DK dL Ef) No(Hq Hr Hv Hw li In Io Iq It Iu Jj Js Jt Li Lj Lu

Nw Nx Oh Ok Om Pc Qa) Lx(Hq Hv Hw Ir Ji Jo Jq Jt Lw Ly Mh Mz Na Nb Nw Oh Ok Om Pc Qa Qd) Ms(Hx Ii Jh Ji Jt Lh Mi Mn Mv Mw My Nb Nr Nw Nx Ny Om On Pa Pc Po) Io(aA Fr Ir Ji Jl Jt Lh Mi Mn Mv Mx My Nt Nv Nw Ny On Pa Pg Qa Qd) Jq(Fr Hw Lh Mg Mi Mr Mv Nd No Nr Nt Nv On Pa Pc Pe Pg Po Wm) Oh(Hw Hx Il Jh Lh Mn Mz Nb Nt Nv Nw Oi Ok Om Pa Pe Pg Po Qa) Mz(Fr Hw Iu Lw Mg Mi Ml Nt Nv Ok Om Pa Pc Pe Pg Wm) Fr(aA Hv Hw Ir Jl Jt Lh Na Ng No Nt On Pz Qa) Pc(aA Hu Hx Jh Ji Lh Nv Oi Ok Om Pe Pg Po Qa) Nw(Hv Hw Mb Mg Mi Mr Na Nt Ok Pa Pe Qa Wm) Om(aA Hw Mi Mr Ng Nm No Nt Oy Pa Pe Qa) On(aA Hu Ii Mw My Ng Nm No Ns Of Oy Pz) Jh(Hu Hx In Iv Lz Mx Na Nf Nr Ns Oy) Ji(aA Hw Il Lh Mi Nm No Nt Pa Pg Wm) Nv(Hv Hw Lw Mi Mr Ok Pa Pe Qa Qd) Mn(Hv Hw In Ir Lw Lz Md Na Ni) Nb(Hx Mh Ml My Ny Oy Qa Qd) Lw(aA Hx Lh Mx Pa Pe Po) Qa(It Mg Mi Mr Pa Pg Po) Ok(Md Mg Mi Nt Pa Pg) Qd(Hx Mb Pa Po Wm) Lh(aA Ii Jl Jo Ly) Pg(aA Hw Jt Oy Oz) Mw(Hu My Ns Oy) Mg(aA Hx Oi) Pa(Hv Na Ni) Po(Mh Oy) No(Jl Oz) Nt(Ik Jo) WmLy NrIm HvIt HxIr IlJm NyOi OzPe} Nj{Mu(aA Et Fr Hw Hx Ih Im Ir Is Iu Iv Ji Jl Jn Jo Jp Jq Jr Jt Lh Lv Lx Md Mi Mm Mp Mr Ms Mt Mz Nb Nf Ng Nn No Nr Nt Nv Nw Og Oh Oi Ok On Pa Pb Pe Pg Po Qa Qd Qe) Mp(aA Et Fr Hq Hv Hw Hx Ii Ij Im In Ir Is Jk Jn Jp Jq Jr Jt Lh Lu Lv Lx Ma Mi Mj Mr Mt Mv My Mz Nb Nn No Nq Nr Ns Nv Nw Nx Ny Ok Om Pa Pe Pg Po Qa Qd Qe) Nq(aA Hu Hv Hw Hx Ih Ii Ij Im In Ir Is Jk Jn Jp Jq Jr Jt Lh Lv Lx Mi Mj Mq Mr Ms Mt Mx My Mz Na Nb Ng No Nr Nv Nw Og Oh Ok Om Pa Pe Po Qa Qd Qe) Mt(aA Et Hv Hw Im In Io Is Jj Jk Jq Lu Lv Lx Ma Mb Md Mi Ml Ms Mz Na Nb Nf Ni Nn No Nr Nt Nv Nw Ny Og Oh Oi On Pa Pb Pe Pg Po Qa Qd Qe) Jq(aA Et Fr Hw Hx Il Im Is Jg Jk Jo Jp Jr Lh Lv Lx Ma Mg Mi Mr Mv My Nb Nd Nn No Nr Nt Nu Nv Nw Ok Om Pa Pe Pg Po Qa) Nv(aA Et Hv Hw Im In Io Ir Is Iv Ji Jn Jo Jp Jr Jt Lv Lw Lx Ma Mi Mz Na Nf Ni Nn No Nr Nw Og Oh Ok Om Pe Qa Qd Qe) Nn(aA Fr Hu Hv Hw Hx Ii Ij Il Im In Jk Lh Lv Lx Ma Md Me Mi Mq Mr Mx Mz Nb Nd No Nr Nt Ny Om Pa Pc Pe Po Qa) Jk(aA Et Hw Hx Im Io Ir Iv Jn Jr Jt Lu Lv Lx Md Mi Mr Mz Na Nb Nf No Nw Og Oh Ok Oy Pa Pe Po Qa Qd Qe) Mz(Fr Hx Im Ir Is Iv Jg Jn Jp Jr Lh Lv Lx Ma Mg Ml Mv My Nb No Nt Nw Oh Ok Om Pe Pg Po Qa Qd) Po(Hw Im Ir Jh Jp Jr Jt Lu Lv Lw Ma Mg Mh Mi My Na Nb Nf Ni Og Oh Ok Oy Pa Pb Pc Qa Qe) aA(Et Fr Hx Il Is Jg Ji Jl Jn Jr Lh Lv Lw Ma Mg Mi Mm My No Nt Om On Pa Pc Pe Pg) Nb(Et Hx Im Ir Is Jh Jn Jp Jr Lv Lx Ma Mh Ml Ms Mx No Nw Ny Oh Ok Pb Qa Qd Qe) Fr(Hv Hw In Ir Is Jj Jo Jr Jt Lh Mi Mq Mx Na Nf Ni No Nt Oh On Pe Pg Pz Qa) Lv(Hw Ii Ij Io Lu Mb Md Mi Mq Mr Mv My Na Nd Nf No Nr Nt Nw Oh On Pa Pe) Lx(Hv Hw Hx Ij In Jo Jr Jt Ly Ma Mg Mh Mq Mv My Na Nf Ni Nr Oh Om Pa) Mi(Et Hx Im Ir Is Jg Ji Jl Jn Jp Jr Ma Ms Nw Ok Om Pe Pg Qa Qd Qe) Oh(Hu Hx Il Ir Is Jn Jp Jr Lh Mn Mv Mw My Nw Ok Pe Qa Qd Qe) Pa(Et Im Ir Is Jg Jh Ji Jn Jp Jr Ma Mg Nw Ok Om Qa Qd Qe) No(Et Is Jg Ji Jn Jp Jr Lh Ma Mg My Ok Om On Pg Qa) Nt(Et Io Is Ji Jn Jp Jr Mm Ne Nw Og Ok Om Pg Qa Qd) Hw(Ir Is Jn Jp Jr Ma Mn Mw Nw Om Pe Pg Qa Qd Qe) Lu(Et Hx Im Is Ji Jn Jr Ma Nw Ok Om Qa Qd Qe) Nf(Et Ir Is Jl Jn Jp Mw Nw Ok Pg Qa Qd Qe) On(Et Hu Is Jj Ma Ms Mw My Ni Ns Og Oy) Qd(Ii In Io Jh Mb Md Mq Mw My Na Nd) Jp(Ii In Io Jr Ma Md Mq Mv My Nd Nw) Nw(Im Io Lh Mq My Na Nd Ni Ok Qa) Ma(Hx Ii Jr Lh Ny Ok Pe Qa) Md(Hx Is Jn Mn Mw Ok Qa Qe) Nd(Ir Jn Jr Ok Om Qa Qe) Jr(Im Jj Jt Lh Mb Pe) Mw(Hu Mx Nr Ns Oy) Io(Ir Is Ji Qa Qe) Ni(Hx Is Jl Pg) Im(Hx Jj Mj Pe) Mv(Hx Mx Pe) My(Jn Ok Qa) Qe(Ii Mq Na) Om(Lh Mr Ms) Mb(Is Pg) Mh(Jl Lh) EtPz NrMn MgMx MrHx JjPe NyPb} Lv{Jj(Et Fr Hu Hw Hx Ih Ii Ij Il Im Io Ir Is Iu Iv Jg Jh Jk Jl Jm Jn Jo Jp Jq Jr Jt Lh Li Lu Lw Lx Ma Mb Md Mg Mi Mm Mn Mp Mr Mt Mu Mv Mw My Mz Nb Nd Nf Nl Nn No Nq Nr Nt Nv Nw Nx Ny Oh Om On Pa Pc Pd Pe Pg Po Qa Qd Qe) Mm(aA Et Hu Hw Hx Ii Il Im In Io Ir Is Iv Ji Jk Jl Jn Jo Jq Jr Lh Lu Lx Mi Mr Mt Mu Mz Na Nb Nf No Nr Nt Nv Nw Ok Om On Pa Pe Pg Po Pz Qa) Jn(aA Et Fr Hw Io Jg Jk Jo Jp Lh Lu Lw Lx Ma Mg Mi Mp Mr Mt Mu Mz Nb Nn No Nq Nr Nt Nv Nw Og Oh Ok Om Pa Pc Pe Pg Po) Oh(Et Fr Hw Hx Il Io Is Iu Iv Jg Jh Ji Jl Jo Jp Jr Lh Lw Lx Ma Mb Mg Mi Mr Mt Mu Nq Nr Nv Nw Og Ok Om Pa Pc Pe Po) Jq(Fr Hw Hx Im Io Is Iu Jg Jk Jo Jp Lh Lx Ma Mg Mi Mp Mr Mt Mu Mv My Nb Nd Nn Nq Nr Nt Nv Og Ok Pa Pc Pe Pg Po) Mt(Et Fr Hw Io Is Iu Jl Jo Jr Lh Lw Lx Mb Mg Mh Mi Ml Mp Mr Mu My Mz Nf Nn Nr Nw Ny Og Oi Ok Pb Pc Pe Po) Jp(Hw Hx Io Ir Is Iu Iv Jk Jo Jr Jt Lu Lw Lx Mb Mg Mi Mp Mr Mz Na Nb Nf Nn Nq Nr Nt Nv Ok Pa Pc Pe Pg Po) Io(aA Et Fr Hx Ir Is Iv Jg Ji Jl Jr Js Lh Lx Ma Mb Mi Mr Mu Mx Mz Nn No Nv Nw Ok Om On Pe Pg Po Qa) Nn(aA Et Fr Hu Hw Hx Il Im Is Iu Iv Ji Jo Jr Lh Lu Lx Mi Mr Mu Na Nr Nt Og Oi Ok On Pa Pe Pg) Og(aA Hx Ii Il Im Is Iv Jg Jh Ji Jk Jo Lh Mq Mu Mw My Nb Nq Nr Nv Nw Nx Ok Om On Pa Pc Po) Jr(aA Hw Jg Ji Jk Jo Lh Lu Lw Lx Ma Mg Mi Mp Mr Mu Mz No Nq Nt Nv Nw Ok Om Pa Pc Pe Pg) Et(aA Hw Hx Ji Jk Lh Lu Lx Mi Mp Mr Mu Mz Nf No Nq Nt Nw Oi On Pa Pc Pe Pz) Ji(aA Fr Hw Il Jk Lh Lu Lx Mi Mp Mr Ms Mu No Nq Nt On Pa Pc Pe Wm) Is(Fr Hw Lh Lu Lx Mg Mi Mp Mr Ms Mu Mz Nf Nq Nt Nw Ok Pa Pc Pe) Nw(Hw Iu Jk Jo Lu Lw Lx Mg Mi Mp Mr Na Nq Nr Ok Pa Pc Pe) Ok(Iu Lx Mg Mi Mp Mu Mz Nf Nq Nv Pa Pc Pg Po) On(aA Hu Ms Mu Mw My Ng No Ns Of Oy Pb Pz) Mp(Hq Hx Iv Jg Jh Jl Mz No Nr Om Pc Pe) Ma(aA Hx Iv Lu Mb Mr Mz Ng Pa Pc Pe) Jg(aA Hu Hx Iv Ms Mx My Mz Ng Oy) Mu(aA Jl Lh Mi Ng Nt Pa Pb Pe) Jh(Hu Hx Ir Iv Li Mb Mi My Oy) Pb(Hx Lh Ny Om Pa Pe Pg) Jl(Lh Mg Mi Mz Nq Pc) Lx(Hq Hw Mb Om Pc) aA(Fr Mc Mg Nq Pc) Om(Ir Lu Mi Pa) Fr(Hw Mz Ng) Mb(Iv Li Pe) Lh(Lw Mz Pc) Nq(Hx Ng) Mx(Lw Pc) Im(Lu Pg) PoOy MeHv HxPc} Jr{Jj(Hw Hx Il Is Iu Jg Jh Jk Jo Jp Lh Lu Lw Lx Ma Mg Mi Ml Mn Mp Mr Mt Mu Mv My Nb Nd Nn No Nq Nt Nv Ok Om On Pa Pc Pe Pg Po) Io(aA Et Hr Hx Im Is Iu Jg Jh Ji Jk Jl Jo Jp Jt Lh Lw Ma Mi Mm Mn Mp Mt Nm Nt Nv Nw Oh Ok On Pa Pc Pg Qa) Nn(aA Et Fr Hu Hw Ji Jo Jq Lh Lj Lu Lx Mi Mm Mr Ms Mu My Ng No Ns Nt Og Oi Ok On Oy Pa Pe Pg Qc) Og(Et Fr Hx Is Iu Jg Jh Jk Jl Jo Lh Lw Mg Mi Mr Mt Mu Mv Mw Nb Nm Nq Nr Nv Om On Pa Pc Pe Po) Jq(Is It Jg Jk Jo Jp Js Lh Lu Lx Ma Mg Mi Ml Mm Mp Mr Mt Mv Nd Nq Nt Nv Pa Pc Pe Pg Wm) Pc(aA Et Hw Ji Jk Jo Jp Lh Lu Lx Ma Mg Mi Mp Mr Ms Mt Mu Mz Nd No Nt Ok Om Pa Pe Pg) Ma(aA Hw Jg Ji Jk Jp Lh Lw Lx Mb Mi Ml Mp Mr Mt Mu No Nt Nv Nw Ok Om Pa Pe Pg) Lw(aA Is Jk Jl Jo Jp Lh Lu Lx Mr Mt Mu Nd No Nt Nv Nw Om Pa Pe) Ji(aA Jk Lh Lu Lx Mi Ml Mm Mp Ms Mu No Nq Nt Pa Pg Qc Wm) Ml(Hw Jo Lh Lu Mr Mt Mv Mz Nb Nr Ns Om Pa Pe Po Qa) Mg(aA In Jp Lh Lu Lx Mr Ms Ng No Nt Ok Pa Pe Pg) Mt(Hx Jo Lx Mh Mi Mp Mr My Ny Ok Oy Pa Pb Pe) Jp(Hw Jo Lu Lx Mi Mp Mr Nt Nv Oh Ok Pa Pe) Et(aA Lh Lu Mi Mm Mp Mu No Nq Nt On Pz) Nq(aA Hu Ms Mu Mv My Ng No Ns Ok Oy) Mm(aA Lh Lu Mr Mu No Nt On Pa Pe Pg) In(Hw It Iu Jk Jo Lh Mi Mr Nb Nt Wm) Jg(aA Hu Lu Ms My Ng Ns Oh Oi Oy Pz) Oh(Hw Im Jh Jk Lu Mr Nd Om Pa Pe) Mp(aA Hq Lh Mu No Ns Nt Ok Om) On(Hu Ii Ms My Ng Ns Oy Pz Qc) Wm(Fp Ik Jm Js Ly Mj Mx Nw) Mh(Ii Iu Jk Lh Lx Nb Pa Po) Mu(aA Lh Mi No Ns Nt Ok Pg) It(Hw Ij Is Jo Jt Na Nt Qa) Ms(Jh Jk Jo Mb Mw Nb Om) Pb(Lh Nb Ny Om Pe Pg Po) Jk(aA Ng Ns Ok Oy) Mw(My Ng Ns Oy) Mz(Iu Js Lj Nd) Jh(Hu My Ns Oy) Ok(Lx Nd Nv Pa) Om(aA Lx Mi Oy) Fr(Ng Oy Qc) Nw(Hw Jo Qc) aA(Lh Me Pg) Lu(Is Me) NoJl NsMq NtNe MkPa MvMy NdJt IiLh IrJs QcQd LiLj} Io{Et(aA Hw Hx Ih Il Ir Is Iu Iv Ji Jk Jl Jn Jq Jt Lh Lu Lw Lx Mh Mi Mp Mr Mt Mx Mz Nb Nc Nf Nk Nl Nn No Nq Nr Nt Nv Nw Oh On Pa Pc Pe Pg Po Qa Qb Qd Qe) Mt(aA Hw Hx Ir Is Iu Iv Jg Ji Jj Jk Jl Jn Jo Jp Jq Lh Lw Mb Mg Mi Mm Mn Mp Mr Na Nb Nm Nn Nr Nt Nv Nw Nx Oh Pa Pc Pe Pg Qa Qe) Jp(Hw Hx Ij Ir Is Iu Iv Ji Jk Jl Jn Jo Jq Lh Lw Lx Mb Mg Mi Mm Mp Mu Mx Nb Nl Nn Nq Nt Nv Nw Nx Ok Pc Pe Pg Po Qa Qb) Ji(aA Fr Hw Hx Il Is Iu Jg Jk Jl Jo Jt Lh Lu Lw Lx Mi Mm Mp Mr Ms Mu My Nl Nn No Nq Nt Nv Oh On Pa Pc Pe Pg Qe) Pg(aA Hq Hw Im Ir Is Iu Iv Jg Jj Jl Jn Jq Jt Lh Lw Mi Mm Mp Mz Ng Nm Nn Ns Nt Nw Og Oh Ok Oy Oz Pb Pc Qa) Is(aA Fr Hw Jj Jl Jo Jq Jt Lh Lw Lx Ma Mg Mi Mm Mp Mr Ms Mu Mz Nn No Nq Nt Nv Nw Og Oh Ok Pa Pc Pe) Jn(aA Hw Hx Iu Jg Jh Jk Jl Lh Lx Ma Mg Mi Mm Mp Mu Mv My Nb Nn No Nq Nt Nv Nw On Pa Pc Qa) Nw(Hw Hx Ir Jk Jo Lh Lw Lx Mg Mi Mm Mp Mr Ms Mx My Nd Nk Nl Nn Nq Nv Og Pa Pc Pe Qa Qe) Jl(aA Fr Jj Jq Jt Lh Lw Ma Mg Mi Mm Mp Mu Mz Nm Nn No Nq Nt Og Oh Ok Pc Qa) On(aA Hu Iu Jj Lw Mi Mm Mp Ms My Ng Nn No Ns Nt Of Og Oy Pb Pc) Mm(aA Hu Hx Ii Ij Ir Jk Lh Nv Ny Pa Pe Qa Qb Qe) Lh(aA Im Jg Jj Mp Nn) Nv(Jj Mx Nn Og) Fr(Mx Nl) Hx(Jg Ma) Qa(Jg Jj) NnaA MpNy MxNx JjJk} Et{Pz(Fr Hw Hx Il Ir Is Iu Iv Ji Jk Jl Jn Jq Jt Lh Lu Lw Lx Mi Mp Mr Mt Mu Mv

Figure 34 Continued

Figure 34 Continued

Lh{Mp(Hq Mk Mz Ns) Jo(Jk Mi Nt Om) Mu(Mh My Pc) LxMh MwMy IiJk} cD{Cq(aX bZ dE dI) bG(aJ aP cS) Dk(cS dI) bH(aO dF) AwdI cKcU cXfR} mF{nR(mU mW nI) mP(kC mU nT) oP(kG nB nI) kC(mI mT) oQ(nB oO) nNmU} dH{aP(aO bB bF bZ cE cU) aJ(bF cS cU) dN(bG cU) AncS} Wm{Ly(Mz No Nw Ny) Ik(Jh Mu Nv Qd) Ns(Nw Qd) MmNw} hR{hW(hX iB jD jH jQ jR) iB(jD jH) jI(hA jU) hXjH} cU{bE(Ad cZ) cK(bU cF) AncM AxDc aJbR cXfR} dN{bG(aY bE cE cS) Cq(DB) bFcE cXfR} cS{AxDc DdbF DkbU aUbA aVcF bGbR} Mm{Lu(Hx Nx Pe) IkPe PzJk} Mw{Hu(Mx Nl Oh) NsNl LuMy} Ax{Dc(aX bC bH dI)} Lx{Mh(Ij Jo) MaMb HxJh} Nw{Ma(Hx Mb) Oi(Mg My)} Mk{Mu(Pa Pe) NqPe} bA{bJ(aI Bg) bEbG} bU{dI(Aw Cq) ExcI} jI{hAjP hWjG jUjV} Dd{bF(aX cE)} Mp{Nx(Hq Pa)} AnaOaX AwBoEx DkaLbE NqMyHx MaMbPe HuJkOm nTlXkG hVhWjR

Constrained panels with 3 analytes, where 1.0E-7 >= 'AUC p-value' > 1.0E-8. Contains 2,408 panels of 645,860 total panels evaluated. : Jp{Io(aA Ih Ii Im Js Jt Ma Mq Mv Mz Nm No Nu Ny Oh Om Pa Qd Qe) Nq(Hu Hv Hw Ij Ir Iv Jj Lw Mi Mr My Mz Nr Ns Oy Pb Pe Qa) Mp(Hv Hw Ir Iv Jj Jk Jo Mr Mu Na Nf Ni Nn Nr Ns Nw Ok Pc) Ms(Ij Iu Jg Jo Lh Lw Mb Mg Mi Mu My Nv Nx Om Pc Po Qb) Pb(Hw Ii In Jo Mg Mq Mt Mu Nb Nu Om Pe Po) Mm(Hw Ii Ij Il Jk Lx Mx Nb Po Pz Qb Qe) Qa(Jk Lw Lx Ma Mg Mi Mr Nv Oh Pa Pc Pz) Jj(Hw Hx Ij Im Jo Lh My Nn Nv Pa Qb Qe) Nn(Hu Hv Ir Iv Mi Mr Mz Nf Nr Ok) Ma(In Lh Lx Mt Mx Nv Pa Pe Po Qb) Mt(Lw Mh Mi My Nr Ny Oh Pc) Mg(In Jq Mx Ng Og Pa Pe) Pc(Il In Mx Oi Pa Pc Po) Jn(Hw Jo Lu Mr Nt Oh) Og(Ij Lh Lx Mu Nx Po) Lw(Lh Mx Pa Pe Po) Jq(Is Lx Nd Nv Pe) Ng(Lx Mu Nv Po) Jk(Hu Oi Ok Pz) Pa(Iv Mu Nm Ok) Nj(Lu Mb Na) Po(Mh My) Lx(Iv Jo) Mi(Nv Pe) Mw(Hu Ns) Hx(Lu Oh) Jg(Mx Oi) MfaA MhLh MuHw OkPe} Og{Jg(aA Hr Ii Ij Il In Io Ir Jk Jq Lx Mg Mp Mw Mx Ok Pa Po Qa Qe) Mu(Hw In Iu Jh Jk Jo Jq Lw Mi Mp Mt Nn Nr Nw Pa Pe Qb Qe) Mw(Ih Il Im Ir Iu Iv Jk Jo Mg Mn No Nt Nx Om Pe Po Qa Qe) Nx(Hw Il Ir Iu Iv Jh Jk Mg Mi Mt Mx Nt Nv Nw Qa Qd Qe) Hx(Im Jj Jk Lw Lx Mg Mn Mt Mv Nt Nu Nv Qa) Nn(Ii Iu Lx Mi Mr Mv Nr Pa Po Qe) Nq(Hw Il Ir Jq Mp Nv Nw Ok Qe) Lx(Jh Jk Jo Mg Mi Mp Mv Nv Ny) Ip(In Lw Mb Md Na Nf Nm Oh Pd) Jn(Iu Mi Mv Nm Nt Nw Pa Pc Pe) Jk(aA Io Iv Lh Mm Mt Ok Om) Lv(Ij Jt Li Mg Nm Ny Pd) Jh(Hw Ii Iu Jo Nk Nr Po) Pg(Ir Jt Mv Mz Ns Nt Pc) Mm(Ii Ij Lh Mt Nb Qe) Nv(Ij Ir Jo Mn Mt Nw) Is(Jo Jq Mz Nf Nr) Om(Il Ir Ji Lh Pa) Mv(aA Lh Nw Pe) My(Jq Nj Nw Ok) Qe(Fr Ma Ok) Po(Lz Ny) Mt(Jt Nf) Nj(Mi Nb) Ij(Nw Ok) FrJt MaLh MgJi IlNw} Mt{Jj(Hw Lx Ma Mg Mi Mm Mp Nd Nn Nt Om Pa Pe Po Qa) Lw(Et Is Lu Lx Mr Mu Mz Nb Nv Nw Ny Pa Pe Po) Mp(Et Hv In Ir Mr Mu Nb Ni Nw Ok Om Pa Pe) Pc(Et Hv Hw Lu Mi Mr Mz Nf Ni Nr Nw Ok Po) Pa(Hv Lv Ma Mk Mm Mu Mz Ni Nq Oh Ok Om) Lx(Hq Hv Jo Ly Mh Mz Ng Ni Nn Om Pb) Oi(aA Iu Jt Ma Mr Ms Mz Nr Oh Qd) Mm(In Ir Jq Lh Mz Nb Nv Ok Pe) Nn(Hu Hv Hw Ij In Ir Om Pe) Nq(Hv Hw In Ir Lv Mr Mz Pe) Jq(aA Jo Ma Md Ml Mr Nt Pb) Mu(Hu Jo Ml Mr Mz Pe) Ng(Jg Jh Jo Mw Om Pg) Et(Hw My Nt Ny Pb) Lv(Im Jk No Nt Pg) Mb(Iv Mg Nw Qd) Mi(Hv Ly Mz Om) Ms(In Jh Nf Oh) Ik(Iv Jk Nt Om) Nv(Hv Mh Ny Oe) Pb(In Is Nr Oy) Mz(Mg Mr Pe) Nb(Ma Oh Oy) Io(Jt Ma Qd) Lh(aA Ly My) Mh(Is Nj) Ml(Nr Pe) Hu(Jg Jk) Jn(Jo Nt) Lj(Li Qa) NsNd MgJo MyJi NiNk HvNw HwOm IrJs PzJg} Ip{Jo(Jg Jq Jt Ma Mg Mm Ms Mz Nj Nn Nq Nv Nw Pa Pb Qd) Pc(Hw Il Im Ir Iv Mi Mv Mx Nb No Nr Nt Nw Pa Qd Qe) Lu(Hv Hw In Iu Iv Jt Lz Mb Na Nf Nm Nr Pb Qd) Lw(Hw Il Im Ir Iv Jh Mr Ms Mv Nb No Nr Nw Qd) Oh(Hv Ii Ij Im In Ir Iv Mr Mv My Na Nr Nx Qd) Mg(Io Ir Mr Ms Mx No Pa Pe Qd) Jt(Ma Mm Mp Nn Nq Nv Pa Po) Pb(Hv Il In Li Mw Na Nq Nx) Mm(Hv Md Na Nf Ni Nq) Mi(Hv Na Ni Pe Qd) Iu(Io Jh Mn Ms Nw) Md(Hw Jg Mv Mx) Nf(Mp Nn Pa Qd) Nr(Nw Oz Qd) Mb(Iv Li Ms) Mv(Ir Iv Na) Ij(Ms Nd Nj) Mp(Na Ni) Mw(Io Ng) My(Jh Lz) Hw(Pa Pe) Ir(It Nw) Jl(Jj Jr) WmIk NnIv MaNa MkPa MrMz NgJh IhOi} Jj{Qe(Hw Hx Ii Io Jg Jq Lx Ma Mi Mm Mu My Mz Nb Nd Nt Ok Pa Po) Hx(Im Jg Jh Jo Jq Mg Mp Mu Mv Nn Ny Ok Qa Qd) Il(Jh Mg Mn Mv Mw My Nj Nn Nq Ny Pd Qa) Nv(Hw Ir Jq Lx Mi Mr Mu No Nt Om Pc Qd) Ij(Lu Lx Mi Mm Mp Mv My Nd Nn Nw Pa) Jn(Hw Iu Jg Lu Mi Nd Nt Om Pd Pe Po) Qa(Lx Ma Mg Mi Mp My Nn Nq Pa Po) My(Im Ir Jq Lx Ma Ny Qb Qd) Nq(Ir Mx Nj Nw Nx Ny) Pe(Jq Mg Mp Mu Nn Om) Jo(Ir Mn Nw Pb Qd) Lh(Ml Mm Nj Om Pb) Nx(Ir Mp Nn Pa Po) Qb(Ma Mg Mm Mu) Is(Jh Nf Om) Jk(aA No Oh) Fr(Hw Mp) Ma(Ir Mx) NnIr MgPa MmHu MuNj JqJr} Lv{Io(Ih Im Jh Jt Li Lz Mn Nc Nl Ny Qb Qd Qe) Im(Mb Mi Mz Nb Nf Nw Oh Pa Pc Pe Po) Mp(Hw Ir Jo Lu Mr Nf Ns Pa Po Qa) Jg(Hw Ih Iu Lu Mb Nr Ns Oi Pz Qa) Oh(Ii Jk Mw My Nf No Nt Oi Pg Qa) Om(Hw Iu Lw Mr Ms Mz Nq Ok Oy Pc) Ma(Hw Ih Ir Jk Lw Nb Nf Nr Qa) Jh(Hw Lu Lw Mz Nf Nr Pa Pc Qa) Nn(Ii Ir Ms Mz No Po) Lx(Ir Lw Ly Mg Mz) Iv(Lw My Nf Nq Pc) Nw(Mb My Nt Qa Wm) Lu(Hx Jq Ok Qa) Pb(Jk Mr Nr Po) Fr(Na No Nt) Mb(Ih Mh Qd) Mu(Mr Mz No) Nf(Jl Nl Pg) Hx(Iu Lw Mg) Mz(Pg Wm) NoMg NtJl NgJo NjIl HqPf JkOk PcPg} Nj{Ma(In Io Jk Jt Mr Mu Mv My Nq Nt Om) Mz(Hw Iu Jh Jo Jt Lw Mi Mq Nd) Oh(Fp Hw Im Jg Mj Nr Nt Ny Om) Mv(Hw Im Ms Na Nb Nd Nr Pa) Mn(Ij In Lu Mj Mq Na Nd) Mw(In Mj Ms My Na Nd Nu) Jh(Hw Ii Mj Mp Nd Nn Nr) Jk(Ih In Js Mq Ms Ni Nr) My(Hx Ir Md Mx Ny Pa) Nq(Iv Mb Nf Nt Oy) Nb(Lw Md Mg Nd Nv) Jg(Hw Io Lu Md Nf) Mp(Iv Jo Nf Nt) Mu(Ik Lw Na Pc) Hx(Hw Jt Nd Nf) Po(Iv Mb Md) Im(Hw Ii Nr) Pe(Ik Lj Mb) Nn(Na Nf) Lu(Ij Ir) Ms(Ii Ij) Ni(Qd Qe) Lh(Ly Pb) Nw(Jo Jt) Pa(Nv Nx) WmJq MdIr MiIo HvNy} Is{Ma(aA Jq Lh Lw Lx Nw Oi Ok Pa Pc Po) Pc(Hw Jq Lh Lu Lx Ni Oi Ok Pa Pe) Mm(Hw Jq Lh Lx Mr Mz Nf Ni Pa) It(Hv Ij In Ir Jn Jo Mz Na Qa) Lw(Lh Lu Lx Nq Nw Oi Pa Pe) Nn(Hw Jo Mi Mr Ni No Pe) Mp(aA Hw Mu Mz Ni Nw Om) Nq(Hw Jm Jq My Mz Pe) Mg(aA Jq Lu Mz Ok Pe) Ms(aA Jh Mz Nb Nf Nt) Mu(aA Ik Lh Ng Oi) Jg(Hu My Ng Ns Oy) Lx(Jm Jq Ly Mh) Jh(Hu My Ns Oy) Pa(Jq Mh Mk Ok) Pb(Jo Nr Ny Om) Po(Mh Oy) Lu(Oi Ok) Hw(Ml Nw) Om(Mi Oh) MhNb MvOy MwNg NdJm NvOi} Jn{Lw(Hw Hx Io Jk Lh Lu Mi Mr Mz Nb Nd Nv Nw Om Pa Pe Po) Ms(Hx Jh Lh Mg Mi Mn Mv My Nv Nx Pa Po) Pc(Lh Lu Mi Nd Nv Nw Ok Om Pa Pe Po) Ma(Jg Jq Lu Mr Mz No Nr Oi Om) Io(Jo Mr Nd Nm Nr Ok Pe) Jg(Hw My Mz Ng Ns Oh Oy) Mg(aA In Ng Nw Ok Pa) Jh(Hu My Ns Oi Oy) Nt(Mp Mu Nn Nq) Ml(Hw Ii Mz Nr) Nw(Lu Mh Nd Pe) Pb(Lh Nb Ny Pe) Jk(Hu Mz Oh) Ok(Mi Nd Nv) Om(Lu Mi Oh) No(Mp Mu) It(Hw In) Lh(aA Mh) WmJm PoOh LxLy IuOi LiLj NvOe} Pb{Fr(Hv Hw In Iv Mq Mr Mz Na Nb Nr Nt Om Pe Qa) Jl(Hw Jt Lw Md Mz Na Nf No Ny Ok) Om(Hw Iv Jo Lh Mx Nv Pa Po Qa Qe) Pe(Jh Jk Jo Jq Lw Mg Nq Nt Nx Qa) Mu(Hw Ir Jo Jq Nv Nx Pa Qa Qe) Ny(Et Hq Jq Lw Lx Oh Po) Qa(Jk Ma Mg Nv Nw Pa) Nw(Hx Io Jk Jo Lh) Ok(Il Jk Ma Mg Nq) Nb(Jq Mm Mp Nn) Po(Mg Mm Nn) Lx(Hv Ij My) Hx(Jh Jk Mi) Lh(Io Mg Nq) Mr(Ma Mp) Ij(Jg Jh) Ji(Jo Pd) Nv(Io Jq) EtJo NqNr LwPa MiJh MwOy} Io{Nv(Hw Im Iv Jo Jq Lh Lw Mi Mp Mr Na Ng No Ns Oh Pa Pc Pe Qa) Nw(aA Hv Iu Iv Jt Mb Mq Mv Nm No Nr Nt Oh Ok Qd) Qa(Hx Jh Lh Lw Ma Ml Mp Nn Nx Ok) Ir(Jg Jh Ma Mn Mp Nn Nq Nx Om) Jg(aA Mi Mx Nl Pa Pe Qb) Mm(Il Mn Mx Mz Nb Nx) Ma(Lh Mx Qb Qe) Hx(Lw Mn Mp Ok) Nx(Im Mp Ny Qb) Jk(aA Jq Lh) Ny(Nb Nl Nn) Qe(Jh Lh) Pg(Ik Qd) NnPa LwPe MhLh MiMn MpIj MyaA NkOk} Nn{Oi(Ij Iu Jg Jk Jo Mn Mp Nr Nt Om Pa Pe Po Qa Qb) Pg(Hw Jo Mr Ms Mu My Mz Ni Ns Pc Qa) Hu(aA Et Hw Hx Ij Il Mx Ny Pa) Ms(aA Lh Nb Nx Ok Po) Pc(aA Mq Mr Nb Po) Et(Mi Mr No Nt) Il(Ij Lw Ns Ok) Ji(Ma Mr No Nt) Jq(Mi Mp Mu Nr) aA(In Mg Mx Mz) Hx(Ma Ni Ok) Jl(Jr No Nt) Nw(In Pa Qa) Fr(Lh Ng) Lu(Ny Qb) Ok(Pa Pe) LwMx MaLh MpNx MwOy MyNv} Jq{Et(Lh Lx Mi Mr Mu Nd No Nt Pc) Pc(Hx Il Jl Mp Nv Pg Po) Ma(Ji Lh Nv Pa Pe Po) Mm(aA Hx Ji Nv Pa Qa) Po(Md Mh Ms Ny) Nq(Mr My Ng Nr) Ml(Hw Hx Nb Qa) Mp(Fr Hq Ji Mr) Mu(Lh Ms Pa Pe) Lx(Md Mg Mh) Jk(Hu Ms Ok) Pg(Mi No Pa) Nu(Nd Nv) Hw(Jg Jh) Il(It Ok) Qa(Jg Qc) WmLy MgPa MiJl MwOy NdJi ImNv QcQe} Oy{Mw(Lh Lu Lw Lx Ml Mm Mr Mu Mz Nd Nf Nq Nv Nx Oh Pe Pf) Pg(Jk Jo Lh Mg Mi Mv Mz Nb Nf Nq Nw Pa Pe Po) Et(Jh Mu Mv Nb Nq Om Po) Lx(Hw Hx Ij Jk Mh) Jl(Jg Jk Nb Om Pa) Hx(Jh Ma Om) Jk(Lh Oh Om) Pe(Fr Mm Om) Po(Ji Lj) Mu(Pa Qb) FrPa NqJi MpLh} Ms{Nw(Ij Jg Jh Lh Mg Mm Mp Mu Mw My Ok Om) Mw(Hx Jh Mi Mp Mu Mx Mz No Ny Ok) Fr(Ij In Jh Jo Lh Mr Nb Pe) Lx(Mg My Nq Nx) Hx(Ma Mp Ok Om) Lh(Jg Ma Mu Om) Mm(Ij Nr) NqaA MuNx MxJg NfJl IvOm JhPg} Ng{Jg(Et Fr Hx Il Ji Jl Mp Nq Nv Pe Po) Fr(Ih Jk

Figure 34 Continued

Lx Md Mr Mu Nb Nf Om) Nq(Lr Jh Mp My Nv Nw Pe Qe) Om(Et Hx Jl Lh Pa Pe) Mm(Jk Lh Pe) Mu(Lh My Qb) Mv(Jl Mp Pg) Lx(Mg Nx)
Mw(Jl Pg) Nv(Ma Mp) NwPg} Ma{Hx(aA Lw Lx Mm Mp Mu My Mz Oi Ok Om Pc) Lh(aA Ji Jo Lw Ml Mu) Mb(Et Ir Md No Nv) Ji(Mi Mr
Nt Pc) Jl(Jr Mz Nf No) Ik(Pe Wm) Nx(aA Pa) EtMr MpaA NaPg InNv PzQe QaNw NyPc} Et{Pc(Lx Mi Mr Nf No Nr Nt Nw) Lw(Lx Mr Nf
Nq Po) My(Jg Jh Mv Nb Om) Mp(Hw Nf No Nw) Nq(Hu Ir Ok) Mz(Fr Mi Nt) No(Ji Mu) Hw(Fr Nw) Oh(Om Pe) aA(Mg Mu) NtNw}
Mm{aA(Hx Ij Jk Lw Mu Mz Nv Pe Qa) Lu(Ij In Jk Nw Qa Qb Qe) Hu(Hr Jk Mj) Qe(In Pa Pz) Lx(Ij Ji) Qa(Nv Pe) Nw(Hx Jk) Ok(Il Pa) WmQd
MzPe lnNv JiLh JlJr} cD{Ef(aJ aO bB bV cS dF) bH(aJ aP bA dM FR) Cq(aP bL cU dN) bG(aA bW dE dl) Ex(bB bE De) dA(aO Aw bQ)
Dk(aX bW) AnaX AwbS BgdI FwdK bVcK} Jl{Nb(Hx Ml My Ny Of) Pc(Lh Nf Ni Nt Ok) Jr(Mh Mp Mu Nq) Lw(aA Mg Mu) Mz(Mg Mi Nq)
My(Jg Om) Ok(Mp Nq) NoMg LxLy MiNi NdHq OfOm} Pg{Ly(Lh Lx Mi Mr Nt) My(Mv Mw Nq Om) Mp(Mk Mz Ns) Jg(Hu Ik Ns) Jm(Iu
Nt) Nw(Hw Mh) Om(Of Oh) LuLw MiHq IkJh OkPc OzPe} Lh{Jo(Hw Mg Ml Mp Nv) Ii(Fr Nv Nw Qa) My(Jh Nq Om) Pc(aA Ji Oi) Lw(aA
Mu) Mh(Nw Om) Mp(Nw Ok) FrHu MlMz JgOi} Hx{Mu(Lw Mp My Of Oh Pc) Jh(Hw Lw Mp Oh Pc) Nq(Hu Hv Lw Oh) Om(Ml My Ny)
Lx(Ij Mh) Jg(Oi Pz) MhNw} bE{Ef(Ad As Cq Cu Cw dD) cU(Cq Cw Dc Dd Dk) Ex(al cJ dK) Bg(bA bV) CqdD albA bGcT bQdH} aA{Lw(Fr
Il Nq) Mg(Oi Pa) Pc(Il Jo) bG(cJ dN) AxEf CqCx NqQa MuHu bFcJ bHcU cSdH mFmP jKlM} Nw{Oi(Iv Jk Mu Mv Qe) Wm(Ik Oh) Nq(In
Qa) Ml(Hw Mz) My(Il Jk) LwJk LxQa MhPe} An{aX(aH al Cq) aO(bC bJ) cJ(bZ Ef) cS(bR Cq) dK(cU dF) dN(Bg bH)} Mp{Hq(Hu Mu Nv
Ny) Ns(Nv Nx) Jh(Nx Qe) Ny(Pa Pc) NrMk MzPf OzPa} My{Mw(Mv Nq Nx Om) Ji(Jg Jh Mv Nb) Lx(Hq Ij Nx) NqNy JhNv} cJ{bH(aO Cv
Dk) Dc(Ax dN) AddI CqdE CvcS DbEf ExbU cFcK} Fr{In(Hu Ml Of) On(Mv Mw Ns) bU(dA dI) MkPe bFcE} Dd{Ax(aJ aP dF Gl) bF(dK
dN) aObJ cUdE} Ef{cl(bV cS Gl) Ex(aV Ax) dB(Bn Cp) bAbR} Lx{Mh(Jh Nd Nx) Ml(Hw Ij) Ny(Ij Nx)} bJ{aO(aM aN bA Cq) bA(bB Ch)
DccU} dH{aP(bG bQ dN) Awdl aJbB bQdN cKcU} Ex{bR(cU dK) AxDc BodK bBcl bUcP} Ji{Pc(Hu Hw Mr Pe) NqHu MhMr} cS{bR(dA
dM) AsdB CqDb aUcT bAcY} Wm{Ik(Mi Mz Nb Ny) MIMz} Mu{Oi(Iv Qb) Mxlk Hulj PzQe} Jg{Pz(Pe Qa Qe) Oi(Pe Qa)} Pa{Mk(Nq Om
On) MhOm JhNx} dl{Aw(cL Dk) CqdB DecL DkbU} bG{dK(bA Cu dM) aJdN} cU{DcdE bRdA cKcL cNfR} mF{nMkC nRnT nIoQ kGkK}
Nq{HuQb IlJm NyPc} Jh{Ny(Hv Pc) PoMh} bU{dA(aO Aw) bVcK} fR{Cq(CX) cMcX} jR{hVjP hWjD jEjF} Mw{LwNl HuHv} li{Jk(No
Pe)} bC{CxDc aOcL} LuJrJt aPbFcE nUnBoQ iBjDjP jHjUjV Constrained panels with 3 analytes, where 1.0E-6 >= 'AUC p-value' > 1.0E-7. Contains 3,592 panels of 645,860 total panels evaluated. :

Og{Jg(Hv Hw Ih Iu Iv Jh Jo Js Lu Lw Ma Md Mi Mj Mq Mr Mt Mu Mz Nb Nn No Nq Nr Nt Nw Oh Om Pd Qd) Jk(Hu Hw Ij Ir Jh Jo Lw Ma
Mg Mi Mp Mr Mv Mz Nb Ni Nm Nn No Nq Nr Nt Nv Oh Pa Pc Pe Pg Po) Jh(Il Ir Iv Jp Lz Mh Mj Mm Mp Mr Mt My Mz Nb Nj No Nt Nu Nw
Ny Ok Pe Qa Qe) Po(Hw Hx Jo Jq Lw Lx Ma Mg Mi Mm Mp Mu My Nq Nw Oh Ok Pb Pc Pe Qa Qe) Om(aA Hw Iu Jt Lw Lx Mg Mi Mm Mp
Mr Mt Mu Mz Nb Nn No Nq Nt Oh Pc Pe) Nw(Hw In Iv Jp Lh Lu Lw Lx Ma Mg Mt Mz Nn Nu Ok Pa Pe Qa Qe) Nv(Hw In Iv Jt Lw Mr Mv
Mz Nb Nf Nr Nt Oh Pa Pc Pe Qe) Mu(Ih Ij Ir Iv Lx Mg Mm Mr Mv Mz Nb Nf Nq Nt Oh Pc) Hx(Ir Iu Iv Mi My Mz Nm No Oh Pc Pd Pe Qd
Qe) Nq(Hv Ii Iv Lx Mi Mq Mr Mz Nb Nr Pa Pe Qa) Ny(Hw Io Mg Mi Mq Mt Mv My Nj Nt Nu Nx Pb) Mv(Ii Jp Lv Mr Mz Nb No Nr Ok Pa
Qe) Lw(Il Jn Jp Lh Lv Mi Mp My Pe Qe) Qe(Im Io Iv Jq Lx Mg Mp Mt Nm) Nn(Ij Iv Mp Mq Mz Nb Nt Qb) Jn(Ii Jo Jq Jt Mr Mz Nb Nr) Jp(Ii
Il Iu Jo Mt Nb Nm Pa) Nx(Ij Ma Mr My Mz Nu Oh Pa) Mg(Ir Jq Lh Mz Pa Pe Qa) Lx(Hv Hw Ij Ir Jq Nt) Mw(Hw Ij Js Jt Nb Qd) Ma(Il Iv Pa Pe
Qb) Mp(Ii Ij Mi Nb Nt) Mt(Ml Nt Pb Qa) Ok(Il Iv Nk Pc) Mm(Il Pa) My(Mz Wm) Jq(Iv Lh) Pc(Lh Qa) NmIl NrNj MnIr NbPg IjJj JiJo}
Jp{Ma(Hr Hw Ii Ij Ir Iv Jk Jo Jq Lw Mb Mm Mr Mu Mz Nb Nd No Nr Nx Ok Pc Qe) Pc(Hr Hw Ii Im Ir Iv Jk Jo Jq Lh Lx Mi Mu Mz Nb Nd Nt
Nv Qd Qe) Lw(Hw Im Ir Iu Iv Jo Lu Lx Mi Mr Mu Mz Nb Nd Nt Nv Nw Qe) Mg(Hv Hw Ir Iv Jj Lu Mb Mr Mz Nb Nf No Nr Oh Ok Qe)
Mm(Fp Hr Hv Iv Jo Jt Mh Mr Na Nf Ni Nr Nt Ok Pd) Ms(Ih Ii Jh Jk Jt Mn Mq Mr Mv Mz Nb Nm Nr Pa Pe) Jj(Hq Ih In Ir Iu Iv Jm Lx Mi Mv
Mx Nt Nx Ny Po) Pa(Hv Hw In Ir Jk Jo Mf Mk Mz Na Ni Oh Om Pb) Lx(Hq Hv Hw Ir Mu Mz Na Ni Nm Oh Ok Om Pb) Oh(Il In Iv Jk Lh Mu
Nt Nv Oi Pe Po) Io(In Jg Jh Md Mr Na Nd Nf Nr Pd) Nv(Hv Hw Ir Jo Mz Ni Oy Pb) Nn(Jo Mu Na Ni Nt Om Qd) Nq(Jo Na Nf Ni No Ok Om)
Iu(Ij In Jq Mu Mx Mz Nw) Jk(Hw Ir Jt Ng Ni Nr Qd) Nb(Hx Mh Ml My Nd Ny) Pb(Mr Mz Nr Nx Ny Pd) Mi(In Ir Jq Mz Om) Mp(Jt No Nt Om
Pd) Lu(Ij Im Nx Qe) Mu(Iv Jo Mr Nr) Hw(Jq Mz Nw Om) Nt(aA Jq Ne) Ml(In Mt Mz) Nd(Ij In Nx) Ni(Nj Qb) Qd(Mb Qc) Jg(Mq Pz) Jn(Jt Nr)
Jo(Jq Ng) PoOy NsJh Mhli MrJq MvMy IhOi ImQe} Jj{My(Fp Hq Hu Hw Ih Iv Jg Jh Jm Lu Lw Mg Mi Mm Mn Mp Mw Mz Nj Nn No Nt Ok
Pa Po) Mn(Hw Ir Iu Lu Mg Mp Ms Mu Mv Mx Nn Nq Nt Nx Ok Pa Qb Qd) Qa(Hw Iu Jg Jt Lw Ml Mr Mu Mz Nb Nd No Nt Oh Om Pc Pe)
Nq(Fp Hr Ih Ii Im In Jg Jh Jo Mp Mw Ok Om Po Qd) Il(Ih Im Ir Iv Jq Mi Mp Mu Nr Nt Pa Po Qb Qd) Nx(Hw Ih Iu Iv Jg Jh Ma Mg Mu Mv
Mw Mx Nu Ny) Qe(Ij Iu Lw Md Mr Mv Nf No Nr Oh Om Pc Pd) Ma(Hr Ih Ij In Iv Jo Lh Lu Nk Nl Pa Po) Mt(Iu Jg Jl Lw Mr Mz Nb Nf No Nr
Oh Pc) Jo(Ih Im Jh Jq Mw Mz Ny Ok Om Pa Po) Hx(Ir Iv Lw Lx Mz Nt Nu Pc Pd Po) Qd(Io Jg Lx Mg Mp Mv Mw Nd Nn Po) Mv(Im Ir Mx Nj
Nw Ny Pa Qb) Ij(Hw Iu Iv Jg Mg Mr Mu No) Jn(Jh Jl Lw Mr Nb No Nr Pc) Ir(Jg Jh Mg Mp Mu Mw Om) Pe(Iu Lw Mi Nt Oh Pc) Po(Jq Mg
Mp Mu Ok) Om(Iv Lu Ms Nl Pa) Mu(Fr Jq Nw Ny) Qb(Jg Lu Mp Nn) Nt(Fr Nj Ny) Mg(Nw Ny Ok) Jg(Io Lh Oi) Jl(Is Jr Mm) Mw(Ms Pa)
NnLh MpHu NdNw NjHq IhOk ImPa} Ms{Jg(aA Fr Hw Ii Ij Il In Io Ir Iv Jo Jq Lu Lx Mi Mm Mp Mu My Mz Nb Nn Nq Nv Nx Oi Ok Pa Pe
Po Qa Qb Qd Qe) Nq(Hu Hw Ir Iv Lh Lv Mb Mm Mp Mr Mu Mz Nb Nx Ny Ok Om Pe Pg Po Qa Qb Qe) Nw(Hv Hw Ii In Iu Iv Jo Lw Lx Mb
Mi Mr Mv Mz Na Nb Nr Nt Nv Pa Pc Pe) Mw(aA Hw Ir Iv Lv Lx Ma Mn Mq Na Nl Nm Nn Nr Nt Nu Oh Oy Po Qa Qe) Om(aA Fr Hw Ir Iu Jq
Lw Lx Mi Mm Mp Nb Nn Nv Oh Pa Pb Pc Pe Qa Qe) Mu(aA Fr Iv Jo Lx Mg Mm Mn Mp Nb Nn Nv Ok Pa Pb Pe Po Qb Qe) Nn(Fr Ii Ir Mi
Mp Mr Mz Nr Nv Ny Oz Pa Pe Qe) Mp(Ii Jo Lu Lx Mi Mm Nb Nt Nu Pe Po) Jn(Iu Jo Jt Lw Mb Mr Mz Nb Nr Oh Pe) Hx(Jh Jq Lw Lx Mn Nx
Pb Pc) Jq(Hw Lh Lx Mi Mn My Pc) Fr(Jt Lw Mi Nm Nt Pc) Lh(Jh Lw Mh Pb Pg) Nx(Im Ma Mx Po Qa) Ok(Jh Jk Mg Mv My) Mm(Jk Mn My
Qb) Po(Jh Lw Ma) Pg(Mg Pa Pc) Lx(Lw Mn) Ma(Ij Mb) My(aA Nj) NtMb NuNv Nflp NjPa} Ma{Lx(Hw Ij In Ir Jo Jq Lw Mh Nn Nv Nw Nx
Oh Pc Qe) Mb(Hx Ih Io Iv Jk Mu Mx Nn Ny Pa Po Qa Qb Qd Qe) Nw(Hv Hw Ij In Ir Iv Jk Jo Jq Lh Mr Nr Pa Pe) Mt(Hv Hw In Ir Is Lw Mr
Mz Nf Nr Pb Pe Po) Qb(Jh Lu Lw Mi Mm Mp Mq Mu Nb Nn Oh Oi Pc) Pa(Io Iv Jg Jh Lw Mk Nb Ng Nn Oh Ok Om) Hx(Hw Ir Iv Jg Mi No
Nq Nt Oh Qa) Pe(Io Is Jg Lw Mm Mp Nn Ok Pc Pg) Nj(Ij Im Md Mq Na Nd Nf Nr Oh) Nv(Hv Hw Im Lw Mi Mz Na Nn Nr) Ir(Ik Jg Mm Mp
Nn Oi Ok Om) Pb(Hw Ii Jo Nb No Nr Nx Om) Is(Hw Mi Mr Mz Nf No Nt) Jq(aA Hw Mp Nd Nq Qa Qe) Ny(Hv Hw Lw Md Nd Nr Oh) aA(In
Io Jg Jk Mu Om) Mx(Jg Lw Nq Oi) Jk(Hu Io Ok Oy) Lh(Mh Mm Mz Pc) Po(Jh Lw Pc) Nn(Hw Il Oi) Lv(Iu Jt Na) Iv(Ik Io Oi) Qe(Mm Mp Oi)
Mw(My Oy) Qa(Ml Mm) Jn(Jo Nt) Nx(Im Mp) Pg(Hw Mr) NoJi Mylo MzNl IjIk} Pb{Om(Ir Iu Jt Lu Lw Lx Mh Mi Mm Mp Mr Mu Nb Nn No
Nq Nr Nt Nw Oh Ok Pc Qd) Mu(Fr Hv Ii Iu Iv Lw Lx Mh Mi Mn Mp Mq Nb Nr Nt Nw Ok Pd Po Qd) Po(Ij Im Jh Jk Mp Nq Nr Nt Nw Nx Pc
Pe Qa Qd Qe) Nw(Hv Hw Ij In Mq Mt Mv Mz Ni Nq Nr Nu Ok Pe) Lx(Hx Im In Jk Jo Mg Nj Nr Nt Nx Qa Qe) Nq(Hr Ii Jq Mi Mq Mr Mt Nb
Nu Nx) Pe(Hw Im Jt Mb Mi Mz Nb No Pc Qd) Hx(Jg Li Lw Mg Mn Mt Ni Nx Ok) Qa(Hw Jo Mq Mr Mt Nb Nr Ny Pd) Fr(Jt Mp Mt Nf Ni No
Ny Ok) Ij(Hw Iu Li Mg Mq Mr No Pa) Hw(Jg Jh Lv Mp Pa Qe) Jk(Im Lh Mi Mz Nb Qe) Nt(Io Jg Jh Ok Pa) Ip(Md Mg Nf Oz Pd) Jg(Mi Mq
Mx Pa) Lh(aA Jq No Pc) Ny(Iu Mm Mx Pc) Nr(Jn Mm Mw) Mt(Ii Na Pa) Nb(Im Jh Qd) Lv(Jo Pd) Mw(Mx Mz) Jq(Mi Pa) Ok(Pa Qe) NoMg
ImNv JnJo} Mt{Mm(Hv Hw Ij Iv Jk Jt Lx Mr Mu Na Nf Ni No Nr Nw Po Qa) Hw(Is Lw Lx Md Mg Mh Mi Mp Mu Mz Ns Nw Oh Pa Pg)
Qa(Lw Lx Mg Mi Ml Mp Nn Nv Nw Oh Pa Pc Pg Qc) Oh(Hv In Jo Lx Mr Mu Nf Nr Nt Om Pe Po) Nn(Ii Jo Mi Mr Mu Na Ni Nr Nt Ok Po)

DkbU bGbR dFdG} Hu{Mw(Lz Nd) ImJk} Qd{Mb(Im Mh) WmLy} nB{nR(mW oQ} kGoQ} nC{kG(kC kO) mPmU} Dc{CxaJ bGdN}
Dd{BgdN bFdE} Mf{aA(Il Pa)} Iv{Jk(In Oi)} hR{hXlO jHIM} BoExcP CwbFcE EtNsMq MgIkPe NcNeJi iBjFjR

Constrained panels with 3 analytes, where 1.0E-5 >= 'AUC p-value' > 1.0E-6. Contains 4,705 panels of 645,860 total panels evaluated. :
Ma{Jj(Hv Hw Ii Iu Jp Lx Mb Mg Mi Mp Mu Mv Mz Nb Nc Nd Nf Nn Nq Nr Nt Nu Ny Om Pd Qd) Qe(Hv Hw Jg Jk Jo Lw Mi Mr Mt Mu Mz
Na Nb Nf Nn Nq Nv Nx Oh Ok Pa Pc Pe Po) Lx(Hv Ik Iv Jg Jk Ly Mm Mq Mu Mz Na Nb Nf Ng Nm Nr Og Ok Oy Pb Qa) Hw(Io Ir Iv Jg Jh
Lw Md Mi Mm Mn Mp Mu Ng Nq Nx Om Pa Pc Pe Po Qa) Nb(Hx Im Io Ir Iv Lw Ml Mm Mp Ms Mu My Nd Ng Nn Nv Og Oi Pc) Pa(Hv Ij In
Ir Jo Md Mm Mp Ms Mu Mz Ni Nm Nq Nv Pb Pc Po Qa) Po(Ik Im Ir Iv Mh Mm Mp Mu My Ng Nn Ns Oh Ok Oy Qa) Nw(Iu Jt Lw Mi Mm
Mu Mz Na Nd Nn No Nt Ok Pb Pc Wm) Pb(Hr Hv Ij Il In Jk Lu Mq Mu Mx Mz Nt Nu Nv Pd) Mb(Fp Ij Im Jh Js Lu Lz Mn Mr Nj Nt Nx Oh
Ok) Io(Ih Ii Jt Mi Mm Mp Mr Nc Nk Nl Nr Nt Nx Qd) Ng(Ii Iv Jg Jo Lh Mi Mp Mw My Nq Nu Nx Pe) Og(Hr Ii Ij In Jo Mi Mr Mt Mu My Mz
Nr Nt) Mm(Ii Ij In Jk Jq Lu Mx Mz Nv Nx Ok Wm) Qa(Jg Jk Mi Mp Mt Mu Mz Nn Nv Oh Ok Pe) Ir(Jk Lu Lw Mi Mr Mu Mz Nq Nv Pc Pe)
Nn(Hr Ii Ij In Iu Jq Mz Nl Nr Nx) Iv(Jg Jk Jo Lw Mi Mp Nf Nv Nx Oh) Ms(Ii Jg Mi Mr Mu My Nr Pe) In(Jg Mi Ml Mp Nl Nq Oh Pc) Jp(Hv Iu
Jt Md Na Nf Oh Qd) Jk(Hx Ih Ik Lw Mg Mt Oi) Jq(Jg Mi Mr Mu Nr Nt Wm) Mp(Hr Ii Ij Mr Mz Nt) Nv(Jo Mr Nf Nm Ok Pe) Nx(Mg Mi Nd
No Nr Qd) Oh(Hr Ii Il Jh Mx Pe) Lu(Im Jg Lw Pc Qd) Mz(Jg Nq Ok Om Pe) Mt(Jt Na No Ny) Ij(Jg Nl Nq Oi) Nr(Jh Mu Nq) Mg(Jo Lh Pe)
Hx(Jo Jt Qd) Ii(Jg Jh Pc) Il(Lw Mq Pc) Ok(Iu Nd Qd) Om(Ik Nl Pe) Mw(Hu Ns) Na(Ny Qb) Jn(Jl Jt) NoLh NqPe NuIk LwMy MxPc NiNj IuNy
QbJg} Jj{Im(Hv Hw Ii In Jg Js Lu Lw Lx Mg Mh Mi Mj Mn Mp Mq Mr Mu Mw Mx Nb Nd Nn Nr Nu Oh Pc Po) Mn(Ih Ii In Iv Jg Jh Jm Jq Js
Lx Mi Mm Mr Mz Nb Nd Nf Ni Nl No Nr Nu Ny Pd) Il(Fp Hv Hw Ii Iu Js Jt Li Lw Md Mf Mj Mq Mx Mz Nb Nd Nf Nm Nu Og Oh Pc Pf)
My(Hv Ii In Iu Js Md Mf Mh Mq Mr Mx Nc Nd Nf Nk Nl Nm Nr Nu Oh Pd) Jg(Hw Ih Ii In Jo Jp Lu Lx Mg Mi Mr Ms Mx Nb Nn Nr Ny Ok Pa
Pd Po) Mw(Hw In Iu Iv Jm Lu Lx Mg Mi Mm Mp Mr Mx Mz Nb Nd Nj Nn Nr Qb) Po(Hw Ir Iu Jh Jt Lw Lx Mb Mi Mm Mr Mz Nb Nt Ny Oh
Pa Pc Qb) Mv(Hw Ih Ii In Iv Jm Jo Jq Lx Mm Mp Mz Nb Nd Nl Nn Nt Ok Pd) Qd(Hw Ih Ii Ij Iu Iv Lw Mb Md Mi Mr Mu Nb Nf Nr Oh Pa
Wm) Ny(Hw Ii Io Iu Iv Lu Lx Mi Mm Mp Mr Mx Mz Nn Nu Ok Pa Pd) Ir(Hw Jq Lu Lw Lx Mi Mz Nb Nd Nt Ok Pa Pc) Jp(Hr Ii Jh Md Mq Mr
Nb Nd Nf Nm Nr Nu Pd) Om(Hw Iu Jq Lx Mi Mm Mp Mr Mu Nd Nn No Nt) Nq(Hv Hw Iv Jq Js Lx Mz Nb Nr Nt Pa Pd) Ok(Hw Iu Jm Lu Lx
Mi Mr Mu Nd Nv Pa Pd) Qb(Hu Hw Iu Lx Mi Mq Mz Nb Nk Nu Pa Pd) Jo(Iv Lw Lx Mm Mp Mu Nn Nt Oh Pc) Nx(Lx Mi Mr Mz Nd No Nr Pd)
Nn(Fp Ih In Mx Nj Oi Pa) Jh(Ij Iv Lx Mg Mx Pa Qe) Mp(Ih Lx Mi Mx Nj Nt) Mu(Ih Iv Mm Nl Pa Pd) Hx(Hw Iu Jt Mi Nd Oh) Nw(Iu Lx Mr
Nt) Pa(Mf Ni Nj Nr) Mg(Jm Mj Mx) Mm(Ih Jm Js) Jq(Jn Lu No) Jt(Jn Mt Qe) Nu(Hq Ih) Ij(Mz Oh) Jl(Et On) Lh(Lw Pc) WmLv NoPe NtMb
MjNj Hulq} Og{Im(Hw Ii Iv Jo Jq Jt Lx Mi Mj Mr Mt Mu My Mz Nb Nn Nq Nr Nt Nw Pa Pc Pd Pe Po Qd) My(Hw Ii Ij Il Ir Iu Iv Md Mi Mm
Mn Mq Mr Mx Na Nl Nm Nr Nu Pa Qb Qe) Qe(Hw Ii Ij Jo Jt Lu Md Mi Mr Mz Nb Nf Nr Nt Oh Pa Pc Pe) Nm(Hw Lx Mi Mr Mt Mu Mx Nl
Nn Nq Nr Nw Ny Pa Pe Po) Qa(Ii Jk Jo Lw Mi Mr Mu Mv Mz Nb Nf Nr Nt Pa Pe) Ok(Hw Ii Iu Jo Jq Lw Mi Mr Mt Mu Mx Mz Nt Pa Pd) Po(Ii
Ij Ir Iu Iv Mb Mf Mr Mv Mz Nb Nf Nt Pa) Jh(aA Ih Ij Jq Jt Lw Mg Mv Nn Nq Oh Pc Qb Qd) Nw(Ii Ir Iu Jo Mb Mi Mm Mr Nb Nf Nr Nt Ny Pc)
Ny(Hv Il Iu Iv Mr Mx Mz Na Nb Nr Pa Pc Pe) Nq(Fp Ij In Jo Mf Mm Mn Na Nt Oh Qd) Lx(Ii In Iv Lw Mr Mz Na Nf Ni Ns Pc) Mt(Hw Ii Ij Il
Ir Iu Iv Jo Nr Pa Pe) Mv(Hw Ir Iu Iv Jg Jo Mi Mp Mx Nj Nt) Jq(aA Ij Il Iu Jo Mi Ms Mx Nr Pc Pe) Mg(Li Ij Mp Mr Mx Nb Nn No Nr Qb)
Lw(Hu Ir Iu Mx Nn Nr Nt Nx) Mn(Ii Il Iu Iv Mr Mx Nn) Hx(Jo Jt Md Mr Nb Nf Pa) Nt(Io Ir Mb Nb Pa Pe) Nj(Ii Il Iu Oy Pa) Nn(Hv In Jo Jt)
Mi(Hu Il Pe Qb) Iv(Ij Il Ir Mz) Jg(Jt Na Nf Ni) Nx(Lu Nf Nr Pc) Mm(Hr Ih Jo) Mu(Jt No Qd) Jk(Jt Nf Qd) Pc(Hu Ir Pe) Mz(Lh Pe) Qb(Jo Mq)
Wmlp NoIj NuHw MpPa NbLh IlOh IrPd QdNv JoPe} Jg{Ms(Hv Ih Im Iu Jk Js Jt Lw Mb Md Mg Mj Mq Mr Na Nf Ng Ni No Nr Nt Oh Om
Pc) Io(Hu Hv Ii In Jo Js Jt Lw Lz Mb Md Mq Mr My Na Nd Nf Oh Oi Oy Pc Qd) Ng(Ij Iv Jo Jp Lu Md Mg Mm Mr Mv Mx My Mz Nn No Nr
Nw Oi Qb Qd Qe) My(aA Fr Il In Ir Jk Jp Jq Lu Lx Mx Mz Nv Nx Po Qa Qb Qd Qe) Oi(Hw Ih Im Jo Lu Lw Mg Mh Mi Mp Mz Nb Nq Nt Oh
Ok Pa Pc Po) Ns(aA Il Ir Jk Jp Jq Lh Lu Lx Mx Nv Nw Pa Po Qa Qb Qd Qe) Mz(Ir Iu Iv Md Mh Mi Ml Mp Nd Nl Ny Pa Pb Qa Qe) Oy(aA Il
In Ir Jp Lh Lu Mx Nw Nx Qa Qb Qd Qe) Hu(aA Il In Jp Lh Lu Mx Nw Pa Po Qa Qb Qe) Pz(Il Ir Iv Li Mi Mj Mm Mp Mx Nv Oh Po) Pb(Hv Ii
In Jo Mr Nb Nr Nu Ny Ok Po) Lu(Im Ir Mg Mq Nn Qb Qd Qe) Mp(Hw Ir Mx Nr Qa Qd Qe) Ni(Jp Lx Nj Nv Pa Qb Qe) Oh(Hx Il Ir Jh Mx Qa
Qe) Mx(Lw Lx Nn Nq Ok) Pa(Hv Hx Ir Qd Qe) Lx(Ly Mh Qd) Mg(Jk Jo Qb) Mr(Ir Qa Qe) Im(In Mj Qe) Nt(Ir Qa) Lw(aA Qb) Mw(Hx Lh)
Hw(Nv Qe) Ij(Nd Nl) In(Iu Ml) Qd(Lv Ok) Oe(Hx Qb) PoMh NoQa Milr NaNj IiLh IkPe IlPc JkOf} Pb{Jk(Hv Hw Ij In Jo Jt Li Lw Mg Mh
Mq Mr Mt Na Ni No Nq Nr Nu Nx Pa) Nv(Hv Hw Hx Ij In Lx Mg Mz Na Ni Nq Nt Nw Ny Ok Pe Po) Mr(Im Jh Jq Lx Mg Mu Mv My Nt Nw
Ny Pa Po Qe) Ok(Io Iu Jo Lu Lx Mq Mt Mv Mw Mx My Ny Pd Po) Nr(Hx Ij Im Jh Mg Mi Mv Mx My Nj Qb Qd Qe) Hx(Hv Hw Lu Mv My
Mz Nm No Nu Ny Pd Po) Mu(Im In Jt Li Md Mm Mz Na Nf Nm Nq) Lx(Jh Ly Mp Mq Mv Mz Nf Ni Nm Pf) Ij(Ii Lu Mv My Nd Nq Nu Nx Oz
Pd) Jo(Im Jh Mm Mp Mt Nn Nq Qb Qd Qe) Pa(Hv In Jh Mq Na Ni Nm Nw Ny Po) Po(Hw Ir Iv Mb Mz Nb Oh Oy) Nt(Hw Mg Mi Mt Mv Nb
Nq Nx) Ny(Hu Im Mg Mh Mn Mz Nd Nw) Mt(Ir Mm Ms Mz Ns Qe) Nw(Lu Mi Ns Nt Nf Pd) Nx(Il Jh Mg Mx Mz No) Nq(Hv Jt Mz Na No)
Mw(Hv Ms My Ns) Nb(Lv Mn Qb Qe) Hw(Im Mn Mv Qb) Mz(Jh Nn Om) Jl(Ip Is Jr) Pe(Mp Oh Qe) Mq(Mn Pf) NoQa LwLh NfJp IiJh}
Ms{Mn(aA Hw Im Ir Iu Iv Jo Mi Mj Mp Mq Mr Mx Mz Na Nb Nl Nn Nq Nr Nt Nv Nx Ny Ok Pe Po Qa Qd Qe) Mw(Ih Ij Im Iu Jk Jo Js Jt Lz
Mg Mj Mv My Nb Nf Ng Nv Nx Pc Pd Pe Qb Qd) Jh(aA Ir Iv Lx Mi Mm Mx My Nb Nj Nl Nt Nv Nx Pe Qa Qe) Mu(Hw Ih Ij Ir Iu Jt Lw Mi
Mr Mz Nf Nr Nt Oh Om Pc) Hx(Im Iu Iv Jk Jt Mg Mi Mv My Mz Nm Nu Nv Oh Po Qe) Nx(aA Hw Ij Il Ir Iu Iv Jk Mg My Nt Ny Oh Qd Qe)
Nn(Ij Il Iu Iv Jk Jo Jt My Na Nt Pc Qb Qd) Pc(aA Lh Lx Mm Mp Nv Ny Ok Po Qe) Nq(Hv Ii Jo Mi Na Nr Nt Nv Pa) My(Iv Lh Mi Mp Mz Nt
Ny Po) Lw(aA Mm Mp Nv Ok Qa Qe) Mg(aA Lh Mp Mx Nv Po) Nb(Jq Lh Lv Pg Po Qa) Jk(Iv Lh Lx Mp Qe) Jq(aA Jo Jt Lu Mz) Ok(Ih Iu Jo
Mi) Po(Nm Nv Ny) Mp(Ij Iu Pa) Om(Jt Mr Nt) Lx(Ij Mv) Mi(Ny Qa) Mm(Ih Nf) Jp(Md Nf) MbQd MtNy MvaA JoNv JtNw} Pc{Lv(Hw Ih Il
Io Iu Jo Mr Mz Nf Nr Ns Nt Nv Oi Pa Pe) Nv(aA Hv Hw In Ir Iv Jo Lx Na Ng Ni Ns Pa Qa Qe) Ok(Io Ir Iv Jk Jp Jq Mm Mp Mx Om Po Qa Qd
Qe) Nw(Hw Ij Im In Ir Jp Lx Mi Mz Ni Pa Pe Qa) Lx(Hv Hw Im In Ir Jk Jo Mu Om Qa Qe) Jh(Hr Hw Ii Mp Mx Nb Nd Nq Nr Oi Qb) Mu(Hw
In Ir Jq Oi Pa Pe Po Qa Qe) Jp(Hv Ij Lu Mr Na Nf Ni No Nr Om) Mp(aA Hx Il Ir Mj Nn Nr Qa Qe) Jq(aA Jo Mg Mr Nd No Nr Nt) Nq(Hw In Ir
Mx Nr Qb Qe) Hu(Hv Im Lw Mm Nx Oi Pa) aA(Jk Mz Nt Oi Om Pe Qe) Lu(Hx Im Jk Nn Qa Qe) Qd(Hx Im Io Mm Oi Om) Ny(Hv Hw Ij Ni
Oi) Nn(Jo Mf No Qb) Im(Hx Io Jk Qe) Jl(Ip Is Jn Mt) Nj(My No Nt) Jk(Io Mx Oi) Om(Hw Iv Nd) Mt(Jt No) Ni(Hx Qe) Ip(Jo Nf) Ir(Oi Pg)
MmIn MwMy MxNx MzLh IvOi JiJo} Mm{Qd(Hv Hw Ij In Jk Jo Lu Lx Mi Mr Mt Mu Na Nb Nf Ni Nq Nr Nt Nw Ok Om Pa Pe Po) Lu(Fp Hv
Ih Im Iv Js Mv Nf Nm Nn Nr Om Pd) Lx(Hq Hv Hw Jo Ly Mz Nb Ng Nw Ok Om) In(Il Im Mi Mp Mu No Nq Nr Pa Pd Qb) Io(Im Iv Jo Jt Md
Mv Nl No Pd) Mz(Lh Mi Mp Mr Mu Nn Nq Nt) Nv(Hv Iv Jo Jt Mi Na Nf Ok) Pa(Hv Hw Ij Im Jo Mu Ng Nw) Il(Hv Ij Jo Jt Lw Mx Nf) Ir(Hw
Mi Mr Nf Ni Nt Po) Jq(Mi Mr Mu Nn Nq Nr Nt) Om(aA Hw Iv Mr My Ng Oy) Nw(Hw Jo Mu Nf Nr Ok) Qb(Hv Hw Ij Jo Na) Nq(Ii Ij Mh Mx)
My(Fp Mw Nb Ng) Qa(Mi Mu No Nt) Nb(Hx Im Ny) Ok(Iv Mi Po) aA(Jl No Pd) Ns(Mw Po) Ng(Mw Nt) Hx(Jo Nf) Jh(Hr Mh) Jk(Jt Na)
WmIp NnIj LwMx MpIi MuLh IsJl QeJt} Jh{Ng(Iu Jk Jo Jp Lx Mg Mp Mv Mw Mx Nl Nt Nw Ny Pe Qa) Oh(Hw Ii Im In Ir Lx Mp Mx Mz Nd
Nr Ok Pe Qa Qd) Hu(Il Ir Jp Lh Mn Nv Nw Pe Po Qa Qb Qe) My(aA Hx Ir Jp Lx Nw Nx Ny Pe Qa Qe) Oy(Fr Ij Ir Jp Mj Mx Nk Nw Qa Qb
Qe) Iv(Hw Ik Io Lx Mb Mp Mz Nb Pa Po) Ns(Il Ir Mn Mx Nw Pe Qa Qb Qe) Lu(Ij Ir Mn Mw Nj Ny Qb) Mp(Hv Ii Jo Mr Na Nf Nr) Lw(Fp Hw

Mz Qa) Ij(Hx Mh Ny) My(Mv Nx) Ng(Mn Nx) MhHx ImQe} Mz{Ml(Hx Ir Mh Mx Nb Nl Nt Pe Qa) Lh(Hx Nf Ny) Fr(Nt Oy) Qe(Im Qc) MhNx HxNy IpJl IuJn QaLj} An{aX(Bg Co Cu Cw De dN) bZ(bA cE cL cM Cq) Ax(dK Gl) Bg(bC dK) dE(Aw Cq) DbEf albH} Mv{My(Fr Ir Lh Pa Pe) Ng(Hx Il Nt Pa) Oy(Ip Ok Qa) Oi(Ir Qe) NrMh MbQd MkPa MlQa ImNx} Nb{Im(Hx Mh Ml My Ny Qd Qe) Fr(Hx Mh My Ny Of) Mh(Ny Qa) Ml(Ir Ny) MyJn QaOy OfPg} bH{Dc(aG aX bC) dF(aA cC cY) dN(Ad Cp De) aO(bA Cu) bR(bA bV) aJcM bBbV cXfR} dA{cA(al aO bZ Ef) bQ(aO Aw bZ) bU(al cG Ef) cL(aO Aw De) bR(bZ cG) cFdK} cK{dF(bQ bR cA cC cF) cF(bW cG Cq) bC(bR cL) bQ(cC cL) bU(al Ex) EfbR} Ax{Cu(Dd Ef Ex Gl) Dc(aJ bW dK) Dd(aA bA) Ex(Bo Cp) Gl(Cw dN) CsFr} Mn{Ni(Ir Mi Mx Ny Pa Qe) Lu(Im Mx Ny Qa) Hw(Hx Ir) Oi(Iv Mx)} Qa{It(Hv In Ir Iu Iv Nt) Ml(Md Ny Pa Pe) Ok(Lu Pa) MkPa} Qe{Im(Hx Jt Lu Mj Ni) Ok(Mi Nd Nt Pa) Lu(Hx Nx) NiHx OiPd} bG{dK(aM As Aw Bn Cp Cv Cw) Dd(aX dN) cR(bA cT) DedN bRbW} Db{Ef(aN Cq Cu Cv Dc Dd) Cq(aA aJ aP bC) bC(Aw dF)} Wm{Ly(Md Mi Nh) Ik(aA No Nx) Ip(Jm Js Nf) Jn(Fp In) QdJm} mF{kC(kF nU oP oQ) nM(aA kG) mP(nA nB) mU(nU oP) lWmI mWnl} Fr{Oy(Hw Jo Mi Nt Nx) Dg(bC bW) MiNi MyNf NgJt HuJo} Jl{Mh(Is Jn On) Oz(Ip Is Jr) On(Oi Pz) MiJn JraA} Nt{Ik(Ir My Pe Pg) Ne(Hx Pg) Lh(Ii Ng) LyPa} Ny{Nd(Hv Mq Ni) Oi(Iv My Pd) MqMy NiPa IiLh} Bg{Dc(Ad bC dN) Dd(Ad aX dK) dN(aJ Dk)} fR{cX(As Aw Bn Dc Dd De) Cx(bC Dd)} Ex{Ar(Aw bU) cP(bB Dk) BoDe CsCu DcbU} Jn{Jo(It Lu) Pa(Jt Mk) NsMq NdHq IrJs} Ok{My(Md Pz) Qd(Pa Pz) LuHx NeNl NiNk} aA{Cx(bM Dk) mP(nN nT) EfbR nBkF jHjI} Ip{Ns(Mq Pd) MiJo NeNl NfIu} bA{bW(aU cY) CtEf aVcF bRbZ} dK{DcbZ DdDk bBdM bQcL bRbS} Im{My(Iv Lu Md) LuMb} Nx{Pa(Mk Ng Qd) NdQd} Pe{Ik(Iv Pg) InJo LjOy} aO{aX(Ad Cw) bC(cE Dd)} dE{dF(aM cC) AwBo EfbR} dN{bS(bR bU) DdDe cNdM} Cq{aCaX bWdB bZcE} aJ{BnCx aVcF dFdG} mP{nTlX mUnH mWnB} Dk{aXbB bWdB} Nm{LuHx IlJm} Ni{NkJi IuPg} nO{nRnK kGoQ} iB{hVjR hWjG} jF{hRjE jHjR} EfaNcI NoMbMf NuLyPa InQbJo nNnRmU nCkGkK Constrained panels with 2 analytes, where 1.0E-7 >= 'AUC p-value' > 0. Contains 351 panels of 16,788 total panels evaluated. : Jr(aA Et Fr Hw Hx Im Ip Is Jg Jh Ji Jj Jk Jo Jp Jq Jt Lh Lu Lv Lw Lx Ma Mg Mi Mm Mp Mr Mt Mu Mv Mz Nb Nd Nj Nn No Nq Nt Nv Nw Oh Ok Om On Pa Pc Pe Pg Po) Ip(aA Et Fr Hx Im Ir Is Jg Jh Ji Jj Jk Jn Jp Jq Lh Lu Lv Lx Ma Mm Mn Mp Mt Mu Mv Mw Mz Nb Nn No Nq Nv Nw Ny Ok Om On Pa Pe Pg Po Qa Qd Qe) Et(aA Fr Hw Hx Il Io Ir Is Ji Jk Jn Jq Lh Lu Lv Lw Lx Mi Mm Mp Mt Mu Mz Nb Nn Nq Nr Nt Nv Nw Oh Om On Pa Pc Pe Pg Po Pz Qa Qe) Ji(aA Fr Hw Il Io Is Iu Jk Jl Lh Lu Lv Lx Ma Mi Mp Mr Ms Mt Mu Nd Nn No Nq Nv Og On Pa Pe Pg) Mt(Hv Hx Jn Jp Jq Lh Lv Lw Lx Mb Mi Mp Ms Mu Mz Nb Nj Nn Nq Nv Ny Oi Pa Pb Pc Pe Pg Po) Lv(aA Fr Hx Is Iv Jh Jj Jl Jn Jp Jq Lh Lx Ma Mm Mp Mu Mx Nj Nn Nw Oh Ok Om On) On(aA Fr Hu Io Jj Jq Mm Ms Mw My Ng Nn No Ns Of Og Oi Oy Pb Pz) Jl(aA Io Jj Jq Lh Lw Ma Mg Mi Mp Mu Nn Nq Nt Og Oh Om Pb Pc) Is(Fr Io Jj Jp Lh Mg Mm Mp Ms Nn Nq Nv Og Ok Om Pg) Jn(Fr Jg Jh Jk Jp Lx Ma Mm Mp Mu Nn Nq Ok Pg) Nj(aA Fr Lh Lx Mp Mu Mz Nb Nn Nq Nv Po Qa) Pg(aA Io Jj Jp Jq Mm Mu Nn Nw Og Ok Pb) Fr(aA Hx Lh Mx Ng) Ny(Jh Lx Mp Nn Nq) Mw(Hu Og Oh Oy) Jq(Jk Mp Nq Po) Lh(Jj Mp Mu Nn) Jp(Mp Nn Nq) hR(hW iB jI) Mu(Hx Og) Jj(Jk Nv) aA(Nn Nq) EfdK MmPe IoNw bGdN Constrained panels with 2 analytes, where 1.0E-6 >= 'AUC p-value' > 1.0E-7. Contains 214 panels of 16,788 total panels evaluated. : Is(aA Hw Jo Jq Lu Lw Lx Ma Mi Mr Mt Mu Mz Nf Nt Nw Oh Oi Pa Pc Pe Po) Mt(aA Hw Ir Iu Jj Ma Mg Mm Mr Na Nf Nr Nt Nw Oh Ok Om Qa Qd) Ip(Hv Hw Ij Iv Jt Mi Mj Mr Mx My Na Nj Nr Nt Nu Nx Og Oh) Jn(aA Hx Io Jj Lh Lw Mg Mz Nv Nw Om Pa Pc Pe Po Qa) Hx(Jh Jp Jq Lx Ma Mm Nj Nn Nq Nw Og Ok) Jp(Lh Lx Mg Mm Mu Mx Nv Pa Pe Po Qa) Pg(Hw Lh Lv Lw Mi Mz No Oh Oy Pc Qa) Fr(Hu Hw In Ir Iv Jj Jq Pb Pe Qa) Lv(Im Ir Mi Mr Mz No Nv Ny Po) Lx(Ij Jh Jo Jq Mp Nx Og Oy) Om(Ir Lh Mx Og Pa Pb Pe Qe) Mu(aA Hw Jq Mp Nv Pa Qb) Nn(Hw Il Jq Mx Pa Pc) Mm(aA Hu Ij Ji Qc) Lh(aA Jq Ma Nw Og) Et(Md Mr Nf No) Nj(Jk No Ny Pf) Jh(Nb Pa Po Qe) Jl(Jr Mz No Ok) Nv(Im Io Jq Og) Mp(Ij Mj Nx) Mw(Hv Md Pa) Qa(Io Jj Nw) Po(Og Oy) Ma(aA Ny) Ji(Nt Pc) Jj(Pe Qe) Pb(Ny Pe) AncS EfcD NqQb IlOk JgOg JkNw bHdN jDjP Constrained panels with 2 analytes, where 1.0E-5 >= 'AUC p-value' > 1.0E-6. Contains 372 panels of 16,788 total panels evaluated. : Jp(aA Hw Ii Ij Im In Io Ir Iu Iv Jk Jo Jq Lw Ma Mi Mq Mv Mz Nb Nd No Nr Nt Nu Nx Ok Om Pc Qd Qe) Jh(Hw Ii Ij Il In Ir Jg Jq Mi Mj Mn Mp Mx Mz Nd Nj Nn Nq Nr Nx Ok Pe Qa Qb) Nn(Hv Ii Ij In Ir Iu Lw Lx Mi Mp Mu Nd Nr Nv Nw Nx Oi Om Pe Qa Qb Qe) Jq(Hw Il Im Iu Jg Jn Mg Mi Mm Mv My Nb Nd Nj Nt Nu Nw Om Pa Pe Qa Qe) Nw(Hw In Ir Iv Jo Lu Lx Ma Mg Mm Mp Ms Mu Mv Mz Nq Ok Om Pa Pe) Lv(Hw Ih Jg Li Lu Md Mw My Nf Nq Nr Nt Pa Pc Pe Qa Qe) Lx(Hv Hw Im Jk Lw Mg Mh Mq Mu My Nv Oh Ok Om Pc Qa Qe) Mm(In Ir Jk Lh Mz Nv Nx Ny Om Pa Po Qa Qb Qd) Mp(aA Fr Hx Ir Lw Mx My Mz Nr Nv Ok Om Qa Qe) Ok(Fr Io Ir Iv Jk Mx Om Pa Pb Pe Po Qa Qe) Nq(Hw Ij Ir Mx Ng Nr Nv Og Om Pa Pe Qe) Mw(In Mj Mq Ms Mx Nd Nf Nj Nl Nr Ns Pc) Ip(Ii In Iu Jl Jo Js Lw Lz Md Mg Nf Pc) Jn(Hw Jl Lu Mi Mr Mv Nb Nd No Nr Nt Oh) Ny(Hv Hw Jg Lw Mq Mv Mx My Nd Nu Oh Pc) Fr(cJ dN Hv Jo Lw Mq Mz Na No Nt Oh) Ma(Ir Iv Mx Nv Pa Pe Po Qa Qb Qe) Jg(aA Hx Io Ir Lu Ms Mx Pe Qa Qe) Om(aA Hw Iv Mi Ms Mz Nl Nv Qa Qd) Mu(Hv Ir Iu Ms Nr Pb Pe Qa Qe) Lh(Lw Mh No Oh Pb Qa) aA(cJ cU Mg My Nx Qa) Im(Jj Jk Nj Nx Qe) cU(aJ An bA Dc dK) Mt(Jl Jo Jt No) Jj(Hx Ir Po Qd) Ef(bA cT dN) Nj(Mn My Nt) Qa(Hx Lu Nv) Nx(Hx Ms Og) Pg(Ir Jt Nt) cS(bG Cq Dd) Is(Jl No) Ji(Jo Wm) Og(Jk Qe) Oh(Pe Po) jD(hW iB) AnaX AwdI CqdN DdbF DkcJ IvNv aPdH bGdK nRmF hRjH Constrained panels with 2 analytes, where 1.0E-4 >= 'AUC p-value' > 1.0E-5. Contains 553 panels of 16,788 total panels evaluated. : Jg(Hv Hw Ii Ij Im In Iu Jj Lw Lx Ma Md Mi Mm Mp Mr Mz Nb Nd Nf Ni Nn Nq Nr Nt Nx Oh Oi Ok Pa Po Qb Qd) Jk(aA Hx Ir Iv Lv Lw Ma Mh Mi Mp Ms Mx Mz Na Nb Ng Ni Nn No Nq Nx Oh Oi Pa Pc Pe Po Qa Qe) Ma(Hr Hv Hw Ii Ij Im In Jj Jq Lu Lx Mb Mi Mp Mu Mz Nb Nl Nn Nq Nr Nx Ok Om Qd) Po(aA Hw Im Ir Lw Lx Mb Mg Mh Mi Mp Mr Mu Mz Nn Nq Nt Pa Pb Pc Pe Qa Qe) Nv(aA Hv Hw Ir Jo Jt Lw Mi Mr Mz Nf Ni Nr Nt Oe Oh Ok Pa Pb Pc Pe Qd Qe) Jh(Hv Ih Im Iu Iv Js Li Lw Lz Md Mg Mh Mm Mq Mr Nf Nt Og Oh Pc Qd) Qe(aA Hv Hw Hx Iv Lw Mg Mi Mr Mz Na Nb Nd Ni Nt Nx Oh Pa Pc Pe) Mm(Fp Hw Ii Il Im Jl Js Lu Lx Mh Mj Mu Mx My Nb Nr Nt Ok Pf) Im(Hx Iv Lu Lw Mj Mp Mu Mv My Mz Nb Nn Nq Nt Pa Pc Pe Qd) Qa(Jo Jt Lw Md Mg Mi Mn Mr Mz Nb Nd No Nq Nt Oh Pa Pc Pe) Ok(Hw Iu Jj Jq Mg Mi Mr Mu My Mz Nb Nd Nn Nq Nt Oh Qd) Lx(aA Hq In Ir Iv Ly Mr Mv Mz Na Nb Ni Nm Nq Pa Qd) Nw(aA Hv Iu Jt Lw Mb Mi Mr Na Nd No Nr Nt Oh Pc Wm) Hx(aA Ir Lu Lw Mg Mi Mn Ms Mv Mz No Nt Oh Pc Qd) Mu(Ih Iv Jj Jo Lw Mh Mi Mz Nb Ng Nt Oh Om Qd) cS(aO As Aw bA Bn Cp CU Cv Cw Dc Dk dM dN) Mp(Hq Hv Hw Mi Mr Mv Nb Nq Nt Pa Pe Qb Qd) Om(Iu Jj Jt Lw Mr My Ng No Nt Of Oh Oy Pc) Jp(Hv Jj Jt Lu Md Mh Mr Na Nf Ni Nm Oh) Ny(In Iu Md Mg Mh Mr Na Nf Nr Nx Og Pa) Nq(Hv Ih Ii In Iv Jj Mz Nb Nx Oh Qd) Lv(Ii Ij Il Io Iu Jo Jt Mb Mv Na Qd) aA(bF bH Ij Il Jo kG Lw Mn Nt Pc Pe) Nn(Hu Lu Me Mq Mr Ms Mz Nb Nt Qd) Mw(Hw Ii Il Iu Jj Mh Na Nm Nu Qd) Nj(Fp Ij Jt Mi Mj Mv Nr Pa Qb) Oh(Hu Hv Hw Il Mj Mx My Nb Nr) Jj(Ij Il Jo Mn Mv My Nx Qb) Mn(Hw Ir Lw Mx Nb Pa) Og(Ij Mi Mt My Nt Pe) dN(aJ An Bg cJ Dd Dk) Cq(aX cD dB dE Fr) Ir(Lw Mg Mv My Pc) Jq(Iv Jo Mr No Nr) Pe(Lw Mg Mz Nt Pc) An(aO bZ cJ Ef) Mx(Ij Mv Nb Nx) Qd(Lh Mb Nx Wm) cU(Cp Dd Dk fR) mF(mP mT nM oP) Fr(Bo Jt Oy) My(Lw Md Pa) Mz(Mg Ml Wm) Jl(Et Mh On) aO(bC bH Ef)

Figure 34 Continued dK(dF Ex Gl) Hu(Lw Pc) Ij(Mi Pa) Jn(Jo Jt) Lh(Ms Pc) Nx(No Pa) aP(bG cJ) cD(bQ Ex) DcaX DedI WmIp NsPf Ntlo NuMd MlMt aIcK aJbG bAbJ bHdF cXfR jHjP Constrained panels with 2 analytes, where 1.0E-3 >= 'AUC p-value' > 1.0E-4. Contains 544 panels of 16,788 total panels evaluated. : Mn(Hv Ih Ii Il In Iu Lu Lz Md Mg Mh Mj Mq Mr Ms Mv My Na Nf Ni Nl Nm Nr Nu Oh Pc Pd Qb) Qd(aA Hw Ii Io Jk Jo Jt Lu Lw Md Mg Mi Mr Mv Mz Nb Nd Nf Nr Nt Oh Pa Pc Pe Po) Im(Hv Hw Ii Ij In Iu Jo Jt Mb Md Mg Mh Mq Mr Mx Na Nf Nr Og Oh Pd) My(Fp Hv Ih Iv Jg Lu Lz Mh Mq Mr Ms Mw Mx Nd Nl Nq Nr Nu Nx Qb) Mm(Hr Hv Ih Iu Iv Jo Jt Ma Md Mi Mp Mr Mv Ma Nf Nn No Nq Pd) Lw(Fp Hw Ij Il Lv Ma Mi Mv Mx Mz Nb Nq Nr Nt Nx Oh Qb) Jj(Fp Hq Ih Ii Iv Jm Js Lx Mg Mj Mp Mx Nn Nt Ny Pa Pd) Nq(Hu Jo Js Mh Mi Mq Mr Ms Na Nf Nm No Nt Oy Pc) Ma(Ih Iu Jo Js Jt Md Mh Mq Mr Na Nf No Nt Oh Pc) Mv(Ij Iu Iv Js Md Ms Mz Nr Nx Og Oh Ok Pa Po Qe) Ir(aA Hw Jo Jt Lu Md Mi Mr Mz Nb Nd Nf Nt Oh Pa) Jg(Hu Ih Iv Jo Js Lz Mg Mh Mq Na Ng No Ns Oy Pc) Mp(Ii In Iv Jo Js Jt Na Nf Ni No Ns Pc Pd) Mz(aA Hw Il Iu Iv Mi Nd Nl Nt Og Oh Pa Pb) Qb(Hw Iu Jo Lu Md Mg Mi Mq Nm Nr Og Oh Pc) An(Aw Ba bC Bg bV Co Cq Cu Cw De dF dK) Jk(Hv Hw Jo Jt Mg Mq Mr Nf Nr Nt Oe) Nj(Hw Ih Ii Il Js Mr Mx Nm Oh Pd) Ij(Iu Lu Md Mg Ms Nd Nf Nr Oh Pc) Nx(Hw Iu Iv Lu Mg Mi Mw Nd Nr Oh) cJ(Aw BG cK Cq Cu Dc Dd Ex Gl) dI(Ad aI aM bB Bg Bn Cp Cu Dc Dk) bA(aO bE BG bH bZ Dc De Dk) Hx(Hw Iu Iv Jo Jt Md Mr Pa) Qe(Ii In Jo Jt Lu Md Nf Nr) aA(bB bG Cq Ef Jq Mi nR Ok) cU(Ad aM As Bg Bn Cu Cv Cw) Dd(aO Aw aX bZ dF Dk Fr) Og(Hq Ii Il Iv Nb Nm Nr) Nn(Iv Mf Na Nf Ni No) Nu(Hq Hv Ih Iu Mj Nd) Jh(Jo Jt Lu Na Ns Pd) Oh(Ii In Iu Mq Nt Pa) Aw(aP AX bH dN) Dc(Ax bC bH dN Fr) Ef(aN cS dE dF Gl) Po(Iv Jo Jt Nb Nf) Mg(Lv Mx Ng No Pa) Mu(Jt Mr Nf No Pc) aO(aM cK Cw Dk dM) dK(Ax Bg bQ bZ Dk) Ad(aX cS Fr Gl) Cq(aJ aP bE Db) De(bV cS dF dN) Lu(Jq Mw Ny Ok) Nb(Lv Ml Ms Pb) Bg(aJ aP cD) Nm(Il Mx Pa) Ny(Ii Iv Pd) Ok(Md No Pc) Pb(Lx Mr Nr) bB(bH bV cK) bE(aL bQ dF) bF(aM Cu Cw) mF(ml nN oQ) Dk(aX bC) Wm(Jq Ly) Fr(Cw Jl) Nt(Mi Pc) Mw(Ih Iv) Mx(Ii Nr) Jt(Lx Pe) bG(bC bW) bH(bV fR) bQ(cC dH) hW(jH jR) CpdN CuaX ExbU GlcD NoJo MbPf MdHv MfPa MhMt MiPe MjHu IlPd JlOz JqPc aIdA cSdF nRnC lXkG mPmU hRlM iBjH jFjR Constrained panels with 2 analytes, where 1.0E-2 >= 'AUC p-value' > 1.0E-3. Contains 457 panels of 16,788 total panels evaluated. : Jj(Hu Hw In Iq Iu Jh Jt Li Lu Md Mh Mi Mr Nb Nc Nd Nf Nj Nl No Nr Nu Oy Pf Wm) Ih(Hv Hw Ii Il In Jo Lu Lw Mg Mh Mj Mq Ms Mv Na Nb Nd Nm Nr Og Oh) Dd(aA aI aJ An aP bA bC bE BG bH bL bV bW DE dI fR Gl) Mg(Fp Hv Ii Il Iv Js Lu Md Mh Mj Mr Ms Nb Nd Nr Nt Og Oh) Iv(Hw Iu Jo Jt Lu Lw Mb Md Mi Mr Nb Nr Oh Pa Pc) Lw(Iu Jo Js Lu Lz Mh Mj Mr Ms Nd No Og Pa) Ad(aJ aO aP bC bE bF bH bV bZ cJ dE dK) Dc(aJ aP Ba Bg bJ bW bZ DE dF dK Ef) Cw(aP aX BG bH bZ cJ dE dF dI Gl) Nm(Fp Hv Iu Lu Lz Md Mh Mj Nd Nl Oh) Pa(Hv Hw Jo Js Jt Mq Ms Mx Na Ni Og) Dk(aA aJ An aP bV bW bZ cD dF Di) My(Hw Ii In Iu Js Li Na Nf Pc Pd) Nj(Hv Iu Lu Lz Md Mh Na Nd Nf Nu) cJ(bH bV Cp Cv dA DE dI Ef) dK(aI Ar bB Bc bF bH cE cK cT) An(aA aJ aP bA bE bW fR Gl) Mv(Hv Hw Ii Mq Mr Na Nb Nf) Qb(Hv Ii In Na Nd Nf Ni Pd) Oh(Fp Jo Js Md Mr Na No Wm) Pc(Fp Il Js Lu Mm Mz Nb Nx) aM(aJ bH bL bQ bZ cK dF Gl) As(aO aX Ba bF bZ dI Gl) Bg(aA Ar aX bC bV cT dE) Ex(Ax bB bE Bo bR De Ef) Nu(In Lu Lz Mb Mh Mq Na) Jt(Jg Ms Mz Nn No Nq Nt) Og(Hr Hu Iu Jo Mf Mj Mr) cD(bG bS cG cK Co dA dG) Cu(aJ aO bC bZ dE Gl) Hv(Il Mh Mi Mx Nd Nl) cT(bC bH bJ bW cK cR) Cp(aP aX bH bZ dE) Lu(Fp Il Iu Js Pd) Md(Hw Il Mx Nb Nr) Ni(Hq Mi Mm Nk Nq) Jo(Ms Mx Mz Nn Pb) aA(Aw Co De Gl No) aI(aX bE bH dE dM) bG(bE cR dE dM fR) Bn(aX bF bH bZ) Ef(aJ aP Cv Fr) Wm(Ik Iq Js Nf) Mb(Fp Hu Mh Mj) Nb(Hx Mh Nd Ny) Aw(aJ bA dE) Cq(bV bZ Gl) De(aJ aP dM) No(Mf Mi Mz) Nr(Iu Js Mz) Pd(In Mw Pb) bB(Ar bA bC) bE(cZ dD Gl) Co(bV dM) Cv(bH bZ) Nt(Nc Nf) Ms(Ii Jh) Na(Il Nl) Hw(Js Pb) Nx(Lz Mh) bR(dG dI) fR(bC Bo) iB(jP lM) AobV FpIu MiIo MqJs MrMz MwNg NlIn HuJk IjIl JhOy aNbL cCdI cFcK cGcL nNmU nRmW nTmP mFnI nBoQ hRhX hVjR jEjF

Figure 34 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Wm | % | 8.5E-2 | 6.7E0 | 2.5E1 | 4.4E1 | 1.4E2 | 7.4E1 | 5.4E-2 | 8.5E-2 | 1.0E3 | 1.9E2 | 124 | 7 | 124 | 7 | 0.71 |
| Po | pg/ml | 3.0E-1 | 2.8E1 | 8.7E0 | 7.6E1 | 2.6E1 | 8.3E1 | 8.0E-3 | 2.6E-2 | 2.7E2 | 2.2E2 | 258 | 10 | 258 | 10 | 0.80 |
| Et | ng/ml | 1.5E3 | 4.0E3 | 1.8E3 | 3.9E3 | 1.1E3 | 9.1E2 | 7.9E1 | 1.8E3 | 4.7E3 | 5.0E3 | 257 | 10 | 257 | 10 | 0.92 |
| Fp | ng/ml | 1.4E1 | 3.9E1 | 2.5E1 | 4.3E1 | 2.8E1 | 3.6E1 | 6.0E-3 | 3.4E0 | 1.3E2 | 1.3E2 | 261 | 10 | 261 | 10 | 0.69 |
| Fr | ng/ml | 3.8E4 | 6.0E5 | 1.2E5 | 5.4E5 | 1.8E5 | 2.9E5 | 1.9E2 | 2.2E4 | 8.4E5 | 8.4E5 | 264 | 11 | 264 | 11 | 0.86 |
| Nm | pg/ml | 1.4E4 | 4.9E4 | 3.7E4 | 1.3E5 | 8.8E4 | 2.4E5 | 1.0E-9 | 1.0E4 | 9.6E5 | 8.2E5 | 261 | 10 | 261 | 10 | 0.77 |
| Nn | pg/ml | 1.8E2 | 6.1E3 | 1.8E3 | 2.4E4 | 8.0E3 | 3.9E4 | 1.0E-9 | 2.3E1 | 9.5E4 | 1.1E5 | 261 | 10 | 261 | 10 | 0.83 |
| No | pg/ml | 1.7E1 | 2.3E2 | 3.3E1 | 3.4E2 | 5.6E1 | 3.6E2 | 1.0E-9 | 4.4E0 | 5.6E2 | 9.1E2 | 261 | 10 | 261 | 10 | 0.77 |
| Nq | pg/ml | 2.0E0 | 4.6E1 | 2.4E1 | 1.2E2 | 7.7E1 | 1.9E2 | 1.0E-9 | 1.0E-9 | 6.7E2 | 6.3E2 | 261 | 10 | 261 | 10 | 0.78 |
| Nr | pg/ml | 2.0E0 | 1.2E1 | 2.3E1 | 2.4E2 | 8.0E1 | 4.5E2 | 1.0E-9 | 1.0E-9 | 9.8E2 | 1.4E3 | 261 | 10 | 261 | 10 | 0.70 |
| Ns | pg/ml | 1.0E-9 | 1.0E-9 | 9.7E0 | 3.6E-1 | 7.4E1 | 1.1E0 | 1.0E-9 | 1.0E-9 | 1.1E3 | 3.6E0 | 261 | 10 | 261 | 10 | 0.52 |
| Nt | pg/ml | 1.2E2 | 1.9E2 | 1.4E2 | 4.8E2 | 1.0E2 | 5.7E2 | 1.5E1 | 7.5E1 | 8.8E2 | 1.7E3 | 261 | 10 | 261 | 10 | 0.70 |
| Nu | pg/ml | 2.4E1 | 9.1E1 | 5.9E1 | 1.2E2 | 8.8E1 | 1.2E2 | 1.0E-9 | 1.0E-9 | 6.3E2 | 3.7E2 | 261 | 10 | 261 | 10 | 0.68 |
| Lu | pg/ml | 1.0E4 | 7.8E3 | 1.7E4 | 7.4E3 | 4.5E4 | 5.1E3 | 9.4E2 | 5.2E2 | 5.6E5 | 1.7E4 | 261 | 10 | 261 | 10 | 0.39 |
| Lv | pg/ml | 1.0E-9 | 5.9E1 | 1.6E1 | 6.4E1 | 3.2E1 | 6.9E1 | 1.0E-9 | 1.0E-9 | 2.6E2 | 1.9E2 | 261 | 10 | 261 | 10 | 0.69 |
| Lw | pg/ml | 1.0E-9 | 1.0E-9 | 4.6E-1 | 8.2E0 | 5.3E0 | 1.4E1 | 1.0E-9 | 1.0E-9 | 8.0E1 | 4.0E1 | 261 | 10 | 261 | 10 | 0.64 |
| Lx | pg/ml | 1.0E-9 | 1.3E3 | 1.9E2 | 3.3E3 | 6.1E2 | 6.8E3 | 1.0E-9 | 1.0E-9 | 6.2E3 | 2.2E4 | 261 | 10 | 261 | 10 | 0.82 |
| Ly | pg/ml | 1.0E-9 | 1.0E-9 | 9.6E0 | 7.8E0 | 1.8E1 | 1.9E1 | 1.0E-9 | 1.0E-9 | 1.1E2 | 6.0E1 | 261 | 10 | 261 | 10 | 0.51 |
| Lz | pg/ml | 1.0E-9 | 1.0E-9 | 3.2E0 | 1.3E1 | 2.9E1 | 2.3E1 | 1.0E-9 | 1.0E-9 | 4.3E2 | 6.2E1 | 261 | 10 | 261 | 10 | 0.63 |
| Ma | pg/ml | 5.2E2 | 3.6E3 | 2.6E3 | 3.8E3 | 6.8E3 | 2.6E3 | 1.0E-9 | 3.3E2 | 6.5E4 | 7.5E3 | 261 | 10 | 261 | 10 | 0.78 |
| Mb | pg/ml | 2.6E1 | 1.8E1 | 3.3E1 | 2.2E1 | 1.9E1 | 1.2E1 | 9.2E0 | 4.1E0 | 2.1E2 | 4.7E1 | 261 | 10 | 261 | 10 | 0.25 |
| Mc | pg/ml | 1.0E-9 | 1.0E-9 | 7.3E-2 | 1.0E-9 | 8.5E-1 | 0.0E0 | 1.0E-9 | 1.0E-9 | 1.3E1 | 1.0E-9 | 261 | 10 | 261 | 10 | 0.49 |
| Md | pg/ml | 1.0E-9 | 1.0E-9 | 4.9E-1 | 3.7E0 | 4.3E0 | 9.2E0 | 1.0E-9 | 1.0E-9 | 6.5E1 | 2.9E1 | 261 | 10 | 261 | 10 | 0.66 |
| Me | pg/ml | 3.1E1 | 3.3E1 | 3.1E1 | 4.1E1 | 2.6E1 | 5.2E1 | 1.0E-9 | 1.0E-9 | 3.2E2 | 1.8E2 | 261 | 10 | 261 | 10 | 0.50 |
| Mf | pg/ml | 1.0E-9 | 1.0E-9 | 7.8E-1 | 4.8E1 | 4.4E0 | 1.4E0 | 1.0E-9 | 1.0E-9 | 5.6E1 | 4.5E0 | 261 | 10 | 261 | 10 | 0.51 |
| Mg | pg/ml | 1.4E0 | 1.3E1 | 7.4E0 | 1.2E1 | 1.5E1 | 1.3E1 | 1.0E-9 | 1.0E-9 | 1.5E2 | 3.7E1 | 261 | 10 | 261 | 10 | 0.61 |
| Mh | pg/ml | 1.0E-9 | 5.2E-2 | 1.0E0 | 3.4E0 | 7.4E0 | 6.6E0 | 1.0E-9 | 1.0E-9 | 1.1E2 | 1.8E1 | 261 | 10 | 261 | 10 | 0.66 |
| Mi | pg/ml | 1.0E-9 | 1.0E-9 | 1.1E0 | 4.7E1 | 9.2E0 | 1.0E2 | 1.0E-9 | 1.0E-9 | 1.2E2 | 3.2E2 | 261 | 10 | 261 | 10 | 0.69 |
| Mj | pg/ml | 1.0E-9 | 1.0E-9 | 5.8E0 | 4.6E1 | 3.1E1 | 7.7E1 | 1.0E-9 | 1.0E-9 | 4.6E2 | 2.1E2 | 261 | 10 | 261 | 10 | 0.63 |
| Mk | pg/ml | 2.1E0 | 3.4E0 | 1.8E1 | 6.7E1 | 1.1E2 | 1.6E2 | 1.0E-9 | 1.0E-9 | 1.3E3 | 5.0E2 | 261 | 10 | 261 | 10 | 0.55 |
| Ml | pg/ml | 1.0E-9 | 1.0E-9 | 1.2E1 | 5.3E1 | 1.3E2 | 1.6E2 | 1.0E-9 | 1.0E-9 | 2.1E3 | 5.1E2 | 261 | 10 | 261 | 10 | 0.56 |
| Mm | pg/ml | 6.2E2 | 3.0E3 | 1.1E3 | 2.9E3 | 1.3E3 | 2.0E3 | 1.0E-9 | 3.6E2 | 6.4E3 | 6.5E3 | 261 | 10 | 261 | 10 | 0.81 |
| Mn | pg/ml | 6.4E0 | 1.8E1 | 1.2E1 | 1.9E1 | 2.8E1 | 1.3E1 | 1.0E-9 | 5.5E0 | 3.5E2 | 5.1E1 | 261 | 10 | 261 | 10 | 0.77 |
| Mp | pg/ml | 1.0E-9 | 3.6E1 | 1.4E1 | 9.4E1 | 5.1E1 | 1.5E2 | 1.0E-9 | 1.0E-9 | 6.3E2 | 5.0E2 | 261 | 10 | 261 | 10 | 0.84 |
| Mq | pg/ml | 1.0E-9 | 1.0E-9 | 2.4E0 | 1.6E1 | 1.4E1 | 3.5E1 | 1.0E-9 | 1.0E-9 | 1.8E2 | 1.0E2 | 261 | 10 | 261 | 10 | 0.57 |
| Mr | pg/ml | 1.0E-9 | 9.9E0 | 2.8E1 | 7.6E2 | 1.4E2 | 1.2E3 | 1.0E-9 | 1.0E-9 | 1.5E3 | 3.4E3 | 261 | 10 | 261 | 10 | 0.68 |
| Ms | pg/ml | 3.3E2 | 2.2E2 | 4.6E2 | 3.6E2 | 5.1E2 | 3.5E2 | 1.0E-9 | 1.0E-9 | 3.3E3 | 9.8E2 | 261 | 10 | 261 | 10 | 0.46 |
| Mt | pg/ml | 4.8E-1 | 7.6E1 | 9.7E0 | 3.8E2 | 4.9E1 | 1.0E3 | 1.0E-9 | 2.8E-1 | 7.1E2 | 3.2E3 | 261 | 10 | 261 | 10 | 0.86 |
| Mu | pg/ml | 1.0E-9 | 3.9E0 | 1.9E0 | 7.7E0 | 1.6E1 | 1.1E1 | 1.0E-9 | 1.0E-9 | 2.3E2 | 3.5E1 | 261 | 10 | 261 | 10 | 0.80 |
| Mv | pg/ml | 1.0E-9 | 1.1E2 | 7.8E1 | 2.9E2 | 3.8E2 | 3.7E2 | 1.0E-9 | 1.0E-9 | 4.5E3 | 9.2E2 | 261 | 10 | 261 | 10 | 0.72 |
| Mw | pg/ml | 3.7E1 | 1.2E3 | 3.0E2 | 1.9E3 | 1.5E3 | 2.1E3 | 1.0E-9 | 1.0E-9 | 1.8E4 | 5.3E3 | 261 | 10 | 261 | 10 | 0.84 |
| Mx | pg/ml | 1.0E-9 | 7.3E-1 | 4.1E-1 | 3.0E0 | 2.1E0 | 6.1E0 | 1.0E-9 | 1.0E-9 | 3.2E1 | 2.0E1 | 261 | 10 | 261 | 10 | 0.72 |
| My | pg/ml | 1.0E-9 | 2.0E2 | 4.0E2 | 4.1E2 | 2.8E3 | 6.1E2 | 1.0E-9 | 1.0E-9 | 3.9E4 | 1.9E3 | 261 | 10 | 261 | 10 | 0.73 |
| Mz | pg/ml | 1.2E1 | 8.3E1 | 2.6E1 | 3.8E2 | 5.1E1 | 6.7E2 | 1.0E-9 | 1.0E-9 | 5.5E2 | 1.9E3 | 261 | 10 | 261 | 10 | 0.73 |
| Na | pg/ml | 1.0E-9 | 1.0E-9 | 5.1E-1 | 5.5E0 | 1.6E0 | 1.3E1 | 1.0E-9 | 1.0E-9 | 9.6E0 | 4.2E1 | 261 | 10 | 261 | 10 | 0.61 |
| Nb | pg/ml | 2.2E0 | 1.2E1 | 3.7E0 | 3.9E1 | 1.1E1 | 6.7E1 | 1.0E-9 | 1.0E-9 | 1.5E2 | 2.1E2 | 261 | 10 | 261 | 10 | 0.70 |
| Nc | pg/ml | 3.4E2 | 1.2E1 | 5.1E2 | 2.3E2 | 7.7E2 | 4.6E2 | 1.0E-9 | 1.0E-9 | 9.2E3 | 1.3E3 | 261 | 10 | 261 | 10 | 0.31 |
| Nd | pg/ml | 2.5E1 | 3.9E1 | 2.8E1 | 2.4E2 | 7.8E1 | 6.6E2 | 1.0E-9 | 1.0E-9 | 1.2E3 | 2.1E3 | 261 | 10 | 261 | 10 | 0.66 |
| Ne | pg/ml | 4.2E2 | 2.0E2 | 5.3E2 | 2.6E2 | 6.0E2 | 2.5E2 | 1.0E-9 | 1.0E-9 | 7.0E3 | 7.3E2 | 261 | 10 | 261 | 10 | 0.33 |
| Nf | pg/ml | 1.0E-9 | 1.0E-9 | 2.1E0 | 2.8E1 | 8.8E0 | 5.1E1 | 1.0E-9 | 1.0E-9 | 8.2E1 | 1.3E2 | 261 | 10 | 261 | 10 | 0.58 |
| Ng | pg/ml | 1.7E1 | 4.7E1 | 1.0E2 | 9.7E1 | 2.0E2 | 1.3E2 | 1.0E-9 | 1.0E-9 | 1.6E3 | 4.2E2 | 261 | 10 | 261 | 10 | 0.54 |
| Nh | pg/ml | 6.0E1 | 3.1E1 | 8.1E1 | 3.9E1 | 7.8E1 | 2.9E1 | 1.0E-9 | 4.1E0 | 5.6E2 | 8.9E1 | 261 | 10 | 261 | 10 | 0.31 |
| Ni | pg/ml | 1.0E-9 | 1.0E-9 | 8.6E1 | 1.8E2 | 1.3E2 | 3.4E2 | 1.0E-9 | 1.0E-9 | 7.1E2 | 1.1E3 | 261 | 10 | 261 | 10 | 0.51 |
| Nj | pg/ml | 6.2E0 | 3.4E0 | 9.9E0 | 7.9E0 | 1.1E1 | 8.8E0 | 1.0E-9 | 1.0E-9 | 6.8E1 | 2.2E1 | 261 | 10 | 261 | 10 | 0.42 |

Figure 35

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nk | pg/ml | 1.7E1 | 8.2E0 | 3.2E1 | 2.0E1 | 4.0E1 | 2.7E1 | 1.0E-9 | 1.0E-9 | 2.0E2 | 6.9E1 | 261 | 10 | 261 | 10 | 0.43 |
| Nl | pg/ml | 4.2E1 | 1.0E1 | 5.6E1 | 2.9E1 | 7.9E1 | 4.5E1 | 1.0E-9 | 1.0E-9 | 1.1E3 | 1.4E2 | 261 | 10 | 261 | 10 | 0.31 |
| Hq | pg/ml | 1.2E0 | 1.2E1 | 2.0E2 | 3.1E2 | 2.1E3 | 8.7E2 | 1.0E-9 | 6.2E-2 | 2.8E4 | 2.8E3 | 259 | 10 | 259 | 10 | 0.72 |
| Hr | pg/ml | 8.4E1 | 9.5E2 | 5.1E2 | 2.0E3 | 1.0E3 | 2.8E3 | 1.0E-9 | 1.0E-9 | 8.4E3 | 8.9E3 | 259 | 10 | 259 | 10 | 0.67 |
| Hu | pg/ml | 1.4E1 | 4.5E2 | 5.9E3 | 1.1E3 | 4.5E4 | 2.0E3 | 1.0E-9 | 1.0E-9 | 6.3E5 | 6.5E3 | 259 | 10 | 259 | 10 | 0.66 |
| Hv | pg/ml | 1.3E0 | 3.0E0 | 3.1E0 | 9.8E1 | 1.1E1 | 2.8E2 | 1.0E-9 | 1.0E-9 | 1.6E2 | 8.9E2 | 259 | 10 | 259 | 10 | 0.69 |
| Hw | pg/ml | 5.5E0 | 1.2E1 | 1.6E1 | 1.0E3 | 5.0E1 | 2.9E3 | 1.0E-9 | 5.1E-1 | 6.4E2 | 9.4E3 | 259 | 10 | 259 | 10 | 0.62 |
| Hx | pg/ml | 8.8E0 | 5.1E1 | 6.1E1 | 2.6E2 | 5.8E2 | 4.4E2 | 1.0E-9 | 3.9E0 | 9.3E3 | 1.3E3 | 259 | 10 | 259 | 10 | 0.78 |
| Ih | ng/ml | 7.3E1 | 5.9E2 | 2.4E2 | 8.0E2 | 4.3E2 | 8.8E2 | 1.0E-9 | 5.7E0 | 3.6E3 | 2.8E3 | 260 | 10 | 260 | 10 | 0.72 |
| Ii | ng/ml | 9.0E1 | 3.5E2 | 2.0E2 | 1.2E3 | 4.4E2 | 1.6E3 | 7.3E-1 | 2.3E0 | 5.2E3 | 4.5E3 | 260 | 10 | 260 | 10 | 0.74 |
| Ij | ng/ml | 8.7E1 | 1.4E2 | 2.0E2 | 2.6E3 | 6.1E2 | 7.6E3 | 2.8E0 | 4.6E1 | 6.4E3 | 2.4E4 | 257 | 10 | 257 | 10 | 0.72 |
| Ik | ng/ml | 1.2E1 | 1.8E1 | 1.7E3 | 6.8E1 | 1.3E4 | 1.4E2 | 5.9E-1 | 5.5E0 | 1.2E5 | 4.6E2 | 257 | 10 | 257 | 10 | 0.55 |
| Il | ng/ml | 3.8E2 | 7.0E2 | 1.3E3 | 3.1E3 | 2.8E3 | 4.7E3 | 1.0E-9 | 7.1E1 | 1.2E4 | 1.2E4 | 255 | 10 | 255 | 10 | 0.67 |
| Im | ng/ml | 2.3E2 | 7.0E2 | 4.7E2 | 1.7E3 | 7.6E2 | 2.3E3 | 1.4E1 | 1.5E2 | 6.0E3 | 6.2E3 | 257 | 10 | 257 | 10 | 0.77 |
| In | ng/ml | 3.3E0 | 2.3E0 | 1.9E1 | 4.8E2 | 8.2E1 | 1.4E3 | 1.0E-9 | 1.0E-9 | 1.1E3 | 4.5E3 | 260 | 10 | 260 | 10 | 0.49 |
| Io | ng/ml | 1.1E4 | 1.4E4 | 2.2E4 | 1.4E4 | 5.1E4 | 1.0E4 | 1.0E-9 | 1.5E3 | 7.1E5 | 3.3E4 | 260 | 10 | 260 | 10 | 0.50 |
| Ip | ng/ml | 1.3E1 | 4.8E1 | 2.2E1 | 4.4E1 | 2.7E1 | 1.4E1 | 1.0E-9 | 2.1E1 | 2.3E2 | 5.8E1 | 260 | 10 | 260 | 10 | 0.80 |
| Iq | ug/ml | 1.2E-1 | 2.6E-1 | 7.7E-1 | 2.7E1 | 2.7E0 | 6.8E1 | 1.0E-9 | 1.0E-9 | 3.4E1 | 2.2E2 | 260 | 10 | 260 | 10 | 0.68 |
| Ir | ug/ml | 4.1E-1 | 4.0E0 | 2.5E0 | 6.5E1 | 1.2E1 | 1.2E2 | 1.0E-9 | 3.4E-1 | 1.6E2 | 3.7E2 | 259 | 10 | 259 | 10 | 0.79 |
| Is | ng/ml | 2.2E0 | 4.0E1 | 8.1E0 | 6.6E1 | 1.7E1 | 8.1E1 | 1.0E-9 | 9.9E-1 | 1.5E2 | 2.6E2 | 260 | 10 | 260 | 10 | 0.85 |
| It | ng/ml | 2.1E0 | 8.2E0 | 1.5E1 | 8.0E1 | 6.8E1 | 2.1E2 | 1.0E-9 | 1.0E-9 | 8.3E2 | 6.8E2 | 260 | 10 | 260 | 10 | 0.66 |
| Iu | ng/ml | 1.8E2 | 6.6E2 | 1.1E3 | 5.2E3 | 3.4E3 | 1.0E4 | 1.0E-9 | 8.5E0 | 2.9E4 | 2.4E4 | 260 | 10 | 260 | 10 | 0.64 |
| Iv | ng/ml | 1.4E1 | 7.6E1 | 5.2E1 | 9.1E2 | 2.5E2 | 1.5E3 | 1.0E-9 | 1.0E0 | 3.8E3 | 3.8E3 | 259 | 10 | 259 | 10 | 0.75 |
| Pz | ng/ml | 4.2E3 | 6.9E3 | 5.9E3 | 6.6E3 | 6.3E3 | 4.4E3 | 1.6E1 | 1.1E3 | 7.0E4 | 1.3E4 | 256 | 10 | 256 | 10 | 0.59 |
| Qa | ng/ml | 3.8E3 | 1.5E4 | 7.1E3 | 3.6E4 | 8.1E3 | 6.6E4 | 1.5E2 | 2.2E3 | 4.2E4 | 2.2E5 | 256 | 10 | 256 | 10 | 0.78 |
| Qb | ng/ml | 1.1E2 | 4.0E2 | 2.4E2 | 4.0E2 | 3.9E2 | 2.0E2 | 7.9E-1 | 1.3E2 | 4.1E3 | 6.0E2 | 256 | 10 | 256 | 10 | 0.78 |
| Qc | ng/ml | 2.5E2 | 3.1E2 | 4.6E2 | 6.4E2 | 5.8E2 | 8.9E2 | 1.0E-9 | 1.3E1 | 4.3E3 | 2.8E3 | 256 | 10 | 256 | 10 | 0.53 |
| Qd | ng/ml | 1.0E4 | 2.6E4 | 2.9E4 | 7.8E4 | 1.3E5 | 8.6E4 | 2.4E2 | 3.5E3 | 2.0E6 | 2.3E5 | 256 | 10 | 256 | 10 | 0.72 |
| Qe | ng/ml | 1.0E3 | 4.3E3 | 2.1E3 | 5.5E3 | 6.3E3 | 5.4E3 | 7.6E0 | 5.7E2 | 9.7E4 | 1.8E4 | 256 | 10 | 256 | 10 | 0.78 |
| Jg | ng/ml | 5.5E2 | 2.2E3 | 8.4E2 | 2.4E3 | 9.9E2 | 1.9E3 | 5.8E0 | 2.8E2 | 7.1E3 | 7.1E3 | 259 | 10 | 259 | 10 | 0.83 |
| Jh | ng/ml | 3.0E0 | 7.8E1 | 2.4E1 | 1.2E2 | 9.4E1 | 1.5E2 | 1.0E-9 | 1.7E0 | 1.2E3 | 4.9E2 | 259 | 10 | 259 | 10 | 0.83 |
| Ji | ng/ml | 6.3E1 | 3.3E2 | 8.9E1 | 4.2E2 | 9.4E1 | 3.4E2 | 1.1E0 | 1.0E2 | 5.4E2 | 1.3E3 | 259 | 10 | 259 | 10 | 0.92 |
| Jj | ng/ml | 5.5E2 | 1.1E2 | 2.3E3 | 4.5E2 | 2.1E4 | 5.7E2 | 2.0E1 | 1.2E1 | 3.4E5 | 1.4E3 | 259 | 10 | 259 | 10 | 0.31 |
| Jk | ng/ml | 3.0E0 | 6.3E1 | 2.2E1 | 8.5E1 | 5.1E1 | 8.5E1 | 1.0E-9 | 1.3E0 | 3.9E2 | 2.4E2 | 259 | 10 | 259 | 10 | 0.77 |
| Jl | ng/ml | 5.1E-1 | 2.0E1 | 2.1E0 | 1.0E3 | 4.8E0 | 3.1E3 | 1.2E-3 | 1.1E-1 | 4.0E1 | 9.9E3 | 259 | 10 | 259 | 10 | 0.85 |
| Jm | ng/ml | 2.2E1 | 3.2E1 | 6.8E1 | 6.6E1 | 1.7E2 | 1.1E2 | 1.0E-9 | 2.1E0 | 2.1E3 | 3.6E2 | 259 | 10 | 259 | 10 | 0.57 |
| Jn | pg/ml | 3.9E-1 | 1.9E0 | 2.6E0 | 1.4E2 | 1.6E1 | 2.9E2 | 1.0E-9 | 4.2E-1 | 2.4E2 | 7.3E2 | 259 | 10 | 259 | 10 | 0.82 |
| Jo | ng/ml | 4.3E3 | 5.0E3 | 5.1E3 | 1.9E4 | 4.0E3 | 3.1E4 | 2.6E2 | 2.3E2 | 2.4E4 | 1.0E5 | 259 | 10 | 259 | 10 | 0.60 |
| Jp | pg/ml | 7.4E4 | 1.1E5 | 7.7E4 | 1.2E5 | 3.9E4 | 4.4E4 | 2.1E3 | 6.5E4 | 3.8E5 | 2.1E5 | 259 | 10 | 259 | 10 | 0.78 |
| Jq | pg/ml | 9.8E1 | 4.0E2 | 1.6E2 | 1.6E3 | 1.8E2 | 2.7E3 | 5.6E0 | 7.1E1 | 1.1E3 | 8.7E3 | 259 | 10 | 259 | 10 | 0.82 |
| Jr | pg/ml | 4.1E0 | 4.2E1 | 3.4E1 | 1.3E3 | 2.0E2 | 2.7E3 | 1.0E-9 | 6.7E0 | 2.4E3 | 7.4E3 | 259 | 10 | 259 | 10 | 0.87 |
| Js | pg/ml | 1.6E1 | 3.4E1 | 5.4E1 | 6.4E2 | 2.3E2 | 1.2E3 | 1.0E-9 | 6.1E0 | 3.0E3 | 3.0E3 | 259 | 10 | 259 | 10 | 0.71 |
| Jt | pg/ml | 2.6E3 | 4.4E3 | 3.1E3 | 1.1E4 | 2.2E3 | 1.6E4 | 1.5E2 | 1.0E3 | 1.8E4 | 5.2E4 | 259 | 10 | 259 | 10 | 0.67 |
| Lh | pg/ml | 1.5E4 | 4.0E4 | 2.3E4 | 1.6E5 | 2.9E4 | 1.9E5 | 1.0E-9 | 1.8E3 | 2.6E5 | 4.8E5 | 260 | 10 | 260 | 10 | 0.81 |
| Li | pg/ml | 3.9E3 | 4.1E4 | 1.7E4 | 8.4E4 | 6.8E4 | 1.0E5 | 1.3E1 | 5.0E2 | 9.2E5 | 3.1E5 | 260 | 10 | 260 | 10 | 0.73 |
| Lj | pg/ml | 3.1E3 | 4.5E3 | 1.9E4 | 5.5E4 | 5.1E4 | 1.2E5 | 1.0E-9 | 2.3E2 | 4.3E5 | 3.9E5 | 260 | 10 | 260 | 10 | 0.65 |
| Nv | pg/ml | 4.0E3 | 4.5E4 | 1.0E4 | 4.7E4 | 2.0E4 | 3.9E4 | 1.0E-9 | 2.6E3 | 1.6E5 | 1.1E5 | 261 | 10 | 261 | 10 | 0.82 |
| Nw | pg/ml | 1.0E4 | 2.7E4 | 1.4E4 | 6.6E4 | 1.7E4 | 8.0E4 | 1.9E2 | 1.1E4 | 2.1E5 | 2.2E5 | 261 | 10 | 261 | 10 | 0.86 |
| Nx | pg/ml | 2.2E2 | 1.2E3 | 4.4E2 | 1.4E3 | 6.3E2 | 1.1E3 | 1.0E-9 | 1.0E-9 | 3.5E3 | 4.1E3 | 261 | 10 | 261 | 10 | 0.81 |
| Ny | pg/ml | 7.7E0 | 1.7E2 | 1.2E2 | 4.6E2 | 1.5E3 | 8.4E2 | 1.0E-9 | 9.8E0 | 2.5E4 | 2.8E3 | 261 | 10 | 261 | 10 | 0.84 |
| Oe | pg/ml | 3.1E1 | 2.0E1 | 2.6E2 | 3.6E2 | 4.0E2 | 4.8E2 | 1.0E-9 | 1.0E-9 | 2.3E3 | 1.1E3 | 259 | 10 | 259 | 10 | 0.55 |
| Of | pg/ml | 1.9E2 | 3.4E2 | 6.0E3 | 1.5E4 | 2.3E4 | 2.3E4 | 1.0E-9 | 1.1E1 | 1.9E5 | 6.6E4 | 261 | 10 | 261 | 10 | 0.61 |
| Og | pg/ml | 7.6E-2 | 5.5E-2 | 3.9E-1 | 9.7E-2 | 1.6E0 | 1.3E-1 | 1.0E-9 | 1.0E-9 | 1.9E1 | 3.2E-1 | 261 | 10 | 261 | 10 | 0.44 |
| Oh | pg/ml | 2.8E0 | 3.8E1 | 1.7E1 | 1.5E2 | 1.0E2 | 3.5E2 | 1.0E-9 | 4.2E0 | 1.4E3 | 1.1E3 | 261 | 10 | 261 | 10 | 0.87 |
| Oi | pg/ml | 2.5E0 | 3.9E0 | 5.2E0 | 7.0E0 | 7.2E0 | 9.8E0 | 1.0E-9 | 1.0E-9 | 4.2E1 | 3.1E1 | 261 | 10 | 261 | 10 | 0.51 |
| Ok | pg/ml | 4.2E2 | 1.5E3 | 5.3E2 | 2.4E3 | 4.4E2 | 2.3E3 | 1.5E1 | 3.2E2 | 3.2E3 | 7.8E3 | 261 | 10 | 261 | 10 | 0.87 |
| Om | pg/ml | 4.3E2 | 2.9E3 | 8.7E2 | 7.7E3 | 2.3E3 | 1.5E4 | 1.0E-9 | 5.4E2 | 3.0E4 | 5.1E4 | 261 | 10 | 261 | 10 | 0.86 |

Figure 35 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| On | pg/ml | 2.0E2 | 1.4E3 | 3.1E2 | 2.1E3 | 4.3E2 | 2.4E3 | 8.4E-1 | 3.1E2 | 4.5E3 | 8.5E3 | 261 | 10 | 261 | 10 | 0.92 |
| Oy | pg/ml | 4.8E-1 | 2.1E0 | 7.2E0 | 7.0E0 | 3.5E1 | 1.0E1 | 1.0E-9 | 1.0E-9 | 4.0E2 | 3.3E1 | 260 | 10 | 260 | 10 | 0.65 |
| Oz | pg/ml | 1.1E-2 | 1.0E-9 | 3.6E-1 | 2.9E0 | 1.8E0 | 8.8E0 | 1.0E-9 | 1.0E-9 | 2.9E1 | 2.8E1 | 260 | 10 | 260 | 10 | 0.43 |
| Pa | pg/ml | 4.2E-1 | 2.7E0 | 1.5E0 | 3.6E1 | 6.4E0 | 7.4E1 | 1.0E-9 | 1.7E-1 | 8.6E1 | 2.3E2 | 260 | 10 | 260 | 10 | 0.76 |
| Pb | pg/ml | 1.0E-9 | 1.0E-9 | 2.1E0 | 3.4E0 | 3.0E1 | 9.9E0 | 1.0E-9 | 1.0E-9 | 4.9E2 | 3.2E1 | 260 | 10 | 260 | 10 | 0.41 |
| Pc | pg/ml | 9.9E-2 | 1.0E-9 | 4.1E-1 | 4.5E0 | 9.8E-1 | 1.2E1 | 1.0E-9 | 1.0E-9 | 1.4E1 | 3.8E1 | 260 | 10 | 260 | 10 | 0.50 |
| Pd | pg/ml | 1.7E0 | 1.3E1 | 7.3E0 | 2.6E1 | 5.3E1 | 3.7E1 | 1.0E-9 | 7.3E-2 | 8.4E2 | 1.2E2 | 260 | 10 | 260 | 10 | 0.75 |
| Pe | pg/ml | 2.3E1 | 2.5E2 | 1.3E2 | 2.9E3 | 5.0E2 | 4.9E3 | 1.0E-9 | 1.4E1 | 4.7E3 | 1.5E4 | 260 | 10 | 260 | 10 | 0.78 |
| Pf | pg/ml | 1.8E0 | 2.6E1 | 1.5E1 | 7.6E1 | 9.7E1 | 1.3E2 | 1.0E-9 | 6.5E-1 | 1.5E3 | 4.3E2 | 260 | 10 | 260 | 10 | 0.81 |
| Pg | pg/ml | 4.6E0 | 7.7E1 | 8.7E1 | 4.8E2 | 5.8E2 | 7.3E2 | 1.0E-9 | 4.6E-1 | 7.7E3 | 2.2E3 | 260 | 10 | 260 | 10 | 0.82 |
| aA | mg/dL | 9.0E-1 | 2.1E0 | 9.9E-1 | 2.3E0 | 4.8E-1 | 1.4E0 | 3.0E-1 | 5.5E-1 | 4.2E0 | 4.7E0 | 392 | 14 | 392 | 14 | 0.79 |

Analyte panel data:

Unconstrained panels with 3 analytes, where 1.0E-8 >= 'model p-value' > 0. Contains 3,110 panels of 295,240 total panels evaluated. : Et{Jq(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) No(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ji(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) aA(Fp Fr Hq Hr Hu Hv Hw Hx Ih Ii Ij Ik Il Im In Io Ip Iq Ir Is It Iu Iv Jg Jh Jj Jk Jl Jm Jn Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Oh(Fr Hr Hu Hv Hw Hx Ii Ik In Io Ip Iq Ir Iv Jg Jh Jj Jk Jl Jn Jo Jr Lh Lv Lw Lx Ma Mb Md Mi Mj Mk Mr Ms Mt Mu My Mz Na Nb Nc Nd Ne Nf Ng Nh Nj Nl Nn Nq Nr Ns Nt Nu Nv Nw Ny Oe Og Oi Ok Om On Oy Pa Pb Pc Pe Pg Po Pz Qc) Jr(Fr Hr Hw Ik Im Io Ip Iq Iu Jg Jh Jj Jk Jl Jn Lh Lu Lw Lx Mb Md Mi Mj Mm Mq Mr Ms Mt Mu My Mz Nc Nd Nf Nh Nj Nk Nl Nn Nr Ns Nt Nv Nw Ny Og Oi Ok Om On Oy Pa Pb Pc Pe Pg Po Pz Qc) On(Hr Hu Ik Io Ip Iq Jh Jj Jn Lv Lw Lx Mb Mg Mj Mk Ms Mv My Mz Nb Nc Ne Ng Nh Nj Nl Nn Nq Ns Of Og Oi Ok Oy Pa Pb Pc Pz Qc) Pb(Fr Hr Hw Hx Ii Ip Ir Is Jk Jl Jn Lh Lw Lx Mb Md Mr Mt Mu Mz Nb Nf Nh Nn Nr Nt Nv Nw Ny Ok Om Pa Pc Pe Pf Pg Po) Ik(Fr Io Iq Ir Is Iv Jh Jk Jl Jn Lh Lx Lz Md Mr Mt Mu Me Nh Nn Nr Nt Nv Nw Ny Ok Om Pa Pe Pf Pg Po Wm) Mb(Fr Io Iq Ir Is Jh Jl Jn Js Lh Lw Lx Lz Md Mh Mr Mt Mu Mz Ne Nf Nh Nn Nt Nw Ny Ok Om Pa Pe Pf Pg) Nn(Hr Hu Hw Ip Ir Is Jv Jl Jn Lh Lw Lx Mi Mr Mu My Mz Ne Ng Nh Nl Nr Nt Nw Ny Oi Ok Pa Pe Pz) Pc(Hw Io Ip Iq Ir Is Jl Jn Lh Lx Md Mi Mr Mt Mz Ne Nf Nh Nl Ns Nt Nw Ny Ok Pa Pe Pz) Lw(Fr Io Ip Iq Is Jl Jn Lh Lu Lx Mf Mi Mr Mt Mu Mz Nc Nf Nl Ok Pa Pe Po Wm) Fr(Hu Ir Is Jj Jn Ma Mg My Mz Ne Ng Nh Nj Nl Nq Ok Oy Pz) Ip(Io Iq Is Jl Jn Lh Lu Lx Md Mr Mt Mu Mz Nc Nf Nw Ok Pa) Jl(Io Jh Jj Jn Lv Lx Md Mj Mu Mz Nc Nf Nh Nj Oz Pz) Io(Is Iv Jn Lh Lx Mi Mr Mz Nc Nk Nl Pa) Lx(Hu Ir Is Jn Ly Mt Mz Ng Ok Wm) Nw(Hw Lh Nd Nj Nt Ok Wm) Pa(Jn Mu Mz Nc Nj Ok Pz) Om(Hu Jh My Ng Og Oy) Mu(Hu Jn Ng Nj Oy) My(Mt Mw Nb Ny) Ng(Jk Lh Po) Nj(Is Mt Nf) Qc(Iq Mt Mz) Oy(Mw Ny Po) Is(Nc Pz) Jj(Jk Lh) Ok(Jt Pz) MgLh HuJk} On{Ik(aA Fp Fr Hq Hr Hu Hv Hw Hx Ih Ii Ij Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) My(aA Fp Fr Hq Hr Hu Hv Hw Hx Ih Ii Ij Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Oy(aA Fp Fr Hq Hr Hu Hv Hw Hx Ih Ii Ij Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oz Pa Pb Pc Pd Pe Pf Pg Po Pz Qa Qb Qc Qd Qe) Pb(aA Fp Fr Hq Hr Hu Hv Hw Hx Ih Ii Ij Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oz Pa Pc Pd Pe Pf Pg Po Pz Qa Qb Qc Qd Qe) aA(Fp Fr Hq Hr Hu Hv Hw Hx Ih Ii Ij Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl Nm Nn No Nq Nr Nt Nu Nv Nw Nx Ny Oe Of Og Oh Oi Ok Om Oz Pa Pc Pe Po Pz Qb Qc Qd) Hu(Fr Hx Im Io Ip Iq It Iu Jg Jh Ji Jj Jq Jr Lh Lv Lw Lx Mb Mh Mi Mj Ml Mm Mr Mu Mz Nb Nj Nn No Nq Nr Nt Ny Og Oi Pc Pz Qc Qd) Jj(Fr Hx Io Ip Iq Ji Jq Jr Lh Lw Lx Mb Mh Mj Mk Ml Mm Mz Nb Nd Nj Nl Nn No Nq Nt Ny Of Og Oi Pz Qc) No(Hr Ii Il Io Ip Ji Jm Jr Lw Lx Ly Mb Mj Mk Mm Mr Nb Nj Nn Nq Nr Ns Og Ok Pc Po) Ji(Fr Ii Ij Io Js Lv Lx Mb Mh Mj Mk Ml Mm Ms Mv Mz Nb Nr Nx Of Og Oi Pz Qb Qc) Og(Hq Io Ip Jg Jq Jr Lw Lx Mb Mj Mk Nb Nj Nn Nq Nr Pc Pz Qc) Jq(Ii Ij Im Ip Mb Md Mj Mm Nb Nj Ny Of Om Qc) Mb(Im Ip Iq Jr Mq Ms Nj Ns Of Oh Ok) Mj(Ip Jr Ms Ns Ok) Nb(Ip Lw Ms Ok Pz) Qc(Ip Jq Jn Jr Mz) Lx(Ip Jm Ly Ms) Lw(Im Ns Of) Mv(Io Nn) Jt(Ir Ok) WmMk MmJr IoOf IpJm} Ji{Mb(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) No(aA Fp Fr Hq Hr Hu Hv Hw Hx Ih Ii Ij Ik Il Im In Io Ip Iq Ir Is It Iu Iv Jg Jh Jj Jk Jl Jm Jn

Figure 35 Continued

Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) aA(Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Fr(Fp Hq Hr Hu Hv Hw Hx Ii Ij Ik Il Im In Io Ip Iq Ir Is It Iu Iv Jh Jj Jl Jm Jn Jo Jp Jq Jr Js Jt Lh Li Lu Lv Lw Lx Ly Ma Md Me Mf Mg Mh Mi Mj Mk Ml Mm Mn Mq Mr Ms Mt Mu Mv Mw Mx My Mz Na Nb Nc Nd Ne Nf Ng Nh Nj Nl Nn Nq Nr Ns Nt Nu Nw Nx Ny Oe Of Og Oh Oi Ok Om Oy Pa Pb Pc Pd Pe Pg Po Pz Qa Qb Qc Qd) Ik(Hw Io Iq Ir Iu Iv Jg Jh Jk Jl Jo Jr Lh Lx Lz Mi Mj Mk Mm Mr Mt Mu Nb Nn Nr Nt Nv Oh Ok Om Oz Pa Pe Pf Po Wm) Pb(Hw Ii Io Ip Jg Jh Jk Jl Jo Lh Ma Mi Mm Mr Mt Mu Nb Nn Nr Nt Nv Ok Om Pa Pe Po) Qc(Iq Ir Iv Jg Jk Jl Jn Jq Jr Mm Mr Mt Mu Mx Mz Nn Nt Nv Oh Ok Pa) Jl(Fp Ii Ij Im Io It Js Lv Mh Mj Mk Mm Nn Nr Nx Pc Pz Qa Qb Qd) Ok(Fp Ij Io Js Jt Lj Mh Mj Ml Mm Mq Mu Nd Nn Nr Pc Pz Qd) Mu(Ij My Nb Ng Nr Og Oh Oy) Oh(Fp Io Js Mj Mm Qb Qd) Mm(Io Jr Lu Mg Pa) My(Jg Jh Jk Mw) Io(Hw Iq Nt Pa) Mj(Lh Mr Nt) Jk(Ng Og Oy) Nr(Mt Pa) Ij(Hw Jh) Og(Jg Jh) WmMk LxLy MwOy JrJs} aA{Nj(Fp Fr Hq Hr Hw Hx Ii Ij Ik Il Im In Io Ip Iq Ir Is It Jg Jh Jj Jk Jl Jn Jo Jq Jr Lh Lj Lv Lw Lx Ma Mb Mc Md Me Mg Mh Mi Mj Mm Mn Mp Mq Mt Mu Mv Mw My Mz Na Nb Nc Nd Nf Ni Nk Nl Nm Nn No Nq Ns Nt Nv Nw Nx Ny Oe Of Oh Oi Ok Om Oy Oz Pa Pb Pc Pd Pe Pf Pg Po Qb Qd) Pc(Fr Hq Hr Hw Hx Ii Ij Ik Il Im Io Ip Ir Is Iu Jg Jh Jl Jn Jo Jq Jr Lh Lv Lw Lx Ma Mb Mi Mm Mp Mr Mt Mx Mz Na Nb Nf Nm No Ns Nt Nv Nw Nx Ny Of Oh Oi Ok Om Pa Pb Pe Pf Pg Po) Lw(Fr Ik Il Im Ip Is Jg Jh Jl Jn Jq Jr Lh Lv Lx Ma Mb Me Mi Mm Mn Mp Mt Nm Nn No Nv Nw Nx Ny Og Oh Ok Om Pa Pb Pg) Ip(Fr Hr Ik Io Jg Jh Jl Jq Jr Lv Mb Me Mj Mm Mn Mt Mu Nn No Ns Nx Ny Oh Ok Om Oz Pb) Mm(Fr Hr Ij Ik Io Jl Jn Jq Jr Lh Lv Mb Mz No Nv Nw Nx Ny Ok Om Pa Pg) Mb(Fr Jg Jh Jl Jq Jr Lh Lv Lx Mt Nn No Nw Nx Ny Oh Ok Om Pb Pg) Jg(Hu Ik Io Jl Jq Lv My Ng Ns Og Ok Oy Pb) Fr(Hr Hu Ik Jq Jr Lv Ng Nm Nq Nx Ok Pb) Ik(Jh Jl Jq Mt Nv Nx Ny Ok Om) Nn(Hu Jq Jr Lv Nm Nx Ok) Me(Jq Jr Lv Nw Nx Ok Om) Pb(Jq Lh Mt Nx Ok Om) Mw(My Oy) Ok(Hr Mj) HuOm} Ok{Ik(Fr Hq Hr Hx Ii Il Im Io Ip Iq Ir Is Iu Iv Jg Jh Jk Jl Jn Jq Jr Lh Li Lu Lw Lx Ly Lz Mb Md Me Mi Mk Mm Mp Mr Mt Mu Mv Mw Mx Nb Nc Nd Ne Nh Nj Nl Nn No Nq Nt Nv Nw Nx Ny Oh Om Pa Pb Pc Pd Pe Pf Pg Po Qb Qc) Pb(Fr Hq Hr Hx Ii Il Im Io Ip Iq Ir Is It Iu Iv Jg Jh Jk Jl Jn Jq Jr Lh Lw Lx Ma Mb Md Me Mi Mm Mp Mr Mt Mu Mv Mw Nb Nd Nf Nj Nn No Nq Nt Nv Nw Nx Ny Oh Om Oy Pa Pc Pd Pe Pf Pg Po Qc) Mb(Fr Ip Is Jh Jq Jr Lv Lw Lx Md Mt Nh Nn No Nw Ny Oh Pc Pg) No(Mh Mj Mm Mq Nn Pc) Jq(Mm Nd Nn Pc Qc) Fr(Jr Mj) Mw(My Oy) LxLy MmJr} No{Mb(Fr Hu Il Im Ip Is Jg Jh Jj Jl Jn Jp Jq Jr Lv Lw Me Mj Mm Mn Ms Mt Nj Nk Nm Nn Ns Nw Ny Oh Om Pb Pc) Jq(Fr Ik Ip Mj Mm Nj Nn Pb Pc) Pb(Ip Jh Jo Lh Lw Nx Om) Mj(Is Jr Lv Oh Om) Mm(Ip Jn Jr Ms) Nj(Ik Jr Ms Om) Jg(Hu Ik My Ng) Om(Hu Ik Oy) Pc(Ip Jn Jr) Nn(Ip Jr) Mw(My Oy) Jh(Hu Ik)} Jq{Mb(Fr Im Ip Iq Is Iv Jg Jh Jl Jr Lh Li Lv Lx Lz Mi Mm Mr Mt Nd Nl Nn Nt Oh Pa Pc Wm) Mm(Jl Jr Lh Lx Mi Mr Nt Pa) Pb(Fr Jl Lh Mr Pa Pe) Ik(Fr Mr Nt Pa Pe) Fr(My Nj Nl) Pc(Lh Mi Nt) MwMy QcJl} Ik{Om(Iq Ir Iv Jl Lh Mr Mt Nb Nt Pa Pe) Jh(Ir Is Iv Jl Lh Mr Nb Pa Pe) Fr(Ir Is Iv Jn Jr Mr Nb Pe) Mt(Iv Jl Mb Mr Nb Nt Pe) Jl(Jg Lx Mw Ny) Nw(Mr Pe) WmNv LxIv} Pb{Lh(Fr Ip Jg Jh Lw Mm Mt Mu Nn Nw Oh Om Pc) Fr(Hw Ir Is Jo Mb Na Pe) Om(Hw Jl Mr Nb Nr Pe) Mb(Jl Mt Nw Ny Po) Mt(Hw Jo Pe) Jo(Lx Nw) NfJl HwNw} Mb{Nw(Fr Jr Mm My Nj Og Oh Oy Wm) FrJr LxLy} Jr{Fr(Im Ip Nj Qc) MwMy} WmLyNx LxHuJh MjLhOh MmNgNy MwMyNw

Unconstrained panels with 3 analytes, where 1.0E-7 >= 'model p-value' > 1.0E-8. Contains 14,656 panels of 295,240 total panels evaluated. :
Et{Pg(Fp Fr Hq Hr Hu Hv Hw Hx Ih Ii Ij Il Im In Io Ip Iq Ir Is It Iu Iv Jg Jh Jj Jk Jl Jm Jn Jo Jp Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oi Ok Om On Oy Oz Pa Pc Pd Pe Pf Po Pz Qa Qb Qc Qd Qe) Mi(Fp Fr Hq Hr Hu Hv Hw Hx Ih Ii Ij Ik Il Im In Ip Iq Ir Is It Iu Iv Jg Jh Jj Jk Jl Jm Jn Jo Jp Js Jt Lh Li Lj Lu Lv Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nt Nu Nv Nw Nx Ny Oe Of Og Oi Ok Om On Oy Oz Pa Pb Pd Pe Pf Po Pz Qa Qb Qc Qd Qe) Po(Fp Fr Hq Hr Hu Hv Hw Hx Ih Ii Ij Il Im In Io Ip Iq Ir Is It Iu Iv Jg Jh Jj Jk Jl Jm Jn Jo Jp Js Jt Lh Li Lj Lu Lv Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Nh Ni Nj Nk Nl Nm Nn Nq Nr Ns Nt Nu Nv Nw Nx Ny Oe Of Og Oi Ok Om On Oz Pa Pc Pd Pe Pf Pz Qa Qb Qc Qd Qe) Md(Fp Fr Hq Hr Hu Hv Hw Hx Ih Ii Ij Il Im In Io Iq Ir Is It Iu Iv Jg Jh Jj Jk Jm Jn Jo Jp Js Jt Lh Li Lj Lu Lv Lw Lx Ly Lz Ma Mc Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oi Ok Om On Oy Oz Pa Pd Pe Pf Pz Qa Qb Qc Qd Qe Wm) Nt(Fp Fr Hq Hr Hu Hv Hw Hx Ih Ii Ij Il Im In Io Ip Iq Ir Is It Iu Iv Jg Jh Jj Jk Jl Jm Jn Jo Jp Js Jt Lh Li Lj Lu Lv Lw Lx Ly Lz Ma Mc Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nu Nv Nx Ny Oe Of Og Oi Ok Om On Oy Oz Pa Pd Pe Pf Pz Qa Qb Qc Qd Qe) Hw(Fp Fr Hq Hr Hu Hv Hx Ih Ii Ij Ik Il Im In Io Ip Iq Ir Is It Iu Iv Jg Jh Jj Jk Jl Jm Jn Jo Jp Js Jt Lh Li Lj Lu Lv Lw Lx Ly Lz Ma Mb Mc Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nu Nv Nx Ny Of Og Oi Ok Om On Oy Oz Pa Pd Pe Pf Pz Qa Qb Qc Qe) Ir(Fp Hq Hr Hu Hv Hx Ih Ii Ij Il Im In Io Ip Iq Is It Iu Iv Jg Jh Jj Jk Jl Jm Jn Jo Jp Jr Js Jt Lh Li Lj Lu Lv Lw Ly Lz Ma Mc Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nu Nv Nw Nx Ny Oe Of Og Oi Ok Om On Oy Oz Pa Pd Pe Pf Pz Qa Qb Qc Qd Qe) Ny(Fp Fr Hq Hr Hu Hv Hx Ih Ii Ij Il Im In Io Ip Iq Is It Iu Iv Jg Jh Jj Jk Jl Jm Jn Jo Jp Js Jt Lh Li Lj Lu Lv Lw Lx Ly Lz Ma Mc Me Mf Mg Mh Mj Mk Ml Mm Mn Mp Mq Mr Ms Mt Mu Mv Mw Mx Mz Na Nb Nc Nd Ne Nf Ng Nh Ni Nj Nk Nl Nm Nq Nr Ns Nu Nv Nw Nx Oe Of Og Oi Ok Om On Oz Pa Pd Pe Pf Pz Qa Qb Qc Qd Qe Wm) Pe(Fp Fr Hq Hr Hu Hv Hx Ih Ii Ij Il Im In Io Ip Iq Is It Iu Iv Jg Jh Jj Jk Jl Jm Jn Jo Jp Js Jt Lh Li Lj Lu Lv Lx Ly Lz Ma Mc Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nu Nv Nw Nx Oe Of Og Oi Ok Om On Oy Oz Pa Pd Pf Pz Qa Qb Qc Qd Qe) Nf(Fp Fr Hq Hr Hu Hv Hx Ih Ii Ij Ik Il Im In Io Iq Is It Iu Iv Jg Jh Jj Jk Jm Jn Jo Jp Js Jt Lh Li Lj Lu Lv Lx Ly Lz Ma Mc Me Mf Mg Mh Mj Mk Ml Mm Mn Mp Mq Mr Ms Mt Mu Mv Mw Mx My Mz Na Nb Nc Nd Ne Ng Nh Ni Nk Nl Nm Nn Nq Nr Ns Nu Nv Nw Nx Oe Of Og Oi Ok Om On Oy Oz Pa Pd Pf Pz Qa Qb Qc Qd Qe) Iq(Fp Fr Hq Hr Hu Hv Hx Ih Ii Ij Il Im In Io Is It Iu Iv Jg Jh Jj Jk Jl Jm Jn Jo Jp Js Jt Lh Li Lj Lu Lv Lx Ly Lz Ma Mc Me Mf Mg Mh Mj Mk Ml Mm Mn Mp Mq Mr Ms Mt Mu Mv Mw Mx My Mz Na Nb Nc Nd Ne Ng Nh Ni Nj Nk Nl Nm Nn Nq Nr Ns Nu Nv Nw Nx Oe Of Og Oi Ok Om Oy Oz Pa Pb Pd Pf Pz Qa Qb Qd Qe) Mr(Fp Fr Hq Hr Hu Hv Hx Ih Ii Ij Il Im In Is It Iu Iv Jg Jh Jj Jk Jl Jm Jn Jo Jp Js Jt Lh Li Lj Lu Lv Lx Ly Lz Ma Mc Me Mf Mg Mh Mj Mk Ml Mm Mn Mp Mq Ms Mt Mu Mv Mw Mx My Mz Na Nb Nc Nd Ne Ng Nh Ni Nj Nk Nl Nm Nq Nr Ns Nu Nv Nw Nx Oe Of Og Oi Ok Om On Oy Oz Pa Pd Pf Pz Qa Qb Qc Qd Qe) Mt(Fp Fr Hq Hr Hu Hv Hx Ih Ii Ij Il Im In Io Is It Iu Iv Jg Jh Jj Jk Jl Jm Jn Jo Jp Js Jt Lh Li Lj Lu Lv Ly Lz Ma Mc Me Mf Mg Mh Mj Mk Ml Mm Mn Mp Mq Ms Mu Mv Mw Mx Mz Na Nb Nc Nd Ne Ng Nh Ni Nk Nl Nm Nn Nq Nr Ns Nu Nv Nw Nx Oe Of Og Oi Ok Om On Oy Oz Pa Pd Pf Pz Qa Qb Qd Qe Wm) Om(Fp Fr Hq Hr Hv Hx Ih Ii Ij Il Im In Io Ip Is It Iu Iv Jg Jj Jk Jl Jm Jn Jo Jp Js Jt Lh Li Lj Lu Lv Lw Lx Ly Lz Ma Mc Me Mf Mg Mh Mj Mk Ml Mm Mn Mp Mq Ms Mu Mv Mw Mx Mz Na Nb Nc Nd Ne Nh Ni Nj Nk Nl Nm Nn Nq

Figure 35 Continued

Oh(Hr Hv Hw Ij Ik In Ir Is Jj Jl Jn Jo Lj Lv Lw Ly Mh Mr Ms Mu Mz Na Nm Nx Ny) Lw(Ik Im Io Iq Ir Is Jj Jl Jm Jn Jp Lv Ly Mj Mn Ms Mz Nb Ng Ns Nw Ny) Mj(Hr Hv Ir Iv Jj Jl Jn Js Lh Ms Mz Nf Nm Nw Nx Ny Qa) Is(Hr Hu Ik Il Io It Jj Jm Lv Ly Me Mr Ms Mu Nm Nr Qd) Ik(Ir Jl Jn Lh Lv Ms Mu Nm Ns Nw Nx Ny Pe Wm) Jj(Hr Jk Jl Jn Lh Lv Mn Ms Mu Nm Nv Nx Ny Of) Ms(Im Io Jl Lv Me Mr Mu Nm Nx Ny) Lv(Im Jn Me Mr) Hu(Mu Mw Ny) Jm(Me Ny) Jn(Hr Mr) MwNg JlOz} Ok{Fr(Fp Hq Hr Hu Hv Hw Hx Ih Ii Ij Il Im In Io Ip Iq Ir Is It Iu Iv Jg Jh Jj Jk Jl Jm Jn Jo Jp Jq Js Jt Lh Li Lj Lu Lv Lw Lx Ly Lz Ma Mc Md Me Mf Mg Mh Mi Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Om Oy Oz Pa Pc Pd Pe Pf Pg Po Pz Qa Qb Qc Qd Qe) Mb(Fp Hq Hr Hu Hv Hw Hx Ih Ii Ij Il Im In Io Iq Ir It Iu Iv Jg Jj Jk Jl Jm Jn Jo Jp Js Jt Lh Li Lj Lu Ly Lz Ma Mc Me Mf Mg Mh Mi Mj Mk Ml Mm Mn Mp Mq Mr Ms Mu Mv Mw Mx My Mz Na Nb Nc Nd Ne Nf Ng Ni Nj Nk Nl Nm Nq Nr Ns Nt Nu Nv Nx Oe Of Og Oi Om Oy Oz Pa Pd Pe Pf Po Pz Qa Qb Qc Qd Qe) Nn(Fp Hq Hr Hu Hw Hx Ii Il Im In Io Ip Iq Ir Is It Iu Iv Jg Jh Jj Jk Jl Jm Jn Jo Jr Jt Lh Li Lj Lu Lv Lw Lx Lz Ma Mc Md Me Mf Mg Mh Mi Mj Mk Ml Mm Mn Mp Mq Mr Ms Mt Mu Mv Mx My Mz Na Nb Nc Nd Ne Nf Ng Nh Nj Nk Nl Nq Nr Ns Nt Nu Nv Nw Ny Oe Og Oh Oi Om Oy Pa Pc Pe Pf Pg Po Pz Qc) Pb(Fp Hu Hv Hw Ih Ij In Jj Jm Jo Jp Js Jt Li Lj Lu Lv Ly Lz Mc Mf Mg Mh Mj Mk Ml Mn Mq Ms Mx My Mz Na Nc Ne Ng Nh Ni Nk Nl Nm Nr Ns Nu Oe Of Og Oi Oz Pz Qa Qb Qd Qe) Jq(Fp Hr Hv Hw Ij Im Io Ip Iq Is It Iu Jg Jk Jl Jr Js Jt Lh Lj Lw Lx Me Mh Mi Mj Ml Mp Mq Mr Mt Mu Mz Nb Nc Ne Nj Nl Nq Ns Nt Nv Ny Og Oh Oz Pa Pe Pz Qd) Ik(Fp Hu Hv Hw Ih Ij In It Jj Jm Jo Jp Js Jt Lj Lv Ma Mc Mf Mg Mh Mj Ml Mn Mq Ms My Mz Na Nf Ng Ni Nk Nm Nr Ns Nu Oe Of Og Oi Oy Oz Pz Qa Qd Qe) Pc(Fp Im Io Ip Iq Is Jh Jl Jn Jr Lh Li Lj Lx Md Mf Mg Mh Mi Mk Mm Mp Mq Mt Nd Nt Nv Nw Ny Oh Oi Pa Pz Qc) Mm(Im Io Ip Iq Is Jh Jj Jl Jn Jt Lh Lu Lv Lx Md Mg Mi Mq Mt Mu Nd Nm Nt Nv Nw Ny Oh Om Pa Pg Pz) Mj(Ip Iq Is Jh Jl Jn Jr Lh Lx Mi Mt Mu Nd Nq Nt Nv Nw Ny Oh Om Pa Pg) Lw(Im Io Ip Is Jh Jl Jr Lh Lx Mi Mq Mt Nd Nm Nq Nt Nv Ny Og Oh Pa) Mt(Fp Hr Im Ip Jr Li Lj Lx Mh Mi Mk Ml Mp Mq Mr Nb Nd Oh Oi Qc) Ip(Fp Im Jh Jr Lx Md Mh Mi Mq Nd Nv Nw Oh) Mq(Jh Jl Jr Lx Mp Mu Nd Nw Ny Oh Pa) Jh(Jr Jt Lx Mi Mp My Nd Og Oh Oy) Oh(Fp Jg Lj Lx Mh Mi Mu Nd Oi) Jr(Fp Im Lx Mi Mu Nd Qc) Jj(Jk Lx Mi Nd Nq Nv) Nw(Im Mh Ml Mp Nd Qc) Fp(Jl Lx Ny) Jg(Jt My Og) Om(My Og Oy) Lx(Hu Mh) Ly(Mi Nd) Iq(Lj Qc) NqHu MhNy MkPa MwOg MzQc JoNv} Jq{Fr(Hq Hr Hu Hv Hw Hx Ih Ii Ij Il Im In Io Ip Iq Ir Is Iu Iv Jg Jh Jj Jl Jm Jn Jo Jr Jt Lh Li Lj Lu Lv Lw Lx Lz Ma Md Me Mf Mg Mh Mi Mj Mk Ml Mm Mn Mp Mr Ms Mt Mu Mv Mw Mx Mz Na Nb Nc Nd Ne Nf Ng Nh Ni Nk Nm Nn Nq Nr Ns Nt Nu Nw Nx Ny Oe Of Og Oh Oi Om Oy Oz Pa Pc Pd Pe Pf Pg Po Pz Qb Qc Qe) Mb(Fp Hq Hr Hv Hw Hx Ii Ik Il Ir Iu Jj Jk Jn Jo Jp Jt Lj Lu Lw Ma Md Me Mf Mh Mj Mk Ml Mn Mp Ms Mu Mv Mw Mx My Na Nb Nc Ne Ng Nh Nj Nm Nq Nr Nu Nv Nw Nx Ny Og Om Oz Pb Pe Pf Pg Po Qa Qb Qe) Mm(Hr Hv Hw Hx Ik Im Io Ip Iq Ir Is Iu Iv Jh Jj Jn Jo Lu Lv Lz Mf Mh Mt Mx Nb Nc Nd Ng Nl Nm Nr Nv Nw Ny Og Oh Pb Pc Pe Po Qc) Lh(Hr Hu Hx Ii Ij Ik Im In Ip Jg Jh Jj Jl Jr Lw Ly Md Me Mh Mj Ml Mt Mv My Nf Ng Nj Nn Ny Of Og Oh Oy Pg Po Qc) Jl(Hr Ij Ik Im Io Ip Jg Jh Jj Jr Lw Lx Me Mi Mj Mp Mq Mt Nc Nd Nj Nn Nt Og Oh Oz Pc Qd) Mi(Hu Hx Ij Ik In Ip Jg Jh Jj Jr Ly Md Mh Ml Mt My Nf Ng Nj Nn Ny Og Oh Oy Pb Pg) Lx(Hu Ik Ip Jg Jj Jm Ly Md Mh Ml Mt My Nf Ng Nj Nn Ny Og Oh Oy Pb Pc Pg) Pa(Hx Ii Ij Im In Ip Md Me Mh Mk Ml Mt My Nb Nj Nn Ny Og Oh Oy Pc Qc) Nt(Im Io Ip Jg Jh Jj Jr Me Mj Mt Nj Nn Oh Pb Qc) Mr(Ij Im Ip Jg Jh Me Mh Mj Ml Mt Nj Nn Oh Pc Qc) Nn(Hw Ik Im Ip Iq Iu Jo Jr Nd Nl Pb Pc) Pc(Hw Im Ip Iq Iu Jo Mp Mt Nd Nl Oh Pe) Pb(Ii Jk Jo Mt Mu Nb Nr Po) Oh(Ip Iq Iu Jg Jh Nd Pe) Mt(Ik Im Nd Nj Pe) Ik(Iq Mk Po Wm) Pe(Im Ip Nj Qc) Jg(My Ng Og) Me(Is Iv) Nd(Jj Nj) Iq(Im Qc) Oy(Mw Po) WmMy NqHu HwIp} Fr{Jr(Fp Hq Hr Hu Hv Hw Hx Ih Ii Ij Il In Io Iq Ir Is It Iu Iv Jg Jh Jj Jk Jl Jm Jn Jo Jp Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nm Nn Nq Nr Ns Nt Nu Nv Nw Nx Ny Oe Of Og Oh Oi Om Oy Oz Pa Pb Pc Pd Pe Pf Pg Po Pz Qa Qb Qd Qe) Mb(Hu Ih Ik Im Io Ip Iq Ir Is Iv Jj Jl Jn Js Lw Lx Lz Mg Mh Mt Mx My Mz Ne Ng Nh Nj Nl Nq Nt Ny Og Oh Oy) Pb(Hr Hv Hx Ij In Ip Iv Jl Jn Js Jt Lw Mq Mr Mt Mz Nb Nf Nr Nt Nw Nx Ny Oh Om Po Qa) Is(Hu Il Im Ip Ir Jj Jm Jn Lw Ma Mg Mj Mk Mm My Na Nb Ng Nj Nq Nr Og Oh Oy) Ir(Hu Im Ip Jj Jo Lw Mj Mk Ml Mm Mt My Ng Nj Nl Nr Nw Oh Oy Qc) Oh(Hr Hu Hv Hw Ik Ip Iv Jj Jn Jt Lh Lw Na Ng Nj Nq) Ik(Hr Hx Iq Jl Jt Lh Mt Nh Nt Nw Ny Om Po) Jn(Hu Im Ip Jj Lw Mm My Na Ng Nj Nl Oy Qc) My(Hx Ii Lh Mr Mt Mw Nb Nw Ny Om) Ng(Hx Jg Jh Lh Mr Nt Ny Om Pe Po) Oy(Hr Hx Ii Lh Mw Nb Ny Om Pe Po) Jj(Hr Hw Iv Jl Jo Lh Na Nj Nt) Hu(Im Jh Lh Mr Ny Om) Nj(Hw Mz Na) Lw(Iq Lh) NmMg NaNw} Ik{Jl(Im Io Ip Iq Ir Is Iv Jj Jn Jr Js Lh Li Lw Mb Md Mm Mp Mr Mu Mz Nb Nf Nh Nj Nm Nn Nt Nu Nv Nw Oh Pc Pd Pe Pf Po) Mt(Hr Iq Ir Is Jh Jn Jo Jr Jt Lh Li Lw Mj Mk Nj Nr Nv Ny Oh Oz Pa Pg Po) Om(Hw Is Iu Jn Jo Jr Li Lx Lz Mi Mj Mk Mm Mp Mx Nl Nr Nv Og Oh Oz Pf Po) Ny(Iq Ir Is Iv Jh Lh Li Lz Mb Mk Mm Mr Nb Nn Nt Oh Oz Pa Pc Pe Wm) Pe(Ip Is Jg Jn Jr Lw Lx Mm Mu Mw Nj Nn Nv Oh Pb Pc) Jh(Hx Iq Jr Li Lx Lz Mi Mj Mk Mx Nt Nv Oh Pg Po) Lh(Ip Is Jg Jj Jn Jr Lw Mm Mu Nn Nv Nw Oh Pb Pc) Mr(Ip Is Jg Jr Lw Lx Mm Mu Nj Nn Nv Oh Pc) Nb(Ip Is Jg Jr Mm Mu Nn Nv Nw Oh Pb Wm) Lx(Hq Iq Ir Is Jr Jt Mh My Nt Pb Wm) Ir(Ip Jg Mm Mu Mw Nn Nv Nw Pg) Is(Jg Mm Mu Nn Nt Nv Pb Po) Iv(Jg Mm Mu Mw Nn Nv Nw) Jr(Jg Jk Mm Mu Nn Nt Pa) Po(Ip Jg Mm Nj Pb Wm) Nw(Hw Iq Jo Mb Mj Nt) Nt(Li Nn) Nv(Iq Li) MwMy JgOh} Mb{Nw(Fp Hq Hr Hu Hv Hw Hx Ij Im In Io Ip Iq Ir Is Iu Iv Jg Jh Jj Jk Jl Jn Jo Js Lh Li Lj Lu Lv Lw Lx Ly Lz Ma Md Me Mf Mg Mh Mi Mj Ml Mn Mp Mq Mr Ms Mt Mu Mv Mw Mx Mz Na Nb Nc Nd Ne Nf Ng Nh Ni Nk Nl Nm Nn Nq Nr Ns Nt Nu Nv Ny Oe Of Oi Om Oz Pa Pc Pe Pf Pg Po Pz Qb Qc) Mt(Hu Ip Iq Ir Is Iv Jj Jl Jn Jr Lh Lv Lw Mr Ng Nj Nn Ns Nt Of Og Oh Oy) Jr(Im Ip Jg Jh Jl Lh Lw Lx Ma Mm Mr Mu Nj Nm Nn Nt Oh Om) Iq(Ip Is Jg Jh Jl Lv Lw Mm Nj Nn Ny Oh Om) Oh(Ip Is Jg Jh Jl Lh Lv Lx Nj Ny Om) Pb(Is Lh Lx Mr Om Pa Pe) Jl(Im Is Jh Jj Jn Nn) Is(Lw Nj Nn) Ny(Of Og Wm) Lx(Hq Oy) Om(Og Oy) NnIp MmJn JjLh} Pb{Lh(Fp Hq Hr Hx Im Io Iq Ir Is Iv Jj Jk Jl Jn Jp Jr Lv Lx Ly Ma Md Me Mg Mj Mk Ml Mn Mp Mq Mw Mz Nb Nf Ng Nh Nj Nm Nq Ns Nv Nx Ny Oy Oz Pa Pd Pe Pf Pg Po Qb Qc) Jl(Hr Hv Hw Ij In Ip Ir Jg Jh Jj Jn Jo Jr Jt Lw Md Mm Mt Mu Mz Na Nb Nm Nn Nw Nx Ny Oh Pe Po Qa) Mt(Hr Ii Ip Ir Is Iv Jr Jt Lw Mr Mz Na Nb Nr Om Po) Om(Ip Ir Is Iv Jo Jr Lx Mi Nt Nv Og Oh Pa Po) Pe(Ip Jg Jh Lw Mm Mu Nn Nv Nw Nx Ny Oh Pc) Po(Hw Ip Jh Jo Lw Na) Nw(Hr Ir Jt Mr Na Nr) Mu(Ir Is Jr Mr Ny) Mm(Ir Is Jr Ny) Nb(Ip Lw Nn Oh) Lx(Hw Ir Jt) Mr(Ip Jh Lw) Ny(Hw Jo Nr) Mw(Hu My) HwIp IrNv} Jr{Mm(Hr Hv Hw Ii Im In Io Ip Ir Is Iu Iv Jg Jh Jj Jk Jl Jn Jo Lh Lu Lv Lx Mf Mi Mr Mt Mu Mz Na Nb Nf Ng Ni Nj Nn Nr Ns Nt Nv Nw Ny Og Oh Oi Om Oy Pa Pc Pe Pz Qc) Nn(Jp Jl Lh Mi Mr Nt Pe Qc) Mj(Jl Lh Mr Nt) Jg(My Ng Og) Lh(Jj Lw Pc) Mu(Nj Oh) Jl(Jh Pc) Oy(Mw Om) WmJs LxLy MiPc QcNw} Oy{Mw(Ip Iq Ir Is Jl Jn Lh Lx Mt Mz Nv Nw Ny Oh Pa Pe Po) Om(Jl Lh Lx Mi Mr Mt Nb Nd Nt Nv Oh Pa Pe Po) Jh(Jl Lh Po) Jg(Jl Po) MmNy MtNb} Jl{Jh(Hu Jj My Ng Oh Oz) Lw(Im Iq Oh Oz) Mm(Jj Jn Oz) My(Jg Mw Om) Mj(Nf Oh) Jg(Ng Og) Jj(Lh Nn) Oz(Mt Oh) LxLy MzQc OgOm} My{Mw(Ip Iq Ir Is Lh Lx Mt Mz Ny Oh Pa) Om(Lh Lx Mr Nb Oh Pa) Ny(Jg Mm) MtNb JhLh} Ng{Jh(Lh Lx Mi Mr Pa Po) Om(Lh Lx Mi Nd Nt Pa) Jg(Lh Lx Mi Mr Ny) MmLh} Lx{Ly(Hr Ip Ir Is Jo Lh Lw Mr Mt Nj Om Pe) Hu(Ny Om)} Lh{Hu(Jh Mt Mu Nn Om) Jj(Mm Nn Oh) Lw(Jm Oh) MmJn OgOm} Hu{Mi(Jh Om) Ny(Nn Nq) MrJh} Nw{Qc(Iq Ir Jn) Mm(Hw Ir)} Mr{Oh(Lw Mj) OgOm} Og{MmNy OhOm} WmLyNv

Unconstrained panels with 3 analytes, where 1.0E-6 >= 'model p-value' > 1.0E-7. Contains 30,299 panels of 295,240 total panels evaluated. :
No{Jt(aA Fp Hq Hr Hu Hv Hw Hx Ih Ii Ij Ik Il Im In Io Iq Ir Is It Iu Iv Jj Jk Jl Jm Jn Jo Jp Jr Js Lh Li Lj Lu Lv Lw Lx Ly Lz Ma Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nk Nl Nm Nq Nr Ns Nt Nu Nv Nw Nx Ny Oe Of Og Oh Oi Oy Oz Pa Pd Pe Pf Pg Po Pz Qa Qb Qc Qd Qe) Mp(Fp Fr Hq Hr Hu Hv Hw Hx Ih Ii Ij Ik Il Im In Io Iq Ir Is It Iu Iv Jj Jk Jl

Pa Pf Pg Qb Qc Qd Qe) Iv(Fp Hq Hu Hx Ii Il Io Iq It Iu Jk Jm Jp Jr Lh Lj Lu Ma Md Mh Mk Mq Mr Mv Mw Mx My Nb Nd Ne Ng Nh Ni Nk Nq Nr Nv Oe Of Og Oi Oz Pa Pe Pf Pg Qb Qc Qd Qe) Fr(Fp Hq Hx Ih Ii Iq Iu Jk Jp Lh Li Lj Lx Lz Mc Md Mf Mg Mh Mi Ml Mq Mv Mw Mx Nc Nd Ne Nh Nk Nl Nt Nu Nv Oe Of Og Oi Pa Pd Pe Pf Pg Po Pz Qb Qc Qd Qe) Jr(Hq Hx Ih Ii Iu Jk Jp Li Lu Lx Lz Mc Md Mf Mg Mi Ml Mq Mv Mw Mx My Nc Nd Ne Ng Nh Ni Nl Nq Nt Nu Nv Oe Of Og Oi Oy Oz Pd Pe Pf Pg Po Pz Qb Qe) Lh(Fp Hq Hu Hx Ii Il Io Iq It Iu Jh Jk Jm Jp Lu Ma Mh Mk Mq Mr Mv Mw Mx My Nb Nc Nd Ne Ng Nh Ni Nj Nk Nr Nu Nv Oe Og Oi Oy Oz Pa Pf Pg Po Qb Qe) Nj(Fp Hq Hx Ih Ii Io It Iu Jk Lu Lx Lz Ma Mc Mf Mg Mi Mk Ml Mq Nc Nd Ne Ng Nh Nl Nq Nr Nt Nu Nv Of Oi Oy Oz Pd Pe Pf Pg Po Pz Qb Qc Qd Qe) Jh(Fp Hq Hx Ih It Iu Jk Jp Li Lj Lu Lx Lz Ma Mc Md Mf Mi Ml Mq Mv Mw Nc Nd Ne Nh Ni Nk Nl Nt Nu Nv Oe Of Oz Pd Pe Pf Pg Po Pz Qc Qd Qe) Ip(Fp Hq Ih Iu Jk Li Lu Lx Lz Ma Mc Md Mf Mg Mi Ml Mq Mv Mx Nd Ne Ng Nh Nk Nl Nq Nt Nu Nv Of Oi Oy Pd Pe Pf Pg Po Pz Qb Qd Qe) Jm(Hq Hu Hx Ih Ii Io Iq It Jk Jp Lj Lx Ma Md Mg Mh Mi Mr Mv Mw Mx My Nb Nc Nd Nh Ni Nk Nq Nt Nv Oe Of Og Oz Pa Pe Pf Pg Qb Qe) Jp(Hu Hx Ii Il Io Iq It Jg Jk Lj Ma Mf Mh Mk Mq Mr Mw Mx My Nb Nd Ng Nh Ni Nk Nr Nt Nv Oe Of Og Oi Oz Pa Pe Pf Pg Qb Qc Qe) Hu(Hq Hx Ii Il Io It Jk Lx Ma Md Mg Mh Mi Ml Mr Mv Mx My Nb Nh Ni Nk Nq Nt Nv Oe Of Og Oz Pa Pe Pf Pg Po Qb Qe) Il(Hq Hx Ii Io Iq It Jk Lj Ma Md Mh Mi Mr Mv Mw Mx My Nb Nc Nh Ni Nk Nt Nv Oe Of Og Oz Pa Pe Pf Pg Po Qb Qe) Nv(Ii Io Iq Jg Lu Mh Mk Mr Mx My Nb Ne Ng Ni Nk Nr Og Oi Oy Oz Pa Pe Pf Pg Qb Qc) Nb(Hx Io Iq Iu Ma Mh Mk Ml Mr Mw Mx My Ng Nh Ni Nk Og Oy Pa Pf Pg Qb Qe) Nk(Hx Ii Io It Jk Ma Mr Mw Mx My Nc Ne Nh Nl Oe Of Pa Pe Pf Pg Qb Qe) Mr(Hx Ii Io Iq It Jk Ma Mh Mi Mv Mw Mx My Ni Pa Pe Pf Pg Qb Qe) Pa(Hx Io Iq It Ma Mh Mk Mw Mx My Nd Nh Ni Nr Og Oz Pe Qb Qe) Mh(Hx Ii Io Iq Li Lx Ma Md Mw Mx Pe Pf Po Qb Qe) Io(Hx Iq Jk Ma Mi Mv Mw Mx My Oe Of Pf Qb Qe) Nn(Fp Hq Iu Lx Mc Mg Mw Nc Nu Pd Po Pz Qd) Qb(Hx Iq It Ma Mk Mw My Ni Nr Of Pe Qc Qd) Jg(Fp Jk Lz Mc Md Mf Mi Ml Nl Oe Pd Qe Wm) Mw(Iq Mk Mv Mx Nh Ni Og Pf Pg Wm) Ni(Hx Iq Jk Ma My Nc Oe Pf Qe) Ma(Hx Iq It Ng Nr Pe Qe) Iq(Hx Ii Lj Of Pe Qc) Mk(Hx Mx My Pf Qe) Mm(Jk Li Pz Qd) Qe(It Nr Qc Qd) Pf(Hx Nr Og Oz) Wm(Ji My On) Ng(Hx Jk My) MiHq MvMy HxOg IuPe) Ji{Nk(Fp Hq Hr Hu Hv Hx Ih Ii Ij Il Im In Ip Ir Is It Iu Iv Jg Jj Jk Jm Jn Jo Jp Jq Jr Js Jt Lh Li Lj Lu Lv Lw Ly Lz Ma Mc Md Me Mf Mg Mh Mi Mj Mk Ml Mn Mp Mq Ms Mv Mw Mx My Mz Na Nb Nc Nd Ne Nf Ng Nh Ni Nj Nl Nm Nq Nr Ns Nu Nv Nw Nx Ny Oe Of Og Oi Om Oy Oz Pb Pc Pd Pe Pf Pg Po Pz Qa Qb Qd Qe) Mn(Fp Hq Hr Hu Hv Hx Ih Ii Ij Il Im In Ip Ir Is It Iu Iv Jg Jj Jk Jm Jn Jo Jp Jq Jr Js Jt Lh Li Lj Lu Lv Lw Ly Lz Ma Mc Md Me Mf Mg Mh Mi Mj Mk Ml Mp Mq Ms Mv Mw Mx My Mz Na Nb Nc Nd Ne Nf Ng Nh Ni Nj Nl Nm Nq Nr Ns Nu Nv Nw Nx Ny Oe Of Og Oi Om Oy Oz Pb Pd Pe Pf Pg Po Pz Qa Qb Qd Qe) Li(Fp Hq Hr Hu Hv Hx Ih Ii Ij Il Im In Ip Ir Is It Iu Iv Jg Jj Jk Jm Jn Jo Jp Jq Jr Js Jt Lu Lv Lw Ly Lz Ma Mc Md Me Mf Mg Mh Mi Mj Mk Ml Mp Mq Ms Mv Mw Mx My Mz Na Nb Nc Nd Ne Nf Ng Nh Ni Nj Nl Nm Nq Nr Ns Nu Nv Nw Nx Ny Oe Of Og Oi Om Oy Oz Pc Pd Pe Pf Pg Po Pz Qa Qb Qd Qe Wm) Lj(Fp Hq Hr Hu Hv Hx Ih Ii Ij Il Im In Ip Ir Is It Iu Iv Jg Jj Jk Jm Jn Jo Jp Jq Jr Js Jt Lh Lu Lv Lw Ly Lz Ma Mc Md Me Mf Mg Mh Mi Mj Mk Ml Mp Mq Ms Mv Mw Mx My Mz Na Nb Nc Nd Ne Nf Ng Nh Ni Nj Nl Nm Nq Nr Ns Nu Nv Nw Nx Ny Oe Of Og Oi Om Oy Oz Pc Pd Pe Pf Pg Po Pz Qa Qb Qd Qe) Mc(Fp Hq Hr Hu Hv Hx Ih Ii Ij Il Im In Ip Ir Is It Iu Iv Jg Jj Jk Jm Jn Jo Jp Jq Jr Js Jt Lu Lv Lw Ly Lz Ma Md Me Mf Mg Mh Mj Mk Ml Mp Mq Ms Mv Mw Mx My Mz Na Nb Nc Nd Ne Nf Ng Nh Ni Nj Nl Nm Nq Nr Ns Nu Nv Nw Nx Ny Oe Of Og Oi Om Oy Oz Pb Pc Pd Pe Pf Pg Po Pz Qa Qb Qd Qe) Nu(Fp Hq Hr Hu Hv Hx Ih Ii Ij Il Im In Ip Ir Is It Iu Iv Jg Jj Jk Jm Jn Jo Jp Jq Jr Js Jt Lu Lv Lw Ly Lz Ma Md Me Mf Mg Mh Mj Mk Ml Mp Mq Ms Mv Mw Mx My Mz Na Nb Nc Nd Ne Nf Ng Nh Ni Nj Nl Nm Nq Nr Ns Nv Nw Nx Ny Oe Of Og Oi Om Oy Oz Pc Pd Pe Pf Pg Po Pz Qa Qb Qd Qe) Ih(Fp Hq Hr Hu Hv Hx Ii Ij Il Im In Ip Ir Is It Iu Iv Jg Jj Jk Jm Jn Jo Jp Jq Jr Js Jt Lu Lv Lw Ly Lz Ma Md Me Mf Mg Mh Mj Mk Ml Mp Mq Ms Mv Mw Mx My Mz Na Nb Nc Ne Nf Ng Nh Ni Nj Nl Nm Nq Nr Ns Nv Nw Nx Ny Oe Of Og Oi Om Oy Oz Pb Pc Pd Pe Pf Pg Po Pz Qa Qb Qd Qe) Il(Fp Hq Hr Hu Hv Hx Ii Ij Im In Ip Ir Is It Iu Iv Jg Jj Jk Jm Jn Jo Jp Jq Jr Js Jt Lu Lv Lw Ly Lz Ma Md Me Mf Mg Mh Mj Mk Ml Mp Mq Ms Mv Mw Mx My Mz Na Nb Nc Nd Ne Nf Ng Nh Ni Nj Nl Nm Nq Nr Ns Nv Nw Nx Ny Oe Of Og Oi Om Oy Oz Pc Pd Pe Pf Pg Po Pz Qa Qb Qd Qe) Jp(Fp Hq Hr Hu Hv Hx Ii Ij Im In Ip Ir Is It Iu Iv Jg Jj Jk Jm Jn Jo Jq Jr Js Jt Lh Lu Lv Lw Ly Lz Ma Md Me Mf Mg Mh Mj Mk Ml Mp Mq Ms Mv Mw Mx My Mz Na Nb Nc Ne Nf Ng Nh Ni Nj Nl Nm Nq Nr Ns Nv Nw Nx Ny Oe Of Og Oi Om Oy Oz Pc Pd Pe Pf Pg Po Pz Qa Qb Qd Qe) Oe(Fp Hq Hr Hu Hv Hx Ii Ij Im In Ip Ir Is It Iu Iv Jg Jj Jk Jm Jn Jo Jq Js Jt Lh Lu Lv Lw Ly Lz Ma Md Me Mf Mg Mh Mj Mk Ml Mp Mq Ms Mv Mw Mx My Mz Na Nb Nc Ne Nf Ng Nh Ni Nj Nl Nm Nq Nr Ns Nv Nw Nx Ny Of Og Oi Om Oy Oz Pc Pd Pe Pf Pg Po Pz Qa Qb Qd Qe Wm) Ly(Fp Hq Hr Hu Hv Hx Ii Ij Im In Ip Ir Is It Iu Iv Jg Jj Jk Jm Jn Jo Jq Jr Js Jt Lu Lv Lw Lz Ma Md Me Mf Mg Mh Mj Mk Ml Mp Mq Ms Mv Mw Mx My Mz Na Nb Nc Ne Nf Ng Nh Ni Nj Nl Nm Nq Nr Ns Nv Nw Nx Ny Of Og Oi Om Oy Oz Pd Pe Pf Pg Po Pz Qa Qb Qd Qe Wm) Mx(Fp Hq Hr Hu Hv Hx Ii Ij Im In Ip Ir Is It Iu Iv Jg Jj Jk Jm Jn Jo Jq Jr Js Jt Lu Lv Lw Lz Ma Md Me Mf Mg Mh Mj Mk Ml Mp Mq Ms Mv Mw My Mz Na Nb Nc Ne Nf Ng Nh Ni Nj Nl Nm Nq Nr Ns Nv Nw Nx Ny Of Og Oi Om Oy Oz Pd Pe Pf Pg Po Pz Qa Qb Qd Qe Wm) Nh(Fp Hq Hr Hu Hv Hx Ii Ij Im In Ip Ir Is It Iu Iv Jg Jj Jk Jm Jn Jo Jq Jr Js Jt Lu Lv Lw Lz Ma Md Me Mf Mg Mh Mj Mk Ml Mp Mq Ms Mv Mw My Mz Na Nb Nc Nd Ne Nf Ng Ni Nj Nl Nm Nq Nr Ns Nv Nw Nx Ny Of Og Oi Om Oy Oz Pd Pe Pf Pg Po Pz Qa Qb Qd Qe) Hv(Fp Hq Hr Hu Hx Ii Im In Ip Ir Is It Iu Iv Jg Jj Jk Jm Jn Jo Jq Jr Js Jt Lh Lu Lv Lw Lz Ma Md Mf Mg Mh Mj Mk Ml Mp Mq Ms Mv Mw My Mz Na Nb Nc Nd Ne Nf Ng Ni Nj Nl Nm Nq Nr Ns Nv Nw Nx Ny Of Og Oi Om Oy Oz Pc Pd Pe Pf Pg Po Pz Qa Qb Qd Qe) Lz(Hq Hr Hu Hx Ii Ij Im In Ir Is It Iu Iv Jj Jk Jm Jn Jo Jq Jr Js Jt Lh Lu Lv Lw Ma Md Me Mf Mg Mh Mi Mj Mk Ml Mp Mq Ms Mv Mw My Mz Na Nb Nc Nd Ne Nf Ng Ni Nj Nl Nm Nq Nr Ns Nv Nw Nx Ny Of Og Oi Om Oy Oz Pd Pe Pf Pg Po Pz Qa Qd Qe Wm) Ni(Fp Hq Hr Hu Hx Ii Ij Im In Ip Ir Is It Iu Iv Jg Jj Jk Jm Jn Jo Jq Jr Js Jt Lu Lv Lw Ma Md Me Mf Mg Mh Mj Mk Ml Mp Mq Ms Mv Mw My Mz Na Nb Nc Ne Nf Ng Nj Nl Nm Nq Nr Ns Nv Nw Nx Ny Of Og Oi Om Oy Oz Pd Pe Pf Pg Po Pz Qa Qb Qd Qe) Qe(Fp Hq Hr Hu Hx Ii Ij Im In Ip Ir Is It Iu Iv Jg Jj Jk Jm Jn Jo Jq Jr Js Jt Lu Lv Lw Ma Md Me Mf Mg Mh Mj Mk Ml Mp Mq Ms Mv Mw My Mz Na Nb Nc Ne Nf Ng Nj Nl Nm Nq Nr Ns Nv Nw Nx Ny Of Og Oi Om Oy Oz Pd Pe Pf Pg Po Pz Qa Qb Qd) Nw(Fp Hq Hr Hu Hx Ii Ij Im In Ip Ir Is It Iv Jg Jj Jk Jm Jn Jo Jq Jr Js Jt Lu Lv Lw Ma Md Me Mf Mg Mh Mj Mk Ml Mp Mq Ms Mv Mw My Mz Na Nb Nc Ne Nf Ng Nj Nl Nm Nq Nr Ns Nv Nx Ny Of Og Oi Om Oy Oz Pd Pe Pf Pg Po Pz Qa Qb Qd Wm) Mq(Fp Hq Hr Hu Hx Ii Ij Im In Ip Ir Is It Iv Jg Jj Jm Jn Jo Jq Jr Js Jt Lu Lv Lw Ma Md Me Mf Mg Mh Mj Mk Ml Mp Ms Mv Mw My Mz Na Nb Nc Nd Ne Nf Ng Nj Nl Nm Nq Ns Nv Nx Ny Of Og Oi Om Oy Oz Pc Pd Pf Pg Po Pz Qa Qb Qd Wm) Ne(Fp Hq Hr Hu Hx Ii Ij Im In Ip Ir Is It Iu Iv Jg Jj Jm Jn Jo Jq Jr Js Jt Lu Lv Lw Ma Md Me Mf Mg Mh Mj Mk Ml Mp Ms Mv Mw My Mz Na Nb Nc Nd Nf Ng Nj Nl Nm Nq Nr Ns Nv Nx Ny Of Og Oi Om Oy Oz Pd Pe Pf Pg Po Pz Qa Qb Qd) Pd(Fp Hq Hr Hu Hx Ii Ij Im In Ip Ir Is It Iu Iv Jg Jj Jk Jm Jn Jo Jq Jr Js Jt Lu Lv Lw Ma Md Me Mf Mg Mh Mj Mk Ml Mp Ms Mv Mw My Mz Na Nb Nc Nf Ng Nj Nl Nm Nq Ns Nv Nx Ny Of Og Oi Om Oy Oz Pe Pf Pg Po Pz Qa Qb Qd) Me(Fp Hq Hr Hu Hx Ii Ij Im In Ip Is It Iu Jg Jj Jk Jm Jn Jo Jq Js Jt Lv Lw Ma Md Mg Mh Mj Mk Ml Mp Ms Mv Mw My Mz Nb Nc Nd Nf Ng Nj Nl Nm Nq Nr Ns Nv Nx Ny Of Og Oi Om Oy Oz Pb Pc Pe Pf Pg Po Pz Qa Qb Qd Wm) Mw(Fp Hq Hr Hu Hx Ii Ij Im In Ip Ir Is It Iu Iv Jg Jj Jm Jn Jo Jq Jr Js Jt Lu Lv Lw Ma Md Mf Mg Mh Mj Mk Ml Mp Mv Mz Na Nb Nc Nd Nf Ng Nj Nl Nm Nq Nr Ns Nv Nx Ny Of Oi Om Oz Pc Pe Pf Pg Po Pz Qa Qb Qd Wm) Qa(Fp Hq Hr Hu Hx Ii Im In Ip Ir Is It Iu Iv Jg Jj Jm Jn Jo Jq Js Jt Lu Lv Lw Ma Md Mf Mg Mh Mj Mk Ml Mp Ms Mv My Mz Na Nb Nc Nf Ng Nj Nl Nm Nq Nr Ns Nv Nx Ny Of Og Oi Om Oy Oz Pc Pf Pg Po Pz Qb Qd Wm) Hu(Fp Hq Hr Hx Ii Ij Im In Ip Ir Is It Iu Iv Jj Jm Jn Jo Jq Jr Js Jt Lu Lv Lw Ma Md Mf Mg Mh Mj Mk Ml Mp Ms Mv My Mz Na Nb Nc Nf Ng Nj Nl Nm Nr Ns Nx Ny Of Og Oi Om Oy Oz Pb Pe Pf Pg Po Pz Qb Qd) Jm(Fp Hq Hr Hx

Pg) Hu(Iq Is Nd Nq Nt Nv Ny Pa Pe Pg Po) Mr(Ip Jn Lv Lw Ly Mg My Mz Pc) My(Mi Mw Nb Ny Pa Pe Po) Ip(Iq Ir Is Mz Nt Pe) Iq(Lv Lw Nt Pe) Mi(Jn Ly Mg) Nt(Jn Mz) Ir(Lv Pc) Pa(Jn Mk) LwIs} Jj{Nv(Hr Hw Im Io Ip Iq Ir Is Iv Jg Jk Jn Jo Jt Lw Mi Mr Mu Mz Na Nd Nf Nj Nm Nt Pc Pe Qc) Ny(Hw Ip Jo Lw Mi Ml Mp Mr Mu My Nd Nm Nt Pc) Nt(Ip Is Jg Jk Jn Lw Mu Mz Nj Nm Pc) Mr(Ip Is Jg Jk Jn Lw Mu Nm Pc) Mu(Ir Is Jn Pg) Ip(Jk Pe Pg Po) Mi(Jk Jn Nm) Pg(Jg Nm) JkJo} Lw{Is(Hw Im Io Ip Iq Ir It Jm Lu Mf Mi Mr Mu Mz Nf Nt Nv Ny Og Pa Pe Po) Mr(Im Ip Iq Jg Jm Jn Lv Ly Mz Ng Ny Og) Iq(Im Lv Mu Nt Nv Ny Pa Pe Qc Wm) Mi(Jm Jn Ly Ng Oy) Ny(Ir My Ng Og Wm) Mz(Im Nt Pa) Ir(Im Mu Nv) Jn(Nt Pa) WmPc PoOy} Jg{Ng(Hq Hx Ip Ir Is Jk Jn Mp Mu Mz Nd Nt Nv Pa Pe Pg Po) Og(Hx Ip Ir Is Jn Mr Mx Mz Nb Ny Pa Pe Po) My(Hx Is Jn Mr Mz Nb Nv Pa Pe Pg Po) Oy(Is Mi Mr Mw Nb Nv Ny Pa Pe Pg) Ip(Ir Is Mr Mz Pe) Nt(Jn Mz) Is(Hu Ms) WmNy IrJt} Ny{Pc(Hu Iq Ir Is Mr Mv My Ng Nt Of Og Oy Pe Wm) My(Me Mi Mr Mu Nb Pa Po) Oy(Mi Mr Mu Nb Pa Pe Po) Ng(Mi Mp Mu Nd Pa) Hu(Mi Mu Mw Nd Wm) Iq(Il Ip Mj Qc) Og(Ip Mi Nm Pa) Wm(Ly Mj Mr) LyMi} Mw{Oy(Hq Hr Hx Ih Ii Iv Jk Lz Md Mi Mr Mu Mx My Nb Nd Nf Nt Nx Pf Pg Qb) My(Hu Hx Ih Iv Jn Jp Js Mi Mr Mx Nb Nf Nt Nv Nx Pe Pg Po) Og(Ir Is Jn) Hu(Hx Wm)} Mu{Is(Hu Ip Iq Ir Mz Ng Nj Og Oy Pa) Ir(Ip Lv Nj Og Pc) Ng(Mi Nt Pa) Nj(Iq Jn Mz) Oy(Nb Pa Po) Iq(Ip Lv) MyNb} Pc{Is(Hw Iq Mi Mr Mz Nf Nt Pe) Mz(Im Mi Mr Nt Pa Pe) Jn(Mi Mr Nt Pa Pe) Ir(Im Mi Nv) Ip(Mr Pe) PoOy MyNb} Ip{Jn(Mi Mr Nt Pa Pe) Mz(Mr Nt Pa Pe) Nb(My Og Oy) Iq(Hw Nt Pe) PoOy LyMr IrNv} Mz{Nj(Mi Nt Pa) Mj(Mr Nt) WmNv NqHu MlPa IsQc} Is{Nt(Io Jm) Mj(Mr Pe) PoOy MiJm IqQc} Nv{Nb(My Oy) WmJm ImIr} Jn{Nj(Nt Pa) MjMr} Wm{Ly(Nb Pa)} Iq{LvIm QcNx} PoMjOy

Unconstrained panels with 3 analytes, where 1.1E-6 >= 'model p-value' > 1.0E-6. Contains 1,935 panels of 295,240 total panels evaluated. : aA{In(Fp Hv It Jt Lu Ly Mc Md Mf Mk Ml Ms Ng Nk Oe Oy Pz) Qe(Fp Iu Jm Jp Js Lj Lu Lz Mc Mk Ml Mq Ms Nc Nk Nr Nu) Hw(Hv It Js Jt Lj Ly Mc Mf Mk Ms Na Ni Nr Nu Qc Qd) Iq(Hu It Jp Lz Mf Mh Ml Mv Ne Ng Nk Nl Nr Oe Og Oy) Qa(Hv Ih It Jp Lz Md Ml My Nc Ne Ng Og Oz Qc Qd) Mg(It Lu Lz Mf Mj Mk Mq Ms Mv Nc Ni Nk Oy) Iv(Hu It Jp Js Lz Mf Mq Nc Ne Ng Ni Nk Nr) Li(Ih Jp Js Lu Ly Lz Mc Mf Ml Ms Nr Nu Oe) Og(Hv Iu Jm Jt Md Mh Mv Mx My Nd Nh Ns) Pd(Ih It Jp Js Md Mv Nc Ne Ng Ni Nl) Ns(Hu Ih It Jj Lu Lz Mj Ml Ng Ni) Mh(Ih Jj Jp Jt Md Mv Nk Oe Oy Pz) Hv(Hu Ih It Jj Md Mj Na Ne Oy Pz) Mx(Ih Jj Jp Mf Mq Ne Ni Nr Oy) Iu(Hu Js Mf Mq Mv My Ni Nr Oz) Jt(Jj Lz Mj Mv My Na Ne Nl Oz) Nq(Jm Lu Ly Ml Ms Nc Nk) Nh(Ih Jj Jp Js Lz Nr Oy) Oz(Jj Jm Md Mf Ne Nl Nr) Nd(Lu Mj Nl Oe Oy Pz) Jm(Jp Js My Ng Ni) Md(Lz Ml Nc Ne) My(Mf Ni Nr) Na(Lj Qc Qd) Mv(Ne Oy) Qd(Nb Oi) MjJs NcNk QcOi} No{Qa(Ij Iu Li Lj Lz Mc Md Mf Mg Ni Nl Nt Oy Pd Pe Po Pz) Nv(Hq Hx It Iu Lx Ma Mf Mi Mq Mv Mw Nd Nh Nq Qe) Ij(Hw Iu Lj Lx Lz Mc Mf Mg Ni Nt Pd Po Pz Qc) Iv(Ih Li Lx Lz Mc Mf Mg Mi Ml Nc Nt Nu Oy Pd) Jp(Hq Ih Iu Lu Lz Md Mi Mv Nc Ne Nq Oy Pd Qd) My(Hx Ii Iq Ma Mx Nd Nh Nr Pe Pf Qe) Il(Jm Li Mf Mg Mk Ml Mq Ne Nq Nr Nu) Lh(Ih Li Lj Lz Mc Md Ml Nt Of Pd Qc) Hu(Ih Iq Li Lj Mq Nd Ne Oi Pd Qc) Qb(Ii Lj Mq Mx Nd Nh Og Oi Oz Pf) Jm(Li Mf Mk Mq Ne Nl Nu Oi Pd Po) Pa(Ii Iu Jk Md Mq Mv Ng Of Oi Pf) Iq(It Jk Lz Mq Nk Og Pf Pg Qe) Nb(Ii Jk Lu Md Nc Nr Oz Pe) Ma(Ii Mk Mw Mx Og Oi Oz) Nk(Ih Mh Mv Ni Nt Og Oz) Hw(Lj Lz Mf Ni Nt Qd) Hx(Mx Nh Nr Oy Qe) Io(It Ni Oz Pe Pg) Qd(In Jo Ly Me Na) Js(Iu Md Nu Po Pz) Mr(Li Md Mq Nh) Jk(Mh Mk Nr Og) Jo(Lz Mf Po Pz) Mw(It Oi Qe) Ly(Oy Pz) Mx(Ni Nr) Ng(Ii Of) Oi(Ni Oe) Pe(Mk Oz) Pf(It Lj) WmFr PoIn MhMl IiOy} Ok{Jn(Hu Ii Iv Jm Ly Mn Ms My Ne Nh Nk Nr Nu Oe Oy Oz Pd Qa Qb) Md(Hv Il Jm Jp Lu Mn Mw Nf Nh Nk Nr Oe Of Oz Po) Io(Hv Jp Js Ly Mk Mn Mv Nh Ni Nr Oy Pd Qa) Pg(Hq Hv Iu Iv Jm Lu Mf Nj Nu Oe Of Qb Qd) Jo(Ii Li Mn Mv Mw Nb Nl Nx Oi Pd Qb Qc) Jj(Hu Hv Jp Js Ly Ms Na Ng Oe Qd Qe) Lu(Hq Li Lj Mz Nb Nf Nj Nm Oi Qb) Mz(Hx Il In It Iv Mk My Ns Po) Nf(Hx Iv Ma Mk Mr Nb Ng Oy Pf) Hr(Ij Jp Ly Lz Nh Nu Nx Pd Qc) Pz(Hx It Lv Ly Ml Mw Nb Og Pd) Qc(It Mc Me Nb Ne Nh Nk Nu Qe) Mj(In Lz Nk Nm Nr Ns Nx Oz) Oi(Li Mw Mx Nb Nj Ns Oe Pd) Me(Il Iu Ly Ma Mg Nj Pf) Nc(Hx Ir Iu Ly Nm Ns Qb) Nt(Ne Ni Nl Nx Qd Qe) Lv(Hq Ir Iu Iv Mf Nm) Mh(Ly My Na Nu Oz Qd) Jk(Jp Oe Po Qa Qd Qe) Fp(It Lj Mn Mv Ne) Hw(It Mk Nj Pf) Li(Ij Ma Mg Ml) Mr(Lj Nb Nj) My(Hq Ii Ng) Og(Iu Nm Pe) Po(Hu Nj) Ma(Lj Pf) Mg(Nx Oy) Ml(Hq Qb) Nb(Hq Iv) Ng(Ir Pf) LzLj IiOy IrIt} Fr{Js(Hv Il Iq Lz Ml Ms Nn Ns Nv Oe Oi Oz Qb) Mt(It Lx Me Mg Mu Mx Nb Ni Ns Ny Oi Qc) Jt(Hw Hx Ij Lj Ml Nm Nu Nv Om Pe Qc) Nw(Ih Io Jh Lx Mi Mk Mp Nq Nu Pz) Nf(Hr Iq Jh Ms Mx Nb Nq Nr Pc) Iq(Hx Ma Mk Mq My Ne Nh Oy) Jo(Lx Mx Nh Nn Nq Ny Of Og) Nm(Io Lv Lx Nq Ny Pa Qa) Nt(Hq Ij In Lv Mm Nb Nn) Lw(Jp Mj Mv Ni Oi Pf Pz) Mr(Hq Ij In Ml Nb Nc Ni) Hr(Io Jg Mi Mj Mv Nd Ns) Hw(Hv It Mc Nx Oe Pg Po) Jl(Lv Ms Mu Nd Pa Qb Qc) Om(Hv Jh Lx Nc Nq Ny Pe) Ip(Ii Mh Mk Mu Nx Pc) Qa(Mi Nr Ny Og Pa Pe) Nj(Mn Mu Nv Po Qb) Nl(Ih Lv Me Mg Pe) Hu(Io Lv Mq Nc Pg) Lh(Ij In Lx Pf Qc) Pb(My Nq Oi Pc) Ma(Ij Mi My) Ml(In My Ny) Ng(Lv Oz Qe) Hv(Hx Io Ms) Ih(Mc Ni Ny) Im(Mp Mq Mx) Mi(Hq Ly) Ij(Mg Og) Ik(Lj Mf) It(Mm Oy) NnMu NqPe MsNy MxJh MzQd} Jr{Nn(Ih Ij Jp Li Mg Mh Mn Mq Ne Nh Nu Oe Of Qa) Mt(Hq Lu Md Mq Ne Nk Nu Nx Pd Pf Pg Pz Qa) Jg(Ii Il Iv Jn Lz Nb Nc Ni Nm Of Oz Pg) Jh(Hq Ih It Li Mc Mw Nq Nu Nx Qb Qd Qe) Mb(Il Mj Mq Nc Ng Nu Of Og Qa Wm) Jl(Ii Iu Iv Jt Lv My Nb Nc Po Qa) Mu(Fp Jn Lz Mv Nh Oi Pf Pg Po) Oh(Io Iq Jp Jt Lu My Na Nx Pb) Lx(Fp Jn Jo Lv Ma Mp Ns Pe) Mi(Il Io Is Js Lv Ma Me Mp) Om(Fp Hr Hx Ir Me Mh Nc Nm) Ip(Hr Is Jo Mp Nd Nm) Lw(Hr Hw Jj Nd Qc) Mr(Io Ly Mh Nv) Qc(Mz Nv Ny Pe) Jq(Hr Jj Nb Pb) Nm(Lu Pb Pe) My(Nb Nq Ny) Im(Jj Mj Mp) Nw(Io Jn Og) Pe(Hr Jj) PoMj NqNg NfPc} Jl{Lw(Il It Mc Me Mh Ml Mn Mv Mw Ni Qa) Iq(Hr Ij Il Ir Is Lx Md Mz Nf Nw Ny) Mz(Fp Hw Iu Mn Mr Ms Ne Pf Pg) Md(Io Ir Me Mj Nf Nm Ns) Mt(It Jk Mc Nl Nu Nx Qb) Om(In Jk Js Mp Mu Nq Pd) Nf(Lv Ma Mp Ms Nl Nr) Jn(Iv Mr Mx Nr Nx Pf) Nw(Hx Is Iv Me Mi Nc) Lx(Io Js Jt Nj Oy) Mb(Hu Mg Pg Po Qd) Im(Jm Mq Ng Oi Pa) Nn(Lv Nd Ne Ns) Ip(Hv In Js Mh) Ir(It Jo Nm Nt) Jj(Fp Jm Oe Qe) Lh(Me Mg Mq Mu) Oz(Me Mj Na Nv) Nj(Hw Na Pa) Jg(Mu Nc Nl) Oh(Jk Qd Qe) Nm(Mm Oy) Mh(Mm Pc) Mj(Hv Iv) Io(Nc Ny) MvMy QePb PaPc} Mt{Ir(Hq Hv Il Jn Jo Mf Mg Nc Nx Oz Pz Qd) Ip(Hu Hv Jg Lx Mm Nc Nn Nw Og Oi) Lh(Hv Hw Ij Jt Ma Mw Nf Nh Ni Pa) Pb(Jm Lj Ly Ma Mf My Og Oy Pz Qe) Hr(Hw Iq Iv Mr Nt Pe Qc) Hw(Ij Jg Lv Lx Mj Nr) Nt(Iq Jh Lv Mm Nr) Is(Ij Mp Mq Nf Ny) Pc(Im Lx My Nr Ns) Pe(Io Iq Jh Nr Qc) Nn(Jn Jt Oi Pa) Na(Lw Mi Mr Pa) Ng(Ii Jo Mm) Nj(Mu Nb Om) Nw(Jn Oh Oy) Lw(Io Pd) Iq(Jo Lz) Qc(Jn Mr) Og(Hx Pa) Oh(Mm Nb) FpIv LxMz MkOm MvJg JjPa} Lh{Nn(Fp Hq It Li Lj Lu Mc Mn Mx Nt Nx Qa Qb Qd) Ik(Hx Ij Il Lj Lu Ml Nb Nc Ni Nk Nl Ns Oe) Oh(Ih Ij Iu Mi Mw Mx Nt Pd Pe Qa) Jj(Ih Iv Lx Mw My Nh Oy) Lw(Hq Ih Md Nc Ne Ns) Is(Hr Jn Mq Mz Om Oy) Nw(Hv Ii Iv Jm Lv Nh) Ip(Hr Hu Mg Mj Ng) Jh(Hx Ir Mj Ml Ny) Mm(Mh Nh Pf Qb) Pc(Jp Nv Pa Pf) Ly(Im Nh Ny) Jg(Il Io Iq) Jn(Jm Og Oy) Mu(My Og) NqHu MbNg MjJs IjOm} Jq{Nd(Ih Ij Il Mc Mg Mk Mq Nq) Im(Jn Mk Na Nf Nx Pd) Jg(In Jk Li Nh Nq Qa) Nv(Hw Ij Ir Jo Nr Qc) Ny(Jh Lz Md Mu My Nw) Ip(Io Jn Lu Mh Mk) Iq(Hr Ih Iv Lu Nr) Is(Hq Ii Js Ml Nb) Iu(Jk Li Lv Ma Pg) Me(Lz Mu Pf Po) Nl(Ik Jj Jk Jo) Pc(Ij Mq Ng Nx) Wm(Jk Nf Pa) Nb(Ij Ml Oy) Nc(Nq Pf Po) Jo(Hr Ij Pf) Og(Hx Ii Nw) Mu(Lv Qe) Jh(Mh Na) PoMp NrNw LzNj HqJj} Oh{Om(Hq Ih Ii Il Ly Lz Mn Nn Oz Pf Pg Po Qa Qb Qe) Jg(Jm Js Lu Md Mf Nb Nm Nq) Mb(Fp In Io Mp Nf) Nw(Ij Im Is Mz Nd) Nt(Ir Jn Mm Pc) Ip(Hx Jp Nx Pc) Jh(Jm Mh Nk Oz) Ny(Is Nd Of Pa) Nm(Lx Nv Pe) Lw(Jo Mf Pb) Mu(Ii Nl Qa) Mz(Mi Nj Qc) Hw(Jp Mi Nv) Lv(Iq Pa) Mr(Is Jn) Ik(Jt Pg) Pe(Im Is) NjIi HrNv HvPa IrJj} Nw{Hw(Fp Ir Jt Ne Nh Pf) Nt(Im Iv Js Lv Ny) Ir(Iu Md Mr Nq Nv) Jo(Jn Me Mk Nl Ns) Na(Jg Mh Mj Nl) Hr(Mh Mi Nj Wm) Mm(Io Iq Mi) Hv(Ip Ml Qc) Nr(Lw Nn) Lx(Hu Ik) Mx(Ik Lw) Im(Mz Nm) Io(Is Iv) Jh(Mv Pe) Jt(My Og) Pb(Iu Mq) MhIi MiHx MrJj MuJn JkOg} Ik{Ny(Lv Ma Me Mn Mz Oi Pd) Pe(Hr In Lz Nr Oi Pd) Mr(Hq Ly Mb Md) Mu(Jt Lz Nr Qe) Iv(Jn Lv Mv Nq) Jh(Hq Im Jt Nd) Om(Mf Mg Oe Oi) Po(Jk Ma Mv) Nt(Jp Lw Qd) Nb(Im Iq Lv) Lx(Ng Pf) Nj(Iq Nv) Is(Mv Mz) MmPg IrJn} Om{Og(Lv Mg Mk Nx Oz) My(Lu Nd Nj Nl) Oy(Hv Nh Oe Qa) Pb(Ma Ml Nq Qd) Mb(Lz Mr Mz) Iq(Hu Lx Lz) Lw(Is Mr) Nd(Hq Hu) Ng(Hw Qe) Ip(Hw Mi) Jj(Im Ml) Of(Hx Ir) NnPe NtMz LxNy

Figure 35 Continued

MrMv NjIs IIPa} Nn{Ir(Hu Mu Nd Og Pa Qc) Is(Ii Io Mj Na Nd Pc) Mb(Ih Jp Js Ne Pf) Pe(Mh Nm Nv Og) Mr(My Nj Pc) Jj(Jk Na Nb) Nt(Hu Jm) Lw(Iq Ny) PoNg MiNa NyOf} Mm{Ir(Iq Jt Lw Mg Mp Nd Pf) Is(Il Mn Mx Nl Qa) Mr(Iq Mg Nf) Mz(Io Iu Nj) Iv(Lv Mu Nv) Jj(Hw Pa) Jn(Jk Nf) Ny(Im Jm) LxMb MwMy NbOg IqPe} Pb{Ny(Hv Ii Lx Lz Mi Ni Nj) Ir(Hq Lw Ma Mw) Mi(Jo Mu Mz) Nb(Im Mq Oy) Nv(Hv Ip Lw) Ii(Jh Mz) Pe(Mx Oy) PoIl Mals MjIm Mrlj NfPa} Mb{Iq(Ih Il Lz Md Qa Qe) Is(In Iv Mv) Jg(Jj Ng Nt) Jn(Im Nv Pa) Lx(Hu Pc) Mu(Jj Nj) Jh(Hu Mi) Ny(Ml Mr) NtNj Lvlm Iplv} Lx{Ly(Lj Lu Lz Md Mw Nk Oi Qb Qc) Mh(Ny Pg) Mz(Hu Ml) Is(Jg Jn) LwIq MuNg HqJh JgOg JmNy} Jj{Jg(Hw Is Mi Pa) Nv(Hv Il Iu Nr) Ny(Hx Iq Nj Og) Is(Lw Mi) WmOn NmMu ImPg IrJk} Lw{Mr(Nv Oy Pc) Is(Jg Jn Pc) Ng(Pa Po) Iq(Hx Ip) WmMz NtNy MiHq NbOg} Jh{Ng(Jg Nb Nf) Iq(Hw Mr Nj) My(Mz Nv) WmJi PoOf NtOy LvMz HwIp PcPe} Is{Pc(Io Ir Mu Og Pa) Mi(Io Ly) MjMz MuMy NfNj IoNv} Wm{Ji(Hq Hr Hx Ij Jp Lj Mz Nd Nu Pz)} Ny{My(Ip Nq Pe) Nt(Hu Jm) NqOy MuOg MwPc ImIq} Jg{Ng(Hw Nf) MgMr MwMy HxOy IpIq} Pc{Mr(Ir Ly) Pe(Im Iq)} Mw{My(Pf Qe) MiNg} Nj{MiJn MuPa} PoMhOy NqHuJn IqQcNv Unconstrained panels with 2 analytes, where 1.0E-6 >= 'model p-value' > 0. Contains 899 panels of 7,381 total panels evaluated. : Et(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ji(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) On(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) No(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) aA(Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Ok(Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Nj Nk Nl Nm Nn Nq Nr Ns Nt Nu Nv Nw Nx Ny Oe Og Oh Oi Om Oy Oz Pa Pb Pc Pd Pe Pf Pg Po Pz Qa Qb Qc Qd Qe) Fr(Hr Hu Hv Hw Ih Ij Ik Im In Ip Iq Ir Is Iv Jj Jl Jn Jo Jq Jr Js Jt Lh Lw Mb Mr Mt Mx Mz Na Ne Nf Ng Nh Nj Nl Nm Nt Nw Ny Oh Om Pb Pe Qa) Jl(Hw Ik Im Io Ip Iq Ir Is Jg Jh Jj Jn Jq Jr Lh Lw Lx Mb Md Mm Mt Mu Mz Na Nf Nm Nn Nt Nw Oh Om Oz Pb Pc) Jq(Hw Im Ip Iq Is Iu Jg Jh Jo Jr Lh Lx Mb Mi Mm Mp Mr Mt Mu Nd Nn Nr Nt Nv Nw Oh Pa Pc Pe Pf Po Wm) Jr(Jg Jh Lh Lx Mb Mi Mm Mr Mt Mu Nn Nt Nw Oh Om Pc) Mt(Hw Ik Ip Ir Is Iv Lh Lw Mb Mr Nt Oh Pb Pe) Lh(Ik Ip Is Jh Jj Jn Lw Mm Nn Nw Oh Pb Pc) Oh(Jg Jh Mb Mr Mu Ny Om Pe) Nw(Hw Ir Jo Mb Na Nt) Nn(Ir Is Mb Mr Pe) Mm(Ir Is Jn Ny) Ik(Mr Ny Om Pe) Is(Lw Mb Mu) Om(Og Oy Pb) Pb(Ny Pe) LwMr LxLy MbIq JjNv Unconstrained panels with 2 analytes, where 1.0E-5 >= 'model p-value' > 1.0E-6. Contains 800 panels of 7,381 total panels evaluated. : Mt(Fp Hq Hr Hu Hv Hx Ih Ii Ij Il Im In Io Iq It Iu Jg Jh Jj Jk Jm Jn Jo Jp Js Jt Li Lj Lu Lv Lx Ly Lz Ma Mc Md Me Mf Mg Mh Mi Mj Mk Ml Mm Mn Mp Mq Ms Mu Mv Mw Mx My Mz Na Nb Nc Nd Ne Nf Ng Nh Ni Nj Nk Nl Nm Nn Nq Nr Ns Nu Nv Nw Nx Ny Oe Of Og Oi Om Oy Oz Pa Pc Pd Pf Pg Po Pz Qa Qb Qc Qd Qe) Jl(Fp Hq Hr Hu Hv Hx Ih Ii Ij Il In It Iu Iv Jk Jm Jo Jp Js Jt Li Lj Lu Lv Ly Lz Ma Mc Me Mf Mg Mh Mi Mj Mk Ml Mn Mp Mq Mr Ms Mv Mw Mx My Nb Nc Nd Ne Ng Nh Ni Nj Nk Nl Nq Nr Ns Nu Nv Nx Ny Oe Of Og Oi Oy Pa Pd Pe Pf Pg Po Pz Qa Qb Qc Qd Qe) Fr(Fp Hq Hx Ii Il Io It Iu Jg Jh Jk Jm Jp Li Lj Lu Lv Lx Ly Lz Ma Mc Md Me Mf Mg Mh Mi Mj Mk Ml Mm Mn Mp Mq Ms Mu Mv Mw My Nb Nc Nd Ni Nk Nn Nq Nr Ns Nu Nv Nx Oe Of Og Oi Oy Oz Pa Pc Pd Pf Pg Po Pz Qb Qc Qd Qe) Nw(Hr Hv Hx Ij Ik Im In Io Ip Iq Is It Iu Iv Jg Jh Jj Jk Jn Js Jt Lv Lw Lx Me Mh Mi Mm Mp Mr Mu Mx My Mz Nc Nd Ne Nf Nh Ni Nj Nl Nm Nn Nr Nu Nv Ny Og Oh Oi Om Oy Pa Pb Pc Pe Pf Pg Po Qa Qc Wm) Jq(Fp Hq Hr Hv Hx Ii Ik Il Io Ir Iv Jj Jk Jn Jp Jt Li Lu Lv Lw Lz Ma Me Mh Mj Mk Ml Mn Mv Mw Mx My Mz Na Nb Nc Ne Nh Nj Nl Nm Nq Nu Nx Ny Oe Of Og Om Oz Pb Pd Pg Qa Qb Qc Qe) Lh(Hr Hu Hx Ih Il Im In Io Iq Ir Iv Jg Jk Jm Jo Jp Js Lv Ly Ma Mb Me Mg Mh Mj Mk Ml Mn Mp Ms Mu Mw Mx My Mz Nc Ne Nf Ng Nh Nj Nm Nv Ny Of Og Om Oy Pa Pf Pg Qa Qb Qd Qe) Is(Hr Hw Ii Ik Im In Io Ip Iq Ir Jg Jh Jj Jm Jn Jo Jp Jr Jt Lu Lx Ma Md Mi Mp Mr Mz Na Nb Nd Nf Nj Nm Nr Nt Nv Nx Ny Og Oh Oi Om Pa Pb Pc Pe Pf Pg Po) Jr(Hq Hr Hw Hx Ii Ik Im Ip Iq Ir Iu Iv Jj Jk Jo Jp Jt Lu Lv Lw Ma Md Me Mn Mp Mw Mz Nb Nd Nf Nj Nm Nq Nr Ns Nv Nx Ny Oz Pa Pb Pe Pf Pg Po Qc) Om(Hu Hw Ih Im Ip Iq Ir Iu Iv Jj Jn Lj Lv Lx Lz Mb Mg Mi Mm Mr Ms Mv Mx My Mz Nd Ne Ng Nj Nl Nn Nt Nv Ny Of Pa Pe Pf Qe) Oh(Hr Hv Hw Hx Ii Ij In Ip Iq Ir Iv Jj Jk Jn Jo Jp Jt Lv Lw Lx Md Mi Mm Mz Na Nb Nf Nj Nm Nt Nv Nx Oi Pa Pg Po Qa) Ny(Hu Hw Hx Im Ip Iq Ir Iv Jh Jj Jn Lw Lx Lz Mb Mi Ml Mp Mr Mu My Mz Nd Ng Nj Nn Nt Of Og Oy Pa Pc Pe Pf Wm) Nn(Hr Hu Hv Hw Hx Ii Ik Ip Iq Iv Jj Jn Jo Jt Lv Lw Lx Mi Mz Na Nb Nf Nt Nv Pa Po) Jh(Hu Hw Ik Ip Iq Ir Iv Jj Jn Lv Lx Mb Mi Mr Mz Ng Nt Pa Pe) Mz(Im Ip Jg Lx Mb Mi Mm Mr Mu Nt Nv Pa Pc Pe Pg) Ir(Ik Im Ip Jg Lw Lx Mb Mi Mp Mu Nv Pa Pc Pg) Mr(Ip Jg Jj Jn Lv Ly Mb Mm Mp Mu Nv Pb Pc) Jg(Hw Ip Iq Iv Jj Jn Lx Mb Mx Nt Pa Pe) Jn(Lw Lx Mb Mi Mu Nt Nv Pa Pc Pe Po) Nt(Ik Ip Iq Jj Lw Mb Mm Mu Pc) Nv(Ik Ip Iq Iv Lw Mb Pb Pe Wm) Mb(Iv Lx Mu Pa Pe Pf Pg) Ik(Iq Iv Lx Nb Pf Pg Po) Iq(Ip Lw Mu Nx Pe Pg) Mm(Hw Iv Js Pa Pe) Mu(Iv Jj Pa Pe) Po(Ip Oy Pb) Pe(Ip Lw Pc) Mw(My Oy) Jj(Jk Pg) Ok(Ni Of) Pa(Lw Nj) WmNo LxJt NbPb HwIp Unconstrained panels with 2 analytes, where 1.0E-4 >= 'model p-value' > 1.0E-5. Contains 1,347 panels of 7,381 total panels evaluated. : Mr(Fp Hq Hr Hu Hv Hw Hx Ih Ij Il Im In Io Iq Ir It Iu Iv Jk Jm Jo Jp Js Jt Lh Li Lj Lu Lx Ma Md Me Mg Mh Mi Mj Mk Ml Mn Mq Ms Mv Mw Mx My Na Nb Nc Ne Nf Ng Nh Ni Nj Nk Nl Nm Nq Ns Nt Nx Oe Of Og Oi Oy Oz Pa Pd Pe Pf Pg Po Qa Qb Qd Qe) Nn(Fp Hq Ih Ij Il Im In Io It Iu Jg Jh Jk Jm Jp Js Li Lj Lu Ly Lz Ma Mc Md Me Mf Mg Mh Mj Mk Ml Mm Mn Mp Mq Ms Mu Mv Mw Mx My Nc Nd Ne Ng Nh Ni Nj Nk Nl Nm Nq Nr Ns Nu Nx Oe Of Og Oh Oi Oy Oz Pb Pc Pd Pf Pg Pz Qa Qb Qc Qd Qe) Pe(Hq Hr Hu Hv Hw Hx Ih Il Im In Io Ir Iv Ij Ik Jo Jp Js Jt Lh Li Lj Lu Lv Lx Ly Ma Md Me Mg Mh Mi Mj Mk Ml Mn Mp Mq Ms Mv Mw Mx My Na Nb Nc Nd Ne Nf Ng Nh Nj Nl Nm Nq Nr Ns Nt Nx Of Og Oi Oy Oz Pa Pd Pf Pg Po Qa Qb Qd Qe) Nv(Hr Hu Hv Hw Hx Ih Ii Ij Im In Io Iu Jg Jh Jm Jo Jp Js Jt Li Lj Lv Lx Ly Lz Me Mh Mi Mj Mm Mn Mp Mu Mx My Na Nb Nc Nd Ne Nf Ng Nh Ni Nj Nl Nm Nr Ns Nt Nu Nx Ny Of Og Oi Oy Pa Pc Pd Pf Pg Po Qa Qb Qd Qe) Ny(Fp Hq Hr Hv Ih Ii Ij Il In Io It Iu Jg Jk Jm Jo Jp Js Jt Li Lj Lu Lv Ly Ma Mc Md Me Mf Mg Mh Mj Mk Mn Mq Ms Mv Mw Mx Na Nb Nc Ne Nf Nh Ni Nk Nl Nm Nq Nr Ns Nu Nx Oe Oi Oz Pd Pg Po Pz Qa Qb Qc Qd Qe) Om(Fp Hq Hr Hv Hx Ii Ij Il In Io It Jg Jh Jk Jm Jo Jp Js Jt Li Lu Lw Ly Ma Mc Md Me Mf Mh Mj Mk Ml Mn Mp Mq Mu Mw Na Nb Nc Nf Nh Ni Nk Nm Nq Nr Ns Nu Nx Oe Oi Oz Pc Pd Pg Po Pz Qa

Figure 35 Continued

Qb Qc Qd Wm) Oh(Fp Hq Hu Ih Ik Il Im Io It Iu Jm Js Li Lj Lu Ly Lz Ma Mc Me Mf Mg Mh Mj Mk Ml Mn Mp Mq Ms Mv Mw Mx My Nc Nd Ne Ng Nh Ni Nk Nl Nq Nr Ns Nu Oe Of Og Oy Oz Pb Pc Pd Pf Pz Qb Qc Qd Qe) Jh(Hr Hv Hx Ih Ii Ij Im In Iu Jg Jo Jp Js Jt Li Lj Lu Lw Lz Md Mg Mh Mj Mm Mn Mp Ms Mu Mx My Na Nb Nc Nd Ne Nf Nh Nj Nl Nm Nr Ns Nx Og Oi Oy Oz Pb Pc Pd Pf Pg Po Qa Qb Qd Qe) Ir(Hq Hr Hw Hx Ii In Io Iq It Iv Jj Jk Jm Jn Jo Jp Jt Li Lu Lv Lz Ma Md Me Mn Mv Mw Mx My Mz Na Nb Nd Ne Nf Nh Nj Nm Nq Nr Nt Nx Of Og Oi Oz Pb Pd Pf Po Qa Qb Qc Qe) Is(Fp Hq Hu Hv Hx Ih Ij Il It Iu Iv Jk Js Li Lj Lv Ly Lz Mc Me Mf Mg Mh Mj Mk Ml Mn Mq Ms Mv Mw Mx My Nc Ne Ng Nh Ni Nk Nl Nq Ns Nu Oe Of Oy Oz Pd Pz Qa Qb Qc Qd Qe) Mz(Hq Hw Hx Ii Ik Iq Iu Iv Jj Jk Jn Jo Jp Jt Li Lv Lw Lz Ma Md Me Ml Mn Mp Mv Mw Mx My Na Nb Nc Nd Ne Nh Nj Nl Nm Nq Nr Nx Og Oz Pb Pd Pf Po Qa Qb Qc Qe Wm) Mu(Hr Hu Hv Hw Hx Ih Ii Ik Im In Ip Iu Jg Jo Jp Js Jt Li Lj Lv Lw Lx Lz Md Mh Mi Mj Mm Mn Mp Mx Na Nb Nf Ng Nj Nl Nm Nr Nx Og Pb Pc Pf Pg Po Qa Qb Qd Qe) Jr(Fp Hu Hv Ih Ij Il In Io It Jm Jn Js Li Lj Ly Lz Mc Mf Mg Mh Mj Mk Ml Mq Ms Mv Mx My Na Nc Ne Ng Nh Ni Nk Nl Nu Oe Of Og Oi Oy Pd Pz Qa Qb Qd Qe Wm) Jg(Hr Hv Hx Ih Ii Ij Ik Im In Io Iu Jo Js Jt Lu Lv Lw Lz Md Mg Mh Mi Mp Mq My Na Nb Nd Ne Nf Ng Ni Nl Nr Nx Og Oi Pf Pg Po Qa Qb Qd Qe Wm) Lx(Hq Hr Hu Hv Hw Ih Ij Im In Ip Iq Iv Jj Jm Jo Jp Js Lh Lv Lw Mh Mm Mp Na Nb Nf Ng Nh Ni Nj Nm Nr Nt Nx Oy Pa Pb Pc Pf Qa Qe) Nw(Fp Hq Hu Ih Ii Il Jm Jp Li Lj Lu Ly Lz Ma Mc Md Mf Mg Mj Mk Ml Mn Mq Ms Mv Mw Nb Ng Nk Nq Ns Nx Oe Of Oz Pd Pz Qb Qd Qe) Nt(Hr Hv Hw Hx Ih Im In Io Iv Jk Jm Jo Jp Js Jt Lh Li Lv Ly Ma Md Mi Mn Mp Mw Mx Na Nf Nj Nm Nx Pa Pb Pf Pg Po Qa Qb Qe) Lh(Fp Hq Hv Hw Ii Ij It Iu Jt Li Lj Lu Lz Mc Md Mf Mi Mq Mv Na Nb Nd Ni Nk Nl Nq Nr Ns Nu Nx Oe Oi Oz Pd Po Pz Qc Wm) Jn(Hq Hr Hv Hx Ii Ik Im Io Ip Iq Iu Iv Jj Jk Jo Jp Jt Lu Lv Lz Ma Md Mn Mp Na Nb Nd Nf Nj Nm Nq Nr Nx Oz Pd Pf Pg) Po(Hu Hv Hw Hx Ih Im Iq Iv Jj Jo Jp Js Jt Lv Lw Ly Mb Mh Ml Mm Mp Mv My Na Ng Nh Nj Nm Ns Of Og Pa Pc Pf Qa Qe) Iq(Hr Hv Hw Hx Ih Ii Ij Il Im In Iv Jk Jo Jt Lv Mi Mm Mn Mp Na Nb Nf Nj Nm Nr Pa Pc Pf Qa) Pa(Hr Hv Hw Ik Im In Ip Iv Jj Jo Jp Js Jt Lv Ma Mp Na Ne Nf Nh Ni Nm Nx Pb Pc Pf Qa) Mm(Hr Hv Hx Ih Ii Ij Im In Ip Jj Jo Jt Lu Lv Mb Mi Mx Na Nb Nf Nr Nx Pf Pg Qa Qe) Mi(Hq Hv Hw Ik Im Ip Iv Jj Jo Jp Js Jt Lv Lw Ly Mb Mp Na Nj Nm Nx Pc Pf Qa) Jq(Hu Ih Ij In It Jm Js Lj Ly Mc Md Mf Mg Mq Ms Nf Ng Ni Nk Ns Oi Oy Pz Qd) Ip(Hx Ii Iv Jj Jk Jo Jp Js Jt Lw Mb Md Mp Na Nb Nf Nr Nx Pf Pg Qa) Pf(Hr Hv Hw Hx Ii Im Iv Jj Jo Jt Lv Lw Na Nb Nf Nm Nx Pb Pc Qa) Iv(Im Jj Jk Jp Lv Lw Ma Md Me Mp Nf Nm Nx Pc Pg) Mb(Hx Im Jk Jp Li Lv Lz Ma Mp Mx Qa Qb Qd Qe) Pg(Hr Hw Im Jo Js Jt Lw Na Nf Nm Pb Pc Qa) Lw(Hx Ii Im Jp Li Mx Nb Nf Nr Wm) Wm(aA Fr Jl Jp Mt Nb Nx Ok) Nf(Im Jk Lv Mp Nj Nr Pc Qe) Jj(Hq Hx Ii Il Jo Jt Nm Nx) Im(Hw Jo Jt Mj Nb Nr Nx) Pc(Hw Hx Jo Jt Qa) Mp(Hw Jo Jt Nb) Nb(My Og Oy) Ii(Ik Oy Pb) Jt(Nd Pb) NmHx MjIk MwOg HwJp JoPb

Unconstrained panels with 2 analytes, where 1.0E-3 >= 'model p-value' > 1.0E-4. Contains 1,576 panels of 7,381 total panels evaluated. : Pg(Fp Hq Hu Hv Hx Ih Ii Ij Il In Io It Iu Jk Jm Jp Li Lj Lu Lv Lx Ly Lz Ma Mc Md Me Mf Mg Mh Mi Mj Mk Ml Mn Mp Mq Ms Mv Mw Mx My Nb Nc Nd Ne Ng Nh Ni Nj Nk Nl Nq Nr Ns Nu Nx Oe Of Og Oi Oy Oz Pa Pd Pf Po Pz Qb Qc Qd Qe Wm) Iv(Fp Hq Hr Hu Hv Hw Hx Ih Ii Ij Il In Io It Iu Jm Jo Js Jt Li Lj Lu Ly Lz Mc Mf Mg Mh Mj Mk Ml Mn Mq Ms Mv Mw Mx My Na Nb Nc Nd Ne Ng Nh Ni Nj Nk Nl Nq Nr Ns Nu Oe Of Og Oi Oy Oz Pb Pd Pz Qa Qb Qc Qd Qe) Pf(Fp Hq Hu Ih Ij Il In Io It Iu Jk Jm Jp Js Li Lj Lu Ly Lz Ma Mc Md Me Mf Mg Mh Mj Mk Ml Mn Mp Mq Ms Mv Mw Mx My Nc Nd Ne Ng Nh Ni Nj Nk Nl Nq Nr Ns Nu Oe Of Og Oi Oy Oz Pd Pz Qb Qc Qd Qe) Qa(Hq Hr Hv Hw Hx Ih Ii Ij Ik Il Im In Io Iu Jj Jk Jm Jn Jo Jp Js Jt Li Lu Lv Lw Lz Ma Md Me Mh Ml Mn Mp Mv Mw Mx My Na Nb Nc Nd Ne Nf Nh Nj Nl Nm Nq Nr Nx Of Og Oi Oz Pb Pd Qb Qc Qe) Pa(Fp Hq Hu Hx Ih Ii Ij Il Io It Iu Jk Jm Li Lj Lu Ly Lz Mc Md Me Mf Mg Mh Mi Mj Mk Ml Mn Mq Ms Mv Mw Mx My Nb Nc Nd Ng Nk Nl Nq Nr Ns Nu Oe Of Og Oi Oy Oz Pd Pz Qb Qc Qd Qe Wm) Jt(Fp Hq Hr Hw Hx Ih Ii Ik Il In Io It Iu Jk Jo Jp Js Li Lj Lu Lv Lw Lz Ma Mb Md Me Mg Mh Mn Ms Mv Mw Mx My Nb Nc Ne Nf Ng Nh Nj Nk Nl Nm Nq Nr Ns Nx Og Oi Oy Pd Qb Qd Qe Wm) Iq(Fp Hq Hu Io It Iu Jj Jm Jp Js Li Lj Lu Ly Lz Ma Mc Md Me Mf Mg Mh Mj Mk Ml Mq Ms Mv Mw Mx My Nc Nd Ne Ng Nh Ni Nk Nl Nq Ns Nu Oe Of Og Oi Oy Oz Pb Pd Pz Qb Qc Qd Qe Wm) Po(Fp Hq Hr Ii Ij Il In Io It Iu Jk Jm Li Lj Lu Lx Lz Ma Mc Md Me Mf Mg Mi Mj Mk Mn Mq Ms Mw Mx Nb Nc Nd Ne Nf Ni Nk Nl Nq Nr Nu Nx Oe Oi Oz Pd Pz Qb Qc Qd Wm) Mm(Fp Hq Hu Ik Il Io It Iu Jg Jk Jp Li Lj Lw Lz Ma Md Me Mf Mg Mh Mj Ml Mn Mp Mq Ms Mv Mw My Nc Nd Ne Ng Nh Ni Nj Nl Nm Nq Ns Nu Og Oi Oz Pb Pc Pd Qb Qd) Mi(Fp Hr Hu Hx Ih Ii Ij Il In Io It Iu Jk Jm Li Lj Lx Lz Ma Md Me Mh Mj Mn Mq Mv Mw Mx My Nb Nc Ne Nf Ng Nh Ni Nl Nq Nr Ns Of Og Oy Pb Pd Qb Qd Qe) Jn(Fp Hu Hv Ih Ij Il In It Jm Js Li Lj Ly Mc Me Mf Mg Mh Mj Mk Ml Mq Ms Mv Mw Mx My Nc Ne Ng Nh Ni Nk Nl Ns Nu Oe Of Og Oi Oy Pb Pz Qb Qc Qd Qe Wm) Nt(Fp Hq Hu Ii Ij Il It Iu Lj Lu Lz Mc Me Mf Mg Mh Mj Mk Ml Mq Ms Mv My Nb Nc Nd Ne Ng Nh Ni Nk Nl Nq Nr Ns Nu Oe Of Og Oi Oy Oz Pd Pz Qc Qd) Lx(Fp Hx Ii Il Io It Iu Jk Li Lj Lu Lz Ma Mc Md Me Mf Mg Mj Mk Ml Mn Mq Ms Mv Mw Mx My Nc Nd Ne Nk Nl Nq Ns Nu Oe Of Og Oi Oz Pd Pz Qb Qc Qd) Nf(Fp Hq Hr Hw Hx Ih Ii Ik Il Iu Jj Jo Jp Li Lu Lz Ma Mb Md Me Mh Mj Mn Mv Mw Mx My Mz Na Nb Nc Nd Ne Nh Nl Nm Nq Nx Og Oz Pb Pd Qb Qd Wm) Ip(Hq Hr Hv Ih Ij Ik Im In It Iu Li Lu Lv Lz Ma Me Mh Mj Mn Mv Mw Mx My Nc Nd Ne Nh Nj Nk Nl Nm Nq Nu Of Og Oz Pb Pc Pd Qb Qd Qe Wm) Mp(Hq Hr Hv Hx Ih Ii Ij Ik Im In Iu Jj Jk Jp Js Li Lu Lv Lw Lz Md Mh Mj Mx Na Nc Nd Ne Nh Ni Nj Nl Nm Nr Nu Nx Pb Pc Pd Qb Qd Qe) Nb(Hq Hr Hv Hw Hx Ih Jj Jk Jo Jp Js Li Lj Lv Lz Ma Mb Md Mh Ml Mn Ms Mv Mw Mx Na Nc Nd Ne Ng Nh Nj Nl Nm Nx Of Pc Pd Qb Qd Qe) Mu(Fp Hq Ij Il Io It Jk Jm Lu Ly Ma Mc Me Mf Mg Mk Ml Mq Ms Mv Mw My Nc Nd Ne Nh Ni Nk Nq Ns Nu Oe Of Oi Oy Oz Pd Pz Qc) Jg(Fp Hq Hu Il It Jk Jm Jp Li Lj Ly Ma Mc Me Mf Mj Mk Ml Mn Ms Mv Mw Nc Nh Nj Nk Nm Nq Ns Nu Oe Of Oy Oz Pb Pc Pd Pz Qc) Lw(Fp Hq Hr Hv Hw Ih Iu Jj Jk Jo Js Lj Lu Lv Lz Ma Mb Md Mh Mj Mn Mv Mw Na Nc Nd Ne Nh Nl Nm Nq Nx Og Pb Pc Qb Qd Qe) Hx(Hv Hw Ih Ii Ik Im Iu Jk Jo Jp Js Li Lj Lv Lz Ma Md Mn Mw Mx My Na Nc Nd Ne Nh Nj Nq Nr Nx Og Oy Pb Pd Qb Qd Qe Wm) Jo(Hq Hw Ih Ii Ik In Jk Jp Js Li Lj Lu Lv Lz Ma Mb Md Mn Mv Mw Mx My Nc Nd Ne Nh Nj Nl Nm Nq Nr Nx Og Qb Qd Qe) Mz(Fp Hr Hu Hv Ih Ij Il In Io It Jm Js Lj Lu Ly Mc Mf Mg Mh Mj Mk Mq Ms Ng Ni Nk Ns Nu Oe Of Oi Oy Pz Qd) Ii(Hw Ih Im Jk Jp Js Li Lj Lv Lz Ma Mb Mh Ml Mn Mr Ms Mx My Na Nc Nd Ne Ng Nh Nj Nm Of Og Pc Pe Qb Qd Qe) Jk(Hr Hu Hv Hw Ih Ij Ik Im In Jh Jp Js Li Lv Lz Md Mh Mj Mx Na Ng Ni Nj Nm Nr Nv Nx Og Oi Pb Pc Qe) Mb(Fp Hq Hw Ih Ij Il Iu Jj Js Lj Md Mh Mj Mn Mv Mw My Nc Nd Ne Nh Nj Nl Nm Nq Nr Nx Pb Pc Pd Wm) Ir(Fp Hu Hv Ih Ij Il Iu Js Lj Ly Mc Mf Mg Mh Mj Mk Ml Mq Ms Nc Ng Ni Nk Nl Ns Nu Oe Oy Pz Qd Wm) Nx(Hq Hr Hw Ih Ik Iu Jp Js Li Lv Lz Ma Mh Mv Mw Mx Na Nc Nd Ne Nh Nl Nm Nr Og Pb Pc Qb Qd Qe) Hw(Hq Ih Iu Jj Js Li Lv Lz Ma Md Mn Mv Mw Mx My Nc Nd Nh Nj Nl Nm Nq Ns Pb Pd Qb Qd Qe) Jh(Fp Hq Il Io It Jm Ly Ma Mc Me Mf Mk Ml Mq Mv Mw Ni Nk Nq Nu Oe Of Pz Qc Wm) Jp(Hq Hr Hv Ih Ij Im In Iu Jj Js Li Lv Lz Md Mx Na Nd Nh Nm Nr Pc Pd Qb Qe) Nv(Fp Hq Il It Lu Ma Mc Md Mf Mg Mk Ml Mq Ms Mv Mw Nk Nq Oe Oz Pz Qc) Nr(Ih Ik Jj Js Li Lv Ma Md Mn Mr Mw Mx Nd Nj Nm Nq Pb Pc Qb Qd Qe) Im(Hq Hr Hv Ij Ik In Jj Js Li Lv Lz Ma Md Mn Mx Na Nm Oz Pc Pd Qe) Qe(Hq Hr Hv Ik In Jj Js Lv Ma Md Mx Na Nd Ne Nh Nm Og Pc Pd) Jj(Hr Ih Ij Iu Js Li Lv Ma Md Mn Mv Mw Mx Nd Nq Of Pd Qb) Nm(Hq Ih Js Li Lu Lv Lz Md Mh Mx Na Nd Ne Nl Nq Pc Qb) Pc(Hq Hr Hv Ih Ij In Js Lv Lz Md Mx Na Pd Qd Wm) Pe(Fp Ij It Iu Jm Lz Mc Mf Ni Nk Nu Oe Pz Qc) Lv(Hr Ih Iu Js Li Lz Md Mw Mx Na Nc Pd) Na(Hq Ih Li Lz Ma Mn Mx Nd Nj Nq Qb) Js(Hq Iu Li Ma Mn Nd Nq Qb) Mr(Lz Mc Mf Nd Nu Pz Qc) Wm(Ih Is Mw Nn Oh Qd) Ma(Hr Hv Ih In Mx Qb) Li(Hr Hv Ik In Md Nd) Mx(Hq Hr Ik Md Mn) Lz(Hr Hv In) Ih(Hq Hr Mj) Ik(Pd Qd) NqHu MdQb MjIl MnNh HqHv HrQd PbPd

Figure 35 Continued

Unconstrained panels with 2 analytes, where 1.0E-2 >= 'model p-value' > 1.0E-3. Contains 1,424 panels of 7,381 total panels evaluated. : Js(Fp Hr Hu Hv Ih Ij Ik Il In Io It Jm Lj Lu Ly Lz Mc Md Me Mf Mg Mh Mj Mk Ml Mq Ms Mv Mw Mx My Na Nc Ne Nf Ng Nh Ni Nj Nk Nl Ns Nu Oe Of Og Oi Oy Oz Pb Pd Pz Qc Qd Wm) Li(Fp Hq Hu Ih Ij Il Io It Iu Jm Lj Lu Ly Lz Ma Mc Me Mf Mg Mh Mj Mk Ml Mn Mq Ms Mv Mw Mx My Nc Ne Ng Nh Ni Nj Nk Nl Nq Ns Nu Oe Of Og Oi Oy Oz Pb Pc Pd Pz Qb Qc Qd Qe) Nr(Fp Hq Hr Hu Hv Hw Ii Ij Il In Io It Iu Jm Lj Lu Ly Lz Mc Me Mf Mg Mh Mj Mk Ml Mq Ms Mv My Na Nb Nc Ne Ng Nh Ni Nk Nl Ns Nu Oe Of Og Oi Oy Oz Pd Pz Qc Wm) Lv(Fp Hq Hu Hv Ij Ik Il In Io It Jm Lj Lu Ly Ma Mc Me Mf Mg Mh Mj Mk Ml Mn Mq Mv My Nd Ne Nh Ni Nj Nk Nl Nq Ns Nu Oe Of Og Oi Oy Oz Pb Pz Qb Qc Qd Wm) Mx(Fp Hu Hv Ih Ij Il In Io It Iu Jm Lj Lu Ly Lz Mc Me Mf Mg Mh Mj Mk Mq Ms Mv Mw My Nc Nd Ne Nh Ni Nj Nk Nl Nq Ns Nu Oe Of Og Oi Oy Oz Pb Pd Pz Qb Qd) Nm(Fp Hr Hu Hv Ij Ik Il In Io It Iu Jm Lj Ly Ma Mc Me Mf Mg Mj Mk Ml Mn Mq Ms Mv Mw My Nc Ng Nh Ni Nj Nk Ns Nu Oe Of Og Oi Oy Oz Pb Pd Pz Qc Qd Wm) Qe(Fp Hu Ih Ij Il Io It Iu Jm Lj Lu Ly Lz Mc Me Mf Mg Mh Mj Mk Ml Mn Mq Ms Mv Mw My Nc Ng Ni Nj Nk Nl Nq Ns Nu Oe Of Oi Oy Oz Pb Pz Qb Qc Qd Wm) Im(Fp Hu Ih Il Io It Iu Jm Lj Lu Ly Mc Me Mf Mg Mh Mk Ml Mq Ms Mv Mw My Nc Nd Ne Ng Nh Ni Nj Nk Nl Nq Ns Nu Oe Of Og Oi Oy Pb Pz Qb Qc Qd) Jp(Fp Hu Ik Il Io It Jm Lj Lu Ly Ma Mc Me Mf Mg Mh Mj Mk Ml Mn Mq Ms Mv Mw My Nc Ne Ng Ni Nj Nk Nl Nq Ns Nu Oe Of Og Oi Oy Oz Pb Pz Qc Qd) Ma(Fp Hq Ij Ik Il Io It Iu Jk Lj Lu Lz Md Me Mg Mh Mj Mn Mp Mq Mv Mw My Nc Nd Ne Ng Nh Ni Nj Nk Nl Nq Ns Nu Og Oi Oz Pb Pc Pd Qd) Hq(Fp Hr Hu Hx Ii Ij Ik In It Iu Jk Lj Lu Lz Md Me Mh Mj Mn Mq Mv Mw My Nc Nd Ne Ng Nh Ni Nj Nl Nq Ns Nu Og Oy Pb Pd Qb Qd Wm) Hv(Fp Hr Hw Ih Ii Ik Il It Iu Jj Jo Jt Lj Lu Mb Md Me Mh Mj Mn Mv Mw My Nc Nd Ne Nf Nh Nj Nl Nq Nx Of Oy Oz Pb Pd Qb Qd Wm) Jk(Fp Il Io It Iu Jm Lj Lu Ly Mc Me Mf Mg Mk Ml Mn Mq Ms Mv Mw My Nc Nd Ne Nh Nk Nl Nq Ns Nu Oe Of Oy Oz Pd Pz Qb Qc Qd Wm) Na(Fp Hr Hw Ij Ik Il Iu Jj Jm Jo Jt Lj Lu Mb Md Me Mh Mj Mk Mv Mw My Nc Ne Nh Nk Nl Ns Nu Of Og Oi Oy Oz Pb Pd Pz Qd Wm) Nx(Fp Hu Ii Ij Il In Io It Jm Lj Lu Ly Mc Md Me Mf Mg Mj Mk Ml Mn Mq Ms My Ng Ni Nj Nk Nq Ns Nu Oe Of Oi Oy Oz Pd Pz Qc) Hw(Fp Hr Hu Ij Ik Il In Io It Jm Lj Lu Ly Mc Me Mf Mg Mh Mj Mk Ml Mq Ms Ne Ng Ni Nk Nu Oe Of Og Oi Oy Oz Pz Qc Wm) Ii(Fp Hr Hu Ij Il In Io It Iu Jm Lu Ly Mc Md Me Mf Mg Mj Mk Mq Mv Mw Nb Ni Nk Nl Nq Ns Nu Oe Oi Oz Pd Pz Qc Wm) Qb(Hr Ih Ij Ik In Io It Iu Lu Lz Mc Mh Mj Mn Mq Mv Mw My Nc Nd Ne Nh Ni Nj Nl Nq Nu Of Og Oi Oz Pb Pc Pd Qd Wm) Hx(Fp Hr Hu Ij Il In Io It Jm Lu Ly Mc Me Mf Mg Mh Mj Mk Ml Mq Ms Mv Ng Ni Nk Nl Ns Nu Oe Of Oi Oz Pz Qc) Jo(Fp Hr Hu Ij Il Io It Iu Jm Ly Mc Me Mf Mg Mh Mj Mk Ml Mq Ms Ng Ni Nk Ns Nu Oe Of Oi Oy Oz Pd Pz Qc Wm) Mp(Fp Hu Il Io It Jm Lj Ly Mc Me Mf Mg Mk Ml Mn Mq Ms Mv Mw My Ng Nk Nq Ns Oe Of Og Oi Oy Oz Pz Qc Wm) Pd(Fp Hr Ih Ij In It Iu Lj Lu Lw Lz Md Mh Mj Mn Mv Mw My Nc Nd Ne Ng Nh Ni Nj Nl Nq Ns Og Oi Oz Qd Wm) Pc(Fp Hu Ik Il It Iu Jj Lj Lu Me Mh Mj Mn Mq Mv Mw My Nc Nd Ne Nh Ni Nj Nl Nq Ns Nu Of Og Oi Oz Pb) Lw(Hu Ij Ik Il In Io It Jm Ly Mc Me Mf Mg Mk Ml Mq Ms My Ng Ni Nj Nk Ns Nu Oe Of Oi Oy Oz Pz Qc) Md(Fp Hr Ih Ij Ik Il In It Iu Lj Lz Mh Mj Mn Mv Mw My Nc Nd Ne Nh Nj Nl Nq Ns Nu Oz Pb Qd Wm) Qd(Ih Ij Il In Io Iu Jj Lu Lz Mh Mj Mn Mq Mv Mw My Nc Nd Ne Nh Ni Nj Nl Nq Nu Of Oz Pb Qa) Nb(Fp Hu Ij Il In Io It Iu Jm Lu Ly Mc Me Mf Mg Mj Mk Mq Ni Nk Nq Ns Nu Oe Oi Oz Pz Qc) Ih(Fp Ij Ik Il In Iu Lu Lz Me Mh Mn Mq Mv Mw My Nc Nd Ne Nh Ni Nj Nl Nq Nu Of Oi Oz) Nf(Hu Ij In Io It Jm Lj Ly Mc Mf Mg Mk Ml Mq Ms Ng Ni Nk Ns Nu Oe Of Oi Oy Pz Qc) Hr(Fp Ij Ik Il Iu Lj Lu Mh Mj Mn Mv Mw My Nc Nd Ne Nh Nj Nl Nq Nu Og Oz Pb Wm) Ip(Fp Hu Il Io Jm Lj Ly Mc Mf Mg Mk Ml Mq Ms Ng Ni Ns Oe Oi Oy Pz Qc) Jj(Fp Hu In It Jm Lj Lu Lz Mh Mj Mq My Nc Ne Nh Nj Nl Nu Oy Oz Pz Wm) Mn(Fp Ij Ik In Iu Lu Lz Mh Mj Mq Mv Mw My Nd Ne Ni Nj Nl Nq Pb Wm) Qa(Fp Hu It Lj Ly Mc Mf Mg Mj Mk Mq Ms Ng Ni Nk Ns Nu Oe Oy Pz Wm) Ij(Ik Iu Jt Lu Lz Mv Mw My Nc Nd Ne Nh Nj Nl Nq Og Oz Pb Wm) In(Fp Iu Lj Lu Mh Mv Mw My Nc Nd Ne Nh Nj Nl Nq Oz Pb) Mi(Lu Mc Mf Mg Mk Ml Ms Nd Nk Nu Oe Oi Oz Pz Qc Wm) Jt(Hu Jm Ly Mc Mf Mj Mk Ml Mq Ni Nu Oe Of Oz Pz Qc) Wm(Ik Iv Lx Ly Mj Mm Mr Mu Mv My Nt Oy Pe Pf) Lz(Ik It Iu Mj Mv Mw My Ne Nh Ni Nj Nq Of) Mw(Ik Iu Lu Mh Mj Mq Nd Ne Ng Nh Nj Nl) Mm(Jm Ly Mc Mk Nk Oe Of Oy Pz Qc) Mv(Ik Iu Mh Nc Nd Ne Nh Nj Nl Og) Nq(Lj Mh Mj Ne Nh Nj Nl Pb) My(Mh Ne Nh Nj Nl) Nd(Lj Mj Nh Ni Nj) Ik(Fp Mk Nh Oz) FpIu MjNj NcNi Unconstrained panels with 2 analytes, where 5.0E-2 >= 'model p-value' > 1.0E-2. Contains 684 panels of 7,381 total panels evaluated. : Mv(Fp Hu Il Io It Jm Lj Lu Ly Mc Me Mf Mg Mj Mk Ml Mq Ms Mw My Ng Ni Nk Nq Ns Nu Oe Of Oi Oy Oz Pb Pz Qc) Nd(Fp Hu Ik Il Io It Iu Jm Lu Ly Lz Mc Me Mh Ml Mq My Nc Ne Ng Nk Nl Nq Ns Nu Oe Of Og Oi Oy Oz Pb Pz Qc) In(Fp Hu Hv Ij Ik Il Io It Jm Ly Mc Me Mf Mg Mj Mk Ml Mq Ms Na Ng Ni Nk Ns Nu Oe Of Og Oi Oy Pz Qc Wm) Lz(Fp Hu Il Io Jm Lj Lu Ly Mc Me Mf Mg Mh Mk Ml Mq Ms Nc Ng Nk Nl Ns Nu Oe Og Oi Oy Oz Pb Pz Qc Wm) Nq(Fp Ik Il Io It Iu Jm Lu Ly Me Mf Ml Mq Ms Mw My Nc Ng Ni Nk Ns Nu Of Og Oi Oy Oz Pz Qc Wm) Ij(Fp Hu Hv Il Io It Jm Lj Ly Mc Me Mf Mg Mh Mj Mk Ml Mq Ms Ng Ni Nk Ns Nu Oe Of Oi Oy Pz Qc) Mn(Hu Il Io It Jm Lj Ly Mc Me Mf Mg Mk Ml Ms Nc Ng Nk Ns Nu Oe Of Og Oi Oy Oz Pz Qc) Mw(Fp Hu Il Io It Jm Lj Ly Mc Me Mf Mg Mk Ml Ms Nc Ni Nk Ns Nu Oe Of Oi Oz Pb Pz Qc) Nh(Fp Il Io It Iu Lj Lu Ly Me Mh Mj Ml Mq Nc Ni Nj Nl Ns Nu Of Og Oi Oy Oz Pb Pz) Md(Hu Io Jm Lu Ly Mc Me Mf Mg Mk Ml Mq Ms Ng Ni Nk Oe Of Og Oi Oy Pz Qc) Hr(Hu Io It Jm Ly Mc Me Mf Mg Mk Ml Mq Ms Ng Ni Nk Ns Oe Of Oi Oy Pz Qc) Iu(Ik Il Io It Jm Lj Lu Me Mh Mj Mq My Nc Ne Ni Nj Nl Nu Of Og Oi Oz Pb) Hv(Hu Io Jm Ly Mc Mf Mg Mk Ml Mq Ms Na Ng Ni Nk Ns Nu Oe Og Oi Pz Qc) Qd(Fp Hu It Jm Lj Ly Mc Me Mf Mg Mk Ml Ms Ng Nk Ns Oe Og Oi Oy Pz Qc) Ih(Hu Io It Jm Lj Ly Mc Mf Mg Mk Ml Ms Ng Nk Ns Oe Oe Oy Pb Pz Qc) My(Fp Ik Il Io It Lj Lu Me Mj Ml Mq Nc Ng Ni Nk Nu Og Oi Oz Pb) Pd(Hu Il Io Jm Ly Mc Me Mf Mg Mk Ml Mq Ms Nk Nu Oe Of Oy Pz Qc) Qb(Fp Hu Il Jm Lj Ly Mc Mf Mg Mk Ml Ms Ng Nk Ns Oe Oe Oy Pz Qc) Jj(Ik Io Ly Mc Me Mf Mg Mk Ml Mq Ms Ng Ni Nk Ns Oe Og Oi Pb Qc) Nj(Fp Ik Il It Lj Lu Mh Mq Nc Ne Ni Nl Nu Of Oy Oz Pb Wm) Hq(Il Io Jm Ly Mc Mf Mg Mk Ml Ms Nk Oe Of Oi Oz Pz Qc) Fp(Il It Lu Me Mh Mj Mq Nc Ne Ni Nl Of Oi Oy Oz Pb) Mh(Ik Il It Lu Mj Mq Nc Ne Ni Nl Nu Of Oy Oz Pb) Pc(Io Jm Ly Mc Mf Mg Mk Ml Ms Ng Nk Oe Oy Pz Qc) Wm(Il Im It Li Lj Ma Me Ml Mq Mx Ni Pb Pz Qc) Na(Hu Io It Ly Mc Mf Mg Ml Mq Ms Ng Ni Oe Qc) Nl(Ik Il Io Lj Lu Me Mj Mq Ni Nk Nu Of Oy Oz) Ma(Hu Jm Ly Mc Mf Mk Ml Ms Oe Of Oy Pz Qc) Ne(Ik Il It Lj Lu Me Mj Mq Ni Of Oy Oz Pb) Mj(Hu It Lu Mq Nc Ni Nu Of Oz Pb) Il(Ik Lj Lu Mq Nc Ni Nu Og Pb) Nc(Ik Lj Lu Mq Nu Of) Oz(It Lj Lu Ni Ns Pb) Ik(It Lj Nu Of) Lu(It Lj Mq) Mx(Ml Ng Qc) Lv(Ms Ng) Mq(Ns Pb) Ni(Lj Nk) Of(Lj Og) NuPb Constrained panels with 3 analytes, where 1.0E-8 >= 'model p-value' > 0. Contains 1,005 panels of 295,240 total panels evaluated. : Et(Pb(aA Fr Hr Hw Hx Ii Ip Ir Is Ji Jk Jl Jn Jr Lh Lw Lx Mb Md Mr Mt Mu Mz Nb Nf Nh Nn No Nr Nt Nv Ny Ok Om On Pa Pc Pe Pf Pg Po) Mb(aA Fr Io Iq Ir Is Jh Ji Jl Jn Jq Jr Js Lw Lx Lz Md Mh Mr Mt Mu Mz Nf Nh Nn No Nt Nw Ny Oh Ok Om On Pa Pc Pe Pf Pg) Ik(Fr Io Iq Ir Is Iv Jh Ji Jk Jl Jn Jr Lh Lx Lz Md Mr Mt Mu Nb Ne Nh Nn Nr Nt Nv Ny Oh Ok Om Pe Pf Pg Po Wm) Pc(aA Hw Io Iq Ir Jl Jn Jq Jr Lh Lx Md Mi Mr Mz Ne Nf Nl No Ns Nt Nw Ny Ok Pa Pe Pz) Lw(aA Fr Io Ip Iq Jl Lh Lu Lx Mf Mi Mr Mt Nc Nf Nl Oh Pe Po) Nn(Hu Hw Ip Jl Jq Jr Lh Lx Mr Ng Nl No Ok Pa Pe Pz) Io(Ip Is Iv Ji Jl Jn Lh Mi Mr Nc Nk Nl Pa) Ip(aA Iq Jn Jr Lu Mz Nc Nf Oh On) On(Hu Jj My Ng Og Oy Pz) Jq(Lx Mi Nc Nd Qc Wm) Om(Hu Jh My Ng Og Oy) My(Mt Mw Nb Ny) Nj(aA Nf No Pa) Pz(Fr Ji Jl Oh) Qc(Iq Ji Jr Mz) Jk(Hu Jj Ng) Oy(Mw Ny Po) Fr(Jn Jr) Lx(Jn Ly) Nw(Hw Wm) PoNg NoMj JiaA} Ji{Ik(Fr Hw Io Iq Ir Iu Iv Jg Jh Jk Jl Jo Jr Lh Lx Lz Mi Mj Mk Mm Mr Mt Mu Nb Nn No Nr Nt Nv Oh Ok Om Oz Pa Pe Pf Po Wm) Pb(aA Fr Hw Ii Io Ip Jg Jh Jk Jl Jo Lh Ma Mb Mi Mm Mr Mt Mu Nb Nn No Nr Nt Nv Ok Om On Pa Pe Po)

Figure 35 Continued

Qc(aA Fr Iq Ir Iv Jg Jk Jl Jn Jq Jr Mb Mm Mr Mt Mu Mx Mz Nn No Nt Nv Oh Ok On Pa) Mb(aA Fr Io Iq Jh Jl Jq Mt Mu Nn No Oh Ok) aA(Fr Ih Js Lw Me Mj Mm Nj Nn Pc Qd) Mj(Jl Lh Mr No Nt Oh Ok On) Io(Hw Iq Jl Mm Nt Oh Ok Pa) Nr(Fr Jl Mt Mu No On Pa) Mm(Jr Lu Mg No Oh Pa) Ij(Fr Hw Jh Mu Ok On) My(Fr Jg Jh Jk Mw) Og(Jg Jh Jk On) No{Ii Pc Qd) Ok(Fp Jt Nn) Oy(Fr Jk Mw) Ml(Fr On) Js(Jr Oh) WmMk NnJl LxLy NgJk} On{Pb(aA Hr Hu Hv Hw Ij In Io Ip Ir Jj Jn Jo Jq Jr Lh Lw Mb My Na Nf Ni No Nr Oi Ok Om Pe Pz Qc) Mb(aA Ip Iq Jj Jq Jr Ms Ng Nj No Ns Of Og Ok Oy) Mj(aA Hu Ik Jj Jr Ms My Ng No Ns Og Ok Oy) Qc(Hu Ik Ip Iq Jj Jn Jq Jr My Mz Ng Oy) Hu(Hx Im Io Lx Mh Ml Nn No Ny Pz) Lx(Ip Jj Jm Ly Ms My Ng Oy) Nb(aA Lw Ms My No Og Ok Pz) Ik(Ih Io Iq Jh Nj Om Pz) Oy(Ih Io Jg Jh Mm Mw Qd) My(Io Jg Jh Mw Nj Qd) No(Ii Il Jj Mr Nj) Ng(Io Jg Me Ml Mm) Lw(aA Im Ns Of) Jq(Ij Im Mm Of) Io(Mv Of Og) Jt(Ir Ok) aA(Nj Pc) WmMk NnMv MmJr IpJm} aA{Mb(Fr Ip Jg Jh Jl Jq Jr Lh Lv Lw Lx Mm Mt Nj Nn No Nw Nx Ny Oh Ok Om Pb Pc Pg) Nj(Fr Ik Ip Jg Lv Lw Me Mm Mt Mu Nm Nn Nv Oh Om Pc) Jg(Hu Ik Io Ip Jl Jq Lv Lw My Ng Ns Og Oy Pb) Pc(Hr Ik Ip Jl Jq Jr Lv Mt Nm No Nx Ny Ok) Mm(Hr Ip Jl Jn Jq Jr Lv Lw Nx Ny Ok Om) Lw(Fr Ip Jl Lv Mt Nx Og Oh Ok Pb) Ik(Fr Jh Jl Mt Nv Nx Ny Ok Om) Nn(Hu Ip Jq Jr Lv Nm Nx Ok) Pb(Fr Ip Jq Lh Mt Nx Ok Om) Me(Jq Jr Lv Nw Nx Ok Om) Fr(Hu Ip Jq Jr Ok) Mw(My Oy)} Ok{Pb(Fr Hq Ik Ip Jh Jk Jl Lh Lw Lx Mb Md Mm Mp Mt Mu Mw Nb Nn No Nq Nv Nw Ny Oh Om Pa Pc Pg Po) Ik(Fr Jh Jk Jq Jr Li Lx Md Mt Mw Nj Nl Nn No Nv Nw Ny Om Pc Pg Po Qc) Mb(Fr Is Jh Jq Jr Lw Lx Md Mt Nh Nn No Nw Oh Pc Pg) No(Mh Mj Mm Mq Nn Pc) Jq(Mm Nd Nn Pc Qc) Fr(Jr Mj) Mw(My Oy) LxLy MmJr} Mb{Jq(Fr Im Ip Iq Is Iv Jg Jh Jl Jr Lh Li Lv Lx Lz Mi Mm Mr Mt Nd Nl Nn No Nt Oh Pa Pc Wm) No(Fr Il Ip Is Jg Jh Jj Jr Lv Me Mm Mt Nj Nn Ns Nw Ny Oh Om Pb Pc) Nw(Fr Jr Mm My Nj Og Oh Oy Pb) Pb(Fr Jl Mt Ny Po) FrJr LxLy MtIk} Ik{Om(Iq Ir Iv Jl Lh Mr Mt Nb No Nt Pa Pe) Jh(Ir Is Iv Jl Lh Mr Nb No Pa Pe) Fr(Ir Is Iv Jn Jq Jr Mr Nb Pe) Mt(Iv Jl Mr Nb Nt Pe) Jl(Jg Lx Mw Ny) Jq(Mr Nt Pa Pe) No(Jg Nj) Nw(Mr Pe) WmNv LxIv} Pb{Lh(Fr Ip Jg Jh Jq Lw Mm Mt Mu Nn No Nw Oh Om Pc) Fr(Hw Ir Is Jo Jq Na Pe) No(Ip Jh Jo Jq Lw Nx Om) Om(Hw Jl Mr Nb Nr Pe) Jq(Jl Mr Pa Pe) Mt(Hw Jo Pe) Jo(Lx Nw) NfJl HwNw} No{Mj(Is Jq Jr Lv Oh Om) Mm(Ip Jn Jq Jr Ms) Nj(Jq Jr Ms Om) Pc(Ip Jn Jq Jr) Nn(Ip Jq Jr) Hu(Jg Jh Om) Mw(My Oy) Jg(My Ng) OmOy} Jq{Mm(Jl Jr Lh Lx Mi Mr Nt Pa) Fr(My Nj Nl) Pc(Lh Mi Nt) MwMy QcJl} Jr{Fr(Ip Nj Qc) MwMy} LxHuJh MjLhOh MmNgNy MwMyNw

Constrained panels with 3 analytes, where 1.0E-7 >= 'model p-value' > 1.0E-8. Contains 1,477 panels of 295,240 total panels evaluated. :
Ik{Jl(Fr Im Io Ip Ir Is Iv Jj Jn Jq Jr Js Lh Li Lw Mb Md Mm Mp Mr Mu Nb Nf Nh Nj Nm Nn No Nt Nv Nw Oh Pc Pe Pf Po) Mt(Fr Hr Iq Ir Is Jh Jn Jo Jq Jr Jt Lh Li Lw Mj Mk Nj No Nr Nv Ny Oh Oz Pa Pg Po) Om(Fr Hw Is Iu Jn Jo Jr Li Lx Lz Mi Mj Mk Mm Mp Mx Nl Nr Nv Og Oh Oz Pf Po) Ny(Fr Iq Ir Is Iv Jh Lh Li Lz Mb Mk Mm Mr Nb Nn No Nt Oh Oz Pa Pc Pe Wm) Lh(aA Fr Ip Is Jg Jj Jn Jq Jr Lw Mm Mu Nn No Nv Nw Oh Pc) Pe(Ip Is Jg Jn Jr Lw Lx Mm Mu Mw Nj Nn No Nv Oh Pb Pc) Lx(aA Hq Iq Ir Is Jh Jq Jr Jt Mh Mr My Nt Pb Wm) Jh(Hx Iq Jr Li Lz Mi Mj Mk Mx Nt Nv Oh Pg Po) Mr(Ip Is Jg Jr Lw Mm Mu Nj Nn Nv Oh Pc) Nb(Ip Is Jg Jr Mm Mu Nn Nv Nw Oh Pb Wm) Et(Hr Hw Hx Il Li Lu Mh Mj Nc Nl) No(Ip Ir Is Mu Nm Nn Ns Nw Nx Wm) aA(Jk Jn Jr Li Ma Mu Mw Nn Pg Po) Fr(Hr Hx Iq Jt Nh Nt Nw Oh Po) Ir(Ip Jg Mm Mu Mw Nn Nv Nw Pg) Is(Jg Mm Mu Nn Nt Nv Pb Po) Iv(Jg Mm Mu Mw Nn Nv Nw) Jr(Jg Jk Mm Mu Nn Nt Pa) Po(Ip Jg Jq Mm Nj Pb) Nw(Hw Iq Jo Mb Mj Nt) Jq(Iq Mi Mk Nn Wm) Nt(Li Nn) Nv(Iq Li) MwMy JgOh} Pb{Jl(aA Fr Hr Hv Hw Ij In Ip Ir Jg Jh Jj Jn Jo Jr Jt Lh Lw Md Mm Mt Mu Mz Na Nb Nm Nn No Nw Nx Ny Oh Pe Po Qa) Fr(Hr Hv Hx Ij In Ip Iv Jn Js Jt Lw Mq Mr Mt Mz Nb Nf No Nr Nt Nw Nx Ny Oh Om Po Qa) No(Hr Hv Hw Ii Ij In Ir Is Jg Jn Jt Lv Ms Mt Mu Mw Mz Na Nb Nf Nj Nm Ny Pe Qa) aA(Hr Hw Hx Ii Ij In Ir Jh Jo Lv Lx Me Mw Mz Na Nb Nf Nn Ny Pa Pe Pg Po) Mt(Hr Ii Ip Ir Is Iv Jq Jr Jt Lw Mr Mz Na Nb Nr Om Po) Om(Ip Ir Is Iv Jo Jr Lx Mb Mi Nt Nv Og Oh Pa Po) Et(Hq Hv In Io Iv Jh Jo Lu Mi Na Nc Ne Pd Pz) Pe(Ip Jg Jh Lw Mb Mm Mu Nn Nv Nw Nx Ny Oh Pc) Jq(Ii Jk Jo Lx Mi Mu Nb Nn Nr Nt Po) Ji(Hq Hx Ir Is Iu Lu Lx Oy Oz Qc) Po(Hw Ip Jh Jo Lw Na) Mr(Ip Jh Lw Mb Mu Nw) Lh(Jj Jr Ma Mb Ny Pa) Ir(Lx Mm Mu Nv Nw) Ny(Hw Jo Mm Mu Nr) Nb(Ip Lw Nn Oh) Nw(Hr Jt Na Nr) Lx(Hw Jt Mb) Is(Mb Mm Mu) Mw(Hu My) MbPa MuJr HwIp} Jq{Mb(Fp Ir Iu Jo Jp Me Mh Mp Mu Mx Ne Nh Nj Nm Nq Nv Nw Ny Pe Pf Po Qa Qb Qe) Mi(Hu Hx Ij In Ip Jg Jj Jr Ly Md Ml Mt My Nf Ng Nj Nn Ny Og Oh Ok Oy Pg) Pa(Hx Ij Im In Ip Md Mh Mk Ml Mt My Nb Nj Nn Ny Og Oh Oy Pc Qc) Lx(Hu Ip Jg Jj Jl Ly Md Mh Ml Mt My Nf Nj Nn Ny Oh Ok Pc) Mm(Fr Hw Im Io Ip Iq Is Iu Iv Lu Nd Ng Nl Nr Og Oh Pe) Nn(Hw Im Ip Iq Iu Jl Jo Jr Lh Mr Nd Nl Nt Pe) Pc(Hw Im Ip Iq Iu Jl Jo Mp Mr Mt Nd Nl Oh Pe) Oh(Fr Ip Iq Iu Jg Jh Lh Mr Nd Nt Pe) Fr(Hu Im Jj Jr Nd Ng Oy Qc) Lh(Ii Ip Jj Mj Ml Nj Og Qc) Mr(Im Ip Me Mj Mt Nj Qc) Mt(Im Jl Nd Nj Pe) Nt(Io Ip Jj Nj) Me(Is Iv Jl Ok) Im(Iq Jl Ok Pc) Ip(Hw Jl Pe) Jg(My Ng Og) Nd(Jj Nj) Qc(Iq Pe) Oy(Mw Po) WmMy NqHu MjJl MpOk NjPe} Fr{Mb(Ih Im Ip Iq Ir Is Iv Jj Jn Mt Mz Ne Ng Nh Nj Nl Oh Oy) Ng(Hx Is Jg Jh Jn Jr Lh Mr Nt Ny Om Pe Po) Oh(Hr Hu Hv Hw Ip Ir Iv Jj Jn Jr Lw Na Nj) My(Hx Ii Is Lh Mr Mt Mw Nb Nw Ny Om) Oy(Hr Hx Ii Is Lh Mw Nb Ny Om Pe Po) Jj(Hr Hw Is Iv Jl Jo Lh Na Nj Nt) Nj(Hw Ir Is Jn Mz Na No) Hu(Im Is Jh Lh Mr Ny Om) Lw(Iq Is Jn Lh No) Jn(Ip Mm Nl Qc) No(Jr Mj) NmMg MmJr NaNw IpIr} Ok{Mj(Iq Is Jl Jn Jr Lh Lx Mi Mt Mu Nd Nn Nq Nt Nv Nw Ny Oh Om Pa Pg) Mq(Ip Jl Lx Mp Mu Nn Ny Oh Pa Pc) Jr(Fp Ip Jh Lw Lx Nd Nn Pc Qc) Fp(Jl Lx Mt No Ny Oh) Lw(Im Lx Mi Nm Og Oh) Nw(Im Mh Mm Mp Nd Qc) Pc(Im Lx Mi Mt Nd Nn) Qc(Iq Mt Mz Nn) Jg(Jt My Og) Jj(Jk Nq Nv) Om(My Og Oy) Nn(Lj Oi) Ly(Mi Nd) Mh(Lx Ny) Iq(Lj Mb) Nv(Jo Mm) Oh(Ip Jh) NqHu MkPa MwOg} Mb{Jr(Im Ip Jg Jh Jl Lh Lw Lx Ma Mm Mr Mt Mu Nj Nm Nn Nt Oh Om) Iq(Ip Is Jg Jh Jl Lv Lw Mm Mt Nj Nn Nw Ny Oh Om) Oh(Ip Is Jg Jh Jl Lh Lv Lx Mt Nj Ny Om) Nw(Im Lv Lw Lx Ml Nd Nl Nt Ny Of) Mt(Ip Ir Is Jj Jl Lv Ng Nj Oy) Jl(Im Is Jh Jj Jn Nn) Is(Lw Nj Nn) aA(Ma Mu Nm) Lx(Hq Oy) Ny(Of Og) Om(Og Oy) NnIp MmJn JjLh} Ji{Ij(Hr Ir Iv Jg Jk Jo Ma Mt Na Nb Nr Nv Ny Om Pe) Ml(Ii Jg Lh Lx Mi Mr Nt Ny Pa Po Qc) My(Ii Nb Nq Nv Ny Om Pa Po) Oy(Ii Jg Nb Nv Om Pa Po) Qc(Hr Hw Jh Lh Pc Pf) Mj(Iq Is Mi Nl Pe) Jk(Hu Ms Mv Nr) Og(Mw Nb Nv Om) Pa(Hx Mh Mk Nn) Me(Iv Lu Mf) Ii(Hx Lh Mr) Wm(Et Nv) Nn(Hw Mr) Iq(Js Lj) Jg(Ms Ng) PoMh NqHu NrPf LxNf MiIo MmNl JnJs} No{Mj(Hr Hv Ip Ir Iv Jl Jn Js Lh Ms Mt Mz Nf Nw Nx Ny Qa) Nj(Ip Is Jg Jh Jj Jn Lv Lw Ly Mh Mm Mt Mz Nf Nk Nn Oh) Jg(Il Ip Jj Jm Jr Ns Og Oy) Mm(Ir Is Jj Jm Lv Mz Om) Pc(Hr Is Jh Ms Nk Om) Jj(Jl Lv Nm Nx Ny) Nn(aA Jn Lv) Lw(Is Mt Oh) Ng(Jh Mw Om) Me(aA Jm) Hu(Mu Mw) Ip(Jh Jr) MyOm IsQd JhJr JlOz} On{Mj(Im Iq Ir Jn Mu Mv Mw Mx Oh) Ij(Hv Hw In Ir Iv Jn Jr Na Qa) Qc(Ir Js Lj Mt Of Oh) Il(Iq Lx Mi Nt) Lw(Io Mf Mg) Mk(Iq Pa Pe) Nd(Hq Jm Ly) Jt(Iv Jn Jr) Pc(Mn Mu Mw) Mi(Jm Ly) Nb(Im Io) Nj(Mn Oi) NmMg NnMu NUm IiLh IoJh} Oy{Mw(Ip Iq Ir Is Jl Jn Jr Lh Lx Mt Mz Nv Nw Ny Oh Pa Pe Po) Om(Jl Jr Lh Lx Mi Mr Mt Nb Nd Nt Nv Oh Pa Pe Po) Et(Jh Jk Nb Nv) Jh(Jl Lh Po) Jg(Jl Po) MmNy MtNb} Jl{Jh(Hu Jj Jr My Ng Oh Oz) Oz(aA Lw Mm Mt Oh) Mj(aA Jr Nf Oh) Lw(Im Iq Oh) Mm(Jj Jn Jr) My(Jg Mw Om) Nn(Jj Jr) Jg(Ng Og) LxLy MeaA MzQc JjLh JrPc OgOm} Et{Io(Hw Iq Ir Nt Ny Pe Qb) My(Jg Jh Jk Mv Po) Ng(Jg Jh Mw Nq Nv) Wm(Md Mg Mz Na) Jj(Il Nj Nv Pg) Nt(Jn Mt) Og(Jg Mw) NqHu MgMv MiJn MkPa IqPz} aA{Me(Hr Hu Jn Lh Lx Mf Nm Nv Ny Pg) Nn(Hr Jn Mf Mu Mx Nw Ny) Hu(Jk Mu Mw Nq) Nm(Jr Lv Oh) Lv(Jh Oh) Mw(Ng Og) LxLy IoNv JhJr} Jr{Nn(Ip Lh Mi Mr Nt Pe Qc) Lh(Jj Lw Mj Mm Pc) Mm(Ip Mr Ns) Jg(My Ng Og) Mj(Mr Nt) Mu(Nj Oh) WmJs LxLy MiPc QcNw} My{Mw(Ip Iq Ir Is Lh Lx Mt Mz Ny Oh Pa) Om(Lh Lx Mr Nb Oh Pa) Ny(Jg Mm) MtNb JhLh} Ng{Jh(Lh Lx Mi Mr Pa Po) Om(Lh Lx Mi Nd Nt Pa) Jg(Lh Lx Mi Mr Ny) MmLh} Lx{Ly(Hr Ip Ir Is Jo Lh Lw Mr Mt Nj Om Pe) Hu(Ny Om)} Lh{Hu(Jh Mt Mu Nn Om) Jj(Mm Nn Oh) Lw(Jm Oh) MmJn OgOm} Hu{Mi(Jh Om) Ny(Nn Nq) MrJh} Nw{Qc(Iq Ir Jn) Mm(Hw Ir)} Mr{Oh(Lw Mj) OgOm} Og{MmNy OhOm}

Figure 35 Continued

Constrained panels with 3 analytes, where 1.0E-6 >= 'model p-value' > 1.0E-7. Contains 3,321 panels of 295,240 total panels evaluated. :
Ik{Fr(Hv Hw Ii Ij Im In Ip It Jg Jh Jo Js Li Lw Lx Lz Md Mi Mj Mk Mq Mx Na Ne Nf Nj Nl Nm Nr Nu Nv Nx Oz Pa Qa Qb Qd) Nw(Hr Hv Ii Is Iu Jg Jh Jk Jn Jr Jt Li Lz Mi Mk Mm Mu Mv Na Nm Nn Nr Nu Nv Oh Om Oz Pa Pf Pg Po Qa Wm) Is(Hq Hw Ii Io Ip Iq Ir Iv Jk Jo Jq Jr Li Lw Lz Ma Md Mi Mj Mk Mw Nj Nm Nq Nr Nx Oh Pa Pc Pf Pg) Jh(Fp Hw Ii Ip Iu Jn Jo Jq Lv Mb Mh Mp Mu Mz Na Nc Ne Nf Ng Nj Nl Nn Nr Nu Nx Oz Pf Qa Qb Qd Qe) Po(Hu Hx Im Ir Iv Jj Jn Jr Li Lv Lw Mh Ml Mr Mu My Nb Nh Nm Nn Nt Nv Ny Oh Oy Pc Pe Pf Qd) Nv(Im Ip Jg Jj Jn Jo Jq Jr Jt Lw Lx Lz Mb Mj Mk Mm Mu Mz Nm Nn Nr Nt Oh Oz Pa Pc Pf) Lx(Hu Hx Ip Jg Jn Jo Lh Li Lw Mb Mj Mk Ml Mm Mu Mv Nb Nh Nm Nn Ny Oh Oy Oz Pa) Ir(Hq Im Iv Jk Jq Jr Li Lv Lw Ma Mi Mp Mv Nb Nj Nm Nq Nt Nx Oh Pa Pb Pc Pe Pf) Nt(Ip Iq Iv Jg Jj Jn Js Ma Mm Mp Mu Mw Mx Mz Nf Nj Nx Oh Pb Pc Pe Pf Pg) Jr(Ii Im Ip Iq Iu Iv Jo Li Ma Mi Mj Mk Mp Nj Nm Nq Ny Oh Oz Pf Pg) Iv(Ip Jk Jq Li Lw Ma Me Mp Mr Nb Nj Nm No Nx Oh Pc Pe Pf Pg) Pe(Jj Jk Li Lv Ma Mb Mk Ml Mp Mr Nh Nm Nx Pf Pg Wm) Nn(Hw Hx Ii Ip Iq Jn Jo Jt Mb Mi Mj Mz Om Pa Pg) Jq(Hw Jg Jk Jo Li Lz Mj Mp Mu Nb Nq Nr Oz Pf Pg) Iq(Ip Jg Li Lv Lw Ma Mm Mu Mw Nx Oh Pc Pf Pg) Mr(Im Jk Jn Li Lv Ma Mp Mw Nm Nx Pb Pf Pg) Nb(Jk Jn Li Lw Ma Mp Nh Nj Nm Nx Pc Pf Pg) Mu(Jn Mb Mi Mt Nj Ny Oh Om Pa Pf Pg) Jg(Hx Jn Lz Mi Mj Mt Mx Nr Ny Pa Pg) Om(Hq Im Ip Mb Nd Ne Nu Pb Pg Qe) Ny(Ip Jj Jo Jt Mj Nj Nr Pb Pf) Pa(Jn Li Lw Mm Mz Nj Nx Oh Wm) Mt(Hw Hx Ip Lz Mi Nm) Pg(Ij Jn Jt Li Mb Wm) Jn(Jk Mi Mk Mm) Lh(Li Nj Pf) Ii(Li Oh) Jk(Hu Jj) NoMw LzNx MbPf MiLi JoOh} Pb{Po(Hr Hv Ij In Ir Is Iv Jg Jj Jn Jr Jt Lv Ly Mh Mm Mp Mq Mu My Mz Ng Ni Nj Nm Nn Nv Nw Nx Ny Oh Oy Pa Pc Qa) Nb(Hv Hw Hx Ij In Ir Is Jg Jh Jn Jo Jr Lv Mb Ml Mm Mp Mu My Mz Na Nf Nm Nv Nw Nx Ny Og Pa Pc Pf Pg Qa) Nw(Hv Hx Ii Ij Im In Ip Is Iv Jh Jk Jn Jq Jr Lw Mi Mm Mu Mz Nf Nh Nt Nu Nx Oh Om Pa Qa) Mr(Hw Ir Is Jg Jj Jl Jn Jr Lv Ly Ma Mm Mp Mz Nf Nm Nn Nv Nx Ny Oh Pa Pc Pf Qa) Is(Hw Ii Ip Ir Jg Jh Jl Jo Jq Lw Lx Md Mz Nf Nn Nr Nv Nx Ny Oh Pa Pc Pe Pf) Ny(Hu Io Ip Ir Jh Jj Jq Jr Jt Lw Mt Nm Nn Oh Om Oz Pa Pc Pf Wm) Nv(Hr Hw Iv Jh Jj Jl Jn Jo Jq Jr Jt Mb Mu Mz Nf Nr Oh Wm) Mz(Ip Jg Jh Jk Jo Lx Mm Mu Nn Nr Nt Oh Oz Pa Pe Pg) Ir(Ii Ip Jg Jh Jk Mb Mi Mp Nn Nq Nx Oh Pa Pf Pg) Om(Hx Ii Iq Iu Jj Jn Lz Mm Mx Nd Nl Oz Pf Pg Qe) Mt(Hv Hx Ij In Jn Mu Nf Nj Nm Nt Nx Oh Pa Qa) Pe(Ih Jk Jn Jr Lv Ma Mj Mn Mp Nf Nj Pa Pg Qd) Mu(Hw Ii Ip Iv Jn Jo Jt Mb Nr Nt Nx Oh Pa) Jh(Fr Hw Ip Jo Jq Jr Lx Mb Mi Nf Nr Nt Pa) Jq(Hq Hw Hx Ip Iu Jg Mp Nq Oz Pf Pg) Pa(Fr Hw Jg Jl Jn Jo Jr Jt Lw Na) Nn(Hw Ii Ip Iv Jo Jt Mb Na) Fr(Ii It Jj Me Mx Nm) Hw(Jg Jr Mi Mm Oh Pf) Jo(Ip Jj Jr Oh Pc Pf) Nr(Ip Jg Lw Mm Nx) Lx(Hv Iv Jn Na Qa) Mb(Iq Oh Pf Pg) Ii(Ip Jr Oh Pf) Jl(Im Mp Ni Pc) Jj(Jk Pg) Oh(Ip Jt) MmIv MwOy JkJr} Nw{Mm(Hr Hv Ij In Ip Is It Iv Jl Jn Jo Js Jt Lh Me Mr My Mz Na Ng Ni Nr Nt Oh Pe Qa) Nn(Hr Hu Hv Hw Im Ip Ir Is Iv Jl Jn Jo Jt Mr Mu Mv My Na Ng Nt Og Oy Pe Qa) My(Hr Ii Jg Jh Jk Jo Lh Mi Mr Mt Mu Nb Nt Ny Om Pa Pe Po Wm) Lw(Fr Im Iq Is Iu Iv Jr Lh Lx Mi Mr Nd Nl Nt Og Oh Pa Pe) Im(Hr Hv Hw Ir Iv Jl Jn Jo Jq Jr Jt Mj Na Nr Pc Qa) Lh(Hu Hx Jj Ly Md Mh Mj Ml Mv Ng Ny Og Oy Pc Pg Po) Oy(Fr Hr Ii Jg Jh Jk Jo Mi Mr Mu Nb Om Pe Po) Oh(Hr Hv Hw Ip Ir Iv Jo Jt Na Nm Nt Oi Qc) Wm(Ip Ji Jo Jr Lv Ly Mk Nb Nv Nx Ny Om) Pc(Hr Hv Hw Ir Iv Jn Jo Jr Mr Na Nt Pe) Nd(Hr Hv Ir Is Iv Jn Jq Jr Jt Na Qa) Og(Fr Hr Jg Jh Mr Mu Mw Nb Om Pe) Qc(Hr Is Iv Jq Js Jt Mt Mz Qa) Fr(Hr Hu Hv Hw Jo Mv Ng Qa) Mi(Hu Hv Jn Jr Ly Mh Na Ng) Mp(Hr Hv Ir Jn Jq Jt Na) Nt(Hu Jj Jn Jr Ly Nj) Ip(Hr Hw Is Jr Mr Pe) Lx(Hv Ir Jn Jt Na) Mh(Jl Mr Nr Pe Po) Mu(Hu Is Iv Ng Nj) Ng(Jg Jh Jk Om) Hu(Jh Jk Nq) Ml(Hw In) Iu(Jn Jq) Jl(Na Oz) Pe(Hx Ny) NmJr LyMr MvOm NjJq HwIj JnPa} Jj{Nn(Hr Hw Hx Ip Ir Is Iv Jn Jo Jr Lv Lx Mb Mi Mr Mz Nj Nl Nt Nv Nx Ny Om Pa Pe Pg Po) Nt(Ip Is Jg Jh Jk Jl Jn Jr Lh Lw Mb Mm Mt Mu Mz Nj Nm Nv Ny Oh Ok Om Pc) Oh(Hr Hw Ii Ip Jk Jl Jo Lx Mb Mi Mr Mu Nm Nv Nx Ny Of Pa Pe Pg Po) Jr(Ip Jg Jh Jk Jl Jo Lx Mb Mi Mr Mu Nd Nm Nq Nv Ny Of Om Pg) Lh(Im Ip Is Jg Jh Jk Jn Lw Ly Mt Mu Nj Nm Nv Ny Ok Om Pc) Mr(Fr Ip Is Jg Jh Jk Jn Lw Mm Mt Mu Nm Nv Ny Pc) Ny(Fr Ip Jl Jo Lw Lx Mb Mi Ml Mm Mp Mu My Nd Pc) Jh(Hw Ip Iq Ir Is Lv Lx Mb Mi Nd Nv Pa Pe Pg) Mt(Hr Hw Jk Jl Jo Lv Lx Mi Mu Nm Om Pc Pg) Lx(Ip Ir Is Jg Jk Jl Jn Jt Mb Nm Om) Nv(Ip Ir Jl Jq Mb Mm Mu Nm Pc) Fr(Hv Ip Jt Lw Mz Nl Nm Nx) Om(Hw Ip Is Jl Mb Mi Nd Nl) Pg(Ip Jg Jq Mb Mm Mu Nm Ok) Jk(Ip Jl Jo Jq Mb Mi Mm) Mm(Ir Iv Jn Mz Pe) Jq(Hw Jo Mu Nq Po) Jl(Ip Jg Nm Oz) Mu(Ir Is Jn) Mi(Jn Nm) Ip(Pe Po) MbPe} Ip{Oh(Hr Hw Ii Iq Ir Is Iv Jg Jh Jl Jo Jr Jt Lh Lw Md Mi Mm Mr Mt Mu Mz Na Nb Nm Nt Nv Ny Om Pa Pe Po) Jr(Hw Jg Jh Jk Jl Jq Lh Lx Ma Mi Mn Mr Mt Nj Nt Ny Om Pa Pc Pe Po Qc) Fr(Hr Hv Hw Iq Jl Js Jt Lh Ma Mr Mz Na Ne Nf Ng Nj Nt Pe) Nn(Hr Hu Hw Iq Jr Is Iv Jl Jn Jt Lh Mr Mz Na Nt Ny Pa Pe) Mb(Ir Is Jg Jh Jl Jn Lh Lx Mr Mu Mz Nt Nv Ny Om Pf) Jq(Im Iq Is Iu Jg Jh Jo Lz Mp Mt Nd Nj Nr Po Wm) Jh(Iq Ir Is Jl Lh Mr Mz Ng Nt Og Pe) Om(Iq Ir Is Jl Lx Mr My Ng Nt Og Oy) Mm(Ir Iv Jl Jn Lh Mr Mz Ny Pe) Mz(Jg Jl Lh Lx Mr Nt Pa Pe) Mt(Hr Hw Ir Iv Mr Nt Pe) Iq(Hw Jl Lh Mu Nt Ny Pe) Jg(Ir Is Jl Mr Ng Og Pe) Jn(Lh Lx Mi Mr Nt Pa Pe) Jl(Im Md Nf Oz Pc) Mr(Lw Ly Pc) Nb(My Og Oy) Ir(Lx Mu Nv) Is(Lx Mu) Lh(Ly Pc) WmJi PoOy NyOg PcPe} Mb{Ny(Hu Im Ir Iv Jh Jn Jr Lh Lv Lw Lx Lz Mm Mu My Mz Ng Nh Nj Nn Nt Oy Pc Pf) Ir(Im Io Jg Jh Jl Lh Lv Lw Lx Ma Mm Mu Nj Nn Nv Oh Om Pc Pf) Jn(Jg Jh Lh Lv Lw Lx Ma Mi Mr Mu Nn Nt Oh Om Pc Pf) Nn(Hu Im Iv Lh Lv Lx Mi Mr Mz Nj Nt Nv Pa Pe) Is(Io Jg Jh Jr Lh Lv Lx Mm Mu Mz Om Pc Pf) Iq(Im Jr Lh Lx Ma Mu Nt Nv Nx Pc Pg Po) Jh(Iv Lh Lv Lx Lz Mh Mr Mz Ng Nt Pa Pe) Oh(Im Iv Jp Lw Mi Mr Mu Nl Nt Nv Pa Pe) Jg(Iv Jl Lh Lx Lz Mr Mx Mz Pa Pe) Om(Im Iv Jl Lh Lx Ms My Ng Nt Of) Mz(Im Jl Lh Lv Lx Mm Nt) Jl(Io Lw Mm Nh Oz Pc) Jr(Lv Mi Nq Pa Pc Pf) Lh(Im Lv Lw Mu Nj Pf) Lx(Iv Ng Nj Of Pg) Mr(Lv Lw Mm Pc) Iv(Lw Mm Mu) Pe(Mm Nj Pc) Oy(Mw Po) LvMu NjPa ImNv} Fr{Ng(Hr Hw Ih Ii Ij Im In Jl Jo Jt Lw Lx Md Mi Mm Mt Mu Mw Nb Nd Ne Nf Nh Nl Nm Nv Nx Pa Qb) Hu(Hr Hv Hw Hx In Jl Jo Lx Ma Md Mt Mu Mx Ne Nf Nh Nl Nn Nt Nv Nx Pe Po Qa Qb) Nj(Hr Hv Ih Ij Im In Iq Jo Js Jt Lh Mr Mt Mx Nf Nh Nr Nt Ny Pe Qa) Oy(Ij In Jg Jh Jo Lx Ma Md Mr Mt Mu Mx Ne Nf Nh Nr Nt Nv Nx Pa Qb) My(Hr Ij In Jg Jh Jl Lw Lx Md Mx Ne Nf Nr Nt Nv Nx Pa Pe Po Qb) Lw(Im Iv Jl Mf Mr Mx Nl) Om(Ma Mg Ms Mv Nl Of Og) Mv(Hx Mt Nb Nf Ny) Nl(Ij In Mz Nf Nm) Iq(In Jo Lv Na Qc) Lx(Hq Jm Ly Nq) Og(Hx Nb Nx Ny) Ly(Lh Mr Nt) Mg(Hx Jo Lh) Im(Hr Jl Mz) Jm(Lh Mi Nt) Of(Hx Nb Ny) Mk(Pa Pe) Mx(Mf Mj) WmJq MhMr MzQc NcNi JlOz} Jq{Nj(Hw Im Iq Iu Jk Jr Mp Mu Nb Nn Nq Nr Nv Ny Oh Oz Pf Po) Jg(Hu Hw Im Iq Iu Jh Jr Lz Md Mp Ms Mu Mv Nd Nl Ns Oy) Im(Hw Is Iu Jh Jo Jr Mj Nb Nc Nl Nr Nv Oh Oz Po) Po(Hx Ij In Md Mh Ml My Ng Ny Of Og Om Pc) Mu(Iq Iu Lz Mp Ng Nl Nn Og Oh Oy) Jr(Hw Iu Jk Jo Lx Me Mp Nd Nq Pc) Wm(It Ji Mj Mr Na Nt Nv Nx Oy) Jh(Hw Iq Is Iu Lz Mp Nd Ng Nl) Qc(Ir Is Li Mj Mt Nr Oh Qe) Pc(Ir Is Lz Mx Nr Nv Ny) Nn(Hu Ir Is Lz Mp Nr) Nl(Ma Me Mp Nq Om Pf) Ii(Ij Md Ml My Ny Oy) Og(Jk Mr Mw Nb Nq Pe) Me(Ir Jo Nr Pe) Lx(Ij In Is) Mp(Hw Iq Is) My(Nb Nq Om) Pe(Ij Mh Ml) Md(Mt Nb) Hx(Ij Ml) Iv(It Qd) Jk(Hu Oy) NqOy MtOh NdIs NgPa IqQd} Om{Ng(Im Iq Ir Is Iu Iv Jl Jh Jr Mm Mp Mr Mt Mu Nl Nn Nv Ny Oh Pe Po) My(Hw Hx Ii Iq Ir Is Iv Jg Jn Jr Mi Mm Mt Mw Mz Nn Nt Nv Ny Pe Po) Oy(Hq Hw Hx Ii Iq Ir Is Iv Jk Jn Mm Mw Nl Ny Pg) Of(Jl Jr Lh Lx Mi Mr Mt Nd Nt Nv Ny Pa Pe Po) Og(Hx Iq Ir Is Jr Lx Mi Mt Nb Nl Nt Ny Pa) Lh(Hx Il Ly Md Mg Ml Ms Mv Ny) Nt(Hu Iq Jn Jr Ly Mg Nj Nn) Lx(Hq Ir Is Jm Jr Mg Mv Pg) Mr(Hu Hx Mg Mh Ml Mm Ny) Hu(Im Is Mt Nn Nq Nv) Jl(Im Mh Mm Oh Oz) Mg(Mi Mm Mt Pa) Iq(Lw Mm Nj Qc) Ir(Ij Im Mm Nn) Jr(Im Mi Oh Qc) Mi(Ly Mv) Melv MkPa MsIs MtMv HwIj} Mt{Pc(Hr Hu Hw Iq Ir Iv Jl Jn Jo Jr Lh Mi Mr Mu Na Ng Nt Oi Oy Pa Pe) Oy(Hr Hx Ii Jg Jh Jl Jo Lh Mi Mr Mu Ny Pa Pe Po) Lw(Iq Ir Is Iv Jl Lh Mf Mr Nt Oh Pa Pe) Ng(Jg Jh Lh Lx Mi Mu Mw Nb Nm Ny Pa Po) Nj(Hr Hw Iq Jr Mi Mz Na Nt Oi Pa Pe) Hu(Jg Jh Jk Lx Mi Mr Mu Nn Nq Nt Ny) Og(Hr Ii Jg Jh Mw Nb Ny) Nn(Hw Jo Jr Mr Na Pe) My(Ii Jg Jh Jl Ny Pa) Nt(Jm Jn Ly Mk) Mm(Ir Is Iv Mz) Qc(Iq Ir Jr Mz) Ly(Lh Mi Mr) Mj(Jl Jr Lh) Mk(Lh Pa Pe) Jn(Lx Mi Pa) Oh(Hr Hw Pe) Mh(Jl Mr) Iq(Lj Lv) Jm(Lx Mi) JlJr} Oh{Lw(Hw Hx Ii Im Iq Ir Is Iu Iv Jr Lu Lx Mi Mu Nb Nl Nt Nv Ny Pa Pe Po) Jr(Hr Jg Jh Jl Js Lh Lx Mi Mj Mr Nm Nt Pa Pc Pe Qc) Mj(Hw Hx Ii Ir Is Iv Mz Nt Nv Ny Pe) Jg(Hr Hw Ir Jl Lh Mr My Ng Og Oi Pe) Lx(Hr Hw Ir Is Jn Jt Mz Na) Mm(Hw Ir Iv Lh Mr Mz Na Ny) Mu(Hu Hw Ir Is Iv Jn Lv Nj) Jh(Hu Hw Lh Lv Mr Ng Oy Pe) Pc(Hw Ir

Figure 35 Continued

Lh Mr Mz Pe) Nj(Hw Mi Nb Nt Pa) Og(Ii Mw Nb Ny) Mi(Ir Jn Na) Pa(Jn Mz Na) Nt(Jm Mz) Mh(Jl Mr) My(Ii Nb) Ir(Im Nv) Oi(Nv Ny) Oy(Ii Nb) LvMr} Mm{Ir(Hx Im Io Is Jh Jl Jn Lh Lu Lv Lx Mi Mr Mu Mz Nv Ny Pa Pc) Mz(Im Is Iv Jh Jl Lh Lv Lx Mi Mr Nl Nt Nv Ny Pa Pe) Jl(Hv Hw Im In Io Iq Is Iv Js Lh Na Nf Ny Pz Qa) Jn(Io Lu Lx Mi Mr Ng Nt Nv Ny Pa Pe) Mr(Io Is Jh Jm Js Lv Lw Ly Ng) Ny(Hu Io Iq Is Iv Mg Mv Of) Ng(Lx Mi Nb Nv Pe Po) Lh(Io Iq Is Jm Ly Mg) Oy(Mw Nb Pe Po) Iq(Hw Lv Na) Is(Hw Io Nf) Iv(Io Lx Pa) NtJs LxLy MkPe MyNb} Jh{Og(Hx Iq Ir Is Jl Lh Lx Mi Mr Mz Nb Ny Pa Pe Po) Oy(Hx Ii Iq Is Lx Mi Mr Mw Nb Nv Ny Pa Pe Pg) Ng(Hx Iq Ir Is Iu Jr Nd Nt Nv Ny Pe Pg) Hu(Iq Is Nd Nn Nq Nt Nv Ny Pa Pe Pg Po) Mr(Jn Jr Lv Lw Ly Mg My Mz Nn Pc) Lx(Ir Is Jm Jn Jr Ly Mg My Mz) My(Mi Mw Nb Ny Pa Pe Po) Lh(Il Iq Jr Ly Mg Nj Of) Mi(Jn Jr Ly Mg) Iq(Lv Lw Nt Pe) Ir(Lv Nn Pc) Nt(Jn Mz) Is(Lw Nn) Pa(Jn Mk)} Nn{Ny(Hw Ir Is Jl Jr Mr Mu Mv My Ng Nt Og Oi Oy) Is(Hu Hw Im Jl Lw Lx Mi Mr Nt Oi Pe) Jl(Hu Im Ir Jn Mf Mu Na Oi Oz Pc) Lx(Hw Ir Iv Jn Jr Jt Na Ng) Jr(Hr Hw Im Iu Jo Ns Pa) Mr(Hu Jn Lv Lw Ly Ng) Lh(Jn Lw Mk My Ng Oy) Nt(Ir Jn Lv Lw Mz) Oy(Ii Mw Nb Pe Po) Pe(Hu Jn Lv Mk) My(Ii Mw Nb) Ng(Ii Jg Mi) Pa(Jn Lw Na) Nv(Hu Ir) MiJn MzNj NbOg} Jg{Ng(Hq Hx Ir Is Jk Jn Mp Mu Mz Nd Nt Nv Ok Pa Pe Pg Po) Oy(Is Jr Lh Lx Mi Mr Mw Nb Nv Ny Ok Pa Pe Pg) My(Hx Is Jn Lh Lx Mr Mz Nb Nv Pa Pe Pg Po) Og(Hx Ir Is Jn Lh Mr Mx Mz Nb Ny Pa Pe Po) Lx(Hu Ir Jm Jn Jr Ly) Jr(Hu Jl Ns Nt) Lh(Hu Jn Jo Mg) Nt(Jn Mz) Ms(Is Jl) HuIs IrJt PzJl} Lw{Is(Im Io Iq Jl Lh Lx Mf Mi Mr Mu Nv Ny Pa) Jr(Im Iu Jk Jl Lx Mi Mr Nq Nt Ny Pa Pe) Iq(Im Lh Lv Mr Mu Nt Nv Ny Pa Pe Qc) Jl(Io Jn Lh Mf Mz Nf Og) Jn(Lh Lx Mi Mr Nt Pa) Mz(Im Lh Mr Nt Pa) Ny(Ir Mr My Ng Og) Mi(Jm Ly Ng Oy) Lx(Ir Jm Ng) Lh(Ly Ng Og) Mr(Im Ly) Ir(Im Nv) PoOy} Pc{Ny(Hu Iq Ir Is Jl Jr Mr Mv My Ng Nt Of Og Oy Pe) Jr(Hr Hw Im Iu Jo Lx Mr Nd Ns Nt Pa Pe) Is(Hw Iq Jl Lh Lx Mi Mr Mz Nf Nt Pe) Mz(Im Jl Lh Lx Mi Mr Nt Pa Pe) Jn(Jl Lh Lx Mi Mr Nt Pa Pe) Ir(Im Jl Lx Mi Mu Nv) Jl(Im Lh Nf Oz) Lh(Hu Iq Ng) PoOy MyNb} Jl{Mj(Iq Ir Is Jn Js Lh Mr Mx Mz Ny) Im(Ir Jn Jr Mz Nf Nm Oz) Oy(Md Mu Nb Ny Po) Oz(Mp Mu Nm Ok Pf) Mi(Jm Ly Mk Ng) Mh(Iq Nf No) Qc(Iq Jn Jr) Og(Mw Nb Ny) Nt(Jm Ly) Mq(Hw Na) Nj(Md Nf) Hu(Lh Nq) NmMg LxJm LyLh MkPa MyNb IoIs} Mw{Oy(Hq Hr Hx Ih Ii Iv Jk Lz Md Mi Mr Mu Mx My Nb Nd Nf Nt Nx Pf Pg Qb) My(Hu Hx Ih Iv Jn Jp Js Mi Mr Mx Nb Nf Nt Nv Nx Pe Pg Po) Og(Ir Is Jn Jr No) Ng(Lh Lx Ok) Hu(Hx Lx Ny) NoIl} Ny{My(Lh Lx Me Mi Mr Mu Nb Pa Po) Oy(Lh Lx Mi Mr Mu Nb Pa Pe Po) Ng(Lh Lx Mi Mp Mu Nd Pa) Hu(Lh Mi Mu Nd Wm) Og(Lh Mi Nm Pa) Wm(Ly Mj Mr) Mj(Iq Jr) LyMi IqQc} Ok{Mj(Hq Jk Md Mr Nf Pe Po) Fp(Is Jn Lh Pa Pe Pg) Me(Io Lu Mf) Mh(Lh Pa Po) My(Mv Nb Nq) Jk(Hu Ng Oy) Jo(Hq Lh Pg) Pa(Nr Pe) LyLh MzLj NbOy NfQc} Jr{Nj(Im Jk Lh Lx Mi Nt Nv Pa) Nm(Im Lx Mi Pa Qc) Mj(Lx Mi Pa Pe Wm) Im(Hr Pe) Qc(Iq Pa) Jm(Lx Nt) WmFp PoOy NqHu LuMe LyMi} Lx{Ly(Ii Iv Jn Jt Mu My Na Nh Nm) Is(Il Ir Jm Mj Mz) Mh(Hq Ns) Nb(Hu Oy) Ir(Mu Nj) Jn(Jm Js) MzNf} Mu{Nj(Iq Ir Is Jn Lh Mz) Ng(Is Lh Mi Nt Pa) Oy(Lh Nb Pa Po) Lv(Iq Ir) LyLh MyNb IsOg} Mj{No(Hw Ij In Jo Jt Mp Mx Na Qb) Lh(Iq Is Jn Mz) Mr(Is Jn Mz) PoOy NtMz IsPe} Lh{Ly(Is Nj No) Nj(Iq Mz) Hu(No Nv) NmJo JnJs} Wm{Ji(aA Mf Mh Mq Mr) Nv(Jm Mz)} Mz{Nj(Mi Nt Pa) NqHu MlPa IsQc} Is{Nt(Io Jm) PoOy MiJm IqQc} Nv{Nb(My Oy) ImIr} No{MeIo HuJk} Nj{Jn(Nt Pa)} Iq{LvIm QcNx} IjJiPg

Constrained panels with 3 analytes, where 1.0E-5 >= 'model p-value' > 1.0E-6. Contains 4,497 panels of 295,240 total panels evaluated. : Pb{Ii(Hw Ik Im Iq Jg Jh Jj Jn Jo Jp Jt Li Lv Lw Ma Mb Mm Mp Mx My Mz Na Nf Ng Nr Nv Nx Og Oy Pa Pc Pg Qa) Mu(Hr Hv Hx Ih Ij In Iq Jg Jh Js Li Lv Lw Lx Lz Md Mh Mi Mm Mp Na Nf Nj Nm Nn Pd Pf Pg Qa Qb Qe) Pa(Hr Hv Hx Ij In Ip Iv Jj Js Lv Lx Ma Mm Mp Nf Ni Nj Nm Nn Nr Nt Nv Nx Oh Pc Qa) Nb(Hq Hr Im Iq Jj Jk Jp Js Jt Li Lx Ma Md Mh Mq Ne Nh Ni Nj Nr Oy Pd Po) Ir(Hq Hw Hx Im Jo Jp Jq Jr Lv Lw Ma Me Mn Mw Mz Nd Nm Nr Nt Oy Oz Pc Pd) Jh(Hr Hv Hx Ij In Iv Jn Js Jt Lv Lw Lz Mh Mx Na Nn Nx Pf Pg Qa Qb Qe) Jo(Hq Hx Im Iq Jg Jk Jn Jp Li Lv Lw Ma Md Mi Mm Mp Mr Mw Nf Nr Nx Pg) Mz(Hq Hw Hx Im Iu Iv Jr Lv Lw Ma Mb Mi Mp Nd Nj Nm Nq Nx Pc Pf) Nv(Hv Ij Im In Io Ip Jg Js Lw Lx Mi Mm Na Ni Nm Nn Nw Pc Pf Qa) Nn(Hr Hv Hx Ij In Jn Lw Lx Md Mi Mq Nf Ni Nr Nt Nx Pg Qa) Ip(Hx Iv Jg Jk Jn Jt Lx Mb Mi Mp Na Nf Nt Nx Pf Pg Qa) Oh(Hq Hv Hx Ij In Iv Jk Lx Mi Mq Na Nf Nr Nx Pg Qa) Lx(Hr Ij In Jg Lw Mm Mp Mq Nf Nm Nr Nt Nx Pc) Is(Hq Hr Io Jr Jt Lv Ma Mi Mp Nm Nq Oy Pd Pg) Mb(Hx Im Iv Jg Jk Jn Jp Li Mi Mm Nr Nt Qa) Hw(Iq Jk Jn Jp Lw Ma Mp Nm Nt Nx Pc Pd Pg) Pf(Hr Hv Hx Ij In Iv Jg Jt Na Nf Nr Nt Nx) Pg(Hr Hv Jg Jn Jt Mm Mr Na Nf Nm Nr Qa) Mi(Hv Ij In Jg Jn Jt Lw Mm Na Nx Qa) Nr(Im Jk Jn Jp Jr Lv Md Mp Nf) Nt(Io Jg Jn Jt Lw Mm Mp Nf Nx) Jt(Hq Im Jk Jr Mm Mp Nq Pc) Jg(Hr Hx Iv Mx Na Nf Qa) Nw(Hq Iu Mq Ni Nm Qc Wm) Mm(Hv Hx In Na Nf Qa) Mr(Hv Ij In Jk Md Na) Jq(Li Lu Ma Mw Pd) Nx(Iq Iv Jj Jr Lz) Nf(Jk Jr Lw Oz) Hx(Jj Jr Lw Ma) Iv(Ik Lw Ma) Mj(Ik Im) HqJj JkJn JrOz} Ik{Mu(Fp Hr Hv Hw Hx Ih Ii Ij Im Ip Iu Jg Jj Jo Js Jt Li Lv Lz Md Mj Mk Mm Mn Mp Mx Mz Nf Nh Nl Nm Nn Nr Nu Nx Oz Pd Qa Qb Qd Qe) Pf(Hr Hw Hx Ii Ip Jg Jj Jk Jn Jo Jt Lv Lw Lx Md Mi Mj Mm Mx Mz Na Ne Nh Nj Nm Nn Nx Oh Pa Pg Qa Qe) Jg(Hq Hr Hv Hw Ii Io Ip Jo Js Jt Li Lu Lv Mb Md Mh Mk Mp Mz Na Ne Nf Nn Nx Oz Pd Qa Qb Qd Qe) Pa(Hr Hv Hw Ij Ip It Iv Jk Jo Js Jt Lv Ma Mb Md Mj Mp Mw Mx Na Nb Nf Nh Nm Pc Pg Qa Qd) Lx(Hr Hv Hw It Jk Js Lv Lz Md Mp Mq Mz Na Ne Ng Nj Nr Nw Nx Og Pc Pg Qa Qd Qe) Oh(Hq Hx Ij Im Jk Jn Jt Li Lu Ma Md Mi Mj Mk Mx Ne Nh Nj Nm Nx Of Oz Pg) Nn(Hr Hv Iu Li Lv Lw Md Mk Mx Na Ne Nh Nj Nl Nm Nr Nx Oz Qa Qd) Jn(Hq Ii Ip Iq Ir Is Iv Jo Li Lz Ma Mj Mp Mv Nd Nm Nq Nr Oz Pc) Nb(Hx Im Iq Lh Lv Me Ml Mv Mw Mx My Nq Nt Qa Qb Qe) Pg(Im Ip Jo Js Lw Lz Mj Mk Mm Mx Mz Nj Nm Nr Oz Pc) Iv(Hq Ii Im Iq Jt Lv Mb Mi Mj Mk Mv Nh Nq Oz Wm) Nv(Fp Hr Hv Io Jp Js Mi Nj Nu Nx Pd Qa Qd Qe) Iq(Ii Ij Jj Jk Jo Md Mp Mz Na Nj Nm Qa) Mj(Im Ip Li Lw Ma Md Mm Mp Nj Nx Pc) Mi(Ip Jk Jt Lw Mm Nh Nm Pc Qa Wm) Jq(Hq Ii Jt Lu Mh Mv Mx Nl Nu) Wm(aA Ir Jr Mr Mt Mz Nx Qd) Nw(Im In Ip Mp Mx Nd Nj Nx) Li(Hx Ip Jk Jo Mk Nx Oz) Lz(Ii Ir Jk Jo Jr) Mm(Hx Ii Mx Nr Qd) Mz(Jk Jo Mk Mp Oz) Jt(Im Ip Jr Mp) Nt(Jp Lw Qd) Ii(Ip Pc Qd) Hq(Jj Jr) NrJr LwMx MkNx MpIs IpJk JjJo} Mb{Ip(Hw Hx Ii Im Iv Jj Jk Jp Js Jt Li Lj Lv Lz Ma Md Mh Mi Mm Mp Mx Nb Nc Ne Nf Nh Nj Nl Nq Nr Pa Pc Pe Pg Po Qa Qd) Im(Iv Jg Jh Jn Jp Js Jt Li Lj Lv Lw Lx Lz Ma Mh Mi Mj Mm Mr Mu Nb Nf Nj Nt Nx Pa Pc Pe Pf Pg Po Qd) Mm(Hx Ih Io Jh Jj Js Li Lj Lu Lv Lx Lz Mh Mi Mu Mx Nb Nf Nt Nv Om Pa Pf Pg Po Qa Qb Qd Qe) Mz(Iu Iv Jk Lw Ma Mi Mp Mr Mu Nd Nh Nj Nl Nm Nq Nv Om Pa Pc Pe Pf Pg Po Qa Qb Qe) Jg(Ih Jj Js Lj Lv Mg Mh Mi My Nf Ng Nt Nv Oy Pf Pg Po Qa Qb Qd Qe) Lv(Ih Iv Jj Jp Js Li Lx Lz Ma Mh Mi Nf Nh Nl Nt Om Pa Pf Po) Mu(Ih Jj Js Lj Lx Lz Mi Mr Ng Nj Nl Nt Og Pa Pe Pg Qb Qd Qe) Jh(Hu Ih Js Lj Mi Mx Nf Nj Nl Nv Og Oy Pf Pg Po Qa Qb Qd Qe) Iv(Ir Jj Jn Jp Lz Ma Md Me Mp Mr Nf Nj Nv Pa Pc Pf Pg Po) Jj(Hq Hx Ii Il Jn Li Lz Ma Mi Mr Nm Nq Nx Pa Pf Po) Jn(Jp Lz Mp Nd Nj Nm Nq Nv Nx Pa Pe Pg Po Qa) Lx(Hu Jm Jp Js Lj Lw My Nh Nv Pc Pf Qd Qe) Mi(Jp Js Li Lj Lw Ly Nj Om Pc Qa Qd Qe) Nt(Jp Js Lj Lw Ma Mp Nf Nj Pc Pf Po) Om(Hu Ih Lj Lz Mg Mr Nl Pf Qd Qe) Mr(Jp Ly Ma Mp Nj Nv Ny Pf) Pa(Jp Js Lw Ma Mk Mp Nh Pc) Po(My Ng Nh Nj Of Og Pc) Ir(Hx Md Nx Pe Pg Qa Qb) Pf(Hq Nj Nn Ns Nv Oy Pd) Lz(Jp Mp Nj Nv Nx Pc) Ma(Ih Js Qb Qe) Nj(Jp Nv Pg Qa) Lh(Jo Js Ng Nh) Lw(Jp Mx Nv) Oy(Nb Pe Pg) Mx(Li Pc) Nv(Js Pc) Pg(Nn Ns) NqHu MyNb} Jj{Mu(Hq Hr Hw Hx Ih Ii Il Ip Iq Iu Iv Jg Jo Jt Lv Lx Mi Mm Mn Mp Mz Nd Nf Nj Nl Nm Nr Nx Pa Pe Pf Po Qb Qe) Mm(Hq Hr Hv Hw Hx Ih Ii Ij Il In Ip Iq Jo Js Jt Lu Lv Lx Md Mi Na Nb Nf Nr Nx Oh Pa Pd Pf Po Qa Qe) Jg(Hq Hr Hw Hx Il Io Ip Iq Ir Is Iu Iv Jn Jo Lv Mi Mp Mx Mz Nd Nf Nr Nx Pa Pd Pe Po) Ip(Hq Hr Hw Hx Ii Il Iq Ir Iv Jn Jo Jt Lw Md Mi Mn Nb Nd Nf Nm Nq Nr Nx Pa Pf) Lx(Hr Hv Hw Hx Ih Ii Iv Jo Js Lv Lw Mh Mn Mp Mz Na Nj Nx Of Pc Pe Pf Qa Qe) Nm(Hq Hw Hx Il Iq Ir Is Iv Jn Jq Lu Lv Mz Nd Nf Nq Nx Pa Pe Pf Po) Mi(Ii Ir Is Iv Jo Js Jt Lv Lw Ly Mp Mz Nj Nx Pc Pf Qa Qe) Po(Hx Im Ir Is Jh Jn Jr Lv Lw Mh Ml Mp My Nj Oy Pc) Jo(Im Iq Ir Is Jh Jn Lv Lw Mp Mz Nf Nq Pa Pc Pf Pg) Oh(Hq Hv Hx Iq Iu Iv Jt Lv Md My Na Nb Nd Nf) Jh(Hq Hr Hx Il Iu Iv Jn Lz Mz Nf Nl Nx Qe) Jn(Hq Hr Hw Ii Lw Mp Nd Nq Of Pc Pg) Pa(Hr Hw Ii Iv Jt Lv Lw Nj Nx

Figure 35 Continued

Figure 35 Continued

Jt Lh Mi Mr Mz Nb Nf Nm Nv Nx Pa Pe Po Qe) Lv(Ih Iv Js Jt Mi Mp Mr Mz Nf Nt Pa Pe) Hu(Mi Mr Nq Nt Nv Om Pa Pg Po Qb) Oy(Hx Ii Mi Mr Nv Nx Pe Pg) Pa(Iv Jn Js Mk My Mz) Mi(Hq Js Jt Ly) My(Ii Lh Nv Po) Nt(Jn Js Ly) Mz(Ml Nl Pe) Mr(Jn Ly) NmMg MeIv MpIr IqNx} Mz{Lv(Hw Iu Iv Jo Mi Mr Nl Nm Nr Pa Pe) Qc(Iq Ir Iv Jr Mr Nv Oh Om Pa Pe Qe) Ml(Ii Mi Mr Nb Nq Nr Om Pe Po) Mi(Ly Mp My Nf Oh Oy) Om(Md Mv Nd Nl Nt Of) Pa(Hx Mh Mp My Og Oy) Wm(Fp Ly Mj Mk) My(Ii Nb Nq Po) Mh(Ii Pe Po) Mp(Ir Pe) Mw(Mv Og) Iv(Js Me) Jk(Hu Oy) PoHx MjIs IiOy} Nv{Ng(Lh Mi Mr Mw Nb Nf Nm Pa Pe Po) Oy(Hr Ii Lh Mi Mr Nf Nm Pa Pe Po) Hu(Hr Io Mi Mr Nf Nq Nt Pa Po) Io(Is Iv Jn Jt Na Nm Nt) My(Ii Lh Mt Nf Po) Og(Hr Mw Nb Nf Nm) Nm(Jn Mg Oh) Mi(Hq Jm Ly) Iq(Hw Na Qc) Pa(Jn Js Mk) Mr(Jn Ly) NtJm MjIs MvOm HrOh IjJq QcJr} Nb{My(Hx Iq Is Jn Jp Jr Lh Ma Me Mp Mv Nc Ne Nh Nl Nm Nq Pa Pf Pg Po) Oy(Iq Is Jk Jn Jq Jr Lh Ma Me Mp Mv Ne Nh Nm Nq Pa Pf Pg) Og(Is Jn Jr Me Mp Nm) Mt(Mh Mv Of) Fr(Mg Ms) Lv(Iq Oh) Jq(Ij Ml) WmNa NqHu MhJl NdJn IqQc OhOi} Om{Nd(Hq Hu Jm Jn Lj Ly Mg Ns) Pa(Hu Hx Il Jn Mh Ml Ms Mv) Of(Hw Hx Iv Jn Mx Nl) Mi(Hx Il Jm Jn Ml) Pe(Hx Mg Mk Ml Ms) Po(Hx Mh Ml Mv) Mr(Ii Ly Ms Mv) Mg(Iu Iv Nl) Mp(Hq Ns) Nf(Ml Mv) Hu(Iv Jn) Ij(Iv Jn) MsHw} Iq{Lv(Hr Hw Hx Ii Iv Jo Lh Mi Mp Mr Na Nm Nr Nt Oh Pa Pe Po Qc) Oh(Hr In Lj Mj Na Nx Qc) Mp(Hw Jo Mr Na Nt) Qc(Jn Pg Qa Qe) Na(Mi Pa Pg) Jr(Lj Nx Qd) Nm(Mr Pg) Mw(Mv Og) Hw(Mn Pg) NtNx IiOy} Oh{Pa(Hr Hv In Jt Lv Ni Nm Oi Qa) Mi(Hr Hv Jt Lv Ly Nm Qa) Oi(Hx Jk Jn Lv My Nm Nx) Lv(Hr Ii Nm) Jn(Iu Mj Nt) Po(Mh Oy) Mw(Ms Ng) Ni(Nc Nl) Hu(Jk Nq) MhIi MjJo HrJp} Mw{Og(Hx Iv Lh Mr Mx Pa Pe Po Qe) Ng(Is Jl Jq Jr Mi My Nd Nt) Oy(Il Jo Jp Js Mp Nl Qa Qe) My(Ii Lz Mp Nd Pf Qe) Mv(Jq Mt) Hu(Lh Ml) MdJq} Me{Iv(Ir Is Jl Jn Jr Lh Lv Ma Pf) Jq(Hv Io Lu Lv Mf Mh Mx) Lh(Io Jm My Ng Og) Ir(Hx Jr Lv Pg) Mf(Is Jr Mt) Io(Is Jr) PoNg HvIs} Po{Ng(Jk Jn Lv Ma Mh Mp Nm Nq) Fr(Mg Mv Of Og) Mh(Jn Mt Ns Oy) My(Jn Mt Ns Pf) Og(Is Jn Nm) Oy(Jn Lv Nm) Mj(Ir Jr) LvIr} Mi{Ly(Fr Ir Is Jn Lv Nh Nm Nx Pe Pf Pg Qa) Jn(Is Jm Js Lv Mp) Ir(Jm Lv Mp) Ng(Jk Nm) FrHq MtMy IoIs} Jr{Wm(Jm Ly Mk Na) Nq(My Ng Ns Oy) Mj(Hx Ii Nr Pf) Mp(Hr Ir Ns) Qc(Ma Nf Pf) Hr(Ma Nd) Jk(Ng Og)} Is{Pa(Il Io Jm Jn Mk) Nm(Io Jt Og) Hu(Jk Nq) Ii(Og Oy) Jm(Nd Pg) NtIl MjPf NaIt QcJn} Lh{Mj(Ih Ir Js Mx Pf Qb) Ma(Hu Mg Ng) Nm(Mg Ng) Mk(Pa Wm) Hu(Jk Nq) MvMy NgJk} Jn{Nt(Io Jm Lv Mp) Lv(Mr Pa Pe) Mp(Mr Pa Pe) Mj(Pa Pe) Nd(Ir Jm) NqHu MtQc} Jq{Nq(Ms Nc Ng) Ii(Hx Mh Og) Nm(Io Og) Jk(Ij Ng) MjQd NlIo HxOg QaQc} Nm{Mr(Jo Mg Ng) Ng(Jk Pa) Og(Hx Pa) Pe(Jo Mg)} Nt{Mp(Io Jm Js Nf) Jm(Ir Pg) LvNf LyPf IoJp} Mt{Hx(Ii My Ng Og) Ii(Mh Ng) LyNd JkOy} Ir{Ma(Hx Iv Mr) Nq(Hu Jm) Pa(Lv Mk) MjMp} Jl{Mq(Hv Qa) Nd(Ly Mk) MhLi MvMy NcNk} Mr{Ly(Lv Mp) Ng(Jk Ma) NqHu} Nq{Hu(Hx Jt Pe)} Lv{Nf(Pa Pe) JsPa} Wm{NoMh MkJp} Fr{MgNx NdJm} IiOyPf

Constrained panels with 2 analytes, where 1.0E-6 >= 'model p-value' > 0. Contains 337 panels of 7,381 total panels evaluated. : Fr(aA Et Hr Hu Hv Hw Ih Ik In Ip Iq Ir Is Iv Ji Jj Jl Jn Jo Jq Jr Js Jt Lh Lw Mb Mr Mt Mz Na Ne Nf Ng Nj Nl Nm No Nt Nw Ny Oh Ok Om Pb Pe Qa) Jq(aA Et Hw Im Ip Iq Is Iu Jg Jh Jl Jo Jr Lh Lx Mb Mi Mm Mp Mr Mt Mu Nd Nn No Nr Nt Nv Nw Oh Ok On Pa Pc Pe Pf Po Wm) Et(aA Hw Io Ip Iq Ir Is Ji Jl Jn Jr Lh Lw Lx Mb Md Mi Mr Mt Mu Mz Nf Nn No Nt Nw Ny Oh Ok Om On Pa Pc Pe Pg Po) aA(Ik Ip Jg Jh Ji Jl Jr Lh Lv Lw Lx Ma Mb Me Mm Mt Mu Nj Nm Nn No Nv Nw Nx Ny Oh Ok Om On Pc Pg) Ok(Ik Im Ip Jh Ji Jl Jr Lw Lx Mb Mi Mm Mp Mq Mt Mu Nd Nn No Nw Ny Oh Om On Pa Pb Pc) No(Ip Is Jg Jh Ji Jj Jl Jn Jr Lv Lw Mb Mm Ms Mt Nj Nm Nn Ny Oh Om On Pb Pc) Jl(Ik Im Ir Jg Jh Ji Jj Jn Jr Lh Lw Mb Mm Mt Mz Nf Nm Nn Nw Oh Om Oz Pb) Mt(Hw Ik Ip Ir Is Iv Ji Jr Lh Lw Mb Mr Nt Oh Pb Pe) Ji(Hw Ik Io Iq Lx Mb Mm Mu Nn Nt Oh On Pa Qc Wm) Jr(Jg Jh Lh Lx Mb Mi Mm Mr Mu Nn Nt Nw Oh Om Pc) On(Hu Ik Ip Jj Lw Mb Ms My Ng Ns Of Og Oy Pb) Lh(Ik Ip Is Jh Jj Jn Lw Mm Nn Nw Oh Pb Pc) Oh(Jg Jh Mb Mr Mu Ny Om Pe) Nw(Hw Ir Jo Mb Na Nt) Nn(Ir Is Mb Mr Pe) Mm(Ir Is Jn Ny) Ik(Mr Ny Om Pe) Is(Lw Mb Mu) Om(Og Oy Pb) Pb(Ny Pe) LwMr LxLy MbIq JjNv Constrained panels with 2 analytes, where 1.0E-5 >= 'model p-value' > 1.0E-6. Contains 357 panels of 7,381 total panels evaluated. : Oh(Hr Hv Hw Hx Ii Ij In Ip Iq Ir Is Iv Jj Jk Jn Jo Jp Jt Lv Lw Lx Md Mi Mm Mz Na Nb Nf Nm Nt Nv Nw Nx Oi Pa Pg Po Qa) Om(Hu Hw Im Ip Iq Ir Is Iv Jj Jn Jq Lh Lx Lz Mb Mg Mi Mm Mr Ms Mt My Mz Ng Nl Nn Nt Nw Of Pa Pe) Nn(Hr Hu Hv Hw Hx Ii Ik Ip Iq Iv Jj Jn Jo Jt Lv Lw Lx Mi Mz Na Nb Nf Nt Nv Nw Ny Pa Po) Nw(Hr Hv Ik Im In Ip Is Iv Jh Jn Jt Lw Lx Mi Mm Mp Mr Mu Mz Nd Nm Nr Pb Pe Qa Wm) Ny(Hu Ip Iq Ir Is Jh Jj Jn Jq Jr Lh Lw Mb Mr Mu My Mz Ng Nt Of Og Oy Pc Pe Pf) Is(Hw Ik Io Ip Iq Jg Jh Jr Lx Mi Mr Mz Nf Nt Nv Pa Pb Pc Pe Po) Jh(Hu Hw Ik Ip Iq Ir Iv Jj Jn Lv Lx Mb Mi Mr Mz Ng Nt Pa Pe) Jr(Hr Im Ip Iu Jj Jk Jo Lw Ma Mp Nb Nd Nj Nm Nq Nv Pa Pe Po) Mz(Im Ip Jg Lh Lx Mb Mi Mm Mr Mt Mu Nt Nv Pa Pc Pe Pg) Ir(Ik Im Ip Jg Jq Lw Lx Mb Mi Mp Mu Nv Pa Pc Pg) Jg(Hw Ip Iq Iv Jj Jn Lh Lx Mb Mr Mx Nt Pa Pe) Mb(Iv Jn Lh Lx Mr Mu Nt Nv Pa Pe Pf Pg) Mr(Ip Jj Jn Lv Ly Mm Mp Mu Nv Pb Pc) Iq(Ik Ip Lh Lw Mt Mu Nt Nv Nx Pe Pg) Jn(Lw Lx Mi Mu Nt Nv Pa Pc Pe Po) Jq(Iv Jj Jk Lz Nj Nl Nq Oz Pg) Ik(Iv Lx Nb Nt Nv Pf Pg Po) Nt(Ip Jj Lw Mm Mu Pc) Mt(Hr Jj Jo Jt Na Nj) Pe(Ip Lw Mm Mu Nv Pc) Mm(Hw Iv Js Pa) Mu(Iv Jj Lh Pa) Nv(Ip Iv Lw Pb) Po(Ip Oy Pb) Mw(My Oy) Nj(Lh Pa) Jj(Jk Pg) LwPa LxJt LyLh NbPb HwIp Constrained panels with 2 analytes, where 1.0E-4 >= 'model p-value' > 1.0E-5. Contains 484 panels of 7,381 total panels evaluated. : Lx(Hq Hr Hu Hv Hw Ih Im In Ip Iq Iv Jj Jm Jo Jp Js Lv Lw Mh Mm Mp Mu Na Nf Ng Ni Nm Nr Nx Oy Pb Pc Pf Qa Qe) Mu(Hr Hv Hw Hx Ih Ik Ip Jg Jo Js Jt Lv Lw Lz Mi Mm Mp Na Nb Nf Ng Nj Nm Nr Nv Nx Og Pb Pf Pg Po Qa Qb Qe) Jg(Hr Hv Hx Ih Ik Im Io Jo Js Jt Lv Lw Lz Mi Mp My Na Nd Ne Nf Ng Nn Nr Nv Og Oi Pf Pg Po Qa Qb Qe) Iq(Hr Hv Hw Hx Ih Ii Ij Im In Iv Jk Jo Jt Lv Mi Mm Mn Mp Mr Mz Na Nb Nf Nj Nm Nr Pa Pc Pf Po Qa) Pf(Hr Hv Hw Hx Ii Im Ip Ir Iv Jh Jj Jn Jo Jt Lv Lw Mi Mm Mr Mz Na Nb Nf Nm Nt Nx Pa Pb Pc Qa) Mm(Hr Hv Hx Ih Ii Ij Im In Ip Jh Jj Jo Jt Lu Lv Mb Mi Mx Na Nb Nf Nr Nv Nx Pg Po Qa Qe) Jh(Hx Ih Jo Js Jt Lw Lz Mh Mx My Na Nd Nf Nn Nr Nv Og Oy Pb Pg Po Qa Qb Qe) Mi(Hq Hv Hw Ik Im Ip Iv Jj Jo Jp Js Jt Lv Lw Ly Mb Mp Na Nj Nm Nx Pc Qa) Mz(Hw Ir Iu Iv Jk Jn Jo Lv Lw Ma Ml Mp Nd Nj Nl Nm Nq Nr Pb Po Qe Wm) Ip(Hx Ii Iv Jj Jk Jn Jo Jp Js Jt Lw Mb Md Mp Na Nb Nf Nr Nx Pa Pg Qa) Pa(Hr Hv Hw Ik Im Iv Jj Jo Js Jt Lv Mp Na Nf Nh Nm Nt Nx Pb Pc Qa) Ir(Hq Hx Iv Jj Jk Jn Li Lv Ma Mr Mw Nd Nq Nt Pb Pe Po Qb) Im(Hw Iv Jn Jo Jt Lw Mb Mj Mr Nb Nf Nr Nv Nx Pe Pg Po) Po(Iv Jj Jt Lv Lw Mb Mh Mp My Ng Nj Nm Of Og Pc) Jn(Hw Ii Ik Jj Jk Jo Lv Ma Mp Nb Nd Nm Nq Nr Pg) Iv(Jj Jk Jp Lv Lw Ma Md Me Mp Nf Nm Nx Pc Pg) Mb(Hx Jk Jp Li Lv Lz Ma Mp Mx Qa Qb Qd Qe) Nv(Hr Hv Hw Jo Js Jt Na Nf Nm Nt Pc Qa) Pg(Hr Hw Jo Js Jt Lw Na Nf Nm Pb Pc Qa) Nt(Jp Js Lv Ly Mp Nf Nj Nm Nx Qa) Jj(Hq Hx Ii Il Jo Jt Nm Nx Pe) Lw(Hx Ii Jp Li Mx Nb Nf Nr) Nf(Jk Lv Mp Nj Nr Pc Qe) Mp(Hw Jo Jt Nb Pe) Pc(Hw Hx Jo Jt Qa) Nn(Js Oi Qa) Nb(My Og Oy) Ii(Ik Oy Pb) Wm(aA Jr) Nm(Hx Mr) Jp(Hw Mr) Jt(Nd Pb) Pe(Lv Nj) MjIk MwOg JoPb Constrained panels with 2 analytes, where 1.0E-3 >= 'model p-value' > 1.0E-4. Contains 504 panels of 7,381 total panels evaluated. : Jp(Hq Hr Hv Hx Ih Ii Ij Im In Iu Jj Jk Jo Js Jt Li Lv Lz Md Mp Mx Na Nb Nd Nf Nh Nm Nr Nx Pc Pd Qa Qb Qe) Jk(Hr Hu Hv Hw Ih Ik Im Jo Js Jt Li Lv Lw Lz Mh Mi Mm Mp Mx Na Nb Ng Nj Nm Nr Nx Og Pb Pc Qa Qe) Mb(Fp Hq Ih Ii Iu Jj Jo Js Jt Lj Lw Md Mh Mn Mv Mw Nb Nd Ne Nf Nh Nj Nl Nm Nq Nr Nx Pc Pd) Nm(Hq Hw Ih Ii Im Ip Js Li Lu Lv Lz Md Mh Mp Mx Na Nb Nd Ne Nf Nl Nq Nr Pc Qa Qb Qe) Jj(Hr Hw Ih Ij Im Iu Js Li Lv Lw Ma Md Mn Mp Mv Mw Mx Nb Nd Nf Nq Nr Of Pd Qa Qb Qe) Lv(Hr Hw Hx Ih Ii Im Ip Iu Jo Js Jt Li Lw Lz Md Mp Mw Mx

Figure 35 Continued

Na Nb Nc Nr Pc Pd Qe) Qe(Hr Hv Hw Ii Im Ip Iq Jn Jo Js Lw Ma Md Mi Mp Mx Na Nb Nd Nr Nx Og Pc Pd) Lw(Hq Hr Hw Ih Iu Jo Js Jt Lu Lz Ma Md Mh Mm Mp Ne Nl Nq Nx Qa Qb Qd) Nf(Hq Hw Hx Iu Jo Jt Li Lz Ma Mi Mn Mx Nb Nc Nh Nl Oz Pb Qa Qb Wm) Pc(Hq Hr Hv Ih Ii Ij Im In Ip Js Lz Md Mp Mx Na Nb Nr Nx Pd Qd) Ma(Hr Hv Hw Hx Ih Ii Im In Ip Iq Js Jt Mx Na Nb Nr Nx Qa Qb) Li(Hr Hv Hw Hx Ii Ik Im In Ip Js Md Mi Mp Na Nb Nd Nr Nx) Mp(Hr Hv Hx Ii Ij Im In Js Md Mx Na Ne Nh Nr Nx Qa) Ip(Hq Hr Hv Ij Im In Lz Mn Mv Mw Mx Nc Nh Nj Pb Wm) Hw(Hq Hx Ih Iv Js Lz Md Mn Mx Nd Nj Nq Nx Pb Qb) Js(Hq Hx Ii Im Iu Jo Mn Nb Nd Nq Nr Nx Pf Qb) Mi(Hr Hx Ih Ij In Ng Nh Ni Oy Pb Po Qb Qd) Qa(Hq Hx Ii Ik Im Iv Md Mn Nb Nd Nj Nx Pb) Nr(Ih Ik Md Mn Mx Nd Nj Nq Nx Pb Qb Qd) Nb(Hx Ih Ml Mx Nd Ne Nh Nj Of Po Qb) Ii(Hx Ih Im Lz Mx My Nh Nj Og Qb Qd) Na(Hq Ih Im Lz Mn Mx Nd Nj Nq Qb) Mm(Io It Lz Md Me Mh Ni Qb Qd) Im(Hq Hr Hv Hx Ij In Md Pd) Nx(Ih Ik Iu Lz Mx Nc Nd Pb) Iq(Hq Lj Lz Md Mw Qc Wm) Jt(Hq Hx Ik Lz Md Nq Qb) Mx(Hq Hr Ik Jo Md Mn) Hx(Ik Iv Jo Og Pb) Lz(Hr Hv In Jo) Ih(Hq Hr Jo Mj) Qb(Iv Jn Jo Md) Ik(Jo Pd Qd) Iv(Nd Pb) Qd(Hr Wm) NqHu

Nb Nc Nd Ne Nh Nk No Nr Ns Nv Nx Og Oi Om Pa Pc Pd Pe Pf Pg Po Qb) Nv(Hq Hr Hu Hv Hw Ii Ij Im In Io Ir Is Iv Jh Jj Jm Jo Js Lh Lu Lw
Lx Ly Me Mf Mg Mh Mr Mt Mu Mx My Mz Na Nb Ne Nf Ng Nh Nq Ns Nu Nx Og Oi Om Oy Pa Pe Po Pz Qc) Nx(Hu Im Io Iq Jh Jj Jl Jp Lh
Lu Lw Lx Ly Lz Ma Mf Mg Mh Mi Mp Mr Ms Mt My Mz Nc Nd Nf Ng No Ns Og Oi Oy Pa Pc Pf Po Pz Qb Qc) Lh(Hx Il Io Is Iu Jh Jl Jm Jt
Lu Ly Mf Mh Mj Ml Mn Mp Mq Mr My Nc Nk Ns Nt Nu Oe Oi Om Oy Pa Pe Pf Pg Qb Qc) Jl(Hr Hu Ij Io Jm Jo Lu Mf Mj Mr Mx My Nb Nd
Ne Ng Nh Nl No Nq Ns Og Oi Pe Qc) Mt(Hr Hu Hx Io Ir Is Iv Ma Mk My Mz Ng No Oy Pa Pg Qc Qe) Io(Hw Hx Ii Ir Is Iv Mi Mr Mz Nb Om
Pa Pe Pg Po Qb Qe) Pg(Hr Iq Is Jh Jj Jm Jp Mz Nf Ng Ns) Om(Mf Og Pa) Mw(My Oy) Nb(My Oy) MzQc NgJk HxOg IrJh JgPa} Nx{Lx(Fp
Hq Hr Hu Hv Hw Hx Ih Ii Ij Il Im In Io Iq Ir It Iu Iv Jh Jm Jn Jo Js Lu Lv Lw Ly Ma Mc Md Me Mf Mg Mh Mi Mj Mk Ml Mn Mp Mq Mr Ms
Mu Mv Mx My Mz Na Nb Nd Ne Nf Ng Ni Nn No Nq Nr Ns Nu Oe Of Og Oi Oy Oz Pc Pe Pg Pz Qc) Im(Fp Hq Hr Hu Hv Hw Ih Ii Ij Il Io Iq
Ir Is Iv Jh Jm Jn Js Lh Lj Lu Lv Lw Ly Lz Mc Md Me Mf Mg Mh Mi Mk Ml Mq Mr Ms Mt Mu Mx My Mz Nb Nd Nf Ng Nh Nk Nl Nn No Nr
Ns Nt Nu Ny Oe Og Oy Oz Pc Pe Pg Po Pz Qa Qb Qd) Jh(aA Fp Hq Hr Hv Hx Ij Il In Io Iq Ir Is It Iu Jg Jk Jl Jm Jn Js Lu Lv Lw Ly Lz Ma Mc
Md Me Mf Mi Mj Mk Ml Mn Mp Mq Mt Mu Mw Mx My Mz Nb Nc Nd Nf Ng Ni Nl Nm Nq Nr Ns Ny Of Og Oi Oy Oz Pc Pd Pg Po Pz Qb
Qc) Mu(Hq Hr Hu Hv Hw Hx Ii Ij Il In Io Iq It Jk Jm Jn Jo Js Lh Lu Lw Ly Lz Mc Md Me Mf Mi Mj Mk Ml Mp Mq Mr Mv Mx My Mz Na Nb
Nd Nf Ng Nh Ni Nk Nl No Nq Nr Ns Nu Ny Oe Of Og Oy Oz Pc Pd Pe Pg Po Pz Qc) No(Hq Hu Hv Hw Hx Ii Ij Il In Io Iq Iu Jm Jn Lh Li Lj Lu
Lw Ly Lz Mc Md Me Mf Mg Mh Mi Mj Ml Mp Mq Ms Mt Mx My Na Nb Nd Ne Nf Ng Nh Ni Nl Nn Nq Nt Oe Of Og Oy Pa Pc Pd Pe Pf Pg
Po Pz Qa Qc Qd) Mt(aA Fp Hu Io Iq Jj Jl Jm Ly Mg Mj Mk Mq My Nb Nc Ng Nl Nn Ns Nu Og Oi Oy Pc Qc) Po(Hu In Io Jm Lw Ly Ma Me
Mh Mj Mp Mq My Na Ng Nn Oe Og Oy Qc) aA(Fp Hr Is Jg Jj Lw Ly Me Mj Ml Nb Nc Nl Nn Ny Og Om Pc Qc) Is(Hu Io Jl Jm Lv Ly Mj Mq
Ms My Ng Nn Ns Og Oy Pc) Mp(Hq Jm Jn Js Ly Mj Mk Mz Ng Ns Of Og Oy Pd) Jj(Hr Iq Mx Nl Nv Ny Pa Qb) Om(Iq Mf My Nb Ns Og Oy
Qc) Nn(Hu Iv Mi Mr Nd Pa Pe) Io(Iq Jg Jp Mx Mz Ny Og) Jg(Mg My Og Oy) Nq(Hu Jm Ng) Ly(Mr Pa Pe) Mw(My Oy) Ny(Ii Og) LwMx
MkPa NaOg Inlq} Ny{Io(Hr Hw Ij Il Im In Is Jg Jh Jj Jl Jm Jn Jo Jp Lh Lu Lv Lw Lx Ly Ma Me Mi Mn Mp Mr Mt Mu Mx My Na Nb Nc Nd
Ng Nh Nk Nl Nm Nn Nq Ns Og Oi Om Oy Oz Pa Pc Pe Pf Pg Po Qb Qc) Jh(Hq Hu Hx Ii Ij Il Im In Jg Jk Jl Jm Jo Lu Lv Lw Ly Ma Mc Md Me
Mf Mh Mk Ml Mn Mp Mt Mu Mx My Nb Nc Nd Ng Ni Nl Nn Nq Ns Og Oi Oy Pc Pg Qb Qc) Jj(Hq Hr Hx Ij Il Im Jo Lv Lw Lz Md Me Mh Mj
Ml Mn Mp Mt My Nb Nc Nd Nl Nn Nq Ns Nv Og Oy Pa Pc Pd Pg Qc) Mt(Fp Hu Ij Il Im Jg Jl Jm Lv Lw Ly Me Mj Mk Mn Mp Mx Nc Ng Nh
Nl Nm Nn Nq Nr Ns Og Oi Oy Pc Qc) Mj(aA In Iq Ir Is Jl Lh Lx Ma Mi Mp Mr Mu Mx Mz Na Nb Nc Nf Nn No Og Oi Om Oy Pa Pe Pf Po)
Om(Hq Hx Ij Il Im Jm Lu Ma Md Mf Mh Mk Ml Mp Mq My Ng Nl Nn Nq Ns Og Oi Oy Pz Qc) Is(Hu Il It Jg Jl Jm Js Lw Lx Ly Me Mk Mp
Mq Mu My Nb Ng Nn Og Oy Pc Qb Qc Qd) Nn(aA Hr Hu Im Jm Jn Mf Mk Mx Na Nb Ng Nl Og Oi Oy Qc) Nb(aA Im Jg Lw Ma Mn Mp Mu
Mx Na Nm No Nq Pc Pf Po) Mp(Hq Hu Ii Il Im Jm Ly Ng Nl Ns Og Oy Qc) Mu(Hu Ii Jm Jn Lh Ly My Ng Nl Nq Og Oy Qc) Jg(Hr In Mk Mx
My Ng Ni Nl Og Oi Oy Pa Qc) Pc(aA Hr Ii Im In Mk Mx Na Og Oi Pz Qc) Me(aA Ii Im Jm Mf Mx Na Ng Og Oi) Ng(Im Jk Jl Jn Lw Lx Ma Nq
Pf) Im(Hu Jm Lw Ly Nc Nh Og Pg) Qc(Iq Ir Jn Lw Mz No Pf) Lx(Hq Hu Jm Ly Mh Oy) Lw(aA Ii Mx Og Oi) Jm(Lh Mi Nd Nq Po) Jl(Ii Og Oi
Oy) Mw(My Og Oy) Hr(aA Ma Mx) Lh(Hu In Ly) Ii(Nc Nm) NoQd NqHu} Mt{Jl(Fp Hq Hr Hu Hw Hx Ih Ii Ij Il In Io Is Iu Jk Jm Jo Lh Lu Lw
Lx Ma Mc Me Mf Mi Mj Mk Ml Mn Mr Ms Mv Mw Mx Nc Nd Ng Nh Nl Nm Nq Ns Nu Nv Of Og Pd Pg Po Qb Qc Qd) Hr(Fp Hu Ij Io Jg Jh
Jj Jn Lv Lw Lx Ly Ma Me Mj Mk Mn Mp Mq My Nb Nc Nf Ng Nm Nn Nr Ns Nv Og Oi Om Oy Pc Pf Qb Qc) Nb(aA Hw Ii Ij In Ir Is Iv Jg Jo
Lh Mi Mr Mu Mz Na No Nt Nv Om Pa Pe Po Qc) Mj(Hw Hx Ii Iq Ir Is Iv Jn Jo Lh Mp Mr Mx Mz No Nv Om Pa Pe Pg Po) Qc(Hq Hu Hx Iq Ir
Jg Jh Jn Lh Lv Lw Mn Mr Mz Nm Nn Nv Om Pc Pe Pg) Mk(Hq Hx Jg Jh Jn Jo Lh Lv Mn Mp Nc Nl Nm Nn Nv Om Pa Pc Pg) Hu(Hq Hx Io Jg
Jh Jk Jn Jo Lh Lx Mi Mn Mp My Nq Nv Pg) Om(aA Io Jh Lh Lv Ma Mf Mr Mx My Ng Nl Nq Nv Og Oy) Io(Hx Jg Jh Jn Jo Lh Lv Me Mp Nc
Nl Nv Pc Pg) Ly(Hx Lh Lv Lx Mi Mr Nd Nl Nv Pa Pg Po) Ng(Hq Hx Jh Jn Lh Mn Mp Nm Nn Nv Of Pg) Jg(aA Hx Lv Ma Mf Mx Nl Nq Nv
Oy Pd Pg) Jn(Fp Jh Jm Js Lw Mu Nn Oi Oy Pc Qd) Hx(Jh Lv Lw Me My Nn Og Oy Pc) Nv(Jh Jj Jm Nq Oi Oy Pc) Lv(Jh Nc Nl Nm Nq Og)
Nl(Jh Lw Mn Nm) Oy(Hq Jh Mw Pg) aA(Lw Me Nn Pc) Nq(Jh Mn Nn) Mr(Lh No Pe) Pg(Jj Jm Nr) Mf(Me Pc) FpLh NcNk} Om{Nb(aA Hq
Hw Ii Im Ir Is Iv Jg Jl Jm Lh Lu Lv Lx Mf Mi Mn Mx Nd Nf Nl Nn No Nv Pg Po Qb Qe) Lh(Fp Hq Hu Ii Il Io Jk Jm Jt Lv Lw Ly Ma Mf Mh Mj
Mk Ml Mq Mr My Nf Ng Nn Oy Pa Pc Qc) Nl(aA Hu Io Jl Jm Lv Mf Mp Mq My Ng Nk Ns Nv Og Oy Oz Pa Pg Qc) Jn(aA Fp Ij Io It Jt Lx Mf
Mj Mp Mu Mv Mx Nd Nq Ns Og Oi Po Qc) Io(Hr Hx Is Lv Lx Mf Mi Mr Mx Nd Nv Oy Pa Pe Pg Qb Qe) Nv(Hu Ii Im Is Jj Jm Ml Mv Mx My
Ng Og Oi Oy Qc) Qc(aA Hq Hr Hx Iq Ir Lv Mf Mr Mx Mz Oy Pg) Mj(aA Iq Is Lx Mi Mr Mx No Pa Pe Po) Og(Hr Hx Is Jh Jl Lv Ma Mf Oe Qb
Qe) Ng(aA Jl Lx Mi Mr Nd Nq Pe Pg Po) Oy(Hq Hr Hx Il Jl Lv Mf Mw Mx Pg) Mf(Hq Hr Lv Mx Ns Pc Pg Qb) Jm(Hx Lx Mi Mr Nd Pg Po) Lv(Hr Is Jh Mx Nc Oi) Hu(Lx Mi Mr Nd Nq Pa) Pg(Hr Ii Mk Mx My Oi) Ly(Lx Mi Mr Nd Pa) Hr(Lx Mq Nd Oi) My(Hx Jl Mw) Nq(aA Jl) Pa(Is Mk) MxOz HxOi JhJl} Jh{Jl(Fp Hq Hr Hu Hv Hw Hx Ii Ij Il In Io Iq Ir It Iu Jg Jk Jm Jn Jp Js Lh Lj Lu Lv Lw Lx Lz Mc Me Mf Mi Mj Mk Ml Mn Mr Mu Mv Mw My Mz Na Nd Ne Nf Ng Nh Ni Nk Nl Nm Nq Nr Ns Nu Nv Of Og Oi Oy Pd Pe Pf Pg Po Qc Qd) Lv(Hr Hu Io Is Iv Lh Mf Mg Mp Mx My Nc Ne Ng Nh Nk Nl Nq Og Oy) Nv(Hu Im Io Jj Jm Lh Mg Mk Mx My Na Nb Ng Nl Nq Ns Og Oi Oy Pz) Jn(Hr Io It Jt Mj Mp Mu Nn Nq Og Pc Qc) Lh(aA Hu Io Jm Jt Ly Mj Mp Mq Nb Ng Nn) Pg(aA Hr Hu Io Jm Mf Mk My Ng Oy Qc) Ng(Hx Is Mi Nd Pa) Hx(Io My Og Oy) aA(Hr Me Nb Pc) Is(Hu Io Pa) Mw(My Oy) Hr(Nn Og) OgPa} Is{Lv(Fp Hr Hu Hx Ii Io Iq Ir It Iv Jg Jk Jl Jm Jn Js Lh Ly Me Mf Mi Mj Mk Mn Mp Mq Mr Mu Mv Mx My Mz Nb Nc Ng Nh Nl Nm No Ns Og Oy Pa Pc Pe Po Qb Qc Qd) Jl(Fp Hu Ii Il Io Iv Jm Ly Me Mk My Ne Ng Nh Nk Nq Nv Og Oy Pa Qb Qc Qd) Nv(Hr Hu Io Jm Ly Mj Mk My Nb Ng Nr Og Oi Qb Qc Qd) Mj(aA Hq Hx Lh Lx Mn Mp Mr No Pa Pe Pg Po) Jg(Hr Io Jt My Nb Ng Oy Pa Pg) Io(Me Mn Mp Nm Nn Pc Pg) Pg(Il Im It Jm Nr) Nn(aA Jn Lx Qc) Lx(Iu Lw Mi) Me(aA Mf) Mp(Mk Mq) Mw(My Oy) NoMr LwaA LyLh MvMy MzQc} Lh{Mu(Fp Hq Hu Hv Hw Hx Ii It Iu Jm Jn Lw Ly Mc Md Me Mf Mh Mj Ml Mq Mr Mv My Nb Nf Nk Nq Ns Nt Oe Oy Pd Po Qc) Lx(Hq Hu Hx Ii Il Md Mh Mi Ml Mv My Oy) Mj(aA Im Jg Jl Jn Ma Mp Mz Nn No Pf Qb) Nn(In Io Mf Mk Nf Nk Oe Qc) Jg(Hu Io Jt Ly My Ng Oy) aA(Hr Jj Me Mr Nb Pc Qc) Lw(Im In Jt Na Oe Qc) Im(Lv Mq Nv Pg) In(Hq Ly Me Pc) Mw(My Oy) Jj(Io Qc) NmJt NqHu LyJl QbJm} Jn{Lx(Hq Hr Hu Hx Il Ir Iv Jm Lj Lw Ly Mh Mj Ml Mu My Na Nf Nn Ns Oy Pc Pg Qc) Mu(Fp Hu Hx Im Jm Lv Me Mj Mp Mq Mx Nl Nv Og Oy Pg Qc) Qc(Jg Jl Jp Lw Me Mp Nn No Pc Pf Po) Mp(Hq Jm Js Ly Me Ng Nn) Jg(Hr Io My Og Oi Oy) Mj(Mr No Pe Po) aA(Lw Me Nn Pc) Im(Nn Pc Pg) Nq(Hu Jm) Mw(My Oy) Mx(Lw Pc) Io(Nn Nv) PoOy NoMe NgJk JjNv} Nv{Jj(Hq Hr Hu Hv Hx Ih Ij Il Im In Io Iq It Iv Jg Jo Lu Lv Lw Ly Ma Mc Me Mf Mg Mh Mj Mk Ml Mp Ms Mx My Nc Ne Ng Nh Ni Nl Nm Nn Ns Of Og Oy Pa Pc Pd Pf Pg Qb Qc Qd) Im(Hr Hu Io Jm Ly Ng Nn Og Pc) Lx(Hu Jm Ly Ng) Mu(Hu Nb Ng Og) Jg(Io Nb Ng Og) Mx(Io Lw Mj) NoMj MwOy NbaA} Mw{Oy(aA Hr Hv Hw Hx Ih Ij Im In Io Iq Ir It Iu Jg Jk Jp Js Jt Lj Lw Lx Lz Ma Mc Md Me Mf Mg Mi Mj Mk Ml Mn Mp Mq Mr Mu Mx Mz Nc Nd Ne Nf Nh Ni Nk Nl No Nq Nr Ns Nu Oi Oz Pa Pc Pd Pf Po Qb) My(Ma Mx Nl Og) Mx(Hu Lw) HuJs} Jg{Io(Hr Hx Mi Mr Mx Nb Nc Nl No Og Pa Pe Pg Po Qb) Ng(Lx Mp Mr Nd Nq Pa Pe Pg Po) Hr(aA Lx Og Oi Pa) Nb(aA No) MzQc HxOg} Lx{Jo(Il Io Mh Mj My Oy Oz) Mj(Hw Ir Iv Js Nr) Ly(Nh Oe Pg) Nb(Hw Ir Iv) Hu(Ij Of) Jm(Jl Qb) Oy(My Pg) MaHr MhNl MrIv NcNk HqPg QcJs} aA{Me(Hr Hx Ij Il Jo Nd Ne Nh Nl Nq Pg) Lw(Hr Jo Mx Nb Nl Pg) Pc(Hr Jo Nb Nd Nl Nq) Nn(Hr Nb Nd Nl Pg) Pg(Mj Nb)} Pg{Im(Hr Hu Il Io Ir Jm Ly Mz Ng Nn Og Oy Pc) Mu(Hu Jm Ly Nq) Mx(Io Lw Mj) NoMj HrJj} Jl{Og(Hr Io Mj Nd Nh Pa) Nl(Io Jj Jm

Figure 35 Continued

Ly Nk) Mj(Mx No Pa) Nd(Im Oi) Qc(Iq Mz) IoPa} Nn{Nl(Hr Io Nk) Mf(Hw Mx) Qc(Ir Pe) MjPe HrOg} Po{Mj(Hw Js Oy) Ly(Nb Qc) LwNb QcOy} No{Mj(Hx Mp Qb) Nb(Lv Mn) QbJm} Ma{Lv(Hr Mx) Hx(Io Ng)} LvNlJj MjHxPf MuOeOg

Unconstrained panels with 3 analytes, where 3.3E-8 >= 'AUC p-value' > 1.0E-8. Contains 7,141 panels of 295,240 total panels evaluated. : Oh{Jg(aA Fp Hq Hv Hw Ih Ii Ij Im Ir Is It Iv Jk Jn Jo Jp Js Lw Lx Ly Lz Mc Md Me Mg Mi Mj Mk Ml Mn Mp Mq Mr Mv Mz Na Nb Nd Ne Nf Ni Nk Nm Nn Ns Oe Of Om Oz Pa Pd Pe Pf Po Pz Qb Qe) Mt(aA Hq Hv Hw Ih Ii Ij Il In Ir Jj Jn Jp Li Lu Lz Mc Md Mf Mg Mh Mi Mn Mr Ms Mu Mv Mw My Mz Nb Nc Nd Ne Nh Ni Nk Nm Nn Og Pa Pc Pd Pe Pf Po Pz Qd Qe) Nh(aA Fp Hu Hv Hw Ii Ij In Ir It Jm Jn Jo Js Lx Lz Mc Me Mf Mg Mh Mi Mm Mn Mp Mr Ms Mv Na Nb Nd Ni Nl Nm Ns Nu Of Og Oz Pd Pe Pf Po Pz Qb) Nw(aA Hv Ih Im Iq Ir Is Iu Jj Jk Jn Jp Js Li Ly Mc Md Me Mf Mg Mp Mq Ms Mv Mw Mz Na Nc Nd Nf Ni Nk Nn Nq Nr Nu Oe Oz Pc Pf Pz Qc) Mm(Hq Hu Hv Ii Ij Il In Ir Is It Iv Jm Lu Lx Md Me Mf Mi Mj Mn Mp Mq Mr Ms My Mz Nf Ng Nm No Nq Ns Oe Og Om Pd Pe Po Qb Qc Qe) Lw(Hv Hw Ii In Ir Is It Iu Iv Lj Lx Lz Ma Mc Mg Mh Mj Mk Ml Mn Mp Mr Ms Mw Nb Nd Ne Nm Nr Ns Nu Oy Oz Pa Pd Pe Pf Po Qb) Jh(Ih Iq Ir Is It Iu Jk Jp Js Jt Ly Lz Md Me Mg Mj Mp Mq Mu Mw Mz Na Nf Ni Nk Nn Nt Of Oz Pz Qa Qe) Jl(Il Im Iq It Iu Jk Jm Jp Js Jt Lx Md Mg Mi Mn Ms Mu Mv Mw Mz Na Nf Nm Nn No Nt Nu Oe Of Pz Qa Qe) Om(Fp Ii Il Im It Iu Iv Jm Js Ly Ma Mc Me Mh Mi Mn Mq My Nc Nd Nm Nr Ns Oi Oy Oz Pf Po Qb Qe) Hx(Hv Hw Ih Ij Im In Ir Is Iu Iv Jj Jo Jp Md Mi Mn Mw Mz Na Nb Nf No Pa Pd Pz Qa Qe) Io(Hu Ih Il It Iu Jk Js Jt Lu Ly Ma Md Me Mh Mj Ml Mq Ms Mu Ne Nf No Nu Oy Oz Pf Qa) Of(Hq Hu Hv Ij Il In Iv Jj Lh Lx Ly Ma Mc Mf Mp Mw Mx Nd Ne Ni Nn No Ns Oi Pc Pd Qc) Jo(aA Hu Il In It Lh Lu Ma Mc Me Mh Mi Nl Nm Nn Nq Nr Ns Nu Oi Ok Oy Pc Pf Po Qe) Nl(Fp Ih Im Iq Jp Jt Li Lu Lz Md Mk Ml Mn Mp Mq Nd Nf Ni Nq Nu Pc Pd Pz Qb) Jq(Il In Ir Iu Jm Jp Js Li Lu Lz Ma Mc Md Mh Mz Nc Nf Nr Nt Oy Pe Pz Qa Qb) Nm(Fr Hq Hu Hw Jm Lh Lj Lu Mf Mn Mp My Ns Nv Oe Og Oi Oy Qb Qc) Mx(Hr Hu Hv Ii In Ir Iv Jm Lj Lx Ma Mi Ml Ms Mw Nb Ns Og Po) Hq(Hv Ij In Ir Is Iv Jn Lj Ly Mf Mh Mw Na Nb Nc Oy Pc Qc) Qc(Hv Hw Ii Ij Il In Jm Lx Md Ms Mw Ng Ni Nr Pd Qd) aA(Hu Ih Is Lu Lv Ly Lz Mh Mw Nc Ne Nv Og Oy Oz Pa) Lh(Hv Hw Im Iq Ir Is Jk Jp Md Mz Na Nc Nu Qa Wm) Pg(Ih Ii Iq Iu Jp Li Md Mv Mw My Pa Pf Qd Qe) Lx(Il Ma Mh Ms My Nd Nk Oe Og Oy Oz Pd Qe) Mf(Hv Hw Ij Il In Ir Iv Ms Mw Ni Nn Og Wm) Po(Fp Il Lj Ma Mh Mn Mv Ns Og Oz Pa Qb) Nb(Ly Me Mh Ml Mq Nr Ns Oz Pa Pd Qb Wm) Ng(Il Jk Lj Mg Mv My Nd No Nq Og Ok Pd) Jm(Hw In Ir Is Js Lj Ms Nq Nr Pd Qb Qc) Pe(Il Lj Ma Mc Mh Mn Ms Ne Nr Oe Pa Qb) Hu(Hv Ii Il In Iv Ni No Nq Pa Pd Qe) Jn(Ij In Ir Md Me Mq Mz Nf Oy Pz Qa) No(Iq Mk Ml Nd Nv Oe Ok Qd) Iv(Il It Lj Me Mq Ne Pd Qb) Og(Hv Hw In Lj Ni Oe Pd Qe) Pb(Im Jj Li Ly Nq Oy Oz Qd) Ml(Hv Ij Mj Na Nf Ni Nr) Ir(Js Me Mk Mq Ne Nr Pd) Is(Fp Hr It Lj Mk My Ne) Nv(Iq Iu Jk Jt Li Mw Qe) Hw(Fp Ij Me Mk Ms Nr) Ii(Il It My Nf Nr Oy) Mr(Fp Mh Nk Oy Pa) Hr(Iu Jj Jt My Qd) Ik(Fp Im Md Ms Nn) Qe(Il Lj Lv Oi) Pa(Mi Mj Nd Wm) Pc(Mn Mw Nn Pd) Ns(Ms Mz Ni) My(Jj Md Mi) Ne(Lj Ly Mp) Wm(Jp Mz) Fp(Hv In) Fr(Jt Qd) Nq(Jk Mu) Js(In Lj) NnOk LvLi MiNd MjJk MpNi MsIl MwPd NfLj OeOi} Ok{Nc(Hr Hu Hw Ih Ii Ij Ir Jg Jj Jk Jo Jp Js Li Lu Md Mf Mi Mn Mp Mr Ms Mu Mv Mw Mz Na Nd Ne Nf Ng Nl Nm Nn No Nq Nr Nt Of Oz Pc Pc Po Qa Qd Qe) Mt(aA Hr Hv Hw Hx Ih Ii In Iq Iv Jk Jp Js Lu Lv Lx Lz Mc Mi Mn Mp Ms Mu Mv Mw Mx Na Nd Nh Nq Nv Nw Nx Of Pa Pd Pf Pz Qb Qe) Om(Hq Hu Hv Hx Ir Iu Iv Jl Jp Lh Li Lj Lw Lx Lz Ma Mc Md Mi Mk Mn Mp Ms Mv Mw Nd Nf Ni Nv Oz Pc Pd Pe Pf Qa Qe) Ny(Fr Hq Hr Hv Hw Hx Ih Im In Ir Jg Jp Js Lv Lz Ma Mg Mi Mn Mu Mv Mx Nd Nf Ni Nk Nm Nq Nv Oe Pe Qb Qe) Nl(Hq Hv Il In Iv Jg Jk Jl Jo Js Lh Lu Mc Mf Mg Mk Mp Mu My Mz Nf Nh Nv Of Oy Oz Pe Pf Pz Qa Qe) Me(Hw Ii In Iq Iu Jl Jm Lv Mg Mi Mk Mp Mw Mz Nd Nf Nn Nq Nr Nu Of Pa Pc Pd Pe Pf Pz Qd) Mq(Fr Hq Hu Hv Ih Ij Ir It Iv Jg Lj Lx Ly Mc Mh Mp Mu Mw My Nn Nq Nv Pa Pc Pe Pf) Io(Hv Ij Im In It Jj Lj Lu Lw Lz Md Mf Mg Mk Ms Mu Mv Mx Mz Na Ne Nf No Nr Qd) Og(Fr Hu Ii Ij It Iv Li Lv Lx Ly Mc Mn Mu Mv Mx Nd Nm Nu Of Oi Pf Po Pz Qd Qe) Pg(Hr Hw Ij Ir Iu Jl Jp Lh Lu Ma Mi Mp Ms Mv Mx Mz Na Nd Ne Nf Nm Nq Nv Pa Po) Jl(Hu Hx Il Jm Jn Jt Lh Ly Ma Mg My Ne Nu Nw Of Oi Oy Pa Pf Pz Qb Qc Qe) Pa(Fp Hr Hw Ih Iv Jg Jk Jm Lh Mc Mg Mk Mn Mu Ne Nh Ni Nk Nu Oy Po Pz) Ml(Fr Hv Ih Ij Ir Jm Lw Lz Mc Md Mf Mg Mz Na Ne Nf Nk Oe Of Pc Pf) Jt(Ij Iq Ir It Iv Jm Jp Lx Mp Mr Mu My Mz Nq Nt Of Oi Po Qc Qd) Fp(Hr Hv Ii Jm Ly Mc Mf Mh Mz Na Ni Nm Of Oi Oz Pd Qa Qd Qe) Mj(Hu Hv Hw Ij It Jg Li Mf Mn Na Ni Nm Nn Of Oz Pc Pz Qc Qe) Nh(Fr Hu Il Jm Lh Lv Mi Mp My Nk Nm Nn Nq Nu Nv Oy Oz Qc Qd) Ns(Hu Hx Ir Iv Jo Js Mk Mr Ms Mv Mx Nn No Nu Of Oy Pz Qe) Jh(aA Hr Ih Ij Im Iq Ir Md Mg Mz Nf No Nr Nt Of Pz Qa Qe) Jn(Hw Ii Iq Ir Iu Jj Js Li Md Mf Mr Mu Mv Nf No Nt Pe Po) Nx(Hv In Is Iv Jj Li Lj Ma Mc Mg My Ne Ni Nr Nw Oi Pc Qc) Lw(Hu Hx Ii Iu Jm Lj Ly Ma Mf Mh My Nd Nk Oe Oi Oy Qb) Nw(Fr Ij In Iu Jj Jk Md Mh Mk Ms Mv Mw My Nr Nt Oy) Qc(Hq Hr Jg Lh Li Lj Mg Mz Ne Oi Pc Pd Pe Pf Qb) Oi(Hq Il Iv Jg Jk Lh Ly Mw My Nk Pc Pd Pf Qb) Oy(Jk Lh Lj Lx Ma Mp Mv Nk Nq Nv Oe Qb) Mg(Hr Is Jk Lh Mp Mw My Nk Nv Pf) Qb(Il Jm Lj Lu Ly Ma Mh Oe Pz Qd) Nb(aA Iq Ir Iu Lz Mx Na Nf Nr) Nk(Il Jm Li Mc Mw My Nn Nu Pz) Is(Iq Iu Jg Jk Jo Md Mu No Pz) Ly(Fr Hq Hx Lj Pe Po Qd) Oe(Hu Hx Il Lj Ma Mw My) Nn(Hq Il Iv Lu Pc Qa) Jq(Hr Hw Iq Iu Lz Mk) Nv(Hu Im Lh Lj Lx Mc) Nu(Hq Jk Ma Pe Pf) Mr(Im Mp Nq Nt) My(Hq Ma Mb Ne) Il(Hr It Lj Mh) Qd(Hx Lx Pe Pf) Jm(Lh Mi Nd Nq) No(Iq Lx Mz) Ng(Jg Nd Po) Hu(Jk Lx Mw) Pz(Hq Hr Pf) Fr(Mx Ne) Ma(Hx Of) Mb(Mf Mv) Na(Lj Nd) Lh(Pc Wm) NqMu HrJj JoJr LjPc} Jr{Pg(Hr Hx Ij Il It Iv Jk Jm Jp Lj Mc Mg Mh Mk Ml Mn Mq Mr Mx My Nb Nc Nd Ne Nh Nk Nl Oe Of Pa Pe Pf Pz Qa Qd) Nv(aA Hq Hv Hw Ih Ii Ij It Iv Jp Lh Li Lj Lz Mf Mi Mr Mv Mw Mx Nb Nd Nf Ni Nk Nu Oz Pa Pb Pd Pe Qa Qe) Lh(Hq Hw Hx Ih Ii Ij Jo Jt Lj Lz Mc Md Mi Mk Mx Mz Ne Nh Nk No Nq Nt Nx Oe Oi Pa Pd Pe Qb Qd) Is(Hv Hw Ir Iu Iv Jn Jo Jt Lu Lz Md Mh Ms Mw Mx Na Ne Nf Ni No Nt Nu Oe Oi Oz Pd Pe Pz Qe) Lv(Fp Hu Hx Il Iv Jk Jp Lz Mc Mh Mi Mq Mr Mw Mx Na Nd Ne Ng Nk Ns Oi Pa Pe Po Pz Qb Qd) No(Hv Hw Ij In Io Jo Jp Js Lj Mf Mg Mi Mk Mx My Na Nd Ne Nt Nu Oe Oz Pd Pe Qa Qb Qe) Mn(Hv Hw Ih Ii Ij Iu Jm Jn Jo Jp Lz Md Mf Mg Mq Ms Mw My Mz Nc Nf Nr Nu Oe Of Oz) Ny(aA Hq Hv Hw Iq Ir Iu Iv Jo Li Lz Mf Mr Ms Mv Mw Mz Nf Nr Nu Oe Oz Pd Pe Qa Qe) Pf(Hw Ii Iq It Jj Li Lz Mf Mg Mh Mv Mw My Nb Nc Ne Ni Nk Nr Nu Oe Of Oy Qa Qe) Ml(aA Hr Hu Hw Ii It Jp Jt Li Lj Mc Mg Mk Mq Mw My Nd Nk Nu Oi Qa Qd Qe) Po(Fp Hq Hv Ii It Jj Jn Jp Mc Mk Mw Mx Na Nd Nu Oe Oz Pd Qa Qb Qd) Nx(Hr Hv Hw Ii Il Iu Jm Li Lj Mf Ms Mv Mw Nb Nc Nf Nk Nr Nt Of Oz) Nh(Il In It Jj Jp Jq Lj Mi Mr Mv Mw Mx My Na Nd Nl Pa Pe Qb Qd) Nc(Hu Hv Hx Il Iv Jj Jp Lj Mc Mr Mw My Nb Nd Oe Og Pe Qb Qd) Jq(Ih Ij Io Ir Iu Jn Jp Lj Mc Md Mk Nf Ng Nk Nr Ns Nu Og Qe) Nl(Fp Hu Js Li Mc Mh Mv Mx Na Nd Ne Nk Og Oi Qa Qb Qd) Io(Fp Hw Ii Il Iq Jn Jo Lj Mc Mg Mh Mv Nb Ng Qd Qe) Og(Hr Hw Hx Il Jp Lj Mc Mh Mx Nd Ng Ns Oe Of Qb Qd) Jj(Fp Iq Iu Jp Lj Lw Mg Mi Mv Mw Mx Ns Pc Pe Qe) Pa(Fp Hu Il Jm Jp Js Lz Mh Mi Mq Nb Nk Ns Qb) Mj(Hq Hr Hv Ih Mc Md Ms Ns Nu Oi Oz Pz Qa) In(Hx Il Iv Jo Mg Mh Mw Mx Ne Ng Nk Nu Qb) Jk(Hw Ij Iq Ir Iu Jo Md Mw Mz Nf Nu Qa Qe) Jp(Hr Hu Hx Ii Il Lj Mi My Ng Nk Oi Qb) Nm(Hq Iu Li Lu Md Ms Mz Nf Nk Nr Nt) Fp(aA Li Mi Mv Mw Na Nd Ns Qb) Mw(Ir Jn Mh Na Ng Oi Pz Qb) Hx(Mq Nd Ng Ns Oi Oy Qb Qd) Jl(Jn Jt Md Ms Mz Nf Nt Qa) Nq(Iu Li Lj Ms Pd Qe) Mi(Il Js Li Mh Nk Qb) Mr(Hu Il Js Nb Nk Qb) Mv(Lj Mx Ng Ns Oi Qb) Qc(Hv Ij Lu Ly Nr Oy) Nt(Im Lw Lx Nb Pc) Me(Hq Jo Li Pd) Mx(Js Ng Nk Oi) Nd(Hq Js Ng Ns) Pe(Hu Il Nb Qb) Mq(Iv Nb Nr) Hr(Ir Iu Nr) Im(Ni Oi Oy) Jt(Lx Ma Pc) Ly(Lw Pb) Ii(Hu Oy) NsNe LxIu MpJo MuaA MzLj NaQb NfPb IkIr ItIv} Nw{Nl(aA Hq Il Im It Iv Jj Jo Jp Lj Lu Lx Me Mh Mi Mj Mm Mn Mp Mq Mu Mw Mx My Mz Nm Ns Nv Oe Oy Oz Pc Pf Pg Pz Qd Qe) Mt(Hq Hv Hx Ii Ij Im In Iv Jn Jp Li Lu Lx Ma Mc Mf Mi Mr Ms Mu Mv Na Nb Nf Nm Nu Nv Ny Oz Pa Pd Pe Pf Pg Po Pz) Om(Fr Hx Ii Ij Is Iv Jg Jh Jl Jm Jn Js Lw Lx Ly Mc Me Mf Mh Ml Mp Mr Mz Nc Nd Nf Ns Ny Oi Oz Pc Pd Pe Po Qb Qd) Is(Fp Fr Hq Hu Hv Hw Ii Ij In Ir It Iv Js Ly Mk Ml Mq Mr Na Ng Nm Nv Ny Of Oz Pa Pe Pg Po Qa Qb) Lh(Fp Hq Hx Ij Im In Jg Jn Jo Li Lu Lz Mc Mf Mk Ml Mn Mp Nk Nq Nr Ns

Figure 35 Continued

Figure 35 Continued

Lu Lx Ly Ma Md Mi Mj Mk Ml Mn Nc Nd Nh Nu Oi Pf Po Qb Qc Wm) Oy(aA Hv Ir Is Iv Jh Jk Jn Jo Lx Mi Mm Mn Mp Mr My Nb Nd Nf Nq Og Pa Pe Po Qb Wm) Lh(aA Hv Hx In It Jn Lu Mc Md Me Mn Mp Mu Mx Nq Nr Ns Nu Og Oi Oz Pd Pg Po Qb) Qc(Il Io Is Jh Jo Lx Lz Ma Mi Mp Nb Nc Nd Nf Ns Og Pe Po Qb Qe) Mf(Hv Ii Iq Is Jo Lu Lx Me Mh Mj Ml Mn Mp Mq My Mz Nf Nv Pe) Io(Hq Hw Iq Ir Iu Jg Jh Jl Jo Ma Mn Mp Mq Nb Ns Nx Og Po) Hr(Im Jg Jh Lw Ma Mc Me Mh Ml Mm Mn My Nc Nq Ns Pc Pz) Jn(Hq Ii Jk Lz Ma Mc Me Mh Mk Ml Mn Mu Nc Nh Nn Nu Qd) Mx(Fp Jh Jl Jm Lu Mn Mp Mq Nc Ns Nx Og Oi Pa) Lv(Hx Jl Lx Ml Mp Mq My Nd Ng Nh Ns) Nb(Iq Iu Jk Lz Mp Mu My Mz Nr) Nv(Hx Ly Md Mg Mh Mj Mk Nq Pz) Mm(Hx Ma Mp Ns Oi Pg Qb Qe) Og(aA Hu Ir Mp Mq Nd Ns Oz) Ng(Hx Iu Jk Mp Nj No Pa) aA(Fp Hu Jt Ml Mr Pa Qd) Wm(Iq It Jh Oe Pg Pz) Mk(Hx Lx Mi Pe Po) Ly(Mp No Pe Po) Mq(Jo Pa Pe Po) Nj(Jm Jo Ne Ni) Hx(Md Me Ml Nc) Jl(Mj Ne Nh Pa) Pg(Hu Ij Im Lu) Ma(Lx Mi Mp) Jm(No Pa Pe) Mj(Ir Qb) Nf(Lx Mi) Jt(Ir Mr) NnPc Melv Mllq ImNx Islt QbOi} Mb{Nv(Hq Hv Hx Ii Ij Il It Iv Jk Mc Me Mf Ml Mn Mq Mv My Na Nb Nk Nl Nm Oz Pd Qe) Pf(Hv Hw Im It Iu Jm Jo Js Lz Mf Mh Mi Mj Mr Mv Mw Nc Nn Nq Nr Of Pc Pd Qa Qc) Pe(Hr Ih Im Ir Jk Js Lh Lj Lz Me Mf Mi Mw Mx Na Nc Nf Nl Pa Pz Qa Qc Qe) Pg(Iv Jm Lj Lu Mr Ms Nj Ns Of Oy Pc Po Qa Qb Qd Qe) Jg(Hx Iq Iv Jj Lh Lu Lv Mp Mr Ne Nf Ng Qd) Jn(Hw Hx Iu Lu Mf Mv Mw Nb Nf Nl Ns Og Qe) Nn(Ih In It Jj Lh Lu Ma Mg Mx Oy Qb) Ir(It Me Mh Mw Ni Nq Nt Oe Po Pz Qc) Jh(Im It Jm Jo Jt Lj Ly Me Mq Mv Nu) Mm(Ih Iv Jj Mh Mz Pb Po Qa Qb Qe) Qd(Ik Io Jj Lv Lw Ma Mh Mu Nh Po) Md(Ih Im Io Mz Nc Ng Oy Oz Pa) Mp(Ih Lw Lz Mr Mx Ne Nf) Mu(In Jt Ms Na Ni Of Pz) Nh(Hq Ih Jk Jp Lh Qb Qe) Lx(Iu Jo Lz Mn Mq Mw) Ma(Lz Mr Ne Nf Nx) Mz(Ne Nm Nt Og Oi) Nj(Iv Jk Jp Qe) Lw(Hx Pa Qa) Pb(Hq Lz Nr) Wm(Hq Im) Lv(Js Mr) Ly(aA Lh) My(Mw Po) Jj(Jk Pd) Pa(Jp Nm) NbOy HrJl IoLh} Ls{Jl(Hq Hx Ih Im Jk Jo Jp Lh Lj Lu Lx Ma Mc Mf Mi Mn Mr Mu Mv Mx Na Nb Nd Ni Nl Nm Nr Ns Pd Pf Pg Po Qe) Lv(Hq Hv Hw Ih Il Iu Jj Jo Jp Jt Li Lj Lz Ma Mc Mh Ml Ms Na Nd Ne Nf Nq Nr Nt Of Oz Pf Pz Qe) Nx(Fp Ij Il In Iq It Jg Jj Lw Lx Me Mf Mk Ml Mm Mp No Nv Pg Qb Qc) Nv(Ih Ii Im Jh Jj Lu Mc Mf Mh Ms Na Nc Ne Nh Nm Nn Nq Pz) Pg(Hr Hu In Jh Jj Lx Ly Me Mk Mp My Ng Nn Og Oy Qb Qc) Jh(Hr Hx Jm Jo Lh Ly Mc Nb Nc Ne Nh Nk Nl Nq Qc) Jg(Hq Hu Hx It Jm Lh Lu Mf Mj Og Oi Qc) Mm(Hr Ii Ij Ik In Jm Mr Mz Nb) Io(Hq Hx Iv Jp Lw Ne Nh Og Pf) Ik(Jj Jk Mg Mu Nf Nl Nq Pc) Lh(aA Hu Il Jm Lw Mp Mq Nn) Pb(Hu Iq Iu Jj Ly Lz Mk Pz) Lx(Hu Hx Jm Mp Mr Nb Oe) Nj(Jj Jm Ni Oy Pz Qd) Nn(Hr Hx Mf Mp Pc) Lx(Hr Hx It Mf Og) Wm(Mq No Pa Pd) Mp(Ne Nh Og Qc) Mj(li Mi Mv) Hu(Jk Mw Nq) Og(Hq Hx Mn) Ly(Nd Po) Qc(Iq Jn) Pc(aA Hx) NmJt MuNb HqJm} Nj{Jh(Fp Hr Hv Il Im Io Iu Iv Jo Li Ma Md Mh Mj Ms Mw My Na Nc Ne Nh Nl Ns Pc Pd) Pf(Hw Im Iv Jk Lw Md Mf Mx Na Nd Nf Nm Oe Pa Pg Qa Qb Qe) No(Hv Hw Ih Ij Ir Jj Jn Jo Jt Lu Mc Mu Na Nd Nh Oy Pe) Nv(Hu Hw Hx Iq Iv Jm Jn Lh Ly Mi Mr Nb Nf Nm Oy Qb Qe) Nn(Jk Lj Mc Mg Ml Ms Mv Mw Ns Of Pc Pe Qd) Qe(In Iu Ma Mc Md Mg Mj Mw Mx Nk Nr Oz Pz) Jp(Hv Ih Iu Jg Jo Js Lu Lw Ma Md Mn Ms Pg) Hx(Io Ir Jn Lv Lw Md Na Og Oi Pa Pe) Ir(Hw Ma Mj Mm Nf Nk Nm Nr Oe Qb) Jg(Hv Im In Lv Mf Mj Nd Nr Nt Qa) Pa(Il Jk Jm Mj Mn Ms Nx Oi Po) Lx(Ih Lh Mg Mu Mz Ne Nh) Mp(Hv Lv Lw Mr Ns Pe) Lh(Ik Mw Nm Nq Qa) Mx(Hq Jk Lv Nx) Nb(Ms Na Nm Qb) Jn(Ik In Io Nd) Po(Iq Lu Mg) Im(Hr Mv Qd) Qa(Mf Mi Ml) Pe(It Ma Qb) Lv(Jj Mz) Mr(Mn Qb) Mu(Ik Pb) Nf(Mm Mw) WmNx NaHq IvPb} Pb{Jl(Fp Hu Ih Iq Iu Jk Lj Ly Lz Mc Me Mg Mj Mk Ms Mv Nc Nd Ng Nq Oe Of Oy Qb Qd Qe) Po(Lu Mc Mi Ml Mn Na Ne Nf Ns Og Oz Pd Qc) Ir(Hw Hx Ij In Lv Lz Mh My Na Nd Pc Qe Wm) Nv(Hx In Jg Jm Jn Lw Mp Mq Ng Nm Nu Og Oi) Jh(Fp Iq Iu Jg Jk Jp Lz Mn Nh Nm Og Oz) Nx(Fp Hr Ih Lu Ly Nd Ne Nh Nl Nq Ns Pc) Qa(Il Iu Jg Jo Jp Ma Ml Mr Mx No Oz) Jn(Jk Lw Mj Mk Mp Nc Nl Oz Pf Pg) Pa(Io Js Lx Mm Mp Mq Mx Nr Nt Wm) No(Ij Jk Lv Ly Me Mg Nc Nh Pz) Pe(Hw Ij Il Ly Lz Mh Oy Qe) aA(Hq Il Jk Lv Lx Mh Mp Nh) Pf(Hv Ij Lw Mq Mx Na Pg) Jg(Io Jt Mi Mp Mq Qb) Hx(Ik Iv Jp Mn Nt) Ii(Hr Io Jj Na Qe) Mp(Ij It Mi Pg) Mr(Im Jk Mk Qe) Nb(Jk Mw Oz Pd) Nn(Mq Mx Pg) Mu(Il Iv Pd) Nm(Hr Nr) Lx(Na Ni) Mn(Hw Nr) Iv(Oe Qe) Jt(Ma Wm) Pg(Hv Jm) LvMx Mjlm MwHu HwJk} Mm{Lv(Fp Hq Ii Ij In It Jg Jt Mc Me Ml Mq Ms Mu Mw My Mz Na Nf Ng Ni Nl Nu Oe Of Oy Oz Qa Qc Qe) Nv(Hx Il Iq Jg Jk Li Lz Ma Mc Md Mi Mj Mn Mp Mq Ms Mv Mw Nc Nd Nk Nl No Nr Pd Pf Pg Qa Qb) Lh(Hq Ij In Iq Jg Jk Li Lx Lz Ma Mc Md Mg Mi Mk Mu Mv Mx Nb Nm Nq Og Oz Pd Po Qe) Jl(Fp Ii Il Jp Jt Lj Lw Lx Mc Md Mi Nr Nu Po Qd) Io(Hq Hr Jg Jh Jk Jt Lx Nr Nt Pf Qa) Nx(Fp Jg Mc Mk Mu Nn Nq Of Oz Pg) Ik(Hv Iq Jg Jk Lu Mu Mz Pe Qd) Pg(Hq Hu Im Ir Ly Mk Oy) Hx(Jh Jj Lw Mp Ng Oi) Jh(Iv Og Pa Qb Qe) Wm(Hv Ii Jt Qb) No(aA Ly Mp Oz) Pa(Iv Oz Pe Po) Po(Hu Ly) Ng(Ir Of) aA(Fp Ni) MpHr IrOi QeOg} Wm{Mz(Il In Iv Jg Jk Jt Lz Ma Mn Nb Ne Nn Nr Of Og Qa Qb Qd Qe) Pg(Fp Hw Io Lj Mc Md Mg Mj Mn Mq Ms Ni Nq Nr Ns Nu Oe Qc Qe) Pd(aA Hq Hx Js Lv Ma Mr Ms Mx Nh Ni Nk Oi Pa) Nx(Hw In Iu Jo Li Lj Me Mj Mr Nc Nl Ns Pe) Lh(Iu Jn Lu Mr Ms Mu Mv Nd Nl Nr Oe Pe) Pa(aA Hu Hx Il Jn Ma Mx Nc Nd Nf Nr Oe) No(aA It Lx Md Mn Nc Nh Ni Nm Qc) Lx(Hx Io Ir Iu Jm Mc Mg Of Oy) Jp(Hq Hu Io Iu Md Mh Ne Og Qb) Nb(Hx Ij Il It Og Oy) Ir(Fp Jh Mj Mr Oy) aA(Mn Mr Nn Og Pz) Mw(Ly Mx Nf Pz) Jn(Jg Mi Nq Of) Lw(Jt Pz Qe) Hx(Ih Ma Nn) Mk(Jg Qa) Ik(Iq Mn) Iv(Jg Lv) PoHr LyQb MfJh MqPe IhOy JkJm JoOn} Ik{Hv(Hu Hx Jm Li Lz Mh Mi Mp Ng Nl Nm No Nr Nt Og Qb) Jh(Hv Ij Jj Jk Jp Ly Ma Mq My Mz Na Nd Nm Ns Oy) Nn(Il Ir Iv Lu Mi Mj Mk Nb Ne Nm Nr Oz) Jg(Ih Ij Jj Jt Lw Mp My Ng Og Pd Qa) Pf(aA Ii Ij Il Mn Mw Ne Nm Pa Pg Qe) Lh(Fp Hq Jp Lw Mn Mw Nm Nq Po Qe) Pg(Iv Jm Lz Ma Mi Mk Mp Mr No Pa) Jn(Hw Li Mn Mw Na Nl Nt Pa Qe) Ma(aA Ir Iv Jo Lv Mi Qb) Po(Iv Mj Mn Nm Nu Qc) Lx(Mw Ne Oi Pz) Mp(Hw Ij Nh Nl) Nx(Hx Nm Qb Qe) Mx(Hq Lv Nm) No(Oe Qb) Hx(Jj Nm) aA(Li Mn) MiMw MuOf} Nx{Im(Hx In It Iu Jj Ma Mj Mn Mp Nc Ne Ni Nv Of Oi Pd Qc) aA(Hu Jn Lh Ma Mn Mp Mq Mr Mu My Nf Ng Oy Pg Qd) Jh(Hu Hw Ii Jo Jp Mg Ms Mv Nh Nn No Nu Nv Oe) Po(Hq Hx Ii Mc Mf Ml Mx Nb Ns Nu Pd) Og(Hx Jl Ma Mr Mx Mz Nn Nq Oe Pf Qb) No(Fp Ih Ir Js Ma Mz Ns Nu Qb) Mu(Ih Iu Lv Ma Mn Ms Nc Ne) Lx(Lz Nh Pd Qa Qb) Jj(Hx Il Jn My Pg) Nn(Hw Jn Nl Nr) Mr(Ln Jm Mp Na) Ma(Hr Hx Mx) Pf(Hr Ng Nl) Ly(Mi Nd) Mp(Nb Pe) Mx(Lv Pc) Na(Lh Mz) In(Lh Qb) Io(Mi Qb) NdJm IiJl IqQc JgOi} Jn{Mu(Hq Il Io Iv Jo Jp Js Lu Lw Ly Mf Ml Mn Mr My Nh Ni Nn Nq Ns Pc Pd Po) Lx(Fp Hv Hw Ij Lz Mc Mi Mx Mz Nd Ng Nl Nq Og Qa Qd) Mp(Ln Io Jg Ml Mw Mz Na Ns Oy Pc) Jh(Il Jg Jk Lv Lw Mn Nd Ng Oy Po) Nn(Hr Js Mf Mj No Oi Pe Po) Lw(Hr Hx Lh Mf Na Nl) Jg(aA Hu Il Mf Ns Pz) Po(Hu Jm Ly Me) Qc(Jk Ma Nm Nq) Nm(Io Jt) Nq(Mj Ng) Lv(Jj Na) Im(Jm Nv) MaHr MeMx MiMj OiPc} Jh{Lv(Hx Iq Ir Jm Jo Js Lx Lz Ma Mh Mi Mr Mz Nn No Ns Of Pf Pg Qb) Nv(Hr Hx Il Lu Lx Lv Mf Mp Nc Of Pa Pf Qc) Pg(Hx Il Im Jj Ly Mu Mx Na Ns Og) Lh(Lw Me Mk Mr My Og Oy Qb) Jl(Jt Li Md Ms Nt Oe Qa) Ng(Hq Iu Lx Mp Mr Po) Nn(aA Hx Nl Nq) Hr(Jg Qb Qe) Hx(Jg Ma Mk) Og(Jo Mp Nl) Pa(Jg Mp Oy) Ly(Lx Mi) Nb(No Po) Io(Mn Qb) LwaA MkQb} Nv{Jj(Fp Hw Ii Ir Iu Jm Jp Js Lh Li Lj Lx Lz Md Mi Mn Mq Mv Mz Na Nb Nd Nf Nk Nq Nr Nu Oi Oz Pe Po Pz Qa Qe) Im(Lw Mh My Nc Nh Nl Oy) Io(Hu Mu Na Ng Nl Og) Mx(Jg Jm Nn Oi Pc) Mu(Hr Jm Nq Oy) Nn(Ng Oi) Lx(Hq Oy) NoJm MzQc} Jl{Io(Iv Jg Jj Lh Ma Me Mj Mp Mx Nc Ne Nh Nm Nn Pf) Nd(aA Jm Lh Lx Mu No Pa Qc) Og(Il Im Lw Me Mp Mw Nl Nm) Hr(Im Lx Ma Mj Mq Nn) Mj(Mr Nf Nh Pf) Pa(Im Jg Jj Oi) Nb(Iv Jg No) Nm(Jt Mg) Nq(Jg Nn) Jm(Lh Mi) LwMx NcNk NgLh Nhlm} Lh{Mu(Il In Iq Js Lu Lz Mi Mp Mx Nd Nl Pc Pg) In(Hu Lv Mj Mp Mq Mr Qb) Im(Fp Il Jj Ly Mr Nn) Jg(Mg Mk Mv Nb Oi) Mj(Io Jp Na Pa) Nn(Hu Mv Pc) aA(Hu Lw Ml) Ma(Hu Io) NoMq LvLy LwJm LxNa MnIo JjJo} Pg{Im(Hq Iq Iv Js Lu Lw Lx Me Mh Mi Mr Mx My Nb Nc Ne Nf Nh Nk Nl Ns Pe Pz Qb Qc) Mu(Hr Io Mx Ng Og Oy) Jg(Mg Mx Nb Og) aA(Ly Mr Pc) Lx(Jo Ng) MxPc NlJj} Jg{Io(aA Hq Hw Ii Iq Ir Iv Lx Mp Mz) Pa(aA Hu Iv Jm Lx Mx Nl Oi) Ng(Iq Iu Jk No) Hr(Lw Mg No) Hx(Mk Oi) NqaA LvMx LxLy IrJt} Lx{Jo(Fp Hx Me Ml Mq Nn Pd) Hr(Me Mn Oy Pf) Ly(Ne Qe) My(Il Ms) Ir(Mr Qc) Oe(Lw Mp) Oy(Il Of) NfJs HuHx HwIn JkJm} Mw{Oy(Il Iv Jo Mh Na Nm Nn On Oe Og Pe) LzHu MuNl MyHr NbaA} aA{Me(Io Ir Of Og) Pc(Il Mx Nh Oe) Nn(Jo Nq) Lw(Il Nh) MnNb} Po{Ly(Me Nl) MaHr Mjlj NcNk QbJm LjOy} Hr{Pf(Io Lv Mj Og) LvJj} Lw{Mx(Ii Of) Oe(Mi Mr)} Ma{Hx(Hu Jm Mj Oy)} Mp{MiOe Mjlr MkPe} MzQbQc

Figure 35 Continued

Unconstrained panels with 2 analytes, where 1.0E-6 >= 'AUC p-value' > 0. Contains 1,209 panels of 7,381 total panels evaluated. : Et(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Ji(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Wm) Jn(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe Wm) Oh(aA Fp Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Lh Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nd Ne Nf Ng Nh Ni Nj Nk Nl Nm No Nq Nr Ns Nt Nu Nv Nw Nx Ny Oe Of Og Oi Ok Om Oy Oz Pa Pb Pc Pd Pe Pf Pg Po Pz Qa Qb Qc Qe) Jr(Fp Fr Hr Hu Hv Hw Hx Ih Ii Ij Ik Il Im In Io Ip Iq Ir Is It Iu Iv Jg Jh Jj Jk Jl Jm Jn Jp Jq Js Lh Li Lj Lv Lw Lx Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nu Nv Nw Nx Ny Oe Of Og Oi Ok Om Oz Pa Pb Pc Pe Pf Pg Po Pz Qa Qb Qc Qd Qe Wm) Ok(Fp Fr Hq Hu Hv Hw Hx Ih Ii Ij Ik Il Io Ip Iq Ir Is It Iu Iv Jg Jh Jj Jk Jl Jm Jn Jq Js Jt Lh Li Lj Lu Lv Lw Lx Ly Lz Ma Mb Mc Me Mf Mg Mh Mi Mj Ml Mm Mn Mp Mq Mr Ms Mt Mu Mw Mx My Mz Na Nb Nc Nd Ne Nf Ng Nh Ni Nj Nk Nl Nm Nn No Nq Nr Ns Nu Nv Nw Nx Ny Oe Of Og Oi Om Oy Oz Pa Pb Pc Pd Pe Pf Pg Po Pz Qa Qb Qc Qd) Nw(aA Fp Fr Hq Hr Hu Hv Hw Hx Ii Ij Ik Il Im In Io Ip Iq Ir Is It Iv Jg Jh Jl Jm Jn Jo Jq Js Lh Lv Lw Lx Ma Mb Mc Md Me Mf Mh Mi Mj Mm Mn Mp Mq Mr Mt Mu Mv Mw Mx My Mz Na Nb Nd Nf Ng Nj Nl Nm Nq Nr Ns Nv Nx Ny Oe Of Og Oi Om Oy Pa Pb Pc Pe Pf Pg Po Pz Qa Qb Qc Qd Qe Wm) Mt(Fp Fr Hq Hr Hu Hw Hx Ii Ik Il Im Io Ip Jg Jh Jj Jk Jl Jm Jn Jo Jp Jq Lh Lj Lv Lw Lx Ly Ma Mb Mk Mm Mn Mp Mx My Nb Ng Nj Nl Nm Nn Nq Ns Nv Nx Ny Og Oi Om Oy Oz Pb Pc Pd Pe Pg Po Qb Qc Qe Wm) Om(aA Fr Hq Hr Ik Il Io Ip Ir Is Jh Jl Jn Jo Jq Lh Lv Lx Ma Mb Mf Mi Mm Mn Mp Mq Mr Mx Nb Nc Nd Nj Nl Ns Nv Nx Ny Og Oi Oy Pa Pb Pe Pg Po Qb Qc Qe) Fr(aA Hr Hu Ij Ik Il Ip Is Jh Jm Jn Jo Jq Lh Ly Mb Mf Mh Mm Mp Mx Nc Ne Ng Nh Nj Nl Nq Nv Nx Ny Oe Og Oi Oy Pb Pg Qb Wm) Jq(aA Hw Hx Ii Im Ip Iq Is Jg Jh Jk Jl Lh Lv Lx Mb Mi Mm Mn Mp Mr Mu Nb Nd Nl Nn No Nq Nv Nx Ny Pa Pe Pg Po Qb Wm) Ny(Ii Ik Im In Io Ip Is Jg Jh Jj Jl Jm Lw Lx Ly Ma Mb Me Mj Mm Mp Mu Mx Na Nb Nc Ng Nj Nn Og Oi Oy Pb Pc Pf Wm) Ip(aA Hx Ir Is Iv Jg Jh Jj Jk Jl Jn Jp Lh Lx Ma Mi Mm Mn Mp Mr Mu Mz Nn No Nv Nx Pe Pf Pg Po) Is(Hq Hx Ik Io Jg Jl Lh Lv Lw Lx Ma Mb Me Mj Mk Mm Mn Mp Nj Nm Nv Nx Og Pb Pc Pg) Jl(Hr Im Io Jg Jh Jj Mb Mj Mm Mx Ne Ng Nh Nj Nl Nn Og Oi Pa Pb Pf) Nj(aA Hx Ir Jg Jh Jn Jp Lx Mp Nn No Nv Pa Pf Po Qa Qe) Mm(aA Hx Ir Jh Jn Lh Lv Nb Nv Nx Pa Pe Pg Po Qe) Mb(aA Ir Jh Jn Lh Lx Md Mu Nn No Nv Pe Pf Pg) Nx(aA Im Jg Jh Lx Mp Mu Mx No Og Pb Pf Po Wm) Wm(Ih Jn Jp Lh Lx Mz Nb No Nv Pa Pd Pg) Jh(Hx Ik Jn Lh Lv Mp Nv Og Pa Pb Pg Qb) Pb(Hx Ir Iv Jn Lh No Nv Pe Pf Po Qa) Jg(aA Hr Hx Ik Io Jn Lx Mp Pa) Lh(aA Ik Im In Mp Mu Nn) Lx(Ij Jn Jo Js Oe) Mu(Hw Ij Jn Nv Pg) Ik(Nn Nv Pf Pg) Nv(Im Jj Mx) Pg(aA Im Jj) Nn(Hr Jn) MaHx MeaA MpJn MwOy Unconstrained panels with 2 analytes, where 1.0E-5 >= 'AUC p-value' > 1.0E-6. Contains 681 panels of 7,381 total panels evaluated. : Jl(aA Fp Fr Hq Hu Hv Hw Hx Ih Ii Ij Il In Iq Ir It Iu Iv Jk Jm Jn Jo Jp Js Jt Lh Li Lj Lu Lv Lx Ly Lz Ma Mc Md Me Mf Mg Mh Mi Mk Ml Mn Mp Mq Mr Ms Mu Mv Mw My Mz Na Nb Nc Nd Nf Ni Nk Nm No Nq Nr Ns Nt Nu Nv Nx Oe Of Oy Pc Pd Pe Pg Po Pz Qa Qb Qc Qd Qe) Is(aA Fp Hr Hu Hv Ih Ii Ij Il Im In Iq Ir It Iu Iv Jh Jj Jk Jm Jn Jo Jp Js Jt Li Lj Ly Lz Mc Md Mf Mg Mh Mi Ml Mq Mr Ms Mt Mu Mv Mw Mx My Mz Na Nb Nc Nd Ne Nf Ng Nh Ni Nk Nl Nn No Nq Nr Ns Nt Nu Oe Of Oi Oy Oz Pa Pd Pe Pf Po Pz Qa Qb Qc Qd Qe Wm) Fr(Hq Hv Hw Hx Ih Ii Im In Io Iq Ir It Iu Iv Jg Jj Js Lu Lw Lx Lz Mc Md Mg Mi Mj Mk Mq Mr Mu Mv Mw My Mz Na Nb Nd Nf Ni Nk Nm Nn Nr Nu Of Oz Pa Pc Pe Pf Po Pz Qa Qc Qe) Om(Fp Hv Hw Hx Ih Ii Ij Im In Iq It Iu Iv Jg Jk Jm Jp Js Lu Lw Lz Mc Md Me Mh Mj Mk Ml Ms Mu Mv Mw My Mz Na Ne Nf Ng Nh Ni Nk Nm Nn No Nq Nr Nu Oc Oz Pc Pd Pf Pz Qa Wm) Mt(aA Hv Ih Ij In Iq Ir It Iu Iv Js Jt Li Lu Lz Mc Md Me Mf Mg Mh Mi Mj Ml Mq Mr Ms Mu Mv Mw Mz Na Nc Nd Ne Nf Nh Ni Nk No Nr Nt Nu Oe Of Pa Pf Pz Qa Qd) Ny(aA Hr Hu Hx Ij Il Jp Lh Lu Lv Mg Mh Mk Ml Mn My Nd Ne Nh Ni Nk Nl Nm No Nq Ns Nx Of Pa Pg Po Pz Qa Qb Qc) Jg(Hq Il Iv Jh Lh Lu Lv Lw Mb Md Mi Mm Ms Mu Mx Mz Nb Ne Nh Nl Nn No Nv Og Oi Oy Pb Pe Pf Pg Po Qb Qe Wm) Nw(Ih Iu Jj Jk Jp Jt Li Lj Lu Ly Lz Mg Mk Ml Ms Nc Ne Nh Ni Nk Nn No Nt Nu Oz Pd) Mm(Hr Hv Hw Ii In Io Iv Js Lu Lw Lx Mb Md Mp Mr Mu Mz Nf Nn No Nr Pf Qa Qb) Jh(aA Hr Il Io Ir Iv Jo Lx Mh Mi Mn Mr Mx Nc Ne Ng Nh Nl Nn Oi Oy Pf Po Qe) Mp(Hr Hu Ij Ir It Js Lw Lx Mb Mf Mi Mu Mx Nc Nh Nl Nn Nv Pe Pf Pg Qb) Ip(Hq Ih Ik Im Iq Jt Li Lz Mb Mj Mv Mw Mx Na Nb Nc Nm Pa Pb Pd Qa Qe) Jq(Hq Hv Il Iu Lu Lw Lz Ma Mg Mv Mw Mx Nc Nm Nr Nt Nu Pd Pf Qe) Nn(aA Hu Hx Io Mx Nh Nl Nq Nx Og Oh Oi Oy Pb Pc Pg Qb) Lx(Hr Hw Hx Ik Io Ir Iu Iv Mk Mn Mw Mx Nm Nr Oy Pz Qb) Jn(Ik Jk Jp Lv Lw Ma Me Mn Mx No Nq Nx Pe Pf Po Qc) Nx(Ik In Io Iq Ir Jj Jp Ma Mr Mz Na Nq Pe Qb) Ok(aA Hr Im In Jp Md Mk Mv Nt Qe Wm) Mb(Iq Lz Ma Mr Mz Pa Po Qa Qd) Jr(aA Hq Jo Jt Lu Ly Nt Oy Pd) Mu(Hx Il Jo Mw Nj Pb Qb) Nv(aA Io Jm Ng Og Oi Pf) Po(Ly Ma Me Oe Oy Wm) Mw(Ij Ir Js Mf Mg Mi) Lh(Lw Ly Ma Mj Na No) Oh(Jj Jt Li Nc Qd Wm) aA(Lw Mn Pb Pc Wm) Pb(Ii Pa Pg) Wm(Ir Qd) Mx(Ii Pg) Nj(Nb Pg) Hr(Ma Pf) HxPf IkQe Unconstrained panels with 2 analytes, where 1.0E-4 >= 'AUC p-value' > 1.0E-5. Contains 929 panels of 7,381 total panels evaluated. : Nv(Fp Hq Hr Hu Hv Hw Hx Ii Ij Il In Iq Ir It Iv Jn Jo Jp Js Lh Li Lj Lu Lv Lw Lx Ly Lz Ma Mc Md Mf Mg Mh Mi Mj Mk Mn Mq Mr Ms Mw My Mz Na Nb Nc Nd Ne Nf Nh Ni Nk Nl Nm Nn No Nq Nr Ns Nu Nx Ny Oe Of Oy Oz Pa Pc Pe Pg Po Pz Qa Qb Qc Qe) Nn(Fp Hq Hv Hw Ih Ii Ij Il Im In Iq Ir It Iu Iv Jj Jk Jm Jo Jp Js Jt Li Lj Lu Lv Lw Lx Ly Lz Ma Mc Md Me Mf Mg Mh Mi Mj Mk Ml Mn Mq Ms Mu Mv Mw My Mz Na Nb Nc Nd Ne Nf Ng Ni Nk Nm Nr Ns Nu Oe Of Oz Pa Pd Pe Pf Po Pz Qa Qc Qd Qe) Jh(Fp Hq Hu Hv Hw Ih Ii Ij Im In Iq It Iu Jj Jk Jm Jp Js Jt Li Lj Lu Lw Ly Lz Ma Mc Md Me Mf Mg Mj Mk Ml Mq Ms Mu Mv Mw My Mz Na Nb Nd Nf Ni Nk Nm No Nq Nr Ns Nt Nu Oe Of Oz Pc Pd Pe Pz Qa Qc Qd Wm) Jg(Fp Hu Hv Hw Ih Ii Ij Im In Iq Ir It Iu Jj Jk Jm Jo Jp Js Jt Li Lj Ly Lz Ma Mc Me Mf Mg Mh Mj Mk Ml Mn Mq Mr Mv Mw My Na Nc Nd Nf Ni Nk Nm Nq Nr Ns Nt Nu Oe Of Oz Pc Pd Pz Qa Qc Qd) Mp(aA Hv Hw Hx Ih Ii Ik Il Im In Iu Iv Jj Jk Jm Jp Lv Lz Ma Mc Md Me Mh Mj Mn Mq Mr Mv Mw My Mz Na Nb Ne Nf Ni Nm No Nq Nr Ns Nu Oy Oz Pa Pb Pc Pd Po Qa Qe Wm) Pg(Hq Hr Hu Hv Hw Hx Il Io Iq Ir Jm Jn Jp Js Lh Lu Lw Lx Ly Ma Mc Me Mf Mh Mi Mr My Mz Na Nc Nd Ne Nf Ng Nh Nk Nl No Ns Nx Oe Of Og Oy Pa Pc Pe Pf Qb Qc) Mm(Fp Hq Ih Ij Ik Il Iq It Jj Jk Jo Jp Jt Li Lj Ma Me Mh Mi Mj Ml Mn Mq Ms Mv Mw Mx Nb Nd Ne Nf Ng Nh Ni Nj Nm Ns Nt Nu Og Oi Pd Qd Wm) Nx(Fp Hq Hu Hv Hx Ih Ik Jm Js Lh Lj Lu Lw Ly Lz Md Mg Mi Mn Ms Mw Nb Nd Ne Nf Ng Nh Ni Nj Nk Nm Ns Nt Nu Oe Oy Oz Pa Pc Qa Qc Qd Qe) Jn(aA Hq Hr Hu Hw Hx Ii In Io Iq Ir It Iu Iv Jj Jq Lh Li Lz Mg Mi Ml Mr Mv Mw My Mz Na Nb Nc Nd Nh Nl Nm Nr Ns Ny Oe Og Oi Pe Qa) Mw(aA Hu Hv Hw Ik In It Jm Jp Lh Lw Lz Mc Md Mh Mj Mk Mr Mx Mz Nb Nc Nd Nf Nj Nl Nq Nr Ns Ny Oe Og Oz Pc Pe Pf Po Wm) Ny(Fp Hq Hv Hw Ih Iq Ir It Iu Iv Jk Jo Js Jt Li Lj Lz Mc Md Mf Mi Mq Mr Ms Mv Mz Nf Nr Nt Nu Oe Oz Pd Pe Qd Qe) Ip(Fp Hr Hv Hw Ii Iu Jm Js Lj Lu Lv Lw Md Mh Mk Mq Ms My Nd Ne Nf Nh Nj Nl Nq Nr Nt Nu Og Oy Oz Pc Qb Qd Wm) Jq(Hr Ih Ij Ik Io Ir Iv Jj Jm Jo Jp Js Li Ly Me Mh Mj Mk Ml Ms My Mz Ng Nj Nk Of Og Oy Pb Pc Pz Qa Qd) Pf(aA Hu Il Im Io Jp Lh Lv Lw Lx Ly Mk Mn Mu Mx Nb Nc Ng Nh Nl Nm Ns Oe Og Oi Oy Po Qb Qe) Lx(Hu Ih Ii Im It Jk Jp Lw Ly Ma Mc Mh Ml My Nc Nd Ne Nh Nk Nl Nu Oi Pb Pd Pe Qe) Lh(Hq Hu Il Io It Iu Jj Jo Jp Lv Me Mn Mq My Mz Nj Nm Nr Ns Oe Oy Pa Pc Po Qb Qc) Mu(aA Hr Ii Ir Iu Iv Jp Js Ma Mf Mk Mn Mv Mx Nc Nh Nm Oz Pa Pd Pe Qe Wm) Ma(aA Fr Hw Ik Ir Iv Jp Lv Mi Mr Mx Mz Nb Ne Nj No Pa Pe Qa Qb Qe) Po(Hr Hu Hw Ij Ik Im In Io It Iu Jm Jp Js Mn Mx Nm Nr Qb Qc) Fr(Fp Jk Jp Jt Li Lj Lv Me Ml Mn No Ns Nt Pd Qd) Mb(Ih Im Iv Jk Jp Js Li Lv Lw Mh Mx Nf Nh Qb Qe) Qb(aA Ik Im Jj Jp Lv Lw Mz Nj Nm No Pb) Hx(Ik Im Jj Jp Lw Mn Nm No Og Wm) Om(Hu Jj Jt Li Lj Ly Mg Nt Of Qd) Nm(aA Ik Ir Mx Nj No Pa Pb) Mn(Hr Io Ir Mx Mz Nh Nj No) Jp(Hr Ii Ik Iv Lv Nl Nq Pb) Jk(aA Ik Im Jj Mx Nj Wm) Nq(Hw Ij Js Ly Nj Oe) Ir(Jj Lv Lw Pc Qc) Pb(Mr Nb Nr Nt Qe) Mx(Hq Lv Lw Pe) Nj(Hq Im Pd Qd) Jj(Hq Il Pa Qe) Wm(Jl Md Qe) No(Hr Mj Oe) Ik(aA Qa) Is(Hw Lu) LwQe MjPe NlQa HraA JoOk Unconstrained panels with 2 analytes, where 1.0E-3 >= 'AUC p-value' > 1.0E-4. Contains 1,133 panels of 7,381 total panels evaluated. : Jp(aA Fp Hq Hu Hv Hw Ij Il Im In Io Iq Ir It Iu Jj Jk Jm Jo Js Li Lw Lz Mc Md Mf Mh Mi Mj Mk Mn Mq Mr Ms Mv Mx My Mz Na Nb Nc Nd Ne Nf Ng Nh Nk Nm No Nr Ns Nt Nu Oe Of Og Oi Oy Pa Pc Pd Pe Pz Qa Qc Qe) Ir(aA Fp Hr Hu Hv Hw Hx Ih Ii Ij Il Im In Io Iq It Iu Jk Jm Js Jt Lh Lj Mc Mf Mg Mh Mi Mj Ml Mq Mr Ms Mv Mx My Mz Na Nb Nc Nd Ne Ng Nh Nk Nl Nq Nr Ns Oe Of Og Oi Oy Oz Pe Pf Po Pz Qa Qb Qd Qe) Pf(Fp Hq Hv Hw Ih Ii Ij In Iq It Iu Iv Jj Jk Jm Jo Js Jt Li Lj Lu Lz Ma Mc Md Me Mf Mg Mh Mi Mj Ml Mq Mr Ms Mv My Mz Na Nc Nd Nf Ni Nk No Nq Nr Nt Nu Of Oz Pa Pc Pd Pe Pz Qa Qc Qd) Qb(Fp Hq Hr Hv Hw Hx Ih Ii Ij Il In Io Iq It Iu Iv Jk Jm Jn Js Lz Md Mf Mg Mh Mi Mj Mk Mn Mq Mr Ms Mv Mw Mx Na Nb Nc Nd Ne Nf Nh Nl Nq Nr Nt Nu Of Og Oi Pa Pc Pe Qa Qd Qe Wm) Ma(Fp Hq Hu Hv Ih Ii Ij Il Im In Io Iq It Jj Jk Jo Js Jt Li Lj Lu Lw Lz Md Me Mh Mj Mk Ml Mn Mq Mv Mw My Na Nc Nd Nf Nh Ni Nl Nm Nq Nr Ns Nt Nu Of Og Oz Pb Pc Qd Wm) Qe(aA Hq Hr Hu Hv Hx Ii Il Im In Io Iv Jk Jn Lh Lv Mc Me Mh Mi Mj Mn Mr Mw Mx My Mz Na Nb Nc Nd Ne Ng Nh Nk Nl Nm No Nq Ns Og Oi Pa Pc Pe Pg Po Pz Qa Qc) Qa(aA Fp Hr Hu Hx Ii Il Im Io Iu Iv Jj Jm Lh Lv Lw Lx Mc Md Me Mf Mh Mi Ml Mn Mr Mu Mw Mx My Mz Na Nb Nc Ne Nh Nm Nq Ns Og Oi Pa Pe Pg Po Qc Wm) Im(aA Hq Hr Ih Ii Ik Io Iq Iv Jj Jm Jn Js Lu Lv Lw Lz Mh Mi Mm Mn Mr Mu Mv Mw My Nb Nc Ne Nh Nl Nm No Nq Of Og Pa Pb Pc Pd Pe Wm) Lh(Fp Hr Hv Hw Hx Ii Ij Iq Iv Jk Jm Js Li Lj Lu Lx Lz Mc Md Mf Mh Mi Mk Ml Mr Mx Nb Nd Nf Ng Nh Ni Nk Nq Nt Nu Og Oz Pd Pe Pz Qd) Hx(aA Hq Hr Hu Ih Il Io Iv Jk Jm Lj Lv Ly Mb Md Me Mk Ms Mw Mx My Mz Na Nc Nd Ne Ng Nh Nk Nq Ns Nt Oi Oy Pa Pc Pe Po Pz Qd) Lx(aA Fp Hv Il In Iq Jj Jt Li Lj Lu Lv Lz Md Me Mf Mi Mj Mq Mr Ms Mu Mv Mz Na Nb Nf Ng Ni Nq Ns Nt Og Oz Pa Pc Po Qc Qd) Nm(Fp Hq Hr Hv Ih Io Iq Iv Jj Jk Js Lu Lv Lw Lz Mb Md Mg Mh Mn Mr Mw Mz Nb Nc Nd Ne Nf Ng Nh Nl Nq Og Oi Pe Pg Wm) Po(Fp Hq Hv Ih Il Jj Jk Jo Lu Lw Lz Mc Md Mh Mi Mj Mk Ml Mq Mu Mv My Nd Nh Ni Nk Ns Nu Og Oi Oz Pa Pc Pd Pe Pz) Pg(Fp Ih Ii Ij In It Iu Iv Jk Jo Jt Li Lj Lv Lz Md Mg Mj Mk Ml Mn Mq Ms Mv Mw Nb Ni Nq Nr Nt Nu Oi Oz Pd Pz Qd) Jn(Fp Hv Ih Ij Il Jm Jo Js Jt Lj Lu Ly Mc Md Mf Mh Mj Mk Mq Ms Ne Nf Ng Ni Nk Nu Of Oy Oz Pa Pd Pz Qd) Mn(Hv Hw Ih Ii Ik Il Iq Iv Jj Jk Js Lu Lv Lw Mb Md Mi Mj Mr Mw Na Nb Ne Nf Ni Nl Nq Nr Og Oi Pa Pe) Mu(Fp Hq Hv Ih Ik Io Iq It Jk Jm Li Lv Lw Ly Lz Mc Md Mh Mi Mj Mq Nd Ne Nk Nl Nq Nr Nu Og Oy Qd) Nx(Hr Hw Ii Ij Il It Iu Iv Jt Li Lv Mb Mc Me Mf Mh Mj Mk Ml Mq Mv My Nc Nl Nr Of Oi Pd Pz) aA(Hq Hu Ih Ij Il Io Iv Jj Jo Li Lv Mf Mg Mh Mv Mx My Nc Ne Ng Nh Nl Nq Of Og Oz Pa Pd Pz) No(Hq Ik Iv Jk Jo Li Lu Lv Ly Me Mg Ms Mw Mx My Nc Nd Ne Nh Nl Nm Nu Of Og Pa Pd Pz) Mw(Hr Ih Ii Io Iq Iu Iv Jj Jk Lu Lv Ly Mb Me Ml Mq Mv My Na Nu Oi Pa Pb Pd Pz Qc) Mp(Fp Hq Io Iq Jo Jt Li Lj Lu Ly Mg Mk Ml Ms Nd Ng Nk Nt Oe Of Og Oi Pz Qc Qd) Mm(Hu Iu Jm Ly Lz Mc Mf Mg Mk Nc Nd Nk Nl Nq Oe Of Oy Oz Pb Pc Pz Qc) Ip(Hu Ij Il In Io It Jo Ly Mc Me Mf Mg Ml Ng Ni Nk Ns Oe Of Oi Pz Qc) Jk(Hr Hu Io Iv Jm Ly Mg Mz Na Nc Ne Ng Nh Nl Nv Og Oi Oy Pa Pb) Jq(Fp Hu It Jt Lj Mc Md Mf Mq Na Ne Nf Nh Ni Ns Oe Oi Oz Qc) Mb(Fp Hq Hw Ii Jj Lj Mi Mv Nb Nc Nd Ne Nq Nt Pb Pd Wm) Pe(Hr In Jj Lw Ly Me Mk Ml Mq Na Nj Nq Oe Oz Qc Wm) Nq(Hr Hv Io It Iu Jm Lw Mf Mi Mx Nc Nl Nr Oy) Jj(Hr Ih Ii Iv Jo Li Lv Mv Mx My Nh Nl Of Pd) Pa(Hr Ik Iv Li Lv Lw Ly Mx Na Nh Og Oz Pc) Wm(Hq Ij Iq Iv Js Jt Lw Ly Mr My Nn) Nj(Fp Ii Iv Jt Li Lv Mv Mx Mz Nt) Nv(Ih Iu Jt Me Ml Mv Nt Pd Qd) Pb(Hr Hw Ij Jt Li Mj Mx Mz Pd) Lw(Hr Hv Hw Iv My Nd) Ik(Hq Jl Li Nt Pd Qd) Mx(Ih Ij Mv Nb Pd) Lv(Iv Nc Ne Nh) Ii(Ln Ly Na) Iv(Hq In Nd) Mc(Mz Nb) Mr(In Nn) FrMs NtLy NgJg NhHq LiOi Unconstrained panels with 2 analytes, where 1.0E-2 >= 'AUC p-value' > 1.0E-3. Contains 1,271 panels of 7,381 total panels evaluated. : Pd(Hq Hr Hu Hv Hw Hx Ih Ii Ij Il In Io Iq It Iu Iv Jk Jm Js Lj Lv Lw Ly Lz Ma Mc Me Mf Mh Mi Mj Mk Mn Mq Mr Ms Mv My Na Nb Nc Nd Ne Nf Ng Nh Ni Nk Nl Nm Nq Nr Ns Nu Oe Of Og Oy Oz Pa Pc Pe Pz Qa Qb Qc Qe) Iv(Fp Hr Hu Hv Hw Ii Ij Il Io Ir Iu Jm Js Jt Li Lj Ly Lz Mc Md Me Mf Mg Mh Mi Mj Mk Ml Mq Mr Ms Mv My Mz Na Nb Nc Ne Nf Ng Nh Ni Nk Nl Nq Nr Ns Nt Nu Oe Of Og Oi Oy Oz Pc Pe Po Pz Qc Qd) Pa(Fp Hq Hu Hv Hw Ih Ii Ij Il In Io Iq Ir It Iu Jm Jo Js Jt Lj Lu Lz Mc Md Me Mf Mg Mh Mk Ml Mq Mr Ms Mv My Nb Nc Nd Ne Ng Ni Nk Nl Nq Nr Ns Nt Nu Oe Of Oi Oy Pe Pz Qc Qd) Jk(Fp Hq Hv Hw Ih Ii Ij Il In Iq It Iu Jo Js Jt Li Lj Lu Lv Lw Lz Mc Md Me Mf Mh Mi Mj Mk Ml Mq Mr Ms Mv My Nb Nd Nf Ni Nk Nq Nr Ns Nt Nu Oe Of Oi Oy Pe Pz Qc Qd) No(aA Fp Hu Hv Hw Ih Ii Ij Il In Io Iq Ir It Iu Jj Js Jt Lj Lw Lx Lz Mc Md Mf Mh Mi Mk Ml Mq Mr Mu Mv Mz Na Nb Nf Ng Ni Nk Nq Nr Ns Nt Oi Oy Oz Pc Pe Po Qa Qc Qd) Ii(aA Fp Hr Hu Hv Hw Ih Ij Ik Il Io Iq Iu Jm Js Li Lw Lz Mc Md Me Mf Mi Ml Mr My Mz Nb Nc Nd Nh Nl Nm Nq Ns Nu Og Oy Oz Pc Pe Po Pz Qc Qd Wm) Im(Fp Hu Hv Hw Ij Il In It Iu Jo Jt Li Lj Ly Lz Mc Md Me Mf Mg Mj Mk Ml Mq Ms Mx Mz Na Nd Nf Ng Nk Ns Nt Nu Oe Oi Oy Oz Pz Qc Qd) Mn(Fp Hq Hu Ij In It Iu Jm Jo Jt Li Lj Ly Lz Mc Me Mf Mg Mh Mk Ml Mq Ms Mv My Nc Nd Ng Nk Ns Nt Nu Oe Of Oy Oz Pb Pc Pz Qc Qd Wm) Mb(Hr Hu Hv Ij Ik Il In Io It Iu Jm Jo Jt Lu Ly Me Me Mf Mg Mj Mk Ml Ms My Na Ng Nj Nk Nl Nr Ns Nu Oe Of Og Oi Oy Oz Pc Pz Qc) Li(Hq Hr Hu Hx Ih Il Io Ir Lu Lv Lw Ly Md Mf Mg Mw Mx My Mz Na Nb Ne Ng Nh Ni Nl Nm Nq Ns Nt Oe Of Og Pe Po Pz Qa Qb Qc Qd Qe) aA(Fp Hv Hw In Iq It Iu Jm Js Jt Lj Lu Ly Lz Mc Md Mi Mj Mk Ml Mq Mr Ms Mz Na Nb Nd Nf Ni Nk Nr Ns Nt Nu Oe Oi Oy Pe Po Qc Qd) Nq(Fp Hu Ih Il In Iq Jj Lu Lz Mc Md Me Mg Mh Mj Mk Mq Mr Mv My Mz Na Nb Nd Ne Nf Ng Nh Ns Nu Of Og Oi Oz Pc Po Pz Qd Wm) Pe(Fp Hq Hu Hv Hw Ih Ij Ik Il Io Iq It Jm Jo Js Jt Lj Lv Lz Mc Md Mh Mi Mr Mv Mz Nb Nc Nd Nh Ni Nk Nr Ns Nt Of Oi Pz) Nm(Hu Hw Ij Il In It Iu Jm Jo Jt Lj Ly Mc Me Mf Mj Mk Ml Mq Ms Mv My Na Ni Nk Nr Ns Nt Nu Oe Of Oy Oz Pc Pz Qc Qd) Qa(Hq Hv Hw Ih Ij Il In Iq It Jo Js Jt Lj Lu Ly Lz Mg Mj Mk Mq Ms Mv Nd Nf Ng Ni Nk Nr Nt Nu Oe Of Oy Oz Pc Pz Qd) Qe(Fp Hw Ih Ij Iq It Iu Jm Jo Js Jt Lj Lu Ly Lz Md Mf Mg Mk Ml Mq Ms Mv Nf Ni Nr Nt Nu Oe Of Oy Oz Qd) Mz(Fp Hq Hr Ik In It Jj Js Lj Lv Lw Md Mg Ml Mu Mv Mx Nb Nc Nd Ne Nh Ni Nl Ns Nu Oe Of Og Po Pz Qc) Hx(Fp Hv Hw Ij In Iq It Iu Jo Js Jt Lu Lz Mc Mf Mg Mh Mi Mj Ml Mq Mr Mv Nf Ni Nl Nr Nu Oe Of Of Oz Qc) Hq(Fp Hr Hu Ih Il Io Ir Jm Js Lj Lw Lx Ly Mh Mw My Na Nc Ne Ng Nk Nl Nu Og Oy Oz Pb Pc Pz Qd) Mv(Hr Ih Ij Ik Il Io It Iu Js Lh Lw Md Mr Nc Ne Ng Nh Ni Nl Nr Nt Oe Og Oi Oy Pb Qd Wm) Mx(Fp Hv Ik Il Io Iq Js Jt Lj Md Me Mg Mh My Nc Nd Ne Nh Nk Nl Nr Oe Of Og Oy Pz Qd Wm) Jj(Fp Hu Hw Ij Iq Iu Jm Js Lu Lz Md Mh Mi Mr Mu Nb Nc Nd Ne Nf Nj Nr Nt Nu Pz Qd Wm) My(Fp Hv Ih Ij Ik Iq Js Lv Md Mf Mu Nc Nd Ne Ng Nh Nj Nr Nt Oe Og Oi Oy Pb Qb Qd) Lv(Fp Hr Hv Ih Ij Il Iq Js Lz Md Mh Mi Mr Nf Ng Nl Nr Nu Og Pb Pc Pd Qd Wm) Mu(Hu In Jt Lj Lu Me Mg Ml Mr Ms Na Nb Nf Ng Ni Ns Nt Of Oi Pc Pz Qc) Lw(Fp Hu Ih Ij Il Iq Iu Jo Js Lz

Figure 35 Continued

Mh Mi Mj Mr Nc Ne Nl Nr Nu Oe Qd) Nh(Fp Ih Ik Il Iq Lz Mh Mi Mr Mw Na Nb Nc Nj Nr Nt Pb Pc Qd Wm) Ij(Hr Hv Hw Ik In Io Lz Md Me
Mi Mj Mr Na Nd Nf Nr Og Qc) Qb(Hu Jo Jt Lj Lu Ly Mc Me Ml Ng Ni Nk Ns Oe Oy Oz Pz Qc) Nj(Hr Hv Ih Il Iq Js Lj Lu Lz Md Mi Mj Mr
Ne Nr Nu Oy) Qd(Fp Hr Io Jo Jp Me Mh Mw Na Nc Nd Nl Og Pb Pc Po Qc) Wm(Hr Ik Il It Lj Lz Mi Mj Nf Nl Nr Og Oy Pf Pz Qc) Po(Iq Jt Lj
Mf Mr Ms Na Nb Nc Ne Nf Ng Nl Nt) Ma(Iu Jm Ly Mc Mf Mg Ms Ng Nk Oe Oi Oy Pz Qc) Ih(Fp Hr Hv Ik Jp Lh Na Nd Nu Oe Of Og Pb Qc)
Nb(Fp Hu Ik Il Io Nc Nd Ni Nu Pz Qc) Ir(Ik Jo Lu Ly Lz Md Me Mk Nf Ni Nu) Mw(Fp Il Jt Ms Ne Ng Ni Nk Nt Of) Hr(Fp Ik Io Lj Me Mh Nc
Nd Nt Og) Jp(Jt Lj Lu Ly Me Mg Ml Ni Oz) Nl(Fp Hv Ik Lh Lj Ly Na Nd) Pb(Fp Hv Il Iq Jo Js Mi Nu) Md(Fp Hv Mg Nd Nu Oe Of) Ik(Fp Il Js
Jt Ne Nr Nu) Lh(Jt Mg Ms Nc Ne Of Oi) Mr(Io Me Mj Mk Oe) Nc(Hv Mi Na Nk Nu) Oe(Iq Js Mi Nr) Ml(Hv Mi Nr) In(Hv Hw Jq) Lx(Jm Mg)
Pc(Il Ne) NnNt NrLy NuIo MeHv MiMk NaJs NdIt JlOz JoNx

Unconstrained panels with 2 analytes, where 5.0E-2 >= 'AUC p-value' > 1.0E-2. Contains 1,029 panels of 7,381 total panels evaluated. : Nt(Fp
Hq Hu Hv Hw Ih Ii Ij Il In Io Iq Ir It Iu Jm Jn Jo Js Jt Lj Lv Lw Lz Mc Md Me Mf Mg Mh Mi Mj Mk Mq Mr Ms Mx Mz Na Nb Nc Nd Ne Nf
Ng Ni Nk Nl Nq Nr Ns Oe Of Og Oy Oz Pc Pd Pz Qc Qd Wm) Fp(Hu Hv Hw Ij Il In Io Iq It Iu Jm Jo Js Jt Li Lj Lu Ly Lz Mc Me Mf Mg Mh
Mi Mj Mk Ml Mq Mr Ms Mv Na Nc Nd Ne Nf Ng Ni Nk Nr Ns Nu Oe Of Og Oi Oy Oz Pc Pd Pz Qc Wm) Ih(Hw Ij Il In Io Iq It Iu Iv Jm Jo Js
Jt Lj Ly Lz Mc Md Mf Mg Mh Mi Mj Mk Ml Mq Mr Mz Nb Nc Ne Nf Ng Ni Nk Nl Nr Ns Oi Oy Oz Pc Pz Qd) Nh(Hr Hu Hv Hw Ij In Io It Iu
Jm Jo Js Jt Lj Lu Lw Ly Mc Md Me Mf Mg Mj Mk Ml Mq Ms Nd Ne Nf Ng Nk Nl Ns Nu Oe Of Og Oi Oy Oz Pz Qc) Qd(Hu Hv Hw Ij Il In It
Iu Jm Js Jt Lj Lu Ly Lz Mc Md Mf Mg Mi Mk Ml Mq Mr Ms Mz Nb Ne Nf Ng Ni Nk Nr Ns Nu Oe Of Oi Oy Oz Pd Pe Pz) Nc(Hu Hw Ij Ik Il
In Io Iq It Jm Jo Js Jt Li Lj Ly Lz Mc Md Me Mg Mj Mk Ml Mq Mr Ms Nd Ne Nf Ng Ni Nl Nr Oe Of Og Oi Oy Pb Wm) Nb(Hq Hr Hv Hw Hx
Ij In It Iu Jm Jo Js Jt Lj Lv Lw Ly Lz Mc Md Mf Mh Mi Mk Ml Mq Ms Mv My Na Ne Nk Nl Nr Ns Og Oi Oy Oz Pc) Ne(Hr Hu Hv Hw Ii Ij Il
In Io Iq It Jm Js Jt Lj Ly Lz Md Me Mg Mh Mi Mj Mr Na Nd Nf Nl Nr Ns Nu Of Og Oi Oy Pb Pe Pz) My(Hr Hu Hw Il Io It Iu Jm Jt Lj Lu Ly
Lz Mc Me Mg Mh Mj Mk Ml Mq Ms Mv Mz Na Nf Ni Nk Nl Ns Nu Of Oz Pz Qc) Hq(Hv Hw Ii Ij In Iq It Iu Jo Jt Lu Lv Lz Mc Md Me Mf Mg
Mj Mk Ml Mq Mr Ms Mv Nd Nf Ni Nq Nr Ns Oe Of Oi Qc) Js(Hr Hu Hv Hw Ij Il In Io Iq Jm Jt Li Lj Lz Mc Md Mf Mg Mh Mi Mj Ml Mq Mr
Nd Nf Ni Nk Nl Nr Nu Of Oi Oy Pz) Li(Hv Hw Ij In Iq It Iu Jm Jo Jt Lj Lz Mc Me Mh Mi Mj Mk Ml Mq Mr Ms Mv Nd Nf Nk Nr Nu Oy Oz
Pc Pd Wm) Lv(Hu Hw Ii Io It Iu Jo Jt Lj Lu Lw Ly Mc Me Mf Mj Mk Ml Mq Ms Mv Na Nd Ni Nk Nq Oe Of Oi Oy Pz Qc) Mz(Hu Hv Hw Ij Il
Io Iq Iu Jm Jo Jt Ly Lz Mc Mf Mh Mi Mj Mk Mq Mr Na Nf Ng Nk Nr Oi Oy Oz Pa Pc Pd) Nl(Hr Hu Hw Ij In Io Iq It Jt Lz Mc Md Mg Mh Mi
Mj Ml Mq Mr Nf Ng Nj Nr Ns Nu Oe Og Oi Oy Pb Pe) Jj(Hv Ik In Io It Jt Lj Lw Ly Mc Me Mf Mg Mj Mk Ml Mq Ms Na Ng Ni Nk Ns Oe Og
Oi Oy Oz Pb Pc Qc) Mv(Hu Hv Hw Ii Iq Jm Jt Lj Lu Ly Lz Mc Me Mf Mg Mh Mi Mj Ml Mq Ms Na Nd Nf Nk Ns Nu Of Oz Pz) Mx(Hr Hw It
Iu Jo Lu Ly Lz Mc Mf Mi Mj Mk Ml Mq Mr Ms Na Nf Ng Ni Ns Nu Oi Pc Qc) Nr(Hr Hu Hv Hw Ii Il Io Iq Jm Lj Lz Mc Md Me Mg Mi Mk Mr
Na Nd Nu Og Oy Oz Pz) Iq(Hr Ij Ik Il Io It Iu Iv Jm Lz Mc Md Mg Mh Mj Ni Ns Nu Of Og Oi Qc) Jt(Hr Ii Il In Io Lw Md Me Mh Mi Mq Ms
Na Nd Nq Oe Of Og Oi Oy Pd Qc) Hv(Hu Il Io It Iu Jm Ly Mc Mg Mh Mi Mr Nd Ng Ns Nu Oe Og Wm) Ij(Hu It Jm Lj Lu Ly Mc Mf Mg Mh
Mk Ml Mq Ms Ng Ns Nu Oi Oy) Md(Hr Hw Il Jm Jo Lj Lw Lz Me Mh Mi Mq Na Nk Pb Pc Pd Pz) Mr(Hr Ik Lj Ly Mf Ml Nd Ng Ni Nk Nu Of
Og Oi Oy Oz Pz) Mh(Hu Il It Iu Mg Ms Na Ni Nj Nu Oe Of Pb Pz Wm) Mi(Hr Ik Il Io Lj Ly Mc Nd Ng Ni Nu Of Og Oy Oz) Ii(Hx It Lj Lu Mj
Mk Mq Ms Nf Ng Ni Nk Oe Of Oi) Hr(Hu Il Lu Lz Mf Mg Ms Ng Ni Ns Of Oi Oy Pc) Wm(Hw Iu Lu Mf Mk Ml Nd Ng Ni Nk Ns Oi Pc) Nu(It
Iu Lz Mf Ms Nd Ng Ns Oe Og Oi Oy) Lj(Il Io Iu Lw Lz Mj Mw Nd Nq Of Oi Pb) Pb(It Iu Lw Lz Mq Na Nf Nq Of Oy Oz) Il(Io Lu Ly Lz Ms
Na Nf Nk Og Pz) Lw(It Lu Mf Na Nf Of Og Oy Pz) Nj(Hu Hw In Iu Jo Na Nd Nf Of) Pe(Iu Mf Mg Nf Ng Og Oy Pc) Ik(Hw Iu Iv Jo Nq Of Oy)
Nq(Jo Ml Ms Ni Qc) Mj(Io Nd Oe Og Pz) Iu(Jm Ly Nd Ng Pc) Pd(Jo Lu Mg Ml Oi) Na(Hu Jm Nk Og) Of(Lz Og Pc Po) Mg(Nd Ng Po) Nf(In
Oe Pa) Hw(Me Og Pz) It(Iv Nk Oe) Jo(In Iv Mw) Lu(Iv Pc) Lz(Ni Oz) Mb(Mq Ni) NoJm MuOe PzOi Constrained panels with 3 analytes, where 1.0E-8 >= 'AUC p-value' > 0. Contains 5,087 panels of 295,240 total panels evaluated. : Pb{Et(aA Fr
Hq Hr Hv Hw Hx Ii In Io Ip Ir Is Iv Jh Ji Jk Jl Jn Jo Jr Lh Lu Lw Lx Mb Mi Mr Mt Mu Mz Na Nb Nc Ne Nf Nh Nn No Nr Nt Nv Ny Ok
Om On Pa Pc Pd Pe Pf Pg Po Pz) Ip(aA Fr Hr Hv Hw Hx Ii Ir Is Iv Jg Jh Ji Jj Jk Jn Jo Jp Jq Jt Lh Lx Mb Mi Mp Mr Mt Mu Mz Na Nb Nf Nn
No Nr Nt Nv Nw Nx Ny Oh Ok Om On Pa Pe Pf Pg Po Qa) Is(Fr Hq Hr Hw Ii Ik Io Ir Jg Jh Ji Jo Jq Jr Jt Lv Lw Lx Ma Mb Md Mi Mm Mp Mr
Mt Mu Mz Nb Nf Nm Nn No Nq Nr Nv Nw Nx Ny Oh Om Oy Pa Pc Pd Pe Pf Pg Po) Nx(aA Fr Hq Hw Hx Ii In Iq Ir Iu Iv Jg Jh Jj Jk Jl Jp Jr Jt
Lx Lz Ma Mb Mi Mj Mm Mp Mr Mt Mu Mx Mz Nb Nn No Nr Nt Nw Oh Oz Pa Pe Pf Pg Po Qa) Po(aA Fr Hr Hv Hw Ij Ik In Ir Iv Jg Jh Ji Jj Jl
Jn Jo Jq Jr Lw Ly Mb Mh Mm Mp Mq Mt Mu My Mz Ni Nj Nm Nv Nw Ny Oh Ok Om Oy Pa Pc Qa) Mb(aA Fr Hx Ih Ii Iq Ir Iv Jg Jh Ji Jk
Jn Jp Lh Lx Ma Md Mi Mp Mr Mt Mu Mz Nb Nn No Nt Nv Nw Ny Oh Ok Om On Pa Pe Pf Pg Qa Qb Qd Qe) Jh(aA Fr Hr Hw Hx Ii Ir Iv Ji Jo
Jq Jr Jt Lh Lv Lx Mh Mi Mj Mp Mq Mr Mx Mz Na Nb Nn No Nr Nt Nv Nw Ny Ok Pa Pd Pe Pf Pg Qa Qb Qe) Om(aA Fr Hw Hx Ii Ik Iq Ir Iu
Iv Ji Jj Jn Jo Jr Lh Lx Lz Mi Mm Mr Mt Mx Nb Nd Nl No Nr Nt Nv Nw Ny Og Oh Ok On Oz Pa Pe Pf Pg Qe) Nw(Fr Hq Hr Hv Hw Hx Ii Ij In
Ir Iv Jl Jn Jo Jq Jr Jt Lh Lw Mi Mq Mr Mu Mz Na Nb Nf Ni Nm Nn Nr Nt Nu Nv Oh Ok Pe Qa Qc Wm) Fr(aA Hr Hv Hw Hx Ii Ij In Ir It Iv Ji
Jn Jo Jq Js Jt Lh Lw Me Mq Mr Mt Mx Mz Na Nb Nf Nm No Nr Nt Ny Oh Ok Pa Pc Qa) Mt(aA Hr Hv Hw Hx Ii Ij In Ir Iv Ji Jn Jo Jq Jr Jt Lh
Lw Mr Mu Mz Na Nb Nf Nj Nm No Nr Nt Ny Oh Ok Pa Pe Qa) Pa(aA Hr Hv Hw Hx Ii Ij Ir Iv Jg Ji Jj Jl Jn Jo Jq Jr Jt Lh Lv Lw Ma Mr Mu Na
Nb Nj Nm Ny Oh Ok Pe Qa) Ji(aA Hq Hw Hx Ii Io Ir Iu Jg Jk Jo Lh Lu Lx Ma Mi Mm Mr Mu Nb Nn No Nr Nt Nv Ok On Oy Oz Pc Qc) Jq(aA
Hw Hx Ii Ir Iu Jg Jk Jo Lh Lu Lx Mi Mp Mr Mu Mw Nb Nn No Nq Nr Nt Nv Ny On Oz Pd Pe Pf Pg) Oh(Hq Hv Hw Hx Ii Ij In Ir Iv Jk Jo Jt Lh
Lx Mi Mq Mr Mu Mz Na Nb Nf Nr Nv Ny Ok Pe Pg Qa) Nv(Hr Hv Hw Ii Ij Im Io Ir Iv Jj Jo Jt Lx Mm Mr Mu Mz Na Nb Nn Nr Ok Pe Pf Qa
Wm) Ny(aA Hu Hw Ik Io Ir Jj Jo Jr Jt Lh Lw Mm Mr Mu Nb Nm Nn No Nr Ok Oz Pc Pe Pf Wm) On(aA Hr Hu Hv Hw Ij In Io Ir Jj Jn Jo Jr Lh
Lw My Na Nf Ni No Nr Oi Ok Pe Pz Qc) Pg(aA Hr Hw Hx Ii Im Ir Iv Jg Jj Jo Jt Mm Mq Mr Mu Mz Na Nb Nr Ok Pe) Ir(Im Jg Jk Jl Jp Jr Lw
Lx Ma Mi Mm Mn Mp Mu Mw Nm Nn Nq Pf) Jl(Hr Im Jg Jn Jo Jr Jt Lh Md Mr Mu Na Nb Ni Nm No Ok Pe) Ok(aA Hq Ik Jk Lh Lw Lx Md
Mm Mp Mu Mw Nb Nn No Nq Pc) Mm(Hv Hw Hx Ii Iv Jo Jt Lh Mr Mu Nb Nr Pe Qa) Jg(aA Hr Hw Hx Ii Iv Jo Lh Mr Mx Mz Nb No Nr
Pe) Nn(aA Hr Hw Hx Ii Iv Jt Lh Mr Mz Na Nb Nr Pe) Jr(Hw Hx Ii Jk Jo Jt Lh Mr Mu Mz Nb Nr Oz Pe) Pf(Hr Hw Hx Ii Iv Jo Jt Lv Mr Mz Nb
Nm Nr Qa) Lx(Hr Hw Hx Ii Iv Jn Jo Js Jt Lw Mq Nm Qa) Mu(Hr Hw Hx Ii Ij Jn Jo Lh Nr Pe Qb Qe) Ma(Hr Hw Hx Ii Iv Jo Lh Mr Nb Nr Pe)
Mp(Hr Hw Hx Ii Iv Jo Mr Mx Nb Nr Pe) Mw(aA Hw Iv Jn Mj Mx My No Nr Oy) Pe(Jk Jn Lw Mj Mn Nj Pc Qd) No(Hr Ii Jo Lh Ms Nj Nm)
Jp(Hr Hw Ii Iv Jo Nb Nr) aA(Hr Hx Ii Jo Lh Lw Me) Iv(Mn Nm Nq Qa Qb) Nr(Jn Nq Qa Qb) Nb(Im Ij Nj Nm) Hw(Jn Lw Nq Qb) Mi(Ij Jn Qa)
Hx(Jj Lw Nm) Ii(Im Mx Nj) Lh(Jj Lw Pc) Mr(Jn Nm) Qa(Nj Pc) JjJo} Ik{Jh(aA Et Fr Hw Hx Ii Ip Iq Ir Is Iu Iv Ji Jn Jo Jq Jr Lh Li Lv Lx Lz
Mb Mh Mi Mj Mk Mp Mr Mt Mu Mx Nb Nc Ne Ng Nj Nl Nn No Nr Nt Nu Nv Nw Nx Ny Oh Ok On Oz Pa Pe Pf Pg Po Qa Qb Qd Qc) Nw(Fr
Hr Hv Hw Ii Im In Ip Iq Ir Is Iu Iv Jg Jk Jn Jo Jr Jt Lh Li Lx Lz Mb Mi Mj Mm Mp Mr Mu Mv Mx Na Nb Nd Nj Nm Nn No Nr Nt Nu Nv Nx
Oh Ok Om Oz Pa Pe Pf Pg Po Qa Wm) Jg(aA Fr Hq Hr Hw Hx Ii Io Ip Iq Is Ji Jk Jn Jo Jq Jr Lh Li Lu Lv Lx Lz Mb Mh Mi Mj Mk Mt Mu Mx
Mz Nb Ne Nh Nn No Nr Nt Nv Nx Ny Oh Oi Oz Pa Pe Pf Pg Po Qb Qd Qe) Om(aA Et Fr Hq Hw Im Ip Iq Ir Is Iu Iv Ji Jn Jo Jr Lh Li Lx Lz Mb
Mi Mj Mk Mm Mp Mr Mt Mu Mx Nb Nd Ne Nl Nn No Nr Nt Nu Nv Nw Nx Ny Oh Ok On Oz Pa Pe Pf Pg Po Qe) Jr(aA Et Fr Hq Ii Im Ip Iq Is Iu Iv Ji

Jh Nq Po) Oh(Ir Jt Na Nt) Hu(Jg Lx Mi) Im(Jl Jo Jq) Jn(Lx Mi Nd) Pc(Hw Iv Jo) Ml(In Nb) Hx(Nb Po) Jg(Ns Og) Of(Jj Og) NtLy MkPa MvJh NaJl NcIo NdIs HwIj IuJq} Mm{Oh(Hv Ij In Ir Iv Jj Js Jt Lu Mr Mz Na Nf Qa) Io(Hr Iq Jg Jk Jt Mh Nc Nr Nt) Jh(Hv Hx Js Mh My Pa Qa Qb Qe) Lv(Ii In Jo Jt Mu Mz Na Nf) Om(Iq Ir Mr Ms My Nl Oy) Hx(Jj Lw Ng Nn Oy Pf) Pg(Hq Hv Im Js Na Oy) Is(Hw Ir Mr Mz Nf) Lh(Iq Ir Mg Mz Ng) Pa(Hr Iv Jj Me Na) Nv(Iq Jt Qa Qe) Po(My Og Oy) Nj(Mi Nf Nt) Lx(Ij Iv) Ly(Mi Nt) Ng(Hq Of) LuLw MkPe MxNx NfQe HrPf HuJk IjOg IlJj} Jq{Pa(Hx Ij Im In Md Mh Ml My Oy Qc) Mi(Hx Ij Jg Jj My Ng Ny Og Oy) Im(Is Jg Jh Mr Nb Nl Pe) Jj(Hq My Nd Nl Nq Pg Po) Mu(Iq Iu Lz Nl Oh) Ii(Ij Md Mh Ml My) Jg(Hw Lx Md Mp Nd) Og(Hx Mr Nm Po) Oh(Iq Iu Nt Pe) Nb(Ij My Ny) Nl(Io Ma Pf) Jh(Hw Is Iu) Pc(Is Jo Nr) Ij(Hx Pc) Qc(Mr Pe) Jr(Iu Jo) PoNg NnIr LxJl MeHv MpIq IvQd} Om{Oy(Hw Ii Iq Ir Is Iv Jk Jn Lx Mi Mr Nb Nd Oh Pa Pe Po) My(Ii Is Iv Jn Lx Mi Mr Nb Oh Ok Pa Pe Po) Ng(Im Iq Ir Is Iu Jk Jn Mp No Pa) Lh(Hx Md Mg Mv Ny Og) Fr(Ma Mg Mv Of) Hu(Im Mt No Ny) Og(Iq Ir Lx Mi) Nl(Jj Mg Nn) Ny(Mv Nv Of) Me(aA Iv) Mt(Mg Mv) Of(Jl Nv) MkPe MrIi MsIs HwIj} Jg{Ng(Hx Ii Im Iq Iu Jk Jl Md Mt No Nt Ok) Io(aA Hw Ih Ir Iu Iv Nd Ne Nr) Og(Fr Is Jl Mp Mt Pg Qb) Hu(Hx Is Jn Ny Pa Pg) Ns(Is Jn Mt Ny) Mg(Hr Hx Lh Pg) Oh(Hw Ir Mr Pe) Oy(Hx Nv Ok Pg) Pa(Iv Jj Mk Oi) Mv(Lh Mt Ny) Lw(Hx Mx) My(Ok Pg) Jn(Mp Nd) Jt(Ir Iv) Ny(Mw Of) Oi(Hx Qb) LxLy MsMt JjPg} Jh{Lv(aA Hw Ih Iq Ir Jj Jn Lx Lz Mi Mr Mz Nf Nn Pa Pe) Ng(Hq Iu Iv Jn Lx Mp Mr No Nt Pe Po Qb) Og(Ii Is Lh Mt Mx Pg Qb Qe) Nj(Im Ms My Na) Hu(Mr Nn Nq Pa) Oy(Lh Mp Pa Qb) Ly(Lx Mi Mr) Hx(Lw Nn Pc) Pg(Jj Jn Nn) My(Lh Mp) Iq(Is Qc) Nx(Mg Ms) Pa(Iv Mk) LxJm NdJn IlLh NyOf} Oh{Lw(Hw Ii Im Iq Ir Is Iu Iv Lx Mr Nb No Pa Pe Po) Pc(Hv Hw In Iv Jo Mi Mr Nn Pe) Lx(Hv Hw Ir Is Iv Jn Nm) Jj(Hq Hr Hx Jo My Of) Nm(Mi Nv Oi Pa) Mh(Ii Mr Po) Ni(Nc Nl Pa) Jn(Mi Oi Pa) Lv(aA Wm) Mt(Hw Pe) Mw(Ng Og) Hu(Mu Nq) Ii(My Oy) NtJm MdMl MiHv InPa JkOi} Nj{Nv(Hw Iq Jn Mi Nf Ni Nr Nt Qa) Qa(Ii Mi Nd Nf Nq Pa) Pa(Hr Hv Ir Nf Pf) Lx(Ih Mu Mz Ni) Md(Hx Jp Mp Qe) Im(Hr Ii Ir Mv) No(Jj Jn Lw) Na(Hq Jk Jp) Po(Iq Jj) Nm(Mi Nb) Lv(Mx Mz) Mp(Mz Ns) Nf(Ir Pf) Jp(Ih Lu) NnJj MuIv MwHr MyNb HwPf HxIq} Ny{Lx(Hx Jj Jn Lw My Na Pc Pg) Hu(Io Jk Mi Mr Nd Pa) My(Lw Me Mt Nn Pc) Ng(Lh Nd Nm Pc) Oy(Jk Lw Nq Pc) Nn(Mr Mu Mv) Me(Hv Ir Iv) Mp(Jn Mz) Io(Nt Of) Jj(Lh Mi) NmOg LwMf LyNd MkPa MvPc ImJn} Jn{Nn(Hw Lh Lv Mi Mr No Nv Pa Pe Po) Lw(Lh Mf Mi Mr Nd Pe Po) Jj(Hq Hx Lv Mp Nx) Hr(Im Ma Pf) Jk(Hu Og Oy) Pc(Mp No Po) Ng(Lx Nq) Qc(Iq Is) PoMy FrNl NmIo MjJl MrMu ImNv} Fr{Ng(Hw Ih Ij Mi Mw Nd Nm Nv) Oy(Hx Ii Ij Mr Nr Nv Pe Qb) Nl(Ij In Lw Mz Nf Nm) Hu(Hx Im Mx Nv Qb) Lw(Is Mf) Mg(Lh Nm) My(Hx Qb) NtLy MfMx NdJm HrIm JjNx} Nv{Im(Hv Ir Iv Jo Js Lw Mz Nf) Io(Hu Lw Na Ng Og Pa) Ng(Nn Pf Po) Jj(Ir Lh Mr) Lx(Hq Oy) Mu(My Oy) Is(Lw Pc) Qc(Iq Mz) Og(Hr Mw) NnOi MtMy MxPc} Mt{Oy(Ii Jk Jl Jo Lh Lx Nb Pc Po) Pc(Hu Jo Lh Ng Oi) Nn(Hu Jo Oi) Nt(Ly Mk) Lv(Iq Jj) Lw(Lh Mf) Lx(Jm Ng) Hu(Mr Mu) WmNu PoNg MkPe MwOg} Is{Lw(Io Lh Mf) Hu(Jk Nn Nq) Og(Mw Nm Pc) Lx(Jm Pc) Jj(Hq Pg) Pa(Io Mk) NmJt NoQd LyMi MjMz MwNg NdJm IqQc LhPc} Nx{Nn(Iu Ng Nl Nr Og) Jj(Hq Il Im Lz) Og(Hx Mi Nq Pa) Ly(Mi Nd Nt) Im(Nc Pf) Qc(Iq Mz) PoOf NqOy MxPc} Ok{Mq(Lx Mp Mu Nn No Pa Pc) Nn(aA Mj Pc) Lw(Im Lx Mi) Jk(Hu Jj Oy) Pa(Fp Mk Nr) Mz(Lj Qc) LxMh JjLh} Jl{Mj(Iq Ir Mr Mz Nf) Og(Lw Mw Nb) Nm(Jj Mg) Mi(Jm Ng) NnOi LwIo NcNk HuLh} Pg{Im(Hw Iv Jj Js Lw Na Nf) Mu(My Ng Oy) WmMk NmJj NnNa LxJm MxPc} Mw{Oy(Ii Il Iv Jo Nn Pe Qa) My(Ir Mi Mr Ng) Ng(aA Jr) HuIm} Lx{Hr(Mp Oy Pf) Nn(Jm Jo) Ly(Lh Nm) Hx(Hu Oy) MyIj JkJm} Jj{Jr(Hw Iu Mi Mr Mu Po) Lv(Hr Jo Mx) ImLh} Lh{Nn(Hu Lw My) Lw(Jm Ly) Ma(Hu Ng) Mj(Ir Mx)} Hx{Ma(My Og Oy) Og(Nm Nn)} Jr{Nt(Jm Lw Pc) IqLj} Nn{Lw(Mx Nl) MkPe} Me{aA(Hu Mf) IoIr} Qb{Jm(Mi Nd) MzQc} Wm{MkJs NaIv} Mp{MjIr JkOy} LvMaNl

Constrained panels with 3 analytes, where 1.0E-6 >= 'AUC p-value' > 1.0E-7. Contains 2,089 panels of 295,240 total panels evaluated. :
Pb{Mu(Hq Hv Ih Iu Jt Lv Lx Mh Mi Mm Mn Mp Mr Nn No Pf Qa) Jk(Hr Hv Hx Ij Jg Jj Jo Lw Mm Mp Mq Mz Nm Nr Pa Pf) Ii(Hv Hw Ik Iq Ir Iv Jn Jo Js Li Lw Nf Nh Ni Oy) Mp(Hv In Jt Lw Lx Mm Mz Na Nh Nu Oz Qa) Hq(Hw Ip Ir Jg Jo Jq Jt Mm Mx Nb Nr) Nr(Hx Ir Jj Lw Lx Mx My Nj Pd) Mb(Ij Im Jl Js Li Mn Mv Mx Nm) aA(Hw Ij In Ir Mz Na Nb Nf Pe) Mi(Hx Lv Lw Mm Nn Nv Pf Pg) Lx(Ik Jp Lv Mm Mz Nn Pf) Ma(Hv Mq Mx Mz Na Nu Qb) Nb(Ik Jo Na Ne Nh Ni Po) Pd(Hw Ip Iv Jg Jj Jn Mm) Nf(Ir Jg Jh Nn Pf Pg) No(Hv In Jt Mz Na) Mr(Ir Jj Lv Lw Pc) Nn(Jn Lw Ni Pa) Jg(Ij In Md Ni) Pc(Iv Nv Pa Pg) Mq(Mm Nq Qb) Mw(Js Nm Qe) Hv(Hx Jp Qe) Im(Hw Ip Jt) Jo(Mn Qb Qe) Oz(Ij Ir Js) Nt(Ik Pg) Lu(Ip Mm) Lw(Jh Mx) Md(Hx Pf) Jj(Hw Of) Jn(Hx Jt) Jp(Jt Nu) PoNg NmMz NqHr LvIp LzIj MeIr MnQa MvNx NiPg InJh IuNw JiJl NvPa} Ik{Mm(Fp Iv Jo Li Lz Md Me Ml Mr Mx Nb Ne Nt Nu Pd) Ma(Hq Ii Iq Lz Mj Nb Nl Nt Nu Pa Qa Qd) Qe(Hx Ii Im Li Lz Mi Nh Nm Nq Nr Nv Pa) Mp(Ir Iv Mi Mr Nb Nj Nm Nu Pd Pe Qa) Nv(aA Fp Iq Jo Lw Mk Mr Mz Oz Pe Qd) Nn(Hv Iu Jt Li Lw Mu Mz Na Qa Qd) Ip(Hq Jo Li Lu Md Mk Ne Nq Pd Qd) Pf(Hw Iq Jt Lw Md Mu Mz Na Nt Qa) Jn(Hq Iq Iv Mj Mk Nb Nd Oz Pd) Pg(Jo Js Jt Lw Mz Nb Nm Nt Pc) Nx(Hw Iu Jk Jt Lj Nd Nl Pc) Nm(Jk Lz Mi Ne Nh Nl Pa) Lx(aA Hx Lv Mh My Ny Qa) Po(Fr Hx Lv Mh Ml My) Mw(Hu Ih Is Lz Mq My) Im(Hq Hx Jg Jk Pd Wm) Jj(Hq Il Jk Jo Pe) Mb(Jk Li Lz Pa) Hx(Jp Li Lv Nh) Jg(Fp Js Mr Nf) Fr(Iq Nb Pa) Mx(Ii Ij Nt) Nj(Hq Nb Nt) Qb(Ii Lz Pa) Mn(Mu Ne) Qa(Mi Pa) Lh(Li Pc) WmNq LvIv MdIs MuPd NfJh NhJk IlJp JiJl} Mm{Lx(Hr Hv Hw In Ir It Jo Js Jt Ly Me Mz Na Ni Nr Ns Oy Qa) Jh(Hr Hw In Jo Jt Mr Mz Na Nb Nf Ng Nr Pe) Jj(Hq Hr Hw Ir Iv Jk Jo Lh Mz Nf Of Pe Qe) Pa(Hv Hw Ij In Ir Jn Jo Jt Nf Ng Ni Oy Qa) Lw(Ii Io Iq Lz Mf Mh Mr Mx Nb Po Qb Qe) Hx(Hv Iq Ir Js Mb Mg Na Nb Nf) Pf(Hv Hw Ij In Jo Na Nb Nf Ng) Po(Hq Hv Js Mk Na Ng Ns Qa) Mb(Iq Js Li Lj Lz Nb Nt) Ir(Im Lu Mi Mu Mz No Pc) Om(Hu Hw Ih Iv Mg Ng No) Qb(Hr Lu Md Mu Na Ni) Qe(Hr Ij In Md Mu Na) Io(Ih It Md Mx Nl) Ng(Hu Jg Mu Mw) Nt(Jm Lv Oh) Lu(Ij In Jg) Ms(Mw Nb No) Pg(In Jo Jt) Mg(Jo Pe) Mu(Hr Iv) Ni(Nc Nv) Iq(Oh Pe) Og(Jk Mw) NnIv NoIs LyMr MiHr MzIm NbJs NfJg IhIj IiOy} Jg{My(Fr Hr Hx Io Ir Jh Jl Lx Mb Mp Mt Mw Nv Oi Om Pa Qb) Oy(aA Fr Hr Ii Il Io Ir Jh Jl Lx Mb Mr Mx Pa Pe Po Qb) Og(aA Il Ir Jh Jk Jo Lh Lv Lw Mw Mx Pa Qe) Ng(aA Hq Il Ir Jn Mi Mu Mx Nb Nf Nx) Jj(Hq Hr Hx Il Io Is Jn Lh Lv Nx) Hu(aA Io Lx Md Nn Nq Nv Nx Po) Hr(Ih Im Iq Lv Lz Mi Nd Pf) Oi(Ih Iq Ir Iv Mp Mz Nn Qe) Lx(Hv Hw Is Iv Jn Mh Nq) Mb(Im Lj Mi Nt Po) Lw(aA Io Nl Qb) Mg(Fr Io Jo Mp) Ms(Is Jn Nx Ny) Pa(Hw Ir Mz Na) Jm(Mi Nd No) Jq(Iq Iu Lz) Ly(Mi Mr) Na(Nv Pg) Io(Jt Nt) NsJh LvaA MkPe MpHv MuQb HxOf IlLh ImNx IqQc PzQe} Nw{Pc(Hv Im In Iq Ir Jn Lx Mi Mr My Mz Na Nd Nr Og Oi Pe Qa) Nn(Hu Im Ir Jn Lx Mi Mr Mu Mv My Nd Ng Nr Og Oy Pe Qa) Im(Hw Ir Iv Jn Jt Mj Mz Na Nm Nr Ok Qa) Og(Ii Ij In Jk Lw Mr Mu Mw Nf Nm Pe Po) My(Ii Ij In Mi Mu Nb Nf Nm Nq Pa) Ny(Ii Ij In Mi Nb Nf Pe Po) Nd(In Ir Iv Mz Na Ok Qa) Oy(Ii Mi Mu Nb Nf Nq Pg) Ml(Ii Ij Mz Nf Po) Mu(Hu Is Iv Mv Ng) Lw(Iq Iu Lu Mr) Mh(Ii Nf Nr Pa) Lx(Ir Mz Na) Mi(Hx Na Ng) Mv(Ii Jk Po) Hu(Jh Nq Nt) Md(Ij In) Mp(Jt Mz) Ni(Nc Nl) Hx(Ii Pe) Iq(Lj Lz) Jn(Iu Pa) Om(Ms Of) NsMq NgIi JjLh} Mb{Nh(Fp Hx Im Jj Js Lw Lz Mh Mi Nb Nf Nm Nq Nx) Lw(Ii Im Jk Li Lj Lv Nb Ne Nq Nr Nt Nx) Jj(Iu Js Lz Ma Mi Mr Mu Ne Nm Nq Nt Po) Jp(Hx Iv Jk Lz Mh Mi Mr Nf Qb Qe) Nm(Ih Js Lu Lz Mh Ne Nf Qb) Lv(Im Lj Mh Mp Ne Nj Qa Qe) Mz(Iv Lh Mi Nd Nq Pc Qa Qe) Nt(Iq Jn Js Ma Mp Nn Po) Ma(Lj Mh Mi Mx Nj Nl) Qd(Hx Mi Nd Nf Pa Pc) Nn(Im Iv Mi Mr Pa) Ip(Hw Im Nl Nr Pc) Qb(Ir Jn Lz Mh Mp) Md(Fp Jt Mx Nl) Po(Im Iv Pc) Nj(Lh Mr Nf) Js(Lh Nq Nx) Pa(Im Mp Pc) Ne(Mw Qe) Nx(Jn Lz) LyMr MiMp HxOg IrIv JiJl} Ip{Pa(Hr Hv Iq Ir Iv Jn Js Lv Md Mz Nf Og Pc Qa) Iq(Hv Hx Iv Jk Lh Mi Mr Nb Nt Pc Pe Qa) Pc(Hv Iv Jj Lu Mi Mr Mz Nh Pe Qa Qe) Lv(Im Iv Jn Js Lz Mi Na Nf Wm) Mi(Hv Ir Iv Jn Nf Ng Oy Qa) Nc(Hv Ij In Md Mv Nf Ni) Nm(Im Lu Lz Mx Ne Qb) Jk(Ir Js Lw Na Nf Nh) Jn(Hw Ii Mr Nb Nt Pe) Nq(Hr Hv Js Na Nj) Md(Im Iv Mx Na Nj) Jj(Hv Jt Mu Na Qa) Nt(Ir Mz Nj Nn) Lw(Im Iv Li Nb) Mz(Hw Lh Mr) Hr(Li Nj Pg) Hv(Lz Me Mn) Im(Ii Na Nf) Jt(Nv Pf Pg) Mw(Ms Ne) MaIh MeIv MpJo MvNe NfNj IiOg} Jh{Og(Hw Iq Ir Iv Lw Lx Lz Mh Mi Mr Mw Mz Nb Nf Nn Nr Nt Pc Pe Po) Oy(Hq Hr Hw Ii Is Iv Jo Lx Mh Mi Mr Mx Nb Nc Nl Nn Pe Pf Po Qe) Hu(Hw

Figure 35 Continued

Hx Iq Iu Iv Jk Jn Lu Lz Mp Mx Nd No Nt Pe Pf Po Qb Qe) Ng(Hw Ii Iq Ir Jk Jq Lz Mu Mx Nf Nn Pf Qe) My(Jo Mh Mr Nb Nn Pa Qb Qe) Jj(Hq Hx Il Jn Nl Nx Pa) Nn(Ir Is Jo) Mg(Hx Lh Nj) Ms(Hx Pa Qb) Of(Hx Lh Pg) Lv(Nr Nt) Lw(Is Mx) Me(Hv Iv) Hr(Im Pc) Iq(Jq Lh) LyNd LzJq MiJm MkPe IrPc} Jj{Nx(Hw Ir Iu Iv Lx Ma Mi Mn Mp Mv Mw Mz Nc Nd Nm Nn No Nq Pf) Jn(Hr Jo Lh Lx Mi Nd Nm Nn Nq Of Pg Po) Mt(Hw Jk Jo Lh Lx Mi Mr Nm Om Pc) Nj(Lx Mi Mr Mu Nt Of Pd Pe) Nt(Jl Jq Jr Nv Ny Ok) Lv(Hx Il Mp Nc Nn Pa) Nm(Fr Hq Hx Is Oh) Pg(Iq Ir Jo Mz Nn) Mp(Hq Hr Il Nl) Lh(Fr Jl Ly Oh) Hr(Hq Ma Pf) Is(Fr Jo Om) Ny(Mr Mu No) Jl(Lx No) Oh(Ii Jk) Pa(Nn Of) FrJo MuNv NlQb} Om{Pa(Hx Im Jn Lw Mh Ml Mv Nn Ny Og) Lx(Hq Ir Is Mg Ml Mv Ny Pg) Nn(Hu Hw Ir Mi Mu My Ng) Po(Hx Md Mh Ml Mv Ny) Nt(Hu Ly My Ng Og Oy) Mi(Hx Il Jn Ml Mv Ny) Mr(Hx Mh Ml Mv Ny Og) My(Hw Iq Ir Jq No) Mg(Im Nd Nj Pe) Nd(Hq Mz Ns) Nf(Md Ml Mv) Im(Ir Iv Jn) Of(Hx Mt Nl) Pe(Hx Ml Ny) Mp(Hq Ns) Ij(Hv Ir) NoOy MsLh MzNl NbOg NgIv HuIs} Nj{Mp(Hw Ih Ii Ij Im In Iq Na Nd Nf Nr Nt) Mu(Ii Jo Jt Md Mi Mx Nt Pe) Pa(Hw Iq Iv Jo Jt Ni Nt) Nf(Jk Jn Ma Nm No Pg) Im(Jn Mi My Mz Pe) Qb(Hw Jk Jn Md Na) Lv(Iq Jn Mi Pc) Jk(Iq Mi Mz Qa) Nq(Ir Mx Na) Ma(Hw Jn Nr) Hx(Ih Nd Nr) Nm(Lu Md) Mn(Hw Na) Mz(No Pg) Qa(Iq Md) NtPf LyLh MsMw NbOy NiQe HwPe IjJp} Pc{Ny(Hu Hw Iq Ir Iv Jn Mi Mr Ms Mu Mw Mz Ns Of Pe) Is(Hw Iq Ir Mi Mr Mz Nf Nt Oi Pa Pe) Oh(Ij Im Iq Ir Lu Mz Na Nf Oi Pa Qa) Mt(Hw Iq Ir Iv Mi Mr Mz Na Pa Pe) Jn(Hr Hw Lh Mi Mr Nd Pe) Ok(aA Im Lx Mi Nd No) Nx(Jp Mp Og Pf) Nn(Nr Pa) Hr(Ma Pf) Jq(Ir Nt) Nv(Ng Og) NmaA LxJo MpNh} Nn{Hu(aA Fr Hr Hx Jl Lu Lx Nv) Is(Hw Im Mi Mr Nt Oi Pe) Nx(Iq Lz Mu My Oy Pf) Ny(Hw Iq Ir Iv Lw Of) Mt(Hw Mr Na Pe) Ng(Hx Ii Lx Pg) Hr(Lv Lx Nv Pf) Hx(My Oi Oy) Nv(Na Og Oy) Mf(aA Jl) Jn(Ii Nd) NmaA NoOk NqLx MiJm MwMy NaJl NbOi NiNl IqQc LhOy} Fr{Ng(Ii In Jl Lw Lx Md Mr Mu Nf Nt Pa Pe Po) Hu(aA Hv Hw In Jl Lx Md Mr Mu Nf Pe Po) Oy(In Lx Md Mu Nf Pa Po) My(Ij Lw Md Mt Nr Nv) Hx(Mg Mv Of) Jm(Lx Mi Nt) Lw(Im Iv) Mk(Pa Pe) Og(Nb Po) NoMj NqLx MiHq MtMv MzIm IqJo OkaA} Lw{Mt(Iq Ir Is Iv Mr My Pa Pe) Is(Iq Mi Mr Mu No Pa) Ny(Iq Ir Mi Mr Pa Pe) Jn(Ir Jk Nb Nq) Mp(Ir Js Mf) Hx(Im Og Pf) Oh(Lu Mu Nt) Mx(Ir Jp) Hr(Jp Ma) Jl(Im Mf) Og(aA Nx) LxJs MkPa NgNv NlPf IqQc OkaA} Lx{My(Hq Hx Mw Ng Nv) Hr(Hq Hu Jp Mh Og) Nm(Hu Jm Ng Oy) Ij(Md Mh Ml Oy) Oh(Jt Mz Na Qa) Ly(aA Is Jo) Mp(Hu Hw Oy) Jm(Mn Qa Qe) Mh(Hx Js) Ng(Jk Of) Jn(Is Mt) Ny(Ml Mv) MeaA HqHx HwOy} Oy{Ny(Lh Mi Mr Pa Pe Po) Mt(Mi Mr Mu Pa Pe) Nb(Is Jl Jq Jr Ok) Po(Is Jl Mh Nv) Mu(Hr Hx Jl Qb) Mw(Nt Pg Qe) Nv(Io Lh Pf) Nx(Jk Mi Pa) Wm(Ly Md) Ii(Is Jq) HxPf} Ng{Nv(Hr Ii Lh Mi Mr Mw Nb Nm Pa Pe) Ny(Iu Mi Mr Nt Pa Pc Po) Mt(Ii Mi Mu Mw Nb Pa) Nm(Hx Jk Lh Pa Po) Mu(Is Jq Qb) Jk(Lh Mp) Pa(Jq Nx) WmHq MwJl} Og{Nx(Hr Iu Nf Nm Qe) Ny(Lh Mi Mr Pa Pe) Mu(Hx Is Lh Qb) Mw(Hr Jn Mp Mx) Nb(Is Mt Nv Oh) Ii(Is Mt Oh) Po(Is Nv) Mp(Hr Hx) Jq(Pa Pe) NmHr MiNv HxPf} Im{Jq(Hw Iq Iu Jo Mj Nc Nr Oz) Jl(Ir Jn Mz Nf Nm) Nv(Hw Jt Mj Na Nm) Ir(Lh Ny Oh) Pg(Jo Jt Nm) Nb(Mp Oh) Hr(Ma Pf) Jn(Nm Oh) LvNc MwMy MzNy} My{Mw(aA Hx Ih Iq Jl Jp Js Mt Nf Pf Po) Mt(Ii Jl Mi Nb Pa Po) Nq(Nx Ny Ok) Po(Me Ny) Mv(Jl Ok) Nb(Is Ok)} Mi{Oh(Ir Jt Mz Na Qa) Ly(Jq Nv Ny Pg) Jm(Is Jn Mt Nv) Mp(Iv Jn) Hr(Ma Pf) Io(Is Nv) HuNv} Pa{Oh(Hv Mz Na Oi Qa) Mk(Jl Lh Mu) Il(Is Ny) Ok(Mh Pe) NmIo MjJn IsJm JqNy} Hu{Nq(aA Hx Jl Nv) Mu(aA Hx Qb) Nt(Mt Ny) Mw(aA Lh) Jk(Ma Mp) MxNx LhNv} Nm{Io(Hx Jq Mp Mx Nl Nv) Mg(Hx Mp Nv Ny) aA(Me Oh) MzQc} Mj{No(Hr Jo Ms Mx) Ir(Pf Po) Jq(Qc Qd) Js(Jl Lh) IqLh IsPf} Me{Jn(Io Lu Mf) aA(Lv No Nv) Is(Hv Iv) MhJq IoLh IvJl} Hr{Mp(Hq Jp Lv Mx Ns) Ma(Iq Qb Qe) LvJp NdJr} Iq{Qc(Pg Qa Qb Qe) Lj(Mt Ok) WmLv InOh QdJq} Mh{Mt(Ii Mr Nb Po) Po(Jn Ok) NoOk JqPe} Jm{Nt(Is Jl Mt Ny Qb) Nd(Jn Nv) NqIr} Oh{Mu(Hw Ir Is Iv) Jn(Iu Nt) MsMw NbOi} Jq{Ii(Hx Lh Ny) NqNc NrQc NdIs HxNy} Wm{Lv(Jn Mx Nf Qd) MkNf} Io{Nl(Jp Mp) NtIs IvNv QbJp} Ma{Hx(Ir Jn Js) IhNx} Ly{NoLh MpIi MrNv} Qc{Mz(Qa Qe) QeJn} Mp{MuHw HqPd} Mt{Ii(Hx Ny)} Jo{Ok(Lh Pg)} Nx{MnNh NdJp} MuNyOf MvMwNf JnJsLh

Constrained panels with 3 analytes, where 1.0E-5 >= 'AUC p-value' > 1.0E-6. Contains 2,223 panels of 295,240 total panels evaluated. : Jg{My(aA Hq Hv Hw Ih Ii Ij Im In Iq Iv Jk Jo Js Lv Md Mi Mr Mu Mx Mz Nd Ne Nf Nn No Nq Nr Pe Pf Po Qe) Oy(Hv Hw Ih Ij Im In Iq Iv Jk Jo Js Lu Lv Md Mi Mp Mu Mz Nb Nd Ne Nf Nh Nn No Nq Pf Qe) Og(Hv Hw Ih Ii Ij Im In Iq Iu Iv Js Lx Lz Mi Mr Mz Nn No Nr Pd Pe Pf Po Qa) Hu(Hv Im Iq Ir Iv Jk Jo Js Lu Mi Mr Mu Mx Mz Nd Ne Nh No Pf Qe) Ng(Hw Ih Iv Jh Jo Js Lu Lv Mw Mz Nn Nr Om Pd Pf Qb Qe) Jj(Hw Iq Iu Iv Jo Lx Mi Mp Mr Mx Nd Nf Pd Pe Po) Ns(aA Iv Jo Md Mi Mp Mx Ne Nh Nl No Nv Pf Qe) Mg(Ii Iu Iv Lx Mh Mi Mr Nd Nr Nt Pd Pe Pf Po) Lv(Ih Im Iq Jn Js Lx Lz Mi Mr Nf Oi) Ms(Hx Iv Jh Jl Mp Mx Nb Nv Nw Pa Po) Lw(Im Iq Iu Lu Lx Lz Mi Nb Pa) Lx(Hq Ir Jm Js Mv Mz Na Qa) Mi(Hv Ir Iv Jn Js Mz Ni Nn) Im(Hv Ir Jn Js Mz Nb) Nd(Hv Ir Js Mz Ni) Jn(Lh Mr Pa Pe Pg) Po(Hx Mh Mv Ny) Oi(Lz Mu Nr Qa) Mv(Jq Mr Nf) Mz(Ml Mr Pe) Ni(Lz Nc Nl) Mw(Hx Lh) Na(Pf Qb) Iq(Pe Pz) Iv(Ik Me) Js(Mp Mu) HxIi JoLh} Ik{Jk(Fp Hx Ii Iq Ir Iv Jo Jp Li Lz Mi Mj Mk Mp Mr Na Nb Ng Nr Og Oz Pa Pe Qe) Nm(Fp Hq Hv Ii Io Iq Ir Iv Lu Ma Mh Mj Mr Mv Mw Nq Nr Oz Pe Qa Qd) Ma(Fp Hv Ih Ij Iu Js Jt Li Mh Mk Mp Mz Na Nj Oz Pd) Iv(Ii Im Ir Jt Mi Mk Mr Mw Nb Nh Nj Nt Oz Pa Pe) Im(Ii Ij Ir Lz Mi Mr Mu Mv Nb Nr Pa Po Qa) Mp(Fp Hq Ii Iq Jo Jp Lu Mh Mm Mv Pa Qd) Hx(Js Jt Lz Mi Mk Mv Mx Nr Oz Pa Pc Qd) Qa(Ii Iq Jo Li Lz Mj Mk Mu Nb Nr Oz) Qb(Jo Jt Li Mk Mw Nb Ne Nh Nu Oz Qd) Jp(Hq Ii Jo Mi Mv Mx Nr Nt Nu) Lx(Is Jt Lw Mv Nt Og Pg) Nh(Hq Ii Mi Mv Nb Pa Pe) Nj(Iq Jl Mi Mr Mv Mx Pd) Ij(Ip Li Lz Mi Mv Nr Pa) Qe(Jo Jt Mk Mv Nb Ne Oz) Wm(Li Ly Mh Mx Nf Pc) Mu(Fp Ih Iu Mx Nt Nu) Ir(Jn Lv Lz Nb Pb Pe) Nx(Hq Jo Js Mv Nc) Po(aA Jj Lw Pe) Mn(Lu Mj Nl Nr) Jl(Et Is Mb Om) Lv(Mr Ne Pe) Mm(Mk Ni Oz) Mw(Iu Mh Nu) Nv(Nb Pc Pd) Jq(Jt Mj) Pe(Mr Nt) NnMd LwMx NbLh JjPf JnJt} Jj{Mm(Hv Ih Ii Ij In Iq It Js Jt Lu Lx Md Mi Mr Mx Na Nb Nd Nl Nr Pd Pf Po Qa) Lv(Hq Hw Ih Iv Jp Lx Ma Mi Mn Mr Mw My Nd Nf Nm No Nq Of Pe Pf Po) Of(Ih Im Iq Ir Iv Jq Lx Lz Mb Mn Mp Mw Mx Nc Nf Nl Pf Qb Qe) Oh(Hv Hw Iq Iu Iv Jt Lx Md Mi Mr Mu Na Nb Nd Nf Nt Pa Pe Po) Jh(Hr Hw Iq Ir Is Iu Iv Jo Lh Lx Lz Mi Mr Nd Nf Pe Po Qe) Mp(Hw Hx Iv Jo Lx Mi Mr Nb Nj Pd Pe Po Qe) Mb(Hu Ij Jm Mv Mw Mx Nb Nd Nf Nl) Jo(Hq Hx Ir Jk Jq Mn Nn Pa Qb Qe) Fr(Hv Hw Iv Jt Lw Mr Mz Na Nt) Nm(Il Ir Iv Jq Lh Mx Nl Pa Qb) Nj(Hw Jp Md Mv Mx My Nb Nf Nq) Jn(Hw Ii Iu Lw Mr Mu Nb Nt Pc) Hx(Hq Iq Iv Lw Ma Nn Pc Pf) Mn(Hr Il Mx My Ne Nh Nl) Hr(Lx Nn Nq Pa Qb Qe) Hq(Ih Im Iv Qa Qe) Is(Lh Lx Mi Nd Po) Nt(Lh Mt Nx Pg) Mu(Jq Mt Nx Pg) Nn(Lh Nl Po) Ma(Nl Qb Qe) My(Im Nl Qb) Om(Lh Lx Mi) Jk(Jq Lh) Pa(Ii Iv) NqOk LwIp MrPg HwJq IlJp NxPc} Pb{Mz(Hq Hw Ir Iv Jo Mi Mr Mu Nb Nj Nr Oz Pa Pc Pe) Nf(Hx Jk Jn Jp Ma Mb Mp No Nx Pa Pe Qe) Nt(Hq Hr Io Ir Jk Jn Lx Mu Na Nm Qa) Lw(Iu Jo Lz Ma Mb Mj Mu Mw Nb Nx Qa) Nr(Hr Hv Ii Ij Iq Iv Li Lv Na Pc) Mw(Hv Im In Iu Jt Lz Mb Oz Qb Qd) Md(Hw Iv Jo Jp Mm Mp Mu Nn Nx) Jk(Im In Jp Jt Lx Ma Mi Qb Qe) Hq(Hr Im Jp Mp Mq Na Nm Qa) Li(Hr Hw Hx Iv Jo Mp Mu Nb) Pd(Hx Im Jp Jt Ma Mp Na Qa) Mi(Im Iv Jp Js Ma Qb Qe) Ij(Jp Lv Ma Nb Nq Qb Qe) In(Jp Lx Ma Mu Pa Qe) Na(Ih Iv Mn Mu Nm) Hw(Ih Iv Lv Oz Qd) Ii(Hx Jt My Ng Og) Nq(Ip Jo Jt Mb) Nb(Hr Jn Pc Qa) Nm(Lu Oz Qa) Ma(Jn Mp Ne) Mb(Fp Il Mj) Mu(Iq Lz Mj) Im(Jo Mq Qa) Jl(Is Jq Om) Pc(Ip Lx Pf) Lv(Hr Jt) Mp(Mh Ni) Hv(Lx Qb) Jo(Hx Nn) Nx(Jn Js) Pa(Pf Pg) MmNi MnMq IhPe} Mm{Im(Hr Hv Hw Ii Ij In It Js Jt Lw Mb Md Me Mh Mj Na Nb Nf Nr) Mi(Hv Hw Ij In It Jm Js Jt Mb Me Mz Na Ng Ni Oy Qa) Iq(Hr Hv Hw Ii Ij In It Iv Jo Lx Nb Nr Nt Pa Qa Qc) Ng(Ii Ij Il Jo Lu Lw Lx Mr Mv Nd Nq Nt Pd Pe) Ih(Hr Hw Ii In Jh Jo Lw Me Mu Na Nb Ni) Mu(Hv Hw In Jo Js Jt Na Nf Nr) Lz(Hr Ij In It Na Ni) Mr(Ir Jm Js Mb Mz Pc) Hw(Js Nf Nn Ns Nt Pc) Lu(It Jt Me Na Pc) Mg(Ii Jh Jk Jt Nb) Mx(Hr Hu Mb Md Mf) Mz(Iv Nl No Pa Pe) Nt(Hv Js Na Qa) Lx(Hq Jm Nf Pg) Hr(Jp Md Pc Qd) Pe(Js Nf Oy Pc) Nr(Js Nf Nn) Ns(Md Mq Pd) Ni(Jk Mh Pc) Po(Of Pg) Ii(My Og) Iv(Me Nf) Pa(Js Mk) NoJm LwNl MdMj MwHu NbOg HxQa QbJo JkOy JtPf} Mb{Im(Iq Ir Iv Jk Jp Js Lj Lz Ma Mh Mp Mr Mz Nf Nj Nx Qa Qb Qe) Js(Hq Hx Ii Jk Jp Lz Mh Mi Mn Mw Nd Nj Pa Qb Qe) Pc(Ih Iq Iv Jp Lz Ma Mp Mr Nf Nh Qa Qb Qe) Lv(Hx Ii Jk Jt Li Mi Mx Nb Nm Nq Nt Pa) Lj(Hq Ii Md Mi Nd Nh Nm Nq Nt Nx Pa) Mx(Hq Jk Jp Li Mn Nj Nm Qb Qc) Nf(Iv Jk Mh Mn

Figure 35 Continued

Ne Nt Qa Qb Qe) Mi(Ly Nm Oy Qa Qb Qe) Ih(Hq Ii Jk Mh Nb Nq) Lz(Iv Jk Qa Qd Qe) Nj(Fp Hx Mv Mw Qb) Jl(Et Is Jr Oh Oz) Mh(Jk Mn Nq Nx) Mz(Iu Mr Nl Pa) Lw(Iu Jt Nl) Hx(Ir Mp Nm) Iv(Jn Me Mr) Qa(Ir Jn Pa) Nh(Ii Jt) Nl(Mw Qe) Iq(Lh Po) Pa(Mk Qe) LuMn MpNb JkOy NxOg} Jh{Lw(Iq Ir Iv Lx Lz Mf Mh Mi Mr Nb Nl Pa Po) Lx(Hq Hw Ir Is Iv Jn Mg Mv My Mz Nn Of) My(Ii Lz Mi Mt Mz Nd Nf Nr Nt Pe Po) Pc(Hw Ii Im Iv Jo Mi Mr Mx Nf Oy Pe) Mg(Iu Jo Mi Mp Mr Nd Nm Pa Pe Po) Oy(Iq Lz Md Mu Mz Nd Nf Nr Nt) Nn(Hw Ii Mi Mr Mu Nr Pa) Mi(Hq Ir Jn Js Mz) J

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.6E1 | 1.3E2 | 8.5E1 | 1.5E2 | 5.6E1 | 1.0E2 | 7.0E0 | 1.6E1 | 4.0E2 | 4.8E2 | 260 | 38 | 260 | 38 | 0.72 |
| Ad | ug/mL | 4.6E-2 | 8.3E-2 | 7.2E-2 | 4.5E-1 | 8.7E-2 | 1.7E0 | 6.8E-4 | 7.8E-4 | 5.4E-1 | 8.5E0 | 150 | 24 | 150 | 24 | 0.63 |
| Af | ng/mL | 1.3E0 | 7.7E-1 | 1.1E1 | 4.1E0 | 4.7E1 | 6.5E0 | 1.7E-3 | 1.7E-3 | 5.3E2 | 2.3E1 | 150 | 24 | 150 | 24 | 0.44 |
| Aj | ug/mL | 1.4E0 | 2.9E-1 | 2.4E0 | 1.6E0 | 2.5E0 | 2.3E0 | 1.5E-3 | 1.3E-3 | 6.1E0 | 6.1E0 | 150 | 24 | 150 | 24 | 0.39 |
| Al | mg/mL | 8.3E-5 | 1.2E-4 | 2.6E-4 | 4.0E-4 | 4.3E-4 | 5.1E-4 | 4.3E-6 | 7.6E-6 | 1.8E-3 | 1.8E-3 | 150 | 24 | 150 | 24 | 0.58 |
| An | U/mL | 6.0E1 | 9.5E1 | 2.1E2 | 5.1E2 | 5.6E2 | 1.6E3 | 2.8E-1 | 6.4E-1 | 5.5E3 | 7.8E3 | 150 | 24 | 150 | 24 | 0.58 |
| Ao | pg/mL | 9.1E1 | 1.2E2 | 5.7E2 | 4.2E2 | 3.8E3 | 9.4E2 | 1.5E0 | 4.1E0 | 3.9E4 | 4.5E3 | 150 | 24 | 150 | 24 | 0.60 |
| Ap | ng/mL | 3.3E1 | 4.8E1 | 4.7E1 | 7.3E1 | 5.3E1 | 7.0E1 | 2.0E0 | 4.4E0 | 3.3E2 | 2.4E2 | 150 | 24 | 150 | 24 | 0.61 |
| Ar | ng/mL | 5.9E-1 | 2.4E0 | 2.7E0 | 5.5E0 | 6.9E0 | 1.0E1 | 3.4E-3 | 3.4E-3 | 5.1E1 | 5.0E1 | 150 | 24 | 150 | 24 | 0.70 |
| As | ng/mL | 8.7E-3 | 3.7E-3 | 1.2E-2 | 6.3E-2 | 1.7E-2 | 2.5E-1 | 1.7E-3 | 1.7E-3 | 1.3E-1 | 1.2E0 | 150 | 24 | 150 | 24 | 0.47 |
| Aw | pg/mL | 1.6E1 | 1.8E1 | 1.7E1 | 2.0E1 | 5.7E0 | 8.6E0 | 2.9E-2 | 1.1E1 | 4.2E1 | 5.1E1 | 150 | 24 | 150 | 24 | 0.58 |
| Ax | ng/mL | 1.7E0 | 9.0E0 | 1.9E1 | 9.8E1 | 8.2E1 | 2.1E2 | 1.3E-2 | 1.0E-4 | 7.7E2 | 8.5E2 | 150 | 24 | 150 | 24 | 0.68 |
| Ba | ng/mL | 8.2E1 | 4.6E2 | 5.2E2 | 1.9E3 | 1.4E3 | 3.5E3 | 1.1E0 | 3.1E0 | 8.1E3 | 1.5E4 | 150 | 24 | 150 | 24 | 0.65 |
| Bb | ng/mL | 3.9E0 | 1.4E1 | 6.3E0 | 1.5E1 | 7.7E0 | 1.2E1 | 4.1E-3 | 3.5E-1 | 4.9E1 | 4.8E1 | 150 | 24 | 150 | 24 | 0.74 |
| Bc | ng/mL | 3.3E1 | 9.5E1 | 1.2E2 | 2.1E2 | 2.3E2 | 3.0E2 | 4.9E-1 | 2.9E0 | 1.2E3 | 1.0E3 | 150 | 24 | 150 | 24 | 0.66 |
| Bg | ng/mL | 1.1E-1 | 1.7E-1 | 6.9E0 | 1.6E0 | 3.7E1 | 2.3E0 | 5.3E-4 | 2.4E-2 | 4.0E2 | 8.0E0 | 150 | 24 | 150 | 24 | 0.59 |
| Bn | ng/mL | 5.6E-2 | 5.6E-2 | 1.3E0 | 3.0E0 | 2.1E0 | 1.2E1 | 5.6E-2 | 5.6E-2 | 8.6E0 | 5.8E1 | 150 | 24 | 150 | 24 | 0.47 |
| Bo | ng/mL | 1.3E0 | 1.6E1 | 1.5E1 | 1.7E1 | 1.1E1 | 1.3E1 | 1.6E-2 | 1.6E-2 | 5.0E1 | 5.3E1 | 150 | 24 | 150 | 24 | 0.53 |
| Ch | uIU/mL | 1.0E0 | 9.6E-1 | 3.9E1 | 5.1E0 | 1.9E2 | 1.1E1 | 3.4E-3 | 1.4E-1 | 1.8E3 | 5.0E1 | 150 | 24 | 150 | 24 | 0.47 |
| Co | pg/mL | 4.6E1 | 6.5E1 | 2.3E2 | 2.0E2 | 1.4E3 | 4.2E2 | 1.5E-1 | 8.8E0 | 1.7E4 | 2.1E3 | 150 | 24 | 150 | 24 | 0.64 |
| Cp | ng/mL | 2.2E1 | 2.3E1 | 2.7E1 | 8.7E1 | 2.1E1 | 2.6E2 | 6.0E-1 | 1.0E1 | 1.3E2 | 1.3E3 | 150 | 24 | 150 | 24 | 0.58 |
| Cq | ng/mL | 2.9E-2 | 3.3E-2 | 1.1E-1 | 2.2E0 | 4.6E-1 | 1.0E1 | 8.0E-4 | 8.0E-4 | 5.1E0 | 4.9E1 | 150 | 24 | 150 | 24 | 0.58 |
| Cs | ng/mL | 5.6E1 | 2.4E2 | 4.2E2 | 9.5E2 | 1.7E3 | 1.6E3 | 8.9E-1 | 8.3E-1 | 1.8E4 | 5.1E3 | 150 | 24 | 150 | 24 | 0.68 |
| Ct | ng/mL | 3.4E-1 | 3.0E-1 | 4.0E1 | 5.2E1 | 1.2E2 | 1.2E2 | 1.3E-2 | 1.1E-4 | 6.2E2 | 4.7E2 | 150 | 24 | 150 | 24 | 0.49 |
| Cu | ng/mL | 2.5E-1 | 4.1E-1 | 4.9E-1 | 4.6E0 | 9.2E-1 | 1.4E1 | 1.9E-2 | 1.7E-2 | 9.0E0 | 6.6E1 | 150 | 24 | 150 | 24 | 0.66 |
| Cv | ng/mL | 4.5E0 | 1.7E1 | 2.5E1 | 5.9E1 | 6.3E1 | 1.1E2 | 2.0E-2 | 5.1E-2 | 5.3E2 | 4.7E2 | 150 | 24 | 150 | 24 | 0.61 |
| Cw | mIU/mL | 3.1E-2 | 5.3E-2 | 4.2E-2 | 3.3E-1 | 3.5E-2 | 1.4E0 | 8.9E-4 | 4.1E-3 | 2.3E-1 | 6.8E0 | 150 | 24 | 150 | 24 | 0.63 |
| Cx | ng/mL | 1.1E0 | 1.5E-2 | 5.3E1 | 3.2E1 | 1.0E2 | 7.9E1 | 9.3E-5 | 9.3E-5 | 3.9E2 | 2.8E2 | 150 | 24 | 150 | 24 | 0.39 |
| Db | ug/mL | 7.5E0 | 7.8E0 | 8.9E0 | 7.7E0 | 7.9E0 | 4.4E0 | 4.5E-1 | 1.0E0 | 5.9E1 | 1.9E1 | 150 | 24 | 150 | 24 | 0.50 |
| Dc | nmol/L | 2.0E-2 | 4.4E-2 | 5.8E-2 | 8.0E-1 | 1.6E-1 | 2.9E0 | 5.2E-6 | 2.1E-3 | 1.6E0 | 1.4E1 | 150 | 24 | 150 | 24 | 0.68 |
| Dd | ug/mL | 6.7E-2 | 2.8E-1 | 1.7E-1 | 4.5E-1 | 2.5E-1 | 7.6E-1 | 4.8E-4 | 3.4E-3 | 1.6E0 | 3.6E0 | 150 | 24 | 150 | 24 | 0.62 |
| De | ng/mL | 3.4E-3 | 3.4E-3 | 7.8E-2 | 1.3E-1 | 1.3E-1 | 2.8E-1 | 3.4E-3 | 3.4E-3 | 9.2E-1 | 1.1E0 | 150 | 24 | 150 | 24 | 0.48 |
| Dg | ng/mL | 3.7E1 | 4.1E1 | 4.7E1 | 5.7E1 | 4.0E1 | 4.3E1 | 7.1E-1 | 1.9E0 | 1.9E2 | 1.2E2 | 150 | 24 | 150 | 24 | 0.57 |
| Di | pg/mL | 2.0E0 | 3.0E0 | 2.4E0 | 3.2E0 | 2.2E0 | 1.8E0 | 1.8E-1 | 1.8E-1 | 1.3E1 | 9.0E0 | 150 | 24 | 150 | 24 | 0.66 |
| Dk | uIU/mL | 1.4E-2 | 2.2E-2 | 5.3E-2 | 1.2E-1 | 1.6E-1 | 2.5E-1 | 1.1E-4 | 1.1E-4 | 1.6E0 | 9.8E-1 | 150 | 24 | 150 | 24 | 0.58 |
| Dl | ng/mL | 1.9E2 | 2.6E2 | 2.9E2 | 3.9E2 | 2.7E2 | 3.7E2 | 5.5E0 | 4.4E0 | 1.3E3 | 1.6E3 | 150 | 24 | 150 | 24 | 0.58 |
| Dp | ng/ml | 2.3E0 | 1.7E0 | 5.6E0 | 3.3E0 | 9.1E0 | 4.9E0 | 3.7E-3 | 3.7E-3 | 5.6E1 | 1.4E1 | 121 | 14 | 121 | 14 | 0.38 |
| Dr | pg/ml | 2.2E1 | 3.4E1 | 4.1E1 | 1.2E3 | 5.4E1 | 3.3E3 | 7.5E-1 | 7.5E-1 | 2.5E2 | 1.0E4 | 62 | 10 | 62 | 10 | 0.68 |
| Du | pg/ml | 1.4E2 | 9.6E2 | 9.3E2 | 4.0E3 | 2.9E3 | 8.6E3 | 1.2E0 | 1.2E0 | 2.0E4 | 2.4E4 | 50 | 7 | 50 | 7 | 0.65 |
| Ef | ng/ml | 1.0E-1 | 2.4E-1 | 8.0E-1 | 1.6E0 | 1.8E0 | 3.0E0 | 5.7E-4 | 5.7E-4 | 1.0E1 | 9.9E0 | 130 | 17 | 130 | 17 | 0.58 |
| Wm | % | 8.5E-2 | 8.5E-2 | 1.5E1 | 7.5E1 | 9.9E1 | 2.5E2 | 5.4E-2 | 8.5E-2 | 8.7E2 | 1.0E3 | 140 | 18 | 140 | 18 | 0.52 |
| Ed | pg/ml | 5.2E-1 | 6.1E1 | 3.0E1 | 9.5E1 | 5.8E1 | 1.3E2 | 5.2E-1 | 5.2E-1 | 5.0E2 | 4.8E2 | 121 | 14 | 121 | 14 | 0.71 |
| Tj | pg/mL | 3.7E-1 | 5.0E-1 | 3.9E1 | 3.4E1 | 2.2E2 | 6.9E1 | 3.7E-1 | 3.7E-1 | 2.3E3 | 2.5E2 | 129 | 16 | 129 | 16 | 0.58 |
| Po | pg/ml | 1.4E-1 | 5.6E0 | 8.4E0 | 2.5E1 | 2.7E1 | 4.8E1 | 8.0E-3 | 2.6E-2 | 2.7E2 | 2.2E2 | 308 | 45 | 308 | 45 | 0.67 |
| Ti | ug/mL | 3.2E0 | 9.0E0 | 4.6E0 | 8.7E0 | 3.9E0 | 6.1E0 | 1.2E-1 | 9.7E-1 | 1.6E1 | 1.8E1 | 76 | 8 | 76 | 8 | 0.69 |
| Em | ng/ml | 9.2E-3 | 2.6E-2 | 4.7E-2 | 2.2E-1 | 9.0E-2 | 5.3E-1 | 8.4E-4 | 8.4E-4 | 5.0E-1 | 1.9E0 | 79 | 13 | 79 | 13 | 0.54 |
| Et | ng/ml | 1.3E3 | 3.0E3 | 1.6E3 | 2.8E3 | 1.1E3 | 1.2E3 | 7.5E1 | 5.9E2 | 4.8E3 | 5.0E3 | 307 | 45 | 307 | 45 | 0.78 |
| Eq | pg/ml | 2.3E2 | 3.1E1 | 3.6E2 | 2.5E2 | 3.8E2 | 5.2E2 | 1.0E0 | 1.0E0 | 1.5E3 | 1.4E3 | 50 | 7 | 50 | 7 | 0.32 |
| Th | ug/mL | 1.2E0 | 1.6E0 | 1.7E0 | 2.3E0 | 1.5E0 | 2.2E0 | 1.2E-1 | 2.6E-3 | 7.5E0 | 5.9E0 | 76 | 8 | 76 | 8 | 0.54 |
| Fa | ng/ml | 4.0E1 | 8.2E1 | 1.2E2 | 1.6E2 | 4.1E2 | 2.1E2 | 2.6E-1 | 6.0E-1 | 3.7E3 | 7.3E2 | 118 | 13 | 118 | 13 | 0.64 |
| Ez | ng/ml | 3.8E0 | 4.4E0 | 1.4E1 | 3.0E1 | 2.6E1 | 5.6E1 | 1.3E-2 | 1.3E-2 | 1.6E2 | 2.0E2 | 121 | 14 | 121 | 14 | 0.57 |
| Fb | ng/ml | 2.5E1 | 2.8E1 | 2.2E1 | 2.8E1 | 1.2E1 | 9.7E0 | 6.6E-1 | 4.6E0 | 4.3E1 | 4.1E1 | 119 | 13 | 119 | 13 | 0.64 |
| Ex | ng/ml | 7.5E-2 | 1.6E-1 | 1.8E-1 | 5.9E-1 | 3.2E-1 | 1.1E0 | 3.5E-5 | 1.7E-4 | 2.2E0 | 4.1E0 | 92 | 13 | 92 | 13 | 0.65 |
| Fc | pg/ml | 2.2E-1 | 6.3E0 | 2.0E1 | 5.4E1 | 8.2E1 | 1.1E2 | 2.2E-1 | 2.2E-1 | 4.5E2 | 3.1E2 | 51 | 7 | 51 | 7 | 0.69 |

Figure 36

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fd | pg/ml | 5.3E1 | 4.9E2 | 5.7E2 | 7.0E3 | 1.4E3 | 1.1E4 | 4.5E-1 | 9.8E-1 | 9.2E3 | 2.5E4 | 51 | 7 | 51 | 7 | 0.67 |
| Fi | pg/ml | 2.5E-1 | 6.1E1 | 8.1E1 | 1.7E2 | 3.0E2 | 2.1E2 | 2.5E-1 | 2.5E-1 | 1.8E3 | 5.3E2 | 51 | 7 | 51 | 7 | 0.69 |
| Fn | ng/ml | 2.1E-1 | 9.5E-1 | 3.7E0 | 6.0E0 | 6.9E0 | 8.4E0 | 1.1E-14 | 2.1E-1 | 3.7E1 | 2.7E1 | 121 | 14 | 121 | 14 | 0.57 |
| Fp | ng/ml | 1.2E1 | 3.4E1 | 2.2E1 | 3.7E1 | 2.6E1 | 3.3E1 | 6.0E-3 | 1.2E0 | 1.3E2 | 1.3E2 | 310 | 45 | 310 | 45 | 0.66 |
| Fr | ng/ml | 3.1E4 | 1.1E5 | 1.1E5 | 2.6E5 | 1.8E5 | 2.7E5 | 1.9E2 | 1.8E3 | 8.4E5 | 8.4E5 | 315 | 47 | 315 | 47 | 0.72 |
| Fw | pg/ml | 2.2E0 | 1.2E1 | 4.4E1 | 6.8E1 | 2.7E2 | 1.3E2 | 1.2E-1 | 1.2E-1 | 3.0E3 | 4.4E2 | 132 | 17 | 132 | 17 | 0.67 |
| Fy | ng/ml | 3.4E1 | 1.1E2 | 5.9E1 | 1.9E2 | 7.0E1 | 2.3E2 | 1.2E-1 | 7.0E0 | 5.0E2 | 6.5E2 | 120 | 12 | 120 | 12 | 0.68 |
| Gh | pg/ml | 2.3E0 | 3.9E0 | 2.3E1 | 1.2E1 | 5.7E1 | 1.7E1 | 2.9E-2 | 2.9E-2 | 3.2E2 | 4.6E1 | 51 | 7 | 51 | 7 | 0.54 |
| Gb | % | 4.1E1 | 6.2E1 | 4.6E1 | 1.0E2 | 4.0E1 | 1.0E2 | 2.2E0 | 2.5E1 | 2.3E2 | 3.0E2 | 51 | 7 | 51 | 7 | 0.71 |
| Gc | ng/ml | 9.5E1 | 2.0E2 | 1.5E2 | 2.9E2 | 2.0E2 | 2.2E2 | 6.4E0 | 6.5E1 | 1.2E3 | 6.7E2 | 62 | 10 | 62 | 10 | 0.72 |
| Gd | ng/ml | 3.3E1 | 2.7E1 | 3.4E1 | 3.2E1 | 1.8E1 | 2.3E1 | 3.0E0 | 9.6E0 | 8.1E1 | 8.0E1 | 72 | 10 | 72 | 10 | 0.43 |
| Gn | U/ml | 2.1E-1 | 2.8E-1 | 1.3E0 | 1.2E1 | 4.0E0 | 3.6E1 | 5.6E-3 | 2.7E-2 | 3.0E1 | 1.1E2 | 61 | 10 | 61 | 10 | 0.58 |
| Gl | pg/ml | 9.2E3 | 8.9E3 | 1.2E4 | 1.5E4 | 9.4E3 | 1.2E4 | 9.1E1 | 5.2E2 | 3.2E4 | 3.2E4 | 132 | 17 | 132 | 17 | 0.58 |
| Gp | U/ml | 1.1E0 | 5.1E-1 | 2.6E0 | 1.3E0 | 3.5E0 | 1.9E0 | 1.5E-2 | 1.5E-2 | 2.0E1 | 7.3E0 | 132 | 16 | 132 | 16 | 0.37 |
| Gz | ug/ml | 1.4E0 | 1.2E0 | 5.7E0 | 3.3E0 | 5.8E0 | 4.3E0 | 4.2E-2 | 1.0E-1 | 2.5E1 | 1.1E1 | 84 | 10 | 84 | 10 | 0.44 |
| Ha | ng/ml | 2.0E0 | 5.5E0 | 7.6E0 | 1.7E1 | 1.7E1 | 3.4E1 | 1.7E-2 | 1.7E-2 | 1.0E2 | 1.0E2 | 119 | 14 | 119 | 14 | 0.61 |
| Nm | pg/ml | 1.2E4 | 3.2E4 | 2.9E4 | 9.4E4 | 7.5E4 | 1.6E5 | 1.0E-9 | 1.0E-9 | 9.6E5 | 8.2E5 | 311 | 45 | 311 | 45 | 0.66 |
| Nn | pg/ml | 1.4E2 | 4.9E2 | 1.4E3 | 1.4E4 | 6.9E3 | 5.0E4 | 1.0E-9 | 1.0E-9 | 9.5E4 | 3.1E5 | 311 | 45 | 311 | 45 | 0.68 |
| No | pg/ml | 1.3E1 | 3.9E1 | 2.9E1 | 1.2E2 | 5.7E1 | 2.1E2 | 1.0E-9 | 1.6E0 | 5.6E2 | 9.1E2 | 311 | 45 | 311 | 45 | 0.75 |
| Nq | pg/ml | 1.5E0 | 5.3E0 | 1.9E1 | 5.8E1 | 6.9E1 | 1.4E2 | 1.0E-9 | 1.0E-9 | 6.7E2 | 6.3E2 | 311 | 45 | 311 | 45 | 0.64 |
| Nr | pg/ml | 1.3E0 | 6.6E0 | 2.0E1 | 7.8E1 | 7.6E1 | 2.3E2 | 1.0E-9 | 1.0E-9 | 9.8E2 | 1.4E3 | 311 | 45 | 311 | 45 | 0.67 |
| Ns | pg/ml | 1.0E-9 | 1.0E-9 | 8.6E0 | 8.0E-2 | 6.8E1 | 5.3E-1 | 1.0E-9 | 1.0E-9 | 1.1E3 | 3.6E0 | 311 | 45 | 311 | 45 | 0.47 |
| Nt | pg/ml | 9.9E1 | 1.5E2 | 1.3E2 | 2.5E2 | 9.9E1 | 3.0E2 | 9.8E-1 | 5.5E1 | 8.8E2 | 1.7E3 | 311 | 45 | 311 | 45 | 0.68 |
| Nu | pg/ml | 1.2E1 | 5.9E1 | 5.3E1 | 8.8E1 | 9.2E1 | 9.5E1 | 1.0E-9 | 1.0E-9 | 6.3E2 | 3.7E2 | 311 | 45 | 311 | 45 | 0.67 |
| Lu | pg/ml | 1.0E4 | 1.0E4 | 1.6E4 | 1.2E4 | 4.2E4 | 1.0E4 | 7.7E2 | 5.2E2 | 5.6E5 | 5.7E4 | 311 | 45 | 311 | 45 | 0.51 |
| Lv | pg/ml | 1.0E-9 | 7.3E0 | 1.5E1 | 2.9E1 | 3.1E1 | 3.9E1 | 1.0E-9 | 1.0E-9 | 2.6E2 | 1.6E2 | 311 | 45 | 311 | 45 | 0.62 |
| Lw | pg/ml | 1.0E-9 | 1.0E-9 | 3.9E-1 | 6.7E0 | 4.9E0 | 2.7E1 | 1.0E-9 | 1.0E-9 | 8.0E1 | 1.8E2 | 311 | 45 | 311 | 45 | 0.57 |
| Lx | pg/ml | 1.0E-9 | 1.6E2 | 1.6E2 | 9.9E2 | 5.6E2 | 3.3E3 | 1.0E-9 | 1.0E-9 | 6.2E3 | 2.2E4 | 311 | 45 | 311 | 45 | 0.72 |
| Ly | pg/ml | 1.0E-9 | 1.0E-9 | 9.6E0 | 5.9E0 | 1.8E1 | 1.4E1 | 1.0E-9 | 1.0E-9 | 1.1E2 | 6.0E1 | 311 | 45 | 311 | 45 | 0.44 |
| Lz | pg/ml | 1.0E-9 | 1.0E-9 | 3.2E0 | 5.1E0 | 2.7E1 | 1.5E1 | 1.0E-9 | 1.0E-9 | 4.3E2 | 6.2E1 | 311 | 45 | 311 | 45 | 0.56 |
| Ma | pg/ml | 3.7E2 | 1.6E3 | 2.1E3 | 4.5E3 | 6.0E3 | 7.7E3 | 1.0E-9 | 2.4E1 | 6.5E4 | 3.6E4 | 311 | 45 | 311 | 45 | 0.69 |
| Mb | pg/ml | 2.5E1 | 2.8E1 | 3.2E1 | 3.2E1 | 1.8E1 | 1.4E1 | 9.2E0 | 4.1E0 | 2.1E2 | 6.4E1 | 311 | 45 | 311 | 45 | 0.52 |
| Mc | pg/ml | 1.0E-9 | 1.0E-9 | 6.1E-2 | 1.0E-9 | 7.8E-1 | 0.0E0 | 1.0E-9 | 1.0E-9 | 1.3E1 | 1.0E-9 | 311 | 45 | 311 | 45 | 0.49 |
| Md | pg/ml | 1.0E-9 | 1.0E-9 | 6.3E-1 | 9.2E-1 | 5.5E0 | 4.5E0 | 1.0E-9 | 1.0E-9 | 6.8E1 | 2.9E1 | 311 | 45 | 311 | 45 | 0.53 |
| Me | pg/ml | 3.1E1 | 3.7E1 | 3.0E1 | 3.5E1 | 2.4E1 | 2.8E1 | 1.0E-9 | 1.0E-9 | 3.2E2 | 1.8E2 | 311 | 45 | 311 | 45 | 0.59 |
| Mf | pg/ml | 1.0E-9 | 1.0E-9 | 6.8E-1 | 3.6E-1 | 4.1E0 | 1.1E0 | 1.0E-9 | 1.0E-9 | 5.6E1 | 4.5E0 | 311 | 45 | 311 | 45 | 0.51 |
| Mg | pg/ml | 9.3E-1 | 1.8E0 | 6.1E0 | 1.3E1 | 1.1E1 | 2.8E1 | 1.0E-9 | 1.0E-9 | 9.2E1 | 1.5E2 | 311 | 45 | 311 | 45 | 0.55 |
| Mh | pg/ml | 1.0E-9 | 1.0E-9 | 1.2E0 | 1.2E0 | 8.0E0 | 3.7E0 | 1.0E-9 | 1.0E-9 | 1.1E2 | 1.8E1 | 311 | 45 | 311 | 45 | 0.58 |
| Mi | pg/ml | 1.0E-9 | 1.0E-9 | 8.7E-1 | 2.4E1 | 8.3E1 | 9.1E1 | 1.0E-9 | 1.0E-9 | 1.2E2 | 5.2E2 | 311 | 45 | 311 | 45 | 0.60 |
| Mj | pg/ml | 1.0E-9 | 1.0E-9 | 5.9E0 | 1.6E1 | 3.2E1 | 4.3E1 | 1.0E-9 | 1.0E-9 | 4.6E2 | 2.1E2 | 311 | 45 | 311 | 45 | 0.59 |
| Mk | pg/ml | 9.1E-1 | 3.9E0 | 1.6E1 | 2.0E1 | 9.7E1 | 7.7E1 | 1.0E-9 | 1.0E-9 | 1.3E3 | 5.0E2 | 311 | 45 | 311 | 45 | 0.54 |
| Ml | pg/ml | 1.0E-9 | 1.0E-9 | 9.3E0 | 2.3E1 | 1.2E2 | 9.2E1 | 1.0E-9 | 1.0E-9 | 2.1E3 | 5.1E2 | 311 | 45 | 311 | 45 | 0.52 |
| Mm | pg/ml | 4.7E2 | 1.1E3 | 9.8E2 | 1.9E3 | 1.3E3 | 2.2E3 | 1.0E-9 | 1.0E-9 | 1.0E4 | 1.0E4 | 311 | 45 | 311 | 45 | 0.66 |
| Mn | pg/ml | 5.5E0 | 1.1E1 | 1.1E1 | 1.4E1 | 2.6E1 | 1.0E1 | 1.0E-9 | 1.1E0 | 3.5E2 | 5.1E1 | 311 | 45 | 311 | 45 | 0.70 |
| Mp | pg/ml | 1.0E-9 | 8.8E0 | 1.1E1 | 9.4E1 | 4.1E1 | 3.6E2 | 1.0E-9 | 1.0E-9 | 6.3E2 | 2.4E3 | 311 | 45 | 311 | 45 | 0.64 |
| Mq | pg/ml | 1.0E-9 | 1.0E-9 | 2.2E0 | 6.7E0 | 1.3E1 | 2.0E1 | 1.0E-9 | 1.0E-9 | 1.8E2 | 1.0E2 | 311 | 45 | 311 | 45 | 0.54 |
| Mr | pg/ml | 1.0E-9 | 2.8E0 | 2.1E1 | 2.0E2 | 1.2E2 | 6.3E2 | 1.0E-9 | 1.0E-9 | 1.5E3 | 3.4E3 | 311 | 45 | 311 | 45 | 0.62 |
| Ms | pg/ml | 3.3E2 | 2.6E2 | 4.7E2 | 4.3E2 | 5.4E2 | 7.3E2 | 1.0E-9 | 1.0E-9 | 3.3E3 | 4.7E3 | 311 | 45 | 311 | 45 | 0.45 |
| Mt | pg/ml | 1.7E-1 | 1.6E0 | 7.6E0 | 1.0E2 | 4.4E1 | 4.8E2 | 1.0E-9 | 1.0E-9 | 7.1E2 | 3.2E3 | 311 | 45 | 311 | 45 | 0.67 |
| Mu | pg/ml | 1.0E-9 | 1.0E-9 | 1.5E0 | 2.9E0 | 1.5E1 | 9.3E0 | 1.0E-9 | 1.0E-9 | 2.3E2 | 4.8E1 | 311 | 45 | 311 | 45 | 0.55 |
| Mv | pg/ml | 1.0E-9 | 1.0E-9 | 6.5E2 | 1.1E2 | 3.5E2 | 2.5E2 | 1.0E-9 | 1.0E-9 | 4.5E3 | 9.2E2 | 311 | 45 | 311 | 45 | 0.58 |
| Mw | pg/ml | 3.0E1 | 1.2E2 | 2.7E2 | 5.9E2 | 1.4E3 | 1.2E3 | 1.0E-9 | 1.0E-9 | 1.8E4 | 5.3E3 | 311 | 45 | 311 | 45 | 0.72 |
| Mx | pg/ml | 1.0E-9 | 1.0E-9 | 3.3E-1 | 1.1E0 | 2.0E0 | 3.2E0 | 1.0E-9 | 1.0E-9 | 3.2E1 | 2.0E1 | 311 | 45 | 311 | 45 | 0.60 |
| My | pg/ml | 1.0E-9 | 1.0E-9 | 3.5E2 | 1.6E2 | 2.6E3 | 4.1E2 | 1.0E-9 | 1.0E-9 | 3.9E4 | 1.9E3 | 311 | 45 | 311 | 45 | 0.56 |
| Mz | pg/ml | 1.1E1 | 3.0E1 | 2.4E1 | 1.2E2 | 5.0E1 | 3.4E2 | 1.0E-9 | 1.0E-9 | 5.5E2 | 1.9E3 | 311 | 45 | 311 | 45 | 0.75 |
| Na | pg/ml | 1.0E-9 | 1.0E-9 | 6.7E-1 | 1.5E0 | 1.9E0 | 6.4E0 | 1.0E-9 | 1.0E-9 | 9.6E0 | 4.2E1 | 311 | 45 | 311 | 45 | 0.52 |
| Nb | pg/ml | 2.1E0 | 3.3E0 | 3.5E0 | 1.3E1 | 1.0E1 | 3.5E1 | 1.0E-9 | 1.0E-9 | 1.5E2 | 2.1E2 | 311 | 45 | 311 | 45 | 0.63 |

Figure 36 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nc | pg/ml | 3.4E2 | 5.3E1 | 5.2E2 | 4.0E2 | 7.4E2 | 6.2E2 | 1.0E-9 | 1.0E-9 | 9.2E3 | 3.2E3 | 311 | 45 | 311 | 45 | 0.41 |
| Nd | pg/ml | 2.7E1 | 3.7E1 | 2.7E1 | 8.1E1 | 7.1E1 | 3.1E2 | 1.0E-9 | 1.0E-9 | 1.2E3 | 2.1E3 | 311 | 45 | 311 | 45 | 0.63 |
| Ne | pg/ml | 4.2E2 | 4.0E2 | 5.2E2 | 4.8E2 | 5.6E2 | 5.8E2 | 1.0E-9 | 1.0E-9 | 7.0E3 | 3.6E3 | 311 | 45 | 311 | 45 | 0.46 |
| Nf | pg/ml | 1.0E-9 | 1.0E-9 | 2.5E0 | 6.7E0 | 9.0E0 | 2.6E1 | 1.0E-9 | 1.0E-9 | 8.2E1 | 1.3E2 | 311 | 45 | 311 | 45 | 0.49 |
| Ng | pg/ml | 1.2E1 | 1.7E1 | 9.0E1 | 8.5E1 | 1.9E2 | 1.3E2 | 1.0E-9 | 1.0E-9 | 1.6E3 | 5.3E2 | 311 | 45 | 311 | 45 | 0.54 |
| Nh | pg/ml | 6.3E1 | 5.5E1 | 8.1E1 | 6.7E1 | 7.5E1 | 8.1E1 | 1.0E-9 | 4.1E0 | 5.6E2 | 5.1E2 | 311 | 45 | 311 | 45 | 0.42 |
| Ni | pg/ml | 9.4E0 | 1.0E-9 | 8.3E1 | 1.0E2 | 1.3E2 | 2.1E2 | 1.0E-9 | 1.0E-9 | 7.1E2 | 1.1E3 | 311 | 45 | 311 | 45 | 0.45 |
| Nj | pg/ml | 7.2E0 | 6.7E0 | 1.1E1 | 9.2E0 | 1.2E1 | 9.5E0 | 1.0E-9 | 1.0E-9 | 6.9E1 | 4.6E1 | 311 | 45 | 311 | 45 | 0.46 |
| Nk | pg/ml | 1.8E1 | 1.2E1 | 3.1E1 | 3.6E1 | 3.6E1 | 5.3E1 | 1.0E-9 | 1.0E-9 | 2.0E2 | 2.0E2 | 311 | 45 | 311 | 45 | 0.48 |
| Nl | pg/ml | 4.3E1 | 3.9E1 | 5.8E1 | 4.6E1 | 7.8E1 | 4.9E1 | 1.0E-9 | 1.0E-9 | 1.1E3 | 2.3E2 | 311 | 45 | 311 | 45 | 0.43 |
| Hl | pg/ml | 4.6E0 | 1.1E1 | 3.2E1 | 5.3E2 | 5.5E1 | 1.4E3 | 1.0E-9 | 1.0E-9 | 3.0E2 | 3.6E3 | 51 | 7 | 51 | 7 | 0.57 |
| Ho | pg/ml | 1.8E1 | 3.3E1 | 2.2E1 | 1.1E2 | 2.0E1 | 1.4E2 | 1.0E-9 | 7.6E0 | 8.7E1 | 3.9E2 | 51 | 7 | 51 | 7 | 0.67 |
| Hp | ng/ml | 1.6E0 | 6.9E0 | 9.0E1 | 3.8E2 | 2.7E2 | 4.7E2 | 1.0E-9 | 8.8E-1 | 8.9E2 | 8.9E2 | 51 | 7 | 51 | 7 | 0.72 |
| Tz | pg/ml | 4.2E3 | 7.2E3 | 7.9E3 | 1.8E5 | 1.7E4 | 5.5E5 | 1.0E-9 | 6.3E2 | 1.7E5 | 2.1E6 | 121 | 14 | 121 | 14 | 0.63 |
| Ua | pg/ml | 3.3E3 | 7.1E3 | 3.2E4 | 1.6E4 | 1.9E5 | 2.6E4 | 1.0E-9 | 1.4E3 | 2.1E6 | 9.9E4 | 121 | 14 | 121 | 14 | 0.62 |
| Ub | pg/ml | 5.7E2 | 3.2E2 | 8.7E2 | 6.9E2 | 1.2E3 | 1.1E3 | 1.0E-9 | 2.3E0 | 9.8E3 | 4.1E3 | 121 | 14 | 121 | 14 | 0.37 |
| Ue | pg/ml | 2.7E1 | 2.6E1 | 3.5E1 | 4.5E1 | 3.1E1 | 4.5E1 | 9.8E-2 | 4.5E0 | 2.7E2 | 1.4E2 | 121 | 14 | 121 | 14 | 0.51 |
| Uc | pg/ml | 7.1E2 | 1.1E3 | 1.3E3 | 5.7E3 | 1.6E3 | 1.5E4 | 1.0E-9 | 4.1E1 | 9.4E3 | 5.7E4 | 121 | 14 | 121 | 14 | 0.57 |
| Ud | pg/ml | 1.0E-9 | 1.0E-9 | 3.2E0 | 3.8E0 | 3.5E1 | 1.4E1 | 1.0E-9 | 1.0E-9 | 3.9E2 | 5.3E1 | 121 | 14 | 121 | 14 | 0.53 |
| Hq | pg/ml | 1.2E0 | 9.1E-1 | 1.7E2 | 7.2E1 | 2.0E3 | 4.1E2 | 1.0E-9 | 1.0E-9 | 2.8E4 | 2.8E3 | 309 | 45 | 309 | 45 | 0.51 |
| Hr | pg/ml | 9.3E1 | 8.6E1 | 6.8E2 | 4.2E2 | 1.4E3 | 1.4E3 | 1.0E-9 | 1.0E-9 | 1.2E4 | 8.9E3 | 309 | 45 | 309 | 45 | 0.42 |
| Hu | pg/ml | 4.8E0 | 6.5E1 | 5.1E3 | 6.4E2 | 4.2E4 | 1.4E3 | 1.0E-9 | 1.0E-9 | 6.3E5 | 6.5E3 | 309 | 45 | 309 | 45 | 0.60 |
| Hv | pg/ml | 1.5E0 | 9.2E-1 | 2.5E0 | 2.7E1 | 5.7E0 | 1.3E2 | 1.0E-9 | 1.0E-9 | 6.9E1 | 8.9E2 | 309 | 45 | 309 | 45 | 0.47 |
| Hw | pg/ml | 6.4E0 | 5.7E0 | 1.5E1 | 2.4E2 | 4.7E1 | 1.4E3 | 1.0E-9 | 4.6E-1 | 6.4E2 | 9.4E3 | 309 | 45 | 309 | 45 | 0.48 |
| Hx | pg/ml | 8.8E0 | 1.2E1 | 5.6E1 | 7.3E1 | 5.3E2 | 2.2E2 | 1.0E-9 | 1.0E-9 | 9.3E3 | 1.3E3 | 309 | 45 | 309 | 45 | 0.58 |
| Ib | ng/ml | 3.9E-2 | 2.8E-2 | 1.1E0 | 4.1E0 | 4.7E0 | 1.5E1 | 1.0E-9 | 1.0E-9 | 3.6E1 | 5.6E1 | 119 | 14 | 119 | 14 | 0.49 |
| Ic | U/ml | 2.2E2 | 2.2E2 | 9.0E2 | 2.6E2 | 6.0E3 | 1.4E2 | 2.4E0 | 2.5E1 | 6.5E4 | 4.2E2 | 119 | 14 | 119 | 14 | 0.62 |
| Id | U/ml | 6.2E-1 | 1.2E0 | 1.3E0 | 3.3E1 | 2.0E0 | 1.2E2 | 1.0E-9 | 3.3E-1 | 1.3E1 | 4.3E2 | 119 | 14 | 119 | 14 | 0.68 |
| Tt | pg/ml | 1.7E2 | 1.7E2 | 1.7E2 | 1.9E2 | 5.4E1 | 8.6E1 | 4.3E1 | 1.1E2 | 3.6E2 | 4.4E2 | 111 | 13 | 111 | 13 | 0.53 |
| To | pg/ml | 1.6E0 | 1.8E0 | 2.1E0 | 2.6E0 | 2.9E0 | 3.1E0 | 1.0E-9 | 1.0E-9 | 2.3E1 | 1.2E1 | 117 | 14 | 117 | 14 | 0.55 |
| Tr | pg/ml | 3.2E0 | 5.2E0 | 8.5E0 | 1.2E1 | 3.0E1 | 2.0E1 | 1.0E-9 | 6.3E-1 | 3.1E2 | 7.6E1 | 115 | 13 | 115 | 13 | 0.61 |
| Tn | pg/ml | 3.0E1 | 5.4E1 | 1.2E2 | 2.7E2 | 3.3E2 | 6.0E2 | 1.0E-9 | 1.3E1 | 2.0E3 | 2.3E3 | 117 | 14 | 117 | 14 | 0.67 |
| Tv | ng/ml | 1.2E1 | 8.7E0 | 2.7E1 | 5.4E2 | 7.9E1 | 1.9E3 | 1.0E-9 | 1.0E-9 | 7.9E2 | 7.1E3 | 117 | 14 | 117 | 14 | 0.44 |
| Ih | ng/ml | 5.8E1 | 2.6E2 | 2.1E2 | 6.4E2 | 3.7E2 | 8.1E2 | 1.0E-9 | 2.4E0 | 2.5E3 | 3.6E3 | 310 | 45 | 310 | 45 | 0.69 |
| Ii | ng/ml | 7.8E1 | 1.3E2 | 2.0E2 | 4.1E2 | 4.8E2 | 8.7E2 | 7.3E-1 | 7.5E-1 | 5.2E3 | 4.5E3 | 310 | 45 | 310 | 45 | 0.62 |
| Ij | ng/ml | 7.3E1 | 1.6E2 | 1.7E2 | 8.3E2 | 5.9E2 | 3.6E3 | 2.8E0 | 9.5E0 | 6.4E3 | 2.4E4 | 307 | 44 | 307 | 44 | 0.75 |
| Ik | ng/ml | 1.1E1 | 1.3E1 | 1.4E3 | 1.7E2 | 1.2E4 | 3.5E2 | 5.9E-1 | 6.2E-1 | 1.2E5 | 1.5E3 | 307 | 44 | 307 | 44 | 0.55 |
| Il | ng/ml | 3.3E2 | 5.2E2 | 1.2E3 | 2.3E3 | 2.8E3 | 3.9E3 | 1.0E-9 | 1.0E-9 | 1.2E4 | 1.2E4 | 305 | 44 | 305 | 44 | 0.59 |
| Im | ng/ml | 2.0E2 | 7.0E2 | 3.5E2 | 1.6E3 | 5.2E2 | 2.6E3 | 1.4E1 | 2.2E1 | 6.0E3 | 1.5E4 | 306 | 45 | 306 | 45 | 0.80 |
| In | ng/ml | 3.6E0 | 3.0E0 | 2.0E1 | 1.3E2 | 9.2E1 | 6.7E2 | 1.0E-9 | 1.0E-9 | 1.1E3 | 4.5E3 | 310 | 45 | 310 | 45 | 0.50 |
| Hb | ng/ml | 2.1E1 | 5.1E1 | 3.1E1 | 7.0E1 | 3.1E1 | 6.0E1 | 4.8E-1 | 4.5E0 | 2.0E2 | 1.9E2 | 122 | 14 | 122 | 14 | 0.72 |
| Hc | pg/ml | 6.7E2 | 5.2E2 | 3.3E3 | 1.7E3 | 1.1E4 | 3.6E3 | 1.0E-9 | 1.0E-9 | 1.0E5 | 1.4E4 | 122 | 14 | 122 | 14 | 0.45 |
| Hf | ng/ml | 1.8E2 | 2.6E2 | 4.0E2 | 3.3E2 | 5.7E2 | 3.1E2 | 1.0E-9 | 1.0E-9 | 3.2E3 | 9.9E2 | 122 | 14 | 122 | 14 | 0.51 |
| Io | ng/ml | 7.7E3 | 2.0E4 | 1.9E4 | 2.4E4 | 4.8E4 | 2.3E4 | 1.0E-9 | 6.2E2 | 7.1E5 | 1.0E5 | 310 | 45 | 310 | 45 | 0.65 |
| Ip | ng/ml | 8.4E0 | 3.0E1 | 2.0E1 | 3.2E1 | 2.6E1 | 2.1E1 | 1.0E-9 | 3.3E-1 | 2.3E2 | 7.8E1 | 310 | 45 | 310 | 45 | 0.69 |
| Iq | ug/ml | 9.9E-2 | 3.1E-1 | 4.5E1 | 7.3E0 | 7.7E2 | 3.3E1 | 1.0E-9 | 1.0E-9 | 1.4E4 | 2.2E2 | 310 | 45 | 310 | 45 | 0.66 |
| Ir | ug/ml | 3.5E-1 | 1.7E0 | 4.3E0 | 2.0E1 | 3.3E1 | 6.1E1 | 1.0E-9 | 3.5E-2 | 5.1E2 | 3.7E2 | 309 | 45 | 309 | 45 | 0.73 |
| Is | ng/ml | 1.8E0 | 9.8E0 | 7.9E0 | 3.1E1 | 3.3E1 | 5.1E1 | 1.0E-9 | 3.3E-2 | 5.5E2 | 2.6E2 | 310 | 45 | 310 | 45 | 0.68 |
| It | ng/ml | 1.8E0 | 5.4E0 | 2.2E1 | 3.9E1 | 1.0E2 | 1.3E2 | 1.0E-9 | 1.0E-9 | 1.1E3 | 6.8E2 | 310 | 45 | 310 | 45 | 0.69 |
| Iu | ng/ml | 1.6E2 | 2.4E2 | 1.3E3 | 2.5E3 | 4.1E3 | 6.3E3 | 1.0E-9 | 1.0E-9 | 2.9E4 | 2.4E4 | 310 | 45 | 310 | 45 | 0.57 |
| Iv | ng/ml | 1.1E1 | 2.6E1 | 8.6E1 | 3.3E2 | 9.0E2 | 9.4E2 | 1.0E-9 | 1.0E-9 | 1.6E4 | 3.8E3 | 309 | 45 | 309 | 45 | 0.66 |
| Iz | ng/ml | 1.2E2 | 2.0E2 | 3.8E2 | 3.0E2 | 7.5E2 | 3.2E2 | 1.5E0 | 8.8E-1 | 6.1E3 | 1.0E3 | 122 | 14 | 122 | 14 | 0.54 |
| Yd | ng/ml | 2.7E-1 | 7.6E-2 | 4.3E-1 | 1.9E-1 | 5.4E-1 | 2.0E-1 | 6.6E-3 | 1.7E-2 | 2.3E0 | 5.6E-1 | 51 | 7 | 51 | 7 | 0.37 |
| Wb | pg/ml | 2.7E4 | 3.5E4 | 3.3E4 | 1.4E5 | 1.9E4 | 2.3E5 | 4.9E3 | 1.4E4 | 8.4E4 | 6.4E5 | 51 | 7 | 51 | 7 | 0.67 |
| Vz | pg/ml | 3.5E0 | 5.0E0 | 4.5E0 | 6.0E0 | 4.1E0 | 7.5E0 | 1.0E-9 | 7.6E-2 | 2.1E1 | 2.2E1 | 51 | 7 | 51 | 7 | 0.54 |
| Si | ng/ml | 1.2E0 | 2.7E0 | 1.8E0 | 3.2E0 | 2.4E0 | 2.2E0 | 8.6E-3 | 5.6E-1 | 1.0E1 | 6.0E0 | 51 | 7 | 51 | 7 | 0.72 |
| Sf | mIU/mL | 1.5E1 | 2.0E1 | 4.9E1 | 2.8E1 | 1.1E2 | 2.7E1 | 6.2E-1 | 6.7E0 | 7.2E2 | 8.3E1 | 51 | 7 | 51 | 7 | 0.56 |

Figure 36 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Sh | mIU/mL | 1.6E1 | 1.0E1 | 4.5E1 | 1.0E1 | 9.2E1 | 5.5E0 | 7.8E-2 | 4.2E0 | 5.7E2 | 2.1E1 | 51 | 7 | 51 | 7 | 0.40 |
| Sj | ng/ml | 4.4E-1 | 4.3E-1 | 4.3E-1 | 4.1E-1 | 9.8E-2 | 6.1E-2 | 2.5E-1 | 3.4E-1 | 7.2E-1 | 4.8E-1 | 51 | 7 | 51 | 7 | 0.48 |
| Rc | pg/ml | 6.6E3 | 7.2E3 | 7.9E3 | 6.5E3 | 6.1E3 | 3.3E3 | 3.9E2 | 1.1E3 | 3.9E4 | 1.3E4 | 121 | 14 | 121 | 14 | 0.48 |
| Rb | pg/ml | 7.1E-1 | 1.9E0 | 2.7E0 | 6.0E0 | 4.1E0 | 1.5E1 | 1.0E-9 | 1.0E-9 | 2.0E1 | 5.6E1 | 121 | 14 | 121 | 14 | 0.55 |
| Zw | 2.5ng/ml | 5.6E0 | 4.7E0 | 9.1E0 | 1.9E1 | 1.1E1 | 2.9E1 | 1.4E-1 | 7.7E-1 | 5.9E1 | 6.3E1 | 51 | 7 | 51 | 7 | 0.51 |
| Zx | 2.3mU/ml | 1.2E-1 | 1.8E-1 | 3.0E-1 | 2.4E-1 | 5.4E-1 | 2.0E-1 | 3.2E-2 | 7.7E-2 | 2.9E0 | 6.7E-1 | 51 | 7 | 51 | 7 | 0.64 |
| Pz | ng/ml | 3.2E3 | 1.0E4 | 5.4E3 | 7.0E3 | 6.1E3 | 4.8E3 | 1.6E1 | 4.0E1 | 7.0E4 | 2.5E4 | 306 | 45 | 306 | 45 | 0.62 |
| Qa | ng/ml | 3.4E3 | 9.4E3 | 6.4E3 | 1.8E4 | 7.5E3 | 3.3E4 | 1.5E2 | 6.8E2 | 4.2E4 | 2.2E5 | 306 | 45 | 306 | 45 | 0.71 |
| Qb | ng/ml | 1.0E2 | 2.1E2 | 2.1E2 | 4.4E2 | 3.9E2 | 6.5E2 | 7.9E-1 | 1.8E1 | 5.3E3 | 4.1E3 | 306 | 45 | 306 | 45 | 0.69 |
| Qc | ng/ml | 1.8E2 | 6.5E2 | 4.0E2 | 7.9E2 | 5.4E2 | 8.1E2 | 1.0E-9 | 1.0E-9 | 3.8E3 | 4.3E3 | 306 | 45 | 306 | 45 | 0.67 |
| Qd | ng/ml | 8.2E3 | 2.3E4 | 2.3E4 | 6.2E4 | 1.2E5 | 8.8E4 | 1.5E2 | 1.7E3 | 2.0E6 | 4.3E5 | 306 | 45 | 306 | 45 | 0.73 |
| Qe | ng/ml | 7.8E2 | 2.4E3 | 2.0E3 | 3.4E3 | 5.9E3 | 3.5E3 | 1.0E-9 | 8.8E0 | 9.7E4 | 1.8E4 | 306 | 45 | 306 | 45 | 0.70 |
| Jd | ng/ml | 8.8E-1 | 2.6E0 | 3.9E0 | 5.0E0 | 1.5E1 | 6.6E0 | 1.0E-9 | 1.0E-9 | 1.2E2 | 2.1E1 | 121 | 14 | 121 | 14 | 0.64 |
| Je | ng/ml | 1.0E-9 | 2.8E-1 | 1.7E0 | 2.4E0 | 5.0E0 | 3.5E0 | 1.0E-9 | 1.0E-9 | 4.6E1 | 1.1E1 | 121 | 14 | 121 | 14 | 0.57 |
| Jf | ng/ml | 1.0E-9 | 1.0E-9 | 1.3E0 | 4.8E-1 | 2.3E0 | 1.1E0 | 1.0E-9 | 1.0E-9 | 1.2E1 | 3.7E0 | 121 | 14 | 121 | 14 | 0.41 |
| Jg | ng/ml | 4.0E2 | 1.2E3 | 7.3E2 | 1.5E3 | 9.3E2 | 1.3E3 | 5.8E0 | 5.4E1 | 1.0E4 | 7.1E3 | 309 | 45 | 309 | 45 | 0.71 |
| Jh | ng/ml | 2.6E0 | 9.4E0 | 2.0E1 | 4.5E1 | 8.5E1 | 9.2E1 | 1.0E-9 | 1.0E-9 | 1.2E3 | 4.9E2 | 309 | 45 | 309 | 45 | 0.66 |
| Ji | ng/ml | 5.3E1 | 1.4E2 | 7.6E1 | 2.4E2 | 7.7E1 | 2.5E2 | 1.1E0 | 2.3E1 | 5.3E2 | 1.3E3 | 309 | 45 | 309 | 45 | 0.75 |
| Sr | pg/mL | 3.8E2 | 2.4E3 | 7.9E2 | 3.4E3 | 1.1E3 | 5.3E3 | 1.0E-9 | 9.7E1 | 5.5E3 | 2.1E4 | 120 | 14 | 120 | 14 | 0.76 |
| Ss | pg/mL | 9.3E4 | 4.9E4 | 1.5E5 | 1.2E5 | 1.8E5 | 1.5E5 | 2.7E3 | 7.8E3 | 1.3E6 | 5.7E5 | 120 | 14 | 120 | 14 | 0.41 |
| St | pg/mL | 2.4E7 | 1.0E8 | 6.0E7 | 1.8E8 | 1.3E8 | 4.2E8 | 1.0E-9 | 3.4E6 | 1.2E9 | 1.7E9 | 119 | 14 | 119 | 14 | 0.71 |
| Wc | ng/ml | 1.0E-9 | 1.0E-9 | 5.9E-2 | 3.5E-1 | 1.0E-1 | 6.8E-1 | 1.0E-9 | 1.0E-9 | 5.2E-1 | 1.8E0 | 51 | 7 | 51 | 7 | 0.51 |
| Wd | ng/ml | 9.3E0 | 1.8E1 | 2.7E1 | 1.2E2 | 5.8E1 | 1.9E2 | 1.0E0 | 3.5E0 | 2.9E2 | 4.1E2 | 51 | 7 | 51 | 7 | 0.69 |
| We | ng/ml | 3.2E-1 | 4.9E-1 | 1.1E0 | 3.8E0 | 1.8E0 | 8.4E0 | 1.0E-9 | 1.5E-1 | 9.7E0 | 2.3E1 | 51 | 7 | 51 | 7 | 0.61 |
| Wg | ng/ml | 1.0E-9 | 1.0E-9 | 3.2E-4 | 7.6E-2 | 2.3E-3 | 2.0E-1 | 1.0E-9 | 1.0E-9 | 1.6E-2 | 5.3E-1 | 51 | 7 | 51 | 7 | 0.56 |
| Wh | ng/ml | 1.0E-2 | 2.0E-2 | 4.3E-2 | 7.3E-2 | 9.6E-2 | 1.2E-1 | 1.0E-9 | 1.0E-9 | 4.2E-1 | 3.4E-1 | 51 | 7 | 51 | 7 | 0.59 |
| Wf | ng/ml | 1.0E-9 | 1.0E-9 | 1.0E-1 | 3.3E-1 | 2.1E-1 | 8.6E-1 | 1.0E-9 | 1.0E-9 | 1.2E0 | 2.3E0 | 51 | 7 | 51 | 7 | 0.40 |
| Ra | pg/ml | 1.0E-9 | 1.0E-9 | 3.8E-1 | 5.3E0 | 9.3E-1 | 1.7E1 | 1.0E-9 | 1.0E-9 | 3.8E0 | 6.4E1 | 121 | 14 | 121 | 14 | 0.55 |
| Qz | pg/ml | 9.8E0 | 1.1E1 | 5.2E1 | 4.7E1 | 8.7E1 | 7.8E1 | 1.0E-9 | 1.0E-9 | 4.5E2 | 2.3E2 | 121 | 14 | 121 | 14 | 0.50 |
| Qy | pg/ml | 3.6E-1 | 6.9E-1 | 7.6E0 | 5.4E1 | 4.5E1 | 2.0E2 | 1.0E-9 | 1.0E-9 | 4.3E2 | 7.3E2 | 121 | 14 | 121 | 14 | 0.66 |
| Qx | pg/ml | 1.0E-9 | 1.0E-9 | 2.8E0 | 1.2E1 | 1.8E1 | 2.9E1 | 1.0E-9 | 1.0E-9 | 1.9E2 | 1.1E2 | 121 | 14 | 121 | 14 | 0.55 |
| Qw | pg/ml | 1.0E-9 | 5.7E-1 | 3.0E0 | 1.0E0 | 9.9E0 | 1.6E0 | 1.0E-9 | 1.0E-9 | 6.6E1 | 5.6E0 | 121 | 14 | 121 | 14 | 0.54 |
| Qv | pg/ml | 1.9E4 | 1.1E4 | 3.8E4 | 1.5E4 | 9.5E4 | 1.5E4 | 1.0E-9 | 8.5E2 | 9.4E5 | 5.0E4 | 121 | 14 | 121 | 14 | 0.35 |
| Qu | pg/ml | 6.2E0 | 2.5E1 | 9.0E1 | 1.1E2 | 1.8E2 | 2.0E2 | 1.0E-9 | 1.0E-9 | 9.8E2 | 7.3E2 | 121 | 14 | 121 | 14 | 0.54 |
| Qt | pg/ml | 1.3E1 | 1.1E1 | 4.5E1 | 4.4E1 | 1.0E2 | 7.8E1 | 1.0E-9 | 1.0E-9 | 7.1E2 | 2.2E2 | 121 | 14 | 121 | 14 | 0.48 |
| Qh | ng/ml | 1.8E1 | 3.7E1 | 4.4E1 | 1.1E2 | 7.2E1 | 2.0E2 | 2.5E-1 | 3.3E0 | 4.6E2 | 8.0E2 | 121 | 14 | 121 | 14 | 0.68 |
| Qg | ng/ml | 7.3E0 | 8.1E0 | 1.4E1 | 1.4E1 | 2.6E1 | 2.1E1 | 1.5E-1 | 3.3E-1 | 2.7E2 | 8.1E1 | 121 | 14 | 121 | 14 | 0.47 |
| Jj | ng/ml | 5.6E2 | 2.5E2 | 2.1E3 | 4.7E2 | 1.9E4 | 5.0E2 | 2.3E0 | 8.7E0 | 3.4E5 | 1.9E3 | 309 | 45 | 309 | 45 | 0.35 |
| Jk | ng/ml | 2.6E0 | 5.1E0 | 2.0E1 | 3.3E1 | 4.8E1 | 5.7E1 | 1.0E-9 | 1.2E-1 | 3.9E2 | 2.4E2 | 309 | 45 | 309 | 45 | 0.61 |
| Jl | ng/ml | 4.8E-1 | 8.9E-1 | 2.0E0 | 2.2E2 | 4.8E0 | 1.5E3 | 1.2E-3 | 9.0E-2 | 4.0E1 | 9.9E3 | 309 | 45 | 309 | 45 | 0.65 |
| Jm | ng/ml | 1.8E1 | 4.5E1 | 6.1E0 | 1.1E2 | 1.4E2 | 3.1E2 | 1.0E-9 | 4.0E-1 | 1.4E3 | 2.1E3 | 309 | 45 | 309 | 45 | 0.61 |
| Jn | pg/ml | 3.0E-1 | 8.4E-1 | 3.4E0 | 3.8E1 | 3.6E1 | 1.4E2 | 1.0E-9 | 1.0E-9 | 6.2E2 | 7.3E2 | 309 | 45 | 309 | 45 | 0.70 |
| Jo | pg/ml | 3.7E3 | 4.7E3 | 4.7E3 | 8.4E3 | 3.9E3 | 1.6E4 | 2.0E1 | 2.4E1 | 2.4E4 | 1.0E5 | 309 | 45 | 309 | 45 | 0.55 |
| Jp | pg/ml | 6.9E4 | 9.9E4 | 7.1E4 | 1.0E5 | 3.5E4 | 5.7E4 | 5.8E2 | 2.8E4 | 1.9E5 | 3.8E5 | 309 | 45 | 309 | 45 | 0.71 |
| Jq | pg/ml | 9.4E1 | 1.4E2 | 1.6E2 | 5.5E2 | 2.0E2 | 1.4E3 | 1.0E0 | 5.6E0 | 2.0E3 | 8.7E3 | 309 | 45 | 309 | 45 | 0.61 |
| Jr | pg/ml | 3.6E0 | 1.5E1 | 5.5E1 | 3.6E2 | 6.1E2 | 1.4E3 | 1.0E-9 | 1.0E-9 | 1.1E4 | 7.4E3 | 309 | 45 | 309 | 45 | 0.68 |
| Js | pg/ml | 1.4E1 | 2.3E1 | 6.6E1 | 2.6E2 | 5.8E2 | 7.4E2 | 1.0E-9 | 2.7E0 | 1.0E4 | 3.0E3 | 309 | 45 | 309 | 45 | 0.71 |
| Jt | pg/ml | 2.3E3 | 4.3E3 | 2.8E3 | 6.9E3 | 2.2E3 | 9.9E3 | 2.2E1 | 1.5E2 | 2.2E4 | 5.2E4 | 309 | 45 | 309 | 45 | 0.69 |
| Xa | pg/ml | 1.0E-9 | 2.4E1 | 8.6E0 | 2.7E2 | 1.7E1 | 4.7E2 | 1.0E-9 | 2.9E0 | 9.6E1 | 1.2E3 | 51 | 7 | 51 | 7 | 0.83 |
| Ye | pg/ml | 1.0E-9 | 1.0E-9 | 4.5E0 | 1.0E0 | 1.4E1 | 2.7E0 | 1.0E-9 | 1.0E-9 | 6.9E1 | 7.2E0 | 51 | 7 | 51 | 7 | 0.43 |
| Tm | pg/ml | 1.0E-9 | 1.0E-9 | 2.7E0 | 1.2E0 | 4.5E0 | 3.2E0 | 1.0E-9 | 1.0E-9 | 1.8E1 | 8.4E0 | 51 | 7 | 51 | 7 | 0.42 |
| Tl | pg/ml | 1.1E-1 | 1.0E-9 | 3.1E-1 | 3.6E0 | 4.0E-1 | 9.3E0 | 1.0E-9 | 1.0E-9 | 1.8E0 | 2.5E1 | 51 | 7 | 51 | 7 | 0.42 |
| Ju | mIU/ml | 1.0E1 | 1.2E1 | 2.5E1 | 1.8E1 | 3.6E1 | 1.7E1 | 1.7E-1 | 1.9E0 | 2.3E2 | 6.0E1 | 121 | 14 | 121 | 14 | 0.56 |
| Jv | mIU/ml | 1.6E1 | 1.3E1 | 4.1E1 | 2.3E1 | 6.5E1 | 2.7E1 | 1.7E-2 | 1.1E0 | 4.4E2 | 8.9E1 | 121 | 14 | 121 | 14 | 0.48 |
| Jy | ng/ml | 1.6E-3 | 2.4E-3 | 2.3E-3 | 5.5E-3 | 4.0E-3 | 1.0E-2 | 1.0E-9 | 5.3E-4 | 3.9E-2 | 4.1E-2 | 121 | 14 | 121 | 14 | 0.65 |
| Kc | pg/ml | 2.3E1 | 2.8E1 | 4.4E1 | 6.2E1 | 5.2E1 | 8.6E1 | 1.0E-9 | 1.0E-9 | 2.7E2 | 3.2E2 | 122 | 14 | 122 | 14 | 0.54 |
| Kd | pg/ml | 1.0E-9 | 1.0E-9 | 1.8E2 | 3.7E3 | 6.1E2 | 1.0E4 | 1.0E-9 | 1.0E-9 | 4.8E3 | 3.8E4 | 122 | 14 | 122 | 14 | 0.64 |

Figure 36 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ke | pg/ml | 1.2E4 | 3.6E4 | 1.4E4 | 5.7E4 | 9.9E3 | 8.1E4 | 6.7E2 | 3.5E3 | 5.5E4 | 3.2E5 | 122 | 14 | 122 | 14 | 0.79 |
| Kf | pg/mL | 6.3E0 | 6.8E0 | 7.0E0 | 1.2E1 | 6.1E0 | 2.0E1 | 1.0E-9 | 1.0E-9 | 4.4E1 | 7.8E1 | 122 | 14 | 122 | 14 | 0.55 |
| Kg | pg/mL | 9.6E2 | 1.0E3 | 1.8E3 | 5.3E3 | 2.6E3 | 1.1E4 | 7.7E1 | 1.3E2 | 2.2E4 | 3.6E4 | 122 | 14 | 122 | 14 | 0.46 |
| Ki | pg/ml | 6.0E1 | 7.6E1 | 6.9E1 | 9.2E1 | 5.1E1 | 6.4E1 | 1.0E-9 | 1.3E1 | 2.9E2 | 2.5E2 | 122 | 14 | 122 | 14 | 0.62 |
| Kj | pg/ml | 8.6E2 | 6.9E2 | 1.3E3 | 2.3E3 | 1.4E3 | 4.1E3 | 6.6E1 | 3.3E1 | 8.8E3 | 1.5E4 | 122 | 14 | 122 | 14 | 0.43 |
| Kk | pg/ml | 6.9E0 | 1.0E1 | 1.3E1 | 2.3E1 | 1.5E1 | 2.2E1 | 1.0E-9 | 2.0E0 | 8.1E1 | 5.9E1 | 122 | 14 | 122 | 14 | 0.64 |
| Kl | pg/ml | 1.8E4 | 1.6E4 | 2.8E4 | 2.2E4 | 2.7E4 | 1.7E4 | 2.3E2 | 6.2E2 | 1.3E5 | 5.1E4 | 122 | 14 | 122 | 14 | 0.47 |
| Kn | pg/ml | 2.9E1 | 5.7E1 | 6.4E1 | 4.5E2 | 9.8E1 | 1.3E3 | 1.0E-9 | 1.0E-9 | 6.3E2 | 4.9E3 | 122 | 14 | 122 | 14 | 0.60 |
| Ko | pg/ml | 3.4E2 | 6.8E2 | 4.8E2 | 8.1E2 | 5.7E2 | 1.0E3 | 1.0E-9 | 1.5E2 | 3.8E3 | 4.1E3 | 122 | 14 | 122 | 14 | 0.65 |
| Kp | pg/ml | 3.6E2 | 3.6E2 | 3.6E2 | 1.3E3 | 2.5E2 | 3.5E3 | 1.0E-9 | 3.7E1 | 9.8E2 | 1.3E4 | 122 | 14 | 122 | 14 | 0.56 |
| Kq | pg/ml | 3.2E2 | 6.1E2 | 4.4E2 | 1.3E4 | 4.8E2 | 4.2E4 | 1.6E0 | 7.0E1 | 3.6E3 | 1.6E5 | 117 | 14 | 117 | 14 | 0.75 |
| Kr | pg/ml | 2.9E-1 | 2.5E0 | 2.0E0 | 3.2E1 | 3.8E0 | 1.1E2 | 1.0E-9 | 1.0E-9 | 2.3E1 | 4.2E2 | 117 | 14 | 117 | 14 | 0.62 |
| Ks | pg/ml | 1.4E4 | 2.0E4 | 2.0E4 | 2.2E4 | 1.8E4 | 1.8E4 | 5.1E1 | 4.2E2 | 7.9E4 | 5.0E4 | 117 | 14 | 117 | 14 | 0.53 |
| Ps | ng/ml | 1.3E2 | 1.2E3 | 6.5E2 | 2.3E3 | 2.1E3 | 2.6E3 | 1.6E0 | 3.5E2 | 1.2E4 | 7.6E3 | 51 | 7 | 51 | 7 | 0.90 |
| Kx | ng/ml | 2.8E-4 | 9.0E-3 | 7.2E-3 | 1.9E-2 | 1.5E-2 | 2.4E-2 | 1.0E-9 | 1.0E-9 | 1.0E-1 | 6.5E-2 | 121 | 14 | 121 | 14 | 0.67 |
| Ky | ng/ml | 1.2E-1 | 3.7E-1 | 3.8E-1 | 6.4E-1 | 7.6E-1 | 7.8E-1 | 1.0E-9 | 1.0E-9 | 5.1E0 | 2.7E0 | 121 | 14 | 121 | 14 | 0.66 |
| Kz | ng/ml | 1.0E-9 | 2.4E-3 | 3.5E-3 | 7.5E-3 | 5.7E-3 | 8.8E-3 | 1.0E-9 | 1.0E-9 | 1.6E-2 | 2.5E-2 | 121 | 14 | 121 | 14 | 0.61 |
| Rz | ng/ml | 3.4E-1 | 3.3E-1 | 8.4E-1 | 1.5E0 | 1.2E0 | 2.7E0 | 4.6E-3 | 1.7E-2 | 6.7E0 | 7.5E0 | 51 | 7 | 51 | 7 | 0.54 |
| Ry | ng/ml | 1.6E-2 | 2.3E-2 | 2.4E-2 | 7.4E-2 | 2.6E-2 | 1.2E-1 | 1.0E-9 | 8.5E-3 | 1.2E-1 | 3.5E-1 | 51 | 7 | 51 | 7 | 0.64 |
| Rx | ng/ml | 1.0E-9 | 3.5E-5 | 1.4E-3 | 2.1E-3 | 2.3E-3 | 3.0E-3 | 1.0E-9 | 1.0E-9 | 8.6E-3 | 7.6E-3 | 51 | 7 | 51 | 7 | 0.63 |
| Ld | pg/ml | 1.0E-9 | 4.2E0 | 3.4E0 | 8.0E0 | 8.6E0 | 9.2E0 | 1.0E-9 | 1.0E-9 | 6.9E1 | 2.9E1 | 122 | 14 | 122 | 14 | 0.72 |
| Lh | pg/ml | 1.1E4 | 2.0E4 | 2.1E4 | 5.8E4 | 2.7E4 | 1.0E5 | 1.0E-9 | 1.3E3 | 2.6E5 | 4.8E5 | 310 | 45 | 310 | 45 | 0.65 |
| Li | pg/ml | 3.1E3 | 2.0E4 | 1.8E4 | 5.1E4 | 9.4E4 | 8.5E4 | 1.2E1 | 8.4E1 | 1.3E6 | 4.1E5 | 310 | 45 | 310 | 45 | 0.77 |
| Lj | pg/ml | 2.4E3 | 1.5E4 | 1.9E4 | 3.9E4 | 5.7E4 | 6.5E4 | 1.0E-9 | 8.9E1 | 4.3E5 | 3.9E5 | 310 | 45 | 310 | 45 | 0.70 |
| Lp | pg/ml | 1.1E1 | 1.1E0 | 6.6E1 | 4.5E2 | 1.8E2 | 6.0E2 | 1.0E-9 | 1.0E-9 | 1.1E3 | 1.4E3 | 51 | 7 | 51 | 7 | 0.51 |
| Lt | pg/ml | 1.0E-9 | 1.0E-9 | 1.7E0 | 1.0E0 | 5.9E0 | 0.0E0 | 1.0E-9 | 1.0E-9 | 2.5E1 | 1.0E-9 | 51 | 7 | 51 | 7 | 0.46 |
| Rv | ng/ml | 5.0E-4 | 5.8E-4 | 1.2E-3 | 3.3E-3 | 2.5E-3 | 5.2E-3 | 1.0E-9 | 1.0E-9 | 1.6E-2 | 1.2E-2 | 51 | 7 | 51 | 7 | 0.51 |
| Ru | ng/ml | 1.0E-9 | 1.0E-9 | 1.0E-2 | 1.1E-1 | 5.2E-2 | 1.6E-1 | 1.0E-9 | 1.0E-9 | 3.1E-1 | 3.5E-1 | 51 | 7 | 51 | 7 | 0.70 |
| Rt | ng/ml | 8.0E-2 | 5.1E-2 | 1.2E-1 | 1.2E0 | 1.4E-1 | 2.8E0 | 2.2E-3 | 1.3E-3 | 6.3E-1 | 7.4E0 | 51 | 7 | 51 | 7 | 0.41 |
| Yl | pg/ml | 1.2E1 | 1.5E1 | 1.7E1 | 4.8E1 | 1.7E1 | 7.7E1 | 1.0E-9 | 1.0E-9 | 7.9E1 | 2.2E2 | 51 | 7 | 51 | 7 | 0.59 |
| Rm | ng/ml | 1.8E1 | 5.4E1 | 4.7E1 | 7.2E1 | 8.5E1 | 8.3E1 | 2.2E-1 | 2.3E-1 | 6.5E2 | 2.5E2 | 120 | 14 | 120 | 14 | 0.62 |
| Rh | ng/ml | 1.7E2 | 1.7E2 | 4.7E2 | 1.4E3 | 1.6E3 | 4.5E3 | 7.5E0 | 2.5E1 | 1.7E4 | 1.7E4 | 120 | 14 | 120 | 14 | 0.48 |
| Ri | ng/ml | 4.4E-2 | 1.0E-9 | 4.0E0 | 1.7E0 | 8.3E0 | 4.2E0 | 1.0E-9 | 1.0E-9 | 4.9E1 | 1.6E1 | 120 | 14 | 120 | 14 | 0.37 |
| Rg | ng/ml | 1.0E-9 | 1.0E-9 | 8.9E-2 | 1.7E-2 | 4.5E-1 | 5.5E-2 | 1.0E-9 | 1.0E-9 | 3.3E0 | 2.1E-1 | 120 | 14 | 120 | 14 | 0.49 |
| Rj | ng/ml | 1.0E-9 | 1.0E-9 | 9.1E-1 | 2.0E1 | 2.0E0 | 7.2E1 | 1.0E-9 | 1.0E-9 | 1.1E1 | 2.7E2 | 120 | 14 | 120 | 14 | 0.51 |
| Rf | ng/ml | 3.5E-1 | 1.0E0 | 7.7E-1 | 3.1E0 | 1.3E0 | 5.2E0 | 2.1E-2 | 7.0E-2 | 9.9E0 | 1.7E1 | 120 | 14 | 120 | 14 | 0.71 |
| Ql | pg/ml | 1.7E0 | 1.0E1 | 1.1E1 | 2.4E1 | 2.2E1 | 2.8E1 | 1.0E-9 | 1.0E-9 | 1.8E2 | 9.3E1 | 121 | 14 | 121 | 14 | 0.67 |
| Qm | pg/ml | 1.7E0 | 2.5E1 | 1.9E1 | 3.4E1 | 3.5E1 | 3.5E1 | 1.0E-9 | 1.0E-9 | 1.9E2 | 1.0E2 | 121 | 14 | 121 | 14 | 0.65 |
| Qn | pg/ml | 6.1E-1 | 8.5E-1 | 7.5E0 | 2.6E0 | 2.8E1 | 4.1E0 | 1.0E-9 | 1.0E-9 | 2.2E2 | 1.2E1 | 121 | 14 | 121 | 14 | 0.53 |
| Nv | pg/ml | 3.4E3 | 7.8E3 | 9.1E3 | 1.9E4 | 1.9E4 | 2.8E4 | 1.0E-9 | 1.6E2 | 1.6E5 | 1.2E5 | 311 | 45 | 311 | 45 | 0.70 |
| Nw | pg/ml | 8.6E3 | 2.0E4 | 1.2E4 | 3.2E4 | 1.6E4 | 4.3E4 | 1.9E2 | 4.5E3 | 2.1E5 | 2.2E5 | 311 | 45 | 311 | 45 | 0.80 |
| Nx | pg/ml | 2.2E2 | 4.2E2 | 4.1E2 | 6.9E2 | 6.1E2 | 8.2E2 | 1.0E-9 | 1.0E-9 | 3.5E3 | 4.1E3 | 311 | 45 | 311 | 45 | 0.59 |
| Ny | pg/ml | 5.7E0 | 2.0E1 | 1.0E2 | 1.3E2 | 1.4E3 | 4.2E2 | 1.0E-9 | 1.0E-9 | 2.5E4 | 2.8E3 | 311 | 45 | 311 | 45 | 0.73 |
| Oa | pg/ml | 1.6E2 | 7.9E2 | 4.2E2 | 1.0E3 | 7.0E2 | 1.0E3 | 1.0E-9 | 1.0E-9 | 4.5E3 | 3.4E3 | 121 | 14 | 121 | 14 | 0.68 |
| Op | pg/ml | 4.5E5 | 4.0E5 | 4.5E5 | 3.9E5 | 1.6E5 | 1.7E5 | 5.2E4 | 9.4E4 | 7.5E5 | 6.6E5 | 51 | 7 | 51 | 7 | 0.41 |
| Oe | pg/ml | 4.7E1 | 1.0E-9 | 2.6E2 | 1.6E2 | 3.9E2 | 3.0E2 | 1.0E-9 | 1.0E-9 | 2.3E3 | 1.1E3 | 310 | 44 | 310 | 44 | 0.43 |
| Of | pg/ml | 1.4E2 | 9.7E1 | 5.3E3 | 3.2E3 | 2.1E4 | 1.1E4 | 1.0E-9 | 1.0E-9 | 1.9E5 | 6.6E4 | 311 | 45 | 311 | 45 | 0.47 |
| Og | pg/ml | 7.7E-2 | 1.7E-2 | 3.9E-1 | 7.4E-2 | 1.6E0 | 1.5E-1 | 1.0E-9 | 1.0E-9 | 1.9E1 | 8.0E-1 | 311 | 45 | 311 | 45 | 0.35 |
| Oh | pg/ml | 2.4E0 | 7.2E0 | 1.4E1 | 4.0E2 | 9.1E1 | 2.4E3 | 1.0E-9 | 1.0E-9 | 1.4E3 | 1.6E4 | 311 | 45 | 311 | 45 | 0.63 |
| Oi | pg/ml | 2.0E0 | 2.0E0 | 5.1E0 | 4.7E0 | 8.0E0 | 6.8E0 | 1.0E-9 | 1.0E-9 | 6.7E1 | 3.1E1 | 311 | 45 | 311 | 45 | 0.50 |
| Ok | pg/ml | 3.6E2 | 6.7E2 | 5.0E2 | 1.3E3 | 5.0E2 | 1.6E3 | 1.5E1 | 5.3E1 | 4.2E3 | 7.8E3 | 311 | 45 | 311 | 45 | 0.73 |
| Om | pg/ml | 4.0E2 | 7.9E2 | 7.9E2 | 2.3E3 | 2.1E3 | 7.6E3 | 1.0E-9 | 7.0E1 | 3.5E4 | 5.1E4 | 311 | 45 | 311 | 45 | 0.66 |
| On | pg/ml | 1.6E2 | 3.3E2 | 2.7E2 | 8.6E2 | 4.0E2 | 1.4E3 | 1.0E-9 | 1.6E1 | 4.5E3 | 8.5E3 | 311 | 45 | 311 | 45 | 0.73 |
| Or | pg/ml | 1.2E1 | 1.9E1 | 3.6E1 | 9.6E1 | 6.9E1 | 1.7E2 | 1.0E-9 | 1.0E-9 | 4.4E2 | 5.1E2 | 123 | 14 | 123 | 14 | 0.56 |
| Ow | pg/ml | 4.2E1 | 9.8E1 | 1.9E2 | 5.1E2 | 7.9E2 | 8.5E2 | 1.0E-9 | 1.0E-9 | 8.1E3 | 3.0E3 | 123 | 14 | 123 | 14 | 0.63 |
| Ou | pg/ml | 5.1E2 | 7.7E2 | 1.1E3 | 2.3E3 | 1.9E3 | 3.0E3 | 1.0E-9 | 1.0E-9 | 1.1E4 | 8.2E3 | 123 | 14 | 123 | 14 | 0.56 |
| Ul | ng/ml | 1.0E-9 | 1.0E-9 | 1.0E0 | 5.5E0 | 4.3E0 | 1.6E1 | 1.0E-9 | 1.0E-9 | 2.9E1 | 5.6E1 | 122 | 14 | 122 | 14 | 0.54 |

Figure 36 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Uo | ng/ml | 1.0E-9 | 1.0E-9 | 7.7E-2 | 5.1E-2 | 2.1E-1 | 1.7E-1 | 1.0E-9 | 1.0E-9 | 1.3E0 | 6.3E-1 | 122 | 14 | 122 | 14 | 0.46 |
| Uk | ng/ml | 1.0E-9 | 1.0E-9 | 6.3E-3 | 3.2E-3 | 3.2E-2 | 8.6E-3 | 1.0E-9 | 1.0E-9 | 3.2E-1 | 3.1E-2 | 122 | 14 | 122 | 14 | 0.49 |
| Um | ng/ml | 1.0E-9 | 1.0E-9 | 2.3E-1 | 2.1E-1 | 6.1E-1 | 6.2E-1 | 1.0E-9 | 1.0E-9 | 3.6E0 | 2.3E0 | 122 | 14 | 122 | 14 | 0.45 |
| Uf | ng/ml | 5.8E-2 | 9.6E-2 | 1.4E-1 | 5.0E-1 | 2.0E-1 | 1.3E0 | 1.0E-3 | 3.5E-3 | 1.1E0 | 5.1E0 | 122 | 14 | 122 | 14 | 0.62 |
| Uh | ng/ml | 2.2E0 | 6.3E0 | 3.1E0 | 8.1E0 | 3.0E0 | 5.1E0 | 3.6E-2 | 7.1E-1 | 1.5E1 | 1.8E1 | 122 | 14 | 122 | 14 | 0.81 |
| Un | ng/ml | 1.7E0 | 3.2E0 | 1.9E0 | 4.7E0 | 1.2E0 | 6.2E0 | 3.4E-1 | 1.0E0 | 8.0E0 | 2.5E1 | 122 | 14 | 122 | 14 | 0.71 |
| Ug | ng/ml | 1.1E1 | 9.1E0 | 2.1E1 | 2.5E1 | 2.4E1 | 4.5E1 | 1.2E0 | 1.0E0 | 1.4E2 | 1.6E2 | 122 | 14 | 122 | 14 | 0.44 |
| Ur | ng/ml | 1.1E-1 | 1.0E-9 | 2.9E-1 | 1.0E0 | 5.0E-1 | 2.4E0 | 1.0E-9 | 1.0E-9 | 3.0E0 | 7.3E0 | 121 | 14 | 121 | 14 | 0.36 |
| Up | ng/ml | 1.0E-9 | 1.0E-9 | 2.9E-3 | 1.8E-1 | 8.9E-3 | 6.3E-1 | 1.0E-9 | 1.0E-9 | 5.3E-2 | 2.4E0 | 121 | 14 | 121 | 14 | 0.54 |
| Us | ng/ml | 3.6E-3 | 1.0E-9 | 1.7E-2 | 1.3E-1 | 4.4E-2 | 4.4E-1 | 1.0E-9 | 1.0E-9 | 3.6E-1 | 1.7E0 | 121 | 14 | 121 | 14 | 0.42 |
| Uv | ng/ml | 3.1E-3 | 1.0E-3 | 1.5E-2 | 3.2E-2 | 4.4E-2 | 1.1E-1 | 1.0E-9 | 1.0E-9 | 3.5E-1 | 4.1E-1 | 121 | 14 | 121 | 14 | 0.40 |
| Ut | ng/ml | 6.7E-1 | 1.7E0 | 2.6E0 | 9.4E0 | 6.0E0 | 1.8E1 | 1.0E-9 | 4.0E-1 | 5.2E1 | 6.5E1 | 121 | 14 | 121 | 14 | 0.73 |
| Uu | ng/ml | 7.1E0 | 4.9E0 | 7.7E0 | 5.4E0 | 5.2E0 | 3.1E0 | 5.4E-1 | 8.1E-1 | 2.9E1 | 1.2E1 | 121 | 14 | 121 | 14 | 0.38 |
| Uw | ng/ml | 2.3E0 | 4.0E0 | 2.8E0 | 9.0E0 | 2.5E0 | 1.3E1 | 1.0E-9 | 1.7E0 | 9.8E0 | 3.9E1 | 52 | 7 | 52 | 7 | 0.73 |
| Vb | ng/ml | 1.1E0 | 1.1E0 | 1.0E0 | 1.7E0 | 4.3E-1 | 2.1E0 | 8.5E-2 | 2.6E-1 | 2.0E0 | 6.4E0 | 52 | 7 | 52 | 7 | 0.48 |
| Vc | ng/ml | 1.0E-9 | 1.0E-9 | 4.1E-3 | 1.0E-9 | 1.8E-2 | 0.0E0 | 1.0E-9 | 1.0E-9 | 1.1E-1 | 1.0E-9 | 52 | 7 | 52 | 7 | 0.46 |
| Uy | ng/ml | 1.3E0 | 1.0E0 | 6.0E0 | 2.2E1 | 1.7E1 | 2.7E1 | 8.7E-2 | 2.0E-2 | 9.9E1 | 6.4E1 | 52 | 7 | 52 | 7 | 0.54 |
| Uz | ng/ml | 1.0E-9 | 1.0E-9 | 8.4E-3 | 4.8E0 | 6.0E-2 | 1.2E1 | 1.0E-9 | 1.0E-9 | 4.4E-1 | 3.3E1 | 52 | 7 | 52 | 7 | 0.63 |
| Ux | ng/ml | 1.8E2 | 1.6E2 | 1.9E2 | 1.8E2 | 1.4E2 | 1.5E2 | 4.5E0 | 4.0E1 | 4.8E2 | 4.9E2 | 52 | 7 | 52 | 7 | 0.47 |
| Va | ng/ml | 1.5E1 | 3.2E0 | 2.5E1 | 3.2E0 | 2.9E1 | 1.5E0 | 3.1E-1 | 1.2E0 | 1.2E2 | 5.7E0 | 52 | 7 | 52 | 7 | 0.21 |
| Vh | ng/ml | 1.1E-2 | 2.7E-2 | 1.9E-2 | 1.4E-1 | 2.5E-2 | 3.2E-1 | 3.9E-4 | 3.5E-3 | 1.2E-1 | 8.6E-1 | 52 | 7 | 52 | 7 | 0.69 |
| Vi | ng/ml | 3.3E-3 | 4.3E-2 | 9.4E-3 | 3.0E-1 | 1.8E-2 | 6.7E-1 | 1.0E-9 | 1.6E-2 | 1.2E-1 | 1.8E0 | 52 | 7 | 52 | 7 | 0.91 |
| Vp | ng/ml | 1.0E-9 | 1.0E-9 | 1.3E-1 | 3.9E0 | 5.5E-1 | 1.3E1 | 1.0E-9 | 1.0E-9 | 3.9E0 | 4.9E1 | 122 | 14 | 122 | 14 | 0.54 |
| Vt | ng/ml | 6.0E0 | 1.1E1 | 7.7E0 | 2.5E1 | 6.4E0 | 3.9E1 | 5.6E-1 | 1.9E0 | 3.2E1 | 1.6E2 | 122 | 14 | 122 | 14 | 0.73 |
| Vu | ng/ml | 1.0E-9 | 3.6E-1 | 1.5E0 | 2.1E0 | 3.3E0 | 3.9E0 | 1.0E-9 | 1.0E-9 | 2.2E1 | 1.3E1 | 120 | 12 | 120 | 12 | 0.57 |
| Vq | ng/ml | 1.5E2 | 7.2E2 | 6.6E2 | 1.4E3 | 1.5E3 | 1.8E3 | 9.2E-1 | 6.5E-1 | 1.2E4 | 4.9E3 | 98 | 10 | 98 | 10 | 0.64 |
| Vo | ng/ml | 2.6E1 | 2.5E1 | 2.5E1 | 2.2E1 | 5.4E0 | 7.0E0 | 4.9E0 | 1.9E0 | 4.8E1 | 3.0E1 | 122 | 14 | 122 | 14 | 0.41 |
| Vs | ng/ml | 1.0E-9 | 1.0E-9 | 4.4E0 | 3.9E1 | 1.1E1 | 1.3E2 | 1.0E-9 | 1.0E-9 | 8.9E1 | 4.5E2 | 120 | 13 | 120 | 13 | 0.45 |
| Vv | ng/ml | 2.9E0 | 2.6E0 | 6.0E0 | 6.8E0 | 9.9E0 | 1.2E1 | 1.0E-9 | 1.0E-9 | 8.4E1 | 4.4E1 | 122 | 13 | 122 | 13 | 0.46 |
| Vw | ng/ml | 3.6E1 | 5.7E1 | 3.4E1 | 4.7E1 | 1.7E1 | 2.4E1 | 2.5E0 | 1.1E1 | 6.7E1 | 6.9E1 | 52 | 7 | 52 | 7 | 0.70 |
| Oy | pg/ml | 4.8E-1 | 4.3E-1 | 6.5E0 | 3.0E0 | 3.2E1 | 7.0E0 | 1.0E-9 | 1.0E-9 | 4.0E2 | 3.3E1 | 310 | 45 | 310 | 45 | 0.44 |
| Oz | pg/ml | 1.7E-2 | 1.0E-9 | 3.5E-1 | 7.2E-1 | 1.7E0 | 4.2E0 | 1.0E-9 | 1.0E-9 | 2.9E1 | 2.8E1 | 310 | 45 | 310 | 45 | 0.36 |
| Pa | pg/ml | 3.8E-1 | 7.4E-1 | 1.3E0 | 9.6E0 | 5.9E0 | 3.7E1 | 1.0E-9 | 1.0E-9 | 8.6E1 | 2.3E2 | 310 | 45 | 310 | 45 | 0.63 |
| Pb | pg/ml | 1.0E-9 | 1.0E-9 | 1.8E0 | 8.1E-1 | 2.8E1 | 4.7E0 | 1.0E-9 | 1.0E-9 | 4.9E2 | 3.2E1 | 310 | 45 | 310 | 45 | 0.39 |
| Pc | pg/ml | 6.3E-2 | 1.0E-9 | 4.0E-1 | 8.4E0 | 9.2E-1 | 4.9E1 | 1.0E-9 | 1.0E-9 | 1.4E1 | 3.3E2 | 310 | 45 | 310 | 45 | 0.42 |
| Pd | pg/ml | 1.6E0 | 2.4E0 | 6.5E0 | 9.4E0 | 4.8E1 | 2.1E1 | 1.0E-9 | 1.0E-9 | 8.4E2 | 1.2E2 | 310 | 45 | 310 | 45 | 0.58 |
| Pe | pg/ml | 2.0E1 | 6.9E1 | 1.1E2 | 7.8E2 | 4.6E2 | 2.5E3 | 1.0E-9 | 1.0E-9 | 4.7E3 | 1.5E4 | 310 | 45 | 310 | 45 | 0.74 |
| Pf | pg/ml | 1.4E0 | 7.7E0 | 1.5E1 | 2.8E1 | 9.4E1 | 6.7E1 | 1.0E-9 | 1.0E-9 | 1.5E3 | 4.3E2 | 310 | 45 | 310 | 45 | 0.73 |
| Pg | pg/ml | 3.4E0 | 1.1E1 | 6.9E1 | 1.8E2 | 5.3E2 | 4.4E2 | 1.0E-9 | 1.0E-9 | 7.7E3 | 2.2E3 | 310 | 45 | 310 | 45 | 0.71 |
| Ph | ng/ml | 1.5E-1 | 2.1E-1 | 3.5E-1 | 6.8E-1 | 5.1E-1 | 1.4E0 | 1.0E-9 | 1.0E-9 | 2.8E0 | 5.4E0 | 123 | 14 | 123 | 14 | 0.53 |
| Pi | ng/ml | 1.9E-1 | 3.5E-1 | 2.9E-1 | 6.5E0 | 3.8E-1 | 2.2E1 | 1.0E-9 | 2.1E-2 | 3.2E0 | 8.2E1 | 123 | 14 | 123 | 14 | 0.65 |
| Pj | ng/mL | 5.1E0 | 7.3E0 | 5.9E0 | 8.7E0 | 4.4E0 | 5.7E0 | 4.0E-1 | 6.6E-1 | 3.1E1 | 2.3E1 | 123 | 14 | 123 | 14 | 0.66 |
| Pk | ng/ml | 8.8E-3 | 1.2E-2 | 1.5E-2 | 1.2E-1 | 2.9E-2 | 4.0E-1 | 1.0E-9 | 1.3E-4 | 2.5E-1 | 1.5E0 | 123 | 14 | 123 | 14 | 0.65 |
| aA | mg/dL | 8.8E-1 | 1.0E0 | 9.9E-1 | 1.5E0 | 4.9E-1 | 1.0E0 | 3.0E-1 | 5.0E-1 | 4.2E0 | 4.7E0 | 475 | 62 | 475 | 62 | 0.66 |
| aC | mg/mL | 2.2E0 | 2.4E0 | 2.6E0 | 2.9E0 | 1.3E0 | 1.6E0 | 7.5E-1 | 1.0E0 | 7.4E0 | 6.7E0 | 151 | 25 | 151 | 25 | 0.54 |
| aD | ug/mL | 3.1E0 | 2.3E0 | 4.8E0 | 4.2E0 | 4.8E0 | 4.0E0 | 7.5E-1 | 9.2E-1 | 3.5E1 | 1.8E1 | 151 | 25 | 151 | 25 | 0.43 |
| aE | mg/mL | 5.8E-1 | 5.5E-1 | 6.0E-1 | 5.5E-1 | 1.7E-1 | 1.4E-1 | 1.8E-1 | 2.2E-1 | 1.2E0 | 9.6E-1 | 151 | 25 | 151 | 25 | 0.41 |
| aF | ng/mL | 2.2E0 | 2.9E0 | 5.2E0 | 4.1E0 | 8.1E0 | 4.2E0 | 4.3E-3 | 4.3E-3 | 5.0E1 | 1.5E1 | 151 | 25 | 151 | 25 | 0.51 |
| aG | mg/mL | 1.4E-1 | 1.2E-1 | 1.6E-1 | 1.4E-1 | 9.0E-2 | 5.5E-2 | 3.2E-2 | 6.8E-2 | 4.8E-1 | 2.5E-1 | 151 | 25 | 151 | 25 | 0.45 |
| aH | ug/mL | 7.6E1 | 5.9E1 | 8.0E1 | 6.1E1 | 4.2E1 | 2.3E1 | 8.9E0 | 1.1E1 | 2.0E2 | 1.1E2 | 151 | 25 | 151 | 25 | 0.39 |
| aI | ug/mL | 1.8E2 | 1.4E2 | 1.8E2 | 1.5E2 | 6.2E1 | 5.0E1 | 3.2E1 | 7.6E1 | 3.4E2 | 2.7E2 | 151 | 25 | 151 | 25 | 0.38 |
| aJ | ug/mL | 2.4E0 | 3.6E0 | 3.1E0 | 4.7E0 | 2.2E0 | 4.5E0 | 8.2E-1 | 1.4E0 | 1.4E1 | 2.3E1 | 151 | 25 | 151 | 25 | 0.62 |
| aK | ng/mL | 1.3E0 | 1.3E0 | 2.0E0 | 1.6E0 | 2.0E0 | 1.5E0 | 2.9E-4 | 1.3E-1 | 1.0E1 | 6.5E0 | 151 | 25 | 151 | 25 | 0.46 |
| aL | mg/mL | 7.4E-1 | 7.3E-1 | 7.8E-1 | 6.8E-1 | 2.6E-1 | 2.4E-1 | 2.2E-1 | 2.7E-1 | 1.7E0 | 1.1E0 | 151 | 25 | 151 | 25 | 0.41 |
| aM | U/mL | 1.8E1 | 2.5E1 | 3.5E1 | 1.0E2 | 4.9E1 | 2.1E2 | 4.2E-2 | 4.2E-2 | 3.5E2 | 8.2E2 | 151 | 25 | 151 | 25 | 0.58 |
| aN | U/mL | 1.5E1 | 1.4E1 | 2.4E1 | 3.5E1 | 3.7E1 | 6.6E1 | 2.5E-3 | 2.5E-3 | 3.8E2 | 3.3E2 | 151 | 25 | 151 | 25 | 0.51 |
| aO | pg/mL | 4.9E1 | 1.5E2 | 4.3E2 | 4.9E2 | 1.0E3 | 7.5E2 | 6.0E-2 | 6.2E0 | 6.6E3 | 2.4E3 | 151 | 25 | 151 | 25 | 0.60 |

Figure 36 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aP | ng/mL | 1.6E0 | 1.9E0 | 2.2E0 | 3.7E0 | 2.5E0 | 5.4E0 | 4.5E-1 | 7.8E-1 | 2.8E1 | 2.8E1 | 151 | 25 | 151 | 25 | 0.61 |
| aQ | ng/mL | 2.5E-1 | 2.4E-1 | 3.6E-1 | 2.9E-1 | 3.3E-1 | 2.0E-1 | 2.0E-4 | 5.1E-2 | 2.0E0 | 9.0E-1 | 151 | 25 | 151 | 25 | 0.47 |
| aR | ng/mL | 1.8E0 | 1.7E0 | 2.9E0 | 3.7E0 | 4.0E0 | 4.2E0 | 2.6E-1 | 6.5E-1 | 3.4E1 | 1.7E1 | 151 | 25 | 151 | 25 | 0.54 |
| aS | ng/mL | 3.7E-1 | 4.1E-1 | 1.0E0 | 9.6E-1 | 2.8E0 | 1.2E0 | 4.2E-3 | 6.0E-2 | 3.3E1 | 4.9E0 | 151 | 25 | 151 | 25 | 0.54 |
| aU | pg/mL | 6.8E1 | 5.8E1 | 1.0E2 | 8.6E1 | 1.1E2 | 1.0E2 | 7.4E-2 | 7.4E-2 | 7.0E2 | 5.1E2 | 151 | 25 | 151 | 25 | 0.45 |
| aV | ng/mL | 5.9E-1 | 3.7E-1 | 1.1E0 | 6.9E-1 | 2.8E0 | 6.2E-1 | 7.6E-4 | 9.1E-2 | 3.3E1 | 2.4E0 | 151 | 25 | 151 | 25 | 0.45 |
| aW | pg/mL | 2.0E1 | 1.8E1 | 2.3E1 | 1.9E1 | 3.6E1 | 1.1E1 | 7.2E-2 | 7.2E-2 | 4.2E2 | 4.7E1 | 151 | 25 | 151 | 25 | 0.46 |
| aX | ng/mL | 8.2E0 | 7.1E0 | 1.4E1 | 3.2E1 | 2.1E1 | 6.7E1 | 3.0E-1 | 7.7E-1 | 2.2E2 | 3.1E2 | 151 | 25 | 151 | 25 | 0.49 |
| aY | pg/mL | 5.3E1 | 4.7E1 | 7.7E1 | 6.9E1 | 1.1E2 | 7.9E1 | 4.1E-1 | 4.1E-1 | 1.2E3 | 3.9E2 | 151 | 25 | 151 | 25 | 0.47 |
| aZ | pg/mL | 2.2E2 | 4.4E2 | 5.4E2 | 1.5E3 | 1.2E3 | 2.2E3 | 1.7E0 | 1.5E1 | 1.2E4 | 7.9E3 | 151 | 25 | 151 | 25 | 0.65 |
| bA | pg/mL | 1.3E1 | 4.6E1 | 5.4E1 | 2.0E2 | 1.2E2 | 3.6E2 | 3.0E-2 | 2.0E0 | 9.4E2 | 1.5E3 | 151 | 25 | 151 | 25 | 0.67 |
| bB | ng/mL | 2.8E2 | 2.4E2 | 3.1E2 | 2.5E2 | 1.8E2 | 1.4E2 | 2.1E0 | 3.3E1 | 9.5E2 | 5.7E2 | 151 | 25 | 151 | 25 | 0.40 |
| bC | ng/mL | 3.2E2 | 3.3E2 | 6.2E2 | 8.6E2 | 8.0E2 | 1.3E3 | 1.4E1 | 5.0E1 | 4.7E3 | 4.0E3 | 151 | 25 | 151 | 25 | 0.51 |
| bE | mg/mL | 5.1E0 | 5.2E0 | 5.4E0 | 5.8E0 | 2.1E0 | 2.7E0 | 1.8E0 | 1.3E0 | 1.2E1 | 1.2E1 | 151 | 25 | 151 | 25 | 0.53 |
| bF | pg/mL | 3.5E1 | 6.4E1 | 3.6E2 | 2.5E2 | 1.4E3 | 5.5E2 | 5.0E-2 | 8.9E0 | 1.1E4 | 2.2E3 | 151 | 25 | 151 | 25 | 0.62 |
| bG | ng/mL | 1.6E0 | 1.8E0 | 3.1E0 | 3.2E0 | 4.5E0 | 3.8E0 | 1.1E-1 | 1.6E-1 | 3.0E1 | 1.5E1 | 151 | 25 | 151 | 25 | 0.53 |
| bH | pg/mL | 5.7E-1 | 5.7E-1 | 6.4E0 | 5.3E0 | 2.5E1 | 6.7E0 | 5.7E-1 | 5.7E-1 | 2.8E2 | 2.3E1 | 151 | 25 | 151 | 25 | 0.56 |
| bI | ng/mL | 4.0E-3 | 4.0E-3 | 9.4E-2 | 8.6E-2 | 2.0E-1 | 1.8E-1 | 4.0E-3 | 4.0E-3 | 9.8E-1 | 6.2E-1 | 151 | 25 | 151 | 25 | 0.49 |
| bJ | mg/mL | 1.9E0 | 1.9E0 | 2.4E0 | 2.2E0 | 2.0E0 | 1.9E0 | 2.5E-4 | 2.5E-4 | 1.1E1 | 8.9E0 | 151 | 25 | 151 | 25 | 0.47 |
| bL | ng/mL | 4.1E0 | 3.5E0 | 9.4E0 | 8.2E0 | 1.2E1 | 8.4E0 | 4.6E-2 | 4.6E-2 | 6.0E1 | 3.0E1 | 151 | 25 | 151 | 25 | 0.52 |
| bM | mg/mL | 1.8E0 | 1.7E0 | 2.2E0 | 1.8E0 | 1.5E0 | 1.2E0 | 1.4E-1 | 1.6E-2 | 8.6E0 | 5.2E0 | 151 | 25 | 151 | 25 | 0.43 |
| bN | ng/mL | 3.4E1 | 2.4E1 | 1.3E2 | 5.1E1 | 3.0E2 | 6.4E1 | 1.4E-1 | 5.9E-1 | 1.9E3 | 2.5E2 | 151 | 25 | 151 | 25 | 0.41 |
| bO | ng/mL | 4.0E-2 | 4.0E-2 | 8.4E0 | 1.3E1 | 1.8E1 | 3.1E1 | 4.0E-2 | 4.0E-2 | 1.2E2 | 1.3E2 | 151 | 25 | 151 | 25 | 0.45 |
| bP | mg/mL | 5.2E-1 | 5.7E-1 | 7.7E-1 | 6.0E-1 | 7.4E-1 | 3.6E-1 | 4.9E-2 | 9.2E-2 | 4.8E0 | 1.6E0 | 151 | 25 | 151 | 25 | 0.48 |
| bQ | pg/mL | 2.1E1 | 5.9E1 | 1.5E2 | 6.7E1 | 1.1E3 | 5.7E1 | 1.5E-1 | 1.5E-1 | 1.3E4 | 2.2E2 | 151 | 25 | 151 | 25 | 0.70 |
| bR | ng/mL | 1.2E-2 | 1.2E-2 | 1.7E-1 | 9.8E-2 | 7.6E-1 | 1.3E-1 | 1.2E-2 | 1.2E-2 | 8.7E0 | 3.9E-1 | 151 | 25 | 151 | 25 | 0.52 |
| bS | pg/mL | 9.4E-1 | 9.4E-1 | 9.6E0 | 8.6E0 | 4.3E1 | 2.0E1 | 9.4E-1 | 9.4E-1 | 3.9E2 | 7.2E1 | 151 | 25 | 151 | 25 | 0.52 |
| bU | ng/mL | 6.8E-2 | 1.6E-1 | 1.9E-1 | 1.7E-1 | 5.7E-1 | 1.8E-1 | 1.3E-2 | 1.3E-2 | 6.6E0 | 6.5E-1 | 151 | 25 | 151 | 25 | 0.55 |
| bV | pg/mL | 4.9E2 | 5.5E2 | 6.2E2 | 7.3E2 | 9.3E2 | 5.1E2 | 1.6E2 | 2.7E2 | 1.2E4 | 2.2E3 | 151 | 25 | 151 | 25 | 0.60 |
| bW | pg/mL | 3.2E2 | 3.2E2 | 5.0E2 | 6.6E2 | 5.7E2 | 9.9E2 | 8.4E1 | 1.5E2 | 4.8E3 | 3.9E3 | 151 | 25 | 151 | 25 | 0.54 |
| bX | ng/mL | 2.5E-5 | 3.0E-3 | 2.6E-3 | 2.7E-3 | 3.2E-3 | 2.9E-3 | 2.5E-5 | 2.5E-5 | 1.3E-2 | 7.8E-3 | 151 | 25 | 151 | 25 | 0.52 |
| bZ | pg/mL | 2.7E2 | 6.4E2 | 2.1E3 | 1.4E3 | 7.6E3 | 1.9E3 | 1.5E-1 | 1.0E2 | 5.8E4 | 7.4E3 | 151 | 25 | 151 | 25 | 0.60 |
| cA | pg/mL | 6.0E-1 | 6.0E-1 | 4.3E0 | 2.6E0 | 3.0E1 | 5.3E0 | 6.0E-1 | 6.0E-1 | 3.7E2 | 2.1E1 | 151 | 25 | 151 | 25 | 0.52 |
| cB | ng/mL | 4.5E-2 | 4.7E-2 | 7.1E-2 | 9.4E-2 | 8.0E-2 | 1.2E-1 | 1.7E-3 | 1.7E-3 | 3.8E-1 | 4.3E-1 | 151 | 25 | 151 | 25 | 0.50 |
| cC | pg/mL | 4.1E1 | 3.9E1 | 4.6E1 | 4.1E1 | 5.2E1 | 3.0E1 | 1.0E0 | 1.0E0 | 4.5E2 | 1.1E2 | 151 | 25 | 151 | 25 | 0.49 |
| cD | pg/mL | 4.9E0 | 5.5E0 | 1.4E1 | 6.1E0 | 4.9E1 | 6.5E0 | 3.3E-1 | 3.3E-1 | 4.8E2 | 3.3E1 | 151 | 25 | 151 | 25 | 0.50 |
| cE | pg/mL | 5.5E1 | 9.9E1 | 2.8E2 | 1.9E2 | 6.3E2 | 2.3E2 | 1.2E-1 | 1.4E1 | 3.8E3 | 1.1E3 | 151 | 25 | 151 | 25 | 0.62 |
| cF | pg/mL | 5.3E-1 | 5.3E-1 | 1.6E1 | 1.3E1 | 3.1E1 | 1.9E1 | 5.3E-1 | 5.3E-1 | 2.7E2 | 6.5E1 | 151 | 25 | 151 | 25 | 0.48 |
| cG | pg/mL | 5.3E1 | 1.1E2 | 1.7E2 | 1.8E2 | 8.6E2 | 2.3E2 | 7.8E0 | 2.4E1 | 1.0E4 | 1.1E3 | 151 | 25 | 151 | 25 | 0.66 |
| cH | uIU/mL | 3.6E0 | 2.5E0 | 8.1E0 | 4.7E0 | 1.8E1 | 7.2E0 | 8.6E-3 | 8.6E-3 | 1.6E2 | 3.4E1 | 151 | 25 | 151 | 25 | 0.40 |
| cI | ng/mL | 6.0E0 | 9.6E0 | 1.4E1 | 1.7E1 | 2.0E1 | 2.6E1 | 3.2E-2 | 5.1E-1 | 1.2E2 | 1.2E2 | 151 | 25 | 151 | 25 | 0.52 |
| cJ | ug/mL | 6.7E1 | 4.6E1 | 1.0E2 | 7.2E1 | 1.1E2 | 7.5E1 | 6.9E0 | 5.6E0 | 6.4E2 | 3.4E2 | 151 | 25 | 151 | 25 | 0.41 |
| cK | ng/mL | 3.8E-3 | 3.8E-3 | 2.4E-2 | 1.8E-2 | 1.2E-1 | 4.3E-2 | 3.8E-3 | 3.8E-3 | 1.5E0 | 2.1E-1 | 151 | 25 | 151 | 25 | 0.52 |
| cL | pg/mL | 2.2E2 | 2.0E2 | 5.6E2 | 4.1E2 | 2.1E3 | 5.6E2 | 3.1E1 | 6.7E1 | 2.4E4 | 2.8E3 | 151 | 25 | 151 | 25 | 0.58 |
| cM | pg/mL | 2.7E2 | 2.8E2 | 2.9E2 | 2.7E2 | 1.7E2 | 1.0E2 | 2.5E1 | 5.7E1 | 1.1E3 | 4.5E2 | 151 | 25 | 151 | 25 | 0.50 |
| cN | pg/mL | 1.2E2 | 1.2E2 | 1.3E2 | 1.3E2 | 9.0E1 | 3.6E1 | 3.8E1 | 7.9E1 | 1.1E3 | 2.0E2 | 151 | 25 | 151 | 25 | 0.51 |
| cO | pg/mL | 2.1E2 | 2.8E2 | 4.2E2 | 3.5E2 | 1.6E3 | 3.0E2 | 5.4E1 | 9.6E1 | 1.9E4 | 1.5E3 | 151 | 25 | 151 | 25 | 0.59 |
| cP | ng/mL | 2.4E3 | 2.4E3 | 2.5E3 | 2.5E3 | 9.5E2 | 1.0E3 | 6.2E2 | 1.0E3 | 5.6E3 | 4.7E3 | 151 | 25 | 151 | 25 | 0.50 |
| cQ | ng/mL | 4.9E-2 | 7.1E-2 | 1.2E-1 | 1.6E-1 | 2.1E-1 | 2.3E-1 | 2.0E-3 | 2.0E-3 | 1.3E0 | 8.7E-1 | 151 | 25 | 151 | 25 | 0.54 |
| cR | ng/mL | 3.0E2 | 4.6E2 | 5.8E2 | 6.9E2 | 8.5E2 | 6.3E2 | 2.0E1 | 8.6E1 | 7.7E3 | 2.2E3 | 151 | 25 | 151 | 25 | 0.60 |
| cS | ng/mL | 2.9E2 | 3.8E2 | 4.1E2 | 8.8E2 | 4.3E2 | 1.5E3 | 4.1E1 | 9.7E1 | 2.5E3 | 7.1E3 | 151 | 25 | 151 | 25 | 0.57 |
| cT | ng/mL | 4.6E1 | 9.6E1 | 1.3E2 | 3.2E2 | 2.5E2 | 5.0E2 | 3.6E0 | 1.1E1 | 2.1E3 | 1.5E3 | 151 | 25 | 151 | 25 | 0.62 |
| cU | ng/mL | 5.7E1 | 9.8E1 | 9.5E1 | 1.2E2 | 1.5E2 | 9.7E1 | 6.2E0 | 1.7E1 | 1.6E3 | 3.9E2 | 151 | 25 | 151 | 25 | 0.64 |
| cV | ng/mL | 1.9E-1 | 2.1E-1 | 8.0E-1 | 2.6E-1 | 4.0E0 | 1.9E-1 | 2.5E-2 | 6.8E-2 | 4.7E1 | 9.3E-1 | 151 | 25 | 151 | 25 | 0.53 |
| cW | mIU/mL | 4.8E-2 | 6.3E-2 | 8.9E-2 | 8.8E-2 | 3.6E-1 | 8.9E-2 | 4.8E-3 | 1.4E-2 | 4.5E0 | 3.9E-1 | 151 | 25 | 151 | 25 | 0.57 |
| cX | ng/mL | 1.4E-1 | 6.9E-2 | 2.1E0 | 3.1E-1 | 6.0E0 | 5.6E-1 | 2.3E-4 | 2.3E-4 | 2.8E1 | 2.5E0 | 151 | 25 | 151 | 25 | 0.45 |
| cY | ng/mL | 7.4E0 | 8.1E0 | 1.1E1 | 9.1E0 | 1.1E1 | 8.2E0 | 1.7E-1 | 6.0E-1 | 6.1E1 | 3.6E1 | 151 | 25 | 151 | 25 | 0.47 |

Figure 36 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cZ | ug/mL | 1.3E1 | 1.2E1 | 1.5E1 | 1.4E1 | 6.8E0 | 7.1E0 | 2.3E0 | 3.3E0 | 4.6E1 | 3.0E1 | 151 | 25 | 151 | 25 | 0.46 |
| dA | pg/mL | 3.1E2 | 3.6E2 | 3.9E2 | 3.9E2 | 4.8E2 | 2.1E2 | 1.0E2 | 1.1E2 | 5.8E3 | 8.8E2 | 151 | 25 | 151 | 25 | 0.55 |
| dB | ug/mL | 1.8E1 | 1.7E1 | 1.9E1 | 1.7E1 | 2.1E1 | 8.6E0 | 2.1E0 | 2.2E0 | 2.5E2 | 2.8E1 | 151 | 25 | 151 | 25 | 0.48 |
| dC | nmol/L | 3.4E1 | 3.2E1 | 3.8E1 | 3.5E1 | 1.7E1 | 1.4E1 | 7.8E0 | 1.5E1 | 1.4E2 | 6.5E1 | 151 | 25 | 151 | 25 | 0.45 |
| dD | ug/mL | 3.4E1 | 3.0E1 | 3.6E1 | 3.3E1 | 1.1E1 | 1.1E1 | 1.4E1 | 1.6E1 | 7.4E1 | 6.0E1 | 151 | 25 | 151 | 25 | 0.40 |
| dE | | 4.1E-1 | 7.0E-1 | 5.4E-1 | 8.4E-1 | 5.6E-1 | 8.0E-1 | 8.4E-3 | 8.4E-3 | 2.7E0 | 2.9E0 | 151 | 25 | 151 | 25 | 0.62 |
| dF | ng/mL | 2.4E2 | 3.7E2 | 3.3E2 | 4.7E2 | 2.4E2 | 3.0E2 | 7.5E1 | 1.1E2 | 1.3E3 | 1.2E3 | 151 | 25 | 151 | 25 | 0.67 |
| dG | ng/mL | 1.2E1 | 1.4E1 | 1.7E1 | 2.0E1 | 1.9E1 | 1.9E1 | 3.0E0 | 4.8E0 | 1.8E2 | 8.7E1 | 151 | 25 | 151 | 25 | 0.57 |
| dH | pg/mL | 7.9E0 | 1.1E1 | 2.2E1 | 1.3E1 | 6.6E1 | 1.4E1 | 4.0E-2 | 4.0E-2 | 6.7E2 | 7.6E1 | 151 | 25 | 151 | 25 | 0.57 |
| dI | pg/mL | 4.6E-1 | 4.6E-1 | 4.0E0 | 2.6E0 | 2.7E1 | 4.2E0 | 4.6E-1 | 4.6E-1 | 3.3E2 | 1.9E1 | 151 | 25 | 151 | 25 | 0.55 |
| dJ | ng/mL | 2.0E0 | 2.1E0 | 2.2E0 | 2.0E0 | 1.1E0 | 1.1E0 | 3.2E-2 | 3.2E-2 | 5.6E0 | 4.0E0 | 151 | 25 | 151 | 25 | 0.48 |
| dK | uIU/mL | 1.5E0 | 7.4E-1 | 2.2E0 | 1.7E0 | 3.7E0 | 2.6E0 | 2.8E-4 | 1.4E-2 | 3.9E1 | 1.1E1 | 151 | 25 | 151 | 25 | 0.35 |
| dL | ng/mL | 8.8E2 | 8.4E2 | 1.0E3 | 1.2E3 | 5.7E2 | 8.8E2 | 2.8E2 | 4.3E2 | 3.8E3 | 4.8E3 | 151 | 25 | 151 | 25 | 0.52 |
| dM | pg/mL | 9.6E2 | 1.1E3 | 1.3E3 | 1.9E3 | 1.5E3 | 1.5E3 | 3.7E2 | 6.3E2 | 1.5E4 | 5.8E3 | 151 | 25 | 151 | 25 | 0.62 |
| dN | ug/mL | 1.0E2 | 1.1E2 | 1.0E2 | 1.2E2 | 4.0E1 | 6.0E1 | 2.4E1 | 4.7E1 | 2.8E2 | 3.3E2 | 151 | 25 | 151 | 25 | 0.56 |
| dR | pg/ml | 1.5E3 | 8.3E2 | 2.2E3 | 1.1E3 | 2.1E3 | 1.2E3 | 1.4E2 | 1.3E2 | 9.8E3 | 5.3E3 | 116 | 17 | 116 | 17 | 0.32 |
| dX | ng/ml | 8.1E-2 | 8.2E-2 | 1.3E-1 | 1.4E-1 | 2.0E-1 | 1.5E-1 | 2.6E-3 | 2.6E-3 | 1.2E0 | 4.2E-1 | 51 | 10 | 51 | 10 | 0.55 |
| eF | ng/ml | 4.1E0 | 4.7E0 | 5.2E0 | 6.8E0 | 4.4E0 | 6.5E0 | 2.0E0 | 2.0E0 | 4.6E1 | 2.9E1 | 116 | 17 | 116 | 17 | 0.56 |
| eC | pg/ml | 2.9E2 | 2.5E2 | 3.6E2 | 3.7E2 | 2.6E2 | 5.4E2 | 9.9E0 | 1.9E1 | 1.6E3 | 2.0E3 | 105 | 12 | 105 | 12 | 0.36 |
| eD | pg/ml | 2.2E2 | 2.4E2 | 7.4E2 | 2.6E2 | 1.6E3 | 1.5E2 | 5.2E-1 | 5.9E1 | 8.3E3 | 4.9E2 | 87 | 8 | 87 | 8 | 0.53 |
| eM | ng/ml | 2.8E0 | 2.8E0 | 5.0E0 | 4.7E0 | 6.6E0 | 5.7E0 | 6.9E-1 | 8.8E-1 | 3.9E1 | 2.3E1 | 66 | 13 | 66 | 13 | 0.51 |
| eP | ng/ml | 3.7E-3 | 3.7E-3 | 1.2E0 | 1.2E0 | 4.1E0 | 3.1E0 | 3.7E-3 | 3.7E-3 | 2.8E1 | 1.0E1 | 51 | 10 | 51 | 10 | 0.49 |
| fP | ng/ml | 2.7E2 | 2.4E2 | 3.3E2 | 3.0E2 | 1.9E2 | 1.5E2 | 1.8E0 | 9.5E1 | 1.0E3 | 6.0E2 | 113 | 14 | 113 | 14 | 0.47 |
| fR | ng/ml | 1.3E5 | 2.5E5 | 2.1E5 | 3.0E5 | 1.7E5 | 2.3E5 | 3.6E4 | 1.9E2 | 6.9E5 | 8.7E5 | 95 | 20 | 95 | 20 | 0.63 |
| gC | ng/ml | 2.3E2 | 2.8E2 | 2.5E2 | 3.1E2 | 1.1E2 | 1.5E2 | 8.3E1 | 1.5E2 | 6.4E2 | 5.9E2 | 38 | 9 | 38 | 9 | 0.60 |
| gL | pg/ml | 6.5E4 | 7.7E4 | 7.2E4 | 9.3E4 | 3.4E4 | 5.0E4 | 1.1E4 | 4.4E4 | 1.9E5 | 2.2E5 | 116 | 17 | 116 | 17 | 0.63 |
| gP | U/ml | 2.8E2 | 2.7E2 | 2.9E2 | 2.8E2 | 1.3E2 | 8.3E1 | 1.2E1 | 1.3E2 | 1.1E3 | 4.4E2 | 115 | 17 | 115 | 17 | 0.48 |
| gW | ng/ml | 6.1E2 | 3.4E2 | 9.4E2 | 6.6E2 | 1.1E3 | 9.0E2 | 2.3E0 | 1.5E2 | 6.1E3 | 3.1E3 | 89 | 10 | 89 | 10 | 0.40 |
| tF | pg/mL | 1.3E3 | 1.0E3 | 1.3E4 | 4.4E3 | 4.1E4 | 7.3E3 | 1.2E1 | 1.8E1 | 2.8E5 | 2.4E4 | 106 | 13 | 106 | 13 | 0.50 |
| hA | ng/ml | 2.5E0 | 3.6E0 | 1.4E1 | 1.8E1 | 5.1E1 | 3.6E1 | 1.7E-2 | 2.0E0 | 3.5E2 | 1.1E2 | 87 | 9 | 87 | 9 | 0.68 |
| nM | pg/ml | 1.0E-9 | 1.0E-9 | 1.0E-9 | 1.5E2 | 0.0E0 | 4.8E2 | 1.0E-9 | 1.0E-9 | 1.0E-9 | 1.5E3 | 64 | 10 | 64 | 10 | 0.55 |
| nN | pg/ml | 1.2E3 | 3.7E3 | 3.7E3 | 2.4E4 | 1.3E4 | 4.7E4 | 8.1E1 | 6.3E2 | 1.0E5 | 1.5E5 | 64 | 10 | 64 | 10 | 0.77 |
| nO | pg/ml | 2.4E1 | 3.4E1 | 3.8E1 | 3.7E1 | 4.9E1 | 2.3E1 | 4.0E0 | 1.2E1 | 3.1E2 | 8.9E1 | 64 | 10 | 64 | 10 | 0.60 |
| nR | pg/ml | 1.6E1 | 4.4E1 | 6.6E1 | 2.4E2 | 1.4E2 | 5.9E2 | 1.0E0 | 4.7E0 | 8.2E2 | 1.9E3 | 64 | 10 | 64 | 10 | 0.63 |
| nT | pg/ml | 6.5E1 | 1.1E2 | 1.0E2 | 2.1E2 | 1.1E2 | 2.6E2 | 1.0E-9 | 3.9E1 | 6.4E2 | 9.2E2 | 64 | 10 | 64 | 10 | 0.68 |
| nU | pg/ml | 3.5E1 | 1.0E2 | 8.9E1 | 2.0E2 | 2.1E2 | 2.8E2 | 1.0E-9 | 1.0E-9 | 1.5E3 | 9.2E2 | 64 | 10 | 64 | 10 | 0.73 |
| lW | pg/ml | 1.0E-9 | 1.0E-9 | 1.1E1 | 7.9E0 | 3.1E1 | 1.3E1 | 1.0E-9 | 1.0E-9 | 1.7E2 | 3.9E1 | 64 | 10 | 64 | 10 | 0.54 |
| lX | pg/ml | 9.1E2 | 7.3E2 | 1.0E3 | 9.3E2 | 5.6E2 | 7.3E2 | 2.3E2 | 1.9E2 | 2.6E3 | 2.5E3 | 64 | 10 | 64 | 10 | 0.42 |
| lY | pg/ml | 1.9E1 | 1.7E1 | 2.0E1 | 1.9E1 | 1.8E1 | 1.5E1 | 1.0E-9 | 5.7E-1 | 1.2E2 | 4.5E1 | 64 | 10 | 64 | 10 | 0.48 |
| mE | pg/ml | 1.0E-9 | 3.5E-1 | 2.6E0 | 2.3E0 | 8.0E0 | 3.3E0 | 1.0E-9 | 1.0E-9 | 5.7E1 | 9.2E0 | 64 | 10 | 64 | 10 | 0.56 |
| mF | pg/ml | 2.7E-1 | 4.0E-1 | 7.4E0 | 1.5E0 | 3.3E1 | 3.2E0 | 1.0E-9 | 1.0E-9 | 2.5E2 | 1.0E1 | 64 | 10 | 64 | 10 | 0.51 |
| mH | pg/ml | 3.1E0 | 4.3E0 | 5.4E0 | 5.5E0 | 8.2E0 | 5.3E0 | 4.0E-1 | 9.0E-1 | 5.3E1 | 1.9E1 | 64 | 10 | 64 | 10 | 0.56 |
| mI | pg/ml | 1.0E-9 | 2.3E1 | 1.1E1 | 7.0E1 | 2.6E1 | 1.4E2 | 1.0E-9 | 1.0E-9 | 1.8E2 | 4.6E2 | 64 | 10 | 64 | 10 | 0.70 |
| mM | pg/ml | 3.4E1 | 4.2E1 | 8.1E1 | 8.7E1 | 1.6E2 | 1.4E2 | 1.0E-9 | 1.0E-9 | 1.1E3 | 4.7E2 | 64 | 10 | 64 | 10 | 0.51 |
| mP | pg/ml | 1.5E1 | 1.6E1 | 1.8E1 | 1.1E2 | 1.6E1 | 2.5E2 | 1.0E-9 | 7.5E0 | 1.2E2 | 8.1E2 | 63 | 10 | 63 | 10 | 0.54 |
| mS | pg/ml | 1.6E3 | 1.3E3 | 1.8E3 | 1.6E3 | 9.9E2 | 1.1E3 | 1.0E-9 | 1.0E-9 | 5.1E3 | 3.5E3 | 64 | 10 | 64 | 10 | 0.43 |
| mT | pg/ml | 5.0E1 | 6.0E1 | 1.3E2 | 3.1E2 | 2.3E2 | 5.7E2 | 1.0E1 | 1.6E1 | 1.4E3 | 1.7E3 | 63 | 10 | 63 | 10 | 0.54 |
| mU | pg/ml | 2.2E0 | 3.8E0 | 6.5E0 | 5.7E0 | 2.8E1 | 6.6E0 | 1.0E-9 | 1.2E0 | 2.2E2 | 2.3E1 | 63 | 10 | 63 | 10 | 0.64 |
| mW | pg/ml | 2.2E3 | 1.9E3 | 2.4E3 | 3.2E3 | 1.3E3 | 3.1E3 | 1.0E-9 | 1.3E3 | 6.2E3 | 1.1E4 | 63 | 10 | 63 | 10 | 0.48 |
| mY | pg/ml | 6.5E2 | 8.8E2 | 8.6E2 | 1.6E3 | 9.7E2 | 2.3E3 | 1.0E-9 | 1.9E2 | 5.6E3 | 8.0E3 | 64 | 10 | 64 | 10 | 0.58 |
| mZ | pg/ml | 1.9E2 | 9.4E1 | 3.9E2 | 1.5E2 | 4.9E2 | 1.6E2 | 1.0E-9 | 1.1E1 | 3.1E3 | 5.5E2 | 63 | 10 | 63 | 10 | 0.29 |
| nA | pg/ml | 1.5E0 | 1.9E0 | 7.7E0 | 3.2E0 | 1.5E1 | 3.6E0 | 1.0E-9 | 1.0E-9 | 6.5E1 | 9.1E0 | 63 | 10 | 63 | 10 | 0.45 |
| nB | pg/ml | 2.8E2 | 3.5E2 | 3.0E2 | 3.8E2 | 1.6E2 | 2.4E2 | 3.0E1 | 1.3E2 | 8.2E2 | 9.6E2 | 64 | 10 | 64 | 10 | 0.59 |
| nC | pg/ml | 1.0E-9 | 5.5E2 | 1.0E4 | 1.9E3 | 5.5E4 | 3.1E3 | 1.0E-9 | 1.0E-9 | 3.8E5 | 9.1E3 | 64 | 10 | 64 | 10 | 0.68 |
| nD | pg/ml | 7.9E0 | 5.8E0 | 1.5E1 | 9.3E0 | 3.5E1 | 1.0E1 | 1.0E-9 | 1.0E-9 | 2.6E2 | 2.8E1 | 63 | 10 | 63 | 10 | 0.46 |
| nF | pg/ml | 1.0E-9 | 1.0E-9 | 3.4E0 | 1.3E0 | 1.4E1 | 4.2E0 | 1.0E-9 | 1.0E-9 | 9.3E1 | 1.3E1 | 64 | 10 | 64 | 10 | 0.49 |
| nH | pg/ml | 1.8E-1 | 4.7E0 | 2.1E2 | 2.5E1 | 1.3E3 | 4.0E1 | 1.0E-9 | 1.0E-9 | 1.0E4 | 1.2E2 | 63 | 10 | 63 | 10 | 0.69 |

Figure 36 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nI | pg/ml | 4.6E1 | 1.0E-9 | 7.9E1 | 1.0E-9 | 1.6E2 | 0.0E0 | 1.0E-9 | 1.0E-9 | 1.2E3 | 1.0E-9 | 64 | 10 | 64 | 10 | 0.20 |
| nJ | pg/ml | 1.7E-1 | 7.6E-1 | 3.2E0 | 9.4E-1 | 1.7E1 | 1.0E0 | 1.0E-9 | 1.0E-9 | 1.3E2 | 3.0E0 | 64 | 10 | 64 | 10 | 0.52 |
| nK | pg/ml | 1.0E-9 | 1.8E1 | 1.6E1 | 2.0E1 | 3.5E1 | 2.1E1 | 1.0E-9 | 1.0E-9 | 2.2E2 | 6.2E1 | 63 | 10 | 63 | 10 | 0.63 |
| nL | pg/ml | 1.0E-9 | 1.7E1 | 3.0E2 | 1.1E2 | 1.8E3 | 2.3E2 | 1.0E-9 | 1.0E-9 | 1.4E4 | 7.3E2 | 64 | 10 | 64 | 10 | 0.68 |
| hR | pg/ml | 2.7E4 | 2.6E4 | 2.9E4 | 2.9E4 | 1.2E4 | 9.4E3 | 1.0E-9 | 1.8E4 | 5.8E4 | 4.3E4 | 81 | 8 | 81 | 8 | 0.49 |
| hV | pg/ml | 4.4E2 | 4.4E2 | 4.5E2 | 4.4E2 | 2.3E2 | 2.3E2 | 1.0E-9 | 9.5E1 | 1.2E3 | 7.4E2 | 81 | 8 | 81 | 8 | 0.50 |
| hW | pg/ml | 1.8E3 | 3.1E3 | 2.1E3 | 7.6E3 | 1.1E3 | 1.3E4 | 1.0E-9 | 1.5E3 | 7.3E3 | 4.0E4 | 81 | 8 | 81 | 8 | 0.76 |
| hX | pg/ml | 1.0E3 | 1.3E3 | 1.1E3 | 1.2E3 | 9.5E2 | 3.8E2 | 2.5E0 | 7.0E2 | 8.6E3 | 2.0E3 | 81 | 8 | 81 | 8 | 0.67 |
| iA | pg/ml | 1.6E2 | 1.8E2 | 2.5E2 | 2.8E2 | 2.8E2 | 2.5E2 | 1.5E1 | 5.6E1 | 1.8E3 | 8.7E2 | 105 | 14 | 105 | 14 | 0.55 |
| iB | ng/ml | 4.9E0 | 8.4E0 | 6.2E0 | 1.0E1 | 4.8E0 | 6.4E0 | 3.3E-2 | 2.4E0 | 2.4E1 | 2.2E1 | 87 | 9 | 87 | 9 | 0.70 |
| iC | U/ml | 3.1E-1 | 5.3E-1 | 1.2E0 | 7.7E-1 | 5.9E0 | 8.3E-1 | 1.0E-9 | 6.8E-2 | 5.5E1 | 2.8E0 | 87 | 9 | 87 | 9 | 0.63 |
| iH | ng/ml | 1.6E5 | 1.8E5 | 1.6E5 | 1.6E5 | 4.9E4 | 5.5E4 | 2.9E3 | 7.7E4 | 2.6E5 | 2.4E5 | 105 | 14 | 105 | 14 | 0.52 |
| iJ | ng/ml | 4.9E4 | 3.8E4 | 5.6E4 | 4.6E4 | 3.7E4 | 2.2E4 | 1.8E3 | 1.2E4 | 2.5E5 | 9.3E4 | 105 | 14 | 105 | 14 | 0.43 |
| hB | ng/ml | 4.6E-1 | 6.2E-1 | 6.1E-1 | 8.5E-1 | 4.9E-1 | 5.5E-1 | 1.2E-1 | 2.9E-1 | 3.2E0 | 2.4E0 | 105 | 14 | 105 | 14 | 0.69 |
| hC | pg/ml | 5.1E3 | 8.9E3 | 7.7E3 | 1.2E4 | 1.2E4 | 1.4E4 | 4.1E1 | 3.0E2 | 1.1E5 | 5.7E4 | 105 | 14 | 105 | 14 | 0.61 |
| hF | pg/ml | 1.0E-9 | 1.0E-9 | 3.8E1 | 1.0E-9 | 3.9E2 | 0.0E0 | 1.0E-9 | 1.0E-9 | 4.0E3 | 1.0E-9 | 105 | 14 | 105 | 14 | 0.50 |
| hG | pg/ml | 6.8E3 | 6.7E3 | 7.4E3 | 8.9E3 | 3.1E3 | 5.3E3 | 1.8E3 | 3.6E3 | 1.8E4 | 2.0E4 | 105 | 14 | 105 | 14 | 0.53 |
| iO | ng/ml | 3.8E5 | 4.2E5 | 4.2E5 | 4.2E5 | 2.0E5 | 2.0E5 | 1.1E4 | 1.0E5 | 1.1E6 | 8.2E5 | 105 | 14 | 105 | 14 | 0.51 |
| iP | ng/ml | 5.3E4 | 4.6E4 | 5.8E4 | 5.0E4 | 4.8E4 | 1.9E4 | 1.0E-9 | 2.2E4 | 4.4E5 | 7.0E4 | 105 | 14 | 105 | 14 | 0.46 |
| iZ | ng/ml | 1.6E3 | 2.1E3 | 1.8E3 | 2.5E3 | 8.5E2 | 1.1E3 | 6.6E2 | 1.1E3 | 5.7E3 | 4.6E3 | 103 | 14 | 103 | 14 | 0.70 |
| rC | pg/ml | 1.5E3 | 1.9E3 | 2.2E3 | 1.7E3 | 2.4E3 | 9.5E2 | 1.0E-9 | 6.0E2 | 1.5E4 | 2.9E3 | 79 | 7 | 79 | 7 | 0.49 |
| rB | pg/ml | 3.1E1 | 7.7E1 | 4.7E1 | 1.1E2 | 6.1E1 | 1.2E2 | 1.0E-9 | 1.0E-9 | 3.9E2 | 3.2E2 | 79 | 7 | 79 | 7 | 0.65 |
| jD | ng/ml | 2.9E1 | 5.0E1 | 3.8E1 | 9.1E1 | 3.8E1 | 9.8E1 | 1.0E-9 | 7.6E0 | 1.9E2 | 2.9E2 | 87 | 9 | 87 | 9 | 0.66 |
| jE | ng/ml | 1.0E-9 | 1.0E-9 | 5.2E0 | 9.4E0 | 1.2E1 | 1.5E1 | 1.0E-9 | 1.0E-9 | 6.2E1 | 3.5E1 | 87 | 9 | 87 | 9 | 0.57 |
| jF | ng/ml | 4.2E1 | 7.7E0 | 5.0E1 | 3.1E1 | 5.4E1 | 4.7E1 | 1.0E-9 | 1.0E-9 | 2.1E2 | 1.2E2 | 87 | 9 | 87 | 9 | 0.40 |
| jG | ng/ml | 4.3E3 | 4.2E3 | 4.5E3 | 4.6E3 | 2.0E3 | 1.5E3 | 6.7E2 | 2.5E3 | 9.6E3 | 7.9E3 | 87 | 9 | 87 | 9 | 0.52 |
| jH | ng/ml | 7.5E1 | 1.2E2 | 7.9E1 | 1.4E2 | 4.3E1 | 1.2E2 | 1.3E1 | 3.3E1 | 2.4E2 | 4.3E2 | 87 | 9 | 87 | 9 | 0.70 |
| jI | ng/ml | 7.3E1 | 1.2E2 | 7.6E1 | 1.6E2 | 3.2E1 | 1.2E2 | 1.9E1 | 4.4E1 | 1.9E2 | 4.4E2 | 87 | 9 | 87 | 9 | 0.75 |
| rA | pg/ml | 2.4E1 | 2.0E1 | 3.1E1 | 2.7E1 | 2.8E1 | 1.8E1 | 1.0E-9 | 1.2E1 | 2.0E2 | 6.8E1 | 85 | 8 | 85 | 8 | 0.48 |
| qY | pg/ml | 1.8E1 | 9.0E0 | 4.1E1 | 1.3E1 | 5.8E1 | 9.0E0 | 8.7E-1 | 2.1E0 | 3.3E2 | 2.7E1 | 85 | 8 | 85 | 8 | 0.32 |
| qX | pg/ml | 5.5E1 | 7.8E1 | 7.0E1 | 9.0E1 | 4.8E1 | 6.2E1 | 1.0E-9 | 2.3E1 | 2.3E2 | 2.1E2 | 85 | 8 | 85 | 8 | 0.59 |
| qW | pg/ml | 7.8E0 | 6.8E0 | 1.2E1 | 9.4E0 | 1.6E1 | 8.6E0 | 1.0E-9 | 1.0E-9 | 1.2E2 | 2.2E1 | 85 | 8 | 85 | 8 | 0.48 |
| qV | pg/ml | 1.8E3 | 1.8E3 | 2.5E3 | 2.2E3 | 2.0E3 | 1.6E3 | 1.0E2 | 6.3E2 | 1.1E4 | 5.6E3 | 85 | 8 | 85 | 8 | 0.47 |
| qU | pg/ml | 8.1E1 | 8.7E1 | 1.9E2 | 2.5E2 | 3.1E2 | 3.7E2 | 1.0E-9 | 1.9E1 | 2.1E3 | 1.1E3 | 85 | 8 | 85 | 8 | 0.56 |
| qT | pg/ml | 4.1E1 | 3.4E1 | 6.7E1 | 5.7E1 | 7.3E1 | 5.4E1 | 1.0E-9 | 6.9E0 | 4.9E2 | 1.6E2 | 85 | 8 | 85 | 8 | 0.46 |
| jK | ng/ml | 1.6E3 | 1.2E3 | 1.7E3 | 1.3E3 | 6.2E2 | 6.3E2 | 2.8E2 | 7.5E2 | 4.1E3 | 2.9E3 | 87 | 9 | 87 | 9 | 0.26 |
| jL | ng/ml | 2.0E2 | 2.9E2 | 2.7E2 | 3.3E2 | 2.1E2 | 1.8E2 | 5.6E1 | 1.5E2 | 9.6E2 | 6.3E2 | 87 | 9 | 87 | 9 | 0.66 |
| jM | ng/ml | 7.1E4 | 4.9E4 | 7.6E4 | 6.8E4 | 3.9E4 | 5.2E4 | 4.6E3 | 1.3E4 | 1.8E5 | 1.4E5 | 87 | 9 | 87 | 9 | 0.41 |
| jO | pg/ml | 2.2E5 | 2.6E5 | 2.8E5 | 2.7E5 | 1.7E5 | 1.6E5 | 6.0E4 | 9.8E4 | 1.1E6 | 6.5E5 | 87 | 9 | 87 | 9 | 0.50 |
| jP | pg/ml | 2.5E5 | 4.9E5 | 2.8E5 | 3.9E5 | 1.4E5 | 1.9E5 | 3.6E4 | 1.3E5 | 7.1E5 | 5.5E5 | 87 | 9 | 87 | 9 | 0.66 |
| jQ | pg/ml | 2.3E3 | 1.2E3 | 3.2E3 | 2.7E3 | 2.9E3 | 2.8E3 | 5.0E0 | 4.9E2 | 1.3E4 | 9.2E3 | 87 | 9 | 87 | 9 | 0.44 |
| jR | pg/ml | 5.7E3 | 3.3E3 | 1.0E4 | 9.5E3 | 1.2E4 | 1.4E4 | 1.0E-9 | 3.0E1 | 6.8E4 | 4.6E4 | 87 | 9 | 87 | 9 | 0.42 |
| jT | pg/ml | 1.8E5 | 1.6E5 | 1.8E5 | 1.5E5 | 7.2E4 | 5.1E4 | 7.1E4 | 7.5E4 | 5.5E5 | 2.2E5 | 87 | 9 | 87 | 9 | 0.34 |
| jU | mIU/ml | 5.5E0 | 5.8E0 | 1.2E1 | 1.4E1 | 1.9E1 | 1.8E1 | 8.1E-2 | 1.2E0 | 1.1E2 | 5.3E1 | 87 | 9 | 87 | 9 | 0.51 |
| jV | mIU/ml | 1.9E0 | 1.9E0 | 4.1E0 | 3.5E0 | 5.7E0 | 3.6E0 | 2.7E-3 | 2.1E-1 | 3.2E1 | 1.0E1 | 87 | 9 | 87 | 9 | 0.49 |
| jY | ng/ml | 9.7E-4 | 2.6E-3 | 7.7E-3 | 7.4E-3 | 3.4E-2 | 9.4E-3 | 1.0E-9 | 1.0E-9 | 3.0E-1 | 2.6E-2 | 87 | 9 | 87 | 9 | 0.60 |
| kC | pg/ml | 1.0E2 | 1.0E2 | 2.0E2 | 1.4E2 | 3.7E2 | 1.6E2 | 2.1E1 | 3.6E1 | 2.7E3 | 5.9E2 | 64 | 10 | 64 | 10 | 0.46 |
| kE | pg/ml | 1.4E5 | 1.3E5 | 1.4E5 | 1.4E5 | 3.7E4 | 5.5E4 | 3.8E4 | 7.9E4 | 2.3E5 | 2.7E5 | 64 | 10 | 64 | 10 | 0.45 |
| kF | pg/mL | 6.6E1 | 5.8E1 | 6.7E1 | 7.9E1 | 2.3E1 | 3.9E1 | 2.7E1 | 4.0E1 | 1.5E2 | 1.4E2 | 64 | 10 | 64 | 10 | 0.53 |
| kG | pg/mL | 8.3E3 | 8.9E3 | 1.1E4 | 3.3E4 | 9.5E3 | 4.9E4 | 1.3E3 | 1.1E3 | 5.8E4 | 1.6E5 | 64 | 10 | 64 | 10 | 0.55 |
| kI | pg/ml | 2.1E2 | 1.6E2 | 2.2E2 | 1.9E2 | 1.2E2 | 1.0E2 | 4.4E1 | 1.0E-9 | 6.7E2 | 3.5E2 | 64 | 10 | 64 | 10 | 0.45 |
| kK | pg/ml | 1.2E2 | 1.4E2 | 1.6E2 | 1.6E2 | 1.6E2 | 8.9E1 | 6.4E0 | 2.9E1 | 9.1E2 | 2.9E2 | 64 | 10 | 64 | 10 | 0.57 |
| kN | pg/ml | 1.2E3 | 8.1E2 | 1.6E3 | 1.4E3 | 1.7E3 | 2.0E3 | 2.1E2 | 3.8E2 | 1.0E4 | 7.0E3 | 64 | 10 | 64 | 10 | 0.34 |
| kO | pg/ml | 7.1E3 | 7.3E3 | 9.8E3 | 8.0E3 | 1.8E4 | 2.6E3 | 3.8E3 | 5.0E3 | 1.5E5 | 1.3E4 | 64 | 10 | 64 | 10 | 0.55 |
| kP | pg/ml | 6.2E3 | 4.0E3 | 7.0E3 | 5.3E3 | 4.3E3 | 4.0E3 | 9.6E2 | 1.6E3 | 2.7E4 | 1.5E4 | 64 | 10 | 64 | 10 | 0.34 |
| kQ | pg/ml | 4.2E3 | 5.3E3 | 5.2E3 | 6.7E3 | 3.9E3 | 5.2E3 | 5.6E2 | 1.4E3 | 2.5E4 | 2.2E4 | 105 | 14 | 105 | 14 | 0.60 |
| kR | pg/ml | 2.2E1 | 1.5E1 | 3.7E1 | 3.2E1 | 1.0E2 | 3.3E1 | 1.0E-9 | 2.9E0 | 1.0E3 | 1.1E2 | 105 | 14 | 105 | 14 | 0.46 |

Figure 36 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| kS | pg/ml | 8.8E2 | 8.9E2 | 9.9E2 | 1.0E3 | 5.8E2 | 6.6E2 | 8.2E1 | 3.2E2 | 3.2E3 | 2.5E3 | 105 | 14 | 105 | 14 | 0.47 |
| rZ | ng/ml | 1.4E-3 | 8.2E-3 | 1.1E-2 | 2.4E-2 | 3.6E-2 | 3.9E-2 | 1.0E-9 | 1.0E-9 | 3.0E-1 | 1.1E-1 | 80 | 7 | 80 | 7 | 0.60 |
| rY | ng/ml | 6.1E-2 | 7.6E-2 | 6.5E-1 | 8.4E-1 | 3.0E0 | 4.8E-2 | 1.0E-9 | 2.8E-2 | 2.0E1 | 1.6E-1 | 80 | 7 | 80 | 7 | 0.59 |
| rX | ng/ml | 1.0E-9 | 1.0E-9 | 1.3E-1 | 2.7E-2 | 6.0E-1 | 4.7E-2 | 1.0E-9 | 1.0E-9 | 3.7E0 | 1.2E-1 | 80 | 7 | 80 | 7 | 0.61 |
| lK | pg/ml | 6.8E1 | 3.6E1 | 1.5E2 | 9.7E1 | 1.8E2 | 1.5E2 | 1.0E-9 | 2.3E0 | 7.4E2 | 4.8E2 | 86 | 9 | 86 | 9 | 0.38 |
| lL | pg/ml | 1.6E3 | 2.5E3 | 2.9E3 | 2.8E3 | 5.0E3 | 1.7E3 | 7.5E1 | 8.8E2 | 4.2E4 | 6.8E3 | 87 | 9 | 87 | 9 | 0.63 |
| lM | pg/ml | 1.2E3 | 3.1E3 | 3.7E3 | 1.5E4 | 6.3E3 | 2.3E4 | 9.5E0 | 2.6E2 | 4.2E4 | 6.7E4 | 87 | 9 | 87 | 9 | 0.63 |
| lN | pg/ml | 1.0E-9 | 3.0E0 | 3.3E0 | 4.2E0 | 6.9E0 | 6.2E0 | 1.0E-9 | 1.0E-9 | 4.3E1 | 1.9E1 | 87 | 9 | 87 | 9 | 0.59 |
| lO | pg/ml | 1.0E-9 | 1.0E-9 | 1.9E0 | 1.5E1 | 1.4E1 | 4.6E1 | 1.0E-9 | 1.0E-9 | 1.3E2 | 1.4E2 | 86 | 9 | 86 | 9 | 0.55 |
| nW | pg/ml | 1.1E5 | 1.1E5 | 1.1E5 | 1.1E5 | 2.8E4 | 3.2E4 | 5.8E4 | 3.6E4 | 1.9E5 | 1.5E5 | 105 | 14 | 105 | 14 | 0.50 |
| nY | pg/ml | 2.2E3 | 3.5E3 | 2.6E3 | 3.4E3 | 1.5E3 | 2.0E3 | 5.1E2 | 6.3E2 | 1.0E4 | 8.1E3 | 105 | 14 | 105 | 14 | 0.63 |
| oO | pg/ml | 8.7E4 | 8.9E4 | 9.9E4 | 1.3E5 | 6.0E4 | 1.2E5 | 1.5E4 | 3.3E3 | 3.0E5 | 4.0E5 | 58 | 9 | 58 | 9 | 0.53 |
| oP | pg/ml | 1.3E5 | 1.4E5 | 1.4E5 | 1.7E5 | 8.1E4 | 1.6E5 | 2.4E4 | 2.4E4 | 4.2E5 | 5.7E5 | 58 | 9 | 58 | 9 | 0.51 |
| oQ | pg/ml | 2.9E3 | 4.0E3 | 3.5E3 | 7.3E3 | 3.0E3 | 9.5E3 | 7.7E2 | 9.1E2 | 2.1E4 | 3.2E4 | 58 | 9 | 58 | 9 | 0.64 |
| oE | pg/ml | 2.0E2 | 7.7E2 | 4.5E2 | 9.6E2 | 6.0E2 | 9.7E2 | 1.0E-9 | 1.0E-9 | 2.8E3 | 3.4E3 | 105 | 14 | 105 | 14 | 0.67 |
| oF | pg/ml | 1.2E4 | 2.3E4 | 2.6E4 | 4.5E4 | 3.9E4 | 4.4E4 | 3.5E2 | 2.0E3 | 2.5E5 | 1.4E5 | 105 | 14 | 105 | 14 | 0.69 |
| oH | pg/ml | 3.9E1 | 2.3E1 | 8.1E1 | 4.9E1 | 1.2E2 | 7.7E1 | 4.3E-1 | 1.1E1 | 8.6E2 | 3.1E2 | 105 | 14 | 105 | 14 | 0.40 |
| oK | pg/ml | 8.4E2 | 1.2E3 | 1.6E3 | 1.7E3 | 1.9E3 | 1.6E3 | 8.8E1 | 2.3E2 | 1.2E4 | 5.9E3 | 105 | 14 | 105 | 14 | 0.54 |
| oN | pg/ml | 5.5E2 | 5.4E2 | 9.9E2 | 6.4E2 | 2.0E3 | 3.4E2 | 1.1E2 | 2.8E2 | 1.8E4 | 1.5E3 | 105 | 14 | 105 | 14 | 0.52 |
| pF | pg/ml | 5.8E-1 | 5.8E-1 | 1.7E0 | 7.5E-1 | 8.5E0 | 4.1E-1 | 1.0E-9 | 1.8E-1 | 8.7E1 | 1.3E0 | 105 | 14 | 105 | 14 | 0.54 |

Analyte panel data:

Unconstrained panels with 3 analytes, where 1.0E-10 >= 'model p-value' > 0. Contains 21,412 panels of 17,842,327 total panels evaluated. :
Im[Og(AA Et Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oy Oz Pa Pb Pc Pd Pe Pf Pg Po Pz Qa Qb Qc Qd Qe) Oy(AA Et Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oz Pa Pb Pc Pd Pe Pf Pg Po Pz Qa Qb Qc Qd Qe) Pb(AA Et Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oz Pa Pc Pd Pe Pf Pg Po Pz Qa Qb Qc Qd Qe) Po(aA Et Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oz Pa Pc Pd Pe Pf Pg Pz Qa Qb Qc Qd Qe) Et(aA Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oz Pa Pc Pd Pe Pf Pg Pz Qa Qb Qc Qd Qe) Fp(aA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oz Pa Pc Pd Pe Pf Pg Pz Qa Qb Qc Qd Qe) Fr(aA Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oz Pa Pc Pd Pe Pf Pg Pz Qa Qb Qc Qd Qe) Nm(aA Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nn No Nq Nr Ns Nt Nu Nv Nw Nx Ny Oe Of Oh Oi Ok Om On Oz Pa Pc Pd Pe Pf Pg Pz Qa Qb Qc Qd Qe) Nn(aA Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Oh Oi Ok Om On Oz Pa Pc Pd Pe Pf Pg Pz Qa Qb Qc Qd Qe) No(aA Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nq Nr Ns Nt Nu Nv Nw Nx Ny Oe Of Oh Oi Ok Om On Oz Pa Pc Pd Pe Pf Pg Pz Qa Qb Qc Qd Qe) Nq(aA Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nr Ns Nt Nu Nv Nw Nx Ny Oe Of Oh Oi Ok Om On Oz Pa Pc Pd Pe Pf Pg Pz Qa Qb Qc Qd Qe) Nr(aA Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Ns Nt Nu Nv Nw Nx Ny Oe Of Oh Oi Ok Om On Oz Pa Pc Pd Pe Pf Pg Pz Qa Qb Qc Qd Qe) Ns(aA Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nt Nu Nv Nw Nx Ny Oe Of Oh Oi Ok Om On Oz Pa Pc Pd Pe Pf Pg Pz Qa Qb Qc Qd Qe) Nt(aA Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nu Nv Nw Nx Ny Oe Of Oh Oi Ok Om On Oz Pa Pc

Mw Nm Nn Nt Nu Ok Om Oz Pb) Jg(Ih Ip Is It Jn Js Jt Lj Lw Mi Mw Mz Ok Qa Qb Qd) Ok(Ih Ip It Jm Jt Oz Pb Qb) Nm(Ih Ip Is Js Qa Qb Qd) Ih(Ip Jt Ma Nt Nu) Ip(Jt Nt Qd) QbJt QdOz} Jj{Ij(Fp Fr Hr Hu Hx Ih Ik Io Ip Ir Is It Iv Jg Jl Jm Jn Jp Js Jt Lh Lj Lw Lx Ma Md Me Mh Mi Ml Mm Mn Mp Ms Mw My Mz Nc Nd Ni Nm Nn Nr Ns Nt Nu Nv Ny Oe Of Ok On Oy Oz Pb Pc Pf Pg Qa Qb Qc Qd) Ir(Ih Ip Jg Jp Jt Ma Mn Mp Mw Nm Nt Nu Ok On Oz Pb) On(Ih Ip It Jm Jn Js Jt Lj My Nu Oe Of Oy Oz Pb) Ih(Ip Jg Jp Js Jt Ma Mi Mw Nm Nt Nu Ok Qd) Ip(Jg Js Jt Mn Mw Nt Oz Qd) Jt(Hr Jn Lj Mw Nt Oz Qb) Nt(Jm Js Mw) Ok(It Jm Oz) Qd(Ik Oz) Jg(Js Qb) ItJp} On{My(Hr Ih Ij Ip Ir It Jg Jh Jn Jp Js Jt Lj Ma Me Mg Mw Mz Nk Nn Nq Nr Ns Nt Nu Ny Oe Of Oy Oz Pb Pc Qb Qc Qd) Oy(Fp Hr Ih Ij Ip Ir It Jg Jh Jn Jp Js Jt Lj Ma Mn Mt Mw Mz Nr Ns Nt Nu Ny Oe Of Oz Pb Qb Qc Qd) Of(Hv Ij Ip Ir It Jt Lj Ns Oe Om Oz Pb Qa Qd) Oe(Ih Ij Ir Jn Jt Lj Ns Oz Pb Qd) Hr(Hv Hw Jt Qa) Pb(Ij Ip Ir Lj) Lj(Ns Oz) IkQd} Ij{Jp(My Oe Of Oy Pb) Mi(My Of Oy Pb) Mt(My Of Oy) Jg(My Of Oy) Ok(Hr Of Pb) MpOy IkQd IpPb} Ir{Jp(Lw Oe Oy Oz Pb) Jg(Ik Oe Of Oy) Ok(Hr Oe Oz Pb) Ma(Oy Pb) NtIk HrJt IpOz} Qd{Ik(Ip Jg Jp Ma Mw Nt Nu Ok Oz) Oz(Ip Jp Ok) OkPb} Hr{Jt(Fp Ip Lj Lx Mz Qb) Ok(Ih Ip Js Lj)} Ok{Pb(Ih Ip Jp Lj) NsNd IpOz} Jg{Ih(Oe Oy) MtMy QbOe} Jp{Oz(Ip Lj Mi) MiPb} NsNtNd

Unconstrained panels with 3 analytes, where 1.0E-9 >= 'model p-value' > 1.0E-10. Contains 10,539 panels of 17,842,327 total panels evaluated. : Nw{Fr(Fp Hq Hw Hx Ii Ik Il In Io Iq Is Iu Iv Jg Jh Jk Jl Jm Jo Jp Jq Jr Js Lh Lu Lv Lx Ly Lz Ma Mb Mc Md Me Mf Mg Mj Mk Ml Mm Mn Mp Mq Mr Ms Mt Mu Mv Mw Mx Mz Na Nb Nc Nd Ne Nf Ng Nh Ni Nj Nk Nl Nm Nn Nq Nr Nt Nv Nx Ny Oh Oi Ok Om On Pa Pc Pd Pe Pf Pg Po Pz Qb Qc Qd Qe) Mq(Fp Hq Hw Hx Ii Ik Il In Io Iq Is Iu Iv Jg Jh Jk Jl Jm Jo Jp Jq Jr Js Lh Lu Lv Lw Lx Ly Lz Ma Mb Mc Md Me Mf Mg Mj Mk Ml Mm Mn Mp Mr Ms Mt Mu Mv Mw Mx Mz Na Nb Nc Nd Ne Nf Ng Nh Ni Nj Nk Nl Nm Nn Nq Nr Nt Nv Nx Ny Oh Oi Ok Om On Pa Pd Pe Pf Pg Po Pz Qb Qc Qd Qe) Iu(Fp Hq Hw Hx Ii Ik Il In Io Iq Is Iv Jg Jh Jk Jl Jm Jo Jp Jq Jr Js Lh Lu Lv Lw Lx Ly Lz Ma Mb Mc Md Me Mf Mg Mj Mk Ml Mm Mn Mp Mr Ms Mt Mu Mv Mw Mx Mz Na Nb Nc Nd Ne Nf Ng Nh Ni Nj Nk Nl Nm Nn Nq Nr Nv Nx Ny Oh Oi Ok Om On Pa Pc Pd Pe Pf Pg Po Pz Qb Qc Qd Qe) Mt(Fp Hq Hw Ii Ik Il In Io Iq Is Iv Jg Jh Jk Jl Jm Jo Jp Jq Jr Js Lh Lu Lv Lw Lx Ly Lz Ma Mb Mc Md Me Mf Mg Mj Mk Ml Mm Mn Mp Mr Ms Mu Mw Mx Mz Na Nb Nc Nd Ne Nf Ng Nh Ni Nj Nk Nl Nm Nn Nq Nr Nt Nv Nx Oh Oi Ok Om On Pa Pc Pd Pe Pf Pg Po Pz Qb Qc Qd Qe) Mx(Fp Hq Hw Ii Ik Il In Io Iq Is Iv Jg Jh Jk Jl Jm Jo Jp Jq Jr Js Lh Lu Lv Lx Ly Lz Ma Mb Mc Md Me Mf Mg Mj Mk Ml Mm Mn Mp Mr Ms Mu Mv Mw Mz Na Nb Nc Nd Ne Nf Ng Nh Ni Nj Nk Nl Nm Nn Nq Nr Nt Nv Nx Ny Oh Oi Ok Om On Pa Pd Pe Pf Pg Po Pz Qb Qc Qd Qe) Nl(Fp Hq Hw Ii Ik Il In Io Iq Is Iv Jg Jh Jk Jl Jm Jo Jp Jq Jr Js Lh Lu Lv Lx Ly Lz Ma Mb Mc Md Me Mf Mg Mj Mk Ml Mm Mn Mp Mr Ms Mu Mv Mw Mz Na Nb Nc Nd Ne Nf Ng Nh Ni Nj Nk Nl Nm Nn Nq Nr Nt Nv Nx Ny Oh Oi Ok Om On Pa Pd Pe Pf Pg Po Pz Qb Qc Qd Qe) Mb(Fp Hq Hw Ii Ik Il In Io Iq Is Iv Jg Jh Jk Jl Jm Jo Jp Jq Jr Js Lh Lu Lv Lx Ly Lz Ma Mc Md Me Mf Mg Mj Mk Ml Mm Mn Mp Mr Ms Mu Mv Mw Mz Na Nb Nc Nd Ne Nf Ng Nh Ni Nj Nk Nm Nn Nq Nr Nv Nx Ny Oh Oi Ok Om On Pa Pc Pd Pe Pf Pg Po Pz Qb Qc Qe) Io(Fp Hq Hx Ii Ik Il In Iq Is Iv Jg Jh Jk Jl Jm Jo Jp Jq Jr Js Lh Lu Lv Lx Ly Lz Ma Mc Md Me Mf Mg Mj Mk Ml Mm Mn Mp Mr Ms Mu Mv Mw Mz Na Nb Nc Nd Ne Nf Ng Nh Ni Nj Nk Nm Nn Nq Nr Nv Nx Ny Oh Oi Ok Om On Pa Pc Pd Pe Pf Pg Po Pz Qb Qc Qe) Nq(Fp Hq Hw Ii Ik Il In Iq Is Iv Jg Jh Jk Jl Jm Jo Jp Jq Jr Js Lh Lu Lv Lw Lx Ly Lz Ma Mc Md Me Mf Mg Mj Mk Ml Mm Mn Mr Ms Mu Mw Mz Na Nb Nc Nd Ne Nf Nh Ni Nj Nk Nm Nn Nr Nv Nx Ny Oh Oi Ok Om On Pa Pc Pd Pe Pf Pg Po Pz Qb Qc Qd Qe) Lv(Fp Hq Ii Ik Il In Iq Is Iv Jg Jh Jk Jl Jo Jp Jq Jr Js Lh Lu Lx Ly Lz Ma Mc Md Me Mf Mg Mj Mk Ml Mm Mn Mp Mr Ms Mu Mv Mw Mz Na Nb Nc Nd Ne Nf Ng Nh Ni Nj Nk Nm Nn Nr Nt Nv Nx Ny Oh Oi Ok Om On Pa Pd Pe Pf Pg Po Pz Qb Qc Qd Qe) Nh(Fp Hq Hx Ii Ik Il In Iq Is Iv Jg Jh Jk Jl Jm Jo Jp Jq Jr Lh Lu Lx Ly Lz Ma Mc Md Me Mf Mg Mj Mk Ml Mm Mn Mp Mr Ms Mu Mv Mw Mz Na Nb Nc Nd Ne Nf Ng Ni Nj Nk Nm Nn Nr Nv Nx Ny Oh Oi Ok Om On Pa Pc Pd Pe Pf Pg Po Pz Qb Qc Qe) Qe(Fp Hq Hv Hw Hx Ii Ik Il In Iq Is Iv Jg Jh Jk Jl Jm Jo Jp Jq Jr Js Lh Lu Lx Ly Lz Ma Mc Md Me Mf Mg Mj Mk Ml Mm Mn Mr Ms Mu Mw Mz Na Nb Nc Nd Ne Nf Ng Ni Nj Nk Nm Nn Nr Nv Nx Ny Oh Oi Ok Om On Pa Pd Pe Pf Pg Po Pz Qb Qc Qd) Ne(Fp Hq Ii Ik Il In Iq Is Iv Jg Jh Jk Jl Jo Jp Jq Jr Js Lh Lu Lx Ly Lz Ma Mc Md Me Mf Mg Mj Mk Ml Mm Mn Mp Mr Ms Mu Mv Mw Mz Na Nb Nc Nd Nf Ng Ni Nj Nk Nm Nn Nr Nv Nx Ny Oh Oi Ok Om On Pa Pc Pd Pe Pf Pg Po Pz Qb Qc) Pz(Fp Hq Hv Hw Hx Ii Ik Il In Iq Is Jg Jh Jk Jl Jm Jo Jp Jq Jr Js Lh Lu Lx Ly Lz Ma Mc Md Me Mf Mg Mj Mk Ml Mm Mn Mr Ms Mu Mz Na Nb Nc Nd Nf Ng Ni Nj Nk Nm Nn Nr Nv Nx Ny Oh Oi Ok Om On Pa Pc Pd Pe Pf Pg Po Qb Qc) Jr(Fp Hq Hw Hx Ii Ik Il In Iq Is Iv Jg Jh Jk Jl Jm Jo Jp Jq Js Lh Lu Lx Ly Lz Ma Mc Md Me Mf Mg Mj Mk Ml Mm Mn Mr Ms Mu Mz Na Nb Nc Nd Nf Ng Ni Nj Nk Nm Nn Nr Nv Nx Oh Oi Ok Om On Pa Pd Pe Pf Pg Po Qb Qc Qd) Lu(Fp Hq Ii Ik Il In Iq Is Iv Jg Jh Jk Jl Jo Jp Jq Js Lh Lx Ly Lz Ma Mc Md Me Mf Mg Mj Mk Ml Mm Mn Mp Mr Ms Mu Mv Mz Na Nb Nc Nd Nf Ng Ni Nj Nk Nm Nn Nr Nv Nx Ny Oh Oi Ok Om On Pa Pd Pe Pf Pg Po Qb Qc) Om(Fp Hq Ii Ik Il Iq Is Iv Jg Jh Jk Jl Jm Jp Js Lh Lw Lx Ly Lz Ma Mc Me Mf Mg Mj Mk Ml Mm Mn Mp Mr Ms Mu Mw Mz Na Nb Nc Nd Nf Ng Ni Nj Nk Nm Nn Nr Nt Nv Nx Oh Oi Ok On Pa Pc Pd Pe Pf Pg Po Qb Qc Qd) Mg(Fp Hq Ii Ik Il In Iq Is Iv Jg Jh Jk Jl Jm Jo Jp Jq Js Lh Lx Ly Lz Ma Mc Md Me Mf Mj Mk Ml Mm Mn Mp Mr Ms Mu Mw Mz Na Nb Nc Nd Nf Ni Nj Nk Nm Nn Nr Nv Nx Oh Oi Ok On Pa Pd Pe Pf Pg Po Qb Qc) Nb(Fp Hq Ii Ik Il In Iq Is Iv Jg Jh Jk Jl Jm Jo Jp Jq Js Lh Lx Ly Lz Ma Mc Md Me Mf Mj Mk Ml Mm Mn Mp Mr Ms Mu Mz Na Nc Nd Nf Ng Ni Nj Nk Nm Nn Nr Nv Nx Oh Oi Ok On Pa Pd Pe Pf Pg Po Qb Qc) Mj(Fp Hq Hx Ii Ik Il In Iq Is Iv Jg Jh Jk Jl Jm Jp Jq Lh Lx Ly Lz Ma Mc Md Me Mf Mk Ml Mm Mn Mp Mr Ms Mu Mv Mz Na Nc Nd Nf Ng Ni Nj Nk Nm Nn Nr Nv Nx Ny Oh Oi Ok On Pa Pd Pe Pf Pg Po) Mr(Fp Hq Hw Ii Ik Il In Iq Is Iv Jg Jh Jk Jl Jo Jp Jq Js Lh Lx Lz Ma Mc Md Me Mf Mk Ml Mm Mn Mp Ms Mu Mz Na Nc Nd Nf Ng Ni Nj Nk Nm Nn Nr Nt Nv Nx Oh Oi Ok On Pa Pd Pe Pf Pg Qb Qc) Mu(Fp Hq Hx Ii Ik Il In Iq Is Iv Jg Jh Jk Jl Jp Jq Js Lh Lx Ly Lz Ma Mc Md Me Mf Mk Ml Mm Mn Ms Mv Mz Na Nc Nd Nf Ng Ni Nk Nm Nr Nv Nx Ny Oh Oi Ok On Pa Pd Pe Pf Pg Po Qb Qc) Nj(Fp Hq Ii Ik Il In Iq Is Iv Jg Jh Jk Jl Jo Jp Jq Lh Lx Ly Lz Ma Mc Md Me Mf Mk Ml Mm Mn Ms Mv Mz Na Nc Nd Nf Ng Ni Nk Nm Nn Nr Nv Nx Ny Oh Oi Ok On Pa Pd Pe Pf Pg Po Qb Qc) Lx(Fp Hq Ii Ik Il In Iq Is Iv Jg Jh Jk Jl Jm Jo Jp Jq Js Lh Lz Ma Mc Md Me Mf Mk Ml Mm Mn Mp Ms Mz Na Nc Nd Nf Ng Ni Nk Nm Nn Nr Nv Nx Oh Oi Ok On Pa Pd Pe Pf Pg Po Qb Qc) Ma(Fp Hq Ii Ik Il In Iq Is Iv Jg Jh Jk Jl Jo Jp Jq Js Lh Ly Lz Mc Md Me Mf Mk Ml Mm Mn Mp Ms Mz Na Nc Nd Nf Ni Nk Nm Nn Nr Nv Nx Ny Oh Oi Ok On Pa Pd Pe Pf Pg Po Qc) Pg(Fp Hq Ii Ik Il In Iq Is Iv Jg Jh Jk Jl Jo Jp Jq Js Lh Ly Lz Mc Md Me Mf Mk Ml Mm Mn Ms Mz Na Nc Nf Ng Ni Nk Nm Nn Nr Nv Nx Ny Oh Oi Ok On Pa Pd Pe Pf Po Qb Qc) Mc(Fp Hq Ii Ik Il In Iq Is Iv Jg Jh Jk Jl Jp Jq Lh Ly Lz Md Me Mf Mk Ml Mm Mn Ms Mv Mz Na Nc Nd Nf Ng Ni Nk Nm Nn Nr Nv Nx Ny Oh Oi Ok On Pa Pd Pe Pf Po Qc) Mk(Fp Hq Ii Ik Il In Iq Is Iv Jg Jh Jk Jm Jp Jq Js Lh Ly Lz Md Me Mf Ml Mm Mn Ms Mv Mz Na Nc Nf Ng Ni Nk Nm Nn Nr Nv Nx Ny Oh Oi Ok On Pc Pd Pf Po Qb Qc) Nf(Fp Hq Hx Ii Ik Il In Iq Is Iv Jg Jh Jk Jl Jp Lh Ly Lz Md Me Mf Ml Mm Mn Ms Mv Mz Na Nc Nd Ng Ni Nk Nm Nn Nr Nv Nx Ny Oh Oi Ok On Pa Pd Pe Pf Po Qc) Jk(Fp Hq Hx Ii Ik Il In Iq Is Jg Jl Jo Jp Jq Js Lh Ly Lz Md Me Mf Ml Mm Mn Ms Mz Na Nc Nd Ni Nk Nm Nr Nv Nx Ny Oh Oi Ok On Pa Pd Pe Pf Po Qb Qc) Lh(Fp Hq Ii Ik Il In Iq Is Iv Jg Jh Jl Jm Jo Jp Jq Js Ly Lz Md Me Mf Ml Mm Mn Mp Ms Mz Na Nc Nd Ng Ni Nk Nm Nn Nr Oh Oi Ok On Pa Pd Pe Pf Qb Qc) On(Fp Hq Hw Ii Ik Il In Iq Is Iv Jg Jh Jl Jo Jp Jq Js Ly Lz Md Me Mf Ml Mm Mn Ms Mv Mz Na Nc Nd Ni Nk Nm Nn Nr Nt Oh Oi Ok On Pa Pd Pe Pf Qb Qc) Lz(Hq Ii Ik Il In Iq Is Iv Jg Jh Jl Jp Jq Ly Md Me Mf Ml Mm Mn Ms Mv Mz Na Nc Nd Ng Ni Nk Nm Nn Nr Nv Nx Ny Oh Oi Ok Pa Pd Pe Pf Po) Na(Fp Hq Ii Ik Il In Iq Is Iv Jg Jh Jl Jo Jp Jq Js Ly Me Mf Ml Mm Mn Ms Mz Nc Nd Ng Ni Nk Nm Nn Nr Nv Oh Oi Ok Pa Pd Pe Pf Po Qc) Iq(Fp Hq Ii Ik Il In Is Jg Jh Jl Jm Jo Jp Jq Js Ly Md Me Mf Ml Mm Mn Mz Nc Nd Ni Nk Nm Nn Nr Nv Oh Oi Ok Pa Pd Pe Pf Po Qb Qc) Mf(Fp Hq Ii Ik Il In Is

Nk Nt Nu Of Oi) Js(Hu Il Jo Lj Ly Lz Mh Nk Of Oi) Nt(Hu Jo Ly Mh Nd Of Oi Qc) Hu(Is Jg Jh Lj Mw Nq) Of(Is Jg Lj Mt Nb Om) My(Jg Mt Nb) Qc(Il Lj Lz) Mh(Mr Mt) Jg(Ng Oi) Lj(Qa Qb) MkPa NdPf IsIv} No{Ip(Fp Fr Hq Hr Hu Hv Hw Hx Ii Ij In Io Iq Ir Is Iu Iv Jg Jh Jk Jl Jm Jn Jo Jp Jq Jr Js Lh Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Nt Nu Nv Nx Ny Oh Oi Ok Om On Pa Pc Pd Pe Pf Pg Po Qa Qb Qc Qd) Og(Fp Fr Hq Hr Hu Hv Hw Hx Ii Ik Il In Io Iq Iu Iv Jh Jk Jl Jo Jp Jq Jr Lh Lj Lu Lv Lx Ly Lz Ma Mb Mc Md Me Mf Mg Mh Mj Mk Ml Mm Mn Mp Mq Mr Ms Mt Mu Mv Mx My Mz Na Nb Nc Nd Ne Nf Ng Nh Ni Nj Nk Nl Nq Nr Nt Nv Nx Ny Oe Of Oh Oi Om Oy Pa Pc Pd Pe Pf Pg Po Pz Qa Qb Qc Qd Qe) Jj(Fp Fr Hq Hr Hu Hv Hw Hx Ii Il In Io Iq Iu Iv Jh Jk Jl Jo Jp Jq Jr Lh Lj Lu Lv Lx Ly Lz Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni Nk Nl Nq Nr Nv Nx Ny Of Oh Oi Om Pa Pc Pd Pe Pf Pg Po Pz Qa Qe) Ir(Hq Hr Hu Hv Hx Ih Ii Ij Il In Io Is It Iu Iv Jg Jk Jn Jo Jp Jq Jt Lj Lv Ly Lz Ma Mc Me Mf Mg Mh Mi Mj Mm Mn Mp Ms Mt Mu Mw My Mz Na Nc Nd Ne Nf Ng Nh Ni Nj Nk Nm Nn Nt Nu Nx Of Oh Oi Ok On Pa Pc Pd Pf Po Qc Qd) Ns(Fp Hq Hr Hu Hv Hw Ii Ij In Io Iq Is It Iv Jg Jl Jm Jn Jo Jp Jq Jr Js Lj Lu Lv Ly Lz Ma Me Mf Mg Mh Mi Mj Mm Mn Mq Ms Mt Mw My Mz Nb Nc Nf Ng Ni Nj Nk Nm Nn Nt Nu Ny Of Oh Oi Om Pa Pc Pd Pe Pf Pg Qa Qb Qc Qd) Oy(Fr Hr Hu Hv Hw Ik Il In Iq Is It Iv Jh Jm Jn Jo Jp Jq Js Lh Lj Lv Ma Me Mg Mh Mi Mm Mn Mp Ms Mt Mw My Mz Nb Nc Nd Ni Nj Nk Nm Nt Nu Ny Oe Of Oh Om Pa Pc Pe Pf Pg Qa Qb Qc Qd) Lw(Fp Hq Hr Hu Ih Ii Ij Ik Il In Is It Iv Jg Jn Jo Jp Js Jt Lj Ly Mf Mh Mi Mk Mn Ms Mt Mu Mw My Mz Nc Nd Ng Ni Nj Nk Nn Nt Nu Nx Ny Oe Of Oh Oi Ok On Pa Pc Pd Pf Qa Qb Qc Qd) Pb(Fr Hq Hr Hx Ii Il Io Iq Iu Jh Jk Jm Jr Lu Lx Ly Lz Mb Mc Md Mf Mj Mk Ml Mq Mu Mv Mx My Na Ne Nf Ng Nh Nl Nq Nr Nv Nx Ny Oi Pd Po Pz Qe) Oe(Hr Ik In Io Iq It Iv Jg Jl Jm Jp Jq Js Lj Mc Mg Mh Mi Mm Mn Mp Mw Mz Nb Nc Nd Ni Nj Nk Nm Nn Nt Nu Ny Oh Ok Om Pc Pf Qa Qb Qc Qd) Jt(Hq Hu Hv Hx Ih Ii Ij Ik In Is It Iu Iv Jn Jp Lj Mg Mh Mi Mj Mp Ms Mw My Mz Na Nd Ng Nj Nk Nn Nr Nu Nx Oh Oi Ok Pc Po Qb Qc Qd) Ih(Hq Hr Hu Ii Ij Ik In It Jg Jn Jo Jp Jq Ma Mh Mi Mj Mm Mp Ms Mw My Mz Nd Nj Nk Nm Nn Nt Nu Of Oh Oi Ok On Pc Pf Qc Qd) Oz(Fr Hw Il Io Iq Iu Jh Jk Jm Jr Lh Lu Lx Lz Mb Mc Md Mg Mj Mk Ml Mq Mt Mu Mx Na Nb Nl Nq Nr Nv Om Pd Po Pz Qe) It(Hq Hr Hu Ii Ij Ik Jg Jn Jo Jp Jq Ly Mh Mi Mp Mw My Mz Nd Nk Nm Nn Nu Of Oh Ok On Pc Qc) Ik(Hr Is Iv Jg Jn Jp Jq Js Lj Lv Mh Mi Mp Mw Nj Nm Nn Nt Nu Ok On Pc Qa Qb Qc) Ij(Hq Hr Hu Hx Ii Jn Jo Jp Lj Mh Mi Mm Mp Ms Mw Nd Ng Nk Nn Nu Ok Pc Qc Qd) Ok(Hu Jn Jo Jp Js Lj Mh Mp Mw My Nd Nk Nn Nu Of Pc Qb Qc Qd) Jn(Hq Hr Hu Jp Mh Mi Mp Nd Nk Nm Nn Of Oh) Of(Jg Jp Jq Js Mi Mt Mz Nb Om Qd) On(Hr Hu Lj Mh Mk Mv Ng Nv Po) My(Jh Mi Mt Mw Nb Nm Nn) Hr(Hv Hw In Jo Js Nm Qa) Mh(Js Mi Mt Mz) Nn(Hu Pc) Mi(Hq Jp) NmNg NcNk HuJg IlQd JoJs JpLj} On{Og(Fp Fr Hq Hr Hu Hv Hw Hx Ii Ik Il In Io Iq Is Iu Iv Jh Jk Jl Jo Jq Jr Lh Lu Lv Lx Ly Lz Ma Mb Mc Md Me Mf Mg Mh Mk Ml Mm Mn Mp Mq Mr Ms Mt Mu Mv Mx Mz Na Nb Nc Nd Ne Nf Ng Nh Ni Nj Nk Nl Nn Nq Nr Nt Nv Nx Ny Oh Oi Om Pa Pc Pd Pe Pf Pg Po Qa Qe) Oy(Fr Hq Hu Hv Hw Hx Ii Ik Il In Io Iq Is Iu Iv Jk Jl Jm Jo Jq Jr Lh Lu Lv Lw Lx Ly Lz Mb Mc Md Me Mf Mg Mh Mi Mj Mk Ml Mm Mp Mq Mr Ms Mu Mv Mx Na Nb Nc Nd Ne Nf Ng Nh Ni Nj Nk Nl Nm Nn Nq Nv Nx Oh Oi Ok Om Pa Pc Pd Pe Pf Pg Po Pz Qa Qe) My(Fp Fr Hq Hu Hv Hw Hx Ii Ik Il In Io Iq Is Iu Iv Jk Jl Jm Jo Jq Jr Lh Lu Lv Lw Lx Ly Lz Mb Mc Md Mf Mh Mi Mj Mk Ml Mm Mn Mp Mq Mr Ms Mt Mu Mv Mx Na Nb Nc Nd Ne Nf Ng Nh Ni Nj Nl Nm Nv Nx Oh Oi Ok Om Pa Pd Pe Pf Pg Po Pz Qa Qe) Jj(Fp Hq Hr Hu Hv Hw Hx Ik Il In Io Iq Is Iu Iv Jg Jo Jp Jq Jr Lh Lv Lw Lx Ly Lz Ma Mc Md Mf Mg Mh Mi Mk Ml Mn Mp Mr Ms Mu Mv Mw Mz Nc Nd Ng Ni Nj Nk Nm Nn Nr Ns Nt Nv Nx Ny Oh Oi Ok Pc Pe Pf Pg Po Qa Qb Qc Qd Qe) Of(Fp Hq Hr Hu Hw Ih Ik In Io Iq Is Iv Jg Jk Jm Jn Jo Jp Jq Js Lw Ly Ma Mh Mi Mk Ml Mn Mp Ms Mt Mv Mw Mz Nb Nd Ng Nj Nk Nm Nn Nt Nu Nv Nx Ny Oh Oi Ok Pc Pe Pf Qb Qc) Oe(Fp Hq Hr Hu Hv Ik Ip Iq Is It Iv Jg Jl Jm Jo Jp Jq Js Lw Lx Ly Ma Mc Mg Mh Mi Mk Ms Mw Mz Nc Nd Ng Nk Nm Nn Nt Nu Nx Ny Oh Ok Pa Pc Pe Pg Qa Qb Qc Qe) Lj(Hr Hu Ih Ii Ij Ik Ip Ir It Jg Jp Jt Lw Ma Mh Mi Mp Ms Mw Nk Nu Nx Oh Ok) Pb(Fp Ih It Jn Jp Js Jt Lw Mi Ms Mz Ng Ns Nt Ok Pe Pf Qa Qb Qd) Ir(Hr Hu Ii Ik Ip Jk Jo Jp Lw Ng Nk Ns Nu Nx Oz) Oz(Ih Ip It Jt Mi Ng Ns Qd) Ns(Ih Ip Jp Jt Nd Qd) Ng(Ij Ip Jg Jt) Hr(In Jq Mz Ok) Hu(Ij Ip Jp Qd) NdHq IhIp IjIk IlQd ItJp JoJt} Jj{Ir(Fp Fr Hr Hu Ii Ik Il Io Iq Is It Iv Jh Jk Jl Jm Jn Jo Jq Js Lh Lj Lv Lw Lx Lz Mc Me Mg Mh Mi Mj Mm Mr Ms Mt Mz Nc Nd Ng Ni Nj Nk Nn Nq Nr Ns Nv Ny Oe Oh Om Oy Pa Pc Pe Pf Pg Po Pz Qa Qb Qc Qd) Ij(Hq Hv Hw Ii Il In Iq Iu Jh Jk Jo Jq Jr Lu Lv Ly Lz Mb Mc Mf Mg Mj Mk Mq Mr Mt Mu Mv Mx Na Nb Ne Nf Ng Nh Nj Nk Nl Nq Nx Oh Oi Om Pa Pd Pe Po Pz Qe) Jt(Fp Fr Il Is It Iv Jg Jl Jm Jp Js Lh Lx Ma Mh Mi Mj Mn Mp Mz Na Nm Nn Nr Nu Nv Ny Oe Og Ok Pb Pe Pf Pg Qa Qc Qd) Ih(Fp Fr Io It Jn Jo Jq Lh Lj Lv Lw Lx Mg Mm Mn Mp Mr Mz Ng Nk Nn Nq Nr Ns Nv Ny Oe Og Om Oz Pb Pe Pg Po Qa Qc) Js(Fr Ik Il It Jm Jn Jp Lh Lj Lw Ma Mn Mw Mz Nm Nn Nu Ny Og Ok Oz Pb Qa Qb Qd) Nt(Iq Is It Jg Jn Jp Lh Lj Ma Mn Mz Nd Nm Nr Ny Ok Oz Pb Qa Qb Qc Qd) Ok(Il Ip Jn Jp Lj Mi Mp Mw Nn Nr Nu Oe Og Pb Pe Pg Qa Qb Qc Qd) Jg(Fp Il Is It Jm Jn Lj Mi Mw Nr Oe Og Oz Pb Pe Pg Qa Qc Qd) Ip(Il It Jm Jn Jp Lh Lj Ma Mi Nr Nu Nv Ny Pb Qa Qb) Qd(Il It Jm Jn Jp Lw Ma Mi Mn Mw Nm Nn Nu Oe Og Pb) Qa(Ik Jn Jp Ma Mn Mw Nm Nu Oe Og Oz Pb) Jm(Jn Jp Lh Ma Mw Nm Nu Oz) Jn(Jp Lh Ma Mn Mw Nm Nu) It(Fr Lh Ma Mw Nm Nu) Qb(Jp Ma Nm Oz) Oz(Jp Lh Ma) Lj(Jp Ma) AaIm NuMw LhPb} Ji{Mq(Hq Hv Hw Ii In Iq Iu Jh Jk Jr Lh Lu Lv Lw Mb Me Mg Mj Mk Mt Mu Mx Na Nb Ne Nj Nl Nq Nv Oh Pd Pg) Mg(Hq Hv Hw In Iq Iu Jh Jk Jr Lh Lu Lv Lw Mb Me Mj Mk Mt Mu Mx Na Nb Ne Nj Nl Nq Nv Oh Pd Pg) Iu(Hq Hv Hw In Iq Jh Jk Jr Lh Lu Lv Lw Mb Me Mj Mk Mt Mu Mx Na Nb Ne Nj Nl Nq Nv Oh Pd Pg) Jr(Hq Hv Hw In Iq Jh Jk Lh Lu Lv Lw Mb Me Mj Mk Mt Mu Mx Na Nb Ne Nj Nl Nq Nv Oh Pd Pg) Mx(Hq Hw In Iq Jh Jk Lh Lu Lv Lw Mb Me Mj Mk Mt Mu Na Nb Ne Nj Nl Nq Nv Oh Pd Pg) Nl(Hq Hw Iq Jh Jk Lh Lu Lv Lw Mb Me Mj Mk Mu Na Nb Nj Nq Nv Oh Pd Pg) Nj(Hq Hw Jh Jk Lh Lu Lv Lw Mb Me Mj Mk Mt Mu Na Nb Nv Oh Pd Pg) Lh(Hw Iq Jh Jk Lu Lv Lw Mb Me Mj Mk Mt Mu Na Nb Nq Pd Pg) Mj(Hq Ii Jh Jk Lv Lw Mb Mc Mk Mu Na Nb Ne Nv Oh Pd) Na(Hq Jh Jk Lv Lw Mb Me Mk Mu Nb Ne Nv Oh Pd Pg) Jk(Hw Iq Jh Lv Lw Mb Me Mk Mt Mu Nb Nq Pd Pg) Lv(Hq Jh Lw Mb Me Mk Mu Nb Nv Oh Pd) Mu(Hq Jh Lw Mb Me Mk Nb Nv Oh Pd) Mk(Hq Jh Mb Me Nb Nv Oh Pd) Jh(Lw Mb Me Nb Nv Pd) Mb(Lw Me Pd) Me(Lw Nv) HqPd} Og{Ir(Fp Hr Hu Ih Ik Il In Io Iq Is It Iv Jh Jl Jm Jn Jo Jq Js Lh Lj Lv Lx Me Mh Mp Mr Mt Mv Mz Nb Nd Ni Nk Nq Nr Ns Nv Ny Oe Oh Oy Pa Pc Pe Pf Pg Po Qa Qb Qc Qd) Jg(Fp Hv Il Iv Jl Jm Jp Jq Lh Lx Mn Mp Mr Mt Mx Nb Nd Nm Nr Ns Nt Nu Nv Ny Of Om Oz Pa Pb Pe Pg Po Qc Qe) Jt(Fp Fr Hr Is It Iv Jm Jn Jp Js Lj Lw Lx Ma Mi Mj Mn Mt Mw Mz Nm Nn Nr Nt Nu Nv Ny Om Oz Pb Po Qa Qc Qd) Ok(Fp Hr Il Iq Is Iv Jn Jp Jq Js Lj Lw Mi Mp Mt Mw Mz Nb Nd Nm Nn Nr Ns Nt Nu Ny Of Om Pa Pe Qa Qc Qd) Ip(Is Jn Jp Jq Js Lw Mi Mn Mw Mz Nb Nu Om Oz Qa) Jp(Ih Is It Jn Js Lj Lw Mi Nm Nt Oz Qa Qb Qd) Qd(Ih Ik Jn Lw Ma Mi Mt Mw Nn Nt Nu Pb) Nm(Jl Jn Lj Mw Nt Om Pe Qe) Ih(Fr Lw Mi Mm Mw Ny Om Oz) Nt(Is Js Lj Mw Qa Qb) Ij(Lv Mj Mx Ng Nl Oi) Lw(Js Qa) Oz(Om Qa) AaQc FrJs NuIs MaQb} Ir{Jp(Fp Hq Hr Hu Ih Ii Ij Ik Il Ip It Jg Jn Jo Jq Jt Lj Lx Ma Mh Mi Mj Mm Mn Mp Ms Mw My Mz Nd Ne Ng Nh Nk Nm Nn Ns Nt Nu Nx Of Oh Oi Ok Pc Qc) Oe(Fr Ij Io Ip Jt Lw Lx Ma Mm Mn Mp Mw Nm Nn Nt Nu Om Oz Pb Qd) Oz(Fr Hr Jg Jt Lw Ma Mi Mm Mn Mp Mw Nm Nn Nt Nu Pf Qd) Pb(Fr Ij Ip Jg Jt Lw Mi Mm Mn Mp Mw Nm Nn Nt Nu) Oy(Fr Ip Jh Lw Mm Mn Mp Mw Nn Nt Ok) Ik(Fr Ij Ip Ma Mi Mw Nu Ok Qd) Jg(Hr Jo Lw Mi Mp My Ng Ns Oi) Ok(Ip Jo Mw Nn Ns Nu Of) Hr(Hw Jq Lh Lw Mw Mz) Lw(Ma Mw Nu) Jo(Jt Ma Nt) Ns(Mp Nd) Mw(Ip My) MaOf MnIp MtMy} Ok{Pb(Fp Fr Hr Is It Jg Jn Js Jt Lx Ma Mi Mn Mp Mw Mz Nn Nr Ns Nt Nu Oe Of Pe Pg Qa Qb) Hr(Fp Is It Jn Jp Jt Mi Mw Mz Nr Ns Nu Oz Qa Qb Qc Qd) Oz(Ih Ij It Jn Jp Js Lj Mi Oe Of Pe Qa Qb) Of(Ih Ip It Jg Jp Js Jt Mi Mt Qa Qd) Ih(Ip Jg Jp Ma Ns Nu Oe Oy) Lj(Ij Ip Jp Mi Mp Ns Oe) Oe(Ij Jn Jp Qa Qb Qd) Oy(Ij Ip Jp Pe Qd) Jo(Ij It Js Jt) Ip(Jp Mw Qd) Ij(Ik My) Jp(It Ns) NdHq IlQd} Jp{Pb(Fp Ih Ip Is It Jn Jq Js Jt Lh Lj Lw Mz Nt Pe Qa Qb Qd) Oz(Aa Fp Ih Ij It Jq Js Jt Lw Mp Nt Pe Qa Qb) Lj(Ij Ip It Jq Jt

Figure 36 Continued

Lw Mi Mp Nn Nt Oe) Ih(Ip Jt Lw Mi Nk Ns Nt Oe Oy) Ij(Hr Hu Ik Jo Lw Mi Mp Ng) It(Ip Jt Lw Mi Nk Ns) Oe(Is Jt Nt Qa Qb Qd) Mi(Hq Ip Ns Oy) Jt(Hr Ip Of Oy) Qd(Il Oy) Aalm NsMp NtIp MtMy} Qd{Oz(Fr Ih Ij Il Jg Jn Jq Jt Lh Lj Lw Lx Ma Mi Mp Mr Ms Mw Mz Nd Nn Nr Ns Nt Nu Oe Of Pa Pc Pe Qc) Ik(Fp Fr Jn Jt Lh Lj Lw Lx Mi Mm Mn Mz Nm Nn Nr Ns Ny Oe Oy Pb) Pb(Ij Ip Jg Jt Lh Lw Ma Oe) Jg(Il My Ng Oe Of Oy) Oe(Ih Ij Jt) Ma(Il Oy) Ip(Il Oy) NsNd HrJt} Ij{Pb(Fr Ih Ik Jg Jt Lh Lj Lw Lx Ma Mm Mp Mw Nn Nt Oe) Oy(Fr It Jh Jt Lh Lw Lx Mm Mw Nn Nq Pa) My(Fr Lx Mm Mw Nn Nq) Lj(Jg Lw Mi Mm Mp Oe) Of(Fr Jt Lh Lx Mp) Jg(Ik Jo Ng Oe) Mi(Hr Ik Oz) Jt(Hr Jo Oe) BbJo NnHu NtIk MzHr IpOz UhbN} Jg{Ih(Ip Lj Lw Mi My Ng Nk Ns Of Oi Oz Pb) Of(Ip Js Jt Mi Mz Nb Qa Qb) My(Ip Js Mi Mz Qb) Oy(Js Mi Mt Pe Qb) Lj(Lw Mi Mp Oe) Qa(Ik Oe Pb) Js(Jo Ng Oe) Nd(Hq Ns) MiPb} Jt{Hr(Fr Ih Is It Jl Jn Js Lh Mi Mp Mr Mt Mw Nd Nt Nu Oz Pa Pb Pe Po Qa Qc) Lj(Mh Mj Oe Oz Pb) Fr(Of Oz Pb) Ip(Jo Oz Pb) Oe(Ih Qa Qb) Aj(Im Nk) NtJo MtOf} Ip{Oz(Aa Ih Js Mi Nt Qa) Pb(Ih Mi Nt Qa) Hr(Jq Mz Qa) Nt(Ih Ik) MaIh} Uh{bN(Cu Hv It Jn Jq Jr Kd Ke Lw Ml Na Qa Vt) UrUu} Aa{Im(Hr Ii Jo Mm Of Oi Oz Pc Qc) Qc(Oy Oz)} Ih{Ma(Oe Oy Oz Pb) Fr(Oe Oz Pb) Nt(Oe Oz) Mi(Oz Pb)} Hr{Jq(Mr Pa Pe) Qa(Mi Mr)} Ke{FyVs NxUu UvbN} Ti{Nb(hB hC)} Mi{Lj(Ik Oz)} Qa{Pb(Ma Oe)} NtNdHq Unconstrained panels with 3 analytes, where 8.7E-9 >= 'model p-value' > 1.0E-9. Contains 18,049 panels of 17,842,327 total panels evaluated. : Et{Mx(Fr Hq Hr Hu Hv Hw Hx Ii Il In Io Iq Iu Iv Jg Jh Jk Jl Jm Jp Jr Lh Lu Lv Lx Ly Lz Ma Mb Mc Md Me Mf Mg Mh Mj Mk Ml Mm Mn Mp Mq Mr Ms Mt Mu Mv My Na Nb Nc Ne Nf Ng Nh Ni Nj Nk Nl Nm Nn Nq Nr Nt Nu Nv Nx Ny Oh Oi Om On Pa Pc Pd Pe Pf Pg Po Pz Qe) Na(Fr Hq Hu Hv Hw Hx Ii Ik Il In Io Iq Iu Iv Jg Jh Jk Jl Jm Jp Jr Lh Lu Lv Lx Ly Lz Ma Mb Mc Md Me Mf Mg Mh Mj Mk Ml Mm Mn Mp Mq Mr Ms Mt Mu Mv My Nb Nc Ne Nf Ng Nh Ni Nj Nk Nl Nm Nn Nq Nr Nt Nu Nv Nx Ny Oh Oi Om On Pa Pc Pd Pe Pf Pg Po Pz Qe) Nf(Fr Hq Hu Hv Hw Hx Ii Ik Il In Io Iq Iu Iv Jg Jh Jk Jl Jm Jp Jr Lh Lu Lv Lx Ly Lz Ma Mb Mc Md Me Mf Mg Mh Mj Mk Ml Mm Mn Mp Mq Mr Ms Mt Mu Mv My Nb Nc Ne Ng Nh Ni Nj Nk Nl Nm Nn Nq Nr Nt Nu Nv Nx Ny Oh Oi Om On Pa Pc Pd Pe Pf Pg Po Pz Qe) Mc(Fr Hq Hr Hu Hv Hw Hx Ii Ik Il In Io Iq Iu Iv Jg Jh Jk Jl Jm Jo Jp Jr Lh Lu Lv Lx Ly Lz Ma Mb Md Me Mf Mg Mh Mj Mk Ml Mm Mn Mp Mq Mr Ms Mt Mu Mv My Nb Ne Ng Nh Ni Nj Nk Nl Nm Nn Nq Nr Nt Nu Nv Nx Ny Oh Oi Om Pa Pc Pd Pf Pg Po Pz Qe) Fr(Hq Hr Hu Hv Hw Hx Ii Ik Il In Io Iq Iu Iv Jg Jh Jk Jl Jm Jp Jr Lh Lu Lv Lx Ly Lz Ma Mb Md Me Mf Mg Mh Mj Mk Ml Mm Mn Mp Mq Mr Ms Mt Mu Mv Nb Ne Nh Ni Nj Nk Nl Nm Nn Nq Nr Nt Nu Nv Nx Ny Oh Oi Om On Pa Pc Pd Pe Pf Pg Po Pz Qe) Po(Hq Hu Hv Hw Hx Ii Il In Io Iq Iu Iv Jg Jh Jk Jl Jm Jp Jr Lh Lu Lv Lx Ly Lz Ma Mb Md Me Mf Mg Mh Mj Mk Ml Mm Mn Mp Mq Mr Ms Mt Mu Mv Nb Nc Ne Nh Ni Nj Nk Nl Nm Nn Nq Nr Nt Nu Nv Nx Ny Oh Oi Om On Pa Pc Pd Pe Pf Pg Pz Qe) Hx(Hq Hr Hu Hv Hw Ii Ik Il In Io Iq Iu Iv Jg Jh Jk Jl Jm Jo Jp Jr Lh Lu Lv Lx Ly Lz Ma Mb Md Me Mf Mg Mh Mj Mk Ml Mm Mn Mp Mq Ms Mu Mv Nb Ne Ng Nh Ni Nj Nk Nl Nm Nn Nq Nr Nt Nu Nv Nx Ny Oh Oi Om Pa Pc Pd Pe Pf Pg Pz Qe) Io(Hq Hr Hu Hv Hw Ii Ik Il In Iq Iu Iv Jg Jl Jm Jo Jp Jr Lh Lu Lv Lx Ly Lz Ma Me Mf Mg Mh Mj Mk Ml Mm Mn Mp Mq Mr Ms Mt Mu Mv My Nb Nc Ne Ng Nh Ni Nj Nk Nl Nm Nn Nq Nr Nt Nu Nv Nx Ny Oh Oi Om On Pa Pc Pd Pf Pg Pz Qe) Me(Hq Hr Hu Hv Hw Ii Ik Il In Iq Iu Iv Jg Jh Jk Jl Jm Jp Jr Lh Lu Lv Lx Ly Lz Ma Mb Md Mf Mg Mh Mj Mk Ml Mm Mn Mq Mr Ms Mt Mu Mv Nb Ne Ng Nh Ni Nj Nk Nl Nm Nq Nr Nt Nu Nv Nx Ny Oh Oi Om Pa Pc Pd Pe Pf Pg Pz Qe) Nj(Hq Hr Hu Hv Hw Ii Ik Il In Iq Iu Iv Jg Jh Jk Jl Jm Jp Jr Lh Lu Lv Lx Ly Lz Ma Mb Md Mf Mg Mh Mj Mk Ml Mm Mn Mq Mr Ms Mt Mu Mv Nb Nc Ne Ng Nh Ni Nk Nl Nm Nn Nq Nr Nu Nv Nx Ny Oh Oi Om Pa Pc Pd Pf Pg Pz Qe) Jg(Hq Hr Hv Hw Ii Ik Il In Iq Iu Iv Jh Jk Jl Jm Jp Jr Lh Lu Lv Lx Ly Lz Ma Mb Md Mf Mh Mj Mk Ml Mm Mn Mp Mq Mr Ms Mt Mu Mv Nb Nc Nc Nh Ni Nk Nl Nm Nn Nq Nr Nt Nu Nv Nx Ny Oh Om On Pa Pc Pd Pf Pg Pz Qe) Jl(Hq Hu Hv Hw Ii Ik Il In Iq Iu Iv Jh Jk Jm Jp Jr Lh Lu Lv Lx Ly Lz Ma Mb Md Mf Mg Mh Mj Mk Ml Mm Mn Mq Mr Ms Mt Mu Mv Nb Ne Ng Nh Ni Nk Nl Nm Nq Nr Nt Nu Nv Nx Ny Oh Oi Om On Pa Pc Pd Pf Pg Pz Qe) Jr(Hq Hr Hu Hv Hw Ii Il In Iq Iv Jh Jm Jp Lh Lu Lv Lx Ly Lz Ma Mb Mf Mg Mh Mj Mk Mm Mn Mp Mq Mr Ms Mt Mv My Nb Nc Ne Ng Nh Ni Nk Nl Nm Nn Nq Nr Nt Nu Nv Nx Ny Oh Oi Om On Pa Pc Pd Pe Pf Pg Pz Qe) Mf(Hq Hr Hu Hv Hw Ii Ik Il In Iq Iu Jh Jk Jm Jo Jp Lh Lu Lv Lx Ly Lz Ma Mb Md Mg Mh Mj Mk Ml Mm Mn Mq Mr Ms Mt Mu Mv My Nb Ne Ng Nh Ni Nk Nl Nq Nr Nu Nv Nx Ny Oh Oi Om Pa Pc Pd Pf Pg Pz Qe) Ms(Hq Hr Hu Hw Ii Ik Il In Iu Iv Jh Jk Jm Jp Lh Lu Lv Lx Ly Lz Ma Mb Md Mg Mh Mj Mk Ml Mm Mn Mq Mr Mt Mu Mv My Nb Ne Ng Nh Ni Nk Nl Nm Nq Nr Nu Nv Nx Ny Oh Oi Om Pa Pc Pd Pf Pg Pz Qe) Nb(Hq Hv Hw Ii Il In Iq Iu Iv Jh Jk Jm Jp Lh Lu Lv Lx Ly Lz Ma Mb Md Mh Mj Mk Ml Mm Mn Mq Mr Mt Mu Mv Ne Nh Ni Nk Nl Nm Nn Nq Nr Nt Nu Nv Nx Ny Oh Oi Om On Pa Pc Pd Pf Pg Pz Qe Rt) In(Hq Hu Hv Hw Ii Ik Il Iq Iu Iv Jh Jk Jm Jp Lh Lu Lv Lx Ly Lz Ma Mb Md Mg Mh Mj Mk Ml Mm Mn Mq Mr Mt Mu Mv Ne Nh Ni Nk Nl Nm Nq Nr Nt Nu Nv Nx Ny Oh Oi Om Pa Pc Pd Pf Pg Pz Qe) Nl(Hq Hr Hu Hv Hw Ii Ik Il Iq Iv Jm Jp Lh Lu Lv Lx Ly Lz Ma Mb Mg Mh Mj Mk Mm Mn Mp Mr Mt My Nc Ne Ng Nh Ni Nk Nm Nn Nq Nr Nt Nu Nx Ny Oh Oi Om On Pa Pc Pd Pe Pf Pg Pz Qe) Il(Hq Hv Hw Ii Ik Iq Iu Iv Jh Jk Jm Jp Lh Lu Lv Lx Ly Lz Ma Mb Md Mh Mj Mk Ml Mn Mq Mr Mt Mu Mv Ne Nh Ni Nk Nm Nq Nr Nt Nu Nv Nx Ny Oh Oi Om On Pa Pc Pd Pe Pf Pg Pz Qe) Ny(Hq Hr Hv Hw Ii Ik Iq Iu Iv Jh Jk Jm Jp Lh Lu Lv Lx Ly Lz Ma Mb Md Mg Mh Mj Mk Ml Mn Mq Mr Mu Mv Ne Nh Ni Nk Nm Nn Nq Nr Nt Nu Nv Nx Oh Oi Om Pa Pc Pd Pf Pg Pz Qe) Nx(Hq Hr Hu Ii Ik Iq Iu Jh Jk Jm Jo Jp Lu Lv Lx Ly Lz Ma Mb Md Mg Mh Mj Mk Ml Mm Mn Mq Mt Mu Mv My Ne Ng Nh Ni Nk Nm Nq Nr Nu Nv Oh Oi Om Pa Pc Pd Pf Pz Qe) Om(Hq Hu Hv Hw Ii Ik Iq Iv Jh Jm Jp Lh Lu Lv Lx Ly Lz Ma Md Mg Mh Mj Mk Mm Mn Mp Mr Mt Mv Nc Ne Nh Ni Nk Nm Nn Nr Nt Nu Oh Oi On Pa Pc Pd Pe Pf Pg Pz Qe) Nm(Hq Hu Hv Hw Ii Ik Iq Iu Jh Jk Jm Jp Lh Lu Lv Lx Ly Lz Ma Mb Md Mh Mj Mk Ml Mm Mn Mq Mr Mt Mu Mv Ne Nh Ni Nk Nq Nr Nu Nv Oh Pa Pc Pd Pf Pg Pz Qe) Ly(Hq Hr Hu Hw Ii Ik Iq Iu Jh Jk Jm Jo Jp Lu Lv Lz Ma Mb Md Mg Mh Mj Mk Ml Mm Mn Mq Mt Mu Mv My Ne Ng Nh Ni Nk Nq Nr Nv Oh Oi Pc Pd Pf Pg Pz Qe) Ma(Hq Hr Hw Ii Iq Iu Jh Jk Jm Jp Lh Lu Lv Lx Lz Mb Md Mh Mj Mk Ml Mn Mp Mq Mr Mt Mu Mv Ne Nh Ni Nk Nn Nq Nr Nu Nv Oh Oi Pa Pc Pd Pf Pg Pz Qe) Mj(Hq Hr Hu Hv Hw Ii Ik Iq Iv Jm Jp Lh Lu Lx Lz Mg Mh Mk Mm Mn Mp Mr Mt My Nc Ne Ng Nh Ni Nk Nn Nr Nt Nu Oh Oi On Pa Pc Pd Pe Pf Pg Pz Qe) Qe(Hq Hv Hw Ii Iq Iu Iv Jh Jk Jm Jp Lh Lu Lv Lx Lz Mb Md Mh Mk Ml Mn Mq Mr Mt Mu Mv Ne Nh Ni Nk Nq Nr Nt Nu Nv Oh Pa Pc Pd Pe Pf Pg Pz) Lz(Hq Hu Hw Ii Iq Iu Jh Jk Jp Lh Lu Lv Lx Mb Md Mg Mh Mk Ml Mn Mp Mq Mr Mt Mu Mv Ne Nh Ni Nk Nq Nr Nu Nv Oh Oi Pa Pc Pd Pf Pg Pz) Hq(Hr Hu Hv Hw Ii Ik Iq Iv Jk Jm Jo Jp Lh Lu Lv Mg Mh Mk Mm Mn Mq Mr Mt My Ne Ng Ni Nk Nn Nq Nr Nu Nv Oh Oi Pa Pc Pd Pf Pg Pz) Lu(Hr Hu Hv Hw Ik Iq Iv Jm Jo Jp Lh Lx Mg Mh Mk Mm Mn Mp Mr Mt My Nc Ne Ng Ni Nk Nn Nr Nt Nu Oh Oi On Pa Pc Pd Pe Pf Pg) Lv(Hr Hu Hv Hw Ik Iq Iv Jm Jo Jp Lh Lx Mb Mg Mh Mm Mn Mp Mr Mt My Nc Ne Ng Ni Nk Nn Nr Nt Nu Oh Oi On Pa Pc Pd Pe Pf Pg) Mq(Hr Hu Hv Hw Ik Iq Iv Jm Jo Jp Lh Lx Mg Mh Mm Mn Mp Mr Mt My Nc Ng Ni Nk Nn Nr Nt Nu Oh Oi On Pa Pc Pd Pe Pf Pg) Nq(Hr Hv Hw Ik Iq Iv Jm Jo Jp Lh Lx Mg Mh Mm Mn Mp Mr Mt Mu Mv Nc Ni Nk Nn Nr Nt Nu Oh Oi On Pa Pc Pd Pe Pf Pg) Nv(Hr Hu Hv Hw Ik Iq Iv Jm Jo Jp Lh Lx Mg Mh Mm Mn Mp Mr Mt My Nc Ng Ni Nk Nn Nr Nt Nu Oh Oi Pa Pc Pd Pe Pf Pg) Mb(Hr Hu Hv Hw Ik Iq Iv Jm Jo Jp Lh Lx Mg Mh Mm Mn Mp Mr Mt My Nc Ng Ni Nn Nr Nt Nu Oh Oi On Pa Pc Pe Pf Pg) Md(Hr Hu Hv Hw Ik Iq Iv Jm Jo Jp Lh Lx Mg Mh Mm Mn Mp Mr Mt My Nc Ng Ni Nn Nr Nt Nu Oh Oi On Pa Pc Pe Pf Pg) Iu(Hr Hu Hv Hw Ik Iq Iv Jm Jo Jp Lh Lx Mg Mh Mm Mn Mp Mr Mt My Nc Ng Ni Nn Nr Nt Nu Oh Oi On Pa Pc Pe Pf Pg) Pz(Hr Hu Hv Hw Ik Iq Iv Jm Jo Jp Lh Lx Mg Mh Mk Mm Mn Mp Mr Mt My Nc Ng Ni Nn Nr Nt Nu Oh Oi Pa Pc Pe Pf Pg) Ml(Hr Hu Hv Hw Ik Iq Iv Jm Jo Jp Lh Lx Mg Mh Mm Mn Mp Mr Mt Nc Ng Ni Nn Nr Nt Nu Oh Oi On Pa Pc Pe Pf Pg) Nh(Hr Hu Hv Hw Ik Iq Iv Jm Jo Jp Lh Lx Mg Mh Mm Mn Mp Mr Mt My Ng Ni Nn Nr Nt Nu Oh Oi On Pa Pc Pe Pf

Figure 36 Continued

Pg) Jk(Hr Hu Hv Hw Ik Iq Iv Jm Jo Jp Lh Lx Mg Mh Mm Mn Mp Mr Mt My Nc Ni Nk Nn Nr Nt Nu Oh Oi Pa Pc Pe Pf Pg) Ne(Hr Hu Hv Hw Ik Iq Iv Jm Jo Jp Lh Lx Mg Mh Mk Mm Mn Mp Mr Mt My Ng Ni Nn Nr Nu Oh Oi On Pa Pc Pf Pg) Ii(Hr Hu Hv Hw Ik Iq Iv Jm Jo Jp Lh Lx Mg Mh Mk Mm Mn Mp Mt My Nc Ng Ni Nk Nn Nr Nu Oh Oi Pa Pc Pf Pg) Jh(Hr Hu Hv Hw Ik Iq Iv Jm Jo Jp Lh Lx Mg Mh Mm Mn Mp Mr Mt Nc Ng Ni Nn Nr Nt Nu Oh Oi Pa Pc Pe Pf Pg) Mu(Hr Hv Hw Ik Iq Iv Jm Jo Jp Lh Lx Mg Mh Mm Mn Mp Mr Mt My Nc Ng Ni Nr Nt Nu Oh Oi Pa Pc Pe Pf Pg) Mv(Hr Hu Hv Hw Ik Iq Iv Jm Jo Jp Lh Lx Mg Mh Mm Mn Mp Mr Nc Ng Ni Nr Nt Nu Oh Oi Pa Pc Pe Pf Pg) Pd(Hr Hu Hv Hw Ik Iq Iv Jm Jo Jp Lh Lx Mg Mh Mk Mm Mn Mr Mt My Nc Ng Ni Nk Nn Nr Nu Oh Oi Pa Pc) Mk(Hr Hu Hv Hw Ik Iq Iv Jm Jo Jp Lh Lx Mg Mh Mm Mn Mt My Ng Ni Nk Nn Nr Nu Oh Oi Pc Pf Pg) Nk(Hr Hu Hv Hw Ik Iq Jm Jo Jp Lh Lx Mg Mh Mm Mn Mr Mt My Ng Nn Nr Nu Oh Oi Pa Pc Pf Pg) Mn(Hr Hw Iq Iv Jm Jp Lh Lx Mh Mr Mt Ni Nr Oh Pa Pc Pf Pg) Oh(Hr Hu Ik Iq Jp Lh Lx Mh Mp Mt Ni Nn Nr Nu Pa Pf Pg) Pf(Hr Hw Iq Jm Jp Lh Lx Mh Mr Mt Ni Nr Nu Pa Pe Pg) Lh(Hv Hw Iq Jp Lx Mh Mr Mt Ni Nr Nt On Pa Pg) Iq(Hw Jm Jp Lx Mh Mr Mt Ni Nr Pa Pc Pg) Jp(Hr Ik Lx Mh Mt Ni Nr Nu Oi Pa Pg) Mr(Hv Hw Lx Mt Nr Nt On Pa Pg) Pa(Hw Lx Mt Ni Nr Nt On Pg) Pg(Hw Jm Lx Mh Mt Ni Nr) Aa(Im Of Og Oy Oz Pb) Mg(Hr Hu Ik Jo My Oi) Nr(Hw Lx Mh Mt Nu) Ni(Hr Hu Jm Lx Mt) Yd(aY Ed Im Sr) Oi(Hu Ik My Ng) Lx(Hw Mt) AjJt NnMt MyNg HrHu HvHw ImYe} No{Nn(Eq Fp Fr Hq Hr Hv Hw Hx Ii Il In Io Iq Is Iu Iv Jg Jh Jk Jl Jm Jo Jp Jq Jr Js Lh Lj Lu Lv Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Ng Nh Ni Nj Nk Nl Nm Nq Nr Nt Nu Nv Nx Ny Of Oh Oi Om On Pa Pd Pe Pf Pg Po Pz Qa Qb Qc Qd Qe Rz Wf Wh Zw) Is(Fp Fr Hq Hr Hu Hv Hw Hx Ih Ii Ij Il In Io Iq It Iu Iv Jg Jh Jk Jl Jm Jn Jo Jp Jq Jr Js Lh Lj Lu Lv Lx Ly Lz Ma Mb Mc Md Mc Mf Mg Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Nt Nu Nv Nx Ny Of Oh Oi Ok Om On Pa Pc Pd Pe Pf Pg Po Qa Qb Qc Qd) Qc(Fp Fr Hq Hr Hu Hv Hw Hx Ii Il In Io Iq Iu Iv Jg Jh Jk Jl Jm Jn Jo Jp Jq Jr Js Lh Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Nt Nu Nv Nx Ny Of Oh Oi Om On Pa Pc Pd Pe Pf Pg Po Pz Qa Qb Qd Qe) Nm(Fp Fr Hq Hu Hv Hw Hx Ii Ij Il In Io Iq Iu Iv Jg Jh Jk Jl Jm Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Nh Ni Nj Nk Nl Nq Nr Nt Nu Nv Nx Ny Of Oh Oi Ok Om On Pa Pc Pd Pe Pf Pg Po Qa Qb Qd Qe) Qd(Fp Fr Hq Hr Hu Hv Hw Hx Ii In Io Iq It Iu Iv Jg Jh Jk Jl Jm Jn Jo Jp Jq Jr Js Lh Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nq Nr Nt Nu Nv Nx Ny Oh Oi Om On Pa Pc Pd Pe Pf Pg Po Pz Qa Qb Qe) Js(Fp Fr Hq Hu Hv Hw Hx Ih Ii Ij Il In Io Iq Ir It Iu Iv Jg Jh Jk Jl Jm Jn Jp Jq Jr Jt Lh Lj Lu Lv Lx Ly Lz Ma Mb Mc Md Me Mf Mg Mi Mj Mk Ml Mm Mn Mp Mq Mr Ms Mt Mu Mv Mw Mx My Mz Na Nb Nc Nd Ne Nf Ng Nh Ni Nj Nk Nl Nq Nr Nt Nu Nv Nx Ny Oh Oi Om On Pa Pc Pd Pe Pf Pg Po Qa Qb) Jp(Fp Fr Hq Hr Hu Hv Hw Hx Ii Il In Io Iq Iu Iv Jg Jh Jk Jl Jm Jo Jq Jr Lh Lu Lv Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nq Nr Nt Nu Nv Nx Ny Oh Oi Om On Pa Pc Pd Pe Pf Pg Po Pz Qa Qb Qe) Mi(Fp Fr Hr Hu Hv Hw Hx Ii Il In Io Iq Iu Iv Jg Jh Jk Jl Jm Jo Jq Jr Lh Lj Lu Lv Lx Ly Lz Ma Mb Mc Md Me Mf Mg Mj Mk Ml Mm Mn Mp Mq Mr Ms Mt Mu Mv Mw Mx Mz Na Nb Nc Nd Ne Nf Ng Nh Ni Nj Nk Nl Nq Nr Nt Nu Nv Nx Ny Oh Oi Ok Om On Pa Pc Pd Pe Pf Pg Po Pz Qa Qb Qe) Jn(Fp Fr Hv Hw Hx Ii Il In Io Iq Iu Iv Jg Jh Jk Jl Jm Jo Jq Jr Lh Lj Lu Lv Lx Ly Lz Ma Mb Mc Md Me Mf Mg Mj Mk Ml Mm Mn Mq Mr Ms Mt Mu Mv Mw Mx My Mz Na Nb Nc Ne Nf Ng Nh Ni Nj Nl Nq Nr Nt Nu Nv Nx Ny Oi Om On Pa Pc Pd Pe Pf Pg Po Pz Qa Qb Qe) Jq(Fp Fr Hq Hu Hv Hw Hx Ii Ij Il In Io Iq Iv Jg Jh Jk Jl Jm Jo Jr Jt Lj Lu Lv Lw Lx Ly Lz Ma Mc Md Me Mf Mg Mh Mj Mk Ml Mm Mn Mp Mr Ms Mu Mv Mw My Mz Na Nc Nd Ne Nf Ng Nh Ni Nj Nk Nr Nt Nu Nv Nx Ny Oh Oi Ok Om On Pa Pc Pd Pe Pf Pg Po Qa Qb) On(Fp Fr Hq Hv Hw Hx Ii Ij Il In Io Iq Iu Iv Jg Jh Jk Jl Jm Jo Jr Jt Lh Lu Lv Lx Ly Lz Ma Mb Mc Md Me Mf Mg Mj Ml Mm Mn Mp Mq Mr Ms Mt Mu Mw Mx Mz Na Nb Nc Nd Ne Nf Nh Ni Nj Nk Nl Nq Nr Nt Nu Nx Ny Oh Oi Ok Om Pa Pc Pd Pe Pf Pg Pz Qa Qb) Nu(Fp Hq Hr Hu Hv Hw Hx Ii Il In Io Iq Iv Jg Jl Jm Jo Jr Lh Lj Lu Lv Lx Ly Lz Ma Mc Me Mf Mg Mh Mj Mk Mm Mn Mp Mr Ms Mt Mu Mv Mw Mx My Mz Na Nb Nc Nd Ne Nf Ng Nh Ni Nj Nk Nr Nt Nx Ny Of Oh Oi Om Pa Pc Pd Pe Pf Pg Po Qa Qb) Ik(Fp Fr Hq Hu Hv Hw Hx Ii Il In Io Iq Iu Jh Jk Jl Jm Jo Jr Lh Lu Lx Ly Lz Ma Mb Mc Md Me Mf Mg Mj Mk Ml Mm Mn Mq Mr Ms Mt Mu Mv Mx My Mz Na Nb Nc Nd Ne Nf Ng Nh Ni Nk Nl Nq Nr Nv Nx Ny Of Oh Oi Om Pa Pd Pe Pf Pg Po Pz Qe) Ok(Fp Fr Hq Hv Hw Hx Ii Il In Io Iq Iu Iv Jg Jh Jk Jl Jm Jr Lh Lu Lv Lx Ly Lz Ma Mb Mc Md Me Mf Mg Mj Mk Ml Mm Mn Mq Mr Ms Mt Mu Mv Mx Mz Na Nb Nc Ne Nf Ng Nh Ni Nj Nl Nq Nr Nt Nv Nx Ny Oh Oi Om Pa Pd Pe Pf Pg Po Pz Qa Qe) Nd(Fp Fr Hr Hu Hv Hw Hx Ii Il In Io Iv Jg Jl Jm Jo Jr Lh Lj Lu Lv Lx Ly Lz Ma Mb Mc Me Mf Mg Mh Mj Mk Mm Mn Mp Mr Ms Mt Mu Mv Mw My Mz Na Nb Nc Ne Nf Ng Nh Ni Nj Nk Nq Nt Nx Ny Of Oh Oi Om Pa Pc Pd Pe Pf Pg Po Qa Qb) It(Fp Fr Hv Hw Hx Il In Io Iq Iu Iv Jh Jk Jl Jm Jr Lh Lj Lu Lv Lx Lz Ma Mb Mc Md Me Mf Mg Mj Mk Ml Mm Mn Mq Mr Ms Mt Mu Mv Mx Na Nb Nc Ne Nf Ng Nh Ni Nj Nl Nq Nr Nt Nv Nx Ny Oi Om Pa Pd Pe Pf Pg Po Pz Qa Qb Qe) Mp(Fp Hq Hr Hu Hv Hw Ii Il In Io Iq Iu Iv Jg Jl Jm Jo Jr Lj Lu Lv Lw Ly Lz Ma Mc Md Me Mf Mg Mh Mj Mk Mm Mn Ms Mt Mu Mv Mw My Mz Na Nc Ne Nf Ng Nh Ni Nj Nk Nt Nv Nx Ny Of Oh Oi Om Pa Pc Pd Pe Pf Pg Po Qa Qb) Ij(Fp Fr Hv Hw Il In Io Iq Iu Iv Jg Jh Jk Jl Jm Jr Lh Lu Lv Lx Ly Lz Ma Mb Mc Md Me Mf Mg Mj Mk Ml Mn Mq Mr Mt Mu Mv Mx Mz Na Nb Nc Ne Nf Nh Ni Nj Nl Nq Nr Nt Nv Nx Ny Oh Oi Om Pa Pd Pe Pf Pg Po Pz Qa Qb Qe) Jg(Fp Hq Hr Hv Hw Hx Ii Il In Iq Iv Jh Jk Jl Jm Jo Jr Jt Lh Lj Lv Lx Ly Lz Mc Md Me Mf Mg Mh Mj Mk Mm Mn Mr Ms Mt Mu Mv Mw Mz Nc Ne Nh Ni Nj Nk Nq Nt Nx Ny Oh Oi Pa Pc Pd Pe Pf Pg Po Pz Qa Qb) Mh(Fp Fr Hq Hr Hu Hv Hw Ii Il In Io Iq Iv Jl Jm Jo Jr Lh Lj Lu Lv Lx Ly Lz Ma Mc Me Mf Mg Ml Mm Mn Mr Ms Mw Mx My Nb Nc Ne Ng Nh Ni Nj Nk Nq Nt Nx Ny Of Oh Oi Om Pa Pc Pd Pe Pf Pg Qa Qb) Ih(Fp Fr Hv Hw Hx Il Io Iq Iu Iv Jh Jk Jl Jm Jr Lh Lj Lu Lv Lx Ly Lz Mb Mc Md Me Mf Mg Mk Ml Mn Mq Mr Mt Mu Mv Mx Na Nb Nc Ne Nf Ng Nh Ni Nl Nq Nr Nv Nx Ny Om Pa Pd Pe Pg Po Pz Qa Qb Qe) Mz(Fp Hq Hu Hv Hx Ii Il In Io Iv Jl Jm Jo Lj Lv Ly Lz Ma Mc Md Me Mf Mg Mj Mk Ml Mm Mn Ms Mt Mu Mv Mw My Na Nc Ne Nf Ng Nh Ni Nj Nk Nt Nv Nx Ny Oh Oi Om Pa Pc Pd Pe Pf Po Qa Qb) Mw(Hq Hr Hu Hv Hw Ii Il In Io Iv Jl Jm Jo Lh Lj Lu Lv Ly Lz Ma Me Mf Mg Mj Mk Mm Mn Mr Ms Mt Mu Mv Nb Nc Ne Nf Ng Nh Ni Nj Nk Nt Nx Ny Of Oh Oi Pa Pc Pd Pe Pf Pg Qa Qb) Oe(Fp Fr Hq Hu Hv Hw Hx Ii Il Iu Jh Jk Jo Jr Lh Lu Lv Lx Ly Lz Ma Mb Mc Md Mf Mj Mk Ml Mq Mr Ms Mt Mu Mv Mx My Na Ne Nf Ng Nh Nl Nq Nr Nv Nx Of Oi Pa Pd Pe Pg Po Pz Qe) Jt(Aj Fp Fr Hw Il Io Iq Jh Jk Jl Jm Jr Lh Lu Lv Lx Ly Lz Ma Mb Mc Md Me Mf Mk Ml Mm Mn Mq Mr Mt Mu Mv Mx Nb Nc Ne Nf Nh Ni Nl Nq Nt Nv Ny Om Pa Pd Pe Pf Pg Pz Qa Qe) Pc(Fp Hq Hr Hu Hv Hw Ii Il In Io Iv Jl Jm Jo Lh Lj Lv Ly Lz Ma Me Mf Mg Mj Mm Mn Mr Ms Mt Mu Mv My Nb Nc Nf Ng Ni Nj Nk Nt Nx Ny Of Oh Oi Om Pa Pd Pe Pf Pg Po Qa Qb) Li(Fp Fr Hw Hx Io Iq Iu Jh Jk Jl Jm Jr Lh Lu Lv Lx Ma Mb Mc Md Me Mg Mk Ml Mq Mr Ms Mt Mu Mx Na Nb Nc Ne Nh Ni Nl Nq Nr Nv Nx Ny Om Pa Pd Pe Pg Pz Qe Wf Wh Yd) Hu(Fp Fr Hq Hr Hv Hw Ii Il In Io Iq Iv Jh Jk Jl Jm Jo Lh Lj Lv Lx Ly Lz Ma Me Mg Mm Mn Mr Ms Mt Mu Mx Nb Nc Ni Nj Nk Nq Nt Ny Of Oh Oi Om Pa Pe Pf Pg Qa Qb) Qa(Hq Hv Hx Ii Il In Ir Iv Jk Jl Jm Jo Lj Lv Ly Lz Ma Md Me Mf Mg Mj Mm Mn Ms Mt Mu My Na Nc Ne Nf Ng Nh Ni Nj Nk Nt Nx Of Oh Oi Pa Pd Pf Po Qb) Lw(Fr Hv Hw Hx Io Iq Iu Jh Jk Jl Jm Jr Lh Lu Lv Lx Lz Ma Mb Mc Md Me Mg Mj Ml Mm Mq Mr Mv Mx Na Nb Ne Nf Nh Nl Nq Nr Nv Om Pe Pg Po Pz Qe) Hr(Fp Hq Ii Il Iq Iv Jl Jm Jr Lh Lj Lv Ly Ma Me Mf Mg Mm Mn Mr Ms Mt My Na Nb Nc Nf Ng Ni Nj Nk Nt Ny Of Oh Oi Om Pa Pe Pg Qb) Oy(Aa Fp Hq Hx Ii Io Iu Jk Jl Jr Lu Lx Ly Lz Mb Mc Md Mf Mj Mk Ml Mq Mr Mu Mv Mx Na Ne Nf Ng Nh Nl Nq Nr Nv Nx Oi Pd Po Pz Qe) Of(Hq Hv Hw Ii Il In Io Iq Iv Jh Jm Jo Lh Lj Lv Ly Lz Ma Me Mg Ml Mm Mn Mr Ms My Nc Ni Nj Nk Nq Nt Ny Oh Pa

Figure 36 Continued

Pe Pf Pg Qb) Qb(Hq Hv Hw Ii Il In Ir Iv Jk Jo Lj Lv Ly Lz Ma Me Mf Mg Mj Mm Mn Ms Mt My Nc Ne Ng Ni Nj Nk Nt Nx Oh Oi Pa Pd Pf)
Nk(Fp Hq Hv Hw Ii Il In Io Iv Jm Jo Lj Lv Ly Me Mg Mm Mn Ms Mt My Ng Ni Nj Nl Nt Ny Oh Oi Om Pd Pe Pg) Ir(Fp Fr Hw Iq Jh Jl Jm Jr
Lh Lu Lx Mb Md Mk Ml Mq Mr Mv Mx Nb Nl Nq Nr Nv Ny Om Pe Pg Pz Qe) My(Hv In Iv Jl Jm Jo Lh Lv Ma Me Mg Ml Mm Mn Mr Ms
Mv Nc Ni Nj Nq Nt Ny Oh Om Pa Pe Pf Pg) Ns(Fr Hx Il Iu Jh Jk Lh Lx Mb Mc Md Mk Ml Mr Mu Mv Mx Na Ne Nh Nl Nq Nr Nv Nx Po Pz
Qe) Nj(Hq Hv Hw Ii Il In Iq Iv Jo Lj Lv Ly Ma Mf Mg Mm Mn Mt Nb Ng Ni Nt Nx Ny Oh Oi Pe Pf) Iv(Hq Hv Ii In Jo Lj Ly Ma Me Mj Mm
Mn Ms Nc Ng Oh Oi) Lj(Hq Hv Ii In Lv Ma Mg Mm Mn Mt Nc Nq Nt Oh Pf) Ng(Ma Me Mg Mm Mn Mt Nc Nt Ny Om) Oh(Lv Ma Mm Mn
Nc Nt Ny Oi) Mm(Hq Hv In Nt Oi Pe) Jo(Hv Lv Ma Mg Mn Nt) Po(Lh Mr Nb Pe) Va(aW cL Cx Vq) Nt(Li Ly Oi) Mt(Hx Mv Ny) Nc(Ly Ne
Ni) Yd(aU Ld Ow) Aa(Oz Pb) Nb(Hx Ii) Ip(Pz Qe) Kd(Wf Wh) Pd(Pe Pg) aW(Rz Sh) FcOz LvLy MeMf MkPa MnMs IlNy ImYe} Li{Yd(aA aC aE AF AJ aN aR AS aU aV Aw AX aY aZ bA bE bF bJ bL bM BO bR bS bW bZ cG cH cL Co Cq cS CV cW DD dF dG dH dL Dr Du Ed Eq Ex Fn Fr Gb Gc Gl Hb Hl Hp Hq Ib Ic Ih Im Io Ip Iq Je Jh Jj Jo Ke Kg Ko Kq Kx Ld Lx Ma Mf Mg Mh Ml Mm Mu Mw Mx Nb Nt Nu Nw Ny On Oz Pb Pc Pe Pi Pj Ps Qd Ql Qm Qy Rc Rg Rt Rz Si Sj St Tn Ub Uh Um Un Uo Ur Uv Vc Vi Vt Wb Zw) Js(Du Fp Fr Hq Hv Hw Hx Ii In Io Iq Is Iu Iv Jg Jh Jk Jl Jm Jn Jq Jr Lh Lu Lv Lx Ma Mb Mc Md Me Mf Mg Mi Mj Mk Ml Mm Mn Mp Mq Mr Ms Mt Mu Mv Mw Mx My Mz Na Nb Nc Nd Ne Nf Ng Nh Ni Nj Nl Nm Nn Nq Nr Nt Nu Nv Nx Ny Oh Om Pa Pc Pd Pe Pf Pg Po Pz Qa Qb Qc Qd Qe) Nt(Fp Fr Hq Hv Hw Hx Ii Il In Io Iq Is Iu Iv Jg Jh Jk Jl Jm Jr Lh Lj Lu Lv Lx Lz Ma Mb Mc Md Me Mf Mg Mi Mj Mk Ml Mm Mn Mp Mr Ms Mt Mu Mv Mw Mx My Na Nb Nc Ne Nf Ng Nh Ni Nj Nk Nl Nm Nn Nr Nu Nv Nx Ny Oh Om On Pa Pc Pd Pe Pf Pg Po Pz Qa Qb Qe) Qd(Fp Fr Hq Hv Hw Hx Ii In Io Iq Is Iu Iv Jg Jh Jk Jl Jm Jo Jr Lh Lu Lv Lx Ly Ma Mb Mc Md Me Mf Mg Mj Mk Ml Mm Mn Mp Mq Mr Ms Mt Mu Mv Mw Mx My Na Nb Nc Ne Nf Ng Nh Ni Nj Nl Nm Nn Nq Nr Nv Nx Ny Oh Om Pa Pc Pd Pe Pf Pg Po Pz Qa Qb Qc Qe) Oe(Du Fp Fr Hq Hu Hv Hw Hx Ii Il In Io Iq Iu Jh Jk Jl Jm Jo Jr Lh Lu Lv Lx Ly Lz Ma Mb Mc Md Me Mf Mg Mh Mj Mk Ml Mm Mn Mp Mq Mr Ms Mt Mu Mv Mx My Na Nc Ne Nf Ng Nh Ni Nj Nk Nl Nn Nq Nr Nv Nx Ny Of Oh Oi Om Oy Pa Pc Pd Pe Pf Pg Po Pz Qe) Mz(Fp Fr Hq Hv Hw Ii Il In Io Iq Is Iu Iv Jg Jh Jk Jl Jm Jo Jr Lh Lu Lv Lx Lz Ma Mb Mc Md Me Mf Mg Mj Mk Ml Mm Mn Mp Mq Mr Ms Mt Mu Mv Mx Na Nb Nc Nd Ne Ng Nh Ni Nj Nk Nl Nm Nn Nq Nr Nv Nx Ny Oh Om Pa Pc Pd Pe Pg Pz Qa Qb Qc Qe) Jn(Du Fp Fr Hq Hv Hw Hx Ii Il In Io Iq Is Iu Iv Jg Jh Jk Jl Jm Jr Lh Lu Lv Lx Lz Ma Mb Mc Md Me Mf Mg Mj Mk Ml Mm Mn Mq Mr Ms Mt Mu Mv Mx My Na Nb Nc Ne Nf Ng Nh Ni Nj Nl Nn Nq Nr Nv Nx Ny Oh Om Pa Pc Pd Pe Pf Pg Po Pz Qa Qb Qe) Hr(Aa Fp Fr Hq Hu Hx Ii Il Io Iq Iu Jg Jh Jk Jl Jm Jr Lj Lu Lv Lx Ly Lz Ma Mb Mc Md Me Mf Mg Mh Mj Mk Ml Mm Mn Mp Mq Ms Mt Mu Mv Mx My Na Nc Ne Nf Ng Nh Ni Nj Nk Nl Nn Nq Nr Nu Nv Nx Ny Of Oh Oi Pa Pc Pd Pf Pg Po Pz Qe) It(Du Fp Fr Hq Hv Hw Hx Ii Il Io Iq Is Iu Iv Jh Jk Jl Jm Jr Lh Lu Lv Lx Lz Ma Mb Mc Md Me Mg Mj Mk Ml Mm Mq Mr Ms Mt Mu Mv Mx My Na Nb Nc Ne Nf Ng Nh Ni Nj Nl Nn Nq Nr Nv Nx Ny Oh Om Pa Pc Pd Pe Pf Pg Po Pz Qa Qb Qe) Qc(Aa Fr Hq Hu Hv Hw Hx Ii In Io Is Iv Jg Jh Jl Jm Jo Lh Lv Lx Ly Ma Mb Mc Me Mf Mg Mh Mj Ml Mm Mn Mp Mr Ms Mt Mv Mw My Na Nb Nc Nd Ne Nf Ng Nh Ni Nj Nk Nm Nn Nq Nu Nv Nx Ny Of Oh Oi Om Pa Pc Pd Pe Pf Pg Qa Qb Vi) Oy(Du Fp Fr Hq Hu Hv Hw Hx Ii Il In Io Iq Iu Iv Jk Jl Jm Jo Jr Lh Lu Lv Lx Ly Lz Mb Mc Md Me Mf Mg Mh Mj Mk Ml Mm Mq Mr Ms Mu Mv Mx My Na Nc Ne Nf Ng Nh Ni Nj Nk Nl Nn Nq Nr Nv Nx Ny Of Oh Oi Pc Pd Pf Po Pz Qe Vi) Mi(Fp Fr Hv Hw Hx Ii Io Iq Is Iu Iv Jh Jk Jl Jm Jr Lh Lu Lv Lx Ma Mb Mc Md Me Mf Mg Mj Mk Ml Mm Mn Mp Mq Mr Ms Mt Mu Mv Mx Na Nb Nc Ne Nf Ng Nh Ni Nj Nk Nl Nm Nn Nq Nr Nv Nx Ny Oh Oi Om Pa Pd Pe Pg Pz Qa Qb Qe) Is(Fp Hq Hv Hw Ii Il In Io Jg Jh Jk Jl Jo Jq Lh Lj Lx Ly Lz Ma Mb Mc Me Mf Mg Mj Mk Ml Mm Mn Mp Mr Ms Mt Mu Mv Mw My Na Nb Nc Nd Ne Nf Ng Nh Ni Nj Nk Nm Nn Nu Nx Ny Oh Oi On Pa Pc Pd Pe Pf Pg Po Qa Qb Rt) Du(aA AF Aj AX bC bM Ch cQ Cs Ct cV cX De Dg dH dJ Dr Ed Eq Ex Fp Fr Hf Hx Ih Ij Im Ir Iv Jl Ju Ki Kl Kz Lj Mr Ms Mv Mw Ng Nh Oa Ow Oz Pb Pc Pe Ps Qa Qb Qt Qu Rg Rm Rz Ug Uu Ux Va Tm) Ns(Fp Fr Hq Hx Ii Il In Io Iq Iu Jh Jk Jl Jm Jo Jr Lh Lu Lv Lx Lz Mb Mc Md Me Mg Mj Mk Ml Mm Mq Mr Ms Mt Mu Mv Mx My Na Nb Nc Ne Nf Ng Nh Ni Nj Nk Nl Nq Nr Nv Nx Oh Om Pa Pd Pe Pf Po Pz Qe) Vi(Af Aj AN AO aW aX aY Bc Bg bL Ch cQ cR Cu cX DG dH Dk Ed Ef Eq Ez Fr Gl Ik Jd Jm Kd Kj Kl Kx Lj Mf My Ng Nx Of Oz Pb Pc Ql Qn Qt Qu Ru Rz Ss Ua Ul Uu Uv Uw Ux Vb Vs Vw Wd Zw Th) On(Fp Fr Hw Hx Il In Io Iq Iu Iv Jg Jh Jl Jm Jr Lh Lu Lv Lx Lz Ma Mb Mc Md Me Mf Mj Ml Mm Mn Mp Mq Mr Mt Mu Mx Na Nb Nc Ne Nh Ni Nj Nl Nm Nn Nq Nr Ny Om Pa Pd Pe Pf Pg Pz Qa Qb Qe) Mw(Eq Hq Hv Hw Ii Il In Io Iv Jg Jl Jo Lh Lj Lv Lx Ly Lz Ma Mc Me Mf Mg Mh Mm Mn Mp Mr Ms Mt Mv My Nb Nc Nd Ne Nf Ng Nh Ni Nj Nk Nm Nn Nu Nx Ny Of Oh Oi Pa Pc Pe Pf Pg Qa Qb Wf) Ok(Fp Fr Hq Hw Hx Ii Iq Iu Jg Jh Jk Jl Jm Jr Lh Lu Lv Lx Ma Mb Md Me Mf Mk Ml Mm Mq Mr Ms Mt Mu Mv Mx Na Nb Nc Ne Nh Ni Nj Nl Nm Nq Nr Nv Nx Ny Oh Om Pa Pd Pe Pg Pz Qa Qe) Jq(Fp Fr Hw Hx Iq Iu Jh Jk Jl Jm Jr Lh Lu Lv Lx Mb Mc Me Mg Mk Ml Mm Mq Mr Ms Mt Mu Mv Mx Na Nb Nc Ne Nh Ni Nj Nl Nn Nq Nr Nv Ny Oh Om Pa Pd Pe Pg Pz Qa Qe) Nd(Hu Hv Hw Il In Io Iv Jg Jl Jo Lh Lj Lv Lx Ly Lz Ma Mc Me Mf Mh Mk Mm Mn Mp Mr Ms Mt My Nb Nc Nf Ng Ni Nj Nk Nm Nn Nu Ny Of Oh Oi Pa Pc Pd Pe Pg Qa Qb) Hu(Eq Fr Hv Hw Ii Il In Io Iv Jl Jo Lh Lv Lx Ly Lz Ma Mc Mf Mg Mh Mm Mn Mp Mr Mt Mu Mx Nb Nf Ni Nk Nm Nn Nu Nv Ny Of Oh Oi Om Pa Pc Pe Pf Pg Qa Qb Ux) Lj(Fp Hq Hv Hw Il In Io Iq Iv Jg Jl Jm Jo Jr Lh Lx Ly Ma Mc Me Mf Mg Mh Mn Mp Mr Ms Mt Mv Mx My Nb Nc Nf Ng Ni Nj Nk Nm Nn Nu Ny Oh Oi Pa Pc Pe Pg Qe) Qa(Hq Hv Ii Il In Io Iv Jg Jl Jo Jt Lx Ly Lz Ma Mc Me Mf Mh Mj Ml Mm Mn Mp Ms Mt Mv My Ne Nf Ng Nh Nk Nm Nn Nu Ny Of Oh Oi Pa Pc Pd Pe Pf Pg Qb) Qb(Hq Hv Hw Ii Il In Io Iv Jg Jh Jl Jo Lh Lx Ly Lz Ma Mc Mf Mh Mj Ml Mm Mn Mp Mr Ms Mt My Nb Ne Nf Ng Ni Nk Nm Nn Nu Of Oh Oi Pa Pc Pe Pf) Jt(Aj Fp Fr Hw Hx Io Iq Jg Jh Jl Jm Jr Lh Lu Lv Mb Md Me Ml Mm Mq Mr Mt Mu Mx Nb Nc Ne Nh Ni Nj Nl Nm Nn Nq Nr Nv Ny Oh Om Pa Pd Pz Qe) Ed(Dr Eq Fc Fd Fi Gb Gd Gh Gn Hl Ho Lp Op Ps Rt Ru Rv Rx Ry Rz Sf Sh Uw Ux Uy Va Vb Vh Vw Vz Wb Wc Wd Wc Wf Wh Yl Zw Zx Ye Tm Tl Xa) Nu(Hv Hw Ii Il In Io Iq Iv Jg Jl Jo Lh Lx Ly Lz Ma Mf Mg Mh Mm Mn Mp Mr Mt My Nb Nc Nf Ng Ni Nk Nm Nn Ny Of Oh Oi Pa Pc Pe Pf Pg) Iv(Hq Hv Hw Il In Io Jg Jl Jo Lh Lx Ly Lz Ma Mb Mc Mf Mg Mh Mm Mn Mp Mr Mt My Nb Nf Ng Ni Nk Nm Nn Ny Of Oh Oi Pa Pc Pe Pf Pg) Nm(Hq Hv Ii Il In Io Jg Jl Jo Lh Lx Ly Lz Ma Mc Mf Mg Mh Mn Mp Mr Mt My Nb Nc Nf Ng Nk Nn Ny Of Oh Oi Pa Pc Pe Pf Pg Qe) Ip(Fp Fr Hx Iq Iu Jh Jk Jm Jr Lu Lv Mb Mc Md Me Mj Mk Ml Mq Mu Mv Mx Na Ne Nh Ni Nj Nl Nq Nr Nv Om Pd Po Pz Qe) Mp(Hq Hv Hw Il In Io Jg Jl Jo Ly Lz Ma Mc Mf Mg Mh Mk Mn Mt Mv My Nb Nf Ng Ni Nk Ny Of Oi Pc Pd Pe Pf Pg Po) Jp(Aa Fp Fr Hx Io Iq Iu Jg Jh Jk Jr Lu Lv Ma Mb Md Mk Ml Mq Mu Mx Na Nc Nj Nl Nq Nr Nv Om Pd Po Pz Qe) Jg(Hq Hv Hw Ii Il In Jl Jo Lh Lx Ly Lz Mc Mf Mg Mh Mn Mr Mt Mv Ni Nk Nn Nx Oh Pa Pc Pe Pf Pg) Mh(Hv Hw Ii Il In Io Jl Jr Lh Lx Ly Ma Mf Mn My Nb Nf Ng Nn Nr Ny Of Oh Oi Pa Pc Pe Pg) Of(Aa Hv Hw Il In Io Jh Jl Jo Lh Lx Ly Lz Ma Mf Mm Mn Mr Nk Nn Nv Ny Pa Pc Pe Pf Pg) Ih(Fp Hx Iq Iu Jm Jr Lu Mb Md Mg Mk Mq Mu Mv Mx Na Nc Nl Nq Nr Nv Pz Qe) Mn(Hq Hv Hw In Jo Ly Lz Mc Mf Mg Mr My Ng Ni Nk Nn Oh Oi Pc Pe Pf) Ij(Fp Fr Iq Iu Jm Jr Lu Lv Mq Mx Na Nb Nl Nq Nr Nv Om Pz Qe) Oi(Aa Hv Il Io Lh Lz Ma Mm Mt Nb Nn Ny Oh Pc Pe Pf Pg) bM(Lp Ps Rt Ru Rv Rx Si Uy Va Vb Vh Vz Wc We Wf Wh) Ly(Hv Il In Lh Lx Lz Mr Mt Nb Nf Pa Pc Pe Pg) Oz(Iu Jk Lu Md Mj Mk Ml Mu Nj Nl Nq Pd Po Pz) Wb(AN aW aX aY Ch cR cX Gl Qn Us Uv Th) Lw(Fr Iu Lv Md Mm Mq Nj Nl Nq Nv Om Pz) Eq(aY Ba bJ Cx Im Iz Jk Nb Ny Qy St) Pc(Aa Il Lh Lz Ma Mt Nf Nn Oh Pe Pg) Rt(Af aX cC Ch cV cX De Kd Ki Nb) My(Jh Lh Lx Ma Mr Nn Nq Om Pa) Af(Fc Ru Rv Rx Uy Vh Vz We) Dr(Jy Kd Kx Qn Ru Us Uv Th) Nb(Jo Mv Ng Po Rx Uw Ux We) aX(Rx Va Vw Vz Wd Wh Zw Tl) Jo(Aa Hv Hw In Lh Ma Mr) Po(Lh Lx Mr Pa Pe) Nf(Hv In Lh Mt Nn) Hp(aN Gl Rx Us Uv) Im(Aa Ux Wf Zw Ye) Ps(aN Gl Rx Us Uv) Va(aE aV aY dL Fr) Ma(Hv Il Mg Ng) Mm(Fc Hv Mf Ng) Ny(Il Rx We Wf) Pe(Lz Mk Pd Pf) Mt(Mv Ng Pf)

Figure 36 Continued

Figure 36 Continued

Qw Rc Rt Ss Tv Ua Ug Uh Ur Vs Vt Vw Yl Wm) Hu(Gh Op Rz Sj Uw Ux Uy Uz Va Vb Vc Vh Vi Vw Vz Wb Wc Wd Wg Wh Yd Yl Zw Zx Tm Tl Xa) bS(Fi Ps Rz Sf Uw Ux Uy Uz Va Vb Vc Vh Vi Vw Vz Wb Wc Wd Wg Wh Yd Yl Zw Zx Tm Tl Xa) Qw(Fi Gn Rz Uw Ux Uy Uz Va Vb Vc Vh Vi Vw Vz Wb Wc Wd Wg Wh Yd Yl Zw Zx Tm Tl Xa) Qv(Fd Gc Gn Hl Ho Hp Lp Op Ps Rt Rv Sf Ux Uy Uz Va Wb Wc Wh Yd Yl Zw Zx Tl Xa) Qt(Du Fd Gh Hl Ho Rt Ru Rv Ry Uw Uy Uz Va Vb Vh Vi Vc Wd Wg Wh Yd Yl Tl Xa) cl(Fc Fi Gb Gh Hl Rz Si Sj Ux Va Vc Vw Vz Wc Wd Wh Yd Yl Zw) Xa(Af aJ Cx dG Dk dM Ha Hc Ib It Jl Nv Oy Qn Rj Ug Ur Vp) Zw(aH aU Ax Ch Cs Ij Ji Js Kx Ld Ml Oe Pe Qx Ra Ua) Qn(Gn Rz Uw Ux Uy Uz Va Vb Vh Vi Vz Wc Wg Yd Yl Tl) Ug(Gn Hl Ho Rt Ru Ry Uw Uz Vb Vh Vi Wc Wg Yl Tl) aJ(Du Fd Hl Ho Op Rt Ru Ry Uz Va Vh Vi Wc Wg Tl) Hc(Gn Hl Ru Uw Uz Vb Vh Vi Wc Wd Wg Yl Tl) Rt(Cu Dc Dd Fy Ho Hv Ij Iv Jt Mi Oy Ur) Uz(Af Bn Cx Dk dM Gn Ib Nv Oy Rj Ur Vp) Aj(Gb Ho kl kO nA Nk Si Vb Vh Wd Ti) Ux(bP Ch Cw Ld Mg Mt Nn Oe Pd Uf Vq) Vi(Af CX Dk Hb Ib Nv Oy Ur Vt) Cx(mS Rz Va Vh Wc Wg Yl Tl) Yd(Ch Gc Ic Ji Ke Nw Oe Vt) Oy(Fc Hl Ho Uw Vh Wc Wg Tl) Fd(Iv Jn Js Mi Pc Ur Vp) Iz(Gb Ho kP lW mF nA Wd) Va(aG bM bP cX Hb Pc Ua) Af(nD Vh Wc Wg Yl Tl) Ch(Sj Vb Vh Vw Wc Wd) Wh(aH Cu Cw lv Ld Pd) Ry(Cq Dc lj Kd Nb) Lp(bP Dd Kd Pc Ur) Yl(bP Ib lj Oe Pc) Ho(Bg Kj Ua Ur) Rz(aG bP Oe Ri) Gc(Ri Ua Uv) Vz(Ic lj Oe) Ji(Uw Vh Wm) Wg(Bn Ib Nv) Ke(De Kf Pb) Wd(Bg Pb) Rv(bP Ua) Cvkl GbPb HlSr IbTl IjUw WbaU WcUr RxVt RuPc VwbP} Ir{Ok(Fp Fr Hq Hu Hv Hw Hx Ih Ii Ij Il In Io Iq Is It Iu Iv Jg Jh Jk Jl Jm Jn Jq Jr Js Jt Lh Lj Lu Lv Lw Lx Ly Lz Ma Mb Mc Md Me Mf Mg Mh Mi Mj Mk Ml Mm Mn Mp Mr Ms Mt Mu Mv My Mz Na Nb Nc Nd Ne Nf Ng Nh Ni Nj Nk Nl Nm Nq Nr Nt Nv Nx Ny Oh Oi Om On Pa Pc Pd Pe Pf Pg Po Pz Qa Qb Qc Qd Qe) On(Fp Fr Hq Hv Hw Hx Ih Ij Il In Io Iq Is It Iu Iv Jg Jh Jl Jm Jn Jq Jr Js Jt Lh Lu Lv Lx Ly Lz Ma Mb Mc Md Me Mf Mg Mh Mi Mj Mk Ml Mm Mn Mp Mq Mr Ms Mt Mu Mv Mw Mx Mz Na Nb Nc Nd Ne Nf Nh Ni Nj Nl Nm Nn Nq Nr Nt Nv Ny Oh Oi Om Pa Pc Pd Pe Pf Pg Po Pz Qa Qb Qc Qd Qe) Jg(Fp Fr Hq Hu Hv Hw Hx Ih Ii Ij Il In Io Ip Iq Is It Iu Iv Jk Jl Jm Jn Jq Js Jt Lh Lj Lv Lx Ly Lz Ma Mb Mc Mf Mg Mh Mj Ml Mm Mn Mr Ms Mt Mu Mv Mw Mz Na Nc Nd Ne Nh Ni Nj Nk Nm Nn Nq Nt Nu Nx Ny Oh Pa Pc Pd Pe Pf Pg Pz Qa Qb Qc Qd) Oz(Aa Fp Hu Hv Hw Ih Ij Ik Il In Io Iq Is It Iu Iv Jh Jl Jn Jo Jq Js Lh Lj Lu Lv Lx Ly Lz Mc Me Mf Mg Mh Mq Mr Ms Mt Mv My Mz Na Nb Nd Ne Nf Ng Nh Ni Nj Nk Nq Nr Ns Nv Ny Of Oh Oi Om Oy Pa Pb Pc Pe Pg Po Qa Qc) Ma(Fp Fr Hq Hr Hu Hv Ih Ii Ij Il In Io Ip Iq It Iu Iv Jk Jl Jn Jq Js Jt Lh Lj Lx Lz Mc Mf Mg Mh Mi Mj Mm Mn Mp Mr Ms Mt Mw My Mz Nd Ng Nh Ni Nj Nk Nm Nn Ns Nt Nu Nx Oh Oi Pa Pc Pe Qa Qb Qc Qd) Jp(Fr Hv Hw Hx In Io Iq Is Iu Iv Jh Jk Jl Jm Jr Js Lh Lu Lv Ly Lz Mb Mc Md Me Mf Mg Mk Ml Mq Mr Mt Mu Mv Mx Na Nb Nc Nf Ni Nj Nl Nq Nr Nv Ny Om Pa Pd Pe Pf Pg Po Pz Qa Qb Qd Qe) Mw(Fr Hq Hu Hw Ih Ii Ij Il In Io It Iv Jk Jn Jo Jq Js Jt Lh Lj Lv Lx Ly Mf Mh Mi Mj Mm Mn Mp Mr Ms Mt Mz Nd Ne Ng Nh Nj Nk Nm Nn Ns Nt Nu Nx Of Oh Oi Pc Pf Qc Qd) Pb(Aa Fp Hr Hw Ih Ik Il In Io Iq Is It Iv Jh Jl Jn Jo Jq Js Lh Lj Lv Lx Mg Mh Mq Mr Ms Mt Mz Nb Nd Ne Ni Nk Nq Nr Ns Nv Ny Of Om Oy Pa Pc Pe Pf Pg Po Qa Qd) Lw(Fp Fr Ih Ij Ik Il In Io Ip It Iu Iv Jn Jo Js Jt Lh Lj Lx Mf Mh Mi Mm Mn Mp Mr Ms Mt My Mz Nd Ni Nk Nm Nn Nq Ns Nt Ny Of Oi Pa Pc Pe Pf Qc Qd) Oc(Fp Hr Ih Ik Il In Iq Is It Iv Jh Jl Jn Jq Js Lh Lj Me Mg Mh Mi Mj Mr Mt Mz Nb Nd Ni Nk Nq Nr Ns Nv Ny Oh Oy Pa Pc Pe Pf Po Pz Qa Qb) Og(Aa Hq Hv Hw Hx Ii Iu Jk Jr Lu Ly Lz Mb Mc Md Mf Mj Mk Ml Mq Ms Mu Mx My Na Nc Ne Nf Ng Nh Nj Nl Nx Of Oi Pd Pz Qe) Nt(Fr Hr Hu Ih Ii Ij Il In Io Ip It Jq Jt Lj Ly Mh Mi Mm Mn Mp My Mz Na Nd Ne Nh Nk Nn Ns Nu Of Oi Pc Qc Qd) Mi(Fr Hq Hr Ih Ij Il In Io Ip Iu Jn Jo Jt Lj Lx Ly Mh Mj Mm Mn Ms My Mz Nd Nk Nm Nn Ns Nu Of Oy Pc Qd) Nu(Fr Hr Ih Ij Il In Io Ip It Jn Jo Jq Jt Lj Lx Ly Mh Mm Mn Mp Mz Nd Nk Nm Nn Ns Of Oi Oy Pc Qd) Jj(Hq Hv Hw Hx In Iu Jr Lu Ly Mb Md Mf Mk Ml Mq Mu Mv Mx My Na Nb Ne Nf Nh Nl Nx Of Oi Pd Qe) Ip(Fr Hr Ih Ij Il In Io It Iv Jn Jo Jq Js Jt Lj Lx Ly Mh Mm Mp Mz Nd Nk Nm Nn Ns Of Pc Qd) Jt(Fp Fr Ii Ij Ik In It Iu Iv Js Lj Lx Mh Mj Mm Mn Mp Ms My Mz Na Nk Nn Ns Of Oy Qd) Oy(Aa Hr Ih Ij Ik Io Jn Jq Js Lh Lx Mg Mt Mz Nd Nm Nq Ns Nv Om Pc Pe Pf Pg Qd) Fr(Hr Hu Ih Ii Ij Il It Jn Jo Mh Mm Mn Mp My Mz Nd Ng Nk Nm Nn Ns Of Oi Pc) Mn(Hr Ij Ik In It Jo Jq Lj Mh Mm Mp Ms My Mz Nd Nk Nm Nn Ns Of Oi Pc Qd) Ik(Fp Hr Iv Jn Js Lh Lj Lv Lx Mg Mm Mp Mt Mz Nm Nn Ns Om Pc Pf) Mp(Hq Hr Ij In Io Iu Jn Jo Jq Lj Mk Mz Nk Nm Of Pd Qc Qd) Nn(Hr Hu Ij Io Lj Mf My Mz Nk Nm Ns Oi Pc Qd) Mm(Fp Hr Ih Ij Iu Jn Jo Lj My Mz Nk Ns Of Qd) Hr(Hv Ij In Jo Lx Mr Nb Nm Om Pe Qa Qd) Ij(Hu In It Jo Lj My Of Pc Qd) Qd(Il Nk Ns Pc) Mh(Lx Mt Mz) Of(Mt Nm Om) Va(Bo dI Ld) Nq(Hu My) CxmS NmJo MtZw MyJh NdHq YdKe UhbN} Jj{Js(Fp Hr Hu Hv Hw Hx Ii In Io Iq Is Iu Iv Jh Jk Jl Jo Jq Jr Lu Lv Lx Ly Lz Mb Mc Md Me Mf Mg Mh Mi Mj Mk Ml Mm Mp Mq Mr Ms Mt Mu Mv Mx My Na Nb Nc Nd Ne Nf Ng Nh Ni Nj Nk Nq Nr Ns Nv Oe Of Oh Oi Om Oy Pa Pc Pd Pe Pf Pg Po Pz Qc Qe) Ok(Fp Fr Hr Hu Hv Hw Hx Ii Ik In Io Iq Is Iu Iv Jg Jh Jk Jl Jo Jq Jr Lh Lu Lv Lw Lx Ly Lz Ma Mb Mc Me Mf Mg Mh Mk Mm Mn Mq Mr Ms Mt Mu Mx My Mz Nb Nc Nd Ne Ni Nj Nk Nl Nm Nq Ns Nv Nx Ny Of Oh Oi Om Oy Pa Pc Pf Po Qe) Qd(Fp Fr Hr Hu Hv Hw Ii In Io Iq Is Iu Iv Jh Jk Jl Jo Jq Lh Lj Lv Lx Ly Lz Mb Mc Me Mf Mg Mh Mj Mm Mp Mr Ms Mt Mz Nb Nc Nd Nf Ng Ni Nj Nk Nq Nr Ns Nv Nx Ny Of Oh Oi Om Oy Pa Pc Pe Pf Pg Po Qa Qb Qc Wm) Jt(Hq Hu Hv Hw Hx Ii Ik In Io Iq Iu Jh Jk Jo Jq Jr Lu Lv Lw Ly Lz Mb Mc Md Me Mf Mg Mk Ml Mm Mq Mr Ms Mt Mu Mv Mx My Nb Nc Nd Ne Nf Ng Nh Ni Nj Nk Nl Nq Ns Nx Of Oh Oi Om Oy Pa Pc Pd Po Pz Qe) Ih(Aa Hq Hr Hu Hv Hw Hx Ii Ik Il In Iq Is Iu Iv Jh Jk Jl Jm Jr Lu Ly Lz Mb Mc Md Me Mf Mh Mj Mk Ml Mq Ms Mt Mu Mv Mx My Na Nb Nc Nd Ne Nf Nh Ni Nj Nl Nx Of Oh Oi Oy Pa Pc Pd Pf Pz Qb Qe) Qa(Fp Fr Hr Hu Ii Il In Io Is It Iv Jl Jm Jo Jq Lh Lj Lv Lw Lx Lz Mc Me Mf Mg Mi Mm Mp Mr Ms Mt Mz Nb Nd Ng Ni Nj Nk Nn Nq Nr Ns Nv Ny Oh Om Oy Pa Pc Pe Pf Pg) Jg(Fr Hu Hv Hw Ii Ik In Iq Iv Jl Jo Jp Jq Jr Lh Lv Lw Lx Lz Ma Mf Mh Mj Mn Mp Mr Ms Mt Mx My Mz Nb Nc Nd Ng Ni Nm Nn Nq Ns Nu Nv Ny Of Oh Oi Oy Pa Pc Pf Po Qe) Nt(Fp Fr Hv Hx Ii Ik Il Io Iu Iv Jk Jl Jq Lw Lx Ly Mb Me Mi Mm Mp Mt Na Nc Ni Nj Nn Ns Nu Nv Oe Og Om Oy Pc Pe Pf Pg Po Pz Qe) Ip(Aa Fp Fr Hv Hw Ii Io Iq Is Iv Jk Jl Jo Jq Lw Lx Lz Mg Mp Mr Mt Mz Nb Nc Ni Nm Nn Nq Og Om Pa Pc Pe Pf Pg Po Qc Qe) Jn(Fp Fr Ii Il It Iv Jk Jl Jo Jq Lj Lw Lx Mg Mi Mm Mp Mr Mz Nd Nn Nq Nr Nv Ny Og Om Oz Pb Pe Pf Pg Po Pz Qb Qc Qe) Jp(Fp Iq Is Jo Jq Lh Lw Lx Ma Mi Mn Mp Mr Mw Mz Nm Nn Nr Nu Ny Pb Pe Pf Pg Po Qc) On(Fr Ii Jh Jk Jl Lu Mb Me Mj Mm Mq Mt Mx Na Nb Ne Nf Nh Nl Nq Om Pa Pd Pz) Mw(Ii Iq Is Iv Jo Jq Lh Lj Ma Mi Mn Mz Nm Nr Nv Ny Oz Pe Pg Qb Qc) Jm(Fp Fr It Jo Jq Lj Lw Lx Mi Mn Mp Mz Nn Nr Nv Ny Oe Og Om Pb Pg) Qb(Aa Fr It Jo Jq Lh Lw Mg Mi Mm Mn Mp Mz Nn Nr Nu Nv Ny Og Pb) Lj(Is It Jo Lh Lw Mg Mi Mm Mn Mp Nm Nq Nu Nv Ny Om Oz) Nm(Fp Il Is Iv Lh Mi Mn Mz Nr Nu Oz Pb Pe Pg Po) Ma(Fp Hv Ii Il Is Iv Jq Lh Mi Mz Nr Nu Pb Qc Qe) Oz(Aa Fr Is Jl Lx Mn Nr Nv Ny Pe Pg) Nu(Ii Is Jq Lh Mi Mn Mz Nr Nv Ny) It(Aa Jl Lx Mi Mn Mz Nr Nv Ny Om) Is(Fr Lh Mn Nr Oe Og Pb) Ny(Il Lh Lw Mi Mn Nr Pe) Aa(Nw Pb Qc) Nr(Mi Mn Mz) Lh(Lw Mi Mn) Cx(kP mS) Xa(aW aY) Nv(Og Pb) WmJi EqNn FrPb MiMn HpaW IjVa} Ok{Og(Fr Hq Hu Hv Hw Hx Ii Ik In Io Iu Jh Jk Jl Jo Jr Lh Lu Lv Lx Ly Lz Ma Mb Mc Md Me Mf Mg Mh Mj Mk Ml Mm Mn Mq Mr Ms Mu Mv Mx My Na Nc Ne Nf Ng Nh Ni Nj Nk Nl Nq Nv Nx Oe Oh Oi Oy Pc Pd Pf Pg Po Pz Qe) Ih(Fp Fr Hq Hu Hv Hw Ii Ij Ik In Io Is It Iv Jn Jo Jq Js Jt Lh Lj Lw Lx Ly Mc Mf Mg Mh Mi Mj Mm Mn Mp Mr Ms Mw My Mz Nd Ne Ng Nh Nk Nm Nn Nq Nr Nt Nx Ny Oh Oi On Pa Pc Pd Pe Pg Qa Qb Qc Qd) Pb(Hu Hv Hw Hx Il In Io Iq Iu Iv Jh Jl Jm Jo Jq Lh Lv Lw Ly Lz Mc Mf Mg Mh Mk Mm Mq Mr Ms Mt Mx My Nb Nc Nd Ng Ni Nk Nm Nq Nv Nx Ny Oh Oi Om Oy Oz Pa Pc Pf Po Qc Qe) Hr(Fr Hv Hw Hx Ik Il In Io Iq Iu Iv Jg Jl Jm Jo Jq Lh Lw Lx Lz Ma Mc Mg Mh Mk Mn Mp Mr Ms Mt My Nb Nc Nd Ni Nm Nn Nq Nt Nv Ny Oe Of Oi Om Oy Pa Pc Pe Pf Pg Po Qe) Oz(Fp Fr Hv Io Iq Is Iv Jg Jl Jo Jq Jt Lh Lw Lx Ly Lz Ma Mg Mh Mn Mp Mr Ms Mt Mw Mx My Mz Nc Nd Ng Nm Nn Nr Ns Nt Nu Nx Ny Oi On Oy Pa Pc Pf Pg Qc Qe) Qd(Fp Hu Hv Ij Io It Iv Jg Jn Jo Jp Js Jt Lj Lw Lx Ly Lz Ma Mc Me Mf Mh Mi Mj Mm Mn Mp Ms Mw My Mz Nc Nd Ni Nk Nn Nq Ns Nt Nu Nx Ny Oi On Pc Qb Qc) Ip(Fp Fr Hu Ij Ik Il Io Is It Iv Jg Jn Jo Jq Js Jt Lw Lx Ly Ma Mg Mh Mi Mn Mp Ms My Mz Nc Nd Ni Nn Nr Ns Nt Nu Nx Ny Oe On Pc Pe

Figure 36 Continued

Figure 36 Continued aY(Vz Yl) BgWd EqQy Thli NuWh LxHq MwUw ItJt WfKi VcbM UxbJ} Vi{Lj(aF aK aU aW AX bC bE bG bJ bW cC cN CO cP cS cV Cx
cY De dI dJ DK dM Ez Gc Ho Iu Kc Kd Kg Kj Kq Ld Mg Mi Mj Mk Mm Mp Mt Mu Mv Na Nn Nq Oz Pa Pc Pd Pj Qn Qy Rc Rv Rx St Uf Uk
Ur) cV(Af aO Bn Bo Ct CX Ed Ef Ex Hc Ib Ic Je Lu Mf Nv Nx Oe Of Oi Ow Oz Qn Rc Rj Rt Rx Sr Uu Va Vp Vt We Wf Wh) Ch(aW aX bC
bJ bW Co cS Ef Gc Jh Kc Kq Mg Mi Mm Mq Mt Mu Nn Nq Pd Pj Qy Uf) aO(aW bG Bn Bo cU Gp Ib Je Ld Lx Mf Mq Oe Ow Oz Pf Rj Rx Sh
Sr Uh Ur Uu Wf) Bg(bC bJ bW Co Cx De Gc Kc Kg Ld Mg Mi Mt Mu Mv Nm Nn Nq Om Qy Ue Wd) Nn(Aj aX Dg Ed Eq Hc Iz Kl Ng Of Qu
Rz Sh Ss Uu Wf) aF(aZ cQ Eq Gl Gp Ki Lx Ml Ow Pf Rz Ss Uu Vb Vt) aW(Aj Cs Eq Fp Hc Kg Kj Kl Kz Oy Rz Sh Uu Ux Vo) Yd(cQ Gc Ji Kc Ld Ow Oz Pc Pj) Af(Gc Kq Mi Mw Om Ow Qa Vt) Hc(aN bJ Cx Mw Qg Qy Rx Sr) aY(bB Ld Mk Ow Pf Ur) Dk(Ke Ld Qa Qe Vt) Sr(cQ Ii Oz Va Wf) Qn(Nw Oa Qa Sh Vt) Aj(bJ Kc Kd Qy) Bn(Fn Gc Jn Sh) Nx(Ke Ld Nq Ow) Uv(Gc Ld Mq Pj) Wf(Cx Mw Rx) Of(Ho Kc Om) Ow(dF Lv Zw) Oz(Bo Ed Pe) Eq(dK Qy) Fw(Ld Ur) Sh(Oe Pf) Uu(Mw Qy) CxOa GlKz IzKc QaaN SsbJ KdRt LpUr UpVt} Jt{Hr(Hu Hw Hx Ik Il In Iq Iu Iv Jg Jm Jo Jq Jr Lu Lv Lw Lz Ma Mf Mg Mh Mj Mk Mm Mn Mq Ms Mx My Na Nb Nc Nf Ng Ni Nj Nk Nm Nn Nq Nr Ns Nv Ny Oe Of Oh Oi Om Oy Pc Pf Pg Qe) Ip(Fp Fr Ih Ii Ik Il It Iv Jg Jn Js Lj Lx Ma Mg Mh Mi Mj Mn Mp Ms Mw My Mz Na Ng Ns Nt Nu Oe Of Oy Pc Qa Qb Qc) Lj(Fr Ih Ii Ik In It Iv Jg Jn Jo Js Lw Lx Ma Mi Mm Mn Mp Ms Mt Mw Mz Na Nd Nk Nn Nq Ns Nt Nu Ny Of Oy Pc Qb) Jo(Bb Fp Fr Ih It Jg Jn Js Lh Lx Ma Mi Mn Mp Mw Mz Nm Nr Nu Nv Ny Oz Qa Qb) Oz(Aa Fp Ih It Iv Jg Jn Js Lx Ma Mi Mp Mw Mz Nt Nu Oe Of Pe Pf Pg Qa Qb) Pb(Fp Ih Jg Jn Js Lx Ma Mi Mn Mp Mw Mz Nt Nu Nv Ny Oe Pe Pf Pg Po Qa Qb) Ih(Fp Fr It Jg Ma Mh Mi Mj Ms Mw Mz Nk Nt Nu Oy) Oy(Fp Fr Jg Jn Lx Ma Mp Mt Mw Pe Pf Pg Qa Qb) Oe(Fp Fr Is Jg Jn Js Lx Ma Mw Mz Nt Nu Ny) Of(Fp Jn Lx Ma Mi Mp Mw Mz Nd Nt Nu Qa Qb) Qb(Ik It Jg Ma Mj Ms Mz Nk Ns) Lx(Ii Mh Mj My Po) Aj(Bb Fr Mw Nw) My(Fr Jg Mt Nq) Ik(Fp Nt Qa) Fr(It Ng) Ns(Mp Nd) Mg(Jg Ma) Mj(Fp Js) Ms(Mw Mz) Yd(Ji Nw) CxnN NbRt NdHq NgJg UhUu} Yd{Ke(aW Ax bG bJ bN bU Cs cT Db Dr Fy Hf Hw Ih Jn Js Kq Kx Ld Lj Lx Lz Mg Mh Ml Mt Na Nb Nn Oa Oh Ow Pe Pf Pi Pj Ps Pz Qa Qx Ra Rf Ru Sr Va Vh Vq Zw Xa Wm Ti) Ji(aW aY Bb cP Cx Ed Fc Fw Ic Ih Is Jg Jk Jn Ks Mk Mt Mw Nb Nt Ny Oa Pc Pz Qa Qy Si Sr St) Ow(aF aO aX aY bF bR cG dH Dr Ed Eq Hb Hx Jk Jl Kq Nb Nw Ny Oz Pb Pc Pe Pi Ps Un Wb) Kq(aR aZ bL Ch CX dG Gn Gp Hf Is Lu Lx Mh Pf Pj Qb Rj Uh Vs Th) Ld(Dc Ed Fw Ih Is Jg Jn Ko Mt Nb Ny Pe Pz Qa Qc Qe Qh Sr St Uh) Mt(aM aX bV Ed Eq Hb Ki Lj Nw Or Oz Pb Pc Pj Uh Vt) Nw(aW Gc Jh Mv Nm Nn Oe Om Or Pj Qy Rx Sr) Qa(aG aJ aN Bn Bo Cx Dd Gc Hb Ic Pj Uh) Pe(aK aU Cx Gc Ha Mp Nq Oz Pc Ur Vt Wf) Gc(Iv Mv Mw Nn Oa Ry Ut) Nb(Mk Mp Nq Ou Pj Uh Un) Pj(Is Jl Jn Nv Oa Ut) Nn(aX aZ Ed Eq Hb) Is(Oz Pc Qy Un) Qy(Lh Lx Oh) Om(Aj Oy Pb) Uh(Cu Ni Ps) Ut(Hb Hc Oz) Sr(aG Ur) ChJh DdMq NtVt LxbJ MwOi PsRx PfaY} Jg{Ih(Fp Fr Hq Hr Hu Hv Hw Ii Ik Il In Is It Iv Jk Jl Jn Jo Jq Js Lh Lu Lv Lx Ly Lz Ma Mc Me Mf Mg Mh Mm Mn Mp Mq Mr Ms Mt Mv Mw Mz Nb Nd Ne Nh Ni Nj Nm Nn Nr Nt Nu Nx Ny Oh Pa Pc Pd Pe Pf Pg Po Pz Qa Qb Qc) Lj(Hu Ik Ip It Jn Jq Js Lh Lx Mw My Mz Nd Ng Nn Ns Nt Of Oh Oi Oy Oz Pb Pc Qa Qb) Of(Is It Jn Jq Lh Lw Lx Mp Mt Mw Nt Oe Om Oz Pb Pe Qc) Oy(Ip Is Jn Jq Lh Lw Lx Mp Mz Nb Pa Pf Pg Po Qa) Mi(Hq Hu Ik Ip It Jn Jo Js Mz Ng Ns Oe Oz Qb) My(Is Jn Jq Lh Lx Mp Mr Mw Nb Nq Qa Qc) Ng(Ip It Jn Lw Mp Mw Mz Nd Nt Nu Qa Qb) Oe(Fp Ip Is Jn Jq Lx Mw Mz Nd Nt Oz Pb) Pb(Fp Ip Jn Jq Js Lh Lw Mz Pe Qb) Qa(Hr Hu Ip Jo Lw Ns Oi Oz) Js(Hu Ik Ip Lw Ns Oi Oz) Qb(Hu Ik Lw Ns Oi Oz) Mz(Hr Ip) Ld(Va Zw) EdSh NnHu NsMp HrJq IpOz KeUu} Nb{Rt(aC aF Ao Ap aU aW aX Bb bC bE bJ bW cC cG cL CO cP cS Cu Cw Cx cZ Dd De dK Ef Ez Fi Gb Gc Ho Hv Hw Is Iu Jh Ji Jo Kc Kd Ke Kg Ko Kq Ld Ma Mg Mi Mm Mp Mt Mu Mv Na Nm Nn Nq Nw Om Ow Pd Pj Qy Qz Rz Ue Uf Un Vq Wd Ti) Tl(Af aJ aN aW Bn Bo bS CX Dk dM Ib It Jl Ld Ny Oe Oz Qn Qv Rj Rx Uh Ur Vp Wf) Eq(aW CO cS cZ Ez Jh Ld Mg Mq Mt Nn Pd Ue Uf Vq) Bo(Uw Ux Vh Vw Vz Wc Wd Ye Xa) We(aW cV Ke Kq Ld Mq Mw Nn Nq) Ld(Uw Ux Uy Va Vb Vh Vz Zw) Ur(Fc Fi Gh Gn Lp Si Uy Zw) Rx(aL cH cV Iv Lu Oa) Ti(Aj Kl Uc Uu Vs) Sr(Hl Ry Vz Yl Zw) Gc(Ed Up Us Uu) Wd(Aj De Kj Us) Zw(Ow Pe Po) Of(Fr Ma Vh) cV(Lp Wf Ye) Aa(Oz Qc) Mq(Uw Wh) Uh(bN Dr) Un(Ru Va) Us(Fi Rz) ArHo FdIv NhWf HlVq HrQa HbVa UxPj} Ed{Xa(Af aW Ba Bn bQ bZ cP cV cW CX DK Ez Gn Io Ld Mk Na Nj Nk Nn Oe Oi Oz Pc Qn Qv Rc Sh Vq Vt) Nn(Dr Du Eq Fi Gb Gd Gh Gn Hl Ho Ps Rt Rv Rx Rz Sh Ux Va Vz Wb Wf Yl Zw Ye Tl) Ld(Du Eq Fc Fi Gd Gh Gn Op Rt Ru Ux Va Vw Wc Zw Zx Ye Tl) Va(Ba Cu Ez Ji Mg Na Ni Nk Nw Ow Pd Vq) Ru(aG bH cV Cx dE Kq Kz Pa Vt) Dr(aQ CX Hq Ow Vt) Ps(cN CX Oe Oz Qn) Ba(Fi Gb Gd Lp) Gn(aM Mq Ni) Oz(Wd Wh Zw) Pd(Fc Fi Wc) Cu(Rt Wc) Eq(Ez Mq) Gd(Ni Ow) Sh(Ih Qt) Ye(Ez Mq) FiMg GcQw NiRt WdPb KeLh RvPf OpOw} Ih{Ma(Fp Hu Hv Hw Ik It Jn Jo Jq Lh Lj Lw Mh Mi Mr Ms Mw My Mz Ng Nk Nm Nn Ns Nt Nu Of Oi Pc Pe Qa Qc) Mi(Fr Hr In Ip Jn Lj Ms Mw Mz Nk Nm Ns Nt Nu Ny Oe Of Oy Qc) Ip(Fr Hr Il Jq Lh Lw Mm Mn Mp Mw Mz Nk Nn Nu Oe Oy) Nt(Fr Ik Lj Lw Ly Mw Mz Nd Nk Ns Oy Pb Qc) Oe(Lx Mm Mw Nu Ny Om Qa) Va(aG aZ bM Cx Hb Ld Ur) Hr(Hw Jo Jq Lh Mz Qa) Nu(Fr Jq Lw Oz Pb) Aa(Oy Oz Pb Qc) Fr(Lw Ns Oy) Sh(Jv Sr) Lj(Lw Mm) Uu(Gc Rx) MtMy MwOz ZwLd LhPb} Qa{Hr(Jl Jq Lh Lw Lx Ma Mn Mw Mz Nt Oz Pa Pb Pc) Af(Ux Vb Vh Vw Vz Wb Yl Zw Zx Tm Tl) Pb(Aa Fr Lh Lw Mi Mn Mw Mz Nk Nt) Uh(Cw Ha Ii Jo Lh Nk Ou Uu Vs) Zw(aN BN Cx Kr Qv Us Uu) Oz(Aa Fc Fr Ma Mi Nt Oe Rt) Bn(Vb Vh Vz Wb Wc We) aN(Ux Wb Wd We Wh Zx) Ma(Ik Ip Oe Of Oy) Wf(aY bJ Mw Nu Us) Mi(Ik Oe Of Oy) Rt(dG Ex Oi Pc) Wb(aW Dk Qn) Oe(Ik Nt Nu) Aa(Oi Oy) Aj(Bb Rx) Cx(We Zx) Mt(My Of) Ur(Lp Ru) Us(Rv Sh) aY(We Ye) BbJo DrQn FcUu NsNd NtIk IpOy RzUv VabM} Nn{Eq(aE Af aS aX aY aZ Ba bE bH bJ bM BO bQ cB cE Co Cu Cx cZ dD dI Dk dL Dr Du Ef Em Fn fR Hl Hp Hu Ib Iz Jd Je Jf Jh Jk Jn Jy Kq Ld Lx Mh Mr Ms Mt Mu Mv Mw Mx Ni Nj Nq Nt Nu Nv Nw Ny Ps Ql Qy Rc St Ua Un Uo Wb Wd Ti) Wb(aX Kl Ng Qu Sh Ss Vt) Dr(Kl Qu Sh Ss Vb Vt) Aj(Hp Ps Vb Wd) Aa(Oz Pb Qc) Hp(aZ Kl Ng) aX(Va Vw Zw) Sh(aE Qy) Ke(De Vs) Kl(Ps Vw) AdnD DgPs MwWf ZwUn KdRt} Oz{Aa(Fp Fr Hr Hu Hv Is It Iv Ji Jm Jn Jr Js Lu Lv Lx Lz Mi Mj Mk Mr Mt Mw Nc Nu Of Oi Pe Pf Pg Po Qb Qe) Ip(Fp Fr Iv Jn Jq Lh Lj Lw Lx Lz Ma Mn Mp Mr Mt Mw Mz Pe Pf) Mi(Fr Jn Js Lx Ma Mn Mw Mz Nt Ny Qb) Ps(aZ Fw Lj Mh Ml Mx Oa Pe Us Va Vs) Fr(It Jn Jq Js Lj Nt) Lj(Lw Ma Mp Nt) Sr(Rt Vh Xa) nI(nC nH nL) Fw(Sh Sj) Nt(Mw Vb) Ma(Js Qb) Mt(Eq My) DuPe FcIv LwJs WbOw XacV OaVw} Va{Ps(Af aJ aR aZ bM Bn Bo bS CX dB dG Dk Hc Hu Ib Ki Oe Oi Pc Qn Qt Qw Rj Rx Uh Uu Vp Vq Vt Wf Ye) Sr(aG aN bM bO cF Dr Or Uo Uv Vt Vz Yl) Ld(Al aX Bb Dc Fw Il Jm Kd Lp St) Un(aN aY cD Fc Fi Fw Jm Ow Pa Ru) Cx(Hv Hx It Ke Pe Xa) aN(Ji Ke Nw Pe Vt) Ch(Ef Kq Qy Ut) Nw(aD aY Us) Af(Om Pe) Qy(Eq Vt) Rm(Bo dI) NtVt MtaX HbJn IsdD IuaZ StdI KdQm KeaD KqUv NyVq OwdL PebM} Pb{Aa(Hr Ip Is It Iv Ji Js Lx Lz Mi Mr Mt Mu Pe Pg Po Qb Qc Qe) Ip(Fr Jn Jq Js Lh Lj Lw Lx Ma Mn Mr Mw Mz Pe) Mi(Fr Jn Js Lh Lj Lx Ma Mn Mw Mz Nt Ny Qb) Nt(Fr Js Lj Ly Ma Mw Mz Nd Qb) Ma(Jn Js Lh Lj Mz Pe Qb) Ke(Af Cx Ii Mm Nx Us Uv) Fr(It Jn Jq Js Mz Oe) Lj(Lh Lw Mp) LwJs IsOe JnLh UhbN nHnI} Mw{Wf(aW Ax bA cT dK Em Fy Jn Lx Mh Nr Ow Pe Pf Ru) Sh(aN aW bA Gp Il Nd Oe Oi Ow Pa Pf Ru) Ru(Af aZ Ch Hc Qw Vt Wh) Ip(Jq Js Mi Nt Oy) Eq(Ez Ld Mt Ow) Mi(Hq Ik Lj) Ch(Vb Vw) Nt(Ik Lj) Hr(Jq Mz) Wh(cT Ml) Uh(Bg Oy) Uu(Gh Vz) DrVs LwLj MhZw MtMy LdUy UwPe} Lj{Mi(Hq Il Ip Jn Jq Lw Ma Mm Mn Mz Nt Nu Oy) Du(Cu Iv Kq Ld Mq Mt Pd) Lw(Ip Jn Js Ma Nt Nu) Qy(Dr Gh Yl Ye Tl) Nt(Ik Ip Ma Nd) Wb(Gc Mg Ow Si) Ma(Ik Ip Jq) Ld(Vb Vw Zw) Hr(Jq Mz) Ps(dI Pc) DrKc NsMp MhMt VzSr ZwJh RxNy RtPi} Oa{Rx(bM bO dI Dr Du Hp Hx Ld Mu Ni Ny Uo Ur Wb) Gc(Af bM bO Cq dD dI Dr Iq Uo Wb) Rt(Ho Ji Kd Mi) Cx(Uz Vw Xa) Zw(Ic Mt Sr) Wf(Hu Jh Qy) Fc(Cv Ur) Qy(Sh Ye) Pj(Dr Wb) AfVw HuYc} Uh{bN(Ad aM As Bn Cp Cq Cw Dc Hw Id In Iv Ji Kn Kp Kq Kr Mz Nf Ny Om Pi Pk Ra Rj Sr Tv Up Vp Vv) Uu(It Jq Ke Kq Lw Na Sr) Ke(Af Jo Kf Lh) Kq(De Uv) DraW} Cx{nN(Ad Aj Bg Cv Dc Iz Jo Kj Kl Kn mS Nm Of) mU(Ad Aj Ef Iz Kj Of) mI(Ad Aj Kj mS) mS(aJ aW kI) Pe(Vc Wf) mZ(kG Ld) KeLh KjnL LpUr NxnI} Aa{Qc(Hr Hu Ip Is It Iv Jo Nk Nw Of Oi Pa Pc) Oy(Ip Js Lx Mt Pe Pf Pg Qb Qe) Nw(Hr Jm Jo Of Pc) Ip(Hr Jo Pc) Oi(Qb Qe) MyJh} Ke{Nx(Ad Bg bL bN De dK Jo Kj Ld Lh

Figure 36 Continued

Mm Uv Vo) Lh(Ml Qn Uu Uv Vo) Ru(Af Dr Jo Wb) Il(Jo Ph Uu) Uv(De Kf Ph) Vo(bN De) DraW UuPh} Ow{Wb(aF aO cV cX Kl Lv Oi Pc Qn) Dr(An aY cX Nx Oi Qn) Zw(Hp Nu Qy Uo) Af(Eq Ho Vh) Qy(Eq Sh Ux) Kl(Gb Hp Vw) EqHu RxNy} Pe{Du(aO cA cK Gh Hc Nd Vc Wf) Wf(aN aY Bn Hu Kx Lv Qy) aN(Gh Vc Wh) BnVc MzHr ZwLd WhQy PsPc LpUr YlaY} Kq{Ru(Af Aj Bg Kl Of Tn) Nx(Eq Uw Wd Wf Wh) Ch(Ps Rx Wc Wd) Lp(Bg Ur Uu) De(Aj oH) Rx(aF Uv) AfUy BgTm} aW{Dr(Hb Ld Or Qg Qx Tz Vt) Wb(Cs Ld Ml Mq Qx) Ny(Eq Fi Ry Rz Yl) CsDu EqNv XaLd KgmS KlPs} Ip{Nt(Jo Jq Lw Ly Mz Nd Of Oy Qc) Mi(Hq Il Jn Oy) Js(Il Jo Lw Oy) MtMy HrHw} Jn{Rx(bJ Hp Mq Nc) Fc(Ur Uu) Mi(Hq Ik) Wf(Nj Qy) AjnN FrOe MtMy MzHr ZwUf UuUx} Lp{Ur(cR Fp Iv Jl Ld Mq Mv Nw Ps Ql Sr) Ld(Uv Zx) IvaY QyUu} Dr{Ru(Ji Mk Mq Rh) Kd(Mk Mq Tz) Th(Ji Mk) Sr(aU aV) Pf(Sh Vt) FwLd} Js{Lw(Fr Hr Nu Oy) Ma(Jo Of Oy) Fr(Oe Oy) Nt(Ik Jo) BbJo MtMy HwjE} Eq{Mt(aN aX Qy St) Mq(Bb Fw Ph) Qy(Nr Oh Pf) Mu(Nr Pf) UtaF} nN{Aj(Af bJ Bn De nI) Jo(aF bU cH nI) nI(Cv Nm) AfhB HbKj} Ps{Uu(cX Hu Oe Qy Sr) Us(Ho Kd) ExMl SrRx NyVp OeVs OiaY} Hr{Jq(Fr Jl Lh Mi Nt) Mz(Fr Jo Nt Qb) HvLh} Wb{Pf(aF aO cV Hc) Mk(Pa Ru) FwLd JiRu SraU OhaF} Rt{Jm(Cu Ho Hv) Kd(Hw Mq Ql) Is(Dd Sr) MiQb} Xa{Qy(Ch Uu) FcOi SrPc LdaY NxUn VtaN} Ru{Aj(Ef Jh) Mr(Ld Pa) EmLd NuNw IvUr} Uu{Gc(Hu Ny St) Qy(Fd Ho) FwWd} Jh{Ch(Rx Uy Tm) Mi(My Oy)} Oe{Is(Fr Nt Nu) Qb(Ma Nt)} Mt{aX(Op Zw) AfWe FrWc} Rx{Ny(aF Ld Mq Ur)} aN{Fp(Fi Ho Ti) AjmI} Wm{Ji(Jo Nk Qc)} Ma{MiHq MzOf QbOy} Sr{HuSh SfUv ZwUr} Kd{We(Mv Ql) MqUy} Nt{Ik(Is Qb)} Ho{AfPf LdUv} Iv{ThLd VbaY} Qy{MxSh ZwOh} dM{bCjQ hAjK} nI{CvQc OymI} DdMqUy FcRmUr GlWfUt NsLxMh NuTmNw LtNxUn

Unconstrained panels with 2 analytes, where 1.0E-8 >= 'model p-value' > 0. Contains 795 panels of 121,819 total panels evaluated. : Im(AA Et Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Ye) Et(aA Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ji(aA Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nw(aA Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) No(aA Fp Fr Hq Hr Hu Hv Hw Hx Ih Ii Ij Ik Il In Io Ip Iq Ir Is It Iv Jg Jh Jj Jl Jm Jn Jo Jp Jq Jr Js Jt Lh Li Lj Lu Lv Lw Lx Ly Lz Ma Mc Md Me Mf Mg Mh Mi Mj Mk Mm Mn Mp Mr Ms Mt Mu Mv Mw Mx My Mz Na Nb Nc Nd Ne Nf Ng Nh Ni Nj Nk Nm Nn Nq Nr Ns Nt Nu Nx Ny Oe Of Og Oh Oi Ok Om On Oy Oz Pa Pb Pc Pd Pe Pf Pg Po Qa Qb Qc Qd) Li(aA Hr Hu Hv Hw Ih Ij Ik Il In Io Ip Ir Is It Iv Jg Jj Jn Jo Jp Jq Js Jt Lh Lj Lw Lx Ly Lz Ma Mf Mh Mi Mm Mn Mp Mr Mt Mw My Mz Nb Nd Nf Ng Nk Nm Nn Ns Nt Nu Ny Oe Of Og Oh Oi Ok On Oy Oz Pa Pb Pc Pe Pf Pg Qa Qb Qc Qd) aA(Fp Fr Ih Ij Io Ip Iq Ir Is It Jg Jm Jn Jp Js Jt Lh Lj Lw Lx Ma Me Mg Mi Mm Mn Mw Mz Nj Nm Nr Ns Nt Nu Ny Oe Og Ok Om On Oz Pb Po Qa Qb Qc Qd Qe) Ir(Fr Ip Jg Jj Jp Jt Lw Ma Mi Mm Mn Mp Mw Nn Nt Nu Oe Og Ok On Oy Oz Pb) On(Hu Ih Ip It Jj Jt Lj My Ng Ns Oe Of Og Oy Oz Pb Qd) Ok(Hr Ih Ij Ip It Jj Jp Js Lj Of Og Oz Pb Qa Qd) Qd(Ij Ik Ip Jg Jj Jp Jt Oe Og Oz Pb) Jj(Ih Ij Jg Js Jt Nt Qa) Jp(Ih Ij It Jt Lj Mi Oz) Jt(Hr Ip Lj Og) Ij(Mi Og Pb) Aa(Oz Qc) Ih(Jg Ma) JgOg Unconstrained panels with 2 analytes, where 1.0E-7 >= 'model p-value' > 1.0E-8. Contains 413 panels of 121,819 total panels evaluated. : aA(Hr Hu Hv Hw Hx Ii Ik Il In Iu Iv Jh Jj Jk Jl Jo Jq Lu Lv Ly Lz Mc Mh Mj Mk Mp Mr Ms Mt Mx My Nb Nc Nd Ng Ni Nk Nn Nq Nv Nx Of Oh Oi Oy Pa Pc Pe Pf Pg Pz) Ir(Aa Fp Hr Hu Ih Ij Ik Il In Io Iq Is It Iv Jh Jn Jo Jq Js Lh Lj Lv Lx Mg Mh Mr Ms Mt Mz Nd Ne Nj Nk Nm Nq Ns Nv Ny Of Oh Om Pa Pc Pe Pf Pg Qa Qc Qd) Li(Aa Fp Fr Hq Hx Ii Iq Iu Jh Jk Jl Jm Jr Lu Lv Mb Mc Md Me Mg Mj Mk Ml Mq Ms Mu Mv Mx Na Nc Ne Nh Ni Nj Nl Nq Nr Nv Nx Om Pd Po Pz Qe Yd) On(Fp Hr Hv Ij Ik Is Iv Jk Jn Jo Jp Jq Js Lw Ly Ma Mh Mi Mp Ms Mv Mw Mz Nd Nk Nm Nn Nt Nu Nx Oi Ok Pc Pe Qa Qb Qc) Qd(Aa Fr Ih Il It Iv Jn Jq Js Lh Lj Lw Lx Ma Mi Mm Mn Mp Mr Ms Mt Mw Mz Nd Nm Nn Ns Nt Nu Ny Of Oy Pa Pc Pe Qc) Ok(Fp Fr Io Is Iv Jg Jn Jo Jq Jt Lw Lx Ma Mi Mn Mp Mw Mz Nd Nn Nr Ns Nt Nu Ny Oe Oy Pc Pe Qb Qc Qe) Jt(Aj Fp Fr Ih Ij It Jg Jn Jo Js Lx Ma Mi Mw Mz Nt Nu Ny Oe Of Oz Pb Qa Qb Qc) Jp(Aa Fp Ip Is Jj Jn Jq Js Lh Lw Mp Mw Mz Nm Nn Ns Nt Oe Og Oy Pb Qa Qb Qc) Ij(Fr Hu Ih Ik Ip Jg Lj Lw Lm Mm Mp Mw My Oe Of Oy Oz Qa) Aa(Et Hr Ih Ip Jj Js Nw Og Oy Pb Pc Qa Qb Qe) Jj(Ip Is Jm Jn Lh Ma Mw Nm Nv Ny Qb) Ih(Fr Ip Lw Mi Mm Mw Nt Nu Og Oz) Qa(Hr Ip Jg Lw Ma Mi Oe Og Oz Pb) No(Iu Jk Mb Ml Mq Nl Nv Pz Qe) Jg(Ip Js Lj Lw Mi Mz Oe Of Qb) Ke(Kf Lh Mm Nx Pb Uu Uv Vo) Ip(Js Mi Mw Nt Og Oz) Js(Fr Lw Ma Og Oz) Lj(Lw Ma Mi Nt Vi) Mi(Jn Mw Oz) Og(Is Nt Om) Eq(Im Nn) WmJi ImSh Unconstrained panels with 2 analytes, where 1.0E-6 >= 'model p-value' > 1.0E-7. Contains 908 panels of 121,819 total panels evaluated. : Aa(Fp Fr Hq Hu Hv Hw Hx Ij In Iq Is It Iv Jg Jh Ji Jk Jl Jm Jn Jo Jq Jr Jt Lh Lj Lu Lv Lx Lz Ma Mg Mi Mj Mk Mn Mp Mq Mr Ms Mt Mu Mw My Mz Nb Nc Nd Nf Nj Nk Nl Nn No Nq Nr Ns Nt Nu Ny Oe Of Oi Ok Pa Pe Pf Pg Po Pz) Qd(Bb Fp Hq Hr Hu Hv Hw Hx Ii In Io Iq Is Iu Jh Jk Jl Jm Jo Jr Lu Lv Ly Lz Mb Mc Md Me Mf Mg Mh Mj Mk Ml Mq Mu Mv Mx My Na Nb Nc Ne Nf Ng Nh Ni Nj Nk Nl Nq Nr Nv Nx Oh Oi Om Pd Pf Pg Po Pz Qa Qb Qe Wm) Ok(Hq Hu Hv Hw Hx Ii Ik Il In Iq Iu Jh Jk Jl Jm Jr Lh Lu Lv Ly Lz Mb Mc Md Me Mf Mg Mh Mj Mk Ml Mm Mq Mr Ms Mt Mu Mv Mx My Na Nb Nc Ne Nf Ng Nh Ni Nj Nk Nl Nm Nq Nv Nx Oh Oi Om Pa Pd Pf Pg Po Pz) On(Fr Hq Hw Hx Ii Il In Io Iq Iu Jg Jh Jl Jm Jr Lh Lu Lv Lx Lz Mb Mc Md Me Mf Mg Mj Mk Ml Mm Mn Mq Mr Mt Mu Mx Na Nb Nc Ne Nf Nh Ni Nj Nl Nq Nr Nv Ny Oh Om Pa Pd Pf Pg Po Pz Qe) Jp(Fr Hr Hu Hv Hw Ik In Iq Iu Iv Jg Jl Jm Jo Jr Lu Lv Lx Lz Ma Me Mg Mh Mj Mm Mn Mq Mr Ms Mt Mx My Na Nb Nc Nd Nf Ng Ni Nj Nk Nq Nr Nu Nv Ny Of Oh Om Pa Pc Pe Pf Pg Po Qe) Jt(Hu Hx Ii Ik In Io Iq Is Iu Iv Jl Jm Jq Lh Lu Lv Lw Ly Lz Mf Mg Mh Mj Mm Mn Mp Mr Ms Mt Mx My Na Nb Nc Nd Ng Nj Nk Nm Nn Nq Nr Ns Nv Oh Oi Om Oy Pa Pc Pe Pf Pg Po Qe) Ij(Aj Fp Hr Io Is It Iv Jl Jn Jo Jq Js Lh Lx Lz Ma Mn Mr Ms Mt Mz Nd Ng Nm Nn Ns Nt Nu Ny Oh Pa Pc Pe Po Qb Qc Uh Va Wc Wf Yd Th) Ir(Hq Hv Hw Hx Ii Iu Jk Jl Jm Jr Lu Ly Lz Mb Mc Md Me Mf Mj Mk Ml Mq Mu Mv Mx My Na Nb Nc Nf Ng Nh Ni Nl Nr Nx Oi Pd Po Pz Qb Qe) Ke(Ad Af Aj bG bN Cv De dK Dp eC fP Hq Hr Ii Il Im Iz Jh Jj Jm Jo Jv Kj Kl Ne Nv Of Ou Oy Oz Ph Qc Qn Ss Tr Uh Up Ur Us Vp Vs Yd) Ih(Fp Hv Io Is It Iv Jl Jn Jo Jq Js Lh Lj Lv Lx Mn Mp Mr Mt Mz Nk Nm Nn Nq Ns Nv Ny Oe Om Oy Pb Pc Pe Pg Po Qa Qc Va) Jg(Fp Hu Hv Hw Ik Is It Iv Jn Jq Lh Lx Lz Mg Mn Mp Mr Mw My Nd Ng Nn Ns Nt Nu Oh Oi Oy Oz Pb Pe Po Qc Qe) Uh(aA As Cq Cu Cw Dc Hv Hw Id In It Iv Ji Jn Jq Jr Kd Kq Lw Ml Mz Na Nb Nf Pi Qa Ra Rj Sr Tv Up Vp Vt Vv) Js(Fp Hr Ik Is It Iv Jn Jo Lh Lj Lx Mh Mi Mm Mn Mp Ms Mw Mz Nm Nn Ns Nt Nu Ny Oe Oy Pb Pc Qa Qb Qc) Qa(Fr Ik It Iv Jn Jq Lh Lj Lx Mm Mn Mp Mr Mt Mw Mz Nd Nk Nm Nn Ns Nt Nu Ny Oh Oy Pa Pc Pe Yd) Mi(Fp Fr Hq Ik Io Is It Iv Jj Jq Lh Lw Lx Ma Mn Mz Nm Nn Nr Ns Nt Nu Nv Ny Og Pb Qb Qc Qe) Nt(Fr Ik Iq Is It Jn Jq Lw Lx Ly Ma

Figure 36 Continued

Mn Mw Mz Nd Ns Ny Oz Pb Qb Qc) Lj(Fr Ip Is Jj Jn Jq Lh Mg Mm Mn Mp Mw Mz Nm Nn Nq Nu Nv Om Oz) Ip(Fr Is Iv Jn Jq Lh Lw Lx Ma Mn Mp Mz Nu Ny Pb Qb Qc) aA(Hq jK Jr Mb Md Mf Ml Mq Mu Mv Na Ne Nf Nh Nl Pd) Jj(Bb Fr Ii It Jl Lx Mn Mz Nn Nr Nu Om Pe Po Qe) Jn(Fr Jq Lh Lw Lx Ma Mm Mp Mw Mz Nn Nu Og Oz Rx) Fr(Is It Jq Lw Mz Oe Og Oy Oz Pb Qb) Ma(Is It Jq Lw Mz Og Oz Pb Qb Qc) Og(Jl Lh Lx Mw Mz Nm Nv Ny Qb) Is(Lw Mw Mz Nm Nu Oe Oz Pb) Im(Aj Ux Uz Va Vi Yl Xa) Li(Dr Du Eq Va Vi Wb Th) Lx(It Jq Lw Mz Oz Pb) nl(ml nK nN nT Oz Ur) Mw(Jq Lw Mz Sh Wf) Aj(Et Ji Kq No) Ed(Dr Ru Vi Xa) Yd(Ji Kq Ow Pe) Va(No Pe Ps Sr) Mz(Hr Nu Qb) Nb(Rt Tl Ti) Jq(Hr Nu Qb) Oa(Gc Rx Ti) Lw(Ny Qb) Wf(Pe Vi) Kq(Dc Uu) Ow(Dr Wb) Pb(Lh Nv) WmNw NnSh MtMy JrjK PsOz

Unconstrained panels with 2 analytes, where 1.0E-5 >= 'model p-value' > 1.0E-6. Contains 1,766 panels of 121,819 total panels evaluated. :
Ke(aA aC aD aE aF aG aH aI aJ aK AL aM AN AO AP aQ AR AS aU aV AW AX aY aZ BA BB BC bE bF Bg bH bI bJ bL bM Bn BO bP bQ bR bS bU bV bW bX bZ cA cB cC cD cE cF cG CH cI cJ cK cL cM cN CO CP CQ cR CS CT CU cV CW CX cY cZ dA DB DC DD dE dF DG dH DI dJ Dk DL dM dN DR Ed Ef Et Ez Fn Fp Fr Fw Fy Gl GP gW Ha HB Hc Hf Hu Hv Hw Hx Ib Ic Id Ih IJ Ik In Io Ip Iq Ir Is It Iu Iv Jd Je Jf Jg Ji Jk Jl Jn Jp Jq Jr Js Jt Ju Jy Kc Kd Kg Ki Kk Kn Ko Kp Kq KR KS Kx Ky Kz Ld Li Lj Lu Lv Lw Lx Ly Lz Ma Mb Mc Md Me Mf Mg Mh Mi Mj Mk Ml Mn Mp Mq Mr Ms Mt Mu Mv Mw Mx My Mz Na Nb Nc Nd Nf Ng Nh Ni Nj Nk Nl Nm Nn No Nq Nr Ns Nt Nu NW Ny Oa OE oF Og OH Oi Ok Om ON Or Ow Pa Pc Pd Pe Pf Pg Pi Pj Pk Po Pz Qa Qb Qd Qe Qg Qh Ql Qm Qt Qu Qv Qw Qx Qy Qz Ra Rb Rc Rf Rg Rh Ri Rj Rm Ru Sr St Tn To Tt Tv Tz Ua Ub Uc Ud Ue Uf Ug Uk Ul Um Un Uo Ut Va Vt Wm Tj Th) Qa(Bb Fp Hq Hu Hv Hw Hx Ii Il In Io Iq Is Iu Jh Jk Jl Jm Jo Jr Lu Lv Ly Lz Mb Mc Md Me Mf Mg Mh Mj Mk Ml Mq Ms Mu Mv Mx My Na Nb Nc Ne Nf Ng Nh Nl Nj Nl Nq Nr Nv Nx Of Oi Om Pd Pf Pg Po Pz Qb Qc Qe Rt Ru Rx Ur Uw Uy Va Vi Wb We Wf Wh Zw Ye Wm) Js(Bb Hq Hu Hv Hw Hx Ii Il In Io Iq Iu jD Jh JK Jl Jm JQ JR jT jY Lu Lv Ly Lz Mb Mc Md Me Mf Mg Mj Mk Ml Mq Mr Mt Mu Mv Mx My Na Nb Nc Nd Ne Nf Ng Nh Nl Nj Nk Nl Nq Nr Nv Nx Of Oh Oi Om Pa Pd Pe Pf Pg Po Pz Qe Rt Uh Ur) Ij(Hc Hq Hv Hw Hx Ii Il In Iq Iu Jh Jk Jm Jr Lu Lv Ly Mb Mc Md Me Mf Mg Mh Mj Mk Ml Mq Mu Mv Mx Na Nb Nc Ne Nf Nh Ni Nj Nk Nl Nq Nr Nv Nx Oi Om Op Pd Pf Pg Pz Qe Rt Rx Sh Ur Uu Uw Uy Vb Vc Vh Vi Vo Vz Wb We Wh Zw Xa Ti) Jg(Aj Fr Hq Hr Hx Ii Il In Io Iq Iu Jh Jk Jl Jm Jo Jr Lu Lv Ly Ma Mb Mc Md Me Mf Mh Mj Mk Ml Mm Mq Ms Mt Mu Mv Mx Na Nb Nc Ne Nf Nh Ni Nj Nk Nl Nm Nq Nr Nv Nx Ny Om Pa Pc Pd Pf Pg Pz Uu) Mi(fR Hr Hu Hv Hw Hx Ii Il In Iq Iu Jh Jk Jl Jm Jo Jr Lv Ly Lz Mc Md Me Mf Mh Mk Ml Mm Mp Mq Mr Ms Mt Mv Mx My Nb Nc Nd Ne Nf Ng Ni Nj Nk Nq Oe Of Oh Om Oy Pc Pd Pe Pf Pg Po Pz Uh) Ji(aD aE AF aH aK AN aQ Ar aU aV aW Ax aY aZ BA Bb Bc BG bM BN bO bP cB cD cE CH cI cK cN Cs cT Cu cV Cw CX cY dA Db De dG dH Di dJ dK DL jT Ur Uu Uv Va Vo) Ih(Bb Hq Hr Hu Hw Hx Ii Ik Il In Iq Iu Jh Jk Jm Jr Lu Ly Lz Mb Mc Md Me Mf Mg Mh Mj Mk Ml Mq Ms Mu Mv Mx My Na Nb Nc Nd Ne Nf Ng Nh Ni Nj Nl Nr Nx Of Oh Oi Pa Pd Pf Pz Qb Qe) Im(aU Bb CH Cu De Di Dr Du Fc Fd Fi Gb Gd Gh Hl Ho Hp Lp Lt Op Ps Rt Ru Rv Rx Ry Rz Sf Si Sj Uh Uw Uy Vb Vc Vh Vw Vz Wb Wc Wd We Wf Wg Wh Yd Zw Zx Tm Tl Ti Th) Is(Bb cV cX Fp Hr Hu Hv Hw Ik Il Io It Iv jK Jn Jq jT Lh Lv Lx Ly Mg Mm Mn Mp Mr Ms Mt Nd nl Nn Nr Ns Nv Ny Of Oh Om Oy Pa Pc Pe Pf Pg Po Qb Qc Uh Ur Va Yd) Uh(Ad aM bA BN Cp Dd dK Dr Hx Ir Jj Jo Jt Kn Kp Kr Ld Me Mj Mt Nl Nk Nm Nr Ny Oe Oh Oi Om Ou Pb Pe Pk Qd Qe Rb Rf Uc Ud Ul Un Ur Us Uu Vs) Nt(Fp Hr Hu Hv Hw Hx In Io Iv Jl Jo Jr Lh Lz Me Mm Mp Mr Mt My Na Nc Ne Ng Ni Nj Nk Nm Nn Nq Nr Nu Nv Oe Of Oh Oi Om Oy Pc Pe Pf Pg Po Qe Va) Li(Aj Fc Fd Fi Gb Gd Gh Ho Hp Lp nl Op Ps Rt Ru Rv Rx Ry Rz Sf Sh Uw Ux Uy Uz Vb Vc Vh Vw Vz Wc Wd We Wf Wg Wh Yl Zw Zx Ye Tm Tl Xa Ti) Fr(Fp Hr Hu Hv Hw Ik In Io Iq Iv Lh Lx Ma Mm Mn Mp Mr Mt Mw Mx My Nb Nc Nd Ng Ni Nj Nm Nn Ns Nu Ny Of Oh Pa Pc Pe Pg Qc) Jn(Fp Hv Hw Ik Io It Iv Jl Lv Mn Mr Ms Mt Nb Nd nl Nm Nq Nr Ns Nv Ny Oe Oh Om Oy Pa Pb Pc Pe Pf Pg Po Qb Qc Qe Rt Va Wf) Pe(Du Fc Gh Ha Ip Jq kP Lj Lw LX Ma Mm Mn Mw Mz nD nl Ny Og Oz Pb Qb Rt Ru Sh Ux Uy Vc Vi Vz Wb Wc Wh Yl Zw Xa) Ip(Fp Hr Hv Hw Il Io Iq It Jh Jl Ly Lz Mm Mr Mt Mx Nb Nc Nd Nm Nn Nq Nr Ns Nv Oh Om Oy Pa Pc Pf Pg Po Qe) Lj(Fc Gb Ho Hv Hw Ik Io It Iv Jh Jl Jo Lv Lx Mr Mt Nb Nd Ns Ny Oe Og Oh Pa Pb Pc Pg Po Ps Qb Qc Vw Wd Ti) Vi(aF aO aW bF Bg Bn Ch cV Gc Hc Iv Kz Ld Lz Ml Mq My Nb Nx Oa Of Ow Oz Qx Rt Sh Sr Tn Ur Uu Va Vt Yd) Aa(aA li Ik Il Io Iu Lw Ly Mb Mc Md Me Mf Mh Ml Mm Mv Mx Na Ne Ng Nh Ni Nm Nv Nx Oh Om On Pd) Jq(Fp Io It Iv Jj jK Jl jO jT Lh Lw Mm Mn Mp Mt Mz Nm Nn Nr Nv Ny Og Oz Pa Pb Po Qc Qe Ur Wm) Qd(aD aH Aj aQ aZ BA bM bN bP cH CX De dJ jK jQ jR jT Ld Ou Ra Ru Ur Uu Uv Va Vo Yd) Lx(Hq Hv Hw Ik Io Iv Jl Lh Ma Mm Mn Mp Mr Mt Mw Nb Nm Nn Ns Nu Ny Oe Om Oy Pa Pc Qb Qc) Nw(Ad AF Aj As aW aZ Bb bN bO CH Cp Cq Cu Cw CX Dc Dd De Dg dH Di dK Va Yd) Mz(Fp Io It Iv Lh Lw Mm Mn Mp Mt My Nf Nm Nn Nr Nv Ny Of Om Oz Pb Pc Po Qc Qe Wm) Jt(Bb Ct Hq Hv Hw Il Jh Jk Jr Mb Mc Md Me Mk Ml Mq Mu Mv Ne Nf Nh Ni Nl Nx Pd Pz) Ma(Fp Hv Hw Ik Iv Jl Lh Mn Mp Mr Mt Mw Nb Nm Nn Ns Nu Ny Oe Of Oy Pa Po Qe) Mw(Fp Hv Ik It Iv Jl Lh Mm Mn Mp Mr Mt Nm Nn Ns Nu Nv Ny Om Oz Pb Qb Qc) Jp(Hq Hx Ii Il Io Jh Jk Ly Mb Mc Md Mf Mk Ml Mu Mv Ne Nh Nl Nx Oi Pd Pz) Lw(Fp It Iv Jj Jl Lh Mn Mr Mt Nm Nr Nu Nv Og Oz Pa Po Qc Qe) Qb(Bb Lh Mm Mn Mp Mr Mt Nm Nn Ns Nu Nv Ny Oe Om Oy Oz Pb Pc) Jj(Fp Io Iv Jk Jo Kq Mm Mp Mt Pf Pg Pz Qc Sr Ut) Ny(Fp It Iv Lh Mn Mp Mr Nm Nn Nu Oz Pb Qc Rx) nI(aA Cx kG Lz mP Mq nC nH nL nU Oh Pb Pf Qc) Va(Ed Fw Gc Ir Ld Nb Oa On Ow Qe Rm St Un) Jr(iC jD jE jO jQ jR jT jV jY IK IM IN) Oz(Fp Iv Jl Lh Mn Mp Mt Nv Om Pg Po Xa) Og(It Iv Jk Mn Mt Nb Nn Nr Nu Po Qe) Kq(Ch Iz Jo Kl Mm Of Ss Uv Vo Wf) Nu(It Jl Lh Mn Mp Nn Nv Om Qc) Bb(aA Aj Jo Ml Mt No Qc Qe) Mn(Fp It Lh Nm Nn Pb Po Qc) Nb(Eq Lp Ru Rx Wd We Wf Yd) It(Jl Lh Mm Mp Nn Nv Om) Sr(Aj Dr Sh Ur Uu Wf Yd) Cx(kP ml mS mU mZ nN) Ed(Gc Gd Ps Uw Wd Ti) No(Ur Uu Vc Wf Wm Th) Qc(Cu Lh Mm Mp Nv Om) Wb(Ld Ml Mq Oh Pf) Lh(Hr Iv Mm Nm Of) Mt(Eq Of Oy Yd) Nv(Nm Ns Oe Oy) Om(Oe Of Oy Pb) Aj(nN On Ut) Fp(Mm Mp Nm) Oa(Dr Fc Ho) Ur(Ir Lp Vt) Pb(Jl Pg Po) aA(cX dH jT) Cu(Hr Rt) Mr(Ru Wf) Iv(Rt Ru) Xa(Ld Mq) DrLd NmJl NsMp MlIM YdOn VtbN Unconstrained panels with 2 analytes, where 1.0E-4 >= 'model p-value' > 1.0E-5. Contains 3,531 panels of 121,819 total panels evaluated. :
Qd(aC Ad aE AF aG aI aJ aK AL aM AN AO AP AR AS aU aV AW AX aY bB BC bE bF BG bH bI bJ bL Bn BO bQ bR bS bU bV bW bX bZ cA cB cC cD cE cF cG Ch cI cJ cK cL cM cN CO CP CQ cR CS CT CU CV CW cY cZ dA DB DC DD dE dF DG dH DI DK DL dM dN Dp DR Ed Ef Eq Ez Fn fP GP HA Hb Hc Hf fB IC Id iJ Iz JD JE JF jG jH jI jL jM jO jP JU JV JY Kc Kd Kf Kg Ki Kj Kk KI Kn Ko Kp Kq Kr kS Kx Ky Kz lK IL IM IN lO nI nW Oa oE oH Or Ow Ph Pi Pj Pk Qg Qh Ql Qm Qn Qt Qu Qv Qw Qx QY Qz Rb Rc Rf Rg Rh Ri Rj Rm Sh Sr Ss St To Tr Tt Tv Tz Ua Ub Uc Ud Ue Uf Ug Uk Ul Um Un Uo Up Us Ut Vi Vp Vs Vt Ye Xa Ti Th) Vi(aA Ad Af Aj aM aN aP AR aS aU AX aY aZ bE bG bJ bL bN Bo bQ bW bZ cC cE cH CO cQ Cs Ct Cv CX cZ De dF Dg DI DK Dp DR EF Eq Ex Ez Fn FP Fr Fw Gd Gh GL GP HB hC hF hG Ho Hq Hr Hv Hw Hx iA Ic IH iJ iO iP Ir Is It Iu IZ Jd Jh Ji Jj Jk Jl Jm Jn Jo Jp Js Jy Kc Kd Ke Ki Kj Kl kQ kR kS Lp Lu Lv Lx Mb Me Mf Mg Mh Mi Mk Mm Mn Mp Mr Mt Mu Mw Mx Na Nc Nd Nf Ng Nh Ni Nk Nn No Nq Nr Ns Nu Nv NW nY OE oF Og OH Oi OK ON Op Oy Pa Pb Pc Pd PF Ph Pj Ps Qb Qc Qe Qg Ql Qn Qu Qv Qw Qy Ra Rb Rc Rf Rh Rj Ru Rv Rx Rz Si Sj Ss St Tv Tz Uf Ug Uh Ul Um Un Up Us Ut Uv Uw Ux Uy Vb Vc Vo Vp Vq Vs Vw Wc Wd We Wh Zw Zx Tl Xa Wm Th) Uh(Aa aE AF Aj aL An Ao Ap Ar aU AW Ax aY BB BG bL bM Bo bV cA CH cM cQ Cs cT CV CX DB De Dg dJ Dk dL dM dN Dp dR Ed EF Et Ez Fn FP Fr Fw Fy GL GP Ha HB HC hG Hq Hr Hu iA Ib IH Ii iJ Ik Il Io IP Iq IZ Jf Jg Jh Jl Jm Jp Ju Jv Jy Kc Kf Kg Ki Kj Kk Kl Ko kQ kS Kx Kz Lh Li Lj Lu Lv Lx Ly Lz Ma Mb Mc Md Mf Mg Mk Mm Mn Mq Mr Ms Mv Mw Mx My Nc Nd Ne Ng Nh Nj Nl Nn No Nq Ns Nt Nu NW Nx Oa oE OF Ok ON Or Ow Oy Oz Pa Pc Pd Pf Pg

Hv Io Jl Mr Nm Nr Oy Pb Pd) Hb(Cu Fy Ih Kd Ml Mu Na Un Ut Vt) Mm(Hv Hw Jl Mr Nm Nr Pa Pb Pg) Ho(Ar Cs Lz Mh Ml Mx Oh Qx Rt)
Ih(bM Cu jK Rx Sh Wf Yd Ye) Jl(Hr Io Nr Ns Oe Oh Oy Pc) Nm(Hv Mr Mx Nr Pa Pb Pg) Ld(Lp Na Ru Uy Wf Ye Th) Ut(Ch Iz Kl Sh Uu Wf
Yd) nN(Ad Af Cv Jo Kj Oy Pb) Cu(dH Gd Jo Jp Nk Pb) Ml(jD jl jK jT Kd Lp) Ru(Cs Fw Hv Kz Vt Wb) Rt(Ax Cq Fy Hv Mx) Oh(Eq Fc Gb Sh
Yd) On(Bg De Uu Wf Wm) Nr(Mr Pb Sh Wf) Ir(jK Rx Uu Wf) Jh(Ch Oy Wf Yd) Vt(aY Gp Ou Th) Cs(Fc Ti Th) Mr(Io Pb Rx) Jo(Hr Kd Pb)
Un(bN Pb Uu) Ax(Rx Th) Fy(Ou Vs) Mx(Sh Wb) jl(jT Nk) ArLp TiKd EqQy FdaW FwSh NsNd WbQx OyPg dMjK

Unconstrained panels with 2 analytes, where 1.0E-3 >= 'model p-value' > 1.0E-4. Contains 8,751 panels of 121,819 total panels evaluated. :
Kq(aA aC aD aE AF aG aH al aK AL AN AO AP aQ AR As aU aV AW AX aZ BA BB BC bF bG bJ bM Bn BO bP bQ bR bS bU bW bZ cA
cB cC cD cE cF cG cJ cK cL cM cN CO CP CQ CS CT Cu CV CW CX cY cZ dA DB DC DD dE dF dG dH DI dJ DK DL dM dN dR Du eC Ed
eF Et Ex Ez Fb Fc Fd Fi Fn FP Fw Fy Gb Gc Gd Gh GL Gn GP Gz Ha hB hC HF hG Hl Ho Hp Hr Hu Hv Hw Hx iA Ib Ic Id IH Ii iJ Ik Il In IO
IP Iq Ir Is It Iu Iv iZ Jd Je Jf Jg Jh Ji Jk Jl Jm Jn Jp Jq Jr Jt Ju Jv Jy Kc Kd Kf Kg Kj Kk Kl Kn Ko Kp kQ KR KS Kx Ky Kz Lh Lp Lt Lu Lv Lw Lx Ly
Lz Ma Mb Mc Md Me Mf Mh Mi Mj Mk Mn Mp Mq Mr Ms Mt Mu Mv Mw Mx Na Nb Nc Nd Ne Nf Nh Nl Nj Nl Nm Nn Nq Nr Ns Nt Nu Nv
nW Nx NY Oa Oe oF Og Oh OK Om On Op Or Ow Oz Pa Pc Pd Pe PF Pg Ph Pi Pj Pk Po Ps Pz Qa Qe Qg Qh Ql Qm Qn Qt Qu Qv Qw Qx Qy
Ra Rb Rc Rf Rg Rh Ri Rm Rv Rx Ry Rz Sf Si Sj St Tr Tv Ua Uc Uf Ug Uk Ul Um Un Uo Up Ut Uw Uy Uz Vb Vc Vh Vi Vp Vt Vw Vz Wb
Wc Wd We Wh Yl Zw Zx Ye Tm Tl Xa Wm Tj Ti Th tF) Sr(aA aC Ad aE aF aH al aK AL An Ao Ap aQ Ar As aV AW Ax aZ BA BB Bc BG
bL bM Bn BO bR bS bU bW bZ cA cC cE cF CH cJ cM cN Co Cp CQ Cs CT Cu CV Cw CX cY cZ dA Db Dc DD De DG dH Di dJ DK Dl dN
dR Du eC Ed Ef Ez Fd Fi Fn FP Fw Fy Gb Gh GL Gn gP Ha Hc Hp Hr Hu Hv Hw Hx Ib Id Ih Ii IJ Ik Il In Io Ip Ir Is It Iu Iv IZ Jf Jh Jk Jl Jm Jn
Jp Jr Js Jt Ju Jv Jy Kc Kd Kf Kg Kj Kk Kl Kn Ko Kp Kr kS Kx Ky Kz Lh Lj Lu Lv Lw Lx Ly Lz Ma Mb Mc Md Me Mf Mg Mi Mj Mk Mn Mp
Mq Mr Ms Mt Mw Mx My Na Nb Nd Ne Nf Ng Nh Ni Nk Nl Nm Nn No Nq Nr Ns Nt Nu Nv nW Nx Ny Oa oE OF Og OH Ok Om ON Or Ow
Oy Oz Pa Pc Pd Pe pF Pg Ph Pi Pj Pk Po Pz Qa Qb Qe Qg Qh Ql Qm Qn Qt Qu Qv Qw Qy Qz Ra Rb Rc Rf Rg Rh Ri Rj Rm Rz Si Sj Ss St Tn
To Tv Tz Ua Uc Ud Uf Ug Uk Ul Um Un Uo Up Us Ut Uw Vp Vs Vt Wg Zx Ye Tm Wm) Xa(aA Ad aF AJ aM AN aO aP aR AS AX aZ Ba bE
bF BG bJ bL bM BN bP bR bS bW cA cC cD cE cF CH CO Cp CQ CS CT CU CV Cw cX cZ dA Db DC DD De Dg dH DI dK Dp dR Du Ef
Em Eq Et Ex Ez Fc Fd Fi Fn fP Fy Gb Gc Gh GL Gn Gp Gz Ha HB Hc Hf Hl Ho Hp Hq Hr Hu Hv Hw Ib Ic Id Ik Il In Ir It Iu IZ Jd Je Jf Jh Ji Jl
Jm Jo Jp Jq Jr Js Jt Jv Jy Kc Kf Kg Ki Kj Kk Kn Ko Kp KR Kx Ky Kz Lh Lp Lw Mb Md Me Mf Mg Mj Mk Mm Mp Mr Ms Mu Mv My Mz Na
Nc Nd Ne Nf Ng Nh Ni Nj Nk Nl Nm Nq Nr Ns Nt Nv Nw OE OF Og Om On Op Or Ou Oy Pa Pc Pd Pg Ph Pi Pj Pk Po Ps Qc Qg Qn Qu Qv
Qw Qy Ra Rb Rc Rf Rj Rm Rv Ry Rz Sf Si Sj Ss St Tv Tz Ub Uf Uh Uk Ul Un Uo Up Ur Us Ut Uu Uv Ux Uy Uz Vc Vo Vp Vq Vz Wb Wc
Wf Wh Yd Yl Zx Ye Tl Wm Tj Ti Th) No(aC aD aG aH al aJ AL AN AO AP aR aS Aw Ax aY bA bB BC bE bF bH bl bJ bL Bn Bo bP bQ bR
bU bV bW bX bZ cA cB cC cD cF cG cl cJ cK cL cM cN CO cP cQ cR CS cT cU cV cW cY cZ dB dC dD dE dF dJ Dk DL dM dN DR Du eC
ED Ef Eq Ez Fd Fi Fn fP fR Fy Gb Gc Gd Gp hA hB HC HF hG Hl Hp hW hX iA IB IC Id iH iJ iO iP iZ JD JE JF jG jH jl jL jM jO jP jQ jR jT
JU JV JY Kc Kd Kf KG Ki Kk KN Ko Kp kQ KR KS Kx Ky Kz IL IM IN IO Lp Lt IX nD nN nW nY Oa oF oH oK oO OP Or pF Pi Pj Pk Ps
Qg Qh Ql Qm Qn Qt Qu Qv Qw Qx Qy Qz Ra Rb Rc Rf Rg Rh Ri Rj Rm Rt Rv Ry Rz Sf Si Sj St Tn To Tv Ua Ub Uc Ud Ue Uf Ug Uk Ul Um
Un Uo Up Us Ut Uw Ux Uz Vb Vh Vp Vv Vw Vz Wc Wd We Wg Yl Zx Ye Tm Tl) Dr(aA aD aJ Ao aP Ar aV Ax aY aZ BA Bb bH Bn bQ bS
bW cH CO Cp Cq cS cT CU CX Dp dR Du Em Eq Et Ex Ez Fc Fd Fi Fn Fp Fr Fw Fy Gb Gc Gd Gh gL Gp Gz Ha HB Hc Hf Hl Hp Hq Hv Hw
Hx Ib Id Ih Il In Iq Ir Is It Iv IZ Jd Je Jf Jg Jh Ji Jk Jm Jn Jo Jp Jr Js Jt Ju Jv Jy Kf Kg Ki Kj Kk Kl Kn Ko Kp Kr Ks Kx Ky Kz Lh Lp Lt Lu Lx
Lz Ma Mg Mh Mj Mk Mm Mn Mp Mr Mt Mu Mv Mx Mz Nc Ne Ni Nj Nk Nl Nn Nq Nr Nt Nv Nw Nx NY OE oF Og Oh Oi Om On Op Or Ou
Pa Pb Pc Pd Pe Pg Ph Pi Pj Pk Po Qa Qc Qe Qg Qh Ql Qm Qn Qt Qu Qv Qz Ra Rb Rc Rf Rg Rh Ri Rj Rt Rv Rx Ry Rz Sf Sh Si Sj Ss Tn To Tv
Ua Ub Uc Ud Ue Ug Uk Ul Um Un Uo Us Uu Uv Uw Ux Uy Uz Vb Vc Vh Vo Vp Vs Vw Vz Wb Wc Wd We Wf Wg Wh Yd Yl Zw Zx
Ye Tm Tl Wm Ti Th) Qa(aC AD aE AF aG aH al aJ aK AL aM AN AO AP aQ AR AS aU aV AW AX aY aZ BA bB BC bE bF BG bH bl bJ
bL Bn BO bP bQ bR bS bU bV bW bX bZ cA cB cC cD cE cF cG CH cl cJ cK cL cM cN CO CP CQ cR CS CT CU CV CW CX cY dA DB DC
DD DE dF DG dH DI dJ DK Dl dM dN Dp eC Ed Ez Fn fR Fy Gc Gd Gp Gz Ha Hc Hf Ib Ic Id iJ iP IZ Jd Je Jf jK jT Ju Jv Jy Kc Kd Kf KG Ki
Kj Kk Kl KN Ko KP Kr KS Kx Ky Kz lM lX mZ nA nD nN nW Oa oE oF oH oN Or Ow pF Ph Pi Pj Pk Qg Qh Ql Qm Qn Qt Qu Qv Qw Qx
QY Qz Ra Rb Rc Rf Rg Rh Ri Rj Rm Ss St Tn To Tv Tz Ua Ub Uc Ud Ue Uf Ug Uk Ul Um Un Uo Up Ut Vp Vq Vt) Ij(aC AD aE aG aH al aJ
aK AL aM AN aO AP aQ AR AS aU aV Aw Ax aY BA bB BC bE bF bG bH bl bL Bn BO bP bQ bR bS bU bV bW bX bZ cA cB cC cD cF
cG cH cl cJ cK cL cM cN CO CP CQ cR CS cT cU Cv CW Cx cY cZ dA DB DC DD DE dF DG dH dl dJ DK DL dM dN dR dX Ed Ef EM eP
Ez Fn fP fR Fw GL Gn GP Gz Ha Hb Hf Ic Id iJ iP iZ Jd Je Jf jl jK Ju Jv Jy Kc Kd Kf Kg Ki Kk Kn Ko Kp Ks Kx Kz nl nW nY Oa oE oF oH
oN Or Ow pF Ph Pi Pj Pk Qg Qh Ql Qm Qn Qt Qu Qv Qx Qy Qz Ra Rb Rf Rg Rh Ri Rj Rm St Tn Tv Tz Ua Ub Uc Ud Ue Uf Ug Uk Ul Um
Un Uo Up Ut Vp Vv Wm Tj) Is(aC AD aE aG aH al aJ aK aL aM AN AO AP aQ AR AS aU aV Aw AX aY aZ bA bB BC bE bF BG bH bl bJ
bL Bn BO bP bQ bR bS bU bV bW bX bZ cA cB cC cD cE cF cG CH cl cJ cK cL cM cN CO CP CQ cR CS cT CU Cv CW cY cZ dA DB DC
DD dE dF DG dH dl dJ DK DL dM dN Dp Du ED Eq Ez Fc Fd Fi fR Fy Gb Gd Gh Gp Gz Hb Hl Ho Hp hR hV hW hX Iz Jv Kd Ki Kj Kk Kl
Ko Lp Lt Op Ow Pj Pk Ps Ql Qn qT qU QV QW qX Qy RA Rf Rm Rv Ry Rz Sf Sj Ss Tz Uf Un Up Us Ut Uv Uw Ux Uy Uz Vb Vc Vh Vp
Vs Vt Vw Vz Wd Wc Wg Wh Yl Zx Ye Tm Tl Ti Th) Mz(aD aE AF aH Aj aK AN Ap aQ Ar aU aV aW AX aY aZ BA bB BG bM BN bO bP
Ch cJ cP Cs Ct Cu cV CX dA De dH Di dJ dK dR eD EF Ez Fn fP Fw Fy GL gP gW HA hB Hc Hf hG Hq hR hV hW hX IB IC Id iJ Iz JD JE
JF jG jH jl jL jO jP jQ jR jT JU JV JY Kc Kd Kf Kg Ki Kj Kk Kl Kn Ko Kp Kr KS Kx Ky Kz IK IL IM IN Lu Mb Mf Mk Mu Na Nc Nh nW
Nx nY Oa oE oF oH Oi oN Or Ow Pd pF Ph Pi Pj Pk Qg Qh Ql Qm Qn Qt Qu Qv Qw Qx Qy Qz Ra Rb Rc Rf Rg Rh Ri Rj Rm Ru Ss St Tn To
Tr Tv Ua Ub Uc Ud Ue Uf Ug Uk Ul Um Un Uo Up Ut Va Vi Vo Vp Vs Yd Tj) Bb(aC AD aE AF aG aH al aJ aK AL AN AO AP aQ AR AS
aU aV AW aX aY Ba bB BC bE bF bG bH bl bJ bL bM Bn BO bP bQ bR bS bU bV bW bX bZ cA cB cC cD cE cF cG cl cJ cK cL cM cN CO
CP CQ cR CT cU CV CW cY cZ dA DB dC dD DE dF DG dH dl dJ Dk DL dM dN Fp Fr Fy Hq Hr Hu Hw Hx Ii Ik Il In Io Ip Iq Jg Jh Jk Jl
Jm Ld Lh Lu Lv Lx Ly Lz Ma Mb Mc Md Me Mf Mg Mh Mj Mk Mn Mp Mq Mr Ms Mu Mv Mx Na Nc Nd Ne Nf Ng Nh Ni Nj Nk Nl Nm NN
Nq Nr Ns Nt Nu Nv Nx Ny Of Og Oh Ok Om On Pa Pc Pd Pf Pg Po Pz Ur Uu Va Vi Vo Vt) Pe(aF aK aM aQ aU aV aX aZ BA BG bL bM bN
bO bZ cD cE CH Ct Cu Cv cX Dc dH Di dJ dK Dp Ed Fn fP fR Fy Gn Gz Hb Hc Hq Hu Hv Hw Hx Ii Il In Iq Iu Iz Jf Jh jl JK Jm Jo Jr Jv Kd kE
kF kG KI Kj kK KJ KO Kz Ld Lu Lv lW LY Lz Mb Mc Md ME MF Mg MH ml Mj Mk Ml mM mP Mq Mr MS mT MU Mv mW Mx MY mZ
Na NB NC Nd Ne NF Ng NH Ni NJ NK NL nM nO Nq nR nT nU nW Nx OE OH Oi oP Ow Pa Pd PF Pg Ph Pi Pk Pz Qg Qv Qw Qy Ra Rc Rf
Rg Rm Ss Tv Tz Uf Um Un Us Ut Uv Vp Vt) Mt(Ad AF aH aL aN aQ As aV aY aZ BA bC bF BG bL BN bO bP bQ bR bS bU bW bZ cA cC
cD cE cF cG CH cK cL cN CO Cs Ct CU CV CX dA Dc Dd De DI dJ Dp Du eD Fc Fd Fi fR Gb Gd Gh Gp hA Hl Ho Hp HR Hu HW iB Ii Il In
Io Iq Iu jD jG Jh jl JK Jm JO jQ JR jT jY Kd IK Lt Lv Ly Lz Mc Md Me Mf Mg Mj Ml Mq Ms Mx Na Nb Nc Nd Ne Nf Ng Nh Ni Nj Nk Nl Nq
Nr Nx oE Oh Oi oN Op Pa Pc Pf Pg Pz qY Rf Rg Rt Ru Rv Rx Ry Rz Sf Si Sj Tz Ur Uw Uy Vb Vc Vh Vt Vw Wc Wd We Wg Wh Zx Ye Tm

Figure 36 Continued

Wm Ti Th) Vi(aC aD aE aG aH al aJ aK AL An Ao Ap aQ As aV Aw BA bB BC bH bI bM bO bP bR bS bU bV bX cA cB cD cF cG cI cJ cK cL cM cN CP Cq cR cS cT cU CW cY dA DB DC DD dE dG dH dJ DL dM dN Du Em Et Fc Fd Fi fR Fy Gb Gn Gz Ha Hf Hl Hp Hu Ib Id Ii Ik Il In Io Ip Iq Je Jf Jg Jq Jr Jt Ju Jv Kf Kg Kk Kn Ko Kp Kr Ks Kx Ky Lh Lt Lw Ly Ma Mc Md Mj Ms Mv Ne Nj Nl Nm Nt Ny Om Or Ou Pg Pi Pk Po Pz Qh Qm Qt Qz Rg Ri Rm Ry Sf To Ua Ub Uc Ud Ue Uk Uo Uz Vh Vz Wb Wg Yl Ye Tm Tj Ti) nI(Af aG aH al aJ aM aN aP Ar aW aX aZ bB bM bN bQ bR bZ cF cH cK cO cR CS CU cW dE dF dK Dp dR Et Ez Fa Fr Fw Gp hB Hq Hr Hu Hv iA Ib Ii Ik In Io Ip Iq It Iu iZ Jg Jh Jk Jm Jo Jq Jt kC KE Kj kN kO Ky Ld LW lX Yl Mb Mc Md ME Mf Mg MH Mk MM Mn MS Mu My mZ NA Nc ND Ne Nf Ng Ni NJ Nk Nl Nm Ns Nv Nw Nx Ny Oa Oe OF Og Oi Ok Om On oO oP Ow Pc Pd Pi Pk Pz Ql Qm Qn Qu Qv Qw Qx Qy Rb Rc Rf Rh Ri St To Tv Tz Ub Ue Uf Ug Ul Un Up Ut Uu Uv Vo Vp Vs Vt Vu Vv Wm) aA(aC aD Af aG al AJ aK AL aN AO AP AR AS aU aV Aw AX aY BA BC bE bF bG bH bI bJ bL bM Bn bQ bR bS bU bW bX bZ cA cB cC cD cE cF cG Ch cI cK cL cM CO CP CQ cR CS cT CU Cv CW cY cZ dA dB dC dD De dF dG DI dJ Dk DL dM dN Dp dR fR Gc hA Ho hV iB iC jG jH jI jL jM jP jU jV jY Kd kG kI Ko kP Ld lM lN lO lX ml mS mZ nA nC nD nJ nK nL nN nT nW oE oO oP oQ Ou Pi Pj Pk Ps qT qU qV qW qX rA rC Rf Ru rX rY rZ Si Tz Un Ur Ut Va Vt Ti) Qc(aC AD aE AF aG aH al aK aL aM AN AO AP aQ AR AS aU aV AW Ax aY bB BC bE bF BG bI bJ bL BN bO bP bQ bS bV bZ cA cB cD cE cG CH cI cJ cL cM Co CP CQ cR CS cU CV Cw CX cY DB dC DD DE dF dH dJ DK Dl dM dN Ed Hr Hu Hx Ii Ik Il In Iq Iu jI JK Jm Jr Kd Ki Kk Kn kP IM Ly Lz Mc Md Me Mh Mj Mk mP Mq Ms Mu Mv Mx My mZ Na NC Nd Nf Ng Ni Nj Nk Nl nN Ns nU Nx Oe Oh Ou Oy Pi Pz qY Ra Rf Tz Un Up Ur Ut Uu Vp) Nw(Dp eD Eq Ez Fb Fc Fd Fi Fn fR Fw Fy Gb Gd Gl HA Hb Hc Hf Hl Ho Hp hW hX IB IC Id iJ Iz Jd JE JF jG jL jM jO jP jQ jR JU jV JY Kc Kd Kf Kg Ki Kj Kl Kn Ko Kp Kr Ks Kx Kz Ld IL IM lN lO Lp Lt Oa oE oN Op Or Ou Ow Ph Pi Pk Ps Qg Qh Ql Qm Qt Qu Qv Qx Qy Qz Rb Rc Rf Rg Rh Ri Rj Rm Rt Rv Rx Ry Sf Sh Sj Ss St Tn To Tr Tt Tv Ua Ub Uc Ud Ue Uf Ug Uk Um Un Uo Us Ut Uw Uy Uz Vb Vc Vh Vs Vv Vw Wb Wc Wd We Wf Wg Wh Yl Zw Zx Tm Tl Tj) Vt(aE Af aH al aL aQ aU aW aZ bB Bc bF bL bM Bn bS cE cH Cs cT Cu CX cY dA De dJ dK Dp dR eC Ed Et Ez Fb Fi Fp Fw Fy Ho Hp Hq Hr Hv Ih Il In Ip Ir It Iv Jf Jg Jm Jn Jo Jp Jq Jr Js Jt Ki Kj Ko Kz Ld Li Lj Lp Lt Lx Ly Lz Ma Mg Mi Ml Mm Mn Mq Mv Mw Na Nb Nd Nc Nk Nn Nq Nr Nt Nu nW Nx Ny Oa OE Of Oh Oi On Ow Oy Oz Pb Pg Pi Pj Pk Qb Qe Qg Qh Qm Qn Qv Qw Qy Ra Rf Rg Rh Ri Rx St Tz Uf Ug Um Un Uo Up Us Ut Uu Uv Uy Uz Vo Vp Wb We Wf Yd Yl Wm Ti) Et(aC AD aE AF aG aH al aJ aK AL aM AN AO AP aQ AR AS aU aV AW AX aY BabB BC bE bF bG bH bI bJ bL Bn BO bP bQ bR bS bU bV bW bX bZ cA cB cC cD cE cF cG cH cI cJ cK cL cM cN CO CP CQ cR cS CT cU CV CW CX cY cZ dA DB dC DD DE dF dG dH DI dJ DK DL dM dN Dp Ed Fy Hb IZ jG jH jI jK jO Kd Ki Kj Kl Ld IK Oa Pi Pk Qv Ra Rf Ss Tz Un Up Ur Ut Uv Va Vp Yd) Ps(AF Aj aM aO aP aW Ax bB bQ bR cO Cs CU cV CX Dg dR Eq Ez Fp Fw Fy Gc GL hB Ho Hu Hv Hw Hx Ih Il Io iZ Jh Ji Jj Jm Jr Js Kd Ke Kg Ki Kl Kx Kz Ld Lh Lx Lz Me Mg Mh Mi Mk Mr Mu Mx Na Nf Ni Nk Nq Nr Nt Ny OE Oh Om On Oy Pa Pb Pc Pd Po Qb Qd Qe Qg Ql Qn Qw Ra Rc Ri Rt Ru Rv Sh St Tz Ua Ub Uc Ud Ue Uf Ug Uh Uk Ul Um Un Uo Up Ut Uv Uw Ux Uy Uz Vb Vc Vh Vp Vq Vw Vz Wb Wc Wd We Wf Wg Wh Yl Zw Zx Ye Tm Tl Wm) Mi(AD aE AF aH aK aL aN Ap aQ Ar aS aU aV aW Ax aY aZ BA BC bF BG bH bL bM BN BO bP bQ bR bU bV bW bZ cA cB cC cD cE cF cG CH cI cK cL cM cN CO CP CU CV CW CX cY cZ dA Dc Dd DE dF dG dH DI dJ dK Du Em eP Eq Ex Fc Fd Fi Fy Gb Gc Gh Gn Gz Hb Hl Ho Hp jK kP Lp Lt mZ Op Rf Rv Rx Ry Rz Sf Sh Si Sj Uw Ux Uy Uz Vb Vc Vh Vw Vz Wb Wd We Wf Wg Wh Yd Yl Zw Zx Ye Tm Tl) Jq(aD aE aF aH aM aN Ap aQ Ar aU aV aW AX aZ BA Bc Bg bM BN bO bP cB CH cI CS CT CU cV Dc De Di dJ DK Dp dR eC ED Ef Ez Gp Ha Hc Hq hR HV hW hX Ib Ii In Iz Jr Ju Jv Kd Kf Ki Kj Kl Ko Kz Lu Mb Mc Mf Ml Mu Na Ne Ng Nh Nx Oa oE oF Oi Ou Pd Pi Pj Pk Qg Qh Ql QT QV QW QY RA Rb Rc Rf Rg Rh Ri Rj Ru Ss St Tn Tr Tt Tv Tz Ua Ue Uf Ug Uk Ul Um Un Uo Up Us Ut Va Vp) Ji(dR eC eD EF Ez Fb Fn fP fR Fw Fy Gb Gd GL GP gW hB HC HF hG Ho Hp hR hV hW hX iA Ib Ic Id iH iJ iO iP IZ Jd Je Jf Jy Kc Kd Kg Kk Kl Kn Ko Kp kQ KR KS Kx Ky Kz Lp nW nY Oa oF oH oK oN Op Or Ow pF Ph Pi Pj Pk Qg Qh Ql Qm Qn qT QU qV qW QX qY Qz rA Rb Rh Rj Rt Rv Rx Sh St Tn To Tr Tt Tv Ub Uc Ud Ue Ug Uk Un Uw Ux Uy Uz Vb Vc Vh Vv Vw Vz Wc Wd We Wg Wh Yl Zx Tl Tj Ti) Mw(Ad aE AF aH al aK aL aM AN Ao Ap aQ Ar aS aU aV AW AX BA bB Bc bF BG bH bJ bL bM BN bO bP bR bS bV bZ cC cD cE cG cH cI cJ cK Co CP Cq cR CS CT cU CV Cw CX cY Db DD De dF dH Di dJ dK Dl Du Fc Fi Fy Gb Gc Gd Gh Hb Hl Ho Hp Hq Iz jI JK Kd Lt Mb Mc Md Mk Ml Mu Mv Ne Op Ou Pd Rv Ry Rz Sf Si Sj Un Ur Uw Vb Vc Vh Vw Vz Wc Wg Zw Tm Tl Ti Th) Jt(aC AD aE aF aG aH al aJ aK AL aM AN AO AP aQ AR AS aU aV AW AX aY BabB BC bE bF bG bH bI bJ bL Bn BO bP bQ bR bS bU bV bW bX bZ cA cB cC cE cF cG cH cI cJ cK cL cM cN CO CP CQ cR CS cT cU CV CW cX cY cZ dA DB DC DD DE dF dG dH dI dJ DK dL dM dN Em Gd Gp Hb jK Kj Ld qY Rf Rt Ru Rx Uu Wf Wm Th) Li(AD aE AF aH aK aL aM AN Ao aQ Ar As aU aV AW aX aZ BA Bc BG bL bM BN bO bP bS bZ cB cD cE CH cJ Co Cp Cq CS CT CV Cw CX cY Dc Dd DE Dg dH Di dJ dK Dl Dp eM eP fR Hb jl jK Jy kC Kd kE kF kG Kl Kj kK Kl kO Ld lW lY mE mF mH ml mP mT mU mY nB nC nF nH nI nJ nK nL nM nN nO nR nT nU oP Ou Pk Qv Ra Rf Rg Ss Tz Un Us Uu Vo) Cu(Aa aD Af aH Ao Ap aQ Ar aW Ax aZ BA bL bM BN Ch cJ cK CS cT cV CX Dc Dd dE Di dK Dp Eq Fr Hq Hv Hx Ik In Io Ip Iq Ir It Jg Jh Jl Jm Jn Js Kj Ld Lj Lu Lw Lx Ly Ma Md Me Mg Mj Mk Ml Mm Mr Mu My Nb Nd Ne Nf Ng Nh Nj Nl Nn Nq Nr Ns Ny OE Of Og Oi Ok Om On Ou Oy Pa Pc Pd Pf Pg Po Qe Rf Ru Rx Sh Us Ut Uu Vb Vo Vs Vz Wb Wc We Wf Yd Tl Ti Th) Qe(aH Aj aQ aZ BA bN CX Di Eq Fc Fd Fy Hb Ho Hq Hr Hu Hv Hw Hx Ii Ik Il In Iq Iu jD Jh Jk Jl Jm Jo jQ Jr jT Ld Lp Lt Lu Lv Ly Lz Mb Mc Md Me Mf Mg Mh Mj Mk Ml Mq Ms Mu Mv Na Nb Nc Nd Ne Nf Ng Nh Ni Nj Nk Nl Nq Nr Nx Of Oh Oi Ou Pa Pd Pf Pg Pz Rt Rv Sh Un Us Ut Uu Uv Uw Ux Uy Uz Vb Vc Vh Vo Vs Vw Vz Wb Wc Wd We Wg Wh Yl Zw Zx Ye Tm Tl) Va(Ad aE aF aH aM Ao Ar aW aZ BA bR Co Cp Cq CT Cw Cx Dd Dk Dl Ef Eq Ex Fc Fd Fi Fp Fy gL Ha hB Hf Hu Id Il In Iq IZ Jd Jg Jk Jl Jm Jp Jr Kc Kd Kf Kk Kn Ko Kp Ks Kx Ky Kz Lh Lp Lz Mf Mg Mj Mk Ml Mn Mp Mr Mu Mv Ng Nh Ni Nm Nq Of Ok Or Ou Oz Pa Pc Pg Ph Pi Pj Pk Pz Qg Qh Qm Qx Ra Rf Ru Ry Tn Tv Ua Uc Uf Uh Up Uw Vh Vp Vs Vw Wb Wc Wd Tj Ti) Lw(Af aH Aj ar aV aW Ax aY aZ BA BG bM bN bP bS cD cE CH cK cN Cs cT CX dA Dc De dG dH DI dJ ED Gp hA Hq hR hV hW HX iB iC Ii Ik In Iu jD jE jF jG jH jI jK jL jM jO jP jQ jR jU jV jY IK IL IM lN lO Lu Ly Mb Mc Md Me Mf Mg Mk Ml Mq Ms Mu Mv My Na Nd Ne Nf Ng Nh Nj Nk Nl Nx Oe Of Oi Pd qY Tz Ur Wm) Uh(aC aD aG aH al aJ aK Al aN aO aP aQ aR aS aV aX aZ Ba BC bE bF bH bI bJ bO bP bQ bR bS bU bW bX bZ cB cC cD cE cF cG cI cJ cK cL cN CO cP cR cS Ct cU cW cY cZ dA dC dD dE dF dG dH DI Dl eC Ex Fa Fb HF Ho Ic iO Iu Jd Je Jk kG kR Ks Ky Lp Mh Mp Mu mZ Nv nY Og oH oK pF Pj Qm Qu Qz Rh Rm Ru Uz Wg Yd Tj tF) Ur(Ad Aj As bA bN cH Cq Cs cT Cw Dk Ed Fb Fd Fp Fw Gp Ha Hb Ho Hw Hx Id Ii Ip Jh Jj Jl Jm Jo Jp kC kE kF KG kI Kj kK KN kO KP Kr Ld Lh Lj lW lX lY ME mF mH ml Mj mM mP Mr mS mT mU mW mY mZ nA NB nC nD NF nJ nK nL NM nN nO nR nT nU Oa Ok Om On Pb Pk Po Qb Qh Ra Rb Rf Rj Tn Tv Tz Ul Us Vs) Js(aH aK aL aM aQ aU aV aX aZ BA bM bN bO CH Ct Cv CX cY Dc dE dH Di dJ Dp Du ED Eq Fd Fi Fn Fy Gb Gh Hl Ho Hp hR hV hW hX Jf Ju Kd Ki Kj Ko Lp Lt Op Ou Ow qU Qv qX Qy Rf Rv Ry Rz Sf Sh Si Sj Tz Uf Un Ut Uu Uv Uw Ux Uy Uz Vb Vc Vh Vp Vs Vw Vz Wd We Wg Wh Yl Zw Zx Ye Tm Tl Wm Ti Th) Jj(aH Al Ao Ap As AW Ax aZ BA Bc cH Cp Cq Cs cT Cv Cw CX Di Dk Ed Ez Fn Fw Fy Ha Ho Hu Hw Hx Id In Jd Jh jI Jr Jy KG Kj Kn Ko KP Ks Kx Kz Ld lM Lv Lz Mh Mq Mu Mv Nc Nd Nf Ng Ni Nj Nl Ns Oa Og Oh Pb Pc Pi Pj Pk Ql Qm Qn QY Ra Ri Rj Rm St Tn Tr Tt Tv Ua Uc Ue Uf Ug Ul Up Vp Vq) Ny(Aj Dk Du Eq Fc Fd Fi Gb Gc Gd Gh hA Hb Hc Hl Ho Hp Hq HX IB Ii Iq Iu jD jH jI JK Jm jQ jR jT Ld IL IM lN Lp Lt Lu Ly Mb Mc Md Me Mf Mj Mk Ml Mq Mu Mv My Na Ne Nf Ng Nh Nk Nl Nx Oi Op Pd Pz Rv Ry Rz Sf Sh Si Sj Tz Uw Ux Uy Uz Vb Vc Vh Vw Vz Wb Wc Wd We Wg Wh Yl Zw

Fi Gb Hp Io kG kN kP Lp lX mI mP nC Og Uz Wb Wc Wd) St(Eq Fd Gc Oi Rx Sh Uw Uy Uz Vh Wb Wc Wd Wg Yd Yl Ti Th) Lj(aZ Eq Gc Gh Jy Lt Op Rv Sf Sj Uy Vc Vz Yd Zw Ye Tm Wm) Io(Hw In Iq Jo Lv Mg Mh Ms Nb Nd Nq Ns Oe Oy Pa Pb Pc) bA(aH aM aZ bM bO cH cS cV cX Dd dE Di dK Fr Jg Pb Rt) Wb(Ar aW Ex hB Jh Kx Mh Mk Ni oE oF Pa Pd Ql Ra Rm) Rf(aE dJ Ed Gp gW Il Na Oe Oi Pi Tz Up Uv Vo Vp) Pb(cT Hw Ii Iq Jh Jk Mg mI Mj Nq Nx Og Pa Pc Pz) Gc(dR Ha Hx iZ Nb Ni Qv Qw Qx Ra Sh Uu Yd) Lp(aW hB Kx Mh Mk Ni oE Ql Qv Qx Qy Uf Vq) Og(Hu Hw Il In Lv Mj Mu Mv Nc Nq Nx Pc) Nb(bM Em fR Gn Hr Hx Iq jK jT lK Oe) Jh(Bg Eq Gd Hc Iz My Sh Ux Uy Uz) Fr(aF aZ Bg bO cE CH cV Dd) Tz(bN dK Fc Ko Ni Ra Wd Ti) Qy(Du Fd Rv Sh Ux Uz Wc Yd) Jo(Ad Dd kG Kn mI mP Pi Up) Rx(Cq Ha Hx In Na Pi Ql Rm) Rt(Cp Dd Fd Hw In Pi Tv Vp) Gp(iZ Kn Pi Ra Up Vp) Mu(aZ Eq oE oH Ou Pi) Qx(Fc Fd Fi Gb Hp Wf) Us(kG kP mI mS mU nU) Uu(Cp Dk Ef Ko Tn Uc) Uz(Ar cX hB Mk oE Ql) jK(Iq Lv Md Mj Ok Pc) Jg(aZ Bg Ch Kl Wm) Ed(eM kG kP Vs) Eq(Mg Nq Pd Uf) Fd(Ar Mh Mk Ql) Lv(Iq jD jT Nd) Yd(Il Nq Ql Vq) Sh(Il Jv Rm Vq) Uy(hB Mk Mv Ql) aZ(Aa aM Dd Nk) hW(jD jH jT Nk) Af(mI mU Uw) Ti(Ar hB Mj) Na(Dp Kj Ou) Hr(Cp Hw In) Si(aP hB iZ) Wf(Cp Mj Tn) Pa(Oy Pc Pz) Pi(Dp Ou Wc) aW(Hp oQ Yl) Bo(kP mS) Dd(Ba cS) Th(Ar Ql) Gd(aM Cw) Nq(Ch Hu) Oe(Jk Pz) Ok(bN Wm) dR(Ex fR) mZ(kG Ma) iZ(aH aL) qY(Iq Mj) oE(Jy Vq) AagW DiIp MkRy NdHq KjkG NxmP VoPj aNnK aPdH cXfR dKoQ jHjT

Constrained panels with 3 analytes, where 1.0E-10 >= 'model p-value' > 0. Contains 3,432 panels of 17,842,327 total panels evaluated. :
Et{Oy(aA Fp Hw Ih Ij Il Im Ip Iq Ir Is It Jh Ji Jm Jn Jq Js Jt Lh Li Lj Lw Lx Mi Mp Mr Mt Mw Mz Nb Nc Nd Ni Nn No Nr Ns Nt Nw Oe Of Og Ok On Pa Pc Pe Pf Pg Qa Qb Qc Qd Qe) Oe(aA Fp Hw Ih Ij Ik Il Im Ip Iq Ir Is It Ji Jj Jm Jn Jq Js Jt Li Lj Lw Mi Mp Mr Mw Mz Nb Nc Nd Ni Nn No Nr Ns Nt Nu Nw Of Oh Ok On Oz Pa Pb Pe Qa Qb Qc Qd Qe) Og(aA Fp Hv Hw Ih Ij Il Im Ip Iq Ir Is It Jg Ji Jj Jm Jn Jq Js Jt Lh Li Lj Lw Mi Mr Mt Mw Mz Nb Nc Nd Nm Nn No Nr Ns Nt Nu Nw Of Ok On Oz Pa Pb Pe Qa Qb Qc Qd) Pb(aA Fp Hv Hw Ih Ij Im Ip Ir Is It Ji Jj Jn Jp Jq Js Jt Lh Li Lj Lw Lx Mh Mi Mp Mr Mt Mw Mz Nb Nc Nd Nn No Nr Ns Nt Nw Of Ok On Pa Pe Pf Pg Qa Qb Qc Qd) Of(aA Fp Hv Hw Ih Ij Il Im Ip Iq Ir Is It Ji Jj Jm Jn Jq Js Jt Lh Li Lj Lw Ma Mi Mp Mr Mt Mw Mz Nb Nc Nd Nn No Ns Nt Nw Ok Om On Oz Pe Qa Qb Qc Qd) Oz(aA Fp Hv Ih Ij Im Ip Ir Is It Ji Jj Jn Jo Jq Js Jt Li Lj Lw Mh Mi Mp Mr Mw My Mz Nc Nd Ng No Nr Ns Nt Nw Ok On Pa Pe Pf Pg Qa Qb Qc Qd) Jj(Fp Ih Ij Il Im Ip Iq Ir Is It Ji Jm Jn Js Jt Li Lj Lw Mi Mw Mz Nc Nd Nn No Nr Ns Nt Nu Nw Ok On Pe Pg Qa Qb Qc Qd) Ns(aA Fp Ih Ij Im Ip Ir Is It Ji Jn Jq Js Jt Li Lj Lw Mi Mp Mw Mz Nc Nd Nn No Nt Nw Ok On Pe Qa Qb Qc Qd) Jo(Fp Hv Hw Ih Ij Im Ip Ir Is It Ji Jn Jq Js Jt Lh Li Lw Mi Mr Mw Mz Nc No Nr Nt Ok On Pe Qa Qb Qc Qd) Nd(aA Fp Hq Ih Ij Ip Ir Is It Iv Ji Jn Jq Js Jt Li Lj Lw Mi Ms My Mz Nc Ng No Nt Ok Pe Qa Qb Qc Qd) My(Fp Ih Ij Im Ip Ir Is Ji Jn Js Jt Li Lw Mi Mt Mw Mz Nb Nn No Nw On Qa Qb Qc) Ip(aA Fp Ih Ij It Jn Jq Js Jt Li Lw Mg Mi Mm Mw Mz Nc No Nt Ok Qa Qb Qc Qd) Hr(Fp Hv Hw Ih Ij Im In Ir Is Ji Jn Jq Js Jt Li Lw Mi Mz Ok Pe Qa Qb) It(aA Ih Ij Ik Ir Ji Jn Jt Li Lj Lw Mi Mm Mw Mz No Nw Ok On Qa Qc) aA(Ih Ij Im Ir Ji Jm Jn Js Jt Li Lj Lw Mw Mz No Nw Qb Qc) Lw(Fp Ij Ir Is Jn Js Li Lj Mw Mz Ng No Qa Qb Qc Qd) Ik(Fp Ij Im Ir Is Jn Js Jt Li Lj Mi Mw No Nt Qa Qd) Li(Hu Ih Ij Im Ir Ji Jn Jq Mg Mm Ng Nw Oi Qc) Mw(Hu Ij Ir Jn Jq Jt Mi Mm Mz Ng Oi Qc) Nw(Hu Ih Ij Im Ir Jn Jt Lj Mh Mm Ng Nx) Ng(Ij Im Jg Jn Jt Mi No On Qa Qb) Qc(Ih Ij Im Jn Jt Mi Mp No Nt Ok) Oi(Fp Ih Ij Ir Jn Js Jt Mz Nn Qa) Lj(Ih Ij Im Ji Mi Mm Mp No On) Nx(Ih Ij Im Is Ji Jn Js Qb) Mi(Hq Ih Ij Im Jn Qb) No(Ih Ir Jn Mm Qb) Hu(Ij Im Nn On Qb) Jt(Fp Jn Mg Mz Qb) Im(Hq Ji Mm Qd) Fp(Jq Mz Nc) Ij(Mg Mp Qd) Nc(Mz Nk) Ji(Jq Ms) MkPa MmQa IhIi QdJn PdPe} Im{Of(aA Hv Ij Ip Ir Jg Ji Jl Jo Jp Jq Js Jt Lh Li Lv Lw Ma Mi Mn Mp Mr Mt Mz Nb Nk Nm Nn No Ns Nt Nu Nw Oh Ok Om On Oz Pa Pb Pc Pe Qc Qd) Oy(AA Fr Ip Ir Jg Jh Ji Jj Jl Jp Jq Js Jt Lh Li Lw Ma Mi Mn Mp Mr Mt Mw Mz Nb Nn No Nt Nw Oe Og Oh Ok On Pa Pc Pe Pf Pg Qc Qd) Pb(AA Fr Hv Hw Ij Ip Ir Ji Jj Jl Jo Jp Jq Js Jt Lh Li Lj Lw Mi Mp Mr Ms Mt Mz Nb Nn No Nr Nt Nu Nw Oe Og Ok On Pa Pc Pc Qa Qd) Oe(aA Ih Ij Ik Ip Ir Jg Ji Jj Jl Jp Jq Js Jt Li Lj Lw Mi Mp Mr Mt Mz Nb Nn No Nt Nu Nw Og Oh Ok On Oz Pa Pc Pe Qc Qd) Hu(aA Fr Ij Ip Jg Jh Ji Jp Jq Js Jt Lh Li Lw Mi Mp Mr Mt Mu Mz Nb Nn No Nq Ns Nt Nu Nw Oh Ok On Oz Pa Pc Pe Qc Qd) Og(AA Ij Ip Ir Jg Ji Jj Jl Jp Jq Js Jt Li Lw Mi Mr Mt Mz Nb Nm Nn No Ns Nt Nu Nw Ok Om On Oz Pa Pc Pe Qc Qd) Nk(aA Hv Ih Ir Iv Ji Jp Jq Js Jt Lh Li Lj Lw Mi Mp Mt Mz Nc Ni Nj Nn No Nt Nu Oh Ok On Pc Pe Qa Qc Qd) Hr(Hv Hw Ij In Ip Ir Ji Jl Jn Jo Jq Js Jt Lh Li Lw Mi Mr Mt Mz Nb Nf Nm No Nr Nt Nw Ok Om On Pa Pe Qa) Oz(aA Ip Ir Ji Jj Jl Jp Jq Js Jt Li Lj Lv Lw Mi Mp Mr Mz Nn No Nr Ns Nt Nw Ok On Pa Pc Pe Qd) Ik(Fp Hv Ij Ip Ir Iv Ji Js Jt Lh Li Lj Lv Mi Mp Mr Mt Nb Nn No Ns Nt Nu Ok On Pa Pe Qa Qd) Ns(aA Ir Jg Jp Jq Js Jt Li Lj Lw Mi Mp Mt Mz Nd Nn No Nt Nu Nw Oh Ok On Pc Pe Qc Qd) My(Fr Ij Jg Jh Ji Jt Lh Lw Lx Mi Mr Mt Mw Mz Nb Nm Nn Nq Nw Om On Pa Pe) Ng(Fr Jg Jp Jt Lh Li Lw Ma Mg Mi Mm Mp Mt Nb Nm Nn Nt Nu Nw On Pa Pc Pe) Jj(aA Ij Ip Ji Js Jt Li Lw Mi No Nt Nu Nw On Qc Qd) Hq(Ij Ir Ji Jt Lh Li Mi Nd No Nw Ok On Qd) Lw(aA Ip Jp Li Lj Mf Mz No Nw On Qc Qd) Ip(aA Jq Li Nn No Nt Nu Ok Pc Qc) Jp(Ij Jq Jt Li Mi Mp Nn No Pc Qd) Mh(Is Lx Mr Mt Nb No Nw Pa Pe) Jt(aA Ii It Jk Jo Li Ms Nw Nx) Qc(Mp Ms Nn Nt Nu Ok Pc) Nw(aA Ir It Nu Nx Qd) Ji(aA Ii Jq Ms Nx) Li(aA Ij Jq Mi Qd) Lj(Mp Nn On Pc) Nx(Js Lv Nt Ok) Mt(Hx Mv Ny) Jk(Ir Nb On) aA(Me Nj Nm) Hx(Nb Pe) It(Hv Jn) Jo(Nt Ok) On(Mv Mw) TiKl NnOi NoOh NuJq MeMf MiMs MkPa MzPc} Nw{Oy(aA Fp Hv Hw Ih Ij Ip Ir It Jg Jh Ji Jm Jn Jo Jt Li Lj Lw Mg Mh Mi Mp Mt Mw My Nb Nd Nm Nn No Nq Ns Nt Nu Oe Og Ok On Oz Pf Qa Qd) Of(aA Hv Hw Ih Ij In Ip Ir It Jg Ji Jn Jo Jq Jt Li Lw Mh Mi Mp Mr Mt Mw Mz Nb Nd Nm No Ns Nt Nu Ok Om On Oz Pb Pc Pe Qa) Mh(aA Fp Hu Hv Hw Ih Ij In Ip Ir Is It Ji Jj Jm Jn Js Jt Li Lj Mi Mr Mt Mw No Nr Ns Nt Nu Oe Oz Pe Qa) My(aA Ih Ij Ip Ir It Jg Jh Ji Jm Jn Jt Li Lw Mg Mi Mp Mt Mw Nb Nm Nn No Nq Ns Nt Nu Og On Oz Pb Pc) Hr(Fp Hv Hw Ih Ij In Ip Ir Iv Ji Jn Jo Jq Jt Li Lj Lw Me Mi Mw Mz Na Nm No Nt Ok Pc Pe Qa) Oz(AA Fp Hu Hx Ih Ij Ip Ir It Ji Jj Jn Jt Li Lj Mi Mp Mv Ng No Ns Nt Nu Ny Oe Og Qa Qd) Pb(AA Fp Hv Hw Ih Ij Ip Ir It Ji Jj Jn Jo Jt Li Lj Mi Mw No Ns Nt Nu Oe Og Ok Qa) Oe(aA Ih Ij Ip Ir Is It Ji Jm Jn Jt Li Lj Mi Mw No Ns Nt Nu On Pc Qa Qb Qd) Og(aA Ih Ij Ip Ir It Jg Ji Jm Jn Jt Li Lw Mg Mi Mw Nm Nn No Ns Nt Nu On Qa) Nx(Hv Hw Ih Ij In Ip Ir Is It Ji Jn Jo Jq Js Jt Lw Mi Mz Nm Nt Ok Qa) Jj(Ih Ij Ip Ir It Iv Ji Jm Jn Jo Js Jt Li Lj Mw Nn No Nr Nt Nu Qa) Ns(aA Hx Ih Ij Ip Ir It Ji Jn Jt Li Lj Lw Mp Mw Nd Nn No Nt Nu) Hu(Ih Ij Ip Jm Jn Jt Li Mi Mp Mw Nn No Nq Nt Nu On Qa) aA(Ih Ij Ip Ir It Ji Jm Jt Li Lj Lw Me Nm Nu) Mv(Ij Ji Jn Mi Mp Mt Mw Nn Nq Nt Nu On) Ij(Hx Ii Ik Li Lj Md Ml Mw Ng Nv Ny) Nt(Hx Ik Ip Lj Ly Nd Ng Nv Ny Po) Ji(Hx Ir It Jq Lj Md Ml Ms Nu Ny) Jt(Ii Ip It Jo Lj Md Mj Ng Nv Ny) Ip(Ih Li Lj Lw Mw No Nu Pc) Md(Hv Hw In Jo Jq Mz Qa) Mi(Hq Hx Ih Lj Nv Ny Pg) Ng(Jg Jm Mg Mw Nm Nn Nu) Nd(Hq Ly Mk Ms Pd Pg) Li(Ih Ik It Lj Lw Pf) Ny(Hv Hw In Mz Pc Qa) Po(Hw Lh Mr No Pe) Nu(Ih Ir It Lj Lw) Nn(Mu Mw Oi Pc) Lw(Lj Mf No) Mk(Jl Pa Pe) Mp(Lj Nv Pc) Ms(Jn Ly Mw) Hx(Hv Hw It) Ii(Ih Ir Jo) Om(Hv Hw In) Ml(In Mz) Ik(Ir It) Jn(Jr Js) On(Mw Nv) NmMf NoOh LyIt NcNk PdPe} Ji{Jq(aA Hr Ih Ij Ip Ir Is It Jg Jm Jn Jp Js Jt Li Lj Ma Mw My Mz Nm No Nt Nu Nx Ny Of Og Ok Oz Pb Qc Qd) Nx(aA Fr Hr Ih Ij Ip Ir Jg Jm Jn Jp Js Jt Li Lj Lx Ma Mn Ms Mw Nd Nk No Nr Nt Nu Og Ok On Oz Pb) Oy(Fr Ih Ij Il Ip Ir Jg Jh Jm Jn Jp Jt Li Lj Lx Ma Ms Mw Nd Nk No Nr Nt Nu Ok On Oz Pa Pf Qd) Ms(aA Hr Ih Ij Ik Ip Ir Jg Jj Jn Jp Jt Lj Ma Md Mh Mw My Mz Nd Nk No Nu Of Og Oz Pb Qc) Hr(aA Fr Hw Ih Ij Il Ip Ir It Jg Jl Jn Jp Jt Li Lj Mr Mw No Nr Nt Nu Og Oz Pa Pb Pe) Nk(aA Ih Ij Ir It Iv Jg Jm Jn Jp Jt Li Lj Md Mw My Nc Ni No Nt Nu Of Pb Qa Qc Qd) Og(aA Fr Ih Ij Il Ip Ir It Jg Jm Jn Jp Jt Li Lj Ma Mw My Nm No Nt Nu Of Ok Oz Pb) Jj(Fr Ih Ij Ip Ir It Jg Jm Jn Jp Jt Li Lj Ma Md Mw My Nm No Nr Nt Nu Oz Pb) Of(aA Fr Ij Il Ip Ir Jg Jn Jp Jt Li Ma Mi Mt Mw Nd Nm No Nt Nu Ok On Oz Pa) My(aA Fr Ij Il Ip Ir Jg Jh Jn Jp Jt Li Ma Mt Mw No Nt Nu On Oz Pa) Oe(aA Fr Ih Ij Ip Ir Jg Jn Jp Jt Li Lx Ma Mw No Nt Nu Ok On Qa Qd) Ik(Fp Fr Hu Ij Ir It Iv Jg Jn Jt Li Lj Lx Ma No Nr Nt Nu Qd) Pb(aA Fr Ih Ij Ip Ir Jg Jn Jp Jt Li Lj Lx Ma Mw No Nt Nu Pf)

Lx Lz Mg Mh Ml Mt Na Nb Nn Oa Oh On Ow Pe Pf Pi Pj Ps Pz Qa Qx Ra Rf Ru Sr Va Vh Vq Zw Xa Wm Ti) Ji(aW aY Bb cP Cx Ed Fc Fw Ic Ih Is Jg Jk Jn Ks Mk Mt Mw Nb Nt Ny Oa Pe Pz Qa Qd Qy Si Sr St) Ow(aA aF aO aX aY bF bR cG dH Dr Ed Eq Hb Hx Jk Jl Kq Nb No Nw Ny Oz Pb Pc Pe Pi Ps Qd Un Wb) Kq(aR aZ bL Ch CX dG Gn Gp Hf Is Lu Lx Mh Pf Pj Qb Rj Uh Vs Th) Ld(Dc Ed Fw Ih Is Jg Jn Ko Mt Nb No Ny Pe Pz Qa Qc Qe Qh Sr St Uh) Mt(aM aX bV Ed Eq Hb Ki Lj Nw Or Oz Pb Pc Pj Uh Vt) Nw(aW Gc Jh Mv Nm Nn Oe Om Or Pj Qy Rx Sr) Qa(aG aJ aN Bn Bo Cx Dd Gc Hb Ic Pj Uh) Pe(aK aU Cx Gc Ha Mp Nq Oz Pc Ur Vt Wf) Gc(Iv Mv Mw Nn Oa Ry Ut) Nb(Mk Mp Nq Ou Pj Uh Un) Pj(Is Jl Jn Nv Oa Ut) Nn(aX aZ Ed Eq Hb) Is(Oz Pc Qy Un) Et(aY Ed Sr) Qy(Lh Lx Oh) Om(Aj Oy Pb) On(Oe Rx Vt) Uh(Cu Ni Ps) Ut(Hb Hc Oz) Qd(Ic Ti) Sr(aG Ur) ChJh DdMq NoaU NtVt LxbJ MwOi PsRx PfaY} Ir{Hr(Fr Hv Ik In Ip Jo Js Lx Ma Mi Mm Mn Mp Mr Nb Nm Nn Nt Nu Oe Om Pc Pe Qa Qd) Oy(Aa Io Jn Jq Js Lh Lx Mg Mi Mt Mz Nm Nq Nu Nv Oe Om Pc Pe Pf Pg Qd) Ik(Fp Iv Jn Js Lh Lv Lx Mg Mm Mn Mp Mt Mz Nm Nn Nq Ns Om Pf Qa) Mi(Hq Ip Iu Lj Lw Ma Mh Mn Mw My Mz Nm Nn Ns Nu Oe Of Qd) Mp(Fr Hq Ip Iu Lj Mk Mn Mw Mz Nk Nm Nu Of Pd Qd) Nn(Hu Ip Lj Mn Mw My Mz Nm Ns Nt Nu Oi Pc Qd) Pb(Aa Fp Jn Lh Lj Lx Mt Mz Nq Om Pc Pe Pf Qd) Nu(Fr Ip Jo Jq Ma Mn Mw Mz Nd Nk Ns Qd) Oe(Ih Jn Mg Mh Mt Mz Nd Nq Nv Ny Pc Qa) Ns(Fr Lw Lx Ma Mm Mn Mw Nm Nt Qd) Ip(Fr Jg Jo Lw Ma Mm Mz Nd Nt Qd) Nt(Lw Ly Mh Mn Mw Nd Nk Of) Oz(Aa Lj Lv Lx Mz Pc) Lw(Fr Lj Mn Mz Qd) Jg(Hu Lj Mw Nd Nk) Of(Fr Mn Mt Nm Om) Mm(Lj Mn Nk Qd) Mh(Lx Mt Mz) My(Jh Nq Om) Va(Bo dI Ld) Ma(Ih Mw) Nk(Mw Qd) Hu(Fr Nq) Jo(Mn Nm) On(Mk Mv) CxmS MtZw NdHq QdPc UhbN} Nb{Rt(aC aF Ao Ap aU aW aX Bb bC bE bJ bW cC cG cL CO cP cS Cu Cw Cx cZ Dd De dK Ef Et Ez Fi Gb Gc Ho Hv Hw Is Iu Jh Ji Jo Kc Kd Ke Kg Ko Kq Ld Ma Mg Mi Mm Mp Mt Mu Mv Na Nm Nn Nq Nw Om Ow Pd Pj Qy Qz Rz Ue Uf Un Vq Wd Ti) Tl(Af aJ aN aW Bn Bo bS CX Dk dM Ib It Jl Ld Ny Oe Oz Qn Qv Rj Rx Uh Ur Vp Wf) Eq(aW CO cS cZ Ez Jh Ld Mg Mq Mt Nn Pd Ue Uf Vq) Bo(Uw Ux Vh Vw Vz Wc Wd Ye Xa) We(aW cV Ke Kq Ld Mq Mw Nn Nq) Ur(Fc Fi Gh Gn Lp Si Uy Zw Ti) Ld(Uw Ux Uy Va Vb Vh Vz Zw) Ti(Aj Ar Kl Uc Uu Vs) Rx(aL cH cV Iv Lu Oa) Sr(Hl Ry Vz Yl Zw) Gc(Ed Up Us Uu) Wd(Aj De Kj Us) Zw(Ow Pe Po) Of(Fr Ma Vh) cV(Lp Wf Ye) Mq(Uw Wh) Qd(Oe Pb) Jg(My Oy) Uh(bN Dr) Un(Ru Va) Us(Fi Rz) AaQc ArHo Fdlv NoHx NhWf HlVq HrQa HbVa IpPb UxPj} aA{Ns(Fp Fr Iq Is Iv Jm Jq Me Mg Mm Mt Nc Ni Nj Nn Nv Om Pb Pc Pe Pf Pg Po Pz Qe) Oy(Fp Ii Io Iq Is Jh Jo Jq Me Mi Mm Mp Mt Nn Nu Nv Om Pc Pe Pf Pg Po Pz Qe) Me(Fr Hu Il Io Iq Is Iv Jm Jq Lv Mg Mp Mt Nj Oe Om Pc Pe Pf Pg Po Qe) Oe(Ii Il Iv Jk Jl Jo Jq Mm Mp Mt Nn Nx Pc Pe Pf Pg) Nj(Fp Fr Is Lh Mg Mp Nk Nn Om Pe Pf Pg Po Qe) Mg(Fp Hr Hu Ik Iq Is Jm My Nd Ng Of Qe) Hr(Fp Hv Hw Ii In Jm Lh Mi Om Pe Po) Pb(Ii Il Iv Jo Jq Lv Mt Nn Nx Pc Pz) Cx(kP IX ml mU nK Uz Wb We Xa) Mm(Fp Iq Iv Jm Jq Pe Pf Pg Qe) Mp(Fp Hq Io Iv Jq Mk Pc) Nn(Eq Hu Mu My Pc Sh) Mi(Hq Io Lh Lx Qe) Nd(Fp Hq Iv Lh Lv) Hu(Fr Mu Nq Om) Io(Fp Jm Lx Po) Of(Jo Mt Om Pz) Pc(Fp Pe Pf Pg) Iq(Fp Iv Lv) Nk(Nc Ni) Rx(Ps Qa) TiLj GcOa MyOm KeRu cXnl} On{Hu(Fr Hr Hx Ih It Jg Jn Js Lx Ma Md Mh Mi Mk Ms Mw Mz Nm Nn Nr Ns Nt Nu Ny Oz Pb Qa Qb Qc) Ns(Hr Hx Ik It Jg Jn Js Lw Lx Ma Mh Mi Mk Mn Mp Ms Mv Mw Ng Nt Nu Nv Ny Qa Qb Qc) Ip(Hr Ii Ik It Jn Jo Js Lw Mi Ms Mv Mw Nu Nx Pc Qa Qc Qd) Ng(Ih It Jn Js Lw Ma Mg Mi Mw Nd Nm Nt Nu Qc Qd) It(Hr Ii Ik Jo Lw Ly Mi Ms Mv Nd Nk Nu Nx Qc) Oz(Fp Hr Iv Jn Js Lw Ms Mv Mw Pe Pf Qa Qb Qc) Ih(Hr Ii Jo Lw Mi Ms Mv Nk Nu Nx Oi) Jn(Hr Ik Jo Lw Mi Ms Mv Mw Nk Nx Qc) Js(Hr Ii Ik Jo Lw Ms Mv Nk Nx) Qd(Hr Lw Mk Mv Mw Nk Nu Nx) Pb(Hv Jg Jq Ma Mh Mv Nu Qc) Lw(Fp Hr Ms Nu Qc) Mi(Hq Hr Jo Ms) Ik(Fp Ms Nt Qa) Mv(Hr Jg Lj) Of(Fr Lx Nr) Nt(Jo Ly) Ms(Nd Qc) Mw(Jg No) Hr(Jo Pe) EqNn FcUu NkQa ZwLj KdRt} Jg{Lj(Hu Ik Ip It Jn Jq Js Lh Lx Mw My Mz Nd Ng Nn No Ns Nt Of Oh Oi Oy Oz Pb Pc Qa Qb Qd) Of(Is It Jn Jq Lh Lw Lx Mp Mr Mt Mw Nd Ns Nt Oe Om Oz Pb Pe Qc) Mi(Hq Hu Ik Ip It Jn Jo Js Mg Mw Mz Nd Ng Ns Oe Oz Qa Qb Qd) Oy(Ip Is Jn Jq Lh Lw Lx Mp Mw Mz Pa Pf Pg Po Qa) My(Is Jn Jq Lh Lx Mp Mr Mw Nq Nt Pe Qa Qc) Oe(Fp Ip Is Jn Jq Lx Mw Mz Nd Nt Oz Pb Po) Ng(Ip It Jn Lw Mp Mw Mz Nd Nt Nu Qa Qb) Pb(Fp Ip Jn Jq Js Lh Lw Mz Nt Pe Qb) Ip(Hu Jq Js Lw Mz Oz Qa Qb Qd) Qa(Hr Hu Jo Lw Ns Oi Oz) Qd(Hu Ih Jo Lw Nd Ns Oi) Qb(Hu Ik Lw Ns Oi Oz) Js(Hu Ik Lw Ns Oi Oz) Ih(Hu Ik Jo Nu) No(Mv Nd) Hr(Jq Mz) Ld(Va Zw) EdSh FpIk NnHu NsMp MtMv KeUu OzPe} Qd{Oy(Aa Fr Ih Jn Jq Js Lh Lw Lx Mg Mi Mm Mn Mp Mr Mt Mw Mz Nd Nm Nn Nt Nu Oe Om Pa Pc Pe Pf Pg) Pb(Aa Fr Hw Ih Jn Jo Jq Lx Mi Mm Mn Mp Mr Mt Mw Mz Nm Nn Nr Nt Nu Om Pa Pc Pe) Oe(Fr Ip Is Jn Lh Lw Lx Lz Ma Mi Mm Mn Mp Mr Mw Mz Nd Nm Nn Nt Nu Ny Pa Pc) Mi(Hq Ih Ip Jn Lj Lw Ly Ma Mw My Mz Ns Nu Of) Ik(Ih Io It Iv Js Mp Mt Nd Nv Om Pc Qa Qb Qc) Ip(Ih Jn Lw Ma Mn Mw Mz Nn Nt Nu Of) Lw(Ih Jn Lj Ma Mw Mz Ns Nt Nu) Ih(Ma Mm Mw Nk Nn Ns Nt Nu) Nt(Jo Ly Mw Nd Ns Of) Hr(Hw Jo Jq Lh Mz) Nn(Eq Hu Jn Oi) Ru(Af Dr Ur Uu) Ns(Ma Mp Mw) Dr(Kd Th) Ma(Jn Of) Mt(My Of) AaOz AjBb NuJq MwMy NdHq} Nn{Eq(aE Af aS aX aY aZ Ba bE bH bJ bM BO bQ cB cE Co Cu Cx cZ dD dl Dk dL Dr Du Ed Ef Em Fn fR Hl Hp Hu Ib Iz Jd Je Jf Jh Jk Jn Jy Kq Ld Lx Mh Mr Ms Mt Mu Mv Mw Mx Ni Nj No Nq Nt Nu Nv Nw Ny Ps Ql Qy Rc St Ua Un Uo Wb Wd Ti) Ed(Dr Du Fi Gb Gh Gn Hl Ho Ps Rt Rv Rx Rz Sh Ux Va Vz Wb Wf Yl Zw Ye Tl Xa) Wb(aX Kl Ng Qu Sh Ss Vt) Dr(Kl Qu Sh Ss Vb Vt) Aj(Hp Ps Vb Wd) No(Rz Wf Wh Zw) Hp(aZ Kl Ng) aX(Va Vw Zw) Aa(Oy Pb) Sh(aE Qy) Ke(De Vs) Kl(Ps Vw) AdnD DgPs MwWf Ihlp ZwUn KdRt} Qa{Hr(Fr Ih Jl Jn Jq Lh Lw Lx Ma Mn Mt Mw Mz Nm Nt Oz Pa Pb Pe) Pb(Aa Fr Lh Lw Mi Mm Mn Mr Mw Mz Nk Nt Pe) Af(Ux Vb Vh Vw Vz Wb Yl Zw Zx Tm Tl) Oe(Fr Ih Ip Jn Ma Mi Nt Nu Oz) Uh(Cw Ha Ii Jo Lh Nk Ou Uu Vs) Zw(aN BN Cx Kr Qv Us Uu) Oz(Aa Fc Fr Ma Mi Mn Nt Rt) Bn(Vb Vh Vz Wb Wc We) aN(Ux Wb Wd We Wh Zx) Ma(Ih Ik Ip Of Oy) Wf(aY bJ Mw Nu Us) Mi(Hq Ik Of Oy) Rt(dG Ex Oi Pc) No(Mh Nk Of) Ip(Mn Nt Oy) Wb(aW Dk Qn) Aa(Oi Oy) Aj(Bb Rx) Cx(We Zx) Mt(My Of) Ur(Lp Ru) Us(Rv Sh) aY(We Ye) BbJo DrQn FcUu NsNd NtIk LwOy RzUv VabM} Va{Ps(Af aJ aR aZ bM Bn Bo CX dB dG Dk Hc Hu Ib Ki Oe Oz Qt Qw Rj Rx Uh Uu Vp Vq Vt Wf Ye) Ed(Ba Cu Ez Ji Ld Mg Na Ni Nk Nw Ow Pd Vq) Sr(aG aN bM bO cF Dr Or Uo Uv Vt Vz Yl) Ld(Al aX Bb Dc Fw Ih Il Jm Kd Lp St) Un(aN aY cD Fc Fi Fw Jm Ow Pa Ru) Cx(Hv Hx Ih It Ke No Pe Xa) Ih(aG aZ bM Hb Ur) aN(Ji Ke Nw Pe Vt) Ch(Ef Kq Qy Ut) No(aW cL Vq) Nw(aD aY Us) Af(Om Pe) Qy(Eq Vt) Rm(Bo dI) NtVt MtaX HbJn IsdD IuaZ StdI KdQm KeaD KqUv NyVq OwdL PebM} Oz{Aa(Et Fp Fr Hr Hu Ih Is It Iv Ji Jn Jr Js Lx Lz Mi Mk Mr Mt No Of Pe Pf Pg Qb Qc) Ip(Fp Fr Is Iv Jn Jq Lh Lj Lw Lx Lz Ma Mn Mp Mr Mt Mw Mz Pe Pf Pg Qb) Mi(Fr Iv Jn Js Lx Ma Mn Mw Mz Nt Nu Ny Qb) Ps(aZ Ed Fw Lj Mh Ml Mx Oa Pe Us Vs) Fr(It Jn Jq Js Lj Nt) Nt(Js Lj Ly Mw Vb) Ed(Wd Wh Zw Xa) Lj(Jq Lw Ma Mp) Sr(Rt Vh Xa) nl(nC nH nL) Fc(Iv No) Fw(Sh Sj) Ma(Js Qb) Mt(Eq My) Ih(Mw Nu) DuPe LwJs WbOw XacV OaVw} Pb{Aa(Et Fp Fr Hr Ih Ip Is It Iv Ji Js Lx Lz Mi Mr Mt Mu No Pe Pg Po Qb Qc Qe) Mi(Fr Jn Js Lh Lj Lx Ma Mn Mw Mz Nm Nt Nu Ny Qb) Ip(Fp Fr Jn Jq Js Lh Lj Lw Lx Ma Mn Mr Mw Mz Pe) Nt(Fr Ih Is Jn Js Lj Ly Ma Mw Mz Nd Qb) Ma(Fp Jn Jq Js Lh Lj Mr Mz Pe Qb) Fr(It Jn Jq Js Lj Lw Mz Oe) Ke(Af Cx Ii Mm Nx Ou Us Uv) Ih(Lh Mw Nu Om Pe) Lj(Lh Lw Mp) EdWd LwJs LxMz IsOe JnLh UhbN nHnl} Ed{Xa(Af aW Ba Bn bQ bZ cP cV cW CX DK Ez Gn Io Ld Mk Na Nj Nk Oe Oi Pc Qn Qv Rc Sh Vq Vt) Ld(Du Eq Fc Fi Gh Gn Op Rt Ru Ux Vw Wc Zw Zx Ye Tl Ti) Ru(aG bH cV Cx dE Kq Kz Pa Vt) Dr(aQ CX Hq Ow Vt) Ps(cN CX Oe Qn) Ba(Fi Gb Lp) Cx(kE lX mS) Gn(aM Mq Ni) Pd(Fc Fi Wc) Cu(Rt Wc) Eq(Ez Mq) Sh(Ih Qt) Ye(Ea Mq) Ow(Gd Op) FiMg GcQw NiRt KeLh RvPf} Ih{Mi(Fr Hr In Ip Jn Lj Lw Ma Ms Mw Mz Nk Nm Ns Nt Nu Ny Oe Of Oy Qc) Ip(Fr Hr Jn Jq Lh Lj Lw Mm Mn Mp Mw Mz Nk Nu Oe Oy Pc) Nt(Fr Ik In Lj Lw Ly Ma Mm Mw Mz Nd Nk Ns Oy Qc) Ma(Ik Jq Lj Lw Ms Mz Ns Nu Of Oi Qc) Oe(Lx Mm Mw Nu Ny Om) Hr(Hw Jo Jq Lh Mz) Fr(Lw Ns Nu Oy) Aa(Oy Qc) Nu(Jq Lw) Sh(Jv Sr) Lj(Lw Mm) Uu(Gc Rx) AjBb MtMy ZwLd} Lj{Mi(Hq Hr Jn Jq Lw Ma Mm Mn Mw Mz Ns Nt Nu Ny Oy) Nt(Ik Ip Jq Lw Ly Ma Mw Nd Oe) Lw(Hr Ip Jn Js Lh Ma Mw Nu) Du(Cu Iv Kq Ld Mq Mt Pd) Qy(Dr Gh Yl Ye Tl) Ma(Ik Ip Jq Mz) Wb(Gc Mg Ow Si) Jq(Hr Mp Nu) Ld(Vb Vw Zw) Ps(dI Pc) DrKc NsMp MhMt MzHr VzSr ZwJh RxNy RtPi} Mw{Wf(aW Ax bA cT dK Em Fy Jn Lx Mh Nr Ow Pe Pf Ru) Sh(aN aW

Figure 36 Continued bA Gp Il Nd Oe Oi Ow Pa Pf Ru) Ru(Af aZ Ch Hc Qw Vt Wh) Ip(Jn Jq Js Mi Nt Oy) Eq(Ez Ld Mt Ow) Ch(Vb Vw) Mi(Hq Jn) My(Js Mt) Hr(Jq Mz) Wh(cT Ml) Uh(Bg Oy) Uu(Gh Vz) DrVs NoHu NtIk MhZw LdUy UwPe} Uh{bN(Ad aM As Bn Cp Cq Cw Dc Hw Id In Iv Ji Kn Kp Kq Kr Mz Nf Ny Om Pi Pk Ra Rj Sr Tv Up Vp Vv) Uu(It Jn Jq Ke Kq Lw Na Sr) Ke(Af Jo Kf Lh) Kq(De Uv) nI(Nx Ub) DraW ItJo} Oa{Rx(bM bO dI Dr Du Hp Hx Ld Mu Ni Ny Uo Ur Wb) Gc(Af bM bO Cq dD dI Dr Iq Uo Wb) Rt(Ho Ji Kd Mi) Cx(Uz Vw Xa) Zw(Ic Mt Sr) Wf(Hu Jh Qy) Fc(Cv Ur) Qy(Sh Ye) Pj(Dr Wb) AfVw HuYe} No{Mp(Hq Of Pc Pd Pf) My(Mg Mz Nq Om Pc) Is(Hr Hu Iv Of Oh) Mh(Jq Nj Qb Qc) Nk(Js Ni Nj Qb) Nd(Nj Nt Pd) Of(Hv Jo Nm) Po(Lh Pe) Hr(Mi Om) Kd(Wf Wh) aW(Rz Sh) AaOy NuJq MgNg MkPa MuHu JsOh} Ke{Nx(Ad Bg bL bN De dK Jo Kj Ld Lh Mm Uv Vo) Lh(Cx Fy Ml Qn Uu Uv Vo) Ru(Af Dr Jo Wb) De(eC Uv Vo) Il(Jo Ph Uu) Uv(Kf Ph) Uu(Mm Ph) DraW JonN VobN} Cx{nN(Ad Aj Bg Cv Dc Iz Jo Kj Kl Kn mS Nm Of) mU(Ad Aj Ef Iz Kj Of) mI(Ad Aj Kj mS) mS(aJ aW kI) Pe(Vc Wf) mZ(kG Ld) DpnC KjnL LpUr NxnI} Aa{Oy(Et Fr Ip Iv Js Lx Mt Pe Pf Pg Qb Qe) Qc(Hr Hu Iv Jo Nk Nw Of Oi) Hr(Ip Nw Qb) Of(Et Js Nw) Ip(Jo Pc) Oi(Qb Qe) MyJh NwPc} Ow{Wb(aF aO cV cX Kl Lv Oi Pc Qn) Dr(An aY cX Nx Oi Qn) Zw(Hp Nu Qy Uo) Af(Eq Ho Vh) Qy(Eq Sh Ux) Kl(Gb Hp Vw) EqHu RxNy} Pe{Du(aO cA cK Gh Hc Nd Vc Wf) Wf(aN aY Bn Hu Kx Lv Qy) aN(Gh Vc Wh) BnVc MzHr ZwLd WhQy PsPc LpUr YlaY} Kq{Ru(Af Aj Bg Kl Of Tn) Nx(Eq Uw Wd Wf Wh) Ch(Ps Rx Wc Wd) Lp(Bg Ur Uu) De(Aj oH) Rx(aF Uv) AfUy BgTm} Js{Lw(Fr Hr Ip Ma Nu Oy) Ip(Hr Jo Nt Oy) Fr(Ik Oe Oy) Ma(Jo Of Oy) Nt(Ik Jo) BbJo NsNd MtMy HwjE} aW{Dr(Hb Ld Or Qg Qx Tz Vt) Wb(Cs Ld Ml Mq Qx) Ny(Eq Fi Ry Rz Yl) CsDu EqNv XaLd KgmS KlPs} Jn{Rx(bJ Hp Mq Nc) Mi(Hq Ip Oy) Fc(Ur Uu) Fr(Oe Oy) Wf(Nj Qy) AjnN NsMp MtMy MzHr ZwUf UuUx} Nt{Ip(Jo Jq Lw Ly Mz Nd Of Oy Qc) Mz(Hr Of) Ik(Is Qb) Oe(Is Qb) MtMy HrJq} nN{Aj(Af bJ Bn De nI Ql) Jo(aF bU cH Hb Ko nI) nI(Cv Nm Ug) AfhB HbKj} Hr{Mz(Fr Is Jo Lh Mr Qb) Jq(Fr Jl Lh Mi Nu Qb) Lh(Hv Lw) HwIp} Lp{Ur(cR Fp Iv Jl Ld Mq Mv Nw Ps Ql Sr) Ld(Uv Zx) IvaY QyUu} Dr{Ru(Ji Mk Mq Rh) Kd(Mk Mq Tz) Th(Ji Mk) Sr(aU aV) Pf(Sh Vt) FwLd} Eq{Mt(aN aX Qy St) Mq(Bb Fw Ph) Qy(Nr Oh Pf) Mu(Nr Pf) UtaF} Ps{Uu(cX Hu Oe Qy Sr) Us(Ho Kd) ExMl SrRx NyVp OeVs OiaY} Wb{Pf(aF aO cV Hc) Mk(Pa Ru) FwLd JiRu SraU OhaF} Rt{Jm(Cu Ho Hv) Kd(Hw Mq Ql) Is(Dd Sr) MiQb} Mi{Hq(Ip Lx Ma) Jh(My Oy) IpOy OfOm} Xa{Qy(Ch Uu) FcOi SrPc LdaY NxUn VtaN} Ru{Aj(Ef Jh) Mr(Ld Pa) EmLd NuNw IvUr} Uu{Gc(Hu Ny St) Qy(Fd Ho) FwWd} Mt{aX(Op Zw) AfWe FrWc MyIp} Rx{Ny(aF Ld Mq Ur) ChJh} aN{Fp(Fi Ho Ti) AjmI} Nu{IpJq IsOe TmNw} Ma{Qb(Oe Oy) MzOf} Sr{HuSh SfUv ZwUr} Kd{We(Mv Ql) MqUy} Ch{Jh(Uy Tm)} Ho{AfPf LdUv} Iv{ThLd VbaY} Qy{MxSh ZwOh} dM{bCjQ hAjK} nI{CvQc OymI} DdMqUy EtMeMf FcRmUr FrIsOe GlWfUt NsLxMh LtNxUn

Constrained panels with 3 analytes, where 1.0E-7 >= 'model p-value' > 1.0E-8. Contains 8,868 panels of 17,842,327 total panels evaluated. : Ij{Hr(Aa Bb Fp Fr Hu Hv Hw Is Iv Jg Jl Jn Jo Js Lx Ma Mm Mr Mt Mw My Nd Nm Nn Ns Nt Nu Oy Oz Pa Pc Po Qc Uh) Mz(Hu Hx Ih Ik Ip Jg Jn Jo Js Jt Lw Lx Ma Md Mh Ml Mm Mp Ms Mw Nf Nn Nt Nu Ny Oe Oh Oz Pc Qa Qc) Oz(Fc Fp Hu Ik Is Iv Jl Jn Jq Js Lh Lz Mn Mr Ms Mt Nd Nn Ns Nu Oh Pa Pc Pe Pf Qb Qc Rt Vh Yd) Jo(Aa aF cX dK Fr Hu iH Jn Js Ke Kg Kq Ld Lh Lw Lx Ma Mn Mw My Nm Nn Nu nW Ow Qa Qy Va Vs) Qc(Fr Hu Ih Ik Ip Jg Jn Jq Jt Lh Lx Ma Mm Mn Ms Mw My Nd Nn Ns Nt Nu Oe Of Pc) kS(Eq Fc Gd Hl Ho Lp Rt Rv Rx Si Uw Ux Va Vb Vh Vi Wc Wd We Wf Wh Yd Yl Zw) Ik(Hu Is It Jl Jn Jq Lh Lz Mn Mr Ms Mt Nd Nm Ns Nv Ny Oh Pc Pe Pf Po Qb) Of(Aa Hu Ih Io Is Iv Jl Jn Js Mn My Nm Nq Nv Ny Oe Oy Pc Pg Po Qa Uh) Lx(Hx Ih Ip Jk Jn Jq Lw Ly Md Mh Mp Mv Mw Nd Ng Nn Ns Nu Ny Pc Qa) Nn(Fp Ih Ip Jg Jk Jn Js Ma Ms Mu Mv Mw Ng Ns Nt Nu Oi Pc Qa) My(Aa Bb Ih Is Jl Jn Js Me Mg Mn Mv Nd Nv Oe Oh Pe Po Qa Uh) Hu(Ih Is It Iv Jn Jq Js Lh Ma Mn Mr Mt Nd Nt Nu Nv Oe Pc Qa) Rt(aF dR eF fP gL gP hB hG iA iH iJ iZ kR nW nY oE oF pF Wc) Vi(eF gL gP hB hC hG iA iH iZ kQ kR nW nY oE oH oK oN Tn) Nu(Ip Is Jn Jq Js Jt Lw Ly Ma Mn Mp Mw Nd Ng Ns Qa Wf) Oe(Io Iv Jl Jq Lh Ma Mn Mr Nd Nm Nv Ny Oh Pa Pc Pe Po) Mp(Fr Jk Jn Jq Js Jt Lw Ly Mk Ms Mw Ng Pd Pg Qa) Uh(Af Aj Bg Cw Hc Ii Im Jj Mm Nk Ou Oy Pb Ur Uv) Mw(Ih Is Iv Jg Jn Jq Lw Mm Ms Ng Ns Nt Pc Wf) Ip(Fr Jn Jq Js Ly Lz Ma Mm Mn Nd Ng Nt Qa) Aj(Bb Et Im Jg Jp Jt Mi Mt Nk Nw Qd Wc) Ns(Fr Ih Jg Jn Js Jt Lj Lw Ma Mm Nt Qa) Yd(bH cM dR Im Ke Mj Mt Mu Nb Pc Qd Tj) Lw(Fp Fr Jn Jt Lh Ma Mr Ms Ng Nt Qa) Jj(Aa aF aW Bb bO cE cX dH Uu Wc) Vh(dR fP iA oF oK oN pF Qy Vc) iZ(Fc Fd Gn Hl Rx Sh We Wf Zw) Fr(It Jk Jn Jq Jt Mv Nd Qa) Ih(In Jt Lj Ms Nk Nt Pc Zw) Wc(aY aZ bN Mg oF oK Ps Wb) Js(It Ma Mh Mm Ms Nm Nt Pc) Mt(Hx Md Mh Mv Ny Zw) Wb(hC kQ Nd nW Ok Pg) We(fP iA oF oK oN pF) Va(aY hG Hp Lv oF oK) Oy(Aa Fp Is Iv Jn Oh) Mm(Fp Jn Jq Qa Qb) Zw(cV hG oF oK Sh) Jg(Jq Jt Mg Mv Oi) Nt(Jq Ly Nd Ng) Ma(Jn Jq Nd Ng) Hx(Lh Mr Pa Pe) Lj(Lh Mn Nq Oh) Up(Hc Vb Vc Yl) Fc(oF oH pF) Ms(Jn Jt Nd) Nb(On Zx Tl) Ii(Jt Ke Lh) Qa(It Nk Nm) Xa(aY fP oF) Aa(Og Pc) Dr(kQ nW) Th(Cv Li) Ng(Lh Nm) Hc(Ur Vo) Is(It Iv) Vz(aW kQ) Wh(Ed Im) Wf(bM Uu) Qy(Uw Vb) Vc(aA Ad) DuhB EqMu GnhG MkPa HloF JhOn JnJt RxfP UuUx VbaY} Jj{Mn(Fp Fr Hv Hw Ii Il Iq Iu Iv Jk Jl Jo Jq Lw Lx Mg Mp Mr Mt Mx Mz Nn Ns Nv Og Om Pb Pf Pg Po Qc Qe) Nr(Aa Fr Ii Il Io Iq Iv Jk Jl Jo Jq Lh Lj Lw Lx Mg Mm Mp Mr Nn Nv Og Om Pb Pe Pg Po Pz Qc Qe) Fr(Fp Hv Ii Io Iq Iv Jo Jp Jq Lj Lw Mi Mp Mr Mz Nc Ni Nm Nn Ns Ny Oe Og Oy Pe Pg Qc Qe) Mw(Aa Bb Fp Hv Hw Il Io Iu Jk Jl Lw Mg Mr Ms Mt Nc Nn Og Om Pa Pf Po Pz Qe Uh) Mz(Fp Hr Ii Is Iv Jk Jl Jo Jq Lh Lj Lw Lx Mi Mp Nn Nv Ny Om Oz Pe Pf Pg Po Qe) Nm(Hv Hw Ii Jk Jl Jo Lw Ma Mg Mt Mx Nb Nc Nd Nn Nq Nv Og Om Pa Pf Qc Qe) Nu(Aa Fp Il Io Iq Iv Jk Jl Jo Lw Lx Mp Mr Nn Og Om Oz Pb Pe Pf Pg Po Qc) It(Fp Ii Io Is Iv Jk Jo Jq Lw Mg Mm Mp Mr Mt Nn Oz Pe Pf Po Pz Qc Qe Uh) Lj(Il Io Iq Iv Jk Jl Lx Mr Mt Nb Nd Nn Nx Pa Pb Pc Pe Pg Po Pz Qb Qc Qe) Ny(Fp Hv Hw Iv Jl Jo Jq Lv Lx Mg Mr Nd Nn Ns Nv Oe Og Pb Pf Pg Po Qc Qe) Uh(bN Cu Hv Im In Iv Jn Jq Jr Jt Kd Ke Ml Na Nb Qa Ra Sr Ul Up Ur Vp) Aa(Et Hr Hu Ir Is Iv Jk Jm Js Jt Mg Mk Nb Nn No Pc Pe Pg Qa Qd Qe) Lx(Ii Io Iq Is Iv Jl Jo Jq Lw Ma Mi Mp Mr Nn Oe Om Pb Pg Qb Qc) Mi(Fp Ii Io Is Iv Jk Jl Mt Nn Nv Om Pb Po Pz Qc Qe) Jm(Hv Hw Io Is Iv Jl Ke Lv Mg Mr Mt Pf Po Pz Qb Qc) Ma(Hw Iq Jl Jo Mp Mr Nc Nn Ns Nv Og Oy Pg Po) Is(Fp Iv Jo Lw Mg Mm Mp Nn Nv Pe Pf Pg Po Qc) Qe(Jo Jp Jq Lw Mp Nn Og Om Oz Pb Pg) Nv(Fp Iq Iv Jp Lw Ns Oe Oy Pe Qc) Qb(Bb Io Jh Mr Nq Ns Oe Pe Pg) Oz(Fp Ii Iv Jk Jo Jq Mt Nn Pf) Pb(Ii Jk Jl Jo Mt Om Pe Pg Po) Qc(Ii Jl Jo Lw Mp nN Om Po) Jp(Hv Hw Il Mg Oe Og Om Pc) Lh(Iq Jq Mp Nd Nn Ns Oe Pe) Fp(Ii Io Jq Lw Mm Om) aA(Il Iu Jk Jl Nx Pf) Bb(cX Ih Im Js Qd) Cx(mU nC nH nL) Nn(Iv Jo Jq Pe) Im(Ar kP Wf) Io(Jq Pe Po) Pz(Ip Pe Pg) Og(Ii Jk Jl) nI(mI nK nN) Il(Ke Om) Iv(Ii Om) DeKq PoJq TiNb LwJl MmPe MtMy HrJo IpJh JnPa} Jg{Ng(Fp Fr Ik Iq Is Iv Jl Jm Jq Lh Lx Ma Mg Mn Mr Mt My Nb Nm Nn Nq Nr Ns Nv Ny Oe Of Oh Om Oy Oz Pa Pb Pc Pe Pf Pg Po Qc Qe) Pb(Fr Hv Hw In Is It Iv Jl Jo Lx Lz Ma Mg Mh Mn Mp Mr Mt Mw Mx My Nb Nd Nn Nr Ns Nu Nv Oi Oy Pa Pf Pg Po Qc Qe) Oz(Fp Fr Hu Hv Is It Iv Jl Jn Jq Lh Lw Lx Lz Mh Mp Mr Mw Mx My Mz Nd Nn Nr Ns Nt Nu Oh Oy Pa Pf Pg Po Qc Qe) It(Fp Fr Hu Ik Ip Jn Jo Jq Js Jt Lh Lw Lx Mg Mp Mr Mw My Mz Nd Nn Ns Nt Nu Oe Oh Oi On Oy Pe Qa Qc) Oy(Aa Fp Fr Hv Hw Il Iq Iv Jh Jl Lz Mn Mr Mx My Nd Nn Nq Nr Ns Nt Nu Nv Ny Oe Of Oh Om Pc Qc Qe) Mz(Fp Hu Hx Ik Jn Jo Jp Jq Jt Lw Md Mh Ml Mp Mv Mw Nd Nf Ns Nu Ny Oh Oi Ok On Qa Qb Qc Uu) My(Fp Fr Hv Il Iv Jh Jl Lw Lz Ma Ml Mn Mx Nd Nn Nr Ns Nu Nv Ny Oe Oh Oi Om Pa Pg Po Qe) Oe(Fr Hv Hw Ik Iq Iv Jl Lh Lw Mg Mp Mr Mx Nb Nn Nr Ns Nu Nv Ny Oh Pa Pe Qc Qe) Lw(Fp Ik Is Iv Jn Jp Lh Lx Lz Mf Mg Mi Mr Mw Mx Nd Ns Nt Nu Oi Pa Pe Qc) Jn(Hu Ik Ip Jo Jq Jt Lh Lx Mg Mp Mr Ms Mw Nd Nn Ns Nt Oi On Pe Qc) Mp(Fp Hq Hu Hv Ik Ip Jo Jp Jq Js Jt Mg Mk Mw Ok Pd Qa Qb Qc) Ip(Fp Ik Iv Jo Lz Mg Mn Mr Mw Nd Nn Ns Nt Nu Oi On Pc Qc) Of(Aa Fp Hu Hv Hw Ik Iv Jl Mn Mx Nn Nu Nv Oh Pa Pg Po) Ns(Fp Hw Ik Is Jq Jt Lh Lx Mn Mw Nn Nt Nu Pe Qc) Hu(Fp Is Jp Jq Jt Lh Lx Mr Mw Nd Nq Nt Ok Pe Qc) Ik(Is Iv Jq Jt Lx Mw Mx Nt Ok Pe Po Qc) Oi(Aa Fp Is Jq Jt Mi Mw Nn Oh Ok On Uu) Nd(Fp Is Iv Jq Jt Ms Nt Ok Qa Qb Qc) Aj(Im Js Jt Li Mi

Figure 36 Continued

Mt Mw No Qd) Qc(Fp Jp Jq Jt Lh Lx Mi Mw Nt) Jq(Fp Jo Jp Mw Nt Nu Qb Uu) Hr(Hv Hw Js Lh On Pe) Jo(Lh Nt Ok Pe Qb) Jt(Fp Lx Ms Mw Qa) Jp(Mw Pe Qa Qb) Ok(Fp Mg Mi Mw) On(Jh Jk Mg Mk) Uu(Ji Qd Sr Uh) Js(Mg Mh Mv) Cx(mU nN) Nt(Ly Mw) Mk(Pa Pe) Nb(Rt Ti) Nk(Qa Qb) Is(Iv Mh) EqMq LxHq MiMv PdPe} Og{Jn(Fp Is It Iv Jh Jl Jm Jo Jq Lj Lx Mg Mm Mn Mp Mr Nd Nn Nq Nr Ns Nv Ny Oz Pa Pb Pc Pe Pg Po Pz Qb Qc Qe) Fr(Fp Hv Il In Iq Iv Jm Jp Lh Lj Mn Mp Mr Mt Mw Nb Nc Ni Nn Ns Nu Ny Om Oy Pa Pb Pe Qc Qe) Mz(Aa Fp Hr Io It Iv Jk Jl Jm Jq Lh Lj Lw Lx Mg Mm Mn Mp Mt Nb Nn Nr Nv Oz Pb Po Pz Qc Qe) Ny(Fp Il It Iv Jl Jq Lh Lj Lx Ma Mg Mn Mp Mr Mt Mw Nb Nn Nr Nu Om Oz Pa Pe Qb Qc) Mi(Aa Fp Hq Hu Ii Il Io Iv Jh Jk Jl Jm Jq Lw Me Mm Mt Nn Ns Pb Pe Po Pz Qc Qe) Lw(Fp Il Io It Iv Jl Jm Lh Lx Mn Mr Mt Nb Nm Nn Nv Om Oz Pa Pe Po Pz Qc) Ma(Fp Hv Iv Jl Jm Jp Lh Lx Mr Mt Mw Nb Nn Ns Nu Nv Om Pa Pb Pe Po Qc Qe) Mw(Aa Fp Iq Jl Jm Lj Lx Mg Mn Mp Mr Nn Nr Nv Oz Pa Pb Pe Po Qc Qe) Qb(It Iv Jh Jl Jo Lj Lx Mm Mn Mp Mr Nn Nq Ns Nv Oz Pa Pb Pc Pe Po) Nm(Hu Hv Ii Io Iq Jh Jk Jr Lz Mf Mj Mp Mx Nc Nn Nq Ns Oz Pb Pz) Nu(Aa Iq It Jl Lh Lj Lx Mn Mr Mt Nb Nn Nt Nv Oz Pe Po Qe) Ip(Hv Hw Io Iq Jm Jo Lz Mm Mv Mx Nc Nd Ni Nq Oh Pc Pf Pg) Jq(Fp Is It Iv Jl Jm Lh Lj Lx Mg Mm Mn Nr Nv Oz Pa Po Qe) Om(Fp Il Jl Lh Lx Mn Mp Mr Mt Nb Nn Nr Oy Pa Pe Po Qe) Is(It Iv Jh Jm Lx Me Mm Mp Mr Ns Nv Pa Pc Pe Po Qc) Lj(Iv Jh Jk Jl Jo Js Lh Lx Mm Mn Mp Nb Nn Nq Nv Oz) Jp(Hv Hw Il In Iq Jh Jl Jo Mn Nq Nr Oh Pc Pg Qe) Nt(Fp Ik Jl Lh Me Mm Nb Ni Nr Nv Pe Po Qe) Lx(It Iv Lh Mr Mt Nb Nn Oz Pb Pe Qc) Nv(It Iv Jm Mn Mt Nb Nn Ns Oz Pb Qc) Jl(It Iv Jm Js Mg Mn Mt Oz Pb Qc) Lh(Hr It Iv Jm Mn Oz Pb Qc) Aa(Fp Iq It Mu Nb No) Mn(It Mt Nb Oz Po Qc) Js(Iv Jm Mp Mr Ns Pe) Po(It Nb Oz Pb) Mt(It Iv Jm Qe) Pe(Mm Oz Pb) QeOz XaNx} Ke{Uv(aE AF aJ Ar aW aY bG bL cN dG dH dI dJ dK Ez Hq iJ Il Im Kl Md Mj Mm Ne Nn Nv oN Ra Rg St Uh Ur Uu Vo Vp Vs Wm) Uu(aE Af bG BN cH Cx De dH dJ dK Dp fP GP Hr Ii Jm Jo Kf Kn Mj Ne Nl Pb Po Qc Rg Sr St Ug Up Ur Us Vo Vp Yd) Jo(aE aW aY bG BN cH De dK Ez Im Jm Kf Ky Lh Li Lj Mi Ne Nn Nt Oh Pb Ph Pi Qc Qv Qy Ra Sr St Ug Ur) Vo(aE AF aW aY bG Bn cH dJ dK Gp Hr Il Im Jm Kf Kn Mj Ne Nk Or Ou Pb Pe Ph Qc Qy Rg Uh Up Us Vp Vs) Uh(Ad aF Aj BG Cw De dK Dp Gl Hc Hq Ii Im Iz Kg Kj Kl Mm Nk Nv Nx Ok Ou Oy Pb Ph Up Ur Vp Vs) Yd(Ap aY BA Bg bM Ch cV Cx De eF Fw gL iH Ik Is Jt Kn KR Mv Nj No oE oF oK Oz Pb Qz Rx) Mm(AF aW bG bN cH De dJ dK Il Im Jm Kf Lh Ne Nk Nn Oh Ou Oz Ph Qc Qy Up Us Vp Vs Wm) Lh(Af bN cX De fP Hb Ii Il Im Jm Kf Kj Ld Lj Lz Nn oE Oh Pb Pe Qb Qc Sr Us Wm) Nx(aE Aj aW aY bG cA cK Cp Cw Hc Hq Ii Iz Jd Jh Jt kS Ou Oy Qz Rc Tn Up Vs) Kf(aE Af bN cH Cv Cx dJ dK Dp Ed Il Jm Nn oE Oh Oz Pb Qc Ur Wm) Pb(aY BN Cv cX De dK Jh Kj Ms Mt Ne Nn Pd Qn Up Ur Vv) De(bN dK dR Ez fP Ii Il Kq kS Mu oE Oz Qy Uf Up Ur) Il(Ad Aj BG Ii Iz Jh Kj Ok Oy Tn Up Ur Vp Vs) Im(Ad Aj Dr Hq Ii Iz Jh Kj Nv Oy Ph Vp Vs) Ph(Af bN Fy Jm Lj Nn Oa Oh Qc Qn Rf Ur) Vs(Af cT Cx eC Ed oE Oh Qa) bN(Aj Ii iJ Oi Oy Ur Us) Nn(Aj Iz Kj Kl Oy Uf) Af(bG Jv St Up Vp) Ii(aE eC Jm No Sr) Aj(aW bG Ez Up) Dr(Jm Kd) Fy(Ok Po) Kj(bG dK) Up(Kl Qc) Us(dK Oz) eC(Cu oN) NbZx JmUr RuVh} Jt{Ns(Fp Is It Iv Jn Jo Js Lw Lx Ma Mi Mj Mn Ms Mt Mw Mz Nn Nt Nu Nv Ny Oe Oy Pe Po Qa Qc) My(Aa Aj Fp Is It Iv Jh Jn Lh Lw Ma Mi Mn Mp Mw Mz Nn Nt Nu Nv Ny Om Pa Pe Po Qa Qb Qc) Oy(Aa Is It Iv Jh Jl Js Lh Lw Mi Mn Ms Na Nd Nm Nn Nq Nr Nt Nu Nv Ny Om Pa Po Qc Qe) It(Fp Ik Is Iv Jn Lx Ma Mi Mj Mn Mp Ms Mw Mz Na Nd Ng Nn Nt Nu Ny Oe Of Pb Qc) Jo(Aa Bg Ch Co Is Iv Jl Jq Mh Mj Mr Ms Mt Na Nd Nn Om Pa Pb Pe Pf Pg Po Qc Uh) Aj(bE BG bM bN cB cD CH cR Cx Hr Ip Ma Mf Mi Ne Nj Nl Nn Om Pb Qc) Of(Aa Is Iv Jh Jl Js Lh Mh Mj Mn Mr Na Nm Nn Nr Om Pa Pb Pe Pg Po Qc) Qc(Fr Iv Lw Lx Ma Mh Mi Mj Mn Mp Ms Mw Mz Nd Nt Nu Ny Oe Oz Pb) Nu(Fp Ik Is Jn Jq Js Lw Lx Ma Mi Mn Mp Mw Mz Ng Ok Qa Qb) Iv(Fp Ih Ik Is Js Ma Mi Mj Mp Mw Mz Na Nd Ng Ny Oe Pb) Mj(Fr Is Jl Jn Lh Lz Mp Mr Mz Ng Nt Oe Pa Pe Po) Mi(Fp Hq Ii Iu Jn Lx Ma Mh Ms Mw Mz Ny Oe Qb) Mp(Fp Hq Ii Ik Jn Mk Ms Mw Mz Ng Ny Oe Pd) Oe(Jl Mh Mn Mt Na Nm Nn Nr Om Pe Po) Pb(Is Jl Lh Lw Mr Ms Mt Nm Nn Nr Pa) Lx(Hq Ih Iu Jn Ma Mk Mw Mz Ng Ny) Fp(Ii Jn Lw Ma Mh Mw Na Nd Nk) Nt(Ii Iu Ly Mg Mw Mz Nd Ng Qb) Ms(Is Js Ma Mn Nd Nn Ny Pe Qa) Mh(Is Js Mt Mz Ng Pa Qa Qb) Ik(Fr Is Jn Ma Mt Nr Pe Po) Mz(Fr Jr Ma Mw Na Nn Qa) Ng(Mn Mt Mw Nd Nn Nv Ny) Ii(Ih Js Lh Nd Pa) Aa(Hr Lz Oi Qb) Ma(Jn Js Mw Qa) Fr(Hu Mg Qb) Nn(Hu Oi Pc) Mw(Jn Js Ok) Nd(Mk Ok Pd) Ih(In Jn Na) Uh(bN Qa Ur) On(Mv Nb) Oz(Is Po) CtIm NqHu LwNy NaQb PdPe} Lj{Mm(Hv Ip Is It Iv Jn Jq Js Lh Lw Lx Ma Mn Mr Mt Mw Mz Nb Ns Nt Nu Oe Om Oz Pb Pe Pg Qa Qc Qd) Mp(Fr Hq Hv Ih Io Ip Is It Iv Jn Js Lw Ma Mn Mw Mz Nb Nm Nt Nu Ny Om Oy Pc Pd Pf Qa Qc Qd) Oz(Ih Is Iv Jl Jn Js Lh Lx Mg Mn Mr Mt Mw Mz Nb Nm Nn Nq Nu Nv Ny Om Pa Pe Pg Qa) Lw(Fr Io Is It Iv Jl Jq Lx Mn Mr Mt Mz Nb Nm Nn Nq Ns Nv Ny Oy Pa Pe Qa Qb Qc) Ma(Hv Is It Iv Jn Js Lh Lx Mr Mt Mw Nb Nm Nn Ns Nu Oe Of Oy Pc Qa Qb Qc Qd) Ip(Fr Is Iv Jn Jq Js Lh Lx Mg Mn Mr Mt Mw Mz Nb Nm Nn Nq Nu Ny Om Oy Pc Pe) Pb(Ih Is Jl Jn Jo Jq Js Lx Mg Mn Mr Mt Mw Mz Nb Nm Nn Nq Nu Nv Om Pe Pg Qa) Vi(Af aS aY Bn cX cZ dR hC iH Ii iJ iO Jl kR Ni nW Oe Oi Rf Vp Vt Wf Zw) Ih(Fr Jn Jq Lh Lx Mg Mn Mt Mw Mz Nk Nm Nn Nq Ns Nu Ny Oe Om Oy Pc) Jq(Fr Ir Iv Jn Lh Lx Mg Mn Mw Mz Nd Nm Nn Nq Ny Pa Qa Qd) Nm(Fr Hr Ir Is Jn Js Lx Mf Mi Mn Mw Mz Nn Nq Nt Qd) Nt(Fr Hr Is Jn Js Mn Mt Mz Nn Ns Nu Oy Pc Qc Qd) Mw(Is Iv Jn Js Lh Lx Mt Mz Nn Nu Oe Oy Qa Wf Ye) Nn(Is Jn Js Lh Mi Mn Mz Nu Ny Qa Qd) Hr(Hw Ir Jo Lh Nb Om Pe Qa) Dr(hC Kq Ld Ow Rx Sr Vq) Fr(Is It Jn Js Mz Oe Oy) Nu(Is Jn Js Lh Mn Mz Qa) Mi(It Iv Mh My Of Om Qa) Nq(Hu Ir Jn Mz Qd) Jh(Du Hu Oy Vz Wf) Oe(Is Jn Js Nv Om) Mg(Ik Ir Js Mz) Mh(Ir Is Lx Nb) Ti(bM Nb Qy) Ns(Ir Nd Nv) Mt(My Oy Wb) Mz(Jn Mn Pc) Jn(Lh Lx) Rx(Hp Nb) Om(Ik Oy) Pc(Ir Qd) nI(Cx Ur) EqQy GbhB GchG MnQa NdHq HuYe IsIv YdKq WbLd VzPd SiaA ZwQl NvOy} Im{Aj(Ad aE Bb cH Cu dB Et Fd Ih Ip Is Iv Jh Ji Jn Jp Jq Jr Mb mF Mi Mt Mw Nb No Nw Oi Pb Rt Uz Vi Wc Wg Yl Tl Xa) nY(Eq Fd Gb Gd Gh Gn Hl Ho Hp Lp Rt Rx Rz Sf Sh Si Sj Ux Va Vb Vw Vz Wc Wd We Wf Wh Yl Zw Ye Tm) gP(Du Eq Fd Fi Gh Hl Ho Hp Lp Op Rt Rv Rx Rz Sf Ux Va Vb Vh Vi Vw Wc We Yl Zw Zx Tl Xa) Uh(As Cq Cu Dc Hv Hw In It Iv Jn Jq Jr Kd Lw Ml Mz Na Nb Oi Pi Qa Ra Rj Up Uu Vp Vv) Dr(Cx Ed Ef Ha Hf Hl Hp Ld Lp Ne Nh Op Or Ou Oy Ph Qu Qx Rg Rx Ry Tz Vp Wh Zw) Ry(Cu Cx Hv In Iv Jn Jr Js Kn Mi Na Pi Qn Tv Up Uz Vp Xa) Xa(aG Bn bX Ct cX fP Hb Kl Ld My Pa Pb Rt Ua Wh) Eq(dR Et Ic iH iJ iO iP Lu Ma oE Ow Pd Pj Rj) Rt(Af Cq Cx Hc Jn Jr Js Kd Mr Nb Pi Qn Up) iP(Fc Fd Gb Gc Lp Ps Rz Si Sj Va Wb Wd Yl) Wf(aH Aw eF hB hC hG Hx kQ No) Rx(Ch Iv Js Kd kQ Me Mi Na Ny) Qn(Du Fd Gh Hl Ho Op Ru Rv Sj) Cx(Du Fd Hl Op Ru Rv Uw Vb) We(Ad Id Lw Mr Oy Ra Rj Wg) Uz(aG aH bX cX Hl Ld My Ua) Wh(Ml Mt Nf Pe Ra Ua Vi) Oy(Fd Gb Ru Si Vb Wd Yl) Sh(aC bQ cM cU dK Mz) Vi(Bn dR Ld Li My Ua) Dc(Ji Kq Mt Nw Oi) Hl(Af Hu Ib oF Ur) Rv(aJ dR Hu Ml Qx) Ux(bC Dd Gc Kg Mi) Gd(cH Cu Mi Mt) Yd(aK dR Ow Pc) Wb(dR Ld Oe Ua) Zw(dR Lx Mt oE) Ye(fP iZ nW pF) Kl(Gc Ru Sj Vb) nA(Ba Ks Qv Ug) Ch(Hp Si Ti) Dd(Fd Va Wd) Qw(Gh Op Sj) Qt(Gb Gn Op) Rz(aJ Cw Li) Yl(aJ Ki Ld) Ur(kI nI Wg) Fd(Hv Jr) Ua(Ps Sf) Uy(aJ cX) Va(Vq Vt) AfnJ CuJo DgTi FcdR FyVs MiWd NkaU HoPb HuRu IbVh VzJi WcLd UgnD UwPe} Oz{Ih(Fp Hv Is Iv Jl Jn Jo Jq Js Lh Lv Lw Lx Mm Mn Mp Mr Mt Mz Nm Nn Nr Ns Nv Ny Oe Om Pa Pc Pe Pf Pg Po Qa Qc Rx Vi) Fr(Fp Hu Hv Is Iv Jl Lh Lw Ma Mn Mp Mr Mw Mz Nd Ng Ns Nu Oe Of Oy Pa Pe Pf Pg Qb Qc) Vi(bF BG CH dR eF fP Fw gL hB HC iA iJ Iv iZ kQ nY oE oF oH oK oN pF Wf) Mi(Fp Hq Hr Io Is It Jl Jq Lh Lw Ms Mt Nm Nn Nr Ns Nv Of Om Pe Pf Pg Po Qc Qe) Qa(It Iv Jn Jq Js Lh Lw Lx Mm Mp Mr Mw Mz Nk Nm Nn Ns Nu Ny Om Pa Pe Pf Pg Yd) Nt(Fp Ik Iq Is It Jn Jq Lw Lx Ma Mn Mp Mz Nd Nn Ns Ny Oe Pe Pf Pg Po Qb Qc) Js(Hr It Iv Jl Jn Lh Lx Mm Mn Mp Mr Ms Mt Mw Mz Nm Nn Ns Nu Oe Pa Pc Pe Pf) Ip(Hr Hv Hw It Jl Lv Mm Mx Nb Nn Nq Nr Nu Nv Ny Oh Om Pa Po Qc Qe) Ma(Fp Hv Is It Iv Jn Jq Lh Lw Lx Mr Mw Mz Ns Nu Of Pa Pe Qc Qe) Jn(Fc Jq Lh Lw Lx Mm Mp Mr Mw Mz Nu Pe Pf Pg Ps) Ps(aA Ax aY cH Ez GL iZ Kl Li No Uu Vb) Lx(Fc Hq Is It Jq Lw Mp Mr Mz Oe Pe) Pe(Fc Jq Mm Mn Mw nI Va Zw Xa Th) Jq(Fp Hr Iv Mn Mp Mw Nu Qb) nI(Cx Li mI Mq nK Nx Pc Pf) Is(Iv Lw Mp Mw Mz Nu Oe) Ed(Gh Ru Rz Uw Ux Vw) No(Rx Rz Va Wd Wh Xa) gL(Rt Rx Sj Va Wc Wh) Sr(Rx Sf Sh Va We) Iv(Lp Mw Ru Th) Yd(Kq Mw Nq Om) Qd(Ba Bb De Ru) Mz(Hr Mw Qb) Nb(Rt Wf Ti) Fc(It Jr) Lw(Fp

Figure 36 Continued

Figure 36 Continued

Vb Vh Vw Vz Wb Wd Wh Yd Yl Zw Zx Tl Xa) Yd(aO aP BG bQ cE Ch cO cU eF Ez Hc iA Ik iZ Jl Kl KR kS Ms Mv Ng oE oF oH Oi oK oN
Oy pF Qu Qv Tj) Du(aN aP Bn cC Dd Dp Gd Hp Is Jk kQ Mm No Nr oE Oh Un Wb) Dr(aY Cx Ef Gl iO Jd Nx Oa Oe Oi Ul) Wb(Cx Fw Il iO
Jm Kd Nx Oh Pf Ru Rx) Th(Aj bC bO bW Fp Hx Iv Jn No Pk) Rt(aF bA Hf Ir Oh) Va(aZ bO dD St Uo) Eq(Bn Fc Jh) Jo(Bb mZ nl) Ps(Dg Kl
Vs) Ux(aE aY Qy) Aa(Ip Mm) Aj(Bb Fc) Ti(Dg Nb) No(Rz Wd) Sf(aA hG) Zw(Cx Nu) aN(Fd Xa) nl(nK Ur) iZ(Wf Ye) ChVw FrWh FyVs
WcaX TmaY VccC} Ip{Jn(Fr Hr Ik Iv Jq Lh Lw Lx Ma Mm Mn Mp Mr Ms Nd Nm Nn Ns Nt Nu Oe Oy Pe Qc) Ma(Fp Hv Is It Iv Jo Jq Js Lh
Lw Mn Mr Ns Nt Nu Of Oy Pe Qb Qc) Mn(Fp Fr Is It Jo Jq Js Lh Lw Mr Nn Ns Nt Nu Of Oy Pc Pe Qc) Lw(Fp Fr Hr Is It Iv Jq Lh Lx Mr Nu
Ny Oy Pa Pe Qb Qc) Jq(Fp Fr Io It Iv Lx Mm Mp Nn Ny Oy Pa Qb Qc) Oy(Fr Is Jh Lh Lx Mt Nb Nv Om Pe Pf Qb) Js(Aa Fr Ik Mm Mp Ms
Nm Nn Nu Oe Of) Nt(Fr Hr Iq Nn Ns Nu Oe Pc Qb) Aa(Iv Mm Nb Nc Nu Of Qb) Fr(Hu It Iv Oe Of Qc) Hr(Hv Jo Lh Mr Pe) Lx(Hq It Oe Qc)
Of(Lh Mt Nb Om) Nu(Is It Qc) Mp(Hq Ns Qc) Nd(Hq Ns) NnHu MkOn MyNb IsOe JoLh} Nt{Ly(Fr Ik Is It Jn Jq Js Lw Lx Mn Mp Nd Ns Oe Ok Qb Qc) Nd(Fr Is It Jn Jq Js Lw Ma Mn Nj Ny Oe Ok On Qb Qc) Ik(Fp Fr Iq It Iv Jn Jq Lw Lx Ma Mn Ns Ny Ok Po Qc) Qc(Fr Is It Jn Jq Js Lw Ma Mn Mp Ns Oe Ok Oy) Oy(Fr Is Jh Jn Jq Js Lw Lx Ma Mn Mt Qb) Ns(Fr Is Jn Jq Js Lw Ma Mn Mp Ny Qb) Ma(Jn Jo Jq Js Lw Ng Oe Of Qb) Fr(Hu It Jn Jq Lw Ng Oe Of) Js(Hr Lw Mh Mm Nh Oe Of Oi) On(Hr Jk Mk Mv Nv Nx Oi) Jn(Jq Lw Nn Oe Qd) Of(Is Jq Mt Nb Om) Oe(Iq Jq Lx Ny) Lw(Is Ny Qb) Ok(Jo Mn My) Is(Iv Jo) Qb(Jq Nk) NnQd NuJq} Nb{Ti(Ad Bg Cq Dg Ed eF hG iZ Jo nY Oa oE Of Pz Ss Tn Un Uv Vt) Rt(Aw Fc Fy iH Iv Kj Ks Mf Mq Oe Pa Si Sr Uk Vh) Rx(aF aO bG hB iA It Kz Ld Mq Nf oH Rb Us Wf) Tl(gP Ha Hc iP nY Oi Pa Pc Qw Ug Vq Vt Ye) My(aA Fr Ir Ma Mt Ok Qd Wd) Of(aA Ir Jn Lx Nu Ny Om Qd) Wf(Ed Iv Mq Nn Pe Us) Eq(iH Kc Kg Mu Qy) Oy(Aa Fr Ma Ok Wd) Ux(Ap aW cO Mm) Hr(aA Jq Qd) Wd(Ar Mq Qy) Wc(Co Mv Om) Bo(Uz Wg) Fc(Ar kS) Gc(oE Ur) Mh(Ir Qd) Yd(Et Nw) Ye(Mq Pe) Ru(Pa Ur) AaQb BbJo DrEd GhUn MjQd HlaW HoUs SioE RyoH OeaA} Ok{Nd(Fp Fr Iv Lw Ly Ma Ms Nm Nn Nu Ny Pd Qc) Jo(Is Jm Jq Lh Ma Mp Nm Nn Ns Nu Pe Pg) Nu(Fp Is Jq Lw Ma Mn Mp Nn Ny On) Fp(Ik Io Jq Lw Ma Mn Ny Pc) Mp(Hq Ik Io Lx Mk Nr Ny Pd) Ma(Ik Iv Lw Mg Nn Oe Qc) Oy(Io Nm Nq Nv Pa Pc Qe) Lx(Hq Ly Mh My Nn Qc) Mt(Hx Mh Mv Ny Oi) My(Fr Jh Lh Om Pa) Ik(Is Iv Nr Pe Pg) Nn(Io Mn Nr Ny) Is(Iv Lw Mh Nx) Ns(Fr Io Nc) Hu(Fr Mu Nq) Pd(Pe Pf Pg) Mh(Mr Pa) Qc(Mn Ny) Nx(On Pg) Pc(Pe Pg) NqNg NrMg LwNy LyMr MkPa MvOn NcNk IoOe JhOf} Aa{Hr(Et Fp Ir Is It Iv Ji Jn Js Lx Lz Mk Mr Mt Mu Nn Nq Oy Pc Po Qd Qe) Pc(Et Ir Is It Iv Js Lx Lz Mr Mt Nn No Oi Pe Pg Qb Qd Qe) Oy(Hu Is It Jh Ji Jm Lz Ma Mg Mj Mp Mr Mu Nr Nu Po) Oi(Et Hu Ir Is It Iv Ji Jn Js No Pe Pg Po Qd) Jo(Et Ir It Js Ma Mg Nn No Po Qd Qe) Of(Hu Ir Is Iv Ji Mt No On Qb Qd Qe) Mt(Hx Md My Nf Pa) Nk(Ji Nc Qb Qe) Nw(It Mm My Nx) Ji(Jq My Nx) Et(Jm Mm) Oe(Js Qb) NqMy NuIt MjQd MmQc NdIv HxIs} Pe{Zw(Ax aY cA cK cV dR fP hG iA iH iJ iZ kR kS Nd Nn nY oE Oh Ow pF Ra Ru Up Uu Uv Vc Wf) Yd(Bn Dd gP Hc iH iP Iu Kd Mt Nw nY Pj) Wf(aA bM GL Ha kS Mp Nx Po Us Uv Va) Du(aF dR hB hC iH iJ iP oE pF Va) Va(aZ Bn Bo dL fP Hc Ne Oi Pc) On(Ik Mh Mk Nx Pc Pd) Hr(Hv Jn Js Lw Qd) aY(Uz Vc Wg Tl) Mm(Jn lX Oy) Fc(aN oH) Ma(Of Oy) Ir(Mh Of) Qd(Lz Mj) Jo(kP lX) Vc(bM Ha) nI(It kP) CxmS DrkQ FrOy LwJn NdRt VzKd XafP YekS RuUr} Jn{Lw(Fp Fr Hr Lh Lx Ma Mn Mr Ms Ns Nu Ny Oy Pa Qb Qc) Rx(Af aN BO Cq cV Dr fP hB NI Pa Uo Uv Vz) Ma(Ik Jq Lh Mr Nn Ns Nu Oe Of Oy Qb Qc) Fr(Hu Ik It Jq Mp Nd Ng Nm Ns Nu Of) Qd(Lh Mm Mp Nm Ns Nu Pc) Oe(Is Js Lh Lx Mm Nu Nv) Va(Bn gP Hc Qw Vp Wf) Oy(Jh Lh Lx Mt) Hq(Lx Mp Nd) Wd(Af Bg Us) Rt(aW Cx Uk) Of(Lh Mt Om) Ns(Ir Nd) Hr(Jq Lh) Jo(Bb nN) NnHu NuJq MkOn MmJs MpQc IinN YdOw VzaW UsnI} Js{Nu(Hr Ik It Jo Jq Ly Ma Mm Mn Mp Nm Nn Ns Oe Oy) Fr(Hr Hu It Jo Mh My Ng Nm Ns Of Oi) Oy(Jh Lh Lx Mm Mn Mp Mt Nm Nn Pc Pf) Oe(Is Lw Lx Ma Mm Mt Nm Nn Ny Qb) Ma(Ik It Mh Ms Nm Ns Qb Qc) Hr(Hv Hw Jo Jq Lh Mm Mr Nm) Of(Lh Lw Lx Mm Mt Om Qd) Jo(Ir Lh Lw Mm Mp Nm) Ns(Lw Mm Mp) Mh(Ir Lx Mt) Nm(Mf My) Mm(It Nk) Hq(Mp Nd) Ir(It Nk) On(Mk Oi) AjBb CxRt NnHu LwMs LxIk WeQy} On{Mv(Fp Fr Hq Is Iv Lx Ma Mn Mt Nm Nn Nr Nu Ny Qb Qc) Hr(Fp Lh Mr Ms Nm Nu Ny Qb Qc) Mk(It Lx Ma Mp Nd Nu Pa Qb) Qb(Ii Ik Lw Ma Ms Nk Nx) Nu(Ik Jo Jq Ly Ms Qc) Fp(Ly Nd Nk Nm Oi) Mh(Ik Is Mr Mt Nk) Iv(Ik Jo Nd Nk Nx) Nn(Jk Mu Oi Pc) Jo(Hv Jq Ms Nm) Yd(dR Ji Ow) Nx(Is Jq Qc) Ny(Ml Mt Ng) Mp(Hq Pg) Ms(Jq Ly) Nk(Nc Qc) Va(fP gP) DeQd NmMf NsMd LxHq MnHu MtHx IkIs LpUr PdPf} Yd{Ow(aE Aj bZ cL Dd dF fP Gb Gc Gz Hp Jh Ma Mt Mv oH oK oN Qy St Vc) Kq(Af aX eF Eq fP Gc Hb iO iP Ml NW oE Oi Op Pc) Mt(fP Fr Gc Is Lu Lx Lz Ml Qb Qx Tz Yl) Ji(bN Gp Il iP Iz Jh Kd kR Nn No Nv Or) Gc(Is Ld Lx Mq Ny Ps) Nw(bJ Co Kg Mg Si Uf) Is(aF bG bH Mj Ur) No(dR Nq) Sr(Gp Ug) BgOm DcMq QbLd QdVq JhPj QydR NyaW OiUt} Qd{Ns(Fr Jq Lh Lx Mm Mn Nm Nn Nu Oy Pc) Of(Fr Lh Mm Mn Mr Nm Nu Ny Om) Bb(De Jo Nk Oe Oi Oy) Hr(Hv In Mr Nm Nr Om) Mh(Is Lx Mr Mt) My(Jh Nm Nq Om) Nn(Mf Nu Pc) Ly(Lx Mr Nd) Mj(Lh Mr Pa) Mt(Hx Mv Ny) Hu(Jh Mu Nq) jT(Ik Ml Mu) De(Ji Nw) Nm(Lx Mf) Nu(Ma Mn) Nd(It Ms) Nk(Nc Ni) Jq(Mm Mp) Ru(Hl Oy) Pa(Lz Mk) AjEt AxZw WmIk FrIt FyVs MeMf MgNg IsIv JhOy JoLh} Ed{Ru(aQ cO cP cR cX Iu Jd Ji Kd Mq Mr Mu Mv Nc Ne Nf Ni Nk Nn Nq Pc Qy Ur) Xa(aN bC bN cN dR Gz Hc Ib Id Ne Ni Ow Vp) Dr(aU aW Cp cV dR Kd Nc Pf Qw) Ba(Fc Gc Yl) Cx(mZ nH nU) Fi(Cw Ni Nk) Na(Gb Gn Rt) Sh(Pz Qy Ti) Wf(Jh Mr) Vb(aQ dR) nI(Tv Ur) oE(Wd Wh) TiOa EtVa ThLd FcNi FdKq SjOw JiWc VwdR} Cx{nN(aL Dg Ef Ez Ii nI Oe Oi Qv Ss Uc Uf Ug Ur Us Uu Vo Vs) Ur(kI kK mI mT mU mZ nC nH nL) mU(Bg Jo Ld Uc Ue Uu Vo) iZ(Gb Gc Ho nI Ps Uw Xa) mS(Ar gL Mb Nn nT Sr) aA(Uy Vh Tl) Dr(Oa Ow) Ld(lX Uy) AxnI MhkP IomZ SrVa KdLp RtNy UsnU UunT VomI aZkG eMlW} Kq{De(Ad Bg bL cA cK Hb Hc Iz Jo Ld Mm My Ng Nw nY oE Ou Oy Tn Ur Uu Uv Vo) Rx(aO Bg eF fP gL gP iA iO iP iZ kQ kR nY oE oF oH oK pF) Aj(aE aW bG Ug Vp) Af(Gh Vz Tm) Ru(Oy Uu Uv) Bg(Fc Th) Wf(aY Gl) ChHp FckR JonN YeNx TmUu UvbN} nI{Ur(aN aW aZ Bb cX Dc Dd Fw Il iO Jm Jy Mx mZ Nd nK NN Nx Oa Pa Pf Ph Qb Qc Ul) nK(aA kG kI Kj kK Lz mI mU mY nF nM nN nT nU) mI(aA Jo kI oQ) Qc(kG Oy Uu) Sr(Nv Tv Uu) Nx(Lh nN Oh) CvUl IiIs JoPf UuPg OynN aAkP cXkK} Mt{My(Fp Fr Io Is It Iv Jh Lh Lx Ma Mn Nm Nr Ns Nu Nv Ny Om Qb Qc) Of(Fr Hv Jo Jq Lx Ma Mn Nm Ny Om) Oy(Fr Is Jh Lx Ma Mn Nv Ny Om Qb) Ir(Hx Mv Ny) aA(Hx Mh Mv) fP(Va Ye Xa) Aj(Bb Et) BbJo DrkR EqNy NsNd IsOe RtaX} Va{Sr(aC aE Af hG Jf Ni Nk Nw Vq) Ps(dR fP gP iP Jl oE Ow Rc Vs) Ow(bM Dr fP No St Wb) Vq(fP hC iH iZ Nu oH) No(Cw nW Vt) Is(Af hG Ld) Si(Dr hB hC) Dd(Mq Ql) Jh(Ch Vt) Ld(Qc Qh) Un(aW Ul) gL(aH Pc) AfGc AjOm StdR QyfP PfoK} Ma{Qb(Hu Hv Ik It Jq Lw My Ng Nm Nn Ns Nu Of Qc) Lw(Fp Is It Iv Mr Ns Nu Of Oy Qc) Jq(Fp Hr It Ns Nu Of Oy Qc) Is(Ik Mh Oe Of Oy) It(Ik Nu Oy Qc) Ns(Mp Nd Qc) Oy(Lh Lx Qc) Of(Lh Om) FpIk NdHq WbOw JomZ} Fr{It(Hu Ik Jq Lw Mn Nd Ng Ns Nu Oe Of Oy Qc) Lw(Is Iv Ng Ns Nu Oe Of Oy Qb Qc) Oy(Is Jq Mn Nm Pf Pg Qb Qc) Jq(Hu Ns Nu Oe Of) Is(Hu Ik Mh) Ns(Mp Nd) Hr(Hv Hw) Oe(Iv Qb) NmNg NnHu NdHq OfOm} Nn{Eq(Bn cV De fP hB hC hG Iv iZ Me Mq oE Om Qw) Sh(bM No Ny Vw Zw) aX(Hp Op Rx Wd) fP(Gb Wb Zw Xa) Rt(Fd Pi Xa) Aj(Wb Xa) Wf(aA Ny) Qu(Hp Zw) Ps(Ez Vs) Rz(Ny Wb) Ux(aE No) DrVw GbKl HlOa IsOe YeiZ LpUr} Ir{Of(Io Jh Lh Lx Nq Nv) Nm(Mf My Nd Pc) Mh(Is Jq Lh Mr) Iv(Hr Is Nd Nk) Ns(Io Om Pc) Mg(Jo My Ng) Hu(Jh Mu Om) Me(Mf My) Nd(Fp Ms) It(Hv Jq) Jo(Lh Om) LxHq MkPa MvMy NiNk IoPc RtUt} No{nW(Du Ps Rt Rx Wh Zw Zx Xa) Rx(gL gP hB hC iJ iO) dR(Fc Gh Ru Uy Zw) Aj(Bb Et Mg Nk) hB(Fc Fi Ti) Wf(gL Pf) iH(Gn Zw) ThkR GcUp ShhC WhaU YegL LpUr} iZ{cX(Fi Gb Gc Gh Ho Ps Si Uw Vw Wc Wd We) Rx(Hb Lx Ps Xa) Gc(Af bQ oE) Uy(Ji Ld Pj) Si(bQ oE) Ps(Oe Qn) Lp(Ld Ur) Ru(Ji Un) AfUw EqaW LxZw ShPf YeOm} Dr{Ow(Af aN aW Fw Gl Hu Kl Lv Oe Qw Qy Zw) Pf(HC iA iH Kd kQ kS nW oK oN pF Uk) Oa(aW Gp Ic Kc Mm nW) hB(Il Kd) MhQy RxOh} Hr{Jq(Fp Il Is It Iv Lx Mn Mp Nr Ny Po Qe) Lh(Hw Is It Nm Qb) aA(Il Jl Mr Nx) Hv(Jl Lx Pa) Hw(Is Jl Lx) Lw(Is Mr) QbJo} Wb{Pf(dR fP gP hB hC iH iP kQ kS nW oE oK oN pF) Ow(dH Gl Hu Ml Oe Qw Qy) Oh(Ic Pc Qy) MqaN IcOa LdRu aYhB} Nu{Jq(Fp Is It Lx Mn Mp Ns Oe Of Oy Qb Qc) Lw(Is It Qb Qc) Is(Ik Sh Zw) Ns(Mp Nd) AjnN MnIt ShOw QbOe NwUy OfOm}

Figure 36 Continued

Oa{Rx(aA Af hG Je Jy Lx Nj Vz) Ur(Fi Lp Ru Zx Ti) Ti(aA Af aY) Gc(hG Jo Rt) Sh(gL Hu Sr) AfSi HlaW ZwLd SrRv} Oe{Is(Lh Lw Lx Mm Mn Mp Nm Nv Ny Om Oy Pa Po) Qb(Lx Mm Nm Om) Ps(nY Us Vo) LxJq XaVs} Lp{Ld(bR dR gL hG nY oF oH oN pF) Ur(Cu hB Jd Jh Jy Nv Oh Qe) Mq(Rj Wf Ye)} Wf{Mr(Fw Il Jm Nr Ru Th) Kd(Ld Mq) Ny(aW gL) AxQy BoSr ChJh FwaM NraS IvaY} aA{Oy(Il Jk Lv Nx) Ml(Hx jT My) Lv(Ly Pc) My(Jh Nq) Hu(Jh Nv) NsIl MrNi jKjT} Xa{Sr(fP oK) Qy(Bg Vs) Kd(Ld Rt) aN(hB Mq) AfOw AjaW BnNy ChJh RxpF LdNx aYhB} Rx{Ny(aW cV cZ It Iu Iv Na) St(kQ oF) gL(Pc Ps) HpOw QehG QyoF} Ns{Mp(Is Jq Lx Mn Ny Qb Qc) Nd(Fp Is Iv Jq Lx Om)} Bb{Jo(Cu Dd Is Iv Ji Jr Ml) Aj(Et Is Ji Qe) MyJh} Kd{Mq(Eq Vz We Ye) Rt(Is Mv Ut) hB(Eq Sh Vc) Ql(Uy Ye)} Ru{Iv(aS Pc Rt) Ur(Cu Ny Qe) Oy(Jh Nq) JibM QyaZ LdkQ} aW{Ur(kI kP mS nA) Ny(Sh Sj) BomS HpNw IvRt} nN{Jo(Af Dg Dl Nh Qc) Aj(cX tF) BoVv CvtF} Lx{Oy(Jh Jq Lw Om) LwQc MhIs NdHq OfOm} Ow{Af(Fd Gb Uy Uz Wc) Hp(Pc Us) DuFp} hB{aY(Fd Ho Ps Uz) Il(Sh Vc) Uy(Mv Qy)} Nk{Ji(Aj bA bN cT) Jr(jK jQ jR)} Eq{Mq(Al Il) MgNy HuLd StcO QyoF} Ml{jT(Ji Jq Jr Lw Nw)} Sr{Sh(dL Uv) Uu(Et We) AjaE} Ps{Qn(nY Uu) MhPc HvUs VscX} Ld{Zw(Pf St) Uy(It nY) FikR} Iv{Rt(aY Jm) ThUr WcVq} Of{Om(Lh Mp Nd Qb)} Oy{Lw(Is Qb) Jh(Lh Qb)} Mq{FdaN IlWe JmYe} Qy{Oh(Fc Gd) DeJq} gL{Pc(Rt Wc) WdaX} Fp{NdHq VhaY} Pf{AjWd GbhG} jK{HqJr cWdM} ThQeUr FwShaM GcNyVp NrRtaF JiUvbN WcPdaZ VoaNmI

Constrained panels with 2 analytes, where 1.0E-8 >= 'model p-value' > 0. Contains 343 panels of 121,819 total panels evaluated. : aA(Et Fp Fr Ih Ij Im Io Ip Iq Ir Is It Jg Ji Jm Jn Jp Js Jt Lh Li Lj Lw Lx Ma Me Mg Mi Mm Mn Mw Mz Nj Nm No Nr Ns Nt Nu Nw Ny Oe Og Ok Om On Oz Pb Po Qa Qb Qc Qd Qe) Li(Et Hr Hu Ih Ij Ik Im Ip Ir Is It Iv Jg Ji Jj Jn Jp Jq Js Jt Lj Lw Mi Mp Mw Mz Nd Nm No Ns Nt Nu Nw Oe Og Ok On Oy Oz Pb Qa Qb Qc Qd) Et(Fp Ih Ij Im Ip Ir Is It Ji Jj Jn Jo Jq Js Jt Lj Lw Mi Mp Mw My Mz Nc Nd Nn No Ns Nt Nw Oe Of Og Ok On Oy Oz Pb Pe Qa Qb Qc Qd) Im(Aa Hu Ik Ip Ir Ji Jj Jp Jq Js Jt Lj Lw Mi Mp Mt Mz Nn No Ns Nt Nu Nw Oe Of Og Oh Ok On Oy Oz Pb Pc Qc Qd Ye) Nw(Hu Ih Ij Ip Ir It Ji Jj Jn Jt Lj Lw Mh Mi Mp Mw My No Ns Nt Nu Oe Of Og Oy Oz Pb Qa) No(Ih Ij Ip Ir Is It Ji Jj Jn Jp Js Jt Lw Mi Nm Nn Ns Oe Og Ok Oy Oz Pb Qc Qd) Ir(Fr Ip Jg Ji Jj Jp Jt Lw Ma Mi Mm Mn Mp Mw Nn Nt Nu Oe Og Ok On Oy Oz Pb) Ji(Hr Ip Jg Jj Jn Jp Jq Lj Ma Md Ms Mw My Nk Nu Nx Of Og Oy Oz Pb) On(Hu Ih Ip It Jj Jt Lj My Ng Ns Oe Of Og Oy Oz Pb Qd) Ok(Hr Ih Ij Ip It Jj Jp Js Lj Of Og Oz Pb Qa Qd) Qd(Ij Ik Ip Jg Jj Jp Jt Oe Og Oz Pb) Jj(Ih Ij Jg Js Jt Nt Qa) Jp(Ih Ij It Jt Lj Mi Oz) Jt(Hr Ip Lj Og) Ij(Mi Og Pb) Aa(Oz Qc) Ih(Jg Ma) JgOg Constrained panels with 2 analytes, where 1.0E-7 >= 'model p-value' > 1.0E-8. Contains 242 panels of 121,819 total panels evaluated. : Ok(Fp Fr Io Is Jg Jn Jq Jt Lw Lx Ma Mi Mn Mp Mw Mz Nd Nn Nr Ns Nu Ny Oe On Oy Qb Qc Qe) Jp(Aa Fp Ip Is Jj Jn Jq Js Lh Lw Mp Mw Mz Nm Nn Ns Nt Oe Og On Oy Pb Qa Qb Qc) Jt(Aj Fp Fr Ih Ij It Jg Jn Jo Js Lx Ma Mi Mw Mz Nt Nu Ny Oe Of Oz Pb Qa Qb Qc) Qd(Aa Ih Ir Jn Jq Lh Lw Lx Ma Mi Mm Mn Mp Mw Mz Nm Nn Ns Nt Nu Oy Pc) Ij(Fr Hu Ih Ik Ip Ir Jg Lj Lw Mm Mp Mw My Oe Of On Oy Oz Qa) Aa(Et Hr Ih Ip Ir Jj Js Li Nw Og Oy Pb Pc Qa Qb Qe) On(Hr Ik Jn Js Lw Mi Ms Mv Mw Mz Nu Qa Qb Qc) Jj(Ip Is Jm Jn Lh Ma Mw Nm Nv Ny Qb) aA(Iv Jq Mp Mt Nn Nv Oy Pc Pe Pg Pz) Ih(Fr Ip Lw Mi Mm Mw Nt Nu Og Oz) Qa(Hr Ip Jg Lw Ma Mi Oe Og Oz Pb) Jg(Ip Js Lj Lw Mi Mz Oe Of Qb) Ir(Hr Io Lj Lx Mz Nm Ns Pc) Ke(Kf Lh Mm Nx Pb Uu Uv Vo) Ip(Js Mi Mw Nt Og Oz) Js(Fr Lw Ma Og Oz) Lj(Lw Ma Mi Nt Vi) Mi(Jn Mw Oz) Og(Is Nt Om) Eq(Im Nn) ImSh YdLi Constrained panels with 2 analytes, where 1.0E-6 >= 'model p-value' > 1.0E-7. Contains 481 panels of 121,819 total panels evaluated. : Ih(Fp Hv Io Is It Iv Jl Jn Jo Jq Js Lh Lj Lv Lx Mn Mp Mr Mt Mz Nk Nm Nn Nq Ns Nv Ny Oe Om Oy Pb Pc Pe Pg Po Qa Qc Va) Uh(aA As Cq Cu Cw Dc Hv Hw Id Ij In It Iv Ji Jn Jq Jr Kd Ke Kq Lw Ml Mz Na Nb Nf Pi Qa Ra Rj Sr Tv Up Vp Vt Vv) Jg(Fp Hu Hv Hw Ik Is It Iv Jn Jp Jq Lh Lx Lz Mg Mn Mp Mr Mw My Nd Ng Nn Ns Nt Nu Oh Oi Oy Oz Pb Pe Po Qc Qe) Ke(Ad Af Aj bG bN De dK Dp eC fP Ii Il Im Iz Jh Jj Jm Jo Kj Ne Nv Ou Oy Oz Ph Qc Up Ur Us Vp Vs Yd) Mi(Aa Fp Fr Hq Io Is It Iv Jj Jq Js Lh Lw Lx Ma Mn Mz Nm Nn Nr Ns Nt Nu Nv Ny Og Pb Qb Qc Qe) Ij(Aa Aj Fp Hr Is Iv Jn Jo Jq Js Lh Lx Ma Mn Mz Nd Nm Nn Ns Nt Nu Ny Oh Pc Qb Qc Va Wc Wf Yd) Js(Hr It Jn Jo Lh Lj Lx Mm Mn Mp Ms Mw Mz Nm Nn Ns Nt Nu Ny Oe Oy Pb Pc Qa) Nt(Fr Ik Iq Is It Jn Jq Lw Lx Ly Ma Mn Mw Mz Nd Ns Ny Oz Pb Qa Qb Qc) Lj(Fr Ip Is Jj Jn Jq Lh Mg Mm Mn Mp Mw Mz Nm Nn Nq Nu Nv Om Oz Qa) Qa(Fr Jn Jq Lh Lx Mm Mn Mp Mw Mz Nk Nm Nn Ns Nu Ny Oy Pc Yd) Ip(Fr Is Iv Jn Jq Lh Lw Lx Ma Mn Mp Mz Nu Ny Pb Qb Qc) Jj(Bb Fr Ii It Jl Lx Mn Mz Nn Nr Nu Om Pe Po Qe) Jn(Fr Jq Lh Lw Lx Ma Mm Mp Mw Mz Nn Nu Og Oz Rx) Jt(Aa Is Iv Lw Mj Mn Mp Ms Mt Nn Ns Oy Pe) Fr(Aa Is It Jq Lw Mz Oe Og Oy Oz Pb Qb) Jp(Hv Hw Iv Lx Ma Mr Nu Ny Oh Pc Pe Po) Aa(Is It Iv Ji Lz Mw Nb Nn No Nu) Ma(Is It Jq Lw Mz Og Oz Pb Qb Qc) Og(Jl Lh Lx Mw Mz Nm Nv Ny Qb) Is(Lw Mw Mz Nm Nu Oe Oz Pb) Lx(It Jq Lw Mz Oz Pb) Im(Aj Ux Uz Va Vi Xa) Li(Dr Du Eq Va Vi Wb) nI(mI nK nN nT Oz Ur) Mw(Jq Lw Mz Sh Wf) Aj(Et Ji Kq No) Ed(Dr Ru Vi Xa) Yd(Ji Kq Ow Pe) Va(No Pe Ps Sr) Mz(Hr Nu Qb) Nb(Rt Tl Ti) Jq(Hr Nu Qb) Oa(Gc Rx Ti) Lw(Ny Qb) Wf(Pe Vi) Kq(De Uu) Ow(Dr Wb) Pb(Lh Nv) jK(aA Jr) BbQd NnSh MtMy PsOz Constrained panels with 2 analytes, where 1.0E-5 >= 'model p-value' > 1.0E-6. Contains 731 panels of 121,819 total panels evaluated. : Uh(Ad aM bA BN Cp Dd dK Dr Hx Im Ir Is Jj Jo Js Jt Kn Kp Kr Ld Me Mi Mj Mt Nl Nk Nm Nr Ny Oe Oh Oi Om Ou Pb Pe Pk Qd Qe Rb Rf Uc Ud Ul Un Ur Us Uu Vs) Jn(Fp Is It Iv Jl Mn Mr Ms Mt Nb Nd nI Nm Nr Ns Nv Ny Oe Oh Om Pa Pb Pc Pe Pf Pg Po Qb Qc Qe Rt Va Wf) Lj(Fc Gb Ho Hv Hw Io It Iv Jh Jl Jo Lv Lx Mr Mt Nb Nd Ns Ny Og Oh Pa Pb Pc Pe Pg Po Ps Qb Qc Vw Wd Ti) Jq(Fp Io Is It Iv Jj jK Jl jO jT Lh Lw Mm Mn Mp Mt Mz Nm Nn Nr Nv Ny Og Oz Pa Pb Pe Po Qc Qe Ur Wm) Vi(aF aO aW bF Bg Bn Ch cV Gc Hc Iv Kz Ld Lz Ml Mq My Nx Oa Of Ow Oz Qx Rt Sh Sr Tn Ur Uu Va Vt Yd) Ip(Fp Hv Hw Io Iq It Jl Lz Mm Mr Mt Mx Nb Nc Nd Nm Nn Nq Nr Nv Oh Om Oy Pa Pc Pe Pf Pg Po Qe) Lx(Hq Hv Hw Io Is Iv Jl Lh Ma Mm Mn Mp Mr Mt Mw Nb Nm Nn Ns Nu Ny Oe Om Oy Pa Pc Pe Qb Qc) Ma(Fp Fr Hv Hw Ik Iv Jl Lh Mn Mp Mr Mt Mw Nb Nm Nn Ns Nu Ny Oe Of Oy Pa Pe Po Qe) Mz(Fp Io It Iv Lh Lw Mm Mn Mp Mt My Nf Nm Nn Nr Nv Ny Of Om Oz Pb Pc Pe Po Qc Qe) Mw(Fp Fr Hv It Iv Jl Lh Mm Mn Mp Mr Mt Nm Nn Ns Nu Nv Ny Om Oz Pb Pe Qb Qc) Is(Bb cV cX Fp Iv jK jT Lh Mm Mn Mp Ms nI Nn Ns Ny Oy Pc Pe Qc Ur Va Yd) Qd(Aj Ba bM bN bP cH De jK jQ jR jT Ld Ou Ra Ru Ur Uu Uv Va Vo Yd) Pe(Fr Gh Ha kP Lw lX Mm Mn nD nI Nt Ny Og Oz Pb Qb Ru Sh Vc Wh Zw) Lw(Fp It Iv Jj Jl Lh Mn Mr Mt Nm Nr Nu Nv Og Oz Pa Po Qc Qe) Qb(Bb Lh Mm Mn Mp Mr Mt Nm Nn Ns Nu Nv Ny Oe Om Oy Oz Pb Pc) Fr(Fp Hu Hv Iv Lh Mn Mp Mr Nc Nd Ng Nm Nn Ns Nu Ny Of Qc) Va(Ed Fw Gc Ir Ji Ke Ld Nb Nt Nw Oa On Ow Qa Qe Rm St Un) nI(aA Cx Js kG Li Lz mP Mq nC nH nL nU Oh Pb Pf Qa Qc) Jj(Fp Io Iv Jk Jo Kq Mm Mp Mt Pf Pg Pz Qc Sr Ut) Ny(Fp It Iv Lh Mn Mp Mr Nm Nn Nu Oz Pb Qc Rx) Bb(aA Aj Ih Ji Jo Js Jt Ml Mt No Qa Qc Qe) Oz(Fp Iv Jl Lh Mn Mp Mt Nv Om Pg Po Xa) Nu(It Jl Lh Mn Mp Nn Nt Nv Og Om Qc) Ij(Hc Op Rt Rx Sh Ur Uu Vc Vo Wb) Ji(aW bN cB cX De jT Ur Uu Uv Vo) Kq(Ch Iz Jo Kl Mm Of Ss Uv Vo Wf) Nw(aF Aj aW bN Cu CX dH dK Yd) Og(It Iv Jk Mn Mt Nb Nn Nr Po Qe) Nt(Fp Mm Mp Mt Nm Nn Oe Oy Qe) Mi(Hr Mm Mt Nj Of Om Oy Po) Mn(Fp It Lh Nm Nn Pb Po Qc) Js(jD jK jQ jR jT jY Rt Ur) It(Jl Lh Mm Mp Nn Nv Om) Sr(Aj Dr Sh Ur Uu Wf Yd) Cx(kP mI mS mU mZ nN) Qc(Cu Lh Mm Mp Nv Om) Ke(aE aY Dr oE oN Ru) Aj(Jg Li nN On Ut) Im(aU cH Cu De Dr) Wb(Ld Ml Mq Oh Pf) Qa(Rt Rx Ur Wf Zw) Lh(Hr Iv Mm Nm Of) No(Ur Uu Vc Wf) Mt(Eq Of Oy Yd) Nv(Nm Ns Oe Oy) Om(Oe Of Oy Pb)

Figure 36 Continued

Ed(Gc Ps Ti) Fp(Mm Mp Nm) Nb(Lp Rx Wf) Jg(Mx Pa Uu) Ur(Ir Lp Vt) Pb(Jl Pg Po) aA(cX dH jT) Cu(Hr Rt) Dr(Ld Oa) Mr(Ru Wf) Iv(Rt Ru) Xa(Ld Mq) CtJt NmJl NsMp MllM YdOn JrjT VtbN

Constrained panels with 2 analytes, where 1.0E-4 >= 'model p-value' > 1.0E-5. Contains 1,307 panels of 121,819 total panels evaluated. : Kq(Ad aY Bg bL bN cH Dg Dp Dr Ef Eq Fr Hb Hc Hq Ij Im Js Kg Kj Ld Li Lj Mg Ml My Mz Ng Nk No Nw oE oH Oi oN Ou Oy Pb Qb Qc Rt Ru Sh Sr Tn Tz Ur Us Ux Va Vs) nI(Bo Cv cX Ed Fp Hw Ih Il Im Ir Ji Jj Jl Jp Jr kF Lj Lx Ma mF Mi Mj Ml Mp Mr Mt mU Mv Mw Mx Mz Nb Nh Nn No Nq nR Nt Nu oE oQ Pa Qb Qd Qe Rj Sr Um Us) Va(Ax Cs Cu Dc Dr Gb Hb Ho Hp Hv Hw Hx Ic Ii It Iu Iv Jh Js Jt Lj Lx Mi Mq Mt Mw Mx Na Nn Nr Nu Nv Ny Oh Om Pd Pf Po Qb Qc Ql Qy Si Tz Ut Vq Vt Xa) Qc(Aj aX aZ BA bM cT Dc Di Fp Fy Hv Hw Io It Iv Jh Jl Jo kG Ld Lv Mg Mr Mt Nb Nm Nn Nq Nr Og Oz Pa Pb Pc Pe Pf Pg Po Qb Qe Sr Uh Vt) Bb(aM Ax aZ bA Bg bN CH CS Cu CX Dc Dd Di dK Et Hv Ij Ir It Iv Jn Jp Jq Jr Li Lj Lw Mi Mm Mw My Mz Nb Oe Oi Oy Oz Pb Pe) Xa(Af Ar aW aY Bo Cx Dr Fp Fw Hx Ih Iv Jj Kd Kl Lj Lz Mh Mi Ml Nn Nu Nx Oi Ow Pb Pf Qb Qd Ql Qx Rt Ru Rx Sh Sr Vs Vt) Ur(Cp Cu Dc Dd Fy Hv Ih Il Im In Iq It Iv Jn Jr Jt Kd Li Mi Ml Mz Na Nr Nt Nw Ny Pe Pg Pi Ps Qe Uc Un Up Ut Vp) Vi(Af Aj Ar aY bG bJ cE cH Cs Cx Dk Dp Eq Fp Ic Ih Iz Ji Kd Ke Kl Mh Mi Mk Mx Nn Pj Qb Qd Qn Qw Rc Uv Vo Vp Vs) Nn(Fd Fp Hb Hu Hv Io Iv Jl Kd Lh Lp Lw Mp Mr Mt Nm Nr Nv Oe Om Oz Pb Pc Pe Po Ps Qe Ux Uy Uz Vc Wb Wf Yd) Mw(Aj aZ Ch Cu Dc Dr Eq Hc Hw Io Iq Ld Lv Ms Mx My Nb Nj Nr Oe Oh Oy Pa Pc Pf Pg Po Qe Ru Uh We Yd Yl Ye) Mt(Aj bM dG dH Fp Hb Hv HX Ik It Iv Jl Lh Mh Mm Mn Mp Mr Mv Nm Ns Nu Ny Oe Om Pb Pe Po Qe Ux Wb Wf) No(aQ aU aZ bM bO cX dH Dp Fc Gh Ha Hb Iz jK Kl kP Ld oN Ou Ow Sh Ss Tz Uh Uv Vo Vs Vt Wh Yd) Mz(cH Dp Ed Gp Hb Hv Hw Hx jK Jl Jo Ld Md Mh Mr Nb Ns Oh Ou Oy Pa Pf Pg Pz Sr Tz Us Uu Uv Vt) Nu(Fp Hv Hw Io Iq Iv Jo Ly Lz Mm Mr Mx Nb Nd Nm Nr Ns Oe Oh Oz Pa Pb Pc Pe Pf Pg Po Ps Qe) Iv(Fp Io Iq It Jl Mm Mn Mp Mr Nd Nm Nr Nv Om Pa Pb Pc Pe Pf Pg Po Qb Qe Vb Vc Wc Wf Th) Sr(Af aU aY bN Dp Et Gp Hb Hq Im Jo Jq Ki Ld Li Ml Mm Nw Oe Oi Ou Pb Ps Qd Rt Ru Uv Vo) Jj(Ad Co Cu Dc Dd Fb Hb Hv Il Iq Iu jK Kd Mg Mj Mr Mx Nb nN Nq Nx Oz Pa Qh Rf Tz Un Vt) Dr(aW Ho Ic Kc Kd Lj Mi Ml Mq Nb Nd Oz Pf Ps Qb Qd Qw Qx Qy Rm Ru St Tz Uf Ut Vq Vt) Pe(Aj Fp Gc Hr Io It Jl kC kN Lh Mp nA Nm Nr Ns Nv Of Om oN Ou Oy Pc Po Qe Uu Vo Vs) Om(Aj Fp Hr Hu Ik Io Jl Lh Lw Mm Mn Mp Mr My Nd Ng Nm Nr Ns Ny Oh Pc Po Qe Yd) Mn(Aj Hv Hw Iq Jl Mm Mp Mr Ms Mx Nb Nd Nr Ns Nv Oe Oh Oy Pa Pc Pf Pg Qe) Ij(aF aX aZ Bg bM bN cE Ch Ct Dp Ib Iz Kj Kl Ld Ou Qw Rc Ss Us Uv Vs Vt) Ny(Hv Hw Jl lK Lv Mm Nb Nd Nr Ns Oe Oh Oy Pa Pc Pf Pg Po Qe Rt Ru Wf Yd) Lw(Hb Hr Hv Il Io Iq jK jT Lz Mj Mm Mp Mx Nb Nc Ns Oy Pb Pf Pg Pz) Aj(Ad Ba Cu Dc Fr Fy Ih Ir Is Jp Jq Js Ma Mi Ok Qa Tn Uh Un Vt) It(Fp Hv Io Jh Mr Nb Nd Nm Nq Nr Oz Pa Pb Pc Pf Pg Po Qb Qe Rx) Hb(aA Cu Fy Ih Im Ji Jn Jq Jr Js Kd Ml Mu Na Qa Qd Un Ut Vt) Uh(aE cH Cs cT eF Fy Ib Ih iZ Ki Ko Li Mq Nt Nw oE Ut Uv Vo) Qe(bM Fp Io jK Lh Mm Mp Mr Nm Ns Oe Oy Oz Pb Pc Ru Rx Yd) Po(Hr Hv Ik Io Lh Mm Mp Mr Nd Nm Ns Oe Oy Pc Qb Wf) Fp(Ik Io Iq Jl Lh Mr Nd Nv Og Oh Pb Pc Pg Qb Ti Th) Jq(Af CX Ld Mr Nd Ns Oy Pc Pf Pg Pz Qn Uu Uv Vo) Oz(bA Cu Ho Hv Io Lp mI Mm Mr Nb Nm nN Nr Og Pa Pf) Is(aF aW bN jD Ld Mh Ou qY Rt Ru Rx Sh Uu Vo Wb) Ps(Ar Ml Oi Pf Qv Qx Qy Rx Us Uu Vo Vs Vt Yd) Ru(Cs Fw Hv Ji Jn Kz Ld Lj Lx Mi Mq Nw Vt Wb) Mm(Hv Hw Jl Mr Nb Nm Nr Nv Og Pa Pb Pf Pg) Mp(Hq Hv Io Jl Lh Mr Nm Nr Nv Og Oy Pb Pd) Et(aZ bA Bg bM bN Ch Cs Cu Dc Dg Uu Vo) Im(iP Kd Ld mF nA Ou Qw Un Uu Vo Vs Vt) Qb(Cu Di Hv Io Jh Jl Jo Lv Mg Nb Oh Pa) Pf(Eq Fd Ho Hp kN kP Lp lX Nm Pb Sh Yd) Ld(Ji Jn Jr Js Lp Na Qa Uy Wf Ye Th) Lh(Hv Io Jo Ly My Nd Nr Ns Nv Oe Oy) Og(Ii Io Iq Jh Jm Jo Mg Mr Pa Pg Pz) Ho(Ar Cs Lx Lz Mh Ml Mx Oh Qx Rt) Nw(Ed jH jI jK Jv Ra Ul Uu Vo Vt) aA(Ad aH aM cH cV Cx Dc Dd qY rB) Qa(bM bN dL Ou Us Uu Uv Vo Vs) Qd(gP oE qY Sh Us Vs Ye Ti Th) Nm(Hv Mr Mx Nb Nr Pa Pb Pg) Wf(Ir Jh Kc Mq Nr Nt On Ut) Cu(dH Ih Jo Jp Li Nk Pb) Lx(kP Mh Of Oh Vc Wb Yd) Ji(jK jO Jv Ou Us Vs Wb) Js(Fc jE Rx Us Wb Wc Yd) Rt(Ax Cq Fy Hv Jr Mi Mx) Nv(Hu Hv Ma Mr My Nd Of) nN(Ad Af Cv Jo Kj Oy Pb) Ml(jD jI jK jT Kd Lp) Mq(Eq Fd Lp Uy Uz Ye) Jl(Hr Io Nr Ns Oe Oy) Ut(Ch Iz Kl Sh Uu Yd) Nb(aZ My Of Oy Pb) Li(kP lX mZ nD Vs) Nr(Ma Mr Pb Sh) Ih(bM jK Rx Sh) Jt(Bg bM bN Ch) Mr(Io Pb Rx) Ir(jK Rx Uu) Yd(Jh Nt Oh) Wb(Ke Lj Qx) Jo(Hr Kd Pb) On(Bg De Uu) Un(bN Pb Uu) Vt(aY Gp Ou) Ax(Rx Th) Cs(Fc Th) Eq(Ow Qy) Fy(Ou Vs) Mi(bS Wc) Nd(Ma Ns) Jh(Ch Oy) jI(jT Nk) jK(dM Jn) ArLp CxnL EdZw FdaW FwSh HpOw WcKe LjUw OyPg Constrained panels with 2 analytes, where 1.0E-3 >= 'model p-value' > 1.0E-4. Contains 2,181 panels of 121,819 total panels evaluated. : Va(aA Ad aE aF aH aM Ao Ar aW aZ BA Bb bR Co Cp Cq CT Cw Dd Dk Dl Ef Et Fc Fd Fi Fp Fy gL Ha hB Hf Hu Id Il In Iq IZ Jd Jg Jk Jl Jm Jp Jq Jr Kd Kf Kk Kn Ko Ks Kx Lh Lp Lz Mf Mg Mj Mk Ml Mn Mp Mr Mu Mv Mz Ng Nh Ni Nm Nq Of Ok Or Ou Oz Pa Pc Pg Pi Pj Pk Pz Qg Qh Qm Qx Ra Rf Ru Tn Tv Ua Uc Uf Uh Up Uw Vh Vp Vs Vw Wb Wc Wd Tj Ti) Hb(Ad aE Aj As bN cA cH Cp Cq Cw Dc Dd dK Ed Et Fw Hv Hw Id Ij Il In Ip Ir Is It Iv Jl Jo Jp Jt Jv Kg Ki Kn Kp Kr Kx Ld Li Lj Mi Mj Mq Mw Mx Nb Nf Ni Nm nN Nr Nt Ny Oa Oe Oh Oi Om Pb Pd Pe Pg Pi Pk Qe Qv Ra Rf Rj Ru Tv Uc Uf Ul Up Ur Us Uu Vo Vp Vs) Jj(aH Al Ao Ap aW Ax aZ BA Bc cH Cp Cq Cs cT Cv Cw cX Di Ed Ez Fw Fy Ho Hu Hw Hx Id In Jh jI Jr Jy KG Kj Kn Ko KP Ks Kx Kz Ld lM Lv Lz Mv Nc Nd Ng Ni Nj Oa Og Oh Pb Pc Pi Pj Pk Ps QY Ra Rm St Tn Tr Tt Ua Uc Uf Ug Up Ur Vp Vq) Ur(aA Ad Aj As bA Bb bN cH Cq Cs cT Cw Dk Ed Et Fd Fp Fw Gp Ha Ho Hw Hx Id Ii Ip Jh Jl Jm Jo Jp Kg Kj Kn Kp Kr Ld Lh Lj Lw Me Mj Mr Mt Mw Nb Nf Nm Oa Ok Om On Pb Pk Po Qb Qc Qh Ra Rb Rf Rj Tn Tv Tz Ul Us Vs Xa) Mt(aH aV aY aZ bF Bg bN bP bQ bR bS bU bZ cA cD cE cG cK cL cN CO Cu dA dI Dp Dr Gp hA Hw Io Iq jK Jo Ly Md Ml Nb Nd Nr oE Oh oN Pa Pc Pg qY Rf Rg Tz) Ld(aA Bb Cu Dc Ed Et Fd Fy Gc Gp Ho Hv Ih Il In Ir Iv Jm Jp Jt Kd Kz Li Ly Me Ml Mu Mx Nb nI NN Nt Ny Pe Pg Pi Pk Qb Qe Rf Tz Un Ut Uw Uz Vp Vt Vw Wc) Ru(aA Ar aZ Cp Cu Fd Fp Gc Ha Ho Hp Hw Hx Ir Jh Jl Jq Jr Jt Kd Kn Ky Lz Mj Mk Mv Mz Nt Nu oE Om Ou Oz Pc Pd Pi Po Ps Qb Ql Qy Rm Sh St Tz Uh Un Vo Vq Tm) nN(aM aP Bb Bg bM Bn Bo CH Cq Cs cX Dc De Fp hB Hu Im Iv IZ Jn Jr Kg kl Ks Ky Lx Lz Mb Me Ml Mq MU My mZ nA Nh No Nu Of Pf Ph Qa Qc Qd Us Vs) Kd(aE Aj aU aW aY bL bN bS cH Cx dJ dK Dp Ed Et Gc Gp Hr Is Kj Ko Li Lj Mu Mw Ne Nk Nw oE Oh Ou Pb Ps Qb Qc Qy Rf Rt Rx Sr Tz Ut Uu Uy Vo Wc Wf) Oz(cT Dc Fc Fd Fi Gb Gc Hp Hu Hw Ii In Iq Jh Jk Jm Jo Jr kG kP Lv Lz Mg Mh Mj mP mT Mv Mx mZ NC Nd Nq Ns Nx Oh Pc Pz Si Uw Uz Vq Vw Wb Wd) Dr(Ao aY BA Bb bH bW Co cS cU Cx dR Em Fw gL hB Ih Is It Ji Jm Lh Lx Lz Mg Mk Mn Mp Mu Mx Ne Nn Nq Nw oE oF Oh Oi Pc Pe Qa Qc Qe Wf) Ut(aA Af Bg bL bN cH Ct Cu De Dp Ed Eq Gc Hc Im Iv Jn Jo Jr Kj Lj Lp Mg Ml Ne Ng Nk Oe Oi Ou Oy Pb Qb Qc Rf Rt Ss Tz Us Uv Vo Vs Vt Wb) Ho(aA Af Aj aM aP aW aZ bM Bo CX De Dp Fp Gp hB Il iZ Jo Kj Kx Nu Nw Oy Pb Qb Qv Qw Qy Ra St Tz Uh Us Uu Wb Wc Wf Ye Xa Wm) Vt(aA Bc bL Cx dK Dp eC Ed Et Fy Hr Ih Il Is Jo Jr Js Ko Li Lj Lp Ml Mw Ne nI Nk Nt oE Oh Pb Pe Qe Rf Rx Sr Tz Vo Wb Wf Yd) Dc(aX aZ BA bM cS CX Di dK Dp Ed Fr Gp Hr Ih Jg Jo Jp Li Ly Mi Ml Mn Nb Nk Nq Oe Og Oi Ou Pb Qb Qy Rt Tz Us Uu Vo) Xa(aF Aj aM Ax bJ Ch Cs cX Dp Eq Gl hB Hv Il Ir Ji Kz Mk Nc Ni Nk Nr Nw Of Pc Qc Qy Rc Rj St Uh Ul Un Uu Wf Yd) Cu(AA Ar aZ Ba bN cK cS cV Cx dK Dp Fr Ik Jg Kj Lw Ly Ml Mn Mr Nb nl oE Ou Rf Rx Us Uu Vo Vs Wc Wf Yd Ti) Qc(aE aH aM Aw cH Cp Cv cX Dd dK Ed jK Ki Kk Kn lM mP Mx mZ Nd Nj Ns Nx Oh Ou Pi qY Ra Rf Tz Un Up Uu Vp) Qb(Ad aE Aj aL aQ aX aZ BA bM bN cT Cv Dd dK Fy jD jH jI jK jT kG Ko lM qY Rf Rx Sr Un Vw Wb Wd Ti) Aj(Ap Co Cw Dd Ip Iv Jk Jn Jr Jy KG Kn Ko Lw Mg Mu Mz Nb Nq Nt Nv Ny Pi Qe Rf St Tr Ua Uc Up) Rf(aA aE dJ Ed Et Gp Hv Il Im Ir Is Iv Jn Jp Jq Jr Js Jt Li Mi Ml Na Oe Oi Pi Tz Up Uv Vo Vp) Un(aA aE aU aY cH dK Dp eC Ed Et Gp Il Jm Jo Js Li Lp Ml Ne nI Nk Oe Oi Ou Ow Ss Tz Vo Wf Yd) Ps(aA aF aM aW bR Cs cU cV cX Fp gL hB Il iZ Kl Kx Lz Mh Mk Ni Nt Oe Pb Pc Po Qn Qw Ra Rc) Im(Dp gP Id Iz jK kC kG Kl Kj Kl KN Ko kP Kr mI mP Ow Pi Qn Qv Ra Rc Ss Tz Up Vp) Ml(aX aZ bA bM bN

Figure 36 Continued eC Ed Fb Fd Fi Fy Gb Gp Hp jH jV kG Ko lK ml mP nC nM Ou qY Tz Uf) Nn(Hw Id In Iq Jh jK Jo Kj Kl Ko Lv Mf Mm Mu Mx Nb Nd Ns
oH Ou Oy Pa Pf Pg Pi Pz) Sr(aA aE aQ aW CH Cx dK eC Ed Fn Hc In Is Jr Kj Kl Nk oE oN Ow Oy Qa Ss Tz Vs) Io(Hv Hw In Iq Jo Lv Lz Mg
Mh Mm Mx Nb Nd Nm Nq Nr Ns Oc Oh Oy Pa Pb Pc Pf Pg) nI(Af aH al aP Ar bB cH Cs cU dR Fw hB iA Kj Kq Ky oF Ow Pk Qv St Ug Uu
Vo Vv) aA(Af Ax Ba Co Di Dp dR Gc kG kl Ko kP Kq lX mZ nK oE Ou Pi Pj Pk Si Tz Ti) Lz(Fc Fd Fi Gb Hp It Iv jl kG kN kP Lp lX ml mP
nC Nm Og Om Uz Wb Wc Wd) Fy(Aa aF bG bN cH De dJ Dp Et Gp Jo Lu Mw Nk Nw oE oN Pb Pj Qy Rx Tz) Gc(dR Fp Ha Hx Iv iZ Lj Lx
Mw Ni No Nu Ny Oh Pf Qv Qw Ra Sh St Uu Yd) Wb(Ar aW Cs Ex hB Jh Kx Lh Mh Mk Ni Nr Nu oE oF Om Pa Pd Po Ql Ra Rm) aZ(Aa aM
bA Dd Fr Ih Ir Jg Jq Jr Js Li Lj Lw Mn Mu Mz Nk On Pe Qa Qe) Nm(Ch Hr Hw Iq jK Lv Mf Mh Mj My Nc Nd Nq Ns Oe Of Oh Oy Pc qY Tz)
Hv(Dp Fp Hr Iq Iv Mg Nq Nr Og Oh Pa Pb Pc Pf Pg Pz Qe Rx Wc Wf Ti) Mr(Hr Iq Jh jl jK Ly Mh Ni Nq Ns Oe Of Oh Oy Pc Pf Pg Pz Rt Wc)
jK(Ij Iq Jt Lh Li Lv Lx Md Mi Mj Mq Nb Nt Ny Oh Ok Pc Pe Qa) bA(aH aM bM bO cH cV cX Dd Di dK Fr Ih Ir Jg Mw Pb Qe Rt) Nr(Fp Hw
Iq Jh kP Lv Nb Nd Ns Oe Oh Oy Pa Pc Pg Rt Vc) Jr(aX Ba bM bN Dp Gp Ko Mm Mp Ou Pj Ql Rx Us Wc Wf Yd) Og(Bb Hu Hw Il In Lv Mj
Mu Mv Mx Nc Nq Nx Oh Pb Pc Pf) On(aF Ao aW bF bN bZ cE CH Ct dH Eq Kl Rt Sh Ss Vo) Qa(Ba dG eC Gp Hc jT kG kN kP Kq lM lX mZ
nA nD qY) Uu(Bb Cp Dk Ef Ih Jp Js Jt Ko Li Nt Om Pg Qe Tn Uc) Pe(aQ aV aX bM bN dH dK Dp Kl Mk oE PF Pg Rg Ss) Et(cE Ed IZ jl jO
Ki Kl Pi Pk Qv Ss Tz Uv Yd) Lp(aW hB Kx Mh Mk Ni Nu oE Ql Qv Qx Qy Uf Uh Vq) Pb(cT Hw Ii Iq Jh Jk Mg ml Mj Mx Nq Nx Pa Pc Pz)
Pf(Gb Iq kG Mp mZ Nb nD Ns Op Oy Pa Pc Rv Zx Ti) Tz(bN dK Fc Ih Ko Li Lw Ni Nt Ny Om Ra Wd Ti) Ir(bM bN CX Di jQ jT lK Lt Ou Rt
Sh Us Vo) Jq(aF aW bM BN De Dp eC Ed Kj oE Ou qY Us) Js(aQ aX Ba bM bN Ct Di Dp Kj Ou Qv Vv Vo Vs) Mp(Hw In Iq Jh Jo Mk Mm
mZ Nb Nj Pc Pg Pz) Yd(Il Jl Jp Lh Mz Nq Nv Po Ql Qy St Uh Vq) Qe(bN cX Di jD jQ jT Nd Oh Ou Pa Us Vo Vs) Kq(aE Af bG Ct eC Ed Gp
Na Ne Nx Oh Qw We) Fp(Fc Hw Jh Jo Mg Nb Nc Nq Ns Pa Pz Uy) Lw(Bg bM bN bP cD Ch Cs Cx dH Ed Gp qY) It(Hw Iq Jo Lv Mg Mx Ns
Oh Pz Sh Uy Ye) Iv(Dp Hw Jh Jo ml Nb Nq Ns Oe Oh Ou Us) Rx(Cq Cs Ha Hx In Jt Ke Na Nw Pi Rm St) Uz(Ar CX hB Jh Mk Nu oE Ql Qy
St Uh) Is(Dp Ed Iz Kj Kl Qn Qv Rm Us Uv Vs) Li(bM bN bO Cv cX dH Dp Kl Rg Us Vo) Fr(aF Ax Bg bO cE CH Cs cV Dd) Mi(aH aV aY bL
bN De dH cP kP mZ) Sh(Il Jh Jv Nt Nu Om Qy Rm St Vq) Rt(Cp Dd Fd Hw In Jt Om Pi Tv Vp) Pg(hA hX Iq jH jl Ns Oe oN Pc Vo) Eq(Jh Mg
Mu Nq Nt Om Pd St Uf) Mw(aL Bg bM bN cT Cv Dd Iz Ou) Ih(aH AL aQ bN Ct Di dJ Vo) Jo(Ad Dd kG Kn ml Mm mP Pi Up) Bb(aH In Lv
Ly Mn Mu Of Vo) Fd(Ar Cx Mh Mk Nu Ql Qx Qy) Gp(iZ Jn Jt Kn Pi Ra Up Vp) Mz(aH aW bM bN CX De Vo) No(dR eC eD kG lX nD Vv)
Nt(Dp Kj Ss Uv Vc Vo Wh) Jn(aX Ba bN Dp lK Ou Us) Jp(BG bM bN CH Cs) Mm(In Iq Lv Mj Mx Ns) Nb(bM Hr Hx Iq jT Oe) Ij(Ef Jd Ki
Ow Qx Vv) Jh(Bg Gd Hc Iz My Uy) Wf(Cp Jt Mj Om Qx Tn) Nw(Kl Kz oE oN Ou Pi) Us(kG kP ml mS mU nU) qY(Iq Jl Jt Mj Mq) Ny(Dk
Hc hX Ib jl) mZ(kG Ma Mq Qd Uh) kP(Bo Ed Nu Oh Qd) Ch(Jg Mn Nq Om) Lv(Iq jD jT Nd) Mu(oE oH Ou Pi) Qy(Du Rv Ux Wc) Uy(hB Mk
Mv Ql) Pa(Oh Oy Pc Pz) hW(jD jH jT Nk) kG(Ed Kj Nu Uh) Af(ml mU Uw) Bg(Jg Mn Om) Po(Fc Vc Wh) Ti(hB Mj Oh) Na(Dp Kj Ou)
Hr(Cp Hw In) Si(aP hB iZ) Qx(Fi Gb Hp) Pi(Dp Ou Wc) aW(Hp oQ Yl) lX(Lx Oh Qd) Ba(Cs Dd) Gd(Cw Jt) Jg(Cs Kl) Jy(Lj oE) Oe(Jk Pz)
Om(Hc Wh) dR(Ex fR) iZ(aH aL) AaAx BomS DdcS Dilp ThQl FwNk NqHu NumI MkRy MnbM MxPc NdHq JieC StOi WgUh JtKj NxmP
OkbN OweM VoPj aNnK aPdH cXfR dKoQ jHjT Unconstrained panels with 3 analytes, where 0.0E0 >= 'AUC p-value' > 0. Contains 50,000 panels of 17,842,327 total panels evaluated. :
Im{Sh(aA aC AD AF aG aH aI AJ aK AL aM AN AO AP aQ AR AS aU aV AW AX aY aZ BA BB BC bE bF BG bH bI bJ bL bM BN BO bP
bQ bR bU bV bW bX bZ cA cB cC cD cE cF cG CH cI cJ cK cL cM cN CO CP CQ cR CS CT CU CV CW CX cY cZ dA DB DC DD DE dF
DG dH DI dJ DK DL dM dN Dp dR Du Ed EF Eq Et Ex Ez Fc Fd Fn FP FR Fw Fy Gb Gc Gd Gh GL Gn GP Gz Ha HB HC HF hG Hl Ho Hp
Hq Hr Hu Hv Hw Hx iA Ib Ic Id IH Ii IJ Ik Il In IO IP Iq Ir Is It Iu Iv IZ Jd Je Jf Jg Jh Ji Jj Jk Jl Jm Jn Jo Jp Jq Jr Js Jt Ju Jv Jy Kc Kd Ka Kf Kg
Ki Kj Kk Kl Kn Ko Kp kQ KR KS Kx Ky Kz Ld Lh Li Lj Lp Lt Lu Lv Lw Lx Ly Lz Ma Mb Mc Md Mf Mg Mh Mi Mj Mk Ml Mm Mn Mp Mq
Ms Mt Mu Mv Mx My Mz Na Nb Nc Nd Ne Nf Ng Nh Ni Nj Nk Nl Nm Nn No Nq Nr Ns Nt Nu Nv NW Nx NY OE OF Og OH Oi OK Om
ON Op Or Ou Ow Oy Oz Pa Pb Pd Pe PF Pg Ph Pi Pj Pk Po Ps Pz Qa Qb Qc Qd Qe Qg Qh Ql Qm Qn Qt Qu Qw Qx Qy Qz Rb Rc Rf Rg Rh Ri
Rj Rm Rt Ru Rv Rx Ry Rz Si Sj Sr Ss St Tn To Tv Tz Ua Ub Uc Ud Ue Uf Ug Uh Uk Ul Um Un Uo Up Ur Us Ut Uu Uv Uw Ux Uy Uz Va Vb
Vc Vh Vi Vo Vp Vq Vs Vt Vw Vz Wb Wc Wd We Wf Wg Wh Yd Yl Zw Zx Ye Tm Tl Xa Wm Tj Ti Th) Eq(aA aC AD aE AF aG aH aI AJ
AL aM AN AO AP aQ Ar AS aV Aw AX aY aZ BA BB Bc bE BG bH bI bJ bL bM BN BO bQ bR bS bU bV bW bZ cA cB cC cD cE cF cG
CH cJ cK cM cO CP CQ cR CS CT cU CV cW CX dA DB DC dD DE dF DG dH DI dJ DK DL dN Dp dR Du Ed EF Em Et Ex Ez Fc Fd Fi Fn
FP FR Fw Fy Gb Gd Gh GL Gn gP Gz Ha HB HC Hf hG Hl Hp Hq Hr Hv Hw Hx iA Ib Ic Id Ih Ii Ij Ik Il In Io IP Iq Ir Is It Iu IZ Jd Je Jf Jg Ji Jj
Jk Jl Jm Jn Jo Jp Jq Jr Js Jt Ju Jv Jy Kc Kd Ke Kf Ki Kj Kk Kl Kn Ko Kp kQ KR KS Kx Ky Kz Ld Lh Li Lj Lp Lt Lu Lv Lw Lx Ly Lz Ma Mb
Mc Md Me Mf Mg Mh Mi Mj Mk Ml Mn Mp Mq Mr Ms Mu Mw Mx My Mz Na Nb Nc Nd Ne Nf Ng Nh Ni Nj Nl Nm Nn No Nq Nr Ns Nt
Nu Nv NW Nx NY Oa OF Og OH Oi Ok Om On Op Or Ou Ow Oy Oz Pa Pb Pd Pe PF Pg Ph Pi Pj PK Po Ps Pz Qa Qb Qc Qd Qe Qg Qh Ql Qm
Qn Qt Qu Qv Qw Qx Qy Qz Ra Rb Rc Rf Rg Rh Ri Rj Rm Rt Ru Rv Ry Rz Sf Si Sj Sr Ss St Tn To Tv Tz Ua Ub Uc Ud Ue Uf Ug Uh Uk Ul
Um Un Uo Up Ur Us Ut Uu Uv Uw Ux Uy Uz Va Vb Vc Vh Vi Vo Vp Vq Vs Vw Vz Wb Wc Wd We Wf Wg Wh Yd Yl Zw Zx Ye Tm Tl Xa
Wm Tj Ti Th) Va(aA aC AD aE AF aG aH aI AJ aK AL aM AN AO AP aQ AR AS aU aV AW AX aY aZ BA BB BC bE bF BG bH bI bJ bL
bM BN BO bQ bR bS bU bV bW bX bZ cA cB cC cD cE cF cG CH cI cJ cK cL cM cN CO CP CQ cR CS CT CU CV CW cY cZ dA DB DC
DD DE dF DG dH DI dJ DK DL dM dN DR Ed Em Et Ez Fc Fd Fi Fn FP Fr Fw Fy Gb Gc Gd Gl Gn GP Gz Hb Hc Hf Hl Ho Hp Hq Hr Hu Hv
Hw Hx Ib Ic Id Ih Ii Ij Ik Il In Io IP Iq Ir Is It Iu Iv Iz Jf Jg Jh Ji Jj Jk Jl Jm Jn Jo Jp Jq Jr Js Jt Jy Kd Ke Kf Kg Ki Kj Kk Kl Kn Ko Kp Kq Kr Kx
Ky Kz Ld Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu Mv Mw Mx My
Mz Na Nb Nc Nd Ne Nf Ng Nh Ni Nj Nk Nl Nm Nn No Nq Nr Ns Nt Nu Nv Nw Nx NY Oa OE Of Og Oh Oi Ok Om On Or Ou Ow Oy Oz Pa
Pb Pd Pe Pf Pg Ph Pi Pj Pk Po Ps Pz Qa Qb Qc Qd Qe Qg Qh Ql Qm Qn Qt Qu Qw Qx Qy Qz Ra Rb Rc Rf Rg Rh Ri Rj Rm Rt Ru Rv Rx Ry
Rz Si Sr Ss St Tn To Tv Tz Ub Uc Ud Ue Uf Ug Uh Uk Ul Um Un Uo Up Ur Us Ut Uu Uv Uw Uy Uz Vb Vc Vh Vi Vo Vp Vq Vs Vt Vw
Vz Wb Wc Wd We Wf Wg Wh Yd Yl Zw Ye Tl Xa Wm Tj Ti Th) Ux(aA AD aE AF aG aH aI AJ aK AL aM An AO AP aQ AR AS aU aV
AW AX aY aZ BA BB BC bE Bg bI bJ bL bM Bn BO bP bQ bR bS bV bW bX bZ cB cC cE cG cH cI cJ cL cM cN CO Cp CQ CS CT CU CV
cW CX cY cZ dA DB DC Dd De dF DG DI dJ DK DL dM dN DR Du Ed Ef Em Et Ex Ez Fc Fd Fi Fn Fp Fr Fw Fy Gb Gc Gd Gh Gn GP Gz
Hb Hf Hl Ho Hq Hr Hu Hv Hw Hx Ic Id Ih Ii IJ Ik Il In Io IP Iq Ir Is It Iu Iv Jd Jg Jh Ji Jj Jk Jl Jm Jn Jo Jp Jq Jr Js Jt Jy Kc Kd Ke Kf Kg Ki Kj
Kk Kl Kn Ko Kp Kq Kr Kx Ky Kz Ld Lh Li Lj Lu Lv Lw Lx Ly Lz Ma Mb Mc Md Me Mf Mg Mh Mi Mj Mk Ml Mm Mn Mp Mq Mr Ms Mu
Mv Mw Mx My Mz Na Nb Nc Nd Ne Nf Ng Nh Ni Nj Nk Nl Nm Nn No Nq Nr Ns Nt Nu Nv Nw Nx NY OE OF Og Oh Oi Ok Om On Or Ou
Ow Oy Pa Pb Pc Pe Pf Pg Ph Pi Pj Pk Po Ps Pz Qa Qb Qc Qd Qe Qg Qh Ql Qt Qu Qv Qw Qx Qy Qz Ra Rb Rc Rf Rg Ri Rj Rm Rt Ru Rv Rx
Ry Rz Sr Ss St Tn To Tv Tz Ua Ub Uc Ud Ue Ug Uh Uk Ul Um Un Uo Up Ur Us Ut Uu Uv Uw Uy Uz Vb Vc Vh Vi Vo Vp Vs Vt Vw Wc
Wd We Wf Wg Wh Yd Yl Ye Tl Xa Wm Tj Ti Th) Xa(aA Ad AF aG aH aI Aj aK AI aM AN AO AP aQ AR AS aU AW AX aY aZ BA BB Bc
bF BG bH bJ bL bM BN BO bP bR bU bV bX cA cD cE cF CH cI cK cN CO Cp CQ Cs Ct CU CV CW cX cY DB DC DD DE Dg dH DI dK

Yl Zw Zx Ye Tm Tl Xa Wm Tj Ti Th) Ps(aA aC AD aE aF aG aH al Aj aK AL aM AN AO AP aQ Ar AS aU aV AW AX aY BA BB BC bE bF
BG bH bI bJ bL bM bN bO bP bQ bR bU bV bW bX bZ cA cB cC cD cE cF cG CH cI cJ cK cL cM cN CO CP CQ cR CS CT CU CV CW cY
cZ dA Db DC DD DE dF Dg dH DI dJ dK DL dM dN Dp DR Du Ed Ef Em Eq Et Ex Ez Fc Fd Fi Fn Fp FR Fw Fy Gb Gc Gd Gh Gl Gn GP Gz
Ha Hb Hf Hl Ho Hp Hq Hr Hv Hw Hx Ic Id Ih Ii Ik Il In Io Ip Iq Ir Is It Iu Iv Iz Jd Je Jf Jg Jh Ji Jj Jk Jl Jm Jn Jo Jp Jq Jr Js Jt Ju Jv Jy Kc Kd Ke
Kf Kg Kj Kk Kl Kn Ko Kp Kq Kr Ks Kx Ky Kz Ld Lh Lj Lp Lt Lu Lv Lw Lx Ly Lz Ma Mb Mc Md Me Mf Mg Mh Mi Mj Mk Ml Mm Mn Mp
Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx NY Oa Of Og Oh Ok
Om On Op Or Ou Ow Oy Oz Pa Pb Pd Pf Pg Ph Pi Pj Pk Po Pz Qa Qb Qc Qd Qe Qg Qh Ql Qm Qn Qu Qv Qx Qy Qz Ra Rb Rc Rf Rg Rh Ri Rj
Rm Rt Ru Rv Rx Ry Rz Sf Sh Si Sj Ss St Tn To Tv Tz Ua Ub Uc Ud Ue Uf Ug Uk Ul Um Un Uo Up Ur Us Ut Uv Uw Ux Uy Uz Vb Vc Vh Vo
Vp Vs Vw Vz Wb Wc Wd We Wg Wh Yd Yl Zw Zx Tm Tl Xa Wm Tj Ti Th) No(aC aD aE AF aG aH aJ aK AN AO Ap aQ aS aU AX aY aZ
Ba BB bC bE bG bH bI bJ bM Bn BO bP bQ bS bW bZ cA cC cD cE cJ cK cN CO cP cQ CS CU cV cW cX cY cZ Db Dc Dd De dG dI dJ DK dM
DR Ed Ef Et Ex Ez Fc Fi Fw Gc GP Hb Hc Ho Hq Hr Hu Hv Hx Ib Ic Ih Il iP Ir Is It Iu Iv Jg Jh Ji Jk Jl Jm Jn Jo Jr Jt Kc Kd Ke Kg Ki Kj Kq Ld
Lh Lj Lx Lz Ma Mb Mf Mg Mi Mj Mk Ml Mm Mp Mq Ms Mt Mu Mv Mw My Na Nb Nd Ne Ng Ni Nk Nm Nn Nq Nu Nv NW Nx nY Oa Oe
Of Oh Oi Om On Op Ou Ow Oz Pa Pb Pc Pd Pf Pg Ph Pj Pz Qa Qb Qc Qd Qe Ql Qn Qt Qu Qv Qw Qx Qy Qz Rc Rh Rj Rm Ru Rx Rz Sh Si St
Tz Uc Ue Uf Ug Uh Uk Ul Un Uo Ur Ut Uv Ux Vc Vh Vo Vp Vq Vt Wc Wd We Wf Wh Zw Ye Ti Th) Ih(aA aC aD aE Af aH AJ aK aN Ao aP
AR aU aV aW aX aY Ba bB Bc bJ bM Bn BO bP bQ bS bX cD cE cF Ch cI cJ cL cN CO cP cQ Cu CV CW cX dB Dc DD De dG dI Dk dL dM
Dr Du Ed Eq Et Fc Fi Fr Fw Gb Gc Gp Hc Hf Hl Ho Hq Hr Hu Hv Hw Ib Ic Ik In Io IP Iq Ir Is It Iu Iv Jh Ji Jj Jk Jn Jo Jq Jr Js Jt Ju Jv Kd Ke Kg
Kl Ko Kp Kq Lh Lp Lu Lv Lx Lz Mf Mg Mh Mi Mj Mk Ml Mm Mp Mq Ms Mt Mu Mv Mw Mx My Na Nb Nd Nh Nj Nm Nn Nq Nt Nu Nw
Ny Oe Oh Oi Om On Op Or Ou Ow Oy Oz Pa Pb Pc Pd Pf Pg Ph Pj Po Qa Qb Qc Qd Qg Qm Qn Qt Qv Qw Qx Qy Ri Rj Rt Rv Rx Sh Si Ss St
To Tv Tz Ua Ue Uf Ug Uh Uk Un Uo Us Ut Uu Uv Uy Vh Vp Vq Vs Vt Wd Wf Zw Ye Wm Ti) Ed(aC Ad aE aK aM Ao ApaQ aU aW Ax bA
bB BC bG bJ bQ cC cl Co CS CT Cw CX Db Dc dK DI dN Dr Ef Et Fi Fy Gc Hb Hf Ho Hq Hu Hv Hx Ii Il iO Iq Ir Is It Iu Iv Iz Jd Jg Jh Jl Jn Jp
Js Jt Jy Kd Ke Kf Kg Kj Kk Kn Kq Kx Ld Lh Lv Lx Lz Ma Mf Mh Mi Mk Ml Mm Mp Mq Mr Mt Mu Mv Mw Mz Nb Nd Nf Ng Nj Nm Nq Nr
Nt Nv Ny Oa Of Oh Oi Ok Om On Ou Oz Pf Pi Po Pz Qa Qd Qe Ql Qt Qv Qx Qy Ra Rf Rh Rm Ru Rz Si Ss St Tn Uc Uf Un Ut Uw Ux Vb Vh
Vo Vt Vw Wd Wh Zw Xa Wm Tj Ti) Nb(aC aE AF aG aH aN aO Ap Ar aS aU aW aY aZ bC bE bF BG bJ Bn Bo bW bX cC cD cF cL CO
CV Cw Cx cZ Dd Dk Dr Et Ez Fc Fi Fr Fw Gb Gc Gp hB Hc Hl Hv Hx iA Ic Ik Ir Is It Iu Iv Jh Ji Jj Jk Jl Js Jt Kc Kd Ke Kg Ko Kz Lj Lx Lz Mg
Mi Mk Ml Mm Mp Mq Ms Mt Mu Mv Mw Mx My Na Nf Ng Nm Nn Nu Nw Nx Oe Of Og Oh Om Ow Oy Oz Pa Pc Pd Pf Pj Po Qa Qb Qd Ql
Qm Qn Qt Qw Qx Qy Rb Rt Sh Si St Tn Tz Ue Uf Uh Ur Us Vh Vp Vq Vt Wd We Wf Tl Ti) Un(aD aE AF Al An Ap aV aW AX aZ BA Bb bE
bJ bL bM BN BO bU cK CT CX Dc Dd dE Di dK dL Dr Ex Gc Gl Gp Hu Hw Ic II Io Ir Is It Iu Iv Jf Jg Jh Jk Jn Js Jt Ju Kd kQ Ks Ld Lj Lp Lt
Lx Lz Mf Mh Mt Mw Mx Na Ng Nn Nr Nt Nu Nv Nx Ny Oa Of Og Oh Oi On Or Oz Pb Pd Pf Pz Qa Qb Qc Qe Qm Qn Qt Qu Qw Qy Ra Rc
Rg Rm Rx Sf Si St To Tv Ub Uf Ug Uh Uk Ul Us Ut Uv Ux Vo Vq Vz Wc Wf Yd Xa Wm Th) Ow(aA aD aE AF AJ aN aO aX aY aZ bE bF bJ
bL bM Bn BO bP bQ bR cE cL cQ cS cV cW Cx Dc DD De dF dG dH dK Dr Eq Ez Fd Fr Fw Gb Gc Gz Ha Hb Hp Hu Hv Hw Hx Io Ir Is It Iv
Jg Jh Jk Jl Jn Jp Jt Ke Ki Kl Ko Kq Ks Ld Lj Lv Ma Mm Ms Mu Mv Mw Nd Nt Nu Nw Ny Oa Oi On Oz Pb Pc Pi Pk Qa Qb Qd Qe Qm Qw Qy
Rc Rg Rm Rv Si St Tz Ub Uh Uo Uv Vq Vt Wb Yd) Nw(aC aD aE AF al Aj aO Ar aV aW Ax aZ BA Bb Bc bE bG bJ bL bM BN BO bP cD cE
cM cP cR CV cW CX cZ dA DD De dG dH dl DL dN Dp Dr Du EF Ex Fc Fi Fw Gc Gh GL hB Hu Ic Ir It Iu Iv Jg Jh Jm Jn Jt Ju Jv Kd kQ
Ld Lj Mq Mw Mx Nr Nt Nu Ny Oa Ou Pa Pd Pi Pk Qa Qm Qn Qu Qy Rc Rg Rm Ru Sf Sh Si St Ub Uk Ul Us Uv Wf Ya Tm) St(aC aD aE aF
aG aK Ap aQ Ar aU aW aX aY aZ Ba Bb bC bE bG bJ bM Bn Bo bS bW cC cL CO Cu cV Cw cY cZ Dd De dJ dK DR Et Ez Fc Fi Fw Gb Gc
Hb Ho Hu Hv Ic iJ Ik Ir Is It Iu Iv Jh Ji Js Kc Kd Ke Kg Kj Kz Lx Mg Mi Mk Mm Mp Mq Ms Mt Mu Na Nn Nt Nu nW Oe Oh Oi Om Oz Pd Pf
Pg Pj Qd Qt Qw Qy Qz Rz Si Uf Uh Uk Ur Vh Vq Vt Wc Wd Wf) Is(aA aC AD aE AF Aj aN aO Ar aS aW aY aZ bE bF BG bJ bM Bn BO bZ
CH Cq CV cW Cx cZ dD Dk Dr eF Fc fP Fr Fw Gb Gc gP Hb Hc Hl Hq Iu Iv Jj Jl Jp Jy Ke Ld Lj Lv Mf Mj Mn Mq My Nt Nu Nx Og Oz Pd
Qm Qw Qy Rb Rg Rt Rv Sh Tn Uh Uo Ur Us Uu Uv Vp Vq Vt Wb Wf Yd Zx) Qa(aA aC aD aE Af aG AJ aN aV aW aY aZ bJ Bn BO bP
bS cD cF Ch cV cW CX DD De dl Dk Dr Ex Fc fP Fr Fw Gc Gl gP Hb Hc Hl Hu Ib Ic Ip Iv Jh Ji Jj Jm Ke Ld Mi Mj Ms My Nt Nu Nv Oe Oi
Oy Oz Pc Pd Qn Qt Qw Qy Rt Sh Si Tn Ua Uh Uo Ur Us Uu Uv Vp Vq Vs Vt We Wf Zw Ye) Ld(aE aY aZ BA bM Cu Cx Dd Dr Fd Fi Fy Gc
Hb Ho Hp Hq Hu Hv Hw Hx Ii Il In Io Ip Iq It Iu Iv Ji Jk Jn Js Jt Ke Kn Ko Lj Mi Mr Mw Mx Na Nr Nt Nu Ny Oa Of Oh On Oz Pa Pc Pg Pi Pz
Qb Qc Qd Qe Qh Qy Rm Tv Tz Uc Uh Vq Vt Wb Xa) Jn(aC AF aG aJ aN aW aY aZ bE bG bJ bM Bn bO cO cP cV CW CX Dd Dk dM Dr
Fc Gc gP Hc Ib iP It Iu Iv Ji Jl Kc Mg Mi Mj Mp Mq Na Nn nY Oe Oi Oz Pa Pc Pd Pj Qn Qv Qw Rj Rx Si Uf Uh Uo Us Vp Vq Vt Wf Ye)
Rm(aA aC aE AF aG aN aO aS aW aY aZ bE bG bJ bM Bn bO bS bX Ch Cq cV Cx DD Dk Dr Fc Gb Gc Hb Hc Ic Iu Iv Ji Jl Ke Mi Mj Mp Mq
Ms My Nf Og Oz Pa Pc Pd Pj Qm Qn Qw Rt Rv Sh Si Uf Uh Ur Uu Vp Vq Vt Wf Zw) Ir(aA aC aD AF aG aN aW aY aZ bE bJ bM Bn bO CV
cW Cx cZ DD Dr Fc Gc Hb Hu Iu Iv Jh Ji Ke Mg Mi Mp Mq Ms Mt Mu Mw Na Nn Nt Nu Oz Pd Ql Qm Qy Rt Si Uf Uh Uo Vt Wb Wd Wf)
Oa(aC aG aN aW aZ bM Bo Cx Dd dl Dr Fc Fw Gb Gc Hb Hu Ic Iu Jh Ji Ke Ko Kq Mi Mk Mp Mt Na Nn Nt Nu Oe Pd Pf Pj Qm Qy Rx Si Uf
Uh Ur Vq Ti) Ke(aE Af aV AW aY BA bJ bL bM BN bO cD cV dL Dr Fc Fw Gl Hw Il Iv Jm Lj Mw Nd Ne Nr Nt Nu Oh Oi Oz Pa Pf Qm Qy
Rt Ru Us Uv) Gc(aE Af aY bM Bn bO cG CX dA De Dr Hp Hu Hx Iv iZ Jh Jm Jr Kk Lj Lv Mt Mw Nt Nu Ny Oh Oi Pj Qb Qt Qv Qw Qy Rf Tz
Yd) Cx(aA Ax Cq cT Cu Dc Dd Dr Fd Fw Gb Ha Ho Hp In It Iv Ji Jq Jr Js Jt Mi Mr Mw Mx Na Nh Ny Pi Qd Qe Tv Up Vp Vt) Vq(ar aV aY
aZ bJ bL cX dD dE Fp Fw gL hB hG Iv Jh Lj Mq Mw Nd Nr Nt Nu nY oK Qb Qd Ql Qm Qw Qy Rf Si Tz) Qy(aH Aj aX aZ bM bS CH cT Dr
Hb Hu Iv Ji Js Ki Kl Lj Lx Ny Oh Oi Oz Pc Qb Qt Qw Sh Si Ua Uh Ye) On(aD AF aO aY bF BG Bn Bo CH cV cW eF Fr Fw Hc iP Iv Jy Lj
My nY Og Qw Tn Us Uv Vt Wf Yd) Mw(aE Af aG aH Aj aN aZ bM Bn bS Ch De Dr gP Hb Hc Hu Iv Iz Lx Nu Oi Oz Qn Qw Sh Ua Uh Vt Wf
Ye) Fw(Af aM aY aZ bJ BO cG Dr Hb Hx Iv Jh Ji Jj Ki Lx Ms Mt Na Oi Oz Ql Sh Vt) Qd(Af Aj aN aZ bA bM Bn bO Ch cT De Dr Hu My Nu
Oz Qn Qw Ru Ua Uh Us Uu Vp Wf) Ji(aD aE Af aV aY bJ bL bM bN bO cD Dr Fc Hp Jm Lj Lv Nt Nu Ny Qm Ru Uv Yd) Vt(aD aN aV aY bJ
Bn Dp Ef Hw It Iu Iv Jh Jt Mv Na Nn Nr Nu Qm Qw Rc Rg Ub) Nt(aX cH dB Eq Fr Hb Lj Lx Lz Ml Oh Oz Pb Pc Qb Qs Si Tz Uh) Iv(aN aW
aY aZ bR Dc Hb Il Jm Jp Ny Oz Pc Pj Qc Qm Si Uh Ti) Lj(aC aE aG Ba cE Cu Dr Hu It Jh Kq Mt Nu Om Pd Pf Qt Si) Ny(Af aN aW Bn dR Fc
Ic Iu Mk Mp Na Nn Oh Pd Qn Si Ur Wf) Oh(aC aE aF aY bJ bM bO Dd Dr Gb Hu Nu Pc Pi Qm Wb) Si(aA aE aM bM bN bO Dr Hp Jm Mr Nu
Qm Wb Yd Xa) Dr(aW cQ Mf Nn Nr Om Pf Qb Qc Qe Tz Uh) Qe(aC Af aN aY aZ bM Bn BO Nu Uo) Js(aE Af aY bM BO cW Dd Oz Pc Uh)
Kq(aD Aj aO aY Bn cD cV cW Fr kQ Yd) Lx(aF aN aY bE bM bO Dd Fc Nu) Mt(aE aY cH fP Fr Hx Iu Qb) Ch(Ef Iz Jh Nn Nq Om) Qm(Bb
Dc Ho Hv Mi Na) Pf(aF aO aY bM bO fP) Af(Hw It Jt Nv Uc) Nn(aE aZ bM Eq fP) Nr(aC aE aS bO Hb) Nu(Dc Hb Hx Oz Pc) Mq(Al aX Dc
Dd Jm) Qb(aC aG Ba Na Pd) Xa(aN aY Bo cV Jh) Om(Aj aY Eq fP Uv) Uh(Hp Hw It Pi Ql) Cu(aY Bo fP Of) Hx(aN aW Fc Ic) Ut(Aj aY fP
Wf) Hb(Hw iZ Tz) Ql(Dc Dd Jm) Oz(gL Hp It) aN(Cs Jq Po) Bn(Jq Mr) Eq(Ba Jh) Ic(aE iZ) Wf(Jh Mr) Nv(aG gP) AraE BoHa DcUr DdMl
FcTz FpaW MfWb MsJm ItcX IubM PcgL PdaX aSbA} Yd{Ke(aA aC AD aE AF aG aH al AJ aK AL aM AN AO AP aQ AR AS aU aV Aw
aX aY aZ BA BB BC bE bF Bg bH bI bL bM Bn BO bP bQ bR bS bV bW bX bZ cA cB cC cD cE cF cG CH cI cJ cK cL cM cN CO CP CQ cR

Vc Vh Vo Vp Vq Vs Vt Vw Vz Wb Wc Wd We Wf Wg Wh Yl Zw Zx Ye Tm Tl Xa Wm Tj Ti Th) Wf(aA aC AD aE AF aG aH al AJ aK AL
aM AN AO AP aQ AR AS aU aV Aw aX aY aZ Ba BB BC bE bF BG bH bI bJ bL bM BN BO bP bQ bR bS bU bV bW bX bZ cA cB cC cD cE
cF cG CH cI cJ cK cL cM cN CO CP CQ cR CS CT CU CV CW CX cY cZ dA DB DC DD DE dF DG dH DI dJ Dk DL dM dN Dp Dr Du EF
Eq Et Ex Ez Fc Fd Fi Fn Fp FR Fw Gb Gc Gd Gh Gl Gn Gp Gz Ha HB Hc Hf Hl Ho Hp Hq Hr Hu Hv Hw Hx Ib Ic Id Ih Ii Ik Il In Io Ip Iq Ir Is
It Iu Iv Iz Jd Je Jf Jg Jh Ji Jj Jk Jl Jm Jo Jp Jq Js Jt Ju Jv Jy Kc Kd Ke Kf Kg Ki Kj Kk Kl Kn Ko Kp KR Ks Kx Ky Kz Ld Lh Lj Lp Lt Lu Lv Lw
Ly Lz Ma Mb Mc Md Me Mf Mg Mj Mk Ml Mm Mn Mp Mq Mr Ms Mt Mu Mv Mx My Mz Na Nc Nd Ne Nf Ng Nh Ni Nj Nk Nl Nm No Nq
Ns Nt Nu Nv Nw Nx Ny OE OF Og Oh Oi Ok Om On Op Or Ou Oy Oz Pa Pb Pc Pd Pg Ph Pi Pj Pk Po Ps Pz Qb Qc Qd Qe Qg Qh Ql Qm Qn
Qt Qu Qv Qw Qv Qz Rb Rc Rf Rg Rh Ri Rj Rm Rt Rv Rx Ry Rz Sf Si Sj Sr Ss St Tn To Tv Tz Ua Ub Uc Ud Ue Uf Ug Uh Uk Ul Um Un
Uo Up Ur Us Ut Uu Uv Uw Ux Uy Uz Vb Vc Vh Vo Vp Vq Vs Vt Vw Vz Wb Wc Wd We Wg Wh Yl Zw Zx Ye Tm Tl Xa Wm Tj Ti Th)
We(Aj As Ax Ch cT Cu Cw Dc Dr Fy Gc Hv Hw Id Ih In Ir Is Iv Jq Jr Js Jt Kd Kn Kq Kr Lw Mi Ml Mr Mt Mz Na Ny Oi Ow Pi Ps Qa Qw Qx
Ra Ru Sr Tv Uc Up Vh Vp Vt Wg Ye Xa) Aj(Du Eq Fc Fd Fi Gb Gh Hl Ho Hp Lp Lt Op Ps Rt Ru Rv Rx Ry Rz Sf Si Sj Uw Ux Uy Uz Vb Vc
Vh Vw Vz Wb Wc Wd Wg Wh Yl Zw Zx Ye Tm Tl Xa Ti Th) Ch(Du Eq Fc Fd Fi Gb Gh Hl Ho Hp Lp Lt Op Ps Rt Rv Rx Ry Rz Sf Si Sj Uw
Ux Uy Uz Vc Vh Vw Vz Wb Wc Wd Wg Wh Yl Zw Zx Ye Tm Tl Xa Ti Th) Uu(Dr Du Eq Fc Fd Fi Gb Gc Gd Gn Hl Ho Hp Lp Lt Op Ps Ru
Rx Ry Rz Sf Si Sj Uw Ux Uy Vb Vh Vw Vz Wb Yl Zw Zx Ye Tm Tl Xa Ti Th) Ye(aA AF Ax aY Bg cH Cs cV gL Hc Ih iJ It IZ Jn Js kR Ld Lj
Lz Mh Ml Mq My Nx oE OF Oh oK Ow Ps Qa Sr) Ow(Dr Du Fc Fd Gd Ho Hp Lp Op Ps Ru Rv Rx Ry Rz Sj Uw Ux Uy Uz Vb Vc Vz Wb Wd
Wh Yl Zw Zx Tm Xa) Dr(Eq Hc Ib Iz Kd Ke Ki Kj Kl Ld Qn Qw Qx Rt Ru Rx Sr Tz Uh Us Uy Vb Vt Th) Rt(Ax bA Cq cT Cu Dc Fy Ho Iq Ir
Is Iv Jn Js Kd Lj Mi Na Oi Pi Qw Sr Xa) Eq(Af aU aW Bn cO cS Cx dK Mg Mh Mi Mp Mq Mu Oh Oi Oz Qn Qy Ru Sr) Ru(cV fP Hu Iz Jj Jk
Kl Kz Ld Lj Mr Nw Oh Oy Oz Sr Uh Un) Qw(Fd Fi nI Ps Si Uy Vc Wc Wd Wh Yl Xa Ti Th) Lj(Du Fc Fd Hl Lp Nw Op Ps Rx Wb Yl Zw Ti
Th) Af(Fd Gh Lp Ps Uw Vh Vw Wd Wg Yl Zw Zx Xa) Yl(aZ Gl Hc Iz Kl Ld My Oz Ua Vs Vt) nI(Ib Jj Jo mI nN nT Nx Oz Pb Ur Us) Zw(Ax
Cs Js Ld Lx Lz Ml Oh Qa Ra) Wh(Ax bA Cs Ld Lx No Nr Qx Ra Xa) Ps(Bg Iz Oi Oz Rx Ua Uh Us Vs Vt) Xa(Bg Iz Ld My Oi Oy Oz Ua Us)
Oh(Du Fc Rx Rz Uy Vz Wb Zx Tm) Ti(aZ Bg Iz Kl My Ss Vt) Rx(aA Ax Cs Iz Jn Js Ny) Nw(Ih Ir It Ns Og Oz Pb) Uy(Kd Ld Lz Mh Ml Qx
Ur) Sr(Gc Hl Ux Vb Vc Wc) Iz(Fd Gn Hp Vz Th) Lp(Kd Oz Qv Ur Vt) Bg(Ho Rz Uh Wd) Wb(Ld Lz Mh Ml) Zx(aZ Oi Oz) De(Uh Vc) Th(Ax
Cs) Ml(Rv Uw) Mt(Ux Wd) Us(mT nD) Oz(Gh Tl) GdOi NnRz MiWd JjUh LdUz UxaW} Qa{Zw(aA aC Ad AF aI AJ AN Ar aV aW Ax aY aZ Ba bC bE BG bJ bM BN BO bQ bS bV cB cG Ch cJ cN cO Cq Cs CV cX cZ dA Db dD De dH dI DK dM Dr Em Ez Fc Fd Fn Fy Gd Gl Gn Gz Hc hG Hl Hu Ib Ic Id Ih Io Ip Iv Jf Jh Jj Jl Jm Jn Jo Jq Jr Kd Ki Kj Kk Kl Ko Kx Ld Lj Lv Lx Lz Mb Mf Mg Mh Mj Mk Ml Mq Mt My Na Nc Ne Nf Ni Nj Nk Nl Nn No Nr Nt Nu Nv Nx Oe Oh Oi On Ow Oy Oz Pa Pb Pd Pf Qc Qd Qe Qn Qt Qw Qx Qy Rf Rg Rh Rj Rt Ru Rx Sh Sr Ua Uc Uh Ul Uo Up Ur Uv Vp Vq Vs We Wf Wh Yl Ye Xa Wm) Wf(aA aC AF AN aO aQ aW Bb bE bM BN Bo cB cN Cq cT cV CX Db dD De dF dG dH dI Dk dL Dp Dr Du Ex Fc Fn Fp Fw Gl Hl Hu Ih Il Iq Is It Iv iZ Je Jh Jl Jm Jn Jo Jq Kd Ki Kl Kr Ky Lh Lj Lu Lv Ma Mj Mq Mr Mt Mu Mz Ni Nj Nn No Nr Nt Nu Nw Nx Ny Oe Oi Ok Ou Oy Oz Pa Pb Pc Pf Po Ps Qn Qv Qw Qy Rg Rt Ru Rx Sj Sr Tn To Ub Uc Ul Uo Up Ur Uu Uv Vp Vs Wb Wc) Rt(aD aE Af AJ aN aP aR Ax aY aZ bA Bb bM Bn bP bS Ch cN Cp Cq Cu Cv CX Dc Dd dH dI dL Dp Dr Du Em Eq Ez Fd fP Fr Fw Fy gP Gz Hc Ho Hu Hv Ib Il In Iq Ir Is Iv Jm Jn Jr Js Jt Kd Ki Kl Kn Lj Me Mi Mj Mr Mx Nj Nl Nr Nv nY Oe Pb Pg Ph Pi Qd Qh Ql Qn Qt Qv Qw Rb Ri Sr Ss Tv Tz Ua Ub Uh Ul Uo Up Ur Us Uu Uv Uy Uz Vp Vq Vs Vt Wb Wc Yl Ye Xa Tj) Dr(Ez Fc Fd Gh HC Hp Ib Ic Id Jd Jv Kc Kd Ke Kg Ki Kl kQ Kr Kx Ld Ne nW Or Ow Pj Ps Qg Ql Qm Qv Qw Qx Qy Rc Rf Rj Rm Ru Rx Si Sr Tn To Tv Tz Ua Uc Ue Uf Ug Uh Uk Ul Um Un Up Ur Us Uu Uv Uw Uy Vb Vc Vh Vo Vp Vq Vs Vt Vw Vz Wc Wd We Wh Ye Tm Ti Th) Rx(AD AF aN aO aY aZ Bg bM Bn bO bZ Ch Co cV dD Dg Eq fP Fr gP Hc Hp Iv Iz Jf Jn Kd Kl kS Lj Lv Ma Mj My Nv Nx Ny Of oK Op Ou Oy Oz Qn Qu Qw Sh Sr Tn Ub Uo Us Uu Uv Uw Ux Vp Vs Vt Wb We Zx) nI(Ad Af Aj Cv CX Hq Ii Il In It Iu Jj Jo Jp Jq Jr Jt kC kG kI kN kP Lu LX lY mF mI Mm Mr nA nC ND nH nK nL Nm NN nT Nv Nx Ny Oe Of Oh Oi oO oP oQ Oy Oz Pb Pz Qn Tv Ur Us Uu) Uv(Du Eq Fc Fd Fi Gb Gc Gd Gh Gn Hl Ho Hp kG Lp Lt Op Ps Ru Rv Ry Sf Sh Si Sj Uw Ux Uy Uz Vb Vc Vh Vw Vz Wb Wc Wd We Wg Wh Yl Zx Ye Tm Tl Xa Ti Th) Oz(Du Eq Fd Fi Gb Gh Hl Ho Hp Lp Lt Nw Op Ps Ru Rv Ry Rz Sf Sh Si Sj Uw Ux Uy Vb Vc Vh Vw Vz Wb Wc Wd We Wg Wh Yl Zx Ye Tm Tl Xa Ti Th) We(AF aN aO aW aY bM cV CX Dd dG Dk dL Du Ex Fc Fn Hu Hw Il Iv Jh Jl Jq Kd Ky Mi Mj Mt Nn Nt Nu Oe Pc Qn Qw Qy Rg Us Vp) Ye(aA AF aN aO aW aY bJ bM Bn cV Cx dD dF Dp Gl Hu iZ Je Jl Jq Ky Lv Mj Mz Nu Nx Ok Ou Qn Qy Rg Tn Uc Up Us Vp Vs Wb) Af(Du Eq Fc Fd Fi Gb Gh Hl Ho Hp Lp Lt Op Ps Ru Rv Ry Rz Sf Sh Si Sj Uw Uy Uz Vc Vz Wc Wd Wg Wh Yl Tm Tl Xa) Wb(An aY bS Ch cV CX Hc Ib Ic Jl Jq Kd Kr Ld Lj Mh Mj Nv Nx Oe Oi Ow Qe Qw Rj Ru Uh Ur Us Uu Vp Vs) Us(Du Eq Fc Fd Gc Gd Gh Hl Ho Hp Lp Op Ps Ru Ry Sf Uw Ux Uy Uz Vb Vc Vh Vw Vz Wc Wd Wg Wh Yl Zx Xa) Uw(aN Ap aW aY bM Bn Bo Cw CX Dk Fc Fn Iv Mi Mj Mt Nn Nt Pj Qn Qy Sr Ur Vp Vq) Vs(Du Fc Fi Gb Gc Gn Hl Ho Op Ps Ru Rv Ry Rz Sh Si Uh Uy Uz Vb Vh Vw Wd Yl Xa) aN(Du Eq Fd Gh Ho Op Ru Rv Rz Sh Uy Uz Vb Vc Vh Vw Vz Wc Wg Yl Tm Tl Xa Th) aY(Du Eq Lp Ps Sh Ux Uy Vb Vc Vh Vw Vz Wc Wd Wg Wh Yl Zx Tm Tl Xa Ti) Bn(Du Eq Fi Op Ps Ux Uy Uz Vc Vh Vw Wd Wg Wh Yl Zx Tm Tl Xa Th) Uu(Du Fi Gb Gc Gn Hl Ho Op Ps Ru Rz Si Uh Ux Vb Vw Wd Zx Ti Th) Cx(Eq mS mZ Ux Uy Uz Vb Vc Vh Vw Vz Wc Wd Wg Wh Yl Tm Tl Xa) Qn(Du Eq Ux Uy Uz Vb Vc Vh Vw Vz Wc Wd Wg Wh Yl Zx Tm Tl Xa) Vp(Du Eq Fd Gd Hl Hp Lp Ps Ru Rv Ux Uy Uz Wc Wh Yl Tl Xa Th) Eq(aW cO dI Jh Kg Mg Mi Mj Mt Mu Nn Qy Uf Ur) Dk(Du Ux Uy Uz Vc Vh Vw Wc Wd Wg Zx Tl Xa) Ru(aA bM Iq Kl Kz Mj Oy Pa Pc Qv Sr Uo) Uy(bM Bo Cq Cv dD dI Ex Hl Iq Kd Ld Ur) Fc(dR hG Nx oH Oi Pb Uo Ur Ux Vc Wh) Uh(bN Cw Ha Hq Ii Jo Lh Ur Wc Ti) Du(BG Kl Lj Mj Nv Oy Sh Ur) Wh(bM Bo cX dI Iv Jq Nt Nu Oe) Ti(aA Kd Kl Lj Oi Pc Vt) aW(Hp Rz Sh Ux Vz Yl Xa) bM(Fd Ps Vc Vz Wc Yl Tm) Th(Iv Kd Oi Pc Sr Ur) Wd(Aj Bg Ch De dI Pb) Kl(Gn Ry Rz Ux Vb Vw) Nw(Hr Ns Of Og Pb) Sh(Jv Nu Qy Sr) Zx(cX Oe Oi Pc) Gc(Kr Ne Up) Mj(Ps Ry Tl) Hl(Oi Sr Ul) Oe(Ux Vh Vz) Ur(Ex Tm Tl) Aj(nN Vb) Ch(Vb Vw) Gd(Ex Qy) Iv(Fd Wc) Jj(kP lX) Ps(aZ Hc) Vc(Bo dI) Ux(cX Qy) Pc(Yl Xa) FihG GbPb GlRv SrVh TlcX} Cx{nN(aA aC Ad Af aH aI Aj AL aM AN Ao Ap aQ Ar aS aV aW Ax aY aZ BA BB BC bG bL BO bU bV bW cA cC cD cE cF cG CH cJ cK cM CO CP cQ cR cS CT Cu dA Db dC DD DE DG dJ DK Dl Dp dR Ef Ez Fb Fp Fr hB HC Hq Hr Hv Hw iH Ii Il In Io Iq It Iu iZ Jd Jf Jg Jh Jj Jk Jl Jm Jq Jr Js Jt kC kE KF KG kI kK Kl kN kO kP KR Ks Ky Ld Lh lW LX lY Lz Ma Mb Me Mg MH mI Mj Mk Ml MM Mn Mp Mq Mr MS Mt mU MZ Na nB Nc ND Ne Ng Nh NI NJ Nk Nl Nn NR Ns NT nU Nv Nx NY OE oF Og OH Oi OK Om ON Oy Oz Pb Pf Pg Ph Pz Qu Qw Qy Qz Rc Rm St To Tv Ub Ue Uf Ug Up Uv Vp Vq Vu Vv tF) mS(aA aF aH AN aP AR aU Ax aY bA bB bE bF BG bI bJ bM BN Bo bP bR bU bV cA cE cF CH cI cO CS cT CU CV CW cZ dB dD dG dJ DK DL Dp dR Et Ez Fa Fp Fw gL GP hC Hq Hr Hu Hv Hw Hx iA Ib Ih iJ Io iP Iq Is Iu Iv iZ Je Jf Ji Jk Jm Jq Jr Js Jt kC kF kG kP Kx Kz Ld Lj Lx Ly Lz Ma Mb ME mF Mg MH Mi Mj Ml MP Mq Mr Mt MU Mx mY mZ Na NC ND Nf NH NI NJ nK NL Nm Nn NO Nr NT Nu Nx nY OE OF OH Oi Or Ow Oz Pa Pb Pd Pf Qb Qc Qd Qe Qm Qv Qw Ra Rb Rf Rh Rj St Tv Ub Uh Up Ur Us Uu Vq Vs Vt Wm tF) nI(aA AD Af aH AJ aM aN aP Ar bB BG Bo cE CH Cs Ct Cv cW dB Di Dp dR eM Fp Ha hC Hq Hu Hx Ib Ih Ip Iq Ir Is iZ Jf Jh Jj Jk Jn Jo Jr Js Kf kG KP Ld Lj Ly Mb MF Mh mI Mq Ms mU Mx mY mZ Ng nK No nT Nu NY OE Of Oh Oi Oy Oz Pb Pz Qb Qc Qd Qe Qg Qw Qz Rb Rj Sr St Tv Ub Ug Uh Um Ur Us Uu Uv Vs Vt Vu Vv) mU(aC Af Aj Al Ao Ap Ar Bb BG Bo cD Ch cL cN Co Cp Cq Cv Dc Dd De Dg Dk Dl Dp Ef Ez hB HC Hu Hw Ii Il Io It Iu IZ Jg Jh Jj Jk Jo Jq Jt Jv Kf KG Kj kK Kl Kn kR Ld mF Mg

Figure 36 Continued

Rj Uf Up Ut Vp Vt Wb Wd Wh Zw) Mr(Al aN aW Bb Bo Gh Gp Ic Ih Il Ir Jg Jk Jm Jp Lp Mt Mx Nd Nu Nv Nw Nx Ny Om On Pa Pf Pz Qb Qc Qd Qe Qy Rj Rt St To Uh Us Ut Uv Uy Vt Zx Tm) Ny(aF AN aW bJ cS Hu Ih Io Iv Jh Ld Mg Mk Mq Mt Mv Ni Nq Nt Nu Oe Pd Pf Qw Qy Rt) Nr(aA aS Bo Gz Jd Jh Jy Kq Ld Mq Mt Mu Nq Nw Qd Qy Rh Un Ur Ut Vt) Kq(Af AN aW Bn Ch Fc Fw Il Jm Kd Kl Lp Nu Pf Qn Qw Qy Us Vs) Qy(Ax Cs Ex Ir Is Iv Js Ld Lx Mj Ml Mq Mt Mx Oh Po Qv) Pf(aA aF aO bF Dd Gb Hv Ih Jh Nt Pi Un Wb) Mq(Bb Dd Fw Hu Ih Il Ir Lp Mx Uy) Jh(Ch De Eq Fw Kk Mx Of Pb Uu Vb) Hu(Cs Ir Js Ld Lx Oh On Qe) Iv(aN aW aY Gp Ih Nx Of Th) Ut(AF aY Bn De Pb Uu Uv) Nt(Ml Mx Nw Qb Qd Qx Vt) Mt(aX Fr Hx Ih Mx Pb Uv) Ir(Bo Jd Jy Ld Ni Nu Rt) On(aN aY Gl Ki Nu Uv Zw) Fw(aM Hx Ih Ld Mv) Nu(Is Nw Qe Vt) Ld(Bb Il Lp Wb) Ih(aA Pc Vt) Ch(Nq Wd) Qe(aA aN) Kd(Jd Jy) Ke(Nj Nx) Ps(cV cX) Nw(cX Qw) Om(Pb Uv) MlQd MxbJ IsaF JsaY VtaN} Rt{Is(Ad aF As Ax Cp Cq Cs Cu Cv Cw Dc Em Fw Hl Ho Hv Hw In Iv Jn Jr Js Jt Kd Ke Kg Kl Kn Kq Mi Mr Mt Mx Na Nr Nt Nu Ny Pc Ph Pi Pk Qy Ub Up Uz Xa) Jn(aW Bn bQ cL CO cP Cu cX Dd Fc Fi Fw Ho Hv Hw Il Iv Kd Kg Kq Ld Mf Mg Mi Mp Mt Mu Na Om Pc Pd Ph Qv Qy Uf Uh Uk Vq Wd) Cu(AF aX aY aZ bL Di Fw Il Jk Ju Kd Lp Mf Mx Nv Ny Oh Pa Pb Pc Pf Qb Qc Qe Qh Qn St Ul Vs Wc Xa Th) Iv(aF aW aY Dc Fw Gc Ih Il Jg Jk Jm Jt Kd Kq Ks Mf Nw Nx Ny Oh On Pa Pc Qb Qc Qe Qh Qy St Ul Vt) Ny(Af aW bS cX Gc Ho Hv Ib Il Ji Kd Ld Mf Mg Mi Mk Mt Oe Pd Qn Rj Uf Vp Vq) Kd(aF Ba Cs Fp hC Ih It Jl Js Kq Mt Nr Nt Nv Nw Oh Ps Uf) Mi(Fw Ih Jk Jm Js Kq Mf Mx Nr Nv On Pf Ps Qe Rm St Xa) Js(aF aW aY bN Dd Fc Fw Ho Hu Il Jk Kq Nt Qy) Xa(aW Dc Fw Ho Jm Nx Oi Pa Vt) Pi(aW Ih Jm Nr Nw Oh On Pf) Ho(Ba Ih Il Ng Oh On Qb) Hv(Fw Ih Il Nr Pf Ps St) Mx(Jh Kq Ld Mq Mt Om) Qy(Ax bA Fy Oh Uu) Jk(Ax Fy Jr Nr) Jm(Ji Kq Mq Mt) Oh(aF Dd Hu Pc) Ut(Ch Cq Dc Iq) aW(Fd Fp Fy Jr) Fw(Hx Na On) Kq(Ax Ch Lp) aF(Na Nr On) Cq(Nv Ps) Mq(Dd Il) Mt(aX Fr) Ih(Pc Uu) Ir(bQ Up) ChJh CpPb FyNv NtOi LxPc HwLp IlhB QebQ JtdR} Ld{Lp(bR eF fP gP hB hC hF iA iH iJ Il iO iP kQ kR kS Md Nu nW oE oK Pc Qy Ri Rj Tz Ua Ub Uc Ud Ue Uf Ug Uh Uk Ul Um Un Uo Up Us Ut Uu Uw Ux Uy Uz Vb Vc Vh Vo Vp Vq Vs Vt Vw Vz Wb Wc Wd We Wg Wh Yl Zw Ye Tm Tl Xa) Wb(Af aZ bL Bn cF Ch cX Gh Gl Gp Hu Ih Il iO Jg Jm Mh Mt Mx Nr Nu Nx Ny Oh Pa Pc Pf Pz Qb Qc Qn Qy St Ul Us Uv Vs Th) Xa(AF AN aO aX Bb Bn Ch cV cX De Dg Fw Gl Hu Il Jg Jm Kl Lv Nu Nx Ny Oi Pb Pc Qn Qy Ul Uv Uy Vs Zw) Uy(Af cX Dd Fi Fw Gc Hw lH Il iP Ir It Iv Jg Jn kQ kR Mx Nh Nr Nu Ny oE oH pF Qe Qw Qy St Vq) Zw(Al bX Dc Fw Ih Il Ir Is Jk Jm Jn kR Mt Nr Nt Ny Oh On Pf Qb Qd Qe Qy St Vq) Fw(Du Eq Fc Fi Gd Op Ux Uz Vc Vw Vz Wc We Wh Yl Zx Ye Tm Tl Ti Th) Th(aA Cs Cu Dd Fb Fp Iv Jn Kd Mr Ny Pi Qd St Tz Un Vp) Ny(Du Eq Fd Ps Uw Vz Wc Wd We Wh Yl Zx Ye Tm Tl Ti) Qy(Eq Fd Fi Ho Ps Ux Uz Wc Wh Yl) Il(Gc Hp Op Sh Uz Wh Yl Zx) Kd(Gc Ps Uw Ux Uz Vh We Ti) Mx(Du Ux Vz Tl) Ho(kR Nu Pc) Wc(aW Bb Qn) Jm(Uz Vw Ye) Af(nN We) Fd(aW Gl) Nr(Vc Vz) Jg(Ux Wh) Ke(Nx Uv) Ps(Jn Pc) Uz(aW bL) TiUh EqHu FikR SfaA} aW{Xa(Af Aj Ar aX Bo Ch Cs Dg Eq Fp Gd HB Hx Iv Jj Jo Kg Kj Kl Lz Mq Nw Ny Oi Or Oy Pa Ph Ql Qx Sh Vs Vt) Ny(Du Eq Fc Fd Gh Hl Ho Hp Lp Lt Op Ps Rv Sf Sh Si Sj Ux Vb Vw Vz Wb Wc Wd We Wh Zw Zx Ye Tm Tl Ti Th) Cs(Eq Fc Fd Fi Gh Hl Ho Hp Lp Lt Op Ps Ry Rz Sf Sh Si Sj Vz We Yl Zw Zx Ye Tm Tl) Wb(Ar Ex Fp hB Is Iv Ji Jn Jr Js Ke Kx Lh Lx Mj Ml Mx Nw Oh Or Pf Qb Ql) Eq(aA aP Cu Ef Fp Hx Iv Jh Jl Jn Kq Mt Mv Nq Nw On Ps Qd St Ut) Fp(Du Fc Fd Gb Hl Ho Hp Ps Sh Uw Ux Uy Uz Vz Wc Wd Yl Ye) Ur(kC kK kN lY mE mH mI mY mZ nD nJ nK nN nO nR nT) Iv(Fc Fi Hl Lp Ps Rz Sh Ux Vb Vc Vz Wc Yl Ye) Hp(Ar Jj Js Lx Lz Ml Nw Oh Pf Qd Qx Tz) Kj(Fd kP lX mS mW mZ nD) Ps(aA Dg iZ Kl Pc Qy Vo) Sh(Dk Jn Kq On Qd Ut) Vz(Ax Jn Js Mj Mx) mS(Bo Ug Um Us Uu) Cv(kI mZ nA nD) Jn(Ux Vb Yl Ye) Ke(Jo Uv Vo) kP(aA Jj Kg) Ux(iZ Kq) nN(Aj Jo) nD(Bo Uh) FdMq HlJs HxYe ItYl SiaA JjLp KgmZ NwOp lXhB} Nw{Nu(Eq Fp Hu Ir It Jj Jn Js Lp Mm My Ns Oe Og Oy Pb Qb Qc Sh Ux Uy Vz Wd Wh Yl Zw Ye Th) Pb(aA Et Fp Ih In Ip Ir It Iv Ji Jj Jn Jo Js Jt Lw Mi Ms My Nm Ns Nt Oe Of Og Qb Qd) It(aA Et Fp Hr Hu Hx Ih Ii Ik Ir Jj Jm Jq Mh My Nd Nk Ns Nx Oe Of Og Oy Pc Qc) Og(Et Fp Ih Il Ip Iq Ir Iv Jh Ji Jm Jn Js Jt Nr Ns Po Qb Qc Qd) Ir(Hr Hu Hx Ii Jj Jl Jq Mh Mj My Nh Ns Nv Nx Oe Of Oy) Ml(iC jF jG jH jK jO jP jQ jR jT jU jV jY lN) Js(Ii jD jE Jj jK JQ jR jT jY My Ns Wc) Ns(Fp Ih Il Jm Jn Nd Nr Of Qb Qc Qd) Hr(Fp Hv Hw In Ji Jo Jt Mz Nm) Ih(Ii Jj Jq Ms My Nx Oe Qc Zw) Jr(hA iC jF jK jL jO jP jT) Of(aA Et Ip Jg Jt Nm Qd) Fp(Hu Jj My Oe Oy) Jj(Il Ip Jm Qb) Wc(Iv Jn Mi) Kd(Uy Ti Th) Nx(Ji Jn Xa) Oe(aA Et Qb) Aj(Jt nN) My(Il Qb) Hq(jK Nd) WmMm ThIv MsJn HujK IlOy IpaA IsjT ZwRa JgUu JiJq LpVp} Uu{Uh(Aa Ad As Bn Cp Cq Cu Cw Dc Dd Hv Hw Id In Ir Is It Iv Jg Jn Jq Jr Jt Kd Ke Kj Kp Kq Kr Lw Ml Mz Na Nf Nm Nt Ny Om Pb Pi Ra Rb Rj Tv Uc Ul Un Up Ur Us Vp Vt Vv) Gc(Hu Ih Ir Iv Iz Jg Jh Jk Jn Kq Mt Nu Nv On Pf Ps Qd Qy Ut) Ke(aE bL BN dJ Fc fP Il Jg Lp Mm Nx Ug Ur Uv Wc Ti Th) Qy(Du Fi Hl Hp Lp Ry Si Uw Vh Wc Wd We Wg) Ps(aF aO cV cX Hu Jg Jh Kd Mt Nr Pz Qn Qw) Ti(Ir Is Iv Kq Ny On Qd Qe Ut) Ih(Fi Gb Ho Lp Si Uw Vw Wd Zx) Si(iZ Jg Jn Kq Ny St) Th(Ef Jh Kq On Ut) Fi(Jn Ny On St Ut) Jg(kI kP mS Mz Qd) Wd(Ir Jn Ny Qc St) Xa(aY cV Hu Jh) Kq(De Sf Ur Tm) Fc(Is Qd Ut) Ho(Jn Ny St) Lp(Mq On Ut) Vw(Qb Qd St) Pf(Gb Hp Wb) Rz(Jn Ny) GpHp QdUx JhUy UwaY aNmI} Ur{Lp(aF aL Ao aP AR aS aV Ax aY Ba bE bJ BN Bo bP bR bZ CO CS Ct cU cV cZ DC Dk dN Du Ef Et Ez Fd Fw Fy Gc Gz Ha HB Hp Hr Hu Hv Hw Hx Ih Ii iO Ir Is It Iu Iz Jd Ji Jk Jn Jr Jy Ke Ki Kk Kz Lh Lx Lz Ma Mf Mg Mh Mj Mk Ml Mr Mt Mu Nc Nd Ne Nf Nh Ni Nk Nl Nq Nt Nu Nv Ny Oe Of Om On Op Or Ou Pa Pf Pz Qb Qd Qm Qw Qy Ra Rf Rj Rm Si Tn Tz Ua Uf Un Uw Vq Vt Wd Wh Wm) Uh(Hv Ir It Jj Jn Jr Kd Na Nm Tv Up Vp) Th(Ax Cs Ir Iv Jn Js Jt Kc Ny Qe Xa) Jm(Fd kC kI mS Xa) nN(Af Bn cX De tF) Ih(Eq Gc Sh Uy) Ir(Fc Wb Wh Ti) Ny(Fc Uy Ti) mW(Af Bn cX) Fw(Ps Sh) Qe(Tm Ti) kN(Mf Pf) EqJk MxWh XaaY KegW PsOi aNkP cXmZ} Mq{Wb(Af aN aY bL Bn Ch cX Dd De Fw Gp Ic Il Jm Mh Nx Oe Oh Pa Pb Pf Qn Uh Us Th) Kd(Du Fc Fd Fi Gb Gc Gh Gn Hl Ho Hp Lp Lt Op Ps Ry Rz Sf Sh Si Sj Uz Ti Th) Eq(Al Ba Dd Fi Hu Ic Il Iz Jg Jk Jm Jn Jp Lp Mt Mx Nr Nt Pf Pz Qy) Xa(aN aX aY Bo Ch Dd De Fw Gl Il Jm Kl Nx Oi Pb Vs Th) Il(Hl Rv Sh Uw Ux Uz Vz We Wh Zw Zx Ye) Lp(aJ iP Oi Pb Rj Ua Ug Uh Us Vp We Ye) Dd(Ux Uz Vh Vz Wc Wd We Wh Yl Zw Ye) Zw(Ih Is Jm Jn Lx Mt Nr Oh Vq) Uy(Af aN aX aZ Bo Ch cX Pb) Ye(Al Fw Ih Jm Jn Mx Ny) Jm(Fd Rv Ux Uz We) Ch(Gb Uw Vw Wd) Fw(Fc Rv Sh Ux) Al(Sh We Wh) Fd(Af aN Pb) Ps(Oi Pb Us) Du(Ax Mx) Wh(Ih Nr) ThIv MxTl JnUw} Ps{Us(aF aO cV cX Gc Hu Ir Iv Jh Jn Kg Kj Kq Mt Mu Oe Oi Pc Qe Qn Qw Qy Rc Up Ut Vt) Oi(AF aN aO aY bJ Bn cV cX dI Hu Iv Jl Lv Nu Qn Qy Vp) Vs(aF cV cX Hu Hv Ic Iv Jh Mg Mt Nt Nu Oe Qn Qy) Oe(hB iZ Nu Ua Uv Vb Vo Vt Wc Wh) Pc(Ar Ax Cs gL Ih Kx Lx Mh Ml Oh) Vp(aA Iv Jn Js Kd Mx Ny Qe Rc) Qy(Aj Bg Ch Ef Kl Mh Ml Oh) Vt(Af aN aY BN cX Qn) Mi(Bg Pb Ua Uv Wc) Mt(aX Gl Kl Pb Uv) Qn(iZ Uh Vo Wc Wh) Pf(aO aY Kl Vo Zw) Nu(Mh Ml Qx Rc) Uh(aF cV cX Qw) Zw(Ax Cs Ml) Jh(Bg Ch Pb) aY(Ar hB Iv) cX(Vo Wc Wh) Lx(aO Mj) Ye(aF cV) Kd(Vo Wc) Kl(Ez Mg) Uv(Iv Kq) gL(fP Ki) BgWd CvFw UaHu IciZ PbPd} nN{Jo(Ad aE Af aG aI AN Ao AP Ar AS Ax Ba bB bE bF bH bI bJ bL BN bR bU bW bX cA cI cN cR Cs Cu CV CW cX cZ Db Dc DE Dg Dk Dl Ef eM hB hC Ih Iv iZ Jn Jr Kc Kf Kl Kp Nh Nu nY oE oF Pb Pf Pj Qc tF) Aj(aF aN Ar bR cA cH cI cR Cs cV cX Dk Et hB Is iZ Jg Jp Jy Kk Ko Kp Kq Lz mZ nD Ni Nt Nu On Qn Ri St Un Vt tF) Cv(An Cp hB Hv Hx Ip Is Jj kI Kj mZ nD Oy Pb Uv tF) Kj(Af cN De Dp Ko nD Nu Qm) Jj(Hb Il iZ Ml Nh Qc Us) Ad(Dp hB Jp mZ) Af(Lz mS Ou Ph) Bo(Qu Ug) Nq(Bg Us) hB(Oi Vv) DeUg DpKg NuPh IiJn JpUs JrNx} Xa{aY(Aj aM Ar Bo Et Fp Hx Iv Kz Lx Ml Mr Og Oi Pf Qe Qx Rc Un Vt) Af(Cu Fw Is Jn Kd Ke Nv Ny Om On Pf Qc Qd Uh Ut) Ch(bJ cV Ef Jh Mg Mi Mt Mu Nq Pd Qd Ql Qy Uf Ut) Qy(Aj Bg Eq Kl Mh Oh Oi Rc Sh Vs) Kd(Aj Ar Dp Fp hB Hx Iv Jj St) Jh(Aj Bg Eq Iz Kl Pb Uv Vs) Nx(Ar Iv Ji Jj Ke Og Pa Vt) Ny(Bn cX Ic Oe Oi Qn Vp) Vs(Ap Kq Mt Pd Pf Qd Vq) Oi(bJ cV Fw Iv Nu Ql) Mt(aX fP Fr Gl Uv) Kq(Gl Kl Of Uv) Pf(aO Hc Kl Of) aF(aX Is Oh St) aN(aM Qd Sh Vt) Bo(cQ cV Nd) Bg(Mv Nq) Sh(Fw Jv) Qd(Dk Pb) Uh(iZ Nl) Vt(Bn Us) Pc(Ih Oh) dC(gL Nu) AjHu AnhB EqcO MkfP JjJm QlPb} jT{Qd(aA Fr Hq Hu Hv Hw Ik Il In Is jG jH Ji Jj JK Jn jO JQ Jr Js lK lN Lv Lw Md Mh Ml Mu My Mz Ng Ni Nj Nk Pb Pf Pz Qb qV qY) Is(aA Et Hr Hu Hw Hx iC Ii Ik It Iu jD jH Jj JK Jm Jo Js jV jY lK Mb Mg Mk Ml Mr Ms Mu Mv Mx My Nd Ng Ni

Figure 36 Continued

Nk Nr Of Oy Pb) Jr(Et Hq Hr Hu hV Hw iC li jD JK Lz Mb Ms Mu My Nc Ng Nk Nv Of Oy Qb) Js(Et hV ln Ji Jj jK Jm Jo Jq jY IK Lv Mb Ml
My Nd Ng Nk Oe Of Oy Qb) Ml(aA Et jH Jl Jq lM Lv Lw Md Mt Mz) Qb(aA jH Jl Jj Jq Lw Mz) LzJq aAjK} Qy{Oh(Du Eq Fc Fd Fi Gb Gc
Gd Gh Gn Hl Ho Hp Lp Lt Op Rv Ry Rz Sf Sh Si Sj Uw Ux Uy Uz Vw Vz Wc Wd Wg Wh Yl Zx Ye Tm Tl) Eq(Ax bA cO Cs cU dR Fy Ih Is
Iv Jn Js Lx Mh oE oF On Qv St) Sh(Fw Ih Ir Is Iv Jn Js Ju Lx Nr Pf Qb Rm Sf) Ux(Ax Cs Fy Ih Lx Ml Nr oF Pf) Ax(Rz Vb Vw Wh Zw Ye)
Js(Uw Vb Vw Wh Zw Ye) Cs(Vb Wh Zw Ye Th) Iv(Vb Wc Wd We) Lp(Ar Lz Ml Qv) Ch(Du Gc Uw) Lx(Rz Vc Zw) Mh(Fd Ho Uz) Ye(Fp
Mx Qb) Aj(Du Vh) Nr(Rz Vb) Ml(Uz Wb) FyRz GdcH LzUz HoKj WeJn VwoF} Mt{Eq(AF AN aY Ba bG bl bJ cH Ex Fw Hq Hu Hw Hx Ih
Is It Iz Jk Jm Jn Kq Ky Lv Mi Mu Ng Nv Ny Of On Pc Pf Pz Qd Qn Uf Ut Uv We) aX(Sh Uw Ux Uy Vb Vh Vw Vz Wb Wc Wd We Wh Yl Zx
Ye Tl) Ux(aS bG bl bJ cH Fr Hq Hw Hx Ih Il It Qt St Vq) Fr(Uw Uy Vb Vc Vh Vw Vz Wb Wd We Wh Zw Ye) Zw(fP Ih Jn Mx Oh Qb Qx St)
We(Aj Bg Ch Kl Mx Ny Pb St) Wb(Ch Mh Mx Oh Qb Qx) Ch(Uw Vz Wd) Uv(eM Gc Lt) aY(Tm Tl) AjTi DeUh ThIv MkhX MxVz WcfP
WdNy UyhB} Kc{gW(aJ aP Ar aX bL bN BO bV cB cQ Cu CW DB DE dG dI dJ dN Fn fP Gl gP Ha hB hG Hq Hu Hx iH Iu Jh Jk Jp Kn Lh
Lx Me Mh Mj Nj Nk Nl Nv Nx oF Oh oN Or pF Ph Qt Qv Rj Rm St Ue Uf Ug Vp tF) Nx(aE bL bN De Fy Hq Jo Mm Pb Uh Up Uv Vo) bN(Aj
li Iz Jj Kj Mm Uh Uv Vo) Zw(Ax Ih Mh Oh Pf Ra Wm) Uv(Af De oE Uh Th) eC(De Gz Lh oN Vs) Vo(Bn De Il oE) Th(Cs Fp Ub) Mm(oE Pb)
Jo(Il Uh) Vs(Fy oE) DeUh WbOh UsPb} Kq{Uv(Ex Fd Fi Gb Gc Gd Gh Gn Gz Hl Ho Hp Lt Op Rv Ry Sh Si Sj Uh Uw Ux Uy Uz Vz Wb Yl
Zw Zx Ye Tm Tl Ti Th) Ch(Du Eq Fc Fd Fi Gc Gh Gn Hl Ho Lp Lt Op Rv Rz Sf Sj Uy Uz Vc Vh Vz Wg Wh Yl Zw Zx Ye Tm Tl) Sh(aY Fw
Il Jm Ju Jv Sf) Aj(bN De Fc Ug Tm Ti) Eq(aF aO aY cV Jn Qn) Ux(aF aN Bn Qn Us Vp) Th(aF aO Cs Iv) Zw(Ax Mh Oh) aY(Rz Wd Wh)
Ye(aF iZ) Uh(bN De) AfUz BgWg BnRz ExVo GdkR MhWb WeNy UyhB} Wb{Pf(aO aY bF BG bZ cE CH eF Gc gL hF hG Hq iA Ic iJ iO Iv
IZ Jy Kd Kl kR Lu Mi Mj Ml My nY oF Og oH Qw Rc Sh Vt Zx) Oh(aN aO cV cX Fw Gc Hu Ic Ji Kc Kd Mi Mk Ml Nu Oe Oi Pc Pj Qn)
Ml(aF Bb bN Fi Fw Gp Hu Il Jk Kd) Mh(Ho Hv Jh Kd Kg Kj Mi Pd) Is(aF cV Ic Jl Qn Vp) Mk(Fw Jm Kd Mx Ul) Lz(Fw Kd Ul) Js(Oe Qn Vp)
Ch(Jh Nq) Lx(aF aO) Qx(Fw Kd) Jn(Uh Vp) aY(hB Iv) ArKd IhPc} Uh{bN(Aa Ad aM As bA Bn Cp Cq Cu Cw Dc Dd Fy Hv Hw fb Id In Ir Is
It Iv Ji Jn Jo Jq Jr Js Jt Kd Kn Kp Kr Lw Mj Ml Mz Na Nf Nm Nr Ny Om Pb Pi Pk Ra Rb Rj Tv Uc Ud Ul Un Up Us Vp Vs Vt Vu Vv) Vs(Cu
Fy Is It Iv Ml Nr Ra Up) Ra(Cw Hq Jj Jo Pb Uv) Ml(Cw Hq Jo Lh) hB(Lp Uy Th) It(Jo Up) Iv(Wc Th) Pb(Lw Vv) FcJn IsJo WcJs UvkG UwiZ
mFmS} jK{Js(aA Et hA Hq Hr Hu Hw iC In jG JM Jo Jq jY IK Lw Mg Mk Ms My Nd Ng Of Oy Pb Qd qT) aA(cS cW hA Hq Hu iC jE jG jL
jO jQ IK IN Mz Of Oy Pb) Jr(Et Hq Hr Hv Hw Hx jG Jh jO IN Me My Mz Oi Pb) dM(bA bC bF bG bL bQ cE cG cL cW dG dH hA IO) Qd(Fr
Hq Hu jH IN Mk) Mz(Jj Ml) jO(Ji Jq) MkIs HqPg HuNy} Iv{aY(Eq Fc Fd Fi Rv Ry Si Uw Ux Uy Vc Vh Vw Vz Wc Wd We Wg Wh Yl Zw Zx
Ye Tm Tl Ti) Th(Ar bR Fp Jj Kx Ky Mr Mz On Ql Ub Un Vt) Wc(AN aZ Gc Kd St Um Vq) Vb(aN Ic Il Jm Nx) Gc(Nc Uv Uy Vs) Zw(Ih Ir Is
Jn) Vc(aZ Fw Nx Pf) Fd(Ih Ny St) We(Jn Ny) FcPb ShJv JnYe UyaZ} Ch{Nq(Eq Fi Gd Rz Uw Ux Uy Uz Vb Vc Vh Vw Vz Wc Wd We Wg
Wh Yl Zw Zx Ye Tm Tl Ti Th) Jh(Eq Fc Gd Op Sh Uw Ux Uz Vb Vc Vh Vw Vz Wc Wd We Wg Wh Yl Zw Zx Ye Tl) Wd(Co iZ Jn Ny On St
Ut) Ef(Wc Ye) Hp(Uf Ut) CuWc FcUt MvYe QdVw} Pf{Sh(aA aY bM bO Dd Fw Hp Hu Jv Nt Ny Pi) Rv(aA aF aO fP iZ kS oH oK oN pF)
Hp(aF aO aY fP oN Vt) Ho(aA aY bM Kg Uv) Vz(aF aO iA Kd Mi) Gb(aF Bg fP Hc) Zw(aO bF Hx Ih) aY(Fd Op Uz Zx) Eq(aA Mi Uf) Gd(aO
oN pF) Wd(Aj Bg) Jj(kN kP) AfFd SiaA JokP VwfP} Jn{Fc(Qv Rj Ug Us Uv Vp Vs Vt Ye) Eq(CO Jh Kc Kg Mg Mi Mu Uf) Wd(Aj Bg Hc
Pb Us Vs) Rz(fP Gl Kl Us Vs) Zw(Ar Lx Rj Vq) Ti(Ar hB Us) Af(Uw Vh) Gc(Us Uv) Ho(Us Vs) Ye(aF Nu) Vp(Du Fd) ArTh BoUy MiWe
linT ShUk RvRj UxaF} Sh{Fw(aM bJ cX Il Jy Mv Nf Nu Oy Pa Pb Pc Tm) Jv(Ba Fy Hw Il It Iz Ng On Qt) Ut(AF Bn cX Il Nx Uv) Nu(Gc Ir Is
Oh Qc) Il(Ar Jh Qd Ql Un) Om(AF) DdLz GlOn MvJm MxbJ HuOh IhPc IsVp QdUs} Ny{Vp(Gc Rz Sf Uw Vw Wd Ti Th) Ti(Bn Nu Oe Oi
Qn Vt) Eq(Co cS Mg Mi Mu Uf) Qn(Gc Ho Lp Wd Zw) Th(Ar Oe Vt) Gc(Kr Up Us) Mk(Fc Uy We) Ho(Kj Mh Us) Wd(Bg Bn Oi) We(Mg
Mi) Ye(aF Nu) BnWh FcLz WcVq RzOi} Js{jY(Et In jD Jj Jm jQ jR Ml Nk Qb Qd) Nk(jF jQ IK IL qY) Et(iC jE jO Of) Wc(aN aY Bo Pc)
My(jD jE) Hw(jE IK) In(jQ jR) Jm(IL qY) Jo(jR jV) AfWd FcPc GlRz NijQ HqjD HuWe IhZw} Is{Af(Uw Ux Uy Vh Vw Vz Wd Zw Zx)
Nu(Eq Rz Ux Vb Vz Wh Zw Ye) Zw(aF Ar Ax Cs Ih Nt Ra) aF(Vb Vz Wc We Ye) Vp(Du Eq Ye) Us(mS nD) Uv(kG Ti) cV(We Ye) BgWd}
Et{Ml(jF jH jO jU IK IN) Of(Ir It Ji Pb Qc) jO(aA Jq Jr Qd) It(Jj Oe Og) Ir(Oe Og) Jr(iC jG) aA(Ip Oe) ThFp HrJi IhJj QbOg} Zw{Ih(Ji Lx Ml
On Pc Ql Qx) Oh(Hv Jh Mi Nt Nu Om Ql) Qd(Ax Cs Ml Ra) Nt(Ml Qb Qx) Ql(Ax Lx Nr) Jk(Ar Lx) AxJh QeRa} Ho{Af(iZ Ml Mx Nr Oh Qx)
Uv(Ar Lx Lz Ml Qx) bM(Lz Mh Ml Oh Qx) Gl(Cu On) Oh(aN aY) aA(Lz Ml) DeiZ FwPb LxaY IhKj aNhB} Eq{St(aX cO cZ Mg Mi Mu Uf)
Fw(cO Ez Ni) iZ(Co dK Mg) Mu(Oh On) Jk(cS Mg) Pc(gL Ih) aF(bQ Ut) MiOn JgcO KdhB cXgL} Th{Cs(aY bJ Jh Kc Kd Mu Mv Nq Qd Uf
Un) Vt(aN Ax bN Us) Ar(Hv Kd Qd) Ax(Ql Un) Fp(Un Vq) Kd(hB Ql) AjJh} Wd{Bg(Fw Mx Nr Oh Om On Rm St) Aj(Fw lh Il Qc St) Pb(Fw
gL Ih) Af(Mx Oh) CuGl FpaN NrHc JmOy OiiZ} Pc{Ih(Hl Hp Lp Lt Ry Sj Ux Vb Vz Wc Wh Zx Ye) Oh(Fc Gb Rv Rz) gL(Sj Wc Wh) Fc(Cs
Lx) LxHp} Af{hB(mE ml mU nU) Fw(Uw Vc Vh) Gc(Ut Uz Vp) iZ(Si Ti) CuUy GbOh MxUw aPkN} Us{Jp(mF mS mU mW nT) Nq(kN mT
nU) Nd(kG mF) mS(Pi Ut) Gclh MvkN lrWc mUhB} cX{aA(kP ml Uw Vh We Tl) iZ(Fi Gc Rz Si Vh Ti) FwVc dKoO} Kd{Uy(aZ Qb St Vt)
Ti(Ar Fp Ql) Wc(St Un) Ql(Gn Hl) GcNf JhWe} Ml{Mz(jH jY lM lN) Ji(jQ jR IN) Qd(Du Uw) jU(Ma qY) NxjV} aN{Fp(Fc Si Uy Ti) Qe(Ux
Vz Yl Ye) Jo(ml nK) LxVc} hB{aY(Fd Fi Lp Uz Wc) Fi(kR Pi) Il(Hl Si) NrSi JhUy} Qd{Nk(jQ jR IN) Mu(jQ jR) qY(jH Nj) CsDu GcKr
RaUw} Vq{Ux(gL Hu Nu Qw) Jo(nC nL) Lp(Aj Cv) FpUy} Qc{Jj(kP nC nH nL) kG(aA Jo Kg mZ)} Fc{Lx(aO Hc oN) Oh(aF aO) AjUt
FwaM} Gc{Uv(Ih Jr On) NrhG NuVt NeaA StQv} Fw{aM(Gh Op Zx) AxYl GdQl SjoE} Lp{Ql(Qv Vp) MkVz JihG JoUf UyVt} Ti{Fp(aA aY
Jm) QeVp aZiZ} Wc{Cu(aY Uv) MiSt JiaA PdaZ} Jo{mZ(Ez Ma Mg) JtfR} Oh{Hu(Rv Vz) NuVc NxkP} Uy{AjJh FpaG JyiP PjiZ}
dM{bC(jQ jR) bBiC cZhA} Du{ArMi CsKc QeVp} Nk{Jr(jQ jR) aAjR} Ji{NuOg JgOf UvbN} We{MiSt IrUt OmUv} aY{Lx(Gh Vc) FpUw}
Cu{BnVb GlSi} Ye{CoiZ NvaF} aA{dK(kl oO)} AaPzgW AjJtbN BoNrVc NtQbWh HwJrhR IhJjkP SiOiiZ JhJqjO RzaXgL VsaZkG Unconstrained panels with 2 analytes, where 1.0E-8 >= 'AUC p-value' > 0. Contains 2,497 panels of 121,819 total panels evaluated. . Vi(aE AF
aG AJ aK aM AN aO AP aQ AR AS aU aV aW AX aY aZ BA BB BC bF BG bH bJ bL bM BN BO bP bR bS bU bV bW bZ cA cB cC cD cE
cF CH cJ cK cL cM cN CO cP cQ cR cS Ct cU CV cW CX DB Dc Dd De dF dG dH Di DK dL dM dN Dp dR Ed EF Eq Et Ex Ez Fc Fi Fn FP
Fw Fy Gc Gd Gh GL GP Ha HB HC hF hG Ho Hq Hr Hv Hw Hx iA Ib Ic Id IH Ii IJ Ik Il Im IO iP Iq Ir Is It Iu Iv IZ Jd Je Jh Ji Jj Jk Jl Jm Jn Jo
Jp Js Ju Jy Kc Kd Ke Kf Kg Ki Kk Kl KQ kR KS Kx Kz Ld Li Lj Lp Lu Lv Lx Lz Mb Md Me Mf Mg Mh Mi Mk Ml Mm Mp Mq Mr Mt Mu
Mv Mw Mx My Na Nb Nc Nd Ne Nf Ng Nh Ni Nj Nk Nl Nm Nn No Nq Nr Ns Nt Nu Nv NW Nx NY Oa OE OF Og OH Oi Ok Om oN Op Ow
Oz Pa Pb Pc Pd Pe PF Ph Pi Pj Po Ps Pz Qa Qb Qc Qd Qe Qg Qh Ql Qn Qt Qu Qv Qw Qx Qy Qz Ra Rb Rc Rg Rh Ri Rj Rm Rt Ru Rv Rx Rz
Sf Sh Si Sj Sr Ss St Tn Tv Tz Ua Ub Uc Ue Uf Ug Uh Uk Ul Um Un Up Ur Us Uu Uv Uy Va Vb Vc Vo Vp Vq Vs Vt Vw Wc We Wf Wh Yd
Zw Ye Tm Tl Ti Th) Im(AA Aj Du Eq Et Fc Fd Fi Fp Fr Gb Gd Gh Hl Ho Hp Hq Hr Hu Hv Hw Hx Ih Ii Ij Ik Il In Io Ip Iq Ir Is It Iu Iv Jg Jh Ji
Jj Jk Jl Jm Jn Jo Jp Jq Jr Js Jt Lh Li Lj Lp Lt Lu Lv Lw Lx Ly Lz Ma Mb Mc Md Me Mf Mg Mh Mi Mj Mk Ml Mm Mn Mp Mq Mr Ms Mt Mu
Mv Mw Mx My Mz Na Nb Nc Nd Ne Nf Ng Nh Nl Nj Nk Nl Nm Nn No Nq Nr Ns Nt Nu Nv Nw Nx Ny Oe Of Og Oh Oi Ok Om On Op Oy
Oz Pa Pb Pc Pd Pe Pf Pg Po Ps Pz Qa Qb Qc Qd Qe Rt Ru Rv Rx Ry Rz Sf Sh Si Sj Uw Ux Uy Uz Va Vb Vc Vh Vw Vz Wb Wc Wd We Wf
Wg Wh Yd Yl Zw Zx Tm Tl Xa Ti Th) Li(AA Du Eq Et Fc Fd Fi Fp Fr Gb Gd Gh Hl Ho Hp Hq Hr Hu Hv Hw Hx Ih Ii Ij Ik Il In Io Ip Iq Ir Is It

Ns Oe Ok Oy Oz Pb Pf Qc Va Wd) Xa(Af Aj aN Ar aZ cX Fc Fp hB Hx Kl Mt Mx Nu Ow Pb Pf Qy Uu) Ok(aA Hu Ih Il Iv Jo Lz Mn Ms My Nd Ng Ni Ns Pf Pg Qc Qe) Va(Ao Ar Cw Dc Dd Ef Et Fp Hx Jm Ko Ld Lh Mq Pz Ql Rf Uc) nl(Ar bB cX Fp Jj Jl kK Kq Mq mU nC Nh nO Nq oQ Rj St Vo) No(Aa Aj Bb Fi Gh Hv Jl Jo Jq Jr jT Mq Mx Ur Uu Vo) Ke(Af Aj De Dp Dr fP Fy Im Jo Kj oE Pb Rt Up Vs) Ih(aA Fr Ip Lp Ma Nu Ux Vb Vz Wb We Wh Yd Zw) Is(Aa Fc Jp jQ Og Op qY Uu Ux Vb Vh We Wg Wh) Pf(Aa Fc Hr Hu It kP Lw Mi My Oi Oz Pb Pd Qc) Jj(Fr Io It Jp Lh Ma Nr Nt Nv Pg Qc Sr) Nn(Gb Ho Rz Sf Sj Uy Vz Wc Ye Tm) Qa(aA Ik Ip Jt Ma Nk Oe Oy Oz Pb) Og(It Iv Jl Mn Nt Nv Om Po Qb Qe) Aa(Et Hr Iq It Iv Jp Nb Pg Qb) aA(Io Jp Jt kP Lh Mm Nj Nt Qb) Qe(Nm Rt Ru Sh Ur Yl Zw Ye) Jg(Fp It Ng Ns Oe Oz Pb Qc) Sr(Du Fd Gb Rz Uu Zx Tm) Jp(Fp Lz Ns Nt Nu Oe Oy) Jt(Fp Hr Ip It Jo Pb Qb) Cx(kN lW lX nD nK nO) Mt(Lp Ru Vb Vc Vz Ye) Ow(Du Gd Gn Ry Sj Vc) Fr(Ip Oe Oy Pb Qc) Qb(Ma Nm Nt Oz Wd) Rt(Fw Kd Mi Nr Ut) Ip(Fp Nt Nu Pb) Wb(Fw Ld Mq Nr) Kq(Rz Uw Uy Vw) Rx(Cs Dr Mr Mx) Pg(Nm Oy Oz Pb) nN(Af Dp Kg Us) It(Ma Mn Nv) Sh(Jh Qy Rm) Ru(Mv Nq Ut) Ur(Dc kN mZ) Aj(Bb Ut) Dr(Kd Rm) Gc(Im iZ) Nt(Qc Wf) Mq(Fi Ho) Hp(Oh Oz) Jq(jO jT) Jr(jO qY) Ld(Hl Yd) Uy(hB Ql) jK(Lw Mr) ArHo BomS TiFp EtUu EqSt ThNb FwWf NqLp NuMn LikP UsmU VtbN jljT Unconstrained panels with 2 analytes, where 1.0E-6 >= 'AUC p-value' > 1.0E-7. Contains 1,719 panels of 121,819 total panels evaluated. : Ps(aC Ad aG aH aK AL aM An Ao Ap aQ aR AS aU aV Aw BA bE bF bH bQ bX bZ cA cB cE cG cK cL Co Cp Cq cT Cv CW cY dA DB DC Dd dF dG dH dJ dK dL dM Dp eF Eq Ex Ez Fc Fd FP Fw Gc Ha Hb hG Hl Hw Id Ii Ik In IP Iq Is It Iu Je Jf Jh Ji Jj Jk Jl Jo Jt Ju Jv Ke Kl Kp kQ Kx Lp Lt Lv Lw Ly Ma Mc Md Mk Mm Mn Mp Mr Ms Mu Mz Nd Ne Nq Nr Ns Nt Nv nW Of Og oH OK Om On Pd Pg Ph Pi Qc Qe Qg Qh Qm Qt Qu Rb Rf Rg Tn To Ub) Nw(AD aE Af aG aH aJ aK AL AN aO Ap aQ AR As aU aV Aw Ax aY aZ BA bB Bc bE bF Bg bL Bn Bo bP bQ bS bX bZ cD cE cG CH cI cJ cK cM cN Co CP Cq Cs cT CU CV Cw cY Db Dc Dd DE dG Di dJ Dk DL Ed Fd Fi Gb Gd Gh Hl Ho Hp jQ jR Jv IK IN Lt qY Rt Rv Sf Sj Sr Ur Us Ut Uw Uz Vb Vc Vh Vz Wd We Zw Ye Tm Tl) Ok(Aa Fr Hq Hv Hw Hx Ii Ik In Io Iq Is Iu Jg Jh Jk Jl Jm Jp Jq Jr Jt Lh Lu Lv Lw Ly Ma Mb Mc Md Me Mf Mg Mh Mi Mj Mk Ml Mm Mp Mq Mr Mt Mu Mv Mx Na Nb Nc Ne Nf Nh Nj Nk Nl Nm Nn Nq Nt Nu Nv Nx Oh Oi Om On Pa Pc Pd Po Pz Uh Va) Uh(Aa AF aH Aj aL aM An Ax bL Bo bV Cs De dJ dK dR Ed eF Fn Fp gP Ha hB hC Hq Hr Ih Il Im Iq iZ Jh Jo Jt Kg Kk kQ kS Lh Li Mg Mi Mj Mm Mw Ne No Oa Oe OH On Pd Pg Ph Qd Qe Qv Re Rf Ri Ru Tt Ue Ug Un Ut Va Vs Vu) Qd(De Hq Hv Hw Hx Ii Il In Iq Is Iu Jh Jk Jl Jm JO Jq Jr Lh Lu Lv Lz Mb Mc Md Mf Mg Mh Mi Mj Mk Ml Mp Mq Mr Mt Mu Mv Mx Na Nb Nc Nf Ng Nl Nq Nr Nv Oh Oi Om Pa Pc Pd Pe Pg Po Pz Qa Qb Qc Qe Rt Ux Vc Wf Zx Xa) On(Aa Fr Hv Hw Hx Ii Ik Il In Io Iq Is Iu Jh jK Jl Jm Jo Jq Jr Lh Lu Lv Lw Lz Ma Mc Md Me Mf Mg Mh Mi Mj Ml Mm Mp Mq Mt Mv Mw Mx Na Nb Ne Nf Nh Ni Nl Nn Nq Nv Nx Oh Om Pa Pd Po Pz Qa Qe Wb Wh Xa) Aa(Fp Fr Hq Hu Hx Il Jg Jh Jk Jl Jm Jo Jq Jr Jt Lh Lj Lv Lw Ly Lz Ma Mb Md Mg Mh Mi Mj Mk Mn Mp Mq Mr Ms Mt Mu Mv My Mz Nd Nf Nh Nj Nk Nl Nn Nq Nr Ns Nt Nu Nv Ny Oe Of Og Oi Om Po Pz) Ny(Du Fi Fr Gb Gh Hl Hp Hu hX Ik Il Iv Jg Jh Jn Js jT Lp Lt Lv Ly Lz Ma Mb Mc Mf Mn Mp Ms Nb nl Nn Nq Nr Nt Oh Op Oy Pa Pd Pg Qa Qb Qe Ry Sf Si Sj Ux Uz Vb Vh Vw Vz Wb Wc Wh Yl Zx) Jp(Fr Hr Hu Ik Il In Iq Iu Iv Jg Jm Jq Jr Jt Lu Lv Lw Lx Ma Mb Mi Mm Mn Mp Mq Ms Mt Mw Mx My Mz Nb Nc Nd Ng Nk Nm Nn Nq Nv Of Oh Om Pa Pf Pg Po Qe Rx Yd) Js(eD Fp hW Ik Il In It Iv Jh jL Jn Jo jP IM Lv Lw Lx Ly Me Mi Ml Mp Ms Mt My Mz Na Nc Nd Ne Nf Nh Ni Nj Ns Nu Nv Oi Om Oy Pg Po Pz Qa Qb qU qW qX Yd Zw) Mw(Aj Bb Bg Ch Fi Fp Fr Ho Hp Hq Hr Hu Ik Io Iq Is Jh Jt Lw Ly Lz Ma Mb Mi Mt Nb Nc Nd Nm Nr Nu Nv Oe Pa Pe Pg Qe Rv Si Zw Ti) Ir(Fc Hv Hw Hx Ih Is Jh JK Jl Jm Jq Jr Lh Lu Lz Mb Md Mf Mg Mi Mk Mq Mr Mu Mv Mx Nb Nc Nl Nq Oh Om Pa Pc Pd Pe Pg Qb Ur Ti) Pf(Hq Ih Ik Il In Ip Iq Iv Jg jK Jr Lj Lu lX Mb Mc Mf Ml Mn Mp Mr Nb Ne Ng Nj Nk Nu Nx Of Oh Oy Pa Pe Pg Qa Qe Vc Wf Yd Zw) Lx(Fd Gb Gh Io Iq Is Iv Jh Jr Jt Lw Ly Ma Mc Mh Mi Mk Mr Mt Nb Nc nl Nm Nn Nq Nr Nt Nu Of Oh Op Pg Qa Qb Qe Rx Wf Zw Xa) Ih(Du Eq Fc Fp Hr Ln Io jK Jn Lt Mm Mn Nd Nm Nt Nv Oy Pb Pg Qa Qc Rt Ry Sf Sj Uw Uy Uz Vc Vh Vw Wc Wd Wg Yl Zx Tm) Jg(Fr Hu Hx Ik Il Iq Is Iv Jq Lw Ly Lz Ma Mf Mg Mi Mn Mp Mt Mx My Nc Nd Nm Nr Nt Nu Nv Oi Pg Po Qe) Pe(aA Hv Hw Ii Iq Iu Jh JK Jo Jq Jt Lh Lv Lz Mg Mj Mq mS Mu Mv Mx NA Nl Om oP Pc Pg Pz Ur Uu) Is(Du Fi Fr Gd Hl Ip Jj jR Jt Lj Lt Ma Nu Oe Oz Pb Ry Rz Sf Ur Uw Uy Uz Vw Wd Yl Tm Ti) nl(Af aH aJ aP Fr Ha hB Hx Iv iZ kP Ky mF Ml mP Mr Mv Mx nR Nx Ow Pg Qm Qv To Ug Um Vt) Qe(aA Ip jK jT Lj Lw Ma Mi Nu Oz Pb Uu Uw Ux Uy Uz Vb Vc Vh Vw Wc Wd We Wg Wh Zx Tl) Jn(Du Fd Gd Gh Hl Ip Jh Jt Lt Me Mt Nd Ns Nt Nv Oy Pg Po Qa Qb Qc Rv Ry Rz Si Sj Th) Mz(cX Fr Hu Hv Hw Ik In Io Iv JT Mh Ml Mr Ms Mt Mx Nc Nf Nl Nr Oe Pg Po Qa Us) Iv(aA Fi Fr Ip Jt Lj Lp Ma Nm Oz Qa Sh Uw Ux Vz Wb We Wg Wh Yd Zw Zx Ye) Ke(aA aF Ao aW bL Bn Ch cX dK Ed Ik Jq Kg Ld Lh Lj Mp Ms Of Oy Oz Qn Wf) Ow(Fd Fi Gh Hl Ho Lp Rz Sf Si Uy Uz Vb Vh Vw Wc Wf Wg Wh Yl Zx Ye Tl Th) Qa(Bb Fr Hu Io It Ly Me Mm Mn Ms Nd Ne Ni Nj Nm Ns Nt Nu Nv Of Qc Vs) Kq(Dr Fc Gc Gh Iz Jj Jo Lt Ry Si Sj Ss Vb Vc Vo Wd Zw Zx Ye Xa Ti) Pg(aA Fr hA Hr It jO jQ jR jT Lw Me Mi Mn Mp My Nd Ns Nu Of Qc Va) Fw(Fc Fi Gh Ho Hp Lt Sf Si Sj Uz Vh Wc Wd Wg Wh Yl Zx Ye Tl Ti) aA(Bb Hr Iq Jm jT Lw Me Mp Nc Ni Nn Ns Nv Oe Og Oy Pb Pz Si Va) Fr(Aj Hu Ik Io Jt Mi Mn My Nc Nd Ng Ni Nj Nm Ns Nt Nu Of Qb) Vi(al Ao cG dA dD dJ Dr Du Hp In Ky Mj Ms Ou Qm Uo Ut Yl Tj) Mt(Fi Gh Ip It jK Lt Op Oz Sj Uw Uy Uz Vw We Yl Zx Tm Th) Xa(aF aM aW Dp Eq Ic iZ Nr Nx oE Qc Ql Rc Rj Rm Sh St Un) Va(Dk Dl Dr Ho Hu Il lZ Mr Mv Nm Ou Pi Po Qm Tn Uf Vh) Nn(Fc Fi Gh Hl Lj Lt Ru Rx Ry Si Wd We Wg Wh Yl Zx Tl) Lj(Io It Jh Jl Jq Lh Mg Nb Nq Nx Og Om Oz Pb Qb Qc) Mn(Fp jK Jq Lw Ma Mi Nm Ns Nt Nv Oy Oz Pb Qb Qc) Nu(Iq It Jj Jt Ma Nd Nv Oz Qb Qc Sh Si Wf) Ji(Aj Bb bN jK Oi qY Ru Us Uu Uv Wc Wf Wm) Ip(Io It Mi Nd Nm Nr Nv Po Qb Qc) No(Gd Hb Iz kP nW Rz Ss Ux Wm) jK(Im Jj Jq Ma Md Nb Nm Nv Qc) Fc(Ax Cs Fp It Mr Mx St Tz) Jt(Mg Mr Ng Oe Of Oy Oz Qc) Og(Iq Jk Lh Ma Mi Nm Nq Nr) Oh(Gb Ho kP Lt Op Rv Ry Yl) iZ(Ho Lp Ru Rz Uw Vc Wd Tl) Cx(kE kG mE mF mW mY nU) Nt(Eq Ik Ly Nd Oz Pb Sh) Yd(Cu Lh Pj Qy Si St Vt) Rx(Ax Fy Ha Jh Nr St Ut) Nv(Fp Ns Oe Oz Pb Qb Qc) nN(Bg cX De Jj Kl Ks Vs) Gc(Nb Oz Qv Qw St Uv) Ma(Fp Mi Mx Ns Oz Pb) Im(Db Dr Gn Hb Ou Qt) Li(Aj lX mZ qY Vo Wm) Ru(Hx Jd Jh Jl Ld Qy) Nm(It Jj Nr Of Qc) Ij(Bb bN Dr jT Ur) Wb(Ar Ml Qb Qx Rm) Wf(Jl Nr Rm Un Vt) Rt(Cp Dd Fy Hv Mx) Ut(Ch Dr Eq Uu Ux) Jj(Ii Iq Po Pz) Ld(Eq Hb Ux Zw) Aj(Ba Om Sr) Bb(Et Jo Oy) Mq(Eq Ry Wh) Mx(Gb Vw Wh) It(Io Oz Qc) St(Ux Wh Ti) Af(mU Uw) Ar(Fd Uz) Cs(Lp Uy) Po(Oz Pb) Th(Ed Vt) Nr(Sh Vz) Qb(Mm Pb) Qy(Dr Ux) Jr(iC jQ) Ur(Iq Sr) dK(oO oQ) gL(Eq Vc) BoHo CuWc FdhB FpUy FyHb GdNb MeMi HrLh ShOm QckG JlLp UskP OzPa dMIK Unconstrained panels with 2 analytes, where 1.0E-5 >= 'AUC p-value' > 1.0E-6. Contains 2,426 panels of 121,819 total panels evaluated. : Uh(aC al AO Ap aQ Ar aS aU Aw BB Bc BG bI bO bP cA cC CH cK cM cQ CV CX cY DB dE dF DG dH Di Dk DL dM dN Dp Et Ez fP Fr Fw GL Gp Hb Hc hG Hp Hu iA Ii iJ Ik Io Iz Jd Jf Jg Jk Jl Jp Ju Jv Kf Ki Kj Kl Ko kR Kx Kz Lj Lu Lv Ly Lz Ma Mb Mc Md Mf Mk Mn Ms Mv Nc Nd Ng Nh Nj Nk Nl Nn Ns Nv nY OF Oi oN Ou Ow Oy Oz Pa PF Po Pz Qb Qc Qh Qm Qn Qt Qw Qy Qz Rg Rh Rm Ss Tn To Tr Tz Ub Uf Uk Um Uo Uv Vo Xa Wm Ti) Nw(aC al aM aP aS aX bC bG bH bI bJ bM bR bU bV bW cA cB cC cF cL cO cQ cR cS Ct cW cZ dA dB dC dD dF dI dM dN Dp Du Eq Ez Fn hA Iz Jd Je JF jG jM jP Ju jV Ld lL lO nl Oa Qg Qh Ql Qm Qu Qv Qx Qy Qz Ra Rc Rf Rg Rh Ri Rj Ry Rz Si Ss St Tn Tr Tt Tv Tz Ua Ub Uc Ud Uf Uk Ul Um Un Uo Up Vp Vt Vv Vw) Ps(aD aE al aX Bb BC bI bJ bM bN bU bV bW cC cD cF cJ cM cO cP cQ cR cS Cu cZ DE Dl Dk Dl dN Dr Ef Em Et Fi Fr Fy Gb Gn Gz hC HF Ho Hp Hr Hx iA Ib Ic iH iJ iO Jd Jg Jp Kc Kf Kg Kn Ko Kr KS Ky Lu Mb Mg Na Nf Nh Ni Nj Nm oN Op Ou Oy Pa pF Pj Pk Ql Qz Rh Rm Ry Sf Si St Tj Ti) Qa(Aj Fp Gz Hq Hv Hw Hx Ii Il In Iq Is

Figure 36 Continued

Iu Jh JK Jl Jm Jo Jq Jr jT Ke kP Ld Lh Lu Lv Lw lX Lz Mb Mc Md Mf Mg Mh Mi Mj Mk Ml Mp Mq Mr Mt Mu Mv Mx My NA Nb Nc nD Nf Ng Nh Nl Nn Nq Nr Nx Oh Oi Om Pa Pc Pd Pe Pg Po Pz Qb Qe qY Ur Uu) Fr(Fp Hq Hr Hv Hw Hx Ii Il In Iq Iu Jh Jk Jl Jm Jq Jr Lh Lu Lv Lw Lx Ly Lz Ma Mb Mc Md Me Mf Mg Mh Mj Mk Ml Mm Mp Mq Mr Ms Mt Mu Mv Mx Na Nb Ne Nf Nh Nk Nl Nn Nq Nr Nv Nx Oh Oi Om Pa Pc Pd Pe Pf Po Pz Qe) Ke(AD aE aH aY Bg bW cH Cu Cv dH Dk dR Ef Eq Gl Gp Ha Hc Hq Hr Ib Ii Il Iu Iz Jh Jm Jv Kf Kn kS Ly Md Mk Ml Mw My Mz Ne Ng Nl Nn No Nv Oe Oh Pi Pk Qc Qv Qw Qy Rf Rh Ri Sr Ss Ua Uf Vp Vv Xa Wm Th) aA(Aa aW cX dK Fp Gc Hb Hq Hu Hw Hx Ii Is Iu Jj Jk Jl Jo jQ JR Lu Lv lX Ly Lz Mb Mc Md Mf Mg Mh Mi Mk Ml Mq Ms Mt Mu Mv My Na Nb Nd Ne Nf Ng Nh NK Nx Of Oh Oi Om Pa Pc Pd Pf Po rB Ru Rx Uw Ti) Pg(eD Fp Hq Hu HX iC Ik Il In Io Ip Iq Is Iv jD jG Jq Jr Jt Lh IL IN Lu Ly Lz Ma Mb Mc Md Mf Ml Mm Mq Mr Mt Mv Mx Nb Ne Ng Nh Nj Nk Nn Nr Nv Nx Oe Oh Oi Pa Pc Pd Qb Qe Ur Uu) Js(Aj Bb Du Hq Hu HV Hw Hx Ih Ii Iq Is Iu jl Jk Jl Jm Jq Jr Ld Lh Lu Lz Mb Mc Md Mf Mg Mh Mj Mk Mq Mr Mu Mv Mx Nb Ng Nk Nl Nn Nq Nr Nx Oh Pa Pc Pd Pe Qe Rv Sh Us Vc Vs Xa) Mn(Aj Hq Hr Hu Hv Hw Ik Il In Io Iq Is Iu Iv Jh Jl Jr Jt Lh Lu Lv Lz Mb Mc Md Mf Mm Mp Mq Mr Ms Mt Mx My Nb Nc Nd Ng Nh Nj Nk Nn Nq Nr Nx Oe Of Oh Oi Om Pa Pd Po Qe Va) nI(al aZ bQ bZ cH cR Cs cU dE dF dK Dp Et Hw iA Iq Jh Ji Jk kF Kj kO Ld Lh Lu Lv Lz mE MH Mj mY mZ nB nJ Nt Nv nY Oa oF On Pi Pk Po Ql Qy Rc Tv Ub Ue Un Ut Uv Vu) Qe(Aj Bb bN Du Fc Fd Fi Gh Hl Hp Hr Hu Ih Ik Il Io It Iv Jn Jq Jt Lp Lt Me Mm Mp Mt My Mz Nd Ne Nj Nk Nn Ns Nt Nv Oc Of Op Ou Oy Qc qY Rv Rz Sf Sj Vo Vz Tm) Lx(Eq Fp Ii Ik Il In Iu JK Jl Jm Jq Lh Lu Lv lX Lz Md Mf Mg Mj Ml Mm Mp Mq Ms Mt Mv Mx My Ne Nf Ng Nh Ni Nj Nk Nl Nv Nx Oi Om Pa Pd Po Pz Rv Vc Wc Yd) Jg(Hq Hr Hv Hw Ii In Io Iu Jh Jk Jl Jm Jo Jr Jt Lh Lu Lv Mb Mc Md Me Mh Mj Mk Ml Mm Mq Mr Ms Mu Mv Na Nb Ne Nf Nh Ni Nj Nk Nl Nn Nq Nx Oh Om Pa Pc Pd Pz) Ih(Fd Fi Gb Gh Gz Hp Hq Ik It Iv Jh Jt Lh Lv Lw Ly Mh Mi Mp Mr Ms Mt My Ne Nh Nk Nn Nr Ns Oe Of Om Op Pa Pd Pe Po Qb Ru Rv Rz Si Ur Tl Ti Th) Xa(aO aP aS aX bG bJ Bn Ch cQ Ct cU Cv dC Dg dR Et fP Gc gL Ha It Jh Ji Jm Jo Kd kR Kz Mh Mk Mr Nf Nt Of Oy Qb Qv Qw Ru Sj Ul Us Uv Vo Vq Wf) Mz(Bb cH De Dp Ed Fp Gp gW Hb hR Ii Iq Is Iu jD Jh jL jQ jR Ld Lh lK IN Lv Mf Mg Mj Mk Mm Mv Ng Nh Ni Nk Nt Nv Om Pc Pz Qb qY Rx Uu Va Wm) Mw(Ao Ar aZ Bc bS Co Cv dK Ii Il jK Jq Jr Ld Lh Lu Lv Mc Md Mf Mh Mj Ml Mm Mp Mq Mr Mv Mx Ne Ng Nh Ni Nj Nl Nn Nq Oh Oi Om Pd Po Th) Jn(Eq Fp Hp Hr Ik Il In Io Iq Is It Iv Jm kP Lh Lp Lu Lv Lw Ly Lz Mc Mi Ml Mp Ms My Nc Ng Nh Ni Nj Nk Nn Nr Of Oh Oi Om Pa Pd Pe Pz) Lj(Hr Hu Hv Hw Hx Ii Ik In Iq Iu Jk Jm Jo Jr Lv Ly Lz Mc Md Mf Mj Mq Mr Ms Mu Mv Mx My Nc Nd Nj Nk Nl Nr Ns Oe Oh Oy Pa Pc Pe Po Pz) Ny(Fd Fp Hv Hw Hx Ii In Io Iq Is Iu Jm Jt Lh lK IN Lu Md Mh Mj Ml Mm Mq Mu Mx Na Nc Ne Nf Ng Nh Ni Nj Nk Nl Nv Nx Oi Om Pc Po Pz Uy) Pf(Eq Gd Hv Hw Hx Ii Io Is Iu Jh Jj Jq Jt kN Lh Ly Lz Ma Md Mj Mq Ms Mt Mx nA Nc nD Nf Nh Nl Nn Nq Nr Nv Oe Op Pc Pz Qb Ux Uy Uz Vw Wd) Jp(Bb Hq Hv Hw Hx Ii Io Jh Jk Jl Jo Lh Ly Mb Mc Md Me Mf Mg Mj Mk Ml Mr Mu Mv Na Ne Nf Nh Ni Nj Nl Nr Nx Oi Pc Pd Pz Uu Va) Nv(Hq Hr Hu Ik Il Io Iv Jk Jq Jr Jt Lw Ly Lz Ma Mi Mk Mp Mr Ms Mt Mx My Nc Nd Ne Ng Nj Nk Nm Nn Nr Nt Of Om Oy Pa Pe Sh Wf) Ip(Hr Ik Il Iq Jh jK Jl Jq Jr Lh Lv Lw Ly Lz Mf Mh Mj Mm Mp Mr Ms Mv Mx Nb Nc Ni Nj Nn Nq Ns Oe Of Oh Om Oy Pa Pc Pe Pz) Ma(Aj Hu Hv Ik Il In Io Iq Jl Jq Jr Jt Lh Lv Lw Mh Mj Mp Mr Ms Mt My Nb Nc Nd Ng Ni Nj Nm Nr Nt Oe Of Om Oy Pa Pe Po) Qb(Bb Di Fp Gb Hr Ik Io It Iv Jh jK Lh Lv Lw Ly Mi Mp Mt Nd Nk Nn Nr Ns Oe Om Op Oy Po Pz Qc Ru Sh Uw We Wf Yd Ye Ti) Qd(aD aE Aj Bb bN Du Eq Fc Fd Gh Hp iB jF Ld lM Lp Lt mZ Op qT qV Rz Sj Uu Uw Uy Uz Vw Wd Wg Wh Tm Tl Wm Ti) Va(aE aG aH Al aP aX aZ Co Cp Cs Fc Fi Fy gL hB Hv Jq Ju Kf Kk Ks Mg Mi Mk Mp Mx Nh Nq Pc Pd Qh Ua Uw) Kq(Ad Bg Ch Du Ef Fd Fi Gb Gd Gn Hl Ho Hp Kj Mm Of oH Op Pb Rv Sf Ur Uv Uz Vh Vs Vz Wb We Wg Yl Tm) Is(Aj Bb bN Fd Fp Gb Gh Ho Hp Hr Ik Io It jV jY Ld lN Lp Nd Nm Nr Ns Nt Of Oy Qc Si Sj Tl Th) Iv(Du Eq Fc Gb Gh Hl Hp Io Iq It Jj Lt Me Nd Nr Pb Qc Rv Ry Rz Sf Si Vh Vw Wd Tm Tl) Ur(Bb Dd Fw Fy Gc Ho Il lm Ji Jr Jt kC Kd kK kP ml mS NB nK nL Nt nU Qc Qh Ut Vt) Aa(gW Hv Hw Ii Ik In Io Iu Lu Mc Me Mf Ml Mm Mx Na Nc Ne Ng Ni Nm Nx Oh Pa Pd) Nt(Fp Hb Io Iq It jK Jo Jq Jt Mc Mi Mp Ni Ns Oc Of Pe Po Rx Rz Uu Ux Vw Wh Th) No(aE aW bN cX dA De dK Fy Gc Ha Hc jO jQ jR Ki Ld oN Ou Ow Qt Uv Vs Vv) Nu(Fi Fp Io Lp Ly nN Nr Oe Om oO oP Pb Pe Po Ru Rv Rx Ry Uw Uz Vc Wb We) It(Fp Hr Iq Jh Lh Lv Lw Mi Mm Nb Nd Nq Nr Ns Om Pa Pb Pc Po Ru Ry Sh Wf) Jj(Dc Fb Fp Hb Il Jk Jl jT Ks Mt nC Nn Om Oz Pj Qh qY Rf St Ut Vq Vt Wm) Jt(Ct In jK Jl Jq Lh Lv Lz Mm Mp Ms Mt Mx My Na Nj Nk Nr Ns Oi Pa Pc Po) Bb(aH Ar Ax aZ bA bL bN Cs Cx dE dF Dp lm Li Lz Ml Mq Nb Og Pb Pe Uu) Oz(Fc Fi Fp Ho Jh Jl Lh Ml Mm Mp mZ Nb nC Nm NN Nr Og Om Si Vw) Im(aF aU aW Bg bJ bN bO cB cD cH Cs Ct cX dB De Di Dl fR Ld mZ Ow) Oh(Du Eq Fd Fi Hl jK Ru Rx Rz Sf Si Sj Vc Vw Wd We Wf Zx Ye Tm Tl) Mt(Du Fc Fd Hl hX Iq jQ jR Nd Nm Oe Og Pe Rv Ry Sf Si Vh Wg Tl) jK(cK Et Ii Ij Il Iq Iu Jl Li Lv Lz Mi Mp Nn Nq Nr Oi Ok Pc Pd) Fw(Du Eq Fd Gb Gd Hl Lp Op Rv Rx Ry Rz Uw Ux Uy Vb Vw We Zw) Pe(Gd Jl jT kE kG Ld lY mM mW mZ Nq Nr Po Qc Qg Ss Vo Vs Wm) Nn(Du Gd Hb Hr Ik Nd Ns Oe Of Oy Pb Pc Rt Rv Uw Vb Vh Vw) Qc(bN Di dK Fp Il Jl Ld Lh Lv Mi Mm Mp Nd Om Pa Pb Po) Sr(aE bN Ct dA Ha Hb Hc Hq Iz Jo Ld Mg Oe Qt Ss Uv Vo) Ji(aD Af aW aY bA Bn bO bP CX dL Fc jD Up Vo Th) On(Aj De Eq Fc Ho Lp Op Ru Si Uu Uy Vc Vz We Zx Ye) Fp(Du Fi Ho Io Lp Lw Mm Nd Nm Og Om Pb Rx Vc Wf) Ij(aZ Ch Ct Gc Gn Hb He Ld Ou Qt Qw Uu Vs) Ir(Aj Hp jT Lt Rz Sh Uu Vc Vw Wc Wd Wh Th) Og(Hx Ii Il Io Jh Lw Mm Mp Mr Mv Mx Nb Pa) iZ(Fc Fi Gb Ry Sf Uy Vb Vh Wb We Ye Ti) Ow(Em fR Gc Lt Rt Ru Uw Wd We Tm Ti) nN(As Bo Ct hB mZ Nh Oy Ph Tv Uu Vv) Cx(Fd Gb Ho kF kO mM nB nF nJ nR) Et(Bg bN Ch cV Dg jO Kl Uv Vo Wm) Ut(Gd Hb Lp Uv Uz Vc Vs Wb Wh Ye) Dr(dR hB Li Nb oE Ru Si St Vq) Ld(Ed Gc Gp Hp Jr Uz Wf Wh Yl) Pb(Jr Lh Mm Mr Nb Nm Nr Om Pa) Jl(Fc Gh Rt Uy Vc Wb Zw Ye) Ru(aZ Dk Gc Hb Mq Po Rh St) Aj(Ad Ap Dc Ok Tn Tr Uc) Li(bO Fy kN mW nA nD Vs) Mq(Gb mZ Si Uz Wf Zw) Mr(Fi Gh Rt Ry Sf Si) Jr(hR jE jG jR jV lN) Gc(hB Sh Ub Us Vt) Nr(kP Mi Mm Oe Oy) Jh(Gd Iq Nd Oy Uy) St(Ho Rz Sh Sj Uz) Wf(Cs Cu Hx Mx Tn) Un(bN Rx Uu Yd Th) Rt(Hw Na Pi Tn) Cu(Rx Vb Th) Po(Hr Io Oe) Fi(Ar Cs Ql) Nm(Iq Oy Pa) Mx(Hp Rv Vz) Ho(aZ Kj Ql) Wb(aP oE Vt) Uy(Ar Jy Qy) Bo(mU mZ) Ed(Hb lX) Gd(Cw Om) Ml(jT jV) Hr(Iq Pa) Yd(Ou Uw) Sh(Ju Vq) Rx(Hx Na) Lp(Jy Kd) Vt(Lt Ti) cX(oQ Uw) dM(jQ jR) mS(oE Us) jl(bN rB) qY(Jq Lz) CsVb EqPd GbhB GnNb LvjT Milo HpaW llVz SioE WdaZ KoUu LhOf RfgW UxVq aNnK Unconstrained panels with 2 analytes, where 1.0E-4 >= 'AUC p-value' > 1.0E-5. Contains 3,733 panels of 121,819 total panels evaluated. :
Ke(aC aK AL AN aO aQ aS Aw AX aZ BB BC bF bG bH bJ bM bO bP bR bS bU cA cD cE cF cG cK cM cN Co Cp CQ cR cS CT cV cY DC Dd DG Di dJ DL dN Du Et Ez Fn Fp Fr Fw gL gP Hb hC Hf Hp Hu Hv Hw Hx Ic Id Ih IJ IO IP Iq Ir Is It Iv Jd Je Jf Ji Jk Jl Jn Jp Jr Js Jt Ju Jy Kc Kd Kk Kl Ko Kp Kq Kr Ks Ky Kz Li Lu Lv Lw Lz Ma Mb Mc Mf Mg Mj Mn Mq Mr Mt Mv Mx Na Nb Nc Nd Nf Nh Ni Nj Nm Nq Nr Ns Nt Nu Oa Og oH Oi Ok Om oN Or Ou Pa Pd Pg Ph Pj Po Pz Qb Qd Qe Qg Qh Ql Qm Qu Qz Ra Rb Rc Rg Rj Rm Sh Si Tn To Tv Tz Ub Uc Ud Ue Ug Uk Ul Um Un Uo Ut Ux Vb Vt We Zx Ye Ti) No(aC AD AF aG aH aJ aK Al AN AO AP aQ AR As aU aV Aw Ax aY Ba bB Bc bE bF BG bI bL bM Bn BO bP bQ bS bZ cA cB cC cD cE cG CH cJ cK cL cM cN CO CP CQ cR Cs Ct Cu CV Cw Cx cY DB DC DD dF dG dH Dl dJ Dk DL dN Dp Ed Ez Fb Fn fR hG Ib iH iP jD Jf jG jM Ju Jv Kc Kf Kj Kk Kl kN Ko Kq KS Kx lK IN lX oE pF Ph Pj Pk Qn Qv Qw QY Rc Rg Rh Ri Rm Sr Tv Uc Ue Uf Uo Us Ut Vt) lm(aC AD aE Af aG aH aI aJ aK AL aM AN AO AP aQ AR AS aV Aw aX aY aZ BA bB BC bE bF bG bH bI bL bM Bn Bo bP bQ bR bS bU bV bW bX bZ cA cC cE cF cG Ch cJ cK cL cM cN CO CP CQ cR cS cT CU CV CW Cx cY cZ dA DC DD dE dF DG dH dI dJ DK dL dM dN Ex Fb Gz Iz kC Ki Kk kN Ko KP mF ml nD Qw Rf Uu Vo Vs Wm) Et(aC aD AF aG aI aK Al aM aN AO Ap AR As aU AW Ax aZ BA Bc bF bG bL bM BO bP bQ bS bU bZ cB cD cE cH cI cJ cK cM cN Co CP Cq cR CS cT CU Cv CW

Oh(Gd Gh Gz Lp Og Pb Rt Uw Ux Uy Uz Vb Vh Wc Wg Wh Ti) hB(bN Fc Hp kP lX mE ml nK nU Rv Ry Si Sj Vc Wf Yd Yl) Aj(Bc Co Cu Cw Dd Fy Jk Jp kG Ko Nq nU Rf Uf Un) Mm(Hr Il Io Iq Jq Lh Mi Mj Mx Nb Ng Ns Oe Oy Pa) Lp(aM aP Bo bZ cO gL Ha Hx Jd Jh Kx Mx Qy Rt Un) Ar(aE Cu Dc dK Gb Hp Ru Sh Wc We Yd Yl Ti Th) Gc(dR Fc Fw gL Ha Nc Ni OE Ri Ry Ux Vo Vq) Mq(Fc Gh Hp kE kN kP Og qY Sf Ux Vb Wc Yl Ye) Io(Iq Jq Lw Mh Mp Mx Nb Nd Ns Of Pb Ps) Jp(aW BG bN bO Cs Cx Hb mZ Ou Wm Ti) Ru(aP Bo Cu gL Ha Hq Id Mp Nh Ou Tz Vq) Og(Hw Iu Jm Jq Lv Lz Mj Mu Nc Nx Pb Pz) Sh(Cu Dk Ef Hw Hx Iz Jg Jk Mv Sf Uf) Jh(Eq Nb Ns Of Pa Pb Ux Vb Wd Wh Ye) Wf(aM aP Ax gL Ha Hw Kd Ok Pi Qy Uw) Dr(Fc Fi Fw Ic Kk oF Pj Qw Rt Uy) Lh(Ik Iq Jo Mi Nd Ns Oe Oy qY Wb) Uu(Aa Dc Fr Gb ml Ok Si Tn Uc Uw) aP(Fc Gd Hp Rx Ry Sf Si Vc Yd Ye) Cx(Aa kl lY mH mP nA nM Uz Wc) Ml(Fd Gb Hp iB jH kG lM nU qY) oE(Hb Ho kP Rf Sj Un Uw Uy Vq) Bo(Fd kG kP mF ml nD nK Uw) Cs(Gb Ho Rt Ry Wb We Ti Th) Hx(Fc Fi Rt Ry Uy Vh Ti Th) gL(Fd Fi Gd Hp Ry Si Uy Wg) Ed(eM Ex ml mS nA nL Rf) Eq(aW Ba Hu Jk Mg Nq Vq) Hb(bA dK Fw Il Jv Oa Qv) Wb(aJ Kk Kx Mf Mk oF Ql) Jq(Hr jG jP jQ jR lN Me) Pb(Ho Iq Mi Mp Nq nU Wd) dM(hA iB jE jl jP jU lM) Lz(Fd Gb Hp kN kP lX) Mx(Ho Me Rz Uw Ux Uy) Rt(Ax bA Fd Ha In Kn) Fc(aZ Cu Ex Mj Qx) Hp(cU Mh Qx Tz Vq) Iq(Lv Nj Ns Oe Oy) Yd(Co cU Mv Ql Tn) Qy(Du Rv Rz Uz Ye) Ps(cI fR Jy Kz Mv) Un(Gp Uv Uy Wc Ti) Gb(Mh Ql Qx Rx) Nb(fR Hr kP Me) Nd(bQ Lv Mi Nq) mZ(Cv kG Lu Us) Af(kG ml nU) Fr(bO De Jo) Kd(bN Uy Wc) Rx(Dk Il Kn) aZ(bQ Ry Ti) dR(Ex fR mF) qY(jl Mj Nf) Aa(Fy Vo) Cv(mU nU) Th(Fa Fw) Fd(Ql Qx) Gd(aM Vq) Mi(Hr Jm) Kj(kG nU) Us(Ho kN) Uy(Jd Mv) bQ(dH oN) ml(Jo Nx) rB(jD jT) oQ(cF cN) AxZw BnmU DcbN FiQx FyVs HaZx NqYe LwhX MeMj MpOe HvWc HwVb RyQl RfVo OweM UfUx aHnK hWjT

Constrained panels with 3 analytes, where 4.9E-15 >= 'AUC p-value' > 0. Contains 50,000 panels of 17,842,327 total panels evaluated. :
Vi{Af(aA aJ aM Ao AP aR AS aU aW aX aY bF BG bJ bP bW bZ cC cE cH Co Cp Cq Cs Cu Cw Dc De dJ dL Dr Ed Eq Et Ez Fn Fp Fw Gp Hc Ho Hq Hw Ic Id Ih Im In Ir Is Iv Iz Ji Jp Jq Jr Js Jt Kc Kd Ke Kg Kn Kr Kz Ld Lj Lu Lw Lx Lz Mf Mg Mh Mk Ml Mm Mq Mr Mt Mu Mx My Na Nf Nm Nn Nq Nv Nw NY Oa OH Om On Pb Pd Pf Pi Pj Pk Ps Qa Qb Qc Qe Ql Qw Qx Qy Ra Rc Rj Rz Sh Tv Uc Ud Uf Uh Un Up Ut Uz Vp Vq Vt Wd Wf Wg Yd Zx) Nx(aF aK aM AO aQ As aU aW Bn Bo bW cC cJ CO CP Cq Cs Cu Cw cX dA Dc De Dr Ed Em Eq Et Ez Fp Gp hB Hc Hl Ho Hv Ib Id Ij Il Im Is Iv Jh Ji Jq Jr Jt Kc Kd Kg Ki Kl Kn Kq Kr Kz Lh Lt Lw Lx Mf Mg Mi Mk Ml Mm Mp Mq Mt Mu Mv Mw Mx Nb Nf Nn Nw oE Oh Om Ou Oz Pc Pd Pe Pf Pi Pk Qa Qb Qc Qd Qx Qy Ra Rb Rc Sh Si Sr Tv Ue Uf Uh Ul Up Ur Uu Uv Uz Va Vq Vt Wd Wg Yl Ti) Of(aF Ao As aU aW aX bC bJ bW bZ cC cE CO CQ CS CU Cw Cx De dK Dr Ed Ef Em Eq Ez Fi Fw Gc Gp Hl Hu Hv Ic Id Ij Im In Iv Jh Ji Jr Js Kd Ke Kg Kj Kq Kr Ld Lw Ma Mf Mg Mi Mk Ml Mm Mp Mq Mr Mt Mu Mv Mw Mx Nf Nq nW oH Ow Oz Pc Pd Pf Pi Pj Pk Qa Qc Qd Qe Qx Qy Qz Ra Rj Rx Rz Sh Si Sr Uf Up Ut Uz Vq Vt Wd Wg Tl) Kd(Ad aL aO Ar aS aY bF BG bJ Bo bZ cE CH cO Cs CV Dg Dk Dp Ed Eq Fp Gc Gl Hb Hc Hq Hx iA Id Ih Iu Iv Iz Ji Jj Jk Jl Jo Jp Ke Kg Kj Kl Kp Ks Kx Kz Lu Lz Mh Mk Ml Mt Mx My Nf Nn Nu Nv Oa oE Oh Ok Oy Oz Pa Ph Pj Qb Qd Qg Ql Qu Qw Qx Qy Rb Rt Rz Sh Sr Ss Tn Tz Ur Us Uu Ux Vo Vp Vs Vt Wc We Wf Yd Tl) aY(aM aP Ar aS aW Ax bF bJ Bo cC cO cQ Cs cU CX cZ dL Dp Du Ed Eq Et Fn Fp Gc Hb Hv iA Ic Id Ih Ir Is Iu Iv Je Ji Jj Jn Ke Ki Kz Lj Lu Lx Lz Mb Mf Mh Mi Ml Mp Mq Mr Mt Mx Nc Nf Nk Nn Nq Nu Oa Oe oF Oh Oi Oz Pb Pe Pj Po Qa Qb Qc Qd Qe Qg Ql Qn Qx Rc Rg Rj Rt Rx Sh Sj Sr Tz Un Ur Uu Va Vq Vt Wf Wh Tl) We(Ad aM As aU aW bW cE CO Cp Cq Cu Cw Cx Dc Dd De Dr Em Ez Fw Gc gL Hl Ho Hu Hv Hw Id Ij In Is Iv Jh Ji Jl Jn Jq Jr Js Jt Kc Ke Kg Kn Kq Kr Ld Li Lw Mg Mi Ml Mm Mp Mq Mr Mt Mu Mv Mw Mx Nb Nf Nm Nn Ny Og Om Ow Pb Pd Pi Pj Pk Qa Qd Qe Qx Qy Ra Rj Tv Ua Uf Ul Up Ut Uz Vh Vp Vt Wd Wg Tl Xa) aF(Ad aH Aj aM Ar aW aX Bg Bn Bo Ch Ct cU cV Cx De Dg Di Ed EF Fn Fr Gc Gd Gp HB Hc Hf Hu In iO Ir Is Iz Ji Jj Jo Ke Kg Kj Kl kR kS Ld Li Lp Lz Mf Mh Ml Mp Mv Mx My Ng Nw Oa Oe Oh Oi Oz Pb Pe Ph Pj Qa Qb Qg Qu Qw Qx Rg Rj Rt Rx Sh Tv Tz Ua Uh Ur Us Uv Ux Va Vo Vs Vw Wd Wf Yd Yl Ye Th) aW(aA Ad Ar Ax aZ bF BG bQ bZ cE cH cV dF Dg Dk Dp Dr Ed EF Fr Gc Gd Gl HB Hq Hx Id iJ Iv Iz Jg Ji Jj Jo Jp Js Kl Kp kR Ld Lu Lz Me Mh Ml Mq Mx My Nd Nf Nv Nw Oa Og Oz Pa Pb Pc Ph Qb Qd Qg Ql Qu Qw Qx Rh Rt Sr Ss Tn Tz Ur Uv Va Vb Vs Vt Wf Yd) Uv(AP Ar aU aX bF bG bJ bW cC cH CO Cw Cx Dp dR Du Ef Et Ez Fp hB Hv Ic Ih Ij Ir Is Iu Iv Jd Jh Ji Jn Js Kc Ke Kz Li Lu Lx Lz Mg Mk Ml Mm Mp Mt Mu Mv Mw Nf Nm Nn No Nq Oh Om Ow Pa Pd Pe Pj Po Qd Qe Qg Ql Qx Qy Rc Rx Si Sr Uf Uh Ur Vp Vq Tl) Gc(aA Ad Aj aN aO Ar Ax bF bG bN Bo bZ cE cH cV De Dk Dr Ed Ef Eq Fp Fr Gl Hc Hq Ih Im Iv IZ Jl Jo Jp Jq Jy Kj Kl Kr Ld Lj Lu Lv Mh My No Nu Nv Oa Og Ok On Op Ou Oy Oz Pe Qn Qw Rb Rt Ru Sh Sr Ss Tn Up Us Ut Uu Ux Va Vo Vp Vs Wf Yd Zx) Uu(aC aL aN Ap aS Bb bC bE bG bJ Bn bW cE cH Co cP cV Cx cZ dF Dk Dl Ed Fc Fi Fw Gh Gp hC Ho Hu Hv Hw Ic Ih Im Iu Iv Jg Jh Ji Jl Jt Kc Ke Ld Mg Mi Mm Mq Mt Mu Na Nm Om Ow Pd Pj Pz Qa Qc Qd Qe Ql Qz Si Sr Tn Ue Uf Uk Vp Vq Vt Wd Yd Ye) Nn(Ad Aj AO bF bG bQ bZ cE cG cH Co CS Ct cV De dF Di Dk EF Eq Ez Fr Gl Hb Hq Hu iO Jj Jo Jy Kg Kj kR Lz Ma Mg Mh Ml Mv Mx My Mz Nv Oa Og On Oy Pb Pc Ph Qb Qg Qt Qw Qx Qz Rt Sh Tn Tz Ua Us Ux Vb Vo Vs Vt Vw Wd Wh Yd Zw) Bn(aK aQ As aU aZ Bg bP cC cE Cq Cs Cw Dg dJ Dp Dr Ed Eq Fn Fp Hc Hv Hw Id Im Is Iz Ji Jq Jr Js Kz Ld Li Lj Lw Lz Mi Mk Ml Mp Mq Mx My Nw Ny Oa Oh Oi Or Ow Oz Pc Pe Ph Pi Qb Qd Qe Qg Ql Qx Ra Rc Rh Tn Tz Ur Uz Va Vp Vt Wg Yd) Mi(Ad Aj aN Ao Ar aX bF bL cE cG CH Co Cp Ct De Dg Dk Dp Eq Fr Gl Hq Hu Iz Jh Jj Jl Jo Kf Kg Kj Kl Ko Kq Kr Lz Mh Ml Mu Mv Mx My Mz Ng Nv Oa Ok Om Oy Pb Pg Qb Qn Qu Qw Qx Qz Rt Ru Rz Ss Tn Ua Uc Ut Ux Vb Vo Vp Wc Yd) Pj(aA Ad Aj AO aZ Bg bZ cE cG CH Co De dF Dg Dk Dp Ed Ef Eq Fr Gl Hc Hq Im IZ Jd Jm Jn Jo Jp Kg Kj Kl kQ Lp Mx My Mz Ng Nv Oa Ok On Op Ou Oy Pb Qb Qn Qz Ru Rz Sh Ss Tn Up Us Ux Uy Va Vb Vo Vs Vw Wd Wf Wh Zw Th) Qy(Ad Aj Ao Ar AX aZ bF Bg bL bZ cE cG cH Co Ct De Dg Dp Fr Gl hB Hq Hu Ib Ir Iz Jj Jo Kg Kj Kl kR Lu Lz Mh Ml Mu Mv Mx My Ng Nv oE oF Oi Pb Ph Qb Qu Qw Qx Qz Rt Ru Rz Sh Ss Tn Ua Us Ux Va Vb Vo Vs Wd Wf Yd Tl) Dk(AJ aM aP aS bP cQ Cs Ct cX dF Dp Eq Fn Fp Hb Hv Ih Ij Ir Is Iu iZ Je Js Kl Kz Ld Lz Mf Mh Mj Mk Ml Mp Mq Mt Mw Mx Nb Nf Nq Nw Oa Oe Oi Ou Ow Oz Pa Pc Pe Pf Ph Qb Qc Qg Ql Qx Rc Rh Rt Rx Ss Uh Ur Va Wh) Vp(Aj Ax aZ Bg cE cQ Cs Cu dF Dp Eq Fn Fp Hv Hx Ij Im Ir Is Iz Ji Jn Jq Jr Js Ke Kl Kz Lj Lp Mp Mr Mx Nb Nj Nw NY Oa Oh Oi Op Ow Oy Oz Pi Ps Qa Qb Qc Qd Qe Qw Rc Rh Sh Ss Tz Uh Ux Va Vb Vo Vt Wf Wh Yd Tl) Vs(Ap aU aX bC bE bF bG bJ bW cC cH CO cV Cw cZ Dl Ez gL Ho Hv Hw Ic IH Ij Im iO Is It Iu Iv Jh Ji Jn Js Jt Kc Ke Kg Kz Ld Mg Mk Mp Mq Mt Mu Mw Na Nm Og Oh Ow Pd Pe Ps Qa Qd Qe Ql Qw Sh Sr Uf Vq Vt Xa) Bg(aN Ao Ap aU aX bE cO cQ cS cV CX cZ Ef Ez gL Gp Ho Ib Ic Ih Ij Il Im Iu Iv Jd Jh Ji Jo Jt Ke Ki Mf Mk Ml Mm Mp Mq Mw nW Oe Oi Ow Oz Pb Pd Pe Pf Pk Qa Qn Qw Rc Rt Rz Si Sr Uf Uh Ur Us Va Vq Wc) Ld(Aj AN aX Bb bF bZ cE cG CH Cx cY De dF Dg Ef Eq Ex Ez Fr Gh Gl Hc Hq Ic Im Iz Jd Jl Jm Kj Kl kQ kR Lp Lv Ma Mw Mx My Nv Oa On Ou Pb Pc Po Ql Qt Ru Sr Ss Tn Ua Uk Ul Us Uy Va Vo Wd Wf Zw Th) Mq(Ad Aj aN aX bF bG bL bZ cH Cx De Di Ef Eq Ex Ez fP Fr Fw Gl Hc Hu Ic Iz Jd Jl Jm Jy Kl kR Mh Ml Mx My Mz Nv Og Oi On Oy Oz Pb Qn Qt Qw Qz Ru Sh Ss Tn Ua Ul Us Ut Uw Ux Uy Vo Vt Wd Wf Wh Yd Th) Gl(aP Ar aS aU aX bC bG bJ bW cC cH CO cZ dL Du Ez Fw gL Ho Hv Ic iH iO Iu Iv Jh Ji Jn Js Kc Ke Kg Lu Mg Mk Mm Mp Mt Mu Na Nf Nw Og OH Ow Pd Pe Qd Qe Ql Qw Sh Sr Uf Uh Un Ur Vq Vt Tl) Yd(aG aQ aU bW cB cC cJ Co cP cQ CX dA dM Gp Hb Hc Hv Ij Is Iu Kc Kg Ki Kq Kz Lu Lz Mf Mg Mk Ml Mm Mp Mt Mu Nq OE Oh Oi Om Pa Pe Pf Qa Qd Rc Rj Rt Rx Sh Si Sr Uf Uh Un Ur Va Vq Vt Ti) Aj(Ap aS aU aX bC bE bG bW cC CO cS Cw Cx De dK Ez Fi Fw gL Ho Hu Hv Hw Ic IH Im Iu Iv Jh Jl Jt Ke Kg Kj Kq Mg Mm Mt Mu Mv Mw Nm Nq Nu oH Om Ow Pd Pe Qd Ql Qz Rx Rz Sr Ue Uf Vq Wd) Kl(AP aU aX bC bE bG bJ bW CO cS Cx cZ Dg dK Dl Ez gL Gp Ho Hv Ic Ih IJ iO Iu Iv Jh Ji Jn Js Jt Kc Ke Kg Kq Kz Li Mg Mm Mp Mt

Lu(aM An bP Cs Dp Fp Qg) Mh(aU dK Hf Kz Mp Op Rv) Hq(aU cS cU Kq Mp Mv Mw) Wc(dR hG iH Jn Jr Js Si) Rz(Ap aX bC bE Ez iH Kg) Ux(Ap aX bE Ez Iu Kg Mm) kQ(aM Cs Et Fp Kz Nd Po) Jd(Ar Fp Iu Kz Nf Ql) Vb(bE Hw iH Iu Jt Nm) bN(Hb Nw Ph Qg Qx Tz) Mw(oF Oy Ua Wd Zx) Jj(dK Iu Lp Uk Ul) Kf(Cw Hw Jt Nm Om) Pg(Ij Jn Js Mr Tz) aM(Jp Jy Og On Zx) aS(Ax Cs Js Oh Ul) dR(aQ Cp Fc Ir Nr) An(Hx Js Kz Nf) Fr(aU cS Ez Kq) Gp(bQ Jp Mn Nf) Lv(Fn Is Lx Oh) Qe(Cv Jp On Rb) Kg(aU bC Mm Wd) Oa(cN Cv dM Iu) Oy(Ih Mp Si Ue) aX(cS Ng Ua Wd) bE(aZ eF Oh Vw) dK(Dp Hb Ph Qg) Ap(eF iJ iO) Ar(Jk Ul Vc) Nl(Gh hG Si) It(Ib Rj Ye) Zx(In Qg Qx) aP(dG gP iP) dl(Ih Ir Qg) Ao(Kq Mm) Dp(Jy Og) No(Ii nY) Mp(cG Ou) Ij(Kp Uw) Sj(Nd pF) Qa(On Uw) Qc(iA Rb) Qx(Dd Op) Jq(Is Nw) Rj(Lp Og) Ul(Kz Tl) aA(Je Si) bC(Ng Wd) bP(gP iP) bZ(cU Kq) cT(oF pF) CqhG CscP CvIr EzbQ FdJs MriP TzRg IbXa TvJn IhKp IliA RvOh NwOu NynY OncU VwiH aUcY bAoF cRfP} Va{Uh(aA Ad aE aM As Ax BA bU cH Cp Cq Cs Ct Cu Cw dA Dc Dd Dl Dr Ef Em Ex Fc Fd Fw Gb Ha hB hC Ho Hp Hu Hv Hw Hx Ib Id Ih In iO Iq Ir It Iu Iv IZ Jd Je Jh Jk Jn Jo Js Jt Kd Kq Ld Lh Lp Lw Mb Mi Ml Mq Mr Mw Mx Mz Nb Nf Nh Ni Nm Nn No Nr Nt Nu Nv Ny Oa Of Oh Om On Pa Pb Pd Ph Pi Pk Po Qa Qc Qd Qe Ql Qm Qx Qy Ra Rj Rm Ru St Tv Tz Uc Ud Ug Ul Um Uo Up Ur Ut Uz Vb Vh Vp Vs Vt Vw Wb Wd We Wg Yl Xa) Ld(aE aF Ao Ax aY aZ BA bM bR bX cH cQ cT Cu Cv Dd Dr Ed Fd Fi Fy Gb Gc Gp Ha Hb Ho Hp Hq Hu Hv Hw Hx Ii Il In Io Ip Iq Is It Iu Iv Iz Ji Jk Jl Jn Jp Jq Jr Js Jt Ke Ki Kn Ko Kq kR Ks Li Lx Mg Mi Mj Mr Mt Mw Mx Na Nh Nj Nm No Nr Nt Nu Nv Nw Ny Oa Of Og Oh Ok Om On Ow Oz Pa Pc Pf Pg Ph Pi Pk Ps Pz Qa Qb Qc Qd Qe Qh Qu Qy Rm Rt Ru Si Sr Tv Tz Uc Uf Up Ut Uy Vp Vq Vs Vt Wb Wc Xa Tj) Ed(aM Ao aW Ax bA BC bJ bQ cI CS CT Cw Dc dK Dr EF Et Fy Gc gL Hb Hf Ho Ih iJ Il iO Ir Is It Iu Iv Iz Jg Jh Jn Jp Js Jt Kd Ke Kg Kj Kk Kn Ko Kq Kx Lh Lx Lz Ma Mf Mh Mi Mk Ml Mp Mt Mw Nd Nf Nj Nr Nt Oa oE OF Oh Oi Om On Pf Po Ps Pz Ql Qt Qv Qy Ra Rf Rh Rm Rz Si Ss St Tn Uc Uf Un Ut Ux Vb Vh Vt Vw Wd Wh Zw Xa Wm Tj Ti) Cx(Ax BA Cp Cq cT Cu Cw Dc Dd Dk Dr Em Et Fd Fp Fw Fy Gb Gc Ha Hb Ho Hp Ii Ij In Iq Ir Is It Iu Iv Jg Jh Ji Jl Jn Jp Jq Jr Js Jt Kn Ko Kq Li Lp Lx Mi Mj Mr Mv Mw Mx Mz Na Nb Nh Nr Nt Nv Nw Ny Ok Om Pd Pe Pg Ph Pi Pk Po Qd Qe Qy Sr Tv Tz Uc Un Up Ut Uw Uz Vp Vq Vs Vt Wc Tj) Qm(aE Al Ax BA Bb Cp Cq CT Cu Dc Dd Fd Fi Fy Gb Ha Hb Ho Hv Hx Ic Ii Il In Iq Ir Is Iu Iv Iz Jg Jh Ji Jk Jl Jm Jq Jr Js Jt Ke Kn Lj Lp Lx Mi Mr Mt Mx Mz Na Nb Nm Nn Nr Nt Nv Nw Oa oF Og Oh Om Ow Oz Pa Pd Pf Pg Ph Pi Qb Qc Qh Si Sr Tn Tv Tz Uc Ut Uy Vp Vq Vs Vt Wb Xa) Qy(aE Af aG aH Aj Ar AX aZ bA bM bS CH cR cT Dc DR Fw Gc gP Hb Hu Hx Ii iP Ir Is It Iu Iv Ji Jj Jm Jq Js Kd Ke Ki Kl Lx Mh Mi Ml Mp Mr Mt Mx Na Ng No Nr Nu Nw Ny oE oF oH Oi Ow Oy Oz Pc Pk Po Qb Qe Qn Qt Qu Qv Qw Qx Rf Sh Si Ss St Tz Ua Un Uu Vq Wf Yd Ye Xa Tj) Vt(aD aE AF aN aV Ax aY BA bE bJ BN Bo cT cV Dd dL Dp Dr Ef Fw gL Gp hB Hp Hu Hw Hx Ic Ih Il Im It Iu Iv Jf Jg Jh Jn Js Jt Ju Kq Ks Lx Lz Mq Mt Mv Mw Na Nb No Nr Nu Ny Oh On Pd Pe Pf Pi Qa Qc Ql Qw Ra Rc Rf Rg Rm Ru Si St Tz Ub Us Ut Uy Vb Vq Xa Wm) Hb(aE aW BA bJ bL CT Cu Dr Fc Fi Fw Fy gL Ha hB Ho Hp Hu Hv Hw Hx Im Ir Iu Iv iZ Jd Jg Jh Jk Jm Jr Jt Lj Lp Mf Mi Mq Mr Mt Mv Mw Na Nd Ni Nn Nr Nt Nu Nv Oa Og Oh Om Pa Pd Pf Pi Ps Qa Qb Qc Qe Qg Ql Qw Ra Rg Rm Ru St Tz Ug Ut Wd Yd) Vq(Af Aj aK Ar aV aY aZ bJ bL bO cN Cs cV cW cX cY dD dH Dp Dr Eq Fp Fw hB Hp Hw Hx Ic Ih Im Io Ip It Iv Jh Jn Js Ju Lj Lx Lz Ml Mq Ms Mt Mv Mw Mx Nb Nd No Nr Nt Nu Oa Oh Oz Pk Qb Qd Qe Ql Qw Rf Rm Sf Si Sr St Tz Ub Uo Ut) aN(aA Ax Cp Cq Cs Cu Cw Dd Fd Fp Fy Gb Ha Ho Hr Hv Hx Ii In Ir Is Iu Iv iZ Jh Jl Jn Jq Jr Jt Kd Kq Lh Li Lx Mi Mj Mq Mr Mt Mv Mw Mx Mz Nb Nh No Nt Nv Ny Oa Om On Ow Pe Pi Pk Po Ps Qa Qb Qd Qe Si Tv Uc Ut Vp Vs Xa) aY(Ad aP bB Cu Cw Dc Dk Dr Ef Et Fw Fy Gc hB Hw Ii Ij Ir Is It Iu Iz Ji Jl Jn Jr Js Jt Ke Kf Ko Kq Kx Lh Lx Mq Mt Mv Mx Nh Nn Nr Nu Nv Oh Ok Om On Ou Ow Pd Pe Pf Pg Ph Pi Po Qd Qe Ql Rm Tn Uc Uf Ut Uw Vh Xa) St(aC aF aG aK Ap aQ aU aW Ba bC bG bJ bM Bo bW cC cL CO Cw dK dR Ez Fc Fi Gc Ho Hv Ic iH iJ iO Iu Iv Ji Kc Kd Ke Kg kR Kz Li Mg Mi Mm Mp Mq Mt Mu Na Nn Nt nW Oe Om Ow Pd Pj Rz Si Sr Uf Un Ur Wd Wf) Nu(aE aG aX bG cH Cu Cw Dc Dr Et Gc Ho Hq Hv Hw Hx Ic Ij Il Is It Iu Iv Jh Ji Jm Jq Js Ke Ki Kq Lu Lx Mg Mi Mp Mv Mw Na Nw Ny Oa Of Oh Oi Om On Ow Oz Pb Pc Pz Qb Qc Qd Qe Qh Qx Si Tz Ut Vh We) aZ(Ar Ba bU Cu Cw Dc Dl Fc Fw Ha Ho Hv Hw Hx Ic IJ Im iO Ir It Iv Iz Jh Js Jt Kq Li Mf Mi Mq Mv Mw Na Ni Nm Nn Nr Nt Nv Nw Oa Om On Ow Pd Pe Pf Pi Qa Qb Qc Qd Qe Ql Rm Ue Uf Ut Uw Vw Wd Xa) Qb(aC aE aG Ao Ap aW Ba Bb bJ bM bO Cu Cw Dd Dl Dr Et Fc Fi Gb Gc gL Ho Hu Ic iO It Iu Jg Jh Jt Kc Ko Kq Mg Mi Mk Mp Mq Mt Mu Mv Na Ni Nt Om Pd Pf Pi Pj Ql Rg Ri Si Ub Uf Ur Vb Vw Wd Xa) Bo(Ax bA Cp Cq cT Cu Dc Dd Dr Fd Fw Fy Gb Ha Ho Hv Hx Ih Ii In Is It Iv Jl Jn Jq Jr Js Jt Kd Kn Kq Lp Mi Mj Mr Mw Mx Mz Na Nr Nw Ny Oa Ok Om On Ow Pa Pe Pi Po Qa Qd Qe Sr Tv Uc Vs Xa) No(aC AF aG aK aU Ba bC bG bJ Bn bW cE cN CO cP cQ cV Cw dJ Fc Gc gP Hc Ho iH iP Iu Ji Kc Kd Ke Kg Kq Li Mf Mg Mi Mm Mp Mt Mu Na Nn Nq NW nY Oi Ow Oz Pc Pd Qn Si Uf Un Wf) bJ(aA Ax bA Cs cT Cu Cw Dc Dd Dk Dr Et Fw Gc Ho Hv Hx Ii In Iq Ir Is It Ji Jl Jn Jp Jq Jr Js Jt Kd Ke Kn Ko Lj Lp Lx Mi Mj Mr Mt Mx Nh Nr Nw Ny Oh Po Qc Sr Tv Vp Vs Xa) Ql(aD aE Af Al AX bA Bb bM Bn Ch CQ cT Cu Dc Dd Fd Fi fP Fw Fy Ho Hv Ic Il In Iq Iv Jm Jr Jt Ki Kn Lp Lu Mi Mr Mx Na Nb Nr Oh Oi Oz Pa Pc Pg Pi Qh Si Tz Up Vs) Jh(aE Af aG aH Aj aM Ar AX Bg bM CH Dd De Di Dr Eq Fc fP Fw Gc Ha Hc Ic Ii Ir Iu Iv Iz Jm Kd Lx Lz Mh Ml Mx Oa oE Oh Ow Oz Pc Pj Qc Qe Qw Sh Uu Uv Wf Yd Xa) Ny(AF Ap Ar aW bC Bn bS cO dR Fc Fi Gc Gp Ho Hw Ib Ic iH iJ iP Iu Iv Ji Kc Li Lu Lx Lz Mf Mg Mi Mk Ml Mp Mq Mt Na Nn Nt oE Oh Ow Oz Pd Pj Qv Qw Rj Si Uf Ur Wf) Dr(aF Ao Ap Bb cQ Dc Fw Gc Gh Gp Hu Hv Ic Ih Il Im Iq Ir Is Iu Jg Ji Jm Jn Js Ke Kq Lh Lu Lx Mf Mn Mp Mw Nd Nr Oh Om Ow Pa Pz Qc Qd Qe Qg Rm Ru Si Tz Uc Ut) Oz(aP Ar Ba Cu Dd Ef Fi Fp Gb gL Ha hB Hc Hp Hu Hw Hx Ic Ih Ii Ij Ik Ir It Iu Iv IZ Jg Jk Jn Jr Js Nr Nt Nv oF Om Pd Pe Pi Ps Pz Qd Rm Si Sr Tn Tz Ua Ut) Af(aA Cw Dd Dk Et Fw Gb Gc Ha Hw Ih Ii Ir Is It Iu Jg Ji Jn Jq Js Jt Ke Kf Ko Lh Mr Mw Nh Nm Nn Nr Nv Nw Ok On Ow Pf Pz Qc Qd Qe Rm Si Sr Tz Uc Ut Uw Xa) bM(Co Cw Et Gc Hw Ic Ih Ii Im Ir Is Iu Ji Jn Js Jt Ke Kq Kx Lj Lx Mf Mk Mq Mt Mw Nn Nr Nw Oa Oh Om On Ow Pd Pf Po Ps Pz Qc Qd Qe Rm Si Tz Uc Ut Uw Vh) Iv(aF Bb Bn bR cQ Dc Dd dG dL Em Et Fw Gb Gc Gp Ic Il Is It Jg Ji Jm Jp Jt Ko Kq kR Mf Mt Mw Ne Nr Nt Nw Oh On Pa Pb Pc Pf Pj Qc Qe Si Wf Xa Ti) Si(aA aE aM Ba bN bO fR Fw gL hG Hp Hw Hx Ih Ir It iZ Jl Jm Jn Jr Js Lj Lx Mr Mt Mw Nb Ni Nt Nv NW Oa Oh On Pf Pi Ps Qe Rm Wb Yd Xa) Nw(aD aV aW bL Bn bO cD cV cW Dd Dp eF Ex Fc Fw Gl Hu Ic Im It Iu Jm Jt Ju Kd Nb Nr Nt Ow Pa Pd Qu Rc Rg Ru Sf Sr Ub Ul Us Uv Wf Yd) Lj(aC aE aG aH AO Ba bO cE Cu Cw Dd Dl Et Fc Fi Gb Gc It Iu Iz Jd Jg Ji Jt Ke Ko Kp Mp Mv Na On Pg Ps Pz Qt Qw Uc Uf Un Vo Vw) Kq(AD aF Aj aO Ar aW aX bF bG bL Bn bZ cD cH cS cV cW Dk Fc Fr Fw Gl Hq Ic Iz Jm Jy Kl Lu Mh Mx Oa Og Oh Qw Rt Tn Us Ux Vs) Om(aE aF Aj aO Aw AX Bn bO CH Cs cV De Ef Eq fP Fr Hc Hx Ic Iz Lz Mh oE Of OH Oy Pk Qn Qu Qw Rf Sh Tz Us Uv We Wf Yd) On(aD aE aF Aj aO bF BG Bn bZ cD CH cV cW Dk Eq Fc Fr Fw Gl Hc Hq Ic iP Iu Iz Jl Jy Kl My Og Qw Sh Tn Ur Us Uv Wf Yd) aE(Ar cU Et Fp Gc Gp hB Ic Ij Is Ji Js Jv Ke Ko Lh Lx Lz Mf Mk Ml Mn Mq Mt Mw Nn Nr oE oF Oh Ow Pe Pf Pj Po Sr Tz Un Ut) Nt(aX bG bV cH dB Dc Eq fP Fr Gc Hf Hx It Ji Js Ke Ki Lh Lx Lz Mh Ml Mw Mx Oa Oh Oi Or Ow Pb Pc Ph Qc Qg Qx Tz Un) Nv(aF Aj aO aW Bn bS cE Ch Cs cV cW cX dR Eq fP Fr gP Hc Hx Ic iP Iu Lz Mh Na nY oE Oh Oi Pj Pk Ps Qn Qw Sh Ur Wf) Dd(Ar Bn Cs Fp gL hB Hx Ih Im It Jn Jr Js Lx Lz Mh Mk Ml Mq Mt Oa Oh Ow Pe Pf Po Ps Qa Qt Qx Rf Rm Tz Un Ur) Mw(aG aH aX bA Bn bS Ch cT cV cX Dc Dk Eq fP Fw Gc gP Hc Hu Ic iP It Lx Mt My Na nY Oi Ow Qn Qw Ua Us Wf Ye) Ic(aA aM aP Ba bO cM Cu Ha hB hC Hp Hq Hu Hw Hx Ii It iZ Jl Jm Kz Lh Mq Mr Nb Nf Oa Pf Qt Tz Ut Wb Yd Xa) Qd(aD Aj aW bA Bn bO bS Ch cT De Fc Fr Fw gP Hu iP Kr Mh Ml My oE Oh Oi Ow Qn Qw Ru Ua Us Uu Uv Vp Wf Ye) Is(aA aC aD aF aO bF BG Bn bO CH cV dD Fc fP Hc Jl Lv My Nx Of Qw Rg Sh Tn Uo Up Us Uv Vp Wf Yd) Ar(Ao BA Bb Cp Cq Cu Dc Ef Ho Hu Hv Hw Hx Il Iq Jg Jk Jm Jt Kd Lp Mi Mv Na Oi Pi Pz Qc Tz Ua Ut) Gc(Bn bO cG cX dA De dR Hp Hu Hx Ih Im Ir iZ Jm Jn Jr Kk Lv Mt Nb Oa Oh Oi Pj Qt Qv Qw Rf Rm Un Yd) Ow(aX bO cS cW dD dH Eq Fw Gb Hp Hx Ih Im Io Ir iZ Jm Jn Ma Nb Oa Pi Pk Ps Rc Rg Rm Ub Uo Uv Wb) Hp(Ao aW Bn bS cQ cX Dc Gp

Figure 36 Continued

Ij Il Ji Lh Lu Lx Lz Mf Mg Mh Mk Ml Mp Nn Oi Pf Pj Qc Qn Qx Ti) Oh(aC aF aO bE bG bO bR dD dH fP Gb Hu It Iu Jg Jk Jt Ke Mq Mt Mv Pc Pd Pi Pj Pz Ub Uo Wb) iZ(aG Ap BB bR bS Co cQ Cw Dc Et Il Iu Ji Ko Lu Mg Mk Mm Mp Na Nm Oe Pj Qn Uf Vh Ye Ti) Tz(aG aH aW Ba bO Cw cX Fc Fi Gb Ho Hw iJ Iu Jg Jt Kd Ko Mt Nf Ni Nm Nn oE Pc Pd Pj Uf) Jn(aC aG aJ aW Bn bS cP cX Dk dM Fc fP gP Hc Ib iP Ji Jl Kc nY Pa Pc Qn Qw Rj Vp Wf Ye) Nb(aC aG aS bG Bn cC Cw Fc Fw hB Hc iA It Iu Ji Jl Ke Li Mp Ms Nm Pd pF Pj Qw Vp Wf) Un(aD Al aW bA bL cT Gp Ih Il Im Ir It Jg kQ Mx Nn Nr Nx Oa Og Pf Qc Rm Sr Ul Us Uv) Pe(aD aJ BN bO bS cX dD dL Du Fc gP Hc Ib iP Mj Ne Oi Pc Qn Qw Rj Uo Vp Vs Wf Ye) Hx(aF aG Ao aW Bn cD cQ cX Fc Fw Gp Hu Ii Jm Mf Mt Nn Pa Pf Pj Pz Qc Rj Ru Rx) Ps(aG aW Ch cW dR fR gP Ha Ij Jl Kl Mh Ml My nY Qn Rc Rj Rx Sh Ss Ua Us Vp Vs) bO(Cw Fw Ii Il Ir Iu Ji Js Jt Ke Lh Li Lx Mt Nn Nr Pf Pj Po Qa Qc Qe Rm Uc Ut) Ba(aF Aj aO cQ cX Dg dR Eq fP Hf Ki Kl Lz Mh Mk Ml Nd oK Or Ph Qg Qx Rz Ss) It(aW Bn bS cQ cV cX dR Fc gP Hw Ki Mf Mi Mp Mt Oi oK Pc Qn Qw Rj Rx Ur Wf) Ih(aH aJ bS cI cN cX Hc Hl IP Ji Ke nY Oe Oi Pc Pj Qn Qv Qw Rx Wf Ye) Jm(Cu Fp Gb gL hB Hv iO Iu Jd Ji Ke Mi Mk Mp Mq Mr Ms Mv Nq Pd Pj Ue Wd) fP(Ao Cu Cw Ef Fr Fw gL Hw Im Iz Js Kf Mt Nh Pf Qa Tn Uc Uf Ut Uw Xa) Gb(aM Ao cX dR Jr Ki Lh Lz Mf Mh Mk Ml Mt Nn Oa Oi Pf Qg Qt Qw Qx) Mq(Al aX bA Bb cQ cT Dc Fd Ho Ii Iq Ir Jk Jt Ki Ks Nr Pa Qc Xa Tj) cV(Cu Cw Et Ii Ir Ji Jl Jp Js Ko Lh Mt Nn Nr Ok Pf Qa Sr Ut Uw Xa) Ha(aG aW cX gL Gp Hf Lz Mk Ml Ms Nd Oi Pf Qt Qw Qx Ru Ur) Ke(aV AW bA bL bN cD Fc Fw Gl Im Ir Oa Pa Rm Ru Us Uv) Pj(aA dR Fp Hu Jl Jr Kd Lp Mt Nr Oa Oi Pk Qt Qw Rm Wb Yd) Qa(aC aD Bn cD dD Ex Fc Fr gP Hc Hl iP Qw Uo Ur We Wf) Ji(aD aV bL BN cD Fc Fw Im Lv Nr Oa Og Ru Uv Wb Yd) Sr(aA aC aH aM An cM Cq hC Jf Ki Nc Ni Nk Nl oK Sh Wb) Jk(CH Cs Dp Eq Jj Lx Lz Mh Mk Ml oE Qx Rf Sh Ur Wf) Ut(aF Aj aO cH Eq Hc Iz Jj oE Pk Qw Sh Ur Us Uv Wf Yd) hB(aF Al Bb bR Cp cQ Dc Fi Ho Hv Jq Lu Mi Na Pi Pz Vs) Hw(aH Aj Bn bR cQ cX De Eq Lh Mb Mt Nr Pb Pc Rf Wf) Rm(aC bG Bn bX dD Dk Fc Hc Mj Pa Qw Rv Sh Ur Vp Wf) Fw(aM bS cG cX dR Jj Ki Lx Ms Mt Na Oa Oi Sh Vz) Jt(cX Dg dR Eq Gd Jr Kl Lh Lz Ml Ph Qx Rt Sh Wf) Im(aG aH aJ aR cI dB gP iP Ki nY oE Qn Qt Ss) Qc(aA dR Fp hG Hu iO Jj Mi Mp Ms Mt Rf Sh Uo) Js(aC aF bE Bn bS cP cQ cW dD Ex Fc Mj Mt Pc) Li(aD Aw cC Co cR cS dD dH Fc Gl Uo Us Uv Wb) Nr(aA aC aG aS bG cF Mi Ms Pc Rh Sh Uo Ur) Ij(aO aS bN cZ Je Jo Lv Pc Rh Rt Uu Vc Vz) Jg(Aj bX Cs Dg dR Eq Fp Kl Mk Mv oK Sh Vo) Oa(aC aD aG Fc Iu Ko Mp Oe Pd Pf Uf Ur Ti) aF(aA Cu Dc Ii Jl Jq Lh Lx Mj Mt Ou Po Qx) Hu(Ax Cs Fp Iu Lx Lz Mh Ml Mx oE Pk Rf) Xa(aS aW Bn cQ cW cX Ju Nd Oi Qw Ru Vs) Eq(Ao aW Co Iz Mg Mt Ng Nq Pd Uf Wd) Qe(aC aD aG Bn Fc Hl Ms Uo Us Vp Wf) Jl(aO aW bG Bn cH cX Fc Lz Og Qw Wf) Ir(aC aD bE Bn Cv cW Mp Ms Uo Wf) cQ(aA Ax Cs Cu hC Nf Pd Pk Qx Ra) Mv(aW Bb Ch dE Fc Ii Kd Nx Pa) Iu(aA aX Io Ms Mt Oi Pa Pf Th) Cu(Aj aO bL cW cX Of Us Wf) Fp(aG aW Bb Fc Il Pa Pc Pz) Pf(bF bG oN Pi Pk Rv Uo Wb) Ao(Ch Kd oE oH Pc Pk Rf) Bn(Ii Jq Jr Lx Mr Nh Po) Nn(bR cF cH cR Jq oH Pk) Mt(aO bG bV cH Fr Lu Uo) aX(Co Ez Ho Mg Pd Uf Wd) Lx(aD bE cP Fc oF Wb) Mr(aW Ju Qn Ru Ul Wf) Rf(Bb Fi Ho Mi Pc Pz) aA(Dc Dp Il Jf Mf Vh) Ef(aH Aj CH Yd) Ii(aD bE cW cX Ur) gL(aI bR Dc Ki Pc) kR(Cw Ho Mi Ou Pd) Mx(aC bE cZ Db) Lh(aD aO Rg Wb) cX(Cw Dk Ko Nh) hC(Et Kd Pz Uc) Ch(Iz Ua Wd) Dc(Rt Ur Wf) Fc(Cs Et Po) Fd(Lz Ml Qx) Sh(Ju Jv Mn) Uw(cW dR gP) Ax(aC cP) De(Ho Hv) Mi(bL Uv) Wb(Mf Mk) Jq(bE bN) Ko(Mh Oi) Ks(Jj Ms) Pc(oF Pd) aD(Et Po) aS(bA cT) cE(aO pF) AjIz CpRt CscP CwUv DkOg NqKd NdKz UaoE HvUs IoPd ZxiJ JraW UfbL aHiO} Yd{Uh(Ad aM As Ax bA Bn Co Cp Cq Cs cT Cw Dc Dd De Dk Dl dN Dr EF Em Et Ex Fw Fy Gb Gn Ha hB hG Hl Ho Hu Hv Hw Hx Ib Id Ih IJ Il Im In Is It Iv Iz Jd Jh Ji Jk Jl Jn Jo Jq Jr Js Jt Jy Kd Kf Kg Kj Kn Ko Kp Kr Ld Lh Lp Lw Mg Mi Mj Ml Mq Mr Mu Mv Mw Mx My Mz Na Nf Ni Nm Nn No Nr Nt Nv Nx Ny oF Oh Om On Ou Ow Oy Pb Pd Pe Pf Ph Pi Pk Po Qa Qd Qe Ql Qx Ra Rb Rj Rt Ru Si Sr Tn Tv Uc Ul Un Uo Up Us Ut Uw Uz Vb Vh Vp Vq Vs Vt Vw Wd We Wg Tl Xa Ti) Gc(aA Af aH aQ Ar aW Ax aZ bA bB bQ bR cH CO Cp CS cT Cu CX DR Ed Ef Ez Fp FR Fw Fy gL Ha Hu Hv Hx Ic Ih Im Ir Is Iu Iv Jd Jh Ji Jk Jl Jn Jp Jr Js Jy Kd Ke Ki Kk Ko Kq Kx Ky Kz Ld Lh Lj Lv Lx Mg Mi Mk Mp Mq Mr Mt Mv My Mz Na Nb Nf Ni No Nq Nr Nt Nu Nv Nw NY Oa OE Oh Om On Ou Ow Oz Pc Pd Pf Pk Po Ps Qb Qd Qe Ql Qv Qw Qx Qy Rf Ri Rm Ru Sh St Tn Un Ur Ut Uw Xa) Nq(aA aE aH AX bA Bc bR Cp Cq Cs cT Cu Cw Dc Dd Dr Ed Eq Et Fd Fw Fy Gb Ha Hf Hx Ic Ih Ii Ij Ik Il Iq Ir Is It Iv Jh Jk Jl Jn Jp Jr Js Jt Kd Kn Ko Ld Lh Lj Lp Lx Mi Mj Ml Mn Mr Mt Mx Mz Na Nm No Nr Nt Nv Nw Ny Oa oE Oh Oi Ok Om On Oz Pa Pf Pg Ph Pi Pj Po Ps Pz Qa Qe Qh Qx Ra Rb Rm Ru Ry Sh Si Sr St Tn Tv Ub Uf Ul Ut Uw Vh Vp Vq Vs Vt Xa Tj) Ld(Ad aH AL Ap AX aZ bA Bb bR bX cB cE Co Cp Cs cT cU Cw Cx Dd Dk Ed Et Fi Fy Gb Gp Ha Hb Ho Hq Hu Hv Hw Ic Ii Il Io Ip Ir It Jh Ji Jk Jl Jm Jp Jq Jr Js Jt Jv Kf Kn Kp Kq kR Lh Lj Lx Mg Mj Mm Mn Mw Mx Nm Nn Nr Nt Nv Nw Oa Oh Ok Om On Ou Ow Pa Pd Pf Pg Ph Ps Pz Qb Qd Qe Qh Qy Rm Si St Tn Tz Uc Uf Un Ut Uw Vh Vq Vt Wf Xa) Nw(aF Ap aX aY bE bJ bU CO Cu CX cZ Dd De Dg dI dK Dl dR Ed Ef Et Ez Fi Fr Fw Gb Gd gL Ho Hu Hv Hw Ic IH iJ Il Im iO Ir Is It Iu Iv Iz Jd Ji Jn Kc Kd Ke Kg Kj Ko Lj Mg Mi Mk Mm Mp Mq Mu Mw Na Nb Nh No Nr Nt Nu On Or Oz Pd Pe Pf Ps Pz Qd Qe Ql Qn Qw Qz Ru Rx Rz Si Ue Uf Ut Vh Vq Wd Wf Wm Ti Th) Ut(aE AF aG AJ aM aO aQ aW aY aZ bF BG Bn Bo bR bS bZ cE cG Ch cL cQ CX Dc Dd dH dM DR Eq Et fP gP Hq Hx Ib Ic Ih Ik Il iP Ir Ji Jj Kd Ki Kl Lu Lx Lz Mh Mk Ml Nb No Oa oE Oi oN Oy Oz Pb Pc Pi Po Qb Qe Qn Qv Qw Qx Qy Rt Rx Sh Si Ss St Tz Um Un Ur Uu Uv Vc Vp Vq Vt We Wf Ye Ti) On(AF aG Aj aN aO aQ aU aW aY aZ bF BG Bn Bo bR bS Ch Co cP cQ Ct cW CX Ed Eq Et Fw Gl Gp Hb Hc Hv Ic Ih Ji Jj Kc Kd Kg Ki Lj Lu Lx Lz Mg Mh Mi Mk Ml Mp Mq Mt Mu Nb Nn nW Oa Of Om Ow Oz Pc Pf Pj Qb Qd Qe Qn Qw Qx Qy Rj Rt Sh Si Tz Uf Ug Um Un Ur Uu Uv Vp Vq Vs We Wf Ti) Jh(Af aH aI aM Ar aW AX aZ bB Bg cH cQ Cs CX dR Et FP Fw Gp Hb Hc Hf Ic Ih Ij Il Ir Is Je Ji Jn Js Ki Lh Lj Lx Lz Mh Mk Ml Mx No Nr Ny oE Oh Oi Or Ou Ow Oz Pb Pc Pf Pj Po Ps Qa Qb Qc Qe Qg Qt Qv Qw Qx Rg Rj Ru Rv Rx Si Sr Ss St Tz Un Ur Us Vb Vo Vq Vs Vt Wf Ye Ti) Om(AF aH aM Ax aY aZ bG bL Bo bR bS cE cG Ch Cs cV Cx dH DR Ed Eq Et fP Gp Hb Hc Hf Hx Ic Ih Ip Ir Is Iz Ji Jj Jn Jo Jp Js Ki kR Lh Lx Lz Mb Mh Mk Ml Mx Nb No Ny Oa oE Oh Oi Or Oy Pc Pe Pf Pj Po Qb Qe Qm Qx Qy Rt Ru Sh Sr St Tz Un Ur Uu Uv Vb Vc Vq Vt Ye) Is(aA AF aM Ap aW aY bC bE bG bH bJ bM bN Bo bW Co CV Cx cZ dI DR Ed Ez Gz Hc hG Hv Ik Im Iq Jd Jj Kc Kd Ke Kg Kk Kz Mg Mh Mi Mj Mm Mp Mq Mt Mu Mv Mw Mx Nb Ni Nn No Nt Nu oE Og Ow Pd Pe Pj Qd Ql Rj Rm Rt Rv Rx Sh Sr Uf Ug Ur Uu Vt Wb Zw Ye Ti) Nn(aE aF aG aH Aj aO aR aY bF Bg bM bR bS bZ cF cL Cu Dc Dd dH DR Et Ez Hb Hv Hx Ic Ih Ij Ir Ji Jj Jn Jp Jq Jr Js Kd Ki Lu Lx Ma Mi Ml Mw Mz Nb No Ny OH Oi oK oN Or Oy Oz Pb Pc Pe Pi Pj Ps Qb Qd Qe Qx Qy Qz Si Sj Sr Ss St Tz Un Vc Vq Vt Wb) Ps(Aj aK Ar aU aW aZ bB Bo Ch cN cU cV CX dR Ed Et Fw Gh Gp Hc Hp Ic Ij Il Ji Kd Ki Kl Lh Lj Lx Lz Mf Mh Mk Ml Mq Mt Mw Oa OE oF Oh Oi Ou Oz Pa Pc Pf Pj Po Qb Qd Qe Ql Qv Qw Qx Qy Rc Rj Ru Rx Sh Si Sr Ss Un Ur Us Uu Vo Vq Vs Vt Wf Ye Ti) Mt(aE aH aI AN aO aS aY bB bG bI bJ bR bV CH cP cV Cx DC dH dK Eq Et Fr Hb Hf Hx Ic Ih Il Im In Ir Jf Jn Jq kR Lh Lu Lx Lz Ml Mw Mx Nb No Ny Oa Oh Oi oK Op Ou Ow Oy Pb Pe Pf Ph Qa Qb Qc Qd Qe Qg Qm Rm Si Sr St Tz Un Vb Vc Vq Yl) Qy(aH aI aQ Ar Ax bB bO cH Cs CU dD Du Eq Et Ex Fp Fw Hx Ih Ir Iv Ji Jl Jn Jq Jr Js Ke Kq kS Kx Kz Lx Lz Mh Mj Mk Ml Mq Mr Mv Mx Mz Nb No Nr Nv Ny oE oF Oh Oi Or Ou Ow Oz Pe Pf Pg Po Qa Qb Qe Qh Ql Qv Qx Rc Rf Rm Rv Si Sr Tz Un Vt Xa) Qd(aW Ax BA bQ bS Ch cN Cs cT Cu CX DR Et Fw Fy GP Hb Hf Hu Ih Ij Il iP Jn Js Kx Lj Lx Lz Mf Mh Mk Ml Na Nb No Nr Ny Oa OE Oh Oi Oz Pe Pf Pj Qn Qv Qw Qx Ra Rf Rh Rj Ru Rx Si Sr St Ua Uf Ur Us Uu Vh Vq Wf Yl Ye Xa Wm) Ke(AF Aj aO Ap aY BA Bc bF Bg bL bM Bn bP bR CH Cu cV Cx De dH Di dK Dl Ed Ez Fw Ik Il Jl Jt Kg Kn Kr Mm Mp Mq Ms Mz Nc Nd Ne Ni Nj Nk No Nr Ns Nt Ny Oi Oz Pb Pj Pk Qe Ql Qv Qw Qz Rx Ry Sh St Tv Uf Uu Uw Vp We Tl Tj) Ow(aE Aj aR aZ BG bM bQ bS bZ cE cL cM cO cS cU Dc Dd dF Dk dL Gb Gz Ha Hp Hq Hv iA Ih Ij Im Io Ir It iZ Ji Jn Jp Kd Ko kS Lp Ma Mf Mv Mw Mz Nt Oa oF Oy PF Pj Pk Pz Qa Qe Qt Qu Ri Rz Si Sj Sr St Tz Ua Ub Um Vc Vq Vt) Pj(aP Ax bA Cq Cs Cu Dc dR Et Ex Fd Fp Fr Fw Fy Hu Hv Id Ih Ij Im Ir It Iv iZ Jd Ji Jk Jn Jp Jq Jr Js Kd Kk Lh Lj Lp Lx Mi Mj

Figure 36 Continued

Mq Mr Mv Mw Mx Mz No Nr Nv Ny Oa Oh Ou Pe Pf Pg Po Qb Qe Qh Qv Rm Sr St Tv Tz Un Uw Vp Vt Xa) Ji(aA aN Ap aY aZ Ba Bc bE bJ bM bN cF Cp cX cZ Dc Dd dK Dl Dr Ex Fy gL GP Hu Il It IZ Jl Jm Jv Kd Ko Lj Lp Lv Mp Mv Nd Nm No Nr Nu Nv Nx Of Og Oh Or Oz Pa Pb Pf Ph Pi Pz Qc Qe Rg Ri Rj Rm Ru Rv To Ul Vq Th) Sr(AF aH aI aK aM AN Ao aQ aU aW aZ bB bH Bo bR Co Cv CX cY dJ dR Ez Gp Hv Hx Ic Jj Jn Jo Jp Kc Kd Kg Ki Kk Ko Kq Ky Kz Lx Mg Mi Mm Mp Mq Mu Mv Mw OE Oy Oz Pa Pc Pd Qa Qe Qv Qw Rt Sh Si Uf Ug Vt Wd Xa) Ij(aA aE aO aS aU aW bC bH bR bZ cC cE cM Co cT cV cZ De dF dG dH dJ dM Ed Ef Gz Hc Ho Hu Hv Im Jk Jn Kc Kd Kg Kj Kk Lu Mg Mi Mj Mp Mq Ms Mu Mv Mw Nb Oi oN Oz Pc Pd pF Pi Qa Qe Ri Rt Rv Uf Um Un Ur Vc Wb Wd Tj) Kq(Aj aO aW aY bS cG cQ cV cW dB Dc Dd De Di Dl dR Ed Fw Gl Hq Ib Ic Ih Ik Il In Iv Jj Jm Jn Ko kR Lh Lj Mb Mf Mx Nb Nd No nY Oa Oe Oh Op Ou Pe Qc Qe Qn Qw Rm Rt Ru Rx Rz Si St Ua Ul Us Ux Vp Vt Vw Ye Ti) Mw(Af aG aJ aK aQ aU aW aZ bB Bn bR bS cN cT CX De dR Et GP Hb Hc Hf Hu Ib Ic Il iP Ir Jj Jn Jp Kd Ki Kx Lv Lx Lz Mh Mk Ml Na No Nr Oe Oz Pb Pf Qe Qn Qv Qw Qx Ru Rx Si Tz Ua Un Ur Vq Vt Yl Ye Ti) Si(aA aM aP Ar Ax bB bJ Bo bQ bZ CO Cs Cu Dp Dr Ed Et Ex Fp FR Fw hB Im It Iv Jj Jl Jn Js Jy Kx Ky Lj Lx Mk Ml Mq Mr Mv Mz Ni No Nu Nv Ny Oa Oh Oz Pc Pf Qa Qe Ql Qv Qx St Un Ur Uu Vq Ye Xa) Mq(aF aR aX aZ bA Bb bR Cp cQ cT Cx Et Fd Fy Gb Gp Ha Hb Ho Ic Ih Ii Il Iq Ir Jk Jl Jn Jp Jq Jt Kn Ko Ks Lu Lx Mn Mz No Nr Nt Ny Oa Oh Ok Pa Pc Pe Pf Pz Qb Qc Qe Qh Rb Rm St Tz Un Vq Vs Vt) Pe(AF aN aO aQ aW aX aY bC bH bM Bn bS bW CO cQ cV Cw cX dA Dd De dI dK dM dR Et Ez Gp Hc Ib iJ Iu Kc Kd Kg Kj Mg Mi Mk Mm Mu Mv Na Nd oE Pd Qn Qv Rj Rv Sh Uf Ug Uu Vc Vp Vq Zw) Pf(aF aO bF bJ bM bR Co Cp Cu Dd Ef Fd Gb Ha Hb Hp Hu Hv Hx Ih Jk Jl Jn Kg Ko Mg Mi Mp Mu Mv Mz Na Nb No Nt Nv Ny oN Oz Pc Pd pF Pi Qe Ri Rv St Ua Uf Un Vc Vq Vt Vz Wb Wd Xa) Et(AF aO Ar aW aY aZ bJ bL Bn bR Co cP cQ cV CX dH dI dR Ed Fc FP Fw Hu Hw Ic Ih Iv Jd Jn Js Ko Lh Lj Mk Mn Mu Mv Nb Nd No Nr Nu Nv Ny Oa Oz Qe Qw Rm Ry St Tz Vt) Ny(Ap Ar aU aW aX bB bC bJ Bo bW bZ CO cS CU Cw CX dR Ez Fw Gp Ho Hv Ic Iu Kc Kg Lh Lv Ma Mf Mg Mi Mk Mm Mp Mu Mv OE Ou Pd Po Qv Rj Rx Rz Uf Vq Wd Wf) Qe(aC aG aN Ao Ar aW aZ bJ bM Bo bQ bZ cE CO cP Cu Cv Cx dI Ez Fw gL Gn Gp Ha Hl Hu Ic Kd Kg Lx Mg Mi Mk Ml Mm Mp No Nt Nu Oe Oz Pd Ql Qx Rj Rx Uf Un Ur Ti) Lx(aF Ao Ap aW aX bC bE bW Co Cu Cx Dd De dI Ef Ez Fw Ho Hu Hv Ih Im Iu Jk Jn Kc Kd Kg Kj Ko Mg Mh Mi Mm Mp Mu Mv Nb Nt Nv Oz Pc Pd Ql Rh Ua Uf Vq Vt Wd) Jn(aF aG Ap aU bC bS bW bZ cE CO cQ cV Cw CX Dd dM dR Ez Hb Ho Ib iP Kc Kg Lh Mg Mi Mk Mm Mp Mu Mv Ou Oz Pa Pc Pd Qw Rj Uf Un Vp Vq Vt Wd Wf Ti) Nb(aG aH aI Ao Ap aU aW bB bW bZ CO cQ cS CU CX Ez Fi Gp Hb Hl Jd Kc Kg Lh Mg Mi Mm Mu Mv Nh Oe Oh Op Pc Pd Ql Qm Rx Rz Uf Ug Vq Ti) Qa(aW aZ bM bP bS cE cP cQ cV Cw cX dG dI Dk dM dR Ex Fc Gn GP Hc Ib iP Kd Ko Mj Mk nW Oe Oi Oz Pc Qn Qw Rj Rx Un Ur Vp Vq Vt Wf Zw Yc Ti) No(aF aK aQ aV aW aX bC bW CO cQ cS cV Cx cY De dJ dK Ef Ez Ho Hv Kc Kd Kg Kj Kz Mg Mi Mk Mm Mp Mu Mv Ou Pc Pd Ql Rx Uf Ur Vq Vt Wd Wf) Oh(aA aE aF Ap aW bE bG bJ bM Bo bR bW Co Dd Ef Ez Gb Gz Hv Im Jd Jk Kc Kg Mg Mi Mp Mu Mv Nt Nv Oz Pd Ua Uf Un Ur Vq Vt Wb Wd Xa) Li(aJ aO aP aX aZ BG bM bQ cE Ch cO cS cU dD dH dL Ez Fn fP Hc Hl Ik Jl Jp Kl Kr Mv Ng Oi Oy Qu Qv Qz St Tj) Vq(Ar aZ Dk dR Ed Fp Fw hB Hu Hv Ic Im Iv Jj Jr Kk Ky Lh Lz Mk Ml Mv Nu Nv Oa Or Ou Oz Qb Ql Qw Qx St Un Vt Xa) Vt(Ap aW Ba bN Cp Cu Ef Fw Fy Gp Hw Ic Ih Il It Ks Mg Mm Mv Na Nr Nv Oz Pd Ql Ra Rf Ru Tn Uf Xa Wm) St(aU aW bC cC CO cS cU dK dR Ez Fw Ho Hv iO Kd Kg Kz Mi Mk Mm Mp Mu Mv Ou Pd Po Uf Un Wd) Im(aG aH aI aJ aK aQ aU bB cI cX cY dB dR Hb Hf Jp Lh Lv Mk OE Oi Or Ou Pc Rc Un Ti) Js(aF aG aY bG bM Bo bW Co Dd Gb Hv Jk Kc Kg Mg Mi Mp Mu Mv Nt Oz Pc Ql Uf Un Wd) Oz(Cp CU Dk Ef Hq Hw Jd Jl Jp Lh Mk Mp Nv Ou Pg Po Rm Tn Tz Un Uw) Cx(Cp Cu Fy Jl Jp Jq Jr Jt Mi Mj Na Nv Ou Pg Pi Po Tn Un Uw Xa) Lh(aF aY Co Gb Ih Jt Kd Lu Mg Mi Mm Mp Mr Mu Nt Nu Pd Pi Uf Wd) Ql(aZ bA Cq Cu Dc Dd Fw Fy Gp Hv Ih Il Ir Jk Jp Kd Mi Nr Qh Xa) Qb(aW Co Cu Cw Ef Ez Hv Ih Kg Mg Mi Mp Mu Mv Nt Pd Uf Vw) Hb(Co Cu Ef Fr Fw Ih Kg Mg Mi Mu Mv Nr Nt Oa Pd Wd Xa) Nv(Af aO aW cX dR Hv Hx Ic Iu Lu Mk Mv OE Oi Qn Qw) Un(aW aY bA bQ Fw Gp Ic Ih Il Lj Mx Nr Oa oE Pz Ru Xa) Ml(Ap Bb Cu Dd Gb Ho Hu Ih Jk Jt Ko Mi Nt Ua Uf) Tz(aW Cw Ez Ho Hv Kd Mg Mm Mp Mv Nt oE Pd Uf) Fw(aG aM Ao aZ Cu dR Ef Jj Jl Jp Mv Po Xa) Qx(Cp Dd Gb Ho Hv Ih Jk Kd Ko Mi Nt Ua Uf) Ou(Ao Ap aW Ax aY Co Ih Mg Mm Nt Pd Ru) Mk(Gb Ha Hu Ih Jk Ko Nt Oa Pc Xa) Ed(Co Iu Mg Mp Mv Pd Uc Uf Ti) Ar(Ho Hv Ih Jk Jp Mi Pi Uf) Jl(aW cP cQ cX Gp Kd Oe Rx) Oa(aG Ao aZ Ic Kc Mm Mp Uf) Cu(aZ Bo cX Gp Ic Lj Wc) Ih(aH aZ bB cO Jj Rx Ur) Jp(aF aW bR cX Iv Mz Rx) Lz(Cp Gb Ho Jk Mi Nt) Uw(Af cX dR Ic Iv Nr) Co(aX aZ Ch Eq Mj) Po(aW aY Hu Jk Nd) Xa(aY aZ cQ Ic Rx) Ur(Dc Ii Jk Nr Rm) Kd(Cs Fp Mv Qm) Uf(aX aZ Hf Mj) Nt(In Mj Or) Mi(Bo Hf Op) Mx(Ao Mp Mv) Ic(Hv Iv Mr) Gp(Hx Iv) Jd(kR Oi) Jq(aW bJ) Lj(Ao Mp) Rm(Qv Rx) AnIv ApOr DkaW DpJk TiFp GnHv MgaX MjMv NdKz QcJj WdaZ aFaH aYbB bRcU} Rt{Is(aA Ad aF aM AN aO Ar As Ax bA bF Bn cH Cp Cq Cs Cu CV Cw CX dA Dc dN Dr Ed Em Eq Fc Fd Fp Fw Fy Gb Gn Gp Ha hB hG Hl Ho Hr Hu Hv Hw Hx Id Ii Im In Ir Iv iZ Je Jh Ji Jn Jo Jq Jr Js Jt Kd Ke Kf Kg Kj Kk Kl Kn Ko Kp KQ Kr Ld Lh Lw Me Mi Mj Ml Mq Mr Mt Mw Mx Mz Na Nf Ni Nm Nn No Nr Nt Nu Ny Oa Of Oi Ok Om On Op Oz Pb Pc Pd Pe Ph Pi Pk Po Qn Qv Qx Qy Ra Rb Rg Rj Ru Ry Tv Ub Ul Un Uo Up Ur Us Ut Uw Uz Vb Vh Vp Vs Vt Wc Wg Yl Tl Xa) Oa(Ad As Aw Ax aY BA Bn bQ cC cE Cp Cq Cu Cx Dc Dd De dJ dK Dl Dr Ef Em Fc Fd Fi Fy Gb Gc Gn hB Hv Hx Id Ii IJ In iO Ir Iv Jg Jh Jn Jo Jq Jr Js Jt Ke Kf Kg Kj Kk Kn Ko Kp Kq Kr Ld Li Lw Me Mj Mq Mr Mt Mv Mx Mz Na Nf Nh Nm Nn Nr Nt Nx Ny Ok Om On Pb Pd Pe Ph Pi Pj Pk Ql Ra Rb Rj Ru Si Sr Tv Ub Uc Ue Uf Uk Ul Un Up Ut Uz Vb Vh Vp Vs Vt Vw Wc Wd We Wg Xa Ti) Kd(aF aW Ax BA bC bJ Bn Bo bQ bU bZ CO Cp cR CS cT Cu Cw Dr Ed Ef Et Ez Fp Fr Fw Fy Gc gL Ha hC hG Ho Hu Hx Ih Im In It Iu Iv IZ Ji Jk Jl Jn Jr Js Jt Ke Kk KQ Ks Kx Lh Lj Lx Ma Mf Mg Mm Mr Mt Mw Mx Mz Na Nf Ng Nk Nm No Nr Nt Nv NW Ny OF Oh Om Ow Pd Pe Pf Pi Pj Ps Pz Qa Qc Qd Qe Qy Rm Sr St Tn Ua Uc Uf Uh Uw Vw Wc Wd Wh) Ny(AF aK aU aW aX bB bJ Bn bS bW CO Cp Cq cS CU Cw CX dK DR Ez Fi Fw Fy Gc gL Gp Ho Hv Hw Ib Ic IH IJ Il Im In IO Ir Iu Iv Je Jh Ji Jk Jo Jr Jt Kc Ke Kg Kq Ld Li Lx Mf Mg Mi Mk Mm Mp Mt Mu Mv Mw Na Nm Nn Nq Nr Nt OE oF Oh Oi Om On Or Ow Oz Pd Pe Pf Ph Pi Pj Qe Qn Qv Qy Rc Rj Si Sr Uf Uh Ur Vp Vq Wf Xa) Ho(AF Al Ar aW Ax BA Bn bQ cT Cx Dc De Dr Ed Fw Fy gL Ha hB Hx Ih Ij Il Ir It iZ Jg Jh Jk Jl Jn Jp Js Kk Kq Ks Ky Ld Li Lj Lp Lx Mh Mq Mt Mw Mx Mz Ng Nk Nn No Nr Nt Nu Nv Nw Oh Ok Om On Ow Oz Pa Pb Pe Pf Ps Pz Qa Qb Qc Qe Qh Ra Rf Rm Ru Ry Sr St Tv Uh Ut Wc Ye Xa Wm) Sr(aK aN aQ aU Ax aZ bA Bc bI bQ bR cH cM Cq Cu Cx cY DB Dc DR Ed Fd Fy Ha Hf Hq Hv Hx In Io It Iv Jk Jl Jn Jr Js Jt Kk Ko Kq KS Kz Li Lp Lt Mi Mr Mt Mw Mx Na Nb Nv Nw Oh On Op Ow Pb Pc Ph Pi Ps Qa Qb Qd Qe Qh Qy Ri Rm Ry St Tv Ub Ut Uv Vp Wb We Wf Xa) Iv(aF aN aW aY aZ Ba Bb bL Bn bR Cw Cx Dc dE Ed Fw Fy Gc Hu Ih Il Ir It Jg Jk Jm Jn Jp Jr Js Jt Ke Kf Kk Kn Kq kR Ks Li Lj Mf Mi Mt Mw Nb Ng Nm Nn Nr Nt Nv Nw Nx Oh Om On Ow Oz Pa Pb Pc Pf Ps Qa Qb Qc Qd Qe Qh Qy Rm Ru Ry St Uc Uh Ul Ut Uv Vq Vt Wf Xa Th) Li(aF Al Ax bA Cp CQ cR CT Cu Dc Dd dE Dg Em Eq Fd fP Fr Fy Ha Hf Hp Hv Hx Ih Ij Il In Iq Ir It Jl Jm Jn Jq Jr Js Jt Ju Ke Kn Ks Lj Lp Me Mg Mi Mj Mr Mw Mx Mz Ng Nr Nw Ow Oz Pb Pc Pe Pg Ph Pi Pk Ps Qb Qd Qe Qh Qt Qu Rb Rg Rm Tv Tz Uz Vp Wc Xa Tj) Xa(aF aW Ax aY Bn Bo Cq Cu Cx Dc Dd dE Di dK Ed Fc Fi Fw Gl Hv Hx Ih Il Im In Ir Jk Jm Jr Js Jt Ke Kn Kq Ks Lj Lp Mf Mi Mr Mt Mw Mx Na Nb Nn Nv Nw Nx Oh Oi Om On Ow Oz Pa Pc Ph Pi Ps Qa Qb Qc Qd Qe Qy Ru Sh St Tv Uh Ul Up Ut Uy Vq Vt Th) Dc(aA aF aP aQ aR aW AX bJ bQ cK cO Cp Cq cS Cx De DR Ed Fw Fy gL Ha Hu Hv Hw Ih In Jh Jn Jr Kg Kq Ks Ky Kz Lj Lt Lx Mi Mk Mr Mt Mu Mw Na Nb Nf Ng Nn Nq Nt Nu Nw Oh On Ow Oz Pd Pf Qa Qd Qe Qy Ri Tv Ub Uf Ur Ut Vp Vq Vw) Ed(Ad Af As Aw bA Bc bJ Bn Cp Cq Cw CX dN Dr eF Fc Fy Gn Gp Hv Hw Id In Iq Ir Jh Ji Jo Jr Js Jt Ke Kf Kg Kj Kk Kn Kq Ld Lh Lw Md Mi Mr Na Ne Nr Om On Pb Pd Ph Pi Qa Qe Qx Ra Rj Tv Uc Un Up Ur Ut Uw Uz Vb Vh Vt Wg) Im(Af aG Aj aL aR Ax aZ bA Bg Bn bX Cp Cq CX Dd De dG Dk Dl dM Em Fd fP Gd Hb Hc Hw Ib In Ir Iz Jn Jq Jr Js Kf Ki Kj Kn kQ Mr Mx Mz Nb Nr Nv nY Oi Oy

Figure 36 Continued

Pa Pb Pe Ph Qn Rb Ry Tv Ug Uh Uu Uz Vo Vp Vs Wc We Wf Wh Zw) Mi(AF aH Ar AX Ba bL Bo bQ CX Fw Fy gL Ha hB Ih Ii Ij Ir iZ Jh Jk Jl Jm Jn Js Ju Kk Kq kR Ks Lp Mf Mt Mw Mx Nn No Nr Nt Nu Nv Nw oE Oh On Ow Oz Pa Pe Pf Ps Pz Qa Qc Qd Qe Qh Qy Rm Ru Ry St Uh Ut Vq) Qe(aA Ax bA bQ bR Cp Cq Cu Dd Dr Em Fd Fy hB Hv Hw Hx Il In Jh Ji Jo Jq Jr Js Jt Ke Kn Kq Mj Mq Mr Mt Mw Mx Mz Na Nf Nn No Nr Nt Nu Oi Om Oz Pa Pd Pe Ph Pi Qv Qy Ra Rb Ri Ru Tv Uc Ul Uo Up Uz Vh Vs Vt Wg) Fw(aA Ax bA Cp Cq Cu Cv Cw Dd dR Fd Fp Fy Hv Hw Hx Ih In Ir It Jh Ji Jl Jn Jr Js Jt Ke Kn KQ Kz Mr Ms Mt Mv Mw Mx Mz Na Nb Ni Nq Nr Nt Nw Oi On Pd Ph Pi Po Ps Qa Ra Rb Rm Ru Sh Tv Un Up Ut Uz Vp Vs) Jn(AF aU aW bG Bn bQ bW cE cL CO cP Cq Cu cX Dd De DR Ez Fc Fi gP Hv Hw Ih Ij Il Jr Kc Ke Kg Kj Kq Ks Ld Mf Mg Mp Mq Mt Mu Mw Na Nb Nn Nq Om Ow Pc Pd Pe Ph Ps Qa Qv Qy Ru Rx Uf Uh Uk Vq Wd) Nr(aA aF aU aW aY cM CO cQ cV Cx Dd Dr Ez Fd Fy Gc Hu Hv Hw Hx Ih iJ iO Ji Jk Jt Ke Kg Kn Kq Ks Ld Lj Mg Mp Mt Mu Mw Nn Nq Nv Nw Om On Ow Oz Pc Pi Ps Qc Qd Ql Qy Rh St Tv Uf Uh Un Ut Vq Vt Wf) Mx(aF Ao aU aX Ba bC bE bJ Bn bW CO cS Cu Cw Cx cZ dR Ef Ez Hu Hv Hw Ih Iz Jh Jk Kc Ke Kg Kk Kq Ld Mg Mp Mq Mt Mu Mv Mw Nb Nn Nq Nt Nv Om On Ow Pd Ps Qa Qd Ql Qy Rz Ua Uf Ut Vq Vt Wd) Nb(Af aN aZ Ba Bn Bo bQ cN CQ cU cV cX Dg Eq Fc Fy gL It Jd Jk Jr Js Kj Kn Ks Kz Lv Lx Mb Mf Mk Mq Mw Ng Nt Oe OH On Ou Oz Pa Pc Pe Pi Pz Qa Qd Qv Rx Ry Tz Ug Uh Uk Ut Vh Vq Wc) Hv(AF Al aN Ax BA bL Bn bQ Cx Fy hB Ih Ij Il Ir It Jk Kk Kq Ks Lj Mf Mt Mw Nn No Nt Nu Nv Nw oE Oh On Ow Oz Pa Pb Pe Pf Ps Pz Qa Qb Qc Qh Rm Ru St Uh Us Ut Vq Wc Tj) Kq(AO aW AX aY aZ bA Ch cT Cu cV Dd Dg Eq Fd Fy Ih Il In Ir Jd Jm Jr Js Jt Lj Lp Lv Mr Na Ni Oh Oi Oz Pa Pb Pg Pi Ps Qb Qd Qh Rm Ru Ss Tv Tz Up Ux Uz Vp Wb Tj) Qa(aD Af aJ aR Ax aY aZ bM Bn bP bS Ch Cq Cu CX Dd dL Eq Fd fP Fr Fy gP Hc Ib Ij Il Jm Jr Js Ki Kl Kn Mr Nv nY Oe Pb Ph Pi Qn Qt Qv Qw Uh Ur Uu Vq Wf Zw Ye Tj) Mw(aL Ax bA Bc bH Cp Cq cT Cu Cv Dd Dr Em Fd Fy gP Ij In Iq Ir It Jq Jr Js Jt Ke Kn Lp Mr Mt Na Nx oF Oi Oy Pa Pg Pi Ps Qh Rm Ru Tv Up Uy Uz Vp Vq Wc We Yl Tj) Lj(aC Af aG aN aY bA bE bJ bQ cO Cp Cq Cu cV Cw Cx Dd dI Em Fd Fy Gb Hx Ij In Ir Ji Jo Jq Jr Js Jt Ke Kj Mr Na Nt Om On Ph Rx Tv Uc Up Ur Uz Vb Vp Vs) Pi(aF aI aN aW Ba CX dK Fy hB Ih Il It Jg Jk Jm Js Jt Kf Kk Ks Mf Mn Mt Ng No Nt Nv Nw oE Oh Om On Ow Pf Ps Pz Qb Qc Qy Rm Ru St Uc Uh Us Vq) Ij(Ad aF aO aR aW aY Bg cA cK CQ Cu cV cW dR Fc Gh Hc Ii In Jk Jr Lv Mj My Nn No Oi Op Ow Oz Pc Pe Qb Qm Qy Rc Rh Tn Uv Vc Vs Wf Wh) Ih(aA Ax bA bQ cM Cp Cq Cu Dd DR Fd Fy Ha Hw Hx In Ji Jr Js Jt Ke Kg Kj Kn kQ Mr Mt oF Oz Pc Ph Qv Rb Tv Ub Up Ut Uu Uz Vp) On(aF aO Ax aY bA CH cV Dd Dr Fd Fy Ha Hc In Jm Jr Jt Ke Kl Kn Lp Mr Op Ow Oz Pc Ph Ql Qm Qn Sh Tv Uv Uy Vp Vq Vt Wf Zw Tj) Nn(Af Aj Ax bA Cu cV Dd Dr Em Fd Fy Ha Hc Hp Hx In Iq Ir It Jr Js Jt Kj Kn Lp Me Mr Oy Pg Pk Ps Rb Tv Up Uz Vp We Wf Tj) Ir(aR bQ bR Co Cx De dI dR Ez Hu Hx Jh Jk Kg Kj Kk Ko Ld Lt Mg Mp Mt Mu Nq Nu Om Ow Oz Pd Qd Qw Qy Ry Uf Up We Wf) Jt(AF aW aY bJ Bn bQ Cx dR Ha Hu Il iZ Jk Jl Jm Kk Mf Mt No Nt Nu Nv Nw Oh Om Ow Oz Pf Ps Qb Qv Ru St Ut Uu Vq) Dd(aF Ax Ba bQ Cs Ct Cx Ez Fy gL hB Jr Js Kk Ks Ld Lx Mq Mt No Nt Nu Nv Nw oE oF Oh Om Ow Oz Pf Ql St Tn Ut) Cu(AF aX aY aZ bL cW Cx Fd Ha Il Jk Ju kR Ks Lp Mf Nv Og Oh Ow Oz Pa Pb Pe Pf Qb Qc Qh St Ul Vs Wc Th) Fy(aF aW aY bJ Bn Cq Cx Fc Fd Hu Jk Jm Ld Lp Mt Mu Nt Nv Nw Oh Om Ow Oz Pc Ps Qb Qc Qd Qy Rm St Ut Vt) Js(aF aW aY bN Bo Cq dK Dr Fc Hu Il Jh Jk Jm Kg kS Ld Mj Mt Nt Nu Nv Om Ow Oz Ph Qy St Uh Ut Vp Vq) Ps(bA bQ Cp Cq Hw Il In Jr Ke Kg Kn Mt Na Nt Oe Oi Pa Pd Ph Ra Rc Rx Uk Ul Ut Uy Uz Vh Vp Wg Tl) Jr(aF aW Bn bQ Cx Fc Fi Hu Jk Ke Kk Ks Mf Mt Nt Nv Nw Om Ow Oz Pf Qb Qd Qy Ru St Ut Vq) Ax(aF aW cP Cx dK Fc Fd Fi Hu Iz Jk Ke Kk Ks Mt Nt Nv Nw Om Ow Oz Pc Qd Qy Uh Ut Vq) Ow(Af aY bA Cp Cs Em Fd Ha Hp Hw Hx In It Jq Kn Lp Lv Me Mj Mr Na Rb Tv Up Uz Vp) Nt(aO bA Cs Em Fd fP Il In Jq Mj Mr Nd Nw Oh Oi Oz Pc Pg Qb Qd Qh Rm Tv Up Vq) Pe(aF aK aO aU aY cA cK CQ dK Gc Gh gP Jk Jm My Nd Pc Rc Rh Ul Uy Vt) Ke(aF aY bL Il In It Jm kR Ks Nd Oh Oi Oz Pa Pb Qb Qh Ru St Tv Ub Wf) Lp(Ez gL hB Hw Jh Ji Ld Mg Mq Mt Na Nv Om Oz Pd Ql Qy Uf Ut Uw Vq Vw) Cq(bB Fp Ha Hx Iu Jk Kk Ks Mf No Nv Oh Oz Pf Qb Qd Rm St Uh Ut Vq) Mr(aF aW aY CX Il Jk Jm Kk Ks Mf Mt Nv Nw Oh Qy Ru St Vq Wf) In(aF aW Cx hB Jk Kk Ks Mt Nv Nw Om Oz Pf Qb Qc Qd Qy St Uh Vq) Ut(aA Aj bA CH Eq Il Iq Kn No oE Oz Qb Rm Sh Uy Vq Vt Wf Tj) Il(aA Cp Cs Dr hB hC hG Hw Hx iZ Jh Ji Kz Pd Ql Un Vt) Cp(aF aW bG hB Jm Ks Oh Oi Oz Pb Qb Ru St Uv Vq) Fd(aF aW Bn Cs Cx Ks Mt Nv Nw oF Oh Om Oz Qy) Mt(aX bA Fr Ha Hw Hx Iq Jm Kn Qh Vp Vq Tj) Tv(AF aW Cx Jk Ks Mf Oz Pf Qy St Uh Vq) Om(aF Aj bA Bg Ch Dr Jm Kn Oz Pb Wb Wf Tj) Na(aF Cx Fc Ha hB IZ Kk Ks Oz Ph Vq) No(aK aU dK Gc Gh iH iJ Jk Kj Ph Wf) Dr(Bb Fi Hu Jg Jk Lx Oh Qc St Vq) Qy(Aj bA Ch cT It Mh oF Uu Uz Vp) Kn(aF aW Cx Jk Nv Nw Oh Oz Qd) Vq(Cs hC It iZ oF Pk Up Ur Vp) Hw(bA Jk Jm Oh Qh St Uh Uy) Oz(Hp Iq Jk Lx Ph Rm Tn Vs) Qd(bA oF Pa Ph Ul Us Tj) aF(bA Ii Jq Mz Ok Rb Vp) Ha(aW bA gL Nv Ph Ru) Jm(Jh Ji Kz Ld Mq Pd) Af(hB iZ Nw Pf Uc) Cs(Bb Fi Jk Ks) Lx(aY Jk Pc Ph) Jh(bA Ch Qb Qh) Nw(aY bA Bn Ph) Vp(aW Cx Ks Pf) iZ(Cx Gp Pg Uh) Hx(Hu Pf Ph) Qh(Mq Nu Pd) aW(Kj kQ Ld) Fp(aY Pa) It(oE Uh) Jk(bA oF) Oh(Em Hu) AlMq ChEf CwiA CxJq UcUu TnaO IqKk WbRu QbJi QcaA JlPh KsVt NvOi PbgL PcoF aYhB aZbJ} Im{Wf(aH aJ aK aL aM Ap AS Aw bB Bc bE bI Bn bQ bV cH cJ Cp CQ Cs Cu Cv Cx cY cZ DB Dc Dd De dG dL Dr Du Em Eq Et Ex Fd Fn Fp Fw Fy Gb Gc Gn Gp Ha HC hG Hl Hv Hw Hx Ib Id IJ In Is It Jh Ji Jj Jn Jo Jp Jq Jr Js Jt Kd Ke Kf Kj Kk Kn Ko Kq KR Kx Lh Lp Lw Lx Mb Me Mi Mj Ml Mr Mt Mu Mw Mx Mz Na Nf Ni Nm No Nt Nx Ny OF Ok Om Or Ou Pa Pd Pe Pg Ph Pi Pk Po Qa Qe Qx Ra Rj Ru Rv Ry Tn To Tv Uc Ud Ue Um Un Uo Up Us Ut Uu Uv Uy Uz Vh Vp Vs Vt Wc Wg Tl Xa Ti) Zw(Ad aK aM An aQ As bA bB cH Cs cT Cv Cw cY dB Dc dF DR Du Et Ex Fy Gn gP hB hC Hf Hl Hw Hx Id Ij Ik Ir Is Iv Ji Jo Kp Kq Kr Kx Ld Lh Lw Lx Mf Mk Mq Mt Mz Nf Ni Nr nY oF Oh Om On Ow Pb Pd Pf Po Qa Rc Rj Ru Sr Uc Ul Uo Us Vh Vq Vs Wg Tl) Gd(Ad aK As Aw cH Cp Cu Cw cY Dd De dN dR Fd Fn Fy Gc Gn Hl Ho Id iJ Jh Jo Jq Jt Kd Kc Kg Kj Kn Kp Kq Kr Ld Mg Mi Mq Mt Nf nY Ok Om On Pd Pi Pk Qx Ra Rb Rj Ru Sr Tv Uc Ud Ue Uk Ul Um Un Uo Up Us Ut Uw Uz Vb Vh Vp Vs Vt Wc We Wg Yl Tl Xa) Wh(Ad Aj aM Ar As cI Cp Cq Cv Dc Dd Dr Em hB Hc Hl Hv Hw Id Ij In Jj Jn Jo Jq Jr Js Kd Ke Kn Kp Kq Kr Kx Ld Lh Lw Mi Ml Mq Mr Mt Mz Na Nb Nf Nr NY Ok Om Pb Pe Ph Pi Pk Po Qa Qv Qx Ra Rj Sr Tv Ua Un Up Us Uu Uz Vp Vs Wg Tl Xa) Pb(AA Du Et Fc Fd Fr Gb Hl Ho Hv Hw Ij Ip Ir Ji Jj Jl Jo Jp Jq Js Jt Lh Li Lj Lw Mi Mp Mr Ms Mt Mz Nb nI Nn No Nr Nt Nu Nw Oe Of Og Ok On Pa Pc Pe Qa Qd Ru Rv Ry Uw Vb Vh Wc Wd We Wg Yl Tl Xa) Eq(Af aG aJ aP aX Ba Bn bQ bS bW bZ cE CO cS CX De Dk dR Ef Et Ez gP Hb Hc Ib Ic iP Kc Ki Kj Ld Li Lu Ma Mg Mi Mu Nn Nq nY Oi Ow Pd Pj Qn Qt Qv Qw Qy Ri Rj Sh Uf Ug Uh Ur Uu Vq) Oy(AA Dr Du Et Fd Fi Fr Gb Hl Ip Ir Jg Jh Ji Jj Jl Jp Js Jt Lh Li Lw Ma Mi Mn Mp Mt Mw Mz Nb Nn No Nt Nw Oe Og Ok On Pa Pc Pe Pf Pg Qc Qd Ru Ry Si Uw Uz Vb Vh Wc Wd We Wg Yl Xa Ti) Ux(aG aH aJ aU aW bB bC bP bQ bW cE cI Co cS Cu CX cY Dd Dr Et Ez Fc Gc gP Ho Ic iH IJ iO Iv Ji Kc Kg Ki Kq Ld Li Mg Mi Mk Mm Mu Mv Ni Nn Nq nY OE Oi Qv Ri Un Wd Ti) Xa(Ad Af aG aH Aj aN aR aZ Bg Bn Bo bX Cq Ct cX dC Dl dM fP gP Hb Hc Hl Ib Ip Iz Jg Jj Jk Kf Ki Kj Kl Ld Lp Lz Mw My Oz Pa Pz Qt Qv Rc Rx Ry Ss Ua Uh Us Uu Uw Vo Vp Vs Yl) nA(Ad Af Al aM As Ba Bg Cp Ct Cu Cv Dc Dd De DK Dp Ef Ez Gl Ha Hc Jd Jj Kg Kj Kl Kn Lz Oz Ph Qh Qn Qt Qu Qw Qz Rc Rj Rm Ss Tn Tv Ua Uc Ue Uf Ur Us Uu Uv Vo Vq Vs Vu Vv) Rx(aA AX bA Ch Cq cR Cs cT Cu Db Dc Dd DR Em Fd Ha Hv Hx IJ In Ir Is It Iv Jn Jq Jr Js Jt Kd Kn Lp Me Mi Mp Mr Mx Na Nb Ny oH Oi Pi Ps Qu Rm Tv Up Uz Vp) Ry(Ad Af Aj As Cp Cu Cw Cx Dr Em Hc Hv Hw Ib Id In Iv Iz Jn Jq Jr Js Kd Ke Kn Kp Kq Kr Lw Mi Mr Mz Na Ny Om Pe Pi Pk Qn Ra Rj Tv Ug Uh Up Us Uu Vp Vs Wg Tl) We(Ad aG Aj As aZ CX Dc Dd De Dr Em Hc Hv Ib Id Ij Iz Jq Kd Ke Kn Kp Lw Ml Mr Mt Mz Nb Nf Ny Om Pi Pk Qa Ra Rb Rj Ug Uh Un Uu Vh Vp Vs Wg Tl) Of(aA Dr Et Gc Hv Ij Ip Ir Jg Ji Jl Jo Jp Jq Js Jt Lh Li Lv Lw Ma Mi Mn Mp Mr Mt Mz Nb Nk Nm Nn No Ns Nt Nu Nw Oh Ok Om On Oz Pa Pc Pe Qc Qd Uz) Yl(Af aG aH AJ aR Ax aZ Bn cN Cu CX De Dk fP Fr Fy Hb Hc Ic Iv Iz Jt Ki Ld Mw Na Nr Nv nY Oi Pc Pe Qn Qv Qz Tz Ua Ug Uh Ur Uu Vq Wb Tj) Dr(aR Dl dR Ed Ef Gl Ha Hf iA Iz Ke Ki Kl kS Lu Nc Nd Ne Nh Nj Nk Nl oF Og Oi

Figure 36 Continued

Figure 36 Continued iZ Jn Jr kP Kq Ky Li Lj Ly Mq mS mU Mw Mz Nd oE Oy Oz Pk Qm Rf St Uh Vt) Oz(Aj aN aW aZ bG cF cU Ed Fw Ij Jl Jr Ky Li Lz ml Mk Mq Mu Mw Mx Nb nC nH nL Nq Nu oE Ow Pf Pk Qd Ql Qw Ri Um) Jo(aW bZ Fr Fw Hw Ih Ij Ir Is kF Kq Li Ma ml mP Mq Mt Mw Mz Nn No NT nU oE On Ow Pf Qd Qe Qu St Uf Uh Vq) nL(aA aH al bB Ed Is Ji Jn Jr kG kK Ky Lh Li Lv Lx Lz MP Mq mU Mx mY Mz nR nT NU oO oQ Qb Qd Qe Vt) Li(Ad Aj Ao aR As Co Hc Ii Ik It Iz Kl Kn kP mF ml Mm Ne nT Oy Qt Qv Qz Rc Ss Tn Uc Ue Vs Wm) Ed(aW cH cN dK Fn Hb Hq iA Kc Lv ME mF ml Mz Nc Nw oE oF Oy Pk Qv Qw Qz Rc To Uh Ur Vp) Is(Ad Aj Hq Ii It Iz Jq Jt Jv kG Kl Kn kP Lu mF Mm nC nH Nm nT Nu Pz Rc Ss Ub Uc Ue Vs) Oy(aA aH aN Aw bB Bo bQ bZ Fw Hw Ir mP Nb Nn No Nq nT nU oE Ow Pf Pg Pi Qd Qu Uh Ut) mF(aG aH bB Bo dR Hb iA Jl Jr Js Lh Lx Mj Mx Nh oE oO oQ Ow Pf Qb Qm St Tz Uh Un Vt) Aj(aW Ez Fr Fw Il Kq Ma ml Mq Mt Mw Nn NT nU Ow Pf Qd Qe Qu St Tn Uf Ut Vq) Rc(aA aH aN bQ dF Dk Fb Fw hB Ih Jn Lh Lj mU Mw No Nv Nw On Ow Pf Pg Pk Qm St) kP(aA Ih Ir Jl Jn Jr Js Ky Lx Lz Ma Mq Mw Mx Mz Nb Nn No Nr Ny oQ Pf Pk Qe) Uh(aA As aY aZ bN cB dH Fn iZ kC kF kK Ko Mn Mp mU Nd Nj nR Pk Qn Up Vs) St(Ad Bn cN dJ dR Id Ii It Iu Iz Jr Jv kG Kl lX Mb Mr Nm Nv Oe Qn Rm) oE(aN Ar cJ cQ Hq kG kK kR Ky Ld lW Mz Of Pi Pk Qw Ue Um Vs Wm) ml(aA Ad Bo Ct Dg hB Kg kl Kl Ky Lj Lz MY oQ Qb Ss Uc Ue) Qn(aJ Cs Fp hB iZ Jn Kq Ky Lj mU Nw Qb Qd Qe Ql Tz Un Vt) Ow(Ad Ao Bg Ch Ct Dp Hc Ib Ii Iz Kn Kp Of Ok Qw Qz Ss Vs) Fw(Ad dR Hq Ib Ii Iz Jr kG Ky Oe Oi Pz Qv Qw Ss To Ur) Nn(Ad Hc Ii Iz Jr Jt Kg Kl Kn Mg Nm Qz Ss Uc Ue Vs Wm) nT(aA Jn Jr Lj Lz Mw Mx Mz nC Nd NH Nw Of Pf Qb) Kq(Ad Ao aR Bg Ch Ik It Iz Kl mT Qz Ss Uc Ue Vs) nH(aA Jn Jr kG Lz Mh Mq mU Mx mY nU oO oQ Qb Vt) Ur(aN aW Dc Il iO Jm Lj Mx mZ Nd Pa Pf Ph Ul) nC(aA aH bB Ji Jn Jr kG kK mU Mx oQ Qb Qd) Mw(aA Ib kG Ml Nm Nu Of Qt Qv Qw Ue Vs) Bo(AN aW Ch Dd Hq kG Me oF Ub) Jn(Hc Ib Ii Lu Oe Qv Qw Ss Up Vs) Jr(Il Jm Kd Lj Mt No Nu Oe Qe Qv) Vt(cF Fn kG Mz Nu Pi Pk Qv Ub Ue) Um(aH aW bB bG cN Ij Kp Pk Qm) aN(Dp dR Gz iA Kp Ks oQ Ql Qv) Mq(aR Ml mW Pa Qt Qv Uc Vs) Ue(aW bB Kc Kz Mp Nw Pj) Qe(Ii It kG Mm Mr Nm Pz) Vs(bB bZ Co Fr Jh kF Nq) aH(Ar Bg Ld Oe Of Pi Ri) Ad(Cw Fr Lj Mt No Pf) aA(bB dR kG lX Ml Mz) aW(Dp Gz Kg Ky To Ub) mU(Ib Lu Ne Qw Vp) kG(aZ Fp Lj Ml Qb) No(Ii It Iz Mm) Nu(aR Il Js Ml) Mt(Ii Nm Of Ss) Qd(Ao Ch Lu Nm) Ky(aZ kN lX Ul) Ql(Bn Hr Oe Oi) Pf(Hc Ii Lh Ok) dK(Ar oO oQ Un) Iz(Fr Nq Ut) Ss(kF Nt Nw) Qv(aY Oa Pk) Oe(Js Qm Tz) bB(bM mE Of) hB(Bn mE Nd) Ml(kF nU) Ub(Ke Nw) Un(aZ Pa) Pi(aI mS) Pk(Ib Jf) oQ(cF oP) ArId ChUt DeQy NqJh NrPz MvOf NdTo HrQm IiJs RboF QbkF QzbZ KgVq PakK aJbM dRiZ nUmZ} Ru{Ld(aA aP AX aZ Bb Cp Cq Cs Cu Dd Dk Dr Ed Fd Fp Fy Gb Gc Gd gL Gp Ha Hb Ho Hp Hv Hx Ih Ij In Ir Is It Iv iZ Jh Ji Jl Jn Jp Jr Js Jt Kd Ke Kn Kq Lx Me Mi Mj Mt Mw Mx My Mz Na Nb Nj No Nr Nt Nu Ny Oa Oh On Oy Pc Pe Pg Pi Pk Po Ps Qc Qd Qe Qh Qy Rb Sr St Tv Tz Uf Uh Un Up Uz Vp Vq Vs Vt Vw Wb Wc Yl Xa Tj) Kq(aA Ad aF AO Ar AX aY aZ bF bM bQ bR bZ cE CH Co Cs cV De dF Dg Dp Dr EF Ez FP Fr Gd Gl HB Hc Hq Hx Iv Iz Jj Jn Jo Js Kf Kg Kj Kz Lz Ma Mh Ml Ms Mv Mx My Ng No Nu Nv Ny oE Oh Oz Pa Pc Qb Qw Qx Qz Rz Sh Sr Ss To Tz Ul Ur Us Uu Ux Vb Vc Vo Vs Vt Wb Wf Wh Zw Xa) Vt(aA AF aN aY aZ bM bN bR Cp Cs Cu CX Dp Dr Fi Fp Fw Ha Hf Ho Hp Hq Hu Hv Hw Hx Ij Is It Iv iZ Jh Jn Kz Lj Lt Mi Mr Mt Mv Na Nb Nh No Nr Nt Nu Nw Ny Oa On Oz Pc Pe Po Ps Qd Qe Qv Qw Qy St To Ub Uf Uh Ur Ut Wb Wf Xa Th) Mw(aA aG aH Aj aM Ar aX aY Bg bR cH cM Cs cV Di Dr Ed Eq FP Fw Gc Gd Hb Hu Hx Ir Is Iz Ji Jj Jk Kj Kl Kn Kz Lx Mi Mk Mr Ms Mu Mz Nd Ne No Nu Nw Ny oE Oy Oz Pc Po Ps Qu Qz Ss To Tz Ua Uh Ul Un Ur Us Uu Vc Wb We Yl Xa) Qd(aA AF Aj aO Ar Ax aZ Bg bM bN bO Ch Cs cV CX Ed Eq fP hB HC hG Hl Ij Iv Iz Jf Jj Kj Kl Kz Lj Lz Ml Mq Mr My Nb Nf Ni Nu oE Oh Ow Oy Oz Pa Pb Pc Ql Qu Qv Qx Ra Rf Sh Sr St To Ua Ur Us Uv Vs Wf Zw Xa Wm) Ed(Af aG aM Ao aQ aU aW bC bH bJ Bn bW bX bZ CO cP cR cX cY dI dR Ez Fw Gp Hx Iu Jd Jh Ji Jy Kc Kd Ke Kg Mg Mi Mm Mp Mq Mr Mt Mu Mv Na Nc Ne Nf Ni Nk Nn Nq Om Oz Pa Pc Pd Qw Qy Rh To Uf Ug Ur Wd Xa Tj) Fp(aE aG aM aY aZ bR CH cM CO cV Cx Dr Fw Gc Ho Hv Hx Ih Is Jh Ji Jj Kc Ke Kz Mg Mi Mk Mp Mr Mt Mz Nb Nd Ni Nn No Nq Nt Nu Nw Ny Om On Ow Oz Pc Pd Pj Ps Ql Qy Sh Sr St To Tz Uf Uh Un Ur Vc Vq Wb Wf Xa) Iv(aA Af Aj aM aS aZ bJ bM bR cM cQ CV Cx Dr fP Gc Hc In Ji Jj Jo Jy Ke Kp Ky Kz Li Lj Lz Mk Ml Mq Mr Ms Mz Nb Nd Ne Nf Nk Nl Nu Nw Ny Oa oE Of Ow Oy Pa Qa Ql Qm Qx Qy Rh Sh Sr To Tz Uh Un Vb Vc Wf Xa) Mq(aA AX aZ Ch Cp Cq Cs Cu Dc Dd Em Eq Fd Fy Ha Hb Hv Hx Ij In Ir Is Jn Jq Jr Js Jt Kc Kn Lx Me Mi Mj Mr Mx Nj No Nr Nw Ny Oa Oy Pe Pg Pi Qe Qh Rb Rv Sr St Tv Tz Uh Up Uz Vp Vq Wb Wc Xa Tj) Ur(Ax Cp Cq Cs Dd Dr Fd Fw Fy Ha Ho Hp Hv Hx Ih Ii Ij In Iq Ir Is It Ji Jl Jn Jq Jr Js Kd Ke kQ Lj Lx Mi Mr Mx Nb Nh No Nr Nw Ny Oa On Pe Pg Pi Po Ps Qb Qe Qh Rm Sr St Tv Tz Un Vp Vq Wb Xa) Ke(aF Aj aM aY bM bR Ch Cs cV fP GL hB Hc Hf hG Hp IZ Jj Kf Kg Kj Kl Ko Kp Kz Lj Mn Mr Nb Nc Ne Nf Ni Nl Nu Nx Oa oE Op Oy Oz Pc Sh Sr To Ub Ul Up Uu Uv Vh We Wf Wh Xa) Nw(aA AF aO bJ Bn Cs cV CX Dd dH dI Dp Dr Em gL Ho Hp Hu Hv Hw Ij Ik iZ Jh Jn Kz Li Lj Lz Me Mi Mr Mt Nb Nd Nh No Nt Oe oN Oz Pa Pc Qn Qw Qy Rv Sj Sr To Uu Vq Wb Zw) Un(aA AF Aj aO aY aZ bN cH Cs CX Dp Dr Ex Fw Gl hB Hc Hf Is Jn Jr Jy Kl Kp Ky Kz Lj Lp Lz Me Nh Nu Ny Oa oE oF Op Ow Oz Pa Pc Qw Sh St To Ug Uu Wb Wc Wf Yl Zw Tm Xa) Kz(aA Aj aX aZ Bo Cs Cu DK Fw Gc Hb Hv Hx Ij Is Jd Jh Ji Jj Jl Jn Jp Li Lj Mr Mt Mv Nb Nd No Nq Nt Nu Ny Oa Om On Pe Ps Qa Qe Qy Sr St Uh Ut Zx) Qy(Aj aX aZ Ch Cs Dg Eq Ex fP Fw Gd Hb Hx Is iZ Ji Jj Jn Jr Ki Kl Lx Lz Mj Nb Ny Oh Oi Oy Oz Pe Po Ps Qb Qe Sh Sr Ss St Tz Uh Uu Ux Vo) Ql(aA Ax aZ Cq Cs Cu Dc Dd Dr Fd Ha Hv Ij Is Jn Jr Js Jt Kd Kn Lp Lx Me Mi Mr Mx Mz Na Nb Nj No Nr Pg Pi Ps Qh Tv Tz Up Uz Vp Wb Zw Xa) Dr(aP Ar Cs cU dR Et Gc hB Hv Ij Is Jn Js Ky Lh Lx Lz Mp Mt Nb Nq Oh Om On Ou Ow Oz Pe Po Qa Qc Qe Qx Rx Si Sr Tz Uh Ut Tl) Mr(Af Aj Ar aZ Bc Bo Cv CX dI dM dR Gc Hb iP Ji Li Lz Mk Ml Nb Nq oE Ow Oz Pc Ph Pj Qb Qv Rh Rx Ry Ug Uh Wf Zw) Ny(AF Ar aX bJ bW CO CX Gc Ho Hv Jh Ji Kc Li Mg Mi Mk Mp Mt Mu Ni Nq Oz Pa Pc Pd Pj Qv Rx To Uf Vq Wf) aZ(aF bJ bW Co cS Cx Ef Ez Fw gL Ho Hv iO Iu Jh Kc Kg Li Mg Mi Mp Mt Mu Nf Ni Nq Nt Nu Om Oz Pd Pj Qe Uf Vq Wd) Cs(aF bE bJ bW Co cV Cx Ez Gc Ho Hv Jh Kc Kg Mg Mi Mp Mt Mu Mv Ni Nn Nq Nt Om Oz Pc Pd Rh Rz Sr Uf Uh Vq Wd) Nq(aA aF Aj aO Bg bR Ch Eq fP Fw HC Hx iZ Jn Kd Lj Me Mx No Oa oE Oy Oz Pi Qu Sh Sr Vc Wb Tm Xa) Hv(aA aH Aj Ar bM Ch Eq fP Gd Gl hB Hc Hl iZ Jj Jo Lj Nb No Nu oE Oy Oz Pa Pc Qm Sh Sr St Uu Wf Xa) Li(Aj bO cF Dg Eq Gd HC Hf Hp Hx iZ Jn Jo Kg Kj Kl Me Mg Mm Ng Oy Pc Pe Pk Ps Qu Uu Ux Wb Zw Xa) Xa(Ad Af Aj Ar aS bA Bo cQ cT cV Cx Dp Gz HB Hx Ji Jj Jo Kl Og Oz Pa Pc Rh Rx Ry Uh Vs) Pe(aA AF aO aY bM cA cK CV dI Gc Gh Hc hG Ii Nf Pa Pc Qv Rh Sh Tn To Ug Uu Uv Vz Zw) iZ(aG aQ aU bR Co cQ Cu dR Et Gc Hb Ho Hw Kc Kg Lu Mi Mk Mp Mz Na Om On Ou Pc Pd Pj Si Uf) Wb(aM Ar Cx Dp Gc Ij Is Js Lh Lj Lx Lz Ml Mp Mt Oh Ou Ow Pf Po Qa Qb Qe Qg Qx Sr Tz Uh) Jh(Af aX Bg Ch Dg Ef Eq fP Gd Hc Iz Jj Kj Kl Ng Nu oE Oh Oy Oz Pc Qu Sh Ss Uu Vo Wf Wh) Fw(aA Af Aj aY bM bO cQ cV Cx dR Gd Hc Hx Ji Jj Ms Nf Oy Pa Pb Pc Rh Sh Ug Vo Wf) Hx(aN Ar Bo cO cV Cx Gc Hu Ih Lx Mi Mk Mt Nu Ow Oz Pc Pf Qv Qw Rx Ug Uh Um Zw) Ps(aO Ar CX gL hB Jj Lz Me Mk Nu Oz Pa Pc Qb Qn Qv Qx Rx Sh Sr Uh Uu Vo Vs) Oz(Cu Dd Dk Ef Hq Id Ik Is It Ji Jk Jl Jr Mv Om On Po Qe St Tz Uh Ut Vq) Mi(aA Aj Ar aX Bo Cx Eq Gd HB Jj Jn Jo Kj Nb No Or Qa Qb Qm St Uv) Sr(aA Aj bH bM Gd Hf Hl Ji Jj Ky Mv Og Oy Pa Pc Rh Sf To Ug Uo Vo Vz) No(aF aO Em Ez Gc Hc Ho iH iO Mk Mp Ow Pa Pc Rh Sh To Ug Wf Zw) Ij(aA Aj bM Cq Cv Hf Ii Jj Kp Nc Nf Ni Pa Pc Rh Sh To Ug Zw Tj) Ji(aA aE Af aY bM bO hB Hf hG Je Jf kS Lj Nb Ni Nu Oa Uu Uv Zw) Is(aA Af Ar aY bJ bM Cq CV Cx Jj Nc Nf Ni Pa Pc Sh Wf Zw) Qa(aA AJ bM bO Cq Hc Iq Jf Jj Kl Ni Oy Pa Pc Qv Sh Uo Zw) Mt(aX bM Dp Eq Fr Hc Iz Kg Kj Kl Me Oy Pc Sh St Zw Tm) hB(Ax Cp Cu Gb Ho In Jn Jt Kn Mz Na On Pi Po Qe Uh Vq) Nb(aS bW cC cP Cv Gc Jj Kp Mp Mu Nf Pa Pc Ph Rh) Lj(aC aG aN bE bJ bM cO cV Cx dI Jd Jy Mp Rx Uf) Jn(Ar bJ cO CV Jj Mu Nf Ni Pa Pc Uf Ug Zw) Cu(Af Aj Ar Cx Gl Hc Jj Kl Kp Pa Uu Vo Vs) Nt(Aj Dg Hb Jo Lz Ml Or Pc Ph Qb Qx Tz Uh) Pc(It Jd Jl Js Mv Nu Oa On Po Qe St Ut) Af(Et Gc Js Oh On Ou Ow Po Qe Vq) Nu(Gz Hb Jq Mj Nh Ou Qb Qe Tz Uh) Mv(Aj Ch Hc Jj oE Oy Sh Uu Wf Wh) aA(cQ Cx Gc Lx Mk Po Qe Si Uh Vq) Jj(Ef Fi Gc Ho Om Ou Qe

Figure 36 Continued oN Pc pF Pi Qd Qe Un Vq Vt Wb Wd) Nt(aM aX aZ cH Eq Fw In Is Ji Js Ke Ki Ld Lh Li Lj Lx Lz Mj Ml Mq Mx Oa Oh Oi Or Ow Pc Pe Ph
Qb Qd Qe Qg Qx Tz Vt) Nr(aA aS bH bJ Bo cT Cx Ed Fw Gz Hu Hv Is Jd Jy Kq Ld Li Mq Mu Mv Ni Nq Nv Oa Oz Qd Qe Ql Qm Rh Uh Un
Ur Vt) Jn(AF aM aS aW aY bG bH bJ BN cO cV Db dI Ed Fc Fw gL iZ Jd Je Ki Mq Mr Mu Nc Ni Nl Nq Nu oH Rj Rx Wb) Pe(aA aD aE AF
An aY bM Bo Dd De Dr Ed Ex Fc Gl Gn Hu Id iZ Je Ji Jk Jm Jq Ky Lz Mu Nj Nx Oa Po Um Zw) Ld(Al AX Bb Cp Cq Dd Ha Ho Hu Hw Ii Il
Iq Jg Jk Jm Jp Js Ki Lp Om Pc Pg Ph Pi Qh Tn Tv Uv Uy Vt Wb) Mq(aE Al Bb Cp Cq Dd Ed Fd Fw Ha Hu Il Iq Jg Jk Jp Jt Ki Lp Lx Nu Oa Pg
Pz Qd Qe St Tv Uy Wb) Kq(AN aQ aW Bn Cx Ed Fc Fw gL Il iZ Jm Kd Ki Kl kR Li Lp Mh Ml Nu Oa Po Qn Qw Us Vs) Om(aA AF aN aY
BN Ch cL cV CX Dc dH Dr Eq Fw Hx iZ Ni Nu Oa Of Oy Oz Pb Ur Uv) Mr(aN aW Bb Bo Cx Ed Ic Il iZ Jm Li Lj Lp Mx Nu Nx Oa Oz Pa Pz
Qc Rj Rx St Us) iZ(aQ Aw bB Co Cp Cu Et Gc Ho Is Ji Js Ke Mn Mx Oh Ow Pd Po Qe Si Uh Ti) Fw(aA aM Cu Et Hp Hu Hx It Je Ji Jl Ke Mv
Na Nf Ni Po Qe Ql St Un Wd) Nu(aM Et Hx Is Ji Jl Ke Li Lx Mj Mx Nv Oa Po Qb Qc Qd Qe Qh St Un Vt) Oa(aC Cp Dl Ef Gb gL Hw Ib It Iz
Jd Jg Jy Mu Ni Ql Qw Ue Vb Vw Wd) Cx(Cp Cu Dc Dd dM Dr Ed Ii Ji Jq Jr Jt Ke Lj Mi Mz Ok Pi Un Vt) Hu(Ax Cs Dr Ex Hx Is Ji Jl Js Li Lx
Ml Mx oF Oh Po Qe Qx) Qd(aA Ax bQ Cs cX Il Js Kd Kk Ml Mx Ni Oz Pa Qx Tn) Ke(Af aN aW aY bJ BN De gL Nj Nx Rx Us Uv Wc)
Qe(aA aN bJ Bo bQ dl Dp fR gL Gn Je Ni Oe Qw) Nv(aF Cs cX Dr Fp Hx Lj Lx Mx Ni Oe Oz Qn Qw) Vt(aF aN bJ Bn Cu Dp gL Il It Lx Pk
Rg Rh Wm) Ed(Af Bc Bn fR It Mu Nf Po Tn Ur Uw Wd) Mx(aY bH bJ cZ Jd Mv Ni Nq Ql Wb Wd) Ni(aZ Il Is Kd Lj Lx Oh Qb St Uh) Lx(Dd
Dr Fc Hp Ib Jc Jk Mu) Is(aM fR Je Oz Qw Ub Wb) Jk(Ar Cs Fp Ml Oz Qx) Js(aY bJ Bo Mu Nq Wb) Ql(Bb Cq Il Ki Lp Uy) gL(aM Eq Ib Ml
Rm Un) Cu(Bo Gl Oz St Uv) Kd(Cs It Jd Jl Jy) Po(aN aY bM Uv) Wd(Ch Eq Oz Pb) Lj(fR Ib Je Uw) Mv(Dc Ul Uy) St(aP Cw Hw) Li(cC Hp
Ib) Un(aW aY Il) Af(Ow Uw) Bo(Dr Tn) Cs(Bb bJ) Dd(Ml Nq) Fc(It Jr) Hx(Il Qw) Jd(kR Pa) Jl(cV Qw) Ul(Fp Nq) Oz(oF Tn) aY(Ji Ow)
hB(aF Lp) ChEf DrGc Eqlz MuOh HvaN} Rx{Lj(aA Ad aE aP As Aw Ax BA Bc Bg Bn cM Cp Cq Cs CT Cu Cv Cw Dc Dd Dk Dl dM Dr Ef
Em Fd fR Fy Gb Gn Ha hG Hl Ho Hp Hv Hw Hx Ib Id Ih Ii Ij In iO Iq Ir Is It Iv IZ Je Jg Jh Ji Jk Jl Jn Jo Jp Jq Jr Js Jt Jy Kd Ke Kf Kj Kk Kn Kp
kQ Kr Lh Lp Lw Md Me Mi Mj Ml Mr Mu Mw Mx My Mz Na Nd Nf Ni Nm No Nr Nt Nv Nw Of Ok On Ou Oy Pa Pb Ph Pi Pk Po Qa Qd Qe
Ql Qt Qx Ra Rb Rg Rj Rm St Tn To Tv Ua Uc Ul Un Uo Up Ur Ut Uw Uz Vb Vh Vp Vs Vt Vw Wb Wc Wd We Wg Tl} Ih(aA aC Aj aK Ap
Ax bA Bg cA cK cM Cq Cs Cu Db Dc Dd Dg DR Em Fd Fp Fy Gc Gh Ha hB hC hG Hp Hv Hx In Ip Is Iv Ji Jj Jn Jq Jr Js Jt Kd Ke Kl Ky Kz
Ld Li Me Mi Mj Ml Mq Mr Ms Mw Mx Na Nb Nd Nw Ny oE oF Oh Oi Or Oy Oz Pb Pc Pi Pk Qd Ql Qv Qx Rc Rh Sh Sr Tv Tz Ub Up Ux Uy
Uz Vc Vp Vt Wb) Nw(aA aF aO Ax bA bF cE Ch Cp Cq Cs Cu cV CX dA Dc Dd Dp Dr Em Fd Fp Fy gL Ha Hp Hv Hx Ij In Ir It Iv iZ Jh Jr Js
Jt Kd Kn kQ kS Li Lp Me Mi Ml Mr Mw Mx Na Nb No Nr Nt Nu Oh Oi Op Pi Qb Qd Qe Qn Qw Qx Ra Rg Sr Tv Ub Up Vp Tj) Ny(Af aO AR
aW Ax aY Ba bE bF BG bJ Bn cE CH Cs cV CX cZ dE Dr Du Ed Fp Fc Gc Hc Hx Ic Ij It Iu Iv Jn Kx Kz Li Lu Lz Mh Mi Mk Ml Mt My Na Nb
Nn Nu Nv Nx Og Oh Op Oz Pd Pe Pj Qa Ql Qv Qx Ra Rf Rg Sh Sr Uf Uu Vp Tl Wm) Nb(aF aO aP AR aS aY bE bF BG bJ Bn Bo bX bZ cE
Ch cO cZ Fp Fw Ha Hb Hc Hx Ij It Iu Jl Js Jy Ke Kp Kx Kz Lz Ml Mw My Mz No Nx Of Og Oh Ow Oy Pa Pe Pj Pk Po Qb Ql Qw Rb Sh Sr Tn
Un Us Uv Vq Vt) iZ(Ax Bb Cu Cw Dc Dd Et Fy Gc Ii Ij Il In Ir Is It Iv Jg Ji Jp Jq Jr Js Jt Kd Ke Kn Ks Li Lu Mg Mi Mm Mn Mr Mx Mz Na Nh
Nr Oh Ok Om On Oz Pe Po Qe Qh Rb Rm Si Sr St Tn Tv Uf Up Uy Vp Vq Vs Vt) St(aA aP Ax bA Cp Cq Cs Cu Dc dM Dr eF Fd Fp Fy gL Ha
hB hG Ho Hv Hx Id Ij In iO Ir Is It Iv Jj Jr Js Jt Kd Ke Kn Kz Li Me Mi Mj Mq Mr Mx Na Nr pF Pi Qd Qv Ra Sh Sr Tv Un Uu Uz Vp Vt)
Qa(AD AF aO aY aZ Bg bM bO bZ Ch Co cV dD Dg Dr Ed Eq fP Fr Hc Hp Iv Iz Jf Kd Kl Li Lv Ma Mj My Nv Nx Of Op Ou Oy Qu Qw Sh Sr
Tn Uo Uu Uv Uw Ux Vs Vt Wb We Zx) Is(aA AF Aj aN aO Ax aY bF BG bJ bM Bn bZ CH Cs cV Cx dA Dr Fp Hc hG Hp It Iv Je Jj Kz Ld Li
Lv Mf Mq Mr Mw No Og Op Ql Rg Sh Sr Ub Uu Uv Vo Vt Wb) Qe(aA Af aY bA bM Cs cT dA Dr Fy gL hB Hp Hx Iv Jj Js Kd Ld Mi Mr
Mx Na Nf Nl Nu Op Ow Oz Pi Ql Qx Qy Ra Sr Uo Up Uu) Ir(aA Af aN bM bO Cs cX dl Dr Fp hB hG Hp Hx Iv Ky Kz Ld Li Mh Mq Mt Mv
Mw Nf Nl Nu Ow Oz Pc Ql Qw Qy Sh Uo Ur Vz Wb) Jn(aC AF aN aO aS aV aY bM BO bX Cq cV Cx cZ dD dl Dr Hc Hf Jf Kz Ld Li Nc Nf
Nl Oa Oz Pa Pk Uo Uv Vp Vt Vz Wb) Js(aA aE AF aN aO aY bJ bM bO cV Cx Dr hG Hp Hu Hx Jh Jk Ld Li Mq Mu Mw Ne Nl Nu Ow Oz Pc
Qd Qy Sr Uo Uv Vt Vz Wb) Oa(aA Af aY bH bJ dD Em Gc Hx Iq Je Jh Jj Jk Jy Kq Ld Li Lx Mh Mi Mq Mt Mw Na Nj Nk Nu Op Pi Ql Qy To
Ub Ur Vz) No(aK aO Ax Bg cA cE cK Cs Cu Fc Gc Gh HC Hv Hx Iv Jr Kd Kz Mr Mx My Na Nd nW Oz Pi Qb Rh Rm Sh Tz Vc) Mw(aA Ax
bA Ch Cq Cs cT Cu Dc Dr Fd fP Fr Hv Hx Iq It Iv Jr Kd Lp Mi Mr Na oH Pi Qb Qu Qz Rm Sh Tv Ux Yl) Ij(aA AF Aj aO aY Bg cA cE cK cQ
cV dF Dr Fc Gh Hc Hp Iz Jo Lv My Nd Ok Op Ql Rh Sh Tn Uv Vc Vt Wh) hB(Ax Cp Cq Cu Dc Fd Ha Hv Ii In Jp Jq Jr Jt Ke Kn Lp Me Na Nj
Pe Pg Pi Qd Qh Rb Tv Tz Uz Vp Vq Vs Wb) On(aF Aj aO Ax aY bF BG bZ CH Cq cV Fp Hc Iv Jr Kd kR Mi Mx My Og oH oN Op Pi Qb Sh
Tn Uv Wb) It(aA Af bM DR Ed hG Hp Iv Jh Jj Jk Kd Kq Ld Mt Nd Nl Nn Nu oE Oh Ow Oz Pc Qb Qw Rm Sr Uu Vt) Hx(aA aN Ax Bo Fw Hr
Hu Iv Kd Kc Li Lp Mt Mx Mz Nn Nr Nu Oh Ow Qb Qw Rm Ry Sr Tz Um Ut Vt) Sr(aA Ax DR Fc Hc hG Hp Hv Jk Kz Na Oi Op Oy Oz Pb Pc
Qb Qd Qy Rm Tz Uo Uv Vc Wb) Mr(AF aN aY Bn cV CX fP gP Hc Jm Kd Li Lp Mf Ow Oz Pb Qb Qn Qy Rm Uh Uv Vt) Kq(Aj AO Ax aY
cE cG Cq cR cV Ef Fr Hc Hv Iz Jr Kd Lp Lv My Nd Og Qb Rm Tn Ux) Qd(aA Ao Ax bA Bg Ch Cs cT dA DR gL hG Iv Mq Na oE oF oK Qx
Ra Rf Sh Ub Uu) Rm(aA aE Dr Ed Fp Fw gL Ha hG Iv Jj kQ Kz Li Nu oE Oz Pc Qy Ub Ur Vt Wb) Dr(aY Bb cQ Cx Gc Iq Jm Kd Mf Mn Oh
Oz Qb Qc Qh Qt Qw Si Tz Vt) Mq(AX Bb Dc Dd Ed I'd Fy Ha Hv In Iv Jt Kd Kn Lp Pi Qh Tv Wb) Li(aZ bB bN bO cQ cV dD Dg Fr Iq Kg Kl
Ma Mg Mm Pi Tz Ub Uo Wb) Ow(Ax Cq Cu Dc Dd Fd Hp Hv In Iv Jr Me Mi Na Op Pi Tv Ub Up Vp) Cs(aN aY Bb bJ cV Hu Jg Jh Jk Kd Ke
Oz Pc Pi Pz Qy Vt Wb) Cx(Ax Cq Cu Dc Fd Fy Ha Hv In Iv Jr Kd Mi Na Pi Up Vp) Ke(AF Aj Ax Ch cV Fc gL Nd Nx oE Ou Oz Pb Ub Uv
Vc) Pe(aO Bg cA cE cK cQ Fc Gh Hc hG Hp Jk My Nd Tn Uv Vc) Mx(aY bE bJ cZ Hp Jh Ld Mv Nl Nt Ql Qy Un Vt Wb) Qy(Ax bA cT Cu
Dc Fy Hv Iv Jr Kd Kn Mi Na Vp) Oh(aA aE aF bM Dd fP Hp Nt pF Pi Un Vt Wb) Oz(Ax Fp Ha Hp Iv Jr Jt Kn Na oF Pi Un Tj) Kd(Fp Jh Jl Ld
Mv Nf Nq Nu Ql Ur) Ax(aY Hp Hu Ld Mu Pc Pi Un Vt) Fy(Af aY Hp Ld Pc Ql Rh Un Vt) Qb(aA Iv Jh Ni Nt Pi Ri Ub Vw) Cu(AF aO aY Gl
Ld Of Uv) Fp(aE Jg Lp Pa Pi Qc Uy Vt) Ql(Dc Dd Ed Jt Lp Nr Qh Wb) Nu(Dc Gc Hv Jq Jr Tz Uz) Na(AF Ar aX Ba Lp Pc Vt) Jh(Aj aX Bg Eq
fP Hc Iz) Iv(aA AF aO Pb Pc) Ut(Aj Ch Eq fP oE Sh) hG(Ha Il Ji Qh Tz Vq) Mt(aX Ed Fr Kl Vs) Ld(In Jt Kn Pi Wb) aA(Gc Iq Pz Qc Si) Vt(bA
Nr Nt Ub) Ed(aW Mg Uf) Ml(Ha Pi Wb) Hp(Lx Nn Pf) Qx(Dd Pi Wb) Jl(aO cV nW) Jt(Aj Jo Kj) Un(Af gL oE) Ar(Lp Pi) Jp(fP oE) Jr(aY bJ)
Om(Aj Uv) Ur(Dc Fw) dR(Ha Vq) BaEq ChEf NnaX NtMj LxaO MvLp TnfP PcoF} Cx{mU(aC Af Aj Al Ao Bb BG cD Ch cL Co Cp Cq Cv
Dc De Dg Dk Dl Dp Ef Ez hB HC Hu Ii Il Io It Iu IZ Jg Jh Jj Jk Jo Jq Jt Jv Ke Kf KG Kj Kl Kn kR Ky Ld mF Mg Ml Mm MS Mt My mZ Nd
Ng Nm Ns Nu Nx nY Of Og Oh Oi Om Oy Oz Pb Pe Pz Qh Qt Qv Qw Qy Qz Rc Rj Rm Ss Tv Ua Ub Ue Uf Ug Uh Up Us Uu Uv Vq Vs Vv)
nN(aC Ad Aj aL Ao Ap aY aZ Ba Bb Bc bW cF Ch cQ Ct Cu dD Dg dJ Dl Dp dR Ef Ez Fb Gz HC Hq Hw Ii Il Iq It Iu iZ Jg Jh Jj Jk Jm Jr Jt Kf
Kg Kl kO kP Kr Ks Ky Ld Ma Mg mH Mj MM mS mZ NJ Nn nR Nx Oe Oi OK Oy Ph Pz Qu Qy Qz Rc Rm To Tv Ub Ue Uf Ug Uh Uv Vq Vu Vv
tF) nC(Ad Af Aj Ao Ap Bb bF Bg cE CH Co Cp Cs Dd De Dg Ef HC Hq Hr Hu Ib Iz Jd Je Jf Jg Jh Jj Jk Jo Jt Kf Kg Kj Kl KR Ks Kx Ld Lj Lz
Mb Mh Ml Ms Mv Mw My Nx Oa Oe Of Oh Oi Ok Om Oy Oz Pb Pg Qb Qg Qu Qw Qy Qz Rb Rc Ss Tv Uc Ue Ug Uk Um Us Uu Vo Vs Vt
Vv) mZ(aA aH Ar aU aW aX bB bE bG bJ Bo cO cS cU Cv dB Dc dK dN Dp dR Ed Ez Fp gL hB iJ Io Iu Jf Jj Jr Ju Jv Kc kF Kg kK kP Kq Kx
Kz Ld Li Mb mF Mg Ml MP Mq MT Mu Na nL Nn nO NU Nx nY Oa Oe Og Oi Oz Pd Pe Qa Qd Qv Rb Ub Uf Ug Uh Um Up Ur Us Uu Vo)
nL(Ad Af aH Aj aN bA Bb Bg CH Cp Cs Ct Dd De Dg Dp Ed Ef Fw Hc Hu Ir Iz Jg Jh Jj Jk Jo Jt Kf Kg Kl Kn Kr Kx Ld Lj Ly Lz Mb Mh Ml
My Nm nT Oa Of Oh Oi Oy Oz Pb Qa Qb Qg Qu Qw Qy Qz Rb Rc Rg Ss Tv Ua Ue Ug Uh Um Ur Uu Uv Vo Vs Vt) mS(aA aP Ar Ax bB bJ

Sr Vt) Eq(Kq Mt Nn Ow Qy) nN(Ad Aj Cv Jo Kj) Nn(Fd Ux Uz Vc) Iv(Vb Vc Wc Th) Kq(Aj De Uu Ux) jK(dM Is Jr Ny) Ed(Gc Zw Ti) Ip(Ma Mn Oz) Ld(Fd Ho Uy) Ti(Nb Oa) Fr(It Oz) Gc(Oa Uu) Lx(Hq It) Mq(Fd Uy) Mt(Ny Ux) Qa(Hr Zw) hB(Fi Ho) jT(Is Jr) AjJt ThFp NsNy MaQc MrWc NbTl HpOw IhOz IlYl SiiZ QbVw UsnU

Constrained panels with 2 analytes, where 1.0E-7 >= 'AUC p-value' > 1.0E-8. Contains 451 panels of 121,819 total panels evaluated. : Uh(Ad aE bA BN Cp Cq Cu Cw Dd Fy Hx Ib Ji Jj Kd Kn Kp Kq Kr Ld Me Mq MZ Nm Nt Nw oE Om Pb Pe Pk Rb Uc Ud Ul Ur Us Vt) Mz(aA Ih Ip Ir Jg Jj Jn Lj Ma Mi Mn Mp Nb nI Nm Of Oh Ok On Pa Ur Uv) Mw(AA Ih It Iv Jg Js Lx Mn Ms My Ns Nt Ny Ok Oz Pb Pf Qa Qb Qc) Lx(aA Ih Ip Ir Jg Jj Jn Lj Ns Ny Oe Ok Oy Oz Pb Pe Qc Qd Va) Lj(aA Fr Ih Ip Jj Jn Lw Mi Mm Mn Mp Mt nI Nt Nu Ny Pg Qa) Va(Ao Ar Cw Dc Dd Ef Et Fp Hx Jm Ko Ld Lh Mq Pz Ql Rf Uc) Ny(Ih Ip It Jj Jp Lw Mi Mr Nd Nm Nu Oe Ok Oz Pb Pe Qc) nI(Ar bB cX Fp Jj Jl Js Kq Mq mU nC Nh Nq oQ Rj St Vo) Jn(Fr Jg jK Ma Mm Mn Nm Nu Oe Ok On Oz Pb Pf Qd) Xa(Af Aj Ar cX Fp hB Hx Kl Nu Ow Pb Pf Qy Uu) aA(Ih Io Jp Jt kP Lh Mm Nj Nt Ok On Qa Qb Qd) Ke(Af Aj De Dp Dr fP Im Jo Kj oE Pb Up Vs) Qd(Aa Ih jR Jt Lw Mm Mn Nn Ns Nt On Ye) Jj(Fr Io It Jp Lh Ma Nr Nt Nv Pg Qc Sr) Js(Fr Hr Ip jD Jt Mn Nt Oe On Ur Uv Vo) Og(Is It Iv Jl Mn Nt Nv Om Po Qb Qe) Aa(Et Hr Is It Iv Ji Jp Nb No Qb) Qa(Ij Ip Jt Ma Nk Oe Oy Oz Pb) Jg(Fp It Ng Ns Oe Oz Pb Pe Qc) Jp(Fp Is Ns Nt Nu Oe On Oy Pe) Qb(Ij Jt Ma Nm Nt On Oz Wd) Nw(aF bN CX dH dK Fy jH) Ip(Fp Fr Ih Jt Nt Nu Pb) Pe(Io Iv kN Mm Mp Nn Oy) No(Aj Bb Gh Ur Uu Vo) Jt(Fp Hr It Jo On Pb) Ok(Ih Mn Nd Ns Qc Qe) Pf(It kP Lw Oz Pb Qc) Fr(Ih Oe Oy Pb Qc) Ir(Io Lw Mm Mp Nn) Ps(Cs Pc Po Ra) Rt(Kd Mi Nr Ut) On(Hr Ih Ms Ng) Pg(Nm Oy Oz Pb) nN(Af Dp Kg Us) Aj(Bb Ij Ut) Is(Ij qY Uu) It(Ma Mn Nv) Wb(Ld Mq Nr) Sh(Jh Qy Rm) Qe(Nm Ru Ur) Ji(De jO jT) Uy(hB Nn Ql) Cs(Rx Vi) Dr(Kd Rm) Nq(Lp Ru) Nt(Qc Wf) Nu(Ih Mn) Mr(jK Rx) Jq(jO jT) Uu(Et Sr) ArHo BomS DcUr TiFp EqSt GciZ LwjK MaIh MvRu HpOz IjVo LikP UsmU VtbN jIjT Constrained panels with 2 analytes, where 1.0E-6 >= 'AUC p-value' > 1.0E-7. Contains 613 panels of 121,819 total panels evaluated. : Mw(Aj Bb Bg Ch Fp Fr Io Iq Is Jp Jt Lw Ma Mi Mt Nb Nm Nr Nu Nv Oe On Pa Pe Pg Qe Uh) Uh(Aj aM Cs dK eF Ih Im iZ Jo Jt Li Mi Mj No Oe Oh Qd Qe Rf Ru Un Ut Va Vs) Nu(Aa Fr Iq Is It Jg Jj Js Jt Lx Ma Nd Nv Ok Oz Pf Pg Qa Qb Qc Qe Sh) Mn(Fp Fr Ih Jg Jq Lw Lx Ma Mi Nm Ns Nt Nv Ny Oy Oz Pb Pf Pg Qa Qb Qc) Va(aA Dk Dl Dr Ho Hu Il lZ Mr Mv Nm Ok Ou Pg Pi Po Qm Tn Uf Vh) Lx(Io Is Iv Jp Js Jt Lw Ma Mh Mi Mr Nb nI Nm Nn Nt Of Oh Qa Qb) aA(Bb Iq Iv Jm jT Lw Me Mp Nn Ns Nv Oe Og Oy Pb Pe Pg Pz Qe Si) Fr(Aa Aj Hu Is Iv Jt Mi Mz Nc Nd Ng Nm Ns Nt Ny Of Ok Qa Qb) Jg(Hu Ik Is Iv Jp Jq Lw Lz Mg Mi Mp Mx My Nd Nt Oi Ok Po Qe) Lj(Io Is It Iv Jh Jl Jq Lh Mg Nb Nn Nq Og Om Oz Pb Qb Qc) Ny(hX Iv Jn Js Lv Ma Mp Nb Nn Nr Nt Oh Oy Pa Pg Qa Qb Qe) nI(Af aH aJ aP hB Ky mF Ml mP Mr Mv Mx nR Ow Qv Ug Um Vt) Mz(cX Hv Hw Io Iv Jp Js Jt Mh Mr Mt Nf Nr Pg Po Qa Us) Ip(Io Is It Iv Jn Mi Mt Nd Nm Nr Nv Pf Po Qb Qc Qe) Xa(aF aM aW Dp Eq Nr Nx Qc Qd Ql Rc Rj Sh St Un) jK(Ih Im Ir Ji Jj Jq Md Mt Nb Nm On Pe Qc Qe) Jn(Ih Js Jt Mt Nd Ns Nt Nv Pg Po Qa Qb Qc) Jp(Iv Jq Jt Lw Ma Mi Mp Nm Nn Oh Ok Po Yd) Oz(Gc Is It Iv Jt Ke Ma Mt Nt Nv Pa Po Qe) Pf(Iq Iv lX Mp Mr Nb Nj Oh Oy Pa Pe Yd) Ih(Fp Io Mm Nm Nt Nv Oy Pb Pg Qa Qc) Js(It Jo Lw Mi Mp Ms Ns Oy Qa Yd) Ok(Io Is Jq Jt Lw Ma Mi Mp Nn On) Jj(Ii Iq Is Kq Nm nN Po Ps Pz) Og(Aa Iq Jk Lh Ma Mi Nm Nq Nr) Pe(Jq Jt Lh nA Om Pc Pg Ur Uu) Nt(Eq Ik Ly Nd Pb Ps Qa Sh) Ji(Aj Bb bN qY Ru Us Uu Uv) Ma(Fp Is Iv Mi Ns Pb Qe) Yd(Cu Lh Pj Qy Si St Vt) Jt(Aa Is Iv Oe Of Oy Qc) Nm(It Iv Nr Of Qa Qc) Qd(De Jq Lh Mi Mp Pc) Ru(Hx iZ Jh Jl Ld Qy) Nv(Fp Ns Oe Pb Qb Qc) Nw(Cu Ed Ho Jv Sr Ur) Pg(hA It Lw Mp Ns Qc) Bb(Et Ij Jo Oy Qa) Wb(Ar Ml Qb Qx Rm) Qe(jT Lw Mi Pb Uu) Kq(Dr Iz Jo Ss Vo) Ps(aM Fp Kl Kx Mk) Rt(Cp Dd Fy Hv Mx) On(Ik Lw Mi Mv Qa) Ur(Ij Iq Ir Is Sr) nN(Bg cX De Ks Vs) Aj(Ba Li Om Sr) No(Hb Iz kP Ss) Wf(Ke Nr Un Vt) Rx(Ax Fy Ha St) Ut(Ch Dr Eq Uu) Aa(Lz Mi Nn) Fc(Cs Fp Tz) Gc(Qv Qw St) Ho(Bo iZ Oh) Im(Dr Hb Ou) It(Io Mt Qc) Qa(Mm Ns Vs) Ke(dK Lh Oy) Li(lX mZ Vo) Pb(Is Po Qb) Af(mU Uw) Ar(Fd Uz) Eq(gL Mq) Hb(Fy Ld) Ir(Mi Pc) Sh(Nr Om) Qy(Dr Ux) dK(oO oQ) kP(Oh Us) CuWc FdhB FpUy MmQb HrLh IjbN IsOe QckG Constrained panels with 2 analytes, where 1.0E-5 >= 'AUC p-value' > 1.0E-6. Contains 839 panels of 121,819 total panels evaluated. : Va(aE aH aZ Co Cp Cs Fc Fi Fy gL hB Hv Jp Jq Kf Kk Ks Mg Mi Mk Mn Mp Mx Mz Nh Nq Pc Pd Qh Ua Uw) It(Fp Ih Iq Iv Jh Jn Lh Lv Lw Mi Mm Nb Nd Nq Nr Ns Nt Om Pa Pb Pe Po Qb Qe Ru Sh) Mn(Aj Hv Hw Iq Is Iv Jl Jt Lh Mm Mp Mr Ms Mt Mx Nb Nd Nn Nr Oe Oh Om Pa Po Qe) Ma(Aj Fr Hv Ik Jl Jq Jt Lh Lw Mp Mr Mt Nb Nd Nm Nr Nt Nv Oe Of Oy Pa Pe Po) Qb(Bb Di Fp Io Iv Jh jK Lh Lv Lw Mi Mp Mt Mz Nn Ns Oe Om Oy Po Qc Ru Xa Ti) Jj(Dc Fb Fp Hb Il Iv Jk Jl jT Ks Mt nC Nn Om Oz Pf Pj Qh qY Rf St Ut Vq Vt) Bb(aH Ax aZ bA bN Cs Cx Dp Is Jp Js Li Ml Mz Nb Og Pb Pe Qd Qe Ur Uu) Qc(Di dK Fp Is Iv Jl Ke Ld Lh Lv Mi Mm Mp Nd Om Pa Pb Pe Po Qe Uh Ur) Oz(Fc Fi Fp Ho Jh Jl Lh Ml Mm Mp mZ Nb nC Nm NN Nr Og Om Si Vw) Ip(Iq Jl Jq Lh Lw Lz Mm Mp Mr Mx Nb Nc Nn Nq Oh Om Oy Pa Pc Pe Pg) Nn(Fr Hb Ih Jg jK Jn Js Mw Nd Ns Nv Oe Oy Pb Pc Pf Pg Qa Qe) Mz(cH De Dp Ed Fp Gp Hb Is Ld Lh Mm Nt Nv Om Pc Pz Qe qY Uu) Ur(Dd Fw Fy Ho Ih Il Im Ji Jr Jt Kd Kq Nb Nt Pg Qa Qh Ut Vt) Fp(aA Fr Ho Io Is Jn Lw Mm Nd Nm Nt Nu Ny Og Om Pb Pg) Qe(Aj bN Io Iv Jn Jq Mm Mp Mt Nd Ns Nt Oe Ou Oy qY Vo) Ld(Ed Gc Gp Ij Im Is Jr Js Mw nI No Pe Qa Qd Sr Uz Wf) Ih(Iv Js Jt Lh Lv Lw Mi Mp Mr Mt Nk Ns Oe Om Pe Po) Nv(Hu Iv Jq Ke Lw Mi Mp Mr My Nd Nm Of Oy Pe Sh Wf) Qa(Aj jK Jq jT kP Lh Lw lX Mi Mp nA nD Pc qY Uu) aA(cX Gc Hb Is lX Mg Mi Mt nK Om Pc Po rB Ru Ti) Nt(Hb Iq Is jK Jq Jt Mi Mp nI Ns Oe Pe Uu Wh) Og(Hx Ii Il Io Jh Lw Mm Mp Mr Mt Mv Mx Nb Pa) Nu(Io Lp Ly nN Nr Oe Om Pb Pe Po Ru Uz Wb) Mw(aZ Cv Jq Lh Lv Mm Mp Mr Mx Nj Oh Om Po) Jn(Is Iv kP Lh Lw Mi Mp Ms Nr Oh Om Pa Pe) Pf(Eq Hv Hw Io Jh Jq kN Mx Nc nD Op Pc Pz) nI(cH Cs cU Hw iA Ji kF Kj Lz Mj oF Pk Un) Aj(Ad Ap Dc Ir Is Js Ok On Qd Tn Tr Uc) Lx(jK Jl Jq Lh lX Mm Mp Mt Om Pa Vc Yd) Xa(bJ Ch Ji Kd Kz Mh Mk Of Ru Uh Ul Wf) Kq(Ad Bg Ch Ef Kj Mm Of oH Pb Uv Vs We) Lj(Hv Hw Jo Lv Mr Nd Ns Oh Pa Pc Pe Po) Pg(hX Io Iq Iv Jq Mm Mr Mt Nr Oe Pc Uu) Ke(Ad aE aY Ii Il Iz Jh Jm Kf Ne Vp) jK(Ij Iq Jt Li Lv Lz Mi Mp Oh Ok Pc) Sr(aE bN Hb Hc Hq Jo Oe Ss Uv Vo) Ny(Hv Hw Is Jt Lh lK Mm Om Pc Po) Dr(dR hB Li Nb oE Ps Ru St Vq) No(cX Gc Ha oN Ou Ow Uv Vs Vv) Ij(aZ Ch Ct Hb Hc Ou Qw Uu Vs) Uh(cH Hp Ki Ko Nk Oi Ou Uv Vo) Pb(Iv Lh Mm Mr Nb Nm Nr Om Pa) nN(Bo hB mZ Nh Oy Ph Tv Uu Vv) Et(Bg bN Ch Dg jO Kl Uv Vo) Pe(Fr Jl Mt Nr Po Ss Vo Vs) Jg(Hv Hw Jt Lh Mr Oh Pa) Fr(Hv Jq Lh Lw Mp Mr) Nr(Iv kP Mi Mm Oe Oy) Mt(hX Iq Jt Nd Nm Oe) Jp(Hv Hw Lh Mr Pc Uu) Ru(aZ Gc Hb Mq Po St) Sh(Gc Ir Ju St Vq) Jh(Gd Iq Nd Oy Uy) Ut(Hb Lp Uv Vs Wb) Uu(Ir Ko On Qd Un) Nm(Iq Is Oy Pa) Ho(aZ Cx Kj St) Im(aU cH De Ow) Js(Lh Pc Us Vs) Jt(Ct Mp Ms Ns) Po(Hr Io Oe) Mq(mZ Uz Wf) Is(bN Ns Oy) Iv(Io Iq Nd) Yd(Ou Un Uw) Wb(aP oE Vt) Qd(bN mZ Ti) Ji(aW cX Vo) Rx(Cu Hx Na) Li(bO nD Vs) Rt(Hw Mr Pi) Nw(Ra Ul Vt) iZ(Uy Ye Ti) jT(Ir Lv Ml) Cx(Fd Gb) Eq(On Pd) Gc(hB Ub) Wf(Cu Tn) cX(oQ Uw) mS(oE Us) qY(Jq Lz) BomZ CwGd DeOn EdHb GbhB MiIo MljV NiPs HpaW HrPa IrLt SioE StUz WdaZ LhOf UnbN UxVq aNnK Constrained panels with 2 analytes, where 1.0E-4 >= 'AUC p-value' > 1.0E-5. Contains 1,011 panels of 121,819 total panels evaluated. : Qc(aH Aj aZ BA Bb cH cT Cu cX Dc Dd Dr Hw Io Jh Jq Ki Lw Mg Mr Mt Mx Nb Nj NN Nq Nr Ns Nx Oh Oz Sr Un) Bb(aM Bg CH cS Cu cX Dc Dd Di dK Ih Ir It Iv Jn Jq Jr Jt Lj Lv Ly Mi Mm Mn Mt Oe Of Oi Oz Va) Jj(Ad Co Ed Fi Fw Iu Jh Jo Kd Ko kP Ld Mi Mm Nc Ng Ni nL Nq Oa Og Pa Pb Pk Qy Rm Tn Tz Ua Uc Un) Ld(Dc Et Fw Il Ir Ji Jn Jp Jq Kd Kq Li Lj Mt mZ nN Nr Ny Oh Pg Pi Pk Qb Qe Qh St Ut Uw Wc Ye)

Figure 36 Continued

Ur(AA aE Ed Et Fd Ip It Iv Jn Jp Jq Li Lj Na Nr Ny Oa On Pi Qd Rf St Uc Un Xa) Sr(Af aQ aY CH Cx Dp Et Gp In Ki Kj Kl Li Mm Mz Nk oE Oi oN Ow Oy Pb Vs) Nu(Fd Gc Ho Iv Jl Jq kP Lh Lw Mi Mm Mp Mr Mt Mx mZ Nb Nm Nn Ns Nt Oh Pa) Va(Ad aF aM bA Cq cT Id Jd Jr Kd Kx Lp Mf Na Of Oz Pk Qg Vs Vw Wb Ti) Ut(aY Bg bL bN cH De Gc Hc Iz Kj Lj Mg Ng Oe Oi Oy Pb Qw Ss Us Vo) Aj(Bc Co Cu Cw Dd Fy Ih Jk Jp kG Ko Mt Mz Nm Nq nU Pe Rf Uf Un) Mm(Io Iq Is Iv Jl Jq Lh Mi Mj Mr Mt Mx Nb Nn Ns Nt Nv Pa Pf Po) Oz(Dr Fd Gb Io Iq Jk Jq kP Lv Lz Mj Mr Mx Nd Nq Oh Uw Vq Wb Wd) Nm(Hr Io Jl Jq Lh Mh Mi Mj Mp Mx Nb Nd Nq Ns Nt Oe Oh Om Po) Kq(Af bL bN Hb Hc Hq Kl Mg mZ Ne Ng No Nw oE Oi Ou Oy Qw Tn) Et(aZ bA bM cE Cs Cu Dc Ed Fy Hb Iz Lp Qv qY Ru Sh Ss Wb) Nn(Io Is It Jq Jt Lv Lw Ma Mf Mi Mp Mr Mu Nb Nt Pa Po) Nr(Fp Hb Io Iq Jh Jq Lv Lw Mp Mr Mt Nb Nd Ns Om Pa Vc) Ru(aP Ar Cu gL Ha Hq Ir Lx Mp Nh Nt Nv Om Ou Rm Tz Vq) Mt(Fp Ik Io Iv Jq Lw Ly Mi mZ Nb Ns Nt Om Pb Po Uv) Qb(bN Hv Jl Jo Jq jT lM Mg Mr Nb Oh Pa Pc Pe qT qY) Uu(Aa Dc Fr Gb Ih Im Js Li mI Mw Ok Om Si Tn Uc Uw) Qe(aZ bM Fp Hb Hv jQ Lh Mr Oh Om Pa Pc Pe Us Vs) Og(Hw Iu Jm Jq Jr Lv Lz Mj Mq Mu Nc Nx Oh Pb Pz) nN(Bn Fp Iz Jn Jr kI Mb Ml Of Pb Qv Ug Vo Vp) Po(Ik Iv Jq Lh Lw Mr Nd Ns Om Oy Wb Wf Yd) Gc(dR Fc Fw gL Ha Lj Mw Nc Ni OE Ri Ry) Im(Cu Iz kC Ki kN Ko kP mF mI Qw Rf Vo Vs) Hb(dK Fw Ih Il Jp Js Jv Li Oa oE Pe Qa Qv) Is(Ih Iv Iz Lh Lw Mi Mp Ms Pc Pe Uv Vo Vs) Jl(Fp Hr Ih Io It Jn Mw Mz Ny Oe Oy Pb Ti) bN(hB Ir iZ Jp Jr Js Jt Kd Li Mw Mz Pe Qa) aA(Ad aH cH cV Cx dH dR Ho Jq mZ oE qY) Fp(Ik Iq Iv Jh Jq Lh Mi Mp Nc Ns Pz) Io(Iq Jq Lw Mh Mp Mx Nb Nd Ns Om Pb) Wb(aJ Cs Ji Kk Kx Lh Mf Mk Nv oF Ql) Vt(Cx dK Dp eC Gp Hr Lp Mz No oE Rx) Sh(Dk Ef Hw Iz Jg Jk Mn Mv Sf Uf) Xa(Cs Dr Hv Il Ir Lz Ml Ni Qx Yd) Li(aZ Cu Cv cX Dc dH Dp Kd lK Rf) kP(Bo hB Ih Ir iZ Lx Lz Mq Nb oE) Eq(aW Ba Hu Jh Jk Mg Nq Om Vq) Mw(aL bA cT Dc Dr Hv Hw Pc Vo) Ij(aF Bg bM Dp Iz Ki Ow Us Uv) Qa(Dr Hc kG kN mZ Ou Us Uv Vo) Lh(Iv jK Jo Mi Nd Ns Nv Oe Oy) Rt(Ax bA Fd Ha In Jr Kn Lp Om) No(aQ aU bM bO dH Dp Kl lX) Hp(Ar cU gL Lz Mh Ml Qx Tz) It(Jq Lz Mp Mr Mx Oh Pz Uy) Nw(jI Kd Kl Kz oE oN Ou Pi) Pb(Ho Iq Jh Mi Mp Nq Oh Wd) Fd(Bo gL Lz Ml Pf Ql Qx) Mz(aH aW Cx Jo Jq Vo Wf) Lp(aM cO gL Kx Pf Qy Un) Om(Hr Iv Nd Ns Oe Of Oy) Ho(Cs Mx oE Pf Uh Us) Yd(Co Mv Nt Ql Tn Uh) Wf(Hw Kd Ok Pi Qy Uw) Vo(Aa Ir On Pg Rf St) Pe(bM kC Kl oN Ou pF) nI(dR Il kG Mp Pa Vv) qY(jI Mj Ml Mq Mr Nf) Hv(Ip Lx Nv Pg Wc) Iq(Lv Nj Ns Oe Oy) Iv(Jh Lw mZ Ns Pa) Jp(BG Cs mZ Ou) Js(aZ bM Dp Kj Qv) kG(Af Bo Kj Ml mZ) Dr(Fw Ic oF Qw) Gb(Lz Mh Ml Qx) Nt(Lw Oy Ss Vc) Mr(Hr Jn jQ jR) Qd(bP cH Uv Vs) Qy(Du Lj Rv Uz) Jq(Hr Ih Jn Ny) Jt(Lw Mi Mj Rx) Ke(bG oN Ou Ph) hB(lX nK Si Vc) Af(mI nU Ny) Ar(aE Cu dK) Cx(Aa Uz Wc) Ti(aZ Oh Pf) Nb(Hr Jh Jn) Hw(Ip Lx Ma) Ji(cB eC Vs) Jr(Ba Ns Rx) Pc(Jn Lx Mn) dR(Ex fR mF) jK(Mj Mq Na) oE(Pg Sj Uw) Cv(mZ nU) Ed(Ex Rf) Fi(gL Qx) Fy(Aa Vs) Lz(kN lX) Ml(jH lM) Ih(Ct Nq) Si(aP gL) Jh(Ns Pa) Kd(Uy Wc) Rx(Dk Kn) aZ(Fc Ry) bQ(dH oN) mI(Jo Nx) rB(jD jT) oQ(cF cN) BnmU BoUw ChMn CsTh FrbO GpUn LumZ LvNd MiHr MqYe MvUy IbNy ZxPf KjnU OweM UfUx UhmS UvPg aHnK hWjT

Constrained panels with 2 analytes, where 1.0E-3 >= 'AUC p-value' > 1.0E-4. Contains 1,678 panels of 121,819 total panels evaluated. : Jj(aH Al Ao Ap aW Ax aZ Ba Bc bN Cp Cq Cs Cu Cv cX Dd Di dK dR Ez Fy Gc Ho Hu Hv Hw Hx Id In jD Jq Jr Jy Kp Kx Kz Lp Lv Lw Lz Mg mI Mj Mp Mr Mv Mx Nb Nd Nj nT Nx Oh Pi Ra Ru Ry Si Tr Tt Uf Ug Up Ur) Hb(Ad aE As aW bN cH Cu Cw Dc Dd Fc gL Hv Hw In Ip Ir Is It Iv Ji Jl Jn Jr Jt Kd Kp Kx Lj Lw Mi Ml Mq Mt Mu Mw Mx Na Nb Nf Ni Nm nN Ny Oe Oh Om Pd Pg Pi Qd Ra Rf Rj Uc Uf Ul Un Ur Uu Vo Vt) Aj(aH Ao bA Bg cG dF Dg dK Dl Ez Fb Fw gL Id Ii Ip Iq Jh Jy Kd Kg Kj Ld Lj Lw Lx Mg Mi Mp mU Nb NT Nv Ny Oa Pg Pj Po Pz Qb Qh Ql Qy St Tt Ua Uw Vq Vt Wd) Ld(aA aE aH BB cH Cp Cu dJ Dr eC Fy Ih Ip It Iv Jf Jm Jt Kz lX Ly Me Mi mS Mx Na Nb Nn Nt OE Oi Pj Rf Tz Un Up Vt Vw Th) Gc(Ar bA bQ cH cT Fp fR Gd hC Hx Il Iv Kd Kk Ky Kz Lx Mr Mz Nn Nq Nr Nt Ny Oh Oi Oy Pc Pe Pf Pk Qy Ra Rf Uy Vp Wb Wm) Uu(aH cE cG Cp dF Dk Ef Fw Gp Ho Id Jh Jl Jq Jt Kd kG kP Lh Lx Mn mP mS Mt Nb Nr Nv Ny Pj Qb Qc Qh Rf St Ua Uf Vh) Ur(bA bN cH Cp Cq Cs cT Cu DK Fp Gb Ha Hp Ii Jl Jm Kn Ko Me Mi Mr Mw Nm Oh Ok Pd Po Qb Ry Si Tn Tt Tv Up Uw) mZ(bQ bZ cO cX dK Ez Ih Is Jn Jr Kz Ly Ma Mg Mi Mp Mv Mw Mz Nb nC Nq nR Pb Pd Qe Qv Sr Ug Ut) kP(Af aP Ax Cs Ed gL Iq Is Iv Lw Ma Mh Mi Ml Mp Mt Nn Nt oF Ow Pa Pb Pc Po Qd Sr Vp) Kq(aA aE aY bG cH Ct Dg Dp eC Ed Gp Ij Im Js Kg Li Lj Ml My Mz Nx oN Qb Qc Sr Us) Ru(aM Cx Dd Ex Gb hB Hp Hw Jr Kd Kx Ky Kz Mi Mk Mz oE Or Oz Pc Pg Pi Qc Ql Uf Wb) Vt(aA aY Bc bL Ed Et Fy Ij Im Jo Js Ko Li Lj Ml Mw Nc Nk Nt Ou Pe Qe Rf Sr Ut Vo) Yd(aH bB Cp Cw Dk Ef Fr Hu Hw Ic Iz Jd Jg Jk Jt Ko Mn Mp Mz Na Pg Qh Tz Uf) Oz(Ax aZ BA Cu Dc dF Di Hu Hw Ii Il Jm Jo Jr Lw Mg Mh Mv Nc Ns Nx Pz Ti) bN(Aa Bc Cu Fr Fy Id Ih Jg Jn Jq Ko Lw Mn Mp Ny Oa oF Oi Ok Om On Or Ou St) oE(Bb cE Dc Fb Fd Fy Gb Hp Jp Jq Jr Jy Kd kG Kn Lp Mt Mw Ny Oe Pe Qd Ut Vw) Wf(Bc Cp Dc Dd Dk Dr Ex Gb Hv Id Ii Jd Jr Jt Kk Lh Mj Na Ph Pk Uc Uh Wd) Pb(aH bA Cs Di Hu Ii Jk Jm Jo Jq Lv Lw Mg Mh mI Mu Mv Mx Nc Nd Nx Pz Un) aZ(Aa Ar Di dK Fi Gb Hl Ih Jr kG Mn Nb Nk No On Pe Rt Uw Uz Vb Vh Wc Wg) Va(aW Ax bR Ct Fd Hf iJ In Iq Kn Mj Ml Ng Ni oF Or Pa Qx Up Vp Wd Tj) Mw(bM Cu Dd Dp dR Ed Fy Gp Hc hX Id Iz Ki Kk lK mI Ou Pk Qv Ra Rf) Sh(cE cU Cw Dc Dd Fr Hq Hu Ic Il Jp Jt Ko Ok Pg Ph Pz Qh Si Uc Uw) Dp(aA cE Fw Ho Ih Is Jp Kd Lj Mt Nt Oa Pe Qb Qe Rf Un Ut Uw) Mr(Fp hW iB Io Iq Iv jD Jh jI Lw Mp Mt Nb Ni Nm Of Oh Om Pa) Qc(aE aM Aw aX bM Cp Cv Ed Fy Hv Jo Kk lM Ou Pc qY Rf Ut Wb) Uh(Du Em Fd Gn Hl kG Lp Op Rt Ry Uw Uz Vb Vh Wc We Wg Yl Tl) nN(Bb bM Ch Cq Dc Im Iv iZ Ky Lz Me Mq nA No Pf Qa Qb Qd Up) Dr(aW Bb cU gL Ih Is Kc Lx Mn Nd Nc Nw Oi Pc Pe Pf Qe Tz) Sr(aA aU aW dK eC Ed Fn Im Is Jq Jr Kd lX Ml mS Ou Qa Qd) Om(De Hu Ik Jl Lh Lw Lz Mi Mm Mp My Ng Nn Oh Pc Wb Wh Yl) Cx(bA Cu Cv Dc fR Ir iZ Jq Kd Lw Ny Uw Vh We Wg Yl) Di(aA Ar Ax Ba Bc Ch Cs Dc Fr Ih Ip Ir Js Lj Lx Qe) Mt(Ed Hw Jl Jo Lh Md Mp Mv My Nn Of Oh Oy Pa qY Vo) Im(gP Id iP kG kI Kl Kn Kr mP nA nM Qv Ss Un Ut Ye) Rf(aE aU Bb dK Et Gp Il Is Js Lj Mi Oc Pi Qb Qe Uv) On(aF Ao aW bF Bg CH Ct cX dH Hc Iz Ou Ss Uv Vs) Nq(Fd Fp Hl Io Iq Lv Nb Nc Nj Ns Oe Pa Ry Uy Uz) Wb(aM bB bQ cU dR Ex Fr gL Hf Ic Il Ke Lz Qv Ti) Ut(aA Af Cs Ct Ed Jo Ki Kl My Ne Of oN Ou Qb Vv) bA(bM bO cH cV cX Dc dK Fr Ip Lu Mn Qb Qe Rx Vs) Ar(Ad aH aX Ba bM cH Cp cS cT Cw cX Dd Lu Nd) Qv(Bb Ed Fw Gb Ho Hp Ih Ir Is Lp Qb Qe Si St) Oh(Fp Io Iq Iv Jh kN Lv lX nD Nr Ns Pa Pc qY) dK(Ax Cs dF Dk dM dR Ed iZ kI Nd Or Pe Tz Un) Eq(bQ Co Ef Et Ez Fr Jg Mu Nv Qt Qu Tn Uf) Us(Bb Ih Ir Is Jn Jq Jr kG Li mI Na Nt Qd) Lz(Fc Fi Ho iB Io Iq Iv JH nC Nm Nu) Ij(aX cE Ef Ib jH Kj Kl lX Qx Rc Ss Vv) Jo(Ad Dc Fp Fy Hr Ih Io It nT Oa Og Pf) Jp(CH Cu Dc Ed Hc Kl nT Pk Ra Ss Vs) Oe(Cs Dc Ii Io Iv Jh Jk Nb Pz Qm St Un) aA(Af aM Ax Ba Co Cu Dc Dd kG kI Ou Pj) Lw(Bb Cs Iq Jl jT Lh Mm Nm Pa Pz qY) Mp(Iq Iv Jh Jl Lh Mm Nb Ns Pc Po Pz) Nd(Ax Cs Hu Jr Mj Mv Mx Nj Ns Og Pz) Qb(aE aL aQ Ba cT Ho iB jH kG lK Rx) Jq(aW eC Is Iv Jl Lh Pz Qn Rt Uv Wm) Vo(Bb Fw Ih Il Jg Kx Mn Nt Ok Pj Tr) cX(Aa Ax bQ Dc dF fR Ir Is mU nL Qe) Ed(Bb cH Ip Is kG Kk Ko Pg Ql Un) Hv(Bb Fp Ih Io It Lh Mm Nm Og Rx) mS(Af Bn Fw gL Gp oF Ow Ri Rj Um) iZ(aE aH aI aL bB dD dR Et Gp kG) Ch(Co dR Fr Jg Jh Jt Uf Uw Wd) Nn(Fp Iq Iv Jh Lh Mx Nm Nr Pz) Nb(Fp Hx Iq Iv kG Ns Of Oy Pz) Ho(Af aM aP Lx Mh Ml Qx Qy Xa) Rx(Cp Cq Dc Fd Hp Kd Pi Tz Vp) Rt(Bo Cw Ok Ph Rb Tv Up Vp Vs) Ou(Fw Ir Is Ji Js Lj Mz Qd St) Un(aE aY cH eC Et Il Li Ss Vs) Io(Hw In Lh Lv Mg Oy Pa Pc) Pe(aQ aV dH dR Fp Gp hX Rg) mI(Iv Jn kI Mb Mh Mq Nu Oy) Cs(aH aK aX Ba dE Ip Jg) Nt(Hc Iz Kj Kl oP Uv Vs) Nk(Ax Dc Fw Fy hW jI St) Lp(bB cU Ky Mk Nf Ni Vq) Uw(aF cV Gp Il Oi Pc Qw) aE(Id Lj nY Oa oF Pj St) Ti(bB Fa hB hC nY Tz) Et(jI Kd Ki Pk Tz Vv) Fr(aF Ax Bg cT Kl Ss) Lv(jD JH Mm Nm Pz) Mi(Iv Of Oy Po qY Xa) Mn(Bg bM cH Cu Dc jD) Is(aW Kj Kl lX Mh Rm) Og(Hu In Mg Ni Nj Ns) Pa(Fp hX Iq Ns Of Oy) cU(Aa aH Gb Ry Uy Vc) dR(Gb gL No nT Oi Pg) jT(aD aM jH Jn Md Mj) Bb(fR In Mu My Ss) Fc(Ky Mh Mk Mv Qh) Mm(Hw In Jr Nm St) Qe(jD jR lX qT Qy) Js(aQ aX Ba Ct eC) Vs(Jn Jr Nr Pg Tn) Pc(Ax Fp Ih It Po) Fy(cH dJ Gp Pj) No(eC kG nD Tz) Lx(bS lK oN qY) Ml(Fi hW jK nC)

Figure 36 Continued

Hp(bB Co Il Mk) Hw(Fp It Nm Nu) Iq(Ms Mx Nc Pz) Qa(Ba bM dG dL) Qd(Ba bM IX Th) Jg(Bg Dg Kl Ss) Jh(Mj Mx Nc Uz) Wc(Bo Jr Pi Qy) Li(bM Kl Rg Tz) Ny(Ao aW Bn jI) Oa(Gp Jy Ko Pj) gL(Em eP Gn Yl) Aa(Af Ax Cu) Ih(aL bM dJ) Si(aM fR oF) Jl(Iv Nr Ns) Lh(Ly My Nr) Lj(aH Ba Jy) Ql(Jr Uz Th) Oi(Co Qh Tn) Pg(jH jI oN) aX(iB IM Wd) dF(cV Lu oN) kG(Fp Jn Uv) Bo(Uz Vh) Fd(bJ Qy) Gp(Id Kx) Nm(Mf Nc) Ma(kN nI) Mg(Fp It) Mk(Ry Uy) Hr(Dc Ii) Ir(jQ jR) Ss(Ko Tn) Jt(Bg Gd) Yl(aM Qy) aN(iB nL) bQ(bZ cE) dH(cG fR) hB(Il mF) jG(cZ dD) jH(qY rB) oQ(aW oP) AdnU AfVh CoUx CunI EfUy PolX EzNg FwLu GzOw NukI MdjR MxPz MzTz InPi IpoF ItYe ZxKz StcH JkOy JnqY KjmP KlKo UzbJ VpmU aOjO

Figure 36 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 8.1E1 | 8.1E1 | 9.4E1 | 7.9E1 | 6.8E1 | 4.4E1 | 7.0E0 | 1.6E1 | 4.8E2 | 1.5E2 | 288 | 7 | 288 | 7 | 0.45 |
| Ad | ug/mL | 4.7E-2 | 9.1E-2 | 1.3E-1 | 8.4E-2 | 6.6E-1 | 5.6E-2 | 6.8E-4 | 7.8E-4 | 8.5E0 | 1.5E-1 | 165 | 7 | 165 | 7 | 0.60 |
| Af | ng/mL | 1.2E0 | 8.7E-1 | 1.0E1 | 3.0E0 | 4.5E1 | 4.4E0 | 1.7E-3 | 1.5E-1 | 5.3E2 | 1.2E1 | 165 | 7 | 165 | 7 | 0.42 |
| Aj | ug/mL | 1.1E0 | 4.8E-1 | 2.3E0 | 1.9E0 | 2.5E0 | 2.6E0 | 1.5E-3 | 1.3E-3 | 6.1E0 | 5.8E0 | 165 | 7 | 165 | 7 | 0.44 |
| Al | mg/mL | 8.3E-5 | 7.7E-4 | 2.6E-4 | 6.3E-4 | 4.4E-4 | 6.1E-4 | 4.3E-6 | 7.8E-6 | 1.8E-3 | 1.5E-3 | 165 | 7 | 165 | 7 | 0.60 |
| An | U/mL | 6.1E1 | 9.0E1 | 2.5E2 | 1.7E2 | 8.0E2 | 1.6E2 | 2.8E-1 | 2.2E1 | 7.8E3 | 4.6E2 | 165 | 7 | 165 | 7 | 0.61 |
| Ao | pg/mL | 9.4E1 | 1.4E2 | 5.3E2 | 1.0E3 | 3.6E3 | 1.6E3 | 1.5E0 | 4.1E0 | 3.9E4 | 4.5E3 | 165 | 7 | 165 | 7 | 0.60 |
| Ap | ng/mL | 3.2E1 | 1.4E2 | 4.7E1 | 1.3E2 | 5.2E1 | 9.7E1 | 2.0E0 | 4.4E0 | 3.3E2 | 2.4E2 | 165 | 7 | 165 | 7 | 0.74 |
| Ar | ng/mL | 6.8E-1 | 2.3E0 | 2.8E0 | 9.1E0 | 6.7E0 | 1.8E1 | 3.4E-3 | 2.5E-1 | 5.1E1 | 5.0E1 | 165 | 7 | 165 | 7 | 0.66 |
| As | ng/mL | 8.7E-3 | 1.7E-3 | 2.0E-2 | 5.5E-3 | 9.7E-2 | 6.8E-3 | 1.7E-3 | 1.7E-3 | 1.2E0 | 1.9E-2 | 165 | 7 | 165 | 7 | 0.35 |
| Aw | pg/mL | 1.6E1 | 2.2E1 | 1.7E1 | 2.2E1 | 6.2E0 | 4.9E0 | 2.9E-2 | 1.4E1 | 5.1E1 | 2.9E1 | 165 | 7 | 165 | 7 | 0.80 |
| Ax | ng/mL | 2.0E0 | 1.6E1 | 2.4E1 | 1.8E2 | 9.0E1 | 3.2E2 | 1.2E-2 | 1.0E-4 | 7.7E2 | 8.5E2 | 165 | 7 | 165 | 7 | 0.70 |
| Ba | ng/mL | 8.3E1 | 1.2E3 | 5.9E2 | 3.5E3 | 1.5E3 | 5.3E3 | 1.1E0 | 4.1E0 | 8.1E3 | 1.5E4 | 165 | 7 | 165 | 7 | 0.79 |
| Bb | ng/mL | 4.0E0 | 1.9E1 | 6.9E0 | 1.8E1 | 8.3E0 | 1.6E1 | 4.1E-3 | 3.5E-1 | 4.9E1 | 4.8E1 | 165 | 7 | 165 | 7 | 0.74 |
| Bc | ng/mL | 3.5E1 | 1.6E2 | 1.2E2 | 3.6E2 | 2.3E2 | 3.9E2 | 4.9E-1 | 2.9E0 | 1.2E3 | 9.9E2 | 165 | 7 | 165 | 7 | 0.73 |
| Bg | ng/mL | 1.1E-1 | 5.9E-1 | 6.5E0 | 1.5E0 | 3.5E1 | 1.7E0 | 5.3E-4 | 3.1E-2 | 4.0E2 | 4.1E0 | 165 | 7 | 165 | 7 | 0.61 |
| Bn | ng/mL | 5.6E-2 | 2.1E-1 | 1.5E0 | 3.5E-1 | 4.9E0 | 3.8E-1 | 5.6E-2 | 5.6E-2 | 5.8E1 | 1.1E0 | 165 | 7 | 165 | 7 | 0.50 |
| Bo | ng/mL | 1.3E1 | 1.7E1 | 1.5E1 | 1.8E1 | 1.1E1 | 5.9E0 | 1.6E-2 | 9.7E0 | 5.0E1 | 2.6E1 | 165 | 7 | 165 | 7 | 0.64 |
| Ch | uIU/mL | 1.0E0 | 1.1E0 | 3.6E1 | 4.6E0 | 1.8E2 | 9.1E0 | 3.4E-3 | 5.9E-1 | 1.8E3 | 2.5E1 | 165 | 7 | 165 | 7 | 0.52 |
| Co | pg/mL | 4.7E1 | 6.1E1 | 2.2E2 | 4.2E2 | 1.3E3 | 7.5E2 | 1.5E-1 | 8.8E0 | 1.7E4 | 2.1E3 | 165 | 7 | 165 | 7 | 0.61 |
| Cp | ng/mL | 2.2E1 | 4.0E1 | 3.5E1 | 5.5E1 | 1.0E2 | 4.3E1 | 6.0E-1 | 1.1E1 | 1.3E3 | 1.4E2 | 165 | 7 | 165 | 7 | 0.72 |
| Cq | ng/mL | 3.0E-2 | 8.4E-2 | 4.0E-1 | 5.2E-1 | 3.8E0 | 8.6E-1 | 8.0E-4 | 8.0E-4 | 4.9E1 | 2.3E0 | 165 | 7 | 165 | 7 | 0.69 |
| Cs | ng/mL | 6.0E1 | 2.1E2 | 4.7E2 | 9.9E2 | 1.7E3 | 1.9E3 | 8.3E-1 | 5.7E0 | 1.8E4 | 5.1E3 | 165 | 7 | 165 | 7 | 0.64 |
| Ct | ng/mL | 3.3E-1 | 1.4E1 | 4.0E1 | 7.3E1 | 1.2E2 | 1.5E2 | 1.1E-4 | 1.1E-4 | 6.2E2 | 4.2E2 | 165 | 7 | 165 | 7 | 0.61 |
| Cu | ng/mL | 2.6E-1 | 2.9E0 | 8.7E-1 | 5.1E0 | 5.2E0 | 7.2E0 | 1.9E-2 | 1.7E-2 | 6.6E1 | 2.1E1 | 165 | 7 | 165 | 7 | 0.83 |
| Cv | ng/mL | 5.2E0 | 1.2E1 | 2.6E1 | 4.1E1 | 6.4E1 | 5.2E1 | 2.0E-2 | 1.0E-1 | 5.3E2 | 1.4E2 | 165 | 7 | 165 | 7 | 0.59 |
| Cw | mIU/mL | 3.6E-2 | 9.1E-2 | 8.3E-2 | 9.0E-2 | 5.2E-1 | 4.5E-2 | 8.9E-4 | 1.1E-2 | 6.8E0 | 1.5E-1 | 165 | 7 | 165 | 7 | 0.80 |
| Cx | ng/mL | 7.7E-1 | 7.4E-3 | 5.1E1 | 4.6E-1 | 9.9E1 | 6.6E-1 | 9.3E-5 | 9.3E-5 | 3.9E2 | 1.7E0 | 165 | 7 | 165 | 7 | 0.32 |
| Db | ug/mL | 7.5E0 | 6.7E0 | 8.8E0 | 7.9E0 | 7.7E0 | 3.6E0 | 4.5E-1 | 4.3E0 | 5.9E1 | 1.5E1 | 165 | 7 | 165 | 7 | 0.49 |
| Dc | nmol/L | 2.0E-2 | 1.9E-1 | 1.4E-1 | 3.1E-1 | 1.1E0 | 4.6E-1 | 5.2E-6 | 2.1E-3 | 1.4E1 | 1.3E0 | 165 | 7 | 165 | 7 | 0.78 |
| Dd | ug/mL | 7.1E-2 | 6.0E-1 | 1.9E-1 | 5.4E-1 | 3.6E-1 | 5.1E-1 | 4.8E-4 | 6.4E-3 | 3.6E0 | 1.5E0 | 165 | 7 | 165 | 7 | 0.69 |
| De | ng/mL | 3.4E-3 | 2.1E-1 | 7.6E-2 | 3.0E-1 | 1.4E-1 | 4.0E-1 | 3.4E-3 | 3.4E-3 | 9.2E-1 | 1.1E0 | 165 | 7 | 165 | 7 | 0.69 |
| Dg | ng/mL | 3.6E1 | 8.7E1 | 4.6E1 | 7.0E1 | 4.0E1 | 4.8E1 | 7.1E-1 | 1.9E0 | 1.9E2 | 1.2E2 | 165 | 7 | 165 | 7 | 0.65 |
| Di | pg/mL | 2.0E0 | 3.3E0 | 2.4E0 | 3.9E0 | 2.2E0 | 1.2E0 | 1.8E-1 | 2.7E0 | 1.3E1 | 5.4E0 | 165 | 7 | 165 | 7 | 0.76 |
| Dk | uIU/mL | 1.4E-2 | 2.8E-2 | 5.4E-2 | 1.7E-1 | 1.6E-1 | 3.6E-1 | 1.1E-4 | 6.6E-3 | 1.6E0 | 9.8E-1 | 165 | 7 | 165 | 7 | 0.58 |
| Dl | ng/mL | 2.0E2 | 4.7E2 | 2.9E2 | 4.7E2 | 2.8E2 | 3.9E2 | 5.5E0 | 4.4E0 | 1.6E3 | 1.1E3 | 165 | 7 | 165 | 7 | 0.64 |
| Po | pg/ml | 3.0E-1 | 2.8E1 | 9.6E0 | 4.3E1 | 2.9E1 | 6.8E1 | 8.0E-3 | 2.6E-2 | 2.7E2 | 2.2E2 | 339 | 9 | 339 | 9 | 0.81 |
| Et | ng/ml | 1.4E3 | 3.0E3 | 1.7E3 | 3.0E3 | 1.2E3 | 1.6E3 | 7.5E1 | 5.9E2 | 4.8E3 | 5.0E3 | 338 | 9 | 338 | 9 | 0.75 |
| Fp | ng/ml | 1.3E1 | 3.8E1 | 2.4E1 | 3.8E1 | 2.7E1 | 3.9E1 | 6.0E-3 | 1.3E0 | 1.3E2 | 1.2E2 | 341 | 9 | 341 | 9 | 0.60 |
| Fr | ng/ml | 3.5E4 | 5.5E5 | 1.2E5 | 4.0E5 | 1.8E5 | 3.2E5 | 1.9E2 | 7.0E3 | 8.4E5 | 8.4E5 | 346 | 11 | 346 | 11 | 0.78 |
| Nm | pg/ml | 1.2E4 | 1.2E5 | 3.4E4 | 1.5E5 | 8.9E4 | 1.7E5 | 1.0E-9 | 1.0E-9 | 9.6E5 | 4.4E5 | 342 | 9 | 342 | 9 | 0.73 |
| Nn | pg/ml | 1.5E2 | 6.8E2 | 1.7E3 | 4.1E4 | 8.0E3 | 1.0E5 | 1.0E-9 | 1.0E-9 | 9.5E4 | 3.1E5 | 342 | 9 | 342 | 9 | 0.76 |
| No | pg/ml | 1.5E1 | 8.3E1 | 3.6E1 | 1.5E2 | 8.1E1 | 2.2E2 | 1.0E-9 | 1.6E0 | 9.1E2 | 7.0E2 | 342 | 9 | 342 | 9 | 0.73 |
| Nq | pg/ml | 1.9E0 | 1.9E1 | 2.1E1 | 1.2E2 | 7.4E1 | 2.0E2 | 1.0E-9 | 1.0E-9 | 6.7E2 | 5.9E2 | 342 | 9 | 342 | 9 | 0.69 |
| Nr | pg/ml | 1.5E0 | 1.2E1 | 2.3E1 | 2.1E2 | 8.3E1 | 4.4E2 | 1.0E-9 | 1.0E-9 | 9.8E2 | 1.4E3 | 342 | 9 | 342 | 9 | 0.69 |
| Ns | pg/ml | 1.0E-9 | 1.0E-9 | 7.8E0 | 4.0E-1 | 6.5E1 | 1.2E0 | 1.0E-9 | 1.0E-9 | 1.1E3 | 3.6E0 | 342 | 9 | 342 | 9 | 0.52 |
| Nt | pg/ml | 1.0E2 | 2.4E2 | 1.4E2 | 3.7E2 | 1.3E2 | 3.7E2 | 9.8E-1 | 8.0E1 | 1.7E3 | 1.2E3 | 342 | 9 | 342 | 9 | 0.77 |
| Nu | pg/ml | 1.7E1 | 1.0E2 | 5.6E1 | 1.3E2 | 9.3E1 | 8.6E1 | 1.0E-9 | 7.8E0 | 6.3E2 | 2.9E2 | 342 | 9 | 342 | 9 | 0.79 |
| Lu | pg/ml | 1.0E4 | 1.0E4 | 1.5E4 | 1.0E4 | 4.0E4 | 7.2E3 | 5.2E2 | 3.0E3 | 5.6E5 | 2.7E4 | 342 | 9 | 342 | 9 | 0.51 |
| Lv | pg/ml | 1.0E-9 | 4.3E1 | 1.5E1 | 5.2E1 | 3.2E1 | 3.7E1 | 1.0E-9 | 7.3E0 | 2.6E2 | 1.1E2 | 342 | 9 | 342 | 9 | 0.85 |
| Lw | pg/ml | 1.0E-9 | 1.0E-9 | 4.7E-1 | 2.4E1 | 5.1E0 | 5.9E1 | 1.0E-9 | 1.0E-9 | 8.0E1 | 1.8E2 | 342 | 9 | 342 | 9 | 0.66 |
| Lx | pg/ml | 1.0E-9 | 4.8E2 | 2.4E2 | 9.0E2 | 1.3E3 | 9.4E2 | 1.0E-9 | 1.0E-9 | 2.2E4 | 2.8E3 | 342 | 9 | 342 | 9 | 0.84 |
| Ly | pg/ml | 1.0E-9 | 1.0E-9 | 9.2E0 | 5.2E0 | 1.8E1 | 8.5E0 | 1.0E-9 | 1.0E-9 | 1.1E2 | 2.4E1 | 342 | 9 | 342 | 9 | 0.48 |
| Lz | pg/ml | 1.0E-9 | 1.0E-9 | 3.5E0 | 5.6E0 | 2.6E1 | 1.6E1 | 1.0E-9 | 1.0E-9 | 4.3E2 | 4.7E1 | 342 | 9 | 342 | 9 | 0.57 |

Figure 37

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ma | pg/ml | 3.9E2 | 3.4E3 | 2.2E3 | 9.2E3 | 6.0E3 | 1.3E4 | 1.0E-9 | 2.4E1 | 6.5E4 | 3.6E4 | 342 | 9 | 342 | 9 | 0.70 |
| Mb | pg/ml | 2.5E1 | 2.7E1 | 3.2E1 | 3.2E1 | 1.8E1 | 1.5E1 | 4.1E0 | 1.6E1 | 2.1E2 | 5.3E1 | 342 | 9 | 342 | 9 | 0.50 |
| Mc | pg/ml | 1.0E-9 | 1.0E-9 | 5.6E-2 | 1.0E-9 | 7.4E-1 | 0.0E0 | 1.0E-9 | 1.0E-9 | 1.3E1 | 1.0E-9 | 342 | 9 | 342 | 9 | 0.49 |
| Md | pg/ml | 1.0E-9 | 1.0E-9 | 6.6E-1 | 5.1E-1 | 5.5E0 | 1.3E0 | 1.0E-9 | 1.0E-9 | 6.8E1 | 4.0E0 | 342 | 9 | 342 | 9 | 0.57 |
| Me | pg/ml | 3.1E1 | 2.7E1 | 3.1E1 | 2.4E1 | 2.4E1 | 1.6E1 | 1.0E-9 | 1.0E-9 | 3.2E2 | 5.0E1 | 342 | 9 | 342 | 9 | 0.39 |
| Mf | pg/ml | 1.0E-9 | 1.0E-9 | 6.2E-1 | 1.4E-1 | 3.9E0 | 2.8E-1 | 1.0E-9 | 1.0E-9 | 5.6E1 | 6.8E-1 | 342 | 9 | 342 | 9 | 0.53 |
| Mg | pg/ml | 9.4E-1 | 2.0E0 | 6.2E0 | 3.2E1 | 1.2E1 | 5.4E1 | 1.0E-9 | 1.0E-9 | 9.2E1 | 1.5E2 | 342 | 9 | 342 | 9 | 0.58 |
| Mh | pg/ml | 1.0E-9 | 1.0E-9 | 1.2E0 | 2.4E0 | 7.6E0 | 6.0E0 | 1.0E-9 | 1.0E-9 | 1.1E2 | 1.8E1 | 342 | 9 | 342 | 9 | 0.59 |
| Mi | pg/ml | 1.0E-9 | 9.3E0 | 1.9E0 | 7.9E1 | 1.9E1 | 1.7E2 | 1.0E-9 | 1.0E-9 | 3.2E2 | 5.2E2 | 342 | 9 | 342 | 9 | 0.82 |
| Mj | pg/ml | 1.0E-9 | 2.0E0 | 6.3E0 | 4.5E1 | 3.2E1 | 7.3E1 | 1.0E-9 | 1.0E-9 | 4.6E2 | 2.1E2 | 342 | 9 | 342 | 9 | 0.70 |
| Mk | pg/ml | 1.8E0 | 5.6E0 | 1.5E1 | 6.4E1 | 9.2E1 | 1.7E2 | 1.0E-9 | 1.0E-9 | 1.3E3 | 5.0E2 | 342 | 9 | 342 | 9 | 0.65 |
| Ml | pg/ml | 1.0E-9 | 1.0E-9 | 1.1E1 | 2.6E-1 | 1.2E2 | 7.7E-1 | 1.0E-9 | 1.0E-9 | 2.1E3 | 2.3E0 | 342 | 9 | 342 | 9 | 0.44 |
| Mm | pg/ml | 5.5E2 | 2.2E3 | 1.0E3 | 3.2E3 | 1.3E3 | 3.3E3 | 1.0E-9 | 1.0E-9 | 1.0E4 | 1.0E4 | 342 | 9 | 342 | 9 | 0.68 |
| Mn | pg/ml | 5.9E0 | 1.2E1 | 1.1E1 | 1.4E1 | 2.5E1 | 1.1E1 | 1.0E-9 | 1.1E0 | 3.5E2 | 3.7E1 | 342 | 9 | 342 | 9 | 0.67 |
| Mp | pg/ml | 1.0E-9 | 2.7E1 | 1.3E1 | 3.3E2 | 5.0E1 | 7.7E2 | 1.0E-9 | 1.0E-9 | 6.3E2 | 2.4E3 | 342 | 9 | 342 | 9 | 0.79 |
| Mq | pg/ml | 1.0E-9 | 1.0E-9 | 2.4E0 | 1.8E1 | 1.4E1 | 2.9E1 | 1.0E-9 | 1.0E-9 | 1.8E2 | 7.4E1 | 342 | 9 | 342 | 9 | 0.64 |
| Mr | pg/ml | 1.0E-9 | 1.1E1 | 3.2E1 | 4.8E1 | 1.8E2 | 1.1E3 | 1.0E-9 | 1.0E-9 | 2.2E3 | 3.4E3 | 342 | 9 | 342 | 9 | 0.66 |
| Ms | pg/ml | 3.2E2 | 2.6E2 | 4.6E2 | 7.6E2 | 5.3E2 | 1.5E3 | 1.0E-9 | 1.0E-9 | 3.3E3 | 4.7E3 | 342 | 9 | 342 | 9 | 0.44 |
| Mt | pg/ml | 2.7E-1 | 1.2E1 | 1.8E1 | 6.7E1 | 1.8E2 | 9.9E1 | 1.0E-9 | 1.0E-9 | 3.2E3 | 3.1E2 | 342 | 9 | 342 | 9 | 0.76 |
| Mu | pg/ml | 1.0E-9 | 1.0E-9 | 1.4E0 | 6.4E0 | 1.4E1 | 1.6E1 | 1.0E-9 | 1.0E-9 | 2.3E2 | 4.8E1 | 342 | 9 | 342 | 9 | 0.61 |
| Mv | pg/ml | 1.0E-9 | 2.5E0 | 6.7E1 | 1.9E2 | 3.4E2 | 3.5E2 | 1.0E-9 | 1.0E-9 | 4.5E3 | 9.0E2 | 342 | 9 | 342 | 9 | 0.67 |
| Mw | pg/ml | 3.7E1 | 6.6E2 | 2.7E2 | 1.2E3 | 1.4E3 | 1.7E3 | 1.0E-9 | 1.0E-9 | 1.8E4 | 5.2E3 | 342 | 9 | 342 | 9 | 0.76 |
| Mx | pg/ml | 1.0E-9 | 1.0E-9 | 4.1E-1 | 1.2E0 | 2.2E0 | 2.2E0 | 1.0E-9 | 1.0E-9 | 3.2E1 | 6.6E0 | 342 | 9 | 342 | 9 | 0.65 |
| My | pg/ml | 1.0E-9 | 1.1E2 | 3.2E2 | 4.7E2 | 2.4E3 | 7.8E2 | 1.0E-9 | 1.0E-9 | 3.9E4 | 1.9E3 | 342 | 9 | 342 | 9 | 0.69 |
| Mz | pg/ml | 1.1E1 | 1.1E2 | 3.5E1 | 9.6E1 | 1.3E2 | 7.4E1 | 1.0E-9 | 3.5E0 | 1.9E3 | 2.0E2 | 342 | 9 | 342 | 9 | 0.80 |
| Na | pg/ml | 1.0E-9 | 1.0E-9 | 7.6E-1 | 2.0E0 | 2.9E0 | 2.9E0 | 1.0E-9 | 1.0E-9 | 4.2E1 | 6.4E0 | 342 | 9 | 342 | 9 | 0.63 |
| Nb | pg/ml | 2.2E0 | 8.1E0 | 3.9E0 | 3.5E1 | 1.2E1 | 6.7E1 | 1.0E-9 | 5.4E-2 | 1.5E2 | 2.1E2 | 342 | 9 | 342 | 9 | 0.74 |
| Nc | pg/ml | 3.1E2 | 1.3E1 | 5.1E2 | 3.8E2 | 7.4E2 | 5.1E2 | 1.0E-9 | 1.0E-9 | 9.2E3 | 1.4E3 | 342 | 9 | 342 | 9 | 0.43 |
| Nd | pg/ml | 2.7E1 | 3.9E1 | 3.3E1 | 4.9E1 | 1.3E2 | 4.9E1 | 1.0E-9 | 7.2E-1 | 2.1E3 | 1.5E2 | 342 | 9 | 342 | 9 | 0.66 |
| Ne | pg/ml | 4.2E2 | 3.2E2 | 5.1E2 | 6.3E2 | 5.4E2 | 1.1E3 | 1.0E-9 | 1.0E-9 | 7.0E3 | 3.6E3 | 342 | 9 | 342 | 9 | 0.41 |
| Nf | pg/ml | 1.0E-9 | 1.0E-9 | 3.1E0 | 9.4E-1 | 1.3E1 | 1.9E0 | 1.0E-9 | 1.0E-9 | 1.3E2 | 4.8E0 | 342 | 9 | 342 | 9 | 0.50 |
| Ng | pg/ml | 1.2E1 | 9.6E0 | 9.0E1 | 7.1E1 | 1.8E2 | 9.5E1 | 1.0E-9 | 1.0E-9 | 1.6E3 | 2.6E2 | 342 | 9 | 342 | 9 | 0.52 |
| Nh | pg/ml | 6.2E1 | 2.9E1 | 7.9E1 | 8.5E1 | 7.2E1 | 1.6E2 | 1.0E-9 | 4.5E0 | 5.6E2 | 5.1E2 | 342 | 9 | 342 | 9 | 0.34 |
| Ni | pg/ml | 1.0E-9 | 1.0E-9 | 8.5E1 | 5.1E1 | 1.4E2 | 1.2E2 | 1.0E-9 | 1.0E-9 | 1.1E3 | 3.5E2 | 342 | 9 | 342 | 9 | 0.38 |
| Nj | pg/ml | 7.2E0 | 4.4E0 | 1.1E1 | 6.2E0 | 1.2E1 | 6.5E0 | 1.0E-9 | 1.0E-9 | 6.9E1 | 1.7E1 | 342 | 9 | 342 | 9 | 0.37 |
| Nk | pg/ml | 1.8E1 | 1.0E-9 | 3.2E1 | 2.0E1 | 3.9E1 | 3.2E1 | 1.0E-9 | 1.0E-9 | 2.0E2 | 8.3E1 | 342 | 9 | 342 | 9 | 0.36 |
| Nl | pg/ml | 4.2E1 | 9.3E1 | 5.6E1 | 3.9E1 | 7.5E1 | 6.0E1 | 1.0E-9 | 1.0E-9 | 1.1E3 | 1.8E2 | 342 | 9 | 342 | 9 | 0.34 |
| Hq | pg/ml | 1.1E0 | 9.1E0 | 1.6E2 | 2.7E1 | 1.9E3 | 5.8E1 | 1.0E-9 | 1.0E-9 | 2.8E4 | 1.8E2 | 340 | 9 | 340 | 9 | 0.66 |
| Hr | pg/ml | 9.1E1 | 2.7E2 | 6.6E2 | 6.0E2 | 1.4E3 | 1.1E3 | 1.0E-9 | 1.6E1 | 1.2E4 | 3.4E3 | 340 | 9 | 340 | 9 | 0.56 |
| Hu | pg/ml | 1.1E1 | 9.5E2 | 4.6E3 | 1.3E3 | 4.0E4 | 1.9E3 | 1.0E-9 | 1.0E-9 | 6.3E5 | 5.9E3 | 340 | 9 | 340 | 9 | 0.72 |
| Hv | pg/ml | 1.4E0 | 3.0E0 | 5.2E0 | 2.4E1 | 4.9E1 | 5.3E1 | 1.0E-9 | 3.8E-1 | 8.9E2 | 1.6E2 | 340 | 9 | 340 | 9 | 0.66 |
| Hw | pg/ml | 6.4E0 | 5.6E1 | 4.3E1 | 9.3E1 | 5.1E2 | 1.6E2 | 1.0E-9 | 4.6E-1 | 9.4E3 | 5.0E2 | 340 | 9 | 340 | 9 | 0.69 |
| Hx | pg/ml | 8.8E0 | 2.4E1 | 5.5E1 | 1.9E2 | 5.0E2 | 4.1E2 | 1.0E-9 | 8.8E0 | 9.3E3 | 1.3E3 | 340 | 9 | 340 | 9 | 0.78 |
| Ih | ng/ml | 6.3E1 | 3.9E2 | 2.5E2 | 7.2E2 | 4.6E2 | 7.3E2 | 1.0E-9 | 2.4E0 | 3.6E3 | 1.9E3 | 341 | 9 | 341 | 9 | 0.68 |
| Ii | ng/ml | 8.1E1 | 4.5E2 | 2.1E2 | 8.3E2 | 5.1E2 | 1.4E3 | 7.3E-1 | 7.5E-1 | 5.2E3 | 4.5E3 | 341 | 9 | 341 | 9 | 0.65 |
| Ij | ng/ml | 7.8E1 | 3.1E2 | 2.5E2 | 6.1E2 | 1.4E3 | 7.2E2 | 2.8E0 | 9.5E0 | 2.4E4 | 1.9E3 | 337 | 9 | 337 | 9 | 0.77 |
| Ik | ng/ml | 1.1E1 | 3.7E1 | 1.3E3 | 3.3E2 | 1.2E4 | 4.8E2 | 5.9E-1 | 6.2E-1 | 1.2E5 | 1.5E3 | 337 | 9 | 337 | 9 | 0.62 |
| Il | ng/ml | 3.6E2 | 1.3E3 | 1.3E3 | 4.1E3 | 2.9E3 | 5.2E3 | 1.0E-9 | 1.9E-1 | 1.2E4 | 1.2E4 | 335 | 9 | 335 | 9 | 0.64 |
| Im | ng/ml | 2.1E2 | 7.0E2 | 4.5E2 | 2.7E3 | 7.8E2 | 4.8E3 | 1.4E1 | 2.2E1 | 6.2E3 | 1.5E4 | 337 | 9 | 337 | 9 | 0.79 |
| In | ng/ml | 3.4E0 | 8.8E0 | 3.3E1 | 1.1E2 | 2.6E2 | 2.1E2 | 5.4E-1 | 4.5E3 | 5.9E2 | 341 | 9 | 341 | 9 | 0.61 |
| Io | ng/ml | 9.4E3 | 2.0E4 | 1.9E4 | 2.7E4 | 4.6E4 | 3.1E4 | 1.0E-9 | 1.0E3 | 7.1E5 | 1.0E5 | 341 | 9 | 341 | 9 | 0.61 |
| Ip | ng/ml | 1.0E1 | 3.0E1 | 2.1E1 | 3.6E1 | 2.6E1 | 2.1E1 | 1.0E-9 | 9.8E0 | 2.3E2 | 7.1E1 | 341 | 9 | 341 | 9 | 0.73 |
| Iq | ug/ml | 1.0E-1 | 3.0E0 | 4.1E1 | 6.3E0 | 7.4E2 | 7.9E0 | 1.0E-9 | 1.0E-9 | 1.4E4 | 2.1E1 | 341 | 9 | 341 | 9 | 0.75 |
| Ir | ug/ml | 3.7E-1 | 5.0E0 | 5.6E0 | 3.5E1 | 3.8E1 | 5.1E1 | 1.0E-9 | 3.5E-2 | 5.1E2 | 1.3E2 | 340 | 9 | 340 | 9 | 0.77 |
| Is | ng/ml | 2.0E0 | 4.2E1 | 9.4E0 | 7.0E1 | 3.4E1 | 8.5E1 | 1.0E-9 | 2.2E-1 | 5.5E2 | 2.6E2 | 341 | 9 | 341 | 9 | 0.77 |
| It | ng/ml | 2.1E0 | 5.4E0 | 2.3E1 | 6.7E1 | 1.0E2 | 1.8E2 | 1.0E-9 | 1.0E-9 | 1.1E3 | 5.5E2 | 341 | 9 | 341 | 9 | 0.66 |
| Iu | ng/ml | 1.6E2 | 2.4E3 | 1.3E3 | 8.3E3 | 4.1E3 | 1.0E4 | 1.0E-9 | 1.0E-9 | 2.9E4 | 2.4E4 | 341 | 9 | 341 | 9 | 0.72 |

Figure 37 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Iv | ng/ml | 1.3E1 | 1.3E2 | 9.8E1 | 9.1E2 | 8.8E2 | 1.7E3 | 1.0E-9 | 5.0E0 | 1.6E4 | 3.8E3 | 340 | 9 | 340 | 9 | 0.74 |
| Pz | ng/ml | 3.5E3 | 1.0E4 | 5.6E3 | 7.9E3 | 6.0E3 | 4.1E3 | 1.6E1 | 4.0E1 | 7.0E4 | 1.3E4 | 337 | 9 | 337 | 9 | 0.67 |
| Qa | ng/ml | 3.6E3 | 2.3E4 | 7.5E3 | 2.1E4 | 1.4E4 | 1.2E4 | 1.5E2 | 9.4E2 | 2.2E5 | 3.2E4 | 337 | 9 | 337 | 9 | 0.80 |
| Qb | ng/ml | 1.1E2 | 3.9E2 | 2.4E2 | 4.6E2 | 4.4E2 | 4.7E2 | 7.9E-1 | 3.2E1 | 5.3E3 | 1.6E3 | 337 | 9 | 337 | 9 | 0.69 |
| Qc | ng/ml | 2.0E2 | 7.5E2 | 4.5E2 | 7.2E2 | 6.0E2 | 5.2E2 | 1.0E-9 | 3.2E1 | 4.3E3 | 1.4E3 | 337 | 9 | 337 | 9 | 0.67 |
| Qd | ng/ml | 8.8E3 | 9.4E4 | 2.4E4 | 1.4E5 | 1.1E5 | 1.3E5 | 1.5E2 | 1.9E3 | 2.0E6 | 4.3E5 | 337 | 9 | 337 | 9 | 0.84 |
| Qe | ng/ml | 9.1E2 | 6.0E3 | 2.0E3 | 6.4E3 | 5.6E3 | 6.1E3 | 1.0E-9 | 5.7E1 | 9.7E4 | 1.8E4 | 337 | 9 | 337 | 9 | 0.71 |
| Jg | ng/ml | 4.6E2 | 1.7E3 | 7.8E2 | 1.7E3 | 9.5E2 | 1.2E3 | 5.8E0 | 8.4E1 | 1.0E4 | 3.9E3 | 340 | 9 | 340 | 9 | 0.75 |
| Jh | ng/ml | 2.9E0 | 3.0E1 | 2.1E1 | 6.2E1 | 8.6E1 | 9.3E1 | 1.0E-9 | 1.0E-9 | 1.2E3 | 2.9E2 | 340 | 9 | 340 | 9 | 0.76 |
| Ji | ng/ml | 5.7E1 | 3.5E2 | 8.9E1 | 3.3E2 | 1.1E2 | 2.6E2 | 1.1E0 | 2.3E1 | 1.3E3 | 6.9E2 | 340 | 9 | 340 | 9 | 0.74 |
| Jj | ng/ml | 5.3E2 | 1.7E2 | 1.9E3 | 3.7E2 | 1.8E4 | 4.0E2 | 2.3E0 | 8.7E0 | 3.4E5 | 1.0E3 | 340 | 9 | 340 | 9 | 0.32 |
| Jk | ng/ml | 2.6E0 | 4.9E1 | 2.0E1 | 7.1E1 | 4.8E1 | 8.6E1 | 1.0E-9 | 1.2E-1 | 3.9E2 | 2.4E2 | 340 | 9 | 340 | 9 | 0.74 |
| Jl | ng/ml | 4.8E-1 | 1.2E0 | 2.1E0 | 1.1E3 | 4.9E0 | 3.3E3 | 1.2E-3 | 2.5E-1 | 4.0E1 | 9.9E3 | 340 | 9 | 340 | 9 | 0.76 |
| Jm | ng/ml | 1.9E1 | 6.8E1 | 6.8E1 | 8.3E1 | 1.7E2 | 8.8E1 | 1.0E-9 | 4.0E-1 | 2.1E3 | 2.5E2 | 340 | 9 | 340 | 9 | 0.61 |
| Jn | pg/ml | 3.5E-1 | 1.9E0 | 7.3E0 | 2.9E1 | 6.2E1 | 7.8E1 | 1.0E-9 | 1.0E-9 | 7.3E2 | 2.4E2 | 340 | 9 | 340 | 9 | 0.75 |
| Jo | pg/ml | 3.8E3 | 6.3E3 | 5.1E3 | 1.0E4 | 6.6E3 | 1.2E4 | 2.0E1 | 2.4E1 | 1.0E5 | 3.6E4 | 340 | 9 | 340 | 9 | 0.62 |
| Jp | pg/ml | 7.1E4 | 1.1E5 | 7.4E4 | 1.2E5 | 4.0E4 | 3.1E4 | 5.8E2 | 6.8E4 | 3.8E5 | 1.6E5 | 340 | 9 | 340 | 9 | 0.82 |
| Jq | pg/ml | 9.6E1 | 4.0E2 | 1.9E2 | 5.3E2 | 5.2E2 | 5.4E2 | 1.0E0 | 1.3E1 | 8.7E3 | 1.7E3 | 340 | 9 | 340 | 9 | 0.75 |
| Jr | pg/ml | 4.7E0 | 3.4E1 | 8.9E1 | 3.2E2 | 7.6E2 | 8.0E2 | 1.0E-9 | 1.0E-9 | 1.1E4 | 2.4E3 | 340 | 9 | 340 | 9 | 0.80 |
| Js | pg/ml | 1.5E1 | 2.7E1 | 8.3E1 | 4.0E2 | 6.0E2 | 9.7E2 | 1.0E-9 | 2.7E0 | 1.0E4 | 3.0E3 | 340 | 9 | 340 | 9 | 0.69 |
| Jt | pg/ml | 2.4E3 | 5.9E3 | 3.1E3 | 1.3E4 | 3.5E3 | 1.4E4 | 2.2E1 | 1.5E2 | 5.2E4 | 4.1E4 | 340 | 9 | 340 | 9 | 0.75 |
| Lh | pg/ml | 1.3E4 | 3.7E4 | 2.4E4 | 8.9E4 | 4.2E4 | 1.3E5 | 1.0E-9 | 2.0E3 | 4.8E5 | 4.1E5 | 341 | 9 | 341 | 9 | 0.70 |
| Li | pg/ml | 3.5E3 | 3.8E4 | 2.0E4 | 1.0E5 | 9.1E4 | 1.4E5 | 1.2E1 | 8.4E1 | 1.3E6 | 4.1E5 | 341 | 9 | 341 | 9 | 0.78 |
| Lj | pg/ml | 2.9E3 | 1.5E4 | 2.1E4 | 2.6E4 | 5.9E4 | 4.1E4 | 1.0E-9 | 8.9E1 | 4.3E5 | 1.3E5 | 341 | 9 | 341 | 9 | 0.61 |
| Nv | pg/ml | 3.9E3 | 1.6E4 | 9.6E3 | 3.6E4 | 1.9E4 | 4.2E4 | 1.0E-9 | 1.6E2 | 1.6E5 | 1.2E5 | 342 | 9 | 342 | 9 | 0.79 |
| Nw | pg/ml | 9.6E3 | 2.9E4 | 1.4E4 | 3.8E4 | 1.9E4 | 2.6E4 | 1.9E2 | 4.5E3 | 2.1E5 | 7.8E4 | 342 | 9 | 342 | 9 | 0.81 |
| Nx | pg/ml | 2.2E2 | 8.1E2 | 4.3E2 | 9.2E2 | 6.3E2 | 8.8E2 | 1.0E-9 | 1.0E-9 | 4.1E3 | 2.3E3 | 342 | 9 | 342 | 9 | 0.66 |
| Ny | pg/ml | 6.5E0 | 8.0E1 | 1.1E2 | 1.7E2 | 1.3E3 | 2.1E2 | 1.0E-9 | 1.0E-9 | 2.5E4 | 6.1E2 | 342 | 9 | 342 | 9 | 0.82 |
| Oe | pg/ml | 3.1E1 | 1.0E-9 | 2.5E2 | 1.7E2 | 3.8E2 | 3.8E2 | 1.0E-9 | 1.0E-9 | 2.3E3 | 1.1E3 | 340 | 9 | 340 | 9 | 0.37 |
| Of | pg/ml | 1.3E2 | 2.1E2 | 5.1E3 | 3.1E3 | 2.1E4 | 8.0E3 | 1.0E-9 | 1.0E-9 | 1.9E5 | 2.4E4 | 342 | 9 | 342 | 9 | 0.55 |
| Og | pg/ml | 6.5E-2 | 6.6E-2 | 3.6E-1 | 8.3E-2 | 1.5E0 | 9.9E-2 | 1.0E-9 | 1.0E-9 | 1.9E1 | 3.2E-1 | 342 | 9 | 342 | 9 | 0.45 |
| Oh | pg/ml | 2.5E0 | 1.3E1 | 1.8E1 | 1.8E3 | 1.1E2 | 5.3E3 | 1.0E-9 | 1.0E-9 | 1.4E3 | 1.6E4 | 342 | 9 | 342 | 9 | 0.64 |
| Oi | pg/ml | 1.9E0 | 1.0E-9 | 5.0E0 | 3.6E0 | 7.9E0 | 5.5E0 | 1.0E-9 | 1.0E-9 | 6.7E1 | 1.6E1 | 342 | 9 | 342 | 9 | 0.43 |
| Ok | pg/ml | 3.9E2 | 2.2E3 | 5.5E2 | 2.4E3 | 6.5E2 | 2.3E3 | 1.5E1 | 5.3E1 | 7.8E3 | 7.0E3 | 342 | 9 | 342 | 9 | 0.75 |
| Om | pg/ml | 4.2E2 | 1.3E3 | 9.4E2 | 2.0E3 | 3.4E3 | 1.9E3 | 1.0E-9 | 7.0E1 | 5.1E4 | 5.6E3 | 342 | 9 | 342 | 9 | 0.75 |
| On | pg/ml | 1.8E2 | 7.5E2 | 3.0E2 | 2.0E3 | 4.4E2 | 2.7E3 | 1.0E-9 | 1.6E1 | 4.5E3 | 8.5E3 | 342 | 9 | 342 | 9 | 0.82 |
| Oy | pg/ml | 4.7E-1 | 5.3E-1 | 6.1E0 | 7.6E0 | 3.1E1 | 1.2E1 | 1.0E-9 | 1.0E-9 | 4.0E2 | 3.3E1 | 341 | 9 | 341 | 9 | 0.54 |
| Oz | pg/ml | 4.5E-3 | 1.0E-9 | 3.3E-1 | 3.2E0 | 1.6E0 | 9.3E0 | 1.0E-9 | 1.0E-9 | 2.9E1 | 2.8E1 | 341 | 9 | 341 | 9 | 0.43 |
| Pa | pg/ml | 3.9E-1 | 7.1E-1 | 1.7E0 | 3.0E1 | 7.9E0 | 7.4E1 | 1.0E-9 | 1.0E-9 | 1.0E2 | 2.3E2 | 341 | 9 | 341 | 9 | 0.66 |
| Pb | pg/ml | 1.0E-9 | 1.0E-9 | 1.7E0 | 2.3E-1 | 2.6E1 | 6.4E-1 | 1.0E-9 | 1.0E-9 | 4.9E2 | 1.9E0 | 341 | 9 | 341 | 9 | 0.48 |
| Pc | pg/ml | 4.8E-2 | 1.0E-9 | 3.9E-1 | 3.7E1 | 9.0E-1 | 1.1E2 | 1.0E-9 | 1.0E-9 | 1.4E1 | 3.3E2 | 341 | 9 | 341 | 9 | 0.46 |
| Pd | pg/ml | 1.6E0 | 1.5E0 | 6.7E0 | 1.2E1 | 4.7E1 | 2.0E1 | 1.0E-9 | 6.3E-3 | 8.4E2 | 5.5E1 | 341 | 9 | 341 | 9 | 0.56 |
| Pe | pg/ml | 2.1E1 | 2.2E2 | 1.4E2 | 2.0E3 | 6.3E2 | 4.9E3 | 1.0E-9 | 3.3E0 | 6.7E3 | 1.5E4 | 341 | 9 | 341 | 9 | 0.80 |
| Pf | pg/ml | 1.6E0 | 1.4E1 | 1.6E1 | 3.2E1 | 9.3E1 | 4.9E1 | 1.0E-9 | 1.0E-9 | 1.5E3 | 1.5E2 | 341 | 9 | 341 | 9 | 0.74 |
| Pg | pg/ml | 3.9E0 | 2.2E1 | 7.2E1 | 4.0E2 | 5.2E2 | 5.1E2 | 1.0E-9 | 1.9E0 | 7.7E3 | 1.3E3 | 341 | 9 | 341 | 9 | 0.77 |
| aA | mg/dL | 9.0E-1 | 1.4E0 | 1.0E0 | 2.1E0 | 5.3E-1 | 1.3E0 | 3.0E-1 | 8.9E-1 | 4.2E0 | 4.7E0 | 518 | 15 | 518 | 15 | 0.83 |
| aC | mg/mL | 2.2E0 | 4.1E0 | 2.6E0 | 3.7E0 | 1.3E0 | 2.2E0 | 7.5E-1 | 1.0E0 | 7.4E0 | 6.7E0 | 166 | 8 | 166 | 8 | 0.63 |
| aD | ug/mL | 3.0E0 | 2.8E0 | 4.7E0 | 3.0E0 | 4.8E0 | 1.1E0 | 7.5E-1 | 1.8E0 | 3.5E1 | 4.7E0 | 166 | 8 | 166 | 8 | 0.43 |
| aE | mg/mL | 5.7E-1 | 5.6E-1 | 5.9E-1 | 5.5E-1 | 1.7E-1 | 1.0E-1 | 1.8E-1 | 4.1E-1 | 1.2E0 | 6.9E-1 | 166 | 8 | 166 | 8 | 0.43 |
| aF | ng/mL | 2.2E0 | 2.9E0 | 5.0E0 | 5.5E0 | 7.8E0 | 5.7E0 | 4.3E-3 | 4.3E-3 | 5.0E1 | 1.5E1 | 166 | 8 | 166 | 8 | 0.56 |
| aG | mg/mL | 1.4E-1 | 9.2E-2 | 1.6E-1 | 9.7E-2 | 8.7E-2 | 2.5E-2 | 3.2E-2 | 6.9E-2 | 4.8E-1 | 1.5E-1 | 166 | 8 | 166 | 8 | 0.27 |
| aH | ug/mL | 7.2E1 | 5.9E1 | 7.8E1 | 6.5E1 | 4.1E1 | 1.8E1 | 8.9E0 | 5.0E1 | 2.0E2 | 1.0E2 | 166 | 8 | 166 | 8 | 0.45 |
| aI | ug/mL | 1.7E2 | 1.3E2 | 1.8E2 | 1.4E2 | 6.2E1 | 2.3E1 | 3.2E1 | 9.7E1 | 3.4E2 | 1.8E2 | 166 | 8 | 166 | 8 | 0.28 |
| aJ | ug/mL | 2.3E0 | 5.5E0 | 3.1E0 | 7.6E0 | 2.2E0 | 6.6E0 | 8.2E-1 | 2.2E0 | 1.4E1 | 2.3E1 | 166 | 8 | 166 | 8 | 0.83 |
| aK | ng/mL | 1.3E0 | 5.6E-1 | 2.0E0 | 1.7E0 | 2.0E0 | 2.2E0 | 2.9E-4 | 1.3E-1 | 1.0E1 | 6.5E0 | 166 | 8 | 166 | 8 | 0.42 |
| aL | mg/mL | 7.4E-1 | 5.3E-1 | 7.7E-1 | 5.9E-1 | 2.6E-1 | 2.3E-1 | 2.2E-1 | 3.2E-1 | 1.7E0 | 9.2E-1 | 166 | 8 | 166 | 8 | 0.30 |
| aM | U/mL | 1.8E1 | 4.0E1 | 4.0E1 | 1.5E2 | 7.8E1 | 2.4E2 | 4.2E-2 | 4.2E-2 | 8.2E2 | 6.8E2 | 166 | 8 | 166 | 8 | 0.70 |

Figure 37 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aN | U/mL | 1.4E1 | 2.4E1 | 2.5E1 | 2.7E1 | 4.3E1 | 2.6E1 | 2.5E-3 | 7.4E0 | 3.8E2 | 8.8E1 | 166 | 8 | 166 | 8 | 0.60 |
| aO | pg/mL | 5.3E1 | 1.6E2 | 4.2E2 | 6.9E2 | 9.8E2 | 8.5E2 | 6.0E-2 | 3.2E1 | 6.6E3 | 2.1E3 | 166 | 8 | 166 | 8 | 0.70 |
| aP | ng/mL | 1.6E0 | 4.6E0 | 2.2E0 | 7.1E0 | 2.4E0 | 8.6E0 | 4.5E-1 | 1.6E0 | 2.8E1 | 2.8E1 | 166 | 8 | 166 | 8 | 0.87 |
| aQ | ng/mL | 2.4E-1 | 3.0E-1 | 3.6E-1 | 3.5E-1 | 3.2E-1 | 2.6E-1 | 2.0E-4 | 5.2E-2 | 2.0E0 | 9.0E-1 | 166 | 8 | 166 | 8 | 0.53 |
| aR | ng/mL | 1.7E0 | 3.4E0 | 2.9E0 | 4.4E0 | 4.0E0 | 4.2E0 | 2.6E-1 | 6.5E-1 | 3.4E1 | 1.4E1 | 166 | 8 | 166 | 8 | 0.66 |
| aS | ng/mL | 3.7E-1 | 5.2E-1 | 1.0E0 | 8.2E-1 | 2.7E0 | 8.2E-1 | 4.2E-3 | 8.0E-2 | 3.3E1 | 2.6E0 | 166 | 8 | 166 | 8 | 0.58 |
| aU | pg/mL | 6.6E1 | 3.9E1 | 1.0E2 | 1.1E2 | 1.0E2 | 1.7E2 | 7.4E-2 | 7.4E-2 | 7.0E2 | 5.1E2 | 166 | 8 | 166 | 8 | 0.39 |
| aV | ng/mL | 5.9E-1 | 3.6E-1 | 1.1E0 | 6.2E-1 | 2.6E0 | 7.5E-1 | 7.6E-4 | 1.5E-1 | 3.3E1 | 2.4E0 | 166 | 8 | 166 | 8 | 0.39 |
| aW | pg/mL | 1.9E1 | 2.5E1 | 2.3E1 | 2.4E1 | 3.4E1 | 1.4E1 | 7.2E-2 | 7.2E-2 | 4.2E2 | 4.7E1 | 166 | 8 | 166 | 8 | 0.61 |
| aX | ng/mL | 7.5E0 | 4.7E1 | 1.3E1 | 8.4E1 | 2.0E1 | 1.0E2 | 3.0E-1 | 2.5E0 | 2.2E2 | 3.1E2 | 166 | 8 | 166 | 8 | 0.76 |
| aY | pg/mL | 5.3E1 | 6.0E1 | 7.5E1 | 1.0E2 | 1.1E2 | 1.2E2 | 4.1E-1 | 2.7E1 | 1.2E3 | 3.9E2 | 166 | 8 | 166 | 8 | 0.56 |
| aZ | pg/mL | 2.3E2 | 1.3E3 | 5.7E2 | 2.9E3 | 1.2E3 | 3.3E3 | 1.7E0 | 7.5E1 | 1.2E4 | 7.9E3 | 166 | 8 | 166 | 8 | 0.75 |
| bA | ng/mL | 1.3E1 | 1.3E2 | 6.3E1 | 3.1E2 | 1.4E2 | 4.8E2 | 3.0E-2 | 4.7E0 | 9.4E2 | 1.5E3 | 166 | 8 | 166 | 8 | 0.82 |
| bB | ng/mL | 2.8E2 | 1.8E2 | 3.1E2 | 2.2E2 | 1.8E2 | 8.2E1 | 2.1E0 | 1.3E2 | 9.5E2 | 3.8E2 | 166 | 8 | 166 | 8 | 0.35 |
| bC | ng/mL | 3.2E2 | 1.3E3 | 5.9E2 | 1.9E3 | 7.7E2 | 1.9E3 | 1.4E1 | 5.8E1 | 4.7E3 | 4.0E3 | 166 | 8 | 166 | 8 | 0.68 |
| bE | mg/mL | 5.2E0 | 5.3E0 | 5.4E0 | 6.6E0 | 2.1E0 | 3.5E0 | 1.3E0 | 2.6E0 | 1.2E1 | 1.2E1 | 166 | 8 | 166 | 8 | 0.57 |
| bF | pg/mL | 3.5E1 | 6.6E1 | 3.5E2 | 7.1E1 | 1.4E3 | 4.2E1 | 5.0E-2 | 1.4E1 | 1.1E4 | 1.5E2 | 166 | 8 | 166 | 8 | 0.65 |
| bG | ng/mL | 1.6E0 | 1.8E0 | 3.1E0 | 4.7E0 | 4.4E0 | 5.8E0 | 1.1E-1 | 1.6E-1 | 3.0E1 | 1.5E1 | 166 | 8 | 166 | 8 | 0.55 |
| bH | pg/mL | 5.7E-1 | 6.9E0 | 6.2E0 | 8.5E0 | 2.4E1 | 9.0E0 | 5.7E-1 | 5.7E-1 | 2.8E2 | 2.3E1 | 166 | 8 | 166 | 8 | 0.63 |
| bI | ng/mL | 4.0E-3 | 4.0E-3 | 9.5E-2 | 7.3E-2 | 2.0E-1 | 1.4E-1 | 4.0E-3 | 4.0E-3 | 9.8E-1 | 3.9E-1 | 166 | 8 | 166 | 8 | 0.51 |
| bJ | mg/mL | 1.9E0 | 2.2E0 | 2.4E0 | 2.8E0 | 2.0E0 | 2.5E0 | 2.5E-4 | 8.7E-1 | 1.1E1 | 8.9E0 | 166 | 8 | 166 | 8 | 0.56 |
| bL | pg/mL | 3.7E0 | 1.4E1 | 9.1E0 | 1.3E1 | 1.2E1 | 7.8E0 | 4.6E-2 | 3.2E0 | 6.0E1 | 2.4E1 | 166 | 8 | 166 | 8 | 0.72 |
| bM | mg/mL | 1.8E0 | 1.1E0 | 2.2E0 | 1.4E0 | 1.5E0 | 1.2E0 | 1.8E-2 | 1.6E-2 | 8.6E0 | 3.8E0 | 166 | 8 | 166 | 8 | 0.33 |
| bN | ng/mL | 3.3E1 | 3.0E1 | 1.2E2 | 6.1E1 | 2.9E2 | 7.9E1 | 1.4E-1 | 6.7E0 | 1.9E3 | 2.5E2 | 166 | 8 | 166 | 8 | 0.49 |
| bO | ng/mL | 4.0E-2 | 4.0E-2 | 9.6E0 | 4.0E-2 | 2.0E1 | 0.0E0 | 4.0E-2 | 4.0E-2 | 1.3E2 | 4.0E-2 | 166 | 8 | 166 | 8 | 0.33 |
| bP | mg/mL | 5.2E-1 | 5.4E-1 | 7.5E-1 | 6.5E-1 | 7.1E-1 | 5.0E-1 | 4.9E-2 | 9.2E-2 | 4.8E0 | 1.6E0 | 166 | 8 | 166 | 8 | 0.48 |
| bQ | pg/mL | 2.1E1 | 8.1E1 | 1.4E2 | 7.8E1 | 1.1E3 | 4.9E1 | 1.5E-1 | 2.2E1 | 1.3E4 | 1.4E2 | 166 | 8 | 166 | 8 | 0.77 |
| bR | ng/mL | 1.2E-2 | 1.2E-2 | 1.6E-1 | 9.2E-2 | 7.2E-1 | 1.5E-1 | 1.2E-2 | 1.2E-2 | 8.7E0 | 3.8E-1 | 166 | 8 | 166 | 8 | 0.47 |
| bS | pg/mL | 9.4E-1 | 9.4E-1 | 9.0E0 | 2.1E1 | 4.1E1 | 3.1E1 | 9.4E-1 | 9.4E-1 | 3.9E2 | 7.2E1 | 166 | 8 | 166 | 8 | 0.64 |
| bU | ng/mL | 7.0E-2 | 2.0E-1 | 1.9E-1 | 1.8E-1 | 5.4E-1 | 1.5E-1 | 1.3E-2 | 1.3E-2 | 6.6E0 | 4.1E-1 | 166 | 8 | 166 | 8 | 0.59 |
| bV | pg/mL | 4.8E2 | 6.7E2 | 6.2E2 | 8.8E2 | 9.0E2 | 5.8E2 | 1.6E2 | 2.1E2 | 2.2E3 | 2.2E3 | 166 | 8 | 166 | 8 | 0.75 |
| bW | pg/mL | 3.1E2 | 6.2E2 | 4.7E2 | 1.4E3 | 5.0E2 | 1.6E3 | 8.4E1 | 2.5E2 | 4.8E3 | 3.9E3 | 166 | 8 | 166 | 8 | 0.74 |
| bX | ng/mL | 2.5E-5 | 1.6E-3 | 2.6E-3 | 2.7E-3 | 3.2E-3 | 3.1E-3 | 2.5E-5 | 2.5E-5 | 1.3E-2 | 7.2E-3 | 166 | 8 | 166 | 8 | 0.52 |
| bZ | pg/mL | 2.7E2 | 1.8E3 | 2.0E3 | 2.4E3 | 7.2E3 | 2.5E3 | 1.5E-1 | 1.4E2 | 5.8E4 | 7.4E3 | 166 | 8 | 166 | 8 | 0.72 |
| cA | pg/mL | 6.0E-1 | 6.0E-1 | 4.1E0 | 4.0E0 | 2.9E1 | 7.3E0 | 6.0E-1 | 6.0E-1 | 3.7E2 | 2.1E1 | 166 | 8 | 166 | 8 | 0.56 |
| cB | ng/mL | 5.1E-2 | 1.8E-2 | 7.5E-2 | 7.0E-2 | 8.8E-2 | 1.0E-1 | 1.7E-3 | 1.7E-3 | 4.3E-1 | 2.6E-1 | 166 | 8 | 166 | 8 | 0.39 |
| cC | pg/mL | 4.3E1 | 2.9E1 | 4.6E1 | 2.8E1 | 5.1E1 | 2.2E1 | 1.0E0 | 1.0E0 | 4.5E2 | 5.9E1 | 166 | 8 | 166 | 8 | 0.36 |
| cD | pg/mL | 4.9E0 | 4.4E0 | 1.3E1 | 5.1E0 | 4.6E1 | 3.7E0 | 3.3E-1 | 8.8E-1 | 4.8E2 | 9.6E0 | 166 | 8 | 166 | 8 | 0.48 |
| cE | pg/mL | 6.0E1 | 1.2E2 | 2.7E2 | 1.4E2 | 6.1E2 | 9.4E1 | 1.2E-1 | 3.2E1 | 3.8E3 | 2.8E2 | 166 | 8 | 166 | 8 | 0.63 |
| cF | pg/mL | 2.5E0 | 5.3E-1 | 1.6E1 | 9.0E0 | 3.0E1 | 1.4E1 | 5.3E-1 | 5.3E-1 | 2.7E2 | 3.8E1 | 166 | 8 | 166 | 8 | 0.44 |
| cG | pg/mL | 5.3E1 | 1.8E2 | 1.7E2 | 3.2E2 | 8.2E2 | 3.4E2 | 7.8E0 | 4.0E1 | 1.0E4 | 1.1E3 | 166 | 8 | 166 | 8 | 0.80 |
| cH | uIU/mL | 3.3E0 | 4.2E0 | 7.7E0 | 7.8E0 | 1.7E1 | 1.1E1 | 8.6E-3 | 8.6E-3 | 1.6E2 | 3.4E1 | 166 | 8 | 166 | 8 | 0.52 |
| cI | ng/mL | 6.1E0 | 6.1E0 | 1.4E1 | 1.3E1 | 2.2E1 | 1.6E1 | 3.2E-2 | 1.1E0 | 1.2E2 | 4.1E1 | 166 | 8 | 166 | 8 | 0.49 |
| cJ | ug/mL | 6.7E1 | 3.1E1 | 1.0E2 | 4.3E1 | 1.0E2 | 5.2E1 | 6.9E0 | 5.6E0 | 6.4E2 | 1.7E2 | 166 | 8 | 166 | 8 | 0.28 |
| cK | ng/mL | 3.8E-3 | 3.8E-3 | 2.2E-2 | 3.5E-2 | 1.2E-1 | 7.2E-2 | 3.8E-3 | 3.8E-3 | 1.5E0 | 2.1E-1 | 166 | 8 | 166 | 8 | 0.57 |
| cL | pg/mL | 2.1E2 | 2.1E2 | 5.3E2 | 6.9E2 | 2.0E3 | 9.4E2 | 3.1E1 | 6.7E1 | 2.4E4 | 2.8E3 | 166 | 8 | 166 | 8 | 0.58 |
| cM | pg/mL | 2.7E2 | 2.3E2 | 2.9E2 | 2.3E2 | 1.7E2 | 6.8E1 | 2.5E1 | 1.3E2 | 1.1E3 | 3.1E2 | 166 | 8 | 166 | 8 | 0.40 |
| cN | pg/mL | 1.2E2 | 1.3E2 | 1.3E2 | 1.4E2 | 8.6E1 | 4.0E1 | 3.8E1 | 8.6E1 | 1.1E3 | 1.9E2 | 166 | 8 | 166 | 8 | 0.60 |
| cO | pg/mL | 2.1E2 | 4.7E2 | 4.0E2 | 5.8E2 | 1.5E3 | 4.4E2 | 5.4E1 | 9.6E1 | 1.9E4 | 1.5E3 | 166 | 8 | 166 | 8 | 0.75 |
| cP | pg/mL | 2.4E3 | 2.9E3 | 2.5E3 | 2.8E3 | 9.5E2 | 1.4E3 | 6.2E2 | 1.4E3 | 5.6E3 | 4.7E3 | 166 | 8 | 166 | 8 | 0.58 |
| cQ | ng/mL | 5.0E-2 | 1.3E-1 | 1.3E-1 | 1.8E-1 | 2.1E-1 | 1.7E-1 | 2.0E-3 | 2.0E-3 | 1.3E0 | 3.9E-1 | 166 | 8 | 166 | 8 | 0.62 |
| cR | ng/mL | 3.3E2 | 8.4E2 | 5.8E2 | 1.0E3 | 8.3E2 | 7.7E2 | 2.0E1 | 1.1E2 | 7.7E3 | 2.2E3 | 166 | 8 | 166 | 8 | 0.71 |
| cS | ng/mL | 2.8E2 | 8.8E2 | 4.1E2 | 1.9E3 | 4.2E2 | 2.4E3 | 4.1E1 | 1.4E2 | 2.5E3 | 7.1E3 | 166 | 8 | 166 | 8 | 0.75 |
| cT | ng/mL | 4.9E1 | 1.5E2 | 1.5E2 | 3.8E2 | 2.9E2 | 5.1E2 | 3.6E0 | 1.9E1 | 2.1E3 | 1.5E3 | 166 | 8 | 166 | 8 | 0.71 |
| cU | ng/mL | 5.8E1 | 1.9E2 | 9.4E1 | 2.1E2 | 1.5E2 | 1.0E2 | 6.2E0 | 9.8E1 | 1.6E3 | 3.9E2 | 166 | 8 | 166 | 8 | 0.89 |
| cV | ng/mL | 2.0E-1 | 1.8E-1 | 7.6E-1 | 2.6E-1 | 3.8E0 | 1.5E-1 | 2.5E-2 | 9.7E-2 | 4.7E1 | 4.9E-1 | 166 | 8 | 166 | 8 | 0.53 |
| cW | mIU/mL | 4.8E-2 | 1.0E-1 | 8.8E-2 | 1.1E-1 | 3.5E-1 | 8.7E-2 | 4.8E-3 | 3.3E-2 | 4.5E0 | 2.9E-1 | 166 | 8 | 166 | 8 | 0.70 |

Figure 37 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cX | ng/mL | 1.2E-1 | 3.8E-2 | 1.9E0 | 1.2E-1 | 5.7E0 | 1.4E-1 | 2.3E-4 | 1.1E-2 | 2.8E1 | 4.1E-1 | 166 | 8 | 166 | 8 | 0.41 |
| cY | ng/mL | 7.5E0 | 4.4E0 | 1.1E1 | 9.2E0 | 1.1E1 | 1.2E1 | 1.7E-1 | 6.0E-1 | 6.1E1 | 3.6E1 | 166 | 8 | 166 | 8 | 0.40 |
| cZ | ug/mL | 1.3E1 | 1.1E1 | 1.5E1 | 1.5E1 | 6.8E0 | 7.9E0 | 2.3E0 | 7.1E0 | 4.6E1 | 3.0E1 | 166 | 8 | 166 | 8 | 0.45 |
| dA | pg/mL | 3.1E2 | 4.1E2 | 3.8E2 | 4.6E2 | 4.6E2 | 2.5E2 | 1.0E2 | 1.7E2 | 5.8E3 | 8.8E2 | 166 | 8 | 166 | 8 | 0.62 |
| dB | ug/mL | 1.8E1 | 2.0E1 | 1.8E1 | 2.1E1 | 2.0E1 | 5.7E0 | 2.1E0 | 1.5E1 | 2.5E2 | 2.8E1 | 166 | 8 | 166 | 8 | 0.62 |
| dC | nmol/L | 3.5E1 | 2.7E1 | 3.8E1 | 2.7E1 | 1.7E1 | 6.4E0 | 7.8E0 | 1.5E1 | 1.4E2 | 3.8E1 | 166 | 8 | 166 | 8 | 0.27 |
| dD | ug/mL | 3.4E1 | 2.9E1 | 3.5E1 | 3.1E1 | 1.1E1 | 7.0E0 | 1.4E1 | 2.3E1 | 7.4E1 | 4.3E1 | 166 | 8 | 166 | 8 | 0.35 |
| dE | ng/mL | 4.1E-1 | 9.9E-1 | 5.4E-1 | 1.2E0 | 5.5E-1 | 9.3E-1 | 8.4E-3 | 3.0E-1 | 2.7E0 | 2.9E0 | 166 | 8 | 166 | 8 | 0.75 |
| dF | ng/mL | 2.4E2 | 3.8E2 | 3.4E2 | 5.1E2 | 2.5E2 | 2.5E2 | 7.5E1 | 2.8E2 | 1.3E3 | 8.9E2 | 166 | 8 | 166 | 8 | 0.75 |
| dG | ng/mL | 1.2E1 | 2.0E1 | 1.7E1 | 2.6E1 | 1.9E1 | 1.9E1 | 3.0E0 | 6.7E0 | 1.8E2 | 6.5E1 | 166 | 8 | 166 | 8 | 0.70 |
| dH | pg/mL | 8.0E0 | 1.3E1 | 2.1E1 | 1.9E1 | 6.3E1 | 2.3E1 | 4.0E-2 | 8.3E-1 | 6.7E2 | 7.6E1 | 166 | 8 | 166 | 8 | 0.65 |
| dI | pg/mL | 4.6E-1 | 1.7E0 | 3.7E0 | 4.9E0 | 2.6E1 | 6.5E0 | 4.6E-1 | 4.6E-1 | 3.3E2 | 1.9E1 | 166 | 8 | 166 | 8 | 0.66 |
| dJ | ng/mL | 2.0E0 | 2.0E0 | 2.1E0 | 2.2E0 | 1.1E0 | 1.2E0 | 3.2E-2 | 5.7E-1 | 5.6E0 | 4.0E0 | 166 | 8 | 166 | 8 | 0.51 |
| dK | uIU/mL | 1.3E0 | 3.8E-1 | 2.2E0 | 1.2E0 | 3.6E0 | 2.1E0 | 2.8E-4 | 1.4E-2 | 3.9E1 | 6.1E0 | 166 | 8 | 166 | 8 | 0.26 |
| dL | ng/mL | 8.7E2 | 1.0E3 | 1.1E3 | 1.2E3 | 6.3E2 | 6.1E2 | 2.8E2 | 6.3E2 | 4.8E3 | 2.3E3 | 166 | 8 | 166 | 8 | 0.62 |
| dM | pg/mL | 9.7E2 | 2.2E3 | 1.3E3 | 2.7E3 | 1.5E3 | 2.0E3 | 3.7E2 | 7.1E2 | 1.5E4 | 5.8E3 | 166 | 8 | 166 | 8 | 0.72 |
| dN | ug/mL | 9.8E1 | 1.4E2 | 1.0E2 | 1.3E2 | 4.4E1 | 3.6E1 | 2.4E1 | 6.6E1 | 3.3E2 | 1.7E2 | 166 | 8 | 166 | 8 | 0.72 |
| fR | ng/ml | 1.5E5 | 2.9E5 | 2.1E5 | 3.5E5 | 1.7E5 | 2.6E5 | 3.6E4 | 1.9E2 | 6.9E5 | 8.7E5 | 106 | 9 | 106 | 9 | 0.68 |

Analyte panel data:

Unconstrained panels with 3 analytes, where 1.0E-8 >= 'model p-value' > 0. Contains 19 panels of 590,601 total panels evaluated. : Ml{Qd(aA It Ji Jj Jt Lv Lw Mi Ms Nu Nw Oe Ok On) LvMi} Mi{Ms(Hq Lx Nf) LvHq}

Unconstrained panels with 3 analytes, where 1.0E-7 >= 'model p-value' > 1.0E-8. Contains 308 panels of 590,601 total panels evaluated. :
Mi{Lv(aA Fp Hw Ih Ii Ij Ik Il Im In It Iu Jj Jl Jo Jp Js Lu Lw Lx Ly Lz Md Mf Mg Mh Mm Mn Mr Ms Mt Mw Mx Nb Nd Ne Nf Ng Nh Ni Nj Nk Nl Nm Nn Ns Nu Nx Ny Oe Of Og Oh Oi Ok Om On Oy Oz Pb Pc Pd Pf Pg Po Qd Qe) Ml(aA Hq Hu Hv Hx Ij In Ir Is Iv Ji Jj Jl Jo Jp Jq Jt Lw Lx Ly Mg Mj Mm Mn Mr Ms Mz Nb Nd Ne Nf Ng Nh Nj Nm Ns Nu Nx Ny Oe Of Oh Ok On Pc Pd Pf Pg Qa) Nj(aA Hq Im Jj Jl Jo Mg Mm Mn Ms Nb Ne Nf Nh Nn Nu Of On Pb Pc Pd Pf) Nf(aA Hu Hx Ij Il Im In Iu Jt Nb Ok) Ms(Jo Lu Ly Nd Pd) Hq(Hu Il Nb Nk Pg) Of(Il Jt Mw Nb) Qd(Im Lj) Jo(Iu Nk) Jt(Md Pb) LxIl NbPd} Ml{Qd(Et Fp Fr Hq Hr Hu Hv Hw Hx Ih Ii Ij Ik Il Im In Io Ip Iq Ir Is Iu Iv Jg Jh Jk Jl Jm Jn Jo Jp Jq Jr Js Lh Li Lj Lu Lx Ly Lz Ma Mb Mc Md Me Mf Mg Mh Mj Mk Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nv Nx Ny Of Og Oh Oi Om Oy Oz Pa Pb Pc Pd Pe Pf Pg Po Pz Qa Qb Qc Qe) Lv(aA Ir Is Ji Jt Ok) Ji(Hu Hv In Iv Jt) Jt(Im Jo) Ok(In Qa) OfOn} Qd{Im(Lj Lv Lw Mx Nk On) Lv(Ik Lj Mf)} Lv{On(Of Pb) NjaA OkPb} aX{CuCx aAcX} cU{dH(aJ aP)}

Unconstrained panels with 3 analytes, where 1.0E-6 >= 'model p-value' > 1.0E-7. Contains 2,760 panels of 590,601 total panels evaluated. :
Mi{Nk(aA Et Fp Fr Hr Hu Hv Hw Hx Ih Ii Ij Ik Il Im In Io Ip Iq Ir Is It Iu Iv Jg Jh Ji Jj Jk Jl Jm Jn Jp Jq Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jo(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jp Jq Jr Js Jt Lh Li Lj Lu Lw Lx Ly Lz Ma Mb Mc Md Me Mf Mg Mh Mj Mk Mm Mn Mp Mq Mr Mt Mu Mv Mw Mx My Mz Na Nb Nc Nd Ne Nf Ng Nh Ni Nl Nm Nn Nu Nv Nw Nx Ny Oe Of Og Oh Oi Ok Om On Oy Oz Pa Pb Pc Pd Pe Pf Pg Po Pz Qa Qb Qc Qd Qe) Pd(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jp Jq Jr Js Jt Lh Li Lj Lu Lw Lx Ly Lz Ma Mb Mc Md Me Mf Mg Mh Mj Mk Mm Mn Mp Mq Mr Mt Mu Mv Mw Mx My Mz Na Nc Nd Ne Nf Ng Nh Ni Nl Nm Nn No Nq Nr Ns Nt Nu Nv Nw Nx Ny Oe Of Og Oh Oi Ok Om On Oy Oz Pa Pb Pc Pe Pf Pg Po Pz Qa Qb Qc Qd Qe) Hq(aA Et Fp Fr Hv Hw Hx Ih Ii Ij Ik Im In Io Ip Iq Ir Is It Iu Iv Jg Jh Ji Jj Jk Jl Jm Jn Jp Jq Jr Js Jt Lh Li Lj Lu Lw Lx Ly Lz Ma Mb Mc Md Me Mf Mg Mh Mj Mk Mm Mn Mp Mq Mr Mt Mu Mv Mw Mx My Mz Na Nc Nd Ne Nf Ng Nh Ni Nl Nm Nn No Nq Nr Ns Nt Nu Nv Nw Nx Ny Oe Of Og Oh Oi Ok Om On Oy Oz Pa Pb Pc Pe Pf Po Pz Qa Qb Qc Qd Qe) Ms(aA Et Fp Fr Hr Hu Hv Hw Hx Ih Ii Ij Ik Il Im In Io Ip Iq Ir Is It Iu Iv Jg Jh Ji Jj Jk Jl Jm Jn Jp Jq Jr Js Jt Lh Li Lj Lw Lz Ma Mb Mc Md Me Mf Mg Mh Mj Mk Mm Mn Mp Mq Mr Mt Mu Mv Mw Mx My Mz Na Nb Nc Ne Ng Nh Ni Nl Nm Nn No Nq Nr Ns Nt Nu Nv Nw Nx Ny Oe Of Og Oh Oi Ok Om On Oy Oz Pa Pb Pc Pe Pf Pg Po Pz Qa Qb Qc Qd Qe) Of(aA Fp Fr Hr Hu Hv Hw Hx Ih Ii Ij Ik Im In Io Ip Iq Ir Is It Iu Iv Jg Jh Ji Jj Jk Jl Jm Jn Jp Jr Js Lh Li Lj Lu Lw Lx Ly Lz Ma Mc Md Me Mf Mg Mh Mj Mk Mm Mn Mp Mq Mr Mt Mu Mv Mx My Mz Na Nc Nd Ne Nf Ng Nh Ni Nl Nm Nn No Nq Nr Ns Nt Nu Nv Nw Nx Ny Oe Og Oh Oi Ok Om On Oy Oz Pa Pb Pc Pe Pf Pg Po Qa Qb Qc Qd Qe) Nf(Et Fp Fr Hr Hv Hw Ih Ii Ik Io Ip Iq Ir Is It Iv Jg Jh Ji Jj Jk Jl Jm Jn Jp Jq Jr Js Lh Li Lj Lu Lw Lx Ly Lz Ma Mb Mc Md Me Mf Mh Mj Mk Mm Mn Mp Mq Mr Mt Mu Mv Mw Mx My Mz Na Nc Nd Ne Ng Nh Ni Nl Nm Nn No Nq Nr Ns Nt Nv Nw Nx Ny Oe Og Oh Oi Om On Oy Oz Pa Pb Pe Pf Pg Po Pz Qa Qb Qc Qd Qe) Nu(aA Fp Fr Hr Hu Hv Hw Hx Ih Ii Ij Ik Il Im In Ip Iq Ir Is It Iu Iv Jj Jl Jn Jp Jq Jr Js Jt Lh Li Lj Lu Lw Lx Ly Lz Ma Mb Md Me Mf Mg Mh Mj Mk Mm Mn Mp Mq Mr Mt Mu Mv Mw Mx My Mz Nb Nc Nd Ne Ng Nh Ni Nl Nm Nn No Nq Nr Ns Nt Nv Nw Nx Ny Oe Og Oh Oi Ok Om On Oy Oz Pb Pc Pf Pg Po Pz Qc Qd Qe) Nj(Et Fp Fr Hr Hu Hv Hw Hx Ih Ii Ij Ik Il In Io Ip Iq Ir Is It Iu Iv Jg Jh Ji Jk Jm Jn Jp Jq Jr Js Jt Lh Li Lj Lu Lw Lx Ly Lz Ma Mb Mc Md Me Mf Mh Mj Mk Mp Mq Mr Mt Mu Mv Mw Mx My Mz Na Nc Nd Ng Ni Nl Nm No Nq Nr Ns Nt Nv Nw Nx Ny Oe Og Oh Oi Ok Om On Oy Oz Pa Pe Pg Po Pz Qa Qb Qc Qd Qe) Pf(aA Fp Hr Hu Hv Hw Hx Ih Ii Ij Ik Il Im In Ip Ir Is It Iu Iv Jj Jk Jl Jp Jq Jt Li Lj Lu Lw Lx Ly Lz Ma Mb Md Me Mf Mg Mh Mj Mk Mm Mn Mp Mq Mr Mt Mv Mw Mx My Mz Nb Nc Nd Ne Ng Nh Ni Nl Nm Nn No Nq Nr Ns Nw Nx Ny Oe Og Oh Oi Ok Om Oy Oz Pa Pe Pg Po Pz Qa Qd Qe) Im(aA Fp Fr Hr Hu Hv Hw Hx Ii Ij Il In Ip Iq Ir Is It Iu Iv Ji Jj Jl Jn Jp Jq Jr Jt Lh Li Lu Lw Lx Ly Lz Ma Mb Md Me Mf Mg Mh Mj Ml Mm Mn Mp Mq Mr Mt Mu Mv Mw Mx My Mz Nb Nd

ApbQ aEfR} cS{aZ(Af Aj Al An Ar As Ax Bb Bn bO cE Cq Cu Cv cX Dc Dd Dg Di Dk Dl) bM(Ax bA bO Cq CX dD dH) Ax(aL As Bb cB Cs) Cx(Aj aL bA Bb) Cu(As Bn cV) AdDc AjcJ aPdH bAcX} aP{dH(aD al aL aZ bA bC bM bN bO bP bQ bW cB cG cP CX dA dE dG dL) dG(al aL cJ CX) Cx(aZ cJ Dd) aZbO cEcG} Mg{Ng(Is Jg Jk Jl Jp Mr Nb Nw Oz Pa Pe Pg) Jj(Ir Jl Nu Pg) Jl(Im Jo Of) Of(Nb Pa) Mhls NfNw Nklm} Cu{Cx(aU Ba bE cK dC DE dH dK) cJ(Bn Cq Cw Dc dE) Ad(cK dH dK) As(cK De dH) BnDe DccK} aZ{cJ(Al Ap Ax Ba Bn Cx Di Fr) Cx(aJ bA bC bW De) bW(Bn bO cE) aJ(bO cX)} Im{Nb(Lw Nf Nj Nk Of Pb) Lw(Hu Jl Jp) Mp(Jl Jp Nj) Nn(Jl Nj) Pg(Hq Jj)} Jj{Pg(Hq lu Mm Nf Nj Nl Nu Of) Nu(lu Jk Nl Pe) NtNj MmPe} Lw{Of(Jl Nb Pa Pe Pg) Jl(Jo Ms Pb) NbPb HqPg IsJr} As{Ax(bW Dc dK) DebA DkdK} Nb{Of(Jh Nu Pg) Pb(Nj Nu)} bA{BnDe CxaU bWcE cCdE} cG{cE(Bn CX) CxbF} Mm{Pe(Ng Oy) Mhls} Pg{Hq(Mp Pa) JlOf} Nf{Nw(Hv In)} AxaLbE Unconstrained panels with 2 analytes, where 1.0E-7 >= 'model p-value' > 0. Contains 4 panels of 14,763 total panels evaluated. : Mi(Lv Ml Nj) MlQd Unconstrained panels with 2 analytes, where 1.0E-6 >= 'model p-value' > 1.0E-7. Contains 120 panels of 14,763 total panels evaluated. : Mi(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mj Mk Mm Mn Mp Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qc Qd Qe) Lv(aA Qd) Ml(Ji Jt) ImQd Unconstrained panels with 2 analytes, where 1.0E-5 >= 'model p-value' > 1.0E-6. Contains 67 panels of 14,763 total panels evaluated. : Lv(Hx Im Ir Is Iu Ji Jj Jl Jp Jt Lw Mg Mm Mp Mz Nl Nn Nr Nu Nw Oh Ok On Pe Qa Qe) Qd(aA Ik Il In Iu Lj Lw Lz Mf Mg Mm Mp Nb Nu Ok On Qc) Ok(Mg Ml Mp Nf Of Pb) Jt(Hw Md Na Nf Pb) On(Nf Oe Of Pb) aA(cU Mg Nj) Mi(Et Qb) MlIs NfJi aPdH aXcX Unconstrained panels with 2 analytes, where 1.0E-4 >= 'model p-value' > 1.0E-5. Contains 484 panels of 14,763 total panels evaluated. : Qd(Et Fp Fr Hq Hr Hu Hv Hw Hx Ih Ii Ij Io Ip Iq Ir Is It Iv Jg Jh Ji Jj Jk Jl Jm Jn Jo Jp Jq Jr Js Jt Lh Li Lu Lx Ly Ma Mb Mc Md Me Mh Mj Mk Mn Mq Mr Ms Mt Mu Mv Mw Mx My Mz Na Nc Nd Ne Nf Ng Nh Ni Nj Nk Nl Nm Nn No Nq Nr Ns Nt Nv Nw Nx Ny Oe Of Og Oh Oi Om Oy Oz Pa Pb Pc Pd Pe Pf Pg Po Pz Qa Qb Qe) Lv(Et Fr Hq Hr Hu Hv Hw Ih Ii Ij Ik Il In Io Ip Iq Iv Jg Jh Jk Jm Jn Jo Jq Jr Js Lh Li Lj Lx Ly Lz Ma Mb Md Me Mf Mj Mk Ml Mn Mq Mr Ms Mt Mu Mv Mw Mx My Na Nb Nc Nd Ne Nf Ng Nh Ni Nj Nk Nm No Nq Ns Nt Nv Nx Ny Oe Of Og Oi Om Oy Oz Pa Pb Pc Pg Po Qb Qc) On(aA Hq Hr Hu Im Ip Ir Is Iu Iv Jh Ji Jj Jo Jp Jt Lw Lx Ma Md Me Mg Ml Mm Mp Ms Mv Mw My Mz Ng Nj Nk Nl Nm Ns Nt Nu Og Oh Oi Ok Om Oy Pc Pe Po Qa) Ok(aA Hr Hv Hw Hx Ij Il Im In Ip Ir Is Iu Iv Jk Jl Jn Jo Jp Jq Lw Lx Ma Md Mm Mz Na Nb Ni Nj Nk Nl Nn Nq Nt Nu Nw Ny Oh Om Pa Pc Pe Pg Po) aA(aX aZ bC bO bW cB cG cJ cS cV CX dB dC dE Fr Hx Ij Il Im Ip Ir Is Iu Iv Ji Jt Lw Lx Ma Ml Mm Mp Mz Nk Nl Nt Nu Nw Oe Pe Pg Po) aX(aJ Al An Ar Aw Ax bA Bb Bo cJ Cp Cq Cs CU Cx Dc Dd De dH Di Dl Fr) cS(Af Aj aL Ar As Ax aZ bA Bb Bc bM bO CU CX Dc Di Dk Dl dM) Jt(Hr Hv Ij Im In Jj Jn Jo Jp Jq Mz Ni Nu Nw Ny Of Om) Ji(Hw Ij In Iu Jq Md Mm Mp Mz Ni Nk Nl Nu Om Pb) Lw(Im Ir Is Iu Iv Jl Jp Nt Nu Nw Pa Pe Pg Po) cU(aC aG aJ aP As aZ bF bM bZ cE dE dH dK) Im(Ir Iu Iv Jl Jp Mp Nb Nn Pe Pg) aP(aZ cB cE cJ cV CX dC dG) Jj(Jk Jl Nt Nu Pe Pg Po) Nw(Iu Ml Mp Nf Nl Nu) Mm(Ir Is Iv Pe Qa) Ml(Iv Mj Pe Qa) Mp(Ir Is Iv Jp) Cu(As Cx dE) Nu(Ir Is Jp) Mg(Ir Is Jl) aZ(aJ bO Cx) Nb(Of Pb) NnPe HqPg aJbC bAdE Unconstrained panels with 2 analytes, where 1.0E-3 >= 'model p-value' > 1.0E-4. Contains 1,673 panels of 14,763 total panels evaluated. : aA(aC aD aE aF aG aH aI aJ aK AL aM aN aO AP aQ aR aS aU aV aW aY bA BB bE bF bG bH bI bJ bL bM bN bP bQ bR bS bU bV bX bZ cA cC cD cE cF cH cI cK cL cM cN cO cP cQ cR cT Cu cW cY cZ dA dD De dF dG dH dI dJ dK dL dM dN Et Fp fR Hq Hr Hu Hv Hw Ih Ii Ik In Io Iq It Jg Jh Jj Jk Jl Jm Jn Jo Jp Jq Jr Js Lh Li Lj Lu Ly Lz Mb Mc Md Me Mf Mh Mj Mk Mn Mq Mr Ms Mt Mu Mv Mw Mx My Na Nb Nc Nd Ne Nf Ng Nh Ni Nm Nn No Nq Nr Ns Nv Nx Ny Of Og Oh Oi Om Oy Oz Pa Pb Pc Pd Pf Pz Qa Qb Qc Qe) cS(aC AD aE aF aG aH aI aJ aK AI aM AN AO AP aQ aR aS aU aV AW aX aY Ba bB bC bE bF BG bH bI bJ bL BN Bo bP bQ bR bS bU bV bW bX bZ cA cB cC cD cE cF cG CH cI cJ cK cL cM cN CO CP CQ cR Cs CT CV CW cY cZ dA DB dC DD DE dF DG dH dI dJ dK dL dN FR) aP(aC aD aE aF aG aH aI aJ aK AL aM aN aO aQ aR AS aU aV AW AX aY bA BB bC bE bF bG bH bI bJ bL bM BN bO bP bQ bR bS bU bV bW bX bZ cA cC cD cF cG cH cI cK cL cM cN cO cP cQ cR cT Cu cW cY cZ dA dB DD DE dF DI dJ dK dL dM dN Fr) aX(AD aE Af aG aH aI Aj aL aM aN AO Ap aR AS aU aV aY aZ Ba bB BC bF BG bH bJ bL bM BN bO bP bQ bR bS bV bW bZ cA cB cC cD cE cF cG CH cK cM CO cP cQ cR CT CV CW cZ DB dC dD dE dF DG dI DK dL dM fR) Ji(Et Fr Hr Hu Hv Hx Ih Il Im Ip Ir Is It Iv Jg Jh Jj Jk Jl Jm Jn Jo Jp Jr Js Jt Li Lw Lx Lz Ma Mb Mf Mg Mj Mk Mq Mr Ms Mt Mv Mx My Na Nb Nc Nd Ne Nh Nj Nn No Nq Nr Ns Nt Nv Nw Nx Ny Oe Of Og Oh Oi Ok Oy Oz Pa Pc Pd Pe Pg Po Pz Qa Qb Qe) Nw(Et Fr Hq Hu Hv Hw Hx Ij Il Im In Ip Ir Is Iv Jj Jk Jl Jo Jp Jq Jr Li Lj Lx Ly Ma Md Me Mf Mg Mh Mj Mk Mm Mq Mr Ms Mt Mv My Mz Na Nb Ne Ng Nh Ni Nj Nk Nm Nn Nq Nr Ns Nt Ny Oe Of Og Oh Oi On Oy Oz Pa Pb Pc Pe Pf Pg Po Qa Qe) Ok(Et Fp Fr Hq Hu Ih Ii Ik Io Iq It Jg Jh Jj Jm Jr Js Jt Lh Li Lj Lu Ly Lz Mb Mc Me Mf Mh Mj Mk Mn Mq Mr Ms Mt Mu Mv Mw Mx My Nc Nd Ne Ng Nh Nm No Nr Ns Nv Nx Oe Og Oi Oy Oz Pd Pf Pz Qa Qb Qc Qe) On(Et Fp Fr Hv Hw Hx Ih Ii Ij Ik Il In Io Iq It Jg Jk Jl Jm Jn Jq Jr Js Lh Li Lj Lu Ly Lz Mb Mc Mf Mh Mj Mk Mn Mq Mr Mt Mu Mx Na Nb Nc Nd Ne Nh Ni Nn No Nq Nr Nv Nx Ny Oz Pa Pd Pf Pg Pz Qb Qc Qe) Pe(Et Fp Fr Hq Hr Hv Hx In Ip Ir Is Iu Iv Jg Jh Jk Jl Jo Jp Jq Jt Li Lj Lx Ly Lz Ma Md Mf Mg Mh Mp Mq Ms Mz Na Nb Ne Nf Ng Ni Nj Nk Nl Nm Nq Ns Nt Nu Oe Of Og Oh Oi Oy Oz Pa Pb Pc Pd Pf Pg Po Qa) Is(Et Fr Hv Hx Ij Im In Ip Ir It Iu Iv Jj Jk Jl Jo Jp Jr Js Jt Lh Li Lx Ly Ma Me Mf Mh Mq Mr Ms Mz Nb Ne Nf Ng Nh Ni Nj Nk Nl Nm Nn No Nq Nr Nt Nv Oe Of Og Oh Oi Oy Oz Pa Pc Pg Po Qa) Jt(Et Fr Hu Hx Ih Il Ip Ir It Iu Iv Jg Jh Jk Jl Jr Li Lw Lx Ma Mb Mf Mg Mj Mk Mm Mp Mr Ms Mt Nb Nd Ne Ng Nh Nj Nk Nl Nn No Nq Nr Nt Nv Nx Oe Og Oh Oi Oy Oz Pa Pc Pd Pg Po Qa Qb Qe) cU(aF aI AL aM Ap aU aV aY BA Bb bC bE Bg bI bJ bL Bn bO bP bQ bR bU bW cA cB cC cD cF cG cJ cK cL cM cN cO cR cT Cu Cw CX dA dB DC Dd De dG DI dJ dM FR) Nu(Et Fr Hv Hw Hx Ih Ij Im Ip Iu Iv Jk Jl Jq Lh Li Lx Ly Ma Mg Mj Ml Mm Mp Mq Mr Mz Nb Nd Nj Nk Nl Nn No Nq Nr Nt Nv Oe Oh Om Pa Pc Pg Po Qa) Lw(Et Fr Hu Hv Hx Ii Ij Il In Ip Jg Jj Jk Lh Li Lx Ma Me Mg Mj Mm Mp Mq Mr Ms Mx Mz Nb Ni Nj Nk Nl Nn No Nq Nr Nv Oe Og Oh Oz Pc Qa Qb Qe) Mm(Fp Hu Hv Hw Hx Ih Ii Ij Il Im In Ip Iu Jj Jk Jl Jp Jq Jr Js Lh Li Lx Me Mj Mr Mz Nb Nk Nl No Nr Nt Nv Oe Om Pa Pg Po Qb) Ir(Et Fr Hv Hx Ip Iu Iv Jg Jj Jk Jl Jo Jp Li Lx Ma Ml Mq Mr Ms Mz Nb Nf Nj Nk Nl Nn Nq Nr Nt Nv Oe Og Oh Oi Oz Pa Pc Pg Po) Mp(Et Fr Hq Hu Hv Hx Ii Ij Il In Ip Iu Jg Jj Jk Jl Jq Li Lx Md Me Mg Mj Mr Mz Nb Nd Nj Nk Nl No Nr Nt Om Pa Pg Po Qa Qb) Im(Et Fr Hu Hv Hw Hx Ii Ij Ip Jj Jk Jq Js Lh Li Lx Mg Mj Mk Mq Mr Mv Mz Ni Nj Nk Nl No Nr Nt Nv Oe Oh Oz Pa Pc Po Qa Qe) Nt(Et Fr Hq Hv Hx Ip Iu Iv Jl Jo Jp Jq Li Lx Ly Mg Ml Mz Nb Nd Nf Ng Nj Nk Nl Nm Nn Oe Og Oh Oi Pc Pg Po Qa) Cu(aC AD Af aG AJ Al An Ap aU aZ BA Bb bC bE bJ Bn BO bW cE cJ Cp Cq cV Cw cX dB DC dK Fr) aJ(aC aD aG aI aL aM aU bA Bb bM bN bO bP bR bW cB cC cE cG cJ cO cR cV CX dB dC DE dG dH dK dL) Jl(Et Hr Hv Ij Ip Iu Iv Jo Jp Jq Li Lx Ma Ml Ms Mz Nb Nj Nk Nl Nm Nn Oe Of Og Oh Oi Pb Pc Pg Po Qa) Pg(Et Hv Ip Iu Iv Jo Jp Li Ly Mg Ml Mz Nb Nf Ng Nj Nk Nl Nm Nn Nr Ns Oe Of Oh Oy Pa Pb Pc Po Qa) Mz(Et Fr Ip Iu Iv Jj Jp Li Lx Ma Mg Ml Ms Nb Nf Nj Nk Nl Nn Nq Nr Oe Oh Pa Pc Po Qa) bA(aC aG

Figure 37 Continued

Ap AS aZ bC bE bF bJ bL bM bO bS bW cC cE cJ cR cT cV CX dB dC dK Fr) Jp(Hv Hw Hx Ij In Ip Iu Iv Jj Jq Li Mg Mq Mr Nb Nj Nl Nm Nn Nr Oe Oh Pa Pc Po Qa) Iv(Et Fr Hx Ip Iu Jj Li Lx Ma Mg Nb Nj Nk Nl Nn Nq Oe Oh Pa Pc Po Qa) Mg(Hv Hx Ip Iu Jj Li Lx Mj Mr Nb Ng Nk Nl No Nr Oz Pa Po Qa) Qa(Et Fr Ip Iu Jj Ma Nb Nf Nj Nk Nl Nn Oe Oh Pa Pb Pc Po) aZ(Al Ap Ax Ba Bb bC Bn bW cJ cX DE Di dK dM FR) Po(Et Ip Iu Ml Nb Nf Nj Nk Nl Nm Nn Oe Og Oh Pa Pc) bC(As Ax Ba Bb bM Bn bO cT CX Dc dE dK FR) Nn(Et Hv Hx Ij Ip Iu Li Lx Mr Nb Nj Nl Nr Pa) Fr(Bg cE Ch cJ cV Cx dC dE dK Iu Nj Nk Nl) Jj(Hx Ij Il In Ip Iu Lh Li Lx Nb Nl Nv) dE(bO bW cC cG cJ Cp Cx DC dK dM) Nb(Ip Iu Li Lx Ml Nf Nj Nl Oe Oh) Lv(Fp It Lu Mc Mh Pd Pf Pz) Iu(Et Hv Hx Ij Ip Li Lx Oe) Pc(Hv Hx Lx Mr Nj Nr Pa) Oh(Hv Hx Lx Mr Nr Pa) cJ(Ap Ax Ba Bb Cx Di) Nl(Et Jq Li Lx Om) Hx(Et Li Oe Og) Ap(Ax bO Cx) Ml(Hv Jq Nr) Oe(Et Lx Nv) Pa(Ip Lx Nj) cG(bF Bn cE) dK(Ax bM Dk) Nk(Et Ip) bW(As Ax) CwCx NgJg aLbE Unconstrained pan Mv Mw My Na Nc Nd Ne Nf Ng Nh Nm Ns Nx Ny Of Oi Om Oy Pb Pd Pf Pz Qc) cU(AD aE Af aH Aj aK AN AO aQ AR aS AW Ax bB Bc bG bH bN Bo bS bV bX CH cI Co CP CQ Cs Ct CV cW cY cZ Db dD dF Dg Dk DL dN) Nv(Hq Hu Hv Hw Ih Ij Il In Ip Jo Jq Jr Lh Ly Ma Me Mj Mk Ml Mq Mr Ms Na Nd Ne Nf Ng Ni Nj Nk Nm No Nq Nr Ns Nw Of Og Oh Oi Om Oy Oz Pa Pb Pc Pe Qe) Is(Fp Hq Hr Hu Hw Ih Ii Ik Il Io Iq Jg Jh Jm Jn Jq Lj Lu Lz Mb Mc Md Mj Mk Mn Mt Mu Mv Mw Mx My Na Nc Nd Ns Nx Ny Om Pb Pd Pf Pz Qb Qc Qe) dK(aC aG al AL aM Ar As Aw aY BB Bc bL BO bQ bS bV bZ cB cC cG cJ cO Cp cR cT CW CX dB DC DD De dF DI Dl dM fR) Pa(Hq Hr Hu Hv Hw Ih Ij In Jg Jh Jj Jk Jn Jq Jr Js Lh Ly Ma Me Mj Ml Mq Ms Mt Mv Nf Ni Nk Nm No Nq Ny Oe Of Og Oi Om Oz Pb Qb Qc Qe) Pc(Fp Hu Hw Ih Ii Ij Il In Ip Jg Jh Jj Jk Jn Jq Jr Js Lh Ma Me Mj Mk Mn Mq Ms Mt Mv Mx My Ni Nk Nm No Ny Oe Oh Oi Om Oz Qb Qc Qe) Pe(Hu Hw Ih Ii Ij Ik Il Io Iq It Jm Jn Jr Js Lh Lu Mb Mc Me Mj Mk Mn Mr Mt Mu Mv Mw Mx My Nc Nd Nh No Nr Nx Ny Om Pz Qb Qc Qe) cG(aC aG Al aM As aV Ax aY Bb bE Bg bJ bM BO bQ bR bU bZ cA cC cD cF cJ cL cN CO cR CX dB DC dH DI dM fR) Oh(Fp Hu Hw Ih Ii Ij Il In Ip Jg Jh Jj Jk Jq Jr Js Lh Ma Me Mj Mk Mq Ms Mt Mv My Ni Nj Nk Nm No Ny Oe Oi Om Oz Qb Qe) Ip(Hu Hv Hw Ih Ii Ij Il In Jg Jh Jk Jq Jr Js Lh Ma Me Mj Mk Ml Mq Mr Mt Mv Na Ni Nj Nm No Nq Nr Oe Og Oi Om Oz) Jj(Hu Hv Hw Ih Ii Ik Iq Jg Jh Jm Jn Jq Jr Js Ma Mj Mn Mq Mr Mt Mv Mx My Nj Nk Nm No Nq Nr Nx Ny Om Oz Qb Qc Qe) cJ(aC Ad Af Aj Al An Ao Ar As Aw Bc Bg bM Bn BO bS Ch Co Cp Cq Cs Ct Cv Cw cX Db Dc Dd De Dg Dk Dl dM) Nr(Hv Ih Ij In Jg Jh Jk Jq Jr Js Lh Ma Mj Mk Mq Ms Mt My Ni Nj Nk Nm No Nq Ny Oe Og Oi Om Oz Qb Qe) Nw(Fp Hr Ih Ii Ik Io Iq It Jg Jh Jm Jn Js Lh Lu Lz Mb Mc Mn Mu Mw Mx Nc Nd No Nx Om Pd Pz Qb Qc) Mr(Hq Hv Ih Ij Jg Jh Jk Jq Jr Js Ly Ma Mj Ml Mq Mt Nf Nj Nk Nm No Nq Ny Oe Of Og Om Qb Qe) Jt(Fp Hq Ii Ik Io Iq Jm Js Lh Lj Lu Ly Lz Mc Me Mh Mn Mq Mu Mv Mw Mx My Nc Nm Ns Pf Pz Qc) aA(Ad Af Aj An Ao Ar As Aw Ax Bc Bg Bn Bo Ch Co Cp Cq Cs Ct Cv Cw Db Dc Dd Dg Di Dk Dl) Cx(Af aG AL aM aU aV Aw Ax Bb Bc bO bV Cp Cq cT Cv DC Dd De dF DI dM fR) No(Hv Hw Ih Ij Il In Jg Jk Jq Jr Ma Me Ml Mq Ms Nf Ni Nj Nk Nm Nq Oe Oi Om Oz) Nj(Hv Hw Ih Ii Ij Il Jg Jk Jq Jr Js Lh Ma Mj Mq Mv My Na Nm Nq Oe Om Oz) aP(Ad Af Aj An Ao Ar Bc Bg Bo Ch Co Cp Cq Cs Ct Cv Cw Db Dc Dg Dk Dl fR) bO(aC aG Al aM As Aw Ax Bb bL bM cO cT cX dB DC Dd De dF DI dM fR) Ij(Hv Jg Jo Jq Jr Lh Ma Mj Ml Mq Ms Nf Nk Nm Nq Oe Of Og Oi Oz Pb) Ji(Fp Hq Ii Ik Io Iq Lh Lj Lu Ly Mc Me Mh Mn Mu Mw Ng Nm Pf Qc) Jq(Hu Hv Il Jg Jk Lh Ma Mj Mk Mq Ms Mv Nf Nk Nq Oe Og Oz Qe) Dc(Af aG Al As aV Ax Bb bM Bn bV cE Ch DC DI fR) Hv(Ih Il Jg Jk Lh Ma Mj Mq Nf Nk Nm Nq Ny Oe Om Oz) aX(aC aF aK aQ aW bE bl bU bX cI cL cN cY dA dJ dN) Bb(aG Al aM aU aV Aw Ax bE bV cX DC DI fR) Ax(aC aG aL As aU aV Aw bE bM Cs cY dC Di) Jk(Lh Ma Me Mj Mq Ng Nk Nm Oe Of Og Oi Oy) dM(aC aD aG al aL aM aU bM cB cO cR cX dC) Dc(AD aG As aU aV bE Bn Bo dC Di) Nk(Hw Jg Jh Lh Ma Mj Mq Nm Nq Nx Om) Oe(Hw Jg Lh Ma Mj Mt Nm Om Qb Qe) fR(Ao bF bS cB cC cE Co cV cX dC) Di(aG AL As aU Bc cX dC) aM(aD aG bJ bL bM bZ cO cX) Ml(Hw Ii In Jo Js Lh Om) Nm(Il Ma Mj Nq Og Oz) Aw(As aV Bg Bn dC) Jg(Hw Mj My Of Og) Om(Ih Nf Ng Of Og) aC(al aL cT dF) aG(aR bS cX dI) cE(bQ bZ cO dF) dC(Bc bV cX dN) As(Cp Cw dF) Ma(Hw Ih Lh) Mw(My Of Og) bF(bQ bZ cO) Bn(Cp Cw) Mq(Ih Il) Nf(Lh Mt) Oz(Mj Pb) bM(cT dN) AdCw AlaL HqLh NyPb cCdl cXdF Constrained panels with 3 analytes, where 1.0E-8 >= 'model p-value' > 0. Contains 19 panels of 590,601 total panels evaluated. : Ml{Qd(aA It Ji Jj Jt Lv Lw Mi Ms Nu Nw Oe Ok On) LvMi} Mi{Ms(Hq Lx Nf) LvHq}

Constrained panels with 3 analytes, where 1.0E-7 >= 'model p-value' > 1.0E-8. Contains 72 panels of 590,601 total panels evaluated. : Mi{Ml(Hq In Is Jj Jl Jo Jt Ms Nj Ok Qa) Nf(aA Hu Hx Jt Nb Ok) Hq(Hu Il Nb Nj Nk Pg) Ms(Lu Ly Nd) Jo(Iu Lv Nk) Jt(Md Of Pb) Nb(Of Pd) LvNj LxIl MwOf QdLj} Ml{Lv(aA Ir Is Ji Jt Ok) Ji(Hu Hv In Iv Jt) Qd(Jp Nb Oi Pa) Jt(Im Jo) Ok(In Qa) OfOn} Lv{Qd(Im Lj Mf) On(Of Pb) NjaA OkPb} Im{Qd(Lj Nk On)} aX{CuCx aAcX} cU{dH(aJ aP)}

Constrained panels with 3 analytes, where 1.0E-6 >= 'model p-value' > 1.0E-7. Contains 331 panels of 590,601 total panels evaluated. : Lv{Im(Hx Iu Jj Jl Jp Jt Lw Ml Mm Mp Nb Ni Nk Nl Nn Nr Nu Oh On Pc Qe) Jj(Hx Il In Ir Is Iu Jk Jl Jm Jt Mg Ml Mm Nl Nn Nu On Pg Qe) Ok(Hr Hv Hw Ij In Iu Jo Jq Md Mg Mm Mp Mz Nf Ni Nk Nn Of Om) Ml(Hv Hw Hx Iu Iv Jq Mj Mz Nb Nr Nw On Pe Qa Qe) Jt(Hr Hv Hw Ij In Jo Jq Md Na Nf Ni Ny Of Om Pb) On(Jo Lw Mm Mw My Nf Ng Nj Oe Og Oi Oy Qd) Mm(aA Jl Jo Ng Nw Qd Qe) Lw(Iu Jl Qd) Ji(Md Nf Pb) aA(Mg Of Qd) NbOf QdPf} Mi{Jt(Hr Hv Hw Ij In Jo Jq Mz Na Ny Om Qa) Ok(Hr Hw Jq Md Mz Of Om Pb) Po(Il Jk Jl Nb On Pa) Nu(Hq Jo Mm Ne) Lx(Iu Nk On Qd) Ng(Hu Iu Jk Mg) Of(Hu Hx Jk Jl) Pb(Jl Nb Oz) Nk(Jj Ly) Hq(Mg Qd) Jo(Hu Nb) NoaA MkOz MmJp NeNl IsJr QcQd} Ml{Ji(Hw Hx Ij Il Ir Is Jl Mj Ms Nb Nk Nr Nu Ok Pe Po Qa) Jt(Ii In Jj Mg Ms Ng Nu Oe Oi Ok Qa) Ok(Hv Ij Is Iv Mg Nb Nu) Is(Lw Mg Mm Nu Oe) On(Jj My Ng) Nu(Ir Qa) LwIv QaOe JjPe NyOf} Jt{Im(Hw Ij In Jq Md Mz Na Nf Ny Of Om Pb) Ok(Hw Jq Md Nf Of Pb) Jo(Hw Jq Na Nf Pb) Ji(Jq Nf) OfOn} Qd{On(Lj Lz Nf Nj Oe Oi Po Qc) Lj(aA Jj Nj Nu Oc Ok) Lz(Jl Pa) Ms(Im Lw) Ok(Nf Pb) MmPz NjaA ImIu InJj} Of{On(Lz Mg Mh Mw Nf Nj Nu Oi Pc Pf Pg) Ok(Jk Mg Mw Nb)} aX{cK(Aj Ax Bc Cu Dc) dH(aA aP bA cU) cJ(Aj Ax Cx) aA(bV dI) AxbQ} aA{cU(bQ cV cX dC dH dK) CxcJ MgNj bCcX} Cu{cJ(Ad As Cx) CxcS} Nf{Ji(Ms Nu) MgOk} Pb{Ok(Nb Qa) OiOn} cU{dH(bW cS) aJdG} CxaZcS MgNgOn aPcOdH Constrained panels with 3 analytes, where 1.0E-5 >= 'model p-value' > 1.0E-6. Contains 1,296 panels of 590,601 total panels evaluated. : Lv{Ml(Ih Ij In Jl Jn Js Li Lw Lx Mg Mr Na Nk Nl Nm No Nt Nu Ny Oh Pa Pc Po) Jj(Hw Ih Ij Ip Iq Jp Li Lw Mp Mz Nb Nd Nr Nt Nv Nw Pa Pe Po Qa) Nu(Hx Ir Is Iu Ji Jl Jp Jt Lw Ly Mp Nk Nl Nn Nw Oh Pc Qe) Nn(Hu Hx Ir Jl Jp Mz Nj Nk Nr Oi Pa Pe Qe) Ji(Hv Hw Ij In Iu Jl Jq Mz Ni Nk Nl Of Om) Jo(Hw Ir Iu Jk Jl Mg Nr Nt Nv Pe Pg Po) Nw(Lw Md My Nf Nk Ny Oe Of Og Pb) Mp(Hq Hx Ir Jl Jp Mz Nj Qe) Nk(Et Ip Jq Lw Mg Nb Nd Nm) Of(Hx Jk Jl Mw Nr Om Pa Pg) Pc(Jl Jp Mr Nr Pa Pe Qa) Lw(Hx Jp Mf Nl Pa Qe) Mg(Ir Jl Ng Nl Nr Qe) Oe(Jl Nb Nr Nv Pa Qe) Oh(Jl Jp Mr Nr Pa Pe) Ly(Mr Nl Nl Nt Pa) Nb(Nf Nj Og Pb) Is(Iv Jr Js Mh) Nf(Hx Mt Qa) Jp(In Iu Nl) Pb(Jl Nr Oz) Nd(Nj Nl) Jg(Ng Og) Jt(Jn Mz) FpPe MfLi MwMy NjPa HqPg ImIr} Ok{Hr(Hv Hw Hx Il Iu Iv Jl Jt Mg Mk Mp Nb Nf Nl Nu On Pe Pg Qd) Pb(Hv Hx Ij In Iu Jk Jl Mg Mk Mp Mw Nu Ny Oi On Oz Pe Pg) Nf(Hv Hx Ij Ip Iu Ji Mk Mp Nb Nn Nq Nu Oe Pe Pg Qa) Mg(Hw Ij In Jo Jq Md Ng Ni Nk Nl Nx Om Pd Qd) Nu(Hv Hw Ij In Iu Jq Md Mz Ni Nk Nl Of Om) Qd(Hw Jn Jq Md Mm Mp Mz Ni Nk Of Om Qa Qc) Ml(Hx Ip Ir Js Mj Mk Mp Nn Oe Pe Pg) Jt(Hv Ij In Jo Mz Na Ni Ny Om) Of(Hu Hx Ij Il Iu Mp Nq Pa Pg) Mp(Hq Hw Jq Md Nj Nx Om) Nb(Hw Jq Md Mz Ni Ny Om) Om(Hx Ij Ip Pg Qa) Md(Iu Lw Nn Pg) Hw(Ij Iu Pg Qa) Jq(Ji Lw Nn) Nk(Ip Mm) Is(Ir Jr) Jo(Iu Pg) NnNj NhNl NiIp HqPg} On{Ml(Hu Hv In Ir Iv Jn Jq Jr Js Lw Md Mv Mw Mz Nj Ns Nu Oe Og Oi Oy Pb Qa) Nu(Im Jj Jo Mm My Nf Ng Nj Nk Oe Og Oi Oy Pb Po) Of(Hu Hv Ij In Iq Jh Jk Lj Lw Me Mm Mt Mx Mz Qd) Nj(aA Hr Im Jj Lw Mp My Nf Ng Oe Og Oi Oy Pb) Nf(Hv In Ji Jj Jt Me Mg Ng Oe Og Oi Pb) Oi(Hq Hr Md Mg Mk My Ng Nn Nx Oy Po) Mg(Im Jj Jo Mv My Oe Og Oy Pb) Pb(Hv Jt Lw Lz Me Mh Oe Pf) Qd(Jo Mm Ms Oh Pf) Jt(Hr Jo Md Ny Om) Lw(Im Mm Ms Nx) Lz(My Ng Og Oy) Mh(Jj My Ng Oy) Pf(My Ng Og Oy) Mz(My Ng Oy) Hr(Hv Oe Qa) Im(Nk Oe Og) Po(Li Pe) Mm(Ip Oe) NkJj} Jt{Jo(aA Hr Hv Ij Im In Jn Md Mp Ms Mz Nt Nu Ny Of Om Pe Pg Po Qd) Of(aA Fr Hx Ir Ji Jj Jl Jn Jp Jr Js Mp Mr Mw Nt Nu Pa Pe Pg) Qd(Hr Hv Hw In Ir Jn Jq Jr Md Ms Mx Na Nf Pb) Im(Hr Hv Ir Jn Jp Jr Ni Nj Nk Nl Nu Qa) Jj(Hr Hv Hw Ij In Jq Md Na Nf Ny Om Pb)

Figure 37 Continued

Nu(Hr Hw Ij In Jq Md Na Nf Om Pb) Ji(Hv Hw Ij In Md Mz Ny Om Pb) aA(Hr Hw Jq Md Na Nf Ny Pb) Oi(Hw In Jq Md Na Nf Pb) Hr(Hx Jl Pa Pe Pg Po) Mg(Hw In Jq Na Nf) Ms(Hw Md Nf Pb) Oe(In Jq Na) Nf(Nw Pe) NgJq Hwli Irls PbPe} cU{cE(aA aC aG aI aJ aL AP Aw BA bL bM bW cG cS dE dK FR) bF(aC aG aJ aL aP BA bL bM bW cG cJ cS cX dE dK fR) aA(aF aG aX bE bJ bV cJ cK cS Cx dA dE dG) As(aV Aw bW Cp cS Cw Dd Di dK Fr) dH(aC aG Ap BA bL bM dE dK fR) cS(aY aZ Bb bM bQ bR bZ cC Cx) aJ(aZ bM bQ bR bZ cB cC dE) bZ(aC aG bW dE dK fR) aX(aY bQ CX Dd) dE(aE aG cC dC dK) aP(bQ cC dG) bR(bS bW dK) Ba(aV bQ) aC(aY bA) dK(bM cL) ApbQ} aX{Ax(aI aL As aU Aw Bb bV cB cE cQ cV CX dC dH dI dK dN) Cu(Ad An As Bn Bo bQ bV cE cJ Cq cV Cw cX Dc Dg dH) Cx(aA aJ aL aP aZ bA bO bV Cp Cq cT DC Dd dH) cX(aJ aL aO aP aZ bA bO dC Dd dM) dH(aI AJ aL Bc Cs cZ Dc dM) aA(bQ cB cJ cV dC) Dc(Ad As cJ dC) Cq(aL As bM) Dd(aI aL Bo) bA(bV cV dI) Dk(cK dK) BnCp aLbV aPdI} Ml{Qa(aA Et Im Ir Is Iv Jj Jl Jq Lw Ma Mg Mj Mm Mp Mz Nb Nj Nm Nn Nw Oh Om Pc Pe) Iv(Im Ir Jj Jq Ma Mg Mm Mp Mt Nn Nu Nw) Is(Im Jj Jq Ma Mp Ms Nm Nn Po) Jq(aA Jl Mj Nb Nr Nu Pa Pe) Nw(aA Hv In Ir Mj Mm Ns Nu) Jj(Ij Ir Nt Pg Po) Lw(aA Hv In Mj) Nb(Im Ng Of) aA(Ij In Nj) Mj(Im In) IqIr} Qd{Jj(Iu Jk Lz Mf Mg Nb Nk Nl Nt Nu Pg Qc) Mm(In Lj Lw Mf Mg Nb Nk Nt Nu Qc) Lz(aA Mr Nb Nr Nw Oe Oz Pe) Mf(Ma Mg Mp Nu Oe Pz) Ji(Jq Ms Mz Nf Nk Pb) Jo(In Iu Mg Nr Nt Pg) Jl(Lw Nn Oe Oz Qc) Nj(Mp Nn Oh Pc) Mg(aA Ng Nk) Nb(Oe Of Pb) Lw(Nk Qc) Lj(Ms Pz) Oe(In Pa) Oi(Nn Pc) aA(Nf Qc) NuNk HqPg IsJr PaPf} Ji{Nf(aA Hu Hv Hw Hx Il In Iu Jk Jp Mr Nb Nk Nr Nt Pa Pe Pg Po) Pb(Hx Il In Iu Jk Jl Ms Nb Nk Nr Nt Nu Oz Pe Pg) Of(Jk Jl Mk Mw Nb Nr Oz Pa Pe) Nu(Hw Jq Md Mz Ni Nk Om) Md(Iu Jk Ms Nb Nk) Nk(Hw Jq Mz) Jq(Iu Ms) MzJp HrJl IvJr} aA{bC(bV cB cJ cV Cx dB dC dE dH) cX(aU aZ bO bW cG cJ cS dC dE) Lw(Il Md Mg Nf Nj Nk Nl Nu) cJ(Af aZ bJ Bn dE) Cx(aU cS Cw De) Mg(Mu Nf Ng Oi) Nj(Iu Ma Mp Nu) dE(cB cC cV dC) cS(cB dH) NfIj HqPg aLbE aZbO} cS{bM(Ax bA bO Cq CX dD dH) Ax(aL As aZ Bb cB Cs) aZ(Af Bn bO cE cX) Cx(Aj aL bA Bb) Cu(As Bn cV) AdDc AjcJ bAcX} Mg{Ng(Is Jg Jk Jl Jp Mr Nb Nw Oz Pa Pe Pg) Jj(Ir Jl Nu Pg) Jl(Im Jo Of) Of(Nb Pa) MhIs NfNw NkIm} Cx{Cu(aU Ba bE cK dC DE dH dK) aZ(aJ aP bA bC bW cJ De) aP(cJ Dd dG dH) cG(bF cE) aUbA} Im{Nb(Lw Nf Nj Nk Of Pb) Lw(Hu Jl Jp) Mp(Jl Jp Nj) Nn(Jl Nj) Pg(Hq Jj)} Cu{cJ(Bn Cq Cw Dc dE) Ad(cK dH dK) As(cK De dH) BnDe DccK} aP{dH(aD aZ bM cB cG dE dG) dG(aI aL cJ cX) aZbO cEcG} Jj{Pg(Hq Iu Mm Nj Nl Nu) Nu(Iu Jk Nl Pe) NtNj MmPe} Lw{Of(Jl Nb Pa Pe Pg) Jl(Jo Ms Pb) NbPb HqPg IsJr} aZ{bW(Bn bO cE) cJ(Ax Di Fr) aJ(bO cX)} As{Ax(bW De dK) DebA DkdK} Nb{Of(Jh Nu Pg) Pb(Nj Nu)} Mm{Pe(Ng Oy) MhIs} Pg{Hq(Mp Pa) JlOf} bA{BnDc bWcE cCdE} Nf{Nw(Hv In)} cE{cG(Bn cX)} AxaLbE Constrained panels with 3 analytes, where 1.0E-4 >= 'model p-value' > 1.0E-5. Contains 3,483 panels of 590,601 total panels evaluated. : Im{Nk(aA Et Hv Hx Ij Ip Ir Is Iu Iv Ji Jj Jl Jp Jq Lh Li Lw Ma Mj Mm Mp Mq Mz Nm Nn Nr Nt Nu Nw Oe Oh Pc Po Qa Qe) Nj(Hv Hw Hx Ii Ij Ir Is Iu Iv Ji Jk Jl Jp Lw Mg Mj Mq Mr Mz Na Nr Nt Nu Nv Nw Oh Oz Pa Pc Pe Pg Po Qa) Nu(Hv Hx Ir Iu Iv Jj Jl Jp Lw Mg Mj Mm Mp Mq Mz Nb Ni Nl Nn Nr Nw Oe Oh Pa Pc Pg) Nn(Hu Hv Hx Ij In Ir Is Iu Iv Jj Jp Mj Mr Mz Nl Nr Oi Oz Pa Pe Pg Po Qa Qe) Oh(Hu Hv Hx Ij In Ir Is Iv Jl Jp Mj Mk Mr Mz Nl Nr Nt Nw Oz Pa Pe Po Qa Qe) Pc(Hu Hv Hx Ij In Ir Is Iv Jl Jp Mj Mk Mr Mz Nl Nr Nt Nw Oz Pa Pe Po Qa Qe) Lw(Hv Hx Ij Il Ir Is Iu Iv Mj Mk Mr Mz Nl Nr Nt Nw Oz Pa Pe Pg Po Qa Qe) Mg(Hv Ir Is Iu Iv Jj Jp Mj Mr Mz Ng Ni Nl Nr Nw Oz Pa Pe Qa Qe) Mp(Hq Hu Hv Hx Ij Ir Is Iv Jj Mj Mz Nb Nd Nr Nw Pa Pe Po Qa) Mm(Hv Hx Ij In Iv Jl Jp Mj Nl Nr Nw Oe On Pa Qe) Jp(Hv Hw In Ir Iu Iv Jl Mj Nb Nl Nr Nt Pe Pg) Nl(aA Hv Ij Ji Jj Ma Mq Mz Nb Nr Nw Po) Iu(Hv Ij Iv Jj Me Mz Nw Oe Pe Pg) Ml(Hv Ij Ir Jq Nr Pe) Nf(Lh Mt Nt Pe Pg Qa) Jj(Ij In Iv Lh Nb Nr) Oe(Jl Nr Pa Po) Mh(Is Mj) Nb(Md Om) Hq(Nt Pa) Jl(Of Pg) Jr(Is Mj) Pe(Fp Pf) MkaA NiJi OfPa} cU{As(aA aG aJ aK aL AP Ar aU Ax BA Bb bC bF bO cE cJ cM Cq Cu Cx cY Dc DE dH Dl) bW(aV aY Bg Bn bP bQ bU cA cC cD cF cG cK cL cN CO dA dI) dK(aC aG aJ aP aV AX aY aZ bA Bb Bn bP bQ bU cC cF cG Dk) Ba(aF aG aY aZ Bg bM Bn bR bU bZ cB cC cD cG cJ cK cL) bA(aF aG aX aZ bE bJ bM bQ bR bZ cB cC CX dC dF dG) bQ(aC aE aG aL Aw Bb bC bL bM cJ cM Cu Di FR) bZ(aI aL AP Aw Bb bL bM cG cJ cO Cu CX Fr) cC(aG aL Ap aX aZ bC bL bM bS cM CX Fr) aP(aZ bM bR bV cB cJ cN cV cX dA dC dI) dH(aL Aw aZ Bb bC bS cG cJ cM Cu Cx Fr) Cx(aG aJ Ap aV Bb bF cE cJ Cw Dd) aC(aG aJ aL aV bR cL cN cT cX) aZ(aG aY bJ Bn bO cJ cN cX Fr) Bb(aG aJ aV bF cE cJ dC dE) bR(aG aL bC bL bM cM cX dC) Bn(aU Aw cJ Cp Cu Dd De) cE(aX cJ cM Ct Cu cX De) Dd(An bJ Bo Cq dE) aJ(aG cN cX dC dL) bM(aG bE cJ cN dC) aV(aE cM cX dC) aX(bV cJ dC dI) bF(aI aO Aw Fr) dE(Aw aY Cp cS) Ap(cJ cK Dg) cN(aG cM fR) Bg(Aw Fr) aL(bE bJ) cL(cS dC) AldJ DicJ FrbG aGcX cMdI dFfR} Ml{Nb(aA Hu Hv Ij In Ip Ir Iv Jj Jn Jp Jr Js Li Lw Lx Ma Md Mg Mm Mw My Mz Nf Nj Ns Nt Nu Nw Oe Og Oi Oy Pb Pe Po) Nw(Hu Hw Hx Ij Iu Jj Jl Jq Js Lw Ma Me Mg Mp My Mz Nf Ng Nj Nk Nl Nr Nt Oe Og Oi Oy Pb Pe) Jq(Fr Hu Hv Hw Hx Ii Il In Ip Ir Iu Jj Jo Jp Lh Li Lx Mr Ms Mz Nl No Nt Oe Oz Pg Po) Hv(aA Et Fr Ip Ir Iu Iv Jj Jp Ma Mg Mj Mm Mp Mz Nm Nn Nt Nu Oh Pc Po) aA(Hw Hx Ip Ir Iv Jp Jr Js Li Ma Mj Mq Mz Nm Nr Nu Oe On Pe Pg Po) Iv(Et Fr In Ip Iu Jl Jp Li Lx Mj Mz Nm Oe Oh Om Pc Pe Pg Po) Ir(Et Fr Jl Jp Lw Lx Ma Mg Mj Mm Mp Mz Nn Nt Oe Om Pe Po) Pe(Jl Jp Lw Ly Lz Ma Mg Mj Nj Nn Nu Oh On Pc Pf) Mz(In Iu Jj Jl Li Lw Mg Mj Nl Nn Nr Nt Nu Po) In(Et Fr Jj Jl Jp Li Mg Mm Mp Nn Nr Nu) Lw(Hx Ii Ij Jl Js Li Mr Nr Nt Po) Mj(Ij Jj Jp Js Mg Nj Nu Oe Pc Po) Jj(Hx Jl Jo Lh Li Nr Nv) Jl(Js Mg Nm Nu) On(Ip Jh Mm Pc) Po(Nu Oe) Nr(Mg Nn) NuHx HqPg} Ji{Mz(aA Hu Hv Hx Il In Is Iu Iv Jk Jl Mr Ms Nb Nl Nr Nt Ok On Pa Pe Pg Po) Hr(aA Hw Hx Il Is Iu Iv Jk Jt Mr Ms Nb Nk Nr Nt Nu On Oz Pa Pe Pg Po) Ny(Hw Hx Ii Il In Iv Jk Jl Mr Ms Nb Nr Nt Nu On Pa Pb Pe Pg Po) Om(Hu Hv Hw Hx Il In Iu Jk Jl Mg Ms Nb Nk Nl Nr Nt On Pa Pe Pg) Of(aA Hu Hw Hx Ii Il In Iu Jp Mg Mp Mr Ms Nk Nl Nt Nu Pg Po) Jl(Hv Hw Hx Ij In Jo Lh Mg Mm Mp Ms Na Nj Nu Oe Pe) Md(Hw Hx Il In Mg Mp Nl Nr Nt Ok On Pg) Ms(Hv Hw Ij In Is Jn Jr Na Ni On Qa) Ij(Il In Iu Jk Nk Nl Nr Nt Nu Pg) Nt(Hv Hw In Jo Na Ni Nj Pd) Pa(Hx Ii Lh Nj Oe Pb Pd Po) Nu(Hv In Iu Jj Jn Mm Nl) Nl(Hw In Jq Mm Nh Pb) Jn(aA Hv Is Iv Jp Jt) In(Il Iu Jj Nk Nr) Pb(Hu Hv Hw Ii Jo) Mg(Jj Ng Nk Pd) Mm(Il Iu Jp Nk) Is(Ir Jq Jr Js) Nr(Hw Jo Na) Iu(Hw Jj Jo) Pg(Hq Jo Nx) Nn(Nj Oi) Hv(Jq Nk) Iv(Ir Qa) Jt(Ni Qa) On(Nx Po) Pd(Oz Pe) MpNj HwJq IlJj JrJs} Jj{Mg(Hv Hx Ij Il In Ip Is Iu Iv Jk Jp Jt Lh Li Lw Lx Mj Mr Mz Nb Nk Nl Nr Nt Nv Nw Oz Pa Pe Po Qa Qb) Nu(Hv Hw Hx Ii Ij Il In Ip Ir Is Iv Jl Jm Jp Jt Li Lw Mp Mz Nb Ne Nk Nn Nv Nw Pa Po Qa) Nl(Et Fr Hx Ij In Ip Ir Is Iv Jk Jl Jp Jq Jt Li Lw Lx Ma Mp Mz Nv Nw Om On Pe Po Qa) Iu(Hx Ij In Ip Is Iv Jg Jk Jl Jp Jt Li Lw Lx Ma Mz Nb Nv Nw Om On Pc Po Qa) Mp(Hu Hx Ij Il In Ip Ir Is Iv Jk Jl Jt Mz Nj Pe Po Qa) Nk(Ij Ip Ir Is Iv Jk Jl Jt Lw Mz Nv Nw Om Pe Po Qa) In(aA Ip Is Jl Jp Li Lw Lx Ma Mm Nn Nv Nw Po Qa) Il(aA Ip Jp Jt Li Lw Mm Nn Nw Oh Ok Pc Qa) Lw(Hx Ip Ir Iv Jk Jl Nb Nv Pe Po Qa) Jt(Ip Ir Jn Jo Jr Lx Mz Ni Nj Po Qa) Ij(Ip Md Mm Nf Ni Nn Of Om Pb) Ip(Hx Iv Jk Jl Nb Nt On) Oe(Is Jk Jl Nv Po Qa) Nj(Jk Jl Pe Qa) Qa(Jl Nn Pc) Iv(Nn Pc) MhIs HrOn JkPe JmOk} aA{Nf(Hv Hw Hx Il In Ir Iv Jq Li Mp Mt Mz Nb Nm Nt Nw Oe Om Pe Pg Po Qa) Cx(Af aM aV Aw aZ bO bW cB cG Cq Cu dC Dd dE) Oe(Hx Il Ir Is Iu Jk Jl Lx Mm Nk Nt Nu Po Qa) cV(aI aL aP aZ bA bB bO cB cG cJ cS dD) Ij(Hr Hw Jt Md Mm Mz Ni Of Om Pb) bJ(aL aM bA bB cB cG dC) Jt(Hv Ir Jn Mz Ni Om) cE(aI bB bZ cG cJ cO) cS(aZ bV cJ dB dE dG) De(Af As Bn cX dE) Lw(Hr Hw Jq Na Pb) Nk(Ip Ma Mz Nm Nu) aD(aI aL aM bB cB) bC(Af As Bn bQ dA) bE(bA bO cB cJ dD) bW(aZ cB dB dE dH) bO(cJ dB dC dE) dH(bZ cG cO dE) Nm(Hw Md Pb) Mm(In Nw Pg) Mp(Hq Jp Nd) Mz(Iu Nl Ok) Of(Mw Nb Pg) aZ(Al dC dK) Nu(Ip Ne) Is(Jr Mh) Qa(Hw Pb) bQ(cG cO) cB(bS dC) dB(dC dK) ApcJ AwBn DdaX NnOi MaNl MuHu NbPb InJp JoPg} Nu{Mp(Hq Hx Ir Is Iv Jl Jp Mz Nb Nd Nj Nw Pa Pe Qa) Oe(Hx Ir Is Iu Jl Mg Mm Mz Nb Nl Nw Pa Pg Po Qa) Lw(Hx Ir Is Iu Jl Jp Mr Nb Nk Nl Nw Oi Pa Qa) Nn(Hx Iv Jl Jp Mr Nj Nk Oi Ok Pa Pe Qa) Mm(Hv Hx Ir Is Jl Jt Lx Mz Nk Nl Nw Qa) Jt(Hv Jn Jp Mz Ni Nj Nk Nw Ny) Pc(Hx Jl Jp Mz Nj Pa Pe Qa) Mg(Ir Jl Mz Ng Nk Nl Qa) Oh(Hx Jl Jp Nj Pa Pe Qa) Nf(Hx Jq Mz Nb Nw Qa) Nk(Et Ip Jq Mz Nw) Is(Ir Iv Jr Js

Figure 37 Continued

Mh) Ne(Ir Iu Jp Nl) Jo(Ir Jl Ok Pg) Of(Hx Jl Pa Pg) Nb(Md Nj Og) Mz(Iu Nl) Ng(Jg Pg) Qa(Hw Pb) LyNl NjPa HqPg HxOg IuJp JlPb PePf}
Mg{Ng(Fr Hu Hx Ii Ij Il Ip Ir Iu Iv Jt Lh Lw Lx Mj Mw Mz Nj Nk Nl No Nr Nt Nv Po Qa Qb) Nw(Iv Md Mm Mv My Nk Nl Oe Of Og Oi Pb)
Nk(Ip Iv Jp Jt Lw Mz Nr On Pc Qa) Jl(Hr Jp Mm Mz Nj Oe Og Oi Pb Qa) Is(Ir Iv Jo Jr Js Ms Oe Og Oi) Nf(Hx Mr Mz Nb Pa Pe Pg Qa) Jo(Ir Iv
Nr Nt Pc Pg Qa) Jp(

Figure 37 Continued

Cq Dk) aA(aM Dk) dK(Ar dF) fR(bC Cu) BabO CqFr aJaU} Og{Jg(Hv Hw Hx Ij Il Im In Ip Ir Is Iu Iv Ji Jl Jq Lw Mg Mp Mz Nb Nk Nl Nn Nr Nu Oh Pc Pe Pg Po Qa Qe) Nb(Hr Hw Ip Is Iv Ji Jk Jp Lx Ma Md Mz Nk Nn Nt Nw Pg Po Qe) Mg(Ii Ij Il Ip Jk Jq Lw Mj Mr Nv Pg Po Qb Qe) Mw(Im Ip Ir Is Iu Iv Ji Lw Mm Mz Nl Nu Qe) Hx(Fr Im Ip Iu Jp Ma Nm Nn Nw Oh Pc) Nm(Il Iu Iv Jk Jl Nk Pa Po) Ij(Fr Iu Nk Nu Nw Pa Pc) Qe(Iv Lw Mm Mp Nt Nu Om) Jk(Ip Jl Lw Nu Nw Pc) Om(Iu Nk Nl Nu) Lw(Hu Il) InNw JqPa} bC{cX(aC aG Bb bF Bg bM bO cC cE cT Cu dC dK dM) cE(al aL aO BB bL bQ bZ cO cT dF fR) Bn(aL Aw Ba bO cG Dd De dF dK Fr) Aj(Ao Aw Bb cK Cp dC Dd dH Fr) Cu(An cK Cp Cq Cw dA dB Dc dH) Bb(aJ Ax Bg bO Ch cK dC dK) Fr(aV bF Bg bQ Ch cK dB dH) cC(aL aO bL cG cT dF dM) Dd(AD An Bo Cq Cw) dM(aC bM cB dB dC dK) aL(aC bE Bg bJ dB) bM(Al Ba cJ dC) bF(aO cO dF) cT(aC bJ dB) Ba(bO Dg) Dc(dB dC) dH(aO cG) AxcB BgaI ChDi aDaM aPbQ bOdK dBdC} Bn{Aw(aL aP aV Ax Ba Bc Bg bO cG Ch cJ cM Cq cT DC Dd dI dK Fr) De(aV Ax Ba Bb bO bV cG Cp Cq cT DC Dd dF Di dK dM FR) aA(aK aM aU aV bO cB cG Cp Cq Cw DC Dd) bA(aM aV Bb cB cG Cp Cw Dd Di Fr) cJ(aJ bV cG Cp Cq Cw Dc Dd Dk Fr) Cu(aJ Ao aP bE bV cC cV fR) Cp(aJ aP Ba cG dI dK Fr) cG(bZ Cq Dc dH Di dK) Fr(aM aU Cq Dc Dd) aJ(aU dC Dd) Dc(aU dC) aPaU} Ng{Jg(Hx Ip Ir Is Iu Iv Ji Jl Jt Mm Mz Nb Nl Nn Nq Nt Nv Oh Pc Pe Po Qa) Jk(Et Fr Iu Ji Jp Li Mw Nb Nm Nn Nt Nu Oh Pa Pc Po) Mp(Fr Ii Il Iu Mg Mw Nb Nm Om Pg) Nq(Hx Im Jl Jp Jt Nb Nu Nw Pe) Iu(Fr Mv Mw Nm Nt Nv Om Pg) Fr(Hx Ij In Nb Nt) Mg(Et Hv Ni Om Qe) Mm(Hu Mv Mw Om Pd) Lw(Hu Mv Mw Oz) Nm(Pa Pg) Ma(Jt Nb) Mw(Im Nu) NbHr JpPg LjPe} Jo{Mg(Hw Ij Ip Iu Jk Jq Js Lh Mj Mr No Nv Oz Pa Po) Jl(Ij Ip Iu Iv Jk Jq Nl Nn Nv Oh Pc Po) Nt(Et Hw Hx Ij Jk Li Mz Nm Oh Pc Qa) Hw(Et Im Ip Jg Jp Lw Nu Qa) Pg(Et Ip Mp Mz Nl Nn Oh Pc) Iu(Et Ij Iv Jq Nv Om Po) Iv(Jk Lh Ma Nv Om) Pe(Fp Ip Ji Nm Po) Nb(Ip Ir Po Qa) Jk(Et Ji Mp Nu) Nv(Nl Nr Nu) In(Et Mp) Ji(Mr Oz) PoNm NrJq LwMd NlOm HrHx} bA{cV(aG aI aJ aM Aw bO cC cR cT Di) De(aS bF Bg bI bJ bM CT dC) cE(aG aI Aw Bb bL bS bZ cR Fr) cX(aG Ap aU bO cC cT Di) cO(bQ bR bZ cC cF dH) Ap(bQ cK dC Dg dH) Di(aF aU bE cJ dC) Fr(aF bF bG dC) bS(bR cB cC dH) Bb(aG bE dC) Dd(Ad An bJ) cC(aS bL dI) dH(aA cG cT) dK(Ax bJ cR) Af(Aw cJ) aM(aD dB) bF(bZ Co) bO(bJ dC) bQ(aP cG) AlbM AwCt BcdB aJdG} Cu{cE(aD aG An Ao aP Ba Bo bZ CO Cp Cq Cw Dc dI Fr) Cq(aJ Ao aP aU Aw Ba bE bV cG cV dC FR) Dc(aJ Ao aP Ba bQ bV Cw dC De Fr) Cw(Ad aP Ba cK De dH Fr) An(aJ aP Ba De FR) bQ(Ap cG cO dI Fr) Af(aU Ba cJ De) Aj(Ao aU bE dC) cX(AP bG dC) dH(Ap cG cO dI) Cp(Ao Aw Fr) dI(cC cK dA) dC(Bb dB) ApcK AxCs aAcV bFcO} Nb{Hr(Hv Hw Hx Ip Ir Is Iv Li My Mz Nk Nm Nr Pe Pg Po) Md(Ij Ip Jp Lx Mg Mp Mz Nm Nt Nw Pe Pg Po Qa) Mg(Hq Hx Ip Mh Mv Mw My Nk Ny Oi Om Oy) Nw(Mh My Ny Om Oy Po) Nk(Ip Lx Ma Nm Nu) Ny(Ij Mz Pe Pg Qa) Ip(Iu Mm Nn Nu) Om(Ij Nm Qa) Po(Pe Pg) Nu(Oh Pc) Nl(Ma Ne) Hq(Nd Pa) LxOh HwQa JiPd OyPg} aA{Aw(AD Af An bJ Bo Cq cV Cw dB) Dc(AD An bE bJ cV dB dC Dd) Dd(AD An bJ Bo Cp Cq Cw) Af(aK Ao aU aV Co Cq dC) Ap(bV cB cK cV dC Dg dH) Ax(Bb bE Cs cV dC De dK) Al(aV bO cB cG De Di) cV(Ba Cw De Di Fr) De(AD bJ) Co(bF cE) Cw(Ad An) Li(Lz Pf) bR(bS cG) dC(Bb Di) BacB DkdK EtMm JrJs bFcO} Nk{Ip(Et Fr Hv Iu Iv Jl Jp Jq Li Lx Ma Mz Nm Nn Nr Nt Om Pa) Nm(Fr Hv Hx Iu Iv Jp Li Lx Ma Nn Nu Pa Po) Ma(Hv Hx Ij Iu Jp Jq Mr Mz Nr Pa) Mg(Et Hv Lx Me Pa Pg Po) Nu(Fr Ij Ly Mq Oh) Nn(Ij Oi Om) Jq(Fr Jp Ms) Mp(Md Nd) Ij(Fr Jp) Is(Ir Iv) Om(Oh Pc) EtMz LiLj} dK{bM(Al Ap Ar Aw aY Ba bB Bc bO bQ cG cJ Cq cR cT Dc De dF Di dM) Ax(aL aO aP aU Aw bB cB cG dC De Fr) Ar(aI aL Ap aV bB Di) aL(Al Ap cR Di dM) Aj(Aw Ba cG Fr) dM(aG bO cR dC) Ad(Dc Dd) Bb(cJ dC) Di(Al bO) bF(bQ cG) bS(bR cB) cR(cG cX) dB(Bc Dc) BgDk FraO bQcE} Is{Jn(Hv Ij Im Ip Ir Iv Jq Li Lx Me Mg Mz Nm Nn Nu Po Qa) Ir(Fr Iu Jp Js Li Mz Nm Nn Nt Oh Pc Pe Po Qa) Js(Im Jp Jt Li Mz Nm Nn Nt Oh Pc Pe Po) Iv(Im Jp Jt Ms Nn Nt Oi Pe Po) Jr(Nw Oh Oi Pc) Oh(Lx Ms) EtMm LzJl MwMy NaJi NeNl ImLh LiLj} Mm{Et(Im Ip Iu Jk Jl Jp Jt Li Lw Lx Mg Mp Mz Nl Nn Nt Nu Nv Oh Pc Pg Po Qa) Jp(In Jq Li Lx Me Nl Po) Im(Hu Hw Il Lh Me Mr) Nt(Hq Ip Li Mp Nd) Me(Il Ip Lw Nl) Nu(Li Ma Nv) Jg(Ip Lw Mp) Oz(Hq Lz Ns) Mw(My Oy) Ji(Mg Mp) Li(Ip Lj) LwMf LxMz HqPa} Oi{Nn(Et Fr Hu Hv Hx Ii Ij Il In Ip Iu Jk Jq Jr Jt Li Lw Lx Mp Mr Nl Nm No Nr Nv Om Oz Pg Qb) Pc(Et Hu Iv Jg Jk Jt Mg Nt Nu Nv Om Qa) Mg(Ih Ip Mj No Nr Nt Nu Pa Qb) Oh(Hu Jg Jk Jl Om) Lw(Hu Jg Jk) Nt(Hq Ly) Jg(Mp Nu) JlNw} aJ{aD(Aw bO bR cB cX Dd De dH Di) Ax(aU bM cB Cs dC De) cV(aL Ap Aw Ba Di Fr) cE(aI Ap bQ bZ cO) dG(aG Aw bQ dF Fr) Di(aU cJ cX dC) dH(Ap bP bZ dI) dL(aI aL aM cJ) Dd(Ad An bM) Af(aU Aw) Aj(Aw De) Al(bO cB) Ap(cJ cK) cC(dB dI) dC(Bc Dc) DebM aMbJ bFcO} Ap{cE(aI aL Ar Aw bO bZ cD Ch cJ cO cT De dF FR) Ax(aU aV Bg bO cC Cs dC De Dg) Bg(Aw cK Cp cV cX dC De dH) Ad(cJ cK Cp Dc Dd) Dg(Ba bO cG cJ Fr) cK(aP bV Ch dI) Ch(Dc Di) AlbO DicJ bVdH} Mp{Md(Hu Hx Ii Ij Il In Jg Jk Lw Mw Om Pg) Nd(Hu Hv Il Iu Jk Lh Lw Nl No Oz Pg) Oz(Mk Ns Oy Pd Pf Pg) Lw(Hu Ms Ns Pd) Lx(Lh No Nt) Ms(Jq Jt Nn) Jg(My Ns Oy) Mw(My Oy) Hw(Hv Qa) NrPc NtLy LzMr} cJ{Ax(Ba Bb bE bF bM cE cX dC De) Dc(Aj bE bJ Bo cV dB) Di(Ba Bb bE bM bO cX) Aw(Af Aj dB) Ba(bM bO cE) Bb(bV cX dI) Bc(bE bJ cX) De(Af bM cX) Al(bM bO) Dd(Ad bJ) Fr(Bg Ch) ArcE} Pa{Hq(Hx Iu Jq Lz Ma Nl Nq Nt Nv Po) Ip(Im Mg Nn Nu Oh Pc) Qa(Hw Im Nn Oh Pc) Mz(Nn Oh Pc) Nu(Ly Mg) Lx(Oh Pc) Ma(Nl Nm) Jq(Hr Ms) Jt(Hx Po) NnPc LzLi MhNw IjIm} cG{cX(Bg bZ cC cL cR dH) bF(aP Ax cO cS Fr) bJ(aM bO Dc Dd) bQ(Af aP Ax Fr) cC(bH bM bS dM) dH(Af Ax cS dM) Ad(Dc Dd) Al(aV bM) Bg(Bb Fr) cE(bS fR) AfbZ AxdC bMbO} Jl{Hr(Hx Ij In Ir Iu Jq Li Pc Pg Po Qa) Oh(Ip Lx Mz Nw Pc Pg Po) Pc(Ip Lx Mz Pg Po) Nn(Ip Lx Nw Po) Li(Lj Mh Pf) NqMk MsJq NdHq HwQa HxJt} Fr{Dd(aD Aj An bJ Bo Cp Cq cV Cw Dc) Aj(aG aU bE bG dC De) cV(aV Ch cT dC) dC(Bg cE Dc) Ax(bE bG) Ch(cB De) Hq(Hx Nt) AdDc DecE NuNl NiIm aVbE} aP{Dd(Ad An bJ bM Bo Cp Cq Cw Dc dL) De(aD Aj bQ dG) Aw(Af bQ cE) Ax(aU Cs dC) Ad(Cp Dc) Bb(cK dG) Di(bQ dC) AfaU CobF CpdG DlaD aMdN bQcO} Nu{Ly(Ip Jk Mr Ni Nt) Oh(Hv Ip Iv Mr Po) Pc(Hv Ip Iv Mr Po) Md(Mq Qa) Mw(My Oy) Ne(Ih Iv) Nl(Et Nh) Hq(Nd Nt) NrMg IjQa IvJr} Lw{Oz(Hq Lz Mk Nd Ns Oy Pd Pf) Hv(Ij In Jq Na Ni) Hu(Mu Nn Oh Pc) Ij(Hw In Md Om) Mw(My Oy) EtIl MdLh MsJi HrHw} dC{Bb(Ax BO bV Cs cX dB DI dN) Dc(Ad Aj BO cX dB Di) cX(bO cR cW dM) Ax(Aw De) bM(dM dN) AjBa bOdM} Qa{Hw(Im Iu Mr Nm Nn Nr Nt Nw Oh Pc Pe Pg) Md(Mg Nm Nn Oh Pg) Ij(Mg Nt Pg) Pe(Hr Ji) MgOm InPg IvJr LiLj} My{Mw(Im Ip Ir Ji Jp Lx Mg Mz Nl Nn Nw Oh Pc Pg Po) Jg(Hx Nn Pg Po) MgHx JkNw} Ba{De(Af Aj Ax Bg cE Ch) Aj(aU bE cV) Ax(aU bM cB) Ad(Dc Dd) bO(bM cX) cE(aI bZ) ChDi DgcS} Im{Ni(Et Ma Me Mq Mv) Nd(Lh No Nt) Hq(Lh Mr No) Oz(Ij Ip Mj) Lx(Lh Nt) NsMq MkIp HuJk} Hv{Nm(Hr Hw Ij In Md Na Ni Nl Om) Ip(Mg Nl Nn Oh Pc) Md(Nn Pc) MaNl} cE{cS(bG bQ bZ cO fR) aX(bQ cO fR) bZ(Aw Cp De) fR(aU cL) AxDe bOcO bQcX} Mg{Hq(Lh Lx Mr Nt Oz) Me(Iu Ni) Hx(Md Mv) NrNl MaJt MsJq IvJr OyPg} Ax{De(aC aD Af Bb bF bM Cs) Bb(aG aU aV bE) AwCs aUcX} Ad{Dc(aG aV Aw Bb bO Cw cY De Di) Dd(Aw De)} Pc{Nr(Ip Lx Nn Oh) Lx(Mr Pe) Ip(Hu Mr) Oz(Nn Oh) EtIl} Nl{Ma(Hx Jq Nm Nr) Ne(Ir Iv Nt) NmJp NtLy LiLj} aX{bQ(cO cZ) bS(bR dI) cC(bH bL) cT(bM cV) aOdI cVcZ} bO{bM(Al bE dM) cX(aG dM fR) AlDi DdbJ aLbE bFcO} Ji{Pd(Jk Jt Mr Nr) Iv(Js Na) Nx(Jk Nv) MsJt} Hr{Pe(Ij Jq Nm Po) Hx(Iu Nm Nr) NrJq} Nw{Mh(Iv Nr) Mv(Jk Nq) NtLx MdIj JkOy LiLj} Hq{Nt(Ip Lx Nn Po) Pe(Lj Nq) MrNd} Pg{Oy(Jg Mw Nm) Oz(Lz Mk) Pf(Li Lx)} Bb{dI(aV cB cC cK) ChDe DiaG} Oh{Lx(Mr Pe) Ip(Hu Nr) EtIl MrJp} aL{bE(aN cX dM) bJ(aM Dd) cCdI} Li{Lj(Ir Iv Mz Pe) LzOz} cS{dH(bQ cO dF) CpCw bRbS} Nn{MeIu MsJq HuJk IrJp} Po{LzOz IvJr JgOy} Jp{NsMq MaIn MsJq} aM{bJ(cT dF) aDdM} cX{aUdM bFbQ cCfR} Hu{MdMw MuIr} Jq{MsIu IvJr} AfDecT AlChDi HxJgOy IiInOn

Constrained panels with 2 analytes, where 1.0E-7 >= 'model p-value' > 0. Contains 4 panels of 14,763 total panels evaluated. : Mi(Lv Ml Nj) MlQd

Figure 37 Continued

Constrained panels with 2 analytes, where 1.0E-6 >= 'model p-value' > 1.0E-7. Contains 8 panels of 14,763 total panels evaluated. : Mi(Hq Ms Nf) Lv(aA Qd) Ml(Ji Jt) ImQd Constrained panels with 2 analytes, where 1.0E-5 >= 'model p-value' > 1.0E-6. Contains 62 panels of 14,763 total panels evaluated. : Lv(Hx Im Ir Is Iu Ji Jj Jl Jp Jt Lw Mg Mm Mp Mz Nl Nn Nr Nu Nw Oh Ok On Pe Qa Qe) Qd(aA In Lj Lw Lz Mf Mg Mm Mp Nb Nu Ok On Qc) Ok(Mg Ml Mp Nf Of Pb) Jt(Hw Md Na Nf Pb) On(Nf Oe Of Pb) aA(cU Mg Nj) Mls NfJi aPdH aXcX Constrained panels with 2 analytes, where 1.0E-4 >= 'model p-value' > 1.0E-5. Contains 226 panels of 14,763 total panels evaluated. : aA(aX aZ bC bO cJ cS CX dC dE Hx Ij Ip Ir Is Iu Iv Ji Jt Lw Ma Mm Mp Mz Nl Nt Nu Nw Oe On Pe Pg Po) Ok(Hr Hv Hw Ij In Iu Jp Jq Md Mm Na Ni Nj Nk Nl Nn Nu Oh Om On Pc Pg) Jt(Hr Hv Ij Im In Jj Jn Jo Jp Jq Mz Ni Nu Nw Ny Of Om) On(Hr Im Jj Lw Ml Mm Mv Mw My Ng Nj Nk Nu Og Oi Oy) Ji(Hw Ij In Iu Jq Md Mm Mp Mz Ni Nk Nl Nu Om Pb) cU(aC aG aJ aP As aX aZ bF bM bZ cE cS dE dH dK) Lw(Im Ir Is Iu Iv Jl Jp Nt Nu Nw Pa Pe Pg Po) Lv(Li Ml Mr Nb Nd Nk No Pa Pc Pg Po) cS(aL Ax aZ bA Bb bM bO Cu CX dM) Im(Ir Iu Iv Jl Jp Mp Nb Nn Pe Pg) aP(aZ cB cE cJ cV CX dC dG) aX(aJ Ax bA cJ Cu Cx Dc Dd dH) Jj(Jk Jl Nt Nu Pe Pg Po) Nw(Iu Ml Mp Nf Nl Nu) Mm(Ir Is Iv Pe Qa) Ml(Iv Mj Pe Qa) Mp(Ir Is Iv Jp) Cu(As Cx dE) Nu(Ir Is Jp) Mg(Ir Is Jl) aZ(aJ bO Cx) Nb(Of Pb) NnPe HqPg aJbC bAdE Constrained panels with 2 analytes, where 1.0E-3 >= 'model p-value' > 1.0E-4. Contains 536 panels of 14,763 total panels evaluated. : Im(Et Hu Hv Hw Hx Ii Ij Ip Is Jj Jk Jq Js Lh Li Lx Mg Mj Mk Mm Mq Mr Mv Mz Ni Nj Nk Nl No Nr Nt Nu Nv Nw Oe Oh Oz Pa Pc Po Qa Qe) Nu(Et Fr Hv Hx Ih Ij Ip Iu Iv Jl Jq Li Lx Mg Mm Mp Mq Mr Mz Nb Nj Nk Nl Nn Nr Nv Oe Oh Pa Pc Pe Pg Po Qa) Jp(Hw Hx Ij In Ip Ir Is Iu Iv Ji Jj Jl Jq Li Mg Mm Mr Nb Nj Nl Nm Nn Nr Nt Oh Pa Pc Pe Pg Po Qa) Mg(Hv Hx Ip Iu Iv Ji Jj Jt Li Lw Lx Mj Mr Mz Nb Ng Nk Nl No Nr Nw Oz Pa Pc Pg Po Qa) Mm(Hv Hx Ij Il In Ip Iu Jl Jq Jr Jt Li Me Mj Mr Mz Nb Nk Nl Nr Nt Nw Oe Pa Pg Po Qb) Mp(Et Hq Hu Hv Hx Ij Ip Jj Jl Jq Jt Li Lx Mr Mz Nb Nd Nj Nl Nr Nt Pa Pe Po Qa) Nn(Et Hv Hx Ij Ip Ir Is Iu Iv Jl Li Lw Lx Mr Mz Nb Nj Nl Nr Nt Pa Pg Po Qa) Lw(Et Fr Hv Hx Il Ip Jj Jk Li Lx Mj Mr Mz Nb Nk Nl No Nr Nv Oz Qa) aZ(Al Ap Ax BA Bb bC Bn bW cJ Cu cX DE Di dK dM FR) Jj(Hx Ij Il In Ip Ir Is Iu Iv Ji Lh Li Lx Mz Nb Nl Nv Qa) Fr(bA bC Bg cE Ch cJ cU cV Cx dC dE dK Iu Iv Nj Nk Nl) Pc(Hv Hx Ir Is Iv Jl Lx Mr Mz Nj Nr Nt Nw Pa Pe Po Qa) Cu(AD An Ba bC bE bJ Bn Bo cJ Cq cU cV cX dB dK) Oe(Et Hx Ir Is Iu Iv Ji Jl Lx Mz Nb Nt Nv Nw Po Qa) Oh(Hv Hx Ir Is Iv Jl Lx Mr Mz Nb Nr Pa Pe Po Qa) bA(aC aG Ap As bC bE bJ bM bW cT cU CX dC dK) Iu(Et Hv Hx Ij Ip Iv Li Lx Mz Nb Pe Pg Po Qa) cU(Ap aV Ba Bb bJ Bn bQ bR cC cJ cL Cx Di) dE(aJ bC bO bW cC cG cJ Cp Cx DC dK dM) bC(As Ba Bb bM Bn bO cT CX dK fR) Ji(Hr Hv Jl Jn Nj Nt Ny Of Pa Pg) Jt(Ir Jl Jr Lx Nj Nk Pe Pg Po) Mz(Iv Jl Ml Nj Nk Nl Nt Pg) aJ(Bb bM bO cB CX dC De) aX(aJ aL bO bV dC dK dM fR) Nb(Ip Li Lx Ml Nf Nj Nl) Nt(Hq Ip Ir Is Nj Nw) Nl(Et Jq Li Lx Om Po) Jl(Ip Lx Nj Pb Po Qa) cJ(Ap Ax Ba Bb Cx Di) Ml(Hv Ir Jq Nr Po) Ap(aA Ax bO Cx) Is(Iv Jr Js Mh) Qa(Nf Nj Pa Pb) Nk(Et Ip Nw) Hx(Et Li Og) Pa(Ip Lx Nj) Pg(Ir Iv Of) aA(Al Bb De) cG(bF Bn cE) dK(Ax bM Dk) Nw(Ir Iv) bW(As Ax) CwCx DeaP NgJg PePf aLbE Constrained panels with 2 analytes, where 1.0E-2 >= 'model p-value' > 1.0E-3. Contains 459 panels of 14,763 total panels evaluated. : Jj(Et Fr Hu Hv Hw Ih Ii Jg Jm Jn Jq Jr Js Ma Mj Mn Mq Mr Mt Mv Mx My Nj Nk Nm Nn No Nq Nr Nx Ny Oh Om Oz Pa Pc Qb Qc Qe) Nj(Hv Hw Hx Ih Ii Ij Il Ip Iu Jg Jk Jq Lh Lx Ma Mj Mq Mr Mv Na No Nq Nr Nv Oh Om Oz) Cx(aG aL aM aU aV Aw Ax Ba Bb Bc bO bW cG Cp Cq cT DC Dd De dF Di dK dM fR) Pc(Et Fr Hu Ii ij Il In Ip Jg Jk Jq Lh Li Nb Nk Nl No Nv Om Oz Qb) Oh(Et Hu Ii Ij Il In Ip Jg Jk Jq Lh Li Mp Nk Nl No Nv Om Oz Qb) Oe(Fr Hw Ij Jg Jk Jq Lh Li Ma Mg Mr Mt Nm No Nv Om Pa Qb Qe) bO(aC aG Al Aw Ax Ba Bb bM bW cG cJ cX DC De Di dK dM fR) dE(aG al aL aM Ap aU Aw Ax Ba Bb cO cT Cw cX Dd De dF Di fR) Nk(Hv Hw Ij Jg Jh Jq Lh Lx Ma Mj Mq Nb Nm Nn Nq Nr Nx Om) bW(Aj aM Ba Bb bF Bg bM Bn bP cE cF cR cT dB Dc Di dM) Ax(aC aG aL As aU aV Aw Ba Bb bM cG Cs cY dC De Di) dK(aL Ap Ar Aw Ba Bb Bc cG cR cT Dc De dF Di dM) Di(aG aJ AL As aU Ba Bb Bc cG DC) Nl(Hv Hx Ij Ip Jg Ma Mq Nm No Nr Nv Pa) Ip(Fr Hv Hx Ij Jk Jq Li Mr No Nr) aG(aM aR aZ Bb bS cG cX Dc dl dM) Nm(Fr Hv Il Ma Mj Nq Og Oz Pa) Ml(Hw Hx Ii Ij In Jo Js Li Om) cG(aC As Bg bJ bM cC cX dH dM) dC(Aw Bb Bc bV cX Dc dM dN) Nn(Hu Il In No Oi Om Oz) Jq(Iu Mr Ms Nf Nr Oz Pa) aM(aD bJ bL bM bZ cO cX) cE(Ap aZ bQ bZ cO dF fR) As(Aw Cp Cw Dc De dF) Ma(Hv Hw Hx Mr Nr Pa) Og(Ij Jg Jk Mw Nb Om) aC(al aL cJ cT dF dM) bM(Ba cJ cT De dM dN) Dc(Ad aU aZ Ba cJ) Bb(aU aV dl fR) Bn(Aw Cp Cw De) Of(Jg Mw Om Pa) bF(bQ bZ cO Fr) cX(cJ dF dM fR) Lx(Hx Mr Nr) Nf(Lh Mt Om) Al(aL De) Ap(Bg Dg) Aw(aJ aV) Ba(AJ) Et(Hv Nb) Mq(Ih Il) My(Jg Mw) Iu(Nv Om) Pa(Hv Ij) Pb(Ny Oz) aZ(cC cR) dM(aU bC) AdCw AfDe CofR FrHx NqNr MdNb MgQb NgJk HwQa LiLj bScJ cCdI Unconstrained panels with 3 analytes, where 1.0E-8 >= 'AUC p-value' > 0. Contains 9,939 panels of 590,601 total panels evaluated. : Lv(Mi(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Hx(aA Et Fp Fr Hq Hr Hu Hv Hw Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Qd(aA Et Fp Fr Hq Hr Hu Hv Hw Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qe) Jp(aA Et Fp Fr Hq Hr Hu Hv Hw Ih Ii Ij Ik Il Im In Io Ip Iq Ir Is It Iu Iv Jg Jh Ji Jj Jk Jl Jm Jn Jo Jq Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qe) Nw(aA Et Fp Fr Hq Hr Hu Hv Hw Ih Ii Ij Ik Il Im In Io Ip Iq Ir Is It Iu Iv Jg Jh Ji Jj Jk Jl Jm Jn Jo Jq Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qe) aA(Et Fp Fr Hq Hr Hu Hv Hw Ih Ii Ij Ik Il Im In Io Ip Iq Ir Is It Iu Iv Jg Jh Ji Jj Jk Jl Jm Jn Jo Jq Jr Js Jt Lh Li Lj Lu Lw Lx Ly Lz Ma Mb Mc Md Me Mf Mg Mh Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qe) Mz(Et Fp Fr Hq Hr Hu Hv Hw Ih Ii Ij Ik Il Im In Io Ip Iq Ir Is It Iu Iv Jg Jh Jj Jk Jl Jm Jn Jo Jq Jr Js Lh Li Lj Lu Lw Lx Ly Lz Ma Mb Mc Md Me Mf Mg Mh Mj Mk Ml Mm Mn Mp Mq Mr Ms Mt Mu Mv Mw Mx My Na Nb Nc Nd Ne Nf Ng Nh Ni Nj Nk Nl Nm Nn No Nq Nr Ns Nt Nu Nv Nx Ny Oe Of Og Oh Oi Om On Oy Oz Pa Pb Pc Pd Pe Pf Pg Po Pz Qa Qb Qc Qe) Im(Et Fp Fr Hq Hr Hu Hv Hw Ih Ii Ij Ik Il In Io Ip Iq Ir Is It Iu Iv Jg Jh Ji Jj Jk Jl Jm Jn Jo Jq Jr Js Jt Lh Li Lj Lw Lx Ly Lz Ma Mb Mc Md Me Mf Mh Mj Mk Ml Mm Mn Mp Mq Mr Mt Mu Mv Mw Mx My Na Nb Nc Nd Ne Nf Ng Ni Nj Nk Nl Nm Nn No Nq Nr Ns Nt Nu

Figure 37 Continued

Nv Nx Ny Oe Of Og Oh Oi Ok Om On Oy Oz Pa Pb Pc Pd Pe Pf Pg Po Pz Qa Qb Qc Qe) Nu(Et Fr Hq Hr Hu Hv Hw Ih Ii Ij Ik Il In Ip Iq Ir Is It Iu Iv Jg Jh Ji Jj Jk Jl Jm Jn Jo Jq Jr Js Jt Lh Li Lj Lu Lw Lx Ly Lz Ma Mb Mc Me Mf Mh Mj Mk Ml Mm Mn Mp Mq Mr Mt Mu Mv Mw Mx My Na Nb Nc Nd Nf Ng Ni Nj Nk Nl Nm Nn No Nq Nr Ns Nt Nv Nx Ny Oe Of Og Oh Oi Ok Om On Oy Oz Pa Pb Pc Pd Pe Pg Po Pz Qa Qb Qc Qe) Jj(Et Fp Fr Hq Hr Hu Hv Hw Ih Ii Ij Ik Il In Io Ip Iq Ir Is It Iu Iv Jg Jh Ji Jk Jl Jm Jn Jo Jq Jr Js Jt Lh Li Lu Lw Lx Ly Lz Ma Mb Mc Md Me Mf Mg Mj Mk Ml Mm Mn Mp Mq Mr Mt Mu Mv Mw Mx My Na Nb Nc Nd Ne Nf Nh Ni Nj Nk Nl Nm Nn No Nq Nr Ns Nt Nv Nx Ny Oe Of Oi Ok Om On Oz Pa Pb Pd Pe Pf Pg Po Pz Qa Qb Qc Qe) Is(Et Fp Fr Hq Hr Hu Hv Hw Ih Ii Ij Ik Il In Io Ip Iq Ir It Iu Iv Jg Jh Ji Jk Jl Jm Jn Jo Jq Jr Js Jt Li Lj Lu Lw Lx Ly Lz Ma Mb Mc Md Me Mf Mh Mj Mk Ml Mm Mn Mp Mr Ms Mt Mu Mw Mx My Nb Nd Ne Nf Ng Nh Ni Nj Nk Nl Nm Nn No Nq Nr Ns Nt Nx Ny Oe Of Og Oh Oi Ok Om On Oy Oz Pa Pb Pc Pd Pf Po Pz Qa Qb Qc Qe) Pe(Et Fp Fr Hq Hr Hu Hv Hw Ih Ii Ij Ik Il In Io Ip Iq Ir It Iu Iv Jg Jh Ji Jk Jl Jm Jn Jo Jq Jr Js Jt Lh Li Lj Lu Lw Lx Ly Lz Ma Mb Mc Md Me Mf Mh Mj Mk Ml Mm Mn Mq Mr Mt Mu Mv Mw Mx My Nb Nd Ne Nf Ng Ni Nj Nk Nl Nm Nn No Nq Ns Nv Nx Ny Oe Of Og Oh Oi Ok Om On Oy Oz Pa Pb Pc Pd Pf Pg Po Pz Qa Qb Qc) Po(Et Fp Fr Hq Hr Hu Hv Ih Ii Ij Ik Il In Io Ip Iq Ir It Iu Iv Jg Jh Ji Jk Jl Jm Jn Jo Jq Jr Js Jt Li Lj Lu Lw Lx Ly Lz Ma Mb Mc Md Me Mf Mh Mj Mk Ml Mm Mn Mp Mq Mr Mt Mv Mw Mx My Na Nb Nc Nd Nf Ng Ni Nj Nk Nl Nm Nn Nq Nr Ns Nt Nv Nx Ny Oe Of Og Oh Oi Ok Om Oy Oz Pa Pb Pc Pd Pf Pz Qa Qb Qc Qe) Qa(Et Fp Fr Hq Hu Hv Hw Ih Ii Ij Ik Il In Io Ip Iq It Iu Iv Jg Jh Jk Jl Jm Jn Jo Jq Jr Js Lh Li Lj Lu Lw Lx Ly Lz Ma Mb Mc Md Me Mf Mg Mh Mj Mk Ml Mm Mn Mp Mq Mr Ms Mt Mu Mv Mw Mx My Na Nb Nd Ne Nf Ng Ni Nj Nk Nl Nm Nn No Nq Nr Ns Nt Nv Nx Oe Of Og Oh Oi Om On Oy Oz Pa Pb Pc Pd Pf Pg Pz Qb Qc) On(Et Fp Fr Hq Hr Hu Hv Hw Ih Ij Ik Il In Io Ip Iq Ir It Iu Iv Ji Jl Jm Jn Jo Jq Jr Js Jt Lh Li Lj Lu Lw Lx Ly Lz Ma Mb Mc Md Me Mf Mg Mh Mj Mk Ml Mm Mn Mp Mq Ms Mt Mw Mx My Na Nb Nc Nd Ne Ng Ni Nj Nk Nl Nm Nn No Nr Ns Nt Nv Nx Oe Of Og Oh Oi Ok Oy Oz Pa Pb Pc Pd Pf Pg Pz Qb Qc Qe) Ji(Et Fp Hq Hu Ih Ii Ik Il Io Ip Iq Ir Iu Iv Jg Jh Jk Jl Jm Jo Js Jt Lh Li Lj Lu Lw Lx Ly Lz Mb Mc Md Mf Mh Mj Mk Ml Mn Mp Mq Mr Ms Mt Mu Mv Mw My Nb Nc Nd Ne Nf Ng Nh Ni Nj Nk Nl Nm Nn Nr Ns Nt Nv Nx Oe Of Og Oh Oi Om Oy Oz Pa Pb Pc Pf Pg Pz Qb Qc Qe) Ok(Et Fp Hq Hu Hw Ih Ii Ik Il Io Ip Iq Iu Iv Jg Jk Jl Jm Jq Jt Li Lj Lw Lx Ly Lz Ma Mb Mc Md Mf Mg Mh Mj Mk Ml Mm Mp Mq Mr Mt Mu Mw Mx My Na Nb Nd Ne Nf Ng Nh Ni Nj Nk Nm Nn Nq Nr Ns Nt Nv Nx Oe Of Og Oh Oi Oy Pa Pb Pc Pf Pg Pz Qb Qc Qe) Ml(Et Fp Fr Hr Hv Hw Ih Ii Ij Il In Ip Iq Ir It Iu Iv Jg Jk Jl Jn Jo Jq Jr Js Jt Lh Li Lj Lw Lx Ly Lz Ma Md Me Mh Mj Mk Mm Mp Mq Mr Mt Mv Mx Na Nb Nc Nd Ni Nj Nk Nl Nm No Nq Nr Nt Nv Ny Oe Oh Oi Om Oz Pa Pg Qb Qc Qe) Ir(Et Hq Hr Hv Ih Ii Ij Ik Il In Ip Iq Iu Iv Jg Jh Jm Jo Js Li Lj Lw Lx Ly Lz Ma Mb Mf Mg Mh Mm Mp Mq Mu Mx Nb Nd Nf Ng Ni Nj Nk Nm Nn No Nq Ns Nt Oe Of Og Oi Oy Oz Pb Pf Pz) Lx(Et Fr Hq Hv Hw Ih Ii Ij Il In Ip Iq It Iu Iv Jg Jh Jl Jn Jo Jq Jr Jt Li Lw Ly Ma Me Mf Mj Mm Mp Mq Mr Na Nb Nd Ng Ni Nj Nk Nl Nm Nn No Nr Nt Nv Oe Oi Pa Pb Pc Pg Qe) Mm(Fp Hu Hv Hw Ih Ii Ij Ik Il In Ip Iq It Jk Jn Jo Jq Js Jt Lj Ly Me Mf Mg Mj Mp Mr Mx Nd Nf Ng Ni Nj Nk Nl Nm Nn No Nr Nx Oe Of Og Oh Oi Oy Pc Pf Pg Pz Qb Qc) Jq(Et Hq Hu Hv Ik Il Ip Iq Iu Iv Jh Jk Jl Jo Li Lj Lu Lw Ly Mb Mc Md Me Mf Mp Ms Mt Mu Nb Nd Ne Nf Ng Nh Ni Nj Nk Nm Nn Ns Nx Oe Of Og Oa Pa Pb Pf Pg Pz Qb Qc) Nm(Et Hu Hv Ih Ii Il In Ip Iq It Iu Iv Jk Jl Jr Js Jt Li Lj Lu Ly Mf Mj Mk Mr Mv Mx My Na Nd Nf Ni Nj Nk Nl Nr Ns Nx Ny Oe Oi Oy Pf Pg Qb Qe) Oe(Et Fr Hv Hw Ih Ii Ij Il In Ip Iq Iu Iv Jg Jh Jk Jl Jn Jr Jt Lh Li Ly Mb Me Mf Mr Nb Nd Ni Nk Nl No Nr Nt Nv Ny Om Oz Pa Pg Qb Qc Qe) Ip(Et Fr Hv Hw Ih Ij Il In Iq Iu Iv Jg Jk Jl Jo Jt Li Lw Ly Mf Mp Mr Nb Nd Ni Nj Nk Nl No Nr Nt Oi Om Oz Pa Pg Qb Qe) Nd(Et Hv Hw Ij Il Iq Iv Jg Jk Jt Li Ly Ma Me Mf Mr Ms Na Nf Ni Nj Nk Nl Nn No Nr Nt Nv Ny Om Oz Pf Pg Qc Qe) Lw(Et Fu Hv Ih Ii Ij Il In Iq Iu Jk Jr Jt Li Mp Mr Ms Mv Mx My Na Nb Ni Nl No Nr Nt Pg Qe) Ly(Et Hv Hw Ih Ij Il In Iq Iu Iv Jk Jl Jt Li Mb Mf Mr Ni Nk Nl No Nr Nt Nv Oi Om Pg Qb Qe) Oi(Et Fr Hw Ih Iq Iu Iv Jg Jk Jl Jt Li Ma Mp Mq Mu Nb Nl Nn No Nq Nr Nt Nv Om Pg Qc Qe) Iq(Et Hq Hv Ij In Iv Jg Jh Jt Li Lz Ma Md Mf Mp Mq Ms Nf Ni Nj Nk No Nt Og Om) Nv(Hq Hu Il In Iv Jo Jt Md Me Mf Mh Mn Mr My Ne Nf Ng Nj Nk Ns Of Og Oy Pb Pf) Li(Hv Hw Ij Ik Il In Jk Jo Jt Mb Mf Mh Ne Nf Ng Nh Ni Nj Nk Of Og Pf Pg) Et(Hv Ij Ik Il In Iu Jo Jt Mb Mf Mp Nf Ng Ni Nj Nk Nr Of Og Oy Pf Pg) Mf(Fr Hv Hw Ij Iu Jk Jl Jn Jt Ma Mp Ni Nn No Nq Nt Om Pg Qc Qe) Nj(Fr Hv Hw Ij Iu Jg Jh Jt Ma Mb Md Mp No Nt Ny Om Pg Qc Qe) Jt(Ii Ik Jo Mb Mg Mh Mp Ms Nf Ng Nh Ns Nx Of Og Pb Pc Pf) Nk(Fr Hv Hw Ij Iv Jg Jh Jl Ma Md No Nt Ny Om Oz Qc) Ik(Hv Hw Ij Il Iu Iv Jk Jl Mj Mp Mr Nt Ny Om Pg Qc Qe) Og(Hv Hw Ij Il Iu Jg Jk Mr Mw Nl No Nr Nt Om Pg Qe) Ni(Fr Hv Ij In Iu Jg Jk Ma Mp Nn Nt Ny Om Qc Qe) Oz(Hw Ii Il Iu Jk Jl Mr Nb No Nr Pa Pg Qe) Jo(Hv Hw Ih Ij Iu Iv Jk Jl No Nt Pg Qe) Of(Hw Il Iv Jg Jk Mr Nb No Nr Om Pg Qe) Fr(Hv Ij Il In Mr Ng Nl Nr Oy Pg Qe) Mp(Hq Jn Jr Mg Mr Nf Ng Nl Pc Qb) Ng(Iu Jg Jk Jl Nl No Om Pg Qe) Jl(Fp Hq Ii Md Mh Nf Pb Pf) No(Hq Hw Ij In Mh Pf) Hv(Fp In Iu Nl Ny Qe) Pb(Jg Mr Na Nb Nr Ny) Pg(Fp Ii Jm Nf Oy Pf) Ma(Ij Mr Nl Nr) Qe(Ii Ms Nx Pf) Nn(Mg Pc Qb) Ij(Ns Pf Qc) Iu(Mg Oy Pc) My(Jg Mw) Qc(Il In) Om(Ms Pf) Oy(Hw Jg) MbIv MdNl OhPc} cU{aA(aC AD aE AF aG aH aI AJ aK AL aM AN aO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT Cu CV CW CX cY cZ dA DB DC DD DE dF DG dH DI dJ DK DL dM dN FR) bF(aC AD aE AF aG aH aI AJ aK AL aM AN aO AP aQ AR AS aU aV AW AX aY aZ BA BB BC bE BG bH bI bJ bL bM BN BO bP bQ bR bS bU bV bW bX bZ cA cB cC cD cE cF cG CH cI cJ cK cL cM cN CO CP CQ cR CS CT CV CW CX cY cZ dA DB DC DD DE dF DG dH DI dJ DK dL dM dN FR) bA(aC AD aE AF aG aH aI AJ aK aL aM AN AO AP aQ AR AS aU aV AW AX aY aZ Ba BB BC bE BG bH bI bJ bL bM BN BO bP bQ bR bS bU bV bW bX bZ cA cB cC cD cE cF cG CH cI cJ cK cL cM cN CO Cp CQ cR CS CT CV CW CX cY cZ dA DB DC DE dF DG dH DI dJ DK DL dM dN FR) As(aC AD aE AF aG aH aI AJ aK AL aM AN Ao AP aQ AR aS aU aV AW AX aY aZ Ba BB BC bE BG bH bJ bL bM Bn BO bP bQ bS bU bV bW bX bZ cA cC cD cE cF cG CH cI cJ cK cL cM cN CO CP CQ cS CT cV CW CX cY cZ dA dB DC DD DE dF DG dH DI dJ DK DL dM FR) dE(aC AD aE AF aG aH aI AJ aK AL aM aN aO AP aQ AR aS aU aV AW AX aY aZ Ba BB bC bE BG bH bI bJ bL bM BN BO bP bQ bR bS bU bV bW bX bZ cA cB cC cD cE cF cG CH cI cJ cK cL cM cN cO CP CQ cR CS CT cV cW CX cY cZ dA DB DC DD dF DG dH DI dJ DK dL dM dN) dK(AD aE AF aG aH aI AJ aK AL aM AN Ao AP aQ AR aS aU aV AW Ax aY aZ Ba BB BC BG bH bI bJ bL bM BN BO bP bQ bR bU bV bW bX bZ cA cC cD cE cF cG CH cI cJ cK cL cM cN CO CP cQ CS cT Cu CV CW CX cY cZ dA dB DC DD dF DG dH DI Dk DL dM dN FR) aP(AD aE AF aG aH aI AJ aK aL aM AN aO aQ aR aS aU aV AW AX aY aZ Ba BB bC bE Bg bH bI bJ bL bM BN BO bP bQ bR bS bU bV bW bX bZ cA cB cC cD cE cF cG CH cI cJ cK cL cM cN CO cP CQ cR CS CT cV cW CX cY cZ dA DB dC dD dF DG dH DI dJ Dk dL dM fR) aJ(AD aE AF aG aH aI Aj aK aL aM AN aO aQ aR aS aU aV AW AX aY aZ bB bC bE BG bH bI bJ bL bM BN BO bP bQ bR bS bU bV bW bX bZ cA cB cC cD cE cF cG CH cI cJ cK cL cM cN CO cP CQ cR CS CT cV cW CX cY cZ dA DB dC dD dF DG dH DI dJ dL dM dN fR) Cx(AD aE Af aG aH aI aK AL aM AN Ao Ap aQ Ar aS aU aV AW AX aY aZ Ba BB BC bE Bg bH bJ bL Bn BO bQ bR bU bV bW bX bZ cA cC cD cE cF cG CH cI cJ cK cL cM cN CO CP CQ CS cT Cu cV CW cX cY dA dB DC DD De Dg dH DI dJ Dk dL dM dN FR) fR(AD aE Af aG aH aI Aj aK aL aM AN Ao aQ AR aS aU aV AW AX aY Ba bB bC Bg bH bI bJ bL bM BN BO bP bQ bR bS bU bV bW bX bZ cA cB cC cD cE cF cG CH cI cJ cK cL cM cN cO CP CQ cR CS CT cV CW cX cY cZ dA Db dC dD dF dG dH DI dL dM dN) aI(aC AD aE aG aH aK AL aM AN Ao Ap aQ AR aS aU aV AW Ax aY aZ Ba BB BC bE Bg bH bJ bL bM Bn bO bP bQ bR bU bV bW bX bZ cA cC cD cE cF cG CH cI cK cL cM cN CO Cp cQ CS cT cV CW cX cY cZ dA DB DC dD Dg dH DI Dk dL dM dN) cX(AD aE Af aG aH aK AL aM aN AO Ap aQ aR aS aU aV AW Ax aY aZ Ba BB bC bE Bg bH bJ bL bO bP bQ bR bU bV bW bX bZ cA cC cD cE cF cG CH cI cJ cK cL cM cN cO CP CQ CS cT cV CW cY cZ

Figure 37 Continued dA dB DC DD De Dg dH Dl dL dM dN Fr) aG(aC aD aE aH aK aL aM aN aO aQ aS aU aV AW aX aY aZ Ba BB bC bE BG bH bI bJ bM BN bO bP bQ bR bS bU bV bW bX bZ cA cB cC cD cE cF cG CH cI cJ cK cL cM cN CO cP cQ cR cS cT cV cW cY cZ dA dB dC DD dF DG dH DI dJ dM dN) cE(aC aD aE aH Aj aK AL aM aN AO Ap aQ aU aV Aw aX aZ Ba BB BC bE BG bH bJ bL bM Bn BO bQ bR bS bU bV bW bZ cC cD cG cI cJ cK cL cM CO CP CQ cR cS CT cV CW cY dB DC DD De dF DG DI dL dM dN Fr) bL(aD aE Af aH aK aL aM aN aQ aR aS aU aV AW Ax aY aZ BB bC Bg bH bJ bM BN bO bP bQ bR bS bU bV bW bX bZ cA cC cD cF cG CH cI cJ cK cL cM cN cO Cp CQ Cs cT cV cW cY cZ dA dB dC DD Dg dH DI dL dM dN) cS(AD aE Af aH Aj aK AL aM An Ao Ap aR aS aU aV Aw Ax aY aZ Ba BB Bg bJ bM BN BO bP bQ bR bU bX bZ cA cB cC cD cF cG Ch cL cM cN CO Cq cR Cs cT Cv Cw cZ dA DB dC DD dF DG dH DI dL dM) cM(AD aE Af aH AL aM AN AO Ap aQ aS aV AW Ax aY aZ Ba BB Bc Bg bH bJ bM Bn bO bQ bR bU bV bW bX bZ cA cC cD cF cG cH cI cJ cL cN CO Cp Cs cT CV CW cZ dB dC De dF Dg dH DI dM dN Fr) Aw(AD Af aH aK AL aM AN Ao Ap AR aS aU aV AX aY aZ Ba BB BC Bg bJ bM Bn BO bQ bR bU bV bW bX bZ cA cC cD cG CH cJ cK cL cN CO Cp Cs cT CV CW cY dC dH DI Dk Dl dM dN) Di(aD aE aH aK AL aM AN Ao Ap aQ aU aV AX aY aZ Ba Bb BC Bg bJ bM Bn bO bQ bR bU bW bX bZ cA cC cD cG CH cJ cK cL cN CO CP cQ Cs cT CV cW cY dA dB DC Dd Dg dH dI dM) Ba(AD aE Af aH aL An aQ aU aV Ax aY aZ BB Bg bJ bM BN BO bP bQ bR bS bU bV bZ cA cB cC cD cF cG Ch cJ cK cL cN CO Cp cQ Cs Ct Cv cY dA dB dC Dd dF DG dH dI Dk dL dN) dC(aC aD aE aF aK aL aM aO Ap aQ aS aU aV aW aY aZ BB bC bE BG bH bJ bL bM Bn bO bQ bR bU bW bX bZ cA cC cD cF cG cH cI cJ cK cL cN cO Cp cT cV cW cY cZ dA dB Dd dH dI dL dM Fr) cT(aC aD aE Af aH aL aM An Ap aS aU aX aY BB bC bE Bg bH bJ bM Bn BO bQ bR bU bW bZ cA cC cD cF cG cJ cL cN cO Cp cQ cR cV CW dA dB De dF dH dI Dl dM dN) bZ(aC aD aE aH aK aL aM aO Ap aQ aS aU aV aX BB bC bE bG bH bJ bM bO bQ bS bV bW cC cD cG cJ cK cN cO Cp cR Ct CW cY dB DD dF dG dI dL dM dN Fr) cJ(aC Ad aE Af Aj AL aM An Ao Ap Ar Ax aY Bb Bc Bg bJ bM Bn BO bQ cA cC cF Ch cL Co Cp Cq Cs Ct Cu Cv DB Dc Dd De Dg dH Dk Dl dM Fr) Bb(AD Af aH Aj aL An Ap aQ aU aV AX aY bB bC Bg bJ Bn bO bQ bR bU bV cA cC cD cG Ch cK cL cN CO Cv cY dA dB Dg dH dI dN) Ap(AD Af aH Aj aL aS aV aY aZ Bg bJ bM Bn BO bP bQ bR bU cA cD cF cG Ch cK cL cN CO Cq cR dA DB Dd dF Dg dH dL) bW(aD aE Af aH Aj aL aM aS aV aY aZ bB Bg bM Bn bO bP bQ bR bU cA cC cD cF cG Ch cL cN CO cZ dA dB DD dG dH dI dL) aV(Ad aE Af Aj Al aM An Ao Ar Ax Bc Bg bH bJ bM Bn BO bS Ch cK Co Cp Cq Cs Ct Cv Cw Db Dc Dd De Dg Dk Dl Fr) aD(aE Af aL aM aY bB bH bJ Bn bO bQ bU bV cA cC cD cI cL cN cO Cp cQ cV cW cZ dB dD dH dL dM dN Fr) aE(aL aN aO aW aX aY bC bH bJ bO bQ bR bU bV bX cA cC cD cG cL cN cO cV cW cY cZ dB Dd dI dM dN) cN(aL aM aO aX aZ bB bC bJ bM bO bS bV cG cI cK Cp cQ Ct cW dA dB Dc DD dF dG dM Fr) aX(Aj aL aM Ax aY aZ bM bQ bR bU bV cA cC cG cL Cp Cq Cu dA dB Dc Dd dH dI dM) bO(AL aM Ax aY bC bH bJ bM Bn bQ bR bU bV cA cC cG cI cL Cp cV cW dB dH dM) dB(aC AL aY bJ bM Bn bQ bS cA cC cH cL Cp cQ Ct cW Dc DD dH dM Fr) dM(aH aL aM aN aQ aU aY bB bC bJ bQ bR bU cA cC cD cL dA dH) cW(Af aL Ax aY bH Bn bQ cA cC cD cG cH cI cL Cp cV dH dI) bS(aY bJ bQ bR bU cA cB cC cD cF cG cK cL cO dA dH dI) Fr(Aj aL aY aZ Bg bM Bn bQ bR cD Ch cK dA Dg dH) bB(aW Ax Bg bH bM Bn bQ cA cD cI cL cQ cV dH dN) aL(aC aM aY bC bE bH bJ cA cC Cp De dN) bQ(aO bH bJ cC cG cK Cq Ct dF dG dH) Bn(aK Al aU cG Cp Cq Ct cu cY Dd) Dd(Ad AN aU aY bC Bg cL Cs) aZ(aO aY bC bE bH cC Cq dN) aO(aS bJ cH cI cV dH) aU(Af Al Ax Bg Ch Cp) bM(aH bC bE cA Cq dN) cK(cA cC cD cL Ct dH) Bg(cG Cp Ct cY) Cu(Ad An Cq Dc) aY(aC bC bJ cG) dH(aC cG Ct dG) Ax(Cs Dc) Cp(Ch cY) bC(cA cL) cC(bV Ct) AdDc AfCq AlcD aSbJ cGcL} aA{cJ(aC AD aE AF aG aH aI AJ aK AL aM AN AO AP aQ AR AS aU aV aW AX aY aZ BA BB BC bE bF BG bH bI bJ bL bM BN BO bP bQ bR bS bU bV bW bX bZ cA cB cC cD cE cF cG CH cI cK cL cM cN CO CP CQ cR CS CT CV CW CX cY cZ dA DB DC DD DE dF DG dH DI dJ DK DL dM dN FR) Cx(aC AD aE AF aG aH aI AJ aK Al aM AN AO AP aQ AR AS aU aV AW AX aY aZ BA BB BC bE bF BG bH bI bJ bL bM BN BO bP bQ bR bU bV bW bX bZ cA cB cC cD cE cF cG CH cI cK cL cM cN CO CP CQ cR CS CT CV CW cX cY cZ dA DB DC DD DE dF DG dH DI dJ DK DL dM dN FR) bC(aC AD aE AF aG aH aI AJ aK aL aM aN aO aP aQ aR AS aU aV AW AX aY aZ bA bB bE bF BG bH bI bJ bL bM BN BO bP bQ bR bS bU bV bW bX bZ cA cB cC cD cE cF cG CH cI cK cL cM cN cO cP cQ cR cS CT cV CW cX cY cZ dA DB dC dD DE dF DG dH DI dJ DK dL dM dN fR) cS(aC AD aE AF aG aH aI AJ aK aL aM aN aO AP aQ AS aU aV AW AX aY aZ bA bB bE bF BG bH bI bJ bL bM BN BO bP bQ bR bS bU bV bW bX bZ cA cB cC cD cE cF cG CH cI cK cL cM cN CO cP CQ cR cT cV cW cX cY cZ dA DB dC dD dE dF DG dH DI dJ dK dL dM dN fR) aX(aC aD aE AF aG aH aI aJ aK AL aM aN aO aP aQ aR AS aU aV aW Ax aY aZ bA bB bE bF bG bH bI bJ bL bM BN bO bP bQ bR bS bU bV bW bX bZ cA cB cC cD cE cF cG cH cI cK cL cM cN cO cP CQ cR cT cV cW cX cY cZ dB dC dD dE dF dG dH dI dJ dK dL dM dN fR) dK(aD aE AF aG aH aI aJ aK aL aM AN aO aP aQ AR aS aU aV aW Ax aY aZ bA bB Bc bF bG bH bI bJ bL bM BN BO bP bQ bS bU bW bX bZ cA cC cD cE cF cG cH cI cK cM cN cO cP CQ Cs cT cV cW cX cY cZ dB dC dD dE dF dG dH DI dJ Dk DL dM) Mi(Fr Hq Hr Hu Hv Hx Ih Il Im Ip Ir It Iu Iv Jg Jh Ji Jk Jl Jm Jn Jp Jq Jr Js Li Lj Lw Lz Mb Mc Md Mf Mk Ml Mm Mn Mp Mr Ms Mt Mu Mv Mw My Mz Na Nb Nc Nf Ng Ni Nj Nk Nm Nn No Nq Ns Nt Nu Ny Of Og Oh Oi Om On Pb Pd Pf Qc Qe) dE(aD aE aF aG aI aK aL aU aV aW aZ bA bB bE bF bJ bM bN bO bR bU bW cB cC cD cE cF cG cL cM cN cR cT cV cX cY dB dC dD dG dH dL) cX(aC aD aG aK aM Ap aR aU aZ bE bG bO bR bW cB cC cD cF cG cL cM cN cV dB dC De) bW(aD aG aI Aj aL aM aR aZ bA bF bM bO bP cD cE cF cG cI dB dC dD dG dH dL) aG(aD aH aW aZ bJ bN bO cD cE cF cV dB dC dD dH dI) aU(aD Af aK aM aP aQ aZ bA bJ bP cA cE cR dB dC dH dI) dC(al aP aW bA bB bJ bL bO cF cG cV dB dI dN) Qd(Ik It Jo Lz Ml Ms Nj Nm Nn Of Oh Pz) bO(aF aM Ap aR Aw aZ bE bJ cB cG dB De) cG(Af bF bJ Bn cE cN cV dB dG dH dL) Nj(Ij Im Ip Lx Mg Mp Pe Pg Po) Ap(Af aI Aj aL Bn dD Dg dH) De(Af Aj aL Ax bA Bn cE dH) Hu(Im Ip Lw Ml Mp Oe Og) Aw(Af Ax bF Bn cV dH) aZ(al aW bJ bL cR dB) Jp(In Ip Iu Mp Oe) aP(aD bR dG dH) bE(al aL bA dD) dB(aM aR cC cO) Ms(Ji Jt Mz) Ip(Nb Nu Oe) Of(Mp Mw On) bJ(aL aM dD) Ng(Mg Mp) aF(aM bA) cM(cV Di) cZ(al aL) dH(bQ dl) NuOe LwIm MaOi aCdD bRdl cAcB cVdN} Mi{Ms(Et Fp Fr Hq Hr Hu Hv Hw Hx Ih It Ij Ik Il Im In In Io Ip Iq Ir Is It Iu Iv Jg Jh Ji Jj Jk Jl Jm Jn Jo Jp Jq Jr Js Jt Lh Li Lj Lu Lw Lx Ly Lz Ma Mb Mc Md Me Mf Mg Mh Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Hu(Fp Fr Hq Hr Hv Hw Hx Ih Ii Ik Il Im Io Ip Iq Is It Iu Jg Jh Ji Jj Jk Jl Jm Jn Jo Jp Jq Jr Js Lh Li Lj Lu Lw Lx Lz Ma Mb Mc Md Mf Mg Mh Mj Mk Ml Mm Mn Mp Mq Mr Mt Mu Mv Mw Mx My Mz Na Nb Nc Ne Nf Ng Nh Ni Nj Nk Nl Nm Nn No Nq Nr Ns Nt Nu Nv Nw Nx Ny Oe Of Og Oh Oi Om On Oy Oz Pa Pb Pc Pd Pe Pf Pg Po Pz Qa Qb Qc Qe) Jp(Et Fr Hq Hr Hv Hw Hx Ih Ik Il Im In Io Ip Ir Is It Iu Jg Jh Ji Jk Jl Jm Jn Jo Jq Jr Js Li Lj Lw Lx Lz Mb Mc Md Mf Mg Mh Mk Ml Mm Mn Mp Mq Mr Mt Mu Mv My Mz Nb Nc Ne Nf Ng Nh Ni Nj Nk Nm Nn No Nq Ns Nt Nu Nw Nx Ny Oe Of Og Oh Oi Om On Pb Pc Pd Pe Pf Pg Po Pz Qc Qe) Oh(Hq Hr Hv Hw Hx Ih Ik Il Im In Io Ip Ir Is Iu Iv Jh Jk Jm Jn Jr Jt Lh Li Lj Lu Lw Lz Ma Mc Mk Ml Mm Mp Mq My Mz Na Nb Ne Nf Ng Ni Nk Nl Nm Nn No Nr Ns Nu Nw Ny Of Og Ok Om On Pb Pc Pd Pe Pg Qa Qb Qd Qe) Mg(Et Fp Hv Ih In Ip Iq Is It Iu Jg Jk Jl Jm Jn Jq Js Jt Li Lj Lw Lz Ma Mb Mc Mk Ml Mp Mz Nb Nc Ne Nh Nj Nk Nm Nn No Nr Nt Nu Oi On Oz Pa Pe Pf Pz Qa Qb Qc Qe) Ni(Fp Fr Im Io Ip Iq It Jl Jn Jo Jq Js Lj Lz Mb Mc Mf Mk Ml Mm Mn Mr Mt Mu Mv My Nb Nc Ne Nf Ng Nh No Nq Nr Nu Nx Of Og Oi Om Oz Pb Pd Pe Pf Pz Qb Qc Qe) Pd(Hx Ii Im Ir Jl Jn Jq Jr Lh Lw Lz Mb Mc Mf Ml Mp Mr Mt Mu Mv My Nb Nf Ng Nk Nn No Nq Nr Ns Og Oi Om On Pa Pb Pc Pe Pg Po Qe) Ng(Et Hx Im It Ji Jl Jq Lh Lz Mf Ml Mp Mr Nb Nf Nk No Ns Nu Nv Of Og Oi Om On Pa Pb Pg Po) It(Hx Ij Il In Ip Ir Jk Mm Nb Ne Nh Nk Nu Og Oi On Pa Pe Qa Qb Qd Qe) Og(Fr Hx Jl Jq Lz Mf Ml Mr Mv Nb

Figure 37 Continued

Nf No Nq Nu Of Oi Pa Pb) Mm(Hx Im Ip Jh Lh Li Mh Ml Nb Ne Nu Nv Nw On Qd) Pa(Ik Iq Jq Js Ml Mr Mt Mv My Nf No Of Pf) Nu(Fr Jg Ji Ml Mr Mt Mw Nk Nq Oe Oi Pz) Nq(Hx Ml Mp Mr Nb Ne Nf Nh Nk Qd) Of(Hx Mh Ml Nb Nv Ny Oi Pg Po Qd) Ne(Fp Ii Jj Jo Mw Nj Oy Oz Pz) Mr(Hx Ip Jl Lh Mb Nb Oi Pe) Qd(Ik Jj Jo Mw Nj Nm Nn Pz) Im(Fr Ji Jo Js Nk Nn Pz) Nh(Fp Ii Mw Nj Oz Pz) Il(Fp Ji Mb Mn On Pz) Pe(Fp Jq Js Mw No Pf) Ji(Is Lz Mf Nb On) Jo(Hw Ij Lh Pg Po) Nk(Mb Nc Nw Pc) Hx(Hr Ml Mu Mw) Oi(Ml Nb Nf Qc) Ny(Ml Nf Pb) Mn(Jk Pg) Js(On Qe) PoHq NmNw NoLh MbJk MjIk MvJl NjNl IiIj OyPg} bA{bW(aC AD aE AF aG aH aI AJ aK aL aM AN aO AP aQ aR AS aU aV AW AX aZ Ba bB BC bE bF Bg bH bJ bL bM BN BO bP bQ bR bU bV bX bZ cA cB cC cD cE cF cG CH cL cN CO CP Cq cR CS CT CV CW CX cY cZ dA Db DC dD DE dF DG dH DI dJ DK DL dM FR) cS(aC Ad aE Af aI AJ aK aL aM An Ao Ap aQ Ar AS aU aV Aw AX aY aZ Ba BB Bc bF BG bI bJ bL bM BN BO bP bQ bR bS bU bV bX bZ cA cC cD cE cF cG CH cI cL CO CP Cq cR Cs CT cV Cw CX cY cZ DB Dc DE dF Dg dH DI DK DL dM Fr) De(AD AF aI Aj aK AL aM AN Ao aP aQ Ar As aU aV AX aZ BB BC bF Bg bJ bL bM BN BO bP bQ bR bS bU bV bX cA cB cC cD cE cF cG Ch cI cJ cK cL cM cN CO Cp Cq Cs CT cV Cw CX cY dA Dc dE dG dH Di dJ DL dM dN Fr) aX(aC aD aE Af aG aI AJ AI aM An aO AP AS Aw Ax aY aZ Ba Bb Bc bF Bg bH bI bJ bL bM Bn BO bR bU bV cA cC cE CH cL cM cN Cp Cq cR Cs CT Cu cV cW CX DB DC Dd dE dF Dg dH DI Dk dM dN Fr) bC(aC Af aI AJ aM AP As Aw aZ Bb bF Bg bJ bL bM Bn BO bR bV cB cC cD cE cF Ch cR CT CX dB dE dF dH DI dK DI Fr) Ap(Ad AF aI Aj aU AW bF Bg bJ bO cD cF Ch cJ cK Ct CV CX Dg dH Di) Cx(aG aK aP aU aV Aw aZ bE bG bJ bO cB cC cG cJ cR Cu Cw cY dC dE Di dK Fr) aU(Af Aj aP aQ Ar As Aw Ax Bc Bg bJ Bn Bo CT cX dE Di Dk Fr) Fr(bF Bg bJ Bn bQ cB cC cD cE cJ cV dA dB dC dF dH Di dK) dE(aF aG aI aP AW bJ bO cB cC cJ cV cX dC dK) aP(aD aF Aw bJ bO bR cC cP cX dG dH Di dK) cC(aF bJ bL cG cO cV cX dB DI dK fR) bJ(aI aL Aw bB bO cG cO cX Di dK) cX(aG aZ bE cG cR dC Di dK) dK(aJ Ax Bc Bn cT Di Dk) Aw(AF Bn cJ cV) Di(aF aW Bn cJ cV) cE(bZ cG CO) cJ(Af Bn Bo) bE(aI aL) bF(cG Co) AdCu BncG aFcR cOdH cTdC} aP{dH(aD aE AF aG aH aI aJ aK aL aM AN aO Ap aQ aR aS aU aV AW aX aY aZ BB bC bE bF bG bH bI bJ bL BN BO bP bQ bR bS bU bV bW bX bZ cA cB cC cD cE cF cG cH cI cJ cK cL cM cN CO cP cQ cR cS cT cV cW CX cY cZ dA dB dC dD DE dF dG DI dJ dK dL dM dN Fr) dG(aC aD aE AF aG aH aI AJ aK aL aM aN aO aQ aR aS aU aV AW aX aY aZ bB bC bE bF bG bH bI bJ bL bM BN BO bP bQ bR bS bU bV bW bX bZ cA cB cC cD cE cF cG cH cI cJ cK cL cM cN cP cQ cR cS cT cW CX cY cZ dA dB dC dD DE dF DI dJ dK DL dM Fr) dK(aD aE Af aG aH aI AJ aK aL aM aN aQ As aV aW Ax aZ bB bF bG bJ bM BN bO bP bS bU bW bX cA cD cE cF cH cJ cL cM cN cP cQ cS cT cW CX cY cZ dA dB dC dD dF Dg Di dJ Dk dL dM) Cx(AD aG aI aL aQ As aU aV Aw Ax aZ bB bC bF Bg bM bN bO bP bR bZ cB cC cD cE cF cI cJ cK cM CP Cq cS cT Cu cV Cw cX dA dB DC DD De Dg Di dL) dL(aD aE Af aG aI aL aQ aU aV AW aX bB bF bO bR bW cB cC cD cF cI cJ cM cN cP cS cX dA dB dC dD dJ) aL(aD Af aU AW aX bC bE bF bJ Bn bO bR bW cC cD cF cN cP cR cS cX cZ dA dB dC dE dF Di) aD(Af aI aU aX aZ bC bF bJ bN bO bR cC cD cE cF cJ cM cN cS cX dB dC dD dE Di) bO(aE aX aZ bF bM bN bP bR bX cB cE cF cJ cN cP cS cX dB dC dE Di) cJ(Af Aj An As Aw Ax Bb bM Bn Bo bP bR cE cF cN cX DC Dg Di) cE(aE aG aI aO aU Aw bB bF bR cB cG cP cS cX dA dB dC dD) aX(aE aO aS aY bM bX cD cF cL cN cT cW dB dC) dC(Af aZ bF bN bR cB cX dA dB dE) aI(aH aZ bF bJ bP cS dB dE dF) bR(Af bC bM bN bP bX cF cX) cS(aE Af As bM bP cT cX dD) cF(aE aZ cB cP cX dB) bM(aF bW cD dA dB) cX(aG aZ cB cC dA) Aw(Af Aj Bg Bn) dD(bF bJ dE) Af(cD Di) Aj(aU bW) aE(dB dE) bP(cP dB) AsbC DgDi aZcN bXcB} Qd{Ik(Fp Hq Hr Hu Hv Hx Ih Ii Il Im In Io Ip Iq Ir Iu Iv Jg Jk Jl Jm Jn Jo Jp Jq Jr Js Jt Lh Lj Lx Ly Lz Mc Md Me Mf Mg Mj Mk Ml Mn Mp Mq Mr Ms Mt Mu Mv Mw Na Nb Nc Nf Ng Ni Nj Nk Nl Nm Nn No Nq Nr Ns Nt Nu Nv Nx Of Og Oh Oi On Oy Oz Pa Pb Pc Pd Pe Pf Pg Po Pz Qb Qe) Jj(Fp Hq Hr Hu Hv Hw Hx Ii Ij Im In Io Ip Iq Is It Iu Jg Jh Jk Jl Jm Jo Jp Jt Lh Li Lj Ly Lz Mc Md Me Mf Mk Ml Mp Mr Ms Mt Mu Mw Mz Nb Nd Ne Nf Ng Nh Ni Nj Nk Nn Nr Ns Nu Nv Ny Of Og Oh Oi Oy Oz Pa Pb Pc Pd Pe Pg Po Pz Qa Qb Qc Qe) Pz(Et Fp Fr Hq Hu Hv Hx Ii Il Im Ip It Iu Iv Jg Ji Jk Jl Jo Jp Jt Lh Lj Lw Ly Lz Mc Md Mf Ml Mm Mp Mr Ms Mw Nb Nf Ni Nj Nl Nm Nn Nq Nr Ns Nt Nu Nv Nw Nx Of Oh Oi Ok On Oy Oz Pa Pc Pe Pg Qb) Jo(Fp Hu Hw Hx Ii In Ip It Iu Iv Jg Jk Jl Jp Jt Lh Lw Ma Md Mf Mg Ml Mp Mq Mr Ms Nb Ni Nj Nk Nl Nm Nn No Nq Nr Nt Nu Nv Nx Oh Ok On Oz Pa Pc Pe Pg Po Qb) Ml(Fp Hq Hu Ip Iq It Jm Jp Ly Md Mg Mh Ms My Nf Ng Ni Nj Nk Nl Nn Nq Ns Nu Nw Of Og Oh Oi Oy Pf Qe) Ms(Fp Hq Il Im Ip It Ji Jp Jt Lw Mz Nj Nm Ns Nu Nw Oe Of Oi Ok On Oy) Oh(Iu Ji Jt Lj Lw Lx Mm Mp Nb Nn Nv Nw Ok On Pc) Im(Fp Hq Hu Jp Ni Nj Nk Ns Of Og Pf) Il(Ii Iu Jl Jp Nb Nj Ns Of Pa Pf) Nn(Lj Lw Mp Nb Nv Nw On) Mm(Lw Mg Mp Nt Nu Ok On) Nu(It Jp Nj Nm Of) Nj(It Jp Of) Nm(Ip Nw) Of(It Jp) Pf(Pe Pg)} Ms{Ji(Et Fp Fr Hq Hu Hv Hw Hx Ih Ii Ij Ik Il Im In Io Ip Iq Ir Iu Iv Jg Jh Jk Jl Jm Jp Jq Jt Lh Li Lj Lu Lw Ly Lz Ma Mb Mc Md Me Mf Mg Mh Mj Mk Ml Mm Mn Mp Mq Mr Mt Mu Mv Mw Mx My Mz Na Nb Nc Nd Ne Nf Ng Nh Ni Nj Nk Nl Nn No Nq Nr Ns Nt Nu Nv Nw Nx Of Og Oh Oi Om On Oy Oz Pa Pb Pc Pc Pf Pg Po Pz Qb Qc Qe) Ok(Hq Hu Hx Ii Ik Il Ip Iu Iv Jg Jk Jl Jp Js Jt Lh Lj Lu Lw Ly Lz Ma Mc Me Mg Mh Ml Mm Mn Mp Mq Mr Mt Mu Mv Mw My Mz Nb Nd Ne Nj Nm Nn Nq Nr Ns Nt Nu Nv Nx Oe Og Oh Oi On Oz Pa Pc Pf Pg) On(Et Hv Hx Ih Ij Im In Ip Iq It Iu Iv Jl Jp Jt Li Lw Ly Lz Ma Md Me Mh Ml Mm Mp My Mz Nd Nj Nl Nm Ns Nt Nu Nw Of Og Oy Pb Pc Pe Pg Qa) Jt(Et Fp Fr Hr Ii Im Ip Jp Lw Ly Ma Mh Ml Mm Mx Nd Nn Nq Ns Nt Nu Nw Oe Of Og Oi Pb) Lw(Hv Hw Hx Ij Im Iv Jl Jp Mz Nb Nt Nu Pe Pg) Jp(Fr Im Is Iu Ma Mp Mz Nm Nt Pe) Mz(Iu Mg Mp Nm Nn Nq Nw) Is(Iv Jr Mh Ml) Nw(Mp Nj Nu Oe) Nm(Hv Iu Mr) Im(Ih Jj Nb) MlQa MpJl IjJj} aX{Ax(aD aI aL As Aw aY aZ bF bO bQ bR bV bW cA cB cC cE cH cJ cK cN Cs cT Cx dA dC Dd dH dI dK) Dd(aC AD Af aI Aj aL An As aZ bJ bM Bn BO bQ cH cJ cK Cp Cq cT Cw Cx dB dD dH dI) cJ(Ad Af Aj Al An Ao Ap As Bb Bn Bo Ch Co Cp Cq Cs Cu Cx Db Dc Dg Di Dk) aJ(aD aE aI aL aY bM bO bP cE cH cN cT cX cZ dB dD dG dH dL) Cu(aC AD aI Aj aL An As Bn Bo Cp Cq Cw CX Dc Dg) Cq(Af aI Aj aL As aZ Bb bM Bn bO cK Cx dH) Cx(aC aD aI aL aZ bO Cp cT DC dH Di) aL(aC Al As aU Aw bM Cp cR DC Di) cZ(aE aK aQ bG bL bM bO bS cY dC) cT(bG bM bO bP cR cY dD dE dM) Dc(aC Ad aI Aj As Bn Cw Dg) dD(aQ aU aZ bG bM cY dJ dM) Cp(aC Ad aI Aj As Bn Cw) dM(aE aS aY bO bR dB dH) aZ(aO Bn cR Cv cY) bG(aE bM bO bP dH) bM(aI aS bO dJ) bO(aW dJ) AscK BbaC aIaU} dK{Ax(aC Ad aE AF aG aH aI AJ aL aM AN Ap aQ Ar AS aU aV AW aY aZ Ba BB Bc bF bG bI bJ bL bM BN BO bP bQ bR bU bV bW bX bZ cA cB cC cD cE cG CH cI cJ cK cO CP cQ cR CS CT CV CW CX cZ dA DB Dc DD DE dF DG dH Di dJ Dk DI dM dN FR) Dk(Ad Af aI AJ aL As aZ BB Bc bF Bg bL bM Bn BO bP bV cD cE Ch cJ Co Ct CX dB dE Di dM) dM(aE Af aH aI aL aV aZ bF bL BN bO bP bU bV cD cE cJ cM cV CX cZ dB dD dG dH) aJ(aD aE Af aI Aj aL aZ bM bO bP cJ cM CX dB dC dD dG dH dL) aZ(Af Al aO Ar aU Bc Bn bO bS bV Cq Cv CX dN Fr) aL(Ar Bc bH Bn bS Cs Cx Dc dE Di FR) Cu(Ad Aj As Bn Cq Cx Dc) Bc(aI cJ cT Cx dB) dF(Af cE Cx) AjFr CxDd} cS{aL(Ad Af AJ aK Al aM An Ao Ap aQ Ar As aU Aw Ax Ba Bb Bc Bg bM Bn Bo cC Ch Co Cp Cq cR Cs Ct Cu Cv Cw CX cY Db Dc Dd DE Dg Di dJ Dk Dl dM Fr) Aj(aE Af aH aI As Aw Ax aZ Ba BB Bc bL bM bO bP bR cB cJ cK Cp cT Cu cV CX cZ dB Dc DD dF Di Dk Dl Fr) Ax(Ad Af aI Ao As Aw bM bO bQ bR bU cD cE cK Co cP Cs CX dB DI) aZ(Ad Af aK aO Ap As Aw Ba Bg Bo Ch Cq Ct Cv Cx Db Dd Dg Di) As(Af aI bE bM bO bP cJ Cq cT Cu cZ Dc dF Di Dk dM) Af(aE aI Aw Bc bM bO cB cJ cT Cu Cv cZ dB dF) Cx(aI Bb bO cB cJ cT Cu Dc dF Di) bM(aI aS bO Cq cT cX dB dD Dg dJ) Cu(Ad An Bo Cp Cq Cw Dc) Bb(aC Ad aI Ap dD Dg) aJ(aD aI cX dD dH) Di(cJ cT dD) dM(aI cX) AdDc AocJ BcdD BnCq CtcT DgDl aWbO} Jp{Im(Il In Iu Jk Mj Mm Mp Nb Ne Nk Oe Pa Pg) Pe(Ii Jj Jo Lw Ml Nj Nu Oe Oi Oz Pf) On(Hv In Mb Mm Mp Nx Of Og Oi Pb) Oe(Hw Hx In Iu Mp Nu Pa Pg Po) Ne(Iu Ji Ma Mp Nm Nn Nu) Nh(Ji Ma Mp Nm Nn Nu) Il(Ji Lw Ma Mp Nm Nn) Oi(Iu Ma Mg Mp Nn Nq) Lw(Hu Hv Jk Pg) In(Jj Mm Nn Nu) Po(Jj Jo Mm) Nm(Hv Jk Pg) Ml(Is Nu Qa) Of(Jk Mw Pa) Ng(Mg Mp) Hw(Jj Jo) Qa(Nf Pb) Ji(Hu Pg) NuPg MmLi MwMy IjJj} Cx{Cu(AD aG aI aJ aO aU aV Aw bB bC bE bO bW cC cG cJ cK cR cT

Figure 37 Continued dB dC dE dF Di dJ dN fR) cJ(aJ aZ Ba Bb Bc bO bV cT Cw Dc Dd dE dF Di dM Fr) aJ(aD Aw aZ bC bM cD cM dC dG Di) cG(Ad bF Bg bO
cE dB Dg dH Di) Aw(Al Ax aZ bO Dd Dk) cT(Ap bC bW De Di Fr) aL(Ap bC bE bW De) aZ(aO bC bE bW dN) Cw(Ad bO) bC(Bb Dc) AjBa
AsFr BcdC DdDi DedF bOdE} On{Nj(Et Hw Ij Im Ip Li Lx Mh Ml My Nb Ns Nw Of Oy Pb Pc Pe Pg) Of(Hu Jj Mb Ml Mm Nn Ns Nu Oh Oz
Pz) Pb(Hu li Mb Mm Ns Nu Oh Pz) Nu(Ml Mm Om Og Oi) Mb(Ml Nd Og Oi) Mm(Et Im Ip Nw) Hu(My Ng Og Oy) li(Ij Mh My Pe) Pf(Im Pe
Pg) MlPz ImJo OzPg} aL{bW(Af Aj Al aM aQ As Ax Bg Bn Ch Co Ct Cv Di Dk dN) bE(aJ Al An Ax Bc Bn Cp Cq Cs Dc Dd Di dM) bC(aJ
As Aw Ba Bg Bn Ch Cp Di dM) Ap(Aj bJ cE Ch dB Dg Di) aJ(aD dC dE dG) Aw(Bn dI) Fr(As cE) DecT cCdE} Jj{Po(Hu Hv Ij In Ip Jt Mf Ml
Nb Ni Nj Nu Nw Pe Pg) Pe(Fp Hu Im Ip Lj Ml Nb Nf Nu Nw Oz) Ij(Hu Ip Lh Ml Nu Nw) Pg(Hu Ip Ml Nu Pc) In(Ip Lx Nu Nw) Qa(Hu Ml Nu)
Hw(Hu Nw) NuJk} Cu{Ad(aI Ap aU Aw Bb bC bO cF cJ cK cX dB dC De dH Di) As(aG aO Aw bC bW cJ cK Cv cX dC dH) cJ(Aj An Bn bO
Cq Cw cX Dc Dl) bC(Aj An Cp Cw) Aw(Bn Cp Cq) Bn(aO dC) CpbW} Nj{Im(Hw Iu Jl Lw Mj Mp Nb Nd Ni Nr Nv Pa Pe Pg) Mm(Il Jk Ne
Nh Pa Pe Pg) Pe(li Lj Lw Ml Ok Oz) Nv(Ml Mp Of Pb) Pg(Ji Lw Nw Ok) Nd(Ma Nm Nn) Lw(Hu Hw) Nw(Il Jk)} aJ{cJ(aD Af As bM Bn cX
dG dH Di dL) dG(aD aG aI aZ bM cG dC) aZ(aI cF cX dD dH) dC(al bO cX dB) dH(aD Aw cB cG) aD(al cX) bC(As cX) AwBn aEdE aldL
bMcD} Aw{Ax(Ad As aZ Ba bB bF Bg Bn BO cC cD cE Ch cJ Co cR Cs dB Dk) As(Ar BC) Bn(Bc bO Dk) Aj(bW Fr) Bg(Ar Dk) Ch(Dk Fr)
aZ(bO bV) cEcG} Nw{Mm(Im Ip Iu Jh Ji Jk Jt Li Lx Ma Mg Ml Mp Nn Nq Nt Nu Og Po) Nu(Nk Nm Oe) Jo(Hw In Pe) li(In Pg) Pf(Pe Pg)
NmIp HuOe} Aj{bW(aG Al Ax aZ bM bP cJ Cq cT dC Dd) cJ(Ap Ba bC Cw Fr) Fr(Ba dC Dd) Ap(Ax aZ) bC(Bb Dc) cG(Bn cE) BacX}
Hu{Lw(Hx li Im It JI Mj Mr Nb Nr Pg) Ok(Ne Nm Oe Of Og) Ji(Ng Og Oi) NmNg MlIs MpIm} aZ{cJ(An Ap Ar Ax Bn Di Fr) Ap(Ad aI Dg)
dN(bO bS dC) Fr(Ad Dg) aO(bW cX) AfbW AsbC bLcX} Pe{Pf(Et Im Jg Ji Jt Lw Ml Mm Nm Ok Oz) Jo(Et Iu Ml Mm Oz) li(Fp Jt) MmOh}
bC{As(al Bb bO cB cT Dc Di Fr) cT(bM Ct) AdDc BbDg} cG{cE(Ad Af aO bL cT cX Di Dl) cX(bF bO) AdAx BnDg} Nu{Mm(Im Is Nv Qa)
Ml(Is Mz Qa) Hx(Oe Og) MzOe Nilm} cJ{Di(Ax Bc bO Ch Dc) Fr(cE cT dB) AdDc ApDg} Pg{li(Ji Jt Lw Ok) Lw(Mm Oh) Pf(Ji Ok) MmJo}
Ad{Dc(Ap aU bW De Fr) Ap(Ax Dd)} Im{Ns(Iu Mj) Mm(Jt Lh) MjJo NbNi} Ax{As(aU bW De) ApDl aKaU} Po{Jo(Iu Ji Jt)} cT{AfbW FrcE
cCdE} Ml{MbIs QaOf} AfBabO BcdBdC liIlOk Unconstrained panels with 3 analytes, where 1.0E-7 >= 'AUC p-value' > 1.0E-8. Contains 6,862 panels of 590,601 total panels evaluated. :
Lv{Li(Et Fp Fr Hq Hr Hu Ih Ii Io It Iv Jg Jh Jl Jm Jn Jr Js Lh Lj Lu Lz Ma Mc Md Me Mj Mk Mm Mn Mp Mq Mr Mt Mu Mv Mw Mx My Na
Nb Nc Nl Nn No Nq Nr Ns Nt Nv Nx Ny Oh Om Oy Oz Pa Pb Pc Pd Pz Qb Qc Qe) Iq(Fr Hr Hu Hw Ih Ii Ik Il Io It Iu Jk Jl Jm Jn Jo Jr Js Lh Lj
Lu Mb Mc Me Mh Mj Mk Mn Mr Mt Mu Mv Mw Mx My Na Nb Nc Ne Ng Nh Nl Nn Nq Nr Ns Nv Nx Ny Of Oh Oy Oz Pa Pb Pc Pd Pf Pg Pz
Qb Qc Qe) Nv(Et Hr Hv Hw Ih Ii Ij Ik Io Ip Ir Is It Iu Jg Jl Jm Jn Jq Jr Js Lh Lj Lw Lz Mb Mc Mj Mk Mm Mp Ms Mt Mu Mv Mw Mx Na Nb
Nc Nh Ni Nl Nm Nn No Nq Nr Nt Nx Ny Oh Om Oz Pa Pc Pd Pg Pz Qc) Qe(Et Fp Hq Hr Hu In Io It It Iu Iv Jl Jm Jn Jq Jr Js Lj Lz Ma Mb Mc
Md Me Mh Mj Mk Mn Mp Mq Mr Mt Mu Mw Mx Na Nb Nf Nk Nl Nn No Nq Nr Ns Nt Oh Oy Pb Pc Pd Pe Pg Pz Qa Qb Qc) Ni(Hq Hr Hu
Hw Ih Ii Ik Il It Iv Jh Jl Jn Jr Js Jt Lh Lj Mb Mc Md Me Mg Mj Mk Mq Mr Mt Mu Mv Mw Mx My Na Nb Nc Nf Nj Nk Nl No Nq Nr Ns Nx Og
Oh Oi Oy Oz Pa Pb Pc Pg Pz Qb) No(Et Hr Hu Hv Ih Ii Ik Il It Iu Iv Jg Jh Ji Jk Jg Jr Js Jt Lj Lu Lz Ma Mb Mc Md Mk Mn Mp Mq Mu My Ne
Nf Nh Nm Nn Nq Ns Nt Nx Ny Oh Ok Om Pa Pb Pc Pd Pg Po Qb Qc) Et(Fp Hq Hr Hu Hw Ih Ii Io It Jg Jh Jk Jl Jm Jn Jr Js Lh Lj Lu Ma Mc
Md Me Mh Mj Mk Mm Mn Mr Mt Mu Mx My Nb Ne Nh Nl Nn Nq Ns Nx Ny Oh Om Pa Pb Pc Pd Pz Qb) Nd(Fp Fr Hq Hr Hu Ih Ii Ik In Io It
Iu Jh Jl Jn Jo Jr Js Lh Lj Lw Lz Mc Md Mg Mh Mj Mk Mq Mt Mu Mv Mw Mx My Nb Nc Ng Nq Ns Nx Of Og Oh Oi Oy Pb Pc Pz Qb) Jt(Fp
Fr Hq Hr Hu Hv Hw Il Io Ir Iu Iv Jg Jk Jl Jm Js Lh Lj Lu Lz Ma Mc Md Me Mk Mt Mu Mw Mx Na Nb Ne Nk Nl Nn Nq Nt Oh Oy Oz Pa Pg Pz
Qb Qc) Ip(Hq Hr Hu Ii Ik Jh Jm Jn Jr Js Lh Lz Ma Mb Me Mh Mj Mk Mn Mq Ml Mv Mw Mx My Na Nc Ne Nf Ng Nn Nq Ns Nx Ny Of Og Oh
Oy Pb Pc Pd Pf Pz Qc) Jq(Fp Fr Hr Hw Ih Ii Ij In Io Ir It Jg Ji Jm Jn Jr Js Lh Lz Ma Mg Mh Mj Mk Mn Mq Mr Mv Mw Mx My Na Nc Nl Nq
Nr Nt Ny Oh Oi Om Oy Oz Pc Pd) Pg(Hr Hu Hv Ij Il In Io Ir Is It Iu Jg Jh Jl Jr Lj Lu Lz Ma Mb Md Mh Mn Mq Mr Mt Mu Mw Mx My Nb Nk
Nl Nn Ns Nt Nx Ny Pa Pb Pd Po Pz Qb Qc) Lx(Fp Hr Hu Ik Io Jk Jm Js Lh Lj Lu Lz Mb Mc Md Mg Mh Mk Mn Mt Mu Mv Mw Mx My Nc Ne
Nf Nh Nq Ns Nx Ny Of Og Oh Om Oy Oz Pd Pf Pz Qb Qc) Oe(Hq Hr Hu Ik It Jm Js Lj Lw Lz Ma Mc Md Mj Mk Mn Mp Mq Mt Mu Mv Mw
Mx My Na Nc Nf Ng Nj Nn Nq Ns Nx Of Og Oh Oi Oy Pb Pc Pf Pz) Ir(Fp Fr Hu Hw Io It Jk Jl Jn Jr Lh Lu Mc Md Me Mj Mk Mn Mr Ms Mt
Mv Mw My Na Nc Ne Nh Nl Nr Nx Ny Oh Ok Om Pa Pc Pd Qa Qb Qc) Ij(Fp Hq Hu Hv Ii In Io It Iu Iv Jg Jk Jl Js Lj Lu Mb Mc Md Mh Mn
Mp Mq Ms Mt Mx Nf Ng Nm Nn Nt Nx Of Oh Oi Oz Pb Pc Pz Qb) Mm(Hq Hr Io Iu Iv Jg Jh Ji Jl Jr Lh Lu Lw Lz Mb Mc Md Mh Mk Mn Mt
Mu Mv Mw My Na Nb Nc Ne Nh Nq Ns Ny Om Oz Pa Pb Pd Qc) Hv(Hq Hw Ih Ii Io Iv Jg Jh Ji Jk Jl Jn Jr Lh Lj Lu Ma Mb Mp Mr Mt Nb Ng
Nn Nq Nr Ns Nt Nx Of Oi Ok Om Oy Pa Pf Qb Qc) Nm(Fp Hq Hw Ik Io Jg Jh Jm Lh Mb Mc Md Me Mh Mn Mp Mt Mu Mw Nb Nc Ne Ng Nh
Nn Nq Nt Og Oh Om Oz Pa Pb Pc Pz Qc) Jl(Hr Hu Jg Jh Jm Jn Jr Lh Lj Lw Lz Mc Mk Mn Mq Mr Mx Na Nb Ne Nj Nl Nr Ns Nx Ny Of Og
Om Oy Pa Pd Pz Qb) Lw(Fp Hq Iv Jg Jh Jm Js Lh Lj Lu Ly Md Me Mf Mj Mk Mq Mt Mu Mw Nc Nf Nn Nq Ny Oh Pa Pc Pz Qb Qc) Ly(Fr Hr
Ii Jg Jh Jm Jo Jr Js Ma Me Mj Mk Mp Mq Mt Mv Mw Mx My Na Nb Ng Nj Nn Ny Og Pa Qc) Om(Hq Hu Il In Iu Iv Jh Jm Jo Jr Js Lj Mb Mc
Mp Mr My Ne Nf Nl Ns Nx Ny Ok Oy Pb Pd Qb Qc) Nk(Ih Il In Iu Jk Jn Jo Jr Mb Me Mf Mg Mp Mq Mt Mu Mw My Na Nc Nn Nq Nx Og Oi
Pz Qb) Nl(Hq Hw Ik Il In Iu Jg Jn Jo Jr Lj Mb Mf Mt Mu Mw Nc Ne Nn Nq Ny Ok Pa Pb Pz Qb Qc) Nt(Hq Hw Il In Iu Jk Jn Jr Mb Mp Mr Ne
Nf Ng Nr Nx Ny Of Oy Oz Pa Pb Pd Pe Pf Qb) Mr(Hq Hr Ii In Iu Jg Jh Jn Jr Lj Lz Mb Mf Mq Mt Mu Nj Nn Nq Ns Nx Ny Oi On Pc) Nj(Ih Il In
Iv Jk Jn Jr Lh Lj Mf Mg Mk Mq Mt Mw My Na Nb Nn Nq Nr Pa Pz Qb) Hw(Fp Fr Hq Hr Ii Io Iv Jg Jh Ji Jk Lu Ma Mb Mh Mp Nf Ng Ns Pb Pf
Po Qb Qc) Ny(Il In Iu Iv Jg Jh Ji Jk Jn Jo Jr Ma Mb Me Mf Mp Nf Ng Nr Oi Ok Qa Qc) Nr(Hq Hr Ii In Iu Jg Jn Jo Jr Lj Lz Mb Mf Mh Mp Na
Nn Pe Qb Qc) Ml(Hq Hu Jh Jm Mb Mf Mn Mu Mw My Ng Nn Ns Nx Of Og Oy Pc Pf) Qb(Fr Ik In Iu Iv Jg Jh Jo Ma Mf Mg Mq Nq Of Og Oh
Pc Pf Qc) Jn(Fr Hq Hu Il In It Jg Jr Me Nb Nf Ng Nn Nx Oh Oi Oz Pb Pc) Mp(Hu li Il In It Jg Jk Lj Mb Md Me Mx Nn Oh Oy Pe Qc) Oi(li Il
In Jh Jr Js Lh Mb Mg Mt Mv My Na Oh Oz Pa Pc) Mf(Ih Il Iv Jg Jh Jr Js Lj Md Me Mg Mq Mu Mv My Na) Iu(Fr Il In It Iv Jg Lz Mb Mc Nf
Nq Ns Nx Of Pf Qc) Jk(Fp Fr Hq Hu Ii Iv Lj Ma Nf Ns Nx Oy Pb Pf Pz Qc) Jr(Fr Il In It Mb Me Mu Nf Nn Nq Nx Oh Pb) Ok(Fr Hr Ji Jo Js Lh
Lu Me Mn Mv Mz Oz Pd) Jg(Hu Ii Ik Il In It Md Mw Nf Nh Ns On) Iv(In Jh Ma Ne Ng Ns Nx Og Oz Pa Pf) Fr(Ik It Ji Jo Me Mj Nf Of Og Oz)
Il(Hq Jh Jo Ma Mb Nn Ns Pb Pc Pf) Qc(Ik Jh Jo Mb Ne Ng Of Og Pa) Ji(Hq Mb Me Mg Mx Mz Na Nq Pd) Jj(Lj Mh Ms Ng Og Oh Oy Pc)
Nu(Fp Io Md Mg Ne Nh Pf) Ik(In Js Ma Mq Mv Nn Pa) Is(Lh Mg Mq Mv Na Nc Pe) Po(Lh Mg Ms Mu Ne Nh) Ng(Js Ma Mv Mw Nn Nq)
In(Jh Ma Nb Nn Nx Pf) Of(Ii Js Lh Ma Mw Pz) On(li Mu Nf Nh Nq) Pe(Mg Ms Na Nc Nh) Im(Lu Mg Ms Nh) Qa(Hr Mg Nc Nh) Jo(li Mq Mv
My) Og(Ih li Nb Pa) Nn(lt Me Nf) Mb(Ma Me Na) Mq(Oy Oz) Na(Md Nf) Pb(Oz Pa) LzMj MaPf MeJh MsMy} cU{cN(aC aH aK Al aN aQ
aR aS aU aV aW Ax aY bE BG bH bl BN Bo bP bR bU bX cA cC cE cF CH cJ cL cO Cq cR Cs cV Cw cY cZ De Dg dl DL dN) dB(Af aH aM
aN Ao aR aS aU aV AW Ax aZ bB BC bE Bg bH bl bN bP bR bU bV bX cD cF cG Ch cl cK CO cP Cq cR cV Cw dA Db De Dg dl dL dN fR)
bZ(aF Aj Al aN Ao AR aW Ax aY aZ Bc Bg bI BN Bo bP bR bU bX cA cB cF CH cl cL Co cP CQ Cu cV cZ dA Db Dc De Dg dH dJ Dk Dl)
cT(Ad aF Aj aK aN aO aQ AR aV aW Ax aZ Ba Bc bG bl bN bP bV bX cB CH cl cK Co Cq Cs Ct Cv cY cZ Db Dc Dg Dk dL Fr) aD(aH aK
Al aN aQ AR aS aV aW Ax aZ BC Bg bl bM Bo bR bX cF cG CH cJ cK cP Cq Cs cY dA Dc Dd De Dg dl Dl) cC(aC aH aK Al aM aO Ap

Figure 37 Continued aQ aU aV aW bB bC bE bG bH bJ bM bU cG cI cL CP CQ cV cY cZ dA Dc dD dF dG dH dL dN Fr) bO(aC Ad aH aK aN aQ aS aU aW aX aZ
bB bE Bg bP bX cD cF CH cK cO cP CQ Cs Cw cY cZ dA Dc dD Dg dI dL dN Fr) Bb(aE aJ aK aM aN Ao Ar aW aZ Bc bH bM bN Bo bS bW
cF cH cI CP CQ cR cV cW Db dD De dF dJ Dk dL dM FR) Dd(Ar AW Ax aZ bA bB bE bG bH bJ Bo bQ bR bU bX cA cD cG cH cI cK CO
CQ cR Cv Cw cZ dA Db dD Dg dH dI) dH(aE aH aK AL aM aN aV aW aZ bC bE bG bH bJ bN Bo bV cE cH cI CP CQ cV cY dA Dc dF dI dL
dN) dM(aK aO Ap aS aV aW aZ Ba bG bH bM Bn bP bV bW bX cB cF cG cH cI cK cO Cp cQ cV cW cY cZ dF dI dL dN) Di(Ad Af Aj Ar aS
aW bB bE bG bH bI Bo bS bV cF cI Cq cR Cu Cw cZ Db dD De dF dG dJ Dk DL dN Fr) Ap(aE aG Al aM AN Ao aP aQ aU aW Ax Ba bB BC
bN bS bW cB cH cI Ct Cv cW cY cZ dG dI Dk fR) cL(aC aK AL aM aO aU aV aZ bE bH bJ bM bR cD cH cO Cp CQ Ct cV Cw cY dA dD dF
dG dI dL Fr) cW(aH aK aN aQ aS aU aV aW aZ Ba bB bC bJ bM bR bU bV bW bX cF cJ cO cQ cS cY cZ dA dF dL dN) Cp(Ad aG aH aJ An
aP aQ aY bC bJ bQ bR bU bV bW cA cD cG cI cK CO CS dA Dg dI) Fr(Ad Af aG aH aJ An aP aQ aU Aw Ax Ba bP bU bV cA cB cF cG CO
cS cY dE dF dG dI) bH(aH aK aN aO aQ aS AW Ba bM bR bU bV bW cA cD cG cI cJ cO cQ cS cV cY dD dI dN) dC(Af aH Al aN aR aX Bc
bI bN Bo bP bS bV cB Co cP CQ cR Cv Cw Db Dc dD dF Dg dN) bJ(aH aU aW aX aZ bB bM Bn bR bU bV bW cA cD cF cG Ch cK cO cQ
cY cZ dA dD dF dI) cE(Ad AF An AR aS aW aY bI bN bP bX cA cB cF CH Cs Cu cZ dA Db dJ Dk Dl) Al(aE aG aH AN aQ aX aY bA bB Bg
bL bQ cA Ch cK cO cR Cs cY dA dD dJ fR) Ba(aF AJ aK aM aN Ao AR aW aX BC bW bX cH cI cP cV Cw cZ Db De Dl) aL(aH aK aN Ao
aR aS aU aV aW Bn bR bU bV cD cF cG cH cO cR Cw cY cZ Dc dI) bB(Ad aE AN aS aV aY aZ bC bU bV bX cF cG CH CO Cs cZ dD Dg dI)
cM(aF Aj aK aN Ar aU bC bE Bo bP Ch cK cQ cR cY dA Db Dc dD Dk DL) cS(aN aQ Ar aW BC bE bI bS bV bW cH cI cK cQ Ct cV cY Dc
De Dk Dl) bQ(aC aM aZ bE bM BN Bo bR cH cI cP cQ cV cZ Dc dD dI dL dN) Aw(aE aF aO aQ aW bP cF cI cP cQ cR Cw cZ dA Dc dD De
Dg dL) bL(Ad aF aG An aO Ar aX bE bG bI cB Co cP cR Cw Db De dF Dk) cA(aH aM aW Ax aZ bV cG cH cI CQ cR Ct cV dA Db dD dG dI)
Bn(aH aQ AX bC Bg bI Bo bS Ch cK Cs cX dA Db De dF dI) aY(aH aM aO aV bE bM cH cK cQ cV Cw Dc dD dF dG dI dN) cI(aE aM aU aV
aW aZ bR bU bV cD cG cJ cQ cV dA dD dI) cX(aC An Ar aX Bc bG bI bM bN Bo bS Co cR Cv dF Dk) aE(aC aH aK aM aQ aS aU aZ bE Bg
cH cK cQ dA dD) aO(aF aM As aU aW bC bR bU bX cD cG cO cQ cZ dK) bW(aN aU aW Ax bC bN Bo bV cB cV cY dF Dg dN) Cx(Aj aR
bG bI bM bN bP bS Ct Cv cZ Db Dl) cJ(aH aI aV bP bR bU cD cG cO cQ cR dA dI) dD(aC aS aV aZ bA bC bE bV cD cH cO cQ cV) fR(aC aF
aZ bE bG Co Dc DE Dg dJ Dk Dl) aG(Ad AF Aj An aR Ax Bo Cq Cv Db dL) aU(Ad aM An Ao aQ aV bM Co Cs Cw Dg Dk) bM(aC aK aQ
bN bR bU cD cH cO cY dA) As(bI bN bR cB cR Cs Cu Cv Db dN) aI(Af bI bN bS cP cR Cv De dF Dl) bU(aC aZ cD cG cK CQ Ct dG dI)
cG(aC aV bR cD cF CO Ct dI) Ax(aH An bC bG bV Ch Cu De) aX(Af An aS Bg Bo Ch Db Dg) dK(aC bS cB Cq cR Ct Db De) Cw(AJ Bg cD
Ch cK Cs) aM(aH aK aQ bC bV cD cY) bR(aZ bC cK Cq Ct Dc dI) dE(An Ao Bc Co Cv De Dl) aP(Ar Bc bG Cv De dN) cV(aS bC cH CQ dF)
cY(Af Ao Bo Ch Co Dk) aV(aC aQ aZ Cu dA) dI(Bg cD cK Ct dG) Cq(An Bo bV cD) aJ(Ar De Dk Dl) aZ(aC cF cR De) bC(Af aS Bg cZ)
dA(aC cK Ct Dc) Cu(Aj bA bF) cO(cK cR dG) Ao(aA bF) Bg(aH bS) Ct(cD Co) bV(Af cH) AjaK BccK ChDe DcdJ DlbF aCaS bAcP bEcZ
cDdG} aP{Cx(aC aE AF aH AJ aK aM AN Ap AR aW aY Bb bG bH bI bJ bL Bn Bo bQ bS bU bV bW cA cG CH cN CO cR Cs Ct Cv cW cY
cZ Db dF dI Dk dM Fr) cJ(Ad aE aI AL aM Ao Ap aU aY aZ bA bB Bc bF Bg bJ bN bQ bX bZ cB cC Ch cI Co CP Cq cR Cs CT Cv Cw dA
Db dD DE dF Dk Dl Fr) aD(aC aE aF aG aH aM aN aO aQ aS aV Aw aY bB bE bM Bn bP bQ bS bU bW bX bZ cA cB cH cI cL cQ cR cT cV
dA dF dJ) dC(aE aF aG aI aO aQ AS aU aV bA bE bJ bL bM Bn bP bQ bV bW bZ cC cD cF cI cK cL cM cN cO cQ cR cS cV dD dF) aL(aE aF
aG aH aM aN Ap aS aV aY aZ bG bN bP bS bU bV bX bZ cA cB cG cH cI cL cO cV cW De dI dJ dM) bR(aE aG aI aM aN aO aQ aU aV aX
bF bH bJ Bn bS cA cD cH cI cK cN cP cS cT cV cW cZ dB dE dI dJ dM) dL(aA aF aH aO aS aY aZ bA bC bE bG bJ bM bN bP bQ bS bU bZ
cA cE cG cH cL cR cT cY dE Di dM) bO(aA AF aG aI aM As aU aV Aw aY bB bC bE bG bJ bQ bW bZ cD cI cR cT cV cW cZ dA dD dF)
dK(Ad aF An Ar aU Aw aY BC bE Bg bH bL Bo bQ bZ cC cG Ch cI cK cO Cq Cs Ct Cv dE dI dN) aI(Af aG As aU aV Aw bA bB bC bG bM
BN bW bX bZ cC cD cF cN cP cR cT cX cZ Di) cX(aA aE aM As aU aV aX bB bC bG bJ bM bN bP bQ bZ cD cI cM cP cT dB dD) cF(aA Af
aU Aw bA bF bJ bM bP bQ bV cD cE cM cN cR cT dD dE Di) dD(aA aG aH As aX aZ bC bE bM bN bP bQ cC cD cN cP dB dF Di) cT(aE AF
aU Aw bC bF bJ Bn bW cC cD cN cP dB dE Di) aX(aG aV aZ bE bF bG bJ bS bU bZ cE cH cP cR dI) cD(aA aE Aw aZ bA bF Bn bP bX cE
cN cP dB dE Di) dG(Ad An Ap Ar As Bb Bc Bg Ch cO Cs CV Dk dN) dH(aC Ad Ao As Ax Ba bM Cp Cq Ct Cw Db Dg Dl fR) cB(aA aE Af
aM aN bA bF bH bM bN bP bS cN dE) cE(aA aH bC bJ bL bN bQ bV bW cC cN dE Di) dB(aA Af aG aM aU aZ bA bF cC cM cN cS Di)
aE(aU aV aZ bA bC bF bM bN bP bX cI cN) bP(Af aU bB bC bF bN bW cC cI cN dA) aA(aF aG Aw aZ bE bG bN cC cG dE) bA(aW bF bN
bV cN cR cV dA dF) Af(aU aZ bC Bn cK cM De Dg) Aw(Ax aZ bF Ch cN Ct Dg Di) bM(bC bF bG bJ bQ bV cC cV) Di(Aj As Ax aZ Bg Bn
Ch) cP(aM Ax bF bN cN) aU(aK As cY Dg) aZ(aO bJ bW cR) Cu(Ad An Bn) Aj(bC De) aG(cN dE) aS(bC bJ) AdBb AscK AxdA aObF bJcN
bNcR cCdE cScZ} aA{aG(aE aF aI aK aL aN aO aQ aS aU aV aY bA bB bE bF bI bL bM Bn bQ bR bX bZ cA cB cC cG cH cI cK cL cN cR
cW cY dA dG Di dL) dE(aC Af aH aJ aM aN aO aQ aR aS Aw aY bG bH bI bL bP bQ bS bV bZ cA cH cI cK cO cQ cW cZ dA dF DI dJ dN)
cG(aD aF aH aI aL aM aN aO aU aW aZ bA bE bL bM bN bP bQ bS bU bZ cB cC cD cF cK cL cR cZ dD dF) Mi(Et Fp Hw Ij Io Iq Is Jo Jt Lh
Lx Ma Mq Ne Nh Nr Nv Nw Nx Oe Ok Oz Pc Pe Pg Pz Qa) dC(AF aH aJ aL aM aN aR aV Aw bE bF bH BN bP bX cA cB cE cO cR cW dD
De dH Di) bW(aC Af aH aJ aN aO aV bB bE bJ BN bR bS bU bX bZ cA cC cK cL cR cT cV cW fR) cX(aF aI aQ aV Aw aY bA bB bF bJ bM
bN bQ bZ cA cE cO cR cW cZ dA dD dH dI) bO(aC aD aL aU aW bB bG bL BN bZ cA cE cL cO cP cR cV cZ dH dI) Ip(Fp Hv Im In Iu Jj Lj
Lw Ma Ml Mp Mz Ni Nk Nm Of Og) aU(Aj aL aN aR aV bM BN bS bX cF cV cY dG dJ dL) aZ(AF Aw bB bH bQ bZ cC cD cF cM cN cO dD
Di dN) dK(aC Ad bE Bg bV cB Ch cL Cp Cv Cw dA Dc Dd dN Fr) Nu(Hv Hx In Iu Jp Lw Ma Mk Mp Mz Nb Nj Nk Po Qd) dB(aF aL Ap bE
bJ Bn cA cD cE cF cM cR cV De dI) Nj(Hu Hw Hx Iu Li Ma Mk Ml Mm Nb Nn Nq Nw Qa) Jp(Hu Hw Hx Il Im Ma Mg Ml Mq Ms Nb Nn Nq
Pe) De(aD aI Al bF bP Ch cS cT dD Di Dk) Ap(Ad Aw bA bC Bo cD Ch cK Di dL) Mp(Hq Lz Ml Nf Oe Og Oi Pb Pf) aI(aC aD aF aM aR bG
bJ cV dI) Qd(Fp Il Im Jj Mw Ni Nq Ns) bJ(aQ aR bA cB cF cM cY Di) cR(aD aL aM bF bN cV dH Di) Hu(Iu Mz Nm Nn Of Ok Oz) Oe(Iu Lh
Lx Mz Nb Nw Po) bC(Al Ar Ba Bb Co Cp Dl) aM(aW bL Bn cP cV dD) aX(Aj Bb Cp Dc Dd Di) bE(aD bM cF cM cV dH) cB(bM bS bZ cE
cO dI) cS(Al An Ao AR Cp) aF(aD aL aR cA dD) dI(Aw cC cD cV dD) Cx(aL bS Cu fR) Ms(Nw Ok Om On) Iu(Im Ml Nb Og) Aw(cE cK cM)
Di(Af Bn cV) Po(Jj Oh Oi) Pe(Fp Jj Pf) aD(aR cM dN) cO(cD cE dG) As(Cw Fr) Mg(Ni Oi) Ml(Is Qa) Mm(Nw On) aL(bG cV) bZ(cE dH)
AfbG CucJ NnOi MaNi IjJj OnPb aJdG bLcD cZdD} bA{bC(AD aE aF aG aK aL An aO aQ Ar aS aU aV AX aY bB bE bI bP bQ bU bZ cA cG
cH cI cL cN CO Cp Cq CS Cu Cw cY dA Db DC DG dL dM) De(aE aG aJ aO Ap aR aW aY Ba bH bZ cH cP cQ cR Cv cW DB dC DD dF dI
dK) Fr(aD AF aI aM An Ap aV AW aZ bE Bo bR cF Ch cI cK cM cP Ct cX cZ dG) cS(aD aF aG aH Al aN aO aR aW bE cB cK cM cN cQ Cv
cW dA dC dD dG dJ dN fR) aU(aC Ad aJ Al aM An Ba Bb bM bS cE Ch Co Cp Cq cR Cs Cw cY Dc Dd Dl fR) aX(Ad aF Ao bE bN bP bQ bS
cB cF cI cJ Co Cv Cw cY dA dD dJ dK Dl fR) Ap(aL An Ao Ar aV Ax Ba BN Bo bQ cC cE cI cR cT dB dE DK) dE(aE aJ aL aS aZ bB bE bF
bM bR cD cE cF cG cO cR cT dH Di) dK(AF aI Ar aZ Bb bF bL bM bS cO cR Cu Dl dM) bW(Al Ao Ar Bb bG bI cI cJ cK cM cQ dB Dd dN)
Cx(aC aF aI aJ aS BB cD Cp cT cV dB dJ) cC(aI aZ bH bI BN bO bQ bZ cB cJ cT dN) bJ(aF aG aJ aM aZ bM cB cJ cR dC Dd) cX(aC aJ aM
Aw bO cB cJ cT dB) Di(Af aG aS aZ bF bO cG cZ) cJ(AJ As Bb Ct Dl) cO(bF bQ cD cF dF dG) aF(aC aM Ax bS cT) Aw(Ax bF Bg cE) aG(aJ
cE cT cV) cT(bB bE cB) Bn(Cp cY) aI(aC cZ) bM(bO dC) AfbE aJcB bOdC cGdH cRcV} Mi{Ng(Ip Jm Js Jt Lj Lw Mb Mc Mk Mu Mv Mw

Ba(bJ dC De Di) Fr(Al As Ax cT) cG(Ax bF) AsbC CudC DcDe} Nw{Mm(Fr Hq Jo Lj Lw Md Mh Mq Nf Nm Ny Of Oh Pb Pc Pf) Oe(Hv In Ni Nk) Ml(In Ip) Mp(Nn Oh) Jo(Pg Po) NcNk} cG{cE(aG aI aQ aU bG bM Bn BO bQ Cq dB dC dD dE Dg dJ) Ad(bF Bn Dc) aObF} Cu{Ad(aG aH aV bB bE bR bW cC cD cI Cp cR Dl) Cq(bC dC) bO(cX dE) AnbW AsbZ DcbC} As{bC(aO aS aU aV Ax bB bM dF) Fr(aI bO cT dB dD Dg) AraU AxDi} Jo{Po(Ml Mp Nb Nt Oe Pg) Ij(Et Iu Mm Mp) Pg(Et Ji Li) EtIn MmIl} Pg{Nm(Ii Lw Ok Pf) Mm(Nn Oh Oy) Lw(Mb Oz) PzOk} Ml{Po(Of Og) Is(Ip Og) Qa(Mb Pz) NyOe} cT{De(Af Bc) Fr(Bn cD) bW(bM Di) BbbC} aI{Ap(Ax Dg) AxDe bCdM bQcE} Ad{AxDe BacX BbbC DcdC} bM{bC(bO Cq) bW(bO dB)} Mp{LxOh NfNg NyPb} Po{LwMm IiJt} Hx{Og(Jg Nm)} Ny{Pb(Mu Oe)} cX{BbbC dDdE} ApDgDi FrdBdC LxJtOh

Unconstrained panels with 3 analytes, where 1.0E-6 >= 'AUC p-value' > 1.0E-7. Contains 12,576 panels of 590,601 total panels evaluated. : cU{Ax(Ad aE Af Aj aK Al aM aN aQ Ar aS aW aY aZ bE Bg bH bJ Bo bQ bR bU bX cC cD cE cF cG cH cI cK cL CO CP CQ cR Ct cV Cw cY cZ dA Db dC dD Dg dH dI dJ Dk dM dN) bV(Ad aH aK Al AN Ap aQ AR aS aU aV aW aY aZ BC Bg bM BN Bo bQ bR bU bX cB cD cG Ch cJ cK cL cO cP cQ Cs Ct cV Cw cY cZ dA Db De dF Dg dI Dk DL dN) cD(aC aH aN Ao aQ Ar aS aU aV aW aX aY aZ BC bE BG bI Bn Bo bP bQ bR bX cA cC cF CH cN CO cP cQ cR Cs CV cY cZ dA Db Dc De dF Dg dH Dk DL dN) Al(Ad Af AJ aL aP Ar aS aW aZ Ba Bb bE bG bH bJ bM bN Bo bP bR bS bU bW bX cB cF cG cH cI Co Cp CQ CT CV cZ Db Dd De dF Dg dI Dk DL dN Fr) Bg(aC Af Aj aK aL aN aQ AR aS aY aZ Bc bE bH bI bJ bM Bo bP bQ bU bX CH cI cK cL CO cP Cq cR Cs cV cW dA Db Dc dD De dF DG dH Dk DL dM dN) cO(aC aH aK aM aN Ao aQ aR aS aU aV aW aX aY aZ bC bE bG bI Bn bP bR bU bX cA cC cF CH cI Co cP CQ Cs Ct cV Cw cY cZ Dc De dF Dg dH dI Dk dL dN) Bn(aC Ad aE Af Aj aM AN Ao AR aS aW aY aZ Bc bE bG bH bM bN bP bR bU bX cC cF cH cI cL Co cP cQ cR CV Cw cZ Dc dD DG dH dJ Dk dL dN) cF(aC aE aH aK aM aN aR aS aU aV aW aX aY bC bE bH bM bQ bR bU cA cC cH cI cK cL CP CQ cR Ct cV Cw cY cZ dA Dc DD dG dH dI dL dN) bR(aC aH aK aM aN Ao aQ aR aS aU aV aW aY bB Bc bE bG bI bN Bo bP bU bX cA cB cC CH cP cQ cR cV Cw cY cZ dA Db dD dF dG dH dL dN) aH(aC Ad Af aK AN Ao aQ aR aS aU aV aW aZ BC bE Bo bQ bU bX cG CH cI cL Co cQ cR Cs cV Cw cY dA Dc De Dg dI Dk dN) aQ(aC Af Aj aK aL AN Ao aW aY aZ bB BC bJ bQ bU bW bX cA cG CH cI cJ cL Co cQ Cs cV Cw cY dB Dc Dd Dc dH dI dN) aZ(Aj aK aL aM AN AR aS aU aW bG bM bN Bo bP bX cG CH cJ cK Co CP Cs Ct CV Cw cY cZ dA Db Dg dI Dk dL) bX(aL aM aN aS aU aV aW aY Bb bC bH bJ bM Bo bQ bU bW cA cC cG CH cI cJ cL Cp CQ cV Cw cY cZ dD dH dI dN Fr) aX(aC AD aI aN aO Ap aR aW Bc bG bI bN bP bS cB cH cI cM Co cP cQ CS Ct Cv Cw cZ dD De dG DK DL Fr) aY(aK aN Ao aR aS aU aW Bc bG bH bI bN Bo bP bQ bU cB cC Ch cI cL Co cP Cq cR Cs Ct cY cZ dA Db De Dg dH dL) cA(aC Ad Af aK aN Ao AR aS aU aV bE bG bI bN Bo bP bQ cC Ch cL Co cP Cs Cw cY cZ Dc De dF Dg dH Dk dL dN) bU(aK aM aN Ao aS aU aV aW BC bE bG bI Bo bP bQ CH cL Co cP cR cV Cw cY cZ dA Dc dD De Dg dH dL dN) bJ(aC Ad Af Aj aK aM aN aR BC bE bG bH bI bN Bo bP cB cH cI cP Cq cR Cs Ct cV Db Dc DG dL dN Fr) cK(aC Ad Af aL aM Ao Ar aW bB bH bM Bo bW cG CH cI cJ Co Cq cR Cs cV cW Db Dc dD De DG Dk Dl dN) cY(aC Ad Aj aK AN aU aV aW bB BC bP bQ cG cH cI cJ cR Cs CV Cw DB De dF Dg dI DL dN) Fr(aK aM aN Ao Ap Ar aW bB Bc bG bH bN Bo bS cH cI CP cQ Cs Ct Cv cW Db Dc De DL dM dN fR) dI(aC aK aM aN Ao aS aU aV aW bC bE bI bM Bo bP cC cH Co cP CQ cR cV Cw cZ dA Dc dD Dg dL dN) bQ(Af aK aL AN Ao AR aS aU aV aW BC bG bI bP cB Ch cL cN Co cR Cs Cw dA Db De Dg Dk) cG(aK aM aN aS aU aW bC bE bI bM bN Bo bP CH cP CQ cR cV Cw cZ dA Dc dD dF Dg dL dN) Cp(aE Af aK aM aN Ao Ap AR aW Bc bE bH bM Bo bP bS cH cP Cq cR Cv Db Dd dJ Dk dL dN) cL(Ad aF aN Ao aR aS aW Bc bG bI bN Bo bP cB Ch cI Co cP cR Cs Cv cZ Db Dc De Dg dH dN) Cw(aD aE aG aK aM aN aP aR aW BB bH bM bP bS cC cH cI Co Cv dA DE Dg dH Dk dM) Cq(aC Ad aI Aj aN aS aU AW Ba bB bH cH cI cQ cR Cs Cv cZ dA Db dD Dg dJ dM dN) Ch(aE Af aK aS aW bC bH Bo cC cI cQ Cs Ct cV cW cZ dA Db dC dD dF Dg dH dM dN) aU(aD aK aN Ar aS aW bB BC bH Bo cH cJ cQ cR CV cZ Db Dc De dH DL dN) bO(AF An AO AR Bc bG bI bN Bo bS cB Co cR Ct Cv Db Dd De dF dG Dk Dl) dA(aL aM aN Ao aS bB BC bE bH bI Bo cH Co cP cQ cR cV Db dD DG dL dN) cJ(aF aK aN aR aS aW bB bE bG bI bN bS bW cB cH cP cS cV cZ dD dG dL dN) dH(Ad aF Aj An Ao AR aS Bc bI bM bP cB cN cR Cs Cu cZ Db dD De Dg dJ) aC(aD AJ aP Aw BB bL bP bS cB cM cS cV Cx cZ Dd dF dG Di dL dM) aO(aD aI aN Ap aR Ba BB bE bG bI bN bS bW cP cR cW Cx dF Di dL fR) cC(aF Aj AN Ao aR aS Bc bI bN Bo bP cB cH Co cR Cs Cu Db Dd dJ Dk) aL(Ad An Ar bB Bc bG bI bM bP bS cI cP cQ Cs cV Db Dd Dg Dk DL) bC(Ad Aj aK aN aV aW Bc bH bP cH cI Co cR Cs Cv De dF DL dN) bM(aM aN Ao aR aS aW bG Bo bP bS cI cP cQ cR Ct cV cZ dD De dJ) cW(Ad Aj An AR Bc bG bN Bo bP bS cP cR Cs dD De DG Dk) aV(aK aN aS aW bE bI bN bP cH cP cQ cR cV dF dG dJ dL dN) bW(Ad aF aK An Bc bS cH cI cP cQ cR Cs Ct Cv Db De Dk Dl) dM(Ad AF Aj An aR bE bI bN bS cP cR Cs dD De DG dJ) Dc(aG AJ AP Ba Bb bE bG bL Bo cI Co Cv Dd De Dg) dN(Ad Af aK aN aR aS aW cH cI cQ CS cV cZ DD dL) aD(Ad aF Aj An Ao bE bG bN bP bS Co Ct Cv Db dF Dk) aE(Ad An Ao AR bG Bo Co cP cR Cs Db dF Dg Dk dL) dB(Ad Aj aK An Ar bG Bo cB Cs Cv cZ dF dG dJ Dk Dl) bB(Af Ao AR Bc bE bN Bo bP cP cR Cv Db Dk dL) cN(Ad AF Aj An Ao Ar Bc cB Co cP Cu Cv Db Dk) aM(aN aR aS aW bG bH bS cB cP cQ cV cZ dD dJ) Ap(aF aJ Ar bG bH bL cP cQ Cs cV dD De Dl) Bb(aF aR aS bE bG bP cB Cs Ct cZ Dd dG Dl) cQ(aK aN aR aS aW bE Bo cH Ct cZ Dg dL) dC(Ad Aj An Ao Ar Cs Ct Cu Dc dG dJ Dl) bL(Aj Ao Ba Bc Bo cS Ct Cv dG dJ Dl) bH(Af Aj bG bS cB cH Cs cZ dF dL) cV(aN aW bE bG cP cR cZ Dd De dL) aK(Ad Af AN aW cH cI Co Dg) aS(aN aW Ba bE bI cH cI cZ Dd) dD(aN aR aW Ba Co Cs cT cZ Dg) aG(Ao Ar Bc Cs Ct De Dk Dl) aI(aF Aj bG Bo cB Ct Dd dG) bS(Aw bI bP cM cR cT Dd dG) cX(aF Aj cB Ct Db dG dJ Dl) cH(Af aN aW cI cP cR cZ) Ao(Ad AJ aP Bo cT) Aw(Aj bI bN Db dF dJ) Di(aF aR bN bP cB Ct) cM(aR bG bI bN cB cP) Ba(bE bG bI cR dJ) Cv(aJ Bo bZ cE fR) Cx(aF cB cR dF dG) cI(aN Co cR cZ dL) An(Bc Bo bZ De) Dd(Af aJ dJ fR) cP(aN cR cS cT) Bc(AJ fR) Co(Dc Dg dL) Cs(Af bZ Dg) aW(aN cZ De) Ad(bZ Dg) Bo(aN Db) bP(aR cR) cS(aF bG) cT(dG dJ) dK(bE dJ) AfbZ AjCt DlaP} Lv{Ih(Fr Hq Hr Hu Hw Ii Ij Ik Il In It Iu Iv Jg Jh Jk Jl Jm Jn Jr Js Jt Lu Ma Mb Mc Md Me Mh Mj Mp Mq Mr Ms Mt Mu Mw My Na Nb Ne Nf Ng Nl Nn Nq Nr Ns Nt Nx Ny Of Oh Om Oy Pa Pb Pc Pd Pf Pg Pz Qb Qc Qe) Jh(Fr Hq Hr Hu Ii Ij Ik It Iu Jg Jk Jm Jn Jo Jr Js Lj Ma Mb Mc Md Mh Mj Mk Mn Mp Mq Mt Mu Mv Mw Mx My Na Nb Nc Nf Ng Nl Nn Nr Ns Nt Nv Nx Og Oh Ok On Oy Oz Pa Pb Pc Pd Pz Qe) Qc(Et Fp Fr Hq Hr Hu Ii Io It Iv Jg Jl Jm Jn Jr Js Lh Lj Lu Lz Ma Mc Md Me Mh Mj Mk Mn Mq Mr Mt Mu Mv Mw Mx My Na Nb Nc Nf Nh Nn Nq Ns Nt Nx Oh Oy Oz Pb Pc Pd Pf Pz) In(Fp Hq Hr Hu Hw Ii Il Io It Ji Jk Jl Jm Js Lh Lj Lu Lz Mb Mc Md Me Mf Mg Mh Mj Mk Mn Mq Mt Mu Mv Mw Mx My Na Nc Ne Nf Ng Nq Ns Of Og Oh Ok Oy Oz Pa Pb Pc Pd Pz) Fr(Et Fp Hq Hr Hu Ii Io Iv Jg Jl Jm Js Lh Lj Lu Lw Lz Mb Mc Md Mk Mm Mn Mp Mq Mt Mu Mv Mw Mx My Na Nb Nc Nh Nm Nn No Nq Ns Nt Nv Nx Ny Oh Om Pa Pb Pc Pd Pf Pz) Jk(Hr Il Io It Iu Jg Jl Jm Jn Jr Js Lh Lu Lz Mb Mc Md Me Mg Mh Mj Mk Mn Mq Mr Ms Mt Mu Mv Mw Mx My Na Nb Nc Ne Nh Nl Nn Nq Nr Nv Oh Om On Pa Pc Pd Pg Qb Qe) Iv(Et Fp Hq Hr Hu Ii Il Io It Jg Jl Jm Jn Jr Js Lh Lj Lu Lz Mc Md Me Mh Mj Mk Mn Mp Mq Mr Mt Mu Mw Mx My Na Nb Nf Nh Nl Nn Nq Nr Nt Oh Oy Pb Pc Pd Pg Pz) Ny(Hq Hr Hu Hw Ii Ij Ik Io It Jm Js Jt Lh Lj Lu Lz Mc Md Mh Mj Mk Mn Mq Mt Mu Mv Mw Mx My Na Nc Ne Nh Nn Nq Ns Nx Of Og Oh On Oy Oz Pa Pc Pd Pf Pz Qb Qe) Jn(Fp Hr Ii Ij Ik Io Jm Jo Jt Lh Lj Lu Lw Ly Lz Ma Mb Mc Md Mh Mj Mk Mn Mq Mt Mu Mv Mw Mx My Na Nc Ne Nh Nm No Nq Ns Of Og Ok Om Oy Pa Pd Pf Pg Pz Qb) Qb(Fp Hq Hr Hu Ii Il Io It Jm Jr Js Lh Lj Lu Lz Mb Mc Md Me Mh Mj Mk Mn Mr Mt Mu Mv Mw Mx My Na Nb Nc Ne Nf Ng Ns Nv Nx Oi Oy Oz Pa Pb Pd Pz) Hw(Hu Ij Il It Iu Jl Jm Js Lh Lj Lw Lz Mc Md Me Mg Mj Mk Mn Mq Mr Ms Mt Mu Mv Mw Mx My Na Nc Ne Nh Nn Nq Nr Nx

Figure 37 Continued

Figure 37 Continued dA dI dJ dM) cF(aF aG aH aJ aK aM aN aO aQ aR AS aV aW aY BB bC bE bG bI BN bS bU bW bZ cA cG cH cI cL cQ cS cW cY cZ dA dF
dI dJ dM) cX(aC aF aJ aK aN aO aQ aR aS AW aY bE bF bI bL bU bV bW bX cA cG cH cK cL cN cO cQ cR cV cW cY cZ DE dF DI dJ dM
dN) aI(aC aF aK aM aN aO Ap aQ aS aW AX aY bE Bg bI bL bQ bS bU bV cA cG cH cI cK cL cM cO Cq cV cW cY dA Dg dI dJ dM) Di(Ad
aG aJ aM An aQ aV aW bC bF bJ bL bM bN Bo bP bQ bR bZ cC cI cK cN CP Cq Cs Ct cV CW Db dC dE dF dM) dC(aC aH AJ aK aM aN aR
AW aY BB bC bG bH bI Bo bS bU bX cA cG cH cP cT cW cY cZ Dg dI dJ dM dN fR) cE(aF aJ aK aL aN aQ aR aS aV aW aZ bE bH bM Bo
bP bU bX bZ cH cI cK cL cM Co cQ cR cT cV cY De dI dJ dM) Aw(Ad aM AN Ao As aV aY Bc bJ bM bN Bo bP bQ bR bU bZ cC cH cK cL
Co cP Cq cR CS cV Cw dE dF dM) bO(aC aH aJ aK aN aO aQ aR aS aW Bb bH bI bL Bn Bo bS bU bV cA cC cG cH cK cL cM cO cQ cY De
dI dJ dM) aG(Af aH aN aQ aS aU aV aZ bB bC bF bJ bM BN bP bQ bW bX bZ cC cD cI cP cR cS cT cV dA dF Dg) bR(aF aH AJ aK aR aS
aW Ax aY aZ bB bG bI bL bQ bU bV bW bZ cC cG cL cM cO cQ cR cY dA dF dK) bP(aF aH aM aN aO aQ aV aW aX aY aZ bE bG bJ bM
bQ bU bV bZ cA cH cL cR cT cW cY cZ dE dF dJ) cN(Af aH aM aO aQ aU aV aW aY bB bC bF bG bM BN bU bV bX cA cH cI cR cS cW
dA dE dF dJ) aZ(aH aM aQ aV aW aY bB bC bE bH bM bN bQ bS bU bZ cA cC cH cI cP cS cT Cv cW dA dE dI) Af(Ad aH aM Ap aQ AS aV
Ba bB bF bG bI bJ bN Bo bU bW bZ cI cP Cq cY dA dE dF dM) aD(AJ aK aR As aW Ax Bb bG bH bI bL bV cG cK cO cP cW cY cZ De Dg
dI dM dN) cT(aH aK aL aM aO aV aW aY bB bE bG bN bQ bU bX cA cG cI cL cR cV cY cZ dA dF) aX(aC aF aJ aK aQ aR As aU aW bI bL
bQ bV bW cA Cq Cx cY dA dE dF dJ dM) aL(aC aJ aK An aO aQ aR BB bH bI bM Bo bQ cK Co Cp cQ Ct cY Dg Fr) bN(aH aM aO As aU
aV aY bB bC bF bG bJ bM bV bZ cC cD cG cI cM dA dE) cD(aF aH aM aQ AS aU aV Ax bB bC bJ bS bW bZ cA cI Cq cR cS dA) cP(aH Aj
aQ aU aV aY bB bC bJ Bn bQ bU bX bZ cA cC cL cS dA dE) cS(aS aW Ax aY bB bF bJ bQ bU bV bX bZ cA cH cL cW dA Dg dI) dE(aF aK
aN aO As aV bB bF bI bJ bM bU bV cG cI cV Cx dA dI) dK(aC Al AO Ap aR aS Bb bV Co Cp cR cV Cw Db Dc Dl FR) dL(aJ aK aM aN aR
bH bI Bn bV bX cK cO cQ cV cW dF dI) Cx(Al AO aS Ba Bc bE bX cL cQ dJ Dl dN fR) As(aF Ap aQ aV aW bB bJ Bn Bo bW cC De Fr)
aU(Ad aM aN aQ aS bF bM Bn bX bZ cI cR dJ) bB(aM bC bF bJ bM Bn bU bX bZ cC cR dF) bF(aH aS aV bC bJ bL bX cG cI cR dA) Dg(Ap
aQ Ba Bb bC Bn bW cG De dG) dH(Aj Ar Bc Bg Ch Cs Cv Dc Dd Dk) bM(aW bE cG cI cK cM cQ cR dI) dA(aM bC Bn bQ bS bX cM cR)
dG(Al Ax Cq Ct Db Dd fR) Bn(Aj aV Bo cI cK cM) bC(aO bJ bQ bZ cZ dI) bX(bJ bQ bU bV bZ cR) cI(aM aV Ax bJ cM) bJ(aO cM cR)
Ap(Ad Aj) Ax(Cs dM) aS(bW cR) cC(bL fR) CuDc aFaO aMaY aNcR bQcM} Jp{Nu(Et Fp Fr Hq Hr Hu Hv Ik Io Iq Ir Is It Iu Iv Jg Jh Jj Jk Jl
Jn Jo Jq Jr Js Jt Lh Lj Lw Lx Ly Lz Ma Mb Mc Md Me Mf Mg Mh Mj Mk Mn Mr Mt Mu Mw Mx My Na Nb Nd Nf Ni Nk Nm No Nq Nr Ns
Nt Nv Nw Nx Ny Oh Ok Om Pa Pc Pf Qa Qb Qc Qe) Qd(Hr Hu Hw Hx Ii Ij Io Ip Iq Ir Iu Iv Jh Ji Jl Jm Jn Jq Jr Jt Lh Li Lu Lx Ly Lz Ma Mc Mf
Mg Mh Mj Mk Mn Mp Mq Mr Mt Mu Mv Mw Mx My Mz Nb Nc Nd Ne Nh Ni Nk Nl Nm Nn No Nq Nr Nv Nw Nx Oh Om Pa Pb Pc Pd Pe Pf
Pg Po Qa Qb Qc Qe) Mp(Fp Fr Hr Hu Hv Ii Ij Io It Jg Ji Jj Jl Jm Jn Js Lj Lu Lw Lx Lz Ma Mb Mc Me Mf Mh Mj Mk Mn Mr Mt Mu Mv Mw
Mx My Nb Nc Ni Nj Nm Nn No Nq Nr Ns Nv Nx Ny Oh Ok Oz Po Pz Qa Qe) Oe(Fp Hq Hr Hu Ih Ik Iq Is Jg Jk Jm Jo Jq Js Li Lj Lu Ly Lz Mb
Md Mg Mh Ml Mm Mr Mu Mv Mw Mx My Na Nd Ne Nf Ng Nh Ni Nk Nl Nq Ns Nx Ny Of Og Oh Oz Pb Pc Pd Qa Qb Qc Qe) Im(Fp Fr Hq
Hr Hu Hv Ii Ij Ir Ji Jm Jn Jo Jr Lj Lu Lx Ly Lz Ma Mb Mc Md Mf Mg Mh Mk Mn Mq Mr Mt Mw Mx My Nf Ng Nj Nl Nm No Nq Ns Nt Of
Ok Oz Pb Pf Po Pz Qa Qb) On(Fp Fr Hq Hu Hx Ii Ik Il Io Ip Iq Jg Ji Jl Jm Jr Js Lh Lj Lw Lz Mc Md Me Mf Mg Mh Mj Mk Mq Mr Mt Mz Ng
Nk Nm No Nq Nr Ns Nv Nw Oh Oy Oz Pc Pf Pz Qb Qc Qe) Pe(Fp Fr Hq Hr Hu Hv Hx Ik Il Io Ip It Iu Iv Jl Jm Js Jt Lh Lz Ma Mc Me Mf Mg
Mh Mm Mn Mq Mw Mx My Mz Nb Nf Ng Nk Nn No Nq Ns Nt Nv Nw Oh Ok Oy Pa Pb Pc Qc) Nn(Fp Fr Hu Ii Ij Io Ip Ji Jl Jo Jr Lu Lz Mb
Md Mf Mm Mt My Nb Nc Nf Nk Nm Ns Of Oh Oz Pb Pc Pf Pg Po Qb Qe) Iu(Fp Hq Hr Hu Hv Hx Ii Ij Il In Io Ip Ji Jk Jr Lj Lu Mf Mh Mm Mz
Nc Nf Nj Nk Nm Ns Of Pa Pb Po Qb) Lw(Fp Ij Ik In Jr Lu Ma Mb Mg Mj Mk Ml Mq Mz Na Nk Nq Nt Nx Of Og Oi Po Qa Qe) Ji(Hx Ii Ip Lj
Ly Mb Mf Mk Ml Mn Mw Nd Ng Nj Nm Nr Ns Nx Of Pa Po Qb Qc Qe) Po(Hq Hr Ii In Ip Lj Mf Ms Mz Nb Ne Nf Ng Nj Nm Ns Og Oi Ok Oz
Pb Pz) Pg(Fr Hr Hv Hx In Ip Lh Lj Ma Mg Mm Ms Mz Nf Ng Nj Nq Ns Nt Of Og Pf) Nm(Fp Hw Ip Lu Ly Mb Mc Mj Mk Ml Mm Mu Mz Nf
Ng Nk Of Oi Pb Qb) Hx(Fr Ii Il In Io Ip Jj Lj Ma Mg Mm Ms Ne Nq Nt Oh Oi Pa Pc) In(Hv Ii Jr Lu Mg Mj Mq Ms Ng Nq Nt Nw Of Oh Oi Pc
Qa) Ip(Hv Hw Ij Il Jj Jk Jo Ma Ml Mz Ne Ng Nh Nk Of Ok) Ma(Ii Ij Jo Ly Mf Mj Mx Mz Nf Nk Nr Ns Of Og) Ml(Hv Ij Il Iv Mq Mx Mz Nb
Nq Nr Nt Nw Pa) Ne(Fr Iv Jg Jj Jr Mf Mq Nb Nl No Oh Om Pc) Il(Fr Jt Mg Mq Mz Nq Of Og Oh Ok Oz Pc) Ms(Hw Ij Jk Jl Jr Li Mq Mt My
Oh Pc) Oi(Fr Hv Ij Iv Jt Nb Nv Nw Oh Pc Qa) Mz(Hu Hw Mg Nj Nq Of Og Pa) Nh(Fr Iv Jj Jt Mq Nb Oh Pc) Nt(Jg Mm Nk Of Og Oz Pz) Ir(Ii
Is Jj Jo Nj Of Pz) Nq(Jo Nf Of Og Pa Qb) Mi(Lu Ly Me Mx Oy Pa) Mm(Hu Is Jq Lx Ng Nj) Jj(Hv Ik Li Lx Mk) Hw(Ii Ng Nj Og) Is(Iv Jr Js Of)
Jk(Jo Oh Ok Pc) Ij(Nj Og Pz) Of(Jl Mk Nr) Fr(Ng Pa) Nw(Nj Nk) Og(Mw Pa) Pb(Nb Ny) LxHq HuOk QaJo} bA{Ap(aD aE aG aH aJ aM aN
aO aS aZ BB Bc bE bH bI bL bM bP bR bS bU bV bZ cA cB cG cH cL cM cN CO Cp Cq Cs CW cY cZ Db dD dF dG dI dJ DL dM dN) dE(aC
aD aH aK aM aN aO aQ aR aV Bb bG bH bI bL BN bP bQ bS bU bV bX bZ cA cI cK cL cM cN Cp cQ cW cY cZ dA dB dD dF dG dI dJ dL
dM dN Fr) Fr(Ad aE aG aH Aj aK aL Ao aQ AR As Ax aY Ba BB bG bL bN bO bP bU bV bZ cG cH cN CQ cR Cs Cv CW cY Db Dg dI dJ Dk
dL dM) Di(aI aJ aK aM An aO aQ aR As aV Aw Ax Bb Bc bE BG bI bN Bo cB cD cE cF Ch cK cM cN cO cR Ct cY dB dC dH dJ Dk Dl)
bJ(aC aE Af aH aK aN aO aR aV Bb bE bF bG bH bL BN bR bZ cD cE cF cL cM Co Cp cT cV CW cY dB dH dJ DL dN fR) Cx(aD Af AL aM
aQ aR As Ba Bc bF Bg bH bI bL bM Bo bP cE cF cH cM cO Cq Cv cZ Dc Dd Dg dI Dl dN fR) aF(Af aG aI AJ Al aO Ar As aZ BB Bc bE Bg
bL bM Bn BO cF cG cO Ct Cw cX Db DC Dk Dl dN) cC(aD Af aG aJ aL aM aN aR AW bB bE bF bM Bo bS bV bX cA cE cF Co cR cW dA
dD dH) cJ(aC Ad An Ao Ar Ax Ba BC Bg bM Ch Co Cp Cq cR CS Cu Cv Cw Db Dc Dd Dg DK) dK(aE aG aL aM aS bB bH bI bN BO bP bZ
cA cB cD cE cF cG cI cV dB DC dH) bC(aH aN Ao aR aW Ba bG bH bN bS bX cK cM cP CV cW cZ dD dJ Dk dN) cO(aM As aU aV Aw aX
aZ bE BN bO bR bU bZ cB cN cR cV cX dB dC dI) aX(aK aL aN aQ AR aU aV aW bB bG bZ cD cG cP cQ cZ dG dL) aJ(aD aI aL aZ bE bO
bR cD cF cG cM cR cV dB dC dG dH) aU(aK Ao aS bF bI bL bO cF cK CV DB Dg dH dM dN) cX(aD aI aR aS Ba BB bF bG bL bM cD cE cF
cZ dN fR) cR(aG aI aW aZ bE bF bM bO cB cE cG cT dB dC dH) bE(aG Ax aZ Bb Bc bL bM Bn bO cB cV dD Dl) Aw(An As aV aW aZ BO
cD CT De) bO(aC aG aM aS Bn cB cE cT cV) Bn(aG aV bG cB cV dB dC) aZ(aG aI aW bH bL Cv dC) cG(Af As bR cD cF cN dB) De(aH bG
cZ Dg fR) cT(aD aI bF cV dB) aG(Af bF bM cB) cV(aC aI Bo dN) dC(aC Bb bL dB) bM(bL dB dN) bW(aY bS Cu) Af(bG cY) cB(bL bS)
cS(bH Dd) AsCw AxCu CoaV aCdB bFbZ} Mi{Nq(Fr Hq Hw Im Io Ir It Iv Jh Jk Jr Js Lj Lw Lz Mb Mc Mh Mk Mu Mv Mw Nj Nn No Nr Nt
Nv Nw Nx Oe Om On Oz Pb Pf Pz Qa Qc Qe) Oi(Et Fp Fr Hq Hr Hw Il Im Io Iq Is Iv Jg Jr Js Lj Lw Mc Md Mn Mw Nh Nj Nn Nr Nt Nv Nx
Oe On Oz Pb Pc Pe Pz Qe) Nu(Hq Hr Ik Im Io Is Iu Jh Jj Jq Lh Lj Lz Mb Md Mk Mp Mv My Na Nc Ne Nn No Nv Ny Om On Pa Pb Pe Pf Qd
Qe) Nk(Fr Hq Hv Ih Ii Ik Il Jh Jo Jq Js Lj Lu Lz Mf Mh Mk Mu Mv Mz Na Nf No Nt Nx Om On Oy Pb Pe Pf Qb Qc) Og(Fp Ii Il Iq Is Iu Jg Jk
Jm Jn Jr Js Lh Li Md Mn Mq Mt Mw My Nh Nj Nn Nw Nx Ny On Oz Pf Pz Qc) Mm(Hv Hw Ih Il In Ir Is Iv Jl Jm Jn Jq Jr Js Lj Lw Lz Mb Mc
Mf Mt Mv My Na No Nx Om Pa Pb Qe) Ni(Et Hr Hw Hx Il Is Iu Jg Jh Jr Lh Li Lu Lx Ly Md Mj Mq Mz Nd Nj Nn Ns Nt Nv Ny Pa Pc Pg Po)
Ng(Fp Hq Hr Hv Hw Ii Is Iu Jh Jk Jn Li Lx Md Mn Mq Mt Mx My Ne Nt Nx Ok Oz Pc Pf Pz Qd) Ml(Hv Hw Ip Iq It Mn Mv Mz Nb Nc Nf Nh
Nj Nl Nr Nw Oe On Pc Pe Pz Qd) Mr(Fp Hv Iq Ir Jo Js Lz Mf Mw Ne Nh Nj Nn Nr Nt Nx Oe On Oz Qa Qe) Hx(Fp Hq Hw Jn Jo Jq Jr Lx Md
Mh Mk Mt Mv My Mz Na Ny Oe Om Po Pz) Of(It Jh Jl Jm Js Lh Li Lz Mc Mf Mv Mw Nh Nx Oe Oy Oz Pb Pd Qc Qe) Nb(Fp Fr Ih Ip Jo Js
Mb Mf Mn Mu Nf Nh Nj Nn No Nx Oe Pb Qd) Nf(Hr Hv Ij Im It Jr Lh Mb Mf Mn Ne Nh Nv Nx Pc Pe Pz Qc) Ip(Fp Fr Hv Ii Il Ji Jj Jk Mb Mn

Nj Nm Ok Oz) Og(Im Ir Is Ji Jl Jt Nr Pe Qe) Po(Im Lw Mf Nd Nf Ng Nm Of) Ml(Im Iv Lx Mj Nb Ny Pa) Nk(Et Is Ji Lw Mm Ok Om) Lw(Hu Il
In Ni Pe) Im(Ng Nj Of Pa Pz) Ji(Hu Il Mm Nh Ni) Is(li Mh Nj Pf) Jo(Hw Ij Ir Jk) Pe(Fp Ii Ik Oz) Ms(Jl Nb Om) Lx(Mm Nj) Mp(Jr Ng) NmHv
MmLi NbPb NgJg NjJl HuOk} cJ{Cu(aD aE Af aI aK aL aN AO aQ AR aV aW Ax aY Bb Bc bF Bg bH bJ bL bM bN bP bQ bR bS bW bX bZ cA cC cD cF cG Ch cK cL cM cN CO cP cR CT cV cW cY dA Db dC De DG dH dI dJ DK dM) Di(AD aG aN Ap AR aV Ba Bb bC bF Bg bM Bo bS bZ cA cD cF cG cO cR Cs cT CV cW dB dF dK FR) Cx(aC aG aN AR aU aV Ax bL bM bQ bZ cB cC Cq cX dB De dI Dk Dl dN) Fr(Af aG AL aV Bb bF Bg bM BO bV cB cF cI Co cV Dc Dd) Bb(Af Aj Al Ar aZ Bn bO bS cA cE cX dC dE dI Dk dN) Bc(aD Aj As aV Bn BO cB cD cI Cp cT cX Dc) Ax(aC As aU aV bE bG BO cB cG cI dB) aZ(Ad Af Aj Ao As Ch Cp Cq Ct Db Dg) Dc(Af aV bJ Bn bV bW cE cX dK) Ba(Af Bn bO cE cV cX dE Dg) bO(Al Ap As Aw Bo Dd dM) dE(Af Aw Bo cC Db Dd Dk) Af(Aw bV cG dF dK) As(Aw bC bV cG Dk) Ap(Ao bV cT) Bn(cT dF dM) bM(Al Cq Dd) Aj(cG Cp) bV(Bo De) AwBg CsdK bQcE} Cx{cG(aH Aj aN Ao aS aV aY Ba bJ bM Bo bP bQ bR bU cA cC CH cI cK cM cN CO Cq Cs CV cW cX dC Dd DE dI dK dL dN) Cu(aE aK Al Ao aQ AR As aY bF Bg bJ Bn bR bU bZ cA cB cD cE Ch cL cN cP Cs cZ dA DD dG Fr) Aw(aN As aV Bb BC bF bS bV cE Cs cT dC dD fR) Di(aG aL Ax Ba Bb Bc bO bW Ch Cw dF dK dM FR) aZ(Af aU aV Ba bH bL cT Cw dE dI FR) Fr(aD Aj Bg bO cB Ch Cq Dd Dg dK) bO(Ap Bb Bc bW Dd dF dI dK fR) Cw(Aj aK aL aN As cE dC dM) dF(aU bF Bg cC Cp Cq dB dC) bC(Aj aS cB Cp Cv dB dM) Dc(Ad aU aV bW dC dK) dE(aI aL aV Bb Cp cT) fR(cD cE cM Cq Dd dK) bW(Ax bP Cp dC Dd) Ap(aI Ax dC Dg) dK(aG aI Al Ar) Bb(aL bV cF) De(aS dD dM) aU(Ax bV dM) Cp(aL cQ) Dd(aI cD) dB(Ba Bc) AlaV ArdC bFbQ bVcB} dK{Dk(aE aG aH aK Al aM AO Ap aQ aR aU AW Ba bC bG bH bR bX bZ cC cF cL cM cN cO Cp CQ cR Cs Cv CW cY cZ dA DC De dG dH dI dJ DL dN) Bc(aE aG aH Al aN aQ aV Aw bF Bg bL bM bN bQ bR bV cB cD cE Ch cL cQ cV cX dA Dc Dd dF dH Dl dM) dM(Ad Aj aK An aO aU bB bC bH Bo bQ bR bS cA cB cF cG CH cI Cs cT cW cY Dl) aZ(aI aL aQ Bg bM Bo bQ bW bX cC cF cO CW cZ dC dD dE dF dG Di) aL(Ad aG aN Bb bC Bg bO bQ bV bZ cK CO Cq dF DG dJ dN) Ar(aI As bM cB Cp) Ax(Al Ao bC cL Cq) Dc(aI bO cX dF Di) Aj(bC Bg Cw dF) Fr(aI bP dB dD) bM(aN bC bO fR) cE(bG cG fR) cX(aG bL Cs) Al(Bb Bo) Dd(Af Bn) aI(bS fR) bV(Bb Dl) CuDg bPdF} Ms{Mz(Hu Hw Ih Ii Ij In Ir Is Jl Lh Ly Me Mj Mk Ml Mq Mr Mu Mv Mw Na Nd Nl No Nr Ns Nv Oe Og Oh Oz Pa Pc Pd Pg Po Qc) Nw(Fr Hu Ih Ii Ij Is It Iv Jk Jl Jn Ma Me Mk Ml Mq Mr Mv My Nd Nm Nq Nr Nt Oh Om Pa Pc Pe Po Pz Qa Qb Qe) Lw(Et Fp Fr Ip Iq Is Jg Jh Jn Jq Jr Js Lx Me Mk Mq Mr Mv Na Nn No Nq Ny Pa Pz Qe) Jt(Hv Ik Il Iq Ir Jh Jk Jl Lx Mn Mp Mv Na Nh Nj Nr Ny Oz Pc Pg Po Qb) Ok(Fp Hv Hw Ij Iq Ir Is It Mk Na Nc Nk Nl Ny Oy Qb) Nm(Hu Ii Il In Iv Js Lx Mn Mw Nb Nf Nj Pa Po) Mp(Hx Ir Lx Ly Mv Mw No Nq Om) Hx(Fr Hr Iu Jq Ma Mm Nt Om) Iu(Ip Iv Jg Jq Lx Ma Ml) Fr(In Pg) Ml(Iv Ny) NtHq MmJl MwMy NdIv IiPg ImJg NyPb OeOm PePf} Nj{Pe(Fp Hr Hu Hv Hx Ik Ip Iu Jg Jl Jm Jo Jt Lh Ly Lz Ma Mc Mf Mh Mj Mn Mq Mr Mu Mw Mx Mz Nc Nf Ng Nq Nr Nt Oe Of Oh Oi Om Pa Pc Pf) Im(Fr Hr Hv Io Iq Jh Jk Jm Jo Lx Lz Ma Mb Mc Mk Mm Mr Mw Mx My Nm Nq Nw Nx Ok Oz Pc Pf Po Qe) Nv(Fp Ij Ik Iq It Iu Jn Lj Lu Lx Mc Mh Mj Mq Ny Om Oz Pf Po Pz Qe) Nw(Fr Hu Hw Ij Ip Lj Ml Mq Mz Nk Nq Of Og Pc Po) Po(Fr Hq Ji Lw Mm Mp Mz Nb Nd Nn Oe Og Pa) Mm(Hv Hw In Iu Jl Mx Nb Ni Nk Nr) Pg(Fr Ii Jg Ma Ml Nd Om Oz) Nd(Fr Iu Jt Mq Nq Nt) Lw(Hv Hx Jl Ny Qe) Ok(Hx Il Jk Nb Pa) Et(Jk Ne Nh Pa) Nm(Hw Hx Ij Lh) Lx(Ml Nn Of Pa) Om(Hx Il Jk Ne) Fr(Hw Ij Ng) Ny(Mp Pb) MlIs MzIp HuJi IuNx JgOg} aL{Ap(aG aI Ao AS aW Ax aY aZ bB bE bI bL bM bN bR bS bU bV cA cF cH cI cK cM cN Co Cq cR cT cV cW cZ dA Db dH dI Dk) bW(AD aH Aw aZ Ba Bc bL BO cE cF Cp cT Cw cX Db DE Dg Dl dM fR) bE(aH Aj aN Ao Aw aZ Ba BG bH bL bO bS Co Cv Cw cX Db dE Dg dJ Dl) bC(Ad Aj aK Al Bc bL Bo cC Cq Cs Cv cX cY Db dE Dg Dl Fr) Aw(Ax Ba Bg bH bJ bL bO bS bV bZ cE cG cO Di Fr) Fr(aZ bF Bg bJ Bn cD cF Ch cI Cq cT cX Dg Di) De(aD Al aQ Ax Ba bF bL bO bS Ch cX dI dN) Di(Ba Bb bJ bL cZ dE dI) dE(bJ Cp cX dC dN) cG(bJ Bn dN) dI(As cC Cp) AdCu bJdN} Nw{Oe(Hx Ii Il Im Ip Iu Jk Jl Lh Mk Ml Mp Mr Mz Nb Ne Nf Nh Nr Nv Oi Oz Pa Pe Pg Po Qe) Nk(Fr Hr Hu Hv Ii In Io Ip Iu Ji Jo Ma Mg Ml Mp Mu Mz Nm Nn Nq Ns Og Pz) Ml(Hw Hx Ij Is Jk Lx Mj Nm Og Oi Pg Po Qa) Jo(Hu Hv Hx Ij Il Ip Iu Jk Mp Nb Nt) Mm(Et Is Jg Mt Mv Na Nl Ok Om Oz) In(Hr Hv Ip Nb Nx Of Og Pb Pz) Og(Hu Hx Ij Il Jk Pe Pg) Nm(Iu Jt Mp Nt Qa) Nb(Hv Im Oi Pe) Nn(Iu Mg Oi) Hu(Ip Nf Oi) Ii(Hx Il Pe) Hv(Ne Nh) Iu(Of Oh) Pg(Nv Pz) MgOi NfQa NiIm JkOf JtOh OzPe} aZ{dN(Aj aQ Ax Ba bG bH bN Bo cA cH cI CQ Ct dA dB dE dI Dk) cX(aF aG aI Ap Ba bS cC Cq cT dE dF FR) Di(aG bC bL bO bV bW cT dC Fr) aI(aH Ba bH bL bW cC Cq Cv Fr) aO(Ap bC bF bL bS dC dE dI) bO(bC bE bH bL cC dC dE) Aw(Al Ba cE cT Cv dF) bW(aU bM Ch cT Dg) Ap(bI cT dD) Fr(As dB dC) cC(bL bQ dE) Aj(Co dI) Ba(Ad dB) aG(bH dE) bS(dB dD) dC(bH dE) bQcE} Im{Nk(Hq Hw Hx Ij Ip Jg Jk Jm Jo Jt Lw Ma Mj Mm Mq Mu Mv Mw Nm Nq Nr Nt Nv Oh Om Oz Pa Pc Pe Po) Ni(Hu Hx Ip Lh Mj Mq Mw Mz Nm Nn Nt Nv Of Oh Pa Pe Pg) Nl(Ii Il Iu Jk Lj Lw Md Mf Mp Mw Mx Nn Nr Po) Nb(Ip It Nf Ng Oe Og Pf Pg) Og(Hx Ii Iu Mp Nr) Fp(Mj Nr Po) Iu(Lu Mb Ng) Ns(Ii Mr) Hu(Ji Ok) Ny(Ml Pb) Pf(Mj Pa) LwMm} Aw{Ax(aD aE aN Ap aQ aW aY Bb bE bG bM bS bV bW bX bZ cA cB cH cN cO cQ Cv cX dC De DG dH dI dL dN) Bn(Al aV bS cG Ch cT DC Dd Fr) Bc(aD Bo cD cK cT Cw dB) bO(Af Ar bF Bg bV cX) cE(Ar bQ bV dF Fr) Al(Af bF Bo Ch) Ar(aD bF cD) Bg(bC bS dF) Fr(Af As dB) bV(aI bF Ch) Aj(Ba fR) AdDd AfbC AsbS ChDi bFdF bWcT cGcX cMdM} Hu{Lw(Fp Hq Ih Ik In Io Ip Iq Jh Js Jt Lh Lj Lu Lz Mc Md Mh Mk Mq Mv Ng Ni Nk Nl No Ns Nv Oe Of Oh Ok Pc Po Qe) Ok(Ii Il Ip Iu Lj Mf Nb Nd Ng Nh Nn Ns Oh Oi Pc Pe) Ji(Hx Ip Mf Mp Ne Nh Ni Nk Nm Nx Oe Of Pf Pg) Nm(Hx Lx Mf Mr Nb Nf Nr Oi Pa) Ml(Jq Qa) Mm(Nk Oe) Is(Iv Jr) Jt(Ng Oe) Oi(Iu Mp) JoPe} Cu{Ad(aD Af Aj aK aM aN aQ aW Ax aY Ba bF bI bJ bL bN bP bS bU cA cB cE cG cH cL cN cO cT cY cZ dA Dc Dd dE dI dJ Dk FR) bO(aD aG aV bF bJ Bn Bo bQ cE cV dB dC) As(aD aU Ba bE bQ bV cC cG Cw Fr) Bn(aD aU bB bC bE dF) cX(dB dC dE Di) Dc(bW dC) De(Aj Cp) CqaD CwbW} Po{Ml(Fp Hq Ik Ip Is Iv Jm Jr Lj Lw Mb Mh Mz Nb Nf Ng Nl Oe Oi Oy Oz Pd Pf Pz) Jo(Et Hw Hx Ij Ip Ir Iv Lh Lw Ma Mg Mz Nk Nl Nm Nn Nq Nv) Lw(Hq Hw Ik Jq Lj Lu Of Og Oh Om Pf) Of(Jl Lj Mf Mw Nb Nf Pe) Og(Ji Lj Mf Nf Nm) Ng(Lj Mg Mp Oe) Nf(Lj Oe) EtMm MpOi NbPb IiOk LjOe} cG{cX(AD aI aN aO aQ As Ax Bg bL bM bZ cC cF cQ cT dB dC Dd dE Dg dH Di dM) cE(aD aE Al An Ao AS Ax bJ bP bS bV bX CH cK cR dF Dk dM dN fR) Di(Af Aj bF Bn bO Ch cT Dg) Af(Ad bF bO bV dB Dg) Aj(bJ cV dH Dl) bF(bO dE Dg Dl) Ad(Bb dH) As(Ax bC) Dg(Ap Fr) BnbO} Pe{Pf(Hq Hv Ik Ip Ir It Iv Jh Jm Jq Ly Lz Mf Mg Mh Mx Mz Nb Nf Nl Nn No Nq Nt Nv Of Oi Pb Qa) Jo(Fr Hw Iv Jq Lh Li Lz Mk Mq Mz Nb Nl Nq Nt Nv Oe Og Oh Oy Pc) Oz(Fp Ii Ip Is It Nf Oe Og) Nm(Ii Lw Mm Ok) Ml(Is Og Ok) Ii(Lj Nb Nl) Fp(Ji Oe) LwIt LxPb MaOf MmOy} Aj{bW(aE aM Ap As Ba bB bC bL bO bV cB cK cX dB Dc Dk FR) Ba(aI Ap aU Ax bC bL Bn bO cC cE cM Cq cV dB dE Dg) Fr(aD aE aI bC bO bR cF cM Cq cV cX dB Di) Ap(aO aS bL bM Dc Di Dl) De(Al Ax) bC(aI dF) BbdN CpdE CwbO DcaU} Fr{cT(Af aI bC bF Bg bJ Bo bQ bR cC cF Ch Ct cX dB dC dF Dg dH Di) As(aC aS aV Bg bI Bo bV cK Cq Dc Di) dB(aD aI Bg bO cE Ch Cq Db) Dg(aG Ap Ba) cE(aI dD) ChaD NgNi cXdC} Pg{Lw(Hv Ip It Ml Mn Mw Of Og Oi) Jo(Ip Iu Jg Jt Mg Nm Ok Om) Ok(Mb Ml Mw Of Og Oy Oz) Mm(Ii Ng Nk Nm Oi Pz) Ji(Nm Oy Pz) Oz(Is Ml Oc) Ii(Iu Mz) Og(Jg Nm) NnOi MlIs LiPf} Lx{Ml(Hq Iv Jr Mp Mr Nb Ny Pa) Mp(Mm Mn Ng Nn Pf) Hq(Jm Lw Mc) Iu(Jo Ng Oh) Mm(Mz Ok) Lj(Lw Mr) Pb(Ny Pa) NtJo MjOf JiOh JlOe} Ax{aU(Ad aI aO aQ bI bV cR dB) bW(bR cB cD cE cT dH) Ba(cD cP dB) Ap(bI cI) Di(cR Cs) aI(bE dE) AsCo BbdC DecX bCbM cCdB} bC{As(bL Bo Cp Cq cZ dB dD dE dG dM fR) Bb(aI bO cD Ch dB dC) Di(aI Ch cT) bM(aI aS dB) dM(bO cX dB) cTcX} cT{bW(aM Bc Bn cE Ch cX dE) Ap(Af bO cE cX Dg Di) De(bM Bn cX) Di(bJ cV cX) cE(bZ cO) BcaU aIdE} Mp{Ng(Jl Lu Mf Mh Mr Mw Nm Ny Pd) Oi(Hx Jg Jl Nb) Mm(Mz Nv Ok) Ny(Ml Nf) Oh(Mz Ok) HxJo JlOf} Ml{Is(Il Lh Md Oc Of Pf) Qa(Et Ip Md Ng Oy Pf) Lw(Hw Hx) MbNb MgJt NgIu JlOe NyOf} Jo{Nt(Ij Ip Jk Nv Qa) Ij(Lh Nn Nq Om) Hw(Et Ip Om) Hx(Ip Mm) EtIl NbOm JtNv} bO{dE(aG cC Cp cX DC) Ba(Bn cX) Di(Al Dc) dM(aU cB) ApDg BcdB BnCw

Figure 37 Continued cXdC} dC{cX(Bb bW cW dE Di) Bb(bV Di dN) ApDg BcBo DcDi aldE bMbW dBdM} Hx{Og(Ip Ji Lw Mm Nt Ok) Hr(Ip Nm) NnOi LwMb MzOe JgOf} Mb{Lw(Il Jk Pa) Ok(Jk Ne Nh) NmPa MhIs NgIu} Ny{Pb(Hw Iu Ma Mw Nm Nn Nq Og Pd)} Di{Ad(Ba Dc Dd) As(Ar Dd Dk) al(dE dI)} Ap{Dg(aG aO bV dF) AfBn DbdB alcE} Mm{Nk(Hv Ip Oi) Et(Mz Qa) IIPz IpLi} Ba{Ad(Dc Dd) Dg(bW cX) AfdD alcE} Oe{Et(Ni Nk) MzIv NbOk NgJg JlOz} Of{Nb(Jh Ma Nm) Jh(Nr Pa) JgPa} dE{aI(Bb cE cX) cC(bV dM) cBdM} Jl{Lw(Ii Oh) NmOg MgNg} bM{bW(aI Ch Cq dD)} cE{bQ(bB cX dB) cXdF} As{bV(aU Cw) ArDe} Ip{Nk(Ji Ok) LwHv} Ng{NmHv MgMw} Ii{MhIs IlJt} AdDcaG IlJgOg cCdBdM Unconstrained panels with 3 analytes, where 7.8E-6 >= 'AUC p-value' > 1.0E-6. Contains 20,623 panels of 590,601 total panels evaluated. : aA{Ma(Fp Fr Hq Hr Hw Ih Ii Ij Ik Im Io Is It Iu Iv Jg Jh Ji Jl Jm Jo Js Jt Lh Lj Lx Ly Lz Mb Mc Md Me Mf Mh Mj Mk Mn Mp Mq Mr Mt Mu Mv Mw Mx My Nc Nd Ne Nf Nh Nl Nm Nn No Nq Nr Ns Nv Nw Nx Oh Ok On Oz Pa Pb Pc Pd Pe Pf Qa Qd Qe) Qd(Et Fr Hr Hv Hw Hx Ih Ii Ij In Io Is Iu Iv Jg Jh Ji Jk Jl Jm Jn Jq Js Jt Lh Li Lu Lw Lx Ly Mb Mc Md Me Mf Mg Mk Mm Mn Mp Mq Mr Mu Mv Mx My Na Nc Nd Ne Nf Nh Nl No Nr Nt Nv Nw Nx Ny Og Ok Om On Oy Pa Pb Pc Pd Pe Pf Pg Qe) Po(Fr Hq Hr Hu Hv Hw Hx Ih Ii Ik Il Im In Io It Iu Iv Ji Jl Js Jt Li Lj Lw Lx Ly Lz Mb Mc Md Me Mf Mg Mh Mi Mk Mm Mp Mq Mr Mw Mx My Na Nd Nf Ng Ni Nk Nl Nm Nq Ns Nt Nw Ny Of Ok Om Oy Pb Pc Pf Qa Qe) Iu(Fp Fr Hr Hw Ih Ii Ij Ik Io Iq It Jg Jh Jl Jm Jo Jr Js Lh Lj Lu Lx Ly Mc Md Mg Mj Mk Mm Mn Mq Mr Mt Mv Mw Mx My Na Nc Nd Ne Ng Nh Nk Nl No Nq Nr Nt Nv Nw Nx Ny Oh Ok On Oy Pa Pb Pc Pd Pf Pz Qe) Di(Ad aE aF AJ aN AO aQ Ar AS aV aY Bb BG bL bM bN Bo bR bS bU bZ cA cF cH cI cK cL CO CP Cq Cs CT CW cZ DB Dc DD dF DG dJ Dk DL dM Fr) Nu(Et Fp Fr Hq Hr Ii Ik Io Ir Is It Jg Jh Jj Jl Jm Jn Jq Jr Li Lj Lx Ly Lz Mb Mc Md Me Mh Mm Mn Mr Ms Mt Mv Mx Na Nc Nf Ng No Nr Nt Nx Oh Ok Om Oy Oz Pa Pb Pc Pf Pz Qb Qc) Jp(Et Fp Hq Hr Ih Ii Io Iq Is It Jg Jh Jj Jk Jl Jm Jn Jo Jq Jr Js Li Lu Lx Ly Mc Md Me Mf Mh Mn Mr Mt Mv Na Nc Nd Nf Ng Ni Nl No Nr Nv Nw Nx Ny Ok Om Pd Pf Pz Qb Qe) Oe(Fr Hr Hw Ih Ii Ij Il Im Io Ir Jh Jl Jm Jq Js Li Lj Lz Mb Mc Md Me Mf Mh Mj Mn Mq Mr Mu Mv Mw Nf Ni Nj Nk Nl No Nq Nr Ns Ny Og Oh Oi Pa Pb Pd Pz Qa Qc Qe) Nj(Hq Hr Ih Ii Ik Io It Jl Jm Jn Jq Js Lj Lu Lw Ly Lz Mc Md Me Mh Mj Mn Mr Mt Mv Mx My Na Nc Ne Nf Nh No Nr Ns Nx Of Oh Oi Ok Oz Pb Pc Pf Pz Qb Qc Qe) Nb(Et Fp Fr Hq Hv Ij Il In Iv Jg Jj Jo Jt Lh Lj Lw Lx Ly Lz Me Mf Mh Mk Mq Mv Mw Mx My Nd Ni Nk Nq Ns Nt Nv Of Oi Ok Om On Oy Pa Pd Pf Pg Qa Qe) bZ(aC aH aK aN aO Ap aQ AS aV aW aY bA bB bG bI bL bM BN bP bQ bU cA cC cF cH cI cK cL cN cO cP cR cT cV cW cY cZ dA De dF dI dJ dL) Hu(Et Fr Hw Ih Ii Ij Il Io Iq Ir It Iv Jh Jn Jq Jr Js Lh Lu Lx Mb Me Mj Mk Mn Mr Mt My Na Nc Ne Nh Ni Nk Nl No Nr Nv Nx Om Pa Pz Qa Qe) cL(aC aD aE AF aH aJ aK aM aN aO Ap aQ aR aV AW aY bA bB bE bG bL bM BN bP bQ bR bU cA cB cC cH cK cN cV cW cY De dF dG dI dL) Aw(aC AD aE aJ aK An AS aU aW BB Bc bE bG bH bI bM bQ bU cB cG cH cI CO CP Cq cT CW cY Db Dc De dF dG dJ dL dM) Mp(Fp Fr Hw Ih Ij Il Iv Jg Jh Jm Jo Jr Lj Lu Mb Mh Mj Mm Mn Mq Mr Mu Mv My Na Nd Ne Nh Nl Nt Nv Nw Nx Ny Ok Oy Oz Pe Pg Pz Qe) cO(aC AF aH aJ aK aM aP aQ aR As aU aV aW bG bL BN bP bQ bS bU bV bX cA cF cH cI cN cR cT cW cY cZ dF dI dJ dL) cD(aC aE aH aI aK aL aN aQ aS aV aW aY BA bB bF bH bI bN bP bR bS bU bX cC cE cF cN cP cW cY dD dF dG dH dL Fr) aC(aD aE AF aH aJ aK aM aP aQ aR aV aW aZ bA bB bE bF bL bM BN bP bQ cC cE cG cK cN cR cY dF dI dN) cM(aH aM aN aO aQ aU aY BA bF bH bM BO bP bR bU bV bW cA cC cG cH cI cK cN CP cZ dC De dJ dM fR) Mg(Fp Hv Hx Ij Il Is Jk Jt Lw Lx Mb Mf Mj Mk Ml Mm Mu Mv Ne Nl Nn Nq Ns Nw Oh On Oy Pc Pd Pe Pg Qa Qe) bL(aE aH aI aJ aK AP aQ aV aW aY bA bB bF bG bM BN bR cF cH cI cT cW cY cZ dD dF dG dH dI dJ dL) aR(aJ aK aN aO aW aY bG bH BN Bo bP bQ bS bU bV bX cA cH cI cK cT cW cZ dA dF dG dJ dL dM dN fR) dD(Af aI aJ aK aL aN aO aS aV aY BA bB bH bM bN bR bS bU cA cC cF cI cK cP cW cY dF dG dH dL Fr) cB(aD aE Af aH aK Al aQ Ar aS aV bB Bc bI bQ bR bU bV cI cK cP cT cY dA De dF dG dJ Dk dM FR) Pg(Fp Hv Hx Im In Is It Ji Jt Lj Mf Ml Mm Mx Mz Nk Nl Nm Nn Ns Nw Of Og Oh Oi Ok On Oy Pb Pf) aF(Af aJ aK aN aQ AS aV aW BN bP bU bV bX cC cH cI cK cN cP cY cZ dA De dF dG dJ dL dM) cV(Af aJ aN AP aQ aS aW aY aZ bH BN Bo bP bS bU bX cH cN cQ cT cW dA dF dG dH dJ dL Fr) Pe(Et Hx Ii Im In It Iv Ji Jt Lj Lw Mb Mf Mk Mm Mw Nk Nl Nm Nn Nq Nw Of Og Oi Ok On Oy Pb) aD(Af aH aO aQ aS aV bA bF bH bM BN bP bQ bR bU cA cC cE cI cK cN cQ dA dF dG dH dJ dL) dI(aJ aK aN aO AP aS aY bE bG bJ bM Bo bP bQ bV bX cH cI cK cN cT cW cZ De dF dJ dL dM) Mz(Et Hv Hx Im In Iv Jg Lh Lw Lx Mb Mk Ml Mm Mq Ni Nk Nl Nm Nn Nq Ns Nt Nv Og Om On Pd) aI(Af aH aJ aK aL aN aS aY BA bB bF bH bM bP bU bX cA cC cF cI cN cP dF dG dH dL Fr) Ap(aJ Al aM An aP Ar aS aY Ba bB Bc Bg bI bR bU cG cI cP cR Cs Ct cW cZ De dF dJ dM) Fr(aE Af aG aH Aj An aU aV aX bB Bg Bo cG Ch cI cK cT cX dA Db DE Dg dL fR Og) Ml(Ii Il Im In Iv Jg Jh Ji Jt Lh Mb Me Mf Mm Mq Mt Mu Mv Mw Nk Nl Nq Nt Ny Og Qe) aL(aJ aN aO aS aV aY aZ bB bF bH bI bM BN bP bR cA cE cF cI cK cN cP dF dG dH) bJ(Af aJ aS Ba bG bH bI Bn bP bS bU bV bX cE cH cK cN cP cQ dA Dd dG dJ dL dM fR) aZ(aN aQ aS bA bF bG bI bN Bo bS bU bV bX cH cI cK cT Cv cW cY cZ dG dJ dL dM) cR(aE Af aJ aO aS bE bH bI bQ bS bU bV bX cH cI cP cQ cT Cw cZ dA dF dJ dL dM) De(aH aJ aK aO aP aU aX Bb bG bH bU bV bW cG Co Cp Cs Cv cW cY dA Dc dF fR) aW(aE aH aJ aK aN aQ As aV aY Ba bF BN bR cC cE cK cP cT cY dF dG dH dL) cF(aE Af aH aK aN aO aQ aV aY bA bF bG bM BN bR cA cC cE cP cW cY dH fR) Hx(Et Hr Im In Jj Jt Lj Lw Lx Mb Mm Mq Nk Nm Nn Nt Nw Of Ok On Oz Pb) bB(aE Af aK aN aO aS bA bF bG bH bI bN bS bX cC cH cI cP cT dF dG dL) bE(aJ aM aO aS aY bG bU bV bX cC cI cP cQ cT cW cZ dA dF dJ Dk dM dN) dB(aH Al aO aQ Ax bI bQ bR bU bV bX cI cN cP CQ Cw cZ dA Dc dG dM) Og(Hv Hw Il Iv Jg Jl Lh Lw Lx Mb Mk Mm Mq Mu Mv Nt Nw Ok Om Pd Qe) aP(aH aJ aN aO AS aY bH bI bS bU bV bX cA cH cK cQ cT cW cZ dJ) cX(Ad Al An Ao Ax Bb Bn Bo bS Ch Co Cp Cq Ct Cu Cw Dd Dg DI fR) dE(Aj Al An As Ax Ba Bb Bc Bg Bo Co Cs Ct Cu Cw Dc Dd Dg Dk DI) aM(aH aY bA Bo bP bQ bS bU bV bX cA cE cT cW dA dG dJ dM fR) bO(aK Al An aQ As aV bI Bo bQ bS bV cH Co Cp cQ cW cY Dd dJ) dC(Aj An As Ax Bb Bc bV cN Co Cp CQ Cu Cw Db Dc Dd Dk fR) Nm(Hw Il Jq Lh Lj Lx Lz Md Mk Mq Nf Nk Nn Nq Ns On Pa Pb) Bn(aE aK aN Ax aY bA bN Bo cA Co Cp CW cY Dd dH dN) In(Et Hv Im Iv Jg Jj Lw Lx Mb Mk Mm Mq Mu Nn Nq Nt On) aG(Ad Aj As Ax Ba Bg Bo Ch Cp Cq Ct Cv Cw Db Dg fR) bN(aE aH aJ aK aO aQ aV bA bG bR cA cC cE cW cY dN) Im(Ii Lh Lx Me Mj Mk Mq Ni Nl Nn Nr Nv Nw Oi Pf) Ip(Hr Iq Ir Jk Jq Li Lz Ms Na Nc Nf Nh Oy Pf Qc) On(Hv Iv Ji Jt Lz Mb Mh Mq My Ns Nw Oh Oi Oz Pc) aJ(aE aH aK aQ bA bG cA cC cE cP cT cY dA dL) bW(Ad Ax aY Bg bH bI Co CQ Ct Cv Cw Dg dN) cG(Ad Aj An Ax Bo Ch Cp cQ Ct Cw Db Dk dN fR) cW(aE Af aH aN aO bF bG bM bR cE cP cZ dG dH) Nn(Hv Jt Li Lx Lz Mf Mh Nf Ni Nw Ok Pa Pc) cC(aE aH aQ aV aY bF bP bX cE cP cZ dH fR) bA(aE bF bH bM bR cE cP cT cZ dF dG dH) Af(aK aQ aV Bo bR Co Cp Cq Ct cY dN) Ji(Il Jl Jo Lx Mb Mx Na Nk Nx Of Pa) aU(Al Bc bH bI bV cQ dA Db dF Dk dN) cA(aE aH aK aQ aV bG cE cI cY dA dH) Lw(Il Jk Lx Mb Mk Mm Nq Nt Of Qa) Jj(Hw Jk Lh Li Lx Mk Nw Om Qa Qe) bM(aH aK aN aV bF bG bR cY dH dN) Oi(Iv Jk Lh Li Lx Mq Nt Nw Ok) cE(aE aH aK aQ aV aY bR dN fR) dH(aH aK aN aY Ba bF bV fR) Mi(Ik Lu Me Mh Mj Pa) Mm(Hv Il Lx Mj Mk Ng) Jt(Lx Mb Mk Nq Of Pc) Nw(Hv Il Mk Ne Nf Ni) aH(aN aY bG bH cZ dL) aX(Ar Bc Co Cs Cu Cw) cY(aN bF bS cP dG dL) Nk(Li Lx Nt Om Pc) bQ(bR cK cN dL dN) Ba(Aj Bo cS Ct) Jo(Lh Om Qa Qe) aN(aQ bG bR cP) aY(aV bG bR cN) Ms(Jg Lu Mn) bF(aO aQ dN) Dd(As Bo) Nq(Of Pc) Ni(Mq Nt) Is(Jr Mh) Jh(Nf Pb) Oz(Il Jl) bG(bS Dk) bR(aK bH) cS(Ct Dc) dN(cN dL) AodK CocK LxLj LzLi MfMu MwMy HwQa NyPb aQcZ aVdG} Ip{Po(Fp Fr Hu Hv Hw Hx Ih Ij Ik Il Io Iq Ir Is It Iv Jg Jh Jk Jl Jm Jn Jq Jr Js Jt Lh Li Lu Lx Ly Lz Ma Mb Mc Md Me Mg Mh Mj Mk Mn Mq Mr Mt Mu Mv Mw Mx My Nc Nd Nh Ni Nk Nl No Nq Nr Nt Nv Nw Nx Ny Oh Om Oy Pa Pc Pd Pe Pf Pg Qa Qb Qc Qe) Mz(Fp Fr Hq Hr Hv Hx Ih Ii Ij Ik Io Iq It

Figure 37 Continued

Iv Jg Ji Jj Jk Jl Jo Jr Js Lh Lj Lu Lx Ly Lz Mb Mc Md Me Mf Mh Mj Mk Mm Mn Mq Mr Mu Mw Mx My Nb Nd Ne Nf Ng Nh Ni Nk Nl No Nr Ns Nt Nv Nx Ny Oh Oi Om Oz Pb Pd Pf Pz Qa Qc Qe) Ip(Fp Fr Hq Hr Hu Ih Ii Ik Io Ir Iv Jg Jh Jl Jm Jq Jr Jt Lh Lj Lu Lx Ly Lz Mb Mc Md Me Mf Mg Mh Mj Mk Mm Mn Mq Mr Mt Mu Mv Mw Mx Na Nb Nd Nf Ni Nj Nl No Nq Nr Ns Nt Nv Nw Nx Og Oh Om Oy Oz Pa Pb Pc Pd Pf Pz Qa Qb Qc Qe) Pg(Et Fp Hu Hw Ih Ij Ik Il Io Ir Is It Iv Jg Jh Jk Jl Jm Jn Jq Jr Js Jt Li Lu Lx Lz Mb Mc Md Me Mf Mh Mj Mk Mn Mq Mr Mt Mu Mv Mw Mx My Nb Nc Nd Ne Nh Nk Nl No Nr Nv Nw Nx Ny Oh Om Oy Pa Pb Pc Pd Pe Pz Qa Qb Qc Qe) Hx(Fp Hq Hu Hv Hw Ih Ij Ik Iq Ir Is It Iv Jh Jk Jl Jm Jn Jo Jr Js Jt Lh Lu Lx Ly Lz Mb Mc Md Me Mf Mh Mj Mk Mn Mq Mr Mt Mu Mw Mx My Na Nd Nf Ng Nh Ni Nj Nk No Nr Ns Nv Nw Nx Ny Ok Oz Pb Pd Pf Pz Qa Qb Qc Qe) In(Et Fp Hq Hr Hu Hw Ih Ij Ik Il Io Iq Ir Is It Iv Jh Jk Jl Jm Jn Jo Jq Js Lh Li Lj Lx Ly Lz Mc Md Mf Mh Mk Mn Mu Mv Mw Mx My Na Nb Nc Nd Ne Nf Nh Ni Nj Nk Nl No Nr Ns Nv Nx Ny Om Pa Pb Pd Pf Pz Qb Qe) Ma(Fp Hq Hr Hu Hv Ik Io It Iu Jg Jh Ji Jj Jl Jm Jn Jr Jt Lh Lj Lu Lx Lz Mb Mc Md Me Mh Mk Mn Mr Mt Mu Mw My Nb Nd Ni Nj Nm Nn No Nq Nv Nx Ny Oh Ok Oy Oz Pb Pc Pd Pf Pz Qa Qb Qc Qe) Nm(Hq Hr Ih Ii Ik Io Ir It Iv Jg Jh Jl Jm Jn Jo Jr Js Lh Lj Lw Lx Mc Md Mf Mh Mn Mq Mr Mt Mv Mw Mx My Na Nb Nd Ni Nj No Nq Nr Ns Nt Nv Nx Ny Oh Ok Om Oy Oz Pc Pd Pf Pz Qa Qe) Lw(Fr Hq Hr Ih Ii Io Iq Ir It Iv Jg Jh Ji Jl Jm Jn Js Jt Lh Lj Lx Ly Lz Mc Md Me Mf Mh Mm Mn Mr Mt Mu Mv Mx My Nb Nc Nd Nf Ng Ni Nj Nr Ns Nv Ny Oh Om Oz Pb Pc Pd Pf Pz Qb) Ij(Fp Fr Hq Hr Hu Hv Ik Il Io It Iv Jg Jl Jm Jr Js Lh Lj Lu Lx Ly Mb Mc Mf Mg Mh Mj Mm Mn Mq Mr Mw My Nb Nd Ne Ng No Nq Nr Ns Nt Nv Nw Of Oh Pa Pb Pc Pe Pf Qa Qc Qe) Iu(Fr Hw Ih Iq Ir Is It Iv Jg Jj Jl Jn Jq Js Jt Lh Lx Ly Lz Mb Mc Md Me Mj Mk Mn Mp Mr Mt Mu Mw Mx My Nb Nd Ni Nn Nq Nr Nt Nv Nw Nx Ny Oh Ok Oz Pc Pd Pf Pz Qa Qc Qe) Il(Et Fp Hq Hr Hu Hv Hw Ih Ii Io Iv Jg Jl Jm Jq Jr Lh Lj Lu Lx Ly Lz Mb Mc Md Mh Mj Mk Mn Mv My Na Nc Nd Nf Ng No Nr Ns Nt Nv Nw Nx Ny Oi Om Pa Pb Pd Qa Qb Qc Qe) Ne(Et Fp Hq Hr Hv Ih Ii Ik Io Jn Jo Jq Js Lh Li Lj Lu Lx Lz Mb Md Me Mh Ml Mn Mr Ms Mu Mv Mw My Na Nf Ng Nh Nj Nk Nr Ns Nv Nw Nx Of Og Pa Pb Pd Pe Pf Qa Qc Qe) Ji(Et Fp Hq Hr Ih Ik Io Iq Ir Is It Iv Jg Jj Jl Jm Jo Jt Lh Lu Lx Lz Mc Md Me Mg Mh Mj Mm Mq Mr Mt Mu Mv Mx My Na Nf Ni No Nq Nt Nv Nw Ny Oh Om Oy Oz Pb Pc Pf) Nn(Hq Hr Hv Hw Ih Ik Iq Ir Is It Jg Jh Jj Jk Jm Jn Jq Js Jt Lh Lj Lx Ly Mc Me Mh Mj Mk Mn Mr Mu Mv Mw Mx Nd Ni Nj No Nq Nr Nt Nv Nw Nx Ny Ok Om Pd Pz Qa Qc) Nt(Et Fp Hq Hr Hv Hw Ii Ik It Jj Jl Jo Jt Lj Lz Md Mf Mh Mn Mp Mr Mt Mu Mw Mx My Nb Nc Nf Ni Nj Nl Nq Nr Ns Oh Ok Om On Oy Pa Pb Pc Pf Qa Qb Qd) Nq(Fp Fr Hq Hr Hu Hv Ii Io Jg Jh Jk Jl Jm Jr Lx Mb Mc Md Me Mf Mj Mn Mr Mt Mv My Nb Nd Nj Nk No Nr Ns Nv Ny Ok Oy Oz Pb Pf Pz Qa Qe) Ml(Fp Fr Hw Ih Ii Ik Ir Jg Jj Jk Jl Jq Jr Lh Li Lu Lx Mf Mg Mk Mm Ms Mu Mw Nf Ng Nh Nk No Ns Nv Ny Og Oh Oi Ok Pc Qb) Qa(Hq Hu Hv Io It Jk Jm Lh Lj Lu Ly Lz Mb Mf Mh Mj Mn Mq Mt Mw Nb Ng Nk Nr Ns Nv Nw Of Og Oh On Pa Pc Pe Pf Qb) Pe(Et Hw Ih Iq Ir Jg Jh Jk Jn Jq Jr Li Lu Lx Ly Mb Md Mj Mk Mr Mt Mu Mv Na Nc Nd Nh Ni Nl Nx Ny Om Pd Qb Qe) Pa(Fp Hr Hv Hw Io Iv Jg Jn Jr Jt Lj Lz Mf Mg Mh Mk Mm Mn Mq Mr Ms Nf Ng Ns Nv Ny Oh Oi Ok Om On Oz Pc Qb) Og(Fr Hv Ii Ik Ir Is Iv Jg Jh Jk Jl Jr Jt Mg Mj Mm Mq Nb Nh Nk Nr Nv Oh Ok Om Pc Qb Qe) Im(Et Ih Ik Io Iq Is It Iv Jg Jh Jq Js Lh Me Mu Mv Na Nc Nd Nw Nx Ny Om Oy Pd Qc Qe) Ms(Et Fp Hv Ih Ik Iq Jg Jh Jn Js Lh Lx Mj Mk Mv Mw Na Nb Nd No Nr Nv Nx Ny Qb Qc) Of(Fr Hv Hw Ii Iq Iv Jg Jq Jr Jt Lh Li Lx Mg Mj Mm Mq Mr Mu No Nv Ok Oz Qb) Oi(Et Ii Ik Ir Is Jg Jk Jl Js Lh Li Lx Lz Mj Mk Mv My Na No Nr Oe Ok Om) Mp(Et Hw Ih Ik Iq Ir Is Iv Jh Jq Jt Lh Ly Md Mg Mq Na Nl Nw Om Oy Qc) Jj(Fp Hr Hu Ih Iq Is Iv Jl Jm Jq Jt Mg Mj Mm Nb Nw Ny Oe Om On Qb Qe) On(Et Ih It Iv Jn Jo Jt Li Lu Lx Ly Mw Mx Na Nc Nd Ni Nl Ny Pd Qd) Mm(Hr Hv Hw Jt Ly Mb Me Mg Mj Mx Nf Ni Nr Nu Ok Oy Pz Qb Qd Qe) Fr(Hr Hv Hw Ii Mj Mk Mr Mx Nb Nf Ni Nj Nk Nr Oh Pc Pz Qd Qe) Nh(Et Ih Jg Jq Jr Lh Li Md Mf Mh Mu Mv Na Nl No Nv Nw Om) Nk(Et Hw Ir Is Iv Jg Li Lx Mg Mq Mu Nc Ns Ok Om Oz) Oe(Et Io It Jh Jn Jr Mc Me Mf Mn Mt Nc Pf Pz) Hv(Hw Ir Lh Lj Mq Ng Ns Nv Nw Oh Pc Qb) Nu(Ih Ii Jm Li Lu Mv Nj Nl Oy Pd Pz) Jk(Hu Iv Jr Jt Me Mg My Ng Nj Pz Qd) Ok(Et Jg Ly Mb Mg Mq Nb Nj Nx Pz Qd) Ng(Is Iv Jh Jl Jr Mq Mv Mw My) Mg(Jo Ly Mf Mj Nf Ni Nj Qb) Nb(Fp Hq Ir Is Jr My Nw Oz) Mq(Jo Jr Nf Ni Nj Ns Qb) Qd(Et Ih Is Jg Mb Me Na) Hu(Ir Jt Mu Nw Oh Pc) Hw(Lj Ns Nw Oz Pf Pz) Jr(Md Mk Ns Nv Oh Pc) Nj(Et Is Li Lx Om) Jo(Is Iv Jl Li Om) Pz(Is Li Nw Om) Oz(Iv Jl Nr Pb) Ii(Iv Jl Jt) Ir(It Jm Lj) Oh(Fp Pc Qb) Pb(Jl Mw Nr) Jt(Li Mb) Pc(Fp Qb) LzMj MwIs NfJq} aP{dA(aF aH AJ aK Al aN aO aQ AR AS aU aV aW aY bB Bc bE bG bH bI bJ bL bU bV bW bZ cA cC cG CH cI cK cL cO cQ cV cW cY cZ dF Dg DI dJ Dk dM) cD(Ad AJ aK Al AN aO aR aW aY Bb Bc bE BG bH bI bL Bo bQ bU bV cC cG CH cK cL cM CO cQ Cs cV CW cY cZ Db dF Dg dI dJ Dk dM dN FR) As(aC Ad aE aG aH aJ aL aN aS aY aZ Bb bE bF BG bH bI bM bP bQ bU bV bZ cB cE cG CH cI cL cM cN CO CP Cq cV Cw cY Dd Dg dI dJ Dk dL dM) cI(aF aH aJ aK aN aO aQ aR aS AW aY bB bC bE bG bH bI bL bQ bS bU bV bW bX bZ cA cC cG cH cL cO cP cQ cR cS cV cW cY cZ dF dI dJ dM) Af(aF AJ AN aO AR aW AX aY Bb bE Bg bH bM bQ bS bV bX cA cC cE cG CH cL cO Cp cR Cs Ct CV CW cX cZ Db dI dJ Dk) Di(aF aH aK Al aN aO Ap AR aS aU aX aY Ba BB bE bG bH bI bS bU bV bW cA cG cH cL cM CO cR Cv cY cZ Dc Dd De dI dJ Dk Dl Fr) aV(aF aH AJ aK aM aN aQ aS aU aW aY bB bC bE bG bJ bM Bo bQ bS bU bV bW bX bZ cA cC cG CH cL cR cS cW cY cZ dF Dg dI dJ dM) Bn(aF aH aJ aK AN Ap aQ aS Ax aY aZ Bb bC bE bF Bg bI bJ bM bN bP bU bZ cE cG Ch cL Cp Cq cS cV cX cY Db Dc Dd DE dF dM) dE(aC aH aJ aM aQ aR aS aU aW aY Bb bC bE bG bH bL bQ bS bW bX bZ cA cH cK cL cM cO Cp CQ cR cS cW cY cZ Dd dF dJ dM dN) Aw(aF aG aH aJ aK Al aO Ap aQ AR aU aW Ba BB bC bH bL bS bW cA cB cG cM cO Cp Cv cW cY cZ Db Dc dJ Dk Dl FR) cR(aF aH aK aM aO aQ aR aW aY bC bE bG bI bL bQ bS bU bV bW bZ cA cC cG cH cK cL cM cP cQ cS cV cW cY cZ dF dI dJ dM) aU(aH aJ aW Ax aY aZ bB bC BG bI bJ bL bQ bS bU bV bW cA cB cC cG CH cK cL cO cQ cS cV CW cZ dF dI dM fR) bX(aF aH aK aM aN aO aQ aR aS aW aY aZ bE bG bI bM bN bP bS bW cA cC cF cG cH cK cL cM cQ cV cW cY cZ dF dI dJ dM) bB(aH AJ aK aN aO aQ aR aS aW Ax aY bE bG bH bI bL bQ bS bV bW cA cG cH cK cL cM cO cV cW cY cZ Dg dI dJ dM) cP(aF aJ aK AN aO aS aW bE BG bI bL bM Bo bS bV bW cG CH cK cM Cp CQ Ct cV cW cY cZ dF Dg dI dJ dM) bF(aF aJ aK aM aN aQ aR aW aY bE bG bH bI Bo bQ bS bU bV bW bZ cA cC cH cL cM cO cQ cV cW cY cZ dF dI dJ dM) bJ(aF aH AJ aK aN aQ aW aY bE bG bH bI bL bQ bS bU bV bW bZ cA cC cG cH cL cQ cV cW cY cZ dF dI dJ dM) aM(aF aG aJ aK aN aO aQ aR aW aX bC bG bL bM bQ bU bV bW cA cC cE cG cH cK cL cS cV cW cY De dI dJ dM) bN(aF aJ aK aN aQ aR aS aW aX bE bH bI bL Bo bQ bS bU bW cA cH cK cL cO cQ cS cW cY cZ dF dI dJ dM) cB(aF Al An Ao aS aX Bc bE BG bI Bo bU bW Ch Cp CQ CS Ct Cv Cw Db Dc De dF Dl dN FR) aG(Ad aF AJ aK aO aW aY bE bG bH bI bL bS bU bV cA cG cH cK cL cM cO cQ cW cY cZ dI dJ dM) cC(aF AJ aN aO aQ aS aX bC bG bQ bS bV bW bZ cF cG cH cK cL cN cO cQ cS cV cW cY cZ dF dJ) cT(aC aJ AN Ap aQ aR aS bA Bb bH bI bL bM Bo bS bV bZ cH cK cM cO cQ Ct cW De dI dJ dM Fr) aQ(aF aH AJ aN aR aW aY bC bG bM bQ bS bU bW bZ cA CH cL cS cW cY dF dI dJ dM) bM(aC aH aJ aK aN aO aR aS aY Bb bI bL bS bU bZ cA cH cL cO Cq cW cY cZ dF dJ dM) cN(aF AJ aK aN aR aS Ax bE bI bL bQ bS bW bZ cG cK cL cM cQ cV cY cZ Dg dI dM) aZ(aC aF aJ aK aR aS bG bI bL Bo bV cG cK cL cM cO cQ cV cY cZ De dF Dg dJ dM) bC(Ad aF aH aK aN aW aY bG Bo bS bU bV bW cA cG CH cL cO cW cY dF dJ dM) bO(Ad Aj An Ap Ax Bc Bg Ch Cp Cq Ct Cu Cv Cw Db Dc Dd Dg Dk Dl dN FR) dB(aC Ad An Ap Ax Bb bE Bg bH Bo bV Ch cK cL Cp Cq Db De Dg dI Dl dN Fr) aH(aF aJ aN aO aW aY bE bG bQ bU bW bZ cA cG cH cL cS cW cX cZ dF dJ) aI(Ad AJ aL An aR Ba Bb bH Bo Ch Co Cp cQ Ct Cw Db De Dk Dl dN fR) bG(aF aJ aN aO aS aW aY bS bU bW bZ cA cE cH cL cQ cS cW cY cZ dJ) cX(Ad Aj An Ap Ax Ba Bb Bg bH Bo bS Ch Cp Cq Cu Db Dc Dd Dg FR) bP(aJ aK An aR aS bH bI bL Bo bS cG cK cM cO cQ cV De Dg dI dM) bW(aN aW bL bQ bS bU bV bZ cA cG cH cL cO cS cW cY cZ dF dI dJ) aD(Ad An Ao Ap Ar Bc Bg Bo Ch Co Cq Ct Cv Db Dd Dk Dl FR) bR(Ad An Ar Bc bE Bg Bo Ch Cq Cs Ct Cv Cw Db Dg Dk dN FR) bZ(aK aN aO aW aY bE bS bU cA cG cH cQ cV cW cY cZ dI dJ dM)

Figure 37 Continued dC(Ad An Ao Ap Ax Bc Bg Ch Co Cp Cq Ct Cv Cw Db Dc De Dl Fr) bQ(aF aN aO aW bE bL bS bU bV cA cG cO cQ cV cZ De dl dJ) cM(aE aF AJ aL aX bA bE bL Bo bV cK cQ cS cV dD Dg dl) dL(aC Ad Aj Ap Ax Bb Bg bL Bo Ch Ct cZ Db Dd De Dg dN Fr) aL(Ad Aj Ar Ax Ba Bc Bg bL Ch Cq Cs Cv Cw Db Dk Dl) cK(Ad Aj An Ap bA Bb Bg Bo cF Ch Co Db dD De Dg Fr) cS(Ad aJ aK aN Ap bE Bg bL bS cG Ch cQ cY Db dF dJ) cE(aC aY Bb bI bS cA cO Cp Cq cW cZ dF dN FR) aE(aC aF Aj aR Ax bI bL Bo bV cO cQ Dg dN fR) bA(aC Ad An aS Ax Bb Bg bS Co Cp Cs Ct Dl) bU(aW aY bE bS cA cG cH cL cW cZ dF dJ) cF(aC An Ap Ba bH bL Bo Ch cO cV Dg dN) cG(Aj aN aY cA cL cO cV cW dD dF dI) Dg(aF aW aX Bo Cp Cw cY Dl dM Fr) dD(Aj An Ap aR Bb Bg bH bI Bo cO) Aj(aF aW AX Bo Co dM Fr) bV(aF aJ aY bL cQ cV dF dI) aW(aN aY cA cL cW cZ dI) aX(aN Ax cJ Cp cZ Dc dK) aS(aF aO bE bS cQ cV) aY(bS cA cH cL cZ) dF(aK aN cY cZ dI) aF(aN bS cQ cZ) aO(bE bL cV dM) dG(Ba Co Cp Dc) dI(aJ bE cQ cV) Ad(Ax Dc De) Cu(Cq cU Cw) Dd(Bo cU dK) cY(aJ cA cZ) Ax(bE De) bS(cA cL) cV(bH bL) dK(bI De) AldH ApBo cHcW} cU{Co(aC Ad Af Aj aL AN Ao AR aS aW Bc bE bG bH bI bJ bM bN Bo bP bR bS bV bX cF CH cP CQ cR Cs CV cW cZ Db dF dG dH dJ Dk Dl dM dN) bE(aC Ad aF Aj aM AN Ap aQ aR AW aX BC bG bH bI bN Bo bP bS bV bW bX cB CH cI cK cP Cq cR Cs Cv CW Db dF DG Dk DL dN Fr) Ar(Ad Af aH Aj AN aQ aS aW aX aY bC bG bH bJ Bo bR bU bW bX cC cF cG CH cI cL cO CQ Cs cV Cw cY dA Db Dc De Dg dI dJ Dk dL dM dN) An(Ad Af Aj aM aN Ao aS aW aY bC Bg bH bJ bM bR bU bX cA cD cF cG CH cI cK cL cO cP Cs CV Cw cZ dA Dc dD dF Dg dI Dk DL dN) bG(aC Af aK aQ aS aU aV AW bB BC Bg bI Bo bP bS bV bW bX cF cG CH cI cK Cp CQ cR Cu Cw cY cZ dA dD dF dI Dk DL dN) Cv(Ad aE aH aK aL aM aN Ao aQ aW aY Bc Bg bH bJ bM bQ bR bU bV cA cC cF cG CH cI cK cO cQ Cs cW dA Db De Dg dH dI dL dM dN) bP(aE aH aK aM aN Ao aQ aS aU aW Ax Bc bH bI bN Bo bV bX cB cF CH cI cK cP CQ Cs Ct cV cZ dA Db Dc dD De dF dG dL dN) Db(Ad Af aH Aj aK aN Ao aQ aS BC bH bM bU bX cF cG cH cI cO cP cQ Cs Ct cV CW cZ Dc dD De Dg dI dJ Dk dL dM dN) cP(aC Ad Af aH aK Al aQ aR aS aU aW bC bH bI bN Bo bS bX cB Ch cI cK CQ Cs Cw cY cZ Dc dD De dF Dg Dk DL dN) Bo(aC Ad Af Aj aK aL aM aQ aR aS aW BC bH bI bS cF cH cI cO cR Cs Ct cV Cw cZ dD De Dg dJ Dk DL dM dN) Dk(Ad Af aK aN Ao aQ aS aW aY BC bJ bR bU bX cF cG CH cL cQ Cs cV dA DC De Dg dH dI dJ dM dN Fr) Aj(aN aS aW aY bB bM bO bQ bR bU bV bX cA cD cF cG CH cI cK cL cO Cp cQ dA DD dF Dg dI DL dN) aR(aC aK Al aN Ao Ap aQ aS aU aV aW Ax bC bH bN bU bW bX cD cG CH cI cK Cq cR cV cY cZ dA De dI dL) Dl(aH aM aQ aS Ax aY aZ Bc bH bJ Bn bQ bR bU bX cA cC cF cG Ch cL cO Cp CW dA Dc De Dg dH dI dM) bN(aC aE aH aL aN aQ aS aU aW Ax bC Bg bH bI bU bX cD cF CH cI cK cO CQ cR cV cY dA dD dI dN) cB(aD aE aL aN aV AW aZ BC Bg bM Bn bU cA cD cF cG cI cK cO cQ cR CW cY dA Dc DD dI dN) dF(aK aL aM aN aQ aS aU aW aX aZ bB Bc bM bU bX cF cH cI cJ cK Cp CQ cR Cw cZ dA Dd dG dI dL dN) Ad(Af aM aN aQ aS aW aY aZ Bc Bg bH bQ bR bU bX cC cD cF cG CH cI cO cQ Cs Cw dA dD De dI dL) aF(aC aE AL aM aS aU aV aX aY bC Bg bH bJ bM Bn bQ bR bU cA cD cG cO CQ cW dB Dd dI dN Fr) dJ(aC aD aE aI aL Ap aY aZ Bc Bg bJ bO bQ bR bS cA cD Ch cJ cL cM cN cO CS Cu CW dI Fr) bI(aC aH Al aN Ap aQ aU aW Ax aZ BB bH bM bV bW bX cF cH cI cK cQ cR cV cW dD dL dN Fr) Af(aE aL aN Ao aS aW aY Bc bR bU bX cC cD cG cI cL cO cQ cV cZ dA Dc dD De Dg dH dI dL) Ao(aK aN AX aZ Bg bJ bS bW bX cF cG CH cI cQ cV CW Dc Dd De DG dL dM dN) Dc(aE aK Al aM aN aS aW aZ bB BC bH bM bS bV bW bX CH cQ cR Cs cW cY dG dM) De(aK aM aN aS bB Bc bH bJ bR bX cC cF cG cH cI Cp cQ Cs cZ dA Dd Dg dI dL dN) bS(aE aH aN aQ aS aU aW Ax aZ bB bC bV bX CH cI CQ Ct cV cY cZ dD dL dN) Bc(Al aM aN Ax aZ bM cA cF cG CH cI cO cR Cs cV Cw cZ Dg dI dL dM dN) aC(aK Al aM aN aO Ap aU aW Ax Ba bV bW bX CH cI Cp cQ cR cW Dg dN) dG(aD aE aH Al aO aU Aw aZ bB bH bM bV cG cI cM Cp cR Cw cY Dd dN) Cs(aK aM aN aS aW bM bR bU bX cF cG cH cI cQ cV cZ dA dI dL) aO(aK AL aQ aV bM Bn bV cA cF cJ cS cY dA dB DD dI dN) cR(aK aM aN aQ aS aW aX bH bV bX Ch cQ Ct Cw cZ dD dL dN Fr) Cu(aG aL Aw aY Bg bO bQ bR cD cL cM cS cX dB dE Dg fR) Dg(aM aN aQ aS aW bH bR bX cC cF cH cI cV cZ dL dN) aX(aH aK aQ aU aV bB bC bH bW bX cJ cV cW cY dN) dL(aH aK aN aQ aS aW Ax bM bX CH cK Cq cZ dD) cZ(aH aK aN aQ aV Bg cK Cp Cw cY dA Fr) Cw(Al Ap aS bC bJ bW cQ cW dD Fr) aK(Al Ap aS bB bX cD cK cV dA dD) Ch(aL aM aN bM cF cH Cq Dd dI) Fr(aE aI aS bC bL bW Cq cV Dd) cK(aH aN aQ aS aU bC bX cQ cY) Ct(aH aU bB cH cM cW cY dM) Bg(aM aW bR cA cC cF cQ) Cq(aH aL aQ cM cW cY) dA(aQ aU aW bX cO cY) dD(aH aL aQ aU Cp cY) Dd(bM cM cT cW cY) Al(aM bC cW dM) Cp(aS bB cQ cV) aM(bB cH dN) cA(aY Bn bU) cF(aQ bV bX) Ap(bX dN) aS(aQ cY) cQ(aZ cY) AxaL aEbM aHbB bQcO} Qd{Nb(Et Fr Hq Hr Hu Hv Hw Hx Ih Ij In Io Ip Iq Ir Is Iu Iv Jg Jh Ji Jk Jl Jm Jn Jq Jr Js Jt Lh Li Lj Lu Lw Lx Ly Ma Mb Mc Md Me Mf Mg Mh Mk Mm Mn Mp Mq Mr Mu Mv Mw Mx My Mz Na Nc Nd Ne Nf Ng Nh Ni Nk Nl No Nq Nr Ns Nt Nv Nx Ny Oe Of Oi Ok Om On Oy Pa Pb Pc Pd Pe Pg Qa Qb Qe) Fp(Et Fr Hq Hr Hx Ii In Io Iq Ir Iv Jg Jh Ji Jl Jm Jn Jr Js Lh Li Lj Lu Lw Lx Ly Lz Ma Mc Md Mf Mh Mj Mk Mm Mn Mp Mr Mt Mu Mw Mx Nd Ne Nf Ng Nh Ni Nk Nm Nn No Nq Nr Ns Nv Nw Nx Ny Oe Og Oh Oi Ok On Oy Oz Pa Pb Pc Pd Pe Pf Pg Po Qb Qe) Nw(Et Hq Hr Hv Hw Hx Ih Ii Ij In Io Ip Iq Ir Is Iu Iv Jh Jl Jm Jn Jq Jr Js Jt Lh Li Lu Lx Ly Mb Mc Md Me Mf Mh Mj Mk Mn Mp Mq Mt Mu Mv Mw Mx My Mz Nc Nd Ne Ng Nh No Ns Nx Ny Oe Og Om Oy Oz Pb Pc Pd Pe Pf Pg Po Qa Qb Qc Qe) It(Et Fr Hr Hw Ih Ii Ij Ik Im Io Iq Is Jg Jh Jk Jl Jm Jn Jq Js Lh Li Lu Lx Ly Lz Ma Mb Mc Me Mg Mh Mj Mk Mm Mn Mq Mr Mt Mu Mv Mw Mx My Na Nc Nd Ne Nh Nn No Nq Nr Nv Nx Ny Oh Om Pb Pc Pd Pe Pf Pg Po Qa Qb Qc Qe) Lj(Et Hq Hr Hu Hv Hw Hx Ih Ii Ij In Ip Iq Is Iv Jg Jh Ji Jl Jm Jn Js Jt Lh Li Lu Lw Lx Ly Lz Mb Mc Md Me Mf Mi Mj Mk Mm Mn Mr Mx Mz Nd Ne Nf Ng Ni Nk Nq Ns Nx Ny Og Oi Ok Om On Oy Oz Pa Pb Pe Pg Po Qa Qb Qe) Mf(Et Hq Hr Hu Hv Hw Hx Ih Im Io Ip Iq Ir Iv Jg Jl Jm Jn Jr Js Lu Lw Lx Ly Ma Mb Mc Md Mh Mi Mm Mn Mp Mt Mx Mz Nd Nf Ng Ni Nm Nn Ns Nv Oe Og Oh Oi Ok Om On Oy Pa Pb Pc Pg Po Qa Qb Qc) Ni(Et Fr Hq Hu Hv Hx Io Ip Iq Iv Jg Jh Jn Jr Js Li Lu Lx Ly Lz Ma Mc Md Mh Mm Mn Mt Mu Mx My Nd Nf Ng Nn No Ns Nt Nx Ny Om On Oy Pa Pb Pd Pe Pf Po Qa Qb Qe) Of(Hr Hw Ih Ij In Io Iq Ir Jl Jm Jn Jq Jr Js Li Lz Mb Mc Me Mh Mj Mk Mn Mt Mu Mv Mw Mx My Na Nc Nd Ne Ng Nh Ny Oe Og Om On Oz Pa Pb Pe Pf Qa Qe) Iv(Hu Hv Hx Ij Im Ip Jg Jh Lh Lw Lx Ly Lz Mb Mc Md Mi Mm Mn Mt Mx Mz Nd Ne Nf Ng Nm Ns Nv Nx Oe Og Oi Ok Om On Oz Pa Pb Pd Pf Po Qb Qe) Mz(Et Hq Hu Hv Hw Im In Ip Jg Jh Jl Jm Js Lu Lx Ly Lz Mb Mc Md Mh Mj Mm Mx Nd Nk Nm Nn Ns Nv Nx Og Oh Oi Om Pa Pc Pf Pg Po Qa Qb) Ip(Et Hq Hr Hu Hv Hx Il In Jl Jm Jn Jr Js Lu Lx Ly Md Mi Mm Mt Mx Nd Nf Ng Nk Nv Ny Oe Og Oi Ok Oy Pa Pb Po Qa Qb Qe) Md(Hq Hr Hv Hw Im Iq Jl Jm Jn Jr Js Lx Ly Mc Mh Mn Mt Mx Nd Ne Nf Ng Nk Ns Ny Oe Og Oi Oy Pa Pb Pd Pf Qa Qb) Hv(Et Hq Hr Hu Hx Im Jm Jn Jr Js Lu Lw Ly Lz Mc Mh Mm Mt Mx Nd Nf Ng Nk Nm Ns Oe Og Oi Oy Oz Pb Qa Qb) Oz(Fr Hw Hx Ii In Is Iu Jg Jk Jl Jn Jr Js Lh Mb Mi Mq Mr Mw Nd Nf Nl No Nr Nt Nv Ok On Pb Pc Pg Po) Og(Et Hu Hx Il In Jg Jl Js Jt Lw Mi Mw Mx Nd Nf Nk Nm Nr Ns Nv Ok Om On Oy Pa Pe Po Qb Qe) Hu(Et Fr Hq Hx Ji Jm Js Lx Ly Mp Mt Mx Nd Nf Ng Nk Nm Nn Ns Oe Oh Ok On Oy Pc Qb Qe) Hx(Et Hq Hr Ii Il Im Iq Jn Lw Lz Mi Mr Mt Mw Mx Nf Ng Ok Pb Qa Qb) Nk(Et Fr Hq Il Ji Jm Js Lw Lx Ly Mm Mt Nm Oe Oi Ok Oy Qa Qb Qe) Ns(Hq Js Jt Lu Lw Lx Mt Mx Nd Nf Ng Nm Oe Oi Ok Oy Pa Qb) Nj(Hw Ij In Ir Jq Lz Mb Me Mg Mh Mj My Na Nl Nt Om) Nf(Hq Im Lh Ly Mi Mp Mt Nd Nn Nv Oh Om On Po Qb) Oi(Et Il Jg Lw Lx Mi Mm Mp Nm Nv Oh Ok On Qb) Mi(Fr Hq Hr Ji Li Mh Mn Mx Oy Pd Pf) Im(Et Js Lh Me Mk Mx Nd Ng Nv Oe Pg) On(Hq Hr Jt Mr Mw Ng Oy Pb Pc Qa Qb) Mt(Jg Lw Lx Lz Mm Nm Nt Nv Ok Po) Nu(Is Iu Jk Jq Mg Na Nl Nq Nt) Ii(Iu Jl Lh Lz Mr Nr Nv Ok Pa) Nd(Ik Il Js Lx Lz Mx Oy Qb) Pf(Ih In Jo Lz Mg Mj Na Nt) Ng(Jg Mg Mm Mp Mw Nm Qb) Il(Ih Mx Nl Pg Qb Qe) Lx(Hq Jn Mx Oe Qb) Ik(Is Li Mb Nh Oe) Po(Hq Mx Qa Qb) Nm(In Mg Mp Nt) Ml(Ji Jq Jt Ne) Mm(In Jn Mw Nq) Ok(Jt Mr Mw Pg) Hr(Jl Pa Pe) Jo(Is Mb Mj) Lw(Pg Qb) Lz(Jl Pa) Mp(Nq Pc) Ms(Ij Qc) Jn(Nt Nv) HqNv InQb JlPb OyPg} Lv{Nc(Fp Hq Hr Hu Ih Ii Ik Io It Iv Jl Js Jt Lh Lj Lu Lz Mc Md Me Mg Mh Mj Mk Mn Mq Mr Mt Mu Mv Mw Mx My Na Nb Ne Nf Ng Nh Nr Ns Nx Of Oh Oy

Figure 37 Continued

Og Pb) On(Mb My Nx Og Pc Pz) Nm(Ji Lw Mg) Mp(Nf Ng Ni) Pz(Iv Nt Qa) Og(Iv Qa Qe) Jt(Ii Nn) Of(Mw Pa) Oh(Is Lw) MaNi MgNg QaPb} aX{Dc(aE aG aH aK Al aM AN aQ aR aV Aw aY Ba BB bE bF Bg bJ bM bN bP bR bZ cA cC cF cG CH cI cK cN Cp cQ cR cS cV cW cX cY dA Dd dE dG dH Dk dN) Ax(Ad AF aG aH aK Al aM aN aO Ap AR aW Ba Bb bC bE BG bI bJ BN bP bS bU bX bZ cF cG Ch cI cL Co cP cQ Cu CV cW cY Db dE dG dJ Dk dM) Cq(AD aG aK aM AO Ap aQ aS aU AW Ba bF bG bJ bL bP bR bS bU bX bZ cA cC cF cG cH cL cM cN cQ cR Cs Cv cW cY Db dC dE dF DG DK dL Fr) Dd(aF aG aK Al Ao Ap aQ AR AW Ba bC bG bH bI bS bU bX bZ cG cM cN Co cP cR Cs cY dF dG dJ Dk dL dM Fr) cX(aE aF aG Al An AS AW Bb bH bP cC cF Cp Cs Cv cW cZ dA dB De dF dG dN Fr) dD(aC Af aG Aj An aR Aw bE Bg bI Bn Bo cD cE Ch cI cN cP Cu DB dC dG dH Di fR) aI(aC AD Ao Ap ArY aZ Bc bH bO cC cE Co CT Cv Cw dB De dF dH DI FR) bO(aL aM Ap Ar Ba Bb Bc Bg bP bS cJ Co Cs Ct Cv Cw cY dB DE dF DI FR) cT(AD aF aH Ap Ar aV Aw aY aZ Ba Bg bU bX Ch Co Cs Cv Cw dB dC De Dl Fr) aO(aC aE aG aS aW aY bG bI bS bZ cD cF cH cI cL cP cY dB dE dF dJ) cZ(Al As aV Aw aY aZ Bb bI Bn Bo bU cC cD cE cI cN Cu dE dF DG Di) bL(aC aG aN aY bE bF bJ bN bP bS bU cD cE cF cL Cp cR Db dC dF dH) bM(aF aG aH aQ aZ bC bF bI bJ bR bS bU bW cD cI cL Cp cR cW dH dN) dM(aK aN aQ aR As aU aV aW bC bG bJ bS bW cB cJ cR Cx dE dF dJ dK) Cu(aG aH aM aS aU aV Aw bB Bg bI bP bR cB cD cE cI dB dC Di dK) Di(aD aE Af aG aH Aj Al AN bE bF Bn cE Cp cV DB dF Dg) aC(Ad Af Aj An Ao aZ Bc Bg Bn Bo Cs Ct Cv Db De Dg Dk Dl Fr) aZ(aG aL aQ Aw Ba Bo cC cF Ch Cp Cs DB dF Dg Dk) dF(Aj aU aY bF bJ bP bR cE cL cY dB dC dE Dg dH) Cp(aD Al aS aV aY bE Bg Bo cE CH dB dE) aE(Aj aK aQ aS aW bE bN cH cL cW dE dG dN) bG(aG aQ aW aY bI bJ bU bV cE cR dA) dC(Af Aj aM AN Bb BN Bo dB dE) As(Al aN Ar aV aY bE Bo cG CS) Aj(aG aH Al Bb cG cS cV Cw) aL(Ao bV cJ cS cV dI dJ fR) aS(aG Al aN aQ bJ bN bP cY) Cx(bV cO cV dI Dl FR) Dk(Ad bQ bV cE dB Dg dI) dH(Aw Bc Bn Ch Db Dg dJ) Af(Aw Bn cG cS dB) Bb(aH Cv dB Dg) cK(Al Bn Ch Cv) aY(An Aw fR) Al(bQ bV) Dg(aG cG) bP(bS dB) cH(aM Ch) AwBn BcdI DbdB aGdJ aUaV bRbS cCdE} Jj{Jk(Et Fp Hq Hr Hu Hw Ih Ii Ik Il Im Io Ir It Iu Iv Jg Jh Jl Jm Jo Jq Jr Js Jt Lh Li Lj Lu Lw Ly Lz Ma Mb Mc Md Me Mf Mg Mh Mj Mk Mm Mn Mp Mq Mr Mt Mu Mv Mx My Na Nc Nd Ne Nf Ng Nk Nm Nn No Nq Nr Ns Nt Nv Nx Ny Of Oh Oi Ok Om On Oy Pa Pb Pc Pd Pf Pz Qa Qc Qe) Qa(Et Fp Hq Hr Hw Ih Ii Ik Il Im Io Iq Iu Iv Jg Jh Jl Jm Jn Jo Jq Js Li Lj Lu Lw Ly Lz Ma Mb Mc Md Mg Mh Mj Mk Mp Mq Mr Mt Mu Mw Mx My Na Nd Ne Nf Ng Nh Nj Nk Nm Nn No Nq Nr Ns Nt Nv Nx Ny Of Og Oh Oi Ok Om On Oy Oz Pa Pb Pc Pd Pf Pz Qb Qc Qe) Hw(Et Fp Hq Hx Ih Il Io Ir It Iu Jh Jl Jm Jq Js Li Lj Lu Ly Mb Mc Md Mf Mn Mu Na Nd Nh Ni Nn No Nr Ns Nv Nx Ny Oe Of Oh On Oy Oz Pa Pb Pd Pf Pg Qb Qe) Im(Fp Hq Hr Io Ir It Jg Jh Ji Jm Lj Lu Lx Lz Ma Mb Mc Mh Mk Mq Mu My Mz Nd Ne Nh Nl Nq Nv Oe Oh On Oy Oz Pb Pc Pd Pf Pz Qb) In(Hr Hu Hx Ih Iq Ir Is Iv Jg Ji Jl Jq Lw Mg Mk Mn Mq Mt Mw My Nd Nm No Nq Nr Nt Nx Oe Og Oh Pd Pf Pz Qe) Ip(Et Ih Ii Ik Iq Is Iu Iv Jh Ji Jq Jt Li Md Mj Ml Mn Mp My Nd Ne Nh Ni Nt Ny Ok Om Pa Qb Qe) Pg(Hx Ii Il It Jl Jn Jo Jr Js Mb Me Mj Mn Mt Mv Mw Na Nc Ne Nh Nk Nl Nr Nt Oh Oi Om Pa Pd Pf) Lx(Ih Ii Ir Iv Ji Jl Jr Jt Lh Ma Me Mg Mj Mk Mr Mv My Mz Ni Nl Nn Nq Nr Nt Oi Pa Pd) Hx(Et Hr Hv Ik Ir Iu Jh Lh Ma Mk Mm Mz Nf Nn Nv Of Pb Qe) Il(Fr Ij Iu Iv Jg Jh Ji Jq Ma Mg Mm Mp Mz Nb Nt Ny Om) Mz(Hv Ik Is Iu Iv Jl Lh Li Mk Ml Mp Nb Oe) Hu(Et Ih Iq Is Jm Js Lw Mm Mp Nv Ny Om Qb) Li(Hv Jl Lh Mj Ml Nb Ne Ni Nk Oi On Qb) Ij(Iq Ir Jm Jr Mj Mt Nc Ni Nk Nl Nt) Nv(Hv Iu Iv Jt Me Ml Mm Mp Nb Nk Oi) Jl(Hr Ji Ma Mk Mm Mp Nm Oe Of Og) Nb(Et Ir Is Jq Lh Ny Om Qb) Lh(Hv Ir Me Mk Ne Oi Qb) On(Hv Iu Lz Mh My Nj Nn) Ml(Ir Is Iv Mk Qe) Pe(Is Ms Nk Nl Nt) Nh(Iv Nt Om) Ir(Hv Mp Oe) Qe(Jg Ok Om) Et(Ne Nk) Ms(Ih Po) MjMm MkOk MpJm NkOm HvNy IsOe} cS{bM(aC Ad aH Ao aU aV aW aY aZ Ba Bb BC bI bJ Bn bQ bS bU bV bW bX bZ cA cC cG cI cJ cK cL cM cN Co cQ cR Ct CV CW dA dE dG) Cx(Af aK aQ aU aY Ba Bc bF bG bI bJ bL bN bQ bR bS bV bW bZ cC cF cH cI cL cM cN CQ cR Cs Cv CW dA dE Dg dK dN Fr) Di(aD aG aH Al An Ao aS Aw bB bF BG Bn Bo bQ cB cD cE cK cL Co Cp Cq Db DC dF Dg dH Dk dM) Af(Ad aK aM Ap aQ Ar aU aV aY bH bJ bL bN bR bW cC cI CP CQ Ct cX Dc De Dl dN FR) aL(aI aR aS aZ bI bL bN bQ bU bV bW cB cD cI cJ cK cN cP cQ cV cW dA dD dG dI fR) bO(aG aI Al aM An aU aZ bL cJ Co Cp Cs Ct Cu Cv cY cZ DB dD dF Dg Dk Dl FR) As(aD aE aG aM Ao Ap aV aY Ba bB Bg bH bI bZ cA cG cP cQ CV cW dA dI dN fR) dM(Ad aG aH aO aS Aw aY aZ bB bF bQ bU bZ cH cI cJ cP cZ dA dE DG dI dL) Aw(aC aE aH An aS aV BB bE BG Bo bP bQ cD cK cL cZ DB dF dH) cT(aI aM An Ao Ap Ar Ba bF Bg bJ bL bS bW Co Cp Cs Cw Db De dF Dl fR) Ax(aD aE aG Ap aR aU aV aY Bb bF cA cC cF cG cN cR Cw dA DE dH) cX(aG aI aM AO BG Bo bP bQ bS cB cG Ch Co Cp CQ Ct Dk fR) Aj(aF aK Ao Ap aQ AR bC bH bN bV cI cM Co Ct cY dI dJ dN fR) Bb(aD aE aH Bg Bo bP bQ bR bU cD Ch cL CQ Ct cZ Db dF dL) aI(AD aH Al aM Ap Ar aU Ba bF bP cE Cq Cw dC DE Dg Dk) Ch(aD aE aH aS bB Bc bE bG bP bR cK cZ DD dF) aE(aZ Bc BG Bn Bo Co cZ Db Dd dE dF Fr) Bc(Ap bB bP cK Cq cZ dA dC dG dK dL) Dd(Bo bQ bR bU cH cK cL cR cZ dB dF) dB(aM An Ao Ap Ar Bg Bn Co Cs Dk) Ao(aH aS bB bE cB cG cZ dF) aZ(aG aQ bL bX cC dF Dk Fr) dD(Ba Bo cE Cp cR Ct dE Dk) cJ(Al Ar Bg Cs Cu Cv Db) cE(bG Bo bQ cG Cp) cZ(Ad aM Bg Cv Db) Bn(bB bE cB Dc) dH(Cp dF FR) Dc(aD Ct dE) Dg(cG dF Fr) Dk(Bg cD dK) Ad(Ba Cp) Bo(aC dC) Co(aH Cp) aS(Bg Cv) bR(bG bS) AnaD ArcB CtaC DbdE bFdF} cJ{Fr(aF aH aK aM AN Ao aQ Ar aU Aw aY Ba bB BC bI bJ bL bN bP bQ bR bU bW bZ cC cD cG cH cK cL cM cN cP Cq cR Cs Cu Cv CW cY Db DE dF dG dH dI dJ Dk DL dM dN) Di(aE aF aH aI aK aM An aO aQ aS aU Aw aY bB bH bI bJ bN bP bQ bR bW bX cB cC cI cK cM cN Co CP CQ Ct Cw cY cZ dA DD De DG dH dI dJ DL dN) Dc(aD aF aG aL Ap AR aU Aw Ax Bb bC bF Bg bH bL bM bZ cC cD cF cG Ch cI cO Cp Cq cR Ct CV cY cZ DB dC De Dk dM dN) Cx(aD Af aI Aj aK aL aM An AO As aY bB bE bF bG bH bJ Bn Bo bS bW cE cF Ch cI cL cM cN cO cP cV cW cY dA dG dH dL) Bc(AF aG aI aK aL aM Ap aU Ax Ba Bb bE bF Bg bJ bL bM bN bR bU bV bW cC cF cG cK cR Cs cV cY dC Dd DE dG dH) Bb(Ad aG aN aR As Aw bF Bg bH bJ bL Bo bZ cD cF cG Ch cI cO cP cQ Cs cT cV dB Dd dF Dg dK Dl dM) Cu(aC aF aG aH Al aM Ap aS aU Aw Ba bB bC bE bG bI bU cB cH cI Cp cQ Cs Cv cZ DD dF dL dN fR) Ax(AD aG Aj aK Ba bB bC bJ bL bM Bn bP bV bW cC cD Cp cR Cs cV Cw cX cY dC De dJ dN fR) Ap(Af Al AN Ar aS bL bM Bn cE Ch Co Cs cX dB dE dF Dk dM) Bn(aG AL Ar bC bL bO bQ cO Cp Cs Cw dC Dd dE dG dK fR) dE(Ad Al An Ao As aZ bO Ch Cq Cs Cw cX dC De Dl dM) Aj(Al Ar bJ bL bV bZ cO cX Dd dF dI dK dM fR) dM(Af aG aM As Aw Bo cB cE cR cX dB De) bO(Af Ar aZ bM Cp Cq Cs Cw cX Dk) Aw(aL Ar aV bF bM Cs cV cX dB) As(Ar aV bL bS bW Cw dF dI) Ba(aL aV bF Bg bM Bo dB Dk) Ar(aV cB cE cG Cp dC) Bo(Al bC cG cT Dd dK) cX(Al aM aZ Cp cR Cs) Af(bC cT dI fR) Cs(aV bJ cG Dc) Dk(aV cB Cp dB) bV(An Ch Db Dl) Al(aV dB dK) cE(cG Cp fR) Dd(Ad bJ) bC(Ch Ct) bM(Cp dN) BgcG aOaZ bFbQ} Cx{Cw(aD aE aF aG aH aI An AO Ar aS Aw Ax Ba BB Bc bF Bg bI bM BN Bo bV cC cD cG Ch cK cM Co Cp Cq Cs Ct Cv cX cY DB Dc DD dF Dg DK FR) Aw(aD Af aG aH aI Aj aK An Ao Ap aS Ba bH bL BN bP bQ bU bW bZ cD cK cL cM CO CP Cq Cv cW cX DB Dc DE dG dH Dl Dl) cG(aE AF aG aK Al An aO aQ AR aW BB Bc bH bL BN bX CP cQ cR cY dA Db dG Dl dM FR) Cu(aF Aj aL AN aS aW Ax bI bL bM bN bP bS cF cH cI cM CO Cq Ct Cv cX Db Dc Dg dH Dl dM) dF(aD Af aK aM As aV Ax BB bG bH bL bN bR bW cA cB cD cF cK cM cR cY Dd dE dH dI Fr) Di(aD aH aI aN aO Ap As aV bB bF bV bZ Cp Cq cR Cv DE dG dI) Dd(aG aL aO Ap aU aZ bB bM Bo bV bZ cC dB dC DE dJ dN) Fr(aE aG aH aI aV Ax bB bC bF bL Bo cD cE Cp cX Db Dc dD) Ap(aG Al An aS Bb bL Bo bV Cq Cs DB Dc dD dM fR) aZ(aG Ao Ar Bb bO bQ bS bZ Co Cp cR Ct cY dB dG dL) Bb(aG aH aI Aj aO bQ bW cM Cq cR cW dD dI dK) Ba(aI aL Bc bF Bg Bo bW cD cE Ch cM dC dK) Dc(aG aK bE Bo cO cR cY cZ dB DE dN fR) fR(Af aK aU aV bC bF Bn cB Cp dC De dH) Bc(aD Af aG aU aV bB bC Cp cT De) dE(aG Aj Ax Bo cB cC dB dC dD Dk) bC(aD aO aV Ax bB bL bO dK Dl) bV(Af As aV bB Bn cC Cp dB dC) bW(aD Al bM cB cF Cq Cv cX dD) dK(aV bL bP bS cA cP cT dG) bO(aG Al Bn Cp Cq cT De) Al(aU bB Bo cD dB) De(bL bP Cs dC Dk) aV(Bn bQ cT dC dI) Cq(bM cC cR Cv) cT(aG cO cR cY) dM(cB cD dB dC) Cp(cR dC) aL(aU dI)

Figure 37 Continued

Nt(Ni Qe) Lw(Hv Hw) Is(Iv Jr) MmIl JiNv JlOz} cE{bQ(aG aO bJ bL bM cB cD cV dE dF fR) dF(Ap bL dC DE) fR(cC dC) AdBa ApdD DecT} Lw{Mb(Hv Ii Iu Jl) Mm(Jl Li Nt Nv) Ni(Iu Nn Nt) Ny(Mu Mw Pb) Il(Ii It) NmJl MwJk IuOh} dE{Dc(aF aU aV cC cD dC) cC(dC dD dF) Cp(Bc Ch) cB(bV cT) dC(dF dM) aUdM bMcT} Ng{Iu(Hr Jh Md Nm Ns Nt Ny) Mg(Jg Jk Nt) Nn(Nb Ny) MmIj MwMy} Pb{Ny(Fp Hq Ik Jh Mc Mq Pc) Pa(Jh Nm Nn) Qa(It Ns) NmNb HvNv} dB{dM(aG aU cM cR dN) Bc(aD aU cD) bV(Bn cC) AfBa DcdC bFbQ bScC} Ap{Dg(aD aS Ba bI dD) cT(Bc Bn Ch Ct Dk) AfdD ChaC} Ok{Il(Mb Oz Pz) Nn(Mm Oh) Ii(Jl Mj) Jk(Oz Pf) HrHw} As{aU(Bc bS dF) Cp(Ar bV) DdbZ DebV} Nn{Mz(Mg Mm Oh) Nf(Jr Ny) MfJr MmQa} Ad{Dc(bE bZ Cw cY) BaCp BnCw} Nm{Iu(Ni Ns) NtMz MbHv NlPa JiJl} Is{Mb(Iv Jr Js) It(Jr Js) MdIr} Mm{EtNv MgJt MzNi IlOy JlOh} Nf{Qa(Et It Md Ns) MgJt} Ji{Mb(Il Jk) NsNe IiIl ItPa} dC{dM(aU cB) BndF BoDc bMdN} Af{Ba(bV dF Dk) DedF} cT{cC(bL cO fR) bMdN} Bn{bV(aU bB) BaDg} Ii{Ij(Iu Lh) MzIu} bF{bQ(aO bM cV)} cB{dM(aG cM) bRbS} aU{DdaK aDdM} NsHwQa NtMgIu MaMzNi MuNyPc

Unconstrained panels with 2 analytes, where 1.0E-7 >= 'AUC p-value' > 0. Contains 111 panels of 14,763 total panels evaluated. : cU(aA aD aE aG aI aJ aL aO AP As Aw BA BB bF bH bL bO bW bZ cE cM cN Cp cS cT cW CX dB dC Dd dE Di dK dM fR) Lv(aA Et Hx Im Iq Ir Is Ji Jj Jl Jp Jq Jt Li Lx Mi Mm Mz Nd Nm Nu Nv Nw Oe Ok On Pe Po Qa Qd Qe) Mi(aA Hu Jp Mg Ms Ng Ni Og Oh Pd) aA(aG aX bC bW cJ cS Cx dE dK) aP(aD aL aX bR Cx dG dH dK dL) Ms(Ji Jt Ok On) Qd(Ik Jj Pz) bA(bW cS De) Ax(Aw dK) dKdM Unconstrained panels with 2 analytes, where 1.0E-6 >= 'AUC p-value' > 1.0E-7. Contains 149 panels of 14,763 total panels evaluated. : cU(aH aK AI aM aN aQ aS aU aV aW AX aY aZ bC Bg bJ bM Bn bQ bR bU bV bX cA cC cD cG cH cI cJ cL cO CQ Cs cV Cw cY cZ dD dH dI dN Fr) Lv(Fr Hv Hw Ih Ij Il In Ip Iu Iv Jh Jk Jn Jr Lw Ly Me Ml Mp Mr Ni Nj Nk Nl No Nr Nt Ny Om Pg Qb Qc) aP(aE aI aZ bA bO bP cB cE cF cJ cN cX dB dC dD) aA(aM Ap aU Aw aZ bO cG cX dB dC De Hu Ip Mp) Qd(Jo Jp Ml Ms Nj Nu) aX(aJ bA cT Cx cZ dD) On(Jp Mb Mm Nj Pz) Mi(Mm Nq Of Oi) bA(Ap bC dE Fr) Jj(Ij Pe Po) Jp(Im Mp Nu) cS(Af Aj Ax) dK(aJ Dk) ApaL CucJ CxcG NuMz LwHu NjNv aZdN Unconstrained panels with 2 analytes, where 1.0E-5 >= 'AUC p-value' > 1.0E-6. Contains 270 panels of 14,763 total panels evaluated. : aP(aA AF aG aH aM aQ As aU aV AW aY bB bC bF bG bJ bM bN bQ bU bV bW bX bZ cA cC cD cH cI cL cP cR cS cT cW cY dA dE DI) Lv(Hq Hr Hu Ii Ik It Jg Jm Js Lh Lj Ma Mb Md Mf Mj Mk Mn Mq Mt Mv Mw Mx My Na Nb Nc Nf Nn Nq Ns Nx Og Oh Oi Oy Oz Pa Pc Pf) cU(aC Ad Af Aj An Ao AR Bc bE bG bI bN Bo bP bS cF Ch cK Co cP cR Cv dA Db Dc De dF Dg Dk DL) aA(aD aF aL aR aW bE bJ bZ cB cD cL cM cO cR cV dD DI Fr Iu Jp Ma Nj Nu Oe Po Qd) Jp(Hx Ij Il In Ip Iu Ji Lw Ma Mz Ne Nm Nn Nq Oe Pe Pg Po) Mi(It Jl Ml Mr Mv Nf Nh Nk No Nu Pa Pz Qc) Qd(Fp Hv Ip It Iv Lj Md Mf Mz Nb Ni Nw Of) aJ(aD aL aZ bA bM bO cB cJ cS Cx dC dG) bA(aU bJ cC cR CX dC Di dK) Nw(Ij In Ms Nj Nk Nu Oe Pe) Nu(Hx Ip Is On Po Qa) aX(Ax bG bM Cq Dd dM) Im(Jj Ni Nj Nk Nl) Cu(Ad bO Cx dE) Fr(aL As cJ cT) Jj(Hw Jk Pg Qa) cS(aL As bM Cx) Po(Ml Of Og) Lx(Hq Jm Pb) On(Ml Of Pb) Pe(Jo Nj Pf) Nm(Hu Ms) cG(cE cX) AjBa BcdK DicJ LwPg MlNy MsMz HuOk Unconstrained panels with 2 analytes, where 1.0E-4 >= 'AUC p-value' > 1.0E-5. Contains 638 panels of 14,763 total panels evaluated. : Qd(Et Fr Hq Hr Hu Hw Hx Ih Ii Ij Il Im In Io Iq Ir Iu Jg Jh Ji Jk Jl Jm Jn Jq Jr Js Jt Lh Li Lu Lw Lx Ly Lz Ma Mb Mc Me Mg Mh Mi Mj Mk Mm Mn Mp Mq Mr Mt Mu Mv Mw Mx My Na Nc Nd Ne Nf Ng Nh Nk Nl Nm Nn No Nq Nr Ns Nt Nv Nx Ny Oe Og Oh Oi Ok Om On Oy Oz Pa Pb Pc Pd Pe Pf Pg Po Qa Qb Qc Qe) aA(aC aE Af aH aI aJ aK aN aO aQ aS aV aY BA bB bF bG bH bL bM BN bR bX cA cC cE cF cH cI cK cN cP cT cW cY dA dF dG dH dL fR Hv Hx Ij In Iv Jg Jt Lh Lw Lx Mg Mk Ml Mq Mu Mv Mz Nb Nk Nm Nn Nq Nt Nw Og Ok On Pe Pg) Jp(Fp Fr Hr Hv Hw Ii Ir Is Iv Jg Jj Jk Jl Jq Jr Jt Lh Li Lu Lx Mg Mj Ml Mm Mq Ms Mw My Nb Ng Nh Nk No Nr Ns Nt Nv Nw Og Oh Oi Ok Om Pa Pc Qa Qb Qe) aP(aC Ad AJ aK AN aO Ap aR aS Ax Bb bE Bg bH bI bL Bn Bo bS cG cK cM cO CQ cV cZ De dF Dg dJ dM dN) aJ(aE aG aI aM As aU Aw bB bC bJ bN bP bQ bR cC cD cE cF cG cM cR cT cV cX dB dD dE dH Di dL) Lx(Fp Hx Jh Jj Jn Jr Lj Lu Lw Mc Md Me Ml Mp Mq Mz Nb Nf Nj Nk Nl Nu Nw Ny Oe Of Pa Pc Pf) Mi(Fp Fr Hv Im Ip Iq Jn Jo Jq Js Lz Mb Mf Mn Mt Mu Mw Nb Ne Nj Nw Nx Oe Om On Oz Pe Pf) Po(Fp Hq Hr Ii Ik Ip Ji Jm Jo Jr Lj Lw Mf My Mz Nf Ng Nj Nl Nm Nw Oe Oi Oy Pb Pf) bA(aC aF aG aI aM aS Aw aZ bE bL bM Bn bO bZ cB cE cF cG cJ cO cT cV dN) Nw(Hu Hv Hw Hx Il Ip Iv Jj Jk Mk Ml Mz Nb Ne Nh Ni Oi On Pg Qa) Nu(Ij Im Ir Ji Jj Jl Jq Jr Lw Ly Ml Mp Nk Nm Oe Oi Pe Pg) On(Hv Hw Hx Ii Im Ip Lz Mh Mn My Ni Nk Nl Oe Og Pc Pe Pg) Lv(Fp Io Jo Lu Lz Mc Mg Mh Ms Mu Ne Ng Nh Of Pb Pd Pz) aX(aE Af Aj aO AS aZ bL Bo Cp Cu cX Dc dF Dg Di dJ) Aw(AL Ar aZ Bn bO Ch cS Cx Dk dM Fr) Pe(Et Ii Jg Lj Lw Ml Mm Nm Oe Og Ok Oz) Jj(Hx In Ip Ir Is Jl Lh Mz Nv) Pg(Im Ji Jo Mm Nj Nm Oe Ok Oz) Fr(Aj Cx dB Dg dK Ms Nj Nk) Mp(Hu Hx Im Jr Ml Nf Ny Oi) Oe(Hx Iv Jl Mz Nt Nv Ok) cS(Bb Bc Ch cT Dd Di dM) aL(bC bE bW Dc dK dN) aZ(aO bL bQ dE Di dK) cJ(Ax Ba Bb Bc Cx Dc) Nj(Jl Mm Mz Nt Qa) Hx(Hr Im Lw Nm Og) cG(Af bF Bn bO Di) cU(aF cB Ct dG dJ) Cx(Ba Cw dF fR) Ms(Ir Is Iu Qa) Ny(Hq Lw Mw Pb) bC(As Bb bM dM) Aj(Ap bW Cw) Cu(aG cX dB) Mz(Hu Ip Ml) Oi(Iu Nq Nt) Ap(aI cT) Ax(aU Di) Lw(Hv Hw) Nk(Et Mm) Im(Nb Ok) Qa(Ip Ml) bW(bM cT) dE(aI Dc) CwbO DibV NnJr HuJi IjJo JgOg bQcE dFdK Unconstrained panels with 2 analytes, where 1.0E-3 >= 'AUC p-value' > 1.0E-4. Contains 1,862 panels of 14,763 total panels evaluated. : Cu(aA aC aD aE AF aH aI AJ aK AL aM AN AO AP aQ AR AS aU aV AW Ax aY aZ BA BB BC bE bF BG bH bI bJ bL bM BN Bo bP bQ bR bS bU bV bW bX bZ cA cB cC cD cE cF cG CH cI cK cL cM cN CO CP CQ cR CS CT cU CV CW cY cZ dA Db DC DD De dF DG dH DI dJ DK DL dM dN FR) aA(Aa Al An Ao As Ax Bb Bg bI Bo bP bQ bS bU bV Co Cp CQ Ct Cw cZ Db Dc Dd Dg dJ Dl dM dN Et Fp Hq Hr Hw Ih Ii Ik Il Im Io Iq Ir Is It Jh Ji Jj Jk Jl Jo Jq Jr Js Li Lj Lu Ly Lz Mb Mc Md Me Mf Mh Mj Mm Mn Mr Mt Mw Mx My Na Nc Nd Nf Ni Nl No Nr Ns Nv Nx Ny Of Oh Oi Om Oy Oz Pa Pb Pc Pd Pf Pz Qa Qe) Qa(Et Fp Fr Hq Hr Hu Hv Hw Hx Ii Ij Ik Im In Io Iq It Iu Iv Jg Jh Jl Jm Jn Jo Jq Jr Js Lh Li Lj Lu Lw Lx Ly Lz Ma Mc Md Me Mf Mh Mi Mj Mk Mm Mn Mp Mq Mr Mt Mu Mv Mw Mx Mz Na Nb Nc Nd Nf Ng Ni Nk Nm Nn No Nq Ns Nt Nv Nx Ny Oe Of Og Oh Oi Om On Oz Pa Pb Pc Pd Pe Pf Pg Po Pz Qb Qc Qe) Pe(Fp Fr Hq Hr Hu Hv Hw Hx Ih Ij Ik Il Im In Io Ip Iq Ir It Iu Iv Jh Ji Jk Jl Jm Jn Jq Jr Js Jt Lh Li Lu Lx Ly Lz Ma Mb Mc Md Me Mf Mg Mh Mj Mk Mn Mp Mq Mr Ms Mt Mu Mv Mw Mx My Mz Nb Nc Nd Ne Nf Ng Ni Nk Nl Nn No Nq Nr Ns Nt Nv Nx Ny Of Oh Oi Om Oy Pa Pb Pc Po Pz Qb Qc Qe) Nw(Et Fp Fr Hq Hr Ih Ii Ik Im Io Iq Ir Is It Iu Jg Jh Ji Jl Jm Jn Jo Jq Jr Js Jt Lh Li Lj Lu Lw Ly Lz Ma Mb Mc Md Me Mf Mg Mh Mj Mm Mn Mp Mq Mr Mt Mu Mv Mw Mx My Na Nc Nd Nf Ng Nl Nm Nn No Nq Nr Ns Nt Nv Nx Ny Of Og Oh Ok Om Oy Oz Pa Pb Pc Pd Pf Pz Qb Qc Qe) Mz(Et Fp Hq Hr Hv Hw Hx Ih Ii Ij Ik Im In Ir Is It Iu Iv Jg Jh Jk Jo Jq Jr Lh Li Lj Lu Lw Ly Ma Mb Mc Md Me Mf Mg Mh Mi Mj Mk Mm Mp Mq Mr Mt Mu Mw My Na Nb Nd Nf Ni Nk Nl Nm Nn Nq Nr Ns Nt Nv Ny Of Og Oh Oi Om On Oy Pa Pb Pc Pd Pg Qe) Po(Et Fr Hu Hv Hx Ih Ij Im In Io Iq Ir Is It Iu Iv Jg Jh Jk Jl Jn Jq Jt Lh Li Lu Lx Ly Lz Ma Mb Mc Md Me Mh Mj Mk Mm Mn Mp Mq Mr Mt Mu Mv Mw Mx Na Nb Nc Nd Nh Ni Nk Nn No Nq Nr Ns Nt Nv Nx Ny Oh Ok Om Oz Pa Pc Pd Pg Qb Qc Qe) Nu(Et Fp Fr Hq Hu Hv Hw Ih Ii Il In Io Iq It Iu Iv Jg Jh Jk Jn Jo Js Jt Lh Li Lj Ma Mb Md Mc Mf Mj Mk Mm Mn Mq Mr Mt Mv Mw Mx My Na Nb Nc Nd Ne Nf Ng Nh Ni Nj Nl Nn No Nq Nr Ns Nt Nv Nx Ny Of Og Oh Ok Om Oy Pa Pc Pz Qb Qc Qe) Lx(Et Hr Hu Hw Ii Ij Ik Il Im In Io Ip Iq Ir Is It Iu Iv Jg Ji Jk Jl Jo Jq Jt Lh Li Ly Lz Ma Mb Mf Mh Mj

Figure 37 Continued

Mk Mn Mr Mt Mu Mv Mw Mx My Na Nc Nd Ne Ng Ni Nm Nn No Nq Nr Ns Nt Nv Og Oh Oi Ok Om On Oy Oz Pd Pg Pz Qb Qc Qe) bA(aD aE Af aH aK aL AN aO aQ aR As aV aW aY Ba BB Bc bF BG bH bl bN Bo bP bQ bR bS bU bV bX cA cD CH cI cK cL cM cN Co CP cQ Ct cW cY cZ dA dB Dc DD dF DG dH dI dJ DL dM fR) On(Et Fp Fr Hq Hu Ih Ij Ik Il In Io Iq It Iu Iv Ji Jj Jk Jl Jm Jq Jr Js Jt Li Lj Lu Lw Ly Ma Mc Me Mf Mj Mk Mp Mq Mr Mt Mw Mx Na Nb Nd Nm Nn No Nq Nr Ns Nt Nx Oh Oi Ok Oy Pa Pd Pf Qc Qe) Nv(Fp Hq Hu Hv Hw Hx Ii Ij Il Im In Ip Iq It Iu Iv Jh Ji Jk Jl Jn Jq Js Jt Lj Lu Lw Ma Mb Md Me Mf Mj Mk Ml Mn Mp Mr Mt My Na Nb Nd Nf Ng Nm Nn Nq Nr Ns Nt Of Og Oi Om Pa Pb Qb Qe) aJ(aC AF aH aK aN aO Ap aQ aR aS aV aW Ax aY Ba bE bF bG bH bl bL Bn bS bU bV bW bX bZ cA cH cl cK cL cN cO CP cQ cW cY cZ dA De dF dI dJ dM dN Fr) cG(AD aG al Aj aL aM aO aQ As Aw Ax aZ Bb Bg bJ bL bM Bo bP bR bS bV bZ cC cD cF Ch cL Cp CQ cR cT cV cY dB DC dD dE dF Dg dH DK dM dN fR) Im(Fr Hr Hu Ii Ij Ik Io Ip Iq Ir Iu Jh Jk Jl Jt Lh Li Lw Lz Mb Mc Md Me Mf Mj Mk Ml Mq Mr Mw Mx Na Nc Nd Nf Ng Nm Nn Nr Ns Ny Of Og Oh Oz Pa Pc Qe) Jp(Et Hq Hu Ih Ik Io Iq It Jh Jm Jn Jo Js Lj Ly Lz Mb Mc Md Me Mf Mh Mk Mn Mr Mt Mu Mv Mx Na Nc Nd Nf Ni Nj Nl Nx Ny Of Oy Oz Pb Pd Pf Pz Qc) aX(Ad aG al AL aM An Ap Ar Aw Ba Bb Bc bE Bg Bn bO bP bS Ch cJ cR Cs Ct Cv DB dC Dk Dl FR) cS(aE aG aI Al aM An AO aZ BG bL Bn BO bQ Co Cp Cs Ct Cv cX cZ Db Dc dD dF Dg Dk Dl FR) Mi(Et Hr Ih Ii Ij In Io Ir Iu Jh Jj Jk Jm Li Lj Lu Lw Mc Mh Mk Mp Mq Mx My Nn Nr Nt Oy Pb Qb Qe) Ip(Et Fr Hv Hx Ij Ir Is Iu Iv Jg Ji Jk Jq Jt Li Lw Mp Nb Nd Nj Nk Nm No Nt Ok Om Pg) Ny(Iu Jh Jj Jr Ma Mb Mc Me Mf Mk Mq Mr Mt Mu Nf Ng Nj Nm Nn Nq Ns Oe Of Oh Pa Pc Pf) Aw(Af al Aj aN As aV Ba Bb BC bF Bg Bo bS bV cE cJ Cs cT cX Dc dD dF DI) Fr(aD Af aG al aP aZ Bg BO bV cB cD Ch Cq cX dC dD Di Hx Ij Ng Ni Oe Oi Pg) Li(Hw Hx Ij Il In Ir Jh Jj Jk Jq Mf Ml Nd Ne Nf Ng Nh Nj Nk Oe Og Oi Pa Pg Qb) aZ(aC aG al Ap Ba Bb bC bH bO bV bW bZ cC CO Cq cR cT Cv dC De dF fR) Hx(Et Hu Iu Jg Jh Ji Jo Jq Jt Ma Ml Mm Ms Nf Nj Nl Nn Nt Of Oi Ok Om) Nt(Hv Ij Ir Jj Jl Jo Lw Mf Ml Nd Ne Ng Nh Ni Nk Of Og Ok Pg Qb) Cx(aG Ap Bb BC Bn bQ bV bW Cp Cq cT DC Dd DE Di dK) Mp(Hq Ir Jh Jl Lu Lw Mf Ng Ni Nj Nk Og Pa Pb Pc Pd Pf Pg) aP(Al Ao Ar Ba Bc Ch Co Cp Cs Ct Cv Cw Db Dc Dd Dk Dl fR) Di(aG al AL As Ba bC bO bW Ch cT Cw DC dF dK dM) Pg(Et Ii Iu Iv Jg Jq Jt Ma Ml Ms Nl Of Og Oi Om Oy Pf) Nj(Et Hw Ij Ir Is Jg Ji Jk Jt Lh Mt Nd Nm Ok Om) cJ(Aj Al Ap Ar As Bn Bo Cp Cq Cs Cw Dd dE Dk dM) dK(aG al Al Ar bG bL bM bO bS bV Cs cX Dc dG fR) Ij(Et Jg Jh Jq Lw Ly Ma Ml Mm Nd Nm No Og Qc) Jl(Hr Ii Iu Jo Lw Ma Ml Ms Nm Of Og Oi Ok Oz) Jr(Iu Jh Lw Mc Ml Mq Mt Mw Nb Nm Nq Oe Pa Pb) dE(aG aL Ba bO cC Cp cT cX dC DD dF dM) Jj(Et Hv Ih Il Iv Jg Jm Jq Mk Om Qb Qe) Dc(Ad aG Ap aU aV bC BO bW cO dC) Ir(Et Hu Hv It Jh Jo Ml Mm Oe Og Om) Ok(Il Jk Mb Mk Ml Nb Ne Nk Og Pa Qe) Jt(Hu Ii Ml Nd Ng Oe Of Og Oi Pc) bV(As Ax Ba Bb Bn bQ cC Cp cR De) dC(al Bb Bc bO bW cO cX dF dM fR) Oe(Et Is Iu Jg Jn Lh Nb Nr Om) Ba(Ad al aL aV bO cX dB Dg) Cw(Ad al As Bg Bn Bo cE Db) Om(Hw Il In Ms Ne Nk Og Pa) fR(aD bC bO cC cE cM cV cX) Mm(Hu Hv Hw Il In Ni Oi) Nb(Hu Is Jh Ji Lw Ml Oi) Nm(Hv Hw Ii In Nr Pa) Nn(Hu Mf Nf Ng Ni Of) Is(Hv Jo Ml Of Og Qd) al(aC aM bC bQ cO De) bO(aG Ap Bb bQ bW cO) cT(Bb bC bM cO cX De) Iv(Jo Ml Nd Og Oi) bW(Ax bP Ch DD) Ap(Ax dD dF Dg) Et(Il In Ni Oi) Iu(Hu Mb Ng Of) Ji(Ni Nk Ns Oi) Jq(Hu Hw Mk Ms) bQ(bF cD cX dB) dM(aG aU cB dB) Bb(aG aL dN) Lw(Lh Nr Qe) Mw(Md Ml My) dF(aM cE cX) Ax(cR dN) Jg(Il Ng) Jh(Iq Pa) aL(aC bL) BoDd MaNk HuOh aGcX aObC bMdN

Unconstrained panels with 2 analytes, where 1.0E-2 >= 'AUC p-value' > 1.0E-3. Contains 3,579 panels of 14,763 total panels evaluated. : Fr(Ad aE aF aK Al aM AN AO Ap aQ Ar aU aV aW Ax aY Ba BB BC bF bl bL bM BN bP bQ bR bU bW bX bZ cC cE cF cG cI cK cM cN Co CP cQ cR Cs Ct CV CW cY dA Db Dc Dd dE dF dG dH Dk Dl dM dN fR) Hq Hr Hv Hw Ih Ii Il In Iq Ir Is It Iu Iv Jh Jj Jk Jl Jq Jr Js Jt Lh Li Lw Lx Mb Mc Me Mf Mh Mj Mk Ml Mp Mr Mx My Mz Nb Nc Nf Nl Nr Ns Nt Nv Ny Of Og Ok Oy Pa Pb Pf Qb Qe) Is(Et Fp Hq Hr Hu Hw Hx Ih Ii Ij Ik Il Im In Io Iq Ir Iu Iv Jg Ji Jj Jk Jl Jm Jn Jq Jr Js Jt Lh Li Lj Lu Lw Ly Ma Mb Mc Md Me Mf Mg Mh Mi Mj Mk Mm Mn Mp Mq Mr Mt Mu Mv Mw Mx My Na Nc Nd Ne Nf Ng Nh Ni Nk Nl Nm Nn No Nq Nr Ns Nt Nv Nx Ny Oh Oi Ok Om On Oy Oz Pa Pb Pc Pd Pe Pf Pg Pz Qa Qb Qc Qe) Ir(Fp Hq Hr Hw Hx Ih Ii Ij Ik Il In Io Iq Iu Iv Jg Ji Jk Jl Jm Jn Jq Jr Js Lh Lj Lu Lw Ly Lz Ma Mb Mc Md Me Mf Mg Mh Mj Mk Mn Mq Mr Mt Mu Mv Mw Mx My Na Nb Nc Nd Ne Nf Ng Nh Ni Nk Nl Nm Nn No Nq Nr Ns Nv Nx Ny Of Oh Oi Ok On Oy Oz Pa Pb Pc Pd Pf Pg Pz Qa Qb Qc Qe) Ba(aD aE AF aG aH aJ aK Al aM AN aO aQ AR AS aW Ax aY Bb bC bF Bg bH bl bJ bL bM BN Bo bP bQ bR bS bU bW bX cC cD cE cG cH cI cK cL cM cN Co CP CQ CS CT CV CW cY cZ dA Db DC DD dF dG dH dI dJ DK dL dM dN fR) Jq(Et Fp Hq Hv Ih Ii Ik Il Im In Io Iq It Iu Iv Jg Jh Jk Jl Jm Jn Jr Js Lh Lj Lu Lw Ly Ma Mc Md Me Mf Mg Mj Ml Mm Mn Mp Mq Mr Mt Mu Mv Mw Mx My Nb Nd Ne Ng Nh Ni Nj Nk Nm Nn No Nq Nr Ns Nt Nx Ny Oe Of Og Oh Oi Ok Om Oz Pa Pb Pc Pd Pf Pz Qb Qc Qe) Cw(aD aE AF aG aH aJ aK AL AN aO Ap aQ AR AS aU aV AW Ax aY aZ bA BB Bc bF bl bJ bL bM bN bP bQ bR bY bW bX cC cD cF cG CH cI cK cM cN cO CP CQ CS CT cV cW cX cY dA dB DC dD dE dF dG dH dJ DK DL dM) Et(Fp Hq Hr Hu Hv Hw Ih Ii Ik Im Iq It Iu Iv Jg Jh Ji Jk Jl Jm Jn Jo Jr Js Jt Lh Li Lj Lu Lw Ma Mb Mc Md Me Mf Mh Mj Mk Ml Mn Mp Mr Mt Mv Mw Mx My Nb Nc Nd Ne Nf Ng Nh Nl Nm Nn No Nq Nr Ns Nt Nv Nx Ny Of Og Oh Ok Om Oy Pa Pb Pd Pf Pz Qb Qe) fR(aC aE AF aG aH aI AJ aK AL aM aN aO aQ aR as aU aV AW Ax aY BB bE bF bG bH bl bJ bL bM BN bP bQ bR bV bW bX bZ cA cB cD cF cH cI cJ cK cL cN cO CP cQ cR cT cW cY cZ dA dB Dc DD DE dF dG dH Dl dJ dL dM dN) Nt(Fp Hq Hr Hu Hw Ih Ii Ik Il Im In Io Iq It Iu Iv Jg Jh Ji Jk Jm Jn Jr Js Jt Lh Li Lj Lu Ly Lz Ma Mb Mc Md Me Mg Mh Mj Mk Mm Mn Mp Mq Mr Ms Mt Mu Mv Mw Mx My Na Nb Nc Nf Nl Nm Nn No Nq Nr Ns Nx Ny Oh Om Oy Oz Pa Pb Pc Pd Pf Pz Qc Qe) Ij(Fp Hq Hr Hu Hv Hw Hx Ih Ii Ik Il In Io Iq It Iu Jk Jl Jm Jn Jr Js Lh Lj Lu Lz Mb Mc Md Me Mf Mg Mh Mj Mk Mn Mp Mq Mr Ms Mt Mu Mv Mw Mx My Na Nb Ne Nf Ng Nh Ni Nk Nl Nn Nq Nr Ns Nx Ny Oe Of Oh Oi Om Oy Oz Pa Pb Pc Pd Pf Pg Pz Qb) Jl(Fp Hq Hu Hv Hw Hx Ih Ik Il In Io Ip Iq It Iv Jg Jh Jk Jm Jn Jr Js Jt Lh Li Lj Lu Ly Lz Mb Mc Mf Mh Mi Mj Mk Mm Mn Mp Mq Mz Nb Nc Nd Nf Ng Ni Nk Nl Nn No Nq Nr Ns Nx Ny Oh Om Oy Pa Pc Pd Pf Pz Qb Qc Qe) Li(Fp Hq Hr Hu Hv Ih Ii Ik Io Iq It Iu Iv Jg Ji Jm Jn Jo Jr Js Jt Lh Lj Lu Lw Ly Lz Ma Mb Mc Md Me Mg Mh Mj Mk Mm Mn Mp Mq Mr Ms Mt Mu Mv Mw Mx My Na Nb Nc Ni Nl Nm Nn No Nq Nr Ns Nv Nx Ny Of Oh Ok Om Oy Oz Pb Pc Pd Pf Pz Qc Qe) Hx(Fp Hq Hv Hw Ih Ii Ik Il In Io Iq It Iv Jk Jm Jn Jr Js Lh Lj Lu Ly Lz Mb Mc Md Me Mf Mg Mh Mi Mj Mk Mn Mq Mr Mt Mu Mv Mw Mx My Na Nb Nc Nd Ne Ng Nh Ni Nk No Nq Nr Ns Nx Ny Oh Oy Oz Pa Pb Pc Pd Pf Pg Pz Qb Qc Qe) Jg(Hq Hr Hv Hw Ih Ii Ik Im In Io Iq It Iu Iv Ji Jk Jm Jo Jr Js Jt Lh Lj Lw Ly Ma Mb Mc Md Me Mf Mi Mj Mk Ml Mn Mp Mq Mr Ms Mt My Nb Nd Ne Nf Nh Nk Nl Nm Nn No Nq Nr Nv Nx Ny Of Oh Oi Ok Om Pa Pb Pc Pd Pf Pz Qb Qc) Dc(aC aD aE AF al AJ aK aL aM AN AO aQ AR AS aW Ax aZ BB Bc bE bF BG bH bJ bL BN bQ bR bV bZ cB cC cD cE cF cI cK cL cM Co Cq cR Cs CV cX cY cZ DB DD De dF DG dI dJ dL dN) Di(aD aE Af aH aK aM AN aO Ap aQ AR aU aV aY BB Bc bF Bg bJ bL bM Bn Bo bP bQ bS bU bZ cA cB cC cD cE cF cH cK cL cM cN cO CP CQ Cs Ct CV CW cX cY cZ DB DD DE DG dI Dk DL dN) Om(Fp Hq Hr Hu Hv Ih Ii Ik Im Io Iq It Iu Iv Jh Jk Jm Jo Jr Js Lh Lj Lu Lw Ly Ma Mb Mc Md Me Mf Mh Mj Mk Ml Mn Mp Mr Mt Mu Mw Mx My Nd Nf Ng Nh Ni Nl Nm Nn No Nq Nr Ns Nx Ny Of Oh Oi Oz Pb Pc Pd Pf Pz Qb Qc Qe) Pg(Fp Hr Hu Hv Ih Ik Il In Io Iq It Jh Jk Jm Jn Jr Js Lh Lj Lu Ly Lz Mb Mc Md Me Mf Mg Mh Mi Mj Mk Mn Mq Mr Mt Mu Mv Mw Mx My Na Nb Nc Nd Ne Nf Ng Nh Ni Nk Nn No Nq Nr Ns Nv Nx Ny Oh Pa Pb Pc Pd Pe Pz Qb Qc Qe) Aw(AD aE aF aG aH aK aM An AO Ap aQ aS aU aY bB bH bl bJ bL bM bN bP bQ bR bU bW bX bZ cA cB cC cD cF cH cl cK cL cM cN CO CP CQ cR Ct CV cW cY dA DB dC Dd DE DG dH dJ dK DL dN) Ip(Fp Hu Hw Ih Ii Il In Io Iq It Jh Jn Jo Jr Js Lh Lj Ly Lz

Figure 37 Continued

Ma Md Me Mf Mg Mj Mk Ml Mm Mn Mq Mr Ms Mt Mu Mv Mw Mx My Na Nc Nf Ni Nl Nn Nq Nr Nx Ny Oe Of Og Oh Oi Oz Pa Pd Pf Pz Qb Qc Qe) dE(aC aD aE AF Aj aM aN aO Ap aR aS aV aW AX BB bC bF bG bH bJ bL bM BN Bo bP bQ bS bU bV bW bZ cB cD cE cF cM cN cO cP CQ cR CS cV cW cZ dA dB dG dH dJ DK DL dN) Jh(Hq Hw Ih Ii Il Iu Iv Ji Jj Jk Jm Jn Js Jt Lh Lw Ly Lz Mb Mc Md Mf Mj Mk Ml Mn Mq Mr Ms Mt Mw Mx My Nd Ne Nf Ng Nh Ni Nj Nk Nm Nn No Nr Ns Oe Of Og Oh Oi Ok Pb Pc Pf Pz Qb Qc Qe) bQ(aD aE AF aG aH Aj aK aL aM aO aQ AS aV BB Bg bl bJ bL bM BN bP bR bU bX bZ cA cB cC cF cG cI cJ cK cL cM cN Cp cR cT cV cW cY dC dD dH dI dJ dK DL dM dN) dF(aC aD aE AF aG al aK AL aN aO aR As aU Ax aY BB bC bE bF Bg bJ bL bM BN BO bR bV bW cA cB cC cD cF cH cJ cK cM cO Cp Cq cR cT cV cW cY dB dD De dH dI dN) Jr(Hq Hr Hu Ih Ii Ik Il Im Iq It Jj Jk Jn Jo Lh Lu Lz Ma Mb Md Me Mf Mg Mi Mj Mk Mm Mr Ms Mu Mv Mx My Na Nd Nf Ng Ni Nj Nk Nl No Nr Ns Nv Nx Of Og Oh Oi Oy Oz Pc Pf Pz) Ok(Hq Hr Ih Ii Ik Iq Iu Iv Jj Jm Js Jt Lh Lj Ly Ma Mc Md Me Mf Mg Mh Mi Mj Mm Mn Mp Mq Mt Mu Mv Mw Mx My Na Nd Nf Nh Ni Nl Nm Nn No Nq Nr Ns Nv Nx Of Oi Oy Pb Pf Qb) cG(aC aE aF aH aK Al AN Ao Ap AR aS aU aV aW aX aY bB BC bG bH bl bN bU bX cA cB cH cI cJ cK cM cN CO cP CS Ct Cv cW cZ dA Db Dd De dG dl dJ DL) bV(aC AD aE Af aG aH al Aj AL aM An aO Ap aU bB bF BG bl bJ bL bM bN BO bP bR bW bZ cB cD cE cF cJ cL cM cO cT cV cX DB dC dD Dg Dk Dl dN) Nm(Fp Hq Ih Ik Il Io Iq It Iu Iv Ji Jk Jm Jn Js Lh Lj Lu Ly Mb Me Mf Mh Mi Mj Mk Ml Mn Mp Mr Mt Mw Mx My Nb Nd Nf Ng Ni Nk Nl No Oe Oi Oy Pf Qb Qc Qe) Mp(Fp Hr Hw Ii Io Iq It Iv Ji Jj Jk Jm Jn Js Jt Lj Mb Mc Md Me Mh Mj Mk Mm Mq Mr Mt Mu Mv Mw Mx Na Nb Nc Nl Nn No Nq Nr Ns Nx Oe Of Oh Oy Pz Qb Qc) Ny(Fp Hr Hu Hw Ih Ii Ik Il Io Iq It Iv Jk Jm Jn Jo Lh Lj Lu Ly Lz Md Mi Mj Mm Mn Ms Mv Mx My Na Nc Nd Ne Nh Ni Nk Nl No Nr Nv Og Oi On Oz Pd Pz) aZ(AD aE aH aM An Ao aQ AR aU aW aY bB Bc bE Bg bJ Bo bS cD cF Ch cJ cK cM cN Cp cQ Ct cV cW CX cY DB DD DG dH dl Dl dM) Jt(Fp Hq Hr Il Iq Iu Iv Jj Jk Jm Js Lh Lj Lu Lw Ma Mb Mc Mf Mh Mi Mj Mk Mm Mn Mt Mu Mw Mx Na Ne Nf Nh Nk Nn No Nr Ns Pa Pb Pf Qb Qc Qe) Iv(Hr Hu Hv Hw Ik Il Im In Iq Iu Ji Jk Lh Lj Lw Ly Ma Md Mf Mi Mj Mm Mn Mt Nb Ne Nf Ng Nh Ni Nj Nk No Ns Nx Of Pa Pb Qb Qc Qe) Jk(Hr Hv Hw In Iq Iu Ji Jo Js Lh Lj Lw Ly Ma Md Mf Mj Ml Mm Mr Ms Nb Nd Nf Ng Nk Nl Nn No Nq Ns Nx Oe Of Og Oh Oi Pb Qa Qc) aG(aC al AL aN aO Ap aR AS Ax aY bB BC bL bM bS bU bW bZ cC cE cJ cO CP cR Cs cT cW dA dB dC DD dG dl dL dN) cS(AD aH aK Ap aQ Ar aS aU aW bB bE bF bP bR bS cB cC cE cJ cK cL cM cN cO CQ cR cW cY dA dB dC De dH dl dJ dK dN) Im(Fp Hq Hv Hw Ih Il In It Ji Jm Jn Jo Js Lj Lu Ly Ma Mg Mh Mm Mn Ms Mt Mu Mv My Ne Nh No Nq Nx Oe Oi Oy Pb Pf Pz Qb) dK(aE Af Aj aM AN aO As aW aX BB bC bF BN Bo bP bR bW bZ cA cB cC cO CP cR cT cW cZ dA dB dC DD dJ Dl) Ji(Ih Ii Il Io Iq Iu Jj Jm Lh Lj Lu Ly Mb Mf Mj Mk Ml Mm Mt My Nd Ne Nf Ng Nh Nl No Nr Nx Oe Of Og Oy Pa Pb Qe) Nv(Hr Ih Ik Io Jm Jo Lh Ly Lz Mc Mg Mh Mi Mm Mq Ms Mu Mv Mw Mx Nc Ne Nh Ni Nk Nl No Nx Oh On Oy Oz Pc Pd Pf Pz Qc) Bb(aD aH al AJ Al aM aN aO Ap aR aV Ax bM Bn Bo bW bZ cB cE cF Ch cl cM cO CQ cR cV cW cX DB DD dI) No(Hr Hu Hv Hw Ik Il In Iq Iu Jj Ma Md Mk Ml Mt Mu Mz Nb Nd Ne Nf Ng Nh Nj Nk Nn Nq Ns Oe Of Og Oi Pa Qb) cJ(Ad Af al aL aM An AO Bg bL bM bO bS bW bZ Ch CO cR CT Cv cW cX DB dC De DG Dl dN) dM(aC aD aF al aL aM aO Ap aR As aV bB bE bJ bL bO bW bZ cC cD cL cM cO cR CX cY dD De dl dN) Mt(Hq Ik Iq Ij Jn Lj Lu Lw Lz Ma Mc Md Mf Mk Ml Mr Ms Nb Nd Ni Nk Nn Nr Ns Oe Of Oi Pa Pb Pc) al(aD Al aR As aU Ax Bc bF bJ bL bM Bn bO bS bW bZ cA cC cE cK Cp cR cT cW CX dA dI dN) aX(aC aD aF aH aN Ao aV aW aY bB bF bH bJ bN bZ cB cC cE cF cH cI cL CO cP cW De dG dH) bW(aD aE AF Al aM AN aO AS bB Bc BG bL cF cM Cp CQ cR Cs cX cZ dB dH Dk dL) cO(aD aE Aj aL aM aN aO AS Ax bB Bc bF bL bM cE cH cM CP cW CX dB DD dN) dC(aL aN aO Ap Ar Ax bB bC bH bL bM Bn Bo bS bZ Cp cR Cs cT cW dA dB dG dI DL dN) Nn(Iq It Jj Jn Lw Mc Mh Mj Mr Ms Mu Mw Mx Nb Nd Nj Nk Nr Ns Oe Oi Pa Pb Pc Pf Qb) bO(aC aL aM aO aR As Ax BC bH bL bM bZ cC Cp Cq cR cT cW Cx dA Dd De dG dI dN) Ap(Af aH Al AN aO AS aV BC bl bL bM Bn Bo Ch Cp Cq Cs cX DB Dd Dk) Lw(Fp Ih Ii Ik Il In Iq Iu Jn Js Lj Me Mj Mk Mq Mr Ms Mv Mw Mx My Na Nj Nk Qb) Jj(Fp Hq Hu Ii Ik Iq Iu Jn Js Lj Ma Mj Mn Mv Mw Mx My Nb Ni Nk Nx Pa Pd Pz Qc) Cx(Af aK AL AO AR aU aV aY bB bL bZ cC cR cW cX cY dB DG dI dL dN) Iu(Hr Io Jn Jo Lj Lu Ma Md Mf Ml Mb Nd Nf Ni Nj Nl Ns Nx Og Oy Pz Qb Qc) Iq(Hq Jn Lh Ly Mc Md Mk Ml Mm Mq Ms Mw Mz Nj Nq Ns Oe Of Og Pb Pf Pz) bZ(aE Aj aL aO AS Ax bB bF bL bM cE cM Cp Cq cR cT cX dB DD dN) Bc(aA aD aF aJ aK Ao aU aV bB Bo cB cD Cp cT cX cY dB Dd De dI) Nb(Fp Hw In Lh Lj Ma Mb Mh Mk Ms My Ng Ni Nk Ns Nx Of Pb Pd Qe) Oe(Hu Hv Hw Ii Il Js Ma Mj Mk Mm Mn Mr Mw Nl Nq Nx Pa Pf Qb Qc) Ax(aC aK aO As aV bA bB bC bE cB cC CP Cs cY dB De Dg dJ) Mz(Il Io Jm Jn Js Lz Mn Mv Mx Nc Ne Ng Nh Nx Oz Pf Pz Qb Qc) aJ(Ad Aj Al An Ao Ar Bg Bo Ch Co Cq Cs Ct Cv Db Dd Dg Dk Dl) aL(Al aM aO aU bH bJ Bn bS cC cK Co Cp Cq cR cT cW cX dG dl) Mi(Hq Hw Ik Il Lh Lx Ly Ma Md Me Mj Na Nc Nd Nl Ns Pc Po) Mm(Fp Ih Ii Jm Js Lj Lx Mj Mk Mx Ng Nl Nr Oy Pa Qb Qe) Hu(Ih It Js Lh Mj Mq Mr Mw Mx My Nd Nk Nl Nx Pa Pc Pf) Ma(Hw li Il In Lh Mj Mk Ms Mx Ni Nj Nl Nr Oi Pa Qb) Jn(aA Mc Mq Mr Ms Mw Nj Nk Nr Ns Oh Oi On Pa Pb Pf) bL(aM aN aO aR bC bM cB cC cE cR cT cW cX De dI dN) Cp(Aj aO AR As aV bC Bn cA cW cX dl Dk dN) Nu(Hr Ik Jm Lu Lz Mc Mg Mh Ms Mu Oz Pb Pd Pf) aA(Ad Aj Ar Ch Cs Cv Dk Jm Ms Ne Ng Nh Qb Qc) Lh(Fp Hv In Jo Lj Mb Ml Nk Of Og Oi On Qb) On(Hr Jo Md Mg Mu Nc Ne Nf Ng Nh Oz Qb) bC(Af Aj aS Bo cB cC cR Ct cX cZ dD Dl) cT(aM aR aU bJ Bn Bo cB cC cR cW Dl dN) Al(aK aU aV bA bB Bo cD cR cY dB De) Mw(Mb Mc Ni Nj Ns Of Og Oy Pa Pf) Qa(Ih Il Mb Mg My Ne Nh Nl Nr Oy) Ms(Ih Js Mj Mn Mv Nq Nx Po Qe) Nj(Hv Js Nx Pa Pf Pz Qb Qc Qe) aO(aM bF bJ cB cE cV cW cX dl) bA(Ad Aj Ao Ar Cq Cs Cv Db Dk) dl(Af Aj As bM Bo cB cR dD) Nx(Fp Hv Il In Lx Nk Nr) Po(Hw Il Js Mg Ne Pz) Ml(Ih Js Mj Nr Qb Qe) Nl(Fp Hv Il Lj Nc Pa) As(Ar aU aV Dd De) Nq(Nf Ng Ni Pa Qb) Lx(Hv Ih Js Mg Nh) bS(aU bB cB cR dB) cX(aR cW De dG dN) dD(aC cW De dG dN) Cs(aU aV cY De) Dd(aV bJ bM dB) Pf(Hq Md Ns Pb) Mj(Jm Mr Qc) Nk(Hw Pz Qc) Ih(Nd Og Oi) Oz(Mr Nr Pa) Pe(Na Nh Pd) dB(cC cR dG) Mv(Ng Pa) Hw(Jo Oi) Il(Nd Qc) aD(dG dN) aM(aV dG) aU(Ar Dk) CqbM NrOg Mbli MgQb MqOi PaPb cRdN Constrained panels with 3 analytes, where 1.0E-8 >= 'AUC p-value' > 0. Contains 1,681 panels of 590,601 total panels evaluated. : cU{As(aA aG aJ aK aL AP Ar aU aV Aw Ax BA Bb bC bF bO bW cE cJ cM Cp Cq cS Cw Cx cY Dc Dd DE dH Di dK Dl Fr) cE(aA aC aG al aJ aL AP Aw aX BA Bb bL bM bW cG cJ cM cS Ct CX DE dK FR) Cx(aA aG aJ aP aU aV aX bA Bb bE bF bQ bR bZ cC cD cJ cL cS Cw dC Dd dH Di dJ) dK(aA aG aJ aP aV Ax aY aZ bA Bb bF bM Bn bP bQ bR bU bZ cC cF cG cL dE dH Dk) bW(aV aY bF Bg Bn bP bQ bR bU bZ cA cC cD cF cG cL cN CO dA dG dH dl) Aw(aY bF Bg bJ Bn bQ bR bU bZ cA cC cD cG cK cL cN CO dE dH dl) Ba(aG aV aY aZ bF Bg bM Bn bQ bR bU bZ cB cC cD cG cJ cK cL dH) bA(aF aG aX aZ bE bF bJ bM Bn bQ bR bZ cB cC cX dC dF dG dH) cM(aV aY Bg Bn bQ bR bU cA cC cD cF cG cL cN CO dB dH dl) aP(aZ bF bM bQ bR bV bZ cB cC cJ cN cV cX dA dC dG dH dl) aA(aF aG aX bE bJ bQ bV cJ cK cS cV cX dA dC dE dG dH) bZ(aC aG al aJ aL Ap Bb bL bM cG cJ cO cS cX dE FR) bF(aC aG al aJ aL aO Bb bL bM cG cJ cS cX dE FR) dC(aJ aV aY Bb bJ bM Bn bO bR cL cX dB dE Di Fr) aG(aC aJ aZ Bb bM bQ bR cC cN cX Dd dE dH Di) dH(aC aJ Ap aX Bb bL bS cG cJ cS dE FR) bQ(aE aJ Ap aX Bb bL cL cS cW Di FR) Bn(aK aU Bb cJ Cp Cq Cu cY Dd Di Fr) cC(aJ aL aX aZ Bb bL bS cS cX dE Di) aJ(aZ bM bR cB cN cX dE dG dL) aY(aC aL aX aZ bC cJ cS cW dE) Bb(aV Bg bJ bR cJ cK cS dE) Fr(aZ Bg bR cD Ch cK cN dA) aE(aV bU cA cG cN cO dE dl) cX(aV aZ bR bU cD cF cJ cL) Di(Al Bg bJ cD cJ cK cN) Dd(Ad An aX dB dE) aL(aC bE bJ cA cN) cS(aZ bM bR cL dE) cN(aZ bC bM fR) Ap(cJ cK Dg) Bg(aU Cp cY) Cu(An Cq Dc) aX(bV dl) bC(cA cL) bE(bM cT) bR(bL bS) cJ(bM cL) AlaU AxCs CpdE aCcT dFfR} Lv{Ml(aA Hv Hw Hx Ih Ii Ij Im In Ir Is Iu Iv Ji Jj Jl Jn Jq Js Jt Li Lw Lx Mi Mj Mr Mz Na Nb Nk Nl Nm No Nr Nt Nu Nw Ny Oh Ok On Pa Pe Po Qa Qd

JgOg JIPg} bW{Aj(Bg bJ bQ bU bZ cA cC dA De dl dK) aL(aV bE bQ bU cG cL cN dA dG) aZ(Al Ax bJ bP bR bZ cD cL dH) Ax(Ba cC cK cO dC dE dG) cT(bF Bg bP cC cD cF) Dc(Bn Bo cE dB dC) dM(bP cD cE dE dH) bM(Al aM cB Cs) bO(Al bP cX dE) Bb(cJ dC) Cu(cE dB) aM(bP cX) bQ(bF dH) AlDi ArcB FrdB aOcE bPdK bRbS dCdE} cE{Cu(aD aG Ap bC Bo bZ cG Co Cq cS Fr) cO(aI aJ aL Aw aZ bO cG dC) bZ(aG aL aZ bL Cp DC) fR(aU aX aZ bC cL cS) aI(aC bC bL cL dI) dF(aG Bb bJ bO Co) Aw(Bb Bo dE dI) De(aL Ax aZ bQ) aZ(Ap bL Di) bQ(bC dC dM) Ax(Ap cJ) Co(aL cT) bA(Bb bS) BacX aOcJ aXcG bBbS bCcT dCdG} Bn{Cq(Ap aZ bM cG cJ De Di dK Fr) Cp(aJ aL bC bO cG cS Fr) De(aJ Ax bV cG Dc dF dM) aZ(aI aJ BA bC Di Fr) Aw(Ba Bb Bg dE dK) Cu(aJ Ao bV FR) Dc(aU bC cO dC) aU(aJ cT dM) aL(Cw dN) aV(dF fR) bC(cG dF) BcdC DifR DkcJ aAcK aIdI aJaM bZcG} Nu{Ji(Hr Hv Hw Iu Jl Jq Md Mz Nl Ny Om) Nk(Ij Jt Mg Mq Nb Oh) Nl(Et Fr Lw Ly Mm Nh) Ne(aA Ih Ir Iu Iv) Ok(Hr Iu Jq Ni Nn) Ng(Jk Mg Mw Nq) Ly(Jk Mr Nt) Mp(Hq Jl Nb) Ir(Lw Mg Mm) Pe(Nn Oh Pc) Md(Nb Qa) Jo(Jt On) NnPa MgQa MwOy HqPg HrJt IsJn} dE{cX(aM Ba Bb bC cB Cp cR Dk dM fR) dC(Ar Aw BC Cp Cs dN) aL(Ax aZ Ba Cq Dc) bO(aM bC De dK fR) cC(bC Cs Di dK) Aw(aV Bc Bg) Ax(aU aV Bb) Dc(Ad aZ De) dK(Bc bM cG) Al(aK aV) Cq(bM cD) aM(aJ cJ) bF(bQ dF) dM(aZ bC) AdCp AjCw BbDi CucV DeaI aFaO} Jo{Nt(Et Iu Ji Jl Jq Jt Lw Mm Mp Nm Ok On) Iu(Et Jk Jl Jq Lh Mi Om) Nv(Jl Me Mg Mr Nb Nl Nr) Iv(Jl Ma Mg Mp Om On) Pg(aA Is Nl Nn On) Jl(Ij Lw Nm Nn) Lh(In Jk Nm Nr) Ma(In Jk) Mg(Ij Qa) Jt(Mi Ms) FrHw MpJk NbIp NlOm HrHx} Og{Jg(Hw Ir Iv Ji Jk Lw Mj Mp Nl Nn Nr Oh Pc Qa) Qe(Et Fr Ip Lx Mm Nv Ok Om) Mg(Jl Mz Nw On Pe Po) Mw(Et Ir Iv Jq Lx Mz) Nb(Lx Mz Nt Nw Pg) Il(Ip Lw Nm Om) Nm(Iv Mj) Hx(Oh Pc) Ij(Fr Ip) IpJk OmPa OnPf} Qd{Ok(Hr Hw Jn Jq Md Mg Mp Mz Ni Om Qa Qc) Jt(Hr Hv Hw Ir Jn Jr Md Mx Na) Is(Ir Iv Jn Jr Js Mh Mx) Lz(Mr Nb Nr On Oz Pe) Qc(aA Jl Lw Mi Mm On) Ji(Jq Mz) Jl(Lw Nn) PoOn LxMi MgNk MwMy HqPg IvJr PaPf} Ng{Mg(Fr Hu Ir Lx Mr Mz Ok Pa Qa) Nq(Hx Iu Jg Nb Nm Nw Pe) Jk(Et Li Lx Ma Mm Nw Om) Jg(Iu Jl Mz Nb Nt Qa) Mw(Et Hu Li Lx Mm) Fr(Hx Ij Nb Nt) Mp(Ii Iu Om Pg) Iu(Nv Om Pg) NtMm LwPg LjPe OmPa} dC{aZ(aI Ar Ax Bb Bc Dc dM) bM(bV cG cT dF dG dM) cX(aM Ar Bo cT Cw dK) Ax(aJ aU bO cG) Bb(Cs Cu dI dK) Aj(Ap BC) Aw(aV Bg Ch) bO(Bo bV cG) Ar(dB dK) Bc(aJ aX) Dc(aJ bC) cB(bS bV) AlDi FrcV bCdM cGcL cOdB} Nk{Ip(Hv Iu Iv Jq Jt Li Ma Mg Nb Nn Om Pa) Nm(Fr Hv Hx Li Lx Po) Lw(aA Et Fr Hx Lx Mz) Ij(Fr Jp Ma Mm) Ji(Hr Hw Jq Mz) Nn(Oi Ok Om) Mg(Mz On Pe) Ma(Hx Mz) Hr(Ok On) Jg(Ns Oi) Jq(Jp Ms) LxNb MpHq} aX{dI(aI aO bS Cs cT cZ Dc dF) bV(aI Aj Bc cT Cu cZ Dc) bQ(aL Bb Cs Cu Dc Di) cV(aI aP Bb Cs cT Cu) dH(Ar bO bP Cs Cu) Ar(bB cB dK) Cu(aY cK) cJ(aZ bM) AlaV AxdN DecZ DkaU aLdK bLcC} aA{Cw(Ad aM An bJ Cq cV) Lw(Hr Hw Jq Md Na) Dc(aD bE bJ cV) Ij(Hr Hw Md Mm) Al(aV aZ cG) Jt(Jq Md Na) aM(Ad An Cq) Ap(bV cB) Co(aZ bF) Ji(Jn Mz) AfAo AxCs BacB BoCp CucV EtMm MuHu LiPf} bO{Al(aG aJ Ap aV Bb bM cG cY De) cX(aC Bb BC Di dM) bM(aG Ba bE Cq dN) Cw(aD bJ cV) bC(Ba dB dK) bF(aO cO dF) aC(aL Ax) bJ(aL cT) BbDi BcaV DcbE aQaU aZdM bQcC bScB bZcO} Oi{Nn(Et Fr Ii Il Ip Ir Is Iu Jk Jr Li Nl No Om Oz Qa) Mg(Ip Iv Jl Nt) Jg(Ip Mj Oh Pc) On(Hr My Nx Oy) Nw(Lw Oh Pc) Nt(Hq Ly) Hu(Lw Oh) Om(Oh Pc) NaJt QaPc} cX{cC(aL bC bL bV cW) aG(aR bC dI) aM(aO aZ bL) bV(Bb cB De) cR(aL Cq dF) Ba(aV Bg) aU(Ax Dc) bL(cJ cT) AlaV BcDi CvaZ aCdD aDcW aLdN bCdK bMcT bQdH bScB} cG{Af(aY bR bU cC cN cO) Ax(bF bM bQ bZ dH) bF(aZ cO cS Fr) dM(bJ bQ cC cN) Al(aV Di) Dc(bJ dB) Fr(Bg bQ) aZ(bJ cC) dH(bS cS) BcbQ CqCu bMcC} Cu{cV(aJ AP BA cS dK Fr) Cw(Ad Ba Dc De fR) dK(aD aZ bJ Bo dB) dG(aJ aP cU) fR(An Cq Dc) AfBa AnDe CqaJ bCdB cKcU cSdH} Aw{Bg(aD Af aG Bo bZ cO dI) Ch(Ad Ap Bb bJ Bo) aV(aD Al dB dI) Af(Bb dK fR) bS(bQ bR cK) Aj(Bc dK) bF(bZ dI) bJ(Bc cT) cVfR} Ok{Pg(Hv Hw Ij In Jq Md Mz Na Nx Ny Om) Hr(Il In Ip Jk Jl Po) Ij(Hw Jq Md Mz) Jp(Mz Oh Pc) Nb(Jq Na) Pe(Mz Ny)} Jp{Oh(Ir Is Iv Jl Mr Nr) Pc(Ir Is Iv Jl Mr Nr) Mg(Iu Iv Jl Nl Nr) Nl(Lw Mm Nm) EtMm NnIv MwOy JiJn} Ax{aU(aD aJ Ap aZ Ba bE) Ap(aV cC Cs) Bb(aG bC bE) De(aD aJ bM) Cs(aJ cR) Di(aC aG) aIcZ aJdG aVbE bFcJ} aL{bJ(bH cO Cp Cw) cC(bH bS cO dB) aC(bH Di dN) aD(Cw fR) bF(bZ cO) bS(bR dB) AfDe DccZ DicV aHfR cRdK cUdG} bM{cJ(bC bS bV De dK dM) Al(aU De Di) bE(aI cT dD) Di(cT dK) aJ(cV dH) bQ(cC dK) CqdB aUdM bJcT bScB} Hr{Hx(Ji Jq Jt Nb Nr Oz) Po(Ji Jl Jt Nb) Pe(Jl Jt Nb Nm) Hw(Ji Lw) Jl(Iu Nm) Pg(Ji Jt) OnPc} aZ{aU(Al aQ Ba Di) Bb(bC Cv dK) cO(bF bJ cC) Al(aI De) Cv(Ap Cw) AfbA aCaI bCcL bRbS cCdI cJdM} Hq{Nt(Ip Lx Nd Nw Pa Po) Mp(Hu Hx Mz Nl On Pe) Po(Pa Pg) Pe(Lj Mm) FrPg LxMa} On{Mh(Hu My Ns Oy) Lz(Li My Oy) Pf(Li My Oy) Mz(My Oy) PoPe LwNx MgMu HvHw IsOh} cT{bJ(aI Bb bC cO) cO(bF bQ dH) aC(aI bC) aU(Af aQ) cV(Ap Fr) BcbE DebF bCcC bScB} Di{Al(aG aU De) Ba(bF Bg) Dc(aD bJ) aU(aJ dM) cV(bV fR) BbaG ChDe bEcJ bFdF} Is{Po(Ir Iv Jr Js Mh) Pc(Ir Jr Js) Ms(Oh Pc) Nw(Jr Mh) EtMm} Dc{dB(aV bC cO dK) Ad(aJ fR) aI(bE cZ) BoDe aDaJ aVbJ bEcJ} De{Af(Al bV cJ dM fR) aD(aJ bV dM) AjfR aPcV bFdF} Mm{Et(Iu Jl Jt Lw Nl Nt) Jg(Ip Lw Mp) NtLi NbIp} My{Mw(Ip Lx Mz Nl Nw Po) Jg(Hx Ij Pg Po)} bC{bF(aI aO dF) Aj(Ao Cp) cC(bL dM) BbaJ BgcJ ChFr} Ms{Jq(Jl Oh Oz Pa Pc) Mp(Nn Oh) InJt JiJn} Pg{Ji(Ij Md Mz Ny Om) Oy(Iu Jg Mw) IjQa} Ap{bV(bQ cK dH) Dg(dK fR) aJ(cK dH) AjCp} Nw{Mh(Iv Jl Nb Nr Pa) MdNb MvJk IrLj} Pc{Lx(Jl Mr Pa Pe) Nn(Jl Nr Pa) NrMp} aI{aD(aM dM fR) cV(Ba fR) BgdI aCdM aGaH} bS{cB(aG cJ dM fR) dK(aG cJ) BbcD bAbR} Cw{Ad(bA cJ Fr) Aj(An Cq) CpcS bJcJ} Bb{aG(Al dI) cV(aP bV) aVdI bFbQ} Cp{Ad(aP bV) AjdK CtcS cJdB} Mg{Jt(Hw Ir Ma) Pe(Oy Pd)} Mp{Jl(Lx Lz Mk Mz) LzPe} dM{AfaU aCcJ bLcC cBdI cRdK} Al{cB(bV fR) AdBa aVdK} aM{aJ(Af bJ) bA(aD Bo)} Lw{EtIl MdHx IuPe} Mz{NnPa HuJi LiLj} Nb{PoMd LxOh IpIu} Ni{FrMe NmHv MaIp} Oy{Jg(Ij Po) LxMw} Bc{aDaU bEdD} Li{LzPa IrLj} aP{CobF FrcV} dK{AraV bPcO} AfaUdF BabFdB NmNaHv NtHwQa MaNlPa MiMkOz aCbVcJ aJcCdI bQcSdH

Constrained panels with 3 analytes, where 1.0E-3 >= 'AUC p-value' > 1.0E-4. Contains 2,810 panels of 590,601 total panels evaluated. : Ml{Jq(Et Fr Hx Ii Il Im In Ip Ir Is Iu Iv Jj Jl Jo Lh Li Mj Mp Mr Nb Nl No Nr Oz) Iv(Et Fr Hv In Iu Ji Jl Ma Mm Mt Nb Nm Nn Nr Oh Ok Om Pc) Ij(Hx Ii Iu Jl Lh Mg Mj Mp Mq Mr No Nr Oe Oh Pa) Ma(Ii Ip Iu Lh Li Mr Mx Nk Nl No Pa Qb) Nb(Hv Jn Jr Mm Mp My Ng Nj Og Oi Oy) Hv(Et Fr Ji Jl Li Mm Mp Nt Oe Pg) Lw(Fp Ii Ir Is Jo Li Mr Mx Om) Nr(Et Ji Jj Jn Mp Mt Nj Nn) Js(Et Fr Hx Li Lx Nt Ok Om) In(Ip Lh Mp Nl No Nx Qc) Jj(Fp Jg Mv Mw Mx Ny Pa) Ok(Ir Ji Jt Mg Mi Mp Nn) Nm(Fp Lh Me Mr Mx Qb) Ii(Et Lx Mm Mp Oe) Jn(Fr Jl Lh Mq Pa) Jo(Im Ip Jt Lx Oe) Om(Hw Ih Iu Mr Oe) Mw(Hu Ng Ns Oy) Ir(Fr Ji Mg Mj) Ny(Ih Mm Mx Nk) Et(Hw Jl Me) Jr(Fr Iu Lh) Nt(Li Ly) Hw(Jg Lx) Is(Ji Mg) Jl(Ji Pg) FrMe MdOn MiJt MjNj MkOf MqQb MxJg IuLi} Of{Mk(Et Fr Ij Ip Jg Ji Jk Jq Li Ma Nj Nl Nm No Nt Om Pg) Pa(aA Hx Ij Im Ip Is Iv Jk Jl Jq Ma Mm Mp Mz Nm Pg) Mw(Ij Il Im Ip Ir Is Iu Jk Jq Li Mj Mm Ns Ny Og) Jg(Is Iu Iv Jq Lh Mp Mr Nl No Nt Nv Oe Oz) Jt(Fr Ir It Jl Jn Jo Jr Js Mp Mr Nr Nt Ok) Jk(Fr Ji Jl Jq Lh Mr Mz Nb No Nr Oz Pe) Ij(Lh Lw Mp Mr Nb Nm No Nr Nt Oz Pe) Om(Iu Iv Lh Mp Mr Nj Nr Nt Nv Oz) Jl(Et Hx Ip Is Iv Ji Jq Mz Ny) Ji(Ii Il In Nb Nr Nt) Oz(Et Hx Ip Lx Mz Qa) Pe(Ir Is Jq Lw Mg Pg) Fr(Hw Ii In Nt Nv) Nr(Et Hx Nq Qa) Nb(Lw Lz Mh Nq) Ok(Iu Mi Mp Nq) Mg(Nv Nw Pg) Hv(Lw Nm Nv) Jq(Hx Lh Nt) Mr(Et Ma) Jo(aA Jj) Lj(Nw On) NoJh NtLw MtNw MvHx HwaA QaLh} Nf{Om(aA Hw Ir Iv Jj Jq Lw Mz Nn Nr Nv Oe Og Oh Pc) Mt(aA Et Fr Hx Ij Ip Jp Li Lx Mz Nt Nu Qa) Jq(aA Et Hx Ij Ip Li Lx Mz Nn Nq Nt Nw Qa) Nt(aA Im Ji Lw Mp Nb Nm Nn Oh Pc) Qa(Fr Iu Jl Mg Mr Nb Nq Oh Pa Pc) Mp(Ii Ij In Jg Lh Nb No Ns Ok) Mz(Fr Ir Jo Lh Mg Mr Nb Nr Pa) Nn(Ij Ir Mr Mu No Ok Pg) Ji(Hv Il In Jk Nb On Pa) Lh(Hx Ij Ip Ir Lx Nm Nu) aA(Hv Hw In Ir Iv Jo Li) Fr(Hv Hw Ij In Ir Mr) Nb(Hx Ip Li Oe Pe) Jt(Im Jj Mi Nw Oi) Nq(Im Ir Jr Pa) Ij(Mg No Oe Og) Ok(Iu Mi Mk Nu) Mw(Jj Ng Ns) Nm(Hw Ii) Lw(Jo Nw) Me(Nv Nw) Hv(Li Mm) Hx(Jg Pa) Im(Hw Pa) On(Ng Oi) Pg(Iu Mg) JjJo NyPb} Dd{Bn(aG aU aZ Ba Bb bM bO bV bW bZ cO dC DE dL dN fR) bJ(aG aJ aU Aw Bb bM bV bZ cG cO cY dC dF dK FR) As(aO Ar aZ Ba Bb bL bM bQ cO dC DE dF dN fR) Ad(aG aJ aL aZ bA Bb Bc bM dE dF dN fR) An(aL aU aV bA bM bO bZ cG De dF dN fR) Cw(aA aI aJ aL aV bA bW cG cS Fr) Bo(Bb bC bE bZ cO dE dI fR)

Figure 37 Continued

Figure 37 Continued

Ns) PoOn Nllp HwNv} Ap{cK(cG Ch dM) Ad(cJ Cw) Ar(aV dK) Bg(cJ Di) CsdC} Mw{My(Et Ir Jg Li Nt Pg) On(Lz Mh) Oy(Ip Jk)} Hr{Ij(Lh Mr Nr Pe) On(In Iv Ns) Hw(Jq Om) JlPg} aX{bQ(al Ar cZ dF) bV(bP Cs dF) AraU aIdK dGdH} aZ{bF(bZ Co Fr) cG(cD cL) CofR CsdC aLbJ cJdK cNdM} cC{dB(cJ cT dK) aI(bU dA) aL(bU cK) dK(bL bQ) bHcG} Mm{Me(Il Ip Nw Pa) Jl(Ij Mz Nu) MzNl LiLj} Di{Ar(aU dC) Ch(aD Ao) aDcW aGaR aQaU bFbZ} De{Af(Bb bO Fr) AjaG BaCh aQaV bJcT} Po{Mi(Il Jk) On(Nu Oi) LzOz IvJr} aU{Dk(bF Bg) fR(aD bJ) AfaQ CsdC} Cw{Ad(aJ bJ Bo) AfBa aVbJ} Jg{Oy(Hx Il Jk) MyIp IuOi} Li{Lj(Iv Jl Nw Pe) LzMj} aA{Ij(Mz Ni Om) BgCo JrJs} bF{bZ(bO dK) dF(Bb Co) ArcJ} dC{Ar(aV cB) BaBo CsaV bJbQ} Lx{NsMq NtNw MiIl IvJr} aD{dM(aL cW) DlbV cBfR} Bb{cG(Bg Ch) AfCq} Ma{Nl(Hx Nr) MfMj} Md{NmIj NuMq OiOn} aG{aH(bB fR)} AjFrbG DkaVdB NmMeNi NqMvNw NtNeNl NuIvJr MkOiOn HuIpJk aJbPdH bJbVcJ dGdKdL Constrained panels with 2 analytes, where 1.0E-7 >= 'AUC p-value' > 0. Contains 56 panels of 14,763 total panels evaluated. : Lv(aA Hx Im Ir Is Ji Jj Jl Jp Jt Li Mi Mm Mz Nd Nu Nw Ok On Pe Po Qa Qd Qe) cU(aA aG aJ AP As BA Bb bF bZ cE cS Cx dE Di dK) aA(aX bC cJ cS Cx dE) aP(Cx dG dH) Ax(Aw dK) bA(bW cS) MiMs dKdM Constrained panels with 2 analytes, where 1.0E-6 >= 'AUC p-value' > 1.0E-7. Contains 60 panels of 14,763 total panels evaluated. : cU(aV aX aZ bJ bM Bn bQ bR cC cJ cL dH Fr) Lv(Iu Lw Ml Mp Mr Nk Nl No Nr Pg) aA(Ap aZ bO cX dC De Ip Mp) aP(aZ cB cE cJ cX dC) bA(Ap aX bC dE Fr) Nu(Jp Mz Qd) Jj(Ij Pe Po) Cx(aX cG) Nj(Nv On) Jp(Im Mp) AxcS CucJ DkdK MlQd MmOn aJaX Constrained panels with 2 analytes, where 1.0E-5 >= 'AUC p-value' > 1.0E-6. Contains 81 panels of 14,763 total panels evaluated. : Jp(Hx Ij In Ip Iu Ji Lw Nm Nn Pe Pg Po) Nu(aA Hx Ip Is Nw On Po Qa) aA(Iu Ma Nj Oe Po Qd) aJ(aZ bM bO cB Cx dC) Lv(Nb Nn Oh Pa Pc) Im(Jj Ni Nj Nk Nl) bA(bJ CX dC dK) Ml(Mi Ny On Po) Jj(Hw Jk Pg Qa) Cu(Ad Cx dE) Qd(Lj Mf Nb) aX(Ax Dd dM) cS(aL bM Cx) Nw(Nk Oe) On(Of Pb) cG(cE cX) cJ(Di Fr) AjBa BcdK LwPg MiNf PePf aCcU Constrained panels with 2 analytes, where 1.0E-4 >= 'AUC p-value' > 1.0E-5. Contains 177 panels of 14,763 total panels evaluated. : Jp(Hw Ir Is Iv Jj Jl Jq Jt Li Mg Mm Nb Nr Nt Oh Ok Pa Pc Qa) Nu(Ij Im Ir Ji Jj Jl Jq Lw Lx Mp Nk Oe Pe Pg) aA(Hx Ij Iv Jt Lw Mg Mz Nt Nw On Pe Pg) Lx(Hx Jj Lw Mp Nb Nj Nk Nl Oe Pa Pc) Qd(Im In Lw Lz Mg Mm Mp Ok On Qc) Jj(Hx In Ip Ir Is Jl Lh Mz Nv) Oe(Hx Iv Jl Mz Nt Nv On Po) Cx(Aw Ba cJ Cw dF FR) Nj(Fr Jl Mi Mz Nt Qa) bA(aC aG aZ bE bM cT) Im(Hx Mp Nb On Pg) aJ(Aw bC cX dE Di) Lw(Hv Hx Pe Po) Ml(Mz Nw Pe Qa) Nk(Et Fr Mm On) bC(As Bb bM dM) cG(bF Bn bO Di) cJ(Ax Ba Bb Dc) dK(aL aZ dF Fr) Cu(aX cX dB) Og(Hx Jg On) Pg(Ji Mm Ok) bW(Aj bM cT) dE(aI aZ Dc) Aw(Bn bO) Ax(aU Di) Mp(Hu Hx) aL(bE dN) aP(cV De) aX(cX Dc) cS(Bb dM) DiaZ PoNl LvMg MmPe MyOn IvNw NyPb bQcE Constrained panels with 2 analytes, where 1.0E-3 >= 'AUC p-value' > 1.0E-4. Contains 373 panels of 14,763 total panels evaluated. : Im(Hu Ii Ij Ip Ir Iu Jk Jl Jt Lh Li Lw Lx Mj Mk Mq Mr Mz Nn Nr Nv Nw Oh Oz Pa Pc Pe Po Qa Qe) Nu(Et Fr Hv Ih Iu Iv Jt Li Mm Mq Mr Nb Nj Nl Nn Nr Nv Oh Ok Pa Pc) Cx(aG Ap Bb BC bW Cp Cq cT DC Dd DE Di dK) Cu(aD An As aZ Ba bC bE bJ Bn Bo Cq cS cU cV dK) Ip(Fr Hv Hx Ij Iu Jk Jq Li Lw Mp Nb Nj Nk No Nt) Jj(Et Hv Ih Il Iv Jg Jm Jq Li Nt Ny Om On Qb Qe) Oe(Et Fr Ir Is Iu Jg Jr Lh Li Nb Nr Ny Om Qa) bO(aG Ap aX aZ Ba Bb bW cS DC dE Di dK fR) Mz(Iu Iv Lw Mg Mm Mp Nk Nl Nn Nt Oh Pc Pg) dE(aG aL Ba cC cG cJ Cp cT cX dC Dd dF dM) Nj(Hw Hx Ij Jg Ji Jk Jp Jt Lh Mp Ok Om) Qa(Hw Iu Jl Lw Mm Mp Nf Nn Oh Pa Pb Pc) aZ(aG Ap Ba Bb bC bW cC cR cS De FR) Nw(Ir Iu Jt Lw Mg Mm Mp Nf Nl Nt Pc) cG(aG As Ax Bg bJ bM cC dH dK dM) Di(aG AL As Ba bW DC dK) Ml(Hx Ij Ir Is Iv Jt Li Nb Ok) Po(Iu Jl Jt Mm Mp Nn Oh Pc) Hx(Et Fr Iu Li Ma Mm Nl Nn) dC(aX Bb Bc cX Dc dF dM Fr) Lx(Iu Jl Jt Mr Nn Nr Oh) Pe(Iu Jt Mg Mp Nn Oh Pc) aA(Al Bb Ir Is Ji Mm Nl) Lw(Jl Nb Nr Nt Nv On) cX(aG bQ cS cT dF fR) Dc(Ad aG aU bW dK) Mm(Hv Ij Il In Ir) Mp(Hq Ir Jl Pa) Nk(Ji Ma Ok Om) On(Mw Oi Ok Oy) Pg(Iu Iv Jt Of) aX(aI aL cJ fR) Ap(Ax cJ Dg) As(Aw bA Cw) bM(cT dK dN) Cw(Ad Bn) Fr(Bg Ch) Nm(Hv Pa) Hu(Nn Oh) Jp(Mr Nl) Og(Ij Om) aC(aI aL) aG(Bb dM) aJ(Ba De) bC(cT fR) bW(Ax bP) cE(dF fR) ArdK AwaV BoDd NtIr MsJq MwMy NgJg NiJi IuNv JtOf aUdM bFbQ Constrained panels with 2 analytes, where 1.0E-2 >= 'AUC p-value' > 1.0E-3. Contains 402 panels of 14,763 total panels evaluated. : Jj(Fr Hu Ii Iu Ji Jn Jr Js Jt Ma Mj Mn Mp Mt Mv Mx My Nb Nk Nn No Nx Pa Qc) Oe(Hu Hw Ii Ij Il Im Jh Ji Jk Jq Js Ma Mm Mr Mt Nm No Nq Nx Pa Qb) Nn(Et Ij Ip Ir Is Jl Li Lw Mr Nb Nj Nk No Nr Nt Oi Ok Om Pa Pg) Mm(Im Ip Is Iv Ji Jl Jq Jr Jt Li Mj Nl Nr Nt Ok Pa Qb) Mp(Et Ij Is Iv Ji Jq Jt Li Mr Nb Nl Nr Nt Oh Ok) Mg(Hx Im Ip Ir Is Jl Li Lx Nu Ok Pg Po Qa Qb) Nl(Et Fr Hv Ij Ip Jg Ji Li Ma Nm Nv Ok Om Pa) Oh(Et Hx Ij Ip Ir Is Jg Jk Jl Jq Li Nv Om) dE(aM Ap Aw Ax Bb bC bW cO Cw Di dK FR) As(Ar Ax bQ bW bZ cO Cp Dc Dd De dF dI) Lw(Et Fr Il Ir Is Iu Iv Jk Li Mj Mr Nk) Pc(Hu Hx Ij Ir Is Jg Jl Jq Li Nt Nv Om) Iu(Et Fr Ij Iv Ji Jq Li Nb Nj Ok Om) Ax(aC aG aV Ba Bb bO Cs cY dC De) Nk(Hw Ij Jg Jh Jq Jt Lh Nb Nm Nx) Im(Et Hv Hw Is Iv Jq Js Mv No Nt) cX(aL aO aZ BC bL bV cJ cW dM) Ok(Hr Jq Md Na Nf Ni Of Pb) bM(Ba bO bQ cJ cO Cq dC dF) bW(aM Ba Bb Bg cF cR dB dM) dK(Aw aX Ba Bb bC cR cT) Cx(aL aU aV aZ bO dM) Ma(Hw Ii Ni Nj Nr Pa) Ml(Ji Jq Js Mj Nr Om) dC(Ar Aw Bo bV Cw dN) Al(aL aU aV cY De) Bb(aJ aV Dl fR) Fr(bC bF cE cV Iv) Is(Iv Jr Js Mh Nt) Ji(Nf Nt Of Pa Pb) Jq(Mr Nj Nr Oz Pa) Jt(Hr Jl Na Nf Pb) aC(bO cG dD dF dM) Nb(Et Li Of Pb) Ip(Jl Mr Nr Pa) bF(aO bZ cO dF) bO(bC cJ De dM) Mw(Of Og Oy) Nj(Hv No Pa) On(Hr Nf Ng) aG(aR bS dI) aZ(cJ Dc dM) bJ(aL Cw Dd) cB(bS bV dI) Ba(bC Dc) Bc(aV Di) Nm(Il Mj) Hq(Mi Nt) Jg(My Of) Jk(Ng Og) Om(Nf Of) aM(bL cO) cC(bL bQ) cE(bZ cO) cJ(bS bV) BnCp CwaD DiaU EtHv MzJl IjPa IrPg LiLj aLcR aXdH

Figure 37 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.5E1 | 1.3E2 | 8.5E1 | 1.6E2 | 5.7E1 | 1.0E2 | 7.0E0 | 2.5E1 | 4.0E2 | 4.8E2 | 238 | 34 | 238 | 34 | 0.75 |
| Ad | ug/mL | 4.8E-2 | 9.2E-2 | 7.2E-2 | 5.3E-1 | 8.8E-2 | 1.9E0 | 6.8E-4 | 8.1E-3 | 5.4E-1 | 8.5E0 | 121 | 20 | 121 | 20 | 0.66 |
| Af | ng/mL | 1.3E0 | 7.7E-1 | 1.1E1 | 4.0E0 | 5.1E1 | 6.8E0 | 1.7E-3 | 1.7E-3 | 5.3E2 | 2.3E1 | 121 | 20 | 121 | 20 | 0.44 |
| Aj | ug/mL | 1.1E0 | 2.9E-1 | 2.3E0 | 1.6E0 | 2.4E0 | 2.3E0 | 1.5E-3 | 2.3E-3 | 6.1E0 | 6.1E0 | 121 | 20 | 121 | 20 | 0.40 |
| Al | mg/mL | 8.3E-5 | 1.2E-4 | 2.5E-4 | 3.7E-4 | 4.2E-4 | 5.1E-4 | 4.6E-6 | 7.6E-6 | 1.8E-3 | 1.8E-3 | 121 | 20 | 121 | 20 | 0.60 |
| An | U/mL | 6.2E1 | 1.1E2 | 2.4E2 | 5.9E2 | 6.2E2 | 1.7E3 | 6.1E-1 | 6.4E-1 | 5.5E3 | 7.8E3 | 121 | 20 | 121 | 20 | 0.59 |
| Ao | pg/mL | 9.2E1 | 1.2E2 | 6.7E2 | 1.9E2 | 4.2E3 | 1.9E2 | 2.8E0 | 1.7E1 | 3.9E4 | 6.9E2 | 121 | 20 | 121 | 20 | 0.61 |
| Ap | ng/mL | 3.2E1 | 4.6E1 | 4.2E1 | 5.8E1 | 4.3E1 | 5.2E1 | 2.0E0 | 6.4E0 | 2.9E2 | 2.1E2 | 121 | 20 | 121 | 20 | 0.60 |
| Ar | ng/mL | 5.7E-1 | 2.4E0 | 3.1E0 | 6.0E0 | 7.6E0 | 1.1E1 | 4.1E-2 | 3.4E-3 | 5.1E1 | 5.0E1 | 121 | 20 | 121 | 20 | 0.71 |
| As | ng/mL | 9.4E-3 | 1.1E-2 | 1.3E-2 | 7.5E-2 | 1.8E-2 | 2.7E-1 | 1.7E-3 | 1.7E-3 | 1.3E-1 | 1.2E0 | 121 | 20 | 121 | 20 | 0.51 |
| Aw | pg/mL | 1.6E1 | 1.7E1 | 1.7E1 | 1.9E1 | 5.8E0 | 9.3E0 | 2.9E-2 | 1.1E1 | 4.2E1 | 5.1E1 | 121 | 20 | 121 | 20 | 0.54 |
| Ax | ng/mL | 2.2E0 | 8.0E0 | 2.2E1 | 1.2E2 | 9.1E1 | 2.2E2 | 1.3E-2 | 1.2E-2 | 7.7E2 | 8.5E2 | 121 | 20 | 121 | 20 | 0.68 |
| Ba | ng/mL | 8.1E1 | 3.2E2 | 5.5E2 | 1.1E3 | 1.5E3 | 2.1E3 | 1.1E0 | 3.1E0 | 8.1E3 | 8.1E3 | 121 | 20 | 121 | 20 | 0.63 |
| Bh | ng/mL | 3.9E0 | 1.4E1 | 6.2E0 | 1.4E1 | 7.7E0 | 1.0E1 | 4.1E-3 | 1.4E0 | 4.9E1 | 3.7E1 | 121 | 20 | 121 | 20 | 0.75 |
| Bc | ng/mL | 3.3E1 | 8.0E1 | 1.2E2 | 1.8E2 | 2.3E2 | 2.9E2 | 4.9E-1 | 5.6E0 | 1.2E3 | 1.0E3 | 121 | 20 | 121 | 20 | 0.66 |
| Bg | ng/mL | 1.1E-1 | 3.9E-1 | 8.2E0 | 1.8E0 | 4.1E1 | 2.5E0 | 5.3E-4 | 2.4E-2 | 4.0E2 | 8.0E0 | 121 | 20 | 121 | 20 | 0.62 |
| Bn | ng/mL | 5.6E-2 | 5.6E-2 | 1.2E0 | 3.5E0 | 2.1E0 | 1.3E1 | 5.6E-2 | 5.6E-2 | 8.6E0 | 5.8E1 | 121 | 20 | 121 | 20 | 0.45 |
| Bo | ng/mL | 1.3E1 | 1.5E1 | 1.5E1 | 1.6E1 | 1.1E1 | 1.4E1 | 1.6E-2 | 1.6E-2 | 5.0E1 | 5.3E1 | 121 | 20 | 121 | 20 | 0.51 |
| Ch | uIU/mL | 1.2E0 | 9.4E-1 | 4.7E1 | 5.8E0 | 2.1E2 | 1.2E1 | 3.4E-3 | 1.4E-1 | 1.8E3 | 5.0E1 | 121 | 20 | 121 | 20 | 0.44 |
| Co | pg/mL | 4.6E1 | 6.5E1 | 2.7E2 | 2.0E2 | 1.6E3 | 4.5E2 | 1.5E-1 | 2.0E1 | 1.7E4 | 2.1E3 | 121 | 20 | 121 | 20 | 0.66 |
| Cp | ng/mL | 2.2E1 | 2.2E1 | 2.8E1 | 9.7E1 | 2.1E1 | 2.8E2 | 6.0E-1 | 1.0E1 | 1.3E2 | 1.3E3 | 121 | 20 | 121 | 20 | 0.56 |
| Cq | ng/mL | 3.0E-2 | 3.3E-2 | 1.2E-1 | 2.6E0 | 5.1E-1 | 1.1E1 | 8.0E-4 | 8.0E-4 | 5.1E0 | 4.9E1 | 121 | 20 | 121 | 20 | 0.56 |
| Cs | ng/mL | 7.2E1 | 3.1E2 | 4.9E2 | 1.1E3 | 1.9E3 | 1.7E3 | 1.0E0 | 8.3E-1 | 1.8E4 | 5.1E3 | 121 | 20 | 121 | 20 | 0.69 |
| Ct | ng/mL | 3.3E-1 | 3.0E-1 | 4.6E1 | 4.0E1 | 1.3E2 | 1.1E2 | 1.5E-2 | 1.1E-4 | 6.2E2 | 4.7E2 | 121 | 20 | 121 | 20 | 0.48 |
| Cu | ng/mL | 2.6E-1 | 3.7E-1 | 4.4E-1 | 5.0E0 | 6.6E-1 | 1.5E1 | 2.8E-2 | 5.4E-2 | 4.5E0 | 6.6E1 | 121 | 20 | 121 | 20 | 0.64 |
| Cv | ng/mL | 3.9E0 | 1.7E1 | 2.2E1 | 5.9E1 | 5.9E1 | 1.2E2 | 2.0E-2 | 5.1E-2 | 5.3E2 | 4.7E2 | 121 | 20 | 121 | 20 | 0.62 |
| Cw | mIU/mL | 3.1E-2 | 5.0E-2 | 4.2E-2 | 3.8E-1 | 3.5E-2 | 1.5E0 | 8.9E-4 | 4.1E-3 | 2.3E-1 | 6.8E0 | 121 | 20 | 121 | 20 | 0.62 |
| Cx | ng/mL | 9.5E-1 | 1.5E-2 | 4.8E1 | 3.8E1 | 9.6E1 | 8.6E1 | 9.3E-5 | 9.3E-5 | 3.9E2 | 2.8E2 | 121 | 20 | 121 | 20 | 0.40 |
| Db | ug/mL | 7.3E0 | 7.8E0 | 8.5E0 | 7.8E0 | 7.9E0 | 4.9E0 | 4.5E-1 | 1.0E0 | 5.9E1 | 1.9E1 | 121 | 20 | 121 | 20 | 0.52 |
| Dc | nmol/L | 2.1E-2 | 2.4E-2 | 6.1E-2 | 9.3E-1 | 1.7E-1 | 3.1E0 | 5.2E-6 | 3.3E-3 | 1.6E0 | 1.4E1 | 121 | 20 | 121 | 20 | 0.66 |
| Dd | ug/mL | 6.9E-2 | 2.8E-1 | 1.7E-1 | 4.7E-1 | 2.5E-1 | 8.2E-1 | 4.8E-4 | 3.4E-3 | 1.6E0 | 3.6E0 | 121 | 20 | 121 | 20 | 0.64 |
| De | ng/mL | 3.4E-3 | 3.4E-3 | 8.3E-2 | 1.1E-1 | 1.4E-1 | 3.0E-1 | 3.4E-3 | 3.4E-3 | 9.2E-1 | 1.1E0 | 121 | 20 | 121 | 20 | 0.41 |
| Dg | ng/mL | 3.7E1 | 3.7E1 | 4.6E1 | 5.3E1 | 3.9E1 | 4.1E1 | 7.1E-1 | 2.3E0 | 1.9E2 | 1.2E2 | 121 | 20 | 121 | 20 | 0.55 |
| Di | pg/mL | 2.0E0 | 2.8E0 | 2.4E0 | 3.1E0 | 2.2E0 | 1.9E0 | 1.8E-1 | 1.8E-1 | 1.3E1 | 9.0E0 | 121 | 20 | 121 | 20 | 0.62 |
| Dk | uIU/mL | 1.6E-2 | 2.8E-2 | 5.8E-2 | 1.4E-1 | 1.8E-1 | 2.7E-1 | 1.1E-4 | 1.1E-4 | 1.6E0 | 9.8E-1 | 121 | 20 | 121 | 20 | 0.61 |
| Dl | ng/mL | 2.0E2 | 3.0E2 | 3.0E2 | 3.9E2 | 2.8E2 | 3.6E2 | 5.5E0 | 2.0E1 | 1.3E3 | 1.6E3 | 121 | 20 | 121 | 20 | 0.59 |
| Dp | ng/ml | 2.2E0 | 1.8E0 | 5.6E0 | 3.5E0 | 9.5E0 | 5.0E0 | 3.7E-3 | 3.7E-3 | 5.6E1 | 1.4E1 | 100 | 13 | 100 | 13 | 0.41 |
| Dr | pg/ml | 1.7E1 | 3.9E1 | 4.0E1 | 1.3E3 | 5.5E1 | 3.4E3 | 7.5E-1 | 7.5E-1 | 2.5E2 | 1.0E4 | 49 | 9 | 49 | 9 | 0.69 |
| Du | pg/ml | 1.6E2 | 9.6E2 | 1.1E3 | 4.0E3 | 3.2E3 | 8.6E3 | 1.2E0 | 1.2E0 | 2.0E4 | 2.4E4 | 41 | 7 | 41 | 7 | 0.63 |
| Ef | ng/ml | 9.4E-2 | 2.4E-1 | 7.8E-1 | 1.4E0 | 1.8E0 | 2.9E0 | 5.7E-4 | 5.7E-4 | 9.5E0 | 9.9E0 | 108 | 15 | 108 | 15 | 0.59 |
| Wm | % | 8.5E-2 | 2.7E-1 | 1.8E1 | 8.4E1 | 1.1E2 | 2.6E2 | 5.4E-2 | 8.5E-2 | 8.7E2 | 1.0E3 | 114 | 16 | 114 | 16 | 0.55 |
| Ed | pg/ml | 1.1E0 | 6.8E1 | 3.1E1 | 9.9E1 | 6.1E1 | 1.3E2 | 5.2E-1 | 5.2E-1 | 5.0E2 | 4.8E2 | 100 | 13 | 100 | 13 | 0.70 |
| Tj | pg/mL | 3.7E-1 | 3.7E-1 | 4.6E1 | 3.6E1 | 2.4E2 | 7.1E1 | 3.7E-1 | 3.7E-1 | 2.3E3 | 2.5E2 | 104 | 15 | 104 | 15 | 0.58 |
| Po | pg/ml | 2.1E-1 | 4.5E0 | 8.7E0 | 2.6E1 | 2.7E1 | 5.0E1 | 8.0E-3 | 2.6E-2 | 2.7E2 | 2.2E2 | 227 | 41 | 227 | 41 | 0.66 |
| Ti | ug/mL | 3.0E0 | 9.0E0 | 4.3E0 | 8.7E0 | 3.7E0 | 6.1E0 | 1.2E-1 | 9.7E-1 | 1.4E1 | 1.8E1 | 61 | 8 | 61 | 8 | 0.71 |
| Em | ng/ml | 1.3E-2 | 2.6E-2 | 5.5E-2 | 2.8E-1 | 9.8E-2 | 6.0E-1 | 8.4E-4 | 8.4E-4 | 5.0E-1 | 1.9E0 | 63 | 10 | 63 | 10 | 0.55 |
| Et | ng/ml | 1.4E3 | 3.0E3 | 1.7E3 | 2.8E3 | 1.1E3 | 1.3E3 | 7.9E1 | 5.9E2 | 4.3E3 | 5.0E3 | 226 | 41 | 226 | 41 | 0.76 |
| Eq | pg/ml | 1.6E2 | 3.1E1 | 3.7E2 | 2.5E2 | 4.0E2 | 5.2E2 | 1.0E0 | 1.0E0 | 1.5E3 | 1.4E3 | 41 | 7 | 41 | 7 | 0.31 |
| Th | ug/mL | 1.2E0 | 1.6E0 | 1.9E0 | 2.3E0 | 1.6E0 | 2.2E0 | 1.2E-1 | 2.6E-3 | 7.5E0 | 5.9E0 | 61 | 8 | 61 | 8 | 0.52 |
| Fa | ng/ml | 4.0E1 | 9.5E1 | 1.3E2 | 1.8E2 | 4.5E2 | 2.1E2 | 2.6E-1 | 6.0E-1 | 3.7E3 | 7.3E2 | 98 | 12 | 98 | 12 | 0.69 |
| Ez | ng/ml | 4.1E0 | 4.6E0 | 1.4E1 | 3.2E1 | 2.5E1 | 5.8E1 | 1.3E-2 | 9.5E-2 | 1.6E2 | 2.0E2 | 100 | 13 | 100 | 13 | 0.59 |
| Fb | ng/ml | 2.7E1 | 2.9E1 | 2.2E1 | 3.0E1 | 1.2E1 | 6.7E0 | 6.6E-1 | 2.2E1 | 4.3E1 | 4.1E1 | 99 | 12 | 99 | 12 | 0.68 |
| Ex | ng/ml | 9.0E-2 | 1.6E-1 | 1.7E-1 | 3.2E-1 | 2.6E-1 | 4.2E-1 | 3.5E-5 | 1.7E-4 | 1.5E0 | 1.2E0 | 76 | 11 | 76 | 11 | 0.62 |
| Fc | pg/ml | 2.2E-1 | 6.3E0 | 1.2E1 | 5.4E1 | 6.1E1 | 1.1E2 | 2.2E-1 | 2.2E-1 | 3.9E2 | 3.1E2 | 42 | 7 | 42 | 7 | 0.70 |

Figure 38

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fd | pg/ml | 3.8E1 | 4.9E2 | 5.5E2 | 7.0E3 | 1.5E3 | 1.1E4 | 4.5E-1 | 9.8E-1 | 9.2E3 | 2.5E4 | 42 | 7 | 42 | 7 | 0.68 |
| Fi | pg/ml | 2.5E-1 | 6.1E1 | 6.1E1 | 1.7E2 | 2.9E2 | 2.1E2 | 2.5E-1 | 2.5E-1 | 1.8E3 | 5.3E2 | 42 | 7 | 42 | 7 | 0.72 |
| Fn | ng/ml | 2.1E-1 | 1.7E0 | 4.2E0 | 6.4E0 | 7.4E0 | 8.6E0 | 1.1E-14 | 2.1E-1 | 3.7E1 | 2.7E1 | 100 | 13 | 100 | 13 | 0.57 |
| Fp | ng/ml | 1.3E1 | 3.8E1 | 2.3E1 | 4.0E1 | 2.7E1 | 3.3E1 | 6.0E-3 | 1.2E0 | 1.3E2 | 1.3E2 | 230 | 41 | 230 | 41 | 0.68 |
| Fr | ng/ml | 3.4E4 | 1.1E5 | 1.2E5 | 2.5E5 | 1.9E5 | 2.7E5 | 1.9E2 | 1.8E3 | 8.4E5 | 8.4E5 | 233 | 42 | 233 | 42 | 0.70 |
| Fw | pg/ml | 8.5E-1 | 1.5E1 | 4.8E1 | 7.6E1 | 3.0E2 | 1.3E2 | 1.2E-1 | 1.2E-1 | 3.0E3 | 4.4E2 | 108 | 15 | 108 | 15 | 0.72 |
| Fy | ng/ml | 3.6E1 | 1.1E2 | 6.1E1 | 1.9E2 | 7.3E1 | 2.3E2 | 1.2E-1 | 7.0E0 | 5.0E2 | 6.5E2 | 99 | 12 | 99 | 12 | 0.68 |
| Gh | pg/ml | 2.0E0 | 3.9E0 | 2.1E1 | 1.2E1 | 5.8E1 | 1.7E1 | 2.9E-2 | 2.9E-2 | 3.2E2 | 4.6E1 | 42 | 7 | 42 | 7 | 0.57 |
| Gb | % | 4.4E1 | 6.2E1 | 4.4E1 | 1.0E2 | 3.1E1 | 1.0E2 | 2.2E0 | 2.5E1 | 1.4E2 | 3.0E2 | 42 | 7 | 42 | 7 | 0.70 |
| Gc | ng/ml | 8.3E1 | 2.5E2 | 1.5E2 | 3.1E2 | 2.2E2 | 2.2E2 | 6.4E0 | 6.7E1 | 1.2E3 | 6.7E2 | 49 | 9 | 49 | 9 | 0.76 |
| Gd | ng/ml | 3.4E1 | 2.7E1 | 3.5E1 | 3.5E1 | 1.7E1 | 2.5E1 | 3.0E0 | 9.6E0 | 6.9E1 | 8.0E1 | 59 | 8 | 59 | 8 | 0.46 |
| Gn | U/ml | 2.4E-1 | 2.7E-1 | 1.4E0 | 1.3E1 | 4.4E0 | 3.8E1 | 5.6E-3 | 2.7E-2 | 3.0E1 | 1.1E2 | 48 | 9 | 48 | 9 | 0.54 |
| Gl | pg/ml | 1.0E4 | 8.9E3 | 1.2E4 | 1.4E4 | 9.5E3 | 1.1E4 | 9.1E1 | 5.2E2 | 3.1E4 | 3.1E4 | 108 | 15 | 108 | 15 | 0.55 |
| Gp | U/ml | 1.2E0 | 1.6E-2 | 2.4E0 | 1.2E0 | 3.2E0 | 2.0E0 | 1.5E-2 | 1.5E-2 | 1.8E1 | 7.3E0 | 108 | 15 | 108 | 15 | 0.35 |
| Gz | ug/ml | 1.4E0 | 1.5E0 | 5.6E0 | 3.6E0 | 5.8E0 | 4.5E0 | 4.2E-2 | 1.0E-1 | 2.5E1 | 1.1E1 | 70 | 9 | 70 | 9 | 0.46 |
| Ha | ng/ml | 1.9E0 | 6.2E0 | 8.3E0 | 1.9E1 | 1.9E1 | 3.5E1 | 1.7E-2 | 1.7E-2 | 1.0E2 | 1.0E2 | 98 | 13 | 98 | 13 | 0.66 |
| Nm | pg/ml | 1.4E4 | 3.2E4 | 3.4E4 | 8.7E4 | 8.5E4 | 1.6E5 | 1.0E-9 | 1.2E3 | 9.6E5 | 8.2E5 | 230 | 41 | 230 | 41 | 0.63 |
| Nn | pg/ml | 1.5E2 | 4.3E2 | 1.8E3 | 1.5E4 | 8.0E3 | 5.2E4 | 1.0E-9 | 9.5E0 | 9.5E4 | 3.1E5 | 230 | 41 | 230 | 41 | 0.67 |
| No | pg/ml | 1.5E1 | 3.9E1 | 3.0E1 | 1.3E2 | 5.7E1 | 2.2E2 | 1.0E-9 | 4.3E0 | 5.6E2 | 9.1E2 | 230 | 41 | 230 | 41 | 0.75 |
| Nq | pg/ml | 1.7E0 | 6.6E0 | 2.4E1 | 6.3E1 | 7.9E1 | 1.4E2 | 1.0E-9 | 1.0E-9 | 6.7E2 | 6.3E2 | 230 | 41 | 230 | 41 | 0.64 |
| Nr | pg/ml | 1.5E0 | 9.1E0 | 2.2E1 | 8.5E1 | 8.3E1 | 2.4E2 | 1.0E-9 | 1.0E-9 | 9.8E2 | 1.4E3 | 230 | 41 | 230 | 41 | 0.68 |
| Ns | pg/ml | 1.0E-9 | 1.0E-9 | 1.1E1 | 1.0E-9 | 7.8E1 | 0.0E0 | 1.0E-9 | 1.0E-9 | 1.1E3 | 1.0E-9 | 230 | 41 | 230 | 41 | 0.47 |
| Nt | pg/ml | 1.1E2 | 1.5E2 | 1.4E2 | 2.6E2 | 1.0E2 | 3.2E2 | 1.5E1 | 5.5E1 | 8.8E2 | 1.7E3 | 230 | 41 | 230 | 41 | 0.65 |
| Nu | pg/ml | 2.4E1 | 5.0E1 | 5.7E1 | 8.8E1 | 8.8E1 | 9.9E1 | 1.0E-9 | 1.0E-9 | 6.3E2 | 3.7E2 | 230 | 41 | 230 | 41 | 0.63 |
| Lu | pg/ml | 1.0E4 | 1.0E4 | 1.7E4 | 1.1E4 | 4.8E4 | 1.0E4 | 9.4E2 | 5.2E2 | 5.6E5 | 5.7E4 | 230 | 41 | 230 | 41 | 0.51 |
| Lv | pg/ml | 1.0E-9 | 4.5E0 | 1.7E1 | 2.8E1 | 3.4E1 | 3.9E1 | 1.0E-9 | 1.0E-9 | 2.6E2 | 1.6E2 | 230 | 41 | 230 | 41 | 0.58 |
| Lw | pg/ml | 1.0E-9 | 1.0E-9 | 5.1E-1 | 6.4E0 | 5.7E0 | 2.8E1 | 1.0E-9 | 1.0E-9 | 8.0E1 | 1.8E2 | 230 | 41 | 230 | 41 | 0.55 |
| Lx | pg/ml | 1.0E-9 | 1.6E2 | 1.8E2 | 1.0E3 | 6.3E2 | 3.5E3 | 1.0E-9 | 1.0E-9 | 6.2E3 | 2.2E4 | 230 | 41 | 230 | 41 | 0.71 |
| Ly | pg/ml | 1.0E-9 | 1.0E-9 | 1.0E1 | 6.2E0 | 1.8E1 | 1.4E1 | 1.0E-9 | 1.0E-9 | 1.1E2 | 6.0E1 | 230 | 41 | 230 | 41 | 0.44 |
| Lz | pg/ml | 1.0E-9 | 1.0E-9 | 3.2E0 | 5.6E0 | 3.0E1 | 1.6E1 | 1.0E-9 | 1.0E-9 | 4.3E2 | 6.2E1 | 230 | 41 | 230 | 41 | 0.58 |
| Ma | pg/ml | 4.7E2 | 1.6E3 | 2.4E3 | 4.5E3 | 6.6E3 | 8.0E3 | 1.0E-9 | 2.6E1 | 6.5E4 | 3.6E4 | 230 | 41 | 230 | 41 | 0.67 |
| Mb | pg/ml | 2.6E1 | 2.8E1 | 3.3E1 | 3.1E1 | 1.9E1 | 1.4E1 | 9.2E0 | 4.1E0 | 2.1E2 | 6.4E1 | 230 | 41 | 230 | 41 | 0.49 |
| Mc | pg/ml | 1.0E-9 | 1.0E-9 | 8.3E-2 | 1.0E-9 | 9.1E-1 | 0.0E0 | 1.0E-9 | 1.0E-9 | 1.3E1 | 1.0E-9 | 230 | 41 | 230 | 41 | 0.49 |
| Md | pg/ml | 1.0E-9 | 1.0E-9 | 5.5E-1 | 1.0E0 | 4.5E0 | 4.7E0 | 1.0E-9 | 1.0E-9 | 6.5E1 | 2.9E1 | 230 | 41 | 230 | 41 | 0.52 |
| Me | pg/ml | 3.0E1 | 3.7E1 | 3.0E1 | 3.5E1 | 2.7E1 | 2.9E1 | 1.0E-9 | 1.0E-9 | 3.2E2 | 1.8E2 | 230 | 41 | 230 | 41 | 0.59 |
| Mf | pg/ml | 1.0E-9 | 1.0E-9 | 8.4E-1 | 3.9E-1 | 4.7E0 | 1.1E0 | 1.0E-9 | 1.0E-9 | 5.6E1 | 4.5E0 | 230 | 41 | 230 | 41 | 0.51 |
| Mg | pg/ml | 1.2E0 | 2.0E0 | 6.9E0 | 1.4E1 | 1.3E1 | 2.9E1 | 1.0E-9 | 1.0E-9 | 9.2E1 | 1.5E2 | 230 | 41 | 230 | 41 | 0.55 |
| Mh | pg/ml | 1.0E-9 | 1.0E-9 | 1.1E0 | 1.4E0 | 7.9E0 | 3.8E0 | 1.0E-9 | 1.0E-9 | 1.1E2 | 1.8E1 | 230 | 41 | 230 | 41 | 0.59 |
| Mi | pg/ml | 1.0E-9 | 1.0E-9 | 1.2E0 | 2.5E1 | 9.7E0 | 9.5E1 | 1.0E-9 | 1.0E-9 | 1.2E2 | 5.2E2 | 230 | 41 | 230 | 41 | 0.58 |
| Mj | pg/ml | 1.0E-9 | 1.0E-9 | 5.9E0 | 1.7E1 | 3.2E1 | 4.5E1 | 1.0E-9 | 1.0E-9 | 4.6E2 | 2.1E2 | 230 | 41 | 230 | 41 | 0.59 |
| Mk | pg/ml | 1.7E0 | 3.9E0 | 1.9E1 | 2.2E1 | 1.1E2 | 8.0E1 | 1.0E-9 | 1.0E-9 | 1.3E3 | 5.0E2 | 230 | 41 | 230 | 41 | 0.54 |
| Ml | pg/ml | 1.0E-9 | 1.0E-9 | 1.2E1 | 2.5E1 | 1.4E2 | 9.6E1 | 1.0E-9 | 1.0E-9 | 2.1E3 | 5.1E2 | 230 | 41 | 230 | 41 | 0.53 |
| Mm | pg/ml | 5.7E2 | 1.1E3 | 1.0E3 | 1.9E3 | 1.2E3 | 2.2E3 | 1.0E-9 | 5.2E1 | 6.4E3 | 1.0E4 | 230 | 41 | 230 | 41 | 0.63 |
| Mn | pg/ml | 5.9E0 | 1.1E1 | 1.2E1 | 1.4E1 | 2.9E1 | 9.7E0 | 1.0E-9 | 2.4E0 | 3.5E2 | 5.1E1 | 230 | 41 | 230 | 41 | 0.70 |
| Mp | pg/ml | 1.0E-9 | 8.8E0 | 1.3E1 | 9.9E1 | 4.7E1 | 3.8E2 | 1.0E-9 | 1.0E-9 | 6.3E2 | 2.4E3 | 230 | 41 | 230 | 41 | 0.63 |
| Mq | pg/ml | 1.0E-9 | 1.0E-9 | 2.4E0 | 7.4E0 | 1.4E1 | 2.1E1 | 1.0E-9 | 1.0E-9 | 1.8E2 | 1.0E2 | 230 | 41 | 230 | 41 | 0.55 |
| Mr | pg/ml | 1.0E-9 | 3.6E0 | 2.7E1 | 2.1E2 | 1.4E2 | 6.6E2 | 1.0E-9 | 1.0E-9 | 1.5E3 | 3.4E3 | 230 | 41 | 230 | 41 | 0.62 |
| Ms | pg/ml | 3.5E2 | 2.6E2 | 4.7E2 | 3.5E2 | 5.3E2 | 3.4E2 | 1.0E-9 | 1.0E-9 | 3.3E3 | 1.5E3 | 230 | 41 | 230 | 41 | 0.45 |
| Mt | pg/ml | 3.4E-1 | 1.6E0 | 9.4E0 | 1.1E2 | 5.2E1 | 5.0E2 | 1.0E-9 | 1.0E-9 | 7.1E2 | 3.2E3 | 230 | 41 | 230 | 41 | 0.67 |
| Mu | pg/ml | 1.0E-9 | 1.0E-9 | 2.0E0 | 3.2E0 | 1.7E1 | 9.7E0 | 1.0E-9 | 1.0E-9 | 2.3E2 | 4.8E1 | 230 | 41 | 230 | 41 | 0.56 |
| Mv | pg/ml | 1.0E-9 | 1.0E-9 | 8.2E1 | 1.2E2 | 4.0E2 | 2.6E2 | 1.0E-9 | 1.0E-9 | 4.5E3 | 9.2E2 | 230 | 41 | 230 | 41 | 0.58 |
| Mw | pg/ml | 3.0E1 | 1.2E2 | 3.2E2 | 6.2E2 | 1.6E3 | 1.3E3 | 1.0E-9 | 1.0E-9 | 1.8E4 | 5.3E3 | 230 | 41 | 230 | 41 | 0.73 |
| Mx | pg/ml | 1.0E-9 | 1.0E-9 | 3.9E-1 | 1.2E0 | 2.2E0 | 3.3E0 | 1.0E-9 | 1.0E-9 | 3.2E1 | 2.0E1 | 230 | 41 | 230 | 41 | 0.61 |
| My | pg/ml | 1.0E-9 | 7.5E0 | 4.5E2 | 1.7E2 | 3.0E3 | 4.3E2 | 1.0E-9 | 1.0E-9 | 3.9E4 | 1.9E3 | 230 | 41 | 230 | 41 | 0.58 |
| Mz | pg/ml | 1.1E1 | 3.0E1 | 2.4E1 | 1.3E2 | 5.2E1 | 3.5E2 | 1.0E-9 | 1.0E-9 | 5.5E2 | 1.9E3 | 230 | 41 | 230 | 41 | 0.75 |
| Na | pg/ml | 1.0E-9 | 1.0E-9 | 5.3E-1 | 1.7E0 | 1.7E0 | 6.7E0 | 1.0E-9 | 1.0E-9 | 9.6E0 | 4.2E1 | 230 | 41 | 230 | 41 | 0.53 |
| Nb | pg/ml | 2.1E0 | 3.5E0 | 3.7E0 | 1.4E1 | 1.2E1 | 3.6E1 | 1.0E-9 | 1.0E-9 | 1.5E2 | 2.1E2 | 230 | 41 | 230 | 41 | 0.64 |

Figure 38 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nc | pg/ml | 3.4E2 | 5.3E1 | 5.3E2 | 3.8E2 | 7.8E2 | 6.2E2 | 1.0E-9 | 1.0E-9 | 9.2E3 | 3.2E3 | 230 | 41 | 230 | 41 | 0.39 |
| Nd | pg/ml | 2.3E1 | 3.5E1 | 2.7E1 | 8.5E1 | 8.2E1 | 3.3E2 | 1.0E-9 | 1.0E-9 | 1.2E3 | 2.1E3 | 230 | 41 | 230 | 41 | 0.64 |
| Ne | pg/ml | 4.2E2 | 4.0E2 | 5.2E2 | 5.0E2 | 5.9E2 | 6.0E2 | 1.0E-9 | 1.0E-9 | 7.0E3 | 3.6E3 | 230 | 41 | 230 | 41 | 0.46 |
| Nf | pg/ml | 1.0E-9 | 1.0E-9 | 2.4E0 | 7.3E0 | 9.4E0 | 2.7E1 | 1.0E-9 | 1.0E-9 | 8.2E1 | 1.3E2 | 230 | 41 | 230 | 41 | 0.51 |
| Ng | pg/ml | 1.7E1 | 4.8E1 | 1.1E2 | 9.2E1 | 2.1E2 | 1.3E2 | 1.0E-9 | 1.0E-9 | 1.6E3 | 5.3E2 | 230 | 41 | 230 | 41 | 0.53 |
| Nh | pg/ml | 5.9E1 | 5.5E1 | 8.1E1 | 7.0E1 | 7.6E1 | 8.4E1 | 1.0E-9 | 4.1E0 | 5.6E2 | 5.1E2 | 230 | 41 | 230 | 41 | 0.44 |
| Ni | pg/ml | 2.2E0 | 1.0E-9 | 8.5E1 | 1.1E2 | 1.3E2 | 2.2E2 | 1.0E-9 | 1.0E-9 | 7.1E2 | 1.1E3 | 230 | 41 | 230 | 41 | 0.46 |
| Nj | pg/ml | 6.1E0 | 6.7E0 | 9.9E0 | 9.3E0 | 1.1E1 | 9.6E0 | 1.0E-9 | 1.0E-9 | 6.8E1 | 4.6E1 | 230 | 41 | 230 | 41 | 0.50 |
| Nk | pg/ml | 1.8E1 | 1.2E1 | 3.1E1 | 3.6E1 | 3.6E1 | 5.4E1 | 1.0E-9 | 1.0E-9 | 2.0E2 | 2.0E2 | 230 | 41 | 230 | 41 | 0.49 |
| Nl | pg/ml | 4.2E1 | 3.9E1 | 5.6E1 | 4.7E1 | 8.2E1 | 5.1E1 | 1.0E-9 | 1.0E-9 | 1.1E3 | 2.3E2 | 230 | 41 | 230 | 41 | 0.45 |
| Hl | pg/ml | 1.7E1 | 1.1E1 | 3.8E1 | 5.3E2 | 6.0E1 | 1.4E3 | 1.0E-9 | 1.0E-9 | 3.0E2 | 3.6E3 | 42 | 7 | 42 | 7 | 0.53 |
| Ho | pg/ml | 1.8E1 | 3.3E1 | 2.4E1 | 1.1E2 | 1.9E1 | 1.4E2 | 1.1E0 | 7.6E0 | 8.7E1 | 3.9E2 | 42 | 7 | 42 | 7 | 0.64 |
| Hp | ng/ml | 1.6E0 | 6.9E0 | 8.8E1 | 3.8E2 | 2.6E2 | 4.7E2 | 1.0E-9 | 8.8E-1 | 8.9E2 | 8.9E2 | 42 | 7 | 42 | 7 | 0.70 |
| Tz | pg/ml | 4.1E3 | 7.6E3 | 7.5E3 | 1.9E5 | 1.7E4 | 5.7E5 | 1.0E-9 | 6.8E2 | 1.7E5 | 2.1E6 | 101 | 13 | 101 | 13 | 0.68 |
| Ua | pg/ml | 3.2E3 | 7.8E3 | 1.4E4 | 1.7E4 | 2.8E4 | 2.7E4 | 1.0E-9 | 1.4E3 | 1.4E5 | 9.9E4 | 101 | 13 | 101 | 13 | 0.65 |
| Ub | pg/ml | 5.3E2 | 3.2E2 | 8.2E2 | 7.3E2 | 1.2E3 | 1.1E3 | 1.0E-9 | 2.3E0 | 9.8E3 | 4.1E3 | 101 | 13 | 101 | 13 | 0.41 |
| Ue | pg/ml | 2.7E1 | 2.7E1 | 3.5E1 | 4.9E1 | 3.2E1 | 4.5E1 | 9.8E-2 | 1.1E1 | 2.7E2 | 1.4E2 | 101 | 13 | 101 | 13 | 0.55 |
| Uc | pg/ml | 7.7E2 | 1.4E3 | 1.4E3 | 6.1E3 | 1.8E3 | 1.5E4 | 1.0E-9 | 1.9E2 | 9.4E3 | 5.7E4 | 101 | 13 | 101 | 13 | 0.60 |
| Ud | pg/ml | 1.0E-9 | 1.0E-9 | 3.9E0 | 4.1E0 | 3.9E1 | 1.5E1 | 1.0E-9 | 1.0E-9 | 3.9E2 | 5.3E1 | 101 | 13 | 101 | 13 | 0.53 |
| Hq | pg/ml | 1.2E0 | 1.1E0 | 2.2E2 | 7.9E1 | 2.3E3 | 4.3E2 | 1.0E-9 | 1.0E-9 | 2.8E4 | 2.8E3 | 228 | 41 | 228 | 41 | 0.53 |
| Hr | pg/ml | 8.4E1 | 9.0E1 | 5.6E2 | 4.6E2 | 1.1E3 | 1.5E3 | 1.0E-9 | 1.0E-9 | 8.4E3 | 8.9E3 | 228 | 41 | 228 | 41 | 0.46 |
| Hu | pg/ml | 1.3E1 | 6.5E1 | 6.7E3 | 6.5E2 | 4.8E4 | 1.4E3 | 1.0E-9 | 1.0E-9 | 6.3E5 | 6.5E3 | 228 | 41 | 228 | 41 | 0.57 |
| Hv | pg/ml | 1.5E0 | 9.3E-1 | 2.6E0 | 2.9E1 | 5.5E0 | 1.4E2 | 1.0E-9 | 1.0E-9 | 6.9E1 | 8.9E2 | 228 | 41 | 228 | 41 | 0.48 |
| Hw | pg/ml | 5.5E0 | 6.5E0 | 1.6E1 | 2.6E2 | 5.3E1 | 1.5E3 | 1.0E-9 | 5.1E-1 | 6.4E2 | 9.4E3 | 228 | 41 | 228 | 41 | 0.51 |
| Hx | pg/ml | 8.9E0 | 1.2E1 | 6.7E1 | 7.8E1 | 6.1E2 | 2.3E2 | 1.0E-9 | 1.0E-9 | 9.3E3 | 1.3E3 | 228 | 41 | 228 | 41 | 0.57 |
| Ib | ng/ml | 3.6E-2 | 3.3E-2 | 1.2E0 | 4.5E0 | 5.1E0 | 1.5E1 | 1.0E-9 | 1.0E-9 | 3.6E1 | 5.6E1 | 98 | 13 | 98 | 13 | 0.50 |
| Ic | U/ml | 2.2E2 | 2.2E2 | 1.1E3 | 2.6E2 | 6.6E3 | 1.4E2 | 2.4E0 | 2.5E1 | 6.5E4 | 4.2E2 | 98 | 13 | 98 | 13 | 0.61 |
| Id | U/ml | 5.5E-1 | 1.3E0 | 1.3E0 | 3.5E1 | 2.0E0 | 1.2E2 | 1.0E-9 | 3.8E-1 | 1.3E1 | 4.3E2 | 98 | 13 | 98 | 13 | 0.71 |
| Tt | pg/ml | 1.7E2 | 1.7E2 | 1.8E2 | 2.0E2 | 5.4E1 | 8.7E1 | 4.3E1 | 1.1E2 | 3.6E2 | 4.4E2 | 91 | 12 | 91 | 12 | 0.53 |
| To | pg/ml | 1.6E0 | 1.8E0 | 2.0E0 | 2.5E0 | 2.1E0 | 3.2E0 | 1.0E-9 | 1.0E-9 | 9.9E0 | 1.2E1 | 96 | 13 | 96 | 13 | 0.53 |
| Tr | pg/ml | 3.3E0 | 6.9E0 | 9.5E0 | 1.3E1 | 3.2E1 | 2.1E1 | 1.0E-9 | 6.3E-1 | 3.1E2 | 7.6E1 | 94 | 12 | 94 | 12 | 0.62 |
| Tn | pg/ml | 3.3E1 | 5.5E1 | 1.1E2 | 2.9E2 | 3.1E2 | 6.2E2 | 2.4E0 | 1.9E1 | 2.0E3 | 2.3E3 | 96 | 13 | 96 | 13 | 0.70 |
| Tv | ng/ml | 1.2E1 | 1.0E1 | 2.9E1 | 5.8E2 | 8.7E1 | 2.0E3 | 1.0E-9 | 1.0E-9 | 7.9E2 | 7.1E3 | 96 | 13 | 96 | 13 | 0.46 |
| Ih | ng/ml | 6.3E1 | 3.3E2 | 2.0E2 | 6.6E2 | 3.3E2 | 8.1E2 | 1.0E-9 | 4.2E0 | 2.1E3 | 3.6E3 | 229 | 41 | 229 | 41 | 0.72 |
| Ii | ng/ml | 8.1E1 | 1.3E2 | 2.0E2 | 4.4E2 | 4.6E2 | 9.0E2 | 7.3E-1 | 2.3E0 | 5.2E3 | 4.5E3 | 229 | 41 | 229 | 41 | 0.63 |
| Ij | ng/ml | 7.8E1 | 1.7E2 | 1.8E2 | 9.0E2 | 6.3E2 | 3.8E3 | 2.8E0 | 4.3E1 | 6.4E3 | 2.4E4 | 227 | 40 | 227 | 40 | 0.76 |
| Ik | ng/ml | 1.2E1 | 1.4E1 | 1.8E3 | 1.8E2 | 1.4E4 | 3.6E2 | 5.9E-1 | 2.7E0 | 1.2E5 | 1.5E3 | 227 | 40 | 227 | 40 | 0.55 |
| Il | ng/ml | 3.6E2 | 5.7E2 | 1.2E3 | 2.5E3 | 2.6E3 | 4.0E3 | 1.0E-9 | 1.0E-9 | 1.2E4 | 1.2E4 | 225 | 40 | 225 | 40 | 0.61 |
| Im | ng/ml | 2.0E2 | 7.0E2 | 3.7E2 | 1.3E3 | 5.7E2 | 1.6E3 | 1.4E1 | 8.7E1 | 6.0E3 | 6.2E3 | 226 | 41 | 226 | 41 | 0.81 |
| In | ng/ml | 3.3E0 | 3.3E0 | 1.6E1 | 1.4E2 | 7.7E1 | 7.0E2 | 1.0E-9 | 1.0E-9 | 1.1E3 | 4.5E3 | 229 | 41 | 229 | 41 | 0.53 |
| Hb | ng/ml | 2.1E1 | 5.9E1 | 3.2E1 | 7.5E1 | 3.2E1 | 5.9E1 | 4.8E-1 | 1.6E1 | 2.0E2 | 1.9E2 | 102 | 13 | 102 | 13 | 0.77 |
| Hc | pg/ml | 7.0E2 | 5.5E2 | 3.4E3 | 1.8E3 | 1.2E4 | 3.7E3 | 1.0E-9 | 1.0E-9 | 1.0E5 | 1.4E4 | 102 | 13 | 102 | 13 | 0.46 |
| Hf | ng/ml | 2.0E2 | 3.3E2 | 4.3E2 | 3.5E2 | 6.0E2 | 3.2E2 | 1.0E-9 | 1.0E-9 | 3.2E3 | 9.9E2 | 102 | 13 | 102 | 13 | 0.50 |
| Io | ng/ml | 1.1E4 | 2.0E4 | 2.1E4 | 2.3E4 | 5.4E4 | 2.0E4 | 1.0E-9 | 6.2E2 | 7.1E5 | 9.9E4 | 229 | 41 | 229 | 41 | 0.63 |
| Ip | ng/ml | 1.2E1 | 3.0E1 | 2.1E1 | 3.3E1 | 2.7E1 | 2.2E1 | 1.0E-9 | 3.3E-1 | 2.3E2 | 7.8E1 | 229 | 41 | 229 | 41 | 0.69 |
| Iq | ug/ml | 1.1E-1 | 3.1E-1 | 7.0E-1 | 7.9E0 | 2.7E0 | 3.4E1 | 1.0E-9 | 1.0E-9 | 3.4E1 | 2.2E2 | 229 | 41 | 229 | 41 | 0.66 |
| Ir | ug/ml | 3.6E-1 | 1.7E0 | 2.0E0 | 2.2E1 | 1.1E1 | 6.4E1 | 1.0E-9 | 9.4E-2 | 1.6E2 | 3.7E2 | 228 | 41 | 228 | 41 | 0.74 |
| Is | ng/ml | 2.0E0 | 9.8E0 | 6.7E0 | 3.2E1 | 1.3E1 | 5.3E1 | 1.0E-9 | 3.3E-2 | 1.1E2 | 2.6E2 | 229 | 41 | 229 | 41 | 0.69 |
| It | ng/ml | 1.8E0 | 5.7E0 | 1.3E1 | 4.2E1 | 6.3E1 | 1.3E2 | 1.0E-9 | 1.0E-9 | 8.3E2 | 6.8E2 | 229 | 41 | 229 | 41 | 0.72 |
| Iu | ng/ml | 1.7E2 | 2.5E2 | 1.1E3 | 2.5E3 | 3.6E3 | 6.4E3 | 1.0E-9 | 1.0E-9 | 2.9E4 | 2.4E4 | 229 | 41 | 229 | 41 | 0.58 |
| Iv | ng/ml | 1.3E1 | 3.1E1 | 3.5E1 | 3.6E2 | 7.8E1 | 9.8E2 | 1.0E-9 | 1.0E-9 | 7.7E2 | 3.8E3 | 228 | 41 | 228 | 41 | 0.66 |
| Iz | ng/ml | 1.2E2 | 2.1E2 | 3.5E2 | 3.2E2 | 7.3E2 | 3.3E2 | 1.5E0 | 8.8E0 | 6.1E3 | 1.0E3 | 102 | 13 | 102 | 13 | 0.60 |
| Yd | ng/ml | 2.2E-1 | 7.6E-2 | 4.4E-1 | 1.9E-1 | 5.7E-1 | 2.0E-1 | 6.6E-3 | 1.7E-2 | 2.3E0 | 5.6E-1 | 43 | 7 | 43 | 7 | 0.38 |
| Wb | pg/ml | 2.7E4 | 3.5E4 | 3.4E4 | 1.4E5 | 1.9E4 | 2.3E5 | 6.3E3 | 1.4E4 | 8.4E4 | 6.4E5 | 43 | 7 | 43 | 7 | 0.67 |
| Vz | pg/ml | 3.8E0 | 5.0E0 | 4.8E0 | 6.0E0 | 4.3E0 | 7.5E0 | 1.0E-9 | 7.6E-2 | 2.1E1 | 2.2E1 | 43 | 7 | 43 | 7 | 0.52 |
| Si | ng/ml | 1.1E0 | 2.7E0 | 1.8E0 | 3.2E0 | 2.5E0 | 2.2E0 | 8.6E-3 | 5.6E-1 | 1.0E1 | 6.0E0 | 42 | 7 | 42 | 7 | 0.72 |
| Sf | mIU/mL | 2.0E1 | 2.0E1 | 5.5E1 | 2.8E1 | 1.2E2 | 2.7E1 | 7.8E-1 | 6.7E0 | 7.2E2 | 8.3E1 | 42 | 7 | 42 | 7 | 0.53 |

Figure 38 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Sh | mIU/mL | 1.7E1 | 1.0E1 | 5.0E1 | 1.0E1 | 1.0E2 | 5.5E0 | 7.8E-2 | 4.2E0 | 5.7E2 | 2.1E1 | 42 | 7 | 42 | 7 | 0.35 |
| Sj | ng/ml | 4.4E-1 | 4.3E-1 | 4.4E-1 | 4.1E-1 | 9.4E-2 | 6.1E-2 | 2.5E-1 | 3.4E-1 | 7.2E-1 | 4.8E-1 | 42 | 7 | 42 | 7 | 0.44 |
| Rc | pg/ml | 6.9E3 | 7.6E3 | 7.7E3 | 6.9E3 | 5.4E3 | 3.0E3 | 5.5E2 | 2.1E3 | 2.7E4 | 1.3E4 | 100 | 13 | 100 | 13 | 0.51 |
| Rb | pg/ml | 7.8E-1 | 2.4E0 | 2.6E0 | 6.4E0 | 4.1E0 | 1.5E1 | 1.0E-9 | 1.0E-9 | 2.0E1 | 5.6E1 | 100 | 13 | 100 | 13 | 0.56 |
| Zw | 2.5ng/ml | 7.2E0 | 4.7E0 | 9.7E0 | 1.9E1 | 1.1E1 | 2.9E1 | 2.4E-1 | 7.7E-1 | 5.9E1 | 6.3E1 | 43 | 7 | 43 | 7 | 0.49 |
| Zx | 2.3mU/ml | 1.3E-1 | 1.8E-1 | 3.3E-1 | 2.4E-1 | 5.8E-1 | 2.0E-1 | 3.2E-2 | 7.7E-2 | 2.9E0 | 6.7E-1 | 43 | 7 | 43 | 7 | 0.61 |
| Pz | ng/ml | 3.5E3 | 1.0E4 | 5.7E3 | 7.1E3 | 6.4E3 | 4.8E3 | 1.6E1 | 3.3E2 | 7.0E4 | 2.5E4 | 225 | 41 | 225 | 41 | 0.61 |
| Qa | ng/ml | 3.6E3 | 9.4E3 | 6.5E3 | 1.8E4 | 7.4E3 | 3.5E4 | 1.5E2 | 6.8E2 | 4.2E4 | 2.2E5 | 225 | 41 | 225 | 41 | 0.71 |
| Qb | ng/ml | 1.1E2 | 2.1E2 | 2.1E2 | 4.6E2 | 2.9E2 | 6.8E2 | 7.9E-1 | 1.8E1 | 2.8E3 | 4.1E3 | 225 | 41 | 225 | 41 | 0.69 |
| Qc | ng/ml | 2.0E2 | 6.5E2 | 4.1E2 | 8.2E2 | 5.1E2 | 8.3E2 | 1.0E-9 | 1.0E-9 | 3.8E3 | 4.3E3 | 225 | 41 | 225 | 41 | 0.67 |
| Qd | ng/ml | 9.5E3 | 2.3E4 | 2.6E4 | 6.4E4 | 1.4E5 | 9.2E4 | 2.4E2 | 1.7E3 | 2.0E6 | 4.3E5 | 225 | 41 | 225 | 41 | 0.73 |
| Qe | ng/ml | 7.9E2 | 2.5E3 | 2.1E3 | 3.4E3 | 6.7E3 | 3.4E3 | 7.6E0 | 8.8E0 | 9.7E4 | 1.8E4 | 225 | 41 | 225 | 41 | 0.72 |
| Jd | ng/ml | 8.9E-1 | 2.7E0 | 4.1E0 | 5.3E0 | 1.6E1 | 6.7E0 | 1.0E-9 | 1.0E-9 | 1.2E2 | 2.1E1 | 100 | 13 | 100 | 13 | 0.67 |
| Je | ng/ml | 1.0E-9 | 1.0E-9 | 1.9E0 | 2.6E0 | 5.5E0 | 3.6E0 | 1.0E-9 | 1.0E-9 | 4.6E1 | 1.1E1 | 100 | 13 | 100 | 13 | 0.56 |
| Jf | ng/ml | 1.0E-9 | 1.0E-9 | 1.4E0 | 5.1E-1 | 2.4E0 | 1.1E0 | 1.0E-9 | 1.0E-9 | 1.2E1 | 3.7E0 | 100 | 13 | 100 | 13 | 0.40 |
| Jg | ng/ml | 5.2E2 | 1.2E3 | 8.0E2 | 1.5E3 | 9.9E2 | 1.4E3 | 5.8E0 | 5.4E1 | 1.0E4 | 7.1E3 | 228 | 41 | 228 | 41 | 0.69 |
| Jh | ng/ml | 2.9E0 | 9.4E0 | 2.4E1 | 4.8E1 | 9.8E1 | 9.6E1 | 1.0E-9 | 1.0E-9 | 1.2E3 | 4.9E2 | 228 | 41 | 228 | 41 | 0.65 |
| Ji | ng/ml | 5.8E1 | 1.4E2 | 8.0E1 | 2.3E2 | 8.0E1 | 2.4E2 | 1.1E0 | 2.3E1 | 5.3E2 | 1.3E3 | 228 | 41 | 228 | 41 | 0.75 |
| Sr | pg/mL | 3.8E2 | 2.4E3 | 8.2E2 | 3.6E3 | 1.2E3 | 5.5E3 | 1.0E-9 | 9.7E1 | 5.5E3 | 2.1E4 | 99 | 13 | 99 | 13 | 0.80 |
| Ss | pg/mL | 1.0E5 | 5.5E4 | 1.5E5 | 1.2E5 | 1.8E5 | 1.5E5 | 2.7E3 | 1.4E4 | 1.3E6 | 5.7E5 | 99 | 13 | 99 | 13 | 0.44 |
| St | pg/mL | 2.4E7 | 1.0E8 | 6.6E7 | 2.0E8 | 1.4E8 | 4.4E8 | 1.0E-9 | 3.4E6 | 1.2E9 | 1.7E9 | 98 | 13 | 98 | 13 | 0.75 |
| Wc | ng/ml | 1.0E-9 | 1.0E-9 | 4.4E-2 | 3.5E-1 | 7.5E-2 | 6.8E-1 | 1.0E-9 | 1.0E-9 | 3.0E-1 | 1.8E0 | 43 | 7 | 43 | 7 | 0.52 |
| Wd | ng/ml | 9.5E0 | 1.8E1 | 2.2E1 | 1.2E2 | 4.7E1 | 1.9E2 | 1.0E0 | 3.5E0 | 2.9E2 | 4.1E2 | 43 | 7 | 43 | 7 | 0.69 |
| We | ng/ml | 3.2E-1 | 4.9E-1 | 9.5E-1 | 3.8E0 | 1.3E0 | 8.4E0 | 1.0E-9 | 1.5E-1 | 5.5E0 | 2.3E1 | 43 | 7 | 43 | 7 | 0.61 |
| Wg | ng/ml | 1.0E-9 | 1.0E-9 | 1.0E-9 | 7.6E-2 | 0.0E0 | 2.0E-1 | 1.0E-9 | 1.0E-9 | 1.0E-9 | 5.3E-1 | 43 | 7 | 43 | 7 | 0.57 |
| Wh | ng/ml | 1.1E-2 | 2.0E-2 | 3.2E-2 | 7.3E-2 | 7.0E-2 | 1.2E-1 | 1.0E-9 | 1.0E-9 | 3.5E-1 | 3.4E-1 | 43 | 7 | 43 | 7 | 0.60 |
| Wf | ng/ml | 1.0E-9 | 1.0E-9 | 1.1E-1 | 3.3E-1 | 2.3E-1 | 8.6E-1 | 1.0E-9 | 1.0E-9 | 1.2E0 | 2.3E0 | 43 | 7 | 43 | 7 | 0.40 |
| Ra | pg/ml | 1.0E-9 | 1.0E-9 | 3.9E-1 | 5.7E0 | 9.6E-1 | 1.8E1 | 1.0E-9 | 1.0E-9 | 3.8E0 | 6.4E1 | 100 | 13 | 100 | 13 | 0.57 |
| Qz | pg/ml | 9.4E0 | 1.2E1 | 5.1E1 | 5.1E1 | 8.8E1 | 8.0E1 | 1.0E-9 | 1.0E-9 | 4.5E2 | 2.3E2 | 100 | 13 | 100 | 13 | 0.53 |
| Qy | pg/ml | 3.6E-1 | 7.1E-1 | 8.9E0 | 5.8E1 | 4.9E1 | 2.0E2 | 1.0E-9 | 1.0E-1 | 4.3E2 | 7.3E2 | 100 | 13 | 100 | 13 | 0.72 |
| Qx | pg/ml | 1.0E-9 | 1.0E-9 | 3.2E0 | 1.3E1 | 1.9E1 | 3.6E1 | 1.0E-9 | 1.0E-9 | 1.9E2 | 1.1E2 | 100 | 13 | 100 | 13 | 0.56 |
| Qw | pg/ml | 1.0E-9 | 6.8E-1 | 3.3E0 | 1.1E0 | 1.1E1 | 1.6E0 | 1.0E-9 | 1.0E-9 | 6.6E1 | 5.6E0 | 100 | 13 | 100 | 13 | 0.56 |
| Qv | pg/ml | 1.8E4 | 1.2E4 | 3.0E4 | 1.6E4 | 5.1E4 | 1.5E4 | 1.0E-9 | 8.5E2 | 3.7E5 | 5.0E4 | 100 | 13 | 100 | 13 | 0.40 |
| Qu | pg/ml | 7.0E0 | 3.7E1 | 9.6E1 | 1.2E2 | 1.9E2 | 2.0E2 | 1.0E-9 | 1.0E-9 | 9.8E2 | 7.3E2 | 100 | 13 | 100 | 13 | 0.56 |
| Qt | pg/ml | 1.5E1 | 1.4E1 | 4.8E1 | 4.8E1 | 1.0E2 | 8.0E1 | 1.0E-9 | 1.0E-9 | 7.1E2 | 2.2E2 | 100 | 13 | 100 | 13 | 0.49 |
| Qh | ng/ml | 1.8E1 | 3.8E1 | 4.7E1 | 1.1E2 | 7.6E1 | 2.1E2 | 4.3E-1 | 1.2E1 | 4.6E2 | 8.0E2 | 100 | 13 | 100 | 13 | 0.71 |
| Qg | ng/ml | 7.2E0 | 7.8E0 | 1.1E1 | 1.4E1 | 1.3E1 | 2.2E1 | 1.5E-1 | 3.3E-1 | 7.5E1 | 8.1E1 | 100 | 13 | 100 | 13 | 0.48 |
| Jj | ng/ml | 5.8E2 | 2.6E2 | 2.5E3 | 4.9E2 | 2.2E4 | 5.0E2 | 2.0E1 | 1.2E1 | 3.4E5 | 1.9E3 | 228 | 41 | 228 | 41 | 0.35 |
| Jk | ng/ml | 3.0E0 | 5.1E0 | 2.3E1 | 3.4E1 | 5.3E1 | 5.9E1 | 1.0E-9 | 3.8E-1 | 3.9E2 | 2.4E2 | 228 | 41 | 228 | 41 | 0.61 |
| Jl | ng/ml | 5.1E-1 | 1.0E0 | 2.2E0 | 2.5E2 | 5.1E0 | 1.6E3 | 1.2E-3 | 9.0E-2 | 4.0E1 | 9.9E3 | 228 | 41 | 228 | 41 | 0.63 |
| Jm | ng/ml | 2.1E1 | 4.5E1 | 5.8E1 | 1.2E2 | 1.2E2 | 3.2E2 | 1.0E-9 | 9.2E-1 | 1.0E3 | 2.1E3 | 228 | 41 | 228 | 41 | 0.61 |
| Jn | pg/ml | 3.5E-1 | 8.4E-1 | 1.6E0 | 4.1E1 | 5.5E0 | 1.5E2 | 1.0E-9 | 1.0E-9 | 5.8E1 | 7.3E2 | 228 | 41 | 228 | 41 | 0.70 |
| Jo | pg/ml | 4.2E3 | 5.1E3 | 5.0E3 | 8.9E3 | 3.9E3 | 1.6E4 | 2.6E2 | 2.3E2 | 2.4E4 | 1.0E5 | 228 | 41 | 228 | 41 | 0.54 |
| Jp | pg/ml | 7.2E4 | 8.7E4 | 7.5E4 | 1.0E5 | 3.4E4 | 5.9E4 | 2.1E3 | 2.8E4 | 1.9E5 | 3.8E5 | 228 | 41 | 228 | 41 | 0.67 |
| Jq | pg/ml | 9.7E1 | 1.4E2 | 1.5E2 | 5.7E2 | 1.7E2 | 1.5E3 | 5.6E0 | 5.6E0 | 1.1E3 | 8.7E3 | 228 | 41 | 228 | 41 | 0.60 |
| Jr | pg/ml | 2.9E0 | 1.5E1 | 2.5E1 | 4.0E2 | 1.4E2 | 1.4E3 | 1.0E-9 | 1.0E-9 | 1.9E3 | 7.4E3 | 228 | 41 | 228 | 41 | 0.67 |
| Js | pg/ml | 1.5E1 | 2.7E1 | 4.1E1 | 2.8E2 | 1.4E2 | 7.7E2 | 1.0E-9 | 6.1E0 | 1.6E3 | 3.0E3 | 228 | 41 | 228 | 41 | 0.72 |
| Jt | pg/ml | 2.5E3 | 4.3E3 | 2.9E3 | 7.0E3 | 2.0E3 | 1.0E4 | 1.5E2 | 8.7E2 | 1.3E4 | 5.2E4 | 228 | 41 | 228 | 41 | 0.68 |
| Xa | pg/ml | 6.1E-1 | 2.4E1 | 8.1E0 | 2.7E2 | 1.7E1 | 4.7E2 | 1.0E-9 | 2.9E0 | 9.6E1 | 1.2E3 | 43 | 7 | 43 | 7 | 0.83 |
| Ye | pg/ml | 1.0E-9 | 1.0E-9 | 5.3E0 | 1.0E0 | 1.5E1 | 2.7E0 | 1.0E-9 | 1.0E-9 | 6.9E1 | 7.2E0 | 43 | 7 | 43 | 7 | 0.42 |
| Tm | pg/ml | 1.0E-9 | 1.0E-9 | 3.1E0 | 1.2E0 | 4.7E0 | 3.2E0 | 1.0E-9 | 1.0E-9 | 1.8E1 | 8.4E0 | 43 | 7 | 43 | 7 | 0.41 |
| Tl | pg/ml | 1.3E-1 | 1.0E-9 | 3.5E-1 | 3.6E0 | 4.1E-1 | 9.3E0 | 1.0E-9 | 1.0E-9 | 1.8E0 | 2.5E1 | 43 | 7 | 43 | 7 | 0.40 |
| Ju | mIU/ml | 1.2E1 | 1.2E1 | 2.7E1 | 1.9E1 | 3.8E1 | 1.7E1 | 1.7E-1 | 5.5E0 | 2.3E2 | 6.0E1 | 100 | 13 | 100 | 13 | 0.55 |
| Jv | mIU/ml | 1.8E1 | 1.3E1 | 4.4E1 | 2.5E1 | 6.8E1 | 2.7E1 | 1.7E-2 | 2.9E0 | 4.4E2 | 8.9E1 | 100 | 13 | 100 | 13 | 0.47 |
| Jy | ng/ml | 1.6E-3 | 2.6E-3 | 2.4E-3 | 5.8E-3 | 4.4E-3 | 1.1E-2 | 1.7E-4 | 5.3E-4 | 3.9E-2 | 4.1E-2 | 100 | 13 | 100 | 13 | 0.70 |
| Kc | pg/ml | 2.3E1 | 2.6E1 | 4.1E1 | 5.7E1 | 4.9E1 | 8.8E1 | 1.0E-9 | 1.0E-9 | 2.7E2 | 3.2E2 | 102 | 13 | 102 | 13 | 0.52 |
| Kd | pg/ml | 1.0E-9 | 1.0E-9 | 2.1E2 | 4.0E3 | 6.7E2 | 1.1E4 | 1.0E-9 | 1.0E-9 | 4.8E3 | 3.8E4 | 102 | 13 | 102 | 13 | 0.66 |

Figure 38 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ke | pg/ml | 1.2E4 | 4.4E4 | 1.4E4 | 6.1E4 | 9.6E3 | 8.3E4 | 6.7E2 | 1.3E4 | 5.5E4 | 3.2E5 | 102 | 13 | 102 | 13 | 0.85 |
| Kf | pg/mL | 6.3E0 | 7.0E0 | 7.0E0 | 1.3E1 | 6.1E0 | 2.0E1 | 1.0E-9 | 1.0E-9 | 4.4E1 | 7.8E1 | 102 | 13 | 102 | 13 | 0.60 |
| Kg | pg/mL | 9.9E2 | 1.0E3 | 1.6E3 | 5.7E3 | 1.6E3 | 1.2E4 | 7.7E1 | 1.3E2 | 8.1E3 | 3.6E4 | 102 | 13 | 102 | 13 | 0.49 |
| Ki | pg/ml | 5.8E1 | 7.8E1 | 6.8E1 | 9.4E1 | 5.5E1 | 6.7E1 | 1.0E-9 | 1.3E1 | 2.9E2 | 2.5E2 | 102 | 13 | 102 | 13 | 0.64 |
| Kj | pg/ml | 8.8E2 | 7.3E2 | 1.4E3 | 2.4E3 | 1.4E3 | 4.2E3 | 6.6E1 | 3.3E1 | 8.8E3 | 1.5E4 | 102 | 13 | 102 | 13 | 0.47 |
| Kk | pg/ml | 6.8E0 | 1.0E1 | 1.3E1 | 2.2E1 | 1.5E1 | 2.2E1 | 1.0E-9 | 2.0E0 | 8.1E1 | 5.9E1 | 102 | 13 | 102 | 13 | 0.63 |
| Kl | pg/ml | 1.9E4 | 1.8E4 | 2.9E4 | 2.3E4 | 2.7E4 | 1.7E4 | 2.3E2 | 3.0E3 | 1.3E5 | 5.1E4 | 102 | 13 | 102 | 13 | 0.49 |
| Kn | pg/ml | 2.9E1 | 6.3E1 | 6.4E1 | 4.9E2 | 1.0E2 | 1.3E3 | 1.0E-9 | 1.0E-9 | 6.3E2 | 4.9E3 | 102 | 13 | 102 | 13 | 0.64 |
| Ko | pg/ml | 3.4E2 | 7.4E2 | 5.0E2 | 8.6E2 | 5.9E2 | 1.0E3 | 1.0E-9 | 1.5E2 | 3.8E3 | 4.1E3 | 102 | 13 | 102 | 13 | 0.68 |
| Kp | pg/ml | 3.6E2 | 3.6E2 | 3.7E2 | 1.4E3 | 2.5E2 | 3.6E3 | 1.0E-9 | 3.7E1 | 9.8E2 | 1.3E4 | 102 | 13 | 102 | 13 | 0.54 |
| Kq | pg/ml | 3.2E2 | 6.6E2 | 4.4E2 | 1.4E4 | 5.0E2 | 4.4E4 | 1.6E0 | 2.9E2 | 3.6E3 | 1.6E5 | 97 | 13 | 97 | 13 | 0.80 |
| Kr | pg/ml | 3.8E-1 | 2.9E0 | 2.1E0 | 3.4E1 | 3.9E0 | 1.1E2 | 1.0E-9 | 1.0E-9 | 2.3E1 | 4.2E2 | 97 | 13 | 97 | 13 | 0.64 |
| Ks | pg/ml | 1.4E4 | 2.2E4 | 2.1E4 | 2.4E4 | 1.9E4 | 1.7E4 | 5.1E1 | 9.9E2 | 7.9E4 | 5.0E4 | 97 | 13 | 97 | 13 | 0.57 |
| Ps | ng/ml | 1.4E2 | 1.2E3 | 5.5E2 | 2.3E3 | 1.9E3 | 2.6E3 | 5.5E0 | 3.5E2 | 1.2E4 | 7.6E3 | 42 | 7 | 42 | 7 | 0.90 |
| Kx | ng/ml | 1.0E-9 | 1.3E-2 | 7.7E-3 | 2.0E-2 | 1.6E-2 | 2.5E-2 | 1.0E-9 | 1.0E-9 | 1.0E-1 | 6.5E-2 | 101 | 13 | 101 | 13 | 0.67 |
| Ky | ng/ml | 1.5E-1 | 2.7E-1 | 4.2E-1 | 6.5E-1 | 8.2E-1 | 8.1E-1 | 1.0E-9 | 1.0E-9 | 5.1E0 | 2.7E0 | 101 | 13 | 101 | 13 | 0.63 |
| Kz | ng/ml | 1.0E-9 | 4.7E-3 | 3.4E-3 | 8.1E-3 | 5.5E-3 | 8.9E-3 | 1.0E-9 | 1.0E-9 | 1.4E-2 | 2.5E-2 | 101 | 13 | 101 | 13 | 0.63 |
| Rz | ng/ml | 3.3E-1 | 3.3E-1 | 6.6E-1 | 1.5E0 | 8.4E-1 | 2.7E0 | 4.6E-3 | 1.7E-2 | 3.4E0 | 7.5E0 | 42 | 7 | 42 | 7 | 0.55 |
| Ry | ng/ml | 1.6E-2 | 2.3E-2 | 2.4E-2 | 7.4E-2 | 2.7E-2 | 1.2E-1 | 1.0E-9 | 8.5E-3 | 1.2E-1 | 3.5E-1 | 42 | 7 | 42 | 7 | 0.64 |
| Rx | ng/ml | 1.0E-9 | 3.5E-5 | 1.5E-3 | 2.1E-3 | 2.4E-3 | 3.0E-3 | 1.0E-9 | 1.0E-9 | 8.6E-3 | 7.6E-3 | 42 | 7 | 42 | 7 | 0.63 |
| Ld | pg/ml | 1.0E-9 | 3.6E0 | 3.7E0 | 8.1E0 | 9.3E0 | 9.5E0 | 1.0E-9 | 1.0E-9 | 6.9E1 | 2.9E1 | 103 | 13 | 103 | 13 | 0.70 |
| Lh | pg/ml | 1.3E4 | 2.0E4 | 2.3E4 | 6.0E4 | 3.0E4 | 1.1E5 | 1.0E-9 | 1.3E2 | 2.6E5 | 4.8E5 | 229 | 41 | 229 | 41 | 0.64 |
| Li | pg/ml | 3.3E3 | 2.0E4 | 1.4E4 | 5.4E4 | 6.6E4 | 8.8E4 | 1.3E1 | 1.9E2 | 9.2E5 | 4.1E5 | 229 | 41 | 229 | 41 | 0.78 |
| Lj | pg/ml | 2.5E3 | 1.6E4 | 1.7E4 | 4.2E4 | 5.2E4 | 6.8E4 | 1.0E-9 | 1.8E2 | 4.3E5 | 3.9E5 | 229 | 41 | 229 | 41 | 0.73 |
| Lp | pg/ml | 1.2E1 | 1.1E0 | 4.5E1 | 4.5E2 | 1.1E2 | 6.0E2 | 1.0E-9 | 1.0E-9 | 5.8E2 | 1.4E3 | 42 | 7 | 42 | 7 | 0.52 |
| Lt | pg/ml | 1.0E-9 | 1.0E-9 | 2.0E0 | 1.0E-9 | 6.5E0 | 0.0E0 | 1.0E-9 | 1.0E-9 | 2.5E1 | 1.0E-9 | 42 | 7 | 42 | 7 | 0.45 |
| Rv | ng/ml | 5.0E-4 | 5.8E-4 | 1.2E-3 | 3.3E-3 | 2.5E-3 | 5.2E-3 | 1.0E-9 | 1.0E-9 | 1.6E-2 | 1.2E-2 | 42 | 7 | 42 | 7 | 0.49 |
| Ru | ng/ml | 1.0E-9 | 1.0E-9 | 1.2E-2 | 1.1E-1 | 5.7E-2 | 1.6E-1 | 1.0E-9 | 1.0E-9 | 3.1E-1 | 3.5E-1 | 42 | 7 | 42 | 7 | 0.69 |
| Rt | ng/ml | 8.0E-2 | 5.1E-2 | 1.2E-1 | 1.2E0 | 1.2E-1 | 2.8E0 | 2.2E-3 | 1.3E-3 | 5.8E-1 | 7.4E0 | 42 | 7 | 42 | 7 | 0.42 |
| Yl | pg/ml | 1.2E1 | 1.5E1 | 1.7E1 | 4.8E1 | 1.8E1 | 7.7E1 | 1.0E-9 | 1.0E-9 | 7.9E1 | 2.2E2 | 43 | 7 | 43 | 7 | 0.59 |
| Rm | ng/ml | 1.7E1 | 7.0E1 | 4.8E1 | 7.7E1 | 9.1E1 | 8.3E1 | 2.2E-1 | 4.4E0 | 6.5E2 | 2.5E2 | 99 | 13 | 99 | 13 | 0.67 |
| Rh | ng/ml | 1.7E2 | 1.6E2 | 3.0E2 | 1.5E3 | 5.0E2 | 4.7E3 | 7.5E0 | 2.5E1 | 3.8E3 | 1.7E4 | 99 | 13 | 99 | 13 | 0.45 |
| Ri | ng/ml | 4.4E-2 | 1.0E-9 | 3.4E0 | 1.6E0 | 6.9E0 | 4.3E0 | 1.0E-9 | 1.0E-9 | 4.5E1 | 1.6E1 | 99 | 13 | 99 | 13 | 0.36 |
| Rg | ng/ml | 1.0E-9 | 1.0E-9 | 1.1E-1 | 1.7E-2 | 4.9E-1 | 5.7E-2 | 1.0E-9 | 1.0E-9 | 3.3E0 | 2.1E-1 | 99 | 13 | 99 | 13 | 0.46 |
| Rj | ng/ml | 1.0E-9 | 1.0E-9 | 9.1E-1 | 2.1E1 | 2.1E0 | 7.5E1 | 1.0E-9 | 1.0E-9 | 1.1E1 | 2.7E2 | 99 | 13 | 99 | 13 | 0.53 |
| Rf | ng/ml | 3.4E-1 | 1.1E0 | 7.1E-1 | 3.3E0 | 1.2E0 | 5.4E0 | 2.1E-2 | 1.9E-1 | 9.9E0 | 1.7E1 | 99 | 13 | 99 | 13 | 0.77 |
| Ql | pg/ml | 1.7E0 | 1.2E1 | 1.2E1 | 2.6E1 | 2.4E1 | 2.9E1 | 1.0E-9 | 1.0E-9 | 1.8E2 | 9.3E1 | 100 | 13 | 100 | 13 | 0.69 |
| Qm | pg/ml | 2.0E0 | 2.7E1 | 1.9E1 | 3.7E1 | 3.6E1 | 3.4E1 | 1.0E-9 | 1.0E-9 | 1.9E2 | 1.0E2 | 100 | 13 | 100 | 13 | 0.69 |
| Qn | pg/ml | 6.0E-1 | 1.1E0 | 5.9E0 | 2.8E0 | 2.4E1 | 4.2E0 | 1.0E-9 | 1.0E-9 | 2.2E2 | 1.2E1 | 100 | 13 | 100 | 13 | 0.61 |
| Nv | pg/ml | 3.8E3 | 7.7E3 | 1.0E4 | 1.9E4 | 2.1E4 | 2.9E4 | 1.0E-9 | 3.3E2 | 1.6E5 | 1.2E5 | 230 | 41 | 230 | 41 | 0.68 |
| Nw | pg/ml | 9.5E3 | 1.9E4 | 1.3E4 | 3.2E4 | 1.7E4 | 4.4E4 | 1.9E2 | 5.1E3 | 2.1E5 | 2.2E5 | 230 | 41 | 230 | 41 | 0.78 |
| Nx | pg/ml | 2.2E2 | 4.2E2 | 4.5E2 | 6.6E2 | 6.4E2 | 8.3E2 | 1.0E-9 | 1.0E-9 | 3.5E3 | 4.1E3 | 230 | 41 | 230 | 41 | 0.56 |
| Ny | pg/ml | 5.7E0 | 1.9E1 | 1.3E2 | 1.4E2 | 1.6E3 | 4.4E2 | 1.0E-9 | 1.0E-9 | 2.5E4 | 2.8E3 | 230 | 41 | 230 | 41 | 0.71 |
| Oa | pg/ml | 1.4E2 | 9.1E2 | 4.5E2 | 1.1E3 | 7.5E2 | 1.0E3 | 1.0E-9 | 4.9E0 | 4.5E3 | 3.4E3 | 100 | 13 | 100 | 13 | 0.72 |
| Op | pg/ml | 4.4E5 | 4.0E5 | 4.3E5 | 3.9E5 | 1.6E5 | 1.7E5 | 5.2E4 | 9.4E4 | 7.5E5 | 6.6E5 | 42 | 7 | 42 | 7 | 0.44 |
| Oe | pg/ml | 4.9E1 | 4.7E0 | 2.8E2 | 1.7E2 | 4.1E2 | 3.1E2 | 1.0E-9 | 1.0E-9 | 2.3E3 | 1.1E3 | 229 | 40 | 229 | 40 | 0.43 |
| Of | pg/ml | 2.0E2 | 9.7E1 | 6.8E3 | 3.5E3 | 2.5E4 | 1.1E4 | 1.0E-9 | 1.0E-9 | 1.9E5 | 6.6E4 | 230 | 41 | 230 | 41 | 0.45 |
| Og | pg/ml | 8.2E-2 | 1.7E-2 | 4.4E-1 | 7.8E-2 | 1.7E0 | 1.5E-1 | 1.0E-9 | 1.0E-9 | 1.9E1 | 8.0E-1 | 230 | 41 | 230 | 41 | 0.35 |
| Oh | pg/ml | 2.7E0 | 7.2E0 | 1.7E1 | 4.4E2 | 1.1E2 | 2.5E3 | 1.0E-9 | 1.0E-9 | 1.4E3 | 1.6E4 | 230 | 41 | 230 | 41 | 0.62 |
| Oi | pg/ml | 2.6E0 | 2.4E0 | 5.4E0 | 5.1E0 | 7.4E0 | 7.0E0 | 1.0E-9 | 1.0E-9 | 4.2E1 | 3.1E1 | 230 | 41 | 230 | 41 | 0.49 |
| Ok | pg/ml | 4.1E2 | 6.4E2 | 5.1E2 | 1.1E3 | 4.4E2 | 1.4E3 | 1.5E1 | 1.1E2 | 3.2E3 | 7.8E3 | 230 | 41 | 230 | 41 | 0.71 |
| Om | pg/ml | 4.2E2 | 7.2E2 | 8.9E2 | 2.4E3 | 2.4E3 | 8.0E3 | 1.0E-9 | 1.1E2 | 3.0E4 | 5.1E4 | 230 | 41 | 230 | 41 | 0.65 |
| On | pg/ml | 1.9E2 | 3.3E2 | 3.0E2 | 8.6E2 | 4.5E2 | 1.5E3 | 8.4E-1 | 2.7E1 | 4.5E3 | 8.5E3 | 230 | 41 | 230 | 41 | 0.71 |
| Or | pg/ml | 1.2E1 | 1.9E1 | 4.0E1 | 1.0E2 | 7.4E1 | 1.7E2 | 1.0E-9 | 1.0E-9 | 4.4E2 | 5.1E2 | 103 | 13 | 103 | 13 | 0.55 |
| Ow | pg/ml | 4.2E1 | 1.2E2 | 1.4E2 | 5.4E2 | 3.7E2 | 8.8E2 | 1.0E-9 | 1.0E-9 | 2.7E3 | 3.0E3 | 103 | 13 | 103 | 13 | 0.63 |
| Ou | pg/ml | 5.6E2 | 6.2E2 | 1.2E3 | 1.9E3 | 2.0E3 | 2.9E3 | 1.0E-9 | 1.0E-9 | 1.1E4 | 8.2E3 | 103 | 13 | 103 | 13 | 0.52 |
| Ul | ng/ml | 1.0E-9 | 1.0E-9 | 9.3E-1 | 5.9E0 | 3.9E0 | 1.6E1 | 1.0E-9 | 1.0E-9 | 2.3E1 | 5.6E1 | 101 | 13 | 101 | 13 | 0.54 |

Figure 38 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Uo | ng/ml | 1.0E-9 | 1.0E-9 | 7.7E-2 | 5.5E-2 | 2.1E-1 | 1.7E-1 | 1.0E-9 | 1.0E-9 | 1.3E0 | 6.3E-1 | 101 | 13 | 101 | 13 | 0.46 |
| Uk | ng/ml | 1.0E-9 | 1.0E-9 | 7.2E-3 | 3.4E-3 | 3.6E-2 | 8.9E-3 | 1.0E-9 | 1.0E-9 | 3.2E-1 | 3.1E-2 | 101 | 13 | 101 | 13 | 0.50 |
| Um | ng/ml | 1.0E-9 | 1.0E-9 | 2.4E-1 | 2.3E-1 | 6.2E-1 | 6.4E-1 | 1.0E-9 | 1.0E-9 | 3.6E0 | 2.3E0 | 101 | 13 | 101 | 13 | 0.45 |
| Uf | ng/ml | 6.1E-2 | 9.6E-2 | 1.4E-1 | 5.4E-1 | 2.0E-1 | 1.4E0 | 1.0E-3 | 2.1E-2 | 1.1E0 | 5.1E0 | 101 | 13 | 101 | 13 | 0.66 |
| Uh | ng/ml | 2.2E0 | 7.2E0 | 3.2E0 | 8.3E0 | 2.9E0 | 5.2E0 | 3.6E-2 | 7.1E-1 | 1.3E1 | 1.8E1 | 101 | 13 | 101 | 13 | 0.81 |
| Un | ng/ml | 1.7E0 | 3.8E0 | 1.9E0 | 4.9E0 | 1.2E0 | 6.4E0 | 3.4E-1 | 1.0E0 | 8.0E0 | 2.5E1 | 101 | 13 | 101 | 13 | 0.73 |
| Ug | ng/ml | 1.0E1 | 9.8E0 | 2.1E1 | 2.7E1 | 2.5E1 | 4.6E1 | 1.2E0 | 2.1E0 | 1.4E2 | 1.6E2 | 101 | 13 | 101 | 13 | 0.49 |
| Ur | ng/ml | 1.1E-1 | 1.0E-9 | 3.1E-1 | 1.1E0 | 5.4E-1 | 2.5E0 | 1.0E-9 | 1.0E-9 | 3.0E0 | 7.3E0 | 100 | 13 | 100 | 13 | 0.38 |
| Up | ng/ml | 1.0E-9 | 1.0E-9 | 3.1E-3 | 1.9E-3 | 9.7E-3 | 6.6E-1 | 1.0E-9 | 1.0E-9 | 5.3E-2 | 2.4E0 | 100 | 13 | 100 | 13 | 0.56 |
| Us | ng/ml | 4.1E-3 | 1.0E-9 | 1.8E-2 | 1.4E-1 | 4.7E-2 | 4.6E-1 | 1.0E-9 | 1.0E-9 | 3.6E-1 | 1.7E0 | 100 | 13 | 100 | 13 | 0.43 |
| Uv | ng/ml | 3.1E-3 | 1.6E-3 | 1.3E-2 | 3.5E-2 | 3.3E-2 | 1.1E-1 | 1.0E-9 | 1.0E-9 | 2.3E-1 | 4.1E-1 | 100 | 13 | 100 | 13 | 0.42 |
| Ut | ng/ml | 7.0E-1 | 1.9E0 | 2.7E0 | 1.0E1 | 6.4E0 | 1.8E1 | 1.0E-9 | 4.6E-1 | 5.2E1 | 6.5E1 | 100 | 13 | 100 | 13 | 0.75 |
| Uu | ng/ml | 7.2E0 | 5.2E0 | 7.7E0 | 5.8E0 | 5.1E0 | 2.9E0 | 5.7E-1 | 2.2E0 | 2.9E1 | 1.2E1 | 100 | 13 | 100 | 13 | 0.39 |
| Uw | ng/ml | 2.3E0 | 4.0E0 | 2.7E0 | 9.0E0 | 2.2E0 | 1.3E1 | 1.0E-9 | 1.7E0 | 7.9E0 | 3.9E1 | 43 | 7 | 43 | 7 | 0.73 |
| Vb | ng/ml | 1.1E0 | 1.1E0 | 1.1E0 | 1.7E0 | 4.2E-1 | 2.1E0 | 8.5E-2 | 2.6E-1 | 2.0E0 | 6.4E0 | 43 | 7 | 43 | 7 | 0.48 |
| Vc | ng/ml | 1.0E-9 | 1.0E-9 | 3.2E-3 | 1.0E-9 | 1.7E-2 | 0.0E0 | 1.0E-9 | 1.0E-9 | 1.1E-1 | 1.0E-9 | 43 | 7 | 43 | 7 | 0.47 |
| Uy | ng/ml | 1.3E0 | 1.0E0 | 5.8E0 | 2.2E1 | 1.7E1 | 2.7E1 | 8.7E-2 | 2.0E-2 | 9.9E1 | 6.4E1 | 43 | 7 | 43 | 7 | 0.55 |
| Uz | ng/ml | 1.0E-9 | 1.0E-9 | 1.0E-2 | 4.8E0 | 6.6E-2 | 1.2E1 | 1.0E-9 | 1.0E-9 | 4.4E-1 | 3.3E1 | 43 | 7 | 43 | 7 | 0.63 |
| Ux | ng/ml | 2.0E2 | 1.6E2 | 2.0E2 | 1.8E2 | 1.3E2 | 1.5E2 | 4.5E0 | 4.0E1 | 4.6E2 | 4.9E2 | 43 | 7 | 43 | 7 | 0.44 |
| Va | ng/ml | 1.6E1 | 3.2E0 | 2.7E1 | 3.2E0 | 3.0E1 | 1.5E0 | 3.1E-1 | 1.2E0 | 1.2E2 | 5.7E0 | 43 | 7 | 43 | 7 | 0.21 |
| Vh | ng/ml | 1.1E-2 | 2.7E-2 | 1.9E-2 | 1.4E-1 | 2.6E-2 | 3.2E-1 | 1.0E-3 | 3.5E-3 | 1.2E-1 | 8.6E-1 | 43 | 7 | 43 | 7 | 0.71 |
| Vi | ng/ml | 3.1E-3 | 4.3E-2 | 9.3E-3 | 3.0E-1 | 1.9E-2 | 6.7E-1 | 1.0E-9 | 1.6E-2 | 1.2E-1 | 1.8E0 | 43 | 7 | 43 | 7 | 0.92 |
| Vp | ng/ml | 1.0E-9 | 1.0E-9 | 1.1E-1 | 4.2E0 | 4.7E-1 | 1.4E1 | 1.0E-9 | 1.0E-9 | 3.9E0 | 4.9E1 | 101 | 13 | 101 | 13 | 0.55 |
| Vt | ng/ml | 6.1E0 | 1.2E1 | 8.0E0 | 2.6E1 | 6.7E0 | 4.0E1 | 5.6E-1 | 1.9E0 | 3.2E1 | 1.6E2 | 101 | 13 | 101 | 13 | 0.75 |
| Vu | ng/ml | 1.0E-9 | 4.5E-1 | 1.7E0 | 2.3E0 | 3.6E0 | 4.0E0 | 1.0E-9 | 1.0E-9 | 2.2E1 | 1.3E1 | 99 | 11 | 99 | 11 | 0.59 |
| Vq | ng/ml | 1.3E2 | 9.2E2 | 6.4E2 | 1.5E3 | 1.6E3 | 1.8E3 | 9.2E-1 | 1.8E1 | 1.2E4 | 4.9E3 | 81 | 9 | 81 | 9 | 0.72 |
| Vo | ng/ml | 2.5E1 | 2.6E1 | 2.5E1 | 2.4E1 | 5.8E0 | 3.9E0 | 4.9E0 | 1.7E1 | 4.8E1 | 3.0E1 | 101 | 13 | 101 | 13 | 0.45 |
| Vs | ng/ml | 1.0E-9 | 1.0E-9 | 4.3E0 | 4.3E1 | 1.1E1 | 1.3E2 | 1.0E-9 | 1.0E-9 | 8.9E1 | 4.5E2 | 99 | 12 | 99 | 12 | 0.46 |
| Vv | ng/ml | 3.2E0 | 3.1E0 | 6.0E0 | 7.4E0 | 1.0E1 | 1.2E1 | 1.0E-9 | 1.0E-9 | 8.4E1 | 4.4E1 | 101 | 12 | 101 | 12 | 0.49 |
| Vw | ng/ml | 3.6E1 | 5.7E1 | 3.3E1 | 4.7E1 | 1.7E1 | 2.4E1 | 2.5E0 | 1.1E1 | 6.7E1 | 6.9E1 | 43 | 7 | 43 | 7 | 0.71 |
| Oy | pg/ml | 5.1E-1 | 4.3E-1 | 7.9E0 | 3.3E0 | 3.7E1 | 7.3E0 | 1.0E-9 | 1.0E-9 | 4.0E2 | 3.3E1 | 229 | 41 | 229 | 41 | 0.45 |
| Oz | pg/ml | 3.9E-2 | 1.0E-9 | 3.9E-1 | 7.9E-1 | 1.9E0 | 4.4E0 | 1.0E-9 | 1.0E-9 | 2.9E1 | 2.8E1 | 229 | 41 | 229 | 41 | 0.36 |
| Pa | pg/ml | 4.1E-1 | 7.9E-1 | 1.4E0 | 1.0E1 | 6.6E0 | 3.8E1 | 1.0E-9 | 1.0E-9 | 8.6E1 | 2.3E2 | 229 | 41 | 229 | 41 | 0.63 |
| Pb | pg/ml | 1.0E-9 | 1.0E-9 | 2.4E0 | 8.8E-1 | 3.2E1 | 4.9E0 | 1.0E-9 | 1.0E-9 | 4.9E2 | 3.2E1 | 229 | 41 | 229 | 41 | 0.38 |
| Pc | pg/ml | 1.6E-1 | 1.0E-9 | 4.4E-1 | 9.2E0 | 1.0E0 | 5.2E1 | 1.0E-9 | 1.0E-9 | 1.4E1 | 3.3E2 | 229 | 41 | 229 | 41 | 0.42 |
| Pd | pg/ml | 1.7E0 | 2.9E0 | 7.6E0 | 1.0E1 | 5.6E1 | 2.1E1 | 1.0E-9 | 1.0E-9 | 8.4E2 | 1.2E2 | 229 | 41 | 229 | 41 | 0.59 |
| Pe | pg/ml | 2.1E1 | 6.9E1 | 1.2E2 | 8.5E2 | 5.2E2 | 2.6E3 | 1.0E-9 | 1.0E-9 | 4.7E3 | 1.5E4 | 229 | 41 | 229 | 41 | 0.74 |
| Pf | pg/ml | 1.7E0 | 7.8E0 | 1.5E1 | 3.0E1 | 1.0E2 | 7.0E1 | 1.0E-9 | 1.0E-9 | 1.5E3 | 4.3E2 | 229 | 41 | 229 | 41 | 0.74 |
| Pg | pg/ml | 4.0E0 | 1.6E1 | 9.0E1 | 1.9E2 | 6.2E2 | 4.6E2 | 1.0E-9 | 1.0E-9 | 7.7E3 | 2.2E3 | 229 | 41 | 229 | 41 | 0.70 |
| Ph | ng/ml | 1.4E-1 | 2.4E-1 | 3.5E-1 | 7.3E-1 | 5.3E-1 | 1.4E0 | 1.0E-9 | 1.0E-9 | 2.8E0 | 5.4E0 | 103 | 13 | 103 | 13 | 0.58 |
| Pi | ng/ml | 1.9E-1 | 3.5E-1 | 2.9E-1 | 6.9E0 | 4.0E-1 | 2.3E1 | 1.0E-9 | 2.1E-2 | 3.2E0 | 8.2E1 | 103 | 13 | 103 | 13 | 0.65 |
| Pj | ng/mL | 4.9E0 | 7.4E0 | 5.9E0 | 9.3E0 | 4.6E0 | 5.4E0 | 4.0E-1 | 4.3E0 | 3.1E1 | 2.3E1 | 103 | 13 | 103 | 13 | 0.71 |
| Pk | ng/ml | 9.0E-3 | 1.3E-2 | 1.4E-2 | 1.3E-1 | 2.9E-2 | 4.2E-1 | 1.0E-9 | 1.3E-4 | 2.5E-1 | 1.5E0 | 103 | 13 | 103 | 13 | 0.67 |
| aA | mg/dL | 8.8E-1 | 1.0E0 | 9.8E-1 | 1.4E0 | 4.7E-1 | 1.0E0 | 3.0E-1 | 5.0E-1 | 4.2E0 | 4.7E0 | 351 | 54 | 351 | 54 | 0.64 |
| aC | mg/mL | 2.1E0 | 2.4E0 | 2.4E0 | 2.6E0 | 1.2E0 | 1.3E0 | 7.5E-1 | 1.0E0 | 7.2E0 | 5.5E0 | 121 | 21 | 121 | 21 | 0.53 |
| aD | ug/mL | 3.1E0 | 2.4E0 | 4.6E0 | 4.5E0 | 4.1E0 | 4.3E0 | 7.5E-1 | 9.2E-1 | 3.1E1 | 1.8E1 | 121 | 21 | 121 | 21 | 0.45 |
| aE | mg/mL | 5.9E-1 | 5.1E-1 | 6.0E-1 | 5.4E-1 | 1.8E-1 | 1.5E-1 | 1.8E-1 | 2.2E-1 | 1.2E0 | 9.6E-1 | 121 | 21 | 121 | 21 | 0.39 |
| aF | ng/mL | 2.2E0 | 2.9E0 | 5.5E0 | 3.7E0 | 8.5E0 | 4.0E0 | 4.3E-3 | 4.3E-3 | 5.0E1 | 1.5E1 | 121 | 21 | 121 | 21 | 0.47 |
| aG | mg/mL | 1.4E-1 | 1.3E-1 | 1.6E-1 | 1.4E-1 | 8.4E-2 | 5.7E-2 | 5.0E-2 | 6.8E-2 | 4.8E-1 | 2.5E-1 | 121 | 21 | 121 | 21 | 0.46 |
| aH | ug/mL | 7.2E1 | 5.9E1 | 7.8E1 | 6.1E1 | 4.0E1 | 2.5E1 | 1.5E1 | 1.1E1 | 2.0E2 | 1.1E2 | 121 | 21 | 121 | 21 | 0.40 |
| aI | ug/mL | 1.7E2 | 1.4E2 | 1.7E2 | 1.6E2 | 6.1E1 | 5.3E1 | 4.7E1 | 7.6E1 | 3.4E2 | 2.7E2 | 121 | 21 | 121 | 21 | 0.41 |
| aJ | ug/mL | 2.4E0 | 3.0E0 | 3.1E0 | 4.0E0 | 2.2E0 | 2.7E0 | 8.2E-1 | 1.4E0 | 1.4E1 | 1.1E1 | 121 | 21 | 121 | 21 | 0.59 |
| aK | ng/mL | 1.3E0 | 1.4E0 | 2.0E0 | 1.7E0 | 1.9E0 | 1.5E0 | 2.9E-4 | 1.3E-1 | 1.0E1 | 6.5E0 | 121 | 21 | 121 | 21 | 0.47 |
| aL | mg/mL | 7.2E-1 | 7.4E-1 | 7.6E-1 | 7.0E-1 | 2.3E-1 | 2.3E-1 | 2.2E-1 | 2.7E-1 | 1.7E0 | 1.1E0 | 121 | 21 | 121 | 21 | 0.46 |
| aM | U/mL | 1.7E1 | 2.3E1 | 3.3E1 | 8.8E1 | 4.8E1 | 1.9E2 | 4.2E-2 | 4.2E-2 | 3.5E2 | 8.2E2 | 121 | 21 | 121 | 21 | 0.58 |
| aN | U/mL | 1.5E1 | 1.4E1 | 2.5E1 | 3.9E1 | 4.0E1 | 7.1E1 | 2.5E-3 | 2.5E-3 | 3.8E2 | 3.3E2 | 121 | 21 | 121 | 21 | 0.51 |
| aO | pg/mL | 6.2E1 | 7.2E1 | 4.5E2 | 4.3E2 | 1.1E3 | 7.4E2 | 6.0E-2 | 6.2E0 | 6.6E3 | 2.4E3 | 121 | 21 | 121 | 21 | 0.55 |

Figure 38 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aP | ng/mL | 1.6E0 | 1.9E0 | 2.0E0 | 2.5E0 | 1.3E0 | 1.7E0 | 5.4E-1 | 7.8E-1 | 6.6E0 | 6.1E0 | 121 | 21 | 121 | 21 | 0.58 |
| aQ | ng/mL | 2.4E-1 | 2.4E-1 | 3.5E-1 | 2.9E-1 | 3.3E-1 | 2.1E-1 | 2.0E-4 | 5.1E-2 | 2.0E0 | 9.0E-1 | 121 | 21 | 121 | 21 | 0.48 |
| aR | ng/mL | 1.9E0 | 1.4E0 | 3.1E0 | 3.4E0 | 4.2E0 | 3.8E0 | 2.6E-1 | 6.6E-1 | 3.4E1 | 1.7E1 | 121 | 21 | 121 | 21 | 0.52 |
| aS | ng/mL | 4.0E-1 | 4.0E-1 | 1.2E0 | 9.4E-1 | 3.1E0 | 1.2E0 | 4.2E-3 | 6.0E-2 | 3.3E1 | 4.9E0 | 121 | 21 | 121 | 21 | 0.49 |
| aU | pg/mL | 6.8E1 | 6.1E1 | 1.0E2 | 9.7E1 | 1.1E2 | 1.1E2 | 7.4E-2 | 7.4E-2 | 7.0E2 | 5.1E2 | 121 | 21 | 121 | 21 | 0.49 |
| aV | ng/mL | 5.9E-1 | 5.2E-1 | 1.1E0 | 7.5E-1 | 3.0E0 | 6.6E-1 | 7.6E-4 | 9.1E-2 | 3.3E1 | 2.4E0 | 121 | 21 | 121 | 21 | 0.48 |
| aW | pg/mL | 2.0E1 | 1.7E1 | 2.4E1 | 1.8E1 | 4.0E1 | 1.2E1 | 7.2E-2 | 7.2E-2 | 4.2E2 | 4.7E1 | 121 | 21 | 121 | 21 | 0.44 |
| aX | ng/mL | 8.0E0 | 3.3E0 | 1.1E1 | 1.4E1 | 1.0E1 | 2.4E1 | 3.0E-1 | 7.7E-1 | 5.4E1 | 1.1E2 | 121 | 21 | 121 | 21 | 0.42 |
| aY | pg/mL | 5.3E1 | 4.6E1 | 8.0E1 | 5.3E1 | 1.2E2 | 4.3E1 | 4.1E-1 | 4.1E-1 | 1.2E3 | 2.0E2 | 121 | 21 | 121 | 21 | 0.42 |
| aZ | pg/mL | 2.2E2 | 3.0E2 | 5.7E2 | 9.9E2 | 1.3E3 | 1.3E3 | 1.7E0 | 1.5E1 | 1.2E4 | 4.7E3 | 121 | 21 | 121 | 21 | 0.62 |
| bA | ng/mL | 1.4E1 | 3.8E1 | 5.7E1 | 1.5E2 | 1.1E2 | 2.6E2 | 3.0E-2 | 2.0E0 | 9.4E2 | 9.4E2 | 121 | 21 | 121 | 21 | 0.61 |
| bB | ng/mL | 2.7E2 | 2.7E2 | 2.9E2 | 2.6E2 | 1.6E2 | 1.6E2 | 1.2E1 | 3.3E1 | 8.1E2 | 5.7E2 | 121 | 21 | 121 | 21 | 0.44 |
| bC | ng/mL | 3.2E2 | 2.9E2 | 5.8E2 | 7.1E2 | 7.4E2 | 1.1E3 | 2.7E1 | 5.0E1 | 4.7E3 | 4.0E3 | 121 | 21 | 121 | 21 | 0.49 |
| bE | mg/mL | 5.0E0 | 5.1E0 | 5.2E0 | 5.4E0 | 1.8E0 | 2.3E0 | 1.8E0 | 1.3E0 | 1.2E1 | 1.1E1 | 121 | 21 | 121 | 21 | 0.51 |
| bF | pg/mL | 3.5E1 | 5.4E1 | 4.3E2 | 2.9E2 | 1.6E3 | 5.9E2 | 5.0E-2 | 8.9E0 | 1.1E4 | 2.2E3 | 121 | 21 | 121 | 21 | 0.61 |
| bG | ng/mL | 1.7E0 | 2.3E0 | 3.4E0 | 3.6E0 | 4.9E0 | 4.0E0 | 1.1E-1 | 2.4E-1 | 3.0E1 | 1.5E1 | 121 | 21 | 121 | 21 | 0.54 |
| bH | pg/mL | 5.7E-1 | 5.7E-1 | 7.2E0 | 5.5E0 | 2.8E1 | 6.7E0 | 5.7E-1 | 5.7E-1 | 2.8E2 | 2.3E1 | 121 | 21 | 121 | 21 | 0.57 |
| bI | ng/mL | 4.0E-3 | 4.0E-3 | 1.0E-1 | 7.5E-2 | 2.1E-1 | 1.8E-1 | 4.0E-3 | 4.0E-3 | 9.8E-1 | 6.2E-1 | 121 | 21 | 121 | 21 | 0.46 |
| bJ | mg/mL | 1.7E0 | 1.9E0 | 2.1E0 | 2.2E0 | 1.8E0 | 2.1E0 | 2.5E-4 | 2.5E-4 | 1.1E1 | 8.9E0 | 121 | 21 | 121 | 21 | 0.51 |
| bL | ng/mL | 4.3E0 | 3.2E0 | 9.1E0 | 7.9E0 | 1.1E1 | 8.4E0 | 4.6E-2 | 4.6E-2 | 4.9E1 | 3.0E1 | 121 | 21 | 121 | 21 | 0.50 |
| bM | mg/mL | 1.9E0 | 1.7E0 | 2.3E0 | 1.8E0 | 1.5E0 | 1.2E0 | 2.4E-1 | 1.8E-2 | 8.6E0 | 5.2E0 | 121 | 21 | 121 | 21 | 0.42 |
| bN | ng/mL | 3.9E1 | 2.1E1 | 1.3E2 | 4.4E1 | 3.0E2 | 5.3E1 | 1.4E-1 | 5.9E-1 | 1.9E3 | 1.9E2 | 121 | 21 | 121 | 21 | 0.36 |
| bO | ng/mL | 4.0E-2 | 4.0E-2 | 7.3E0 | 1.5E1 | 1.5E1 | 3.3E1 | 4.0E-2 | 4.0E-2 | 7.1E1 | 1.3E2 | 121 | 21 | 121 | 21 | 0.48 |
| bP | mg/mL | 4.9E-1 | 5.2E-1 | 7.3E-1 | 5.5E-1 | 7.1E-1 | 3.1E-1 | 8.2E-3 | 9.2E-2 | 4.8E0 | 1.2E0 | 121 | 21 | 121 | 21 | 0.47 |
| bQ | pg/mL | 2.1E1 | 5.9E1 | 1.7E2 | 6.6E1 | 1.2E3 | 5.8E1 | 1.5E-1 | 1.5E-1 | 1.3E4 | 2.2E2 | 121 | 21 | 121 | 21 | 0.69 |
| bR | ng/mL | 1.2E-2 | 1.2E-2 | 1.7E-1 | 1.0E-1 | 8.4E-1 | 1.3E-1 | 1.2E-2 | 1.2E-2 | 8.7E0 | 3.9E-1 | 121 | 21 | 121 | 21 | 0.55 |
| bS | pg/mL | 9.4E-1 | 9.4E-1 | 1.0E1 | 6.9E0 | 4.8E1 | 1.7E1 | 9.4E-1 | 9.4E-1 | 3.9E2 | 7.2E1 | 121 | 21 | 121 | 21 | 0.52 |
| bU | ng/mL | 5.5E-2 | 1.6E-1 | 2.0E-1 | 1.7E-1 | 6.3E-1 | 1.8E-1 | 1.3E-2 | 1.3E-2 | 6.6E0 | 6.5E-1 | 121 | 21 | 121 | 21 | 0.56 |
| bV | pg/mL | 4.7E2 | 5.3E2 | 5.5E2 | 7.2E2 | 2.7E2 | 5.5E2 | 1.8E2 | 2.7E2 | 1.6E3 | 2.2E3 | 121 | 21 | 121 | 21 | 0.56 |
| bW | pg/mL | 3.3E2 | 3.1E2 | 4.8E2 | 5.2E2 | 5.7E2 | 8.0E2 | 8.4E1 | 1.5E2 | 4.8E3 | 3.9E3 | 121 | 21 | 121 | 21 | 0.50 |
| bX | ng/mL | 2.5E-5 | 3.1E-3 | 2.4E-3 | 2.9E-3 | 2.9E-3 | 2.9E-3 | 2.5E-5 | 2.5E-5 | 1.2E-2 | 7.8E-3 | 121 | 21 | 121 | 21 | 0.54 |
| bZ | pg/mL | 2.9E2 | 3.6E2 | 2.2E3 | 1.3E3 | 8.1E3 | 2.0E3 | 1.5E-1 | 1.0E2 | 5.8E4 | 7.4E3 | 121 | 21 | 121 | 21 | 0.58 |
| cA | pg/mL | 6.0E-1 | 6.0E-1 | 4.7E0 | 2.7E0 | 3.4E1 | 5.6E0 | 6.0E-1 | 6.0E-1 | 3.7E2 | 2.1E1 | 121 | 21 | 121 | 21 | 0.52 |
| cB | ng/mL | 3.7E-2 | 5.1E-2 | 6.0E-2 | 1.0E-1 | 6.9E-2 | 1.3E-1 | 1.7E-3 | 1.7E-3 | 3.7E-1 | 4.3E-1 | 121 | 21 | 121 | 21 | 0.55 |
| cC | pg/mL | 4.1E1 | 4.6E1 | 4.7E1 | 4.3E1 | 5.6E1 | 3.2E1 | 1.0E0 | 1.0E0 | 4.5E2 | 1.1E2 | 121 | 21 | 121 | 21 | 0.52 |
| cD | pg/mL | 4.9E0 | 5.9E0 | 1.6E1 | 6.7E0 | 5.5E1 | 6.9E0 | 3.3E-1 | 3.3E-1 | 4.8E2 | 3.3E1 | 121 | 21 | 121 | 21 | 0.53 |
| cE | pg/mL | 6.5E1 | 1.3E2 | 2.9E2 | 2.1E2 | 6.8E2 | 2.5E2 | 1.2E-1 | 1.4E1 | 3.8E3 | 1.1E3 | 121 | 21 | 121 | 21 | 0.63 |
| cF | pg/mL | 5.3E-1 | 5.3E-1 | 1.6E1 | 1.3E1 | 3.3E1 | 2.0E1 | 5.3E-1 | 5.3E-1 | 2.7E2 | 6.5E1 | 121 | 21 | 121 | 21 | 0.48 |
| cG | pg/mL | 5.3E1 | 9.0E1 | 1.9E2 | 1.3E2 | 9.6E2 | 1.1E2 | 7.8E0 | 2.4E1 | 1.0E4 | 4.1E2 | 121 | 21 | 121 | 21 | 0.63 |
| cH | uIU/mL | 3.4E0 | 2.5E0 | 8.6E0 | 4.8E0 | 1.9E1 | 7.6E0 | 8.6E-3 | 8.6E-3 | 1.6E2 | 3.4E1 | 121 | 21 | 121 | 21 | 0.40 |
| cI | ng/mL | 5.9E0 | 6.9E0 | 1.3E1 | 1.6E1 | 2.0E1 | 2.7E1 | 3.2E-2 | 5.1E-1 | 1.2E2 | 1.2E2 | 121 | 21 | 121 | 21 | 0.51 |
| cJ | ug/mL | 5.9E1 | 6.2E1 | 9.6E1 | 8.1E1 | 1.1E2 | 7.9E1 | 6.9E0 | 7.2E0 | 6.4E2 | 3.4E2 | 121 | 21 | 121 | 21 | 0.48 |
| cK | ng/mL | 3.8E-3 | 3.8E-3 | 2.2E-2 | 1.9E-2 | 1.3E-1 | 4.7E-2 | 3.8E-3 | 3.8E-3 | 1.5E0 | 2.1E-1 | 121 | 21 | 121 | 21 | 0.53 |
| cL | pg/mL | 2.2E2 | 2.0E2 | 6.3E2 | 3.2E2 | 2.4E3 | 2.8E2 | 3.1E1 | 1.1E2 | 2.4E4 | 1.3E3 | 121 | 21 | 121 | 21 | 0.58 |
| cM | pg/mL | 2.6E2 | 2.8E2 | 2.9E2 | 2.8E2 | 1.8E2 | 1.0E2 | 4.2E1 | 5.7E1 | 1.1E3 | 4.5E2 | 121 | 21 | 121 | 21 | 0.54 |
| cN | pg/mL | 1.2E2 | 1.2E2 | 1.4E2 | 1.2E2 | 9.9E1 | 3.2E1 | 3.8E1 | 7.9E1 | 1.1E3 | 2.0E2 | 121 | 21 | 121 | 21 | 0.50 |
| cO | pg/mL | 2.1E2 | 2.4E2 | 4.5E2 | 3.4E2 | 1.8E3 | 3.1E2 | 5.4E1 | 1.3E2 | 1.9E4 | 1.5E3 | 121 | 21 | 121 | 21 | 0.59 |
| cP | ng/mL | 2.5E3 | 2.3E3 | 2.6E3 | 2.5E3 | 9.8E2 | 1.0E3 | 6.2E2 | 1.0E3 | 5.6E3 | 4.7E3 | 121 | 21 | 121 | 21 | 0.48 |
| cQ | ng/mL | 4.9E-2 | 6.7E-2 | 1.2E-1 | 1.6E-1 | 2.1E-1 | 2.5E-1 | 2.0E-3 | 2.0E-3 | 1.3E0 | 8.7E-1 | 121 | 21 | 121 | 21 | 0.51 |
| cR | ng/mL | 2.9E2 | 4.2E2 | 5.6E2 | 6.3E2 | 9.0E2 | 6.1E2 | 2.0E1 | 8.6E1 | 7.7E3 | 2.2E3 | 121 | 21 | 121 | 21 | 0.58 |
| cS | ng/mL | 2.6E2 | 2.5E2 | 3.8E2 | 5.1E2 | 3.9E2 | 5.6E2 | 8.0E1 | 9.7E1 | 2.5E3 | 2.4E3 | 121 | 21 | 121 | 21 | 0.54 |
| cT | ng/mL | 5.3E1 | 9.4E1 | 1.5E2 | 3.0E2 | 2.7E2 | 4.8E2 | 4.2E0 | 1.1E1 | 2.1E3 | 1.5E3 | 121 | 21 | 121 | 21 | 0.57 |
| cU | ng/mL | 5.9E1 | 8.0E1 | 1.0E2 | 1.1E2 | 1.7E2 | 8.4E1 | 6.2E0 | 1.7E1 | 1.6E3 | 3.3E2 | 121 | 21 | 121 | 21 | 0.59 |
| cV | ng/mL | 2.2E-1 | 2.1E-1 | 9.5E-1 | 2.6E-1 | 4.4E0 | 2.0E-1 | 3.4E-2 | 6.8E-2 | 4.7E1 | 9.3E-1 | 121 | 21 | 121 | 21 | 0.48 |
| cW | mIU/mL | 4.8E-2 | 4.2E-2 | 9.4E-2 | 7.5E-2 | 4.1E-1 | 8.2E-2 | 4.8E-3 | 1.4E-2 | 4.5E0 | 3.9E-1 | 121 | 21 | 121 | 21 | 0.53 |
| cX | ng/mL | 1.7E-1 | 6.9E-2 | 2.5E0 | 3.4E-1 | 6.6E0 | 6.1E-1 | 2.3E-4 | 2.3E-4 | 2.8E1 | 2.5E0 | 121 | 21 | 121 | 21 | 0.46 |
| cY | ng/mL | 7.4E0 | 8.9E0 | 1.1E1 | 9.8E0 | 1.1E1 | 8.4E0 | 1.7E-1 | 6.0E-1 | 6.1E1 | 3.6E1 | 121 | 21 | 121 | 21 | 0.50 |

Figure 38 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cZ | ug/mL | 1.2E1 | 1.2E1 | 1.4E1 | 1.4E1 | 5.7E0 | 7.5E0 | 2.8E0 | 3.3E0 | 3.0E1 | 3.0E1 | 121 | 21 | 121 | 21 | 0.47 |
| dA | pg/mL | 3.1E2 | 3.6E2 | 3.8E2 | 3.9E2 | 5.2E2 | 2.2E2 | 1.0E2 | 1.1E2 | 5.8E3 | 8.8E2 | 121 | 21 | 121 | 21 | 0.54 |
| dB | ug/mL | 1.9E1 | 1.5E1 | 1.9E1 | 1.6E1 | 2.3E1 | 8.9E0 | 2.1E0 | 2.2E0 | 2.5E2 | 2.8E1 | 121 | 21 | 121 | 21 | 0.43 |
| dC | nmol/L | 3.4E1 | 3.6E1 | 3.8E1 | 3.6E1 | 1.8E1 | 1.4E1 | 7.8E0 | 1.5E1 | 1.4E2 | 6.5E1 | 121 | 21 | 121 | 21 | 0.49 |
| dD | ug/mL | 3.3E1 | 2.9E1 | 3.4E1 | 3.2E1 | 1.0E1 | 1.1E1 | 1.4E1 | 1.6E1 | 7.4E1 | 6.0E1 | 121 | 21 | 121 | 21 | 0.41 |
| dE | ng/mL | 4.1E-1 | 7.0E-1 | 5.1E-1 | 6.9E-1 | 5.4E-1 | 6.4E-1 | 8.4E-3 | 8.4E-3 | 2.7E0 | 2.4E0 | 121 | 21 | 121 | 21 | 0.59 |
| dF | ng/mL | 2.5E2 | 3.7E2 | 3.4E2 | 4.6E2 | 2.5E2 | 3.1E2 | 7.5E1 | 1.1E2 | 1.3E3 | 1.2E3 | 121 | 21 | 121 | 21 | 0.63 |
| dG | ng/mL | 1.2E1 | 1.4E1 | 1.7E1 | 1.8E1 | 2.0E1 | 1.7E1 | 3.0E0 | 4.8E0 | 1.8E2 | 8.7E1 | 121 | 21 | 121 | 21 | 0.55 |
| dH | pg/mL | 7.7E0 | 1.1E1 | 2.2E1 | 1.0E1 | 6.9E1 | 5.1E0 | 4.0E-2 | 4.0E-2 | 6.7E2 | 2.3E1 | 121 | 21 | 121 | 21 | 0.57 |
| dI | pg/mL | 4.6E-1 | 4.6E-1 | 4.3E0 | 1.7E0 | 3.0E1 | 2.4E0 | 4.6E-1 | 4.6E-1 | 3.3E2 | 8.4E0 | 121 | 21 | 121 | 21 | 0.53 |
| dJ | ng/mL | 1.9E0 | 2.2E0 | 2.1E0 | 2.1E0 | 1.1E0 | 1.1E0 | 3.2E-2 | 3.2E-2 | 5.1E0 | 4.0E0 | 121 | 21 | 121 | 21 | 0.51 |
| dK | uIU/mL | 1.5E0 | 8.6E-1 | 2.3E0 | 2.0E0 | 4.0E0 | 2.8E0 | 2.8E-4 | 4.7E-2 | 3.9E1 | 1.1E1 | 121 | 21 | 121 | 21 | 0.39 |
| dL | ng/mL | 8.8E2 | 8.2E2 | 1.0E3 | 1.1E3 | 5.9E2 | 9.0E2 | 2.8E2 | 4.3E2 | 3.8E3 | 4.8E3 | 121 | 21 | 121 | 21 | 0.50 |
| dM | pg/mL | 9.5E2 | 1.1E3 | 1.3E3 | 1.8E3 | 1.6E3 | 1.6E3 | 3.7E2 | 6.3E2 | 1.5E4 | 5.8E3 | 121 | 21 | 121 | 21 | 0.62 |
| dN | ug/mL | 9.8E1 | 1.1E2 | 1.0E2 | 1.2E2 | 3.7E1 | 6.3E1 | 2.4E1 | 4.7E1 | 2.2E2 | 3.3E2 | 121 | 21 | 121 | 21 | 0.54 |
| dR | pg/ml | 1.3E3 | 9.3E2 | 2.1E3 | 1.2E3 | 2.2E3 | 1.3E3 | 1.4E2 | 1.3E2 | 9.8E3 | 5.3E3 | 97 | 15 | 97 | 15 | 0.34 |
| dX | ng/ml | 5.2E-2 | 8.2E-2 | 1.3E-1 | 1.5E-1 | 2.2E-1 | 1.5E-1 | 2.6E-3 | 2.6E-3 | 1.2E0 | 4.2E-1 | 38 | 7 | 38 | 7 | 0.60 |
| eF | ng/ml | 4.1E0 | 4.3E0 | 4.8E0 | 5.2E0 | 2.2E0 | 3.2E0 | 2.0E0 | 2.0E0 | 1.2E1 | 1.5E1 | 97 | 15 | 97 | 15 | 0.51 |
| eC | pg/ml | 3.0E2 | 2.7E2 | 3.7E2 | 3.9E2 | 2.6E2 | 5.6E2 | 7.1E1 | 1.9E1 | 1.6E3 | 2.0E3 | 90 | 11 | 90 | 11 | 0.38 |
| eD | pg/ml | 2.1E2 | 2.4E2 | 7.2E2 | 2.6E2 | 1.5E3 | 1.5E2 | 5.2E-1 | 5.9E1 | 7.0E3 | 4.9E2 | 74 | 8 | 74 | 8 | 0.53 |
| eM | ng/ml | 3.0E0 | 2.6E0 | 4.4E0 | 4.9E0 | 4.6E0 | 6.5E0 | 6.9E-1 | 8.8E-1 | 2.6E1 | 2.3E1 | 52 | 10 | 52 | 10 | 0.49 |
| eP | ng/ml | 3.7E-3 | 3.7E-3 | 1.4E0 | 1.6E-1 | 4.6E0 | 4.0E-1 | 3.7E-3 | 3.7E-3 | 2.8E1 | 1.1E0 | 38 | 7 | 38 | 7 | 0.39 |
| fP | ng/ml | 2.8E2 | 2.6E2 | 3.4E2 | 3.1E2 | 2.0E2 | 1.6E2 | 1.8E0 | 9.5E1 | 1.0E3 | 6.0E2 | 96 | 13 | 96 | 13 | 0.46 |
| fR | ng/ml | 1.5E5 | 2.1E5 | 2.0E5 | 2.7E5 | 1.6E5 | 3.6E4 | 1.9E2 | 6.3E5 | 6.8E5 | 75 | 16 | 75 | 16 | 0.59 |
| gC | ng/ml | 2.2E2 | 2.8E2 | 2.5E2 | 2.8E2 | 1.1E2 | 1.2E2 | 8.3E1 | 1.5E2 | 6.4E2 | 4.8E2 | 31 | 7 | 31 | 7 | 0.58 |
| gL | pg/ml | 6.3E4 | 7.7E4 | 7.0E4 | 8.7E4 | 3.1E4 | 4.0E4 | 1.1E4 | 4.4E4 | 1.6E5 | 1.7E5 | 97 | 15 | 97 | 15 | 0.64 |
| gP | U/ml | 2.8E2 | 2.7E2 | 2.9E2 | 2.7E2 | 1.3E2 | 7.8E1 | 1.2E1 | 1.3E2 | 1.1E3 | 3.9E2 | 96 | 15 | 96 | 15 | 0.47 |
| gW | ng/ml | 5.2E2 | 3.1E2 | 8.5E2 | 6.7E2 | 1.0E3 | 9.5E2 | 2.3E0 | 1.5E2 | 6.1E3 | 3.1E3 | 73 | 9 | 73 | 9 | 0.41 |
| tF | pg/mL | 1.3E3 | 1.4E3 | 1.4E4 | 4.7E3 | 4.4E4 | 7.6E3 | 1.2E1 | 1.8E1 | 2.8E5 | 2.4E4 | 91 | 12 | 91 | 12 | 0.49 |
| hA | ng/ml | 2.6E0 | 3.6E0 | 1.6E1 | 1.8E1 | 5.5E1 | 3.6E1 | 1.7E-2 | 2.0E0 | 3.5E2 | 1.1E2 | 74 | 9 | 74 | 9 | 0.65 |
| nM | pg/ml | 1.0E-9 | 1.0E-9 | 1.0E-9 | 1.7E2 | 0.0E0 | 5.1E2 | 1.0E-9 | 1.0E-9 | 1.0E-9 | 1.5E3 | 54 | 9 | 54 | 9 | 0.56 |
| nN | pg/ml | 1.2E3 | 3.8E3 | 4.1E3 | 2.7E4 | 1.4E4 | 4.9E4 | 1.1E2 | 1.3E3 | 1.0E5 | 1.5E5 | 54 | 9 | 54 | 9 | 0.80 |
| nO | pg/ml | 2.4E1 | 4.3E1 | 3.7E1 | 3.8E1 | 5.0E1 | 2.4E1 | 4.0E0 | 1.2E1 | 3.1E2 | 8.9E1 | 54 | 9 | 54 | 9 | 0.61 |
| nR | pg/ml | 1.7E1 | 4.2E1 | 7.6E1 | 2.6E2 | 1.5E2 | 6.3E2 | 1.0E0 | 4.7E0 | 8.2E2 | 1.9E3 | 54 | 9 | 54 | 9 | 0.60 |
| nT | pg/ml | 6.7E1 | 1.2E2 | 1.0E2 | 2.3E2 | 1.1E2 | 2.7E2 | 1.0E-9 | 8.5E1 | 6.4E2 | 9.2E2 | 54 | 9 | 54 | 9 | 0.72 |
| nU | pg/ml | 4.2E1 | 1.2E2 | 8.4E1 | 2.2E2 | 2.1E2 | 2.9E2 | 1.0E-9 | 1.0E-9 | 1.5E3 | 9.2E2 | 54 | 9 | 54 | 9 | 0.75 |
| lW | pg/ml | 1.0E-9 | 1.0E-9 | 1.3E1 | 8.8E0 | 3.4E1 | 1.4E1 | 1.0E-9 | 1.0E-9 | 1.7E2 | 3.9E1 | 54 | 9 | 54 | 9 | 0.55 |
| lX | pg/ml | 9.0E2 | 5.3E2 | 9.4E2 | 9.3E2 | 5.1E2 | 7.7E2 | 2.3E2 | 1.9E2 | 2.3E3 | 2.5E3 | 54 | 9 | 54 | 9 | 0.43 |
| lY | pg/ml | 1.9E1 | 2.0E1 | 2.1E1 | 2.0E1 | 1.9E1 | 1.5E1 | 1.0E-9 | 5.7E-1 | 1.2E2 | 4.5E1 | 54 | 9 | 54 | 9 | 0.52 |
| mE | pg/ml | 1.0E-9 | 7.0E-1 | 2.8E0 | 2.5E0 | 8.6E0 | 3.4E0 | 1.0E-9 | 1.0E-9 | 5.7E1 | 9.2E0 | 54 | 9 | 54 | 9 | 0.59 |
| mF | pg/ml | 1.4E-1 | 2.7E-1 | 8.4E0 | 5.5E-1 | 3.6E1 | 6.4E-1 | 1.0E-9 | 1.0E-9 | 2.5E2 | 1.7E0 | 54 | 9 | 54 | 9 | 0.47 |
| mH | pg/ml | 3.0E0 | 5.3E0 | 5.2E0 | 5.7E0 | 8.1E0 | 5.5E0 | 4.0E-1 | 9.0E-1 | 5.3E1 | 1.9E1 | 54 | 9 | 54 | 9 | 0.57 |
| ml | pg/ml | 1.0E-9 | 3.0E1 | 1.1E1 | 7.8E1 | 2.8E1 | 1.5E2 | 1.0E-9 | 1.0E-9 | 1.8E2 | 4.6E2 | 54 | 9 | 54 | 9 | 0.75 |
| mM | pg/ml | 3.8E1 | 6.3E1 | 9.3E1 | 9.6E1 | 1.7E2 | 1.5E2 | 1.0E-9 | 1.0E-9 | 1.1E3 | 4.7E2 | 54 | 9 | 54 | 9 | 0.50 |
| mP | pg/ml | 1.5E1 | 1.6E1 | 1.7E1 | 1.2E2 | 1.7E1 | 2.6E2 | 1.0E-9 | 7.5E0 | 1.2E2 | 8.1E2 | 53 | 9 | 53 | 9 | 0.57 |
| mS | pg/ml | 1.6E3 | 1.4E3 | 1.7E3 | 1.7E3 | 9.6E2 | 1.2E3 | 1.0E-9 | 1.0E-9 | 5.1E3 | 3.5E3 | 54 | 9 | 54 | 9 | 0.49 |
| mT | pg/ml | 5.0E1 | 6.1E1 | 1.3E2 | 3.4E2 | 2.5E2 | 5.9E2 | 1.0E1 | 3.1E1 | 1.4E3 | 1.7E3 | 53 | 9 | 53 | 9 | 0.58 |
| mU | pg/ml | 2.2E0 | 4.1E0 | 7.2E0 | 6.1E0 | 3.0E1 | 6.8E0 | 1.0E-9 | 1.2E0 | 2.2E2 | 2.3E1 | 53 | 9 | 53 | 9 | 0.70 |
| mW | pg/ml | 2.2E3 | 1.9E3 | 2.4E3 | 3.4E3 | 1.3E3 | 3.2E3 | 1.0E-9 | 1.3E3 | 6.2E3 | 1.1E4 | 53 | 9 | 53 | 9 | 0.51 |
| mY | pg/ml | 6.3E2 | 1.1E3 | 8.7E2 | 1.7E3 | 1.0E3 | 2.5E3 | 1.0E-9 | 1.9E2 | 5.6E3 | 8.0E3 | 54 | 9 | 54 | 9 | 0.59 |
| mZ | pg/ml | 2.1E2 | 9.1E1 | 4.0E2 | 1.3E2 | 5.2E2 | 1.6E2 | 1.2E1 | 1.1E1 | 3.1E3 | 5.5E2 | 53 | 9 | 53 | 9 | 0.25 |
| nA | pg/ml | 1.5E0 | 3.4E0 | 6.8E0 | 3.6E0 | 1.4E1 | 3.7E0 | 1.0E-9 | 1.0E-9 | 6.5E1 | 9.1E0 | 53 | 9 | 53 | 9 | 0.52 |
| nB | pg/ml | 2.8E2 | 4.0E2 | 3.1E2 | 4.1E2 | 1.7E2 | 2.3E2 | 3.0E1 | 1.5E2 | 8.2E2 | 9.6E2 | 54 | 9 | 54 | 9 | 0.63 |
| nC | pg/ml | 1.0E-9 | 7.8E2 | 1.2E4 | 2.1E3 | 6.0E4 | 3.2E3 | 1.0E-9 | 1.0E-9 | 3.8E5 | 9.1E3 | 54 | 9 | 54 | 9 | 0.74 |
| nD | pg/ml | 6.7E0 | 6.4E0 | 1.3E1 | 1.0E1 | 3.5E1 | 1.0E1 | 1.0E-9 | 1.0E-9 | 2.6E2 | 2.8E1 | 53 | 9 | 53 | 9 | 0.53 |
| nF | pg/ml | 1.0E-9 | 1.0E-9 | 3.2E0 | 1.5E0 | 1.4E1 | 4.5E0 | 1.0E-9 | 1.0E-9 | 9.3E1 | 1.3E1 | 54 | 9 | 54 | 9 | 0.51 |
| nH | pg/ml | 1.8E-1 | 5.1E0 | 2.4E2 | 2.8E1 | 1.4E3 | 4.1E1 | 1.0E-9 | 1.0E-9 | 1.0E4 | 1.2E2 | 53 | 9 | 53 | 9 | 0.76 |

Figure 38 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nI | pg/ml | 4.6E1 | 1.0E-9 | 6.1E1 | 1.0E-9 | 7.8E1 | 0.0E0 | 1.0E-9 | 1.0E-9 | 3.5E2 | 1.0E-9 | 54 | 9 | 54 | 9 | 0.19 |
| nJ | pg/ml | 2.5E-1 | 1.1E0 | 3.4E0 | 1.0E0 | 1.8E1 | 1.0E0 | 1.0E-9 | 1.0E-9 | 1.3E2 | 3.0E0 | 54 | 9 | 54 | 9 | 0.56 |
| nK | pg/ml | 1.0E-9 | 2.0E1 | 1.1E1 | 2.2E1 | 2.3E1 | 2.2E1 | 1.0E-9 | 1.0E-9 | 1.0E2 | 6.2E1 | 53 | 9 | 53 | 9 | 0.69 |
| nL | pg/ml | 1.0E-9 | 2.5E1 | 3.4E2 | 1.3E2 | 1.9E3 | 2.4E2 | 1.0E-9 | 1.0E-9 | 1.4E4 | 7.3E2 | 54 | 9 | 54 | 9 | 0.74 |
| hR | pg/ml | 2.7E4 | 2.6E4 | 2.9E4 | 2.9E4 | 1.1E4 | 9.4E3 | 1.0E-9 | 1.8E4 | 5.8E4 | 4.3E4 | 68 | 8 | 68 | 8 | 0.48 |
| hV | pg/ml | 4.4E2 | 4.4E2 | 4.3E2 | 4.4E2 | 2.2E2 | 2.3E2 | 1.0E-9 | 9.5E1 | 9.6E2 | 7.4E2 | 68 | 8 | 68 | 8 | 0.52 |
| hW | pg/ml | 1.9E3 | 3.1E3 | 2.1E3 | 7.6E3 | 1.2E3 | 1.3E4 | 1.0E-9 | 1.5E3 | 7.3E3 | 4.0E4 | 68 | 8 | 68 | 8 | 0.74 |
| hX | pg/ml | 1.1E3 | 1.3E3 | 1.2E3 | 1.2E3 | 1.0E3 | 3.8E2 | 2.5E0 | 7.0E2 | 8.6E3 | 2.0E3 | 68 | 8 | 68 | 8 | 0.65 |
| iA | pg/ml | 1.8E2 | 1.8E2 | 2.6E2 | 3.0E2 | 2.9E2 | 2.5E2 | 1.5E1 | 6.2E1 | 1.8E3 | 8.7E2 | 90 | 13 | 90 | 13 | 0.56 |
| iB | ng/ml | 5.2E0 | 8.4E0 | 6.5E0 | 1.0E1 | 4.9E0 | 6.4E0 | 3.3E-2 | 2.4E0 | 2.4E1 | 2.2E1 | 74 | 9 | 74 | 9 | 0.68 |
| iC | U/ml | 3.6E-1 | 5.3E-1 | 1.4E0 | 7.7E-1 | 6.4E0 | 8.3E-1 | 1.0E-9 | 6.8E-2 | 5.5E1 | 2.8E0 | 74 | 9 | 74 | 9 | 0.61 |
| iH | ng/ml | 1.7E5 | 1.8E5 | 1.6E5 | 1.6E5 | 5.0E4 | 5.6E4 | 2.9E3 | 7.7E4 | 2.6E5 | 2.4E5 | 90 | 13 | 90 | 13 | 0.49 |
| iJ | ng/ml | 5.0E4 | 3.8E4 | 5.7E4 | 4.7E4 | 3.8E4 | 2.3E4 | 1.8E3 | 1.2E4 | 2.5E5 | 9.3E4 | 90 | 13 | 90 | 13 | 0.43 |
| hB | ng/ml | 4.8E-1 | 5.6E-1 | 6.3E-1 | 8.3E-1 | 5.1E-1 | 5.7E-1 | 1.2E-1 | 2.9E-1 | 3.2E0 | 2.4E0 | 90 | 13 | 90 | 13 | 0.67 |
| hC | pg/ml | 5.3E3 | 1.0E4 | 7.8E3 | 1.3E4 | 1.2E4 | 1.5E4 | 4.1E1 | 3.0E2 | 1.1E5 | 5.7E4 | 90 | 13 | 90 | 13 | 0.63 |
| hF | ng/ml | 1.0E-9 | 1.0E-9 | 4.4E1 | 1.0E-9 | 4.2E2 | 0.0E0 | 1.0E-9 | 1.0E-9 | 4.0E3 | 1.0E-9 | 90 | 13 | 90 | 13 | 0.49 |
| hG | pg/ml | 6.9E3 | 6.6E3 | 7.7E3 | 8.7E3 | 3.1E3 | 5.5E3 | 1.8E3 | 3.6E3 | 1.8E4 | 2.0E4 | 90 | 13 | 90 | 13 | 0.48 |
| iO | ng/ml | 3.9E5 | 4.1E5 | 4.4E5 | 4.1E5 | 2.0E5 | 2.1E5 | 9.8E4 | 1.0E5 | 1.1E6 | 8.2E5 | 90 | 13 | 90 | 13 | 0.46 |
| iP | ng/ml | 5.4E4 | 4.4E4 | 6.0E4 | 4.9E4 | 5.1E4 | 1.8E4 | 7.1E3 | 2.2E4 | 4.4E5 | 7.0E4 | 90 | 13 | 90 | 13 | 0.43 |
| iZ | ng/ml | 1.6E3 | 2.2E3 | 1.8E3 | 2.5E3 | 8.0E2 | 1.1E3 | 7.5E2 | 1.1E3 | 5.7E3 | 4.6E3 | 88 | 13 | 88 | 13 | 0.72 |
| rC | pg/ml | 1.4E3 | 1.9E3 | 2.2E3 | 1.7E3 | 2.5E3 | 9.5E2 | 1.0E-9 | 6.0E2 | 1.5E4 | 2.9E3 | 66 | 7 | 66 | 7 | 0.50 |
| rB | pg/ml | 2.9E1 | 7.7E1 | 4.9E1 | 1.1E2 | 6.6E1 | 1.2E2 | 1.0E-9 | 1.0E-9 | 3.9E2 | 3.2E2 | 66 | 7 | 66 | 7 | 0.64 |
| jD | ng/ml | 3.5E1 | 5.0E1 | 4.2E1 | 9.1E1 | 3.9E1 | 9.8E1 | 1.0E-9 | 7.6E0 | 1.9E2 | 2.9E2 | 74 | 9 | 74 | 9 | 0.64 |
| jE | ng/ml | 1.0E-9 | 1.0E-9 | 4.7E0 | 9.4E0 | 1.1E1 | 1.5E1 | 1.0E-9 | 1.0E-9 | 6.2E1 | 3.5E1 | 74 | 9 | 74 | 9 | 0.58 |
| jF | pg/ml | 2.8E1 | 7.7E0 | 4.6E1 | 3.1E1 | 5.2E1 | 4.7E1 | 1.0E-9 | 1.0E-9 | 1.9E2 | 1.2E2 | 74 | 9 | 74 | 9 | 0.42 |
| jG | ng/ml | 4.0E3 | 4.2E3 | 4.4E3 | 4.6E3 | 2.0E3 | 1.5E3 | 6.7E2 | 2.5E3 | 9.6E3 | 7.9E3 | 74 | 9 | 74 | 9 | 0.54 |
| jH | ng/ml | 7.5E1 | 1.2E2 | 7.9E1 | 1.4E2 | 4.4E1 | 1.2E2 | 1.3E1 | 3.3E1 | 2.4E2 | 4.3E2 | 74 | 9 | 74 | 9 | 0.71 |
| jI | ng/ml | 7.3E1 | 1.2E2 | 7.9E1 | 1.6E2 | 3.2E1 | 1.2E2 | 3.8E1 | 4.4E1 | 1.9E2 | 4.4E2 | 74 | 9 | 74 | 9 | 0.74 |
| rA | pg/ml | 2.4E1 | 2.0E1 | 2.7E1 | 2.7E1 | 2.1E1 | 1.8E1 | 1.0E-9 | 1.2E1 | 1.1E2 | 6.8E1 | 72 | 8 | 72 | 8 | 0.50 |
| qY | pg/ml | 1.5E1 | 9.0E0 | 3.9E1 | 1.3E1 | 5.7E1 | 9.0E0 | 8.7E-1 | 2.1E0 | 3.3E2 | 2.7E1 | 72 | 8 | 72 | 8 | 0.35 |
| qX | pg/ml | 5.5E1 | 7.8E1 | 6.6E1 | 9.0E1 | 4.4E1 | 6.2E1 | 1.0E-9 | 2.3E1 | 1.7E2 | 2.1E2 | 72 | 8 | 72 | 8 | 0.60 |
| qW | pg/ml | 7.4E0 | 6.8E0 | 9.2E0 | 9.4E0 | 8.9E0 | 8.6E0 | 1.0E-9 | 1.0E-9 | 3.6E1 | 2.2E1 | 72 | 8 | 72 | 8 | 0.51 |
| qV | pg/ml | 1.6E3 | 1.8E3 | 2.3E3 | 2.2E3 | 2.0E3 | 1.6E3 | 1.0E2 | 6.3E2 | 1.1E4 | 5.6E3 | 72 | 8 | 72 | 8 | 0.50 |
| qU | pg/ml | 7.7E1 | 8.7E1 | 1.9E2 | 2.5E2 | 3.2E2 | 3.7E2 | 1.0E-9 | 1.9E1 | 2.1E3 | 1.1E3 | 72 | 8 | 72 | 8 | 0.57 |
| qT | pg/ml | 3.9E1 | 3.4E1 | 6.6E1 | 5.7E1 | 7.6E1 | 5.4E1 | 1.0E-9 | 6.9E0 | 4.9E2 | 1.6E2 | 72 | 8 | 72 | 8 | 0.46 |
| jK | ng/ml | 1.5E3 | 1.2E3 | 1.6E3 | 1.3E3 | 6.3E2 | 6.3E2 | 2.8E2 | 7.5E2 | 4.1E3 | 2.9E3 | 74 | 9 | 74 | 9 | 0.27 |
| jL | ng/ml | 1.9E2 | 2.9E2 | 2.7E2 | 3.3E2 | 2.0E2 | 1.8E2 | 5.9E1 | 1.5E2 | 8.1E2 | 6.3E2 | 74 | 9 | 74 | 9 | 0.66 |
| jM | ng/ml | 6.8E4 | 4.9E4 | 7.3E4 | 6.8E4 | 3.8E4 | 5.2E4 | 4.6E3 | 1.3E4 | 1.7E5 | 1.4E5 | 74 | 9 | 74 | 9 | 0.43 |
| jO | pg/ml | 2.3E5 | 2.6E5 | 2.7E5 | 2.7E5 | 1.5E5 | 1.6E5 | 7.6E4 | 9.8E4 | 7.7E5 | 6.5E5 | 74 | 9 | 74 | 9 | 0.49 |
| jP | pg/ml | 2.6E5 | 4.9E5 | 3.0E5 | 3.9E5 | 1.4E5 | 1.9E5 | 6.1E4 | 1.3E5 | 7.1E5 | 5.5E5 | 74 | 9 | 74 | 9 | 0.63 |
| jQ | pg/ml | 2.2E3 | 1.2E3 | 3.0E3 | 2.7E3 | 2.7E3 | 2.8E3 | 5.0E0 | 4.9E2 | 1.3E4 | 9.2E3 | 74 | 9 | 74 | 9 | 0.45 |
| jR | pg/ml | 5.5E3 | 3.3E3 | 9.4E3 | 9.5E3 | 1.1E4 | 1.4E4 | 1.0E-9 | 3.0E1 | 5.6E4 | 4.6E4 | 74 | 9 | 74 | 9 | 0.44 |
| jT | pg/ml | 1.8E5 | 1.6E5 | 1.8E5 | 1.5E5 | 6.1E4 | 5.1E4 | 7.1E4 | 7.5E4 | 3.5E5 | 2.2E5 | 74 | 9 | 74 | 9 | 0.35 |
| jU | mIU/ml | 5.5E0 | 5.8E0 | 1.2E1 | 1.4E1 | 2.0E1 | 1.8E1 | 8.1E-2 | 1.2E0 | 1.1E2 | 5.3E1 | 74 | 9 | 74 | 9 | 0.50 |
| jV | mIU/ml | 2.0E0 | 1.9E0 | 4.1E0 | 3.5E0 | 5.8E0 | 3.6E0 | 2.7E-3 | 2.1E-1 | 3.2E1 | 1.0E1 | 74 | 9 | 74 | 9 | 0.48 |
| jY | ng/ml | 1.1E-3 | 2.6E-3 | 8.8E-3 | 7.4E-3 | 3.7E-2 | 9.4E-3 | 1.0E-9 | 1.0E-9 | 3.0E-1 | 2.6E-2 | 74 | 9 | 74 | 9 | 0.59 |
| kC | pg/ml | 1.0E2 | 9.6E1 | 2.0E2 | 1.4E2 | 4.0E2 | 1.7E2 | 2.1E1 | 3.6E1 | 2.7E3 | 5.9E2 | 54 | 9 | 54 | 9 | 0.45 |
| kE | pg/ml | 1.5E5 | 1.4E5 | 1.4E5 | 1.4E5 | 3.5E4 | 5.8E4 | 4.1E4 | 7.9E4 | 2.3E5 | 2.7E5 | 54 | 9 | 54 | 9 | 0.44 |
| kF | pg/mL | 6.8E1 | 5.2E1 | 6.9E1 | 7.9E1 | 2.2E1 | 4.1E1 | 3.5E1 | 4.0E1 | 1.5E2 | 1.4E2 | 54 | 9 | 54 | 9 | 0.46 |
| kG | pg/mL | 8.6E3 | 8.8E3 | 1.1E4 | 3.2E4 | 1.0E4 | 5.2E4 | 1.9E3 | 1.1E3 | 5.8E4 | 1.6E5 | 54 | 9 | 54 | 9 | 0.49 |
| kI | pg/ml | 2.1E2 | 1.8E2 | 2.2E2 | 2.0E2 | 1.1E2 | 1.1E2 | 4.4E1 | 1.0E-9 | 6.7E2 | 3.5E2 | 54 | 9 | 54 | 9 | 0.45 |
| kK | pg/ml | 1.2E2 | 1.2E2 | 1.6E2 | 1.5E2 | 1.5E2 | 9.2E1 | 2.1E1 | 2.9E1 | 9.1E2 | 2.9E2 | 54 | 9 | 54 | 9 | 0.54 |
| kN | pg/ml | 1.2E3 | 7.4E2 | 1.7E3 | 1.4E3 | 1.8E3 | 2.1E3 | 2.1E2 | 3.8E2 | 1.0E4 | 7.0E3 | 54 | 9 | 54 | 9 | 0.33 |
| kO | pg/ml | 7.1E3 | 7.6E3 | 1.0E4 | 8.2E3 | 1.9E4 | 2.7E3 | 3.8E3 | 5.0E3 | 1.5E5 | 1.3E4 | 54 | 9 | 54 | 9 | 0.58 |
| kP | pg/ml | 5.6E3 | 3.5E3 | 6.8E3 | 5.3E3 | 4.3E3 | 4.3E3 | 9.6E2 | 1.6E3 | 2.7E4 | 1.5E4 | 54 | 9 | 54 | 9 | 0.35 |
| kQ | pg/ml | 4.4E3 | 4.9E3 | 5.5E3 | 6.7E3 | 4.1E3 | 5.4E3 | 5.6E2 | 1.4E3 | 2.5E4 | 2.2E4 | 90 | 13 | 90 | 13 | 0.57 |
| kR | pg/ml | 2.4E1 | 1.5E1 | 4.0E1 | 3.4E1 | 1.1E2 | 3.4E1 | 1.0E-9 | 5.5E0 | 1.0E3 | 1.1E2 | 90 | 13 | 90 | 13 | 0.47 |

Figure 38 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| kS | pg/ml | 8.8E2 | 8.7E2 | 9.9E2 | 1.0E3 | 5.9E2 | 6.9E2 | 8.2E1 | 3.2E2 | 3.2E3 | 2.5E3 | 90 | 13 | 90 | 13 | 0.47 |
| rZ | ng/ml | 1.8E-3 | 8.2E-3 | 7.7E-3 | 2.4E-2 | 1.6E-2 | 3.9E-2 | 1.0E-9 | 1.0E-9 | 9.4E-2 | 1.1E-1 | 67 | 7 | 67 | 7 | 0.60 |
| rY | ng/ml | 6.4E-2 | 7.6E-2 | 5.0E-1 | 8.4E-2 | 2.5E0 | 4.8E-2 | 1.0E-9 | 2.8E-2 | 2.0E1 | 1.6E-1 | 67 | 7 | 67 | 7 | 0.56 |
| rX | ng/ml | 1.0E-9 | 1.0E-9 | 1.2E-1 | 2.7E-2 | 5.9E-1 | 4.7E-2 | 1.0E-9 | 1.0E-9 | 3.7E0 | 1.2E-1 | 67 | 7 | 67 | 7 | 0.60 |
| lK | pg/ml | 7.1E1 | 3.6E1 | 1.4E2 | 9.7E1 | 1.7E2 | 1.5E2 | 1.0E-9 | 2.3E0 | 7.0E2 | 4.8E2 | 73 | 9 | 73 | 9 | 0.37 |
| lL | pg/ml | 1.5E3 | 2.5E3 | 3.0E3 | 2.8E3 | 5.4E3 | 1.7E3 | 7.5E1 | 8.8E2 | 4.2E4 | 6.8E3 | 74 | 9 | 74 | 9 | 0.63 |
| lM | pg/ml | 1.2E3 | 3.1E3 | 3.9E3 | 1.5E4 | 6.7E3 | 2.3E4 | 9.5E0 | 2.6E2 | 4.2E4 | 6.7E4 | 74 | 9 | 74 | 9 | 0.63 |
| lN | pg/ml | 1.0E-9 | 3.0E0 | 3.2E0 | 4.2E0 | 7.2E0 | 6.2E0 | 1.0E-9 | 1.0E-9 | 4.3E1 | 1.9E1 | 74 | 9 | 74 | 9 | 0.60 |
| lO | pg/ml | 1.0E-9 | 1.0E-9 | 2.2E0 | 1.5E1 | 1.5E1 | 4.6E1 | 1.0E-9 | 1.0E-9 | 1.3E2 | 1.4E2 | 73 | 9 | 73 | 9 | 0.54 |
| nW | pg/ml | 1.1E5 | 1.1E5 | 1.1E5 | 1.1E5 | 2.7E4 | 3.3E4 | 5.8E4 | 3.6E4 | 1.8E5 | 1.5E5 | 90 | 13 | 90 | 13 | 0.52 |
| nY | pg/ml | 2.3E3 | 3.5E3 | 2.6E3 | 3.3E3 | 1.6E3 | 2.0E3 | 5.1E2 | 6.3E2 | 1.0E4 | 8.1E3 | 90 | 13 | 90 | 13 | 0.60 |
| oO | pg/ml | 9.2E4 | 1.0E5 | 1.1E5 | 1.4E5 | 6.1E4 | 1.2E5 | 2.0E4 | 3.3E3 | 3.0E5 | 4.0E5 | 48 | 8 | 48 | 8 | 0.54 |
| oP | pg/ml | 1.3E5 | 1.4E5 | 1.5E5 | 1.9E5 | 8.4E4 | 1.7E5 | 4.2E4 | 2.4E4 | 4.2E5 | 5.7E5 | 48 | 8 | 48 | 8 | 0.54 |
| oQ | pg/ml | 3.2E3 | 4.8E3 | 3.9E3 | 8.0E3 | 3.2E3 | 1.0E4 | 7.7E2 | 9.1E2 | 2.1E4 | 3.2E4 | 48 | 8 | 48 | 8 | 0.65 |
| oE | pg/ml | 2.1E2 | 8.9E2 | 5.0E2 | 1.0E3 | 6.2E2 | 1.0E3 | 1.0E-9 | 1.0E-9 | 2.8E3 | 3.4E3 | 90 | 13 | 90 | 13 | 0.66 |
| oF | pg/ml | 1.4E4 | 2.5E4 | 2.8E4 | 4.7E4 | 3.9E4 | 4.5E4 | 4.3E2 | 2.0E3 | 2.5E5 | 1.4E5 | 90 | 13 | 90 | 13 | 0.67 |
| oH | pg/ml | 3.9E1 | 2.4E1 | 8.5E1 | 5.2E1 | 1.3E2 | 8.0E1 | 4.4E0 | 1.1E1 | 8.6E2 | 3.1E2 | 90 | 13 | 90 | 13 | 0.41 |
| oK | pg/ml | 9.0E2 | 1.5E3 | 1.6E3 | 1.8E3 | 1.9E3 | 1.7E3 | 8.8E1 | 2.3E2 | 1.2E4 | 5.9E3 | 90 | 13 | 90 | 13 | 0.54 |
| oN | pg/ml | 5.6E2 | 5.7E2 | 1.1E3 | 6.7E2 | 2.1E3 | 3.4E2 | 1.1E2 | 3.3E2 | 1.8E4 | 1.5E3 | 90 | 13 | 90 | 13 | 0.54 |
| pF | pg/ml | 6.0E-1 | 5.7E-1 | 1.9E0 | 7.1E-1 | 9.1E0 | 4.0E-1 | 1.0E-9 | 1.8E-1 | 8.7E1 | 1.3E0 | 90 | 13 | 90 | 13 | 0.50 |

Analyte panel data:

Unconstrained panels with 3 analytes, where 1.0E-10 >= 'model p-value' > 0. Contains 8,031 panels of 15,247,928 total panels evaluated. :
Im{Et(AA Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Fp(AA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nn(AA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) No(AA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ns(AA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Nt Nu Nv Nw Nx Ny Oe Of Og Oh Oi Ok Om On Oy Oz Pa Pb Pc Pd Pe Pf Pg Po Pz Qa Qb Qc Qd Qe) Lw(AA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Nt Nu Nv Nw Nx Ny Oe Of Og Oh Oi Ok Om On Oy Oz Pa Pb Pc Pd Pe Pf Pg Po Pz Qa Qb Qc Qd Qe) Lz(AA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lx Ly Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Nt Nu Nv Nw Nx Ny Oe Of Og Oh Oi Ok Om On Oy Oz Pa Pb Pc Pd Pe Pf Pg Po Pz Qa Qb Qc Qd Qe) Mw(AA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lx Ly Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni Nj Nk Nl Nm Nq Nr Nt Nu Nv Nw Nx Ny Oe Of Og Oh Oi Ok Om On Oy Oz Pa Pb Pc Pd Pe Pf Pg Po Pz Qa Qb Qc Qd Qe) Nc(AA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lx Ly Ma Mb Mc Md Me Mf Mg Mh Mi Mj Mk Ml Mm Mn Mp Mq Mr Ms Mt Mu Mv Mx My Mz Na Nb Nd Ne Nf Ng Nh Ni Nj Nk Nl Nm Nq Nr Ms Mt Mu Mv Nw Nx Ny Oe Of Og Oh Oi Ok Om On Oy Oz Pa Pb Pc Pd Pe Pf Pg Po Pz Qa Qb Qc Qd Qe) Nk(AA Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lx Ly Ma Mb Mc Md Me Mf Mg Mh Mi Mj Mk Ml Mm Mn Mp Mq Mr Ms Mt Mu Mv Mx My Mz Na Nb Nd Ne Nf Ng Nh Ni Nj Nl Nm Nq Nr Nt Nu Nv Nw Nx Ny Oe Of Og Oh Oi Ok Om On Oy Oz Pa Pb Pc Pd Pe Pf Pg Po Pz Qa Qb Qc Qd Qe) Hu(AA Fr Hq Hr Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lx Ly Ma Mb Mc Md Me Mf Mg Mh Mi Mj Mk Ml Mm Mn Mp Mq Mr Ms Mt Mu Mv Mx My Mz Na Nb Nd Ne Nf Ng Nh Ni Nj Nl Nm Nq Nr Nt Nu Nv Nw Nx Ny Oe Of Og Oh Oi Ok Om On Oy Oz Pa Pb Pc Pd Pe Pf Pg Po Pz Qa Qb Qc Qd Qe) Hv(AA Fr Hq Hr Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lx Ly Ma Mb Mc Md Me Mf Mg Mh Mi Mj Mk Ml Mm Mn Mp Mq Mr Ms Mt Mu Mv Mx My Mz Na Nb Nd Ne Nf Ng Nh Ni Nj Nl Nm Nq Nr Nt Nu Nv Nw Nx Ny Oe Of Og Oh Oi Ok Om On Oy Oz Pa Pb Pc Pd Pe Pf Pg Po Pz Qa Qb Qc Qd Qe) Ip(AA Fr Hq Hr Hv Hw Hx Ih Ii Ij Ik Il In Io Iq Ir Is It Iu Iv Jg Jh Ji Jj Jk Jl Jm Jn Jo Jp Jq Jr Js Jt Lh Li Lj Lu Lv Lx Ly Ma Mb Mc Md Me Mf Mg Mh Mi Mj Mk Ml Mm Mn Mp Mq Mr Ms Mt Mu Mv Mx My Mz Na Nb Nd Ne Nf Ng Nh Ni Nj Nl Nm Nq Nr Nt Nu Nv Nw Nx Ny Oe Of Og Oh Oi Ok Om On Oy Oz Pa Pb Pc Pd Pe Pf Pg Po Pz Qa Qb Qc Qd Qe) It(AA Fr Hq Hr Hw Hx Ih Ii Ij Ik Il In Io Iq Ir Is Iu Iv Jg Jh Ji Jj Jk Jl Jm Jn Jo Jp Jq Jr Js Jt Lh Li Lj Lu Lv Lx Ly Ma Mb Mc Md Me Mf Mg Mh Mi Mj Mk Ml Mm Mn Mp Mq Mr Ms Mt Mu Mv Mx My Mz Na Nb Nd Ne Nf Ng Nh Ni Nj Nl Nm Nq Nr Nt Nu Nv Nw Nx Ny Oe Of Og Oh Oi Ok Om On Oy Oz Pa Pb Pc Pd

Iu Jg Jh Jk Jl Jm Jo Lh Lu Lv Lx Ly Ma Mb Mc Md Me Mf Mg Mh Mj Mk Ml Mm Mn Mq Mr Ms Mt Mu Mv Mx My Na Nb Nd Ne Nf Nh Ni Nj Nl Nm Nq Nr Nu Nv Nx Ny Oh Oi Ok Om On Pa Pd Pf Pg Po Pz Qa Qb Qe) Oh(aA Fr Hq Hr Hw Hx Ii Ij Ik Il In Io Iu Jg Jh Jk Jl Jm Jo Lh Lu Lv Lx Ly Ma Mb Mc Md Me Mf Mg Mh Mj Mk Ml Mm Mn Mq Mr Ms Mt Mu Mv Mx My Na Nb Nd Ne Nf Nh Ni Nj Nl Nm Nq Nr Nu Nv Nx Ny Oi Ok Om On Pa Pd Pf Pg Po Pz Qa Qb Qe) Ok(aA Fr Hq Hr Hw Hx Ii Ij Ik Il In Io Iu Jg Jh Jk Jl Jm Jo Lh Lu Lv Lx Ly Ma Mb Mc Md Me Mf Mg Mh Mj Mk Ml Mm Mn Mq Mr Ms Mt Mu Mv Mx My Na Nb Nd Ne Nf Nh Ni Nj Nl Nm Nq Nr Nu Nv Nx Ny Oi Om On Pa Pd Pf Pg Po Pz Qa Qb Qe) On(aA Fr Hq Hr Hw Hx Ii Ij Ik Il In Io Iu Jg Jh Jk Jl Jm Jo Lh Lu Lv Lx Ly Ma Mb Mc Md Me Mf Mg Mh Mj Mk Ml Mm Mn Mq Mr Ms Mt Mu Mv Mx My Na Nb Nd Ne Nf Nh Ni Nj Nl Nm Nq Nr Nu Nv Nx Ny Oi Om Pa Pd Pf Pg Po Pz Qa Qb Qe) aA(Fr Hq Hr Hw Hx Ii Ij Ik Il In Io Iu Jg Jh Jk Jl Jm Jo Lh Lu Lv Lx Ly Ma Mb Mc Md Me Mf Mg Mh Mj Mk Ml Mm Mn Mq Mr Ms Mt Mu Mv Mx My Na Nb Nd Ne Nf Nh Ni Nj Nl Nm Nq Nr Nu Nv Nx Ny Oi Om Pa Pd Pf Pg Po Pz Qa Qb Qe) Mt(Aa Fr Hq Hr Hw Hx Ii Ij Ik Il In Io Iu Jg Jh Jk Jl Jm Jo Lh Lu Lv Lx Ly Ma Mb Mc Md Me Mf Mg Mh Mj Mk Ml Mm Mn Mq Mr Ms Mu Mv Mx My Na Nb Nd Ne Nf Nh Ni Nj Nl Nm Nq Nr Nu Nv Nx Ny Oi Om Pa Pd Pf Pg Po Qa Qb) Pa(Aa Fr Hq Hr Hw Hx Ii Ij Ik Il In Io Iu Jg Jh Jk Jl Jm Jo Lh Lu Lv Lx Ly Ma Mb Mc Md Me Mf Mg Mh Mj Mk Ml Mm Mn Mq Mr Ms Mu Mv Mx My Na Nb Nd Ne Nf Nh Ni Nj Nl Nm Nq Nr Nu Nv Nx Ny Oi Om Pd Pf Pg Po Qa Qb) Mn(Fr Hq Hr Hw Hx Ii Ij Ik Il In Io Iu Jg Jh Jk Jl Jm Jo Lh Lu Lv Lx Ly Ma Mb Mc Md Me Mf Mg Mh Mj Mk Ml Mm Mq Mr Ms Mu Mv Mx My Na Nb Nd Ne Nf Nh Ni Nj Nl Nm Nq Nr Nu Nv Nx Ny Oi Om Pd Pf Pg Po Qa Qb) Ij(Fr Hq Hr Hw Hx Ii Ik Il In Io Iu Jg Jh Jk Jl Jm Jo Lh Lu Lv Lx Ly Ma Mb Mc Md Me Mf Mg Mh Mj Mk Ml Mm Mq Mr Ms Mu Mv Mx My Na Nb Nd Ne Nf Nh Ni Nj Nl Nm Nq Nr Nu Nv Nx Ny Oi Om Pd Pf Pg Qa Qb) Ik(Fr Hq Hr Hw Hx Ii Il In Io Iu Jg Jk Jl Jm Jo Lh Lu Lv Lx Ly Ma Mb Mc Md Me Mf Mg Mh Mj Mk Ml Mm Mq Mr Ms Mu Mv Mx My Na Nb Nd Ne Nf Nh Ni Nj Nl Nm Nq Nr Nu Nv Nx Ny Oi Om Pd Pf Pg Po Qa Qb) Nr(Fr Hq Hr Hw Hx Ii Il In Io Iu Jg Jh Jk Jl Jm Jo Lu Lv Lx Ly Ma Mb Mc Md Me Mf Mg Mh Mj Mk Ml Mm Mq Mr Ms Mu Mv Mx My Na Nb Nd Ne Nf Nh Ni Nj Nl Nm Nq Nu Nv Nx Ny Oi Om Pd Pf Qa Qb) Nb(Aa Fr Hq Hr Hw Hx Ii Il In Io Jh Jk Jl Jo Lu Lv Lx Ly Ma Mb Mc Md Me Mf Mg Mh Mj Mk Ml Mm Mq Mr Ms Mu Mv Mx My Na Nd Ne Nf Nh Ni Nj Nl Nm Nq Nu Nv Nx Ny Oi Om Pd Pf Pg Qa Qb) Jl(Fr Hq Hr Hw Hx Ii Il In Io Jg Jh Jk Jm Jo Lh Lu Lv Lx Ly Ma Mb Mc Me Mf Mg Mh Mj Mk Ml Mm Mq Mr Ms Mu Mv Mx My Na Nd Ne Nf Nh Ni Nl Nm Nq Nu Nv Nx Ny Oi Om Pd Pf Pg Qa Qb) My(Aa Fr Hq Hr Hw Ii Il In Jg Jh Jk Jo Lh Lu Lv Lx Ly Ma Mb Mc Md Me Mf Mg Mh Mj Mk Ml Mm Mq Mr Ms Mv Mx Na Nd Ne Nf Nh Ni Nm Nq Nu Nv Nx Ny Oi Om Pd Pf Pg Po Qa Qb) Mr(Aa Fr Hq Hr Hw Hx Ii Il In Io Jg Jk Jo Lu Lv Lx Ly Ma Mb Mc Md Me Mf Mg Mh Mj Mk Ml Mm Mq Ms Mu Mv Mx Na Nd Ne Nf Nh Ni Nl Nm Nq Nu Nv Nx Ny Oi Pd Pf Qa Qb) Nx(Aa Fr Hq Hw Ii Il In Io Jg Jk Jo Lh Lu Lv Lx Ly Ma Mb Mc Me Mf Mh Mj Mk Ml Mm Mq Ms Mx Na Nd Ne Nf Ni Nm Nq Nu Nv Ny Oi Om Pf Pg Po Qa Qb Qe) Mj(Aa Fr Hq Hr Hw Hx Ii Il In Jg Jk Jo Lu Lv Lx Ly Ma Mb Mc Md Me Mf Mg Mh Mk Ml Mm Ms Mu Mv Nd Ne Nf Nh Ni Nm Nu Nv Ny Oi Pd Pf Qa) Ms(Fr Hq Hr Hw Ii Il In Jg Jk Jo Lh Lu Lv Lx Ly Ma Mb Mc Me Mf Mh Mk Ml Mm Mq Mx Na Nd Ne Nf Nh Ni Nm Nq Nu Oi Om Pd Pf Po Qa Qb) Mb(Fr Hq Hr Hw Il In Jg Jk Jo Lh Lu Lv Lx Ly Ma Mc Me Mf Mh Mk Ml Mm Mq Mu Mx Na Nd Ne Nf Ni Nj Nm Nu Oi Pd Pf Pg Qa Qb) Jk(Aa Fr Hr Hw Ii Il In Jg Jo Lh Lu Lv Lx Ma Mc Mf Mh Mk Mm Mq Mv Mx Na Nd Ne Nf Ni Nm Nq Nu Nv Oi Om Pf Pg Po Qa Qb) Mh(Aa Fr Hq Hr Hw Il In Io Jg Jo Lh Lu Lx Ly Ma Mc Me Mf Mm Mq Na Nd Ne Nf Nh Ni Nm Nq Nu Ny Oi Pd Pf Po Qa Qb) Ne(Fr Hq Hr Hw Il In Jg Jo Lh Lu Lv Lx Ma Mc Mf Ml Mm Mq Mx Na Nd Nf Ni Nl Nm Nu Oi Pd Pf Pg Po Qa Qb) Lu(Aa Fr Hq Hr Hw Il In Jg Jo Lh Lx Ly Ma Mc Me Mf Mm Mq Mv Na Nd Nf Nh Ni Nm Nu Oi Pd Pf Qa Qb) Aa(Hq Hr Hw Hx Ii Il In Io Iu Jg Jh Jo Lx Md Mf Mk Mq Ni Nu Nv Oi Pd Pf Pg Po Pz Qa Qb Qe) Il(Fr Hw In Jg Jo Lh Lv Lx Ly Ma Mc Mf Mm Mq Na Nd Nf Ni Nm Nu Ny Oi Pd Pf Po Qa Qb) Nm(Fr Hq Hr Hw In Jo Lh Lx Ly Ma Mc Mf Mg Mm Na Nd Nf Ni Nu Oi Pd Pf Qa Qb) Qa(Hq Hr Hw In Jg Jo Ly Ma Mc Md Me Mf Mm Mu Nd Nf Nh Ni Nu Oi Pd Pf Qb) Hw(Fr Hq Hr Jg Jo Lx Ly Ma Mc Mf Mm Mu Nd Nf Nh Ni Nu Oi Pd Pf Qb) In(Fr Hq Hr Hx Ly Ma Mc Md Mf Mm Nd Nf Ni Nu Ny Oi Pd Pf) Lh(Hq Hr Hx Ii Jo Ly Ma Mc Mf Mm Mu Mv Nd Nf Nu Ny Oi Pd) Ly(Fr Jo Lv Lx Ma Mc Mf Mm Mq Nd Nf Nu Oi Pf Po) Oi(Fr Hq Hr Jg Jo Ma Mc Mf Mm Nf Nu Pf) Mc(Fr Jo Lx Ma Mf Mm Na Nd Nu Pf) Mf(Fr Jg Lv Ma Me Mm Mx Nu Pf) Hq(Fr Jg Jo Lx Ma Mm Nd Pf Po) Hr(Ii Jo Na Nf Nu Om Po) Ma(Na Nd Nu Pd Qb) Mm(Me Na Ni Pf Qb) Pd(Jo Nu Pf Pg) Nu(Nd Nh) Pf(Na Nd) FrMu MvJg} Li{Ji(aA Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Pb(AA Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pc Pd Pe Pf Pg Po Qa Qb Qc Qd Qe) aA(Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pc Pd Pe Pf Pg Po Pz Qa Qb Qc Qd Qe) Ik(Et Fp Fr Hq Hr Hu Hv Hw Hx Ih Ii Ij Il In Ip Iq Ir Is It Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Mm Mn Mp Mq Mr Ms Mt Mu Mv Mw Mx My Mz Na Nb Nc Nd Ne Nf Ng Nh Ni Nk Nm Nn No Nq Nr Ns Nt Nu Nv Nw Nx Ny Oe Of Og Oh Oi Ok Om On Oy Oz Pa Pc Pd Pe Pf Pg Qa Qb Qc Qd Qe) Ih(Et Fp Hq Hr Hu Hv Hw Ii Ij Il In Ip Ir Is It Iv Jj Jk Jn Jo Jp Jq Jr Jt Lj Lw Ly Lz Ma Mb Mc Md Me Mf Mh Mi Mj Mk Mn Mp Ms Mt Mv Mw My Mz Nc Nd Ne Nf Ng Nh Ni Nj Nk Nl Nm No Ns Nt Nu Nv Nw Nx Oe Of Og Oh Oi Ok Oy Oz Pa Pc Pd Pf Po Qb Qc) Jj(Et Ii Ij Il In Ip Ir Is It Iv Jm Jn Jq Js Jt Lj Lw Lz Mb Mc Mf Mh Mn Mw Mz Nc Nd Nm No Ns Nt Nw Oe Og On Oz Pc Qb Qc) Og(Et Ij Il In Ip Ir Is It Iv Jg Jm Jn Jq Js Jt Lj Lw Mb Mw Mz Nb Nd Nm No Ns Nw Ok On Oz Qb Qc) It(Aa Et Hu Ij Il Ip Ir Is Iv Jo Jp Jq Jt Lj Lw Ly Mb Mf Mh Mw Nd Nk No Ns Nw Oe Oi Oy Oz) Et(Hu Ij Il Ip Ir Is Iv Jn Jo Jq Js Lj Mw My Nc Nd Ng Ns Nw Nx Oe Of Oi Oy Oz Pc Qc) Nw(Hu Ij Il Ir Is Iv Jn Jt Ly Mf Mh Mv Mw My Ng Ns Nv Nx Oe Of Oi Oy Oz Pc Po Qc) Ir(Hr Hu Ij Il Ip Jo Lj Ly Mf Mh Mw Nk Ns Oe Of Oi Oy Oz) Ij(Hr Hu Is Jo Ly Mw My Ng Ns Oe Of Oy Oz) Is(Hr Hu Mw My Ns Oe Of Oy Oz) Mw(Hu Iv Ng Ns Oe Oy) Oe(Il Iv Jn Jq Jt) Hr(Iv Jq Jt Ok) Oz(Aa Ip Iv Ns) Of(Iv Jt Nb) Oy(Aa Ip On) Nd(Hq Ns) AaQc IlIp JoJt} Ji{Nx(aA Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Ny Oe Of Og Oh Oi Ok Om On Oy Oz Pa Pb Pc Pd Pe Pf Pg Po Pz Qa Qb Qc Qd Qe) aA(Et Fp Fr Hq Hr Hu Hv Hx Ih Ii Ij Ik Il Io Ip Iq Ir It Iu Iv Jg Jj Jl Jm Jn Jo Jp Jq Jr Js Jt Lh Lj Lu Lv Lw Ly Lz Ma Mb Mc Md Me Mf Mg Mh Mj Mk Ml Mm Mn Mp Ms Mu Mv Mw My Mz Nb Nc Nd Ne Nf Ng Nh Nj Nk Nl Nm Nn No Nr Ns Nt Nu Nv Nw Ny Oe Of Og Oh Oi Ok Om On Oy Oz Pa Pb Pc Pd Pe Pf Pg Po Pz Qa Qb Qc Qd) Og(Et Fp Fr Hr Hv Ih Ij Ik Il In Ip Iq Ir Is It Iv Jg Jj Jk Jm Jn Jp Jq Js Jt Lj Lv Lx Ma Mb Md Me Mf Mg Mi Mm Mn Ms Mv Mw My Mz Nc Nd Nk Nm Nn No Nq Nr Ns Nt Nu Nw Ny Oe Of Ok On Oy Oz Pa Pb Pc Pe Pf Po Pz Qa Qb Qc Qd Qe) Pb(Et Fp Fr Hr Hw Ih Ij Il Ip Ir Is It Iv Jg Jj Jl Jm Jn Jp Jq Js Jt Lj Lx Lz Ma Md Mf Mm Mn Mp Mr Ms Mw My Mz Nc Nd Nk Nm Nn No Nq Nr Ns Nt Nu Nw Ny Oe Of Ok On Oy Pa Pe Pf Pg Po Qa Qb Qc Qd Qe) Mw(Et Hr Hu Hx Ih Ij Ik Ip Ir It Jj Jn Jq Lj Md Mf Mh Ml Ms Mv My Ng Nk No Ns Ny Oe Of Om Oy Oz Qc) It(Et Hr Hx Ik Ip Ir Jj Jp Jq Lj Ma Md Mf Mh Ms My

Figure 38 Continued

Nd Nk No Ns Nu Nw Ny Oe Of Of Oy Oz Qc) Lj(Et Hr Ih Ij Ik Ip Ir Jj Jn Jp Jq Jt Ma Mf Ms Nd Nk Nm No Ns Nw Oe Oy Oz Pc Qc) No(Et Hr Hx Ik Ip Ir Jj Jq Md Mh Ms My Nk Ns Nv Ny Oe Of Om Oy Oz Po Qc) Et(Hr Ih Ir Iv Jj Jm Jn Jq Md Ms My Nd Ng Nk Ns Ny Oe Of Om Oy Oz) Of(Fr Ij Il Ip Ir Jg Jn Jp Jt Ma Mt Nd Nm Nu Nw Pa) Hr(Ij Il Ip Ir Is Iv Jn Jt Ms Ok Pe) Ir(Ik Jj Jq Ms My Nk Oe Oy Oz Qc) My(Ij Il Jg Jn Jq Jt Nu Nw) Ij(Jj Jq Ms Oe Om Oy) Jq(Ih Is Jn Nm Nw) Oe(Ih Is Jn Jt Nw) Ms(Ih Jn Nw) Oy(Il Jg Nw) Nd(Hq Ns) Jj(Ih Jn) MdNw NcNk}
Nw{Pb(aA Et Fp Fr Hq Hr Hu Hv Hw Hx Ih Ii Ij Ik Il In Io Ip Iq Ir Is It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pc Pd Pe Pf Pg Po Qa Qb Qc Qd Qe) It(aA Et Hq Hr Hu Hv Hw Hx Ih Ik Ip Ir Is Iv Jj Jl Jm Jn Jo Jp Jq Jr Js Jt Lj Ly Mb Md Mf Mh Ml Mn Ms Mv Mw My Nc Nd Ng Nk Nn No Ns Nu Nv Nx Ny Oe Of Og Oy Oz Pa Pc Pd Po Qa Qb Qc) aA(Et Hu Hv Hx Ih Ij Ip Ir Jj Jl Jm Jn Jt Lj Md Me Mh Mw My Nm Ns Nv Oe Of Og Oy Oz Pc Qc) Og(Et Hv Ih Ij Il Ip Ir Is Iv Jg Jm Jn Jo Js Jt Lj Mw Nm No Ns Oz Pc Qa Qb) Oz(Ih Ip Ir Is Iv Jj Lj Mv Mw My No Ns Oe Of Oy) My(Et Ih Ij Il In Ir Jg Jh Jn Jt Mw Nb) Oe(Et Ih Ij Ir Is Iv Jn Jt Lj Mw) Of(Ij In Ir Iv Jn Jo Jt Mw Nb) Ir(Ik Jj Mh Mw Ns Nx Oy) Lj(Et Ih Ij Ik Jt Mw) Oy(Ih Ij Jn Jt Mw) Ns(Jn Jt Nd) Hr(Hw Iv Jt) Jj(Ih Ij Mw) Hu(Ij Mw) EtIh NdHq HxIv JtNx} Et{It(aA Fp Fr Hq Hr Hu Hv Hw Hx Ih Ii Ij Ik Il In Io Ip Iq Ir Is Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qe) Lj(aA Hq Hr Hu Hv Hw Ih Ii Ij Ik Il In Io Ip Ir Is Iv Jj Jm Jn Jo Jq Js Jt Lw Lx Ly Lz Mb Mc Mf Mh Mi Mj Mp Ms Mt Mw Mz Nb Nc Nd Ne Ni Nk Nn No Nq Ns Nt Nx Oe Of Og Oh Oi On Oy Oz Pa Pb Pc Pe Pf Pg Qb Qc) aA(Ih Ij Ip Ir Jm Jn Js Mw Ns Oe Of Og Oy Oz Pb Pc Qb Qc) Oe(Fp Ih Ij Il Ir Is Iv Jn Js Mw No Pb Qa Qb) Og(Ih Ij Ir Is Jm Jn Js Mw No) Pb(Ih Ij Ir Is Jn Js Mw No Qb) Ij(Hu Jj My Ng Of Oy) Ir(Ik Jj Mw Of Oy Oz) No(Ih Ns Oy Oz) Mw(Ih Jj Of Oy) Ih(Jj Oy) NsNd NbOf HrIv JjJn} Ij{Og(aA Fp Fr Hr Hu Ih Ik Ip Iq Ir Is It Iu Iv Jg Jj Jl Jm Jn Jo Jp Jq Jr Js Jt Lh Lj Lw Lx Lz Me Mg Mi Mm Mn Mp Mr Mt Mw Mz Nb Nc Nd Ni Nm Nn No Ns Nt Nu Ny Of Oh Ok Om On Oy Oz Pa Pb Pc Pe Pf Po Qa Qb Qc Qd) aA(Hr Hu Hv Hx Ih Ii Ik Ip Iq Ir It Jh Jj Jk Jn Js Jt Lj Lw Ly Lz Ma Md Me Mh Mj Mk Mm Mn Ms Mu Mv Mw My Mz Nb Nc Nd Ne Nf Ng Nh Nk Nm No Nr Ns Nv Nx Ny Oe Of Oi Om Oy Oz Pb Pc Pd Po Qb Qc Qd) Oy(Jg Jj Lx Mi Mp Mt Mw Nn No On Pa Pb) Jj(Ir It Lj Mw My No Oe Of Pb) Of(Jg Mi Mt Mw Nb No On) My(Jg Mi Mt No On) Oe(Ih Ir Lj No Pb) Pb(Ir Lj Mw No) fR(Nc Nh) UhbN} aA{It(Ip Ir Jg Lj Mn Mw Nm No Og Oz Pb) Ip(Ir Jn Lj Mw Oe Og Oz Pb) Lj(Jg Mg Mw Nm Oe Oz Pb) Ir(Mw Oe Og Oz Pb) Oe(Ih Mw Nm) Pb(Jn No) NmOg} bN{Uh(As Cp Cq Cu Cw Dc Hv Hw Id In It Jn Jq Jr Kd Ke Kq Lw Ml Na Nb Om Pi Pk Qa Ra Up Vp Vt) Ke(Nx Uv)} No{Pb(Ih Ip Ir Is It Jj Jn Jt Mw Ns Oe) It(Ik Jj Ns Og Oz) Ns(Nd Oz) Ih(Jj Oe) Ir(Oe Og) IpOz} Ir{Oe(Ik Jg Jt Mw Nn On Oz Pb) Og(Ip Jg Jt Mn Mw Nm Pb) Mw(Ik Jj Oy Pb)} Aa{It(Jj Mw Qc) QcOg} Mw{Jj(Ih It) IsOg} Og{IhJg JtLj} DeKqUh

Unconstrained panels with 3 analytes, where 1.0E-9 >= 'model p-value' > 1.0E-10. Contains 6,987 panels of 15,247,928 total panels evaluated. : Ji{Ir(Fp Fr Hq Hu Hv Hw Hx Ih Ii Ij Il In Io Ip Iq Is Iu Iv Jg Jh Jk Jl Jm Jn Jo Jp Jr Js Jt Lh Lu Lv Lw Lx Ly Lz Ma Mb Mc Md Me Mf Mg Mh Mi Mj Mk Ml Mm Mn Mp Mq Mr Mt Mu Mv Mx Mz Na Nb Nc Nd Ne Nf Ng Nh Ni Nj Nl Nm Nn Nq Nr Ns Nt Nu Nv Nw Ny Oh Oi Ok Om On Pa Pc Pd Pe Pf Pg Po Pz Qa Qb Qd Qe) Et(Fp Fr Hq Hu Hv Hw Hx Ii Ij Ik Il In Io Ip Iq Is Iu Jg Jh Jk Jl Jo Jp Jr Js Jt Lh Lu Lv Lw Lx Ly Lz Ma Mb Mc Me Mf Mg Mh Mi Mj Mk Ml Mm Mn Mp Mq Mr Mt Mu Mv Mx Mz Na Nb Nc Ne Nf Nh Ni Nj Nl Nm Nn Nq Nr Nt Nu Nv Nw Oh Oi Ok On Pa Pc Pd Pe Pf Pg Po Pz Qa Qb Qc Qd Qe) No(Fp Fr Hq Hu Hv Hw Ih Ii Ij Il In Io Iq Is Iu Iv Jg Jh Jk Jl Jm Jn Jo Jp Jr Js Jt Lh Lu Lv Lw Lx Ly Lz Ma Mb Mc Me Mf Mg Mi Mj Mk Ml Mm Mn Mp Mq Mr Mt Mu Mv Mx Mz Na Nb Nc Nd Ne Nf Ng Nh Ni Nj Nl Nm Nn Nq Nr Nt Nu Nw Oh Oi Ok On Pa Pc Pd Pe Pf Pg Pz Qa Qb Qd Qe) It(Aa Fp Fr Hq Hu Hv Hw Ih Ii Ij Il In Io Iq Is Iu Iv Jg Jh Jk Jl Jm Jn Jo Jr Js Jt Lh Lu Lv Lw Lx Ly Lz Mb Mc Me Mg Mi Mj Mk Ml Mm Mn Mp Mq Mr Mt Mu Mv Mx Mz Na Nb Nc Ne Nf Ng Nh Ni Nj Nl Nm Nn Nq Nr Nt Nv Oh Oi Ok Om On Pa Pc Pd Pe Pf Pg Po Pz Qa Qb Qd Qe) Lj(Fp Fr Hq Hu Hv Hw Hx Ii Il In Io Iq Is Iu Iv Jg Jh Jk Jl Jm Jo Jr Js Lh Lu Lv Lw Lx Ly Lz Mb Mc Md Me Mg Mh Mi Mj Mk Ml Mm Mn Mp Mq Mr Mt Mu Mv Mx My Mz Na Nb Nc Ne Nf Ng Nh Ni Nj Nl Nn Nq Nr Nt Nu Nv Ny Of Oh Oi Ok Om On Pa Pd Pe Pf Pg Po Pz Qa Qb Qd Qe) Hr(Fp Fr Hu Hv Hw Hx Ih Ii Ik In Io Iq Iu Jg Jj Jk Jl Jm Jo Jp Jq Jr Js Lh Lu Lv Lx Ly Lz Ma Mb Mc Md Mf Mg Mh Mi Ml Mm Mn Mp Mr Mt Mv My Mz Na Nb Nc Nd Ne Ng Nh Ni Nj Nk Nm Nn Nq Nr Ns Nt Nu Nv Nw Ny Oe Of Oi On Oy Oz Pa Pc Pd Pf Pg Po Pz Qa Qb Qc Qd Qe) Mw(Fp Fr Hq Hv Hw Ii Il In Io Iq Is Iu Iv Jg Jh Jk Jl Jm Jo Jp Jr Js Jt Lh Lu Lv Lw Lx Ly Lz Ma Mb Mc Me Mg Mi Mj Mk Mm Mn Mp Mq Mr Mt Mu Mx Mz Na Nb Nc Nd Ne Nf Nh Ni Nj Nl Nm Nn Nq Nr Nt Nu Nv Nw Oh Oi Ok On Pa Pc Pd Pe Pf Pg Po Pz Qa Qb Qd Qe) My(Fp Fr Hu Hv Hw Ih Ii Ik In Io Ip Iq Is Iv Jh Jj Jk Jl Jm Jp Jr Js Lu Lv Lx Ly Lz Ma Mb Mc Md Me Mf Mg Mh Mi Mm Mn Mp Mr Ms Mt Mv Mz Nb Nc Nd Ne Nh Nj Nk Nm Nn Nq Nr Ns Nt Nv Ny Oe Of Oi Ok Om On Oy Oz Pa Pc Pe Pf Pg Po Pz Qa Qb Qc Qd Qe) Ms(Fp Fr Hu Hv Hx Ik Il Io Ip Iq Is Iv Jg Jj Jl Jm Jo Jp Jq Js Jt Lv Lx Ly Lz Ma Mb Mc Md Me Mf Mh Mi Ml Mm Mn Mr Mt Mv Mz Nc Nd Ne Nf Nh Ni Nj Nk Nm Nn Nq Nr Ns Nt Nu Nv Ny Oe Of Ok Om On Oy Oz Pa Pc Pd Pe Pf Po Pz Qa Qb Qc Qd Qe) Of(Fp Hu Hv Hw Hx Ih Ii Ik In Io Iq Is Iv Jh Jj Jk Jl Jm Jo Jq Jr Js Lh Lu Lv Lx Ly Lz Mb Mc Md Mf Mg Mh Mi Mk Mm Mn Mp Mr Mu Mv Mz Nb Nc Ne Nh Ni Nj Nk Nn Nq Nr Ns Nt Nv Ny Oe Ok Om On Oy Oz Pc Pe Pf Pg Po Pz Qa Qb Qc Qd Qe) Jj(Fp Fr Hv Hw Hx Ik Il Ip Iq Is Iv Jg Jm Jp Jq Jr Js Jt Lx Ly Lz Ma Mb Mc Md Mf Mh Mi Ml Mm Mn Mp Mv Mz Nc Nd Nh Nj Nk Nm Nn Nq Nr Ns Nt Nu Nw Ny Oe Ok Om On Oy Oz Pa Pc Pe Pf Po Pz Qa Qb Qc Qd Qe) Jq(Fp Fr Hu Hx Ik Il Io Ip Iq Iv Jg Jm Jp Jr Js Jt Lx Ly Ma Mb Md Mf Mh Ml Mm Mn Mv Mz Nc Nd Nf Nk Nn Nq Nr Ns Nt Nu Ny Oe Ok Om On Oy Oz Pc Pe Pf Po Pz Qa Qb Qc Qd Qe) Oe(Fp Fr Hw Hx Ik Il Io Ip Iq Iv Jg Jk Jl Jm Jp Js Lx Ly Ma Mb Md Mf Mh Ml Mm Mn Mt Mz Nc Nd Nk Nm Nn Nq Nr Ns Nt Nu Ny Ok Om On Oy Oz Pa Pc Pf Po Pz Qa Qb Qc Qd Qe) Pb(Hq Hu Hv Hx Ii Ik In Io Iq Iu Jh Jk Jo Jr Lh Lu Lv Lw Ly Mb Mc Me Mg Mh Mi Mj Mk Ml Mq Mt Mu Mv Mx Na Nb Ne Nf Ng Nh Ni Nj Nl Nv Oh Oi Om Oz Pc Pd Pz) Nw(Fp Hu Hv Hx Ih Ii Ij Ik Il Ip Is Iv Jh Jm Jn Jt Lv Ly Mf Mh Ml Mp Mv Nc Nd Nf Ng Nh Nk Nm Ns Nt Nu Nv Ny Oh Oi Om Oz Pa Pc Pd Pg Po Qa Qb Qc Qd) Oy(Fp Fr Ih Ik In Ip Is Iv Jh Jk Jm Jn Jp Js Jt Lx Ma Md Mf Mi Mn Mr Mz Nc Nd Nk Nm Nn Nq Nr Ns Nt Nu Ny Ok On Oz Pa Pc Pe Pf Po Pz Qa Qb Qc Qd Qe) Jn(Fp Fr Hu Hv Hx Ih Ij Ik Il Ip Iv Jm Jp Jt Ly Lz Ma Md Mf Mh Ml Mv Mz Nc Nd Nf Ng Nh Nk Nm Nn Ns Nt Nu Ny Oi Om Oz Pc Pf Po Qa Qb Qc Qd) Og(Hq Hu Hw Hx Ii Io Iu Jh Jl Jo Jr Lh Lu Lw Ly Lz Mc Mh Mj Mk Ml Mp Mq Mr Mt Mu Mx Na Nb Ne Nf Ng Nh Ni Nj Nl Nv Oh Oi Om Pd Pg) Md(Fp Fr Ih Ij Ik Il In Ip Iv Jg Jm Jp Js Jt Ma Mf Mt Mz Nd Nk Nm Nn Ns Nt Nu Ny Oz Pa Pc Pf Qa Qb Qc Qd) Ip(Fp Hu Hx Ih Ij Ik Il Iv Jo Jp Jt Ly Lz Ma Mf Mh Ml Mv Nc Nd Nk Nm Nn Ns Nt Nu Ny Om Oz Pc Pf Qc Qd) Ns(Fp Fr Hx Ih Ij Ik Il Is Iv Jg Jm Jp Jt Ma Mf Mh Ml Nc Nk Nm Nn Nt Nu Ny Oz Pc Pf Qa Qb Qc Qd) Ih(Fp Fr Hx Ii Ij Ik Iv Jg Jp Jt Ma Mf Mh Ml Mz Nd Ne Nh Nk Nm Nn Nu Nv Ny Oi Om Oz Pc Pf Qc) Oz(Fp Fr Hx Ij Is Iv Jp Jt Lz Ma Mf Mh Ml Mv Mz Nd Nk Nm Nn Nu Ny Ok Om Pf Qa Qc Qd) Nk(Fp Hx Ij Il Iv Jm Jp Jt Mf Mh Ml Nm Nn Nu Ny Om Pc Qa Qb Qc Qd) Ij(Fp Hu Hx Ik Il Jo Ly Mf Mh Ml Mv Nc Nd Ng Nm Nv Ny Pc Qc Qd) Ik(Fp Iq Is Iv Jg Jt Lz Ma Nm Nn Nt Nu Pf Qa Qc Qd) Hx(Fp Il In Iv Jp Jt Ma Mf Nm Nt Nu Pa Pc Qa Qc) aA(Hw In Is Jh Jk Lx Mi Mq Mr Mt Mx Na Ni Nq Qe) Qc(Aa Il Iv Jt Ma Mh Ml Mv Nm Nu Ny Om Qd) Nm(Fp Iv Jo Mf Mh Nc Nd Ng Ny Om Pc) Ny(Fp Il In Jp Ma Mf Nu Pa Pc Qa) Om(Fp Fr Il Jg Jp Jt Ma Nn Nu Qa) Mh(Fp Il Jp Ma Mf Nu Pa Qa Qd) Mv(Fr Il Jg Ma Nn Nu) Mf(Jm Jt Ma Me Nu) Pc(Jp Jt Ma Nu Pf) Nd(Fp Iv Pd Pg) Ng(Jg Jt Ma Nu) Pa(Ii Mk

Figure 38 Continued

Figure 38 Continued

Ng Of Oi Pc Qb Qc Qd) Of(Hv Ii In Mi Mz Ok Om On Qa) Ik(Io Iu Ml Nj Nl Po Pz) Hr(Hv Hw In Jr Mz Qa) My(In Jg Mz Nb On) Ly(Mi Nc Nt) Ng(Jg Nd On) Lz(Iq Qc) Mh(Mz Ok) TibM ThaA MkPa MzOi NcNk PzPb JoOk PdPe} Nw{Ir(Et Fp Fr Hq Hr Hu Hv Hw Hx Ih Ii Ij Il In Io Ip Is Iu Iv Jg Jh Jk Jl Jm Jn Jo Jp Jq Jr Js Jt Lh Lj Lu Lv Lw Lx Ly Lz Ma Mb Mc Md Me Mf Mg Mi Mj Mk Ml Mm Mn Mp Mr Ms Mt Mu Mv Mz Na Nb Nc Nd Ne Nf Ng Nh Ni Nk Nl Nm Nn No Nq Nt Nu Nv Oh Oi Ok Om Pa Pc Pd Pe Pf Pg Po Pz Qa Qb Qc Qd Qe) aA(Fp Fr Hq Hr Hw Ii Ik Il In Io Iq Is Iu Iv Jg Jh Jk Jo Jp Jq Jr Js Lh Lu Lv Lw Lx Ly Lz Ma Mb Mc Mf Mg Mi Mj Mk Ml Mm Mn Mp Mq Mr Ms Mt Mu Mv Mx Mz Na Nb Nc Nd Ne Nf Ng Nh Ni Nj Nk Nl Nn No Nq Nr Nt Nu Nv Nx Ny Oh Oi Ok Om On Pa Pd Pe Pf Pg Po Pz Qa Qb Qd Qe) Og(Fp Fr Hq Hr Hu Hw Hx Ii Ik In Io Iq Iu Jh Jj Jk Jl Jp Jq Jr Lh Lu Lv Lw Lx Ly Lz Ma Mb Mc Md Me Mf Mg Mh Mi Mk Mm Mn Mp Mq Mr Ms Mt Mu Mv Mx My Mz Na Nb Nc Nd Ne Nf Nh Ni Nk Nl Nn Nq Nr Nt Nu Nv Nx Ny Oe Of Oh Ok Om On Oy Pa Pd Pe Pf Pg Po Pz Qc Qd Qe) Ih(Fp Hq Hr Hu Hv Hw Hx Ii Ij Il In Ip Iq Is Iv Jg Jk Jl Jm Jn Jo Jp Jq Jr Js Jt Lw Ly Lz Ma Mc Md Me Mf Mh Mj Ml Mn Mp Ms Mv Mw Na Nc Nd Ne Ng Nh Ni Nk Nm Nn No Ns Nt Nu Nv Nx Ny Of Oi Ok Pa Pc Pd Pf Pg Po Pa Qb Qc Qd) Lj(Hq Hr Hu Hv Hw Hx Ii Il In Ip Is Iv Jg Jj Jl Jm Jn Jo Jp Jq Jr Js Lw Ly Lz Mb Mc Mf Mg Mh Mi Mm Mn Mp Ms My Na Nc Nd Nk Nm Nn No Nq Ns Nt Nu Nx Of Oh Oi Ok Oy Pa Pc Pd Pe Pf Po Qa Qb Qc Qd) It(Aa Fp Fr Ii Ij Il In Io Iq Iu Jg Jh Jk Lh Lu Lv Lw Lx Lz Ma Mc Me Mg Mi Mj Mk Mm Mp Mq Mr Mt Mu Mx Mz Na Nb Ne Nf Nh Ni Nj Nl Nm Nq Nr Nt Oh Oi Ok Om On Pe Pf Pg Pz Qd Qe) My(Fp Hu Hv Hw Ii Ip Iq Is Iv Jj Jk Jl Jm Jo Jp Jq Jr Js Lh Lw Ly Mg Mi Mm Mp Mr Mt Mz Nc Nd Nm Nn No Nq Nr Ns Nt Nu Oe Ok Om On Oy Pa Pc Pe Pf Po Pz Qa Qb Qc Qd Qe) Oz(Aa Et Fp Hu Hv Hw Hx Ij In Iq Jl Jm Jn Jo Jq Jr Js Jt Ly Lz Mc Md Me Mf Mh Mi Ml Mn Mp Ms Mu Na Nc Nd Ng Nm Nn Nr Nt Nu Nv Nx Ny Oi Ok Pe Pf Qa Qb Qc Qd) Oy(Aa Et Fp Hu Hv Hw Il In Ip Is Iv Jg Jh Jj Jk Jm Jo Jq Jr Js Lw Mg Mh Mi Mn Mp Ms Nb Nc Nd Nn No Nq Nr Ns Nt Nu Oe Of On Pa Pc Pe Pf Qa Qb Qc Qd) Ns(Et Fp Hu Hv Hw Hx Ij Il Ip Is Iv Jj Jm Jo Jr Js Ly Mh Mp Mw Nc Nn No Nt Nu Ny Oe Of Pc Qa Qb Qc) Mw(Aa Et Hv Hw Hx Ij Ik Ip Is Iv Jn Jr Js Jt Ly Md Mh Mp Ms Mv Nc Ng No Nt Nv Nx Ny Pa Pc Qa Qc) Oe(Fp Hu Hv Hw Hx Il Ip Iq Jg Jj Jl Jm Jo Jq Jr Js Ly Mh Nc Nn No Nt Nu Pc Pz Qa Qb Qc Qd Qe) Iv(Et Hu Hv Ii Ip Jj Jk Jl Jm Jn Ly Md Mh Mk Ms Mv Nc Nd No Nv Nx Ny Om Pc Pd Po Qc) Jn(Et Hr Hu Hv Hx Ij Ik Ip Is Jj Jt Ly Md Mh Ms Mv Nc Nd Ng No Nv Nx Ny Oi Om Pc) Jt(Et Fp Hu Hx Ii Ip Jj Jo Md Mh Mj Ms Mv Nc Ng No Nv Ny Oi Om Pc Qb Qc) Of(Et Hv Hw Il Is Jj Jm Jq Jr Js Mi Mz Nc No Nt Ok Om Pc Pe Qa Qb) Ij(Et Hr Hx Ik Jh Jk Ly Md Mh Ml Ms Mv Nc Ng Nv Nx Ny Pc Qc) Jj(Et Fp Hv Hx Il Ip Is Jm Js Mh Mn Nc Nn No Nt Nu Ny Pc Qa) Et(Fp Hu Is Jm Js Mh Ms Mv Nc Ng No Nv Nx Pc) No(Hu Hx Ik Mh Ms Nv Pc Po) Nx(Hv Hw Is Jo Jq Jr Js Qa) Hu(Il Is Mh Nn Nt Pc) Aa(Jm Pb Pc Qb Qc) In(Hr Hx Md Ny Om) Hv(Hr Md Ny Om) Is(Hx Ms Nv Pc) Md(Hw Qa) Mh(Js Pc) Hr(Jo Qa) Qd(Ik Il) Nv(Mi Nt) NcNk PzPb} Et{Ih(Fp Fr Hq Hr Hu Hv Hw Hx Ii Ij Ik Il In Io Ip Iq Ir Is Iv Jg Jh Jk Jl Jm Jn Jo Jp Jq Jr Js Jt Lh Lu Lw Lx Ly Lz Ma Mb Mc Md Me Mf Mg Mh Mi Mj Mk Ml Mn Mp Mr Ms Mt Mv Mx My Mz Na Nb Nc Nd Ne Ng Nh Ni Nj Nk Nl Nm Nn Nr Ns Nt Nu Nv Nx Ny Of Oh Oi Ok Om Oz Pa Pc Pd Pe Pf Pg Pz Qa Qb Qc Qd) aA(Fp Fr Hq Hr Hu Hv Hw Hx Ii Ik Il In Io Iq Is Iu Iv Jg Jh Jj Jk Jl Jo Jp Jq Jr Jt Lh Lu Lv Lw Lx Ly Lz Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni Nj Nk Nl Nm Nn No Nq Nr Nt Nu Nv Nx Ny Oh Oi Ok Om On Pa Pd Pe Pf Pg Po Pz Qa Qd Qe) Ir(Fp Hq Hr Hu Hv Hx Ii Ij Il In Io Ip Is Iu Iv Jh Jk Jl Jm Jn Jo Jq Jr Js Jt Lv Lw Lx Ly Lz Ma Mb Mc Md Me Mf Mg Mh Mi Mj Mk Mn Mp Ms Mt Mv My Mz Nb Nc Nd Ne Ng Nh Ni Nk Nl Nm Nn No Nr Ns Nt Nu Nv Nx Ny Oh Oi Pa Pc Pd Pe Pf Pg Po Pz Qb Qc) Lj(Fp Fr Hx Iq Iu Jg Jh Jk Jl Jp Jr Lh Lu Lv Ma Md Me Mg Mk Ml Mm Mn Mq Mr Mu Mv Mx My Na Nf Ng Nh Nj Nl Nm Nr Nu Nv Ny Ok Om Pd Po Pz Qa Qd Qe) Oe(Hv Hw In Ip Iq Jj Jm Jq Jt Lx Lz Mz Nc Nd Nn Nr Ns Nt Ny Of Og Oh On Oy Oz Pa Pc Pe Pf Qc Qd Qe) Pb(Fp Hv Hw Il In Ip Iv Jj Jq Jt Lz Mh Mr Mz Nc Nd Nn Nr Ns Nt Of Og Ok Pe Pf Pg Qa Qc Qd Qe) No(Hr Hu Ij Ik Ip Is Iv Jj Jm Jn Js Ms Mw My Nc Nd Ng Nv Nx Of Pc Qb Qc) Ij(Fp Hr Ik Ip Is Iv Jh Jk Jn Jo Lz Ms Mv Mw Nc Nd Ns Nx Oz Qc) Jn(Hu Ip Is Iv Js Ms Mw My Mz Nc Nd Ng Ns Nx Of Oy Oz Qc) Og(Fp Il In Ip Iv Jq Jt Mz Nb Nn Ns On Oz Qa Qb Qc Qd Qe) Oy(Fp Il Ip Is Iv Jm Js Nc On Pe Pf Pg Qa Qb Qc Qd) Mw(Fp Hu Ik Ip Is Iv Jq Js Ms Mv Nc Ng Ns Oz Qc) Jj(Fp Il Ip Is Iv Jm Js Jt Nc Nn Oz Qa Qb Qc) Of(Fp Il In Ip Is Iv Jq Js Jt Mz Om Oz Qa Qb) Js(Ik Ip Jo My Ng Ns Nx Oi Oz) Oz(Fp Ip Is Iv Qb Qd) Ns(Fp Is Iv Qb Qc) My(Is Nb On Qb) Iv(Hx Nd Qc) Aa(It Qc) Ik(Fp Qd) Is(Hr Hu) Pd(Pe Pf) NdHq IlQd JoJt} aA{Ij(Fp Fr Hq Hw Il In Io Is Iu Iv Jg Jl Jm Jo Jp Jq Jr Lh Lu Lv Lx Mb Mc Mf Mg Mi Ml Mp Mq Mr Mt Mx Na Ni Nj Nl Nn Nq Nt Nu Oh Ok On Pa Pe Pf Pg Pz Qa Qe Ti) Ip(Fp Hr Hu Hv Ih Ik Il Io Jg Jj Jm Jp Js Jt Lw Lx Ly Lz Ma Md Me Mg Mm Mn Ms My Mz Nc Ni Nj Nm Nn No Nr Ns Nt Nu Ny Of Oi Ok Oy Pa Pc Pd Pf Qb Qc Qd) Ir(Hr Hu Ih Ik Io Iu Jg Jj Jn Jp Js Jt Lj Lw Ma Md Me Mg Mj Mm Mn Mp My Mz Nd Ne Nh Nk Nm Nn No Ns Nu Nv Ny Of Oi Ok Oy Pa Pc Pd Qc) It(Fp Fr Hu Ih Ik Iq Is Jj Jm Jn Jp Js Jt Lw Lx Ly Lz Ma Md Me Mg Mm Mz Nd Ne Nh Nr Ns Nu Ny Oe Ok On Oy Pc Pd Qa Qb Qc Qd) Lj(Hv Ih Ik Jj Jn Js Jt Lw Ma Me Mh Mm Mn Mp Mz Nd Nk Nn No Ns Ny Og Ok On Oy Pc Qc) Pb(Ih Jg Js Jt Ma Mn Mw Mz Nm Ny Oe Ok On Qa Qb Qc Qd) Mw(Hu Ih Ik Jj Jn Js Jt Nm No Ns Of Og Oy Oz Qc) Oe(Is Jg Jm Jn Js Jt Nn No Ny Ok On Qa Qb Qd) Nm(Ih Jj Jn Js Mz Ns Of Oy Oz Qb Qc) Jt(Hr Ih Jj Jn Mz Ns Of Og Oz Qb Qc) Ih(Jg Jj Ma Me No Og Oz Qc) Jn(Me Mz No Ns Og Oz Qc) Oz(Js Mn No Ok Qc Qd) Og(Jg Jm Js No Qc) Jg(Hu My Ns) No(Ns Oy) TiOa GcNe IkQd PflX} Ij{Jj(Aa Fp Hr Hu Hx Ih Ik Ip Iq Is Iv Jg Jm Jn Jp Js Jt Lx Ly Lz Ma Md Mh Mi Ml Mm Mn Mp Ms Mv Mz Nc Nd Nm Nn Nr Ns Nt Nu Ny Ok Om On Oz Pf Qa Qb Qc Qd) Og(Hq Hv Hw Hx Ii Il In Io Jh Jk Lu Lv Ly Ma Mb Mc Md Mf Mh Mj Mk Ml Mq Ms Mu Mv Mx My Na Ne Nf Ng Nh Nj Nk Nl Nq Nr Nv Nx Oe Oi Pd Pg Pz Qe) Oy(Fr Ih Ik Ip Iq Ir Is Iv Jh Jn Jp Jq Jt Lh Lj Lz Mm Mn Mr Mz Nb Nd Nq Nt Oe Ok Oz Pc Pe Pf Pg Po Qc) Pb(Aa Fp Fr Hu Ih Ik Ip Iq Is It Iv Jn Jp Jt Lh Lx Lz Ma Mi Mm Mp Ms My Nd Nn Of Ok On Pf Qa Qd) Of(Fr Hu Ih Ir Is Iv Jp Jt Lh Lx Lz Mm Mp Mr Mz Nd Nn Nt Ok Pa Pe Po) My(Fr Ih Is Jp Jt Lx Mm Mp Mw Nb Nn Nq Ok Pa) Lj(Hu Ih Ik Is Jp Jt Mi Mm Mp Mw Nn No) No(Hr Hu Ih Ik It Mw Ns Oz) Mw(Aa Hu Ih Ir Oc) Oe(Is Jt Qd) Hr(Iv Ok) AaQc ThUr NnHu NlfR IkQd KcbN} Aa{Qc(Fp Hr Hu Ih Ik Il Io Ip Iq Ir Is Iv Jj Jm Jn Jp Js Lu Lw Lx Lz Ma Md Mf Mg Mj Mk Mp Mq Mr Mt Mu Mw My Nc Nd Ni Nk Nn No Nq Ns Nu Nx Ny Oe Of Of Oy Oz Pa Pb Pc Pf Pg Qa Qb) It(Fp Fr Hq Hr Hv In Ip Jl Jm Jn Jo Jp Jr Js Lz Ma Md Mq Mr Mt Mu Nd Nk Nn No Nx Og Oy Oz Pb Pc Pf Po Qa Qb Qd Qe) Mw(Fp Hr Ih Ip Ir Iv Jj Jn Js Lu Lz Mq Mr Nu Nx Oe Of Og Oi Oy Oz Pb Pc Qb) Qb(In Ip Jj Lu Mq Mu Ni Nk Nn Nx Oe Of Og Oi Oy Oz Pb Pc) Pb(Fp Ih Ip Ir Js Lx Lz Mq Mr Mt Mu Nn No Oe Pf Qa) Oy(Ip Ir Js Lx Lz Mr Mt Nn No Pe Pf Pg Qa Qe) Oz(Fp Ip Js Lz Mr Mt No Pf Qa) Qa(Jj Nk Nx Oe Of Og Oi) Js(Hr Ip Jj Mq Oe Of Og) Og(Fp Jm Qd Qe) Lz(Ip Jm Pc) Jj(Ih Ip Iv) FpHr MyJh IhOe IpPc QeNx} Ir{Og(Fp Fr Ih Ii Ik Il In Io Is It Iv Jh Jj Jm Jn Jp Jq Js Lj Lw Lz Ma Mb Mc Me Mg Mi Mm Mp Mt Mv Mz Nb Nd Ne Nh Nk Nn Nq Ns Nt Nu Ny Oe Ok Om On Oz Pa Pc Pe Pf) Oe(Fr Hr Ih Il Io Ip Is It Iv Jj Jn Jp Jq Js Lj Lw Lx Ma Mb Mc Mf Mg Mi Mm Mn Mp Mt Nd Nh Nm Nq Ns Nt Nu Ny Ok Om Oy Pc Pf Pz Qc Qd) Pb(Fr Ik Ip Is It Jg Jj Jn Jp Jt Lj Lw Ma Mn Mp Ne Nk Nm Nn Ns Ok On Pc Pf) Mw(Hq Hr Hu Il Ip Is It Lj Ms My Ng Nk No Ns Of Oi Oz Qc) Jj(Ih Ik Il Ip It Jg Jt Ma Mn Nm Nn No On Oz) Oy(Jh Jp Ma Mn No On) No(Ik It Ns Oz) Hr(Iv Jt Ok) Ik(Lj Qd) NsNd MyJg IpOz UhbN} No{Pb(Fp Hu Hv Hw Ii Ik Il In Iq Iv Jg Jl Jm Jo Jp Jq Jr Js Lh Lj Lw Ly Lz Ma Me Mf Mg Mh Mi Mm Mn Mp Mr Ms Mt My Mz Nb Nc Nd Ne Nh Ni Nk Nm Nn Nt Nu Ny Of Og Oi Ok Om On Oy Oz Pa Pc Pe Pf Pg Qa Qb Qc Qd) It(Hu Ih Ip Is Iv Jg Jn Jp Jt Ly Mh Ms Mw My Nd Ne Nk Nn Oe Of Ok Oy Pa Pc Pd) Ns(Ih Ik Ip Is Jj Jn Jt Mw Nc Oe Og Oy) Og(Ih Ip Is Jg Jm Jn Jt Mw Nm Oz) Oz(Ih Is Iv Jj Jn Jt Mw Oe Of) Jj(Ip Is Jn Js Jt Mw Nm) Oy(Ih Ip Is Jn Jt Mw) Oe(Ip Is Jn Jt Mw) Th(Kc Kd Ke Ld) Ti(Bo Kd Nb) Mw(Ih Ik Ip) Hr(Iv Jt) Ih(Ip Nk) NdHq IkQd JtOf KeVs} Jj{It(Fr Ih Ii Ip Jg Jn Jp Js Jt Lj Mn Nm Nn Ok On) Ih(Ip Jg Js Jt Lj Ma Nm Nn Oe Pb) Mw(Ip Is Iv Jn Js Jt Lj Nm Nt) Jt(Ip Jn Lj Qb) On(Lj Pb)}

Figure 38 Continued bN{Uh(Ad aM Bn Dd Iv Jt Kn Kp Kr Mz Nf Ny Pb Rb Rj Sr Tv Uc Un Vs Vu Vv) Ke(Af bG Bn CH De Il Jv Lh Ne Nk Pb Ph Qc Qy) DeKq}
Og{Mw(Ih Ip It Iv Jg Jn Js Jt Lj) Ih(Ip Jt Lj Ma Nm Ok On) Jg(Ip Is It Js Lj Qb) Jt(Fp Ip It Jn Pb Qb) Is(Ip It Lj Nm) It(Ok On) Lj(Mg On)}
Oe{Ih(Fr Is Jg Jt Lj Ma Mw Nm Nn Ok On) Is(Jg Lj Mw Pb) Jt(Lj Qb) On(Lj Pb) QaPb} Ke{Nx(aW bL De Il Pb Qy Uu Vp) De(Ez Kq Qy)
Lh(Ed Nr Rh) Il(Ph Vp) Qy(Bg Ch) NnVs} Mw{Is(Ik It Lj Of Pb) Pb(Ip Iv Jn Ok) Lj(Ih Ik Jt) Of(Iv Jt Nb) Hrlv IkQd} Pb{Is(Fr Ip It Lj Ma)
Lj(Jt Ok On) It(Ok On)} Jt{Lj(Hr Ih Ik) MtOf HrIh} Pe{IX(Lv IW mZ Nb)} Ti{Nb(Ar Of)} Ik{Qd(It Lj)] DeKqOu ThIvLd NsNdLj HrItOk Unconstrained panels with 3 analytes, where 1.0E-8 >= 'model p-value' > 1.0E-9. Contains 19,487 panels of 15,247,928 total panels evaluated. : Ji{Js(Aa Fp Fr Hq Hu Hv Hw Hx Ih Ii Ij Ik Il In Io Ip Iq Is Iu Iv Jg Jh Jk Jl Jm Jn Jo Jp Jr Jt Lh Lu Lv Lw Lx Ly Lz Ma Mb Mc Me Mf Mg Mh Mi Mj Mk Ml Mm Mn Mp Mq Mr Mt Mu Mv Mx Mz Na Nb Nc Nd Ne Nf Ng Nh Ni Nj Nk Nl Nm Nn Nq Nr Ns Nt Nu Nv Nw Ny Oh Oi Ok Om On Oz Pa Pc Pd Pe Pf Pg Po Pz Qa Qb Qc Qd Qe) Ok(Fp Fr Hq Hu Hv Hw Hx Ih Ii Ij Ik Il In Io Ip Iq Is Iu Iv Jg Jh Jk Jl Jm Jn Jo Jp Jr Jt Lh Lu Lv Lw Lx Ly Lz Ma Mb Mc Md Me Mf Mg Mh Mi Mj Mk Ml Mm Mn Mp Mq Mr Mt Mu Mv Mx Mz Na Nb Nc Nd Ne Nf Ng Nh Ni Nj Nk Nl Nm Nn Nq Nr Ns Nt Nu Nv Nw Ny Oh Oi Om On Pa Pc Pd Pe Pf Pg Po Pz Qa Qb Qc Qd Qe) Is(Fp Fr Hq Hu Hv Hw Hx Ih Ii Ij Il In Io Ip Iq Iu Iv Jg Jh Jk Jl Jm Jn Jo Jp Jr Jt Lh Lu Lv Lw Lx Ly Lz Ma Mb Mc Md Me Mf Mg Mh Mi Mj Mk Ml Mm Mn Mp Mq Mr Mt Mu Mv Mx Mz Na Nb Nc Nd Ne Nf Ng Nh Ni Nj Nk Nl Nm Nn Nq Nr Nt Nu Nv Ny Oh Oi Om On Pa Pc Pd Pe Pf Pg Po Pz Qa Qb Qc Qd Qe Yd) Mz(Fp Fr Hq Hu Hv Hw Hx Ii Ij Ik Il In Io Ip Iq Iu Iv Jg Jh Jk Jl Jm Jo Jp Jr Jt Lh Lu Lv Lw Lx Ly Lz Ma Mb Mc Me Mf Mg Mh Mi Mj Mk Ml Mm Mn Mp Mq Mr Mt Mu Mv Mx Na Nb Nc Nd Ne Nf Ng Nh Ni Nj Nk Nl Nm Nn Nq Nr Ns Nt Nu Nv Nw Ny Oh Oi Om On Pa Pc Pd Pe Pf Pg Po Pz Qa Qb Qc Qd Qe) Qb(Aa Fp Fr Hq Hu Hv Hw Hx Ih Ii Ij Ik Il In Io Ip Iq Iu Iv Jg Jh Jk Jl Jm Jo Jp Jr Jt Lh Lu Lv Lw Lx Ly Lz Ma Mb Mc Me Mf Mg Mh Mi Mj Mk Ml Mm Mn Mp Mq Mr Mt Mu Mv Mx Na Nb Nc Nd Ne Nf Ng Nh Ni Nj Nl Nm Nn Nq Nr Nt Nu Nv Ny Oh Oi Om On Oz Pa Pc Pd Pe Pf Pg Po Pz Qa Qc Qd Qe) Jm(Aa Fp Fr Hq Hu Hv Hw Hx Ih Ii Ij Ik Il In Io Ip Iq Iu Iv Jg Jh Jk Jl Jo Jp Jr Jt Lh Lu Lv Lw Lx Ly Lz Ma Mb Mc Me Mg Mh Mi Mj Mk Ml Mm Mn Mp Mq Mr Mt Mu Mv Mx Na Nb Nc Nd Ne Nf Ng Nh Ni Nj Nl Nm Nn Nq Nr Nt Nu Nv Ny Oh Oi Om On Oz Pa Pc Pd Pe Pf Pg Po Pz Qa Qc Qd Qe Rt) Qe(Aa Fp Fr Hq Hu Hv Hw Hx Ih Ii Ij Ik Il In Io Ip Iq Iv Jg Jh Jk Jl Jn Jo Jp Jr Jt Lu Lv Lx Ly Lz Ma Mb Mc Md Me Mf Mh Mi Mj Mk Ml Mm Mn Mp Mq Mr Mt Mu Mv Nb Nc Nd Ne Nf Ng Nh Ni Nj Nk Nl Nm Nn Nq Nr Ns Nt Nu Nv Nw Ny Oh Oi Om On Oz Pa Pc Pd Pe Pf Pg Po Pz Qa Qc Qd) Jg(Fp Fr Hq Hu Hv Hw Hx Ii Ij Il In Io Ip Iq Iu Iv Jh Jk Jl Jn Jo Jp Jr Jt Lh Lu Lv Lw Lx Ly Lz Ma Mb Mc Me Mf Mg Mh Mi Mj Mk Ml Mm Mn Mp Mq Mr Mt Mu Mx Na Nb Nc Nd Nc Nf Nh Ni Nj Nk Nl Nm Nn Nq Nr Nt Nu Nv Nw Ny Oh Oi On Oz Pa Pc Pd Pe Pf Pg Po Pz Qa Qc Qd Yd) Fr(Fp Hq Hu Hv Hw Hx Ii Ij Ik Il In Io Ip Iq Iu Iv Jh Jk Jl Jo Jp Jr Jt Lh Lu Lv Lw Lx Ly Lz Ma Mb Mc Me Mf Mg Mh Mi Mj Mk Ml Mm Mn Mp Mq Mr Mt Mu Mx Na Nb Nc Nd Ne Nf Ng Nh Ni Nj Nk Nl Nm Nn Nq Nr Nt Nu Nv Nw Ny Oh Oi On Pa Pc Pd Pe Pf Pg Po Pz Qa Qc Qd) Ml(Fp Hq Hu Hv Hw Hx Ii Ik Il In Io Iq Iu Iv Jh Jk Jl Jo Jp Jr Jt Lh Lu Lv Lw Lx Ly Lz Ma Mb Mc Md Me Mf Mg Mh Mi Mj Mk Mm Mn Mp Mq Mr Mt Mu Mv Mx My Na Nb Nc Nd Nc Nf Ng Nh Ni Nj Nl Nm Nn Nq Nr Nt Nv Ny Of Oh Oi Om On Oy Pa Pc Pd Pe Pf Pg Po Pz Qa Qd) Nc(Fp Hq Hu Hv Hw Hx Ih Ii Ik Il In Io Iq Iu Iv Jh Jk Jl Jo Jp Jr Jt Lh Lu Lv Lw Lx Ly Lz Ma Mb Mc Md Me Mf Mg Mh Mi Mj Mk Mm Mn Mp Mq Mr Mt Mu Mv Mx Na Nb Nd Ne Nf Ng Nh Ni Nj Nl Nn Nq Nr Nt Nu Nv Ny Oh Oi Om On Oz Pa Pc Pd Pe Pf Pg Po Pz Qa Qc Qd) Nt(Fp Hq Hu Hv Hw Ih Ii Ij Il In Io Iq Iu Iv Jh Jk Jl Jo Jp Jr Jt Lh Lu Lv Lw Lx Ly Lz Ma Mb Mc Me Mf Mg Mh Mi Mj Mk Mm Mn Mp Mq Mr Mt Mu Mv Mx Na Nb Nd Ne Nf Ng Nh Ni Nj Nk Nl Nm Nn Nq Nr Nu Ny Oh Oi Om On Oz Pa Pc Pd Pe Pf Pg Pz Qa Qc Qd Yd) Mv(Fp Hq Hu Hv Hw Hx Ih Ii Ik In Io Iq Iu Iv Jh Jk Jl Jo Jp Jr Jt Lh Lu Lv Lw Lx Ly Lz Mb Mc Md Me Mf Mg Mh Mi Mj Mk Mm Mn Mp Mq Mr Mt Mu Mx Na Nb Nd Ne Nf Ng Nh Ni Nj Nk Nl Nm Nq Nr Ns Nv Ny Oe Oh Oi Om On Oy Pa Pc Pd Pe Pf Pg Po Pz Qa Qd) Nn(Fp Hq Hu Hv Hw Hx Ii Ij Il In Io Iq Iu Iv Jh Jk Jl Jo Jp Jr Jt Lh Lu Lv Lw Lx Ly Lz Ma Mb Mc Me Mf Mg Mh Mi Mj Mk Mm Mn Mp Mq Mr Mt Mu Mx Na Nb Nd Ne Nf Ng Nh Ni Nj Nl Nm Nq Nr Nu Nv Nw Ny Oh Oi On Pa Pc Pd Pe Pf Pg Po Pz Qa Qc Qd) Pf(Fp Hq Hu Hv Hw Hx Ii Ij Il In Io Iq Iu Iv Jh Jk Jl Jo Jp Jr Jt Lh Lu Lv Lw Lx Ly Lz Ma Mb Mc Me Mf Mg Mh Mi Mj Mk Mm Mn Mp Mq Mr Mt Mu Mx Na Nb Nd Ne Nf Ng Nh Ni Nj Nk Nl Nm Nq Nr Nu Nv Nw Ny Oh Oi Om On Pa Pe Pg Po Pz Qa Qc Qd) Qa(Aa Fp Hq Hu Hv Hw Ih Ii Ij Il In Io Ip Iq Iu Iv Jh Jk Jl Jo Jp Jr Jt Lh Lu Lv Lw Lx Ly Lz Ma Mb Mc Me Mf Mg Mi Mj Mk Mm Mn Mp Mq Mr Mt Mu Mx Na Nb Nd Ne Nf Ng Nh Ni Nj Nl Nm Nq Nr Nu Nv Oh Oi On Pa Pc Pd Pe Pg Po Pz Qc Qd) Lx(Fp Hq Hu Hv Hw Hx Ih Ii Ij Ik Il In Io Ip Iq Iv Jh Jl Jn Jo Jp Jr Jt Lh Lu Lv Ly Lz Ma Mb Mc Md Me Mf Mh Mi Mj Mk Mm Mn Mp Mr Mu Nd Ne Nf Ng Nh Ni Nj Nk Nm Nq Nr Ns Nu Nv Nw Ny Oh Oi Om Oz Pa Pc Pd Pe Pg Po Pz Qc Qd) Qd(Aa Fp Hq Hu Hv Hw Hx Ih Ii In Io Iq Iu Iv Jh Jk Jl Jo Jp Jr Jt Lh Lu Lv Lw Ly Lz Ma Mb Mc Me Mf Mg Mi Mj Mk Mm Mn Mp Mq Mr Mt Mu Mx Na Nb Nd Ne Nf Ng Nh Ni Nj Nl Nm Nq Nr Nu Nv Ny Oh Oi Om On Pa Pc Pd Pe Pg Po Pz) Il(Fp Hq Hu Hv Hw Ih Ii Ik In Io Iq Iu Iv Jh Jk Jl Jo Jp Jr Jt Lh Lu Lv Lw Ly Lz Ma Mb Mc Me Mf Mg Mi Mj Mk Mm Mn Mp Mq Mr Mt Mu Mx Na Nb Nd Ne Nf Ng Nh Ni Nj Nl Nm Nq Nr Nu Nv Oh Oi On Oz Pa Pc Pd Pe Pg Po Pz) Jp(Fp Hq Hu Hv Hw Ii Ij Ik In Io Iq Iu Iv Jh Jk Jl Jo Jr Jt Lh Lu Lv Lw Ly Lz Ma Mb Mc Me Mf Mg Mi Mj Mk Mm Mn Mp Mq Mr Mt Mu Mx Na Nb Nd Nc Nf Ng Nh Ni Nj Nl Nm Nq Nr Nu Nv Nw Oh Oi On Pa Pd Pe Pg Po Pz Qc) Om(Hq Hr Hu Hv Hw Hx Ii Ik In Io Iq Iu Iv Jh Jk Jl Jo Jr Lh Lu Lv Lw Ly Lz Mb Mc Md Me Mf Mg Mh Mi Mj Mk Mm Mn Mp Mq Mr Mt Mu Mx Na Nb Nd Ne Nf Ng Nh Ni Nj Nl Nq Nr Ns Nv Ny Oh Oi On Oy Pa Pc Pd Pe Pg Po Pz) Nd(Hu Hv Hw Hx Ii Ik In Io Iq Iu Jh Jk Jl Jo Jr Jt Lh Lu Lv Lw Ly Lz Ma Mb Mc Me Mf Mg Mh Mi Mj Mk Mm Mn Mp Mq Mr Mt Mu Mx Na Nb Ne Nf Ng Nh Ni Nj Nk Nl Nq Nr Nu Nv Ny Oh Oi On Pa Pc Pe Po Pz Qc Yd) Iv(Aa Fp Hq Hu Hv Hw Ii Ij In Io Iq Iu Jh Jk Jl Jr Jt Lh Lu Lv Lw Ly Lz Mb Mc Me Mf Mg Mh Mi Mj Mk Mm Mn Mp Mq Mr Mt Mu Mx Na Nb Ne Nf Ng Nh Ni Nj Nl Nq Nr Nu Nv Ny Oh Oi On Pa Pc Pd Pe Pg Po Pz) Pc(Aa Fp Hq Hu Hv Hw Ii Ik In Io Iq Iu Jh Jk Jl Jo Jr Lh Lu Lv Lw Ly Lz Mb Mc Me Mf Mg Mh Mi Mj Mk Mm Mn Mp Mq Mr Mt Mu Mx Na Nb Ne Nf Ng Nh Ni Nj Nl Nq Nr Nv Oh Oi On Oz Pa Pd Pe Pg Po Pz Qc) Ma(Fp Hq Hu Hv Hw Ii Ij In Io Iq Iu Jh Jk Jl Jo Jr Jt Lh Lu Lv Lw Ly Lz Mb Mc Me Mg Mi Mj Mk Mm Mn Mp Mq Mr Mt Mu Mx Na Nb Ne Nf Nh Ni Nj Nk Nl Nm Nq Nr Nu Nv Nw Oh Oi On Pa Pd Pe Pg Po Pz) Mh(Hq Hu Hv Hw Hx Ii Ik In Io Iq Iu Jh Jk Jl Jo Jr Jt Lh Lu Lv Lw Ly Lz Mb Mc Md Me Mg Mi Mj Mk Mm Mn Mp Mq Mr Mt Mu Mx Na Nb Ne Nf Ng Nh Ni Nj Nl Nq Nr Nv Ny Oh Oi On Oy Pd Pe Pg Po Pz) Fp(Aa Hq Hu Hv Hw Ii In Io Iq Iu Jh Jk Jl Jo Jr Lh Lu Lv Lw Ly Lz Mb Mc Me Mf Mg Mi Mj Mk Mm Mn Mp Mq Mr Mt Mu Mx Na Nb Ne Nf Ng Nh Ni Nj Nl Nq Nr Nu Nv Oh Oi On Pa Pd Pe Pg Po Pz Qc) Nu(Fc Hq Hu Hv Hw Ii Ij In Io Iq Iu Jh Jk Jl Jo Jr Jt Lh Lu Lv Lw Ly Lz Mb Mc Me Mg Mi Mj Mk Mm Mn Mp Mq Mr Mt Mu Mx Na Nb Ne Nf Nh Ni Nj Nl Nm Nq Nr Nv Oh Oi On Pa Pd Pe Pg Po Pz) Hx(Hq Hu Hv Hw Ii Ik Io Iq Iu Jh Jk Jl Jo Jr Lh Lu Lv Lw Ly Lz Mb Mc Md Mc Mg Mi Mj Mk Mm Mn Mp Mq Mr Mt Mu Mx My Na Nb Ne Nf Ng Nh Ni Nj Nl Nq Nr Nv Ny Oh Oi On Oy Pd Pe Pg Po Pz) Mf(Aa Hq Hu Hv Hw Ii Ik In Io Iq Iu Jh Jk Jl Jo Jr Lh Lu Lv Lw Ly Lz Mb Mc Mg Mi Mj Mk Mm Mn Mp Mq Mr Mt Mu Mx Na Nb Ne Nf Ng Nh Ni Nj Nl Nq Nr Nv Oh Oi On Pa Pd Pe Pg Po Pz Qc) Nk(Aa Hq Hu Hv Hw Ii Ik In Io Iq Iu Jh Jk Jl Jo Jr Lh Lu Lv Lw Ly Lz Mb Mc Me Mg Mi Mj Mk Mm Mn Mp Mq Mr Mt Mu Mx Na Nb Ne Nf Ng Nh Ni Nj Nl Nq Nr Nv Oh Oi On Pa Pd Pe Pg Po Pz) Jt(Hq Hu Hv Hw Ii Ij In Io Iq Iu Jh Jk Jl Jr Lh Lu Lv Lw Ly Lz Mb Mc Me Mg Mi Mj Mk Mm Mn Mp Mq Mr Mt Mu Mx Na Nb Ne Nf Nh Ni Nj Nl Nm Nq Nr Nv Ny Oh Oi On Pa Pd Pe Pg Po Pz Yd) Oz(Aa Hq Hu Hv Hw Ii Ik In Io Iq Iu Jh Jk Jl Jo Jr Lh Lu Lv Lw Ly Mb Mc Me Mg Mi Mj Mk Mm Mn Mp Mq Mr Mt Mu Mx Na Nb Ne Nf Ng Nh Ni Nj Nl Nq Nr Nv Oh Oi On Pa Pd Pe

Figure 38 Continued

Pg Po Pz) Ns(Hq Hu Hv Hw Ii In Io Iq Iu Jh Jk Jl Jo Jr Lh Lu Lv Lw Ly Lz Mb Mc Me Mg Mi Mj Mk Mm Mn Mp Mq Mr Mt Mu Mx Na Nb Ne Nf Ng Nh Ni Nj Nl Nq Nr Nv Oh Oi On Pa Pd Pe Pg Po Pz) Qc(Hq Hu Hv Hw Ii In Io Iq Iu Jh Jk Jl Jo Jr Lh Lu Lv Lw Ly Lz Mb Mc Me Mg Mi Mj Mk Mm Mn Mp Mq Mr Mt Mu Mx Na Nb Ne Nf Ng Nh Ni Nj Nl Nq Nr Nv Oh Oi On Pa Pd Pe Pg Po Pz) Ny(Hq Hu Hv Hw Ii Ik Io Iq Iu Jh Jk Jl Jo Jr Lh Lu Lv Lw Ly Lz Mb Mc Me Mg Mi Mj Mk Mm Mn Mp Mq Mr Mt Mu Mx Na Nb Ne Nf Ng Nh Ni Nj Nl Nq Nr Nv Oh Oi On Pd Pe Pg Po Pz Yd) Nm(Hq Hu Hv Hw Ii In Io Iq Iu Jh Jk Jl Jr Lh Lu Lv Lw Ly Lz Mb Mc Me Mg Mi Mj Mk Mm Mn Mp Mq Mr Mt Mu Mx Na Nb Ne Nf Nh Ni Nj Nl Nq Nr Nv Oh Oi On Pa Pd Pe Pg Po Pz) Md(Aa Hq Hu Hv Hw Ii Io Iq Iu Jh Jk Jl Jo Jr Lh Lu Lv Lw Ly Lz Mb Mc Me Mg Mi Mj Mk Mm Mn Mp Mq Mr Mu Mx Na Nb Ne Nf Ng Nh Ni Nj Nl Nq Nr Nv Oh Oi On Pd Pe Pg Po Pz) Ik(Hq Hu Hv Hw Ii In Io Iu Jh Jk Jl Jo Jr Lh Lu Lv Lw Ly Mb Mc Me Mg Mi Mj Mk Mm Mn Mp Mq Mr Mt Mu Mx Na Nb Ne Nf Ng Nh Ni Nj Nl Nq Nr Nv Oh Oi On Pa Pd Pe Pg Po Pz) Ih(Aa Hq Hu Hv Hw In Io Iq Iu Jh Jk Jl Jo Jr Lh Lu Lv Lw Ly Lz Mb Mc Me Mg Mi Mj Mk Mm Mn Mp Mq Mr Mt Mu Mx Na Nb Nf Ng Ni Nj Nl Nq Nr Oh On Pa Pd Pe Pg Po Pz Yd) Ip(Aa Hq Hv Hw Ii In Io Iq Iu Jh Jk Jl Jr Lh Lu Lv Lw Mb Mc Me Mg Mi Mj Mk Mm Mn Mp Mq Mr Mt Mu Mx Na Nb Ne Nf Ng Nh Ni Nj Nl Nq Nr Nv Oh Oi On Pa Pd Pe Pg Po Pz) Ij(Hq Hv Hw Ii In Io Iq Iu Jh Jk Jl Jr Lh Lu Lv Lw Lz Mb Mc Me Mg Mi Mj Mk Mm Mn Mp Mq Mr Mt Mu Mx Na Nb Ne Nf Nh Ni Nj Nl Nq Nr Oh Oi On Pa Pd Pe Pg Po Pz Yd) Jn(Hq Hw Ii In Io Iq Iu Jh Jk Jl Jo Jr Lh Lu Lv Lw Mb Mc Me Mg Mi Mj Mk Mm Mn Mp Mq Mr Mt Mu Mx Na Nb Ne Ni Nj Nl Nq Nr Nv Oh On Pa Pd Pe Pg Pz Yd) Lz(Aa Hq Hu Hv Ii Io Iq Jl Jo Jq Jr Lh Lu Lv Ly Mb Mc Me Mj Mk Mm Mn Mp Mr Mt Ne Nf Ng Nh Ni Nj Nq Nr Nv Nw Oe Oh Oi On Oy Pa Pd Pe Pg Po Pz) Oy(Aa Hq Hu Hv Hw Ii Io Iq Iu Jl Jo Jr Lh Lu Lv Lw Ly Mb Mc Me Mg Mj Mk Mm Mp Mq Mt Mu Mx Na Nb Ne Nf Ng Nh Ni Nj Nl Nv Oh Oi Pd Pg) Mn(Hq Hu Hv Hw Ii In Io Iq Jh Jl Jo Jr Lu Lv Ly Mb Mc Mi Mk Mm Mp Mr Mu Ne Nf Ng Nh Ni Nj Nq Nr Nv Nw Oh Oi Pa Pd Pe Pg Po Pz) Jq(Aa Hq Hv Hw Ii In Iu Jh Jk Jl Jo Lh Lu Lv Lw Mc Me Mg Mi Mj Mk Mp Mq Mr Mt Mu Mx Na Nb Ne Ng Nh Ni Nj Nl Nv Oh Oi Pa Pd Pg) Oe(Aa Hq Hu Hv Ii In Iu Jh Jo Jr Lh Lu Lv Lw Mc Me Mg Mi Mj Mk Mp Mq Mr Mu Mx Na Nb Ne Nf Ng Nh Ni Nj Nl Nv Oh Oi Pd Pe Pg) Pz(Hq Hu Hv Hw Ii Io Iq Jh Jl Jo Jr Lu Lv Ly Mb Mc Mi Mk Mm Mp Mr Mu Ne Nf Ng Nh Ni Nj Nq Nr Nv Nw Oh Oi Pa Pd Pe Pg Po) Po(Hq Hu Hv Hw Ii Io Iq Jh Jl Jo Jr Lu Lv Ly Mb Mc Mi Mk Mm Mp Mr Mt Mu Ne Nf Ng Nh Ni Nj Nq Nr Nv Oi On Pd Pe Pg) Nw(Aa Hq Hw In Io Iq Iu Jk Jl Jo Jr Lh Lu Lw Mb Mc Me Mg Mi Mj Mk Mm Mq Mr Mt Mu Mx Na Nb Ne Ni Nj Nl Nq Nr On Pe) Jj(Aa Hq Hu Ii In Io Iu Jh Jk Jl Jo Lh Lu Lv Lw Me Mg Mj Mk Mq Mr Mt Mu Mx Na Nb Ne Nf Ng Ni Nl Nv Oh Oi Pd Pg) Ly(Hq Hu Hv Hw In Io Iq Jl Jo Jr Lu Lv Mb Mc Me Mi Mm Mp Mr Mt Nb Ne Nf Ng Nh Ni Nq Nr Nv Oh Oi Pa Pd Pg) Nf(Hr Hu Hv Hw Io Iq Jl Jo Jr Lu Lv Mb Mc Mi Mm Mp Mr Mt My Ne Ng Nh Ni Nj Nq Nr Of Oh Oi On Pa Pd Pe) Hu(Hv Hw Ii Io Iq Jk Jl Jo Jr Lu Lv Mb Mc Mi Mm Mp Mr Mt Nb Ne Nh Ni Nj Nq Nr Nv Oi On Pa Pd Pe Pg) Nq(Hq Hv Ii Iq Jh Jl Jo Jr Lu Lv Mb Mc Mk Mm Mp Mr Mu Ne Ng Nh Nr Nv Oi Pa Pd Pe Pg) Ms(Hq Hw Ii In Iu Jh Jk Jr Lh Lu Lw Mg Mj Mk Mp Mq Mu Mx Na Nb Ng Nl Oh Oi Pg) Yd(Bb Cx Db Fc Fw Gc Ic Ii Im Jk Ks Lu Lv Mk Mp Mt Mw Nb No Oa Pe Pi Pj Si) Nr(Hv Ii Iq Jl Jo Jr Lu Lv Mb Mc Mi Mk Mm Mp Mr Ne Ng Nh Nv Oh Oi Pa Pd) Ng(Hv Io Iq Jk Jl Lv Mb Mc Me Mi Mm Mp Mr Mt My Ne Nh Of On Pa Pe) Mm(Hv Ii Iq Jl Jo Jr Lu Lv Mb Mc Mr Ne Nh Nv Oh Oi Pa Pd Pe) Iq(Hv Ii Io Jo Lu Lv Mb Mc Mj Mk Mt Ne Nh Nv Oh Oi Pa Pd) My(Hq Iu Jo Lh Lw Mj Mk Mq Mu Mx Na Ni Nl Oh Pd) Mr(Aa Hv Ii Io Jo Lv Mb Mc Ne Nh Ni Nv Oi Pd) Of(Aa Hq Iu Lw Me Mj Mq Mx Na Nl Oh Oi Pd) Hr(Aa Hq Jh Lw Me Mj Mk Mq Mu Mx Nl Oh) Pe(Hv Ii Jo Lv Mb Mk Nb Nh Nv Oi Pa Pd) Aa(Ir Lu Mq Mw Nb No Nx Og Pb) Im(Hl Rt Rv Sh Uw Vh Wf Zw Ye) Mp(Hq Hv Jo Lv Mk Nv Pd Pg) On(Hv Ii Jo Lv Nh Nv Oi) Mi(Hq Ii Jo Lh Nv Pg) Pa(Jo Lh Mj Nb Nv Pg) Hv(Jo Jr Mb Nh Oi) Jl(Ii Mk Nb Nv) Hw(Ii Jo Nv) Oi(Io Mc Mt) Vi(Lj Sr) bN(Qy Uv) NoRx MbNv MtNh NbRt JoJr KeNx PdPg] Li{Qc(Fp Fr Hq Hr Hv Hw Hx Ii In Io Iq Jg Jh Jk Jl Jm Jo Jp Jr Js Jt Lh Lj Lu Lv Lw Lx Ly Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni Nj Nk Nl Nm Nn No Nq Nr Nt Nu Ny Of Oh Oi Ok Om On Oy Pa Pc Pd Pe Pf Pg Po Pz Qa Qb Qd Qe Vi) Ok(Aa Fp Fr Hq Hv Hw Hx Ii Il In Io Iq Iu Iv Jg Jh Jk Jl Jm Jp Jq Jr Js Jt Lh Lj Lu Lv Lw Lx Ly Lz Ma Mb Mc Md Me Mf Mg Mi Mj Mk Ml Mm Mn Mp Mq Mr Ms Mt Mu Mv Mx My Mz Na Nb Nc Nd Ne Nf Ng Nh Ni Nj Nk Nl Nm Nn No Nq Nr Nt Nu Nv Nx Ny Oh Oi Om On Pa Pc Pd Pe Pf Pg Po Pz Qa Qb Qd Qe) Pc(Fp Fr Hq Hr Hv Hw Hx Ii In Io Iq Iu Jg Jh Jk Jl Jm Jo Jp Jr Lh Lj Lu Lv Lx Ly Lz Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni Nj Nk Nl Nm Nn Nq Nr Nt Nu Nv Nx Ny Of Oh Oi Om On Oy Oz Pa Pd Pe Pf Pg Po Pz Qa Qb Qd Qe Vi Yd) Mf(Fp Fr Hq Hr Hv Hw Hx Ii Il In Io Iq Iu Jg Jh Jk Jl Jm Jo Jp Jr Jt Lh Lj Lu Lv Lx Ly Lz Ma Mb Mc Md Me Mg Mh Mi Mj Mk Ml Mm Mn Mp Mq Mr Ms Mt Mu Mv Mx My Mz Na Nb Nc Nd Ne Nf Ng Nh Ni Nj Nk Nl Nm Nn Nq Nr Nt Nu Nv Nx Ny Of Oh Oi Om On Pa Pd Pe Pf Pg Po Qa Qb Qd Qe Vi Yd) Jp(Fp Fr Hq Hr Hv Hw Hx Ii Il In Iq Iu Jh Jk Jl Jm Jo Jr Js Jt Lh Lj Lu Lv Lw Lx Ly Lz Ma Mb Mc Md Me Mg Mh Mi Mj Mk Ml Mm Mn Mp Mq Mr Ms Mt Mu Mv Mx My Mz Na Nb Nc Nd Ne Nf Ng Nh Ni Nj Nk Nl Nm Nn No Nr Nt Nu Nv Nx Ny Of Oh Oi Om On Pa Pd Pe Pf Pg Po Pz Qa Qb Qd Qe) Oi(Fp Fr Hq Hr Hu Hv Hw Hx Ii In Io Iq Jg Jh Jk Jl Jm Jo Jr Lh Lj Lu Lv Lx Ly Lz Ma Mb Mc Md Me Mg Mh Mi Mj Mk Ml Mm Mn Mp Mq Mr Ms Mt Mu Mv Mx My Na Nb Nc Nd Ne Nf Ng Nh Ni Nj Nk Nl Nm Nn Nq Nr Nt Nu Nv Nx Ny Oe Of Oh Om On Oy Pa Pd Pe Pf Pg Po Pz Qa Qb Qd Qe) Mz(Aa Fp Fr Hq Hv Hw Hx Ii Il In Io Iq Iu Jg Jh Jk Jl Jm Jo Jr Js Jt Lh Lj Lu Lv Lw Lx Ly Lz Ma Mb Mc Md Me Mg Mh Mi Mj Mk Ml Mm Mn Mp Mq Mr Ms Mt Mu Mv Mx Na Nb Nc Nd Ne Nf Ng Nh Ni Nj Nk Nl Nm Nn No Nq Nr Nt Nu Nv Nx Ny Oh Om On Pa Pd Pe Pf Pg Po Pz Qa Qb Qd Qe) No(Aa Fc Fp Fr Hq Hr Hv Hw Hx Ii In Io Iq Iu Jg Jh Jk Jl Jm Jo Jr Js Lh Lj Lu Lv Lx Ly Lz Ma Mb Mc Md Me Mg Mi Mj Mk Ml Mm Mn Mp Mq Mr Ms Mt Mu Mv Mx Na Nb Ne Nf Nh Ni Nj Nk Nl Nm Nn Nq Nr Nt Nu Nv Nx Ny Oh Om On Pa Pd Pe Pg Pz Qa Qd Qe Rx Vw Wf Wh Yd Zw Ye Tl) Qb(Fp Fr Hq Hr Hv Hw Hx Ii In Io Iq Iu Jg Jh Jk Jl Jm Jo Jr Js Lh Lj Lu Lv Lx Ly Lz Ma Mb Mc Md Me Mg Mh Mi Mj Mk Ml Mm Mn Mp Mq Mr Ms Mt Mu Mv Mx My Na Nb Nc Nd Ne Nf Ng Nh Ni Nj Nk Nl Nm Nn Nq Nr Nt Nu Nv Nx Ny Of Oh Om On Pa Pd Pe Pf Pg Po Pz Qa Qd Qe) Ly(Aa Fp Fr Hq Hr Hv Hw Hx Ii In Io Iq Iu Jg Jh Jk Jl Jm Jo Jr Jt Lh Lj Lu Lv Lx Lz Ma Mb Mc Md Me Mg Mh Mj Mk Ml Mm Mn Mp Mq Mr Ms Mt Mu Mv Mx My Na Nb Nd Ne Nf Ng Nh Ni Nj Nk Nl Nm Nn Nq Nr Nu Nv Nx Ny Of Oh Om On Oy Pa Pd Pe Pf Pg Po Pz Qa Qd Qe) Nd(Fp Fr Hv Hw Hx Ii Il In Io Iq Iu Jg Jh Jk Jl Jm Jo Jr Js Lh Lj Lu Lv Lx Lz Ma Mb Mc Md Me Mg Mh Mi Mj Mk Ml Mm Mn Mp Mq Mr Ms Mt Mu Mv Mx My Na Nb Nc Ne Nf Nh Ni Nj Nk Nl Nm Nn Nq Nr Nt Nu Nv Nx Ny Of Oh Om On Pa Pd Pe Pf Pg Po Pz Qa Qd Qe) Lw(Aa Fp Fr Hq Hv Hw Hx Ii In Io Iq Iu Jg Jh Jk Jl Jm Jq Jr Jt Lh Lj Lu Lv Lx Lz Ma Mb Mc Md Me Mg Mh Mi Mj Mk Ml Mm Mn Mp Mq Mr Ms Mt Mu Mv Mx Na Nb Nc Ne Nf Nh Ni Nj Nk Nl Nm Nn Nq Nr Nt Nu Nv Nx Ny Oh Om On Pa Pd Pe Pf Pg Po Pz Qa Qd Qe) Il(Fp Fr Hr Hv Hw Hx Ii In Io Iu Jg Jh Jk Jl Jm Jo Jr Lh Lj Lu Lv Lx Lz Ma Mb Mc Md Me Mg Mh Mi Mj Mk Ml Mm Mn Mp Mq Mr Ms Mt Mu Mv Mx Na Nb Nc Ne Nf Nh Ni Nj Nk Nl Nm Nn Nq Nr Nt Nu Nv Nx Ny Oh Om On Pa Pd Pe Pf Pg Po Pz Qa Qe Vi) Of(Fp Fr Hq Hr Hu Hw Hx Io Iq Jg Jh Jk Jl Jm Jo Jr Lh Lj Lu Lv Lx Lz Ma Mb Mc Md Me Mg Mh Mj Mk Ml Mm Mn Mp Mq Mr Ms Mt Mu Mv Mx My Na Nc Ne Nf Ng Nh Ni Nj Nk Nl Nm Nn Nq Nr Ns Nt Nu Nv Nx Ny Oe Oh Oy Pa Pd Pe Pf Pg Po Pz Qd Qe Vi) Js(Fp Fr Hq Hr Hw Hx Ii In Io Iq Iu Iv Jg Jh Jk Jl Jm Jq Jr Jt Lh Lu Lv Lx Ma Mb Md Me Mg Mi Mj Mk Ml Mm Mn Mp Mq Mr Ms Mt Mu Mv Mx Na Nb Nc Ne Nf Ng Ni Nj Nk Nl Nm Nn Nq Nr Nt Nu Nv Nx Ny Oh Om On Pa Pd Pe Pf Pg Po Qa Qd Qe) Nc(Fp Hq Hr Hu Hv Hw Ii In Iq Jg Jk Jl Jm Jo Jr Jt Lh Lj Lu Lx Lz Ma Mb Mc Md Me Mg Mh Mi Mj Mk Ml Mm Mn Mp Mq Mr Ms Mt Mu Mv Mx My Na Nb Ne Nf Ng Nh Ni Nj Nl Nm Nn Nq Nr Nt Nu Nv Nx Ny Oh Om On Pa Pd Pe Pf Pg Po Pz Qa Qd Qe) Ng(Aa Fp Fr Hq Hr Hu Hv Hw Ii In Io Iq Jh Jk Jl Jm Jo Jr Lh Lj Lu Lx Lz Ma Mb Mc

Oh Oi Ok On Pa Pe Pf Pg Pz Qb Qd Qe Ru Th) Ns(Aa Fr Hq Hr Ii Ik In Io Iq Iu Jg Jh Jk Jl Jp Jq Lh Lu Lv Lw Lx Lz Ma Mb Mc Md Me Mf Mg Mi Mj Mk Ml Mm Mn Mq Mr Mt Mu Mv Mx Mz Na Nb Ne Nf Ng Nh Ni Nj Nk Nl Nm Nq Nr Nv Nx Oh Oi Ok Om On Pa Pd Pe Pf Pg Po Pz Qd Qe) Mw(Fp Fr Hq Hr Ii Il In Io Iq Iu Jg Jh Jk Jl Jm Jo Jp Jq Lh Lu Lv Lw Lx Lz Ma Mb Mc Me Mf Mg Mi Mj Mk Ml Mm Mn Mq Mr Mt Mu Mx Mz Na Nb Nd Ne Nf Nh Ni Nj Nk Nl Nm Nn Nq Nr Nu Oh Oi Ok Om On Pd Pe Pf Pg Po Pz Qb Qd Qe) Nc(Aa Fp Hq Hr Hv Hw Hx Ik Il In Ip Iq Jg Jh Jk Jl Jm Jo Jp Jq Jr Js Lh Lu Lw Ly Lz Mb Mc Md Me Mf Mh Mi Mk Ml Mn Mp Mv Mx Mz Na Nd Ne Ng Nh Ni Nl Nm Nn Nq Nr Nt Nu Nv Nx Ny Oh Oi Ok Pa Pd Pe Pf Pg Po Qb Qc Qd Qe) Oe(Aa Fr Hq Hr Ii Ik In Io Iu Jh Jk Jp Lh Lu Lv Lw Lx Lz Ma Mb Mc Md Me Mf Mg Mi Mj Mk Ml Mm Mn Mp Mq Mr Mt Mu Mv Mx Mz Na Nb Nd Ne Nf Ng Nh Ni Nj Nk Nl Nm Nq Nr Nv Nx Ny Oh Oi Ok Om On Pa Pd Pe Pf Pg Po Yd) Js(Aa Fp Hq Hr Hv Hw Hx Ii Ik Il In Ip Iq Jg Jh Jk Jl Jm Jo Jq Jr Lh Lu Lw Ly Lz Mb Mc Md Me Mf Mi Mj Ml Mm Mn Mp Mu Mv Mz Na Nd Ne Nf Ng Nh Ni Nk Nm Nn Nr Nt Nu Nv Ny Oh Oi Ok Om Pa Pd Pf Pg Po Qb Qc Qd) Mh(Aa Fp Hq Hr Hv Hw Hx Ii Il In Ip Iq Jg Jh Jk Jl Jm Jo Jp Jq Jr Lh Lw Lx Ly Lz Mc Md Me Mf Mg Mi Mn Mp Mr Mt Mv Mx My Mz Na Nb Nd Ng Ni Nm Nn Nr Nt Nu Nx Ny Oh Oi Ok Pa Pd Pe Pf Pg Po Pz Qb Qc Qd Qe) Hx(Aa Fp Hv Hw Ii Ik Il Ip Iq Jl Jm Jo Jq Jr Lh Lu Lw Lx Ly Lz Mb Mc Md Me Mf Mg Mi Ml Mn Mp Mr Mt Mv Mx My Mz Na Nb Nd Ne Ng Ni Nk Nm Nn Nr Nt Nu Nv Nx Ny Oh Oi Ok Om Oy Pa Pd Pe Pf Qb Qc Qd) Hv(Aa Fp Hq Hw Ii Ik Il In Ip Iq Jh Jl Jm Jo Jq Jr Lu Lw Ly Lz Mb Mc Me Mf Mi Mj Ml Mm Mn Mp Mu Mv Mz Na Nd Ne Nf Ng Nh Ni Nk Nm Nn Nr Nt Nu Nv Oh Oi Ok Pa Pd Pf Pg Po Qb Qc Qd) Oy(Fr Hq Hr Ii Ik Io Iq Iu Jl Jp Lh Lu Lv Lx Ly Lz Ma Mb Mc Md Me Mf Mj Mk Ml Mm Mq Mr Mt Mu Mv Mx Mz Na Ne Nf Ng Nh Ni Nj Nk Nl Nm Nv Nx Ny Oh Oi Ok Om Pd Pg Po Pz Qe) Mv(Fp Hq Hr Hw Il In Ip Iq Jg Jh Jk Jl Jm Jo Jp Jq Jr Lj Lw Lx Ly Me Mg Mi Mn Mp Mr Mt My Mz Na Nb Nd Nn Nq Nr Nt Nu Nx Ok On Pa Pd Pe Pf Po Pz Qb Qc Qd Qe Yd) Aa(Fp Hq Hr Hw Ih Il Io Ip Iq Ir Jg Jh Jk Jl Jo Jp Jq Jr Lj Lu Lz Md Mf Mg Mq Mr Mt Mu My Nb Nk Nn Nq Nu Nv Nx Og Oi Pa Pd Pe Pf Pg Po Pz Qd Qe) Jm(Fp Hr Hw Ii Ik Il In Ip Iq Jo Jq Jr Lu Lw Ly Lz Mb Mc Md Me Mf Mi Ml Mn Mp Mz Na Nd Ne Ng Ni Nk Nm Nn Nt Nu Nv Nx Ny Oh Oi Ok Pa Pd Qb Qc Qd) Oz(Fr Hq Hr Ii Ik Il Io Iu Jg Jh Jk Jp Lh Lu Lv Lw Lx Ma Mb Mg Mj Mk Mm Mq Mr Mt Mx Mz Nb Ne Nf Nh Ni Nj Nk Nl Nq Oh Om On Pa Pd Pg Po Pz Qe) Ip(Fp Hq Hr Hw Ik Il In Jh Jk Jl Jo Jp Jq Jr Lw Ly Lz Md Me Mf Mi Mn Mp Na Nd Ng Ni Nn Nt Nu Nv Nx Ny Ok Pa Pd Pc Pf Pg Qb Qc Qd) My(Fr Hq Hr Ik Io Iu Lu Lv Lx Lz Ma Mb Mc Md Me Mf Mj Mk Ml Mm Mq Mu Mx Na Ne Nf Ng Nh Ni Nj Nk Nl Nv Nx Ny Oh Oi Pd Pg) Lj(Fp Fr Io Iq Iu Jh Jk Lh Lu Lv Lx Ma Md Me Mj Mk Ml Mq Mr Mt Mu Mx Mz Nb Ne Nf Ng Nh Ni Nj Nl Nr Nv Ny Om On Pg Pz Qe) Fp(Hq Hr Hw Ik In Iq Jh Jl Jo Jq Jr Lw Ly Mb Mc Md Mi Ml Mp Nd Ng Nm Nn Nt Nu Nv Nx Ny Oi Pa Pd Pf Pg Po Qb Qc Qd) Ng(Hw Il In Iq Jg Jk Jl Jo Jp Jq Jr Lw Ly Mg Mi Mm Mn Mp Nd Nm Nn Nr Nt Nu Ny Og Ok Pe Pf Po Pz Qb Qc Qd Qe) Jr(Hr Ii Ik Il Jh Lw Ly Lz Mc Md Mf Mi Ml Mm Mn Mp Nd Nf Nm Nn Nr Nt Nu Nv Ny Oh Oi Om Pa Pd Po Qb Qc Qd) Ih(Fr Ik Io Iu Jh Lh Lu Lv Lx Mb Mg Mi Mk Mm Mq Mr Mt Mu Mx Mz Nb Nf Nj Nl Nq Nr Oh Om On Pe Pz Qe Zw) Nt(Hq Hr Hw Ii Ik Iq Jh Jk Jo Jq Ly Md Mk Ml Nd Ne Nu Nx Ny Pa Pd Pg Po Qb Qc Qd Yd) Ny(Hw Il Iq Jo Jq Lw Ly Me Mi Ml Mn Mp Mr Mz Na Nb Nd Nn Nu Ok Pa Pe Pf Qb Qc Qd) Hw(Ii Ik Il Jh Ly Lz Mi Ml Mn Mp Nd Nf Nm Nn Nu Nv Oi Om Pa Pd Po Qb Qc Qd) Qb(Ik Il In Jo Jq Lw Ly Md Mi Ml Mp Na Nd Nk Nm Nn Nu Nv Nx Oi Ok Pa Qc) Nx(Il In Iq Lh Lw Me Mi Mn Mp Mz Na Nm Nn Nr Nu Ok On Pe Qc Qd) Qc(Ik Il In Jo Jq Lw Ly Md Me Mp Na Nd Nn Nu Nv Ok Qd Qe) Qd(In Lw Ly Lz Mb Md Mf Mi Mp Nd Nk Nn Nu Nv Oi Pa Pd) Yd(Ao Fw Gc Im Jh Kg Kj Mt Nm Nn Om Or Ow Pj Rx) Md(Il Jo Jq Lw Me Mi Mp Mz Na Nd Nn Nu Ok Pe) Ly(Il In Jo Jq Lx Lz Mi Mp Nd Nu Ok Pe) Nv(Il Jo Jq Mp Nd Nn Ok On Pe) Jo(Ii Ml Nd Nn Nu Om Po) Ir(Iq Mq Mx Nj Nr On) Jq(Hr Ml Mp Nd Nu Om) Pa(Il Mk Nd Nr Pf) Po(Mi Mr Ok Pe) Hr(Me Mz Na Ok) Iq(Ik Il Lz Mj) Og(Mj Ml Nj Oi) Mk(Jl Nd Pe) Pd(Nd Pe Pf) Pg(Mi Mp Nd) Nn(Mu Oi) Nu(Ru Tm) Hq(Mi Mp) Im(Sh Ye) DeKq DrKd NmMf LzIk MlIn NbRt IlJk ZwPe SrVi KebN} Aa{Qa(aA Et Fp Fr Hq Hr Hu Hv Hw Hx Ih Ii Ij Ik Il In Io Ip Iq Ir Is Iu Iv Jg Jh Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nl Nm Nn No Nq Nr Ns Nt Nu Nv Ny Oh Ok Om On Pa Pc Pd Pe Pf Pg Po Pz Qb Qd Qe) Js(aA Et Fp Fr Hq Hu Hv Hw Hx Ih Ii Ij Il In Io Iq Ir Is Iu Iv Jg Jh Jk Jl Jm Jn Jo Jp Jq Jr Jt Lh Lj Lu Lv Lw Lx Ly Lz Ma Mb Mc Md Me Mf Mg Mh Mi Mj Mk Ml Mm Mn Mp Mr Ms Mt Mu Mv Mx My Mz Na Nb Nc Nd Ne Nf Ng Nh Ni Nj Nk Nl Nm Nn No Nq Nr Ns Nt Nu Nv Nx Ny Oh Oi Ok Om On Pa Pc Pd Pe Pf Pg Po Pz Qb Qd Qe) Qb(aA Et Fp Fr Hq Hr Hu Hv Hw Hx Ih Ii Ij Ik Il Io Iq Ir Is Iu Iv Jg Jh Jk Jl Jm Jn Jo Jp Jq Jr Jt Lh Lj Lv Lw Lx Ly Lz Ma Mb Mc Md Me Mf Mg Mh Mi Mj Mk Ml Mm Mn Mp Mr Ms Mt Mv Mx My Mz Na Nb Nc Nd Ne Nf Ng Nh Nj Nl Nm No Nq Nr Ns Nt Nu Nv Ny Oh Ok Om On Pa Pd Pe Pf Pg Po Pz Qd Qe) Mw(aA Et Fr Hq Hu Hv Hw Hx Ii Ik Il In Io Iq Is Iu Jg Jh Jk Jl Jm Jo Jp Jq Jr Jt Lh Lj Lv Lw Lx Ly Ma Mb Mc Md Me Mf Mg Mh Mi Mj Mk Ml Mm Mn Mp Ms Mt Mu Mv Mx My Mz Na Nb Nc Nd Ne Nf Ng Nh Ni Nj Nk Nl Nm Nn No Nq Nr Ns Nt Nv Ny Oh Ok Om On Pa Pd Pe Pf Pg Po Pz Qd Qe) Lz(Et Fp Fr Hq Hr Hu Hv Hw Hx Ih Ij Il In Iq Ir Is Iv Jg Jh Jj Jk Jl Jn Jo Jp Jq Jr Jt Lj Lu Lw Lx Ly Ma Mb Mc Md Me Mf Mg Mi Mj Mk Mn Mp Mq Mr Ms Mt Mu Mv My Mz Nb Nc Nd Nf Ni Nk Nn No Nq Nr Ns Nt Nu Nx Ny Oe Of Og Oi Om On Pa Pd Pe Pf Pg Po Pz Qd Qe) It(aA Hu Hw Hx Ih Ii Ij Ik Il Io Iq Ir Is Iu Iv Jg Jh Jk Jq Jt Lh Lj Lu Lv Lw Lx Ly Mb Mc Me Mf Mg Mh Mi Mj Mk Ml Mm Mn Mp Ms Mv Mx My Mz Na Nb Nc Ne Nf Ng Nh Ni Nj Nl Nm Nq Nr Ns Nt Nu Nv Ny Oe Of Oh Oi Ok Om On Pa Pd Pe Pg Pz) Oy(Et Fp Fr Hr Hu Hv Ih Ij Il In Io Iq Is Iv Jg Jh Jj Jk Jl Jm Jn Jp Jr Jt Lh Lj Lu Lv Ma Md Mg Mh Mi Mj Mk Ml Mn Mp Mq Ms Mu Mv Mx Mz Na Nb Nc Nd Nf Ni Nk Nq Nr Ns Nt Nu Nv Nx Ny Oe Of Og Oi Ok Om On Oz Pb Pc Pd Po Pz Qd) Pb(aA Et Fr Hr Hu Hv Il In Io Iq Is Iv Jg Jh Jj Jk Jl Jm Jn Jp Jr Jt Lh Lj Lu Lv Lw Ma Mb Md Me Mf Mg Mh Mi Mj Mk Ml Mn Mp Ms Mv Mx My Mz Na Nb Nc Nd Nf Nh Ni Nk Nq Nr Ns Nt Nu Nx Ny Of Og Oi Ok Om On Oz Pe Pg Po Qd Qe) Oz(Et Fr Hr Hu Hv Ih Ij Il In Io Iq Ir Is Iv Jj Jl Jm Jn Jo Jp Jr Lj Lu Lv Lw Lx Ma Md Me Mf Mg Mh Mi Mj Mk Ml Mp Mq Ms Mu Mv My Nb Nc Nd Ni Nk Nn Nq Nr Ns Nt Nu Nx Ny Oe Of Og Oi Ok Pe Pg Po Qd Qe) Og(Et Fr Hq Hr Hu Hv Hw Ih Ij Il Ip Iq Ir Is Iv Jg Jh Jj Jk Jl Jn Jo Jp Jr Jt Lj Lu Lx Ma Md Mg Mh Mi Mj Mk Mp Mq Mr Mt Mu Mv Nb Nn No Nq Nr Ns Nt Nu Nx Ny Oe Om Pc Pe Pf Pg Po Pz) Ip(Et Fp Fr Hq Hr Hu Hv Hx Ih Ij Il In Iq Ir Is Iv Jg Jh Jl Jm Jn Jo Jp Jq Jr Jt Lu Lx Ma Md Mg Mh Mj Mk Mq Mr Ms Mt Mu Nb Nc Nn No Nq Nu Nx Oe Of Pa Pe Pf Pg Po Qd Qe) Jj(Et Fp Fr Hr Hu Hv Il Iq Ir Is Jk Jl Jm Jn Jp Jr Jt Lj Lu Lx Ma Md Mg Mh Mj Mk Mn Mp Mq Mr Mt Mu Mv Nb Nc Nd Nn No Nq Nr Ns Nt Nu Nx Ny Oe On Pc Pe Pf Pg Po Pz Qd Qe) Qc(aA Fr Hq Hv Hw Hx Ii In Iu Jg Jh Jk Jl Jo Jq Jr Jt Lh Lj Lv Ly Mb Mc Me Mh Mi Ml Mm Mn Ms Mv Mx Mz Na Ne Nf Ng Nh Nj Nl Nm Nr Nt Nv Oh Ok Om On Pd Pe Po Pz Qd Qe) Qe(Et Fp Hr Hu Ih Ii Ij Il In Io Iq Ir Iv Jm Jn Jo Jp Jq Jr Lu Lw Lx Ma Md Mf Mg Mj Mk Mq Mr Ms Mt Mu My Nb Nc Nd Ni Nk Nn No Nq Ns Nu Nv Oe Of Oh Oi Pa Pc Pf) Fp(Et Hq Hu Hv Hw Hx Ih Il In Iq Ir Iv Jg Jh Jk Jl Jm Jn Jo Jp Jq Jr Jt Lu Md Mg Mq Mr Mt Mu Nb Nc Nd Ni Nk Nn No Nx Oe Of Oi Pa Pc Pd Pe Pf Pg Po Pz Qd) Pc(Et Fr Hr Ih Ij Il Iq Ir Is Iv Jm Jn Jp Jr Lj Lu Lx Ma Md Mh Mj Mk Mp Mq Mr Mt Mu Nb Nc Nd Ni Nk Nn No Nq Nr Ns Nu Nx Ny Oe Of Oi Pe Pf Pg Po Qd) Mr(Et Hq Hr Hu Hv Hw Hx Ih Il Iq Ir Iv Jg Jh Jk Jl Jm Jn Jo Jp Jq Jr Jt Lu Ma Md Mg Mk Mq Ms Mt Mu Nb Nc Ni Nn Nx Oe Pa Pd Pe Pf Pg Po Pz Qd) Ih(Et Fr Hq Hr Hu Hv In Iv Jm Jn Jo Jp Jq Jr Lj Lu Lx Ma Md Mf Mj Mk Mq Ms Mt Mu My Nb Nc Ni Nk Nn No Nu Nx Of Oi Pa Pe Pf Pg Po Qd) Mq(Et Fr Hq Hr Hu Hv Il Iq Ir Iv Jg Jk Jl Jm Jn Jo Jp Jq Jr Jt Lj Lu Lx Md Mk Mt Nb Nc Nk No Nu Nx Oe Of Pe Pf Pg Po Pz Qd) Ir(Et Hq Hr Hx In Iv Jm Jn Jo Jp Jq Lu Ma Md Mf Mk Mu My Nb Nc Nk Nn Nx Oe Of Oi Pa Pe Pf Pg Po Qd) Iv(Et Hr Hv Il In Iq Jl Jm Jn Jo Jp Jr Lj Lu Lx Md Mu Nc Nd Nn No Nx Oe Of Oi Pe Pf Pg Po Pz Qd) Et(Hr Ij Il Is Jm Jn Lj Lu Lx Md Mj Mk Mt Mu My Nb Nc Nd Nk Nn No Nu Nx Oe Of Oi Pe Pf Pg) Qd(Hr Ij Ik Il In Io Jm Jn Lu Md Mj Mk Mt Mu My Nb Nc Nd Ni Nk Nn Ns Nu Nx

Figure 38 Continued

Oe Of Oi Pf) Jn(Fr Hr Il In Jm Jp Jq Lj Lu Lx Ma Md Mk Ms Mt Mu Nb Nc Nk Nn No Nx Oe Of Pf Po) Hr(Fr Hv Ij Jl Jr Lj Lu Lx Ma Md Mj Mk Mt Mu Nc Nn No Nq Po) Mt(Hv Jm Jo Jp Jr Md Mu Nn Nx Oe Of Oi Pa Pe Pf Pg Po) Oe(Fr Ij Iq Is Jk Jl Jm Jp Jr Lj Lx Nn No Nq Pf Po) Nn(Hv Iq Jl Jm Jo Jp Jr Lu Lx Md Nc No Pf Po) Ij(Hq Hu Hw Hx Jk Jo Jp Jr Md My Nf Nv Nx Of) Jm(Fr Jp Lu Lx Ma Md Mk Mu Nc Ni No Of Po) No(Il Jr Lu Md Mu Nc Nk Nx Of Oi Pf) Md(Jp Jr Lx Mj Mk Ml Nc Pf Po) Pf(Iq Mk Mu Nb Nx Oi Pa Pd) Po(Lu Mu My Nk Nx Of Oi) Jp(Is Lj Lu Mu Nk Nu Of) Nc(Iq Mu Ni Nk) Iq(Lu Ms Nb) Nq(My Of) Mu(Jr Mj) Is(Jq Nx) LxNx NbJl IlLj JhOf} No{Ir(Fp Fr Hq Hr Hu Hv Hw Hx Ih Ii Ij Il In Io Ip Iq Is Iu Iv Jg Jh Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni Nj Nk Nl Nm Nn Nq Nr Nt Nu Nv Nx Ny Of Oh Oi Ok Om On Pa Pc Pd Pe Pf Pg Po Pz Qa Qb Qc Qd Qe Rx) Ih(Fp Fr Hq Hr Hu Hv Hw Hx Ii Ik Il In Io Iq Is Iu Iv Jg Jh Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni Nj Nl Nm Nn Nq Nr Nt Nu Nv Nx Ny Of Oh Oi Ok Om On Pa Pc Pd Pe Pf Pg Po Pz Qa Qb Qc Qd Qe Rx) Jj(aA Fp Fr Hq Hr Hu Hv Hw Hx Ii Ik Il In Io Iq Iu Iv Jg Jh Jk Jl Jm Jo Jp Jq Jr Lh Lj Lu Lv Lw Lx Ly Lz Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni Nj Nk Nl Nn Nq Nr Nt Nu Nv Nx Ny Oe Of Og Oh Oi Ok Om On Oy Pa Pc Pd Pe Pf Pg Po Pz Qa Qb Qc Qd Qe) Oz(Fc Fp Fr Hq Hr Hu Hv Hw Hx Ii Ik Il In Io Iq Iu Jg Jh Jk Jl Jm Jo Jp Jq Jr Js Lh Lj Lu Lv Lw Lx Ly Lz Ma Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni Nj Nk Nl Nm Nn Nq Nr Nt Nu Nv Nx Ny Oh Oi Ok Om On Oy Pa Pc Pd Pe Pf Pg Po Pz Qa Qb Qc Qd Qe) Ns(Fp Fr Hq Hr Hu Hv Hw Hx Ii Il In Io Iq Iu Iv Jg Jh Jk Jl Jm Jo Jp Jq Jr Js Lh Lj Lu Lv Lw Lx Ly Lz Ma Mb Mc Md Me Mf Mg Mh Mi Mj Mk Ml Mm Mn Mp Mq Mr Ms Mt Mu Mv Mx My Mz Na Nb Ne Nf Ng Nh Ni Nj Nk Nl Nm Nn Nq Nr Nt Nu Nv Nx Ny Of Oh Oi Ok Om On Pa Pc Pd Pe Pf Pg Po Qa Qb Qc Qd Qe) Rx(Ao Ap Aw Ba Bb Bc Bg Ch Co Cp Cs Cx Dc De Ez Gc Gp Hf Ho Hq Hu Hv Hw Hx Id Ij Im Is Iu Iz Jd Jg Jh Jk Jn Js Kc Kd Ke Kg Kj Kk Kl Kn Kq Kz Ld Lx Ma Mf Mg Mh Mi Mm Mp Mq Mr Mt Mu Mv Mw My Na Nc Ne Nf Nk Nn Nq Ny Oh Om Ow Oy Pa Pd Pe Pf Ph Pi Ql Rz Si Yl Ye Xa) Et(Fp Fr Hq Hv Hw Hx Ii Il In Io Iq Iu Jg Jh Jk Jl Jo Jp Jq Jr Jt Lh Lu Lv Lw Lx Ly Lz Ma Mb Mc Md Me Mf Mg Mh Mi Mj Mk Ml Mm Mn Mp Mq Mr Nt Mu Mv Mx Mz Na Nb Ne Nf Nh Ni Nj Nk Nl Nm Nn Nq Nr Nt Nu Nv Nx Oh Oi Ok Om On Pe Pf Pg Po Pz Qa Qd Qe) It(Fp Fr Hq Hr Hv Hw Hx Ii Il In Io Iq Iu Jh Jk Jl Jm Jo Jq Jr Js Lh Lj Lu Lv Lw Lx Lz Ma Mb Mc Md Me Mf Mg Mi Mj Mk Ml Mm Mn Mp Mq Mr Mt Mu Mv Mx Mz Na Nb Nc Nf Ng Nh Ni Nj Nl Nm Nq Nr Nt Nu Nv Nx Ny Oh Oi Om On Pe Pf Pg Po Pz Qa Qb Qc Qd Qe) Ij(Fc Fd Fp Hl Hp Hq Hv Hx Ii Il In Ip Iq Is Iv Jh Jk Jn Jo Jp Jq Jr Js Jt Lw Ly Lz Md Me Mf Mh Mi Mj Mk Ml Mm Mn Mp Ms Mu Mv Mz Nc Nd Ne Nf Ng Nh Ni Nk Nm Nn Nv Nx Ny Oh Oi Ok Om Pa Pc Pd Pg Po Qb Qc Qd Rt Va Vh Wc We Zw Xa) Og(Fp Hq Hu Hv Hw Ii Ik Il In Iq Iu Iv Jh Jl Jo Jp Jq Jr Js Lh Lj Lw Ly Lz Ma Mc Md Me Mf Mg Mh Mi Mm Mn Mp Mr Ms Mt My Mz Nb Nc Nd Nc Nh Ni Nj Nk Nn Nq Nr Nt Nu Ny Oe Of Oh Ok Om On Oy Pa Pc Pd Pe Pf Pg Qa Qb Qc Qd Qe) aA(Fp Fr Hr Hu Hv Ii Ik In Io Iq Is Iu Iv Jg Jm Jq Jr Js Jt Lu Lw Ly Lz Ma Mc Md Me Mf Mg Mh Mj Mk Mm Mn Mp Ms Mu Mv My Mz Nc Nd Ne Ng Nh Ni Nj Nk Nm Nn Nr Nt Nu Nv Nx Ny Of Oh Oi Ok On Pa Pc Pd Pf Po Qa Qb Qc Qd) Oe(Fc Fp Hq Hu Hv Ii Ik Il In Io Iq Iv Jg Jl Jm Jp Jq Jr Js Lj Lw Ly Lz Mb Md Me Mf Mg Mh Mi Mm Mn Mp Ms My Mz Nb Nc Nd Ne Ni Nk Nm Nn Nt Nu Ny Of Oh Ok Om On Oy Pa Pc Pd Pe Pf Ps Pz Qa Qb Qc Qd Qe Wh) Is(Hq Hr Hu Hv Hx Ii Ik Il In Ip Jk Jl Jn Jt Lj Lw Ly Lz Md Me Mf Mg Mh Mj Mk Mm Mn Mp Ms Mv Mw My Mz Nc Nd Ne Ng Nh Ni Nk Nm Nn Nr Nu Nv Nx Ny Of Oh Oi Pa Pc Pd Po Qb Qc Zw) Jn(Hq Hr Hu Hv Ii Ik Il In Ip Iv Jg Jp Jq Js Jt Lj Lw Ly Md Me Mf Mh Mi Mj Mm Mp Ms Mw My Mz Nc Nd Ne Ng Nh Nk Nm Nn Nx Of Oh Oi Ok Pa Pc Pd Qb Qc Qd) Ip(Hq Hr Hu Hv Ii Ik Il In Iv Jg Jo Jq Jr Js Jt Lj Lw Ly Lz Mf Mh Mj Mn Mp Ms My Mz Nc Nd Ne Ng Ni Nk Nm Nn Nv Nx Of Oh Ok Pa Pc Pd Qb Qc Qd) Oy(Ik Il In Iv Jg Jh Jm Jp Jq Js Lj Lw Me Mg Mh Mi Mm Mn Mp Ms Mz Nc Nd Nk Nm Nn Ok Om On Pc Pe Pf Pg Qa Qb Qc Qd) Pb(Fr Hq Hr Hx Io Iu Jh Jk Lu Lv Lx Mb Mc Md Mj Mk Ml Mq Mu Mv Mx Na Nf Ng Nj Nl Nq Nr Nv Nx Oh Pd Po Pz Qe) Mw(Hq Hu Il In Iv Jq Jr Js Jt Lj Lw Ly Mh Mp Ms My Mz Nc Ng Nk Nm Nn Of Oh Oi Ok Pa Pc Pd Qb Qc Qd) Zw(Ap Co Cu Ez Ho Io Kc Kd Kg Ld Lx Ma Mg Mi Mp Mt Ni Nn Om Ow Pd Pe Pf Rz) Jt(Hu Ii Ik Jo Lj Mh Mj Ms Mv Nc Nd Ne Ng Nk Nv Nx Oi Pc Qb Qc) Nn(Hu Ik Iv Lj My Pc Rz Sh Vw Wd Wf Wh Ye Th) Kd(Fd Gc Gd Gn Hl Ho Hp Lp Op Ry Rz Sh Yl Ye) Ik(Fp Iq Iv Js Lj Lz Nc Nm Of Qa Qb Qc) Fc(Af Bn Cx Gp Lj Lu Mn Ow Pc Pf Si) Of(In Iv Jg Jq Js Mz Nb Ok Om On) Th(aF Cw Iv Kg Mg Qy Uh Ur Wd) Lj(Iv Jg Jq Lw Mi Mp Ok On) Ho(Aj De Gl Gp Ib Ki Ye) Ke(bN Kf Lh Nx Ph Rm Yd) Hr(Hv In Jq Mz Ok Qa) Mg(Fd Rt Va Vw Wc) Cx(Hl Sf Sj Xa) Gp(Fi Hp Rz Sf) Sh(Bb Im Jg Pf) Ye(Ap Bb Hu Im) My(Jg Nb On) Yd(Ld Nq Ow) Uh(Gd Va Ti) Gc(Ph Qn) Hu(Jg Wf) Iv(Hx Nr) Xa(Bn Qn) Rz(De Ib) Ld(Lp Tm) BbHl FiGn MhOk MkRu NcNk NgJg IlQd ImWf PsVp OmUw VaVt VwPd PelX} Et{Is(Fp Fr Hq Hv Hw Hx Ii Il In Io Ip Iq Iu Iv Jg Jh Jk Jl Jm Jo Jp Jq Jr Js Jt Lh Lu Lv Lw Lx Ly Lz Ma Mb Mc Md Me Mf Mg Mh Mi Mj Mk Ml Mm Mn Mp Mq Mr Ms Mt Mu Mv Mx Mz Na Nb Nc Nd Ne Nf Ng Nh Ni Nj Nk Nl Nm Nn Nq Nr Nt Nu Nv Nx Ny Oh Oi Ok Om On Pa Pc Pd Pe Pf Pg Po Pz Qa Qb Qc Qd Qe) Js(Fp Fr Hq Hr Hu Hv Hw Hx Ii Ij Il In Io Iq Iu Iv Jg Jh Jk Jl Jm Jp Jq Jr Jt Lh Lu Lv Lw Lx Ly Lz Ma Mb Mc Md Me Mf Mg Mh Mi Mj Mk Ml Mm Mn Mp Mq Mr Ms Mt Mu Mv Mx Mz Na Nb Nc Nd Ne Nf Nh Ni Nj Nk Nl Nm Nn Nq Nr Nt Nu Nv Ny Oh Ok Om On Pa Pc Pd Pe Pf Pg Po Pz Qa Qb Qc Qd Qe) Mw(Fr Hq Hr Hv Hw Hx Ii Il In Io Iq Iu Jg Jh Jk Jl Jm Jo Jp Jr Jt Lh Lu Lv Lw Lx Ly Lz Ma Mb Mc Md Me Mf Mg Mh Mi Mj Mk Ml Mm Mn Mp Mq Mr Mt Mu Mv Mx Mz Na Nb Nd Ne Nf Nh Ni Nj Nk Nl Nm Nn Nq Nr Nt Nu Nv Nx Ny Oh Oi Ok Om On Pa Pc Pd Pe Pf Pg Po Pz Qa Qb Qd Qe) Jn(Fp Fr Hq Hr Hv Hw Hx Ii Ik Il In Io Iq Iu Jg Jh Jk Jl Jm Jo Jp Jq Jr Jt Lh Lu Lv Lw Lx Ly Lz Ma Mb Mc Md Me Mf Mg Mh Mi Mj Mk Ml Mm Mn Mp Mq Mr Mt Mu Mv Mx Na Nb Ne Nf Nh Ni Nj Nk Nl Nm Nn Nq Nr Nt Nu Nv Ny Oh Oi Ok Om On Pa Pc Pd Pe Pf Pg Po Pz Qa Qb Qd Qe) Iv(Fp Fr Hq Hu Hv Ii Ik Il In Io Ip Iq Jg Jh Jk Jl Jm Jo Jp Jq Jr Jt Lu Lv Lw Lx Ly Lz Ma Mb Mc Md Me Mf Mg Mh Mi Mj Mk Ml Mn Mp Mq Mr Ms Mt Mv My Mz Na Nb Nc Ne Ng Nh Ni Nk Nm Nn Nq Nr Nt Nu Nv Nx Ny Oh Oi Om On Pa Pc Pd Pe Pf Pg Po Pz Qa Qb Qd Qe) Ij(Fr Hq Hv Hw Hx Ii Il In Io Iq Iu Jg Jl Jm Jp Jq Jr Jt Lh Lu Lv Lw Lx Ly Ma Mb Mc Md Me Mf Mg Mh Mi Mj Mk Ml Mm Mn Mp Mq Mr Mt Mu Mx Mz Na Nb Ne Nf Nh Ni Nj Nk Nl Nm Nn Nq Nr Nt Nu Nv Ny Oh Oi Ok Om On Pa Pc Pd Pe Pf Pg Po Pz Qa Qb Qd Qe) Jj(Fr Hq Hr Hu Hv Hw Hx Ii Ik In Io Iq Iu Jg Jk Jl Jo Jq Jr Lh Lu Lw Lx Ly Lz Ma Mb Mc Me Mf Mh Mi Mj Mn Mp Mr Ms Mt Mx My Mz Na Nb Nd Ne Nf Ng Nh Ni Nj Nk Nl Nm Nq Nr Ns Nt Nu Nv Ny Of Og Oh Oi Ok Om On Oy Pa Pc Pd Pe Pf Pg Po Qd Qe) Qb(Fp Hq Hr Hu Hv Hw Hx Ii Ik Il In Io Ip Iq Jh Jk Jl Jm Jo Jq Jr Jt Lu Lv Lw Lx Ly Lz Ma Mb Mc Md Me Mf Mg Mh Mi Mk Mn Mp Mr Ms Mt Mu Mv My Mz Na Nb Nc Nd Ne Ng Nh Ni Nk Nm Nn Nr Nt Nu Nv Nx Ny Oh Oi Ok Pa Pc Pd Pe Pf Pg Pz Qa Qc Qd) Og(Fr Hq Hu Hv Hw Hx Ii Ik Io Iq Iu Jg Jh Jk Jl Jo Jr Lh Lw Lx Ly Lz Ma Mb Mc Md Me Mf Mg Mh Mi Mj Mk Ml Mn Mp Mq Mr Ms Mt Mv Mx My Na Nc Nd Ne Nf Ng Nh Ni Nj Nk Nl Nm Nq Nr Nt Nu Nv Ny Of Oh Ok Om Oy Pa Pc Pd Pe Pf Pg Po) Pb(Fr Hq Hr Hu Hx Ii Ik Io Iq Iu Jg Jh Jk Jl Jm Jo Jp Jr Lh Lu Lv Lw Lx Ly Ma Mb Mc Md Me Mf Mg Mi Mj Mk Ml Mm Mn Mp Mq Ms Mt Mu Mv Mx My Na Nb Ne Nf Ng Nh Ni Nj Nk Nl Nm Nq Nu Nv Nx Ny Oh Oi Om On Oy Oz Pa Pc Pd Po Pz) Oe(Fr Hq Hr Hu Hx Ii Ik Io Iu Jg Jh Jk Jl Jo Jp Jr Lh Lu Lv Lw Ly Ma Mb Mc Md Me Mf Mg Mh Mi Mj Mk Ml Mm Mn Mp Mq Mr Ms Mt Mu Mv Mx My Na Nb Ne Nf Ng Nh Ni Nj Nk Nl Nm Nq Nu Nv Nx Oi Ok Om Pd Pg Po Pz) Qc(Fp Hr Hu Hv Hw Ik Il In Ip Jm Jo Jq Jr Jt Lw Lx Lz Mf Mh Mi Mj Mn Mp Mr Ms My Mz Nc Nd Ng Nk Nm Nn Nr Nt Nu Nx Ny Of Oi Oz Pc Pd Pe Pf Qa Qd) Oy(Fr Hu Hv Hw In Iq Jh Jk Jq Jr Jt Lh Lw Lx Lz Ma Mh Mi Mn Mp Mr Ms Mt Mx My Mz Nb Nd Nf Ng Ni Nm Nn Nr Ns Nt Nu Ny Of Oh Ok Om Oz Pa Pc Pd Qe) Oz(Fr Hr Hu Hv Hw Il Iq Jl Jm Jo Jq Jr Jt Lx Lz Mf Mh Mi Mn

Rx(Kq Ny) IvJn QaPb} Jj{Ih(Fp Fr Hv Il Iq Is Iv Jm Jn Jo Jp Jq Jr Lh Lx Lz Mc Mg Mi Mm Mn Mp Mr Ms Mz Nd Ng Nk Nq Nr Ns Nt Nu Nv Ny Ok Om On Oz Pa Pf Pg Po Pz Qa Qc Qd Rx) It(Fp Il Is Iv Jk Jl Jm Jo Jq Lh Lx Ma Mi Mm Mp Mz Nd Nr Nt Nu Nv Ny Om Oz Pb Pf Po Pz Qa Qb Qc Qd Qe) Jt(Fp Hr Il Is Jm Js Mn Mz Nm Nn Nr Ny Oe On Oz Pb Pf Qa Qc Qd) Js(Ik Il Ip Jg Jm Jn Mm Mn Nm Nn Nt Nu Ny Oe Ok On Oz Pb) Jn(Il Ip Is Iv Mn Nm Nn Nt Ok On Oz Pb Qd) On(Ip Is Iv Jm My Ns Oe Of Oy Oz) Nm(Fp Il Is Iv Jm Pb Qa Qb) Ip(Il Is Iv Mn Nn Nt Oz Pb) Is(Jg Mn Nn Oz Pb) Qd(Ik Il Oz) Iv(Nn Ru) Qa(Oe Pb) DeKq IlNy SrVi XaKd OkPb} Vi{Sr(Fp Fr Hr Hu Hv Hw Hx Ih Ii In Ip Iq Is It Jg Jk Jl Jm Jn Jo Jp Jq Jr Js Jt Lh Lu Lv Lx Lz Mb Me Mf Mg Mh Mj Mk Ml Mm Mn Mp Mr Ms Mt Mu Mx My Nf Ng Nj Nk Nm Nq Nr Nt Nu Nv Ny Oe Of Oh Oi Ok On Oy Oz Pa Pb Pc Pf Po Ps Pz Qa Qb Qd Qg Qh Qt Qu Qv Qw Qx Qy Qz Rb Rc Rt Rv Ss Tn To Tv Tz Ua Ub Uc Ug Uh Ul Um Un Uw Ux Va Vb Vh Vo Vp Vs Vt Vw Wc We Wf Wh Wm Ti Th) Nn(Ng Of Qu Ss Ua Wf) Lx(Jl Lv Mj Vp) Of(Hw Om Pf) Uu(Uk Ti) Vt(Up Va) Vs(Hw Vq) ThIv NqNx UaQy UfUv} Pb{Is(Fp Ih Jg Jn Jp Js Jt Lh Lw Lx Lz Mm Mn Mz Nm Nn Nr Ns Nt Nu Ny Ok On Pf Po Qa Qb Qd) Ih(Fr Ip It Iv Jg Jn Jp Jt Lh Ma Nm Nn Oe Ok On Pf Qd) Jt(Fp Fr Hr Ip It Jn Js Lx Nn Oe On Pf Qa Qb Qd) Ok(Fp Hr Ip Iv Jn Js Nn Oe Pf Qa Qb Qd) On(Ip Iv Jn Js My Ns Of Oy) Ip(Iv Jn Js Nn Qa Qd) It(Fr Jp Js Nn Qa) Iv(Fr Jn Ma Nn Qa) Qd(Ik Il Jn Oe) Yd(Mt Om Ow) Fr(Jn Js) Qa(Jn Ma) DeKq JsOe} Nb{Rt(Hv Hw Is Iu Jh Jo Jt Ma Mg Mi Mm Mp Mt Mu Mv Na Nm Nn Nq Om Pd Qy Qz Ue Uf Un Wd Ti) Bo(Fc Fd Fi Gb Hl Ho Lp Rz Sf Si Vz Wb Ye Tm Tl Xa) Tl(Af Bn Cx Dk Ib It Jl Ld Ny Oe Oz Qn Rx) Fc(Ar Kx Ld Lp Lx Lz Mk Ml) Yd(Ld Mk Mp Nq Ou Ow Pj) Ti(Aj Ch hB HC Uu) Ld(Fi Gh Lp Rz Vz Zw) Mq(Uw We Wh) Rx(Iv Lu Oa) Of(Jg On Vh) Ar(Fi Ho) Zw(Ow Po) We(Nn Nq) Kj(Ho Rz) Un(Ru Va) FdIv NhWf UhfR} Oe{Ih(Fp Il Ip It Iv Jn Jp Js Lx Mm Mn Nt Nu Nv Ny Om Oz Po Qa Qd) Is(Fr Ip It Jn Jp Js Jt Lx Ma Mm Nm Nn Ny Ok On Oz Qa Qd) On(It Iv Jn Js Jt Ns Of Oy Oz Qa Qb Qd Yd) Jt(Fp It Jn Js Nn Ny Qa Qd) Qa(Ik Iv Jg Jn Ok) Qd(Ik Il Jn Oz) Ok(It Jn Js Qb) Jg(Js Qb) Ps(Va Vs) DrOa NnJn ShNv} Yd{Kq(Ch Cx Gn Gp Hf Ib Is Lu Lx Mh Ow Pf Pj Si) Ld(Dc Fw Gc Ih Is Jg Jn Ko Mt Nr Ny) Ow(Dr Hb Hx Jk Jl Ny Oz Pc Pi Wb) Pj(Is Jl Jn Jq Jr Lx Mt Nv Oa Om) Gc(Iv Mq Mv Nn Ny Oa Ry Sh) Lx(Hu Jh Mu Nt Wb) Mt(Hb Ki Or Oz Pc) Nt(Lz Ml) Hb(Co Nn) Is(Oz Pc) Om(Aj Oy) ChJh DdMq MkNy RxOn NvOz} It{Ok(Ih Ip Is Jn Jo Jp Nd Nx Of Oy Oz Qb) Jp(Ih Ip Is Iv Js Jt Ns Oz) On(Ik Ms My Nk Ns Of Oy Oz) Jt(Fp Hr Ih Ip Jo Of Qb) Is(Fr Ma Nm Nn Oz) Ih(Fr Jg Ma) Rx(Af Ny) FrOz HrIv VaVt} Rx{Ny(Ar Ih Iu Iv Kx Kz Ld Mq Na Oa Ow Pd Tl Xa) Oa(Dr Hl Hp Hx Je Ld Mh Mu Ni Nu Pi Wb) Ih(Aj Dd Hx Pk) Jn(Bo Hp Mq Nc) Ch(Jh Kq) Ow(Dr Hp) KdQl KqNx} Ld{Lp(Af Ap Bn Bo Cx Dp Hl Hu Ik Iv Ki Ks Nu Pa Pc Qn Zx) Zw(Ih Il Jg Lx Nr Nv Oa) Nr(Dr Fc Hp Vz Wb) Fw(Dr Sj Wb) Ed(fR Gd) DraW FcJn FiHu KdRy} Kq{De(aE Aj bL bW Ch dN Ed Fc Fw Hb Ho Hw In Ki Kl Lp Lz Mg Ng Nk oH Oi Ow Pa Qb Qc Qn Qt Rf Ss Uo Uu) Af(Fi Lp) Bg(Lp Tm) UhVp} Jt{Of(Fp Fr Ih Jn Lx Mp Nd Nn On Qa Qb) Hr(Fp Ip Is Jn Js Lx Lz Mz Qa Qb) Ih(Fp Ip Jo Ma Ms My Ng Oy Oz) Ik(Fp Qd) Ip(Jo Oz) NsNd QbOy} Oz{Is(Fr Ip Jn Ma Nm Pf Qd) Ps(Mh Ml Mx Va Vs) Ih(Fr Ip Ma Ok) Ip(Iv Ok Qd) Fw(Sh Sj) Qd(Ik Il) Sr(Rt Vh) FcIv NtVb MyOn HrOk WbOw QaRt XaNy nCnl} Dr{Ow(An aY cX Nr Nx Oi Qn) Kd(Bo Lh Lx Mk Mq Pf) Oa(Gc Gp Pj) Nn(Kl Sh) Lx(Qn Zw) Pf(Ic Sh) MkLp KlOm OraW} Ed{fR(aW Ba Mg Na Ni Nk Nn Ow Pd Vq) Gd(Ba Cw Kx Mg Na Ni Nn Ow Pd) Gb(Ba Lx Nn Pf)} On{My(Ih Ip Jg Jh Jn Ns) Oy(Ih Ip Jg Jn Nm Qb) Of(In Is Iv Jn Om) ThaY NsNd HrIv IkQd} Wb{Ow(Kl Lv Ml Oi Pc Qn) Lx(Bb Bn Kd Ky) Nn(Kl Ng Sh) Pf(Hc Ic Lu) Oa(Gc Pj) MhOm MkPa} Sh{Nn(Fn Fr Hu Jh Ny) Hu(Is Lx Ow Pf) Cx(Fw Oa) Dd(Ml Pf) AfNv FwMv NqKd HpPf IhJv IlJd} Uh{bN(Is Jo Js Ko Md Mj Ni Nm Nr Ok Ul Ur Us) Qa(Nk Ou Vs) PsVa} Va{Ps(Hu Oi Pc Qt Qw Vp Vt Wf) Vt(Nt Qy Rc Sr) Un(Jm Pa Ru) SrUo} Jg{My(Ih Is Js Qb) Ih(Ng Oi Oy) Js(Ng Of Oy) Is(Of Oy) NsNd IkQd IvOf} Hr{Iv(Fr Ih Ip Jn Nn Ok Qa Qb) Ok(Ih Ip Is Jn Js Qb)} Oa{Gc(Af Bo Cq Iq Jo) Af(Si Ti) Cx(Fc Xa) Zw(Ic Mt) Ye(Hu Jh) CvFc} Qd{Ik(Fp Ip Jn Js Ma Nm Nn Nr Nt Ny Ok) NsNd IlIp} Ch{Jh(Fc Fi Ho Lp Rz Tm) Nq(Gz Lp) RzNy} Rt{Sr(Hx Is We) Qa(Oi Pc) NrQy MiQb HvJm IlIv} Ih{Ma(Ip Iv Ns Oy) Oy(Fr Ok) AjFc MtMy} Zw{Lx(Cx Hp Je Nt) Ow(Hp Nu) NrQl NtOh} Jn{Af(Fi Ho) Bo(Fc Fi) Wf(Nj Qy) CxOp NsNd} Ny{Fc(Mk Pf) DeHo GcKr KdLp PsVp} Af{Ho(Ow Pf) Lp(Mq Ow) GbPf} Nd{Ns(Fp Is Nt Ok) HqOk} Hp{Nn(Aj Kl Ng) KlOw} Sr{Gd(An aW) QaUw} Xa{AdKd BoFw FcOi} Nu{FcLx QaWf} AjCxHo BoGbNr ThIvJp FrMtWc FwNtYl LxQyUx MqHlKd MrRuPa HuQwPs QcnIoQ bCdMjQ bMcHnN

Unconstrained panels with 3 analytes, where 2.4E-8 >= 'model p-value' > 1.0E-8. Contains 15,495 panels of 15,247,928 total panels evaluated. : Li{Du(aA AF Aj aP AX bC bH bM Ch cQ cR Cs Ct cV cX De Dg dH dJ Dr Ed Eq Ex Fp Fr Hf Hx Ih Ij Im Ir Is It Iv Ji Jl Jn Jr Js Ju Ki Kl Kq Kz Lj Lx Mj Mr Ms Mv Mw Mx Ng Nh No Nr Nw Ny Oa Oe Oh Ow Oy Oz Pb Pc Pe Pk Po Ps Qa Qb Qt Qu Rf Rg Rm Rz Sr Tz Ug Un Uu Ux Va Yd Tm Xa) Vi(Af Aj Al AN AO aW aX aY Bc Bg bH bL bM Bn Bo bU cC Ch cP cQ cR Ct Cu CV CX Dd DE DG dH Dk Ed Ef Eq Ez Fc Fi Fw Gh Gl Ib Jd Ju Jy Kd Ki Kj Kl Kr Kx Ow Ql Qn Rx Rz Sf Us Ut Uu Uv Yd Zw Tj) Ne(dX eP Fp Fr Hq Hr Hw Hx Ii Io Iq Iu Jg Jh Jk Jl Lh Lu Lv Ma Md Me Mg Mj Mk Ml Mm Mq Mr Ms Mt Mu Mv Mx Na Nb Nf Nh Ni Nj Nk Nl Nm Nn Nq Nr Nu Nv Nx Oh Om Pd Pf Pg Po Pz Qe) Hw(Fp Hq Hx Ii In Io Iq Jg Jh Jk Jl Jm Jr Lh Lu Lx Ma Md Me Mg Mj Mk Ml Mm Mp Mr Ms Mt Mu Mv Mx Nb Nf Nh Ni Nj Nm Nn Nq Nr Nu Nv Nx Ny Oh Om On Pa Pd Pe Pf Pg Po Pz Qa Qe) Yd(aC aE aF aJ aN aR aS aU aV aX aY aZ bA bE bF bJ bL bM bO bR bS bW bZ cG cH cL cS cV cW dD dF dG dH dL Ed Eq Ex Gb Ps Qd Qy Rc Rg Rt St Tn Ub Uh Um Un Uo Ur Uv Vc Vt) Jm(Fp Hq Hr Hx Ii Io Iq Jg Jh Jk Jl Lh Lu Lx Lz Ma Md Me Mg Mj Mk Ml Mm Mp Mq Mr Ms Mt Mu Mv Mx Na Nb Nf Nh Ni Nj Nm Nn Nq Nr Nu Nv Nx Ny Oh Om Pa Pd Pe Pf Pg Po Pz Qe) Mp(Fp Fr Hr Hx Ii Io Iq Iu Jg Jh Jk Jl Lh Lu Lv Lx Ma Md Me Mg Mi Mj Ml Mm Mq Mr Ms Mt Mu Mx Na Nb Nf Nh Ni Nj Nl Nn Nq Nr Nu Nv Nx Oh Om On Pa Pd Pe Pg Po Pz Qe) Ny(Eq Fp Fr Hx Ii Io Iq Jg Jh Jk Jl Lh Lu Lv Lx Ma Md Me Mg Mj Mk Ml Mm Mq Mr Mt Mu Mx Na Nb Nf Nh Ni Nj Nl Nm Nn Nq Nr Nu Nv Oh Om On Pa Pd Pe Pf Pg Po Qa Qe) Iq(Fp Fr Hq Hr Hv Hx Ii Io Jg Jk Jl Jr Lh Lu Lx Ma Md Me Mg Mi Mk Ml Mm Mr Ms Mu Mv Mx Na Nb Nf Nh Ni Nj Nm Nn Nr Nu Nv Nx Oh Om On Pa Pd Pe Pg Po Pz Qa Qe) Nm(Fp Fr Hx Ii Io Iu Jg Jh Jk Jl Lh Lu Lv Lx Ma Md Me Mj Mk Ml Mm Mq Mr Mt Mu Mv Mx Na Nb Nf Nh Ni Nj Nl Nn Nq Nr Nu Nv Oh Om On Pd Pf Pg Po Pz Qe) Nk(Fp Fr Hq Hr Hx Io Iu Jg Jh Jk Jl Lh Lu Lv Lx Ma Md Me Mg Mj Mk Ml Mm Mq Mr Mt Mu Mv Mx Na Nb Nf Nh Nj Nl Nn Nq Nr Nu Nv Nx Oh Om Pd Pf Pg Po Pz) Pe(Fp Fr Hq Hx Ii Io Jg Jh Jk Jl Lh Lu Lv Lx Ma Md Me Mg Ml Mm Mq Mr Ms Mt Mu Mv Mx Na Nb Nf Nh Ni Nj Nl Nn Nq Nr Nu Nv Nx Oh Om Pa Pf Pg Pz Qa Qe) Hv(Fp Fr Hx Ii Io Iu Jg Jh Jk Jl Lh Lu Lv Lx Ma Md Me Mg Mk Ml Mm Mq Mr Ms Mt Mu Mx Na Nb Nf Ni Nj Nl Nn Nq Nr Nu Nv Nx Oh Om Pd Pf Pg Po Pz Qe) Pa(Fp Fr Hx Ii Io Jg Jh Jl Lh Lu Lv Lx Ma Md Me Mg Mi Ml Mm Mq Mr Ms Mt Mu Mx Na Nb Nf Nh Ni Nj Nl Nn Nq Nr Nt Nu Nv Nx Oh Om On Pd Pg Pz Qe) Hq(Fp Hr Hx Ii Io Jg Jh Jk Jl Jo Lh Lu Lx Ma Md Me Mg Mj Mk Ml Mm Mr Ms Mt Mu Mv Mx Na Nb Nf Nh Ni Nn Nq Nr Nu Nx Oh Om Pd Pf Pg Po Pz Qe) Mc(Fp Fr Hx Io Iu Jg Jh Jk Jl Lh Lu Lv Ma Mb Md Me Mg Mj Mk Ml Mm Mq Mr Mt Mu Mx Na Nb Nf Nh Ni Nj Nl Nn Nq Nr Nu Nv Nx Oh Om Po Pz) Ii(Fp Hx In Io Jg Jh Jk Jl Lh Lu Lx Ma Md Me Mg Mj Mk Ml Mm Mr Ms Mt Mu Mx Na Nb Nf Nh Ni Nj Nn Nr Nu Nv Nx Oh Pd Pf Pg Po Pz Qe) Ed(Dr Eq Fc Fd Fi Gh Gn Hl Ho Lp Op Ps Rt Ru Rv Rx Ry Rz Sf Sh Uw Ux Uy Va Vb Vh Vw Vz Wb Wc Wd We Wf Wh Yl Zw Zx Ye Tm Tl Xa) Lz(Fp Fr Hx Io Iu Jg Jh Jk Lh Lu Lv Ma Md Me Mg Mj Mk Ml Mm Mq Mr Mt Mu Mx Na Nb Nf Nh Ni Nj Nl Nn Nq Nr Nu Nv Oh Om Pd Po Pz) Mv(Fp Fr Hr Hx Io Jh Jl Jo Lh Lu Ma Md Me Mg Mj Mk Ml Mm Mr Ms Mx My Na Nf Ng Nh Ni Nj Nq Nr Nu Nv Nx Oh Om Pd Pf Pg Po Pz Qe) Ms(Fp Hr Io Jg Jl Jo Lh Lu Lx Ma Md Me Mg Mj Ml Mm Mr Mt Mx My Na Nf Nh Ni Nj Nn Nq Nr Nu Nx Oh Om Pd Pf Pg Po Pz Qe) Pg(Fp Hr Io Jg Jk Jl Lh Lu Lx Md Me Mg Mj Mk Mm Mr Mt Mu Na Nb Nf Nh Ni Nn Nt Nu Nv Nx Oh On Pf Po Pz

Figure 38 Continued

Qa Qd Qe) Jo(Fp Fr Hx Io Iu Jh Jk Lu Lv Ma Md Me Mg Mj Mk Ml Mm Mq Mt Mu Mx Nf Nh Nj Nl Nq Nr Nv Nx Om Pd Po Pz Qe) Mb(Fr Hx Io Iu Jg Jh Lh Lu Lv Ma Md Mj Mk Ml Mm Mq Mr Mt Mu Na Nb Nf Nh Nj Nl Nn Nq Nr Nu Nv Om Po Pz) Mn(Fp Fr Hx Io Iu Jg Jh Lh Lv Lx Ma Md Me Mj Ml Mm Mq Mr Mt Mu Mx Nb Nf Nh Nj Nl Nq Nr Nv Om Po Pz Qe) Qa(Fp Fr Hx Io Iu Jg Jh Lh Lu Lv Lx Ma Mg Mk Ml Mm Mq Mr Mt Mu Mx Na Nb Nj Nl Nq Nr Nu Nv Om Po Pz Qe) On(Fp Fr Hx Io Iu Jg Jh Jl Lh Lu Lv Lx Ma Me Mj Ml Mm Mq Mr Mt Mx Na Nb Nf Nj Nl Nn Nq Nr Nu Om Pz Qe) Ni(Fp Io Jg Jh Jk Jl Lh Lu Lx Ma Md Me Mg Mj Ml Mm Mr Mt Mx Na Nb Nf Nh Nn Nu Nx Oh Pd Pf Po Pz Qe) Lj(Fr Hx Io Iu Jh Jl Lh Lu Lv Ma Md Me Mj Mk Ml Mq Mr Mu Mx Na Nf Nh Nj Nl Nq Nr Nu Nv Om Pd Po Pz) Qd(Fp Fr Hx Io Iu Jg Jh Lh Lu Lv Ma Md Mk Ml Mm Mq Mr Mu Mx Na Nf Nj Nl Nq Nr Nv Om Po Pz Qe) Nx(Dr Fp Hr Io Jg Jl Lh Lx Ma Me Mg Mj Ml Mm Mr Mt Mx Na Nb Nf Nh Nn Nr Nu Oh Om Pd Pf Pz Qe) Hr(Fp Io Jg Jk Lu Lx Ma Md Me Mg Mj Ml Mm Mq Mt Mu Mx Nh Nj Nn Nr Nu Oh Pd Pf Po Pz Qe) Jl(Fp Io Jg Jk Lu Lx Ma Md Me Mg Mi Mj Ml Mm Mt Na Nb Nf Nh Nn Nt Nu Nv Oh Pd Pf Po Qe) Jr(Fr Hx Io Iu Jg Jh Jk Lh Lu Lv Ma Mk Mq Mr Mt Mu Mx Na Nb Nj Nl Nq Nr Nv Om Pz Qe) Nn(Fp Io Jg Jk Lh Lx Md Me Mg Mi Mj Mr Mu Na Nb Nf Nh Nq Nu Nv Oh Pd Pf Po Qe) Nt(Fp Fr Io Iu Jg Jh Lh Lu Lv Lx Ma Ml Mm Mq Mr Mx Na Nb Nj Nq Nr Nu Om Pz Qe) Lx(Fp Hx Io Jg Jk Md Me Mg Mi Mj Mk Mt Na Nb Nf Nh Nu Nv Oh Pd Pf Po Qe) Mi(Fp Fr Io Iu Jg Jh Lh Lu Lv Ma Ml Mm Mq Mr Mt Mx Nb Nj Nl Nr Om Pz) bM(Fc Fi Lp Ps Rt Ru Rv Rx Si Uw Uy Va Vb Vh Vw Vz Wc We Wf Wh Yl Zw) Pf(Fp Io Jg Jk Lh Md Me Mg Mj Mk Mm Mr Mx Na Nb Nf Nh Nu Oh Po Qe) Mg(Fp Io Jg Lh Ma Me Ml Mm Mr Mt Na Nb Nf Nh Nu Oh Pd Pz Qe) Mh(Fr Io Iu Jg Jh Lu Lv Ma Mj Mk Mm Mq Mu Nj Nl Nq Nv Om Pz) Nb(Eq Hx In Jh Jk Md Me Mj Mk Ml Mu Nf Nh Nu Nv Oh Pd Qe) In(Fr Iu Jg Lh Lu Lv Ma Mq Mr Mx Na Nj Nl Nq Nr Pz) Oh(Fp Io Jg Jk Lh Md Me Mj Mr Mt Na Nf Nh Nu Pd Qe) Nh(Fp Io Jg Lh Me Mr Mt Mx Na Nf Nu Pd Qe) aX(Fc Gb Hp Rt Rx Va Vw Vz Wb Wd Wh Zw Tl) Eq(aY Ba bJ Cx Hu Im Iz Jh Jk Mw Qy St) Ps(Af aN aY Bn cC Ch De Fc Gl Rx Us Uv) Pd(Fp Jg Lh Ma Me Mr Mt Mx Na Nf Nu Qe) Mr(Hx Jk Md Me Mj Mk Nf Nu Nv Qe) Mt(Hx Jk Md Me Mj Na Nf Nu Po Qe) Ng(Hx Iu Lv Md Mk Mq Mu Mx Nl) Lh(Jk Md Me Mj Mk Nf Nu Nv Po) Rt(Af cC Ch CV cX De Kd Ki) Na(Jk Md Me Mj Nf Nu Po Qe) Wb(aN aW aY cR cX Us Uv Th) Af(Ru Rv Uy Vh We) Fc(aA aZ cV dK Un) Va(aE aV aY aZ dL) Nu(Jk Me Mj Nf) Jg(Jh Jk Jp Mu) aA(Fi Ru Rx Uy) Hp(aN Us Uv) Ke(Kf Pb Ph) bO(Fi Lp Uy) cV(Gh Hl Vz) Cx(Rv Ux) Iu(Of Qc) Jp(Io Nq) ChVw MfPz MjMx VzSr SjUs ZwdA QyRz LdUy LpdD} Aa{Qd(aA Et Fr Hq Hu Hv Hw Hx Ii Iq Is Iu Jg Jh Jk Jl Jo Jp Jq Jr Jt Lh Lj Lv Lw Lx Ly Ma Mb Mc Me Mf Mg Mh Mi Ml Mm Mn Mp Ms Mv Mx Mz Na Ne Nf Ng Nh Nj Nl Nm No Nq Nr Nt Nv Ny Oh Ok Om On Pa Pd Pe Pg Po Pz Qe) Qe(aA Fr Hq Hv Hw Hx Ik Is Iu Jg Jh Jk Jl Jt Lh Lj Lv Ly Mb Mc Me Mh Mi Ml Mm Mn Mp Mv Mx Mz Na Ne Nf Ng Nh Nj Nl Nm Nr Nt Ny Ok Om On Pd Pe Pg Po Pz) Pc(aA Hq Hu Hv Hx In Io Jg Jh Jk Jl Jo Jq Jt Lh Lv Lw Ly Mb Mc Me Mf Mg Mi Ml Mn Ms Mv Mx My Mz Na Ne Nf Ng Nh Nj Nl Nm Nt Nv Oh Ok Om On Oz Pb Pd Pz) Ir(aA Fr Hu Hv Hw Ih Ii Ij Ik Il Io Iq Is Iu Jg Jh Jk Jl Jr Jt Lj Lw Lx Mc Me Mg Mh Mj Ml Mn Mp Ms Mt Mv Nd Nf Ng Nh Ni Nj No Nq Ns Nu Nv Ny Pd Pz) Mq(aA Hw Hx Ij In Io Is Jh Lh Lv Lw Ly Ma Me Mf Mg Mh Mi Mj Ml Mn Ms Mu Mv Mx My Mz Nd Nf Ng Ni Nj Nl Nn Nq Nr Ns Nt Nv Ny Oi Ok Om On Pa Pd) Jn(aA Hq Hu Hv Ii Ij Io Iq Is Jg Ji Jl Jo Jr Lh Lv Lw Me Mf Mg Mh Mi Mj Ml Mn Mp Mv My Mz Nd Nf Ni Nj Nq Nr Ns Nt Nu Ny Oi Ok On Pa Pe Pg Pz) Fp(Fr Ii Ij Io Is Lh Lj Lv Lw Lx Ly Ma Mb Mc Me Mf Mh Mi Mj Mk Ml Mm Mn Mp Ms Mv My Mz Na Ne Nf Ng Nh Nj Nq Nr Ns Nt Nu Nv Ny Oh Ok Om On) Mt(Hq Hu Hw Hx Ii Ij Il In Io Iq Is Iv Jg Jh Ji Jk Jl Jq Jt Lj Lu Lw Lx Ma Mf Mg Mh Mj Mk Ms My Nb Nc Nd Nf Ni Nj Nk No Nq Ns Nu Nv Pd Pz) Jj(aA Hq Hw Hx Ii In Io Iu Jg Jh Jo Jq Lh Lv Lw Ly Mb Mc Me Mf Mi Ml Mm Ms Mx My Mz Na Ne Nf Ng Nh Ni Nj Nk Nl Nm Nv Of Oh Oi Ok Om Pa Pd) Nw(aA Fr Ii Ij In Iu Lh Lv Lw Lx Ly Ma Mb Mc Me Mi Mj Mk Ml Mm Mn Mp Ms Mv Mx Mz Na Nd Ne Nf Ng Nh Ni Nj Nl Nm Nr Nt Ny Oh Ok Om On) No(Hq Hu Hv Hw Hx Ii Ij In Io Iq Is Jg Jh Jk Jl Jo Jp Jq Jt Lx Ma Mf Mg Mk Mp Mr Ms My Nb Nd Nf Ni Nq Ns Nu Nv Pa Pd Pe Pg Po Pz) Et(aA Fr Hu Hv Ii In Io Iq Ji Jl Jo Jp Jr Lw Ma Me Mf Mg Mh Mi Ml Mm Mp Ms Mv Mx Mz Na Nf Ng Ni Nj Nm Nq Nr Ns Nt Nv Ny Po) Ih(aA Hw Hx Ii Ij Il Io Iq Is Iu Jg Jh Jk Jl Jt Lv Lw Mc Me Mg Mh Mi Ml Mn Mp Mv Mz Nd Nf Nj Nq Nr Ns Nt Nv Ny Ok Pd Pz) Ip(aA Hw Ii Io Iu Jk Lj Lv Lw Ly Mb Me Mf Mi Ml Mn Mp Mv Mx My Mz Na Nd Nf Ng Ni Nk Nl Nr Ns Nt Nv Ny Oi Ok Om On Pd Pz) Iv(Fr Hq Hu Hw Hx Ij Io Is Jg Jh Jk Jq Jt Lw Ly Ma Mf Mg Mh Mj Mk Ml Mp Ms Mv My Mz Ng Ni Nj Nk Nq Nr Ns Nu Ny Om Pa Pd) Og(aA Hx Ii In Io Jq Lh Lv Lw Ly Mb Mc Me Mf Ml Mn Ms Mx My Mz Na Nc Nd Nf Ng Nh Ni Nj Nk Nl Nm Nv Of Oh Oi Ok On Pa Pd) Mr(Fr Ii Ij In Io Is Iu Lj Lw Lx Ly Mc Me Mf Mh Mi Mj Ml Mn Mp Mv Mx My Nd Nf Nk Nq Nr Ns Nt Nu Nv Ny Of Oi Ok Om On) Nn(Fr Hq Hu Hw Hx Ij Il In Is Iu Jg Ji Jk Jq Jt Lj Mh Mj Mk Ms My Nb Nd Nf Nk Nq Ns Nu Nx Ny Of Oi Pa Pd Pe Pg Pz) Oz(aA Hq Hw Hx Ii Iu Jg Jh Jk Jq Jt Lh Ly Mb Mc Mm Mn Mx Mz Na Ne Nf Ng Nh Nj Nl Nm Nv Oh Om On Pa Pd Pz) Lx(Hq Hu Hv Hx Il In Iq Ji Jl Jo Jp Jq Jr Jt Lu Mk Ms Mu My Nb Nc Nf Nk Ns Nu Nv Of Pa Pe Pf Pg Po Pz) Jm(Hr Hv Ij In Iq Is Jl Jo Jr Lj Lw Mf Mg Mh Mi Mj Mp Ms Mv My Nb Nd Nk Nq Nr Ns Nu Nx Ny Oi Pe Pf Pg) Ji(aA Fr Hv Ij Il In Io Iq Jp Jr Lj Lw Ma Mh Mj Mk Ms Mu My Nc Nd Ni Nq Ns Nu Ny Oi Pe Pf Pg Po Pz) Lj(Hq Hu Hv Ij Ik In Iq Jg Jh Jl Jo Jq Jr Lu Ma Md Mg Mk Mu Nb Nc Nk Nq Nu Nx Pa Pe Pf Pg Po Pz) Hr(Il In Iq Is Jh Jp Lh Me Mg Mh Mi Ml Mp Mv Nb Nd Ni Nr Ns Nu Nx Ny Oe Of Oi On Pe Pf Pg) Ij(Hv Ii Il In Iq Jg Jh Jl Jq Jt Lu Mh Mk Ms Mu Nb Nc Nd Nk Nu Oi Om Pa Pd Pe Pf Pg Po Pz) Jp(Hv Il Io Iq Jl Jr Ma Mg Mh Mj Mk Mp Ms My Nb Nc Ni Nq Nr Ns Nt Nx Ny Oi Pe Pf Pg Po) Po(Hq Hv Il In Iq Is Jo Jr Lw Ma Mf Mj Mk Ms Nb Nc Nd Nf Ni Ns Nu Nv Pa Pe Pf Pg) Mu(Fr Hu Hv Il In Iq Is Jl Jo Jt Lu Md Mh Mk Nb Nf Nq Ns Nu Nx Ny Oe Of Pe Pg Pz) Nc(Fr Hv In Jl Jo Jr Lu Ma Mg Mh Mj Mk Mv Nb Nd Nq Ns Nu Nx Oe Of Pe Pf Pg) Oy(aA Hq Hw Hx Ii Iu Jo Jq Lw Ly Mb Mc Me Mf Mm My Ne Ng Nh Nj Nl Nm Oh Pa) Md(Fr Hu Hv Il Iq Is Jg Jk Jl Jo Jt Lu Ma Ms Nb Nq Nu Ny Oe Pe Pg Pz) Pf(Fr Hv Il In Is Jl Jr Lu Ma Mf Mj Ms My Mz Nd Ni Nk Nq Ns Nu Ny Of) Lz(aA Ii Ik Io Iu Lh Lv Mh Ml Mm Mx Na Ne Ng Nh Nj Nl Nm Nv Oh Ok) Pb(Hq Hw Hx Ii Iu Jo Jq Ly Mc Mm Ne Ng Nj Nl Nm Nv Oh Pa Pd Pz) Lu(Fr Hv Il Is Jg Jl Jo Jr Jt Ma Mj Mk Nb Nd Nq Ns Nx Pe Pg) Iq(Fr Hv Il In Jr Ma Mh Mj Mk Nq Ns Nu Nx Of Oi Pe Pg) Jr(Fr Il In Ma Mg Mj Mk Ms Nb Ni Nk Nq Ns Nu Nx Of) Oe(Hu Hv Il Jg Jt Ma Mj Mk Mv Nb Nu Ny On Pe Pg Pz) Of(Fr Hv Is Jg Jk Jl Jt Ma Mg Mj Mv Ny On Pg Pz) Nx(Fr Hv Jl Ma Mg Mj Mk Nq Nu Ny On Pe Pg) Mk(Hq Hv Il Jl Jo Jt Pa Pe Pg Pz) Nu(Hv Is Jl Ly Ma Mj Nd Pe Pg) Mj(In Jo Jq Mg Ms Nb Nk Pa) Hv(Fr In Ma Nb Ni Nk) Pe(Ma Nb Ny Oi Pa Pd) Fr(Il Jo Nb Oi) Jl(Il In Nk Oi) Nq(Ms Oi Om) Pg(Nb Ny Pa) Mg(Jo My) Hx(Is Ml) MaJo MvMy HuOi IkJs UhbN} Nw{Qd(Fr Hq Hr Ii Io Iq Iu Jg Jh Jk Jl Jo Jp Jq Lh Lu Lv Lx Ma Mc Me Mg Mj Mk Ml Mm Mn Mq Mr Mt Mu Mx Mz Na Nb Ne Nf Nh Ni Nj Nl Nm Nq Nr Oh Ok Om On Pe Pf Pg Po Pz Qb Qe) Qb(Fr Hq Hr Ii Io Iq Iu Jg Jh Jk Jl Jp Lh Lu Lv Lx Lz Ma Mb Mc Me Mf Mg Mj Mk Mm Mn Mq Mr Mt Mu Mx Mz Nb Ne Nf Nh Ni Nj Nl Nq Nr Oh Om On Pd Pe Pf Pg Po Pz Qe) Nu(Hq Hr Ii Ik Il In Iq Jg Jh Jk Jl Jp Lh Lu Lw Lx Lz Mb Mc Me Mf Mi Ml Mn Mp Mr Mu Mx Mz Na Nd Nc Nh Ni Nk Nm Nn Nr Nv Oh Oi Ok Om Pa Pd Pe Pf Pg Po Pz Qe) Hw(Fr Hq In Io Iq Iu Jg Jk Jl Jo Jp Jq Jr Lh Lu Lv Lw Lx Ma Mb Mc Me Mf Mg Mj Mk Mm Mq Mr Mt Mu Mx Mz Na Nb Ne Nh Ni Nj Nk Nl Nq Nr Oh Ok On Pe Pf Pg Pz Qe) Nt(Fr Il In Io Iu Jg Jl Jp Lh Lu Lv Lw Lx Lz Ma Mb Mc Me Mf Mg Mi Mj Mm Mn Mp Mr Mu Mx Mz Na Nb Nf Nh Ni Nj Nk Nl Nm Nn Nq Nr Oh Oi Ok Om On Pe Pf Pz Qe) Jo(Hq Ik Il In Iq Jh Jk Jl Jp Jq Jr Lh Lu Lv Lw Lx Lz Mb Mc Me Mf Mg Mi Mj Mk Mm Mn Mp Mu Mx Mz Nb Ne Nf Nh Ni Nk Nm Nq Nr Oh Oi Ok Pa Pd Pe Pf Pg Qe) Jq(Hq Ii Ik Il In Iq Jg Jh Jl Jp Jr Lu Lv Lw Lx Lz Ma Mb Mc Me Mf Mi Mj Mm Mn Mu Mx Mz Na Nb Ne Nf Nh Ni Nk Nm Nn Nr Oh Oi Ok Pa Pd Pe Pf Pg Po Qe) Ly(Hq Hr Ii Ik Iq Jg Jh Jk Jl Jp Lh Lu Lw Mb Mc Md Me Mf Mg Ml Mm Mn Mr Mu Mx Mz Na Nb Ni Nj Nk Nl Nm Nn Nr Nv Nx Oh Oi On Pa Pd Pf Pg Po Pz Qe) Fp(Fr Ii Il Io Iu Jg Jk Jp Lh Lu Lv Lx Lz

Figure 38 Continued

Ky Ng Oz Qy St Yd) Qy(bQ cO Ld Lx Mh Nr Oh Ow Pf Va) Nt(Fw Is Oh Ow Pf) St(aW Co Jh Mg Rz) Ow(Af Hu Nu Yd) Mq(Bb Fw Ph)
Kq(aY Cx Nx) Ny(aW Mg Rz) cO(Fw Jg Sr) Mu(Nr Pf) Om(Va Yd) BaVa Bblv ChJh CxPd MgcE JgLd JnaF KdQl NvaW OnaY} It{Ok(Fp Fr
Ik Iv Jg Jq Jr Js Jt Lx Ly Mh Mn Mp Ms Mz Nk Nn Ns Pc Pd Qc Qd) Is(Hr Ik Ip Jg Jn Jt Lx Mm Mn Mz Nd Ns Nu Ny Of On Oy Qc) Jp(Fp Jn
Jq Lz Mi Mp Mz Nd Nk Nm Nn Nt Oe On Oy Pc Qb Qd) Jt(Fr Ik Jn Js Lx Lz Mz Nd Ng Nn Ns On Oy Oz Qc Qd) Jj(Hv Io Iq Jr Lz Mc Mg Mr
Mt Nq Ns Og Pa Pc Pg) Og(Jl Jn Jq Lx Ma Mn Mz Nb Nv Ny Po Qc Qe) On(Hu Ip Iv Ly Nd Ng Nx Qc) Pb(Ip Iv Lh Lx Ma Mz Qd) Fr(Ik Iv Js
Oe Oy) Js(Ik Ip Jg Oe) Qd(Il Oe Oz) Nn(Iv Oe) CxVa NsNd NbOf NgJg NkUh IpOz KdRt RxbM LpUr} Nb{Rt(aC aF Ao Ap aU aW aX Bb bC
bE bJ bW cC cG cL CO cP cS Cu Cw Cx cZ Dd De dK Ef Ez Fc Fi Gb Gc Ho Kc Kd Kg Ko Kq Ld Ow Pj Rz Vq) Tl(aJ aN aW bS cX dM Qv
Rj Uh Ur Vp Wf) cV(Hl Hp Lp Op Rx Ry Sh We Wf Ye Xa) Bo(Ps Uw Ux Vb Vh Vw Wc Wd We Wh) Ld(Ru Uw Ux Uy Va Vb Vh We)
Ur(Fc Fi Gh Gn Lp Si Uy Zw) Ti(Bg Iv Jj Jo Uc) Sr(Hl Ry Vz Yl Zw) Wd(Aj De Kj Us) Of(Fr Jn Ny Ok) Og(Ip Jn Js Jt) Gc(Up Us Uu) Hl(aF
aW Vq) Fc(Po Qx) Yd(Uh Un) We(aW Kq) Rx(aL cH) Us(Fi Rz) Ux(Ap Pj) DrUh HoVq HbVa} Jt{Og(Ii Ik In Iq Jh Jk Jl Jp Jr Lh Me Mg Mh
Mi Mj Ml Mm Mp Mr Ms Mx Na Nc Ne Ng Nk Nq Nv Oy Pc Pg) Jj(Fr Ii Iv Jg Jp Lh Lx Lz Ma Mf Mi Mm Mp My Nc Nd Ns Nt Nu Nv Of Ok
Pg Po Qe) Hr(Fr Iv Jl Mp Nn Ns Ny Oe Ok On Oz Pa Po Qc Qd) Pb(Jp Lz Ma Mn Mz Ny Of Ok Po) Qb(Ip Jn Jo Ms My Ng Ns Oz) Oy(Fp Ip
Jn Js Mt On Pf Qd) Of(Ip Is Js Mi Ny Pa Pg) Oe(Fr Ip Lx Mz Qe) Jn(Ip Jo Ng Ns) Fp(Jo Oz) My(Mt On) Nglp QdOz JoJs RtaY} Kq{De(Ad As
aU aW aY aZ Bb bO cE cH Ct Cw Dg Ef Ex Fr Gl Gp Hc Hq Ib Ic Il Ip Jf Jm Jo Kc Ld Lu Ml Mm Mn Mz Ne Nl Nr Nu oE Of Or Oy Pi Qm Qy
Ru Sr Ur Uv) Uv(bN Du Fi Ho Lp Ru Rx Sf Si Va Tm Tl) Yd(aR aZ bL cX dG Qb Rj Uh Vs Th) Ru(Af Aj Bg Kl Of Oy Tn Uu) Ch(Ps Va Vb
Wc Wd) Lp(aY Ur Us Uu Vp) Nx(Uw Wd Wf Wh) Uh(Gl Ou Uu Vs) aY(Gc Rt Rx Sh) Rx(aF cV) Rt(Fw Nr) Uu(Fc Tm) AfUy BgbN UxaN}
Va{Ps(Af aJ aR aZ bM Bn Bo bS CX dB dG Dk Hc Ib Ki Qn Rj Rx Uu Vq Ye) Sr(aC Af aG aN bM BO cF Dr Jf Or Uv Vq Vz Yl) Ld(Al aX
Ba Bb Dc Fw Il Jg Jm Kd Lp St) Ow(aE bM bO dL Dr Un Uo Wb) Cx(Dd Dr Fd Hp Hv Hx Xa) Un(aN aY cD Ex Fc Fi Fw) Ch(Ef On Qy Ut)
Hb(Jn Oa Rm) Si(aE aV bJ) Vt(aE aG aN) Vq(aZ Nu Ny) Rm(Bo dl) aG(Oa Qb) aX(Mt Nn) AfOm PoaN HcNv IsdD IuaZ StdI KdQm OhaC
aSbA} On{Oy(Fp Is Jh Js Mt My Nn Ns Ny Of Oz Pf Qc Qd) Og(Fp Hq Hu Hv Iq Jq Jr Lw My Mz Nk Nu Ok) Of(Hv Hw Ip Jq Jr Js Mt My
Mz Ns Oz) Jj(Fp Hu Ms Nm Nu Ny Pc Qb Qc Qd) Oe(Fp Hq Hu Ip Ly Ms My Pc Qc) My(Js Nm Nn Ny Qb Qc) Pb(Fp Lz Ms Ok Pf Qd)
aY(Rv Sh Vb) Hr(Hv Jn) Yd(Uh Vt) Rt(Fw Kd) Oz(Ip Is) FcUu} Is{Oe(Fp Hr Ii Jj Mn Mt Mz Nr Nt Nu Nv Og Pc Pz Qb Qc) Pb(Hr Iq Mg Mp
Mt Nc Nd Ne Nv Of Om Pc Pg Qc) Og(Ii Il Lh Lx Mt Ns Nv Pc Pf Po Pz Qe) Oz(Fp Hr Jp Lx Lz Mn Nn Ns Ny Of Ok) Jj(Fr Js Ma Mm Ny Ok)
Oy(Fr Ma Nm Nn Pf) Of(Fr Ma Nm Nn) Yd(aF Qy Un) Nm(Hr Ns) Rt(aF Dd) NsJg IkQd} Yd{Ow(aF aO aX aY bF bR cG dF dH Ps Qd Un)
Uh(Cu Hw Jh Ld Mr Mt Ni Nt Pi Ps Sr) Lx(aC aG aN aY bE bJ Gc Qd Qy) Ld(Pz Qc Qe Qh Sr St Uc Vh) Qd(aW Gc Ic Pj Ti) Ut(Gc Hb Hc Oz
Pj) Mt(aM aX bV Vt) Sr(aG aQ Bo Ur) Nt(Qx Tz Vt) Po(aY Gc) Nn(aX aZ) Qy(Lh Oh) GccX PsRx NyaW OaaG PfaY} Jj{Js(Fp Fr Hv Ii Iv Jp
Lw Lz Ma Mc Mg Mp Mz Nh Ns Of Pc Pf Qb Qd) Jn(Fr Ii Jg Jm Lh Ma Mm Mz Nu Ny Qb) Nm(Ip Mn Nr Nt Og Oz Qd) Ok(Il Ip Jm Oz Qb)
Qd(Ip Jg Mn Pb) Nn(Jm Oz Pb) Iv(Jg Jm Ny) Ip(Jg Ny) Xa(aW aY) FcSr HpaW liPb QbJg} Ps{Rx(aF aO cV dA Iv Qn Sr) Nn(Aj Bg De Dg
Kl) Oe(Bg Ch Kl Sh Uu) Us(Ho Hv Kd Oz Sr) Oa(CX Oz Qn) Uu(cX Hu Qy Sr) aY(aM Kx Oi Po) Af(Fw Jn) Sr(Bo Ki) Qn(Ny Oi) Ur(Lp Nr)
Oz(aZ Fw) aW(Iv Kl) ChJh DeOm ExMl LxaN WbOw OicV} Og{Js(Il Iv Jm Jn Jp Lw Mg Mm Nn Ns Nt Nu Ny Om Oz Qd) Jg(Il In Mx Nm
Nn Nr Nt Ny) Ok(Iv Nm Nn Ny Oz Qc Qd) Ip(Il Jq Mn Mz Nm Om) Qd(Iv Jm Nn Pb) Jn(Fr Mz Nt) Nm(Fp Qe) Iv(Ny Qb) OmPb} Dr{Uh(aW
aY Bb Fw Kd Nn Pf) Nn(Qu Ss Vb Vt Th) Sr(aU aV Oe Pf Rx) Ru(Mk Mq Po Qd Rh) aW(Hb Qg Qx Tz Vt) Th(Mk Mt Qd) Kd(Qb Qd Tz)
Qy(Mh Uu) Ow(To Vp) Pf(Rt Vt) BbQx OmUv} Pb{Jn(Jp Js Lh Ma Mr Mz Nn Nt Oe Pf) Ok(Fr Jp Lx Ma Mn Nm Nr Ny) Iv(Jp Js Lx Nm Pf
Qb Qd) Ip(Fr Jp Mn Mz Nt Pf) Js(Jg Jp Ma Nm Pf) Ma(Qb Qd) Oe(Fr Nn) nHnl} Oa{Rx(aC bM bO dI Du fR Gb Uo Ur) Gc(bM bO dD dI Uo)
Cx(Gb Uz Vw Wd) Rt(Ho Kd Mi Pj) Gb(Af cX Qn) Wf(Hu Jh Qy) Qy(Sh Ye) Vw(Af Oz) FcUr ZwSr WdUs YeaC} Sr{Uv(Gn Hl Rt Rx Sf Xa)
Uu(Uh Ux Vz Wb We) Rx(Hx Mv Ny Oy) Sh(aN Hu Zw) Xa(Bo Oz Pc) Rt(bI cH Ph) Wb(aU Ow) Vz(Oe Pf) Ur(Lp Zw) BoRu ChWd HpOe
YlRi} Qd{Ik(Fr Iq Iv Jp Lx Lz Mm Mn Ns Nu Pf Qb Qc) Oe(Iv Jg Js Nn Ok) Il(Jn Nm Ny Ok) Ru(Af Ur Uu) Oz(Iv Jn Ok) NgJg Hrlv}
Ny{aW(Fd Fi Gh Hl Lp Rt Rv Ry Rz Sh Si Sj Ux Vb Vw Vz Yl) Rx(aF cH cV Rg Ur) Hr(Iv Ok) Uu(Gc Ux) WfbJ RtdK} Wb{Pf(aF aO bF bG
cV Qw) aW(Cs Ld Lx Ml Mq Qx) Nn(aX Qu Ss Vt) Ow(aF aO cV cX) Nr(Uh Vt) Ru(Mk Uh) LxaY OhaF} Lp{Ld(aM cX dE Qv Qy Rt To Ur
Us Uv) Ur(cR Cx Fp Iv Jl Mq Mv Nn Ql) CvVq MqaJ IvaY QyUu} Qy{Uu(Du Fd Ho Rt Si Uz Wc Xa) Ch(Uw Vh Xa) Sh(Mx Nn Ow) Fc(Lx
Oh) Zw(Oh Ow) OwUx} Jn{Rt(aW Cx Dd) Oe(Fr Iv Jg) Fc(Ur Uu) Zw(Uf Vq) Rx(aC bJ) Ok(Of Oz) CxRv NkUh WfaY UuUx} Iv{Hr(Jg Jp Js
Nm Oz Po) Oe(Jg Nn Qb) Fr(Of Oz) Ru(Ld Ur) Vb(aY Cx) ThUn} Xa{aY(Ar Bo cU Kx Ld Lx Po) Oz(aZ cV) PzUu KdRt LdaW NxUn VtaN}
Nn{aX(Hp Vw Wd Zw) Aj(Vb Wd) HpaZ HrOk ShaE ZwUn JsOe KdRt KlVw} Uh{bN(Hx Ib Kg Kj Mi Mq Nt Ud) Nk(Jr Js) OuPi UrUu}
Ru{Aj(Ef Jh) Ch(Jh Nq) Mr(Bo Ld) CxHv PobM EmLd MvSh} Rt{Kd(Hw Jl Ld Mq Ql) Cu(aY Jm) HabQ NrKz HoJm} Js{Fr(Oe Oy) Nd(Hq
Ns) Ip(Il Oz) NmOe HwjE ShaY} Lx{aN(Hp Vz Zw) aY(Vw Vz) FcbN FibM ZwUo} Uu{Gc(bQ Hu Nv St) Cx(Gb Ho) FwWd} Mt{aX(Op
Zw) AfWe DucH GhbM MyJg} nl{Oh(nC nL) MqnK NiQc Oyml OznH} Fp{aN(Fi Ho Ti) NdHq HrOk} Ow{Af(Gb Vw) Kl(Gb Vw) ZwUo}
Fw{Af(Uw Vh) AjWd WfaM} Nt{Zw(Qb Qx) NdHq QbYe} Sh{MxbJ HuRm UvUt PfaY} Uy{Mq(Dd Kd) ChJh HuLd} Nr{HrOk ZwaS
WeQl} Fc{QxaZ RmUr} Jg{MzOf QbOy} We{Kd(Mv Ql)} Ld{HoUv HuWh} bN{BbMl HbVt} ChStWd CsDuaW CxNaVb FdQxaY GhcXfR
GlWfUt LzIpOz MgOydX HrIlOk LtNxUn cOnUmZ dMhAjK Unconstrained panels with 2 analytes, where 1.0E-8 >= 'model p-value' > 0. Contains 538 panels of 114,549 total panels evaluated. : Im(AA Et
Fp Fr Hq Hr Hu Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc
Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq
Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe Sh Ye) Ji(AA Et Fp Fr Hq Hr Hu
Hv Hw Hx Ih Ii Ij Ik Il In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh
Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv
Nw Nx Ny Oe Of Og Oh Oi Ok Om On Oy Oz Pa Pb Pc Pd Pe Pf Pg Po Pz Qa Qb Qc Qd Qe) Li(AA Et Fp Hq Hr Hu Hv Hw Hx Ih Ii Ij Ik Il In
Io Ip Iq Ir Is It Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq
Mr Ms Mt Mu Mv Mw Mx My Mz Na Nb Nc Nd Ne Nf Ng Nh Ni Nj Nk Nm Nn No Nq Nr Ns Nt Nu Nv Nw Nx Ny Oe Of Og Oh Oi Ok Om
On Oy Oz Pa Pb Pc Pd Pe Pf Pg Po Pz Qa Qb Qc Qd Qe) Nw(AA Et Fp Hu Hv Hw Hx Ih Ij Il In Ip Iq Ir Is It Iv Jj Jm Jn Jo Jq Jr Js Jt Lj Lw Ly
Md Mh Mn Mp Ms Mv Mw My Nc Nd Ng Nn No Ns Nt Nu Nx Ny Oe Of Og Ok Oy Oz Pb Pc Pf Qa Qb Qc Qd) Aa(Et Fp Ih Ip Ir It Iv Jj Jm Jn
Jp Js Lz Mq Mr Mt Mw No Og Oy Oz Pb Pc Po Qa Qb Qc Qd Qe) Et(aA Fp Ih Ij Ip Ir Is It Iv Jj Jn Js Jt Lj Mw Nc No Ns Oe Of Og Oy Oz Pb
Qa Qb Qc Qd) No(aA Ih Ij Ik Ip Ir Is It Iv Jj Jn Jt Mw Ns Oe Og Oy Oz Pb) aA(Ih Ij Ip Ir It Jn Js Jt Lj Mw Nm Ok Oz Qc Qd) Ir(Ij Ik It Jj Jp Mn
Mw Oe Og Oy Oz Pb) Ij(Jj Lj My Of Og Oy Pb) Mw(Ih Is) Jt(Lj Og) Ke(bN Nx) DuPe IhJj IsLj Unconstrained panels with 2 analytes, where 1.0E-7 >= 'model p-value' > 1.0E-8. Contains 544 panels of 114,549 total panels evaluated. : No(Fp
Fr Hq Hr Hu Hv Hw Hx Ii Il In Io Iq Iu Jg Jk Jl Jm Jo Jp Jq Jr Js Lh Lj Lu Lv Lw Lx Ly Lz Ma Mb Mc Md Me Mf Mg Mh Mi Mj Mk Ml Mm

Figure 38 Continued

Mn Mp Mq Mr Ms Mt Mu Mv Mx My Mz Na Nb Nc Nd Ne Nf Ng Nh Ni Nj Nk Nl Nm Nn Nq Nr Nt Nu Nv Nx Ny Of Oh Oi Ok Om On Pa Pc Pd Pe Pf Pg Po Qa Qb Qc Qd Qe Rx) Aa(Fr Hq Hr Hu Hv Hw Hx Ii Ij Il In Io Iq Is Jg Jh Jk Jl Jo Jq Jr Jt Lh Lj Lu Lv Lw Lx Ly Ma Mb Mc Md Me Mf Mg Mh Mi Mj Mk Ml Mn Mp Ms Mu Mv Mx My Mz Na Nb Nc Nd Ne Nf Nh Ni Nj Nk Nl Nn Nq Nr Ns Nt Nu Nv Nx Ny Oe Of Oi Ok Om On Pa Pd Pe Pf Pg Pz) Ir(Fp Fr Hq Hr Hu Hv Ih Ii Il In Io Ip Iq Is Iu Iv Jg Jl Jn Jo Jq Jr Js Jt Lh Lj Lw Lx Ly Lz Ma Mb Mc Me Mf Mg Mh Mi Mj Mm Mp Mr Ms Mt My Mz Nb Nc Nd Ne Ng Nh Ni Nk Nm Nn Nq Nr Ns Nt Nu Nx Ny Of Oh Oi Ok Om On Pa Pc Pd Pe Pf Pg Qa Qb Qc Qd) Et(Fr Hq Hr Hu Hv Hw Hx Il In Io Iq Jl Jm Jo Jp Jq Jr Lh Lu Lw Lx Ly Lz Ma Mc Me Mf Mg Mh Mi Mj Mk Ml Mn Mp Mr Ms Mt Mv Mx My Mz Na Nb Nd Ne Nf Ng Ni Nk Nl Nm Nn Nq Nr Nt Nu Nx Ny Oh Oi Ok Om On Pa Pc Pd Pe Pf Pg Po Qe) Nw(Fr Hq Hr Ii Ik Io Iu Jg Jh Jk Jl Jp Lh Lu Lv Lx Lz Ma Mb Mc Me Mf Mg Mi Mj Mk Ml Mm Mq Mr Mt Mu Mx Mz Na Nb Ne Nf Nh Ni Nj Nk Nl Nm Nq Nr Nv Oh Oi Om On Pa Pd Pe Pg Po Pz Qe) aA(Fp Fr Ii Iq Is Jg Jm Jp Lh Lw Lx Ma Me Mg Mm Mn Mz Nn Nr Ns Nt Nu Ny Oe Og On Pb Pf Pz Qa Qb Qe) Ke(bG De Gl Il Jv Kf Lh Mp Ne Nk Pb Ph Qy Rh Uh Us Uu Uv Vp Vs) Ih(Fr Ij Ip Is It Jg Jn Jp Jt Lj Ma Nm Nn Oe Og Ok On Pb Qd) Lj(It Iv Jg Jn Jp Jq Js Mi Mp Mw Nt Ok On) Mw(Ij Ip It Iv Jj Jn Js Jt Og Ok Qd) Is(Ij Ip It Jn Nm Oe Og Oz Pb) Qd(Ij Ik It Jj Oe Og Oz Pb) Jt(Fp Hr It Jj Jn Oe Pb Qb) On(It Jj My Oe Of Og Oy Pb) Jj(It Jn Js Nm Qa) Ok(Hr It Jn Og Pb) Ij(Hu Lz Oe Rt) Li(Fr Iu Nl Yd) Qa(Oe Og Pb) Js(It Og Pb) Vi(cV Sr) Pe(lX Zw) DeKq WmJi ItJp

Unconstrained panels with 2 analytes, where 1.0E-6 >= 'model p-value' > 1.0E-7. Contains 754 panels of 114,549 total panels evaluated. : Ke(aA Ad aE AF Aj An AO Ar aU aW aY Bb Bg bL bM Bn bO CH Cp Cs Ct CV Cw CX Dc Dd DG dH DI dJ DK dN Dp eC Ed Et Ez Fn fP Fw Gp Ha Hb Hc Hf Hq Hr Hu Hv Hx Ib Ic Id Ih Ii Ij Ik Im In Ir Iv Iz Jd Je Jf Jh Ji Jj Jk Jl Jm Jn Jo Jp Jq Jr Js Jt Ju Jy Kc Kg Ki Kj Kk Kl Kn Ko Kp Ky Kz Ld Li Lj Lu Lx Ly Mc Md Mg Mh Mi Mj Mk Ml Mm Mn Mr Ms Mu Mw My Mz Na Nd Nf Ng Ni Nj Nl Nn No Nr Ns Nt Nu Nv Nw Oa OE Of Og Oh Oi Ok ON Or Ou Ow Oy Oz Pa Pc Pd Pe Pf Pi Po Qa Qb Qc Qd Qe Qg Qh Ql Qm Qn Qt Qu Qv Qw Qx Qz Ra Rb Rc Rf Rg Ri Rj Rm Sr Ss St Tn To Tr Tt Tv Tz Ua Ub Uc Ud Ue Uf Ug Uk Ul Um Un Uo Up Ur Ut Vo Vt Yd Wm Tj) aA(Aa Hq Hr Hu Hv Hw Hx Ik Il In Io Iu Iv Jh Jj JK Jl Jo Jq Jr Lh Lu Lv Ly Lz Mb Mc Md Mf Mh Mi Mj Mk Ml Mp Mq Mr Ms Mt Mu Mv Mx My Na Nb Nc Nd Ne Nf Ng Nh Ni Nj Nk Nl Nq Nv Nx Of Oh Oi Om Oy Pa Pc Pd Pe Pg Po Uh) Ij(Fc Fp Fr Hc Hl Hr Hx Ik Ip Iq It Iv Jg Jn Jp Jq Jr Js Jt Lw Lx Ly Mi Mm Mn Mp Ms Mz Nc Nd Ng Nm Nn Ns Nt Ny Oh Ok On Ou Oz Pc Pf Qa Qb Qc Qe Rx Sh Uh Ur Uu Va Vh Vs Wb Wc We Zw Xa Ti Th) Ih(Fp Hv Hw Il In Iq Iv Jo Jq Jr Js Lh Lw Lx Lz Mf Mg Mh Mi Mm Mn Mp Mr Ms Mt Mz Nb Nd Ne Ni Nk Nq Nr Ns Nt Nu Nv Ny Oi Om Oy Oz Pa Pc Pe Pf Pg Po Qa Qb Qc) Lj(Fr Ii Ik In Ip Iq Jj Jo Jr Lh Lw Lx Ma Mg Mm Mn Mr Mt Mz Nb Nc Nd Nm Nn Nq Ns Nv Ny Oe Og Oh Om Oz Pa Pb Pc Pe Qa Qc Qd Vi) Is(Fp Fr Hr Hu Ik Jg Jj Jp Js Jt Lh Lw Lx Lz Ma Mm Mn Mp Ms My Mz Nc Nn Nr Ns Nt Nu Ny Of Ok On Oy Pc Pf Qa Qb Qc Qd) Js(Fp Fr Ik Ip Iv Jg Jn Jp Jt Lw Ma Mm Ms Mz Nh Nm Nn Ns Nt Nu Ny Oe Of Ok On Oy Oz Pc Qa Qc Qd) Qd(De Il Ip Iv Jg Jn Jp Jq Jt Ma Mi Mn Mz Nd Nm Nn Ns Nt Ny Ok On Oy Pc Wm) Ir(Hw Hx Jh Jk Jm Lu Lv Md Mk Ml Mq Mu Mv Mx Na Nf Nj Nl Nv Po Pz Qe) Jt(Fp Fr Ik Lz Ms My Mz Ng Nn Ns Ny Of Ok On Oy Oz Pf Qa Qc Qe) Uh(bN Cu Dc Hv Im It Iv Ji Jn Jq Jr Kd Kq Lw Ml Na No Nt Qa Ra Sr Up) Mw(Fp Ik Iq Jp Jq Jr Lz Mi Mz Nt Ny On Oz Pb Qa Qc Sh Wf) Et(Hx Ii Iu Jg Jh Jk Lv Mb Md Mm Mq Mu Nh Nj Nv Pz) Iv(Fr Hr Ip It Jg Jn Jp Ma Nm Nn Ny Ok On Pb Qa Qb) It(Fr Ip Jg Jn Jq Lx Ma Mn Mz Nn Ny Og Qa Qc) Jn(Fr Ip Jp Mm Nn Nt Oe Og On Pb Qa) Ok(Ip Jj Nn Ny Oe Of Oz Qa Qb Qc) Qa(Ik Ip Jg Jq Nm Ns Oy Oz) Jj(Ii Ip Jg Jm Nn Nt Ny Qb) Og(Ip Jg Nm Nn Ny Om Qb Qe) Pe(Fc nI Ru Rx Va Vi Wf Yd) No(Jh Ou Pz Zw Wm Ti Th) On(Hu Ip Ms Ng Ns Oz Qc) Aa(Ik Iu Mm Ng Nm Oh) Li(Dr Du Vi Th) Im(Eq Hb Ou) Ed(Ru Xa) Nn(Eq Pb) Va(Ps Sr) nI(ml nK) WmNw TiNb FrPb JrjK KqUu RxOa LdLp VtbN Unconstrained panels with 2 analytes, where 1.0E-5 >= 'model p-value' > 1.0E-6. Contains 1,570 panels of 114,549 total panels evaluated. : Ke(aC aD aG aH aI aJ aK AL aM aN AP aQ aR AS aV Aw AX aZ BA bB BC bE bF bH bI bJ Bo bP bQ bR bS bU bV bW bX bZ cA cB cC cD cE cF cG cI cJ cK cL cM cN CO cP CQ cR cS cT CU cW cY cZ dA DB dC dD dE dF DL dM DR EF Fa Fb Fp Fr Fy gL gP hB hC hF hG Hw iA iH iJ IO IP Iq Is It Iu Jg Kd KQ KR KS Kx Lv Lw Lz Ma Mb Me Mf Mq Mt Mv Mx Nb Nc Nh Nm Nq nW NY oF oH oK Om pF Pg Pj Pk Pz Ru Rx Va Vi Vu Vv Ti Th) Ij(aF Aj Ao aW aY Bb Bg bN bO cB Ch Ct De Dr Du Eq Fd Fi fR Gb Gh Gn Hb Ho Hp Hq Hv Hw Ib Ii Il In Io Iu Iz Jh Jk Jl Jm Jo Ju Jv Ki Kq Ld Lh Lp Lt Lu Lv Ma Mb Mc Md Me Mf Mg Mh Mj Mk Ml Mq Mr Mt Mu Mv Mx Na Nb Ne Nf Nh Ni Nj Nk Nl Nq Nr Nu Nv Nx Oi Om Op Ow Pa Pd Pe Pg Po Ps Pz Qw Ru Rv Ry Rz Sf Si Sj Us Uw Ux Uy Uz Vb Vc Vi Vt Vw Vz Wd Wf Wg Wh Yd Yl Zx Ye Tm Tl) Qd(Bb Fp Fr Hb Hq Hr Hu Hv Hw Hx Ii In Io Iq Iu Jh JK Jl Jm Jo Jr jT Lh Lu Lv Lw Lx Ly Lz Mb Mc Md Me Mf Mg Mh Mj Mk Ml Mm Mp Mq Mr Ms Mt Mu Mv Mx My Na Nb Nc Ne Nf Ng Nh Ni Nj Nk Nl Nq Nr Nu Nv Nx Of Oh Oi Om Ou Pa Pd Pe Pf Pg Po Pz Qa Qb Qc Qe Ra Sr Uh) Qa(Fc Fp Fr Hb Hr Hu Hv Hw Ii Il In Io Iq Jl Jo Jp Jr Lh Lu Lw Lx Ly Lz Ma Mb Mc Me Mf Mg Mh Mi Mm Mn Mp Mr Ms Mt My Mz Nb Nc Nd Ne Ng Nh Nl Nk Nn Nq Nr Nt Nu Nx Ny Of Oh Oi Om On Ou Pa Pc Pd Pe Pf Pg Qb Qc Rt Rx Va Vs Wf Yd Zw) Jt(Aj Hq Hu Hv Hw Hx Ii Ik Il In Io Iq Iu Iv Jg Jh Jk Jl Jm Jq Jr Lh Lu Lv Lw Ly Ma Mb Mc Md Me Mf Mg Mh Mi Mj Mk Ml Mm Mn Mp Mq Mr Ms Mt Mu Mv Mx Na Nb Nc Nd Ne Nf Nh Ni Nj Nk Nl Nm Nq Nr Nt Nu Nv Nx Oh Oi Om Pa Pc Pd Pe Pg Po Pz Uh) Js(Hq Hr Hu Hv Hw Hx Ii Il In Io Iq Iu Jh JK Jl Jm Jo Jq Jr Lh Lu Lv Lx Ly Lz Mb Mc Md Me Mf Mg Mh Mi Mj Mk Ml Mm Mq Mr Mt Mu Mv Mx My Na Nb Nc Nd Ne Nf Ng Ni Nj Nk Nl Nq Nr Nv Nx Oh Oi Om Pa Pd Pe Pf Pg Po Pz Qb Qe Uh) Ok(Fp Fr Hq Hu Hv Hw Hx Ik Il In Io Iq Iu Jg Jh Jl Jm Jo Jp Jq Jr Lh Lu Lw Lx Ly Lz Ma Mb Mc Mf Mg Mh Mi Mm Mn Mp Mr Ms Mt Mx My Mz Nb Nc Nd Ng Ni Nk Nm Nq Nr Ns Nt Nu Nv Nx Oh Oi Om On Oy Pa Pc Pe Pf Pg Po Qe Uh) Is(Hq Hv Hw Hx Ii Il In Io Iq Iu Iv Jh Jk Jl Jm Jo Jq Jr jT Lu Lv Ly Mb Mc Md Me Mf Mg Mh Mi Mj Mk Ml Mq Mr Mt Mu Mv Mx Na Nb Nd Ne Nf Ng Nh Nl Nj Nk Nl Nq Nv Nx Oh Oi Om Ou Pa Pd Pe Pg Po Pz Qe Uh Va Yd) Uh(Ad aE aM As Bn Cp Cq Cw Dd Dr Et Fw Fy Hw Hx Id In Ir Jo Kg Kn Ko Kp Kr Li Me Mi Mt Mw Mz Nb Nf Ni Nk Nm Nn Nr Nw Ny Oh Om Ou Pb Pc Pf Pi Pk Qe Qy Rb Rf Ri Rj Tv Uc Ud Ul Un Ur Us Ut Vi Vp Vt Vv) On(Fp Fr Hq Hr Hv Hw Hx Ik In Iq Jg Jk Jm Jo Jp Jq Jr Lw Lx Ly Lz Ma Mc Md Me Mf Mg Mh Mi Mk Mm Mn Mp Mr Mt Mv Mx Mz Nc Nd Ne Ni Nk Nm Nn Nr Nt Nu Nv Nx Ny Oh Oi Pa Pc Pd Pe Pf Qb Qe) Lj(Fc Fp Gb Hq Hr Hu Hv Hw Hx Il Io Iu Jh Jk Jl Jm Lu Lv Ly Lz Mb Mc Md Me Mf Mh Mj Mk Ml Mq Ms Mu Mv Mx My Na Ne Nf Ng Nh Ni Nj Nk Nl Nr Nu Nx Of Oi Oy Pd Pf Pg Po Ps Pz Qb Qe Ti) Im(Aj De Dr Du Fc Fd Fi Gb Hl Ho Hp kP Lp Lt mF nI Op Ps Rt Ru Rv Rx Ry Rz Sf Si Sj Uu Uw Ux Uy Uz Va Vb Vh Vi Vs Vw Vz Wb Wc Wd We Wf Wg Wh Yd Yl Zw Zx Tm Tl Xa Ti Th) Jn(Fp Hv Hw Hx Il Iq Jg Jl Jo Jq Jr Lh Lw Lx Lz Ma Mi Mn Mp Mr Ms Mt Mx Mz Na Nb Nc Nd Nm Nq Nr Ns Nu Nv Ny Oh Om Oy Oz Pa Pc Pe Pf Pg Po Pz Qb Qc Qe Rt Rx Va Wf) Pe(Eq Fd Fi Gb Gh Ha Hl Ho Hp It kN kP Lp Lt mF Mw mZ nA nD nN Op Pb Ps Rt Rv Ry Rz Sf Sh Si Sj Uw Ux Uy Uz Vb Vc Vh Vw Vz Wb Wc Wd We Wg Wh Yl Zx Ye Tm Tl Xa) Mw(Bb Fr Hu Hv Hw In Jg Jl Jo Lh Lu Lw Lx Ma Mh Mm Mn Mp Mq Mr Ms Mt Mx My Na Nb Nc Nd Ng nl Nm Nn Nr Ns Nu Nv Oe Of Oh Om Ou Oy Pa Pc Pf Pg Po Qb Qe) Ih(Hq Hr Hu Hx Ii Ik Io Iu Jh Jk Jl Jm Lu Lv Ly Mb Mc Md Me Mj Mk Ml Mq Mu Mv Mx My Na Nc Nf Ng Nh Nj Nl Nx Of Oh Pd Pz Qe Rx Va) No(Bb Du Fc Fd Fi Gb Hb Ho Hp Ki Kl oN Ow Ps Qy Rt Ru Ry Rz Sh Si Ss Ur Uu Uy Va Vi Vs Wb Wc Wd We Wf Wh Yd Yl Zx Ye Tm Tl Xa) It(Fp Hv Iq Jl Jr Lh Lw Lz Mi Mm Mp Mr Mt Mx Nb Nd Nm Nq Nr Ns Nt Nu Nv Om Oz Pa Pb Pc Pf Po Qb Qe) Iv(Fp Iq Jj Jq Lh Lw Lx Lz Mm Mn Mp Mt Mz Nd Nr Nt Nu Nv Oe Of Og Om Oz Pc Pf Po Qc Qe Ru Vi Ti Th) Vi(aF aO Ar aY bF BG Bn CH Dk Ed Hc Jl Ld Mh Mq Nx Oa Of Ow Oz Qw

Figure 38 Continued

Rt Sh Ur Uu Va Vt Wf Yd) Li(bO Eq Fc Fi Gb Hp Lp lX mZ nl Ps Rt Ru Rx Rz Sh Ux Uy Uz Va Vs Wb Wc Wf Zw Xa Wm Ti) Ip(Fp Fr Iq Jg Jp Jq Lx Lz Ma Mi Mn Mz Nc Nn Nt Ny Oz Pb Pf Qb Qc) Jq(Fp Fr Jg Jj jO Jp Lx Lz Ma Nm Nn Nt Nu Ny Og Pb Qb Qc Qe Wm) Kq(Aj Bg bL bN CH Hb Hq lz Kl Lu Of Ou Oy Pb Ss Uv Yd) Pb(Fp Jg Jp Lh Lx Ma Mi Mz Nm Nt Nv Ny Pf Po Qb Qe) Jj(Fp Fr Jk Jp Lh Lx Ma Mm Mn Mz Nr Nv Om Po Qe) Nn(Fp Hu Iq Jp Jr Mz Ns Nt Oe Oy Oz Qb Qc Sh) Va(Ed Gc Ir Ji Lx Nb Nw Oa Ow Rm St Un Vq) Jg(Fp Jr Lz Mi My Mz Ng Ns Oe Oy Qb Qc) nl(Mt nC nH nL nN nT Oh Oz Pf Qc Qe) Qb(Bb Fr Jp Ma Mi Mz Nm Nt Oe Oz) Ny(Fp Iq Jp Lz Mi Mz Nt Oe Qc Rx) Og(Fp Fr li Jl Jp Lx Mz Nt Nv Po) Ji(bN jT Ou Qy Us Uu Uv Yd) Sr(bN Gd Hb Nw Ou Sh Uu Yd) Ed(Dr fR Gd Wd Ti) Lx(Fc Oe Wb Yd Zw) Nb(Of Rt Rx Wf Tl) Oz(Fr Jp Pf Ps Xa) Nm(Fp Lz Mz Qc) Bb(aA bN Ml) Mt(My mZ Yd) Wb(Ld Ow Pf) Jp(Fp Lz Nt) Jr(jQ jR jT) Nw(bN Qy Yd) Oa(Dr Gc Ti) Et(Aj Uu) Fr(Oe Oy) Mr(Ru Wf) Qc(Ma Nt) Rt(Cu Nr) Ow(Dr Yd) Ur(Ir Lp) FpMm MljV MzOf HbaA QeOe

Unconstrained panels with 2 analytes, where 1.0E-4 >= 'model p-value' > 1.0E-5. Contains 3,471 panels of 114,549 total panels evaluated. :
Vi(aA Ad Af Aj aM AN AP aS aU aW AX aZ Bb bC bE bJ bN Bo bW bZ cC cE CO cQ Cs Ct Cw CX cZ De dF Dg dK Dp DR EF Eq Et Ex Ez Fc FP Fr Fw Gb Gc Gd Gh GL GP HB hC hF hG Ho Hq Hr Hv Hw Hx iA Ib Ic IH iJ iO iP Ir Is It Iu IZ Jh Ji Jj Jk Jm Jn Jo Jp Js Jy Kc Kd Kg Ki Kj Kl kQ kR kS Kx Kz Lp Lu Lv Lx Lz Mf Mg Mi Mk Ml Mm Mn Mp Mr Mt Mu Mw Mx My Na Nb Nd Nf Nh Nk Nm Nn Nr Nt Nu Nv NW NY OE oF Og OH Oi OK Om ON Oy Pa Pb Pc Pd PF Ph Pj Po Qa Qb Qd Qe Qg Ql Qn Qu Qv Qx Qy Ra Rb Rc Ru Rv Rx Si Sj Ss St Tn Tz Ua Ue Uf Ug Uk Ul Um Un Up Us Uv Ux Uy Vb Vo Vp Vq Vs We Wh Zx Tl Xa Wm Ti Th) Ij(aC AD aE Af aG aH al aJ aK AL aM aO AP aQ AR AS aU aV Aw AX aZ BA bB BC bE bF bG bH bI bJ bL bM Bn Bo bP bQ bR bS bU bV bW bX bZ cA cC cD cE cF cG cH cI cJ cK cL cM cN CO CP CQ cR CS cT CU CV CW CX cY cZ dA DB DC DD dE dF DG dH DI dJ DK DL dM dN Dp dR Ed Ef Em Ez Fb Fn fP Fw Gc Gd Gl Gp Gz Ha Hf Ic Id iZ Jd Je Jf Jy Kc Kd Kf Kg Kj Kk Kl Kn Ko Kp Kr Ks Kx Ky Kz nl nW Oa oN Or pF Ph Pi Pj Pk Qg Qh Ql Qm Qn Qt Qu Qv Qx Qy Qz Ra Rb Rc Rf Rg Rh Ri Rj Rm Sr Ss St Tn To Tv Tz Ua Ub Uc Ud Ue Uf Ug Uk Ul Um Un Uo Up Ut Uv Vo Vp Wm Tj) Uh(Aa AF aH Aj aL An Ao aP Ar AW Ax aY aZ BA BB Bc BG bJ bL bM BO bV cB CH cM Co cQ Cs CT CV CX dB De dF dG dJ DK DL dM dN Dp Ed EF Ez Fb Fn Fp Fr gL Gp Ha Hb Hq Hr Hu Ib Ih Ii Ik Il Io Ip Iq Iu iZ Jf Jg Jh Jj Jk Jl Jm Jp Ju Jv Jy Kc Kf Ki Kj Kk Kx Kz Ld Lh Lj Lu Lv Lx Ly Lz Ma Mb Mc Md Mf Mg Mj Mk Mm Mn Mq Mr Ms Mu Mv Mx My Nc Nd Ne Ng Nh Nj Nl Nq Ns Nu Nv Nx Oa OE Of Og Oi On Or Ow Oy Oz Pa Pc Pd Pg Ph Pj Po Pz Qb Qc Qg Qh Ql Qm Qn Qt Qu Qv Qw Qx Rc Rg Rh Rm St Tn To Tr Tt Tz Ua Ub Ue Uf Ug Uk Um Uo Uu Uv Vo Vs Vu Xa Wm) Kq(AA Ad aE AF Ao AW aY Ba BC bF bG Bn bO bS bW bZ cA cG Co cQ Cs Ct cV CW Cx DG dH dJ DK dN Dp Dr eC Ed Ef Eq Et Ex fP Fr Fw Gl Gp Hc Hr Hu Hv Ib Ih Im In Ir Is It Iv Jf Jh Ji Jj Jk Jl Jm Jn Jo Jq Jr Js Jv Kc Kd Kf Kg Ki Kj Kz Ld Lh Li Lj Md Mg Ml Mm Mu Mw Mx My Mz Na Nd Ne Ng Nk No Nr Ns Nv NW Nx Oa OE OH Oi ON Or Ow Oz Pe pF Pg Ph Pj Pk Qa Qb Qc Qd Qn Qt Qw Qy Rf Rg Rt Ru Sh Sr Tn Tr Tv Tz Ua Ur Us Ut Ux Va Vo Vp Vs Vt Wf Xa) Im(Ad aE AF aH aI aJ aK AL aM AN Ao aP aQ Ar As aU aV aW aX aY aZ BA Bb BG bJ bL bM BN bO bP bS bZ cB cD cE CH cN Cp Cq Cs CT Cu CV Cw CX cY dA DB Dc Dd Dg dH Di dJ DK Dl Dp Em Fn fR Gc Gd Gh Gn Gz Hc Id iJ iP Ju Jv Jy kC Kd kG Kl Kl KN Ko Ld lX mI mM mP mY mZ nA nC nD nH nK nM nN nT oO oP oQ Ow Pi Pj Pk Qn Qt Qv Qw Qy Ra Rb Rc Rf Ri Rj Sr Ss Tv Tz Ua Un Up Ur Us Vc Vp Vq Vt Wm) No(aF Aj aK aQ bN bO CH cX De dG dH Dp Ed Eq Ez Fa Fb Fn fP Gh Gp Gz Ha hB Hc Hf hG Hl iA Ib Ic Id iH iJ iP Iz Jd Je Jf jK Ju Jv Jy Kc Kd Kf Kg Kj Kk Kn Ko KP Kr KS Kx Ky Kz Ld Lp Lt lX nI nW Oa oE oH Op Or pF Ph Pi Pj Pk Qg Qh Ql Qm Qn Qt Qu Qv Qw Qx Qz Ra Rb Rc Rf Rg Rh Ri Rj Rm Rv Sf Sj Sr St Tn To Tv Tz Ua Ub Uc Ud Ue Uf Ug Uk Ul Um Un Uo Up Us Ut Uv Uw Ux Uz Vb Vc Vh Vo Vp Vt Vv Vw Vz Wg) Qd(AD aE Aj aN aQ aW Ba bM bN bO bP cB cH cT cX dB Dp Dr Ed Ez Fn GP Gz Ha Hc Hf Id iJ iP Iz JD Jf jO jQ jR Ju Jv Jy Kc Kd Kg Ki Kj Kk Kl Kn Ko Kp Kr kS Kx Ky Kz Ld lK lN mZ nK Oa oE oH Or Ow Pi Pj Pk Qg Qh Ql Qm Qn Qt Qu Qv Qw Qx Qy Qz Rb Rc Rf Rg Rh Ri Rj Rm Ru Ss St Tr Tt Tv Tz Ua Ub Uc Ud Ue Uf Ug Uk Ul Um Un Uo Up Ur Us Ut Uu Uv Va Vo Vp Vs Vt Yd Ti Th) Ji(aD AF Aj aN aW aY Bb Bg bM bO cB CH cV cX De Dp eC Ed Ez Fb Fn Fw Gl Gp Ha Hb Hc iC jD jE jG jH jK jO jP jQ jR Ju Jv jY Kc Kd Kf Ki Kj Kl Ko Ld lK lN nI Oa oE Ow Qg Qh Qn Qt Qu Qv Qw Qx Qz Ra Rb Rc Rf Rg Rh Ri Rj Rm Ru Sr Ss St Tn To Tr Tt Tv Tz Ua Ub Uc Ud Ue Uf Ug Uk Ul Um Un Uo Up Ur Ut Vo Vp Vs Vt Wb Ti Th) Qa(Bb Du Eq Fd Fi Gb Gh Gz Hc Hl Ho Hp Hq Hx Iu Jh Jk Jm Ki Ld Lp Lt Lv lX Md mF Mj Mk Ml Mq Mu Mv Mx mZ Na Nf Nj Nl Nv Op Or Ow Pj Po Ps Pz Qe Qw Qy Rf Ru Rv Ry Rz Sf Sh Si Sj Sr Ur Us Uu Uw Ux Uy Uz Vb Vc Vh Vp Vt Vw Vz Wb Wc Wd We Wg Wh Yl Zx Ye Tm Tl Xa Wm Ti Th) Nw(Ad aE AF aH Aj aO aQ Ar As aW Bb BG bM bO cB CH cN Cp Cq Cu cV Cw CX Dc Dd Dc dH Di dK Dp Ed Ez Fn Id jH jI jK Ju Jv Jy Kd Kg Kz Lp Oa Ou Pi Qn Qw Ra Rf Rg Rh Ri Rj Ru Rx St Tv Tz Uc Ud Ue Uf Ug Ul Un Up Ur Us Ut Uu Uv Vp Vt Xa Ti Th) Iv(Bb Gb Hb Hq Hu Hv Hw Hx Ii Ik Il In Io Iu Jh Jk Jl Jm Jo Jr Lu Lv Ly Mb Mc Md Me Mf Mg Mh Ml Mj Mk Ml Mq Mr Ms Mu Mv Mx My mZ Na Nb Nc Ne Nf Ng Nh Nl Nj Nk Nl nN Nq Ns Nx Oh Oi Oy Pa Pd Pe Pg Ps Pz Rf Rt Rx Si Ur Uw Uy Va Vb Vc Wc Wf Xa) Sr(aA aE AF Aj aK aQ aU aY Bg CH dJ Dr Eq Et Fn fR Gp Hl Hq In Is Jj Jn Jq Jr Js Jv Ki Ld Li Lj Lt Ml Mw Mz Ne Nk Nt Oe Oi Op Ow Pb Pe Pj Ps Qb Qc Qt Qy Ra Rf Rt Ru Rv Rx Ry Sf Tz Ur Ux Uy Uz Vb Vh Vt Vz Wb Wd We Wf Zw Tl Xa Ti Th) Pe(Bb bN Dr Em Fp Fr Gc Gd Gn Gz Hb Ip Jg Jj Jp Jq kC kE kF kG kI kK kO lW Lx lY Ma mE mH mI mM Mn mP mS mT mU mW mY Mz nB nC nF nH nJ nK nL NM Nn nO nR NT nU Ny Og oN Ou Ow Oz pF Pj Qb Qc Qe Qy Rf Rg Ur Uu Vs Vt Wm Ti Th) Li(Aj Bb bN Dc De dH Dp Em eP Fd Gc Gd Gh Gn Hb Hl Ho Jy kC Kd kE kF kG Ki Kl kN kP Lt mF mI mM mW nA nC nD nH nK nL nN Op Ou Qn Qy Rf Rg Rv Ry Sf Si Sj Tv Tz Un Ur Us Uu Uw Vb Vc Vh Vt Vw Vz Wd We Wg Wh Yl Zx Ye Tm Tl) Nn(Fd Fr Gb Hb Hq Hr Hv Hw Ii Ik Il In Io Jg Jl Jm Jo Kd Lh Lp Lu Lw Lx Ly Lz Ma Mc Me Mf Mh Mi Mm Mn Mp Mr Ms Mt Mv Mx My mZ Na Nb Nc Nd Ne Ng Nl Nk Nm Nr Nu Nv Ny Of Oh Oi Om Pa Pc Pf Pg Po Ps Pz Qe Uz Wb Yd Xa) Mw(Ad Aj Ax aZ bA Bg bN CH cT Cu Cv Dc Dd De Dr Eq fR Gh Hb Hq Hr Hx Ii Il Io Iu Jh Jk Jm Kd Ki Ld Lv Ly Mb Mc Md Me Mf Mg Mj Mk Ml Mu Mv mZ Ne Nf Nh Ni Nj Nk Nl Nq Nx Oi Pd Ps Pz Ru Rx Uy Va Vt We Yd Yl Ye Xa Ti) Lx(Du Fd Fi Fp Fr Gb Ho Hp Hq Hv Hw Ik Iq Jg Jl Jp Jr kP Lh Lp Lw lX Lz Ma Mi Mn Mp Mr Mt Mz Nb Nc Nd nI Nm Ns Nt Ny Of Op Oy Oz Pa Pc Pf Ps Qb Qc Qe Rt Ru Rv Rx Ry Rz Sh Si Sj Uy Vw Vz Wc Wd We Wf Zx Xa) Ny(Fc Fr Hb Ho Hu Hv Hw Ik Il In Jg Jl Jo Jr Lh Lp Lw Ma Mh Mm Mn Mp Mr Ms Mt Mx Na Nb Nc Nd Ng Nm Nq Nr Ns Nu Of Oh Oy Oz Pa Pc Pf Pg Po Qb Qe Rt Ru Rz Sh Va Wd Wf Yd Ye Xa Ti Th) It(Bb Hb Hq Hr Hu Hw Hx Ii Ik Il In Io Iu Jh Jk Jm Jo Lu Lv Ly Mb Mc Md Me Mf Mg Mh Mj Mk Ml Mq Ms Mu Mv My Na Nc Ne Nf Ng Nh Ni Nj Nk Nl Nx Oe Of Oh Oi Oy Pd Pg Pz Rx Sh Ur Va) Nb(Bb Du Eq Fc Fd Fi fR Gb Gh Hl Ho Ip Jg Jp Lp My nI Nm Og On Oy Pb Ps Qb Ru Rv Ry Rz Sf Sh Si Sj Uw Ux Uy Uz Vb Vc Vh Vw Vz Wb Wc Wd We Wg Wh Yd Yl Zw Zx Ye Tm Xa Th) Jn(Bb Fc Fi Hb Hq Hr Hu Hx Ii In Io Iu Jh Jk Jm Lu Lv Ly Mb Mc Md Me Mf Mg Mh Mj Mk Ml Mq Mu Mv My Nc Nf Ng Nh Nl Nj Nk Nl Nx Of Oi Pd Ru Rv Rz Sh Ur Wd Yd Ye Ti) Jq(Bb Hb Hr iC Il Io Iq jD jE jK JL Jm jQ jR jT Lh lK lN Md Mh Mi Mm Mn Mp Mr Ms Mt Mx Mz Nc Nd Nq Nr Ns Nv Oe Of Ou Oy Oz Pa Pc Pf Pg Po Pz Qy Rf Rh Uf Ur Uu) Jr(Bb eD Fp Fr hA Hb hR hV hW hX iB iC Ip jD jE jF jG jH jI jL jM jO JP jU jV jY lK lL lM lN lO Lz Ma Mi Mm Mn Mp Mz nI Nm nN Nr Nt Nv Pb Pf Qb Qc Qe Rf Ur) Qe(Bb Fp Fr Hb Hv Ik Ip Iq Jg Jo Jp Lh Lw Lz Ma Mi Mm Mn Mp Mr Mt MZ Nc Nd Nm Nr Ns Nt Nu Oh Om Ou Oy Oz Pa Pc Pf Qb Qc Qy Rt Ru Rx Ur Va Yd Ti Th) Hb(bN cH Cu Dc dK Ed Et Fw Fy Hv Hw Id Ih Il In Ir Is Js Jt Kd Ld Lj Lw Mi Ml Mt Mu Mz Na Ni Nr Nt Oe Oh Pf Pi Qy Ra Rf Rj Ul Un Up Ut Va Vp Vt) Qb(Fp Hu Hv Hw Ik Il In Io Iq Jh Jl Jo Lh Lw Ly Lz Mg Mm Mn Mp Mr Ms Mt Mx Na Nc Nd Nl Nk Nr Ns Nu Nv Of

Figure 38 Continued

Oh Om Oy Pa Pc Pf Pg Po Pz Qc Va) Nt(Eq Fp Fr Gz Ik Io Iq Jg Jl Lw Ly Lz Ma Mi Mm Mn Mp Mt Mz Nc Nd Ne nl Nm Nr Ns Oe Of Om Oy Oz Pc Pf Po Rt Ru Sh Tz Ur Va Vb Vt Wf Yd Xa) Jp(Fr Hu Hv Hw In Iq Ju Jg Jl Jm Jo Lh Lw Ma Mh Mi Mm Mn Mp Mr Ms Mt Mx Mz Nc Nd Nm Nr Ns Nu Oe Of Oh Om Oy Pa Pc Pf Pg Po Qc) Oa(Du Et Fc Fd Fi Gb Gh Gn Hl Ho Hp Lp Lt Op Ps Rt Ru Rv Rz Sf Sh Si Sj Uw Uz Vh Vw Vz Wb Wd Wf Yd Yl Zw Zx Ye Tl Xa Th) Is(Bb cV hA iC jD jE jF jG jH jl jK jO jP jQ jR jU jV jY IK IL IM IN IO nK Pj Qy Rt Rx Sh Ur Us Uu Vs Vt Wb Wm Ti) Mz(Dp Fp Fr Gp Hr Hx Iq Lh Lw Lz Ma Md Mi Mm Mn Mp Mt My Nc nl Nr Ns Nu Nv Oe Ou Oy Oz Pc Pf Po Qc Qy Ur Us Wm) Ed(Em Et Fd Gb Gc Gn Hl Ho Lp Nk Ps Rt Rv Ry Rz Sh Si Uw Ux Uy Uz Vb Vc Vh Vw Wc We Wf Wg Wh Yl Zw Zx Tm Tl) Qc(Bb Fp Fr Hv Hw Ik Il Jj Jl Jo Ld Lh Lw Lz Mi Mm Mn Mp Mr Mt Mx nN Nr Ns Nu Nv Og Om Oz Pb Pc Pf Po Rf Vt) Jg(Fr Hu Hv Hw Ik Il In Iq Jl Lh Lw Mg Mh Mn Mp Mr Ms Mt Mx Nc Nd Nm Nr Nu Of Oh Oi Oz Pa Pc Pf Pg Po Uu) Xa(Af Ar aW aY Bo Cx Dr Fc Fw Jj Kd Ke Ld Lj Lz Mh Ml Mq Mt Nr Nx Oi Ow Pb Pf Po Qx Ru Rx Sh Un Va Vs Vt) Ip(Hv Hw Il In Io Jl Jo Lh Lw Mh Mm Mp Mr Ms Mt Mv Mx Nd Ni Nm Nq Nr Ns Nu Nv Oe Oh Om Oy Pa Pc Pg Po) Fp(Fr Ik Io Iq Jl Lh Lw Lz Ma Mi Mn Mp Mr Mt Nc Nd nl nN Ns Nu Nv Oe Oh Om Oz Pa Pc Pf Pg Pz Ti Th) Js(Bb bN hA iC jD jE jF jl jQ jR jT jV jY Ld IK IL IM IN nl Ou qT QY Rt Rx Ur Us Va Vs Vt Wc Wm) On(Ii Il Io Iu Jh Jl Lh Lu Lv Mb Mj Ml Mq Mu Na Nf Nh Nj Nl Nq Om Pg Po Pz Sh Uu Va Wf Yd Wm) Fr(Hu Hv Hw Ik In Iq Jm Lh Lw Lz Mh Mi Mn Mp Mr Mt Mx My Nc Nd Ng Nm Ns Nu Of Oh Pa Pc Pf) Et(aF Ax Bb Bg bM bN bO cB CH Cs Cu cV Dc De Dg iZ Kd Ki Kl Ld Rf Ss Tz Un Ur Vt Wm) Va(Cu Cw Dr Fw Hw Ii Iu Jh Jt Ld Lj Mi Mq Mt Na Nr Nu Nv Oh Om Pd Pf Po Ql Qy Si Tz Vt) Nm(Hv Hw Il Iq Jl Lh Lw Mh Mi Mn Mp Mr Mt Mx Nc Nd Nr Ns Nv Oe Of Oy Oz Pa Pf Pg Po) Ps(aF Ar aW cV CX Fw Kd Lz Mh Mk Ml Mq Mt Nr Nu Oe Oi Pf Qn Qx Qy Rx Us Uu Vo Yd) nI(aA Hw Ih Il Ir Jl kF kG Lj Lz Ma mF Mi Ml MP Mq mU Mx nB Nr NU oQ Pa Pb) Pf(Gb Ho Hp Iq Jj kN kP Lh Lp lX mF Ml Mn mZ nK nL nN Ns nT Og Oy Pc Pd Sh) Lj(Bb Fi Ho Hp Jy Qy Ru Rx Rz Si Uw Uz Vb Vh Vt Vw Wb Wc Wd We Wg Wh Zx Th) Oz(Dr Iq Jj Jl Lh Lp Lz Ma Ml Mn Mp Mr Mt nN Nr Nv Om Pg Po) Ok(Ii Jk Lv Md Me Mj Mk Ml Mq Mu Mv Na Ne Nf Nh Nj Nl Pd Pz) aA(aF aW bI bN cB cN cV cX dH jO jT Pj qY rB Rf Si Vt Wm Ti) Og(Il Iq Jk Jm Jo Lh Lw Ma Mg Mi Mm Mn Mr Mt Nr Nu Pa Pz) Ow(Em Eq Fc Fd Fi Gb Ho Hp Lp Ru Rx Sh Sj Uy Uz Wc Zw Ti) Jj(Bb Hv Il Io Iq jK Jl Jo Lz Mi Mp Mr Mt Nu Pg Pz Ut) Bb(Aj Ax bV Cs Cu Dc Hv Ih Ir Jt Ne Nj Oi Uu) Mt(Eq Gh Iq Lp Mn Oe Of Pb Sh Ux Uz Wb Wf Zw) Ke(Aa Ex Fc gW iZ Lp Rt Sh Vq Wb Wc We Wf tF) Ml(Fb Fi Ho jl jT jU IM Lp nC nH nN Rf Wb) Dr(Ez Jd Kc Kd Ld Qx Qy Ru Tz Uf Ut Vt) Po(Du Fc Ma Mn Ns Oe Of Ru Rx Wb Yd Zw) Ma(Hv Iq Lh Lw Lz Mi Mr mZ Ns Oe Oy) Mq(Eq Fd Lp mZ Ru Uy Uz Wb Wc Wf Ye) Rf(Aa Cu dJ Fw Gp Il Mi Na Qy Tz Vt) Pb(Ii Iq Jl Jo Lz Mm Mn Mr Nr Om Pg) Ut(Aj bN CH Ou Sh Ur Uu Wf Yd) Nr(Fc Iq Mi Rx Sh Vz Wb Wd Wf) Mn(Hv Iq Jl Lh Lz Mi Mr Ns Nu) Ld(Fi Ho Hp Na Ru Uy Wf Ye Th) Ir(jK Ou Qy Rx Us Uu Wf Wm) Lz(Ho Lp Mm nC nN Nv Om) Aa(Ax bN cB Cu CX) Ih(Fc Fi Gz jK Sh Ye) Fw(Nk Ru Sh Si Ti) Qy(CH Eq Un Vt) Om(Oe Of Oy Sh Yd) Ns(Mi Mp Nd Nv) Jh(Ch Eq Sh Wf) Qx(Fd Ho Lp Wb) Kd(bN Gp Ur Wf) Oh(Gb Ho mZ Wb) Un(bN cH Gp Ou) Iq(Ik Il Nv) Vt(Gp Ou Ur) mZ(cO Mp nN) Cu(Ne Ur) Fy(Rt Vs) Mi(Mm Rt) Jt(bN fR) Rx(Mr Na) Lh(Hr Of) Lp(Ar Mk) Nv(Oe Oy) jK(dM Lw) AdAj CsTh CxFd DcNe EqRz GcSh MhHo NhnN IdbN WbKx JlOe KzRu jIjT Unconstrained panels with 2 analytes, where 1.0E-3 >= 'model p-value' > 1.0E-4. Contains 8,927 panels of 114,549 total panels evaluated. :
Sr(Aa aC AD aG aH al aJ AL aM AN AO AP aR AS aV AW AX aZ BA BB BC BE bE bF bG bH bI bJ bL bM Bn BO bP bQ bR bS bU bV bW bX bZ cA cB cC cD cE cF cG cI cJ cK cL cM cN CO CP CQ cR CS CT CU CV CW CX cY cZ dA DB DC DD DE dF DG dH Dl DK DL dM dN Dp dR Du eC Ed EF Em Ex Ez Fb Fc Fd Fi FP Fr Fw Fy Gb Gc Gh GL Gn gP Gz Ha hB HC HF hG Ho Hp Hr Hu Hv Hw Hx iA Ib Ic Id IH Ii iJ Ik Il IO IP Iq Ir It Iu Iv IZ Jd Je Jf Jg Jh Jk Jl Jm Jo Jp Jt Ju Jy Kc Kf Kg Kj Kk Kl Kn Ko Kp kQ KR KS Kx Ky Kz Lh Lp Lu Lv Lw Lx Ly Lz Ma Mb Mc Md Me Mf Mg Mh Mi Mj Mk Mm Mn Mp Mq Mr Ms Mt Mu Mv Mx My Na Nb Nc Nd Nf Ng Nh Ni Nj Nl Nm Nn Nq Nt Ns Nu Nv nW Nx NY Oa oE OF Og OH OK Om ON Or Oy Oz Pa Pc Pd PF Pg Ph Pi Pk Po Pz Qe Qg Qh Ql Qm Qn Qu Qv Qw Qx Qz Rb Rc Rg Rh Ri Rj Rm Rz Si Sj Ss St Tn To Tr Tt Tv Ua Ub Uc Ud Ue Uf Ug Uk Ul Um Un Uo Up Us Ut Uv Uw Vc Vo Vp Vq Vs Vw Wc Wg Wh Yl Zx Ye Tm Wm Tj) Kq(aC aD aG aH al aJ aK AL aM AN aO AP aQ AR AS aU aV AX aZ bA BB bE bH bI bJ bM Bo bP bQ bR bU bV bX cB cC cD cE cF cI cJ cK cL cM cN cO CP Cq cR cS cT CU Cv cX cY cZ dA DB DC DD dE dF DI DL dM dR Du eF Em Ez Fa Fb Fc Fd Fi Fn Fp fR Fy Gb Gc Gd Gh gL Gn gP Gz Ha hB hC HF hG Hl Ho Hp Hw Hx iA Ic Id iH Ii iJ Ik Il IO IP Iq Iu iZ Jd Je Jg Jp Jt Ju Jy Kk Kn Ko Kp kQ KR KS Kx Ky Lp Lt Lv Lw Lx Ly Lz Ma Mb Mc Me Mf Mh Mi Mj Mk Mm Mn Mp Mq Mr Ms Mt Mv Nb Nc Nd Nf Ng Nh Ni Nj Nl Nm Nn Nq Nt Nu NY oF Og OK Om Op Pa Pc Pd Pf Pi Po Ps Pz Qe Qg Qh Ql Qm Qu Qv Qx Qz Ra Rb Rc Rh Ri Rj Rm Rv Rx Ry Rz Sf Si Sj St To Tt Ub Uc Ud Ue Uf Ug Uk Ul Um Un Uo Up Uw Uy Uz Vb Vc Vh Vi Vq Vv Vw Vz Wb Wc Wd We Wg Wh Yl Zw Zx Ye Tm Tl Wm Tj Ti Th tF) Li(aC AD aE AF aG aH al aJ aK AL aM AN AO AP aQ AR AS aU aV AW AX aY aZ BA bB BC bE bF BG bH bI bJ bL bM Bn Bo bP bQ bR bS bU bV bW bX bZ cA cB cC cD cE cF cG CH cI cJ cK cL cM cN CO CP CQ cR CS CT CU CV CW CX cY cZ dA DB dC DD dE dF DG Dl dJ DK DL dM dN dR dX Ed Ef eM Ez Fa Fb Fn fP fR Fw Fy Gl GP Ha hB HC Hf hG iA Ib Ic Id iH iJ iO iP IZ Jd Je Jf jl jK Ju Jv Kc Kf Kg kl Kj KK Kn KO Kp kQ KR KS Kx Ky Kz Ld lW IY mE mH mP mS mT mU mY nB nF nJ nM nO nR nT nU nW nY Oa oE oF oH oN oO oP Or Ow pF Ph Pi Pj Pk Qg Qh Ql Qm Qt Qu Qv Qw Qx Qz Ra Rb Rc Rh Ri Rj Rm Ss St Tn To Tt Ua Ub Uc Ud Ue Uf Ug Uk Ul Um Uo Up Ut Uv Vo Vp Vq Vu) Nw(aC aD aG al aJ aK AL aM AN Ao AP aR aS aU aV Aw AX aY aZ BA bB BC bE bF bH bI bJ bL Bn Bo bP bQ bR bS bU bV bW bX bZ cA cC cD cE cF cG cI cJ cK cL cM cN CO cP cQ cR CS CT cU Cv cW cY cZ dA DB dC dD dE dF DG dl dJ Dk DL dM dN DR Du eC Ef Eq Fa Fb Fc Fd Fi fP Fw Fy Gb Gh GL GP HA Hb Hc Hf Hl Ho Hp hW IB IC iJ IZ JD JE JF jG jL jM jO jP jQ jR jT jU jY Kc Kf Ki Kj Kk Kl Kn Ko Kp Kr Ks Kx Ky Ld IK IL IM IN IO Lt nl nN oE oN Op Or Ow pF Ph Pj Pk Ps Qg Qh Ql Qm Qt Qu Qv Qx Qz Rb Rc Rm Rt Rv Ry Rz Sf Sh Si Sj Ss Tn To Tr Tt Ua Ub Uk Um Uo Uw Ux Uy Uz Vb Vc Vh Vo Vs Vv Vw Vz Wb Wc Wd We Wf Wg Wh Yl Zw Zx Ye Tm Tl Tj) Qd(aC AF aG aH al aJ aK AL aM An AO AP AR AS aU aV Aw AX aY aZ bA bB BC bE bF BG bH bI bJ bL Bn Bo bQ bR bS bU bV bW bX bZ cA cC cD cE cF cG Ch cI cJ cK cL cM cN CO CP CQ cR CS Ct CU CV CW Cx cY cZ dA Db DC DD dE dF DG dH Dl dJ DK DL dM dN dR Du eC eD EF Eq Ex Fb Fc Fd Fi fP Fw Fy Gb Gc Gd Gh GL hA hB hC hF hG Hl Ho Hp hR hV hW hX iA IB IC iH iO iZ JE jF jG jH jl jL jM jP jU jV jY kE Kf kN kP kQ kR Ks IL IM IO Lp Lt lW lX mF ml nC nH nL nN nT nW nY oF oK oN Op pF Ph Ps qT qV qY Rt Rv Rx Ry Rz Sh Si Sj Tn To Uw Ux Uy Uz Vb Vc Vh Vq Vu Vv Vw Vz Wb Wc Wd We Wf Wg Wh Yl Zw Zx Ye Tm Tl Xa Tj) Xa(aA Ad aF aH Aj aM AN aO AP aR AS aU aX aZ Ba Bb bC bE bF BG bJ bM BN bP bQ bR bS bW cA cC cD cE CH CO Cp CQ CS Ct CU CV Cw cX DC De Dg Di dK Dp dR Du Em Eq Et Ex Ez Fd Fi FP Fy Gb Gc Gd Gh GL Gp Gz Ha HB Hc Hf Ho Hp Hu Hv Hw Hx Ib Ic Ih Ii Ik Il In Ir Is It IZ Jd Jh Ji Jl Jm Jn Jo Jr Js Jt Jv Kc Kg Ki Kj Kk Kl Kn Ko kR Kx Ky Kz Lh Lp Me Mf Mg Mi Mj Mk Mm Mp Mr Ms Mu Mv Mx Mz Na Nc Nf Ng Nh Ni Nk Nl Nq Ns Nu Nv OE Of Og Oh Ok Om On Or Ou Oy Pa Pc Pd Pg Ph Pj Pk Ps Qb Qc Qe Qg Ql Qn Qv Qw Qy Ra Rc Rf Rj Rm Rt Rz Sf Sj Ss St Tz Ub Uf Ul Uo Ur Us Ut Uu Uv Uy Vh Vo Vp Vq Vz Wb Wf Yd Yl Zx Ye Tl Wm Tj Ti Th) Ji(aC Ad aE aG aH al aJ aK AL aM An AO AP aQ AR AS aU aV Aw AX aY aZ BA bB BC bE bF bG bH bI bJ bL Bn Bo bP bQ bR bS bU bV bW bX bZ cA cC cD cE cF cG cI cJ cK cL cM cN CO CP CQ cR CS CT CU Cv cW Cx cY cZ dA DB DC DD dE dF DG dH DI dJ DK DL dM dN DR eD EF Ex Fa Fc Fi fP Fy Gb gL gP gW Gz hA hB hC HF hG Ho Hp hX iA IB Ic Id iH iJ iO iP IZ Jd Je JF jl jL jM jU jV Jy Kg Kk Kn Kp kQ KR KS Kx Ky Kz IL

Mb Mf Mh Mn Mw No Nw Oz Pb) Pb(AA Et Ih Ij In Ip Ir Is It Iv Jn Jq Js Jt Lw Mf Mw Mz Nd No Ns Nw Oe Ok) It(AA Et Ih Ip Ir Is Iv Jp Jq
Ly Mb Mf Mh Mw Nd Nk No Ns Nw Oe Oi Oz) Et(aA Hu Ih Ij Ip Ir Is Iv Jn Jo Mw My Ng Ns Oe Of Oi Oy Oz) Nw(aA Hu Ih Ir Iv Ly Mh Mv
Mw My Ng Ns Nx Oe Of Oi Oy Oz Pc) aA(Hu Ih Ij Ip Ir Jn Mh Mw Ns Oe Of Oi Oy Oz Qc) Ir(Hr Hu Lj Mh Mw Nk Ns Oe Of Oi Oy Oz)
Ih(Hu Ip Ly Mh Mw Nk Ns Oe Oi Oy Oz) Ij(Hr Hu Jo Ly My Ng Ns Oe Of Oy Oz) Is(Hr Hu Mw My Ns Oe Of Oy Oz) Mw(Hu Iv Ng Ns Oe
Oy) Hr(Iv Jq Jt Ok) Oe(Iv Jn Jq Jt) Oz(Aa Ip Iv Ns) Of(Iv Jt Nb) Oy(Aa Ip On) Nd(Hq Ns) AaQc JoJt} Nw{Pb(aA Et Fp Hv Hw Ih Ij In Ip Ir Is
It Iv Jj Jn Jo Jr Jt Lj Mw My No Ns Oe Og Ok Qa) Og(aA Et Ih Ij Il Ip Ir Is It Iv Jg Jm Jn Js Jt Lj Mw Nm No Ns Oz Pc) aA(Et Hu Hv Ih Ij Ip Ir
It Jm Jn Lj Md Mw My Ns Nv Oe Of Oy Oz Pc) It(Et Hx Ik Ir Iv Jj Lj Ly Mh Mw My Nd No Ns Oe Of Oy Oz Pc) Oz(Ih Ip Ir Is Iv Jj Lj Mv
Mw My No Ns Oe Of Oy) My(Et Ih Ij Il In Ir Jg Jh Jn Jt Mw Nb) Oe(Et Ih Ij Ir Is Iv Jn Jt Lj Mw) Of(Ij In Ir Iv Jn Jo Jt Mw Nb) Ir(Jj Mh Mw Ns
Nx Oy) Jt(Hr Lj Ns Nx Oy) Mw(Hu Jj Lj Oy) Ih(Et Jj Lj Oy) Ij(Hu Jj Lj Oy) Ns(Jn Nd) Hr(Hw Iv) EtLj NdHq HxIv JnOy} Ij{Og(aA Et Fr Ih Ik Ip Iq Ir Is It Jg Jj Jm Jn Jp Jt Lj Lw Me Mi Mm Mp Mt Mw Nd Nm Nn No Ns Of Ok On Oz Pa Pb Pc Qc) aA(Et Hr Hu Hx Ik Ip Ir It Jj Jk Lj Ly Md Me Mk Ms Mw My Nm Ns Nv Oe Of Oy Oz Pb Qc) Oy(Et Jg Jj Lx Mi Mp Mt Mw Nn No On Pa Pb) Jj(Et Ir It Lj Mw My No Oe Of Pb) Of(Et Jg Mi Mt Mw Nb No On) Et(Hu Lj My Ng Oe Pb) My(Jg Mi Mt No On) Oe(Ih Ir Lj No Pb) Pb(Ir Lj Mw No) fR(Ne Nh) UhbN} Et{It(aA Ih Ik Ip Ir Jj Jn Jo Lj Mw Nd Ng Nk No Ns Oe Of Og Oy Oz Pb Qc) aA(Ih Ip Ir Jm Jn Js Lj Mw Ns Oe Of Og Oy Oz Pb Pc Qb Qc) Oe(Fp Ih Il Ir Is Iv Jn Js Lj Mw No Pb Qa Qb) Lj(Ih Jj Jn Mi Mw Nc Ns Of Og Oy Oz Pb) Og(Ih Ir Is Jm Jn Js Mw No) Pb(Ih Ir Is Jn Js Mw No Qb) Mw(Ih Ir Jj Of Oy) No(Ih Ns Oy Oz) Ir(Jj Of Oy Oz) Ih(Jj Oy) NsNd NbOf HrIv JjJn} aA{It(Ip Ir Jg Lj Mn Mw Nm No Og Oz Pb) Ip(Ir Jn Lj Mw Oe Og Oz Pb) Lj(Jg Mg Mw Nm Oe Oz Pb) Ir(Mw Oe Og Oz Pb) Oe(Ih Mw Nm) Pb(Jn No) NmOg} bN{Uh(As Cp Cq Cu Cw Dc Hv Hw Id In It Jn Jq Jr Kd Ke Kq Lw Ml Na Nb Om Pi Pk Qa Ra Up Vp Vt) Ke(Nx Uv)} No{Pb(Ih Ip Ir Is It Jj Jn Jt Mw Ns Oe) It(Ik Jj Ns Og Oz) Ns(Nd Oz) Ih(Jj Oe) Ir(Oe Og) IpOz} Ir{Oe(Ik Jg Jt Mw Nn On Oz Pb) Og(Ip Jg Jt Mn Mw Nm Pb) Mw(Ik Jj Oy Pb)} Aa{It(Jj Mw Qc) QcOg} Mw{Jj(Ih It) IsOg} Og{IhJg JtLj} DeKqUh

Constrained panels with 3 analytes, where 1.0E-9 >= 'model p-value' > 1.0E-10. Contains 1,722 panels of 15,247,928 total panels evaluated. : Nw{Oy(Aa Et Fp Hv Il In Ip Is Iv Jg Jh Jm Jo Js Lj Lw Mh Mi Ms My Nb Nc Nd Nn No Nq Ns Nt Oe Of On Pc Pf Qa) Ij(Et Hr Hx Ih Ik Jh Jk Ly Md Mh Ml Ms Mv Mw Nc Ng Ns Nv Nx Ny Oz) Of(Et Hv Hw Ih Il Is Jm Jq Jr Js Mi Mz Nc No Ns Nt Ok Om Pc Pe Qa) Jn(Et Hr Hu Iv Ji Jj Jt Md Mh Ms Mv Mw Ng No Nx Ny Om Oz Pc) Ns(Et Hw Hx Ih Is Iv Ji Jr Lj Mh Mp Mw My Nc Nn No Oe Pc) My(Ip Is Iv Jm Js Mg Mi Mt Nc Nn No Nq Nt Nu Oe On Pc) Jj(Et Il Ip Is Iv Ji Jm Js Jt Lj Mh Mn Nc No Nu Pc Qa) Jt(Hu Hx Ih Jo Md Mh Ms Mv Mw Ng Nv Ny Om Oz) Oe(Fp Il Iq Jm Js Ly Nc No Nt Nu Pc Qa Qb) Mw(Aa Et Ih Ip Is Iv Mh Ms Mv Ng Pc) Nx(Et Hv Hw Ih Is Iv Jo Jq Jr Js Qa) Oz(Aa Et Fp Hu Hx Ji Md Mh Ms Ng Ny) Ji(Hr Hx Mh Ml Mv Nv Ny Om Pc) Hu(Et Is Iv Mh Nn No Nt Pc) Iv(Et Ih Lj Md Mh Nv Ny) In(Hr Hx Md Ny Og Om) Is(Et Hx Lj Ms Nv Pc) No(Mh Ms Nv Pc Po) Og(Lw Mg Nn Nt Nu) Aa(It Pb Pc Qc) Mh(Ih Js Lj Pc) Hr(Hv Ir Jo Qa) Nv(Ih Ir Mi Nt) Md(Hv Hw Qa) Nc(Et Lj Nk) Hv(Ny Om) Lj(Mp Pc) EtNg MsIh IrQc} Ji{Jq(Hr Ik Ip Iv Jj Jm Jr Js Jt Ma Md Mh Nk Nn Ny Of Ok Oy Oz Pc Qc Qd) Oz(Fr Hr Ij Ip Is Iv Jj Jn Jp Jt Ma Md Ms My Nm Ns Of Oy Pf Qd) Jj(Hr Il Ip Is Iv Jg Jm Jt Ma Md Ms My Nd Nm Nn Nu Ny Of) Oe(Fr Ik Il Ip Iv Jg Jp Ma Nd Nm Nn Ns Nu Ny Ok Pc Qa Qd) Oy(Fr Ih Ip Jh Jn Jp Jt Ma Nd Nk Nm Nn Nt Nu Ny Pa Pf Qd) Ns(Hr Ih Ij Ip Is Iv Jg Jn Jp Jt Ma Ms Nm Nn Nu Ny) My(Fr Hr Ih In Ip Jh Jp Ma Mt Nk Nm Nn Nt Ny Pa Pc) Nk(Ih Ij Iv Jm Jn Jp Jt Md Ms Nu Ny Of Qa) Md(Ih Ij Ip Jn Jp Ma Mf Nd Nm Nu Pa) Hr(Fr Hw Ih Mf Mr Nm Nt Nu Ny Pa) Ik(Fp Ij Jq Iv Jg Lz Ma Nt Pf Qd) Of(Ih In Mf Nb Nn Nt Ny On Pf) Ij(Hu Hx Jo Mh Ml Mv Ng Ny) Ms(Ip Is Jt Nd Nm Nn Nu) Mf(Hx Jm Jt Me Mh Ny) Om(Fr Il Jg Jp Ma Nn) Pa(Hx Ii Mh Mk Ny Po) Mv(Fr Il Jg Ma) Nt(Hx Nv Po) Ih(Ip Ma Nm) Ny(Jp Ma Pc) Nd(Pd Pg) Ng(Jg Jt) Hx(Il Iv) Jo(Jt Nm) Pc(Ip Pf) NuMh QcQd UhbN PdPf} Et{Pb(Fp Hv Hw Il In Ip Iv Jj Jq Jt Lz Mh Mr Mz Nc Nd Nn Nr Ns Nt Of Og Ok Pe Pf Pg Qa Qc Qd Qe) Oe(Ip Jj Jm Jq Jt Mz Nc Nd Nn Nr Ns Nt On Oy Oz Pc Pe Qc Qd Qe) Ij(Hr Ih Ik Is Jh Jn Jo Lz Ms Mv Mw Nc Nd No Ns Nx Oz Qc) Og(Fp Il In Ip Iv Jq Jt Mz Nb Nn Ns On Oz Qa Qb Qc Qd Qe) Of(Fp Ih Il In Ip Is Iv Jn Jq Js Jt Mz No Om Oz Qa Qb) Oy(Fp Il Ip Is Iv Jm Jn Js Nc On Pe Pf Pg Qa Qb Qc Qd) Mw(Fp Hu Ip Is Iv Jn Jq Js Ms My Nc Ng No Ns Oz Qc) Jj(Fp Il Ip Is Iv Jm Js Jt Nc Nn No Oz Qa Qb Qc) Jn(Ih Ip Is Iv Ms My Nc Nd Ng No Ns Oz Qc) Ih(Ip Iv My Ng Ns Nx Oi Oz Qc) Ns(Fp Ir Is Iv Js Qb Qc) My(Ir Is Js Nb No On Qb) Oz(Fp Ip Is Jv Js Qb Qd) No(Hu Ip Is Nc Ng) Js(Ip Jo Ng Nx) Iv(Hx Nd Qc) Hr(Ir Is) Ik(Fp Qd) Pd(Pe Pf) MzaA NdHq HuIs JoJt} Li{Oy(Il In Iv Jg Jh Jn Jp Jq Js Jt Lw Mf Mi Mz Nb Nd No Ns Ok Pe Pf Pg Qb) Ip(Aa Hu Is Iv Jn Jq Ly Mf Mw My Nc No Ns Oe Of Pc) Oe(Jp Js Lw Mb Mf Mz Nd No Ns Ok On Oz Pc Qa Qb) Of(Aa Hv In Jn Jq Js Lw Mi Mw Mz Ok Om On Qa) Hu(Iv Jh Jn Jq Js Jt Lw Mf Nd No Nq On Oz) Ns(Iv Jn Jp Jq Js Jt Lw Ly Mf Nc No On) Oz(Jl Jn Jp Jq Js Jt Mw Nd No Oi Ok) Oi(Ij Is Jn Jq Js Jt Lw Mw Mz) My(In Jg Jq Jt Mw Mz Nb On) Hr(Aa Hv Hw In Jn Jr Mz Qa) Iv(Hx Jn Jo Lw Ly Mh Mk Nd) Aa(Jj Md Mw Nx Og) Ly(Js Mi Nc No Nt) Ng(Jg Jt Lw Nd On) Mh(Is Mz No Ok) Jq(Md Mw Nd Nx) Lz(Iq Js Qc) Ij(Jk Mv Nd) Th(aA No) Lw(Mf Pc) Is(Mj Pc) Jn(Mw Nd) Jo(Js Ok) PoNo TibM MfJs MkPa NcNk ImlX QbJt PdPe} aA{It(Fr Ih Jj Jn Jp Js Jt Ma Me Mg Mm Mz Nk Nn Ns Ny Oe Ok On Pc Qc) Jt(Hr Ih Ip Ir Jj Jn Lj Mw Mz Ns Oe Of Og Oz Pb Qb Qc) Pb(Ih Jg Js Ma Mn Mw Mz Nm Ny Oe Ok On Qa Qb Qc Qd) Nm(Ih Ip Ir Jj Jn Js Mw Mz Ns Of Oy Oz Qb Qc) Oe(Is Jg Jm Jn Js Nn No Ny Ok On Qa Qb Qd) Mw(Hu Ih Jj Jn Js No Ns Of Og Oy Oz Qc) Ir(Hr Jg Jj Jn Lj Ma Me Mn Nk No Oy) Ih(Ip Jg Jj Lj Ma Me No Og Oz Qc) Ip(Jg Jj Js Mn No Oy Pc Qb Qc) Lj(Jn Lw Ma Me Mm Mn Ns Og Qc) Jn(Me Mz No Ns Og Oz Qc) Oz(Js Mn No Ok Qc Qd) Og(Jg Jm Js No Qc) Ti(Ij Im Oa) Jg(Hu My Ns) No(Ns Oy) GcNe PflX} Ij{Oy(Fr Ih Ik Ip Iq Ir Is Iv Jh Jn Jp Jq Jt Lh Lj Lz Mm Mn Mr Mz Nb Nd Nq Nt Oc Ok Oz Pc Pe Pf Pg Po Qc) Pb(Aa Fp Fr Hu Ih Ik Ip Iq Is It Iv Jn Jp Jt Lh Lx Lz Ma Mi Mm Mp Ms My Nd Nn Of Ok On Pf Qa Qd) Jj(Aa Hr Hu Hx Ih Ik Ip Iq Is Jm Jn Jt Md Mh Ml Mm Mn Mp Ms Nc Nd Nm Nn Ny Oz Qc) Of(Fr Hu Ih Ir Is Iv Jp Jt Lh Lx Lz Mm Mp Mr Mz Nd Nn Nt Ok Pa Pe Po) My(Fr Ih Is Jp Jt Lx Mm Mp Mw Nb Nn Nq Ok Pa) Lj(Hu Ih Ik Is Jp Jt Mi Mm Mp Mw Nn No) No(Hr Hu Ih Ik Ns Oz) Oe(Is Jt Mw Qd) Mw(Hu Ih) Hr(Iv Ok) ThUr NnHu IkQd KebN} Aa{Mw(Ih Ip Ir Iv Jj Js Lu Lz Mq Mr Oe Of Og Oi Oy Oz Pb Pc Qc) Oy(Ip Ir It Js Lx Lz Mr Mt Nn No Pe Pf Pg Qa Qb Qc Qe) Pb(Fp Ih Ip Ir It Js Lx Lz Mq Mr Mt Mu Nn No Pf Qa Qb) Qc(Ih Iv Jj Lz Mq Mr Mu Nk Nn Oe Of Oi Oz) Oz(Fp Ip It Js Lz Mr Mt No Pf Qa Qb) Og(Fp It Jm Js Qa Qb Qd Qe) Qa(Jj Nk Nx Oe Of Oi) Js(Hr Ip Jj Mq Oe Of) Qb(Jj Mu Nk Nx Oe) Lz(Ip It Jm Pc) Ip(It Jj Pc) Ih(Jj Oe) It(Jp Mq) FpHr MyJh IvJj QeNx} Ir{Pb(Fr Ip Is It Jg Jj Jn Jp Jt Lj Ma Mn Mp Nk Nm Nn Ok On Pf) Oe(Fr Ih Io Is Jj Jn Jp Lj Ma Mb Mm Mn Nd Nm Nu Og Ok) Og(Is It Jh Jp Lw Ma Me Mg Mm Nn Ns Ok Om On Oz Pc) Jj(Ih Ip It Jg Jt Ma Mn Nm Nn No On Oz) Mw(Hr Hu It My Nk No Ns Of Oz) Oy(Jh Jp Ma Mn No On) No(It Ns Oz) Hr(Iv Jt Ok) Ik(Lj Qd) NsNd MyJg IpOz UhbN} No{Og(Ih Ip Is Jg Jm Jn Jt Mw Nm Ns Oz Pb) Ns(Ih Ip Is Jj Jn Jt Mw Nc Oe Oy) Jj(Ip Is Jn Js Jt Mw Nm Oz) It(Ip Is Mw Nd Nk Oe Oy) Oz(Ih Is Iv Jn Jt Mw Oe) Oy(Ih Ip Is Jn Jt Mw) Oe(Ip Is Jn Jt Mw) Th(Kc Kd Ke Ld) Ti(Bo Kd Nb) Ih(Ip Mw Nk) Pb(Iv Lw Ok) Hr(Iv Jt) MwIp NdHq IkQd JtOf KeVs} Jj{It(Fr Ih Ii Ip Jg Jn Jp Js Jt Lj Mn Nm Nn Ok On) Ih(Ip Jg Js Jt Lj Ma Nm Nn Oe Pb) Mw(Ip Is Iv Jn Js Jt Lj Nm Nt) Jt(Ip Jn Lj Qb) On(Lj Pb)} Ke{bN(Af bG Bn CH De Il Jv Lh Ne Nk Pb Ph Qc Qy) Nx(aW bL De Il Pb Qy Uu Vp) De(Ez Im Kq Qy) Lh(Ed Nr Rh) Il(Ph Vp) Im(Pb Vs) Qy(Bg Ch) NnVs} Og{Mw(Ih Ip It Iv Jg Jn Js Jt Lj) Ih(Ip Jt Lj Ma Nm Ok On) Jg(Ip Is It Js Lj Qb) Jt(Fp Ip It Jn Pb Qb) Is(Ip It Lj Nm) It(Ok On) Lj(Mg On)} bN{Uh(Ad aM Bn Dd Iv Jt Kn Kp Kr Mz Nf Ny Pb Rb Rj Sr Tv Uc Un Vs) DeKq} Oe{Ih(Fr Is Jg Jt Lj Ma Mw Nm Nn Ok On) Is(Jg Lj Mw Pb) Jt(Lj Qb) On(Lj Pb) QaPb} Mw{Pb(Ip Is Iv

Figure 38 Continued

Jn Ok) Of(Is Iv Jt Nb) Lj(Ih Is Jt) HrIv IkQd IsIt} Pb{Is(Fr Ip It Lj Ma) Lj(Jt Ok On) It(Ok On)} IX{Pe(Im Lv IW mZ Nb) LzIm} Ti{Nb(Ar Of) Im(Ch KI)} Jt{Hr(Ih Lj) MtOf IhLj} Ik{Qd(It Lj)} DeKqOu ThIvLd NsNdLj HrItOk ImmIkI

Constrained panels with 3 analytes, where 1.0E-8 >= 'model p-value' > 1.0E-9. Contains 4,802 panels of 15,247,928 total panels evaluated. : Ij{Rt(Fp Hu Hv Hx Ih Ii Im Io Ip Iq Is Iv Jh Jj Jk Jl Jm Jn Jo Jq Jr Js Jt Lh Lu Lv Lx Me Mf Mg Mm Mn Mq Mr Mt Mu Mw Mx Nb Nc Nd Ne Nf Nh Ni Nj Nk Nl Nm No Nt Nu Nv Nw Ny Oe Oh Oi Ok Om On Oy Pa Pf Ps Pz Qa Qb Qc Qg Qh Qt Qv Qw Qy Sr St Tn To Tz Ua Ue Ug Uh Uk Un Uo Uw Vh Vi Vs Vt Wd We Wh Ti Th) Zw(aA Af Bo Cx Dr Hl Hp Hu Ih Im Je Jj Jk Jn Jo Jr Kk Kl Ld Lv Mh Mt Mu Nb Nj Nl No Nt Nu Nv Nw Ny Oa Pk Ql Sh Sj Vz Wb Tl) Wb(Ad An Bb Bo Dk Dr Fc Fw Gl Hr Ib Ih Im Jd Jm Kd Kr Li Lj Lp Mh Mj Ml Mz Ne Nh Ni Nl Nu Nx Oa Of Or Qm Qn Ry Yd Tm) My(Aa Hr Ik Ip Iq Ir Iv Jh Jl Jn Jq Js Lh Lj Lw Lz Ma Me Mn Mr Mv Mz Nd Nt Oe Oh Om Oz Pc Pe Pf Po Qc Qd) Of(Aa Hp Ii Ik Ip Iq It Jl Jn Jq Js Lj Ma Mn Nm Nq Oe Om Oz Pc Pf Pg Qc Qd Vi Vz Wd We Wh Yd Tl) Hu(Fr Hr Ih Ik Ip Iq Ir Is Jg Jp Jt Lx Lz Mi Mm Mp Nd Nq Oe On Qd Sh Ux Vh Vz We) Oe(Aa Fr Ik Ip Iq It Iv Jg Jn Jp Js Lx Lz Mm Mp Nd Nn Ok On Oz Qa Qb Qc Sh) Yd(An Bo Gc Gz Jh Ji Jj Js Ke Ki Kk Kq Ld Mh Mj Mu Nb Nt Nu Nw Sh) Fc(Af Aj Bo Dr Fi Hl Je Jj Jo Js Kr Ld Mg Mu Nb No Nu Ny Pk Sh) We(aA Hq Im Jh Jo Lh Mj Mw No Nt Nu Oz Pc Pf Qy Ub Um Vc Vi) Vi(Jl Li Lj Mf Mj Mz Nu Nx Og Ok On Rb Sr Tn Ub Vp Wf) Sh(Ad Bo Dd De Gl Ii Im Jq Jv Ki Kj Nl Nu Qn Rx) Hl(Af Bo Fw Im Je Jo Ki Kl Nb Ne Nl No Pe Rx) Lj(Ir It Jg Lw Lx Nc Nd Ns Ok On Oz Pc Vz) No(Fd Hp Jk Mh Ms Ng Po Rx Va Vh Wc Xa) Nu(Ho Rx Rz Ux Vb Vz Wd Wh Yl Ye Xa) Mw(Hr Ik Ip Iq It Lz Ms Ng Ns Oz Uw) Vh(Hx Im Jj Jk Jo Nt Qa Qe Qy Un Vt) Bo(Fd Gb Hp Rz Sf Vz Tm Tl Xa Th) Ih(Hr Ik Ip Jp Lz Mm Ms Nk Oz Vz) Pb(Jl Js Lw Mn Mr Nm Pa Pc Pe Qc) Aa(Hr Jk Lz Md Nv Nx Og Oy Oz) Dr(Kd Ki Kp Nh Nl Qm Qn Rx Xa) Jo(Fd Jt Ou Rx Rz Va Wc Wd Xa) Im(Gh Rv Ry Uw Vz Wf Yl Ye) Vz(aA Bb Ki Mj Nb Nh Or) Rx(Af Hp Je Jj Kl Ld Mg) Ir(Hr Ik Mp Nk Ns Oz) Va(Jj Lv Ms Un Uo Vt) aA(Wc Wf Yl Zx Ye Xa) Ng(Jg Jt Mm Wd) Is(Hr Hx Ms Oz) Vb(Mu Nc Nt Qy) bN(Hb Hc Vs Vt) Gn(Je Kl Ld) Nl(Fi Hp Yl) Ik(Fp Iq Lz) Ad(Gb Sj) Em(Ed Uu) Gd(Kd Or) Mj(Hp Ps) Nd(Hq Ns) Nk(Ch Hc) It(Jp Oy) Qd(Oz Uw) Xa(Af Je) Rv(Vs Th) Ou(Hc Uh) GlSf NtYe LwOy LzOz NbZx NjOp HpIn HrJt HxIv WcUo KeLh KlRz UufR} Im{Wf(aA Hv Hw Ii In Ir Iv Jh Ji Jn Jo Jq Jr Js Jt Lh Li Lw Mb Md Mi Mj Ml Mq Mr Mt Mw Mx Mz Na Nb Nf Ni Nm Nn No Nr Nx Ny Oe Of Oi Ok Om On Pb Pd Pe Pf Po Qa Qv Qx Ra Rb Rt Sr Tn To Tv Uc Ud Ul Un Uo Uw Uz Vb Vh Vi Vp Vs Vt Wc Wd We Wg) Oi(Fc Fi Gb Gh Hl Ho Hp Lp Op Ps Rt Rv Rx Rz Sf Sh Si Sj Uw Ux Uy Vb Vh Vw Vz Wb Wd We Wh Yd Yl Zw Zx Tl Xa Th) We(Hv Hw In Iv Jn Jr Js Mi Nb Oy Pd Pe Qt Qw Rb Tv Ug Un Uz Vi Vp Vs) Ye(Af Bb De Dg Fp Gl Ib Iu Ji Ke Mk Mp Mq Mt Na Nf Ni Nm Og Om Pc Rx) Qn(Dr Fc Fd Fi Gc Gh Gn Hl Ho Lp Op Ry Rz Sf Si Sj Vz Yd Yl Zw Tl Xa) Dr(Fd Hb Hc Hp Ib Ic Iz Je Ki Kl Op Ow Rx Yl) Qt(Rt Ru Rv Uw Uy Uz Va Vb Vh Vi Wc Wd Wg Wh) Ch(Fc Fi Gb Ho Hp Lp Rx Rz Sf Si Sj Yd Zw) Xa(Af Bn Bo Cx Dk Hb Hc Ib It Jl Nv Oy Oz) Ho(Af Aj Bg Bo Cx Dd De Hc Iz Kj Ld Oy) Zw(Ax Cs Ji Js Kx Ld Li Lx Ml Oc Pe Po) Hl(Af Cw Cx Dc Fy Hc Ib Ji Lx Oc Oy) Fd(Af Bo Cx Dd Iv Jn Js Mi Oz Pc) Rt(Hv Iv Ji Jt Mi Oe Ok Oy Qv Ug) Fc(Aj Cx Hb Hu Ki Lu Oe Oy Pb) Rv(Ji Lh Lx Ml Oe Pf Qv Qx Ua) Ux(Li Mg Mt Nn Oe Oz Pd Qv Uf) Vi(Jl Nv Oy Qw Sr Ug Uh Vp Vt) Yd(Gc Ic Ji Ke Li Nw Oe Oz) Ry(Af Cq Cw Cx Dc Hc Kd Nb) Gb(Af Aj Bo Cx Hu My Pb) Ke(bG bN Kf Lh Ph Rx Vp) Lp(Cx Dd Hc Kd Ld Oz Pc) Yl(Af Cx Hc Ib Ki Oe Pc) Ug(Ru Uw Uz Vb Vh Wc Wg) Oy(Si Uw Uz Vh Wc Wg Tl) Qv(Ps Uy Uz Va Wc Wh) Qw(Ru Uw Uy Wd Wg) Rx(Dd Iv Me No Ny) Tl(Af Cx Hc Ib) Uz(Jk Nv Oz Vp) Aj(Fi Si Ti) Wb(Ic Oe Oz) Sh(Kq Mw On) Wd(Hu Pb Ua) Cx(Op Rz) Fi(Jj Ld) Nk(aU Uh) Vz(Ic Oe) Ji(Uw Vh) Wg(Nv Pb) Wh(Iv Pd) Va(Pc Ua) IX(Lx oQ) DdHp DeKq TiGd EmUu GnHc WcVp PsOz RzOe RuPc OuUh} No{Rx(Ao Ap Aw Ba Bb Bc Bg Ch Co Cp Cs Cx Dc De Ez Gc Gp Hf Ho Hq Hu Hv Hw Hx Id Ih Ir Is Iu Iz Jd Jg Jh Ji Jk Jn Js Kc Kd Ke Kg Kj Kk Kl Kn Kq Kz Ld Li Lx Ma Mf Mg Mh Mi Mm Mp Mq Mr Mt Mu Mv Mw My Na Nc Ne Nf Nk Nn Nq Nw Ny Oh Om Ow Oy Pa Pd Pe Pf Ph Pi Ql Rz Si Yl Ye Xa) Zw(Ap Co Cu Ez Ho Io Is Kc Kd Kg Ld Li Lx Ma Mg Mi Mp Mt Ni Nn Om Ow Pd Pe Pf Rz) Fc(Af Bn Cx Gp Li Lj Lu Mn Oe Ow Oz Pc Pf Si) Nn(Hu Lj My Og Oy Pc Rz Sh Vw Wd Wf Wh Ye Th) Kd(Fd Gc Gd Gn Hl Ho Hp Lp Op Ry Rz Sh Yl Ye) Oe(Iv Jg Jj Js Lj Ok On Pc Ps Qa Qb Qd Wh) Of(In Is Iv Jg Jn Jq Js Mw Mz Nb Ok Om On) Og(Aa Iv Jq Js Lw Mg Ok On Qb Qc) Mw(Hu Is Iv Jn Jt Lj Ms My Ng) Th(aF Cw Iv Kg Mg Qy Ur Wd) Hr(Hv In Is Jn Jq Mz Ok Qa) Jt(aA Ip Jn Jo Lj My Ng Qb) Oy(Iv Jg Jh Js Lw Ok On Qd) Ho(Aj De Gl Gp Ib Ki Ye) Yd(Ji Ke Ld Li Nq Ow) Jg(Hu Jj Lj My Ng Sh) aA(Jj Js Me Nm Qb Qc) Mg(Fd Rt Va Vw Wc) Ip(Is Iv Jn Nc Pc) Ke(Kf Lh Nx Ph Rm) Li(Vw Wf Wh Ye Tl) Cx(Hl Sf Sj Xa) Gp(Fi Hp Rz Sf) Iv(Hx Jj Lj Nr) Bb(Hl Sh Ye) My(Is Nb On) Jj(Aa Jm Nc) Lj(Is Lw Ok) Gc(Ph Qn) Hu(Wf Ye) Xa(Bn Qn) Rz(De Ib) Ld(Lp Tm) Uh(Gd Va) AaPc ApYe FiGn MhOk MkRu NcNk IhQc IsJn ShPf PsVp OmUw VaVt VwPd PelX} Lj{Vi(Hw Io Iu Iv Ji Jl Jo Li Ma Mg Mi Mj Mk Mm Mp Mt Mu Mv Mx Na Nm Nn Nq Nv Oe Om Oz Pa Pc Pd Qy Rc Rv Sr St Ue Uf Uh Uk Un Vp Wd Ti) Ih(Aa Fr Ip It Iv Jg Jp Jq Lw Ma Mg Mi Mm Mp Nk Nm Nn Nq Nt Nu Ok On Oz Pb Pc) Mw(Ip It Iv Jg Jn Jp Jq Jr Js Lw Mi Mp Mz Nb Nn Ns Nt Oe Ok On Oy Oz Pb Pc) Ir(Is It Jg Jj Jp Jt Lw Ma Mi Mm Mn Mp Nk Nm Nn Nq Ns On Oz Pc) Is(Hr Ip It Jg Jj Jp Jt Lw Ma Mg Mi Mm Mp Nm Nn Ns On Oz) Jj(Ii Il Ip Iv Jg Jn Jq Js Mg Mi Mn Mp Nm Nq Nt Ok) Og(Aa Ip It Iv Jh Jq Js Lw Mi Nb Nm Nq Nt Ok Om) On(Hu Ip It Iv Jn Mh Mi My Nk Ns Of Oy Oz Pc Zw) Pb(Ip Iv Jg Jp Jq Js Lh Lw Ma Mi Mp Mz Nb Nq Nt) Jt(Ip It Jn Jo Jp Mp Nd Ns Of Oi Oy Oz) It(Ik Iv Jg Jp Jq Mi Mm Mp Nn Ok) Oe(Iv Jg Jn Jp Mg Mi Nt Ok) Iv(Hr Jg Mm Mp Nn Oz) Jp(Jq Mi Mp Nn Nt) Wb(Gc Mg Ow Si) Ke(bN Lh Ph Yd) Li(Iq Jr Ng Qc) Ok(Hr Jn Mh Oz) Fc(Kq Mv Nu) Mi(Jg Jn Jq) Zw(Jh Ld Ql) Gb(Af Bo) Ns(Jg Mp) Hu(Nq Sh) Ik(Mg Nt) Ps(Oz Pc) DeKq DrKc TiaA MpJg MtYd NbOf NdHq RxNy} Yd{Li(aA Af Aj As Aw Ax Bo Co Cq Cv Db Dd Dr Fn Fr Gc Gl Hb Hl Hp Hq Ib Ic Ih Io Ip Iq Je Jh Jj Jo Ke Kg Ko Kq Kx Ld Lx Ma Mf Mg Mh Ml Mm Mu Mw Mx Nb Nt Nu Nw Ny On Oz Pb Pc Pe Pi Pj Ql Qm Rz Si Sj Wb Zw) Ke(Ax Cs Db Dr Fy Hf Hw Ih Il Ir Jn Js Jt Kq Kx Ld Lx Lz Mg Mh Ml Mt Na Nb Nn Nr Nt Oa Oh Ok On Ow Pe Pf Pi Pj Zw Xa) Ji(Bb Cx Db Fc Fw Gc Ic Ih Ii Is Jg Jk Jn Jt Ks Lu Lv Mk Mp Mt Mw Nb Nd Nt Ny Oa Pe Pi Pj Si) Pe(Af Bn Bo Cw Dd Fc Gc Gn Hc Ib It Ld Mg Mj Mm Mp Nq Ow Oz Pc Pj Qn Si Zw Ye) Nw(Ao Fw Gc Jh Jt Kg Kj Mt Mv Nm Nn Nt Oe Om Or Ow Pj Rx) Kq(Ch Cx Gn Gp Hf Ib Is Lu Lx Mh Ow Pf Pj Si) Ld(Dc Fw Gc Ih Is Jg Jn Ko Mt Nb Nr Ny) Ow(Dr Hb Hx Jk Jl Nb Ny Oz Pb Pc Pi Wb) Pj(Is Jl Jn Jq Jr Lx Mt Nb Nv Oa Om) Gc(Iv Mq Mv Mw Nn Ny Oa Ry Sh) Lx(Hu Jh Mu Mw Nt Wb) Mt(Hb Ki Or Oz Pb Pc) Nb(Mk Mp Nq Ou) Om(Aj Oy Pb) Nt(Lz Ml) Hb(Co Nn) Is(Oz Pc) On(Oe Rx) ChJh DdMq MkNy MwOi NvOz} aA{Pb(Fp Fr Ii Il Io Iq Is Iv Jm Jo Jp Jq Ke Lh Lw Lx Lz Me Mg Mi Mm Mt Nn Nr Ns Nt Nu Nv Og Om Pe Pf Pg Po Pz Qe) Oz(Fp Fr Ii Iq Is Iv Jg Jm Jp Lh Lx Lz Ma Me Mg Mm Mz Nn Nr Ns Nt Ny Oe Og On Pe Pf Po Pz Qa Qb Qe) Og(Fp Ii Il Iq Is Lw Ma Mg Mm Mn Mz Nn Nr Nt Nu Ny Ok Om On Pz Qa Qb Qd Qe) Oe(Fp Fr Ii Io Iq Jp Lh Lx Ma Mg Mm Mn Mz Nr Ns Nt Nu Om Pc Po Pz Qc Qe) Oy(Fr Ih Jg Jm Jn Js Jt Ma Mg Mn Mz Nn Nr Ny Ok On Pf Qa Qb Qc Qd) Jg(Jj Jm Jn Js Lz Md Mn Mv Mz Ng Of Oi Qb Qc Qd) Ns(Ih Js Ma Mn Nd Nn Nr Ny Ok On Qa Qb Qc Qd) Qb(Jj Jn Ma Me Mg Mm Mn Mw Mz Nk Ny Ok) Qc(Jm Js Lw Ma Me Mg Mm Mn Mz Ny Ok) Jj(Ii Jm Jn Js Mn Nn Ny Ok On Qa) Mz(Jm Ma Mg Mn Mw Nr Ny Ok Pc) Mn(Ih Jn Nm Ny Pc Qa Qd) Js(Hv Md Me Ne Nh Pc) Ti(Ki Li Pe Pf Qa) Jn(Ih Ma Mm Ok Pc) Jt(Fp Md Me Ng Oi) Hr(Iv Jo Ok Qa) Nm(Fp Oi Qd) Me(Ny Ok Qd) Nk(Ih Qa) Hu(Nn On) Of(Ok On) MwQd IhOk ZwPe} Og{Ih(Aa Fp Fr Il Iq Is It Iv Jh Jj Jn Jp Jq Js Lh Lw Mg Mi Mm Mn Mt Mz Nb Nn Nr Nt Nu Ny Oe Om Oz Pb Pf Po Qa Qc Qd) Is(Aa Fp Fr Jm Jn Jp Js Jt Lw Ma Me Mg Mm Mn Mz Nn Nr Nt Nu Ny Ok Om On Oz Pb Qa Qb Qc Qd) Jt(Fr Il Jg Jj Jm Js Lx Mt Mz Nm Nn Nr Ns Ny Ok Om On Oz Pf Po Qa Qc Qd Qe) Aa(Il Ip Iq Ir Iv Lz Md Mg Mq Mr Mt Mu Nn Nq Nw Oy Oz Pb Pc Pf) On(Ip Iv Jg Jj Jm Jn Js Mw Nm Ns Ny Oe Of Oy Oz Pb Qb

Figure 38 Continued

Qc Qd) Et(Hv Hw Iq Jj Lw Mi Mr Mt Nc Nd Nr Nt Ny Ok Oy Pa Pe Pf) Mw(Iq Jj Jq Mz Nb Nm Nt Ny Ok Om Qa Qc Qd) Jg(Fp Iv Jm Jn Jq Mz Ns Ok Qa Qc Qd Qe) Ip(It Iv Jn Js Nn Nt Ok Oz Qa Qd) It(Fr Iv Jp Js Nm Nn Om Qa Qd) Nm(Iv Jn Js Mz Qa Qb Qd) Ok(Il Jm Jn Js Pb Qa Qb) Qd(Il Jn Oz) Js(Fr Jj Pb) Vi(Oz Sr Uh) Nn(Iv Jn) Rx(Kq Ny) IvJn QaPb} Jj{It(Fp Il Is Iv Jk Jl Jm Jo Jq Lh Lx Ma Mi Mm Mp Mz Nd Nr Nt Nu Nv Ny Om Oz Pb Pf Po Pz Qa Qb Qc Qd Qe) Mw(Fp Ii Il Iq Jg Jm Jo Jq Jr Lh Mi Mn Mz Nc Nn Nr Nu Ny Ok On Oz Pb Qa Qb Qc Qd Vz) Ih(Fp Fr Il Iq Is Iv Jn Jo Jp Mi Mm Mn Nk Nt Nu Ny Ok On Oz Qc Qd Rx) Jt(Fp Hr Il Is Jm Js Mn Mz Nm Nn Nr Ny Oe On Oz Pb Pf Qa Qc Qd) Aa(Fp Il Iq Ir Jm Jn Lu Md Mk Mt Mu Nb Nn Nq Oz Pb Pc Pf Qe) Js(Ip Jg Jm Jn Mm Mn Nm Nn Nt Nu Ny Oe Ok On Oz Pb) Jn(Il Ip Ir Is Iv Mn Nm Nn Nt Ok On Oz Pb Qd) Et(Jq Mn Mz Nr Ns Nt On Oy Pe Pf Qd Qe) On(Ip Is Iv Jm My Ns Oe Of Oy Oz) Nm(Fp Il Is Iv Jm Pb Qa Qb) Ip(Il Is Iv Mn Nn Nt Oz Pb) Is(Jg Mn Nn Oz Pb) Ir(Mm Mp) Iv(Nn Ru) Qa(Oe Pb) DeKq IlNy QdOz SrVi XaKd OkPb} Ke{bN(Ad aE Aj An Bg Cv dK Dp eC Gl Gp Hb iJ Jm Ju Kc Kf Kj Kl Kn Ky Mw Nw Oe Oi Oy St Tr Us Uu Vs) Pb(AF aW Bn CX De dK Fw Il Lh Mw Ne Nj Nk Nl Nn Nt Nu Ou Ow Pd Pe Pf Qy Up Us Uu Uv) Lh(Ax Cx Fw Il Li Lz Ml Mw Nn oE Oh Ow Pe Pf Qa Qc Rf Sr Us Uu Uv Wm) Nx(aE bG cH dB dJ dK Jv kS Ky Ld Li Mp Ne Nk Nn Nr Ou Rh Up Uv Vs) Qy(AF Aj fP Hc Hq Hr Hu Iz Jo Kf Kl Mp Nv Of Oy Uu Vs) Il(BG De Dr Gl Hq Jk Jp Kf Mp Nk Up Us Uu Vs) De(dK eC Jv Mu Nf Nn Rh Uf Uh Up Uv Vp) Af(bG Ez Ju Jv Rh St Ug Uh Vp) Vs(Ed Fw Fy Oh Ow Pf Qa Rh) Uv(Mp Nj Nk Ph Rg Vp) Uu(Ne Nk Ph Rg Ug) Dr(Fw Jm Lp Nr) Kf(cH Fw Jm Mw) Rx(Cx Nb Xa) Ph(Jm Rf Rh) aF(Jv Up Us) Ed(Mj Nk) Gl(Gp Ly) Vp(Qa Qd) NrVz NtMp ZwPe KkOu} Vi{Sr(Fp Fr Hr Hu Hv Hw Hx Ih Ii In Ip Iq Is It Jg Ji Jk Jl Jm Jn Jo Jp Jq Jr Js Jt Lh Li Lu Lv Lx Lz Mb Me Mf Mg Mh Mj Mk Ml Mm Mn Mp Mr Ms Mt Mu Mw Mx My Nf Ng Nj Nk Nm Nq Nr Nt Nu Nv Nw Ny Oe Of Oh Oi Ok On Oy Oz Pa Pb Pc Pe Pf Po Ps Pz Qa Qb Qd Qg Qh Qt Qu Qv Qw Qx Qy Qz Rb Rc Rt Rv Ss Tn To Tv Tz Ua Ub Uc Ug Uh Ul Um Un Uw Ux Va Vb Vh Vo Vp Vs Vt Vw Wc We Wf Wh Wm Ti Th) Li(Fr Ik Il Ir Jm Mb Mf Mh Ml Mn Mu Mx My Ng Nr Nx Oe Of Oh Oy Oz Pb Pc Pf Qc Qt Qu Ru Ss To Ua Uh Uk Ul Uw Ux Va Vb Vs Vw Wd Ti Th) Nn(Ng Of Qu Ss Ua Wf) Pe(Jl Mj Nv Oz Pc Vp) Lx(Jl Lv Mj Vp) Mw(Qw Wc Wf) Of(Hw Om Pf) Uu(Uk Ti) Vt(Up Va) Vs(Hw Vq) ThIv NqNx UaQy UfUv} Et{Of(Aa Hv Hw Jm Jr Lh Lx Lz Mi Mr Mt Nc Nd Nm Nn Nr Ns Nt Ny Ok On Pa Pe Pf Pg Po Qc Qd Qe) My(Fp Il In Ip Iv Jg Jm Jq Jt Lz Mi Mt Mz Nc Nd Nn Nr Nt Oz Pa Pe Pf Qa Qc Qe) Ns(Hw Il Ip Jm Jq Jr Jt Lz Mp Nc Nn On Oy Oz Pe Pf Qa Qd Qe) Oy(Aa Hw In Jh Jq Jt Lz Mt Mz Nb Nd Nn Nr Nt Ok Oz Po Qe) Ng(Il Jg Jm Jt Mi Nc Nd Nn Nr Nt On Oz Pe Pf Qa Qb) Oz(Jq Jt Lz Mi Nc Nd Pe Pf Qa Qc) Hr(Hv Hw In Jn Jq Jt Mz Ok Qa) Ip(Fp Is Iv Jt Lz Nc Qa Qc Qd) Fp(Hu Iv Jm Jt Nc Nd Qc) Nc(Jq Mz Nd Nk Qc Qd) Lz(Ik Jm Jq Jt Pc) Hu(Il Nn Qa Qb) Jt(Mg Mz Nd Qb) Pb(Lh Mi Nb On) Jq(Jm Nd Nx) Is(Nx Qc) Iv(Jo Qb) AaOe MkPa MsQb MwQd PcPf PdPg} Pe{Zw(Ad Af Ba Bc Bn Bo Ch Co Ct Cw Cx Db De Dg Di Dl Dp Fi Fn Gc Hf Hu Hv Ic Ih Is Iv Iz Jh Jk Jl Jm Jn Jo Jr Jt Kc Kf Kg Kj Kk Kl Ko Kq Kr Ks Kx Ld Lp Lu Lv Me Mm Mt Mw Mx Nb Nc Ne Nh Nj Nl Nm Nt Nu Nv Nw Ny Oa Oi Ok Om On Pg Pj Rx Sh Sj Yl Tl Xa) Fc(Af Bn De Gl Kj Nb Ny Pg Yl) Bn(Fd Gb Hl Lp Ry Yl Xa) Bo(Gh Lp Rx Ry Sf Vz Tl) Af(Fi Ho Rx Ry Sj Xa) Qn(Dr Gn Vz Wb Yl Xa) Mw(kN Pb Uw Wf) Qy(Uw We Wf Wh) Nw(Mh Mk Pd Po) Aa(Oz Pb Pc) De(Gb Ho Rz) Dr(Id Kd Tm) Hl(Bb Il Kd) Vz(Cs Il Kd) Ps(Oz Pc Vp) Rt(Il Ru Ul) Lv(Wf Ye) Hu(We Wf) Ji(Pd Po) IX(Mp Nj) AnYl DdSh ExGd GpTl MhLi IdWb JmRv RxNy UhbN VaVt} Aa{Oy(Fp Fr Ih Iv Jh Jm Jp Lu Ma Md Mg Mj Mq Mu Nq Nr Po Qd) Oz(Fr Ih Ir Iv Jp Lu Lx Md Mj Mk Mq Nn Pg Qd Qe) Pb(Fr Is Iv Jn Lu Ma Mj Mk Nq Nu Pg Po Qe) Md(Fp Iv Js Lx Lz Mj Mk Ml Mt Nc Nw Pc) Mq(Ih Ip Iq Ir Iv Jm Lz Mr Mt Nc Nx Pc) Nx(Fp Ih Is Ji Jn Js Lx Mt Nw Pf) Oe(Fr Iq Ir Is Jk Jl Mt Nq Po Qe) Pc(Ir Jn Lu Lx Mj Mr Mt Nn Pf) Hr(Fr Jl Lu Lx Mk Mu Nq Po) Iq(Iv Lu Ms Nb Nc Nw Pf) Ih(In Iv Lu Lz Mr Nw) Of(Jh Nq Nw Po Qd Qe) Nc(Mr Mu Ni Nk Nn) Ip(Fp Iv Mt Nb Nw) Lu(Jn Nn Qa) Lz(Iv Mu Nn) Qe(Mk Nk Oi) Mj(Mu Qd) Mr(Iv Jm) Jn(Nb Pf) DeLi PoNk NqMy MkJm JiJq} Mw{Sh(Ba De Fw Gh Gp Il Jg Jv Nd Nr Oe Oi Om Or Ow Pa Pf Ph Rx Vz) Ih(Ip Is It Iv Jg Jn Jq Jt Ma Ms Nk Nm Ns Nt Ok Oy Oz Pb Qd) It(Ik Ip Iv Jn Jp Jq Jr Js Jt Mz Ns Oe Ok On Oy Oz Pb Qd) Jn(Ik Ip Is Iv Jt Ms Ns Oe Ok Oy Oz Wf) Is(Hr Hu Ip Ms My Ng Ns Oy Oz Qc) Wf(Li Lx Mh Nn Nr Pf Qa Ru) Jt(Hr Ip My Ng Oe Oy Pb) We(Ir Mt Nb Nr Sr Vh) Oe(Iv Js Ok On Qa Qd) Of(Jq Js Mz Ok Om On) Pb(Jq Js Mz Nt Qa Qd) Ip(Iv Js Ok Oy Oz) Oy(Iv Js On Qd) My(Mt Nb On) Ru(Qw Vt Wh) Iv(Hx Oz) ChTi Fplk MhZw MlWh NgJg HrOk WbOw QdOz SrRt RxOa LdLp} Ir{Oy(Fr Ip Is It Jg Jn Jt Lw Mm Mp Mt Nk Nm Nn Nq Ns Ok Pc Pf) It(Fr Ik Jg Jp Jt Ma Mm Mn Nd Nk Nm Nn Ns Ok On Oz) Ns(Ik Ip Jg Jp Jt Ma Mn Mp Nm Nn Ok On Oz Pc) Hr(Hv Hw Ik In Ip Is Jn Jo Jq Mz Nm On Oz) Of(Is Jg Jt Ma Mn Mp Mt Nb Nm Nn Ok Om On) Nk(Ih Jp Jt Mm Mn Mp Nc Ni Nn On Oz) Ik(Fp Fr Jg Jt Lz Ma Mn Mp Nm Nn Nt) Oz(Fr Is Jp Ma Mn Mp Nm Nn Pf) Nn(Hu Ip My Nm Oi Pc) My(Jh Jt Mt Nq On) Jg(Hu Ng Oi) Jt(Jo Ng Oi) Nm(Is Jo) Mn(Ip Ms) Rx(Af Hp) NqHu MaIh MeMf MtZw NdHq HxIv NxOn PdPf} Nw{Md(Jo Jq Jr Js Mi Mp Mz Nd Nn Nt Ok) Mh(Fp In Ip Is Mi Mr Nc Nr Nt Nu Qa) Nx(In Ip Jm Lw Mn Mp Mz Na Nm Nt Ok) Mv(Il In Jm Js Mi Nn Nt Nu Pc Qa) Nv(Hw Il Jo Js Mp Nd Nn On Qa) Ng(Jg Jm Mg Nm Nn Nt Nu Pc) Ny(Hw Js Mi Mz Nt Pc Qa) Hr(Jq Jr Js Mz Na Ok) Hx(Hv Hw Js Mi Nt Pc) Fp(Hu Ly Mb Of Pc) Ms(Ip Js Mn Nc Pc) Nu(Ly Of Ru Tm) Hu(Ip Jm Nc Qa) Ly(Nc Nd Nt) Ip(Nc Of Pc) Po(Mr Nt) Nn(Mu Pc) Mk(Jl Pa) Nd(Of Pg) Iq(Lz Mj) Iv(Ru Th) Qc(Qa Qd) Om(Hw Jq) DeKq DrKd NmMf MlIn NaOf NbRt IhZw RxLi PdPf} Nb{Rt(Hv Hw Is Iu Jh Ji Jo Jt Li Ma Mg Mi Mm Mp Mt Mu Mv Na Nm Nn Nq Om Pd Qy Qz Ue Uf Un Wd Ti) Bo(Fc Fd Fi Gb Hl Ho Lp Rz Sf Si Vz Wb Ye Tm Tl Xa) Tl(Af Bn Cx Dk Ib It Jl Ld Ny Oe Oz Qn Rx) Fc(Ar Kx Ld Lp Lx Lz Mk Ml) Ti(Aj Ch hB HC Uu) Ld(Fi Gh Lp Rz Vz Zw) Li(Mv Rx Uw Ux We) Mq(Uw We Wh) Rx(Iv Lu Oa) Of(Jg On Vh) Ar(Fi Ho) Zw(Ow Po) We(Nn Nq) Kj(Ho Rz) Un(Ru Va) FdIv NhWf JiPa UhfR} Pb{Is(Fp Ih Jg Jn Jp Js Jt Lh Lw Lx Lz Mm Mn Mz Nm Nn Nr Ns Nt Nu Ny Ok On Pf Po Qa Qb Qd) Ih(Fr Ip It Iv Jg Jn Jp Jt Lh Ma Nm Nn Oe Ok On Pf Qd) Jt(Fp Fr Hr Ip It Jn Js Lx Nn Oe On Pf Qa Qb Qd) Ok(Fp Hr Ip Iv Jn Js Nn Oe Pf Qa Qb Qd) On(Ip Iv Jn Js My Ns Of Oy) Ip(Iv Jn Js Nn Qa Qd) It(Fr Jp Js Nn Qa) Iv(Fr Jn Ma Nn Qa) Jn(Fr Qa Qd) Js(Fr Oe) DeKq MaQa QdOe} Li{Fc(Af Ch Dg Dr Hp Hx Jl Kl Kq Mm Ms Ny Pk Sj) Dr(Gl Jy Kd Kx Lp Qn Rx) Of(Hw Jp Jr Mf Mt Nm Nt) Af(Fi Ho Lp Rx Vz) My(Jh Jp Mi Mt Ok) Wb(An Ch Gl Qn Rx) Mh(Mi Mr Nt Pa) Jo(Fi Hr Nm Nt) Ny(Rx We Wf Ye) Nd(Mk Pd Pf) Ng(Jp Mf Mi) Hp(Ch Gl Rx) Fi(Kg Ld) Gb(Cx Ed) Mt(Mv Oy) Iq(Mj Pf) Lp(Cq Ld) Rt(Is Nr) Pd(Pf Pg) DeKq ThbM FrVa LyMz LzQd MfQb MiHq MvOn NaHr NcNe HuUx OiOk nDnL} Oe{Ih(Fp Il Ip It Iv Jn Jp Js Lx Mm Mn Nt Nu Nv Ny Om Oz Po Qa Qd) Is(Fr Ip It Jn Jp Js Jt Lx Ma Mm Nm Nn Ny Ok On Oz Qa Qd) On(It Iv Jn Js Jt Ns Of Oy Oz Qa Qb Qd) Jt(Fp It Jn Js Nn Ny Qa Qd) Ok(It Jn Js Qa Qb) Qd(Ik Il Jn Oz) Qa(Iv Jg Jn) Jg(Js Qb) Ps(Va Vs) DrOa NnJn ShNv} It{Ok(Ih Ip Is Jn Jo Jp Nd Nx Of Oy Oz Qb) Jp(Ih Ip Is Iv Js Jt Ns Oz) On(Ik Ms My Nk Ns Of Oy Oz) Jt(Fp Hr Ih Ip Jo Of Qb) Is(Fr Ma Nm Nn Oz) Ih(Fr Jg Ma) Rx(Af Ny) FrOz HrIv VaVt} Rx{Ny(Ar Ih Iu Iv Kx Kz Ld Mq Na Oa Ow Pd Tl Xa) Oa(Dr Hl Hp Hx Je Ld Mh Mu Ni Nu Pi Wb) Ih(Aj Dd Hx Pk) Jn(Bo Hp Mq Nc) Ch(Jh Kq) Ow(Dr Hp) KdQl KqNx} Ld{Lp(Af Ap Bn Bo Cx Dp Hl Hu Ik Iv Kj Ks Nu Pa Pc Qn Zx) Zw(Ih Il Jg Lx Nr Nv Oa) Nr(Dr Fc Hp Vz Wb) Fw(Dr Sj Wb) DraW FcJn FiHu KdRy} Jt{Of(Fp Fr Ih Jn Lx Mp Nd Nn On Qa Qb) Hr(Fp Ip Is Jn Js Lx Lz Mz Qa Qb) Ih(Fp Ip Jo Ma Ms My Ng Oy Oz) Ip(Jo Oz) FpIk NsNd QbOy} Kq{De(aE Aj bL bW Ch dN Ed Fc Fw Hb Ho Hw In Ki Kl Lp Lz Mg Ng Nk oH Oi Ow Pa Qb Qc Rf Ss Uo Uu) Af(Fi Lp) Bg(Lp Tm) UhVp} Oz{Is(Fr Ip Jn Ma Nm Pf Qd) Ps(Mh Ml Mx Va Vs) Ih(Fr Ip Ma Ok) Ip(Iv Ok Qd) Fw(Sh Sj) Sr(Rt Vh) FcIv NtVb MyOn HrOk WbOw QaRt JiJl XaNy nCnl} Dr{Ow(An aY cX Nr Nx Oi Qn) Kd(Bo Lh Lx Mk Mq Pf) Oa(Gc Gp Pj) Nn(Kl Sh) Lx(Qn Zw) Pf(Ic Sh) MkLp KlOm OraW} On{My(Ih Ip Jg Jh Jn Ns) Oy(Ih Ip Jg Jn Nm Qb) Of(In Is Iv Jn Om) ThaY NsNd Hrlv IkQd} Wb{Ow(Kl Lv Ml Oi Pc Qn) Lx(Bb Bn Kd Ky) Nn(Kl Ng Sh) Pf(Hc Ic Lu) Oa(Gc Pj) MhOm MkPa} Sh{Nn(Fn Fr Hu Jh Ny) Hu(Is Lx Ow Pf) Cx(Fw Oa) Dd(Ml Pf) AfNv FwMv NqKd HpPf IhJv lUd} Uh{bN(Is Jo Js Ko Md Mj Ni Nm Nr Ok Ul Ur Us) Qa(Nk Ou Vs) PsVa} Va{Ps(Hu

Figure 38 Continued

Oi Pc Qt Qw Vp Vt Wf) Vt(Nt Qy Rc Sr) Un(Jm Pa Ru) SrUo} Jg{My(Ih Is Js Qb) Ih(Ng Oi Oy) Js(Ng Of Oy) Is(Of Oy) NsNd IkQd IvOf}
Hr{Iv(Fr Ih Ip Jn Nn Ok Qa Qb) Ok(Ih Ip Is Jn Js Qb)} Oa{Gc(Af Bo Cq Iq Jo) Af(Si Ti) Cx(Fc Xa) Zw(Ic Mt) Ye(Hu Jh) CvFc} Ed{fR(aW
Nk Ow Pd Vq) Gb(Ba Lx Nn Pf) Gd(Ba Cw Kx Ow)} Qd{Ik(Fp Ip Jn Js Ma Nm Nn Nr Nt Ny Ok) NsNd} Rt{Sr(Hx Is We) Qa(Oi Pc) Jm(Hv
Ji) NrQy MiQb IIIv} Ch{Jh(Fc Fi Ho Lp Rz Tm) NqLp RzNy} Ih{Ma(Ip Iv Ns Oy) Oy(Fr Ok) AjFc MtMy} Zw{Lx(Cx Hp Je Nt) Ow(Hp Nu)
NrQl NtOh} Jn{Af(Fi Ho) Bo(Fc Fi) Wf(Nj Qy) CxOp NsNd} Ji{bN(Qy Uv) PoMr FcNu FrHu NnMu NtLy} Ny{Fc(Mk Pf) DeHo GcKr KdLp
PsVp} Af{Ho(Ow Pf) Lp(Mq Ow) GbPf} Nd{Ns(Fp Is Nt Ok) HqOk} Hp{Nn(Aj Kl Ng) KlOw} Sr{Gd(An aW) QaUw} Xa{AdKd BoFw FcOi} Nu{FcLx QaWf} AjCxHo BoGbNr ThIvJp FrMtWc FwNtYl LxQyUx MqHlKd MrRuPa HuQwPs QcnIoQ bCdMjQ bMcHnN

Constrained panels with 3 analytes, where 1.0E-7 >= 'model p-value' > 1.0E-8. Contains 10,767 panels of 15,247,928 total panels evaluated. : Vi{cV(aA AD aE Af aG aH aI AJ aK AL AN AO aP aQ aR aS aU aV AW aX aY aZ bA BB BC bE bF BG bH bJ bL bM Bn BO bP bQ bS bU cB cD cE CH cJ cL cM cN CP CQ cR CS CT CU Cv CW CX cY cZ dA DB Dc DD DE dF DG dH Di dJ DK DL dM dN DR Du Ed EF Em Eq Ex Ez Fc Fd Fi FP FR Fw Gb Gc Gh GL Gn GP Gz Ha HC Hf Hp Hr Hu Hw Hx Ib Ic Id iH Ii Ij Ik Il In IO iP Ir It Iu IZ Jd Jc Jh Jl Jm Jp Jq Js Ju Jv Jy Kc Kd Kf Ki Kj Kk Kl Kn Kp KQ KR Kx Ky Kz Li Lj Lu Lx Ma Mb Me Mf Mg Mh Mj Ml Mn Mq Mr Ms Mu Mv Mw Mx My Mz Na Nb Nd Ne Nf Ng Nh Ni Nk Nl No Nq Nr Nt Nu Nv nW Nx NY Oa OE OF OH Oi ON Op Or Ow Oy Oz Pa Pb Pc PF Pg Ph Pi Po Ps Qa Qc Qd Qe Qh Ql Qm Qn Qt Qv Qw Qz Rb Rc Rf Rh Ri Rj Rm Rt Ru Rx Rz Sf Sh Si Sj Sr Ss Tn To Tv Ua Ub Ug Uh Uk Ul Um Un Up Ur Us Ut Uu Uv Uw Ux Uy Va Vb Vh Vp Vq Vs Vt Vw Vz Wb Wc Wd We Wf Wh Yd Zw Ye Tm Tl Xa Wm Ti Th) Sr(aA Ad AF aG aH aI AJ aK AL aM AN aO aQ AR AS aU aV aW aX aZ BA BB Bc bE BG bL bM BN Bo bP bQ bS bU bV bX bZ cB cC cD cE cF cG CH cI cJ cL cN cO CP CQ Cs Ct cU Cv CW CX cY cZ dA DB dC De dF DG dJ DK DL dM dN Dp dR Du Ed EF Eq Et Ex Ez Fd Fn fP fR Fw Fy Gb Gc Gd Gh GL Gn GP Gz Ha HB Hc Hf Hl Ho Hp iA Ib Ic iP IZ Je Jv Ke Kf Ki Kj Kl Kn Kp kQ KS Kx Ky Ld Lp nW nY oE oF oH oK oN Op Or Ou Ow pF Ph Pi Pj Qn Rg Rh Rj Rx Ry Rz Sh Si Up Ur Us Uu Uv Wb Yl Zw Zx Ye Xa Tj) Li(Af Aj Al AN AO aW aX aY Bc Bg bH bL bM Bn Bo bU cC Ch cP cQ cR Ct Cu Cv CX Dd DE DG dH Dk Ed Ef Eq Ez Fc Fi fP Fw Gh Gl Ib iO Jd Ju Jy Kd Ki Kj Kl KR Kx Nq oE Ow Ql Qn Qz Rt Rx Rz Sf Uc Us Ut Uu Uv Uy Yd Zw Tj) Lj(aC AF aG aK aN Ao Ap aU aW AX bC bE bG bJ Bn Bo bW bZ cC cJ cN CO cP CS Cw CX cY De dI dJ DK dM dR Ex Ez Fc Fi Gb Gc Gp hC Ho Ic iH iJ iO Kc Kd Ke Kg Kj Ko Kq kR Ld nW Oa Or Pj Qn Rf Rx Rz Si Ur Vq) Bn(aO dR Ed Fn fP Gc gL hB hC iA Ij Im iZ Jn Jq Js Ld Lh Lx Ml No Nw nY Oa oF Oh oK oN Ow Pe pF Po Qa Qb Qd Qg Sh Tz Vt) aW(Aj aO Ar Ch Cs dR EF Eq Fp gL hB Hc iA iH iJ iO iP Iv Kg Kj Kl kQ kR kS Kz No oF oH oK oN Oy pF Rz Sh Sj Uu Ux Vo) Bg(Ao Ap aU bC bJ bW CO Cx De Ef Gc Ij Iu Jh Kc Kg Ld Mg Mi Mt Mu Mv Nm Nn Nq Om Pd Qd Qy Qz Rx Rz Ue Uf Vq Wd) Ch(Ao Ap aX bC bJ bW Co cS Ef Gc Ij Jd Jh Kc Kg Kq Mg Mi Mm Mq Mt Mu Nn Nq Pd Pj Qy Qz Rx Rz Ue Uf) iO(Ao Ap aU aX bC bJ bW CO cS De Ez Gc Iu Jh Kc Kg Ki Kq Ld Mg Mi Mm Mt Mu Nn Nq Om Pd Qy Rz Uf) Ij(aA AD aE aF aN aO aY bF bG Bo cH Dk gL Hc iH iZ kS nW oF Op pF Qn Up Us Uu Yd Zw) aO(bG Bo cU Gp Ib Je Ld Lx Mf Mq Oe oF Ow Oz Pf Rj Rx Sh Uh Ur Uu Wf) Dk(aM bP Fp Gc Im Ir Ji Jn Ke Ld Lx Nw Pe Pj Qa Qd Qe Si Uh Vt) Oz(Bo dR Ed eF fP gL hB hC iA iJ iZ kQ nY oE oF oH oK oN pF Yd) aY(Ar bB Bo Gc hB Is Ji Kx Ld Lx Mk Mp Nw Ow Pe Pf Pj Po Ur Vt) Uv(aU Co Gc Iv Kc Kg Kq Ld Mi Mq Mt Mu Mv Nn Om Pj Po Qy) Im(Af aG aJ Bo CX dR gP Hb Hc Ib Jk Qn Sh Ua Ur Uu) aF(aZ cQ Eq Gl Gp Ki Kl Lx Ml oF Ow Pf Rz Ss Uu Vb Vt) Af(Ed Gc gL Hv iZ Kq Mi Mp Mw Om Ow Pe Qa Qd Vt) Oe(dR Ed fP gL hB hC iA iZ nY Oa oF oK oN pF Sh) De(aU Co Ho Kc Ld Mi Mp Mu Nn Om Qd Qy Ue Uf) Eq(Ap bW Co dK Jh Kc Kg Mg Mi Mu Nm Nn Qy Rz) Yd(aU cQ dA dR Gc Ji Ke Ld Lx Ow Pc Pj Uh Ti) Uu(aC Ap bJ Cw Gc gL Hw Jg Kd Mw Nm Nn Pz Qy) gL(Bo cQ dG fP Hp Ki Mf Oy Pb Pf Uh Ti) Nn(Aj aX Dg Ed eF fP Hc Iz Kl Rz Sh) Kd(Aj Ar eF hB iP Jj Jk kS Oy Rt Us) Pe(cP Ct cX Dd dG Du Ex nW oN Qn Zw) Cx(bG Ed Hc hG iZ nY Oa Of Qw Wf) kQ(Gc Iv Ji Kc Mq Nq Pa Pj Qd Uh) Gp(Ed hG Jp No nW nY oE oH pF) Hc(AN bJ bP Mw oH Qg Qy Rx) kR(cO dR Ke Ld Mk Mm Mt Nq Pj) Pf(bF bG hG iA iH oH pF Sh) nW(Ed Mf No Oa Qa Qc Qe Sh) Ap(Aj Dg eF Kl Of Ux Vo) Qn(Ld No Nw Oa Qa Sh Vt) dR(aQ Ed Gh Gl Pb Va Vs) Ow(bF cE dF Lv Nx Zw) oH(aZ cQ Ki Lu Pb Ss) oN(cU Ed Ib Of Uh Va) Kc(Aj eF Iz Of Ua) bJ(Aj EF Kl Ss) Bb(Ar eF kS Rt) Ed(bZ cX hC Ti) Ki(bG hG iH iJ) hB(aN Il Pc Uk) Ef(Co Pj Ue) Lx(Ky Rg Up) Ji(Gl Nx Ou) Jl(cQ Fn Qa) Rx(fP Lu Wf) cX(Iv iZ nY) oF(AN Pc) Ti(iZ oK) Fi(Of Rt) Fw(Ld Ur) Gc(fP iA) Mi(Ua Vs) Qd(Kr Us) Nx(Ke Ld) Vt(Gh Rg) iH(Ml Mx) kS(Jg Uh) pF(dF Va) AjQy GlKz MtfP HoOf QaaN KjdK LpUr PcnY aUiZ} Ij{Rt(aA aC AD aE Af aI aK AI aM aN aP aR As aW aY aZ Ba bB BC bE bH bJ bM BN BO bQ bU bV cB cC cE cF cG cI cJ cL cM cN Cq Ct cV cW CX dA DD De Dg DI DL dM Dp DR Du eF Fc Fd Fi Fn fP fR Fy Gb Gc Gd Gh gL Gn GP hB Hc Hf hG Hl Hp iA Ic Id iH iJ IZ Je Jf Kd Ke Kf Ki Kk Kl Ko Kp Kq KR KS Ld Lp nW nY Oa oE oF Or pF Pi Pj Pk Ql Qn Rf Rm Rx Ry Sh Sj Up Ut Uu Vz Wb Yd Yl Zx Tl Tj) We(aE aF aJ aM AN aO aY bF bG bL Bo bR bS bZ cE cG cL Ct cU Dd dF dG dH dL dM Du Ed Ex fP Gb Hc iA iZ Je Js Ki kS oF oK oN pF Pi Rg Ri Sh Uo Uu Wb Tj) Uu(bN Dr Du Eq Et Fc Fd Fi Gb Gc Gh Gn Hl Ho Hp Ke Nk Op Ps Qy Rv Rx Sf Sh Si Sj Uh Uw Ux Vb Vc Vh Vw Vz Wh Wc Wd Wh Yd Zw Zx Ye Tl Xa) Vh(aA aE aF aN aY bG bJ bM Bo cG cM cU cV cW DD DR Ed fP iA Je Ke kS Mj oF oK oN pF Pi Rh Ri Sh Um Vq Wb) Wb(aD aE aN aW aY bG bM cH cI cP cX dE dK Em Ex Gn hC Hv Ki kQ nW Rb Ru To Up Us Uy Va Vb Vp Vs Wm Th) Hr(aY Bb bN Ch Hw Ik Ip Iq It Jn Jp Jq Jr Js Ke Lh Lz Mi Mp Mr Ms Mz Nt Oe On Oz Pe Qa Qc Qd Uh) It(Fp Fr Hu Ik Ip Iq Is Iv Jq Jr Js Jt Lx Ly Lz Mi Mm Mn Mp Ms Mz Nd Nn Ns Ok Oz Pc Qc Qd) Va(aA aC aE Af aN aS aY bE bJ bM bN bO cF Cq cV cW dD Dr Ed hG Hl Hp Je kS Ld oF oK Pk Sh) Zw(aC aE aN aZ bE bH bJ bM bN bO cF cI cV dD dK hG iZ kS oF oK Ps Qy Rh St Un Uo Wh Tj) Fc(aA aC aE aN aY aZ bH bJ bM bO cM dD dL Ed iZ kS Lx Mh Mw oF oH pF Qy Rh Uo Tj) Ms(Ik Ip Iq Iv Jg Jn Jp Js Jt Lw Lz Mi Mm Mn Mp Nd Nm Nn Oe Ok On Oz Pc Qa Qc Qd) Yd(aC aE aF aM aN aY bE bG bH bJ bU cM dR Gb Jk kS Mt Qd Qy Rh Ri Rv Uh Um Vt Tj) Th(Ar bE bH bJ bN Cq cR Cv fR Hf Ii Jj Ju Ld Mn Nc Ni Nj Pa Rh Rm Ug Un Up) Ik(Fr Ip Is Iv Jg Jn Jp Js Jt Lx Mi Mm Mp Mt Nm Nn Ns Nt Ok On Oz Pf Qa Qc) aY(Eq Fd Gb Gh Hl Ho Hp Lp Op Ps Rv Rx Sf Sh Si Sj Vw Vz Wd Wh Yl Zx Tl Xa) bM(Du Fd Fi Gb Hl Ho Hp Op Rv Rx Rz Sf Sh Si Uw Ux Vc Vw Wc Wd Wh Ye Tl Xa) Oz(Fp Fr Hu Ip Iq Iv Jl Jn Jp Js Jt Lx Mi Mm Mp Ng Nn Ns Ok On Pf Qa Qc) Ke(aF Bg Ch De Gl Hc Hq Jo Kf Mj Mp Nj Nk Nv Of On Ou Oy Ph Up Us Vs) Ng(Fr Ip Iq Is Jn Jp Js Lw Lx Lz Mi Mp Nd Nm Nn Ok On Qc) bN(Dp Eq Iz Jo Ju Ki Kl Ld Ne Nj Nk Ou Ow Qw Tv Ur Uv Vb) Ns(Is Jg Jn Jp Js Jt Lz Mm Mp Nn Oe Ok On Qa Qc Qd) Uh(Af Bg Ch Hc Hq Im Jo Ki My Nj Nk Of Ow Oy Up Vs) kS(Eq Gd Hl Ho Lp Rv Rx Si Uw Ux Vb Wc Wd Wf Wh Yl) Ou(aF Bg CH Ct Im Mn Mw My Oe Of Oy Pb Qd Vs) Qc(Hu Ip Is Iv Jn Jt Lz Mi Mm Mp Mw Nn Ok Qd) Eq(aE aN Bo fR Hu Im Jh Mu Nj Nu Qy Qz Up) Jk(Iq Is Iv Jt Lx Mi Mp Mw Nd Nn Ok On Pa) Jo(Bb Ez Hc Ip Iv Js Mm Mp Nm Ok Or Ow Qy) Rx(aA aC aE aN bE bJ bO cF dD fP iZ Lv Uo) Dr(Hb kQ Ne nW Qv Qw Rb Um Up Us Vp Wc) Jn(Hu Ip Iv Jp Jt Lz Mi Mm Mp Nd Nn Ok) Nk(aF Aj Ao Bg cE Ct De eP Nc Qa Vs) Oe(Fp Jl Mi Mt Nc Nm Nt Ny Oh Pa Qe) Ch(Bb In Mw Ne Nj Nl Ow Qy Ur Wd) Hl(aA aE bE bG bJ cV dD iZ Nt oF) Hc(aE Fb In Nj Ow Qy Rm Tv Up Ur) Ip(Iq Is Iv Jp Js Jt Lz Mp Nc Ok) Hx(Hu Jp Lx Mi Mr Mz Ok Pa Pe) Wc(Af bE bO dD Hp Je Ld oF oK) aN(Ps Sf Sh Sj Ux Vb Vz Yl Tl) Bo(Du Ps Rv Ux Vb Vc Wf Wh) Mp(Hq Iv Jp Ly Mk Mw Pd Pg) Mi(Hq Jp Ly Md Mv Mw Ny) Iv(Hu Jp Lw Ly Mk Mm Nn) Sh(aA dL iZ Kf Up Us Uv) aE(Du Ho Hp Op Ry Uw Vz) Ed(Hp Rv Si Sj Uy Tm) Ne(aF Aj Bg De Gd Gn) Wd(Af Aj Bg Kg Kl Uv) Ok(Hu Ly Mw Nc Nd Nx) Vb(aC aS bE bJ dI fR) Du(Ad hB Li Nl Nu) Fp(Hu Jp Mm Mw Nd) Lz(Is Jp Jt Ly Mh) Mv(Jg Jp Mt Nn On) Rv(aA De Ki Kr Oa) Of(Bb

Figure 38 Continued

Ez Hb Qy Sj) Hp(aA bG cP Up) Vz(aW cP kQ Um) Xa(bJ fP Nl oF) Vs(Im Kq Li Qd) Gn(hG iZ Vo) Lx(Hq Ly Mh) Hu(Pc Pf Qa) Wf(iZ Ki Nu) Ps(Dk Up Us) aA(Fd Fi Sj) fR(Kl Kn Kr) De(Mu Qd) Mm(Is Js) Mw(Jr Nc) Mz(Md Ny) Jp(Js Nn) Op(aZ dL) bJ(Ry Ux) BgQy FdiZ GbKf NmIs MkPa MtNy NldX WhUv YebE YlUs PdPf} Ke{Im(aE Af aJ aP Ar aU bL bO CH Cw dB dJ DK Dr Eq fP Fr Gl gP Ha Hb Hc Hq Hu Hx Ib Jh Jk Ju Jv Kc Kl Kn Ky Mj Mp Ne Nj Nk Nl Nv Ou Ow Oy Qn Qw Qy Rg Rm St Uh Un Up Us Uu We Wf) Il(aA Ad AF bL bO bZ CH Cp Cw Dc Dd dJ DK Dp Ha Hr Ii Jh Jl Jo Jt Ju Jv Kj Kn kS Mj Mn Ne Nj Nl Nv Of Ok ON Ou Oy pF Qh Qw Rg Rm St Tn Tr Ur Ut Uv Vo) Rh(Ad aE aF Ar aY bG bL bM dG dJ Dk fP Gl Hq Hr Jm Jo Kf Kl Kn Ky Lx Mh Mj Mp Ne Nj Nk Nl Nv Nw ON Ou Pb Po Qc Qx Qy St Uh Uv Vp Yd) Vp(aA aE aF Bn CH cT Cu eC Ed fP Fw Fy Hv Ih In Is Iv Jm Jn Jr Js Jv Kl Kp Kq Lj Ms Mw Na No oE Oh Pb Pe Pi Qb Qc Qe Qy Tz Uh Uu) Qy(Ad AO bL Co DG dH DK Dp eC Ef Fr Gl Ib Ii Ik Jj Kg Kj Lj Mg Mj Mu My Ng oE Om On Ou Po Qc Qw Rf Rg Uh Us Ut Uv Vo) Nk(aA aE aF aW cH Cu De dK eC fP Fy Gl Ih In Jm Jn Jr Js Kc Kf Lh Lj Mi Mp Mw Mx Na No Nr Nt Oh Oy Pi Qc Qd Tz Ul Vs) Uv(aF aW aY bG bL cN dB dG dH dI dK Ez Fn fP hB iJ Kf Kn Kq Ky Mc Md Mj Na Ne Nl Nn Nt Nw oN Or pF Ra St Ug Uh Vs) eC(aF aJ aP aW aX aY bG bL bM bO cB CW dB dE dG Gl Kf Kn Lh Lx Mj Mp Nj Nl Nx oF Oh oN Or Ou pF Ph Po Tn Vs) Us(aE An aO Ar aW bG bL CH cV dE dJ dK fP Jm Jv Kn Kp kS Ky Md Na Ne Nl No Nt Nw oN Ph Qw Rg Ug Ur Uu Vs) Mp(aA aE AF aW bG Bn cH cV De dK Ez Fw Jm Jv Kn Kp Kz Lh Mw Ne Nl Nn No Nr Ow Pe Pf Ph Qc Qw St Uh Uu) aF(aA aE aW bG cH Dc De dJ dK Gl Gp Hx iJ Ju Jy Kc Kf Ky Lh Mz Ne Nj Nl Ou Ow Ph Qv St Uh Un Ur Uu Vs) De(aE aU aW bG bJ bO cH dJ dR fP Jm Kf Kg Kn Kp kS Kz Lh Li Mg Mv Mw Ne Nr Nt oE Or Ow Ph Qd St) Yd(aW bA bG bJ bN bU cT eF gL iH kR Mv oE oF oK Ps Pz Qa Qx Ra Rf Ru Sr Va Vh Vq Wm Tj Ti) Kf(aE Af aW Bn bO Cx dJ Ed Gl Ih Jv Kq Kr Li Ml Ne Nn Nr Nt oE Oh Pb Qc Ra Uh Ul Ur Wm) Jm(Af Al bG Dd Dp Hq Ii Jj Ju Jv Kn Kp Lh Mj Ne Nj Nl Nv Ou Oy Rm St Up Ur Uu Vo Vs) Ph(aA Af aW Ax Bn bO Cx dK fP Fw Gl Ih kS Li Ml Mw Nn Nr Nt oE Oh Pb Pe Pf Qa Qc Qe) cH(aA dG dH dK Dp fP Gl Gp Ha Hr Kn Kp Lh Mw Nv oE Ou Qc Rg Rm Tv Ul Up Ur Uu Vs) dK(aA aE Af bL bM bO Ch cV dJ Dp fP Gl Jo Jv Kc Kg Kj Kl Kp Mw Ne Oy Qc Uh Uu) Vs(aA aD aE Af aH Ba Bn cT CX Ih Io Jv Ky Lh Li Mh Mw Ne Nr Nt oE Pe Uh) Uu(aE Ar bG bO dJ Ez fP Gp Hr Jg Kn Mj Mw Nj Nl Nt Po Rm St Ue Uh Up Ur) No(bG dG Dk Dp Gl Gp Ha Hq Hr Jl Kn Lx Mj Nj Nl Nv Ok On Ou Po Rg Up) Gl(aA aE bG cY dJ Ed Jv Ky Kz Ne Nn Nt Oh Or Ow Pb Rg St Uh Up) Jv(aW bG cV cX dH Dk Dp fP Gp Hr Kn Mj Nj Nl Ou Qc Tv Up) Ou(aA Af Bn Gp It Kp Kz Mw Ne Nn Nr Ow Oy Oz Qc Rg Uh) fP(aE An aW bG Dc gL Hx iJ Ju Ky Lh Ne Nj Nn St Up) Nn(Ao Ch Co Fr Hr Hu Kc Kg Kl Mm Nv Oy Po Uf) St(bL Bn Ch Cx Hq Jo Kg Mw oE Of Oh Qc Rf Rx) aW(aA bM Dp Dr Gp Hr Ju Kc Kg Lh Rg Tr Uh Vo) Up(bL Bn Ch Kc Kl Kp Md Na Nv Qc Rg Uh) aE(Af Bn Dk Hr Lj Mw Oy Qc Tr Ur Va Vo) bG(aA Bn bO Cx Kj kS Lh Mw oE Pb Qc Uh) Ne(Af dH dJ Hr Mw Nv oE Qc Rg Uh) Ez(Aj Bg Ch Jo Kg Kj Kl Ng Oy) Nt(Aj Bg bL Ch Dk Hq Hr Nv Oy) Ed(Ha Jl Mr Nj Nl Po Rg Rm) Mj(Fw Fy Lj Nr Oa Qa Qd Tz) Lh(Ar bL Bn dR Fy Hb Qb Qe) Uh(aA bO Hr Kn Nj Nl Nv Pb) Qc(aY Ki Nj Nl Or Qw Ra) Oh(Ar Kn Ky Lx ON Po) Ru(aA Af Dr Jo Kj Wb) Rg(An Bn Kj Lz Ml Vo) Nj(Jr Lj Qe Tz Vo) Rx(bN dA fR Ih Ps) Kn(Lj Na Nr Pb) Ky(Af Hr Ml oE) Cx(Ju Va Wc) Nb(Rt We Ti) Nl(Jn Lj Tz) Hq(Mw Qw Sr) Tr(dJ kS Qx) Qv(Hr Jo Nv) Or(aA Af Vo) Pb(bJ kS oE) Ar(Rf Wm) Bn(Ju Rm) Dp(aA aY) Dr(Kd Th) Po(Fy Pe) Ug(Jo Kj) Va(aD aN) bN(Fc Th) AfdH ChMw DuPe WmKl FwRt GpNu MibL IhRm JyNv KcaA OyPa oEoF} Im{Eq(Af aG aJ aK Ao AP aQ aR aU aW aX Ba bC bF Bn Bo bP bQ bW bX bZ cE Ch cL cN CO cS Cu Cw CX cY cZ Dd De Dk dM DR Et Ez Gc GP Hb Hc Ho Ib Ic iH iJ iO iP Iv Jh Kc Kg Ki Kq Ld Li Lu Ma Mg Mi Mm Mt Mu Mv Nk Nn Nq Nt nY OE Oi Pc Pd Pj Qb Qn Qt Qv Qy Ri Rx Rz Uf Ug Uh Un Ur Uu Vq Vt Wd Wf Ye) Wf(Ad Af aG aI aJ aM An As Ax bA BC bI bJ Bn bV Ch cM Cp CQ Cs Cu Cv Cw Cx Dc Dd dG Dk dM dN Dr Du eF Em Ex Gb hB hC hG Hl Ho Ib Id Jd Je Kd Kf Kg Kk Kn Ko Kp KQ Kr Kx Ld nY Ph Pi Pk Qn Rj Ry Up Ur Us Ut Uu Uv Yl Tl Xa) Uu(Dr Du Et Fc Fd Fi Gb Gc Gn Hl Ho Hp Lp Rt Ru Rv Ry Si Uw Uy Uz Vb Vh Vw Wc Wd We Wg Wh Yl Zw Tl Xa Ti) nY(Em Fd Gb Gd Gh Gn Hl Ho Hp Lp Rt Rx Rz Sf Sh Si Sj Ux Va Vb Vw Vz Wc Wd We Wh Yl Zw Tm) aG(Du Fc Fd Fi Gb Hl Ho Lp Op Rt Rv Ry Rz Uw Uy Uz Va Vb Vh Wc Wd We Wg Wh Yl Ye Tl Xa) gP(Du Fd Fi Gh Hl Ho Hp Lp Op Rt Rv Rx Rz Sf Ux Va Vb Vh Vw Wc We Yl Zw Zx Tl Xa) Dr(Cx Hl Ld Lp Ne Oi Qt Qv Qw Rc Rt Ry Ss Tv Ua Ug Uh Ur Us Vp Vs Vt Vw We Wm) aJ(Du Fc Fd Gb Hl Ho Lp Op Rt Ru Rv Ry Uw Uy Uz Va Vb Vh Wc Wd We Wg Yl Tl Xa) Uh(aA As bN Cq Cu Gb Hv Hw In It Iv Jn Jq Jr Kd Lw Ml Na Ow Qa Ra Up Vp Yl) Qv(Fd Fi Gb Gc Gh Gn Hl Ho Hp Lp Op Sf Sj Wb Yd Yl Zw Zx Ye Tl Xa) We(Ad Af Cp Cq Cu Cw Cx Dc Em Hc Hl Kd Kn Kq Kr Mr Pi Qn Up Xa) Xa(aH aR bX cX dG dM fP Ha Jk Ld Qt Qw Rj Rx Ua Ug Ur Vp) Qn(Du Gb Ps Rt Ru Rv Uw Ux Uy Uz Va Vb Vh Vw Wc Wd Wg Wh) Uz(Af aH Bn Bo bX CX Dk dM Gn Hc Ib Ld Rj Ry Ua Ur) Rt(Af Bo bP Cu CX Dc Dd Dk Fy Hc Ho Ib Kd Ur) Qt(Du Fc Fd Gb Gc Gh Hl Ho Ry Sf Yd Yl Tl Ti) Nk(Aj aK aQ bN cH Cu cY Dc De Di dJ dR Hb) Ye(bX bZ cR cS dR fP Gb iZ nW oE oN pF Ua) Cx(Du Ps Ru Rv Uw Va Vb Vh Wc Wd Wg) bP(Fd Gh Hl Lp Rv Rx Rz Ux Va Vw Yl) cX(Du Fd Gb Ho Lp Op Ps Ry Uy Va Wc) Hb(aA cH Jq Jv Lw Na No Ou Ow Va) iP(Fd Lp Op Ps Rz Si Sj Ux Wb Wd) Hc(Du Gb Ru Uw Vb Vh Wc Wd Wg) Ry(Cu Hv Jr Mi Na Pi Qw Ug Up) Zw(aH aU dR Et oE Qx Ra Ua) Ch(Rv Ux Vb Vh Vw Wc Wd) De(Jq Mt Mu Oi Om Qd Wd) Du(Af aR Li Oi Pe Qw Ua) Hl(Dd Na oF Ok Sr Ug Ur) Gb(Ib Iz Oy Qw Ua Ug) Wc(Af Bo bX Ib Ld Ur) Rx(Kd kQ Mi Na Un Vt) Wd(Aj Bg Iz Mi Oy) Wh(aH Cu Cw Ld Mt) Qw(Fc Gn Op Sh Ti) Ug(Fc Gn Ho Yl Tl) Af(Uw Vb Vh Wg) Gc(Ri Rv Ua Uv) Ou(Ji Jq No Oi) Ur(Fd Ho Lp Wg) Ux(bC Cw Ld Vq) aH(Fi Uy Wb Yl) dR(Fc Rv Wb Yd) Aj(Ne Vb Vh) Ua(Ho Sf Tl) mI(nA Oz Pb) Ti(Hu No) Et(Vs Yd) Fd(Jr Vp) Gd(Fc Sr) Ib(Uw Wg) Sh(aX bM) Rz(aX Ri) Ld(Rv Yl) Va(bM Vq) Pe(kP Uw) aU(Rv Wb) BnWg YdVt KiPs LpRj RuaR VbOy} Pe{Du(aD aE aF An Ap aQ Ar aU Aw aX aY Ba Bb BC bH bJ bM Bn Bo bS bW bX cJ cL cM CO cP CU cW cX cY cZ dB Dd dI dM Dp Et Ez Fi fR Fw Gb Gc Gn Gp hB hC Hu Hv Ic IH iJ iP Iu Iv Jh Jl Jn Jq Kg Kj Ko Kq Kx Kz Ld Li Lp Lu Ma Mb Me Mi Mm Mp Mt Mx Mz Nb Ng Ni Nk Nl Nn No Nq Nt Nv NW oE Oi Om Ou Oz Pa Pb Pc pF Ph Pi Qt Qu Qv Qz Rm Rv Rx Ry Rz Ud Uf Ug Uh Um Ut Ux Va Vo Vp Vq Wd Wf Zw Ye Ti) Zw(aD aE aI aV aX aY aZ bB bC bE bJ bM bN bQ bU bW cB cC cE cG cI cJ cL cO cV cW cX dA dC dD dH dL dR Ed Et fP Gd hG iA iH iJ iZ kR kS nY oE Oh pF Ps Qn Qt Qv Qw Qy Rf Rm Sr St Tz Ua Uc Uf Uk Un Up Ut Uu Uw Vh Vs Vt Wd We Wh Ti Th) Yd(aD aK aP aU aW aY bC bM bS cP cX dM Et Ex gP Ha iH iP Iu Kc Kd Kg Mi Mt Na Nw nY Qv Qw Rj Uf Ug Uh Ur Uu Vp Vq Vt Wf) aY(Eq Fc Fd Gh Hl Ho Lp Lt Op Rt Ry Rz Sf Sh Si Sj Uz Vz Wb Wg Yl Zx Ye Tm Tl Xa) bM(Fc Fd Fi Gh Hl Ho Lp Op Ps Rt Ru Rx Sf Sj Uw Ux Uy Va Vb Vz Wc Yl Zx Tm Tl Xa) Fc(aE aH bN bU cC cX dH dL fR Gd Hx oH Oz Pc Rt St Uu Vh Vs) Pb(Fr Ih Ip It Jn Jp Js Jt Lj Lx Ma Nn Ok On Qa Qd) lX(aA Il Ji kN Lx mM Mu Mz nC nI NR Nt Pf Po) Rt(aD aW bQ cE Cs Dc Ex Jm Kd Ow Qn To Uy Vq) Bn(Eq Ps Ru Uw Va Vb Vw Wd Wg Wh) Ha(bN Fd Gn Ry Rz Sj Uh Wb Yl Tl) Ps(aD Af cX dG Dk Ex Qn Rx) Og(Ih Ip It Jg Jn Lj Mw) Dr(kQ Ru To Ul Uy Th) Gn(Ed Us Uv Vp Vs Tl) Vz(aN aW cX Ex Id Jm) Bo(Hl Ru Uy Vw Wh) Et(Hr Hu Jo Mk Pc) Va(aD Af aZ dL fP) bN(Hb Rx Sf Vs Vt) nI(kN kP nK nL Oz) Ex(Hl Hp Yl Ti) We(Dd Ed Mw Uu) Wf(gL kS Kx Nb) Jj(Ip Jn Lj Nm) Ye(Hu kS Nb Qy) Of(Jg Jt Mw On) Oy(aA Jt Ok On) Af(Eq Ru Uy) Hr(Jn Jq Jt) Rx(aA aE cC) Uw(aD Dd Qg) Pd(aA Ir No) aW(Hl Wb Yl) mF(nC nH nL) Fd(aD Ed) Ih(Oe Oz) Wd(De Uv) Xa(dL fP) Tl(aD Qy) Lj(Nn Oz) Ur(Lp Ru) AaIq GlRv NkUh WbcX ShUv RzUu mZnA nCnD} Lj{Jj(Fr In Iq Jh Jk Jl Jm Jo Jp Lh Lw Lx Ma Mm Mr Mt Mz Nb Nc Nd Nn Ns Nu Nv Ny Og Oh Om Oz Pa Pb Pc Pf Pg Pz Qa Qb Qc Qd) Og(Fr Ii Il In Iq Jk Jl Jm Jn Jo Jp Lh Lx Ma Mm Mn Mp Mr Mt Mz Nn Ns Nu Nv Ny Oh Oz Pa Pb Pc Pz Qa Qb Qc Qd) Pb(Fr Hv Hw Ii In It Jh Jl Jn Jo Jr Lx Mg Mm Mn Mr Mt Mu Nd Nm Nn Nv Ny Oe Om Pa Pc Pf Pg Po Qa Qd) Lw(Ip It Iv Jg Jn Jp Js Lh Lx Ma Mf Mi Mn Mr Mt Mz Nb Nc Nm Nq Ns Nt Ny Oz Pa Qc Qd) Jn(Fr Ip It Iv Jg Jp Jq Lh Lx Ma Mg Mm Mn Mp Mz Nb Nd Nm Nn Nq Ns Nt Oz Pa Pc Qd) Oe(Fr Ii Ip It Jh Jk Jl Jo Jq Js Lh Ma Mm Mt Mz Nb Nm

Figure 38 Continued

Nn Nq Nv Ny Om Pa Pz Qa Qd) Oz(Fr Ip It Jg Jl Jp Jq Js Lh Lx Ma Mg Mi Mm Mp Mz Nb Nm Nn Nq Nt Pa Pf Qa Qd) Nm(It Iv Jp Jq Js Lx
Mi Mp Mt Mz Nb Nc Nd Nn Nq Ns Nt Pa Pc Qa Qb Qd) Ip(It Iv Jg Jp Jq Js Ma Mg Mi Mm Mn Mp Mz Nb Nc Nn Nq Nt Ok Pc Qa Qd) It(Fr Jh
Js Lh Lx Ma Mg Mn Mt Mz Nb Nd Nq Ns Nt Oh Om Pa Pc Qd) Nn(Hu Jg Jq Js Ma Mf Mn Mr Mz Nb Ns Nt Ny Oi Ok Pa Pc Qa Qd) Jq(Hr Iv
Jg Lx Ma Mg Mm Mn Mp Nc Nd Nq Ns Nt Nu Ok Pa) Jg(Hu Jp Js My Mz Nc Nd Ng Nq Nt Oh Oi Oy Qb Qd) Iv(Du Fr Jp Ma Mg Mi Mn Nd
Nq Ns Ny Oh Ok Pc) Mm(Hv In Jp Jr Js Mf Mr Mz Nb Ns Nt Qa Qd) Nq(Aa Jp Jr Js Mf Mz Ns Ok Qc Qd) Ma(Ik Js Mi Mz Nb Ns Nt Qa Qb
Qc) Mg(Jp Jr Js Mf Mz Nc Nd Ns Oy) Du(Cu Jd Kq Ld Li Mq Mt Pd) Nt(Js Ly Mn Nd Ne Ns Pc Qc) Mp(Jr Js Mz Nb Ny Ok Pc Qc) Nb(Hr Hx
Jp Mh My Oy Ti) Ns(Jh Jp Js Mi Ok Qd) Qy(Dr Eq Gh Yl Ye Tl) Gb(bM bO hB Ld) Mi(Js Ly Mn Ok) Jp(Js Lx Oh Pc) Ps(CX dl Qn) Ld(Fc Vh
Vw) Pc(Js Mz Qd) Dr(hC Ow) Mh(Lx Mt) Hr(Jo Mz) Jh(Hu Oy) bM(Vw Wd) GchG MfJs MtMy MwQd NcNk HpRx IhIq IkOm VzSr SiaA SjcE RtPi} Li{Du(aA AF Aj aP AX bC bH bM Ch cQ cR Cs Ct cV cX De Dg dH dJ Dr Ed Eq Ex FP Fr Hf Hx Ih Ir Is It Iv Ji Jl Jn Jr Js Ju Ki Kl KQ Kz Lx Mj Mr Ms Mv Mw Mx Ng Nh No Nr Nw Ny Oa OE Oh Ow Oy Oz Pb Pc Pk Po Ps Qa Qb Qt Qu Rf Rg Rm Rz Sr Tz Ug Un Uu Ux Va Yd Tm Xa) Yd(aC aE aF aJ aN aO aR aS aU aV aX aY aZ bA bE bF bG bJ bL bM bO bR bS bW bZ cG cH cL cS cV cW dD dF dG dH dL Ed eF Eq Ex fP Gb iA iZ kR kS Ms Mv oE oF oH oK oN pF Ps Qd Qy Rc Rg Rt St Tn Ub Uh Um Un Uo Ur Uv Vc Vt) Ed(Dr Eq Fc Fd Fi Gh Gn Hl Ho Lp Op Ps Rt Ru Rv Rx Ry Rz Sf Sh Uw Ux Uy Va Vb Vh Vw Vz Wb Wc Wd We Wf Wh Yl Zw Zx Ye Tm Tl Xa Th) fP(Dr Eq Fc Fd Fi Gb Gc Gh Gn Hl Ho Hp Lp Op Ps Rt Ru Rx Ry Rz Sf Sh Si Sj Ux Uy Va Vb Vh Vw Vz Wb Wd Wh Yl Zw Zx Tl Xa) bM(Fc Fi Lp Ps Rt Ru Rv Rx Si Uw Uy Va Vb Vh Vw Vz Wc We Wf Wh Yl Zw) aX(Fc Gb Hp Rt Rv Rx Va Vw Vz Wb Wc Wd Wh Zw Tl) Dr(Ef iO Nc Ne Nj Nl Nx Ru Sr Us Uv Uy Th) Eq(aY Ba bJ Cx Hu Iz Jh Jk Mw Nb Ny Qy St) Wb(aN aW aY cR cX Fc Il iO Jm Kd Us Uv Th) Ps(Af aN aY Bn cC Ch De Fc Gl Oz Rx Us Uv) Rt(Af cC Ch CV cX De Kd Ki) Fc(aA aZ cV dK Kg Un) Af(Ru Rv Uy Vh We) No(Ru Rz Vs Wd We) Va(aE aV aY aZ dL) Th(Iv Ny Pk Sr) aA(Fi Ru Rx Uy) Hp(aN Us Uv) Uh(bN Ni Nk) bO(Fi Lp Uy) cV(Gh Hl Vz) mZ(kN kP lX) Cx(Rv Ux) nI(nK nL) iZ(Wf Ye) ChVw DeQd TiNb VzSr SfhG SjUs ZwdA QyRz LdUy LpdD UxaY VsaE} No{Rx(aC aE aF aG aK aM aN aP aQ aR aU aV aW aX bC bH bJ bL bP bQ bW bZ cE cJ cL cN cO cP cR cS cU cV cZ dC dK dN Ef Eq Et gL gP hB hC iJ iO nW Ps Pz Qa Qd Qe Qt Qu Qw Qy Qz Rh Rm St Tn Ua Uc Uf Uh Us Ut Uv Uw Uy Vq Vs Vt Wd) aW(Du Eq Fd Fi Gh Hl Ho Hp Lp Op Ps Rv Ry Rz Sf Sh Si Sj Ux Uy Va Vb Vw Vz Wb Wf Wh Yl Zw Zx Ye Tl Xa) Ti(aA aG aN aY bM cE Cw Ed Fw Gp Hu Ki Kq Mg Mu Mw Nn Nq Nx Oa Qv Rh Sr Ur Uu) Zw(aF aK aU bC bG bQ bW cL cO cS cU cV Cx dI dK dR iH Kq Mu nW Uf Vq Vt) Th(Ao aU aX cS De Ez Gc Ho Jd Jh Ji Kq Mu Mv Nq Pj Qd Rz Uf Un) Fc(aI aK aQ aU aZ cQ cW cX cY dR Et fR Gd hB Ug Uh Vt) aU(Du Fd Fi Ps Ru Uy Va Yd Tm Tl) Kd(Eq Rt Si Ux Vb Vw We Wf Wh) Cx(Gb Hp Rv Rz Va Vh Wc Tl) Wd(Ap Ch cX De Gp Ib Ss Us) Ho(bM cW Oe Uu Vs Vw Wm) Uy(cO dR Gc Ld Mk Nq Ur) nW(Du Ps Rt Va Wh Zx Xa) Eq(aF Ap Bb Ch Ib Nn) Rz(bM Ch cX Ic Ss Uu) Ou(aF Hb Mw Oz Qc Uh) Vs(Et Kq Nw Qd Qy Uh) Yd(aG aK dR Et Vt) Wf(aF Bb gL Mw Qy) Of(Hv Jo Lw Nm Qa) Va(aK cL cN Cw Vq) Fi(aK bM cW hB) My(Jh Jq Mg Mt) Hr(Hw Jo Jr Js) Ye(aF gL Mw Qy) Ru(dR Gc Ld Nq) Rt(Bb dK Ow Vq) Uh(bN Nk Rm Wc) Vw(aF Ap Kc Uf) Fd(aK dK Vt) Wh(aF Gp Qn) Ps(cX Ow Qn) Ng(Mg On) Sh(dK hC) Jg(Ms Mv) Qy(Aj Ch) Xa(cX Oe) Vq(Vh Wc) Pd(Nd Pf) DuLd EdSi EtUu GhdR GbcX GniH GpVb LzMh MdJq MeMf MiHq MkPa NbOy NcNe NiNk HbbN LpaG YlVt NvOn nInK} Og{Jn(Fr Il It Jj Jl Jm Jp Jq Js Lh Lw Lx Ma Mg Mi Mm Mn Mp Mr Mt Mz Nb Ns Nt Nu Nv Ny Om Oz Pa Pb Pc Pf Po Qa Qb Qc Qe) Mw(Fp Fr Hv Ii Il In Jl Jn Jo Jp Jr Lh Lw Lx Lz Mg Mh Mi Mn Mp Mr Mt Nn Nr Ns Nu Nv Oz Pa Pb Pc Pf Po Pz Qb Qe) Jg(Hv Ii Il In Iq Jj Jl Jr Lh Lw Lx Lz Mi Mn Mr Mt Mx Nb Nd Nm Nn Nr Nt Nu Nv Ny Om Oz Pa Pb Pf Pg Po) It(Fp Ii Il Iq Jh Jj Jl Jq Jr Lh Lw Lx Ma Mg Mi Mm Mn Mr Mt Mz Nb Nr Nt Nu Nv Ny Pa Pf Po Qb Qc Qe) Ip(Fp Fr Il Jj Jp Jq Lh Lw Lx Mg Mi Mn Mt Mz Nb Nc Nm Nr Nu Ny Om Pa Pb Pf Po Qb Qc Qe) Ok(Fp Fr Hr In Iv Jj Jq Lw Mi Mn Mt Mz Nb Nc Nd Nm Nn Nr Ns Nt Ny Om Oz Pa Pf Qc Qd) Qa(Iv Jj Jq Js Lw Ma Mg Mi Mn Mt Mz Nb Nk Nn Ns Nt Ny Oe Om On Oz) Qd(Iv Jj Jm Jq Js Lh Lw Ma Mg Mi Mn Mt Mz Nb Nn Ns Nt Ny Om Pb Pc) Iv(aA Fr Is Jm Jp Js Lw Lx Ma Mm Mn Nr Ny Om Oz Qb Qc Qe) Nm(Fp Il Jj Jm Jq Mi Mt Nb Nn Nt Ny Om Pa Pb Po Qc Qe) Js(Jm Jp Lw Ma Mc Mg Mm Nb Nn Ns Nt Nu Ny Om Oz Pa Pc) aA(Fr In Io Jo Jp Jq Lh Lx Me Ns Pc Pf Po) Nn(Jj Jm Jq Mz Nb Nt Ny On Oz Pb Qb Qc) Qb(Fr Ih Jp Jq Ma Mg Mz Nb Nt Om) Is(Jj Lh Lx Nb Oe Pf Po Pz Qe) Ny(Il Jq Lw Mi Mt Mz Nb Nt Qc) Om(Il Jm Ns Oz Pb Qc Qe) Ih(Jm Jo Mj Mv Pa) Jq(Fp Fr Il Nu Qe) Fr(Oz Pb) Jj(Ii Jm) On(Fp My) NtQc} Pb{Mw(Fp Fr Hv Hw In Iq Jg Jl Jo Jp Jr Lh Lw Lx Lz Ma Mh Mi Mn Mp Mr Mt Nb Nm Nn Nr Ns Nv Ny Oe Om On Pa Pf Po Qb Qc Qe) Jn(Fp It Jg Jl Jo Jp Jq Js Lh Lw Lx Lz Ma Mi Mm Mn Mp Mr Mz Nb Nd Nm Nn Nr Nt Nu Nv Ny Oe Pa Pf Pg Po Qb Qe) Ih(Fp Hv Hw In Iq Jo Jq Jr Js Lw Lx Lz Mi Mj Mm Mn Mp Mr Mz Nb Nk Nr Nt Nu Nv Ny Om Pa Pg Po Qa Qb Qc) Qd(Fp Fr Hw It Iv Jg Jj Jo Jp Jq Js Lh Lw Lx Ma Mi Mn Mr Mz Nb Nd Nm Nn Nr Ns Nt Ny On Pc Pf) Ok(Fr Jg Jp Jq Jt Lx Lz Ma Mi Mn Mp Mz Nc Nd Nm Nr Ns Ny Of On Pg Po Qc Qe) Qa(Fc Fr Hr Jg Jp Jq Js Lh Mi Mn Mr Mz Nb Ne Nk Nm Nn Ns Nt On Pa Pf Uh) It(Fp Ip Iv Jg Jl Jq Lh Lx Ma Mi Mn Mr Mz Nb Nm Nt Nv Ny Om Pf Po) Js(Fp Iv Jg Jl Jp Lh Lw Ma Mm Mn Mr Mz Ne Nh Nm Nn Ns Nt Ny Pa Pf) Jt(Jo Jp Lz Ma Mn Mp Mr Mt Mz Nd Ng Nm Nr Ns Ny Of Pg Po Qc Qe) Ip(Fp Fr Jg Jp Jq Lh Lx Lz Ma Mi Mn Mr Mt Mz Nb Nt Pf Po Qb) On(Fp Hu Hv Jq Jr Lz Mh Ms Mz Ng Nk Nm Pf Qb Qc) Iv(Fp Hr Jg Jp Lx Mm Mn Mz Nm Ny Pf Po Qb) Jj(Fr Ii Jg Jm Lh Ma Mn Nn Nt Nv Ny Po Qb) Fr(Hv Jq Jr Mr Mz Nt Oe Qb) Mz(Lx Ma Nm Nn Pf) Qb(Jg Jp Ma Nm Oe) Oe(Jg Lx Nn Po) Jp(Fp Jq Nt) Kq(Ou Uh Uu) Ma(Fp Lh) nI(nH nL) EdWd InaA IsQc} Ih{Oz(Fp Iq Is It Iv Jg Jn Jp Jq Js Lh Lz Mi Mm Mn Mp Mz Nm Nn Nt Nu Ny Om On Pf Po Qa Qd) Iv(Fp Fr Hx In Ip It Jg Jn Jp Lz Mm Mn Mz Ne Nk Nm Nn Ns Nu Ny Of On Oy Pf Qc Qd) Oy(Fp Ip Is It Jh Jn Jp Jq Js Lh Lx Mm Mn Mt Nm Nn Nt Nu Ny Om Pf Po Qa Qd) It(Fp Ip Jn Jq Lx Lz Mi Mm Mn Mz Nk Nm Nn Nt Nu Ny On Pc Qc Qd) Ns(Fp Fr Is Jg Jn Jp Jt Mn Mp Nd Nm Nn Nt Nu Ny Ok On) Nk(Fp Fr Jg Jn Jp Jt Mm Nc Nn Nt Nu Ny Ok On Po Qa Qd) Ip(Fp Fr Is Jg Jn Jp Lz Mn Ms Nm Nn Nt Nu Ok On Pc Qd) Is(Fp Fr Hr Jp Ma Ms Nm Nn Nu Ny Of Ok Qc Qd) Jn(Fr Jp Jt Lz Ma Mm Ms Nm Nn Nu Ok On Qd) Oe(Iq Jq Lh Mt Mz Nb Nr Pa Pc Pf Pz Qb) Jp(Fp Iq Js Lz Mi Ms Nm Nn Nt Qc Qd) Rx(aA aE cM Dr kQ Ps Sr Un Uu Xa) Ms(Jg Mm Mn Nm Nn Ny Ok Om On) Nm(Fp Lz Ng Oi Ok Qb Qd) Va(aG aZ bM Cx Hb Ld Ur) Nu(Jq Lz Mn Mz Oi Qc) Ma(Fp Ng Oi Ok Qb Qc) Of(Jg Mt Nb Ok Om On) Fp(Ik Jq Mm Nn) Lz(Jg Jq Jt Ny) Hr(Hw Jo Jq Qa) Fr(Hu Ng Oi) Nt(Ly Ne Qc) Nx(Ok On Qd) Bo(Du Uw) Ed(Sh Ti) Nn(Oi Ok) Hu(Jg On) Qb(Jg Jt) GcUu MtZw MwIq MyNb NgOn IkQd ShSr JtOi PdPf} Jj{Jn(Fp Fr Ii Jg Jm Jo Jp Jq Lh Lw Lx Lz Ma Mi Mm Mp Mr Mz Nc Nd Nq Nr Ns Nu Nv Ny Oe Om Pc Pf Pg Po Pz Qa Qb Qc Qe) Nm(Hv Hw Ip Iq Jq Jr Lh Lx Lz Mi Mn Mr Mx Mz Nc Nd Nn Nr Ns Nt Ny Oe Ok On Oz Pf Pg Po Qc Qd Qe) Is(aA Fp Fr Hr Ii Iv Jm Jp Lh Lx Ma Mg Mm Mz Nr Nt Nu Nv Ny Oe Ok Pf Po Pz Qa Qb Qc Qd) Ip(Fp Fr Ii Jg Jm Jp Jq Lh Lx Lz Ma Mz Nc Nr Nu Nv Ny Ok Pf Po Qa Qb Qd Qe) aA(Fp Fr Il Iq Jo Jq Lh Ma Me Mg Mm Nr Nt Nu Nv Om Pf Po Pz Qe) Iv(Fr Hr Ii Jg Jm Jp Jt Lh Ma Mm Mn Mz Nr Ny Ok Oz Qa Qb Qd) Jm(Fp Fr Jg Jp Jq Lh Ma Mn Mz Nn Nt Nu Ny Oe Ok Oz Pf Qd) Ok(Fp Hr Il Mn Nc Nd Nn Nr Nt Ny Oe Oz Pf Qa Qb Qc Qd) Nn(Eq Hv Ii Il Mn Nr Nt Nu Ny Oe Oz Qa Qb Qc Qd) Qd(Ii Jg Jq Ma Mi Mn Nt Ny Oe On) Mw(Hv Ma Mr Nv Oe Pf Po Pz Qe) It(Iq Jr Lz Mg Mr Mt Nq Ns Pg) Qa(Fc Jg Jq Ma Mn Nt Nu Ny Oz) Jt(Lh Lx Lz Ma Nd Ns Nt Po Qe) Qb(Ii Jg Jq Ma Nt On Oz) Jg(Fp Il Nt Oe Oz) Ii(Fp Mn Oe Oz) Nt(Iq Mn Ny) Xa(aW aY Fc) Ny(Mn Oz) On(Fp Qc) TiNb FcSr FrOz McJs HpaW UhUr} Qa{Af(Du Fc Fi Gb Gh Hl Lp Op Ps Rt Ru Rv Rx Ry Rz Sf Sh Si Uh Ux Vb Vh Vw Vz Wb Yl Zw Zx Tm Tl) Bn(Eq Fc Hl Ho Rt Rv Sf Si Ux Va Vb Vh Vz Wb Wc We Yd Zw Ye) It(Fr Hr Ik Ip Iv Jg Jp Jq Jt Ma Mn Mw Nk Nm Nn Ns Oe Oy Oz) Uh(aY bG Cw De Gl Ha Hq Jo Ki Lh Mj Ne Ow Qy Rm Up Uu Vp Yd) Yd(aG aJ aN Bo Cx Dd dG Gc Hb Ic Ji Ld nW nY Oz Pj) Oe(Ip Jp Jq Js Ma Mi Nk Nm Nn Ns Nt Ny Oz Pc)

Figure 38 Continued

Fc(Aj cX De dH Dr Gd Hl Ip Oy Oz Ur Uu Ye) Zw(aN bN Cx Kr Lz Oh Qv Qx Ra Us Uu Wm) Rt(cN CX Dd dG Ex iP Kd Qn Vq) aN(Eq Ps Rv Sh Ux Wb Wd We Wh Zx) Mw(Hr Hu Ip Jq Ns Of Ok Oy Oz) Jt(Ip Jo My Ng Nk Ns Oi Oy Oz) Hr(Ip Ir Is Jq Mr Nm Ok On) Jg(aA Ik My Ng Ns Of Oy) Cx(Eq Sh Uw Ux We Zx) Hl(aW cX Ex Kd Qn Uk) Of(Iv Mt Nb Ok On) Us(Rv Sh Wc Wf Ye) Oy(Ip Is Ma Ok On) Rx(aA Aj fP hG) Oz(Ip Is Iv Ok) aY(Sh We Wf Ye) De(Gb Ne Rv) Dk(Du Hp Wb) Ik(Ma Nm Qd) aA(Hu Ma Me) Dr(Kd Qn) Nd(Hq Ns) Wb(aW Qn) Wf(bJ iZ) Ye(Nu Rg) Ur(Lp Ru) BbNe FnUw MyOn HxIv HbbN RzUv VabM nDnI} aA{Ns(Fp Fr Ii Il Io Iq Is Jm Jp Lh Lw Lx Lz Me Mg Mm Mp Nc Nt Nu Om Oy Pc Pf Po Pz Qe) Oy(Fp Ii Il Io Iq Is Jh Jo Jp Jq Lh Lw Lx Lz Me Mm Mt Nt Nu Nv Om Pc Pg Po Pz Qe) Me(Fp Hu Ii Il Is Iv Jp Jq Lh Lx Lz Mg Mz Nr Nt Nu Oe Pc Pf Po Qe) Cx(Fd Fi Gb Ho Lp Ps Si Uw Uy Uz Vh Wb Wc We Xa) Pc(Fp Fr Is Jp Lh Lw Lx Lz Ma Mg Mm Nn Nu Pf Po) Lw(Fp Hr Iq Is Iv Jp Md Mz Nr Nu Oe Pz Qb) Mg(Fp Hu Io Iq Is Iv Lz Md My Ng Of Qe) Of(Fr Ii In Jo Jq Lh Ma Mt Nb Om Po) Hu(Fr Ii Jm Lx Ma Mu Nq Nr Om Po) Uh(aE aW bN cH Nk Ou Ra Ue Ti) Hr(Hv Hw Ii In Is Jq Jr Mz) Oe(Il Iu Iv Jk Jq Mt Nv Pf) Ti(Iv Lx Nb Ny Qe Sr) Fp(Iq Is Jm Ma Mm) Nn(Eq Hb Mz Qb Sh) Nt(Iq Ly Nd Ne Qb) Iv(Fr Iq Jp Ma Mm) Lz(Io Jp Jq Pz) Md(Ii Jq Lh Om) Si(aN Nr Pf Ru) Mz(Iq Nc Nu) Jm(Ma Po Qb) Pf(Fi Pd Sh) aW(Eq kP mZ) Mm(Is Jq) My(Mt On) Nc(Ne Nk) Hb(bN Or) Ps(Oz Rx) Ow(Rx Yd) GcOa NrQb NuJq MaIs MljV NdHq JiRu PdPg nInK jKjT} Jt{Of(Hr Il Ip Is Jg Jh Jl Jp Js Lh Lz Ma Mi Ml Mn Mr Mz Nb Nm Nq Nr Nt Nv Ny Ok Om Oz Pa Pf Pg Po Qc Qd Qe) Hr(Fr Il Iv Jl Jp Jq Lh Mi Mp Mr Mt Nd Ng Nn Nr Ns Nt Ny Oe Ok On Oz Pa Pf Po Qc Qd Qe) Oe(Fr Il Ip Iv Jg Jl Jo Jp Lx Lz Ma Mt Mz Nm Nr Ns Nv Ok Oz Pc Pf Po Qc Qe) Ng(Fp Fr Ip Is It Jg Jn Js Lx Ma Mi Mp Nd Nn Ny On Oz Pf Qb Qd) Jo(Fp Fr Jn Js Lx Lz Ma Mw Mz Nm Nn Nr Ny Ok On Oz Qb Qd) Oy(Fp Fr Ip Is It Jn Js Lx Mp Mt Mz Nd Nn Ny On Pf Pg Qd) Ns(Fp Ip Is It Jn Js Lz Mp Mw Nn Ny On Oz Qb Qc Qd) It(Fr Ik Is Jn Js Lx Lz Mn Mz Nd Nn On Oz Qc Qd) Ip(Fp Is Jn Js Lz Ms My Mz Nc Nn Pc Qb Qc Qd) My(Fp Fr Is Jn Js Lx Mt Nn Nq On Qb) Mw(Fp Hu Js Lz Ms Mz Oz Qb Qc Qd) Oz(Fp Fr Jn Js Lz Nn Pf Qb Qd) Jn(Fp Lz Ms Mz Qb Qc Qd) Qb(Fp Ma Ms Mz Nk) Fp(Is Nd Oi) Ms(Js On) Uh(Ou Uu) DeQd LzIk NdHq JsOi RtaY PdPf} Nb{Rt(aC aF Ao Ap aU aW aX Bb bC bE bJ bW cC cG cL CO cP cS Cu Cw Cx cZ Dd De dK Ef Et Ez Fc Fi Gb Gc Ho iH Kc Kd Kg Ko Kq Ld Ow Pj Rz Vq) Ti(Ad Af aY Bg Bo Ct Ed eF Iv Iz Jk Jo Kj Kl Kp Ld Mn My Oa oE Pz Qw Tn Tr Uc Un Ur Uv Vs Vt) Eq(aF Ap aW Bo CO cS cZ Ez iH Jh Ld Mg Mm Mq Mt Nn Pd Rz Ue Uf Vq) Tl(aJ aN aW bS cX dM gP iP nY Pc Qv Qw Rj Uh Ur Vp Wf) Of(Fr Ip It Jn Jp Js Ma Nm Nn Ny Ok Om Qb Qd) Rx(aF aL cH cV hB iA Kz Ld Mq Nf oH) Bo(Ps Uw Ux Vb Vh Vw Wc Wd We Wh) cV(Hl Hp Lp Op Ry Sh We Wf Ye Xa) Ld(Du Ru Uw Ux Uy Va Vb Vh We) Ur(Fc Fi Gh Gn Lp Ru Si Uy Zw) My(Ip Ir It Jg Jn On) Gc(Ed oE Up Us Uu) Sr(Hl Ry Vz Yl Zw) Wd(Aj De Kj Qy Us) Fc(kS Ow Po Qx) Oy(Ir Jg Mw On) Hl(aF aW Vq) We(aW Co Kq) Wf(Mq Mw Nn) Yd(Uh Un) Qd(De Oe) Us(Fi Rz) Ux(Ap Pj) AaMd DrUh EtNg MqYe HoVq HxIr HbVa SioE RyoH} Mw{Ip(Hu Iq Jp Jq Jr Lz Mi Ms My Mz Nc Ng Ns Nt Oe Of Pc Qb Qc Qd) Jq(Fp Hr Hu Jn Lz Md Ms My Ng Nm Ns Nt Oe Ok Oy Oz Qc Qd) Wf(aW Ax bA cT De dK Em Fy gL iZ Ml Oh oK Ow Va) Nt(Hu Ik It Jn Jr Ly My Ng Ns Oe Of Oy Oz Qc) It(Fp Fr Iq Jg Lz Mi Mp Ms Nk Nn Pc Qc) Jn(Hr Hu Jr Js Lz Mi My Mz Ng Of Qc Qd) Oy(Fr Iq Jg Lx Mi Mt Mz Ok Pf Po Ru Uh) Eq(aW dK Ez Ld Mg Mt Nn Ow Pd Rz) Sh(aD aN aW aZ bA cD cE cT kR Ru) Ok(Hu Js Ms My Ng Ns Oz Qb Qc Qd) Of(Jg Jr Lh Lx Mi Mr Mt Po) Ns(Iv Jr Js Mp Nd On Qd) Oz(Iq Jr Js Lz Mi nI Pf) Hu(Iv Jg Js Nn On Qd) Oe(Iq Jg Nm Nn Ny Qb) Ch(Ru Uh Vb Vw Yl) Uu(Du Gh Op Vz Ti) Iv(Nm Qb Qc Qd) Ru(Af Aj aZ Hc) Uh(Bg bN Nk Ou) Js(Ms My Ng) bN(Aa Nk Vt) De(Hc Qd) Hr(Jr Mz) Ik(Lz Mh) Sr(Gn Ye) Xa(Ua Us) On(Ms Ng) AdWe BgTi DcRt DrVs MyJg NkaZ QcQd WhcT YeiZ LdUy OuVt nTnI} Ed{Xa(Af aW Ba Bn bQ bZ cP cV cW CX DK dR Ez Gn Io Ki Kx Ld Mg Mk Na Nj Nk Nn Oe Oi Ow Oz Pc Pd Qn Qv Rc Sh Vq Vt) Nn(Dr Du Eq Fi Gh Gn Hl Ho Ps Rt Rv Rx Rz Sh Ux Va Vz Wb Wf Yd Yl Zw Ye Tl) Ld(Du Eq Fc Fi Gh Gn Ho Op Rt Ru Ux Va Vw Wc Yd Zw Zx Ye Tl Ti) Va(Ba Cu Ez Ji Lx Mg Na Ni Nk Nw Ow Pd Vq) Na(Eq Fc Fi Gn Ho Rt Ux Vh Wc Zw Ye) Ru(aG bH cV Cx dE Kq Kz Nf Nq Pa Vt) Ba(Eq Fc Fi Ho Lp Rt Ux Wc Yl Ye) Dr(aQ CX dR Hq Ow Pf Pz Vt) Gn(aM Hw Ji Kq Mq Ni On Pd Uw) Ye(Ez Jh Mg Mq Ng Pd Qt) Wh(Af CX OE Oz) Ps(cN CX Oe Oz Qn) Pd(Eq Fc Fi Ho Rt Wc) Uw(Af Bn CX Uu) Eq(Ez Mg Mq Rz) Yd(Et Ji Mt Ow) fR(cN Cx Il Oz) Ti(Nu Oa Qw) Cu(Rt Wc) Ni(Rt Si) Sh(Jg Qt) Wd(oE Oz) Vw(cX dR) DuPo FiMg GcQw NjSi SjbQ ZwOz JiWc RvPf OpOw VbdR} Is{Hr(Fp Fr Hv Hw In Ip It Iv Jg Jn Jo Jp Jq Js Lw Mn Mz Nm Nn Ns Ny Oe On Oz Qc) Ns(Fp Fr Ip Ir It Jg Jn Jp Lx Ma Mm Mn Mp Nm Nn Nu Ny Ok On Oz Qc Qd) Oe(Fp Io Iv Mg Mn Mt Mz Nc Nr Nt Nu Nv Om Pc Pf Po Pz Qb Qc) Of(Fr Ip Jn Jp Js Lx Ma Mg Mm Mn Mt Nm Nn Nt Nu Ny Ok Om Oz) Oy(Fr Ip It Jh Jn Jp Js Lx Ma Mm Mn Mt Nm Nn Ny Ok On Pf Qd) Oz(Fp Jg Jp Js Lx Lz Mm Mn Mz Nn Ny Ok On Qb Qc) Ip(It Jg Jn Jp Js Lz Ma Mn Ms Nc Nn Pc Qc Qd) My(Fr Ma Mm Mt Nm Nn Nq Ny Ok On) It(Jg Jn Lx Mm Mn Mz Nd Nu On Qc) Ms(Jg Jn Mn Nm Nn On) Hu(Fr Jg Ma Nn On) Qc(Jg Ma Mm Nm Ok) Jn(Jp Ma Mm Nm Nn) Yd(aF Mt Qy Un) Fp(Ik Mm Nm) Jg(Lz Ng Oi) Nd(Hq Mk) Rt(aF Dd) Va(dD hG) Pc(Mn Nn) EqNt FrNg NmJo NcNk PdPf nInL} Nn{Eq(aC aE Af aS aX aY aZ Ba bE bH bJ bM BO bQ cB cE Co Cu cV Cx cZ dA dD De dI Dk dL Dr Du Ef Em Fn fP fR hB hC hG Hl Hp Hu Ib Iv IZ Jd Je Jf Jh Jk Jn Jy Kq Ld Lv Lx Mh Mr Ms Mt Mu Mv Mx Ni Nj Nq Nt Nu Nv Nw Ny oE On Ps Qd Ql Qm Qt Qw Qy Rc Rz St Ua Un Uo Wb Wd Yd Ti) It(Hu Ik Ip Iv Jn Jp Jq Jr Js Mz Nd Ns Oe Ok Oy Oz Qc Qd) aX(Hp Va Vw Wb Wd Yd Zw) Dr(Qu Ss Uh Vb Vt Th) Iv(Ip Jn Oe Of Oy Oz) Ps(Aj Bg Ch De Dg Kl) Oe(Ip Js Ok Qb Qd) Wb(fP Qu Ss Vt) Ip(Jn Oy Oz) Sh(aE Qy Zw) Ok(Hr Of Oz) On(Hu My Oy) fP(Gb Zw Xa) Aj(Vb Wd) Qd(Jn Oy) Ny(Rz Wf) aZ(Hp Yd) ChGb EtPc MzOf ZwUn YeiZ KdRt KlVw LpUr UhbN} It{Iv(Fr Ip Jg Jn Lx Ma Mm Mn Mz Nd Nm Ny Oe On Oz Pc Qc Qd) Jp(Fp Ik Jn Jq Lz Mi Mp Mz Nd Nk Nm Nt Oe On Oy Pc Qb Qd) Jg(Fp Ik Ip Jn Jq Js Lz My Nd Ng Ns Oe Of Oy Qb Qc Qd) Fr(Hu Ik Ip Jn Jq Jr Js Mn Nd Ng Ns Oe Of Oy Qc) Qd(Ip Jn Jq Ma Mi Mn Nd Nm Ns Oe Oy Oz Pc) Ip(Jn Jq Jr Js Lx Lz Ma Mn On Oz Qc) Js(Ik Ma Mm Nk Nm Ns Oe Oy Oz Pc) On(Hu Ly Mk Mv Nd Ng Nx Qc) Jq(Fp Hr Lx Ma Mn Nm Nu) Uh(Af Ki Ne Nk Ou Ow Uu) Ok(Ik Ly Mh Ns Pc Qc) Ma(Ik Jn Jr Qb Qc) Lx(Ik Oe Oz) Fp(Ik Nd) Ns(Mp Nd) Mt(Eq My) Mz(Hr Of) CxVa MmJn HbbN KdRt RxbM LdRu LpUr OfOm} Va{Ps(Af aJ aR aZ bM Bn Bo bS CX dB dG Dk dR fP gP Hc Ib iP Ki oE Qn Rj Rx Uu Vq Ye) Sr(aC Af aG aN bM BO cF Dr hG Jf Or Uv Vq Vz Yl) Ld(Al aX Ba Bb Dc Fw Il Ir Jg Jm Kd Lp St) Nw(aC aD aE aN aY aZ bM Bo cD Dd Gl Us) Ow(aE bM bO dL Dr fP Un Uo Wb) Cx(Dd Dr Fd Hp Hv Hx Me Xa) Vq(aZ fP hC iH iZ Nu Ny oH) Un(aN aY cD Ex Fc Fi Fw) Ch(Ef Kq On Qy Ut) Si(aE aV bJ hB hC) Jn(gP Hb Vp Wf) On(fP gP Hc Wf) Vt(aE aG aN Jh) Eq(Ba Om Qy) Rm(Bo dI Hb) gL(aH Oz Pc) Mt(aX fP) Ir(Bo dI) St(dI dR) Oa(aG Hb) aN(Ji Po) AfOm HcNv IuaZ QbaG QyfP KdQm KqUv OhaC PfoK aSbA} Yd{Ow(aF Aj aO aX aY bF bR cG cL dF dH Eq fP Gc Hp kR oH oK oN Ps Qd Un) Kq(aR aX aZ bL cX dG eF fP iO iP NW oE Oi Qb Rj Uh Vs Th) Ji(aW aY bJ cP iP kR Nv nW Or Pz Qd Qy Sr St) Uh(Cu Hw Jh Ld Mr Mt Ni Nt On Pi Ps Sr) Mt(aM aX bV Eq fP Fr Gc Lu Qb Vt) Nw(aW aY Co dK Mg Na Pz Qy Sr Ti) Lx(aC aG aN aY bE bJ Gc Qd Qy) Ld(Ir Pz Qc Qe Qh Sr St Uc Vh) Sr(aG aQ Bo dR Et Ur) Ut(dR Gc Hb Hc Oz Pj) Qd(aW Gc Ic Pj Ti) Et(aY Ny Oa) Nt(Qx Tz Vt) Qy(dR Lh Oh) Po(aY Gc) Om(Bg Eq) On(dR Vt) GccX PsRx NvdR NyaW OaaG PfaY} On{Of(Aa Fp Hu Hv Hw Ip Jg Jo Jq Jr Js Ma Ml Ms Mt My Mz Nk Nm Ns Nt Ny Ok Oy Oz Qb Qc Qd) Oy(Fp Hu Iq Iv Jh Jm Js Lz Ma Mi Ms Mt My Ns Ny Oz Pa Pf Pg Qc Qd) My(Fp Hr Jp Js Ma Mt Nm Nq Ny Oe Pc Qb Qc Qd) Ns(Hu Ip Iv Jn Jr Js Lz Ms Oz Qc Qd) Jn(Hr Hu Ip Iv Ms Ng Nx Oz) Oe(Aa Fp Hu Ip Ly Ms Pc Qc) Oz(Ip Iv Ms Ng Qd) Hr(Hv Hw Jq Ok) aY(Eq Rv Sh Vb) Hu(Et Ip Ir) Ms(Et Ip) Rt(Fw Kd) AaNx EqaF FcUu FpIk NdHq NgJg HxIv RxoH} Uh{bN(aE bA cH dL Et Hx Ib Ii Kf Kg Kj Lh Me Mi Mq Mt Mx Nt Nw Oi Pf Pg Ph Qd Qe Qy Ud Ut Uv) Nk(Cu Dd Fw Hv Ji Jn Jq Jr Js Kd Kq Mi Ml Na Nr Nt Pi Qd Sr Ur) Ou(Cu Dc Dd Hv Iv Ji Jn Jq Jr Kd Kq Ml Na Nt Pi Sr Ur) Kq(Af BG bL Gl Hq Nv Ow Uu Uv Vs) Dr(aW aY Bb Fw Kd Pf) Uu(Jq Lw Na Nm Sr Ur) Ml(Fb Ne Qy) Af(Jq Sr) Ne(Jn Ny) Wb(Nr Ru) DeJi ThIv FbRa FyVs

Figure 38 Continued

JqaW RuiZ} Iv{Hr(Fp Iq Jg Jl Jp Jq Js Lh Lw Lx Lz Ma Mm Mn Mp Mt Mz Nd Nm Nr Nv Ny Om Oz Pf Po Qc Qd Qe) Jn(Fr Ip Jp Ma Mm Nd Nm Oe Of Ok Oz Qd) Oe(Fr Jg Jp Js Lx Nm Ny Ok Qb Qd) Oz(Fr Jp Lx Ma Nm Ok Pf Qb Qd Rx) Of(Fr Ir Ma Mt Nm Ny Ok) Th(Mt Un Ur) Ip(Jp Mn Qd) Qb(Ma Nm Ok) Ru(aZ Ld Ur) Oy(Fr Jg Qd) aY(Lp Si Vb) Ps(aW Rx) BbEq CxVb NmJo NsNd MyJg LpUr} Kq{Rx(aF aY cV eF fP gL gP iA iO iP iZ kQ kR nY oE oF oH oK pF Uv) Ru(Af Aj Bg De Kl Of Oy Tn Uu Uv) Uv(bN Du Fi Ho Lp Sf Si Tm Tl) De(aZ cH Ex Lu Ne oE Vs Th) Ch(bN Ps Qy Vb Wc Wd) Uu(Aa Fc Lp Qy Vs Tm) Nx(Eq Uw Wd Wf Wh) aY(Eq Gc Lp Rt Sh) Aj(bN Qy Ug Vp) Lp(Ur Us Vp) bN(Bg cH Hb) Rt(Fw Nr) kR(Fc Uw) AfUy CxEq WdiZ UxaN} Jn{Oe(Fr Ip Jg Jp Js Lx Ma Mm Nm Nt Nv Ny Qb Qe) Ok(Ip Nd Ns Nx Of Oy Oz Qb Qc Qd) Qd(Ip Mi Nd Ns Oy Oz) Rx(aC aN bJ fP hB Nl) Ns(Ir Jg Jp Mp) Oz(Fr Ip Jp Pf) Jg(My Ng Oy) Rt(aW Cx Dd) Of(Mt Mz Om) Fc(Ur Uu) Zw(Uf Vq) Oy(Fr Pf) AfPs BoTi CxRv EqaF MmIr MtMy NdHq HrPa IpJp WdUs WfaY NwVp UuUx} Js{Oe(Fr Ip Jl Jp Lx Ma Mf Mm Nm Ns Nt Nu Ny Oz Pc Pz Qb Qd) Ip(Jg Jp Ms Ns Of Ok Oy Oz Pc) Oy(Fr Jh Jp Ma Nm Ok Pf Qd) Jg(Hu Ik Jo Ms Mv Ns Oi) Of(Fr Mt Nm Ok Om) Ok(Jo Ns Oz) Nd(Hq Ns) Oz(Fr Jp) FpIk NmJo MtMy HwjE ShaY NwVp VtbN PdPf} Ps{Rx(aF aO cV dA gL iZ Qn Sr) Oe(Bg Ch iZ Kl nY Sh Uu) Qn(iZ NY Oa Oi Uu) Us(Ho Hv Kd Mi Oz Sr) aY(aM hB Kx Lx Oi Po) Oz(aZ Fw gL iZ Oa) Uu(cX Hu Qy Sr) Ch(Jh Qy) Cx(iZ Oa) Sr(Bo Ki) Ur(Lp Nr) cX(iZ Oa) AfFw DeOm ExMl LxaN MiVs WbOw KlaW OicV} Eq{Mt(AN aX bG bI Hq Hw Iz Ky Ng Oz Qy St) Qy(bQ cO Ld Lx Mh Nr Oh Ow Pf) Mq(Bb Fw Il Kd Ph) St(aW Co Jh Mg Rz) Nt(Fw Oh Ow Pf) Ny(aW Mg Rz) Ow(Af Hu Nu) cO(Fw Jg Sr) Mu(Nr Pf) Kd(hB Ql) Ld(Hu Jg) aW(iZ Nv) ChJh CxPd MgcE RzaX UtaF} Qd{Oe(Ip Jg Jp Jq Lx Ma Mi Nd Nm Ns Nt Ny Ok Qc) Ik(Fr jT Lz Mm Mn Nu Pf Qc) De(Ad Bb bN Et Ml Ne Nk) Oy(Ip Jg Ma Nm Ok Pf) Oz(Jp Ma Ns Ok Pf Qc) Jg(Hu My Ng Ns) Ru(Af Dr Ur Uu) Ok(Hr Ip Of) Dr(Kd Th) MujT NdHq PfkN} Dr{Pf(HC iA iH kQ kS nW oK oN pF Rt Sr Uk Vt) Ow(Af aN Cx Oe To Vp) aW(Hb Oa Qg Qx Tz Vt) Kd(Et hB Po Qb Tz) Ru(Ji Mk Mq Po Rh) Sr(aU aV Oe Rx) Th(Ji Mk Mt) Qy(Mh Uu) Oa(Mm nW) BbQx FwSi MtkR IlhB OmUv} Oa{Rx(aC bM bO dI Du fR Gb hG Lx Uo Ur) Gc(bM bO dD dI hG Uo) Rt(Ho Ji Kd Mi Pj) Cx(Gb Uz Vw Wd) Ti(aY Bo Ur) Gb(Af cX Qn) Wf(Hu Jh Qy) Sh(gL Qy) Ye(aC Qy) Vw(Af Oz) FcUr IcWb ZwSr WdUs} Wb{Pf(aF aO bF bG cV dR fP gP hB hC iH iP kQ kS nW oE oK oN pF Qw) Ow(aF aO cV cX Hu Oe Sr) aW(Cs Ji Ld Lx Ml Mq Qx) Sr(aU Uu) Ru(Ji Mk) Oh(aF Qy) aY(hB Lx) NrVt} Et{Ng(Lx Mp Mr Ny Pa Qe) Nt(Hu Ik Jo Ly Nd) Hr(Jr Lh Mr Na Nr) Jo(Hw Lh Mr Ok) Lx(Hq Ly My) Nd(Hv Jr Pd) Hu(Jm Nr Pf) In(Hx Md Ny) Uu(Bb Sr) aY(Sh Xa) bN(Kl Vt) AfUy MiHq MrMy MtMv} Ld{Lp(aM Cv cX dE dR GL hG iZ nY oF oH oN pF Qv Qy Rt Rx To Ur Us Uv) Uy(Hu iZ nY Pc) Xa(aW aY Nx) Kd(Gc Rt Rx) Ru(Em kQ Mr) Fw(Gd Hp) FdQn FikR HoUv HuWh} Ok{Hr(Fp Il In Jm Jq Mz Nc Nd Nm Nr Ns Ny Oe Pc Qc) Oe(Fp Il Ip Jg Nc Nd Ny Oz) Of(Fr Ip Jg Mt Nd Ny Oz Qb) Ip(Nc Oy Qb) Pf(Oy Oz Pd) Qb(Oy Oz)} Sr{Xa(Bo fP oK Oz Pc Uv) Rx(Hx Mv Ny Oy Uv) Rt(bI cH Ph Uv) Uu(Hb Ux Vz We) Sh(aN Hu Zw) Uv(Gn Hl Sf) Vz(Oe Pf) Ur(Lp Zw) BoRu ChWd HpOe HbbN WeOz YlRi} iZ{cX(Fi Gb Gc Gh Ho Si Uw Vw Wc Wd We) Cx(Gb Gc Ho Uw Xa) Gc(Af bQ oE) Rx(Hb Lx Xa) Si(bQ oE) Ji(Ru Uy) AfUw LxZw ShPf YeOm RuUn UyPj} Qy{Uu(Du Fd Ho Lp Rt Si Uz Wc Xa) Ch(Ji Nw Rf Ut Uw Vh Xa) De(Ji Jq Ny) Ow(Sh Ux Zw) Fc(Lx Oh) BgJi MxSh ZwOh RxoF UyhB VtbN} Ir{Of(Fr Jh Jq Mi Mz Nd Nq) My(Mc Mg Mi Mv Om) Hr(Jg Lw Om) Ns(Mm Nk) Mh(Lx Mt) Ne(fR Nt) Hu(Jh Mu) Jg(Jo Ms) CxHl MgNg NlfR PaPf} Ny{aW(Fd Fi Gh Hl Lp Rt Rv Ry Rz Sh Si Sj Ux Vb Vw Vz Yl) Rx(aF cH cV Rg Ur) Wf(bJ gL) Uu(Gc Ux) AaOf YegL RtdK} Xa{aY(Ar Bo cU hB Kx Lx Po) Kd(Aj Jo Rt) Oz(aZ cV) aN(hB Vt) AfOw BoCx FcJo MtfP PzUu RxpF NxUn OeVs} nI{nL(Lz Mx nN Oh oO oQ Oz Pf) nK(Mq mY mZ nT) Oh(nC nH Nx) nN(Jo Nm) mI(oQ Oy) NiQc OznH} bN{Hb(Ji Jq Jr Kd Lw Ml Na Vt) Vt(De Gp Kp Ou Pf Qc) Ji(Ju Nj Nk) BbMl FcLx} Aa{Of(Fr Ma Mg Mv) My(Mg Ml Mv) Nx(Ma Mg Mj) Nq(Ms Om) Md(Lu Mu) NuIq} Jg{My(Ip Jq Mt Mz Qc) Of(In Jq Mz) Oy(Ip Mt Qb) Ng(Ip Qb) NdHq} Lp{Ur(cR Cx Fp Jl Mq Mv Nw Ql) Cx(Kd Mq) AraG CvVq MqaJ} Rt{Kd(Hw Jl Mq Ql) Cu(aY Jm) Nr(aF Kz) gL(Oz Pc) HabQ HoJm aYhB} Oz{Ip(Fp Fr Jp Jq Lx Lz Nt Pf) gL(Rx Sj Wc Wh)} Af{Ow(Fd Gb Hp Uz Vh Wc) Fw(Uw Vh) FiLx MtWe JiRu} Ml{jV(Jq Jr Lw Nw qT) jT(Jq Jr Lw) NwjU} Sh{aY(Ji Pf) hB(Il Kd) MvRu MxbJ HuRm NvcX UvUt} Ru{Aj(Ef Jh) Ch(Jh Nq) bM(Ji Po) BoMr CxHv} Uu{Gc(bQ Hu Nv St) Cx(Gb Ho) FcJi FwWd} Lx{aN(Hp Vz Zw) aY(Vw Vz) FibM ZwUo} hB{aY(Fd Ho Uz Wc) Vc(Il Kd) MvUy} Fp{aN(Fi Ho Ti) DuOw NdHq IkIq} Qb{Oe(Jp Ma Nm Nt) Nt(Zw Ye)} Rx{St(kQ oF) Nw(cV Rg) QchG PcgL} Mq{Kd(Gn Uy) ChRz DdUy FdaN} Mt{aX(Op Zw) DucH GhbM YefP} Nw{Vp(Cu Hv Jr) LwMf} Ch{GhNq JhUy StWd} Nr{MrWf ZwaS WeQl} Qx{FcaZ FdaY NtZw} Jq{Hr(Mr Pa) NsNd} Kd{We(Mv Ql) HlQl} Ow{Kl(Gb Vw) ZwUo} Fw{AjWd WfaM} gL{WcPc WdaX} CsDuaW CxNaVb FcRmUr GhcXfR GbPfhG GlWfUt NtNdHq MgOydX NkJrjR LtNxUn cOnUmZ dMhAjK

Constrained panels with 2 analytes, where 1.0E-8 >= 'model p-value' > 0. Contains 244 panels of 114,549 total panels evaluated. : Im(AA Et Hu Ih Ip Iq Ir Is It Iv Ji Jj Jn Jq Jr Js Jt Li Lj Lz Mi Mw Mz Nc Ng Nn No Ns Nw Oe Og Ok On Oy Oz Pb Pc Qc Qd Sh Ye) Nw(AA Et Hu Ih Ij Ip Ir Is It Iv Ji Jj Jn Js Jt Li Lj Mh Ms Mw My Nc No Ns Oe Of Og Oy Oz Pb Pc Qa) Et(aA Fp Ih Ij Ip Ir Is It Iv Ji Jj Jn Js Jt Li Lj Mw Nc No Ns Oe Of Og Oy Oz Pb Qa Qb Qc Qd) Ji(aA Hr Ih Ij Ip Ir Is It Jj Jn Jq Jt Li Lj Md Ms Mw My Nm No Ns Nu Nx Oe Of Og Oy Oz Pb) Aa(Fp Ih Ip Ir It Iv Jj Jn Js Li Lz Mq Mr Mt Mw No Og Oy Oz Pb Pc Qa Qb Qc Qd Qe) Li(aA Hu Ih Ij Ik Ip Ir Is It Iv Jj Jn Jq Js Jt Lw Mw Nd No Ns Oe Og Oy Oz Pb) No(aA Ih Ij Ip Ir Is It Iv Jj Jn Jt Mw Ns Oe Og Oy Oz Pb) aA(Ih Ij Ip Ir It Jn Js Jt Lj Mw Nm Ok Oz Qc Qd) Ir(It Jj Jp Mn Mw Oe Og Oy Oz Pb) Ij(Jj Lj My Of Og Oy Pb) Mw(Ih Is) Jt(Lj Og) Ke(bN Nx) DuPe IhJj IsLj Constrained panels with 2 analytes, where 1.0E-7 >= 'model p-value' > 1.0E-8. Contains 191 panels of 114,549 total panels evaluated. : aA(Fp Fr Ii Iq Is Jg Jm Jp Lh Lw Lx Ma Me Mg Mm Mn Mz Nn Nr Ns Nt Nu Ny Oe Og On Pb Pf Pz Qa Qb Qe) Ke(bG De Gl Il Jv Kf Lh Mp Ne Nk Pb Ph Qy Rh Uh Us Uu Uv Vp Vs) Ih(Fr Ij Ip Is It Jg Jn Jp Jt Lj Ma Nm Nn Oe Og Ok On Pb Qd) Lj(Ir It Iv Jg Jn Jp Jq Js Mi Mp Mw No Nt Ok On) Mw(Ij Ip It Iv Jj Jn Js Jt Og Ok Qd) Ir(Ip Is Jt Ma Mp Nk Nm Nn Ns Ok On) Aa(Fr Ij Iq Lx Md Mj Mu Nc Nn Pf) Et(Il Jm Jq Lz My Mz Nd Pe Qe) Is(Ij Ip It Jn Nm Oe Og Oz Pb) Qd(Ij Ik It Jj Oe Og Oz Pb) Jt(Fp Hr It Jj Jn Oe Pb Qb) On(It Jj My Oe Of Og Oy Pb) Jj(It Jn Js Nm Qa) Ok(Hr It Jn Og Pb) No(Js Qb Qc Rx) Ij(Hu Lz Oe Rt) Qa(Oe Og Pb) Js(It Og Pb) Vi(cV Sr) Pe(IX Zw) DeKq ItJp YdLi Constrained panels with 2 analytes, where 1.0E-6 >= 'model p-value' > 1.0E-7. Contains 391 panels of 114,549 total panels evaluated. : Ij(Fc Fp Fr Hc Hl Hr Ik Ip Iq It Iv Jg Jn Jp Jq Jr Js Jt Lw Lx Ly Mi Mm Mp Ms Mz Nc Nd Ng Nm Nn Ns Nt Ok On Ou Oz Pc Pf Qa Qb Qc Sh Uh Ur Uu Va Vh Vs Wb Wc We Zw Xa) Lj(Fr Ii Ip Iq Jj Jo Jr Lh Lw Lx Ma Mg Mm Mn Mr Mt Mz Nb Nc Nd Nm Nn Nq Ns Nv Ny Oe Og Oh Om Oz Pa Pb Pc Pe Qa Qc Qd Vi) Is(Fp Fr Hr Jg Jj Jp Js Jt Lw Lx Lz Ma Mm Mn Mz Nn Nr Ns Nt Nu Ny Of Ok On Oy Pc Pf Qa Qb Qc Qd) Ih(Fp Iq Iv Jq Js Lh Lx Lz Mi Mm Mn Mz Nk Nt Nu Ny Om Oy Oz Pe Pf Po Qa Qc) Jt(Fr Ip Jo Jp Js Lx Lz Ms My Mz Ng Nn Ns Ny Of Ok On Oy Oz Pf Qa Qc Qd Qe) Ke(aA aE AF aW cH dJ dK eC fP Im Jm Kn Nj Nl oE oN Ou Qc Rg St Up Yd) Uh(aA bN Cu Dc Hv Im It Iv Ji Jn Jq Jr Kd Kq Lw Ml Na No Nt Qa Ra Sr Up) Js(Fr Ip Iv Jg Jn Jp Lw Ma Mm Nm Nn Ns Nt Oe Of Ok On Oy Oz Qd) Iv(aA Fr Hr Ip It Jg Jn Jp Ma Nm Nn Ny Ok On Pb Qa Qb Qd) Mw(Fp Iq Jp Jq Jr Lz Mi Mz Nt Ny On Oz Pb Qa Qc Sh Wf) Qd(De Ip Jg Jn Jp Jq Ma Mi Mn Nm Nn Ns Nt Ok On Oy) It(Fr Ip Jg Jn Jq Lx Ma Mn Mz Nn Ny Og Qa Qc) Jn(Fr Ip Jp Mm Nn Nt Oe Og On Pb Qa) Ok(Ip Jj Nn Ny Oe Of Oz Qa Qb Qc) Jj(Ii Ip Jg Jm Nn Nt Ny Qb) Og(Ip Jg Nm Nn Ny Om Qb Qe) Qa(Ip Jg Jq Nm Ns Oy Oz) On(Hu Ip Ms Ng Ns Oz Qc) aA(Io jK Jq Lz Oy Pc Po) Pe(Fc

Figure 38 Continued nI Rx Va Yd) No(Ou Zw Ti Th) Im(Eq Hb Ou) Li(Dr Du Vi) Ed(Ru Xa) Nn(Eq Pb) Va(Ps Sr) nI(ml nK) TiNb FrPb JrjK KqUu RxOa LdLp VtbN

Constrained panels with 2 analytes, where 1.0E-5 >= 'model p-value' > 1.0E-6. Contains 630 panels of 114,549 total panels evaluated. : Uh(Ad aE aM As Bn Cp Cq Cw Dd Dr Et Fw Fy Hw Hx Id In Ir Is Jo Js Jt Kg Kn Ko Kp Kr Li Me Mi Mt Mw Mz Nb Nf Ni Nk Nm Nn Nr Nw Ny Oh Ok Om Ou Pb Pe Pf Pi Pk Qd Qe Qy Rb Rf Ri Rj Tv Uc Ud Ul Un Ur Us Ut Vi Vp Vt) Jn(Fp Iq Jg Jq Jr Lh Lw Lx Lz Ma Mi Mn Mp Mr Ms Mz Nc Nd Nm Ns Nu Ny Oz Pa Pc Pe Pf Po Qb Qc Qe Rt Rx Va Wf) Vi(aF aO Ar aY bF BG Bn CH Dk Ed Hc Im Iv Jl Ke Ld Mh Mq Nx Oa Of Ow Oz Qw Rt Sh Ur Uu Va Vt Wf Yd) It(Fp Hv Iq Jl Jr Lh Lw Lz Mi Mm Mp Mr Mt Mx Nb Nd Nm Nq Nr Ns Nt Nu Nv Om Oz Pa Pb Pc Pe Pf Po Qb Qe) Mw(Bb Fr Hu Hv Jg Jl Lh Lw Lx Mh Mn Mp Mr Ms Mt Mx Nc nI Nm Nn Nr Ns Oe Of Ou O

Ki Ld Nb Nl No Nu Oa Pe Um Up Ur Us Uu Uv Vp) Yl(Ad AF An aW aY bJ bM bN cV Cx Fw Gl Hv Ii Je Jj Jo Kr Ld Li Lj Nb Nc Nj Nk No
Pe Qn Up Uu Uv) Uw(aA Ad AF aM An aW aY bN cP Gl Je Jo Kq Ld Li Mt Mu Nb Ni Nk No Nt Pe Qa Rb Up Us Uv Vp Vs) Si(aA aC AD Af
An aO aW bE bG cP cV Cx Fw Gl Hu Hv Ih Je Jo Ki Kr Ld Li Nb Nl No Nu Pe Us) Uz(aA Ad aE Af An aY bG bJ bM bN cP Gl Hu Hv Jo Ki
Ld Mj Nb No Nu Of Rb Ri Um Up Us Uu Uv Vp) Fi(aE AF Aj aW aY bG bJ bN Fw Gl Hu Hv Je Jj Jo Ki Kl Kr Ld Lj Nb No Nu Oa Rb Um Us
Uv) Sj(aE Af An bG bJ bM bN cP Fw Gl In Je Jj Jo Ld Lj Mj Nb Nh Nk Nl No Nu Oa Qn Up Us) Lt(aA Ad AF An aS aY bJ bM bN cP Cq Gl
Hu Hv Je Jo Ki Ld Nb Nl No Nu Up Us Uu) Gc(aN aY bO Dg Gl iZ Je Jf Ki Kj Kl Kr Ld Nc Ne Nj Nk Nl Oa Of Rb Us Uv Vp) Hp(Af An aW
bJ Cq Fw Gl Je Jj Jo Kd Kr Ld Li Lj Nb Nu Pe Qn Ug Um Ur Us) bN(Dp Fy Hb Hc Ju Ke Kj Kl Ld Ou Qw Qy Rc Tv Uh Ur Us Uu Uv Vo Vs
Vt) Og(aA Et Ik Ip Is Jg Ji Jj Jm Jn Li Lj Me Mw Nd Ns Nw Oz Pb Qc) Ke(AF De fP Gl Jo Lh Mp Nk Nx Rm Up Uv Vp Vs) Nw(Hr Hu Jj Mw
My Ns Of Oy Oz Pb Qc Rm Vp Vs) Vs(aE Et Ez Kq Ld Li Nk Ou Qd Qy Ue Uh Ut) Gz(AF Ch Hc Jo Of Us Uu) nl(ml nK nT Oz Pb Pc Qc)
Li(Ik Jj lX Of Oy Pb) Hc(Ex Hq Nk Ou Qy) Aa(Ib Jj Pb Qc) Of(Et jT nC Qg) Uh(Hq Ou Up Uu) eP(Nc Ne Nj Nl) Oz(nC nH nL) lX(aA Lz Pe)
Ch(Qy Rm) Et(Lj Pb) Ne(Aj Qt) Nk(dX Qt) Ou(dJ Mw) ExUr NcdX JoVq UudJ PekN} Pe{Fc(aA aC AD aF aG al AJ aK AL aM An AO AP
aQ AR AS aU aV AW AX aZ BA BB BC bE bF BG bH bI bJ bL bM BO bP bQ bR bS bV bW bX bZ cA cB cD cE cF cG CH cI cJ cK cL cM
cN CO CP CQ cR CS CT CU CV CW cY cZ dA DB DC DD dE dF DG Dl dJ DK Dl dM dN Dp DR Du Ed Ef Em Eq Et Ex Ez Fd Fi Fn Fp Fr
Fw Fy Gb Gc Gh Gn Gp Gz HB Hc Hf hG Hl Ho Hp Hq Hr Hu Hv Hw Hx Ib Ic Id Ih Ii Ik Il In Io Ip Iq Ir Is It Iu Iv Iz Jd Je Jf Jg Jh Ji Jj Jk Jl
Jm Jn Jo Jp Jq Jr Js Jt Ju Jv Jy Kc Kd Ke Kg Ki Kk Kl Kn Ko Kp Kq Kr Ks Kx Ky Kz Ld Lh Li Lj Lp Lt Lu Lv Lw Lx Ly Lz Ma Mb Mc Md
Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn No Nq Nr Ns
Nt Nu Nv Nw Nx Oa Oe Of Og Oh Oi Ok Om ON Op Or Ou Ow Oy Oz Pa Pc Pd Pf Ph Pi Pj Pk Po Ps Qa Qb Qc Qd Qe Qg Qh Ql Qm Qn Qt
Qu Qv Qw Qx Qy Qz Rc Rh Ri Rj Rt Ru Rv Rx Ry Rz Sf Sh Si Sj Sr Ss Tn To Tv Tz Ua Ub Uc Ue Ug Uh Uk Ul Um Uo Up Ur Us Uu Uw Ux
Uy Va Vh Vi Vo Vp Vq Vt Vw Vz Wb Wc We Wf Wh Zw Zx Ye Tm Tl Xa Wm Tj Th) Yd(aA aC Ad aE aG aH al Aj AL aM An AO Ap aQ
AR AS aV Aw AX aZ BA BB Bc bE bF BG bH bI bJ bL BN bO bP bQ bR bU bV bW bX bZ cA cB cC cD cE cF cG CH cI cJ cK cL cM cN
CO Cp CQ cR CS CT CU CV cW Cx cY cZ dA DB DC dD DE dF DG dH DI dJ dK DL dN Dp DR Ed Ef Em Eq Et Ez Fd Fi Fn Fp Fr Fw Fy
Gb Gd Gh Gl Gp Gz Ha Hb Hf Hl Ho Hp Hq Hr Hu Hv Hx Ic Id Ih Ii iJ Ik Il In Io Ip Iq Ir Is Iu Iv Iz Jd Je Jf Jg Jh Jj Jk Jl Jm Jn Jo Jp Jq Jr Js Jt
Ju Jv Jy Kc Kd Kf Kg Ki Kj Kk Kl Kn Ko Kp Kq Kr Ks Kx Ky Kz Lh Lj Lp Lt Lu Lv Lw Lx Ly Lz Ma Mb Mc Md Me Mf Mh Mi Mk Ml Mn
Mq Mr Ms Mt Mu Mv Mw Mx My Mz Nb Nc Nd Ne Nf Ng Nh Ni Nj Nk Nl Nm Nn No Nr Ns Nt Nu Nv Nw Nx Ny Oa OE Of Og Oh Oi Ok
Om On Op Or Ou Oy Pa Pb Pd Pf Pg Ph Pi Pk Po Ps Pz Qa Qb Qc Qd Qe Qg Qh Ql Qm Qt Qu Qx Qy Qz Ra Rb Rc Rf Rg Rh Ri Rm Rt Ru Rv
Rx Ry Rz Sf Sh Sj Sr Ss St Tn To Tv Tz Ua Ub Uc Ud Ue Uh Uk Ul Um Un Uo Up Ur Us Ut Uv Uw Ux Uy Uz Va Vb Vc Vh Vi Vo Vs Vw
Vz Wb Wc Wd We Wg Wh Yl Zx Tm Tl Xa Wm Tj Ti Th) Va(aA aC Ad aE aF aG aH AJ aK Al aM An AO AP AR AS aU aV AW AX BA Bb
BC bE bF BG bH bI bJ bL bN BO bP bQ bR bS bU bV bW bX cC cD cE cF cG CH cI cL cM cN CO CP CQ cR CS CT Cu CV CW CX cY cZ
dA DB DC DD DE DG dH DI dJ DK Dl dM Dp Dr Ed Ef Et Ex Fi Fn Fp Fr Fw Gc Gd Gl Gn GP Hb Hc Hl Ho Hq Hr Hu Hv Hw Hx Ib Ic Id Ih
Ii Ik Il In Io IP Iq Ir Is It Iu Iv Iz Jd Jf Jg Jh Ji Jj Jk Jl Jm Jn Jo Jp Jq Jr Js Jt Jy Kc Kd Ke Kg Ki Kk Kl Kr Kx Ky Ld Lh Li Lj Lu Lv Lw Lx Ly
Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl
Nm Nn No Nq Nr Ns Nt Nu Nv Nw Nx Ny Oa Oe Of Og Oh Oi Ok Om On Or Ow Oy Oz Pa Pb Pc Pd Pf Pg Ph Pk Po Ps Pz Qa Qb Qc Qd Qe
Qg Qh Qm Qn Qt Qu Qv Qw Qx Qy Qz Ra Rb Rc Rf Rg Rh Ri Rj Rm Rt Ru Rv Rx Sh Si Sr Ss St Tn To Tv Tz Ua Ub Uc Ud Ue Uf Ug Uh Uk
Ul Um Un Uo Up Ur Us Ut Uu Uv Uw Ux Uy Uz Vb Vc Vh Vi Vo Vp Vq Vs Vw Vz Wb Wc Wd We Wf Wg Wh Yl Ye Tl Wm Ti Th) Rx(aC
AD AF aG aH aI AJ aK AL aM AN aO Ap Ar AS aV AW AX aZ BA BB Bc bE bF BG bH bI bJ bN bO bP bQ bS bU bW bX cB cD cE cG CH
cI cJ cL cM CO cP Cq Cs Ct CU CV CW cX cY cZ dA DB Dc DD De Dg dH DI DK DL dN Dp Dr Ed Em Et Ex Ez Fd Fi Fn FR Fw Fy Gb Gd
Gh Gl Gn Gp Gz HB Hc Hf hG Hl Ho Hp Hq Hr Hu Hv Hw Hx Ib Ic Id Ih Il Ik Il In Io Ip Iq Ir Is It Iu Iv IZ Jd Je Jf Jg Jh Ji Jj Jk Jl Jm Jn Jo Jp
Jq Jr Js Jt Ju Jv Jy Kc Kd Ke Kf Kg Ki Kj Kk Kl Kn Ko Kp Kq Kr Ks Kx Ky Kz Ld Lh Li Lj Lp Lu Lv Lx Lz Ma Mb Md Me Mf Mg Mh Mi
Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx
Oa Oe Of Og Oh Oi Ok Om On Op Or Ou Ow Oy Oz Pa Pb Pc Pd Pf Pg Ph Pk Po Qa Qb Qd Qg Ql Qm Qn Qt Qu Qv Qw Qy Rc Rt Ru
Rv Ry Rz Sf Sh Si Sj Sr St Ub Ud Ug Uh Uk Ul Um Uo Ur Ut Uu Uv Uy Vb Vi Vo Vs Vt Vz Wb Wc Wf Yl Zx Ye Tm Tl Xa Tj Ti Th) Ru(aA
aC aD aE aF aG aH aI AJ aK An Ao AP Ar AS aU aW Ax aZ Ba Bb bC bE bG bH bJ bN BO bP bQ bS bU bW bX bZ cD cE cL cM CO cP Cq
cR cS Cu CV CW cX cY cZ DD De dG dl dJ Dk dL dM Ed Ef Em Et Ex Ez Fd Fp Gb Gc Gd Gh Gl Gn Gp Gz Hb Hc hG Hl Ho Hq Hr Hu Hv
Hw Hx Ib Id Ih Ii Ik Il In Ip Iq Ir Is It Iu Iv Jd Jf Jg Jh Ji Jj Jk Jl Jm Jn Jo Jp Jq Jr Js Jt Ju Jy Kc Kd Ke Kg Ki Kp Kq Ky Kz Ld Li Lj Lp Lu Lv
Lx Lz Ma Mb Md Me Mf Mg Mh Mi Mj Mk Ml Mm Mp Mq Mr Ms Mt Mu Mv Mw Mx My Mz Nb Nc Nd Ne Nf Ng Nh Ni Nj Nk Nl Nm Nn
No Nq Nr Ns Nt Nu Nv Nw Nx Ny Oe Of Og Oh Oi Ok Om On Ow Oy Oz Pa Pb Pc Pd Pf Pg Pj Po Ps Pz Qa Qb Qc Qd Qe Qg Ql Qm Qn Qt
Qu Qv Qw Qx Qy Qz Ra Rb Rc Rh Ri Rj Rm Rv Ry Rz Sh Sr Ss St Tn To Tv Tz Ua Uc Ud Ue Uf Ug Uh Uk Ul Um Un Uo Ur Us Ut Uu
Uv Uw Ux Uy Vh Vi Vo Vp Vq Vs Vt Vw Vz Wb Wc Wd We Wf Wh Yl Zw Ye Xa Wm Ti Th) Vi(aA aC AD aE aF aG AJ Al An aO AP AR
AS aW aZ Bb Bc bF BG bJ bL bM BN BO bP bS bU bW bZ cD cE cH cN cO Cp Cq Cs Cu CV CW dD De dF Dg dH DI dK dL dM Dr Ed Ef
Ez Fd Fn FP Fr Fw Gc Gd Gl Gn GP Gz Hc Hl Hq Hu Hx Ib Ic Id Ih Ii Ik Il IP Iq Is It Iu Iv Iz Jd Jf Jj Jk Jm Jn Jo Jp Jq Jr Js Jy Kd Kf Ki Kl kQ Kr
Ky Ld Lh Li Lj Lu Lv Lx Lz Ma Md Me Mf Mg Mh Mi Ml Mm Mr Ms Mt Mu Mv Mz Na Nb Nc Ne Nh Ni Nk Nl Nm Nn No Nq Nt
Nu Nx NY Oe Of Og Oi Ok On Or Ou Oy Pa Pb Pd Pg Pj Po Ps Qa Qd Qe Qg Qh Ql Qt Qu Qv Qw Qx Qy Qz Rb Rc Rf Rg Rj Rm Rt Rv Sh Ss
Tn To Tv Ua Uc Ue Uf Ug Uh Uk Ul Um Uo Up Ur Us Ut Uu Uv Uw Ux Uy Vh Vo Vq Vs Vt Vw Wc Wd We Wf Wh Ye Tl Wm Ti Th)
Wf(aA aC aD aE AF aG aH aK Al An Ap Ar AS aU aV aW Ba BB Bc bH bJ bM bN BO bQ bU cD cE cF cI cP Cq Cs cU CV cW cX cY cZ Dd
De Dl DL Dr Ed Ex Fp FR Fw Gd Gl Gn Gp Hl Hp Hq Hr Hu Hv Hw Hx Ib Id Ih Ii Il Il In Io Iq Ir Is It Iu Iv IZ Jd Je Jf Jg Jh Ji Jj Jk Jl Jm Jn Jo Jp
Jq Js Kk Ky Ld Lh Li Lj Lp Lu Lw Lx Lz Ma Mb Md Me Mf Mg Mh Mj Mk Ml Mm Mn Mq Mr Ms Mt Mu Mv Mx My Mz Na Nb Nc Nd Ne
Ng Nh Ni Nj Nk Nl Nn No Nq Nr Ns Nt Nu Nv Nw Nx Ny Oa Oe Of Og Oh Oi Ok Om On Op Oy Oz Pa Pb Pc Pd Pf Pg Ph Po Ps Pz Qa Qb Qc
Qd Qg Qn Qt Qu Qv Qw Qz Rg Ri Rt Ry Sr Ss St To Tz Ua Ub Uc Ue Uf Ug Uh Uk Ul Um Uo Up Ur Uu Uy Vh Vo Vp Vs Vt Vz Wb Wc Wd
We Wg Wh Yl Zx Xa Wm Ti Th) Rt(aA aE AF aG aH aI aJ aK AL AN Ap Ar aU aX aY aZ BA Bb bF bN BO bP bS bU cD cL Co cP Cq Cu
Cv Cw cX cY dB Dd DE Di DK Dp Dr Ed Et Ex Fi Fp Fw Gl GP Hc Ho Hq Hr Hu Hw Hx Ib Id Ih Ii Is It Iv Jg Jh Jk Jm Jn Jp Jq Jt Ke Ki
Kq Ks Kx Ky Ld Li Lj Lu Lv Lx Lz Ma Me Mf Mg Mi Mj Mp Ms Mt Mu Mv Mw Nb Nd Ng Ni Nj Nn Nq Nr Nt Nv Nw Nx Ny Oa Oc Of Og
Oh Oi Om On Oz Pa Pb Pc Pd Pf Ph Po Ps Pz Qa Qb Qc Qd Qg Qh Qt Qu Qv Qw Qy Rc Ri Rj Rm Sf Sh Sr Ss St To Tv Tz Ua Ub Uc Ue Uf
Ug Uh Um Un Us Uu Uv Uy Vp Vs Vt Wd Yl Zw Ye Tl Xa Tj Th) nl(aA Et Fp Fr Hq Hr Hu Hv Hw Hx Ih Ii Ik Il In Io Ip Iq Ir Is It Iu Iv Jg Jh
Ji Jj Jk Jl Jm Jn Jo Jp Jq Jr Js Jt kC kE kF kG kI kK kN kO kP Lh Li Lj Lu Lv LW LX LY Lz Ma Mb Mc Md ME MF Mg MH ml Mj Mk Ml
MM Mn MP Mq Mr MS MT MU Mv MW Mx MY MZ NA NB NC ND Ne NF Ng NH Ni NJ NK NL NM NN NO Nq NR Ns NT NU Nv Nw
Nx Ny Oe Of Og Oh Oi Ok Om On oO oP oQ Oy Oz Pa Pb Pc Pd Pf Pg Po Pz Qa Qb Qc Qd Qe) lX(aA Et Fp Fr Hq Hr Hu Hv Hw Hx Ih Ii Ik Il

Us Ut Uu Uv Uw Vh Vp Vs Vz Wb Wc We Wh Yl Zx Tm Tl) Eq(AF aK aN Ap aU aY bC Bn Bo bQ bS bW CO cS cW CX DK Ez Gp Hc Ic Jh
Kc Kg Ki Kq Ld Li Mg Mi Mt Mu Mv Nq Oe Oi Om Ow Oz Pc Pd Qn Qw Qy Rj Uf Uh Uu Vp Vt) Gb(AF aK aN Ap aU aW aY Bb bM Bn Bo
bW CO CW Cx dK Ed Gp Ib Kc Kd Kg Ki Ld Li Lj Mg Mi Ml Mt Mu Nn Nq Oe Oi Ow Oz Pc Pd Pf Qn Qv Qy Uf Uh Vp Vt) Hp(aF aK AN
Ap aU aY Bb bC bH Bn Bo bQ bW CO cW CX cY dK Ez Hu Kc Kg Kq Ld Li Mg Mi Mm Mq Mt Mu Mv Mw Nn Nq Oe Om Ow Oz Pc Pd
Qn Qy Uf Uh Vq Vt) We(aF aK Ap aU aW Bb bC Bn bW CO Cw CX De dK Ez Gp Jh Kc Kg Kj Kq Ld Li Mg Mi Mm Mp Mq Mt Mu Mv Mw
Nn Nq Oe Om Ow Oz Pc Pd Pf Qn Qy Uf Uh Vp Vq Vt) Du(AF aG aK Ap Bb bC Bn Bo bW cJ CO cS Cw CX dR Ez Gp Ji Kc Kd Kg Ki Kq
Ld Mg Mi Mp Mq Mt Mu Nn Nq Oe Om Ow Oz Pc Pd Pf Qd Qn Qy Uf Uh Vp Vt) Fd(aF aG Ap aY Bb bC Bn Bo bQ bW cL CO Cu Cw CX
Ez Gp Hv Iv Kc Kd Kg Kq Ld Li Mi Mp Mt Mu Mv Nn Nq nW Oe Om Ow Oz Pc Pd Ph Qn Qy Uf Uh Vq) Uw(AF aK aN Ap aU aW aY Bb
bC Bn Bo bW CO CX Dk Ez Gp Kc Kd Kg Ld Li Mg Mi Mp Mq Mt Mu Mv Nn Nq Oe Ow Oz Pc Pd Pf Qd Qn Qy Uf Uh Vp Vt) Zx(aF aK aN
Ap aU aY Bb bC Bn Bo bW cL CO CX cY dK Ed Ez Gp Kc Kd Kg Ld Li Mg Mi Mp Mt Mu Nn Nq Oe Om Ow Oz Pc Pd Pf Qn Qy Uf Uh Vt)
Wh(Af aK Ap aU Bb bC Bn bS bW CO Cw CX DK Ez Ib Ic Jd Jh Kc Kg Kq Ld Mg Mi Mq Mt Mu Mv Mw Nq Oi Om Oz Pc Pd Qd Qy Uf Uh
Ur Vp Vt) Tm(aF aG aK Ap aW aY Bb bC Bn bW bZ CO CX Ez Gp Kc Kd Kg Kq Kz Li Mg Mi Mm Mp Mq Mt Mu Mv Nn Nq nW Oe Om
Ow Oz Pc Pd Qn Qy Uf Uh Vt) Ux(AF aK Ap aU Bb bC Bn Bo bW CO cS cW CX dK Gp Ic Kc Kd Kg Kq Ld Li Mg Mi Mt Mu Mv Nn Nq Oe
Om Oz Pc Pd Qn Qy Ss Uf Uh Uu Vp Vt) Hi(aF aK Ap aU aW aY Bb bC Bn Bo bW CO Cw cX dK Ez Fw Gp Kc Kd Kg Kq Ld Li Mg Mi Mt
Mu Nn Nq Oe Om Ow Oz Pc Pd Qn Uf Uh Vq Vt) Lp(AF aK Ap aU aY Bb bC Bn Bo bS bW CO CX dK dR Gp Ib Kc Kg Kq Li Mg Mi Mt Mu
Nn Nq Oe Om Ow Oz Pc Pd Qn Uf Uh Vp Vt) Yl(aF aK aN Ap aU aW aY Bb Bn bW CO Cw CX dK Fw Gp Hu Ic Kc Kg Kq Ld Li Mg Mi Mt
Mu Nn Nq Oe Om Ow Oz Pc Pd Pf Qn Uf Uh) Wb(aF aK aN Ap aU Bb bC Bn bW CO CX dK Gp Kc Kd Kg Kq Ld Li Mg Mi Mt Mu Nn Nq
Oe Om Ow Oz Pc Pd Pf Qn Uf Uh, Vt) Rv(aF aK aN Ap aU aY Bb bC Bn bW CO CW CX dK Gp Kc Kd Ld Li Mg Mi Mt Mu Nn Nq Oe Ow
Pd Pf Qy Sr Uf Uh Vt) Vb(aF aK aN Ap aU Bb bC Bn bW CO cW CX dK Kc Kg Ld Li Mg Mi Mm Mt Mu Mv Nn Nq Oe Om Pd Qy Uf Uh
Uu Vq Vt) Gh(aF aG aK aN Ap aU Bb Bn Bo bQ bW cE CO CX Gp Kc Kd Kg Kq Ld Li Mg Mi Mt Nn Nq Oe Ow Pd Qn Uf Uh Vt) Sf(aF aK
Ap aU aY Bb bC Bn bW CO cX dK Ez Kc Kd Kg Kq Ld Li Mg Mi Mt Mu Nn Nq nW Oe Ow Pd Qn Qy Uf Uh Vt) Wc(aF aK Ap aU aW Bb
Bn bW CO Cw cX Gp Kc Kd Kg Ld Li Mi Mm Mp Mt Mu Nn Nq Oe Om Ow Oz Pc Pd Qy Uf Uh Vt) Vw(aK aU Bb bC Bn bW CO cS CX De
dK Ez Gp Jh Kg Ld Mi Mm Mt Mu Mv Nq Oe Om Oz Pc Qn Qy Uf Uh Vq Vt) Vz(aF aG aK aU Bb Bn Bo CO CX dK dR Gp Iv Kc Kd Ld Li
Mg Mi Mt Nn Nq Oe Ow Oz Pc Pd Pf Qn Uh Vt) Tl(Af aK aN Ap aW aY Bb Bn Bo CO CX Gp Kc Kd Kg Ld Mg Mi Mt Mu Nn Nq Oe Om
Ow Oz Pc Pd Qn Uh Vt) Op(aF aK Ap aU aY Bb bC Bn bW CO CX dK Gp Kc Kg Ld Li Mg Mi Mt Mu Nn Nq Oe Ow Oz Pd Qn Uf Uh Vt)
Ps(Af aG aK aN Bb Bn bQ cL cN CW Cx Dk Ic Jl Kd Ld Li Mg Mi Mp Mt Nn Nq Nw Om Oz Pc Pd Uf Uh Vt) Sj(AF aK aU Bb Bn bQ cE cL
cO cX Gp Kc Kd Li Mg Mi Mt Nn Nq Oe Ow Oz Pc Qn Uh Vt) Ry(Af aK aN aU Bb Bn Bo cO CX dK Gp Kc Ld Li Mg Mi Mt Nn Nq Oe
Ow Oz Pc Qn Uh Vt) Vh(aK aN aU aW Bb Bn Bo cP CW cX Gp Kd Ld Li Mg Mi Mt Nn Nq Oe Oz Pc Pd Uf Uh Vt) Lt(aK aU aW Bb Bn cO
CX Gp Kc Kd Li Mg Mi Mt Nn Nq Oe Ow Qn Uh Vt) Gd(Ed Ez Gp Ic Kc Kd Kg Ki Kq Ld nW Or Ow Qn Qv Qy Sr Uf Vp Vq Vt) Wg(aK
aU aW Bb Bn Bo Gp Kd Ld Li Mg Mi Mt Nn Nq Oe Oz Pc Pd Uh Vt) Em(Ed Ez Ib Ic Kc Kd Kg Kq Ld nW Or Ow Qn Qy Rj Uf Uh Vp Vq Vt)
Uz(aK aU aW Bb Bn Bo Cx Gp Kd Ld Li Mg Mi Mt Nn Nq Oe Uf Uh Vt) Vc(aK aU aW Bb Bn Cx Gp Kd Ld Li Mg Mi Mt Nn Nq Oe Uf Uh
Vt) Gn(Ed Ez Ic Kc Kg Kj Kq Ld nW Ow Qn Qy Uf Uh Vq Vt) Dr(Kc Kd Kg Ld nW Ow Qn Uf Uh Vq Vt) fR(Ed Ez Jd Kg Kq Ow Qy Uf Vt)
nI(kP ml nK nL nN nT Nx Oz Qc) lX(Is Li Mw Pf Qa Qb Qc Qd) Uh(bN Hq Nk Ou Ow Rm Vs) Hb(aW bN dK Hq Oe Qy) Vs(Et Kq Li Nw Qd
Qy) Ou(aF dJ Mw Oe Qc) Qc(kP nN Ow) Uu(bN dJ Et) Ml(jT jV) bN(Ss Vt) mZ(Li Mp) jK(Fr Hu) ChQy DeKq GzOz NxkP] Vi{Lj(aA aC AD
aE Af aH aI aJ AL aM An aO aP aQ AR AS aU aV AW Ax aY aZ BA BB BC bE bF Bg bH bI bL bM bN bO bP bQ bR bS bU bV bX cA cB
cD cE cF cG CH cI cK cL cM CP CQ cR CT CU Cv cW cX cZ dA DB DC dD De dF dG DI dJ dK DL dM dN Dp Dr Du Ed Ef Em Eq Et Fc
Fd Fn Fp FR Fw Fy Gc Gd Gh GL Gn gP Gz Ha Hb Hc Hf Hl Hp Hq Hr Hu Hv Hx Ic Id Ih Ii iJ Ik Il In IP Iq Ir Is It IZ Jd Je Jf Jg Jh Jj Jk Jl Jm Jn
Jp Jq Jr Js Jt Ju Jv Jy Kf Ki Kk Kl Kn Kp Kr Ks Kx Ky Kz Lh Lp Lt Lu Lv Lw Lx Ly Lz Mb Mc Md Me Mf Mh Mj Ml Mn Mq Mr Ms Mw Mx
My Mz Nb Nc Nd Ne Nf Ng Nh Ni Nj Nk Nl Nr Ns Nt Nu Nw Nx NY Oe Of Og OH Oi Ok ON Op Ou Ow Oy Pb Pf Pg Ph Pi Pj Pk Po Ps Pz
Qa Qb Qc Qd Qe Qg Qh Ql Qm Qn Qt Qu Qv Qw Qx Qz Ra Rb Rf Rg Rh Ri Rj Rm Rt Ru Rx Ry Sf Sh Sj Ss Tn To Tv Tz Ua Ub Uc Ud Ug Ul
Um Uo Up Ur Us Ut Uu Uv Uw Ux Uy Uz Va Vb Vc Vh Vo Vs Vt Vw Vz Wb Wc We Wf Wg Wh Yd Yl Zw Zx Ye Tm Tl Xa Wm Tj Th)
Li(aA aC AD aE aF aG aH aI aJ aK aL aM An AP aQ AR AS aU aV AW Ax aZ BA BB BC bE bF BG bI bJ BN bO bP bQ bR bS bV bW bX
bZ cA cB cD cE cF cG cI cK cL cM cN CO Cp Cq CS cT cU CW Cx cY cZ dA DB DC dD De dF dG DI dJ dK DL dM dN Dp Dr Du EF
Em Et Ex Fd Fn Fp fR Fy Gb Gc Gd gL Gn GP Gz Ha Hb Hc Hf hG Hl Ho Hp Hq Hr Hu Hv Hw Hx Ic Id Ih Ii iJ In IO Ip Iq Is It Iu Iv Iz Je Jf
Jg Jh Ji Jj Jk Jl Jn Jo Jp Jq Jr Js Jt Jv Kc Ke Kf Kg Ki Kk Kl Kn Ko Kp Kq Ks Ky Kz Ld Lh Lp Lt Lu Lv Lx Ly Lz Ma Mc Md Me Mg Mi Mj
Mk Ml Mm Mp Mq Ms Mt Mv Mw Mz Na Nb Nc Nd Ne Nf Nh Nj Nl Nm Nn Ns Nt Nu Nv NW Ny Oa Oe Og Oi Ok Om On Op Or Ou Oy Oz
Pb Pd pF Pg Ph Pi Pj Pk Po Ps Pz Qa Qb Qd Qe Qg Qh Qm Qt Qv Qw Qx Qy Qz Ra Rb Rc Rf Rg Rh Ri Rj Rm Rt Rv Rx Ry Sh Si Sj St Tn Tv
Tz Ub Ud Ue Uf Ug Um Un Uo Up Ur Uv Uw Uz Vb Vc Vh Vo Vp Vq Vt Vz Wb Wc We Wf Wg Wh Yl Zx Ye Tm Tl Xa Wm Th) Ed(aC aF
aG aK aM aN Ao Ap aQ Ar aU aW AX aY Ba Bb bC BG bJ bN Bo bQ bS bW bX cD Ch cN CO CS cU Cv Cw Cx cY cZ dB dE Dg dJ DK dM
Dr Et Ez Fc Fd fR Fy Gb Gc Gd Gn Gz Hb Hc Hx Ib Ic Ih Il Io Ir Iu Jh Ji Jj Jl Kc Kd Ke Kg Kq Kz Ld Lp Lu Lx Lz Ma Md Me Mg Mh Mi
Mk Ml Mm Mn Mq Mt Mu Mw Na Nb Nc Ne Nf Nh Ni Nk Nl Nm Nq Nr Nu Nv Nx Of Oh Oi Or Ow Oy Oz Pa Pb Pc Pd Pf Pj Pz Qa Qn Qt
Qv Qw Qx Qy Ra Rb Rh Rt Ru Rv Rx Rz Sh Si Tn Ue Uf Ug Uh Up Ur Uu Va Vp Vq Vt Wd Wf Yd Xa Wm) cV(aC aF aG aK aM Ap Ar As
aV Ax aZ Ba Bg bI bN Bo bR bV bW bX bZ cA cC cD cE cF cG cI cK CO cP CX dC dF dG dI dJ Dk Dp Et Fn Fy Gd Gp Ha HB hF hG Ho Hp
Hq Hu Hv Hx iA Ib Ih iJ Ip Iq Is Iv Je Jf Jg Ji Jj Jk Jl Jn Jo Jr Jt Ke Kg Ki Kl Ko KS Ld Lh Lp Lt Lv Lw Ly Lz Mc Md Me Mi Mk Mm Mp Mt
Nc Nj Nk Nm Nn Ns Nw Oe Og OK Om Ou Ow Pd Pj Pk Ps Pz Qb Qg Qu Qx Qy Ra Rg Rt Rv Ry St Tz Ua Uc Ud Ue Uf Uo Ur Uu Uv Va
Vc Vo Vs Wg Yl Zw Zx Ye Tj) Wf(AF aM aN AP aU aW aY Bb bJ bP bW cN CO cP cQ cS cT cX Dc dF dH Fd Fp Fw Gc Gh Gl Gp Hu Ib Ic
Ih Il Ir Iu Jd Jh Ji Jl Jm Jn Kc Ke Kg Ki Kq Ld Lz Mg Mh Mi Mk Ml Mm Mq Mr Mt Mu Mv Mx Nb Nh Nq Nr Nu Oa Oe Oi Om Ow Oz Pa
Pb Pc Pd Pf Pj Po Ps Pz Qa Qb Qc Qd Qe Qg Qn Qw Qx Qy Rc Ri Rt Rv Sj Tv Ue Uf Uh Ur Us Ut Uu Uv Uy Va Vo Vp Vq Vs Vt Wc Wd Yd
Ti) Sr(aC aD aE Ao AP Aw Ax aY bC bF bH bI bJ bO bR bW cA cK cM Co cR cS cT Cu Dc DD dE dH DI Dr Em Fc Fi hC hF hG Hq Id iH Ii
iJ Ik Il IO Ir Iu Iv Jd Jf Jh Ju Jy Kc Kd Kg Kk Ko Kq KR Kz Lt Lw Ly Ma Mc Md Mi Mq Mv Mz Na Nb Nc Nd Ne Nh Ni Nl Nn Ns Nx Oa Om
Pd Pg Pk Qc Qe Ql Qm Ra Rf Ri Rm Ru Sf Sj St Ud Ue Uf Uh Uy Uz Vc Vq Vz Wd Yd Tm) aF(Ad aH Aj aM Ar aW aX bB BG Bn Bo
Ch cJ Ct cU Cx De Dg Di Dk Dl Ef Fn Fr Gc Gd Gp Hb Hc Hf Hq Hu Ib In iO Ir Is Jz Ji Jj Jo Ke Kj Ld Lp Lu Lz Mf Mh Mk Ml Mn Mp Mu
Mv Mx My Nb Ng Nq Nw Nx Oa Oe Of Oh Oi Oy Oz Pb Ph Pj Qa Qb Qg Qu Qw Qx Rg Rj Rt Rx Sh Tv Tz Ua Ub Uh Ur Us Uv Ux Va Vo Vs
Vw Wd Wh Yd Yl Ye Th) Uu(aL AN Ao aS aU aY Bb bC bE bF BG bJ Bn bP bW cC CH CO cP Cx cZ De dF Dk Dl Ez Fc Fi Fw Gc Gd Gh
Gp hC Ho Hu Hv Ic Ih Il Ir It Iu Iv Iz Jd Jh Ji Jl Jt Kc Ke Kg Kq Ld Lv Mg Mi Mm Mp Mq Mt Mu Na Nq Nq Nx Og Om Or Ow Oz Pc Pd Pf Pj
Pz Qa Qc Qd Qe Qg Ql Qt Qz Rz Si Tn Ue Uf Uh Ux Vp Vq Vt Wd Yd Ye) Dk(aO aP ar aS aU aW BG Bn Bo cJ cQ Cs Ct cU Dg Dp Eq Et Fn

Vh Wc Wd Wg Wh) Ed(Em fR Lt Si Sj Uz Vc Wg) aN(Fd Fi Ho Rv Uz Vc Wc Wd) Em(bO Nc Ne Nj Nl Pc Us) Nr(Ho Uw Vb Vh Wc We Ye)
Sf(aM bN Dg Kg Mm Oa Uv) Wh(aF cX Fr Il Ng Pc Qt) Uh(Aa bL bN bO dJ Hq Nk) nL(kF kO mF Ml nC nD nH) Fd(Bn Bo Gl Ld Us Uv)
Fi(bJ Bo dD Gl Nu Oa) Ye(Ih It Je Nu Oa St) Ke(aF bN Lh Mp Nx Vs) Ho(Gl Kd Ld Us Uv) Ih(Jj Oe Oi Oy) Ik(Ir It Ji Jn)
Tm(Fw Il Jm Kd) Uz(Gl Ld Us Uv) Vs(aE bN Mz Rg) eP(As Nc Nj Nk) nC(kF mF Ml nD) kP(Fr Lh Mz Nx) Bn(Vb Vc Wg) It(aA Et Jj) Wd(Aj
Ng Uv) Oe(Et Ir Jn) Vw(Dg Kl Uu) nH(kF Ml nD) kN(Lz Ml Nx) Gh(bN Ld) Il(Vh Yl) Ji(Nx Of) St(Uw Vh) We(Dd Kd) Tl(aQ Kd) dX(Nc
Nk) AaOy FwYl GlRv NukE IrJj ZxUu QaUw WgUv RyOa VccX VtbN nDnK} Ke{bN(AA aC AD aE AF aG aH aI AJ aK AL aM AN AO AP aQ AR AS aU aV AW AX aY aZ BA BB BC bE bF BG bH bI bJ bL bM Bn BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp dR eC Ed EF Et Ex Ez Fa Fb Fn FP Fr Fw Fy GL GP gW Ha HB HC HF hG Hq Hr Hu Hv Hw Hx iA Ib Ic Id IH Ii iJ Ik Il In IO IP Iq Ir Is It Iu Iv IZ Jd Je Jf Jg Jh Ji Jj Jk Jl Jm Jn Jo Jp Jq Jr Js Jt Ju Jv Jy Kc Kd Kf Kg Ki Kj Kk Kl Kn Ko Kp KQ KR KS Kx Ky Kz Ld Lh Lj Lp Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv NW Nx NY Oa OE OF Og OH Oi OK Om ON Or Ou Ow Oy Oz Pa Pb Pc Pd PF Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Ru Sr Ss St Tn To Tr Tt Tv Tz Ua Ub Uc Ud Ue Uf Ug Uh Uk Ul Um Un Uo Up Ur Us Ut Uu Uv Va Vo Vp Vs Vt Vu Vv Wc Tm Wm Tj Ti Th tF) Nx(aA aC AD aE AF aG aH aI AJ aK AL aM AN AO AP aQ AR AS aV AW AX aY aZ BA BB BC bF BG bH bI bJ bL bM Bn bO bP bQ bR bS bU bV bW bX bZ cA cB cC cD cE cF cG CH cI cJ cK cL cM cN Co CP Cq CS CT CU CV CW CX cY cZ dA DB DC Dd DE dF DG dH DI dJ DK DL dM dN Dp DR eC Ed EF Et Ex Ez Fn FP Fr Fw Fy GL GP Gz Ha Hb HC HF Hq Hr Hu Hv Hw Hx iA Ib Ic Id IH Ii iJ Ik Il In IO IP Iq Ir Is It Iu Iv Iz Jd Je Jf Jg Jh Ji Jj Jk Jl Jm Jn Jo Jp Jq Jr Js Jt Ju Jv Jy Kc Kd Kf Kg Ki Kj Kk Kl Kn Ko Kp Kq KR kS Kx Ky Kz Ld Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nc Nd Ne Nf Ng Nh Ni Nj Nk Nl Nm Nn Nq Nr Ns Nt Nu Nv NW NY Oa OE OF Og OH OK Om ON Or Ou Ow Oy Oz Pa Pb Pc Pd PF Pg Ph Pi Pj Pk Po Pz Qa Qb Qc Qd Qe Qg Qh Ql Qm Qn Qt Qu Qv Qw Qx Qy Qz Ra Rb Rc Rf Rg Rh Ri Rj Rm Ru Rx Sr Ss St Tn To Tr Tt Tv Tz Ua Ub Uc Ud Ue Uf Ug Uh Uk Ul Um Un Uo Up Ur Us Ut Uu Uv Vo Vp Vs Vt Vu Vv Yd Xa Wm Tj) Yd(aA AD AF aI Aj Al aM AN AO aP AR As aV Aw aY aZ Ba Bb Bc bE bF Bg bH bI bL bM Bn BO bP bQ bR bS bW cB cD cE cG CH cI cJ cL cM cN Co Cp CQ cR cS Ct CU CV Cw CX cY cZ dA DB DC DD DE dF Dg dH Di dJ DK Dl Dp dR Du Ed Em Eq Et Ex Ez Fc Fd Fi Fn Fp Fr Fw Gb Gc Gh Gl Gn GP Gz Ha Hb HC hG Hl Ho Hp Hq Hr Hu Hv Hx iA Ib Ic Id Ii Ik In IO IP Iq Is It Iu Iv IZ Jd Je Jf Jg Jh Ji Jj Jk Jl Jm Jo Jp Jq Ju Jv Jy Kc Kd Kf Kg Ki Kj Kk Kl Kn Ko Kp Kr Ks Ky Kz Lh Lp Lt Lu Lv Ma Mb Md Me Mf Mi Mj Mk Mm Mn Mp Mq Mr Ms Mu Mw Mx My Mz Nc Nd Ne Nf Ng Nh Ni Nj Nk Nl Nm Nq Ns Nu Nv Nw NY Oe Of Og oH Oi Om Op Or Ou Oy Oz Pa Pb Pc Pd Pg Ph Pj Pk Po Qb Qc Qd Qe Qg Qh Ql Qm Qn Qt Qu Qv Qw Qy Qz Rb Rc Rg Ri Rj Rm Rt Rv Rx Ry Rz Sf Sh Si Sj Ss St Tn To Tv Tz Ua Ub Ue Uf Ug Uh Uk Ul Um Uo Up Ur Us Ut Uu Uv Uw Ux Uy Uz Vb Vc Vo Vp Vs Vt Vw Vz Wb Wc Wd We Wf Yl Zx Ye Tm Tl Th) De(aE AF aW cH Cx dK dR eC Ed Et Ez fP Fw Gp gW Hr Id Il Jf Jg Jm Ju Jv Kn Kp Kq kS Lh Ly Mj Mp Mq Mu Mw Ne Nf Nk Nl Nn Nt Oa oE Ow Oz Qa Qc Qd Qe Qh Qm Qn Qw Qy Ra Rb Rg Rh Sr Tt Tv Uf Uh Ul Up Ur Us Ut Uu Uv Vp Vs Wm) Uu(aE AF Ap aW Bb bL Bn bO cD CH cV CX dH dJ Ez Fc fP Fw Gp Il Jg Jm Lp Mp Ms Mw Ne Nk Nr Nt oE Og Or Pb Pz Qc Qe Qy Rg Ru Ue Ug Uh Up Ur Us Uv Va Vp Vs Ti Th) Uv(aF aW bL Bn bO CH cN cT cV Cx dK Dr Et Ez Fn fP Hq Ih Il Jp Jv Kq Ld Ma Md Mp Na Ne Nk Nn Nt oE Oh Or Ow Oy Pb Qy Ra Rf Rg Rh Ru Tr Tt Ug Uh Up Ur Va Wm Ti) Dr(Al AN As aW aY Bb bX Ch CX DK Ed Ex Fc Gl Gp Ih Jd Jg Jk Jn Jy Kk Lj Mh Ms Mx Nb Nd Nn Ny Oa Oe Oh Oi Ou Ow Oz Pa Pf Qa Qn Rx Sr Ul Un Us Uy Va) Ru(aE Af Aj aM Ar aY bJ bM Ch cM cV Cx Ed fR Fw Gd Gl Hc Hp Iq Iv Je Jj Kf Kg Kp Kz Ld Mn Mr Nb Nc Ne Ni Nl Nt Nu Ny Oz Rt Sh Sr St To Ub Uk Us Vh We Wf Xa) aF(aA aD aO aW bZ cE cH Cx dF dK eC Ed Et Ez Fw Hr Id Il Ju Jv Jy Kj Kn Ld Lh Lj Lz Mj Mp Mw Ne Nk Nn Nu oE Of Ou Ow Oy Qw Qy Rf Ri Sr Ua Uh Up Ur Us Vp Vs) gW(aJ aP bL Bo bV CW DB dE dI dJ Fn Gl gP Ha hB hG Hq Hx iH Iu Jh Jk Jp Lh Lx Mj Mp Nj Nk Nl Nv oF Oh oN Or pF Ph Rm St Ue Uf Ug Vp) Vs(aA Af aW Ax Bn cH cT CX eC Ed Ez Fw Fy Ih Il Jv Kq Lj Mh Ml Mq Mw Nn Nr Nt Oa oE Oh Ow Pb Pf Qa Qe Ra Rf Rh Sr Tr Tt Us Wm) Rx(aA Af aM aV aW Ax bJ Ch cV Fy Gl Ih Ir It Jn Kj Kz Ld Lj Mq Mr Nc Ne Nf Ni Nj Nl Nr Nt Nu Ny Oa Oh Oz Pf Qa Rt Ub Up Va) Va(Af aG aH aV AW aY BA bJ bM bO cD cT cV dA Ed Fc Fw Gl Ih Ir Jm Ld Nb Nr Nt Nu Oa Ow Oz Ps Qm Qy Sr St Uo Vq Xa) Af(aA aW cH dK Ed Et Ez Fw Il Je Jm Jv Mp Nk Nn Nt Oa oE Oh Or Pb Ps Qy Ra Rf Rh To Ue Ug Uh Ul Up Ur Us Vp Xa Wm) oE(aE aJ aW aY bJ bM Bn bO cB cH cV dG dL fP Gl Hr Ji Jy Kf Kn kS Ky Lh Mp Ne oF Po Qv Qx Qy Tv Up Us Ut Vp) Th(aA Ar aY bJ Bo Cs Cx Ed Fp gL hB hG Iv Kj Kr Ld Lj Mh Nb Nf Ni Nj Nt Nu Ny Oa Oh Qv Rf Rh Tr Ub Ur Us) Lh(Ax Cx eC Ed Fw Fy Il Kq Lj Lz Mh Ml Mp Mw Nn Nr Nt Oa Oh Ow Pb Pf Qa Qe Rf Rh Sr St Tr Tt Uh Us Wm) Pb(aW aY Bn CX dK Ed Fw Gl Il Jv Kf Mp Ms Mt Mw Nj Nk Nl Nr Nt Nu Or Ou Pd Pf Qy Ri Sr Up Ur Us) Mp(aE aW Ax Bn CX Ed Fw Il Jm Jv Kp Lj Mq Mw Nn Nr Nt Ow Oz Pf Qa Qb Qc Qm Qw Qy Uh Up Us) Il(aA bL bO Ch Cq Gl Hq Jo Ju Jv Kg kS Nk Oy Ph Qw Rt Sh Up Ur Us Vo Vp) aW(AA aZ Bn bO Ch Dp fP Hc Hp Jo Jv Kg Kj kS Rt Sh Uh Us Vo Vz Wb Xa) eC(Aa aX bL bO cB cV cW dE dG eF Ex fP Gl Gz Ld Nj Nk Nl oF oN Po Qy Tn) Us(aA bL Bn bO CH dJ fP Jv kS Md Mw Ne Nk Nt Ps Qy Ug Uh Ur Ti) Nb(Du Em Eq Fc Fd fR Hl Sh Si Uw Ux Wc Wd Wf Yl Zx Tl Ti) Up(bL Bn CH Cx fP Fw Ih Lj Md Mw Nr Nt Qa Qc Qc) Ed(bL Bn fR Gl Gn Mj Nk Rt Vp Wc Yl Xa Ti) Qy(Bg bL Bn Ch fP Hc Hq Iz Lj Ng Nk Of Oy) fP(dK Jv Mw Nk Nn Ra Rf Rh Tr Ur Vp Wm) Lj(Bn Du Fc Kn kS Nk Rm Rt Vp Wb Ti) Gl(Nn Nt Oh Ow Rb Rf Rh Tt Vw Wm) Nr(Ch Du Fc Rt Rv Sh Vh Wb We Zw) Mw(aE bL CH Jv Ne Of Sh Wc) Ti(aA aN aY Bo Fw Kr Ny Oa) Cx(Eq Hr Jv Qw Sh Ux Zx) Rt(aY Jm Ms Oa Qa Sr Tv) Nn(Eq Mm Po Sh Ut We) Fw(Bn Hr Nk Nv Vp) Qa(Mj Ne Nk Rm Vp) Wb(Mh Oh Ow Pf) Zw(Ih Nt Oh Pf) kS(Ml Rh Sr Uh) Bn(aE Rg Sr) Ez(Ch Kg Kl) Xa(aY Fc Oz) Dk(Ny Ps) Du(Ax Ih) Po(Oh Tt) Nt(Eq Uy) Nk(Oa Ul) Jv(aY Jm) Kq(bL Vp) Lp(Ld Ur) Oz(Ou Ps) oN(Oh Rh) NeUh TtKl IhRm ShaY QeVp KgdK QmOf aAcH} Ed{Ru(aA aC aE AF aG aH aI AJ aK Al aM AN AO Ap aQ Ar AS aU aV AW AX aY aZ BA BB BC bE bF BG bH bI bJ bL bM BN BO bP bQ bR bS bW bX bZ cD cE cF CH cJ cL cM cN CO CP CQ cR CS CT CU Cv CW cX cY cZ dB Dc Dd De dF DG dH dI DK dL dM dN Dp DR Ef Em Eq Et Ex Ez Fc Fd Fi Fp FR Fw Gb Gc Gd Gn Gp Gz Hb Hc Hf Hl Ho Hp Hq Hu Hv Hw Hx Ib Ih Ii Ik Il In Io Ir Is It Iu Iv Iz Jd Jf Jg Jh Ji Jj Jk Jl Jn Jo Jp Jq Jr Jt Ju Jv Jy Kc Kd Kf Kg Ki Kj Kk Ko Kp Kr Ky Ld Lj Lp Lu Lx Lz Ma Mb Md Mf Mg Mh Mi Mk Ml Mm Mn Mp Mq Mr Ms Mt Mu Mv Mw Mx My Mz Na Nb Nc Nd Ne Nf Ng Nh Ni Nj Nk Nl Nm Nn Nq Nt Nu Nv NW Nx Ny Oa Oe Of Og Oh Oi Om On Or Ou Ow Oy Oz Pb Pc Pd Pf Ph Pi Pj Po Ps Pz Qa Qb Qc Qd Qe Qg Qh Ql Qm Qn Qt Qu Qv Qw Qx Qy Qz Ra Rc Rh Rj Rm Rt Rv Rx Ry Rz Sf Sh Si Sj Sr Ss St Tn To Tv Tz Ua Ub Uc Ue Uf Ug Uh Uk Um Un Uo Up Ur Ut Uu Uw Ux Va Vc Vo Vp Vq Vs Vw Vz Wb Wc Wd Wc Wf Wh Yl Zw Zx Ye Tl Xa Wm Tj Ti) Xa(aC aF aG aH aI aJ aK Al aM AN AO Ap aQ Ar aU aV AX aY aZ Ba Bb BC bE bF BG bH bJ bM bN BO bP bS bU bW bX cC cD cE cG CH cI cJ cL cN CO CQ CS CU Cv Cw cY cZ dA DB Dd DE DG dH DI DL dM Dp Dr Du Ef Em Et Ex Fc Fd Fi Fn fR Fw Fy Gb Gc Gd Gh Gl Gp Gz Ha Hb Hf Ho Hp Hq Hu Hw Hx Ib Ic Id Ih Ii Ik Il In IP Iq Ir Is It Iu Iv Iz Jd Je Jg Jh Ji Jj Jl Jm Jn Jp Jr Ju Jv Kc Kd Kf Kg Kj Kk Kn Ko Kq Kr Ks Kz Ld Lh Lj Lu Lv Lx Lz Ma Mb Md Me Mf Mh Mi Mj Ml Mm Mn Mp Mq Ms Mt Mu Mv Mw Mx My Nb Nc Nd Ne Nf Ng Nh Ni Nl Nm Nq Nr Nt Nu Nv NW Nx Ny Oa Of Oh Om On Op Or Ow Oy Pa Pb Pf Pg Ph Pj Pk Po Ps Pz Ql Qt Qw Qx Qy Ra Rf Rh Rj Rt Rx Ry Rz Sf Si Sj Sr St To Tv Uf Ug Uh Ul Up Ur Us Uu Ux Uy Va Vb Vh Vp Vs Vw Vz Wb Wc Wd We Wf

Figure 38 Continued

Qd Qe Qh Qy St Tz Uh Vq Vt Xa) Is(aA Af Ap aW aY bG bH bJ bN Bo Co Cv dI Gc Iq Jh Jj Kg Mg Mh Mi Mj Mp Mq Mu Mv Mw Mx Ni Nn Nq Nt Nu Om Pj Ql Rt Rv Rx Sh Uf Uh Ur) Sr(aH aK aM aN aU aW aZ bH bR Cx cY dM Et Gp Jj Jp Kc Ki Kk Lj Mi Mp Mq Mv Nq Oe Oz Pa Pc Pj Qd Qy Sh Si Ug Uu Uv) Mw(Af Aj aZ bS Ch CX Et Gc Gp Hb Hu Ib Ic Lz Mh Ml Oe Oh Oz Pj Qn Qw Sh Uh Vq Wf Ye Ti) Gc(Cx Fp Hx Iv Jd Jh Jl Jn Jy Kz Lj Mk Mv Mz Nq Nv Oa Om On Ps Qe Ql Qw Sh St Ut Xa) Qd(bS Ch Cx Dr Il Kx Lz Mh Ml Na Nn Nr Oh Oi Oz Pf Qn Qw Qx Ra Ru Ua Vq Ye Wm Ti) On(Af aQ aW aY aZ bG Bo cP cW Cx dR Et Gl Gp Kc Kd Ki Lu Nq Oz Pj Qn Rt Sh Si) Uh(Dl Dr It Iv Jd Jn Js Jt Jy Mq Mv Nf Ni Nn Nt Om Po Ql Ut Uw Xa) Nn(Aj bS cF Dr Et Ez fP Hb Ny Oi Oz Pc Qu Si Tz Un Vt) Pf(aF aO bF Dd Dr Gb Hb Nt oN Oz Pc Pi Ps Qy Un Wb) Pj(Hu Ih Iv Jh Jn Jr Nv Ny Oa Oh Oi Po Ps Tz Un Vt) Ut(Af Aj aZ bS Ch Cx Lu Oi Oz Pc Sh Si Uu Vq Vt) Et(aY cV cX Fw Ih Iv Lj Nd Oa Oz Si) Nq(Ch Eq Ih Il Ir Jn Nr Ny Oa Oz) Hb(bQ Cu Jh Kg Mq Mv Nt Om) Si(Cu Fr Fw Mk Mq Nu Oa Po) Ny(aU aW Cw Cx dR Gp Mg Rx) Oz(Cu Fw gL Ih Jh Jn Js Ps) Qy(Kx Lj Ml Oh Po Qv Qx) Ps(aW Gp Mk Rc Rx Vt) Mi(Hf Lz Ml Qx) Mk(Ih Jk Oa Qe) Mq(aX Ic Il Vq) Jh(Lj Ml Pb Vt) Jn(Cx Rj Rx Vt) Om(Ch Lz Oy Sh) Nt(In Oh Qb) Un(Gp Nr Ru) aW(Cs Jl Jq) Po(aN Ko) Fw(aM dR) Js(aF Bo) Oa(Ic Rx) aY(bB Iv) CuLj CxPi NdKz I

Ur Us Ut Uv Vp Vs Vt Vu Vv) Hb(AA cH Cu Dc Fw Hv Hw Ih Ir Is It Iv Ji Jn Jq Jr Js Kd Kq Lw Mi Ml Mt Mx Na Nr Nt Ny Pi Pk Qd Qe Rj Ul Up Vt) Vt(aG Aj Bb bC cH De eC Et Gp Hr Ip Is Ji Js Ko Kp Nw Oe Oh Ou Pb Pf Pg Pj Qc Qd Qy Tz Um Ur Uv) Nw(Id Jv Kd Kl Kq Kr Qn Qw Qy Ra Rb Rg Rj Tv Ul Un Up Us Uu Vp) Ji(Gl iZ Kc Kl Kp Lp Ou Qy Ss Tz Um Us Uu Uv Vs) Kq(Aj Bg CH dN Kl Lu Of Oi Ss Uu Uv) Js(Ur Us Vs) Et(iZ Kl) MlKd WfJn JqUv aAjK} Iv{Th(aA AF Ao Ar aY Bc bJ bQ bR cS Cv Cx Et Ez Fr Gb Hb Id Ih Jd Jh Ji Jj Jn Jp Kd Ko Kq Kx Ky Mq Mr Ms Mt Mz Ng Nt Nu Nv Nw Ny Oh Ok On Oz Pc Pf Pj Qe Ql Qy Rj St Ub Uf Uh Un Ur Ut Vt Ti) aY(Du Fc Fd Fi Gb Gh Hl Ho Hp Lt Op Rv Ry Rz Sf Si Sj Uw Ux Uy Vc Vh Vw Vz Wb Wc Wd We Wf Wg Wh Yl Zw Zx Ye Tm Tl Ti) aW(Fi Gb Hl Ho Lp Si Sj Uw Vb Vz Wb Wc Wf Yl Zx Ye) Ti(aA Bo Gp Jp Kd Nx Ny Oz Ug Uh Um Uu Uv Vt) Wc(aN aZ Cx Nw Oz St Uh Vq) Pf(kN kP lX mZ Vc Wb) mZ(kP ml nN Oz Qc) Gc(Kd Uu Uy Vs) Qy(Vb We Wf Ye) Ye(Ih Ny Oz) Vb(aN ll Jm) Uy(aZ Bo Cx) Gp(Hp Wb) Hl(ll Jm) Vz(Nw Oz) Zw(Ir Is) Wf(Jn Ny) Lp(Bo Uh) CxVc FcPb FdNy GnSt IhWe

Qa Qb Qc Qe Ru Rv Rz Si Uh Uy Uz Vc Vh Vw Wc Wg Wh Yl Zw Zx Tm) Qd(aA De Fc Fp Fr Gh Hr Hu Io Is Jg Jm jO Jp jR Jt Lw LX Ly Lz Ma Mc Me Mh ml Mm Mn Ms Mx My Mz Nc Nd Nh Ni Nj Nm NN Ns Nt Nu Nx Ny Of On Pd Pf Qa Rf Rt Uh Ux Wf Yl Xa Wm) Pe(Hv Hw Il In Iq Ir Is It Jj jK Jr kG Ld Lj Lu Lv Lx Lz Mc Md Mg Mh Mi Mj Ml Mm MP Mq Mr Ms mT Mu mW Na NB Nc Nf Ng Nh Ni Nl nM nR nU Nx oN oQ Ou Pc Pf Qw Qy Ur Vq Wm) Js(Bb Du Ed Fp Hb Hc hV hW Ik Il In Io Is jL Jn Jo Jp Jt Ld lM Lx Me Mn Mt My Nc Nd Nc Nh Nm Ns Nt Nu Nx Ny Oi Ok ON Oy Pd Po Pz Qa Qc Qe qU qW qX Sh Up Us Vs Vz Zw Wm) Pf(Eq Fc Gz Hb Hr Hv Hw Hx iI In Io Iq Is Iv Jj jK Jm Jq Jr kE Lu Lx Ly Lz Mb Mc Md Ml Mp Mq Mr Ms mZ Nb Nc nD Ne Nh Ni nK nN Nr nT Nu Nx Ny Oh Pa Qa Qb Sj Uh Yd Zw) Uh(aL aM bB bL bV cQ dJ dK dL dM Ed fR Fw Hr Ib Ii Il Jh Jj Jo Jt Kf Kg Kz Lh Lj Mb Mj Ne Oh On Ow Pd Pg Ph Po Qe Ql Qx Qy Ru Tn To Ue Ug Un Ut Uv Va Vs Vt Vu Xa) Lj(Hu Hv Hw Hx Ii Il In Io Iu Iv Jh Jk Jl Jo Jr Lv Ly Lz Mb Mc Me Mf Mj Mq Mr Ms Mu Mv Mx My Nc Ni Nk Nr Ns Nu Nx Oh Oi Om Oy Pa Pc Po Pz Qb Qe Qy Sf Sj) No(aA Bb Fb Fn Gz Ha Hc Hv Hw Ib Iz Jf Jl Jq jT Ju Kc Kl Ld Lh Lv Ml Mq Mr Mx Na Nq Nt oE Oh Or Pd Pj Qw Rc Ss Tv Ue Up Us Vp Vt Vv) Ir(Fc Hv Hw Ii Iq Is Iv Jh jK Jl Jq Jr Lh Lu Lv Mf Mg Mi Mk Ml Mq Mr Mu Mv Mx Na Nb Nf Ni Nj Nl Nq Nv Oh Om Pg Pz Qa Qb Ur Vz Zw Ti) It(Bb Fp Ik Il Io Ip Iq Is Jg Jh Jm Jn Lw Ly Lz Ma Mc Mi Mr Mt Mx My Nb Nc Ne Ni Nj Nn Nq Nr Ns Nu Oe Of Oh Pa Pd Po Qb Ru Sh Wf) Is(Du Gb Gh Hp Io Ip Jg Jj jQ jY Lt Ma Mn Nd Nv Ny Oe Of Ok Op Qc Ry Sf Uu Ux Uy Uz Vb Vc Vw Wd We Wg Wh Ti) Ij(Bb bO cB Ch Ct De Ex Fb Fn Gd Gl Iz jT Ki Kl kP lX Mv nC Ng nL nW Oi Ph Ql Qn Rf Ss Tv Up Us Uv Vo) Jn(Fd Fp Fr Gh Gz Hl Ho Hp Ip Jp Lt Lx Ma Me Mm Mn Mz Nc Nd Ny Oe Ok On Pg Qa Qc Qe Ry Rz Sj Vw) Kq(aE aW aY dN Dr Ef Fd Gc Hb Hc Hl Ho Hp Hq Kl Li Lu Mg Op Ph Qt Sf Si Sj Uv Vc Vh Wb Wg Ti) Iv(Du Eq Fd Gh Hp kP Mz Nd nH nL nN Op Oz Rv Ry Sj Ux Vh Wb Wd We Wg Wh Yd Zw Zx Ye) Mz(Hb Hu Hw hX Ik Il In Ip Iq Jj Me Mh Mn Mp Mr Mx Nb Nc Nr Nx Oe Qc Ur Us Uv) Im(Bb bN bO dB De Em Gc jK kF Ki kO Ld lY mH mS nB nD nO nR nU oP Rf Ur Uu Vs) Ji(bO Fc In jK Jo jT Lv Mb Mm Mp Nb Nc Ni Nn Pg Ri Rt Rx Ur Uv Vp Vs Wc Th) On(Eq Fp Hl Hp Hu Ip Lz Ms mZ Nc Ng nl Ns Qb Ru Rv Si Uu Vz Wd Wh Zx Ye) aA(Aa Bb Fc Fr Gc Ho Jg Jm JT Ma Mn Nm Nr Nu Og Pb Pj Qa Qb Rx Uw Wd) Xa(Af bG cU cX Eq Ha hB Jh Mx Nr Nt Nu Nv Nx oE Ow Ql Rj Ru Sj Uu Vq) Qa(Ip Jg Jp Jt kE kN kO Ma mM Ms nC nD nH Nk nL Ns nT Of Ok Oy Qc) Nn(Fi Gh Hl Lt iX Og Op Pb Rt Rx Ry Rz Si Vz Wc Wg Zw Zx Tl) Qe(Fc Gh Hu Ik jK jT Lp mF Nk nN Ns Oe Oy Ur Ux Uy Wb Yl Ye) Va(aE Dk Dl Dr Hu Ic II Iz Kf Kk Mg Mq Mr Ok Ou Pg Po Rf Uw) Mt(Fd Fi Gb Hl jK Lt Ny Ry Sf Sj Uw Uz Vc Vw We Wg Yl Tm) nl(aJ aP aZ Fr Hw kK Lx Ml mP Mr Mv Mx mZ nB Nh nO Ny Pb) Ny(De Fd Hr Ip Lx Mn Nd Ns Oe Of Ok Pg Qc Ux Uy Zw) Ow(Fd Fi Gh Hb Ho Ru Sf Si Uy Uz Vc Wc Yl Ye Tm Th) Lx(Gb Hq Hr Ip Jj kP Nd nL Ns Oe Oz Pb Wc) Sr(Aa aE Af cH dJ Et In Jj Oe Ou Pb Qy Ur) Oh(Du Eq Gb Ho Lt nC Op Rv Rx Ry Sj Vz Yl) Li(Dp Jv Kd mW Pj qY St Tv Un Ur Vq Vt) Et(Aj Bb bO cB Ch Hb Kl Lp Rf Uv Wm) Nu(Fi Lp Og Rx Ry Sh Ux Uz We Wf Tl) Nr(Fc Hl Jj Og Ok Rv Rx Vz Wd Wf) Ip(Fp Fr Jg Lz Ma Mn Ok Oz Pb Qb) Qc(Fr Jg Jj jK kG Ma Mn nL Nt Ok) Qb(Fr Ho Jp Jt Ma Nm Oz Pb Wd) St(Fc Gc Gh Ho Ru Rx Sh Sj Ux) Og(Fp Ii Il Iq Jl Mi Mn Nv Po) Fw(Fd Gh Lp Op Ou Rx We Zw) Rx(Cs Fy Jp Nv Ok Un Ut) Lp(aP Jh Jl Jy Kd Nq Nv) Rt(Dd Fy Ha Mx Pi Tn Ut) Oz(Fr Gc Jp ml nC nN Pg) Nt(Gh Rv Rz Uy Vw Yl) Lz(Fd kP lX Mn nH Ok) Jj(Bb Fr li jK Mn Nm) Vi(cB dA dD Ou Uo Ut) Dr(Qy Ru Si Ut Vq) Hb(Ed Il Ld Qy Ut) Yd(Cu Jd Nq Ou Un) Sh(Gc Hu Jg Jk Vq) Pb(Fp Jg Jp Mn Pg) bN(Aa Bb iZ jl Kd) jK(Jq Ma Mr Nb Nm) Mq(Eq Ho kN Vz) Wb(aP Nv Po Qx) Jl(Fi Wf Zw Ye) Ok(Fp Mn Of Oy) Aa(Ax Cx Rf) Ar(Fd Fi Uz) Bb(Aj Ml Ur) Fc(Ex Mx Tz) Gc(iZ Nb Qw) Jr(iC jV nN) Ld(Gh Si Wh) Ru(Hx Jh Po) Uy(hB Jd Ql) mZ(bZ nN Nq) Cx(Fd Gb) Eq(Pd Uf) Fp(Jt Nd) Fr(Oe Oy) Wf(Nv Vt) Qy(Rf Ux) Ut(Ch Ux) Pg(jO Ns) jT(jl Jq) BoHo DcUr EdSj TiiZ ThNb FiQl GbMx MlnU J

Sj St Tz Ub Um Vc Vq Vt) Ps(Aj aK Ar aU aW aZ bB Ch cU cV CX dR Ed Fw Gh Gp Hc Hp Ij Il Jh Kd Ki Kl Lh Lj Lz Mh Mk Ml Mq Mw
Nq Oa OE Oh Oi Ou Oz Pa Pc Pf Po Qb Qv Qw Qx Qy Rc Rj Ru Rx Sh Si Ss Ur Us Uu Vo Vq Vs Vt Wf Ye Ti) Kq(AJ aW aY bF bM bS cQ
cV cW Dc Dd Di Dl dR Ed Ex Fc Fw Gl Hq Ic Ih Ik Il Im In Iv iZ Jj Jm Js kQ kR Lh Lj Mb Mf Ml Mn Mx Nb Nd No nY Oa Oh Op Ou Pe Qc
Qn Rm Ru Rx Rz St To Ul Uu Ux Vt Vw Wf Ye Ti) Ny(aG aK Ao Ap aQ aU aW aX bB bC Bo bQ bS bW bZ cL CO cS CU Cw CX cY dK dR
Ez Gp Ho Ic Jh Kc Kc Kg Lh Ma Mf Mg Mi Mm Mp Mq Mu Mv Na Nq OE Oh Ou Pd Pf Po Qv Qy Rj Rx Rz Si Uf Un Vq Wd Wf Ti) Jh(Af
aH aM Ar AX bB cQ Cs CX De Eq Fw Gp Hb Hc Hf Il Ir Iz Jq Js Ki Kx Lh Lz Mh Mk Ml oE Oh Oi Op Or Ou Oz Pb Pc Pf Po Qa Qb Qc Qe
Qv Qw Qx Rg Rx Ss St Tz Ua Un Us Vb Vo Vq Vs Vt Wf Ye Ti) Ke(aF Aj aO Ar aY Ba Bc bF Bg bL bM Bn bR CH Cu cV Cx Db De Di dK
Dl Ed Ez Fw Ik Kg Kn Kr Mm Mp Mq Ms Mz Nc Nd Ne Ni Nj Nk Ns Oi Op Oz Pb Pk Po Ql Qw Qy Qz Rx Ry Sh St Tv Uf Uu Uw Vp We Tl)
Nq(AX bA Bc Cs cT Cu Dc Dd Dr Eq Fw Fy Ha Hx Ic Ih Ii Ij Il Ir Jk Jl Jn Jp Js Jt Kd Kn Ko Lh Lj Lp Mx Mz Na No Nr Nt Nv Oa Oh Oi Ok
Oz Pa Pf Pi Qa Qe Qx Ru Sh Si St Tz Ub Vh Vq Vt Xa) Mw(Af aG aJ aK aQ aU aW aZ Bn bS cN cT CX dR Gh Gp Hb Hc Hf Hu Ib Ic Il iP Ir
Jn Jp Ki Kx Lv Lz Mh Mk Ml Na Oe Oz Pb Pf Po Qn Qv Qw Qx Ru Rx Si Tz Ua Un Ur Vq Ye Wm Ti) Si(aM Ar Ax bJ bQ Co Cs Cu cX Dr
Ed Ex Fp FR Fw hB Ih Im Jj Jl Jn Js Jy Kx Ky Lj Mk Ml Mq Mr Mv Mz Ni No Nr Nu Nv Oa Og Oh Oz Pf Po Qa Qe Ql Qv Qx St Un Ur Uu
Ye Xa) Qa(aC aW aZ bM Bo bP bS cE cN cP cQ cV CW cX dI Dk dM dR Ex Fc Gn GP Hc Ib Ij iP Kd Ko Mj Mk Oe Oi Oz Pc Qn Qw Qy Rj
Rx Un Ur Vp Vq Vt WfZw Ye Ti) Nb(aH al Ao Ap aU aW bB bW bZ cN CO cQ cS CU CX Ez Fi Gp Hb Hl Jd Kc Kg Lh Mb Mg Mi Mm Mu
Mv Na Nh Oe Oh Pc Pd Pf Ql Qy Rx Rz Tz Uf Ug Vq Ti) Qy(aH al Ar bB cH Cu Eq Ex Fp Fw Hx Ir Iv Jn Jq Jr Js Kx Li Lz Mj Mk Ml Mq Mr
Mx Mz Na oE oF Oh Oi Or Ou Oz Pe Pf Pg Po Qb Qe Qv Qx Rv Vt Xa) Jn(aF Ao Ap aU bC bS bW CO cV CX Dd dM dR Ez Ho iP Jd Kc Kg
Mg Mi Mk Mm Mp Mq Mu Mv Ou Oz Pa Pc Pd Po Qw Rj Uf Un Vq Vt Wd Wf Ti) Ij(aO Ap aS aY aZ bF bR bS bZ cE cL Co cT cZ De dF dG
dH dJ Gp Jd Kc Kd Kg Ko Mg Mp Mq Mv Ni oN Oz Pc Pd Pe pF Pi Uf Un Vc Wd) Pf(aF aO bF bR Co Cp Cu Dd Ef Gb Hb Hu Hv Hx Ih Jd Jk
Jl Kg Mg Mi Mp Mu Mv Na Nt Nv oN Oz Pc pF Pi Ri Rv Uf Un Vc Vq Vt Wb Wd) Qe(aC aG aN Ao aW aZ Bo bQ cE Co cP Cu Cv Cx dl Ez
Fw gL Gn Gp Hl Hu Ic Jd Lz Mg Mi Mk Mp Mq Oe Oz Pd Qw Qx Rj Rx Uf Ur) Nv(Af aG aO aQ aW aZ bS cN CX Gp Hb Hc Hx Ic Ih Ir Ki
Lu Lz Mi Ml Mv Mz Na OE Oh Oi Po Qn Sh Tz Uu Vq Vt Ye Xa Ti) Li(aA aE aO aP aX aZ BG bQ cE Ch CO cS cU dL eF Ez Fn fP Hc Hl Ik
Ip Jl Jp Kc Kl Kr Mv Ng Oi Oy Qu Qv Qz St Tj) Mq(aR aX aZ bA Bb Cp cQ cT Gp Hb Ic Ih Ii Il Ir Jk Jp Jq Jt Kn Ko Ks Mn Mz Oh Ok Pa Pc
Pz Qc Qh Rm St Tz Un Vq Vt) Pe(aG Ao Ap Bn bP bW cE Co cW Dc dK Dp dR Ez Gp Ha Hb iJ Iu Kc Kd Kg Ko Mi Mu Mv Nt OE Pd Ri Rv
Rx Sh Ue Un Ur) Oh(aE aF bE bJ Bo bW cM Co Ef Gb Gz lm Jd Kc Kg Mg Mh Mi Mp Mu Mv Nt Oz Pd Uf Un Ur Vt Wb Wd) Po(aF aN Bb
Bo Cx Dd Du Gb Hb Hu Ic Ih Il Jg Jk Jt Jv Kc Kd Ko Nt Nu Oz Pz St Vt) Tz(aU aW bW Co Cw Ez Fw Ho iJ Jd Kc Kd Kg Mg Mi Mm Mp Mu
Mv Na Oz Pd Uf Wd Ti) Js(aF aY bE bG bM Bo bW Co Dd Hv Jd Kc Kg Mg Mi Mp Mu Mv Oz Pc Ql UfUn Wd) Im(aH al aK aQ aU bB cY
dR Hb Jp Lv Mk OE Oi Ou Pc Rc Un Vq Ti) Hb(bQ Cu dK Ef Fr Fw Ih Jd Kg Mg Mi Mu Mv Nt Oa Pd Tn Wd Xa) Un(aW aY bA Cx Fw Gp
Ih Il Lj Mk No Nr Oa oE Oz Pz Ru Xa Ti) Vq(Ar aZ dR Fp hB Hl Kk Ky Lz Ml Mv Nu Oa Oz Qw Qx Xa) Vt(bN bQ Cp Cu Fw Gp Hw Ic Ih Il
It Mg Mk Mv Tn Xa) St(aU cC Co Cw Hv Jd Kd Kg Mi Mu Mv Ou Pd Wd) Cx(Cp Cu Fy Jl Jp Jr Na Nt Pg Pi Tn Uw Xa) Qx(aF Ap Cp Dd Gb
Ho Ih Jk Jt Kg Ko Mi Uf) Lh(aY Co Gb Ih Jt Kd Ko Lu Mi Mu Nt Oz Pi) Qb(aW Cu Ez Ih Kg Mg Mi Mp Mv Nt Pd Uf) Jd(aY bR Cq Gp Ic Ih
Il Ir kR Oi Pa Pb) Ql(Bb Cq Cu Dc Dd Fw Ih Il Kd Lp Mi Xa) Oz(Cp Cu Dk Ef Hq Jl Jp Mk Ou Pg Tn Uw) No(Ao aQ cJ cQ cY dA Mk Mm
Mp Ou Ti) Nt(In Jq Mh Mj Mk Or Ou Ph Qg) Mk(Ha Ih Jk Ko Lj Oa Pc Pi) Ou(aF Ap aW Ax Ih Mm Nr Ru) Lz(Dd Ho Jg Jk Jt Ko Mi) dR(Cu
Fw Ih Of Qc Uf Uw) Ml(aF Ho Jk Ko Mi Uf) Ic(Hv Iv Mr Nf Oa Xa) Co(aZ Ch Ed Eq Mj) Cu(aY aZ cX Lj Pc) Ji(aW Fw Gp Kd Rx) Ed(lu Mp
Na Ti) Kd(Cs Fp Mv Qm) Rm(aW bG Rx Ur) Oa(Ao Mm Mp Ti) Fw(aM Jj Mv) Hf(aF Mi Uf) Jq(aF aW bJ) Xa(aY cQ cV) aZ(Cw Tn Uf)
Ar(Jk Pi) Lj(Ao Mp) aX(Ez Mg) aY(bB Mz) BoOk DkaW GbMh GpHx MiOp MvMx NdKz HuJr HvQm UwcX} Ps{Af(aA aM aP Ar As aW
Ax Bn bO cC Cp Cq Cs Cu Cv Cw Dc dM Du Ed Em Eq Et Ex Fc Fp Gc Gh gL Ha hB Hu Hw Id Ii Il Ir Iv iZ Jd Jh Ji Jj Jo Jq Jr Js Jt Kd Ke Kg
Kk Kl Kn Kp Kr Kx Ld Lh Li Lj Lw Lx Md Mf Mh Mi Mj Mk Ml Mq Mr Mt Mw Mx Nb Nf Nm Nn Nr Nu Nv Ny Oa Oe Oh Oi Ok Om Oz
Pa Pb Pd Pf Pj Po Qe Qg Qx Qy Rc Ru Sr Tv Uc Ud Uh Ul Un Ut Uw Uz Vh Vt Wg Yl Xa Ti) Rx(aF aG aO aP Ax bA Bc bF cE cH Cp Cq Cs
Cu Cv CX Dd dH dM Dr Du Ed Em Eq Fp Fw gL Ha Ho Hp Hr Hu Hv Hx Ih Ii Ij Im Ir It iZ Jh Ji Jn Jr Js Jt Kd Kl Kn kQ Lj Lp Lv Me Mi Ml
Mq Mr Mw Mx Na Nb No Nr Nt Nu Ny Oa Oe Oi Op Oz Pd Pi Po Qa Qg Qw Qx Qy Ra Rc Rj Ru Ry Sj Sr Tv Ul Un Up Ur Uy Uz Vp Vs Vt
Wc Xa) Us(aF aM aO aU Aw Bb bC bW cC Co Cp Cq cS Cu cV Cw CX Dd De Ef Fc Fi Fp Fw Gc gL Hu Ih Io Ir Iv Jd Jg Jh Ji Jr Kc Kd Ke Kg
Kj Kn Kq Ld Li Mg Mk Ml Mq Mt Mu Mw Na Nb Ni Nn Nq Nr Nt Nu Oa Oe Oi Om On Oz Pc Pd Pe Pf Ph Pi Po Qd Qe Qn Qw Qx Qy Rc Sj
Tn Ul Un Up Ut Uy Vq Vt Wd) cV(aA aH al Aj aK aL aM Ar aU aW aZ bB BG Bo bQ CH Cs cU Cw Cx Ed Ef Eq Fw Gp hB Hc Il Is Iv Iz Ji
Jj Js Kd Ke Ki Kk Kl Ld Lh Lj Lx Lz Mh Ml Mq Mt Mx Nn Nr Oa OE Oh Or Ow Oy Pb Pf Po Qb Qv Qw Qx Ra Rc Rj Ru Sh Sr Ss Ua Uh Ur
Uu Vo Vs Vt Wf Yl Ye Th) Qn(aA Aj aP Ar aW Ax aY BG BO Ch Cs Ct cU Dg EF Eq Fn Fp Fw Gh Gp HB Ij Iv iZ Jj Jn Js Kd Ke Kk Kl
kR Ld Li Lx Lz Mh Ml Mq Mx Nb Ng Nn Nr Nu Nw Oa Oh Ow Oz Pb Pf Po Qa Qb Qd Qe Qg Qw Qx Rc Rj Ru Sh Sj Sr Ss Tz Uh Uu Ux Vo
Vs Vt Wc Wh Ye) Cx(aA aM aP Ar aW Ax BG bO cC cD Ch Cs cU Dg dM Du Eq Ex Fc Fn Fp Fw Gc Gh gL Ha hB In Is Iv iZ Ji Jj Jq Kk Kl
Kq Kx Ld Lh Li Lx Mh Mj Ml Mq Mt Mw Mx Nf Nk Nn Nu Oa oE Oi Op Or Ow Oz Pa Pf Pk Po Qd Qg Qx Rc Ru Rv Sh Sj Sr Un Uu Uy Vo
Vs Vt Yl) Bn(aA aM As Ax bB Cp Cq Cs Cu Cw Dc Dr Du Ed Eq Ex Fw hB Hl Hv Hw Id Iv iZ Jd Jh Ji Jq Jr Js Kd Ke Kk Kl Kn Kp Kx Ld Lh
Li Lj Lw Mi Mj Ml Mq Mr Mw Mx Nn Nr Nu Nv Ny Oa Oi Om Pb Pe Pf Pi Ph Po Qg Ra Rb Rc Sr Tv Ul Un Up Ut Uz Vp Vt Wg Yl Xa)
cX(aA Aj aP Ar aW Ax aZ BG BO Ch Cs Ct Dg Ed Ef Eq Fp Fw Gd Gh GL Gp hB Hc Im Iv Iz Jj Kd Kl kR Ld Li Lx Lz Mh Ml Mq Mx Nc Ng
Nu Nw NY Of Oh Oi Ow Oy Oz Po Qb Qd Qe Qw Qx Rc Rj Ru Sh Sj Sr Ss Uh Ur Uu Ux Vo Vs Vt Wc Wf Wh Ye) Oe(aA Ad aF Aj aP Ar aY
bG bL bN Bo De Dg Eq Fc Fw Gd Gh Gl hB Hc Ik Iv iZ Jj Jo Kj KR Ld Li Lj Lv Me Mh Ml Mq My Ng Nu Ny Oa Oy Oz Pb Pc Pe Ql Qt Qw
Qx Qz Rc Rj Rm Sj Sr Ss Ua Uh Uv Vb Vo Vs Vt Wc Wh Ye) aW(aA aF Aj aM aO Ar Ax bF Ch Cs Dg dH Dp Ed Eq Fp hB Hf hG Hu iH iZ Ji
Jj Ke Ki Kl kQ Ld Li Lj Lz Mh Mj Mk Ml Mq Mr Mw Mx Nd Nu Oi Oy Oz Pa Pb Pc Pf Qb Qd Qg Ql Qv Qw Qx Qy Rc Rv Rz Sh Sj Sr Ur Uu
Vo Vs Vt Yl) aN(aA aM aP Ar As Ax bB Bg Cs Cw dL Du Ed Eq Et Ex Fi Fp Fw Gc hB Hv Hx Ir Is Iv iZ Jh Ji Jq Js Kd Ke Kl Kx Ld Lh Lj
Me Mi Mj Ml Mq Mt Mx Nr Oa oF Oi Om Pf Pk Po Qg Qx Rc Ru Rv Sh Sr Ul Un Uu Uy Vh Vo Vt) aY(aA aH aP Ar bB Cs cU Cw dL Dp Et
Ex Fp Fw Gc gL hB Hv Iv Ji Jq Js Kd Ke Kk Kx Ld Lh Lj Lp Lx Lz Mh Mj Mk Ml Mq Mt Mw Mx Nn Nr Nu Nw oF Oi Or Oz Pf Pj Po Qb Qv
Qx Rc Rv Sh Sj Sr Uh Un Ur Ut Vo Vt Ye) Vs(aF aM AP bQ cN Co cS Cu Ez Fc Fr Ho Hu Hv Hw Ic Ij Il Io Iv Jh Jt Kd Ke Kg Kq Kx Ld Li Lx
Mg Mk Mq Mt Mu Mw Na Nb Ni Nn Nr Nt Nu On Ow Oz Pd Pe Pf Po Qd Qe Qw Qy Rc Ru Sj Uf Vq Xa) aF(aH Aj Ar aZ bB BG Bo bQ Ch
Cs cU Dg Ed Eq Fw Gp hB Hu Iz Ji Jj Kd Ke Ki Kk Kl Ld Lh Lj Mf Mh Mk Ml Mn Oa oE Oi Or Pf Po Qb Qv Qw Qx Rc Rj Ru Sh Ss Ua
Uh Ur Uu Vo Vt Wf Yl Ye) Mw(Aj Ar BG Bo Ch Ct De Dk Ef Eq Fw Gl Gp hB Hc Hu Ib Iz Jj Kd Ki Kj Kl Ld Lj Mh Ml My Ng Nx oE Oi Oy
Pb Pf Qv Qw Qx Rc Rj Ru Sh Ss Ua Uh Ur Uu Uv Vo Vp Vt We Ye) Kd(aA Aj An aY bJ Bo Cs Cv Dc De Dg Dp Eq Fd Fp Gd Gl hB Iv Jj Jl
Jo Ki Kj Kl Kp Kx Lj Lp Lz Mh Mk Ml Nx Oi Oy Pa Pb Pf Qb Qg Qh Qv Qw Qx Sh Sj Ur Uu Vo Vp Wc) Oz(aA Ax aZ bA Bg CH dB Dg dN
Dr Ed Eq Ez Gh Gl Gp Hv Ih Ij Ir Iv Jn Js Kl kR Li Lj Lp Lx Mi Ml Nb Ni No Nr Ny Ow Qa Qd Ru Ss To Tz Uu Uy Vb Vo Vw Wc Tm Xa)
Uu(aO Ap Bb Co cS Cw Fc Fw Gc gL Ho Hu Ic Il Iv Iz Jg Jh Ji Kc Kg Li Lv Mg Mi Mk Mq Mt Nb Nn Nq Nr Nt Nu Pc Pd Pf Pz Qe Qw Qy Ru

Ne Nh Nj Nl Of oH Pk Pz Qn Qv Ug Uo Ur Uu Vo) Wd(Af aG Aj aX aZ Bg Ch CX Dd De Ef fP Fr Hu Mi Mt My nY Oy Qn Qu Qw Qz Ug Uh Uu) Oe(AA Et Ih Ip Iq Ir Is Iv Ji Jl Jn Js Jt Li Lj Mw Nc No Nw Ok On Pa Pe Qc Qd Vz) mZ(In Ji kC kG kI kN Lu Ma mF Mg Mi MP Mr Mv nA nC nH nN Nq nT Nw Oh Oz Pd Pf Qc) Lp(Af aG Ax bP bX Cu Dc Dd Em Hv iP Iv Jn Jr Js Mi Mr Mx Na Nb Pc Pi Qv Ri Ur Uu) Hb(AA aE cH dB Du Em Fn Gh Hq Ju Jv Jy Ki Ld Mz No Nt Ou Ow Qt Ru Ur Vt Tl) Of(Aa Et Ij Ip Iq Ir Is Iv Ji Jt kI Li Mi Mr Mt Mw Mz nA nC nH Nm nT Nw Ok Pe) Fc(Af aR aZ Ch cX De Et Fr Gp Hc Ij Iz Ji Ki Lj Oi Oy Qn Qz Ss Tz Ug Uh Uu) Tl(Af aG Aj aR aZ Bn Bo CX De dG Dk fP Fr Hc Iz Ki Mw My Nv Qn Ug Uh Ur) Vb(aG aR aZ Bo Cw CX De Dk Hc Ib Iz Ki Kj Kl My nY Oy Ug Uh Ur Uu Vo) nA(Il Li Lz Ml MP Mw nC nH nI nK nM NN nT Nu Oh Pa Pc Pe Qc Qd) Ru(Af Aj aZ bM cF CX fP Fr Hc Ib Iz Ki Kl Oy Pc Qn Ss Ug Uh Un Uu) Vh(Af aR aZ Bg Bn Bo cX De Dk Ib Iz Kf Ki Mw Nv Oi Oy Qn Ug Uh Ur Uu) Du(aG AJ aR aZ Bn Bo De fP Fr gP Hc Ib Iz Ki Oy Po Qn Qt Ug Uh) Lj(aA Et Ik Iq Ir Is Iv Ji Jq Jt Lw Mi Mp Mw Nn Ns Nw Ok On Oy Pc) mF(Fp Il In Jm mI Ml Mw nC nH nI nK nL Nq nT Nu Pa Pe Pf Qa Qc Qd) Em(bO Ef Gl Hc Ib Kf Nc Ne Nh Nj Nl Pa Qn Ug Uh Ur Us Vo Vp Vs) Li(AA Et Hq Hu Ik Ip Iv Ji Jk kF kG kN My nD Ng Ns Oi Oy Rz) Wb(Ar bB dB hB Hf iP Kx Ld Lh Mf Mk Ml oE Ow Pf Qv Qx Rc Ua) Hu(aA Et Ij Ip Iq Jg Ji Jt Lz Mw nC nH nK No Nw Ok On Qd) Ye(aG Bb cR cS Dg dR Iu iZ Ji Mk Mp Mq Mt Nm nW Pc pF Qv) Nw(aA Iv Jk Jt Jv My nC Ng nL Ns Nx Ou Oy Oz Qn Qw Vs) mI(Fp Ii Iv Jg Jo Jt kC kF kN lW lY Ml nD Oi Oy Oz) nT(Ii Jo Jr kC kI kN Ml nD Ng nI nJ Oi Oy Oz Qc) Rz(aJ bP Cw cX Dd iJ Nn nY Oi Pd Qu Ri Uf Vq) Oz(aA Ip Is Jl Lz Mw nC nH nI nL No Ns Qd) Ou(Aa aU cH dJ Ju Jv Mw Mz Oi Qw Uh Vs) Oy(AA Et Fi Ji mP Mw nN Pa Pf Qd Si) kN(Hq Il Jr Lx Lz Ml nH No Nu Pe Pf Qc) nK(Jr kC MP Mq Nb nI nM Oh Pc Qd) Et(aA Jk My Ng Ns Nx Qc Qd Uu Vs) Ml(kC mP mT nC nH nI nM nN oO oQ) Aa(Js Lu Lz Mk Mr Mw Oi Qc Uu) Fi(Aj Bg De Ld Oi Qv Ur Uu) Gn(Ef Ib Iz Ki Qv Ug Uh Uu) Ns(aA Jr Jt Lz Mw Nc Nd No) Ng(Ip Iq Jg Jt Mw Nc No Ok) Hr(Hw Ir Iv Ji Jt Mz Ok Pe) Vz(aK Cw dR Il Ji Mg Mh Mk) Si(aA Af Aj Ch Hc Ug Ur Uu) Qc(aA kC kG kI lY nB nI nN) Jk(Ir Is Js Jt Mw No Qd) Op(aR iP Ki Oi Qn Qv Uh) Uy(Bo fP hB Ki Oi Qn Qv) nI(In kI Lz Mp nC nH nL) kC(Hq Il nC nH Nu Oh Pe) Ji(aA Ik Jq Ms My Nx) Jo(kG mP mT nM nN nR) kI(Hq nC nH Nu Pc Pe) Lz(Ip kE nC nD nH) li(mP mT nM nN oQ) Oi(Hp Sf Sh Zx Th) My(Jt Mt On Pa) nD(Nr Oh Pe Pf) nY(eM Sh Sj Tm) Ip(aA Mw Nc) Fp(Ik oQ) Gh(aH gP) Iv(Hx Th) Sf(gP Qn) Sj(Kl Qv) Nx(mP nM) Vs(aE Js) Vw(bP Uu) Pf(nL Pd) mM(In Nu) DeKq LxnL MeaA MkPa MwIk NcNe NdHq HpQv IsjT UgeM PekE} Rx{Lj(aA Ad aE As Aw Ax BA Bb Bc Bg cM Cp Cq Cs CT Cu Cv Cw Dc Dd Dk Dl dM Dr Ef Em Et Fd fR Fy Gb Gn Ha hG Hl Ho Hp Hv Hw Hx Ib Id Ii In Iq Ir Is It Iv Iz Jd Je Jg Jh Jk Jl Jn Jo Jp Jq Jr Js Jt Jy Ke Kf Kj Kk Kn Kp KQ Kr Lp Lw Lx Md Me Mi Mj Mr Mu Mw Mx My Mz Na Nb Nf Ni Nr Nt Nv Nw Of Ok Om On Ou Oy Pb Pd Pg Ph Pi Pk Po Qa Qd Qe Ql Qt Rb Rg St Tn To Tv Ua Uc Ul Un Uo Up Ut Uw Uz Vb Vh Vp Vq Vs Vt Vw Wb Wc Wd We Wg Wh Xa) Ih(aA Af aH Ar AX bA bM cE Ch cJ cM Cq Cs Cu Dc Dg dI DR Ed Em Fd Fp Fw Gb Gd Gz Ha HB hC hG Hp Hv Ii Ij In Ip Is Iv Jd Jf Jh Ji Jj Jn Jp Jq Jr Js Jt Kd Ke Kl Kn Kq Kx Ky Kz Ld Li Lx Me Mi Mj Mr Mt Mw Mx Na Nb No Nq Nr Nt Nw Oa oE oF On Or Ow Oy Oz Pc Pe Pg Pi Pk Po Qa Qd Qe Qt Qv Rv Ry Sh St To Tv Ug Un Up Ur Uu Ux Uy Uz Vo Vp Vt Vz Wb Wc Ye Xa) St(aA aE aP Ax bA cH Cp Cq Cs cT Cu Cw Dc dM Dr eF Em Fd Fp Fy Gb gL Ha Ho Hv Hw Id Ii In Ir Is It Iv iZ Jh Ji Jl Jq Jr Js Jt Kd Kn Kq Li Lp Lx Me Mi Mj Mq Mr Mx Na Nr Nt Nu Nv Oa On Ow Pd Pe pF Pi Po Qd Qv Sr Tv Un Ut Uz Vp Vs Vt Xa) Nw(aA aF aO aP Ax bA bF cE CH Cq Cs Cu cX dA Dd Dl Dr Fp Fy Gb gL Ha Hp Hu Hv Hw Ii In Ir It Iv iZ Jh Jr Js Jt Kd Ke Kn Lp Lv Me Mf Mi Ml Mr Mx Na Nb Nr Nt Nu Og Op Pd Pi Pk Qn Qw Qx Qy Ra Sj Sr Ub Up Uy Vp Xa Tj) Nb(aF aO aP AR aS aY bE bF BG bJ Bn bX bZ cE Ch cO cZ Dl Fp Fw Ha Hb Hc Hx Ir It Iu Ji Jl Js Jy Kp Kx Kz Lz Ml Mw My Mz Nx Oa Of Og Oh Ow Oy Pa Pd Pe Pj Pk Po Qb Ql Qm Qw Rb Sh Sr Tn Un Us Uv Vq Vt Wf Xa) Sr(aA aE Af aG aH Aj aM An aQ Ax aZ bI bM bR cD cM Cx cY Db dR Gp Hb hG Hp Io Is It iZ Jh Ji Jj Jl Js Ke Ki Kk Ko Kq Ky Kz Lt Lx Mr Mw Na No Nr On Oz Pb Pc Qa Qd Qe Qh Qw Qy Rm Sj Uk Uo Wb We Wf Xa) Ke(aA Af Aj aM aN aV aW Ax aY Ba bJ Ch cO Cs cV cZ Dr Fy GL hB Hp Ir It iZ Jn Kj Kz Ld Li Lx Lz Mh Mq Mr Nc Ne Nf Ni Nj Nl Nr Nt Nu Nx Ny Oa oE Oh Ow Oz Pb Pf Pk Qa Ql Qx Ra Ub Up Uu Uv Wm) On(aA aF Aj aO Ax aY aZ Bb bF BG bM bZ CH cV De DR Eq Fr Gb Ha Hc In It Iv Jj Jr Jy Kd kR Li Lp Lu Lv Mf Mi Mx My Na Nu Og oH oN Op Oy Pi Pk Qd Qw Sh Tn Uu Uv Ux Uy Vp Vt Wb Wf Zx) Ny(AP Ax Ba Bc bF BG bJ Bn Ch cO Cs cT Cx cZ dE Dk DL Dr Du Ed Ez Fp Gc Hc Hw Ic Ik Jj Lx Lz Mg Mh Mk Ml Nf Nn Nt Oa Oh Oz Pj Pk Po Ql Qw Qx Ra Rf Rh Ru Sh Uf Uu Vp Vq Wf Zx Wm) Oa(aA aE Af aV Ba Bb Bc bJ cM Cp DD dI Em fR Gb Hb Hx Ij Iq Jd Je Jh Jj Jn Jy Kd Kq Li Lx Mb Me Mi Mq Mr Mt Mv Na Nf Nh Ni Nj Nk Nt Pe Pk Qa Qd Ql Qm Qy Ub Ur Vz Wd Xa) aA(Ax bI cH Cw Dc Et Fy Gc Hb Hw Hx Ii Il Ip Iq Ir Is It Iu Jf Jg Ji Js Jt Kn Kq Lx Mr Mw Na Nr Of Oh Om Oz Pf Po Pz Qb Qc Qd Qe Qh Rf Rm Si Tz Uc Un Ut Vh Vq Vt Xa) Qa(AD AF aO aY bF Bg bM BO bZ Ch cV dA dD De Dr Ed fP Fr Hc Hl Hp Iv Iz Jf Jj Kl Kr Li Lv Mf Mj My No Of Oy Qu Qw Rg Rv Sh Tn Uo Uu Uv Uw Vs Vt Wb We Wf) Mw(aE AX aY bA Bc CH Cq Cs cT Cu Dc Dr Eq Fd Fy Hv Hx In Iq Ir Is It Iv Iz Jj Jr Js Kd Kn Lp Mi Mr Mu Na Nr Nt oH Pi Pk Po Qb Qu Qz Rm Sh Tz Uz Vt Yl Xa) Ir(aN bM bN BO bX cO Cs CX Dr Fp hB hG Hx It Iv iZ Je Jf Jh Jj Ko Kq Kx Kz Ld Li Mh Mq Mr Mt Mv Nf Nq Nt Nu Nv Ow Oz Qd Ql Qw Qy Sh Uo Ur Vz Wb Wf Xa) Xa(Af aN aY aZ bJ bM Bo bU cB cG cI cV CX Ed fP Hp Hu Hv Hx Ii Iv iZ Je Jh Jj Jm Kd Kk kR Ld Li Lv Mt Nl Oi Ow pF Qb Qd Qw Rm Ru Sj Tz Uh Un Vs Vt Th) It(aH aM aW bM Bo cE CX DR Ed Fw Hp Hu Is Iv iZ Jh Jj Jl Kk Kq Ld Mt Mz Nl Nt Nu Nv oE Oh Ow Oz Pc Pf Qb Qd Qe Qt Qw Rm Ry Sh Uh Un Uu Vt) Dr(AP Aw Ax aY Bb Cp Cx Fy Gp Ha Hu Ii Il Iq Is Jg Ji Jn Js Kn Lp Lx Mt Nr Nv Oh Om Oz Pe Pg Qb Qc Qd Qe Qh Qt Qw Rm Ru Si Tz Uh Vt Wf) Kq(Aj AO AX aY aZ bG Bn cE cH cV Dk Ef Eq Fr Ha Hc Hp Hq Iv Iz Jy Kd Li Lp Lu Lv Ma My Na Nq Qb Qd Qu Qw Sh Tz Ut Ux Vt Wb Zx) Qe(aC Af Ar Ax aY bA bJ bM BN bO cB cV Cx cZ dA De dI gL hB Hl Hp Hx Iv iZ Jj Ld Li Mq Na Nl Nr Nt Nu Ow Pk Rf Sh Uo Up Uu) Li(aE aV AX aZ bN bO cQ Cu Dg Fr Ha Hx In Iq Is iZ Je Jl Jm Jn Js Kg Kl Ma Me Mg Mm Mr Nt Oy Pc Pi Pk Qd Qu Rm Tz Un Uo) Mr(AF aV aW aX bJ bM Bn Bo cD Ch CX Ed fP gP Ha Hb Hc iZ Jm Ld Lp Lu Ow Oz Pb Qb Qn Qw Ru Si Uh Uv Vp Wf Ye Th) Is(Af aN aY bF Bg bJ bM Bn CH Cs cV dA hG Hp Iv iZ Je Jh Jj Kz Lv Mf Mq Nt Nu Og Op Ow Pk Rv Sh Ub Uu Uv Vo Vt Wb) Qd(Ar Ax bA Bc Ch Cs cT cV dA dR Eq Fy gL Ha hB hG Iv Jj Js Kx Ld Mq Na Nr Nt Nu oE oF Oh oK Ow Qx Ra Rf Rg Sh Ua Uu) Jn(aC AF aN aO aS aV aY bM bN bO bX cH Cq cV Cx dD dI Hc Hf Iv Jf Kz Ld Nc Nf Nl Oz Pa Pk Qw Uo Uv Vp Vt Vz Wb Wf) iZ(Ax Bb Cu Dc Et Fy Gc Ij Il In Jg Ji Jq Js Jt Kd Kn Lu Mi Mx Na Nh Nr Oh Ok Oz Pe Qh Rb Rm Si Uf Up Vq Vs) Iv(aE Bb Bc bJ bR Cx Et Gb Ha Hb Hx Jg Jh Ji Jl Ky Mz Ng Nt Oh Ok Om Ow Oz Pb Pc Qb Qm Qy Rm Si Uw Vt) Js(aC aE AF aN aY bJ bM BO cV Cx fP Hp Hu Je Jh Ld Mh Mq Mt Nl Nt Nu Ow Oz Pc Qy Sh Uh Uo Vt Wb) Rm(aE BG CH cM Ed Gb gL Ha hG Hx Je Jj Kz Ld Mf No Nt Nu Oy Pi Pk Rg Rv Sh Un Ur Uu Wb) Ow(aE Ax cM Cp Cq Cu Dc Dd Fd Gb Hv Hx In Jr Jt Kd Kn Me Mi Na No Nt Pg Pi Tv Ub Un Vp Wb) hB(Ax Cp Cq Cu Dc Fd Hv Ii In Jp Jr Jt Kn Lp Na Nj Pe Pg Pi Qh Rb Tv Tz Uz Vp Vq Vs Wb Wc) Pe(aD Af aH aX Ba bN bO De dI hG Hp Je Jf Lv Lx Nl Pi Qy Uo Vt Vz Wb Yl) Cx(Ax Cq Cu Dc Fd Fy Ha Hv In Jr Jt Lp Mi Na No Pg Pi Tv Up Vp) Nu(Ax Dc Hv Ii Jq Jr Kd Mi Na Nr Qc Qh Tv Tz Un Uz Vp Vq Vs Wc) Jh(Aj AX CH Cs cV Ef Eq fP Ha Iz Kd Mx Nr Oh Qb Qu Sh Wf) Fy(Af Ar bM Bo Hb Hp Je Jj Ld Mq Oz Pc Ql Qy Rh Sh Un Vt) Jl(aO Bb bF Bg CH Cq cV Dd In Kd Kn Mi nW Og Pi Uy Vp) Nt(aX Dc Hb Hx Ij Ji Jq Jr Mj Oh Pb Pc Qb Sj Un Vq Vt) Oz(aP Ax Cp Cs Cu Fp Ha Hp Hv Kn Na Nr oF Pi Pk Un Tj) No(aN Ao aW cL gL hC Hf Hq Jg Jm Nn nW Pf Pz Rh Vt) Ld(Ax Bb Cu Dd Ha Hv Ii In Jt Kn Lp Mx Na Pi Tv Wb) Oh(aE aF bM Dd fP Gb Ha Hp Hx Je Pc pF Pi Un Vt Wb) Nr(aS bJ cV Hb Hp Je Kz Nf Ql Qm Qy Rh Un Vt Vz) Ax(aE cM Hp Hu Hx Je Mq Nv Pc Pi Qy Uh Un Vt) Cs(aY Bb bJ Hu Jg Jk Kd Pc Pi Pz Qy Vt Wb) Ha(aG aM cX dR Hx Jj Lx Lz Ml Pf Qx Un) Ij(Aj aZ bE Cq cV cW Gd Lv Pk Vo Vt Th) Lx(aC Af bJ bM bO Dd Hp Je Mh Vt Wb) Na(Ar aX bM Bo Nv Pb Pc Qb Qy Uh Vt) Un(Af bA cD cT gL Gp

Figure 38 Continued

Jg Lp Mx Ru) Pi(aM aP Ar Ml Mq Qb Rf Uh Us Vt) Cu(Af aY aZ cV Gl Pb Qb Vt) Mq(Bb Dc Ed Jt Kn Lp Qh Wb) Mt(aE aX Ed Fr Gb Hx Us) Rf(Bb Dd Gb Hv Jt Kd Mi) Ch(Ef Iz Jg Jp Om Ut) Mx(aC aY bE bJ Nl Ql) Hx(Bo Fw Hu Qw Ry Um) Ed(aU aW Bc Ql Uf) Jt(Af Aj Gd Jo Kj) Kd(Ar bJ Mv Nf Qm) Ut(aY fP oE oH Sh) Vt(BA Mv Pd Ub) Wb(Kx Ml Ql Qx) Ji(Af aY Hp Jm) Qy(bA cT Jr Kn) Lp(Ar Mv Nf Ql) Om(Aj Eq Sh Uv) Pk(aZ cX Ii Vq) Qb(Ba Bc Vw) Ok(Af aY cV) hG(Il Tz Vq) Ar(Hv In) Bb(Fp Ql) Bo(In Kn) Po(bM Uv) Fd(Lz Qx) Mz(aY kR) Hp(Et Pf) Tn(aY fP) Hb(aP bQ) Jg(Fp Sh) Ur(Dc Fw) aZ(Cw Hw) AjNv BaEq CqQl DdaP TzfR JpcH JrbJ PcoF} Ru{Ld(aA aP AX aZ Cp Cq Cs Cu Cw Dc Dd Dr Ed Fd Fi Fp Fy Gb Gc Gd gL Ha Hb Ho Hp Hv Hx Ii Ij Ir Is It iZ Ji Jl Jn Jp Jr Js Jt Ke Ki Kn Kq Kz Li Lx Me Mi Mj Mw Mx My Mz Na Nh Nj Nt Nu Ny Oa Ok On Pc Pe Pg Pi Pk Po Pz Qa Qc Qd Qe Qh Qm Qy Rb Sr St Tv Tz Uh Un Up Uz Vp Vq Vs Vt Vw Wb Wc Wh Yl Zw Xa Tj) Kq(aA Ad aF aM AO Ar As AX aY aZ bF bG bM Bn bR bZ cE CH Co Cs cV Dg DK Dp Dr eF Ez FP Fr Fw Gd Gl Hb Hc Hl Hq Hx Iv Iz Jj Jk Jn Jo Jy Kg Kj Kz Li Lv Lz Ma Ml Mn Ms My No Nu Nx Ny Og Oz Pc Pk Qb Qw Qx Rz Sh Sr Ss To Tz Ua Uh Ur Us Ut Ux Vo Vs Vt Wb Wf Wh Zw Xa) Iv(aA aE AF aG aH Aj aM aS aZ bJ Bo Ch cM cQ CV Cx Dr Et fP Fw Gb Gc Hb Hc Hl Hx Ih Ji Jl Jn Jo Jp Jy Ke Kp Ky Kz Li Lj Lx Lz Ml Mq Mr Ms Mt Mz Nb Ne Nl No Nu Ny Oa oE Of On Ow Oy Pj Po Qa Qd Qe Ql Qm Qx Qy Rh Sh Si Sr St Tz Uh Um Un Vb Vc Vt Wf Zx Xa) Ed(aC Af aG Ao aQ aU aW aX bC bH bJ Bn bW bX bZ CO cP cR cX cY dR Et Ez Gp Hb Hx Iu Jd Jh Ji Jy Kc Kd Ke Kg Lz Mg Mi Mm Mp Mq Mr Mt Mu Mv Mw Nc Ne Nf Ni Nk Nn Nq nW Om Oz Pc Pd Qd Qw Qy Rh Si To Uf Ug Ur Wd Xa Tj) Qd(aA aF Aj aO Ar Ax aZ Bg bM bN bO Ch Cs cV CX Eq fP hB HC hG Hl Iz Jf Jj Kj Kl Kr Kz Lj Lp Lx Lz Ml Mq Mr My Nb Nf Ni Nu oE Oh Ow Oy Oz Pa Pb Pc Ql Qu Qv Qx Ra Rf Rh Sh Sr St To Ua Ur Us Uv Vs Zw Xa Wm) Mw(aA aG aH Aj aM Ar aX aY bR cF cH cV Di Dr Eq fP Fw Gc Gd Hb Hu Is Iz Ji Jj Jk Kj Kl Kn Kz Mi Mk Mr Ms Mz Nd Ne Nu Nw oE Oy Oz Pc Pk Po Qu Qz Ss St To Tz Ua Uh Ul Un Ur Uu Vc Wb We Tm Xa) Mq(aA AX aZ Cp Cq Cs Cu Dc Dd Em Eq Fd Fy Gb Ha Hb Hv Ij In Ir Is It Ji Jn Jr Js Jt Ke Kn Lx Me Mi Mj Mr Mx Nj No Nt Ny Oa Ok Oy Pg Pi Qe Qh Rv Sr St Tv Tz Uh Up Uz Vp Vq Wb Wc Xa Tj) Ke(aE Af aM Ar aY bJ bM bN Ch cM cV Cx fP fR Fw Gd Gl hB HC hG Hp Iq iZ Jj Kf Kg Kp Kz Mn Mr Nb Nc Ne Nf Ni Nl No Nt Nu Nx Ny oE Oz Sh Sr St To Ub Uk Up Ur Us Uu Uv Vh We Wf Tm Xa) Ur(Ax Cp Cq Dc Dd Dr Em Fd Fp Fw Fy Ha Hp Hv Hx Ih Ii Ij Ir Is It Jl Jn Jq Jr Js Kd Kn Lj Lx Mi Mr Mx Nb Nh No Nw Ny Oa On Pe Pg Pi Po Qc Qh Rm Sr Tv Tz Vq Vt Wb Xa) Un(aA AF aO aY aZ bM bN cE cH Cs CX Dp Dr Fp Fw Fy Gl hB Hc Hf Is Jn Jr Jy Kp Kx Kz Lj Lp Lt Me Nu Ny Oa oE oF Oz Pc Qn Qw Sh St To Ug Um Uu We Wf Yl Zw Xa) Jd(aA Aj AX aZ Ch Cq Cs Cu Dc Dr Eq Fd Gd Hb Hc Ij In Is It Jn Jr Js Kd Kz Lp Lx Mj Mx Mz Na No Ny Oi Oy Pg Pi Qh Qw Sh Sr Ss Tv Tz Uh Up Ux Uz Vp Wb Wf Wh) Nw(aA AF aN aO aY bN cV CX Dd dF dH dI Dr Fn Fp gL Hp Hu Hw iZ Jh Jn Jr Kz Lj Lv Mi Mr Mv Nb Nd Nh Nt oN Oz Pa Pc Qn Qw Qy Rg Rv Sj Sr To Ub Wb Zw) Vt(aA aF aN bN bQ CX Dr Fp fR Fw Hf Ho Hp Hq Hv Hw Is It iZ Jh Jn Kz Lj Lt Mi Mt Mv Na Nb Nh No Nt Nu Nv Ny Oa On Oz Pc Po Qw Ub Ut Wb Wf Xa) Kz(aA aG aX aZ Bo Ch Cs Cu DK Fp Fw Gc Gd Hb Hv Ij Is It Jh Ji Jj Jn Jp Ki Li Mr Mt Mv Nb No Nq Nt Nu Ny Oa On Qa Qe Qy Sr St Uh Ut Zx) Ny(aF Ap Ar aU aX bC bW CO cS cV cX dR Ez Fc Fp Gc Ho Jh Ji Jc Kg Mg Mi Mk Mp Mt Mu Nq Om Oz Pa Pc Pd Pj Po Qy Rz Sh Ue Uf Uh Wd) Fp(aE aG aM aY aZ bR cH cM cV Cx Dr Et Fw Gb Gc Hx Ih Is Jj Kc Mi Mr Mz Nb Nd Nt On Ow Oz Pc Pd Sh Sr St To Uh Vc Vq Wf Tm Xa) Dr(aP Ar aU Bo cC cU dR Et Gc hB Hv Is Jh Jn Js Kx Lh Lx Lz Mm Mp Mt Nn Nq Nv Om On Ou Ow Pa Qa Qe Ql Qx Si Tz Uh Ut Tl) No(Ao aQ bX bZ cJ CO Cw cY dA De Et Ez Ho iH iO Ji Kc Kg Li Ma Mg Mi Mm Mp Mt Mv Nq Ou Pa Pd Pj Rh Rz Sh Uf Ug Zw) Mr(Af aG Aj Ar aZ Bn bX Cv CX dM dR Hb Ij iP Ji Li Lx Lz Mk Ml Mv oE Ow Oz Pc Pj Qv Qx Rj Ry Ug Uh Us Wf Zw) Fw(aA Af Aj aY aZ bM Bn BO cV Cx Gd Hb Hx Jh Ji Jj Ki Mi Ms Mv Nq oK Oy Pa Pc Qy Rh Sj Uh Vo Wb) Wb(Ar Cx Et Gc Is Jq Js Kx Lh Li Lj Lx Lz Ml Mp Mt Nq Oh Ou Ow Pe Pf Po Qa Qb Qe Ql Qx Si Sr Tz) aZ(aF Ap aU bJ Co Cw Cx Ez Fc gL Hv Jh Kc Kg Mg Mi Mt Mu Ni Nq Nu Om Oz Pd Pj Ql Qy Rz Uf Vq) Cs(aF aY bE bJ Co cV Cx Ez Gc Jh Kc Kg Mg Mi Mp Mt Mu Mv Nn Nq Om Pc Ql Qy Sr Uf Vq Wd) Ji(aE aN aY bN bO cV Cx Fc Gl hB hG Hp Je Jf kS Nb Ni Nt Nu Oa Qy Sr St Uu Uv Zw Xa) Jh(Af aX Bg Ef Eq fP Gd Hc Iz Jj Kj Kl Lx Ng oE Oy Oz Pc Qu Qw Sh Ss Uh Uu Vo Wf) Li(Aj bO cF Dg Eq Gd HC Hf Hp Hx iZ Kg Kj Kl Me Mm Oy Pc Pk Qu Sh Uu Ux Zw Xa) aA(aF aU bB Et Gc Hb Hv Is Iu Js Lh Lx Mi Mk Nq Om Ou Pc Pe Pj Po Qa Qe Ql Sr Uh) Qy(Aj Ch Eq fP Gd Hb Is Jn Jq Jr Kl Oh Oy Oz Po Qb Sh Ss Tz Uh Uu Ux Vo Xa) Xa(Aj Ar aS bA Bo cT cV Gz HB Hv Hx Jj Nq Og Oz Pa Pc Ql Rh Sh Sj Uh) Pe(aG bN BO bX dI Gd hG Hl Jf Kp Lx Ni Pa Qv Rv Sh Ug Uu Vz Yl Zw) Nt(Aj Dg Dp Eq Hb Jj Kj Lh Lx Lz Mj Ml Or Ph Po Qa Qb Qg Qx Tz Uh) Cx(Cp Cu Dd Gb Ha Hx Is It Jl Jr Lj Me Mi Oa Pg Pi Po Qc Tz Uz) Uh(aE bM Fd fR hB Hf hG Hp Hw Hx Je Me Mu Ni Nu Nv Oa On Oz Uo) Sh(Cu Dk Ef Et Gc Hu Ij Is It Jl Jn Jv Mt Nq Nv Om On Qa Ut) Ql(Ax Cq Cu Dd Hv It Jn Jr Js Lp Mi Mx Na Pg Pi Qh Tz Vp Zw) Oz(Cu Dk Hq Hv Id Ik Is It Jl Mv Nq Nv Om Po Qe Tz Ut Vq) Sr(aG Aj bH bM Gd Hf Hl Jj Mv Nq Og Oy Pa Pc Sf To Vz) Ar(Cp Cu Gb Ho Hv Hx Is Jn Jt Mi Nh Pg Pi Vq Vs) Mi(Aj aX Eq HB iZ Jj Jn Jo Kg Kj Or Qm St) Lj(aC aF aG aN bE bJ bM cO cV cZ dI Hv Jy Mv) Oa(aG aY bE Bn Bo cO CV Hl Ms Nq Pc Wf Zw) Af(Cu Et Gc Is Lx Om On Ou Ow Pg Po Qe Vq) Nu(dR Gz Hb Hv Hx Jq Mj Mv Nh Ou Pc Po Tz) Oy(Ef Hv Mp Mt Mv Nn Nq Nv Om Ow Qa Qz Wd) Nb(aS cC cP Gc Hb Hv Kp Mp Nf Pa Pc Rh) Jj(Fi Ho Hv Is Kd Mv Nh Om Ou Ow Ut Vq) Cu(Aj Dg hB Hc Kj Kl Kp Pa Qm Uu Vo) Qa(bM bN bO dD Hl Iq Pa Pc Rv Uo Zw) Jn(aM aS cO cV hB Mu Nf Nq Pa Pc Ug) Mt(aX Eq Fr Hb Hc Kj Kl Me Pc Zw) Is(aY bJ bM Cq Cv Pa Pc Rv Wf Zw) Qe(bM Bo Cv dI hB Hl Iq Pa Pc Vp) Aj(Ho Hv Hw Nq Om Qz Uf Vq Wd) Lx(bE bJ bN bO Hp Ni Pa Rv Zw) iZ(aG aU dR Et Gc Lu Pc Pj Si) Po(aN BO Hp Pc St Uv Zw) Ij(aS Cq Cv cZ Hf Ni Pa Rh) Eq(Mu Nq Om Qz Rz Uf Wd) Mv(Ch cV Hc oE Wf Wh Tm) Hv(aH bM hB Hl Pc Qm St) Ut(aY Ch cV fP Hc oE Wf) Bo(Ha Hx Ih Kn Mz Vq) Nq(aO Bg Hc oE Qu Tm) Om(aX Ch Gd Hc Kl Uv) On(aF Hc Kl Pa Uu Zw) Gc(bM Gd Hx Pk Uu) aX(Co Ez Kc Mg Uf) Ho(hB Jo Kg Kj) Hp(Lz Mk Mp Qx) Tz(bJ bN Ni Rv) Hx(aN Hu Mk Qw) Vq(Cv hB Hl Pa) Hb(cO fR Hu) Ow(aY Gd Zw) Pc(aP It Js) Ch(Ef Mu) Kl(Ef Jg) Nv(cV Hc) Or(aF Gb) Uf(Kg Kj) Pa(Js Rm) Pi(Lz Qx) gL(aH fP) hB(Cp Na) AxRh GdPj GzOh HaaG MxNi NeNh StaF OuaY} Xa{cV(aA aH Aj aM Ar As AX Bn Bo bQ CH Cq Cu Cw Dc Dr Em Fc Fd fP Fw Gn hB hC Hl Hv Hw Hx Id Ii Ij Ik In iO Is Iv Jj Jn Jq Jr Js Kd Ke Kk Kl Kn Kq Kr Ld Lh Li Lj Lw Lx Mi Mj Ml Mq Mt Mw Mx Mz Na Nf Ng Nn No Nr Nv Nw Ny Oa oE Oh Oi Ok Om On Or Pb Pc Pf Ph Pi Pk Qc Qx Ra Rb Rj Sh Ss St Tn Tv Ud Uh Ul Up Us Ut Uu Vh Vp Vs Vt Wg Ye Tj) aY(Aj aM aP Ar aS bB bG bZ cC Ct Cu dL Dp Ed Eq Et Ex Fp Fw Hb Hv Hx iA Ij In Ir Is Iv Ji Js Ke Kl kS Ky Kz Lh Li Lj Lp Lz Mh Mj Mk Ml Mq Mr Mv Mw Mx Nf Nh Nn Nq Nw Ny Oa oF Og Oi On Or Ow Oy Oz Pa Pb Pf Ph Qa Qb Qd Qe Qg Ql Qx Rc Sh Sr St Tz Uh Un Ur Ut Uu Vt) Bo(aF aO aW Ax Bb bJ bR cH cQ Cu Cx Di Ed Fc Ha Hl Ho Hv Hw Ih Ii Il In Ir Iv Jm Jr Kd Kn KQ Ld Li Lj Lp Mi Mq Mr Mt Mw Mx Mz Nc Nd Ne Nk Nl Nn No Nr Nx Ny Oa Oi Ow Oz Pc Pf Pi Qc Qd Qe Ql Qx Qy Rc Sh Ul Uw Uy Vq Vs Vt Th) Fc(Af Aj aM Ar aZ Bg Cs Ct Dg dK dR Eq Et Gd Gh Hb Hf Hx Ih Ir Is Ji Jn Jo Ke Ki Kj Kq kR Kx Ld Li Lj Lx Lz Mh Mk Ml Mq Mt Nb No Nw Ny Oa On Or Oy Oz Pb Pe Pf Ph Po Qa Qb Qd Qe Qg Ql Qx Sh Sj Sr St Tz Uh Un Uu Vb Vs Vt) Vs(aF Ao Ap aW Bb bE bG bJ Bn Co Cu Cw Cx Ed Et Ez Fw Gc Ho Hu Hv Hw Ic Il It Jd Jh Ji Jt Kc Kd Ke Kg Kq Ld Li Mg Mp Mq Mt Mu Mw Nb Nn Nq Nt Nu Nw Oi Om Ow Pd Pe Pf Pg Pj Qd Qe Ql Qt Qy Sr St Uc Uf Uh Ut Uw Vq Vt) Cx(Aj aP Ar aZ BG bJ cC Ct Eq Fp Fw Gd Gl Ha Hx Ir Jj kR Kx Kz Ld Li Lj Lz Me Mq Mr Mt Mw Nf Nh Nn Nu Nw NY Oa Oe Of Oi Ow Oy Oz Pa Pb Qd Qe Rj Sh Sr St Uh Un Ur Us Uu Vb Vo Vt Wc Wf Zx) Ed(aG AN aQ Ba bC bG bM bN bS cN cQ Cu Cw cY dE dG dM Fd Fn Gp Gz Ha hB Hx Ib Id Ii Il iP Kd Ld Lu Lx Lz Md Mf Mh Ml Nc Ne Nf Ni Nl nW Ow Pa Pe Pf Qx Ra Rh Rj Si Sr Ug Uh Uu Vp Wc Wf Zw Wm) Af(aW Bb CU Et Fw Gc gL hB Ho Hv Ih Il Ir Is Jh Ji Kd Kc kR Ld Lj Lx Mi Mk Mm Mr Mt Nh Nn No Nr Nv Nw Ny Oa Oh Oi Om On Ow Pf Pg Pj Po Qb Qc Qd Qe Ql Qy Sr Uc Uh Un Ut Uw Vh Vq Vt Ti) aW(aA Aj aM Ar aS aX aZ

Figure 38 Continued

Bg bM Ch Ct Dg dK dR Eq FP Gd HB Hv Hx iH Iv iZ Ji Jo Kg Kj Kl Kz Mq Mr Mt Mw Nf Ng Nq Nw Oi Or Oy Oz Pa Pb Ph Qd Ql Qu Rf Sh Sj Sr St Uh Un Ur Uu Ux Vt) Ld(aF Al AN aO Ap aX Bb Bg bL Bn bX Ch cX De Dg dH Eq Ez Fi fP Fw Gh Gl Gp Hu Il Jd Jm Kd Kl kR Lv Mw Nn Nu Nx Oi Oz Pb Pc Pf Pz Qc Qn Qy St To Ul Us Uv Uy Vz Zw Ye Th) Nn(Aj Ar aS Bg bM Ch Co De Dg EF Ez Gd Gl Hc Iz Jj Jo Kf Kg Kj Kl kR Ma Mg Ng Nx Of Oi Oy Oz Pb Pc Pk Qt Qu Qw Rz Ss Ua Uh Us Uu Uv Ux Vb We Wf Th) Oz(aA aN bJ bM Bn cB cW cX De hB Hu Ic Ir It iZ Jh Jn Js Ju Jv Ke kQ Mq Mr Mt Mw No Nt Nu Nv Nw Nx Oa Oh Ow Pe Pf Qb Qd Ql Qn Qy Rm Sj St Ul Vq Vt) Kd(aA Aj aM Ar aX Bb Bg Ch Cs Ct Cv De dK Dp Eq Fp Gd HB Hx Iv Jo Kf Kg Kj Kl Lz Nf Nw Ny Og Oi Oy Pb Qb Qx Sh Sr St Tv Un Ur Us Uu Vt Tl) Qy(Aj aM Ar aX Bg CH dC De Ef Eq fP Gl hB Iz Jj Kf Ki Kj Kl Lz Mh Ml Ng oE Of Oi Oy Pb Pf Qb Qv Qw Qx Rc Sh Ss Uh Us Uu Vb Vo Vt We Wf) Fw(Aj aN Ar Bn Cq Cv cX dC FP Gd Hx Iv Jj Jo Ki Kl Kz Lz Mh Mk Ml Mq Mr Ms Nl Of Oi Pa Pb Ql Qv Sh Sj Uh Un Uo Ur Uu Vo Vt) Ch(aF Ao Ap aX bC bE bJ bW Co cS Cu Ef Et Ez Ho Hu Jd Jh Kc Kg Kj Mg Mi Mq Mt Mu Mv Nq Om Pd Qd Ql Qw Qz Rz Sr Uf Ut Vq Wd) Gl(bG bJ cO cS CU Et Ez Jd Jh Ji Ke Kq Li Mi Mk Mq Mt Mw Na Nq Nw Oh Om On Ow Pf Po Qd Ql Sr Uh Un Ur Ut Vq Vt) Nx(Aj aM Ar aS Fp HB Hx Iv Jd Ji Jj Jy Ke Kq Li Lx Mq Mr Mt Mv Mw Nq Nw Ny Og Oi On Pa Pc Qd Ql Sh Sj Uh Ur Vt) Mw(aN Ar BG Bn Cp De Dk fP Gh Hb Hu Ib Iz Kj Kl My Nc Ng Of Oi Oy Pb Qw Rj Sr Uh Ur Vp Vq We Wf Wh Ye) Pc(Ar BG bJ Bn cB Ct cU Dr hB Iv Jh Jn Js Lz Mh Mq Mt No Nu Oa OF Oh Pe Pf Ql Qx Rj St Wf) Sr(aH Aj aM An Bn Ct cX dC Dl Gd gP Hx Io iP Iv Jj Kl Mt Oe Of Oi Oy Pa Pb Sh St Uk Uo Wf) Vt(aF An bJ BN cB cX Dp Dr Gh Il Jm Mt Na Nr Nt Nu Oe Oi Pb Pf Qn Rg Sj Ul Ur Us Wf) fP(bG bZ cS CU Et gL Gp hB Iv Jh Jn Kq Mk Mm Mq Mt Nu On Ow Pf Pj Po Ql Rc Uh Ut Vq) aN(aA aM aP Ar bG Fp Ha Hr Iv Ji kQ kS Kz Li Lj Mq Mt Nw Oa oF Ow Qb Qd Ql Rc Sh Un) Bn(aM Et Hv Hx Ij Jj Ke Kq Lh Lj Mq Mr Mt Mx Nv Nw Ny Oa On Ow Pf Qd Qe St Uh Un) Pb(cU gL Ho Hu Hv Ic Ih Iv Jd Jh Ke Kq Mq Mt Nt Nv Nw Om Ow Pe Pf Po Qd Ql Un Vq) Oi(aA aF Ar aS bE bG bJ bM bN cO Iv iZ Mq Mt Nf No Nt Nu Ny Oa oH Pe Ql Rj Un) Uv(CU Et Is Jh Ji Jn Ke Lh Li Mk Mq Mt Nw Om On Ow Pf Po Qd Ql Uh Ut Vq) Iv(An aZ bG bL dG dH Du Ic Il Jm kQ kR Of Pa Qc Rj St Ul Uy Vq Ti Th) Uh(aA bJ bM bN fR hG Hp Hw Il iZ Je Mq Nb Nf Nl Nu Ny Oa Sj Uo Uu Wb) Uu(Ao Ap bJ cX Gc Hu Hw Ic Iz Jh Mq Mt Nv Om Pf Pz Ql Qw Rm Si Ut) Pe(aJ bS Ct cX dG Dk Ex gP Hc Ib It Jl Kl Kr Qw Rj Vp We Yc Tl) No(bS Dk dM Fi gP Ib Il iP Je Jl Mg nY Oe Qw Rj Vp Vq Wf Ti) Sh(An cX Hu Ic Il Jh Jm Ju Jv Mt Nr Pf Ph Pz Qw Sf Uk Ul) Kl(Ap Cu Ez gL Hw Ij Jg Jh Kq Mg Mq Mt Pd Pf Qd Ql Vh Vq) Ny(An bG bS cX Dk Ib Ic iP Jl Oe Pj Qn Qw Rj Us Vp Vq Wf) aX(aF Ap bC bJ Co cS Ez Ho Jh Kc Kg Kq Mg Mi Mq Mt Mu Pd) Lj(aC aG aS Ax bE bJ bM cO dI Du Ic Ni Oe Rj Ur Us) Eq(aF Ap bE bJ CO dK Ez Jh Kc Mg Nb Nq Om Rz) Mq(Aj aZ bM cR De Hc Jm kR Ng Qn St Ul Us Uy Th) Jj(aF Bb cX Fi Ho Hu Il Jh Jm Nr Qn Uk Ul Vq Th) Ar(aF An Bb Du Ex Hu Il Jg Jk Jm Ul Uy Vq Th) Us(Jd Jh Kq Li Mt Nq Nw Oa Om On Ow Qd Un Ut) Bg(Ef Hu Is Iz Jh Mt Mv Nq Om Pf Qd Ut Wd) Ul(Aj Fp hB Ke Kq Li Mr Nw Qd Ql Sj Un) Mt(aS Aw bG De Of Qw To Ua Vq We Th) Jh(Aj De Ef Iz Ng oE Oy Qw Ss Vo Wd) Aj(Bb Hu Hw Il Jg Jm Nv Pf Vq) St(aF bG bJ dI Gh oH Sj Vp Vq) kR(cO cX dR Fi Jd Kg Mi Nq Om) Nu(dC Hb Lz Mh Ml Qb Qc Qx) Jm(aM Fp hB Nw Pa Ql Un Ur) Oa(cN Cv dD Du Fd Rj Vp Zw) Qd(De Dk Kr Of Qn Ua Vp) Nv(aF Hc Mh Oe Of Qw Wf) Nw(aF Dk Jq Lv Qn Rg Vp) hB(aF An bJ cX dG kQ Uy) iZ(aU cX Ic Lu Pj Vq Ti) Ij(aF Dg Gd Nl Sj Vo) Ow(bJ bM Lv Vp Wc Zw) Un(An Il Nr Qn Uy Th) Qa(dG dH Jl Qe Vp) Li(dI Jo Kj Uo Up) On(aF aO Hc Qw Wf) Pf(aS bM Hc Of Vo) Il(aS Jo Pa Ql) Kq(An Dk iO We) aZ(aF bJ cX Ni) Du(Ml Po Rc) Qb(bG bJ Ni) Ql(Fi Nr Uy) Of(Hu Is Om) cX(gL Hx Qe) De(Om Qe) Nt(cH Mh) Ic(aA aM) Sj(oE Vq) Kj(Bb Ho) aH(bJ gL) AdNb DrQc ThUr FiJo GhaM LxZw LzPh MhWb NiiO NlKe HuoE IhRj JibN KkbJ VqiH aAaS dCgL} Sh{Jv(Ad aM aP AW Ax Ba bG bQ cH CO Cp CS CU Cw cX Dd dK Dl Dr EF Et Ez Fp fR Fy Gc Ha Hq Hu Hw Hx Ih Il Ir Is It Iv Iz Jg Jh Jk Jl Jn Jo Js Jt Jy Kd Kn Kq Kx Ld Li Lj Lx Lz Ma Mg Mi Ml Mq Mr Mv Mw Mx Na Nb Ng Ni Nm Nn Nq Nr Nt Nu Nv Nw Ny Oa OF Oh Om On Ow Oz Pd Pe Pf Po Pz Qa Qd Qe Qt Qx Qy Ra St Tn Tv Uf Ut Uw Vq Vw Wh Wm) Qy(aA aH aI AL Aw AX bA bB bL bQ cE cK cT cU Cv cX Dd dR Ed Eq Et Fp Fw Fy Gc Ha Hq Hx Ih Il Ir Is It Iv Jf Ji Jl Jn Jr Js Ju Kd Ke Kn Kq Ks Kx Lj Lp Lt Lx Mf Mj Ml Mn Mw Na Nb Nh No Nr Nv Nw Ny OE Om On Oz Pa Pd Pe Pf Pg Po Qa Qb Qe Qh Qv Qx Rf Rm Sf Sr Tn Tz Ut Ux Tj) Hu(aF aH Ar Ax bB Cs CU CX Dc dF Ed Et Ex Fw Fy Gc Hb Ih Il Ir Is It Iv Jh Ji Jl Jn Jr Js Ju Ke Kq Ks Kx Ld Lh Li Lz Mf Mh Mk Ml Mm Mn Mt Mw Mx Nb No Nr Nt Nv Nw Ny Oa oE oF Oh Ok Om On Oz Pe Pj Po Qa Qb Qd Qh Qx Sf St Tz Uh Ut Vq) Mw(aG aN Ap aY Bb bF bH Bn bQ cD cE Ch cM cN Cw Cx De dK Fw Gc Gd Gh gL Gn Gp Gz Hf Hq Hr Ib Ic Ij Il Jh Jm Ju Kd Kp kQ kR Kx Kz Mg Mt Mx Nd Nu Nx Oe Oh Oi Op Or Pd Pe Pf Po Pz Qn Sf Sr Uh Ul Us Vo Vz Ye Tm) Ny(AF aN Ao Ap aW aX aY bJ Bn bW cN CO cS cU cV Cw CX dK Ef Ez Fc Fi Fw Gc gL Gp Ho iH Il Iu Jd Jh Kc Kd Kg Kq Mg Mi Mm Mq Mt Mu Mv Nq Nr Nt Nu Oe oH Oz Pd Pf Ph Pj Pz Qn Qz Rz Sr Uf Uk Wd Ti) Fw(AF aM aW bJ bN cO cV CX dB dH dI dJ Dp Dr Et Fp hB Hx Ih Il It Iv Jd Jh Jn Jy Kq Kz Lj Mq Mr Na Nd Nf Nh Ni Nn No Nq Nu Oa Oe Oh Ow Oy Oz Pa Pb Pc Pe Pf Pj Qa Qw St Up Ur Ut Tm Ti) Jh(Af aH Al aW AX aY bL Bo cD Ch CX Dd fP Gl Ih Il Ir Is It Iv Jm Jn Ju Kd Ki Lj Lp Ml Mn Mx No Nr Nw oE Oh Om Ow Oz Pa Pb Pc Pf Ph Qa Qb Qe Qh Rm Sf St Uh Us Vq Vs Wf Th) Nb(AF aN Ap aW bE Bn cO cP cQ Ct cU Cw CX Dd Et Fi Gc Ih Is It Jd Ji Ju Ke Ki Ko Kq Mf Mk Mm Mp Mt Mv Na Nh Nn Nq Nw Oe Oh Om Oz Pc Pd Pe Pf Pj Rm Sf Si Ue Up Ti) Cx(Ax bA Cp Cu Cw Dc Dd dM Et Fy Gb Ih Ij Ir Is It Iv Iz Ji Jn Jq Jr Js Jt Ke Kn Kq Lp Lx Mj Mx Na Nr Nt Nv Om On Ow Pd Pg Ph Pi Qd Sr Tn Ut Vp Vs) Nn(aD aG aN Ao aV aZ bM BO cF Cu Dd De DL Du Ed Ez Gb Gc gL Hb Hp Ij Io It Jg Jt Kd Ko Mv Nt Nu oE Pd Pe Pg Pz Qt Rc Sr Ub Un Uo Vw Zw) Ju(aP Ba bQ Co Cp cS Cu Cw Dd Ef Ez fR Gc gL Ih Iz Jd Jg Jk Jt Kc Kd Kq Ld Li Mg Mi Mq Mr Mu Mv My Nq Nt Nu Nv Om Pd Pf Ph Pz Qa Qd Uf Ut Wd) aY(aH aP cG Co Cs Cu Cw Dk Ef Et Ex Gc Id Ih Ij Ir Is It Ji Jl Jn Jq Ke Mj Mr Mv Mx Mz No Nr Nv Nw Oh Om On Ow Pe Po Qd Qe Rm Sr Tn Un Ut Vh) Ed(Ad Ao Ap Bb Bg Co Dg Dl Ef Fy Gb Gc Gd hB Il It Iu Iz Jg Jk Jt Kl Ko Li Ma Mm Ng Nm Of Or Pf Ph Pj Pz Qa St Tn Uc Uf Ut Uw Vw Wh Ti) Pf(aA AF bJ bM BO dI Fd Gb Gc Ha Hw Hx Ib Ih Is It Iv Iz Jk Jn Ko Ks Mt Nt Nu Nv oK On Pc Pe Pi Pj Qe Rv Sf Sr Ua Ub Un Ut Wb) Dd(aP Ar bZ Et Gc Gp hB Ih Ir Is It Iv Ji Jn Js Kq Kx Ld Li Lj Lx Lz Mh Mk Mq Mt Mx No Nw Oa Oh Om On Ow Po Pz Qa Ql Rm Sr Ut) Sr(aE Af aM An aW bJ bM Bo bQ cE cP dL Ex hB Hc Hf Hq Hr Hv It iZ Kd Ki Kk Nk Nl No Oa Oe Of Oz Pa Pc Qw Rc Uo Uv) Ut(AF Al aN aW Bn Bo cV cX De dH Fc Gl Ih Il It Jm Kd Ki Lp Nr Nu Nx Oe Oz Pb Qn Rg Sf Ul Us Uu) No(aC Ao Ap bJ cP Ef Ex Fi Gc gL Gp hC Hq Il Iu Jm Kc Kd Nm Oe Or Ph Pz Qn Qu Rz Si Ue Uk Ti) Nr(aC aS bJ bM Bo dI Et Gc hB Iv Jd Jy Kq Kz Mq Mt Mu Mv Nq Nt Nv Nw On Pe Pj Qa Qd Ql Qm Un) Om(aA AF Al aN aW bJ BN Bo Ch cV cX De dH Dr Il It Kr Lp Lv Lz Nu Oe Oz Pb Qn Qw Sf Us) Il(Ar Dk Ef Et Fp Gc It Jn Jy Ke Kq Ld Mq Mt Mv Nq Nu Nv Nw On Ow Pe Pj Qa Qd Ql Un) Ih(aA Ar aW bJ Bo cB dI Gc Hq Iv Kd Ke Lp Lz Mt Nq Oe oK Pj Qx Sf Si Uh Ur Us Wf) On(AF Al aN aW Bn Bo cV cX Ex Gl Ij Jm Kd Ki Lp Mx Nu Oe Qn Qw Up Us Uv Zw) Sf(Ba bQ Co cS Cu Cw Ef gL Iz Jd Jg Kq Li Mg Mi Mq Mv Nq Nu Nv Qd Uf Wd) Qa(Af aN bJ dD dG dH dI dL Du Ex Fc Gl Kd Nt Nu nW Oe Po Qw Rg Uv Zw) Ij(aF aW bJ bN cP dI Dp fR Gn Hb Hf In Kd Kf Kr Rb Rc Tv Uk Up Vs) Is(Af aN aO aW bJ bM Bn cV cX dI Gl Lv Nt Nu Oe Oz Qn Qw Up Vp Wb) Jn(aF aN aW bJ BN bQ cO cV cX dI Fi Hw Iv Kd Mt Nt Pc Ph Qn Uk) Nv(aF aN aW Bn cV cX De dH Dp It Iv Jm Kd Mx Oe Oh Oz Pb Ph Qn Qw) Ow(aF aN bJ bM bO cV cX dH Hp It Kd Lp Lv Nt Nu Pz Qn Qw Rg Sj) Mx(aC aF bE bH cZ dI Hw Iz Jd Jk Ke Kq Mu Nt Nu Qd Ql Vq Wd) Kq(aF Al aN aW cX Ex Gl Jm kR Lp Nu Pb To Uk Ul Us Vs Th) Rm(Af aN aW bJ cX dI Dr Kd Mj Mq Mu Oe Qn Qw Ri Ur Vp) Mt(Al aN aW aX bJ Hq Hw It Jm Lp Ng Oz Pb Pc St Vq) Gc(aA Af Al aW bM bQ iZ Jm Kd Lp Nt Nu Pa Ph Qw) Iz(Aj Ch cX dR Ir Lj Lz Oa Oe Oh Oz Ss Uh Uu Ux) Ph(Ar Bo Et hB Ke kR Ld Lz Mq Nw Oa Oz Pe Qx) Jm(Cu Ef Et Fp It Iv Jd Jy Ke Mq Mv Nq Pe) aW(Dk Ef Hx Ib It Jl Ke Mv Nq Oh Pe Qd St) cX(Ba Fy gL It iZ Jk Ke Nw Oa Oh Qd Tz Uw) Kd(Bo Cs Fp It iZ Jd

On Ow Pf Po Qw Sr Tz Uh) St(Ar Ax aZ dR Fp Gd gL Ir Iv Ji Jr Ke Ki Mh Mx Nr Oe Ow Po Qd Tz Uh Uu) aZ(Ax cX Dr Fp Kx Mg Mh Mt Mw Nn Nr On Ow Pf Po Ra Rf Rh Sr Ut Vq Wm) Po(aA aE Af aH aY bM Bn cD CX De Dr Du Ed Gl Gp oH Pb Qw Uv) It(Af Aj Bo Cx dR Gd Hc Ji Jj Ow Pb Pc Pf Rj Ug Uh Uu Vb Vo Vt) Ed(Cu eF Fy Ho Hw Iv Kf Kg Kn Kx Lh Mg Ni Nk Nt Ra Un Vb) Qd(Ax Cx De Fy Kr Kx Mh Nn Nr oE Ow Pf Ra Rf Rh Us Uu Wm) Ke(Ar Ax Dr Fy Mh Mq Nn Nu Ow Pb Pf Ra Rf Rh Ub Uu Wc Wm) Mq(Cq Dc Fy Ir Jp Jr Jt Na Nj Pb Pg Pi Qe Qh Tz Up) Ow(aA Af Aj aY Gd Hb Hp Ki kR Ma Mv oN Oy Pb Sj Tz) Gd(Et Gc Jh Jt Mt Mw On Pj Qe Qy Rm Sr Ut Vh) Tz(Af Ax bN CX Dr Nn Nr Nu Pf Ra Rf Ur Wm) Ir(Af aH Bo Cv Cx Fp Ky Mv Mw Ug Ut Uu Wf) On(Aj Bg De dR Hc Jj Kj Mx Oe oH Oy Ug Ux) Ax(aY Bo Hb Jh Ji Jj Mw Pc Qb Rh Uh Vt) Qe(Af Aj Ar Cv Cx De Dr hB Jj Pf Uu) Ji(bN De Dr fR Jl Nr Pb Qw Ra Wm) Pf(aA aY Gb Hb Hp Mr Oy Pi Sj Wb) Et(aA Af aY Ch De Fp iZ Mw Uu) Sr(aH Aj dR Mv oH Oy Pb Ug Ur) Fp(aE aN aY Gp Il Lu Pb Pi) Nr(Hb Jj Mv Pc Qb Ql Rh Ur) Jh(Aj Ch De Mx Pb Uu Ux Vo) Mt(Aj dR Fr Kz oH Pb Ux) Mv(Af Aj Ch De Mh Mx) Uh(aA Dr fR hB Nn Nu) Ut(Aj Ch Hc Jj Oy Uu) Fy(Bo dK Hb Qb Vt) Mw(Gp Jj Oy Pb Yl) Hb(bQ fR Nn Nu) Uu(Gc Qy Rm Vq) Aj(Mn Tn Vq) Dr(Gp Qb Vt) Jr(CX Wc) aA(CX Rm) Fw(Ni Un) Gp(iZ Rf) Na(Qb Ql) Iv(kR Pb) Pi(Ar hB) aY(aP bB) NnUn NuJq LuiZ MxQl QbUr PcoF} Wf{Nn(aA aE Aj aO Ax bA bR bZ cM Cp Cq Cs Cu Dc Dd Dg Dk Dr Em Ez Fd Fp Gb Gc Ha Hc Ho Hp Hv Hw Hx Ib Id Ih Ii In Ir It Iv iZ Jd Je Jh Ji Jj Jl Jn Jq Jr Js Jt Ke Kn Kq Ld Lp Ma Me Mj Mr Mx Nb Ni No Nr Nt Nv Nw Ny oH Oi Ok Om On Oz Pc Pe pF Pg Pi Pk Po Qd Qe Qu Rb St Tv Ub Un Uo Up Ut Uz Vc Vp Vs Wb Wc) Ny(aF aM AN AP aW aX bC bE bG bW bZ CO cS cV Cw cZ Db Dc Ef Ez Fd Fp Fr Fw Gc Hu Ih Io Iu Iv Jd Jh Kc Kg Ki Mg Mi Mk Mq Mr Mt Mu Mv Mw My Ni Nq Nr Nt Nu Oc Om Pd Pe Pf Po Qd Qw Qy Ra Rz Sr Tv Uf Us Ut Wc Wd) No(aK AN Ap aV Aw aX aY bC bH bQ bW bZ cF Co Cp cR cS Cw cY cZ De dK Ef Ez Fw Gc hC Ho Hq Ih Iu Iz Jd Jg Jh Kc Kg Kq Mg Mi Mq Mr Mt Mu Mv Mw My Nb Nq Om Or Oy Pd Pf Pz Qa Qd Qt Qu Qy Qz Rz Sr Ua Ue Uf Ut Wd) Jh(Af aH aM aW AX aY Bg bL Ch Cx DE Ed Ef Fw Gl Ih Ik Il Ir Iu Iv iZ Jn Ki Kk Ld Lj Lp Lx Mx My Ng Nr Nu Nv Nw Nx nY oE Of Oz Pa Pb Pc Pf Qb Qe Qt Qx Qz Sr Ss Ua Us Uu Uv Ux Uy Vb Vs Vt Wd Ye Th) Mw(aA Aj aL aS BA Bc BG bO bU Ch Cs CT Cu cW dD De Ez Fd Gn Gp Ib Ih Ij Il Ir Jl Jr Js Kk KR Kx Ld Lj Lw Lz Ml Mq Mr Mt Na Nb Ni Nu Oa oE oF Oh Oi Qv Qx Rf Rh Tn Us Uu Uw Uz We Wg Yl Wm) Qy(aM Ax bA Cs cT Cu Cv Dr Du Ex Fp Fy hB Hv Id Ih Ij Ir Is Iv Ji Jn Jq Jr Js Ke Kk Kq Ld Lh Lx Me Mj Ml Mq Mr Mt Mx Mz Nb Nr Nv Nw oF Oh Ok Om On Pf Pk Po Qa Qe Qv Qx Rv Sr Tn Ut Uu Vt) Nb(aF aM AN aP aW bJ bP cO cQ cU CX Db Di Dp Ed Et Gc Gh gL Gz Hl Ii It Iv iZ Jd Jn Jy Ki Kk Kq Kz Mb Mk Mq Mr Mv Nf Nq Nw Oe Of Oz Pc Pe Pf Qa Qd Ql Qv Ug Un Up Us Tm Ti) Ih(aA aM aP Ar Cu Ex Fw gL Hv Id Iv iZ Jd Je Jj Jr Js Kk Lh Me Mj Ml Mq Mr Mt Ni Nt Nu Nv Og Om On Pf Qe Ql Qx Sr Un Ut Uw Vt) Qa(aA aF AN aO bN cV CX dD dG dH dI dL Dp Du Ed Fn GL Hu iZ Je Jq Lu Lv Mz Nt Nu Nx Oe oF Oz Pc Qw Rg Uc Up Uv Wb Zw) Ut(aA AF aM aN aW aY bL Bn Ch cV CX De dH Il It iZ Je Jm Ki Kr Ld Lj Lp Lz Mq Nr Nt Nu Oa Oz Pb Pf Qx Ra Us Uu Uv) On(aA aF aN aY bM Bo CX Dr Fw Gl Hu iZ Jd Je Ki Ld Lp Mq Mx Nr Nu Oa Oe Oz Pf Qn Qw Up Us Uv Uy Vs Wc Zw Th) Jn(AF aM aS aW bG bH bJ bN cO cV Db dI Ed Fw gL Iv iZ Jd Ki Mq Mr Mt Mu Nc Ni Nl Nq Nu oH Rj Wb Wc Zw) Kq(aF AN aW Bn Cx Ed Fw gL Il iZ Jm Ki Kl KR Lp Lv Mp Mz Nr Nu Oa Pf Po Qn Sr Uc Us Uy Vp Vs Wc Th) Mt(aE aM An aX bI Hq Hu Hw Hx Ir Is It iZ Je Ki Lp Mr Nr Nv Oz Pb Pc Pf Qd Qe St Uv Uy Vq Wb We) Pf(aA aF aO bF Cu Dd Dr Gb Hp Hv Hx Ib iZ Jd Je kS Mr Ni Nt oK oN Pc pF Pi Qd Qe Sr Un Vt Wb) Sr(aA aG aM bJ Bo Dp fR Fw hB Hu It iZ Jd Jj Jl Ld Mq Mr Ni Nl Nq Of Qd Uo Vh Wb Wc) Ir(aA aN aS aY bH bJ Bo dI Ed fR Gz Hu iZ Jd Je Jy Ld Mq Ni Nq Nu Nv Nw Qd Qw Wb) Nr(aA aG aM aS bH bJ cT Cx Gz Hu Hv Jd Jy Mq Mu Mv Ni Nq Nv Nw Qd Ql Rh Un) Ld(Al AX Ch Cp Cq Dd Ha Hu Il Iq Jk Jm Js Lp Nt Pg Pi Pz Qh Uy Vt Wb) Nw(aY Bn CV cX Hu Je Jr Jt Kn Lw Nu Oi Om Oz Qn Qw Qx Rg Up Uz Vp Wg) Mr(Ap aW Bb Bo Cx Ed Gn Ic Ij Il Jm Li Lj Lp Nu Nx Oa Oz Pz Us) Pe(aA aE An bB bM cW Ed fR Gl Gn Hu iZ Je Ji Jq Ky Nj Nt Nx Po) Nu(cH Hx Is It Jl Mj Mq Mx Nv Oa Om Qb Qc Qd Qe Qh Rm Vt) Iv(aE AN aO aY bG dG dH Hu Kk kQ kR Of Oi Qd Um Uy Th) Mq(aA Al Bb Ed Fw Hu Il Iq Jk Kd Ki Lp Nt Oa Qd Qe Uy) Cx(Cp Cq Cu dM Dr Ed Jr Lj Lx Mi Mz Ok Pg Pi Un Vp) Hu(aM Ax Cs Ex Hx Is Js Li Lx Ml Mx Oh Po Qe Qx) Oa(Cp Di Ef gL Ib Iz Jd Jg Jy Mu Ni Nt Ql Qw Wd) iZ(Aw Co Cp Et Gc Is Ji Ke Mn Om Ow Qe Si) Nv(aA AF cX Fp Hx Lj Mx Ni Oe Oz) Om(aA aF aM aY cV De Ni Of Oz Pb Sj) Nt(aM cH In Mj Nq Ph Qd Qe Qg Vt) Jd(Il Kd kR Lj Lp Mx Nx Oh Qe Uy) Ed(Af Bc Bn fR It Nf Tn Uw Wh) Ni(aZ Is Lj Mx Oh Qb Qe Uh) Je(Ij Is Js Li Lj Lx Oh Ow) Vt(aN Ax Db Il It Qx Ra Rg) aM(Bb Fw gL Il Is Jv Lp) Ke(bJ Dc gL Nj Nx Uv) Ql(Bb Fw Il Kd Ki Lp) Mv(Fw Lp Mx Ul Uy) bJ(Ij Jq Js Mj Mx) Qe(aA aN fR Qw) Oz(Is Qd Tn Wd) Cu(Gl Ki Uv) Lx(aN Mu Qw) Mx(aY cZ Qd) Jk(Fp Ml Qx) Js(aA aF Wb) Li(cC Hp Ib) Un(aY gL Il) Ch(Ef Wd) Fw(Hx It) Qw(Hx Is) Lj(fR Ib) Ow(Af aY) DrGc HvaN IjdI PzaA QdRa StaP WdPb JlcV aFhB} Dr{Kd(aA aH aI aP Ar aZ Co Cs cU Dp dR Ed Ex Fw Gc Gp Hb hC Hf In Is It Iv iZ Jd Jh Ji Jn Jq Js Kj Kq kS Kx Ky Lj Lz Mf Mh Mj Ml Mt Mv Mw Mx Nb Nn Nq Nr Nv Ny Oa oF Oh Om On Or Ou Ow Pa Ph Qc Qe Qg Qx Rm Sr St Us Ut Vt Wc Tl) Ed(AF aK Ao Ap AW aX aY Bb bC bJ Bn bW bZ CO cQ cS cY dK Ef Et Ez gL Gp hC Ih Iu Jd Jg Jh Ji Kc Ke Kg Kk Kq Lj Ma Mf Mg Mi Mp Mq Mt Mu Mv Mw Nb Ne Nl Nq Oe Oh Om Pd Qa Qd Qt Qw Qy Rz Si Sr Uf Uh Up Ut Wd) Oa(aC aF aN Ao Ap aU AW aX aY Bb bJ Bn Bo bW CO cS cU cV Cw CX Et Ez Fw gL Gn hC Ho Hu Ic Ij Jh Ji Kc Ke Kg Kq Ld Li Mg Mi Mk Mq Mt Mu Mv Mw Nm Nn Nq Om Pd Pf Qn Rz Si Sr Ue Uf Uh Uk Us Wd Zw Ti) Uh(aF Al AN aP As Aw bG bJ bN bO bQ cD Cx dK gL Gp Hu Ib Ih Il iZ Jd Jk Jm Ki kQ kS Lj Lp Ms Mw Mx Nd Ne Nl Nr Nx Oe Pa Pe Ph Qa Qn Qy Rb Uk Up Uy Th) Sr(Af aK An AW aY aZ BB Bo bQ cB cH cO Cx cY dA dJ dR Fn Fw Gp hB Hu Is Ki Kk Ld Lj Lx Lz Mk Ml Mq Mt Mx Nb Nn Nq Nw Oh Om Ow Pc Po Qw Qx Ug Uu) Vt(aF aN Ap aU Aw aY Bb bN Bo bQ cF Co Cw CX dK Fi Fw Gp Hu Ih Il Iv Jg Jm Jn Ld Lp Lx Mn Mt Mw Mx Nb Nr Nt Nu Oe Om Oz Qn Qv Qw Us Ut Th) Ow(AF aO aW bF Bn bX cV Cx dG Fn Fw Gh Gl Gp Hu Il iZ Jm Ki Kl KR Li Lp Lv Mh Ml Mw Mz Nb Nv Oe oN Oz Pc Pf Qw Qy Uc Uv Uy Vs Zw) Th(Ao aP aU Aw bB Bo CO CU dR Et Ez Fr Gc Gp Iv Jd Jh Kq Kz Ld Mi Mm Mq Mw Nq Om On Pj Po Qa Qy Ur Ut) Qy(Af aZ Bo CH cU De Dg Gh Is Jn Kj Kl Lx Ml Mx Nb Nw Ny oF Oh Oi Oz Qb Qc Ss Us Vb Vo Vs Vw) Lj(Ez Fi Gb Hc Ho Ic Iz Jd Ke Kg Kj Kp Kq Ld nW Qm Qt Qu Qw Qz Rz Si Uc Uf Us Ut Vq Wd Zx Tl) Ld(aY aZ Bb Ch Fi Gh Gp Hu Il Ir Is Jm Jn kR Mx Nn Nu Nx Oh Pa Pf Qb Qc Qe Qh Uv Uy) Ut(Af aW aY CH cV CX Fw Gh Gl Hc Ir Jm kQ Mh Mx Nx oE Of Oz Us Uu Uv Uy Vs) Li(Af aW aY cI Dg Ef Gl Jd Lu Nc Nd Ne Nh Nj Nk Nl Nx Oi Rm To Ul) Gh(Aw bZ cE dR Fr Fw Hq Is Kq Mq Mt Mw Nn Nv Om Pf Qa Qe St) Nn(Ez Hb Hc iO Ke Kg Kj kR Ph Qg Qx Qz Rz Tz Uv Vs We Wh) aW(dR hB Hf Ij iZ Ke Kj Kq kS Kx Ky oF Ou Ph Rm Rv Un Vb) Fw(Ez hB Jd Ki Kk Kq Kz Lu Nc Qg Ql Qt Qw Qx Rm Si Up) Mh(Ez Fi Ho Iz Jd Kc Ke Kg Kj Kq Qu Qz Rz Uc Uf Vq Wd) Lp(bB Bo dR Gp Ji Kx Lh Lx Mp Mq Nq Nw Ou Pj Po Ql Ur) Vq(Aj Ar aZ Bo Dp Gp Lz Ml Mx Oe Oz Pf Qw Qx Uu Vb) Tz(aF Ap aY Cx dK Fi Hu Ih Il Jg Mt Mw Nr Oe Oz) Qa(hC Ib Ic kQ Ne nW Or To Uk Ul Us Uy Vp Vs Zw) Qb(Ez Ho iH iO Jd Kc Kg Kq Or Qn Qu Qw Rz Uf Wd) Lx(aY Fi Ho Kc Kg Ky Ne Or Qw Rg Uf Up Vp) Mw(hB Hc Ib Ki Kl kQ oF Qn Qx Ua Us Uy We) Ke(aY Bb dK Gl Jd kQ Ms Nb Nx Pa Pf Un Uy) Om(iO Kf Kj kR Qx Ss Uc Us Uu Vb Vo Vs We) Qc(Ez Kc Ki Kk Qn Qv Qw Rz Uf Um Up Uu) Qd(Jd Jy kQ Kr Nd Qn To Ul Us Uu Uy Vs) Kq(Af aZ Bo Gl Jm kQ kR Ml Mx Nx Us Vs) Oh(Jd Kc Kg nW Qn Qw Uf Uk Ur Vp Zw) Nr(hB Kc Kx Kz Qx Rb Rh Uf Ur Vp) Mx(Ez Ho Jd Kc Kg Kk Qw Rz Uf Wd) Ap(Kj Kl Qx Ss Uu Ux Vb Vo Vw) Hu(HB oE Ph Qg Qx Ss Uu Vb) Ij(cP Hp Kk Nd Ne Nx Tv Ug We) Il(iA Jd Kk Kx Qg Qx Rh Ur Tl) Uy(Bo Et Gc hB Ji Mk Mq Nq Ql) Is(Qn Qw Rm Up Ur Us Vp Zw) Pf(Hc Ho Lu Nd Ne Si Tn Vp) Fi(aZ Bo Jn Lz Ml Nb Qx) Jm(Jd Ou Pa Ql Un Ur Tl) Qn(Ji Jn Js Nv Nw On Qe) aY(cU hB iA Ou Qx Rg St) Gp(Kk Qg Ql Rf Rm Un) Mt(Ib Jd kQ Qx Us Uv) Jg(Kj Qg Qx Uu Vb Vo) Ny(Kc Kg Rz Uf Vp Wd) Ch(Ez Jd Kg Tn Uf) Co(Kl Ss Uv Vb Vs) Nb(Kc Kg Pj Qg Ti) Ih(oF Qx Rc Rj Ur) Ir(Kk Qw Up Ur Us) Si(aP Bo oE Oz Uu) Qe(kQ nW

Figure 38 Continued

Qw Us Vp) St(aF aU cP cU cV) Rm(aF bO Oe Of Oz) Nv(Ic Us Uu Vp Vs) Pe(Fp Ib Jy Nd Ph) kR(aU dR Mp Mq Nq) Cx(Ha hB iZ Um) Jn(Kc Uf Vp Ti) Js(Qw Uf Vp Wc) Vb(aF Bb Cw Jh) aZ(Ho Kc Kg Uf) Nw(Gl Qw Uk) aP(Ic kQ Ti) Bb(Qg Rv) Bo(Ha Kn) Et(Gl Jd) Jh(Us Vs) Uu(Pz Uc) Oz(dR oF) dK(Hb Qx) hB(cQ Vz) iZ(aU Ic) AfTn CwVw PokQ EzaX GcQw NohC NqJy NtQg MlHo JdPa QhcV KjaF KkOe KyNx OnUs VpPg PcoF aNoE} Zw{Lx(aA Ad Af aO As aY bE bF bJ bM bN bO Cp Cq Cs Cu cV Cw cX dA Dc DD dI dN Ed Em fR Gb Gn Gp Ha hB hG Hl Ho Hu Hv Hw Hx Id Ih In It Iv Iz Jd Jg Jh Jk Jn Jr Js Kc Kq Kr Li Lv Lw Mb Md Me Mh Mi Mj Ml Mq Mr Mt Mu Mw Nb Nf Ni Nl Nn No Nr Nu Nv Ny Oa oF Om On Ow Oz Pb Ph Pi Pk Qa Qd Ql Qx Qy Ra Rg Sr Tv Un Up Uz Vp Vq Vs Vt Wb Wg Yl Tl) Ow(aM Ax bO cM Cp Cq Cs Cu cX dA Em fR Ha Hr Hu Hv Hw Hx Ih Ii Ir Is It Iv iZ Je Jh Jl Jn Jr Js Kd Kq Ld Li Lp Me Mi Mq Mr Mt Mu Mw Na Nf Ni No Nr Nt Nu Nv Ny Oa On pF Ph Pi Pk Po Qa Qe Ql Qw Qx Rb Sr St Ul Un Uo Up Ut Uz Vp Vt) No(Af Ao Aw aX Bb bE bJ Bn Bo bZ cC cE cL cQ cU Cw CX cY cZ De dJ dN Ef Et Fi Fy gP iJ Il iO Iu Iv Jh Ke Kj Kq Kx Lh Mf Mk Mm Mq Mu Mv Nc Nq Nt Oe oF Oh Ou Oz Pc Po Qn Qx Qy Ra Sr Uh Ux Vq Wd Ti) Ld(Al AX bX Cp cX Dc Dd Fw Fy Ha Hu Hw Ih Ii Il In Ir Is Iv Jk Jl Jm Jn Jp Js Ke Ki Kn Ko Kp Kq kR Li Lj Mt Mw Nn Nt Nu Nw Ny Oh Ok Om On Pf Ph Pk Pz Qa Qb Qd Qe Qh Qu Qy Rm Sr St Tz Uh Ut Vq Tj) Mt(aN Ar aS Ax bG bI bJ cH Cs cY fP Ha Hw Hx Ih Is It Iv Jm Jn Js kR Kx Kz Li Lj Lz Mh Ml Mq Mw Mx Nf Nn Nr Nw Ny Oa Oh Oy Oz Pb Pe Pf Po Qa Qb Qc Ql Qx Rf Rm Sr St Us Vq Tj) Oa(Ao Ax Ba bQ cI CS Cu dK Dl Ef Et Ez Fy gL Hw Is Iu Jh Jn Js Jt Jy Kj Kq Li Mg Mk Mm Mq Na Ni Nn Nr Nt Of On Pd Pf Pi Pj Po Ql Qx Ra Ri Uf Ut Uw Vb Vq Vw Ti) Ih(aM aP Ar Ax bB cO Cs CU Et Ex hB Hf Hx Is Iv Jd Jh Ji Jj Jn Jp Js Jy Ke Kq Kx Ky Lh Li Mk Ml Mq Na Nb Ni Nn Nq oE oF Oh On Ou Pf Po Qa Ql Qx Ra Sr Ur Ut) Qa(Af Ar aV Ax Ba bJ BN Bo bQ bV cJ cO Cq Cs cV dA De Dk Fn Gn hG Iv Kr Lz Mh Ml Na Nb Ni Nj Nl Nn Nr Nt Oh Oi Oz Qe Qn Qx Rf Rh Sr Up Vp Vs We Wm) Qx(Cp cQ Dd Fd Ha Ho Hu Is Iz Jg Jh Jk Jl Jn Ke Kq Ks Li Lj Mw Nb Nn Nq Nu Nv Nw Ny Om On Pe Ph Qd Qe Qy Rm Si Sr St Ua Uh Ut Vq Vt) Oh(cM Cp Cu fR Gb Ha Hv Is Jd Je Jh Jn Ke Kk Kq Li Mi Mq Mr Mu Mw Nb Ni Nn Nu Nv Om On Oz Pd Pe Po Qd Qe Ql Sr Un Vt) Sr(aM Ax Cs Cx Ez Fp fR Is Iv Jl Jn Js Kk Kq Kx Li Lj Lz Mh Ml Mq Mv Nn Nr On Pf Po Ql Ra Rm St Ut Wm) Li(aN aV aY bJ BN BO cC Cx Hu iJ Is iZ Jl Jm Jn Kr Mw Ni Nn Nt Nu Ny On Pf Rm St Up Uu Vs) Ed(Af aG Ap aU aW Ba Bb bC bJ bZ cO cS CX dR Gp Iu Kc Mu Nc Ne Nl Nq nW Oc Or Pa Pc Qw Ur) Pf(bF fP Ha Ho Hp Hx Is Jh Jj Jl Ke Kq Mq Mw Nf Nt Nu Nv Nw On pF Qd Qe Ql Rg Vq Vt Vz) Nn(aX Cs fP Hx Ir Is It Jj Jl Jn Ke Kq Ml Nb Nw Ny On Po Qb Qd Qe Ql Ra Rm St Tz Vt) Is(aF Ar Ax Cs Dp Fp Iv iZ Kx Lj Lv Lz Mh Ml Mq Nf Ni Nr Nt Nu Oz Po Ql Ra Wm) Jn(Ar bN cO dR Et Ez Hw Iv Kq Mq Nf Nt Po Qe Ql Qv Ra Rc Ri Rj St Uh Ti) On(Ar Ax aY BG cV Ir Iv kQ kR Kx Lz Mh Ml Mq Nr Nu oE Og Ra Us Uu Wm) Ax(Jd Jh Jl Ke Kk Kq Mq Mw Nq Nv Nw Ny Om Qd Qe Ql Qy St Ut) Nr(cV Cx Fp Hx Jh Ke Kx Kz Mq Mv Mw Nf Nv Nw Qd Qm St Un Ur) Nt(Ar Hb In Js Ke Lh Lj Lz Mh Mj Ml Mq Nw Or Ph Po Qg St Tz) Ra(Jl Ke Kq Lj Mw Nb Nv Ny Om Pe Qy Rm St Uh Vq) Cs(bJ Hu Jh Jk Mw Nv Nw Ny Qd Qy Rm Ut Vq) Nb(Fp Ir Kx Kz Lz Mq Nf Ql Rf Tl Wm Ti) Ml(Hu Jh Jk Kq Mw Nv Nw Qd Qy Ut Vq) Po(aN aW aY Cx Il Jm Nu Ny Rm St) Mq(Al Ii Il Ir Jm kR Lj Rm St Vq) Lz(Cp Ke Kq Mw Nv Om Pe Ph) Ar(Fy Jg Jh Jk Kq Nv Nw) Wm(Ke Kq Mw Nv Nw Qd Qe) Kx(aY Hu Mw Nv Ny Qy Vq) Lj(Ba Cu Ef Kq Ni Ql Ut) Pe(Af bM bP Ha Qn Rh) Mh(Kc Kq Nv Om Qd) Mw(Ch Ir Js Rf Rh) Rm(gL Ni Nu Ql Ur) Fw(Af Bo Pc Rf) Iv(Ir kR Uw Vq) Qd(Af Kr Rf Us) Js(bJ Jh Oz Qy) Nw(Fy Rf Rh) Ij(aC dR) Il(iZ Ql) Qy(Ch Uu) Ut(Rf Uu) Vq(Fp hB) CxIr NuLh MkNy NiQb KqkR OzaP} Lp{Cx(aM aP Ar bB bG Bo cC cR Cs Cv Ed Et Fd Fp fR Fw gL hB hC Hx iZ Jd Jh Ji Jj Jl Jr Ju Kk Kq Kx Ky Kz Li Lj Mi Mq Mt Mw Nf Ni Nt Nu Nv Nw nY Oa On Ow Oz Pi Po Qd Ql Sf Sr To Uh Un Ur Ut Uu Vp Vt) Mq(aG aH Aj aN aR aW aX aZ Bg bM Bn Bo bP bS Ch cX Dd De dG Dk dL dM fP Fr GP Hc Hu Ib Ik IP Iz Lz Ml Mw My Nv nY Oe Oi Oy Oz Pb Pf Qn Qt Qv Qw Qx Qz Rj Ua Ug Uh Us Ut Uu Uv Vp Vs We Ye) Ur(aF aL aM aY bE bJ bP Ct cV Dk Ef Ez hB Hu Hx Ih Ii iO Is Iu Iz Jd Ji Jk Jn Jy Ke Ki Kk Kz Lh Li Mr Mt Mu Mw Nc Ne Nf Ni Nk Nl Nq Nv Ny Oa Om On Ou Oz Qb Qd Qm Qy Rf Tn Ua Ug Vt Wh) Ar(aC aE aF aN Ap aU aW aY Bb bG Bo bS Co Cw Et Ez Gp Jg Jh Jk Jp Kc Ke Kg Kq Mg Mi Mm Mp Mt Mu Mv Mw Nn Nq Nw Om On Oz Pc Pd Pj Pz Qy St Uf Uh Vq Wd) Bo(aM Ax bQ cO CS Cu Ez Fw Fy Hx Iv Js Jy Kn Kq Kx Kz Li Lj Lx Lz Mk Ml Mr Mt Mz Na Nf Ni Nn Nt Nw oE Oh On Ow Oz Pf Pj Po Ql Qx Ra Uw Vq Ti) Nb(aF aN Ap aS aW aY Bb bE bG bJ bW cL CO cZ Fi Ho Hv Hw Hx Ih It Iu Jh Kc Kd Kg Mg Mi Mm Mp Mu Mw oH Pa Pc Pd Qy Ue Uf Vq) hB(AF aN aW aY bG Bn bR bS cN Co cV cX dR Gc Ic Ji Kg Mg Mk Mt Mu Na Nn Nq Nt OE Oz Pd Pj Po Qn Qy Rj Si Uf Uh Vq) Oz(aP bJ Cs Cu Fp Ih Ik It iZ Jd Jh Jk Kc Kq Ld Li Mr Mt Mv Ni Nn Nq Nu Nv Nw Om On Pf Po Qd Ql Qy Un Ut) Ny(aF Ap aU aW aX Bb bC bG bJ Bn bW CO cS cV dK Ho iH Jh Kc Kg Kq Mg Mi Mt Mu Om Pd Qy Rz Uf Vt Wd) Ld(aW bR cF cI cK Cq Cv Cw dC Ed Em FP Gc Gh Gl Gn Ij Jj Jp Lj Md Mt Nk Nn Nr Pj Pk Pz Rj Sr Vs) Kq(Ad Aj aN bL Bn Dk Fr Gl Hc Hl IP Iz Jj Jl Jm Jo Kd Kj Mh My Qn Qw Rj Ua Ut Vs Ye) Ql(Af aG Aj aN aZ bG bM Bn bS Dk Hc Ib iP Jj Ki Oe Pa Qn Qv Qw Rj Ug Us Uu Vp Vs Ye) Li(Af aH Aj aN Bg BN Du Gd Gl Iq Jf Jo Kg Kj Kl My Oy Pb Qu Ug Us Uu Uv Vs Vz) Nn(Af aH Aj aM Bg dK Gd Hc Hl Jj Jo Kg Kj Kl Nw Or Oy Pa Pc Qu Qw St Uu Uv Vs) Jd(Af Aj Bg Ch De Dk Hu Ip Lz Ml My Oh Oy Pb Qw Qx Ra Rf Rh Ua Us Uu Ye Wm) Nw(AF aN aW aY bG bJ BN CV cZ dE Jq Kr Lv Qn Qv Ra Rh Us Uu Vp Wm) Oa(Bb Dd dI dK Fi Gb Ho Hv Hw Iz Jg Jk Jt Kc Kd Kj Nt Pc Ph Rg Uk Vw) Uu(Ao bJ Cu Ef Et Gc Ih Jh Ji Ke Mt Om On Ow Pe Pj Qd Qy Sr Ut Vq) Ow(Af aN aY bJ bM Cq Cv Gl Hl Hu Iq Lv Oy Pa Qy Us Uv Vs) Iv(Af aG Aj aZ bS Hb Hc Ji Jj Jm Pb Pc Pj Ug Uh Vt Ye) aY(aM bB Cu Et Hv Is Kx Mi Ok On Pf Qd Qe Un Ut) Af(Cu Et Jh Ji Ke Mt Mw Nv Oh On Pf Pj Po Un) Kd(bJ hC Ih It iZ Jh Jl Mv Mw Nf On Sr) Aj(aW Ef Ez Jh Mg Mt Nq Om Qy Uf Vq) Mt(bJ bM bX Hc Jj Kj Oy Pa Us Vs) Qy(cO Gd Kj Kx Mh Ml Nf oE Qv Qx) Jh(Bg De Fw Jj Kj Oy Qw Ua Us) Cv(aM Cu Ij Nv Oh On Qe St) Mw(Ch Hu Ki Nk Qv Us Uy Vt) bJ(aH dR Ji Lj Lz Ml Pf Qx) bN(Ji Ke Lx Lz Ml Qx Uh Vt) Nu(Dc Hb Lh Lz Ml Qx Uh) Ni(aZ Ij Ji Ke Pa Qb Uh) Qv(Pe Qa Qd Qm Un Vt) Jj(aF aW Ez Kz Mg Om) Pf(bE bM dI Pa Un Vz) Nq(Bg hC Lz Oy Us) Lx(aC bE dI Pa Rv) Mk(aA bM hG Vz Wb) Ih(Fi Hv Ik Pc Ry) Kj(aW Ez Mg Pd Uf) Lj(aC aG cO dI Jk) Cq(Et Ij Ji Qa) Rj(It Mr Mv Qa) On(Bn Hc Us Vp) Pe(aG Ii It Ug) Pj(aA Gd hG iZ) bM(Et Kx Po Qe) oE(aN aS Jy Un) Ez(aX Hl Jo) Mg(Gd Jo Kg) Ij(dI Pa Vz) Ji(aA hG Us) Ed(aG Gp) Po(aN Du) Fp(aF aG) No(dK Ug) Nt(Ct Hb) Nf(Gp Ic) Sr(Hf Jk) Jm(Mr Un) Rh(Ra Wm) Om(Oy Us) Vp(Jl Qa) aA(Et Ti) aH(cZ gL) bE(Ml Qx) cO(bR St) ApGd BnaM CuOf DeQd FwHu GnKz MhUn JnPc JoUf UhfR UyVt bZfP} Wb{Lj(AO aQ aU AW Ba bC bQ bZ cE cL CO Cp cS CU Cw Dd De dK Ef Et Ez Fi hB Ho Hq Ic Il Ir Is Iu Jg Ji Jo Jp Js Jt Kc Kd Ke Kf Kg Kj Ko Kp Ld Lh Li Lx Ma Mf Mi Mk Ml Mm Mp Mq Mt Mu Mv Nd Nm Nn Nq Nw Oe Of Oh Om Ou Pd Pf Pg Ph Pj Po Ql Qm Qx Sr Tn Uc Uf Ul Uw Vb Vh Vq Vt Wd Ti) Pf(aO Ar aU aW aY Bb BG bZ cE CH Ed Fr Fw Gc Ho Hq Hv iA Ih Iv iZ Ji Jl Jy Kd Ke Kg Kl Ld Li Mi Mj Ml Mq My Nn nY Oa oF Og Ow Oz Pd Pj Qx Rc Rg Si Sr Ss Uh Uk Uu Vo Vt Zx) Li(aF Aj Al bL Bn cD cV Cx De Du fP Fw Ik Il Is Iu Jd Jm Jy Ki Kr Kx Lx Mf Mh Ml My Ng Nr Nx Oa OE Oh Ow Oz Pa Pb Pc Qt Qu Rz To Ua Ul Up Uu Vq Vs Ti) Nn(Aj aM Ar aZ Bg bM CH cR Dg Ez Fw Gl Hb Hf Iz Ji Jj Kj Ld Lx Lz Mg Mh Ml Mx Nw oE Oh Oi Oz Pc Ph Qb Qg Qu Qw Qx Qz Rz Tz Ua Uh Us Uu Ux Vs Th) Oh(aN aO aW aY Bb cC cN cV CX Fw Gc Hu Ic Ji Kc Kd Ke Kg Kl Ld Mi Mk Ml Mq Mt Mw Nu nW Oe Oi Oz Pc Pd Pj Qn Qw Rc Sr Uh Uk Ur Vt Ti) Mh(Aw Bb bQ Cp Cw De Fi Fw Ho Hu Hv Is Jd Jg Jh Ji Jt Kd Ke Kg Kj Kk Ko Kq Ld Mi Mq Mt Mu Mw Nb Nt Nv Nw On Ow Pd Qa Sr Uc Ut Wd) aW(aM aP Ar bB Et Ex Fp hB Hf Is iZ Jd Jj Jr Js Ke Kq Kx Lh Mj Mk Ml Mt Mw Mx Nq Nw Oa On Or Ou Ow Po Qb Qe Ql Rm Rv Sr Un Vt) Ld(Af bL Bn bX cF Ch CX Gh Gl Gp Hu Il iO Jg Jm Mt Mw Mx Nu Nx Oa Oz Pa Pc Pz Qa Qb Qc Qn Qy Sr St To Ul Us Uv Uy Vs Th) Lx(AF AN aO Ap cV CX Fi Fw Ic Jl Jm Kc Lv Mi Mj Nx Or Oz Pc Pg Qn Rg Sr Uh Uk Ul Up Vp Th) Mx(Af Ap aU bC Bn bW cV CX dR Et Ez Gp Ji Kg Mf Mg Mp Mt Na Om Pd Rj Rz Uh Vq) Pe(aK aU Bb bS cD Cs Dk Ex Fp Fw Gp Ib Ic It Jl Jm Jy Kd Oe Qw Rj Uh Ul Vq Ye

Figure 38 Continued

Th) Sr(Af aK aQ Ar bB bQ cD CX cY dR Gp Iq Kk Kx Lz Mk Ml OE Oi Qx Rj Ug Uh) Mq(Af aN aY bL Bn Ch CX De Fw Gp Il Jm Nx Oe Oz Pa Pb Qn Uh Ul Us Vs Th) Ml(aF aY Bb bN Cx dK Fi Fw Gp Hu Ih Il Jg Jk Kd Mw Nr Oa Oz Ph Qa Qy Uh) Ow(aY bF cL cV dH Ed Fw Gl Hf Hu Ic Kd Kl Ma Nb Nr Qw Qy Rc Sj Ul Uy Vs) Is(aF aO Ar aY BG Bn Ch cV cX Gl Hc Ic Jl Lv Lz Oe Oz Qn Qw Us Vp) Qa(An bS CX GP Ha Hc Ib Ic iP Jl Nv Oe Oi Oz Qe Qw Rj Uh Vp Ye) Mt(Ar Bg Ch Cx Fr Gh Gl Hc Ir Jm Kj kR Lu Qb Qw Uh Us Uu Vs Th) Oa(bS cN cU Cx Gp Ic Il Ji Mf Mg Mk Mm Oe Oi Oz Si Uh Vq Ti) Qx(aN aY Bb bN Cx Dd dK Fi Fw Gp Hu Il Jg Mw Oz Ph Uh Ul) Ar(aY Bb dK Fw Hu Ih Il Jg Jk Jm Kd Mw Nd Oz Pz Qy Ul) Lz(Bb bQ dK Fi Fw Hu Ih Jg Kd Kk Mw Nm Nr Nu Nv Ph Ul) Cx(aM As dL Et Ex hB Ir Ji Kk Kx Mw oF Po Ut Vt) Js(Af AN Bn cX Jm Kd Oe Oi Oz Pc Qn Rj Uh Vp) Qb(Cw dK Ez Fy Ic Mg Mk Ni Nr Oe Oz Pd Uf Ti) Po(aN Bb Fw Gp Il Jm Kd Nx Oz Pa Qn Ul Th) Jn(Af aU Bn cX Dk dR iP Oe Qn Qw Rc Uh Vp) Nr(dR Hb Hc Ic Ji Ke Lu Mk Oz Si Tz Ur) Ir(aN bR cX dR Iq Lt Oe Oz Up Us Uu) Kx(aY Bb Fw Gp Il Jm Kd Nx Pa Th) Oz(aP hB Mk Nu Nv Nw oF Om Rm) Us(Et Jh Ji Kq Mw Om On Ut) hB(aN aY cX Gp Jm Mf Qy Uh) Fw(cX Et Ji Mk oE Ql Si) Mk(Jm Kd Mw Ul Uy Th) Nw(dK Ic Il Jm Oe Ul) Uh(Ax bA Fy Ih It Ra) Ij(De Kf Tv Uk) Il(iA Ji Jj Ke) Jm(aP Et Ji Ql) aN(Ji Ke Lh Vt) Ch(Co Jd Ut) Th(Et On Ql) Gp(aM Iv Vt) Ih(Ji Lh Oe) Kd(Cs Dp Ex) oE(Gc Hu Qy) Gl(Et Kq) Mw(Hf Ua) Qe(Qn Vp) Om(Ua Uu) aP(aY Ic) TiiZ NoiH KePa OnVp UtUu VtbN PcoF aYbB} Ed{Gn(Ad Af aN As AW bJ bN Cp Cq Ct Cu Cv Cw Cx Dc Dd dN eF Et Gb Gp Hl Ho Hv Hx Id Ii iJ In Iq Ir Iv Jh Jo Jq Jr Js Jt Ke Kf Kg Kj Kk Kn Kq Kr Ld Lh Lw Mi Mr Mt Nf Of Ok Om Pb Ph Pi Po Qa Qe Ql Qx Ra Rb Rj Ry Sr Tn Tv Uc Ul Um Un Uo Up Ur Us Ut Uz Vb Vh Vp Vs Vt Wc Wd We Wg Wh) Ti(aA Af aM aQ Ar bH Bn bQ cR Cs Cx Ez Fa Fp fR Gd gL hB hG Hu Hx Ih Iv iZ Jh Jj Jl Jn Jr Ki Kk Kq Ld Lj Mr Mt Mw Nb Nl Nn No Nu Nw NY Oa Oi On Ow Oz Pe Pf Qv Qw Rf St Vt Wh tF) Si(aM Ar aW Ax Bc bJ bN bQ bZ cJ cO CS Cx cZ De fR Fy gL hB Hu Iv Jj Lj Lz Mh Ml Nb Nc Nj Nk Nl Nr oE oF Oh oK Pf Qv Qx Ra Rf Rh Uu Yl Wm) Gc(aE Af Ar Ba Bc bN bQ cO CX dA dR gL hB hG Hu Hx Iv Jj Jn Kk Lj Lz Mh Mr Nc Nf Nj Nl No Nr Nu Ny oE oF Qt Qv Rf Rh St Up Wm) Ye(aF Ao Ap aW bC bJ Co cR Ef fR Hu Ih iO It Iu Iz Jd Jg Jn Kg Ld Mi Mt Mu Mv Mw Ng Ni Pz Qa Qd Ql Qw Qy Qz Uf Uw Ux Vq Vw Wd Wh) Wh(Af aG aH Aj aN aQ aW aZ Bn bS cD cN cX De Dk dM dR Fi GP Hb Hc Ib iP Ki Mn Ne Nv nY Oi Oz Pb Pc Pj Qn Qw Ug Uh Ur Uu) Yl(aE aF aH aI aK aN Ap aQ aW Ba bJ BN bZ Cp Cx cZ Ez gL Gp Jd Ji Kd Ke Kk Kq Kz Lz Mh Mw Nj Om Or Pc Pz Qd Rh Vt Wm) Wd(Af Aj Ar aW Ax Bg Bn Ch Cs CX De Fi Gp kR Lj Lz Mh Ml No Nr Oe oF Oh Oi Oy Pf Qx Ra Rf Rh St Ua Uu Wc Wm) Gb(Af Ar Ax bJ BN bQ cO Cs CX dR Ez gL Gp kR Kx Lj Lz Mh Ml Na Nj Nr oE oF Oh Oi Ow Qv Ra Rf Rh Wm) Uw(Af aN aW aY bJ bN Bo bQ bS cN cV Cx DE Dk GP Ki Md Mh Ne Nl Oe Oi Oz Pb Qn Qv Ug Ur Vp Vs) Wc(Af aN aW bJ BN Cq Cx Dc Et Gp Ho Hv In Iv Ji Jn Jr Js Ke Kg Kj Kn Ld Mi Mt Na Om Pi Vh Vs) Fi(Ba Cu dK Ez Hw iJ iO Ji Jj Kg Ld Mf Mk Ng Ni Nk Nm Nt Uf Ux Vb Vq Vw) Rz(aH aQ Ax bA Cs cT dA dR Ez Hf Ir Jj Ml Mx Nb No Ny Oa oE oH Oi Oz St) Fd(Af aN aW bJ Cu Cx Gp Jn Js Kq Mr Mw Na Om Qa Qe Tn Uc Ut Vs Vt) Vh(Af aN aW bJ BN CX Gp hG Jj Ki Md Nc Ne Nl Qw Ug Up Ur Uu) fR(aK bS cN CX gP Hp Ic iH Il iP Je nY OE Oi Or Oz Qn Qw Vp) Vb(Af aQ aZ Bn CX Gp Jj Ki Lj Md Ne oE Oz Pb Ug Ur) cM(aF aU aW aX cL cO cS cZ dK Kq Ld Li Nn Nq Pf Qv Ur) Em(AF aN Ap aW bJ BN bZ cV CX Gp Ne Ow Rh) Ho(Af aN bN cD CX De Gp kR Lz Mh Mi Oh Pb Rh Wm) Wg(Af aN Ap aW bJ BN bZ cV CX Gp Md Ne Pb Ur) We(Af aN Ar aW bJ BN CX De Gp Mt Ne Ur) Uz(Af aN Ap aW bJ BN bZ cV cX Gp Md Ne Ur) Vw(Af aQ aZ CX Jj Ki Lj OE Oi Oz Uu) Hl(Af aN Ap aW bJ BN cV Cx Gp Ur) Tl(Af aN Ap aW bJ BN cV Cx Gp Ur) Ry(aN aW bJ bZ Cx dE gL Gp Oe Ur) Sj(Ba cT Et iJ Ma oE Ow Qv Uf) Ux(dR Ez Jj Mg oE oH Oz Uu) Zx(Ba oE oF Ow Rf Rh Wm) Ke(Gl Lh Mj Nj Nk Vp Vs) Th(cS Ez Ld Li Na) Tm(aW cX dK Gz Il) Rv(aW bN cZ Ir Oh) Uy(aG Kd Mv Ni Ur) Du(aN Cx Gp Li) Vz(Mr Nf Nk Pf) Vc(cS cU hB Ma) Gd(Cx Jt Qv) Hp(Gp Oe Ow) Gh(Ld Oz) NbOp NkNw IrLt} No{Wd(AF Aj aN Ap aR aX aY aZ Bg bM Bn Bo bS cD cQ cW dG Dk EF Fr Gl gP Ha Hc Hu Ib Ic Il iP It Je Jl Jm Jy Ki Kl kQ Li Mg Mh Mi Ml My Ng OE Oi Oz Pb Pc Pf Qn Qt Qv Qw Rj Ss Ua Uh Ur Uu Uv Vp Vs Vw We Wh Ye Wm) Rz(Af Aj aN Ap aR aW aX aY aZ Bg bL bM Bn bS cD Ch cQ cW Cx De dG Dk EF Gl gP Ha Hc Ic Il It Je Jl Jm Jy Ki Kl kQ Li Mg Mh Mi Ml Ng Nn Nx OE Oi Oz Pb Pc Pf Qn Qt Qv Qw Rj Ss Ua Uh Ur Us Uv Uy Vp Vs Vw We Wh Ye) Ye(aF An Aw aX aY bC bH bW Co Cp cS cZ De dK Ef Ez hC Hq Ih Iz Jd Jg Jh Kc Kg Kj Kq Mg Mi Mm Mq Mt Mu Mv Mw My Nq Om Oy Pd Pf Pz Qa Qd Qu Qz Sr Ua Uf) Ho(Af aN aR aZ Bo bS cD Ch cP Ct cX dG Dk Dl Gn Ha hB Hc It Jl Kj Kl kQ Lj Mh Ml Nb Oe Oi Oz Pc Pf Qn Qv Qw Rj Ss Ug Ur Us Uv Vb Vp We) Th(aC aF aG Ao aU aX bE bG bJ cC cR cS cZ dA De Et Ez Gb Iv Jd Jh Ji Kg Kj Kq kR Mg Mu Mv Nn Nq Pj Qd Qv Qy Uf Un Ur Vu) Uy(aG aK Ao aQ Bo bW bZ cJ Co cS Cw cY De Et Ez hB iA iO Iv Jd Ji Ke Kg Kq Li Ma Mg Mi Mk Mm Mp Mq Mt Mv Nq Pd Pj Uf Uh) Ti(aA aG aH aK AN aY aZ bH bM cE Cw dR Fw Gp hB Hu iZ Ki Kk Kq Mg Mu Mw Nb Nn Nq Nx Oa oE Ow Qv Rh Sr Ur Uu Wh) We(aF Ap Aw Bb bW Co Cp De Ef Ez Jg Jh Kc Kg Kj Kq Li Mg Mi Mm Mq Mt Mu Mv Nn Nq Om Pd Qy Qz Uf Ut Vq) Wh(Af Ap aU Bn bW Co cX Dk Ef Ez Ib Jd Jh Kc Kg Kq Mg Mq Mu Mv Om Oz Pc Pd Qd Qy Qz Uf Uh) Fi(aG aI aQ aZ cX cY dR Fd Ha Hl Ii Jj Ki kQ Ld Lj Lx Md Ml Nb Nw Ow Pf Qw Ug Uu Vt) lX(Ij Is Iv Jn Jr kI kP Li Lz Ml Mw mZ nI nK Nx Oh Oz Pe Pf Qa Qb Qc Qd) Si(aA AN Bo bQ cE cF Fw Gl hB Kd kQ kS Nx Ri Ug Um Uu Uv) Ke(bL Dk Du Gl Hq Kf Kn kS Lh Mp Nk Nv Nx Po Rm Up Us Vp Vs) Vw(bW Co De Ez iH iJ Jh Kg Mi Mm Mu Mv Nq Om Qy Uf) nI(Il Jr kP mI Ml nC Nd nH Nj nK nL nT Nx Oz Pb Qc) Hp(aF An aY Bb bH bQ Cx Du Jg Me Nt Qy Vq) kP(Ih Il Jr Ml Mw mZ ND Nh Nj Nx Qc Qd) Uh(bN Hq Nk Ou Ow Rm Vs Wc Yl) Uw(Ap aU Dk Li Mq Mv Nn Nq Qn) Fd(Cu Hv Iv Js Kd Mi Ow Vq) Du(cC cJ Cw dR Ji Ld Qd) Gc(kQ Ne nW Oa Qw Rj Up) Ml(Gb jT jV kE nC nH nL) Hb(aE bN dK Hq Oe Ou Qy) Qc(kG nK nL nN oO Ou Ow) Ux(Ap cW Kd Nn oE Ss Uu) Vs(Et Kq Li Nw Qd Qy Uf) Gn(Kj nW Ra Uz Vq Wg) Gb(Cx Ki Lj Oi Pf) Tl(aW Bn CX Qn) Uu(bN dJ Et Ue Vb) jK(Fr Hq Hu hX Mk) Bb(Hl Op Ry Yl) Zx(aK aU dK iH) Rv(Cx dK Mg Pf) Ou(aF dJ Mw Oe) fR(iO Jd Qu Qy) Bo(Uz Vh Wg) Gh(bQ cE Ld) Hl(aW Kd Vq) Wc(aK aU Cw) Tm(Kz Mm Nq) mI(kC mF Oz) mZ(Mp Pd Qd) nK(mF nA nD) kN(Mw Nx Qd) Bn(Uz Wg) Ry(Ib Oe) Yl(aW hC) Ur(cH Hq) bN(Ss Vt) ChQy EmNc GdKd IjOg SfaK JjjT VbdK OznC} Nb{Ti(aA Ad AF Aj aO aS aY bF BG bM Bn Bo bZ CH Cq Cs Ct cV De Dg DK eF Fp Gd Hb Hc hG Hl Hq Iv IZ Jg Jj Jo Jy Ke Kg Kj Kl Kp Kx Kz Ld Li Lj Mn My Nf Nw Nx nY Oa oE Ok Oy Oz Pa Pz Qw Rh Sj Ss Tn Tt Uc Un Ur Us Uu Uv Vo Vp Vs Vt We Tl) We(aF aN Ap aU bE bJ bW cC CO cP cQ cS CU CX Di Ef Et Ez Fi Ho Hu Hv Ih Is It Iu Iv Jd Jh Ji Jn Kc Kg Ki Kk Ko Kz Mg Mi Mm Mp Mt Mu Mv Nh Oe Om Pd Pe Pf Qa Qd Ql Qy Qz Rm Si Ue Uf Un Ut Vq Wd) Hl(aL aN Ap aS aU bE bJ Bn bW cO Cx Ez Fi Fw Ho Hv Hw Ih Iu Iv Kc Kd Ke Kg Kz Li Lj Lw Mg Mi Mp Mq Mt Mu Mw Nf Nm Nn Oa oH Ow Oz Pa Pc Pd Pj Qy Ra Uf Uh Uk Vp Wg) Fi(aA Ad Af Aj Al BG bX CH Cq Cs Ct Cv De Dp Fd Fp Gd Gl hB Iv Jj Jk Jo Kj Kp Kx Kz Lj Lz Mh Ml Mq My Nf Nx oE Of Oy Pb Ph Pk Qu Qw Qx Uc Ug Uu Vp Vs) Wd(Ad AF Ar aW bE Bg bW Ch CO Cp Ct Ez Iz Jd Jh Jj Jk Jo Kc Kf Kg Kl Mg Mh Mi Mq Mt Mu My Ng Nn Of Oy Pb Pd Qw Ss Ua Uc Ue Uf Uu Uv Vs) Tl(Af aG aK aU aY Bo cN CX Dd dG dR Gp Ha Hc Hw Ic iZ Je Ke Kl Kr Li Lw Mi Nv nW Oi Oz Pa Pc Pj Qw Qx Ra Rc Ug Us Uu Uz Vp Vq Vs Vt Wg Ye) Rz(Ad Af Aj Ap Ar aW aX Bg bJ bL Bo Ch cO Ct De Ez fP Gd Gl iJ iO Jk Jo Kf Kl Li Mh Mx My Ng Nn Of Oy Pb Pd Pk Qb Qu Ss Uc Uf Uu Uv Ux Vs) Ho(Af Aj aU aW aX Ch Ct De Dp Gl hB iH Jj Jk Jo Lz Mh Mi Ml Mt My Nn Of Oy Pb Pd Ph Qx Qy Uc Uf Us Uu Uv Vs) Ux(aU aW bJ Bo bW Co cS Ez Iu Jh Kc Ke Kg Kq Mg Mi Mm Mq Mt Mu Nm Nn Om Pd Qy Ue Uf Uu Vq) Gb(Aj aM Bg Ch Ct De Iz Kj Kp Lj Lx Lz Mb Mh Ml My oE Oy Pb Pf Ph Qx Us Uu) Gc(Gl hC Kf Kp Kr Nc Nl nY pF Pk Rj Ss Uc Ug Ur Us Uv Vh Vs Tm) nI(Fp Hq Jj kP Lj mE mF nK nL nN nT Nx Of Oi Oy Oz Pb Qc Qe) Vb(aC aN Ap aW bE cO cZ Ez Iu Mg Nm Nn Pd Pj Ue Uf Vq) Tm(aN aY Bn Dk Hc Ic Jl Lu nW pF Pj Qw Uh Vp) Si(aA aM cV Kf Kp Nf Nu Oz Sf Ug Uk Up Uu) Ye(aP bE Ih It Iv iZ Kz Mq Mr Mw Pe Us) Fd(aF aS bE bJ Hv Kz Mi Mp Qy Vq) Zx(bB In Ji Kc Lh Mk Nq Ou Pf Uh) Rv(aF bE bJ BN cZ dI

Figure 38 Continued

Figure 38 Continued bQ Co Cp Cw De Dk dN Ef Et Fp Fw Gb Gc hB Ho Hq Hv Hw Id iO Iz Jh Ji Jn Jp Jy Kd Kg Kj Kk kR Kz Ld Lx Mg Mi Mr Mt Mu Mv My Nf Ni Nm Nn Nt Ny oF Om On Ou Pf Pi Po Qa Ql Qx Qz Tn Uc Un Ut Uw Vt Vw Wd Wh) Gb(aA aC aG aH aN Ar aY aZ bJ Bn Bo bQ cE Cu CV CX dI dR hG Hl Hr Hu It Iv Mq Nu Nv Nw Ny On Pf Qd Qm Qt Qv Qw St Uh Ut Vt) Hp(aC aG Ap aW bW bZ cE cL cN cO cS cU Cw Cx dI dK Ez Gc Gp Ic Kc Kp Ld Mk Mp Oc Oi Ow Oz Pj Rz Uf Uh Ur) Wd(aA aC aE Af aG aH Aj aN aW aX aY aZ Bg Bo cE Ch Cx De dI Hl Ip It Nu Ny Oe Oi Oz Pb St Uh Ur Us Ye) Vw(Af aH Aj Ar aY aZ BO bX cE CX dI fP HB Kl Nw Or Oz Pc Pf Qm Ri Un Ur Us Uu Vs Vt) Ho(aA aC Af aG aH aN aY aZ bJ bM Bo cB Cx De dI hB Ip Nu Ny Ur Us) Ti(aA Af aY bH bJ bM BO cE hB hG Hq Hu Iv iZ Nq Ny Qd Qy) Fi(aA aC Af aG aZ bM BO dI hB hG Jj Jy Ld Ni Nw Oz Ur) Hl(aC aN aY Ba bE bJ Bo cV Cx Hv Hw Iz Mi Nn Pd Vq) Uw(aC Af aN aY bJ bM Bn BO cV Cx Dd dI Oe Uh Ur) Fd(aC aG aN aY bE bJ Bo cO cV Cx cZ dI Pi Ur) Vz(Fw Hu Ic It Jg Jh Jt Kp Pd Pe Pf Pg Qt Qw) Wc(aC aF aG aN aY bE bJ Bo cO cV Cx cZ dI Ur) Wg(aC aF aG aN aY bE bJ Bo cV Cx cZ dI Ur Us) Rz(aA aE aH aX bM hG Hx Ld Ny Or Pk St Uo Vt) Uz(aC aF aG aN bE bJ Bn Bo cO cZ dI Gn Ur Us) Vh(aC Af aG aN aY bE bJ bM Bn Bo cV Cx dI Ur) Zx(bJ bM bQ cE cO cZ dI fR hG Ld Oz Ri Ur) Tl(aC aG aN aY bE bJ Bo cV Cx cZ Mi Pi Qy) Vb(aC Af aN aY bE bJ bM Bo cV Cx dI Ur) We(aC Af aN aY bE bJ Bo cV Cx dI Ur) Wh(aC aN bM Bo cV Cx Dd dI Tz Ur) Ye(Ef fR Hu Iz Jd Jh Mu Nv Ua) Et(Ij It Nw Oe Og Oy Oz Pb) Si(Af bM dI fR hB hG iZ Oz) Rv(aH hB Hu It Jh Pf Pg) Nw(Ij It Oe Og Oz Pb) Gc(hB iZ Je Ri) Ry(aC aN Bo) Op(aG Jd Nt) Sf(iO Ni) Ld(Gh Ux) Og(Ij Ji) Uy(Kd Mv) EmQy GnPi NjLt SjbQ QcnN YlaN VtbN} Pe{Th(aA aF aV BG bJ bS bU cA cD cF cR Ct dA dG dH Hl Hq Iv Jk Ky Lx Mn Nd Ns oE Of Oy Oz Pa Pf Pg Qw Qz Rg Uk Um Ur Vz Tj) Ye(aA aF aS cW fR gL Gn Hu Ih iZ Je Jg Jk Jm Jq Kx Ky Lz Me Mu Nj Nn Nt Nx Ny Oa Qg Qu Sr St Um) kN(aA Fp Hr Ij Il Jp kC kO kP lX mE mF Mh mI Mt mZ nA nC nD nF nH nJ nL nN Nt Nu Oz Pf Qa Qc Qd) Vz(Al An aW Bb cX dK Ex Fp Fw Gp Ic Id Jm Kd kQ Ni Nr Nx Oe Or Po To Ul Uy Tm) Uy(aA aG bN bO bX cW dI Gd hB hG Hl Jf Jm Jq Kd Ld Lx Qv Ri Ug Ur Uu Yl) Gn(Fn fP Hc Ib iP Ki Kl Kr Ne oN Qt Qw Ra Rj Ua Ur Uv Uw Uz We Wg Wm) nA(aA Hr Ii Il Jo Jq kE Lx mE mM mZ nC nH nK nL nN Nx Oz Pb Po Qc) nD(aA Hr Il Jq kE kP Lv Lx mE mZ nC nH nK nL nN Nr Nx Oz Pb Po Qc) Yl(Al Bb cX Fw Ic Id Il Jm Kd Ky Mj Nt Nx Or Po To Ul Tm) Uw(Ba Bb Is Jg Jk Kq kS Mu Nn Nt Nv Nw Om On Ph Qa Qd Ri) Hl(aF Al An aW Bo cD Di Fw Gp Id Jg Jm kQ Ky Ph Ul Vq) We(Gp Iz Jg Jk kS Mu Nn Nt Nv Oa Oi Ph Qa Qg St Um) lX(aA Il Ji Lx mM Mp Mu MZ nC Nj NR Nt Pf Po) mF(aA Il Ip Jo kP Lx mI MZ nC nH nK nL Oz Po Qc) kC(aA Jo Jq kE Lx mI mZ nC nH nK nL nN Nx Po Qc) Ti(aA Af bM Bn Bo Dg iZ Ny Uk Um Uu Uv Vo) nN(Ii Jo kF kI Lx Ml mM MZ Oi Oy Pb Qc) kP(aA Hr Il Jj Jo kE Lv Lx mZ nC nO Po Qc) nC(kF kI kO Ml nH nL Oi Oz Pb Qc) Gd(Fi Gp kQ Ky Or Rf To Vq) Tl(aE aH cE cY dR hB Mq Um) bN(Ha Hb oN Pj Tv Uh Vs Vt) mZ(kG kI Ma Mg Mp Mt Oz Pd) kE(aA Ij Lz Ml Nu Pb Pf Qd) Wd(aX Bn Ch Kj Pb Po Vs) Hp(aW Dd Oe Qn Vp) Rz(aX Ch Gl Po Uv) Ex(Dp Ks Rg Ur) Fd(aX bM De Ij) Ho(Af Kj Po Uv) Rv(An Nr Oa Pa) mI(kF kI Nx Pb) nL(kO Ml Nu Qc) Aa(Ha Jv Uu) Bo(Sf Uz Wg) Fi(bM De hG) Sj(aD aY cE) Ry(aJ dM Uu) kF(aA Nt Qd) Dd(Op Vh) Em(Nc Nk) Gc(aN Gl) Ha(oN Uh) Id(Uz Wg) Wc(aD Uv) Nx(kI mP) Ux(aF bW) Vw(kS Qy) nH(kO Ml) nK(aA kO) MikG NcSf NkUh HuWh IjVh SiUv JfTm VqVs} Nn{Gb(Af Aj aY Bg bM Bo cF Ch Co cV Cx De Dg EF Ez Fr Gd Gl Hb Hc Iz Jj Jo Kg Ki Kj Kl Ld Lz Ma Mh Ml Ng Oi Oy Pb Qx Rz Uh Uu Ux Vb Vo Vs Vt) Ux(aC aE aG aH aM aY Bb bJ bM bO bR cF cH cM cV Fw Gc Hu Ih Ir It iZ Jg Jh Jn Kn Kq Nt Nu Nv Ny Pc Pd Qd Qe Qy Rm Sr St Ub Vc Vq) Hp(aZ Bg Ch Ct Ef Ez Gl Hc Iz Jj Ki Kj Lz Mg Mh Ml Oi Oy Oz Pc Pf Qu Qw Qx Qz Rz Ss Uh Us Uu Vs Vt Ye) Hl(Aj Ax Bb Cq Cu cV Dc Fw Ha Hc Hv Ir It Jn Jr Kd Me Mi Mr Mx Nr Ny Oa Oy Pi Qe Sr Vq Vt) We(Cp Cq Cu Dc Dd Em Hc Hv In Jn Jq Jr Js Kd Kn Kq Mi Mr Nr Ny Pi Qa Rb Tv Un Up Uz Vp Vs) Fd(Af Aj Ar aY Bg bM Bo cV Cx eF Gl Hc Jo Kg Kj Kl Lz Ma Mg Oy Oz Qx Ur Us Uu Uv Vp Vs) Uz(Af Ar aY bM Bo Cx eF Gl Hc Iz Jo Kg Kj Kl Ld Nu Nx Of Oy Qw Uh Us Uv Vs) Ho(Af Aj aY Bg bM Bo Co cV De eF Gd Gl Hc Jj Jo Kg Kj Ld Oy Pb Uu) Wc(Af Aj aY bM Bo cV eF Gd Gl Hc Is Iz Jo Kg Kj Kl Ld Us Uv Vs) Vc(Af Aj aO BG bM cF Co De Dg Ez Fp Fr Hb Hc iP Iv Qw Wm) mZ(Fp Ii Iv Jo Jr kP lX Ma Mp Mq Mr nA Nh Of Oy Oz Pb Qc Qd) Rz(aA bM Fw Ij It Jl Jn Kq Mi Nv Ny On Pd Qd Uf) Uy(aA Af aH Aj bM cF eF Fp HB Jj Ld Nw Oy Un) Gd(Ez Kd Kq Qy Rm Sr Tv Ub Un Up Vp Vs Ti) Vb(Cq Cu Dd Hc Iv Jt Kd Kn Nr Pi) Ye(aA aE aY cV Ih It Ny St) kP(Fr Hu mM Of Oy Oz Pb) Th(aA Cs Fp Hb Ij Iv) Uw(Aj cV Hc Kl Qa Un) Vw(Ch Dg Kl Ng Qu Ss) Si(aA iZ Kg Nu Uu) Oz(kG kN mI nL Sj) Gc(iZ Kg Kl Uu) Wg(Af Aj cV Uh) Wh(Dd Ny oH Pi) Jo(lX mF mM nK) Yl(bM Fw Kl Ld) Du(Ch Cs Po) Fi(Aj Jj Ld) Hc(Em Vh Tl) Sj(Fw Nu oE) Rv(aX aY Qb) lX(Iv Lz Qa) Ti(aA Kl) Ml(nH nL) Vz(Fw Sr) Wd(Ch Ny) Tl(Kd Uh) Nx(kI nA) Op(aZ Hb) Vh(Aj cV) AaUu EmUh EzTm GhbM NuoP SfaA ZxPc QcnR OfkG UgeM PbkN fRiZ} Sr{Gd(aF aN Ap aU aY BB bG bI bQ cH CO cP Cu Cw Cx cY dK Ez Fw gL Gp Hq Hu Hx Jg Jh Jk Kd Kg Kq kS Ld Mg Mi Mq Mu Mv Nk Nq Nv Om Ow Oz Pc Pd Pf Qa Qt Qw Qy Ri Rz Uf Ut Wd We) Hl(aF aH AN aW Ba bI bQ bR cH CO Cq Cw Ez Fw Fy Hq Hw Hx Ih Il Io Is Iv Jg Jk Kd Ko Kq kS Lt Nf Nr Nv Oa Om On Ow Oz Pf Ph Pi Qa Qe Qt Qy Tn Uk Ut Uv Vq We) Ux(aF Ap aW bG bJ bW CO cR cS Cw Ef Ez iO Iz Jd Jh Kc Kg Kq Ld Mg Mi Mp Mq Mu Mv Nc Ni Nq Om Pd Qy Qz Rz Uf Wd) We(Ad aG Aj Ar Bo Dp dR Gl Gn hB Hx Io Iq Jj Kf Ki Kj Kl Ld Mt Mv Nl Of On Oz St Uk Uo Ut Vh Vo Ye) Vz(aK aL aQ aU aV AW Ax bB bQ cH cY dR Fw Gp Ic Il Kd Kk Ky Mx Nr Oa oE Oi Ow Qw Ry Ug) Ye(aF aN bI Bo Co Cx fR Iv iZ Jd Jh Kc Kg Kk Ko Mg Mq Mu Mv Om Pd Qy Qz Uf Ut Wd) Vh(aH bB bI bR cI Cx dR Et Hx Io Is Iv Ji Ko Kq Lt On Ow Oz Pc Qh St Uk Ut Uv) Sf(Af aH aY aZ bM cD CX Gl Il Jm Oz Pb Pc Ul Us Th) Gn(bI bR Cx dR Hx Io Iv Ko Lt Mt Nf Nv Oz St Uk) Rv(cH Is Kk kS Lz Ml Oa Oh Ow Pb Pf Qb Qx Ri) Wd(Af Aj aX aZ Bg De Gl Ik Kg Kj Ng Oy Pb) Lt(aG aM bJ Bo Dp hB hG Ih Jj Ld Nl Of Uo) Th(aA cR Cs Fp fR Iv Jj Kx Og To Uk Ur) Rz(Af Aj aX aZ Ch Dg Gl Jo Kg Kj Pb) Ry(aM Ar bJ Bo Dp hB Jj Ld Nl Of Uo) Yl(Bn bQ cH Cx fR Hu Nu Oe Pf Qn Up) Uy(Cv Fp hB Kz Ld Mq Mv Nf Nq Ur) bN(cH Et Hb Ji Jq Nw Oi Uh Vt) Wc(aN bI Bo Cu Iv Jr Js Ko) Ho(Aj De Gl Kg Kj) Sj(aN bQ cE Qv Ri) Tl(Af bM Gl Uo Uv) Op(Ld Lz Ml Pf Qx) Uu(dJ Fd Uh Uw Tm) Vb(cO Iv kS Nf Nt) Af(fR Gc Uw) Uz(An Cx Nl) Du(Nq Po) Fi(Bo Jj) Hp(Gp Ug) Zx(Ki Nq) Wg(An Pb) Uw(bM Kq) Vc(cO hB) TiaA EmaN GhhG WhOy cXfR} Ld{Uy(aA AF Al aN AP aX aZ BN Bo bR bU bX cB cF cK Cs cV Cw CX Dc Dd Dp Ef Em Et Fi Fp Gc Gp Ha Hp Hw Ic IH Ii Ij In Io iP Ir It Iv Jg Jh Ji Jk Jn Jp Jt Kc Ki Ko KQ Lt Md Mq Mv Nh Nj Nt Nu Nv Ny oE Of Oh On Ow Oz Pb Pf Pz Qa Qb Qc Qd Qn Qw Qy Rm St Tz Uf Up Ut Vh Vq Yl Tj) Gh(Al Ax cE Cp Cq Cu Dc Dd Fd Fi Fw Fy Ha Hp Hq Hu Hv Ih Ii Il In It Jg Jk Jl Jm Jp Jr Js Jt Ko Kq Mi Mr Mt Mx Nt Nv Nw Ny Oa Om On Pf Pg Ph Pi Pz Qb Qd Rm St Tv Up Vp Vs) Fi(Af Aj Al aM aW aY aZ Bo Ch Cs CX De GL Gp Ih Il Ir It Jg Jj Jm Jn Jp Ki kR Lx Md Nu Nx Ny Oa Oz Pb Pf Pz Qb Qn Qw Qy St Uv Ye) Th(aA Ax Cs Cu Cw Dd Fb Fp Fy Hb Ho Hp Hv Hw Ij Ir It Jn Jr Js Me Mr Ny Pi Qd Tz Un Vp) Ye(aF Al Ax aY bM Cp Cq Cv Fw Ha Ho Hu Hw Ih Ii Il It iZ Jm Js Jt Nt Pg Pz Qh Tj) Fd(Af aN aO Ap aW aY Bn Bo CX Gl Gp Hu Jm Lv Mx Nu Nx oN Oz Pb Qy Us Vp Vs) Ho(Af Ap aW Bn Bo CH CX De Gl Gp Hu Jm Ki kR Nu Oz Pb Pf Pz Qn Qy To) Uz(Ap aW aY bL Bn CX Fw Gl Gp Hu Jg Jm Mn Mt Nd Nu Nx Pc Pz Qy Uv) Hp(aW aX aZ Ch cX Fw Gp Il Jm kR Mh Pf Qn Uh Vt) Sj(Fw Is Jg Jk Oh Ow Pa Pf Qb Qc Qh Vq) Wc(Af aW aY Bb CX Gl Gp Hu Jm Js Qn) Gb(Af aW Ch Fw Gp Hu Jm Pf Qn) Gc(Ch Il Jm Kd Qw Ry Uv Tj) Fw(Du Gd Hl Yl Tm) Ux(Hu Jg Pf Qy Vq) Jm(Hl Vw Yl Tm) aA(Ry Sf Si Ti) Ch(Rz Uw Vw) Gp(Gn Hl Ry) Vz(Iv iZ We) Wh(Jg Pz Qy) Du(Ax Jn) Ij(bN Vs) Zx(Pz Tj) AlSf CqGn DdVb GdIl HlOa HuWd IqRy IrLt QaUw JgRz WeUh VwaW} aA{Ti(aE AF aH aI aK Al aM aN aQ Ar aS aU aW Ax aY bB bI bJ Bn Bo bR cH cQ Cs Cu CX DC dR Et Fa Fp Fw Ha Hb Hq Hu Ic Id Ih Ii Ip Ir Is It Iu Iv Jf Jh Ji Jk Jl Jm Jn Jq Js Ju Kd Ki Kq Kx Kz Lh Lx Lz Mb Me Mf Mh Mj Ml Mt Nq Nr Nv Nw Ny Oh Oi Om On Ou Ow Oz Pc Pf Pg Po Qa Qb Qc Qd Qe Qx Qy Rm Ry Si St To Tz Uh Un Ut Vt Th) Si(aM Ar As aW Ax bI bJ bQ cH Cs cX Fw Ih Il Iv Kx Lx Lz Mf Mh Ml Mq Oa Oh On Oz Pb Qe Qx Ra Rh St Wc Wm) Gc(Gl Ha Ic Kd Ki Kk Kq Nc Nl oE Oz pF Qh

Figure 38 Continued

Qv Qw Qx Ri Rm Ry St Ul Uu Uy Vc Th) jK(bN bO bQ cS cV cW dM Fr hA Hq Hr Hu Ii jL jT Md Mu My Nv Of On rB) Ho(Af Ar bI cH De Gp Lx Lz Mh Ml Mx Oa Oh Oz Pb Pf Qx) Wd(Cx De Gp Ir kR Lx Lz Mh Ml Mx Oz Pb Pf Qb Qx St Uh) Th(aF Ao cS Cw Et Fp Iv Jh Ji Kq Mm Mt On Pj Uf) Uh(aE aF aW bG bN cH dJ Fb Hl Ne Nk Ou Uw Uy) aW(Du Hb kl mS nJ Rv Ry Vc Vh Tm Tl) nK(aZ cX Is kl kP Lz mF Ml Pf Qb Qc) Ry(Af Cx Et Gp Mk Nq Pj Qn Qy) cX(Gh kP mI mU mZ Uw Vh We Tl) Fi(aM Jn Lx Lz Mh Ml Oh Qx) Oz(Ip kP lX mI nL Rz Uw Vh) mZ(aU aX cO cS dK Ma Mg Mp) Qc(kG kP lX mF nL nN Rz) Uy(Et Iv Ji Mk Mm Mq Pj) Cx(Hl Hp Vc Vw Tm Tl) Ij(Fd Hl lX Og Vh Wc) Ye(aF Ih Mq Qa Qe Qy) Uw(Af aN aY bJ Bn Ic) Pf(Gb kE kP mF mI nD) cH(kP mI nN nU Rz) Ml(Fd jT kG mP) Wc(Hv Ji Js Vq) lX(Is Lx Lz Qa) mF(aF mI nL Qa) Hb(bN Il Or) Rz(Ir Oa Qb) jT(Nw Qb rZ) Hp(Ih Qe) Rv(dK Vq) Op(Kd Mi) Vc(cU Gp) cN(kP mU) AfVh BnWg CwVb EtjO GbMh NkjR IlTl IrLt ItNw SjOw WeKq bIkP} Oa{Hl(aF Ao Ap aU aW Bb bC Bn Bo bQ bW CO cS cU Cw De dK Ef Ez Fi Gb Ho Hw Ic Il iO Iu Iz Jg Jo Jt Kc Kd Kg Kj Kq Mg Mi Mk Mt Mu Mv Nm Nr Nt Oe Om Pd Pf Ph Qz Rz Ue Uf Uk Ux Vq Vw Wd Ti) Gb(aN Ar aW aY Bn Bo CV Cx dM Gn Gp Lz Mh Ml Oi Oz Pf Qn Qv Qx Rj Uh Ur Us Uu Vp Vs Ye) Gn(Bn Bo Cp Cq Cw Fi Ho Hv Hw In Jo Kg Kq Lw Nf Nm Nt Om Pd Pi Ra Uo Uz Wd Wg) Ti(Af aH aN aY bJ bM Bo Cv Cx Fw hB hG Hu iZ Me Nu Oe Oi Qy Uh Ur Us Uv) Wd(Af aN aY Bg Bn BO Ch CX dD De Ip Iq Lz Oi Oz Pb Qn Qx Ua Uh Ye) Gc(aC Af aN aY BN bO Cv Cx dD dI Du Iq Jf Jq kS Nu Oz Ur Us Uu Uv) Vw(AJ aZ Bn Bo bS CX Hc Kl Oe Oi Pc Qn Qw Uh Us Uu Vp Vs Vt Ye) Ho(Af aN Ar aY Bn BO Cv Cx De Dp Gl hB Ip Iq Lz Ml Pf Qx Ur Us) Ry(Cp Cq Hv Hw Jo Jt Kd Kr Lw Nf Nm Nr Ny Om Pb Ph Pi Pk Tl) Ye(Ao bE bJ Ef fR gL It Iz Jd Mq Mu Nt Nu Qd Ql Qw Qy Qz) Si(Ar bE bJ Bn Bo Cv Cx dD dI hB hG Iq Nj Qn Ub Us) Rz(Af aX bM BO dD Ip Iq Ml Oi Oz Pc Qx Us) Bn(Em Fd Uw Uz Vb Vh Wc We Wg Wh Tl) Du(Ar cC Cw Fp iO Iv Mk Mq Mt Po Qv) Rv(aH Dp It Jh Ju Jv Kp Pf Qm Qt Qw) Cx(Em Fd fR Uw Vb Vh Wc We Wg Wh) Fi(Af aZ Bo Cv Iq Jj Lz Oz Ur) Fd(Cu Hv Ij Iv Jn Jr Jt Mi) Uw(Af aN aY Bo cV Us Uu Vp) Bo(Uz Vb Vh We Wg Tl) Sj(aG bQ cE Dd Ow Uf) Vh(Af aN aY bM Iq) Uz(Af aN aY Cv) Zx(bE cZ Ur) Wc(aY Cu Vq) Wg(Af aY cV) Vb(Cv Uh Ur) Em(CV) Gh(dI Ni) Hp(aW Gp) Vz(dI Ic) AfGd ThIv WhUh KdUy YlaN cXfR} Pf{Hp(AF Aj aO aU aW aY Bb bF BG bM Bn Bo bS bZ CH cV dR fP Gl gP Hc Hq iH Kc Kd Kg kS Lu Mj Mt Mu oE Oi oK oN Oy Oz Pb Pc Pd Pj Qw Qy Rg Rj Ss Uf Uh Ur Uu Uv Vo Vp Vq Vt Zx) Vz(aF aO Ax aY Bb bF bR Cq Cu cV Fw Gb Gc Ha Ho iA Ih Ii In Ir It Jn Jr Js Jt Kd Me Mr Mx Na Nr Nt Oi Pc pF Pg Pi Qe Tz Ub Uh Vo Vq) Rv(aF aO aY aZ bF BG bL bZ cE Ch cV fP Fw iA Ih iZ Jn Kl kR kS Nw Ny oH oK oN Oz Pc pF Qb Qu Ss Uu Vq) Gb(AF Aj aN aY aZ BG bM BO Ch cV Cx Dg fP Fw Gd Gl Hc Iv Jo Kl Lv Nu Uu Vo Vs Vt) kN(Fp Ii Iv Jj kP lX mE mF Mh Ml nC nH nK nL nN nT Nu Nx Oz Pa Qa Qd) lX(Fp Ih Ij Iv Jn Lv mI mZ nL nN nT Nx Of Og Oz Qa Qb Qd Qe) nL(Iv kC kO kP Ly mF Ml nA nC nD nH nJ Nu Of Oz Pa Qc Qd) Zx(aE aY Dd Hb Hu Jn Kq Mu Nt Nw Ny oK Pc Pi Qd Qy Un) kP(Fr Ih Ir It Iv Lv MF mZ nD Nx Of Og Oz) Fd(Af aY bJ bM Bo Hc kS Mq oK oN Oz Qy Ur) Ho(aY bM Bo iZ Kg Nu Ny Oz Uu Uv Vo) Wd(Af Aj aX Bg Ch De fP Hc Kl Ng Uu) Op(aY Dd Hb Oz Pc Qy Vq Vt) Af(Fi Si Uw Uy Uz Vh Wc) Vw(Aj aY Ch fP Kl oK Uu) Iv(Du kE mZ Vb Vc Th) Fi(Aj aY bM Jj Oz) Gd(oN pF Rg Si Vt) Sj(bM bO Hc kS oK) Ux(aF bJ Mq Nt Qy) mZ(Fp Mq nN Oz Qd) Si(bM iZ Nu Vo) aY(Uy Uz Wc Yl) Gc(iZ Uu Vo) We(Dd Uu Vo) nD(nC nH Nx) Aa(Oy Uu) Fp(kE Uy) Wc(Bo kS) Wh(kS oK) Kz(Du Uy) Uz(Hc Qy) bM(Gh Vh) bN(Uh Vt) fP(fR Rz) mI(lY Oz) DdSf TiNy EmNc NtVb NuoP JonN YeiZ YlcV PakE mFnC} Qa{We(aF aN aO aY Bb bJ bO Cp cV Cw cX Dd dG dH dI dL Du Ex Fn Hu Il Iv Jh Jl Jq Jt Kd Kq Ky Mi Mt Nr Nt Nu Oe Om Oz Pc Pd Ph Qw Qy Rg) Uw(aC Ap aW bE bJ cN Cu Cw Cx dM Ez Gc gL Hu Hw Ij Iv Jh Jl Kq Mg Mi Mq Mt Na Ni Nt Pj Qy Ra Rg Uf Ur Vp Vq Vw) Ye(aC aF AN aO bE bJ bO cV dD dF Dp GL Hu Iv iZ Je Jl Jq kS Ky Lv Mz Nt Nx Ok Ou Qw Qy Tn Uc Uo Up) Hl(aF aN aO aY Bb BN Bo cN cV Cx dG Dk Fi Fw Jm Kr Ky Mj Nv Nx Oi Oz Pb Pc Qn Vp Vq) lX(Jj Lx Lz Md mF Ml MP Mq Mt mY mZ nM nN Nr NT Of Oh Oz Pb Pc) Du(Af Ar bF BG Bo cH iH iO Iv Kl Mj Nv Nx nY Of Oy Tn Uu Vp Vs) mZ(Ii It kG kP Ma mF Mg Mi Mp Mv nA nK nN Oz Pd) Uh(bN Cw De Lh Ne Nk Ou Ow Vs) Uy(Bo Cq Cv dD dI Ex hB Iq Kd) Fi(Ad Aj bM Bo Cq hG Jj Jo) Kl(Gn Op Ry Rz Ux Vb Vw Ti) mF(Ii mI nC nH nK nL nT Nu) Aa(Jj Nk Oe Ou Oy Uu Vs) Gc(Jf Kj Kr Nc Nl Up Uu) Wd(Aj Bg Ch Dc Ef Ua Uv) Ry(aY Jm Kd Kr Mj Nx Vs) Rv(aN aW Bn Gl Jm Nx Uv) Oz(kE kN mI nC nH nL nN) Af(Gh Si Vz Yl Tm Tl) Ex(Dp Gd Hb Qv Tv Ur) Rz(Aj aX Ch De fP Vs) Ti(aY bM Bo Ki Kr) Th(bE Iv Nt Rg Ur) Sj(aD aZ bP Hc Ur) Fd(Hv Iv Js Mi) Ho(De Kj Us Uv) Ux(aC Ap bE bJ) Vs(bN Gb Vb Vw) Nt(kF Vw Wh) Hp(aW Dk Ur) Si(Kr Us Uv) Wg(Bn Bo Pb) nN(Ii Jo Qc) Gh(bM hG) Gb(Kr Pb) Gd(Or Qy) Nu(nD oO) Wh(bJ dI) Nx(mP nM) mI(nA Pb) BnVh BoUz EmNc LzkN MlnC HbbN ZxdG WcaN JjkP TmUr UuVb VcdI} Iv{Th(AF Ao Ap Ar aW Ba bB Bc bG bH bJ bQ bR cR CS Cv Cx Di Em Et Ez Fp FR Fw Gb Gc gL Gn HB Ic Id Ih It iZ Jd Jh Ji Jj Jn Jp Kk Ko Kq Kx Ky Kz Mq Mr Ms Mt Mz Na Ng Nt Nu Nv Nw NY Oh Ok On Ow Oz Pc Pj Qe Ql Qy Rf Rj Ry Si St Ub Uf Uh Um Un Ur Ut Uw Vq Vt Wc Ti) Vb(aN Ap aW Ba Bb bG bJ Dd dK Fw Hu Ic Ij Il It Iz Jg Jh Jk Jm Jt Kd Ng Nt Nx On Pa Pz Qc Qy Ri Si Ul Vq) Wc(aE aF AN aO aY aZ bG dG dH fP Gc Ic Ir Is Jm Kd kQ kR Nw Ow Pa Pz Qc Qy St Uh Um Vc Vq Ti) mZ(kG kP Lu Ma mF Mg MI MP mT Mv Mz nC nK nL nN Nq nR nT nU Oh Oz Pd Qc Qe) Ti(Af aH aN aY bM Bo Cx Fw Gp hB iZ Kk Nx Ny Of Ug Um Uu Uv Ye) Ye(aF Ap aW aY Bb bJ Hu Ih Jg Jh Jn Ny Qc Qd Qy Vq) Si(Af Aj aN aY Bo Ch Fw Gl Kd Nu Nx Of Us Uu Uv) Vz(bM Bo Gb Kq Mr Nw Ny Oz Pc Qd Un Ur Vt) Uy(aN aZ Bo Cx Gc It Kd Mv Nw Ny Qm Qw St) Uw(Af aN aY bM cX Gl Us Uu Uv Vs) Qc(Aa lX nB nC nH nK nL nN) Ry(AN aY aZ Bo kQ Nx Of) Hl(aW Ih Il Jm Nr Pa St) We(Hu Ih Jg Jk Jn Qy St) Vc(Af bQ Cx Fw Jm Kd Nv) Gb(aW aZ Ch Fw Nx Of) Gc(Gl Kd Up Uu Uv Vs) Gn(Kd kR Qy St Uh) nC(kP mF Ml Oz Pb) Fd(Ny Ow Qe St) mF(nH nK nL) Fi(Aj Of) Ml(nH nL) Zx(aN aY) Wd(Pb Qy) Ux(Ap Jg) Oz(nH nL) bN(Hb Uh) nK(Jj Qd) DeHo DuOw GpHp RzPb YlaW NwVp NxmI OpaY nNkP} Ij{Th(AJ aM Ar bE bH bJ bN Cq cR cT Cv gL Gz hB Hf hG Jd Jj Ju Kz Mn Mu Nc Ni Nt Pa Qh Qy Rh Rm Sf Uf Ug Un Up Ur Vz) Vh(An aO bF bR bS bZ cE cL dF dG dH dR Du Ex Gb Gc Ih Kd Kl Mi Mj Mt Ne oH Oz Pc Pk Rg Si Ub Uh Um Vc Vo) bN(Dp Fi Hb Hc Ju Ki Kj Kl Ou Ow Qw Rc Tv Uh Ur Us Uu Uv Vb Vs Vt) Og(Et Ik Ip Ir Is It Jg Ji Jj Jm Jn Me Nd Ns Nw Ok Oz Pb Qc) Gd(Bb Dp Ex Gp Hf Jg kQ Ne Qy Rb Rg Rm Tv Ub Us Vp) Vs(aE Et Ez Gb Ho Kq Nk Nw Ou Qd Qy Uh Wd) Vz(bU Ex Jm Kd kS Nd Ne Nx Ub Us Uy We) Nw(Hr Hu Hx Jj My Ns Of Oy Oz Pb Vp) Hl(aF aW aY Bb Bn cH Cx Jm Kd Vt) Vb(Bn bW Cx dI Jd Jf Mn Ni Nk Ok) Gn(Bn dC dF dG Hp Pk Rh Uo Uv) Op(Ad Cx Gl Hv Kf Ki Kk Nl Pk) Wh(Aj aY Bg Ct Hc Iq Oy Ub) Rv(aZ Bn Cx Dg Gl iZ Kd Ny) Of(Et jT kP lX nC nH nL Pb) Ho(bJ Ch De Kg Kj Nt Qy) Wc(aC aF bJ Dg Jo Kl Vo) We(aC Bo Gl Je Js Nt Uo) Oz(kE kN lX mI nC nH nL) Wd(aY De Dg Gl Kj Us) Uh(Hq Ne Nk Ou Up Uu) Gb(De Dg Dl Kl Kr) Sf(aY Ex fP Jm Kl) Qy(Ch Hc Ux Vw Ye) Nk(Hc Ou Qt Sj) Ye(aC aF bJ iZ) Uy(Cq Cv Gz Pa) Aa(Ib Jj Pb) Du(Ar iA Jj) Et(Oe Oy Pb) Gl(Gc Rz Vw) Ne(Aj fR Qt) Sj(bM Mj Up) Ou(dJ Hc Jv) Ch(Rm Rz) Hp(Je Ug) Jo(nN nT) Yl(aY Up) Vc(dI hB) eP(Nc Nj) fR(Kl Pk) lX(Lz Mq) CqTm DgGc FdaZ FiaF GzeC NtVw MlnH MuUx HqHc SibE ZxKi JjPb KqUw LtbJ UpeM UudJ nNkP} Ho{hB(AF Aj AN aR aW Bg bL Bo cG Ch cV Cx De dG dH fP Gl Ih Jm kR Ny Of Oz Pb Pi St Um Uy Vb) Ny(Af Aj aN Ar Bg bJ Bo CH Cs Dk Fd Ki Kj Lz Mh Ml Mx Oe Qn Qv Qx Us Uu Vp Wc We Ye) Bo(Ar Ax cH Cx De Fw Ih Il Ir Jn kR Lx Lz Mh Ml Mq Mx Nr Nw oE Oh Ow Oz Pb Qx St) Af(Ar Et Fw Gp Ih Is iZ Js Lx Lz Mh Ml Mq Mx Nr Nv Nw Oh Qb Qx Tz Uh) De(aH aZ Fw iZ Jl Jn Mq Mt Mv Nu Nv Nw nY On Qb Qd Qe Qy St) Kj(Cx Ih Is It Jg Jn Jt Ko Kq Mt Nr Nt Nu On Ow Pz Qy St) Us(aZ Cx Ih Jl Jn Kq Mv Nv Nw On Ow Oz Pb Qd Rm St Tz) Ar(aN aX aY aZ Ih Il Jk Jm Kd Mk Oz Pb Qy St Uv) Cx(aX aZ bG Ch Fw Gd Jj Kg kR Oh Oy Oz Pb Ur Wc) Uu(Fw Is It Jg Jn Nr Nv Ow Pz Rm St Uh) Aj(Fw Ih Is Iz Jn Nr Nv On Ow Qy St) Gl(Cu Et Jn Js Kq Lx Nw Oh On Ow) Uv(Jn Js Lx Lz Ml Oh Ow Ql Qx) aY(aH bB Lz Ml Nw Oh Ow Qx Ur) bM(Jn Lx Lz Mh Ml Mx Oh Ow Qx) Ch(It Jd Jn Mq On Ql Qy St) aN(aZ Fw Gd Hx Mq Oh Ow Qb) iZ(Gp Lz Ml Mx Oz Pb Qx Uh) Nu(aX Lz Ml Pb Qb Qx) Fw(Bn Gd Mi Oy

Jo Kj Lz Pb Rj Us) Hl(Kd Ki Kq Qe Vt) Du(Ar Fp Ji Po) Lz(lX nC nH) Vz(lc Oe Uh) Lt(aM Jj Vt) Em(Rj Us) Wc(Jr Pc) Jo(nN nT) Vb(Mi Pd) kI(nC nH) AaQc MqWh IinN RjUz} Kq{Uh(BG bL Hq Mp Ne Uv Vp Vs) Ex(Aj Dp eC Jo Kj oE Oy) Zx(aW Gl Jm Kd Kl Us Vs) eM(aZ Ch De Nx Uv) Gh(aN bM Bo Gl) Gd(aW Jm kQ kR) Wc(Fr Kd Qw Us) Vb(aN Bn Lv Rg) Du(Ax cH kR) Hl(Jm kR Nr) Aj(Ug Tm) Bn(Vw Wg) De(Hb Hw) Gl(Uz Yl) ChdN GniO UcUz VzhB SiKj SjUs KdRy RgVw OibL OuPb} Gb{Bo(Il Ir Is Lx Mh Oh Pz St) Ch(Ez Mg Mq Nq Nv On Qz Ut) Oh(aN bM Gl Kl Us Uv Vs) Mh(fR Jk Mt Nu Nv St) Ar(Gp Il Jm St Ul) Gl(Cu Lx On Po) Jm(Lz Mq Qx Ur) aN(aP Fp Lx Qb) Us(Is Mt On) Nu(Lz Qx) Qb(bQ Ni) St(aW Qv) Nv(Bn Pb) hB(Il Kd) NrJo MqaW MtPb QxJk cXgL} Nr{Vb(aF bE bJ bW Co Ez Jd Kc Mi Mt Mu Om Uf) Hl(aF aS bJ Kz Mg Mi Mp Mq Mu Nf Uf Vq) Vz(aG cV Ic Ji Mk Mp Mq Pj Si Uh Ur) Rv(Hb Lx Lz Qb Qx Tz Uh) Yl(aS bJ cV Hu) Bo(Si Uw Tl) Wh(Jd Mq) Uh(Nk Vs) aS(Lt Ry) hB(Si Vc) AjVw GdPj GnQl WcUn TlbM} Du{Lx(aC aF aO Ar bE bJ bW cV Cw Lv Mj Rg Up Vp) Po(aF Ax Bn Bo Dd hB Jn Kd Ny Ry Uv) Ar(Cp Cu Hv Jn Mi Qe) Cs(Ap bJ Kc Kd Om) Fp(aW Bb Nm Qc Vq) Ax(Jd Ji Mq Nq) Ny(Bn cX Qn) Vp(Is Jn Qe) Mq(Jn Mx) Ut(cH oE) EzMx HaQx MtbG fPgL} Wc{Cu(aZ Bo fP iO Ny Qb Uv Vt) Kd(Ar Ji Mt On St Un) Mq(aN aW Ch Dc Jm) Ny(bS Hv Ib Uh Vq) aZ(aF bJ Jh Mt Pd) Mr(Bn cX Rj Uh) On(aF Hc Jn Qw) Hv(Qb St Us) Ar(aW Jk) Ch(Ef Jh) Is(aO cV) Om(Aj Us) Uh(Hw Jn) Vq(Nu Un) BoOh LxPi MtfP JhUs PcgL aWhB} Is{jT(Hq Hr Hu hX Ik jH Jj JK Jm Jo Mg Mu My Ng Ni Nk Of Oy Pb Pz) nL(Jj mF Of Oy Pb) Sj(hB Nc Nl oE) nC(Jj mF Of Pb) nH(Jj mF Of Oy) Ti(bM Bo Uv) Jo(nN nT) Vw(Uv Vs) BnYl DeRv EtjO LzlX MkjK MqnK HuqY JqTl NxnM OpaN} nN{Qc(Fp Ik It Jj Jo Jr Me Mq mS Nh Ni Of Oy Pa) Nh(Hr Ii Jj Jo kP mF Nm Of Og Oi Oy) kP(cK dM It Jr Lz Mu) aZ(aM aP cH cX nK) Fp(Fr mF Pb) Jo(It Jn Qe) Nu(oO oP) Lz(kN lX) Jr(In Nx) cH(aC bJ) IiJn IlJj aGcX dEkC} Uz{Mq(aN aW bL Ch cX Jm Nu Pa Uv) Bo(Ir Jn Oh On Pz Qe) bJ(aZ Lx Ny Qb St Uh) Ar(aF aW Hu Jg Jk) Bn(Jn Nv Ny On Qe) Mt(cV Gl Pb Us Vs) St(aF aW bG cV) hB(aF aN cX) Us(Jh Ut) NuQx QlaW NvcV OfOn aFaZ} Ti{Bo(Ax Cs Ha Hv Ir Jn Kd Mx Ny Qe Rm St Tv Tz Up Vt) Ny(aM aN bE bG bJ gL hB Ki Mt Nu Ur Vo) Jn(hB Us Uv Vz) Fp(aN Jm Kd) Uv(Jr On Ut) Mt(Aj Dg) bM(Oh Qe) hB(Il Qh) ChNq FaaN StKi} Uw{Ch(aF Co Ef Ez Jd Jh Kg Mg Mi Mq Mt Nq Pd Qz Uf Ut) Bo(cV Ha Il Ir Kd Oh Vq) aZ(aF aN bJ Bn Nu) Ny(Bn Dk Vp) Fp(aN Jm) Gl(Cu Ji) AjHu BnQb NuUh MqJn MtaX OhaN PbgL aHcV bQfP} Rv{Jn(fP gP iP Ki Oh Rj Vq) Mq(Al aW Il Jm Pa) Mx(Bn Hu Jh On) Qx(Il Jk Jm Ny) Ir(aN Up Us) Ny(Lz Mh Oh) gL(Dd fP Qb) Gl(Ji On) Lx(Jm Nx) Qe(aN Us) Nv(Lz Mh) NiQb HuOh KdbJ OnUs PiaN} jK{dM(bA bC bF bG bL bQ bW cE cG cL cO cT cV cW dG dH dN hA iC jM lO) Jr(Fr Hu jG Jk jT Lu My) Mz(Hq Hu jG Mn Of) Hq(Ny Pg) Hu(Ny Pg) jO(Ji Jq) MrjG IlJj IrjT} Hl{Qe(aN aW Bn cX dK Mt Oe Qn Rg Us Vp Vq) Vq(Ax Kd Mx Nu Ny) aW(Ax Cu Hx It Ny) Bo(Jn Lx Oh) Il(hB Kz Mq) aF(aZ Ir Mx) Jm(Kz Mq) Kd(hB It) ApNy MiSt MxbJ UhfR} Si{fR(Aj aW aX Ch Mh Mx Oi Pb Qb Uh) Ch(Ef hB Mq Nq Qz Uf) Nu(cH Nv Pb St) gL(aH bM cX fP) hB(aF De Il Ny) Uv(bQ Lx On) bM(aP oF) AxBo CuGl FpaN NiNy JlUs KjUt} Nu{oP(Iq mU Nv Oh On Pz) Vq(Gd Gh Vb Vw Yl) oO(Hw It Pa Qe) Gh(aH Nv) Ir(kP Lt) Qb(nC nH) Ry(aZ Et) Vb(Cw Dc) Vt(Lt Zx) CuVw EmUh MqWh TlOi YlPc VhaZ} Vz{aW(Ax Cu Fp It Ji Jn Mj Mx) Lx(Bn Hu Jg Rg) Mt(cH kR Kz) Mk(Il Kd) Mq(bM Dd) Ir(aN Us) Jn(Oe Qn) DpKd MhJg HuOh IliA QeaN UnhB} Qc{Aa(It Jj Lz Mq Mr Nk Of Og Oy) nC(Fp Jj Lz mF Mq Pa) Mq(kP nB nH nK) nL(Jj Lx Lz mF) Jj(kP nH) EtjO FpnH LzlX NfnB} Mt{Gh(aE aH bO Hc) Pb(Op Uh Wg Zx) Uv(eM Lt Wg) Vb(Dd Hw It) Gd(kR Vq) Zx(aX Pc) hX(jT Mk) DpEx ItVw JmTm TlbM YlPc} Sj{oE(bQ cE Hu Iz Kd Nv Om Ut) Cw(Ny St) Oh(aE bM) aW(hC Ny) bQ(cH Vt) LxcE StOe OmUs UhhB PcgL} Vb{Cu(aF aN bJ Bn Nx Us) It(Kd Mi Om Pd) aN(Hw Mi Po) Ch(Jd Ut) Jh(Ax De) HwgL StPd NyaW OnaF} jT{Qb(jH Jl Jj Jq Jr Lv Lw Md Mz) Jr(Et hV Jk Mu My Nc) Jj(Il Qe) JijO aXjl bCdM} Yl{gL(cX fP Il Vq) aN(Oh Qe Vt) aW(aZ It Or) Jn(bJ Bn) cV(bQ Il) ArJk ChJd CuNx MxbJ QebM aFaZ} Wg{Bn(Jl Jn Nv Ny On Qe) Bo(Ir Jn Lx Qe) bJ(aZ Lx Ny) Pb(gL Nv) StcV JnRj OfOn aFaZ} Kd{Gd(It Ql Vq) Gn(Fp Nf St) Tl(Jh Mv On) Lt(Ar Jj Jy) Vc(Bo Cs Fp) AjVw NqeM ZxhC} Mq{nK(Jn kC kN) Al(Sf Wh) Ch(Ry Vw) Pb(mI Ry) GdJg MxTl IrLt SfJm NxkN mFmI} Uh{fR(aF cX Gh Ly Ry Ul) Nk(It Jn Jr) Ra(Fb Ne) Vs(Fy It) LwPb RybJ} Vq{Bo(EM Vh) Gd(gL hB Qw) hB(Gh Vc) AjWh EmUs LzOp JjLt JnVh RyUr aZfR} Vw{Ch(Jd Nq Om Ut) Qb(bM dI Pc) Gl(Lx Oh) LxUv MxPc QeVs NyVp VtcX} Et{It(Jj Nd Ng Oe Of Og Pb) eP(cZ Nc Nk) Jr(iC jO) IrOe} Lt{Ir(aS bJ Bo dI Hu Jd Ni) Vt(aN bJ) aW(Mr Un) ArBb MxbJ} aZ{nK(aM aN aS cX) Ry(bJ Ez Pd) TlaF UfeM VhbJ aMnL aPkP cHnU} On{Nx(kC kN kP lX nA) Zx(cX Gl Ki Oe) GhbM OpUs} Vc{gL(cX fP oE) hB(Bb Hv Mi) Bo(Fy Hw) DeJh OhdI} Gh{Qe(bM hB hG) aH(Hw Jh) ChNq PobM NiNy dRfR} Lz{lX(Jk nC Nv Qe) nC(kN kO nD) DdOp mIkN} Wh{Ch(Ef Jh) ArJk BnNy CsHu MxUr HcJn JhoE PcgL} Vh{Bo(Ha Oh) Ch(Jd Mu) aN(Fp Hx) AjHu CwNy MxbJ} Aa{It(Jj Oy Pb) eC(Fb Ki Rf) NkQe QbJj} Gd{Il(Jd Ql) NmQw IcNv IdaW OmkR UsUt} Ry{bJ(Lx Mx Tz) Bo(Ir Oh) RmUr fPgL} nL{Lh(Nx Pb) Oh(Me nD) mF(Ir Qe) LxnD} Sf{Ny(Bn cX Oe Vp) PoUv StOe} dM{bB(hA iC) bC(jQ jR) cZ(hA iC)} eP{Mg(Bg Ch) Mk(As Ne) CuPa NqbL} Zx{Nv(cX Oe) ChJh LxHu OmPb} fR{Tz(aW cX) Ir(Ne Nl) JmKz} kP{Jn(In mU) Oh(mE Nx) ItPa} Gn{Ha(Mi Qx) Hv(St Us)} Qb{mF(nC nH) PbmI jHqY} Tl{ChMu LxbJ QxJk UnaW} Nk{Jr(jQ jR) JijO} eM{BnUt CuUs NqUl} Lx{NxkN nTlX} Il{FpmI JiOg} Qe{mF(nC nH)} Ny{EmPj PbmI} aN{kI(nH nK)} ExUneC JhJqjO LhNxnC aPbMnK

Constrained panels with 2 analytes, where *1.0E-8 >= 'AUC p-value' > 0. Contains 1,026 panels of 114,549 total panels evaluated.* : Va(Ao Ba Cu Cw Dc Ed Et Fw Gb Gc Ha Hb Hp Ih Ii Ij Ir Is It Iu Iv Jg Jh Ji Jk Jl Jn Js Jt Ke Ko Kq Li Lj Lx Mt Mw Nb Nh No Nr Nt Nu Nv Nw Ny Oa Oh Om On Ow Pe Pf Pj Ps Pz Qa Qb Qc Qd Qe Qy Rm Si Sr St Tz Uc Un Ut Vi Vq Vt Xa) Vi(AF Aj aO Ar aW aY bF BG bJ Bn Bo cE CH cV Dk Ed Eq Fw Gc Gh Hc Hq Ih Im Iv Ji Jl Kd Ke Kz Ld Li Lj Lz Mh Mi Ml Mq Mx My Nn Nx Oa Of Og Ow Oz Pj Po Qb Qw Qx Rt Rx Sh Sr Tn Uh Ur Us Uu Uv Vo Vp Vt Wf Yd) Ij(AA Et Fc Fp Fr Hb Hl Hr Hu Ih Ik Ip Iq Is It Iv Jg Ji Jj Jn Jp Js Jt Li Lj Lx Lz Mi Mm Mp Ms Mw My Mz Nc Nd nI Nn No Ns Nt Nw Oe Of Og Ok On Ou Ow Oy Oz Pb Pc Pf Qc Qd Rt Sh Uh Ur Uu Vs Wb Wc We Xa) Im(AA Eq Et Hb Hu Ih Ip Iq Ir Is It Iv Ji Jj Jn Jq Jr Js Jt kC Ke kI kP Li Lj lX Lz mF Ml Mw MZ nA Nc Ng nI NN No Ns nT Nw Oe Og Ok On Ou Ow Oy Oz Pb Pc Qc Qd Sh Ye) Ps(aA AF aN aO Ar aW Ax aY Ch Cs cV CX Ed Fc Fw gL Hu Iv Kd Ki Kl Kx Ld Lj Lz Mh Mi Ml Mq Mw Nn Nu Oe Oi Oz Pf Qn Qw Qx Qy Rc Ru Rx Sh Uh Ur Us Uu Vo Vs Vt Yd) Nw(AA aW bN Ed Et Fc Hu Ih Ip Ir Is It Iv Ji Jj jK Jn Js Jt Jv Li Lj Lp Mh Ms Mw My Nc No Ns Oe Of Og Oy Oz Pb Pc Qa Qy Ru Rx Uh Ul Uu Yd Xa) Li(AA Du Eq Et Fc Hb Hu Ih Ik Ip Ir Is It Iv Ji Jj Jn Jq Js Jt kG kN kP Lp Lw lX Mw mZ Nd nI No Ns Oe Og Oy Oz Pb Uh Vs Wb Yd) Et(aA Fp Ih Il Ip Ir Is It Iv Ji Jj Jm Jn Js Lj Lz Mw My Mz Nc Nd No Ns Oe Of Og Oy Oz Pb Pe Qa Qb Qc Qd Qe Uu Yd) Ke(aA aE AF aW bN cH De eC fP Gl Il Jm Jv Kn Lh Mp Ne Nk Nl Nx oE Pb Qc Qy Rh Rt Ru Rx Uh Up Us Uu Uv Vp Vs Yd) No(Aa Hb Ih Ip Ir It Ji Jj jK Jn Js kP Lj lX Mw nI Ns Oe Og Ou Ow Oy Oz Pb Qb Qc Rx Rz Uh Ur Uu Wd Wf Zw Ti Th) nI(aA Fp Ih Ir Is Iv Jn Js Lj mI Mt mU Mw Mz Nb nC nH nK nL NN Nq Nr nT nU Oh Oz Pe Pf Qa Qb Qc Qd Qe) Aa(Fp Fr Ih Ip Iq Ir It Iv Jj Jn Js Lx Lz Md Mj Mq Mr Mt Mu Mw Nc Nn Og Oy Oz Pb Pc Pf Qa Qb Qc Qd Qe) Uh(aA As bN Dr Hw In Ir Is It Jn Jr Js Kq Ml Mt Na Nf Ni Nr Nt Nu Ny Pe Qa Ra Rf Sr Tv Up Ur) Lj(aA Fc Fi Gb Ho Ih Ip Ir Is It Jg Ji Jn Jp Js Jt Ma Mm Mw Og Ok On Qd Uw Vw Wb Wd Xa Ti) Mw(aA Eq Ih Ip Ir It Ji Jj Jn mI MZ Ny Of Og Oy Oz Pb Pf Qd Ru Sh Wf Yd Ye) Sh(Fw Ih Is Iz Jh Jn Jv Kq Mt Nb Nn Nv Ny Om On Ow Pf Qd Qy Rm Sr Ut) Ji(aA De Hr Ih Ip Ir It Jj Jn jO Jt Md Ms My Ns Nu Nx Of Og Oz Pb Yd) Xa(aM Ar aY Bo cV Cx Ed Fc Fw Iv Jj Ld Mt Nn Oh Oz Pf Rt Rx Sr Vs Vt) Pe(Fc Ha Hr kC kN kP lX mF MZ nA nD nN Ns Of Og Oz Pb Pd Rx Yd Zw) Rt(Cu Dc Ho Ir Is Iv Jn Js Jt Kq Nb Nr Ny On Qa Qe Sr) Yd(Gc Is Jh Kq Lx Mt Nn Nv Om On Ow Qa Qd Qe Sr Ut) Rx(Ih Ir Is It Jl Jn Js Nb Ny Oa On Qa Qd Qe Rm Sr) Pf(Hp Ih It kN kP lX Nd nL Ns Og Pb Pd Rv Wb) Mz(Hr Hx Ih It jK Jr Lw Lz Md Ns Og Oz Pb) Fc(Cs Ih Is Jn Js Lx Nb Ny Oa Oh Po Qa) Ir(aA Ip It Jj Jp

Figure 38 Continued

Ma Nk Oe Og Oy Oz Pb) Qd(It Jj jK jQ jT mZ nL Oz Pb Ru) Js(jE Jj jK jQ jT jY Oe Og Pb Wc) Ed(Dr Gb Gc Ru Si Uw Wd Zw Ti) Wf(Jh Jn Kq Mr Nb Ny On Qa Ut) It(aA Fr Jj Lx Mn Nd Og Ok) Ru(Fp Fw Iv Kq Mr Mv Qe Un) Nn(Eq Fd Lp mZ Uz Vc Wb) Qa(Hr lX mF mZ Og Pb Zw) Dr(Kd Oa Ow Rm Sr Vt) Iv(mZ nK Og Vb Ti Th) Lp(Ar hB Ld Mq Ql Ur) Ih(Jj kP Og Oz Ye) Is(jK jT nL Og Wb) Wb(Lx Mt Oh Ow) Kq(Aj bN Uu Ux) Ld(Fd Fi Ho Uy) Oa(Gc Rz Wd Ti) aA(Ip jK Oz Ti) nN(Fp Ml Nh Qc) mZ(cO Mq Mt Qe) Eq(Mt Nt Qy) Nb(Hl Tl Ti) Sr(bN Gd Uu) Jn(Jj kP Og) Ny(jK Og Rz) On(Oe Og Oz) Jr(jK jT) Ow(Hp Sj) Uu(Gc Jg) bN(Un Vt) ThFp FdMq FihB NtHb LxZw LznC MxWd HrOk IIYl QbVw QeOu WeOm JqjO OhkP dMjK

Constrained panels with 2 analytes, where 1.0E-7 >= 'AUC p-value' > 1.0E-8. Contains 417 panels of 114,549 total panels evaluated. : Uh(Ad aE bA Bn cH Cp Cq Cs cT Cu Cw Dc Dd Et Fy Hv Hx Id Im Iv Ji Jq Kd Kn Kp Kr Ld Lw Me Mi Mw Mz Nb Nm oE Ok Om Pb Pi Pk Rb Ri Rj Uc Ud Ul Us Uu Vp) Lj(Fr Iq Jj Jq Lh Lw Lx Mg Mi Mn Mp Mt Mz Nb Nd Nm Nn Nq Nt Nv Ny Oe Oz Pb Pf Pg Qa Qc) Mw(Bb Bg Ch Fp Hu Is Js Lx Lz Mh Mn Nc Ns Oe Ok Ou Pe Qa Qb Qc Qe) Va(aA Ar Dd Ef Fp Hx Jm Ld Lh Mv Nm Ql Qm Uf Vh) It(Fc Ih Jp Js Jt Nv Ny On Oz Pb Pg Qa Qc Qe) Ij(Aj bN Hc Jq Jr Jv Ld Lw Ly Nm Qa Qb Qw) Js(aA Fr Ip jD Jg Ma Mm Of Oz Qd Qy Ur Yd) Xa(aW Hx Kd Mq Oi On Pb Pc Qe Qy Sh St Un) Pf(Gb Ik Ip Jn Lw Mn Mz Oe Oy Oz Pc Qc Qe) Og(Fr Ip Jg Jt Lx Ok Om Pg Qb Qc Qd Qe) Is(Hr Ji Jt Mz nC nH nK No Oz Pb Qc) Kq(Bg bL Ch Iz Ng Of Ou Oy Pb Ss Vs) Ih(aA Hb Jg Mn mZ Nu Ny Oy Pb Qd) Ir(Jt kP Mn Mp Nm Nn Ns Ok On Wf) Jj(Ip Jg Jm Jt Ny Ok On Qa Qb Qe) Qd(Ik Ip Jn nK Oe Ok Oy qY Ye) Ji(bN Jq Nm Oe Oy Qy Ru Us Uu) Mz(Lx Mi My Nu Ny Of Oy Pa) Nw(aF bO cH cX jH Ra Rg Sr) aA(Hb Jn kP nK Ny Qc Ry Si) Qa(Hb kP nK Oe Ou Oz Vs) Pb(Fr Jn Jt Ny Ok On Qe) Pe(Hb Lw Mn Oe Oy Uu Vs) No(Iv Jt Ki oN Qy Vs) Ke(dK Dr Kf Nj oN Ou) Ru(Hv Jd Jl Ld Nq Vt) Wb(Ar hB Ld Ml Mq) Ps(aM Mk Pc Qv Sj) Rx(Ax Cu Ha Jh Mr) nl(Jl Jr Mq Nu oQ) Aj(Im Jg Jt Sr) Hb(bN Fw Nn Sr) Yd(Jl Ld Pj Vq) Jn(jK nN Oz Ti) Li(bO kF Qy Rf) On(My Of Oy Qc) Et(De Jq Jt) Qb(Jg nH Ok) Lp(Jd Mv Ow) Rt(Cp Kd Mi) nN(aZ cH cX) mZ(Ma Mr Mv) nC(Iv Ml Qc) Eq(Om Rz) Fc(Ax Fp) Nn(Gb Uy) Ho(Ar hB) Qe(Hl Oz) Ok(Oe Oz) jK(Lw Pg) AaUu AfUw TiFp NrkP NtSh LxlX MljV MqUy IvmI SiiZ QcRf WfOm OhnL aZnK Constrained panels with 2 analytes, where 1.0E-6 >= 'AUC p-value' > 1.0E-7. Contains 612 panels of 114,549 total panels evaluated. : It(Bb Fp Ip Iq Is Jg Jn Lw Lz Ma Mi Mr Mt Mx Nb Nn Nq Nr Ns Nu Oh Pa Pe Po Qb Sh) Uh(aM dK fR Fw Ih Il Jj Jo Jt Kg Lj Mj Oh Pd Pf Pg Qd Qe Qy Ru Un Ut Va Vs Vt Xa) Mw(Aj cH Fr Iq Iv Jg Jp Jq Jr Jt Ld Lw mF Mi Mr Ms Mt Mx nK NN Nr Nt On Pa) Pf(Eq Hb Hv Iq Is Iv Jj Jq Jr Lz Ml Mp Mr mZ Nc nK nN Nr nT Ny Pe Qb Yd) Ih(Fi Fp Fr Ip Is jK Jn Jp Js Lh Lx Ma Mm nC Nk Nn Oe Ok On Qa Qc) aA(Bb Fr Gc Ho Jg Jm JT Ma Mn Nm No Nr Nu Og Pb Pj Qa Qb Qd Wd) Jn(Fp Fr Ip Jp Js Lx Ma Mm Mn Mz Nc Nd Ny Oe Ok On Qa Qc Qe) Va(aE Dk Dl Dr Hu Ic Il Iz Kf Kk Mg Mq Mr Ok Ou Pg Po Rf Uw) Mz(Hb Hw Ip Iq Iv Jj Mh Mn Mp Mr Nb Nc Nr Oe Qc Ur Us) Ij(Bb bO cB Ch Ct De Fb Gl Iz Ki Kl kP lX nC Ng nL Us) Qd(Dc Fc Is Jg Jp Jt lX Ma Mn Nm NN Ns Nt On Rf Xa) Lj(Ii Iv Jh Jo Jr Mr Nc Ns Nu Oh Om Pa Pc Pe Qb Qy) Ip(Fp Fr Is Jg Lx Lz Ma Mn Ny Ok On Oz Pb Qa Qb) Js(Bb Hb Is Jp Jt Ld Nm Ns Nt Ok On Oy Sh Us Vs) nI(aP aZ Hw Lx Ml mP Mr Mv Mx nB Nh Nw On Pb) Pe(Iq Jj jK Jr Lx Mm Mp Nc oN Ou Pc Qy Ur) Im(Bb bN bO dB De jK Ki Ld Rf Ur Uu Vs) Sr(Aa aE cH dJ Et In Jj Oe Ou Pb Qy Ur) Kq(aY dN Dr Ef Hb Hc Hq Kl Li Lu Nw Uv) Og(Fp Ii Il Iq Jl Mi Mn Nn Nr Nu Nv Po) Qc(Fr Jg Jj jK kG Ma Mn nL Nt Ny Ok) Is(Ir Jg Jj Ma Mn Ny Oe Of Ok Uu) Qb(Fr Ho Jp Jt Ma Nm On Oz Pb Wd) Xa(Af bG cU Nu Nx Ql Rj Ru Uu Vq) Et(Aj Bb bO cB Ch Hb Kl Lp Rf) Lx(Hq Jj kP nL Ns Ny Oe Oz Pb) Ok(Fp Lz Mn Nr Ny Of Oy Qa Rx) On(Eq Fp Hu Lz Ms mZ Ng Ns Uu) Qe(jK jT mF nN Ns Oe Oy Ur) Nw(Cu De dH Kd Kz oE Ou Qw) Oz(Fr Gc Iv Jp mI nC nN Pg) Qa(Jg Jp Jt Ma Nk Ns Oy) Jj(Bb Fr Ii jK Mn Nm Nr) Sh(Gc Hu Jg Jk St Vq) Ji(bO Fc jT Rx Uv Vs) Li(Dp Kd mW Tv Ur Vt) Ny(De Mn Mt Nd Ns Oe) Pb(Fp Jg Jp Mn Nn Pg) jK(Ir Jq Mr Mt Nb Nm) Bb(Aj bN Ml No Ur) Dr(Ps Qy Ru Ut Vq) Lz(Fd kP lX Mn nH) Hb(Ed Il Ld Qy Ut) Iv(kP Nd nH nL nN) Yd(Cu Jd Nq Ou Un) St(Fc Gc Ho Ru Rx) Rt(Dd Fy Ha Pi Tn) Aa(Ax bN Cx Rf) Eq(Mq Pd Uf) Fp(Jt Nd Ps) Nu(Fi Lp Uz) Wb(aP Po Qx) Wf(Nr Nv Vt) Ke(dJ Ph Rg) Rx(Cs Fy Un) Ru(Hx Jh Po) Oh(Gb Ho nC) mZ(bZ nN Nq) iZ(bN Gc Ti) Ar(Fd Uz) Cx(Fd Gb) Fr(Oe Oy) Nn(lX Wc) No(Kl Ss) Qy(Rf Ux) Ur(Dc Ir) Uy(hB Ql) jT(jI Jq) BoHo ChUt FcTz FwOu GhLd GcQw NqLp NsPg JgOe JhYe JmN KdbN UuPj Constrained panels with 2 analytes, where 1.0E-5 >= 'AUC p-value' > 1.0E-6. Contains 862 panels of 114,549 total panels evaluated. : Qe(aA Bb bN Fp Fr Hb Ip Iq Iv Jg Jp Jq Jr Jt Lw Lx Lz Ma Mi Mm Mn Mp Mr Mz nC nH nL Nm Nn Nt Nu Ny Ok Pc Pe Qy Rf Uu) Hb(cH dK Ez Fy Ir Is Iv Ji Jj Jl Jv Jy Kz Lj Mi Ml Mq Mt Mw Na Ni Nr Oa OE Pd Qd Ra Rf Ru Ul Un Vt) Is(aA Bb Fp Fr Jn Jp Jv kP Ld LX ml Mm mZ Nm nN Nr Nt Nu On Ou Oy Pc Qa Qb Qy Ur Uv Vs) aA(Fp Ii Io Iq Kq Lh Lw Lx Lz Me ml Mm Mz nL NN Ns Nt Oe Ok On Oy Pc Pf Pz Ru Xa) Kq(aF bG cH cV De Fr Gp Ij Jj Jo Kj Lj My Ne Nk Nv Nx oN Ow Qb Qc Qw Rf Ur Vo) Va(Ad aH aP Cp Cs Fi Fy Ho iZ Jp Jq Kd Kp Ks Kz Mi Mk Mp Mx Na Oz Pc Pd Tn Ua) Mn(Fp Fr Iq Iv Jq Lx Ma Mi Mr Ms Mt Nb Nd Nr Ns Nt Nu Oe Oy Oz Pc Po Qa Qb) Qc(Bb bN Fp Ip Jl Jp Jt Ld Lx Mm mZ nH Nm Nn nT Nv Pa Pb Pe Pg Po Qb Sr) Qb(Bb Fp Gb jK Jn ml Mm Ms Mz nC nL Nn Nt Nu Ny Oe Oy Qy Rz Wb Ti) Oz(Fp Hp Iq Jg Jt Mt mU mZ Nb nH Nn Nr nU Nv Ny Og Pa Po Uw Vw Wd) Li(Aj Bb bN cX Dc De Dr fP jK Jy Ki Kl oN Qn Rg Sr Us Vu) Et(aF Bg bN cV Dg Ed Gl iZ jO Ki Ld Oa Pk Ry Sh Ss Wb) Jj(Fp Il Io Iq Jp jT Lh Ma Mt Nn Nt Nv Pg Po Pz qY Vq) Ny(Fp Fr Ib Iq Iv Jr IK Lw Lz Mi Mp Mr Nc Oh Pa Pe Qa) Og(Hw Jh Jk Jp Jr Lh Ma Mp Mr Mt Mv Mx Nb Nm Nq Nt Pa) Mw(bN Cv Gc Gp Jl Ki Lh lX mM Mp Nm Oa Pc Sr Uu Vt) Mz(Fp Fr Gp Hv Io Jg Jt Ld Ma Mt Ok Pc Pz Qy Rx Uu) Pb(Iq Iv Jr Lh Ma ml Mr Mt Nb Nm Nr Nt Nv Om Pa Po) Pe(Bb bN Fb Fr Ih Ip Jg Jq Nr Oh Ow pF Pj Rf Rg) Lx(Iq Iv Jg Jr Jt kN Lw Mi Mr NC Of Ok Oy) Sr(aK aQ aU Ch Gp Jq Ki kS Ld Nk oN Ow Pj Rf) Fp(Fr Ik Jg Jp Ma ml mZ Nc Nm Nv Pf Pg Uy) Lz(Fi Gb Ih Jg Jp Jt kN ml nI nL nN Nv Pg) Ip(Jp Jt Mt Mx Nc Nm Nn Nq Nr Nt Nu Pc Po) It(Iv Jl Jq Jr Lh Mm Mp Nm nN Nt Om Pc Uy) Ji(aY Bb bM cB cX Gl Ju Ld nC nI nL Ou Xa) Ij(aF aW aY Bg cV Ef Ju Kj mZ nH oN Vt) Qa(Bb Iv jK jT Mi Nm Nn Nt On Ow Qy Rf) Qd(Bb bN Iv Jq kP Ld mF Mi Ou Uu Vs Ti) Ok(Fr Iv Jq Mp Ms Nc Nd Ns On Pc Pf Rt) Ih(bN Iq Jq Jt Mi nH nK nL Nm Nt Po) Jt(Hr jK Jn Jo Ng Oe Of On Oy Rx) Ut(Aj bL bN cH De Eq Lj Ou Ur Uu) Pf(Jp Lh Mm Mt Nm Nt Nv Om Uu Zx) Bb(Ax Cs Lj Nb Ne Nj Nk Rf Uu) Fr(Hu Iv Jr Mi Mx Nc Ng Ns Of) Uh(cX Fb Hp iZ Kj Ko Nk Nn Ou) Qy(CH Cs Ir Jq Ru Yd Ye) Xa(Ch Hv Il Kl Mh Po Qx Ul) Ur(Fy Il Iq Nt On Pg Qh Vq) No(bN bO cX De eC mZ nK) Mq(ml nC nH nL Ru Uz Wf) Im(aU cH Dr Fb iP Jv Qw) Sh(Cu Ir Jl Ju Ko Mv Sf) Jn(Jg mZ Nm Nn Ns Nu Po) Js(bN Dp Iv Lw Nn Ou Pj) Ld(Gc Gp Hp Ir Uz Wf Ye) Uu(Ir Nt Om Pg Si Uc Uw) Eq(Co gL Jd Jh Mg Nv) Yd(Jp Lh Si Tn Uw Vt) Ru(Ar aZ iZ Nh Nu Vq) Pg(hA Lw Mx Nu Of Oy) nN(kI Mb Me Mt Nu Oy) nI(aM bB cH cX mF Nt) Fc(aZ Hx Jl Jr Rm) Ml(Fd Hp jT jU nH) Jg(Iv Ng Ns Of Oy) Oe(Mt Nn Nr Nv Rf) mZ(Mi Mp Nr Nt Pd) Aa(cX Ed Fy Ow) Gb(Ar Bo Qx St) Ho(Cx iZ Kj Nu) Lp(aM Bo cO Rt) aZ(nL Uw Wd Ti) bN(Id Ko Rf Tz) jK(Iq Md Oh Pc) Fd(hB Nu Qx) Fw(Lu Nk Rf) Gp(Rf Un Vt) Ir(Lt Ou Ry) Wf(aM Cu Un) Ke(bG St Vu) Rt(Hv Kn Mr) Nw(Fb oN Pi) Aj(Ad Nm) Ar(Hp Wc) Dr(dR St) Ti(Bo Mt) Fi(Cs Qx) Nn(mM Oy) Nk(Qh Vt) Iv(Hr On) Si(aP fR) Rx(Ii Na) Om(De Gd) Ou(On Vt) Uy(Jh Mv) nK(aH aN) kP(Nb Nt) CuWc CxUz DuPo EdPj GcQv NrOy LvjT MaMx MtNd WbKk JyLj LhnL OhlX VcaP nTmF

Figure 38 Continued

Constrained panels with 2 analytes, where 1.0E-4 >= 'AUC p-value' > 1.0E-5. Contains 1,204 panels of 114,549 total panels evaluated. : Hb(Ad aE aM As Bn Cp Cq Cs Cu Cw Dc Dd Fb Fp gL Hv Hw Id In Ip It iZ Jn Jq Jr Jt Kd Kg Ki Kn Kp Kr Kx Lw Mj Mr Mu Mx Nb Nf Nm Nu Ny Oh Om Pb Pg Pi Pk Qb Rh Rj Tv Uc Uf Up Ur Us Uu Vp Vs Wm) Qc(aE bM cX Dc Dd Hw Ii In Iq Iv Jq Jy Ki kP Lh Lz Mi Mp Mr Mt Mx NB Nd Nq Nr Ns Nu Oe Om Ou Oz Qy Un Ur Ut) Rf(aA aE aK aQ aU cH cY dJ dK Ed Fi Il Ir Is Jj Js Kz Mi Mt Mw Mz Ne Nm Nt Pf Pj Qb Qn Rx Tz Uf Un Ur Ut Vt) Fp(Ho Io Iq Iv Jl Jq Jr Lw Lx Ly Lz Mi Mm MP Mt Nb nC Nn Ns NT Nu Oh Om Pa Pc Pe Pj Pz Qy) Qb(bN Fc Hv Iq Iv Jo Jq Jr jT Jv Ld Lh lM Lw Lx Lz Mi Mp Mr nK nN Ns nT Oh Pc Pe Pj Rg Ru Ur Xa) Nr(Iq Iv Jg Jp Jr Ld Lw Ma Mi Mm Mp Mr Mt Nb NC Nd Ns NT Nu Oh Pa Qy Sh Ur Uu Vs Vt) Oz(Fc Fd Fi Ho Ii Il Jh Jj Jl Jq Jr Lh Lz Ma Mi Mm Mp Mr Mx Nd nL Nm Nq Nt Nu Om Si Vq Wb) Va(aF aG aM Ap Bb bJ cC Co gL hB Hv Id Jd Jr Kn Kx Lp Mf Mz Nf Of Pi Qg Qh Ry Vs Vw Wb) Jg(Eq Hu Ik Iq Jp Jq Jr Lw Mh Mi Mn Mp Mx My Nc Nd Nn Nt Ny Oh Ok Pf Po Ur) Bb(aH Bg bV Ch Cu cX Dc Dp Ed Ih Ir Iv Jn Jq Jr Jt Ly Nq Oe Oi Ow Tz Uh) Ma(In Iq Iv Jp Jq Jr Jt kP Lx Lz Mh Mi Mt Nc Nd Ns Nu Oe Ok Oy Pe Pf Po) Sh(bQ Co Cp Cw Dd Dk Ef Hq Hw Ii Ji Jt Kd Ks Mn Mx Ok Pg Ph Pz Qh Si Tn) Ut(Aa AF Bg Cs Fw Hc Iz Jj Ki Ld My Ne Ng Oc Oi Oy Pb Qw Us Uv Vs Ti) Qy(Aa Ar Ax Du Fw Ih iZ Jj Kx Ld Lp Ml Mw Ny Oa oE Pg Rv Un Uz Vt Wf) Jp(aA Fc Fr Iq Iu Iv Jm Jt Lx Mh Mn Mz Nn Ns Nt Ny Oe Ok Oy Pe Po Ti) Ur(aA Dd Fd Fw Ho Ih Ip Iv Jn Jq Jr Jt Kd Lj Mw Nb Pf Qa Qd Tz Vt Xa) bN(aA Dc Fw Fy Ir Is Jq Jt Kn Nb Ok Om On Or Pi Pj Qa Qh St Vs) Nn(Aj De Hu Is jK Jt Kl Lx mF My Mz Nc Ns Ny Of Ok Pc Pf Uu) Ip(Hv Iq Iv Jq Jr Lh Lw Mi Mm Mp Mr Nb Ns Nv Oe Oh Om Pa Pg) Jn(Iq Iv Jq Jr Lh Lw Lz Mi Mp Mr Ms nC nH nK nL Nt Pa Pc Pe) mZ(aA aW bQ cU Hw Ji Jr kG Ly Mg ml Mz Nb nC nT Nu Nv Oh Po) Jj(Fi Fw Iv Jk Jl Jo jR Ks Lp Mm Nc nN Nq Nu Om Pj Qh St) Og(Hv In Iu Jm Jq Lw Lz Mj Mm Mq Mu My Nc Nd Nx Pb Pz) Aa(aJ aW bR cB CU cV De eC Fw Kq Oa oE Qh Rh Uo) Gc(Af Aj Ch DR Fw gL Ha hB Lj Nc Ni Ny Ru Ry Ub) Nt(Dp Fr Ik Iq Lx Ly Mz Nc Nd Ne Ny Of Ou Vs Vt Yd) Qe(Aj aY bM bO cX De Fn Ld Lh lX Ow Pj qY Ra Us Vs) On(bO Ch De Hc Iq Iz Jq Jr Ki Kl Ld nL oN Qw Ss Vs) aA(aF aW cV cX De Iv lX mF Mg nC oE Po rB Sr Vh Th) Mn(Hv Hw Jl Jr Lh Lw Mh Mm Mp Mx Nm Nv Oh Om Pa) Mw(cT Cu Dc Dp Dr Hc Hv Id iZ Kd Qn Ra Tz Un) Mz(cH De Dp eC Jm Lh Mm Nm Nv Pj Po qY Tz Vt) Ml(Fb Fi Gb jH kG Kq lM ml mP mT nL Sr Xa) Ld(Dc Ed Fw Ih Il It Jq Jr Pf Pg Pk Qh Wc) Et(Cu Dr Fb Fc Fw Hp Kd Kq Tz Un Vt Th) Lp(bJ Cx gL Hx Ji Kx Mk Nf Ni Pf St Un) Nv(Hu Iv Jq Jr Mi My Ns Of Oy Pe Uu Ti) Mt(De hX Iq Iv Kd Ki lX mI Nc nK Ns Pe) Pf(bO Fd Ho Jl Jt mF oN Ou pF Po Ti) Pg(Hv hX Iq Jr Mm Nc OE oN Pc Pd) Pj(aE cH Cs Fw Il Ir Lj Na Oa Qa Qv) Fr(bO Hv Iq Jq Jt Lw Lz Mp Mr Nm) Sr(aF aY Im Js Jv Lj Qa Qd Tz Vt) Ny(Hv Hw Jq Jt Lh Mm Mx Nm Pc Uu) nN(aM Ih lj Ir Lj mF Mq No Of Pb) Dr(aW aY Fw hB Kc Nb Nw Wf Xa) Po(Io Iq lX Nd Ns Oe Of Oy Rx) Eq(Ap aW Ba bQ Ez Hu Nq Tn Vq) Uu(Cu Dc Ef Ko Nm Ok Qa Un Vq) Vt(eC Im Js Lj Lt Ne Pe Rx Wb) Ij(Ao cH eC lb jK ml nK nT) Kq(eC Im Na oE Tn Tz Us Vp) Rt(Ax Fd Ii In It Jr Om Tv) Pb(Ii Jk Jl Mi Mm Mp nU Wd) nL(aN cX Ir Js mF Nb No Nw) Aj(Js No Ok Om Tn Tr Uc) Lx(Hw Jq Lh Lz Mp Nm Pa) Wb(Ji Kx Lh Mk oE Om Ql) Jt(Ct Iv Mp Ms My Ns Ok) Ru(gL Ha Hq Kz Mp Ou Tz) cH(Fb Ji No nU Qd St Un) nT(Ih Is Iv Lj Nb Nw) jK(Hq Lz Mi Mj Mq Na) Fc(Lz Mh Mv Qx Uh) Hp(aW cU Lz Mh Qx) Ir(jT lX mF nC We) It(Hv kP nC nH Ye) Qa(bO Fb Jq qY Us) Ji(aW cV eC Ki Ow) St(aE Nk Oe Ou Wd) Wf(Hw Jd Tn Uw Xa) Js(bO eC Fb nC Qn) Of(Lh Nb Nm Om Xa) aZ(Fi Ho nU Ry Vq) ml(Ih kI Lj Nw Nx) De(Dc Jh Nb Pe) Gp(Id iZ No Pe) Nu(kP nC Nd Vq) Im(aK Kd Kl Tv) Is(Lw Ns Ow Us) Yd(cO Ql Rm Tz) Jr(Mr Nd Ns Rx) Li(cB dH Ou Tz) Uh(Rh Ry Uw Wg) nI(aW Il Mp Pa) oE(Fb Jq Qd Si) Cw(Rx Ux Vb) Nm(Mh Mx Ok) Ho(aH Cs Us) Ih(Iv kI Om) Jh(Gd Nd Oy) Wc(Cx Hv Kd) Ye(iZ Mq Mr) Lj(nC Ou Un) Oe(Ii Mm Om) Oh(kN nK Ti) Ar(aE We) Bo(Fd Uw) Th(Cs Kz) Gb(hB Mh) No(dH dR) Lz(jH Xa) Nk(Kd Oa) Iq(Oy Pc) Si(gL hB) Wd(Ax Ch) Rx(Dk Kn) Nw(jl nK) Uy(iZ Kd) Pe(aY bO) bQ(oN Sj) cX(mU Uw) kP(aP Mh) CoeP CxVh DcNl DpVq EdEx TiJl FdQl FwQn FyVs MiOk Mmll MqnK MrjR NfqY HrLh QdVp UfUx VbPd Constrained panels with 2 analytes, where 1.0E-3 >= 'AUC p-value' > 1.0E-4. Contains 1,701 panels of 114,549 total panels evaluated. : Pj(Aj aL aU Cu Dc dK dM Fb Fy Hv Ih Is It Iv iZ Jl Jn Jq Jr Kd Ki Kz Ld Lp Me Mr Mx Nb Nr Nt Nu Ny Oe oF Oh Oi On Ou Pf Pg Pi Pk Qc Qy Ra Sh Tn Tz Ul Un Up Ur Ut Vp Vt) Jj(Dc Ed Fb Fc Gc Ho Hv Hw In Iu Jh Jq Jr Ko Ld Lw Lz Mg Mi Mj Mp Mr Mv Mx My Nb nC Nd Ng Ns Oa Og Pa Pb Pk Rm Ru Ry Si Tn Tz Ua Uc Uf Un) bN(Ad Ar Bc Cs Cu Dd Ed Fb Fr Gp hB Jg Jn Jp Jr Jy Kf kl Kr Kz Ld Lj Lw Mn Mp MZ Nn Nq Ny Oa Pf Pg Ph Pk Qy Rb Rm Tn Tv Uc Up Us Vp) Gc(aH Ar aZ bM bQ cH cU Fc Fp fR hC Hx Iv Jl Kd Kk Ky Kz Lx Mr Nj Nq Nr Nu OE Oh Oi Oy Pc Pf PK Qa Qb Ra Rf Ri Tn Ut Uy Wb Wm) Qy(aA Aj bA BB Bg cT Dc Ed Em Fd Gp Ho Id Il It Iv Jr Kd Kz Lx Lz Mq Mt Na Nf Ng Nk Oe oF Oh Oi Ok Pf Pk Qh St Tz Uu Wc Yl) Ur(aE Ax cH Cp Cs Cu Ed Fb Gb Gp Ha Id Ii It iZ Jl Jm Ko Me Mr Na Nm Nn Nv Ny Oa Oh Ok Om Pi Rm Ry Si St Tn Ua Uc Ug Un Uw) Gp(aA cH Fb Fw Gb Ir Jy Kd Kn Ko Kr Kx Lu Mt Na Nb Nt Oa Pi Pk Qa Qe Qh Ra Rb Rj St Uc Up Ut Uw Vp) Aj(Ap Ba Bc Co Dc Dl Fb Fr Fw Fy Ih Ir Is Iz Ko Ma Mn Nb Nq On Pe Pf Qa Qh St Ua Uf Un Vq Wd) Ld(aA BB cH Cu Dr eC Fb Fp Fy Ip Iv Jf Jn Jp Kd Me Mt Mx Na Nb Nn Ny OE Oh Ok Pi St Tz) Qc(Ad bA cH Cp cT Cu Cv dR Ed Fb Fy Hv Id Jo Jr Kk Kn lM Lw Mg mP Nc Oa qY Tn Uf Uu Vt Wb) Pb(Fw Ho Id Il Io Jh Jm Jo Jq Lw Lz Mg Mh Mj mU Mv Mx mZ NC Nd nH Nq nT Nu Nx Oh Pz Un) Nn(Bg bO Ch eP Hv Iq Iv Jq Jr Jv Ki Lh Lz Mi Mr Ms Nm Nt oN oP Ou Ow Pe Qw Un Vs Vt) Jr(De Hr Io Iq Jp Lw Lz Mi Mm Mt mU Nb nC nK NT Nu Pa Po Ql Rf Ru St Us Wf Ti) St(aQ aU BB Cu Hv In It Iv Jn Kz Me Mi Ml Na Ne Ny oE Oi Ow Pi Ra Tz Uu) Vt(AA aW aY Bb Bc cH dK Dp Fb Fw Ih Il Is Ko Lp Ml Na Oh Ow Pf Qe Rh Ut) Mt(Bb Ed eP Jq Lh Lw Ly Lz Md Mi Mm Mp Mr Nb Nm Nt oE Of Om oP Ou Pa Qw) Uu(Ad Co Cp Fb Fr Gb Id Ih Ii Jp Jq Jt Lh Mn Nb Oh Qh Rm Tn Tz Ua Uf Vh) mZ(aP cS cX dE Fr Ir Jl Js Lj Lu Lx Lz Mj Ml mP Nf NH nL nR Nw Om Qb) Dr(Bb cU Cx gL Ih Is Jd Lp Lx Nd oF Oi Oz Pa Pc Pf Qa Qd Qe Qx Tz Um) Oe(Fb Fw Io Iv Jh Jk Jl Lh Nb Nm Nq Nt Nu Oa Pz Qh Qm Tz Un Uw Vq) Va(aW Ax bA bR Cq cT Cv Fd Hf In Iq Kg Me Mj Ml Ng Pa Qx Up Vp Tj) Wb(aH aM bB bQ Co Cs dR Ex Fr gL Hf Il Jd Ke Lz Mf oF Ru Uw Ti) Lj(Ad aE aH bO cX Dc Fb Kd KG mP mT nH nM nU Ow Qx Ra Tz Vp) Ou(aA Ar Ax Bb Ih It iZ Jp Mz Nb Nr Nv Ny Oa Oh Pg Pi Qb Sh Un) Uh(Du Em Fd Gb Gn Hl Ho Lp Rt Uz Vb Vh Wc Wd We Wf Wh Yd Yl Tl) Jq(aA aW Dc Il Io Jp Mm Mz Nd nL Nm Nr Nt Nu Po Qn Rf Rt Rx) Ru(aH aM Cp Cx Ex Gb hB Hu Hw Mi Mk Mz Pc Pg Pi Ql Uf Wd Tl) Om(bO eP Hu Iq Iv Lz Ms Mx My Nc Nd Nr Ns Nu oE Oy Qw Vs Yl) iZ(aE aH aK aL aZ BB Cx cY dK dR Ip Ji Mn Ne Nr Or Pf Pg) Ti(aH aP bB Fa Ha HB hC Hu Kz Me Mj Mr Mv nY Oz Qw Tz) Sh(Ad Ao Ba cE cU Dc Fr Ic Id Il Jd Jp Kf Lh Nh Ua Uc Uw) Wf(Bc Cp Dd Dk Hv Id Ii Jt Kk Lh Mj Mz Na Ok Pi Qx Vh Wd) nC(aN aZ bR cH cX kl Ly MF Mh ml Mr mS Mv No nT Nw Po) Ns(li Io Iq Iv Jh Jl Lh Mm Mp Nb Nd Nm Nq Nt Nu Og Oz) Yd(bB Cw Dk dR Ef Fr Jk Jt Kg Ko Mk Mn Mp Mz Na Pg Uf) oE(Bb cE Gb Ho Hp Id Jy Kd Kn Lp Ny Pf Qh Sj Ut Uw Uz) Mr(Fp Ii Jg Jp jQ Ma Mp Nb Nc nH Ni nL Of Oh Pa qY) aA(Ad aY bI cB cN Co Cx Dc dH dR Fb hG Ow qY Ue Ut) aZ(Gb Hl kG mE ml mP nH nT Rt Uz Vb Vh Vw Wc We Wg) De(Ad Cv Fr Ir Is It Jt Mn Nv Ok Pg Qa Tn Un Wd) Nm(Iq Iv Jl Jp Lz Ma Nc Nd Nr Nv Oy Pa Pe Pg Po) Nt(Fb Iv Lw lX Lz Ma Mi Mm oN Oy Po Qw Tz Un Us) Nu(Ii Iq Iv Jl kI Lh ml Mp Nb Nc nK Nq nT Oh Pe) cH(Ed Fw Fy ml Mn Oa On Pe Pf Pk Qh Qn Si Tz Vq) Ch(Ad Co Ef Ez Fr Jg Jh Jt Mn Qh Tn Ua Uf Uw) Ne(Ar Ax Bc Cp Cs Cu Dc Dd dF Fw Kd Oa Qh Un) Io(In Iq Lw Lz Mh ml Mp Mx Nb Nd Og Oz Pa Pe) Qb(Di Ez jH Jy kG Ko lK mP mT qY Ri Uf Un Ut) Rf(Cu Fc Hv Iv Jn Jt Kd Kg Ml Na Nk Oi Vp Wd) nK(aG aY bM cO cX Fp It Ji Js Lh Lx Nq On Po) Fb(Aa Cs dK Ed Fw Ih Ir Ji Mw Oi Ow Pf Qe) Nr(Hw Id Jl Kd Ki Kz Lh lX Lz ml Pc Pk Qn) Rx(bA Cp Cq Dc Fd Hp Hv Jg Kd Pg Pi Tz Vp) Oz(Hw Jk Jm Lw Mh Mj Mv Nc nT Oh Pz Ry Wh) Eq(aF cS Cw Ef FR Iz Jk Mu Qu Qz Wd) Jp(bG bO Ed Hv

Figure 38 Continued

Hw Lh Lw Mi Mp Mx Oh Pc) Ut(aY Dp Ed fP Hq Ih Jk Kl Ml Nk oN Ss) nH(cX Fp Ir Ji Js kl Lh Ly mI Mv Nq Nw) nL(aG bQ bR cO Ly Mh mI Mp Mv mY nM nT) kP(Iq Jt Lw Mg Mi Mp Mv On Pa Pc Pg Po) Lz(Ho Iq Is Iv Kd Nb nT Pc Pi Po Vw) Ma(Hv Hw Jl kN Lh Lw Mp Nb nI Of Pa) Mm(In Iq Iv Jl Mh Mi Mx Nc Nd Oy Po) Tz(Aa Ar dJ dK Fi fR Ny On Pg Ql Vw) bO(Ar Cs Fw Ir Is Lx Mn Nb Oh Ok Qd) Jg(Bg Cs Gd Hv Hw Jl Kl Lh Ss Ux) Bb(Fw Id Jv Kl Kz Oa oF Ra Rh) Fp(Jy kG Lh mF Mg mT mY nM nR) Nq(Fc Fd Fi Il Iq Nb Nc Pa Uz) Nk(Ax Dc Ed Fy hW jl Nc Pi Un) Rt(bA Bo Cw Pg Ph Rb Up Vp Vs) On(aF Bg dH Dp Ed Jv lX Ow Us) Uw(Ar aY bM cV Cx dR Il Ki Vo) Pf(aY dH Id Kl Pk Qn Qw Rg Vs) Ml(Fc Ho hW jK Ko nT qY Un) Po(Hu Iv Lh Lw Mi Mp Nc) Nd(Lh Mh Mj Mx Nb Nc Oh) Ho(Af aM aP Ax Mh Mx Qx) Qe(aW dR iJ jD jY qT Tv) Ql(Ed It Iv Jn Na Zw Th) Un(aE aY dK eC Fw Il Jm) nN(bM dE Hu Lx Mf Mu nA) Fc(Fy Hb Il Ky Mk Nh) Ih(bM cB Ko mP Qn Us) Of(Ii Iv Jl mU Pa Uc) Oh(Kd Og oN oP Pa Pc) Oy(Ii Jl Lh Nb nU Pa) aW(Is Jt Jy Kd Mz Ny) jH(Et jT Li Lv Pg qY) Aa(Hb Kx oF Uf Vu) Bo(Hp Ry Uz Vh Wc) Fd(aM aN bJ gL Jd) Fi(aM gL Kk Mh Mk) Lx(Hv lK mI oN Pc) Tn(aY Bg Kl Ng Vs) Iq(Iv Lw Mi Nv Pa) Qa(aY bM cB dL Kq) Qd(bM cB Ra Rh Th) Jn(kG mI nT Qm Us) cX(Ar fR nT Nv Ny) Cu(Mn Nl Ss Vs) Cx(Cv Kd We Wg) Mw(Fy Iz lK Pi) Hp(bB bQ Co Mk) Ir(cB jQ Ko Us) Si(aM bQ oF Qv) Wd(Ar aX Cs Ye) Qh(BG Ni Us) Jy(Cs Lu Na Oa) Lp(aH bB Kz Vq) Pg(Kz Oa Qn Vs) Ed(dK Ip Ko) Fw(Kd Nj Oi) Gb(aH aM aN) Nb(aF Hx lX) Ng(Ez Ow Uf) Jl(Ip Mz Nc) Jo(Fy Mz Og) Lh(Iv mI Ms) Nv(Hv Lw Mp) Ny(Ao Kd Ra) aX(iB lM Rz) jG(bB cZ dD) jT(hW Mj rB) Ar(aH Pi) Bg(Fr Mn) Dp(Is Na) No(nD oO) Mi(Pc Xa) Mk(Ry Uy) Nh(mI nT) Id(aE Il) Ij(Vh Zw) Hb(bS Vw) It(mF nT) Qx(Rv Zw) Kl(Fr Uf) Oa(dJ Ni) Oi(Jd Vq) Ok(cV Us) Vc(cU hB) bQ(aY dH) gL(Em Yl) jD(Lv rB) jI(Et qY) AfVh CoUx DcNj GdJt LudF LwIv MgOg MjqY MpPc MsIi NcJh HwIp HxmI TrKq JiJv WcPi KodK RycU UzbJ PedH aNiB cKmU cZjM nIkG

Figure 38 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.2E1 | 1.1E2 | 8.0E1 | 1.2E2 | 4.9E1 | 8.6E1 | 8.0E0 | 7.0E0 | 2.4E2 | 4.8E2 | 197 | 101 | 197 | 101 | 0.64 |
| Ad | ug/mL | 4.2E-2 | 5.3E-2 | 7.1E-2 | 2.1E-1 | 8.3E-2 | 1.0E0 | 6.8E-4 | 7.8E-4 | 3.7E-1 | 8.5E0 | 106 | 68 | 106 | 68 | 0.55 |
| Af | ng/mL | 1.3E0 | 1.1E0 | 1.3E1 | 5.2E0 | 5.6E1 | 6.8E0 | 1.7E-3 | 1.7E-3 | 5.3E2 | 2.3E1 | 106 | 68 | 106 | 68 | 0.50 |
| Aj | ug/mL | 2.0E0 | 3.0E-1 | 2.7E0 | 1.7E0 | 2.5E0 | 2.3E0 | 1.5E-3 | 1.3E-3 | 6.1E0 | 6.1E0 | 106 | 68 | 106 | 68 | 0.38 |
| Al | mg/mL | 8.7E-5 | 8.5E-5 | 2.6E-4 | 3.0E-4 | 4.4E-4 | 4.5E-4 | 4.3E-6 | 6.6E-6 | 1.8E-3 | 1.8E-3 | 106 | 68 | 106 | 68 | 0.54 |
| An | U/mL | 5.0E1 | 8.4E1 | 2.1E2 | 3.3E2 | 6.3E2 | 9.8E2 | 2.8E-1 | 6.4E-1 | 5.5E3 | 7.8E3 | 106 | 68 | 106 | 68 | 0.61 |
| Ao | pg/mL | 9.1E1 | 9.9E1 | 7.3E2 | 2.6E2 | 4.5E3 | 5.8E2 | 1.5E0 | 4.1E0 | 3.9E4 | 4.5E3 | 106 | 68 | 106 | 68 | 0.56 |
| Ap | ng/mL | 3.4E1 | 3.1E1 | 5.0E1 | 5.1E1 | 5.6E1 | 5.8E1 | 2.0E0 | 2.4E0 | 3.3E2 | 2.9E2 | 106 | 68 | 106 | 68 | 0.49 |
| Ar | ng/mL | 5.3E-1 | 1.3E0 | 2.3E0 | 4.4E0 | 5.8E0 | 9.4E0 | 3.4E-3 | 3.4E-3 | 4.7E1 | 5.1E1 | 106 | 68 | 106 | 68 | 0.63 |
| As | ng/mL | 8.7E-3 | 9.3E-3 | 1.2E-2 | 3.1E-2 | 1.5E-2 | 1.5E-1 | 1.7E-3 | 1.7E-3 | 9.8E-2 | 1.2E0 | 106 | 68 | 106 | 68 | 0.50 |
| Aw | pg/mL | 1.7E1 | 1.7E1 | 1.7E1 | 1.7E1 | 5.8E0 | 6.8E0 | 6.8E0 | 2.9E-2 | 4.2E1 | 5.1E1 | 106 | 68 | 106 | 68 | 0.49 |
| Ax | ng/mL | 1.5E0 | 5.4E0 | 1.5E1 | 5.2E1 | 7.6E1 | 1.5E2 | 1.3E-2 | 1.0E-4 | 7.7E2 | 8.5E2 | 106 | 68 | 106 | 68 | 0.60 |
| Ba | ng/mL | 9.0E1 | 8.9E1 | 5.2E2 | 9.8E2 | 1.4E3 | 2.4E3 | 1.9E0 | 1.1E0 | 8.1E3 | 1.5E4 | 106 | 68 | 106 | 68 | 0.55 |
| Bb | ng/mL | 3.8E0 | 6.0E0 | 6.2E0 | 9.4E0 | 7.7E0 | 1.0E1 | 4.1E-3 | 4.1E-3 | 4.9E1 | 4.8E1 | 106 | 68 | 106 | 68 | 0.58 |
| Bc | ng/mL | 3.1E1 | 6.1E1 | 1.1E2 | 1.6E2 | 2.2E2 | 2.6E2 | 4.9E-1 | 1.0E0 | 1.0E3 | 1.2E3 | 106 | 68 | 106 | 68 | 0.58 |
| Bg | ng/mL | 1.1E-1 | 1.1E-1 | 4.3E0 | 9.2E0 | 1.8E1 | 5.0E1 | 5.3E-4 | 5.3E-4 | 1.5E2 | 4.0E2 | 106 | 68 | 106 | 68 | 0.51 |
| Bn | ng/mL | 5.6E-2 | 9.7E-2 | 1.2E0 | 2.0E0 | 2.0E0 | 7.2E0 | 5.6E-2 | 5.6E-2 | 8.5E0 | 5.8E1 | 106 | 68 | 106 | 68 | 0.54 |
| Bo | ng/mL | 1.3E1 | 1.3E1 | 1.5E1 | 1.6E1 | 1.1E1 | 1.2E1 | 1.6E-2 | 1.6E-2 | 4.8E1 | 5.3E1 | 106 | 68 | 106 | 68 | 0.52 |
| Ch | uIU/mL | 1.0E0 | 9.6E-1 | 3.5E1 | 3.3E1 | 1.9E2 | 1.6E2 | 3.4E-3 | 3.9E-2 | 1.8E3 | 1.2E3 | 106 | 68 | 106 | 68 | 0.46 |
| Co | pg/mL | 4.6E1 | 5.1E1 | 1.4E2 | 3.7E2 | 4.2E2 | 2.0E3 | 1.5E-1 | 1.5E-1 | 3.7E3 | 1.7E4 | 106 | 68 | 106 | 68 | 0.51 |
| Cp | ng/mL | 2.1E1 | 2.2E1 | 2.7E1 | 4.9E1 | 2.2E1 | 1.5E2 | 6.0E-1 | 4.7E0 | 1.3E2 | 1.3E3 | 106 | 68 | 106 | 68 | 0.55 |
| Cq | ng/mL | 2.4E-2 | 3.4E-2 | 8.5E-2 | 9.0E-1 | 2.4E-1 | 6.0E0 | 8.0E-4 | 8.0E-4 | 2.0E0 | 4.9E1 | 106 | 68 | 106 | 68 | 0.57 |
| Cs | ng/mL | 3.8E1 | 1.5E2 | 3.0E2 | 7.9E2 | 1.1E3 | 2.3E3 | 1.0E0 | 8.3E-1 | 1.1E4 | 1.8E4 | 106 | 68 | 106 | 68 | 0.65 |
| Ct | ng/mL | 5.3E-1 | 1.6E-1 | 4.0E1 | 4.4E1 | 1.2E2 | 1.2E2 | 1.3E-2 | 1.1E-4 | 6.2E2 | 6.2E2 | 106 | 68 | 106 | 68 | 0.44 |
| Cu | ng/mL | 2.4E-1 | 3.0E-1 | 4.6E-1 | 2.0E0 | 9.2E-1 | 8.3E0 | 1.9E-2 | 1.7E-2 | 9.0E0 | 6.6E1 | 106 | 68 | 106 | 68 | 0.58 |
| Cv | ng/mL | 4.2E0 | 8.6E0 | 2.7E1 | 3.3E1 | 7.2E1 | 7.1E1 | 2.0E-2 | 5.1E-2 | 5.3E2 | 4.7E2 | 106 | 68 | 106 | 68 | 0.56 |
| Cw | mIU/mL | 3.1E-2 | 4.2E-2 | 4.3E-2 | 1.4E-1 | 3.4E-2 | 8.2E-1 | 8.9E-4 | 2.8E-3 | 1.8E-1 | 6.8E0 | 106 | 68 | 106 | 68 | 0.51 |
| Cx | ng/mL | 8.2E-1 | 6.6E-1 | 5.7E1 | 3.9E1 | 1.1E2 | 8.3E1 | 9.3E-5 | 9.3E-5 | 3.9E2 | 2.8E2 | 106 | 68 | 106 | 68 | 0.49 |
| Db | ug/mL | 7.8E0 | 7.0E0 | 9.2E0 | 7.9E0 | 7.2E0 | 8.0E0 | 4.5E-1 | 8.1E-1 | 4.3E1 | 5.9E1 | 106 | 68 | 106 | 68 | 0.44 |
| Dc | nmol/L | 2.0E-2 | 2.3E-2 | 4.2E-2 | 3.5E-1 | 6.7E-2 | 1.7E0 | 5.2E-6 | 1.1E-3 | 4.8E-1 | 1.4E1 | 106 | 68 | 106 | 68 | 0.58 |
| Dd | ug/mL | 6.4E-2 | 1.2E-1 | 1.6E-1 | 2.8E-1 | 2.4E-1 | 5.1E-1 | 4.8E-4 | 3.4E-3 | 1.6E0 | 3.6E0 | 106 | 68 | 106 | 68 | 0.58 |
| De | ng/mL | 3.4E-3 | 3.4E-3 | 7.0E-2 | 1.1E-1 | 1.4E-1 | 1.9E-1 | 3.4E-3 | 3.4E-3 | 9.2E-1 | 1.1E0 | 106 | 68 | 106 | 68 | 0.56 |
| Dg | ng/mL | 3.9E1 | 3.8E1 | 4.7E1 | 5.0E1 | 3.9E1 | 4.3E1 | 1.0E0 | 7.1E-1 | 1.8E2 | 1.9E2 | 106 | 68 | 106 | 68 | 0.52 |
| Di | pg/mL | 2.0E0 | 2.7E0 | 2.3E0 | 2.7E0 | 2.3E0 | 1.9E0 | 1.8E-1 | 1.8E-1 | 1.3E1 | 9.3E0 | 106 | 68 | 106 | 68 | 0.58 |
| Dk | uIU/mL | 1.4E-2 | 1.6E-2 | 6.0E-2 | 6.5E-2 | 1.9E-1 | 1.6E-1 | 1.1E-4 | 1.1E-4 | 1.6E0 | 9.8E-1 | 106 | 68 | 106 | 68 | 0.53 |
| Dl | ng/mL | 1.9E2 | 2.2E2 | 2.9E2 | 3.3E2 | 2.6E2 | 3.2E2 | 8.9E0 | 4.4E0 | 1.3E3 | 1.6E3 | 106 | 68 | 106 | 68 | 0.53 |
| Dp | ng/ml | 2.4E0 | 1.8E0 | 5.6E0 | 5.1E0 | 8.3E0 | 9.5E0 | 3.7E-3 | 3.7E-3 | 4.6E1 | 5.6E1 | 80 | 55 | 80 | 55 | 0.44 |
| Dr | pg/ml | 1.8E1 | 3.0E1 | 4.2E1 | 4.2E1 | 5.7E1 | 1.9E3 | 7.5E-1 | 7.5E-1 | 2.5E2 | 1.0E4 | 42 | 30 | 42 | 30 | 0.58 |
| Du | pg/ml | 8.2E1 | 2.5E2 | 5.5E2 | 2.2E3 | 1.1E3 | 5.8E3 | 1.2E0 | 1.2E0 | 5.4E3 | 2.4E4 | 31 | 26 | 31 | 26 | 0.59 |
| Dw | ng/ml | 9.2E-3 | 2.3E-2 | 3.9E-2 | 6.0E-2 | 5.9E-2 | 7.6E-2 | 9.2E-3 | 9.2E-3 | 1.9E-1 | 1.9E-1 | 10 | 8 | 10 | 8 | 0.58 |
| Ef | ng/ml | 1.4E-1 | 9.0E-2 | 8.9E-1 | 9.1E-1 | 1.8E0 | 2.3E0 | 1.6E-3 | 5.7E-4 | 1.0E1 | 9.9E0 | 87 | 60 | 87 | 60 | 0.46 |
| Wm | % | 8.5E-2 | 8.5E-2 | 3.9E0 | 5.2E1 | 2.0E1 | 2.0E2 | 5.4E-2 | 8.5E-2 | 2.0E2 | 1.0E3 | 98 | 60 | 98 | 60 | 0.51 |
| Ed | pg/ml | 5.2E-1 | 2.3E1 | 2.3E1 | 5.7E1 | 3.7E1 | 9.9E1 | 5.2E-1 | 5.2E-1 | 1.9E2 | 5.0E2 | 80 | 55 | 80 | 55 | 0.61 |
| Eo | ng/ml | 6.1E0 | 3.0E0 | 6.4E0 | 7.8E0 | 5.2E0 | 1.3E1 | 3.6E-1 | 3.6E-1 | 1.6E1 | 4.0E1 | 10 | 8 | 10 | 8 | 0.41 |
| Yf | ng/mL | 1.5E1 | 1.5E1 | 3.9E1 | 7.1E1 | 5.6E1 | 1.4E2 | 2.9E-1 | 2.9E-1 | 2.4E2 | 5.9E2 | 34 | 25 | 34 | 25 | 0.48 |
| Tj | pg/mL | 3.7E-1 | 3.7E-1 | 2.3E1 | 6.3E1 | 1.0E2 | 3.1E2 | 3.7E-1 | 3.7E-1 | 8.7E2 | 2.3E3 | 88 | 57 | 88 | 57 | 0.54 |
| Po | pg/ml | 1.2E-1 | 2.8E0 | 7.8E0 | 1.7E1 | 2.6E1 | 3.9E1 | 8.0E-3 | 2.6E-2 | 2.7E2 | 2.2E2 | 246 | 107 | 246 | 107 | 0.61 |
| Ti | ug/mL | 2.8E0 | 5.4E0 | 4.1E0 | 6.1E0 | 3.8E0 | 4.6E0 | 1.2E-1 | 4.0E-1 | 1.6E1 | 1.8E1 | 48 | 36 | 48 | 36 | 0.63 |
| Em | ng/ml | 2.9E-3 | 2.6E-2 | 4.1E-2 | 1.1E-1 | 8.3E-2 | 3.2E-1 | 8.4E-4 | 8.4E-4 | 5.0E-1 | 1.9E0 | 53 | 39 | 53 | 39 | 0.58 |
| Et | ng/ml | 1.2E3 | 2.1E3 | 1.5E3 | 2.3E3 | 1.1E3 | 1.2E3 | 7.5E1 | 7.9E1 | 4.8E3 | 5.0E3 | 245 | 107 | 245 | 107 | 0.69 |
| Eq | pg/ml | 2.8E1 | 6.6E1 | 3.9E2 | 2.9E2 | 4.0E2 | 4.0E2 | 1.0E0 | 1.0E0 | 1.5E3 | 1.4E3 | 31 | 26 | 31 | 26 | 0.40 |
| Ew | U/ml | 1.9E0 | 2.1E0 | 2.7E0 | 2.5E0 | 2.3E0 | 1.3E0 | 1.1E0 | 1.3E0 | 8.8E0 | 5.0E0 | 10 | 8 | 10 | 8 | 0.56 |
| Th | ug/mL | 1.2E0 | 1.2E0 | 1.6E0 | 2.0E0 | 1.2E0 | 1.9E0 | 1.3E-1 | 2.6E-3 | 5.4E0 | 7.5E0 | 48 | 36 | 48 | 36 | 0.49 |
| Fa | ng/ml | 3.9E1 | 5.9E1 | 5.6E1 | 2.2E2 | 5.9E1 | 6.0E2 | 2.6E-1 | 6.0E-1 | 2.6E2 | 3.7E3 | 78 | 53 | 78 | 53 | 0.59 |

Figure 39

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ez | ng/ml | 3.8E0 | 4.1E0 | 1.6E1 | 1.5E1 | 3.0E1 | 3.2E1 | 1.3E-2 | 1.3E-2 | 1.6E2 | 2.0E2 | 80 | 55 | 80 | 55 | 0.50 |
| Fb | ng/ml | 2.5E1 | 2.7E1 | 2.2E1 | 2.4E1 | 1.2E1 | 1.0E1 | 6.6E-1 | 8.9E-1 | 4.3E1 | 4.3E1 | 78 | 54 | 78 | 54 | 0.55 |
| Ex | ng/ml | 5.8E-2 | 1.2E-1 | 1.8E-1 | 3.1E-1 | 3.4E-1 | 6.8E-1 | 3.5E-5 | 1.7E-4 | 2.2E0 | 4.1E0 | 63 | 42 | 63 | 42 | 0.60 |
| Fc | pg/ml | 2.2E-1 | 2.2E-1 | 1.8E1 | 3.2E1 | 7.9E1 | 9.5E1 | 2.2E-1 | 2.2E-1 | 4.5E2 | 3.9E2 | 32 | 26 | 32 | 26 | 0.59 |
| Fd | pg/ml | 6.7E1 | 1.6E2 | 4.2E2 | 2.5E3 | 7.9E2 | 6.5E3 | 4.5E-1 | 9.8E-1 | 2.9E3 | 2.5E4 | 32 | 26 | 32 | 26 | 0.54 |
| Fi | pg/ml | 2.5E-1 | 2.5E-1 | 6.7E1 | 1.2E2 | 2.0E2 | 3.7E2 | 2.5E-1 | 2.5E-1 | 8.5E2 | 1.8E3 | 32 | 26 | 32 | 26 | 0.57 |
| Fn | ng/ml | 2.1E-1 | 2.8E-1 | 3.7E0 | 4.3E0 | 7.6E0 | 6.4E0 | 1.1E-14 | 2.1E-1 | 3.7E1 | 2.7E1 | 80 | 55 | 80 | 55 | 0.57 |
| Fp | ng/ml | 1.0E1 | 2.0E1 | 2.0E1 | 3.2E1 | 2.4E1 | 3.2E1 | 6.0E-3 | 2.8E-1 | 1.3E2 | 1.3E2 | 246 | 109 | 246 | 109 | 0.63 |
| Fr | ng/ml | 3.0E4 | 6.1E4 | 1.1E5 | 1.8E5 | 1.8E5 | 2.4E5 | 1.9E2 | 1.3E3 | 8.4E5 | 8.4E5 | 251 | 111 | 251 | 111 | 0.62 |
| Fw | pg/ml | 8.5E-1 | 5.8E0 | 4.5E1 | 4.9E1 | 3.2E2 | 1.4E2 | 1.2E-1 | 1.2E-1 | 3.0E3 | 9.1E2 | 89 | 60 | 89 | 60 | 0.61 |
| Fy | ng/ml | 3.2E1 | 4.9E1 | 5.1E1 | 1.0E2 | 5.5E1 | 1.4E2 | 1.2E-1 | 1.2E-1 | 2.8E2 | 6.5E2 | 79 | 53 | 79 | 53 | 0.59 |
| Gh | pg/ml | 1.3E0 | 5.0E0 | 2.7E1 | 1.4E1 | 6.8E1 | 2.9E1 | 2.9E-2 | 2.9E-2 | 3.2E2 | 1.4E2 | 32 | 26 | 32 | 26 | 0.56 |
| Gb | % | 4.2E1 | 3.8E1 | 4.7E1 | 6.1E1 | 4.2E1 | 6.4E1 | 3.7E0 | 2.2E0 | 2.3E2 | 3.0E2 | 32 | 26 | 32 | 26 | 0.56 |
| Gc | ng/ml | 6.7E1 | 1.3E2 | 1.2E2 | 2.4E2 | 1.3E2 | 2.6E2 | 6.4E0 | 6.9E0 | 7.3E2 | 1.2E3 | 42 | 30 | 42 | 30 | 0.67 |
| Gd | ng/ml | 3.2E1 | 3.1E1 | 3.4E1 | 3.2E1 | 1.8E1 | 1.9E1 | 6.3E0 | 3.0E0 | 8.1E1 | 8.0E1 | 50 | 32 | 50 | 32 | 0.46 |
| Gn | U/ml | 2.1E-1 | 2.1E-1 | 1.5E0 | 4.4E0 | 4.8E0 | 2.1E1 | 5.6E-3 | 5.6E-3 | 3.0E1 | 1.1E2 | 41 | 30 | 41 | 30 | 0.52 |
| Gl | pg/ml | 8.5E3 | 1.4E4 | 1.1E4 | 1.5E4 | 9.0E3 | 1.0E4 | 9.1E1 | 4.0E2 | 3.2E4 | 3.2E4 | 89 | 60 | 89 | 60 | 0.59 |
| Gp | U/ml | 1.2E0 | 1.0E0 | 2.5E0 | 2.2E0 | 3.5E0 | 3.4E0 | 1.5E-2 | 1.5E-2 | 2.0E1 | 1.8E1 | 89 | 59 | 89 | 59 | 0.45 |
| Gz | ug/ml | 9.1E0 | 9.2E-1 | 6.5E0 | 4.0E0 | 6.1E0 | 4.9E0 | 4.2E-2 | 8.9E-2 | 2.5E1 | 1.5E1 | 55 | 39 | 55 | 39 | 0.39 |
| Ha | pg/ml | 1.7E0 | 2.6E0 | 5.9E0 | 1.3E1 | 1.4E1 | 2.6E1 | 1.7E-2 | 1.7E-2 | 1.0E2 | 1.0E2 | 78 | 55 | 78 | 55 | 0.60 |
| Nm | pg/ml | 1.1E4 | 2.0E4 | 2.5E4 | 6.5E4 | 5.6E4 | 1.4E5 | 1.0E-9 | 1.0E-9 | 7.8E5 | 9.6E5 | 247 | 109 | 247 | 109 | 0.62 |
| Nn | pg/ml | 1.4E2 | 2.9E2 | 1.2E3 | 7.2E3 | 4.8E3 | 3.3E4 | 1.0E-9 | 1.0E-9 | 6.0E4 | 3.1E5 | 247 | 109 | 247 | 109 | 0.61 |
| No | pg/ml | 1.3E1 | 2.5E1 | 2.9E1 | 6.8E1 | 5.7E1 | 1.5E2 | 1.0E-9 | 1.0E-9 | 5.6E2 | 9.1E2 | 247 | 109 | 247 | 109 | 0.64 |
| Nq | pg/ml | 1.9E0 | 2.1E0 | 1.8E1 | 3.7E1 | 6.3E1 | 1.1E2 | 1.0E-9 | 1.0E-9 | 6.2E2 | 6.7E2 | 247 | 109 | 247 | 109 | 0.53 |
| Nr | pg/ml | 1.2E0 | 3.0E0 | 2.1E1 | 4.3E1 | 8.0E1 | 1.6E2 | 1.0E-9 | 1.0E-9 | 9.8E2 | 1.4E3 | 247 | 109 | 247 | 109 | 0.59 |
| Ns | pg/ml | 1.0E-9 | 1.0E-9 | 5.2E0 | 1.3E1 | 2.7E1 | 1.1E2 | 1.0E-9 | 1.0E-9 | 2.4E2 | 1.1E3 | 247 | 109 | 247 | 109 | 0.50 |
| Nt | pg/ml | 8.8E1 | 1.4E2 | 1.2E2 | 2.0E2 | 8.9E1 | 2.2E2 | 9.8E-1 | 2.3E1 | 5.9E2 | 1.7E3 | 247 | 109 | 247 | 109 | 0.69 |
| Nu | pg/ml | 9.5E0 | 5.0E1 | 4.5E1 | 8.5E1 | 8.1E1 | 1.1E2 | 1.0E-9 | 1.0E-9 | 4.2E2 | 6.3E2 | 247 | 109 | 247 | 109 | 0.67 |
| Lu | pg/ml | 1.0E4 | 1.0E4 | 1.5E4 | 1.6E4 | 3.1E4 | 5.4E4 | 7.7E2 | 5.2E2 | 3.9E5 | 5.6E5 | 247 | 109 | 247 | 109 | 0.49 |
| Lv | pg/ml | 1.0E-9 | 6.8E0 | 1.2E1 | 2.6E1 | 2.5E1 | 4.4E1 | 1.0E-9 | 1.0E-9 | 2.4E2 | 2.6E2 | 247 | 109 | 247 | 109 | 0.60 |
| Lw | pg/ml | 1.0E-9 | 1.0E-9 | 1.4E-1 | 3.5E0 | 2.0E0 | 1.9E1 | 1.0E-9 | 1.0E-9 | 3.2E1 | 1.8E2 | 247 | 109 | 247 | 109 | 0.54 |
| Lx | pg/ml | 1.0E-9 | 5.5E1 | 1.4E2 | 5.6E2 | 4.8E2 | 2.3E3 | 1.0E-9 | 1.0E-9 | 6.2E3 | 2.2E4 | 247 | 109 | 247 | 109 | 0.64 |
| Ly | pg/ml | 1.0E-9 | 1.0E-9 | 8.9E0 | 9.5E0 | 1.8E1 | 1.7E1 | 1.0E-9 | 1.0E-9 | 1.1E2 | 9.6E1 | 247 | 109 | 247 | 109 | 0.51 |
| Lz | pg/ml | 1.0E-9 | 1.0E-9 | 3.4E0 | 3.7E0 | 2.9E1 | 1.6E1 | 1.0E-9 | 1.0E-9 | 4.3E2 | 1.3E2 | 247 | 109 | 247 | 109 | 0.52 |
| Ma | pg/ml | 3.7E2 | 7.6E2 | 2.0E3 | 3.4E3 | 5.7E3 | 7.4E3 | 1.0E-9 | 1.0E-9 | 6.5E4 | 5.2E4 | 247 | 109 | 247 | 109 | 0.59 |
| Mb | pg/ml | 2.4E1 | 2.9E1 | 3.0E1 | 3.5E1 | 1.8E1 | 1.7E1 | 9.2E0 | 4.1E0 | 2.1E2 | 1.1E2 | 247 | 109 | 247 | 109 | 0.58 |
| Mc | pg/ml | 1.0E-9 | 1.0E-9 | 7.0E-2 | 1.5E-2 | 8.7E-1 | 1.6E-1 | 1.0E-9 | 1.0E-9 | 1.3E1 | 1.7E0 | 247 | 109 | 247 | 109 | 0.50 |
| Md | pg/ml | 1.0E-9 | 1.0E-9 | 6.3E-1 | 7.4E-1 | 6.0E0 | 3.6E0 | 1.0E-9 | 1.0E-9 | 6.8E1 | 2.9E1 | 247 | 109 | 247 | 109 | 0.52 |
| Me | pg/ml | 3.2E1 | 3.0E1 | 3.0E1 | 3.3E1 | 1.6E1 | 3.8E1 | 1.0E-9 | 1.0E-9 | 1.2E2 | 3.2E2 | 247 | 109 | 247 | 109 | 0.48 |
| Mf | pg/ml | 1.0E-9 | 1.0E-9 | 3.4E-1 | 1.3E0 | 1.6E0 | 6.5E0 | 1.0E-9 | 1.0E-9 | 2.0E1 | 5.6E1 | 247 | 109 | 247 | 109 | 0.54 |
| Mg | pg/ml | 9.3E-1 | 1.6E0 | 6.1E0 | 8.8E0 | 1.1E1 | 2.1E1 | 1.0E-9 | 1.0E-9 | 8.8E1 | 1.5E2 | 247 | 109 | 247 | 109 | 0.53 |
| Mh | pg/ml | 1.0E-9 | 1.0E-9 | 1.2E0 | 1.1E0 | 8.5E0 | 4.6E0 | 1.0E-9 | 1.0E-9 | 1.1E2 | 4.2E1 | 247 | 109 | 247 | 109 | 0.58 |
| Mi | pg/ml | 1.0E-9 | 1.0E-9 | 7.9E-1 | 1.1E1 | 8.2E0 | 5.9E1 | 1.0E-9 | 1.0E-9 | 1.2E2 | 5.2E2 | 247 | 109 | 247 | 109 | 0.55 |
| Mj | pg/ml | 1.0E-9 | 1.0E-9 | 6.2E0 | 9.5E0 | 3.5E1 | 3.0E1 | 1.0E-9 | 1.0E-9 | 4.6E2 | 2.1E2 | 247 | 109 | 247 | 109 | 0.54 |
| Mk | pg/ml | 2.0E0 | 2.7E0 | 1.3E1 | 2.4E1 | 6.8E1 | 1.4E2 | 1.0E-9 | 1.0E-9 | 1.0E3 | 1.3E3 | 247 | 109 | 247 | 109 | 0.50 |
| Ml | pg/ml | 1.0E-9 | 1.0E-9 | 1.1E1 | 1.2E1 | 1.3E2 | 6.0E1 | 1.0E-9 | 1.0E-9 | 2.1E3 | 5.1E2 | 247 | 109 | 247 | 109 | 0.53 |
| Mm | pg/ml | 4.4E2 | 7.9E2 | 9.3E2 | 1.5E3 | 1.2E3 | 1.8E3 | 1.0E-9 | 1.0E-9 | 1.0E4 | 1.0E4 | 247 | 109 | 247 | 109 | 0.60 |
| Mn | pg/ml | 5.0E0 | 9.9E0 | 1.1E1 | 1.2E1 | 2.8E1 | 1.1E1 | 1.0E-9 | 1.0E-9 | 3.5E2 | 6.8E1 | 247 | 109 | 247 | 109 | 0.67 |
| Mp | pg/ml | 1.0E-9 | 1.0E-9 | 8.4E0 | 5.0E1 | 2.1E1 | 2.4E2 | 1.0E-9 | 1.0E-9 | 1.8E2 | 2.4E3 | 247 | 109 | 247 | 109 | 0.56 |
| Mq | pg/ml | 1.0E-9 | 1.0E-9 | 2.1E0 | 4.4E0 | 1.3E1 | 1.7E1 | 1.0E-9 | 1.0E-9 | 1.8E2 | 1.0E2 | 247 | 109 | 247 | 109 | 0.52 |
| Mr | pg/ml | 1.0E-9 | 1.0E-9 | 1.8E1 | 1.0E2 | 9.8E1 | 4.4E2 | 1.0E-9 | 1.0E-9 | 1.4E3 | 3.4E3 | 247 | 109 | 247 | 109 | 0.58 |
| Ms | pg/ml | 3.4E2 | 2.7E2 | 4.8E2 | 4.4E2 | 5.4E2 | 6.2E2 | 1.0E-9 | 1.0E-9 | 3.2E3 | 4.7E3 | 247 | 109 | 247 | 109 | 0.45 |
| Mt | pg/ml | 1.0E-9 | 9.5E-1 | 7.5E0 | 4.7E1 | 4.8E1 | 3.1E2 | 1.0E-9 | 1.0E-9 | 7.1E2 | 3.2E3 | 247 | 109 | 247 | 109 | 0.61 |
| Mu | pg/ml | 1.0E-9 | 1.0E-9 | 8.6E-1 | 3.6E0 | 7.2E0 | 2.3E1 | 1.0E-9 | 1.0E-9 | 9.9E1 | 2.3E2 | 247 | 109 | 247 | 109 | 0.53 |
| Mv | pg/ml | 1.0E-9 | 1.0E-9 | 6.9E1 | 7.5E1 | 3.8E2 | 2.0E2 | 1.0E-9 | 1.0E-9 | 4.5E3 | 9.2E2 | 247 | 109 | 247 | 109 | 0.54 |
| Mw | pg/ml | 3.2E1 | 5.9E1 | 3.0E2 | 3.3E2 | 1.6E3 | 8.7E2 | 1.0E-9 | 1.0E-9 | 1.8E4 | 5.3E3 | 247 | 109 | 247 | 109 | 0.57 |
| Mx | pg/ml | 1.0E-9 | 1.0E-9 | 1.9E-1 | 9.8E-1 | 8.1E-1 | 3.7E0 | 1.0E-9 | 1.0E-9 | 9.2E0 | 3.2E1 | 247 | 109 | 247 | 109 | 0.59 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| My | pg/ml | 1.0E-9 | 1.0E-9 | 3.8E2 | 2.0E2 | 2.8E3 | 8.3E2 | 1.0E-9 | 1.0E-9 | 3.9E4 | 8.0E3 | 247 | 109 | 247 | 109 | 0.49 |
| Mz | pg/ml | 9.1E0 | 2.0E1 | 2.2E1 | 7.0E1 | 4.9E1 | 2.2E2 | 1.0E-9 | 1.0E-9 | 5.5E2 | 1.9E3 | 247 | 109 | 247 | 109 | 0.67 |
| Na | pg/ml | 1.0E-9 | 1.0E-9 | 7.4E-1 | 8.9E-1 | 2.0E0 | 4.3E0 | 1.0E-9 | 1.0E-9 | 7.8E0 | 4.2E1 | 247 | 109 | 247 | 109 | 0.51 |
| Nb | pg/ml | 2.1E0 | 2.5E0 | 3.8E0 | 6.9E0 | 1.1E1 | 2.3E1 | 1.0E-9 | 1.0E-9 | 1.5E2 | 2.1E2 | 247 | 109 | 247 | 109 | 0.57 |
| Nc | pg/ml | 3.7E2 | 2.1E2 | 5.6E2 | 3.9E2 | 8.1E2 | 5.0E2 | 1.0E-9 | 1.0E-9 | 9.2E3 | 3.2E3 | 247 | 109 | 247 | 109 | 0.43 |
| Nd | pg/ml | 3.0E1 | 1.3E1 | 2.5E1 | 5.3E1 | 1.7E1 | 2.3E2 | 1.0E-9 | 1.0E-9 | 7.8E1 | 2.1E3 | 247 | 109 | 247 | 109 | 0.46 |
| Ne | pg/ml | 4.5E2 | 3.4E2 | 5.6E2 | 4.2E2 | 6.0E2 | 4.4E2 | 1.0E-9 | 1.0E-9 | 7.0E3 | 3.6E3 | 247 | 109 | 247 | 109 | 0.41 |
| Nf | pg/ml | 1.0E-9 | 1.0E-9 | 2.7E0 | 3.8E0 | 9.4E0 | 1.8E1 | 1.0E-9 | 1.0E-9 | 8.2E1 | 1.3E2 | 247 | 109 | 247 | 109 | 0.47 |
| Ng | pg/ml | 1.3E1 | 9.6E0 | 9.4E1 | 8.0E1 | 2.0E2 | 1.4E2 | 1.0E-9 | 1.0E-9 | 1.6E3 | 8.5E2 | 247 | 109 | 247 | 109 | 0.51 |
| Nh | pg/ml | 6.4E1 | 5.3E1 | 8.7E1 | 6.3E1 | 7.9E1 | 6.4E1 | 1.0E-9 | 3.6E0 | 5.6E2 | 5.1E2 | 247 | 109 | 247 | 109 | 0.40 |
| Ni | pg/ml | 1.0E-9 | 1.0E-9 | 7.8E1 | 1.0E2 | 1.3E2 | 1.6E2 | 1.0E-9 | 1.0E-9 | 7.1E2 | 1.1E3 | 247 | 109 | 247 | 109 | 0.51 |
| Nj | pg/ml | 8.7E0 | 4.7E0 | 1.2E1 | 7.4E0 | 1.2E1 | 8.2E0 | 1.0E-9 | 1.0E-9 | 6.9E1 | 4.6E1 | 247 | 109 | 247 | 109 | 0.37 |
| Nk | pg/ml | 1.8E1 | 1.4E1 | 3.3E1 | 3.0E1 | 3.8E1 | 4.0E1 | 1.0E-9 | 1.0E-9 | 2.0E2 | 2.0E2 | 247 | 109 | 247 | 109 | 0.48 |
| Nl | pg/ml | 4.6E1 | 3.3E1 | 6.3E1 | 4.1E1 | 8.5E1 | 4.0E1 | 1.0E-9 | 1.0E-9 | 1.1E3 | 2.3E2 | 247 | 109 | 247 | 109 | 0.40 |
| Hl | pg/ml | 4.2E0 | 9.6E0 | 3.5E1 | 1.6E2 | 6.2E1 | 7.0E2 | 1.0E-9 | 1.0E-9 | 3.0E2 | 3.6E3 | 32 | 26 | 32 | 26 | 0.50 |
| Ho | pg/ml | 1.5E1 | 2.0E1 | 2.1E1 | 4.8E1 | 2.1E1 | 8.0E1 | 1.0E-9 | 7.6E0 | 8.3E1 | 3.9E2 | 32 | 26 | 32 | 26 | 0.66 |
| Hp | pg/ml | 1.7E0 | 1.6E0 | 1.4E2 | 1.0E2 | 3.3E2 | 2.9E2 | 3.6E-1 | 1.0E-9 | 8.9E2 | 8.9E2 | 32 | 26 | 32 | 26 | 0.48 |
| Tz | pg/ml | 3.5E3 | 6.9E3 | 5.9E3 | 5.5E4 | 7.6E3 | 2.8E5 | 7.4E1 | 1.0E-9 | 5.3E4 | 2.1E6 | 80 | 55 | 80 | 55 | 0.61 |
| Ua | pg/ml | 3.2E3 | 3.7E3 | 4.1E3 | 1.3E4 | 2.4E5 | 2.4E4 | 2.3E2 | 1.0E-9 | 2.1E6 | 1.2E5 | 80 | 55 | 80 | 55 | 0.51 |
| Ub | pg/ml | 6.0E2 | 4.1E2 | 9.7E2 | 6.8E2 | 1.3E3 | 8.3E2 | 1.6E1 | 1.0E-9 | 9.8E3 | 4.4E3 | 80 | 55 | 80 | 55 | 0.41 |
| Ue | pg/ml | 3.1E1 | 2.4E1 | 3.8E1 | 3.4E1 | 3.5E1 | 3.1E1 | 5.2E0 | 9.8E-2 | 2.7E2 | 1.4E2 | 80 | 55 | 80 | 55 | 0.43 |
| Uc | pg/ml | 7.0E2 | 7.9E2 | 1.2E3 | 2.6E3 | 1.3E3 | 7.8E3 | 2.2E1 | 1.0E-9 | 8.3E3 | 5.7E4 | 80 | 55 | 80 | 55 | 0.51 |
| Ud | pg/ml | 1.0E-9 | 1.0E-9 | 4.9E0 | 9.7E-1 | 4.4E1 | 7.2E0 | 1.0E-9 | 1.0E-9 | 3.9E2 | 5.3E1 | 80 | 55 | 80 | 55 | 0.50 |
| Hq | pg/ml | 1.1E0 | 1.3E0 | 9.2E1 | 3.0E2 | 1.3E3 | 2.7E3 | 1.0E-9 | 1.0E-9 | 2.0E4 | 2.8E4 | 247 | 107 | 247 | 107 | 0.51 |
| Hr | pg/ml | 9.8E1 | 8.5E1 | 7.1E2 | 5.2E2 | 1.4E3 | 1.3E3 | 1.0E-9 | 1.0E-9 | 1.2E4 | 8.9E3 | 247 | 107 | 247 | 107 | 0.47 |
| Hu | pg/ml | 1.0E-9 | 2.2E1 | 5.2E3 | 3.0E3 | 4.4E4 | 2.5E4 | 1.0E-9 | 1.0E-9 | 6.3E5 | 2.6E5 | 247 | 107 | 247 | 107 | 0.56 |
| Hv | pg/ml | 1.4E0 | 1.6E0 | 2.5E0 | 1.3E1 | 6.3E0 | 8.8E1 | 1.0E-9 | 1.0E-9 | 6.9E1 | 8.9E2 | 247 | 107 | 247 | 107 | 0.54 |
| Hw | pg/ml | 6.4E0 | 6.1E0 | 1.6E1 | 1.1E2 | 5.1E1 | 9.0E2 | 1.0E-9 | 1.0E-9 | 6.4E2 | 9.4E3 | 247 | 107 | 247 | 107 | 0.49 |
| Hx | pg/ml | 8.4E0 | 1.1E1 | 6.2E1 | 4.8E1 | 5.9E2 | 1.5E2 | 1.0E-9 | 1.0E-9 | 9.3E3 | 1.3E3 | 247 | 107 | 247 | 107 | 0.54 |
| Ib | ng/ml | 4.5E-2 | 2.6E-2 | 1.5E0 | 1.3E0 | 5.6E0 | 7.7E0 | 1.0E-9 | 1.0E-9 | 3.6E1 | 5.6E1 | 80 | 53 | 80 | 53 | 0.44 |
| Ic | U/ml | 2.2E2 | 2.2E2 | 1.2E3 | 2.0E2 | 7.3E3 | 1.6E2 | 2.4E0 | 1.1E1 | 6.5E4 | 7.9E2 | 80 | 53 | 80 | 53 | 0.49 |
| Id | U/ml | 5.8E-1 | 8.2E-1 | 1.0E0 | 1.0E1 | 1.3E0 | 5.9E1 | 1.0E-9 | 1.0E-9 | 6.9E0 | 4.3E2 | 80 | 53 | 80 | 53 | 0.60 |
| Tt | pg/ml | 1.7E2 | 1.7E2 | 1.7E2 | 1.8E2 | 5.0E1 | 6.7E1 | 4.3E1 | 7.3E1 | 3.0E2 | 4.4E2 | 73 | 51 | 73 | 51 | 0.53 |
| To | pg/ml | 1.8E0 | 1.4E0 | 2.4E0 | 1.9E0 | 3.1E0 | 2.4E0 | 1.0E-9 | 1.0E-9 | 2.3E1 | 1.2E1 | 78 | 53 | 78 | 53 | 0.43 |
| Tr | pg/ml | 3.6E0 | 3.2E0 | 5.4E0 | 1.4E1 | 6.3E0 | 4.4E1 | 1.0E-9 | 1.0E-9 | 3.8E1 | 3.1E2 | 76 | 52 | 76 | 52 | 0.53 |
| Tn | pg/ml | 3.1E1 | 4.2E1 | 9.2E1 | 2.0E2 | 2.5E2 | 4.8E2 | 1.0E-9 | 2.4E0 | 1.7E3 | 2.3E3 | 78 | 53 | 78 | 53 | 0.56 |
| Tv | ng/ml | 1.3E1 | 1.1E1 | 2.1E1 | 1.7E2 | 3.9E1 | 9.7E2 | 1.0E-9 | 1.0E-9 | 3.2E2 | 7.1E3 | 78 | 53 | 78 | 53 | 0.48 |
| Ih | ng/ml | 5.6E1 | 1.1E2 | 2.2E2 | 3.8E2 | 3.8E2 | 6.1E2 | 1.0E-9 | 1.0E-9 | 2.5E3 | 3.6E3 | 247 | 108 | 247 | 108 | 0.60 |
| Ii | ng/ml | 6.5E1 | 1.1E2 | 2.1E2 | 2.7E2 | 5.3E2 | 5.9E2 | 7.3E-1 | 7.5E-1 | 5.2E3 | 4.5E3 | 247 | 108 | 247 | 108 | 0.59 |
| Ij | ng/ml | 7.1E1 | 1.1E2 | 1.8E2 | 4.2E2 | 6.5E2 | 2.4E3 | 2.8E0 | 9.5E0 | 6.4E3 | 2.4E4 | 245 | 106 | 245 | 106 | 0.64 |
| Ik | ng/ml | 8.0E0 | 2.0E1 | 1.7E3 | 2.4E2 | 1.4E4 | 4.4E2 | 5.9E-1 | 6.2E-1 | 1.2E5 | 1.8E3 | 244 | 107 | 244 | 107 | 0.61 |
| Il | ng/ml | 3.6E2 | 4.2E2 | 1.3E3 | 1.6E3 | 2.9E3 | 3.1E3 | 1.0E-9 | 1.0E-9 | 1.2E4 | 1.2E4 | 243 | 106 | 243 | 106 | 0.55 |
| Im | ng/ml | 1.9E2 | 3.1E2 | 3.4E2 | 8.8E2 | 5.1E2 | 1.8E3 | 1.4E1 | 2.2E1 | 6.0E3 | 1.5E4 | 244 | 107 | 244 | 107 | 0.66 |
| In | ng/ml | 3.4E0 | 3.4E0 | 2.2E1 | 6.2E1 | 1.0E2 | 4.4E2 | 1.0E-9 | 1.0E-9 | 1.1E3 | 4.5E3 | 247 | 108 | 247 | 108 | 0.51 |
| Hb | ng/ml | 2.1E1 | 3.0E1 | 3.1E1 | 4.1E1 | 3.2E1 | 4.1E1 | 1.6E0 | 4.8E-1 | 2.0E2 | 1.9E2 | 79 | 57 | 79 | 57 | 0.57 |
| Hc | pg/ml | 7.2E2 | 5.8E2 | 3.9E3 | 2.1E3 | 1.2E4 | 7.0E3 | 1.0E-9 | 1.0E-9 | 1.0E5 | 5.9E4 | 79 | 57 | 79 | 57 | 0.43 |
| Hf | ng/ml | 1.6E2 | 2.5E2 | 3.6E2 | 4.4E2 | 5.1E2 | 5.9E2 | 1.0E-9 | 1.0E-9 | 2.5E3 | 3.2E3 | 79 | 57 | 79 | 57 | 0.57 |
| Io | ng/ml | 7.0E3 | 1.2E4 | 1.8E4 | 2.2E4 | 5.1E4 | 2.9E4 | 1.2E2 | 1.0E-9 | 7.1E5 | 2.0E5 | 246 | 109 | 246 | 109 | 0.60 |
| Ip | ng/ml | 8.1E0 | 3.0E1 | 2.0E1 | 2.6E1 | 2.8E1 | 2.2E1 | 1.0E-9 | 1.0E-9 | 2.3E2 | 7.8E1 | 246 | 109 | 246 | 109 | 0.60 |
| Iq | ug/ml | 1.0E-1 | 1.4E-1 | 5.6E1 | 3.4E0 | 8.7E2 | 2.1E1 | 1.0E-9 | 1.0E-9 | 1.4E4 | 2.2E2 | 246 | 109 | 246 | 109 | 0.55 |
| Ir | ug/ml | 3.4E-1 | 7.6E-1 | 4.4E0 | 1.1E1 | 3.6E1 | 4.2E1 | 1.0E-9 | 1.0E-9 | 5.1E2 | 3.7E2 | 245 | 109 | 245 | 109 | 0.63 |
| Is | ng/ml | 1.6E0 | 3.8E0 | 7.7E0 | 1.8E1 | 3.6E1 | 3.7E1 | 1.0E-9 | 1.0E-9 | 5.5E2 | 2.6E2 | 246 | 109 | 246 | 109 | 0.62 |
| It | ng/ml | 1.7E0 | 2.9E0 | 2.2E1 | 2.8E1 | 1.0E2 | 1.2E2 | 1.0E-9 | 1.0E-9 | 1.1E3 | 8.3E2 | 246 | 109 | 246 | 109 | 0.58 |
| Iu | ng/ml | 1.7E2 | 1.5E2 | 1.4E3 | 1.6E3 | 4.3E3 | 4.7E3 | 1.0E-9 | 1.0E-9 | 2.9E4 | 2.4E4 | 246 | 109 | 246 | 109 | 0.50 |
| Iv | ng/ml | 9.5E1 | 2.2E1 | 9.8E1 | 1.6E2 | 1.0E3 | 6.2E2 | 1.0E-9 | 1.0E-9 | 1.6E4 | 3.8E3 | 245 | 109 | 245 | 109 | 0.64 |
| Iz | ng/ml | 1.3E2 | 1.2E2 | 4.6E2 | 2.4E2 | 8.9E2 | 3.2E2 | 1.5E0 | 8.8E-1 | 6.1E3 | 1.7E3 | 79 | 57 | 79 | 57 | 0.45 |
| Yg | pg/ml | 2.5E2 | 2.7E2 | 2.3E3 | 1.0E3 | 9.2E3 | 1.8E3 | 1.0E-9 | 1.0E-9 | 5.0E4 | 8.2E3 | 29 | 25 | 29 | 25 | 0.53 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yh | pg/ml | 2.1E2 | 2.1E2 | 3.8E2 | 5.3E2 | 4.4E2 | 7.5E2 | 1.0E-9 | 1.0E-9 | 1.8E3 | 3.0E3 | 29 | 25 | 29 | 25 | 0.52 |
| Yi | pg/ml | 2.4E2 | 4.5E2 | 5.0E2 | 2.0E3 | 5.4E2 | 5.4E3 | 1.0E-9 | 1.0E-9 | 2.0E3 | 2.6E4 | 29 | 25 | 29 | 25 | 0.57 |
| Yk | U/ml | 1.0E-9 | 1.0E-9 | 2.4E-1 | 2.1E-1 | 6.8E-1 | 5.2E-1 | 1.0E-9 | 1.0E-9 | 3.0E0 | 2.0E0 | 29 | 25 | 29 | 25 | 0.50 |
| Yj | pg/ml | 1.6E2 | 1.1E2 | 3.6E2 | 2.2E2 | 6.1E2 | 3.0E2 | 9.7E0 | 1.0E-9 | 3.2E3 | 1.5E3 | 29 | 25 | 29 | 25 | 0.42 |
| Yd | ng/ml | 1.7E-1 | 2.8E-1 | 3.8E-1 | 4.2E-1 | 4.9E-1 | 5.6E-1 | 6.6E-3 | 1.6E-2 | 1.8E0 | 2.3E0 | 32 | 26 | 32 | 26 | 0.53 |
| Wb | pg/ml | 2.6E4 | 3.5E4 | 3.0E4 | 6.4E4 | 1.9E4 | 1.2E5 | 4.9E3 | 7.5E3 | 8.4E4 | 6.4E5 | 32 | 26 | 32 | 26 | 0.66 |
| Vz | pg/ml | 3.7E0 | 3.2E0 | 4.6E0 | 4.8E0 | 3.8E0 | 5.5E0 | 1.0E-9 | 7.6E-2 | 1.6E1 | 2.2E1 | 32 | 26 | 32 | 26 | 0.48 |
| Si | ng/ml | 1.2E0 | 1.2E0 | 2.2E0 | 1.7E0 | 3.0E0 | 1.6E0 | 1.1E-1 | 8.6E-3 | 1.0E1 | 6.0E0 | 32 | 26 | 32 | 26 | 0.53 |
| Sf | mIU/mL | 1.7E1 | 1.6E1 | 6.7E1 | 2.0E1 | 1.4E2 | 1.9E1 | 6.2E-1 | 1.3E0 | 7.2E2 | 8.3E1 | 32 | 26 | 32 | 26 | 0.44 |
| Sh | mIU/mL | 1.7E1 | 1.2E1 | 5.9E1 | 1.8E1 | 1.1E2 | 1.8E1 | 1.8E-1 | 7.8E-2 | 5.7E2 | 6.1E1 | 32 | 26 | 32 | 26 | 0.44 |
| Sj | ng/ml | 3.8E-1 | 4.4E-1 | 4.1E-1 | 4.5E-1 | 9.3E-2 | 9.3E-2 | 2.5E-1 | 3.2E-1 | 6.1E-1 | 7.2E-1 | 32 | 26 | 32 | 26 | 0.61 |
| Rc | pg/ml | 7.0E3 | 5.5E3 | 8.2E3 | 7.1E3 | 5.6E3 | 6.2E3 | 3.9E2 | 5.5E2 | 2.8E4 | 3.9E4 | 80 | 55 | 80 | 55 | 0.43 |
| Rb | pg/ml | 7.5E-1 | 7.1E-1 | 2.5E0 | 3.8E0 | 3.8E0 | 8.3E0 | 1.0E-9 | 1.0E-9 | 1.6E1 | 5.6E1 | 80 | 55 | 80 | 55 | 0.52 |
| Zq | 2.6ng/ml | 1.8E2 | 3.4E2 | 2.7E2 | 3.5E2 | 2.3E2 | 2.0E2 | 1.4E1 | 1.7E1 | 9.7E2 | 9.7E2 | 31 | 25 | 31 | 25 | 0.64 |
| Zw | 2.5ng/ml | 4.2E0 | 5.4E0 | 9.5E0 | 1.1E1 | 1.2E1 | 1.7E1 | 1.4E-1 | 2.4E-1 | 5.9E1 | 6.3E1 | 32 | 26 | 32 | 26 | 0.48 |
| Zx | 2.3mU/ml | 8.6E-2 | 1.4E-1 | 2.7E-1 | 3.2E-1 | 5.1E-1 | 5.2E-1 | 3.2E-2 | 5.0E-2 | 2.9E0 | 2.1E0 | 32 | 26 | 32 | 26 | 0.59 |
| Pz | ng/ml | 3.1E3 | 5.2E3 | 5.4E3 | 6.1E3 | 6.5E3 | 4.5E3 | 1.6E1 | 4.0E1 | 7.0E4 | 2.5E4 | 245 | 106 | 245 | 106 | 0.59 |
| Qa | ng/ml | 3.0E3 | 6.5E3 | 6.1E3 | 1.2E4 | 7.4E3 | 2.3E4 | 1.5E2 | 4.2E2 | 4.2E4 | 2.2E5 | 245 | 106 | 245 | 106 | 0.64 |
| Qb | ng/ml | 9.7E1 | 1.5E2 | 2.1E2 | 3.1E2 | 4.3E2 | 4.6E2 | 7.9E-1 | 6.7E0 | 5.3E3 | 4.1E3 | 245 | 106 | 245 | 106 | 0.62 |
| Qc | ng/ml | 1.7E2 | 3.7E2 | 4.0E2 | 5.9E2 | 5.6E2 | 6.5E2 | 1.0E-9 | 1.0E-9 | 3.8E3 | 4.3E3 | 245 | 106 | 245 | 106 | 0.62 |
| Qd | ng/ml | 7.5E3 | 1.4E4 | 2.3E4 | 3.9E4 | 1.3E5 | 6.4E4 | 1.5E2 | 1.2E3 | 2.0E6 | 4.3E5 | 245 | 106 | 245 | 106 | 0.67 |
| Qe | ng/ml | 7.6E2 | 1.8E3 | 2.0E3 | 2.6E3 | 6.5E3 | 2.7E3 | 1.0E-9 | 8.8E0 | 9.7E4 | 1.8E4 | 245 | 106 | 245 | 106 | 0.66 |
| Jd | ng/ml | 6.9E-1 | 1.4E0 | 4.8E0 | 2.9E0 | 1.8E1 | 4.4E0 | 1.0E-9 | 1.0E-9 | 1.2E2 | 2.1E1 | 80 | 55 | 80 | 55 | 0.59 |
| Je | ng/ml | 1.0E-9 | 1.0E-9 | 1.9E0 | 1.6E0 | 6.0E0 | 2.5E0 | 1.0E-9 | 1.0E-9 | 4.6E1 | 1.1E1 | 80 | 55 | 80 | 55 | 0.55 |
| Jf | ng/ml | 1.0E-9 | 1.0E-9 | 9.7E-1 | 1.5E0 | 2.2E0 | 2.3E0 | 1.0E-9 | 1.0E-9 | 1.2E1 | 9.1E0 | 80 | 55 | 80 | 55 | 0.56 |
| Jg | ng/ml | 3.6E2 | 7.8E2 | 7.0E2 | 1.1E3 | 9.5E2 | 1.1E3 | 5.8E0 | 1.3E1 | 1.0E4 | 7.1E3 | 247 | 107 | 247 | 107 | 0.65 |
| Jh | ng/ml | 2.4E0 | 4.9E0 | 2.2E1 | 2.6E1 | 9.4E1 | 6.5E1 | 1.0E-9 | 1.0E-9 | 1.2E3 | 4.9E2 | 247 | 107 | 247 | 107 | 0.59 |
| Ji | ng/ml | 4.7E1 | 8.5E1 | 6.8E1 | 1.6E2 | 7.1E1 | 1.9E2 | 1.1E0 | 8.9E0 | 5.3E2 | 1.3E3 | 247 | 107 | 247 | 107 | 0.70 |
| Sr | pg/mL | 3.2E2 | 7.0E2 | 7.5E2 | 1.5E3 | 1.1E3 | 3.0E3 | 1.0E-9 | 1.0E-9 | 5.5E3 | 2.1E4 | 80 | 54 | 80 | 54 | 0.64 |
| Ss | pg/mL | 9.7E4 | 7.4E4 | 1.5E5 | 1.4E5 | 1.6E5 | 2.1E5 | 9.1E3 | 2.7E3 | 7.1E5 | 1.3E6 | 80 | 54 | 80 | 54 | 0.45 |
| St | pg/mL | 2.2E7 | 4.2E7 | 4.6E7 | 1.1E8 | 6.5E7 | 2.7E8 | 7.8E5 | 1.0E-9 | 4.1E8 | 1.7E9 | 78 | 55 | 78 | 55 | 0.58 |
| Wc | ng/ml | 1.0E-9 | 2.1E-3 | 6.0E-2 | 1.3E-1 | 1.2E-1 | 3.6E-1 | 1.0E-9 | 1.0E-9 | 5.2E-1 | 1.8E0 | 32 | 26 | 32 | 26 | 0.55 |
| Wd | ng/ml | 9.9E0 | 8.8E0 | 3.2E1 | 4.8E1 | 6.6E1 | 1.1E2 | 1.0E0 | 1.5E0 | 2.9E2 | 4.1E2 | 32 | 26 | 32 | 26 | 0.50 |
| We | ng/ml | 2.7E-1 | 4.9E-1 | 1.0E0 | 1.8E0 | 1.4E0 | 4.7E0 | 1.0E-9 | 1.0E-9 | 5.5E0 | 2.3E1 | 32 | 26 | 32 | 26 | 0.53 |
| Wg | ng/ml | 1.0E-9 | 1.0E-9 | 5.1E-4 | 2.1E-2 | 2.9E-3 | 1.0E-1 | 1.0E-9 | 1.0E-9 | 1.6E-2 | 5.3E-1 | 32 | 26 | 32 | 26 | 0.50 |
| Wh | ng/ml | 1.0E-2 | 1.0E-2 | 4.9E-2 | 4.4E-2 | 9.8E-2 | 1.0E-1 | 1.0E-9 | 1.0E-9 | 3.6E-1 | 4.2E-1 | 32 | 26 | 32 | 26 | 0.51 |
| Wf | ng/ml | 1.0E-9 | 1.0E-9 | 1.0E-1 | 1.6E-1 | 2.4E-1 | 4.6E-1 | 1.0E-9 | 1.0E-9 | 1.2E0 | 2.3E0 | 32 | 26 | 32 | 26 | 0.53 |
| Ra | pg/ml | 1.0E-9 | 1.0E-9 | 4.5E-1 | 1.5E0 | 9.9E-1 | 8.6E0 | 1.0E-9 | 1.0E-9 | 3.8E0 | 6.4E1 | 80 | 55 | 80 | 55 | 0.47 |
| Qz | pg/ml | 9.3E0 | 1.1E1 | 5.6E1 | 4.5E1 | 9.5E1 | 7.0E1 | 1.0E-9 | 1.0E-9 | 4.5E2 | 2.8E2 | 80 | 55 | 80 | 55 | 0.52 |
| Qy | pg/ml | 3.8E-1 | 4.6E-1 | 5.7E0 | 2.2E1 | 2.8E1 | 1.1E2 | 1.0E-9 | 1.0E-9 | 2.3E2 | 7.3E2 | 80 | 55 | 80 | 55 | 0.51 |
| Qx | pg/ml | 1.0E-9 | 1.0E-9 | 3.9E0 | 3.4E0 | 2.2E1 | 1.5E1 | 1.0E-9 | 1.0E-9 | 1.9E2 | 1.1E2 | 80 | 55 | 80 | 55 | 0.48 |
| Qw | pg/ml | 1.0E-9 | 1.0E-9 | 3.2E0 | 2.2E0 | 9.5E0 | 9.3E0 | 1.0E-9 | 1.0E-9 | 5.6E1 | 6.6E1 | 80 | 55 | 80 | 55 | 0.47 |
| Qv | pg/ml | 2.0E4 | 1.2E4 | 4.3E4 | 2.6E4 | 1.1E5 | 4.6E4 | 1.4E3 | 1.0E-9 | 9.4E5 | 3.3E5 | 80 | 55 | 80 | 55 | 0.40 |
| Qu | pg/ml | 1.0E1 | 1.0E-9 | 8.9E1 | 9.6E1 | 1.7E2 | 2.0E2 | 1.0E-9 | 1.0E-9 | 7.1E2 | 9.8E2 | 80 | 55 | 80 | 55 | 0.47 |
| Qt | pg/ml | 1.2E1 | 1.4E1 | 5.1E1 | 3.6E1 | 1.2E2 | 6.2E1 | 1.0E-9 | 1.0E-9 | 7.1E2 | 2.2E2 | 80 | 55 | 80 | 55 | 0.50 |
| Qh | ng/ml | 1.7E1 | 2.3E1 | 3.6E1 | 7.0E1 | 5.5E1 | 1.3E2 | 2.5E-1 | 4.3E-1 | 3.4E2 | 8.0E2 | 80 | 55 | 80 | 55 | 0.59 |
| Qg | ng/ml | 7.9E0 | 7.1E0 | 1.6E1 | 1.1E1 | 3.2E1 | 1.4E1 | 1.5E-1 | 3.0E-1 | 2.7E2 | 8.1E1 | 80 | 55 | 80 | 55 | 0.44 |
| Jj | ng/ml | 5.5E2 | 3.9E2 | 2.4E3 | 6.0E2 | 2.2E4 | 6.1E2 | 2.3E0 | 8.7E0 | 3.4E5 | 3.4E3 | 247 | 107 | 247 | 107 | 0.41 |
| Jk | ng/ml | 2.6E0 | 2.9E0 | 2.0E1 | 2.8E1 | 4.5E1 | 5.8E1 | 1.0E-9 | 4.3E-2 | 2.8E2 | 3.9E2 | 247 | 107 | 247 | 107 | 0.54 |
| Jl | ng/ml | 4.8E-1 | 6.5E-1 | 1.5E0 | 9.7E1 | 3.5E0 | 9.6E2 | 1.2E-3 | 5.4E-3 | 2.0E1 | 9.9E3 | 247 | 107 | 247 | 107 | 0.60 |
| Jm | ng/ml | 1.6E1 | 3.2E1 | 6.4E1 | 7.7E1 | 1.5E2 | 2.1E2 | 1.0E-9 | 1.0E-9 | 1.4E3 | 2.1E3 | 247 | 107 | 247 | 107 | 0.58 |
| Jn | pg/ml | 2.5E-1 | 5.2E-1 | 3.9E0 | 1.7E1 | 4.0E1 | 9.5E1 | 1.0E-9 | 1.0E-9 | 6.2E2 | 7.3E2 | 247 | 107 | 247 | 107 | 0.62 |
| Jo | pg/ml | 3.5E3 | 4.5E3 | 4.7E3 | 6.4E3 | 3.9E3 | 1.1E4 | 2.0E1 | 2.4E1 | 2.4E4 | 1.0E5 | 247 | 107 | 247 | 107 | 0.55 |
| Jp | pg/ml | 6.7E4 | 8.4E4 | 6.9E4 | 9.0E4 | 3.6E4 | 4.5E4 | 5.8E2 | 4.6E3 | 1.9E5 | 3.8E5 | 247 | 107 | 247 | 107 | 0.66 |
| Jq | pg/ml | 9.2E1 | 1.4E2 | 1.5E2 | 3.4E2 | 2.0E2 | 9.3E2 | 1.0E0 | 5.6E0 | 2.0E3 | 8.7E3 | 247 | 107 | 247 | 107 | 0.58 |
| Jr | pg/ml | 2.7E0 | 8.3E0 | 6.6E1 | 1.6E2 | 6.9E2 | 8.9E2 | 1.0E-9 | 1.0E-9 | 1.1E4 | 7.4E3 | 247 | 107 | 247 | 107 | 0.63 |
| Js | pg/ml | 1.3E1 | 1.9E1 | 7.4E1 | 1.3E2 | 6.5E2 | 4.9E2 | 1.0E-9 | 1.9E0 | 1.0E4 | 3.0E3 | 247 | 107 | 247 | 107 | 0.63 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jt | pg/ml | 2.2E3 | 3.1E3 | 2.8E3 | 4.7E3 | 2.2E3 | 6.9E3 | 2.2E1 | 1.5E2 | 2.2E4 | 5.2E4 | 247 | 107 | 247 | 107 | 0.61 |
| Xa | pg/ml | 1.0E-9 | 5.0E0 | 9.1E0 | 7.9E1 | 1.9E1 | 2.6E2 | 1.0E-9 | 1.0E-9 | 9.6E1 | 1.2E3 | 32 | 26 | 32 | 26 | 0.62 |
| Ye | pg/ml | 1.0E-9 | 1.0E-9 | 6.5E0 | 1.1E0 | 1.7E1 | 3.1E0 | 1.0E-9 | 1.0E-9 | 6.9E1 | 1.4E1 | 32 | 26 | 32 | 26 | 0.42 |
| Tm | pg/ml | 1.0E-9 | 1.0E-9 | 2.8E0 | 2.3E0 | 4.9E0 | 3.8E0 | 1.0E-9 | 1.0E-9 | 1.8E1 | 8.4E0 | 32 | 26 | 32 | 26 | 0.49 |
| Tl | pg/ml | 1.1E-1 | 1.3E-1 | 2.5E-1 | 1.3E0 | 3.6E-1 | 4.8E0 | 1.0E-9 | 1.0E-9 | 1.2E0 | 2.5E1 | 32 | 26 | 32 | 26 | 0.61 |
| Ju | mIU/ml | 1.1E1 | 1.0E1 | 2.8E1 | 1.8E1 | 4.1E1 | 2.2E1 | 2.5E-1 | 1.7E-1 | 2.3E2 | 1.1E2 | 80 | 55 | 80 | 55 | 0.48 |
| Jv | mIU/ml | 1.7E1 | 1.3E1 | 5.0E1 | 2.2E1 | 7.5E1 | 2.7E1 | 2.4E-2 | 1.7E-2 | 4.4E2 | 1.4E2 | 80 | 55 | 80 | 55 | 0.42 |
| Jy | ng/ml | 1.8E-3 | 1.6E-3 | 2.0E-3 | 3.7E-3 | 1.1E-3 | 7.8E-3 | 1.0E-9 | 1.7E-4 | 4.7E-3 | 4.1E-2 | 80 | 55 | 80 | 55 | 0.48 |
| Kc | pg/ml | 2.2E1 | 2.5E1 | 4.1E1 | 5.2E1 | 4.7E1 | 6.6E1 | 1.0E-9 | 1.0E-9 | 1.9E2 | 3.2E2 | 79 | 57 | 79 | 57 | 0.56 |
| Kd | pg/ml | 1.0E-9 | 1.0E-9 | 1.7E2 | 1.1E3 | 6.5E2 | 5.1E3 | 1.0E-9 | 1.0E-9 | 4.8E3 | 3.8E4 | 79 | 57 | 79 | 57 | 0.53 |
| Ke | pg/ml | 1.2E4 | 1.5E4 | 1.3E4 | 2.6E4 | 8.7E3 | 4.4E4 | 1.0E3 | 6.7E2 | 4.6E4 | 3.2E5 | 79 | 57 | 79 | 57 | 0.62 |
| Kf | pg/mL | 5.9E0 | 6.7E0 | 6.5E0 | 9.0E0 | 5.1E0 | 1.2E1 | 1.0E-9 | 1.0E-9 | 2.2E1 | 7.8E1 | 79 | 57 | 79 | 57 | 0.54 |
| Kg | pg/mL | 8.9E2 | 1.0E3 | 1.8E3 | 2.7E3 | 2.8E3 | 6.0E3 | 7.7E1 | 1.3E2 | 2.2E4 | 3.6E4 | 79 | 57 | 79 | 57 | 0.50 |
| Ki | pg/ml | 5.7E1 | 7.3E1 | 6.4E1 | 8.1E1 | 5.0E1 | 5.6E1 | 1.0E-9 | 1.0E-9 | 2.9E2 | 2.5E2 | 79 | 57 | 79 | 57 | 0.62 |
| Kj | pg/ml | 8.4E2 | 7.7E2 | 1.4E3 | 1.5E3 | 1.5E3 | 2.2E3 | 6.6E1 | 3.3E1 | 8.8E3 | 1.5E4 | 79 | 57 | 79 | 57 | 0.47 |
| Kk | pg/ml | 6.8E0 | 8.5E0 | 1.2E1 | 1.7E1 | 1.5E1 | 1.8E1 | 1.0E-9 | 1.0E-9 | 8.1E1 | 6.1E1 | 79 | 57 | 79 | 57 | 0.59 |
| Kl | pg/ml | 2.1E4 | 1.6E4 | 2.9E4 | 2.5E4 | 2.6E4 | 2.6E4 | 4.1E2 | 2.3E2 | 1.1E5 | 1.3E5 | 79 | 57 | 79 | 57 | 0.45 |
| Kn | pg/ml | 2.9E1 | 3.0E1 | 5.7E1 | 1.7E2 | 8.3E1 | 6.5E2 | 1.0E-9 | 1.0E-9 | 3.8E2 | 4.9E3 | 79 | 57 | 79 | 57 | 0.56 |
| Ko | pg/ml | 3.4E2 | 4.0E2 | 4.4E2 | 6.2E2 | 4.6E2 | 8.0E2 | 1.0E-9 | 1.0E-9 | 2.0E3 | 4.1E3 | 79 | 57 | 79 | 57 | 0.57 |
| Kp | pg/ml | 3.4E2 | 3.9E2 | 3.4E2 | 6.2E2 | 2.5E2 | 1.7E3 | 1.0E-9 | 1.0E-9 | 9.4E2 | 1.3E4 | 79 | 57 | 79 | 57 | 0.57 |
| Kq | pg/ml | 3.2E2 | 4.2E2 | 3.7E2 | 3.7E3 | 3.4E2 | 2.1E4 | 5.1E0 | 1.6E0 | 2.1E3 | 1.6E5 | 76 | 55 | 76 | 55 | 0.62 |
| Kr | pg/ml | 1.0E-9 | 9.9E-1 | 1.5E0 | 1.0E1 | 2.8E0 | 5.6E1 | 1.0E-9 | 1.0E-9 | 1.3E1 | 4.2E2 | 76 | 55 | 76 | 55 | 0.60 |
| Ks | pg/ml | 1.4E4 | 1.9E4 | 2.0E4 | 2.2E4 | 1.8E4 | 1.8E4 | 4.5E2 | 5.1E1 | 7.9E4 | 5.1E4 | 76 | 55 | 76 | 55 | 0.53 |
| Ps | ng/ml | 1.5E2 | 2.9E2 | 5.6E2 | 1.2E3 | 1.6E3 | 2.8E3 | 1.6E0 | 5.5E0 | 9.0E3 | 1.2E4 | 32 | 26 | 32 | 26 | 0.59 |
| Kx | ng/ml | 1.4E-3 | 4.5E-3 | 6.0E-3 | 1.2E-2 | 1.4E-2 | 1.9E-2 | 1.0E-9 | 1.0E-9 | 1.0E-1 | 7.9E-2 | 78 | 57 | 78 | 57 | 0.59 |
| Ky | ng/ml | 1.1E-1 | 2.2E-1 | 3.5E-1 | 4.8E-1 | 7.7E-1 | 7.6E-1 | 1.0E-9 | 1.0E-9 | 5.1E0 | 4.4E0 | 78 | 57 | 78 | 57 | 0.58 |
| Kz | ng/ml | 1.0E-9 | 1.0E-9 | 3.9E-3 | 3.9E-3 | 5.9E-3 | 6.7E-3 | 1.0E-9 | 1.0E-9 | 1.6E-2 | 2.5E-2 | 78 | 57 | 78 | 57 | 0.48 |
| Rz | ng/ml | 3.8E-1 | 3.2E-1 | 9.4E-1 | 9.0E-1 | 1.4E0 | 1.5E0 | 1.1E-2 | 4.6E-3 | 6.7E0 | 7.5E0 | 32 | 26 | 32 | 26 | 0.52 |
| Ry | ng/ml | 1.6E-2 | 2.0E-2 | 2.1E-2 | 4.1E-2 | 1.7E-2 | 7.1E-2 | 1.0E-9 | 1.0E-9 | 6.5E-2 | 3.5E-1 | 32 | 26 | 32 | 26 | 0.54 |
| Rx | ng/ml | 1.0E-9 | 1.8E-5 | 1.2E-3 | 1.8E-3 | 2.1E-3 | 2.7E-3 | 1.0E-9 | 1.0E-9 | 8.6E-3 | 8.6E-3 | 32 | 26 | 32 | 26 | 0.56 |
| Ld | pg/ml | 1.0E-9 | 1.0E-9 | 3.1E0 | 4.9E0 | 8.6E0 | 9.0E0 | 1.0E-9 | 1.0E-9 | 6.9E1 | 5.0E1 | 79 | 57 | 79 | 57 | 0.57 |
| Lh | pg/ml | 1.0E4 | 2.0E4 | 1.9E4 | 4.0E4 | 2.6E4 | 7.3E4 | 1.0E-9 | 1.0E-9 | 2.6E5 | 4.8E5 | 247 | 108 | 247 | 108 | 0.64 |
| Li | pg/ml | 2.9E3 | 7.7E3 | 1.6E4 | 3.6E4 | 8.7E4 | 1.0E5 | 1.2E1 | 1.3E1 | 1.3E6 | 9.2E5 | 247 | 108 | 247 | 108 | 0.65 |
| Lj | pg/ml | 2.3E3 | 5.0E3 | 1.7E4 | 3.2E4 | 5.3E4 | 6.7E4 | 1.0E-9 | 1.0E-9 | 4.3E5 | 4.1E5 | 247 | 108 | 247 | 108 | 0.61 |
| Lp | pg/ml | 1.1E1 | 8.0E0 | 9.3E1 | 1.4E2 | 2.2E2 | 3.5E2 | 1.0E-9 | 1.0E-9 | 1.1E3 | 1.4E3 | 32 | 26 | 32 | 26 | 0.49 |
| Lt | pg/ml | 1.0E-9 | 1.0E-9 | 1.2E0 | 1.7E0 | 5.1E0 | 6.2E0 | 1.0E-9 | 1.0E-9 | 2.5E1 | 2.5E1 | 32 | 26 | 32 | 26 | 0.51 |
| Rv | ng/ml | 5.0E-4 | 5.0E-4 | 1.1E-3 | 2.0E-3 | 1.8E-3 | 4.0E-3 | 1.0E-9 | 1.0E-9 | 9.2E-3 | 1.6E-2 | 32 | 26 | 32 | 26 | 0.52 |
| Ru | ng/ml | 1.0E-9 | 1.0E-9 | 1.6E-2 | 2.9E-2 | 6.5E-2 | 9.3E-2 | 1.0E-9 | 1.0E-9 | 3.1E-1 | 3.5E-1 | 32 | 26 | 32 | 26 | 0.53 |
| Rt | ng/ml | 7.6E-2 | 6.7E-2 | 1.0E-1 | 4.3E-1 | 9.5E-2 | 1.4E0 | 6.5E-3 | 1.3E-3 | 3.8E-1 | 7.4E0 | 32 | 26 | 32 | 26 | 0.51 |
| Yl | pg/ml | 1.4E1 | 1.2E1 | 1.6E1 | 2.7E1 | 1.2E1 | 4.4E1 | 1.0E-9 | 1.0E-9 | 4.7E1 | 2.2E2 | 32 | 26 | 32 | 26 | 0.49 |
| Rm | ng/ml | 1.8E1 | 2.0E1 | 4.5E1 | 5.7E1 | 7.2E1 | 1.0E2 | 2.2E-1 | 2.3E-1 | 3.4E2 | 6.5E2 | 80 | 54 | 80 | 54 | 0.52 |
| Rh | ng/ml | 1.7E2 | 1.7E2 | 5.6E2 | 5.7E2 | 1.9E3 | 2.3E3 | 7.5E0 | 2.5E1 | 1.7E4 | 1.7E4 | 80 | 54 | 80 | 54 | 0.47 |
| Ri | ng/ml | 4.4E-2 | 2.2E-2 | 3.9E0 | 3.7E0 | 8.4E0 | 7.6E0 | 1.0E-9 | 1.0E-9 | 4.9E1 | 4.5E1 | 80 | 54 | 80 | 54 | 0.49 |
| Rg | ng/ml | 1.0E-9 | 1.0E-9 | 4.5E-2 | 1.4E-1 | 3.4E-1 | 5.3E-1 | 1.0E-9 | 1.0E-9 | 3.0E0 | 3.3E0 | 80 | 54 | 80 | 54 | 0.53 |
| Rj | ng/ml | 1.0E-9 | 1.0E-9 | 8.0E-1 | 6.0E0 | 1.8E0 | 3.7E1 | 1.0E-9 | 1.0E-9 | 1.1E1 | 2.7E2 | 80 | 54 | 80 | 54 | 0.50 |
| Rf | ng/ml | 4.1E-1 | 3.3E-1 | 7.8E-1 | 1.4E0 | 1.0E0 | 3.1E0 | 2.1E-2 | 2.1E-2 | 6.2E0 | 1.7E1 | 80 | 54 | 80 | 54 | 0.47 |
| Ql | pg/ml | 3.6E0 | 5.5E0 | 1.0E1 | 1.5E1 | 1.8E1 | 2.9E1 | 1.0E-9 | 1.0E-9 | 1.1E2 | 1.8E2 | 80 | 55 | 80 | 55 | 0.54 |
| Qm | pg/ml | 2.4E-1 | 8.6E0 | 1.8E1 | 2.4E1 | 3.5E1 | 3.6E1 | 1.0E-9 | 1.0E-9 | 1.9E2 | 1.8E2 | 80 | 55 | 80 | 55 | 0.57 |
| Qn | pg/ml | 6.1E-1 | 6.1E-1 | 6.4E0 | 7.9E0 | 2.5E1 | 2.0E1 | 1.0E-9 | 1.0E-9 | 2.2E2 | 2.0E2 | 80 | 55 | 80 | 55 | 0.47 |
| Nv | pg/ml | 3.2E3 | 6.2E3 | 7.7E3 | 1.7E4 | 1.5E4 | 2.9E4 | 1.0E-9 | 1.9E1 | 1.3E5 | 1.6E5 | 247 | 109 | 247 | 109 | 0.64 |
| Nw | pg/ml | 8.3E3 | 1.4E4 | 1.2E4 | 2.2E4 | 1.6E4 | 3.0E4 | 2.0E2 | 1.9E2 | 2.1E5 | 2.2E5 | 247 | 109 | 247 | 109 | 0.68 |
| Nx | pg/ml | 1.7E2 | 2.4E2 | 3.7E2 | 6.3E2 | 5.7E2 | 7.5E2 | 1.0E-9 | 1.0E-9 | 3.5E3 | 4.1E3 | 247 | 109 | 247 | 109 | 0.63 |
| Ny | pg/ml | 5.2E0 | 1.2E1 | 1.2E2 | 8.0E1 | 1.6E3 | 3.0E2 | 1.0E-9 | 1.0E-9 | 2.5E4 | 2.8E3 | 247 | 109 | 247 | 109 | 0.64 |
| Oa | pg/ml | 1.4E2 | 2.4E2 | 3.4E2 | 7.0E2 | 5.4E2 | 9.6E2 | 1.0E-9 | 1.0E-9 | 3.0E3 | 4.5E3 | 80 | 55 | 80 | 55 | 0.61 |
| Op | pg/ml | 4.3E5 | 4.4E5 | 4.4E5 | 4.4E5 | 1.5E5 | 1.9E5 | 2.1E5 | 5.2E4 | 7.3E5 | 7.5E5 | 32 | 26 | 32 | 26 | 0.52 |
| Wn | ng/ml | 1.1E1 | 1.1E1 | 1.1E2 | 1.7E1 | 3.6E2 | 1.7E1 | 1.2E0 | 7.6E-1 | 1.8E3 | 5.6E1 | 26 | 14 | 26 | 14 | 0.45 |
| Tk | ng/ml | 1.1E2 | 1.2E2 | 3.1E2 | 3.6E2 | 7.9E2 | 6.2E2 | 3.0E0 | 4.0E0 | 4.2E3 | 2.3E3 | 27 | 17 | 27 | 17 | 0.51 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oe | pg/ml | 4.7E1 | 4.2E0 | 2.5E2 | 2.4E2 | 3.8E2 | 3.8E2 | 1.0E-9 | 1.0E-9 | 2.3E3 | 2.0E3 | 246 | 108 | 246 | 108 | 0.48 |
| Of | pg/ml | 1.6E2 | 8.9E1 | 4.5E2 | 6.3E3 | 1.9E4 | 2.3E4 | 1.0E-9 | 1.0E-9 | 1.9E5 | 1.7E5 | 247 | 109 | 247 | 109 | 0.46 |
| Og | pg/ml | 7.0E-2 | 6.6E-2 | 4.4E-1 | 1.3E-1 | 1.7E0 | 2.9E-1 | 1.0E-9 | 1.0E-9 | 1.9E1 | 2.5E0 | 247 | 109 | 247 | 109 | 0.45 |
| Oh | pg/ml | 2.3E0 | 4.1E0 | 1.5E1 | 1.7E2 | 1.0E2 | 1.5E3 | 1.0E-9 | 1.0E-9 | 1.4E3 | 1.6E4 | 247 | 109 | 247 | 109 | 0.60 |
| Oi | pg/ml | 1.5E0 | 2.6E0 | 4.9E0 | 5.3E0 | 8.2E0 | 6.9E0 | 1.0E-9 | 1.0E-9 | 6.7E1 | 3.1E1 | 247 | 109 | 247 | 109 | 0.54 |
| Ok | pg/ml | 3.4E2 | 6.1E2 | 4.5E2 | 9.3E2 | 4.2E2 | 1.2E3 | 2.9E1 | 1.5E1 | 2.8E3 | 7.8E3 | 247 | 109 | 247 | 109 | 0.69 |
| Om | pg/ml | 3.8E2 | 5.2E2 | 8.0E2 | 1.4E3 | 2.3E3 | 5.0E3 | 1.0E-9 | 1.0E-9 | 3.0E4 | 5.1E4 | 247 | 109 | 247 | 109 | 0.61 |
| On | pg/ml | 1.5E2 | 2.7E2 | 2.5E2 | 5.5E2 | 4.1E2 | 9.7E2 | 1.0E-9 | 1.0E1 | 4.5E3 | 8.5E3 | 247 | 109 | 247 | 109 | 0.66 |
| Or | pg/ml | 1.1E1 | 1.9E1 | 2.1E1 | 7.1E1 | 3.0E1 | 1.2E2 | 1.0E-9 | 1.0E-9 | 2.0E2 | 5.1E2 | 79 | 58 | 79 | 58 | 0.60 |
| Ow | pg/ml | 3.6E1 | 4.7E1 | 2.2E2 | 2.3E2 | 9.6E2 | 5.3E2 | 1.0E-9 | 1.0E-9 | 8.1E3 | 3.0E3 | 79 | 58 | 79 | 58 | 0.53 |
| Ou | pg/ml | 4.2E2 | 5.7E2 | 9.5E2 | 1.6E3 | 1.4E3 | 2.6E3 | 2.2E1 | 1.0E-9 | 9.8E3 | 1.1E4 | 79 | 58 | 79 | 58 | 0.55 |
| Ul | ng/ml | 1.0E-9 | 1.0E-9 | 1.2E0 | 1.9E0 | 4.9E0 | 8.3E0 | 1.0E-9 | 1.0E-9 | 2.9E1 | 5.6E1 | 81 | 55 | 81 | 55 | 0.51 |
| Uo | ng/ml | 1.0E-9 | 1.0E-9 | 8.5E-2 | 6.0E-2 | 2.4E-1 | 1.6E-1 | 1.0E-9 | 1.0E-9 | 1.3E0 | 6.9E-1 | 81 | 55 | 81 | 55 | 0.47 |
| Uk | ng/ml | 1.0E-9 | 1.0E-9 | 7.4E-3 | 3.9E-3 | 3.7E-2 | 1.8E-2 | 1.0E-9 | 1.0E-9 | 3.2E-1 | 1.3E-1 | 81 | 55 | 81 | 55 | 0.44 |
| Um | ng/ml | 1.0E-9 | 1.0E-9 | 3.0E-1 | 1.3E-1 | 7.0E-1 | 4.0E-1 | 1.0E-9 | 1.0E-9 | 3.6E0 | 2.3E0 | 81 | 55 | 81 | 55 | 0.41 |
| Uf | ng/ml | 5.3E-2 | 8.6E-2 | 1.2E-1 | 2.6E-1 | 1.6E-1 | 7.1E-1 | 2.7E-3 | 1.0E-3 | 7.8E-1 | 5.1E0 | 81 | 55 | 81 | 55 | 0.58 |
| Uh | ng/ml | 1.6E0 | 4.1E0 | 2.8E0 | 4.9E0 | 2.9E0 | 4.2E0 | 3.6E-2 | 4.7E-2 | 1.5E1 | 1.8E1 | 81 | 55 | 81 | 55 | 0.66 |
| Un | ng/ml | 1.7E0 | 1.8E0 | 1.8E0 | 2.8E0 | 1.0E0 | 3.5E0 | 3.5E-1 | 3.4E-1 | 4.9E0 | 2.5E1 | 81 | 55 | 81 | 55 | 0.61 |
| Ug | ng/ml | 1.3E1 | 8.8E0 | 2.3E1 | 2.0E1 | 2.5E1 | 2.9E1 | 1.5E0 | 1.0E0 | 1.4E2 | 1.6E2 | 81 | 55 | 81 | 55 | 0.43 |
| Ur | ng/ml | 1.4E-1 | 6.5E-2 | 3.1E-1 | 4.4E-1 | 5.6E-1 | 1.3E0 | 1.0E-9 | 1.0E-9 | 3.0E0 | 7.3E0 | 81 | 54 | 81 | 54 | 0.42 |
| Up | ng/ml | 1.0E-9 | 1.0E-9 | 2.0E-3 | 4.9E-2 | 7.3E-3 | 3.2E-1 | 1.0E-9 | 1.0E-9 | 5.3E-2 | 2.4E0 | 81 | 54 | 81 | 54 | 0.59 |
| Us | ng/ml | 1.8E-3 | 3.9E-3 | 9.5E-3 | 5.8E-2 | 1.9E-2 | 2.3E-1 | 1.0E-9 | 1.0E-9 | 1.2E-1 | 1.7E0 | 81 | 54 | 81 | 54 | 0.58 |
| Uv | ng/ml | 3.1E-3 | 2.5E-3 | 1.7E-2 | 1.6E-2 | 5.0E-2 | 5.9E-2 | 1.0E-9 | 1.0E-9 | 3.5E-1 | 4.1E-1 | 81 | 54 | 81 | 54 | 0.47 |
| Ut | ng/ml | 6.0E-1 | 1.0E0 | 2.3E0 | 4.8E0 | 6.3E0 | 1.0E1 | 1.0E-9 | 1.0E-9 | 5.2E1 | 6.5E1 | 81 | 54 | 81 | 54 | 0.61 |
| Uu | ng/ml | 7.2E0 | 5.8E0 | 8.0E0 | 6.5E0 | 5.3E0 | 4.4E0 | 5.4E-1 | 5.7E-1 | 2.9E1 | 2.3E1 | 81 | 54 | 81 | 54 | 0.41 |
| Uw | ng/ml | 2.1E0 | 2.6E0 | 2.8E0 | 4.5E0 | 2.8E0 | 7.4E0 | 1.5E-1 | 1.0E-1 | 9.8E0 | 3.9E1 | 33 | 26 | 33 | 26 | 0.62 |
| Vb | ng/ml | 1.1E0 | 1.1E0 | 1.1E0 | 1.1E0 | 4.1E-1 | 1.2E0 | 4.7E-1 | 8.5E-2 | 2.0E0 | 6.4E0 | 33 | 26 | 33 | 26 | 0.37 |
| Vc | ng/ml | 1.0E-9 | 1.0E-9 | 6.1E-3 | 5.1E-4 | 2.3E-2 | 2.6E-3 | 1.0E-9 | 1.0E-9 | 1.1E-1 | 1.3E-2 | 33 | 26 | 33 | 26 | 0.47 |
| Uy | ng/ml | 1.3E0 | 1.3E0 | 4.1E0 | 1.3E1 | 1.0E1 | 2.5E1 | 8.7E-2 | 2.0E-2 | 5.1E1 | 9.9E1 | 33 | 26 | 33 | 26 | 0.56 |
| Uz | ng/ml | 1.0E-9 | 1.0E-9 | 1.3E-2 | 1.3E0 | 7.6E-2 | 6.5E0 | 1.0E-9 | 1.0E-9 | 4.4E-1 | 3.3E1 | 33 | 26 | 33 | 26 | 0.52 |
| Ux | ng/ml | 2.0E2 | 1.7E2 | 1.9E2 | 1.9E2 | 1.4E2 | 1.4E2 | 1.2E1 | 4.5E0 | 4.8E2 | 4.9E2 | 33 | 26 | 33 | 26 | 0.50 |
| Va | ng/ml | 1.4E1 | 5.3E0 | 2.5E1 | 2.0E1 | 3.0E1 | 2.5E1 | 3.1E-1 | 3.6E-1 | 1.2E2 | 9.6E1 | 33 | 26 | 33 | 26 | 0.43 |
| Vh | ng/ml | 1.0E-2 | 1.9E-2 | 1.8E-2 | 5.4E-2 | 2.4E-2 | 1.7E-1 | 3.9E-4 | 1.0E-9 | 1.2E-1 | 8.6E-1 | 33 | 26 | 33 | 26 | 0.61 |
| Vi | ng/ml | 4.2E-3 | 4.2E-3 | 7.6E-3 | 8.9E-2 | 8.2E-3 | 3.6E-1 | 1.0E-9 | 1.0E-9 | 3.3E-2 | 1.8E0 | 33 | 26 | 33 | 26 | 0.57 |
| Vj | ng/ml | 2.3E1 | 6.2E1 | 4.8E1 | 9.7E1 | 5.0E1 | 1.4E2 | 4.6E0 | 1.4E0 | 1.8E2 | 6.5E2 | 33 | 25 | 33 | 25 | 0.61 |
| Vp | ng/ml | 1.0E-9 | 1.0E-9 | 1.4E-1 | 1.1E0 | 6.5E-1 | 6.6E0 | 1.0E-9 | 1.0E-9 | 3.9E0 | 4.9E1 | 81 | 55 | 81 | 55 | 0.57 |
| Vt | ng/ml | 5.6E0 | 7.9E0 | 6.6E0 | 1.4E1 | 5.1E0 | 2.2E1 | 9.6E-1 | 5.6E-1 | 3.2E1 | 1.6E2 | 81 | 55 | 81 | 55 | 0.64 |
| Vu | ng/ml | 1.0E-9 | 1.0E-9 | 1.1E0 | 2.3E0 | 2.4E0 | 4.3E0 | 1.0E-9 | 1.0E-9 | 1.6E1 | 2.2E1 | 79 | 53 | 79 | 53 | 0.57 |
| Vq | ng/ml | 1.5E2 | 2.8E2 | 6.1E2 | 9.2E2 | 1.0E3 | 2.1E3 | 9.2E-1 | 6.5E-1 | 5.0E3 | 1.2E4 | 66 | 42 | 66 | 42 | 0.55 |
| Vo | ng/ml | 2.5E1 | 2.6E1 | 2.5E1 | 2.4E1 | 4.3E0 | 7.1E0 | 9.7E0 | 1.9E0 | 3.5E1 | 4.8E1 | 81 | 55 | 81 | 55 | 0.50 |
| Vs | ng/ml | 1.0E-9 | 1.0E-9 | 4.7E0 | 1.3E1 | 1.3E1 | 6.3E1 | 1.0E-9 | 1.0E-9 | 8.9E1 | 4.5E2 | 80 | 53 | 80 | 53 | 0.47 |
| Vv | ng/ml | 2.9E0 | 3.0E0 | 5.9E0 | 6.3E0 | 1.1E1 | 9.2E0 | 1.0E-9 | 1.0E-9 | 8.4E1 | 4.4E1 | 81 | 54 | 81 | 54 | 0.49 |
| Vw | ng/ml | 3.6E1 | 4.2E1 | 3.3E1 | 3.7E1 | 1.7E1 | 2.0E1 | 3.1E0 | 2.5E0 | 6.7E1 | 6.9E1 | 33 | 26 | 33 | 26 | 0.57 |
| Oy | pg/ml | 4.9E-1 | 3.2E-1 | 7.2E0 | 3.5E0 | 3.5E1 | 1.1E1 | 1.0E-9 | 1.0E-9 | 4.0E2 | 9.9E1 | 247 | 108 | 247 | 108 | 0.45 |
| Oz | pg/ml | 7.9E-3 | 1.0E-9 | 2.6E-1 | 7.2E-1 | 3.9E-1 | 3.8E0 | 1.0E-9 | 1.0E-9 | 2.1E0 | 2.9E1 | 247 | 108 | 247 | 108 | 0.46 |
| Pa | pg/ml | 3.8E-1 | 4.5E-1 | 1.4E0 | 4.6E0 | 6.4E0 | 2.4E1 | 1.0E-9 | 1.0E-9 | 8.6E1 | 2.3E2 | 247 | 108 | 247 | 108 | 0.55 |
| Pb | pg/ml | 1.0E-9 | 1.0E-9 | 2.1E0 | 7.3E-1 | 3.1E1 | 4.1E0 | 1.0E-9 | 1.0E-9 | 4.9E2 | 3.2E1 | 247 | 108 | 247 | 108 | 0.47 |
| Pc | pg/ml | 5.3E-2 | 1.0E-9 | 4.1E-1 | 3.7E0 | 1.0E0 | 3.2E1 | 1.0E-9 | 1.0E-9 | 1.4E1 | 3.3E2 | 247 | 108 | 247 | 108 | 0.47 |
| Pd | pg/ml | 1.5E0 | 2.1E0 | 3.8E0 | 1.4E1 | 8.6E0 | 8.2E1 | 1.0E-9 | 1.0E-9 | 9.4E1 | 8.4E2 | 247 | 108 | 247 | 108 | 0.55 |
| Pe | pg/ml | 1.9E1 | 4.1E1 | 9.2E1 | 4.2E2 | 3.8E2 | 1.7E3 | 1.0E-9 | 1.0E-9 | 4.7E3 | 1.5E4 | 247 | 108 | 247 | 108 | 0.62 |
| Pf | pg/ml | 1.4E0 | 2.6E0 | 1.1E1 | 3.1E1 | 4.5E1 | 1.5E2 | 1.0E-9 | 1.0E-9 | 4.8E2 | 1.5E3 | 247 | 108 | 247 | 108 | 0.58 |
| Pg | pg/ml | 3.5E0 | 7.5E0 | 4.8E1 | 1.6E2 | 3.4E2 | 7.9E2 | 1.0E-9 | 1.0E-9 | 4.2E3 | 7.7E3 | 247 | 108 | 247 | 108 | 0.61 |
| Ph | ng/ml | 1.5E-1 | 1.5E-1 | 3.5E-1 | 4.4E-1 | 4.6E-1 | 8.5E-1 | 1.0E-9 | 1.0E-9 | 2.2E0 | 5.4E0 | 79 | 58 | 79 | 58 | 0.50 |
| Pi | ng/ml | 1.9E-1 | 2.4E-1 | 2.9E-1 | 1.8E0 | 4.2E-1 | 1.1E1 | 1.0E-9 | 1.0E-9 | 3.2E0 | 8.2E1 | 79 | 58 | 79 | 58 | 0.57 |
| Pj | ng/mL | 4.9E0 | 6.0E0 | 5.4E0 | 7.3E0 | 3.3E0 | 5.7E0 | 4.9E-1 | 4.0E-1 | 1.6E1 | 3.1E1 | 79 | 58 | 79 | 58 | 0.59 |
| Pk | ng/ml | 7.6E-3 | 1.2E-2 | 1.3E-2 | 4.4E-2 | 3.0E-2 | 2.0E-1 | 1.0E-9 | 1.0E-9 | 2.5E-1 | 1.5E0 | 79 | 58 | 79 | 58 | 0.64 |
| aA | mg/dL | 8.8E-1 | 1.0E0 | 9.8E-1 | 1.2E0 | 4.9E-1 | 7.9E-1 | 3.0E-1 | 4.0E-1 | 4.2E0 | 4.7E0 | 397 | 140 | 397 | 140 | 0.59 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aC | mg/mL | 2.6E0 | 2.0E0 | 2.9E0 | 2.3E0 | 1.3E0 | 1.2E0 | 1.1E0 | 7.5E-1 | 7.4E0 | 6.7E0 | 107 | 69 | 107 | 69 | 0.34 |
| aD | ug/mL | 2.8E0 | 3.2E0 | 4.7E0 | 4.7E0 | 5.2E0 | 3.8E0 | 7.5E-1 | 7.5E-1 | 3.5E1 | 2.1E1 | 107 | 69 | 107 | 69 | 0.52 |
| aE | mg/mL | 5.8E-1 | 5.7E-1 | 5.9E-1 | 6.0E-1 | 1.6E-1 | 1.9E-1 | 2.8E-1 | 1.8E-1 | 1.1E0 | 1.2E0 | 107 | 69 | 107 | 69 | 0.50 |
| aF | ng/mL | 2.2E0 | 2.4E0 | 5.2E0 | 4.9E0 | 8.4E0 | 6.4E0 | 4.3E-3 | 4.3E-3 | 5.0E1 | 3.5E1 | 107 | 69 | 107 | 69 | 0.53 |
| aG | mg/mL | 1.4E-1 | 1.4E-1 | 1.6E-1 | 1.6E-1 | 8.9E-2 | 8.3E-2 | 3.2E-2 | 5.1E-2 | 4.6E-1 | 4.8E-1 | 107 | 69 | 107 | 69 | 0.51 |
| aH | ug/mL | 7.4E1 | 7.1E1 | 7.6E1 | 7.9E1 | 3.8E1 | 4.3E1 | 8.9E0 | 1.1E1 | 2.0E2 | 2.0E2 | 107 | 69 | 107 | 69 | 0.51 |
| aI | ug/mL | 1.8E2 | 1.6E2 | 1.8E2 | 1.7E2 | 5.9E1 | 6.3E1 | 3.2E1 | 4.7E1 | 3.3E2 | 3.4E2 | 107 | 69 | 107 | 69 | 0.43 |
| aJ | ug/mL | 2.5E0 | 2.5E0 | 3.1E0 | 3.7E0 | 2.3E0 | 3.3E0 | 9.5E-1 | 8.2E-1 | 1.4E1 | 2.3E1 | 107 | 69 | 107 | 69 | 0.56 |
| aK | ng/mL | 1.4E0 | 1.1E0 | 2.1E0 | 1.7E0 | 2.0E0 | 1.8E0 | 2.8E-2 | 2.9E-4 | 9.1E0 | 1.0E1 | 107 | 69 | 107 | 69 | 0.44 |
| aL | mg/mL | 7.5E-1 | 7.2E-1 | 7.8E-1 | 7.3E-1 | 2.6E-1 | 2.5E-1 | 2.2E-1 | 2.7E-1 | 1.4E0 | 1.7E0 | 107 | 69 | 107 | 69 | 0.44 |
| aM | U/mL | 1.5E1 | 2.3E1 | 3.2E1 | 6.4E1 | 5.2E1 | 1.3E2 | 4.2E-2 | 4.2E-2 | 3.5E2 | 8.2E2 | 107 | 69 | 107 | 69 | 0.63 |
| aN | U/mL | 1.2E1 | 2.1E1 | 1.7E1 | 3.9E1 | 1.9E1 | 6.1E1 | 2.5E-3 | 2.5E-3 | 9.7E1 | 3.8E2 | 107 | 69 | 107 | 69 | 0.68 |
| aO | pg/mL | 4.8E1 | 7.2E1 | 4.7E2 | 3.9E2 | 1.1E3 | 7.0E2 | 6.0E-2 | 6.0E-2 | 6.6E3 | 3.3E3 | 107 | 69 | 107 | 69 | 0.53 |
| aP | ng/mL | 1.6E0 | 1.7E0 | 2.3E0 | 2.6E0 | 2.8E0 | 3.4E0 | 4.5E-1 | 6.8E-1 | 2.8E1 | 2.8E1 | 107 | 69 | 107 | 69 | 0.55 |
| aQ | ng/mL | 2.5E-1 | 2.4E-1 | 3.5E-1 | 3.6E-1 | 2.8E-1 | 3.7E-1 | 2.0E-4 | 2.0E-4 | 1.1E0 | 2.0E0 | 107 | 69 | 107 | 69 | 0.48 |
| aR | ng/mL | 1.7E0 | 1.9E0 | 3.0E0 | 3.1E0 | 4.4E0 | 3.3E0 | 2.6E-1 | 5.6E-1 | 3.4E1 | 1.7E1 | 107 | 69 | 107 | 69 | 0.56 |
| aS | ng/mL | 3.1E-1 | 5.1E-1 | 9.6E-1 | 1.0E0 | 3.2E0 | 1.3E0 | 4.2E-3 | 4.2E-3 | 3.3E1 | 6.2E0 | 107 | 69 | 107 | 69 | 0.61 |
| aU | pg/mL | 7.6E1 | 5.7E1 | 1.1E2 | 8.9E1 | 1.0E2 | 1.2E2 | 7.4E-2 | 7.4E-2 | 5.1E2 | 7.0E2 | 107 | 69 | 107 | 69 | 0.42 |
| aV | ng/mL | 6.3E-1 | 4.5E-1 | 9.3E-1 | 1.2E0 | 1.0E0 | 3.9E0 | 3.8E-2 | 7.6E-4 | 6.0E0 | 3.3E1 | 107 | 69 | 107 | 69 | 0.46 |
| aW | pg/mL | 1.9E1 | 2.0E1 | 2.1E1 | 2.4E1 | 1.8E1 | 4.9E1 | 7.2E-2 | 7.2E-2 | 1.7E2 | 4.2E2 | 107 | 69 | 107 | 69 | 0.47 |
| aX | ng/mL | 8.9E0 | 7.1E0 | 1.5E1 | 1.9E1 | 2.4E1 | 4.2E1 | 3.0E-1 | 6.2E-1 | 2.2E2 | 3.1E2 | 107 | 69 | 107 | 69 | 0.45 |
| aY | pg/mL | 5.3E1 | 5.4E1 | 6.8E1 | 8.7E1 | 5.7E1 | 1.6E2 | 4.1E1 | 4.1E-1 | 3.1E2 | 1.2E3 | 107 | 69 | 107 | 69 | 0.51 |
| aZ | pg/mL | 2.2E2 | 2.9E2 | 5.3E2 | 9.0E2 | 1.2E3 | 1.7E3 | 1.7E0 | 1.7E0 | 1.2E4 | 7.9E3 | 107 | 69 | 107 | 69 | 0.54 |
| bA | ng/mL | 1.0E1 | 2.7E1 | 4.0E1 | 1.3E2 | 8.6E1 | 2.5E2 | 3.0E-2 | 3.0E-2 | 6.8E2 | 1.5E3 | 107 | 69 | 107 | 69 | 0.65 |
| bB | ng/mL | 2.8E2 | 2.7E2 | 3.1E2 | 2.9E2 | 1.8E2 | 1.8E2 | 2.1E0 | 1.2E1 | 9.5E2 | 8.1E2 | 107 | 69 | 107 | 69 | 0.45 |
| bC | ng/mL | 3.3E2 | 3.2E2 | 5.6E2 | 7.9E2 | 7.2E2 | 1.1E3 | 1.4E1 | 3.5E1 | 4.0E3 | 4.7E3 | 107 | 69 | 107 | 69 | 0.52 |
| bE | mg/mL | 5.3E0 | 4.6E0 | 5.8E0 | 5.0E0 | 2.2E0 | 2.1E0 | 1.8E0 | 1.3E0 | 1.2E1 | 1.2E1 | 107 | 69 | 107 | 69 | 0.39 |
| bF | pg/mL | 3.5E1 | 4.3E1 | 3.2E2 | 3.9E2 | 1.3E3 | 1.5E3 | 5.0E-2 | 2.5E0 | 1.1E4 | 1.0E4 | 107 | 69 | 107 | 69 | 0.54 |
| bG | ng/mL | 1.5E0 | 1.8E0 | 2.9E0 | 3.5E0 | 4.2E0 | 4.8E0 | 1.1E-1 | 1.6E-1 | 2.6E1 | 3.0E1 | 107 | 69 | 107 | 69 | 0.54 |
| bH | pg/mL | 5.7E-1 | 5.7E-1 | 6.3E0 | 6.2E0 | 2.7E1 | 1.6E1 | 5.7E-1 | 5.7E-1 | 2.8E2 | 1.2E2 | 107 | 69 | 107 | 69 | 0.50 |
| bI | ng/mL | 4.0E-3 | 4.0E-3 | 7.5E-2 | 1.2E-1 | 1.5E-1 | 2.5E-1 | 4.0E-3 | 4.0E-3 | 6.8E-1 | 9.8E-1 | 107 | 69 | 107 | 69 | 0.51 |
| bJ | mg/mL | 2.1E0 | 1.8E0 | 2.6E0 | 2.1E0 | 2.0E0 | 2.0E0 | 2.5E-4 | 2.5E-4 | 9.0E0 | 1.1E1 | 107 | 69 | 107 | 69 | 0.41 |
| bL | pg/mL | 4.3E0 | 3.2E0 | 1.0E1 | 7.8E0 | 1.3E1 | 9.6E0 | 4.6E-2 | 4.6E-2 | 6.0E1 | 3.5E1 | 107 | 69 | 107 | 69 | 0.45 |
| bM | mg/mL | 1.6E0 | 2.2E0 | 1.9E0 | 2.6E0 | 1.2E0 | 1.8E0 | 1.4E-1 | 1.6E-1 | 6.2E0 | 8.6E0 | 107 | 69 | 107 | 69 | 0.63 |
| bN | ng/mL | 3.3E1 | 3.5E1 | 1.3E2 | 1.1E2 | 2.9E2 | 2.8E2 | 1.4E-1 | 1.4E-1 | 1.9E3 | 1.9E3 | 107 | 69 | 107 | 69 | 0.49 |
| bO | ng/mL | 4.0E-2 | 4.0E-2 | 9.1E0 | 9.0E0 | 1.6E1 | 2.5E1 | 4.0E-2 | 4.0E-2 | 6.4E1 | 1.3E2 | 107 | 69 | 107 | 69 | 0.42 |
| bP | mg/mL | 5.2E-1 | 5.3E-1 | 7.2E-1 | 7.8E-1 | 6.1E-1 | 8.3E-1 | 4.9E-2 | 9.2E-2 | 3.7E0 | 4.8E0 | 107 | 69 | 107 | 69 | 0.50 |
| bQ | pg/mL | 2.0E1 | 2.4E1 | 6.7E1 | 2.4E2 | 2.4E2 | 1.6E3 | 1.5E-1 | 1.5E-1 | 2.4E3 | 1.3E4 | 107 | 69 | 107 | 69 | 0.56 |
| bR | ng/mL | 1.2E-2 | 1.2E-2 | 1.3E-1 | 2.0E-1 | 3.5E-1 | 4.8E-1 | 1.2E-2 | 1.2E-2 | 3.4E0 | 8.7E0 | 107 | 69 | 107 | 69 | 0.48 |
| bS | pg/mL | 9.4E-1 | 9.4E-1 | 9.1E0 | 1.0E1 | 3.5E1 | 4.8E1 | 9.4E-1 | 9.4E-1 | 3.4E2 | 3.9E2 | 107 | 69 | 107 | 69 | 0.47 |
| bU | ng/mL | 7.0E-2 | 1.0E-1 | 1.6E-1 | 2.3E-1 | 2.3E-1 | 7.9E-1 | 1.3E-2 | 1.3E-2 | 1.8E0 | 6.6E0 | 107 | 69 | 107 | 69 | 0.49 |
| bV | pg/mL | 4.4E2 | 5.5E2 | 6.2E2 | 6.6E2 | 1.1E3 | 4.0E2 | 1.6E2 | 2.3E2 | 1.2E4 | 2.2E3 | 107 | 69 | 107 | 69 | 0.62 |
| bW | pg/mL | 3.2E2 | 3.2E2 | 4.8E2 | 6.0E2 | 4.3E2 | 8.7E2 | 8.4E1 | 1.1E2 | 2.4E3 | 4.8E3 | 107 | 69 | 107 | 69 | 0.52 |
| bX | ng/mL | 2.5E-5 | 2.5E-5 | 2.7E-3 | 2.4E-3 | 3.4E-3 | 2.7E-3 | 2.5E-5 | 2.5E-5 | 1.3E-2 | 8.4E-3 | 107 | 69 | 107 | 69 | 0.49 |
| bZ | pg/mL | 2.7E2 | 3.1E2 | 1.9E3 | 2.3E3 | 5.9E3 | 8.6E3 | 1.5E-1 | 1.5E-1 | 4.4E4 | 5.8E4 | 107 | 69 | 107 | 69 | 0.52 |
| cA | pg/mL | 6.0E-1 | 6.0E-1 | 2.0E0 | 7.2E0 | 3.6E0 | 4.5E1 | 6.0E-1 | 6.0E-1 | 1.6E1 | 3.7E2 | 107 | 69 | 107 | 69 | 0.48 |
| cB | ng/mL | 5.0E-2 | 4.5E-2 | 7.4E-2 | 7.5E-2 | 8.1E-2 | 9.8E-2 | 1.7E-3 | 1.7E-3 | 3.8E-1 | 4.3E-1 | 107 | 69 | 107 | 69 | 0.46 |
| cC | ng/mL | 4.6E1 | 3.5E1 | 4.8E1 | 4.1E1 | 4.5E1 | 5.7E1 | 1.0E0 | 1.0E0 | 3.7E2 | 4.5E2 | 107 | 69 | 107 | 69 | 0.41 |
| cD | pg/mL | 6.0E0 | 4.0E0 | 1.3E1 | 1.2E1 | 4.9E1 | 3.9E1 | 3.3E-1 | 3.3E-1 | 4.8E2 | 2.9E2 | 107 | 69 | 107 | 69 | 0.41 |
| cE | pg/mL | 5.3E1 | 7.0E1 | 2.9E2 | 2.3E2 | 6.2E2 | 5.4E2 | 1.2E-1 | 1.2E-1 | 3.1E3 | 3.8E3 | 107 | 69 | 107 | 69 | 0.54 |
| cF | pg/mL | 8.7E0 | 5.3E-1 | 1.7E1 | 1.4E1 | 2.6E1 | 3.5E1 | 5.3E-1 | 5.3E-1 | 1.4E2 | 2.7E2 | 107 | 69 | 107 | 69 | 0.45 |
| cG | pg/mL | 5.1E1 | 7.0E1 | 1.0E2 | 2.9E2 | 1.6E2 | 1.3E3 | 1.1E1 | 7.8E0 | 1.1E3 | 1.0E4 | 107 | 69 | 107 | 69 | 0.58 |
| cH | uIU/mL | 3.1E0 | 3.7E0 | 6.9E0 | 8.7E0 | 1.7E1 | 1.7E1 | 8.6E-3 | 8.6E-3 | 1.6E2 | 1.2E2 | 107 | 69 | 107 | 69 | 0.53 |
| cI | ng/mL | 5.9E0 | 6.9E0 | 1.2E1 | 1.7E1 | 1.8E1 | 2.5E1 | 3.2E-2 | 2.3E-1 | 1.0E2 | 1.2E2 | 107 | 69 | 107 | 69 | 0.54 |
| cJ | ug/mL | 7.1E1 | 5.1E1 | 1.0E2 | 9.0E1 | 1.0E2 | 1.0E2 | 6.9E0 | 5.6E0 | 6.4E2 | 6.2E2 | 107 | 69 | 107 | 69 | 0.46 |
| cK | ng/mL | 3.8E-3 | 3.8E-3 | 1.7E-2 | 3.1E-2 | 4.4E-2 | 1.8E-1 | 3.8E-3 | 3.8E-3 | 3.4E-1 | 1.5E0 | 107 | 69 | 107 | 69 | 0.48 |
| cL | pg/mL | 2.2E2 | 2.0E2 | 4.0E2 | 7.6E2 | 8.4E2 | 3.0E3 | 3.6E1 | 3.1E1 | 7.1E3 | 2.4E4 | 107 | 69 | 107 | 69 | 0.51 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cM | pg/mL | 2.7E2 | 2.6E2 | 3.0E2 | 2.6E2 | 1.8E2 | 1.2E2 | 2.5E1 | 4.2E1 | 1.1E3 | 6.7E2 | 107 | 69 | 107 | 69 | 0.45 |
| cN | pg/mL | 1.2E2 | 1.2E2 | 1.3E2 | 1.4E2 | 5.2E1 | 1.2E2 | 3.8E1 | 6.3E1 | 3.2E2 | 1.1E3 | 107 | 69 | 107 | 69 | 0.54 |
| cO | pg/mL | 2.1E2 | 2.1E2 | 3.2E2 | 5.4E2 | 3.5E2 | 2.3E3 | 5.4E1 | 8.2E1 | 2.4E3 | 1.9E4 | 107 | 69 | 107 | 69 | 0.48 |
| cP | ng/mL | 2.4E3 | 2.4E3 | 2.5E3 | 2.6E3 | 9.5E2 | 9.6E2 | 6.2E2 | 1.0E3 | 5.6E3 | 4.7E3 | 107 | 69 | 107 | 69 | 0.52 |
| cQ | ng/mL | 4.9E-2 | 6.2E-2 | 1.2E-1 | 1.5E-1 | 1.9E-1 | 2.4E-1 | 2.0E-3 | 2.0E-3 | 1.2E0 | 1.3E0 | 107 | 69 | 107 | 69 | 0.54 |
| cR | ng/mL | 3.9E2 | 3.0E2 | 5.9E2 | 6.1E2 | 6.8E2 | 1.0E3 | 3.6E1 | 2.0E1 | 4.8E3 | 7.7E3 | 107 | 69 | 107 | 69 | 0.47 |
| cS | ng/mL | 2.8E2 | 3.1E2 | 4.5E2 | 5.3E2 | 4.9E2 | 9.4E2 | 4.1E1 | 9.7E1 | 2.5E3 | 7.1E3 | 107 | 69 | 107 | 69 | 0.52 |
| cT | ng/mL | 3.8E1 | 6.6E1 | 9.8E1 | 2.6E2 | 1.5E2 | 4.4E2 | 3.6E0 | 4.2E0 | 8.4E2 | 2.1E3 | 107 | 69 | 107 | 69 | 0.62 |
| cU | ng/mL | 5.6E1 | 8.0E1 | 7.8E1 | 1.3E2 | 8.7E1 | 2.1E2 | 6.2E0 | 1.4E1 | 7.7E2 | 1.6E3 | 107 | 69 | 107 | 69 | 0.61 |
| cV | ng/mL | 1.8E-1 | 2.2E-1 | 7.6E-1 | 6.6E-1 | 4.5E0 | 1.6E0 | 2.5E-2 | 3.4E-2 | 4.7E1 | 9.7E0 | 107 | 69 | 107 | 69 | 0.53 |
| cW | mIU/mL | 4.9E-2 | 4.5E-2 | 1.0E-1 | 7.0E-2 | 4.3E-1 | 6.6E-2 | 4.8E-3 | 4.8E-3 | 4.5E0 | 3.9E-1 | 107 | 69 | 107 | 69 | 0.50 |
| cX | ng/mL | 1.1E-1 | 1.6E-1 | 1.5E0 | 2.3E0 | 5.0E0 | 6.4E0 | 2.3E-4 | 2.3E-4 | 2.8E1 | 2.8E1 | 107 | 69 | 107 | 69 | 0.55 |
| cY | ng/mL | 7.6E0 | 6.7E0 | 1.1E1 | 1.0E1 | 9.8E0 | 1.2E1 | 2.2E-1 | 1.7E-1 | 4.1E1 | 6.1E1 | 107 | 69 | 107 | 69 | 0.45 |
| cZ | ug/mL | 1.4E1 | 1.2E1 | 1.5E1 | 1.4E1 | 6.8E0 | 6.7E0 | 2.3E0 | 2.8E0 | 4.6E1 | 3.0E1 | 107 | 69 | 107 | 69 | 0.44 |
| dA | pg/mL | 3.1E2 | 3.2E2 | 3.5E2 | 4.5E2 | 1.8E2 | 6.8E2 | 1.0E2 | 1.1E2 | 1.3E3 | 5.8E3 | 107 | 69 | 107 | 69 | 0.53 |
| dB | ug/mL | 1.8E1 | 1.8E1 | 2.0E1 | 1.6E1 | 2.4E1 | 9.4E1 | 2.1E0 | 2.1E0 | 2.5E2 | 3.0E1 | 107 | 69 | 107 | 69 | 0.46 |
| dC | nmol/L | 3.5E1 | 3.1E1 | 3.8E1 | 3.6E1 | 1.8E1 | 1.5E1 | 1.0E1 | 7.8E0 | 1.4E2 | 9.1E1 | 107 | 69 | 107 | 69 | 0.46 |
| dD | ug/mL | 3.5E1 | 3.2E1 | 3.7E1 | 3.3E1 | 1.1E1 | 1.1E1 | 1.4E1 | 1.4E1 | 7.4E1 | 6.0E1 | 107 | 69 | 107 | 69 | 0.39 |
| dE | ng/mL | 5.9E-1 | 3.4E-1 | 6.2E-1 | 5.2E-1 | 5.7E-1 | 6.6E-1 | 8.4E-3 | 8.4E-3 | 2.7E0 | 2.9E0 | 107 | 69 | 107 | 69 | 0.42 |
| dF | ng/mL | 2.4E2 | 3.0E2 | 3.1E2 | 4.0E2 | 2.2E2 | 2.9E2 | 7.5E1 | 7.5E1 | 1.2E3 | 1.3E3 | 107 | 69 | 107 | 69 | 0.61 |
| dG | ng/mL | 1.1E1 | 1.3E1 | 1.6E1 | 1.9E1 | 1.4E1 | 2.4E1 | 3.2E0 | 3.0E0 | 9.7E1 | 1.8E2 | 107 | 69 | 107 | 69 | 0.55 |
| dH | pg/mL | 7.9E0 | 8.5E0 | 2.0E1 | 2.2E1 | 4.6E1 | 8.0E1 | 4.0E-2 | 4.0E-2 | 3.1E2 | 6.7E2 | 107 | 69 | 107 | 69 | 0.54 |
| dI | pg/mL | 4.6E-1 | 4.6E-1 | 2.0E0 | 6.5E0 | 5.5E0 | 4.0E1 | 4.6E-1 | 4.6E-1 | 4.2E1 | 3.3E2 | 107 | 69 | 107 | 69 | 0.52 |
| dJ | ng/mL | 2.0E0 | 2.1E0 | 2.2E0 | 2.1E0 | 1.1E0 | 1.1E0 | 3.2E-2 | 3.2E-2 | 5.6E0 | 4.8E0 | 107 | 69 | 107 | 69 | 0.48 |
| dK | uIU/mL | 1.5E0 | 9.7E-1 | 2.4E0 | 1.7E0 | 4.3E0 | 2.0E0 | 2.8E-4 | 1.4E-2 | 3.9E1 | 1.1E1 | 107 | 69 | 107 | 69 | 0.42 |
| dL | ng/mL | 8.2E2 | 9.1E2 | 9.8E2 | 1.2E3 | 5.1E2 | 7.6E2 | 3.4E2 | 2.8E2 | 3.4E3 | 4.8E3 | 107 | 69 | 107 | 69 | 0.60 |
| dM | pg/mL | 9.5E2 | 1.1E3 | 1.3E3 | 1.5E3 | 1.5E3 | 1.5E3 | 3.9E2 | 3.7E2 | 1.5E4 | 9.6E3 | 107 | 69 | 107 | 69 | 0.56 |
| dN | ug/mL | 9.9E1 | 1.0E2 | 1.0E2 | 1.1E2 | 4.3E1 | 4.6E1 | 2.5E1 | 2.4E1 | 2.8E2 | 3.3E2 | 107 | 69 | 107 | 69 | 0.55 |
| dR | pg/ml | 1.7E3 | 1.2E3 | 2.0E3 | 2.0E3 | 1.7E3 | 2.3E3 | 1.4E2 | 1.3E2 | 7.8E3 | 9.8E3 | 74 | 59 | 74 | 59 | 0.42 |
| dU | pg/ml | 7.5E3 | 1.5E4 | 9.9E3 | 1.9E4 | 8.3E3 | 1.9E4 | 3.4E3 | 6.9E2 | 3.5E4 | 8.1E4 | 13 | 20 | 13 | 20 | 0.65 |
| dX | pg/ml | 8.4E-2 | 8.1E-2 | 1.6E-1 | 9.3E-2 | 2.2E-1 | 1.1E-1 | 2.6E-3 | 2.6E-3 | 1.2E0 | 4.2E-1 | 38 | 23 | 38 | 23 | 0.43 |
| dW | ng/ml | 1.2E-1 | 1.7E-1 | 2.2E-1 | 2.2E-1 | 2.4E-1 | 1.7E-1 | 6.4E-2 | 6.8E-2 | 8.0E-1 | 5.9E-1 | 11 | 8 | 11 | 8 | 0.61 |
| eF | ng/ml | 4.3E0 | 4.0E0 | 5.6E0 | 5.1E0 | 5.3E0 | 3.9E0 | 2.0E0 | 2.0E0 | 4.6E1 | 2.9E1 | 74 | 59 | 74 | 59 | 0.47 |
| eC | pg/ml | 3.0E2 | 2.8E2 | 3.8E2 | 3.4E2 | 3.0E2 | 3.0E2 | 9.9E0 | 1.9E1 | 1.6E3 | 2.0E3 | 64 | 53 | 64 | 53 | 0.45 |
| eD | pg/ml | 2.2E2 | 2.1E2 | 6.2E2 | 8.5E2 | 1.5E3 | 1.5E3 | 5.2E-1 | 5.2E-1 | 8.3E3 | 7.0E3 | 60 | 35 | 60 | 35 | 0.51 |
| eO | ng/ml | 4.6E1 | 9.4E1 | 2.9E2 | 1.0E2 | 3.9E2 | 4.6E1 | 2.0E1 | 4.3E1 | 9.9E2 | 1.7E2 | 11 | 8 | 11 | 8 | 0.61 |
| eM | ng/ml | 3.1E0 | 2.6E0 | 4.5E0 | 5.5E0 | 4.7E0 | 8.3E0 | 7.6E-1 | 6.9E-1 | 2.7E1 | 3.9E1 | 46 | 33 | 46 | 33 | 0.47 |
| eP | ng/ml | 3.7E-3 | 3.7E-3 | 7.5E-1 | 1.9E0 | 1.7E0 | 6.0E0 | 3.7E-3 | 3.7E-3 | 8.6E0 | 2.8E1 | 38 | 23 | 38 | 23 | 0.46 |
| eT | ng/ml | 2.4E2 | 3.9E2 | 6.9E2 | 8.2E2 | 8.3E2 | 9.0E2 | 1.0E2 | 7.1E1 | 2.9E3 | 2.9E3 | 33 | 22 | 33 | 22 | 0.59 |
| eQ | pg/ml | 1.0E0 | 1.0E0 | 7.9E1 | 3.6E1 | 1.5E2 | 6.6E1 | 1.0E0 | 1.0E0 | 4.7E2 | 2.2E2 | 13 | 20 | 13 | 20 | 0.47 |
| eW | U/ml | 1.1E-2 | 6.7E-3 | 1.9E-1 | 5.2E-1 | 4.6E-1 | 8.4E-2 | 6.7E-3 | 6.7E-3 | 1.6E0 | 1.9E-1 | 11 | 8 | 11 | 8 | 0.38 |
| fA | ng/ml | 2.0E2 | 2.1E2 | 3.6E2 | 4.9E2 | 4.6E2 | 4.9E2 | 3.9E1 | 4.0E1 | 1.5E3 | 1.4E3 | 13 | 18 | 13 | 18 | 0.57 |
| eZ | ng/ml | 4.7E1 | 5.7E1 | 5.5E1 | 5.9E1 | 2.7E1 | 2.3E1 | 1.8E1 | 2.3E1 | 1.2E2 | 1.1E2 | 33 | 22 | 33 | 22 | 0.57 |
| fB | ng/ml | 5.5E2 | 6.4E2 | 6.5E2 | 6.6E2 | 2.6E2 | 2.7E2 | 3.1E2 | 2.6E2 | 1.3E3 | 1.3E3 | 13 | 18 | 13 | 18 | 0.54 |
| fN | ng/ml | 2.1E-1 | 2.1E-1 | 4.1E0 | 3.5E0 | 1.0E1 | 6.0E0 | 2.1E-1 | 2.1E-1 | 5.4E1 | 2.1E1 | 33 | 22 | 33 | 22 | 0.48 |
| fP | ng/ml | 2.7E2 | 2.7E2 | 3.4E2 | 3.1E2 | 2.0E2 | 1.6E2 | 8.9E1 | 1.8E0 | 1.0E3 | 7.7E2 | 71 | 56 | 71 | 56 | 0.48 |
| fR | ng/ml | 1.3E5 | 1.7E5 | 2.2E5 | 2.4E5 | 1.7E5 | 1.9E5 | 3.9E4 | 1.9E2 | 6.9E5 | 8.7E5 | 71 | 44 | 71 | 44 | 0.55 |
| fY | ng/ml | 2.6E2 | 2.5E2 | 2.5E2 | 2.5E2 | 9.4E1 | 1.2E2 | 6.5E1 | 3.6E1 | 3.9E2 | 4.8E2 | 33 | 22 | 33 | 22 | 0.49 |
| gC | ng/ml | 2.5E2 | 2.5E2 | 2.7E2 | 2.6E2 | 1.2E2 | 8.3E1 | 1.4E2 | 6.4E2 | 5.9E2 | | 23 | 24 | 23 | 24 | 0.45 |
| gL | pg/ml | 6.8E4 | 6.5E4 | 7.6E4 | 7.3E4 | 3.7E4 | 3.8E4 | 1.4E4 | 1.1E4 | 1.9E5 | 2.2E5 | 74 | 59 | 74 | 59 | 0.46 |
| gP | U/ml | 2.7E2 | 2.8E2 | 2.9E2 | 2.9E2 | 1.4E2 | 9.8E1 | 1.1E2 | 1.2E1 | 1.1E3 | 5.2E2 | 74 | 58 | 74 | 58 | 0.53 |
| gW | ng/ml | 6.1E2 | 3.7E2 | 1.0E3 | 7.2E2 | 1.1E3 | 8.8E2 | 2.3E0 | 5.3E1 | 6.1E3 | 4.2E3 | 61 | 38 | 61 | 38 | 0.41 |
| gV | ng/ml | 2.1E1 | 2.2E1 | 2.1E1 | 2.2E1 | 6.8E0 | 8.8E0 | 1.0E1 | 8.1E-2 | 3.7E1 | 3.4E1 | 25 | 13 | 25 | 13 | 0.58 |
| tF | pg/mL | 9.5E2 | 1.9E3 | 1.1E4 | 1.3E4 | 3.9E4 | 3.9E4 | 1.8E1 | 1.2E1 | 2.8E5 | 2.5E5 | 64 | 55 | 64 | 55 | 0.55 |
| gZ | ug/ml | 5.3E-1 | 8.5E-1 | 3.2E1 | 4.6E1 | 1.1E2 | 1.1E2 | 8.7E-2 | 1.4E-1 | 4.1E2 | 4.0E2 | 13 | 20 | 13 | 20 | 0.64 |
| hA | ng/ml | 2.2E0 | 3.0E0 | 1.3E1 | 1.7E1 | 5.0E1 | 5.1E1 | 1.7E-2 | 1.7E-2 | 3.5E2 | 2.9E2 | 60 | 36 | 60 | 36 | 0.60 |
| nM | pg/ml | 1.0E-9 | 1.0E-9 | 1.0E-9 | 4.5E1 | 0.0E0 | 2.6E2 | 1.0E-9 | 1.0E-9 | 1.0E-9 | 1.5E3 | 40 | 34 | 40 | 34 | 0.51 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nN | pg/ml | 1.1E3 | 2.2E3 | 1.8E3 | 1.2E4 | 1.9E3 | 3.1E4 | 8.1E1 | 3.5E2 | 7.1E3 | 1.5E5 | 40 | 34 | 40 | 34 | 0.68 |
| nO | pg/ml | 2.2E1 | 2.9E1 | 3.6E1 | 4.1E1 | 5.1E1 | 4.0E1 | 6.7E0 | 4.0E0 | 3.1E2 | 2.0E2 | 40 | 34 | 40 | 34 | 0.59 |
| nR | pg/ml | 1.5E1 | 2.3E1 | 4.4E1 | 1.4E2 | 6.7E1 | 3.6E2 | 1.4E0 | 1.0E0 | 2.6E2 | 1.9E3 | 40 | 34 | 40 | 34 | 0.59 |
| nT | pg/ml | 4.9E1 | 1.0E2 | 9.2E1 | 1.5E2 | 9.4E1 | 1.8E2 | 1.0E-9 | 1.0E-9 | 4.9E2 | 9.2E2 | 40 | 34 | 40 | 34 | 0.62 |
| nU | pg/ml | 4.4E1 | 4.4E1 | 7.1E1 | 1.4E2 | 1.2E2 | 3.0E2 | 1.0E-9 | 1.0E-9 | 7.5E2 | 1.5E3 | 40 | 34 | 40 | 34 | 0.52 |
| lW | pg/ml | 1.0E-9 | 1.0E-9 | 6.5E0 | 1.6E1 | 1.4E1 | 4.1E1 | 1.0E-9 | 1.0E-9 | 5.5E1 | 1.7E2 | 40 | 34 | 40 | 34 | 0.55 |
| lX | pg/ml | 1.0E3 | 8.0E2 | 1.1E3 | 9.2E2 | 5.8E2 | 5.7E2 | 3.2E2 | 1.9E2 | 2.6E3 | 2.5E3 | 40 | 34 | 40 | 34 | 0.41 |
| lY | pg/ml | 1.9E1 | 1.7E1 | 2.0E1 | 2.1E1 | 1.2E1 | 2.2E1 | 1.0E-9 | 1.0E-9 | 4.8E1 | 1.2E2 | 40 | 34 | 40 | 34 | 0.46 |
| mE | pg/ml | 1.0E-9 | 1.0E-9 | 2.0E0 | 3.3E0 | 4.7E0 | 9.9E0 | 1.0E-9 | 1.0E-9 | 2.8E1 | 5.7E1 | 40 | 34 | 40 | 34 | 0.51 |
| mF | pg/ml | 2.3E-1 | 4.8E-1 | 7.9E0 | 5.1E0 | 3.9E1 | 1.8E1 | 1.0E-9 | 1.0E-9 | 2.5E2 | 1.1E2 | 40 | 34 | 40 | 34 | 0.52 |
| mH | pg/ml | 4.0E0 | 2.9E0 | 4.8E0 | 6.2E0 | 5.2E0 | 1.0E1 | 4.0E-1 | 4.0E-1 | 3.2E1 | 5.3E1 | 40 | 34 | 40 | 34 | 0.47 |
| mI | pg/ml | 1.0E-9 | 1.7E0 | 9.4E0 | 3.0E1 | 1.5E1 | 8.4E1 | 1.0E-9 | 1.0E-9 | 6.1E1 | 4.6E2 | 40 | 34 | 40 | 34 | 0.54 |
| mM | pg/ml | 2.8E1 | 3.8E1 | 5.9E1 | 1.1E2 | 7.8E1 | 2.1E2 | 1.0E-9 | 1.0E-9 | 4.0E2 | 1.1E3 | 40 | 34 | 40 | 34 | 0.52 |
| mP | pg/ml | 1.6E1 | 1.5E1 | 1.6E1 | 4.6E1 | 1.1E1 | 1.4E2 | 1.0E-9 | 1.0E-9 | 5.8E1 | 8.1E2 | 39 | 34 | 39 | 34 | 0.50 |
| mS | pg/ml | 1.6E3 | 1.6E3 | 1.8E3 | 1.7E3 | 8.6E2 | 1.2E3 | 8.8E1 | 1.0E-9 | 3.7E3 | 5.1E3 | 40 | 34 | 40 | 34 | 0.45 |
| mT | pg/ml | 5.0E1 | 6.0E1 | 1.4E2 | 1.7E2 | 2.5E2 | 3.5E2 | 1.0E1 | 1.2E1 | 1.4E3 | 1.7E3 | 39 | 34 | 39 | 34 | 0.50 |
| mU | pg/ml | 2.3E0 | 2.1E0 | 3.2E0 | 1.0E1 | 2.7E0 | 3.8E1 | 1.0E-9 | 1.0E-9 | 1.6E1 | 2.2E2 | 39 | 34 | 39 | 34 | 0.49 |
| mW | pg/ml | 2.5E3 | 1.9E3 | 2.5E3 | 2.5E3 | 1.2E3 | 2.1E3 | 1.0E-9 | 3.7E2 | 4.9E3 | 1.1E4 | 39 | 34 | 39 | 34 | 0.38 |
| mY | pg/ml | 6.5E2 | 6.5E2 | 8.4E2 | 1.1E3 | 8.8E2 | 1.6E3 | 1.0E-9 | 1.0E-9 | 4.2E3 | 8.0E3 | 40 | 34 | 40 | 34 | 0.54 |
| mZ | pg/ml | 1.8E2 | 1.7E2 | 3.8E2 | 3.3E2 | 5.5E2 | 3.4E2 | 1.0E-9 | 1.1E1 | 3.1E3 | 1.2E3 | 39 | 34 | 39 | 34 | 0.49 |
| nA | pg/ml | 2.5E0 | 9.1E-1 | 8.4E0 | 5.6E0 | 1.5E1 | 1.3E1 | 1.0E-9 | 1.0E-9 | 5.7E1 | 6.5E1 | 39 | 34 | 39 | 34 | 0.41 |
| nB | pg/ml | 2.6E2 | 3.0E2 | 3.0E2 | 3.4E2 | 1.5E2 | 2.0E2 | 3.0E1 | 3.8E1 | 6.9E2 | 9.6E2 | 40 | 34 | 40 | 34 | 0.54 |
| nC | pg/ml | 1.0E-9 | 6.6E1 | 1.1E4 | 7.2E3 | 6.1E4 | 3.8E4 | 1.0E-9 | 1.0E-9 | 3.8E5 | 2.2E5 | 40 | 34 | 40 | 34 | 0.52 |
| nD | pg/ml | 9.4E0 | 4.5E0 | 1.3E1 | 1.5E1 | 1.9E1 | 4.4E1 | 1.0E-9 | 1.0E-9 | 1.2E2 | 2.6E2 | 39 | 34 | 39 | 34 | 0.40 |
| nF | pg/ml | 1.0E-9 | 1.0E-9 | 4.8E0 | 1.2E0 | 1.7E1 | 5.2E0 | 1.0E-9 | 1.0E-9 | 9.3E1 | 2.7E1 | 40 | 34 | 40 | 34 | 0.45 |
| nH | pg/ml | 7.4E-1 | 1.3E0 | 8.2E1 | 3.0E2 | 4.2E2 | 1.7E3 | 1.0E-9 | 1.0E-9 | 2.6E3 | 1.0E4 | 39 | 34 | 39 | 34 | 0.54 |
| nI | pg/ml | 4.6E1 | 1.0E-9 | 8.6E1 | 4.7E1 | 1.9E2 | 8.4E1 | 1.0E-9 | 1.0E-9 | 1.2E3 | 3.5E2 | 40 | 34 | 40 | 34 | 0.38 |
| nJ | pg/ml | 6.1E-1 | 1.7E-1 | 1.3E0 | 4.8E0 | 2.6E0 | 2.3E1 | 1.0E-9 | 1.0E-9 | 1.5E1 | 1.3E2 | 40 | 34 | 40 | 34 | 0.45 |
| nK | pg/ml | 1.0E-9 | 1.0E-9 | 1.9E1 | 1.3E1 | 4.1E1 | 2.3E1 | 1.0E-9 | 1.0E-9 | 2.2E2 | 1.0E2 | 39 | 34 | 39 | 34 | 0.49 |
| nL | pg/ml | 1.0E-9 | 1.2E0 | 1.4E2 | 4.4E2 | 6.9E2 | 2.3E3 | 1.0E-9 | 1.0E-9 | 4.3E3 | 1.4E4 | 40 | 34 | 40 | 34 | 0.54 |
| hL | pg/ml | 1.5E4 | 2.5E4 | 2.1E4 | 2.5E4 | 1.5E4 | 1.4E4 | 2.6E3 | 5.1E3 | 7.2E4 | 6.0E4 | 33 | 22 | 33 | 22 | 0.63 |
| hO | pg/ml | 1.6E4 | 1.6E4 | 1.6E4 | 1.6E4 | 2.8E3 | 2.4E3 | 1.3E4 | 1.1E4 | 2.4E4 | 2.1E4 | 33 | 22 | 33 | 22 | 0.50 |
| hP | ng/ml | 4.4E5 | 4.4E5 | 3.8E5 | 6.3E5 | 1.7E5 | 6.9E5 | 4.7E4 | 1.7E4 | 9.0E5 | 2.8E6 | 33 | 22 | 33 | 22 | 0.61 |
| wJ | pg/ml | 1.4E5 | 1.1E5 | 1.5E5 | 1.9E5 | 8.1E4 | 1.5E5 | 1.1E4 | 1.3E4 | 3.6E5 | 5.8E5 | 33 | 24 | 33 | 24 | 0.53 |
| wK | pg/ml | 3.2E4 | 3.6E4 | 4.2E4 | 6.0E4 | 3.0E4 | 9.8E4 | 3.7E3 | 7.5E3 | 1.3E5 | 5.0E5 | 33 | 24 | 33 | 24 | 0.52 |
| wL | pg/ml | 3.9E0 | 8.1E0 | 4.4E1 | 5.7E1 | 1.5E2 | 1.3E2 | 1.0E-9 | 1.0E-9 | 8.4E2 | 4.7E2 | 33 | 24 | 33 | 24 | 0.54 |
| wP | pg/ml | 2.4E4 | 3.4E4 | 3.7E4 | 6.4E4 | 3.9E4 | 7.4E4 | 1.1E3 | 1.3E3 | 1.7E5 | 3.0E5 | 33 | 24 | 33 | 24 | 0.59 |
| wQ | pg/ml | 3.1E1 | 3.6E1 | 5.8E1 | 6.4E1 | 8.2E1 | 1.1E2 | 1.0E-9 | 1.0E-9 | 3.7E2 | 5.1E2 | 33 | 24 | 33 | 24 | 0.56 |
| hR | pg/ml | 2.9E4 | 2.4E4 | 3.1E4 | 2.6E4 | 1.2E4 | 1.0E4 | 1.0E-9 | 4.3E3 | 5.8E4 | 4.9E4 | 54 | 35 | 54 | 35 | 0.37 |
| hV | pg/ml | 5.0E2 | 4.3E2 | 4.7E2 | 4.3E2 | 2.4E2 | 2.2E2 | 1.0E-9 | 8.2E1 | 1.2E3 | 9.6E2 | 54 | 35 | 54 | 35 | 0.45 |
| hW | pg/ml | 1.7E3 | 2.3E3 | 2.0E3 | 3.4E3 | 1.2E3 | 6.4E3 | 1.0E-9 | 1.1E3 | 7.3E3 | 4.0E4 | 54 | 35 | 54 | 35 | 0.63 |
| hX | pg/ml | 1.1E3 | 1.1E3 | 1.2E3 | 1.1E3 | 1.1E3 | 5.4E2 | 2.5E0 | 1.3E2 | 8.6E3 | 2.9E3 | 54 | 35 | 54 | 35 | 0.48 |
| iA | pg/ml | 1.8E2 | 1.2E2 | 2.7E2 | 2.3E2 | 3.0E2 | 2.4E2 | 1.6E1 | 1.5E1 | 1.8E3 | 8.7E2 | 64 | 55 | 64 | 55 | 0.44 |
| iB | ng/ml | 4.7E0 | 6.1E0 | 6.1E0 | 7.5E0 | 5.1E0 | 5.1E0 | 3.3E-2 | 1.6E0 | 2.4E1 | 2.2E1 | 60 | 36 | 60 | 36 | 0.62 |
| iC | U/ml | 3.0E-1 | 3.7E-1 | 1.6E0 | 6.1E-1 | 7.1E0 | 7.2E-1 | 1.0E-9 | 3.7E-2 | 5.5E1 | 3.2E0 | 60 | 36 | 60 | 36 | 0.57 |
| tQ | pg/ml | 1.3E3 | 1.4E3 | 1.4E3 | 1.5E3 | 5.5E2 | 6.4E2 | 3.7E2 | 7.2E2 | 2.5E3 | 3.3E3 | 32 | 21 | 32 | 21 | 0.50 |
| tT | pg/ml | 1.6E1 | 2.1E1 | 1.8E1 | 2.6E1 | 9.4E0 | 1.8E1 | 5.4E0 | 1.0E1 | 4.8E1 | 9.3E1 | 32 | 22 | 32 | 22 | 0.65 |
| tS | pg/ml | 1.0E0 | 7.7E-1 | 1.5E0 | 1.5E0 | 1.8E0 | 2.2E0 | 1.0E-9 | 1.0E-9 | 8.5E0 | 1.0E1 | 32 | 23 | 32 | 23 | 0.48 |
| tX | pg/ml | 9.9E-1 | 1.3E0 | 1.2E0 | 2.5E0 | 1.0E0 | 2.7E0 | 2.5E-2 | 3.2E-1 | 4.4E0 | 1.0E1 | 32 | 22 | 32 | 22 | 0.63 |
| tO | pg/ml | 4.4E0 | 3.9E0 | 4.9E0 | 5.6E0 | 3.4E0 | 4.0E0 | 1.0E-9 | 1.7E0 | 1.4E1 | 1.8E1 | 32 | 23 | 32 | 23 | 0.55 |
| tR | pg/ml | 1.9E-1 | 2.5E-1 | 2.9E-1 | 4.2E-1 | 3.4E-1 | 5.9E-1 | 1.0E-9 | 1.0E-9 | 1.5E0 | 2.5E0 | 32 | 22 | 32 | 22 | 0.55 |
| tU | pg/ml | 9.9E0 | 1.0E1 | 1.1E1 | 1.6E1 | 7.2E0 | 1.8E1 | 1.5E0 | 2.2E-1 | 3.1E1 | 8.0E1 | 32 | 24 | 32 | 24 | 0.53 |
| tN | pg/ml | 2.0E1 | 2.1E1 | 2.5E1 | 4.0E1 | 1.9E1 | 4.3E1 | 1.0E-9 | 1.0E-9 | 8.0E1 | 1.6E2 | 31 | 22 | 31 | 22 | 0.59 |
| tV | pg/ml | 4.5E2 | 1.1E3 | 6.5E2 | 9.9E2 | 5.6E2 | 6.7E2 | 1.9E2 | 5.3E1 | 2.9E3 | 3.1E3 | 33 | 23 | 33 | 23 | 0.67 |
| iH | ng/ml | 1.6E5 | 1.7E5 | 1.6E5 | 1.6E5 | 4.9E4 | 5.1E4 | 7.1E4 | 2.9E3 | 2.6E5 | 2.4E5 | 64 | 55 | 64 | 55 | 0.48 |
| iJ | ng/ml | 5.2E4 | 4.6E4 | 5.8E4 | 5.2E4 | 3.5E4 | 3.6E4 | 5.5E3 | 1.8E3 | 2.5E5 | 2.5E5 | 64 | 55 | 64 | 55 | 0.44 |
| hB | ng/ml | 4.8E-1 | 4.9E-1 | 6.2E-1 | 6.7E-1 | 4.7E-1 | 5.4E-1 | 1.4E-1 | 1.2E-1 | 2.3E0 | 3.2E0 | 64 | 55 | 64 | 55 | 0.53 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| hC | pg/ml | 3.6E3 | 7.5E3 | 6.2E3 | 1.1E4 | 6.8E3 | 1.6E4 | 6.0E1 | 4.1E1 | 3.6E4 | 1.1E5 | 64 | 55 | 64 | 55 | 0.60 |
| hF | ng/ml | 1.0E-9 | 1.0E-9 | 6.3E1 | 1.0E-9 | 5.0E2 | 0.0E0 | 1.0E-9 | 1.0E-9 | 4.0E3 | 1.0E-9 | 64 | 55 | 64 | 55 | 0.49 |
| hG | pg/ml | 6.9E3 | 6.6E3 | 7.5E3 | 7.7E3 | 2.9E3 | 3.9E3 | 1.8E3 | 2.3E3 | 1.8E4 | 2.0E4 | 64 | 55 | 64 | 55 | 0.47 |
| iO | ng/ml | 3.7E5 | 4.0E5 | 4.1E5 | 4.3E5 | 2.1E5 | 1.8E5 | 1.1E4 | 9.8E4 | 1.1E6 | 8.2E5 | 64 | 55 | 64 | 55 | 0.55 |
| iP | pg/ml | 5.4E4 | 5.1E4 | 6.0E4 | 5.5E4 | 5.4E4 | 3.4E4 | 1.0E-9 | 7.1E3 | 4.4E5 | 2.2E5 | 64 | 55 | 64 | 55 | 0.47 |
| iZ | ng/ml | 1.5E3 | 1.9E3 | 1.8E3 | 2.0E3 | 9.1E2 | 8.8E2 | 6.6E2 | 7.5E2 | 5.7E3 | 4.6E3 | 64 | 53 | 64 | 53 | 0.58 |
| yH | pg/ml | 1.2E3 | 9.0E2 | 1.9E3 | 3.0E3 | 2.8E3 | 7.0E3 | 1.0E-9 | 1.0E-9 | 1.5E4 | 2.5E4 | 33 | 22 | 33 | 22 | 0.41 |
| yK | U/ml | 2.1E1 | 1.9E1 | 4.9E1 | 2.8E1 | 8.5E1 | 3.3E1 | 1.0E-9 | 1.0E-9 | 3.8E2 | 1.4E2 | 33 | 22 | 33 | 22 | 0.44 |
| yJ | pg/ml | 4.4E4 | 3.0E4 | 4.6E4 | 3.2E4 | 3.0E4 | 2.1E4 | 9.2E3 | 1.9E3 | 1.4E5 | 8.2E4 | 33 | 22 | 33 | 22 | 0.36 |
| yD | ng/ml | 1.2E-2 | 1.4E-2 | 1.3E-2 | 1.3E-2 | 5.6E-3 | 6.1E-3 | 1.0E-9 | 1.0E-9 | 2.8E-2 | 2.4E-2 | 33 | 24 | 33 | 24 | 0.53 |
| jB | ng/ml | 2.5E5 | 2.2E5 | 2.7E5 | 2.2E5 | 7.0E4 | 7.3E4 | 1.5E5 | 9.9E4 | 3.6E5 | 3.5E5 | 13 | 20 | 13 | 20 | 0.32 |
| wB | pg/ml | 8.8E3 | 1.2E4 | 1.0E4 | 1.4E4 | 7.0E3 | 1.1E4 | 1.7E3 | 1.9E3 | 3.3E4 | 4.2E4 | 33 | 24 | 33 | 24 | 0.59 |
| pY | pg/ml | 5.3E0 | 6.4E0 | 1.1E1 | 7.2E0 | 3.4E1 | 4.0E0 | 2.3E0 | 1.6E0 | 2.0E2 | 1.8E1 | 33 | 22 | 33 | 22 | 0.62 |
| sI | ng/ml | 5.2E-2 | 5.7E-2 | 5.1E-2 | 6.2E-2 | 1.4E-2 | 3.9E-2 | 2.1E-2 | 1.0E-2 | 7.3E-2 | 1.5E-1 | 15 | 14 | 15 | 14 | 0.55 |
| sF | mIU/mL | 1.1E1 | 5.0E0 | 1.5E1 | 1.4E1 | 2.0E1 | 2.2E1 | 6.2E-1 | 1.2E0 | 8.1E1 | 7.5E1 | 15 | 14 | 15 | 14 | 0.36 |
| sH | mIU/mL | 5.2E0 | 1.6E0 | 5.7E0 | 4.6E0 | 6.0E0 | 6.3E0 | 1.0E-9 | 7.9E-2 | 2.5E1 | 2.1E1 | 15 | 14 | 15 | 14 | 0.36 |
| sJ | ng/ml | 1.5E-1 | 1.5E-1 | 4.2E-1 | 6.2E-1 | 8.4E-1 | 1.7E0 | 1.0E-9 | 1.0E-9 | 3.3E0 | 6.4E0 | 15 | 14 | 15 | 14 | 0.50 |
| rC | pg/ml | 1.8E3 | 1.2E3 | 2.3E3 | 1.9E3 | 2.4E3 | 2.2E3 | 1.1E2 | 1.0E-9 | 1.5E4 | 1.1E4 | 53 | 33 | 53 | 33 | 0.42 |
| rB | pg/ml | 3.1E1 | 2.9E1 | 4.6E1 | 6.2E1 | 6.3E1 | 7.6E1 | 1.0E-9 | 1.0E-9 | 3.9E2 | 3.2E2 | 53 | 33 | 53 | 33 | 0.52 |
| zG | 2.5ng/ml | 2.2E-1 | 2.3E-1 | 7.1E-1 | 3.7E-1 | 1.2E0 | 5.8E-1 | 1.0E-9 | 1.0E-9 | 4.8E0 | 2.7E0 | 33 | 22 | 33 | 22 | 0.47 |
| zH | 2.3mU/ml | 9.2E-2 | 8.8E-2 | 1.0E-1 | 9.2E-2 | 5.1E-2 | 3.8E-2 | 1.0E-2 | 2.1E-2 | 3.1E-1 | 1.8E-1 | 33 | 22 | 33 | 22 | 0.44 |
| zI | 2.6ng/ml | 2.2E0 | 2.0E0 | 3.7E0 | 5.7E0 | 4.0E0 | 7.6E0 | 6.3E-1 | 5.4E-1 | 1.6E1 | 2.7E1 | 33 | 22 | 33 | 22 | 0.51 |
| qA | ng/ml | 8.3E6 | 1.2E7 | 1.1E7 | 1.3E7 | 7.8E6 | 6.7E6 | 3.7E6 | 4.3E6 | 3.9E7 | 3.0E7 | 33 | 22 | 33 | 22 | 0.62 |
| qB | ng/ml | 6.2E5 | 7.9E5 | 7.7E5 | 9.7E5 | 5.4E5 | 8.3E5 | 1.9E5 | 2.4E5 | 2.9E6 | 3.8E6 | 33 | 22 | 33 | 22 | 0.56 |
| qC | ng/ml | 3.1E5 | 2.7E5 | 6.5E5 | 7.1E5 | 1.0E6 | 1.1E6 | 2.5E4 | 6.5E4 | 5.2E6 | 4.7E6 | 33 | 22 | 33 | 22 | 0.52 |
| qD | ng/ml | 1.5E7 | 1.5E7 | 1.7E7 | 1.8E7 | 8.8E6 | 8.1E6 | 1.2E6 | 8.7E6 | 4.5E7 | 3.7E7 | 33 | 22 | 33 | 22 | 0.54 |
| jD | ng/ml | 2.4E1 | 4.5E1 | 3.6E1 | 5.5E1 | 3.9E1 | 6.0E1 | 1.0E-9 | 1.0E-9 | 1.9E2 | 2.9E2 | 60 | 36 | 60 | 36 | 0.61 |
| jE | ng/ml | 1.0E-9 | 1.0E-9 | 5.4E0 | 6.0E0 | 1.3E1 | 1.0E1 | 1.0E-9 | 1.0E-9 | 6.2E1 | 3.5E1 | 60 | 36 | 60 | 36 | 0.55 |
| jF | ng/ml | 4.7E1 | 2.1E1 | 5.2E1 | 4.2E1 | 5.3E1 | 5.3E1 | 1.0E-9 | 1.0E-9 | 2.1E2 | 1.9E2 | 60 | 36 | 60 | 36 | 0.44 |
| jG | ng/ml | 4.2E3 | 4.3E3 | 4.5E3 | 4.6E3 | 1.9E3 | 2.0E3 | 6.7E2 | 1.4E3 | 8.9E3 | 9.6E3 | 60 | 36 | 60 | 36 | 0.50 |
| jH | ng/ml | 7.7E1 | 7.7E1 | 7.9E1 | 9.5E1 | 3.9E1 | 7.6E1 | 1.3E1 | 1.5E1 | 2.1E2 | 4.3E2 | 60 | 36 | 60 | 36 | 0.53 |
| jI | ng/ml | 7.3E1 | 8.6E1 | 7.3E1 | 1.0E2 | 3.0E1 | 7.5E1 | 1.9E1 | 3.8E1 | 1.9E2 | 4.4E2 | 60 | 36 | 60 | 36 | 0.61 |
| sK | pg/mL | 3.7E3 | 4.3E3 | 3.8E3 | 5.4E3 | 1.3E3 | 4.7E3 | 1.8E3 | 2.1E3 | 7.1E3 | 2.3E4 | 32 | 21 | 32 | 21 | 0.58 |
| sM | pg/mL | 7.3E4 | 7.4E4 | 7.6E4 | 8.8E4 | 2.2E4 | 4.3E4 | 4.3E4 | 3.9E4 | 1.5E5 | 2.0E5 | 32 | 21 | 32 | 21 | 0.55 |
| sO | pg/mL | 2.4E8 | 2.1E8 | 2.5E8 | 2.2E8 | 8.3E7 | 1.0E8 | 4.9E7 | 6.6E7 | 4.4E8 | 4.2E8 | 32 | 21 | 32 | 21 | 0.41 |
| wC | ng/ml | 1.5E0 | 1.5E0 | 2.1E0 | 1.6E0 | 1.5E0 | 1.0E0 | 3.6E-1 | 6.1E-2 | 6.5E0 | 4.8E0 | 33 | 24 | 33 | 24 | 0.46 |
| wD | ng/ml | 2.1E1 | 2.8E1 | 9.9E1 | 5.4E1 | 3.6E2 | 6.3E1 | 3.8E0 | 2.8E0 | 2.1E3 | 2.9E2 | 33 | 24 | 33 | 24 | 0.66 |
| wE | ng/ml | 4.9E1 | 5.0E1 | 4.9E1 | 5.2E1 | 2.1E1 | 1.9E1 | 8.1E0 | 2.0E1 | 9.4E1 | 8.9E1 | 33 | 24 | 33 | 24 | 0.52 |
| wG | ng/ml | 1.0E-1 | 1.0E-1 | 1.4E-1 | 1.4E-1 | 1.6E-1 | 1.6E-1 | 1.0E-9 | 1.0E-9 | 7.1E-1 | 6.8E-1 | 33 | 24 | 33 | 24 | 0.50 |
| wH | ng/ml | 1.9E-2 | 4.9E-2 | 2.7E-1 | 4.6E-1 | 7.8E-1 | 1.2E0 | 1.0E-9 | 1.0E-9 | 4.2E0 | 5.6E0 | 33 | 24 | 33 | 24 | 0.59 |
| wF | ng/ml | 1.2E-1 | 3.7E-1 | 2.7E0 | 1.7E0 | 1.1E1 | 3.9E0 | 1.0E-9 | 1.0E-9 | 5.7E1 | 1.9E1 | 33 | 24 | 33 | 24 | 0.65 |
| rA | pg/ml | 2.4E1 | 2.4E1 | 3.1E1 | 2.9E1 | 2.9E1 | 2.4E1 | 1.0E-9 | 1.0E-9 | 2.0E2 | 1.1E2 | 59 | 34 | 59 | 34 | 0.47 |
| qZ | pg/ml | 4.6E1 | 5.8E1 | 5.2E2 | 6.0E2 | 2.1E3 | 2.0E3 | 2.8E-4 | 5.9E-4 | 1.0E4 | 1.0E4 | 43 | 26 | 43 | 26 | 0.56 |
| qY | pg/ml | 1.8E1 | 1.4E1 | 4.1E1 | 3.4E1 | 5.1E1 | 6.3E1 | 8.7E-1 | 2.1E0 | 2.3E2 | 3.3E2 | 59 | 34 | 59 | 34 | 0.40 |
| qX | pg/ml | 6.1E1 | 5.8E1 | 7.0E1 | 7.4E1 | 5.1E1 | 4.7E1 | 1.0E-9 | 1.0E-9 | 2.3E2 | 2.1E2 | 59 | 34 | 59 | 34 | 0.53 |
| qW | pg/ml | 7.8E0 | 7.3E0 | 1.3E1 | 8.6E0 | 1.8E1 | 8.4E0 | 1.0E-9 | 1.0E-9 | 1.2E2 | 3.1E1 | 59 | 34 | 59 | 34 | 0.41 |
| qV | pg/ml | 1.8E3 | 1.9E3 | 2.6E3 | 2.4E3 | 2.1E3 | 1.9E3 | 1.7E2 | 1.0E2 | 1.1E4 | 9.6E3 | 59 | 34 | 59 | 34 | 0.48 |
| qU | pg/ml | 4.8E1 | 1.0E2 | 1.5E2 | 2.7E2 | 2.3E2 | 4.1E2 | 1.0E-9 | 1.0E-9 | 1.2E3 | 2.1E3 | 59 | 34 | 59 | 34 | 0.61 |
| qT | pg/ml | 3.9E1 | 4.1E1 | 6.8E1 | 6.1E1 | 8.0E1 | 5.3E1 | 1.0E-9 | 1.0E-9 | 4.9E2 | 2.6E2 | 59 | 34 | 59 | 34 | 0.52 |
| qI | ng/ml | 5.5E4 | 6.4E4 | 6.1E4 | 6.3E4 | 3.3E4 | 2.5E4 | 1.0E4 | 2.5E4 | 1.6E5 | 1.3E5 | 32 | 20 | 32 | 20 | 0.53 |
| qH | ng/ml | 5.5E4 | 6.1E4 | 6.7E4 | 7.5E4 | 4.1E4 | 3.9E4 | 1.5E4 | 3.2E4 | 1.8E5 | 1.8E5 | 32 | 20 | 32 | 20 | 0.57 |
| qG | ng/ml | 1.9E5 | 1.8E5 | 1.9E5 | 1.9E5 | 6.4E4 | 7.8E4 | 3.4E4 | 8.4E4 | 3.0E5 | 4.2E5 | 32 | 20 | 32 | 20 | 0.45 |
| jK | ng/ml | 1.6E3 | 1.4E3 | 1.6E3 | 1.6E3 | 5.3E2 | 7.6E2 | 2.8E2 | 7.0E2 | 3.1E3 | 4.1E3 | 60 | 36 | 60 | 36 | 0.41 |
| jL | ng/ml | 1.7E2 | 2.5E2 | 2.7E2 | 2.9E2 | 2.1E2 | 1.8E2 | 5.6E1 | 6.4E1 | 9.6E2 | 7.6E2 | 60 | 36 | 60 | 36 | 0.58 |
| jM | ng/ml | 6.8E4 | 7.4E4 | 7.5E4 | 7.6E4 | 3.7E4 | 4.5E4 | 2.1E4 | 4.6E3 | 1.8E5 | 1.7E5 | 60 | 36 | 60 | 36 | 0.50 |
| jO | pg/ml | 2.1E5 | 2.6E5 | 2.8E5 | 2.7E5 | 1.8E5 | 1.4E5 | 6.0E4 | 9.6E4 | 1.1E6 | 6.5E5 | 60 | 36 | 60 | 36 | 0.52 |
| jP | pg/ml | 2.4E5 | 3.2E5 | 2.6E5 | 3.4E5 | 1.3E5 | 1.6E5 | 3.6E4 | 1.3E5 | 7.1E5 | 7.0E5 | 60 | 36 | 60 | 36 | 0.64 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jQ | pg/ml | 2.7E3 | 1.8E3 | 3.3E3 | 2.9E3 | 2.8E3 | 3.1E3 | 7.3E1 | 5.0E0 | 1.3E4 | 1.3E4 | 60 | 36 | 60 | 36 | 0.43 |
| jR | pg/ml | 7.1E3 | 4.2E3 | 1.0E4 | 1.1E4 | 1.1E4 | 1.4E4 | 3.0E1 | 1.0E-9 | 6.8E4 | 5.6E4 | 60 | 36 | 60 | 36 | 0.45 |
| jT | pg/ml | 1.7E5 | 1.8E5 | 1.8E5 | 1.8E5 | 7.2E4 | 6.9E4 | 7.1E4 | 7.5E4 | 5.5E5 | 3.5E5 | 60 | 36 | 60 | 36 | 0.52 |
| xA | pg/ml | 3.9E0 | 8.9E0 | 1.0E1 | 1.9E1 | 1.5E1 | 3.9E1 | 1.0E-9 | 1.0E-9 | 6.1E1 | 1.6E2 | 33 | 22 | 33 | 22 | 0.56 |
| yE | pg/ml | 8.1E1 | 9.1E1 | 8.2E1 | 8.9E1 | 2.9E1 | 4.3E1 | 3.6E1 | 6.4E0 | 1.4E2 | 2.0E2 | 33 | 22 | 33 | 22 | 0.55 |
| tM | pg/ml | 4.3E1 | 4.2E1 | 4.0E1 | 4.1E1 | 1.8E1 | 1.9E1 | 1.0E-9 | 1.0E-9 | 8.3E1 | 9.9E1 | 33 | 22 | 33 | 22 | 0.52 |
| tL | pg/ml | 1.0E-9 | 1.0E-9 | 2.2E0 | 4.5E-1 | 1.2E1 | 9.5E-1 | 1.0E-9 | 1.0E-9 | 6.7E1 | 3.6E0 | 33 | 22 | 33 | 22 | 0.57 |
| jU | mIU/ml | 6.2E0 | 3.8E0 | 1.3E1 | 1.0E1 | 2.1E1 | 1.3E1 | 8.1E-2 | 5.3E-1 | 1.1E2 | 5.7E1 | 60 | 36 | 60 | 36 | 0.45 |
| jV | mIU/ml | 2.5E0 | 1.6E0 | 4.7E0 | 2.9E0 | 6.5E0 | 3.4E0 | 2.7E-3 | 2.1E-2 | 3.2E1 | 1.5E1 | 60 | 36 | 60 | 36 | 0.43 |
| jY | ng/ml | 7.3E-4 | 1.8E-3 | 9.0E-3 | 5.4E-3 | 4.0E-2 | 9.9E-3 | 1.0E-9 | 1.0E-9 | 3.0E-1 | 5.1E-2 | 60 | 36 | 60 | 36 | 0.58 |
| kC | pg/ml | 9.7E1 | 1.1E2 | 1.4E2 | 2.5E2 | 1.7E2 | 4.8E2 | 2.1E1 | 3.6E1 | 1.1E3 | 2.7E3 | 40 | 34 | 40 | 34 | 0.56 |
| kE | pg/ml | 1.4E5 | 1.4E5 | 1.4E5 | 1.4E5 | 4.0E4 | 3.9E4 | 3.8E4 | 7.5E4 | 2.3E5 | 2.7E5 | 40 | 34 | 40 | 34 | 0.53 |
| kF | pg/mL | 6.4E1 | 6.8E1 | 6.4E1 | 7.5E1 | 1.8E1 | 3.1E1 | 2.7E1 | 4.0E1 | 1.1E2 | 1.5E2 | 40 | 34 | 40 | 34 | 0.56 |
| kG | pg/mL | 7.5E3 | 9.0E3 | 1.1E4 | 1.7E4 | 1.2E4 | 2.8E4 | 1.3E3 | 1.1E3 | 5.8E4 | 1.6E5 | 40 | 34 | 40 | 34 | 0.58 |
| kI | pg/ml | 1.9E2 | 2.1E2 | 2.2E2 | 2.1E2 | 1.3E2 | 9.6E1 | 6.4E1 | 1.0E-9 | 6.7E2 | 4.6E2 | 40 | 34 | 40 | 34 | 0.53 |
| kK | pg/ml | 1.2E2 | 1.2E2 | 1.6E2 | 1.6E2 | 1.7E2 | 1.2E2 | 6.4E0 | 2.1E1 | 9.1E2 | 4.9E2 | 40 | 34 | 40 | 34 | 0.52 |
| kN | pg/ml | 9.5E2 | 1.2E3 | 1.4E3 | 1.8E3 | 1.6E3 | 1.9E3 | 2.1E2 | 3.8E2 | 1.0E4 | 8.7E3 | 40 | 34 | 40 | 34 | 0.56 |
| kO | pg/ml | 7.0E3 | 7.4E3 | 8.1E3 | 1.1E4 | 3.9E3 | 2.4E4 | 4.0E3 | 3.8E3 | 2.5E4 | 1.5E5 | 40 | 34 | 40 | 34 | 0.50 |
| kP | pg/ml | 6.6E3 | 5.3E3 | 7.4E3 | 6.1E3 | 4.7E3 | 3.6E3 | 1.5E3 | 9.6E2 | 2.7E4 | 1.5E4 | 40 | 34 | 40 | 34 | 0.41 |
| kQ | pg/ml | 4.1E3 | 4.6E3 | 5.1E3 | 5.7E3 | 3.8E3 | 4.3E3 | 5.6E2 | 1.1E3 | 2.5E4 | 2.5E4 | 64 | 55 | 64 | 55 | 0.56 |
| kR | pg/ml | 2.0E1 | 2.7E1 | 4.1E1 | 3.1E1 | 1.3E2 | 2.3E1 | 1.0E-9 | 2.9E0 | 1.0E3 | 1.1E2 | 64 | 55 | 64 | 55 | 0.57 |
| kS | pg/ml | 8.5E2 | 9.2E2 | 1.0E3 | 1.0E3 | 5.7E2 | 6.1E2 | 2.5E2 | 8.2E1 | 3.2E3 | 3.0E3 | 64 | 55 | 64 | 55 | 0.51 |
| pS | ng/ml | 1.6E5 | 1.4E5 | 1.9E5 | 1.6E5 | 1.1E5 | 8.2E4 | 8.5E4 | 6.8E4 | 5.7E5 | 3.6E5 | 32 | 21 | 32 | 21 | 0.43 |
| rZ | ng/ml | 1.0E-9 | 7.1E-3 | 1.0E-2 | 1.4E-2 | 4.3E-2 | 2.3E-2 | 1.0E-9 | 1.0E-9 | 3.0E-1 | 1.1E-1 | 53 | 34 | 53 | 34 | 0.67 |
| rY | ng/ml | 5.8E-2 | 7.0E-2 | 5.5E-1 | 6.7E-1 | 2.6E0 | 3.4E0 | 1.0E-9 | 1.0E-9 | 1.8E1 | 2.0E1 | 53 | 34 | 53 | 34 | 0.58 |
| rX | ng/ml | 1.0E-9 | 1.0E-9 | 1.4E-1 | 1.0E-1 | 6.1E-1 | 5.3E-1 | 1.0E-9 | 1.0E-9 | 3.7E0 | 3.1E0 | 53 | 34 | 53 | 34 | 0.52 |
| lK | pg/ml | 5.8E1 | 7.6E1 | 1.4E2 | 1.4E2 | 1.8E2 | 1.7E2 | 1.0E-9 | 1.0E-9 | 7.4E2 | 6.9E2 | 59 | 36 | 59 | 36 | 0.46 |
| lL | pg/ml | 1.7E3 | 1.7E3 | 2.5E3 | 3.6E3 | 2.8E3 | 6.9E3 | 7.5E1 | 1.2E2 | 1.9E4 | 4.2E4 | 60 | 36 | 60 | 36 | 0.53 |
| lM | pg/ml | 1.4E3 | 9.9E2 | 3.9E3 | 6.1E3 | 6.7E3 | 1.3E4 | 2.7E2 | 9.5E0 | 4.2E4 | 6.7E4 | 60 | 36 | 60 | 36 | 0.43 |
| lN | pg/ml | 1.0E-9 | 1.0E-9 | 2.8E0 | 4.5E0 | 6.7E0 | 6.9E0 | 1.0E-9 | 1.0E-9 | 4.3E1 | 2.4E1 | 60 | 36 | 60 | 36 | 0.58 |
| lO | pg/ml | 1.0E-9 | 1.0E-9 | 5.7E-1 | 7.3E0 | 4.4E0 | 3.1E1 | 1.0E-9 | 1.0E-9 | 3.4E1 | 1.4E2 | 59 | 36 | 59 | 36 | 0.52 |
| zA | ng/ml | 2.1E7 | 2.1E7 | 2.1E7 | 2.1E7 | 6.4E6 | 6.6E6 | 9.1E6 | 1.0E7 | 3.4E7 | 3.6E7 | 32 | 24 | 32 | 24 | 0.51 |
| rW | ng/ml | 1.2E-2 | 1.2E-2 | 2.8E-2 | 4.0E-2 | 3.7E-2 | 8.1E-2 | 1.0E-9 | 1.0E-9 | 1.7E-1 | 3.2E-1 | 33 | 19 | 33 | 19 | 0.47 |
| rV | ng/ml | 1.0E-9 | 1.0E-9 | 1.3E-2 | 1.5E-2 | 5.2E-2 | 3.6E-2 | 1.0E-9 | 1.0E-9 | 2.8E-1 | 1.5E-1 | 33 | 19 | 33 | 19 | 0.60 |
| rU | ng/ml | 7.1E-2 | 9.5E-2 | 2.0E-1 | 1.1E-1 | 4.8E-1 | 1.2E-1 | 1.0E-9 | 1.0E-9 | 2.7E0 | 4.0E-1 | 33 | 19 | 33 | 19 | 0.49 |
| rT | ng/ml | 6.7E0 | 3.7E0 | 6.9E0 | 7.0E0 | 4.0E0 | 5.8E0 | 6.5E-1 | 1.0E0 | 2.1E1 | 2.0E1 | 33 | 19 | 33 | 19 | 0.43 |
| rS | ng/ml | 3.7E0 | 5.2E0 | 5.7E0 | 1.4E1 | 5.5E0 | 2.0E1 | 7.6E-1 | 1.8E0 | 2.5E1 | 7.0E1 | 33 | 19 | 33 | 19 | 0.60 |
| sC | pg/mL | 5.6E3 | 5.9E3 | 1.0E4 | 1.2E4 | 1.1E4 | 1.7E4 | 2.3E3 | 1.7E3 | 5.1E4 | 7.4E4 | 32 | 21 | 32 | 21 | 0.49 |
| yL | pg/ml | 3.0E1 | 3.2E1 | 3.3E1 | 1.0E2 | 2.9E1 | 3.0E2 | 5.6E0 | 9.1E0 | 1.8E2 | 1.4E3 | 33 | 22 | 33 | 22 | 0.60 |
| rP | ng/ml | 1.2E2 | 2.0E2 | 1.9E2 | 2.6E2 | 1.8E2 | 2.4E2 | 1.0E-9 | 1.0E-9 | 1.0E3 | 1.5E3 | 33 | 19 | 33 | 19 | 0.56 |
| rQ | ng/ml | 1.0E-9 | 1.0E-9 | 1.0E-9 | 1.7E1 | 0.0E0 | 4.6E1 | 1.0E-9 | 1.0E-9 | 1.0E-9 | 1.7E2 | 33 | 19 | 33 | 19 | 0.58 |
| rO | ng/ml | 1.5E-2 | 2.5E-2 | 3.9E-2 | 4.0E-2 | 7.4E-2 | 5.0E-2 | 1.0E-9 | 1.0E-9 | 4.0E-1 | 1.9E-1 | 33 | 19 | 33 | 19 | 0.54 |
| rR | ng/ml | 9.5E-1 | 4.0E0 | 9.1E0 | 1.4E1 | 2.1E1 | 2.0E1 | 1.0E-9 | 1.0E-9 | 9.5E1 | 7.5E1 | 33 | 19 | 33 | 19 | 0.58 |
| rN | ng/ml | 7.6E-1 | 6.3E-1 | 9.0E-1 | 1.5E0 | 5.8E-1 | 2.9E0 | 5.1E-2 | 2.1E-1 | 2.3E0 | 1.3E1 | 33 | 19 | 33 | 19 | 0.46 |
| qO | pg/ml | 8.7E3 | 8.2E3 | 1.1E4 | 1.4E4 | 8.8E3 | 1.3E4 | 7.4E2 | 1.9E3 | 3.7E4 | 4.8E4 | 32 | 21 | 32 | 21 | 0.52 |
| qP | pg/ml | 3.6E2 | 3.2E2 | 3.9E2 | 4.4E2 | 2.3E2 | 3.4E2 | 7.0E1 | 1.2E2 | 1.0E3 | 1.5E3 | 32 | 21 | 32 | 21 | 0.50 |
| qQ | pg/ml | 1.5E1 | 1.5E1 | 2.0E1 | 2.8E1 | 4.9E1 | 5.6E1 | 1.0E-9 | 1.0E-9 | 2.8E2 | 2.6E2 | 32 | 21 | 32 | 21 | 0.57 |
| nW | pg/ml | 1.1E5 | 1.1E5 | 1.1E5 | 1.1E5 | 2.9E4 | 2.8E4 | 5.8E4 | 3.6E4 | 1.9E5 | 1.7E5 | 64 | 55 | 64 | 55 | 0.50 |
| nY | pg/ml | 2.1E3 | 2.8E3 | 2.5E3 | 2.9E3 | 1.5E3 | 1.6E3 | 5.1E2 | 6.3E2 | 1.0E4 | 8.1E3 | 64 | 55 | 64 | 55 | 0.60 |
| oO | pg/ml | 9.0E4 | 7.6E4 | 1.0E5 | 1.0E5 | 5.8E4 | 8.2E4 | 1.5E4 | 3.3E3 | 2.6E5 | 4.0E5 | 34 | 33 | 34 | 33 | 0.43 |
| oP | pg/ml | 1.3E5 | 1.3E5 | 1.4E5 | 1.5E5 | 7.1E4 | 1.2E5 | 2.4E4 | 2.4E4 | 3.1E5 | 5.7E5 | 34 | 33 | 34 | 33 | 0.47 |
| oQ | pg/ml | 3.1E3 | 2.9E3 | 3.3E3 | 4.7E3 | 2.1E3 | 6.1E3 | 9.3E2 | 7.7E2 | 1.1E4 | 3.2E4 | 34 | 33 | 34 | 33 | 0.52 |
| oE | pg/ml | 1.4E2 | 3.3E2 | 3.6E2 | 6.9E2 | 5.1E2 | 7.8E2 | 1.0E-9 | 1.0E-9 | 2.8E3 | 3.4E3 | 64 | 55 | 64 | 55 | 0.65 |
| oF | pg/ml | 1.0E4 | 1.9E4 | 2.3E4 | 3.5E4 | 3.4E4 | 4.6E4 | 4.3E2 | 3.5E2 | 1.7E5 | 2.5E5 | 64 | 55 | 64 | 55 | 0.60 |
| oH | pg/ml | 4.0E1 | 3.4E1 | 8.3E1 | 7.1E1 | 1.3E2 | 9.8E1 | 4.3E-1 | 4.4E0 | 8.6E2 | 4.8E2 | 64 | 55 | 64 | 55 | 0.45 |
| oK | pg/ml | 8.2E2 | 8.8E2 | 1.8E3 | 1.4E3 | 2.3E3 | 1.3E3 | 8.8E1 | 1.4E2 | 1.2E4 | 5.9E3 | 64 | 55 | 64 | 55 | 0.50 |
| oN | pg/ml | 5.4E2 | 5.5E2 | 1.1E3 | 7.3E2 | 2.5E3 | 7.3E2 | 1.6E2 | 1.1E2 | 1.8E4 | 5.3E3 | 64 | 55 | 64 | 55 | 0.53 |

Figure 39 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| oW | pg/ml | 2.0E2 | 3.4E2 | 2.7E2 | 8.7E2 | 2.0E2 | 1.7E3 | 7.7E1 | 2.9E1 | 7.3E2 | 7.6E3 | 13 | 20 | 13 | 20 | 0.60 |
| oT | pg/ml | 3.1E2 | 2.7E2 | 3.4E2 | 3.2E2 | 1.6E2 | 1.9E2 | 1.0E2 | 1.1E2 | 7.4E2 | 7.9E2 | 13 | 20 | 13 | 20 | 0.41 |
| oV | pg/ml | 1.5E2 | 8.9E1 | 3.1E2 | 2.5E2 | 3.9E2 | 5.0E2 | 2.1E1 | 1.0E-9 | 1.4E3 | 2.2E3 | 13 | 20 | 13 | 20 | 0.41 |
| oD | pg/ml | 1.7E4 | 1.4E4 | 1.6E4 | 1.5E4 | 5.2E3 | 6.5E3 | 8.7E3 | 6.6E3 | 2.5E4 | 3.2E4 | 13 | 20 | 13 | 20 | 0.40 |
| uL | ng/ml | 3.8E1 | 3.5E1 | 5.4E1 | 4.2E1 | 5.2E1 | 2.3E1 | 1.5E1 | 1.4E1 | 2.9E2 | 1.1E2 | 31 | 21 | 31 | 21 | 0.45 |
| uO | ng/ml | 4.8E-1 | 2.4E-1 | 9.6E-1 | 6.4E-1 | 1.7E0 | 7.6E-1 | 1.0E-9 | 1.0E-9 | 9.3E0 | 2.1E0 | 31 | 21 | 31 | 21 | 0.45 |
| uM | ng/ml | 6.4E-1 | 4.3E-1 | 1.2E0 | 5.0E-1 | 2.3E0 | 5.5E-1 | 1.0E-9 | 1.0E-9 | 1.3E1 | 2.5E0 | 31 | 21 | 31 | 21 | 0.34 |
| uI | ng/ml | 8.5E-2 | 5.4E-2 | 1.3E-1 | 8.4E-2 | 1.2E-1 | 9.2E-2 | 1.6E-2 | 1.5E-2 | 5.8E-1 | 4.3E-1 | 31 | 20 | 31 | 20 | 0.35 |
| uN | ng/ml | 1.4E1 | 1.7E1 | 1.5E1 | 2.0E1 | 5.3E0 | 8.4E0 | 8.0E0 | 1.0E1 | 3.0E1 | 4.1E1 | 31 | 21 | 31 | 21 | 0.66 |
| uG | ng/ml | 1.8E1 | 1.9E1 | 2.2E1 | 2.7E1 | 1.5E1 | 2.8E1 | 6.1E0 | 1.2E0 | 7.9E1 | 1.3E2 | 31 | 21 | 31 | 21 | 0.54 |
| uR | ng/ml | 2.3E0 | 2.0E0 | 2.6E0 | 3.1E0 | 2.2E0 | 2.3E0 | 8.9E-1 | 7.5E-1 | 1.3E1 | 8.3E0 | 33 | 22 | 33 | 22 | 0.53 |
| uP | ng/ml | 2.1E0 | 2.6E0 | 2.4E0 | 2.8E0 | 9.8E-1 | 1.3E0 | 1.2E0 | 9.3E-1 | 6.0E0 | 6.1E0 | 33 | 22 | 33 | 22 | 0.61 |
| uV | ng/ml | 2.3E-4 | 3.2E-3 | 1.7E-2 | 9.4E-3 | 3.9E-2 | 1.3E-2 | 1.0E-9 | 1.0E-9 | 2.0E-1 | 4.3E-2 | 33 | 22 | 33 | 22 | 0.50 |
| uT | ng/ml | 6.3E1 | 8.7E1 | 9.0E1 | 1.1E2 | 9.3E1 | 8.8E1 | 1.3E1 | 2.2E1 | 4.5E2 | 4.1E2 | 33 | 22 | 33 | 22 | 0.66 |
| uU | ng/ml | 1.8E0 | 1.9E0 | 1.9E0 | 2.7E0 | 1.3E0 | 3.9E0 | 5.2E-1 | 5.4E-1 | 6.0E0 | 2.0E1 | 33 | 22 | 33 | 22 | 0.56 |
| uW | ng/ml | 7.3E0 | 8.1E0 | 7.6E0 | 8.5E0 | 2.0E0 | 2.5E0 | 4.4E0 | 5.5E0 | 1.3E1 | 1.6E1 | 31 | 21 | 31 | 21 | 0.62 |
| vB | ng/ml | 2.8E0 | 3.3E0 | 3.2E0 | 3.6E0 | 1.7E0 | 2.7E0 | 1.1E0 | 5.9E-1 | 8.3E0 | 1.0E1 | 31 | 21 | 31 | 21 | 0.53 |
| vC | ng/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 31 | 21 | 31 | 21 | 0.50 |
| uY | ng/ml | 6.1E-1 | 7.5E-1 | 7.9E-1 | 1.3E0 | 5.6E-1 | 1.3E0 | 6.8E-2 | 3.1E-1 | 2.3E0 | 4.4E0 | 31 | 21 | 31 | 21 | 0.59 |
| uZ | ng/ml | 5.8E-1 | 5.3E-1 | 8.1E-1 | 6.2E-1 | 9.4E-1 | 3.9E-1 | 1.0E-1 | 1.7E-1 | 4.9E0 | 1.9E0 | 31 | 21 | 31 | 21 | 0.47 |
| uX | ng/ml | 9.4E0 | 8.3E0 | 1.2E1 | 1.5E1 | 7.3E0 | 1.7E1 | 4.5E0 | 3.6E0 | 4.0E1 | 6.5E1 | 31 | 21 | 31 | 21 | 0.49 |
| vA | ng/ml | 7.0E-2 | 6.3E-2 | 8.3E-2 | 8.0E-2 | 5.9E-2 | 8.1E-2 | 2.4E-2 | 2.5E-2 | 2.7E-1 | 4.2E-1 | 31 | 21 | 31 | 21 | 0.46 |
| vH | ng/ml | 1.2E-1 | 1.2E-1 | 1.4E-1 | 2.4E-1 | 1.2E-1 | 4.1E-1 | 2.0E-2 | 2.1E-2 | 6.6E-1 | 1.9E0 | 32 | 21 | 32 | 21 | 0.52 |
| vI | ng/ml | 1.8E0 | 2.5E0 | 2.0E0 | 3.2E0 | 1.5E0 | 2.7E0 | 6.3E-3 | 8.7E-2 | 6.4E0 | 1.0E1 | 32 | 21 | 32 | 21 | 0.65 |
| vP | ng/ml | 4.3E2 | 2.9E2 | 4.6E2 | 4.8E2 | 3.2E2 | 5.3E2 | 6.7E1 | 9.2E1 | 1.1E3 | 2.4E3 | 33 | 22 | 33 | 22 | 0.46 |
| vT | ng/ml | 7.4E1 | 7.1E1 | 9.0E1 | 8.3E1 | 4.7E1 | 3.5E1 | 4.1E1 | 4.6E1 | 2.4E2 | 1.6E2 | 33 | 22 | 33 | 22 | 0.46 |
| vU | ng/ml | 1.0E-9 | 1.0E-9 | 3.1E1 | 1.9E1 | 4.2E1 | 3.4E1 | 1.0E-9 | 1.0E-9 | 1.3E2 | 1.1E2 | 33 | 22 | 33 | 22 | 0.41 |
| vQ | ng/ml | 3.9E2 | 4.4E2 | 4.2E2 | 4.1E2 | 1.7E2 | 1.6E2 | 7.2E1 | 1.2E2 | 8.4E2 | 6.7E2 | 33 | 22 | 33 | 22 | 0.50 |
| vO | ng/ml | 1.8E3 | 1.6E3 | 1.8E3 | 1.7E3 | 4.2E2 | 5.2E2 | 1.1E3 | 1.0E3 | 2.8E3 | 3.2E3 | 33 | 22 | 33 | 22 | 0.40 |
| vS | ng/ml | 1.3E3 | 1.3E3 | 1.2E3 | 1.3E3 | 4.1E2 | 5.2E2 | 1.0E-9 | 1.0E-9 | 2.1E3 | 2.0E3 | 33 | 22 | 33 | 22 | 0.52 |
| vV | ng/ml | 9.3E2 | 7.8E2 | 9.9E2 | 1.1E3 | 7.3E2 | 1.2E3 | 1.1E2 | 1.0E2 | 2.9E3 | 4.6E3 | 33 | 22 | 33 | 22 | 0.47 |
| vW | ng/ml | 1.2E2 | 1.1E2 | 1.6E2 | 1.8E2 | 1.2E2 | 1.7E2 | 4.3E1 | 6.0E1 | 6.6E2 | 7.7E2 | 33 | 22 | 33 | 22 | 0.49 |
| pF | pg/ml | 7.2E-1 | 5.2E-1 | 1.0E0 | 2.2E0 | 1.3E0 | 1.2E1 | 1.0E-9 | 1.0E-9 | 9.4E0 | 8.7E1 | 64 | 55 | 64 | 55 | 0.41 |
| pH | ng/ml | 6.9E0 | 8.9E0 | 8.6E0 | 1.0E1 | 4.2E0 | 5.7E0 | 3.9E0 | 1.2E0 | 1.8E1 | 2.3E1 | 13 | 20 | 13 | 20 | 0.60 |
| pI | ng/ml | 7.0E1 | 6.8E1 | 7.1E1 | 7.5E1 | 3.3E1 | 4.9E1 | 2.6E1 | 2.3E1 | 1.5E2 | 2.0E2 | 13 | 20 | 13 | 20 | 0.48 |
| pK | ng/ml | 3.9E-1 | 4.9E-1 | 3.9E-1 | 5.0E-1 | 1.7E-1 | 2.0E-1 | 2.0E-1 | 1.7E-1 | 7.7E-1 | 8.6E-1 | 13 | 20 | 13 | 20 | 0.68 |

Analyte panel data:

Unconstrained panels with 3 analytes, where 1.0E-10 >= 'model p-value' > 0. Contains 4,816 panels of 38,239,313 total panels evaluated. :
Ji{Et(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Fp(aA Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nt(aA Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nu Nv Nw Nx Ny Oe Of Og Oh Oi Ok Om On Oy Oz Pa Pb Pc Pd Pe Pf Pg Po Pz Qa Qb Qc Qd Qe) Nu(aA Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nv Nw Nx Ny Oe Of Og Oh Oi Ok Om On Oy Oz Pa Pb Pc Pd Pe Pf Pg Po Pz Qa Qb Qc Qd Qe) Lw(aA Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nv Nw Nx Ny Oe Of Og Oh Oi Ok Om On Oy Oz Pa Pb Pc Pd Pe Pf Pg Po Pz Qa Qb Qc Qd Qe) Mh(aA Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lx Ly Lz Ma Mb Mc Md Me Mf Mg Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nv Nw Nx Ny Oe Of Og Oh Oi Ok Om On Oy Oz Pa Pb Pc Pd Pe Pf Pg Po Pz Qa Qb Qc Qd Qe) Mp(aA Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lx Ly Lz Ma Mb Mc Md Me Mf Mg Mi Mj Mk Ml Mm Mn Mq Mr Ms Mt Mu Mv Mw Mx My Mz Na Nb Nc Nd Ne Nf Ng Nh Ni Nj Nk Nl Nm Nn No Nq Nr Ns Nv Nw Nx Ny Oe Of Og Oh Oi Ok Om On Oy Oz Pa Pb Pc Pd Pe Pf Pg Po Pz Qa Qb Qc Qd Qe) Ms(aA Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr

Is It Iu Iv Jg Jh Jl Jn Jo Jp Jq Jr Js Lv Lw Lx Lz Mb Mc Me Mf Mg Mh Mi Mj Mk Ml Mp Mr Mu Mv Mw Mx Mz Na Nb Nc Nd Ne Nf Nh Ni Nl Nn Nq Nr Ns Nv Nw Nx Ny Oe Oi Om On Oz Pa Pb Pc Pd Pe Pf Pg Pz Qa Qb Qc Qd Qe) Jj(aA Hr Hx Ih Ij Ik Il Io Ip Iq Ir Is It Iu Jg Jk Jl Jn Jp Jq Jr Js Jt Lh Li Lv Lw Lx Mb Mc Me Mf Mh Mi Mp Mr Ms Mt Mu My Mz Nb Nc Nd Ne Ng Nh Nl Nm No Nq Nr Ns Nv Nw Nx Oe Og Om On Oy Oz Pb Pc Pd Pe Pf Pg Po Pz Qa Qc Qe) Nj(Fp Hr Ih Ii Ij Ik Il In Io Ip Iq Ir Is It Iu Iv Jl Jo Jp Js Lw Lx Mb Mc Me Mf Mg Mh Mi Mj Mk Mr Ms Mu Mx My Na Nb Nd Nf Ng Nh Ni Nk Nm Nn No Nr Ns Nv Nx Ny Oe Oi Om On Oy Oz Pb Pc Pd Qa Qb Qe) Im(aA Et Fp Hr Ii Iq Iu Iv Jp Lw Mb Mf Mg Mh Mp Ms Mx Mz Na Nf Ng Nl Nn Nq Nw Nx Oe Om Pb Qd) Og(aA Et Fp Il Ir Iv Lw Mb Mf Mh Mp Ms Mx My Nl Nm Nn Nw Nx On Oy Qa Qb Qd Qe) aA(Et Fp Iv Lw Mb Mh Ms Mx My Mz Ng Nq Oe Oy Qd) Oy(Et Fp Iv Lw Mp Ms Mx Nn Nw Nx On Qb Qd) Et(Fp Hr Iv Mb Mh Ms Mx My Ng Qd) My(Fp Iv Lw Mp Mx Mz Nn Nw On) Ms(Fp Lw Mp Mx Mz Nw Qb Qd) Fp(Hr Iv Lw Nw Nx) Qd(Hr Iu Lw Mj Nq) Ng(Iv Lw Mp Nn) Mb(Mp Nw) Mx(Lw Mj) IvNw} Et{Jj(aA Hq Hr Hu Hv Hw Hx Ih Ij Ik Il Io Iq Ir Is It Jg Jk Jm Jn Jp Jq Jr Js Jt Lh Li Lj Lu Lv Lx Lz Mb Mc Me Mf Mg Mi Ml Mr Mt Mu My Mz Nb Nc Nd Ne Ng Nh Nk Nm No Nq Nr Ns Nv Nw Ny Oe Og Oh Om Oy Oz Pa Pb Pc Pd Pe Pf Pg Po Qc) Of(Hu Hv Ih Ij Ik Il Ir Is It Jg Jl Jn Jq Jr Js Jt Lh Li Lv Lx Mb Me Mf Mh Mi Mp Mr Ms My Mz Nb Nc Nd Ne Ng Nh Nl Nm Nn No Nr Nv Nw Oe Og Oy Oz Pd Pe Qa Qb Qe) Im(Fp Hq Hr Hv Iv Jh Jk Jl Jn Jo Jq Jr Js Jt Lh Lv Mb Me Mf Mg Mi Mp Mr Mx Mz Nb Nc Ne Nf Nh Nl Nm Nn Nq Nv Nw Nx Oe Om Oz Pb Pc Pd Pe Pf Pz Qa Qb Qc Qe) Nj(Hr Ih Ij Ik Ir Iv Jl Jn Jo Jp Jq Jr Js Jt Lh Lj Lv Lx Me Mf Mg Mi Mr Ms Mt Mx My Mz Nb Nd Ng Ni Nk Nm Nn No Nv Nw Nx Oe On Oy Pe Pz Qa Qb Qc Qe) Nu(Fp Hr Ik Ir Iv Jl Jn Jo Jq Jr Lv Lx Me Mf Mg Mi Mp Mr Ms Mx Mz Nd Nl Nn No Nq Nv Nw Nx Oe Pe Pz Qa Qb Qd Qe) aA(Hr Ih Ij Iv Jl Jn Lv Lw Mb Me Mp Ms My Mz Ng Nl Nq Nr Nx Oe Og Oy Qa Qb Qd Qe) Og(Fp Il Iv Jl Lw Mh Mp Ms Mx Mz Nl Nm Nv Nx Qa Qb Qd Qe) Oy(Fp Iv Jl Lw Lx Mh Mp Ms Mx Mz Nl Nn Nv Nx Pg Qa Qb Qe) Fp(Hr Iv Lh Lw Mh Mp Ms Mx My Ng Nl Nn Nx Oe Qd) Qd(

Li Lj Lu Lv Lx Lz Ma Mb Mc Md Me Mf Mg Mh Mi Mj Mk Ml Mm Mn Mq Mr Mt Mu Mv Mw Na Nb Nc Ne Nf Nh Ni Nk Nl Nm No Nr Ns Nv Ny Oh Oi Om On Oz Pa Pb Pc Pd Pe Pf Pg Po Pz) Ms(Fr Hq Hr Hu Hv Hw Hx Ii Ij Il Io Ip Iq Is It Iu Iv Jg Jh Jk Jm Jn Jr Jt Lh Li Lj Lu Lv Lx Lz Ma Mb Mc Md Me Mf Mg Mh Mi Mj Mk Ml Mm Mn Mq Mr Mt Mu Mv Mw My Na Nb Nc Ne Nf Nh Ni Nk Nl Nm No Nq Nr Ns Nv Ny Oh Oi Om Oz Pa Pb Pc Pd Pe Pf Pg Po Pz) Oe(Fr Hq Hr Hu Hv Hw Hx Ih Ii Ij Il Io Ip Iq It Iu Iv Jg Jh Jk Jm Jn Jr Js Jt Lh Li Lj Lu Lv Lz Ma Mb Mc Md Me Mf Mg Mh Mi Mj Mk Ml Mm Mn Mq Mr Mt Mu Mv Mw Na Nb Nc Ne Nf Nh Ni Nk Nl Nm No Nq Nr Ns Nv Ny Oh Oi Om Oz Pa Pb Pc Pd Pe Pf Pg Po Pz Qc) Nx(Fr Hr Hu Hv Hw Hx Ih Ii Il Io Ip Iq Is It Iu Iv Jg Jh Jk Jn Js Jt Lh Li Lj Lu Lv Lx Lz Ma Mb Mc Md Me Mf Mg Mh Mi Mj Mk Ml Mm Mn Mq Mr Mt Mu Mv Mw Na Nb Nc Ne Nf Nh Ni Nk Nl Nm No Nq Nr Ns Nv Ny Oh Oi Om On Oz Pa Pb Pc Pd Pe Pf Pg Po Pz Qc) Ik(Fr Hq Hr Hu Hv Hw Hx Ih Ii Ij Il Io Ip Iq It Iu Jg Jh Jk Jm Jn Jr Jt Lh Lj Lu Lv Lx Lz Ma Mb Mc Md Me Mf Mg Mh Mi Mj Mk Ml Mm Mn Mq Mr Mt Mu Mv Mw Na Nb Nc Ne Nf Nh Ni Nk Nm No Nq Nr Ns Nv Ny Oh Oi Om Oz Pa Pb Pc Pd Pe Pf Pg Po Pz Qc) Mx(Fr Hq Hr Hv Hw Hx Ih Ij Il Io Ip Iq Is Iu Iv Jg Jh Jk Jm Jn Jr Jt Lh Li Lj Lu Lv Lx Lz Ma Mb Mc Md Me Mf Mg Mi Ml Mm Mn Mq Mr Mt Mu Mv Mw Na Nb Nc Ne Nf Nh Ni Nk Nl Nm No Nq Nr Ns Nv Ny Oh Oi Om Oz Pa Pb Pc Pd Pe Pf Pg Po Pz Qc) My(Fr Hr Hv Hw Hx Ih Ii Ij Il Io Ip Iq It Iu Iv Jg Jh Jn Jr Js Jt Lj Lu Lv Lz Ma Mb Mc Md Me Mf Mg Mh Mi Mj Mk Ml Mm Mn Mq Mr Mu Mv Mw Na Nb Nc Ne Nf Ng Nh Ni Nk Nl Nm No Nq Nr Ns Ny Oh Oi Om Oy Oz Pa Pb Pc Pd Pe Pf Pg Po Pz Qc) Li(Hr Hu Hx Ih Ii Il Io Ip Iq Is It Iu Iv Jh Jk Jn Js Jt Lh Lj Lu Lv Lx Lz Mb Mc Md Me Mf Mg Mh Mi Mj Mk Ml Mm Mn Mq Mr Mt Mu Mv Mw Mz Na Nb Nc Ne Nf Nh Ni Nk Nl Nm No Nq Nr Ns Nv Ny Oh Oi Om On Oz Pb Pc Pd Pe Pf Pg Po Pz Qc) On(Fr Hq Hr Hu Hv Hw Hx Ih Ij Il Io Ip Iq Is It Iv Jg Jk Jm Jn Jr Js Jt Lh Lj Lu Lv Lx Lz Ma Mb Mc Md Me Mf Mi Mj Mk Ml Mm Mn Mq Mr Mt Mu Na Nb Nc Ne Nf Nh Ni Nk Nl Nm No Nr Ns Nv Ny Oh Oi Oz Pa Pb Pc Pd Pe Pf Pg Po Qc) Qc(Fr Hr Hu Hv Hw Hx Ih Ii Il Io Ip Iq Is It Iu Iv Jg Jh Jk Jn Js Jt Lh Lj Lu Lv Lx Lz Mb Mc Md Me Mf Mg Mh Mi Mj Mk Ml Mm Mt Mu Mv Mw Na Nb Nc Ne Nf Nh Nk Nl Nm No Nq Nr Ns Nv Ny Oh Oi Om Oz Pb Pc Pd Pe Pf Pg Pz) Is(Fr Hr Hu Hv Hx Ih Ii Il Ip It Iu Jg Jh Jk Jn Js Jt Lh Lj Lu Lv Lx Lz Mb Md Me Mf Mg Mh Mi Mj Mk Ml Mm Mt Mu Mv Mw Na Nb Nc Ne Nf Nh Nk Nl Nm No Nq Nr Ns Nv Ny Oh Oi Om Oz Pb Pc Pd Pe Pg Po Pz) Mz(Fr Hq Hu Hv Hw Ih Ij Il Io Ip Iq It Jg Jh Jk Jm Jn Jr Js Jt Lh Lj Lu Lv Lx Lz Ma Mb Mc Md Me Mf Mg Mi Mj Mm Mn Mq Mr Mt Mu Na Nb Nc Ne Nh Ni Nk Nm No Nr Ns Nv Oh Oi Oz Pa Pc Pd Pe Pf Pg Po) Oy(Fr Hq Hr Hu Hv Hw Hx Ih Ii Il Io Ip Iq It Iu Jh Jk Jm Jr Lj Lu Lv Lz Ma Mb Mc Md Me Mf Mg Mh Mj Mk Ml Mn Mq Mr Mv Mw Nb Nc Ne Nf Nh Ni Nk Nl No Nq Nr Ns Ny Oh Oi Om Oz Pb Pc Pe Pf Po Pz) Iv(Fr Hr Hx Ih Ii Il Ip It Iu Jg Jh Jn Js Jt Lh Lj Lu Lv Lx Lz Mb Mc Md Me Mf Mg Mh Mi Mj Mk Ml Mm Mr Mt Mu Mv Mw Na Nc Ne Nf Nh Nk Nl Nm No Nq Nr Ns Nv Ny Oh Oi Om Oz Pb Pc Pd Pe Pz) Of(Hq Hr Hu Hv Hw Hx Ii Il Io Iq It Jh Jk Jm Jr Lu Lz Ma Mb Mc Md Mg Mh Mj Mk Ml Mn Mq Mr Mt Mu Mv Mw Na Nb Nc Ne Nf Nh Ni Nk No Nq Nr Ns Oh Oi Om Oz Pa Pb Pc Pd Pe Pf Pg Po Pz) Js(Hr Hx Ih Ii Il Io Ip Iq It Iu Jg Jh Jk Jn Jt Lj Lv Lx Lz Mb Md Me Mf Mg Mh Mi Mj Mk Ml Mm Mt Mu Mv Mw Na Nc Ne Nf Nh Nk Nl Nm Nq Nr Nv Ny Oi Om Oz Pb Pc Pd Pe Pf Pg Po Pz) Ng(Hq Hr Hu Hv Hw Hx Ii Il Io Jh Jk Jm Jr Lj Lu Lv Lz Ma Mb Mc Md Mg Mh Mj Mk Ml Mn Mq Mr Mv Mw Nb Nc Ne Nf Ni Nk Nl No Nq Nr Ns Oh Oi Om Oz Pa Pb Pc Pd Pe Pf Pg Po Pz) Nm(Hr Hx Ih Ii Io Ip Iq It Iu Jg Jh Jn Lh Lj Lv Lw Lx Mb Md Me Mf Mg Mh Mi Mj Mk Ml Mr Mt Mu Mv Mw Na Nc Ne Nf Nh Nk Nl No Nq Nv Ny Oi Om Oz Pb Pc Pd Po Pz) Mh(Hr Hx Ih Ii Ij Io Ip Iq It Iu Jg Jh Jn Jt Lh Lj Lv Me Mf Mg Mi Mj Mk Mm Mr Mt Mv Mw Na Ne Nf Nh Nl No Nq Nv Ny Oi Om Oz Pb Pc Pd Pe Po) Mi(Hr Hx Ih Ii Ip It Iu Jg Jh Jn Jt Lj Lv Lx Md Me Mf Mg Mj Mk Ml Mm Mv Mw Na Nc Ne Nf Nh Nl Nq Nr Nv Ny Oi Om Oz Pb Pc Pd Po Pz) Lx(Hr Hx Ih Ii Io Ip Iq It Iu Jh Jn Jp Jt Lh Lj Lv Me Mf Mg Mj Mk Ml Mt Mu Mv Mw Na Ne Nf Nh Nk Nl Nq Ny Oi Om Pb Pd Po Pz) Ih(Hr Hx Ii Io Ip Iq It Iu Jg Jh Jn Jt Lh Lj Lv Me Mf Mg Mj Mk Ml Mt Mv Mw Na Ne Nf Nh Nk Nl Nq Nv Ny Oi Om Oz Pb Pd Pz) Jt(Hr Hx Ii Ip It Iu Jh Jn Lj Lv Mb Me Mf Mg Mj Mk Mu Mv Mw Na Nb Nc Ne Nh Nl Nq Nr Ny Oi Oz Pb Pc Pd Pz) Iu(Hx Jg Jh Jn Lh Lj Lv Me Mf Mg Mk Mm Mt Mv Mw Na Nc Ne Nh Nl No Nq Nv Ny Oh Oi Om Oz Pb Pc Pd) Jn(Hr Hx Ii Il Jh Jr Lh Lj Lv Me Mf Mg Mk Mm Mt Mv Mw Na Ne Nh Nl Nq Nv Ny Oi Oz Pb Pc Pd Pz) Lh(Hr Hx Jh Lj Md Me Mf Mg Mj Mk Ml Mu Mv Mw Na Nb Ne Nf Nh Nl Nq Nr Ny Oi Om Pb Pd Po) Ny(Hr Hx Ii Il Jh Lj Lv Me Mf Mg Mk Mt Mv Mw Na Ne Nf Nh Nl Nq Nv Oi Om Pb Pd Pz) Lj(Hr Ip It Jg Lv Me Mf Mg Mk Mm Mt Na Nc Ne Nh Nk Nl Nq Nv Oi Om Pb Pd Pz) Lv(Ii Ip It Jh Me Mf Mg Mk Mm Mt Mv Mw Na Ne Nh Nl Nq Oi Om Pb Pd Pz) Nv(Hr Hx Ii It Jh Jk Jp Mf Mg Mk Mu Mv Mw Ne Nh Nl Nq Oi Om Pb Pd Pz) Mm(Hr Hx Ii Jh Jp Lw Me Mg Mk Mv Mw Na Nh Nl Nq Oi Om Pb Pd Pz) Mf(Hu Ip It Jh Mg Mk Mt Mv Mw Na Ne Nh Nl Nq Oi Om Pb Pd Pz) Nl(Hr Ip Iq It Jg Me Mg Mk Mt Na Ne Nh Nk Oi Oz Pb Pc Pd) Lw(Fr Hq Hv Hw Ij Jm Jr Lu Ma Mc Mn Mq Nb Ni Oh Pa Pf) Mk(Ip It Jg Me Mg Mt Nc Nh Nq Oi Om Oz Pb Pc Pd Po) Jp(Fr Hq Hw Ij Jg Jm Jr Lu Mc Mn Mq Mr Ni No Pa) Pb(Hr Ip Iq It Jg Mg Mt Na Ne Nh Oi Om Pa Po Pz) Oi(Ii Ij Il Io Ip Iq It Jg Me Mt Na Nh Nq) Nq(Fr Ij Ip Iq Jg Me Mt Na Ne Nh No) Mg(Fr Hx Ij Ip Iq It Jg Me Na Nh) Na(Hx Jh Mv Mw Nh Om Oz Pc Pd) Ip(Hr Ii Mv Mw Nh Om Oz Pd Pz) Mt(Hx Ii Jh Ml Mv Mw) Jg(Jh Mv Mw Nh Pd Pz) Mu(Hu Jh Mv Mw) Nc(Ne Nh Nk) Hx(Mr Nh Pe) Ii(Ij Mr Pe) MvIj NeNh HrPc IqPz} Et{Mx(Fr Hq Hr Hu Hv Hw Hx Ih Ii Ij Ik Il In Io Ip Iq Ir Is It Iu Iv Jg Jh Jk Jl Jm Jn Jo Jp Jq Jr Js Jt Lh Li Lj Lu Lv Lx Ly Lz Ma Mb Mc Md Me Mf Mg Mi Mj Mk Ml Mm Mn Mp Mq Mr Mt Mu Mv Mw Mz Na Nb Nc Nd Ne Nf Nh Ni Nk Nl Nm Nn No Nq Nr Ns Nv Nw Nx Ny Oe Oh Oi Om On Oz Pa Pb Pc Pd Pe Pf Pg Po Pz Qa Qb Qc Qe) Ok(Fr Hq Hu Hv Hw Hx Ih Ii Ij Ik Il In Io Ip Iq Ir Is It Iu Jg Jh Jk Jl Jm Jn Jo Jp Jq Jr Js Jt Lh Li Lj Lu Lv Lw Lx Ly Lz Ma Mc Md Me Mf Mg Mi Mj Mk Ml Mm Mn Mp Mq Mr Mt Mu Mv Mw Mz Na Nb Nc Nd Ne Nf Nh Ni Nk Nl Nm Nn No Nq Nr Ns Nv Nw Nx Ny Oe Oh Oi Om On Oz Pa Pb Pc Pd Pe Pf Pg Po Pz Qa Qb Qc Qe) Mh(Fr Hq Hu Hv Hw Hx Ih Ii Ij Ik Il In Io Ip Iq Ir Is It Iu Jg Jh Jk Jl Jm Jn Jo Jp Jq Jr Js Jt Lh Li Lj Lu Lv Lx Ly Lz Ma Mb Mc Md Me Mf Mg Mi Mj Mk Ml Mm Mn Mq Mr Mt Mu Mv Mw Mz Na Nb Nc Nd Ne Nf Nh Ni Nk Nm Nn No Nq Nr Ns Nv Nw Ny Oe Oh Oi Om On Oz Pa Pb Pc Pd Pe Pf Pg Po Pz Qa Qb Qc Qe) Lw(Fr Hq Hu Hv Hw Hx Ih Ii Ij Ik Il In Io Ip Iq Ir Is It Iu Jg Jh Jk Jl Jm Jn Jo Jp Jq Jr Js Jt Lh Li Lj Lu Lv Lx Ly Lz Ma Mc Md Mf Mg Mi Mj Mk Ml Mm Mn Mp Mq Mr Mt Mu Mv Mw Mz Na Nb Nc Nd Ne Nf Nh Ni Nk Nm Nn No Nq Nr Ns Nv Nw Nx Ny Oe Oh Oi Om On Oz Pa Pb Pc Pd Pe Pf Pg Po Pz Qa Qc) Fp(Fr Hq Hu Hv Hw Hx Ih Ii Ij Ik Il In Io Ip Iq Ir Is It Iu Jg Jh Jk Jl Jm Jn Jo Jp Jq Jr Js Jt Li Lj Lu Lv Lx Ly Lz Ma Mb Mc Md Me Mf Mg Mi Mj Mk Ml Mm Mn Mq Mr Mt Mu Mv Mw Mz Na Nb Nc Nd Ne Nf Nh Ni Nk Nm No Nq Nr Ns Nv Nw Ny Oh Oi Om On Oz Pa Pb Pc Pd Pe Pf Pg Po Pz Qa Qb Qc Qe) Qd(Fr Hq Hr Hu Hv Hw Hx Ih Ii Ij In Io Ip Iq Ir Is It Iu Jg Jh Jk Jl Jm Jn Jo Jp Jq Jr Js Jt Lh Li Lj Lu Lv Lx Ly Lz Ma Mb Mc Md Me Mf Mg Mi Mj Mk Ml Mm Mn Mq Mr Mt Mu Mv Mw Mz Na Nb Nc Nd Ne Nf Nh Ni Nk Nm Nn No Nr Ns Nv Nw Nx Ny Oh Oi Om On Oz Pa Pb Pc Pd Pe Pf Pg Po Qa Qb Qc Qe) Og(Fr Hq Hr Hu Hv Hw Hx Ih Ik In Io Ip Iq Ir Is It Iu Jg Jh Jk Jm Jn Jo Jp Jq Jr Js Jt Lh Li Lj Lu Lv Lx Ly Lz Ma Mb Mc Md Me Mf Mg Mi Mj Mk Ml Mm Mn Mq Mr Mt Mu Mv Mw My Na Nb Nc Nd Ne Nf Ng Nh Ni Nk Nn No Nq Nr Ns Nv Ny Oe Oh Oi Om On Oz Pa Pb Pc Pd Pe Pf Pg Po Pz Qc) Iv(Hq Hr Hu Hv Hw Hx Ih Ij Ik Il Io Ir Is It Iu Jh Jk Jl Jn Jo Jp Jq Jr Js Jt Lh Li Lj Lu Lv Lx Lz Mb Mc Me Mf Mg Mi Mj Mk Ml Mn Mp Mr Mt Mu Mv Mw My Mz Nb Nc Nd Ne Nf Nh Ni Nl Nm Nn No Nq Ns Nv Nw Nx Ny Oe Oh Oi Om On Oz Pa Pb Pc Pd Pe Pf Pg Po Qa Qb Qc Qe) aA(Fr Hq Hu Hv Hw Hx Ii Ik Il In Io Ip Iq Ir Is It Iu Jg Jh Jk Jm Jo Jp Jq Jr Js Jt Lh Li Lj Lu Lx Ly Lz Ma Mc Md Mf Mg Mi Mj Mk Ml Mm Mn Mq Mr Mt Mu Mv Mw Na Nb Nc Nd Ne Nf Nh Ni Nk Nm Nn No Ns Nv Nw Ny Oh Oi Om On Oz Pa Pb Pc Pd Pe Pf Pg Po Pz Qc) Ms(Hq Hr Hu Hv Hw Hx Ij Ik Il Ir Is It Jg Jh Jl Jn Jo Jp Jq Jr Js Jt Lh Li Lj Lu Lv Lx Mb Mc Mc Mf Mg Mi Ml Mr Mt Mu Mv Mw My Na Nb Nc Ne Nf Ng Nh Ni Nl Nm Nn No Nq Nr Ns Nv Ny Oe Oh Oi Om On Oz Pa Pb Pc Pd Pe Pf Pg Po Pz Qc) Oy(Hq Hr Hu Hv Hw Ih Ij Ik Il Io Iq Ir Is It Iu Jg Jk Jm

Nb Nc Ne Nf Nh Nl No Nq Nr Ns Nx Ny Oh Oi Oz Pa Pb Pc Pd Pe Pf Pg Po Pz Qa Qb Qc) Jj(Fr Hq Hr Hu Hv Hw Hx Ih Ii Ij Ik Il In Io Ip Iq Ir Is It Iu Jh Jk Jm Jo Lj Lu Lx Ly Lz Ma Mc Md Me Mg Mj Mk Ml Mm Mn Mq Mr Mt Mu Mv Mw Na Nb Nd Nf Ng Ni Nk No Nq Nr Ns Ny Oe Oh Oi Om Pa Pb Pc Pg Po Pz Qa Qb Qc) Nu(Fp Hq Hr Hu Hv Hw Hx Ik Il In Iq Ir Iu Iv Jg Jh Jk Jm Jn Jo Jr Js Lh Li Lv Lx Mb Me Mf Mg Mh Mi Mp Mr Mt Mv Mw Mz Nc Nd Ne Nf Nh Ni Nl Nm Nn No Nq Nv Oe Oh Om On Oz Pa Pb Pc Pd Pe Pf Pg Pz Qa Qb Qc Qe) aA(Fp Hq Hr Hu Hw Hx Ih In Iq Iv Jg Jh Jk Jl Jn Jp Jq Jr Js Jt Lh Li Lj Lv Lw Mb Me Mh Mi Ml Mp Mr Ms Mt Mu Mx Mz Nc Ne Nf Ng Nh Ni Nl Nm Nn Nq Nv Nx Oe Of Om On Oz Pb Pd Pe Pf Qc Qe) Og(Fr Hr Hw Hx Ih Ii Il Io Ip It Jh Jk Jm Lj Lu Lz Ma Md Mg Mj Mn Mq Mv Mw Na Nd Ng Nk Nr Ny Oe Oi Pz) Jp(Fp Iv Jl Jq Jt Lv Mb Me Mf Mh Mp Mx My Mz Ng Nl Nm Nn Nq Nx Of Oy Pb Qe) Lw(aC Fp Hr Iv Jg Jl Js Mb Mh Ms Mx Mz Ng Nl Nx Of Om On Oy Qe) Ms(Iv Jl Jn Jq Js Jt Lv Mi Mp Mx Mz Nn Nx Of On Oy) Oy(Iv Jg Jl Jt Lh Lv Mp Mx Mz Nl Nn Nv Nx Pg) My(Iv Jl Jt Lh Lv Mi Mp Mx Mz Nm Nn Nv On) Of(Iv Jg Jl Jt Lv Mp Nx) Ng(Jg Mp Nm Nv On) On(Mh Mw) MxJg HrJl aCaN}

Qd{Nu(Fp Fr Hq Hr Hu Hv Hw Hx Ih Il In Io Ip Iq Ir Is It Iu Iv Jg Jh Jk Jl Jm Jn Jo Jp Jq Jr Js Jt Lh Li Lj Lu Lv Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Nh Ni Nk Nl Nm Nn No Nq Nr Ns Nv Ny Oe Oh Oi Om On Oz Pa Pb Pc Pd Pe Pf Pg Po Pz Qa Qb Qc Qe) Jj(Fr Hq Hr Hu Hv Hw Hx Ih Ii Ij In Io Ip Iq Ir Is It Iu Jh Jk Jm Jn Jo Jp Jq Jr Js Jt Li Lj Lu Lv Lx Ly Lz Ma Mb Mc Md Me Mg Mi Mk Ml Mm Mn Mq Mr Mt Mu Mv Mw Na Nb Nc Nd Ne Nf Ng Nh Ni Nk No Nq Nr Ns Ny Oe Of Oh Oi Om Oz Pa Pb Pc Pd Pe Pf Pg Po Pz Qa Qb Qc Qe) Nj(Fp Hr Ih Ij Il In It Iu Iv Jg Jl Jn Jp Jq Jt Lh Li Lv Lx Lz Mc Me Mf Mh Mi Mj Mk Mm Mr Ms Mt Mu Mx My Nb Nd Ne Ng Nh Ni Nk Nm Nn No Ns Nv Nx Oe Of On Oz Pb Pc Pd Pe Pg Pz Qc) aA(Fp Hr Ih Ij Ik Il Iu Iv Jg Jl Jn Jp Li Lv Lw Lz Mb Me Mh Mj Mp Ms Mx My Mz Nd Ne Ng Nh Nl Nm Nn Nq Nv Nx Oe Of On Pd Pe) Og(Fp Ij Ik Il Iv Jl Jp Jq Jt Lh Lv Lx Lz Mf Mh Mi Mj Mp Ms Mx My Mz Nc Nh Nl Nn Nq Nv Oe On Oy Pd) Lw(aC Fp Hr Ik Il Iv Jg Jl Jp Lh Mb Mh Mj Mx Mz Ne Ng Nl Nq Nx Oe Of On) Oy(Ik Il Jg Jl Jp Lh Lx Mi Mp Ms Mx Mz Nl Nm Nn Nv Nx Pd) Ms(Ik Il Jg Jl Jp Mp Mx My Nl Nm Nn Nx Oe On) My(Ik Jg Jl Jp Lh Mp Mz Nm Nn Nv Nx On) On(Mh Mw Ng Nq Oe) Nx(Mp Oe Of) Ng(Jg Nm) Ik(Jg Mh) aC(aN Ji) MpMz} On{Of(Fr Hq Hr Hu Hv Hw Hx Ih Ii Ij Ik Il In Io Ip Iq Ir Is It Iu Jh Jk Jl Jm Jn Jo Jp Jq Jr Js Jt Lh Li Lj Lu Lx Ly Lz Ma Mc Md Mf Mg Mi Mj Mk Ml Mm Mn Mp Mq Mr Mt Mu Mv Mz Na Nb Nc Nd Ne Nf Ni Nk Nn No Nr Ns Nv Ny Oh Oi Oz Pa Pb Pc Pd Pe Pf Pg Po Pz Qa Qb Qc Qe) Jj(aA Fr Hq Hr Hu Hv Hw Hx Ii Ij Ik Il In Io Ip Iq Ir Is It Iu Jg Jh Jk Jm Io Jp Jq Jr Lh Lj Lu Lx Ly Lz Ma Mc Md Mg Mi Mj Mk Ml Mm Mn Mq Mr Mt Mu Mv Mw Na Nb Nc Nd Nf Nh Ni Nk No Nr Ns Nv Ny Oh Oi Om Oz Pa Pb Pc Pd Pe Pf Pg Po Pz Qc) Oy(aA Hq Hr Hu Hx Ih Ii Ij Ik Ir Iu Jn Js Jt Li Lj Lv Lw Lx Mc Me Mf Mh Mk Ml Mm Mp Mr Mt Mu Mx My Mz Na Nb Nc Nd Ne Nf Ng Nq Nr Nv Nx Ny Oe Og Om Oz Pb Pd Pf Pg Po Qa Qb Qc Qe) Nj(Fp Hr Ih Ii Ik In Io Ir Iu Iv Jh Jk Jl Jo Jp Lj Lx Mb Me Mf Mg Mh Mi Mk Mp Mr Ms Mv Mx Mz Nb Nd Ne Nh Ni Nk Nm Nn No Oi Om Pz Qa Qe) Og(aA Fp Ik Il Ir Iv Lv Mb Me Mf Mh Mp Mx My Mz Ne Ng Nh Nl Nq Nx Oe Om Qa Qb Qe) Nu(aA Fp Iv Jh Jk Jl Jo Jq Lv Lw Mb Me Mg Mh Mp Mv Mx Mz Nl Nq Oe Om Pz) My(Fp Iv Jg Jp Lw Mh Ms Mx Mz Nm Nx Oe Qe) Ng(aA Fp Iv Jg Lv Lw Mb Mf Mh Mp Ms Nl Nn) Ms(aA Fp Iv Jn Lw Mh Mx Mz Oe Qb) aA(Fp Mb Mh Mx) Lw(Fp Mb Mh) Mw(Mu Nn)} Nu{Jj(Aa Fr Hq Hu Hv Hw Ih Ii Ik Ip Iq It Jh Jk Jm Jo Jr Lj Ma Mb Md Me Mf Mg Mh Mi Mm Mn Mq Mr Ms Mt Mu My Nb Nc Nd Ne Nh Nq Nr Og Oh Om Oy Oz Pa Pb Pc Pd Pe Pf Pg Po Pz Qc) aA(Fp Hr Ih Ij Ir Iv Jg Jl Jn Jq Js Jt Lh Li Lv Lw Mb Mh Mp Ms Mx My Ng Nl Nm Nv Nx Oy Qa Qb Qe) Lw(aC Fp Ir Iv Jg Jl Jn Jq Js Lh Li Lv Mb Mh Mp Ms Mx My Mz Ng Nl Nv Nx Oy Pe Qa Qb Qe) Nj(Fp Jg Jq Js Jt Lh Li Lx Mi Mp Mr Mx Nd Nm Nn No Nv Nx Pe Qa Qb Qe) Og(Fp Ir Is Iv Jn Js Jt Lh Li Lv Lx Mi Mp Mx Mz Nm Nn No Ny Pe Qb) Jp(Fp Jl Jq Lv Mh Mi Mp Ms Mx My Mz Ng Nm Nn Nv Nx Of Oy) My(Jg Jl Jq Jt Mz Nv Qa Qe) Nx(Fp Jl Mp Ms Mz Of Oy Qa) Jq(Fp Mh Mp Ms Mz Oy Qe) Jg(Jl Mh Mp Mx Of Oy) Ms(Jl Js Mz Qa Qe) Mz(Hx Jl Mp Pb) Oy(Jl Lx Mp Qa) Ng(Jt Nv) FpMp HrJl JiaC} Jj{Jg(aA Ih Ij Ir Is Iv Jn Jp Jq Jr Js Jt Lh Li Lv Lx Mh Mi Mp Mr Ms My Mz Ng Nl Nm Nn No Nx Of Og Oy Pe Po) Jp(Fp Ih Ij Ik Iv Jl Js Jt Lh Li Lv Lw Mh Mp Ms Mx Mz Nd Ni Nk Nm Nn No Nv Oe Of Og Oy Pe Qa Qb Qe) aA(Fp Ih Jg Jl Jn Js Jt Lh Li Lw Lx Mp Mr Mx Nk Nm No Nr Nv Nx Og Qa Qb Qe) Lw(Jg Jl Mr Mx Mz Og Qa Qe) Og(Jg Jl Mz Nm Nv Qa Qe) Mz(Jg Mp Nn) Jg(Mp Of) NkQa NvOy} Jg{Of(Fp Iv Jl Js Lw Mp Mx Mz Ng Nx Og Qa Qb) Og(aA Fp Ij Jl Mh Mp Mx Mz Qa Qb Qe) aA(Fp Lw Mh Mx My Mz Ng Oy Qb) Ng(Lw Mp Nv Qa Qb) Lw(Fp Mx Oy) Oy(Mx Qb) AjbM} Jp{Lw(aA Fp Mb Mh Ms Mx Og Oy) aA(Fp Ih Mh Ms Mx) Ms(Fp Mp Mx) Kx(dX eP) Og(Ij Nm)} Og{Ij(Iv Jl Mp Ms Nl Nx) Nm(Fp Nx Qa Qb Qe) Lw(Qa Qe) QaNx} Ji{aN(Aj bM dE Jo Of) bM(Aj Jo Nh Of)} Aj{Nm(aN bA cT) JtbM} Gz{Kr(qW rB rC)} My{Mz(aN bM) IjaA} nN{cM(dU oD) bUpI} Fp{aA(Mz Nx)} Lw{LicO LjaN} Kx{HvdX OreP} MncWgV

Unconstrained panels with 3 analytes, where 1.0E-7 >= 'model p-value' > 1.0E-8. Contains 18,623 panels of 38,239,313 total panels evaluated. : Et{Nc(Fr Hq Hr Hu Hv Hw Hx Ih Ii Ij Ik Il In Io Ip Iq Ir Is It Iu Jg Jh Jk Jl Jm Jn Jo Jp Jq Jr Js Jt Lh Li Lj Lu Lv Lx Ly Lz Ma Mb Mc Md Me Mf Mg Mi Mj Mk Ml Mm Mn Mq Mr Mt Mu Mv Mw My Na Nb Nd Ne Nf Nh Ni Nk Nl Nm Nn No Nq Nr Ns Nv Nw Nx Ny Oe Oh Oi Om On Oz Pa Pb Pc Pd Pe Pf Pg Po Pz Qa Qb Qc Qe) Jr(Fr Hq Hr Hu Hv Hw Hx Ih Ii Ij Ik Il In Io Ip Iq Ir Is It Iu Jg Jh Jk Jl Jm Jn Jo Jp Jq Js Jt Lh Li Lj Lu Lv Lx Ly Lz Ma Mb Mc Md Me Mf Mg Mi Mj Mk Ml Mm Mn Mq Mr Mt Mu Mv Mw My Mz Na Nb Nd Ne Nf Nh Ni Nk Nl Nm Nn No Nq Nr Ns Nv Nw Nx Ny Oh Oi Om On Oz Pa Pb Pc Pd Pe Pf Pg Po Pz Qa Qb Qc Qe) Ne(Fr Hq Hr Hu Hv Hw Hx Ih Ii Ij Ik Il In Io Ip Iq Ir Is It Iu Jg Jh Jk Jl Jm Jn Jo Jp Jq Js Jt Lh Li Lj Lu Lv Lx Ly Lz Ma Mb Mc Md Me Mf Mg Mi Mj Mk Ml Mm Mn Mq Mr Mt Mu Mv Mw My Na Nb Nd Nf Nh Ni Nk Nl Nm Nn No Nq Nr Ns Nv Nw Nx Ny Oe Oh Oi Om On Oz Pa Pb Pc Pd Pe Pf Pg Po Pz Qa Qc Qe) Qc(Fr Hq Hr Hu Hv Hw Hx Ih Ii Ij Ik Il In Io Ip Iq Ir Is It Iu Jg Jh Jk Jl Jm Jn Jo Jp Jq Js Jt Lh Li Lj Lu Lv Lx Ly Lz Ma Mb Mc Md Mf Mg Mi Mj Mk Ml Mm Mn Mq Mr Mt Mu Mv Mw Mz Na Nb Nd Nf Nh Ni Nk Nm Nn No Nq Nr Ns Nv Nw Nx Ny Oe Oh Oi Om On Oz Pa Pb Pc Pd Pe Pf Pg Po Pz Qa Qb Qe) No(Fr Hq Hr Hu Hv Hw Hx Ih Ii Ij Ik Il In Io Ip Iq Ir Is It Iu Jg Jh Jk Jl Jm Jn Jo Jp Jq Js Jt Lh Li Lj Lu Lv Lx Ly Lz Ma Mc Md Mf Mg Mi Mj Mk Ml Mm Mn Mq Mr Mt Mu Mv Mw Mz Na Nb Nd Nf Nh Ni Nk Nm Nn Nq Nr Ns Nv Nw Ny Oe Oh Oi Om On Oz Pa Pb Pc Pd Pe Pf Pg Po Pz Qa Qe) Lx(Fr Hq Hr Hu Hv Hw Hx Ih Ii Ij Ik Il In Io Ip Iq Ir Is It Iu Jg Jh Jk Jl Jm Jn Jo Jp Jq Js Jt Lh Li Lj Lu Lv Ly Lz Ma Mc Md Mf Mg Mi Mj Mk Ml Mm Mn Mp Mq Mr Mt Mu Mw Mz Na Nb Nd Nf Nh Ni Nk Nm Nn Nq Nr Ns Nv Nw Nx Ny Oe Oh Oi Om On Oz Pa Pb Pc Pd Pe Pf Pg Po Pz Qa Qe) Nh(Fr Hq Hr Hu Hv Hw Hx Ih Ij Ik Il Io Ip Iq Ir Is It Iu Jg Jh Jk Jl Jm Jn Jo Jp Jq Js Jt Lh Li Lj Lu Lv Ly Lz Ma Mb Mc Md Me Mf Mg Mi Mj Mk Ml Mm Mn Mq Mr Mt Mu Mv Mw My Na Nb Nd Nf Ni Nk Nm Nn Nq Nr Ns Nv Nw Nx Ny Oe Oh Oi Om On Oz Pa Pb Pc Pd Pe Pf Pg Po Pz Qa Qe) Pe(Fr Hq Hu Hv Hw Hx Ih Ij Ik Il In Io Ip Iq Ir Is It Iu Jg Jh Jk Jl Jm Jn Jo Jp Jq Js Jt Lh Li Lj Lu Lv Ly Lz Ma Mc Md Me Mf Mg Mi Mj Mk Ml Mm Mn Mp Mq Mr Mt Mu Mv Mw Mz Na Nb Nd Nf Ni Nk Nm Nn Nq Nr Ns Nv Nw Nx Ny Oe Oh Oi Om On Oz Pa Pb Pc Pd Pf Pg Po Pz Qa Qe) Ih(Fr Hq Hr Hu Hv Hw Hx Ii Ij Ik Il In Io Ip Iq Ir Is It Iu Jg Jh Jk Jl Jm Jn Jo Jp Jq

Lh Lv Lx Me Mf Mg Mm Mt Mv Mw Ne Nh Nq Nv Ny Oi Om Pb Pd Pz) Hr(Hx Ii It Iu Jg Jh Lv Me Mf Mg Mk Mt Mv Mw Na Ne Nh Nq Oi Om Pd Pz) Ii(Hx It Iu Jg Jh Lj Me Mf Mg Mk Mv Mw Na Ne Nh Nl Nq Om Pb Pd Pz) It(Hx Ip Iu Jg Jh Jn Lh Me Mm Mt Mv Mw Na Ne Nh Nq Ny Om Pd Pz) Pz(Hx Iu Jh Lh Me Mg Mh Mk Mt Mv Mw Na Ne Nh Nl Nq Oi Om Pd) Hx(Ip Jg Jh Lj Lv Me Mf Mk Mv Mw Ne Nl Nq Oi Om Pb Pd) Jg(Ip Jn Jt Lh Li Lv Lx Me Mf Mm Mt Na Ne Nv Ny Om) Jh(Ip Lj Me Mg Mk Mv Mw Ne Nh Nl Nq Oi Om Pb Pd) Om(Jn Jt Lj Me Mg Mt Mv Mw Ne Nh Nl Nq Oi Pd) Mt(Ip Jt Lh Me Mg Mi Mm Na Ne Nh Nv Pd) Mv(Lj Me Mg Mk Mw Ne Nh Nl Nq Oi Pb Pd) Mw(Lj Me Mg Mk Ne Nh Nl Nq Oi Pb Pd) Mm(Ip Jt Lh Lx Mf Ne Nm Nv Ny) Aj(aN Dc Ji Jp Jt Lw Mz Nm) Me(Ip Mf Na Ne Nh Nv Pb Pd) Ip(Iu Jn Lh Na Ne Nv Ny) Pd(Mg Ne Nh Nq Oi Pb) Lh(Js Jt Lv Mi Nv) Ne(Mg Mk Na Oi) Nv(Jt Lv Lx Na) Nq(Mg Nl Pb) aC(Ji Lw Mz) Aa(Jj Of) NmJt MgOi MkNa} Nw{Mh(Fr Hq Hr Hu Hv Hw Hx Ih Ii Ij Ik Il In Io Ip Iq Ir Is It Iu Jg Jh Jk Jl Jn Jo Jp Jq Jr Js Jt Lh Li Lj Lu Lv Ly Lz Ma Mb Mc Md Me Mg Mi Mj Mk Ml Mm Mn Mq Mt Mu Mw Mz Na Nb Nc Nd Ne Nf Ng Nh Ni Nk No Nq Nr Ns Nv Oe Oh Oi On Oz Pa Pb Pc Pd Pe Pf Pg Po Pz Qa Qb Qc Qe) Mp(Fr Hq Hr Hu Hv Hw Hx Ih Ii Ij Ik Il In Io Ip Iq Ir Is It Iu Jg Jh Jk Jl Jm Jn Jo Jp Jq Jr Js Jt Lh Li Lj Lu Lv Lx Ly Lz Ma Mc Md Mg Mi Mj Mk Ml Mm Mn Mq Mr Mt Mu Mz Na Nb Nc Nd Ne Nf Nh Ni Nk Nn No Nr Ns Nv Ny Oe Oh Oi On Oz Pa Pb Pc Pd Pe Pf Pg Po Pz Qa Qb Qc Qe) Nl(Fr Hq Hr Hu Hv Hw Hx Ih Ii Ij Il In Io Ip Iq Ir Is It Iu Jg Jh Jk Jl Jm Jn Jo Jp Jq Jr Js Jt Lh Li Lj Lu Lx Ly Lz Ma Mc Md Mg Mi Mj Mk Ml Mm Mn Mq Mr Mt Mu Mv Mw Na Nb Nc Nd Ne Nf Nh Ni Nk No Nq Nr Ns Nv Nx Ny Oh Oi On Oz Pa Pb Pc Pd Pe Pf Pg Po Pz Qa Qb Qc Qe) Nm(aC Aj Fr Hr Hx Ih Ii Ij Ik Il In Io Ip Iq Ir Is It Iu Jh Jl Jn Jp Jr Js Lh Li Lj Lu Lv Lw Lx Ly Lz Ma Mc Md Mf Mg Mi Mj Mk Ml Mm Mn Mq Mr Mt Mu Mv Mw Mz Na Nb Nc Nd Ne Nf Nh Ni Nk Nn No Nq Nr Ns Nv Nx Ny Oe Oh Oi On Oz Pb Pc Pd Pe Pf Pg Pz Qa Qb Qc Qe) Me(Fr Hr Hx Ih Ii Ij Ik Il In Io Ip Iq Ir Is It Iu Jg Jh Jl Jn Jp Jr Js Jt Lh Li Lj Lu Lv Lx Ly Lz Ma Mb Mc Md Mf Mg Mi Mj Mk Ml Mm Mn Mq Mr Mt Mu Mv Mw Mz Na Nb Nc Nd Ne Nf Ng Nh Ni Nk No Nq Nr Ns Nv Nx Ny Oe Oh Oi On Oz Pa Pb Pc Pd Pe Pf Pg Qa Qb Qc Qe) Mx(Fr Hq Hr Hu Hv Hw Hx Ih Ii Ij Il In Io Ip Iq Ir Is It Iu Jg Jh Jk Jl Jm Jn Jo Jp Jq Jr Js Jt Lh Li Lj Lu Lv Lx Ly Lz Ma Mc Md Mf Mg Mi Mk Ml Mm Mn Mq Mr Mt Mu Mz Na Nb Nc Nd Ne Nf Nh Ni Nk No Nr Ns Nv Oh Oi On Oz Pa Pb Pc Pd Pe Pf Pg Po Pz Qa Qb Qc Qe) Qd(Fr Hq Hr Hu Hv Hw Hx Ih Ii Ij In Io Ip Iq Ir Is It Iu Jg Jh Jk Jl Jm Jn Jo Jp Jq Jr Js Jt Li Lj Lu Lv Lx Ly Lz Ma Mc Md Mg Mi Mk Ml Mm Mn Mq Mr Mt Mu Mv Mw Mz Na Nb Nc Nd Ne Nf Nh Ni Nk No Nr Ns Nv Ny Oh Oi On Oz Pa Pb Pc Pd Pe Pf Pg Po Pz Qa Qb Qc Qe) Of(aC aN bM Fr Hq Hr Hu Hv Hw Hx Ih Ii In Io Ip Iq Is It Iu Jh Jk Jl Jm Jn Jo Jp Jq Jr Js Lh Li Lj Lu Lx Ly Lz Ma Mc Md Mg Mj Mk Ml Mm Mn Mq Mr Mt Mu Mv Mw Mz Na Nb Nc Nf Ng Ni Nk No Nq Nr Ns Nv Ny Oe Oh Oi Om Oz Pa Pb Pc Pd Pe Pf Pg Po Pz Qa Qb Qc Qe) Mb(Fr Hr Hv Hw Hx Ih Ii Ij Ik Il In Io Ip Iq Ir Is It Iu Jg Jl Jn Jo Jp Jq Js Jt Lh Li Lu Lv Lx Ly Lz Ma Mc Md Mf Mg Mi Mj Mk Ml Mm Mn Mq Mr Mt Mu Mv Mw Na Nb Nc Ne Nf Ng Nh Ni Nk No Nq Nr Ns Nv Nx Ny Oe Oh Oi Om On Oy Oz Pb Pc Pd Pe Pf Pg Qa Qb Qe) Oy(Fr Hq Hr Hu Hv Hw Hx Ih Ik Il Io Ip Iq Ir Is It Iu Jg Jh Jk Jl Jn Jo Jp Jq Jr Js Jt Lh Li Lu Lv Lx Ly Lz Ma Mc Md Mf Mg Mi Mj Ml Mm Mn Mq Mr Mt Mv Mw My Mz Na Nb Nc Nd Ne Nf Ng Nh Ni Nk No Nr Ns Ny Oe Og Oh Oi Om Pa Pb Pc Pe Pf Po Pz Qb Qc) Fp(Fr Hq Hr Hu Hv Hw Hx Ih Ii Ij Ik Il In Io Ip Iq Ir Is It Iu Jg Jh Jk Jl Jm Jn Jo Jp Jq Jr Js Jt Li Lj Lu Lx Ly Lz Ma Mc Md Mg Mi Mk Ml Mm Mn Mq Mr Mt Mu Mz Na Nb Nc Nd Ni Nk No Nr Ns Nv Oh Oi On Oz Pa Pb Pc Pd Pe Pf Pg Po Pz Qa Qb Qc Qe) My(Fr Hr Hv Hw Hx Ih Ii Ik Il In Io Ip Iq Ir Is It Iu Jg Jk Jl Jn Jo Jp Jq Jr Js Lh Li Lj Lu Lx Ly Lz Ma Mc Md Mg Mj Mk Ml Mm Mn Mq Mr Mv Mw Mz Na Nb Nc Nd Ne Nf Ng Nh Ni Nk No Nr Ns Ny Oe Oh Oi Om Oz Pa Pb Pc Pd Pe Pf Pg Po Pz Qb Qc Qe) Lw(aN Fr Hq Hu Hv Hw Hx Ih Ii Ij In Io Ip Iq Is It Iu Jg Jh Jk Jl Jm Jn Jo Jp Jq Jr Js Jt Lh Li Lj Lu Lx Ly Lz Ma Mc Md Mg Mi Mj Mk Ml Mm Mn Mq Mt Mu Na Nb Nd Ni Nk No Nr Ns Nv Oh Oi On Oz Pa Pb Pc Pd Pe Pf Pg Po Pz Qb Qc) Iv(Fr Hq Hr Hu Hv Hw Hx Ih Ii Ij In Ip Iq Ir Is It Iu Jg Jh Jk Jl Jm Jn Jo Jp Jq Jr Js Jt Li Lj Lu Lx Ly Lz Ma Mc Md Mg Mm Mn Mq Mr Mt Mu Na Nb Nc Nk No Nr Ns Nv Oh Oi On Oz Pa Pb Pc Pd Pe Pf Pg Po Pz Qa Qb Qc Qe) Nn(Fr Hr Hu Hx Ih Ii Ij Ik Il Io Iq Ir Is It Iu Jg Jh Jl Jn Jp Jt Lh Lu Lv Lx Lz Ma Mc Md Mf Mg Mi Mj Mk Ml Mn Mr Mt Mu Mz Na Nb Nc Nd Ne Nf Nh Ni Nk No Nq Nr Ns Nv Nx Ny Oe Oh Oi Om On Oz Pb Pc Pd Pe Qa Qb Qe) Og(Fr Hq Hr Hu Hv Hw Hx Ii In Io Ip Iq Iu Jh Jk Jm Jn Jo Jp Jq Jr Js Lh Li Lj Lu Lx Ly Lz Ma Mc Md Mg Mj Mk Ml Mm Mn Mq Mt Mu Mv Mw Na Nb Nf Ng Ni Nk No Nq Nr Ns Ny Oe Oh Oi Oz Pa Pb Pc Pd Pe Pf Pg Po Pz Qc) Lv(Fr Hr Hx Ih Ii Ij Ik Il Io Ip Iq Ir Is It Iu Jl Jn Jt Lh Li Lu Lx Lz Ma Mc Md Mf Mg Mi Mj Mk Ml Mm Mn Mr Mt Mu Mv Mw Mz Na Nb Nc Nd Ne Nf Ng Nh Ni Nk No Nq Nr Ns Nv Nx Ny Oe Oh Om On Oz Pb Pd Qa Qb Qe) Ng(Fr Ih Ij Ik Il Io Iq Ir Is It Iu Jg Jj Jk Jl Jn Jp Jt Lh Li Lu Lx Lz Ma Mc Mf Mg Mi Mj Mk Ml Mm Mr Mt Mu Mv Mw Mz Na Nb Nc Nd Ne Nf Nh Ni Nk No Nq Nr Ns Nv Ny Oe Oh Om Oz Pb Pd Pe Pg Qa Qb Qe) Nx(Hr Ih Ii Ij Ik Il Io Iq Ir Is It Iu Jl Jt Lh Li Lu Lx Lz Ma Mc Md Mf Mg Mi Mj Mk Ml Mm Mn Mr Mt Mu Mv Mw Mz Na Nb Nc Nd Ne Nf Nh Ni No Nq Nr Ns Nv Ny Oe Oh Om On Oz Pb Pd Pe Qa Qb Qe) Qa(Hq Hr Hu Hv Hw Hx Ii Ij Ik Il Io Iq Iu Jg Jh Jk Jl Jn Jp Jq Jt Lh Lz Mc Md Mf Mi Mj Ml Mr Mv Mw Mz Na Nc Nd Ne Nf Nh Ni Nq Ns Ny Oe Oh Om On Oz Pb Pc Pd Pe Pg Pz Qe) Ms(Fr Hq Hu Hv Hw Hx Ii In Io Ip Iq Iu Jg Jh Jk Jm Jo Jp Jq Jr Lh Li Lj Lu Lx Ly Ma Md Mg Mj Mk Mm Mn Mq Na Nb Nk No Nr Nv Oi Pa Pc Pe Pf Pg Po Pz Qc) Ne(aC Hr Ih Ij Ik Il Io Ir Is It Iu Jl Jt Lh Lx Lz Mc Md Mf Mi Mj Mk Ml Mm Mr Mu Mv Mw Mz Nb Nd Nf Nh Ni No Nq Ns Nv Ny Oe Oh Om On Oz Pb Pd Qb Qe) Om(Ih Ij Ik Il Io Ir Is It Jl Jt Lu Lx Lz Mc Mf Mi Ml Mm Mr Mt Mu Mv Mw Mz Na Nb Nc Nd Nf Nh Ni Nk No Nq Nr Ns Nv Ny Oe Oh On Oz Pb Pd Pe Qb Qe) Mf(Ih Ij Ik Il Io Ir Is It Iu Jl Jt Lh Lu Lx Lz Mc Md Mi Mj Ml Mr Mt Mv Mw Mz Nb Nc Nd Nf Nh Ni No Nq Ns Nv Ny Oe Oh On Oz Pb Pd Pe Qb Qe) aA(Fr Hq Hu Hv Hw Hx In Ip Iq Is Jh Jk Jm Jo Jp Jq Jr Js Jt Lj Lu Ly Ma Mg Mk Mm Mn Mq Mu Na Nk No Ns Nv Oi Pa Pc Pe Pf Pg Po Pz Qc) Nh(Ih Ij Ik Il Io Ir Is It Iu Jl Jt Lh Lx Lz Mc Md Mi Mj Ml Mm Mr Mu Mv Mw Mz Nb Nd Nf Ni No Nq Ns Nv Ny Oe Oh On Oz Pb Pd Qb Qe) Oe(Ih Ij Ik Il Ir Is It Jg Jl Jt Lx Lz Mi Ml Mm Mr Mt Mu Mv Mw Mz Nb Nc Nd Nf Ni No Nq Ns Nv Ny Oh On Pb Qb Qe) Mi(aC Hr Hx Ih Ii Ik Il Ir Is It Iu Lh Lz Md Mj Ml Mr Mv Mw Mz Nb Nc Nf Ni Nq Ns Ny On Pb Qb Qe) Mw(Ih Ij Ik Il Ir Is It Jg Jj Jl Jt Lh Lu Lx Mr Mt Mu Mz Nb Nc Nd Ni No Nq Ns Nv Pd Pe Qb Qe) Mv(Ih Ij Ik Il Ir Is It Jj Jl Jt Lh Lu Lx Mr Mt Mu Mz Nb Nc Nd Ni No Nq Ns Nv Pd Pe Qb Qe) Ny(Ih Ij Ik Il Ir Is It Jl Jt Lh Lx Mr Mt Mu Mz Nb Nc Nd Ni Nq Nv On Pd Pe Qb Qe) Jj(Fr Hq Ii In Io Ip Iq Iu Jh Lj Lu Ly Ma Md Mg Mj Mk Mn Mq Na Nf Ni Oh Oi Pa) Qe(Hr Hx Ik Il Iu Jg Jh Jl Jq Jt Lh Mj Mz Nc Nd Nf Ni Nq Ns Oz Pb Pd Pe Pg) Nq(Ih Ij Ik Il Ir Is It Jl Jt Lx Mr Mt Mz Nb Nc Nd No On Qb) Mz(aC Hr Hx Ii Ik Il Ir It Md Ml Nc Nd Nf Ns On Pb Qb) Nd(aC Ih Ij Ik Il Ir It Jt Lz Mr Nc Nf Ni Pb Qb) Ik(Ih Ii Ij Ir Is It Ml Nb Nc Nf On Pb Qb) Pb(Ij Jl Jt Lx Mr Mt Nc On Oz Pd Pe Qb) aC(Aj aM aO aX bV cX Ji Jv Mt Nb Nu Pk) Qb(Hr Hx Il Iu Jg Jl Jt Lh Ni Pd) Nc(Ih Ij Il Ir Is Mr Nb Ni On) Nf(Ih Ij Il Ir It Mr Ni On) Ii(Ih Ij Jl Jt Lh Mr On Pe) Hx(Jl Jt Lh Lx Mr Mt Pe) Hr(Hv Jl Jq Jt Pd Pe) On(Ir Jh Lh Mr Nb Ni) Ml(Ij Lh Lx Mr Pe) Jt(Iu Jh Lh Mj Pz) Il(Ir Is It Nb) bM(Aj aN aS bE) Ir(Iu Ni Ns) aN(Aj dE) MuHu PzJg JnJr} Qd{Ms(Fp Fr Hq Hr Hu Hv Hw Hx Ih Ii Ij In Io Ip Iq Ir Is It Iu Iv Jh Jk Jm Jn Jo Jq Jr Js Jt Lh Li Lj Lu Lv Lx Ly Lz Ma Mb Mc Md Me Mf Mg Mh Mi Mj Mk Ml Mm Mn Mq Mr Mt Mu Mv Mw Na Nb Nc Nd Ne Nf Ng Nh Ni Nk No Nq Nr Ns Nv Ny Of Oh Oi Om Oz Pa Pb Pc Pd Pe Pf Pg Po Pz Qa Qb Qc Qe) Oy(Fp Fr Hq Hr Hu Hv Hw Hx Ih Ij In Io Ip Iq Ir Is It Iu Iv Jh Jk Jm Jn Jo Jq Jr Js Jt Li Lj Lu Lv Ly Lz Ma Mb Mc Md Me Mf Mg Mh Mj Mk Ml Mm Mn Mq Mr Mt Mu Mv Mw My Na Nb Nc Nd Ne Nf Ng Nh Ni Nk No Nq Nr Ns Ny Oe Of Oh Oi Om Oz Pa Pb Pc Pe Pf Pg Po Pz Qa Qb Qc Qe) Nx(Fp Hq Hr Hu Hv Hw Hx Ii Ik Il In Io Iq Ir It Iu Iv Jg Jh Jk Jl Jm Jn Jo Jp Jq Jr Js Jt Lh Li Lu Lv Lx Lz Mb Mc Me Mf Mg Mh Mi Mj Mk Ml Mm Mr Mt Mu Mv Mw Mx Mz Nb Nc Nd Ne Nf Ng Nh Ni Nk Nl Nm Nn No Nq Ns Nv Ny Oh Oi Om On Oz Pa Pb Pc Pd Pe Pf Pg Pz Qa Qc Qe) Lw(Aj aN Fr Hq Hu Hv Hw Hx Ih Ii Ij In Io Ip Iq Ir Is It Iu Jh Jk Jm Jn Jo Jq Jr Js Jt Li Lj Lu Lv Lx Ly Lz Ma Mc Md Me Mf Mg Mi Mk Ml Mm Mn Mp Mq Mr Mt Mu Mv Mw Na Nb

Figure 39 Continued

Nc Nd Nf Nh Ni Nk Nm Nn No Nr Ns Nv Ny Oh Oi Om Oz Pa Pb Pc Pd Pe Pf Pg Po Pz Qa Qb Qc Qe) My(Fp Fr Hq Hr Hu Hv Hw Ih Ij Il In Io Ip Iq Ir Is It Iu Iv Jh Jk Jm Jn Jo Jq Jr Js Jt Li Lu Lv Lx Lz Ma Mb Mc Md Me Mf Mg Mh Mi Mj Mk Mm Mr Mt Mu Mv Mx Nb Nc Nd Ne Nf Nh Ni Nk Nl No Nq Nr Ns Ny Oe Of Oh Om Oz Pa Pb Pc Pd Pe Pf Pg Po Qa Qc Qe) Mp(Fp Hq Hr Hu Hv Hw Hx Ij Ik Il In Io Iq Ir It Iu Iv Jg Jh Jk Jl Jm Jn Jo Jp Jq Jr Js Jt Lh Li Lv Lx Lz Mb Mc Me Mf Mg Mh Mj Mk Ml Mm Mr Mt Mu Mv Mw Mx Nb Nc Ne Nf Ng Nh Ni Nk Nl Nm Nn Nq Ns Nv Ny Oe Of Om On Oz Pb Pc Pd Pe Pf Pg Pz Qc Qe) Ik(Fp Hq Hr Hv Hw Hx Ii Il In Io Iq Ir Is It Iu Iv Jh Jk Jl Jm Jn Jp Jq Jr Js Jt Lh Li Lv Lx Mb Mc Md Me Mf Mi Mj Mk Ml Mm Mr Mt Mu Mx Mz Nb Nc Nd Ne Nf Ng Nh Ni Nk Nl Nm Nn No Nq Ns Nv Ny Oe Of Oh Om On Oz Pa Pb Pc Pd Pe Pf Pg Pz Qc Qe) Mz(aC aN Fp Hq Hr Hw Hx Il In Io Iq Ir Is It Iu Iv Jg Jk Jl Jm Jn Jp Jq Jr Jt Lh Li Lv Lx Lz Mb Mc Me Mf Mh Mi Mj Mk Mm Mr Mt Mu Mx Na Nb Nc Nd Ne Nf Ng Nh Nl Nm Nn No Nq Ns Nv Oe Of Oh Om On Oz Pb Pc Pd Pe Pf Pg Pz Qc Qe) Og(Fr Hq Hr Hu Hv Hw Hx Ih Ii In Io Ip Iq Ir Is It Iu Jh Jk Jm Jn Jo Jr Js Li Lj Lu Ly Ma Mb Mc Md Me Mg Mk Ml Mm Mn Mq Mr Mt Mu Mv Mw Na Nb Nc Nd Nf Ng Ni Nk No Nr Ns Ny Of Oh Oi Om Oz Pa Pb Pc Pe Pf Pg Po Pz Qa Qb Qc Qe) Jg(Fp Hq Hr Hu Hv Hw Hx Il Io It Iu Iv Jh Jk Jl Jm Jn Jo Jp Jq Jr Js Jt Lh Lv Lx Lz Mb Mc Mc Mf Mg Mh Mi Mj Mk Mm Mr Mt Mu Mv Mw Mx Nb Nc Nd Ne Nh Ni Nl Nm Nn No Nq Ns Nv Ny Oe Oh Oi Om On Oz Pb Pc Pd Pe Pf Pg Pz Qc Qe) Nm(aC Aj Fp Hq Hr Hw Il In Io Ir It Iu Iv Jh Jk Jl Jm Jn Jo Jp Jq Jr Js Lh Li Lu Lv Lx Lz Mb Me Mf Mg Mh Mi Mj Mk Mr Mt Mu Mx Na Nb Nc Nd Ne Nf Nh Ni Nl Nn No Nq Ns Nv Oe Of Om On Oz Pb Pc Pd Pe Pf Pg Pz Qc Qe) On(Fp Hq Hr Hu Hv Hw Hx Ii Il In Io Iq Ir It Iu Iv Jh Jk Jl Jm Jn Jo Jp Jq Jr Jt Lh Li Lv Lx Lz Mb Mc Me Mf Mg Mi Mj Mk Ml Mm Mr Mu Mv Mx Nb Nc Nd Ne Nf Nh Ni Nl Nn Ns Nv Ny Oh Om Oz Pb Pc Pd Pe Pg Pz Qc Qe) aA(Fr Hq Hu Hv Hw Hx Ii In Io Ip Iq Ir Is It Jh Jk Jm Jo Jq Jr Js Jt Lh Lj Lu Lx Ly Ma Mc Md Mf Mg Mi Mk Ml Mm Mn Mq Mr Mt Mu Mv Mw Na Nb Nc Nf Ni Nk No Nr Ns Ny Oh Oi Om Oz Pa Pb Pc Pf Pg Po Pz Qa Qb Qc Qe) Nj(Fr Hq Hu Hv Hw Hx Ii Io Ip Iq Ir Is Jh Jk Jm Jo Jr Js Lj Lu Ly Ma Mb Md Mg Ml Mn Mq Mv Mw Na Nc Nf Nl Nq Nr Ny Oh Oi Om Pa Pf Po Qa Qb Qe) Jp(aC Fp Hq Hr Hx Il Io Iu Iv Jk Jl Jn Jq Jr Jt Lh Lv Lx Lz Mb Me Mf Mh Mi Mj Mk Mr Mx Nd Ne Ng Nh Ni Nl Nn Nq Nv Oe Of Om Oz Pb Pc Pd Pe Pz) Mh(Fp Hq Hr Il It Iu Iv Jl Jn Jq Js Jt Lh Lv Lx Lz Me Mf Mi Mj Mk Mm Mr Mu Mx Nd Ne Nf Ng Nh Nl Nn Nq Ns Nv Oe Of Oz Pb Pd Pe Qe) Nl(Fp Il It Iu Iv Jl Jn Jq Jt Lh Li Lv Lx Lz Mb Me Mf Mi Mj Mk Mm Mr Mu Mx Nb Nd Ne Ng Nh Ni Nk Nn Nq Nv Oe Of Oz Pb Pc Pd Pe) Nn(Fp Hu Il Iu Iv Jh Jk Jl Jn Jq Lh Lv Lx Lz Mb Me Mi Mj Mk Mv Mw Mx Nd Ne Nf Ng Nh Nq Ns Nv Oe Of Om Oz Pb Pc Pd) Il(Fp Iu Iv Jl Jn Jt Lh Lv Lx Mb Mf Mi Mm Mr Mx Nd Ne Nh Nq Nv Oe Of Oz Pd Pe Pf) Oe(Fp Iv Jl Jn Jq Jt Lh Li Lv Lx Lz Mb Mf Mi Mj Mm Mt Mx Ne Nh Nq Nv Of Oz) Of(aC aN Fp Iv Jl Jq Jt Lh Li Lv Lx Lz Mf Mi Mj Mm Mx Nd Ne Nh Nq Nv Pd) Im(Fr Hu Ih Ij Ip Is Jo Lj Lu Ly Lz Ma Mg Mn Mq Mv Na Nr Ny Oi Po Qa) Iv(Fp Jl Jq Jt Lh Lv Lx Mf Mi Mj Mm Mx Nd Ne Ng Nh Nq Nv Oz) Jl(Fp Hr Ii Iu Lv Lz Mb Mf Mj Mx Ne Ng Nh Nq Oz Pb) Fp(Jq Jt Lz Mf Mi Mj Mm Mx Nd Ne Nh Nq Nv Oz) Nq(Jt Lh Li Lv Lx Mf Mi Mm Mx Nd Nv Pd) aC(Aj aS Bb bM dB Jj Jt Jv Nb Nh Oi Pk) Mj(Jq Jt Lh Lv Lx Mi Mr Mx Nv Pe) Mx(It Jr Js Lh Lv Lz Mb Mm Oz) Nv(Iu Jk Lv Mb Mf Mv Mw Ng Pb) Lh(Hr Hx Ii Iu Mb Mf Ng Pb) Lv(Iu Lz Mm Nd Ng Oz) Mb(Jq Jt Mi Mm Nd) Ng(Jt Lx Mf Mi Mm) aN(Aj bE bM dE Ji) Lz(Lx Nd Pd Pf) bM(Aj aS bE Ji) Mi(Hx Iu Mf) Nu(Ii Ij) Lx(Hx Iu) Jq(Js Na) MuHu IuJt} Nu{Jp(Fr Hq Hr Hu Hv Hw Hx Ih Ii Ij Ik Il In Io Ip Iq Ir Is It Iu Iv Jg Jh Jk Jm Jn Jo Jr Js Jt Lh Li Lj Lu Lx Ly Lz Ma Mb Mc Md Me Mf Mg Mj Mk Ml Mm Mn Mq Mr Mt Mu Mv Mw Na Nb Nc Nd Ne Nf Nh Ni Nk Nl No Nq Nr Ns Ny Oe Oh Oi Om On Oz Pa Pb Pc Pd Pe Pf Pg Po Pz Qa Qb Qc Qe) Jl(Fp Fr Hu Hv Hw Hx Ih Ii Ij Ik Il In Io Ip Iq Ir Is It Iu Iv Jh Jk Jn Jo Jq Jr Js Jt Lh Li Lj Lv Lx Ly Lz Ma Mb Mc Md Me Mf Mg Mh Mi Mj Mk Ml Mm Mn Mp Mr Mt Mu Mv Mw Mx Nb Nc Nd Ne Nf Ng Nh Ni Nk Nl Nm Nn No Nq Nr Ns Nv Ny Oe Of Oh Oi Oz Pb Pc Pd Pe Pg Qa Qb Qc Qe) Lw(Aa Fr Hq Hr Hu Hv Hw Hx Ih Ii Ij Ik Il In Io Ip Iq Is It Iu Jh Jk Jm Jo Jr Jt Lj Lu Lx Ly Lz Ma Mc Md Me Mf Mg Mi Mj Mk Ml Mm Mn Mq Mr Mt Mu Mv Mw Na Nb Nc Nd Ne Nf Nh Ni Nk Nm Nn No Nq Nr Ns Ny Oe Of Oh Oi Om Oz Pa Pb Pc Pd Pf Pg Po Pz Qc) Jq(Fr Hr Hu Hx Ih Ii Ij Ik In Ip Iq Ir Is It Iu Iv Jg Jh Jn Jo Jr Js Jt Lh Li Lj Lu Lv Lx Ly Mb Md Me Mf Mg Mi Mj Mk Ml Mm Mn Mr Mt Mu Mv Mw Mx Na Nb Nc Nd Ne Nf Ng Nh Nl Nm Nn No Nq Ns Nv Nx Ny Oe Of Oi Om Oz Pa Pb Pc Pd Pe Pf Pg Po Qa Qb Qc) On(Fr Hq Hr Hu Hv Hw Hx Ih Ii Ij Ik Il In Io Ip Iq Ir Is It Iu Jg Jm Jn Jr Js Jt Lh Li Lj Lu Lx Ly Lz Ma Mc Md Mf Mi Mj Mk Ml Mm Mn Mq Mr Mt Mu Na Nb Nc Nd Ne Nf Nh Ni Nk Nm Nn No Nr Ns Nv Nx Ny Oh Oi Oz Pa Pb Pc Pd Pe Pf Pg Po Qa Qb Qc Qe) aA(Fr Hq Hu Hv Hw Hx Ii Ik Il In Io Ip Iq Is It Iu Jh Jk Jm Jo Jr Lj Lu Lx Ly Lz Ma Mc Md Me Mf Mg Mi Mj Mk Ml Mm Mn Mq Mr Mt Mu Mv Mw Na Nb Nc Nd Ne Nf Nh Ni Nk Nn No Nq Nr Ns Ny Oe Of Oh Oi Om Oz Pa Pb Pc Pd Pe Pf Pg Po Pz Qc) Nj(Aa Fr Hr Hu Hv Hw Hx Ih Ii Ij Ik In Io Ip Iq Ir Is It Iu Iv Jh Jn Jo Jr Lj Lu Lv Ly Lz Ma Md Me Mf Mh Mk Mm Mn Mq Ms Mt Mu My Nb Ne Nf Ng Nh Ni Nk Nq Nr Ns Ny Oe Of Oh Oi Om Oy Oz Pa Pb Pc Pd Pf Pg Po Qc) Og(Aa Fr Hq Hu Hv Hw Ih Ii Ik Il Ip It Jh Jk Jm Jo Jr Lj Ma Mb Md Me Mf Mg Mh Mm Mn Mq Mr Ms Mt Mu My Nb Nc Nd Ne Nh Nl Nq Nr Of Oh Om Oy Oz Pa Pb Pc Pd Pf Pg Po Pz Qc) Qe(Fp Hr Ik Il In Ir Is Iu Iv Jg Jn Jr Js Jt Lh Li Lv Lx Mb Me Mf Mh Mi Mk Mm Mp Mr Mx Mz Nd Ng Nh Nl Nm Nn No Nq Nv Nx Oe Of Oy Pb Pc Pd Pe Qa) Mz(aC Fp Hr Ii In Ir Is Iv Jg Jn Jr Js Jt Lh Li Lv Lx Mb Mf Mh Mi Ml Mr Mv Mw Mx Nf Ng Nh Nl Nm Nn No Nv Ny Of Oy Oz Pc Pd Pe Qa Qb Qc) Qa(Fp Hr Ik In Ir Iu Iv Jg Jk Jm Jn Jr Js Jt Lh Li Lv Lx Mb Me Mf Mh Mi Mk Mp Mr Mx Na Nd Ng Nh Nl Nm Nn No Nq Nv Oe Of Oz Pb Pc Pe) Mp(Aa Hv Ih Ij In Ir Is Iv Jn Jr Js Jt Lh Li Lv Lx Mb Me Mf Mh Mr Ms Mx My Nf Ng Nh Nl Nm No Nv Ny Oe Of Pb Pc Pd Pe Qb Qc) Nx(In Ir Is It Iv Jg Jn Jo Js Jt Lh Li Lv Lx Mb Me Mh Mi Mr Mx My Nd Ng Nl Nm Nn No Nv Oe Oz Pa Pb Pc Pd Pe Qb Qc) Jg(Fp Ih Ik Ir Is Iv Jh Jn Jo Jr Js Jt Lh Lv Lx Mb Me Mf Mg Mi Mr Ms Nd Nl Nm Nn No Nq Nv Oe Pe Pz Qb Qc) Im(Fr Ih Ii Ij Io Ip Is It Lj Lu Ly Lz Ma Mc Md Mj Mk Ml Mm Mn Mq Mu Na Nb Nk Nr Ns Ny Oi Po) Mx(Fp Hu Ik In Ir Iv Jn Jr Js Jt Lh Li Lv Lx Mh Ms My Nm Nn No Nv Oy Pe Qb) Jj(Hr Hx Il In Io Iu Lu Ly Lz Mc Mj Mk Ml Mv Mw Na Nf Ng Ni Nk Ns Oe Of Oi) Fp(Ir Iv Jn Js Jt Lh Lv Lx Mf Mi Mm Ms My Ng Nl Nm Nn No Nv Oy Pe Qb) Jt(Hr In Ir Iu Iv Jn Jo Li Lv Lx Mb Mh Ms Nl Nn No Nv Of Oy Qb) Nv(Hu Hx Ir Iv Jh Jn Jr Js Lv Mb Mh Ms Mv Mw Nl Nm Of Pb Qb) Oy(Aa Ij Ir Iv Js Lh Li Lv Mi Mr Mt Mu Nm Nn No Pe Pg Qb) My(Aa Fr Ij Ir Js Lh Li Lv Lx Mi Nm Nn No Pe Qb) Js(In Iv Lh Lv Mb Mh Mi Ng Nm Nn No Oe Of) Lh(Hr Hx Ii Iv Jn Mb Mh Ms Mw Ng Of Qb) Nm(aC Iv Jn Lv Lx Mh Ms Ng Nl No Qb) Aa(Is Iv Ji Lu Mb Me Mh Nb Ne Of) Lv(Ir Iv Jn Li Ms Ng Nl Nn No Qb) Ms(Ij Ir Is Jn Li Mi Nn Qb) Qb(In Mh Mi Ng Nn No) Lx(Hx Jn Mh Ng Pb) Jn(Mh Mi Nn No) Ng(Ij Li Nn) Iv(Is Mi No) Ji(Aj aN) Kq(Ef Iz) LiOf PkaC} Im{Lw(Fr Hq Hu Hv Hw Hx Ih Ii Ij Ik Il In Io Ip Iq Ir Is It Iu Jh Jk Jm Jn Jo Jq Jr Jt Lh Li Lj Lu Lv Lx Ly Lz Ma Mc Md Me Mf Mg Mi Mj Mk Ml Mm Mn Mp Mq Mr Mt Mu Mv Mw Na Nb Nc Nd Ne Nf Nh Ni Nk Nm Nn No Nq Nr Ns Nv Ny Oe Oh Oi Oz Pa Pb Pc Pd Pe Pf Pg Po Pz Qa Qb Qc) Jp(Fr Hq Hr Hu Hv Hw Hx Ih Ii Ij Ik Il In Io Ip Iq Ir Is It Iu Jg Jh Jk Jm Jn Jo Jr Js Lh Li Lj Lu Lx Ly Lz Ma Mc Md Mg Mi Mj Mk Ml Mm Mn Mq Mr Mt Mu Mv Mw Na Nb Nc Nd Ne Nf Nh Ni Nk No Nr Ns Nv Ny Oe Oh Oi Om On Oz Pa Pc Pd Pe Pf Pg Po Pz Qa Qb Qc) Ms(Fp Hq Hr Hu Hv Hw Hx Ih Ik Il In Iq Ir Is Iu Jg Jh Jk Jm Jo Jr Lh Li Lj Lx Mb Mc Me Mf Mg Mh Mk Ml Mm Mq Mr Mt Mu My Nb Nc Nd Ne Nf Ng Nh Ni Nk Nl Nm No Nq Ns Nv Oe Oh Om Oz Pa Pb Pc Pd Pe Pf Pg Po Pz Qa Qb Qc Qe) Jl(Fp Hq Hu Hw Hx Ii Ik Il In Iq Iu Iv Jg Jh Jk Jm Jn Jo Jq Jr Js Jt Li Lv Lx Mb Me Mf Mg Mh Mi Mj Mk Mm Mp Mr Mt Mu Mv Mw Mx Mz Nb Nc Ne Nf Ng Nh Ni Nl Nm Nn Nq Nr Ns Nx Ny Oe Om On Oz Pb Pc Pd Pe Pg Pz Qa Qc Qe) Mx(Fp Hq Hr Hu Hw Hx Ii Ik Il In Iq It Iu Iv Jh Jk Jm Jn Jo Jq Jr Js Jt Lh Li Lv Lx Mb Me Mh Mi Mj Mk Mm Mp Mr Mt Mu Mz Nc Nd Ne Nf Ng Nh Ni Nl Nm Nn No Nq Nv Nx Oe Of Om On Oz Pb Pc Pd Pe Pf Pz Qa Qc Qe) On(Fp Hq Hr Hu Hv Hw Hx Ih Ii Ik Il In Iq Ir Iu Iv Jg Jh Jk Jm Jn Jq Jr Js Jt Lh Li Lj Lv Mb Me Mf Mg Mi Ml Mp Mr Mu Mv Mz Nb Nc Ne Nf Nh Ni Nl Nm Nn Nq Nx Oe Om Oz Pb Pd Pe Pz Qa Qb Qc Qe) Oy(Fp Fr Hq Hr Hu Hv Hw Hx In Iq Iu Jn

Po Pz Qc) Mz(Fp Fr Hr Hx Ih Ii Ij Ik In Ir Iv Jl Jq Js Jt Lh Li Lx Md Mh Mi Ml Mm Mr Ms Mx My Nd Nf Ni Nk Nm No Nv Nx Ny Oe Oy Pb
Pe Qa Qb Qe) Mp(Fp Fr Ih Ij Ik In Ir Iv Jl Jn Jq Js Jt Lh Li Lw Lx Mr Mt Mx Ni Nk Nm Nn No Nv Nx Ny Oe Og Oy Qa Qb Qc Qe) Jg(Fp Ik Iv
Jl Jq Js Lh Lx Mg Mh Mi Mr Mx Nd Ng Nn No Nv Oe Oy Pe Qa Qb Qe) Lw(Fp Fr Ih Ij Ir Iv Jn Js Jt Lh Li Lx Mi Mt Nn No Nv Nx Ny Pe Qb)
Qa(Ik In Iv Jl Jq Jt Lh Lx Mi Mr Ms Mx Nd Ni Nm Nn No Nv Nx Oe Oy) Jl(Fp Hr Ih Ij Iv Js Jt Li Lx Mr Mx Nk Nm Nn No Nx Ny Oy Qb Qe)
Qc(Jq Jt Lh Li Lx Mi Mm Mr Mx Nd Ni Nk Nm Nn No Nv Nx Oy) Og(Fp Fr Ir Iv Js Jt Lh Li Lx Mi Mr Mx Nn No Nx Ny Qb) Nv(Fp Ik Iv Mh
Mi Mr Mx My Ng Ni Nk Nm Nn Oe Of) Lh(Fp Hr Ih Ii Ik Iv Mr Mx Nk Nm Oy) Nm(Fp Iv Js Li Lx Mr Mx No Qb) Jt(Fp Iv Lx Mr Mx Qb)
Fp(Mi Mm Nn Nx) Lx(Mh Mx Oy) Mr(Mm Nd Nn) Mi(Iv Nx) Li(Mx Ni) NoNk Islv} Jp{aA(Hr Ij Ik Ir Iv Jg Jl Jn Jq Jr Js Jt Lh Li Lj Lv Lx Mb
Me Mf Mi Ml Mp Mr Mt My Mz Ne Ng Nh Nl Nm Nn Nq Nr Nv Nx Oe Of Og Oy Pb Pd Pe Pf Po Qa Qb Qe) Lw(aN Hr Ih Ij Ik Ir Is Iv Jg Jl Jn
Jr Js Lh Li Lj Lv Lx Me Mf Mi Ml Mp Mr Mt My Mz Ne Ng Nh Nl Nn No Nq Nv Nx Ny Of Om Pb Pe Qa Qb Qe) Ms(Ih Ij Ir Is Iv Jl Jn Jq Jr Js
Jt Lh Lv Me Mf Mh Mi Mr Mz Nl Nm Nn Nv Nx Of Og Oy Qa Qb Qe) Og(Fp Ik Il Ir Iv Jg Jl Jq Js Jt Lh Li Lv Mh Mi Mp Mx Mz Nn Nv Nx
Qa Qb Qe) Fp(Hr Ik Iv Jl Jq Jt Lv Mf Mh Mi Mp Mx My Mz Nl Nm Nn Nv Nx Of Oy Pb) Mp(Ir Iv Jq Mb Me Mf Mh Mr Mx My Mz Ng Nl
Nm Nq Nx Of Oy Qa Qb Qe) Oy(Jl Jq Jt Lh Lv Lx Mh Mi Mx Mz Nm Nn Nv Nx Qa Qb Qe) Mx(Ik Iv Jg Jl Jq Lv Mb Mh My Ng Nm Nn Nx
Of Pb) Nm(Aj Iv Jl Mb Mh Mr My Ng Nl Nx Of Qb Qe) Mh(Iv Jg Jl Jq Lx Mi My Nl Nn Nx Pb) Of(Ij Iv Jg Jl Jt Mi Nv Nx) My(Jl Jt Mi Nn Nv
Qa Qe) Iz(dE Ic Jv Kq) Aj(aN bM dE) Mb(Jl Jt Mz) Ng(Jg Nn Nv) Or(dX eP Jv) Ef(Kq Wm) dX(Ky Pk) ivJl QaNx JvLj KieP} Jg{aA(Hr Ih Ij
Ik Ir Iv Jh Jl Jn Jq Jr Js Lh Li Lj Lv Lx Mb Me Mg Mi Ml Mp Mr Ms Mt Mv Mw Nc Nd Ne Nh Nl Nm Nn Nq Nr Nv Nx Oe Oz Pb Pd Pe Pf Po
Qa Qc Qe) Of(Hv Hw Ih Ij Ik Ir Is Jn Jq Jr Jt Lh Li Lv Lx Mb Me Mf Mg Mh Mi Mr Ms My Nd Ne Nh Ni Nl Nm Nn No Nq Nv Ny Oe Oh Oy
Oz Pd Pe Pf Pg Po Qe) Og(Ih Il Ir Is Iv Jn Jq Jr Js Jt Lh Li Lv Lx Mb Me Mf Mg Mi Mr Ms Mt My Nd Ne Ng Nh Nl Nm Nn No Nv Nx Oe Oy
Pd Pe Po Pz Qc) Ng(Fp Iv Jl Jn Jq Js Jt Lh Lv Lx Mf Mh Mi Mr Ms Mu Mx Mz Nd Nm Nn No Nx Oy Pd Pe Po Qe) Lw(Iv Jh Jl Jn Js Mb Me
Mg Mh Mp Mr Ms My Mz Nl Nx Oe Qa Qb Qe) Oy(Fp Jl Js Lx Mh Mi Mp Ms Mz Nn Nv Pe Pg Qa Qe) Mx(Fp Hu Ik Mg Mh Mp Ms My Mz
Nm Oe Pz Qb Qe) Mp(Fp Iv Mb Mg Mh Ms My Mz Qa Qb Qe) Ms(Fp Jl Js Mh Mi Mz Qa Qb Qe) My(Fp Jl Lx Mi Mz Qa Qb Qe) Mz(Fp Hx
Mv Ny Pb) Fp(Jq Oe) Qb(Jk Oe) QaJk} aA{Mz(Ih Ij Iv Jl Jn Js Jt Lh Li Lv Lw Lx Mb Mh Mp Ms Mt Mx My Ne Nh Nl Nm Nr Nv Nx Og Qa
Qb Qe) Li(Fp Hr Ih Ij Iv Jl Jn Lv Lw Mb Mh Mp Ms Mx My Ng Nl Nx Of Og Oy Qa Qb Qe) Fp(Hr Ih Ij Iv Jl Jn Js Jt Lv Lw Mp Ms Mt Mx Nl
Nm Nv Og Qa Qb Qe) Ij(Hr Iv Jl Jn Lv Lw Mb Mh Mp Ms Mx Nf Ng Nl Nq Nx Of Oy Qe) Qa(Hr Ik Iv Jn Lv Lw Mb Mh Mp Ms Mx My Ng
Nl Nm Nx Og Oy) Qe(Hr Iv Jl Jn Lv Lw Mb Mh Mp Ms Mx My Nl Nm Nx Og Oy) Jn(Ih Iv Jl Lv Lw Lx Mh Mp Ms Mt Mx Nl Nm Nx Og)
Nx(Iv Jl Lw Lx Mh Mp Ms Mx Nm Og Qb) Qb(Lv Lw Mp Ms Nm Og Oy) Mx(Ih Iv Jt Lw Nm Og) Lw(Ih Iv Js) Ih(Jl Lv) Js(Ms Og) Nv(Mh
Og) HrJl} Og{Ij(Fp Ik In Ir Is Jn Jq Js Jt Lh Li Lv Lx Mb Me Mf Mh Mi Mm Mr Mt Mu Mx My Mz Nc Nd Ne Nf Nh Nn No Nv Ny Of Qa Qb
Qc) Nm(Aj aN Il Iv Jl Js Li Mx Mz Nl Nv) Lw(aN Fp Iv Jl Js Li Mx Mz Nv Nx Qb) Nx(Fp Iv Jl Jt Li Mp Mx Mz Qb Qe) Qa(Iv Jq Jt Mp Ms
Mz) Qe(Iv Jq Jt Mp) Fp(Jt Nv) Mz(aN Wm) Ji(aN bM) IvNv QbJt} Lw{Qe(Aj aN Fp Hr Iv Mb Ms Mx My Mz Nl Nx Oy) aN(Aj bA cT dE Is Ji
Li Mx Mz Nb Oy Qc) Fp(Hr Iv Jl Js Ms Mx Mz Nl Nx) Ms(Jl Js Mx Mz Nx Qa Qb) Qa(Mb Mx My Mz Nx Oy) Iv(Aa Li Mx Mz Nx) Lj(Aj bM
bS cO dE) Li(Aj Mx Mz Nx) bM(Aj bA bE cT) Aa(Mb Me Nb) Mx(Mz Nx) Nv(Mb Oy) AjcT MzNl HrJl} Mz{aN(Aj bA bE bM cT dE Ir Iv Ji
Jo Li Lj Nb Ne Nh Of Oy Qc) Um(hP hR hV hW hX jD jE jM jP jU jV 1L 1M 1N rC rZ) bM(Aj aS bA bE Hr Ji Jo Ne Nf Nh Of) My(Aj aM bA
bL bV cC cT dE) Ms(Jt Mp Nx Qa Qb Qe) Aj(Jt Nh Nm) Mp(Iv Nl)} Ji{aN(Ap aS bA bE bV cT dD Fp Hr Ik Ip Ir Iu Iv Jq Lj Mh Mx My Nb
Nd Ne Nf Ng Nh Oi Oy Pz Qc Qe) bM(aL Ap aS aU bA bE bJ bV cM cT dD dE Ef Hr Ii Ik Iu Jq Lh My Nb Ne Nf Ng Oy Pg Pz) Aj(dE Nh
Nm) dE(Jo Of)} Aj{Nm(aS Ba bE bM bV Cs CU cV Dc dD dE Is Lj Lx Mt Nb Nf Qe) Kq(bM Iz Jh My) Jt(aN dE Mt) Is(aN bM)} Kq{Iz(aN
bM dE Ef Hv Jv Lv Mb Nd Of Or) Jh(bM Ef Jo Of) Ef(aN My)} bU{nN(dU eQ fB gC gZ jB oD oT oV oW pH pK) Ye(mW mZ)} Nx{Ms(Fp Jt
Mp Qa Qb Qe) Fp(Mp Nm) Qa(Of Oy) Qe(Nm Oy) LiOf} Kx{dX(bH Hx Mf oH Or pF Pi) eP(iJ Kp Of Rh)} Nm{Qe(Ms My Ng Oy) FpMp
NgNv HrJl} cM{Ye(nA nK) HpnK IbgC aLdU bOoD} bM{Jo(Cu Jt Ke) KeOf aNcT} Gc{hC(kK nR Oh Rf)} Ti{Qe(dX eP) GpOr} Ms{Mp(Js
Qa) FpJt} Aa{Of(Is Iv)} Gz{KrqT PjrB} FpNvOy LxdXeC IduYvT JvOraW Unconstrained panels with 2 analytes, where 1.0E-8 >= 'model p-value' > 0. Contains 324 panels of 200,124 total panels evaluated. : Ji(aA aC Et
Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc
Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq
Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nt(aA Et Fp Fr Hr Hu Hv Hw
Hx Ih Ii Ij Ik Il Im In Io Ip Iq Ir Is It Iu Iv Jg Jh Jj Jl Jn Jo Jp Jq Jr Js Jt Lh Li Lj Lu Lv Lw Lx Ly Lz Mb Mc Md Me Mf Mg Mh Mi Mj Mk Ml
Mm Mp Mr Ms Mt Mu Mv Mw Mx My Mz Na Nc Nd Ne Nf Ng Nh Nj Nk Nl Nm Nn No Nq Nr Ns Nu Nv Nw Nx Ny Oe Of Og Oh Oi Ok
Om On Oy Oz Pb Pc Pd Pe Pg Po Pz Qa Qb Qc Qd Qe) Et(aA Fp Im Iv Jj Jl Lw Mb Me Mh Mi Mp Ms Mx My Mz Ng Nj Nl Nu Nw Oe Of Og
Ok Oy Qa Qb Qd Qe) Ok(aA Fp Hr Im Iv Jj Jp Lw Mb Mh Mp Ms Mx My Mz Ng Nj Nl Nn Nu Nw Nx Oe Of Og Oy Qb Qd Qe) Nw(aA Fp Im
Iv Jj Lw Mh Mp Ms Mx Nj Nl Nu Of Og Qd) Qd(aA Im Jj Lw Nj Nu Og) On(Jj Nj Nu Of Og Oy) Im(aA Jj Nj Nu Og) NuJj Unconstrained panels with 2 analytes, where 1.0E-7 >= 'model p-value' > 1.0E-8. Contains 324 panels of 200,124 total panels evaluated. : Et(Fr
Hq Hr Hu Hv Hw Hx Ih Ii Ij Ik Il Im In Io Ip Iq Ir Is It Iu Jg Jh Jk Jm Jn Jo Jp Jq Jr Js Jt Lh Li Lj Lu Lv Lx Ly Lz Ma Mc Md Mf Mg Mj Mk Ml
Mm Mn Mq Mr Mt Mu Mv Mw Na Nb Nc Nd Ne Nf Nh Ni Nk Nm Nn No Nq Nr Ns Nv Nx Ny Oh Oi Om On Oz Pa Pb Pc Pd Pe Pf Pg Po Pz
Qc) Ok(Fr Hq Ih Ii Ij Ik Il In Io Ip Iq Ir Is It Iu Jg Jh Jl Jn Jo Jq Jr Js Jt Lh Li Lj Lu Lv Lx Ly Lz Ma Mc Md Me Mf Mg Mi Mj Mk Ml Mm Mn
Mq Mr Mt Mu Mv Mw Na Nb Nc Nd Ne Nf Nh Ni Nk Nm No Nq Nr Ns Nv Ny Oh Oi Om On Oz Pa Pb Pc Pd Pe Pf Pg Pz Qa Qc) Nw(Ih Ij Ik
Il Io Ir Is It Jl Jt Lh Lu Lv Lx Lz Mb Mc Me Mf Mi Ml Mm Mr Mt Mu Mv Mw My Mz Nb Nc Nd Ne Nf Ng Nh Ni Nm Nn No Nq Ns Nv Nx
Ny Oe Oh Om On Oy Oz Pb Pd Qa Qb Qe) Qd(Fp Ik Il Iv Jg Jl Jp Lh Lv Mb Mi Mp Ms Mx My Mz Nl Nm Nn Nq Nv Nx Oe Of On Oy) Im(Fp
Iv Jg Jl Jp Jt Lv Lw Mp Ms Mx My Mz Nl Nx Of On Oy Qe) Nu(aA Fp Jg Jl Jp Jq Js Jt Lw Mp Mz Nj Nx Og Qa Qe) Nt(Hq Jk Jm Ma Mn Mq
Nb Ni Pa Pf) On(aA Fp Iv Lw Mb Mh Ms My Ng) Jp(aA Fp Jj Lw Mx Nj) Jg(aA Jj Of Og) Jj(Nv Qa Qe) aC(Lw Mz Nm) NjaA IjOg JiaN Unconstrained panels with 2 analytes, where 1.0E-6 >= 'model p-value' > 1.0E-7. Contains 425 panels of 200,124 total panels evaluated. : Qd(aC
aN Fr Hq Hr Hu Hv Hw Hx Ih Ii Ij In Io Ip Iq Ir Is It Iu Jh Jk Jm Jn Jo Jq Jr Js Jt Li Lj Lu Lx Ly Lz Ma Mb Mc Md Me Mf Mg Mj Mk Ml Mm
Mn Mq Mr Mt Mu Mv Mw Na Nb Nc Nd Ne Nf Ng Nh Ni Nk No Nr Ns Ny Oh Oi Om Oz Pa Pb Pc Pd Pe Pf Pg Po Pz Qa Qb Qc Qe) Im(aC
Hq Hr Hu Hv Hw Hx Ik Il In Iq Ir Is Iu Jh Jk Jm Jn Jo Jq Jr Js Lh Li Lj Lu Lx Lz Mb Mc Mc Mf Mh Mi Mk Ml Mm Mr Mt Mu Mw Nb Nc Nd
Ne Nf Ng Nh Ni Nm Nn No Nq Ns Nv Oe Oh Om Oz Pa Pb Pc Pf Pg Po Pz Qa Qb Qc) On(Hr Hu Ih Ii Ik Ir It Jg Jh Jk Jl Jn Jp Jq Jr Js Jt
Lh Li Lj Lv Lx Me Mf Mg Mi Ml Mp Mr Mv Mw Mx Mz Nc Ne Nf Nh Ni Nl Nm Nn No Nq Nx Oe Om Pb Pz Qa Qb Qc Qe) Nw(aC aN Fr Hq
Hr Hu Hv Hw Hx Ii In Ip Iq Iu Jg Jh Jk Jm Jn Jo Jp Jq Jr Js Li Lj Ly Ma Md Mg Mj Mk Mn Mq Na Nk Nr Oi Pa Pc Pe Pf Pg Po Pz Qc) Jp(aC Ih
Ir Iv Jl Jq Js Jt Lh Li Lv Lx Mb Mh Mi Mp Mr Ms Mz Nl Nm Nn No Nv Nx Of Og Oy Qa Qb Qe) Nu(Aa Ih Ij Ir Is Iv Jn Jr Lh Li Lv Lx Mh Mi

Figure 39 Continued

Mr Ms Mx Nl Nm Nn No Nv Ny Oy Pe Qb) Nj(Fp Ij Jg Jj Jl Js Jt Lh Li Lw Lx Mi Mp Mr Mx Mz Nm No Nv Qa Qe) aA(Fp Ih Ij Iv Jl Jn Js Li Lx Mx Mz Nv Nx Qa Qb Qe) Jg(Fp Iv Jl Lw Mh Mi Mp Ms Mx Mz Ng Oy Qa Qb Qe) aC(Bb Is Jt Jv Ke Mi Mt Ok Pj Pk Vt) Jj(Fp Ij Iv Jl Js Jt Li Lx Nx Qb) Lw(Aa aN Fp Iv Js Li Mx Qa Qe) Ok(Hu Hv Hw Hx Jk Jm Po) Aa(Js Iv Nb Nt Qe) Qa(Mp Ms Nm Nx Og) Aj(Ji Jt Mz Nm) Qe(Nm Nx Og) Fp(Nm Nx) Mz(aN bM) IzKq JibM KxdX NvOg aNcT

Unconstrained panels with 2 analytes, where 1.0E-5 >= 'model p-value' > 1.0E-6. Contains 653 panels of 200,124 total panels evaluated. : Jp(Aa Aj aN Fr Hq Hr Hu Hv Hw Hx Ii Ij Ik Il In Io Ip Iq Is It Iu Iz Jg Jh Jk Jm Jn Jo Jr Jv Lj Lu Ly Lz Ma Mc Md Me Mf Mg Mj Mk Ml Mm Mn Mq Mt Mu Mv Mw My Na Nb Nc Nd Ne Nf Ng Nh Ni Nk Nq Nr Ns Ny Oe Oh Oi Om Oz Pa Pb Pc Pd Pe Pf Pg Po Pz Qc Uu) Nu(aC Fr Hq Hr Hu Hv Hw Hx Ii Ik Il In Io Ip Iq It Iu Jh Jk Jm Jo Lj Lu Ly Lz Ma Mb Mc Md Me Mf Mg Mj Mk Ml Mm Mn Mq Mt Mu Mv Mw My Na Nb Nc Nd Ne Nf Ng Nh Ni Nk Nq Nr Ns Oe Of Oh Oi Om Oz Pa Pb Pc Pd Pf Pg Po Pz Qc) Jg(Aj Hv Hw Ih Ik Ir Is Jh Jn Jo Jq Jr Js Jt Lh Li Lj Lv Lx Lz Mb Me Mf Mg Mm Mr Mt My Nc Nd Ne Nh Ni Nl Nm Nn No Nv Nx Oe Oh Om Oz Pb Pc Pd Pe Pf Po Pz Qc) On(aC Fr Hq Hv Hw Hx Ij Il In Io Ip Iq Is Iu Jm Jo Lu Ly Lz Ma Mc Md Mj Mk Mm Mn Mq Mt Mu Na Nb Nd Nk Nr Ns Nv Ny Oh Oi Oz Pa Pc Pd Pe Pf Pg Po) Aa(aA Et Fp Ih Im Ji Jj Lu Lv Lx Mb Me Mh Mp Mr Ms Mt Mx Ne Nh Nj Nl Nw Nx Of Og Ok Po Qa Qb Qc Qd) aC(aN bA Cs cT Cu Dc Ed Et Fa Fw Fy Gp Id Ih Kq Lh Li Lj Lx Mm Mp Nb Nd Nt Or Qa Qc Qe Uh Un Wm) Qa(Fp Hr Ik Iv Jl Jn Jq Js Jt Lh Li Lv Lx Mb Mf Mh Mi Mm Mr Mx My Mz Nh Nl Nn No Nv Oe Oy) aA(Fr Ik Ir Jj Jq Jt Lh Lv Lw Mb Mh Mi Mm Mp Mr Mt Nh Nl Nm Nn No Nr Ny Og Po Pz Qc) Lw(Aj bA bE bM Cs cT Ij Jj Jl Jn Jt Lh Lx Mp Mr Mt Mz Nl Nv Nx Ny Og Qb) Qe(Aj aN Fp Iv Jl Jq Js Jt Lh Li Lv Lx Mi Mm Mp Ms Mx Mz Nl Nn No Nv Oy) Nx(Iv Jl Js Jt Lh Li Lx Mh Mi Mp Mr Ms Mt Mx Mz Nj Nm Nn No Nv Og Qb) Im(Fr Ih Ii Ij Io Ip It Ly Ma Md Mg Mj Mn Mq Mv Na Nk Nr Ny Oi) Mz(bE dE Fp Iv Jj Jl Jt Jv Lh Li Lx Mp Ms Mx Nl Nm Nv Qb Wm) Nj(Fr Ih Ir Is Iv Jn Jq Lv Mm Mt Nd Nn Ny Og Pe Po Qb Qc) Mp(Fp Ij Ir Iv Jj Jn Jq Js Jt Li Lx Mx Nl Nm Nv Qb) Iv(Fp Jl Jq Js Jt Lh Li Lx Mi Mx Nm Nn No Nv Og) Jj(bM Fr Ir Is Jn Jq Lh Mt Mx Nl Nm Nn Ny Po) Nv(Fp Jt Lv Mb Mh Ms Mx My Ng Nl Nm Of Oy) Fp(Jl Jq Js Jt Lh Lv Mi Mm Mx Nl Og) Nm(aN Jl Jn Js Li Lx Mx Nl Og Qb) bM(bA cT Is Ke Nw Ok Or Pk Qd Uh) Aj(Dc Et Is Kq Mt Nt Nw Ok Qd) Jl(Jn Js Jt Li Lx Mx Nl Og Qb) aN(bA Dc Is Lj Lx Mt Nb Ok Qc) Jt(Li Lx Mb Ms Mx Nl Og Qb) Ji(Ap bA bE dE Ef Jv Wm) Li(Jq Js Lv Mx Nl Og Qb) Lx(Eo EW Mx) Qd(aS bE Wm) Kq(Ef Jh Of) Og(Js Lh Qb) Jv(Ke Or) GchC MsJs ZxjD QbLh KeOf KxeP Unconstrained panels with 2 analytes, where 1.0E-4 >= 'model p-value' > 1.0E-5. Contains 1,722 panels of 200,124 total panels evaluated. : aC(aA Ad Af AJ Al aM An Ao Ap Ar AX aZ Ba Bc bM bV cG Co Cp Cq cU Cv Cw Cx Dd De dF Dg Di Dk Dl dM Ef Fb Fn Fp Fr Gl Ha Hb Hc Hf Hr Hv Ib Ic Ij Ik In Io Ip Iq Ir It Iu Iv Iz Jd Je Jf Jg Jj Jl Jn Jq Jr Js Ju Jy Kc Kd Kf Kg Ki Kj Kk Kl Kn Ko Kp Kr Kx Kz Ld Lu Lv Ly Lz Mc Me Mf Mg Mh Mj Mk Ml Mn Mq Mr Ms Mu Mw Mx My Nc Ne Nf Ng Nh Ni Nj Nk Nl Nn No Nq Nr Ns Nv Nx Ny Oa Oe Of Og Oi Om Ou Ow Oz Pa Pb Pd Pe Pf Ph Pi Po Qb Qh Ql Qm Qu Qv Qx Qy Rc Sr St Tr Tz Ua Ub Uc Uf Um Up Ur Us Uu Vq Vu Tj) Ji(Ad AF aG aH aK aM An AO AR AS aU AW AX aY aZ Ba Bb bC BG bI bJ bL Bn BO bQ bS bV bX bZ cA cB cC cD cE cG cI cK cL cM cN CO CQ cR CS CT CU CV CW CX dA DB Dc dD De dF Dg dH DI dJ DK DL dM dX eF eP fP gL gP hC iH iJ oE oN Or Rc UM Us Uu Vo Vt wJ wQ) Mz(Aa Af aK aM aO aS Aw aX bA bI bJ bL bO bS bV bZ cC cD cI cK cM cO Cs CT cU cV CX dB dD dJ Dk dL Ed Ef Fr Hr Hx Ih Ij Ik Ir Is Iz Jn Jq Jr Js Lv Mb Mh Mi Ml Mm Mr Mt My Nc Ne Nf Nh Nn No Nr Ny Og Or Pb Pe Po Pz Qc Qv Rc Rf Ua Uc Uh UM Ur Uu vA Vt) Qe(Fr Hq Hr Hu Hv Hw Hx Ih Ij Ik Il In Io Ip Iq Ir Is It Iu Jh Jk Jm Jn Jo Jr Jv Lj Lu Ly Lz Ma Mb Mc Md Me Mf Mg Mh Mj Mk Ml Mn Mq Mr Mt Mu Mv Mw My Na Nb Nc Nd Ne Nf Ng Nh Ni Nk Nq Nr Ns Ny Oe Of Oh Oi Om Oz Pa Pb Pc Pd Pe Pf Pg Po Pz Qa Qb Qc) Aa(bM Fr Hq Hu Hv Hw Ii Ij Ik Il In Io Ip Iq Ir It Iu Jg Jh Jk Jl Jm Jn Jo Jr Js Jt Lh Li Lj Ly Lz Ma Mc Md Mf Mg Mi Mj Mk Ml Mm Mn Mq Mu Mv Mw My Na Nc Nd Nf Ng Ni Nk Nm Nn No Nq Nr Ns Nv Ny Oe Oh Oi Om On Oy Oz Pa Pb Pc Pd Pe Pf Pg Pz) Qa(Aj aN Fr Hq Hu Hv Hw Hx Ih Ii Ij Il In Io Ip Iq Ir Is It Iu Jh Jk Jm Jo Jr Lj Lu Ly Lz Ma Mc Md Me Mg Mj Mk Ml Mn Mq Mt Mu Mv Mw Na Nb Nc Nd Ne Nf Ng Ni Nk Nq Nr Ns Ny Of Oh Oi Om Oz Pa Pb Pc Pd Pe Pf Pg Po Pz Qb Qc) Nv(Hq Hr Hu Hv Hw Hx Ih Ii Ij Ik In Ip Iq Ir Is It Iu Jh Jk Jl Jn Jo Jq Jr Js Lh Li Lj Lx Lz Mc Me Mf Mg Mi Mk Ml Mm Mr Mt Mu Mv Mw Nb Nc Nd Ne Nf Nh Ni Nk Nn No Nq Nr Ns Ny Oe Oh Om Oz Pb Pc Pd Pe Pf Qb Qc) Li(Aj aN bM Fp Hq Hr Hu Hv Hw Ih Ij Ik In Ir Is It Jh Jn Jr Lh Lx Lz Mb Mc Me Mf Mh Mi Mk Mm Mr Ms Mt Mu Mv My Nb Nc Nd Ne Nf Ng Nh Ni Nn No Nq Nr Ns Ny Oe Of Oh Om Oy Oz Pa Pb Pc Pd Pe Pg Po Pz Qc) aA(aN Hq Hr Hu Hv Hw Hx Ii Il In Io Ip Iq Is It Iu Jh Jk Jm Jo Jr Lj Ly Lz Ma Mc Me Mf Mg Mj Mk Ml Mn Mq Ms Mu Mv Mw My Nb Nc Nd Ne Nf Ng Ni Nq Ns Oe Of Oh Oi Om Oy Oz Pa Pb Pc Pd Pe Pf Pg) aN(Aj aM aS aZ Bb bE bM bO bV cD cG cM Cs CU DD dE dF dK Ed Et Fa Fp Ij Im Ir Iv Jj Jl Jn Jq Jt Jv Ke Kq Lh Lv Mi Mp Mx Nd Ne Nt Nu Nx Og On Or Pa Pd Pe Pf Pk Po Qb Uh Un Vt) Js(Fr Hr Hu Ih Ij Ik Il In Ir Is It jD Jh Jn Jq Jr Jt Lh Lv Lx Mb Mc Me Mf Mh Mi Mm Mr Mt Mu Mx My Nb Nc Nd Ne Nf Ng Nh Ni Nl Nn No Ns Ny Oe Of Oy Oz Pb Pc Pd Pe Po Pz Qb Qc) Lw(aM An Ar aS Ax bJ bO bS bV cC cD cE cI cK cO CU cV cX dB Dc dD dE Fr Hr Hu Ih Ik Ir Is Jq Jr Lj Lv Mb Mh Mi Mm Ms Nc Ne Nh Nm Nn No Nr oE Or Oy Pe Po Pz Qc) Lx(Aj bM Dw Fp Hv Hx Ih Ij Ik Ir Is It Jn Jq Jr Jv Lh Lv Mb Me Mf Mh Mi Mm Mr Ms Mt My Nc Ne Ng Nh Ni Nl Nn No Ny Oe Og Oy Pb Pe Qb Qc Wm) Nj(Hv Hw Ii Ik Il In Ip Iq It Jh Jo Jr Lj Lz Ma Me Mf Mg Mh Mj Mn Mq Ms Mu Mv Mw Nb Ne Nh Ni Nk Nl Nq Nr Oe Oh Om Oy Oz Pa Pc Pd Pf Pg Pz) Jt(bM Fr Hr Ih Ii Ij Ik In Ir Is Iu Jn Jq Jr Lh Lj Lv Mf Mh Mi Mj Mm Mr Mt My Na Nc Nd Ne Ng Nh Nm Nn No Nr Ny Of Oy Pd Pe Pf Po Qc) Jg(Fr Hq Hr Hu Hx Ii Ij Il In Io Ip Iq It Iu Jk Jm Lu Ly Ma Mc Md Mj Mk Ml Mn Mq Mu Mv Mw Na Nb Nf Nk Nq Nr Ns Ny Oi Pa Pg) Lh(Aj Hr Hx Ih Ii Ij Ir Is Jl Jn Jq Jv Lv Mb Mf Mh Mi Ml Mm Mp Mr Ms Mt Mv Mw Mx My Nb Ne Nf Ng Nh Nl Nm Nn No Ny Oy Pb Qc) Nx(Fr Hv Ih Ij In Ir Is It Jh Jn Jq Lj Lv Lz Mb Me Mf Mm Nb Nc Nd Ne Ng Nh Nl Nr Ny Oe Of Oh Oy Pa Pd Pe Pf Po Pz Qc) Or(Aj Cs Ed Fn Fw Fy Hf Iz Jj Jo Jp Ke Kq Lj Mk Na Nd Nh Nm Nw Of Og Ou Pj Qd To Uh Um Ur Vt Wm Ti Th) Jl(Fr Hr Ih Ij Ik Ir Is Jq Lv Mb Mf Mh Mi Mm Mp Mr Ms Mt My Nb Nc Ne Nh Nn No Nr Ny Of Oy Po Pz Qc) Nm(bA bM cT Fr Ih Ij Ir Is Jq Jr Lv Mb Mh Mi Mm Mr Ms Mt Nc Ne Ng Nh Nn No Ny Pe Po Qc) Mp(Fr Hu Hv Ih Is Jr Lj Lv Mb Me Mf Mh Mm Mr Ms Mt Nc Ne Nh Nn No Nr Ny Og Oy Po Pz Qc) Mx(Fr Ih Ij Ik Ir Jh Jn Jq Jr Lv Mb Mi Mm Mr Ms Mt Nh Nl Nn No Ny Og Oy Po Pz Qb Qc Vt) Qd(aM Ar Aw aX bA bI bJ bO bS bV cG cM CS CT cU cV cX cZ dB dD dE Dk Ef Iz Jv rB) Fp(Fr Hr Ih Ij Ik Ir Is Jh Jn Mf Mr Ms Mt Nc Nd Ne Nf Nh Nn No Ny Pe Pz Qb Qc) Iv(Fr Ih Ij Ik Ir Is Jn Lv Mf Mh Mm Mr Ms Mt Nd Ne Nh Nl Nr Ny Pd Pe Po Qb Qc) bM(Aj aL aS Bb bE Cs Cu Dc dD Ed Et Fa Fw Fy Gl Jp Jq Kq Lj Mi Mt Nb Qc Un Vt) Jj(bA Cs Cu Dc Fa Ho Ih Ii Ik Jk Jo Kq Lv Mi Mm Mr Ne Nh nN No Nr Pe Pz Vt) Qb(Fr Jn Jq Lv Mb Mf Mh Mi Mm Mr Ms Mt Ne Nh Nl Nn No Ny Oy Pe) Aj(Ad BA cT Cu Fa Fy Ij Im Ke Lj Mi Mn Nb On Pd Qc Vt) Og(bA Dc Fr Ir Is Jn Jq Lv Mi Mt Nl Nn No Ny Po Vt Wm) Nl(Fr Ij Ir Jn Jq Lv Mi Mm Mr Mt Nn No Ny Pe Po) Vt(aS bE Cs dE Gc Jp Jv Lj Nd Nf Qg Qv Um Wm Th) Jn(Fr Ij Jq Lv Mh Mi Mm Mr Ms Mt Nn No Pe Po) Jp(Cs dE Ef Hc Ib Ic Kl Ow Qu Rc Sh Ua Wm) Ij(Lv Mb Mi Mm Ms Mt My Ne Nh Nn No Oy) Jq(Fr Lv Mb Mh Mm Mr Ms Mt Nh Nn Ny Po) Kq(Aw Bg Hc Ib Jd Jo Jv Lj My Om) Lv(Ih Ir Mi Mm Mt Nh Nn No Ny) Mi(Ir Mb Mm Ms Mt Nh Nn Ny) Jv(Cs Dc Fa Lj Nw oE Uh Un) Gc(jV Sf Ub Ue Va Vb Vo) Mt(Ir Mh Ms My Nn No Ny) Uh(Cs fP Lj Nd Rc Wn Wm) Ke(Ap Ef Ik Iz Jo lM) Mm(Ir Mb Mh Mr No) Nw(bA bE Cs dE Wm) bU(dU eQ nN oW pK) Cu(Jo Nb Of Vb) Nn(Ir Mh Ms No) bA(dE Lj My Nb) jD(Jr Yd Tl) Gz(qZ rN) No(Ib Nh) Hv(Hp Ye) Lj(Fn Wm) aM(dW Ew) cT(Ct Nb) FaOf NdSh IbNy KxgV UtnN PkoE cUdH

Figure 39 Continued

Unconstrained panels with 2 analytes, where 1.0E-3 >= 'model p-value' > 1.0E-4. Contains 4,619 panels of 200,124 total panels evaluated. :
Or(aA Ad AF aK Al aM An Ao Ap Ar AS aU aV AW Ax aY BA Bb Bc bE bF Bg bH bI bJ bL Bn BO bP bS bV bZ cA cC cD cE cF Ch cK cM
CO Cp CQ cR CT CU CV CW CX DB DC DD DE Dg Di dJ DK DL Dp Ef Em Et Ez Fa Fb Fp Fr Gc Gh Gl Gn Gp Ha Hb Hc Ho Hp Hq Hr Hu
Hv Hw Hx Ib Ic Id Ih Ii Ij Ik Il Im In Io Ip Iq Ir Is It Iu Iv Jd Je Jf Jg Jh Jk Jl Jm Jn Jq Jr Js Jt Ju jV Jy Kc Kd Kf Kg Ki Kj Kk Kl Kn Ko Kp Kr
Ks Kx Ky Kz Ld Lh Li Lu Lv Lx Ly Lz Ma Mb Mc Md Me Mf Mg Mh Mi Mj Ml Mm Mn Mp Mq Mr Ms Mt Mu Mv Mw Mx My Nb Nc Ne
Nf Ng Ni Nj Nk Nl Nn No Nq Nr Ns Nt Nu Nv Nx Ny Oa OE Oh Oi Ok Om On Ow Oy Oz Pa Pb Pc Pd Pe Pf Pg Ph Pi Pk Po Pz Qa Qb Qc Qe
Qg Qh Ql Qm Qn Qt Qu Qv Qw Qx Qy Qz Ra RB Rc Rf Rg Rh Ri Rj Rm Ry Sf Sh Sr Ss St Tn Tr Tt Tv Tz Ua Ub Uc Ud Ue Uf Ug Uk Ul Un
Uo Up Us Ut Uu Uv Vo Vp Vs Wb Zq Tl Xa Tj) Vt(AA AD AF aG aK aL aM An Ao AP Ar As aU aV AW AX aY BA BC BG bH bI bJ bL BN
BO bP bQ bR bS bU bV cA cC cE cF cG cI cK cL cM cN CO cP CQ cR cS CT CU CV CW CX cZ dA DB DC DD De Dg DI dJ DK DL dN Dp
Du dX Ed EF Em Et Fa Fn FP Fr Fw Fy Gd Gl Gn Gp gV Hf Ho Hp Hr Hu Hv Ib Ic Id Ik Il Im In Iq Ir Is It Iu Iz Jd Jh Jl Jo Jq Jy Ke Ki Ko Kq
Kr Ks Kx Kz Ld Lh Li Lu Lv Lw Lx Ly Lz Mb Me Mf Mg Mh Mi Mj Mk Mm Mn Mp Mt Mu My Na Nb Nc Ne Ng Nh Nj Nl Nm Nn No Nq
Nr Ns Nt Nu Nw Oa OE Of Oh Oi Ok Om Ou Ow Oy Oz Pa Pb Pc Pd Pe Pf Pg Pj Pk Po Qa Qb Qc Qd Qe Qh Qm Qu Qx Qy Qz Ra Rc Rg Rt
Sj Sr Ss St Tn To Tr Tz Ua Ub Uc Ud Ue Uf Ug Uh Uk Un Up Ur Us Ut Uu Uw Ux Uy Va Vb Vc Vi Vj Vo Vp wF Tl Xa Tj Ti) Mz(AD aE aF
aG aH al aJ AL An Ao AP aQ AR As aU aV aW Ax aY aZ Ba BB BC bF BG bH BN Bo bP bQ bR bU bW bX cA cB cE cF cG CH cJ cL cN
Co CP CQ cR cS Cu Cv CW cY cZ dA Db DC Dd dE dF DG dH DI dK Dl dM dN Dp Ez Fa Fn fR Fw Fy Gl Gp Gz Hb Hc Hf hP Hq Hu Hv
Hw Ib Ic Id Ii Il In Io Ip Iq It Iu Jd Je Jf Jh Jk Jm Jo Ju Kc Ke Kg Ki Kj Kk Kl Ko Kq Kr Ks Ld Lj Lu Ly Lz Ma Mc Md Me Mf Mg Mj Mk Mn
Mq Mu Mv Mw Na Nb Nd Ng Ni Nk Nq Ns Oa OE Of Oh Oi Om Ou Ow Oy Oz Pa Pc Pd Pf Pg Ph Pi Pj Pk Qg Qh Ql Qm Qt Qu QW Qx Qy
Qz Ra RB rC Rg Rh Ri Rj Rm rQ rU Sf sK sO Sr Ss St Tn To Tr Tt Tv Tz Ub Ud Ue Uf Ug Uk UL UN UO Up Us Ut Uv uY Vb vl Vo Vp Vs
Vv yJ) aN(Aa AD aE AF aG aH al aJ aK AL An AO AP aQ AR As aU aV AW AX aY Ba bB BC bF BG bH bI bJ bL BN Bo bP bQ bR bS bU
bW bX bZ cA cB cC cE cF CH cI cJ cK cL cN CO CP CQ cR cS Ct CV CW CX cY cZ dA DB dC De DG dH DI dJ Dk DL dM dN Ef Fn Fr Fw
Fy Gl Gp gW Hq Hr Hu Hv Hw Hx Ic Id Ih Ii Il In Io Ip Iq It Iu Jg Jh Jk Jm Jo Jr Js Kr Kx Lu Ly Lz Ma Mb Mc Md Me Mf Mg Mh Mj Mk
Ml Mm Mn Mq Mr Ms Mu Mv Mw My Na Nc Nf Ng Nh Ni Nj Nk Nl Nn No Nq Nr Ns Nv Ny Oa OE Of Oh Oi Om Oy Oz Pb Pc Pg Pj Pz rQ
St tT Tz Ub Um Us Wm) Lw(AD aE AF aG aH al aJ aK AL AO AP aQ aR As aU aV AW aX aY aZ Ba BB BC bF BG bH bI bL BN Bo bP bQ
bR bU bW bX bZ cA cB cF cG CH cJ cL cM cN Co CP CQ cR cS Ct CV CW Cx cY cZ dA Db dC Dd De dF DG dH DI dJ DK DL dM dN Ed
Ef Fa Hq Hv Hw Hx Ii Il In Io Ip Iq It Iu Jh Jk Jm Jo Ke Lu Ly Lz Ma Mc Md Me Mf Mg Mj Mk Ml Mn Mq Mu Mv Mw My Na Nb Nd Nf Ng
Ni Nk Nq Ns Oe Of Oh Oi Om Oz Pa Pb Pc Pd Pf Pg rB Uh Wm) aC(Aa aD aE aF aG aH al aK aL aO aP aQ aR aS aU aV AW aY bB bC bE
bF BG bH bI bJ bL BN BO bP bQ bR bS bU bW bX bZ cA cB cC cD cE cF CH cI cJ cK cL cM cN cO cP cQ cR cS Ct cV cW cX cY cZ dA
DB dC dD dE dG dH dI dJ dK dL dN Dp Ex Ez fP Gc gP Gz hC Hq Hu Hw Hx iH Ii iJ Il iZ Jh Jk Jm Jo Ks Ky Ma Mb Md Mv Na nL nN nO
oE Oh oN Oy Pc Pg Pz Qg Qn Qt Qw Qz Ra Rb Rf Rg Rh Ri Rj Rm Ss Tn To Tt Tv Ud Ue Ug Uk Ul Uo Ut Uv Vo Vp Vs Vv Ti) Qd(AD aE
AF aG aH al aJ aK AL An AO AP aQ aR As aU aV aW Ax aY aZ Ba BB BC bF BG bH bL BN Bo bP bQ bR bU bW bX bZ cA cB cC cD cE
cF CH cI cJ cK cL cN CO CP CQ cR Cu Cv CW Cx cY dA Db DC Dd De dF DG dH DI dJ dK DL dM dN Ed Fa Fn fP Gc Gz HC Hf hR Ib Ic
Id iJ jD Jf Ju jV Ke Ki Kj Kl Kz oE Ou Ow Pj Pk Qg Qt Qu Qv RC Rf Rm rQ rZ Ss To Tr Ua Ub Uc Ue Uh Um Ur Us Uu Vo wQ yJ) Uh(aA
Aj aM Ao Ap AS Aw bA bE Bn bO bV cM Cq Cu cV dB Dc Dd dE dL dR Ed EF Fa Fn Fp Fw Fy Gc gL gP hB hC hF hG Hv iA Ib Ic Id iH iJ
Ik iO iP Ir Is Iu IZ jD Ji Jj Jl Jo Jp Jq Ju Jy Kd Ke Ki Kl Kn Kp KQ KR kS Lh Li Lx Lz Mi Mj Mm Mp Mq Mt Mu Mx Na Nb Ng Nh Nn Nu
nW nY Oa oE OF Og OH oK oN Ou Ow Oz Pa Pb Pd Pe PF Pi Pk Po Qa Qe Qu Qv Rj Tz Ub Uc Un Up Us Uu Vv) Ji(aD aE al aJ AL aP aQ
aV bB Bc bF bH bN bP bR bU bW cF CH cJ CP cY cZ dC Dd dG dN dR eC Ed eM Ex Fa Fn fR Fw gV hB hF hG hP iA Ib Ic iO iP IZ jD Ju jV
Ki Kl kQ kR kS IM nW nY oF oH oK Ou Ow pF Qg Qt Qu Qv Qx Rf Rg Rh Rm rQ rU Sr Ss St tR tT tU tX Tu Ua Ub Uc Ud Ue Uf Ug Uk Ul
UN Uo Up Ur Ut Uv vA Vb Vc Vp Vs Vv wE wF wH wK wL wP yJ zG tF) bM(aA Ad aK aM An Ar Ax aZ Ba bG bJ bO bV cG cM Cp Cq cU
Cv dB Dd dE dF Di DK Ef Fn Fp Fr Gp gW Hr Hv Ic Id Ij Im Iv Iz Jd Jg Jl Jn Jo Jr Js Jv Jy Kd Kf Kn Kp Kr Kx Kz Ld Lh Lv Ml Mn Mp Mr
Mu Mx My Nd Ne Nf No Nt Nu Nx Ny Oa OE Of Og On Ou Oy Pa Pb Pd Pe Pf Pi Pj Po Qa Qb Qe Qg Qh Qv Rj Sr St Tn Tr Tv Tz Ub Uc Um
Up Us Vu Wm) Ke(Ad Af aM Ao aS Aw bE Bg bO Ch cM Co Cp Cs Ct cV Cw dE Dg DL dX Ed eF eP Fa Fn fP HC Hu Hv iA Ib Ic Ii Il Iu JD
Jh Jj Jp Jt Ju jV Ki Kj Kl Lj IN Lv Ly Mg Mj Mk Mm Mw Mx My Nc Nd Ne Nf Ng Nh Nk Nl Nm Ns Nu oE Og Oi oK Om oN Ou Ow Oy Oz
Pg QU qW Qx rB Rc Rf Ss TO Ua Ub Us Uu wF yJ Wm) Mt(aS bA bE bJ bS bV cC cO Cs cT cV Dc dE Ed Fn Fr hP Hq HR Hu Hv Hw Hx Ih
Ik Il In Io Ip Iq Is It Iu Iz jD Jh Jk Jm Jo jP Jr Jv Lj IM Lu Lz Ma Mb Mc Md Me Mf Mg Mk Ml Mm Mn Mq Mr Mu Mv Mw Nb Nc Nd Ne Nf
Ng Nh Ni Nk Nq Nr Ns Oe Of Oh Om Oy Oz Pa Pb Pc Pd Pe Pf Pg Po Pz Qc qW rB Tz uM wQ yJ Wm) Lj(aK aM An aS aU Bb bC bE bJ bO
bS bV cC cG cM Cp Cs cT CU cV cX dB Dc dD DE dF Di dJ dL Dp Ed Fp Fy Gc Gl hC Hf Ho Ib Ic Id IJ Iv Iz Jd Jj Jl Jn Jq Js Ju Jy Ki Lh Li
Lv Lx Mi Mm Mx Nl Nm Nn No Ny oE Ou Pj Qb Qg Qm Qv Qy Rc Rf Rm Sf Sr Tn Tz Ub Uc Um Un Up Ur Us Ut Uu Vi Wb Ye Tl Ti)
bA(aA aM aP aX bE bJ bL bO bS bV cC cD cE cF cG cM Cs Ct cU cX dB Dc dD dL eF Et FP Hr Hu Ih Ii Ik Im In Io Is Iv Iz Jo Jp Jq Jt Jv Lh
Li Lv Lx Lz Mc Me Mf Mg Mh Mk Ml Mm Mn Mp Ms Mu Mw Mx Nc Nd Ne Nf Ng Nh Ni Nj Nk Nl Nn No Ns Nt Nu Nx Oe Of Oi Ok
Om On Oy Pg Pj Pk Qa Qb Qc Qe) Nw(Ad Af aG aH aK aM An AO Ap Ar AS aU AW AX aY bC Bg bI bJ bL Bn bO bQ bS bV bZ cA cC cD
cE cG cI cK cL cM cN CO Cp CQ cR CT CU CV CW Cw CX cZ dA DB Dc DD De Dg DI dJ DK DL gV Iz jD jV IM nN oE Ow qT qU qV qW qX
qY rA rB RC Us) Jj(Ad Al An Ar Ax Bb bS Cp Cq cT cU DD dE Ed Em Fb Fn fR Fw Fy Gc Gd Gl Ha Hu Hv Ic Id Ip It Jd Jh Jm Jr Jv Kf Kr
Ks Kx Ma Mb Me Mf Mg Mh Mj Mn Ms Mu Mv Mw Nb Nc Nd Ng Nq Oa oE Og Oh Om Ou Oz Pa Pc Pd Pf Pg Pi Pj Pk Qc Qh Tz Un Up Us
Vu Wb Tl Wm) Jp(An Ap bE bS Ct CU Dc Dg Dp Ed Eq Ez Fa Fn fR Gz Hf Hp Id Jd Je Ju Ki Kj Kp Kq Kr Kx Kz Ld nN Oa Ou Ph Pi Pj Pk
Qg Qt Qv Qw Qx Qy Qz Rb Rf Rg Rh Rj Rz Sf Si Sr Ss St To Tr Tz Ub Uc Ud Ue Uf Ug Uk Um Un Ur Us Ut Uv Uw Ux Vb Vc Vo Vp Vs
Vu Vv) Aj(aM Ao Ar Ax Bb BC bE cG Cp Cq Cs cU DD dE dF Dk dL Fb Fp Fr Fw Gl Id Ih Ii Io Ir Iv Jd Jk Jl Jn Jq Jr Js Jv Jy Kf Kg Kn Ko
Kp Kr Ks Kx Lv Lz Mg Mm Mp Mq Mr Mu Mx Nn No Nr Nu Nv Nx Ny Oa Og Om Ou Oz Pa Pb Pe Pf Pj Po Pz Qb Uc Un Us Wm) Lx(aS bE
bJ bL bS bV bZ cC cE cO Cs cT cV dE dW eO Fn Fr Hq Hr Hu Hw Ii Il In Io Ip Iq Iu Iz Jh Jk Jm Jo IM Lu Ly Lz Ma Mc Md Mg Mj Mk Ml
Mn Mq Mu Mv Mw Na Nb Nd Nf Nk Nq Nr Ns oE Of Oh Oi Om oN Oz Pa Pc Pd Pf Pg Po Pz qW rB wQ) Mx(Hq Hr Hu Hv Hw Hx Ii Il In Io
Ip Iq Is It Iu Jk Jm Jo Jv Kq Lu Ly Lz Ma Mc Md Me Mf Mg Mh Mj Mk Ml Mn Mq Mu Mv Mw My Na Nb Nc Nd Ne Nf Ng Ni Nk Nq Nr Ns
Oe Of Oh Oi Om Oz Pa Pb Pc Pd Pe Pf Pg qW rB rX rZ uM UN Ur vI Wm) Nm(Ap aS bE bJ bO bV Cs CU cV Dc dD dE Hq Hr Hu Hv Hw Hx
Ii Ik Il In Io Ip Iq It Iu Jh Jk Jm Jo Lu Ly Lz Ma Mc Md Me Mf Mg Mj Mk Ml Mn Mq Mu Mv Mw My Na Nb Nd Nf Ni Nk Nq Nr Ns Oe Of
Oh Oi Om Oy Oz Pa Pb Pc Pd Pf Pg Pz) Jv(Ar aS aW bE bV cT CU cV DD dE Dk Ed Et Fp Fw Fy Gc Gp hC Hv Id Il Im Iq Ir Is Jd Jl Jq Js Kd
Ki Kn Kp Kr Kx Li Lz Mj Mn Mp Mu Na Nn No Nr Nt Nu nY Oa oF Og Oh On Pa Pd Pe Pf Pj Pk Po Qa Qc Qh Qv Sr St Tz Us Vu) Qb(Cs Cu
Gc Hq Hr Hu Hv Hw Hx Ih Ii Ij Ik Il In Io Ip Iq Ir Is It Iu Jh Jk Jm Jo Jr Lu Ly Lz Ma Mc Md Me Mg Mj Mk Ml Mn Mq Mu Mv Mw My Na
Nb Nc Nd Nf Ng Ni Nk Nq Nr Ns Oe Of Oh Oi Om Oz Pa Pb Pc Pd Pf Pg Po Pz Qc) Jl(Hq Hu Hv Hw Hx Ii Il In Io Ip Iq It Iu Iz jD Jh Jk Jm Jo

Figure 39 Continued

Jr Lu Ly Lz Ma Mc Md Me Mg Mj Mk Ml Mn Mq Mu Mv Mw Na Nd Nf Ng Ni Nk Nq Ns Oe Oh Oi Om Oz Pa Pb Pc Pd Pe Pf Pg Qv qW rB Um Ur Uu wQ Wm) Iv(bE dX Hq Hr Hu Hv Hw Hx Ii Il In Io Ip Iq It Iu Jh Jk Jm Jo Jr Lu Ly Lz Ma Mb Mc Md Me Mg Mj Mk Ml Mn Mq Mu Mv Mw My Na Nb Nc Nf Ng Ni Nk Nq Ns Oe Of Oh Oi Om Oy Oz Pa Pb Pc Pf Pg Pz) Fp(cM Hq Hu Hv Hw Hx Ii Il In Io Ip Iq It Iu Jk Jm Jo Jr Lu Ly Lz Ma Mb Mc Md Me Mg Mh Mj Mk Ml Mn Mq Mu Mv Mw My Na Nb Ng Ni Nk Nq Nr Ns Oe Of Oh Oi Om Oy Oz Pa Pb Pc Pd Pf Pg Po Wm) Lh(dE Fr Hq Hu Hv Hw Ik Il In Io Ip Iq It Iu Iz jD Jh Jk Jm Jo Jr lM Lu Ly Lz Ma Mc Md Me Mg Mj Mk Mn Mq Mu Na Nc Nd Ni Nk Nq Nr Ns Oe Of Oh Oi Om Oz Pa Pc Pd Pe Pf Pg Po Pz rB wQ Wm) Gc(cB De eC Ed fP gP gW hG jD Ju kS Ni nW oE oF Pz Qa Qe Qv Qz Rc Rg Sh Tz Ua Uc Ud Uf Ug Uk Ul Um Un Uo Up Us Ut Uu Uv Uw Ux Uy Uz Vc Vh Vi Vp Vq Vs Vu Vv Vw Wc Wd We Wf Wg Wh) Ij(Fr Hq Hr Hu Hx Ih Ii Ik Il In Ip Iq Ir Is It Iu Jh Jq Jr Lz Mc Md Me Mf Mh Mk Ml Mn Mq Mr Mu Mv Mw Nb Nc Nd Nf Ng Ni Nq Nr Ns Ny Oe Of Oh Om Oz Pa Pb Pc Pd Pe Pf Pg Po Pz Qc) Jn(Hq Hr Hu Hv Hw Ih Ik Il In Ip Ir Is Jh Jo Jr Lu Lz Ma Mb Mc Md Me Mf Mg Mn Mq Mu Mv My Nb Nc Nd Ne Nf Ng Nh Ni nN Nq Nr Ns Ny Oe Of Oh Om Oy Oz Pa Pb Pc Pd Pf Pg Pz Qc Sf Sh) Mp(Hq Hr Hw Hx Ii Ik Il In Io Ip Iq It Iu Jh Jk Jm Jo Lu Ly Lz Ma Mc Md Mg Mi Mj Mk Ml Mn Mq Mu Mv Mw My Na Nb Nd Nf Ng Ni Nk Nq Ns Oe Of Oh Oi Om Oz Pa Pb Pc Pd Pe Pf Pg) Kq(Ad Ao Ap aS bE Ch Co Cp Cs Ct Cw dE Dk Ed Fa Fn Fr Hu Hv Ic Id Ii Ik Kj Kl Lv Mg Mv Mw Nd Nf Ng Nh Nq Nu Oa oE Og Oi oN oP Ou Ow Oy Pg Qt Qu Rc Ss Ua Ub Uc Us Uu Wm) Jt((Cs Ct cU dE Hq Hu Hv Hw Hx Il Io Ip Iq It Jh Jk Jm Jo Lu Ly Lz Ma Mc Md Me Mg Mk Ml Mn Mq Mu Mw Nb Nf Ni Nk Nq Ns Oe Oh Oi Om Oz Pa Pb Pc Pg Pz Vb) Cs(aM Bb bE bJ cM cT Dc dE Ed Et Fn Fy Ic Ik Is Jo Jq Ju Li Mi My Nb Nd Nh Nt Nu Oe Of Og Oi Ok Pb Qc Qe Qu Rc Rf To Tz Um Un Up Us Ut Uu wF Wm) Nx(Hq Hr Hu Hw Hx Ii Ik Il Io Ip Iq Iu jD Jk Jm Jo Jr Lu Ly Ma Mc Md Mg Mj Mk Ml Mn Mq Mu Mv Mw My Na Nf Ni Nk Nq Ns Oi Om Oz Pb Pc Pg wJ wQ) Mi(aS bE bS cT Dc dE Fr Hr Hu Hx Ih Ik Ip Is It Jh Jq Jr Ma Me Mf Mh Mn Mr Mu My Nb Nc Ne Nf Ni No Nr Oy Oz Pb Pc Pe Po Pz Qc Wm) Jq(Aa Hr Hu Ih Ik In Ip Ir Is It Jh Jr Ma Me Mf Mu My Na Nb Nc Nd Ne Nf No Nq Nr Oe Of Oh Oy Oz Pa Pb Pc Pd Pe Pf Pg Pz Qc Wm) Js(Hq Hv Hw Hx Ii Io Ip Iq Iu Jk Jm Jo jV Lu Ly Lz Ma Md Mg Mj Mk Ml Mn Mq Mv Mw Na Nk Nq Nr Oh Oi Om Pa Pf Pg qW rB rZ wQ) Po(bS Fr Hr Ih Ik Ir Is Iz jD Jh Jr Lv Mb Mf Mh Mm Mr Ms My Nc Ne Nf Ng Nh Nn No Nv Ny Pe Vb Ye Wm) Fa(aS AW bE cM cV cX dE Ef Fn fP Hf Hr Ib Ic Id Ik Iz Jo Lv Mg Mk Nd Ng Nh Nu Oe Og Oi Ou Pj Qu Qx rB Rf Ur Wm) Li(aS bE cT Dc dE Fn Fr Gd gV Hx Ii Il Io Ip Iq Iu jD Jk Jm Jo Lu Ly Ma Md Mg Mj Ml Mn Mq Mw Na Nk Oi Pf Vb Tl Wm) No(Fr Hr Hu Ic Id Ih Ik Ip Ir Is It Jh Jr Mb Me Mf Mh Mr Ms Mu My Nb Nc Ne Nf Nr Ny oE Oy Oz Pb Pc Pd Pe Pz Qc) Qe(aS bE bJ bS bV cM CT Cu Dc dD dE Di dX Ef eP Fn gV Hp Ii Iz Ow Qv rB Rm Ua Ub Um Ur Us Uu Vb Zw Ye Tl) Ni(Hv Ih Ii Ik Ip Is Jh Jo Jr Ma Mb Me Mf Mh Mn Ms Mu Nb Nd Ne Ni Nk Nq Nr Oh Oy Oz Pa Pc Pd Pf Pg Pz Qc) Nb(aK aM aS Aw aZ Bb bE bJ bO bS bV cC cG cM cU cV cX dB Dc DD dE dL Hp Ir Lv Mm Ny Sf Sh Vb Ye) Is(aM aS Bb bE bI bJ bO bV cM CT cU dB dD dE Fr Ir Lv Mb Mh Mm Mr Ms Ne Nh Nn Ny Pe Vb Ye Wm) cT(aA aM An Ar aX bC bE bL bO cA cC cD cG cM cU dA dB Dc dD dE dL Im My Ng Nt Nu Of Og Ok Qc) Lv(Dw Eo eW Fr Ii Ik Ip It Jh Jr Ma Mb Me Mf Mh Mr Ms Mu Nc Nd Ne Nf Nr Oh Oy Pd Pe Pz Qc) Ny(Fr Hv Hw Ih Ir Jh Jr Mb Me Mf Mh Mm Mr Ms Nc Nd Ne Ng Nh Nn Nr Of Oy Pd Pe Pz Qc uN yJ) Og(Bb Cp Cu Dd Ed Fy Id Ih Ii Ik Il Kr Mm Mr Ne Nh nN Nr Oa Pd Pe Pz Qc Tz Uc Un Us Vu) Nj(gV Hq Hr Hu Hx Io Iu Jk Jm Lu Ly Mb Mc Md Mk Ml My Na Nc Nf Ng Ns Of Oi Pb) Fr(Hv Ih Ir It Jr Mb Mc Mf Mh Mm Mr Ms My Nc Ne Ng Nh Nn Nv Of Oy Pe Qc) Un(aS bE cV dD dE Ef eP Fn Ib Ic Iu Iz Jo Nd oE Of Ou Ow Rc Um Uu Vb Wm) Dc(aM aS bE bJ cU dB dE Hr In Jo My Nf Nh Nu Of Oy Qc Sf Ur Uu Vb Wm) Qa(aS bE bS dD dE Fn Ib Iz jD rB Rm To Ua Ub Uc Um Ur Us Uu Ye Tl Wm) Pk(aM aS aW bE bO bV cC cM cU cV cX dD dE dL dR eF hC iJ oF oN tT wF) Mm(Hu Hv Ih Ik It Jr Me Ml Ms My Nc Ne Ng Nh Ni Nn Nr Oy Pd Pe Qc) Hv(Ho Id Lp Nn Ry Sf Sh Si Sj Vb Vc Vi Wb Wd We Wf Wh Zw Tl Xa) Ir(Ih Jh Jr Mb Mf Mh Mr Ms Nc Nd Ne Nh Nr Ns Oy Pd Pe Pz Qc Wm) Ut(Eq Ho Iz kG kP lX lY mF mM mS nD nJ nL nO nT oP Sf Sh Vb) Nn(Hu Ih Jr Mb Me Mf Mr My Nc Ne Nh Nr Of Oy Pd Pe Pz Qc) Cu(Hp Hr Ik In Iz My Nf Ng Nh Nu Oy Pg Qc Wd Wh Tl Wm) Qc(aM aS bE bJ bS bV cM cU dD dE Ih Ik Mr Ms nN Pe) Nv(Il Io jD Jm Lu Ly Ma Md Mj Mn Mq Na Oi Pa Pg Pz) cM(cU dU Ed fA gZ jB nN nO oD oE oV oW pH pI pK) Fy(dE Ef Gz Ib Ik Iz Jo oE Of Qv Sf Sh Vb) Jr(Hp jU jV nN rB rZ Sf Sh Uy Vb Wf Wh Ye) Wm(Ed Fw Mu Oh Ok On Pa Pe Qv Tz Us wF) Ok(Ap aS bE Ct cU dB dE fR Vb Vc Wh) nO(aK aL cF Dp Ed hC Qv Ug Um Ur Tj) Mb(DW EO EW Ih Mr nN Pe) hC(Hc mI mS nI nJ nN nT Pj Ry Zq) Mr(Ih Mf Ms Nc Ne Nh Nr Pe Pz) bU(fA fB gZ jB oD oT oV pH pI) wF(Dk Dl Ef Kp Kz Pj Qm To Ti) Id(Ed jV lM oE Of rC uI uM) Iz(Mu oE On Ou Tn Tr Uc Us) Gz(bV rB rC rP rV tV Us) Ho(bO Hp Nd Nk Sf Sh Vb) Of(Fb Jd Kf Kr Oa Pj Us) Nh(Ih Mh Ms Nr Pe Pz) Pj(Ik jD jI lN oE Qv) nN(aL bO eC IL Lz nI) Aa(Hr Hx tV tX Vv) lm(bE dE rB wQ yJ) Sf(bR Dk Gp Nd On) Us(Ib Jo Qv Um Ur) Pe(Hr Ih Ne Oy Pz) aA(hR Lu Md Na Nk) aM(Dw EO eW gV) tT(Dl iP Kz rB rC) Ed(dE Mu oE Qv) Mn(dX eM eP gV) Kr(Jo rZ sH sI) On(Ef fR Hp Vb) Et(Ap dE Ef) Nt(aS bE cU) Ms(Ih Nr Pz) Oz(iB jl jP) tX(iP Kz rB) jV(sK Sr Tz) oE(cX Fw Ns) Dk(Hp Sh) Uc(Uu Vb) Ye(kG nK) aL(mI oW) cB(Dr eW) wQ(tV vI) rB(Mj Tz) qX(uI uM) jY(nA nR) IL(kF oQ) BoeW FwVc GlIM GpSh NuWn MdjD MhPz NdTr NeIh QxhW KxeM QmuN bEcU cVhR dAhP sFjM sHuM rQpF

Constrained panels with 3 analytes, where 1.0E-10 >= 'model p-value' > 0. Contains 667 panels of 38,239,313 total panels evaluated. : Ji{Oy(aA Et Fp Hq Im Iv Jg Jl Jp Lw Mh Mp Mr Ms Mu Mx Nj Nn Nt Nu Nv Ok On Pg Qd) My(aA Et Fp Im Iv Jg Jl Jp Lw Mh Mp Mr Mu Mx Nj Nn Nt Nu Nv Ok On Qd) Ii(Et Fp Im Iv Jg Jl Jp Lh Lw Mi Mr Ms Mx Nn Nt Nu Ok Pa Pe Qd Qe) Nt(aA Hx Ik In Jh Jj Jo Mh Ml Ms Mv Mw Ng Ny Oe Of Og Om Pb) Nu(aA Hx Jh Jj Jo Jq Mh Ml Mp Ms Mv Mw Ng Nj Ny Of Og Om Pb) Et(aA Hx Jh Jj Mb Mh Ml Mp Ms Mv Mw Ng Nj Ny Of Og Om Pb) Nj(aA Hx Ik Im In Jj Jo Jp Jq Mx Mz Nk Nn Of Og Ok Om) Mh(aA Fp Hx Ik Im Jl Jp Lx Mb Ml Mr Om Pe Qd Qe) Jp(Hx Im Jh Lh Mb Ml Mp Mv Mw Ng Ny Og Om Pb) Fp(Hr Hx Ik Jh Jj Lh Ml Mv Mw Nf Ny Om Pb) Im(aA Hx Jj Jq Ml Mp Ms Mx Ng Of Og Om) Ok(Hx Jo Jq Ml Mp Mv Mw Ng Ny Of Og Om) Iv(Hx Jj Jo Ml Mp Mw Ng Ny Of Og Pb) Nn(Jh Jj Jo Mp Mv Mw Ng Of Og Om) Mx(aA Jj Jo Jq Mp Ms Of Og Om) Qd(Jh Jq Lh Mp Mv Mw Nq Of Om) Jg(Jh Mv Mw Ng Of Og Om) Ms(aA Jj Jo Nd Of Og) Nb(Jl Mr Oz Pa Pe) Jj(aA Jl Jq Of Qe) Og(aA Jq Lw Nm Of) Mp(aA Jl Lw Ng) Mw(Mr Mu Nv On) Mv(Mr Mu Nv) Jq(aA Lw Of) Mb(Ik Ml) Ng(Lw Nm) Jl(Hr Jo) MuJh QeLh OfaA} Nt{Im(aA Et Ii Ik In Iu Jj Jk Jo Jp Lw Mg Ms Mx My Mz Ng Nj Nq Nw Oe Of Og Ok Om Oy Qd) Jj(aA Et Fp Ih Ik Ir Jl Jp Js Li Lw Mp Mx Mz Nj Nn Nu Nw Nx Ok On Qa Qb Qd Qe) Og(aA Et Fp Ij Ir Jl Jp Jq Lw Mp Mx Mz Nj Nm Nu Nw Nx Ok On Qa Qb Qd Qe) aA(Et Fp Ih Ik Jp Lw My Mz Ng Nj Nw Oe Of Ok Oy Qb Qd Qe) Nw(Ii Ik Jo Lw Mh Ms Mv Mw My Ng Nj Nq Oe Of Om Oy) Ok(Hr Ii Ik Jo Lw Mg Mh Ms My Ng Nj Nq Oe Of Oy Qd) Et(Ik Jh Jo Lw Mg Mh Ms My Ng Nj Nq Oe Of Oy) Qd(Ik Jo Lw Ms My Mz Ng Nj Nq Oe Of Oy) Lw(Jp Mx My Mz Ng Nj Of Oy) Jp(Ms My Ng Nj Of Oy) On(My Ng Of Oy) Ng(Jg Nm) Of(Jg Nx) Oy(Mp Nv) NjIk} Et{Jj(Fp Im Iv Jl Lw Mh Mp Ms Mx Nj Nl Nn Nu Nx Of Ok On Qa Qb Qd Qe) Im(aA Lw Mh Ms My Ng Nj Nu Of Og Oy Qd) Of(aA Fp Iv Lw Mx Nj Nu Nx Ok On Qd) Nj(aA Fp Lw Mh Mp Nu Og Ok Qd) Nu(aA Lw Mh My Ng Og Oy) aA(Fp Mh Mx) Oy(On Qd) IjOg} Ok{Of(aA Fp Im Iv Jj Lw Mf Mp Ms Mx Nj Nl Nn Nu Nx Og On Oy Qd) Nu(Fp Im Jj Ms My Ng Nj Og Oy) Nj(aA Im Jj Mp Mz Nw Og Qd) Jj(Fp Im Iv Mx Nn Qb Qd) Im(My Og Oy) MyQd IjOg} Nu{Jj(Im Jg Jl Jp Lw Nj Nv Nw Nx On Qa Qd Qe) Nw(aA Im Lw Ms My Ng Nj Of Og Oy) Og(Ij Im On Qd) On(Ng Of Oy) Im(Nj Qd)} Im{Og(aA Iv Jj Jl Jp Lw Ms Mx Nj Nl Nm Nw Nx On Qd) Jj(Jl Lw Nj Nw Nx On Qd) Nj(aA Jp Lw Nw Qd)} Nj{Nw(aA Jj Lw Mp Mx My Nd Nn Of Og) On(Jj Of Og Oy) QdJj} Jj{On(Fp Mh Ms Of) QdNx} MsOfOn

Figure 39 Continued

Constrained panels with 3 analytes, where 1.0E-9 >= 'model p-value' > 1.0E-10. Contains 889 panels of 38,239,313 total panels evaluated. :
Nt{Oy(Fp Ij Ik Ir Jg Jl Jq Lh Li Lx Mu Mx Mz Nd Nj Nn Nu Nx Oe Of Pa Pg Qa Qb Qe) Ng(Ij Ik Ir Jl Jq Jt Lh Li Ly Me Mf Mm Mp Mx Mz Nd Nn Nu Nv Nx Ny Qa Qb Qe) My(Fp Ik Ir Jl Jq Lh Li Lx Mp Mt Mx Mz Nd Nn Nu Nv Nx Qa Qb Qe) Of(Fp Ij Ik In Ir Jl Jq Js Jt Li Mp Mx Mz Nj Nn Nv Ny Qa Qb Qe) Ms(Fp Ih Ir Jl Jq Js Lw Ly Mp Mx Mz Nd Nx On Qa Qb Qc Qe) Mz(Hx Ii Ik In Jo Mh Ml Mp Mv Mw Mx Nf Nj Ny Oe Om Pb) Ik(Fp Ir Jp Li Lw Mp Mx Nx Oe Og On Qa Qb Qe) Jo(Ir Jl Jp Jq Js Jt Mp Mx Nx On Qa Qe) Oe(Fp Ir Jl Jp Jq Lw Mx Nx On Qa Qb Qe) Nj(In Jl Ly Mp Mx Nd Nn On Qa Qb Qe) In(Fp Ih Ir Lw Mp Qa Qb Qe) On(Ii Jh Mg Mv Mw Nq Om) Mp(Fp Jp Mx Nq) Nn(Mv Mw Og) Mh(Jl Jq Lx) Ii(Jl Jq Lh) Jp(Mg Mx Nq) Fp(Lw Ly) Mj(Mx Qd) NqQa NuJq LwQe LyQb HrJl HxNw IsIv} Et{Of(Ij Jg Jl Jq Js Jt Lh Me Mh Mi Mp Ms Mz Nl Nm Nn Nv Nw Og Oy Qa Qb Qe) Oy(aA Fp Iv Jl Lw Lx Mh Mp Ms Mx Mz Nj Nl Nn Nv Nx Ok Pg Qa Qb Qe) Og(aA Fp Iv Jl Lw Mh Mp Ms Mx Mz Nl Nm Nv Nx Ok Qa Qb Qd Qe) Ms(aA Fp Ih Iv Lw Mh Mp Mx Mz Nd Nu Nx Ok Qa Qb Qd Qe) aA(Ih Iv Jj Jn Lw Mb Me My Mz Ng Nl Ok Qa Qb Qd Qe) Lw(Fp Hr Iv Mb Me Mh Mx My Ng Nl Qb Qd Qe) Nu(Fp Jl Jq Me Mg Mp Mx Mz Nw Oe Ok Qd) Ng(Fp Iv Mh Mp Mx Nj Nm Nn Nv Ok On Qd) Nj(Jl Mi Mr Mx Mz Nd Nn Nw Qa Qb Qe) Im(Fp Iv Jl Me Mx Mz Nl Nw Nx Ok Pz) Ok(Fp Hr Iv Mb Mh Mx My Qd) Jj(Ih Jn Js Lv Me Mz Nv) Fp(Hr Mp My Nl Nx Qd) Mh(Hr Iv Mp Mx Nl Qd) My(Mx On Qa Qd) Qd(Nq Oe Pz)} Ok{Og(aA Fp Iv Jj Lw Mb Mf Mh Mp Ms Mx Nl Nm Nn Nw Nx On Oy Qa Qb Qd Qe) Im(aA Fp Hr Ii Iv Jp Lw Mb Mh Ms Mx Mz Nf Ng Nl Nq Nw Nx Oe Om Qd) Jj(aA Ih Jg Jl Jp Lw Mf Mh Mp Ms My Nl Nw Nx On Qa Qe) Nj(Fp Hr Jl Jo Jp Lw Mg Mh Mx Nd Ng Nk Nn Oy Qe) Oy(aA Fp Iv Lw Mp Ms Mx Nn Nw Nx On Qb Qd) aA(Fp Iv Lw Mb Mh Ms Mx My Mz Ng Nq Nu) Nu(Hr Ii Lw Mb Mg Mp Nq Nw Qd) My(Fp Iv Lw Mp Mx Mz Nn Nw On) Ms(Fp Lw Mp Mx Mz Nw Qb Qd) Fp(Hr Lw Nw Nx) Ng(Iv Lw Mp Nn) Qd(Hr Lw Mj Nq) Mb(Mp Nw) Mx(Lw Mj) IvNw} Jj{Nu(aA Fp Ij Ir Is Iv Jn Jq Js Jt Lh Li Lv Lx Mp Mx Mz Nl Nm Nn No Ny Qb) Im(aA Fp Iv Jg Jn Jp Js Jt Lh Lv Mf Mh Mp Ms Mx My Mz Nl Nm Nn Nv Qe) Qd(aA Fp Iv Jg Jl Jp Lh Lv Lw Mh Mp Ms Mx My Mz Nl Nm Nn Nv Nw Og On) On(Iv Jn Lw Mb Mx My Nl Nm Nx Og Oy Qa Qb Qe) Nw(Fp Iv Lw Mp Ms Mx Nl Nm Nn Nx Qa Qe) Jg(Fp Jl Lw Mx Nj Qa Qb Qe) Nj(Jl Jp Nv Qa Qe) Nx(Fp Qa Qe)} Im{Nj(Ik In Iu Jl Jt Lh Mi Mp Mr Mx My Mz Ng Ni Nk Nn Nv Of On Oy Qe) Og(Fp Jg Jq Js Jt Lh Lv Mb Mf Mh Mi Mp My Mz Nh Nn Nv Pe Qe) Nw(aA Iv Lw Mb Me Mh Ms Mx My Ng Nl Of Om Oy Qd) Nu(aA Jl Jp Jq Jt Lw Ms Mx My Ng Nx Of Oy) Qd(aA Jp Lw Ms My Oy) Lw(Jp My) On(Of Oy) aA(My Oy) MsJp} On{Of(Fp Iv Jg Lv Lw Mb Me Mh Mw Mx My Ng Nh Nl Nm Nq Nw Nx Og Om Oy Qd) Oy(Fp Iv Jg Jp Mb Ms Nl Nw Qd) Nj(aA Lw Mw My Ng Nu Oe) My(Mb Mf Nu Nw) Og(Ij Lw Ms Nm) Nu(Ms Mw) NmNg} Nu{Og(aA Jg Jl Jp Jq Lw Nj Nv Nx Qa Qe) Qd(aA Lw Ms My Ng Nj Nw Nx Of Oy) Nj(aA Jl Jp Lw Mz) Nw(Fp Me Mh Mp Mx) Jp(aA Lw) MzaA NgJg NvOy} Nw{Ms(aA Fp Iv Lw Mp Mx Og Qd) aA(Fp Iv Mh Mx My Of) Lw(Iv Mb Mx My Og) Nj(Mh Ni Oy Qd) Og(Fp Ij Iv Nm) Of(Iv Nx)} Qd{Nj(aA Lw Mp Mz Og Oy) Og(aA Jg Lw Nm Nx) Lw(Ms My Oy) MsMz JgOf OyaA} aC{Ji(aN bM Jq) Lw(aN Li) Mz(aN Nh) AjNm PkbM} Nj{Jp(aA Lw Mp) Ij(aA Og) MzaA} Og{Ij(aA Lw Nm) LwJg} MzUmrB JgOfaA Constrained panels with 3 analytes, where 1.0E-8 >= 'model p-value' > 1.0E-9. Contains 1,518 panels of 38,239,313 total panels evaluated. : Ok{My(Hr Ij Jg Jl Jn Jp Js Li Lx Mf Mh Mi Mr Mt Mu Nd Nl Nr Nv Nx Qa Qb Qe) Hr(aA Iv Jl Jn Jp Js Lw Mb Mh Mp Ms Mx Mz Nl Nn Nw Nx Og Oy Qa Qb Qe) Mp(aA Et Fp Ii Iv Jo Jp Mg Mh Mx Mz Nl Nq Nw Nx Om Qe) Ng(Fp Jg Jp Mf Mh Ms Mu Mx Nd Nm Nv Nw Nx On Qa Qb Qe) Oy(Ij Jg Jl Jn Jp Js Mh Mk Mu Mz Nl Nq Nv Pg Qa Qe) Mb(Jp Js Lw Mc Mg Mx Mz Nd Nn Nx On Qa Qb Qe) Ms(Ih Iv Jg Jn Jp Js Mg Mh Nd Nn Nx On Qa Qe) Mx(Ii Jo Jp Jr Js Mh Mz Na Nq Nw Nx Om) Nq(Fp Iv Jp Lw Nn Nw On Qa Qb Qe) Ii(Fp Iv Mr Nv Nw Nx On Qb Qd Qe) Nn(Jh Mg Mh Mv Mw Mz Nl Om) Lw(Et Iv Jp Mh Mz Nl Nw Nx) aA(Ih Jg Jn Jp Nw Nx Qb) Fp(Jp Mh Mj Nl Oe Om) Mg(Et Iv Jg Lv Nl) Mh(Jp Lx Nw Nx On) Om(Mz Nw On Qa Qb) Oe(Qa Qb Qd Qe) Og(Jg Jn Jp Js) Nl(Et Mz Nw) Iv(Is Mz Nx) Mw(Mu On) HqIm QeNx} Nu{Lw(aA aC Fp Ir Iv Jg Jl Jn Jq Js Lh Li Lv Mb Mh Mp Ms Mx My Mz Ng Nl Nv Nx On Oy Qa Qb Qe) aA(Fp Ih Ij Ir Iv Jg Jl Jn Jq Js Li Lv Mh Mp Ms Mx My Ng Nl Nv Nx On Qa Qb Qe) Nj(Fp Jg Jq Js Jt Lh Li Lx Mi Mp Mr Mx Nd Nm Nn No Nv Nx Pe Qa Qb Qe) Og(Fp Ir Is Iv Jj Jn Js Jt Lh Li Lv Lx Mi Mp Mx Mz Nm Nn No Ny Pe Qb) Jp(Fp Jl Jq Lv Mh Mi Mp Ms Mx My Mz Ng Nm Nn Nv Nx Of Oy) Im(Fp In Iv Js Lh Lv Mh Mp Mz Nl Nm Nn Nv Oe On Qe) Jj(Aa Fr Ih Ii It Jr Mh Mi Mm Mr Pe Po Qc) Mz(Hx Jl Jq Mp Ms My Nx Pb Qd) On(Fp Jh Mb Mh Mv Mx Nq Oe) My(Jg Jl Jq Jt Nv Qa Qe) Nx(Fp Jl Mp Ms Of Oy Qa) Jg(Jl Mh Mp Mx Of Oy) Jq(Fp Mh Mp Ms Oy Qe) Ms(Jl Js Qa Qe) Oy(Jl Lx Mp Qa) Qd(Mh Mp Nq) Ng(Jt Nv) Jl(Hr Nt) FpMp JiaC} Nw{Oy(aA Et Fp Ij Iv Lw Me Mh Mk Mp Ms Mu Mx Nl Nm Nn Nq Nv Nx Of Oz Pd Pg Qa Qd Qe) My(Et Fp Ij Iv Jt Lv Mb Me Mf Mh Mi Mp Ms Mt Mu Mx Nl Nm Nn Nq Nv Nx Of Qa Qd) Og(aA Ik Jg Jl Jt Mb Me Mf Mh Mp Mx Nl Nn Nx On Qa Qb Qd Qe) Of(Fp Ij Ik Jg Jt Lv Lw Mb Me Mf Mp Ms Mx Nl Nm Nn Qd) Ms(Et Ih Jn Jt Me Mh Mz Nl Nm Nn Nx Qa Qb Qe) Jj(aA Ih Ij Ik Jg Jl Jn Jt Lv Mb Me Mf Mh Qb) Mp(aA Fp Iv Mb Me Mh Mv Mx Ng Nl Nq Om Qd) Lw(aA aC Fp Hr Me Mh Ng Nl Om Qd) Mh(Fp Iv Lx Mr Mx Nl Nm Nx Qd) aA(Ih Jn Mb Me Ng Nl Qd Qe) Nm(Fp Mb Me Mx Ng Nl Om) Mx(Fp Iv Mb Mj Nl Om) Nn(Mb Me Mv Mw Ng) Et(Mb Me Ng Nl) Ng(Iv Nx On) Fp(Nl Om) Nq(Iv Qd) Mb(Mz Nd) On(Mv Mw) aC(aN bM) MeOm NlQd} Et{My(Ih Ij Iv Jl Jn Jq Js Jt Lh Lv Lx Mf Mi Mp Mr Mt Mu Mz Nl Nm Nn No Nv Nx Pe Qb Qe) Ng(Ih Jg Jl Jn Jp Jq Js Jt Lh Lx Me Mf Mi Mr Ms Mz Nd Nl Nx Pe Qa Qb Qe) Mb(Ih Jl Jq Js Jt Lh Mc Mi Mp Mz Nd Nm Nn Nv Nx Og On Pe Qa Qb Qe) Oy(Ih Ij Jn Jp Jq Js Lh Lv Mi Mk Mu No Nq Og Pa Pe Po) Mz(Hr Hx Ii Lw Mp Nl Nn Ny Pb Qb Qd) Ms(Jl Jn Jq Js Me Mi Nl Nn On Qc) Og(Jq Js Me Mf Mi Nn On) Hr(Jl Jq Lh Mr Pe Qa) Mv(Lx Mt Nn Nv On) Qb(Me Mp Nx Oe Om) Mg(Jt Nl Nm Nx) Jo(Js Jt Lh Nx) Oe(Jn Js Nv Qe) Nn(Jh Me Mw) Mp(Iv Me Nl) Mx(Hu Jr Js) Ii(Lh Mr Pe) Nq(Iv Qa) Mw(Nv On) IsIv QaOm QeNx JhOn} Im{Lw(aA aC Fp Hr Iv Jg Jl Js Mb Mh Ms Mx Mz Ng Nl Nx Of Om On Oy Qe) Jp(aA Fp Iv Jl Jq Jt Lv Mh Mp Mx My Mz Ng Nl Nm Nn Nx Of Oy) Ms(aA Iv Jl Jn Jq Js Jt Lv Mi Mp Mx Mz Nn Nx Of On Oy) aA(Fp Hr Iv Jl Jn Lv Mb Mh Mp Mx Mz Ng Nl Nq Of) Oy(Iv Jg Jl Jt Lh Lv Mp Mx Mz Nl Nn Nv Nx Pg) My(Iv Jl Jt Lh Lv Mi Mp Mx Mz Nm Nn Nv On) Qd(Jg Mh Mz Nl Nm Nq Nx Of On) Of(Iv Jg Jl Jt Lv Mp Nx) Ng(Jg Mp Nm Nv On) Nj(Jg Js Nx Qc) On(Mh Mw) MxJg HrJl aCaN} Jj{Jg(aA Ih Ij Ir Is Iv Jn Jq Js Lh Li Lv Lx Mh Mi Mp Mr Ms My Mz Ng Nl Nm Nn Nv Nx Of Og Oy Po) Jp(Fp Ih Ij Ik Iv Jl Js Jt Lh Li Lv Lw Mh Mp Ms Mx Nl Nm Nn Nv Nx Qa Qb Qe) Nj(Fp Ij Js Jt Lh Li Lw Lx Mp Mx Mz Nm Nn Nx Ny Qb) Qa(aA Fp Iv Jl Jt Li Lv Lw Mp Ms Mz Nm Nn Nv) Nx(Iv Jl Js Jt Lh Li Lw Lx Mp Mx Nm Nn Nv Qb) Lw(aC Fp Js Li Mx Nv Qe) Nm(Fp Js Mx Nv Qb Qe) Fp(Jt Mp Nv) Iv(Jl Li Nv) MpQe MwOn IjaA QbJt JibM JlLi} On{Oy(Ii Ik Jn Li Lw Mf Mh Mx My Mz Ne Ng Nh Nm Nn Nx Og Pd Qa Qb Qe) Og(aA Fp Iv Mb Mf Mh Mx My Ng Nl Nq Nx Qa Qb Qd Qe) My(Fp Iv Jg Jp Lw Mh Ms Mx Mz Nm Nx Oe Qd Qe) Nj(Ik Jh Jp Mh Mp Mr Ms Mv Mx Mz Ni Nk Om Qd) Ng(Fp Iv Jg Lv Lw Mb Mf Mh Mp Ms Nl Nn Qd) Ms(aA Fp Iv Jn Lw Mh Mx Mz Oe Qd) Qd(Mh Mw Nq Oe) aA(Fp Mb Mh Mx) Lw(Fp Mb Mh) Mw(Mu Nn) NtNb} Qd{Oy(Jg Jl Jp Lh Lx Mi Mp Ms Mx Mz Nl Nm Nn Nv Nx Og Pd) Lw(aA aC Fp Jg Jp Mb Mh Mx Mz Ng Nl Nq Nx Of) Og(Fp Iv Jl Jp Mf Mh Mp Ms Mx My Mz Nl Nn Nv) My(aA Jg Jl Jp Lh Mp Mz Nm Nn Nv Nx) Nj(Jl Jp Lh Mi Nd Nk Nm Nn Nv Of) aA(Jg Mh Mj Ms Mx Mz Nl Nq Nx Of) Ms(Jg Jl Jp Mp Nl Nm Nn Nx) Mp(Mz Nx) Ng(Jg Nm) NxOf aCaN} Nj{Jp(Fp Ih Jl Jq Jt Lh Lx Mh Mi Mr Ms Mx Mz Nd Ni Nk Nm Nn No Nv Of Og Oy Qa Qb Qe) aA(Fp Ih Jg Jl Jn Js Jt Lh Li Lw Lx Mp Mr Mx Nk Nm No Nr Nv Nx Og Qa Qb Qe) Lw(Jg Jl Mr Mx Mz Og Qa Qe) Og(Jg Jl Mz Nm Nv Qa Qe) Mz(Jg Mp Nn) Jg(Mp Of) NkQa NvOy} aC{Lw(Aj aM bA Bb bM bV cC Cs cT cU cX Ji Jp Lj Mt Mz Nb Ne Nf Nm Og Qc Qe) Ji(Aj aM cX dE Hr Jo Jv Mz Nb Nc Nd Nh Of) Mz(Aj aM bM In

Figure 39 Continued

Li My Nb Nc Ne Nk Nm) Jv(aW Jp Ke Pj Pk Vt) Nm(aN Of Og) bM(Bb Ke Pj) AjJt PjPk cMfA} Nt{My(Jg Js Jt Ly Mf Mu Nm) Lx(Hx Mv Mw Ny Pb Po) li(Is Jt Mr Nv Nx Pe) Jo(Ih Li Nm Nn Nv Ny) Mt(Hx Mh Mv Ny Pb) Mw(Jg Lh Mu Nv) In(Jq Js Nd Nx) Mv(Lh Mu Nv) Nn(Jh Ms) Mg(Jg Jt) Hx(Lh Mi) NqNv LyNx MhLh MsJn MuHu NhNl IkQc IsJs} Jg{Of(Fp Iv Jl Js Lw Mp Mx Mz Ng Nx Og Qa Qb) Og(aA Fp Ij Jl Mh Mp Mx Mz Qa Qb Qe) aA(Fp Lw Mh Mx My Mz Ng Oy Qb) Ng(Lw Mp Nv Qa Qb) Lw(Fp Mx Oy) Oy(Mx Qb) AjbM} Jp{Lw(aA Fp Mb Mh Ms Mx Og Oy) aA(Fp Ih Mh Ms Mx) Ms(Fp Mp Mx) Kx(dX eP) Og(Ij Nm)} Og{Ij(Iv Jl Mp Ms Nl Nx) Nm(Fp Nx Qa Qb Qe) Lw(Qa Qe) QaNx} Ji{aN(Aj bM dE Jo Of) bM(Aj Jo Nh Of)} Aj{Nm(aN bA cT) JtbM} Gz{Kr(qW rB rC)} My{Mz(aN bM) IjaA} nN{cM(dU oD) bUpI} Fp{aA(Mz Nx)} Lw{LicO LjaN} Kx{HvdX OreP} MncWgV

Constrained panels with 3 analytes, where 1.0E-7 >= 'model p-value' > 1.0E-8. Contains 2,715 panels of 38,239,313 total panels evaluated. : Im{Mz(Fp Hr Hx Iq Iv Jg Jl Jn Jq Js Jt Lh Lv Mb Mh Mi Mp Mx Nf Ng Nl Nm Nn Nv Nx Ny Of Om Pb Qa Qe) Nx(Fp Iv Jg Jl Jq Js Jt Lh Lv Mh Mi Mp Mx My Nf Ng Nl Nm Nn Nv Om Pe Qa Qe) Mh(Hq In Iq Iv Jg Jl Jq Js Jt Lh Lx Mp Ms My Nf Ng Nl Nm Nn Nv Oy Pe) Mx(Fp Hu It Iv Jl Jn Jr Js Jt Li Lv Mb Mj Mp Ng Nl Nm Oe Of Om On Qe) My(Fp Jg Jq Js Lx Mm Mr Ms Mt Nh Nl No Oe Of Oy Oz Pd Pe Qa Qe) Ng(Fp Iv Jl Jq Js Jt Lh Lv Lx Mf Mi Mm Ms Mt Nl Nn Oz Pd Pe) Nl(Fp Jg Jl Jn Js Jt Lh Lv Mi Mp Ms Nm Nn Nv Of On Qe) Iv(In Jg Jl Jn Js Jt Lh Li Lv Mp Nm Nn Nv Oe On Qe) Fp(Hr Jg Jq Js Jt Mm Mp Ms Nf Nm Nn Of Om On Oy) Mb(Jl Jq Js Jt Lh Mi Mm Mp Nm Nn Nv Of On Pe Qa) Qe(Jg Jl Jq Js Jt Lh Lv Mp Nm Nn Nv Oy) Of(aC Jq Js Lh Mi Mm Nh Nm Nn Nv Oz Pe) Jl(Hq Ii Il Jg Jk Jn Js Jt Nm Oe Pb) Oy(Jq Js Lx Mi Mk Mu Nm Nq Oz Pd Pe) Lv(Jg Jn Js Jt Li Lw Mp Nm Om On) Nn(Hu Iq Jg Js Mv Mw Nf Oe Om) Hr(Jq Jt Lh Mi Nm Pe Qa) On(Ii Jh Jk Mv Nq Oe Om) Nf(Jq Js Lh Mi Mp Nv) Jt(Ii In Iu Lw Na Oe) Nm(Jn Js Ms Om Qa) Jg(Jq Js Mp Oe Qa) Lh(Hx Ii Ms Mw Pb) Lw(Iq Jn Li Qa) Mi(Hx In Iq Om) Nv(Hq Mw Oe Om) Mp(Hq Iq Om) Pe(Hx Ii Om) aC(Aj bM Jv) AjaN MsNh MtMv InJs JkJp} Jj{Nx(aA Fr Ih Ij Ir It Jm Jn Jq Lj Lv Mf Mh Mi Mm Mr Ms Mt Mz Nc Nd Ne Nh Nl No Nr Ny Og Pd Pe Pf Po Pz Qc) Js(aA Fp Ih Iv Jl Jn Jt Lh Li Lv Lx Mb Mm Mp Ms Mt Mx Mz Nl Nn Nv Ny Qa Qb Qe) Qe(AA Fp Iv Jl Jn Jq Jt Lh Li Lv Lx Mi Mm Ms Mx Mz Nl Nn Nv Ny Og) Jn(aA Fp Ij Iv Jl Jp Jt Lh Li Lv Lw Lx Mp Mx Nj Nl Nm Nn Nv Qa Qb) Mz(aA aC aN bM Fp Ij Iv Jl Jp Jt Lh Li Lw Mp Mx Nl Nm Nn Nv Qb) Jt(aC Ih Iv Jl Lh Li Lv Lx Mb Mp Ms Mt Mx Na Nl Nn Nv Ny Po) Nj(aA Fr Ih Ii Ir Is Iv Jq Mi Mm Mr Mt Nd No Nr Pe Po Pz) Fp(aA Ij Ir Iv Jl Jq Lh Lv Lx Mm Mt Mx Nl Nn Ny Pz Qb) Nv(aA Ih Jl Li Lv Mb Mh Mp Ms Mx My Nl Nn Of Og Oy Qb) Iv(Aa Fr Ij Jq Lh Lw Lx Mm Mp Mx Nm Nn Ny Po Qb) Jl(Ih Ij Lw Lx Mb Mm Mp Ms Mt Mx Nl Nm Nn Ny Qb) Li(aA Ij Ir Is Jq Lh Lv Mf Mp Mx Ne Nl Nm Nn Qb) Jp(aA Ir Is It Jq Jr Lx Mb Mf Mi Mr No Ny Po) Qb(aA Jq Lh Lv Lw Mm Mp Ms Mx Nl Nn) Ij(Lh Lw Mm Mp Ms Mx Nl Nm Nn Og) bM(bA Cu Dc Is Ks Lw Or Pk) Aa(Is Ji Lw Nb Nt Po Qa) Mx(aA Mm Mp Nn Ny Qa) Nl(Lh Lw Lx Mp Nm Qa) Nm(aC Lh Lx Mp) Qa(Jq Lh My Og) Lw(Lh Lx Ny) Mp(Ir Ny) aA(Ih Nr) aC(Is Qd) JiaN UtoP} Nu{Mz(Fp Hr Iv Jg Jr Js Jt Lh Li Lv Lx Mb Mh Mi Ml Mx Nf Ng Nl Nm Nn No Nv Ny Oy Qa Qb Qe) Lv(Fp Ir Iv Jg Jn Js Jt Li Mp Ms Mx My Ng Nj Nl Nm Nn No Nv Nx Oy Qa Qb Qe) Nx(In Ir Iv Jg Jq Js Jt Lh Li Lx Mh Mi Mx My Ng Nm Nn No Nv Pe Qb Qe) Oy(Aa Fp Ij Ir Iv Js Jt Lh Li Mi Mr Mt Mu Mx Nj Nm Nn No Pe Pg Qb Qe) Mp(Aa Ij Ir Iv Jl Jn Js Jt Li Mb Mh Ms Mx My Ng Nl Nm Qa Qb Qe) Mx(Fp Iv Jl Jq Js Jt Lh Li Lx Mh Ms My Nm Nn No Nv Qb Qe) Fp(Iv Jg Jl Js Jt Lh Mi Mm Ms My Nl Nm Nn No Nv Qe) Nm(Iv Jl Jn Js Lx Mh Ms My Ng Nl No Nv Qa Qb Qe) Aa(Is Iv Ji Lu Lw Mb Me Mh My Nb Ne Nj Of Og) Ms(Ij Ir Is Jg Jn Jt Lh Li Mi Nn Nv Og Qb) My(Fr Ij Ir Js Lh Li Lx Mi Nn No Pe Qb) Ng(Ij Jl Jq Js Lh Li Lx Nn Qa Qb Qe) Nv(Iv Jg Jn Mb Mh Mv Mw Nl Of Qb Qe) Nj(Ih Ij Ik In Ir Iv Jn Mh Nk Ny) Lh(Hr Hx Ii Iv Jn Mb Mh Mw Of Qb) Qb(In Jg Jp Jt Mh Mi Nn No) Jg(Jq Mg Mi No Oe Qa Qe) Jl(Iv Jq Mb Mh Of Qa Qe) Jt(In Iv Lx Mb Mh Of Qe) Og(Ih Jr Mf Mh Mr Nl Po) Jn(Lx Mh Mi Nn No) Jq(In Iv Li Mb Qa) Lx(Hx Mh Pb) Iv(Is Mi No) Qe(Jp Mi Nn) Js(In Mh Of) Lw(Mr No) Qa(In Jp) Ji(Aj aN) Kq(Ef Iz) aC(Nw Pk) LiOf} Nj{Mz(Fp Fr Hr Hx Ih In Iv Jl Jq Js Jt Lh Li Lx Mh Mi Ml Mm Mr Ms Mx My Nd Ni Nk Nm No Nv Nx Ny Oy Pb Pe Qa Qb Qc) Mp(Fp Fr Ih Ij Ir Iv Jl Jn Jq Js Jt Lh Li Lw Lx Mr Mx Ni Nk Nm Nn No Nv Nx Ny Og Oy Qa Qb Qc Qe) Jg(Fp Ik Iv Jl Jq Js Lh Lx Mg Mh Mi Mr Mx Nd Ng Nn No Nv Oy Pe Qa Qb Qe) Lw(Fp Fr Ih Ij Ir Iv Jn Js Jt Lh Li Lx Mi Mt Nn No Nv Nx Ny Pe Qb) Jl(Fp Hr Ih Iv Js Jt Li Lx Mr Mx Nk Nm Nn No Nx Ny Oy Qa Qb Qe) Qe(Jq Jt Lh Li Lx Mi Mm Mr Mx Nd Ni Nk Nm Nn No Nv Nx Oy) Og(Fp Fr Ir Iv Js Jt Lh Li Lx Mi Mr Mx Nn No Nx Ny Qb) Qa(In Jq Jt Lh Lx Mi Mr Mx Nd Ni Nm Nn No Nv Nx Oy) Nv(Fp Ik Iv Mh Mi Mr Mx My Ng Ni Nk Nm Nn Oe Of) aA(Fr Ir Iv Lv Ma Mh Mi Mt Nd Ni Nn Ny Po Qc) Nm(Fp Iv Js Lh Li Lx Mr Mx No Qb) Lh(Fp Hr Ih Ii Iv Mr Mx Nk Oy) Jt(Fp Iv Lx Mr Mx Qb) Fp(Mi Mm Nn Nx) Lx(Mh Mx Oy) Mr(Mm Nd Nn) Mi(Iv Nx) Li(Mx Ni) NoNk IsIv JpNx} Jp{Ms(Ih Ij Ir Is Iv Jl Jn Jq Jr Js Jt Lh Lv Me Mf Mh Mi Mr Mz Nl Nm Nn Nv Nx Of Og Oy Qa Qb Qe) Og(aA Fp Ik Ir Iv Jl Jq Js Jt Lh Li Lv Mh Mi Mp Mx Mz Nn Nv Nx Qa Qb Qe) Mp(aA Fp Ir Iv Jq Lw Mb Me Mh Mx My Mz Ng Nl Nm Nq Nx Of Oy Qb Qd) Nm(aA aC Aj Fp Iv Jl Mb Mh Mr Mx My Ng Nl Nx Of Oy Qb Qd Qe) Oy(aA Fp Jl Jq Jt Lh Lv Lx Mh Mi Mx Mz Nn Nv Nx Qa Qb Qe) aA(Ij Ir Iv Jl Jn Li Lv Mb My Mz Ng Nl Nx Of Qa Qb Qe) Lw(aN Iv Jl Me Mr My Mz Ng Nl Nx Of Qa Qb Qe) Fp(Iv Jl Jq Jt Lv Mf Mx My Nn Nx Of Pb Qd) Mh(Iv Jl Jq Lx Mx My Nn Nx Pb Qd) Of(Ij Iv Jg Jl Jt Mi Mx Nv Nx Qd) My(Et Jl Jt Mi Mx Nn Nv Qa Qe) aC(Aj aN bM Ef Iz Mi Ow Pk Qd) Ng(Jg Nn Nv On Qd) Aj(aN bM dE Nt) Iz(dE Ic Jv Kq) Mb(Jl Jt Mz) Mx(Nn Nx Qd) On(Jh Mv Mw) dX(Ky Or Pk) Ef(Kq Wm) Qd(Nn Nq) Jv(Lj Or) IvJl QaNx KieP} aA{Mz(Ih Ij Iv Jl Jn Js Jt Li Lv Lw Lx Mb Mh Mp Ms Mt Mx My Ne Nh Nl Nm Nr Nv Nx Og On Qa Qb Qe) Li(Hr Ih Ij Iv Jl Jn Lv Lw Mb Mh Mp Ms Mx My Ng Nl Nx Og Oy Qa Qb Qe) Fp(Hr Ih Ij Iv Jl Jn Js Jt Lv Lw Mp Ms Mt Mx Nl Nm Nv Og Qa Qb Qe) Jn(Ih Iv Jg Jl Lv Lw Lx Mh Mp Ms Mt Mx Nl Nm Nx Og On Qa Qe) Ij(Hr Iv Jl Lv Lw Mb Mh Mp Ms Mx Nf Ng Nl Nq Nx Of Oy) Qe(Hr Iv Jg Lv Lw Mb Mh Mp Ms Mx My Nl Nm Nx Og On Oy) Qa(Hr Iv Jg Lv Lw Mb Mh Mp Ms Mx My Nm Nx Og On Oy) Nx(Iv Jl Lw Lx Mh Mp Ms Mx Nm Og Qb) On(Ih Iv Lv Lw Me Nl Nq Oe Qb) Jg(Ih Iv Jl Lv Mb Me Mp Ms) Qb(Lv Lw Mp Ms Nm Og Oy) Mx(Ih Iv Jt Lw Nm Og) Lw(Ih Iv Js) Ih(Jl Lv) Js(Ms Og) Nv(Mh Og) HrJl} aC{Pk(aM aN aW bV cC cX dE dJ Iu Ji Ju Ke Li Lw Mm Mp Mu Mz Nc Nd Ne Nk Nm Nn Oi Or Qd Vt) Jv(Ar bM Cs Dc Dd Fy Id Iq Is Iu Kq Lh Li Lj Lx Lz Mt Mz Nr Nw Or Qd Qe Qm Uh Un) Nm(aM aS bA bM bV Cs cT cU cX Hr Is Jo Li Lj Lx Mt Nb Nd Nw Oi Pj Qc Qd Qe) aN(bA Bb cT Dc Is Jt Ke Li Lx Mi Mm Mt Nd Ok Pj Qc) bM(Dc Fy Gp Is Jt Kq Mi Mt Ok Or Qd Uh Un Vt) Qd(Aj aS Bb dB Jt Mz Nb Nh Of Oi) Nw(Aj aM aO bV cX Mi Nb Nd Nc Of) Vt(aS Bc Ne Nf Nh Qg Qx Ub Um Wm) Pj(Aj aM cX Ju Mz Nd Of Or Ow) Bb(aM Is Mi Mt Mz) Aj(Is Jg Mt Ok) Mz(aO Nf Nl Qc) Of(Cu Jt Ke Ok) Nh(Cu Is) Ji(Ef Wm) Kq(Iz Jh) EtLw NeIs JoJt} Jg{Ng(Fp Iv Jl Jn Jq Js Jt Lh Lv Lx Mf Mh Mi Mr Ms Mu Mx Mz Nd Nm Nn No Nw Nx Og Oy Pd Pe Po Qe) Of(Ih Ij Jq Jt Lh Lv Lx Me Mh Mi Mr Ms My Nl Nm Nn No Nv Oy Pe Qe) Og(Ih Ir Is Iv Jq Js Lh Lv Lx Mi Mr Ms Nl Nm Nn Nv Nx Oy Pe) Lw(Iv Jl Js Mb Mg Mh Mp Mr Ms My Mz Nl Ok Qa Qb Qe) Oy(Fp Jl Js Lx Mh Mi Mp Ms Mz Nn Nv Nw Pe Pg Qa Qe) Mp(Fp Iv Mb Mg Mh Ms Mx My Mz Qa Qb Qd Qe) Mx(Fp Hu Ik Mg Mh Ms My Nm Oe Qb Qd) Ms(Fp Jl Js Mh Mi Mz Qa Qb Qe) My(Fp Jl Lx Mi Mz Nw Qa Qb Qe) Qd(Jk Mh Mw Mz Nq Oe Pz) Mz(Fp Hx Mv Ny Pb) Oe(Fp Nw Qb) On(Jh Mv Mw) Jk(Qa Qb) FpJq MhOk MwNw} On{Mw(Fp Iv Jn Li Lw Mb Mf Mh Mx My Mz Nh Nl Nm Nx Qa Qb Qe) My(Hr Ij Jn Jt Lv Mp Mr Mu Ng Nh Nl Om Qa) Mb(Ik Jl Jt Mc Mp Mv Mx Mz Nm Oe Qa Qd) Oe(Fp Iv Lw Mh Mx Nl Nm Nq Nx Om Qe) Lw(Hr Iv Jh Mx Mz Nl Nq Om Qe) Fp(Hr Iv Jh Mp Nl Nm Nq Om) Mx(Hu Ii Iv Mj Nl Nm Nq Om) Mh(Hr Ii Iv Mv Nm Nq Om) Ms(Ih Me Mp Nh Nl Nm Nx) Ii(Et Lh Mr Nw Pe Qd) Qd(Jh Jk Mj Mv) Nq(Iv Mp Nw) Mz(Hx Nl Om) Mv(Nn Ok) Ng(Jt Om) Jh(Nw Ok) NmNl IvOm} Qd{Mh(Jl Lh Lx Lz Mj Mp Mr My Mz Nm Nn Nx) Nq(Iv Jl Lh Li Lx Mi Mm Mp Nm Nn Nv) Mj(Jl Jq Jt Lh Lx Mi Mr Mx

Figure 39 Continued

Figure 39 Continued

Figure 39 Continued cT Cx dK Jv Lj Mh Mi Mx My Nb Nd Ne Oi Oy Qc) Is(aS bA cT dE Jo Lj My Nb Nd Ne Ng Nh Nl Of Oi Oy Qc) bA(aP bL dE Im Ir Li Lj Mi Mx Nb Nd Ne Nt Of Qc Qd) Qd(aS bS cT Ef Lj My Nb Nd Ne Nh Oi Oy) Qc(dD Iu Li Lj Lx Mi Mt Nb Of) Of(Cu Im Jt Ke Kq Nt Ok On) Lj(cM cT Jt Jv Mi Nb) cT(Ct cU Dc dE Mi) Ji(Ef Jv Mm Wm) Cu(Jo Nf Nh) Lx(bS dE Nb) Im(dE Nb) Jt(Jo Ng) Jv(Ke Or) EfKe McLi MhtT NhQa IuQe JhKq cUdH} Mp{Fp(Aa Ir Iv Jn Jq Js Jt Mb Mf Ms Mx Nf Nh Nl Nv Oy Qa Qb Qe) Iv(Aa Ij Ir Jl Jn Jq Js Jt Li Lx Ms Mx Nl Nv Oy Qa Qe) Mb(Aa Ij Ir Jq Js Jt Li Mx Nv Qa Qb Qe) Ms(Aa Ij Ir Jl Jn Jq Jt Li Mx Nv Qb Qe) Nl(Ij Jn Jq Js Jt Li Mx On Qa Qb Qe) Oy(Ij Js Jt Lh Li Nv Qa Qb Qe) My(Ij Jt Li Nv Qa Qe) Aa(Me Mh Nb Ne Of) Mx(Jn Jt Li Qa Qe) Qe(Jq Jt Li Lv) Ng(Jt Nv Qa) On(Me Mv Om) Qa(Jq Lv) QbJt NvOf} Ji{dE(Ap aS bA bV cT cV dD Di Ef Ii Ik Iu Jq Jv Lj Ly Ms My Nb Ne Nh Oe Oi) Jv(Ap aS aW bE Cs eF fP Ic Jo Ki Kz Lj Nh oE Of Or Ou Qv Um) Jo(Aa bA bE Cs cT CU dB dD iH iJ Us Wm) Wm(Ap Ef Ik It Iu Jt Mk Nh Of Oz Uu) Ef(iJ Kq Nb Nh Nk Nt Oz Qd) Aa(Iv Ms Nb Of Oy) eP(bA Ho Vz Wh) Ap(Et Nb Qe) Of(bA cT iJ) dX(Ho Vz) AwNb MybA QxoE cOcU sHpF} Kq{Ef(Ap Aw cC Cs dE Dk Fb Hc iJ Jd Jo Jv Ke Ko Kr Lj Lv Mx Nf No Nt oE Of Om oN Or Pj Qd Qe Uh Vt Wm) Jh(Ad Ap Cw dE Dg Fn Hv Ic It Jv Kl Lv Mb Mg Nd Ng Oi oN Or Pg Ph Qu Vt) Iz(aS bA bI bV cC cX dB Fn Hf Ic Jo Kz Mc Pa Qx Uh Um Us Vt) Of(Aw dE Hc Jd Jv Lj My Om) Jv(Lj My Or) Om(Nd Or) MyJo TldX OyPa} Oy{Nv(Ij Iv Jn Js Jt Li Lv Lx Mb Mh Mi Mm Ms Mt Mx Nh Nl Nn Of Pd Pg Qa Qb Qe) Qa(Aa Fp Iv Jl Jq Jt Lh Li Lv Lx Mi Mm Ms Mx Nl Nn No Pg) Qe(Aa Jl Jq Jt Lh Li Lx Mi Mm Ms Mx Nn) Lx(Ij Iv Jl Jn Jt Mh) Iv(Aa Jl Jt Lh Li) Jl(Ij Jt Li Qb) Jt(Fp Mx Qb) Aa(Is Nt) Ij(Nn Pg) MsJs QbLh LiPg} On{Jh(Hx Ii Ij Jn Jq Js Jt Li Me Mr Mt Nl Nn Pb Qa Qe) Mv(Hr Ij Jn Js Li Lx Mf Mi Mr Mt Nh Nl Qa Qb Qe) Ii(Ih Jl Jq Jt Lx Mi) Qa(Hr Jk Nb Nq Oe Om) Hx(Lx Mi Mr Mt Pe) Nq(Li Mr Qb Qe) Hr(Jl Jq Jt Pe) Jk(Ir Mx Qb Qe) Om(Me Mr Nl Qb) Mw(Jl Mi Pe) Hu(Mf Mu Nn) Lx(Ny Pb) Nb(Jt Qe) Oe(Jn Qb) AaOf} Ms{Js(Fp Ih Iv Jl Jn Jt Li Lv Mi Mm Mt Mx Nh Nl Nn Qa Qb Qe) Qe(Aa Fp Iv Jl Jn Jq Jt Li Mi Mm Mt Mx Nl Nn) Qa(Fp Iv Jl Jn Jq Jt Lh Lv Mi Mx Nl Nn) Jt(Ih Iv Jl Jn Lx Mt Mx Nl Nn Nv Qb) Jl(Fp Iv Jn Li Qb) Fp(Jq Mm Nv) Mi(Jn Qb) Iv(Li Nv) AaIs MxJn QbJq NvOf} Im{Lx(Hq Hr Hx Mv Mw Nf Pb) Jn(Hq Jq Jr Lh Mm Mt Nv) Mr(Hr Hx Ii Mh Nf Om) Mt(Hx Jq Ny Oe Pb) Nf(Ij Li Me Ni Pe) Nv(Iq Jk Mv Pb) Oe(Jr Js Lh) Pb(Mi Oz Pe) Mb(Mc Oz) Me(In Mm) Hr(Hv Pd) Jq(Li Qa) Pe(Il In) AaOf MmQb MuHu NcNi NlLi IuQe sIpF} Kx{dX(aP aW bN Bo dM eP Hu Kd Kn Ky Kr Lt Mn Nf Ni Oe Of Pk Qx Rb Ry Sj Ub Uh Un Uy Vp Vt Vw Wb Zx) eP(Aw bA Bo bS cH cT Fn Hf Hv Ik Jr Kd Kr Kz Lt Pb Pc Pk Rb Un Uy Vt Vv Zx)} Aa{Of(Et Fp Fr Lx Me Mt Nb Ne Nh Nl Nv Nw Qa Qd Qe) Me(Et Is Iv Mm Mt Nb Ne Nt Nw Ok Qe) Nb(In Is Mh Ne Nh Nl Qc Qd Qe) Is(Iv Lu Mb Mh My Ne Nt) Qe(Iu Iv Jo Nq) Nt(Ik Jo Oe) Mh(Iv Ne) NeIv} Jt{Fp(Hr Ii Iv Jl Mb Mj My Ng Nh Nl Of) Mx(Iv Jr Js Mb Mj My Na) My(Lx Mt Nv Qa Qb Qe) Mb(Jl Nv Qa Qb Qe) Iv(Jl Ng Qa Qe) Ii(Jl Lh Lx) Ng(Nv Qa) CuJo LxMh HrJl IuQa NvOf} Or{Jv(bS cO Cs Fw Fy Gp Jd Ke Lj Mk Na Nh Ou Pj Uh) Ke(Ef Iz Of) Um(jV rB) Vj(dX eP) Pj(Jo Of) FnLj FyOu NoIb MgrC OwUh} Iv{Fp(Jl Jq Lh Mi Mm Mx Nn Nv) Jl(Hr Li Lx Qa Qe) Li(Jq Lv Mx Of) Nv(Mh My Ng Of) My(Lh Qa) Jq(Qa Qe) LxMh IiLh IsQd} Gc{hC(bG Gn Gp Hp Hv Mh Mj Mq mZ Nd Nh Om Ow Pj Rm Un Vi) Nd(Ue Va) Hv(Ua Va) bGoE} My{Qa(Jl Jq Lh Li Lv Mi Mm Nn Nv) Nv(Fp Mf Mx Qe) Qe(Li Mi) Jl(Li Lx)} Qd{Mt(Hx Mv Pb) Wm(Ef Of) Nb(Aw bE) Ii(Mr Pe) GzrB LzPe MbMc MibS NaHw JnJr aSdE} cM{Gp(dU fB gZ jB pK) Ef(fA jB) Ed(dU eQ) YemW JvgZ UkjB UtnN bEfA cFpK fRjP} Jl{Hr(Fp Js Li Qa Qe) Li(Mb Mh Nl Of) Fp(Mm Nl) Mb(Qa Qe)} Ke{Jv(Ap eF fP Lj oE Of) Ef(fP iJ oE) DudX IlIz SheP OzlM} Lh{Ii(Js Mx Qa Qb Qe) dX(Wb Zx) MjMx MuMw HrQa sIpF} bU{oW(EF iA Qw) Qw(oD pI) IboD TopH aReQ fAnW} Fp{Mm(Jq Js Lv Mx Nl Qe) Jq(Hr Nl) NvOf} Lx{Mh(Jn Js Mx Qa Qe) Jv(cO oN) UhoN} dX{Po(Ry Zx) Mn(Kc Ld) Un(Ry Sj) IsTl} Ib{No(Jv Of Rf Vt) WnUh UtdU} uM{sH(Lj Oi Pf) Il(sI sJ) MhsI} Nv{Of(Lv Mb Mx Nl) NgQa} Uh{Wn(Db Hb Uu) Jv(Cs Qe)} Jq{Qe(Hr Mb Nl) MbQa} Ut{Eq(nO oO) DpoP VsnO} eP{Un(Du Sf) MnKc WhVt} Js{Is(Mx Nw) JnNw} jM{sH(Mw rU) NisF} pF{Jr(sF sJ) VqjP} Po{oN(Iz Qw)} Gz{KrqV LiqP} Ly{HfjY KrjU} Ok{eQ(Kl Uu)} eC{pH(Jf Up)} TiQvrZ ThNdqB GpRyhC NoRfjB MbMmQa MiLjbS MncEgV TocRoD YknKoH VtaSdE bAcUdH cDsJkR

Constrained panels with 2 analytes, where 1.0E-8 >= 'model p-value' > 0. Contains 144 panels of 200,124 total panels evaluated. : Et(aA Fp Im Iv Ji Jj Jl Lw Mb Me Mh Mi Mp Ms Mx My Mz Ng Nj Nl Nt Nu Nw Of Og Ok Oy Qa Qb Qd Qe) Ok(aA Fp Hr Im Iv Jj Jp Lw Mb Mh Mp Ms Mx My Mz Ng Nj Nl Nn Nt Nu Nw Nx Of Og Oy Qb Qd Qe) Nt(aA Fp Ik Im In Ji Jj Jl Jp Jq Lw Mp Ms Mx Mz Ng Nj Nw Oe Of Og On Oy Qa Qb Qd Qe) Ji(aA aC Hx Ii Im Iv Jj Jp Jq Mh Ml Ms Mw Mx My Nj Nu Ny Of Og Om Oy) Nw(aA Fp Im Iv Jj Lw Mh Mp Ms Mx Nj Nl Nu Of Og Qd) Qd(aA Im Jj Lw Nj Nu Og) On(Jj Nj Nu Of Og Oy) Im(aA Jj Nj Nu Og) NuJj Constrained panels with 2 analytes, where 1.0E-7 >= 'model p-value' > 1.0E-8. Contains 93 panels of 200,124 total panels evaluated. : Im(Fp Iv Jg Jl Jp Jt Lv Lw Mp Ms Mx My Mz Nl Nx Of On Oy Qe) Nu(aA Fp Jg Jl Jp Jq Js Jt Lw Mp Mz Nj Nx Og Qa Qe) Qd(Fp Jg Jl Jp Mh Mp Ms My Mz Nl Nm Nn Nx On Oy) On(aA Fp Iv Lw Mb Mh Ms My Ng Ok) Nw(Mb Me My Nm Nn Oy Qa) Jp(aA Fp Jj Lw Mx Nj) Jg(aA Jj Of Og Ok) Et(Jq Nn Nx) Jj(Nv Qa Qe) Ok(Jn Js Mg) aC(Lw Mz Nm) NjaA IjOg JiaN Constrained panels with 2 analytes, where 1.0E-6 >= 'model p-value' > 1.0E-7. Contains 191 panels of 200,124 total panels evaluated. : Jp(aC Ih Ir Iv Jl Jq Js Jt Lh Li Lv Lx Mb Mh Mi Mp Mr Ms Mz Nl Nm Nn No Nv Nx Of Og Oy Qa Qb Qe) Nu(Aa Ih Ij Ir Is Iv Jn Jr Lh Li Lv Lx Mh Mi Mr Ms Mx Nl Nm Nn No Nv Ny Pe Qb) Nj(Fp Ij Jg Jj Jl Js Jt Lh Li Lw Lx Mi Mp Mr Mx Mz Nm No Nv Qa Qe) aA(Fp Ih Ij Iv Jl Jn Js Li Lx Mx Mz Nv Nx Qa Qb Qe) Jg(Fp Iv Jl Lw Mh Mi Mp Ms Mx Mz Ng Oy Qa Qb Qe) aC(Bb Im Is Jt Jv Ke Mi Mt Nw Ok Pj Pk Qd Vt) Im(Jq Js Lh Mb Mh Mi Ng Nh Nm Nn Nv Pe) Jj(Fp Ij Iv Jl Js Jt Li Lx Nx Qb) On(Lv Me Mp Mw Mx Nl Nm Nq Oe Om) Lw(Aa aN Fp Iv Js Li Mx Qa Qe) Aa(Is Iv Nb Nt Qe) Qa(Mp Ms Nm Nx Og) Aj(Ji Jt Mz Nm) aN(cT Mz Nw Qd) Qe(Nm Nx Og) Fp(Nm Nx) bM(Ji Mz) IzKq KxdX NvOg Constrained panels with 2 analytes, where 1.0E-5 >= 'model p-value' > 1.0E-6. Contains 407 panels of 200,124 total panels evaluated. : aC(aN bA Cs cT Cu Dc Ed Et Fa Fw Fy Id Ih Kq Lh Li Lj Lx Mm Mp Nb Nd Nt Nu On Or Qa Qc Qe Uh Un Wm) Aa(Et Fp Ih Im Ji Jj Jp Lu Lv Lx Mb Me Mh Mp Mr Ms Mt Ne Nh Nj Nl Nx Of Og Ok Po Qa Qb Qc Qd) aA(Fr Ik Ir Jj Jq Jt Lh Lv Lw Mb Mh Mi Mm Mp Mr Mt Nh Nl Nm Nn No Nr Ny Og Po Pz Qc) Nx(Iv Jg Jl Js Jt Lh Li Lw Lx Mh Mi Mp Mr Ms Mt Mx Mz Nj Nm Nn No Nv Og Qb) Qe(Aj aN Fp Iv Jl Jq Js Jt Lh Li Lv Lx Mi Mm Mp Ms Mx Mz Nl Nn No Nv Oy) Lw(Aj bA bE bM Cs cT Ij Jj Jl Jn Jt Lh Lx Mp Mr Mt Mz Nl Nv Ny Og Qb) Jg(Aj Ih Ir Jn Jp Jq Js Jt Lh Lv Lx Me Mg Mr My Nl Nm Nn No Nv Oe Pe) Mz(bE dE Fp Iv Jj Jl Jt Jv Lh Li Lx Mp Ms Mx Nl Nm Nv Qa Qb Wm) Nj(Fr Ih Ir Is Iv Jn Jq Lv Mm Mt Nd Nn Ny Og Pe Po Qb Qc) Iv(Fp Jl Jq Js Jt Lh Li Lx Mi Mp Mx Nm Nn No Nv Og Qa) Qa(Fp Jl Jq Jt Lh Li Lv Mb Mi Mm Mx My Nl Nn Nv Oy) Mp(Fp Ij Ir Jj Jn Jq Js Jt Li Lx Mx Nl Nm Nv Qb) Jj(bM Fr Ir Is Jn Jq Lh Mt Mx Nl Nm Nn Ny Po) Nv(Fp Jt Lv Mb Mh Ms Mx My Ng Nl Nm Of Oy) Jp(Aj aN Is Iz Jn Jr Jv Me My Ng Pe Uu) Fp(Jl Jq Js Jt Lh Lv Mi Mm Mx Nl Og) Nm(aN Jl Jn Js Li Lx Mx Nl Og Qb) bM(bA cT Is Ke Nw Ok Or Pk Qd Uh) Aj(Dc Et Is Kq Mt Nt Nw Ok Qd) Jl(Jn Js Jt Li Lx Mx Nl Og Qb) aN(bA Dc Is Lj Lx Mt Nb Ok Qc) Jt(Li Lx Mb Ms Mx Nl Og Qb) Ji(Ap bA bE dE Ef Jv Wm) Li(Jq Js Lv Mx Nl Og Qb) Lx(Eo EW Mx) Qd(aS bE Wm) Kq(Ef Jh Of) Og(Js Lh Qb) Jv(Ke Or) GchC NuMy MsJs ZxjD QbLh KeOf KxeP

Figure 39 Continued

Constrained panels with 2 analytes, where 1.0E-4 >= 'model p-value' > 1.0E-5. Contains 833 panels of 200,124 total panels evaluated. : aN(Aj aM aS Bb bM bO Cs CU DD dE dF dK Ed Et Fa Fp Ij lm Ir Iv Jj Jl Jn Jq Jt Jv Ke Kq Lh Li Lv Mi Mp Mx Nd Ne Nt Nu Nx Og On Or Pd Pe Pf Pk Po Qa Qb Uh Un Vt) Mz(aM aS bA Cs CT dD Ed Ef Fr Hr Hx Ih Ij Ik Ir Is Iz Jn Jq Jr Js Lv Mb Mh Mi Ml Mm Mr Mt My Nc Ne Nf Nh Nn No Nr Ny Og Or Pb Pe Po Pz Rc Uh UM Uu vA Vt) Lw(Ar aS bO bS bV cC cK cU cV Dc dD dE Fr Hr Hu Ih Ik Ir Is Jq Jr Lj Lv Mb Mh Mi Mm Ms Nc Ne Nh Nm Nn No Nr oE Or Oy Pe Po Pz Qc) Lh(Aj Hr Hx Ih Ii Ij Ir Is Jl Jn Jq Js Jt Jv Li Lv Lx Mb Mf Mh Mm Mp Mr Ms Mt Mw Mx My Ne Nf Ng Nh Nl Nm Nn No Ny Oy Pb) aC(aA AJ aM Ar aX aZ Ba bM bV cG cU Dd dF dM Ij Iv Jg Jj Jq Ju No Oa Og Pd Pf Po Qb Qm Ub Uf Us Vu) Or(Aj Cs Ed Fn Fw Fy Iz Ji Jj Jo Jp Ke Kq Lj Mk Na Nd Nh Nm Nw Of Og Ou Pj Qd To Uh Um Ur Vt Wm Ti) Nm(bA bM cT Fr Ih Ij Ir Is Jq Jr Lv Mb Mh Mi Mm Mr Ms Mt Nc Ne Ng Nh Nn No Ny Pe Po Qc) Lx(Aj bM Fp Hx Ij Ir Jn Jq Js Jv Lv Mb Mh Mi Mr Ms Mt My Ne Nh Nl Nn No Og Oy Pb Pe Qb) Mp(Fr Ih Is Jl Jr Lj Lv Mb Me Mf Mh Mm Mr Ms Mt Nc Ne Nh Nn No Nr Ny Og Oy Po Pz Qc) bM(Aa Aj aL aS Bb bE Cs Cu Dc dD Ed Et Fa Fy Jp Jq Jt Kq Li Lj Mi Mt Nb Qc Un Vt) Jn(Fp Fr Ij Iv Jq Jt Li Lv Mb Mi Mm Mr Ms Mt Mx Nl Nn No Nv Nx Og Pe Po Qb Qe) Jj(bA Cs Cu Dc Fa Ho Ih Ii Ik Jk Jo Kq Lv Mi Mm Mr Ne Nh nN No Nr Pe Pz Vt) Mx(Fr Ih Ij Ir Jq Js Lv Mb Mi Mm Ms Mt Nh Nl Nn No Ny Og Oy Po Pz Qb Vt) Jl(Hr Ih Ij Ir Jq Lv Mb Mh Mi Mm Ms Mt My Ne Nh Nn No Nv Ny Of Oy Qc) Aj(Ad BA cT Cu Fa Fy Ij Im Ke Li Lj Mi Mn Nb On Pd Qa Qc Vt) Qb(Fp Fr Iv Jq Lv Mb Mh Mi Mm Mr Ms Mt Ne Nh Nl Nn No Ny Oy Pe) Jt(Hr Ih Ir Js Lv Mh Mi Mr Mt My Na Ne Ng Nh Nn No Ny Of Oy Po) Nl(Fr Ij Ir Iv Jq Js Lv Mi Mm Mr Mt Nn No Nx Ny Og Pe Po) Nx(Fr Ih Ij Ir Jq Lj Lv Mm Ne Nh Nr Ny Of Oy Pe Po Qc) Fp(Fr Ih Ij Ir Is Mf Mr Ms Mt Ne Nh Nn No Ny Pe Pz) Iv(Fr Ih Ij Ir Is Lv Mh Mm Mr Ms Mt Nh Ny Pe Po Qc) Ji(aS bV Cs cT Cw dD oE Rc UM Us Uu Vo Vt wJ wQ) Og(bA Dc Fr Ir Is Jq Lv Mi Mt Nn No Ny Po Vt Wm) Jp(Cs dE Ef Hc Ib Ic Kl Ow Qu Rc Sh Ua Vt Wm) Mi(Ij Ir Js Li Lv Mb Mm Ms Mt Nh Nn Nv Ny) Vt(aS bE Cs dE Gc Jv Lj Nd Nf Qg Qv Um Wm) Mt(Ij Ir Jq Js Lv Mh Ms My Nn No Ny Qe) Nj(Jh Jr Lj Ma Mh Nb Ni Nk Nr Pa Pd Pz) Qd(bA bJ bS Cs cT dB dD dE Ef Iz Jv rB) Jq(Fr Lv Mb Mh Mm Mr Ms Nh Nn Ny Po) Ij(Lv Mb Mm Ms My Ne Nh Nn No Oy) Js(jD Lv Mb Mh Mm Nh Nn No Nv Oy) Jv(Cs Dc Fa Kq Lj Nw oE Qe Uh Un) Kq(Aw Bg Hc Ib Jd Jo Lj My Om) Li(Ir Mb Mh Ms My Nh Nn Nv Oy) Gc(jV Sf Ub Ue Va Vb Vo) Lv(Ih Ir Mm Nh Nn No Ny) Uh(Cs fP Lj Nd Rc Wn Wm) Ke(Ap Ef Ik Iz Jo IM) Nn(Ir Mh Ms No Nv) Mm(Ir Mb Mh Mr No) Nw(bA bE Cs dE Wm) aA(Ii Lj Ms Nc Ne) Cu(Jo Nb Of Vb) Nv(Me Mr Nh Oe) bA(dE Lj My Nb) Aa(Jr Oy Pc) Qe(Mb Mr Nh) jD(Jr Yd Tl) Gz(qZ rN) No(Ib Nh) Hv(Hp Ye) cT(Ct Nb) nN(bU Ut) EwaM FaOf FnLj NdSh IbNy PkoE cUdH Constrained panels with 2 analytes, where 1.0E-3 >= 'model p-value' > 1.0E-4. Contains 1,488 panels of 200,124 total panels evaluated. : Aj(aM Ao Ar Ax Bb BC bE cG Cp Cq Cs cU DD dE dF Dk dL Fb Fr Fw Gl Id Ih Ii Io Iv Jd Jk Jl Jn Jq Jr Js Jv Jy Kf Kg Kn Ko Kp Kr Ks Kx Lv Lz Mg Mm Mp Mq Mr Mu Mx No Nr Nu Nv Nx Ny Oa Om Ou Oz Pa Pb Pe Pf Pj Po Pz Qb Uc Uh Un Us Wm) Jv(Ar aS aW bA bE bM bV cT CU cV DD dE Dk Ed Et Fp Fw Fy Gc Gp Hv Id Il Im Iq Ir Is Jd Jj Jl Jq Js Kd Ki Kn Kp Kr Kx Li Lz Mj Mn Mp Mt Mu Mx Na Nn No Nr Nt Nu Oa Og Oh On Pa Pd Pe Pf Pj Pk Po Qa Qc Qh Qv Sr St Tz Us Wu) bM(aA aM Ar Ax aZ bJ bO bV cG cM cU Dd dF Di Fn Fp Gp Ic Id Ij Im Iv Jd Jg Jn Jr Kn Kp Kr Lh Lv Mn Mp Mx My Nd Ne Nt Oa oE Of Og On Ou Pa Pb Pd Pe Pf Pi Pj Qa Qb Qe Qh Qv Sr St Tn Tr Tz Uc Um Up Us Vu Wm) Jj(Al Ax bS Cp Cq cT cU DD dE Ed Em Fb Fn Fw Fy Gc Gl Ha Hu Hv Ic Id Ip It Jd Jh Jm Jr Ke Kr Ks Lj Ma Mb Mf Mg Mh Mn Ms Mu Mv Nc Nd Nq Oa oE Oh Ou Pd Pf Pg Pj Qc Qh Tz Uh Un Up Us Vu Wb Tl Wm) Ke(Ad aM aS Aw bE Bg cM Cs cV Cw dE Ed eF Fa Fn fP Hv Ib Ic Iu JD Jh Ju jV Kl Lj lN Lv Mg Mk My Nd Ng Nh Nm Nu oE Og Oi oN Oy Qu Qx rB Rc Rf TO Ub Us Uu yJ Wm) Kq(Ad Ao Ap aS bE Ch Co Cp Cs Ct Cw dE Dk Ed Fa Fn Fr Hu Hv Ic Ii Ik Kj Kl Lv Mg Mv Mw Nd Nf Ng Nh Nq Nu oE Og Oi oN oP Ou Ow Oy Pg Qt Qu Rc Ss Ua Ub Uc Uh Us Uu Wm) Uh(Ap bA bV cM Cu dB Dc dE dL Ed Fa Fn Fw Fy Hv Ib Ic Id Ik Ir Is Iz jD Jl Ki Kl Kr Lw Mm Mt Mx Oa oE Of Og Oh Ow Pb Qa Qd Qe Qv Ub Up Us Uu Vt) Cs(aM bA Bb bE bJ cM cT Dc dE Et Fn Ic Ik Is Jo Jt Ju Lx Mi Mt Nb Nd Nh Nm Nu Of Og Oi Ok Pb To Un Us Uu) Mt(aS bA bE bJ bS bV cC cO cT cV Dc dE Ed Fn hP Is Iz jD jP IM Mb Mm Mr Oy Pb Pe qW rB Tz uM wQ yJ Wm) Lj(aM aS bE bJ bS bV cM cT CU cV cX Dc dD dE Gc hC Ho Ic Id iJ Ju Jy Mm Nl Nn oE Sf Tz Un Us Wb Tl) Vt(cM cV dD Ed Fa fP Fw Fy gV Ho Ic Iu Jl Jo Ly Nn oE Of Oh Ou Ow Oz Qa Qd Qe Tz Ub Ur Us Vb wF) Dc(aM aS bA bE bJ cT cU dB dE Hr In Jo Jp Li Mi My Nb Nf Nh Nm Nu Of Oy Qc Qe Sf Ur Uc Un Us Vu) Jp(Ap bE bS Ct CU Dg Ed Eq Fa Fn Hp Id Jd Oa Ou Qt Rz Sf Si Ss To Uc Um Us Uw Vb Vc Vs) Qe(aS bA bE bJ bS bV cM CT Cu dD dE Di Ef Fn Hp Iz Ow Qv rB Rm Um Ur Us Uu Vb Ye Tl) Is(aS bA bE bJ bV cM CT dD dE Fr Lv Mb Mh Mi Mm Mr Ms Ne Nh Nl Nn No Pe Vb Ye Wm) Fa(aS Aw cV dE Ef Fn fP Hr Ib Ic Ik Iz Ji Jo Lw Mk Mz Nd Ng Nu Or Pj Qd rB Wm) bA(aM aP bL cC Ct cU dB eF Et fP Hu Iz Jo Li Mi Ne Nt Nu Of Ok Or Oy Pj Pk Qc) Ji(Ed Fn hP Ib Ic Iz jD Ju jV Ki IM Ou Ow Qv Rf tT tX uN vA Vb Vc yJ zG) Un(aS bE cV dD dE Ef Fn Ib Ic Iu Iz Jo Mx Nd oE Of Ou Ow Rc Um Uu Vb Wm) Qc(aM aS bE bJ bS bV cM cT CU dD dE Ih Ik Lv Mm Mr Ms Nl nN No Pe) Or(aS AW cC cM cT cV dE Em Gc Ho Ik jV Li Ne oE Ow Oy Qw Qx rB Uu) Wm(aN Cu Ed Fp Fw Ir Jl Jq Lh Lw Mi Mu Mx Ok On Pa Pe Po Qv Tz Us) Lx(aS bE bJ bL bS bV bZ cC cE cO cT cV dE Fn Iz IM oE oN qW rB wQ) aN(Aa Fn Fw Fy Ic Id Kr Mn Mr Oa oE Oi Pj rQ St tT Tz Ub Um Us) Po(bS Hr Ih Ir Iz jD Lv Mi Mm Mr Ms Ne Nh Nn Ny oN Oy rB wQ) Fr(Ih Ir Jr Lv Mb Me Mh Mi Mr Ms My Ne Ng Nh Nn Oy Pe) Qa(aS bE bS dD dE Fn Ib Iz jD rB Rm Ua Um Ur Uu Ye Tl) Qd(Fn hR Ib Ic jD jV oE Qv Rc rQ rZ Ua Ub Us Uu wQ yJ) No(Ic Ih Ir Jq Mb Mf Mh Mi Mr Ms Ne Ny oE Oy Pe Pz) Gc(aC De eC Ed gP gW hG jD Ju Ni oE Qv Rg Sh Us) Mr(Ih Ir Lv Mb Mf Mi Ms Nc Ne Nh Nn Nr Ny Pe Pz) Nb(aS Aw aZ Bb bE cM cU dD dE Hp Nl Sf Sh Vb Ye) cT(aM Ar cU dE dL Fn Li Mi My Ng Nt Nu Nw Of Ok) Iz(Cu Fy Jl Lh Mu Nw oE On Ou Tn Tr Uc Us Ut) Ny(Ih Ir Jn Mb Mh Mm Ms Ne Nh Nn Oy Pe uN yJ) Pk(aM aS aW bE bO cM cV cX dD dE dL iJ tT wF) nN(aC aL bO cM eC hC Jn Jr lL Lz Mb nI Nw) nO(aC aK aL cF cM Dp Ed hC Qv Ug Um Ur Ut) Fy(dE Ef Gz Ib Ik Jo oE Of Qv Sf Sh Vb) Nn(Hu Ih Jr Mb Me Mm My Ne Nh Nr Oy Pe) Mi(aS bE bS dE Ih Jq Mf Mh Nc Ne Ne Nr Pz) Ir(Ih Jn Jq Mb Mh Ms Nc Ne Nh Ns Pd Pe) rB(Im Jl Jr Js Lh Lw Mj Mx Nw tT tX Tz) Nm(Ap aS bE bJ bO bV cU cV dD dE Nr) Mm(Hv Ih Jr Me Ms Nc Ne Nh Nr Oy Pe) Mz(Fn hP Ib Ic Mf oE Ou Pd Sf Vb yJ) Cu(Hp Ik In My Nf Nh Oy Pg Wd Tl) Sf(bR Dk Gp Ho Hv Jn Jr Nd On Ut) Id(Ed Hv jV IM oE Of rC ul uM) Jq(Hr Ih Ij Nd Ne Nr Oy Pe Pz) Ok(Ap aS bE cU dB dE Vb Vc Wh) Pj(hC Ik jD jI lN oE Of Qv wF) Nl(Ih Mf Mh Ms Nk Nr Pd Pz) Li(aS bE dE Fn gV jD Vb Tl) Nw(aS bV cU jD IM oE Rc Us) Pe(Hr Ih Lv Mb Ne Nh Oy Pz) Ho(bO Hp Nd Nk Sh Ut Vb) Jl(jD Qv qW Um Ur Uu wQ) Jr(Hp Ij jV rZ Sh Vb Ye) Of(Fb Ij Jd Kf Kr Oa Us) Ed(cM dE Lw Mu oE Qv) Lv(Mh Ms Nc Ne Nr Pz) Nh(Ih Jn Mh Ms Nr Pz) Us(Gz Ib Jo Qv Um Ur) Ut(Eq IX IY nT Sh Vb) wQ(Im Js Lh Nx tV vI) hC(Hc mS nI nJ Ry Zq) Mx(qW uM uN Ur vI) aC(Aa iJ nL oE Ti) cM(cU Fp gZ oE oW) Gz(bV rP rV vV) Sh(Dk Gp Hv Jn) Jt(Ct cU dE Vb) Kr(Jo rZ sH sI) bE(cU Im Iv Nt) tT(Dl iP Kz rC) jD(Lh Md Nv Nx) wF(Dk Qm To Ti) jV(Js sK Sr Tz) Ef(Et Lw On) Ms(Ih Nr Pz) Oz(iB jl jP) dE(Et Im Lh) tX(Aa iP Kz) oE(cX Fw Ns) Nt(aS cU) Mh(Ij Pz) Ne(Ih Jn) Hp(Dk On) Uc(Uu Vb) Ye(kG nK) aL(mI oW) hR(aA cV) qX(uI uM) IM(Gl Lh) AatV ApEt BoeW FwVc MbIh NgIj ImyJ InQb QxhW JnPd JsrZ QmuN NxwJ OnVb dAhP nRjY sFjM kFlL rQpF Unconstrained panels with 3 analytes, where 2.2E-14 >= 'AUC p-value' > 0. Contains 50,000 panels of 38,239,313 total panels evaluated. : jD{Op(AD aE Af aH AJ aK AL aM AN AP aQ AS aV AW AX aZ bA bB bC bE Bg bH BN BO bR bU bV bX cA cD cF Ch cK cM Co CP Cq

Wh(aG aJ Ao aW Bg bS cB cH Cu CV Et Fy Gp Ha Hf Ib Ic In Is Je JP Jq Kg Ki Kp Kx Li lM Lx Mt Mv Mz Nq Og Oi Om On Or Ou Pg Qn Qw Qy Rb Tn Uh Un Uv Vu Ti) Yi(Ad aG Ao Ax Bg bS cB CH Cv Db Hw In Io Is Iu jE jM JP Jy Kc Kp Kq Kx Li Lx Mh Mt My Nn Nq Og Oi Ok On Or Oy Pg Qc Qh Qz Rb Tn Tz Um Up Ur Ut Uv Xa) Sj(aF aG AO Bg bR bS cB cE cG CH cL cO eD Gp Gz hA Hb Hf iB In Iq Jp jV Kc Kg Kp Kx Ky Li lM Mm Mn Mt Nq Or Ou Oz Pi Pj Ql Qn Qy Rb Tn Uh Un Us Uv Ti) Rt(aG Ao Ax Bg bS cB CH Cu cV Db Hb Il In Is Jj JP jV Jy Kc Kg Kq Ks Kx Lh Li lM Lv Lx Mm Mn Mt Mv Mz Nf Nj Nq Of Oi Ok Or Ou Pg Rb Tn Uc Ur Ut Vt) Fc(aZ Bg bS cB cH CV Cw Gp Hf In Iq jE JP jV Jy Kc Kg Kp Kx Lj lM Lv Lx Mf Mg Mm Mn Mt Mz Nf Nk Nq Nx Oi Ok Or Ou Pg Qc Rb Ri Tn Us Uv Ti) Fd(aE aG bF bG Bn cB Ch Cu Cw Db Dk Ef Gp Ha Hf Hl Ho Jd Jg JP jV Jy Kc Kf Kj Li lM Lv Mf Nd Nf Nj Nr Og Ok On Or Ou Oz Pf Qc Qh Ql Qm Vu Ti) Xa(aG aJ aM Ao Bg cB cH Cu CV DB dG Gp Hf Hl Ic In Iq Jp Jq Kc Ki Kn Kp Kx Li lM Lx Mh Mt Oi Or Ou Pg Qm Qz Rb Rc Tn Uh Up Uv Vq Vu Yh Ti) Va(aG aM Ao aS Bg bS cB CH Cu CV Gz Hb In Iq Is jH jP jV Jy Kc Kp Kq Kx Ky Li Lv Lx Mf Mk Mm Mz Nd Og Oi Ok Oz Pg Pj Rb Tn Un Us Vt Ti) Hl(Ad aE aG Al aM Ao Ax Bg cB Ch Co Cu Db Fy Ha Ho Ic Jl JP jV Kg Kj Kn Kq lM Lx Mg Mm Mn Mt My Mz Nf Nq Ok On Ou Oz Pg Pz Rb Tn Uh Ti) Ho(aG aM Ao Ax aZ Bg bS cB cH cN Db Fy Ha Hb Hf In It Jp jV Li lM Lx Me Mn Mt Mz Nf Nq Nu Ok Or Ou Pg Pj Qc Rb Tn Uc Uh Ut Uv Vq Vt Ti) Yh(aG aM Ao Bg Bn Ch Cv Dc Dk Et Hc Hu Ib In Is jH Ji Jl jP Jy Kg Kp Kq Kx lM Lv Mh Mn My Mz Nu Nx Oi Ok On Or Ou Pg Qc Qy Rb Tn Uc Vp) Wc(Ad aE Al aM Ao Ax aZ Bc bN bP bS cB Db Dg Et Ha Hb Hf Ic In Iq JP Kc Kg Kp Kx Li lM Mn Mz Nf Ni Nw Ou Pj Qh Ql Qm Rb Un Us Ut Ti) We(aG aJ aM aS Ax Bg cB cH Co Cu Db Dd Fy Hc Hf Ib In Is JP Jq Kp Kx Li lM Lx Mf Mv My Nq Og Oi On Ou Oy Qn Qw Qy Un Ut Uv Vp Vu Ti) Fi(aM Bg cB cH cL Cu Cv dB dH eD Gp hA Hf In Iq Jp Jq jV Kc Kg Kp Kq Kx Lh Li Lv Lx Mm Mn Mt Mz Nq Nx Or Ou Pg Pi Qc Rb Tn Uh Us Uv) Wd(aG Ao aW Ax Bg cB cH Cu CV Db Et Fy Gp Ha Hf Ib In Is JP Kc Kx lM Lv Lx Mt Nq Oi Or Ou Oy Pg Qh Qt Rb Uc Uh Uv Vt Vu Ti) Ps(Ad aG Ao Bg cB CH cN Co Cu Cv Fy Gp Ha Hf IB In Is Jh Jl jP jV Kc Kn Kp Li Mn My Mz Nq Nu On Or Ou Oz Pj Rj Uc Uv Vq Ti) Gh(Al aM Ao Bg bS cB Ch Cu CV Cw In Iq Is JP jV Jy Kc Kq Kx Lh Lv Mm Mt Mz Nj Of Og Oi Ok On Or Ou Oz Qc Qz Rb Tn Vt) Ru(aG aM Ao Bg bS cB CH cV Db Gp Hf In Iq JP Jq jV Kc Kp Kx Li lM Lx Mm Mn Mt Nf Nq Nx Or Ou Pj Qc Qh Rb Tn Us Vq Ti) Tm(Ad aG aM Ao aZ Bg bS cB CH cR Cv Et Gp Hb Ic In Iq JP Kc Kg Kp Kx Li lM Mn Ok Or Ou Pg Pj Rb Uh Us Ti) Vb(aG aM Ao Bg cB cH Cv Fy Hf In Iq JP jV Kc Kq lM Lv Mf Mg Mm Mn Mt Mz Nq Oi Ok Or Ou Oz Pj Rb Uh Um Ut Ti) Vj(aC aG aJ Ao aP aR Ax Bg bS CH cN cQ Cs Db Dd Fp In jH Kc Kg Kp Kz Li Lj lM Mn Mx Oi Ok Ow Qb Rb Rf Tn Th) Uz(aG aM Ao Ax Bg bS cB CH Db Gp Hf In JP Jq jV Kc Kp Kx Li lM Lx Mn Mt Nq Nx Or Ou Qc Rb Tn Us Vq Ti) Vw(aJ aM Ao Bg bS cB Cv Cx dI Hb Hf Hu Ic In JP jV Kc Ki Kx Nq Og Oi Ok Or Ou Pj Qn Qw Qz Rb Ua Uh Ut Th) Zw(aE aG Ao Bg bS cB CH Cu Cv Et Fy Gp Ha Hf Ib Ic In jP Kc Kg Kj Kp Kq Kx Li lM Nx Oi Ou Pj Uc Uv Ti) Wb(aE Ao Bg Bn bS cB CH Cu Fy Gz Hf In jP Jy Kc Kp Kq Kx Li lM Lv Oi Or Qm Qn Qy Rb Tn Uh Uv Vt Ti) Wg(aG aM Ao Ax Bg bS cB CH Db Et Gp Hf In Iq JP Kc Kp Kx Li lM Mn Nf Or Ou Qc Rb Tn Us Vq Ti) Yl(Ad aG aM Ao Ax Bg bS cB CH Db Fy Gp Hf Ic In Iq JP Kg Kq Li lM lN Mn Mt Mz Ok Ou Oz Rb Ut) Uy(aM Ao Bg bS cH Db Gp Hf Is JP jV Kc Ki Kp Kx Li Lv Lx Mh Mz Nf Nx Og Oi Or Oz Pj Rb Vq) Gb(aE aM aW bS cH Cv Db Gp Hf Ji JP jV Kc Kp Li lM Lv Nq Nu Oi Or Pj Qc Rj Ut Uv Ti) Yk(aG aM Ax bS cH Et Gp In Iq JP Kc Kp Kx Li lM Mn Nf Ok Pj Us Ut Ti) Gd(aE aM eF fP gL hC In iP Iq iZ JP kQ kS Li Mf Nd Nq Or Ou Ut tF) Yf(aG bS cH Gp Hx In jE jV Kc Kg Lv Mm) pF(sF sH sI sJ) Ti(Ex Gz wF) sK(Ji Lu Qm) aR(kO oQ) ThzA NqsH MzUm NgWn JpfR KrsI QmwF TkrN aSnT bJlY cIoQ} Gc{hC(AA aC AD aE AF aG aH aI AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR DU dX eC Ed EF EM EQ Et Ex Ez FA fB Fc Fd Fi Fn FP FR Fw Fy Gb gC Gd Gh GL Gn GP GZ Ha HB Hc HF hG Hl Ho Hp Hq Hr Hu Hv Hw Hx iA Ib Ic Id IH Ii IJ Ik Il Im In IO IP Iq Ir Is It Iu Iv IZ jB Jd Je Jf Jg Jh Ji Jj Jk Jl Jm Jn Jo Jp Jq Jr Js Jt Ju Jv Jy KC Kd KE KF KG KI Kj Kk Kl KN KO KP KQ KR KS Kx Ky Kz Ld Lh Li Lj Lp Lt Lu Lv LW LX LY Lz Ma Mb Mc Md ME MF Mg MH MI Mj Mk Ml MM Mn MP Mq Mr MS MT MU Mv MW Mx MY MZ NA NB NC ND Ne NF Ng NH NI NJ NK NL NM NN NO Nq Nr Ns NT NU Nv NW Nx NY Oa oD OE OF Og OH Oi OK Om ON oO OP oQ Or oT Ou oV OW Oy Oz Pa Pb Pc Pd Pe PF Pg PH PI Pj PK Po Ps Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tv Tz Ua Ub Uc Ud Ue Uf Ug Uh Uk Ul Um Un Uo Up Ur Us Ut Uu Uv Uw Ux Uy Va Vb Vc Vh Vi Vj Vo Vp Vq Vs Vt Vu Vv Vw Vz Wb Wc Wd We Wf Wg Wh Yd Yg Yh Yi Yj Yk Yl Zq Zw Zx Ye Tm Tl Xa Wm Tj Ti Th tF Yf) jU(aA aC aD AF aI AJ AN Ao Ap aQ AR AS aV aX aY BA bB BC bE bH bI bJ bQ bR bU bV cA cB cC cD cE cF cG CH cJ cK cN CO CP Cq cR CS CT cU cV cW Cx cZ dA DB Dc DD dG dH dI dJ Dk DL dM Dp Dr ED Ef Ex Ez Fa Fd Fp Fr Fw Gd Gl Gp Ha Ho Hp Hu Hw Ij Ik Il Im It Iu Iz Jd JE jF Jg Jl Jj JK Jl jM JP Jq JR jT Ju Jv Kd Ki Kj Kl Ks Kx Ky Kz Ld Lh lL lO Lp Lt Lu Lw Lx Ly Lz Mb Mc Md Me Mh Mi Mj Mk Ml Mm Mn Mp Mq Mu Mw Mx Mz Na Nf Nm Nu Nv Nx Oa Oe Og Oi Ok Om On Op Or Pc Pg Pi Pj Qa Qc Qd Qe Qg Ql Qm Qn Qw Qx Qy Qz Ra Rj Rm Rt Ru Rv Rx Ry Rz Sf Sh St Tv Tz Ua Uc Ud Uf Ug Uk Ul Um Uo Uv Uw Ux Uy Uz Vb Vc Vi Vo Vq Vs Vw Wd Wg Wh Yg Yj Zq Zw Ye Tl Xa Wm Tj Th) lN(aA aC AD aE aH Aj aK Al AN AO aP aQ Ar aS aW aZ bA BB BC bE Bg bI bL bM bO bP bR bW cD cE cG cJ cL cN CO Cp cQ Cs Ct cU Cw cZ dB DC dD dG dH dI dJ Dl dM Dr ED Ef Ex Ez Fa Fc Fi Fp Fw Fy Gb Gd Gh Gl Gp hA Ho Hp Hu Hw IB IC Id Ik Ir Iz JE jH jI jK Jn jO JP Jq jR Jt JV jY Kc Ke Kf Ki Kk Kl Kn Kr Kx Kz Lh Li lK lL lM Lp Ma Md Me Mf Mj Mk Mm Mq Ms Mv Mw Mx Nc Nf Ng Nh Ni Nj Nk No Ns Nt Nu Nv Ny Og Oi Oy Pb Pd Pf Pi Po Pz Qb Ql Qn Qt Qz Rf Rj Rv Ry Rz Sh Si Sj Sr To Ua Ub Uc Ue Uf Ug Uh Uk Um Un Uo Ut Uv Vb Vc Vj Vo Vq Vv Vz Wd We Wf Wh Yd Yk Zq Zw Zx Ye Tj Ti) lM(Ad aG aK aM aN AR aS aV aW Ax Bb BC bE bF Bg bI bJ Bn Bo bS bX bZ cA cC cE cF cG cJ cK cM cO CQ cR CT cV Cx cZ Dd dE dF Dg dH DI Dk DL Dp Dr Ed Ez Fd Fi Fy Gz Ha Hc Hf Hq Hr Hx Ib Ii Il Iq Ir Jd jE Jf JK Jl Jn JO Jq Ju Kd Ke Kf Ki Kj Kn Kp Kq Kz Ld lK lL lO Lt Lw Lx Ly Lz Ma Mc Md Mg Mi Ml Mn Mp Mq Mr Ms Mt Mu Na Nb Nc Nf Ng Nk Nm No Nq Ns Nt Nu Nv Ny Oa Ok Or Ow Pc Pg Pi Pk Qb Qn Qw Qx Qy Ra Rb Rg Rh Ri Ru Rv Sf Tn Ud Ul Um Uw Ux Uy Uz Vc Vi Vp Vs Vt Vz Wb Wg Yl Zx Tm Xa Tj Ti) iC(aE Af aG Ao Ap aV AW Ax Bc bH bJ Bn BO bS bX cB cH cI cM Co Cp Cq cR Cs cV Cx Db dD De Dp Ef Fd Fp Gl Gz Ha Hw Hx Ib Id Ij In Iq Is Iu Jh Ji Jj Jk JL Jo Jp Js Ju Jv jY Kc Ke Kg Ki Kp Kq Ks Kx Kz Li Lp Lx Mb Me Mg Mh Mj Mk Mm Mr Mu Mv Mw Mx Mz Nd Nf Nh Nj Nr Nv Nw Nx Oa Oe On Op Oy Pa Pb Pc Pd Ph Pk Po Qc Qd Qg Qm Qz Rf Rg Rh Rj Rm Rt Rv Rx Ry Sf Sh Si Sr To Ua Uc Uo Uu Vb Vt Vz We Wh Yl Zq Zw Tl Wm Ti Th) hA(Ad aG An AO Ap Ar aU aX aY Bb bL BN bR bS bX bZ cB cE cG cL cO Cp Cq cR CS cU Cv Cx Db dD dF dH Di dJ Ez Fa Fd Fr Gb Gd Gh Hq Hw Ib Id Ih In Io Iq Is Iu Jd jF Jk Jl Jo JP JT Ju Kc Kj Kn Kp Kr Kx Kz Lp Lu Ma Mf Mg Mh Mj Mq Mw Mx Nd Nf Ni Nn No Nr Ny Oa Oi On Ow Oy Pa Pe Pf Ph Pi Pz Qh Qu Qz Rc Rf Rh Ri Rj Rt Rx Ry Rz Sf Si Tv Uc Uf Um Un Ut Uu Ux Vc Vv Vw Vz Wd Wf Zq Zw Ye Tl) jV(aC Af aJ Ar bJ bM cA cC cD cE cF cK cR Ct Dc dF dG dI Dp Ed Fc Fi Fw Fy Gn Hl Hq iB Ic Ih Ir Jj Jn jO jP Kd Kn Kq Kr Kx Ky Kz Ld lO Lp Lt Lv Lw Ly Lz Ma Mc Mf Mi Mj Mp Mq Mr Mu Mv Mw Mx My Na Nc Ne Nf Ni Nk Nl Oe Op Pi Qx Ra Rb Rc Rh Rj Ru Ry Sj To Tz Ud Uk Ul Um Uo Up Us Uu Uv Uz Va Vp Vq Wf Wg Yh Yi Yl Ye Tm Tj Ti) jP(aC aG An Ap aW Ax bN bQ bS bX cB cG cL cO Cq CS cU Cv Cw Db dH dJ dL Ex Ez Fd Fn Fp Gz Hf Hw Ib Id Im In Io Iq Is It Iu Jo Jt Ju Kf Kj Kn Kx Ky Kz Li Lp Ma Mg Mh Mj Mx Mz Nd Nf Nh Ni Nj Nn No Nr Nt Nv Oh Oi Or Ow Oy Pa Ph Pi Qz Rh Ri Rj Rt Rx Ry Rz Sf Sr St Um Ut Uu Vc Vj Vt Vz Wf Wh Ye Tl Ti) iB(Af aG Aj Al aM aW Bb BN bO cB cC cM Cp Cs Cx Dc Dg dJ Dk Dp Ef Ex Fp Gb Gz Ha Hc Hp Hr Id Ii Iq Iu Iz Jd jF Jh Jj Jk Jl Jo Jr Jt Jv

Figure 39 Continued nL nN nO nR oO) mW(Du Gn Hl Ho IL Sh Uy Vb Vz Wc Wd Wf Yg Yl Zx Xa) Ye(kE kG kI kK kN mM mS mY nB nC nI nJ nN nO nT)
Zx(jU kE kG kI kP mU nA nD oO oP oQ) Sh(jM kI mU nA nC nD oE oO oQ) nN(Eq Lp Og Ry Vb Wf Tl Ti) Lp(iC jH jI jU jV nK) Eo(aM cX
Jr Lx Mb) Yg(iB kG mU nA nD) Dw(aM Mb Ml Mn) Wf(kE kN mT mU) Vb(mU nA nK nO) eO(aM bB Lx Mb) rZ(IX mP mT nD) Ew(aM cX
Mb) Wd(kG nA nD) Kx(dX eP gV) eW(aM Bo Lx) Gn(kP oP) Zq(gP hC) dW(Lx Mb) mU(Hl Vz) IL(nT oO) GdoO YknA YdjE KrsI RvjV
UwkE VchA VtgV dXmS] gV[Vt(AA aC AD aE AF aG AJ aK Al aN AO aP aR As aU aV Aw aX aY aZ Ba Bb bE bF Bg bH bI bL bM Bn
BO bP bR bS bX cA cB cC cD cE cF cG CH cJ cK cL cN CO Cp Cq cR cT CU Cw CX cY cZ dA dB DC DD DE dG dH DI dJ DK DL dM Dp
dR dX Ed Ef EM eP Ez Fn FP FR Fw Gd GP Ha Hb Hc Hf Hq Hr Hu Hw Hx Ib Ic Ih Ii Ik Im In Io Ip Is It Iv Iz Jd Je Jf Jg Jh Ji Jk Jl Jm Jn Jo Jq
Jr Js Jv Jy Kc Ke Kf Kg Kj Kl Kn Kp Kr Ks Kx Ky Ld Lu Lv Lw Ly Mb Mc Md Me Mf Mg Mi Mj Mm Mp Mq Mr Ms Mu Mv Mw Mx My
Mz Na Nb Nc Nd Nh Nj Nl Nq Ns Nu Nv Nx Ny Oe Of Og Oi Om On Oy Oz Pa Pb Pg Ph Pi Qa Qb Qc Qd Qe Qg Qh Ql Qn Qt Qu Qw Qy Qz
Rb Rc Rg Rh Ri Rm Sr Ss St Tn Tz Ua Uc Ud Ue Uf Ug Uh Uk Ul Um Un Uo Up Us Ut Uu Uv Vo Vp Vs Vu Vv) Kx(Aa AD aE aJ aK aM AN
AO AP aQ AR aS aU aV AW aX aY aZ Ba bC bF BG bH bI bJ bL bM BN BO bP bQ bR bS bV bX bZ cA cC cD cE cF cG Ch cI cJ cK cL cN
CO cP Cq CS Ct CU cV CW CX cY cZ DB dC DE dF dG dH DI dJ DK DL dM dN Ed Ef eM Et Ex Ez Fa FP fR Fw Fy Gl Ha Hb Hc Hf Hq Hu
Hw Hx Ib Ii Ik Im Io Ip Is Iz Jg Jh Jj Jl Jm Jo Jp Jv Jy Kc Ke Kf Kg Kj Kk Kl Kn Kp Kr Kz Ld Lh Lu Ly Lz Ma Mb Mc Md Mf Mg Mh Mk Ml
Mn Mq Ms Mt Mu Mw Na Nd Nf Ni Nk Nn No Nq Ns Nu Nv Nx Ny Oa Of Og Oh Om Ou Ow Oz Pb Pc Pf Ph Pi Pk Qb Qd Qe Qg Qh Qv Rj
Rm Sr Tn Tv Tz Ub Uc Uf Ug Uh Un Up Us Ut Vo Vp Vq Vs Vu Vv Tj) Mn(aC aD Aj aM aR bM Bo cE cP cX dC dN Dr Dw eC Ed Ex Ez Fb
Gl HC hG Ib iZ Jd Je Jj Jp Jr Ju Kc Ke Kf Kg Ki Kj Kk Ko Kp KR Ks Ky Ld Li Lv Lw Mb Nd Nn NW nY Oa oE Of Ok Or Ou Ow Ph Pi Pj Pk
Qg Ql Qn Qw Rc Ua Ue Ug Ur Us Uu Uv Vp Vq tF) dR(cA cT cV Cw Dc Dr Et Fr Gl Gn hC Hx Ih Ii Im Ir Ji Jk Jl Jp Jr Lh Li Lj Lx Ma Mb Mj
Mk Ml Mp Mw Mz Nm Nw Nx Ny oE Og Oh Ok On Po Qb Qd Qe Qg Qt Qv Qw Qx Qy Ra Rb Rf Rh Ri Rj Rm Sr Tn To Tz Ua Ud Ue Uf Uh
Ul Um Un Uo Up Ur Vp Vs Vu Vv Wm Tj) Jp(Dp eC Fa Fb Fn Fy Hb HC HF Ib Ic Id iH iP IZ Jd Je Jf Jr Ju Jv Jy Kc Kd Ke Kf Kg Ki Kk KI
Kn Ko Kp KQ Kr KS Ky Kz Ld Oa oE oF oK oN Or Ou Ow pF Ph Pi Pj Pk Qh Qm Qn Qu Qv Qw Rg Ss Uc Ug Uu Vo Vv tF) Lx(aM Dp eC
Ed Eo eW Fa Fb fP Gp HB Ib Id iH iO iP IZ Jd Ju Jv Jy Kc Kd Kf Kk Kl Kp KQ kR KS Kz nY oE oH Or Ou pF Ph Pj Qx Rc Rh Rj Sr Ss St Tv
Ua Uc Ud Ue Uf Uk Ul Um Un Uo Uv Vp Vq Wm Tj) aC(aM Dp Dr Ed Fn Hf Ib Ic Id Jd Je Jf Jy Ki Kk Ko Nw Oa Ok Pj Qg Qh Ql Qm Qn Qt
Qu Qv Qw Qx Qz Ra Rb Rc Rg Rh Ri Rm Sr Ss St To Tv Tz Ub Uc Ud Ue Uf Ug Uh Uk Ul Um Un Uo Up Ur Us Ut Uu Vo Vp Vs Vu Vv)
Ki(aH Bc bF bM bQ bX cB cC cD cF cG Co Cq cT CU Dc dF Fb Fw Fy Hw Hx Il Ji Jn Jq Ke Ko Kp Kq Ky Lh Li Mg Mj Mp Mt Mx Na Nn
No Nq Nt Ny Oh Ok On Pa Pc Pk Qa Qb Qc Qh Qv Rf Tn Ue Uf Uh Un Vu Vv) aM(An aW bA Bo Cp Cs cT cZ Dc Dd dK Dr Dw EO EW Fn
Fy Hf iA Ib Is Ji Jn Jr Kc Kd Ke Kn Ko Kp Kr Ky Kz Li Lv Lz Mb Mz Nj Nk Nw Nx Ny OH Ok Ph Pj Qh Ql Uf Ug Vq) Rg(Ad aK aL Ax aZ
bO bW cI Cu Dc dJ Ex Fa Hb Hx Ij Im Is Iu Jr Kc Ko Lh Lv Mh Mk Mz Nb Nm No Nr Ok On Ow Pa Pe Qa Qe Qh Rf Rh Sr St Tz Ue Ug Uh
Un Ut Vu Tj) Nw(aD Aj Ao aW Ax cP Cs cW cX dD Dr eC eF Fw Gd gL Gn gP hB hC hF hG iA iH Ii iJ Io IZ Jv kR kS Lv Mb Ml Nd Nj oE
oF oH oK oN Ou pF Qv Qx Ss To Uc Vo) Vo(Ad Ar Ax bO cI Cu Cw Dc dD Ex Fp Fy Hx Ij Il Ir Is Jd Ke Kg Kl Ko Kq Ky Ma Mf Mh Mj Mk
Ml Mt Mx Nm Ow Pj Po Qa Qe Qh Qv Qx St Uf Uh Vu) dD(Dr Ib Je Jy Kc Kk Ko Oa oH Qg Qh Qm Qt Qu Qv Qw Qx Qy Rc Rf Ri Rj Rm Ss
St Ua Ue Uf Ug Un Ur Us Uu Uv Vq Vu Vv) Ji(aD aW cX dC dN Dr EF Gd gL Gn gP hC hF hG iH iJ iO OI oN Uv) aD(Cu Cw Is Jr Mj
Qb) dH(hB iA iO iP oN Tn) St(dC Gd Ih Io Nd) On(gL iZ kQ nW oH) eC(Et Mt Nc Nf Nk) gP(Qz Rj To Un Uv) iP(aQ Im No Ny Qa) Qu(al bO
Fr Nr) cA(oH oK oN pF) Gd(Kf Pj Rf) Nu(Oa Pj Rf) Ib(al bM Qb) Tn(cX dM Qb) Ko(Af Rc Uu) Vu(Aj Nd Uu) eW(bB Bo Lv) gL(Qz Rf Uv)
nW(Aa Dc Nj) oF(cV dA fR) Cs(Pk To) Eo(Jn Jr) Gp(Af cX) Ue(al cP) Ir(Sr Tv) Ss(bO Cw) Ky(bC To) fP(Je oN) CvSr DcJu EtkQ FaNx
MxUu InJr HbdX QboH QtbB JjKs LdaF RjcZ OmcX UndK UpbM cViH] Eo{Mb(Aa aC Ad aE aF aG aH al AJ aK Al aM aN AO AP aQ aR
AS aU aV AW AX aY aZ Ba bC bE bF bG bH bI bJ bL bM BN BO bP bQ bR bS bV bW bX bZ cA cC cD cE cG CH cJ cK cL cN CO CP Cq
cR CS CT CU CV CW CX cY cZ dA DB DC dD De dF DG dH DI dJ DK DL dM dN dX EM eO eP Et EW FP fR Fw Gd Gl Gp Hq Hr Hu Hv
Hw Hx Ih Ii Ij Ik Il Im Iq Ir It Iu Iv Jg Jh Ji Jj Jk Jl Jm Jn Jo Jp Jq Jr Jt Lh Li Lj Lu Lw Lx Ly Lz Ma Mc Md Me Mf Mg Mh Mi Mk Ml Mm Mn
Mp Mr Ms Mu Mv Mw Mx My Mz Na Nb Nc Nd Ne Nf Ni Nj Nk Nl Nn No Nq Nr Ns Nt Nu Nv Nw Ny Oe Og Oh Ok On Oy Oz Pa Pb Pc Pd
Pe Pf Pg Po Pz Qa Qb Qc Qd Qe) Lx(aA aC Ad AF aG aH al aJ aK AL aM AN AO AP aQ Ar aS aV Aw AX aZ BA Bb BC bE bF Bg bH bI bJ
bL bM BO bP bR bV bX bZ cB cC cD cE cF Ch cI cJ cK cL cN CO cP Cq cR CS CU cV CW CX cY cZ dA dB Dc DE dF DG DI dJ DK DL
dM dN DW Ef EM eO Et eW FP fR Fw Gd Gp Hr Hu Hw Hx Ih Ii Ij Ik Il Im Io Ip Ir Is It Iv Jg Jh Ji Jk Jl Jn Jp Jq Jr Js Jt Lh Li Lj Lu Lv Lw Ly
Lz Ma Mc Md Me Mf Mg Mh Mi Mj Ml Mm Mn Mp Mq Mr Ms Mt Mw Mx My Mz Nc Nd Nf Ng Nh Nk Nl Nm Nn Nq Ns Nt Nu Nv Nw Nx
Ny Oe Of Ok Om On Oy Oz Pa Pb Pc Pd Pe Po Pz Qa Qb Qc Qd Qe) aM(aA AD aE aF aH aI AJ AN AO AP aQ AR AS aU aV AW AX aY aZ
BA BB BC BG bH bI bL bM bN BO bP bQ bR bV bX bZ cA cB cC cD cE cF CH cI cJ cK cL cN CO cP CQ CS CT cU cV CW dA DB Dc Dd
dE DG dH DI dJ DK DL dM dN DW dX EfeM eO eP Et EW Fp Fr Fw Gp Hq Hr Hu Hv Hx Ih Ii Ij Ik Il Io Ip Iq Ir Is It Iu Jg Jh Jj Jl Jo Jp Jt Lh
Lw Ly Ma Me Mf Ml Mn Mr Mt My Na Nb Nd Ne Ng Nh Ni Nl Nm Nn No Nq Nr Nv Nx Of Og Oi Ok On Oy Pa Pb Pc Pg Pz Qa Qc Qe)
Jr(aA aC aF aG Aj aO AR aS aW Ax aZ bA bB bC bE bF bI bN Bo bR bV bW bX bZ cA cB cC cE cF cG cO cP Cq cR CS CT Cu cW Cx dA
DB DC DD dE DG Dk dN dW EM eO Et fP Fr Gd Hr Hu Hw Ih Ik Im It Jg Jj Jk Jl Jm Jn Jp Js Li Lj Lw Ly Lz Ma Mg Mh Mi Mk Ml Mn Mp
Mr Mv Mw Mx Na Nc Ne Ng Nh Ni Nl Nn Nr Nt Nu Nv Nx Oe Og Oh Oi Ok On Oy Pa Pb Pc Pf Qa Qe) Lv(aD aE aF aG al Aj Al aN Ap aS
aV aW aY Ba Bb Bc bF bI bM bR cF Co CP Cq CS Ct Cv cW dA Dc dD DE dH dI EfeM eP eW Fp fR Gl Gp Ih Ii Ij Il In Ip Is Iv Jg Ji Jk Jm Jo
Jp Jq Js Lj Me Mf Mg Mi Mm Mn Mp Ms Mx Nd Nf Nh Nj No Nr Nu Nw Oe Of Oh Ok On Oy Pa Pb Pc Pf Qa Qe) Mn(aC aD aE aG
AL aP AR As aY bA Bb bC bE bH bM Bo Cp cU cW cX Db Dc dF dG dJ dL dN Em eO Hq Hv Hw Hx Ii Ij Il Is It Jn Jp Js Lh Lj Lz Mf Mh Mk

Figure 39 Continued

Mp Mq Ms Mt Nd Ne Nf Nh Nl Nm Nn No Nr Nt Nw Nx Og Om Pe Pf Po Pz Qb Qc Qe) Hx(Aa aD Af Aj aK AL aQ As aV Ax aY bA bC bE bF Bo bQ cG cR cT Cu Cw cX cY cZ Dc Dd Dk Dw eM Fr Gd Ij Im Io Iv Jj Jk Jn Js Jt Lh Mf Mi Mk Mm Mp Mt Mz Nc Ne Nk Nl Oe Oy Pb Pc Pe Po) Ji(Aa aC aH An Ao Ap aW Ax aY bC bI bO bP bV cD cH cP Cs cX dC dD Dg Dl dM dN dX EM eP Fp Hv Ih Iq Ir It Jh Jj Jl Jn Li Lj Mh Mk Mr Mz Nj Nk No Ns Nx Ny Oh Ok Oz Pb Pg Qa Qb Qc Qe) Po(aD aF aI Aj aO AS aX bA bB Bg bJ bM Bn bO bR bS cC cF cQ cS Ct Cx dA Db DE Dg eM Fr Gd Hu Hv Im Ip Lw Ly Mi Mk Mp Mq Ms Mu Mv Mw Nf Ng Nj Nv Oe Of Oy Pg) Qe(Af Aj As AW Ax BB Bg bI Bn BO bS bV cH cP CT CX De Dl dW eM eP Et Fr Gd Hu Hv Ih Ik Ip Jg Jj Jk Ly Mk Ml Mp Mu Mw Mz Nd Nf Ng Nj Nw Oe Oi Ok Om) cX(aA Ad aF Al aO aW bA BB Bg bM BO bR cB cC Ch Co cS Cu Cv Cw Dd Di Dk Dl Et Gp Hv Hw Ii Is Jh Jl Jm My Nj Nm Nt Nx Ny Ok On Pe Qd) Bo(aC aD Af Aj An AO Ap Ax aY bA Bb bS bX cA Ct cV cW Cx cY dC dD Dg Dl dN dW dX eW Hv Hw Jl Jm Jt Lj Mh Mu Ns Nu Nx Ok Oy Pe Pf) Nw(aC Ad Al aW Ax Bb bE Bg bL bN bQ bV bX cO cT cU dD dK eW Gd Ij Il Is Jh Jl Li Lj Mh Mk Ml Mu Nd No Nr Oe Of Oi Oy Pe) aD(aC aE aH aI Aj aL aY aZ bA BB bE bH BN bS cB Cq cT Cu Cx cZ Dc De dX Fr Hu Mf Mi Mk Mw Mz Na Nv Of Oi) Is(aC aI aR aW Ax bA Bg bM cA cD cN cP Ct dM Dw Ew fP Ik In Ir Jg Jl Jp Lw Mk Ml No Oh Oi Pb Pc Qb) bB(aC aG aH Aj Ax bA Bg bM bN bS Cs dC Dl eW Fw Gd Hv In It Jh Jm Jn Li Lj Ml Nd Nr Nu) No(Af aI Aw aX aY bQ bS cB cE cG Cw Cx dA Dc Dd DE dX Fr Hu Lw Mu Nj Nx Oh Ok) bM(Af Aj bE bX Cq Ct Cu Cx Dc Gd Hv Ij Il Jk Jn Lj Mh Mi Ml Mu Mw Mx Nv Oh Oi Pe) Aj(aI cB cI Cu CW Dc Et Gl Hw Ih Ij Iv Jn Lh Mg Mt Nj Oh On Pd Qa Qb) Ml(aI aX cB CW dX Gp Io Mm Mp My Mz Nj Nm Nx Ok Qc Qd) aC(aF aZ bR bS cA cP cW Et Ik Jj Jn Mm Mt Mz Ok Pa) cB(AF An Ax bA Bb BN bS bW cA Cs cT Cx De Oi) Oh(aO As aX bS cL cS cZ Gd Hq Jj Jo Mz Oi Ok Qb) Af(Cu Dc Gp Hw Ij Jl Jn Jq Lj Nj Ny Pe Qc Qd) Gd(Ad Cu CW Gp Iv Jm Mf Mg Mt Nn On Pa) Of(aI Al Ap bC CW Gl Gp Hw Jm Ng Nj On) Cx(Ad al Et Gp Iv Jl Jn Nj Ny Ok On Qd) Jp(aY bE bN bR dD Iv Mh Mr Mu Mx Oe Pg) Lj(As cW cZ dE EM Et Mm Mz Nj Nx Pa) Qb(Ax bA bS Cu DK Hu Hv Js Mw Ok) Bb(Ad Dd Gp Jn Jq Mf Mz Nj Qc) Ok(Bg cA dC Dg Em Hv Jn Jo Mk) Gp(Bg cA Ch dN Ef Iu Jg Jh) Jj(Al Gl Hw Ii Iv Jn Mf Qc) Mu(Et Im Jl Jn Mt Ny Qa) Nj(Bg Ch cP Jl Mh Mr Qa) Mz(Ao dC Iv Mh Mr Nd) Oi(cW Gl Iv Mt Nn Qa) aF(cG cU dC dF Et Mp) bR(aI dF Gl Hw Iv Nk) dL(Cq Cu Dc dG Il Js) Jo(CW Gl Ij Jm) Mh(EM Nx Pa) Hv(Ij Jl On Qa) cA(aI DC Hw) cP(aI aX Dc Jq) Cs(cZ Mp Nx) Et(Ao aY dD) Mm(Ax Mr Nr) Jl(eM Mi Pg) Mf(bP Ng) Mk(aV Qa) Nx(dD Li) bA(cT Lh) cW(aZ Ct) dC(bN cV) dN(Jq Pe) BgOn EfIi NrMp LwIj MrIk NgIv NkHu HwOg PabE aOdF bSeO} eO{aM(AA aC AD aE AF aG aH aI aJ aK AL AN AO Ap aQ AR aU aV AW aX aY aZ Ba BB BC bE bF BG bH bI bJ bL bM bO bP bQ bR bV bW bX bZ cA cB cC cD cE cF cG CH cI cJ cK cN CO Cp CQ cR cS CT CU CV CW cY cZ dA dB DC DD dE dG dH DI dJ DK DL dM dN Dw dX EM eP Fp FR Fw Gl Gp Hu Hv Hw Hx Ih Ij Ik Il In Io Ip Ir Is It Iu Iv Jg Jh Ji Jj Jk Jl Jm Jn Jo Jp Jq Jr Js Jt Lh Li Lj Lw Lx Ly Me Mf Mg Mh Mi Mj Ml Mm Mn Mp Mr Ms Mu Mx My Mz Na Nb Nd Ne Nh Ni Nj Nl Nm Nn No Nq Nr Nu Nv Nw Nx Ny Og Oh Oi Ok Oy Oz Pa Pb Pc Pd Pe Pf Pg Pz Qa Qb Qc Qd) Mb(AA aC AD Af aH aI AJ aK AL AN AO AP aQ As aU AW aX aZ BA bB bE bF BG bH bI bJ bL bM BN BO bP bS bX cA cC cD cE cG cH cI cJ cK cL Cp cR Cs cT CU CV CW Cx cY cZ dA DB dD DE dF DG dJ DK DI dM dN DW dX Ef Em Et EW FP FR Fw Gd Gl Gp Hr Hu Hv Hw Hx Ih Ii Ij Ik Il Io Iq Ir Is Iu Iv Jh Ji Jj Jl Jn Jo Jp Jq Jr Js Jt Lh Lu Lv Lz Mc Md Mf Mg Mh Mk Ml Mm Mn Mp Mr Mv Mw Mx My Mz Na Nb Nc Nd Ne Nf Ng Nh Ni Nj Nk Nl Nn No Nq Nr Ns Nt Nu Nw Nx Ny Of Og Ok Om On Oz Pa Pb Pc Pd Pe Pf Pg Po Pz Qa Qb Qc Qd Qe) Lx(AA aC AD Af aG aI Aj AL An aO Ap Ar aU Aw AX Ba BB BC bF BG bH bJ bM bN bO bP bQ bS bV bZ cA cB cC cD cE cF CH cI cJ cK cL CO Cp CQ cR CS cT CU cV CW CX DB DC DD DE DG Dl dJ Dk Dl DW dX Ef eM Et Ew FP Fw Gd Gl Gp Hq Hr Hw Hx Ih Ii Ij Ik Im Io Ip Iq Ir Is Iu Jg Jj Jk Jn Jq Jt Lh Li Lj Lu Lw Ly Lz Ma Mc Md Me Mg Mi Mm Mv Mw My Mz Na Nc Nd Ne Ng Nh Ni Nm Nn No Nq Nr Ns Nt Nu Nv Nw Nx Ny Og Oh Ok Om On Oy Oz Pa Pb Pc Pd Pe Pf Pg Po Pz Qc Qd Qe) bS(Aa Ad Af Aj Al An Ao Ar As Aw Ax BB Bc Bg Bn Bo bR Ch Co Cq Cs Ct Cu Cv Cw Cx Db Dc DD De Di Dk Dw Em Et Ew Fp Fr Fw Hq Hr Hu Hv Hx Ih Ij Ik Il Im Io Iq Ir It Iu Iv Jg Jh Ji Jj Jk Jl Jn Jo Jq Jr Js Jt Lh Lj Lu Lv Ly Lz Ma Mc Md Mg Mi Mk Ml Mn Mp Mr Ms Mt Mu Mv Mw Mx My Mz Na Nb Nd Ne Ng Ni Nk Nl Nm Nn No Nq Nr Ns Nt Nu Nv Nw Nx Ny Oe Of Og Oh Oi Ok Om On Oz Pa Pb Pc Pd Pf Pg Po Qa Qe) Lv(aC aD aE aF aG aN Ao aP AR aS aU aV aW Ax aY Bc bF bL bM bR bW bZ cB cD cF cG cH cO CS cU Cv cW cX cZ Dc dD dE dF Dg dH dI Dl dM dN dW dX fP fR Gd Gl Gp Hq Hw Hx Ii Ij Il Ip It Jh Ji Jm Jn Jq Jr Jt Lh Lu Ma Mf Mh Ml Mn Mq Mt Mv Nd Nf Nh Nj Nl No Nw Oh Oi Oy Pb Pc Pd Po Qc) Bo(aC aD AF aG aH Aj Al An AO Aw aY bB bC bG Bn bW cA cB cD cG Ch cL cU cV CX dC dD Di dJ dN dW dX eM eW Fp fR Gd Hr Hw Hx Jg Li Lj Ml Mn Mr Mx No Ns Nx Oi Ok Pe Pg Po Qb Qc) bB(aC aE AF aG aH Aj aN AO Ap aW Ax aY BA Bb bE Bg bH bI bN bX cB cC cD cE Ch cI cN Cs cW Cx dC dD dJ dK Dl Em fR Gd Hx Ik Il Io Jh Li Lj Ml Ms Nd Nu Of Oh Po) cB(aD aF aL An AR aY bC bF Bg bM BN bQ bR bV bX bZ cA cD Ch cJ cO CP cT CU Cv cW cX dC dD De dI dK dN Ew Hu Hx Jj Jn Lz Mh Mn Mu Nr Of Oh Pc) Mn(aD aG Aj Al aR As aY Bb bE bM cD cE cL Cp Cs cV cW cX cZ Db DC dG dN Hq Hv Il It Iv Jm Jp Jr Li Lj Mf Mh Mk Ms Ne Nf Nj Nk Nn No Nw Of Oh) aC(aD aH An AS aX aY bA bC bM bN bO bV bZ cP cR cW Cx dF Dg dN eM Et Ew Hr Ik In Ji Jj Jt Lh Lw Mk Mm Ms Mt Mz Nd Nf Nm Nw Oh Ok Pa Po) cX(Aa aD aI Aj Al AN Ax aY Bb Bc bM bR Cq Cu CW dB DC Dd Di Dk Dl Et Gl Hq Ii Ij Iv Jr Jt Mf Mp Nj Nw Nx Of Om Qb Qc Qe) Ji(aF Aj Ao Ap Ax aY bA Bg bM bN bO cH cI cK cN Cs cW dC Dg dN eP Fp Fw Gd In Io Iq Ir Jg Mk Ml Mz Ng Nj Nu Of Po) Po(Af AJ As aY bA bE Bn bO bQ Cx dC dW Ef eM FR Gd Hu Ih Jg Jj Jk Mk Mu Mv Mw Ng Nh Nj Oe Oi Ok Pz) Oh(aA aD aF Aj Ao aW bE bR bW bX dD Dg Dl dW dX Ef FR Ii Jg Jh Jk Jo Ml Mu Mw Nb Nj Nx Oe Of Oy Pz Qa) Nw(aF Aj Ap Ar aY bX Cp cS dC Dg Dl dW Ef Fr Fw Hu Ih Ii Io Jg Jh Jt Mk Ml Mu Ng Of Oi Pz) Of(aA AF Al BC Bg Bn bO cD Ch Co CV CW De dX Iv Jm Jr Lw Mm Mu My Ng Nj Nx) aD(Af aI Ax aY bE cG Cq Cx De Gp Hu Ij Il Iv Jm Js Lj Mh Mk Mp Mx Nj Ok Pe) Mu(aF An aO aQ Ax bF bM bR bZ cL cO dH Et Hq Hx Jj Jn Jp Jr Nk No Qa Qe) Ml(Aa Ar bE bQ bR cG cI cO Dc Em Gl Hw Ij Im Jp Jt Nm Nx On Qc Qe) Af(aF aN aO aW bF bR bW bZ cL cO dB dC dH Gp Hq Il Jq Nj Qe) dC(aH aI AS aY bH bI cG Cx dD Jm Jr Mp Mr Mw Nj Nx Ok) Qe(bO Cq Cx Dk Fr Fw Ik Ip Jh Jj Jk Mw Ng Nj Oe Oi) Aj(Ad aF bM Co cW Hq Is Iv Jr Lh Mz Nj Nn Qc) aY(aX aZ bE bR cR cZ Dc Et Gl Gp Il Jp Pb) aF(aI bR dD Et Gp Iv Jj Jk Mk Mp Nj Oe) Il(aI bM bP cP dW Ef eM Hx Ly Mk Pb) Jp(aO aW bR cS Hu Mh Mv Nb Ne Nh Nx) bR(Bn cA cV Cx dD De dX eW Ns Nx) Bb(Al Dd Gl Gp Ii Jm Jq Jt Nj) bE(bM cP cW Cx Hx Jn Mk Nr Pa) Mv(Cu Iv Jn Jr Lh No Nv Qa) Nj(An Bg bM Cx dD Hx Mh Oy) Lj(aX bC bM cW Mm Mp Nx Pa) Gp(An Ao Bg dN Ef eM Iu) Hu(bM Em Hx Jn Nk Nn No) cW(Ch Cx cZ dD Mh Oi Oy) Jr(aO cS In Nb Nh Nv) Fr(Hx Lh Nn No Qb) Mk(aV bC Dc Gl Jm) Iv(Ct eM In Ng Oi) bM(Cx Gd Mh Oi Oy) Mp(Ar Ax bN Cs) Cx(aN dB Jq) Hx(fR Fw Mf) Jj(bN dX Ip) Li(bQ eM Lw) Nx(dD Mh Oy) Oi(Lh Nn Qb) cZ(Ar Ax cP) Cs(Nm Ok) Ef(Gl On) Et(Ao bN) Gd(Cw Ih) Jm(bZ Jo) dD(bZ cL) dF(aO cS) dL(aJ fR) BgPd DcJo EmMh GlIn NnNv MwJn MzaW HqcA PzOk QbbC LhdW aIbN aPfR} Th{yJ(aA AD aH aL An aO aQ Ar As aV Ax BB BN bV cE cG cH cJ cO Cp Cq cR Ct cU CV cZ dA Dc dF dG dJ Dl dM Dp eC Ed Fa Fb Fn Fr Fw Fy Gl hC hG hL HV Hw Hx IB Id Ii Il In iP Ir Is It Iv iZ Jd jE JH Jn JO Jp Jq Jr Js Jy Kg Kj Kp kQ KR Kz Ld Lv Lw Ly Md Me Mf Mi Mj Ml Mn Mq Mr Ms Mt Mv Mw Mx Na Nb Nc Ne Nf Nj Nn No Nv Nw Nx Ny oE OF Oh OK Om oN Pa Pf Ph Pi Pk Qc Qd Qe qH Qn Qv QX Qy qZ Ra Rb Rj rN rV rX sK sO Sr Tn To Tt tU Tv tX Ub Ud uG Um uN Uo Up uR Us UT uU Uv uX uY uZ vH Vp Vs vT Vv wG wH wP wQ zI tL Ti) wF(Ad aF aG aH aI aN aO Ap aY bB bF bZ cF cG Ch Co cQ Cx dA DG dH DL dN eC Ef eT Ez HR iA Ic Id Ii iO iP Iq Is Iz jE Jg Ji Jl jR Jt Jy Kf Kj Kl Kp lL Ly Ma Mj Mk Mm Mn Mv Mz Nb Nd Ne Nh Nl Nm No Nr Of Oh Oi oN Pf Pk Po Pz qB qH Qu Qv Qy Qz Ra Rf rT rW sK sO Sr tO TR TT Tv Ub Ue Ug UL uM uO Ut Uv uW vH vI VO VS VV vW wG wJ Ti) zA(aA aC aE Af aJ aM aO aW bB bC bI Bn bV bW bZ cI cJ cU cX

Figure 39 Continued iB(cC Ch Ed Gd Iz Jv Qh Ql Rc) Nk(fA fB gC gZ kG oT pH pK) aM(jF jG jK jM jO jT lL lO) lN(Ed Gd Pf Qg Ql Rh Rv Tz) jH(aG cC Ed Gd
Ou Po Rv) bB(dU mE mI nK nL pI) hC(dU eQ jB oV oW Zq) jL(aE Bn Ed Gd Rh Wh) jR(Gd Ld Lx Oi Or Rv) gW(Ed Ky Ou Vj Zx) jF(Ed Fw
Ql Rh Rv) jK(aP Or Ou Po Wh) bG(jB oD oE oT) lL(Ed Fw Ni Po) Oy(kG mT nK) jB(bH mW Up) jG(Fw Ou Po) Mx(oT oV) nK(Og Vb)
jO(Ou Po) oP(hB Ld) EdjT GdlO ZxoV LjcX VtjM cRmW eQnH} iB{Qz(Dr Gb Gd Gh Gn Ho Hp Lp Lt Ps Rt Ru Rv Rx Rz Sf Si Sj Uw Ux
Uy Uz Va Vb Vw Vz Wb Wc Wd We Wf Wg Wh Yg Yh Yi Yj Yl Zx Tm Xa) Hp(aE Af aY bF Bn cB cC Cx De dI dJ Dl Dr Ez jF Jj Jv Kc lM
Mj Mk Mx Mz Nd Nt Oe Oh Oz Pc Ph Ql Qm Rh Tz Ug Va Vz) Sf(bQ bS bX cF Cp Cv DB Dc Dd dE Il Iq jF jM Mf Nd Nh Nm Pb Pj Uv Va
Vq) Lp(Af aM aY Db De Dr jF Jj lM Mj Nd Nh Nt Ql Rh Ug) Wh(aE cC dB dJ Fa Ho Kc Ke Kj Pj Ug Uh Un Vh Vq) Vc(bC cE dF Dk Hx In jF
jO Mu Mw Pb Rf Rm Yg) Gd(aE BC Cs Fp Hu Nd Pj Ua Uh Up Vt) Wc(aG aN BC cC cD Jj Ph Pk Ql Sr Vq) Uw(aW Cp Fa Hu Jd Jh Mu Ny
Oi Qt Qw Ua) Ux(Aj Ax Bg Co Dg Jd Ks Om Oy Qw Rc Tn) Vz(bG bS cN DB dE Ou Rc Sr Uh Up) Zx(Ch Fa Jd Jv lN Mh Nq Oz Qt Qw Rj)
Yg(Bc Bn cP cX dI Kc Nf Pj Uh Vt) Ho(Bg In Iz Jj Ks Oz Ph Qw We) Mj(Em Gb Gh Op Ps Rx Si Vj) Pj(kC kO nC nD nH nJ nL Si) aR(kC kO
nC nD nH nJ nL nN) Mx(Em Gb Gh Op Ps Si Vj) Fd(Ax Ii In Mw Nd Oz) Wf(Af aM Bn Cx Ph Rh) Qw(Fc Fi Hl Uy Vj Vw) Ps(aE aM Db Ez
Nd Ql) Ry(cC Fn Ii Nh Oz Vq) Lt(dJ Fa Nd Nh Oi Oz) Va(Ik Jj Og Rc Rf Rm) Yd(bH Ef Ks Mv) Sj(cC Nd Nh Ph) Zw(aE bF dB Kz) Wd(aE
dB Fa Hl) We(bS dB Kz Uc) Rx(Bc Db Fp Pc) Mh(Rv Uy Vw) Zq(Ib Oi Rc) Uh(Op Vh Vi) bS(Ru Si Yl) Dr(In Rm) Em(Nn Pb) Fc(Jj Mw)
Nd(Uy Vb) Ng(Tk Wn) Wb(Af cC) Rv(Fa Oz) Rt(Nh Oz) Vw(Jd Rc) aS(kC nT) bR(nT nU) fR(Jp Oi) AjkF EzRz FiJj GbVt HlIn YhaE XaPb
TmPh JvOp KimW YldB OmVi OwVj VbcC UyjF VhVq dMoP} Vb{dU(An aW bB Bc bG bH bI bL cH cK Cq Ct Cu Dd Ez Fd Fi Fw Fy Gp
HC Hw Hx Id Ij Il Im In Ip Is It Js Jt Kf Kg kP Kq Ks Ld Li Lt Ma Me Mf Mg Mv MW Mx Na nK nO Nv Ok On Ow Oz Ph Pi Qa Qc Qh Qu
Qz Rz Tn Tz Uf Uk Vq Vv Vw We Wf Yh) nK(aH aI aL An AO bI cG cI Cu Cv Dc Dd Dr Ex Gp Id iJ Il iP Jg Jn Jo kI Ko Ks lY Mb Me Mg
mH Mn Mq Ne nJ Nk Nx Og oH Ok On Op oV Oz Qw Rf Rj Rt Sr To Up Us Va) Ao(eQ fA fB gC gZ kE kF kG kI kK kO kP lW lX lY mE mF
mH mI mS mU mW mY nA nB nD nF nI nJ nM nN nO nR nT oD oO oP oQ oT oV oW pH pI pK) jB(An aS aW bG bH bI Ex Hq Hw Hx Il Kq
Ks Mx NA Ne Ng Nk nO Of Ok Oz Ph Pi Qw Qz To Tv Uk Up Ut) mW(aZ Ba Bc cR Cu Db Dd Dg eC iJ iO Iz Jn Jp Kq Ks Li Mg Ng Nk Ok
Rz Uf Yk) kG(aS bI Cv Dc Dd Hq Hw Il Jo Mg Ne Ng Nk To Up Ux Va Vq) nO(aE Cu Dc Dd Gp iJ iO Jp Ma Mf Ng Nk oV pI Uf Ut) fA(bI
cG Cu Cw Dc Ng Nk Ph Qz Rz Ut) Jo(kI lY mS mU mZ nB nJ oQ oV) iJ(kC lX mE mH mI mZ nA nB oW) Ok(kI mE mI mS mZ nB nR oV)
Cu(gC mE mU mZ oP oV) eQ(Ks Mn On Ph Pi Tn) Nd(iC jL jR jY lK) bI(gZ mE oT oW pH) nA(iP Mg Op oV Uf) Ut(mU oO oP pK) Dd(kC
kN nN) Me(gZ oW pH) Mg(kI mE mF) Il(mS nH nL) Uf(mE mU nH) aW(lY nD oV) Fw(gZ mU) Ma(mU mZ) Mx(oT pI) Vq(kF lY) jF(aH Ql)
lM(In Vt) oW(Mb Wb) oV(bH Uk) oD(cR Kq) pH(Jn Nk) GpmZ MneM RzfB OpnN OilK OnmE VvoP VwkI aGjT bSjI cGnR gZnL}
rZ{lX(aC aD aE aF aG aI aK aM aN aO aP aQ aU aV aW aX aY aZ bA bB bF bH bI bM bQ bS bV bW cA cE cH cJ cQ cT cY cZ dC dD dE dF
dG dJ dL dM dN) mT(aG aJ aP aR aX bH bI bN bO bS bW bZ cA cD cJ cK cL cO cR cX cY cZ dA dF dH dI) mH(aE aM aP aX bC bI bL bO
bP bV cB cD cI cL cR cV cZ dC dD dF dK dL dM dN) aR(kE kG kI kO kP lW mF mI mP mS mU mW mY nB nF nH nI nK nM nN nO oP)
cY(kF kG kK kO kP lY mE mF mI mS mW mY mZ nC nH nI nJ nK nO oP oQ) aQ(kC kE kF kK kN lW mM mS nB nC nF nH nL nM nN nR
oO) aK(kE kF kK kN kP lW lY mM mP nC nD nL nM nO nR oO) bQ(kE kI kK kN kO kP mI mM mY nB nD nF nM nN nO nR) cV(kE kF kI
kK kN kO kP lY mF mM mP nB nI nJ oO) nJ(aF aV bA bG bV bW cE cI cJ cP cQ cT dG dH) nO(aD aH aI aN aV aX aZ bF bR cQ cR dD dI)
oP(aC aF aG aS aU aV bB bG bP bZ cF cI dC) bV(kC kE kG kP mM mW mY nB nD nH nI oQ) mS(aE aF aO aP aU bA bE bN cQ cT dN)
mW(aP aU aV bA bO cK cP cT cW dE dN) bJ(kE kN lW lY mP nD nF nH nM) mY(aD aO aU aV aZ bA bL cQ dC) nI(aH aU aZ bX cJ cQ cT
dH) cP(kE kK kP nB nH nN oO) mU(Aa aO bI bO bP bS cA) aU(kI kO lY mF mI nC) aZ(lY mE mF mI oO) mI(aC aL bF cQ) nK(aE aP aV
bX) aS(kN nB oO) lY(bL bO bW) mF(cQ cT dH) nD(aP aV cD) aC(mP nR) bE(kF oO) nT(aO dN) kK(aP bF) ExsM MzUm aDkG cFnF
cQmP} Zx{lN(aE Af aM An Ar aS aV AX aY BA BC bF Bg bH bI BN bO bW cA cC cD cL cN Co cP cQ Cs Ct cX cZ DB dJ dK dN Ef Ex Ez
Fp Fy Gd Gp Hl Hp Hu Hv Hx Ib iC Id Ih Ik Im Iq It Iu Iz Je Jf Jj Jn Jp Ju Jv Kl Kn Ks Kz Lh Li Lu Ma Me Ms Mu My Mz Nd Ne Nf No Nr
Nw Ny Oe Og Oi Ow Oz Pa Pj Qc Ql Qt Qw Qz Rg Rj Ry Sf Si Sr St To Ua Ub Uk Ux Vc Vz Wc Yg Yi Yk Zq Tm Yf) jF(Af aS aV BA bI bL
BN bO cA Ct cW dN eD Fn Hx iC Id Ik Io Jm Ju Jv Mz Nq Og Po Qb Sf Uk Vu Yk) eD(aL An bI cR Gp Hl Hp Kp Kr Kz lM Ma Mj Mk Mm
Mx Nf Oh Oi Qh Rj Vz) oV(aW bB bL bX Cq Dd Fw Jn Jo Li mM mZ nA nK nL Ph Qu To) lK(aE Af Ap aW bS dJ Dr Nq Oz Pk Qt Qz Rc St
Wc) jH(aG Ib Im Jv Mh Mv Oh Ow Oz Qa Rj Rm St Wc) Jn(dU eQ fA gZ jB mW oD oT oW pH pI pK) iC(aC aG aW cI Jv Kz Nf Pk Rj Rm
Vq Wc) Rj(gW jG jI jK jO jQ jR jY lL lO) oD(aW bB bJ cR Dd eC Li Pi Po Ut) Oz(jG jK jM jO jQ jR jT lM lO) gW(bS cX Dp Hp Nd Nq Oi
Qt Rm) bB(dU fA fB lY mE nK nR pI) jI(bO bS Cx dM Ju Jv Sf) jM(bO Jj Jm Ju Oh Wc Yg) lO(Db Gd Hx Ij Oh Ph Rm) dU(bH hC Hq kQ Mx
Ut) jT(aG It Jv Qb Qw) eQ(bL Ho Mn Ph) jL(Af Jv Qt Qw) jY(bO dL Qt Qw) Rm(jG jO jQ) lM(bW cQ dF) Mx(oT pI) Jv(jQ jR) eC(oT pK)
fA(cI Ip) DbjQ FwmU QblL LhmM bOjG cRmW} Ut{Eq(dU eQ fA gZ jB kC kE kF kG kI kK kN kO kP lW lX lY mE mF mH mI mM mP mS
mT mU mW mY mZ nA nB nC nD nF nH nI nJ nK nL nM nN nR nT nU oD oP oQ oT oV pH pI) dU(aW Bg bH Bo bX Co dE eC Gl Gp hG
Hp Jj Jv Kn Ms mW Nh Ni Nk Ny Of Og Oi Po Qz Ry Rz Si To Ua Uu Uv Uw Uy Vi Vj Vs Wd Wf Wh Yd Yi Xa) Jj(eQ gC jB kI kK kN kP
lW lY mE mF mH mM mW mY nD nL nO nT oD oO oP oQ oT oV oW pK) Yg(gC jB kG kI kO kP lX lY mF mS mU mW nA nB nC nD nK
nN nO oO oP oQ oT) oP(cF Dp eC hC iJ In Jh Jo Ju Nh Of Og Om Qv Ug Ur Vi We Yj Yk Tj) eC(jB kC kF kO lY mS nC nH nJ nL nN nO nT
oT oW pH pI pK) Yk(fA gC jB kG kN lX mF mU mW nA nD oO oQ pH pI pK) mU(Fc Gn Hp Lp Rx Sf Va Vw Wc Wd We Wf Yd Yl Xa)
Vs(eQ fA gC gZ jB nN nO oD oT oV oW pH pI pK) nO(Aj Ct Dp Hp Jh Nh Oi Oy Rx Ug Ur Uw) Ib(eQ fA gC gZ jB lX lY oD oV pH) Yd(eQ
fA gC jB oO oQ oT oV pH pI) We(eQ jB lY mF mW oD oQ oV pK) Vi(jB lX lY nA oO oQ oV pI) oD(Hq Jk Pg Sj Uv Uw Wd Wh) nN(Ef Jh
Nh Og Oy Ur) oV(bH Ua Uu Uv Uw Wd) eQ(cR nW Qw Uu Wd) fB(Nc Ni Nk Nl Uv) oO(Jh Ms Og Oi Om) pK(Bg Kn mM Nh Og) Hp(kG lY
mZ nD) Ur(mM nD nJ nT) oQ(hC Jh Og Om) Ef(lX nD nT) lY(Oi Ua Wh) Wd(mF mZ) Qw(gC lX) Uv(fA oT) jB(dM Rz) CpoT JhfA WhjF
RymY UgnT UupI cRoW nJhC} lM{Lp(aM Ba BC Bn cQ Cs Cv Dd De DL Ex Fd Fw Hr Hv Iq Iv Jn Jq Jr Jt Ke Kf Kn Kp Kr Lh Li Mb Md
Mq Mr Mt Mz Nk Nm Nt Of On Pa Pk Po Qa Rb Rt Ry Un Uw Vi Vq Vs Vt Vu Vv Wc Yh Yi Zq) Hp(Af aM bC cP cQ Cw dG Dl Fd Ho Jd Jh
jI Jl Jt Ke Kf Lh Mz Nd Nm On Po Sr Tn Uw Vt Yg Zq) Zq(bC bS Di Ef Ez Fa Hu Im Jd Je Mv Nn Oa Oz Qn Qw Qy Qz Rm Ua Vp) Uw(aG
bC bS Dk Hu Hx Ib Im In It Mu Mw Ps Qn Qw Qy Ua Ur Vp Vt) Sf(aG bB bS cI Cw dB Dd Kc Nd Nk Pb Pj Vq Vt) Vt(Fd Gh Ps Si Vh Vz Wb
Wd We Wf Yg Yi Yl) dF(Fd Gn mT oO Ps Ry Uy Vc Vi Wb Wd Wf Zw) Yg(cP cQ Ct Dg Ii Jg Nf Pc Qu Rz Vs) Pb(Dr Em Fc Fi Lt Ru Uz Vc
Wg Yj Yk) bC(Fd Gd Ho Op Rx Rz Vi Vw Wh Yd Xa) Pj(kF kO mP mS nA nD nH nJ nL) aG(Fc Fd Fi Rv Ry Uy Wc Yi Yj) Ct(Lt Rt Wd We
Wh Yh Yi) Yj(Dp Io It Nh Ni Oz Yd) Uy(aY Bo bP cB Cq Rj Vq) cQ(Fd Lt Op Rt Ry Wh Yl) Bc(Gd Rx Ry Wb Wc We) In(Fd Hl Ho Rt Ry
Vi) Yd(BA bI bJ Md Mp) bZ(mT mU mY nN nT oO) Gp(Fc Fi Rt Wc Yf) Wh(Fy Ke Kp Ok Uc) Ps(aE Lh On Sr Vq) Ba(Rx Yh Yi) Hl(aE It
Rj) Yk(Kc Nf Vq) Ke(tO tR zG) Rv(Kz Nf Qb) Ux(Qt Rc Ua) Vw(Hu Oi Ua) oQ(aR aZ cI) Cu(Ry Vz) Fd(Ii Nd) It(Ho Vi) Sj(Jj Nd) Zw(Ii Ok)
Wd(Fy Uc) Lh(nN Wc) fR(hR Jp) MzUm RcXa SrWf WeKp JjVa RyVq YlOz OrlY VhPh aDnN aSnT bQkC sJpF} Yg{kG(An bI bQ cG Cq
Cu Dc dF Fw Fy hC Hq Hw Ih Il Im Is Jl Jp Jq Jr Js Kq Lh Lx mE Mn mW Mx nB Ng nK No Nv Nx Ny oD Ok Om On Op Oz Pi Qa Qh Sj Tn
Tz Uf) Jp(eF eM hC iA iJ jH kC kE kF kI kK kN kO kP lL lX lY mE mF mI mM mP mS mU mW mY mZ nA nB nC nF nH nI nJ nK nL nM nN

YdnJ} Vq{iA(tQ wE) NqtN TtuO aXwE bCsK rWpF} aC{Pj(bM Jv Of) Pk(bM Jv) AjNm BbbM} nO{Nk(Hl Lp Ug) DrdD GnRg IqUg UuaL}
IY{aW(Gn Lp) DdDu IjRy bJqV bVhR} Nt{Of(Im Nw On Qd) ImOg} Wd{Uf(mM nR) cG(mZ nR) LdmZ} Qm{uM(Id Vv) NgwD JkuP tRuN} Vi{On(gP nB) KqnB LhnL NvoO} hR{fR(bW cG) kC(bV cV) AanJ} qV{Gd(Cv Ir Kn) cU(kO oQ)} uI{Id(Qw rR) IbIm dMpF iPyJ} Ip{tR(aN iP) UrsK iAvS} Jv{wQ(Cs Oa) QdqQ aNrR} Mn{eM(Aj Vh Yd)} Kr{wJ(aF dD) DkrQ} aW{nH(Rv Yf) LpkI} uM{Ly(Id Un) JkUn} Aa{Mh(tN tV)} Dl{Ng(sK tR)} Du{DdnJ NdUp} Nj{ImOg OfOn} Yj{QaoQ QwmE} Ry{LikI OmN} Rt{mZ(Ur Uu)} Op{RgnH UunA} bG{oE(Ho Tm)} cG{nR(Rv Wh)} wQ{QduT QecT} BaaFuO GnQaoQ NoYiiJ NuImOg RbJkrQ SrKztR OuiAyL UsaLnT

Unconstrained panels with 2 analytes, where 1.0E-8 >= 'AUC p-value' > 0. Contains 695 panels of 200,124 total panels evaluated. : Ji(aA aC aN Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Et(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nt(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nu Nv Nw Nx Ny Oe Of Og Oh Oi Ok Om On Oy Oz Pa Pb Pc Pd Pe Pf Pg Po Pz Qa Qb Qc Qd Qe) Ok(aA Fp Fr Hq Hr Hx Ih Ii Ij Ik Il Im In Io Ip Iq Ir Is It Iu Iv Jh Jj Jk Jl Jo Jp Jr Js Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nu Nv Nw Nx Oe Of Og Oh Oi Om Oy Oz Pa Pc Pd Pe Pf Pg Po Pz Qa Qb Qc Qd Qe) Nw(aA aC Eo Fp Ih Ij Ik Il Im Ir Is It Iu Iv Jj Jn Li Lj Lv Lw Lx Mb Me Mf Mh Mr Ms Mt Mu Mx My Mz Nc Ne Ng Nh Ni Nj Nl Nm Nn Nq Nr Ns Nu Oe Of Og On Oy Pb Pc Pe Qa Qb Qd Qe) Nu(aA Fp Im Ir Iv Jj Jl Jn Jp Jr Lv Lx Mh Mn Ms Mx Mz Nj Nn No Nv Nx Og Oh On Pe Qa Qc Qd Qe) Qd(aA aC Im Iv Jg Jj Jp Mh Ms Mx My Mz Nj Nm Of Og Oy) jD(Gc Lt Op Rv Ry Uw Vh Vi We Wf Yd Ye) bU(dU eQ gZ jB oD oT oW pH pI pK) Gc(hC jF jU jV lL lM Vb) Mb(DW EO EW On) Mz(aC Hr Iv Mn Ms Nj uM) aM(DW EO EW gV) Gz(qZ rB rN rP rQ rV) Jj(Im Jg Jp On Qa Qe) Nj(aA Im Jp On Qe) Dw(cX Lv Lx Mn) Eo(Jr Lv Lx Po) Jp(Fp Im Jr Mx) On(Fp Mh Ms Of) aC(Nm Pj Pk Vt) cM(dU gZ jB oW) jP(Vc Wc Yd Tl) Kx(dX eP gV) eW(Bo cB Lv) Lx(dW eO) Mn(Ew gV) Qe(aA Nm) Kr(sH sI) hA(Vc Tl) wF(Ti Th) jM(sF Sh) kG(Yg Yh) BodW NoIb ImOg YdjE ZxlN QbJg KqOf RvjV VtgV sHuM Unconstrained panels with 2 analytes, where 1.0E-7 >= 'AUC p-value' > 1.0E-8. Contains 334 panels of 200,124 total panels evaluated. : Qd(bM Fp Fr Hq Hr Hw Ij Ik Il Io Ip Ir Is It Iu Jl Jm Jn Jq Js Jt Lh Li Lu Lv Lw Lx Ma Mb Mc Md Mf Mj Mk Ml Mm Mp Mt Mu Mv Mw Na Nc Ne Nf Ng Nh Ni Nk Nl Nn Nq Ns Nv Nx Ny Om On Oz Pb Pe Qc) Nw(aN Fr Hq Hr Hu Hv Hw Hx Ii In Io Ip Iq Jg Jh Jk Jl Jm Jo Jp Jq Jr Js Jt Lh Lu Ly Lz Ma Mc Md Mg Mi Mj Mk Ml Mm Mn Mp Mq Mv Mw Na Nb Nd Nf Nk No Nv Nx Ny Oh Oi Om Oz Pa Pd Pf Pg Po Pz Qc) Nu(Aa Hr Hv Ih Ij Io Ip Is It Jg Jm Jq Js Jt Lh Li Lj Lw Mb Mf Mi My Nb Ny Oe Of Om Oy Pf Pg Qb) Jp(aA aC Iv Iz Jn Js Li Lj Lx Mh Ms My Mz Ng Of Og Oy Qa Qb Qe) Mz(Aj aN Hq Hx Ir Jn Lw Lx Mx Nm Of Pb Qa Qe Um uN) Im(aA aC Fp Iv Jg Mh Mr Ms Mt My Ng Nl Of Oy Qe) Ok(aC Aj Hu Hv Hw Jg Jm Jn Jq Jt Lh Ny On) aC(Bb Et Id Ih Is Jt Jv Kc Li Mt Uh Un) On(Iv Li Lj Mr Mx Ng Nq Og Oy Qb Qe) Nj(Fp Fr Ij Js Li Lx Mr No Nv Qa) Jg(aA Fp Mh Mx Ng Of Og Oy Qa Qe) Mn(dW Lw Lx Md Mi Ms Mx) Jj(Fp Jn Js Li Nv Nx Qb) Mx(Ij Lh Nm Nv Ny Qc) Qe(Aa Eo Lw Ms Nx Og) cM(fA nN pI pK) Aj(Kq Nm Nt) Eo(aD cX Ji) Th(wG yJ zA) Gc(hG oE Vt) aA(Jn Li Qa) aN(bA Li Qc) Fp(Nm Nv) Kq(Ef Iz) Uh(oE Wn) Vb(Cu nK) bU(fA oV) jD(Em Yj) AaMb DwaD GzsM LvdW MsNx IrOg JibM YemZ TleD KelM bBdU sHjM Unconstrained panels with 2 analytes, where 1.0E-6 >= 'AUC p-value' > 1.0E-7. Contains 703 panels of 200,124 total panels evaluated. : Im(aN Fr Hq Hr Hu Ih Ik Il In Iq Ir Is Iu Jh Jk Jl Jm Jn Jq Jr Js Lh Li Lj Lv Lw Lx Mb Mc Md Me Mf Mg Mi Mj Ml Mm Mv Mx Mz Nc Nd Ne Nf Nh Ni Nm Nn No Nq Ns Nv Nx Oh Om On Oz Pa Pb Pd Pe Pf Pg Po Pz Qa Qb Qc) Jp(Ef Fr Hc Hr Hu Ib Ih Ij Ik Il Ip Ir Is It Jg Jh Jk Jl Jq Jv Lh Lv Lw Lz Ma Mb Mc Mf Mg Mi Mk Ml Mm Mp Mq Mr Mt Mu Mv Mw Nb Ne Nh Nl Nm Nn No Nq Nr Nv Nx Ny Oe On Oz Pa Pb Pd Pe Pg Po Qc Sh To Uw Vc Wh) Mz(aA aS bM Fp Hv Hw Ih Ii Ij Il In Io Ip Iq Is It Iu Jg Jj Jl Jm Jr Js Lh Li Lj Lv Ly Lz Mb Mc Md Mf Mi Mj Mk Mt Mu My Na Ne Nf Ni Nl Nn No Ns Nx Ny Oh On Oy Pa Pe Pf Pg Qb Qc rR rU Sr Ur vA yJ) Qe(aC Aj aN Fp Hq Hr Hx Ih Ij Ik Il In Ir Is It Iu Iv Jk Jl Jm Jn Jq Js Jt Lh Li Lj Lu Lv Lx Lz Mb Md Mf Mh Mi Mj Mk Ml Mn Mr Mt Mu Mv Mw Mx My Nc Ne Ng Nh Ni Nk Nl Nn Ns Nv Ny Of Oy Pb Pe Qd) On(aA aC Aj Fr Hq Hr Hx Ih Ij Ik Il Ip Iq Ir Is It Iu Jg Jh Jk Jn Jr Js Lh Lw Me Mg Mj Mk Ml Mt Mu Mv Mw My Nc Ne Nh Ni Nk Nl Nm Nr Ns Nx Ny Oe Oi Om Oz Pb Pc Pz Qa Qc) Nu(aC aN Fr Hq Hu Hw Hx Il In Iq Iu Jh Jk Lu Ly Lz Ma Mc Md Mj Mk Ml Mp Mr Mt Mu Mw Nc Ne Ng Nh Nk Nl Nm Nq Nr Ns Oi Pa Pb Pc Pd Po) Qd(Aj aN Hu Hv Hx Ih Ii In Iq Jh Jk Jo Jr Lj Ly Lz Me Mg Mi Mn Mq Mr Nb Nd No Nr Oe Oh Oi Pa Pc Pd Pf Pg Po Pz Qa Qb) Mn(aN dX EO eP eW Hq Hv Hx Iq Ir Iv Ma Mc Mf Mq Mr Mu No Ns Ny Of Oh Om Pe Pf Pg) aC(aM aN Ar bA bM Cs Cu Ed Fr Fw Gp Hf Kq Lh Lx Mi Mm Nd Ne Nt Or Qc Qm Sr) Nj(Aa Ew Is Jg Jj Jl Lh Mi Mp Mt Mx Nb Nm Nx Ny Og Po Qb Qc) Iv(Aa Fp Fr Ij Jg Jj Lh Li Lx Ms Mx Nm No Nv Nx Of Og Qa) Li(gV Jg Jn Js Lv Lw Mx Ne Ng Nl Nx Ny Of Og Qa Qb) Gc(cC cD hA iB iC jE jK jP kS lK lN Ue Uy Vo) aA(Fp Ih Ij Js Lh Lx Mt Mx Nm Nr Nv Nx Qb) Jg(Aj Jr Js Lj Mg Mr Ms My Po Pz Qc) Nx(Fp Ir Lj Lx Mh Mr Mx Of Og Qa Qb) aN(Bb bO cT dD Di dK Lj Lx Nt Ok Uh) Jj(Aa Fr Ij Ir Is Jt Lh Lx Ny) Fp(Ij Jn Js Jt Lw Mm Og Qa) Aa(Is Ji Me Nb Ne Nt Qa) Mx(Io Ir Jn Js Jt Mm uM) Nv(Lj Mb Mh Mr Of Og Oy) Ji(Aj dE dX uM wJ wQ) jD(Fc Rx Si Ux Vc Zq) Lx(Hx Io Jn Of Oy) Hr(Ir Lh No Pe) Qa(Ms Nm Og Oy) Ye(Hv kG nA nK) Ok(Pb Uw Vb We) Ut(dU nN nO oP) bM(bA Nw Pk Uh) Aj(Cu Et Jt) Bo(Dw EO) Nd(Du Sf Sh) Ij(Mb Ms Og) Js(Mb Ms Of) Lh(Nm No Of) Ny(Lj Mh Of) aL(mI nN oW) hC(nI Ry Zq) jP(Em Rz Sh) Gz(tV uX) Hv(Vh Xa) Yk(gC kG) Kq(Jh oP) Uh(Cs fP) Vb(Jr Jt) bU(fB nN) cM(oT pH) eO(cB Lv) nO(Ug Um) iB(SH) TirT ExsM NmQb TzrB YidX ZxjU WchA NwgV UueQ VcjO Unconstrained panels with 2 analytes, where 1.0E-5 >= 'AUC p-value' > 1.0E-6. Contains 1,279 panels of 200,124 total panels evaluated. : aC(aA Ad Af AJ An Ao Ap aS AX aZ Ba Bc Bo bV cG Cp cT cU Cv Cw Dc Dd De dF Dg Di Dk Dl dM Fa Fb Fn Fp Fy Gl Ha Hb Hv Ij Io Iv Iz Jd Jg Jj Js Ju Kc Kd Kf Kg Ki Kk Kn Ko Kp Kx Kz Lj Lu Ly Mg Mn Mp Mq Mr Mu Mw Mx Nb Nc Nf Nh Ni Nk Nl Nn No Nq Nr Ns Nv Nx Ny Oa Of Og Oi Ow Oz Pa Pd Po Qa Qu St Ub Uf Up Ur Us Vq Wm Tj) Li(Aj Fp Fr Hq Hr Hu Hx Ih Ij Ik In Ip Iq Ir Is Iu Jh Jk Jl Jq Jr Jt Lh Lj Lu Lx Ly Lz Ma Mb Mc Md Mf Mg Mh Mi Mj Mk Ml Mm Mn Mp Mr Ms Mt Mu Mv Mw My Na Nc Nd Nf Nh Ni Nk Nm Nn No Nq Nr Ns Nv Oe Oh Oi Om Oy Pa Pb Pd Pe Pf Pg Pz Qc) Jg(Hr Hu Hw Hx Ih Ij Ik Ip Ir Is It Iu Jh Jk Jl Jm Jn Jo Jq Lh Lu Lv Lw Lx Ly Lz Mb Mc Md Me Mf Mi Mj Mk Ml Mn Mp Mq Mt Mu Mv Mw Nb Nc Nd Ne Nh Ni Nl Nm Nn No Nq Nr Ns Nv Nx Ny Oe Oi Om Pa Pb Pc Pd Pe Pf Pg) Mz(bE bS cC cK Cs dE Ed Ef Hc hP Hu Ik Iz jD Jt Ma Mh Ml Mm Mq Mr Mv Mw Nb Nc Ng Nh Nk Nq Nr Nv OE Og Oi Om Pc Pd Po Pz

Figure 39 Continued

QU Qv Qw Qx Rc Rg Ri Rj Ss St To TR tT Ua Uc Uh Uu Uv wJ Wm) aN(aA aD Aj aL aM Ao Ar aS aU aW Ax Ba bE bJ bM bQ bR bV cC cG cI cM Cs Cu cZ Dd dE Et Gl Hr Ij Io Ir Is Jn Jp Js Jt Jv Kq Lz Mi Mt Mx Nb Nd Ne Nm No Nx Og Oi On Or Oy Pe Qa wE) Jp(Aa Aj bM Cs dE Eq Hp Hq Hv Hw Hx Ic Ii In Io Iq Iu Jd Jm Jo Jt Ki Kl Lu Ly Mc Md Mj Mn Na Nc Nd Nf Ni Nk Ns Oh Oi Om Or Ow Pc Pf Pz Qu Qz Rc Sf Uh Um Uu Vb Vt Vw Yd Zx) Qa(bM Fr Hq Hr Hu Hw Hx Ik Ip Iq Ir Is It Iu Jh Jk Jm Jn Jq Js Jt Lh Lv Lw Lz Mb Mf Mh Mj Mk Ml Mm Mn Mr Mt Mx My Na Nc Ne Nf Ng Nh Ni Nk Nl No Nq Ns Nv Ny Of Om Pb Qe) Qe(bS Fr Hp Hu Hv Hw Ii Io Ip Iq Jh Jo Jr Jv Ly Ma Mc Me Mg Mm Mp Mq Na Nb Nd Nf No Nq Nr Oe Oh Oi Om Oz Pa Pc Pd Pf Pg Po Pz Qb Qc rB Ua Uc Uu Ye Tl) Lx(Aa dX Fp Hq Hr Ih Ij Ip Iq Ir Is It Iu Jh Jr Js Jt Lh Lj Ma Mb Mj Mk Mr Ms Mx My Nc Ne Nh Nl Nm Nn No Ns Nv Ny Oe Og Oh On Pg Qc Ur) On(Hu Hv Hw Ii In Io Jl Jm Jo Jq Jt Lu Lv Ly Lz Ma Mc Md Mf Mi Mm Mn Mp Mq Na Nb Nd Nf Nn No Nv Oh Pa Pd Pe Pf Pg Po Vb) Ij(Fr Ik Im In Ip Iq Ir Is It Jl Jn Lh Lj Lw Md Mh Mi Mm Mn Mr Mt Mu Na Nb Nc Nh Nl Nm Nn No Nv Nx Ny Of Oy) Iv(aA Aj Hr Ik In Ip Ir Jl Jn Jr Js Jt Lj Lv Lw Ma Mf Mh Mi Mm Mr Mt Nh Nj Nk Nn Ny Om Oy Pe Po Qb Qc) Lh(Aj Fp Hq Hw Ih Ik Ir Is Iu Jn Js Lj Lv Lw Ma Mb Mi Mm Mn Mr Ms Mt My Ne Ng Nn Nx Ny Og Oy Qb Qc) Ny(aA Fp Hq Hr Hv Hx Im Io Ir Jh Jn Jr Lv Lw Mc Md Mf Mi Mr Mu Nm Nn No Nx Og Oh Oy Pe Pg Qb Qc) Mn(Aj bS eM Hr Hw Il Im In Io Ip It Jj Jr Lv Ly Lz Me Mh Mk Mt Nh Nj Nm Nn Nx Og Oy Pa Pc Qc) Im(Aa Hv Hw Hx Ii Io Ip It Jo Jt Lu Ly Lz Ma Mk Mp Mq Mu Mw Na Nb Nk Nr Oe Oi Pc) No(aA Aj Eo Hc Ir Iu Jl Jn Js Jv Lw Ms Mx Na Ne Nh Nl Nm Nv Nx Og Pe Pg Qc Qw) Jj(bM Cs Dc Gc Ho Ih Ii Ik Ip Jl Jm Ks Mt Mx Ne Nh Nl Nm Nn Nr Po Pz Uh Tl) Js(Fr Hr In Ir Jl Jt Lj Lv Lw Mf Mh Mm Mr Mt Ne Nf Nh Nm Nv Og Oy Pb Qb Qc) Aa(Et Fp Ih Jr Lv Mh Mp Mr Ms Mt Mx Nh Nl Nw Of Ok Oy Po Qb Qc Qd tV tX) Nv(Hr Ih Ir Is It Jn Lv Ml Ms Mt My Ne Ng Nh Ni Nl Nm Nx Pb Qb Qc) Gc(fP hB jl jR kG nW nY oF Or Qv Sf Ub Uc Ug Un Uu Va Vq Vw) Nj(Ih In Ir Jn Jq Jr Jt Lj Lv Lw Ma Mh Mm Ni Nk Nn Nr Oh Pe) Fp(Hr Ir Is Jl Jq Lv Ma Mf Mi Ms Mt Mx Ne Nh Nl Pz Qb Qc) Nx(Fr Is It Jl Lv Ml Mt Nh Nl Nm Nn Oe Oh Oy Pe Po Qc wQ) aA(Fr Hr Ii Ik Ip Ir Jt Lj Lv Ma Mb Mh Mm Nh Nl Nn Pz Qc) Ji(aS bA bO bV Cs Cw Ef eP eW Jv oE tR Vb wE wF yJ) Aj(Ad BA BC bM Dc Dw Lw Mt Nb Nw Qc) Nu(Ii Ik Me Mg Mm Mq Mv Na Nd Nf Ni Oz Pz) Jn(Fr JI Lj Mh Mr Ms Mt Of Og Oy Qc Vb) Uh(Aw cM gL hC iA Ib Jo Jv Nd Of oN Qv) Nm(Ir Is Jr Lj Mb Mh Mr Ng Og Po) Mx(Fr Ip Is Jr Mb Nn Om Pe Pg Pz) jD(Fd Fi Gh Lp Ru Sh Uy Uz Vj Xa) bM(Bb Cs Ed Is Ke Ok Or Tz Vt) Hv(Du Hp Sh Vw Wb Yi Yl Tl) Of(bA Cs Cu Ir Ke Nn Tz Ut) Gz(jV qU rC rZ uY vW wF) Qb(Eo Fr Jt Lv Ms Mt Og) Jr(bS Mt Rt Sf Va Wh Zw) nO(aL Dp hC Qv Vb Vs Ye) Jt(Mb Mr Ms Nc Ng Og) bB(dW eO EW fB gZ) Cs(Et Jv Og Qd Vt) Ir(Lw Ma Ms Mt Nn) Is(Eo Mb Ms Mt Og) Ut(lX IY rT oE Vb) eO(bR bS cX Oh Po) tT(Dl Kz Qm rB Th) Yc(mW Nb nI nL) Vb(dU Fy iJ mE) aL(IY nL nT pK) Ho(bO eP Hp) Id(lM oE uI) Qc(dD Mp Nn) cM(eQ fB oV) jV(Lp Sh Uw) pF(sH sI sJ) Eo(Hx Oh) Ti(Or rZ) Ew(Bo Lv) Th(Vt wK) Mt(Og Oy) Nd(Eq Uy) To(jB wF) Sf(Dk jP) Qd(aS dE) dD(oT pK) eW(aD Et) gV(Ki Qh) hC(dU jB) sF(Ip Vu) jF(Sh Zx) DuoT EfKe FrOy NnMr MldW HljP IkOg YkmW YjkG KxeM LphA QmuN VtdE PkoE aWrS tXiP sIuM qXuI kFlL

Unconstrained panels with 2 analytes, where 1.0E-4 >= 'AUC p-value' > 1.0E-5. Contains 2,833 panels of 200,124 total panels evaluated. : aC(Aa aF aG Al aO aP aR As aU AW bB bC bF BG bI bJ bL Bn bO bS bW bZ cC cE cF Ch cI cM cN Co Cq cS Ct cV CX DB dD dE dG dH dJ dK dL dN Dp Ef eO Ex Ez Gc Gz Hc Hq Hr Hu Hw Hx Ib Ic Ii iJ Ik Il In Ip Iq Ir It Iu Je Jf Jh Jk Jl Jm Jn Jo Jq Jr Jy Kj Kl Kr Ks Ky Ld Lv Lw Lz Ma Mb Mc Md Me Mf Mh mI Mj Mk Ml mM Ms Mv My Na Ng Nj nL nN nT OE Oh Om Ou Oy Pb Pc Pe Pf Pg Ph Pi Pz Qb Qg Qh Ql Qn Qt Qv Qw Qx Qy Qz Ra Rb Rc Rf Rh Rj Rm Ss Tn To Tr Tt Tv Tz Ua Uc Ud Ue Ug Uk Ul Um Uo Ut Uu Uv Vo Vp Vs Vu) aN(Aa Ad aE AF aG aH aI aJ aK Al An aO AP aQ aR aV Aw aX aY aZ bB bC bF BG bH bI bL BN Bo bP bS bU bW bX bZ cA cB cD cE cF CH cJ cK cL cN CO CP Cq cR cS cU CV CW CX cY dA DB DC De dF DG dH dI dJ Dk DL dN Ed Fa Fp Fr Fw Gc Gp Hu Hv Hx Id Ih Ii Ik Il In Ip Iq It Iu Iv Jg Jj Jk Jm Jo Jq Jr Ke Lh Lu Lv Ma Mb Mc Md Me Mf Mh Mk Ml Mp Mq Mr Ms Mu Mv My Na Nc Nf Ng Nh Ni Nj Nk Nn Nq Nr Ns Nv Ny Oa Oe Of Oh Om Pa Pc Pf Pg Pj Pk Po Pz Qb tT tV Tz Um Up Ur Ut uY Vt yJ) Mz(Aa Ad aE aF aH aJ aK aM AO aP AW Ax aZ bA bF Bg bH bI bJ bL bN bO bP bQ bR bU bV bZ cA cD cE Ch cI cJ cM cN CO Cp cR cS cT cU cV cW cX DB dC dD dF dG dH dJ DK dL dM Dp eP Ez Fn Fr Gz hW Ib Jd Jh JK Jo Jq Jv Ki Kj Kl Kn Ks Lu Me Mg Mp Nd Ou Ow Oz Ph Pi Pj Pk qB Qg Qh qI Qn qQ Qt qW Qy Qz rA RB Rf Rh Rm rN rQ rT rV rY sK sO Tn tO tQ Tt TV tX Tz Ub Ud Ue UG uI Uk UL UO UP uR Us Ut uV uW uY vH vI Vo Vp Vs Vt Vv vW wC wE wK wP wQ zG) Uh(aD Aj aM An Ap Ar bE Bg bV Co Ct dA dL Dp dR Ed EF Fn Fp Fw Fy Gc gP gV Ha Hb Hc Hv Hx Ic Id iH Io Iu IZ JD Jf Ji Ki Kj Kq KR kS Kx Li Lj Lx Mt Mx Nb Nh Nl No Oa oF Og Oh oK Or Ou Ow Oz Pa Pb Pe Pk Po Qe Rc Rg Sr Ss Ua Ub Ue Uk Us Uu Vt Vu wF Wm) Ji(aE AF aG aH aM An AO Ap Ar Aw AX bE Bg bI bJ bL bS cC cD Ch cI cM CO cQ cS CT cU Cv CX DB dD DK dL dM eF eO gV hC Ib iZ jD nY Qv Qx Rc rU sK tO tS tT tU tV Um uN Uu Uw Uy VA Vc wC Wd WG wH wK wL yD zG Wm) Jp(Ap Ar Aw bL bS Dp Ed Ez Fc Fn fR Gz Ha Id Je Jf Ju Ke Kp Kq Kr Kx Ky Oa oE Ou Ph Pi Pj Pk Qm Qt Qv Qw Qx Rf Rg Rh Ri Rj Ry Rz Si Sj Sr Ss Tr Tz Ua Ub Uc Ud Ue Uf Uk Ul Un Uo Ur Ut Uv Ux Uy Vs Vv Vz Wb Wc Wf Wg Yl Zw Ye Tm Tl Xa Wm) Aa(aA bM Fr Hu Ii Ij Ik Il In Io Ip Iq Ir It Iu Jg Jh Jl Jn Jo Js Lh Li Lj Lu Lw Ly Lz Ma Mc Md Mf Mg Mi Mj Mk Ml Mm Mn Mq Mu Mv Mw My Na Nc Nd Nf Ng Ni Nk Nm Nn Nq Nr Ns Nv Nx Ny Oe Og Oh Oi Om On Oz Pa Pb Pc Pd Pf Pg) Js(Aj Hq Hu Hv Hw Hx Ih Ii Ij Ik Il Io Ip Iq Is It Iu jD Jh Jk Jm Jn Jo Jq Jr Lu Ly Lz Ma Mc Md Me Mg Mi Mj Mk Ml Mn Mp Mq Mu Mv Mw My Na Nb Nc Nd Ng Ni Nk Nl Nn Nq Nr Ns Nx Ny Oe Oh Oi Om Pa Pd Pe Pf Pg Po Pz rZ Um) Nv(Aj Cs Fr Hq Hu Hv Hw Hx Ii Ik Il In Io Ip Iq Iu jD Jh Jk Jl Jm Jo Jq Jr Jt Lh Lu Lw Ly Lz Ma Mc Md Me Mf Mg Mi Mj Mk Mm Mn Mp Mq Mu Mv Mw Na Nb Nc Nd Nf Nk Nn Nq Nr Ns Ny Oe Oh Oi Om Oz Pa Pc Pd Pe Pf Pg Po Pz) Fp(Fr Hq Hu Hv Hw Hx Ih Ii Ik Il In Io Ip Iq It Iu Jh Jk Jm Jo Jr Lj Lu Ly Lz Mb Mc Md Me Mg Mh Mj Mk Ml Mn Mp Mq Mr Mu Mv Mw My Na Nb Nc Nd Nf Ng Ni Nk Nn No Nq Nr Ns Oe Of Oh Oi Om Oy Pa Pb Pc Pd Pe Pf Pg Po) Ir(Fr Hq Hv Hw Hx Ih Ii Ik Il In Io Ip Iq Is Iu Jh Jl Jm Jn Jq Jr Jt Lj Lu Lv Ly Mb Mc Md Mf Mh Mi Mk Mm Mp Mq Mr Mu Mw My Na Nb Ne Ng Nh Ni Nl Nq Nr Ns Oh Oi Om Oy Pa Pb Pd Pe Pf Pg Po Qb Qc) Ij(Aj Hq Hr Hu Hv Hw Hx Ih Ii Il Io Iu Jh Jk Jm Jo Jq Jr Jt Lu Lv Ly Lz Ma Mc Me Mf Mg Mj Mk Ml Mp Mq Mv Mw My Nd Ne Nf Ng Ni Nk Nq Nr Ns Oe Oh Oi Om Oz Pa Pb Pc Pd Pe Pf Pg Po Pz Qa Qb Qc) No(bS dE Fr Hq Hv Hw Hx Ic Id Ih Ik Il Io Ip Iq Is It Jj Jm Jq Jr Kd Ki Lj Lu Ly Lz Ma Mb Mc Md Mf Mh Mi Mj Mm Mp Mr Mt Mu Mv Nb Nk Nn Nq Nr Ns oE Of Oh Oi Ow Pa Pc Pd Pf Pk Po Qb Ur Vv) Gc(cB Ed Gd gP gV gW iA iH iO iP iZ jG jH jO jQ jT jY kQ lO Mm mW NB Nh Ni nL oH oK Pz Qb Qe Qh Qt Qz Rc Rg Tr Tz Ua Ud Uf Uk Um Uo Us Ut Uv Uw Ux Vh Vi Vj Vs Vu Vv Wc Wd Wg Wh Th) Lx(Aj aM bJ bM bS dE Fr gV Hu Hv Ib Ii Il Jl Jm Jo Jq Lu Lv Lw Ly Lz Mc Md Mf Mg Mh Mi Ml Mm Mp Mq Mt Mu Mv Mw Na Nb Nf Ng Ni Nk Nq Nr oE Oi Pb Pc Pd Pe Pf Po Pz Qa Qb Qw rB) Cs(Aj aM aS Bb bJ bO cM CU DE Di Fn Fy Hr Ib Iu Iv Jg Jo Jq Jt Ju Lh Li Mi Mk Mn Mt Mx My Nb Nd Nh Nk Nm Nw Oi Ok Om Qa Qc Qe Qw Rf To Uc Um Up Ur Us Ut Uu Vp wF Tl) Lh(dX Fr Hv Hx Ii Il In Io Ip Iq It jD Jm Jo Jq Jr Jt Lu Ly Lz Mc Me Mf Mg Mh Mj Mk Ml Mp Mq Mu Na Nb Nc Nf Nh Ni Nk Nl Nq Nr Ns OE Oh Oi Pa Pb Pc Pd Pf Pg Po Pz wQ) bM(aA aL aS Ax aZ bE bJ bO bV cT CU Dc DD Dr Ef Et Fw Fy Gl Gp Ic Id Im Iv Jd Jg Jq Jv Kd Ki Kq Kz Li Lj Mi Mn Nb Nd Oa Pi Qb Qc Qe Tn To Tv Um Un Uo Ut Vp) Nj(dU Hr Hu Hv Hx Ii Ik Il Io Ip Iq It Iu Jh Jk Jm Lu Ly Lz Mc Md Mf Mg Mj Mk Mq Ms Mu Mv Mw Na Nc Nd Ne Nh Nl Nq Ns Oe Of Om Oy Oz Pa Pb Pc Pd Pf Pg Pz) Qe(aM Ap Ar aS Aw bA Bb bE bI bJ Bn bO cI cM CO Ct cX dD dE Dg Di dK Dl dX EF hG Ib iJ Ki Kl Ow Pk Qu Rc To Ub Ue Ug Um Ur Uv Vb Vo Vs Wb Zw Zx Tm) Ny(Aj Fr Hw Ib Ih Ik Il Ip Is It Iu Jl Jm Jq Jt Lu Lz Ma Mb Mk Ml Mm Mp Mq Ms Mt Mw My Na Nb Ne Nf Ng Nh Ni Nk Nl Nr Ns Oe Oi Om Pa Pb

Figure 39 Continued

Pc Pd Pf Po uN yJ) Qa(Aj dD Hv Ih Ii Il In Io Jl Jo Jr Lj Lu Ly Ma Mc Md Me Mg Mi Mp Mq Mu Mv Mw Nb Nd Nn Nr Oe Oh Oi Oz Pa Pc Pd
Pe Pf Pg Po Pz Qb Qc Qu rB Rm Uc Uu Tl) Aj(aM Ao Ar Bb bV cG cT cU Dd dF dL Fr Fw Fy Gl Ih Ii Im Is Jn Ke Kf Kg Ko Kr Ks Kx Mg Mi
Mm Nd nN nO Nu Nx Ou Pa Pb Pd Pe Pf Po Uc Vt) Iv(bE Hq Hx Ih Ii Il Io It Iu Jh Jm Jq Lu Ly Lz Mb Mc Md Mk Ml Mp Mq Mu Mw My Na
Nb Nc Ne Ng Ni Nl Nq Nr Ns Oe Oh Oi Pa Pb Pd Pf Pg Pz) Mn(aA aH aM Ao Ap bA Bg cC cI Co cQ cT dA Dg fR Ih Ik Is Iu Jh Jl Jm Jn Jq Lj
Lu Mb Mj Ml Mv Nb Ne Ng Ni Nl Nq Nr Oz Pd Po Sh Wm) Nx(Hr Hv Ih Il In Io Ip Iq Iu Jh Jn Jr Jt Lw Lz Ma Mb Mc Md Mf Mi Mj Mq Mu
Mv Mw My Nb Nc Ne Nf Ng Ni Nk Nr Ns Om Pa Pb Pf Pg wJ) Qb(Hq Hr Hu Ih Ik Il Is Iu Jh Jl Jn Jq Lj Lw Ma Mb Md Mf Mh Mi Mk Mm Mr
Mx My Nb Nc Ne Nh Ni Nk Nl Nn Nr Of Oy Pb Po Pz Qc) Hv(Fd Gh Hc Ho Jg Jn Jv Li Lp Nm Qc Ru Rx Ry Sf Si Sj Ux Uz Vb Vc Vi Vj Vt
Vz Wc Wd We Wg Wh Yd Yj Yk Zq Zw Zx Tm) Qc(aM Ar aS bA bE bS cU Fr Ih Ii Ik Is Jj Jl Jt Lj Lv Lw Ma Mh Mi Mm Mr Ms Mt Ne Nh
Nl Nm Og Oh Pa Pe Pg Po) Jj(aA Ax Bb CU Dd Fb Fw Fy Gd Id Io It Jk Jr Kq Kr Kx Lj Lv Ma Mh Mm Mr Ms nN Or Pi Qh Tz Vt Wb Xa)
Lj(aM bA cC cU cX dE dW Fr Ip Is Jl Jq Jt Jv Lv Lw Ma Mh Mm Mp Mr Mt Mx Ne Nh Nl Nn Og Po Pz Rf Wb) Of(aA Ar Bc cT Dd dF Dw
Fa Fb Fr Fy Ha Id Is Jd Jt Ko Kr Kx Mm Mt Nm nN Oa Oh Pj Po Sr Uf Us Vp) Jn(Eo Hp Hr In Ip Is Jh Jr Jt Lv Lw Lz Ma Mb Mf Mm Mu Nb
Ne Nh Ni Nl Nm Nn Nr Oe Pe Pg Po We) Nm(Fr Hr Hu Ih Ik Jl Jq Lv Me Mf Mj Mp Ms Mt My Nb Ne Nh Nl Nn Nr Oh Oy Pe Pg) Jr(aA Em
Fc Fr gV Gz Hp Hr jD Jt Lw Mc Mf Mh Mr Ms Mu Og Oh Pe Pg Sh Wb Wd We) bA(aK aM Ar aU bE bJ bZ cC cD cM Ct dB dE dL Et Mx
My Nb Ni Nt Nu Nw oE Oy Qd) Po(aA bS dW Ih Io Ip Is Jq Jt Li Mm Mt Mx Nh Nl Nn oE Og Oh Om Oy Pe Pg rB) aA(Hu Is It Jl Jm Jq Lw
Me Mf Mi Ml Mr Ms My Nb Nc Ne Nf Ni Og Oh Oi Oy) nN(Ad bE bO cA cF cH Ct dD eC hC IL Mb nI Nk oK qU Rf Rg Ri Rm Ur Uu) Mt(Fr
Ih Io Ip It Jq Jt Lv Mb Mh Mr Ms My Ne Ng Nh Nl Og) jV(Em Gb HL Or Rz sK tX Um Uy Uz Zx Ye) Mm(Ik Jl Jq Lv Mb Me Mh Mr Ms Ne Nl Og)
Ut(eM Jh kG kP mS nD nH nI nJ nL oO Sh Si) nO(bO cF cM Ed Eq Jv Rf Rg Ss Uu Vp Tj) Mr(Ih Ii Io Jq Lv Ma Nh Nl Pe Pg Pz) Kq(Aw Bg Ch
Ct Cw Jo Kl Mg My Qu Uu) dD(dU eQ fB gZ jB oD oV oW pH pI Pk) Nd(Fd Hl Lt Ru Ry Rz Sj Uz Wb Ye) Jt(Hr Ih Jl Jq Lv Mh My Nh Nl)
Og(li Ip Jh Jl Nh Nl Nr Oa Pz) Ok(Co Cw dE eP Gd Hp Uu Vc Wh) Pk(aS cV dE dL iJ kR mW oF oN) bB(eQ jB oD oV oW pH pI pK Sh)
jP(Dr Gz Ho Uw Uy We Wf Zq Zx) Ms(Ih Ik Io Jh Jl Jq Nh Oh) Jv(aS hP Ke Nr Or pY tV wQ) Fy(dX eP Gd Hp Ib Sh Vc) Ke(Aw dX eP Iz Jo
My tO) Vb(Dc hA Ho jB kG mW Vh) Ti(aM nH Qv sK Ue uW) Th(uN uW vT vV wH wL) Gz(qT qY rS rU uG uN) Tl(bO bU cB Ed On Qh)
Nw(aS bE cD dE dX eP) Un(dX Ho Ib tO uM vA) wF(An Bb Pj Qm Ri Uk) kG(Eq Wc Yi Yl Zq Xa) Mb(Jl Jq Ma Mi Mp) Nb(aS Nl Sf Sh Wb)
Pe(Hw Io Lw Lz Oh) cB(Dr DW Eo Ew) tX(dB iA Kz nW rB) sF(cT iB Kr pF uM) sH(cT hW Ip jK vl) Lv(Nh Nl Nr Pz) Mh(dW Ip Jl Nl)
Ye(iB mE nH nU) Or(aS Gp Ho Pj) bO(oP oV Wb Zx) sJ(cT kR uM vl) Ar(aS cT dE) Gd(aM iJ Zq) Id(Iu IN uM) Ik(Jq Lw Mi) Sf(Dc Im Nr)
Sh(Dk jE Nr) eO(aD bE Mu) tT(aW iP rC) qU(kF nA nR) pK(cF dJ eC) Cu(My Wd) Et(Ap Ef) Eq(De Ho) Nu(Jo Wn) Tn(eM eP) Ip(Ma sI)
Yg(cG pH) Kx(eQ oV) Pg(Oh Om) bV(cM My) dE(aM oW) nT(Qv Um) tO(Kr qZ) yJ(iP Qm) jB(cF Qw) rB(Sr Wm) qX(uM zH) qW(cU dM)
oD(cM cR) vI(sI wQ) Cqlb DumW EoMl GllM NkHo TzWb UcUu TopH IhJl Imul YieP YdhA ZxeD WenL WhOn XacD UggV VccG bEml
bHdU dAhP dBtV lYjM rCuN jKuY lLoQ Unconstrained panels with 2 analytes, where 1.0E-3 >= 'AUC p-value' > 1.0E-4. Contains 6,395 panels of 200,124 total panels evaluated. :
Uh(aA Ad aE AF aG aH aI aJ aK AL AO aP aQ aR AS aU aV aW AX aY aZ BA Bb Bc bF bG bH bI bJ bL BN BO bP bQ bR bS bU bX bZ cA
cB cD cE cG CH cI cJ cL cN cO Cp CQ cR cS cT CU CV Cw Cx cY cZ DB DC DD DE dF DG DI dJ DK Dl dM dN eC eP Et Ez Fa Fb Fr Gl
Gp Gz hB HF hG Ho Hq Hr Hu Hw Ih Ii IJ Ik Il Im In iO IP Iq Ir Is It Iv Je Jg Jh jI Jk Jl Jm Jn Jq Jr Js Jt Ju jV Jy Kc Kd Ke Kf Kg Kk Kl Kn
Ko Kp kQ Ks Ky Kz Ld Lh IM Lu Lv Lw Ly Lz Ma Mb Mc Md Me Mf Mg Mh Mi Mj Mk Ml Mm Mn Mp Mq Mr Ms Mu Mv Mw My Na Nc
Ne Nf Ng Ni Nj Nk Nm Nn nO Nq Nr Ns NT Nu Nv NW Nx NY Oe oH Oi Ok Om On Oy Pc Pd PF Pg Ph Pi Pj Pz Qa Qb Qc Qd Qg Qh Ql
Qm Qn Qt Qu Qw Qx Qy Qz Ra Rb Rf Rh Ri Rj Rm sK St Tn TO Tr Tv Tz Uc Ud Uf Ug Ul Um UN Uo Up Ur Ut uY Vo Vp Vs Vv Tk Tj tF)
Cs(aA Ad aE AF aI aK AL An AO AP Ar As aU aV AW AX aZ BA bB BC bE bF Bg bI bL Bn Bo bQ bR bS bV bW bX cA cB cC cD cG Ch cl
cJ cK cL cN CO Cp CQ cR CT CV Cw CX cY cZ dA DB DC DD dF DG dH dI dJ DK DL Dp Ed Ez Fp Fr Gl Ha Hb Hc Hf Hp Hq Hu Hv Hw
Hx Ic Id Ih Ii Ij Ik Il Im In Io Ip Iq Ir Is It Iz Jd Je Jf Jh Jk Jl Jm Jn Jr Js Jy Kc Kd Ke Kg Ki Kk Kl Kn Ko Kp Kq Kr Kz Ld Lj Lu Lv Lx Ly Lz
Ma Mb Mc Md Me Mf Mg Mh Mj Ml Mm Mp Mq Mr Ms Mu Mv MW Na Nc Ne Nf Ng Ni Nj Nl NN No Nq Nr Ns Nt Nu Nx Ny Oa Oe Oh
ON oO Or Ou Ow Oy Oz Pa Pb Pc Pd Pe Pf Ph Pi Pj Pk Po Pz QB Qg Qh Ql Qm Qn Qt Qu Qv Qx Qy Qz Ra Rb Rc Rg Rh Ri Rj Rm sH Sr Ss
St Tn tO Tr Tv Tz Ua Ub Ud Ue Uf Ug UK Ul Un Uo Uv Uy Vo Vs Vu Vv Vw Wb Wn Wm tF) Qe(AD aE AF aG aH aI aJ aK AL An AO aP
aQ aR As aU aV aW AX aY aZ Ba bB BC bE bF BG bH bL bN Bo bP bQ bR bU bV bW bX bZ cA cB cC cD cE cF cG CH cJ cK cL cN CP CQ
cR cS cT CU CV CW Cx cY cZ dA DC Dd De dF DG dH dl dJ Dk dL dM dN Dp dR Du dW eO eP eW Fn fP Fw Fy GL gP gV HC hF iA
Ic Id iH iP Iz Jd Je Jf Ju Ke Kj Kk Ko Kq Kr Kx Ld nW nY oK oN Or Ou Ph Pi Pj Qg Ql Qm Qn Qt Qv QW Qx Rb Rf Rg Rh Ri Rj Rm rZ Sf
Sh Si Ss St Tn Tt Tv Tz Ud Uk Ul Un Up Us Ut Uw Ux Uz VA Vc Vi Vp Vt Vv Vz Wc We wQ Yd Yi YJ Zq Xa Wm Ti) Ji(AD al aJ aK AL aP
aQ aR As aU aV aW aY aZ Ba BB BC bE bF bG bH BN Bo bP bQ bR bU bW bX bZ cA cB cE cF cG cH cJ cK cL cN CP Cq cR Cu cV cW cY cZ
dA DC Dd De dF DG dH Dl dJ DI dN dR Ed eM Ew Ex Fc Fn fP fR Fw Gc Gd gL gP Gz Hc hF Ho hP iA iH iJ iO iP Iz Ju Kj kQ kR kS nW oF
oH oK oN Or Ou Ow pF Pk Ps qB qC Qg qH ql Qt Qu Rf Rg Rm rO rQ rR rT rZ Sf Si sM Sr Ss tN To tQ tX Tz Ua Ub Uc Ud Ue Ug ul Uk uL
Uo uP UR Ut UV UX uY Uz vB vC Vh VI Vo Vp Vs VT vU Vv VW wB Wc wD We Wf Wh wP yL zA zH zI tM Tl Ti tF) Mz(aD Af aI AL An
Ap aQ AR As aU aV aX aY Ba BB BC bO Bn Bo bW bX cB cF cG cH cL cP CQ Ct Cu Cv Cw Cx cY cZ dA Dc Dd De Dg DI Dl dN eC eD eF
eT eZ Fa Fb fN Fw FY Gc GL Gp gW Ha HB hC HF hG hL hO Hp hR hV iA Ic Id iO iP JE JF jO jP jQ jR jT Ju JY Kc Kd Ke Kf Kg Kk Ko Kp
Kq KR kS Kx Ky Kz IK IN nY Oa oH oN Or pS pY qA qC qD qG qH Ql Qm qO qP qT qV qX qY qZ Ra rC rO rP rS rW rX Ry rZ sC sM tN tS
tU Uf Un uU uX uZ VB vC vO vP vQ vS vT VU vV wB wD wF wG wH wL yD yH yK yL zA zH zI yE tL Tj Ti) bM(Ad aK Al aM An Ao Ar
aU Ba Bc bN cC cD cl cM Cq Ct Cv Cw CX cZ DB dC DE dF Di DK dL dM Dp dW Em eW Ez Fa Fb Fd Fn Fp Gc gV gW Ha Hb Hf Ho Hr
Hv Hw Hx Ib Ih Ij Io Ir It Iu Iz Je Jl Jm Jn Jo Jr Js Jt Ju Jy Kc Kf Kg Kk Kl Kn Ko Kp Kr Ks Kx Ky Ld Lh Lv Mh Mp Mt Mx My Ne Nf Ng Nj
Nm No Nt Nu Nv Nx Ny OE Of Og Oi On Ou Ow Oy Pa Pb Pe Pf Ph Pj Po Qg Qh Ql Qm Qn Qu Qv Qx QY QZ Ra Rb Rc Rf Rg Rh Ri Rj Rm
rS rU Sr Ss St Tn Tt Tv Ug Up Us Uz Va Vh Vi Vj Vo Vp Vq Vu Wd We Yg Yh Yk Zq Ti Th Yf) oE(Aa Aj aM aN aO AS aU aY Ba Bb
BO bV bZ cC cD cE Ch cK CO Cp Cq Ct cU Cv Cw CX DB Dc DD De Dg Di dJ DK DL Du dX eC eO eP Ex Fa Fb Fd Fi fP Fw Fy Gb Gc Gd
Gh Gl Gp Hb hC HF Hl Ho iA iH iJ jD Jy Kc Kd Kf Kg Kj Kk Kn Ko kP Ks Kz Ld Lp Lt mS nN nT nY oK oN Op Ps Qg Qh Ql Qn Qy Ra RB
Rm Rt Ru Rv Rx St Tn Tt Tv Ug Up Us Uz Va Vh Vi Vj Vo Vp Vq Vu Wd We Yg Yh Yk Zq Ti Th Yf) oE(Aa Aj aM aN aO AS aU aY Ba Bb

Figure 39 Continued bE bF bO bQ bR bS bU bV cA cB cG Co cP CT cU cV dA dB DC DD dE dI DK Ed Ef Et Fa Fy Gp Gz Ha Hc HF Ho Hr Hv iA Ib Ic Iz Jd Jf Jj Jk Jl Jr Js Jv Kd Kf Kg Ki Kk Kl Ko Kp Kr KS Kx Ky Kz Ld Li Lj Lz Mk Mn Mt Mu Mx My Na Nb Nc Ne nl nO Ns Nu Nv Nw nY Oa Of Og Or Ow Oz Pb Pd Pe Pg Pi QH Qu Qw rC Rf Rg Ry St Tn To Tz Ua Ub Ue Uf ul Uk Un Ur Uu Vp Vq Vs Vu Zq Tl Tj) Aj(Aa aK Al An Ap aS aU aW Ax bE BG bJ bO bW cM Co Cp CQ Ct Cv Cw cX cY dB DD DE Dg Di dJ DK Dl dM Ed Fa Fb Fn Fp Gc Ha Ho Id iJ Il In Io Ip Ir Iz Jd Jh Jj Jk Jl Jo Jq Jr Jv Jy Kc Kd Ki Kj Kn Kp Kz Ld Lj Lv Ly Lz Ma Md Me Mf Mh Mj Mp Mq Mr Ms Mu Mv Mw Mx Nf Ng Nh Ni Nn Nq Nr Ns Oa Oe Of Og Om Or Oz Pg Pi Pj Pk Pz Qb Ql Qm Sr Tn Tr Tz Uf Um Un Up Us Ut Vp Vq Vu wF Wm tF) nN(aD aE Af aG Al AN aP aR AS aZ bA bB bC bL bV cC cP cQ cT cU cV CX cY dB dC dE dG dJ Dl Dp Ed Fr Gl Hw Ii iJ In iO It Je Jf Jk Jm Jn Jo jP Jr Jt JU Jv JY Ki Kl kQ Lh Lu lW Lz Me My nA Nc nD NF NJ nW Og oH Om Or Oy Pk Pz Qc Qd Qg Qh Qm Qt Qu Qv Qw Qx Qy Rb Rh Rj Sr Ss Tn To Tz Ua Ub Uc Ud Ue Ug Uk Ul Um Uo Up Us Uv Vb Vo Vp Vs Vu Vv Ye Ti) Vt(aA aM aU Aw aX bE bJ bL bV cC cM cR CT cV Cw cX DB dD De dJ dK dL Dp Du eF Em Et Fi FP Fw Gd Gh Gn Gp Gz Hf Hl Hp Hu Ib Ic Ik In Iu Iz Jh Jl Jo Jv Ki Kl Ko Kp Kq Kr Ks Kz Ld Lj lM Lv Ly Mb Me Mg Mk Mn Mx My Na Nf Nh Nl NO Ns Nt Nu Of Og Oi oK Ow Pj Pk Qa Qu Qx Rf Rt Si sK To tT Tz Ua Ub Ue Ug Uk UM Ur Un Uw Uy Va Vh Vi Vj Vp Wb We Xa) bA(aA aG aH al aL An aO aS AW aX BB bF bG bH bL bO bQ bS bW cF cG cH cI cJ cL cO cP cU cV cX cY cZ Db DD dF dH dJ eC eF Em FP fR Gc gW HR Hu Hv hW Hx Ib Ih Ii Ij Ik Im Is Iu Iv Iz Jj jK Jn Jo jP jV Li Lx Lz Mc Mf Mg Mi Mj Mr Na Nc Nf Ng Nh Nj Nk No Nx Oe Og Oi Ok Om Pc Pj Pk Po Qb Qh Ur) aN(As Bc cQ Ct dM Dp dR EF Ex Fb Fy gL gW Ha Hb Hf Hq hR HW iB Jd Jh Jl jP Ju jV Kc Kd Kf Kg Ki Kl Kn Ko Kp Kr Ks Kx Ky Kz Ld Lw Ly Mg Mj Mm Mw Nl Ou Oz Pb Pd Ph Pi qD Qg Qh Qm Qu Qv Qx RC Rg rQ rR rY rZ sC Sr St tX Ub Uf Ug Uk uL uM UN uO Us Uu Vp vQ vS vV wJ yH yK zG zH tL Wm Tj Ti) No(Aa aM Ao Ap Ar AS Aw Ax Ba bJ Bo cH Co Db Dg dK Ef eW Ez Gz hC hF hG Hp Hu iA Ii iJ In iO iP Iz Jh Jo Jt Kk Kl Ko KR kS Lv Me Mg Mk Ml Mq Mw My Nc Nf Ng Ni nW nY Oe oF oH oK Om oN Oy Oz Pz Qn Qt Qu Qx Qy Ra Rc Rf Rg Ri Rj Rm Sf Sh Sr To Tv Tz Ud Uk Ul Um Up Uu Uv Vb Vp Wf Zw Ye Wm) Mn(Ad aE AF aG aQ AR AS Aw Ax aY Ba bF bH bI bJ BN BO bQ bU bV cA cD cE cF Ch cJ cK cL cO cP Cq cR cS Ct cU cV CW CX DB dC Dd dE dH DI dK DL dU Fr Gd Gz Hu Id Ii Iz jD Jt Jv Mg Mm Mp Mw My Na NC Nd Nf nH Nk Oe Oi Pb Pk Pz Qb Qw Rg Sf Tz Um Up Vc Vp Wh wQ Yd) Qc(aD aG aK An aR aU Ax aY bC bI bJ bL bN bO bU bV bW cA cD cG cI cL cM cN cR cT Cu cX dA DB DE dF Di dK dL Eo Gc Gd Hq Hr Hu Hw Hx Il In Io Ip Iq It Iu jD Jh Jm Jq Jr kG Lu Ly Lz Mb Mc Md Me Mf Mj Mk Mq Mu Mv My Na Nb Nc Nf Ni Nk Nq Nr Ns nT Of Om Or Oy Oz Pc Pd Pf Pz rB rZ Wb) Jj(Ad Al aM An Ar bB BC bE bJ bS bV Cp Cq Cv DB dD DE dF Di Dk dL Ed EM eW Ex Fa Fc Fi Fn fR Gz Ha hC Hu Il Iu Jd Jh Jo Jq Jv Ke Kf Kg Ki Kk Kn Ko KP Ld Lw Mb Mf Mp Mv Nc Ng nO Nq nR nT Oa Oh Ou Pa Pd Pe Pg Ph Pj Pk Qm Rt Sj Sr St To Uc Uf Un Up Ut Vp Yh Yi Yk Zq) Lj(An aS bE bJ Bn bO bS bV cD cM cQ cT Cu dC dD dF Di dK dL Dp eW Fw Gl Gz hC Hq Hr Hu Hv Ih Ii Ik In IO It Jh Jk Jm Jo Jr Ju Kc Ki Kp KR Lz Mb Md Mf Mg Mi Mj Mq Ms Mu Mw Nc Nd Nf Ng Ni Nq Nr Of Oh Om Or Pa Pd Pe Pf Pg Pk Qg Qm Qu Qv Qw Rc To Tz Ub Uc Up Ur Us Ut Uu Vp) Jr(aM CH cS dX eP Fd Gb Gc Gd Gh Ho Hq Hu Hv Hw Hx Ib Ih Il Io Ip Iq Is It Iu Jh Jl jU Lp Lu Lv Lz Ma Md Mi Mk Mm Mq Mw Na Nb Nc Ne Nf Nh Nk Nl Nn Nr Ns Oe Of Oi Om Op Oy Pa Pc Pf Po Ps Pz Qb rB Ru Rx Ry rZ Si Um Uw Ux Uy Uz Vc Vh Vi Vj Vw Wc Wg Yd Yk Ye Tl Xa) Qd(aG aH aI aL An aO Ap aU Aw Ax aY bB Bc bI bL Bn BO bV bZ cC cD Ch cK cM cN CO cQ cR cS CT Cw Cx cZ dA Db dC Dd De dF Di DK dM Gc Gz hG Hp iA Ib iJ Iz jD jU Kj kR nY Pk QU Qv rB Rc Rf To tT tV Ub UM Ur Uu Uv Wb wQ yJ Ye Wm) Jv(aK An Ar aU bE bJ bV cF cX dD dE dF Di Dk dR ET Fa Fb fN Fp Fr Fy Gc Gl hC hL hO hV Id Is JD Jn Ki KP Kq kR Kx Lh Lx Nb Nd Nt Nw nY Oa oF Pa QA QB qC qD Qh Qm Qv rC rO rP rQ rR rU rW sK tN tT Tz Uf uI UN uV uY vA vI Xa) aC(aD aE aH aI aK aL aQ aV aY bE bH bN bP bQ bR bU bX cA cB cD cH cJ cK cL cO cP cQ cR cW cY cZ dA dC dI DR dU Dw eF EM Eo Ew Fc fP fR gL gP hB hC Ho iH iZ jB kC kF kG lW lX mP nO nU nY oF oN oV oW pK Rg Ri Vv Wb Zq Tl Tk Wn Ti Th) Pk(aE aF aI aL aM aW aX bB bE bI bJ bL bO bV cC cF cG cM cQ cT cU cX cZ dB dC dF dH dJ dR eC eF fP gL gP hB hC hF hG Hv iA iH Ik In iO iP Ir iZ jV Ki kP kQ kS LX Mh Nd nI nJ NW nY Of oH oK oV pF Rg sH Sr tR tT tX Um Us Ut wF tF) Gc(aF Ap bR cF cK cT De Fp Fy Gb Gp hF Ho Hp Hv Ii iJ Ik jL jM Jn Jo Ju kP kR Kx lY Nc Nd Ne nH Nk Nl Nn nO Nu Of Ok Om oN pF Pj Ps Qa Qg Qu Qw Qx Qy Ra Rb Rh Rj Rm Rt Ru Rv Sh Si Sr Ss St Tn To Tt Tv Ul Up Ur Uz Vc Vp We Wf Wm Ti) Is(aM bE Ct dX eP Hp Hq Hu Hv Hw Hx Ih Ii Ik In Io Ip Iq It Iu Jh Jk Jl Jm Jo Jq Lu Lv Lw Ly Ma Mc Md Me Mf Mg Mi Mj Mk Ml Mm Mq Mr Mu Mv Mw Na Nb Nd Nf Ng Ni Nk Nn Nq Nr Ns Oe Oh Oi Oz Pa Pb Pc Pd Pe Pf Pg Ps Pz qW UM Ur Vb Vc) Jn(aM bS dD Du Gd gV Hq Hu Hw Hx Ih Ii Ik Il Io Iq It Iu jB Jk Jm Jq Lp Lu Ly Mc Md Me Mi Mj Mk Ml Mp Mq Mv Mw My Na Nc Nf Ng Nk Nq Ns Oh Oi Om Oz Pa Pb Pc Pd Pf Pz Sf Sh Sj Um Uw Ux Uy Uz Va Vc Vh Vw Wb Wd Wf Wg Wh Zw Ye Xa) Fr(aS Hq Hr Hu Hv Hw Hx Ih Ii Ik Il In Io Ip Iq It Iu Iz Jh Jk Jl Jm Jo Lu Lw Ly Lz Ma Mc Md Me Mf Mg Mi Mj Mk Ml Mm Mp Mq Mu Mv Mw Na Nb Nc Nd Nf Ni Nk Nn Nq Nr Ns Oe Oh Oi Om Oz Pa Pb Pc Pd Pe Pf Pg Po Pz Ss Uu yJ) Lx(aI aJ An aP Ar aS Aw aX Bb bE bH bL Bn bP bR bU bV cA cC cD cF cG cK cL cO CT cV cW cX dA dB dC dD dF DI DK dL dM eP Gz HP Hw Ik In Iz Jk kR lM Me Nd nI Om oN Oz Pa pF Qg qW qY Rf Rm Um Wb Ye Tl Ti) Ok(Ad aM AO Ap Ar aS aU Aw aX bE Bg bI bJ bL bO bS bV cC cD Ch cI cO Ct cU cX DB dD Dg dL dX Ef Eo Fc fR gV Gz Hc Ib Iz Kl kP nI Rc Rt Rv Rx Ry Sf Sh Uy Uz Va Vh Vi Vw Wb Wc Wd Wf Wg Yd Yk Zw Zx Ye Tm Tl) hC(Aa aS aW cP Du Em Et fA Fi fR Fw Fy Gh Gn gZ Ha Hp kC Ke kF kI kN kP Kq Kr Lh Li Lt lW lY mE mF mM mP mW nB nD nF nK nL Nw oO oP oV pH Po rS Rx Rz Sh Sl tT tX Ut Ux Uy Vc Vi We Wf Yd Yj Yk Zw Zx Ye Tm Ti) Po(aS dE Dw Ew hA hG hP Hq Hr Hu Hx Ii In It Iu jD Jh Jl Jm Jo lM Lu Lv Lw Lz Ma Mb Mc Md Mf Mh Mi Mj Mk Ml Mr Ms Mu Mv Mw My Na Nb Nc Ne Nf Ng Ni Nr Ns Oe Oi oN Oz Pa Pb Pd PF Pz qW rZ uM uN Uu wQ) Jt(Aa Ct Hp Hq Hu Hv Hw Hx Ii Ik Il In Io Ip Iq It Iu Jh Jk Jm Jo Kq Lu Lw Ly Lz Ma Mc Md Me Mf Mi Mk Ml Mm Mp Mq Mu Mv Mw Na Nb Nc Nf Ni Nk Nm Nn Nq Nr Ns Oe Oh Oi Om Oy Pa Pc Pd Pe Pf Pg Pz) Nw(Af aM An Ap Ar aU Aw aX bI bJ bL bO bS bV bZ cC cK cM CO CT cU cV CX cZ DB dD De Di dK DL Ef eO eW Hp Ib Iz jD lK lM qT qU QV qW qY rB RC Rf Rm rZ Uu) Nb(aK aM Ar aU aW Bb bE bO bS bV cC cD cT cU cX DB Dd dE dL Eq fR Gh Hp Ik Ip Lp Lv Mt Ne Nh Nn Ry Si Sj Ur Va Vb Vc Vh Vi Vj Vw Wc Wd We Wf Wg Wh Zq Zw Tl Xa Ti Th) Qb(aM Ar aS bS dD Di dW Ew Hv Hw Hx Ii In Io Ip Iq It Jk Jm Jo Lu Ly Lz Mc Me Mg Mj Ml Mp Mq Mu Mv Mw Na Nd Nf Ng Nq Ns Oe Oh Oi Om Oz Pa Pc Pd Pe Pf Pg Qg rB Wb) Ut(Ch Du Em Eq Fc Hc Ho Hp Ib kC kE kN kO Lt lW mF mH mI mM mW Mx MY mZ nA nB nC nF nI nK nU Og Op oQ oV Oy pK Qt Qv Sf Um Uu Uv Ux Uy Va Vc Vw Wb Wd Wh Ye) aM(AA An Ar aS aZ Bb bE bJ bO bV cC cJ cT cU dB Dc DD dK Et Fp Ho Hp Hr Hv Id Ke Kq Kr Kx Li Lp Nt Nx Qa Rt Sj uI Up Uy Vb Yh Yi Yj Zw Zx Ye Tm Tl Xa Th) Mt(aS bE bJ dE Hc Hr Hx Ii In Iq Iu Jh Jk Jl Jm Jo lM Lu Lw Ly Mc Mf Mg Mi Mk Ml Mp Mr Ms Nc Ne Nf Ng Ni Nk Nn Nq Nr Oh Oi Oz Pa Pd Pf qW Sh UM Ur Uu yJ) Nm(aS bV dD Hq Hw Hx Ii Il In Io Ip Iq It Iu Jh Jk Jm Jo Kq Lu Lw Ly Lz Ma Mc Md Mg Mi Mk Ml Mm Mq Mu Mv Mw Nc Nf Ni Nk Nq Ns Oe Oi Pa Pb Pd Pf Pz Vb) Qa(Ar aS Aw bE bJ Bn bS bZ cD cM cO cS Ct Cw dC dE Di dK dL Ef Hp iA Ib Ki Kl Ow Qg Qv Qx Rc Rf Ry Ss To Ua Ue UM Ur Uv Vb Vc Vi Vs Wb Zw Zx Ye Tm) Pe(AA bS dE Hq Hv Hx Ih Ik Ip Iq Iu Jh Jm Lh Lu Lv lX Ma Mb Mc Mf Mh Mi Mj Mk Mm Mu My Na Nf Nh Nk Nl Nn Ns Of Og Oy Oz Pb Pd PF Pg qW uM Ur) Nd(aA bV Fa Fc Fi Fw Gh Gz Ho Hp Ir Iv Kc Kd Ke Ki Kk Kq Kr Kx Ky Lh Lp NY Or Pj Ps Qh Qv Rv Rx Sr St To Um Uw Va Vb Vi Vj Vz Zq Tm Tl Xa Ti) tT(Aa Af An cB Ch Cu Cv dB Dk cC Ef Fa Fb fP hP iA Id iH Il Im Iz jO Js Kc Kn Ko Kr kS Ld Lu Ly nW Ny Oa oK Ou Ow qU qZ rA Tn To Un Vq Wm) Mx(aS bV cD cT Cu Hr jB Jd Jo Ke Lw Mg Mh Mk Mr Ms MW Nc Nf nY Oa Of Og Oi oV Oy Oz Pa Pd rS rY Sr Tz Ue uI Um UN Ur uT Uu vA Tl) aA(Ar bE cD dE Hq Hv Hw Hx Il In

Figure 39 Continued

Io Iq Iu jD Jh Jk Jo Lu Ly Lz Mc Md Mg Mj Mk Mp Mq Mu Mv Mw Na Ng Nk Nq Ns Oe Om Oz Pa Pb Pc Pd Pf Pg) aS(An Bb bO Cu Dc DD dE dF dL Ed Et Fa Fb Fp Fw hW Ih Ij Im Iv Jq jV Kd Ke Ki Kq Kx Lh Mi Mp Mr Ne Nt Nu Nv Ny Og On Pa Pj Un Up) jP(cT dB dD Fd fR Gb Gd Gh Gn Hp kC Lt nA Nx Op Oz Pa Ps Ru Rv Rx Ry Si Sj Um Uz Vh Vi Vw Wb Wg Wh Yg Yh Yi Yj Yl Zw Yc Tm Xa Wm Yf) nO(aK aU bE Bo bU cY dA dD eC Fa Fn Gp Gz Ha Hp Ib Je Jf Ju Jy Ke Ki Kl Kq IL Oa Qg Ql Qm Qu Qw Qz Rm rZ Tn Tz Uk Up Ur Us Vo Vu) Of(Ad An Ao Ax Ba Bb bE bJ bV Cp Dc De Ed Fw Gl Ih Ii Ik Io Ip Jl Kd Kf Kn Ks Nh Nr oF Om Or Ou Pi Qh Qm St Tt Uc Um Un Up Vu) Ke(Ad Ap Bg bV Co dE dL eF eM fP Gz Hc Hp Ib jD jl IN Lv Mk Nc Ne Nh Nk Nl Nu nY Og Oi Or Qx Rc Rf uM uN Uu wF wJ wQ yJ) jV(cT dA Dr Ed eZ Fc Fd Gl Gn Ho hP Ic Id Js Kq Kr Lt Ps qA qB qH Qm qQ rS Rt sH sM Sr Tz uM uN Ux uY Vb Vh Vi Vw Yf) Nn(Hq Hv Hx Ih Io Iq Iu Jl Jm Jq Lw Ly Ma Mc Md Me Mf Mi Ml Mm Mu mW Na Nc Nf Nh Ni Nk Ns Oe Oh Oi Pa Pb Pg Pz) Kq(Ad Ap bE cC Co dE Dk Eq Gd Hc Hp Ib Ik Jk Lv IX Mk Mu Mw Ng Nh Nk Nq Nu Og Oi Om Ph Rf Rm Ss To Ua Uk Vs Tl) Vb(Ao Bc Cw Dd De dF Et Fw Gp Ij Im Jq Kf Kp Lh Mg ml nA Ng nL NL Nt NU Nv Ou Pz Qy Tn Uc Uf Un Vi Vq Vw Wb Zq) Hv(Aa Ed Eq Fc Fi Gb Hl Ib Io Iv Iz Ki Kl Kr Lt Mm Op Ps Rt Rv Rz Sr St Tz UM Ur Uw Uy Va Yg Yh Ti Yf) Or(Aa bE bV cC cM cX dD dE dX Ef eP Et Ik Ki Kr Lv Mk Nh Nt Nu Og Oi Pc Sr To uI UM uN Ur Uu Vw Wb Zq Th) bV(An Ar aX Bb bE bO cC cD cU Cx dB dD dE Ed Ef Et Fp Gz hR iA Iv Iz Kl Li Lz Nc Ni Nk Nt Nu Og Oi Oy Uu) Nl(Hr Ih Ii Ik Io Ip It Jh Jl Jq Lw Ma Mb Me Mf Mi Ml Mp Ms Mu Mv Nc Ne Nh Ni Nk Nr Oe Oy Oz Pb Pd Pz) Ih(bE Hq Hr Ii Ik In Io Ip Jh Jq Lv Lw Ma Mb Md Mf Mh Mi Mj Mm Mp Mu My Ne Nh Nr Og Om Pb Pf Pg Pz) Nx(Hq Hu Hw Hx Ii Ik jD Jk Jm Jo Jq Lu Ly Me Mg Mk Mm Mp Na Nq Oi Oz Pc Pd Pz qW sI tV uN wD wL yJ) Lh(dE Hp Hu Ib Iz Jh Jk Jl jU IM IX Md Mv Mw nI Om Oz qU Qv qW rB rC uI UM Uu Va Vc Yd yJ Zw) Ik(Ho Hr Hx Id In Io Ip It Jl Kx Lu Ma Md Me Mf Mh Mj Mp Mr Mu Mv Ng Nq Nr Oh Om Pa Pf Pg Un) Ar(aU aZ Bb bE bI bJ bO cC cD cG cM CU DC dF dK Et My Nj Og On Qv Rf Um uN Vc wF yJ) rZ(aF Bb cU Dp hR Id Im JD Jf Kr lX mW mY nA nD nI nJ nK nR Oa Pj Qm Qx Sr Uk Um Vq Wm) Li(aU bE bL bS cC cD CO CT cU cX Db dD Di dK dL Ef fR Ib Iz Ki Kl Qu Ur Uu yJ Tl) Un(bE dD dE dK Ef eP Fw Gn Gp Gz Hp Iz Og Qv Rc sK To tR uI Uk Um Uu Wb wF wJ yJ Tl Xa) kG(Dr Em Fc Fi Gb Gd Hl Hp Ic Ru Rv Ry Rz Sf Sh Si Uw Uy Vz Wd We Wf Wh Yd Zw Zx Tm Tl) Lv(dX eP Hr Ii Io Ip It Jl Jm Jq Ma Mb Mh Mi Ml Ms Nc Ne Nf Oh Oi Oy Oz Pb Pc Sr) Og(An Bb Dc De dF Ed Fa Fw Hu Id Io It jB Jd Jm Jq Ma Mr Ne Oh Om Qh Sr Tz Xa Wm) dE(Bb cT CU dD Di Ed Et Fa Fp Fy Gl Gp Id Im Lw Ly Nv Oa oF On qU rC tV Ub Vu) jD(cE dF Et Gb HL Jl Mh Ny Ps Qm Sf Sj sK Tz Uf Vz Wc Wd Wh Yg Yh Yi Yk Yl Yf) Gz(hV iJ jI Nt Nu oF Pi qH qI qV qW qX rA rW Tz Us uU vA vB vI wB wD yL yE tM) Nh(Ho Hr Ii Io Ip It Jh Jl Jm Jq Lw Ma Mb Mf Mh Mi Ml Mm Mp My Ne Nr Oe Om Pz) bO(An cU Dd Ed eQ Iv jB lW mW nD nI NT oD oO oW pK Ps Sj Uw Vh Vw Wd Yi Xa) Ho(bU cB CX dX eM Gp hA Ju Mh Mk Nu Oy Oz Qz Sf Sh Tz Uv Vc Vq Wh Zw Ye) Sh(cB cF Dc Dd De dF Fw Gp iJ jG jQ jR jT jU Kp lK lM mE Nq Nt Nu Qh Xa) Jl(Hc Hp Hr Io Iz Jq lM Lw Mr My Ne Ng Nr Oy Oz Pz qU QW rB Um Ur Ye) Et(aG aO bE bI bJ bS cE CT cU cX dD Dg Di Dl Iz Kl qH Rc uN Uu yJ) Fy(Aw Bg Ch dL EF Em Eq gV Jo kP Qv Rt Rv Rx To Uw Wb We Wh Zw Tl) Ir(bJ Hu It Jk Jo Lz Me Mg Mj Ml Mv Nc Nf Nk Oe Oz Pc Pz UM Wb Tl) Sr(Ed Ef Hc Hr hW Ib Iu Iz lM lN Mv Nf oH Qv Qw rY sH To Uk Um Uu) cT(bE bJ Ct cU Em gL gW hP hR Im Lw My Nf Nt Nu rB sI tV uN wQ yJ) Id(Ad bE bJ dD dL ED Ef hR jK Jo Ki Nu qY rC tO Ub uY vT wF) On(Aw Ct Dk Ef Eq Fc Hp Iz Rt Ry Ss Uu Uw Uy Vc Vi Wb Wd We Zw) aL(dU kC kE kF kI kK kO kP lW lX mF mM mS mT mU mW nF nM nR oQ) cU(An aU aV Bb bE bJ cM cO dD Fp jQ lX My Ne Nt qV qY rB uI wQ) uM(aF dL Fw Gl Im In It Js Kf Ly Mb Md Mq Ni Qm qZ rC rS sK tV) Mh(dD Hu Ii Io It Jh Jm Jq Lw Ma Mr Ne Nr Oh Om Pg Pz Wb Zq) Mm(Hr Hu Ii Il It Jh Mi Mj Ml Nc Ng Nr Om Oy Pa Pd Pg Pz) Io(Ip It Lw Ma Mb Me Mf Mi Mq Mu Ni Nq Oh Om Pa Pd Pf Pg) Iv(aK aU bJ dX eP gV Hu Hw Iq Jk Jo Me Mg Mj Mv Nf Oz Pc) Ye(iJ Im jI jL kE kP lM mF mI mM mS mT mU mY nB nC nJ oV) Ny(bS dU Hu Ii In Iq jB Jk Jo Ly Me Mg Mj Mv Nc Nq Oz Pz) Uu(Cu Dk Fa Fp jB Jd Jg Kf Ko Nr Nt Nu Pa Pj Qh Tn Tz Uf) uN(aF An Bb Bc cM Dg Dl Gl iP Kc Kn Kr Kz Tr uI Ur Vq Wm) Ed(bE cM dD Hf Hp Ko kP mI Ng nH nT Pa Qv Sf uI Wb Zq) Ip(Hr Il Jq Lw Mb Me Mf Mi Mr Ms Mv Ne Nr Oh Om Pf sJ) Nj(Dw dX eM eP eW gV Hq Hw Jo Mb Me Ml My Nf Ng Oi) Tz(Fp hP Ib Iu jI jU lN mS nT Nu rC Um Ur wF Zw Tl) Kr(Ad Ap jI Jo Ki Kl Oi qH qU qW rB rX rY Um wF wJ) Oa(cM cX dC Dp gV Iu Ju kP Nu Rf TO Ub Um Wb) Aa(EF Hq Hr Hw Hx Jk Jm Jq nY Pz tN tO yJ) Gp(DU Eq Fc Gd oV Rt Sf Uw Uy Uz Vi Wb Tl) Ne(bE Hr It Jq Lw Ma Mb Mf Mr Ms Nk Nr Pz tV) dD(Bb cC dL eO fA gV Jo Ng NT Pj Qu wJ yJ) lL(kC kO mE mP mU nB nI nJ nL nR nT nU oP Yd) tV(Ij Il Iz Js Ly Om Qm qQ uT uW vI wP wQ) uI(dL dR Fw hR hW Ib Ic iP iZ Lw Ni Um Wm) Nr(Ib Jh Jq Lw Ma Mb Mr Ms My Oy Qw Ur) Hp(cB Cu iB Im jI Js mM nI Nt Ou Qh Tn) Pj(bE fP jI jK Jo lK lM lN Qv qW sK tX) eC(dU dX eM eP fA gC jB kC kF nJ pH pI) gV(aD bB cB cP Cw DR Oh Ow Rg Tn Vq) yJ(aF Cv Dl dM Im Kn qZ rC uT Vq wD Wm) rB(dM Fa fR hR Im iZ Js Nv uP uW Vp Vu) qX(rS tS uV uZ vU wD wE wJ wP wQ zA zG) Pg(Hq Hx Jh Lw Ma Md Mf Mi Ml Oy Oz) dF(bL Iz Kl My Oy Ry Rz Uw Vc Yg Tl) tO(Cu Dl Fa Gl Kd Kn Ld oF Ou Qm rC) wF(Aw Bo Cv Dl Jf Kn Kz Qw Tv Ur Wm) Nt(bE bI bJ cI cM Ct cX Ef Gd Sf) Kx(bJ Em gC gZ jB oT pI Rf Wb Ti) sK(aW Dl Im iP Qm rC Ri To Tk Th) Fw(Hc Ib Ki lX oV Qv Ug Ur Vc) Mr(Hr Hu Jh Jm Jo Mp Mw Nc Om) Sf(bB cB cF Dd iB jM kP Nu Zx) Js(jU Oz Pc Qv qW tR Ur Uv wQ) bE(cC Eo Ew Fp kF Mi My nL Nu) hA(Fc Gh Hl Lt sH Wg Wh Yl Zx) Cu(Eq Jo Oy Qu Uy Wh Zw Tl) Th(qB qH rT uV wB wP wQ zI) Xa(bU De eP gP iP mW Oi Qw) Um(dL Ha hR iB jI jU Pa Up) nI(kC kF Ma Mj nT qU Uf tF) jY(kF mE mH nA nD nR oQ Tl) Hr(Ii Jo Jq Om Pa Pd Pf) Im(bJ cX dB rC vA vO wQ) Wb(As cB De Gd Mk Nu Rc) Zx(De dX eP gW jE jM oV) Qm(lK tN tR tX uY vU wE) cG(eP Fc Gb Gd Uw Uy Tl) dU(bL Bo cR Kl nL To Wf) mW(Hl Lz Mq Wc Yg Yh Yj) iB(kC kF Lp mH Oz Ry Vc) jB(bH bR cA cD dM Ib nL) jU(Dr kF nT Rv Sj uY Vi) Fa(cM cX Ef Jo Mk Rf) Fp(Bb bJ cM Oz Rc Wm) Jd(Ap Ef Kl Oi Rc Ss) Ur(Cq Ha Mp Us uY Vp) bB(Dw Eo fA oT Uy Vc) cB(Gd Gh Gn Ry Uy Wh) hR(aF cV hW sF sH vI) tX(aW cS Dl jM Ly qZ) qU(dB Em mI nJ oP oQ) lM(dM Nv oQ Uy wB Zq) pK(dK Mk nH Nk nL oO) Mb(gC Ii Jo Lw Pz) Om(Hq Ly Mf Oh Pf) Uf(lX mS Ng oP Rc) cF(Eq nT oP oQ pH) dX(Ki Kp Ky Ou Ow) nK(Gb Lp We Yg Yl) wQ(dM Kn Nv uT Wm) oV(bH Ib Jf nL Ue) Dc(Ct Jo Rt Vc) Ti(Ha oF Ub wH) Nu(aU bJ Di dK) Ms(Ii It Ma Pz) Jq(Hu Jh Oi Pz) Rv(jE jM lN nL) dB(gW jI rS rV) eO(aY cW cZ Il) eW(cW cX Hx Oh) sF(BC Qy vI) rC(An sM uY wJ) wD(aQ cY iA Kz) Ch(rQ rV tN) Du(gL Qy Up) Dw(bN Ct Ml) Eq(Ao Dk iJ) Gd(De mE Vq) Yk(kP oD oT) Zq(gP iP Qz) Vc(jI lK Ou) Oy(Bb Ii Pz) cM(kF nY Sj) dW(aD aI bS) eP(bC Ki Ow) gZ(cD cR Nk) tR(Dl Kn Ld) sI(bC jM Rb) sH(hP iC Vu) uO(aF iP Vq) Ax(bJ oO) Ew(aD aF) Gl(fP lX) Ma(It nD) Ib(rP rV) Kz(hW qA) Nv(qW wJ) Oz(hW jI) dL(Bb wE) nT(Ri Ug) iA(qZ rQ) jM(sJ wB) kP(Vv Yj) oW(bH cQ) DifR DkrQ DlrY FnoT HaNk MppF NivI UcKl QxoF QvKs JoUs TlcC KcqH LpmE RmpH TkqB UkPa UwgP aIfB aWqY aXqZ bJgW bQoP tNiP jQkF

Constrained panels with 3 analytes, where 1.0E-10 >= 'AUC p-value' > 0. Contains 28,393 panels of 38,239,313 total panels evaluated. :
jD{Yd(aC aG aH aI aL aN Ar aS aW Ax aY aZ bC BG bH bI bJ BO bP bR bS bU bV cB cC Ch Co cR cS dB dD DK Dl Dp Ef Fb Fd Fp Fw Gc Gh Gl Gn Hc Hp Ib Ii Ik Im Ip Is It Iv Iz Jd JE Jf jG Jj JK JL JM Jn jO jP JQ jT Ju jV jY Kc Ki Kr Kx Li lN Md Mg Mh Mj Mp Mq Mu Mv Mw Mx My Nc Nd Ne Ng Nj Nk Nl No Nr Ns Nv Oe Of Oi On Oy Oz Pe Pg Pj Po Ps Qd Qt Qw Qz Rc Rf Ss St Tn Ug Uh Uw Vc Vj Vz Wb Wd Wf Yg Yi Yl Ye Tm Ti) Zx(aA aG aP aR aW Ax bA Bg bH bS cB cC Ch cM Co cP cR Cs Ct Cx dB dD Di dK Dp Ed Ef Fd Fn Fp Fw Gb Gl Hp Hq Hu Hx IB Im Is Iu Iv Iz Je jF jH Jk Jl jM Jn jP Jy Kf Ki Kl Ky Kz Lj lN Lt Lu Lx Mh Mj Ml Mq Mt Mu Mv Mw Mx My Ng Nq Nr Nu Nv Nw Oa Oh Oi On Op Oz Qa Qd Ql Qt Qw Qy Qz Rc Rf Ri Rj Ry Rz Ss St Ua Uk Vp Vs Vz Yg Ye Wm Th) Lp(aD aE Af Aw Bc bI bR cH

Figure 39 Continued

Figure 39 Continued oF(sK vO) uW(iP Lu) vA(aN tF) vS(Ip Po) NmrR NdnO HvpS ImuP HfjP StuO YeiB KdtL KryD LhdX OkvQ PhuM PjlN aJuV cMoW cQeZ
zHqX wGkR} Th{yJ(aA AD aH aL An aO aQ Ar As Ax BB bE Bn bV cE cG cH cJ cM Cp Cq cR Ct CV cZ Dc dF dG dJ DL dM eC Ed Fa Fb
Fn Fr Fw Fy Gl hC hG hL HV Hw Hx IB Id Ii Il In Ir Is It Iv iZ Jd jE JH Jn JO Jp Jq Jr Js Jy Kg Kj Kp kQ KR Kz Ld Li Lv Lw Ly Md Me Mf
Mi Mj Ml Mn Mq Mr Ms Mt Mu Mv Mw Mx Na Nb Ne Nf Nj Nn No Nv Nw Nx Ny oE OF Oh OK Om oN Pa Pf Ph Pi Pk Qb Qc Qd Qe Qn
Qv qW QX qZ Ra RB Rj rN rO rV rX sK sO Sr Tn To Tt tU Tv tX Ub Ud uG Um uN Uo Up uR Us UT uU Uv uX uY uZ vH Vp Vs wG wH
wP zI tL Ti) wG(aG aK Ap aU aX Ba bF bI cB Ch Co Cp Ct cV cY Dg Dl Dp dR Et Ez Fy gW iB Ip Is jF JG Jj Jk jM Jn jO jR Jy Kf Kl Kp Ks
Li lM Lx Ma Mj Mk Mm Mn Mx My Nh Nm No Nr Of OH OK Ow Pc Po Pz qH Qv QW qX QY Rc Rg sK tR TT Tv Ua Uc Ue Un uO Ur Ut
Uu vB Vo vP vV wE wH wJ wK wL wQ zA) wF(Ad aF aG aH aI aO Ap aQ aU aY Ba bF cF cG Co Dd DG dH Dk DL dN EF Ez Fn Fy Hb iA
iO Is Iz Jg Jl jR Jy Kf Ki Kj Kl Kp lM Ma Mj Mk Mn Mp Mz Nl Nm No Nq Nr Of Oh Oi oN Pf Po Pz qH Qy Qz Rf sO tO Tr TT Tv Ub Ue Ug
uL uM Ut vH vI VO Vs VV vW wJ wQ) wH(aF aG aK aM Ao Ap aV Aw bI Co Ct cY Dl dR eF EZ fN FY Hc iA iJ iO Jg JO Jy Kf Kj Kp Li
Mg Mj Nc Ng Nq Nr Og Oi Ok Pf Pk Pz Qy Rc rO rR Ss tO Tv Tz Ua Uc Uk uM Ut Uu Vo vT VV wJ wK) tT(Ao bI cH cR Dd De dR Ez fP
Fw Ha Hu jE Jk JM jO jT jY Ks lN My Na Nb Nc Ne Nh Nl Nu Of Oi Ou Pc Pk Pz QV Qw qX Qy rP rR rX rZ sC Tv Ua Ub Uk uL uM Up vI
vT wB wE wK wP yH yL tL xA) vV(aF An Ar Ax bA Bc bJ bV Cs cT Cu Cv Cx dA dR Hw Hx Ij Im In Ir It Ji Jn jO Jq Js jY Kd Kn Kq Kx Ld
lO Lw Ly Mi Mq Mr Mz Nb Nf Ni Pd Pe Pi QV Qx Ra Rm sK Tv Ub Ud UN Uo Vp Vt) zA(Af aM aO Bg Bn bW bZ cI cJ cM cU cX dA De
dF dK dM Dp Fn hA Hu iB Ik jG Jj jK Kp kR Kx Ky Mb Ms Mx Ng oE oF pF qB Qn qT Qv qW qX qY Rf Rg Rh sK sM tU Uf uI uT uW uY
vU wD wP tF) tO(aA AF Ar bJ bV cE cH cR CV Cw cX cZ Dd De dF Dl Fa Fw Gl Ha hC hW JE jH jK Kd Ke Kf Kp kQ lO Mz oE oN Or Ou
qT qX rP tS Up uW vI wP tL) wK(Af aM Ap Bb Bc bE bJ bN cR cW Dd Fb Gl Ik Im iP Iq Je Jj jK kR kS lN Ly Mc Mr Mx Nb No Nr nY oF
qB Qe qT qX rV Sr Ub Up Vt wQ Ti) wQ(aA AF Ao bM Bn Ch cU Cx Ed fN gL hW jG jI jO jP Kl kS Ly Ne Oi Pk Pz qB Qm qU Qy rW rY
Ua Ub uL uM uO Uu uW wC) wB(Af Bn Dd Fn Hv HW IB Ii Ij In Ir Jn Jq Js Lw Md Mi Mq Mr Mt Na Nf Ny Om Ou qH Qn Qv Qx Rj Sr Tv
Ud UT Vv) wP(aE aK aV bI Ch Ct cY dR EZ fY gW iJ jF Jk jM jR Kl Ly Ng Nl Nq Og Oi Pk Qw Qy rR Ss Ua uM Uu) wL(aD aM Ap Ar Ax
bV dA eZ Fn Ha Ib Ic jE Jj jO Ko Lx Mz Nb Nr Ou Pk Qv sK Sr Ub Up Uu Vv) vT(Af aO Ap bZ cD cI cU dM Dp eD hR iB Ik iO iP jK kR Ks
Lu Me qQ Qv Rc rZ sK tX uY) wJ(aA aL aM cM Cv dF Fn IB Id Je Jj Ke Kn lO Mb oF qX sK Up uT uW Vv wD) qH(aW cH cP dE Hu jK Kc
lM Nc Ng oE qB qU Qw tX uP uR uT uU vH vW wD yK zI) tR(cW Dd De Fa Fn Fw Gl iB jE Jj Jp jY kR Ou Pk Qm qX rX Sr uN uV tL) bI(qZ
rS rV sK sM sO tQ tU tX uG uR uT uU uX uY vA vH wD zI) sK(Al aW bN cH eD Gl hR jP Kc Mj Ng oE Oz qB qU Ur vW wC) uN(aW cH eD
Fb jK Jr Kc Ng oE Og Oz qB qU Qv Qw qY Ur Ti) uV(aF Aj Ao cX fN gL lM Ne Ng Of Og Pz Qy rY Ua uM Up Uu) Qv(qI rN rR rT rU rW
sC tU uR uY vP vQ vS vW wD) tL(Ch cY dR gW Hu iA iB iO Jk Kp Nm Nr Of Oh qY) wD(Af aV Cp Ct dR Ib iJ iO JG Jk Jo Li Of) uT(aG Ch
Ct cY dR Hu Ib iJ iO jG Jk jM Kl Li) qB(aS Bc Jj Ly Oi Oz Pk qV qW qX rR uM vI) vW(Af Bn Cx De dF Mx oE Qn qX rX sM) vH(aV Ch dR
Hu Ib jE Jk Jo Li Mj) zI(aV dR hR jG Jj Mg My Og Up) tX(bF dR Fb jE jG jO qX rW) jP(Fd Ho rT Sf Sh Vw Vz Yi) vU(Ao cH Fb jE Nc Nl Pk
vI) Hu(rN rR rW sC tU uG uX) hA(Lp Sf Vw Vz Wc Tm Tl) iC(Gc Lp Rz Ux Vw Zx Tl) uR(aV dR hR jE jR jT Up) Ng(rP rR rV sC uW vI)
zG(Af Bn Dp iP Pk uW) uM(aO cH Fb hW Mx wC) uU(aG aV dR iJ jG jM) tU(aV Cx cY dR Jk) jE(Lp qZ rU Yd tM) jI(Hp Lp Ps Wf Tl) rT(aF
Gl jK Og rS) vP(cW De Ms Nb sM) bB(dU kC kF oV) eC(kF mE nB pH) qZ(Cu Li Md Qw) qX(tN tS yD tM) Sf(iB jT lM) yK(bJ Ly rX) jK(rR
rW uW) jV(Yk Zq Ye) rV(Li Pf Qw) Nd(Du Or) Ne(oD tQ) Nh(oV pI) Nl(mW oD) Lp(jH lO) cR(gC tM) dX(Pe Po) fB(aL dD) nB(cM Nx)
tS(dR Mg) yH(Ap Jj) sM(Og Up) sO(Ch Ib) jO(uP zH) jU(Zx Ye) rW(aD oE) rS(Li Qw) uL(cD hR) vS(Ms rY) AfvO CxxA DpTk FnmW
GpnR MxpI IctM ToeQ RcwC ZqlN WfdU JktQ KcfN OrrN UfeP VvuO OzuW aMwE iOpS yLrR} jV{Lp(Ad aE Af An As bA Bn Bo bU bX
cC cM Cp Cq Ct Cu CW dE dG Dl dM Dr Em Fc Fd Fy Gn Gp Hl Ho Hv Hx Ii In Io Iq Ir Iv jI Jn Jo Jq Kd Kp Kq Kr lO Lw Mb Me Mi Mr Mt
Mz Na Nb Nc Ne Nf Nk Nl Nm No Nr Nu Ny Of Ok Om On Pa Pd Pg Pi Pk Po Qe Ql Ra Rb Rt Sr Tn Tv Uc Ud Up Us Ut Uv Uw Uy Uz Vi
Vp Vq Vs Vv Vw Wc Wg Tm Tl Xa Tj Ti) Gd(Ad An As BC bI Bo cC CP Cq Cu Cw dA dB Dc Dl Em Fd Fy Gb Gn Hl Hv Hx Ii Ij Il In Ir Iv
jE Jn jP Js Jt Kd Kp Kq lO Lw Md Me Mi Mt Na Nb Nf Ni Nm Nr Ny Om Pa Pd Pe Pg Pi Pk Ra Rb Rt Tn Tv Uc Ud Ug Up Ur Us Ut Uv Uw
Uz Vi Vp Vq Vs Vt Vv Wg Zq Ti) Zx(aD aP As Ax aZ Bn cG cQ Ct Cu Dc dD dE dG dN eD Fa Fd Fi HA Id Iv Je Jj Jk Jm Kd Ke Kk Kq Kr
Kz Ld Mh Ml Nd Ne Ng Ni Oa Or Ow Pg Pi Ql Qx Ra Rb Rz Sh Tv Ua Ul Um Uu Uw Uz Vp Tj) Rz(aE Af aO aP Bc Bn bS cP Cu dA dC dF
dG Dk Ex Fy Gh hA Hv iB Id Iq Jd Jg Jh jO jR Kr lK Nu Ok Oy Qt Rh Tz Ux Vw Vz) Wh(aD aI As Aw CP Cq Cu Cv Dc Ex Fd Fy Id Iq Jq Kd
Ke Kk Kn Kx Ld Lv Mt Nb Or Pi Pk Qx Ra Rv Tn Tv Ut Uz Vp Vq) Rv(aK aQ aV bC bE bI bS cC CV cY dB hA Jd jK jP jR Li Lj lK Mh Mu
Nh Nj Nu Qy Rh Ri Sr Ut Vq Vv Wf Ti) Rt(Ad aE cW dK Dr Fc Gb Gn Hb Ho Hw Id Ii jE Ks Md Mh Mz Nk Ok Pa Pb Rb Ri Uc Ur Us Vv
Wc Yi Tj) Sh(Al Ar bS Cu Gh Io Iq Jd jT Ki Lv Mf Mm Mr Nc Ne Ni Nk Nl Nu Pd Qh Qt Up Vz Yl Zq Tm Xa) Zq(aW aX bH bV cF CH Di
dK Ef Ez Gl Iz Jj Jk Kd Kf Ko Ks Mh Oy Qg Qz Ri Ru Ul Ur) Yg(aD aE aG aH aK Ao Bn Cu Ex Fw Id jP Kq Kr Ky Mr Mz Nb Or Ou Ql Sr St
Tz Vu Yf) Xa(aI Ar aW aX Bg bL dB dK Hb Ki Kl Ld Me Og Oi Or Ow Pj Qg Qx Qz Rc Ri Tz Uh Uu) Lt(aD Ar cH cM Cs dJ Ed Ex iB Ij Is Ji
Jq Ke Kk Ld Lh Lx Mj Ml Mp Ou Pe Pf Po Qx) Tm(aG Ar aZ bJ Ch cI Cx Fb Ki Ks Ld Nb Ou Ow Pj Qt Qu Qw Qx Qy Qz Uu Vt Ye Ti) Ur(Dr
Fc Fd Fi Gb Gn Hl Ho Ps Ry Uw Uy Uz Vb Vh Vi Wd We Wf Wg Yj Yk Yl Tl Yf) Vb(Cv dA dK Fy In Iq Ir Jo Mb Mh Ni Nk Nm Ok Pa Pd Sr
Uv Uy Vv Tl) Fd(Bn cF cH De dK Ex Hb Id Ii jI Mh Nt Ok Pe Ph Po Ql Ri Sr) Dr(aP cU dF dK dL Hb Jm jT Ki Ks lL Lz Mh Mp Qm Rh Ri
Tv) Ye(cH dK Ed Fw Hr iB Ir Mr Mz Nc Ne Ni Nk Nl Nw Pe Po Ql) Vi(cC cF Cp cV cY dK Hb Is Ks Mh Of Or Qw Qz Ri Tv Uu) Mh(Em Fc
Gb Gh Gn Hl Ho Ps Ry Uw Uy Uz Vh Vw Yl) dK(Fc Fi Gb Gn Hl Uw Uy Uz Vh Wc Wg Yh Yi Yl Tl) sH(Bc bJ Dk Hf hG Hx iH Iu kR Nq Oy
Pf Pk Rb uM) Hl(aE Ar Cu Cv Hb In Jo Kj Ni Nk Qm Ri Tz) Yl(aK aQ Ar aZ cF CH cR cV Db Kj Ks Ru) Em(Ko kS Lz Mu Nu Of Ph Pj Qm
Ri Tz Ua) Hp(cH Cs Dk Fw It Kn Kr Mq Po Ps Qa Sr) We(Ad Cu Iq Is Ji Jq Lh Mt Mz Nb Ok Uc) Ph(Fc Fi Gb mW Ps Uz Vh Wc Wf Wg Zw)
Gc(Af dG Ed iB Ic Rh Tz Uu Va Ti) Gn(Ar aZ Gp Hb Mp Of Pj Qm Ri Uh) Tv(Fc Ho Uw Uy Uz Vh Wc Wg Tl) Rx(Hf Ld Lx Mk Mp Or Ow
Pf Qx) tX(gL iA iP jM jO nW oK Qm Qy) Yf(Ar jE Oe Qg Rc Sr Uh Un) Yi(Ar Ch Cp Kj Ks Oy Qz Uu) Yj(Fw Io Nc Ne Ni Nk Nl Ou) Uw(aG
Hb Jk Ki Kj Ks Lz Qw) Gb(cF In Jk Ki Lz Rc Tz) Yh(aE Aj aZ Ch Oy Qz Sr) Vz(Ar cB Ks Lv Oi Ql Qz) Wc(cF cQ Mr Po Qm Ri Tz) Ps(cF In
Jk Mu Ua Uu) Uy(aG Hb In lM Qm Ri) Vw(aE dA eD Ng Nu Vv) Fc(Hb In Pj Qm Tz) Fi(cC cF Hb In Lz) Ux(Ar Ji Jj Ng Ow) Tl(Ar cF Ri Tz)
Kr(Ly qH qQ tO) Ru(Ar Hf Kx Lv) Vc(aY cG cU hA) Vh(Jk Ou Ri Un) sK(iP Jf Lu My) Wd(Fy Hf Nb) Or(My Qy Um) Uz(Hb In Ri) Vj(Id Io
Vt) tO(Ke Ld Wm) oQ(bO cH cU) Yk(Ou Qg) Yd(Jj jP) Wb(Fw Ml) Zw(aE Cu) Sr(Ry Wf) Wg(Hb Ri) Kq(qH qQ) Op(dL Pj) qX(rS uI) uM(Id
Mx) AaeF ArRy BnmW CswQ TiEx NgTk SiJi SjRh QwVa LdtR aRnR cHnN dAhP} Gc{hC(Ad Aj aW BG bU cM cQ dJ Dk Dl Ef eQ Gb Gd
Gn Gp Hp Hv Ii jB Jt kF Kn kO Kr kS Kz Mh Mj Mm Mq mS Mv MZ Nc Nd Nh nK Nt Ny Oe Oh Oi Om oO Ow Pj Ql Qv Rf Rm Si Ug Un
Uu Va Vi Yi Yk Tl) Vb(aR cF Cu Dc dF Ed Fc Fw Fy gL hG Ho Hv Jj Jp Jr Jv Kd Lh Mk Mt mW Mx Mz Na Nb Nd nH Ni Nj Oa oF Ok On Or
pH Pk Ry Sf Si Tn Va Vi Vt Vu) hA(aO Ar bS bX cE cG CS Cx dH dJ Fa Fd Gb Gd Ib Id jF Jo Jt Kn Kp Kz Ma Mg Mq Nd Nf Nn No Nr Ny
Oi Ow Pa Pe Ph Rf Rh Uf Um Un Ut Uu Tl) kG(Ad Aj aL aX bB BG bH bI bU cM eC fP Gp Hp Hv Ib Ic Ip Jj Jt Jv Kj Lj Mh Mm Mt mW Mx
nB Ne Nh Nk NL Or Qy Rh Sh Si To Uu Vw Yg) oE(Ad Bb bC BG bU cM cQ CX Dl Ef Gb Gp Hv Jr Ju Jv Kn Mm Ms Mz Nh nL Nm nR Ns
Og Oh Oi Ow Pj Qv Qw Rf Rm Sf Si To Ue Yi) eD(Ar aS bI bJ bS cQ De dL Ed Fb Fp Hb Ic Ii Ir jE jF jK Jo jU Kg Kr Ks Kx Lp Md Mf Ml

Figure 39 Continued

Mx Ns Op Pa Qc Qd Qn Ry To Uv Vz Yj) eC(aA AF aZ bA bG bI cD cF cQ CX De dJ dM Ed eP Gp hG Hv Jo Jr Jv Mk mW Ns Oh Ow Rf Rh
Rm Sh Si Ue Yi) iB(Cp Dg dJ Dk Ef Fp Id Iz Jd Jk Jl Jt Jv Kr Mh Mm Mw My Nh Nq Nw Ok Oy Oz Qd Rc Rm Rx Ry Vi Vo Vz We) hG(Aj
Bb BG bO bU cD cM dJ Dl Ef Gb gP Hp iA Iz Lh Lj Ma Mh Mm Nn Ny Og Oh Om Ow Oy Si Uw Zx) nL(aC aF aL bB bE cD cQ dD Dl Gb
gP Hp iP Jt Jv Or Pe Qv Qy Sh Ug Ur Us Uu Vw Yl) lN(Ar dl Ed Fp Gb Gd Gp Ic Ir Ke Kf Kr Kx Kz Mj Mq Mx Nf Oy Pi Qn Sj Um Tj)
lM(bC bJ cQ CT Cx Dd dE dF Dl Ir Jl Jo Ju Kj Ms Qw Rh Sf Vi Vt Ti) Ue(Aj cF gP Jv Mh Mz Nb Nd Ni Nj Oa Or Ow Pk Qv Ry Sf Si Vq Vt)
nH(Aj cD cQ Dl Gb Jt Jv Nn Pd Pe Pf Pz Qv Qy Ur Us Uu Uy Vv Vw) jP(Cs Db dJ Ib Im Kf Kn Ky Mz Nh Nj Nn No Oh Ow Rh St Vj Ti)
lK(Ap bX cP dJ Ef Ex Ik Jn Kl Kx Nj Nk No Nr Rx Rz Sr St Vj) Hv(Ed Hp Ju Jv nN oF Qz Ri Rm Sf Sh Si Tv Uk Uv Va Vo Vp) Vt(Aa cF Gb
Gd Gp Hb Hp Jr Mm Na Nd Nh Om Ow Qv Si Ut Uw) kS(BG bQ cT Du Ef Fy Ji Jr Jv Lx Na Ok Or Oy Pk Qw Sh) iC(aG cI De Ef Ib Ij jL Js
Ki Kq Ks Nd Nh Nr Nw Pk Ti) jR(Cq Cs cT Fp Hp Id Iq Kx Kz Nf Ng Oi Rf Rx Us Zw Tl) Nd(Ed jL Ju Jv nO Or Qv Rg Sf Sh Si Uk Uu Uy
Va) mW(Ax cM Cs Gd Jj Jt Kj Lj Lx Nl Pd Uu Vo Vw) jl(Ex Jk Jt Lh Li Nn Nr Nt Nw Ok Qd Sr Un Vj) jO(aW Cs Cw Ex Ib Jt Lh Ni No Nq
Ny Rt Ti) oF(bG bU cM dH Gb Hp Jt Mm Nh Nm Oi Tr Uc) jF(aG aV cM cW Gd Jj Kc Lu Ng Qn Ug Tm) lL(Cs dJ Ez Lh Mm Nc Nk Nt Nw
Oi Pe Rz) Gd(eQ jU jY mE nK Sf Ub Us Ut Vq) Or(gL Gp Hp jU Mk Rm Sf Tr Ub Va) nB(aF aL bU cM gC Hp Og oO Oy Ur) Jr(iP Rm Tv Uc
Uu Uv Uy Va Vo) gP(bG cT Ed Oa Pi Pk Qv Um Ut) jL(Em Ih Jn No Og Oh Qt Qz Wh) Jp(Jv Sf Sh Tr Uc Uf Uw Ux) gW(AF bA cQ CX Ni
Oh) jE(aM Cs Kf Ms Nm No Un Wf) jU(al cE Il Ki Mz Pg Vi Yj) kP(cW Gp Jj Jv Kk Nl nW Sh) Ut(Aj Ch Jj Kj Sf Sh Si) nN(Ap bB bU cM Dl
Gb Jt) lY(bX cW Gp kR Nk Nl Uu) Nb(Ju Jv Sf Ua Uk Vq) jY(aP bO Ng Ni Uk Yk) oD(BG Jv Nl nR Zx) Qv(Dp fP iA Uy Tl) Uu(cF Nv Ok
On Pi) Va(Ap Mz Nh Pk Tl) Vq(Ed Ir Lx Ok Qe) gV(aC aU Co Lh Mt) jK(Io Nc Ni Nj Rx) Dl(kE kN mF nK) Gp(iA kF mM mS) Sf(Ap Ho mY
Tl) Ug(fP nA nK nO) Nh(Qc Tz Vi) Ye(mM mY mZ) Jv(jT mE mM) Rg(fP gC nC) aC(Ni Of Pk) nW(eQ oO Rf) oH(cW dX nK) Ed(Hp Ow)
Fy(Uc Vo) Ms(jG jM) Qe(gC Ow) Jj(mI mM) Ur(mE nA) bQ(fP iA) cM(hB nJ) nR(aL bB) mS(Gb Ux) iP(cF No) iZ(Ef Hp) lO(Dr Nm) AdkE
FadX MzUc NgjT UaOn IsRm SiUn ShmE ZxfA QtVo KjiA LpjQ RijG OhnY OkUw UmfP PieQ dAnK} Eo{Jr(aA aC Aj Ax aZ bA bB bF bN Bo bR bU cB cE cG cP Cq cT Cu Cx DC Dd dL dW eM gV Hu Hw Jj Jk Jl Jm Jn Js Lw Ly Mi Mk Mn Mp Mr Mv Mw Mx Nc Ne Ng Nh Ni Nl Nr Nv Nx Oe Oh Oi Ok Oy Pa Pc Pe Po Qa Qe) Hx(Aa aD Af aK Al aM aQ aV Ax aY bA bC bE bF bM Bo cG cI cR cT Cu Cv Cw cX cY cZ Dc Dd Dk Dw eM Hv Ij Im Iv Jj Jn Js Jt Lh Mi Mk Mm Mn Mr Mt Mz Nc Nl Pb Pc Pe Qc) Is(aI aM aP aR Ax Ba bB Bg bM Bo bV cA cD cP Ct cX dD dE dG Dw fP Ik Jg Jl Jn Jp Lv Lw Mk Mn Mr Mv Mz No Nw Og Oh Pb Pc Qb Qe) Qe(Af Aj As Ax aY aZ BB bC Bg Bn Bo bS cT CX De Dl dN dW eP Et Gd Hv Ik Ip Jg Jj Jk Lv Ly Mk Mm Mn Nf Ng Oe Om Pg) Po(Aj As aX bA bB bJ Bn Cu Cx dA Dc Dd DE EM Fr Gd Hv Ip Jn Js Lv Lw Ly Mi Mk Mp Mq Mv Mw Nf Ng Of Oh Oy Pg) No(Af aI aX aY bA bC bQ bS cE cG cT Cu CX dA Dc Dd De dX Gl Iv Ji Jn Js Lv Lw Mi Mn Nw Nx Oh Ok) aM(aD As Ax aZ bA bO cB Cq Dc Dd Dw eM Ew Fw Gp Hv Ij Il Ir Jl Jt Me Mr Na Nr Ok Oy Pg Qa) Nw(aA Ax bL bN bQ bV cO cT cU dD dK dN eO eW Ij Il Iv Jl Li Mk Mn Mr Mu Nr Oh Ok Pc Pe) bM(Aj Bb bX Cq Ct Cu cX Dc Gd Hv Ij Il Jk Jn Jq Mf Mi Ml Mu Mw Mx Nv Oh Oi Pe Pz) Oh(aO As aX bS bZ cL cO cS cU cZ dA Gd Hq Jj Jo Jp Mz Nx Ok Oy Qb Qd) Qb(Aj Ax bA cT Cu Dc DK Hv Ik Il Ji Jp Js Mi Mk Mn Ok Pg) cX(Bo cC cD Co Cu Dk Dl Hv Hw Jh Jl Mg Ms Nt Ny On Qd) Mn(aC aD aP aY dG dN Hw Jn Jp Lh Nd Ne Nl Nn Nr Nx) Af(Ax Cu Dc Hw Ij Jl Jn Js Nr Ny On Pe Qa Qc Qd) Ok(cA Cx dC Dg DL Em Hv Jn Jo Lh Li Lv Mk Pg) bB(aD aG dC Fw Hv In It Jh Jn Js Li Mr Nr Nu) Mz(aD Ao Ar Bb Fp Ij Iv Li Lj Ml Mr Mx Nd) Ji(aY bV cD cP dD dN Em Hv It Mk Mr Nk Ns) Jl(Ax Bo bS Cu Cx cM Hv Iv Jn Js Mi Nj Pg) Jp(bA bN bW cU dD Iv Mr Mu Mx Oy Pg Qc) Cx(Ad Cu Dd Et Iv Jn Nm Ny On Pd Qd) Lv(Cq In Ip Iv Jg Js Mi Mx Nr Pd) Jj(aI bX Gl Hw Ii Iv Jn Js Mf Qc) Aj(Cu cW Gl Hw Jn Js Nv On) dL(Ax aZ Cq Cu Dc Il Js Nj) Ml(bO cM cW dX Io Mm Nx) Ij(bP cA dE Em Hv Jo Lw) aD(aY Bb Bn Cu dX Mf Of) Bo(Ao Bb bX Hw Io Jt) Mb(aR aV Ct dB Ew Hq) Qa(Ax Hv Mk Nj Oi Pg) Jn(Bb cZ dE dF gV Iv) On(Bg Gd Hv Iu Jg Of) bR(aI cG dF Gl Hw Nm) cA(aI Cu Dc Gp Hw Iv) Em(Ax Cu Il Nr Pe) Et(aF Ax dD Hv Nr) Mm(Ax Li Lj Mr Nr) cW(aZ Bg Ct Gd Jo) Mf(Bb bP Gd Ng) Of(aI Gl Hw Ng) Dc(cP Mk Mr) Mp(Cs Li Nr) Nj(Mh Mr Oi) Bb(aK Pd) Gl(Bg Jo) Mt(Ng Oi) Lh(bA cT) Li(As dE) aF(cU dF) cP(aI Qc) dN(Jq Pe) CscZ CuGd EfIi GpJh LwMx HwOg IldE JsbP OicB aOdF bAcT bSeO} Ye{mZ(aK Ao aQ aU bB bZ cG Ch cJ cL Co cS Cu dA DD De dJ Ef Ez Fi Fy Gl Gp hC Ho Hv Hw IJ Im iO Is Iu Jd Jh Ji Jo Jq Jr Kd Ke KG Kj Ko kP Kq Ks Ld Lh Li Lx Ma mE Mg Mh Mi Mm Mn MP MT Mu Mv Mw Na nK nL Nm NN Nq nU Nv Ok Om On oV Ow Pd Ph Pi Pj Qd Qt Qu Qy Qz Rt Rz Tn Uc Uf Up Us Ut Vu) mU(aM Ao aW bB bJ Co Cu Fw Fy Ha Ho Hq Hv Hw Ih Ij Im Is Iu Iv Ji Jo Js Kg Kj Kq Ld Li Lx Mv Mw NA nK Nn Nq Ok Om On Ow Pe Pg Ph Qa Qc Qd Qe Qu Qz Tn Uf Ut Vu Xa) lM(Ad Aj AO bA bO cP cQ Ct Cw dA dD dG Dk Dl Ez Fr Fy Hc iB Iz Jg Jp Jr Jt Ke Kf Lh Li Mg My Mz Ng Nm Nu Nv Of On Pc Pj Po Ql Ss St Tn Ug Uw Vs Vw Wd Wh Zq Tl) iB(aC Af aM aU aY bF bQ cB De dK Dl Ez Hx jE jF Jj jL jU Kc Mk Ml Mx Nf Nh Nt Oe Oh Oz Pc Ph Ql Qm Qn Qz Rh Ug Va Vz Wc) nK(aE aL bB bE cM Cv dB dD dM Fn Hv iA Id iP Jn Jr kI Kn Ks Mb Me mH mM Mx nD nI Nx oH oK oN oV Pd Qz To Tz Up Us Tl) kG(An Ao aS aW bH bI bJ bU cA Cv dB Dd eQ Hq Ih Il Ip Iq Is Jf Jn Mf mM Mx nI Nk Nx Rj To Va Vq Yk) oV(aW bB bH bL bW Cq dB DD Fw iA Id In Jf Jo Ks Me Mf mM nA nO Nx oP Ph To Ut) nL(Cv dD Hq iP Iq Is Jm Jp Jq Jr Lh Me Mf Ng Nk Nx On Qe Rg Rm Tz Vq Tl Ti) jU(Dk Fw Is Ji Jj Kr Lx Mz Nc Ne Ni Nk Nl Nu Nw Pf Po Ql Rh Rv Sr Zx Xa) nI(Dd Gl Hw iP Is Ji Jo Js Jt Kg Ks Lh Mf Mn mT Mx nC Ng Ok On Qm) jP(Bc cB cQ Ct cX Dp Gp Hb Ic Ip Jf Jj Ju Ki Nd Oi Sf Sh Ug Uy Vt) cM(gL hB kC kF kN lY mE mF mH mI mW mY nB nC nJ nO nU) mM(Et Ez Gp Ij jB Ji Jp Jt Kg Kq Lh mP mT Na On Zq) mT(bH Cv dB Hq Hv Jf Mf Mx nR Nx To Tz Tl) Nx(mE mI mP nA nB nH nJ nN nO nU oW) nR(Ao bB cG Cu Ji Kq Ma Mg Ph Tn) mE(bB bR eC hC Jn Mx Nq Oa Tz Wh) jL(aG Ao bI Ct Hf Hx Je Nu Ql Qm) nO(aE cR dD iP Is Nq pI Tz Xa) jI(aC Hp Hx Mk Mw Nh Nn Oi Oz) bU(kE kI mS mY nC nJ nN nW) eP(Co Ho Jd Jk Mt Om Tn Wd) mW(cR eC Fn Jn Jp Jr Li Xa) mY(Ao aW Is Jn Nk Vq Yk) kP(aE Ao bC Jn Mg Ne Vq) nH(dB Hw Ip Nk Rj Tz) nJ(dD Hw Jp Nk On Tn) dU(bB Hq Jf Qz Ut) eC(kC mF mI nA pH) nU(iP Mb Mx Rj Tl) jM(Bn Jq Kc On Uw) oD(aW bJ cR Qz Vu) Nd(jQ jR jT Qe) Hv(Gp Hf Me Mx) eQ(Hw Ks Ph Qz) hA(aP dA dG dM) lY(aW bJ Iu Kg) nA(cR Fn iP Rg) jB(Ex Hq To Tl) Db(jE jH lO) Mk(iC jK jY) Mz(dX jE jG) Ut(eM iJ oE) mS(Is Jo Qe) nC(aW bJ cR) hC(Fy Kc mI) jF(aG Qm Zx) jO(aJ aP Bn) lK(dJ Jq Vc) Dd(gZ nB) Po(jK jY) Tz(eD jQ) mP(dB Ri) AopI MfoT NejE NhQc ZxlN JfnB JijQ JpiJ TlnN OhjY aGjG aWnD cBgW dDmI} Ti{uW(Af aG Ao Ar aS bF bI bP bZ Ch Co Cx Ef Ez hB hR Ib Ih IJ Io Iz Jk JM Jn Jo Js Kj Kl Li Ma Mg Nc Ne Ng Nh Ni Nk Nm Nr Of Oh Or Ow Qd Qv Qy qZ Rc Rh rT rZ sK sM St tO Ua Ue uG uM uO Uu vA vI wE wK yL) rT(aG AP aV aX Bb cE Ch cN cU ED Ef fY gL Hb hL hR Hu HV hX iH Io Iu jK jL Jv Kc Kl lN Lu Mh Mj Ms Nc Ng Nk Nl Oe oF Oi oK oN Pc Pj QB qC qD Qe qQ qT Rc rP rY sK tR Tz uM uR wF wH yJ zG tF) wH(aK Ba Cp cV dR Ef Ez Fy GL Hu Ib Ii Ij Il Io Iz Jg Jk Jm Jn Jo Jt JU Jv Kf Kj Kl Kp Lh Li Ma Nc No Nr Oh Ok Pf Pg Qv qY qZ Rc Rh Ri Tn TR TT Tv Uc Ue Ut Uu Uv Vv wJ) sK(Af aM Bn bP CH cR cV Cx Di eC Ef Hb Hu Ib Ij iP Jn Jv Kj Ko lM Mh Mj Nb Nc Ne Ng Nh Ni Nl Nr Oh Ow Pc Pj qT rB Rf Sr uR UT uV) wF(aI aM Aw bF bI Bn Cp Ct Cu Dg eT Ez gP Hb Ij Jm Ki Ks Lh My Nc Ne Nh oN Pg Qc Qu Qw Ss St tO Tr Uc Uv Vs vT yJ) rZ(Af aR aV Ax dA Dp Ed Ez Hb Ib iZ jI Jm Jo Jt Jv Kj Mg Nb Nc Ng Nh Nl oE Qv Rf Ub Ue Ug Uk Um vI) rQ(Ch Ef Hb Hu Ib Ii Jk Jm Jn Jt Kf Kj Mg Ng No Nr On Pf Rh St Ut) tX(AF cT Cx Hb Ib Ih In jE Jm Jo Js Jt Ks Li Nd Ng Nr oE oF) Af(rX tN tQ tU uM uR uZ vB vQ vT wC wP wQ tL) wD(Ib jE Jk Jt Mg Nc Nl Nr Oh St Ut wJ wK yJ) Rf(rY tO tR tT uV vP vV wB wK wL yH zH zI) nH(Gd hC Li Lj Nl Or Oy Pd Qv Vb Vt Yl) yJ(aL cR De dL hX iZ Nb oF Pc rO Ue uT) rX(aV cN Cx De Ng Oe Og Oh Oi Rc Ue Ug) Bn(sM tQ tR uG uM uV wE wQ yD yL xA) tT(De Hb Ih Io jE Jm Na qO Qv Ue tF) jE(pS vH wE wJ wK wP yH yL

Figure 39 Continued zH tL) uR(aV Cx gW hR Ib Kp Ng Oh qY wQ) wG(cR Hb iP Jj Mx oE Pj Rh tF) Pc(nL qA qB tR uM wK yK zG) wJ(cG cL cQ cR hX oF vQ
wP) rP(Ib Jn Jt Kf Lh Mg Ok Rh) Jv(rC tN tO uO vB wB wQ) Tk(Aw Dp Hb Im Jt Ju Lu) wP(Cx Ib Jk Nc Ng Nr Oh) hC(dU dX jB mS mZ nC
nK) sM(aV bP Fn hR Mx Pj Rc) sO(aV Ch Ib Jk Ng Qv Uu) tU(Hu Ib Li Ng Nr St) vB(cR Hu Io Jk Mg Oh) Hb(qI rO tR tS uT) Qv(nL rO tQ
uT uV) tL(cV Cx Hu iP Nr) oF(qY tO uN yD yK) ul(Jg Jk oE Oy Ua) vQ(Cx Ez Hu Li wK) bP(uN wL yD yE) cM(eQ jB nB nN) rR(bN Kc Rc
Ue) uV(Ib jY Li Ue) uY(Ne Or Sr uL) Gd(jU mE mS) Sf(iB mY nL) Vb(dU IY mS) wK(hA IO Nb) rC(Ez Mg Ng) qB(Nh Oz Tz) qT(Aa tO tR)
uN(bN cN Ue) uT(Nc Rc Uu) Cx(tQ vT) Yl(mS nL) dA(pS rY) nN(bU Hv) iO(yH zH) jU(Lp Vz) jY(wL yK) rO(Qw Rm) uM(hR Ms) vP(cR
hA) AaqY DevV FadX MteP NbrY NdhW NjtN IbrV Rcvl JijM JumY LizA LjtR RhfA OgnB OrqW VcjP PjzI aCaM eCpH iPpS yDlK}
jP{Sh(aC aF aO AR aW bE bI bR bS cA Ch cJ cL cM cQ Db Dg dH Dl Fn Gp Hq Hx Id Jf jM Kc Mf Mk Nf Nj Nm Oh Oz Pa Pd Qm Qw Qy Rg Rx Ub Vo Vs) Em(aF An aO Ax aY bF bQ bR bZ cC cE cG cL cS cU Db dH dJ Ez Fa hA hB Hf Hq Jf jO Kz Ma Mj Mq Mx Nd Nf Nh Nn Oz Pa Pb Pc Ph Pi Qy Um) Yd(Af aK cM Co De Ed Ez Hu Ih Ij It Jj Jp jQ jU Kd Ks Ky Lh Mj Mk Mv Mx Nd Ni Nj Nn No Ok Op Ph Pz Rf Rh Ru Sf Uh Ul Un Vz Zq) Wc(aO bF bH bR bZ cC cE cG cL cQ Ct cU Db Dp Fc Fi hA Hq Ic Jf jO Kz lL Lv Ma Mj Mk Mx Nf Ok Pi Qv Ri Ug Uh Um Zx Tj) Rz(Ap Ba Bc cI cP Ct Dg Dk Fn Ho It Jh Ji Jt Ju Ki Kl Kp Li Mk Ml Nb Nd Ng Nh Oy Oz Pc Pd Qu Sf Uc Up Us Vq Vs Vw) Sf(aC aO aW aY bF bQ bS bZ cC cG cL cM dB dH Dp Dr Ez hA Hq Jf Jh jO Ki lL lM Ma Mf Pa Pi Pk Qw Rg Tz Ug) Vz(bF bS bU cB cC cM dB Dc dJ Dk Dp Gh Hw Jh Jq Kk Kp Nc Ne Ni Nk Nl Ns Og Pd Pz Qt Rh Tz Vq We Yh Yl) Vc(Af aH aM Bn cI Cv dA De Di Dk dN eD Fn Ih It Kc lK Mk Ms Nc Nh Nk Oh Oz Pd Pz Qb Qg Rm) Tl(bC bF Bn bX cC cH cS Db dJ dK ED Ez Gd Gn Jn Jo Kf Kj Ks Ky Mm Ni Oi Rh) fR(Ad aE cM Cp cQ Ct cV Dk Fr Ii Jk Kj Nb Qa Qd Ql Tt Uc Up Us Vs Vv) Dr(Af Ax Bn cQ jF Jh Ju Jv Kp Kz Mk Nf Nh Oz Pc Pd Ph Rj Rm Um Uo) Ho(An Ax aY Db dF Ez Fi Gp Jo lM Ma Om Rt Tv Um) Yh(Ax dD Ez Hp Hq Hu Ij jF Js Mj Nr Oi Ry Ua Wd) Vi(Ax cM Ex Jt Kc Mj Nh Nr Om On Ph Qy Uc Uw Vq) Wf(bF cB cC cX dJ Ez Fa Hu Mj Mx Nf Nn) Uw(aC aW Db Js Nh Nq Ny Om Ow Ph Uf) Vb(aO aY cG Db Ez Jf Jo Ma Nd Ph Um) Zq(aC dJ Ef Ko Mm Ng Nn Oh Qy Rf) Zx(An bF Jv Kz lM Nf Ng Ow Qb Uf) Rv(cM jU Kz Mj Mq Nf Nh Oz Um) Fc(dJ Fi Gp Hr jE Md Um Tj) Uy(aC An Db Hr Jo lM Uf Um) kC(Af aR aS bE bJ bW cP Kf) Fd(aC Ax De Ii jU Ph Ug) Si(cO It Nn Ny Oh Pj Qy) kF(Af aR AS bE bJ cP) Kf(kO nC nD nH nJ nL) Ph(Rt Uz Vh We Wg Xa) Gn(cO Gp Kz Nf Um) Kc(Hp Rt Vj Yk Zw) Vw(bQ cS dJ jU Ng) aR(mP mS mU nD nT) cP(nC nD nI nJ nN) kO(aK AS bE bJ) Yi(Hp Ij Js Om) Yj(dJ Nf Ow Um) Lp(bU dJ Nn Pa) Vj(cQ cX Qm Qy) nT(Af aS bG bJ) nL(AS bE dH) jU(Gd Va Yg Yf) Ax(Uz Wg Xa) Ez(Wd We Wh) Gh(De Nb Nk) Gb(bR dJ Rc) Hl(Db Lu Pz) Kp(Rt Ru Wh) Ry(Jh Ug Vq) Op(Jf Ji Kz) Vh(Db Ic Qy) nN(aD aF Kk) Af(Fi nI) As(nC nJ) Bc(Gd Rx) Yf(Mk Nh) Ma(Sj Ux) Mz(Ef Ib) Nf(Uz Wg) Yg(Om Ow) Wc(Oh Or) Ps(Nn Ow) Um(Uz Wg) Vq(pF tO) aC(nH Yk) sH(Kq Nq) FiUg LuSj HrVa IvsF WdOm UfUx aSnJ bJlW sJpF} sH{Kr(AD Ao aQ As Ba Bc bF bG bM bN cQ cU cY dA dD Dg dM Dp dR Ef Et Ez Fy Gp Ha hO Hq Hu Io Is Iu iZ Jg Jh Jn Jt Jy Kj Kl Kp Ks Me Mg Mh Ml Mm Mn Mr No Oe Of Or Oy Pz qB Qv qY Qz rA Ri Tn tO Tr Tt Uc uI uO Uu uW vV wJ wQ yD yJ zA) jM(Ao aW bJ cB cJ cS Db Dk Gp hC hL hW iB lC Ih Il Io Iu jH Ki kQ Kx Ky lK Lz Ma Mw Ni Nk Nq Nx Or Ow Pf Pg Qx Rg Rm St Um Vt) Iu(Ax eF Ha hR Hx iA Ih Is Ji Js jT Ke Kn lL lM Mr Mx Mz Nx NY Oa Oh Po Qa qB qC QD Qe Qy Rf Rm Sr Tz Vu Tj) uM(aM aR bJ bM Cs CV cX dC Dp eF Fp hO hR Hv Hw Ib Jl jO Kp Ks Li Mt Mx oK Pa PF Qn Qv Ra Ri tV Ub uV vB vW) Vu(aY Bc cG Dk Dp Ef Ib Im Io Is Jd Jk Jr Kp Mk Mw Nk Oe Oh Om On Oy Pa Pe Pf Qh qI rA To tR tX Ut uZ Vv yJ) Dp(Ax bC Cs cY hA hV iB Io Ip Iq Ir Is jE jF Lh Lj Mh Pk Po Qy rU rV rW sC Sr tO Tv vV zG) Kq(Ao aQ As Ba Bc Ct cY dA dR Ez gW Hx Jh Jk Ke kR Ma Of Oy Pg Pk qQ rA Tr vS) iB(Aj aX Bc bJ cC cI Ct cY dB dE Ef Ez hG Hq Hx Ib Jh Jk Mg Og Oy Pf qQ tT vI) hW(aQ aV aX Cv cY dC Di dR Fa HB hR Hx iA Ic jR Mw Mx qQ qX rA) Bc(Aa Ad Dc jE Ke Qg rO rU rV rW Sr Uf uL uN uZ vH Vq vT vV wL) Dk(Cs hO iC Im jE jY Ke Lh Mh Mz Or Po Qd Rf rW Sr Tv uL wH zG) Pk(aX Iq Is It Jc Jh Jk oE Qg Rb tR tU tX yL) Cs(Ct Ef Ib Iq Je Jh Jk Ng Oe Of Oy PF) lo(hR jE Ji jR Js jT lM Mz Qd Qe Rf) Ip(Aj aN Ct Ez Fy Qu Tt Ug Uk Uu Vv) Qy(aC aX cO Jh kR Mg My Nn Oe Of Oy) Ib(dB iH Ii kR Nm Pj qY rU wJ zG) Rb(hA hP qC qD Qv sK tR tX uZ wH) Pf(hA hR iC jF jO jR Ju Qd Tv Uo) dR(fY hA hL jK jQ jR lK rT rU wH) Sr(cG Iv Jd Jh Jk Nk Om Oy Qh) tX(Ax gL hB Pg Ql Qm Tj) tR(Ax Ju Or Ou Ql Qm Tj) vI(aX bC bQ gL Jv lL oK) pF(Hf Ko Ms Mv Nx Uo vS) Rf(Is Jk Ma Of Oh Oy) yJ(dK Jr Pg Qm Qx Rg) jE(Nq Qx Rg rU Uo Vo) Dc(Jh kR Mg Of Oy) Hx(fY hP jK lK lL) Jh(Is Ju Mr Qg) Ks(Js rW vP vS) Oy(Ir Ju Qg Tv) hA(cC wL Tj tF) hO(Hf hG iH Nq) rA(Ax Kd Ny Oa) jK(aQ aV cY qQ) rU(Ez hG hV jR) uZ(iC Ql Qm Tj) Ba(Ke Qg uL) St(Al Lj sC) Ra(iC jO zG) Qh(Bb Ji Lj) Jk(Ju Ph Tv) Jv(Ji Ju kR) Vq(Cq Na qX) tO(Ed Fw Or) lK(bJ Fa Nq) uN(cS Iv Rg) Ao(Ny vQ) Ax(Of qX) Ez(Qg uL) Je(Rm zG) aX(Is Lh) cG(hR Tj) dN(hR uP) hP(kQ qQ) HfJf IqOa IvvS RgzA QnvP PgsK aQfY bCuW iAwH hGyH jRqP qQuL} Ji{cW(aD aN bI cH Cp cR dC dJ dK dM dN eP Ii Iq Ir Is Jj Lv Ly Mm Ms Mw My Nd Ne Ng Nk Ny Og Om On Oz Pz) uM(bI bM cS eD Ef Ex hR Jk jM JO Jt Kp Ly Ms Ni Nq Of Ok Pz qH QX rC rU rY wQ yJ yL) Oy(aA aN Et Fp Hq Im Iv Jg Jl Jp Lw Mh Mp Mr Ms Mu Mx Nj Nn Nt Nu Nv Ok On Pg Qd) My(aA aN bM Et Fp Im Iv Jg Jl Jp Lw Mh Mp Mr Mu Mx Nj Nn Nt Nu Nv Ok On Qd) Nu(aA aC aN Hx Ii Jh Jj Jo Jq Mh Ml Mp Ms Mv Mw Ng Nj Ny Of Og Om Pb) Nt(aA Aj Hx Ii Ik In Jh Jj Jo Mh Ml Ms Mv Mw Ng Ny Oe Of Og Om Pb) Et(aA Hx Ii Jh Jj Mb Mh Ml Mp Ms Mv Mw Ng Nj Ny Of Og Om Pb) Nj(aA dW Hx Ik Im In Jj Jo Jp Jq Mx Mz Nk Nn Of Og Ok Om) Ii(Fp Im Iv Jg Jl Jp Lh Lw Mi Mr Ms Mx Nn Ok Pa Pe Qd Qe) aC(Aj aM aN bM cX dE Ef Hr Jo Jq Jv Mz Nb Nc Nd Nh Of) Mh(aA Fp Hx Ik Im Jl Jp Lx Mb Ml Mr Om Pe Qd Qe) Yk(gC gZ hG jF kG kP lX lY mH mM nL nR oD oO oT) Of(aA aN bM eP Im Iv Jg Jj Jq Ms Mx Nn Og Ok Qd) mZ(Gb Hp Ps Rx Sf Sh Si Uw Ux Va Vb Vj Vw Yg Yi) Jp(Hx Im Jh Lh Mb Ml Mp Mv Mw Ng Ny Og Om Pb) Fp(Hr Hx Ik Jh Jj Lh Ml Mv Mw Nf Ny Om Pb) aN(Aj bM dE Ef Ik Jo Jv Lj Nb Ne Ng Nh Og) mM(Hp Rt Sf Sh Va Vb Wc Wd We Yd Yg Yi Zx) Im(aA Hx Jj Jq Ml Mp Ms Mx Ng Og Om) Iv(Hx Jj Jo Ml Mp Mw Ng Ny Og Pb sF) Ok(Hx Jo Jq Ml Mp Mv Mw Ng Ny Og Om) Yg(gL jL kG lM lY mS nC nH nK nN) Nn(Jh Jj Jo Mp Mv Mw Ng Og Om) Si(gL jK jM lM lN Nd nJ nK Tl) dX(Fa hG Kc Kk Kn Kp Ld Vz Yj) tO(cR cS It Jv oE oF rC Rm rU) Mx(aA Jj Jo Jq Mp Ms Og Om) Qd(Jh Jq Lh Mp Mv Mw Nq Om) Tl(hA hC Ju Jv lN Qz Sf) Ry(hC jR lK nC nH nL nN) Yi(kG mS nC nK nL nN) Jg(Jh Mv Mw Ng Og Om) aA(Jj Jq Mp Ms Og wQ) eP(bA bV Gd Or Un Vv) Hp(Ed gL Ho jQ nI) Sf(iC jF Nd nJ nK) Jl(Hr Jj Jo Mp Nb) bM(Aj aS bJ Ef Jo) eO(cK dC dJ In Ml) lM(Lp Ps We Wh zG) Lw(Jq Mp Ng Og) Ms(Jj Jo Nd Og) Mw(Mr Mu Nv On) Vi(hA hC nC nL) cS(sK uN vA yJ) dW(aE aF dJ Ih) wQ(Il It Jv Ne) oE(Qx Rf sK tR) Mv(Mr Mu Nv) Yd(eQ gC oD) Zw(eD jQ kG) Wc(hA iC lY) Vb(dU mE nK) gV(iH Ju Vv) tX(bI Kz rB) Ex(sM yD) Gd(iJ mE) Nm(Ng Og) Mb(Ik Ml) Nb(Pa Pe) Vz(jR lK) Qc(Jj Lh) We(jY nN) Jq(Jj Og) Rx(nB nR) Rt(eD lN) Uw(nK nN) Uy(lN nJ) wJ(Il It) iA(uO zG) yJ(Ne rC) sI(Pf zG) wF(Dk To) jO(sK uY) vA(Jv Nk) BbEw DwLx EmqU GnoP MpNg MuJh IbuL ShkS WdjF WhjY JorQ LpjQ NydU VclK VhnO VjnL aXsJ bOoV cMgZ eCpH tRrA uYvT} gV{dR(Ad aP Ar cA cP cT Cu cV Cw Dc Fr Gl hC Hx Ih Ii Ij Im Iq Ir Jk Jl Jn Jp Jr Js Lh Li Lj Lx Ma Mb Mj Mk Ml Mt Mw Mz Nm Nw Nx Ny oE Og Oh Om On Po Qb Qd Qe Qt Qw Vt Vv) Rg(Ad aL Ar Ax aZ Ba bH bO cI DD dJ Fa Hb Ij Iu Ko Lv Lz Mh Mk Ml Mr Nm Nr Ok Ow Pd Pe Qx Rf Rh Sr Ub Ue Un Tj) Li(Ad aK aU bC Bg bO Ch cM cO cV Cw dH eM fR hB Jg Ju Jv Ki Mc Mg My Ng Nj Nm Nu Nx Ql Qv Qy) Qh(aK cA cP cW cY Gd Hv Ii Io Jm Jn Js Jv Ki Kr Mf Mh My Ne Nh Nl Pi Rm Ub Ug Up Uu Vo Vp) Vo(Ad aI Ar Ax bA bE bO cI cT Cw dD Fp Ij Ir It Kl Ko Ma Mf Mh Mk Ml Nm Ow Pj Po Qv Qx) Qv(aC aI aK bE bO Cv cZ dD dI Fa Fy Gd Jl Jp Ki No Oa Ok Po Qa Qb Qe Ua Un Us Vu) Ug(aC aM bB bE bO cB cD Cv Cw dD dl Dk Fr gP Jl Mn Mt Mx No Nq Nr Oa Po Qa St Vu) Jv(Cs Cw Dc Et Hb Ir Kn Kq Ky Lh Lj Lx Mp Nw Po Qe St Tn Uf Vu) dD(aD aM Ib Je Jy Qg Qm Qt Qu Qy Ri Rj Ss Ue Ur Us Uu Vq Vt Vv) Kx(aZ Cq Cu cV fR Ii Jm Kl Na

Figure 39 Continued

Figure 39 Continued cH cI cY Kx) Ki(kN lW lY mH mI mW) Or(kK kP lW lY mE mI) fR(Cx gW Hv Kr Lv Oe) aR(lX nC nD nH nO) mP(An bH cC dM Kc) kN(Aj aM As Ax bX) kP(aM Ax Bb Cs Dl) Kx(kO nA nI nJ) lX(aS Bb bN Kf) lY(aM Ax cJ Cs) mE(Cs Dl Kc qU) nH(aG cH dM Ld) nL(aG bM cS cY) Em(Gd Oy Qt) kO(aG Bg cH) Kc(nI nK) dM(kG nI) mZ(Hc qU) tR(Ip Tr) AnmY NgWn HbkK LdnD QmwF UhtT PhmW aJoQ aMlW cHnO} Sf{jM(aD aH aL bJ cI cZ Dc Dk Ex Hf Hv Is Ki Kq Kx Ky Ld Lv Lx Mk Ml Mp Mt Mx Nw Or Ou Pe Pf Pg Po Qa Qe Qg Qh Ql Qx Rv Si Un Up Uw Vi) Nd(bB bR cD Cs Dc Dd Dk Ho Hv Ij Iq Ir Jp Jr Kk Li Lj Nm No Nr Pj Qh Up Zq Xa) nK(aI aK bB cZ dA dB Dd kI kP mH Mn oH Up) jF(aH aM Dr Is Jq Ki Ky Lx Mf Nw Or Ou Xa) kP(Dd Gp Ij Iq Ir Jn Ne Nk oK Up Zq) Mn(eM eQ mE mW mZ nB nR oE pI) jY(aM bS Dc Hf Is Ki Lj Or) aW(jB kI mY nJ nN oD pI) mW(dB Fn Ij Jp Lu Nk) jR(aQ dB Hb Mf Oi Oz) Dd(kI mS nJ oE oT) iC(aM Is Lh Nh Or) oQ(Ij Im Kq Ph Qa) Gp(Hv iA oE Or) Jp(eF fP fR Nk) lN(Hf Jq Ke Tz) pI(bX Mx NO) Up(nB nN oE) jH(cC Pd Ug) jQ(Db Hf Oi) Nh(jK lO) Ij(kO mU) Jn(kI oP) aG(jG jT) aR(gC oD) DbjK FwmU FyeF LvlK MfjG MxkI NkgC UseD aMjI bGoE cFfP cRjT} wF{To(aH aN aW cL cY dA De dN dR gW hP iA iP JF Jk jM jO Lu My Nc Nj No nW Of Qd Qe qH Qm qO qQ qX rB rR sC Sr tQ Un zG) Qm(aN bU cB Ch cQ Cs dB dN eD Ef hP iA Id jF Jk jM jO Kp Mg Mh Of qX rB Tt Uk UM Vt Vv tF) iA(Ap Bb Dg Dl Id Im Ke Kf Ko Kr Pj Ri Uh Ur Vq Wm) jO(Ar Cs Cv Fb Jd Ke Kn Oa Pj Ql Ri Tz Vt Wm) Jk(Bb Dl Fa Iz Ke Kg Pj Ql Tz Ua Un Vt Wm) jM(An Ar Cs Ke Kn Ow Ri Uh Ur) Bb(cG Dk Ef jF Nq rB tO vA) Dl(bC cY Dk dN Mg Ng qH tO) Ke(bI bQ dF Dk Ib Jo vA) rB(Bc Cs Kd Kk Ql Tz Um) aN(Dk Ql Qx Vt tL Wm) dN(Ar Ko Pj Ri Wm) Of(Ax Ks Pj Ri) bQ(Fa Id Um Ur) vA(Jf Pj Un Vt) Dk(hP Im iP) Ib(Kq Ny) Id(bC uM) Tt(Qe Vq) Ri(jG oK) Uh(cB tO) hP(Tz Uk) AnjF CsoK EfQe FaEx TrVq JtPj KdqH KpiP QnnW VttO} Jp{Nj(aA Fp Ih Im Jl Lx Mi Mr Ms Mx Nv Of Og On Oy Qa Qb Qd Qe) nT(Ad Ef Ez Ib Ic Iz Jv Kk Kl Ow Qv Qw Rg Ss To Ug Ur Uu) Iz(aN aW bM dB dE eM Ic Kq Lj Mx nO Of To) eM(Kf Kk Kl Kx Ow Pk Qw Tn Tr Uk Uu) nO(Dp Gd Ib Kl Qw Ss To Ug Uu Uw Vs) Ry(eC eD fP gP mY Nk nL nN oE) Uw(bO mE Mf mW nA Nd NK oE) Im(Fp Mh Ms My Ng Of Og Oy) Eq(iJ nH nJ nN nU oE Ow) Vi(fP mW nH nJ nL nN) Ef(aN bM Kq nN Wm) Qd(Ms My Of Og Oy) To(jB nN pH pK) Vc(Ib Kk lN Ow) fR(Ed Oa Or Uu) Fp(Ms My Og) Gd(iJ Kk mE) Si(eF mW Nd) Sj(Bg Ma Ow) Wc(iC jL jY) Wh(jL Ld Ow) Jv(aN eF Lj) Rz(eD lK Nc) Mx(aA Og) Ib(No Vz) Kn(pH pK) Of(Js Kq) Vj(kG oE) nN(Kl Ri) mW(We Yi) DrlN DueF EwaY NdRx QbOg KkoP rCkC} eQ{Kx(aF aL An aW bG bH bX cQ Du eC Fr Gp Ho Id Ik Iu Jn Ky Lv ME Mk nC nH nL nW Po Rf To Up Tj tF) Uu(AO cG Ch eM Hc Jq Kg Kq Mn Na Ns Nv On Pk Qn Rt Tn To Tz We) Mn(bO cQ cR Gb Gd Jt Kl nW Op Si Uw Ux Vj Vo) Ph(cA Gb Gh Ho Ps Ry Rz Uw Ux Vi Vw Wd We) nW(aL dD dK Id Kg Lt Nj Rf Tn To) nH(Fa Fd Fn Qw Rt Us Vo Vv) On(bO Ef Kl Rz Uc Vo) Ks(Gb Uw Ux Va Wd) Ao(Kj Ux Vo Wf) Ha(Gb Rv Ry) Wf(Jn Me To) Qw(Li nC nL) Kq(Ef Kl Rz) Ld(bL Fn Hu) bU(aR fP Rh) Ho(aL dB) Qg(bH nO) Jn(Lt Uw) Tm(kG Qa) Pi(cA Rv) cD(nN Xa) AabO CqJv DuoT EqcG FdkG NoRf TtIt TopK WdQz JsUw RtcR UpVa} Ew{Mb(aR aV aZ cB cF Cq Cu cW Dd dE Hv Ij Il In Ir Is Iv Jm Jn Jr Js Mc Mi Mq Nc Ni Nj Nl Oe Oi Pc Pg) Nj(aD An aQ Ax bA bS Cs cT cW DC dD Hu Hv Ij Jm Li Lz Me Mg Mk My Nd Nn Nr Oy Oz Pb Pd) aM(aJ Aw bB bC bE bF bM Bn Bo bQ cD cL cQ Dd DK eM Hr Ik Im It Jl Mj Mv Nh Nx Po Qa Qb) Mn(Dc Lh Mt Nd Ni Nw Og Oi Qb Qe) Nk(Aj dC Hu Mu Mv Oy) Lj(Aw aX De eM Fr Mu) bM(bB bE Mk Oi Oy) Of(Ap cW Mf Ng) bR(Af aY cG dN) Ao(Bo Gp Jq) bS(aN aW Hq) cX(Bo bU Dl) Is(dC Ml) Nw(Cs Ng) aF(cG Mm) bB(cP Hx) AfQe AjcW AxMf PoeM GpJh LwcP NdJq IvdC NxcR OecB} jF{aG(Dr Em Fc Fd Gn Hl Ho Rt Ry Uw Uy Uz Va Vh Vi Wf Wg Yl Zq Xa) Lp(Ct Dk Dr Fy Kq Nb Nk On Po Ps Qa Vu Yh Yf) Wh(aH Cu iC Jq Jr Mt Uc Uw Vi Zq) Dr(aV bO Gp iC In Ju jY Rj Uk) Uw(Cq In jY Ni Qw Tv Ua Zw) Vi(Ef Hu In jY Rj Ua We Zw) Zq(aH Io Jv Ni Oi Po Vz) Vc(aO bO cE cJ dD dF iC) In(Gb Uy Yh Yi Yf) Vz(aH aI bB Lh Yl) Xa(Jv Og Oi Qt) Rv(Ba cV Jv Nk) Gd(Fy iJ Uc) Yi(Cq jY Tv) Zw(Jr Mt On) Yf(aI Qn) Po(Uy Yd) Nk(Hl Vj) Yj(Nc Ni) Rt(aH Fy) aR(kO nO) oQ(aS cI) AskF CxlW GnGp HlaI IduI TowD IhPs HfTm IoVj YdbA SjQl WeOn WfVt UyjY PjnT bGlY sJpF} tT{Dl(Aj bU cB cF Ct Dk Ef Jk Jt Kz Ly Mg Mh My Ng Ou Ow Oz To uN Uu yL) Mh(Aa AN Cv cZ dC dD hP iA iP jO Ke Kr kS Ld Qg Qm qU rB rC rS) Kz(aF Ar cH kR Ly Mf Ni Nj oE Pb Pk Po qV qW rB rC rP Sr vI) rC(Ch fP IP Jv kR Lj Mf My Ne oE Qz To) Qm(aW fP Jk Jv Mg Ne Of uN yL) rB(dB Jr Kk Md Mf Mt Oa Oz Um) To(cH hW iP lO oE Pk qV qZ) Vq(bW iA Ib Pk Tr vA) iP(gL Ip Ly Ms rU uI) kR(dE Iz Oa Ou sJ Wm) Mf(hP qU) Ip(aN iA) Jk(Cu Un) Uh(aW Nj) vA(Un Vt) EfrP FbjO LyKr MnJv QzQg KefP PkyL} Nw{Of(aA bM Fp Ij Ik Im Iv Jg Lv Lw Mb Mf Mp Ms Mx My Nj Nl Nm Nn Nx On Oy Qa Qd Qe) Ms(aA Fp Ih Im Iv Jn Lw Me Mh Mx My Nl Nm Nn Nx Og Oy Qa Qb Qd Qe) Og(aA Fp Ij Ik Im Iv Mb Mf Mh Mx Nj Nl Nm Qa Qb Qd Qe) aA(Fp Ih Im Iv Lw Mb Mh Mx My Ng Nj Nl Qd Qe) My(Fp Ij Im Iv Mb Mh Mx Nj Qa Qd Qe) Nj(Im Lw Mh Mp Mx Nd Ni Nn Oy Qd) Fp(Hr Lw Mh Mx Nl Nm Om Oy) Mh(Im Iv Lw Mx Nl Nm Qd) Mb(Im Lw Mx Nd Nm) Iv(Im Mx Ng Nq Oy) Mx(Lw Mj Nm) Aj(aN bM) EmqU NlIm VzjR QdOy} mW{Du(aD aE bU dB Dd eC Fn Gp jB Jn Me mY Nf oE oT To Ud We Yj Tj) jY(Al As bG Bn cG Cq Kc Kd Ki Kj Mj Nn Ph Pi Pk) Jn(Gn Hl Ho Ps Ux Va Vi Vw Wc Wh) Xa(Bg cD cW eC kG Og To) rZ(aR aV bA cT cW dE dN) Nk(Gb Hl Lp Uw Ux We) Yj(Fa Hu Kp Lj Pd Us) cR(Hl Uw We Wf Yi Tm) Li(Ry Vi We Yi Yf) bU(Vz Wc Wd Wf Yl) qX(Bn De Ki Kk Ph) Eq(dB Ha mY oE) Hl(aO Fn Hu Lj) Vi(Cs Ij Lj No) We(Ax Lj No) Kc(lK qU qV) qW(cU Iz Ph) Zq(Gd Uu) qU(cC dB) rY(bA dM) lN(Ke Pj) CujK DdVa DejI TjYi GnHa WcUs KijH RzUu RyLj UyjB PhqY PkjM} sJ{Kr(cY dR eD Fw hO Hx Md Or Pb qU Rc rQ rX Tj tF) Uh(aX Bc cV dB Dp Hf Iu Kz Li Ng Pa Tr Tt) kR(aY bC cT dN dR iA Jk Mv Ni Of pF vI wE) jM(Af aO Bn Cx gP iP Iu oF Qg St) Ip(dH Fy Jy Pi qX Tn Tt Vv) Nq(hP Rh tR tX uN vI yL) Kz(dH dR Ed Ha Qt Qw Vu) aX(bZ Ke Nv Ny Pg Ql) pF(aZ Cs dM oF rW sC) Iu(AR Nv qC Tz) dR(fY qO uI uM wD) wH(Aw Bo cW dB iH) Hx(aI fY jK tV) uM(Ir pY Ql Qy) Hf(bC Hw Vu) iH(hW Pb Pg) vI(aY fP Hq) Bc(cO dH) Tj(dB Mf) Ib(No rU) Nv(Jh Jk) Pa(Pg Ql) FatR MfSr NlhW RbPb KoVq dBoF} nK{Lp(bB bU cR dB dE dJ Jn Jr mH mI nI Nk Nq Qz Rh) Yl(aI bO cD dE Iu mH nJ To Up We Yi Tj) Eq(aL cG cY Dd Gp Jq Nx oE On Tn Us) Vz(aK aL cY cZ Gp oD oH oT Up) Zw(Hu Jn Jr Ks Rg Up Us) aI(Gb Gd Ry Si Uw Ux Yi) Nx(Rz Va Vw Wd We) Rv(dB eC Ik kG) Uw(Cu Kq Lh On) Vi(Jr Lh Or Rh) rZ(aE aO bU bX) Dr(aV bE Qv) Du(oH oT Up) Yf(aM kP lY) Gb(eC Nk Og) Hl(Nl Og Rg) We(Hq Na Tn) Ry(dD oH Or) Rt(Og Rh Uu) Vw(Ao bI Cu) Gd(cA Mn) To(jB pH) Yi(aH dD) Si(dB Up) Va(Dd Up) aL(fB oW) dE(Lt Wc) DlZq SjoH WdmH WfcR QwgC KkoT OpoD cUqX} jB{To(aI aW bG bH bL bM bR bU bX cA cD cQ Ct dK dN Dr Fd Gh Hu Hx Ik Ip mE Mk nW Of Og Oy Oz Pf pK Qw Qz Rc Sr Uu Vs Vv Zq) Qw(aG bG bX cA cF eC gC mE Ne NH NL Pk Uc Uo) aW(Gb Hf Ju Jv Rf Ur Uv Wm) bI(Ps Qz Rf Rm Ue Uw Ux Vo) cD(cF Gp Hf Jf Kk Rf Ub Uv) Ib(Ao Mu Na Nx Ny Pk) Ao(Kl Uc Uu Ux) Rf(bN cA Jn On) Pi(cA Ry Vi We) Eq(Qg Qz Us) Ex(Ct Fa Uu) Mk(bN cF Jn) Mx(Ry Uw Yi) Ny(Mn Pk Vi) bG(cF Hl Tm) Ux(aS Ne) cA(cX Id) dM(Tn Tz) FbLv FrcF WfaS JnVj KlKq VscG aLaO aRbH} lK{Vc(aF aG aH aI aL aM aO bB bE cE cI cJ CU cZ eD Ij Is Jq Ky Ld Lh Lp Lx Mk Ml Mm Mp Nk Or Ou Ow Pf Qx Rv Vq Vt Yl) Yd(bH Bn cB cC cH dJ Ed Ky Ld Or Ou Qx Rz To Vt) Vz(aM bB Is Jq Ld Lv Lx Ml Or Qx Rv Yl) Dr(aM In Jm Jo Ph Qz Rj Rt Uh) Rz(aE aG cV Ky Mt Nd Ux Vq) Rv(Ax cL dB dG dJ Js Mx Oi) Vj(cB Nj Uc Us Vu) Ph(Rt Uw Uz We Wg) dJ(Fc Rx Uw Yj Zq) Vi(cS Hc Jo Tv) aE(Gd Vw Wd Zw) Rx(bS dB Pi) Oi(Va Xa) cU(mT nD) EmHf GpWc TmbS LhfR LpPi cHmT dFoP} iC{Sj(aF aO bS cE cG cL dH Hf Kc Ph Pi Vc) Wc(bI Db Dc Hb Hx Nf Nm Pj Qw Vq Yd) Nh(Fd Gb Gh Lp Lt Rt Ry Si Va) bS(Ru Ry Vc Vz Wd We Wh Yl Xa) Lp(Af bU Db Mk Oh Rh Tz Vu) aR(kO mZ nC nD nH nI nL nR) Va(aM bJ It Ng Oh Oi Rc) Hf(Ru Uy Vc We Yl) aE(Wb Wf Wh Yh Zw) cR(Hl Ho Uw Uy Yd) Nd(Em Lt Op Yd) Kc(Uw Vz Wd Wh) Dr(Jh Nf Pd) Vc(cL Hx Ny) Db(Wb Wh) Nf(Gn Tm) In(Fd Vi) Vz(Mj Mx) Si(Oh Pj) Ru(Kp Vq) Wn(Ct Ng) Ux(aW Ph) cU(kO nN) AfWf BnPs CvHl YfUo HoaG RyOz LtdJ OhVj UycB VhVq} lN{Zq(aE aG aM Ax bR bS bV cL dB dH Dr Ez Io It Jn Jt Kf Ko Ng Ni Nr Oh Om Ow Pi Rc Sr Um Vc Wc Wh Yd Tj) Uy(aM dK eD In Jo Jq Ld Ml Or Po Qm Qx Rv Tz Uh) cU(lX mH mP mT mU

Figure 39 Continued nA nD nJ nO nT) Pj(kI mH mI mZ nA nO nR) aR(kK mM nI nR oQ) Yd(aN Mp Ql Vt) Rv(cQ It Ki Vt) Vj(Bc bS Pa Uw) cW(kK lY nJ nN) Hf(Em Lp Yi) Ql(Lp Vz Yl) Vc(cG Mm Vt) aE(Hl Va Wd) cI(kI mS nA) Gp(Dr Gn) Id(rC uI) Xa(bS Oi) Uw(aW Fd) aS(kK oO) aZ(lY mU) cV(oO oQ) oP(aF dF) InYh KkmT KxmS bElY} jM{Uw(Cq dJ Ef Ib Ih Ko Ks Lp Ng Ny Oi Qt Qz Rc Rf Rj Ua Wd Zw) Lp(Bc Ct Db De dJ Fd Jq Mb Ps Uy Vt Vu Yh Yi) Rv(aG Ba Ct cX It Ju Jv Ki Rj Up) lY(aR BG Cu cV dF Hf Ki Or Ou) Vt(Gb Gd Rx Si Va Wc Wf) Hf(Ho kN Si Va Wb Wd) Zq(Ef Io It Oi Rc) In(Dr Ry Yh Yi) Uy(Gd Hr Ks Mh) cU(mE mT nB nN) Gp(Fc Gn Wc) Rj(Dr Yh Yi) Vi(Jv Om Rm) aR(kO mM oQ) Rx(cQ Ct) Vc(aO cJ) uI(Bn wB) DrbO FyfR MpYd NdSj NgVw IhPs ItYj WdaE XaOi YlaG TkrQ PkkF cHmT tXiP} eC{pH(bE bH bR cO cX dJ Em Eq Ez Gh iA Id Kl Nd Nj Ow Qc Rb Rf Rj Rt Ry Ss To Tr Uh Us Ux Vi Vq Vs Vt Vu Yi Zq Wm) pK(aL aR cF cX dD dJ Fw Hb Hl Ic Id Iv Lt Mk Nf Nj Ns Pk Qg Qn Qv Rf Tn Tt Tv Um Wm) nO(Dp Ed Em gC Qv Ri Tz Ug Um Yl) kF(Dp Ed Eq Fw Ha Kl Rg Ri St) Ry(gC Jr kC kK mE mI oT) kC(Eq Qc Qw Wf Wm) Rv(mE mI nA) Ri(kK nN) nU(Ed Oa) mI(Lt Wf) oW(aL cX) pI(Id Mn) EmkG TneM VhgC VikK} tO{rB(Cu Fa Js Ke Kr Lx Mh Mq Mt No Nr Oa Ou Pd Pe Po Un Wm) Vq(aI aL aM aX bE Bn cT Cv cZ dD De gP Mb rS sK) Mh(Aa AN Cu Cv Dl Ke Kf Kn Kr Ld Pk) iP(Cu Ip Jl Kr Ld Mq Mt Nr Ou Pe Po) Uh(aM cH DL Jv kR oE oF uY) Dl(aF bU dD Mg Mt Ng Oz) Jv(Bb Ke Mn Qd Qm rC rP) Un(cR cT Jk Nq Qg) Ke(cR Ef fP Jh) Vt(cR cZ Pc rC) rC(Id Kr Mx) Po(Ef Hc) Ip(aN dD) Jk(Cu Ou) Kz(oF Sr) AaiO BcyL NeQm KfcB KraF LdrP} qU{mE(aK aQ aR aZ bJ bX Hb Ke Pj) nA(bC bI bR cH cQ cU dB kF Pj) Em(bS fP Lh Lv Lx Mh Mk Ql) qT(kC kF kK lW mI nR nT nU) mT(aG aR bG bZ Cx Gp Hb) kI(bC bI bR Cv cZ dB Dd) kK(aR aS aU bE bJ cV Cx) lW(aK bE bJ qW qY) lY(aU bE bJ Cx qW) qX(kF mP nN nR nT) mS(bR Cv dB Kx) Hb(nI nL nT) Pj(nL nR nU) cU(lX mP nD) bE(kF mH) nD(Aa rZ) qY(kF mI) qW(kC lX) kG(Bn Cx) kO(aG aR) oP(aH bZ) oQ(cI dG) ExuI GdKr IptR KenI bJmH cCnR cQoO dBnJ} jY{aR(kG kI kO lX mF mM mP mT nF nJ nL nO) Wc(aE bC Gn Gp Kc Nd Nf Qb Qm Zq) kF(Af aG AS bM Bn CX Pj) Qm(Dr Fc Rv Uy Uz Wg) aS(kK lW lY mI nB nT) Hf(Lp Ly Ps Yd) Zq(Ib Jn Nn Oh) mH(bC cC Kk Kx) nA(aN cG Hc Kk) Nd(Fd Lp Rt) Kz(Gh tX Vz) Rv(bS Qb Ql) nT(cC Ki Kx) Af(kK Wb) Ry(Jh Pd) Ql(Rx Wb) nU(Cu Kx) DdnO DrbO FiOu MxWd NgWn TotX SiUn SjOh ZwbS QbVa WeJq WhKp KcPs KkmU LhRt LpPa OrlY VccL ViOz bGmT bZoP cCmZ cIoO dFoQ kCrX} aL{fB(aM aP aR bZ cR cW Db dN Fw Im Iv Ju Jv Ld Li Ma mF mI mP mT mY NA Nb Ni nL NN nO nT nU nW oH OW Pe Pj Qa Qd Qe) oW(aG aO aW bB bH bJ bM bN bR bU cA cI dM Eq fP iA Jn kF Ms Mx nR Qe To Uc Uo Vs) pK(Af aO aS bJ bN bR cF dM fP Im Ip Jn Nb Nl nL nU Ny pF Qd To) mI(aM As Eq Lj) nN(As Io Ir) nO(bC Ur Uu) pH(To Yi) LilW UrnL UsnT hXkF} eD{Zq(aW Ax bS Cs Ez Fp Kz Li Mq Nf Ng Oi Oy Qb Rf Rz Um Vc) Yj(aE bS Db Kz Lj Mx Nf Pa Yd) Vc(BC bI cL cU dF Fy Uv) Vw(aW dH Fp Kz Mx Pa Pi Rf) Ax(Hl Ho Rv Uw Wc Xa) Yd(aN aS Fy Jm Ns Uv) oQ(bF bG bO bZ cG cU) Ry(Ad Fy Hf Jh Qy) Ux(bS cL dH Dp Pi) Wc(Kz Nf Ou Qm) Rv(bS Kz Mq Nf) Qb(Gb Ps Wf) bI(Vi Yh Yi) Dp(Lt Wf) Vz(Bc Tz) aE(Hl Zw) bG(kF kK) bS(Vj Xa) BnFd EmMx NfWg IduM UnvA cCnR cHnN fRhR} Ex{sM(dH Dp Gl Ih Im Jd Jr Ke Kf Kn Ko Nx Ny Qd Qm Qy Tz) Dl(eZ rS rU tS tV uG vW wD zI tM) Tz(qI uO uY vS vU yL zA) qZ(aO bF bQ bZ cG Nn Nq) Fa(uN vP vS wG wQ yL) uN(cV dD nW rT rU) Jv(hP qI uW vS) Oa(uP vU wH yK) Qm(uG vW yH) wH(aJ qX Un) tM(aO cG pF) sC(Ke Kk rV) yL(Ad Ld pF) Im(rS rT) Qd(rW yH) Qe(qI rV) Qt(uG uU) hP(Ky Un) yE(Ax Cs) GluG HwrS KeuM KorP VtwJ cNuI cVvW dDyJ wLpF} jI{Lp(aE Af bU cE cR Dr Hx Kc Mk Mx Nd Nh Oh Qw Tz) Vc(aG dF Ha Hu Hx Ib Ih Im Mw Ps Qw Qy Ua) Yd(aG cR Hu Mu Mv Mw Nd Ua) nT(aR aS bR cC cU Dd dE Ki) Rv(Bn bS Kz Mq Nf Oi) Fd(Fa Mx Nd Nh) Wf(aE Db Hu Oh) Ax(Wc Yh Yi) Gd(Fp Kz Nf) oP(aD cF dC) Dr(In Ny) Nd(Ps Vi) Yh(Hu Mw) Vz(dB Ub) Wc(Hx Qw) Wh(Kc Nf) Rt(Cu Dp) Pj(mH mM) DbWb FiaG NhHI ItVa WebS KcPs RxOz ViVq VwaM aRnI aSlY cUmH} bU{oW(aG aN Ap bE Bg cF cO cX cZ eF Fr Hv iA Ic iH In Iz Jf Jk Jr Mk Mx Nd nH Nj nL Nq nY oK Pz Ue Up Uw Wd) nN(Dl Eq Lp mT My Nd nI nO Og Oi Ry Wf) pK(cC eF Gd Gp iA nC nH nL nU Pi Qg To) pH(aG cO eF gL iA Kn Uw Wd) Wf(kE kN mS nC nJ) nO(Gd Gn Yl) rZ(mI mP nD) pI(Ib Jv Qw) Xa(gP kG) nW(fA Ho) oD(Nd Qw) GnkP IbgC ZqgP WdkG WhlY LpjH UwkE} uM{Mx(aF aN cV cX Gp hP Id jK Kc Ly Nc Ni qD qH Qn qX rB rC rQ rS rV Uh yL) rC(An Bn Hv Hw Id Ij In Jq Jr Js Md Me Mj Mq Na Nm Of Or Pb Qa Qe sK) Ly(Bn Id Jl Ke Kf Kr Nx Un Up Vt Wm) Qm(dA Id qX sK uN Vv yK) Tk(Ap Cw jT Kp qD Qu) wQ(Jl Ke Lh Lx Mt Po) Id(cX Gp hR Nq sK) To(Ke Ni Pk qZ Un) Nq(Ha Tj) sK(Gl Vt) IpaN JkUn KehR qXuI} qW{kF(Af aM An bH bJ Bn Cx Kc Kf Ki Kk Ky Or Ph Pj) lY(aF aK aM Bc bG bJ bX Dl Kc Ki Or) cU(Hf lW mE nB nO nT oQ) kN(aA Ad Aj aM As Kc Mr) bH(kC kK kP lW lX nT) nT(aS cF Kc Kk Pj) Or(kC kP lW mF) kK(bG bJ Dl Kc) aR(kO lX nO) cH(kO nN oQ) lW(aK aM aZ) Gd(Dd Lv) Ng(Tk Wn) Kc(kC mF) bJ(mE mI) nN(cY Kk) CxmF DlmE KrbM KztX LhdE PjnI aGkO aMkP aSlX cQoQ fRtF qXuI} Nj{aA(Fp Fr Ih Ij Im Ir Jg Js Jt Lh Li Lw Lx Ma Mr Mt Mx Ni Nk Nm Nn No Nr Nv Nx Ny Og On Po Qa Qb Qd Qe) Im(Ik In Iu Jg Jl Js Jt Lh Lw Mi Mr Mx My Ng Ni Nk Nn Nv Nx Of Og On Oy Qc Qd Qe) On(Ik Jh Mh Mr Ms Mv Mw Mx My Ng Ni Nk Oe Of Og Om Oy Qd) Og(Ij Nv Qa Qd Qe) Nk(fA gZ Qd) FpNx NmQe LpjH cRgZ} jQ{kF(aA Ad Aj As Ba cU dM Kc Ke Kf Ki Kk Kl Or Ph Pj) cU(kC mF mS nA nB nD nF nH nJ nL nN nT oQ) Db(Ho Op Ru Rv Uw Wc Zq) In(Dr Gn Uw Uy Uz Vh Vi) nT(aF bO bV cF Kp Pj) Vz(Ij Ld Lx Ml Qx) Uw(bS Hu Lp Oi Qt) Nf(Rv Uz Wg) Hf(Si Wb Yd) Oi(Vj Zq Xa) aS(kI mS oQ) bG(kK lW lY) Lp(cB Lx) Pj(kC nI) aG(kO Yj) DrRj GpHo MpYd WhaE KikK KzRv VjbS VwPh cHoQ} nO{Um(cA eF Nd Nl Oi Rf Rm Vs) Ug(aE Iq Jr kR Nd Nk Nl pF) Dp(Fy Iq Nd Nh Nl oE Us) Eq(Cu dB Ef Kq Nd oE Ud) Xa(Gp Ib Og Oy pI Rf To) rZ(aX bQ bR cQ cR dD) Gn(pI Rg To Up) Gp(Dr Vz Wb We) In(Ed Oa Pi Vu) Nk(Hl Lp Ss) Rf(Li No oE) Vs(Ma oE Pf) aR(hR qX qY) pI(Du Yl Yf) Kq(Aj Ct) gC(Fc Uy) DdVa DlZq DrdD NdQv IsRm RxUs YlbO cFrB dMhV} oD{Ld(aO bG bX bZ cD Dk Ib To Vi) aW(Du Gh Ju Jv Op Vj Vz Yd Yl) Eq(cR kG Kq Li nN oW) Nl(Fi Ho Lt Rz Wf Yh) Du(bJ nC nH nL nU) Kq(Co Dk Ef Ib Kl) Pi(Ry Vi We Yd Yh) cR(Ib Ny Uv Uw Vj) bJ(bO Jv Nd Qw) Na(Op Si We) Qa(Ps Ry Vi) Lt(aM Nc Ni) Bg(Rz Xa) Ib(kG nL) We(Kg Ph) bG(Wh Tm) bX(Jv Vz) cD(Ju Kd) FcnA NoRf NcWf HvYd ImVi QwiO UubC} tX{iP(bL cS Cv Dk Dl fP hB hP iA Ip jO Kd Kp Kz Mk Nq Nx oE Oy pF Qg rB Rm To uI uO wJ wQ) Kz(aF Bb cH Dl jO Ni nW oE Pk Qm qQ qV rB rC rR Sr) Qm(Ch cR dB Ef iH Jk Jv Mg Mh Ng Of rB uN) rB(Bb iA Ij Jr Js Ke Mx) Mh(Aa bQ nW) Ip(aN cR iA) nW(cR wJ) DlNg EfNy ToqX KdqH VqiA dBoE} qX{uI(Bn Ch Co cT Dk Ef Ez iA Iz Jk Jv Kd Kp Ma Mn Mx Ne Nk No Nq oE pF Qw) kF(Af Aj Bc bH Dl Ko Or Pj) cU(kC kO mF mT nB nD) Kk(mP nD nH nN) Em(Hf In Qt) Gd(bS cR Mh) Pj(kC mP nI) aR(kO lX nN) nT(aZ bH cF) zH(Dk iA Nq) kN(Aj As Iz) Kc(mP mT) Or(kC lY) bG(kK lY) cH(nL oQ) CvzG DdkG NgWn TowD HcmZ IptR} rZ{mS(aE aF aO aP aR bA bE cQ cT dN) nJ(aF aV cE cI cP cQ cV dH) lX(aI bA bB bV cT dD) cQ(mF mI mP mY nI) oP(aG bZ cF cI dC) lY(aH bL bO dC) mY(aR aU bA cY) Ng(Gl Kr Pj) mP(aP aR aZ) mU(Aa bO bP) Kr(aN Of) cP(kK oO) cY(mZ nC) dH(mF nI) nT(aO dN) mM(bQ Pz) nD(aP cD) IduI VqpF aInN aRmT aUmI cFnF cImH cVoO} Eq{kG(Cu dB Dc Dd Fy Ij Iq Jg mY Nf Ng Qc Up Us) mY(Ao bB cG Cu Kq Lh Ma On Ph Rz Tn Uf) Dd(kC kF kN lY nD nH nN oW) nN(Ao Cu On Up Us) mS(Ef Ij Is Kq Ph) Gp(iJ mM mZ oE) Nd(Li Qh Xa) nH(Dc Ij Nk) cG(nR nU) nB(Ao Mn) kI(Fy Ph) AanU CuMk QzgC KlgW RjoW PipI dBmT} Kq{oP(aF Bg bO bV cF Dp Gn In Kk Ks Mf Mh Nh Nq Of Oi Qv Ur Yj) Ef(Aa Aj aN dB dE Dk Hc Jd Jh Ke My Of oN Pj rQ) Of(aN bM Fw Iz Jh Lv Nd Pj Uh) gC(Dk Ib Uu Vi Vj Yd) Iz(Aj aN dE Hv Nd) Vi(lX nA nB nN) Aj(bM Jh My) Wd(Nd nR) IbuO} Tk{rN(Aj Ap dB Ef Ha Jg Jk Kl Ma Mg Ng Oz Pz Qu Tv Uu) sK(aJ Al aW cH Gl Mn Rb Vo) uG(dL Ng Qb Rb To Tt) cB(fN rT uO vH) rV(Ap Cw Ng Uu) Mx(rC rO rQ) aV(fN uO vH) dB(rT sM Uh) Ap(hL qZ) Db(qO rT) qB(Mn Tz) uN(Kd To) CthR HfqQ KkrT UmqA UhdE OzqH cUvB dAvH iHuW} rB{tR(Cu Js Ke Kr Mt Mx Ou Up) aD(kF kN lY mE mF mT) cF(kE kI lW mE mH mI) Tz(Mg Ng Og Um wL) fR(aF Ba cH cN Of) cP(kC kK mF mT) Ng(Cu Fa Un) Qd(hR sK yJ) Um(Po Qa Qe) aS(lY mE mI) cI(kF mT oQ) Mt(wJ yJ) Mx(wC yL) aR(nB nU) mT(cH dK) Cqlb CsyJ FywJ SrwH KetS PktN

Figure 39 Continued dCkC} Wn{Uh(Ap AW Ba bL bM Bo bZ cB cC cU CW DB dC dE Dg Fn Hb hG Ib Ic Id iH Im Iq Iu Jg Kl Kp Kz Mx Na Nm On pF Qu Qx Rb
Rg To Tr Un Us Uu) oE(cB cW Js Kr) Ng(hR jL rC) bV(Ij Js Mx) Ct(hR jL) JraU KrdC} On{Of(Fp Im Iv Jg Lv Lw Mb Me Mh Ms Mw Mx
My Ng Nh Nl Nm Nq Nx Og Om Oy Qd) Ms(Fp Mh Ng Nl Og Oy Qd) Mb(Mw My Ng Og Oy) Mh(Hr Iv Oy Qd) Og(Fp Im Iv Qd) Vi(fP gP
nB) Fp(My Ng) Hv(Wd Wh) Oy(Iv Qe) oP(Gn Yj) AjbM MyQd WelY KnpK} jR{Vz(aH al bB Jq Ke Lh Lx Or Ou Un Yl) Oi(Rv Uw Ux Vj
Vw Zq Xa) Gp(Dr Fc Gn Ho Wc) Rv(cB It Kz Nf Qb) Nd(Gh Lp Sj) Yj(Db dJ Nn) Gb(In Rj) Nf(Uz Wg) Uw(aG aQ) Vc(aF cE) Vj(Lj Qb)
aS(kl mS} DrRj EmaG YhPb ZqcB ZwVq KikF UyaQ PjnI aRoO cUkO} qY{kK(Af Ao Ap As bG bH bX Co Ct Cw Iz Kk Ow} lY(aM Ap bG
bH bX dB Dg dK Or) kF(Ad Aj aM bH bX Kl Or Pj) cU(kC kO mE nL nN oP) IW(Aj aM bH bJ bX Kl) Kl(fR kN) Pj(kC nT) bH(mE ml)
nN(cH Kk) EmUn bXml dMoQ kCrX} jH{Yd(aG Ef In Iz Ks Mu Nd Nn Ph Ua Wh) Pj(kC kO nC nD nH nl nJ nL) Lp(aE Bn bS Dr Kc Lj Mx)
Rv(Mq Oi Oz) Yj(Oz Pb) Zq(Jv Mv) Op(Nn Oh) cC(mT Vw) IY(bG Cs) BcGd CuVz EmOi NfTm InYh HbSi WfaM JqPs RyVq RxbS LjVj
VccG} Im{Og(aA Fp Iv Jg Jl Jq Js Jt Lh Lv Lw Mb Mf Mh Ms Mx My Nh Nl Nm Nv Nx Qd Qe) uI(Ib Jk Jt Kj Ng Ni) Ib(uV wE wQ) Ef(uO wE) Qd(My Oy) Jg(Ng Of) sK(Mj wQ) oP(bO Qv) AjaN DuoT JkvB NypK VigC iAwE} Jv{wQ(Cs cU Fp Fy It Js Mn Oa Qd) rC(rR rW sK tN uN uY) vA(Fa Fy Mt Mx Qd Un) Zq(gP kP mM) bX(gC oT pI) uN(aF Ny Qm) Nk(gC oT) hP(dA Tz) tN(Gp Ly) sK(aW iP) NoIb HvXa YjkP QvUh QmtR aFuO aNrR bBpI cYuI uYvT} kG{Zw(Ao Ih Iq Ir Jn Mf) Yj(bH Il Iq Ir) Ry(Ij Lj Mx Nk) Gn(bH Iq Ir) Hl(aS bH Ip) Hq(Wd We Yh) To(Du pK Rv) Zq(dB Kn Vj) Dd(Du Rv) Nk(Gb Uw) Ho(bH Ip) Il(We Yh) Wd(Ao Jn) Yl(aS Ip) NlOp IhYi WcRj WebI LtbB aRhW dMhV} Qd{Og(aA Iv Jg Mh Ms Mx My Nm Nx Oy) My(aA bM Jg Mx Nm Nv Nx) Jg(aA Mh Ms Ng Of Oy) aA(Mh Mx Of Oy) Ef(bM rC rQ) Nm(Mx Of) Ms(Nx Oy) Ib(No rQ) bM(Aj Iu) wQ(cT uT) MxOy JkrQ NxOf yJrC} jO{Vc(aH aS bA bC bH bI bX cA cI cQ cT dE dI Dp Fy Gp Id Jf Nk Qw Ub Vq) Lp(Cu Ou Vv) dF(Ry Vz Wh) Gl(uN uY) Xa(Oi Rc) aE(Fd Hl) bJ(lW lY) cU(nN Vz) BaRz CuRy NdSj IpsK KcuY rQpF} pH{To(Ar Ax bB bR bX cA cF cI cR Cw Du Ko Kx Li Nh Nk nL No Sr Ub Yj) Yi(bE cR dD Fn iP Lj) cA(Fn Hf Kn Rf Sr Uc) Rm(bH bI bR Jn) Wc(Rj Up Us) Jn(Ps Vi) KnbX LiVi} hV{kF(aJ bA bG bS bX cC cT dM) cU(kC kO nC nJ nL oQ) kO(aD aG bV cI dC) dC(nD nF nJ) bV(nB nT) cI(nL oQ) cV(kC kK) dB(nN nR) dM(mI mZ) QgfR aFkC aHnR aSmI bBnN cCnL cWoQ} iP{yJ(aN bA Ip Ir Is Jl Kr Mq Mt Mx Or Po Qe rC uI Un) tR(Il Ip Kr Ld Or) Xa(BG cD Og) Ry(Ha nN No) Gd(Fy Zq) Rc(sK uI) uN(Ip uI) NoVi MmZq YiRh sKoE} Du{oT(aW bG bH bX Dd Fc Fw Jf Jm Kd Ne Oa Pa Ru To Uy) Nd(Ed Uh Un Up Ur Vt) Gp(iA mM oE Vt) Dd(lY nJ oO) Up(fA nH nL) To(mE nJ) FwmU QagC UkpI} We{lY(bB Fy Ij Il mE Mn) Nx(nA nB nL nN nU) bI(mE nH nL nN) mE(Ld Na Tn) nL(An Il Mn) Ph(fA gC) bB(nA nN) gZ(Fw Mx) oP(Nv Tn) FyjL MnnR NanU HqnN IlnH JhlO OznJ aInA} hW{cF(kC mU nA nC nI nJ nN nT) bQ(kF mS nA nD nF nI) kF(aW bG bS bX dM) cV(mP mS nB nN) aS(mS nN oQ) bG(lY nT) dF(kC kO) AdfR KpuI aFkC aOkO bXmF rQpF} oP{Yj(bQ bZ Cu Fa Fy Jl Jn Jr Js Lx Mx nH nW Ph Pi Qa) Gn(Ao Cu Jn Js Ks Ph Pi) bO(Ch Cw No Nq Tn Vv) Dp(Cu Nv) TjTt InPi OrcF dFjK} Ry{bB(mY nB Nd nL nN oE) nN(Jn Lx Nq Or) oE(Fy Li Oa Xa) Gp(kP nL Or) Ha(gP iJ) No(gP iJ) Mx(oT pI) Ij(lY mS) aE(jL lO) nL(aI Lh) CugW MnnB InjG QegC LikI} Lp{jG(cQ Ct Fd Pa Uc Us Uw Uy Vu Yh Yi) lO(aE Af cC dK Nd Nh Oh Ph Ql Tz) jL(aE Af Ql) aW(kI lY) gW(cB dM) mE(bR cA) jK(Db Jq)} rC{sK(Ch Jk Mx oE) Mg(Ke Or Sr) Ng(Id Ke Un) cF(kC nI nT) Mx(tR uN) Qe(Ef yJ) Or(Jk Of) mT(aJ dB) kF(aR bW) AamU ChuY MarS IptR LiyJ OifR PdkN bFkC qHoE} pK{To(Bo Di Gn hB Hl iO Ld Ug Um Xa) dD(Af cF fP iA nI Nn Ny) Fw(cQ Kn Rm) Tj(aW bJ) DdGn EdiO GpmM TnKn IpaA YibQ WcUp UmiA aEcF fBnL} Zq{Gd(eF iJ kQ mM Nd) Mh(eF iA iJ oK) mM(Dl Qw Qy Ur) kP(Io Ju To) lY(Kl Vj) iJ(Rc Uc) jL(Nn Oh) DlnA EfkS TolX IojG QviA RfnB bOgP dBfA} oW{bB(bG cD cE cQ dD DG iA kI Mk pF Rf) Vi(Jr Ld Nv Ny) bH(cR dD kI Tj) cR(cX Mk oO) Wc(Rj Up) ApKo YfMx FncD MeHf bOcX} hX{cV(kC kI kO mF mS mU nC nD nF nH nJ nL nN nT) bG(kE kI mI mT nB) mF(bO bV cF) aJnR bEkF cIoQ cXmZ dCkC dMnT} Jg{Qb(Jk My Ng Of Og Oy) Of(aA Fp Js Mx Qa) Ng(aA Nx Qa Qe) Og(Fp Mx Qa Qe) Aj(aN bM) Ms(Fp Mx) MxaA MyQe QaOy} Wd{Uf(kI mM mS mZ nR) Cu(kS mM mZ nR) nL(Ao Lh Nx) Fw(fA mU) cG(mZ nR) jL(Fy Hf) lO(aE Kc) EfmZ GpHv LhnI NxnN cBgW lYmE} uI{Id(Cp hP Ng Ni Qw rR tF) Mx(hP Ne Qw) Ic(Fa kR Tj) Of(Fw Kf Tj) dA(hP jK Qw) DkkR WmiA FaIb TtSr cUoE dMpF} fA{nH(Ed Fn Ho Rf Rg Tv) nL(Gb Ho Rf Ru Rv To) bI(Uw Ux Vo Vw) Wf(cH Ip) FdRf NkKn YiYl ZwPi JfcR KkcI} Vq{pF(qQ rR rT rW rY uY wE) wE(aX iA Uu) Tt(uO yK) bC(sK uY) tQ(Ch iA) jK(Rx Rz) NqsK VzjT WhjG bZwB uNuP} gW{cB(Fd Hl Rt Sj Wh Yd) Nd(Gh Hl Sj) Oi(Ho Uw Vj) bS(Uw Vj) dJ(Hl Xa) DbRv FcGp VzKx RzdF RxcQ LtbA VcoF} wQ{Cu(Ef Ib Jh Jk) Ip(aN cT nY vI) Po(Aw cT Ef) Ib(Ke Lh) Jk(Ou Wm) cT(Lh Qe) uT(It Mx) FrIz LxiA NicU TooF} qT{mP(bH bS cU Dd Di Hf Kf Ld Pi) aR(nD nL nN) cU(kC nD nH) kF(Af Aj Or) Gd(dB Lv) AjkN HcmZ} Un{vA(Bn cR Jk Ng uY zG) Jk(tN uO uY vB) Mg(uU wE) Ib(No uX) Wc(jG jL) EfuX NdSi NgrS iAzG uYvT} gZ{Nk(Gb Kn Rc Uw) bB(An bG cD) bI(Uu Vo Wf) nL(Ib Rf Yh) bG(Kx Ub) cR(Fr Jf) AoGd FnnH FwVi MnVh} tR{Dl(aM Mg Ng qQ) Ip(aN cB cR qQ) Kz(Ni Pk Sr) Mx(hP qZ) Qm(dL uN) Uh(aM oE) AaMh KecR LdrR QlkR} Xa{bG(gP oE oF tF) cD(kI mF Nd nY) Ib(lY mS nJ) Og(fP gP iA) Oy(Hv mS) fB(Pz Ua) NeoT QwkS} lO{Wh(aE Af Jh Kc Tz) Db(Gn Wb Wf Zw) Ph(Ux Vw Yd) Ps(aE Bn) Vj(Lj Oh) NfTm HlaE InVa SiPj} Vi{nL(bB Gp Lh Lx oF) nB(bB Cu Lh Mn) Cu(kP nN) No(gP iJ) gC(Qa Qe) FwmU JrnN LdmE LhnH} jL{Wc(Dk Jh Kc Qy Tz Yd) aE(Wb Yh Zw) Fy(Wh Zw) Hf(Gn Tm) AwfR BnYd NdLt NgVw WhKj aRnN} pI{bX(Fy Ju Kx Ld Qw Rg Vo Vv Vz Yl) Kx(An bG bH Rf) DrNh HacC MxYd UodD UkcR} Aj{Nm(aM aN aS BA bM bV cT Nb) bM(Ad Ba Bb Cu Is Jt Pk) Jt(aN dE)} hR{cF(kO nC nD nF nH nJ nL) aS(kC mF mI mS nB nJ) fR(bW cE cL Oh) aRnN} rX{bJ(kK kN lW mE mF mH) bV(lY mE mT) cU(mU nD nI) mT(bA dF) aSlW bEkF cQoQ dMlX} jT{Hf(Ru Vc Yf) mT(Bn Cx Gp) Cu(Fd Gh) Uw(aW Nn) aG(Vc Yd) MamM InYh ZwaE RzdF aRnN} jG{aR(lW mM nC) Gd(bI Uv) It(Rv Vh) Rj(Dr Uy) BnWf CtRx FiOu TzWc YdbA SiPj aSnT} rQ{pF(Aa cE Ke Kk Li qQ) Dk(Aa Kr Ny) Ng(Dl Ke Kf) AdIb NiaN RbJk iAoE} jK{Qx(uN uX uY) Yd(Lh Ou) DbYj DrbO InRt YiPb WbbI VzbB PsaE OuVc UwaW PjkC} dA{hP(Ez Id Pj Uh Uk Um Ur) wJ(Ke Ri Uh) yJ(Ke Uh) RiyL QmuN} Ib{No(Fy Of Or Rf Tz Uh Vt) Qe(rU yK) QmuP NyqA aFuO} gC{Uy(cR Iv Kx) Mb(bG Nk) Qw(iO Li) FcMf MxVw NkHo WhbG KxbX} mE{Gd(aI bB cA cG Jn Jt Mn) rY(aS bJ) HlRg YjQw WhlY} iA{yL(Cu Ip Mq Mt Or Ou Pe Po Wm) FcGp IpvS UhwD} Jk{Cu(tN uO) Wm(uN uY) Tz(tV wP) Qm(uP wP) FauO TowD TrwJ} fB{dD(cR nL Qh Uo) AxQu DdHr GpbJ WfiJ KxbX RvnH PhcI} aN{Ip(uO vA vV yJ) wE(Mh sC Wm) LwLi KrwJ uYvT} rY{mT(bA bG bV dF) bJ(kC kN mF) LyKr aVmH cQoQ} oE{Gp(Fc Ho Wb) qH(Co Tj) HobG RisK UhcB PknI aFuO} uN{Qm(Ne uV wE) EfNy WmUr GlNe MxnW NiTo IqKn} Rg{pF(pY qV rO uY) nA(Yj Zw) OpnH} aF{uO(Ao Ba Hc Hf Jd Kp) KrwJ} bB{Gd(mH mI) nR(Gn Vh) YikK WhlY UynJ} bM{Ke(Of yJ) Pk(aS Of) AaEf JoJt UhfP} mU{Hl(aM Pi Qa Qe) Wc(cG Cu) YjQa} Gp{Hv(Si Vc) DrmS MhWb WhJr VcVt} Ng{Dl(sK tN vI) IlrV QmwD UfmS} eM{Mn(Gn Vh) Tn(Uu Vv) KeRm KxRf} oT{bX(Hf Ju Vz) Nk(Jd Vj) AnKx} uY{vT(Id Or Uh Wm) NeUh QmVv} Aa{tN(Ch Ef Mh) tV(fP Mh)} Po{hP(Mj Nq Oy Pf) UhoN} Mx{Ne(vA vI) sK(hP rS) MjvI} Og{Nm(Fp Qe) Nx(Ir Qe) nNoK} mZ{Rt(Ur Uu) CuUw GdMn SjcD} iJ{Ed(kP nU) Yi(Lj No) GhaM} qV{cU(kC kO) aRoQ bGkO bJlY} Ho{NdcD NkaZ LjcX bOfP} Wh{Nx(nB nL) NdKx cGnR} Us{mS(Dr Fi) nL(Op Rv)} wJ{Ke(cB Kp) dD(Kr Wm)} zG{Cv(Qm Ri Wm) MqpF} To{wD(cY dR) NivU} aW{GnlY RvnH QmsK} Dd{kN(Si Va)} No{EfwE IcOf} Ip{UrsK bItN} Qa{oQ(Gn Yj)} Lj{WbcX OwVw} Uu{OpnA nNoK} nT{TzkP bEcF} pF{MqzH cKvI} DktNkR WmNivU FaNquO GhJnkI GlNevB NmQeaA IzaXtV LiRfkP RvcGnR

Figure 39 Continued

Figure 39 Continued

Ao(Eq Vb) Rh(Wf Ye) oP(bC Kq) DdSf MjWb WhKp KztX RikG VcVq VjmZ aWnJ cPmS dJfB sKjV} Nw{Oy(aA Ij Ik Im Lw Mb Mf Mh Mu Mx Nl Nm Nn Nx On Pd Pg Qa Qb Qe) My(aN Jl Jt Lw Mf Mp Mu Nl Nm Nn Nx On Qb) Ng(Im Jg Jt Lw Mf Nm Qa Qe) Og(aN Jg Jt Lw Me Nn Nx On) aN(aS bE bM dE Nb Ne Of) Mb(Jl Jt Mc Mp Nn Qa) Mh(Lx Mp Nx Pe Qa Qe) Mx(Hu Im Js Nl Om) Eo(Hv Js Qb Qc) Nm(Hr Me Nl Om) Mp(aA Fp Iv Ms) Im(Lw Me Om Qd) Et(Mv Ny Pb) Nq(On Qa Qd) Mw(dW Nn On) Of(Jl Jt Me) bM(aS bE bJ) eO(In Mt Nh) eW(aX cT Hu) Gz(uI vB) Lw(Iv Qd) Hr(Pe Qa) Om(Ih Qa) aA(Jn Me) dX(Fy Pk) eP(Qv Rg) kP(Hp Yg) AjNt NnMv MsJt MuHu NdSf NlQd IbjB cCkF} Vb{mW(bB bZ cS dD Dr Et gL Is Js Jt Kf kG Ld Lx Na Nm Nn Of On Ux) nO(cR cS Ij It Jg Ne Rz Tn Vi Vu Xa) mE(Aa aI aL Cw kG Kx Li Mn Og Op Qw) kG(An Ap dB Fy Ih Jt Nm Op Qw Vt) Cu(aD cE eM Jn Mf Nd Ow Qy) mU(aM bZ cR Cw Li Qa Tn Vw) iJ(aM Lh Ns On Uv Vq) mI(aL bI Ks Op Oz) kI(Fy Jn Js nA Vv) Jr(Nk Nm Vp Vq) Nd(Fy Ho Jt) nN(bI Cv Og) kF(cI eC Yk) Dc(nL Sf) Hv(Jt Qy) Zq(iP mM) Jn(Ut Vh) On(Nk Vt) dB(mT nK) eM(Pi Ut) mF(Vv Vw) mZ(Mg Na) nA(cN iO) nJ(Og Oz) AaoW CsTl TioQ GpUn IsmS QecX JqnK KgnB hBoO} Ti{uR(EZ jM Kl Ma Mg Mn No Of qX Tv tX Uu Vv) wH(Ap Dg Hq Jr Kg Ks Or tO Vo yK) tX(eD Mv Nh Nj Qu rB uN vI) nH(Gp Pc Pf Pg Rg Sf Uk) rZ(bI cR hR Nj qT zG) Ue(jU rC uM wQ Tk) yJ(aW cN dM Jv zA) vB(Ch Nh Nj Nl zG) tT(Jt Pc tQ wE) Tk(Dc Nm St) Or(rX Ub wJ) bP(rY wQ yL) wP(Mg Nh Nj) sK(cM cN tQ) wD(Jg Ma Uu) jU(Ly Qv uV) uW(jF Jg To) Ib(rC vQ) Jv(rX wL) nC(Ju Qv) hR(tR wJ) jD(Nd Og) sO(Kj Kl) uI(Ef Qu) uT(Kf Li) DehW GdnO LxjM NbRh NhjY SfkP RczG JnwB YekG KnwG QntU UuvQ OzwK aFsM aLnB aMrY cYvP mSnJ lMuV uYvT} Ji{bM(bA bE dE Hr Iu Jq Jv Nb Ne Nf Ng Nh Rf Um wQ) uM(aF cB cX Iz jV Kj Mj Ne sK To vA wJ) aN(Ap bA cT Jq Lw Mh Nd Oi) tR(cS hR Kz rB rC tS zG) dE(Aj Ef Jo Jq oE Of) wJ(Ik Kp Ne Nk zG) Ef(iJ Kq tO wF) Tl(bO nN Sh) Vi(hG iZ nH) tX(It rA rU) tO(iP Kz rB) rQ(Ib Ma Ng) Eq(mY nH) Ex(qO tV) Nb(Mr Oz) Si(mE mM) Jv(eF oE) Wn(Um Uu) aW(sK yJ) bI(sK wE) bO(eQ oP) dU(bL To) wQ(cT Po) tT(It rU) sH(Dk Iv) jD(Um wE) jO(uN wL) vA(Ne wF) DeEo NoIb MmeP MsoV MveO MybV NdSh NgrU YinH YdnK SfnN RcqP WcmU WemZ JodB OfoE PesI iAwD iPyJ} gV{dR(Bc cI Co Dk eC Fp Ik Il Iv Jm Jt Lv Mf Mh Ms Nj Nr Pe) Vo(Ap Ba bB bH cV cX cZ Hb Jg Kp Lv Mg Rh Wm) Qv(aL bB Bc Dc Ha Jv Nr Qh Rg) Jv(Ar Ax bO Cv Dd Kd Nj Ow) Ug(aU bR Cs Ir Nn Ow Vq) Li(cY dG fP Jq Jt) St(Aj cB Kr) Oa(Ih Jk Qy) Ow(Ct Ez Kl) Ur(Cs Ha Rg) Uu(aI bO gP) Vq(An Io Mj) Vv(aK cY Qh) gL(Rh Ub Wm) Gd(Jd Jf) Ue(aF Or) Qb(Je Ua) Qu(bM Nn) Ju(Al Cw) Uf(Ao cP) Us(aI aL) gP(Qg Ub) ApKl AxJq CsKg CvRg PoQl EzOr FyaK GpMl LwcX IbIr TnJh HbaM IoVu QeJe QhcQ LjPk RhcZ aDaL} Ut{nO(Ad Ap Ba cA cM Co dM Gz Hw Ik Jg Jt Ju Pz Qz Rc Um We Yk) nN(Ap Bg Dp In Jg Kn Ng Qw Tj) oP(bU cY Gn Hv Mk Mp mU Ub Zw) nT(dA dD Dp Hw Ju lY nD Um) Sh(bS cF cI Dc Hf iP Tl) lX(Co Li Mu Nc Ns Oy Rg) lY(Cp Dp Of Pz Uu Uw) nD(Je Jk Kl Pz Ug Vs) pK(Ad Co Jq nR Pg) mF(Ry Vs Yd Zx) Eq(Hv iP Nd) My(kP oD pI) Nh(mM nJ nL) Si(bS mU Vt) Vi(kI nB oE) dU(cF Ib Vo) oV(Oy Pz Qw) Iz(kP nI) mZ(oT Wf) ChTl DbeQ EfpI NdSf HoHp YkkC RmjB UrdX VveM aLnL bBmM dMoW} On{Oy(Fp Ii Ik Im Jg Jn Li Lw Mf Mx Nl Nm Nx Qa Qb Qd) Mh(aA Ii Im Lw Mv Mw My Ng Nm Nq Og Om) Ms(aA Ih Im Iv Jn Mx My Nh Nx Oc) My(Et Hr Im Mf Mr Nm Oe Og Qa) Fp(aA Hr Iv Mw Nl Nm Nq Om) Og(Ij Mx Nl Nm Nq Nx Qb Qe) Mb(aA Lw Mv Mx Nm Oe) Ng(Iv Jg Nl Nm Qd) Mw(Iv Mu Nn) Hp(Hv nK Vt) Tl(Iz Sh Wd) eQ(Fn Of Ua) Aj(aN Nt) Eo(Bb Dl) Nq(Iv Qd) Nd(Sf Sh) Nj(Lw Mp) Jk(Qb Qd) iJ(Eq Yg) EtMv MxaA RygP RmjB OfaN UwVt ViiP bOoP fRjP} wF{To(aG aZ bC bM bQ Cs Pj Uk uL uM Ur wQ) Bb(Bg Jd jO Mu Mv Ne Oy Qx wJ wQ) Ef(Dl Im Ke Ny Pj rC) Cs(hP iP jE jV nW) Dk(Kn Lh Pj qU rA) An(Dl eC rR Wm) Ar(bQ cY uX vA) Ke(cB Jh Of tO) Qm(bI cF Ma qU) Uh(aZ Ib jE Kp) Pj(Ib Jo My tO) iA(Jv Ql Qx Un) Dl(aQ Of tT) Id(dN hA uL) Kr(bI Ly wJ) Ri(jE Ne qH) jM(Ou Qv Uk) nW(Af Kp Kz) Cv(jE Jk) Jv(qH rC) Kn(Jo uL) Oa(dN zG) Vt(bC vW) jO(hF Ko) AfQe CpKq CwIm LuQn TzHw SrrB QxiP QhJk KyaN RgpF QljD UncY} Hp{Ho(aM bU Im Is Lj Mx Nb Nk Oa Or Qe Qh) Fy(dU Hv iJ kG Nd nL oE Or Qe Vt Vu) nL(Al An bL Iq Ir Is Ks Ng Nk Qh) kG(Ao bI bL Hq Ij Mx Pj Vt) Hv(bU cF Cu Dk Im Jn Nt) mM(hB Ih Ke Na Qc Qm St) Qe(iJ Nd Nh Tl) Vt(De mE Nb Nt) lY(Iu mE Pi Vq) nK(bL Dd Mn nI) kP(Cu Ih Un Zq) nB(Cu Dd Pj) De(Is Mx) Ha(eQ iJ) No(iP kS) Hw(Jr nJ) Im(mW nD) Or(Jt Nt) aW(kE kI) EtNd NqeP IriJ IsbM StmS JloP JmnJ JsdU UnmE PinI bHmT bLnN} sH{hW(Bc bJ bQ iB Pk qO Vu Tj) Bc(Al Dd Lh Mh Pa Po) Ib(Dg iC Ju uI Uv uZ) zG(dL dR Ir jM lM qC) Pk(aM aW dK Of vT) iB(Of Ra Ua Uk) iC(Ch Ef Ua uP) uZ(Cq dE Pg Sr) vI(cY dN jV rA) Dk(hR tQ vS) Dp(eT jR jV) Io(lN Ny Tt) Ir(Iu Jh Of) Vu(hA hP sK) Pf(Ax hV jU) dR(Iu Mh tX) uL(Ch Ct Ef) Cs(Mg tR) My(jM jT) Is(hG Jk) Js(Of Oy) rU(Ed qU) AxdH BobC CpjV TjhP NqjT MaQd MraX NfpF IuLh SrhA JvuI KpjE KqwH KxqD RgrO VssK PajR cCjH gLtT tSjM tXoK} Ye{mZ(aX bC Cq cY Kc mI Ou Pg Wd) mE(aL cI dD iP Jr nI Qw Tl) kG(aO Aw iA iP Mb Qw Tz) oV(cK Cv Li Lt Mn Ng oK) Hv(cF Is Lj Mb Qe Xa) mT(aE iA Lv Me Qw) mU(Fi Ma Mg Mm Wd) nL(aE An Et Ip Jf) mS(aW Jf Kg Ph) nN(aE cX iP) nU(Aa Lv Me) nI(Et Ez Fy) nJ(aL Ou Pi) nK(Aw Lv Ly) iJ(cM Ms Qa) In(eQ jB) Rh(Fy Im) dU(Id nA) mM(oW Pj) mP(iA To) iZ(bU cM) MenH NdLj IhkP QeRm JokI OgnA UfnR UpnB aLmI cRmY dDmW eCkF iAoW} Kq{Ef(Ao bM bV cC Cs Cu cV cX De Et Fb Hu Ko Kr Lh Mp Mv Mw Na Nf No oE Om Ou Sr Uc Uh uN uY vB) Aj(aN cX dB dE Dk Fw Hc Jv Kz Lh Lv Mw Nf Nq Of Om oP Ow) oP(Ad bU Hw Il Jo Ki lW mS Nl Uu We) Of(Ao dE Dk Hc Hf Hu Jd Mw My Pg) Iz(bM cC Lv Mb Tl) Nd(Eq Jh Wh) Bg(mT nO) Ib(No uY) Jh(Hv Mb) Vi(kO nK) jV(My uM) MhtO NgrC WdlY JkrZ JobM JvvA RfmT UhsJ UwmZ VoeQ dDwJ iPyJ} Gz{jV(bI Cs Cu Gl Kr Lx Ly Lz Ml No Oh Pd Up Us Vt) vB(bA cA cU Dg dH Hb Ij Lj Mx Nm Ph pS xA) rZ(cJ cV Nj Pz Qz) Us(eC pY sM xA) uI(aR sO uU uY) uG(aW bS cA iO) uW(bW dD Hb Ny) Je(vI wP yL) nO(bL dB eC) pY(dD Hf Uc) qV(tU Vu tL) qU(Il sK Tz) yE(Jy Qw Ue) Uh(uU vW) rC(jY tL) jD(Lh Qh) qY(Nm qP) qT(bA Vu) uN(Ny Of) AalM ArdX CvqX FwrX NoqW UceT IvuZ JdsM JuwP JyuR KyqB OhtV OziB PjuY cMhL eCkF sKqP yLvA} Qd{Nm(Aj Fp Im Mb Mh Ms Ng Nj Nq Nx Oy) My(aN Jl Jt Lw Mh Mm Mp Mt Nd Nn) Oy(Jl Lv Lw Mp Nj Nl Nn Nv Nx) Nj(Jl Mi Mp Nd Nn Nv Of) aA(Im Lw Mj Ms Nl Nq Nx) bM(aS bE bJ Jo Ne Of Pk) Jg(Im Jk Mx Nq Oe Pz) aN(Aj bE dE Ef Ne Of) Og(Fp Lw Mf Nl Nv) Mh(Im Lw Mj Nx) Ms(Im Lw Nl Nn) Of(Im Iv Mm Nv) Iu(Lh Mi Mp) Nq(Iv rQ) Mx(It Lw) Jv(aS rZ) AjNt AxEo ImNx wJrB iPyJ rCuM sKjU} tO{Mh(Ad Bc Bn cM Cq cZ Dc dD Hf Kd Kp Or Ou Pi Qm) Ke(aM bU cB dL hR Jk Kz rC) Uh(cR dA Kr Ne Or Ou Pk uN) rB(Cs Dc Fw Fy Ip Kn Lh Pb) Kr(aM cR cX Ly Oi rS) Vq(aE As cM dB Fn Hf) rC(Ch dM Ip Ld Un) Jv(Fy Js Ju Ri) Qm(kR Mt oF Vt) Dl(Ld Pc qQ) Ou(jV kR yL) Un(Hc Kz Ld) iP(Il Mx Pd) Aa(Jl Po) bU(Ko Uc) AnrQ AxjV NrKz ToJy KncR LdjE VtzG qZuY} uM{rC(Cq Cu Fw Hx Ih Ir Iv Jn Ke Kn Lh Ma Ml No Om Pe Pk Po Tv Un Vt) Id(bM cB cK cL qX rQ rZ uI wQ yK) Mx(bI fN Qm Qx qZ rY UN) Qm(Of sM uP uU Vt) To(Kp Sr Up Vt) Un(Ef Nq sK Tt) wQ(Im No Nr Nx) aF(Im Or qX) sK(jV Kc Uh) Dk(Mq Po) Ly(Fa Ou) Tk(Kl Nm) qX(Kc rS) CuJk EfPo WmaN GluN NqqZ MdlL KrjV PdpF PkrZ bMrS} Nd{Sf(Al aN Ar Ax bM Du dX Ed Fp Gp Hb Hu Jn Jt Ke Mx Na Nk Oa Or Oz Qe Vz Wb) Sh(aN cD cK Dc Dd Dk Fp Gp Ho Mf Na No Oa Qh Up Vt Vz Xa) Eq(Et Ho Jd Mk Nn Nq Uc Uf) aN(Nt Qc Uh) Ew(bS fP) Zq(Dl Ju) Uy(Kx Nx) Pj(jD Si) eO(eM Mp) fB(aL dD) nO(bO Rf) oV(nL nN) DuPz FyRx MneQ NjaA YgdF YjbB eCpK} tT{Dl(aN Ap Ib Iz Mk Ne Nj Of Qu sK uI) Kz(An jE jO Kn Ne oF Oz Qm qU Ri rS) iP(Il Mk Qg rB Ug wJ wQ) Qm(cB Ch Ef kR Ou rC) Ly(Hf Ko Nx Vt Wm) To(JY Kd kR qX) Uh(cB fP jO) Pk(dJ Qg uI) sI(cO dC hG) rC(cR Id Oy) rB(Js Lj wJ) Po(Aa Ef) Ip(aW rA) Ri(kR Nj) DkkR NqsJ MfkS MhVv NiaN TnSr IzJk QgUn KrjV PiyL} Og{Nj(Fp Fr Ir Is Jg Js Li Mt Nm No Nx Qb) Iv(Eo Fp Ij Ir Jg Nm Nx Qe) Nm(aN Eo Ir Mx Qa Qb) Qe(AA dW Jq Lw Ms) Jg(aA Ij Js Mh Ms Of) Im(aN Mi Mp Nn Pe) Nx(Dw Fp Ij Qa Qb) Fp(Ij Jt Nv) nN(aL bL cC) Xa(Hv mU) Tl(jB nA) Nv(Mb Mx) aA(Ij Li) aN(Bb Nt) pK(cF nL) ExjB NoIb MfIr KelM RtmZ YlnK cRoD dCeW} Aj{Nm(bE bO Cs CU cV Dc dE Fp Fr Im Iv Jg Lx Mx Nf Ns Qe) Nt(Ad cT Cu cV cX Dc Dd dK Fr Im Is Jg Lh Li Mt Nh Nk Qc) bM(bA Bc cT Dc Fy Im Ke Li Mn Mt Or) aN(Ba Bb Cu Et Ir Is Li Mn Qc Qc) nN(bC bU cM) Mn(dU eQ) jB(To Tl) CuNf DkSf EmqX FydE HveO JtdB NxoW bCnO mPqT}

Figure 39 Continued cO{Hu(aP Ax aY cW dG Et Lh Mt Nr Nv Qa) Oh(Ar cW dC eM eW NI) dC(aF bE cV dF Hw) Il(bN cG cW dN) aY(aV Ij Jm Mh) eM(bE Ij Lz Pe) Mu(bG Di fP) An(Iv Jr) Et(aO Mv) Mp(dN Fp) Lh(aW cS) aD(bH bP) aF(Lu Nb) cU(dD Jm) cW(Ij Mx) AlJg ArLw BgQc CwIu FrMv MhHw MmaW NjdF NkbB HqdD QbdW LibC LjbF NxbN bRbX dGfR} Yk{oD(aQ bC bJ bX bZ cL cO cR Cu Fw Kg kP Ks ml Mm Mu My Pj Uh Vu) mW(bL cV dR Pd Pf Pg Qv Tz Xa) oT(cL Dc Hq Nj pH Pk Sj) gC(cR dH oE oN) lY(cJ Dd oE Yd) kG(Jn Op Qt Um) pH(aP bW oO Ux) nA(dD Jn Tz) CqmZ DdkK FwoV NalX HveQ JnkP JrkO UpnH UsnK bWoW cGmU nLiP} oV{Mx(aL bB cQ Hf Ne Nj Nl Vu) Fw(bG cE Iz Kf mF Nc nR) aL(Dr Du Eq Ms mY nW Zx) Mk(Jf Ld Lx nL No Ub) nK(It Lp Nh Nj nY) bO(bX cX Dd oP) nA(Gn Kx Ld Tj) Zx(Ao gZ kQ) Jf(Kx Li Vq) Qu(Hu Ib Ng) Gn(Gp Ph) bH(cF mE) AaYd DrNh FyOu GpNs TzdD InPh YiQl ShoD KxmZ LtbG UrbX bBdK} Qe{Nm(Fp Im Iv Jg Mb Ms Mx My Ng Nx) aA(Hr Jg Lw Mb Mh Ms Mx My Nx Oy) Eo(Dc Hx Iv Jn Js Mr Of) Nj(In Jg Jl Mi Nk Nv Nx) Jg(Im Mg Ms Of Oy) Nx(Et Im Ms My Of) Aa(Iu Of Oy) Ib(rQ Uh) Im(My Oy) Tl(bO Sh) wQ(It vI) rB(rT yJ) MsJs NeaN NgrS ZwJr JoUh NydU} dU{dD(aO cI iA Ib kF Ma Nn nR Ny) bH(aK cF Id Iv Mk Nf nL) Nj(bL bX cA cF Nb nH) Ny(Lh Lx Mx Ng Nn Ow) bL(fP Kx nH nL) Mx(Dp Lt Qz) To(Ax Bc Jf) Fd(Bg Ib) Fw(cR Qy) Zx(iA Js) Jf(nH Uu) aL(iA Ms) bB(aR oW) CqEq FyYd GbHa GpKl MkPe MnJo HqSh IbcK TnUu YgQa dJfP} Et{Eo(cA Iv Jm Mr No) Mg(Jt Lh Lv Nm Nx) Mw(Lx Mt Mu Nn Nv) Mp(Iv Me Nl Qb) Jo(Jt Lh Nm Nx) eW(bM bR Iv Mm) Nn(Jh Me Mv) Lw(Hr Me Nl) Lx(Hx Mv My) Eq(lY mY) Mt(Hx My) Hr(Hv Jt) Of(bM Cs) Vj(lY nL) EfbM NqOy MiHx MrIi MuMy MvNv IjJh IsIv SffP JnJr JvgC Knpl bCsI} nK{Dr(cY cZ dA dJ Ur) Lp(DD Fn Hq) Hl(nW Pd Qw) Yg(Ao cX Ks) Vz(aU dA dE) Zw(dD Jq Lh) Nx(Uw Ux Wh) Cu(Ps Rz) Yf(nW Or) Sf(aX Ij) We(bI Jq) Tl(aH cD) Ry(eC Lh) Yl(mW Nn) oD(cD Si) DdGb DuaJ GdcZ HoUp YiLh YjPd ShnT WhlY QwjB KjRt UxbI ViaH aNrZ cFhW cPjP} Im{Ms(aA Fp Iv Jn Mh Mx Nh Nl Nx Of) My(aA Fp Jg Jl Mr Mt Nv Nx) Of(aA aN Iv Js Nl Nm Nv Nx) aA(Fp Hr Jn Mx Ng Oy) Fp(Nf Nm) Mh(Hq Jg) Oy(Jg Jl) aN(dE wE) uI(Ic Mn) pK(Mm Nn) GnoP MpNj MxvA NgNx IbzI YggC UgnO cTwQ} Ke{lM(Af bM CV dB dL Ib Iz Jh mW Nf Of Oi Qn Qy rC Um) wJ(aN cF cR Ib Jv) oE(Ef Iz Mj Rf yJ) bM(aS Ef Jo wQ) Ef(rQ uO) Ib(uO yK) Jv(aN vA) eP(Mh Pf) fP(Rf tR) tX(cR Kz) yJ(Jn rC) NgrZ HvdX JkrQ cBzG mUqU hRtR} sF{Bc(Dc Dd iB Po rO sK) Kr(lL lN pY tR tL) iB(Ba Dp Iu Qm Rb) aQ(hR hV wD yL) dK(dR Or uN) sK(cY Ju Pg) Iu(jP qD) Pk(iC Jh) cW(hO qC) tX(Bb It) tR(Iv Or) jE(aW Jd) rU(Dp Ed) sC(Je Um) AovQ AxqX BobC TjhA NfpF IpvS JrtS bQvI hWjF} nN{bU(bO Ct Cx eF Ib Ic It Je Lz Nh oK Om) cM(aZ cF Cs Ct Ic Iq Lz Oy Qm) aL(bC Ct Lj lY mI) Eq(Nx oE To Uf) Ry(Ij Lh Mn) Kl(dF Vv) Vi(bB Lh) cH(jT qX) qU(jU nA) lL(aH aJ) AsIn CuPs NoRf MnYg YiiP OybC nIoH} Eo{Oh(bQ cG dH Jn Ng Qc) dL(Ij Iv Mr Nr Pe Pg) Qa(bN Cx Dc eM Mi) Mr(aX Cx No Po) Hv(Cu Lh Mt) Iv(Af Ik Po) Qb(aZ Ij Pa) Jl(As Dc Dd) Ax(Mw No) Mm(Jn Po) aI(In Nr) bN(Ij Pg) AaCx CqNo EmLi NmcA MeMl IsaF JnbJ JoJs} tX{iP(bQ cO cR dB dJ dN Jv Qm Rc Ug uT zI) rB(Hx Kd Kk Mh Mt Ql qQ Uo) Kz(dJ Ip jE Jk Ly Ne Pj) Qm(fP iA Iz Mv yL) Dl(iA Mg Of) nW(dE Lh Uh) To(Pk qQ) cR(Ni Pj) dB(qU rS) BbHu dHiA} mW{We(Jr Mx Ng Oa Xa) Vi(Ax Lx Nq Oa Xa) Du(cA mM nL) Kc(jU qW qX) jI(Af Bn Ph) jY(cK cL cX) De(hA rA) Hl(Nl Oa) Yg(Mn Xa) Yj(Gd Mf) Zq(Dl Vw) lL(cA cV) AaSh AnqW EqUd FaNh GnHu HaRy NkVw IzqX PhqV cChW cKrY} aN{wE(CU Fw Jr Lh qX uY Tj) Qc(aS cM dD Li Nb Of) Ne(Is Lj Qa tV) Jv(Or Uh uY) Bb(bM Oy) Mh(tN tV) Ng(Gl rQ) Jo(Jt Nt) Li(bS Ef) Lj(bS cM) Of(Cu eW) uY(Qx uL) ExtV NivU KrrY UhcM bReW nDjU rCrR} uI{qX(bA bX Dp jU Nl Nx Pf qY Wm) Id(aW Jk Jo Ow Um uN) jE(Cv Fn Jv Uu) Wm(It Ng Of) Ib(eD Lh Un) Mx(jD jK) Ic(Fw Md) Jv(dA dR) Vv(bX iP) oE(aQ Um) DlUu MnhW NijM JedA JoKr KpkR OfOu dHiA iZrC} Mx{uN(bA iP jK Ne Qm rB rS Uh) Jg(Lw Mh My Ng Nj Oy) aA(Jn Jt Li Nv Nx) Nm(Fp Lh Nj Nx) jB(cF Ny) wB(lM Ne) AxWn NtMp MjuT MsNx NfLh NgJt NjNk SfkP JkvI NvOf UnvA bMrS yJrC sKjV} nO{Ug(Dd Ir Iv Nc Nh Qc Tz) Um(Aw cM Jr Nh) bU(Dp Ed Sh Wf) eC(Li Qc Rv Vs) In(Ha Rg Us) Eq(Co Vi) Gn(aW Nx) Iq(aL Qv) Xa(aW Rc) Yl(cF Fw) aS(jI rA) EdcM NcQv IpRx QaRm OadX VsaL} Tl{Cu(Bg Kg Lj oE Sh Vt Wh) bU(Hv Oa Oh Tz) Nk(cF Ed Tz) bO(Is oE Qa) jB(Ba Jf Oy) Fy(oE Rh) Sh(Hv Nb) Li(Jv oE) dX(aE Gp) EqkG NoeQ NaVt QwLj JrUv JyoD RheC OacC OwoP OygL cMhB} rC{Ng(Cu Fa Or Pj rS sK Tz Uf) yJ(Js Kn Kp Wm) sK(Ef Mg Mv Qm) Ib(Dc lO Vu) Id(bC Mg wJ) Jv(qH rS vP) uN(Ip Nx Ql) Ma(uY vI) BarS CuOf DcMg ExuU NeuY JkvH PefR cBmT} Nt{Mt(Hx Mh Mv My Ny Pb) Lx(Mv Mw Ny Pb Po) Mu(Mv Mw My Oy) Lh(Hx Mv Mw Oy) Nn(Jh Me My Nj) Ii(Jt Mr Pe) Nx(Ik In Ly) Nq(Mp Nv) AaOf LwOe MgJt MiHx MveW NhNl IsJs} aL{pK(aR aW bG cA eQ iA Li Mm Ms nH Om) fB(Ez Hw Ir Mi Qu) ml(Du Fa Ib Li) nT(cF Ir Lj) Uu(kF mP) eQ(Fa Jv) lY(aM qU) nL(bC Mb) oW(aS cO) DumE UsmP PjlW qUkK} Jg{Qb(aA Iu Mh Ms Nj Nq Om) Fp(aA Lw My Ng Nj Oy) Ms(aA Mh Ng Oy Qa) Of(Ij Ng Nv Nx Oy) Qa(aA Iu Jk My) aA(Mh My Oy) Ng(Ih Js) ExqD MyJs HvWd} bM{Pk(aU cV dE Jo oE Oi Uh) Of(Bb Fy Jd Oa) Uh(Ap aS bE cM) Or(aS Lv Mk) wQ(cT Kn qZ) Jo(Dw Fy) aS(Is Pj) eW(aR Mw) BbbJ GpSh TneP cVdW zHqX rAkF qUkK} dX{Or(Dg Fr Gn Ko Sr) Vt(bV Cp Nj Ow Ue) Kx(kF mH nA nI) Lh(Gd Jr Rb Un) Ou(Fp Iq mZ Un) Ld(Ar Iq No) Hv(Hb Un) Kc(Mt No) ArKi CpDu YfPk PoQv HoQz} Yg{oD(bZ nL Nq Pe Po) fA(dB Ng Nk Qh) mE(aI Jq Lx Na) bU(kK oE) gC(pH Qa) mS(Js Ma) kG(aF Qt) GlnH MnnB MpeP HxjB QyeD RzfB LhnJ NxmI bZkP cMnC cRpH iJkK} jB{To(Ch Me Pd pH Qv Ug) Rf(dN Fa Fy nW) Nh(Pi Qz Rb) bI(Uc Vv Yi) Ao(Eq Rc) Gb(Dd Ks) Ny(Lh No) nL(dE pF) FaJf NeLt UbaW UcHu IbTn JnRm aGcX bHcF} qU{mT(Bn cC Cu dB dF Or) nA(cM Cv dD jY mI) aG(kC nC nH nL) kF(aK bJ Js) Em(Iq Uh) bE(mE mI) lY(aK qY) aUmH bXnL cHkI cVnH mEqY mZqX nIrZ} rB{yJ(Fa Fy Pe Po Un Wm) Tz(Ez kR Ly Of rZ) Sr(rZ Um yL) mT(aG bF cS) tR(Fw Ip Nr) tN(Jr Js Mh) Po(Ct wQ) Um(Mt Or) NgSt OzuN mZIL} Nj{Nv(Fp Ik Mr Ng Nk Of Oy) aA(Iv Jl Jn Lv Mi Mp) Fp(Jl Jt Mm Nm) No(Jl Nk) Lx(Mh Oy) Qa(Nk Nx) oW(cD cR) GdiJ HvSh JlLi} eQ{Mn(Bb Jo Ju Kn Ld Lu Mm Ms Rc Yi) bO(bC Ms Ng) Uu(Lv lY) cR(Fw tF) nW(Pk Qu) DutF EfmT WmKx TjkG GhJf GdPj NoQw YdKs LdpK} oE{Uh(cM Hc Iz Lw My Ou Qx Rf) qH(Jv Pe Rg Tr) Zq(cQ Oi Rf) Dk(rQ vI) Eq(cF Fy) vA(cU Po) WmsK NoRy YjcM JvPk KztR UycX zHqX} eP{Tn(bC cR Hv Kk Qv) Or(Ao Cw Il Kg Pd) Wd(cG Mp) bV(Kc Mn) AoUy ExVz GpeW HolI HqYi YhUg ShRf SjLi QxiJ QvLd XaUr RtOw cTdR} wQ{cT(Cu Js Mh qX) Po(Dk iP Nq) Ef(Lh No) Ib(Fy No) Ip(dD qX) Jk(Nv Nx) Jv(Fa Mt) Ld(jV qX) tV(iP uT) AruN AwCu WmbC NeNx JhbA KrjV} oD{Zx(aM Ao bC iO mI Nb nL Ow) cR(bX Nh Nl Ns) Eq(mI Ow) cM(Mq oH) CtRz DrnH FwJk FySh YiQa VzPe SiaW SfcD ZqKl XaLi KxbJ} Qm{uN(aW Ch jO Of Qc Ur Vv) tR(aM cR dM Hf qX) Ne(sK tV vU) Mh(tN tV) yJ(dA sM) sK(cH jV) wD(iA Mg) JktN OfrZ dBjD} kG{Rv(aW dB mE) Du(aW Up) Hl(Ir Vq) Yj(Fr Mf) Zq(Kf mM) Wc(dE Up) Yl(cA To) Op(bG Rh) Vi(Ij No) EqUd IbXa IhWd YiOz ZwbH dMqX} lY{Il(Gn Wh Yj) jM(aS bZ cU) We(Is Tn) Vi(Ij Lx) qY(Ky Mj) lN(aS mH) MwIb NkRx ShmE ZqUu WdbZ aMqX bEqW bGqT bUlM cVjY} eW{Gp(bA dL Mg) dC(aQ Nb Qa) Po(aX Mq) Ik(aP cB) Oh(Ly Mg) CtPa CxNo EmMu MabB MtcX MvcC MwQa IlbP IqaQ aXcW dFfP} sJ{kR(aO bI Cx Hx Nq Pz qZ) Hf(dR Pb Pg) Hx(oF wC) Kr(rY wH) hW(Cq Pa) jM(cE rZ) TjKz KpaX PfjE dApF} iP{yJ(aF Js Mi Ou Pb Pe Uv Wm) tR(Cu Dl Mq Nr Ou) Gp(Fc Wb) DrcF FySh NoSf JvtN KptL VanA} Nx{Of(aA Ir Is Iv Lh Lx Nm Nn) Ms(Fp Ij Iv Mr Qa) Dw(cA Gd) Fp(aA Nm) LyzG NgrQ qWkC} eC{pK(bO Di Hv Nb Ne) mS(Jv Um) kC(Ib Ri) kF(Pj Qc) DeSh MkoW ZqRf JlpH RymY RvmH VqmI dJpI gZkQ} rA{aG(nC nD nI nJ) bH(nD nH nJ) Em(Cu fR) IikF LdtR PjnA aFuO aMkO aRlW bOnC bQkC bXmF cKmP dMmE} Sf{kP(bR cA mE Us) Dk(aW cD Oi) kI(bR cA Jf) Ij(iA mM) pI(Fy Ha) DdoW NkJr HvbR UpnL aImE} jU{bC(kC kO nL) kF(aG aM cC) bH(kO nJ) cH(kC nJ) nD(aS Hf) FaLy PzmP aXnL aZkC bVnT cCmZ dAhP} qW{Cu(Ng Of) aM(kK nT) lW(bJ bU) kC(Ky Ns) kF(bE cK) LyKr MjkN aZnT bHkO cUoN cYnR dMeF rQpF} jP{bJ(mI nC nH nL) nH(AS bE) kC(aQ aZ cM) fR(Cu Li) kO(aQ aU) HcmZ aSnC bEnJ bGmT} Hv{Xa(Aw Ow Si Vs) Gp(Eq Rz) Wb(Mh Tr) Sh(Dk Mn) Vc(Fy Nm) EwOf GnJv SibR bBoW ILoQ} Zq{kP(aF Mh Sh Yi) Vj(gC oT) mM(Ps Sh) FaeD FwgP GbmS QwkS QveF KjoK UsgW VoiJ cQfP} dW{Mu(cC cE cL) An(Iv Qc) Is(aG Pg) Jr(dH fP) bB(Mm Pz)

Figure 39 Continued

LycB MhNi MvdC QaaF OyaA bRcO} iA{yL(Bc Cq Il Jy Lw Mi Nr Pd) wB(Ou rQ) WmuT IpwC UhdL VqvW bGvI wPjE jVrQ} uY{jO(Ar Fa Kn Ql Tz Un) My(JV) Ne(Gl jK) Ur(Il jE) AnjE NiTo QljK UhtR VtvT} sI{bC(Ib Nv wP) Hq(hW sO) Rb(hP jK) dE(aY Ny) zG(Cq Nk) DpKs OyvO PaPj hAwP jMxA} qX{tR(Dl Kr Ld Uh Ur) cU(mE nJ) kC(bH Ky) kF(bG In) AruO JvuV PjnD aSlX zHoN} To{pH(bH Bo Ur) Ni(qA rQ) yJ(dA Un) DrmS DukI YjkP YlnH VchB gWwD gZnL jDsK} pF{rQ(bE cU Lx vI wB) Rg(iB vI wD wE) Vq(hA jY) cG(Sh Wd) NsvI QwXa} Ng{Gl(jV lM wE) Uf(kP lM) rZ(Bb Uh) DlvB WmrS NmLx ShkS KorQ TkhV UnuX} Dw{Ct(Hw Mg Mu My Qc) Gd(My Om) Lh(aW Jo) BbMf DgPa MlJh PbbA} Ib{No(Ed Ic Jo Ju Mm Oi Rc Us) FyUh RvnL UnuV PbuO dKrQ} jV{An(qQ uN) Qx(Or sK) hP(dM Pk) tR(Kr Vu) YfUs GdYj LyOa OrOy aWsK} pK{cF(cQ dC) dD(Mm Om) nL(dA Mk) oO(cR dB) TjkR FwkI JncQ RmNv RiUm} oW{bB(cO cR Ma Nn oO) dD(Nn Ny Wm) cX(cQ Oy) EqdB bEbH} Nk{Ew(Fr Mw) Rg(fA gZ) MnSh IdfA SsnT RxgC LpmM bBgZ bVoP} mT{iB(bR dB dE) EqTn KfjT OrlM bZlN cGrY cHjI cWhX cXrX} vA{Jv(dA Is Pd Pe Po) Un(Ef Ne Qu) NidH PzTk VqdB} Cu{oP(Rt Up We) tR(Kz nW) EqmS JkuN RyLj UyeF VwmZ} Ex{tV(Ax Cs Kn Ld) Tz(eZ uT yE) FawL QtsM QleZ} Kx{pI(cR dE Fr Ky) mS(jY qV) DpTk ShkS QgeM jEkI} Of{Mn(bA bS) Nv(aA Fp) CsUh GllM NmLh KrrY PjrZ PkcV} hP{dA(cM Gl Kz Pf) Lx(Ma Nq) DkVp PoMw FyJv MtPf} kF{jQ(bG bH Hu Js Mr) lL(nJ oO) EqcM aZjY bJiB} Du{oT(Al An Lp) gC(aW Ph) pI(bX Fw) bSgL mEoH} Jk{Wm(vH wC) wJ(Nv Qh) DltN IjrQ IlvI cUvH hRwB} iJ{Gd(jG Lh Yj) Ry(Ed Lx) FyRt NoPs YiOr QwgC} mZ{Uf(Sh Vw) Uw(cG Lh) TnWd HclL JljY UpVa} nH{cX(jY lL) fA(Em Ky) DdRv IjVi KkjF OpUs} nL{cU(jM jR) DdRv EqUs WeOz KkgZ YlmU ViaI} Js{Ms(aA Fp) jD(cX sK) EqkI HlmU WnrY} Uh{fP(bE dL Jv) oN(Lx Pe) FwJo aWsK} aF{uO(Aw Ch Cs iH Iz Qy) KzuN} lM{wB(dB Kr Uf) YiUp LhmP LizG OuwD} Gp{Ew(Ax bI) EqtF FdlN WcnD LtkP} bU{mF(Gn Zx) EmnY WdnC WfnD LpnB} uN{Po(Dk Nq) NiTr TzjO IpUr QxcM} Fp{Nm(aA Hr Iv) HrJt JnaA} Ly{Hf(hV lN tV) Kr(iC jD)} Wb{Tr(Dc Lj) DeMh LjUw bOgP} Xa{Bg(gP nY) ShnY RfnW cDgP} Tk{Ap(qB uX) uG(Ih Nl) aVvB} Un{yJ(cT Qg) EfuG MguV UurS} aR{jR(kK mI) YjeD UygC lXjM} nT{FyQv UmkP VvOy cTjQ dEiB} mE{GdaH IlWe JnLp aZjY bXqY} mU{Hl(Jn Qb) YfLi LxZw RvPi} Tn{AxfB YdgC WenJ VinB} Ry{kI(Lj No) MnmY aInB} Pj{rZ(bC Mg) GdgL YdgC} cM{fB(Hq Nh) HlmH RxlW} cU{lXjR nCjQ nDhV iCkC} mS{Yi(Fy Il) QaRm UfUw} tR{Ip(aW bI) KzoF UrqQ} jD{MyJl QxsK KzLh QlwE} lN{nJ(cI dB) IdHf kCrX} rQ{DkKn NijM IdbC JoKr} Eq{mY(Co Uc) cGpI} Ne{GluO LtoT hRwB} Yj{eD(Dr Qy) IqoP} dD{IdwJ IvfB nBlL} nR{YhcG WhUf cCqV} mI{GdMn WfRg bJiB} jY{GnNf KcLp kCrY} kO{aShA bHqV cXlL} Dl{Mg(sK tN)} Ef{KrrZ NysM} Po{NqqQ QwoN} Jn{ZwoP WcnD} aA{MsIh QaOy} aG{fRjQ mPqT} cA{pH(Kl Uu)} fA{QvbI KkcH} gC{QwcR OrbX} mM{WdcG LhlL} nC{HlaW IlWc} jH{AnnD HcnA} qY{aZlW cZfR} AoZxpI BbWhJr DeUwVt YfFajI EmeFlK FwWnaS GhcQgW HalnoT NiOuvU ShUfkP JlTmoP KrUrwJ RvPieM VqaXsK VvwLnW PfbBgZ bGjMkK dGmPrZ Constrained panels with 3 analytes, where 1.0E-8 >= 'AUC p-value' > 1.0E-9. Contains 11,570 panels of 38,239,313 total panels evaluated. : aC{Nd(aM aX bM bV Cs CU cX Et Fa Gc Id Ih Is Iz Jp Jt Jv Kc Kq Li Mi Mt nO Ok On Or Qc Qm Uh Zq) Jp(aM bS Cs cU Ed Eq fP Is Jj Jt Ju Lh Li Mp Mt Nb Ng Nh nO Nw Ok Qc Qe Qu Qx Rc Uu Vs Wm) bM(Aj aM aN aX aZ BA Cs cT Cu Dc Fr Jg Jq Lh Lj Lx Mm Mn Mp Nb No Nu oE Og Pd Qa Qc Qe) Aj(Ad aM Ao Bc dF Dg Dl Fb Fr Fw Fy Gl Io Iv Kf Lh Lx Mg Mi Mn Mp Nu Nx Qa Qm) Jt(aA aM bA Cs Ct Cu Ef Hr Im Jv Li Lj Lx Mi Mt Nb Nc Ne Nh Nk Nw Og Oi Qc) Of(Ad Ap Bc Cp Dc dF Dg Dl Ed Fr Ha Ij Jg Ko Kr Lh Lx Mm Nv Oa Qa Qc Zq) aN(aX Cs cU Dc Dd Ed Fa Fw Fy Gl Ij Jg Jj Mu Mw No Nx Og Oi Pd Pe Pf) Ne(aM aX bA bV Cp cU Dc Kq Lh Lj Lx Mi Mm nJ nL Nt Nu On Po Qa Wm) Li(aA aS aX aZ bA bV Is Jj Jo Mc Mi Nb Nk Nu Oi Ok Or Qc Qe Qx Ub) Et(aO bA bV Cs cX Ih Im Is Jj Jo Lh Lj Mt Nb Ng Oi Pk Qc Qe) Nu(aM aZ bA bV Cs cU cX Dc Gc Jj Kq Lx Ly Mp Og Oi On Qm) Qe(aS aX Bb bS bV cM Cu Ef Im Iu Jo Mm Mt Nh Nk Oi Ok Ow) Jj(aM Cs cU Dd Fb Fn Fy Ih Is Ke Mt Ok Or Qa Qm Vq) cX(Cx Ed Fn Fw Fy Lj Lx Mm Mp Nb Nt oE On Sr Wm) Ih(aM aX aZ bA Bb cM cT Jo Mm Nb Nc Nh Nl Oi) aM(aA bA Cs cT Fy Is jB Kq Lh Lx Mi On Qc) nO(Bo cF Dp Ed hC iJ Iq Ji Ke Nk Nn Nw Uf) Im(aS cM dB Ef Jo Mi Nb Nh Oe Oi Ow Qc) Id(Fy Ib Il Ju jV Na Ns oE Or Ub Wm) Is(bA Bb Hr Mt Nc Nh Nk Nl Og Oi Qc) Jv(Bb Il Jq Kn Ko Kx Na Po St Uf Wm) Pk(Fn Gz Ib Ic iJ Kq oE Uf Un Us Wm) nT(Aa Bo Dd hC Jr Kp Nh Nk No Ok Um) Ef(Fy Ke Kq Lh Mg Mm Nt Ok On Pd) Uh(aW Cs dB iJ Ju Lh Lj Mz Qd Uu) aX(Cs Lh Lj Lx Mm Nb Nk No Nt Qc) Cu(Hr In Jo Ly Nb Nf Nk Og Qc) Mi(bA bS Lj Lx Mt Nb Nk Nw Qd) Or(aW Iz Ke Mk Nh Nm Oi Ou Oz) Ji(Fn iH kF oE oN Ou Rc Uu) Ok(aO Cs Hr Jo Nb Og Oi Qc) Kq(Bg bV dE Hv Jo Oi Om) Un(Ic iJ Nh Ou Pj Rf Wm) Fy(cC Dk Gz Ib Iz Vt) Gc(cZ mW Nc Nk Ub Vt) Lx(Bb bS cC Nk Qc Qx) Pj(Fa hC jD lN Ub Uu) Cs(Fn Ju Ly Mm Nh) Nt(aZ Jo Ly Og Oi) Mt(cE Hr Ly Nb Nh) Qd(iJ Ju Qx Ub Wm) Ke(Ib iJ Iz Jo Ow) Qm(aW Ju Lj mP Oz) Vq(cE Nh OE Uu) Bb(Ao Lj Mp Qc) aS(Fb Fw Mp Qc) bV(Mm Nk Og Oi) eQ(dK nH No nW) nN(Dd In Lz Nl) Mz(Ju vV yH) On(Ao Dk Oy) bA(cC Mm Nk) nL(Mb Nl oV) hC(kG mI mP) jB(bG cA cF) Ar(Oi Qx) Wm(Nm Oz) Ed(Hf Kz) Fw(aF Ly) Ho(bU Gp) Zq(Nn Ow) Qa(Nh Qx) Qc(cM kG) Kc(dB dE) Vt(tO wJ) cU(Jg Mm) iJ(mS Po) kF(Dd Mb) oW(cA cI) TinH LyHf NkfA HvYe IrkG IzLh JfdU KlTk UwhA VijP PemW eCpK nIoH rXoQ} Jp{Ng(aN bM Ih Ij Ir Is Iv Jl Jn Jr Js Jt Jv Lv Lw Lx Mf Mi Mm Mp Mt Mz No Nv Nx Ny On Pd Po Qe) Oy(Ij Ir Iv Jg Jl Jn Jq Js Jt Lh Lv Lx Mf Mh Mi Mp Mr Mt Nl Nm No Nv Nx Og Pd Pe Po Qe) Ef(aW aX bL dB Ed Fb Fn fP Ha Hf Ho Hp Ji Ke Kg Lj Mz nO oE Or Qe Qx Sr Uf Um Un Vu) Jv(aH Aj AW bL dB Dg Eq Gz Hc Ib Ic Ji Jj Jo Ki kP Lz Mg mS oE oK Or Qd To Um Tl) Of(Aa bM Cs dE Fa Hc Hf Ib Ic Id Ih Ik Jn Jq Jt Lh Lv Mf Ms Nl Nn No Oa Ow Pe Qe Tz) Iz(aM cC cX De Fa Hp Hv iH Ik Ke Lx Mp Mt Mu nI Nm NN oE Or Qx Sf Uc Ut Vt Wm) My(aN bM Cs dE Ib Ij Ir Is Iv Jg Jn Jt Lv Lx Mf Mh Mp Mr Nl On Pd Pe Po Rc) Og(aA Ih Ik Is Iv Jq Js Jt Lv Lw Mb Mf Mi Mp Mr Mz Nl Nm No Nv Nx Po) Ms(Ij Ir Is Iv Jl Jq Lh Lv Lw Mf Mi Mp Mr Nl Nm Nn Nv Nx) Vb(As bG bO cE Dd De Du Ir Is Iv Ji Jr Kr Nb Nk Qe Sh Up) Hp(aM bG bM cC Cs De Fw Ik Jj Lj lM Ne Rh Sf Vc Vt) Ib(Cs Ed Eq Ha Ic lY Mz nI Qz Rz Sf To Uh Uw Vt) Mz(aA Dk Hc Hx Iv Jr Kl Lw Mb Ny Pb Qa Uu) Rz(aW bG De iJ Jj Li lN Nh Ni Nk Sf Sh Si) Mb(aA Jl Jq Js Li Lw Mi Nm Nv Qa Qb) Sf(Bg bL cE gP iA Ju Mf Nh oE Or Ow) Eq(bO De Gp hC kG Lh Mm Nc nL Om) Sh(bO cE cK De Hv Ma mM Or Ry Tr) Uw(Ar cE Du Hv Ik Jj Li Or Qu Qw) To(Aj Ic Jj Kl Lj Nd Nl Or Uu) Im(Jl Jq Jt Lv Lw Mp Nn Nx) Si(bG fP fR Hv iA NK Vt) Kl(aN bM Cs dE Kq Kr Lj Vc) Mh(Iv Jl Jq Nn Nx Pb Vc) aA(Ij Ir Iv Jn Lv Nl Nm) nO(Aj Ks Ou Rf Ux Vo Vw) Fp(Iv Jt Mp Nn Nx Pb) Ap(Hc Id Kq Nm Pj) Gc(Ju Uu Uv Vj Vo) Mp(Mx Nq Nu Ok Qd) Yi(eF iJ kG nK oE) Or(aN Aw bM Lv Ow) Vc(Fc Ik Mm Om Qw) nT(Bg cF Gd hC Tr) Nm(Mr Nl Nu Qa) Nn(Mx Nu Qb Qd) Lw(Ok Qb Qd Qe) Ic(Aw Bg bM Lj) Yg(bG bO cE Nc) Uu(fP Lj Mx Qx) aN(Aj dE Hc Ow) nL(lL Vj Wd Yk) Cs(dE Jj Nh) Wh(hC jE lY) Ry(nB Nd nH) On(Jh Mw Nq) Bg(Ho Kq) Mx(Jr Js) Nj(Jt Nx) Hx(Lx Nw) Tr(Gn pH) Hc(dE Lj) Zx(gP mS) Qb(Jt Lv) Qv(eM fR) Jj(Aa bM) Ow(bM Lj) Um(Qu Rc) Vi(eD gP) Vj(iJ lN) nN(Ad cM) lL(kO mM) AjQc FbpH GbiJ GdnA NuNx TzoP UceM HqSj HrPc IvQa YkhC ZwjE JoKr YenI VwmW PkdE bEmI} Mz{Aj(aM bA Bb bC cC cM cT Cu dB Et Jg Ji Jt Jv Lj Mg Nb Nf Nh Nu Ok Oz Qc Qe) Jj(aN Ih Ij Ik Ir Is Jn Jt Lh Lv Lx Mm Mt Mx Ne Nh Nl Nn Nv Pz Qc) Iv(aA bE Fp Jl Lh Li Lv Mb Mi Ml Mm Nh Nl No Nv Nx Pe Qa Qb Qe) Im(aA Fp Hr Jg Jn Js Lh Lw Mb Mt Nc Nf Nl Nm Nv Nx Of Oy Qa) Og(Fp Hx Ij Ik Ir Is Jn Li Lx Mb Mt Ne Nh Nl Nv Nx Pb Qc) Nj(Fr Js Jt Lh Lw Lx Ml Mm Mp Mt Mx My Nm Nn No Pe) aN(bA bM cT Ib Jo jP Ju Li Lj Nf Nl Of rC Uh Uu) Hr(Aw Fp hP Js Lv Lx Mb Mh Ml Nh Nw Ny Po rU) bM(Bb bJ cM dE Ed Iz Ji Jv Nb Ne Oy qW Rf Uh) aA(Fp Ij Jg Jn Li Mb Mt Mx My Nl Nm Qa Qb) Qe(Hx Jg Jq Mb Mi Mx Ne Nl Nn Nv Nx rB) rC(aX Ba cB Ch cI Co dB dE Dk Qu Qw Qx) sK(aF dN eF hR iP jO Jv lL oE qW qX rB) hP(cX dA Hc Iu Jk Mg Mj Mv My Qy uM) vA(aF aW dK Fr Ha jK Mx Ne qX rB Tj) Ms(Jl Jt Li Mi Mm Nc Nn Nv Pe Po) Mx(Hx Jl Jt

Figure 39 Continued

Lh Mi Mm Na Nv Nx) My(Li Lw Mf Mt Nm Nv oE Qb Qy) Of(bA bS Cs Ed Fa Fn Js Nv Wm) Oy(Ir Jn Lw Nv Nx On Qa Qb rQ) Um(Aw Hv Iz Nh oE Rc Ua Uu) qW(cC cI cU dE Hf Kp Qt wC) Ef(bE Dk Jd Ke Kq Nt rO) Hx(Jn Lw Mi Mr Nm Nw Nx) tT(AF aY dK Il Ly Qn) Gc(eC Rm Tr Uu Vq Vs) Iz(aS bA Hv jP rZ Uh) uN(jO Ny Qm rO rV vT) Nm(Fp Jr Ne Ng Qa) Lw(Fp Ij Ir Li Pb) Nf(Lh Lx Nw Pe) Uh(Aw Jo Uc Uu) Pb(Ih Ir Lx Nw) wQ(dH Fr To wB) rQ(bC iA Nq Pf) Nu(Li Mp Wm) Mb(Jg Li On) Ng(Jg rO uL) Hv(Hc Jv rU) Ib(rU uL uO) Ny(Ir Nw yJ) Wn(Ax iO kR) aS(Hc Ne Nh) wL(eF Ow Vv) hR(tR wE yH) zG(dK Qn vI) jP(Aw Cp Hc) uI(It Mn No) Fp(Jn Nx) Mh(Lx Nw) Mp(Ok Qd) Qa(Jg Nl) Wh(jU jV) Jo(Kg Pj) Xa(jV lK) Kr(Ad rX) Lj(Rf Rm) Uu(qV yH) wJ(Fr wB) yJ(Il Ne) rB(Tz wC) jD(Qw Qx) kR(sJ tL) rZ(eF Ic) lM(wB yH) yL(aV dR) vI(Mj Ni) AftX CsRm DeHp FwTk NnIr NdSf YgmS YkkP RcqV ZwjR QbJt QdNx JhQy WcjL QvrU TlhA RzlK RyeD OwvU VvuM PjlN aFuO bCrO tSqQ tOsO uLuY} Jj{bM(aN BA bE Cp Cq cT dD dE Fb Fn Ij Jd Jn Jq Js Ke Kq Kr Li Mn Mx Nb Nt Nx Oa Ok Ou Qc Qe Tz) Jn(aA Fr Ij Ik Ir Js Jt Lv Lw Lx Mf Mh Mm Mr Ms Mt Ne Nl nN Nx Pd Pe Po Pz Qb Rt) Tl(aN bO bU Cs Ed Fp Fy Im Ir Kq Mf Na Nb Ng Nk Nq Oh Ok Qd Tz Uf Xa) Nx(aA Ih It Jm Lj Lv Lw Mf Mm Mr Mt Nc Nd Nn No Ny Og Pd Pe Po) Qb(AA Fp Fr Ij Ik Iv Jo Jq Js Lh Lv Mm Mt Mx Nl Ny Og) Nj(Ii Ip Jm Jq Jr Lj Lv Ma Mi Mm Mn Mp Nb Nn Nq Pe Qc) Fp(AA Fr Ii Ir Is Jq Lv Lx Mf Mg Mm Ms Mx Ne Nh) Jt(aA Ih Ij Is Iv Lh Mb Mh Ms Ne Nh Nl Nv Po Vb) Nm(Ih Ij Ik Ir Is Jr Lh Lx Mt Ne Nl Nn Nr Qc) Mx(Fr Gc Ih Ij Ir Is Iv jB Lh Li Nn Ny Qa Qc) nO(aK aL bB bC bU Cu dA DD Ef Fw Lh Tr Tt) Aa(Et Ih Im Is Li Lx Mb Mt Ne Ok Qc Qd) Js(aA Ih Jl Lv Lw Lx Mm Mt Nl Nn Nv Ny) Ij(aA fR Iv Lh Li Mb Mh Mm Mt Nl Po) Iv(Lv Lx Mh Mm Mt Nl Nn Ny Po Pz) Lh(Ih Ik Ir Is Li Nn Pz Qa Qc) aN(Bb Fw Gc Jv Kr Nu Or Qe Uh) Li(fR Ih Ir Is Jq Mf Ne Nn) Nv(aA Ih Lv My Of Og oP Oy) Gc(cF gP Hv Mf Pi Sf) Qa(fR Jl Lw My Nn Og) Ms(Jl Nn No Ny Pz) Nl(Fr Is Lx No Ny) Ho(cI Dk Gp hC Mk) dX(Fa Ha Ou St Vt) fR(bA Im Kq Nt Ut) Qe(dE Jl Mp Nn) Ok(nT Uw Vc Wh) nN(aL cA hC oK) Wb(De Mf Nd) Cs(Ji Uh) Dc(Jv Sf) Ti(nC sK) Tz(jV oP) Qc(dU Ik) Xa(iP kP) Kq(Ef Jh) Ks(Jv nU) Rt(Gp jU) Nw(Me Mp) Ut(Du eM) aA(Ih Nr) tR(Il Un) jD(nR Vz) DrlN EmjV FyUw NoIb LvNy MnNh MwOn HpjL IdjB ZqhC JidE KrtO UfmS VqwE VwjH PilY PkiJ mErZ iBkF} jV{Rt(An Bc Bo cF Cp cY De Gp Il Ir Iv Jk Kp Kq Kr Lz Mt Nm On Pg Pk Rj Tn Ut Uv Vi Xa) Gz(aG Ax bA cC cU Dc dM Fw iB Kf Kq Ma Mr Mt Mx Nm Nr Nt Nx Ok Pb Pi Qa Uc) Wh(aH bJ Bn cH Dd Dr Em Fa Hl Ko Kr Lh Po Rb Vh Vi) cF(Dr Fc Gn Hl Ho Ry Uy Uz Vb Wd We Wg) Ye(cR Dk Iq Is Ji Jq Kr Mq Qa Qb Qd) Vi(aH Ef Hc Iz Kj Ko Mu Mv Qm Ua We) hP(aF An Id Ji Jr Js Ke Kp Md Ni Or) Ly(Cs Ic Id Nx Or Rg Sr Tz Tm Wm) Rz(cG cL De dL dM Hq jl Tn Uv) Fd(Cu Jk Js No On Qe Tv Vu) Vb(Ad Dr Hl Hw Kp Qm Uc Wc) cY(Dr Gn Hl Uz Wg Yl Tl Xa) Lt(aH cI Js Li Mx Oh Pk) sK(eF Ji Js Ne oK Qd rC) Lz(Fc Hl Ho Uz Vw Wc) Lp(Dd Gb Hw Jt Jy Nj) sH(dR hW Pg Qh Tr yJ) Gd(Fc Ho Uy Vh Wc) Mh(Vz Wc Wd Wf Wg) Uw(cR cV Mu Of Zw) tX(Ch hC Js Kz Lu) Hl(Of Pd Tv Uh) Yg(aI Fy Qt Vq) Wd(Dk Kn Oy Vu) *Jk(Ho Ry Uy Uz) Kj(Dr Gn Vh Tl)* Um(Pd Pk Po rS) *wQ(Fa It Oa Vu) tO(No Oa Uc Un) qQ(Id jK Sr Up) Yf(Ko Md Qw) Em(cM Nd Qb)* Yh(Dk Fw Sh) Zw(Dk Ex Mt) We(Ij Pg Vu) Xa(bS Oy Rx) Ri(Fc Gb Ho) dI(Vz Yl Zq) rS(aW dA dR) uM(An Fw Up) Cu(fR vA) Gh(Ch Ua) Gn(Ks Yj) Tv(Fi Ry) Hb(Gb Tm) Yi(Aj Iz) Sh(bL cU) Jv(Vz Yl) Ke(lM tR) Kr(vA yJ) Qm(Uz Wg) Or(Hr Qw) mW(Af oQ) tT(Ju rC) qZ(iA Rc) qU(nR oP) DrhA WmuN EdId ThYj ExHp MyTz NgUf ZqKi WcOy JmVc TmOg UsqH VvrQ VwPh aNuY zHqX} Gc{nH(bL dB Dg dJ Ib Mh mU Nt Ny oE Pg Sf Ua Uc) Sf(aW bR Dk Gp Jm Lj Mh Mk Nh Qv Vi) Uc(cB Cu dF Is Jl Oa Ok Qh Rg Tz) Va(aN Is Jl Mh Mk Mx Nb Ow Pi Qv) Nh(Ed Jr lX Qb Qd Rg Tn Ub Us) Sh(Fy Gp Jr Or Qh Ub Vi Vu) Jv(cF gC Gp Jr Mt Vu Tl) Ut(Bg Ef iB Jo Kg Of Uv) Uu(Bb Dk Hv Mt Na Ny Tz) Uy(Aa cF Cs Gp Hp Na Ow) nL(aI bL Id Ik Ki mU Ql) Ub(Cv Du Nj Rg Si Vt) Or(cF cX Hv Mh Of Ow) Vq(Ha Is Ji On Pg Po) *Vo(Cu Is Jl mF Na On) gP(aA bM cF De Jn Lj) oF(cE Ma oN Rf Rh Rm) Hp(Ho lY Nb Qa Qh) Rc(hG Jr mS Pi Vi)* eC(aM Bn Nn Ny Op) nB(cX Dl In Jr oD) Rf(hB Jr Nb Oa) Uv(aN Fy Lh Ue) lY(bO Nc Wd Yk) kS(cD Iz Og Po) Mh(mW Us Vt) Mt(Uf Ux Vj) Tz(It Ow Si) Ju(Ho kP Tl) Oa(kP mW Nd) Vi(Aj Ef It) gL(gW Ow Rh) kG(An dB Kn) oE(mW Rh Yg) Hv(Ug Ye) Qv(mF Si) Jr(eQ Rj) Ok(Uf Wh) Us(mS nC) dF(Uf Vs) gW(dG Ny) nO(Gn Nk) mY(Dl Eq) hG(Vw Wd) kI(Ad Ef) CsVt CuUa DuoH EdTr GpnR NnnN MmQe MxUk NeoD NiaN UebO HqOf TniB IojF ItnK YkgC QzTl JlRm JtkQ YeiZ KqjI LjcX RgOw QlnW UnPj PanC PieD aFkP bHmS cGiA} aN{Qc(bA bE bV CU dE Is Iu Jo Lj Lx Mi Mt Mx Ng Nw Og Oi Ok) Lj(Bb Cu dK Jv Mi Nd Nt Nu Nw Nx Og Oi Ok Qd Uh Um Tl) Aj(Ad Ao bA bM cT Dc Gl Lx Mm Mt Nd Nv Nx Ny Qa) Li(aS bA Bb bE dE Ik Jo Nd Ne Ng Nu Of Og Ok Oy) Nw(bA Cs dK eP Jv Mh Mx Nd Nm Oi Oy) Bb(cT dE Jo Lz Nb Nd Ng Nu Of Oi) *Im(bA cM cT* Jo Nb Ne Ng Nx Oy Qe) Nt(aS bA Ef Ik My Ne Ng Oi Oy) Qe(bS Iu Lw Nb Nd Ng Nh Of wE) Og(bA Cu Dd Is Jt Mx Nu Ok Qd) Jv(Gl Iq Jn Na Pk Qm Tz Un) Ok(dE My Nb Ne Ng Nu Oi Oy) Uh(Ap bV Fw Il Ng oE Pk Wm) Qd(aS bM bS Nb Nh Oi Oy) Nu(bA bO cT dK Ir Ne) wE(Ed Nx Ou Qm rQ uN) Lx(bS dE Ne Nk Oy) uM(Il Ir Is Or qX) Ef(Aa Et Ke On) Um(Ed Ji rZ wF) bM(bA Or Pk Tz) Cu(Jo Oy tO) Mn(Nd Ne Oy) Is(aS Nl Of) tT(Il Mf Wm) rR(jU Kc Nx) Ed(Kz Tl) Lw(cK Nf) Ng(Jt Kq) Hp(Ho Jn) Ip(sM uN) Ji(Ju Mm) aS(Ir Nm) wJ(dH tV) tO(Kr Ou) rQ(bC uY) WmuY PobS GldE GzsC NoIb NqtV MhtX MtbE NddD NhQa JhKq JoKe JtOf LhwQ OybA nKoV qXuV} Hp{jD(aH As Gn Hr Ij It Je Js Kd Ld lO Lw Md Mi Pe Pk Ra Ry Ud Uz Vj Wg) Ho(Cs Cu Dr Et Jl Jn jQ Li Mb oE Qa Tz Vt Wb Xa) jQ(Dc Hl Hv Is Li Mb Mt Or Pe Qa Ry Us Tl) iB(cD cS cX Fd Hl Hr Ne Nk Pa Pi Qe Qy) lM(bV dA dM Js Kg Mb Nb Om Us Ut Yh Yi) jI(cR dK Ez Io Nc Ne Ni Nk Nl Qw Qy) Wb(Cs De hG Hv Ir Is kG On Qa Vt) Ed(Dk Kp Nb Nd Ok On Ou Pj Tl) Qe(Ao bI Dk Dr Mb Mn Ns Ut) hC(Ao Bb Cu Dd Ic Kq Pi Qd) Fy(cE jL Qa Qb Sh Vc) Nd(aM Hv On Qa Qh Tn) nL(Ji Lh Mf Qb Qd Uf) iC(aU Oh Qm Ug Vc Ye) jU(Cs Iq Jd Kn Mq Nb) kG(cA Hb Ir Jm Ng Qb) De(Cu Ir Jn Jr Lj) Hv(aM Dc iJ Qy Xa) Vt(Dc Im Jn Jr Ps) nK(Dr Hx lY nT Or) Nk(fA Jr kP nH) jE(Ps Qy St Yh) Cs(mW Qy Vq) Fd(dU jR nI) lY(Ih Ir Mf) mM(Nv Uf Un) jL(Gb Jv Sh) Dk(aM bU) Dr(jF oV) Qd(iJ iP) Qh(Hw Jn) Ok(mW Or) Ut(oP Or) Vq(Jr mE) bL(oV oW) dU(Ij Ny) mS(Uf Ti) mZ(Kq Tn) jR(cM Yi) lO(Ne Pz) CuLv DbjH DdpH NonI HbmE IrkP ZqoE QaiJ JiiZ KseQ UpnB eCnA nOkI} Ji{bM(aL Ap aU cM cT dD Dl fP Ii Ik Iz Lh Mm Og Ow Oy Pg Pk Qg) dE(aS bA bV Ik Iu Jv Ms My Nb Ne Og rC sI) Jv(aS bE fP hP Jo Ki Kz Mk rR rU sK) oE(cM cX Ef Gz Ib My Ry tX Yk Tl) Aj(aM dB Ms Nb Nh Nm Nu Qe) wJ(Fr jO Mt Nx rC tU vT) wQ(dM Fr Hr tV uR vI zG) tO(aW Dl dM lM Mk wH wP) rU(Ib jD Jh Jk Jt Ni qX) Jo(Aa bE Cu iH iJ Ow) Tl(bU Ed Uu Uv Vb Vc) Of(Aa bA bS bV cT iJ) zG(cS Ly Ne rC vA wE) Vb(gL Ho Jn Nd Qy) rQ(Dk Ef iA Jk vA) hP(cS dA jD tR) hC(nT Yg Yk Zw) yJ(Il jO uL wE) sK(Mj Ni rB rC) wF(Kp Ne Um Vv) uM(cK Dk Mx wE) Ib(jD rV Uh) Yd(gZ mE oO) mM(Gb Gn Uw) tX(cS fP iA) Aa(Ms Nb) Aw(Hr Nb) Ef(Nt Nu) Ne(tU tV) Yg(hG oD) Jq(Ap cX) Kz(jD Uu) Ry(eC nB) Uy(Nd nL) Ux(dU eQ) Vi(iC nB) bV(aX fR) nN(cM Rf) nR(Va Wc) mZ(Gd Zw) tT(cS fP) tR(bI iP) uN(Iq Nk) TiwG ThwB GzqB MjqI MybA HoQz IkwL ItwK YiiJ YjoP SiVt QhsI PsnL NyjB OpoD UwdU VclN VoeQ aLmI cRgZ cYvP eCnO eMeP iAwH tVlM} Nj{Fp(Fr Ij Ik Iv Jq Js Lh Lv Lw Lx Mi Mp Mr Mt Mx Nd Ni Nk Nn No Ny) Mr(Fr Jg Jl Js Jt Li Lx Mi Mm Mp Mx Nd Nm No Nx Ny Og Qa Qb Qe) Lx(Hx Ij Jl Lh Mi Mp My Ni Nk No Nx Ny Og Pb Qa Qe) Qa(In Jg Jl Jq Jt Mi Mp Mx Nd Ni Nm No Nv Oy) Qe(Jq Js Jt Lh Li Lw Mm Mp Mx Nd Ni Nn No Oy) Jl(Hr Ir Iv Jg Jn Js Mx Nm Nx Ny Og Oy Qb) Li(Ik In Iv Js Lv Lw Mx Nk Nm Nv Nx Of) Og(Ii Iv Jn Jt Lh Mi Mp Mx Nn Ny Po Qc) No(Iv Jq Lh Lw Mi Mp Nd Ni Nm Nx Ny) Nv(Iv Mh Mi Mx My Nd Ni Nm Nx Oe Qb) Fr(Iv Mi Mx Ni Nk Nx Of Oy Qb) Nx(Hr Mi Ms My Ni Oy Qc) Jg(Js Mg Mh Ng Of Oy) Mx(Ij Ik Jt Mt Ni) Js(In Mi Ms Nm Of) Qb(Jt Ni Nk Nm) oW(bH cQ hC iO) Mi(Mt Ni Ny) Hr(Jt Lh Pe) tT(Qg Qm Wm) tO(Kr Wm Th) Qd(Lh Lw) aA(Mh Qc) bG(dU gZ) jB(cA cD) AaNb TiuO GzyL MpNk MtIk NdNi HvSf TotX IjOy IsIv ShcB RbsI LpjI dUiO nWoV} Im{My(Iv Js Jt Lh Lv Lw Lx Mh Mi Mm Mp Ms Mx Nh Nl Nm Nn Of Pe Qa) Mx(Fp Hu It Iv Jg Jn Jr Js Jt Mb Mj Ng Nl Nm Nx Of Oy Qe) Iv(aA In Jg Jl Lh Lv Mh Ng Nm Nv Nx On Oy Qe sF) Of(Aa Fp Jl Jq Jt Lh Lv Lw Mb Mi Mm Nh Oz Pe) Ng(Fp Js Jt Lw Mf Mh Mm Ms Mt Nl Nm Nv On) Oy(Fp Jq Js Jt Lh Lv Lw Mh Ms Nl Nm Nv Nx)

Figure 39 Continued

Lh Mi Mm Na Nv Nx) My(Li Lw Mf Mt Nm Nv oE Qb Qy) Of(bA bS Cs Ed Fa Fn Js Nv Wm) Oy(Ir Jn Lw Nv Nx On Qa Qb rQ) Um(Aw Hv
Iz Nh oE Rc Ua Uu) qW(cC cI cU dE Hf Kp Qt wC) Ef(bE Dk Jd Ke Kq Nt rO) Hx(Jn Lw Mi Mr Nm Nw Nx) tT(AF aY dK Il Ly Qn) Gc(eC
Rm Tr Uu Vq Vs) Iz(aS bA Hv jP rZ Uh) uN(jO Ny Qm rO rV vT) Nm(Fp Jr Ne Ng Qa) Lw(Fp Ij Ir Li Pb) Nf(Lh Lx Nw Pc) Uh(Aw Jo Uc
Uu) Pb(Ih Ir Lx Nw) wQ(dH Fr To wB) rQ(bC iA Nq Pf) Nu(Li Mp Wm) Mb(Jg Li On) Ng(Jg rO uL) Hv(Hc Jv rU) Ib(rU uL uO) Ny(Ir Nw yJ)
Wn(Ax iO kR) aS(Hc Ne Nh) wL(eF Ow Vv) hR(tR wE yH) zG(dK Qn vI) jP(Aw Cp Hc) uI(It Mn No) Fp(Jn Nx) Mh(Lx Nw) Mp(Ok Qd)
Qa(Jg NI) Wh(jU jV) Jo(Kg Pj) Xa(jV IK) Kr(Ad rX) Lj(Rf

Zq(iP oK) Qe(aS Uh) Kq(Iz Jh) Qm(tN vU) Or(aS Mk) cU(uI vO) AasF WmUh MnwJ NdWb HvVh IduI YdjF LikP RirU NyuY UwjM aQjQ bOeQ cDoD dDfB iAwD iPuN qQuL} oV{bH(bB bN dK Mx Nd Nf Ng nK tF) Jf(Fn Ki Lx mE mF Zx Xa) bO(cI Io Ir Li Mk Nm Qc) Fw(cW Eq Kl Pz Rm) Gp(iA iP kR pI) Mk(Fn Mh Mx Wm) Zx(bJ bW Mn Xa) Wd(Ld Ok Ph Pi) Du(Aa nL tF) Mx(cX Ib Jn) Yg(Ks oD Qu) Kx(mF Uk Uv) nA(Ux Tm Wm) Eq(dB dD) Fy(eF Rf) Mn(Ms Wc) Ib(Ok Pk) Hf(aW Li) Qu(Ba Vs) Ko(Ef Nh) aL(aG pK) mF(Ed To) nK(aF iA) FiPh FnnH QycG QwcF KlOk LdoP LiVj LtnN QnaW bBbE gCpK} Th{wB(Iv Jh Lx Mj Ml Nb Nv Pe Qd wH) vH(Cp gW Kl Kp Oi Qy Uu) wJ(Lx Mr Nb Rj Ub Us) sK(aK bJ dN Li Mx Ua) wL(Md Pb Tz Uk Ur) qH(aD eD Oz Qb Ur) wP(Mg My Tz Vo) wD(Mm Tv Uc Uk) wH(Ii Io Oh Ue) qZ(Fw hW jM Uv) qB(bJ cV fN) sM(dR Hu Ur) uN(Ch eF Jd) Zq(eD iC) Li(tU vA) vI(Bn cM) NmtS MxuO NbwQ NcwC NdVz NlIY IdrN HbVt YdlL QwtQ JkvA LhnB ValK OzeZ cDuL jMrV rXuX} hA{Yd(aS Ax bQ cC Ju Ms Pc Qv To Tz Um Uv) Dr(aF bI Bn Bo Db Ju Md Nn Pd Rm Yj) Zx(aW bG bQ Mj Mq Mx) Um(Nd Ps Si Zq Zw) Wc(aR lN Tz Un) Rz(Bc Kp Kz Nf) Lp(Cu dA Nl Sr) cS(Uy Wd Wh Xa) Hl(An Pa Pz) Zq(bV Di lN) Fc(In jE) Nn(Rv Wf) Yg(Cu Ux) Vz(cU dB) sI(Rb xA) AsmW FiIn FyRx GbOh GnNf MaUx MjRv HoPh HqWf HroO ItSi YjJf WbaY QnVa OrlY VweD aZnL cCsF cPnH fRhB} Kq{Ef(Aw Hv Ib iJ Jl Lj Lv Mx oP Or Qc Qd Qe rZ Tn Um uO Us Vt wL) Jh(Ad bL cC Cw cX dE Ic Jo Kl Lv Mg mT Nm oE oN Qu Uh Uu Vt) Iz(aS bV cX Hf Ic Jo Kz Mc oN Qx Uh Um Us) oP(Ct nI Rf Um Tj) Ib(rC rQ Uh) eP(Ih iJ Or) gC(Eq Ps Vs) lY(Eq Oi Yg) eQ(Ez Rc) AwUh NngZ NdOm HlmU HvdX HxsF YgkO WdmZ JoPj KnpK PsoD RmfR UrwJ VikP} tX{Qm(AW Bo cB Ct Hf Hq Hu Ib jE jM jO Ma Ne Pk rV To Vt zG zI) Aa(fP iA Ih iP Jl Pk sI Vt) To(aM cH dA hW Lu oE rR uW) Kz(Mh My Nw oF Ri rS Uh) jM(bE cZ Kn nW Ri Uh uI) dB(Nq Pk qW rC Uh) iA(cR Kf Nm Pj Uh) nW(Hc Ip Md) Dl(dN qQ) Lu(Af Cx) Ly(Hf Nx) Uh(Bo bQ) iP(sK yJ) sF(Js Rb) jE(Cv Ld) ChrC NqaW MhHf NibI HxsJ IprA RifP} jP{Uw(An Ax bQ cR Li Mm Rf Rm) Hl(aF bV bW dG Vv) aZ(kO nC nD nH nJ) Fi(Cu jE Md Tj) Yh(Jd Qt Rf Tn) Js(Fd Ho Ps Rv) Kk(kO nC nH nL) nD(aS bE bJ dN) Zq(Fa Jn Ks) Rz(cV Ne Ss) fR(Co Cw Ny) kC(As dH Or) Af(lW nH) Em(eF kQ) Ho(Lu Tj) Kf(mM nI) Vs(Ry Yg) aS(mP nA) bE(nC nI) bJ(nA nJ) nL(aK dN) AnFd ArRv FcRc HrSi IjUy WfQz JrVi KxWn LplL RtUg OrkF aJoP cQoQ dHkO} Qd{My(aS bS Lh Lv Lx Mi Nl Pd) Nq(Jl Li Lw Mm Nn Nv wP) Mb(Jl Jt Lw Mm Mp Nv) Mp(Fp Mh Ms Nm Nw) Ng(Jt Mm Nv Nx rQ) Ex(rP sC vW yL) Mj(Jl Lh Mx Nv) Oy(Lh Lx Mi Pd) rC(cR dE Ib sK) Fp(Lw Mm Nn) Mh(Lx Lz Nn) Jl(Hr Ms) Nx(Lw Nn) dE(aS Ly) oE(Qx sK) EfEt NmNl MuHu MxJs NaJq IbUh ToqQ IiLh IpsF ItwQ IuJt ZxjH WnVq bBdU bOoP cNzG hVkC yJrS} gV{Qv(Aa Ad aF aM aQ aV cP Mx) dR(Aa Ap Ba cX Dd No oF Pz) Ug(aQ Bc cK Cq dX Jm Wm) Vo(bV cP Cv Cx Dd Mp Pf) Vv(bA cZ Et Mx Ub) bB(aD bA cX Qh Us) Ur(aI Al bO Vu) Cs(Ef Qz) Nr(eC iP) Mg(Lj oH) Jh(iP Uf) Qy(bO Ir) Qu(aM cX) Qh(Mx Pg) Li(Dd iZ) Rf(cY cZ) Ow(cS Jo) Us(Bo cP) Uu(bH St) Pk(Mb Ml) MaoH MfUv MyVu UabO LjiZ aDaI bWeC} Nw{Oy(Jl Jt Lv Lx Me Mi Mk Mp Nd Nq Nv Oz) My(Lh Lv Me Mi Mt Nq Nv) Mp(Me Mx Ng Nl Nq Ok) Ng(Ik Lv Nn Nx Pd) Pe(Hx Ii Mw Ny Pb) dX(Jr Ky Tz Ub Uo) Lw(Hr Me Nl Om) Mi(Hx Mh Mv Ny) Nn(Jh Me Om) Mv(Mu Nq Nv) Hr(Hv Jl Jt) eP(bA cH cI) Mh(Jl Mr) Hx(Lh Lx) Ii(Lh Mr) sI(Pf rU) MeOm MuMw YgmE UylN VinK aXsJ bOoP} jE{Yf(aM bA bB Bn cJ cT Ih jM Ms Qn Rm Rx Uh) uI(hF hR iP Kp Nk Nx qX) sF(Ik Qx rC Rg rU) Zw(Iz Mt Qy Vs) Wh(bH Bn Hc Uc) Mk(Lp Op Rx) Vc(bO Cu Uo) Ux(Gd Ng Vj) Xa(Ax Oy) Tm(cX Hb) Kc(mW We) Rv(cB jG) Rt(cV Lj) Vi(Ao Cq) sJ(Hf Pa) CtVa DkWd DrcW FiaF FntR GnNr NgZq NlLp UbUw VzJq WfVt RxcQ LduY OpOw} Qe{Nx(Fp In Iv Jq Lw Lx Mh Mi Mx Ng Nl Nn Oy) Nm(Hr Jl Lv Mp Mr Nl Nv Oy) Ms(Aa Iv Jn Jq Jt Lw Mt Nl) Uh(Co Ef Iu Ow Rm) Aa(Iv Jo Me Nb) Lw(Mb Mx My Oy) rC(cR sK zG) Mb(Mi Nv) My(Jq Mi) Ng(Jt rU) Ib(rV wQ) It(Mx yJ) qQ(Nq To) LxMh MpOk NdLp NhZw YikG YjoP ZqOw JkvI RyoE NvOy OzbS dDfP} dU{Jf(bL cF cL Fw mM Nb Pk Vw) Ny(aL Ed Gp Ir Jq oN) Kl(aL dD dI Ma Ow) Uw(Ha Ks Ng Qb Yi) To(cK Fy Jq oF) Yg(Is Ok Qh Tn) bH(aL aQ cK dB) Gp(Bc bJ Jr) Ib(Fw Lh Lt) Zx(Fd Fw Jk) Wf(bX Cu nA) dD(dM Fr nI) Fy(Gd Zw) Lt(bG Qa) Rv(nA nL) Ok(Nn Oe) dJ(Mx nA) mY(cK kP) TzWc IdnH HfaW JnVj RuUs aLeC} Yg{mE(aQ bA Jr Kx oD Oh Tz Yi) pH(dL Jr kG Ks Mb mS Mv Sj) mW(Cq eC Ij Ks nC Nq) nK(bL Na Om Qn) oD(bC eC mI Nn) lY(Et Uf Zq) iJ(Et No Zq) kG(bL Gp Ph) oT(Hq Ng Tv) Fy(nC oH) dF(jO kP) fA(An Tv) nN(Jr Ou) mS(Il Na) jM(Bn cV) AolX FwkI NdQh JseQ OmmU VsjY aEkP aGjG bBeP cMkF} eD{Zx(aF aO bF bG bZ cE cS dH Ks Pi Rg Um) Zq(aX bR bV cB cL cR Kx Pi) Ax(Ps Uz Vi Wd Wf Wg) Vc(Jf Mg Mp Qm Ux Vw) Vw(Ar Cs lN Mq) Gb(Fp Kz Nf) Pa(Rv Ux Vj) aE(Gn Ry Yl) Dr(aS Lp) Yd(dA Ks) Xa(cO Pi) Kz(Uz Wg) EtVz FiOz NmSi NfUz RyQl LpPi LtaS UwcZ aYoQ cUnN iHsJ} iP{yJ(An As cT Cu dK Fa Fy Il Ke Kx Lh Lj Lx Mp No Nr Ny Oh Pd qZ Tz Us Vu wE) tN(Ao Dk Ly Ne Nq oE) uI(aJ dL hR Id iZ jM) tR(Jr Mx Pd Pe Un) sK(Ip jM lL To uO) Gp(Fd Uy Vi) bU(Ho Zq Xa) wQ(bA cT) DkuX EtGd FyVc IluN YjnA ZqcX ZwOk KpwD aFuO dLwE} Uh{oE(Ao Ap dA dB Ef fP Ic Lv Lx sK) oN(cM dA dL Lw Mt Pb Pk Qv Tj) fP(aM aS bV cM Oe Qv Uu) Cs(Ap cM Ib Lh Mm Ow) Qa(Ef Ib Jo Rm) uY(cB Ib jO wQ) sJ(Jk Ma Mf) cM(iH nT) iA(bV Wm) sI(Na Rb) sK(Ef Ne) YfjF FnTk NmJo LyiH IbVt RvjY PkiJ dAtR eCkC wJqX wQuN} rC{yJ(An Cs cT Dl Fa Ip Jr Mt Na Nm No oE Qa Un) Ib(Cq Id Kr Ny Pe Tv) sK(Iz Kj Ma Ne Nq To) Mg(An Cu Kf Vu) Id(uI uN uY zG) Jk(uN uU uX uY) tR(Jr Js Ld Un) Ef(Ke Or uY) wJ(Ke Kn Vt) Ch(rS sC) Oy(Ke Or) kF(bF bQ) rZ(dB dE) uI(aJ kR) DcNg SrJo aGfR dAyL} lL{Yd(aH aM cB Cu dJ Dr Id Lh Or Pk Ua Vt) kF(cN Js nI Ph Pz qW) Vc(bA bW cT Lh Mg) nN(cQ Dd jY Nm Qc) Pz(mM nJ nT) Pk(nC nH nL) cX(nC nJ nL) mY(hW Ph rZ) Dr(It Rj) Rz(Dg Qu) cQ(nH nL) nT(Cx De) kI(bV dD) kO(Bn cN) IcTm QcoQ JlmM QmuN OrmT VacM mEqU qWkC} Ok{Wh(Dd Ho jL Nb nI Rh Vt) Mp(Ii Jo Mg Nl Nx Om) Uw(Ed kI Oi Or Rh) eQ(Eq Rf Rm Rz Vs) Mt(Hx Mv Ny Pb) Vc(Ow Uu Vt) mW(Gn Hl Wc) Eq(gL Nd) Ii(Nd Pg) Zw(mS mZ) Jn(My Oy) Js(Lw Mj) Ry(kI nB) AaMe AdnN PoLx MiHx HleM IsIv YiiJ YjgP WdLi WejY QxrZ JlJo RznK VoeP} jM{Uw(Hu Jh Jt Ju Nk Oh Ph Tv Wh) Uy(Gp Oi Ph Rj Rt) lY(cE Ch Mj Pf qU) uI(Id Ke oF Qv) It(Gb Ps Vj) Lp(Qa Ry Uc) Rv(cQ cT Ih) Vi(Hc Ju Zw) wB(Lw Mi Mq) Ct(Rt Va) Yd(bA dL) Zq(Di Ju) Rj(Hl Yl) Pj(kF nU) FdGp MtZw NbWh NiVj HfkF VzcJ ZxcT QckC PdkN aFwP} sF{Qy(Ax hP Mg My No Ra Sr) Je(aU aV cY Mh) Bc(Li Mh Pk) Tv(Dp Ef Mg) Ir(cY jF Pg) kR(Kr Qg Sr) Ip(Ez No) Iu(Mr Pe) Iv(Lh Mx) jF(Pa Ra) wH(dB qP) rA(rU uL) vQ(Pg Vu) pF(Aa Lz) AxJd CsRm DkiC TjcS MhcC IbvH IntR HfPf RbpY JsuN UmPk bCsI cYjK dKhR gLvI hOhB wJqQ qUrU} Ms{Nx(Ir Jn Jt Lh Li Lj Lx Mh Mi Mt Nn No Ny Oy Pe Qb Qc) Js(Hr Iv Jl Lv Lw Mm Mt Mx Nh Nl Nm Qa Qb) Fp(Ij Iv Jn Jq Jt Lh Lw Nm Nv Qa) Iv(Ij Lh Mx No Nv Qa) Mx(Jt Lh Mm Qc) Mn(Jr Mf) AaIs NlQa dJoW} Eq{Nd(cF Cu De dH Fy Jk Kr Mm Mu Nm No Nt Oa Tn Vz) kG(bX dE Dg Et Ih Il Jn Mn Nk Pk Uf Zq) oE(Ao bC Ho kF nA) mY(bZ Fy Mg Mn) Dc(Gp Jn) Kx(gL pI) Up(nH oW) nK(dR Rt) oF(Ao Cu) EtnL HocF IjlY JnnN RzmS LdoD UfnH cGpF} aL{fB(bW cG cS De dL Gp Ho Lx Mg Mr nH Nt pK Uf) mI(bN Dd Ed Nc nL Oy Pe Wm) lW(Ed Lj My Pe qU) Mb(kC nC nH nJ) nN(Iq Lz oH Oi) nT(Ed Iq nI Um) Pj(kC kF) oW(dH Qw) pK(cV Lh) DunJ IqkG KlkF LjmE UsnL bCmT cMlY mFrX kCrY} dX{Ou(Ax cE Cs Fa Ir Ki Ld Lj Mh Pk) Ld(Cs Dk Fb Hv Nq Pe Qb Vu) Cs(Hb Kc Pj) Kp(Lz Nq Vt) cC(mF nA nC) Fa(Or Ow) Hb(bV Kk) Iv(Jn Lh) Wh(gP nY) Kc(Mx Qb) Un(mH mM) bU(kC mH) CpOr PoHf GdJn HonY UbLh HvVt RgnH QmkN UyiJ PjhG aMnB dCeO} lK{Rz(Ao bJ cZ De Is Jr Kc Ql Qy Us Vt) Zx(bF bZ dH Ez Kr Ow Vv) Ph(Fd Gn Hl Ho Vh Wc Xa) Yd(bJ Ch dI Ml Rv) Rv(dH It Qz Um) Vi(bQ Ma Mh Nf) Dr(Gp Oy Tv) Rt(cM Jo) Vc(jO Rc) cB(Wf Yl) EmcM ZwJq WcKy KkmW LpdJ cVlY} wQ{cT(cU Fa Jr Lj Mt Mx Nr tV) Ip(Ib iZ jI qQ qT Ur) Po(aF bC Tn vI) To(hW Ke qZ) cU(Ar oE rT) vI(Mt Ni Pe) Cu(Dk Mg) Nq(bA Nv) Jk(Jl Tj) Ke(Kp uN) tV(Aa Bb) AruY CsUb DkoF NoUu LxbC MhdC MtuT NeNv NiLd KgLh KnuN KraF QmOz aYbA dGiA} uN{Qm(aF cH Ef Hu Jk oE Oz Qx) Mx(aF cT Jk Ke Ni qZ Ur) Ny(Ch Ib Jk Kj Oh) Qx(aF Gl Kn oF) jO(Dg Kc Kf Mt) Dk(Cu Mq Pe) Wm(aF bC oH) Tr(Jk Ur) Ip(cM iA) aF(Dl Nx) zH(iA nW) FaNq ExTz IlcM KrOe VqbC sIzG} nN{bU(cU nT Or Oy Pj) cM(bC Io Lh lW Nl) Ct(cT Gl Jr Pg) Ry(cA Jr Mx) hW(bQ cL dF) Tt(Uu Vs) Tn(Oi Uu) Rf(Lz Sr) Vv(eC Oy) aW(Ri Rv) nI(iJ Us)

Figure 39 Continued

Figure 39 Continued cDgC} Zx{Jn(kI kP) AogC CumZ HqgZ Lhnl} jK{uY(Kz My) DpLt FnRv NkVh JIoO} Du{IX(To Up) HqoT U

Figure 39 Continued bH bO} CuKl aSjP cHIN} kC{It(IL Qa} jP(aK dN) aZhA cVjU} Pj{Or(Lv Mk) FwJo LyIN cXjD} IY{Et(Uw Vi) NqWd aGIN dBjQ}
mZ{Wd(bF Rz) CuWf WhcG RxUs} hP{Po(Bg Uk) dA(bS Pe) NnMt} o

Figure 39 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 8.3E1 | 6.3E1 | 9.4E1 | 8.5E1 | 6.6E1 | 7.9E1 | 8.0E0 | 7.0E0 | 4.8E2 | 4.0E2 | 268 | 27 | 268 | 27 | 0.43 |
| Ad | ug/mL | 4.8E-2 | 5.0E-2 | 1.3E-1 | 6.6E-2 | 6.9E-1 | 7.9E-2 | 6.8E-4 | 7.8E-4 | 8.5E0 | 3.5E-1 | 150 | 22 | 150 | 22 | 0.46 |
| Af | ng/mL | 1.3E0 | 1.0E0 | 1.1E1 | 5.5E0 | 4.7E1 | 7.2E0 | 1.7E-3 | 1.7E-3 | 5.3E2 | 2.1E1 | 150 | 22 | 150 | 22 | 0.50 |
| Aj | ug/mL | 1.2E0 | 5.0E-1 | 2.4E0 | 1.8E0 | 2.5E0 | 2.3E0 | 1.5E-3 | 1.3E-3 | 6.1E0 | 5.8E0 | 150 | 22 | 150 | 22 | 0.43 |
| Al | mg/mL | 9.0E-5 | 6.4E-5 | 2.6E-4 | 3.5E-4 | 4.4E-4 | 4.9E-4 | 4.3E-6 | 6.6E-6 | 1.8E-3 | 1.5E-3 | 150 | 22 | 150 | 22 | 0.47 |
| An | U/mL | 6.0E1 | 7.2E1 | 2.5E2 | 2.2E2 | 8.2E2 | 4.4E2 | 2.8E-1 | 1.1E0 | 7.8E3 | 2.0E3 | 150 | 22 | 150 | 22 | 0.54 |
| Ao | pg/mL | 9.1E1 | 1.3E2 | 5.6E2 | 4.5E2 | 3.8E3 | 9.8E2 | 1.5E0 | 4.1E0 | 3.9E4 | 4.5E3 | 150 | 22 | 150 | 22 | 0.55 |
| Ap | ng/mL | 3.3E1 | 2.8E1 | 4.9E1 | 5.9E1 | 5.4E1 | 7.3E1 | 2.0E0 | 2.7E0 | 3.3E2 | 2.4E2 | 150 | 22 | 150 | 22 | 0.48 |
| Ar | ng/mL | 6.9E-1 | 7.7E-1 | 2.5E0 | 6.9E0 | 5.7E0 | 1.5E1 | 3.4E-3 | 4.1E-2 | 4.7E1 | 5.1E1 | 150 | 22 | 150 | 22 | 0.54 |
| As | ng/mL | 8.7E-3 | 3.7E-3 | 2.1E-2 | 8.8E-3 | 1.0E-1 | 8.9E-3 | 1.7E-3 | 1.7E-3 | 1.2E0 | 3.3E-2 | 150 | 22 | 150 | 22 | 0.45 |
| Aw | pg/mL | 1.6E1 | 2.0E1 | 1.7E1 | 1.9E1 | 6.3E0 | 5.3E0 | 2.9E-2 | 8.2E0 | 5.1E1 | 2.9E1 | 150 | 22 | 150 | 22 | 0.65 |
| Ax | ng/mL | 2.0E0 | 2.0E0 | 2.3E1 | 7.6E0 | 9.0E1 | 2.0E2 | 1.2E-2 | 1.0E-4 | 7.7E2 | 8.5E2 | 150 | 22 | 150 | 22 | 0.48 |
| Ba | ng/mL | 8.6E1 | 2.1E2 | 5.8E2 | 1.6E3 | 1.5E3 | 3.3E3 | 1.9E0 | 1.1E0 | 8.1E3 | 1.5E4 | 150 | 22 | 150 | 22 | 0.59 |
| Bb | ng/mL | 4.3E0 | 4.0E0 | 7.1E0 | 9.2E0 | 8.3E0 | 1.3E1 | 4.1E-3 | 4.1E-3 | 4.9E1 | 4.8E1 | 150 | 22 | 150 | 22 | 0.47 |
| Bc | ng/mL | 3.6E1 | 5.3E1 | 1.3E2 | 1.6E2 | 2.4E2 | 2.6E2 | 4.9E-1 | 1.0E0 | 1.2E3 | 9.9E2 | 150 | 22 | 150 | 22 | 0.52 |
| Bg | ng/mL | 1.1E-1 | 1.7E-1 | 4.4E0 | 1.9E1 | 1.8E1 | 8.4E1 | 5.3E-4 | 5.3E-4 | 1.5E2 | 4.0E2 | 150 | 22 | 150 | 22 | 0.53 |
| Bn | ng/mL | 5.6E-2 | 3.6E-1 | 1.5E0 | 1.3E0 | 5.1E0 | 2.0E0 | 5.6E-2 | 5.6E-2 | 5.8E1 | 7.4E0 | 150 | 22 | 150 | 22 | 0.60 |
| Bo | ng/mL | 1.3E1 | 2.0E1 | 1.4E1 | 1.9E1 | 1.1E1 | 1.1E1 | 1.6E-2 | 2.2E0 | 5.0E1 | 4.4E1 | 150 | 22 | 150 | 22 | 0.64 |
| Ch | uIU/mL | 1.0E0 | 1.1E0 | 3.1E1 | 6.0E1 | 1.7E2 | 2.5E2 | 3.4E-3 | 1.5E-1 | 1.8E3 | 1.2E3 | 150 | 22 | 150 | 22 | 0.49 |
| Co | pg/mL | 4.8E1 | 4.6E1 | 2.4E2 | 1.9E2 | 1.4E3 | 4.4E2 | 1.5E-1 | 3.6E0 | 1.7E4 | 2.1E3 | 150 | 22 | 150 | 22 | 0.48 |
| Cp | ng/mL | 2.2E1 | 2.2E1 | 3.5E1 | 3.5E1 | 1.0E2 | 3.0E1 | 6.0E-1 | 4.7E0 | 1.3E3 | 1.4E2 | 150 | 22 | 150 | 22 | 0.56 |
| Cq | ng/mL | 2.8E-2 | 4.2E-2 | 4.4E-1 | 2.1E-1 | 4.0E0 | 5.1E-1 | 8.0E-4 | 8.0E-4 | 4.9E1 | 2.3E0 | 150 | 22 | 150 | 22 | 0.60 |
| Cs | ng/mL | 6.0E1 | 1.0E2 | 4.7E2 | 6.6E2 | 1.7E3 | 1.4E3 | 8.3E-1 | 8.9E-1 | 1.8E4 | 5.1E3 | 150 | 22 | 150 | 22 | 0.54 |
| Ct | ng/mL | 3.4E-1 | 4.7E-1 | 4.3E1 | 3.7E1 | 1.3E2 | 9.6E1 | 8.9E-3 | 1.1E-4 | 6.2E2 | 4.2E2 | 150 | 22 | 150 | 22 | 0.53 |
| Cu | ng/mL | 2.5E-1 | 7.5E-1 | 9.0E-1 | 2.0E0 | 5.4E0 | 4.4E0 | 1.9E-2 | 1.7E-2 | 6.6E1 | 2.1E1 | 150 | 22 | 150 | 22 | 0.65 |
| Cv | ng/mL | 5.9E0 | 5.1E0 | 2.8E1 | 2.1E1 | 6.7E1 | 3.7E1 | 2.0E-2 | 7.5E-2 | 5.3E2 | 1.4E2 | 150 | 22 | 150 | 22 | 0.46 |
| Cw | mIU/mL | 3.4E-2 | 4.7E-2 | 8.7E-2 | 5.4E-2 | 5.5E-1 | 4.1E-2 | 8.9E-4 | 2.8E-3 | 6.8E0 | 1.5E-1 | 150 | 22 | 150 | 22 | 0.58 |
| Cx | ng/mL | 8.2E-1 | 3.5E-1 | 5.0E1 | 4.0E1 | 9.8E1 | 9.1E1 | 9.3E-5 | 9.3E-5 | 3.9E2 | 2.8E2 | 150 | 22 | 150 | 22 | 0.44 |
| Db | ug/mL | 7.5E0 | 7.1E0 | 8.8E0 | 8.4E0 | 7.9E0 | 5.2E0 | 4.5E-1 | 8.1E-1 | 5.9E1 | 2.0E1 | 150 | 22 | 150 | 22 | 0.51 |
| Dc | nmol/L | 2.1E-2 | 2.3E-2 | 1.4E-1 | 2.1E-1 | 1.1E0 | 4.3E-1 | 5.2E-6 | 1.1E-3 | 1.4E1 | 1.6E0 | 150 | 22 | 150 | 22 | 0.57 |
| Dd | ug/mL | 7.8E-2 | 4.6E-2 | 2.0E-1 | 2.5E-1 | 3.7E-1 | 3.8E-1 | 4.8E-4 | 6.2E-3 | 3.6E0 | 1.5E0 | 150 | 22 | 150 | 22 | 0.53 |
| De | ng/mL | 3.4E-3 | 1.5E-1 | 7.1E-2 | 1.8E-1 | 1.4E-1 | 2.5E-1 | 3.4E-3 | 3.4E-3 | 9.2E-1 | 1.1E0 | 150 | 22 | 150 | 22 | 0.67 |
| Dg | ng/mL | 3.7E1 | 3.4E1 | 4.8E1 | 4.3E1 | 4.0E1 | 3.9E1 | 7.1E-1 | 7.8E-1 | 1.9E2 | 1.2E2 | 150 | 22 | 150 | 22 | 0.46 |
| Di | pg/mL | 2.0E0 | 2.9E0 | 2.4E0 | 3.1E0 | 2.2E0 | 2.0E0 | 1.8E-1 | 1.8E-1 | 1.3E1 | 9.3E0 | 150 | 22 | 150 | 22 | 0.62 |
| Dk | uIU/mL | 1.4E-2 | 1.5E-2 | 5.4E-2 | 9.1E-2 | 1.7E-1 | 2.1E-1 | 1.1E-4 | 1.1E-4 | 1.6E0 | 9.8E-1 | 150 | 22 | 150 | 22 | 0.55 |
| Dl | ng/mL | 2.2E2 | 1.8E2 | 3.0E2 | 2.7E2 | 2.8E2 | 2.8E2 | 5.5E0 | 4.4E0 | 1.6E3 | 1.1E3 | 150 | 22 | 150 | 22 | 0.46 |
| Dp | ng/ml | 2.4E0 | 1.2E0 | 5.8E0 | 3.3E0 | 9.3E0 | 5.4E0 | 3.7E-3 | 3.7E-3 | 5.6E1 | 1.8E1 | 114 | 19 | 114 | 19 | 0.38 |
| Dr | pg/ml | 2.2E1 | 3.0E1 | 2.3E2 | 7.0E1 | 1.4E3 | 1.2E2 | 7.5E-1 | 7.5E-1 | 1.0E4 | 3.6E2 | 59 | 13 | 59 | 13 | 0.50 |
| Du | pg/ml | 1.6E2 | 1.4E2 | 1.5E3 | 5.1E2 | 4.5E3 | 6.6E2 | 1.2E0 | 1.2E0 | 2.4E4 | 1.8E3 | 45 | 12 | 45 | 12 | 0.46 |
| Ef | ng/mL | 9.5E-2 | 1.2E-1 | 7.9E-1 | 1.6E0 | 1.8E0 | 3.3E0 | 5.7E-4 | 5.7E-4 | 1.0E1 | 9.9E0 | 127 | 18 | 127 | 18 | 0.51 |
| Wm | % | 8.5E-2 | 8.5E-2 | 9.6E0 | 5.2E1 | 6.9E1 | 2.2E2 | 5.4E-2 | 8.5E-2 | 7.7E2 | 1.0E3 | 133 | 22 | 133 | 22 | 0.43 |
| Ed | pg/ml | 2.4E0 | 3.9E1 | 3.1E1 | 7.8E1 | 5.9E1 | 1.1E2 | 5.2E-1 | 5.2E-1 | 5.0E2 | 4.8E2 | 114 | 19 | 114 | 19 | 0.65 |
| Yf | ng/mL | 1.5E1 | 1.7E1 | 3.7E1 | 1.1E2 | 5.4E1 | 1.9E2 | 2.9E-1 | 2.9E-1 | 2.4E2 | 5.9E2 | 47 | 12 | 47 | 12 | 0.54 |
| Tj | pg/mL | 3.7E-1 | 3.7E-1 | 4.0E1 | 3.0E1 | 2.2E2 | 7.3E1 | 3.7E-1 | 3.7E-1 | 2.3E3 | 2.5E2 | 124 | 19 | 124 | 19 | 0.49 |
| Po | pg/ml | 2.1E-1 | 8.4E0 | 9.2E0 | 2.3E1 | 2.9E1 | 4.4E1 | 8.0E-3 | 2.6E-2 | 2.7E2 | 2.2E2 | 317 | 31 | 317 | 31 | 0.68 |
| Ti | ug/mL | 3.0E0 | 5.2E0 | 4.9E0 | 5.2E0 | 4.4E0 | 3.9E0 | 1.2E-1 | 4.0E-1 | 1.8E1 | 1.1E1 | 68 | 15 | 68 | 15 | 0.53 |
| Em | ng/mL | 6.1E-3 | 2.6E-2 | 7.6E-2 | 5.0E-2 | 2.4E-1 | 7.1E-2 | 8.4E-4 | 8.4E-4 | 1.9E0 | 2.4E-1 | 76 | 16 | 76 | 16 | 0.53 |
| Et | ng/mL | 1.4E3 | 2.7E3 | 1.6E3 | 2.3E3 | 1.2E3 | 1.4E3 | 7.5E1 | 7.9E1 | 4.8E3 | 5.0E3 | 316 | 31 | 316 | 31 | 0.64 |
| Eq | pg/ml | 1.6E2 | 1.9E2 | 3.3E2 | 4.1E2 | 3.8E2 | 4.8E2 | 1.0E0 | 1.0E0 | 1.5E3 | 1.4E3 | 45 | 12 | 45 | 12 | 0.53 |
| Th | ug/mL | 1.2E0 | 1.5E0 | 1.7E0 | 2.2E0 | 1.5E0 | 1.8E0 | 2.6E-3 | 2.6E-1 | 7.5E0 | 5.9E0 | 68 | 15 | 68 | 15 | 0.55 |
| Fa | ng/ml | 4.3E1 | 4.2E1 | 1.3E2 | 8.5E1 | 4.2E2 | 1.2E2 | 2.6E-1 | 1.6E0 | 3.7E3 | 4.3E2 | 113 | 16 | 113 | 16 | 0.48 |
| Ez | ng/ml | 3.8E0 | 3.2E0 | 1.4E1 | 2.4E1 | 2.7E1 | 4.9E1 | 1.3E-2 | 1.3E-2 | 1.6E2 | 2.0E2 | 114 | 19 | 114 | 19 | 0.49 |
| Fb | ng/ml | 2.5E1 | 2.6E1 | 2.3E1 | 2.3E1 | 1.1E1 | 1.3E1 | 6.6E-1 | 8.9E-1 | 4.3E1 | 4.3E1 | 114 | 16 | 114 | 16 | 0.48 |
| Ex | ng/ml | 7.4E-2 | 1.4E-1 | 1.8E-1 | 4.8E-1 | 3.1E-1 | 1.1E0 | 3.5E-5 | 1.7E-4 | 2.2E0 | 4.1E0 | 89 | 15 | 89 | 15 | 0.60 |

Figure 40

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Fc | pg/ml | 2.2E-1 | 2.2E-1 | 2.0E1 | 3.8E1 | 7.9E1 | 1.1E2 | 2.2E-1 | 2.2E-1 | 4.5E2 | 3.9E2 | 46 | 12 | 46 | 12 | 0.56 |
| Fd | pg/ml | 8.2E1 | 7.9E1 | 9.5E2 | 2.8E3 | 3.7E3 | 6.6E3 | 4.5E-1 | 9.8E-1 | 2.5E4 | 2.2E4 | 46 | 12 | 46 | 12 | 0.51 |
| Fi | pg/ml | 2.5E-1 | 2.5E-1 | 5.6E1 | 2.3E2 | 1.7E2 | 5.3E2 | 2.5E-1 | 2.5E-1 | 8.5E2 | 1.8E3 | 46 | 12 | 46 | 12 | 0.61 |
| Fn | ng/ml | 2.1E-1 | 2.8E-1 | 4.2E0 | 2.5E0 | 7.5E0 | 4.0E0 | 1.1E-14 | 2.1E-1 | 3.7E1 | 1.6E1 | 114 | 19 | 114 | 19 | 0.54 |
| Fp | ng/ml | 1.3E1 | 1.5E1 | 2.3E1 | 3.2E1 | 2.6E1 | 3.8E1 | 6.0E-3 | 3.0E-1 | 1.3E2 | 1.3E2 | 319 | 31 | 319 | 31 | 0.55 |
| Fr | ng/ml | 3.4E4 | 7.0E4 | 1.2E5 | 2.5E5 | 1.8E5 | 3.0E5 | 1.9E2 | 1.3E3 | 8.4E5 | 8.4E5 | 324 | 33 | 324 | 33 | 0.63 |
| Fw | pg/ml | 2.0E0 | 9.4E0 | 4.9E1 | 3.9E1 | 2.8E2 | 6.7E1 | 1.2E-1 | 1.2E-1 | 3.0E3 | 2.5E2 | 128 | 19 | 128 | 19 | 0.65 |
| Fy | ng/ml | 3.5E1 | 4.3E1 | 6.3E1 | 1.2E2 | 8.8E1 | 1.6E2 | 1.2E-1 | 1.2E-1 | 6.5E2 | 5.3E2 | 113 | 18 | 113 | 18 | 0.57 |
| Gh | pg/ml | 1.3E0 | 6.0E0 | 2.4E1 | 1.1E1 | 6.0E1 | 1.3E1 | 2.9E-2 | 2.9E-2 | 3.2E2 | 4.6E1 | 46 | 12 | 46 | 12 | 0.62 |
| Gb | % | 4.5E1 | 2.6E1 | 5.6E1 | 4.1E1 | 5.5E1 | 4.7E1 | 3.7E0 | 2.2E0 | 3.0E2 | 1.5E2 | 46 | 12 | 46 | 12 | 0.36 |
| Gc | ng/ml | 9.9E1 | 1.2E2 | 1.7E2 | 1.6E2 | 2.2E2 | 1.6E2 | 6.4E0 | 2.7E1 | 1.2E3 | 5.1E2 | 59 | 13 | 59 | 13 | 0.53 |
| Gd | ng/ml | 3.4E1 | 2.8E1 | 3.5E1 | 2.6E1 | 1.9E1 | 1.5E1 | 3.7E0 | 3.0E0 | 8.1E1 | 5.6E1 | 68 | 14 | 68 | 14 | 0.38 |
| Gn | U/ml | 2.2E-1 | 1.3E-1 | 3.2E0 | 5.1E-1 | 1.5E1 | 7.0E-1 | 5.6E-3 | 5.6E-3 | 1.1E2 | 2.2E0 | 58 | 13 | 58 | 13 | 0.44 |
| Gl | | 8.8E3 | 1.8E4 | 1.2E4 | 1.6E4 | 9.3E3 | 1.1E4 | 9.1E1 | 5.3E2 | 3.2E4 | 3.2E4 | 128 | 19 | 128 | 19 | 0.63 |
| Gp | U/ml | 1.2E0 | 1.5E-1 | 2.6E0 | 1.0E0 | 3.6E0 | 1.4E0 | 1.5E-2 | 1.5E-2 | 2.0E1 | 4.2E0 | 128 | 18 | 128 | 18 | 0.34 |
| Gz | ug/ml | 1.5E0 | 8.1E-1 | 5.9E0 | 3.1E0 | 5.9E0 | 4.4E0 | 4.2E-2 | 8.9E-2 | 2.5E1 | 1.1E1 | 78 | 15 | 78 | 15 | 0.36 |
| Ha | ng/ml | 2.0E0 | 2.6E0 | 8.6E0 | 8.8E0 | 2.0E1 | 2.1E1 | 1.7E-2 | 1.7E-2 | 1.0E2 | 9.2E1 | 112 | 19 | 112 | 19 | 0.53 |
| Nm | pg/ml | 1.3E4 | 1.4E4 | 3.5E4 | 5.5E4 | 9.2E4 | 1.1E5 | 1.0E-9 | 1.0E-9 | 9.6E5 | 4.4E5 | 320 | 31 | 320 | 31 | 0.52 |
| Nn | pg/ml | 1.5E2 | 5.9E2 | 1.1E3 | 1.9E4 | 4.4E3 | 5.8E4 | 1.0E-9 | 1.0E-9 | 6.0E4 | 3.1E5 | 320 | 31 | 320 | 31 | 0.63 |
| No | pg/ml | 1.5E1 | 2.3E1 | 3.5E1 | 8.0E1 | 7.8E1 | 1.6E2 | 1.0E-9 | 3.3E-1 | 9.1E2 | 7.0E2 | 320 | 31 | 320 | 31 | 0.59 |
| Nq | pg/ml | 1.9E0 | 4.6E0 | 1.8E1 | 7.3E1 | 6.6E1 | 1.7E2 | 1.0E-9 | 1.0E-9 | 6.3E2 | 6.7E2 | 320 | 31 | 320 | 31 | 0.58 |
| Nr | pg/ml | 1.4E0 | 2.8E0 | 2.3E1 | 7.6E1 | 8.5E1 | 2.5E2 | 1.0E-9 | 1.0E-9 | 9.8E2 | 1.4E3 | 320 | 31 | 320 | 31 | 0.59 |
| Ns | pg/ml | 1.0E-9 | 1.0E-9 | 4.7E0 | 3.8E1 | 2.5E1 | 2.0E2 | 1.0E-9 | 1.0E-9 | 2.4E2 | 1.1E3 | 320 | 31 | 320 | 31 | 0.53 |
| Nt | pg/ml | 1.0E2 | 1.6E2 | 1.3E2 | 2.5E2 | 1.3E2 | 2.6E2 | 9.8E-1 | 3.5E1 | 1.7E3 | 1.2E3 | 320 | 31 | 320 | 31 | 0.69 |
| Nu | pg/ml | 1.7E1 | 7.7E1 | 5.3E1 | 1.0E2 | 8.9E1 | 1.3E2 | 1.0E-9 | 1.0E-9 | 6.3E2 | 6.3E2 | 320 | 31 | 320 | 31 | 0.69 |
| Lu | pg/ml | 1.0E4 | 1.0E4 | 1.4E4 | 2.6E4 | 2.8E4 | 9.9E4 | 5.2E2 | 1.3E3 | 3.9E5 | 5.6E5 | 320 | 31 | 320 | 31 | 0.44 |
| Lv | pg/ml | 1.0E-9 | 1.8E1 | 1.4E1 | 4.2E1 | 2.7E1 | 5.9E1 | 1.0E-9 | 1.0E-9 | 2.4E2 | 2.6E2 | 320 | 31 | 320 | 31 | 0.68 |
| Lw | pg/ml | 1.0E-9 | 1.0E-9 | 5.1E-1 | 7.0E0 | 5.3E0 | 3.2E1 | 1.0E-9 | 1.0E-9 | 8.0E1 | 1.8E2 | 320 | 31 | 320 | 31 | 0.54 |
| Lx | pg/ml | 1.0E-9 | 1.3E2 | 2.4E2 | 5.2E2 | 1.4E3 | 7.4E2 | 1.0E-9 | 1.0E-9 | 2.2E4 | 2.8E3 | 320 | 31 | 320 | 31 | 0.68 |
| Ly | pg/ml | 1.0E-9 | 1.0E-9 | 9.3E0 | 6.9E0 | 1.8E1 | 1.3E1 | 1.0E-9 | 1.0E-9 | 1.1E2 | 4.8E1 | 320 | 31 | 320 | 31 | 0.48 |
| Lz | pg/ml | 1.0E-9 | 1.0E-9 | 3.2E0 | 6.7E0 | 2.7E1 | 1.8E1 | 1.0E-9 | 1.0E-9 | 4.3E2 | 6.2E1 | 320 | 31 | 320 | 31 | 0.56 |
| Ma | pg/ml | 4.0E2 | 4.1E2 | 2.0E3 | 6.5E3 | 5.2E3 | 1.3E4 | 1.0E-9 | 1.0E-9 | 6.5E4 | 5.2E4 | 320 | 31 | 320 | 31 | 0.53 |
| Mb | pg/ml | 2.5E1 | 3.7E1 | 3.1E1 | 4.1E1 | 1.7E1 | 2.2E1 | 4.1E0 | 1.6E1 | 2.1E2 | 1.1E2 | 320 | 31 | 320 | 31 | 0.63 |
| Mc | pg/ml | 1.0E-9 | 1.0E-9 | 5.4E-2 | 5.4E-2 | 7.6E-1 | 3.0E-1 | 1.0E-9 | 1.0E-9 | 1.3E1 | 1.7E0 | 320 | 31 | 320 | 31 | 0.51 |
| Md | pg/ml | 1.0E-9 | 1.0E-9 | 6.7E-1 | 5.9E-1 | 5.6E0 | 2.0E0 | 1.0E-9 | 1.0E-9 | 6.8E1 | 9.8E0 | 320 | 31 | 320 | 31 | 0.55 |
| Me | pg/ml | 3.2E1 | 2.3E1 | 3.1E1 | 2.4E1 | 2.3E1 | 2.9E1 | 1.0E-9 | 1.0E-9 | 3.2E2 | 1.6E2 | 320 | 31 | 320 | 31 | 0.33 |
| Mf | pg/ml | 1.0E-9 | 1.0E-9 | 5.0E-1 | 1.8E0 | 3.5E0 | 6.6E0 | 1.0E-9 | 1.0E-9 | 5.6E1 | 3.7E1 | 320 | 31 | 320 | 31 | 0.58 |
| Mg | pg/ml | 1.1E0 | 5.3E-1 | 6.3E0 | 1.3E1 | 1.2E1 | 3.1E1 | 1.0E-9 | 1.0E-9 | 9.2E1 | 1.5E2 | 320 | 31 | 320 | 31 | 0.51 |
| Mh | pg/ml | 1.0E-9 | 4.0E-2 | 1.1E0 | 1.9E0 | 7.8E0 | 4.3E0 | 1.0E-9 | 1.0E-9 | 1.1E2 | 1.8E1 | 320 | 31 | 320 | 31 | 0.63 |
| Mi | pg/ml | 1.0E-9 | 1.0E-9 | 2.0E0 | 2.4E1 | 2.0E1 | 9.5E1 | 1.0E-9 | 1.0E-9 | 3.2E2 | 5.2E2 | 320 | 31 | 320 | 31 | 0.60 |
| Mj | pg/ml | 1.0E-9 | 1.0E-9 | 5.9E0 | 2.2E1 | 3.3E1 | 4.4E1 | 1.0E-9 | 1.0E-9 | 4.6E2 | 2.1E2 | 320 | 31 | 320 | 31 | 0.65 |
| Mk | pg/ml | 7.2E-1 | 7.4E0 | 1.6E1 | 2.7E1 | 9.5E1 | 9.0E1 | 1.0E-9 | 1.0E-9 | 1.3E3 | 5.0E2 | 320 | 31 | 320 | 31 | 0.63 |
| Ml | pg/ml | 1.0E-9 | 1.0E-9 | 1.1E1 | 1.7E1 | 1.2E2 | 6.4E1 | 1.0E-9 | 1.0E-9 | 2.1E3 | 3.4E2 | 320 | 31 | 320 | 31 | 0.52 |
| Mm | pg/ml | 5.5E2 | 3.8E2 | 1.0E3 | 1.7E3 | 1.3E3 | 2.3E3 | 1.0E-9 | 1.0E-9 | 1.0E4 | 1.0E4 | 320 | 31 | 320 | 31 | 0.54 |
| Mn | pg/ml | 5.7E0 | 1.0E1 | 1.1E1 | 1.1E1 | 2.5E1 | 8.6E0 | 1.0E-9 | 1.0E-9 | 3.5E2 | 3.7E1 | 320 | 31 | 320 | 31 | 0.61 |
| Mp | pg/ml | 1.0E-9 | 7.4E0 | 1.3E1 | 1.1E2 | 5.1E1 | 4.2E2 | 1.0E-9 | 1.0E-9 | 6.3E2 | 2.4E3 | 320 | 31 | 320 | 31 | 0.62 |
| Mq | pg/ml | 1.0E-9 | 1.0E-9 | 2.5E0 | 6.5E0 | 1.4E1 | 1.7E1 | 1.0E-9 | 1.0E-9 | 1.8E2 | 7.4E1 | 320 | 31 | 320 | 31 | 0.56 |
| Mr | pg/ml | 1.0E-9 | 1.0E-9 | 3.2E1 | 1.7E2 | 1.9E2 | 6.2E2 | 1.0E-9 | 1.0E-9 | 2.2E3 | 3.4E3 | 320 | 31 | 320 | 31 | 0.59 |
| Ms | pg/ml | 3.2E2 | 3.8E2 | 4.6E2 | 5.8E2 | 5.2E2 | 9.8E2 | 1.0E-9 | 1.0E-9 | 3.2E3 | 4.7E3 | 320 | 31 | 320 | 31 | 0.48 |
| Mt | pg/ml | 2.2E-1 | 2.3E0 | 9.0E0 | 1.3E2 | 4.6E1 | 5.8E2 | 1.0E-9 | 1.0E-9 | 7.1E2 | 3.2E3 | 320 | 31 | 320 | 31 | 0.65 |
| Mu | pg/ml | 1.0E-9 | 1.0E-9 | 7.6E-1 | 9.8E0 | 6.3E0 | 4.3E1 | 1.0E-9 | 1.0E-9 | 9.9E1 | 2.3E2 | 320 | 31 | 320 | 31 | 0.55 |
| Mv | pg/ml | 1.0E-9 | 1.0E-9 | 6.3E1 | 1.4E2 | 3.4E2 | 3.0E2 | 1.0E-9 | 1.0E-9 | 4.5E3 | 9.2E2 | 320 | 31 | 320 | 31 | 0.59 |
| Mw | pg/ml | 3.7E1 | 6.9E1 | 2.7E2 | 5.0E2 | 1.4E3 | 1.1E3 | 1.0E-9 | 1.0E-9 | 1.8E4 | 5.2E3 | 320 | 31 | 320 | 31 | 0.57 |
| Mx | pg/ml | 1.0E-9 | 1.0E-9 | 2.3E-1 | 2.5E0 | 8.8E-1 | 6.6E0 | 1.0E-9 | 1.0E-9 | 9.2E0 | 3.2E1 | 320 | 31 | 320 | 31 | 0.67 |
| My | pg/ml | 1.0E-9 | 1.0E-9 | 3.3E2 | 2.7E2 | 2.5E3 | 6.0E2 | 1.0E-9 | 1.0E-9 | 3.9E4 | 2.1E3 | 320 | 31 | 320 | 31 | 0.54 |
| Mz | pg/ml | 1.1E1 | 2.9E1 | 2.8E1 | 1.2E2 | 8.5E1 | 3.4E2 | 1.0E-9 | 1.0E-9 | 1.3E3 | 1.9E3 | 320 | 31 | 320 | 31 | 0.67 |
| Na | pg/ml | 1.0E-9 | 1.0E-9 | 7.7E-1 | 1.1E0 | 3.0E0 | 2.4E0 | 1.0E-9 | 1.0E-9 | 4.2E1 | 9.6E0 | 320 | 31 | 320 | 31 | 0.54 |

Figure 40 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nb | pg/ml | 2.1E0 | 3.6E0 | 3.9E0 | 1.3E1 | 1.2E1 | 3.8E1 | 1.0E-9 | 1.0E-9 | 1.5E2 | 2.1E2 | 320 | 31 | 320 | 31 | 0.65 |
| Nc | pg/ml | 3.3E2 | 1.6E2 | 5.3E2 | 3.0E2 | 7.6E2 | 3.7E2 | 1.0E-9 | 1.0E-9 | 9.2E3 | 1.4E3 | 320 | 31 | 320 | 31 | 0.40 |
| Nd | pg/ml | 2.8E1 | 1.1E1 | 3.5E1 | 2.6E1 | 1.4E2 | 3.2E1 | 1.0E-9 | 7.2E-1 | 2.1E3 | 1.5E2 | 320 | 31 | 320 | 31 | 0.48 |
| Ne | pg/ml | 4.3E2 | 2.5E2 | 5.3E2 | 3.7E2 | 5.5E2 | 6.5E2 | 1.0E-9 | 1.0E-9 | 7.0E3 | 3.6E3 | 320 | 31 | 320 | 31 | 0.34 |
| Nf | pg/ml | 1.0E-9 | 1.0E-9 | 2.9E0 | 4.6E0 | 1.2E1 | 2.0E1 | 1.0E-9 | 1.0E-9 | 1.3E2 | 1.1E2 | 320 | 31 | 320 | 31 | 0.50 |
| Ng | pg/ml | 1.3E1 | 6.7E0 | 9.3E1 | 5.6E1 | 1.9E2 | 9.1E1 | 1.0E-9 | 1.0E-9 | 1.6E3 | 3.0E2 | 320 | 31 | 320 | 31 | 0.45 |
| Nh | pg/ml | 6.3E1 | 3.4E1 | 8.1E1 | 6.0E1 | 7.3E1 | 8.9E1 | 1.0E-9 | 4.5E0 | 5.6E2 | 5.1E2 | 320 | 31 | 320 | 31 | 0.36 |
| Ni | pg/ml | 1.0E-9 | 1.0E-9 | 8.2E1 | 1.0E2 | 1.4E2 | 1.5E2 | 1.0E-9 | 1.0E-9 | 1.1E3 | 4.9E2 | 320 | 31 | 320 | 31 | 0.52 |
| Nj | pg/ml | 7.4E0 | 4.4E0 | 1.1E1 | 6.1E0 | 1.2E1 | 5.5E0 | 1.0E-9 | 1.0E-9 | 6.9E1 | 1.9E1 | 320 | 31 | 320 | 31 | 0.38 |
| Nk | pg/ml | 1.8E1 | 3.4E0 | 3.3E1 | 1.7E1 | 4.0E1 | 2.3E1 | 1.0E-9 | 1.0E-9 | 2.0E2 | 8.3E1 | 320 | 31 | 320 | 31 | 0.38 |
| Nl | pg/ml | 4.4E1 | 2.3E1 | 5.9E1 | 3.0E1 | 7.7E1 | 3.7E1 | 1.0E-9 | 1.0E-9 | 1.1E3 | 1.8E2 | 320 | 31 | 320 | 31 | 0.33 |
| Hl | pg/ml | 1.1E1 | 2.3E0 | 1.1E2 | 1.6E1 | 5.3E2 | 2.2E1 | 1.0E-9 | 1.0E-9 | 3.6E3 | 6.1E1 | 46 | 12 | 46 | 12 | 0.40 |
| Ho | pg/ml | 1.7E1 | 2.5E1 | 2.9E1 | 4.8E1 | 5.7E1 | 5.3E1 | 1.0E-9 | 7.6E0 | 3.9E2 | 1.7E2 | 46 | 12 | 46 | 12 | 0.66 |
| Hp | ng/ml | 1.6E0 | 1.7E0 | 1.4E2 | 7.6E1 | 3.2E2 | 2.6E2 | 3.6E-1 | 1.0E-9 | 8.9E2 | 8.9E2 | 46 | 12 | 46 | 12 | 0.49 |
| Tz | pg/ml | 4.1E3 | 9.8E3 | 6.1E3 | 1.5E5 | 7.1E3 | 4.7E5 | 1.0E-9 | 9.8E1 | 5.3E4 | 2.1E6 | 114 | 19 | 114 | 19 | 0.66 |
| Ua | pg/ml | 3.3E3 | 4.3E3 | 3.2E4 | 2.0E4 | 2.0E5 | 2.8E4 | 1.0E-9 | 2.7E2 | 2.1E6 | 9.9E4 | 114 | 19 | 114 | 19 | 0.52 |
| Ub | pg/ml | 5.6E2 | 4.9E2 | 9.1E2 | 5.6E2 | 1.2E3 | 4.6E2 | 1.0E-9 | 2.3E0 | 9.8E3 | 1.4E3 | 114 | 19 | 114 | 19 | 0.42 |
| Ue | pg/ml | 3.1E1 | 1.9E1 | 3.8E1 | 2.5E1 | 3.4E1 | 2.3E1 | 9.8E-2 | 4.5E0 | 2.7E2 | 1.1E2 | 114 | 19 | 114 | 19 | 0.33 |
| Uc | pg/ml | 6.8E2 | 7.9E2 | 1.7E3 | 1.9E3 | 5.4E3 | 2.6E3 | 1.0E-9 | 1.5E1 | 5.7E4 | 9.4E3 | 114 | 19 | 114 | 19 | 0.53 |
| Ud | pg/ml | 1.0E-9 | 1.0E-9 | 3.9E0 | 1.0E-9 | 3.7E1 | 0.0E0 | 1.0E-9 | 1.0E-9 | 3.9E2 | 1.0E-9 | 114 | 19 | 114 | 19 | 0.49 |
| Hq | pg/ml | 1.1E0 | 2.4E0 | 1.7E2 | 1.3E1 | 1.9E3 | 3.3E1 | 1.0E-9 | 1.0E-9 | 2.8E4 | 1.8E2 | 318 | 31 | 318 | 31 | 0.62 |
| Hr | pg/ml | 9.1E1 | 1.1E2 | 6.8E2 | 4.7E2 | 1.4E3 | 9.3E2 | 1.0E-9 | 1.6E1 | 1.2E4 | 3.8E3 | 318 | 31 | 318 | 31 | 0.54 |
| Hu | pg/ml | 5.3E0 | 2.9E1 | 4.0E3 | 9.2E3 | 3.8E4 | 4.7E4 | 1.0E-9 | 1.0E-9 | 6.3E5 | 2.6E5 | 318 | 31 | 318 | 31 | 0.59 |
| Hv | pg/ml | 1.3E0 | 2.8E0 | 5.2E0 | 1.0E1 | 5.0E1 | 3.0E1 | 1.0E-9 | 1.0E-9 | 8.9E2 | 1.6E2 | 318 | 31 | 318 | 31 | 0.67 |
| Hw | pg/ml | 6.3E0 | 1.1E1 | 4.5E1 | 3.5E1 | 5.3E2 | 9.1E1 | 1.0E-9 | 1.0E-9 | 9.4E3 | 5.0E2 | 318 | 31 | 318 | 31 | 0.62 |
| Hx | pg/ml | 8.5E0 | 2.2E1 | 5.6E1 | 9.0E1 | 5.2E2 | 2.4E2 | 1.0E-9 | 1.0E-9 | 9.3E3 | 1.3E3 | 318 | 31 | 318 | 31 | 0.64 |
| Ib | ng/ml | 3.9E-2 | 2.0E-2 | 1.6E0 | 3.3E-1 | 7.0E0 | 1.1E0 | 1.0E-9 | 1.0E-9 | 5.6E1 | 4.7E0 | 113 | 18 | 113 | 18 | 0.43 |
| Ic | U/ml | 2.2E2 | 2.2E2 | 9.4E2 | 2.1E2 | 6.2E3 | 1.6E2 | 2.4E0 | 1.6E1 | 6.5E4 | 4.2E2 | 113 | 18 | 113 | 18 | 0.51 |
| Id | U/ml | 6.8E-1 | 5.4E-1 | 5.0E0 | 1.1E0 | 4.1E1 | 1.3E0 | 1.0E-9 | 1.0E-9 | 4.3E2 | 4.5E0 | 113 | 18 | 113 | 18 | 0.45 |
| Tt | pg/ml | 1.7E2 | 1.8E2 | 1.7E2 | 1.8E2 | 5.9E1 | 5.3E1 | 4.3E1 | 1.0E2 | 4.4E2 | 2.8E2 | 105 | 17 | 105 | 17 | 0.54 |
| To | pg/ml | 1.6E0 | 1.8E0 | 2.2E0 | 2.0E0 | 3.0E0 | 2.0E0 | 1.0E-9 | 1.0E-9 | 2.3E1 | 6.4E0 | 110 | 19 | 110 | 19 | 0.49 |
| Tr | pg/ml | 3.5E0 | 2.7E0 | 9.0E0 | 7.7E0 | 3.1E1 | 1.4E1 | 1.0E-9 | 1.0E-9 | 3.1E2 | 5.4E1 | 108 | 18 | 108 | 18 | 0.45 |
| Tn | pg/ml | 3.2E1 | 5.7E1 | 1.1E2 | 2.7E2 | 3.4E2 | 4.8E2 | 1.0E-9 | 9.0E0 | 2.3E3 | 2.0E3 | 110 | 19 | 110 | 19 | 0.63 |
| Tv | ng/ml | 1.2E1 | 1.2E1 | 9.0E1 | 4.5E1 | 6.8E2 | 9.9E1 | 1.0E-9 | 1.0E-9 | 7.1E3 | 4.3E2 | 110 | 19 | 110 | 19 | 0.52 |
| Ih | ng/ml | 6.3E1 | 1.1E2 | 2.5E2 | 4.7E2 | 4.4E2 | 7.0E2 | 1.0E-9 | 1.4E0 | 3.6E3 | 2.8E3 | 319 | 31 | 319 | 31 | 0.58 |
| Ii | ng/ml | 7.9E1 | 1.2E2 | 2.2E2 | 3.3E2 | 5.2E2 | 8.1E2 | 7.3E-1 | 7.5E-1 | 5.2E3 | 4.5E3 | 319 | 31 | 319 | 31 | 0.56 |
| Ij | ng/ml | 7.8E1 | 1.2E2 | 2.5E2 | 3.4E2 | 1.5E3 | 5.5E2 | 2.8E0 | 9.5E0 | 2.4E4 | 2.0E3 | 315 | 31 | 315 | 31 | 0.61 |
| Ik | ng/ml | 1.0E1 | 9.1E1 | 1.4E3 | 2.8E2 | 1.2E4 | 4.0E2 | 5.9E-1 | 6.2E-1 | 1.2E5 | 1.5E3 | 315 | 31 | 315 | 31 | 0.65 |
| Il | ng/ml | 3.6E2 | 4.9E2 | 1.3E3 | 2.4E3 | 2.8E3 | 4.1E3 | 1.0E-9 | 1.2E0 | 1.2E4 | 1.2E4 | 313 | 31 | 313 | 31 | 0.56 |
| Im | ng/ml | 2.1E2 | 7.0E2 | 4.4E2 | 1.2E3 | 7.8E2 | 2.7E3 | 1.4E1 | 2.2E1 | 6.2E3 | 1.5E4 | 315 | 31 | 315 | 31 | 0.63 |
| In | ng/ml | 3.5E0 | 2.9E0 | 3.4E1 | 4.4E1 | 2.7E2 | 1.2E2 | 1.0E-9 | 1.0E-9 | 4.5E3 | 5.9E2 | 319 | 31 | 319 | 31 | 0.50 |
| Hb | ng/ml | 2.6E1 | 1.8E1 | 3.5E1 | 3.4E1 | 3.4E1 | 4.8E1 | 1.6E0 | 4.8E-1 | 2.0E2 | 1.9E2 | 116 | 18 | 116 | 18 | 0.40 |
| Hc | pg/ml | 6.9E2 | 4.8E2 | 3.0E3 | 4.5E3 | 1.0E4 | 1.2E4 | 1.0E-9 | 1.4E2 | 1.0E5 | 5.0E4 | 116 | 18 | 116 | 18 | 0.49 |
| Hf | ng/ml | 2.0E2 | 1.3E2 | 4.2E2 | 2.4E2 | 5.8E2 | 2.7E2 | 1.0E-9 | 1.0E-9 | 3.2E3 | 8.8E2 | 116 | 18 | 116 | 18 | 0.44 |
| Io | ng/ml | 9.3E3 | 1.0E4 | 1.9E4 | 2.3E4 | 4.7E4 | 3.9E4 | 1.0E-9 | 2.4E2 | 7.1E5 | 2.0E5 | 319 | 31 | 319 | 31 | 0.54 |
| Ip | ng/ml | 9.3E0 | 3.0E1 | 2.1E1 | 2.7E1 | 2.7E1 | 2.1E1 | 1.0E-9 | 5.0E-3 | 2.3E2 | 7.1E1 | 319 | 31 | 319 | 31 | 0.60 |
| Iq | ug/ml | 1.0E-1 | 2.8E-1 | 4.3E1 | 9.2E0 | 7.6E2 | 3.9E1 | 1.0E-9 | 1.0E-9 | 1.4E4 | 2.2E2 | 319 | 31 | 319 | 31 | 0.56 |
| Ir | ug/ml | 3.7E-1 | 8.4E-1 | 5.5E0 | 1.5E1 | 3.8E1 | 3.6E1 | 1.0E-9 | 1.0E-9 | 5.1E2 | 1.3E2 | 318 | 31 | 318 | 31 | 0.63 |
| Is | ng/ml | 1.8E0 | 8.8E0 | 8.4E0 | 3.6E1 | 3.4E1 | 5.6E1 | 1.0E-9 | 1.4E-1 | 5.5E2 | 2.6E2 | 319 | 31 | 319 | 31 | 0.69 |
| It | ng/ml | 2.1E0 | 3.4E0 | 2.1E1 | 5.3E1 | 9.8E1 | 1.7E2 | 1.0E-9 | 1.0E-9 | 1.1E3 | 8.3E2 | 319 | 31 | 319 | 31 | 0.59 |
| Iu | ng/ml | 1.7E2 | 1.4E2 | 1.3E3 | 2.6E3 | 4.2E3 | 6.3E3 | 1.0E-9 | 1.0E-9 | 2.9E4 | 2.4E4 | 319 | 31 | 319 | 31 | 0.52 |
| Iv | ng/ml | 1.1E1 | 2.7E1 | 9.7E1 | 3.4E2 | 9.1E2 | 9.5E2 | 1.0E-9 | 1.9E0 | 1.6E4 | 3.8E3 | 318 | 31 | 318 | 31 | 0.69 |
| Iz | ng/ml | 1.2E2 | 1.1E2 | 3.8E2 | 3.0E2 | 7.6E2 | 4.4E2 | 1.5E0 | 8.8E-1 | 6.1E3 | 1.7E3 | 116 | 18 | 116 | 18 | 0.46 |
| Yg | pg/ml | 2.6E2 | 7.8E2 | 1.7E3 | 1.7E3 | 7.7E3 | 2.4E3 | 1.0E-9 | 1.0E-9 | 5.0E4 | 8.2E3 | 42 | 12 | 42 | 12 | 0.55 |
| Yh | pg/ml | 2.1E2 | 3.3E2 | 3.7E2 | 7.3E2 | 4.8E2 | 8.8E2 | 1.0E-9 | 1.0E-9 | 2.1E3 | 3.0E3 | 42 | 12 | 42 | 12 | 0.63 |
| Yi | pg/ml | 3.2E2 | 5.6E2 | 5.0E2 | 3.6E3 | 4.9E2 | 7.7E3 | 1.0E-9 | 1.0E-9 | 2.0E3 | 2.6E4 | 42 | 12 | 42 | 12 | 0.57 |
| Yk | U/ml | 1.0E-9 | 1.0E-9 | 1.8E-1 | 3.9E-1 | 5.7E-1 | 7.1E-1 | 1.0E-9 | 1.0E-9 | 3.0E0 | 2.0E0 | 42 | 12 | 42 | 12 | 0.58 |

Figure 40 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yj | pg/ml | 1.5E2 | 1.0E2 | 3.4E2 | 1.4E2 | 5.5E2 | 1.3E2 | 9.7E0 | 1.0E-9 | 3.2E3 | 4.7E2 | 42 | 12 | 42 | 12 | 0.36 |
| Yd | ng/ml | 1.9E-1 | 3.3E-1 | 3.6E-1 | 5.7E-1 | 4.2E-1 | 7.7E-1 | 6.6E-3 | 1.6E-2 | 1.8E0 | 2.3E0 | 46 | 12 | 46 | 12 | 0.54 |
| Wb | pg/ml | 2.8E4 | 3.2E4 | 3.6E4 | 8.4E4 | 2.5E4 | 1.8E5 | 4.9E3 | 7.5E3 | 1.5E5 | 6.4E5 | 46 | 12 | 46 | 12 | 0.56 |
| Vz | pg/ml | 3.9E0 | 2.4E0 | 5.1E0 | 3.1E0 | 4.9E0 | 2.7E0 | 1.0E-9 | 3.0E-1 | 2.2E1 | 9.6E0 | 46 | 12 | 46 | 12 | 0.36 |
| Si | ng/ml | 1.3E0 | 9.3E-1 | 2.1E0 | 1.7E0 | 2.6E0 | 1.9E0 | 1.1E-1 | 8.6E-3 | 1.0E1 | 6.0E0 | 46 | 12 | 46 | 12 | 0.47 |
| Sf | mIU/mL | 2.0E1 | 1.0E1 | 5.4E1 | 1.5E1 | 1.2E2 | 1.3E1 | 6.2E-1 | 1.3E0 | 7.2E2 | 4.3E1 | 46 | 12 | 46 | 12 | 0.39 |
| Sh | mIU/mL | 1.7E1 | 1.1E1 | 4.8E1 | 1.3E1 | 9.7E1 | 1.5E1 | 7.8E-2 | 1.4E-1 | 5.7E2 | 5.8E1 | 46 | 12 | 46 | 12 | 0.37 |
| Sj | ng/ml | 4.2E-1 | 4.5E-1 | 4.2E-1 | 4.6E-1 | 8.4E-2 | 1.3E-1 | 2.5E-1 | 3.2E-1 | 6.1E-1 | 7.2E-1 | 46 | 12 | 46 | 12 | 0.59 |
| Rc | pg/ml | 7.0E3 | 5.3E3 | 7.8E3 | 7.5E3 | 5.4E3 | 8.6E3 | 3.9E2 | 5.5E2 | 2.8E4 | 3.9E4 | 114 | 19 | 114 | 19 | 0.41 |
| Rb | | 8.5E-1 | 1.0E-9 | 3.1E0 | 2.7E0 | 6.4E0 | 4.5E0 | 1.0E-9 | 1.0E-9 | 5.6E1 | 1.3E1 | 114 | 19 | 114 | 19 | 0.45 |
| Zq | 2.6ng/ml | 3.0E2 | 3.4E2 | 3.1E2 | 2.9E2 | 2.3E2 | 1.8E2 | 1.4E1 | 1.7E1 | 9.7E2 | 5.0E2 | 45 | 11 | 45 | 11 | 0.51 |
| Zw | 2.5ng/ml | 5.2E0 | 5.0E0 | 1.0E1 | 1.2E1 | 1.4E1 | 1.8E1 | 1.4E-1 | 2.4E-1 | 5.9E1 | 6.3E1 | 46 | 12 | 46 | 12 | 0.47 |
| Zx | 2.3mU/ml | 1.3E-1 | 1.2E-1 | 2.8E-1 | 3.1E-1 | 5.1E-1 | 5.2E-1 | 3.2E-2 | 6.1E-2 | 2.9E0 | 1.9E0 | 46 | 12 | 46 | 12 | 0.54 |
| Pz | ng/ml | 3.4E3 | 7.2E3 | 5.6E3 | 6.3E3 | 6.1E3 | 4.3E3 | 1.6E1 | 4.0E1 | 7.0E4 | 1.3E4 | 316 | 30 | 316 | 30 | 0.58 |
| Qa | ng/ml | 3.5E3 | 1.3E4 | 7.1E3 | 1.5E4 | 1.4E4 | 1.2E4 | 1.5E2 | 4.3E2 | 2.2E5 | 3.6E4 | 316 | 30 | 316 | 30 | 0.69 |
| Qb | ng/ml | 1.0E2 | 2.1E2 | 2.2E2 | 4.5E2 | 4.0E2 | 7.6E2 | 7.9E-1 | 1.3E1 | 5.3E3 | 4.1E3 | 316 | 30 | 316 | 30 | 0.64 |
| Qc | ng/ml | 2.0E2 | 3.6E2 | 4.4E2 | 6.4E2 | 6.0E2 | 6.3E2 | 1.0E-9 | 2.0E1 | 4.3E3 | 2.8E3 | 316 | 30 | 316 | 30 | 0.62 |
| Qd | ng/ml | 8.6E3 | 2.2E4 | 2.3E4 | 7.2E4 | 1.2E5 | 9.4E4 | 1.5E2 | 1.2E3 | 2.0E6 | 4.3E5 | 316 | 30 | 316 | 30 | 0.69 |
| Qe | ng/ml | 8.5E2 | 2.5E3 | 2.0E3 | 3.6E3 | 5.8E3 | 4.1E3 | 1.0E-9 | 5.7E1 | 9.7E4 | 1.8E4 | 316 | 30 | 316 | 30 | 0.63 |
| Jd | ng/ml | 8.6E-1 | 1.5E0 | 4.0E0 | 3.9E0 | 1.5E1 | 5.6E0 | 1.0E-9 | 1.0E-9 | 1.2E2 | 1.8E1 | 114 | 19 | 114 | 19 | 0.56 |
| Je | ng/ml | 1.0E-9 | 1.0E-9 | 1.9E0 | 9.9E-1 | 5.2E0 | 2.5E0 | 1.0E-9 | 1.0E-9 | 4.6E1 | 1.1E1 | 114 | 19 | 114 | 19 | 0.43 |
| Jf | ng/ml | 1.0E-9 | 1.0E-9 | 1.3E0 | 5.8E-1 | 2.4E0 | 1.2E0 | 1.0E-9 | 1.0E-9 | 1.2E1 | 4.1E0 | 114 | 19 | 114 | 19 | 0.42 |
| Jg | ng/ml | 4.6E2 | 7.8E2 | 7.8E2 | 1.1E3 | 9.6E2 | 1.0E3 | 5.8E0 | 2.4E1 | 1.0E4 | 3.9E3 | 318 | 31 | 318 | 31 | 0.59 |
| Jh | ng/ml | 2.7E0 | 6.0E0 | 2.2E1 | 2.9E1 | 8.8E1 | 5.6E1 | 1.0E-9 | 1.0E-9 | 1.2E3 | 2.9E2 | 318 | 31 | 318 | 31 | 0.65 |
| Ji | ng/ml | 5.5E1 | 1.2E2 | 8.5E1 | 2.0E2 | 1.1E2 | 2.1E2 | 1.1E0 | 8.9E0 | 1.3E3 | 6.9E2 | 318 | 31 | 318 | 31 | 0.66 |
| Sr | pg/mL | 3.9E2 | 5.0E2 | 1.0E3 | 1.1E3 | 2.2E3 | 1.2E3 | 1.0E-9 | 1.0E-9 | 2.1E4 | 4.0E3 | 113 | 19 | 113 | 19 | 0.55 |
| Ss | pg/mL | 8.2E4 | 1.0E5 | 1.5E5 | 1.1E5 | 1.9E5 | 8.3E4 | 2.7E3 | 7.6E3 | 1.3E6 | 2.4E5 | 113 | 19 | 113 | 19 | 0.51 |
| St | pg/mL | 2.5E7 | 3.3E7 | 5.3E7 | 1.1E8 | 8.1E7 | 2.6E8 | 1.0E-9 | 9.9E5 | 5.4E8 | 1.2E9 | 112 | 19 | 112 | 19 | 0.53 |
| Wc | ng/ml | 1.0E-9 | 5.4E-2 | 9.1E-2 | 1.0E-1 | 2.8E-1 | 1.8E-1 | 1.0E-9 | 1.0E-9 | 1.8E0 | 6.3E-1 | 46 | 12 | 46 | 12 | 0.62 |
| Wd | ng/ml | 9.5E0 | 1.1E1 | 3.3E1 | 6.1E1 | 7.6E1 | 1.2E2 | 1.0E0 | 2.3E0 | 3.8E2 | 4.1E2 | 46 | 12 | 46 | 12 | 0.58 |
| We | ng/ml | 2.8E-1 | 5.4E-1 | 1.3E0 | 1.6E0 | 3.5E0 | 2.8E0 | 1.0E-9 | 1.0E-9 | 2.3E1 | 9.7E0 | 46 | 12 | 46 | 12 | 0.60 |
| Wg | ng/ml | 1.0E-9 | 1.0E-9 | 1.2E-2 | 1.0E-9 | 7.9E-2 | 0.0E0 | 1.0E-9 | 1.0E-9 | 5.3E-1 | 1.0E-9 | 46 | 12 | 46 | 12 | 0.48 |
| Wh | ng/ml | 9.8E-3 | 2.1E-2 | 4.4E-2 | 5.9E-2 | 9.5E-2 | 1.2E-1 | 1.0E-9 | 1.0E-9 | 3.6E-1 | 4.2E-1 | 46 | 12 | 46 | 12 | 0.61 |
| Wf | ng/ml | 1.0E-9 | 1.0E-9 | 1.4E-1 | 6.5E-2 | 3.9E-1 | 1.4E-1 | 1.0E-9 | 1.0E-9 | 2.3E0 | 4.7E-1 | 46 | 12 | 46 | 12 | 0.47 |
| Ra | pg/ml | 1.0E-9 | 1.0E-9 | 1.0E0 | 3.7E-1 | 6.0E0 | 1.5E0 | 1.0E-9 | 1.0E-9 | 6.4E1 | 6.5E0 | 114 | 19 | 114 | 19 | 0.44 |
| Qz | pg/ml | 9.3E0 | 1.1E1 | 5.2E1 | 4.1E1 | 8.8E1 | 6.1E1 | 1.0E-9 | 1.0E-9 | 4.5E2 | 1.8E2 | 114 | 19 | 114 | 19 | 0.55 |
| Qy | pg/ml | 3.9E-1 | 4.7E-1 | 4.3E0 | 6.2E1 | 2.3E1 | 1.9E2 | 1.0E-9 | 1.0E-9 | 2.3E2 | 7.3E2 | 114 | 19 | 114 | 19 | 0.49 |
| Qx | pg/ml | 1.0E-9 | 1.0E-9 | 3.8E0 | 3.7E0 | 2.1E1 | 8.8E0 | 1.0E-9 | 1.0E-9 | 1.9E2 | 3.1E1 | 114 | 19 | 114 | 19 | 0.54 |
| Qw | pg/ml | 1.0E-9 | 4.5E-1 | 3.0E0 | 1.8E0 | 1.0E1 | 5.1E0 | 1.0E-9 | 1.0E-9 | 6.6E1 | 2.3E1 | 114 | 19 | 114 | 19 | 0.53 |
| Qv | pg/ml | 2.0E4 | 1.2E4 | 4.0E4 | 1.3E4 | 9.8E4 | 1.2E4 | 4.0E2 | 1.0E-9 | 9.4E5 | 5.0E4 | 114 | 19 | 114 | 19 | 0.32 |
| Qu | pg/ml | 8.0E0 | 3.8E0 | 8.7E1 | 1.3E2 | 1.8E2 | 2.2E2 | 1.0E-9 | 1.0E-9 | 9.8E2 | 7.3E2 | 114 | 19 | 114 | 19 | 0.51 |
| Qt | pg/ml | 1.1E1 | 2.0E1 | 4.4E1 | 5.0E1 | 1.0E2 | 7.4E1 | 1.0E-9 | 1.0E-9 | 7.1E2 | 2.2E2 | 114 | 19 | 114 | 19 | 0.59 |
| Qh | ng/ml | 1.8E1 | 2.3E1 | 4.3E1 | 9.6E1 | 6.8E1 | 1.9E2 | 2.5E-1 | 1.6E0 | 4.6E2 | 8.0E2 | 114 | 19 | 114 | 19 | 0.55 |
| Qg | ng/ml | 7.9E0 | 5.3E0 | 1.4E1 | 1.1E1 | 2.7E1 | 1.8E1 | 1.5E-1 | 1.0E0 | 2.7E2 | 8.1E1 | 114 | 19 | 114 | 19 | 0.40 |
| Jj | ng/ml | 5.3E2 | 2.2E2 | 2.0E3 | 5.0E2 | 1.9E4 | 4.8E2 | 2.3E0 | 8.7E0 | 3.4E5 | 2.0E3 | 318 | 31 | 318 | 31 | 0.38 |
| Jk | ng/ml | 2.6E0 | 5.6E0 | 1.9E1 | 4.6E1 | 4.4E1 | 8.5E1 | 1.0E-9 | 4.3E-2 | 2.8E2 | 3.9E2 | 318 | 31 | 318 | 31 | 0.58 |
| Jl | ng/ml | 4.6E-1 | 1.2E0 | 1.9E0 | 3.3E2 | 4.6E0 | 1.8E3 | 1.2E-3 | 5.4E-3 | 4.0E1 | 9.9E3 | 318 | 31 | 318 | 31 | 0.67 |
| Jm | ng/ml | 2.0E1 | 3.3E1 | 6.9E1 | 5.7E1 | 1.7E2 | 7.5E1 | 1.0E-9 | 1.0E-9 | 2.1E3 | 2.9E2 | 318 | 31 | 318 | 31 | 0.52 |
| Jn | pg/ml | 3.4E-1 | 1.1E0 | 5.3E0 | 3.4E1 | 5.0E1 | 1.4E2 | 1.0E-9 | 1.0E-9 | 6.2E2 | 7.3E2 | 318 | 31 | 318 | 31 | 0.63 |
| Jo | pg/ml | 3.8E3 | 5.1E3 | 5.1E3 | 6.2E3 | 6.8E3 | 7.2E3 | 2.0E1 | 2.4E1 | 1.0E5 | 3.6E4 | 318 | 31 | 318 | 31 | 0.52 |
| Jp | pg/ml | 7.0E4 | 8.8E4 | 7.3E4 | 9.4E4 | 3.9E4 | 4.6E4 | 5.8E2 | 4.6E3 | 3.8E5 | 2.1E5 | 318 | 31 | 318 | 31 | 0.66 |
| Jq | pg/ml | 9.5E1 | 1.7E2 | 1.8E2 | 3.8E2 | 5.2E2 | 5.3E2 | 1.0E0 | 7.4E0 | 8.7E3 | 2.4E3 | 318 | 31 | 318 | 31 | 0.62 |
| Jr | pg/ml | 4.4E0 | 1.5E1 | 7.1E1 | 3.4E2 | 6.7E2 | 1.4E3 | 1.0E-9 | 1.0E-9 | 1.1E4 | 7.4E3 | 318 | 31 | 318 | 31 | 0.65 |
| Js | pg/ml | 1.4E1 | 1.9E1 | 7.6E1 | 2.5E2 | 5.9E2 | 7.3E2 | 1.0E-9 | 2.1E0 | 1.0E4 | 3.0E3 | 318 | 31 | 318 | 31 | 0.61 |
| Jt | pg/ml | 2.4E3 | 2.6E3 | 3.1E3 | 5.7E3 | 3.5E3 | 8.7E3 | 2.2E1 | 1.5E2 | 5.2E4 | 4.1E4 | 318 | 31 | 318 | 31 | 0.54 |
| Xa | pg/ml | 7.0E-1 | 5.0E0 | 3.5E1 | 6.3E1 | 1.8E2 | 1.6E2 | 1.0E-9 | 1.0E-9 | 1.2E3 | 5.6E2 | 46 | 12 | 46 | 12 | 0.62 |
| Ye | pg/ml | 1.0E-9 | 1.0E-9 | 4.9E0 | 8.0E-1 | 1.5E1 | 2.1E0 | 1.0E-9 | 1.0E-9 | 6.9E1 | 7.2E0 | 46 | 12 | 46 | 12 | 0.47 |

Figure 40 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Tm | pg/ml | 1.0E-9 | 1.0E-9 | 2.5E0 | 2.8E0 | 4.5E0 | 4.1E0 | 1.0E-9 | 1.0E-9 | 1.8E1 | 8.4E0 | 46 | 12 | 46 | 12 | 0.53 |
| Tl | pg/ml | 1.3E-1 | 1.1E-1 | 8.3E-1 | 2.6E-1 | 3.6E0 | 3.3E-1 | 1.0E-9 | 1.0E-9 | 2.5E1 | 8.2E-1 | 46 | 12 | 46 | 12 | 0.46 |
| Ju | mIU/ml | 1.1E1 | 6.1E0 | 2.6E1 | 1.3E1 | 3.7E1 | 1.6E1 | 1.7E-1 | 6.0E-1 | 2.3E2 | 6.2E1 | 114 | 19 | 114 | 19 | 0.40 |
| Jv | mIU/ml | 1.7E1 | 1.1E1 | 4.2E1 | 2.1E1 | 6.5E1 | 3.6E1 | 1.7E-2 | 7.9E-2 | 4.4E2 | 1.4E2 | 114 | 19 | 114 | 19 | 0.37 |
| Jy | ng/ml | 1.7E-3 | 1.4E-3 | 2.3E-3 | 2.9E-3 | 3.7E-3 | 4.9E-3 | 1.0E-9 | 4.5E-4 | 3.9E-2 | 2.3E-2 | 114 | 19 | 114 | 19 | 0.47 |
| Kc | pg/ml | 2.2E1 | 2.5E1 | 4.2E1 | 6.4E1 | 5.0E1 | 8.4E1 | 1.0E-9 | 6.2E0 | 2.7E2 | 3.2E2 | 116 | 18 | 116 | 18 | 0.56 |
| Kd | pg/ml | 1.0E-9 | 1.0E-9 | 5.3E2 | 3.9E2 | 3.6E3 | 1.2E3 | 1.0E-9 | 1.0E-9 | 3.8E4 | 5.0E3 | 116 | 18 | 116 | 18 | 0.48 |
| Ke | pg/ml | 1.3E4 | 1.3E4 | 1.7E4 | 2.1E4 | 3.0E4 | 2.0E4 | 1.0E3 | 6.7E2 | 3.2E5 | 6.3E4 | 116 | 18 | 116 | 18 | 0.53 |
| Kf | pg/mL | 6.3E0 | 6.7E0 | 7.4E0 | 7.4E0 | 8.9E0 | 5.6E0 | 1.0E-9 | 1.0E-9 | 7.8E1 | 2.1E1 | 116 | 18 | 116 | 18 | 0.53 |
| Kg | pg/mL | 9.9E2 | 7.8E2 | 1.9E3 | 3.8E3 | 3.4E3 | 8.7E3 | 7.7E1 | 1.6E2 | 2.7E4 | 3.6E4 | 116 | 18 | 116 | 18 | 0.44 |
| Ki | pg/ml | 6.0E1 | 7.5E1 | 7.1E1 | 7.6E1 | 5.6E1 | 2.7E1 | 1.0E-9 | 6.0E0 | 2.9E2 | 1.1E2 | 116 | 18 | 116 | 18 | 0.62 |
| Kj | pg/ml | 8.4E2 | 6.1E2 | 1.4E3 | 1.5E3 | 1.8E3 | 2.0E3 | 6.6E1 | 3.3E1 | 1.5E4 | 7.7E3 | 116 | 18 | 116 | 18 | 0.44 |
| Kk | pg/ml | 7.1E0 | 8.2E0 | 1.4E1 | 1.3E1 | 1.6E1 | 1.3E1 | 1.0E-9 | 1.0E-9 | 8.1E1 | 4.8E1 | 116 | 18 | 116 | 18 | 0.52 |
| Kl | pg/ml | 1.8E4 | 1.6E4 | 2.8E4 | 2.2E4 | 2.7E4 | 1.9E4 | 2.3E2 | 2.4E2 | 1.3E5 | 5.0E4 | 116 | 18 | 116 | 18 | 0.44 |
| Kn | pg/ml | 3.0E1 | 3.0E1 | 1.1E2 | 7.3E1 | 4.6E2 | 1.2E2 | 1.0E-9 | 1.0E-9 | 4.9E3 | 4.3E2 | 116 | 18 | 116 | 18 | 0.51 |
| Ko | pg/ml | 3.6E2 | 1.7E2 | 5.1E2 | 3.4E2 | 5.9E2 | 3.5E2 | 1.0E-9 | 1.0E-9 | 4.1E3 | 1.0E3 | 116 | 18 | 116 | 18 | 0.43 |
| Kp | pg/ml | 3.6E2 | 3.2E2 | 4.8E2 | 3.5E2 | 1.2E3 | 2.4E2 | 1.0E-9 | 1.0E-9 | 1.3E4 | 7.9E2 | 116 | 18 | 116 | 18 | 0.48 |
| Kq | pg/ml | 3.3E2 | 4.7E2 | 1.8E3 | 1.0E3 | 1.5E4 | 1.4E3 | 5.1E0 | 1.6E0 | 1.6E5 | 5.5E3 | 111 | 18 | 111 | 18 | 0.56 |
| Kr | pg/ml | 3.8E-1 | 2.3E-1 | 5.9E0 | 1.5E0 | 3.9E1 | 2.0E0 | 1.0E-9 | 1.0E-9 | 4.2E2 | 5.7E0 | 111 | 18 | 111 | 18 | 0.48 |
| Ks | pg/ml | 1.5E4 | 1.0E4 | 2.1E4 | 2.0E4 | 1.8E4 | 1.9E4 | 4.5E2 | 5.1E1 | 7.9E4 | 5.0E4 | 111 | 18 | 111 | 18 | 0.45 |
| Ps | ng/ml | 1.5E2 | 4.6E2 | 5.5E2 | 2.0E3 | 1.4E3 | 3.8E3 | 1.6E0 | 5.5E0 | 9.0E3 | 1.2E4 | 46 | 12 | 46 | 12 | 0.61 |
| Kx | ng/ml | 2.8E-4 | 5.0E-3 | 7.4E-3 | 1.5E-2 | 1.5E-2 | 2.2E-2 | 1.0E-9 | 1.0E-9 | 1.0E-1 | 7.9E-2 | 115 | 18 | 115 | 18 | 0.61 |
| Ky | ng/ml | 1.2E-1 | 4.8E-1 | 3.3E-1 | 7.5E-1 | 6.8E-1 | 1.0E0 | 1.0E-9 | 1.0E-9 | 5.1E0 | 4.4E0 | 115 | 18 | 115 | 18 | 0.68 |
| Kz | ng/ml | 1.0E-9 | 1.0E-9 | 3.9E-3 | 4.6E-3 | 5.9E-3 | 7.9E-3 | 1.0E-9 | 1.0E-9 | 1.8E-2 | 2.5E-2 | 115 | 18 | 115 | 18 | 0.50 |
| Rz | ng/ml | 3.2E-1 | 7.5E-1 | 7.9E-1 | 1.4E0 | 1.2E0 | 2.1E0 | 1.1E-2 | 4.6E-3 | 6.7E0 | 7.5E0 | 46 | 12 | 46 | 12 | 0.57 |
| Ry | ng/ml | 1.6E-2 | 1.6E-2 | 3.3E-2 | 2.1E-2 | 5.5E-2 | 2.3E-2 | 1.0E-9 | 1.0E-9 | 3.5E-1 | 7.5E-2 | 46 | 12 | 46 | 12 | 0.44 |
| Rx | ng/ml | 1.0E-9 | 3.6E-3 | 1.1E-3 | 3.0E-3 | 2.0E-3 | 3.1E-3 | 1.0E-9 | 1.0E-9 | 8.6E-3 | 8.6E-3 | 46 | 12 | 46 | 12 | 0.70 |
| Ld | pg/ml | 1.0E-9 | 1.0E-9 | 3.8E0 | 4.9E0 | 9.0E0 | 8.0E0 | 1.0E-9 | 1.0E-9 | 6.9E1 | 2.9E1 | 117 | 17 | 117 | 17 | 0.55 |
| Lh | pg/ml | 1.3E4 | 3.2E4 | 2.3E4 | 5.3E4 | 4.2E4 | 7.9E4 | 1.0E-9 | 1.0E-9 | 4.8E5 | 4.1E5 | 319 | 31 | 319 | 31 | 0.64 |
| Li | pg/ml | 3.7E3 | 5.4E3 | 1.9E4 | 4.7E4 | 9.3E4 | 9.9E4 | 1.2E1 | 1.3E1 | 1.3E6 | 4.1E5 | 319 | 31 | 319 | 31 | 0.53 |
| Lj | pg/ml | 3.1E3 | 1.2E3 | 2.0E4 | 3.3E4 | 5.6E4 | 7.8E4 | 1.0E-9 | 1.0E-9 | 4.3E5 | 3.9E5 | 319 | 31 | 319 | 31 | 0.48 |
| Lp | pg/ml | 1.3E1 | 2.6E0 | 1.1E2 | 1.3E2 | 2.5E2 | 4.1E2 | 1.0E-9 | 1.0E-9 | 1.1E3 | 1.4E3 | 46 | 12 | 46 | 12 | 0.35 |
| Lt | pg/ml | 1.0E-9 | 1.0E-9 | 1.9E0 | 1.0E-9 | 6.2E0 | 0.0E0 | 1.0E-9 | 1.0E-9 | 2.5E1 | 1.0E-9 | 46 | 12 | 46 | 12 | 0.46 |
| Rv | ng/ml | 5.0E-4 | 5.0E-4 | 1.5E-3 | 1.4E-3 | 3.1E-3 | 2.5E-3 | 1.0E-9 | 1.0E-9 | 1.6E-2 | 9.2E-3 | 46 | 12 | 46 | 12 | 0.53 |
| Ru | ng/ml | 1.0E-9 | 1.0E-9 | 2.6E-2 | 5.9E-3 | 8.7E-2 | 2.0E-2 | 1.0E-9 | 1.0E-9 | 3.5E-1 | 7.1E-2 | 46 | 12 | 46 | 12 | 0.49 |
| Rt | ng/ml | 7.8E-2 | 3.9E-2 | 2.6E-1 | 2.1E-1 | 1.1E0 | 2.6E-1 | 6.5E-3 | 1.3E-3 | 7.4E0 | 6.3E-1 | 46 | 12 | 46 | 12 | 0.47 |
| Yl | pg/ml | 1.3E1 | 5.6E0 | 2.3E1 | 1.3E1 | 3.4E1 | 1.6E1 | 1.0E-9 | 1.0E-9 | 2.2E2 | 4.9E1 | 46 | 12 | 46 | 12 | 0.36 |
| Rm | ng/ml | 1.8E1 | 2.0E1 | 4.9E1 | 5.4E1 | 8.8E1 | 7.3E1 | 2.2E-1 | 2.3E-1 | 6.5E2 | 2.5E2 | 113 | 19 | 113 | 19 | 0.49 |
| Rh | ng/ml | 1.8E2 | 1.4E2 | 4.8E2 | 1.1E3 | 1.7E3 | 3.9E3 | 7.5E0 | 2.5E1 | 1.7E4 | 1.7E4 | 113 | 19 | 113 | 19 | 0.41 |
| Ri | ng/ml | 4.4E-2 | 4.4E-2 | 3.8E0 | 4.2E0 | 7.7E0 | 1.0E1 | 1.0E-9 | 1.0E-9 | 4.9E1 | 4.5E1 | 113 | 19 | 113 | 19 | 0.49 |
| Rg | ng/ml | 1.0E-9 | 1.0E-9 | 9.4E-2 | 1.5E-2 | 4.6E-1 | 4.8E-2 | 1.0E-9 | 1.0E-9 | 3.3E0 | 2.1E-1 | 113 | 19 | 113 | 19 | 0.51 |
| Rj | ng/ml | 1.0E-9 | 1.0E-9 | 3.3E0 | 4.6E-1 | 2.5E1 | 1.0E0 | 1.0E-9 | 1.0E-9 | 2.7E2 | 3.2E0 | 113 | 19 | 113 | 19 | 0.45 |
| Rf | ng/ml | 4.0E-1 | 2.6E-1 | 7.7E-1 | 1.8E0 | 9.8E-1 | 4.2E0 | 2.1E-2 | 2.1E-2 | 6.2E0 | 1.7E1 | 113 | 19 | 113 | 19 | 0.44 |
| Ql | pg/ml | 2.6E0 | 1.1E1 | 1.2E1 | 1.5E1 | 2.4E1 | 1.9E1 | 1.0E-9 | 1.0E-9 | 1.8E2 | 5.5E1 | 114 | 19 | 114 | 19 | 0.56 |
| Qm | pg/ml | 2.0E0 | 4.7E-1 | 2.0E1 | 2.0E1 | 3.6E1 | 3.1E1 | 1.0E-9 | 1.0E-9 | 1.9E2 | 8.6E1 | 114 | 19 | 114 | 19 | 0.51 |
| Qn | pg/ml | 6.1E-1 | 6.1E-1 | 5.6E0 | 1.5E1 | 2.2E1 | 4.7E1 | 1.0E-9 | 1.0E-9 | 2.2E2 | 2.0E2 | 114 | 19 | 114 | 19 | 0.51 |
| Nv | pg/ml | 3.8E3 | 8.9E3 | 8.9E3 | 2.4E4 | 1.8E4 | 3.7E4 | 1.0E-9 | 1.9E1 | 1.6E5 | 1.5E5 | 320 | 31 | 320 | 31 | 0.64 |
| Nw | pg/ml | 9.6E3 | 1.5E4 | 1.3E4 | 2.9E4 | 1.6E4 | 4.0E4 | 2.0E2 | 1.9E2 | 2.1E5 | 2.1E5 | 320 | 31 | 320 | 31 | 0.63 |
| Nx | pg/ml | 2.2E2 | 2.4E2 | 4.3E2 | 6.0E2 | 6.4E2 | 6.8E2 | 1.0E-9 | 1.0E-9 | 4.1E3 | 2.3E3 | 320 | 31 | 320 | 31 | 0.60 |
| Ny | pg/ml | 6.4E0 | 2.0E1 | 1.1E2 | 8.4E1 | 1.4E3 | 1.4E2 | 1.0E-9 | 1.0E-9 | 2.5E4 | 6.1E2 | 320 | 31 | 320 | 31 | 0.64 |
| Oa | pg/ml | 1.6E2 | 1.9E2 | 4.6E2 | 6.7E2 | 7.3E2 | 9.6E2 | 1.0E-9 | 1.0E-9 | 4.5E3 | 3.4E3 | 114 | 19 | 114 | 19 | 0.53 |
| Op | pg/ml | 4.4E5 | 4.5E5 | 4.4E5 | 4.5E5 | 1.5E5 | 2.1E5 | 5.2E4 | 1.4E5 | 7.3E5 | 7.5E5 | 46 | 12 | 46 | 12 | 0.50 |
| Oe | pg/ml | 3.1E1 | 1.0E-9 | 2.5E2 | 2.3E2 | 3.8E2 | 3.8E2 | 1.0E-9 | 1.0E-9 | 2.3E3 | 1.4E3 | 318 | 31 | 318 | 31 | 0.46 |
| Of | pg/ml | 1.4E2 | 1.3E2 | 5.3E3 | 2.5E3 | 2.1E4 | 6.3E3 | 1.0E-9 | 1.0E-9 | 1.9E5 | 2.4E4 | 320 | 31 | 320 | 31 | 0.47 |
| Og | pg/ml | 6.3E-2 | 7.8E-2 | 3.7E-1 | 1.1E-1 | 1.5E0 | 1.8E-1 | 1.0E-9 | 1.0E-9 | 1.9E1 | 9.4E-1 | 320 | 31 | 320 | 31 | 0.49 |
| Oh | pg/ml | 2.4E0 | 6.4E0 | 1.3E1 | 5.8E2 | 9.0E1 | 2.8E3 | 1.0E-9 | 1.0E-9 | 1.4E3 | 1.6E4 | 320 | 31 | 320 | 31 | 0.65 |
| Oi | pg/ml | 1.9E0 | 2.2E0 | 5.0E0 | 5.4E0 | 7.9E0 | 8.2E0 | 1.0E-9 | 1.0E-9 | 6.7E1 | 3.1E1 | 320 | 31 | 320 | 31 | 0.49 |

Figure 40 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ok | pg/ml | 3.9E2 | 6.3E2 | 5.3E2 | 1.3E3 | 6.1E2 | 1.6E3 | 2.9E1 | 1.5E1 | 7.8E3 | 7.0E3 | 320 | 31 | 320 | 31 | 0.62 |
| Om | pg/ml | 4.1E2 | 6.1E2 | 9.5E2 | 1.2E3 | 3.5E3 | 1.4E3 | 1.0E-9 | 1.0E-9 | 5.1E4 | 5.6E3 | 320 | 31 | 320 | 31 | 0.63 |
| On | pg/ml | 1.8E2 | 4.7E2 | 2.8E2 | 9.3E2 | 4.2E2 | 1.6E3 | 1.0E-9 | 1.0E1 | 4.5E3 | 8.5E3 | 320 | 31 | 320 | 31 | 0.68 |
| Or | pg/ml | 9.7E0 | 3.5E1 | 3.2E1 | 1.0E2 | 7.1E1 | 1.4E2 | 1.0E-9 | 1.0E-9 | 5.1E2 | 4.5E2 | 117 | 18 | 117 | 18 | 0.64 |
| Ow | pg/ml | 3.8E1 | 5.4E1 | 1.9E2 | 4.4E2 | 8.0E2 | 8.3E2 | 1.0E-9 | 1.0E-9 | 8.1E3 | 3.0E3 | 117 | 18 | 117 | 18 | 0.60 |
| Ou | pg/ml | 5.1E2 | 1.0E3 | 1.0E3 | 2.6E3 | 1.7E3 | 3.2E3 | 1.0E-9 | 2.0E1 | 9.8E3 | 1.1E4 | 117 | 18 | 117 | 18 | 0.60 |
| Ul | ng/ml | 1.0E-9 | 1.0E-9 | 1.7E0 | 2.2E-1 | 7.0E0 | 9.7E-1 | 1.0E-9 | 1.0E-9 | 5.6E1 | 4.2E0 | 115 | 19 | 115 | 19 | 0.48 |
| Uo | ng/ml | 1.0E-9 | 1.0E-9 | 8.6E-2 | 1.3E-2 | 2.2E-1 | 5.6E-2 | 1.0E-9 | 1.0E-9 | 1.3E0 | 2.4E-1 | 115 | 19 | 115 | 19 | 0.40 |
| Uk | ng/ml | 1.0E-9 | 1.0E-9 | 6.9E-3 | 1.0E-3 | 3.3E-2 | 2.5E-3 | 1.0E-9 | 1.0E-9 | 3.2E-1 | 1.1E-2 | 115 | 19 | 115 | 19 | 0.45 |
| Um | ng/ml | 1.0E-9 | 1.0E-9 | 2.7E-1 | 1.0E-9 | 6.5E-1 | 0.0E0 | 1.0E-9 | 1.0E-9 | 3.6E0 | 1.0E-9 | 115 | 19 | 115 | 19 | 0.35 |
| Uf | ng/ml | 6.0E-2 | 9.5E-2 | 1.2E-1 | 4.6E-1 | 1.8E-1 | 1.1E0 | 2.7E-3 | 1.0E-3 | 1.1E0 | 5.1E0 | 115 | 19 | 115 | 19 | 0.59 |
| Uh | ng/ml | 2.2E0 | 3.4E0 | 3.4E0 | 4.9E0 | 3.2E0 | 4.7E0 | 3.6E-2 | 4.7E-2 | 1.5E1 | 1.8E1 | 115 | 19 | 115 | 19 | 0.59 |
| Un | ng/ml | 1.7E0 | 1.7E0 | 2.1E0 | 2.5E0 | 2.4E0 | 1.9E0 | 3.5E-1 | 3.4E-1 | 2.5E1 | 8.0E0 | 115 | 19 | 115 | 19 | 0.57 |
| Ug | ng/ml | 1.1E1 | 8.9E0 | 2.3E1 | 1.4E1 | 2.8E1 | 1.5E1 | 1.5E0 | 1.0E0 | 1.6E2 | 6.9E1 | 115 | 19 | 115 | 19 | 0.42 |
| Ur | ng/ml | 1.1E-1 | 7.5E-2 | 3.8E-1 | 2.3E-1 | 9.7E-1 | 3.4E-1 | 1.0E-9 | 1.0E-9 | 7.3E0 | 1.0E0 | 114 | 19 | 114 | 19 | 0.45 |
| Up | ng/ml | 1.0E-9 | 1.0E-4 | 2.4E-2 | 5.9E-3 | 2.2E-1 | 1.7E-2 | 1.0E-9 | 1.0E-9 | 2.4E0 | 7.4E-2 | 114 | 19 | 114 | 19 | 0.60 |
| Us | ng/ml | 2.0E-3 | 1.5E-2 | 3.1E-2 | 1.8E-2 | 1.6E-1 | 2.1E-2 | 1.0E-9 | 1.0E-9 | 1.7E0 | 6.4E-2 | 114 | 19 | 114 | 19 | 0.60 |
| Uv | ng/ml | 2.6E-3 | 3.0E-3 | 1.7E-2 | 1.4E-2 | 5.7E-2 | 3.5E-2 | 1.0E-9 | 1.0E-9 | 4.1E-1 | 1.5E-1 | 114 | 19 | 114 | 19 | 0.52 |
| Ut | ng/ml | 6.8E-1 | 1.9E0 | 2.7E0 | 5.2E0 | 8.1E0 | 7.1E0 | 1.0E-9 | 9.2E-2 | 6.5E1 | 2.4E1 | 114 | 19 | 114 | 19 | 0.65 |
| Uu | ng/ml | 7.0E0 | 6.2E0 | 7.5E0 | 6.4E0 | 5.0E0 | 5.3E0 | 5.4E-1 | 8.1E-1 | 2.9E1 | 2.3E1 | 114 | 19 | 114 | 19 | 0.42 |
| Uw | ng/ml | 2.1E0 | 4.0E0 | 3.5E0 | 3.6E0 | 5.9E0 | 2.2E0 | 1.5E-1 | 1.0E-9 | 3.9E1 | 6.4E0 | 47 | 12 | 47 | 12 | 0.61 |
| Vb | ng/ml | 1.1E0 | 1.1E0 | 1.2E0 | 9.2E-1 | 8.8E-1 | 5.1E-1 | 2.8E-1 | 8.5E-2 | 6.4E0 | 1.4E0 | 47 | 12 | 47 | 12 | 0.43 |
| Vc | ng/ml | 1.0E-9 | 1.0E-9 | 4.3E-3 | 1.1E-3 | 1.9E-2 | 3.9E-3 | 1.0E-9 | 1.0E-9 | 1.1E-1 | 1.3E-2 | 47 | 12 | 47 | 12 | 0.51 |
| Uy | ng/ml | 1.4E0 | 9.3E-1 | 8.9E0 | 3.9E0 | 2.0E1 | 1.1E1 | 8.7E-2 | 2.0E-2 | 9.9E1 | 3.8E1 | 47 | 12 | 47 | 12 | 0.36 |
| Uz | ng/ml | 1.0E-9 | 1.0E-9 | 7.1E-1 | 2.6E-2 | 4.8E0 | 9.0E-2 | 1.0E-9 | 1.0E-9 | 3.3E1 | 3.1E-1 | 47 | 12 | 47 | 12 | 0.52 |
| Ux | ng/ml | 1.8E2 | 1.4E2 | 1.9E2 | 1.7E2 | 1.3E2 | 1.6E2 | 1.2E1 | 4.5E0 | 4.8E2 | 4.9E2 | 47 | 12 | 47 | 12 | 0.43 |
| Va | ng/ml | 1.4E1 | 3.4E0 | 2.5E1 | 1.4E1 | 2.9E1 | 2.2E1 | 3.1E-1 | 3.6E-1 | 1.2E2 | 6.2E1 | 47 | 12 | 47 | 12 | 0.33 |
| Vh | ng/ml | 1.1E-2 | 2.0E-2 | 3.7E-2 | 2.1E-2 | 1.3E-1 | 1.7E-2 | 3.9E-4 | 1.0E-3 | 8.6E-1 | 5.8E-2 | 47 | 12 | 47 | 12 | 0.56 |
| Vi | ng/ml | 3.5E-3 | 1.6E-2 | 4.6E-2 | 3.2E-2 | 2.7E-1 | 4.0E-2 | 1.0E-9 | 1.5E-4 | 1.8E0 | 1.2E-1 | 47 | 12 | 47 | 12 | 0.66 |
| Vj | ng/ml | 2.7E1 | 7.5E1 | 5.1E1 | 1.4E2 | 5.5E1 | 1.9E2 | 4.6E0 | 1.4E0 | 2.5E2 | 6.5E2 | 47 | 11 | 47 | 11 | 0.67 |
| Vp | ng/ml | 1.0E-9 | 1.0E-9 | 5.5E-1 | 3.7E-1 | 4.6E0 | 1.3E0 | 1.0E-9 | 1.0E-9 | 4.9E1 | 5.6E0 | 115 | 19 | 115 | 19 | 0.59 |
| Vt | ng/ml | 6.2E0 | 5.7E0 | 9.2E0 | 9.0E0 | 1.5E1 | 9.2E0 | 9.6E-1 | 5.6E-1 | 1.6E2 | 3.8E1 | 115 | 19 | 115 | 19 | 0.48 |
| Vu | ng/ml | 1.0E-9 | 1.5E0 | 1.3E0 | 3.6E0 | 3.0E0 | 4.8E0 | 1.0E-9 | 1.0E-9 | 2.2E1 | 1.3E1 | 112 | 19 | 112 | 19 | 0.64 |
| Vq | ng/ml | 1.6E2 | 1.3E2 | 7.0E2 | 8.7E2 | 1.6E3 | 1.5E3 | 9.2E-1 | 6.5E-1 | 1.2E4 | 4.9E3 | 91 | 17 | 91 | 17 | 0.54 |
| Vo | ng/ml | 2.5E1 | 2.5E1 | 2.5E1 | 2.3E1 | 5.3E1 | 7.2E0 | 4.9E0 | 1.9E0 | 4.8E1 | 3.1E1 | 115 | 19 | 115 | 19 | 0.47 |
| Vs | ng/ml | 1.0E-9 | 4.7E-1 | 7.9E0 | 7.8E0 | 4.4E1 | 1.3E1 | 1.0E-9 | 1.0E-9 | 4.5E2 | 4.9E1 | 113 | 19 | 113 | 19 | 0.57 |
| Vv | ng/ml | 2.9E0 | 2.8E0 | 5.4E0 | 1.0E1 | 9.4E0 | 1.3E1 | 1.0E-9 | 1.0E-9 | 8.4E1 | 4.4E1 | 114 | 19 | 114 | 19 | 0.57 |
| Vw | ng/ml | 3.6E1 | 4.4E1 | 3.4E1 | 3.8E1 | 1.7E1 | 2.5E1 | 3.1E0 | 2.5E0 | 6.7E1 | 6.9E1 | 47 | 12 | 47 | 12 | 0.57 |
| Oy | pg/ml | 4.8E-1 | 2.7E-1 | 6.3E0 | 3.9E0 | 3.2E1 | 9.6E0 | 1.0E-9 | 1.0E-9 | 4.0E2 | 4.0E1 | 319 | 31 | 319 | 31 | 0.48 |
| Oz | pg/ml | 2.5E-3 | 3.3E-2 | 3.3E-1 | 1.2E0 | 1.6E0 | 5.0E0 | 1.0E-9 | 1.0E-9 | 2.9E1 | 2.8E1 | 319 | 31 | 319 | 31 | 0.53 |
| Pa | pg/ml | 3.9E-1 | 4.2E-1 | 1.7E0 | 9.5E0 | 8.1E0 | 4.1E1 | 1.0E-9 | 1.0E-9 | 1.0E2 | 2.3E2 | 319 | 31 | 319 | 31 | 0.55 |
| Pb | pg/ml | 1.0E-9 | 1.0E-9 | 1.8E0 | 1.4E-1 | 2.7E1 | 3.5E-1 | 1.0E-9 | 1.0E-9 | 4.9E2 | 1.9E0 | 319 | 31 | 319 | 31 | 0.52 |
| Pc | pg/ml | 2.0E-2 | 3.0E-1 | 3.7E-1 | 1.1E1 | 9.1E-1 | 5.9E1 | 1.0E-9 | 1.0E-9 | 1.4E1 | 3.3E2 | 319 | 31 | 319 | 31 | 0.57 |
| Pd | pg/ml | 1.6E0 | 1.5E0 | 6.8E0 | 7.4E0 | 4.8E1 | 1.3E1 | 1.0E-9 | 1.0E-9 | 8.4E2 | 5.5E1 | 319 | 31 | 319 | 31 | 0.53 |
| Pe | pg/ml | 2.1E1 | 4.7E1 | 1.4E2 | 6.9E2 | 6.4E2 | 2.7E3 | 1.0E-9 | 3.8E-1 | 6.7E3 | 1.5E4 | 319 | 31 | 319 | 31 | 0.62 |
| Pf | pg/ml | 1.7E0 | 2.4E0 | 1.5E1 | 3.1E1 | 9.3E1 | 8.1E1 | 1.0E-9 | 1.0E-9 | 1.5E3 | 4.3E2 | 319 | 31 | 319 | 31 | 0.57 |
| Pg | pg/ml | 3.8E0 | 9.3E0 | 7.4E1 | 1.5E2 | 5.4E2 | 3.3E2 | 1.0E-9 | 8.4E-1 | 7.7E3 | 1.3E3 | 319 | 31 | 319 | 31 | 0.68 |
| Ph | ng/ml | 1.5E-1 | 1.7E-1 | 3.7E-1 | 4.4E-1 | 6.6E-1 | 6.7E-1 | 1.0E-9 | 1.0E-9 | 5.4E0 | 2.8E0 | 117 | 18 | 117 | 18 | 0.52 |
| Pi | ng/ml | 1.9E-1 | 3.0E-1 | 9.8E-1 | 6.3E-1 | 7.6E0 | 1.1E0 | 1.0E-9 | 1.0E-9 | 8.2E1 | 4.8E0 | 117 | 18 | 117 | 18 | 0.64 |
| Pj | ng/mL | 5.6E0 | 4.4E0 | 6.2E0 | 5.5E0 | 4.3E0 | 5.3E0 | 4.9E-1 | 4.0E-1 | 3.1E1 | 2.3E1 | 117 | 18 | 117 | 18 | 0.41 |
| Pk | ng/ml | 9.0E-3 | 1.4E-2 | 2.7E-2 | 2.0E-2 | 1.4E-1 | 2.6E-2 | 1.0E-9 | 1.0E-9 | 1.5E0 | 1.1E-1 | 117 | 18 | 117 | 18 | 0.58 |
| aA | mg/dL | 9.0E-1 | 1.2E0 | 1.0E0 | 1.6E0 | 5.1E-1 | 1.0E0 | 3.0E-1 | 4.0E-1 | 4.2E0 | 4.7E0 | 487 | 46 | 487 | 46 | 0.72 |
| aC | mg/mL | 2.3E0 | 1.9E0 | 2.7E0 | 2.5E0 | 1.3E0 | 1.6E0 | 7.5E-1 | 9.7E-1 | 7.4E0 | 6.7E0 | 152 | 22 | 152 | 22 | 0.40 |
| aD | ug/mL | 2.9E0 | 3.5E0 | 4.7E0 | 4.1E0 | 4.9E0 | 2.4E0 | 7.5E-1 | 1.6E0 | 3.5E1 | 9.8E0 | 152 | 22 | 152 | 22 | 0.52 |
| aE | mg/mL | 5.7E-1 | 5.7E-1 | 5.9E-1 | 5.9E-1 | 1.8E-1 | 1.4E-1 | 1.8E-1 | 4.1E-1 | 1.2E0 | 1.0E0 | 152 | 22 | 152 | 22 | 0.49 |
| aF | ng/mL | 2.2E0 | 2.7E0 | 4.7E0 | 7.6E0 | 7.3E0 | 9.6E0 | 4.3E-3 | 4.3E-3 | 5.0E1 | 3.5E1 | 152 | 22 | 152 | 22 | 0.58 |
| aG | mg/mL | 1.4E-1 | 1.1E-1 | 1.6E-1 | 1.4E-1 | 8.8E-2 | 7.0E-2 | 3.2E-2 | 6.9E-2 | 4.8E-1 | 3.5E-1 | 152 | 22 | 152 | 22 | 0.43 |

Figure 40 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aH | ug/mL | 7.3E1 | 6.2E1 | 7.7E1 | 7.6E1 | 4.0E1 | 4.1E1 | 8.9E0 | 2.3E1 | 2.0E2 | 2.0E2 | 152 | 22 | 152 | 22 | 0.49 |
| aI | ug/mL | 1.7E2 | 1.5E2 | 1.8E2 | 1.6E2 | 6.2E1 | 5.4E1 | 3.2E1 | 7.5E1 | 3.4E2 | 2.9E2 | 152 | 22 | 152 | 22 | 0.40 |
| aJ | ug/mL | 2.3E0 | 4.0E0 | 3.1E0 | 4.9E0 | 2.2E0 | 4.5E0 | 8.2E-1 | 1.5E0 | 1.4E1 | 2.3E1 | 152 | 22 | 152 | 22 | 0.68 |
| aK | ng/mL | 1.3E0 | 1.3E0 | 2.0E0 | 1.5E0 | 2.0E0 | 1.4E0 | 2.9E-4 | 1.3E-1 | 1.0E1 | 6.5E0 | 152 | 22 | 152 | 22 | 0.45 |
| aL | mg/mL | 7.4E-1 | 7.2E-1 | 7.8E-1 | 6.7E-1 | 2.6E-1 | 2.1E-1 | 2.2E-1 | 3.2E-1 | 1.7E0 | 1.2E0 | 152 | 22 | 152 | 22 | 0.39 |
| aM | U/mL | 1.7E1 | 2.8E1 | 4.0E1 | 8.4E1 | 8.1E1 | 1.5E2 | 4.2E-1 | 4.2E-2 | 8.2E2 | 6.8E2 | 152 | 22 | 152 | 22 | 0.66 |
| aN | U/mL | 1.4E1 | 1.9E1 | 2.5E1 | 2.8E1 | 4.4E1 | 3.0E1 | 2.5E-3 | 4.8E0 | 3.8E2 | 1.3E2 | 152 | 22 | 152 | 22 | 0.59 |
| aO | pg/mL | 4.3E1 | 1.8E2 | 4.0E2 | 6.4E2 | 9.9E2 | 9.0E2 | 6.0E-2 | 2.1E0 | 6.6E3 | 3.3E3 | 152 | 22 | 152 | 22 | 0.68 |
| aP | ng/mL | 1.6E0 | 2.8E0 | 2.1E0 | 4.0E0 | 2.5E0 | 5.6E0 | 4.5E-1 | 1.1E0 | 2.8E1 | 2.8E1 | 152 | 22 | 152 | 22 | 0.70 |
| aQ | ng/mL | 2.4E-1 | 2.4E-1 | 3.6E-1 | 3.2E-1 | 3.3E-1 | 2.4E-1 | 2.0E-4 | 5.2E-2 | 2.0E0 | 9.2E-1 | 152 | 22 | 152 | 22 | 0.49 |
| aR | ng/mL | 1.7E0 | 2.8E0 | 2.8E0 | 4.2E0 | 4.0E0 | 4.0E0 | 2.6E-1 | 5.6E-1 | 3.4E1 | 1.5E1 | 152 | 22 | 152 | 22 | 0.65 |
| aS | ng/mL | 3.7E-1 | 6.0E-1 | 1.0E0 | 1.0E0 | 2.8E0 | 1.2E0 | 4.2E-3 | 2.8E-2 | 3.3E1 | 4.9E0 | 152 | 22 | 152 | 22 | 0.59 |
| aU | pg/mL | 6.8E1 | 4.2E1 | 1.0E2 | 7.7E1 | 1.1E2 | 1.1E2 | 7.4E-2 | 7.4E-2 | 7.0E2 | 5.1E2 | 152 | 22 | 152 | 22 | 0.39 |
| aV | ng/mL | 6.0E-1 | 4.7E-1 | 1.1E0 | 6.6E-1 | 2.8E0 | 5.6E-1 | 7.6E-4 | 1.5E-1 | 3.3E1 | 2.4E0 | 152 | 22 | 152 | 22 | 0.46 |
| aW | pg/mL | 1.9E1 | 2.1E1 | 2.3E1 | 2.0E1 | 3.6E1 | 1.2E1 | 7.2E-2 | 7.2E-2 | 4.2E2 | 4.7E1 | 152 | 22 | 152 | 22 | 0.52 |
| aX | ng/mL | 7.8E0 | 1.3E1 | 1.3E1 | 3.6E1 | 2.1E1 | 7.0E1 | 3.0E-1 | 1.7E0 | 2.2E2 | 3.1E2 | 152 | 22 | 152 | 22 | 0.56 |
| aY | pg/mL | 5.2E1 | 6.3E1 | 7.5E1 | 8.7E1 | 1.1E2 | 8.2E1 | 4.1E-1 | 1.2E1 | 1.2E3 | 3.9E2 | 152 | 22 | 152 | 22 | 0.59 |
| aZ | pg/mL | 2.2E2 | 4.5E2 | 5.0E2 | 1.9E3 | 1.1E3 | 2.6E3 | 1.7E0 | 1.5E1 | 1.2E4 | 7.9E3 | 152 | 22 | 152 | 22 | 0.67 |
| bA | ng/mL | 1.3E1 | 1.0E2 | 6.1E1 | 1.7E2 | 1.5E2 | 3.1E2 | 3.0E-2 | 3.0E-2 | 9.4E2 | 1.5E3 | 152 | 22 | 152 | 22 | 0.69 |
| bB | ng/mL | 2.8E2 | 2.3E2 | 3.1E2 | 2.8E2 | 1.8E2 | 1.9E2 | 2.1E0 | 6.5E1 | 9.5E2 | 7.4E2 | 152 | 22 | 152 | 22 | 0.43 |
| bC | ng/mL | 3.2E2 | 3.8E2 | 5.8E2 | 1.1E3 | 7.7E2 | 1.4E3 | 1.4E1 | 5.0E1 | 4.7E3 | 4.0E3 | 152 | 22 | 152 | 22 | 0.58 |
| bE | mg/mL | 5.2E0 | 4.8E0 | 5.5E0 | 5.4E0 | 2.1E0 | 2.5E0 | 1.3E0 | 2.6E0 | 1.2E1 | 1.2E1 | 152 | 22 | 152 | 22 | 0.46 |
| bF | pg/mL | 3.4E1 | 5.5E1 | 3.3E2 | 3.9E2 | 1.4E3 | 1.3E3 | 5.0E-2 | 1.1E1 | 1.1E4 | 6.3E3 | 152 | 22 | 152 | 22 | 0.60 |
| bG | ng/mL | 1.6E0 | 1.7E0 | 3.0E0 | 4.3E0 | 4.0E0 | 6.9E0 | 1.1E-1 | 1.6E-1 | 2.6E1 | 3.0E1 | 152 | 22 | 152 | 22 | 0.51 |
| bH | pg/mL | 5.7E-1 | 5.7E-1 | 6.6E0 | 4.6E0 | 2.5E1 | 6.5E0 | 5.7E-1 | 5.7E-1 | 2.8E2 | 2.3E1 | 152 | 22 | 152 | 22 | 0.51 |
| bI | ng/mL | 4.0E-3 | 4.0E-3 | 9.1E-2 | 1.1E-1 | 1.8E-1 | 2.7E-1 | 4.0E-3 | 4.0E-3 | 8.8E-1 | 9.8E-1 | 152 | 22 | 152 | 22 | 0.49 |
| bJ | mg/mL | 1.9E0 | 2.0E0 | 2.4E0 | 2.4E0 | 2.0E0 | 2.1E0 | 2.5E-4 | 2.5E-4 | 1.1E1 | 8.9E0 | 152 | 22 | 152 | 22 | 0.51 |
| bL | pg/mL | 3.7E0 | 5.6E0 | 9.5E0 | 7.9E0 | 1.2E1 | 7.1E0 | 4.6E-2 | 4.6E-2 | 6.0E1 | 2.4E1 | 152 | 22 | 152 | 22 | 0.54 |
| bM | mg/mL | 1.8E0 | 1.9E0 | 2.1E0 | 2.2E0 | 1.4E0 | 1.9E0 | 1.8E-2 | 1.6E-2 | 7.9E0 | 8.6E0 | 152 | 22 | 152 | 22 | 0.50 |
| bN | ng/mL | 3.4E1 | 2.6E1 | 1.3E2 | 5.7E1 | 3.0E2 | 7.4E1 | 1.4E-1 | 1.4E-1 | 1.9E3 | 2.7E2 | 152 | 22 | 152 | 22 | 0.44 |
| bO | ng/mL | 4.0E-2 | 4.0E-2 | 9.7E0 | 5.5E0 | 1.9E1 | 2.5E1 | 4.0E-2 | 4.0E-2 | 1.3E2 | 1.2E2 | 152 | 22 | 152 | 22 | 0.36 |
| bP | mg/mL | 5.2E-1 | 5.1E-1 | 7.4E-1 | 7.6E-1 | 7.1E-1 | 6.9E-1 | 4.9E-2 | 9.2E-2 | 4.8E0 | 2.7E0 | 152 | 22 | 152 | 22 | 0.51 |
| bQ | pg/mL | 2.1E1 | 3.1E1 | 1.5E2 | 6.1E1 | 1.1E3 | 5.7E1 | 1.5E-1 | 8.1E0 | 1.3E4 | 1.9E2 | 152 | 22 | 152 | 22 | 0.63 |
| bR | ng/mL | 1.2E-2 | 1.2E-2 | 1.7E-1 | 7.1E-2 | 7.6E-1 | 1.2E-1 | 1.2E-2 | 1.2E-2 | 8.7E0 | 3.8E-1 | 152 | 22 | 152 | 22 | 0.44 |
| bS | pg/mL | 9.4E-1 | 9.4E-1 | 9.8E0 | 8.2E0 | 4.3E1 | 2.0E1 | 9.4E-1 | 9.4E-1 | 3.9E2 | 7.2E1 | 152 | 22 | 152 | 22 | 0.51 |
| bU | ng/mL | 7.0E-2 | 1.5E-1 | 2.0E-1 | 1.3E-1 | 5.7E-1 | 1.2E-1 | 1.3E-2 | 1.3E-2 | 6.6E0 | 4.1E-1 | 152 | 22 | 152 | 22 | 0.49 |
| bV | pg/mL | 4.7E2 | 6.5E2 | 6.1E2 | 7.8E2 | 9.3E2 | 4.9E2 | 1.6E2 | 3.4E2 | 1.2E4 | 2.2E3 | 152 | 22 | 152 | 22 | 0.69 |
| bW | pg/mL | 3.2E2 | 3.3E2 | 4.8E2 | 7.3E2 | 5.2E2 | 1.1E3 | 8.4E1 | 1.1E2 | 4.8E3 | 3.9E3 | 152 | 22 | 152 | 22 | 0.52 |
| bX | ng/mL | 7.0E-4 | 2.5E-5 | 2.7E-3 | 2.3E-3 | 3.2E-3 | 2.8E-3 | 2.5E-5 | 2.5E-5 | 1.3E-2 | 7.2E-3 | 152 | 22 | 152 | 22 | 0.48 |
| bZ | pg/mL | 2.7E2 | 7.2E2 | 1.8E3 | 3.3E3 | 6.8E3 | 9.0E3 | 1.5E-1 | 1.5E1 | 5.8E4 | 4.3E4 | 152 | 22 | 152 | 22 | 0.61 |
| cA | pg/mL | 6.0E-1 | 6.0E-1 | 4.4E0 | 1.8E0 | 3.0E1 | 4.5E0 | 6.0E-1 | 6.0E-1 | 3.7E2 | 2.1E1 | 152 | 22 | 152 | 22 | 0.48 |
| cB | ng/mL | 5.3E-2 | 2.9E-2 | 7.9E-2 | 4.6E-2 | 9.0E-2 | 6.5E-2 | 1.7E-3 | 1.7E-3 | 4.3E-1 | 2.6E-1 | 152 | 22 | 152 | 22 | 0.37 |
| cC | pg/mL | 4.4E1 | 3.6E1 | 4.7E1 | 3.2E1 | 5.2E1 | 2.5E1 | 1.0E0 | 1.0E0 | 4.5E2 | 7.7E1 | 152 | 22 | 152 | 22 | 0.41 |
| cD | pg/mL | 4.9E0 | 5.4E0 | 1.3E1 | 5.9E0 | 4.8E1 | 6.1E0 | 3.3E-1 | 3.3E-1 | 4.8E2 | 2.3E1 | 152 | 22 | 152 | 22 | 0.48 |
| cE | pg/mL | 5.6E1 | 7.9E1 | 2.8E2 | 1.7E2 | 6.3E2 | 2.7E2 | 1.2E-1 | 6.1E0 | 3.8E3 | 1.3E3 | 152 | 22 | 152 | 22 | 0.57 |
| cF | pg/mL | 9.4E0 | 5.3E-1 | 1.7E1 | 5.9E0 | 3.1E1 | 1.0E1 | 5.3E-1 | 5.3E-1 | 2.7E2 | 3.8E1 | 152 | 22 | 152 | 22 | 0.36 |
| cG | pg/mL | 5.3E1 | 1.2E2 | 1.7E2 | 1.9E2 | 8.5E2 | 2.3E2 | 7.8E0 | 2.4E1 | 1.0E4 | 1.1E3 | 152 | 22 | 152 | 22 | 0.67 |
| cH | uIU/mL | 3.2E0 | 5.0E0 | 6.8E0 | 1.4E1 | 1.5E1 | 2.7E1 | 8.6E-3 | 8.6E-3 | 1.6E2 | 1.2E2 | 152 | 22 | 152 | 22 | 0.53 |
| cI | pg/mL | 6.0E0 | 6.7E0 | 1.5E1 | 9.2E0 | 2.2E1 | 1.1E1 | 3.2E-2 | 2.3E-1 | 1.2E2 | 4.1E1 | 152 | 22 | 152 | 22 | 0.45 |
| cJ | ug/mL | 6.7E1 | 3.7E1 | 1.0E2 | 7.7E1 | 1.0E2 | 8.8E1 | 6.9E0 | 5.6E0 | 6.4E2 | 3.4E2 | 152 | 22 | 152 | 22 | 0.41 |
| cK | ng/mL | 3.8E-3 | 3.8E-3 | 2.4E-2 | 1.5E-2 | 1.2E-1 | 4.4E-2 | 3.8E-3 | 3.8E-3 | 1.5E0 | 2.1E-1 | 152 | 22 | 152 | 22 | 0.49 |
| cL | pg/mL | 2.1E2 | 2.2E2 | 5.0E2 | 8.2E2 | 2.0E3 | 1.6E3 | 3.1E1 | 6.7E1 | 2.4E4 | 7.4E3 | 152 | 22 | 152 | 22 | 0.58 |
| cM | pg/mL | 2.7E2 | 2.8E2 | 2.9E2 | 2.7E2 | 1.7E2 | 9.1E1 | 2.5E1 | 1.2E2 | 1.1E3 | 4.4E2 | 152 | 22 | 152 | 22 | 0.50 |
| cN | pg/mL | 1.2E2 | 1.3E2 | 1.3E2 | 1.4E2 | 9.0E1 | 3.3E1 | 3.8E1 | 8.6E1 | 1.1E3 | 2.1E2 | 152 | 22 | 152 | 22 | 0.61 |
| cO | pg/mL | 2.1E2 | 2.5E2 | 4.2E2 | 3.5E2 | 1.6E3 | 3.2E2 | 5.4E1 | 8.2E1 | 1.9E4 | 1.5E3 | 152 | 22 | 152 | 22 | 0.55 |
| cP | ng/mL | 2.4E3 | 2.8E3 | 2.5E3 | 2.8E3 | 9.4E2 | 1.0E3 | 6.2E2 | 1.4E3 | 5.6E3 | 4.7E3 | 152 | 22 | 152 | 22 | 0.57 |
| cQ | ng/mL | 5.0E-2 | 1.0E-1 | 1.3E-1 | 1.4E-1 | 2.2E-1 | 1.5E-1 | 2.0E-3 | 2.0E-3 | 1.3E0 | 4.8E-1 | 152 | 22 | 152 | 22 | 0.58 |

Figure 40 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cR | ng/mL | 3.4E2 | 3.5E2 | 6.1E2 | 5.4E2 | 8.6E2 | 5.9E2 | 2.0E1 | 8.9E1 | 7.7E3 | 2.2E3 | 152 | 22 | 152 | 22 | 0.49 |
| cS | ng/mL | 2.7E2 | 3.3E2 | 4.1E2 | 9.6E2 | 4.3E2 | 1.6E3 | 4.1E1 | 1.2E2 | 2.5E3 | 7.1E3 | 152 | 22 | 152 | 22 | 0.64 |
| cT | ng/mL | 4.9E1 | 1.2E2 | 1.4E2 | 3.3E2 | 2.7E2 | 4.7E2 | 3.6E0 | 1.4E1 | 2.1E3 | 1.5E3 | 152 | 22 | 152 | 22 | 0.64 |
| cU | ng/mL | 5.6E1 | 1.5E2 | 9.1E1 | 1.6E2 | 1.5E2 | 9.3E1 | 6.2E0 | 1.8E1 | 1.6E3 | 3.9E2 | 152 | 22 | 152 | 22 | 0.77 |
| cV | ng/mL | 2.1E-1 | 1.8E-1 | 7.3E-1 | 7.8E-1 | 3.9E0 | 2.1E0 | 2.5E-2 | 3.4E-2 | 4.7E1 | 9.7E0 | 152 | 22 | 152 | 22 | 0.48 |
| cW | mIU/mL | 4.8E-2 | 5.2E-2 | 9.1E-2 | 8.0E-2 | 3.6E-1 | 6.4E-2 | 4.8E-3 | 2.2E-2 | 4.5E0 | 2.9E-1 | 152 | 22 | 152 | 22 | 0.59 |
| cX | ng/mL | 1.1E-1 | 1.1E-1 | 1.7E0 | 2.9E0 | 5.2E0 | 8.2E0 | 2.3E-4 | 9.1E-3 | 2.8E1 | 2.8E1 | 152 | 22 | 152 | 22 | 0.52 |
| cY | ng/mL | 7.5E0 | 6.5E0 | 1.1E1 | 8.2E0 | 1.1E1 | 7.9E0 | 1.7E-1 | 6.0E-1 | 6.1E1 | 3.6E1 | 152 | 22 | 152 | 22 | 0.44 |
| cZ | ug/mL | 1.3E1 | 1.2E1 | 1.5E1 | 1.4E1 | 6.8E0 | 6.9E0 | 2.3E0 | 6.2E0 | 4.6E1 | 3.0E1 | 152 | 22 | 152 | 22 | 0.45 |
| dA | pg/mL | 3.2E2 | 3.0E2 | 3.9E2 | 3.8E2 | 4.8E2 | 1.9E2 | 1.0E2 | 1.7E2 | 5.8E3 | 8.8E2 | 152 | 22 | 152 | 22 | 0.51 |
| dB | ng/mL | 1.8E1 | 2.1E1 | 1.8E1 | 1.9E1 | 2.1E1 | 7.8E0 | 2.1E0 | 2.9E0 | 2.5E2 | 2.9E1 | 152 | 22 | 152 | 22 | 0.60 |
| dC | nmol/L | 3.4E1 | 3.0E1 | 3.7E1 | 3.6E1 | 1.7E1 | 1.7E1 | 7.8E0 | 1.5E1 | 1.4E2 | 9.1E1 | 152 | 22 | 152 | 22 | 0.44 |
| dD | ug/mL | 3.4E1 | 2.9E1 | 3.6E1 | 3.2E1 | 1.1E1 | 8.8E0 | 1.4E1 | 2.0E1 | 7.4E1 | 5.2E1 | 152 | 22 | 152 | 22 | 0.40 |
| dE | ng/mL | 4.7E-1 | 3.8E-1 | 5.6E-1 | 6.4E-1 | 5.6E-1 | 7.7E-1 | 8.4E-3 | 8.4E-3 | 2.7E0 | 2.9E0 | 152 | 22 | 152 | 22 | 0.50 |
| dF | ng/mL | 2.4E2 | 3.5E2 | 3.3E2 | 4.6E2 | 2.4E2 | 2.8E2 | 7.5E1 | 1.3E2 | 1.3E3 | 1.2E3 | 152 | 22 | 152 | 22 | 0.67 |
| dG | ng/mL | 1.1E1 | 1.5E1 | 1.7E1 | 1.9E1 | 1.9E1 | 1.3E1 | 3.0E0 | 6.7E0 | 1.8E2 | 6.5E1 | 152 | 22 | 152 | 22 | 0.62 |
| dH | pg/mL | 8.0E0 | 8.7E0 | 2.2E1 | 1.3E1 | 6.6E1 | 1.6E1 | 4.0E-2 | 8.3E-1 | 6.7E2 | 7.6E1 | 152 | 22 | 152 | 22 | 0.53 |
| dI | pg/mL | 4.6E-1 | 4.6E-1 | 4.0E0 | 2.4E0 | 2.7E1 | 4.5E0 | 4.6E-1 | 4.6E-1 | 3.3E2 | 1.9E1 | 152 | 22 | 152 | 22 | 0.50 |
| dJ | ng/mL | 2.0E0 | 1.8E0 | 2.2E0 | 2.0E0 | 1.1E0 | 1.1E0 | 3.2E-1 | 3.7E-1 | 5.6E0 | 4.5E0 | 152 | 22 | 152 | 22 | 0.44 |
| dK | uIU/mL | 1.4E0 | 8.1E-1 | 2.2E0 | 1.6E0 | 3.7E0 | 1.9E0 | 2.8E-4 | 1.4E-2 | 3.9E1 | 7.3E0 | 152 | 22 | 152 | 22 | 0.41 |
| dL | ng/mL | 8.7E2 | 1.2E3 | 1.0E3 | 1.2E3 | 6.5E2 | 4.5E2 | 2.8E2 | 5.8E2 | 4.8E3 | 2.3E3 | 152 | 22 | 152 | 22 | 0.63 |
| dM | pg/mL | 9.6E2 | 1.2E3 | 1.3E3 | 1.8E3 | 1.5E3 | 1.4E3 | 3.7E2 | 5.2E2 | 1.5E4 | 5.8E3 | 152 | 22 | 152 | 22 | 0.61 |
| dN | ug/mL | 9.8E1 | 1.1E2 | 1.0E2 | 1.1E2 | 4.5E1 | 3.1E1 | 2.4E1 | 6.4E1 | 3.3E2 | 1.7E2 | 152 | 22 | 152 | 22 | 0.59 |
| dR | pg/ml | 1.5E3 | 9.3E2 | 2.1E3 | 1.4E3 | 2.1E3 | 1.4E3 | 1.4E2 | 1.3E2 | 9.8E3 | 5.5E3 | 114 | 17 | 114 | 17 | 0.39 |
| dU | pg/ml | 8.5E3 | 1.3E4 | 1.6E4 | 1.3E4 | 1.8E4 | 1.1E4 | 6.9E2 | 1.7E3 | 8.1E4 | 3.5E4 | 25 | 8 | 25 | 8 | 0.49 |
| dX | ng/ml | 8.1E-2 | 8.2E-2 | 1.3E-1 | 1.2E-1 | 2.0E-1 | 1.3E-1 | 2.6E-3 | 2.6E-3 | 1.2E0 | 4.2E-1 | 51 | 10 | 51 | 10 | 0.53 |
| eF | ng/ml | 4.1E0 | 4.7E0 | 5.2E0 | 6.6E0 | 4.5E0 | 6.2E0 | 2.0E0 | 2.0E0 | 4.6E1 | 2.9E1 | 114 | 17 | 114 | 17 | 0.60 |
| eC | pg/ml | 3.0E2 | 2.7E2 | 3.7E2 | 3.1E2 | 3.1E2 | 1.9E2 | 9.9E0 | 1.1E2 | 2.0E3 | 7.3E2 | 101 | 14 | 101 | 14 | 0.44 |
| eD | pg/ml | 2.2E2 | 4.9E2 | 5.8E2 | 2.0E3 | 1.4E3 | 2.5E3 | 5.2E-1 | 8.3E1 | 8.3E3 | 7.0E3 | 84 | 9 | 84 | 9 | 0.70 |
| eM | ng/ml | 2.7E0 | 3.2E0 | 4.8E0 | 5.8E0 | 5.6E0 | 1.0E1 | 6.9E-1 | 7.6E-1 | 2.7E1 | 3.9E1 | 66 | 13 | 66 | 13 | 0.51 |
| eP | ng/ml | 3.7E-3 | 3.7E-3 | 1.1E0 | 1.5E0 | 4.1E0 | 3.2E0 | 3.7E-3 | 3.7E-3 | 2.8E1 | 1.0E1 | 51 | 10 | 51 | 10 | 0.53 |
| eQ | pg/ml | 1.0E0 | 1.0E0 | 5.5E1 | 4.7E1 | 1.1E2 | 8.8E1 | 1.0E0 | 1.0E0 | 4.7E2 | 2.2E2 | 25 | 8 | 25 | 8 | 0.47 |
| fA | ng/ml | 1.9E2 | 2.4E2 | 4.0E2 | 5.6E2 | 4.7E2 | 5.0E2 | 3.9E1 | 7.5E1 | 1.5E3 | 1.3E3 | 24 | 7 | 24 | 7 | 0.63 |
| fB | ng/ml | 5.7E2 | 6.3E2 | 6.6E2 | 6.4E2 | 2.8E2 | 2.2E2 | 2.6E2 | 3.5E2 | 1.3E3 | 9.2E2 | 23 | 8 | 23 | 8 | 0.50 |
| fP | ng/ml | 2.7E2 | 2.7E2 | 3.3E2 | 2.7E2 | 1.9E2 | 1.4E2 | 3.7E1 | 1.8E0 | 1.0E3 | 5.6E2 | 109 | 16 | 109 | 16 | 0.44 |
| fR | ng/ml | 1.4E5 | 2.2E5 | 2.1E5 | 2.7E5 | 1.8E5 | 2.1E5 | 3.6E4 | 1.9E2 | 6.9E5 | 8.7E5 | 97 | 18 | 97 | 18 | 0.61 |
| gC | ng/ml | 2.3E2 | 2.8E2 | 2.6E2 | 2.9E2 | 1.1E2 | 1.6E2 | 8.3E1 | 9.7E1 | 6.4E2 | 5.9E2 | 38 | 9 | 38 | 9 | 0.57 |
| gL | pg/ml | 6.5E4 | 6.6E4 | 7.2E4 | 8.7E4 | 3.4E4 | 5.1E4 | 1.1E4 | 2.7E4 | 1.9E5 | 2.2E5 | 114 | 17 | 114 | 17 | 0.57 |
| gP | U/ml | 2.7E2 | 2.8E2 | 2.9E2 | 2.9E2 | 1.3E2 | 9.2E1 | 1.2E1 | 6.5E1 | 1.1E3 | 4.4E2 | 113 | 17 | 113 | 17 | 0.57 |
| gW | ng/ml | 5.4E2 | 5.5E2 | 9.6E2 | 5.7E2 | 1.1E3 | 2.5E2 | 2.3E0 | 2.6E2 | 6.1E3 | 9.6E2 | 89 | 8 | 89 | 8 | 0.49 |
| gV | ng/ml | 1.9E1 | 2.2E1 | 2.0E1 | 2.6E1 | 7.4E0 | 5.5E0 | 8.1E-2 | 2.1E1 | 3.7E1 | 3.4E1 | 31 | 7 | 31 | 7 | 0.72 |
| tF | pg/mL | 1.0E3 | 5.3E3 | 9.5E3 | 3.0E4 | 3.4E4 | 6.5E4 | 1.2E1 | 1.8E1 | 2.8E5 | 2.5E5 | 102 | 15 | 102 | 15 | 0.71 |
| gZ | ug/ml | 7.0E-1 | 1.2E0 | 4.2E1 | 3.7E1 | 1.2E2 | 8.3E1 | 8.7E-2 | 1.4E-1 | 4.1E2 | 2.4E2 | 25 | 8 | 25 | 8 | 0.60 |
| hA | ng/ml | 2.3E0 | 5.4E0 | 1.4E1 | 1.7E1 | 5.2E1 | 3.4E1 | 1.7E-2 | 1.8E0 | 3.5E2 | 1.1E2 | 84 | 10 | 84 | 10 | 0.75 |
| nM | pg/ml | 1.0E-9 | 1.0E-9 | 1.0E-9 | 1.2E2 | 0.0E0 | 4.2E2 | 1.0E-9 | 1.0E-9 | 1.0E-9 | 1.5E3 | 61 | 13 | 61 | 13 | 0.54 |
| nN | pg/ml | 1.3E3 | 2.4E3 | 2.5E3 | 2.5E4 | 3.3E3 | 4.8E4 | 8.1E1 | 5.7E2 | 2.1E4 | 1.5E5 | 61 | 13 | 61 | 13 | 0.66 |
| nO | pg/ml | 2.4E1 | 4.3E1 | 3.7E1 | 4.3E1 | 4.8E1 | 3.6E1 | 4.0E0 | 9.7E0 | 3.1E2 | 1.5E2 | 61 | 13 | 61 | 13 | 0.64 |
| nR | pg/ml | 1.5E1 | 6.0E1 | 4.1E1 | 3.2E2 | 6.7E1 | 5.5E2 | 1.0E0 | 3.5E0 | 3.1E2 | 1.9E3 | 61 | 13 | 61 | 13 | 0.79 |
| nT | pg/ml | 7.2E1 | 1.1E2 | 9.7E1 | 2.2E2 | 9.0E1 | 2.7E2 | 1.0E-9 | 2.7E1 | 4.9E2 | 9.2E2 | 61 | 13 | 61 | 13 | 0.65 |
| nU | pg/ml | 3.9E1 | 8.9E1 | 6.2E1 | 3.0E2 | 1.1E2 | 4.4E2 | 1.0E-9 | 1.0E-9 | 7.5E2 | 1.5E3 | 61 | 13 | 61 | 13 | 0.69 |
| lW | pg/ml | 1.0E-9 | 1.0E-9 | 1.1E1 | 1.2E1 | 3.1E1 | 2.2E1 | 1.0E-9 | 1.0E-9 | 1.7E2 | 7.0E1 | 61 | 13 | 61 | 13 | 0.57 |
| lX | pg/ml | 9.0E2 | 9.2E2 | 9.9E2 | 1.0E3 | 5.8E2 | 5.7E2 | 1.9E2 | 4.8E2 | 2.6E3 | 2.5E3 | 61 | 13 | 61 | 13 | 0.54 |
| lY | pg/ml | 2.0E1 | 1.2E1 | 2.1E1 | 1.6E1 | 1.8E1 | 1.4E1 | 1.0E-9 | 1.0E-9 | 1.2E2 | 4.5E1 | 61 | 13 | 61 | 13 | 0.39 |
| mE | pg/ml | 1.0E-9 | 1.0E-9 | 2.8E0 | 1.4E0 | 8.1E0 | 3.1E0 | 1.0E-9 | 1.0E-9 | 5.7E1 | 9.2E0 | 61 | 13 | 61 | 13 | 0.42 |
| mF | pg/ml | 2.7E-1 | 7.1E-1 | 7.4E0 | 2.8E0 | 3.4E1 | 4.5E0 | 1.0E-9 | 1.0E-9 | 2.5E2 | 1.3E1 | 61 | 13 | 61 | 13 | 0.57 |
| mH | pg/ml | 3.1E0 | 3.3E0 | 5.2E0 | 6.6E0 | 7.7E0 | 9.1E0 | 4.0E-1 | 8.3E-1 | 5.3E1 | 3.2E1 | 61 | 13 | 61 | 13 | 0.51 |
| mI | pg/ml | 1.0E-9 | 3.4E0 | 1.2E1 | 5.2E1 | 2.6E1 | 1.3E2 | 1.0E-9 | 1.0E-9 | 1.8E2 | 4.6E2 | 61 | 13 | 61 | 13 | 0.56 |

Figure 40 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| mM | pg/ml | 2.8E1 | 5.9E1 | 6.5E1 | 1.6E2 | 8.9E1 | 3.1E2 | 1.0E-9 | 1.0E-9 | 4.0E2 | 1.1E3 | 61 | 13 | 61 | 13 | 0.58 |
| mP | pg/ml | 1.5E1 | 1.6E1 | 1.6E1 | 9.6E1 | 1.0E1 | 2.2E2 | 1.0E-9 | 8.2E0 | 5.8E1 | 8.1E2 | 60 | 13 | 60 | 13 | 0.61 |
| mS | pg/ml | 1.5E3 | 1.8E3 | 1.7E3 | 1.9E3 | 9.7E2 | 1.2E3 | 1.0E-9 | 1.0E-9 | 5.1E3 | 4.2E3 | 61 | 13 | 61 | 13 | 0.57 |
| mT | pg/ml | 5.7E1 | 4.5E1 | 1.1E2 | 3.3E2 | 2.1E2 | 5.4E2 | 1.0E1 | 1.6E1 | 1.4E3 | 1.7E3 | 60 | 13 | 60 | 13 | 0.52 |
| mU | pg/ml | 2.2E0 | 3.5E0 | 3.0E0 | 2.2E1 | 2.6E0 | 6.1E1 | 1.0E-9 | 1.5E0 | 1.6E1 | 2.2E2 | 60 | 13 | 60 | 13 | 0.65 |
| mW | pg/ml | 2.2E3 | 1.8E3 | 2.4E3 | 3.0E3 | 1.2E3 | 3.0E3 | 1.0E-9 | 3.7E2 | 6.2E3 | 1.1E4 | 60 | 13 | 60 | 13 | 0.46 |
| mY | pg/ml | 6.5E2 | 7.3E2 | 8.7E2 | 1.4E3 | 9.9E2 | 2.1E3 | 1.0E-9 | 7.5E1 | 5.6E3 | 8.0E3 | 61 | 13 | 61 | 13 | 0.60 |
| mZ | pg/ml | 1.5E2 | 3.0E2 | 3.4E2 | 4.3E2 | 4.9E2 | 3.4E2 | 1.0E-9 | 3.9E1 | 3.1E3 | 1.1E3 | 60 | 13 | 60 | 13 | 0.64 |
| nA | pg/ml | 1.5E0 | 2.7E0 | 7.3E0 | 5.9E0 | 1.5E1 | 1.2E1 | 1.0E-9 | 1.0E-9 | 6.5E1 | 4.3E1 | 60 | 13 | 60 | 13 | 0.49 |
| nB | pg/ml | 2.8E2 | 3.0E2 | 3.0E2 | 3.7E2 | 1.5E2 | 2.5E2 | 3.0E1 | 1.3E2 | 6.9E2 | 9.6E2 | 61 | 13 | 61 | 13 | 0.56 |
| nC | pg/ml | 1.0E-9 | 8.3E1 | 1.1E4 | 9.1E2 | 5.6E4 | 1.7E3 | 1.0E-9 | 1.0E-9 | 3.8E5 | 6.1E3 | 61 | 13 | 61 | 13 | 0.60 |
| nD | pg/ml | 6.9E0 | 9.2E0 | 1.4E1 | 1.3E1 | 3.6E1 | 1.3E1 | 1.0E-9 | 1.0E-9 | 2.6E2 | 3.7E1 | 60 | 13 | 60 | 13 | 0.56 |
| nF | pg/ml | 1.0E-9 | 1.0E-9 | 3.6E0 | 1.0E0 | 1.4E1 | 3.7E0 | 1.0E-9 | 1.0E-9 | 9.3E1 | 1.3E1 | 61 | 13 | 61 | 13 | 0.48 |
| nH | pg/ml | 5.6E-1 | 4.2E0 | 2.2E2 | 1.2E1 | 1.3E3 | 2.0E1 | 1.0E-9 | 1.0E-9 | 1.0E4 | 6.9E1 | 60 | 13 | 60 | 13 | 0.61 |
| nI | pg/ml | 3.0E1 | 1.0E-9 | 7.9E1 | 1.8E1 | 1.7E2 | 3.0E1 | 1.0E-9 | 1.0E-9 | 1.2E3 | 8.0E1 | 61 | 13 | 61 | 13 | 0.33 |
| nJ | pg/ml | 1.7E-1 | 6.3E-1 | 3.2E0 | 1.6E0 | 1.7E1 | 2.2E0 | 1.0E-9 | 1.0E-9 | 1.3E2 | 7.0E0 | 61 | 13 | 61 | 13 | 0.55 |
| nK | pg/ml | 1.0E-9 | 1.0E-9 | 1.7E1 | 1.2E1 | 3.6E1 | 2.1E1 | 1.0E-9 | 1.0E-9 | 2.2E2 | 6.2E1 | 60 | 13 | 60 | 13 | 0.48 |
| nL | pg/ml | 1.0E-9 | 2.5E0 | 3.3E2 | 3.8E1 | 1.8E3 | 7.1E1 | 1.0E-9 | 1.0E-9 | 1.4E4 | 2.3E2 | 61 | 13 | 61 | 13 | 0.55 |
| hR | pg/ml | 2.8E4 | 2.1E4 | 3.0E4 | 2.1E4 | 1.2E4 | 3.7E3 | 1.0E-9 | 1.7E4 | 5.8E4 | 2.7E4 | 78 | 9 | 78 | 9 | 0.23 |
| hV | pg/ml | 4.6E2 | 3.7E2 | 4.5E2 | 4.7E2 | 2.4E2 | 2.1E2 | 1.0E-9 | 2.3E2 | 1.2E3 | 8.8E2 | 78 | 9 | 78 | 9 | 0.53 |
| hW | pg/ml | 1.7E3 | 2.4E3 | 2.5E3 | 2.5E3 | 4.4E3 | 1.1E3 | 1.0E-9 | 1.3E3 | 4.0E4 | 4.7E3 | 78 | 9 | 78 | 9 | 0.64 |
| hX | pg/ml | 1.1E3 | 8.4E2 | 1.1E3 | 1.2E3 | 9.4E2 | 7.5E2 | 2.5E0 | 6.6E2 | 8.6E3 | 2.9E3 | 78 | 9 | 78 | 9 | 0.50 |
| iA | pg/ml | 1.7E2 | 1.3E2 | 2.6E2 | 2.1E2 | 2.9E2 | 1.9E2 | 1.5E1 | 2.3E1 | 1.8E3 | 5.5E2 | 101 | 16 | 101 | 16 | 0.45 |
| iB | ng/ml | 4.8E0 | 6.8E0 | 6.4E0 | 7.9E0 | 5.2E0 | 3.9E0 | 3.3E-2 | 2.5E0 | 2.4E1 | 1.5E1 | 84 | 10 | 84 | 10 | 0.68 |
| iC | U/ml | 3.0E-1 | 3.9E-1 | 1.3E0 | 4.8E-1 | 6.1E0 | 3.1E-1 | 1.0E-9 | 1.4E-1 | 5.5E1 | 1.1E0 | 84 | 10 | 84 | 10 | 0.60 |
| iH | ng/ml | 1.6E5 | 1.8E5 | 1.6E5 | 1.7E5 | 5.1E4 | 4.2E4 | 2.9E3 | 8.1E4 | 2.6E5 | 2.4E5 | 101 | 16 | 101 | 16 | 0.54 |
| iJ | ng/ml | 4.8E4 | 4.8E4 | 5.3E4 | 6.6E4 | 3.2E4 | 5.5E4 | 1.8E3 | 1.5E4 | 2.5E5 | 2.5E5 | 101 | 16 | 101 | 16 | 0.55 |
| hB | ng/ml | 4.8E-1 | 5.1E-1 | 6.3E-1 | 6.4E-1 | 5.3E-1 | 3.4E-1 | 1.2E-1 | 2.3E-1 | 3.2E0 | 1.2E0 | 101 | 16 | 101 | 16 | 0.55 |
| hC | pg/ml | 4.0E3 | 1.0E4 | 7.9E3 | 1.0E4 | 1.3E4 | 8.3E3 | 4.1E1 | 2.3E2 | 1.1E5 | 2.6E4 | 101 | 16 | 101 | 16 | 0.62 |
| hF | pg/ml | 1.0E-9 | 1.0E-9 | 4.0E1 | 1.0E-9 | 4.0E2 | 0.0E0 | 1.0E-9 | 1.0E-9 | 4.0E3 | 1.0E-9 | 101 | 16 | 101 | 16 | 0.50 |
| hG | pg/ml | 6.7E3 | 7.0E3 | 7.3E3 | 8.9E3 | 3.2E3 | 3.9E3 | 1.8E3 | 4.5E3 | 2.0E4 | 1.8E4 | 101 | 16 | 101 | 16 | 0.63 |
| iO | ng/ml | 3.8E5 | 4.6E5 | 4.1E5 | 4.7E5 | 2.0E5 | 1.8E5 | 1.1E4 | 1.0E5 | 1.1E6 | 7.7E5 | 101 | 16 | 101 | 16 | 0.62 |
| iP | ng/ml | 5.2E4 | 6.2E4 | 5.8E4 | 5.5E4 | 4.9E4 | 1.6E4 | 1.0E-9 | 2.5E4 | 4.4E5 | 7.0E4 | 101 | 16 | 101 | 16 | 0.54 |
| iZ | ng/ml | 1.7E3 | 2.1E3 | 1.8E3 | 2.0E3 | 8.8E2 | 8.0E2 | 6.6E2 | 8.4E2 | 5.7E3 | 3.4E3 | 98 | 17 | 98 | 17 | 0.60 |
| jB | ng/ml | 2.3E5 | 2.6E5 | 2.4E5 | 2.4E5 | 7.2E4 | 8.5E4 | 9.9E4 | 1.3E5 | 3.6E5 | 3.5E5 | 25 | 8 | 25 | 8 | 0.51 |
| rC | pg/ml | 1.6E3 | 1.2E3 | 2.2E3 | 2.4E3 | 2.2E3 | 3.4E3 | 1.0E-9 | 6.0E2 | 1.5E4 | 1.1E4 | 76 | 9 | 76 | 9 | 0.46 |
| rB | pg/ml | 3.1E1 | 9.2E1 | 4.8E1 | 9.6E1 | 6.4E1 | 9.6E1 | 1.0E-9 | 4.0E0 | 3.9E2 | 3.2E2 | 76 | 9 | 76 | 9 | 0.68 |
| jD | ng/ml | 2.7E1 | 5.8E1 | 3.8E1 | 8.8E1 | 4.0E1 | 8.5E1 | 1.0E-9 | 8.8E-1 | 1.9E2 | 2.9E2 | 84 | 10 | 84 | 10 | 0.74 |
| jE | ng/ml | 1.0E-9 | 4.1E0 | 5.1E0 | 9.9E0 | 1.2E1 | 1.2E1 | 1.0E-9 | 1.0E-9 | 6.2E1 | 2.9E1 | 84 | 10 | 84 | 10 | 0.64 |
| jF | ng/ml | 3.8E1 | 4.7E1 | 4.7E1 | 6.0E1 | 5.3E1 | 5.7E1 | 1.0E-9 | 1.0E-9 | 2.1E2 | 1.5E2 | 84 | 10 | 84 | 10 | 0.58 |
| jG | ng/ml | 4.2E3 | 4.8E3 | 4.4E3 | 5.1E3 | 2.0E3 | 1.7E3 | 6.7E2 | 3.6E3 | 9.6E3 | 9.5E3 | 84 | 10 | 84 | 10 | 0.61 |
| jH | ng/ml | 7.5E1 | 1.2E2 | 8.1E1 | 1.2E2 | 5.2E1 | 8.0E1 | 1.3E1 | 1.5E1 | 4.3E2 | 2.4E2 | 84 | 10 | 84 | 10 | 0.65 |
| jI | ng/ml | 7.3E1 | 1.3E2 | 7.8E1 | 1.2E2 | 4.9E1 | 6.1E1 | 1.9E1 | 5.2E1 | 4.4E2 | 2.6E2 | 84 | 10 | 84 | 10 | 0.77 |
| rA | pg/ml | 2.4E1 | 2.8E1 | 3.0E1 | 3.3E1 | 2.8E1 | 2.1E1 | 1.0E-9 | 1.2E1 | 2.0E2 | 7.1E1 | 82 | 10 | 82 | 10 | 0.59 |
| qZ | pg/ml | 4.8E1 | 2.8E1 | 4.5E2 | 1.5E3 | 1.8E3 | 3.8E3 | 2.8E-4 | 3.2E-3 | 1.0E4 | 1.0E4 | 61 | 7 | 61 | 7 | 0.45 |
| qY | pg/ml | 1.5E1 | 2.2E1 | 3.8E1 | 3.9E1 | 5.7E1 | 5.1E1 | 8.7E-1 | 5.6E0 | 3.3E2 | 1.8E2 | 82 | 10 | 82 | 10 | 0.56 |
| qX | pg/ml | 6.0E1 | 6.9E1 | 7.0E1 | 8.6E1 | 4.9E1 | 5.3E1 | 1.0E-9 | 3.6E1 | 2.3E2 | 2.1E2 | 82 | 10 | 82 | 10 | 0.60 |
| qW | pg/ml | 7.7E0 | 7.7E0 | 1.2E1 | 8.1E0 | 1.6E1 | 6.6E0 | 1.0E-9 | 1.0E-9 | 1.2E2 | 2.1E1 | 82 | 10 | 82 | 10 | 0.45 |
| qV | pg/ml | 1.7E3 | 2.4E3 | 2.5E3 | 2.5E3 | 2.0E3 | 1.8E3 | 1.7E2 | 1.0E2 | 1.1E4 | 5.6E3 | 82 | 10 | 82 | 10 | 0.52 |
| qU | pg/ml | 7.7E1 | 1.3E2 | 1.9E2 | 2.5E2 | 3.1E2 | 3.3E2 | 1.0E-9 | 1.0E-9 | 2.1E3 | 1.1E3 | 82 | 10 | 82 | 10 | 0.59 |
| qT | pg/ml | 3.9E1 | 4.8E1 | 6.4E1 | 8.2E1 | 7.1E1 | 7.8E1 | 1.0E-9 | 2.2E1 | 4.9E2 | 2.6E2 | 82 | 10 | 82 | 10 | 0.57 |
| jK | ng/ml | 1.5E3 | 1.3E3 | 1.6E3 | 1.8E3 | 5.7E2 | 1.1E3 | 2.8E2 | 7.0E2 | 3.6E3 | 4.1E3 | 84 | 10 | 84 | 10 | 0.48 |
| jL | ng/ml | 1.9E2 | 2.6E2 | 2.6E2 | 3.3E2 | 2.0E2 | 2.1E2 | 5.6E1 | 1.3E2 | 9.6E2 | 7.0E2 | 84 | 10 | 84 | 10 | 0.63 |
| jM | ng/ml | 6.7E4 | 8.4E4 | 7.4E4 | 7.8E4 | 4.0E4 | 3.9E4 | 4.6E3 | 1.4E4 | 1.8E5 | 1.4E5 | 84 | 10 | 84 | 10 | 0.55 |
| jO | pg/ml | 2.1E5 | 3.3E5 | 2.6E5 | 3.8E5 | 1.7E5 | 1.3E5 | 6.0E4 | 2.6E5 | 1.1E6 | 6.5E5 | 84 | 10 | 84 | 10 | 0.76 |
| jP | pg/ml | 2.5E5 | 4.3E5 | 2.7E5 | 4.1E5 | 1.4E5 | 1.4E5 | 3.6E4 | 2.2E5 | 7.1E5 | 5.8E5 | 84 | 10 | 84 | 10 | 0.78 |
| jQ | pg/ml | 2.2E3 | 2.3E3 | 3.1E3 | 3.4E3 | 3.0E3 | 2.6E3 | 5.0E0 | 8.4E2 | 1.3E4 | 9.2E3 | 84 | 10 | 84 | 10 | 0.57 |

Figure 40 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jR | pg/ml | 5.5E3 | 9.2E3 | 1.0E4 | 1.3E4 | 1.2E4 | 1.3E4 | 1.0E-9 | 1.6E3 | 6.8E4 | 4.6E4 | 84 | 10 | 84 | 10 | 0.59 |
| jT | pg/ml | 1.7E5 | 2.1E5 | 1.7E5 | 2.1E5 | 7.1E4 | 7.0E4 | 7.1E4 | 1.2E5 | 5.5E5 | 3.5E5 | 84 | 10 | 84 | 10 | 0.66 |
| jU | mIU/ml | 5.9E0 | 5.1E0 | 1.2E1 | 1.2E1 | 1.9E1 | 1.6E1 | 8.1E-2 | 5.3E-1 | 1.1E2 | 5.3E1 | 84 | 10 | 84 | 10 | 0.47 |
| jV | mIU/ml | 2.3E0 | 1.0E0 | 4.3E0 | 2.6E0 | 5.8E0 | 3.4E0 | 2.7E-3 | 2.1E-2 | 3.2E1 | 1.0E1 | 84 | 10 | 84 | 10 | 0.38 |
| jY | ng/ml | 9.5E-4 | 2.3E-3 | 8.0E-3 | 5.7E-3 | 3.4E-2 | 9.0E-3 | 1.0E-9 | 1.0E-9 | 3.0E-1 | 2.6E-2 | 84 | 10 | 84 | 10 | 0.57 |
| kC | pg/ml | 9.6E1 | 1.2E2 | 1.9E2 | 2.0E2 | 3.8E2 | 1.8E2 | 2.1E1 | 3.6E1 | 2.7E3 | 5.9E2 | 61 | 13 | 61 | 13 | 0.59 |
| kE | pg/ml | 1.4E5 | 1.5E5 | 1.4E5 | 1.6E5 | 3.8E4 | 4.2E4 | 3.8E4 | 1.2E5 | 2.3E5 | 2.7E5 | 61 | 13 | 61 | 13 | 0.64 |
| kF | pg/mL | 6.1E1 | 8.2E1 | 6.5E1 | 8.7E1 | 2.3E1 | 3.0E1 | 2.7E1 | 5.2E1 | 1.5E2 | 1.4E2 | 61 | 13 | 61 | 13 | 0.74 |
| kG | pg/mL | 7.6E3 | 1.3E4 | 1.0E4 | 3.1E4 | 9.7E3 | 4.2E4 | 1.1E3 | 3.3E3 | 5.8E4 | 1.6E5 | 61 | 13 | 61 | 13 | 0.73 |
| kI | pg/ml | 1.9E2 | 2.1E2 | 2.2E2 | 2.2E2 | 1.1E2 | 1.2E2 | 4.4E1 | 1.0E-9 | 6.7E2 | 4.6E2 | 61 | 13 | 61 | 13 | 0.53 |
| kK | pg/ml | 1.2E2 | 1.1E2 | 1.6E2 | 1.8E2 | 1.5E2 | 1.4E2 | 6.4E0 | 3.4E1 | 9.1E2 | 4.9E2 | 61 | 13 | 61 | 13 | 0.57 |
| kN | pg/ml | 1.0E3 | 1.4E3 | 1.4E3 | 2.3E3 | 1.5E3 | 2.5E3 | 2.1E2 | 5.8E2 | 1.0E4 | 8.7E3 | 61 | 13 | 61 | 13 | 0.63 |
| kO | pg/ml | 7.1E3 | 7.7E3 | 1.0E4 | 7.6E3 | 1.8E4 | 1.9E3 | 3.8E3 | 4.9E3 | 1.5E5 | 1.2E4 | 61 | 13 | 61 | 13 | 0.54 |
| kP | pg/ml | 6.1E3 | 5.4E3 | 7.0E3 | 5.9E3 | 4.4E3 | 3.6E3 | 1.5E3 | 9.6E2 | 2.7E4 | 1.5E4 | 61 | 13 | 61 | 13 | 0.44 |
| kQ | pg/ml | 4.2E3 | 5.4E3 | 5.3E3 | 5.7E3 | 4.3E3 | 2.7E3 | 5.6E2 | 1.5E3 | 2.5E4 | 1.2E4 | 101 | 16 | 101 | 16 | 0.60 |
| kR | pg/ml | 2.2E1 | 2.6E1 | 3.8E1 | 2.8E1 | 1.0E2 | 1.8E1 | 1.0E-9 | 2.9E0 | 1.0E3 | 6.8E1 | 101 | 16 | 101 | 16 | 0.52 |
| kS | pg/ml | 8.7E2 | 9.2E2 | 9.9E2 | 9.2E2 | 5.9E2 | 5.4E2 | 2.5E2 | 8.2E1 | 3.2E3 | 2.5E3 | 101 | 16 | 101 | 16 | 0.50 |
| rZ | ng/ml | 1.4E-3 | 1.4E-2 | 9.6E-3 | 3.0E-2 | 3.6E-2 | 3.8E-2 | 1.0E-9 | 1.0E-9 | 3.0E-1 | 1.1E-1 | 77 | 9 | 77 | 9 | 0.79 |
| rY | ng/ml | 6.4E-2 | 4.7E-2 | 4.1E-1 | 2.3E0 | 2.1E0 | 6.7E0 | 1.0E-9 | 2.8E-2 | 1.8E1 | 2.0E1 | 77 | 9 | 77 | 9 | 0.52 |
| rX | ng/ml | 1.0E-9 | 1.0E-9 | 1.0E-1 | 3.6E-1 | 5.1E-1 | 1.0E0 | 1.0E-9 | 1.0E-9 | 3.7E0 | 3.1E0 | 77 | 9 | 77 | 9 | 0.52 |
| lK | pg/ml | 5.9E1 | 9.3E1 | 1.4E2 | 1.8E2 | 1.7E2 | 1.9E2 | 1.0E-9 | 1.0E-9 | 7.4E2 | 5.1E2 | 83 | 10 | 83 | 10 | 0.55 |
| lL | pg/ml | 1.6E3 | 4.1E3 | 2.4E3 | 7.9E3 | 2.6E3 | 1.2E4 | 7.5E1 | 6.9E2 | 1.9E4 | 4.2E4 | 84 | 10 | 84 | 10 | 0.77 |
| lM | pg/ml | 1.2E3 | 8.6E2 | 3.6E3 | 1.1E4 | 6.0E3 | 2.1E4 | 2.1E2 | 9.5E0 | 4.2E4 | 6.7E4 | 84 | 10 | 84 | 10 | 0.45 |
| lN | pg/ml | 1.0E-9 | 4.7E0 | 2.9E0 | 8.4E0 | 6.5E0 | 8.3E0 | 1.0E-9 | 1.0E-9 | 4.3E1 | 2.4E1 | 84 | 10 | 84 | 10 | 0.75 |
| lO | pg/ml | 1.0E-9 | 1.0E-9 | 3.6E0 | 1.0E-9 | 2.1E1 | 0.0E0 | 1.0E-9 | 1.0E-9 | 1.4E2 | 1.0E-9 | 83 | 10 | 83 | 10 | 0.48 |
| nW | pg/ml | 1.1E5 | 1.2E5 | 1.1E5 | 1.2E5 | 2.9E4 | 2.2E4 | 3.6E4 | 8.4E4 | 1.9E5 | 1.5E5 | 101 | 16 | 101 | 16 | 0.60 |
| nY | pg/ml | 2.2E3 | 3.6E3 | 2.6E3 | 3.3E3 | 1.6E3 | 1.6E3 | 5.1E2 | 1.2E3 | 1.0E4 | 7.1E3 | 101 | 16 | 101 | 16 | 0.64 |
| oO | pg/ml | 9.1E4 | 5.5E4 | 1.0E5 | 9.8E4 | 6.2E4 | 1.0E5 | 3.3E3 | 3.1E4 | 3.0E5 | 4.0E5 | 55 | 12 | 55 | 12 | 0.36 |
| oP | pg/ml | 1.2E5 | 1.7E5 | 1.3E5 | 2.0E5 | 7.5E4 | 1.5E5 | 2.4E4 | 5.0E4 | 4.2E5 | 5.7E5 | 55 | 12 | 55 | 12 | 0.66 |
| oQ | pg/ml | 2.9E3 | 3.2E3 | 3.3E3 | 7.4E3 | 2.0E3 | 9.4E3 | 7.7E2 | 1.4E3 | 1.1E4 | 3.2E4 | 55 | 12 | 55 | 12 | 0.59 |
| oE | pg/ml | 1.6E2 | 7.0E2 | 4.4E2 | 1.0E3 | 5.8E2 | 9.4E2 | 1.0E-9 | 8.9E1 | 2.8E3 | 3.4E3 | 101 | 16 | 101 | 16 | 0.77 |
| oF | pg/ml | 1.2E4 | 3.2E4 | 2.5E4 | 4.9E4 | 3.5E4 | 6.3E4 | 4.3E2 | 3.5E2 | 1.7E5 | 2.5E5 | 101 | 16 | 101 | 16 | 0.66 |
| oH | pg/ml | 3.6E1 | 3.0E1 | 7.9E1 | 6.9E1 | 1.2E2 | 1.0E2 | 4.3E-1 | 6.3E0 | 8.6E2 | 3.2E2 | 101 | 16 | 101 | 16 | 0.46 |
| oK | pg/ml | 8.4E2 | 9.8E2 | 1.6E3 | 1.6E3 | 1.9E3 | 1.6E3 | 8.8E1 | 2.1E2 | 1.2E4 | 5.9E3 | 101 | 16 | 101 | 16 | 0.54 |
| oN | pg/ml | 5.4E2 | 5.7E2 | 9.8E2 | 7.3E2 | 2.0E3 | 4.4E2 | 1.1E2 | 2.8E2 | 1.8E4 | 1.8E3 | 101 | 16 | 101 | 16 | 0.56 |
| oW | pg/ml | 2.1E2 | 2.9E2 | 3.9E2 | 1.4E3 | 5.2E2 | 2.6E3 | 2.9E1 | 9.3E1 | 2.7E3 | 7.6E3 | 25 | 8 | 25 | 8 | 0.60 |
| oT | pg/ml | 3.0E2 | 2.4E2 | 3.6E2 | 2.2E2 | 1.9E2 | 7.0E1 | 1.0E2 | 1.1E2 | 7.9E2 | 3.2E2 | 25 | 8 | 25 | 8 | 0.23 |
| oV | pg/ml | 1.3E2 | 8.4E1 | 3.2E2 | 1.1E2 | 5.1E2 | 1.1E2 | 1.1E1 | 1.0E-9 | 2.2E3 | 3.3E2 | 25 | 8 | 25 | 8 | 0.39 |
| oD | pg/ml | 1.5E4 | 1.7E4 | 1.5E4 | 1.7E4 | 5.3E3 | 7.7E3 | 6.6E3 | 9.3E3 | 2.5E4 | 3.2E4 | 25 | 8 | 25 | 8 | 0.57 |
| pF | pg/ml | 5.7E-1 | 7.2E-1 | 1.7E0 | 7.1E-1 | 8.6E0 | 4.8E-1 | 1.0E-9 | 4.3E-2 | 8.7E1 | 1.6E0 | 101 | 16 | 101 | 16 | 0.50 |
| pH | ng/ml | 7.6E0 | 1.1E1 | 8.7E0 | 1.3E1 | 4.0E0 | 7.4E0 | 1.2E0 | 3.0E0 | 1.8E1 | 2.3E1 | 25 | 8 | 25 | 8 | 0.64 |
| pI | ng/ml | 6.9E1 | 7.5E1 | 7.4E1 | 7.0E1 | 4.8E1 | 2.7E1 | 2.3E1 | 3.5E1 | 2.0E2 | 1.1E2 | 25 | 8 | 25 | 8 | 0.54 |
| pK | ng/ml | 4.8E-1 | 4.0E-1 | 4.8E-1 | 3.9E-1 | 2.1E-1 | 1.3E-1 | 2.0E-1 | 1.7E-1 | 8.6E-1 | 6.2E-1 | 25 | 8 | 25 | 8 | 0.41 |

Analyte panel data:

Unconstrained panels with 3 analytes, where 1.0E-10 >= 'model p-value' > 0. Contains 5 panels of 23,517,221 total panels evaluated. : Tn{Ss(eM nR nT nU) JjeM}

Unconstrained panels with 3 analytes, where 1.0E-9 >= 'model p-value' > 1.0E-10. Contains 13 panels of 23,517,221 total panels evaluated. : Tn{Al(kI mS) Kl(mW nl) JonT} IN{Tz(Ax Cs) dKhR} Cu{ApYj YgaZ} IdUhIL JlJuoO KjVvnU Unconstrained panels with 3 analytes, where 1.0E-8 >= 'model p-value' > 1.0E-9. Contains 74 panels of 23,517,221 total panels evaluated. : oO{Tn(Ad Al Ao Ap Bb Cv Dd Dg Dl Iz Ke Kg Kj Kl Ks Ok Pj) Kq(Iz Jo Ju Kg Nm Of Pz Ss Ug Vo) Jv(oE oF)} Cu{Yj(Ad Dg Gb Jt Nn Oi Ok Rz Ux Vj Vw) Yi(Dg Jo Kg Kj Kl Mh Nb)} Nn{Iv(Jj Jo Li Ng) Ng(Nt On) MbOk NjaA QdLi OnOy} Tn{oP(Al Hb Ke Kq Ks) Ss(mP nN) oQ(Al Ii) AdnU} Ii{On(eP Yf) IsfR} AwIsdX MbMxaA MuOnOy JuaUlX Unconstrained panels with 3 analytes, where 1.0E-7 >= 'model p-value' > 1.0E-8. Contains 614 panels of 23,517,221 total panels evaluated. : Nn{Iv(aA Hq Hr Ii Im In Iq Is Iu Jh Ji Jl Jm Jt Lh Lj Lu Lv Ma Mb Me Mg Mh Mi Mm Mu Mv Mw Mx My Nd Nf Nj Nk Nl Ns Nt Nu Nx Oe Of Og Oi Ok Oy Pb Pg Qd) Ng(Is Ji Jl Lv Me Nj Nl Nu Nv Nw Ok Pg Qd) Qd(Ik Il Im Jj Jm Jt Lj Lv Mb Me Nj) Nj(Im Is Jj Lv Mx Nd Ok Oy) Me(Is Jh Jj Mv Mx Ok Oy) Jj(Is Lv Nl Nt Nx Pg) Ma(gZ jB oT oV oW) Lv(aA Nl Of Oy) Mb(aA Is Ji Jl) Ok(Jh Of Om Pb) Cu(oW Yi) Li(Is

Ji(Hr Hv Hw Ij In Jn Jo Jq Jr Li Ma Na Nf Nj Nu Ny Of Om) On(Hr Ii Jh Jj Jo Li Ma Mw My Nb Nf Nj Nl Nu Om Pb) Mb(Im Jj Jl Lh Lj Lw Ma Mi Mp Nd Nu Nv Oh Pc Pg) Nj(Im Jj Jl Ma Mi Mp Nd Nw Oh Pc Pg) Jj(Ik Ma Nl Nu Nx Pg) Pg(Ii Jo Li Ng Of) Ma(lm Jo Nl Nu) Nw(Of Oy Pb) MgNg MiHq LdeP hRIN} Kq{Uw(kC kE kF kG kI kK kN kO kP lW lX lY mE mF mH ml mM mP mS mT mU mW mY mZ nA nB nC nD nF nH nI nJ nK nL nM nN nO nR nT nU) Ux(kC kE kF kG kI kK kN kO kP lW lX lY mE mF mH ml mM mP mS mT mU mW mY mZ nA nB nC nD nF nH nI nJ nK nL nM nN nO nR nT nU) Gb(kC kE kF kG kI kK kN kO kP lW lY mE mF mH ml mM mP mS mT mU mW mZ nA nB nC nD nH nI nJ nL nN nO nR nT nU Yi Yj Yk) Yi(kC kG kI kN kO kP lW lX mE mF mM mT mU mW mY nA nB nC ND nH nL nN nR) Vb(kC kF kG kI kN kO kP lW lX lY mE mF mM mT mU mW mZ nA nC nH nN nO nR) oO(Ad Cv Dc Gd Jj Jk Jv Kj Ks Mm Ng Ok Pj Qv Rc) Nm(eM kG kO kP lX mF mH mM mT mU mY nC nH nJ) mE(Ad Al Iz Jj Mm Uy) eP(aO Gd Ik Iz Jp) mT(Rt Uy Va We Yf) kG(dU Hp Nd Yg Zq) nI(Ad Ap Dl) Mm(eM nH) Qe(dU oT) Uy(mF nL) dX(Gd Vo) lY(Al Iz) YgnU ZqmM LioT VamH VwnJ} Ma{Vb(kC kE kF kG kI kK kN kO kP lW lX lY mE mF mH mI mM mP mS mT mU mW mY mZ nA nB nC nD nF nH nI nJ nK nL nM nN nO nR nT nU) Jo(kC kE kF kG kI kK kN kO kP lW lX lY mF mH mI mS mT mW mY mZ nA nB nC nD nF nH nI nJ nK nL nM nO nT) Rt(kC kG kK kP lY mF mH mP mW mZ nA nC nH nJ nL nN nT nU) Of(kE kI mE mM mP mS mU nI nN nR nT nU On oQ) Jt(kG kI kP mE mP mS mU nI nN nR nU) mH(Ad Dg Ps Sf Uw Ux Uy Va Vw Wd Yi) Ny(dU eQ fB gZ jB oD oV oW pH) Ux(kE kI kP lX mP mS mZ nJ nO) oO(Ad Al cF Dd Gd Pj Wb Yd) Jj(kP mM mP mU nN nR nU) aA(Lv Mb Nk Nl Nt Pg) mE(Ad Bb Dg Hr Mm Nf) oV(Fr Hb Js Mm Nm Qh) kI(Gb Nm Uw Uy Yi) nJ(Ad Dg Gb Gd) Nm(kP mU nN) Mm(kP mU nN) kE(Gb Hl Uy) oQ(Dr Li Yd) Fr(mU nN) Mj(kG lY) Va(kC mY) aZ(bS cA) fB(Ar Qe) nI(Ad Dg) NdUm NgOn HlmT QzpK LigZ UymS VwmP} aA{Mb(Et Fp Fr Hq Hr Hv Ih Ij Ik Il Im Io Ip Ir It Jh Jj Jk Jl Jn Jp Jq Js Jt Lh Li Lj Lu Lw Lx Ly Mc Me Mf Mg Mh Mi Mk Ml Mm Mp Mq Ms Mt Mu Mz Na Nb Nc Ne Ng Nj Nk Nl Nm No Nq Nr Ns Nt Nu Nw Nx Og Oh Oi Pa Pc Pe Po Qa Qb) Nj(Et Fp Hr Hv Hw Ih Ij Il Im In Ip Jh Ji Jj Jk Jl Jp Jq Lh Li Lj Lu Lw Lx Ly Lz Mc Mf Mg Mh Mi Mk Mm Mp Ms Mt Nb Ne Ng Nl Nq Ns Nt Nu Nv Nw Nx Of Og Oh Ok On Pa Pb Pc Pe Po Qa) Lv(fR Hq Hr Hv Hw Ii Ij Ik Il Im In Jj Jo Lh Li Lj Lu Md Mf Mg Mh Mj Mk Mu Mw Na Nb Nc Nd Ne Nf Ng Nk Nl Ns Nt Nu Nw Nx Ny Of Oh Om Pb Pg Po Qb Qc) Pg(Hq Hr Jj Jo Lh Li Ng Nl Of) Nt(Hq Hr Jj Jo Li Ng Nk Of) Ji(Hr Hw Om Pb) Mu(Me Ng Nl) Po(Hr Li) Ok(Hr Pb) cU(dH fR) MeMf MzPb OfOn eCoO} kG{Mj(Fr Hp Hr Ii Jj Jk Jt Lh Li lY Mh Mm Mn mW Nb Nm Ns Nv Ny Oe Of Oz Pb Pc Si Uw Ux Uy Vb Yg Yi Zq) dU(Ef Ez Gp Hc Ib Iz Jd Je Jf Ke Kg Kj Kl Kr Qg Qn Qu Rc Ss To Tz Ua Uf Uk Up Ut Uu Vs Vv) Hp(aH Dc Dk Hq Jl Jn Jq Jr Js Ke Ld Nv Nw Ny Oh Om Ou Pf Pg Ps Rm St Tz Ut Vi) Vb(AO bZ Ez Hq Hr Jg Kf Kl Mg Mv mW Mz Nd Nv Om On Op Pg Qt Ut Uu Vv) Yg(Dk Hq Jq Jr Js Ld Nv Nw Om Ou Pf Pg Tz) Yi(Dk Jq Jr Js Ke Ld Lh Nw Ou Pf Pg Tz) Hq(Eq Lp Rz Sh Ux Wd Wf Wh Yk Ye Xa) Uw(Dk Jq Jr Js Lh Nw Ou Pf Tz Ut) Nd(Dp Fn Gp Jd Or Ou Tz Ut) Tz(fP Oe Pb Pc Si) Gb(bW Jr Ps Yd) Gp(aU lW Wd Wh) Si(Jq Jr Ld Pf) Rt(aO Vp Vv) Oh(Li Mb oO) Yj(aF Th) Zq(Jq Jr) Rv(nL Ri) Ux(On Pg) Pf(Pb Pc) IbVi IcaU InYh ShUp KeLi KsPs RzNv OucR oOoQ} On{Of(Hu Ij Ik Iq Iu Jh Ji Jj Jk Jl Jm Jo Jt Lh Li Lu Me Mf Mg Mh Mj Mk Ml Mw My Mz Nb Nc Nd Ne Ng Nh Ni Nk Nl No Nq Ns Nv Nx Oe Oi Ok Oy Pe Pg Po Pz Qa Qb Qc) Mb(Hq Ii Jg Jh Ji Jo Li Lu Lv Ly Mi Ml Mv Mw Nd Nk Nl Nu Og Oi Ok Om Po) Ng(Hr Hu Hw Ii Ik Jk Li Lj Lv Mf Mg Nf Nj Nk Nl Nq Ns Nt Nu Nx Om Pb Pg) Oy(Ii Ik Jk Jt Li Lj Lv Nj Nk Nl Ns Nu Pg) Vb(kF kP lX mI mP mT nH nK nL nN nU) dX(Fy Ii Jj Ks Lv Mm Ug Vo) eP(Ad cU Jj Jo Lv Mm Ug Vo) Ux(mI mP mT nH nK nL nN) Nj(Jj Jo My Om Pb) Yj(Bb Jg Oh Ok Rc) Yi(Ii nB Nd Oh) Pb(Jj Lv Mu Qa) fR(cU Jj Jo Mm) Yg(aZ bG cF) Ad(Gb Ry) Vw(nH nL) EmMm NtJo MuMy NlJj HlRc UtoT} Ut{Hp(kC kE kF kK kN kO kP lW lX lY mE mF mH mM mS mY nB nC nI nJ nN nO nR nT nU) Wb(kK kN lW lX mE mF mM mS mY nC nI nJ nL nT nU) Sh(kO lW mF mI mS nB nC nI nJ nL nN nO nT nU) Al(dU eQ gC gZ jB oD oT oV oW pH pI pK) mE(Gb Ii Rt Rz Si Uw Ux Uy Va Vb Yd) mF(Gb Rt Rz Si Ur Uw Ux Uy Va Vb) Nv(kF kK lY oT oV pI) nJ(Gn Hl Lp Op Wf Ye) Gb(kI kO lX mY nN) nU(Gn Hl Lp Wf Ye) Mm(lX oT oW pI) Iz(dX mH mM nI) kF(Ii Rz Ux Vb) Ur(eP nI oO) kO(Hl Lp Si) pI(Kf Nm Of) Ii(nT oW) Jj(dU eM) Uw(mM mY) oO(Ju Nx) BbmW ChYj GnnT WemY QweP JpdX JveQ LioT LplW UykC UxmM aOdU} Vb{bZ(kC kE kF kI kK kN kO kP lW lX lY mE mF mH mI mM mP mS mT mU mW mY mZ nA nB nC nD nF nH nI nJ nK nL nM nN nO nR nT nU) Rz(kC kF kI kN lW mE mF mI mM mT mW mY mZ nA nB nC nD nH nJ nO nR nT nU) Ez(kE kI kK kO kP lX lY mH mP mS mT mU mW mY nA nB nI nJ nN nO nR nU) Mg(kF kK kO kP lW mF mP mT mU mW mZ nB nC nD nH nI nL nR nU) Mz(kF mI mP nK nN nT nU) mW(cS Mt Ow Vw) Vv(kP lW nR) nC(Ji Lh) nK(aO bF) kF(Co Vi) GpmE OwmH VwmZ cTnU} Vv{oT(Al Bb Hb Ii Io Jd Jh Jm Jq Ju Jv Kf Ks Lh Mm Mn Ms Nm Nv Ny Oe Oh Rc Uv) Lp(kC kE kI kP mF mH mI mS nA nI nJ nO) oW(Al Co Ii Iz Jm Jq Kn Mm Nv Oh Pz Uu) Al(dU eQ gC gZ jB oD oV pH pI pK) Ii(jB oE oQ oV pI pK) Jq(jB oD oV pH) nU(Aj Hl Ug Ur) Nv(jB oV pH) Jo(oE Vu) kP(Rt Ux) oV(Jk Uu) AxoE BbpH DdoO MmgC JjnR JmjB VakC VopI} bZ{Yi(kC kE kI kN kP lW lY mE mF mH mI mS mU nA nI nJ nK nT) Uw(kC kE kI kP mE mF mH mI mS nA nI nJ nT) nI(Gb Ps Ux Uy Va Vw We Yg Zq) mI(Gb Ux Uy Va Yg Zq) Gb(kK mE mF mZ) Rt(lY mT mW nU) mH(Ps Ux Uy Vw) oO(Gc Gd Ju Jv) Zq(kE kI nJ) Ny(fA fB pH) mE(Ux Vw Yd) Yg(nJ nT) Uy(lX nJ) mT(Hl Rv) oV(Ef Fa) QefB UxmP} Gp{Wd(kC kE kK kN kO kP lW lX lY mE mH mI mT mZ nA nC nH nJ nK nN nT) Wh(kE kF kI kK kN kO lW lY mE mH mI mZ nA nB nC nD nJ nK nN) Gd(Hx Mz Nw oF Oh Sf Yh Yi Yj) Ps(lW mE mH nA nJ) Uw(lW mE nA) mH(Vi Yi) AxOh YfnA GbNw SfmI ZqkK KylN UxmE} Tz{Si(Co Ez Kc Li Mm Mu Nq Ow Vu Zq) Qv(Ax cF Hb Jv Li Nd Ns Um) Li(cF lN Mu Qy Uf Um) nU(Gn Hl Lp Sf Sh Uy) Gb(Ao Co Kc Pd Vu) cF(Ax Hb Jv lN Ry) oE(Ax Hb Ns Pc) lN(Id Js Oa) Ax(Oh Rf) Nd(Lp Um) Hp(fR nR) Ib(Eq Ho) Hb(Kc Um) IdlL RznJ RxmS LdeP NvoW} eP{Ld(Ax aZ Cq Dc Ed Fw Ha Hq Hv Ij Il Iq Ir It Jl Js Kd Kr Lx Mi Mj Mr Na No Nr Ny Oh Pi Po Qe Qh Tv Un Up Vp Vu) Fy(Ji Ke Mn Nw Qc) Ji(bA bV cT Mm) Uf(Aj Ij Ou Ph) bA(Aw Mi Nq) Lv(cT Nt) AwLx AxPe MicT NahB KydR NwcU} Lp{Nd(aZ Ed kE kN mP mU mW nB nD nR Pg Vq) Uc(kN lW mT nH nI nJ nR nU) kN(Hq Hv Nb Rh Vu Wh Tj) Hq(kF mE mY nC nL) mT(Jh Qa Qu Qz Vu) nI(aO Aw Lx oE Pg) Vu(lW nC nH) Pf(lW nN) aUlX cLkK gLlW} aZ{Aa(aO Ar aW bI bO cC cK cS Dc De dH Gc Jf Lh Li Mb Mg Ml Nw Ok) bS(Lu Lv Me Mm Mu Ne Ns) Hc(Gb Hp Sh Si Zq) Nb(Ax cF Li Mm) Gb(Ao Co Nt) Si(Ao Co Mg) cU(cE cF dH) Gd(De Mk) YhnC OgcF} Ji{Pb(Hx Jk Lv Mb Mu Nt Nu Ok Pg Qa) Mb(Jk Jl Li Lj Mu Nd Nu Nv) Om(Jk Lj Mu Nt Nu) nC(Ps Uw Ux Yi) Of(Jk Nt Nv) dX(bA cT Fy) Um(Hb Nd) AacF GbYl NtJo NgJk HwQa IdlL UymW} Gb{Jr(Ao Kc Mi MP mT nK nL nN nR Vu Yj Yl) Nw(cF cI Gh Hc Nd nI Ns Nt Pc Vz Yj) Nd(Lx Mi Pg) Ld(kE kI kN) Pg(Li nK) AoEd EzkE LxmY MzYj KcOh OunL PemH} oO{Ju(Ky nR oF Oh oN Ph) Jl(Ur Wb Yd Zx Ye) Jv(hB nR Oh oN) oF(Em fA fB Um) Lx(Gc Wb Zw) Qa(Al Dd) Oh(Qv Um) nR(aJ Mh) oQ(kE Ye) GnaO NsoE MjcF MzYd RfdD UmhB dNfR} Ok{Mb(Jk Jl Lj Mi Mp Mu Nk Nq Nu Nv Oh Pb Pc Pg) Of(Jk Lj Lv Nq Nv Pg) Mu(Jh Ng Om Pb) Rt(nH nI nU) Pb(Lv Mz Pg) Qa(Hw Om) NdRy JomP} Yi{Ld(kI nO nR nU tF) Lx(kF mW mZ Nd) Jr(aW Ho nN nR) Nd(Pe Po Rh) Ow(Hv mH mW) bQ(kE kI mH) Lh(Ii nC) Pe(mH mZ) Pf(kK mZ) mW(Mq Qa) ExnR HvOh cUlY} Uy{mW(Ke Lh Lx Mp Ou Ow Pf Po Qa) Ou(nA nC nD nH nL) Lh(mP nC nH nL) Nw(kN nR nU) Lx(lX nA) Jq(nT nU) mH(kF Ow) nI(cU Mz) MjmP NdPg aUlX} Qa{Al(dU eQ gZ jB mU nA nR oD oT oV oW pH pI pK) Hp(mH mW mY mZ) mW(Uw Ux Yg) Gn(nH nJ) Um(Ax Nd) MmeM JmnR LjfB NwPb} cU{fR(Ao bA cE cT Jn Jo Jr Lh Lv Lx Mm Nw) dH(Aa aJ aO cF cI cS cY) cB(Jo Lh) YglY SibR OyaU mZnI} Nw{Nt(Hq Ng Of Pb) Pb(Ik Li Nj) Mu(My Oy) Hb(Vz Yl) Jk(Ng Of) Uw(mY nJ) Va(kK nU) YfIi FydX MecF MmfR LjOf} Hl{Nd(Ed Ho Hv Ij Lx Pe) nR(bW cE cI cW kE) mW(aJ Lx Mk Ow Pf) nU(nJ Pg Vh Ti) cLkN} Hp{Vi(mI mP mT mU nH nK nL nR nT) Ps(kP lW mH mM mS mW) hC(mU nU) EdNd PgkF} Jj{Nt(Lv Mu Nd Nk Nx Pg) Pg(Ik Mb Nj Nu) fR(Jr Mj Nq) mE(Mu Qu) MbJl NbnR} lN{hR(aG aO aS bW cB cJ jO Mf Mu Nq)

Figure 40 Continued

Nq(Hq Of Om Oy) Ky(Ko Rc) AxMj} Oh{Wm(Jo Li Lj Mm Mu Nd Ns) Ax(nU oE tF) Li(Qy Ra) Um(Lj Nd) DedX MmeM} pH{To(cJ iO kN Lv Mk Ni Pc) Pb(Qt Qx Ra Uf Wm) Ld(Jv Ql) Uf(Mm Oz)} oV{aO(Gl Hb Ib Rc Vt) Ef(cT kF oN Pc) Ez(Jk Li) AlUf EmaF JubF NycT} Lx{Nd(Du Ru Yl) nJ(Rt We Wh) Li(mP nN) kF(Yg Zq) FydX WhnU UwmW} Lh{nC(Ps Rt Uw Ux Va) nH(Rt Ux Va Wf) nJ(Va Vh Vw) UwkF} Ow{Ax(eQ fA gC gZ jB oT pl) mW(Ps Uw Ux) mH(Uw Va) LjpI} Ez{fB(Ar Cs Li Ny) mH(Uw Ux Va Vw) Ny(gC oT) RtmW YlOr} Zq{Jr(mM mW nO) kE(bF bQ dF) Pf(kK mZ) aF(nI nU) GdNd bQkI} dX{Fy(aN Ke Li Mk Mn Mp) Lv(Aw cT Nt) NqbA MnKf StOu} Ld{Yg(nR nU) Yl(kS Or) dU(Ax Co) oT(Jv lW) SfmH RxkN aUjB} lX{aU(Bb Gh Sf Ug Um Va) Yh(Qv Ug) RxbF VaaQ} Nt{Ng(Jk Lv Nq) Jo(Jl Lv Pg) Mz(Nf Pb) MiHq} Rt{aO(mT nH nK nN nU) Mz(nA nI) PfnJ bFnL} Pg{Sh(nC nD nH nL nR) GnnU MiHq MuNg} oE{Ns(cR Fa Je Jf Nd) Ax(Ed Oa) JfPc} Id{lM(Bo Ed Ly Me) lL(Ml Or Qb)} Jr{Uw(nN nR) AlnR lbWg SiVu WdnJ WfnU} Mz{nI(Ux Va) AdcF NqNf NjPb} Jv{oT(Fw Mg Pc) PcoW bUpK} Uw{Pf(kK mZ) GdmW JqnJ PemH} nL{Rv(Lv Ri) Ou(Sf Va) WbVi} kF{Mj(nI Ny) FbNq MmNb UxPf} Yh{Qv(kE mH) Ug(kE mY)} Mm{eM(Ke Qe) UfpK} Nd{Um(Hx Mi) RxkK} Yg{bQ(kE kI mH)} Va{Ou(nA nH) JqnJ} Vi{nJ(Jq Kx) WbnH} eD{Nq(Jm Om) dIlL} gV{Dc(bB dD) BabG} rZ{Mf(jU jV) LijD} Em{aF(oD oW)} Gd{TinC UfnB} Hq{MbMi ZxoP} Wh{UxnR bBnC} Rv{MtmT RinN} Yl{Or(De Kg)} Ny{FyoT cToW} Pc{ExjB UfpK} GhdRkP LvJocF MeaWIL MjWfnH MuNgNv SsRzmH RxbFkE LjPecM UmnUmE

Unconstrained panels with 3 analytes, where 1.0E-5 >= 'model p-value' > 1.0E-6. Contains 27,674 panels of 23,517,221 total panels evaluated. : Is{Yi(AA aC aD aE AF aG aH aI aJ aK aL aM aN Ao aP aQ aR AS aU aV AW aX aY aZ bA BB bC bE bF bG bH bI bJ bL bM Bn bP bQ bR bU bV bW bX bZ cA cB cE cF cG cH cI cJ cK cL cM cN CO cP cQ cR cS CT CV cW CX cY cZ dA DB DC DD DE dF dG dH dI DK dL dM dN Dp Du Ed Ef eM Eq Et Ez Fc Fi Fr Fw Fy Gh Gl Gp Gz HC Hl Ho Hq Hr Hu Hv Hw Ib Ih Ii Ij Ik Io Iq Ir It Iu Iv Jh Jo Jq Jr Jt kF Kg Ki KK Kn Ko Kq Kr Ks Kx Ld Lh Li Lj Lp Lx Ma Md Me Mg Mh Mi Mk Ml Mm Mp Mq Ms Mt Mu Mv mY Mz Na Nb NC Nd Ng NH Ni Nj nL NN nO Nq Ns Nt Nu Nv Nw Ny Oe Og Oi Ok Om On oO oP Or Ou Oy Oz Pb Pc Pd Pg Ph Pj Po Qb Qc Qn Rc Rx Rz Uo Va Vv Vz Wb Yh Yj Yl Tl Xa Tj tF) Ad(aA aC aD aE AF aG aH aI AJ aK aL aM AN AO AP aQ AR aS aV AW aX aY aZ BA BB BC bE bF bG bH bI bJ bL bM BN bO bP bQ bR bS bV bW bX bZ cC cD cE cG CH cI cJ cK cL cM cN CO cP cQ cR CS CT CU CV cW CX cY cZ dA DB DC dD dE dF DG dH DI dJ DK DL dM dN Et Fp FR Gb Hb Hq Hu Hx Ik Il Im Io Ip Iq Iu Iv Jg Jh Ji Jj Jk Jl Jp Jq Lv Lw Lx Ly Lz Mb Mc Md Mf Mg Mh Mi Mj Mk Ml Mn Mp Mq Ms Mt Mw Mx My Mz Na Nb Nc Nd Ne Ng Nh Ni Nj Nk Nl Nn No Nq Nr Nt Nu Nv Nw Nx Ny OE Of Og Oh Oi Ok Om On Oy Oz Pa Pc Pd Pe Pf Pg Po Ps Pz Qa Qb Qc Qd Qe Um Ux Uz Va Vb Vc Vh Vi Vw Vz Wb Wd We Wf Wg Yd Yg Yh Yk Zq Zw Zx Ye Tm Tl Xa) Dd(AA aC aD aE AF aG aH aI AJ aK AL aM AN AO AP aQ AR AS aU aV AW aX aY aZ BA bB BC bE bF BG bH bI bJ bL bM BN BO bP bQ bR bS bU bW bX bZ cA cB cC cD cE cG CH cI cJ cK cL cM cN CO CP CQ cR CS CT CU CV CW CX cY cZ dA DB DC dD dE dF DG dH DI dJ DK DL dM dN Et Fp Fr Gb Hb Hp Hq Hr Hv Hw Hx Ih Ij Ik Il Im In Io Ip Iq Ir It Iu Iv Jg Ji Jj Jk Jl Jn Jq Jr Lu Lv Lw Lx Ly Lz Ma Mb Mc Md Mf Mg Mh Mi Mj Mk Ml Mn Mp Mq Mr Ms Mt Mu Mv Mw Mx My Mz Na Nb Nc Nd Ne Nf Ng Nh Ni Nj Nk Nl No Nq Nr Nt Nu Nv Nw Nx Oe Of Og Oh Oi Ok Om On oO Oy Oz Pa Pb Pc Pd Pe Pf Pg Pz Qa Qb Qc Qd Qe Rx Yl) Aa(aC aD aE AF aG aH aI AJ aK aL aM AN Ao AP aQ Ar AW aY BA bB BC bE bF Bg bJ bL bM BN Bo bP bQ bW bX bZ cG CH cI cJ cL cM cN CO CP Cq cR CS CT Cu cV CW CX cY cZ DB DC dD dE dF Dg DI DK DL dM dN Ed Et Ex Fp Fr Hb Hr Hv Hw Hx Il Io Ip Ir It Jf Jg Jh Ji Jn Jp Jq Jr Kg Lh Li Lj Lw Lx Ly Lz Mc Md Mf Mi Mj Mk Ml Mm Mn Mp Mq Ms Mt Mu Mv Mx Mz Na Nf Ni Nm No Nv Nw Oh On Oz Pc Pd Pe Pf Po Rm Um) In(aA aD aE aF aG aH aI AJ aK aL aM AN AO aP aQ AR AS aU aV AW aX aY aZ BA bB BC bE bF BG bH bI bJ bL bM BN BO bP bQ bS bU bV bW bX bZ cA cB cC cD cE cG cH cI cJ cK cL cM cN CO CP CQ cR CS CT CU CV CW cX cY cZ dA dB DC dD dE dF dG dH DI dJ DK DL dM dN Em eP Gb Gd Iq Ji Jj Jm Ju Lv Mb Mi Mx Mz Nj Nn Ns Nt Nu Ok Ps Qa Qd Um Uw Ux Uy Va Vb Vh Vz Wc Wm) dX(aA aC aH aI aN AO aQ Ar As aU AX aY BA bC bE bF bG bI bJ Bn bQ bS bU bV bW bZ cC cD cE cG CH cI cK CO Cp Cq cS cT CU CV Cx cY dA DB dD De dF dH Di dJ dK dN EM eP Fr Fy Gd Ha Hr Hu Hv Ih Ij Ik Im Io Jf Jh Ji Jl Jo Jp Jr Ld Lh Li Lj Lu Lv Lx Ly Lz Ma Mb Mg Mh Mi Mk Ml Mp Mq Mt Mu Mv Mx Na Nd Ne Ni Nj Nl Nm Nn Nq Nt Nv Nw Ny Of Og Oh Ok Om On Oy Pc Pd Pe Pf Po Qd Rb Ub) Hr(aA aD aE AF aG aH aI AJ aK aL aM AN AO aP aQ Ar AS aU aV AW aX aY BA bB BC bE bF BG bH bI bJ bL bM BN BO bP bQ bS bU bW bX bZ cA cB cC cD cE cG CH cI cJ cK cL cM cN CO CP CQ cR CS CT Cu CV CW CX cY cZ dA DB DC dD dE dF dG dH DI dJ DK DL dM dN eP Iq Iv Ji Jj Jl Jm kG Lj Lv Mb Mx Nj Nn Nt Ok On Qv Rc Um Wm) Jt(aA aC aD aE aF aG aH aI AJ aK aL aM AN aO AP aQ aS aV AW aY aZ BA BB Bc bE bF bG bH bI bJ bL bM BN BO bP bQ bR bS bU bW bX bZ cA cC cD cE cG cH cI cJ cK cL cM cN CO CP cQ cR CS cT CU CV CW cX cY cZ dA DB DC dD dE dF DG dH DI dK DL dM dN eM Hb Hp Ji Jj Jm kF kG Lj Lv Mb Mi Mx Nj Nl nN Ns Nu Oh Ok On Pg Qd Qy Um Yj Wm) eP(aC aI aK aN aO aQ Ar As aU aW aX aY BA bC bF BN bQ bS bU bV bX bZ cA cC cD cE cG cH cK cN Co Cp CS CT CU CV Cx cY dA DB dD De dF dG dH Di dK dM dN EM Ha Hq Hu Hv Ih Ij Im Io Jf Jh Ji Jl Jn Jo Jp Jr Js Li Lj Lu Lv Lx Ly Lz Ma Mb Mf Mg Mh Mi Mk Ml Mn Mp Mq Mt Mu Mv Mx Na Nd Ne Nj Nl Nm Nn Nq Ns Nt Nv Nw Ny Oe Of Oh Ok Om On Oy Pc Pd Pe Pf Qd Rb Ub) Yl(aA aF aK Al aM aN aO Ap aS aV aZ bA Bb bC bF bI bJ bN bO bV cC cD cF cM Cq cS cU Cv cX Dc De Dg DL dN Dp Ef Eq Ez Fd Gh Gp Hl Hq Hv Ib Ic Id Ij Ik Im Ip Iq Ir Iu Iv Iz Jg Jj Jl Jo Jr Js Ke Kg Kl Kn Ko Kq Ks Ld Lh Li Lj Ma Mh Ml Mm Mn Mp Mw Na Nb Nd Ng Nh Nm Ns Nv Nw Ny Of Og Oh Oi Ok Om Op Or Ou Oy Pb Pc Pj Ps Qa Qb Qe Qh Qn Qt Rc Rx Ry Sr Uo Uw Uy Va Vo Zw) Jo(aA aD aE Af aG aH aI AJ aK aL aM aN Ao AP aQ Ar aS aV aY aZ BA bB Bc bE bF BG bH bJ bL bM bN bP bQ bX bZ cE cG CH cJ cK cM cN CO cP cQ cR CT cV cW CX cZ dA DB dC dD dE dF DG dH dI DK DL dM dN eM Hb Id Ik Iq Ji Jj Jl Jm Kg Kr Lj Lv Ma Mb Mh Mi Mx Nj Nk Nl Ns Nu Oh Ok On Pg Qd Qy Rm Uf Vt Vu Vv Yh Wm) Mb(aU aX aZ cC cF Cq Cs cU dJ Et Fp FR Hq Hu Hv Hw Hx Ih Ii Ij Ik Il Im Io Ip Iq Ir It Jg Jh Jk Jl Jn Jp Jq Jr Js kG Lh Lu Lv Lw Lx Ly Lz Ma Mc Md Me Mf Mg Mh Mj Mk Ml Mm Mn Mp Mq Mr Ms Mt Mu Mv Mw My Mz Na Nb Nc Ne Nf Ng Nh Ni Nj Nk Nl Nm No Nq Nr Nt Nv Nw Nx Ny Oe Of Og Oi Om Oy Oz Pa Pb Pc Pd Pe Pf Pg Po Pz Qa Qb Qc Qd Qe) Ii(aA aD aE Af aG aH aI AJ aL aM aN Ao aP aQ Ar Aw aY BA bB Bc bE bF BG bJ bL Bn Bo bP bQ bW bX bZ cG CH cJ cM cN CO cP Ct cV cW Cx cZ dA DB dC dD dE dF dG Di DK dL dM dN Em Fc Hb Hp Ik Iq Ji Jj Jl Jm kF kG Lh Lj Lv Ma Me Mh Mi mP Mu Nj Nk Nl nN nR Ns NU Nv Nw Nx oE Oh Ok On Po Qd Um Uy Yh Wm Yf) Ax(aC aE aH aJ aK aM aN aP AR aU aV aW aX aY aZ bA bC bH bL bM bN bO bP bR bS bU bV cA cB cC cE cH cI cK cL cM cQ cS Ct CV cY dB De dG dH dJ Dk dL dM dN Gp Hp Hx Ib Id Iq Je Jh Jj Kd Kn Ko Kp Lh Lu Lz Ma Md Me Mh Mj Mm Mq Mw Mz Nd Nm Nn Nr Ns Nw Nx oE Pa Pd Pi Pk Po Ra Rj Tv Uc Ud Ul Up Ur Us Vp Vs Vu Vv) Cq(aC aF Aj aK aO Ap aR aS aU aV aW aX aZ Bb BC bH bI BN BO bR bS bU bV cA cB cC cD cE cI cK cL Co cQ CS CU Cv cX cY Dc dE Dg dH DI dJ Dl fR Gb Hb Ih Ij Im Io Iq Iu Iv Jj Lh Lj Ly Ma Mh Mi Ml Mu Mv Mw Mz Nb Nd Ne Ng Nh Ni Nk Nl Nn Nu Nv Nw Nx Ny Oe Of Og Oh Oi Ok Oy Oz Pc Pz Qa Qb Qd Qe) Nn(An As Bo Cp CU Cw Dc Em Et Fp Fr Hq Hu Hv Hw Hx Ih Ij Ik Il Im Io Ip It Jg Ji Jk Jl Jn Jp Jq Jr kF kG Lp Lu Lw Lx LY Lz Ma Mc Md Mf Mg Mi Mj Mk Ml Mm Mn MP Mq Mr Mt Mz Na Nb Nc Nd Ne Nf Nh Ni Nm nN No Nq NR Nv Nw Nx Ny Oh Om On Oz Pa Pb Pc Pd Pe Pf Pg Po Qa Qb Qc Qe Ue Yh Wm) Mx(Et Fp Fr Hq Hu Hv Hw Hx Ih Ij Ik Il Im Io Ip It Iu Jg Jh Ji Jk Jl Jn Jp Jq kG Lh Lu Lw Lx Ly Lz Mc Md Mf Mg Mh Mi Mj Mk Ml Mm Mn Mp Mq Mr Ms Mt Mu Mv Mw My Na Nb Nc Nd Ne Nf Ng Nh Ni Nk Nl Nm Nq Nr Nu Nv

Mg Mh Mi Mj Mk Ml Mm Mn Mp Mq Mr Ms Mt Mu Mv Mz Na Nc Nd Ne Nh Ni Nk Nm No Nq Nr Ns Nt Nv Nw Nx Ny Oe Og Oh Oi Ok Oz
Pa Pc Pd Pe Pf Pg Po Pz Qa Qb Qc Qe) Nj(Et Fp Fr Hq Hr Hu Hv Hw Hx Ih Ii Ik Il In Ip Iq Ir It Iu Jg Jh Jk Jm Jn Jo Jp Jq Jr Js Jt Lh Li Lj Lu
Lw Lx Ly Lz Mc Md Mf Mg Mh Mj Mk Ml Mm Mq Mr Ms Mt Mu Mv Mw My Mz Na Nb Ne Nf Ng Nh Ni Nk Nl Nm No Nq Nr Ns Nu Nv
Nx Ny Oe Of Og Oi Om Oy Oz Pa Pb Pd Pe Po Qa Qb Qc Qe) aA(Et Fp Fr Hq Hu Hv Hx Ih Ii Ij Il Im Io Ip Iq It Iu Jg Jh Jj Jk Jl Jm Jo Jp Jq Jt
Lh Lu Lw Lx Ly Lz Mc Md Mi Mj Mk Ml Mm Mn Mp Mq Mr Ms Mt Mu Mv Mw My Mz Na Nb Nc Nd Ne Ng Nh Ni Nm No Nq Nr Ns Nv
Nw Ny Oe Og Oh Oi Om Oy Oz Pa Pc Pd Pe Pf Po Pz Qa Qb Qc Qe) Pg(Et Fp Hq Hr Hu Hv Hw Ih Ij Ik Il Im In Iq Ir It Iu Jh Ji Jk Jl Jm Jn Jp
Jr Js Jt Lh Lj Lu Lw Ly Lz Mc Md Mf Mg Mh Mi Ml Mm Mn Mp Mq Ms Mu Mw My Na Nb Nc Nd Ne Nf Ni Nk Nl Nm Nq Nr Ns Nt Nu Nv
Nw Nx Ny Oe Og Oh Oi Ok Om Oy Pa Pb Pc Pd Pe Pf Po Pz Qa Qb) Ok(Et Fp Fr Hq Hu Hx Ih Ii Ik Il Im Io Ip Iq It Iu Jg Jh Ji Jj Jk Jl Jm Jp Jt
Lh Lu Lw Lx Ly Lz Mc Md Mf Mg Mh Mi Mj Mk Ml Mm Mn Mp Mq Mr Ms Mt Mu Mv Mw My Mz Nb Nc Nd Ne Ng Nh Ni Nm No Nq Nr
Nv Nw Nx Oe Og Oh Oi Oy Oz Pa Pc Pe Pf Po Pz Qa Qb Qc Qe) Nt(Et Fp Fr Hu Hv Hw Hx Ih Ij Ik Il In Io Ip Iq Ir It Iu Jg Jh Jk Jl Jp Jq Js
Lw Lx Lz Mc Md Mf Mg Mh Mi Mj Mk Ml Mn Mp Mq Mr Ms Mt Mu Mv Mw My Mz Na Nb Nc Ne Nf Nh Ni Nl Nm No Nq Nr Nu Nv Nw
Nx Ny Oh Om Oy Oz Pa Pc Pd Pe Pf Po Pz Qa Qb Qc Qe) Ji(Et Fp Hq Hu Hx Ih Ii Ik Il Im Iq Ir It Iu Jh Jj Jl Jm Jp Js Jt Lh Lj Lu Lw Lx Ly Lz
Mc Md Mf Mg Mh Mi Mj Mk Ml Mm Mn Mp Mq Ms Mu Mw My Mz Nb Nc Nd Ne Ng Nh Nk Nl Nm Nq Ns Nv Nw Nx Oe Og Oh Oi Oy Oz
Pa Pc Pd Pe Pf Po Pz Qa Qb Qc Qe) Lv(Et Fp Fr Hq Hu Hx Ih Ii Ij Il Io Ip Iq It Iu Jg Jh Jk Jp Jq Jt kG Lh Li Lw Lx Ly Lz Mc Md Mf Mj Mk Ml
Mm Mn Mq Mr Ms Mt Mu Mv Mw My Mz Na Nc Ne Nh Ni Nm No Nq Nr Nv Oe Og Oi Oy Oz Pa Pd Pe Pf Po Pz Qa Qb Qe) Me(Fp Hq
Hu Hv Hw Hx Ih Ii Ij Ik Il Io Ip Iq It Iu Jg Jk Jm Jq Jt Li lN Ly Lz Md Mf Mh Mj Mk Mn Mq Mr Mt Mu Mv Mw My Mz Na Nb Nc Ne Ng Nh
Ni Nm No Nr Ny Oe Og Oi Om Oy Oz Pd Pe Pf Pz Qb Qc Qe) Nu(Hr Ih Ii Ik Im In Iq Ir Iu Jl Jm Jn Jo Jr Js Jt Lh Li Lj Lu Lw Ly Mc Mf Mg
Mh Mi Mj Mm Mp Mq Ms Mw My Nb Nc Nd Ne Nf Ng Nk Nl Nq Ns Nv Nw Nx Oe Of Og Oh Oi Oy Oz Pa Pb Pc Pe Po Qa Qb) Mi(Hr Hv
Hw Ih Ii Ij Ik Il Im In Iq Ir Jj Jl Jm Jn Jo Jr Js Li Lj Lu Mh Mq Ms My Nb Nc Nd Ne Nf Ng Nk Nl Ns Nx Of Og Oh Om Oy Pb Pc Pd Qa Qb
Qc) Im(Ik In Iq Ir Jj Jl Jm Jn Jp Jr Js Li Lj Lu Lw Mf Mg Mh Mj Mk Mp Mq Ms Nb Nc Ne Nf Ng Nk Nl Nq Ns Nv Nw Nx Og Oh Oz Pa Pc Po
Qa Qb Qc) Jj(Ih Ij Il Jk Jl Jn Jr Js kG Lh Lj Lu Lw Mf Mg Mh Mj Mp Mq Ms Mu Nb Nc Ne Nk Nq nR Ns Nv Nw Oh Pc Pe Po Qa Qb Qc)
Nl(Et Fr Jl Jm Jn Jo Jr Js Lh Lj Lu Lw Ly Mg Mh Mp Mq Nb Nd Ne Ng Nq Ns Nv Nw Nx Og Oh Oi Pa Pc Po Qa Qb) Jl(Hr Ii Ik Iq Ir Jm Jn Jo
Jr Js Lh Li Lj Lw Mg Mp Ng Nk Ns Nx Of Og Oh Pb Pc Qa) Nw(Hq Hx In Jr Lj Md Mh Ml Mp Mv Mw My Nf Ng Nk Ns Ny Og Om) Qa(Hv
Hw In Iu Jm Jn Jr Li Lj Mp Ns Nx Oh Pb Pc) Jr(Ik Jt Lh Lj Lw Mg Mh Mp Nk Ns Nx Oh Pc Po) Nx(Jn Jo Js Lj Mh Mp Nk Ns Of Oh Pc Qb
Qc) kG(Li Mh Mj Nb nl Nm Nq oO Oz Pb Pc Pf) Ns(Ir Jn Lw Mg Mp Nv oE Oh Pc Po Qb) Mp(Hq Ik Jo Js Lj Mh Nd Ng Nk Qb) Lj(Mh Nk
Oh Pe Po Qb rX rY rZ) lN(In It Nq Qb rC rX rY rZ Tz) aZ(Aa bS cA cF Hr Nb Og) rZ(Hr Hv jV Mr Pb Pd Pe) Po(Jm Jo Li Ng) Um(lL Nd Qv
Tz) Mz(ln Nf Pb) Ng(Mu Nq Nv) Jn(Jt Lw Mh) Lh(Hr Nf Of) Oh(Ik Nk Wm) De(Hr Jo) Nd(Hl Ry) Nv(Of Pb) nl(kF mZ) AxoE MgJo MhJs
NkPc InlL QbJm LddX} aA{Ma(Et Fp FR Hq Hr Hu Hv Hw Hx Ih Ii Ij Ik Il Im In Io Ip Iq Ir It Iu Jg Jh Ji Jj Jk Jl Jm Jn Jo Jp Jq Jr Js Jt Lh Li Lj
Lu Lw Lx Ly Lz Mc Md ME Mf Mg Mh Mi Mj Mk Ml Mm Mn Mp Mq Mr Ms Mt Mu Mv Mw My Mz Na Nb Nc Nd Ne Nf Ng Nh Ni Nm No
Nq Nr Ns Nu Nv Nw Nx Ny Oe Of Og Oh Oi Ok Om On oO Oy Oz Pa Pb Pc Pd Pe Pf Po Qa Qb Qc Qe) Nl(Et Fp Fr Hq Hr Hu Hv Hw Hx Ih Ii
Ij Ik Il Im In Io Ip Iq Ir It Iu Jh Ji Jj Jk Jl Jm Jn Jo Jp Jq Jr Js Jt Lh Li Lj Lu Lw Lx Ly Lz Mc Md Me Mf Mg Mh Mi Mj Mk Ml Mm Mn Mp Mq
Mr Ms Mt Mv Mw My Mz Na Nb Nc Nd Ne Nf Ng Nh Ni Nk Nm No Nq Nr Ns Nt Nu Nv Nw Nx Ny Oe Of Og Oh Oi Ok Om On Oy Oz Pa
Pb Pc Pd Pe Po Qa Qb Qc) Nt(Et Fp Fr Hu Hv Hw Hx Ih Ii Ij Ik Il Im In Io Ip Iq Ir It Iu Jg Jh Ji Jk Jl Jm Jn Jp Jq Jr Js Jt Lh Lj Lu Lw Lx Ly Lz
Mc Md Me Mf Mg Mh Mi Mj Mk Ml Mm Mn Mp Mq Mr Ms Mt Mu Mv Mw My Mz Na Nb Nc Nd Ne Nf Nh Ni Nm No Nq Nr Ns Nu Nv Nw
Nx Ny Oe Og Oh Oi Ok Om On Oy Oz Pa Pb Pc Pd Pe Pf Pg Po Pz Qa Qb Qc Qe) Pg(Et Fp Fr Hu Hv Hw Hx Ih Ii Ij Ik Il Im In Io Ip Iq Ir It Iu
Jg Jh Ji Jk Jl Jm Jn Jp Jq Jr Js Jt Lj Lu Lw Lx Ly Lz Mc Md Me Mf Mg Mh Mi Mj Mk Ml Mm Mn Mp Mq Mr Ms Mt Mu Mv Mw My Mz Na
Nb Nc Nd Ne Nf Nh Ni Nk Nm No Nq Nr Ns Nu Nv Nw Nx Ny Oe Og Oh Oi Ok Om On Oy Oz Pa Pb Pc Pd Pe Pf Po Qb) Mj(Fp fR Hq Hr
Hw Ii Ij Ik Il Im In Iq Iu Jh Ji Jj Jm Jo Jt kG Lh Li Lj Lu Lw Lx Mc Me Mf Mg Mh Mi Mk Mm Mr Ms Mu Mw My Na Nb Nc Nd Ne Nf Ng Nk
No Nq Ns Nu Nw Nx Ny Oe Of Og Oh Oi Ok Om On Pb Pc Po) Lv(Et Fp Fr Hu Hx Ih Io Ip Iq Ir It Iu Jg Jh Ji Jk Jl Jm Jn Jp Jq Jr Js Jt Lw Lx
Ly Lz Mc Me Mi Ml Mm Mn Mp Mq Mr Ms Mt Mv My Mz Nh Ni Nm No Nq Nr Nv Oe Og Oi Ok On Oy Oz Pa Pc Pd Pe Pf Pz Qa Qe) Ik(Et
Hq Hr Hv Il Im In Ji Jj Jl Jo Jp Jq Li Lj Lu Lw Lx Ly Lz Mf Mg Mh Mi Mk Mp Mu Nc Nd Ne Ng Nj Nk Nq Nu Nv Nw Nx Of Og Oh Oi Ok
On Pa Pb Pc Po Qa Qb) Nj(Fr Hq Hu Hx Ii Io Iq Ir It Iu Jg Jm Jn Jo Jr Js Jt Md Me Ml Mn Mq Mr Mv Mw My Mz Na Nc Nf Nh Ni Nk Nm No
Nr Ny Oe Oi Om Oy Oz Pd Pf Pz Qb Qc Qe) Po(Fp Fr Hq Hw Ii In Iq Iu Ji Jj Jm Jo Lh Lj Lu Me Mf Mh Mk Mu Mw Nb Nc Nd Ne Nf Ng Nk
Nm No Nq Ns Nu Nw Nx Ny Oe Of Og Oh Ok Om Pb) Nu(Hq Hr Ij Il Im Ji Jj Jl Jq Li Lj Lu Lw Mc Me Mf Mg Mh Mi Mk Mm Mu Mw Nb
Nc Nd Ne Ng Nk Nq Nv Nw Nx Oe Of Og Oh Oi Ok On Pa Pc) Mf(Hr Hw Ij Il Im Ji Jj Jl Jp Li Lj Lu Mg Mh Mi Mk Ms Mu Nb Nc Nd Ne Ng
Nk Ns Nv Nw Nx Of Og Oh Ok On Pa Pb Qc) Mb(Hu Hw Hx Ii In Iq Iu Jg Jm Jo Jr Lz Md Mn Mr Mv Mw My Nf Nh Ni Ny Oe Of Om Oy Oz
Pb Pd Pf Pz Qc Qe) Ji(eP Hv Ij Il In Iq Ir Jk Jo Jq Jt Lh Li Lj Md Me Mh Mk Mm Mu Mw Na Nc Ne Nf Ng Nk Nm Ns Nx Ny Of) Nk(Et Hr Ij
Il Im Jh Jj Jl Lj Lu Mg Mh Mi Mk Mu Nb Nd Ng Ni Nq Nv Nw Nx Oh Ok On) Nw(fR Hq Hr Hx Li Lj Md Me Mh My Nc Ne Nf Ng Nx Ny Of
Om Oy Pb) Mh(Et Hr Im Jk Jl Jq Lj Mg Mi Ms Mu Nb Nc Ne Nv Nx Ok On) Ok(Hv Hw Ij In Jo Lj Mk Mu Na Nc Nf Nm Ny Of Om) On(Hr Jh
Jj Lh Li Me Mm Mw My Nc Ng Nm Om Oy Pb) Nx(Hr Jj Li Lj Mi Mk Mm Mu Ne Ng Of Qa Qb Qc) oO(bQ cS cT cU cW dD dF kG Kq nR
oQ) Hr(Ij Il Jl Jq Lw Mi Mk Mz Nv Qa) Mu(Jh Jj Mi Mw My Nc Of Oy) cU(bQ bR cB cE cF dA dG) Qa(Hw Ij In Li Lj Pb) Ng(Jk Jl Mg Nq
Nv) Pb(Hx Ij Jq Ml Nv) Mi(Hq Lj Nc Nd) fR(Lx Mp Nq Pf) Hw(Ij Jq Mz) Nv(Hq Nd Of) Ij(Li Of) Lj(eD Im) hR(eD IN) AaaZ WmOh LxLi
MpNd MtNf MzOm JkOf JlLh LdeP} On{Oy(Ax cB De eP Et Fp FR Hq Hr Hu Hv Hw Hx Ih Ij Il Im In Io Ip Iq Ir It Iu Jg Jh Ji Jj Jl Jm Jn Jo Jp
Jq Jr Js Lh Lu Lw Lx Ly Lz Ma Mc Md Me Mf Mg Mh Mi Mj Mk Ml Mm Mn Mp Mq Mr Ms Mt Mv Mw My Mz Na Nb Nc Nd Ne Nf Ng Nh
Ni Nm No Nq Nr Nt Nv Nw Nx Ny Oe Og Oh Oi Ok Om Oz Pa Pb Pc Pd Pe Pf Po Pz Qa Qb Qc Qe) Ng(Et Fp Fr Hq Hv Hx Ih Ij Il Im In Io Ip
Iq Ir It Iu Jg Jh Ji Jj Jl Jm Jn Jo Jp Jq Jr Js Jt Lh Lu Lw Lx Ly Lz Mc Md Me Mh Mi Mj Mk Ml Mm Mn Mp Mq Mr Ms Mt Mv Mw My Mz Na
Nb Nc Nd Ne Nh Ni Nm No Nr Nv Nw Ny Oe Og Oh Oi Ok Oz Pa Pc Pd Pe Pf Po Pz Qa Qb Qc Qe Yj) Mb(Et Fp Fr Hr Hu Hv Hw Hx Ih Ij Ik
Il Im In Io Ip Iq Ir It Iu Jk Jl Jm Jn Jp Jq Jr Js Jt Lh Lj Lw Lx Lz Ma Mc Md Me Mf Mg Mh Mj Mk Mm Mn Mp Mq Mr Ms Mt Mu Mz Na Nb
Nc Ne Nf Nh Ni Nj Nm No Nq Nr Ns Nt Nv Nw Nx Ny Oe Oh Oz Pa Pc Pd Pe Pf Pg Pz Qa Qb Qc Qe) Pb(Hq Hr Hu Hv Hx Ih Ii Ij Ik Im In Iq
It Iu Jg Jh Ji Jk Jl Jm Jo Jq Jt Lh Li Lj Lu Lx Ma Me Mf Mh Mi Mj Mk Ml Mm Mn Mq Ms Mw My Mz Nb Nc Nd Ne Nh Ni Nk Nl Nm No Nq
Ns Nt Nu Nw Nx Ny Oe Of Og Oi Ok Om Oz Pa Pc Pd Pe Pg Po Pz Qb Qc Qe) Of(eP Et Fp Fr Hq Hr Hv Hw Hx Ih Ii Il Im In Io Ip Ir It Jg Jn
Jp Jq Jr Js Lw Lx Ly Lz Mc Md Mi Mm Mn Mp Mq Mr Ms Mt Mv Na Nf Nm Nr Nw Ny Og Oh Om Oz Pa Pc Pd Pf Qe) My(Hq Hr Hu Hw Ii
Ik In Iq Ij Jk Jm Jo Jt Lh Li Lj Lu Lv Ma Me Mf Mh Mj Mr Mv Mw Nb Nc Nd Ne Nf Nk Nl Nm No Nq Nr Ns Nt Nu Nw Nx Og Om Pd Pe Pg
Pz Qa Qb Qc) Nj(Hq Hr Hw Ii Im In Iu Jg Jh Ji Jl Jm Jt Lh Li Lu Lv Ly Ma Md Mg Mh Mi Mj Mk Mm Mn Mu Mw Nb Nd Ni Nl Nm Ns
Nt Nu Nx Ny Oe Og Oh Oi Ok Pa Pe Pg Po Qa Qb) Yi(Aa Ad aK aM aZ bO bS cB cC cF cH cU dJ fR Gb Gd Gz Hv Ib iP Jg Jo Jr Jt Ki kO Ks
Mh Mm Mz Nb Nh oF Ok oO oP oQ Or Ow Rc Rx Sf Sh Si) Jj(eM Hq Hr Hx Ih Ii Ik Iq Jh Li Lj Lu Lv Ma Md Me Mf Mh Mj Ml Mr Mu Mw

Figure 40 Continued lW) Jv(fB oQ) Ug(fR mH) Uy(mT nD) nN(Li Ny) lY(Je Oi) mF(Gd Yi) AlnU ChYf SsmP JofR YeeM LhoP RtmZ YlOr UxnK PcfB}
Kq{Iz(eM kC kE kF kI kK kN kO kP lW lX mF mH ml mM mP mS mT mU mW mY mZ nA nB nC nD nF nH nI nJ nK nL nM nN nO nR nT
nU Um) Al(kC kE kF kI kK kN kO kP lW lX mF mH ml mM mP mS mT mU mW mY mZ nA nB nC nD nF nH nI nJ nK nL nM nN nO nR nT
nU oO) oO(Aj Ap Bb cF Dd Dg Dl Fy Gb Hb li Jg Jq Jt Kl Lh Mh Nv Ny Op Pc Qe Qh Sf Sh Ue Uf Um Ur Uv Vq Vt Yd Yg Yi) Nm(eP kC kE
kF kI kK kN lW lY ml mP mS mZ nA nB nD nF nK nL nM nN nO nR nT nU oP) Yi(Jr kE kF kK lY mH ml mP mS mZ nF nI nJ nK nM nO nT
nU oF oP oQ) Of(kF kI kK kO lX mE mF mH mM mS mT mW mY nB nI nJ nU oQ) mE(Ap Bb Cv Dg Ef Fb li Jk Jo Jt Kl Ny Oi Ue Ug Uu)
Gb(eM fB Lw lX mY nF nK nM oP oQ Vu Vv Yg Yh Yf) Um(Ad Ap Bb cR Dg Ef Hb Ib Jo Li Mm Nd Or Oy) mT(Ad Bb Jk Jt Li Lp Mm Nv
Qe Rc Rx Uu Th) mW(Ad Ap Bb Dg Jg Jj Jt Kl Mm Pz Rc Ss Uu) nI(Bb Bc Dg Ef Fr lt Jj Jt Kl Mm Pz Rc Ss) eP(aR Ax Ef Fy Iu Jj Kf Ld Mm
Ou Vo) nJ(Ad Jj Kl Mm Nv Ps Rv Vb Wf) dX(Fy Jj Jo Jp Kf Mm Ou Ss) lY(Bb Bc Fb Jj Jk Nv Ny Oi) Jj(mZ nO nU oQ) fB(Op Un Vt)
Ad(mM mS) Mm(lX pH) Nd(Yg Yf) Kl(kF nR) eM(Nv Vb) ApYj TrRa YgcT ZqlW SsmP KylN LifA OikF UuoQ VvOy VwnL} Nd{Um(Et Fy Hv Ij Ik Il In Je Jj Jl Jn Jo Jp Jq Jr Js Lj Lv Ly Lz Mb Me Mf Mg Mh Mj Ml Mm Mp Mu Mv Mz Na Nc Ne Nj Nk Nl Nq Ns Nw oE Og Or Ou Ow Pc Pd Pg Po Qb Qe Qh Qv Qx Qy Ra Rc Rf Rh Rj Ub Ue Uf Uk Un Uo Up Vo Vp Vu) Hl(aP Ax Dc Fd Gz Hx In Jl Jn Jr Js Mi Mj Mr Mz Na Nr Ny Oa Pg Pi Po Qa Qe Vi Vq Vv Tj) Lp(Fa FB Fi Gz Hq Jl Lx lY mE mF Mp Nj Nq nU Ps Qe Qh Uf Vu Wb Yi Tj Yf) Lx(Rt Rv Rx Sf Si Uw Uy Uz Vb Vh Vi Wf Wg Yg Yh Yj Yk Zw Tl Xa Yf) Ry(aP cG dF Ed Jl Jr Ld Mi Mj No Nv Nw Oa Ow Pg Po Qe Vp Vv) Yf(Ez Gp Gz Hq Hv Jd Jr Kz Ld Mp Nq Nw Or Ou Ow Pe Po) Yi(Ed Gb Gd Gz Hv Ij Jr Js Kp Kz Ow Rx Sf Sh Va) Gb(Ed Et Ez Gp Jr Mp Nq Ow Pe Uf) Sh(Ao bF Ed Gp Hq Mv Nq Pg Vu Vv) oE(Fa Gp Hc Id Je Jf Kc Qn Vv) Rx(Ax Ed Ez Gp Nj Nw Ow Vv) Nt(Hq Jo Lv Mb Ng Nj Of) Gd(Ez Fi Ho Uf Yl Tl) Mb(Jl Jt Mi Mz Nv Pg) Ed(Gn Ru Sf Si Uy) Gp(Fc Fi Ne Sf Tl) Uy(Js Kd nN Wb) Vu(Hr Qv Va Ye) Oy(De Ho Ou Rz) Pg(Hp Jj Nj Vb) Si(Nw Ow Uh) Jo(cB De Fi) Kp(Fd Ho Xa) Pe(Uz Yg Yj) Po(Du Yj) Ns(bS Qv) Nj(Mi Nw) Ue(Mg Qy) Va(Vv Yh) FiUg HaeD NqSf LvNl LyQv MhRz MndX IdlL JrUz KylN RuOw YlOr UoVi aCaX} Jj{Nt(Et Fp FR Hq Hr Hu Hv Hw Hx Ih Ii Ij Ik Il Im In Io Ip Iq Ir It Iu Jg Jh Jk Jl Jm Jn Jo Jp Jq Jr Js Jt Lh Li Lj Lu Lw Lx Ly Lz Mb Mc Md Me Mf Mg Mh Mi Mj Mk Ml Mm Mn Mp Mq Mr Ms Mt Mv Mw My Mz Na Nb Nc Ne Nf Ng Nh Ni Nj Nl Nm No Nq NR Ns Nu Nv Nw Ny Oe Of Og Oi Om Oy Oz Pa Pb Pc Pd Pe Pf Po Qa Qb Qc Qe) Pg(fR Hq Hr Ih Ii Il Im Jk Jl Jm Jo kF Lh Li Lj Lu Lv Md Me Mf Mh Mi Mj Mk mP Ms MT Mu My Mz Nb Nc Ne Ng Nk Nl nN Nq nR Ns nU Nw Nx Ny Of Om Oy Pb Pc Pd Pf Po Qa) nR(Jq Jr kF kN Li Lx Lz Mb Ml Mu nI Ns oO Pb Pc Pe Pf Qa) fR(bZ Il Im Jk Jl Jn Lv Lx Mi Mp Mu Mv Nv Nw Pf Po Qa) Nx(Ik Jk Jl Lv Mi Mj Mu Nk Nl Nq Nu Nv Po Qa Qb) Lv(Ik Jk Jl mP Mu Nj Nk Nl nN Nq Nu Nw Qa) Mu(kF kN lY Me mF nA nI Nj Nl oO) Mj(dX eP Ik kF nI Nj nN Nu) Nj(Jk Jl Mi Nq Nv Po Qa) Jl(Ik Nk Nl nN Ns Nu) Qa(Ik Lj mZ Ns Pb) Nq(kF kN lY mE) Nv(Mb Nl Nu Of) Vv(kP mP mT nN) Mi(Ik Mb Nl) Mv(kN mE) Mz(Nf Pb) Nb(kF nU) Ij(dX eP) nN(Jr Pf) PoNl FwmZ NuIk MbJk MecF HcoO YimW JneP NwPb UfdX aUlX} Gb{Nw(aD Ao aR aS aW AX Ba Bb Bc bE bI bN bO bU bX Co Ct Cx cZ Db Dl Du Ed Fi Fw Fy Gc gL Hf Hl Ho Hq Hr Hu Ik Il Im Jd Jf Jg Jh Jl Jm Jp Jr Jt Kc Kp Kz Li Lx Mf Mg Mh Mi Mk Mp Mr Mu Mv My Mz Na Nf Nl Nq Nu Ny Oe Ow Oy Oz Pa Pb Pd Pe Pf Pg Qy Rx Ry Rz Ub Uf Uy Vu Vv Vw Yi Zq Tm Tj Th) Jr(Ad An Ap As aW aX bE Bn Co Cp Cq Cv Cw cZ Dc Dd De Dg Dr Du Em Ez Gn Gp Hc Hl Hr Hv Hw Hx Ib Id Ii Ij Im In Ir Jn Jq Kd Kn Kp Kr Li Lw Mg Ml Mr Mu Na Nb Nf Nq nU Ny Ow Pb Pi Pk Qy Rj Ry Rz Uf Um Uo Us Vv Yg Yh Yi Yk Zq Tl Yf) Pg(Ao Co cZ Gc Gp Jh Kc Ld Mg Mh Mi Mk Mp Mt Mu Nq Ns Ow Ql Yj) Ow(Ao Bb Ed Hc Hv Jg Jl Jp Mi mW My Nf Nt Vv Wb Yi Yl) Lx(Ao cF Gc Hc Ho Kc Mi Ml Mp nL oO Vu Vv Yl) Vv(Hv Kc Ke Ld Li Mt Nq Qa Vj Vu) Yi(Ao De Hv Ke Ld Mp Nq Om Ou) Ez(kI mH mS nA nI nJ oO oQ) Jl(Ao Gc Gp Kc Mi oO) Vu(Jq Js Ke Pe Vi) Ao(Ax Fy Js Oa) Yj(Hv Jq Js Ke) Ld(mW nA nR nU) bZ(mM mP oO) Ed(Co Hc) Gp(Gd Ou) Mi(cT Hc) Ho(Hl oP) Yl(Or Ou) EtnL GnnR NqcT MpJp JsoO PfmZ aQnU aWoP} oE{Ns(Ad aO Ap aU aW Ax Bb Bc bG bN BO bS cA cC cH cL Co Cs Ct cW cX dA Dg Dl dR Ed Ez Fb fP Fw Gp Hb Hc Hr iA Ib Id Ii iJ Ik Im iP Iz Jd Jo Jp Ju Jv Kk Kl Ko Kp kQ Kx Ky Lh Li Lv Lx Ly Lz Mb Md Me Mh Mi Mm Mn Mp Mq Mu Mz Ne Nf Ng Nk Nm Nw Nx Ny Oe Of Og Oi Or Ow Oy Oz Pb Pc Pd pF Pg Pj Po Qh Ql Qn To Uf Um Up Vq Vu Vv Tj tF) Vv(Ad Ap Bb cE Dg Dl Ez fP Hb Ij Iu Jd Jf Jm Jt Kl Ks Lh Li Mm Ng Nm Nr Nv Oe Oi Pc Rc Rm Um Uu) Um(aO aR Ax cL Hc Jf Jq Kg Lj Na Ou Oz Pc Pd Pk Ub) Ax(Fa Fb Fw Gp Je Jf Kx Lz Po Qh Qn Vu Tj tF) Jf(Ad cL Iu Jm Jo Nm Oz Pb Pj) Ad(Hc Kg Na Ny) Pc(Je Ne Qn Ra) Ed(Cs Fp Li) Nm(Hc Kg Qn) Mm(Fw Kx) Ne(Ly Nh) Hc(Dg Dl) Kg(Jo Oy) oO(Ju pH) IdJr UoPk} Yi{Jr(aK aM aO aU aX bC bE bH bP bS bU bW bZ cA cC cF cG cH cI cL CO cS cZ De dF dG dH dJ dK dL Ez Fc Fi fR Ha Hb Hv Hw Ib iH IO Jh Ju Jv Kc Kg kP kR Ld Li Mg Mh Mi MP Mq Mt Mu Mv Mz Ni nK nL Nq oF Ou Ow Pd Qb Qy Rc Rf Rx Rz Sf Sh Si Uf Uk Yh Zq Tj) Hv(Ax Du Ha Hp Ib Ih Ii In Iu Jm Li Lj Lp Nf Pf Qx Rf Rx Ry Tt Yg) Lx(cF De hC iH kC kR lY mH mY nC nJ oO pF tF) bZ(fB kF lX mP mY nB nN nU oO oP oQ) Mz(kI lW mS mZ nI oO oP oQ Ou Ow) oF(bG Jq Ke Kg Ld Nv Nw Pg Pi Pk) Ou(Ax cE cT Na Nb Ow Rf) Ld(Jl kN mH mT mW mZ) Nw(bU cF fR Hb mY Rf) oQ(bF bQ Jq Lh mZ Pg) oO(bQ Fy Jl Jv Sf) oP(bQ Ez Gp Js Pi) Ow(mZ Rt tF) Or(cF Rf) bQ(kC mS) DeJs EzmH GpnA NqcT HlnR QabS JqcF LhnN PgeC aFkP} oO{nR(Ax cF cT Dd Hr kE kF kN Lx Lz Mb Ml Mm My Ni Nm No Nu Of oQ Pc Pe Rf Rh Tr) Jv(aO aQ aU Aw bA bF bQ Ch cT dF Dk Hc Jk Mj Mt Mu Nq oQ Ou Qu Uf) Jl(Al Cv Dd Hp Op Qh Qv Rf Rh Rm Rx Sf Sh Ug Um Yg) Ju(aU bF bQ cT dF Dk eC hB Lx Mj Ou Pi) oQ(kF kK kN Lp Lv Mb Mh mZ Oe) Sf(bZ Fy Jr Lx Mz nU Pg Ph) aJ(bQ bR cF cS dF kN Ye) bZ(Jo Op Sh Um Ur Wb Yd) pH(aR cJ Nb nW Pc Rf Rh) Lx(cF fB Hb mP Sh Yj) aO(dL Dp fA Um Ur Yj) Mj(kF kN Mh Rx Ur) cT(aP Ni oD Qv Rj) oF(dU Hr jB oD oW) Tr(Ad Ax Dd dN) aF(cF fA Ni Rz) Qa(Ax cF Rm) Rh(cL dD Mp) Ur(bF Hc oN) Dd(cG Pg) Fy(aU cN) Mh(dF Mu) Nb(kF Ld) bA(fR oD) bV(eC Ni) dG(Rx Ry) GzRf LvmP UeUf YjZw ShPg UgaP VuPc bQnO dLhG} Nw{Pb(Hv Hx Ij Il Iq Jk Jl Lj Lv Mb Me Mh Mi Mu Mz Nb Nk Nl Nq Ns Nu Nv Ny Oz Pg) Nt(dX eP Hx Ii Jo Li Lv Mb Md Mh My Nj Ny Og Om Oy Po) Of(Ik Li Lv Mb Me Mu Nj Nk Nl Nq nR Ns Nu Nv Pg Qa) Lv(Hq My Ng Nj Nk Nl Nu Ny Om Oy) cF(Ad Ax Dg Jo Jt Lh Nm Ry Yg Yl) dX(Aw bA cT Ed Ij Jf Jr Pe) eP(Aw bA cS cT Ij Jr Pe Uf) Yf(Hb Lh Ny Ow Qb Si Va) Yl(Bb Ii Mz Or Ow Rc Si) fR(Jr Me Mh Nm Nq Pf) My(Jk Lj Nj Nq Pg) Ng(Ik Mu Nq Nu Pg) Me(aU Ax Bb cB) Nj(Hq Hx Mh Ny) Yj(Bb Hb Ow Rc) Si(Gp Rx Vu Vz) Uw(eM nC nH) Uy(Ny Ow Rc) Oy(Jk Nq Pg) Hq(Mi Pg) Ry(Hb Rc) Om(Lj Qa) Vw(Ke Ow) nJ(Rt Vi) DeJo WmLi EdHp GdMz NmcB MbJl MmeM IbWg PsnH} Qa{Pb(Hx Ik Im Jl Jm Jq Lj Lv Mb Mi Mt Mu Mz Nb Nj Nq Ns Nt Nu Nv Nx Ny Pc Pg) Um(Cs Fp Hb Ih Ii Ij Iu Jm Jo Ju Jv Lh Mm Mr Ns Ny Qe Qv Rc Rm St) Hw(Ik Im Jl Jm Jq Li Lj Lv Mb Mz Nj Ns Nt Nu Nx) Nt(Ii Ij In Iu Jm Jo Li Ng) Ax(Hr mE mF Rj Ud Vu Vv) Ii(kF mE mP nN nR nU Nx) dX(aJ Aw bA cT dG Ld Lv) Hp(kC kK lY nB nJ Vv) Li(Lv mP nN Ud Vu Vv) Lj(Ij In Lv Mb Of Vu) Al(kI mW mZ nU oQ) Mm(kF mP nN nR nU) Jm(Lv mE mF mZ Nx) Aa(bS cB dG mW) Ns(Lv mP nR nU) eP(bA cT Fy Ld) In(Lv Mz Nx) Ha(jB oT) Mb(Jl Mi) Nf(Mt Mz) Ng(Mu Nq) eM(Uw Yg) nR(Lh Mn) DeJo GnnC MiHq IjNx RmmZ} lN{hR(aC aD aE aF aH aI aJ aK aL aM aN aP aQ aR aU aV aW aX aY bA bB bC bE bF bG bH bI bJ bL bM bN bO bP bQ bR bS bU bV bX bZ cA cC cD cE cG cH cI cK cL cM cN cO cP cQ cR cS cT cV cW cX cY cZ dA dB dC dD dE dF dG dH dI dJ dL dM dN Hu jH Qy) Ky(Ap Ax Bb bC Bo Cp cT cY Dg Ef Id Iu jD jF jG Jt Kl Kr Li lM Ly Me Mf Nt Nx Rb Uc) Nq(eD hV hW hX Jh Jo JT Me Ml Mu Mw My Nf Nr Nx Qb rB rC rZ) Mu(eD hW hX Qb rB rC rZ) Mf(jI Qb rC rX rY rZ) Or(Ax Id Ko Mr Vq) Ax(Ml Qb) MeHf IdQb} eP{Ld(bO cG Cp Cs cT Dd Hw In Ip Jp Jt Li Me Mp Mt Mv Mz Nq Oa oF Ou Ow Pf Ph Qb Qc Sr St Uc Uf Us Vs Vv Tj) Uf(Ad Ax bA Dg Dl Ed Jp Jt Kj Kl kR Lz Mm Qz Vo) Lv(Aw bA cF Cp Di Ij Jn Jq Jr Mi Mv Na Ny Pe) Pe(aU Aw BA cT Dc Em Ik Mm Mp Mz Nj) bA(De dM Ij Lh Li Mk Mp Mt Mv Om Qe) cT(Ao Aw cS Cx De Gc Mk

Figure 40 Continued

Mt Nq Ow Qe) Lx(aU bS Fa Jf Mi Mp Om) Aw(bO Dc Jr Mj Mz oF) Jp(Ed Ow Qh St Vu) Fy(Ir Lh Or) Mp(bV Jr Mj) Qe(aO Iu Mm) Mi(bV Mj) Jq(Cx Mk) Jr(Jf Nh) Ow(Nk Vs) Ou(Na St) cG(cE dH) DcLz MmIj MnKf MtaC ImQw QbdK UnbF VqkR} dX{bA(Aw cB dH dM Ij Jf Jh Lh Li Lv Mi Mk Mp Mt Mu Mv Om Pe Qe) cT(Ao Aw cB cC Cx De dR Gc Li Mi Mk Mp Nq Pe Qe) Lv(cF Cp Cq Di Ij Jn Jq Jr Lx Mi Mv Na Ny Pe) Lx(Ao aU aX bS cS Jq Ld Mi Mp Om Ou Qz) Ld(Ed Hx Ij Jn Jr Mj Mr Pe Po Qe Up) Aw(Ar Cs Dc Ij Jr Mj Mz oF Pe) Jp(Ed Ks Ow Qh St Uf Up Vu Vv) Pe(Ax Ba Fy Ha Mp Ou Qw) Fy(Aa Kr Lh Om Qc) Ou(Mh Uf Vu) Mk(Jq Ny) Qe(aO Iu) Jf(bQ Mz) Ow(Nk Vs) Uf(Aj Jo) CxJq GdMn MjMp MtaC NhJr ImQw QbdK} Nt{Jo(cB De Et Hq Hr Ih Ij Ip Jk Jn Jp Jq Js Jt Lu Lw Ly Mb Mc Mf Mh Mi Mj Mp Mt Mu Mz Ng Nj Nk Nl Nq nR Nv Nx Oe Pa Pc Po) Ng(Et Fr Hq Hu Im Jh Jl Jp Jq Lj Lu Lw Ly Mb Mf Mg Mi Mj Mm Mp Mt Mv Mz Nj Nk Nl Ns Nv Nx Oe Pa Pc Pg Po Qb) Lv(Hq Im Lh Lu Ly Mg Mt Mu Nk Nl Ns Oe Of Pb) Hq(Jl Lx Mb Mp Mt Mu Nq Nv Pg) Of(Jk Jl Mi Mt Mu Mz Nv Pg) Mz(Ij In Mb Om) Mb(Jl Mi) Mu(Me Oy) Ii(Jl Pg) Li(Mi Po) nR(Jt Nm) JqPb} Gp{Gd(An cA De Dr Du Eq Fc Fd Fi Gc Gh Hl Ho Hp In Lp Lt lW Lx Mj Nb Op Or Ps Qv Qx Rx Ry Rz Sh Si Sj St Vi Vq Vu Vz Wb Wh Yd Yg Yk Yl Zw Zx Ye Tm Tl Xa) Wh(eM kP lX mM mS mT mY nH nI nR) mE(Ho Rx Rz Vi Vw We Yh) Wd(eM kI mY nB nD) Vi(fR lW nA nJ) Th(kK kN nR) Yh(mH nI nN) Sf(Ed fR Ou) Sh(Hc mI Ou) Ps(eM fR lX) oP(Hl Rx Ry) Aa(Dc Ed) mH(Uw Xa) oF(Fc Fi) TinR FaZq NmHo HlnU SiJr LpnI YlOr VvfB} nR{Lz(Ii Jo Ju Lh lY Mm Mn Nm Ns Ny Of Pb Pc To) Lx(Al Ii Jm Jo Jt Ju Mm Mn Nm Ns Ny Of) Hl(aR aW cH cJ cM cS Db Jf lX nI Yg Yk) Nm(Li Mb Ml Nb nI Pe Pf) Mm(aU Li Mb Ml Nb Pe Pf) Jo(Ez Li Nb Ni Uf Vv) Pf(Ii Jt Lh Mn Of) Al(Ih Jn Kx Vu) Pe(Ii Li Ny Of) Pc(Hr Mb Ur) cF(Dg oP oQ) Bb(aU Di) Ns(Mb Rb) Ml(Ju Mn) Nb(Ii Jm) Li(lY Of) nI(Jt kF) FwKs NiNk HqSh RbJr SsRz JqOf UgVv VbVi} Mi{Mb(bS Et fR Ih Ij Ik Il Im In Jk Jl Jo Jp Jt Li Lj Lu Lv Ly Mj Mu Mz Nb Nc Ng Nj Nk Nl Ns Nu Nv Nx Og Pc Pg) Hq(Ik Jk Jl Lv Mh Mj Mu Nj Nk Nl Nq Nu Nv Nx Po) Nj(Jo Lv Mu Nb Nu Of Pg) fR(aO Jo Lv Lx Lz Nm Pf) Ng(Ik Jk Mu Nu Pg) Jo(bS cB cF De Ik) Lv(Nl Nu Of) Bo(cF Mm) Me(Mf Mu) Mz(Nf Pb) Of(Ik Pg) Or(Um Yl) bS(Nm Ns) DeOy MjlY MuNl} Mz{Pb(cF Ik Jk Jl Lj Lv Mb Me Mf Mh Mq Mu Nk Nl Nq Ns Nu Nv Nx Ny Pg) Nf(cF Ik Lh Lj Lv Mb Me Mf Mg Mu Nj Nl Ns Nu Nv Pg) Um(Bb cF Hb Jo Ju Li Lj Ly Mu Mv Nq Ns Pc Qv Qy Rc) cF(Aa As Cq Cw Hr Hw Jo Uo) nI(Al Cv Kl Rx Wb) Mb(Jl Mp Nv Pg) Jo(As cB De) Yl(Or Ou) Of(Nv Pg) AaEd AdcB DeHr YjRc} Lx{fR(aU Ax cB Hr Hw Ii Jo Jr Lj Lv Ml Mm Mp Mu Mv No Nq Ns) kF(Hp Ih Ii Jt Li Mm Nm No Ny Oe Of Oi Uw) eM(aU Fa Mm Rf Rt Uw Uy Zq) mP(Ii Jt lY Mm Nm Ns Of) nN(Ii Jt Mm Nm Ny Of) cF(Cs Du Hl Ry Yg) nU(Ii Mm Ns Of) Mu(lY mE) Ii(Fi mU) Lj(jB oT) Lp(kN mW) AxoT NoYl RfpK OekC VwnJ} Lp{Hq(fB kC kE lW lY mF mH mI mM mP mT mW nA nB nD nI nJ nK nO nU) nI(bF bZ Jr kN Mj oN Ou Pf Vp) mT(bZ Co Ef Mv Nq Rz Ua) kN(aU Mb Pe Pf Pg Ps Wd) Uc(mH nB nC nN nO) Hc(Gz Hv mI nB) Vu(fR Jr nJ nL) Pg(mE mF) bZ(lW nN) nU(Ps Vv) oP(bU Jf) HveM YlOr PbkE bFmZ cYlX} Or{Yl(AO aU Aw bA bC bF bQ cF cL CO cS CT dK Ef Hb Hc Ho Hq Jh Jr Ju Kc Kj Li Mg Mp Mt Mu Mv Na Nb Nq Nv Om Ow Pd Pi Rz Uf Wd Zq) Um(Ax cF Fy Hb Hc Ju Jv Lh Lj Mg Mm Na Ns Pc Ub Uf) Oy(Mg Mv Vv) Id(jG lK) MejV JeqT} bZ{fB(aF Qb Qh Qw Rc Rf Rm Sr St To Uh Un Up Us Vq Vt) nI(Gd Hp Op Rx Rz Sf Sh Wb Th) Yg(kP lY mE mF mH nK nU) Hl(kE kN lX mW nJ) Ny(dU eQ gZ oV oW) mH(Gh Rt Sf Va Th) mE(Ur Va Wb Zw) Ax(jB pH) Hp(mI nJ) oV(Rf Rm) ZqmS RymI UwmP UymT UxlX cDpK} Jr{Yj(Hb Ib Ju Jv Ow Rc Rx Sh Si Zq) Yf(Hb Hp Ib Ii Ny Ow Si) Hp(Ed Gz Um Uo Vu Vv) Yg(aO bC cF cG) Si(Hl Ry Um Uo) Em(bO De Ii) Ry(Hb Ju Nv) Ow(Uz Wf Wg) Ib(Uz Wc) Rx(An Id) fR(Ii Jo) AlnU MmnN HlHb SfoP ZqkF WgJm NyUz UoUy UwmP aUlX cSmE} Nq{eD(Hq Ij jG Li lL Ns Of Oy qU qW qY rA rB rC rX rY rZ) Oy(bA bV cB cT De jD lY mE Um) lY(Hr Jh Mk My Of) Ng(Jl Lv Nu Pg) kF(Mb Mm Of) Sh(bH Vv) Om(jD lL) MbJl MmnN HrmE YgcT YkJv bAfR} Jo{De(bS cB cF cT Hr Jl Js Lv Me Mj Nf Oy Pg Po) Pg(Hq Lv Mb Nj Nl Nu Nx) cB(cL cT Lv Mj Po) Uf(eM kN mZ Um) cF(cT Mp Po) Lv(aR nN) Jl(Mb Nj) Vv(mP nN) aU(lX Po) mE(Mu Qu) IdlL UveD VuVs cTnU} Mb{Jl(Hr Ii Im Iu Jm Jt Lh Li Lj Lu Lv Lw Ly Mm Mp Mu Ng Nm Ns Nu Nv Oe Of Og Oi Pc Pg) Nv(Hq Ng Nu Of Pb) Ns(mP nN nU) Ng(Jk Pg) kF(Mj Nb) NuPg MumE aOoV mWoT} Vv{nU(Ad fB Ii Iz Jt Lz Ml Mm Nm Of Oi Uu Vo) Rc(Hl Uy Vi Vj Yj) Rm(jB oT oW pI) Ug(mU nN nT) Mm(oV pI) Ii(gC oP) Oy(Mu Ou) fB(nC nJ) oW(Lh Om) DlnI EdHp HvUy IbpH ShRy OinN OwVj UueQ} aU{lX(Aa Ap Dl Dp Fy Hb Iz Jt Kf Ks Mm Nm Ny Of Pc Pj Rc Rj Rx Tr Ue Uk Uo Ur Uu Vo) kN(Ad Fy Gh Kf Kl Mm Nm) kF(Bb Dg Mm Oi) AwOy} oV{Pc(aF aO bF cS Ez Jv kF Ou Ow Rb) aO(Ko Ou Ow Qm Qn Rf) Al(Fw Kx Ow Rm) Ez(Mm Ny Rf Rm) aF(aR aW Kx Ow) cT(Lh Mm Om Rm) bF(Dp Jv) AxOw HboN LdQl} Lv{Im(Ad Ax cF Nk Nl Nu) nN(lY Mm Nm Ns Of Pc) Ng(Jk Mu Nl Nv) mP(lY nI Ns Pc) Nl(Mt Mu Nu) Of(Jk Nv Pg) Oy(cB cF De) Ns(cB mU) EmcF NuMt MulY nIkF} Pf{nN(Jt Li lY Mm Nm Of Pc) mP(Jt Li lY Mm Nm Of Pc) kF(Mm nI Nm Pc Uw) Mu(lY mE nK) mZ(nI Ry Vb) AlnO MplY HlkN SfmH OfnU PcnT} Mj{kF(Ii Jm Jt Lh Mm Nm Oe Of Oi) Um(Ju Li Lj Rg) lY(Li mP Mu) nI(mZ Of Ur) De(Hr Oy) Hl(mP nU) nN(Mm Of) MuNg WfnL LjeD cFnO} Pg{Ng(Jk Mg Nj Ns Nu) Hp(gL kN mM oQ) Gn(nC nH nL) Of(Lj Mu Nu) kF(Gd Mm Vb) Fd(nC nL) Oy(Lj Mu) nN(Jt Mm) AloW GdnK SioQ ShkC JuoT} fB{Ez(aF Of Op Qb Qe Qh Qv Rc Rf Sr Ss To Un Vo Vt Yg) Yg(bF bQ Pi) Yh(cM Hb) BaHp HqZx QtPc RzaF LhOp} gV{bA(aE aG aH aL aM Ao AW bB bI bL cB cC cH cK Cw Dc dM) cT(Ao bO cV Cw) AwCs BaDc} Me{jV(aW Ba Bc bL CT cX dE Dl Ki Kj Mf) aW(jF jG jI jO jP lM) Id(jI jT lL) NvOf} nU{Hl(bH dI Jf kN Rv) Eq(aO cT) Gn(aF Hv) Ns(Mh Rb) Ur(Ch mE) CvaC GhaQ HpVi HqSh RtbF UgmE aOfR nIkF} Mu{mE(kE Lz Mh Nm Oy) Ng(Jk Jl Nu Po) lY(kE Lz Mh Ml) LznK UeUm JlOy NvOf OmeD jVrZ} Yl{Ld(eF fP gL gP hC iO iP nW nY oF pF) Ou(cE Ju Jv Op Oy Sf) Ow(Hv Li)} Um{Ou(Aa aR Hb Hx Na Qv) Uc(Mp Mv Qy) Li(Mp Uf Vu) Hx(cF Mv) ApjO IdlL HbJq VuVs} eD{Uv(Fp Js Li Lj Mq) Mv(Hq Ns Of) hR(cF jO lL) Lj(Md Qe) FrJm MfJv MyOy bGdI dHlL} Ow{Ax(dU oD oW pH pK) oT(Li mW Ny) Lj(jB pK) Rt(Aa Yj) Pc(jB oD) GdVz SfmH UweM} Hq{Sh(kC kE kN mF mH mI mM nD nK nL oP oQ) GdnK SfoP YekN NyPb} nI{kF(Dl Jl Jt Lu) Sh(bF Yd) aO(Rx Ur) mZ(Cv Lz) oN(Hl oT) GdcG YgLh KytF aFoW} Oy{Hc(Ho Rx Sh Wd Zq) cB(Aw cT De Mv) De(bS cT) Ou(Ef Uf) AwbO JvoT} Id{lL(aM Ed Lh lM Ly Lz Ph Qc Qe Ql) Ly(jI oF) EdjI RblM} Vb{Ez(mM mZ nC nD nH) Rz(kK kO nL nN) kN(Mg Uf) OmnK PeeM} Hp{Ed(aO Dc Ez Hc Ua) Ps(eM mY nC) Vi(eM nJ) JsVu UwkP} Hv{Gn(kN mP nC nH) Uy(eM In Uo Vu) Mh(Du Yj) Yg(aO Tt)} aF{cF(nT oP oQ oW) Rz(kE mZ) mE(oW Zq) NioT YhoQ aPdH aRgC} oT{Jv(Oz Pa Pb Pd) Ny(cT oN) iO(Rf Rm) CsPe EzmW cMoN} Nv{Of(Ik Lj Nj Nu) Yj(Oi Rc) Ry(Ed Oa) NuNg} Yg{bQ(nA oP oQ) cT(Gz Ou) JqcF LdmW PioF} Hl{mW(Hc Js Li Po) Vu(fR kN) bGoF} kF{Nb(Ii Jt Nm Of Oi) NyoD PcoW} Jk{Ng(Et Mg Nl Nu Po) QumE} Ld{Ry(Jl mZ) YjRc RxmS QljB NyeQ} Uf{Jt(kE kI kN mW) MmeM UedI} Pe{eM(Ax Mm Uw) AxmZ LinN LjOf} rZ{Mf(jF jY) hR(jO jP) iCjO jDjT} mE{Qu(Mm Nm Ug Ur) ChUr} Aa{Dc(aX bV cF) dRlX} Yj{Rc(Jq Yh) DeMh RxcT} Lh{nJ(Ru Vi) UwnH VanL} Li{Lz(mP nN) MlnN KefA} bF{Ju(kI oQ) JvkI PcoW} Ax{fA(Fn Mp) LyoF} Vi{Uo(Ny Rc) WbnT} oP{DubB SfJf ShbU} oW{Pc(aO bA) FacT} Mm{MpeM KefA} Tr{RaOu JpfR} Jq{Yfli SiVu} Rt{YhmZ aOnL} Ri{RvnH kCpH} dU{QwcS KchC} kN{NmKe WbaQ} AlRmeQ DeGdHc PoLjOf ThbBnC EzMvlL LyKyjF MhaCaX MqUwmW HrRcVu SfcYlX JuPikI RfPbpH aPcFdH bAdMeM Unconstrained panels with 2 analytes, where 1.0E-7 >= 'model p-value' > 0. Contains 1 panels of 142,491 total panels evaluated. : NnIv Unconstrained panels with 2 analytes, where 1.0E-6 >= 'model p-value' > 1.0E-7. Contains 30 panels of 142,491 total panels evaluated. : Nn(Is Lv Mb Me Nj Nt Ok Qd) Iv(aA Ji Jj Mx Ok On) Qd(Ax Ik Il Im Lj) Mx(aA Lv Me Nt) aA(Lv Mb Nj) On(Ng Of) AaIs CuYi

Figure 40 Continued

Unconstrained panels with 2 analytes, where 1.0E-5 >= 'model p-value' > 1.0E-6. Contains 186 panels of 142,491 total panels evaluated. : Iv(Et Fr Hr Im In Is Jh Jk Jl Jm Jo Jp Jq Lj Lv Lw Ly Ma Mb Mh Mi Mj Mp Mt Mu Mz Nd Ng Nj Nk Nl Nq Ns Nt Nu Nv Nw Nx Oe Og Oh Oi Pa Pc Pg Po Qa Qd) Qd(aA Ad aU aZ Bb bS cB cF fR Is Iu Ji Jj Jl Jm Lh Li Lv Ma Mb Mu Mx Nj Nl Nq Ns Nt Nv Nx Ok On Pz Wm) Is(aA Ad Ax Cq Dd dX eP Iq Jj Jm Lj Lv Mb Mx Nj Ns Nt Nu Ok Um Yi Yl) Nn(aA Im Ji Jj Jl Mh Mi Mj Mx Ng Nk Nl Nu Oy Pg Qa Tz) Mx(Im Ji Jj Jl Ma Mb Mi Mp Nj Nl Nu Ok On Pg) aA(Ik Ji Ma Mf Mh Mj Nk Nl Nt Nu Nx Pg Po) On(Jj Mb Mw My Nj Oy Pb) Mb(Ji Jl Mi Ok) Nt(Jj Jo Ng) Tz(Nd Qv Um) Ji(Hw Om Pb) Oh(kG Um Wm) Cu(Jo Yj) Ma(lY mE) Nw(Gb Pb) aZ(Aa Nb) cU(dH fR) NsoE MjkG NdUm TncM JjPg OkPb Unconstrained panels with 2 analytes, where 1.0E-4 >= 'model p-value' > 1.0E-5. Contains 1,180 panels of 142,491 total panels evaluated. : Qd(aC aD aE aF aG aH al AJ aK AL aM AN AO AP aQ AR AS aV aW aX aY BA bB BC bE bF BG bH bI bJ bL bM BN BO bP bQ bR bU bV bW bX bZ cA cC cD cE cG CH cI cJ cK cL cM cN CO CP CQ cR CS CT CU CV CW cX cY cZ dA dB DC DD DE dF DG dH DI dJ DK DL dM dN dX EfeM eP Et Fp Fr Gd Ha Hb Hq Hr Hu Hv Hw Hx Ib Id Ih Ii Ij In Io Ip Iq Ir It Jg Jh Jk Jn Jo Jp Jq Jr Js Jt Ke kF kG Ko Lu Lw Lx LY Lz Mc Md Me MF Mg Mh Mi Mj Mk Ml Mm Mn Mp Mq Mr Ms Mt Mv Mw My Mz Na Nb Nc Nd Ne Nf Ng Nh Ni Nk Nm nN No NR NU Nw Ny OE Of Og Oh Oi Om Oy Oz Pa Pb Pc Pd Pe Pf Pg Pj Po Qa Qb Qc Qe Qv Ue Um) Is(An As aZ Bn Bo cB cF Cp CU Cw Dc EM Et Fr Gb Hp Hq Hr Hu Hw Ih Ii Ij Ik Il Im In Ir Iu Jh Ji Jk Jl Jn Jo Jp Jt kF kG Kr Lh Li Lu Lw Ly Lz Ma Mc Md Me Mf Mg Mh Mi Mj Mk Mm Mn MP Mq Ms Mt Mu Mw My Mz Nb Nc Nd Ne Ng Nh Ni Nk Nl Nm nN Nq Nr Nv Nw Nx Ny Oe Of Og Oh Oi Om On Oy Oz Pa Pb Pc Pe Pf Pg Po Pz Qa Qb Qc Qe Uy Yg Yj) aA(cU eD Et Fp Fr Hq Hr Hu Hv Hw Ih Ii Ij Il Im In Io Ip Iq Ir It Iu Jg Jh Jj Jk Jl Jm Jn Jo Jp Jq Jr Js Jt Lh Li Lj Lu Lw Lx Ly Lz Mc Md Me Mg Mi Mk Mm Mn Mp Mq Mr Ms Mt Mu Mv Mw My Mz Na Nb Nc Nd Ne Nf Ng Nh Ni No Nq Nr Ns Nv Nw Ny Oe Of Og Oh Oi Ok Om On Oy Oz Pa Pb Pc Pd Pe Qa Qb Qc Qe) Nn(eD Et Fp Hq Hr Hu Hv Ih Ij Ik Il In Io Ip Iq Ir It Iu Jh Jm Jn Jo Jp Jq Jr Js Jt kE kG kl Lh Li Lj Lu Lw Lx lY Lz Ma Mc Mf Mg Mk Mp Mq Mr Ms Mt Mu Mv MW My Mz NA Nb Nc Nd Ne Nf Nh Ni nK No Nq Nr Ns Nv Nw Nx OE Of Og Oi Om On oO Oz Pa Pb Pc Pd Pe Po Qb Qc Qe Ue Um) Mx(Et Fr Hr Hu Hv Hw Ih Ij Ik Il In Ip Iq Ir It Iu Jg Jh Jk Jm Jn Jo Jp Jq Jr Js Jt kG Lh Li Lj lN Lu Lw Lx Ly Lz Mc Md Mf Mg Mh Mj Mk Mm Mq Mr Ms Mt Mu Mv Na Nb Nc Nd Ne Nf Ng Nh Nk No Nq Nr Ns Nv Nw Nx Oe Of Og Oh Oi Oy Oz Pa Pb Pc Pe Po Qa Qb Qc Qe Um) Iv(Fp Hq Hu Hv Hw Hx Ih Ii Ij Ik Il Io Ip Iq Ir It Iu Jg Jn Jr Js Jt Lh Li Lu Lx Lz Mc Md Me Mf Mg Mk Ml Mm Mn Mq Mr Ms Mv Mw My Na Nb Nc Ne Nf Nh Ni Nm No Nr Ny Of Om Oy Oz Pb Pd Pe Pf Pz Qb Qc Qe) Ji(Hr Hv Ij Ik In Iq Jj Jk Jl Jo Jq Li Lj Lv Ma Md Me Mh Mj Ml Ms Mu Na Nb Nc Ne Nf Ng Nj Nk Nl Nm Nq Ns Nt Nu Nv Nx Ny Of Og Oh Ok On Pg Po Qa Qb) Ok(Hr Hv Hw Ij Ik In Jj Jk Jl Jo Lj Lv Ma Me Mf Mh Mi Mj Mp Mu Na Nb Nc Ne Ng Nj Nk Nl Nm Nq Ns Nt Nu Nv Nw Nx Ny Of Oh Om On Pg Po Qa Qb) Nt(Hq Im In Jl Jm Jp Jq Lh Li Lu Lv Ly Ma Mb Me Mg Mh Mi Mj Mm Mp Mt Mu Mz Nd Nj Nk Nl Nm Ns Nw Oe Of Og Oh Oi On Pa Pc Pg Po Qa Qb) Ma(aZ kC kE kF kG kI kK kN kO kP lW lX mF mH ml mM mP mS mT mU mY mZ nB nC nF nH nl nJ nK nL nM nN nO nR nT nU On oO oP oQ Tz Um) Tz(Ax bN cF Gb Hb Hp Hr Ii Iu Jo Ju Jv kG Lh Li Lj lN Mm Mu Mv Nq Ns nU oE Oh Pc Qy Rc Rm Rx Si Uf Uy Va Vu) On(dX eP Hq Hr Ii Ik Im Jg Jh Jo Lv Me Mf Mh Mi Mj Mv Nb Nc Nk Nl Ns Nu Nx Ny Oe Og Oh Om Pg Qa Qb Yi) cU(aJ aV aZ BO bQ bR bU cA cB cC cE cF cI cK cO cS cT cY dA De dI dJ Gd Hr Jj Jo Lh nI oE Oy) Tn(dX eP fB Jo kG kI kP lX mE mF mM mP mS mU mY nN nR nT nU oO oP oQ) Lv(aZ Im Jj Jl kG Mi Mj mP Mt Mu Nk Nl nN Nu Nw Oh Pg Qa) oE(Ad Ax aZ Ed Ef Hb Hc Je Jf Nd Nm Pc Qn Um Vv) nR(Hl Jj Jo Lx Lz Mb Ml Mm Mn nl oO Pe Pf Qa) Pg(Gb Hq Im Jm Jo Mb Mi Ng Nj Nl Nu Of Oy) aZ(aJ bO cF cS Cv Gb Gd Hp Hr Me Og Rx Yh) Qa(Hw In Jj Jm kG Lj Mb Mi Ns Nx Pb Um) Nw(fR Hq My Nj Nl Nu Ny Of Uw Yi Yl) Um(Hx Kq Mj Mp Mu Mv Mz Nq Or Ou Ut) Cu(Ad Gb gV Hl oO Uz Wg Yg Yh Yf) Mi(Hq Ik Me Nj Nk Nl Nu Nx) Oh(dX eP kF oO Qv Ra Rf Rg) kG(Gp Lx Mu Nb Nq Ou Pc Pf) Lx(fR Gb kF mP nN nU) eP(cT Kq Ld Pe Qe Uf) Nd(Lp Qv Rx Sf Sh) Nq(eD lL lN lY) Jj(Jl Nu Nx Po) Mb(Jt mP Nv) Mz(Ad Nf Pb) Jl(Nj Nl Nu) Jr(Gb Yi Yj) IN(hR Ky Mf) oO(aJ Kq oQ) Mj(kF nI) Mu(lY mE) Jo(cB De) Yl(Or Ou) Nv(Nj Of) Vv(nU Va) Pf(mP nN) cT(dX gV) jD(lL rZ) GbOw GdGp NbkF NgJk HvYi IdlL QedX QumE aPdH bAgV nUnI hRrZ Unconstrained panels with 2 analytes, where 1.0E-3 >= 'model p-value' > 1.0E-4. Contains 3,441 panels of 142,491 total panels evaluated. : Tz(AA aC AD aE AF aG aH al AJ aK AL aM AN AO AP aQ AR AS aU aV AW aX aY aZ bA BB BC bE bF BG bH bI bJ bL bM Bn BO bP bQ bR bS bU bV bW bX bZ cA cB cC cD cE cG CH cI cJ cK cL cM cN CO CP CQ cR CS CT CU CV CW CX cY cZ dA DB DC DD DE dF DG dH DI dJ dK DL dM dN Dp Du dX Ed eF Eq Et Ez Fc Fi Fn FP FR Fw Fy Gd Gh Gl Gn Gp Gz Ha Hc Hf hG Hl Ho Hq Hu Hv Hw Hx Ib Ic Id Ih IJ Ik Il Im In Io Ip Iq Ir Is It Iv Iz Jd Jg Jh Ji Jj Jk Jl Jm Jn Jp Jq Jr Js Jt Jy Kc Kd Ke kF Kg Ki Kj Kl Kn Ko Kp Kr KS Kx Ky Kz Lp Lt Lu Lv Lw Lx Ly Lz Mb Mc Md Me Mf Mg Mh Mi Mj Mk Ml Mm Mn MP Mq Mr Ms Mt Mv Mx My MZ Na Nb Nc Ne Nf Ng Nh Ni Nj Nk Nl Nm nN No NR NT Nu Nv Nw Nx Ny Oa Oe OF Og Oi Ok Om On Or Ou Ow Oy Oz Pa Pb Pd Pe Pf Pg Pj Po Pz Qa Qb Qc Qd Qe Qg Qh Ql Qm Qn Qt Qu Qw Qx Qz Ra Rb Rf Rg Rh Ri Rj Rt Rv Ry Rz Sf Sh Sr Ss St Tn To Tr Tt Tv Ua Ub Uc Ud Ue Ug Uh Uk Ul Un Uo Up Ur Us Ut Uu Uv Uw Vb Vj Vo Vp Vq Vs Vt Vv Vz Wc Wf Wg Wh Yd Yg Yh Yi Yj Yl Zq Ye Tm Wm Tj tF Yf) oE(aA aC aD AF aH Aj aK Al aM AN AO AP AR aS aU aV AW aX aY Ba Bb BC BG bH bI BN BO bP bR bS bU bV bZ cA cB cC cD cE cF CH cK cL cM CO CP Cq cR CS CT Cu CV CW CX dA Db Dc Dd DE DG dH DI DK Dl dN Dp Et Ez Fa Fb Fn FP Fr Fw Fy GL Gp Ha HF hG Hq Hr Hv Hw iA Ib Ic Id Ii IJ Ik Im In Io iP Iq Ir Is It Iu Iv Iz Jd Jg Jh Jj Jk Jl Jm Jo Jp Jr Jt Ju Jv Jy Kc Kd Ke Kf Kg Ki Kj Kk Kl Kn Ko Kp Kq KR Ks Kx Ky Kz Ld Lh Li Lj Lu Lv Lw Lx Ly Lz Ma Mb Mc Md Me Mf Mg Mh Mi Mj Mk Ml Mm Mn Mp Mq Mr Mu Mw Mx My Mz Na Nb Nc Ne Nf Ng Nh Nj Nk Nl Nm Nn Nq nR Ns Nt NU Nw Oe Of Oh Oi Ok On Op Oy Pb Pc Pg Po Ry Rz Sf Sh Si Sj Uy Vz Wb Wh Yd Yg Yi Yj Yk Yl Zq Zw Zx Ye Tm Tl Xa Yf) Is(aC aF aH Aj aK Al aM aN aO aP aR aU aV aW aX aY bA Bb BC Bg bH bL bN bO bP bR bS bU bV cA cC cD cE cG cH cI cK cL Co CS Ct CV cW cY dA dB De DG dH Di dJ Dk DL dM dN Dr Du Fp fR Gd Gn Gp Ha Hb Hl Hv Hx Ib Id Io Ip It Jg Jq Jr Js kC Kd kE KN Ko KP Lx lY mE Ml mM Mr mT mU Mv mZ Na Nf nH nl No nR nT nU Pd Pi Qv Ra Rj Rm Rx Ry Tv Uc Ud Ue Ul Uo Up Ur Us Uw Uz Va Vb Vh Vi Vp Vs Vt Vu Vv Wc Wf Wg Yh Yk Tl Xa Wm Yf) cU(Aa aC AD aE aF aG aH al Aj aK aL aM aN aO aP aQ AR AS aU AW AX aY BA BB BC bE bF BG bH bI bJ bL bM BN bP bS bV bW bX bZ cD cG cH cJ cL cM cN Co cP CQ cR Cu cV cW cX cZ DB DC dD dE dF DG Di DK dL dM dN Em Fr gV Hp Hq Ii Im Iv Ji Jm Jr kG Li Lj Lv LY Mb ME mF Mh Ml Mk Mm mZ nA Nb Nd Ne Nf Ng nK Nl Nm Nn nR Ns NU Nw Oe Of Oi Ok oO oV Oz Pa Pb Pd Pe Pf Pg Rx Sf Sh Um Yg Yi) Lv(Ad aR As aU AX BO bS cB cF cK De dX Em eP Et Fp FR Hq Hr Hu Hv Hw Hx Ih Ij Ik Il In Io Ip Iq Ir It Iu Jg Jh Jk Jm Jn Jo Jp Jq Jr Js Jt kC kF Lh Li Lj Lu Lw Lx Ly Lz Ma Mb Mc Md ME Mf Mg Mh Mk Mm Mn Mp Mq Mr Ms mT mU Mv My Mz Na Nb Nc Nd Ne Ng Nh nI Nj No Nq NR Ns nT nU Nv Nx Oe Of Og Oi Om Oy Oz Pa Pb Pc Pd Pe Pf Po Pz Qb Qc Qe Um) Oh(eD EM Et Gb Gd Hp Ik Im Jj Jl Ju Jv kE kl kK kN kO kP lX lY Ma Mb ME Mi Mj mP mS MU mW mZ nA NB nC nF nI Nj NK Nl NN nR nT nU Nv Nw Nx Oe Pg Po Qa Qb Qh Qt Qu Qw Qx Qy Qz Rb Rc Rh Ri Rj Rm Ru Rx Sr Ss Tn To Tv Ub Uc Ud Ue Uf Ug Uh Uk Ul Uo Up Ur Us Ut Uu Uw Uy Uz Va Vb Vh Vo Vp Vs Vt Vu Vv Wc Wf Wg Yi Yj Yf) Qd(Af Aw Cx Db Dp Em Ex Ez Fn fP Fw Fy Gb Gl GP Gz Hc Hf Hp Ic Iz Jd Je Ju Jv KC Kd kE Kf Kl Kj KK Kl KN kO KP Kq Kr Ks Ky Kz Ld Lp lW lX mE mH mM mP mT mU mW mY mZ nA nB nC nF nH nl nL nM nO nT Oa oO oP oQ Or Ou Ow Ph Pi Pk Qg Qn Qy Ra Rc Rf Rj Rm Si Tr Tv Ub Ud Ug Uk Ul Uo Up Ur Ut Uu Uy Vo Vp Vs Vt Vv Tj tF) Mi(As Bo bS cB cF cK Et Fp FR Gb Hr Hu Hv Hw Hx Ih Ii Ij Il Im In Io Ip Iq Ir It Iu Jg Jh Ji Jj Jk Jl Jm Jn Jo Jp Jq Jr Js Jt Lh Li Lj Lu Lw Lx Ly Lz Ma Mc Md Mf Mg Mh Mj Mk Ml Mm Mn Mp Mq Mr Ms Mt Mu Mv Mw My Mz Na Nb Nc Nd Ne Nf Ng Nh Ni Nm No Nq NR Ns Nv Nw Ny Oe Of Og Oi Om Oy Oz Pa Pb Pc Pd Pe Pf Po Pz Qb Qc Qe Um) Pg(Et Fp Fr Hp Hr Hu Hv Hw Hx Ih Ii Ij Ik Il In Io Ip Iq Ir It Iu Jg Jh Jk Jl Jn Jp Jq Jr Js Jt kF kG Lh Li Lj Lu Lw Lx Ly Lz Ma Mc Md Me Mf Mg Mh Mj Mk Ml Mm Mn MP Mq Mr Ms Mt Mu Mv Mw My Mz Na Nb Nc Nd Ne Nf Nh Nl Nk Nm nN No Nq Nr Ns nU Nv Nw Nx Ny Oe Og Oi Om Oz Pa Pb Pc Pd Pe Pf Po Qa Qb Qc Um Vb Yi Yj) Qa(Aa dX eM eP Et Fr Hq Hr Hu Hv Ii Ij Ik Il Im Iq Iu Jh Jk Jl Jo Jp Jq Jt kF kO kP Lh Li Lu Lw lY Lz Ma Mc Md ME MF Mg Mh Mj Mk Mm Mn MP Mq Mr Ms MT MU Mw MZ Nb Nc Nd Ne Ng nl Nj Nk Nl nM nN Nq nT NU Nv Nw Oe Of Og Oi Om Oy Oz Pa Pc Pe Po Pz Yi Yj) kG(aA aF aO Aw Cu Di Em Fd Fw Gb Gd Gn hC Hl Hp Hq Hr Hu Ic Iv Ji Jj Jk Jl Jn Jo Jq Kd Ke Kq Lh Li Lp Lu Ly Lz Mb Mf Mh Ml Mm Mn Mp Mq Mr mU Mv Mw Nd Ne Nl Nm nN NR Ns Nt NU Nv Nw Of Oi Ok On Or Oz Pb Pd Pe Pi Po Qb Rv Uf Ut Vu Vv Yd Yg Yh Yi Yj Ye) On(Et Fp FR Gb Hl Hu Hv Hw Hx Ih Ij Il In Io Ip Iq Ir It Iu Jk Jl Jm Jn Jp Jq Jr Js Jt Lh Li Lj Lu Lw Lx Ly Lz Mc Md Mg Mk Ml Mm Mn Mp Mq Mr Ms Mt Mu Mz Na Nd Ne Nf Nh Ni Nm No Nq Nr Nv Nw Oi Oz Pa Pc Pd Pe Pf Po Pz Qc Qe Ry Um Uw Vb Vh Yg Yj Yl) Nw(Ad aU Ax Bb bS cB cF Dg dX eP Et Gd Hb Hp Hx Ik Im Ji Jj Jl Jt kF Lj Lw Ma Mb Md Me Mf Mh Mj Ml MP Mq Mu Mv Mw Nb Nc Ne Nf Ng Nk nN Nq nR Ns nU Nx Og Om Oy Pc Po Qb Rt Ru Rv Rx Ry Sf Si Um Ux Uy Uz Va Vb Vh Vi Vz Wc We Wf Wg Yj Wm Yf) Um(aR cF cT Cu Dc De Ed Et fP Fr Fw Fy Gp Hc Hv Ij Il Im Iu Iv Jh Ji Jl Jn Jo Jp Jq Jr Lh Li Lj Lu Ly Lz Mf Mg Mh Mk Ml Mm Mw Na Nb Nj nR Ns nU Ok Om Pc Pd Pi Po Qb Qe Qh Qn Qv Qx Qy Rc Rf Rh Tn Ub Uc Ue Uf Un Uo Up Vi Vo Vp Vu Vv tF) nR(aA aF Al cF Cv Gn Hr Ii In Io Ip Iv Ji Jk Jm Jn Jq Jr Jt Ju kC kE kF kl kK kN Lh Li Lu lY Me mF Mh Mj MP Mq mS MU Mx Nb nC Nd nF nH Ni Nj nL Nm NN Nq Ns NT NU Ny Oe Of Og Oi Ok Pb Pc Po Qb Rb To Ug Ur Ut Vv) Jl(Et Gb Hp Hq Hr Ih Ii Ij Ik Im In Iq Iu Jh Jm Jo Jp Jq Js Jt kF Lh Li Lj Lu Lw Lx Lz Ma Me Mf Mg Mh Mj Mk Mm Mp Ms Mt Mu Mw Mz Nb Nc Nd Ne Ng nl Nk Nm nN Nq Ns Nv Nx Oe Of Og Oi Om Oy Pa Pb Pc Pe Po Qb Qc Rx Yi Yj) Ok(dX Et Fp Fr Hq Hu Hx Ih Ii Il Im Io Ip Iq Ir It Iu Jg Jh Jm Jn Jp Jq Jr Js Jt Lh Li Lu Lw Lx Ly Lz Mc Md Mg Mk Ml Mm Mn mP Mq Mr Ms Mt Mv Mw My Mz Nd Nf Nh Ni nN No Nr nU Oe Og Oi Oy Oz Pa Pc Pd Pe Pf Pz Qc Qe) Ji(Ad Bo Cw dX eM eP Et Fp Fr Hq Hu Hx Ih Ii Il Im Io Ip Ir It Iu Jg Jh Jm Jn Jp Jr Js Jt kF Lh Lu Lw Lx Ly Lz Mc Mf Mg Mk Mm Mn Mp Mq Mr Mt Mv Mw My Mz Nd Nh Ni nN No Nr nU Oe Oi Oy Oz Pa Pc Pd Pe Pf Pz Qc Qe) Nt(Et Fp Fr Hr Hu Hv Hw Hx Ih Ii Ij Ik Il Io Ip Iq Ir It Iu Jg Jh Jk Jn Jr Js Jt Lj Lw Lx Lz Mc Md Mf Mk Ml Mn Mq Mr Ms Mv Mw My Na Nb Nc Ne Nf Nh Ni No Nq Nr NU Nv Nx Ny Om Oy Oz Pb Pd Pe Pf Pz Qc Qe) Mj(cB dX eP Et Ik Im Jj Jm kC kE kl kK kN kO kP Lj Lw lX lY Ma Mb ME mF mH ml MM MP MT MU mW mY MZ nA NB NC nF Ng nH Nj Nk NL nN nO Nq Ns nT NU Nv Nx Og oO Pc Po) Nn(cB Fr Hw Hx Ii Jg Jk jP kC kF kK kN kO kP IL lM lN lW lX Ly Md mE mF mH ml Ml MM Mn mP mS mT mU mY mZ nB nC nD nF nl nJ nL NM nN nO nT nU Ny oP oQ oW Pf Pz Qv Ra Wm) Nd(cB De Du Ed Fi Gb Gh Gp Gz Hl Ho Hp Jf Ju Ky Lt Mb Nj Nl Ou Ow Ps Qn Qy Ra Rf Rg Rh Ru Ry Rz Si Tn Ue Uf Uh Uk Uo Ut Uy Va Vj Vp Vu Yi Yl Ye Yf) Tn(Ad Bb Dg dU eQ fR Gb gC gZ Ib Iz jB kC kE kF kK kN kO lW lY mH ml mT mW mZ nA nB nC nD nF nH nl nJ nK nL nM nO oD oT oV oW pH pl pK Uu Vb) Lx(dX eM eP kC kE kl kK kN kO kP lW lX lY mE mF mH ml mM mS mT mU mW mY mZ nA nB nC nD nF nH nl nJ nK NL nM nO nT oO Yi Yj) Nq(Je jG jl Jj jO jT kC kE kF kl kK kN kP lM lW lX Mb mE mF mP mT mU mW MZ nA nC nF Ng nH nl Nj nK NL nT Nu oO Sh) rZ(eD hA hV hW hX iC jE jF jG jH jl jL jM jO jP jQ jR jT jU jV jY lK IL lM lN lO Mx qT qU qW qX qY rA rB rC) nN(aA aF Hr Jj Jo Jq Jr Jt kE kl kN Lh Li Lu Lz Mb Mh Ml Mm Nb Nl Nm Ns Of Oi oO Pc Pe Qb Ut Vv) Nu(Et Fr Im Jk Jq Jt Lh Lw Lz Ma Mb Me Mf Mh Mp Mt Mu Mz Nb Ng Nj Nk Nl Nv Nx Og Pc Pe Po Qb) Mu(eD Jj kE kF kl kK kN IL lN Mb Me mF mS mY nA nC Ng nl Nj nK NL nT oO oP oQ Po Qv Ue) aA(Aa bO cB cF dH fR hR hW Hx iC jD jO jP jT jV kF IL lM lN lO mE Ml mP Nm nU oO Pf Pz) Po(cB Hr Im Jm Jo Li Lj Lu Lw Ma Mb Mp Mt Mz Nb Ng Nj Nk Nl Ns Nv Nx Oe Of Og Pc) Mx(cB Fp Hq Hx Ii Io kF IL Ml Mn Mw My Mz Nl Nm Ny Om Pd Pf Pz Qv qW rY Wm) cB(aP Hr Im Iv Jj Jr Lh Ly Lz Ma Me Mh Mm Mp Nb Ne Ng Nm Ns Oe Og Oy Qb) Pf(fR kE kF kK kP lW lX lY mE mF mM mT mU mZ nC nF nl nK nL nO nT nU) mP(aF Hr Jj Jo Jq kE Lh Lu Lz Mh Ml Mm Nb nl Nm Of oO Pc Pe Qb Ut Vv) Nl(Et Fr Im Jj Jk Jp Jq Lh Lw Ma Mb Mh Mp Mt Mz Nb Nv Nx Pc Pe Qb) Cu(Aa Dg Gd Hp Hr Hw Ii In Jt kl mE Mm nl Nm Oy Pb Uy Vb Vh Yk) Jr(Dr Du dX EM eP fR Gn Hl Hp Rx Ry Uz Wg Yg Yh Yk Yl Tl Yf) Ut(dX eP Jo kF kl kK kN lX lY mE mF Mm mW mY nl nT nU oO Qv Yf) Mb(Et Fr Im Jk Jp Jq Js kF Lh Lw Mm Mp Mt mU Mz Nb nU Pc Qb) Jj(aU cF De fR Ih Ij Ik Im Jk Jq Js kF Ma mU Nj nU Nv Pe Qb) oO(aF aO aP bQ bV bZ cF dF dG eC fA fR hC Mp Mt Nb oF pH) nU(aF Cv Hl Jq Li Lz Mh Ml Mp nA Nb nF Ns Of Pc Pe Ur) Ma(bS cE fB Im Mt mW Mz nA nD Nj Nk Nv Nx oT Qb) kF(Lh Lu Lz Ml Mm Mp Mv nl Nm Oe Of Oi Ou Pc Qb) Mz(As Cq Cw dX Hw Ij In Nj Om Uz Wg Yi Yj Yf) Mp(cF cK dX eP Gd kE kl kN lY mE nl Nj Qv) Gb(Ao Ed Fy Gp Hc Jp Js Ou Pe Vu Vv Yi) Ow(Du Gd Hp Rx Sf Si Uw Vz Yi Yj Yl Yf) cF(aJ aP bA cS ED hR Im Jo Me Mh Or) dX(Aw Dc Fy Ij Jn Jq Ke Kq Ny Pe Uf Vs) De(aP BO bV cS Gd Hr Me Mm Nf Oy) Nj(Et Fr Im Jk Jp Lh Mt Nb Pc Pe) Vu(Dp Gd Hl Hp Hr Jo Lp mE Qv Si) IL(aD aM aX BC bO dl hR jP Mf) lN(aM Dl Fr Id jD jl jO jP Mv Or) Gp(Aa Fi Or Ps Rx Sf Sh Wc Yf) Nv(Hq Im Me Mh Ng Nk Og Pb Ry) Nb(kE kN lY mU nl nT Yi Yj) Jo(aU Ba cG cT Dc Ou Uf tF) Kq(lY mE mT mW nl nJ Yi Yf) Vv(Hp Lp Rx Sf Sh Ux Vb Vj) cD(dl Fr hR jD Lj Mf Mv Pc) gV(aL Aw Ba bO Cw Dc dD) Yi(Js oF Or Ou Rx Vi) cT(EM Gd Je Rx Uo) Mf(jl jO jP Me qW) Yj(bO Hv Js Ou Vi) Uf(Dg kl mE Nm Ue) eP(Aw Dc Ij Jn Ke) oF(fR Gd Gh Hl Yh) Aa(Dc Ed Iv Me) Mh(aX Et Im Nx) Or(As Hr Lw Oy) Ou(Hr Oy Qv Yf) aP(bL bO bR dG) Gd(Ao Aw Hc) Ns(Ir Qv tF) Lz(mU mZ nT) Hv(Lp Yg Yf) Im(aU bS Nk) aF(nl oV oW) Me(aU aX) Ue(Mv Qy) Id(jl lM) Hc(Sh Va) Qb(Jm Nx) Li(lY mE) Oy(Aw Ef) Pc(oV oW) cE(cG dF) cS(BO) eM(Pe Qe) nl(Ky nT) AoSh EdHp YfJq EtNk FrNg HlHo TopH JsUy JvoT LpkN NyPb UoVi bAfR hRjO jDjP Constrained panels with 3 analytes, where 1.0E-10 >= 'model p-value' > 0. Contains 4 panels of 23,517,221 total panels evaluated. : Tn{Ss(nR nT nU) JjeM}

Constrained panels with 3 analytes, where 1.0E-9 >= 'model p-value' > 1.0E-10. Contains 13 panels of 23,517,221 total panels evaluated. : Tn{Al(kl mS) Kl(mW nl) JonT} lN{Tz(Ax Cs) dKhR} Cu{ApYj YgaZ} IdUhIL JlJuoO KjVvnU Constrained panels with 3 analytes, where 1.0E-8 >= 'model p-value' > 1.0E-9. Contains 69 panels of 23,517,221 total panels evaluated. : oO{Tn(Ad Ao Ap Bb Cv Dd Dg Dl Iz Ke Kg Kj Kl Ks Ok Pj) Kq(Iz Jo Ju Kg Nm Of Pz Ss Ug Vo) Jv(oE oF)} Cu{Yj(Ad Dg Gb Jt Nn Oi Ok Rz Ux Vj Vw) Yi(Dg Jo Kg Kj Kl Mh Nb)} Nn{Iv(Jj Jo Li Ng) Ng(Nt On) MbOk NjaA QdLi OnOy} Tn{oP(Hb Ke Kq Ks) Ss(mP nN) AdnU lioQ} On{li(eP Yf) MuOy} MbMxaA JuaUlX

Figure 40 Continued

Constrained panels with 3 analytes, where 1.0E-7 >= 'model p-value' > 1.0E-8. Contains 485 panels of 23,517,221 total panels evaluated. :
Nn{Ng(Is Ji Jl Lv Me Nj Nl Nu Nv Nw Ok Pg Qd) Iv(aA Jm Lj Lv Mb Me Nj Of Og Oi Ok Oy) Nj(lm Is Jj Lv Mx Nd Ok Oy Qd) Me(Is Jh Jj Mv Mx Ok Oy Qd) Jj(Is Lv Nl Nt Nx Pg Qd) Lv(aA Nl Of Oy Qd) Ma(gZ jB oT oV oW) Md(aA Is Ji Jl Qd) Ok(Jh Of Om Pb) Qd(Jm Jt Lj) Cu(oW Yi) Li(Is Tz) On(Mw Of) cT(oV oW) NtJo MzNf KqmE NwOy PdoT bZgZ} Cu{Yi(Aj Ap Ba Bc bL bS Cw Ef Gb Gz Hv Ib Ii In iO Is Jj Jr Jt Kf Ki Kq Ks Lz Ma Ml Mz Nd Oh Oi OK Om Or Ow Ph Rt Rz Ux) Yj(Bb Bc Cw Dl Ef Iz Jg Kl Kq Ma Mm Oh Ow Rc Tr Uf) nI(Ad Bb Dg Jt Nm) oO(Jo Ju Nm Of) In(Gb Op Ry) Yg(aS bl) eM(Ux Vw) GbKd NdHl liUz WgJm} Is{Ax(Aa Ad As Cp Cq Cw Dd Hr Hv Hw li Ij In Ir It Jn Jo Jr Jt Mb Mr Nf Oy Pb) Aa(aZ cC Mb Nb Ns Pa) Yi(Hb Jm Ju Jv Rm Sf) Yl(Gb Ju Jv Sf Sh) Rm(Hp Uy Uz Wg Yh) cF(Ad Dd li Jo Jt) De(Ad li Jo Oy) eM(Rt Uw Ux Vb) Gb(Kc Yj) Mb(aA Iv) Mx(Ir Js) AdIn MmeP HpQa HbUm YjJv WgJm} Tn{Dg(kG mW nl nR) Jj(fR nN nT oQ) eM(Lp Ou Rc Uu) Ss(mM mU nO) Jo(mP nN nU) kG(Ad Ba Bb) Ii(fR oP) Kl(nA nR) Ou(dX eP) nU(Oi Uu) oQ(Mm Pz) AdnI AjdX BbkP EfoO NdRy OkoP UgeP} On{Mb(aA Iv Jj Mx My Ng Of Oy Pb) Of(Iv Lj Lv Mu Mx Nj Nt Nu) Iv(Jj Ng Oy Pb) Mx(Mc Ng Oy) dX(Ha Iz Kf) Mu(Mw Ng) GbYj NdRy IzeP QdLi} aA{Mb(Iv Ji Lv Mj Nd Nv Ok Pg Qd) Nj(Iv Lv Ma Mj Mu Mx Nd Pg) Mx(Iv Lv Ma Me) Iv(Hr Lv Ma) Qd(Li Lj) MzNf} Qd{Li(aZ bH bS cB cU Iv Ok Wm) Ax(aZ bH bS cF cU Oy) cF(Ii Jo Oy) Lj(Iv Mx) MmeM NdLp IiaU JjfR} Ma{Jo(mE mM mP mU nN nR) Ny(oT pI pK) mE(Jj Nm) jB(Ax Lj) oV(Ij Li) GdnA MxIv aZcE cDpK} eP{Ld(bA Hx Jn Jr Nb Nt Pe Pg) Ut(Jj Jp Qv Ug) Jp(Jf Qm) Uf(Jo Ss) MpcT HcKx} Mx{Iv(Jj Lv Mc) Ok(Mb Mc Pb) Nt(Jj Jo) Ji(Mb Pb)} oO{Jv(Jl Ut) Kq(Rm Uu) kG(Mj Nb) pH(Mh oF) AlTr} Iv{Mu(Jj Ng) Ok(Jo Pb) NqNg JiPb JjPg} Li{Oh(Tz Uf Um) oV(bZ cT) QaUm OudX} Gd{kG(Hq Pg) GpZq NdRz PfkF cUnI} Ny{bZ(jB oD oT pI pK) bFoW} bA{gV(aK aQ aS aU bO cV)} Kq{Nm(mE mW nI oQ) IzdX} Ut{Jj(dX mE) IzmS SheM UrmE} Tz{Si(Mg Uf) GbMt LjlN} Qa{AlgC HpeM LjUm OkPb} Lx{AwdX AxjB NdRy} Vv{nU(Jj Jo) NdLp} Aa{aZ(cF Ji)} Mb{MjkG NdOk} Mu{NtNg OfOk} Jp{dX(Jf Qm)} Yl{GbNw ShOu} Pc{aFoW cSdU} cT{NioT JkoV} cU{JjfR aPdH} eM{IjVb OwUx} MjnIkG JvaUlX cFhRlN Constrained panels with 3 analytes, where 1.0E-6 >= 'model p-value' > 1.0E-7. Contains 4,169 panels of 23,517,221 total panels evaluated. : Tn{pK(Ad Aj Al Ap Ba cD Dc Dg Dl dN Dp Ez Hb Ih Ij Io Is It Iz Jg Jj Jo Jt Ju Jv Ke Kf kG Kj Kl Kq Ks Lj Lu Ma mF Nm Ny Oa Of Ok oP Pj Pz Qa Qh Qv Rc St Uc Ug Uu Vo) oT(Ap Bb Bc Cs Cu Dg Fp Hb Ii Io Jd Jg Ji Jj Ju Jv Ke Kf Kl Kn Kq Lh Li Lj Ma Mn mT Nm Ny Ok Pj Qa Qd Qh Qm Rc) oV(Ad aF Ao Ap Bc Cu Dc Hb Ih Ij Io Ji Jk Jm Jt Ke Kf Kn Kq Ma Mn mT Nm Nw Oa Ok Om Pj Pz Qa Qd Qh) pH(Al Ba Bb Bc Bg fP Ib Ih Ii Ji Jj Jk Jl Jo Jq Ke Kj Kl Kn Kq Lh Li Lj Ma Mn nJ Nw Om Ow Qd Ug) Vb(kC kF kG kI kN kO kP lW lX mF mH mI mM mP mT mU mW mY mZ nA nD nJ nK nL nN nO nR nT nU) gZ(Ap Ba Cs Dc Fp Hb Hw Ib Io Jg Jt Ke Kf Kl Kn Kq Lj Ma Mn Nm No Ny Ok oO Pj Qa Qd Qh Vt) Wb(kC kF kK kN kO lW lX lY mE mF mH mM mS mT mU mY mZ nB nC nD nH nI nJ nL nR nT nU) nU(Dg Eq Gd Gn Hl Ii Iz Jg Jj Jt Kj Kl Lp Mb Mm Nv Pz Qu Rz Ur Ux Vw We) oW(Ap Ba Fp Hb Io Jg Jk Jt Ke Kf Kl Kn Li Lj Ma Nm Ny Oa Ok Pj Qa Rc) eQ(Ad Ap Dc Dg Hb Ih Ii Jg Jt Ke Kf Kl Nm Ok Pj Pz Qa Qh Rc St Uu) kI(Ad Gb Ii Iz Jq Kl Ks Mm Nm Ok Ps Pz Rz Si Uw Ux Uy Yg Yi) Rz(kC kG kN kO kP mF mP mT mU mW nA nD nK nL nN nR nT) dU(Ax Bc Ih Ir Jo Kc Ke kG Kj Kn Ma Oa Og Ok Qd Ug Vo) nN(Ad Bb Fy Ii Iz Jg Jt Lp Mm Nn Nv Oh Oi Pz Uu Yg) kP(Gb Jj Jo Jt Kl Mm Nm Oh Ok Pz Rc Ss Uu Ux Yg Yi) gC(Ax Fa Ih Ij Jj Jo Kj Lh Lj Ma Ny Oa Qd Ug Vo) oD(Ax Ba Bc Cs Fp Ii Kn Ks Lj Ma Ny oO Qa Qd Qn) mH(Al Gb Gd Hp Ps Rt Sf Sh Uw Ux Uy Va Vw Yi) jB(Cu Ez Ii Ir Jg Jo Kl Kn Kq Ma Oa Ok Qa Ug) pI(Bc Ii Ij Jj Ke Kj Kn Lj Ma Ny Pz Qa Qd Vo) nT(Fy Hl Ii Iz Jt Kj Mm Nn Oi Rc Ug Uu Vo) Yg(kC kO lX mE mI mS mY nC nI nJ nO nR) Lp(fR kG kO lW lX mT nC nD nH nI nJ nR) mP(Bb Dg Iz Jg Jj Jt Kj Mm Oi Uu) oO(Aa Aj Bg cF Cp Dc Fb Hb Kf Lu) mS(Ad Iz Kl Ks Mm Ok Uw Uy Yi) oQ(Aa Jm Nm Nn Nv Ny Of Oh Ug) mY(Mm Nm Ok Uw Ux Uy Va Yi) Jj(mE mM mT mU nB nO nR) Jo(fR mI mM mT mU nO nR) nA(Al Bb Dg Gb Hp Ok Ux) Rt(fR kC kN kO mW mZ) eM(Ad Bc Hp Jt Kj Ug) kG(Bg Iz Kj Kl Nd Ss) oP(Aa Bb Bg Fb Pj Ug) Uu(fR mM mU nO nR) kC(Gb Uw Ux Va Yi) fR(Ad Iz Mm Ug) mF(Gb Kl Ux Yi) nI(Al Bb Iz Rc) nJ(Hp Ok We Yi) oE(Ad Ib Of Um) Oi(mM mU nR) Al(kE mT) Hp(mE nH) Kl(kF nB) Ux(kN mW) eP(Ld Ur) nR(Nv Rc) BbnB DgkF GbkN GdmW NnOy NdOf HlkO ShnO WenH RymT RxlW UgmE UykE} Is{Ad(Al As aU Bg Bo bU cA cB Cp Cq Cw Dd Hp Hr Hv Hw Ih Ii Ij Ir It Jm Jn Jo Jr Js Jt Lh Li Lj Lp Lu Ma Me Mm Mr Mu Mv Nf Nm Ns Pb Uw Uy Yi Yj Yl) Nn(AA Dd Gb Hp Ii Iq Ir Iu Jh Jm Jo Js Jt Lj Lv Mh Mv Mw My Nk Nl Ns Nt Nu Of Og Oi Ok Oy Um Yj Yl) Jo(Al An aO As aU Bb bC Bn Bo bR bU bV cB cC cL Cp Cq cS CU Cw Dc Dd dJ Hp Iv Nt Um) Iv(Aa Ax Ii Ik In Iq Ir Iu Jj Jm Jt Li Lj Lv Ma Mx Ng Nj Nk Nl Ns Nt Nu Og Qd) Al(Aa As Cp Cq Cu Cw Hr Hv Hw Ii Ij In Ir It Jn Jr Jt Mr Nf nI nO Pb Yi) Ii(Aa An aR As aU Bb bC bR bV cB Cp Cq CU Cw Dc Dd dJ Mx Nt Pg Yl) Yi(aO bN bO bS cC cD cU dJ Gd Hp In Jj kG Lu Oh Ow Qh Rf Sh Si Ye) Ax(An Bn Bo cF CU Dc Im Jq Js Kr Na Nb Ny Of Om Pe Qa Um Yl) Aa(aA aS bO bS bV cA cB cF Cv dJ Gp Iq Iu Jm Lu Mh Nd Ne Oy) Yl(dJ Du Et Gd Hb Hp Ih In It Jm Jt Lp Lu Mz Ow Rf Rm Si Ye) Jm(As Cp Cq Cw Dc Dd Iq Lv Mb Mx Nj Nt Nu Pg Qd Vi Yf) Gb(Ao aX bC Co Dc De Hp Li Mg Mi Mp Mu Qy Uf Uo Vv) Uy(bO Hp Ih Ju Jv mW nC nH nL nN Rf Sf Sh Si) cF(Cp Cq Cw Hr Hw Ij In Ir It Jn Mr Oy Um Uo) Dd(Bb bV De Js Jt Lh Li Lj Me Mm Nm Ns Ny) Mb(Iu Ji Jj Li Lj Mi Mx Nd Ns Nu Oh Ok On) Rm(Dr Gn Hl kC kG lY mE nO Um Vh Vi Tl) Hr(aC Ap aR aZ Bb bR bV cU De Dg Hb) Jj(fR Ik Iq Lj Lv Mu Mx Nj Nt Nu Pg) Jt(aR As aU aX bC bV cB Cq De dJ Nt) Hp(aZ kG Kq Om Ow Qb Qe Rf Ul Uo) Cq(De Js Li Lu Me Mm Nm Ns) Mx(Iq Jr Li Lj Ma Me Nj Ns) In(aC Ap Bb bR Dc Dg Hb) Um(Bb Iu Ju Li Lj Nd Si) Yj(Et Hb Oh Ow Qh Sh) aA(Li Lj Lv Ma Nj) cU(dH fR Js Mr Oy) kG(Lu Oz Pc Uw Yg) Nt(Li Ng Of Pz) Mm(As Bo Cp Cw) Ng(Mu Nq On) Hb(Rj Up Vp) Oy(bC cB Co) As(Js Ns) Cp(De Ns) Hl(mW Nd) Zq(kC kF) Qd(Li Lj) Of(Lj On) eP(Fy Ld) BbIt CwJs IdlL IrOk YgaO SiUo SfnL UxmY} Qd{Li(aO aU bA Bo bV cF cT De dF Gp Ib Ji Jj Jl Jm Lh Lv Ma Mb Mh Mi Mt Mu Mx Nb Nj Nl Nq Ns Nt Nu Nv Nw Nx oE Oh Pc Pg Po Qv Tz Um) Lj(Ad Ao bS cF Iu Ji Jj Jl Jm Lh Lv Mb Mh Mu Ng Nj Nl Ns Nt Nx Of Ok On Pz Um) Ax(aU bN bO bV cB cT De Gp Hb Jo Lh Lu Lv Ma Nd Ns Nw oE Qv Rf Um Wm) Lh(aA aO aU aZ bS bV cB cF cL cU dF Iv Lv Mx Nn Nt On) Ns(aA aU aZ Bb bH bN bS cB cF Iv Lv Mx Nn oE Ok On) Oy(aO aU Aw Bb Bg Bn bV cB cL Cs cU De Hb Nn On) aA(fR Iu Iv Jm Jt Lv Ma Mf Mu Mx Nj Nl Nn Nq Nx) Mx(Iu Jj Jm Lv Ma Mb Me Nj Nx Ok On Pz) Jo(aK aU bS cB cL cU cY De Iv Nn Nt) Jt(aU aZ bH bS cB cF cL Iv Nt Ok On) Ii(aK aZ bC bS cB cL cU cY Nx On) cF(Ad aZ bS cU Dl Ij It Jm Js Ng) Nd(Gb Ha Hl Hp Qv Rm Um Uy) Jm(Iv Lv Mu Nq Nt Nv Nx On) bS(Aa Ad aZ cL Js Lu Mm) Nn(aU Iq Iu Nl Ok Pz) Iv(Iu Jj Lv Ma Mu Pz) On(Jj Mb Ng Nj Pb Pz) Ng(Jk Mu Nq Nt) Hb(Ha Ib Je Um) Js(aU cB cT cU) Ad(aU cB Lv) Bb(aU Hr Um) Mm(Bo cB Nx) Wm(Fp Oh) Nt(Jj Pz) Ma(cE mE) Mb(Ji Ok) cU(dH fR) AaaZ HaLu MeMu HpkG IdoE IucB JjNx LdeP RmOh OkPb UymW} Cu{Yi(Dl Em Eq Fd Gd Gp Hr Iz kC kE kF kI Kn Ko Ld lW mH mI Mj Mm mZ nO Nw Qb Qx Rc Sr Tr Tz Uf Uu Uy Vh Vo Vw Wb) Yj(Aj Ba Bg Fr Fy Hp Ib Jp Kf Kg Lh Mh Ng Nm Ny Om Pj Qu Rt Rx Sr Ss Uh Uu Uw Uy Vb Vo Wb Zq) Gb(aZ Cq Cv Cw Gp Hl Jo kE kF kG kK LW mH mM mY nA nB nC Nd nH nJ nK nL nR nT Um Uo Vu) Jo(aU cB cF De fR Lh Li Lj Lv Ma Me Mg Mm Mu Mv Nd nI Nn oQ Uz Wg) Yg(Aj bL cB cE cF cW dM iO Kg kI MH mI mU nA Nd nT Uo) Rt(Aa Cw Id In Kd mH mT mW mY nA nH nJ nU Um Uo) Uw(In kC kE kF kI lW mH mY mZ nA nO Um Uo) Ux(Cq In Kd kG LW nH nU Ud Um Uo Uz Wg) Va(Cw In kC kF mE mF mH mI mT mU mY nD) oO(aA Ad Gd Jv Nn Oe Rm Vo) Wg(Ad Dg Ib Ii Ks Ma Ow) Vw(In kN kO kP mW nC nH) nI(Ap Bc Dl Jj Kl Of Rc) Cw(Hp Lp Rx Ry Sh Zw) Uy(In kE kI mH mT Uo) gV(An Ar bA Bo CO) Uz(Ad Dg Ks Ma Ow) Hp(Ad aZ Ed kG) Hl(Ib Mz Ow) Zq(kE kI mS) Dg(Hr Yl) Nn(fA Gn) Rz(kG Uo) Ry(Nd Um) EmMm YhKq YkOk SfmH WekE QheQ PsnO RxlW LdeP RvnJ} Nn{Ng(aA Et

Figure 40 Continued

Figure 40 Continued

SsRz UykF} Ax{Ow(eQ fA gC gZ jB oT pI) Oh(nU oE tF) oE(Ed Oa) MjlN QaUm PeeP} Lx{nJ(Rt We Wh) kF(Yg Yi Zq) Li(mP nN) Uy(lX nA) FydX GbmY YimZ WhnU cUfR} oV{aO(Gl Hb Ib Rc Vt) Ef(cT kF oN Pc) Ez(Jk Li) AlUf EmaF JubF NycT} cU{dH(Aa aJ aO cF cI cS cY) lY(Yg Yi) nI(mZ Uy) SibR JocB OyaU} pH{To(cJ iO kN Lv Mk Ni Pc) Pb(Qt Qx Ra Uf Wm) Uf(Mm Oz)} lN{hR(aO aS bW jO Mf Mu Nq) Nq(Hq Of Om Oy) Ky(Ko Rc)} Nt{Jj(Lv Mu Nk Nx) Ng(Jk Lv Nq) Mz(Nf Pb) Jo(Jl Lv) MiHq} Ou{Uy(nA nC nD nH nL) Va(nA nH nL) nL(Gb Sf) UfeP} lX{aU(Bb Gh Sf Ug Um Uy Va) Yh(Qv Ug) RxbF VaaQ} nR{Hl(bW cE cI cW kE) Qa(Al Jm) ExYi NbJj WhUx} Mz{nI(Rt Ux Uy Va) AdcF GbYj NqNf NjPb RtnA} kE{Zq(bF bQ dF) Yh(Qv Ug) bQ(Yg Yi) EzGb RxbF} Oh{Wm(Lj Mu Ns) Li(Qy Ra) GbKc HvYi LjUm} Pf{mZ(Uw Yi Zq) kK(Uw Yi Zq) RtnJ UxkF} eP{Uf(Aj Jj Ph) AwbA FyQc MicT NahB KydR} Ez{fB(Ar Cs Li Ny) Ny(gC oT) YlOr} Id{lM(Bo Ed Ly Me) lL(Ml Or Qb)} Qa{Al(dU mU nA) Gn(nH nJ) MmeM LjfB} nU{Hl(nJ Vh Ti) ZqaF JqUy RtaO UmmE} Fy{dX(aN Li Mk Mp) NyoT} Mj{kF(nI Ny) WfnH JjfR UymP} Jv{oT(Fw Mg Pc) PcoW bUpK} Rt{aO(mT nH nK nN) bFnL} oE{Ns(cR Fa Je Jf) JfPc} Jq{nJ(Uw Va Vi) UynT} Rv{Ri(nL nN) LvnL MtmT} Nq{eD(Jm Om) FbkF} Mm{NbkF QeeM UfpK} Yi{HvOw PemZ bQkI} Jj{mE(Mu Qu) MbJl} Vi{Wb(nH nL) KxnJ} aF{Em(oD oW) ZqnI} gV{Dc(bB dD) BabG} rZ{Mf(jU jV) LijD} Gd{TinC UfnB} Hq{MbMi ZxoP} Yl{Or(De Kg)} Pc{ExjB UfpK} bQ{kI(Yg Zq)} lL{MeaW dIeD} AoEdGb GhdRkP LvJocF MnKfdX MuNgNv HlcLkN YhUgmY WhbBnC LjOwpI NycToW

Constrained panels with 3 analytes, where 1.0E-5 >= 'model p-value' > 1.0E-6. Contains 10,573 panels of 23,517,221 total panels evaluated. : Is{Hp(Ar Ax Bb Cv Cw Dc Dd Hb Ib Ih Ii Ij Im Ir Iv Ji Jq Js Jt Ju Jv Kd Ke Kn Ko Ks Lh Li Lj Ma Ml Mm Mz Nd Ng Nm Ny Oh Ok Oz Pc Pj Qg Ru Rx Ry Sf Sh Si Sr Tr Tv Tz Ud Um Un Up Us Uw Uz Vi Vp Vt Wg Yj Tl Ti) Gb(Ad An aZ bW cF Cq Cv cZ Dd Gp Hc In Ir It Jd Jh Jj Jm Ju Jv Kd kG Kr Ld Mj Ml Mt Mv mY Nd nL Nq Ns oO Ow Pd Qb Rm Rx Ry Rz Sf Sh Ub Ud Ul Um Up Us Uy Uz Vi Vj Vp Vz Wg Zw Tl) Yi(Af Bn cF cS Dc De dF dL eM Fc Fi Gz hC Hv Ib Ik It Iu Iv kF kK Ld Lp mY Mz Na nC Nd NH Ni nL NN nO Nv Og oO oP Oy Pb Qc Rc Rx Uo Va Vv Yh tF) Ax(aR aZ bN cB Ct De Dk Gp Hx Ib Id Je Kd Kn Ko Kp Lz Ma Md Me Mj Mm Mq Mw Mz Nd Nm Nr Ns Nw Nx oE Pa Pd Pi Pk Ra Rj Tv Uc Ud Ul Up Ur Us Vp Vs) Yl(aF Al aM aO aS aV aZ Bb bJ bO cD cU Dc Dd De Dl Hl Hv Ib Ik Iu Jj Jo Kn Ks Lh Lj Mm Nm Ny Og Oh Om Oy Pj Ps Qa Qb Qe Qh Qt Rc Rx Ry Sr Uo Va) Hb(Ad As Bo Cp Cq Cu Cw Dd Du Ha Hv Hw Ib Id Ii Ij Ir It Jn Jo Jr Jt Kd Kn Kr Lw Mr Nb Nf Pb Pi Ra Tv Uc Ud Ul Ur Us Uy Uz Vi Vs Wg Tl) Um(Aa Ad Al aR bN cL Cs dH Fp Ib Id Ii Ij Jm Js Jt Jv Ke Ko Kr Ks Lh Lp Ly Mm Mu Mv Nj Nq Ns Ny oE Oh Pc Pj Qv Qy Rc Rf Ry Sf Sh St) cU(An As Bc Bo bR bS cB cF Cp Cq Cu Cw Dc dG dJ Em Hv Hw Ij In Ir Jn Jr Jt Lh Li Mb Mm Na Nb Nf Nn Nr Nv Nx Ny Of Om Pa Pb Pe Po Yg) cF(An As aZ Bn Bo Cu Dc Em Hv Iv Jj Jm Jq Jr Js Ko Kr Mb Na Nb Nf Ng Nr Ny Of Om Pa Pb Pe Qa Tv Uc Ud Ul Up Ur Us Uy Vp Vs Yg) Ir(aA aC Ap aR aU Bb bO bR bU bV cA cB cD Cv De Dg dJ Dl Ji Jj Jn Jq Mb Mi Mt Mz Nj Nl Nt Nu Oh Qa Qd Rm Sf Si Va Wg) Uy(Al cD cV Dp eM Gh Gp Hv Ib Ii Ik It Iu Jj Jm Ks Lh Lp Mz Nd Nr Ns Ny Og Oh Ow Oy Ps Qb Qe Qt Rc Uo Va Vb Vo Ye) Cw(aC Ap aR aU Bb Bo bR bU bV cB cD Cv De Dg dJ Ih Ij Iu Jj Jt Lh Li Lj Lu Me Mu Nd Ng Nm Nn Ns Nv Ny Oe Of Qd) As(aC Ap aR aU Bb bO bR bU bV cA cB cD Cv Dc De Dg dJ Dl Ih Ij Iu Jj Lh Li Lj Lu Me Ng Nm Nn Nv Ny Oe Of Rm) Cp(aC Ap aU Aw Bb bC bR bU bV cB cD Cv Dg dJ Ih Ij Iu Jj Js Jt Lh Li Lj Lu Me Mu Mv Nd Nm Nn Nv Ny Oe Of Qd) kG(aU Hr Hu Ih Ii Io Jj Jm Jt Lh Li Mb mE Mm Mn MU Mv Mw Mx Nb nI Nm NN Nq nR Ns nU Ny Oe Of Pb Si Zq) Dc(aC Ad Al Ap Bb bV cB De Dg Ij Iu Jj Jn Js Jt Lh Li Lj Lu Me Mm Nm Nn Ns Nv Ny Of Qd Rx Ry Sf Sh Si Uw) Yj(Al Bb bO Cu dJ Ef Gd Ib Iz Jg Jt Lh Mh Mm Nd Ng Nm Ny Oi Om Pj Qv Rc Rf Rx Si Tr Uo Uw Va Zq) Ns(An Bn Bo bS cB Ct Cu Iq Ji Jj Jm Jt Ko Kr Li Lj Lv Ma Mi Ng Nj Nt Nu Of Og Oh Ok On Pg Qd) Ii(Em Fc Ji Jl kF Lh Lv Me Mh Mi mP Mu Nj Nk Nl nN nR NU Nv Nw Nx oE Oh Ok On Po Qd Yh Yf) Ad(aC An Bb bC Bn bR bV Cs Cu dJ Im Iu Iv Jg Jj Jq Mb Mj Na Nb Nn Nr Ny OE Om Pe Ps Qb) Cq(aC Ap aR aU Bb bR bU bV cA cB Cv Dg dJ Ih Ij Iu Jj Lh Lj Mw Nd Ne Nn Nv Ny Oe Of Oy) Jo(Id Ik Ji Jl Kg Kr Lj Lv Ma Mh Mi Mx Nj Nk Nl Nu Oh Ok On Pg Qy Rm Uf Vt Yh) Js(aC Al An aO Ap aU aW aZ Bb Bn BO bR cB cS Cu Cv Dg Dl Iv kF Mb Mt Nt Qd) Of(An Bo cB De Iq Iv Ji kF Lv Ma Mb Mi mP Mu Nj Nl nN Nq nR NU Nv Nw Ok Pg) Jm(aA An Bn Cu Em Id Jj kF Kr Lj Ma mP MU Nk Nl nN nR nU Oh On Uz Vh Xa) Jt(An aZ Bb Bn BO bR bU cC cD cS Cu Ji kF Lv Mi nN Nu Oh Ok On Pg Qd Qy) Ij(aC An Ap aR aU Bb Bn BO bR bU bV cB cD Cu Cv Dd De Dg dJ Ji oE Ok) Li(An Bn Bo Cu Ji Kr Lv Ma Mh Mi Nj Nk Nl nN Nu Nw Og Oh Ok On Pg Po Vu) Ng(Bo Fr Ji Jk Lj Lv Ma Mb Mg Mi Mx Nb Nj Nk Nl Nu Nv Nw Oh Ok Pc Pg) De(An Bn Bo Cu Em Hv Hw It Jn Jq Jr Mr Mw Na Nb Nf Ny Om Pa Pb Pe) Iu(Dd Ji Lj Lv Ma Me Mh Mi Mx Nj Nk Nl Nt Nu Oh On Pg Qd Uz Wg) Iq(aA Ji Lv Ly Ma Mb Mh Mi Mu Nk Nt Nu Oe Og Oh Ok On Pg Qd) cB(Cu Dd Hr Hv Hw In It Jn Jq Jr Mm Mr Nb Nf Nm Ny Om Pb Pe) Yg(aS aZ bA bC bI bJ bO bV cC cT Cu cX dF dJ dM eM Qh Uo) Lj(Bn Bo Ct Cu Ji Lv Mh Mi Nj Nk Nl Nt Nu Oe Og Oh Ok Oy) Bb(Bn Bo Cu Gp Hv Hw Jn Jr Mr Na Nb Nf Ny Oy Pb Pe Qa) On(Hq Hr Jg Jh Jj Lh Mw My Nj Nk Nl Nx Oe Og Om Oy Pb) Mb(aU aX aZ cC Cs dJ Jl Mc Mh Mp Mu Nt Nv Og Oi Pc) In(aU bV Cv dJ Dl Ji Ju Mz Nt Ok Ps Qa Uw Va Vz) Sf(mH oO oQ Uc Ud Uo Up Us Uz Vi Vp Vt Wg Tl Xa) Pb(aC Ap aR aU bO bR bV cD Dg dJ Ji Mz Nw Ok Qa) Al(An Bn Bo Iv Jq Na Nb Ny Om oO Pe Qa Vp Wg) Mu(Iv lY ME Mh My Nj Nk Nl Oe Og Ok Oy Ue) Jj(An Cu Dd Ma Me mP Nk Nl nN Nq nR Nx Oh Pc) Nn(An Bo Cu Em Jr kF Lp lY mP nN nR Ue Wm) Nu(aA Ji Lv Mm Mw Mx Nj Nm Oe Og Oh Ok Pz) Mr(aC Ap aR aU bO bR bV cA cD Cv Dg Dl Qv) Ju(Kr mE mW nI nJ nO nR oO Uz Vi Wg Tl Xa) Rm(Aa Du Em Fd Kr Nd Oh Rt Si Uw Vp Vu Xa) Nf(aC Ap aR aU bR bV cD Cv Dg dJ Dl Mz) Hw(aC Ap aR aU bR bV cD Cv Dg dJ Ji Ok) Bo(Ap cC cD Dg Dl Lh Nd Nm Nv Ny Oy) Dd(dH Lu Nd Ne Nv Oe Oh oO Oy Qd Rx) Hv(aC Ap aU bR bV cD Cv Dg dJ Dl Ok) Jn(aC Ap aU bR bV cD Cv Dg dJ Dl Mx) Jr(aC Ap aU bR bV cD Cv Dg dJ Dl Mt) Uz(bO Cu Ih Jv Nd Ny Ow Qh Rf Sh Si) Nm(An Bn Cu kF Lv mP Nj nN Nt Qy) Uo(dH Lp Ry Sh Uw Ux Va Vh Zq Tm) Mm(An Bn Cu Em kF Kr mP nN Nt) Nj(Lh Ma Mi Nd Nw Oe Og Oh Ok) Nk(aA Ji Lv Ma Mi Ni Og Oh Ok) Si(aZ Ud Ul Up Us Vi Vp Vs Wg) Lu(An Bn Cu Em kF nI nN Ry) Nl(aA Lv Ma Mi Mx Og Oh Ok) Hr(aA cD Dl Ji Jl Ok Qv Rc) Wg(bO Cu Ib Ih Jv Ow Qh Sh) Ny(aC aR aU bR bV Dg kF nN) Oy(AO aU Aw bV cL Ef Nq) Nt(Hq Lh Mg Mw Oe Og Oi) Nd(Du Kr Ry Up Us Vi Vp) Me(An Bn Cu Mf Mi Oh) It(Ap aU bU cA Cv Dg) Qh(Dr Du fB Gn Hl nR) Lh(An Bn Cu Ji Pg Qd) eM(Nv Ry Va Vw We Zq) Og(Lv Nw Oh Ok Pg) Em(bI bO Mz Oh) Ih(kF Rt Uw Vi) Tl(Jv Mz Ow Qb) aC(An aX Pe Qa) aZ(Bc cA Cv Pa) Aa(Ed Jf Kg) Mw(aA Ma Pg) Ji(Jq Nx Om) Jv(Vh Vi Xa) Oh(Iv Lv Wm) Va(mH Qa Yf) bV(Na Nb Pe) oO(cS Cv Sh) An(Qd Rx) Hq(Mi Pg) Tn(gZ oV) Yh(Ks Qb) Qv(Id Tv) Ry(Ld Nv) Lp(Fa Rb) Ok(Nx Om) aA(fR Mh) aU(Nb Om) nI(kF tF) oE(Ko Kr) DlIm EfIb GdGp MacE MyNw UeQy IpmP IvOe ShVt PzQd QaaR JknN OikF OwVi UxVv PfPg aPdG} Qd{cF(Aa Aj Bb bN Bo Co Cq Cs Dd Dg Ef Ha Hb Hr Hw Ib In Iu Je Jh Jj Jv Ke Kj Ko Lv Me Mh Mm Mr Mw Nd Nm Nn Nr Nw Of Oh Pc Pj Qe Ue Um Uo) Um(Ad Ap cR Ef Fp Ha Ib Id Iu Jo Jt Ju Jv Ke Ko Lh Mm Mu Mv Mx Nj Nn Ns Ny oE Oh Or Ou Pc Pj Qv Rc Ue) Hb(aO aU Bo bS cR dA Dl Fp Gp Hr Id In It Jo Lj Lv Mr Mw Nd Ns oE Oh Ou Qv Qw Rf Rj Tz Ue Uh Ur Vp) cL(Ad Al Bb Bc bH bL bR cB cE cK Co Dg dH Dl Hr Ij Iu Jj Jm Js Mm Mr Mw Ng Nm Nn Nv Of Oh Pd Qe) Ns(Ad Aj bO cK Co Cp Cq Cs Dl fP Gd Ha Ib Ji Jj Jl Ke Ko Lh Ma Mu Ng Nj nR Nt nU Nx Pj Pz Qv) aU(aK As Bc Bo Co Cp Cq Cs cU cY Dl Hr Hw Ij In It Iu Jm Lu Me Mm Mr Mw Nf Ng Nm Nv Oh Pd Pe) cU(Al bH bN bR bS cB cK Co Cs dG dI dJ Fp Hr Hw Ij Mm Mr Nm Nn Nv Oh Pd Pe Pg Po Qe) oE(Ad Bb Cs Dl Ef Fp Ha Ii Ij Iu Je Jm Jo Js Jt Ke Ko Kq Lh Nm Nn Ok Pc Pj Qw Rm Vt) Nd(Al Bb bH bN Bo bS cB cK Cs Dl Id Ke Ko Kr Lv Mb Nj Pj Ry Si Tr Ue Up Vt Yf) bS(Al Bb bO Cs Dd De Dl Fp Hr Hw Ij Iu Jm Ke Ko Ma Mr Nf Nm Nn Oh Pd Pj Qe) cB(Aa Bb bN Co Cs

Figure 40 Continued

Op Qh Qv Rf Rh Rm Rx Sf Sh Ug Um Yg Yi) Ju(aU bF bQ cT dF Dk eC hB Lx Mj oE Ou Pi) Sf(bZ Fy Jr Lx Mz nU Pg Ph Yi) oQ(kF kK kN Lp Lv Mb Mh mZ Oe) aJ(bQ bR cF cS cU dF kN Ye) pH(aR cJ Nb nW oE Pc Rf Rh) Lx(cF fB Hb mP Sh Yi Yj) aA(bQ cS cT cU cW dD dF) bZ(Jo Op Sh Um Ur Wb Yd) Ut(Bb Dp Iz Jo Um Uu) aO(dL Dp fA Um Ur Yj) Mj(kF kN Mh Rx Ur) cT(aP Ni oD Qv Rj) Fy(aU aZ cN Yi) Tr(Ad Ax Dd dN) oF(dU Hr jB oD) Qa(Ax cF Rm) Rh(cL dD Mp) Ur(bF Hc oN) Dd(cG Pg) Mh(dF Mu) Nb(kF Ld) Ni(aF bV) Jj(Hc Mu) bA(fR oD) dG(Rx Ry) GzRf LvmP MzYi UeUf YjZw ShPg RzaF UgaP VuPc bQnO bVeC cUoV dLhG} aZ{Aa(Ed Et Gp Hx Im Iv Jn Jq Kc Ke Kg Kq Lv Me Mf Mh Mj Mu Mv Mx Mz Nt oE Pi Pj Po Qa Vu Yh) Hr(aC cB cF cU De Hx Iv Jl Lh Lv Lx Me Mh Mj Mm Mu Mv Mx Mz Ne Nq Ns Po) cF(aJ aP bO cS Ih Jj Jo Lv Lz Me Mh Mx Ng Nw Po Rx Yh) Nb(aC Bb Bc cA cB Jo Jt Lh Lj Lu Mb Me Ne Ng Nm Ns) Si(cS Ef Kc Kg Ld Li Mk Mm Mu Mv Na Nq Nw Ou Ow Yh) Hp(Ao Co cS Dk Ef Ho Ld Mg Mu Mv Nq Nv Nw Ou Ow) Og(aC cB De Im Iv Lj Lv Mb Me Mu Mv Mx Ne Nt) cU(aV bO bQ bR bU cA cC Cv dJ Jo Lh Me Mm Oy) cA(Iv Lh Lj Lu Lv Me Mp Mu Ne Nq Ns) Yg(Co cS Ef Hc Jr Kq Ld Mt Mv Nv) Yh(bO Hb Lu Mt Ni Nj Rx) Rx(Ef Hc Ld Na Nj Nv) bS(Im Lh Lj Mb Mx Nq) Ax(Fp Ih Lv oE Po) Jo(De Iv Lv Nt Po) cE(aO bF Lv Mv Nq) Gd(Aw Ef Hc Jf) Eq(Ib Mh Ow) Hb(Gc oE Yi) Zq(aO dF Pf) Oy(Mu Mv Nq) aC(cS Ih Mu) Ns(nU oE) Me(bO Nw) Mm(Bo Nt) Nj(Fi Lt) Hc(Lp Sf) Yi(Oh Ow) Vw(Ny Ow) gV(Ar bA) CvcS DebO YfUt MhcB MvSh Holb RznJ RyNv YlOu} Ok{Jo(aA cU Ik Jk Jl Lj Lv Me Mf Mh Mi Mj Mu Nc Nj Nk Nl nN Nq nR Nt Nu Nx Pg Qa) Pg(Hq Hr Hv Hw Ii Ij In Jt Lh Li Mx Ng Nj Nk Ns Nu Nx Ny Om Pf) Mu(aA Hr Hv Hw Ij In Jj Lv Me Mh My Nj Nk Nl Nt Nu Ny Oy) Nu(Hr Hv Hw Ij In Jj Jt Li Lv Ng Nj Nk Nm Of Om Pb) Lv(Hr Hv Hw Ij In Jj Ng Nj Nk Nl Nm Ns Nx Oh Om) Nk(aA Hr Hv Hw Ij In Jj Ni Nq Nt Of Oh Om Pb) Nj(Hr Hv Hw Ij In Jj Mi Nq Nw Of Oh Om Pb) Of(aA Ik Jl Me Mj mP Mv Nl nN Ns Nt Nw) Om(aA Jk Lj Me Mf Mh Mi Mz Nl Nq Ns Nt) Hr(Jk Jl Me Mh Mj Mk Nl Nq Nt Po Qa) Pb(Hx Jk Me Mh Ml Nl Nq Ns Nt Nw Ny) Hw(aA Li Me Mf Mh Mz Ng Nl Ns Nt) aA(Hv Ij In Mf Mh Na Nc Nf Ny) Jj(Ik mP Nl nN Nq nR nU) Nm(Lw Mp Nt Oh) Qa(Hv Ij In Li) Nq(Jh Ng Oy) Nt(Jt Li Ng) eP(cU Ld Mp) Nf(Mt Mz) BoMm PoLi MbmP MeMf NgJk IiJl YjRc JtnN KqmE KylN VvoE cUfR} cU{dH(aF aK aL aU aV aX BA Bo bV bW cG cL cT De Hr Iv Jj Jo Jr Lh Lv Mb Me Mh Mi Mp Ns Nw oE) cE(aA aJ aK aL aO aP aQ aU aV bA BO cF cG cI cL cS cT cY De dF dJ Lv oE) cF(aA bQ bR cI cR cT De dJ Hr Jj Jo Lh Lv Me Mi Mm Nw Oy) Jo(aK aU aV bR bS cY De dJ Iv Jq Jr Lv Me Mv Mz Nt) aU(As Co Hq Hr Jj Lh Ly Me Mm Of Pa Pb Pd Pf) Oy(aK Aw cB cY De dJ Hu Jh Lv Mi Mu Mv Nq) Lh(aV Bo bR bS cK cY dJ Lv mE Nw oE) bR(aA aJ aK cI cS cY Hr nI Ns) nI(Aa aL cI cM Cv dD Lp lY) cB(aA Hr Jj Ly Me Mm Ns) De(As aV bQ Gd Hr) bS(Ly Me Mi Mm Ns) eP(Ao Aw Ex Ld Om) oE(Ax fP Ns pF Um) Hr(cY dJ Hx Mz) Yi(Jr Mz Oh Ow) bQ(aA aL cI cY) gV(bA cO Cw Dc) As(aK cY Mz) Gd(Ao Gp Jf) dG(aA aJ aP) dJ(Bo Mb Mm) oV(Ef Lj Ny) cM(nR pK) dI(eD Zq) BoMm GpSh LxdX HlnU YgJr JjcY LiNw PcoW aAdA aVcI} Nw{Mx(Hq Hx In Lj Mb Md Mh Ml Mv Mw My Nf Ng Nk Nl Ns Ny Og Om) Of(aA Ik Li Lv Mb Me Mu Nj Nk Nl Nq nR Ns Nu Nv Pg) Pb(aA Hx Jk Jl Lj Lv Mb Me Mu Mz Nk Nl Ns Nu Nv Pg) Nt(Hx Ii Jo Li Lv Mb Md Mh My Nj Ny Og Om Oy Po) aA(fR Hq Hr Ik Mf My Nc Nf Ng Nk Nl Ny) Lv(Hq Jj My Ng Nj Nk Nl Nu Ny Om Oy) cF(Ad Ax Dg Jo Jt Lh Nm Ry Yg Yi Yl) Yf(Hb Lh Ny Oh Ow Qb Si Va) Yl(Bb Ii Mz Oh Or Ow Rc Si) Nj(Hq Hx Iv Mh My Ny) Yi(bU Hb mY oF Oh Rf) Ng(Ik Mu Nq Nu Pg) Yj(Bb Hb Oh Ow Rc) Me(aU Ax Bb cB) My(Jk Lj Nq Pg) Si(Gp Rx Vu Vz) Uy(Ny Oh Ow Rc) Iv(Jm Mb Ns) Oy(Jk Nq Pg) Hq(Mi Pg) Ry(Hb Rc) Om(Lj Qa) Uw(nC nH) Vw(Ke Ow) nJ(Rt Vi) DeJo WmLi EdHp NmcB IbWg PsnH} Qa{Pb(aA Hx Jj Jl Jm Jq Lj Lv Mb Mi Mt Mu Mx Mz Nb Nj Nq Ns Nt Nu Nv Nx Ny Oh Pc Pg) Um(Cs Fp Hb Ih Ii Ij Iu Jm Jo Ju Jv Lh Mm Mr Ns Ny Qe Qv Rc Rm St) Hw(aA Iv Jl Jm Jq Li Lj Lv Mb Mx Mz Nj Ns Nt Nu Nx Oh) Mx(Hv In Jj Jm Jn Jr Li Lj Mb Ns) Jj(fR Ik Lj Lv mZ Nj nR Ns Nx) Nt(Ii Ij In Iu Jm Jo Li Ng) Ii(kF mE mP nN nR nU Nx) Lj(aA Ij In Iv Lv Mb Of) Hp(kC kK lY nB nJ Vv) Jm(Iv Lv mE mF mZ Nx) Li(aA Iv Lv mP nN Ud) Al(kI mW mZ nU oQ) Ax(Hr mE mF Rj Ud) Mm(kF mP nN nR nU) In(aA Iv Lv Mz Nx) Aa(bS cB dG mW) Ns(Lv mP nR nU) Ij(aA Iv Nx) Ha(jB oT) Mb(Jl Mi) Nf(Mt Mz) Ng(Mu Nq) eM(Uw Yg) eP(Fy Ld) nR(Lh Mn) DeJo GnnC LvOh MiHq HraA HvIv YibS RmmZ} Jj{nR(Jq Jr kF kN Li Lx Lz Mb Ml Mx nI Ns Nt Oh Pb Pc Pe Pf Pg) Mx(Ih Im Jk Jl Jn Jr Lj Mg Mp Mu Nk Nq Ns Nv Pc Po Qb) Nx(aA Ik Jk Jl Lv Mi Mj Mu Nk Nl Nq Nu Nv Pg Po Qb) Pg(fR Hq kF Lj Lv mP mT Mu Nk Nl nN Ns nU Of Pb) Lv(Ik Jk Jl mP Mu Nj Nk Nl nN Nq Nu Oh) fR(bZ Im Jk Jn Lx Mv Nt Pf Po Ut) Nj(Jk Jl Mi Mj Mu Nq Nv Po) Jl(Ik Nk Nl nN Ns Nu) Mj(Ik kF nI nN Nu) Nq(kF kN lY mE) Mu(aA lY Me Nl) Kq(mZ nO nU oQ) Nv(Mb Nl Nu Of) Ut(lX lY mH mZ) Vv(kP mP mT nN) Ik(aA Mi Nu) Mv(kN mE) Mz(Nf Pb) Nb(kF nU) Nl(Mi Po) nN(Jr Pf) FwmZ MbJk MecF YimW aUlX} Yi{Jr(aM bC bE bS bW cF cL CO cS De dJ dL Ez Fc Fi Hb Hv Ib iH iO Iv Jh Ju Jv Kc Kg kP Kq kR Ld Li Mg Mi MP Mq Mt Mu Mv Mz Ni nK nL Nq oF Oh Ou Ow Pd Qy Rc Rf Rx Rz Sf Sh Si Uf Uk) Hv(Ax Du Ha Hp Ib Ih Ii In Iu Jm Li Lj Lp Nf Pf Qx Rf Rx Ry Yg) oF(bG Jq Ke Kg Kq Ld Nv Pg Pi Pk) Ou(Ax cE cT Mz Na Nb Oh Ow Rf) Lx(cF De kC lY mY nJ tF) Mz(kI lW mS mZ nI oQ Ow) Ld(Jl kN mH mT mW mZ) oQ(bF Jq Lh mZ Pg) oP(Ez Gp Js Pi) Ow(mZ Rt tF) Ut(mE mF mM) De(Js Oh) Or(cF Rf) bQ(kC mS) EzmH GpnA NqcT HlnR JqcF LhnN aFkP} Ut{mE(Dp Gd Hr Je Lp Nv Nx Of Og Oi Ps Qz Rx Ug Wd We Yg) kF(Bb Fb Jk Jm Jt Kl Li Mm Ny Oi Rc Ss Uu Yg) mW(Al Cp Gn Jt Ju Rc Sh Uu Uy) nH(Gn Hl Hp Lp Sh Wb Wf Ye) nI(Bb Je Jg Jt Nv Qw Rc Ug) Jk(lX lY mP mU nN nR nU) nA(Hp Nx Si Uw Uy Wb Yg) nN(Li Mm Nv Ny Oh Yg) lX(Bb Jt Nm Nv Of Oh) mT(Gn Lp Sh Uy Wb) mU(Hp Si Uw Ux Wb) Fb(oT oV oW pI) Yg(bH mF mM mY) Lp(mF mI nD) Oh(Jo Li Mm) fR(Ii Jo Ug) nR(Al Bb Nv) mZ(Hp Rt Wb) Yf(Ch Sh) Wf(eM lW) Jv(fB oQ) lY(Je Oi) nK(Hp Ux) AlnU GdmF GnnC YjSh SsmP YeeM LdeP YlOr UgmH UynD PcfB} Oh{Um(Ax Iu Jo Lh Ly Mm Mu Mv Mz Ns Ny Ra Rc Rf Rg Rh St) Ax(cK Ed fP Fw Hb kP mP mZ nN nR Or oT Qz Ra) Ra(Iu Jo Lh Lj Mm Mu Mv Nq Qv Qy Rg Rm) Hv(Du Hp Ru Rx Ry Uy Yg Yj Yl) kF(Ih Ii It Mb Mm nI Nm Of Oi) Lv(Im Mb Nj Nk Nl Nt Nu) Mx(Im Jr Nk Nl Ns Nx) Mb(Jl Mi Nt Nv Pg) Nj(Im Iv Jl Mi Pg) Jo(Nt Qy Rg Uf Vv) nR(Al Ii Jm Mm Of) Li(Ed Kg rZ Uh) Wm(Jp Mc Mi) Ns(Iv oE Rg) Mu(lY Me nK) Gd(De Tj) Nm(mW nF) Ng(Jk Nt) Iv(Im Jm) Rf(mZ Rg) eP(dG dH) MlRx MzNf HlmW YjJr KylN NyoT OudX UynC VvoE mZnI} Mx{Ns(Im Ir Jl Jr Lw Mg Mi Mp Nj Nv Nx Pc Pg Po) Jl(Hr Ii Im Jm Jo Jr Lh Li Lj Ng Nl Nu) Im(Jn Jr Lj Mh Mp Nk Nl Nu Pc Pg) Jr(Jt Lj Lw Mh Mi Nj Nl Nx Po) Lj(Mh Mi Pe Pg Po Qb rY rZ) rZ(Hr Hv jV Mr Pb Pd Pe) Mb(Jt Mc Mm Nb Nq Pa) Nu(Mh Mi Mp Nj Pg) lN(In It Mc Nq Qb) Ng(Mu Nq Nv Po) Jo(De Mg Nx Po) Lh(Hr Nf Of Pg) Mh(Jn Js Nx) Mz(In Nf Pb) Nv(Nj Of Pb) Pg(Jm Oy Pf) Mi(Nk Nl) Mp(Hq Nl) Jn(Jt Lw) Nx(Of Pc) Um(lL Qv) nI(kF mZ) AxoE DeHr PoLi NqNj NkPc InlL QbJm} oE{Vv(Ad Ap Bb cE Dg Dl Ez fP Hb Ij Iu Jd Jf Jm Jt Kl Ks Lh Li Mm Ng Nm Nr Ns Nv Oe Oi Pc Rc Rm Um Uu) Ns(Dg Ed Hb Hr Kk Ko kQ Lh Ly Me Mh Mp Ng Nm Nx Oi Pd To Uf Um Up tF) Um(aO aR Ax cL Hc Jf Jq Kg Lj Na Ou Oz Pc Pd Pk Ub) Ax(Fw Gp Iv Je Jf Kx Lz Po Qh Qn Vu Tj tF) Jf(Ad cL Iu Jm Jo Nm Oz Pb Pj) Ad(Hc Kg Na Ny) Pc(Je Ne Qn Ra) Ed(Cs Fp Li) Nm(Hc Kg Qn) Ne(Ly Nh) Hc(Dg Dl) Kg(Jo Oy) FwMm IdJr UoPk} Kq{mE(Ap Bb Cv Dg Ef Fb Ii Jk Jo Jt Kl Ny Of Oi Ue Ug Uu) Um(Ad Ap Bb cR Dg Ef Hb Ib Iz Jo Li Mm Or Oy) mT(Bb Jk Jt Li Lp Mm Nv Of Qe Rc Rx Uu Th) mW(Ad Ap Bb Dg Jg Jt Kl Mm Of Pz Rc Ss Uu) nI(Bb Bc Dg Ef Fr It Jt Kl Mm Of Pz Rc Ss) lY(Bb Bc Fb Jk Nv Ny Oi) cP(aR Ax Ef Iu Ld) nJ(Kl Mm Nv Ps) Mm(lX pH) Ss(dX mP) Kl(kF nR) fB(Op Un) oQ(Of Uu) AdmM ApYj TrRa IzmI YgcT ZqlW KylN NveM OikF OudX VvOy VwnL} Iv{Ng(Et Fr Jh Jl Lw Mg Mm Mp Mt Mv Ns Nu Nx Pc Po) Jo(cB De Et Fr Jk Jq Lj Lw Mp Nu Nx Pc Po) Li(Et Fr Jl Jp Lx Mj Nq Nt Nv Pe Po) Of(Fr Jk Lh Mt Mv Mz Nb Nt) Og(Jk Jl Lj Nq Nt Nu Nv Pc) Mb(Fr Im Lj Mp Mz Nq Pc) Pb(Hx Jq Mt Nb Nv Ny) Ns(Im In Jl Lj Mu) Jm(Mj Mp Nq Nu Nv) Mz(Hr Hw Ij Om) Hq(Lh Lx Mp Nq) In(Jq Nk Nt Nv) Nt(Ly Oi) Ii(Jq Nb) Im(Lj Pc) Oy(Jk Lj) NqNj MeMf MtNf MuMy HwJq JlLh} nR{Lz(Ii Jo Ju Lh lY Mm Mn Nm Ns Ny Of Pb Pc To) Lx(Al Ii Jm Jo Jt Ju Mm Mn Nm Ns Ny Of) Hl(aR aW cH cJ cM cS Db Jf lX nI Yg Yk) Nm(Li Mb Ml Nb nI Nt Pe Pf) Mm(aU Li Mb Ml Nb Pe Pf)

Figure 40 Continued

Jo(Ez Li Nb Ni Nt Uf Vv) Pf(Ii Jt Lh Mn Of) Al(Ih Jn Kx Vu) Pe(Ii Li Ny Of) Pc(Hr Mb Ur) Bb(aU Di) Gp(Ti Th) Ns(Mb Rb) Ml(Ju Mn) Nb(Ii Jm) Jt(nI Nt) Li(IY Of) DgcF FwKs NiNk HqSh RbJr SsRz JqOf UgVv VbVi nIkF} Mz{Pb(cF Ik Jk Jl Lj Lv Mb Me Mf Mh Mi Mq Mu Nk Nl Nq Ns Nu Nv Nx Ny Pg) Nf(cF Ik Lh Lj Lv Mb Me Mf Mg Mi Mu Nj Nl Ns Nu Nv Pg) Um(Bb cF Hb Jo Ju Li Lj Ly Mu Mv Nq Ns Pc Qv Qy Rc) cF(Aa As Cq Cw Hr Hw Jo Uo) Nt(Ij In Jo Mb Of Om) nI(Al Cv Kl Rx Wb) Mb(Jl Mp Nv Pg) Jo(As cB De) aA(Hr Hw Om) Yl(Or Ou) Of(Nv Pg) AaEd AdcB DeHr YjRc LdeP} aA{Hr(Ij Ik Il Jl Jq Lw Mf Mh Mi Mj Mk Nk Nv Nx) Mu(Jh Mh My Nc Nk Of Oy) Ng(Jk Jl Mg Nq Nu Nv Po) Mf(Mh Mi Nk Nl Nu Pg) Pb(Hx Ij Jq Ml Nv Pg) Mj(fR Li Lj Nl Nu) Po(Lj Mw Nl Of) fR(Lx Mp Nq Pf) Mh(Lj Nu Nx) Nk(Ik Nu Nx) Ij(Hw Li Of) Mi(Hq Ik) Lj(eD Im) Nv(Hq Of) Pg(Ii Mw) hR(eD lN) LxLi MtNf HwJq JkOf JlLh LdeP} Or{Yl(AO aU Aw bA bC bF bQ cF cL CO cS CT dK Ef Gp Hb Hc Ho Hq Jh Jr Ju Kc Kj Li Lp Mg Mi Mp Mt Mu Mv Na Nb Nq Nv Om Ow Pd Pi Rz Uf Wd) Um(Ax cF Fy Hb Hc Ju Jv Lh Lj Mg Mi Mm Na Ns Pc Ub Uf) lN(Ax Id Ko Mr Vq) Oy(Mg Mv Vv) Id(jG lK) FyeP GdGp MejV} Lx{kF(Hp Ih Ii Jt Li Mm Nm No Ny Oe Of Oi Uw) fR(aU cB Hr Hw Lj Lv Mi Ml Mu Mv) mP(Ii Jt lY Mm Nm Ns Of) nN(Ii Jt Mm Nm Ny Of) cF(Cs Du Hl Ry Yg) dX(Ao aX cS Ou Qz) eM(Rt Uw Uy Zq) nU(Ii Mm Ns Of) Ii(Fi mU) Lp(kN mW) AxoT FaeP NoYl NtHq MulY RfpK OekC VwnJ} Jo{De(bS cB cF cT Hr Jl Js Lv Me Mi Mj Nf Nt Oy Pg Po) Nt(cB Hq Jq Ly Mi Mj Mt Mu Ng Nk Nx Po) Pg(Hq Lv Mb Nj Nl Nu Nx) cB(cL cT Lv Mi Mj Po) Mi(bS cF Ik Nj) Uf(kN mZ Um) cF(cT Mp Po) Lv(aR nN) Jl(Mb Nj) Vv(mP nN) aU(lX Po) mE(Mu Qu) NqlN IdlL UveD cTnU} eP{Ld(bO cG Cp Cs cT Dd Hw In Ip Jp Jt Li Me Mp Mt Mv Nq Oa oF Ou Ow Pf Ph Qb Qc Sr St Uc Uf Us Vs Vv Tj) Uf(Ad Ax bA Dg Dl Ed Jp Jt Kj Kl kR Mm Qz Vo) cT(cS Mt Ow) Fy(Ir Lh) bV(Mi Mp) cG(cE dH) DebA UnbF VqkR} bZ{fB(aF Qb Qh Qw Rc Rf Rm Sr St To Uh Un Up Us Vq Vt) nI(Gd Hp Lp Op Rx Rz Sf Sh Wb) Yg(kP lY mE mF mH nK nU) mE(Ur Va Wb Zw) mH(Gh Rt Sf Va) Hl(kE kN mW) Lp(lW mT nN) Hp(mI nJ) oV(Rf Rm) AxpH ZqmS RymI UwmP UymT UxlX cDpK} Mi{Hq(Ik Jk Jl Lv Mh Mj Mu Nj Nk Nl Nq Nu Nv Nx Po) Mb(bS Jl Lj Lv Mu Nk Nt Nu Nv Pg) Ng(Ik Jk Mu Nt Nu Pg) Nj(Lv Mu Nb Nu Pg) Of(Ik Lv Nt Pg) Bo(cF Mm) Lv(Nl Nu) Me(Mf Mu) bS(Nm Ns) fR(aO Pf) DeOy NtLi MjlY MuNl} Nq{lN(Jh JT Me Ml Mu Mw My Nf Nr Nx Qb) Oy(bA bV cB cT De eD jD lY mE Um) eD(Hq Ij jG Li lL Ns Of) lY(Hr Jh Mk My Of) Ng(Jl Lv Nu Pg) kF(Mb Mm Of) Sh(bH Vv) Om(jD lL) NtHq MmnN HrmE YgcT YkJv LpmT bAfR} Gp{Gd(An cA De In lW Mj Nb Qv Qx St Vu Wb) mE(Ho Rx Rz Vi Vw We Yh) Yh(mH nI nN) Sh(Hc mI Ou) Vi(lW nA nJ) oP(Hl Rx Ry) Aa(Dc Ed) Th(kK kN) Sf(Ed Ou) mH(Uw Xa) oF(Fc Fi) FaZq NmHo HlnU SiJr WdnD WheM PslX LpnI VvfB} Jr{Yj(Hb Ib Jv Ow Rc Rx Sh Si Zq) Hp(Ed Gz Um Uo Vu) Yg(aO bC cF cG) Si(Hl Ry Um Uo) Em(bO De Ii) Ry(Hb Ju Nv) Ow(Uz Wf Wg) Ib(Uz Wc) Rx(An Id) Lp(nI Vu) AlnU YfIi MmnN HlHb SfoP ZqkF WgJm NyUz UoUy UwmP aUlX cSmE} Nt{Ng(Fr Hq Jl Jp Ly Mg Mj Mt Mv Nk Nv Pc Pg Po) Hq(Jl Lv Mb Mp Mt Mu Nv Pg) Of(Jk Jl Lv Mt Mu Nv Pg) Lv(Ly Mt Mu Nk) Mu(Me Oy) Ii(Jl Pg) PoLi MbJl JqPb KylN} Vv{nU(Ad Ii Iz Jt Lp Lz Ml Mm Nm Of Oi Uu Vo) Rc(Hl Uy Vi Vj Yj) Rm(jB oT oW pI) Ug(mU nN nT) Mm(oV pI) Oy(Mu Ou) oW(Lh Om) DlnI EdHp IbpH IioP ShRy JpdX OinN OwVj UueQ fBnC} Lp{kN(aU Mb nI Pe Pf Pg Ps Wd) nI(bF Mj oN Ou Pf Vp) Hq(fB lW mF nD nJ) mT(Co Ef Mv Rz Ua) Hc(Gz Hv mI nB) Pg(mE mF) oP(bU Jf) UcnN PsnU VunL PbkE bFmZ cYlX} lN{Ky(Ap Ax Bb bC Bo Cp cT cY Dg Ef Id Iu jD jF jG Jt Kl Kr Li lM Ly Me Mf Nx Rb Uc) Qb(Ax Id Mf Mu) hR(Hu jH Qy) Mf(jI rZ) AxMl MeHf MurC} kF{Mj(Ii Jm Jt Lh Mb Mm Nm Oe Of Oi) nI(Dl Jl Jt Lu Lv nU Pf) Nb(Ii Jt Mb Nm Of Oi) Pf(Mm Nm Pc Uw) aU(Bb Dg Mm Oi) Pg(Gd Mm Vb) Pc(oV oW) NyoD} oV{Pc(aF aO bF cS Ez Jv Ou Rb) aO(Ko Mb Ou Ow Qm Qn Rf) Al(Fw Kx Ow Rm) Ez(Mm Ny Rf Rm) aF(aR aW Kx Ow) cT(Lh Mm Om Rm) bF(Dp Jv) HboN LdQl} Lv{Im(Ad Ax cF Nk Nl Nu) nN(lY Mm Nm Ns Of Pc) Ng(Jk Mu Nl Nv) mP(lY nI Ns Pc) Nl(Mt Mu Nu) Of(Jk Nv Pg) Oy(cB cF Dc) Ns(cB mU) EmcF NuMt MulY} aU{lX(Aa Ap Dl Dp Hb Iz Jt Kf Ks Mm Nm Ny Of Pc Pj Rc Rj Rx Ue Uk Uo Ur Uu Vo) kN(Ad Gh Kf Kl Mm Nm) AwOy} Pg{Ng(Jk Mb Mg Nj Ns Nu) Hp(gL kN mM oQ) Gn(nC nH nL) Of(Lj Mu Nu) Fd(nC nL) Mb(Jl Nu) Oy(Lj Mu) nN(Jt Mm) AloW GdnK SioQ ShkC JuoT} Pf{nN(Jt Li lY Mm Nm Of Pc) mP(Jt Li lY Mm Nm Of Pc) Mu(lY mE nK) mZ(nI Ry Vb) AlnO MplY HlkN SfmH OfnU PcnT} fB{Ez(aF Of Op Qb Qh Qv Rc Rf Sr Ss To Un Vo Vt) Yg(bF bQ Pi) Yh(cM Hb) BaHp HqZx QtPc RzaF LhOp} Mb{Jl(Im Jm Lh Li Lj Lw Mp Ng Ns Nu Og Pc) Nv(Hq Ng Nu Of Pb) Ns(mP nN nU) MumE NgJk mWoT} gV{bA(aE aG aH aL aM Ao AW bB bI bL cB cC cH cK Cw Dc dM) cT(Ao bO cV Cw) BaDc} Um{Ou(Aa aR Hb Hx Na Qv) Mj(Ju Li Lj Rg) Ue(Mp Mu Mv Qy) Li(Mp Uf Vu) Hx(cF Mv) ApjO IdlL HbJq} Me{jV(Ba Bc bL CT cX dE Dl Ki Kj Mf) aW(jG jI jO jP lM) Id(jI jT lL) NvOf} Mu{Ng(Jk Jl Mj Nu Po) lY(kE Lz Mh Mj Ml) mE(kE Lz Mh Nm Oy) LznK JlOy NvOf OmeD jVrZ} nU{Hl(bH dI Jf kN Mj Rv) Eq(aO cT) Gn(aF Hv) Ns(Mh Rb) Ur(Ch mE) CvaC GhaQ HpVi RtbF UgmE aOfR} eD{Uv(Fp Js Li Lj Mq) Mv(Hq Ns Of) Lj(Md Mj Qe) hR(cF jO lL) FrJm MfJv MyOy bGdI dHlL} oT{Jv(Oy Oz Pa Pb Pd) Ny(cT oN Ow) Ow(Li mW) iO(Rf Rm) oN(cM nI) CsPe EzmW NiaF} Oy{De(bS cB cT Mj) Hc(Ho Rx Sh Wd) Ou(Ef Uf Yl) cB(Aw cT Mv) AwbO} Id{lL(aM Ed Lh lM Ly Lz Ph Qc Qe Ql) Ly(jI oF) EdjI RblM} nI{Mj(mZ Of Ur) Sh(bF Yd) aO(Rx Ur) mZ(Cv Lz) GdcG HloN YgLh KytF aFoW} Hv{Gn(kN mP nC nH) Uy(eM In Uo) Mh(Du Yj) Yg(aO Tt) YlOw} Hp{Ed(aO De Ez Hc Ua) Ps(eM mY nC) JsVu UwkP VinJ} Hq{Sh(kN mI mM nD nK oP oQ) GdnK SfoP YekN NyPb} Nv{Of(Ik Lj Nj Nu) Yj(Oi Rc) Ry(Ed Oa) NuNg} Ow{Rt(Aa Yj) Pc(jB oD) GdVz SfmH LiYl LjjB UweM} Ou{Yl(cE Ju Jv Op Sf) dX(Mh Pe) TrRa YgcT} Mj{nN(Mm Of) lY(Li mP) DeHr HlmP WfnL cFnO} Ld{Ry(Jl mZ) YgmW YjRc RxmS YlhC QljB NyeQ} aF{Rz(kE mZ) cF(nT oW) mE(oW Zq) YhoQ aPdH} Hl{mW(Hc Js Li Po) Vu(fR kN) bGoF} Uf{Jt(kE kI kN mW) UedI JpdX VbkN} Pe{dX(Fy Ha) eM(Uw Vb) AxmZ LinN LjOf} Yg{bQ(nA oP oQ) GzcT JqcF PioF} Jk{Ng(Et Mg Nl Nu Po) QumE} rZ{Mf(jF jY) hR(jO jP) iCjO jDjT} mE{Qu(Mm Nm Ug Ur) ChUr} Yj{Rc(Jq Yh) DeMh RxcT} Li{Lz(mP nN) MlnN KefA} Vi{Uo(Ny Rc) WbnT LhnJ} oW{Pc(aO bA bF) FacT} Aa{Dc(aX bV cF)} dX{FyQc JfbQ JpKs} kI{Ju(bF Pi) JvbF} oP{DubB SfJf ShbU} Ax{LyoF MpfA} Jq{YfIi SiVu} Lh{UwnH VanL} Rt{YhmZ aOnL} Ri{RvnH kCpH} dU{QwcS KchC} kN{NmKe WbaQ} AlRmeQ DeGdHc PoLjOf ThbBnC EzMvlL LyKyjF MhaCaX MqUwmW HrRcVu SfcYlX RfPbpH OmVbnK aPcFdH

Constrained panels with 2 analytes, where 1.0E-7 >= 'model p-value' > 0. Contains 1 panels of 142,491 total panels evaluated. : NnIv Constrained panels with 2 analytes, where 1.0E-6 >= 'model p-value' > 1.0E-7. Contains 27 panels of 142,491 total panels evaluated. : Nn(Is Lv Mb Me Nj Nt Ok Qd) Iv(aA Ji Jj Mx Ok On) Mx(aA Lv Me Nt) aA(Lv Mb Nj) Qd(Ax Lj) On(Ng Of) AaIs CuYi Constrained panels with 2 analytes, where 1.0E-5 >= 'model p-value' > 1.0E-6. Contains 148 panels of 142,491 total panels evaluated. : Qd(aA Ad aU aZ Bb bS cB cF Iu Iv Ji Jj Jl Jm Lh Li Lv Ma Mb Mu Mx Nj Nl Nq Ns Nt Nx Ok On) Is(aA Ad Ax Cq Dd Iq Iv Jj Jm Lj Lv Mb Mx Nj Ns Nt Nu Ok Um Yi Yl) Nn(aA Im Ji Jj Jl Mh Mi Mj Mx Ng Nk Nl Nu Oy Pg Qa Tz) Iv(Im Jl Lj Lv Ma Mi Mp Mu Nd Nq Ns Nt Nu Nw Oh Pc Pg) Mx(Im Ji Jj Jl Ma Mb Mi Mp Nj Nl Nu Ok On Pg) aA(Ik Ji Ma Mf Mh Mj Nk Nl Nt Nu Nx Pg Po) On(Jj Mb Mw My Nj Oy Pb) Mb(Ji Jl Mi Ok) Nt(Jj Jo Ng) Tz(Nd Qv Um) Ji(Hw Om Pb) Oh(kG Um Wm) Cu(Jo Yj) Ma(lY mE) Nw(Gb Pb) aZ(Aa Nb) NsoE MjkG NdUm JjPg OkPb cUdH Constrained panels with 2 analytes, where 1.0E-4 >= 'model p-value' > 1.0E-5. Contains 454 panels of 142,491 total panels evaluated. : Is(An As aZ Bn Bo cB cF Cp CU Cw Dc Em Gb Hp Ii Ir Iu Ji kF kG Kr Ma Me Mh Mi mP Ng Nk Nl nN Oe Of Og Oh On Pg Uy Yj) Tz(Ax bN cF Gb

Figure 40 Continued

Hb Hp Hr Ii Iu Jo kG Lh Li lN Ma Mm Mu Mv Nq Ns nU oE Oh Pc Qy Rm Rx Si Uf Uy Va Vu) cU(aA aV aZ Bo bQ bR bU cA cB cC cE cF cI cO cT cY dA De dJ Gd Hr Jj Jo Lh nI oE Oy Qd) Ok(aA Hr Hv Hw Ij In Jj Jo Lv Ma Me Mh Mj Mu Nj Nk Nl Nm Nq Ns Nt Nu Of Oh Om Pg) Qd(Al Cs Dl Ef Ha Hb Ib Id Ke kF kG Ko IY mF nN nR nU oE Pj Qv Ue Um) Lv(aZ Im Ji Jj Jl kG Mi Mj mP Mt Mu Nk Nl nN Nt Nu Nw Oh On Pg Qa) Nn(eD Ik kE kG kl lY Ma mW My nA nK Nx oE Og On oO Po Qb Ue Um) Ji(Hr Hv Ij In Jj Jo Jq Ma Md Mu Nj Nk Nl Ns Nt Nu Ny Of Pg) On(aA Hq Hr Ii Jg Jh Ma Mh Mj Nb Nk Nl Nt Nu Og Om Qa Yi) Qa(aA Hw In Jj Jm kG Lj Mb Mi Mx nR Ns Nt Nx Pb Um) Um(Hx Kq Ma Mj Mp Mu Mv Mx Mz Nq oE Or Ou Ut) Pg(Gb Hq Im Jm Jo Mb Mi Ng Nj Nl Nt Nu Of Oy) aZ(aJ bO cF cS Cv Gb Hp Hr Ma Me oE Og Rx Yh) Nw(aA Hq Mx My Nj Nl Nt Nu Ny Of Uw Yi Yl) nR(Hl Jj Jo Lx Lz Mb Ml Mm Mn nl oO Pe Pf) Nt(Hq Jl Ly Mb Mi Mt Mu Nd Nk Of Oh) Mx(Jr kG lN Mh Nk Ns Nv Nx Oh Pc Po) oE(Ad Ax Ed Hc Je Jf Nd Nm Pc Qn Vv) kG(Gp Lx Ma Mu Nb Nq Ou Pc Pf Tn) Mi(aA Hq Ik Me Nj Nk Nl Nu Nx) Cu(Ad Gb gV Hl oO Uz Wg Yg) Tn(Jo kI mP nN nT nU) Oh(kF oO Qv Ra Rf Rg) Lx(Gb kF mP nN nU) Nd(Lp Qv Rx Sf Sh) Jl(aA Jj Nj Nl Nu) Nq(eD IL IN lY) Ma(kl mU nN) Mb(Jt mP Nv) Mu(aA lY mE) Mz(Ad Nf Pb) Jj(Nu Nx Po) Jr(Gb Yi Yj) lN(hR Ky Mf) oO(aJ Kq oQ) Mj(kF nl) Jo(cB De) Yl(Or Ou) Nv(Nj Of) Vv(nU Va) Pf(mP nN) aA(eD Mk) eP(Ld Uf) gV(bA cT) jD(lL rZ) GbOw GdGp NbkF NgJk HvYi IdlL QumE aPdH nUnI hRrZ

Constrained panels with 2 analytes, where 1.0E-3 >= 'model p-value' > 1.0E-4. Contains 1,088 panels of 142,491 total panels evaluated. : Is(aU aX Bb bO bS Ct Cv De dG Dk Dl Dr Du Gd Gn Gp Ha Hb Hl Ib Id Kd Kn Ko Kp mU nI nR nU Pi Qv Ra Rj Rm Rx Ry Tv Uc Ud Ue Ul Uo Up Ur Us Uw Uz Va Vb Vh Vi Vp Vs Vt Wc Wf Wg Tl Xa) Nw(Ad aU Ax aZ Bb bS cB cF cU Dg Hb Hp Hx Ik Im Jj Jl kF kG Ma Mb Md Me Mf Mh Mj Ml MP Nc Nf Ng Nk nN Ns nU Nx Og Oh Om Oy Pg Po Qa Rx Ry Sf Si Um Uy Va Vz Yj) kG(aA aF aO Aw aZ Cu Di Fw Gn hC Hl Hp Hr Hu Ic Jj Jk Jl Jq Kd Ke Kq Lu Lz Mb Mh Ml Mp mU Mv Mw Nd nI nN nR nU Or Pb Pe Pg Pi Po Qb Rv Uf Ut Vu Vv Yd Yj) Oh(eD Et Gb Hp Ik Im Jj Jl Ju Jv Ma Mb Me Mj Mu mW Nb nF nI Nj Nk Nl nR Nu Nv Nx Pg Po Qa Qb Rm Rx Yi Yj) Um(aR cF cT CU Dc fP Fy Gp Ij Ji Jl Jp Jq Lv Ly Ml Na Nb nR nU Pc Pg Qe Qv Qy Tn Ub Ue Uf Vi Vp Vu tF) aZ(aA aN aO aP Ar cC cE cT De Fi gV Ih Im Iv Jj Jo Lu Mb Mh Mm Mu Mx Ne Nn Nq nR Ns Nt nU Po Si Uy Yi Yf) Lv(Ad As aU AX Bo bS cB cF cK cU De kC kF Ma Mb Mh mU Mz Nb Nd nI Nj Nq nR Ns nT nU Nv Po Qb) nN(aA aF Hr Jj Jo Jq Jr Jt kE kI kN Lu Lz Mb Mh Mj Ml Mm Nb nI Nm Nn Of Ok oO Pc Pe Pg Qa Tz Vv) Nl(Et Fr Im Jj Jk Jp Jq Lh Lw Lx Ma Mb Mh Mj Mp Mt Mu Mz Nb Nd Nq Nu Nv Nx Pc Pe Po Qa Qb) Jl(Gb Hp Hr Im Jm Jo kF Lh Ma Me Mf Mh Mi Mj Nb Ng nI Nk Ns Nx Of Og Pg Po Qa Rx Yi Yj) Nd(cB De Ed Gb Gp Gz Hl Ky Mb Nj Ou Ow Qy Ry Tn Ue Uf Uk Uo Ut Va Vj Vu Yi Yl Ye Yf) mP(aA aF Hr Jj Jo Jq kE Lh Lu Lz Mh Ml Mm Nb nI Nm Of Ok oO Pc Pe Pg Qa Qd Tz Vv) kF(aA Ji Jj Lh Lu Lz Mb Ml Mm Mp Mu Mv Mx nI Nm Nq Oe Of Oi Ou Pc Pf Pg Qa Qb Tz) nR(aA aF Al cF Cv Gn Hr Ji Jt Ju Lh Li Mp Nb Ni Nm Ns Of Pc Rb To Tz Ug Ur Vv) nU(aA aF Cv Hl Ji Jj Jq Li Lz Mb Mh Ml nA Nb nF Ns Nt Of Ok Pc Pe Pf Pg Qa Ur) Nu(Et Im Jq Lh Ma Mb Mh Mj Mp Mt Mu Mz Ng Nj Nk Nq Nv Nx Og Pc Pe Po Qa Qb) Mb(Et Fr Im Jk Jp Jq Js Lh Lw Mj Mm Mp Mt MU Mz Nb Nq Pc Po Qb) Jj(aU cB cF De Ih Ij Ik Im Jk Jq Js Ma Mj MU Nj Nq Nv Pe Qb) oO(aA aF aO aP bQ bV bZ cF cU dF dG fR hC Lx Mj Mt Nb oE oF pH) Nj(Et Fr Im Jk Jp Lh Ma Mj Mp Mt Mu Mz Nb Nq Pc Pe Po Qa) cB(aA aP Im Iv Jr Lz Ma Me Mh Mi Mm Mp Mx Ng Nm Ns Oy Qb) Cu(Aa Dg Gd Hp Hr Hw Ii In Jt Mm nI Nm Oy Pb Uy Vb Vh) cU(As gV Hp Im Iv Jr LY ME Mm oV Pa Sf Sh Yg Yi) Gb(Ao Ed Fy Gp Hc Jp Js Mi On Ou Pe Qd Tn Vu Vv Yi) Qd(fP Gp Hp Ju Jv Kr Lp mE mU Rm Si Uo Uy Vt tF) cF(aA aJ aP bA cS ED hR Im Jo Me Mh Mi Mp Or) lL(aA aD aM aX BC bO dI hR jP Mf Mu Mx Nn) lN(aA aM Dl Fr Id jD jI jO jP Mu Mv Nn Or rZ) Ma(bS cE Im Mi Mt Mz Nk Nv Nx oT Po Qa Qb) Tz(Aa Bb fP Ib Kc Lp mZ nT Pj Uw Vj Yl tF) Yi(Js Kq Lx Mz Nb oF Or Ou Ow Pg Qa Rx Vi) Jr(Dr Du Em Gn Hl Hp Rx Ry Uz Wg Yg Yl Tl) De(aP BO bV cS Gd Hr Me Mm Nf Oy) Mz(As Cq Cw Hw Ij In Nq Om Uz Wg Yj) Jo(aU Ba cG cT Dc oE Ou Uf Ut Vu tF) On(Hl Lh Mm Nm Ry Uw Vb Vh Yg Yj Yl) Nv(Hq Im Me Mh Ng Nk Og Pb Qa Ry) Yj(bO Js Lx Nb Ou Ow Pg Qa Vi) Vu(Dp Gd Hl Hp Hr Lp mE Qv Si) eD(dI Fr hR jD Lj Mf Mu Mv Pc) oE(Dg Hr Iu Jm Me Mp Ne Oz Uo) Mi(As Bo bS cK Mj Mu Nb Ns) Tn(Ad Bb Dg fR Ib Iz Uu Vb) Ow(Du Gd Hp Rx Sf Si Vz Yl) Pg(Hp Ii Lh nI Ns Pb Qa Vb) Gp(Aa Fi Or Rx Sf Sh Yf) Mj(Et Im lY Mp Nk Ns Og) Qv(Mp Mu Mx Nn Ns Ou Ut) Vv(Hp Lp Rx Sh Ux Vb Vj) Nq(Je jT kN lM Ng Sh) gV(aL Ba bO Cw Dc dD) mE(aA Kq Li Qa Uf Ut) nI(aF Kq Ky Mp Mx nT) Po(Li Lj Ng Ns Og) Mf(jI jO jP Me qW) Mu(kE kI Me Ng Ue) cT(Em Gd Je Rx Uo) Nn(jP lM oW Ra) Mh(aX Et Im Nx) Mp(cK kE kN lY) Qa(Hv Ij Iu Pc) Or(As Hr Lw Oy) Uf(Dg kI Nm Ue) aA(Aa bO dH hR) aP(bL bO bR dG) Lz(mU mZ nT) Nb(kE kN nT) Im(aU bS Nk) Hc(Gd Sh Va) Ji(Ad Bo Cw) Ou(Hr Oy Yf) rZ(jP jT Mx) oF(fR Gh Hl) Aw(Gd Oy) Ns(Ir tF) Me(aU aX) Uc(Mv Qy) Id(jI lM) Qb(Jm Nx) Kq(lY mT) Lp(Hv kN) Ut(Mm Yf) Pc(oV oW) Pf(mU mZ) aF(oV oW) cE(cG dF) cS(BO) AaDc AoSh EfOy EdHp EtNk FrNg LxmZ MxqW HlHo TopH JsUy JvoT LilY NyPb UoVi hRjO jDjP Unconstrained panels with 3 analytes, where 1.7E-11 >= 'AUC p-value' > 0. Contains 50,000 panels of 23,517,221 total panels evaluated. : Tn{pK(aA aC aE AF aG aH aI aJ aL AN AO aP AR AS aU aV AW AX aY aZ bA bB BC bE bF BG bH bI bM BN BO bP bQ bR bS bU bV bW bZ cA cB cC cE cF cG Ch cI cJ cK cL cM cO Cp CQ cS CT CU CV Cw CX dA dB dC DD DE dF dG dH DI dJ DK dM dR dU eF eM eQ Et Fn FP Fr Fw GL GZ hB HC HF hG Hq Hr Hu Hv Hw Hx iA Ib Ic Id Ii iJ Ik Il In iO iP Iq Ir Iu Iv iZ Jd Je Jf Jh Ji Jl Jn Jr Jy KC Kd kE kF Kg Kl KK KN KO kQ KR Kx Kz Lv LW LX LY Lz Mb Mc Md ME Mf Mg MH Mi Mj Mk Ml MM Mn MP Mq Mr MS MT MU Mv MW Mx MY mZ NA NB Nc Nd Ne NF Ng Nh Nl Nj NK Nl nM NN No Nq Nr Ns Nt NU Nv Nw Nx Ny oD OE oF Og OH Oi oK oN oO oQ Or oT Ou oV oW Oy Pa Pc Pd PF Pg PH Pl Pk Po Pz Qc Qd Qg Ql Qm Qn Qt Qu Qv Qw Qx Qy Qz Ra Rb Rc Rg Rh Ri Rj Sr To Ua Ub Uc Ud Uh Uk Ul Um Un Uo Up Ur Us Ut Uv Vp Vs Vt Vu Vv Wm Tj tF) oO(aA aC aD aE AF aG aH aI AJ aK AL aM AN aO aP aQ AR AS aU aV AW AX aY aZ BA bB BC bE bF BG bH bI bJ bL bM BN BO bP bQ bR bS bV bW bX bZ cA cB cC cD cE cF cG CH cI cJ cK cL cM cN CO CP CQ cR CS CT CU cV CW CX cY cZ dA DB DC dD DE dF dG dH DI dJ DK dL dM dN Dp dR dU eF EM Ez Fa Fb FP Fr Fw Fy gC GL GP Gz Ha HB HC Hf hG Hr Hu Hw Hx Ib Ic Id IH Ii Ij Il Im In IO iP Ir It Iu Iv Iz jB Jd Jg Ji Jj Jk Jl Jm Jo Jq Js Jt Ju Kc Kd KF kG Ki Kk Kn Ko Kp KQ KR kS Kx Ky Kz Ld Lh Li Lu Lv lY Ma ME MF mH Mj Ml MM Mn MP Ms MT MU Mv Mw Mx Na NB Nc nD Nf Ng Nh nI Nj Nk Nm NN nO Nq NR Ns NT nU Nw NY Oa oE OF Og OH Oi Om On oQ Or oT oV OW Pa Pb Pc Pd PF PH Pi Pk Pz Qb Qc Qd Qe Qg Qm Qn Qt Qu Qv Qw Qx Qy Rc Rj Rm Ss To Ua Uc Ue Ug Uk Um Un Uo Ut Uu Uv Vo Vq Vt Vv Tj) fB(aA aC aD aE Af aH AJ aK aL aM aN AO aP aQ aR AS aU aV AW AX aY aZ bA bB bC bE bF bG bH bI bJ bL bM BN BO bP bQ bR bS bU bV bW bX bZ cA cB cC cD cE cF cG cH cK cL cO Cq cS CT cU Cv cW CX cY cZ dA DD DE DG dH DI dJ DL dN Dp Fa Fn Fw Gz Hf Hq Hr Hu Hv Ib Ik Il Ip Iq It Iu Iv Iz Jd Je Jf Jj Jn Jo Jr Jv Kc Kd kE kF KG Kj kK KN kO Kr Ks Lh Lv Lw LX LY Lz Ma Mb Mc Md ME MF Mg mH MI Mj Ml MM Mn MP Mq Mr mS MT MU Mv mW Mx MY mZ NA NB Nc ND Ne nF Nh NI NJ nK NL nM nN nO Nq NR Ns nT Nu Nw Nx Oa Oe Og Oh Oi Om On oP oQ Or Ow Pd Pe Pf Pg Ph Pi Po Qg Ql Qn Qt Qu Qw Qx Qy Qz Ra Rb Rg Rh Ri Rj Tz Ua Ub Uc Ud Ue Uk Um Uo Ur Us Ut Uv Vo Vp Vs Vu Vv Wm Tj) eP(aC Ad Af aG aH aI AL aN aO aR AS Aw Ax aY BA BB BC bF bI bL BO bR bS bW bX cA cB cC cF cI cJ cN cP cR cS Ct CU Cv cW Cx dA dD DE DG dH Di Dl dM Dp dR Ed Ef Fp Fy Gd Gz Ha hB Hc Hf Hq Hw Hx Ib Ic Ih Ii Ik In Iq Iu Iz Jf Jg Jj Jk Jm Jo Jr Jt Kc Kf Ki Kj Kk Kl Kn kR Ks Kx Ky Li Lv Ly Mb Me Mi Mm Mp Ms Mt Mu Mv Mw Nc Ne Nf Ng Ni Nj Nk Nl Nm Nn Nq Ns Nu Nx Ny Oa Oe OF Og Oi Ok oN Ou Ow Oy Oz Ph Pz Ql Qn Qt Qu Qv Qw Qy Qz Rb Rc Rf Rg Rj Tt Uh Um Uo Ur Us Uu Uv Vo Vp Vs Vv Wm) dX(aC Ad aH aI Al AO Ap aR AS Aw Ax

Figure 40 Continued aY BA Bb Bc Bg bI bL Bo bX cC cH cl cP Ct Cu Cv cW Cx dA dD DG dH Di dK Dl dM Dp dR Ed Ez Fa Fp Fy Gd Ha hB Hf Hq Hw Hx Ii Ik It Iu Iz Jf Jg Jm Jn Jo Jr Jt Kc Kf Ki Kj Kl Kn kR Ks Kx Ky Ld Lv Mb Me Mm Nc Ng Ni Nj Nk Nl Nm Nn Ns Nu Nv Nx Ny Oa Of Og Oh Oi Ok oN Ow Oy Oz Pf Ph Pz Qt Qu Qv Rc Rg Rm To Ug Uh Ur Us Uu Uv Vo Vv) nU(aC Ad Aj Al Ap Ba Bb Bc Bg Cp Cv Dd Dg Dl Dp Du Ef eQ Ez Fb Fc Fd Fi fR Fy Gb Gc Gh Ho Ii In It Iu Iz Jg Jj Jk Jm Jo Jr Jt KG Kj kK Kl Ks Lt Lv Mb mE Mm mT My nA Ng nI nJ Nm Nn Ns Nt Nx Ny Oa Oe Of Og Oh Oi Ok OP oQ oT Ou oW Oy PH Ps Pz Qu Qv Qz Rb Rc Rv Rx Ry Sh Sj Uf Ug Um Ur Uu Uw Uy Va Vi Vo Vs Vv Wd Wf Wh Yd Yh Yi Yj Yk Yl Zw Zx Ye Tm Tl Ti Th Yf) nI(aC Ad aF Aj Al Ao Ap aR aU aV Ax Ba Bb Bc Bg bX cF Co Cp Ct Cv Cw dA dC DG Dl dM Dp dU Ef Eq Fa Fb fP fR Fy Gb gC Gd Gn gZ Hc Hl Hw Ib In Io It Iz Jg Jj Jo Jt Kd Kf Kg Kj Ko Ks Ky Lh Mm Mn Mp mY Nd Ng Nk Nm NT Nx Of Oi Ok Om oT Ou Pc PH Pj Pk Pz Qv Rc Rj Rx Ry Rz Sh Sj Ss Uc Ue Ug Um Uu Uw Ux Uy Va Vb Vo Vw Wd We Wf Wh Yi Yj Zw Ye Tm) oT(Ad AF aG Ao Ar Ax Ba Bb bE bF Bg bH bJ bL cM Cp CQ cV CW DC Dd dl Dk Dl dM dN dU eQ Et Ez Fa fP Fr Gl Hu Hx Ib Ii Ij In iO Ir Is It Jh Jl Jo Jt Jy Ke Kg Kj Ko Ks Li Lu lW lX Mb mF Mh Ml Mm Ms Mt MW Mz Ng Nh nJ Nk Nn No Nq Nr Nt Nv Nw Nx Oa oD Oe Of Oh Oi Ow Pa Pc Qc Qn Qu Qy Rf Rj Sr St Tz Ua Uc Ug Uh Ul Un Uv Vo Vq Vt) gC(Ad aF Aj AO Ap Ar Ba Bc bF Cp CS Cu Cw Dc Dg Dl dM dN Dp eF Et Ez Fb Fp Fr Hb Hq Ib Id IO Ir Is It Iu Jd Jg Jh Ji Jt Ju Jv Kc Ke Kf KG Kl Kn Kq Lu mF MM Mn Ms MT MW Ng Nj Nk Nm Nn No Nr Ns Nv Nw Nx Oe Of Oh Oi Ok On Ou Pc Pf PH Pj Qa Qb Qc Qh Qm Qn Qu Qv Qz Rc Rf St Uv Vq Vt Vv) kI(Aa Ad Aj Ao Ap Ax Ba Bb Bc Bg cM Cp Cs Cu Dc Dg dH Dl Du eC Ef Ez Fa Fb Fp Fy Gd Gn Hb Hl Hp Ii Ij Im It Iz Jg Ji Jj Jm Jo Jq Js Jt Ju Ke Kf Kj Kl Kn Kq Ks Lh Li Lp mF Mm Mn Ng Nh Nk Nm Nn Nr Nt Nv Nw Ny Of Oh Ok On Op Pc Pj Pz Qe Qh Rc Rf Rm Rx Ry Sf Sh Sj Ss Ug Uu Uw Va Vo Vq Vt Vw Wb We Yd Yi Zw Tm) oQ(Ad Aj Ao Ap Ax Ba Bb Bc bF Bg bL bO bX cF cM Cp Cs Cu Cv Dc Dd Dg dH Dl Ef Em Et Ez Fa Fb Fp Fr Fy Hb Ij Im Ir It Iz Jd Jg Jh Ji Jj Jk Jm Jo Jq Js Jt Ju Jv Ke Kf Kg Kj Kl Kn Kq Ks Lh Li Lu Mm Mn Ms MT Ng Nk Nm Nn Nr Nt Nv Nw Ny Oe Of Oh Oi Ok On Pc Ph Pj Pz Qb Qe Qh Qn Rc Rf Rm Ss Uf Ug Uu Vo Vq Vt) oP(Ad Af Ao Ap Ar Ax Ba Bb Bc bF Bg cF cM Cp Cs Cu Cv Dc Dg Dk Dl Dp Ef Em Et Ez Fa Fb FP Fy Hw Ib Ii Ij Ik Im Ir It Iz Jd Jg Jh Ji Jj Jm Jo Jq Js Jt Jv Kf Kg Kj Kk Kl Kn Lh Li Lu Mm Mn Mt Ng Nh Nk Nm Nn Nr Nt Nv Nw Ny Oe Of Oh Oi Ok On Ow Oz Pb Pc Pj Pz Qc Qe Qh Qm Qn Qv Rc Rm Ss Uf Ug Uu Vo Vq Vt) pH(Ad Af aG Ao Ap Ar Ax Bb cJ cM Cp Cs Cu cV Cw DC dF Dg Dk Dl dM Et Ez FP Fr Gl Hb Hw Hx Ib Ii Ij IO Ir Is It Iu Jd Jg Jh Jp Jt Ju Jv Kf kG Kk Ko Ky Lh Lu Lx Mm Ms MT Mw Mz Ng Nj Nm Nn No Nr Nt Nv Ny Oa Oe Of Oh Oi Ok Oz Pb Pc Pj Qa Qc Qh Qm Qn Rc Rf St To Uh Un Uv Vo Vq Vt) dU(Ad aF Aj AO Ap Ar Ba Bg bU cM Cp cQ CS Cu Cv Cw Dc Dg Dl dM dN Dp Et Ez Fp Fr HB Ib Ij IO Is It Iu Jd Jg Jh Ji Jt Ju Jv Kf Kg Kl Kn Kq Lj Lu mF MM Mn Ms MT Mw Ng Nj Nm Nn No Nr Ns Nv Nw Nx Ny Of Oh Oi Ou Pc Pf Ph Pj Qa Qc Qh Qm Qn Qu Qv Qz Rc Rf St Ur Vq Vt Vv) eQ(aF aG Aj Al Ao Ar Ax Ba Bc bF Bg cM Cp Cs Cu Cw Dc Dl Et Ez Fa Fp Fr Gl Hw Ib Id Ij Ik IO Ir Is It Jd Jh Ji Jo Ju Jv Jy kC Kf KG Kj Kn Ko Kq Lj Lu Ma Mm Mn Ms MT Mw Ng Nk Nm Nn No Nr Nt Nv Nw Nx Ny Oa Of Oh Oi Pc Pz Qc Qd Qm Qn Qu Qv Rc Ug Un Uu Vo Vq Vt Vu) jB(Ad aF Aj Al AO Ap Ar Ax Ba Bc bF Bg cF cM Cp Cs Cw Dc Dg Dl Dp Et Fp Fr Hb Ib Ih Ii Ij In IO Is It Jh Ji Jt Ju Jv Kc Ke Kf KG Kj Lj Lu mF MM Mn Ms MT Mw Ng Nj Nm Nn No Nr Ns Nt Nv Nx Ny Of Og Oh Oi Ou Pc Pj Qc Qd Qh Qm Qn Qv Qz Rc Rf St Ur Uv Vo Vq Vt) eM(Ad Af Aj Al Ao Ap Ax Ba Bb Bc Bg Cp Cu Cw Cx dA Dg Dl dM Eq Ez Fb Fd Fy Gb Gd Gn Ha Hl Hp Ii It Iu Iz Jg Jo Jt Kf Kg Kj Kl Kn Ks Ld Ma Mb Mm Ng Nk Nm Nn Nv Ny Of Oh Oi Ok Ou Ph Pz Qu Qv Rc Rg Rm Rx Ry Rz Sh Sj Tt Uf Ug Ur Uu Uw Ux Uy Va Vb Vo Vv Vw Wb We Yg Yj Th) kG(Ad Aj Al Ap aU Ba Bb Bc Bg bW bX Cp cR Cv dC Dg dK Dl dM Eq Fb Fd fP fR Fy Gb Gd Gn Gp Hl Hw Ib In Iz Jg Jj Jo Jt Kf Kg Kj Kl Ko Ks Lh Ma mE Mj Mm Mn Mp Nb Nd Nh Nm NT Of Oi Ok Om Oz Pb Pc pI Pz Rc Rx Ry Sh Sj Ss Tr Tv Ug Uu Uw Ux Uy Va Vo Vw Wb We Yi Th) oD(Ad AF Ao Ap Ar aU bF Bg cM Cp cQ Cu Cw dA Dc Dg Dl dM Dp dR Et Ez Fb Fr Hb Ib Ih Ij In IO Ir Is It Jg Jh Ji Jo Jt Jv Jy Ke Kf Kj Kl Kn Kq Lx MM Mn Ms MT Nf Ng Nm Nn No Nr Nt Nv Nw Oa Oe Of OH Oi Ok Pc Pj Qc Qh Qm Rc Rf St Ug Ur Uv Vo Vq Vt Vu) gZ(Ad AF Al Ao Ar Ax Bc Bg cF cM Cp Cu Cw Dg Dk Dl dM Et Ez FP Fr Gl Hx Ih Ii Ij iO Ir Is It Jd Jh Ji Jl Jm Jo Jv Jy Kj Ko Ks Kz Li Lj Lu MM Ms MT Mw Mz Nf Ng Nk Nn Nr Nv Nw Nx Ny Oa Of Oh Oi Ow Oz Pb Pc Qc Qm Qn Rc Rf St To Ug Uh Un Uv Vo Vq Vu) pI(Ad AF AO Ap Ar Ax Ba bF Bg cM Cp Cs Cu Cw Dc Dg Dl Et Ez Fa Fp Fr Gl Hb Ib Ih IO Ir Is It Iu Jd Jg Jh Ji Jj Jo Jt Ju Jv Kc Kf Kl Kq Ks Lu mF Mm Mn Ms MT Mw Ng Nk Nm Nn No Nr Ns Nv Nw Nx Oa Of Oh Oi Ok Pc Ph Pj Pz Qc Qh Qm Qn Rc Rf St Ug Vq Vt) mS(Aa Ad Aj Ao Ap Ax Ba Bb Bc Bg Cp Cu Dg Dl Ef Ez Fa Fb Fy Gb Gd Gn Hb Hl Hp Ii Im It Iz Jg Ji Jj Jo Jq Jt Ke Kf Kj Kl Kn Kq Ks Lh Li Lp Mm Mn Nm Nn Nr Ny Of Oh Ok On Op Pc Pj Ps Pz Qe Rc Rm Rx Ry Rz Sh Si Ss Ug Uu Ux Va Vb Vo Vw We Zw) mE(Ad Aj Al Ba Bb Bc Bg Cv Dc Dg Dl Dp Eq Fb Fy Gb Gd Gn Hl Ii It Iz Jg Jj Jk Jm Jo Jt Kf Kj Kl Ks Lp Lv Mm Mn Nd Nm Ny Oe Of Oh Oi Ok On Pz Qn Rc Rf Rm Rx Ry Rz Sh Sj Ss Ug Uu Uw Ux Uy Vb Vo Vw We Wf Yi Yj Ye Tm) oV(Ad Aj Ar Ax Ba bF Bg cM Cp Cs Cw Dg Dl Et Ez Fp Fr Ib Ii iO Ir Is It Jd Jg Jh Jl Jo Ju Jv Jy Kg Kj Kl Lj Lu Mm Ms Mt Mw Ng Nk Nn No Nq Nr Nt Nv Nx Ny Oe Of Oh Oi Pc Pz Qc Qm Qn Qy Rc Rm St Ug Un Uv Vo Vq Vt Vu) mH(Ad Aj Al Ba Bb Bc Cp Dg Dl Du Eq Fb Fc Fd Fy Gh Gn Hl Ho Iz Jj Jo Jt Kj Kl Ks Lp Lt Mm Nm Nn Of Oh Oi Ok Op Pc Pz Rc Rt Rv Rx Ry Rz Sj Ss Uu Uz Vc Vh Vi Vo Vz Wc Wd We Wf Wg Wh Yd Yj Yk Yl Zw Zx Ye Tm Xa) kE(Ad Aj Al Ap Ax Ba Bb Bc Bg Dg Dl Du eC Ef Ez Fa Fb Fd Fy Gb Gd Gn Hl Ii Iz Jg Jj Jo Jt Kf Kj Kl Kn Ks Lp Mm Nm Of Oh Oi Ok On Op Ps Pz Rc Rm Rx Ry Rz Sf Sh Si Ss Ug Uu Uw Ux Va Vb Vo Vw Wb We Yi Zw Tm) mT(Ad Af Aj Al Ba Bb Bc Bg bX Cp cS Cv Cx dA DG Dl dM Fy Gb Gd Gn Hc Ib Ii In Iz Jg Jj Jo Jt Kj Kl Kn Ko Ks Mm MP Mu Nm NN Nq Of Oi Ok oW Ph Pz Qy Rc Rx Sh Sj Ss Ug Uu Ux Uy Va Vo Vw Yi Yj Ye) nJ(Ad Aj Al Ap Ba Bb Bc Bg bX Cv Dg Dl Du Eq Fb Fd fP Fy Gb Gc Gd Gh Gn Hl It Iz Jg Jj Jo Jt Kj Kl Ks Lh Mm Mn Nm Of Oh Ok Om Op Pc Pz Rc Rv Rx Ry Rz Sh Ss Uu Uw Ux Uy Va Vo Vw Wf Wh Yj Yl Zx Ye Tl) oW(Ad AF Ao Ar Ax Bc bF Bg Cp Cs Cu Cw Dc Dg Dl Et Ez Fb Fr Gl Ib Ih Ij iO Ir Is It Jd Ji Jo Jv Kg Kj Kn Kq Li Lu Mm Mn Mt Nn No Nr Nt Nv Nw Nx Oe Of Oh Ok Pc Qc Qd Qh Qm Qn Rf St Ug Uv Vo Vq Vt) nT(Ad Aj Al Ap Ax Ba Bb Bc Cv dA Dg Dl Dp Eq Ez Fd Fy Gb Gd Gn Hl Ii It Iz Jg Jj Jk Jm Jo Jt Kj Kl Ks Lp Mm Ng Nm Nn Nv Of Oh Oi Ok Ph Pz Qu Qv Rc Rx Ry Sh Ug Uu Uw Ux Uy Va Vo Vq Vw We Yi Th) mY(Ad Aj Al Ax Ba Bb Bc Bg Dg Dl Fb Fd Fy Gb Gd Gn Hl Ii It Iz Jd Jg Jj Jm Jo Jt Kf Kj Kl Ks Lh Lp Mm Ng Nk Nm Ny Of Oh Oi Ok Ps Pz Qe Rc Rx Ry Rz Sf Sh Si Sj Ss Ug Uu Uw Vo Vw We Yj Zw) nN(Ad Aj Al Ap Ba Bb Bc Bg Dg Dl Eq Ez Fb Fy Gb Gd Gn Hl Ii Iz Jg Jj Jk Jm Jo Jt Kg Kj Kl Ks Mb Mm Ng Nm Nn Nt Ny Of Oh Oi Ok Pz Qu Rc Rx Ry Sh Uf Ug Ur Uu Uw Ux Uy Va Vo Vw Wb We Yi) kP(Ad Aj Al Ap Ba Bb Bc Bg Cp Dg Dl Fb Fy Gd Gn Hl Ii It Iz Jg Jj Jo Jt Kf Kj Kl Ks Lh Li Lp Mm Mn Ng Nk Nm Nn Nv Ny Of Oh Oi Ok On Pc Pz Rc Rx Ry Sh Ss Uf Ug Uu Uw Uy Va Vo Vw Wb We) nR(Ad Aj Al Ap Ba Bb Bc Bg Cv Dg Dl Ez Fb Fy Gb Gd Gn Hl Ii It Iz Jg Jj Jk Jm Jo Jt Kj Kl Ks Mb Mm Mn Ng Nm Nn Nt Of Oh Oi Ok Pz Qu Rc Rx Ry Sh Sj Uf Ug Ur Uu Ux Va Vo Vw We Yi) mU(Ad Aj Al Ap Ax Ba Bb Bc Bg Dg Dl Ez Fy Gb Gd Gn Hl Ii It Iz Jg Jj Jk Jm Jo Jt Kj Kl Ks Lp Mb Mm Nm Nn Nv Of Oh Oi Ok Pz Rc Rx Ry Sh Sj Ss Uf Ug Ur Uu Ux Uy Va Vo Vw We Yi) nH(Ad Aj Al Ap Ba Bb Bc Bg Dg Dl Eq Fb Fc Fd Fi Fy Gb Gd Gn Hl Ho Iz Jg Jj Jo Jt Kj Kl Ks Mm Nm Of Oi Ok Rc Ru Rx Ry Rz Sh Sj Ss Ug Uu Uw Ux Uy Va Vb Vo Vw Wb Wc Wf Yi Yk Ye) kK(Ad Af Aj Al Ap Ba Bb Bc Bg Cx Dg Dl dM eC Fa Fb Fy Gb Gd Gn Hl Hp Ii Iz Jg Jj Jo Jt Kf Kj Kl Kn Ks Lp Mm Nm Of Oh Oi Ok Pc Rc Rx Ry Rz Sj Ss Uu Uw Ux Uy Va Vb Vo Vw We Yi) nA(Ad Aj Al Ap Ba Bb Bc Bg Cp Cv Dg Dl Fb fP Fy Gd Gh Gn Hl Iz Jg Jj Jo Jt Kf Kj Kl Ko Ks Lh Lp Mm Mn Nm Of Oi Ok Ps Rc Rx Ry Sh Si Sj Ss Ug Uu Uw Uy Va Vo Vw Wb Wc We Yk) mM(Ad Aj Al Ap Ba Bb Bc Bg Cv Dg Dl Eq Fd Fy Gb Gd Gn Hl Ii Iz Jg Jj Jk Jm Jo Jt Kj Kl Ks Lp Mm Nm Nn Of Oh Oi Ok Pz Rc Rx Ry Rz Sh Ss Ug Uu Uw Ux Uy Va Vo Vw We Yi) mP(Ad Aj Al Ap Ba Bb Bc Bg Dg Dl Fb

Figure 40 Continued

Fy Gb Gd Gn Hl Ii Iz Jg Jj Jk Jm Jo Jt Kg Kj Kl Ks Lp Mb Mm Nm Of Oh Oi Ok Pz Rc Rx Ry Sh Sj Ss Uf Ug Uu Ux Uy Va Vo Vw Wb We
Yi) nB(Ad Aj Al Ap Ba Bb Bc Bg Dg Dl Fd Fy Gb Gd Gn Hl Ii Iz Jg Jj Jo Jt Kf Kj Kl Ks Lp Mm Nm Of Oh Oi Ok Pz Rc Rx Ry Rz Sh Sj Ss
Ug Uu Uw Ux Uy Va Vb Vo Vw We Yi Yj) nO(Ad Aj Al Ba Bb Bc Dg Dl Eq Fy Gb Gd Gn Hl Hp Ii Iz Jg Jj Jo Jt Kj Kl Ks Lp Mm Nm Of Oh
Oi Ok Ps Pz Rc Rx Ry Rz Sj Ss Tv Ug Uu Uw Ux Uy Va Vo Vw Wb Wd We Yi) nF(Ad Aj Al Ap Ba Bb Bc Bg Dg Dl Eq Fy Gb Gd Gn Hl Ii
Iz Jg Jj Jo Jt Kg Kj Kl Ks Lp Mm Nm Of Oh Ok Pz Rc Rx Ry Rz Sh Sj Ss Ug Uu Uw Ux Uy Va Vb Vo Vw Wb We Yi) nL(Ad Aj Al Ba Bb Bc
Cv Dg Dl Eq Fc Fd Fi Fy Gb Gd Gn Hl Ho Iz Jg Jj Jo Jt Kj Kl Ks Lp Mm Nm Oh Ok Pz Rc Rv Rx Ry Sh Sj Ss Ug Uu Uw Ux Uy Va Vo Vw
Wb We Yi Th) nC(Ad Aj Al Ap Ba Bb Bc Bg Dg Dl Eq Fy Gb Gd Gh Gn Hl Iz Jg Jj Jo Jt Kj Kl Ks Mm Nm Of Oh Ok Pz Rc Rx Ry Rz Sh Sj
Ss Ug Uu Uw Ux Uy Va Vb Vo Vw We Yi Th) lY(Ad Aj Al Ba Bb Bc Bg Cv Dg Dl Eq Fy Gb Gd Gn Hl Ii Iz Jj Jo Jt Kj Kl Ks Lp Mm Nm Of
Oh Oi Ok Pz Rc Rx Ry Rz Sh Sj Ss Uu Uw Ux Uy Va Vb Vo Vw We Yi) mF(Ad Aj Al Ap Ba Bb Bc Ct Dg Dl Eq Fy Gd Gh Gn Hl Hp Iz Jg Jj
Jo Jt Kj Kl Ks Lp Mm Nm Oh Oi Ok Pc Ps Rc Rx Ry Sh Si Sj Ss Ug Uu Uw Uy Va Vo Vw We) ml(Ad Aj Al Ba Bb Bc Dg Dl Eq Fy Gb Gd
Gn Hl Hp Ii Iz Jg Jj Jo Jt Kj Kl Ks Lp Mm Nm Of Oh Ok Pz Rc Rx Ry Rz Sh Sj Ss Ug Uu Uw Ux Uy Vo Vw Wb We Yi) mZ(Ad Aj Al Ap Ba
Bb Bc Dg Dl Eq Fy Gb Gd Gn Hl Iz Jg Jj Jo Jt Kj Kl Ks Lp Mm Nm Of Oh Ok Ps Pz Rc Rx Ry Sh Sj Ss Uu Uw Ux Uy Va Vo Vw We
Yi) nD(Ad Aj Al Ap Ba Bb Bc Bg Dg Dl Du Fb Fy Gb Gd Gn Hl Iz Jg Jj Jo Jt Kj Kl Ks Mm Nm Of Oh Oi Ok Rc Rx Ry Sh Sj Ss Ug Uu Ux Uy
Va Vo Vw We Yi Yj Zw) nM(Ad Aj Al Ba Bb Bc Bg Dg Dl Eq Fy Gb Gd Gn Hl Iz Jj Jo Jt Kj Kl Ks Lp Mm Nm Of Oi Ok Pz Rc Rx Ry Rz Sh
Sj Ss Uu Uw Ux Uy Va Vb Vo Vw Wb We Yi) kF(Ad Aj Al Ba Bb Bc Bg Dg Dl Eq Fy Gb Gd Gn Hl Iz Jg Jj Jo Jt Kj Kl Ks Lp Mm Nm Of Oh
Oi Ok Rc Rx Ry Rz Sh Sj Ss Ug Uu Uw Ux Uy Va Vo Vw We Yi) lW(Ad Aj Al Ba Bb Bc Bg Dg Dl Fy Gb Gd Gn Hl Iz Jg Jj Jo Jt Kj Kl Ks Lp
Mm Nm Of Oh Ok Ou Pz Rc Ry Rz Sh Ss Ug Uu Uw Ux Uy Va Vo Vw We Wf Yi) IX(Ad Aj Al Ap aU Ba Bb Bc Dg Dl Fy Gd Gn Hl Iz Jg Jj
Jo Jt Kj Kl Ks Mm Nm Of Oh Oi Ok Pz Rc Rx Ry Rz Sh Sj Ss Ug Uu Uw Ux Uy Vo Vw We Zw) mW(Ad Aj Al Ba Bb Bc bX Dg Dl Fd Fy Gb
Gn Hl Ii Iz Jg Jj Jo Jt Kj Ks Lp Mm Nm Of Oi Ok Pz Rc Rt Rx Ry Sh Sj Ss Ug Uu Uw Va Vo Vw Wb We Yi) kO(Ad Aj Al Ba Bb Bc Bg Dg
Dl Fy Gb Gd Gn Iz Jg Jj Jo Jt Kj Kl Ks Mm Nm Of Oi Ok Pz Rc Rx Ry Sh Sj Ss Ug Uu Uw Ux Uy Va Vo Vw We Wf Yi) nK(Ad Aj Al Ba Bb
Bc Cv Dg Dl Fy Gb Gd Gn Hl Iz Jg Jj Jo Jt Kj Kl Ks Lp Mm Nm Oh Ok Rc Rx Ry Sh Sj Ss Ug Uu Ux Uy Va Vo Vw Wb We Yi) kN(Ad Aj Al
Ba Bb Bc Dg Dl Fy Gd Gn Hl Iz Jg Jj Jo Jt Kj Kl Ks Lp Mm Nm Of Oh Ok Pz Rc Rx Ry Sh Sj Ss Uf Ug Uu Uw Uy Va Vo Vw We Yi) kC(Ad
Aj Al Ap Ba Bb Bc Dg Dl Fy Gd Hl Iz Jg Jj Jo Jt Kj Kl Ks Lp Mm Nm Of Oh Ps Pz Rc Rx Ry Sh Sj Ss Ug Uu Uy Vo Vw We) fR(Ad Aj
Al Bb Gb Gd Hp Ii Iz Jj Jo Jt Kf Ks Lp Mm Nm Nv Of Ok Rt Ug Uu Va Vb Vo Yg Yi) Nd(Gb Gn Hl Lp Rx Ry Sh Uz Va We Wf Wg Yg Yh
Yi Yj Yk Tl Yf) Rc(Du Gn Hl Ry Uw Vc Vh Yj Yl) Yg(aY cA cK hC iZ oF pF) Gb(cU Ed Mi Qd Tz) Ry(Gd hC oE oF) Yi(Cu oF) AdoE EdHp
GdIb HbQd} kG{Yj(Aa aC Ad aK Al AN aO Ap aQ AS aU aV aX aZ bA Bb bE bF bI bO bQ bW bZ cG cH cL cN cO cR Cs cT CU Cw CX
dA dB DC Dd dF Dg dI Dl Dp DR Ez Fb Fc Fd Fi Fn FP FR Gb Gc Gd Gh Gl Gp HC Hl Hp Hq Hu Hv Hw Ib Ic Ih IJ Ik Il In Io Ip Iq Is Iv Jd Jf
Jg Ji Jl Jo Jp Jq Jr Js Jt Jv Kc KE Kf kl KK Kl KN Ko Kp Kq Kr Ks Ld Lh Li Lj Lv lW LX Lz Ma mE Mf MH ml Mj Mk Ml Mm Mn Mp Mr
mT mU mW Mx mY Mz nA NB nC Nd Nh NI NK Nm Nn nO Nr Ns Nt NU Nv Nw Ny Oa Oh Oi Om ON oO oP Or Ou Ow Oz Pa Pb Pc Pe Pf
Pg Ph Pi Pj Po Qb Ql Qm Qn Qt Rg Rh Rv Ry Rz Sf Sh Si To Tz Up Ut Vb Vp Vw Wb Yd Yg Yh Yi Zw Tj) aU(Ad An Ap Aw Bb Bc Cv Cw
Dd Dk Dl Dp Du Ed Em Eq Ez Fa Fb Fd Fi Fn fP Fw Fy Gb Gh Gl Gn Gp Gz Ha Hb HC Hf Hl Ho Hp Hv Hw Ib Ic Id Io Ir Is Iz Jd Je Jf Ji Jj Jl
Jm Jn Jo Jq Jr Js Ju Jv Jy Kc Kd Ke Kf Kg Ki Kj Kk Kl Kn Ko Kp Kq KR KS Kx Ky Ld Lh Li Lp Lu Lv Lw Lx Lz Ma Mg Mh Mj Ml Mm Mn
Mr Mx My Mz Nb Nd Nk Nm Nn No Nq Ns Nw Ny Oa Oh Oi On Op Or Ou Ow Oy Pb Pc Pe Pf Pg Pi Pj Pk Po Qd Qg Qh Ql Qm Qn Qt Qu
Qv Qw Qx Qy Qz Ra Rb Rc Rf Rg Rh Ri Rj Rm Rv Rx Rz Sh Si Sj Sr Ss St To Tr Tv Tz Ua Ub Uc Ud Uf Ug Uh Uk Ul Um Un Uo Up Ur Us
Ut Uu Uv Uw Ux Uy Vo Vp Vq Vs Vt Vu Vv Wb Yd Yg Yh Yi Yk Zx Ye Tl Wm Tj Ti Th) Nd(aC aF aV bR cF cL Cv dA Db Dd Dp Du Ed
Eq Ez Fa Fb Fc Fd Fi Fn Fw Fy Gb Gd Gh Gn Gp Gz Ha Hb Hc Hf Hl Ho Hp Ib Ic Id Iz Jd Je Jf Ju Jv Jy Kc Kd KE Kf Kg Ki Kj Kk Kl Kn Ko
Kp Kq Kr Ks Kx Ky Kz Ld Lp Lt Lx Mj Nb Nq Oa Op Or Ou Ow Ph Pi Pj Qg Qh Ql Qm Qn Qt Qu Qv Qw Qx Qy Qz Ra Rb Rc Rf Rg Rh Ri
Rj Rm Rt Ru Rv Rx Ry Rz Sf Sh Si Sj Sr Ss St To Tr Tt Tv Tz Ua Ub Uc Ud Ue Uf Ug Uh Uk Ul Um Un Uo Up Ur Us Ut Uu Uv Uw Ux Uy
Va Vi Vo Vp Vq Vs Vt Vu Vv Vw Vz Wb Yd Yg Yh Yi Zw Ye Tl Wm Tj Yf) Hl(aC aF aK aO aQ aS aV aX aY aZ bF bI bO bW bZ Ch cL cM
cP CU cV Cx dB DC dF dI DK dR eF Ez Fc Fd Fn fP Fy Gb gL GP hB HC hG Hp Hq Hv Hw iJ Il In iO Ip Iq Is iZ Jf Ji Jl Jn Jq Jr Js kN KQ KR
kS Ld Lh Lv lW Lx Ma mE Mf MH ml Mj Mk Mn Mp mT mW mY Mz Nb nH nl Nn Nq nR Nt NU Nv NW nY Oa oE oF Oh Om ON oO oP
Or Ou Ow Oy Oz Pa Pb Pc Pf Pg Pi Po Ps Qa Qd Qm Qn Rg Rh Rv Tz Uc Up Ut Vb Vp Vu Vv Yd Yg Yh Tj Th) Hp(aF al aK aL AO aQ aV
aX aZ bA bF bM bN bQ bW bZ cG cL Cp CQ cT cU Cx dA dD dF dl dM dR Ef eM Ex Ez Fd Fn Fw Fy Gn Gp HB HC Hf Hr Hv IH Ij lm In Io
Iq Ir It Jd Jf Ji Jk Jp Jq KK kO Kr kS Ky Lh Li Lv lW Lx Lz Ma Mg mH ml Mj Ml Mp Mq Mr Mt mU Mv Mx Mz Nb nl No Nq nR nT Oa oF
oH Ok ON OP oQ Or Ou Ow Pa Pb Pc Pe Pi Po Qa Qb Qc Qe Qh Ql Qm Qn Rg Rv Tv Ua Uc Uf Un Up Uw Vp Vs Vt Vu Vv Wh Yd Yh Yi
Yk Xa Tj) Vb(aF aH al Aj aL aX aZ Ba bC bF Bg bl bN bQ bV Ch cL Co Cq cS CT CU CX Dc DE dF Dg dl Dk Dp Du Eq Fy Gn Gp Hc Hr In
Iq Is It Iz Jd Jf Jg Jh Jk Jl Jp Jq Jr Js Ke Kg Kj Kk kN Kp Kr Ks Lh Lx mH ml Mn Mp mT Mu My Na Nf nL nR Ns Nt Nw Nx Ny Oe Of Oh Ok
On Or Ou Ow Oy Oz Pa Pb Pc Pd Pe Pf Ph Pi Ps Pz Qa Qb Qc Qd Qm Qn Qu Qz Rc Rg Rm Rt Rv Rz St Tv Tz Ua Uc Uf Up Uw Uy Vh Vi Vo
Vp Vs Vu Vw Wd We Wh Yd Yh Zx Tj) Gb(aD aE aF aH al AO aX aZ BA bB bF bM bN bQ bR bZ cA cD cG cL Cq cT CU cV CX dA dB Dc
dE dF dI Dk Du Em Ez Fd Fn Fw Fy Gn Gp HC Hq Hr Ij In Ip Iq Is It Jd Jf Ji Jk Jl Jn Jq Jr Js Ke kI Kk Kp Kr kS Ld Lh Lp Lv lW Lx Ma Mg
mH ml Mj Mn Mp mT mU mW Mx mY Mz Nb nC Nf nI nR nU Nv Nw Nx Ny Oa Oh Ok Om ON Op Or Ou Ow Pb Pc Pd Pe Pf Pg Pi Po
Qa Qh Qm Qn Qt Rv Tv Tz Uc Up Ut Vt Vv Yg Yh Yi Yk Zq Tl Tj) Yg(aF aH al aO aQ aV Aw aX aZ bA bF BN bQ bW bZ cE cG cL cN CQ
cT CU cV CX dA Dc dF dH dI dM dR eM Ex Ez Fn Fw Fy Gn Gp HC Hr Hv Ij lm In Iq It Jd Jf Ji Jl Jn Jp Jq Jr kI KK Kr kS Lh Lv Lx Lz Ma
Mg mH ml Ml Mp Mq Mr MT mU Mv Mx Mz Nb Nf Nm Nu Ny Oa oF Oh Ok ON oO OP Or Ow Pa Pb Pc Pe Pi Po Ps Qa Qb Qd Qh Qm Qn
Qt Rg Rh Rm Rv St Uc Uw Vi Vp Vt Vu Yd Yi Xa Tj) Mj(Al cF cl cR cY Dr Du Em Et Ex Fb Fd Fi Fr Gc Gd Gh Gn Ha Ho Hq Hr Hw Hx Ic
Ii Ij Io Ip Iv Jj Jk Jl Jm Jo Jp Jr Js Jt Ju Jv kN kO Ky Lh Li Lp Lt Lu lW IY MM Mn Mp mT MW Nb nC Ne nF Ng NH NI nK NL
Nm Nn Ns Nu Nv Nw Ny Oe Of Oi Om On oO Op oQ Oz Pa Pb Pc Pj Ps Qd Qe Rt Rv Rx Ry Rz Sf Sh To Ue Ul Va Vt Vv Vw Vz Wb We Yd
Yh Yk Yl Zw Zx Ye Tm Tl Xa Th tF) Yi(aF aH al aK Al aO aQ aV aZ bA bN bQ bW bZ cG cL cN cO Cq cT CU CX dA Dc dF dH dI dM dR
Et Ex Fd Fn Fw Gl Gp hC Hq Hr Hv Ih Ij lm In Ip Iq It Jd Jf Ji Jj Jl Jn Jp Kf KK Ko Kr KS Lp Lv Lx Ma Mg mH ml Mp Mq Mr MT mU Mv
Mx Mz Nb Nf Nm Nq nR Nv Ny Oa oF Oh Ok Om ON OP Or Ou Ow Pa Pe Po Ps Qa Qb Qd Qe Qh Qm Qn Qt Rg Rh Rv St Uc Un Uw Vi Vt
Wb Yd Xa) Gn(aC aF AN aO Ap aX aZ bH bO bW bZ cD cL cN cT cV Cx dB Dc dD dH DI Em Ez Fc Fd Fn Gd Gp HC Hq Hv Ic In Ip Iq Is Iz
Je Jf Jj Jl Jq Jr Js Jt Ke Ko Kp KQ Kr Ky Ld Lp Lt Lv Lx Ma mE Mf mH ml Mp mT Mx Mz Nb Ng NI Nm Nt NU NW Oa Oh oO Or Ou Ow
Oz Pa Pb Pc Pe Pg Pi Po Ps Qa Qb Qd Qh Ql Qm Qt Qv Qw Qx Qz Ra Rb Rf Rg Rh Ri Rm Sr St Tv Ub Uc Ud Ue Ug Uh Ul Um Un Uo Ur Us Ut
Uv Vo Vp Vq Vs Vt Vu Wm Tj) Gp(Aa aK Al aR Ax aZ bC bM bO bP cL cR dI Dr Du Em Eq Fc Fd Fi FR Fw Gc Gd Gh Ho Ic Jr Kd Lp Lt lW

Gn Hl Ho Hp Ii Iz Jj Kf Ks Lp Lt Mm Nm Nn Nv Of Op Pc Ps Rc Rt Ru Rv Rx Ry Rz Sf Si Ue Ur Uu Uw Ux Uy Uz Va Vb Vc Vh Vi Vq Vw Vz Wb Wc Wd We Wf Wg Wh Yg Yh Yi Yj Yk Yl Zw Zx Ye Tm Xa Th Yf) nU(aC Al Bb Du Em Eq Fb Fc Fd Fi Fy Gb Gd Ho Ii Iz Jj Jk Jm Jo Jt Ju Lt Mm Nm Nv Ny Oa Of Oh On Pc Ps Qe Qz Rc Rt Ru Ry Rz Sf Sh Si Ug Ur Uu Uw Ux Uy Va Vb Vu Vw Vz We Yd Yg Yh Yi Yj Yl Tl Xa Th Yf) eP(Aj aL aO bA bI Bo bS bV cH cN cT cU Cx dD dR Fy Gd Ha Hq Hu Ib Ii Iz Jf Jj Jo Jr Kf Kj Kk Ks Kx Ky Ld Lv Lx Ly Me Mh Mm Ne Nj Nm Nn Nu Nx OF oH Ou Ow Oy Qw Rb Rj Ss Ua Ug Uh Ur Uu Uv Vo Vv) mW(Al Bb Cp Dd Dg Dp Fb Fd Fy Gd Hl Hp Hw Ii Io It Iz Jg Jj Jk Jt Ju Jv Kf Kj Kl Kn Ks Lh Lp Mm Nm Nn Nv Of Oh Ok On oT Pc Pj Pz Rc Rt Rx Ry Rz Sf Si Ur Uu Uw Ux Va Vb Vw Wb We Yg Yi) kF(Al Bb Cp Dg Eq Ez Fb Fy Gb Gd Gn Hl Hp Ii Iz Jg Jj Jk Jm Jo Jt Kl Kn Ks Lh Li Lp Ma Mm Nm Nn Nv Of Oh Oi Ok Om On Pc Pz Rc Rt Rz Sh Si Ss Tv Ur Uu Uw Ux Uy Vb Vw Wb We Yi) mF(Al aU Bb Eq Fb Fd Fy Gc Gd Gn Ha Hl Ho Hp Ii Iz Je Jj Jk Jo Jt Ju Ks Lh Lp Mm Nm Nn Nv Of Oh On Op Pc Ps Rc Rt Rx Ry Sf Si Sj Ss Ur Uu Uw Vw Wd We Yd Yg Yi Yj Yl Zw Zx Tm) lY(Al Bb Cp Dp Fb Fy Gb Gd Gn Hl Ib Ii Io Iz Je Jj Jk Jm Jt Ks Lh Lp Mm Nm Nn Nv Ny Oe Of Oh Oi On Pc Qw Qz Rc Rt Rx Ry Sh Si Ur Uu Uw Ux Uy Vb Wb Wd We Yg Yi) nR(Ad Al Bb Cp Dg Fb Fy Gb Gd Gn Hl Hp Ii Io Iz Jg Jj Jk Jm Jo Jt Kl Ks Lh Lp Ma Mm Mn Nm Nn Nv Of Oh On Pc Rc Rt Rz Sh Si Tr Ur Uu Uw Ux Uy Vb Wb We Yg Yi) lW(Al Bb Eq Fb Fc Fd Fi Fy Gb Gd Gh Gn Hl Ii Iz Jj Jk Lp Mm Nm Nv Of Oh On Rc Rt Rv Rx Ry Si Sj Ur Uu Uw Ux Uy Va Vb Vh Vz Wc We Wf Wh Yg Yi Yk Zx Ye) mT(Al Bb cS Em Fd Gb Gd Gh Hl Hp Ii Iz Jj Jk Ju Lh Lp Mm Nm Nv Of Oh Ps Qz Rc Rt Ru Rv Rx Ry Rz Sf Si Ur Uu Uw Ux Va Vb We Wf Yg Yh Yi Yj Yl Ye Th Yf) mS(Ad Al Bb Eq Fy Gb Gd Gn Hl Hp Ii Iz Jj Jk Jt Ju Jv Lp Mm Nm Nn Nv Of Oh On Pc Pz Rc Rt Rx Ry Sf Si Ur Uu Uw Ux Uy Va Vb Vw Wb We Yg Yi Ye) nA(Al Bb Cp Dp Fb Fd Fy Gb Gd Gn Hl Ii Iz Jj Jk Lh Lp Mm Nm Nv Nx Of Oh Om On Op Pc Rc Rt Rx Ry Rz Sf Sh Sj Ur Uu Ux Va Vb Vw We Yi Yl Zx) kN(Al Bb FB Fy Gb Gd Gn Ha Hl Ii Iz Jj Jk Jo Jt Kl Ks Lp Mm Nm Nv Of Oh Ok On Pc Pj Rc Sh Si Ss Ug Ur Uu Uw Ux Uy Vb We Wf Yg Yi Ye) nT(Al aU Bb Eq Fb Fi Fy Gb Gd Ha Hl Ii Iz Jj Jk Jm Jo Jv Lp Mm Nm Nn Nv Of Oh On Rc Rv Si Ss Ug Ur Uu Uw Ux Uy Vb We Wf Yg Yi Ye) Ii(dU dX eQ fR gC gZ jB kC kE kI kK kO kP lX mH mI mM mP mU mY mZ nB nC nD nF nH nK nL nM nN nO oD oP oQ oT oV pH pI pK) Jj(dX eQ fR gC gZ jB kC kE kI kK kO kP lX mH mI mM mP mU mY mZ nB nC nD nF nH nK nL nM nN nO oD oP oQ oT oV oW pH pI pK) Mm(dU dX eQ fB gC gZ jB kC kE kI kK kO kP lX mH mI mM mP mU mY mZ nB nC nD nF nH nK nL nM nN nO oD oP oQ oV pH pI pK) lX(Al aU Bb Fb Gd Gn Hl Hp Iz Jk Jo Jt Kf Kl Li Lp Nm Nn Nv Of Oh On Pz Rc Rt Ry Sh Si Ur Uu Uw Ux Vb We Yg Yi) nC(Al Bb Fc Fd Gb Gd Gn Hl Hp Iz Jk Lp Nm Nv Of Oh On Ps Rc Rv Ry Rz Si Ur Uu Uw Ux Uy Vb Vw We Wf Yg Yh Yi Ye) nL(Al Bb Fb Fd Gb Gd Gn Hl Hp Iz Jk Lh Lp Nm Nv Of Oh Rc Rt Rv Ry Sh Si Ur Uu Uw Ux Uy Vb Vw Wb We Wf Yg Yi Ye) kK(Al Bb Fb Fy Gb Gn Hl Hp Iz Jk Jq Lh Lp Nm Nn Nv Ny Of Oh On Pc Rc Rx Ry Rz Sh Si Ur Uu Uw Ux Uy Vb We Yg Yi) dX(Aj bA cT dR Fy Gd Ha Hq Ik Iz Jf Jo Jp Kj Ks Kx Ky Ld Lv Mh Nj Nn Nx Of oH Ou Ow Oy Ss Ug Uh Ur Uu Vo Vv) mY(Al Bb Em Fy Gb Gd Gn Hl Iz Jk Jt Ju Jv Lh Lp Nm Nn Nv Of Oh On Pc Rc Rx Ry Sf Sh Si Ur Uu Ux Uy Va Vb Yi) kI(Al Bb Gb Gn Hl Hp Iz Jk Ju Jv Lh Lp Nm Nn Nv Of Oh On Pc Rc Rt Sh Si Ur Uu Uw Ux Uy Va Wb We Wf Yg Yi Ye) nN(Al Bb Fb Fy Gn Ha Hl Hp Iz Jk Jt Li Lp Nm Nn Nv Ny Of Oh Pc Rc Rz Si Ur Uu Uw Ux Uy Vb Vw Wb We Yg Yi) mZ(Al Bb Cp Fb Gb Gn Hl Iz Jk Jt Lp Nm Nv Of Oh Qz Rc Rt Rx Ry Sh Si Ss Ur Uu Uw Ux Uy Va Vb Wb We Yg Yi) fB(Al aO Bb bZ cM Ez Fb Gp Hb Ib Jp Jv Kf Ky Lh Lx Ma Mh Mn Mz Ni Nx Oh Om Ow Pb Pc Pd Qm Rc Ur Vt) mH(Al Bb Fy Gb Gd Gn Hl Iz Jk Lp Nm Nv Of Oh Rc Rt Rz Sh Si Ss Ug Ur Uu Uw Ux Uy Va Vb Wb We Yg Yi) mP(Al Bb Fy Gb Gd Gn Hl Hp Iz Jk Jt Li Lp Nm Nv Oh On Rz Sh Si Ss Ug Ur Uu Uw Ux Uy Vb Wb We Yg Yi) nB(Al Bb Fb Fy Gb Gd Gn Hl Hp Iz Jk Lp Nm Nv Of Oh On Pc Rc Ry Si Ur Uu Uw Ux Uy Vb Wb We Yg Yi Yj) dU(Al Bb Cp Dp eF Fb Ha HB Ib IO Iz Jk Jo Jq Ju Jv Kf Kn Nm Nn Nv Ny Of Oh Om Qh Ur Uu Vo) nO(Al Bb Fb Gb Gd Gn Hl Iz Jk Lh Lp Nm Nv Oh On Rc Ry Si Ur Uu Uw Ux Uy Vb Vw Wb We Yg Yi Ye) mU(Al Bb Fb Fy Gc Gn Hl Iz Jk Lp Nm Nn Nv Of Oh On Rc Rt Rz Sf Sh Ur Uu Uy Va Vb Vw We Yg Yi Tm) nF(Al Bb Fy Gb Gd Gn Hl Hp Iz Jk Lh Lp Nm Nv Of Oh On Rc Rz Sh Si Ur Uu Uw Ux Uy Vb Wb We Yg Yi) kC(Al Bb Fb Fy Gb Gn Hl Iz Jk Lp Nm Nv Of Oh Pc Rc Sh Si Ss Ug Ur Uu Uw Ux Vb Wb We Wf Yg Yi Ye) kE(Al Bb Fb Fy Gb Gd Gn Hl Iz Jk Lp Nm Nv Of Oh On Pc Rc Sh Si Ur Uu Uw Ux Uy Vb Wb We Yg Yi Tm) pI(Ad Al aO Bb Fb Ha Hb Ib iO Iz Jk Jo Jt Ju Jv Kn Lh Li Nn Ny Oa Of Oh Om Pc Pz Rc Rm Uu Vo Vq) nM(Al Bb Fy Gb Gd Gn Hl Hp Iz Jk Lp Nm Nv Of Oh On Rc Rz Sh Si Ur Uu Uw Ux Uy Vb Wb We Yg Yi) kP(Al aU Bb Gb Gn Hl Iz Jk Lp Nm Nn Nv Of Oh Pc Rc Rz Sh Si Ur Uu Uw Ux Uy Vb Wb Wf Yg Yi Ye) mI(Al Bb Fy Gb Gd Gn Hl Hp Iz Jk Lp Nm Nn Nv Of Oh Rc Rt Rz Si Ur Uu Uw Ux Uy Vb Wb Yg Yi) mM(Al Bb Gb Gd Gn Hl Hp Iz Jk Jt Lp Nm Nn Nv Of Oh On Pz Rc Ry Sh Si Ur Uu Uw Uy Vb We Yg) kO(Al Bb Fb Gb Gd Gn Iz Jk Lh Nm Nv Of Oh On Rc Rt Ur Uu Uw Ux Uy Va Vb Wb We Wf Yg Yi Ye) nD(Al Fy Gb Gn Hl Hp Iz Jk Nm Nn Nv Of Oh On Pc Rc Rt Sh Si Ur Uu Uw Ux Vb Wb We Yg Yi) nK(Al Bb Fy Gb Gd Hl Iz Jk Lp Nm Nv Nx Of Oh On Rc Rz Sh Si Ur Uu Uw Uy Vb Wb Yg Yi Ye) oQ(Al Bb Em Fy Hb Io Iz Jk Jo Ju Jv Ke Lh Li Mn Nm Nn Nv Nx Ny Of Oh Om On Pc Ur Uu) nH(Al Bb Gb Gd Hp Iz Jk Nm Nv Of Oh On Rc Rz Sh Si Ur Uu Uw Ux Uy Vb We Yg Yi Ye) oT(Al Bb Cp Fp Hb Ib IO Jd Jk Jm Jv Ke Kf Lh Nm Nn Ny Of Oh Ok Om Pa Pc Pj Qm) oP(Aa Al Bb Fy Hb Iz Jk Jo Jt Ju Jv Lh Mn Nm Nn Nv Ny Of Oh On Pc Rc) oV(Al Bb Cp Fb Ha Io Iz Jk Jm Jq Jv Kf Lh Nm Nn Ny Of Oh Om Pc Uv Vq) pH(Al Fb Ib iO Jk Kn Lh Mn Nn Nv Ny Om Pb Pc Vt) oW(Al Ha Iz Kf Kn Lh Li Nm Nv Ny Oa Of Oh Pc) pK(Dp Fb Ib Io Jk Jv Lh Nn Nv Ny Of Pc Ur) jB(Fb Ha iO Jv Kf Kn Lh Li Nm Nn Nv Pc) oD(Fb Ha Hw Jk Lh Nn Nv Ny Pc Ur Vq) Nd(Gb Hl Ry Sh Wf Yg Yi Tl Yf) eQ(Fb Kf Lh Nn Nv Ny Of Oh Pc) gC(Al Bb Fb Lh Nn Nv Ny Oh Pc) gZ(Fb Jv Lh Nn Nv Ny Of Pc) Yj(Ch Gb Ib Mh Rc Sh) Yi(bH CH oF Rc) Yg(bH dI dM oF) Ib(Gd Wg) Yl(Or Tz) fR(Jo Lp) GnRc MzSh WfNy RybH} Is{Yi(Aa aC AD aE AF aG aH aI aJ aK AL aM AN aO aP aQ aR AS aU aV AW AX aY aZ bA Bb BC bE bF BG bH bI bJ bL bM BN BO bP bQ bR bS bU bV bW bX bZ cA cB cC cD cE cF cG CH cI cJ cK cL cM cN CO cP cQ cR cS CT cU cV cW CX cY cZ dA DB DC Dd DE dF DG dH dI dJ DK DL dM dN DR Du eC Ed EF EM Eq Et Ez fB Fc Fd Fi FP fR Fw Gb Gd Gh GP Gz Ha HB HC HF hG Ho Hp Hr Hv Hw Hx iA Ib Ic Id IH Ii IJ Ik In Io iP Iq Ir It Iu Iv IZ Jf Jg Jj Jk Jm Jo Jp Jr Jt Ju Jv Jy KC Kd kE KF Kg KI Kj kK Kl KN KO KP kQ KR KS Ky Kz Ld Li Lj Lp Lt Lu Lv lW lX LY Lz Ma Mb Md mE MF MH MI Mj Ml MM MP Mq Mr MS MT MU Mv mW mY MZ NA NB NC ND Ne NF Ng NH NI NJ NK NL NM NN NO NR Ns nT nU nW Nx Ny oE oF Og OH Oi oK Om ON Op oQ Ow Oy Oz Pa Pb Pc Pd pF Pg Pj Pk Po Ps Qa Qb Qd Qe Qg Qh Qm Qn Qv Rf Rg Rh Rm Rv Rx Ry Sf Sh Si Sj Tr Uk Ul Um Un Uo Us Uw Ux Uy Vh Vt Vz Wc We Yg Yh Yl Zq Zw Zx Ye Tm Tj Ti tF) Yl(AA Ad AF Aj aK Al aM aO Ap Ar AS aU aV Aw Ax aZ bA Bb Bc bF bH bI bJ Bn bO bP bS bV bX cD cF cL cN cQ cR Cs cT cV Cw CX cY Dd De Dg dJ Dk Dl Dr Du Ef Eq Et Ex Ez Fd Fp Fy Gb Gc Gd Gh Gl Gp Ha Hb HC Hl Hp Hq Hr Hu Hv Hw Ib Ic Id Ih Ii Ij Ik Il Im In Ip Iq Ir It Iu Iv Je Ji Jj Jl Jm Jn Jo Jp Jr Js Jt Ju Jv Kf Kl Kn Ko Kq Ks Kx Ky Kz Ld Lh Li Lj Lp Lu Ly Ma Mb Mf Mh Ml Mm Mn Mr Mw Mz Na Nb Nc Nd Ng Nh Nj Nm Nn No Nr Ns Nt Nv Ny Oa Of Og Oh Oi Ok Om Op Ow Oy Oz Pa Pb Pc Pe Pi Pj Ps Qa Qb Qc Qd Qe Qg Qh Qm Qn Qv Qw Rc Rf Rh Rm Rt Rx Ry Sf Sh Si Sr St Tr Tz Ue Uh Un Uo Uu Uw Uy Va Vo Vt Vw Vz Wc We Wh Yd Zq Zw Zx Ye Tm Tl Ti) dX(AA aC AD aF aH aI AL aN aO aS Aw AX aY aZ bA bB BC bF bH bI bL Bn bO bR bS bU bV bX cA cB cC cD cE cF CH cI cK cN cP CQ cS cT cU Cv cW CX dA dB DD dE dF DG dH Di DK DL dM dN dR Ed eF Em Fy Gd Ha Hb hG Hq Hr Hu Hv Hw Ih Ii In Io Ip Iq Iu Jf Jj Jk Jl Jm Jn Jo Jp Js Jt Kc Kf Kk Kn Kp Kx Ld Lj Lu Lv Lw Mf Mh Mm Ms Nb Nc Nd Nj Nk Nm Ns Nx Oa Og OH Oi Ou Oy Oz Pc Ph Pz Qb Qc Qw Qz Rb Ri Rm Ub Uh Vo Vv Tj) Gb(aA AD Al aN AO Ap aS aX aZ Bb bC bI bJ bO bW cF cG Co cS cU Cv cZ Dc De Ef eM Ez Gp Hc Hp Ii In Ir Jd Jh Jj Jm Ju Jv KC kF Kg kN kP Ld Li lY Mg MI Ml MP mS MT Mu Mv mW mY mZ nC Nd

Figure 40 Continued nH nI nJ nK NL NN nO Nq nR Ns NT nU Nw oP Ow Pb Pd Pg Qa Qb Qd Qe Qy Rm Rx Rz Sf Sh Tv Ub Ud Uf Ul Um Uo Up Us Uy Uz Vj Vp Vu Vv Vw Vz Wd Wg Yg Yh Yj Yk Zq Zw Tl) Uy(Ad Af Ax bB bH Bn bO cF cL cQ cV Cx De Dp Du eM Et Fd Gh Gl Gp Ha Hb Hp Hv Ib Id Ih Ii Ij Ik Im Ir It Iu Ji Jl Jm Jo Jt Ju Jv Jy kC kF kK Kn Ks Kx Kz Lh Li Lj Lp lX lY Ma mH Mm Mq Mr mU Mv mY Mz nA ND Ne Nf Nh nO NR Ns Ny Oh Om Ow Oy Oz Pa Pb Pc Pj Ps Qa Qb Qc Qd Qe Qg Qv Rf Rm Rv Ry Sf Sh Si Um Un Uo Va Vo Wc Yj Zw Ye Tm Tl) eP(AA aC Ad aI Aj AL aO aS Aw Ax aY bA bC bF bI bO bV cC cD cF cH cI cN cS cT cU Cv Cx dB DD DG dH Di dK Dl dN dR Ed Em Fa Gd Ha Hq Hu Hw Ii In Io Iu Jf Jj Jm Jo Jp Jt Kf Kn kR Ld Lj Lu Lv Mm Nd Nj Nk Nm Nn Ns Nx nY Oa Og Oh Oy Pc Pf Pz Qz Rm Ub Uh Vo Vv) Rm(Dr Du Em fB Fd Gn Hl Hp kC kE kF kI kK kN kO kP lW lX lY mE mF mH mI mM mP mS mT mU mW mY mZ nA nB nC nD nF nI nJ nK nL nM nN nO nR nT nU oD oQ oW pK Rt Ry Si Uw Uz Vh Vi We Wg Yg Yh Yj Yk Zq Tl Xa Yf) Hp(Ad Ar Ax Co Ed eM Hb Ih Ii Ij Ji Jo Ju Jv kF Kg Ko Kq Ks Lh Li Lj Ma mF mI Mm mY Mz Nd nI nJ Nn nO nR nU Om Op Ow Pj Ps Qa Qb Qd Qe Qg Rc Rf Si Ul Un Va Vh Vt Vu Zw Ti) Al(dU eQ gC gZ jB kC kE kF kI kK kN kO kP lW lX lY mE mF mH mI mM mP mS mT mU mW mY mZ nA nB nC nD nF nH nI nJ nK nL nM nN nO nR nT nU oD oP oQ oT oV oW pH pI pK) Sf(Ad Du fB kC kE kF kI kK kN kO kP lW lX lY mE mF mH mI mM mP mS mT mU mW mY mZ nA nB nC Nd NF nH nI nJ nK nM nN nO nR nT nU oP Uc Uo Vt Vv Yg Yj) Hl(Ad Hb Hr Jv kC kE kI kK kN kO kP lW lX lY mE mF mH mI mM mP mS mT mU mY MZ nA nB nC ND nF nH nI nJ nK nL nM NN nO nR nT nU Oh Qh) Yj(Ad Ap Ef Et fR Gd Hb Ib Ij Jt Ju Jv Kq Li Lj mE mF Mh Mm mW Mz Nd Ng Nn Ny Oh Oi Om Ow Pj Qa Qb Qe Qh Rf Rx Sh Si Sr Tr Uh Un Vt Zq) Uw(Ad eM Ih In kC kE kF kI kK kN kO kP lW lX lY mE mF mH mI mM mP mS mT mU mW mY mZ nA nB nC nD nF nH nJ nK nL nM nN nO nR nT nU) Yg(Ad aO aZ bA bC bI bJ bQ bV cC cF cQ cU cX dF dJ dM eM Hb Hv Ih Ju Jv lY mE mW mY Mz Nd nJ nU Qa Qb Qe Qh Rf Vz Wc) Ad(Gh Lp mZ nR Op Ps Rx Ry Sh Ux Uz Va Vc Vi Vj Vz Wb Wc We Wf Wg Wh Yh Yk Zq Zw Zx Ye Tm Tl Xa) Lp(Fa Hb kC kK kN lW lX mE mF mH mI mM mT mW mY nB nC ND nH nI nJ nL NN nO nR nT nU Qa) Va(eM Hx Ij In kC kF lW lX lY mE mF mH mS mU mW mY mZ nB nC ND NH nJ nL Qa Uo Vv Yf) nL(Ps Rt Ru Rv Ry Sh Ux Uz Vb Vc Vh Vi Vw Wc Wd We Wf Wg Wh Zq Ti Th Yf) nC(Ps Rt Ru Rv Ry Sh Ux Uz Vb Vc Vh Vi Vw Wc Wd We Wf Wg Wh Ti Th Yf) nH(Gn Ps Rt Ru Rv Ux Uz Vb Vc Vh Vi Vw Wc Wd We Wf Wg Wh Zq Ti Th Yf) Zq(aZ eM kE kK kN lX lY mE mF mM mS mT mW mY mZ nB nD nI nO nT) Qh(Dr DU eQ gC Gn gZ jB nO nR oT oV oW pH pI pK Yk) Ju(Du fB kF kP lX lY mE mW mZ nI nJ nO nR oT pK) Vb(kC kF kK kP lY mS mW mY mZ nA nB nD nJ nN nO) Si(aZ cU Ud Ul Um Uo Up Us Uz Vp Vu Vv Wg) kF(Fa Jt Li Nm Nn Ny Of Ps Rx Sh Ux Vw We) Wg(Hb Ih Ir Jm Jv Ks Lh Mz Nd Qa Qb Qe) Uz(Hb Ih Im Jv Ks Lh Mz Nd Qa Qb Qe Rf) eM(Gd Jt Mm Nn Ny Op Ps Rx Ry Sh Vw We) Hb(Du Gn nI Um Vi Wf Yh Yk Yf) Sh(mH mW mY Mz nB Nd Nf nJ Vt) Ux(kC kP lY mP mT mW nN nO Uo) Nd(Du Rx Ry Vh Vi Xa Yf) Yh(Jv Ks Mz Qa Qb Rc Rf) nJ(Vh Vi Vw Wd We Wf Wh) Ax(aR cB cF fA lN nO) Jm(cD cF oV pK Vi Yf) Jv(Dr Du Gn oT Vi Yk) Ps(Ir mW mY mZ Um Uo) Rx(Dd kC kN lY mE oP) Rt(Ih lY mW mY mZ) Nn(Em fA nN nR) Mz(Dr Em Vi Yk) Ii(Fc fR Gd Yf) Vz(Aa Id In Kn) Ry(In Um Uo Vv) cF(Jo Jt Ng nO) Du(mP nD Uo) Gn(mW mY nO) Yk(mZ Qb Rf) We(mW nN nU) Vh(Hx In Uo) fA(Fa Lj Ny) Gd(Gp mY) Ns(Bb oE) Zw(kC Kn) Wh(nT nU) Wf(kC Ow) Op(Um Uo) nI(Lu tF) lN(Dc Ko) oT(Aa Ny) CvmZ HanO MaoV UemP IdlL IhVi ZxmW QenN WcJt LddU cUfR} Lp{kN(Ad aE AF aG aH aI aJ aK aM aN Ao AP aQ Ar aS aU aV AW aY aZ BA BB bC bE bF BG bJ bM Bn BO bP bQ bR bU bZ cA cB cC cE cG CH cI cK cL cM cN CO Cp Cq cR cS Ct cU cV CW CX cY dA DB DC DD DE dF dG dI dJ Dk dL DR Du Ed Ef Et Ez Fb Fc Fd Fi Fn Fp Fw Fy Gb Gc Gh GL Gp Ha HB Hc Hf Hl Ho Hu Ib Ic Id Ih Ij Ik Im In IO Ip Iq Ir It Iu IZ Jd Jf Jh Ji Jj Jk Jl Jm Jn Jp Jq Jr Js Jt Jy KC Kd Ke KF Kg KI Kk Kl Kn Ko KP Kq Ks Kx Ky Ld Lh Li Lj Lt Lu Lv lW Lx Lz Ma Mb ME MF Mg mH MI Mj Mk Ml mM Mp Mq MS MT MU Mv Mw Mx MY MZ NA nB nC Ne Nf Ng nH nI NK NL Nm NN No Nq Nr nT Nu Nv Nw Ny Oa oF Oh Oi Ok Om On OP Or Ou Ow Oy Oz Pb Pc Pd Pe Pf Pg Pi Pk Po Ps Qa Qb Qc Qd Qe Qg Qh Ql Qm Qn Qt Qu Qv Qx Qy Qz Rb Rf Rg Ri Rj Rm Rv Rx Ry Rz Sf Sh Si Sr St Tv Tz Ua Ub Uf Uh Un Uv Uw Vb Vi Vp Vq Vs Vt Vv Vz Wb Wd Yd Yg Yh Yi Yk Yl Zq Zx Xa Ti Th tF Yf) nI(Al Ao aQ aU aV bA Bg bO bQ bZ cE cF cG Ch cL Co Cp Cq cS cT cU dA Dc dF Di Dk dR Ef eM Fw Fy Gl Gn GP hB HC hF Hq iA Il In iP IZ Jd Jf Jh Jl Jp Jr Jy Kk KQ Kr kS Lh Lv Ma Mf Mj Mu Mv mW My MZ Nb nC Nd Nn Nq NR Nv oF OK Om oN oP Or Ou Ow PF Ph Pi Qa Qd Qh Qu Qw Qz Rg Ri Rz Ua Uc Uf Uv Uw Vi Vs Vu Yd Zx tF) nU(aF aK aO aQ aU Aw aZ bA bO cL Cq cT cU cY dE dH dI dJ Ez Fy Gl Gp HC Hq Hv Jf Jl Jn Jq Jr Js Kk Kq Ld Lh Lv Lx Ma mE mI Mj mT Mz Nb Nd Nv Nw Oh Om oP Ou Oz Pb Pc Pf Pg Ps Qa Qb Qd Qh Qt Qw Qz Rg Rm Rt Rv Tv Ua Ub Un Up Ur Us Uv Uw Va Vh Vi Vo Vp Vs Vu Vv Wd Wh Ti Th) Nd(aU Ax aZ bO cC CO cU dA Ed Et Fa Fb Fi Gd Gz Ho Hq Jf Jl Jr kC kF kI kK kO KP lW LX lY mE mF mH MI mM mS mT mY mZ nA nC nF nH NJ nK nL nM nN nO Nq nR nT Oa oP oQ Pg Ps Qc Qd Qe Qh Qu Qy Rb Rm Rx Tz Ua Uf Uh Um Uo Vj Vp Vq Vu Vv Wb Yi Tj tF Yf) mW(aJ aK aO aP aQ As aU Aw bB bZ cL cU cY dR Ex Gh Hc Hq Hv Jf Jl Jn Jr Js Kk Kq Ky Ld Lv Lx Ma mE Mf Mh Mk Mp Nb Nl oE oF Oh oN oP Ow Pf Pg Po Ps Qa Qd Qe Qt Rg Ri Ua Uc Un Uv Uw Vi Vu Vv Wd Wh) mE(AO aQ Aw bF bQ bZ cE Ch Co cS cU Dk dR EF gL Gp Hc iH iO Iz Jh Jl Kq Lh Lv Lx Ma Mu Mv My Mz Nb Nn Nq Nv oE oF oH Om ON Ou Pf Pg Qa Qd Qt Qu Rz Ua Uc Vi Vu Vv Wh) oP(aF An aO aQ aU bA bB bF bH bX bZ cD cF Ch cI cM Cq cS Ct cU cY dB De dI dJ Gh Gp Hc Ho Hq Hv Id Iz Jp Jr Kq Lx Ma Mj Mv MY Nn nR Nv Ny Of On Ou Oy Pc Pf Pg Ph Rx Ry Vz) lW(AO Aw bF bZ Ch Co cS cU Dk dR Ef Ez Gp Hc Hq iO Iz Jh Jl Jp Jr Jy Kq Lh Lv Lx Ma Mu Mv My Mz Nn Nq Nv OF Om ON Ou Pg Qa Qt Qu Qw Qz Rz Ua Uv Uw Vi Vu Vv Wd Zx) mI(aO aQ aU Aw bC bF bZ cL Co cS cU Ef Ez Fy Gp Hc Hq Iz Jh Jl Jr Kq Lv Lx Ma Mf Mt Mv Ng Ni Nn Nq oF oK ON Ou Pf Pg Pi Qd Qt Qu Rz Ua Uc Uf Vu Wh) mH(aJ aO Aw bF bZ cL cS Ct cU Ez Fy Gp Hc Hq Ih Im Jl Jr Js kF Kq Lx Ma Nn oE oF Oh ON Ow Pe Pf Pg Ps Qa Qt Qu Rz Ua Uc Uf Uw Vi Vq Vu Wh) nH(aO bF cL cU dI Dk Gp Hc Hq Jf Jl Jn Jr Lh Lv Lx Ma Mj Mz Nv oF Om On Ou Pf Pg Pz Qa Qd Qh Qt Qu Qx Qz Rg Rv Tz Ua Uw Vi Vp Vq Vv Wd Wh) mU(aO bF bZ cF cL Co cS dI dR gL Gp HC Hq Id iO Jf Jh Jr Lx Ma My Nb Nn oF Oi Pf Pg Qa Qd Qt Qu Qz Ri Ua Uc Uv Vi Vp Vu Vv Wd Wh) mF(aO aU bF Bg bZ Ch Co dR Ef Gp Hc Hq iO iP Jl Jr Kq Lv Lx Ma Mu My Nn Nq oE oF oK oN Ou PF Pg Qa Qd Qt Ua Uc Vu Wh) mT(Ao bZ cL Co cS cU Ef Eq HC Hq iO Iz Jd Kq Lx Ma Mg Mu Mv Mw My Nn Nq oF Om Ou Pf Pg Qd Qh Qt Rz Tz Ua Uv Vv) Vu(bO cH eM fR Gd Ib kC kE kF kI kK kO kP lX lY mM mP mS mY mZ nA nB nD nF nJ nK nL nM NN nO nR nT Ow Sh) Pg(aH fB Gb iA iH kC kE kF kI kK kO kP kQ lX lY mM mP mS mY mZ nA nB nC nD nF nJ nK nL nM nN nO nR nT oQ pF) lX(aK aO aQ bF bO bZ cE cY dR Gp Hc Hq Jl Lv Lx Ma Nb oE oF Ou Pf Qa Qd Qt Rg Ri Ua Uc Uv Vp Vs Vv) nJ(aQ Aw bF bZ cL cU Gp Hc Hq Jl Jn Jr Lh Lv Lx Ma Mj Mz Nb Nv oE oF Om oN Ou Pf Pi Qa Qd Qt Vi Wh) kE(aO aU Aw bC bF bQ bZ cL Ct cY Ez Hc Hq Jn Kq Lx Ma Nb Nv oN Ou Oy Pb Pf Pi Qa Qt Ua Uc Vs) nR(aO aQ aU Aw bZ cL cM Gn Gp Hc Hl Hq Hv Jr Lx Ma Nb Pc Pf Ps Qa Qt Qv Rg Tz Ua Vv Wh Th) nD(aO aQ bZ cL Ez Hc Hq Jl Jn Jr Lx Ma Mz Nv oE oF Om Ou Pf Ps Qa Qd Qt Qz Rm Uc Vp Vv Wh) nL(aF aQ aU bZ cL dR Gp HC Jl Jr Lx Ma Mj oF Ou Pf Qa Qd Qh Qt Ua Uc Vi Vv Wh) nC(aQ bF cL cU Gp Hc Jf Jn Jr Lx Ma Mj Mz oF Pf Qa Qd Qt Rg Rv Tz Uc Vq Vv Wh) kC(aU bF bZ cL dR Ez Gp Hc Hq Lx Ma Nb oF ON Ou Pf Qa Qd Qt Qz Rz Uc Vv Wh) kI(aO aQ bF bQ bZ cL Ct Gp Hc Hq Hv Jl Jr Lx Ma Ou Oy Pc Pf Qa Qd Qt Uc Wh) Vv(eM fR Hv Ib kF kK kO kP lY mM mP mY mZ nB nF nK nM nN nT Oi pF Rc) mM(aQ Aw bF bZ cS cU Gp Hc Hq Jn Lx Ma Nb oF On Pf Qa Qt Rg Uc) kO(Aw bF cL Gp Hc Hq Jr Lx Ma Mj oF Ou Pf Qa Qd Qt Ua Uc Uv Wh) nO(aO bF bZ cL Hc Hq In Jl Lv Lx Ma Mj Nq oF Ou Pf Qt Uc Wh) mY(bF cL Gp Hc Jn Jr Lv Lx Ma Mj oF Ou Pf Qa Qd Qt Ua Uc Wh) nB(AO bF bZ cL Hc Hq Jl Kq Lx Ma Nv On Ou Pf Qa Qt Ua Uc) kF(bZ cL dB Hc Jf Jn Jr Lv Lx Ma Mj Nb Pf Qa Qd Qt Rg Uc Uv) kP(aO bF bZ cL Gp Hc Hq Jl Lx Ma Mj oF Ou Pf Qa Qt Uc Vp Wh)

Figure 40 Continued nN(aF aO cL Ez HC Hq Jl Kq Lx Ma Mj Nb oF Qa Qt Uc) lY(aO bF Gp Hc Hq Jl Jr Lv Lx oF Ou Pf Qa Qt Ua Uc Wh) mS(aO bF bZ cL Gp Hc
Hq Jl Jr Lx Ma oF Ou Pf Qt Uc Wh) mZ(aO aU bF bZ dR Hc Hq Lx Ma oF oN Ou Pf Qa Uc Vq Wh) nA(bF bZ cL Fy Gp Hc Hq Lx Ma Nn Pf
Qa Qd Qt Uc Uv Vq) kK(aO bF Hc Hq Jr Lx Ma Mj Nv oN Ou Pf Qa Qt Uc Wh) nT(aO bZ cL Hc Hq Jr Lx Ma Mj Ou Pf Qa Uc Uw Wh)
mP(aO hC Hq Jr Lx oF Pf Qa Qh Qt Uc Vi) nK(bZ Hc Hq Jn Lx Ma Mj Pf Qa Qh Uc Vp) nM(bZ cL Hc Hq Jn Jr Lx Ma Pf Uc Wh) nF(bZ cL
Hc Hq Jn Jr Lx Ma Pf Uc Wh) oQ(bF Ct Gp Hq Jf Lx Ma Pf) oF(An aY Gh hB iA Jf Um) eM(Gp Hv Qa Vp) Tz(cF Hb iH) fB(cM Ct Hq) Fa(Jl
Qa) Fb(Nb Uc) Hv(Hc Yi) AdOn GdGp GzHc NbUo QdfR JrRx YlOu dJeC} Kq{eP(aC AD aF Aj aL aO Ap aR Aw Ax bA bF bI bV bX cT cU
Cw DG dH dK DL dR Ef Em Ex Fa Fb Fp Fy Hf Hq Hw Ik Im Iu Iz Jj Jo Jp Jr Jt Kf Kj Kl Kn Ks Kx Ky Ld Li Lj Me Mm Nc Nj Nk Nm Nn Ns
Nv Nx Ny Oa Of Og oH Oi Ou Pf Ph Pz Qe Qw Qz Rm Ss Ue Ug Uh Uu Vo Vq Vv) mE(Ad aF Aj Al Ap Bb Bc Co Cv Cw Dc Dg Dl Ef Fb Fr
Fy Gb Gd Gh Gn Hb Hl Hp Ii Iz Jg Jj Jk Jm Jo Jq Jt Jv Kl Ks Lh Li Mm Ng Nm Nn Nv Ny Of Oh Oi Ok On Pj Ps Pz Qe Rc Rm Rt Rv Rx Ry
Rz Sh Si Ss Ue Uf Ug Un Ur Uu Uw Va Vo Vq Vw Vz Wb We Yd Yg Zq Zw Ti) dX(aC Ad Aj aO Ap aR aS Ax bA bI bX cU Cv Cx DG Dl
dR Ef Fa Fy Gd Hq Ik Iu Jj Jo Jp Jr Jt Kf Kj Kl Kn Ks Kx Ky Ld Mm Nj Nm Nn Nv Nx Oa Of Og oH Oi Ou Ph Pz Qu Rc Rm Ss Ug Uh Ur Uu
Vo Vq Vv) nI(Ad aF Al Ap Bb Bc Cv Dg Dl Ef Fb Fr Fy Gd Gn Hb Hl Hp Ii It Iz Jg Jj Jo Jt Kl Ks Li Mm Ng Nm Nn Ny Of Oi Pj Ps Pz Qe Rc
Rm Rt Rx Sh Ss Ue Uf Ug Uu Uy Va Vb Vo Vq Vw Wb We Yg Yi Zq Ye) mT(Ad Al Bb Bc Dg Ef Fd Fr Fy Gd Gn Hl Ii Iz Jk Jt Kl Li Nm Nn
Nv Ny Of Ps Pz Qe Qh Rc Rf Rm Ru Rv Rx Ry Sf Sh Ss Ug Ur Uu Uw Uz Vc Vh Vi Vo Vt Vw Wb Wc Wd Wf Wg Wh Yd Yg Yj Zq Ti Th)
IY(Ad Al Ap Bb Bc Cv Dg Dl Ef Fb Fr Fy Gd Gh Hl Hp Ii Iz Jg Jj Jk Jm Jo Jt Kl Ks Mm Mt Nm Nn Nv Ny Oe Of Oi Ok Ps Pz Rc Rf Rm Rt
Rx Sh Ss Uf Ug Uu Uy Va Vw Wb We Yg Yi Zq) nJ(Ad Al Ap Bb Dg Fb Gn Hl Hp Iz Jg Jj Jt Jv Kl Lh Li Mm Nm Nn Nv Of Ok Pc Pj Ps Pz
Rc Rm Rt Ru Rv Rx Ry Sf Sh Tr Uu Uy Uz Va Vb Vc Vh Vi Vq Wc Wd We Wf Wg Wh Yg Yi Zq Yf) Nm(dU eM eQ fA fB gC gZ jB kC kE
kF kI kK kN kO kP lW IX mF mH mI mM mP mS mU mW mY mZ nA nB nC nD nF nH nK nL nM nN nO nR nT nU oD oP oQ oT oV oW pH
pI pK) Nn(cM eQ fB gC gZ jB kC kE kF kI kK kN kO kP lW IX mF mH mI mM mP mS mU mW mY mZ nA nB nC nD nF nH nK nL nM nN
nO nR nT nU oD oP oQ oV pH pK) Of(dU eM fB jB kC kE kF kI kK kN kO kP lW IX mF mH mI mM mP mS mU mW mY mZ nA nB nC nD nF
nH nK nL nM nN nO nR nT nU oP oQ) Yg(dF eM fB Gb kC kE kF kI kK kN kO kP lW IX mF mH mI mM mP mS mU mW mY mZ nA nB nC
ND nF nH nK nL nM nN nO nR nT nU) Al(fA kC kE kF kI kK kN kO kP lW IX mF mH mI mM mP mS mU mW mY mZ nA nB nC nD nF nH nK
nL nM nN nO nR nT nU oT oV) Iz(eM kC kE kF kI kK kN kO kP lW IX mF mH mI mM mP mS mU mW mY mZ nA nB nC nD nF nH nK nL
nM nN nO nR nT nU oP oQ) Ad(kC kE kF kI kK kN kO kP lW IX mF mH mI mM mP mS mU mW mY mZ nA nB nC nD nF nH nK nL nM
nN nO nR nT nU oP oQ) Pz(dU eM kC kF kI kK kN kO kP lW IX mF mH mI mM mP mS mU mW mY mZ nA nB nC nD nF nK nL nM nN nO
nR nT oP oQ) Vw(eM kC kE kF kI kK kN kO kP lW IX mF mH mI mM mP mS mU mW mY mZ nA nB nC nD nF nH nK nL nM nN nO nR
nT nU) Zq(eM kC kE kF kI kK kN kO kP lW IX mF mH mI mP mS mU mW mY mZ nA nB nC nD nF nH nK nL nM nN nO nR nT nU)
Rm(dU jB kC kE kI kK kO IX mF mH mI mM mS mU mW mY nA nC nD nF nL nM nN nO nT nU oD oP oQ oT oW pH pI pK) We(eM kC kE
kF kI kK kN kO kP lW IX mF mH mI mM mP mS mU mW mY mZ nA nC nD nF nH nK nL nM nN nO nR nU) Ps(kC kE kF kK kN kO kP lW
IX mF mH mI mM mP mS mW mY mZ nA nB nC nD nF nH nK nL nM nN nO nR nT nU) Uy(kC kE kF kI kK kN kO kP lW IX mH mI mM
mP mS mU mW mY mZ nA nB nC nD nF nH nK nM nN nO nR nT nU) Gd(fB kC kF kI kK kN kO kP lW IX mF mH mI mM mS mW nB nC
nD nF nK nM nN nO nR nT nU Yi Yj) Rt(eM kE kF kK kN kP lW IX mF mH mI mP mS mU mW mY mZ nA nB nC nD nF nH nK nL nM nO nR
nT nU) Jt(kE kF kI kK kN kO lW IX mF mH mM mS mU mW mY nA nC nD nF nH nK nL nM nN nO nR) Yi(eM fB fR Gb Iv kE kF kK MH
mI mP mS mZ Nd nF nK nM nO nT nU oF On pF Sh) Qe(eM eQ fB gC gZ jB kE kI kK kN mS mY nF nL nN nT nU oD oP oQ oV oW pH pI
pK) Hl(kC kE kK kN kO kP lW mF mM mP mS mW mY nA nB ND nH nN nO nR nT nU) Va(kI kK kN kO kP lW mF mI mP mS mU mW mZ
nA nB nC nD nH nK nL nT nU) Rx(kC kE kF kK kN lW IX mP mS mW mY mZ nD nF nK nM nN nO nR nT oQ) Ny(dU eM eQ fA fB gC gZ
jB kE kF kK mY nL nN nT oD oT oV oW pH pI pK) Mm(dU eM eQ fA fB gC gZ jB IX mW nH nO nU oD oT oV oW pH pI pK) Sh(kC kO kP lW
IX mF mH mI mM mP mW nY nB nD nH nL nN nR nU oQ) Rc(eM kK kP IX mF mH mM mU mW mZ nL nO nR oT pK) Jj(dU
jB kC kE kF kI kK kN mM mU mW mZ nA nF nH nK nO nU oQ) Ap(eM kF kN kO lX mF mH mM mU mW mY nA nH nK nL nO nR)
Gb(Aa eM Jr IX mY nF nK nM On Um Uo Vu Vv Yh Yj Yk Yf) Uu(eM fB kC kF kK kN mF mI mM mU mW mZ nA nH nK oQ pK) Fb(dU
eQ fA fB gC gZ kF nK nR oD oT oV oW pH pI pK) Kl(eM kF kN kP IX mM mW mZ nA nC nH nK nL nO nR nU) Vb(eM kE kK mH mI mP
mS mY nB nD nF nK nL nM nT nU) Jo(kF kN lW mF mI mM mU mW mZ nA nF nH nK nO oQ) Dg(eM kF kN kO lX mF mH mM mU mW
nH nL nO nR) Fy(kF kN lX mF mS mW nD nF nH nL nO nR nU) li(kE kF mY nC nD nH nK nL nO nR nT nU pH) Ss(eM kC kF mF mH mM
mP mS mW mZ nD nO oQ) Bb(eM kF kP mW nA nH nK nO nR nU oT pK) Uf(kF mF mH mM mU mW mZ nL nO nR oP oT) Li(dU eQ gC
gZ kE oD oV oW pH pI pK) fB(aF Hp Jv Mz Pc Si Sr To Tv Uh) oT(Jg Ji Jk Ju Jv Lj Ok Om Pc Pj) Wb(mF mI mM mP mW nC nL nU) dU(Cw
Ha Ju Mw Pc Qb Qh Vo) nU(Hp Vh Vo Vq Wf Th Yf) oV(aF aO cT Hb Ld Ma Pc) Oi(kC kF kN mU mW mZ) oQ(bA cT Ju Jv Sf Ug) Ks(nH
nL nO nR oP) Pc(jB nK oP pl pK) mW(Jg Jk Nv Ok Ug) Hp(mF mI nA nT) fA(Ax Fa Fp Lj) pK(Jk Jv Ue Vq) Dl(lW mS nO) Ry(IX mF mI)
mM(aF Ug Uw) Yf(Mz Nd) Ky(lL IN) Rz(kF nO) Rv(nC nL) Pj(mF nA) eM(Nv Ok) oP(Jv Sf) BckF CvnL EfkN GnkE MejV HbeQ SimF
WfnH JknK YlOu OrlN UgmH UwnC VvoW aFoD} Gp{Gd(Ar cA cU De Dr Du Eq Ex Fc Fd Fi Gb Gc Gh Gn Hl Ho Hp Hx iJ In Jr kC kE kF kI kK kN kO kP Ky Lh Lt Lv lW LX lY Mb mE mF Mh mI Mj mM mP mS mT mU mW mY MZ nB nC nD nF nH nI nJ nK nL nM nN nO nR nT nU Nw oF Oh OP oQ Or Ps Qd Qh Qv Qx Rt Ru Rv Rx Ry Rz Sf Sh Si Sj St Uf Un Uw Ux Uy Uz Va Vb Vc Vh Vi Vj Vp Vq Vu Vw Vz Wb Wc Wd We Wf Wg Wh Yd Yg Yh Yi Yj Yk Yl Zq Zw Zx Ye Tm Tl Xa Ti Th Yf) nI(Dr Du Eq Fc Fd Fi Gb Gc Gh Gn Hl Ho Hp Lt Op Ps Ru Rv Rx Ry Rz Sf Sh Si Sj Uw Ux Uy Uz Vb Vc Vh Vi Vw Vz Wb Wc Wd We Wf Wg Wh Yd Yg Yh Yi Yj Yk Yl Zq Zw Zx Ye Tm Tl Xa Ti Th Yf) mH(Dr Du Eq Fc Fd Fi Gb Gc Gh Gn Hl Ho Hp Lt Op Rt Ru Rv Rx Ry Rz Sf Sh Si Sj Uw Ux Uy Uz Va Vb Vc Vh Vw Vz Wb Wc Wd We Wf Wg Yd Yg Yh Yj Yk Yl Zq Zw Zx Ye Tm Tl Xa Ti Th Yf) mI(Dr Du Eq Fd Fi Gb Gc Gh Gn Hl Ho Hp Op Ps Rt Ru Rv Rx Ry Rz Sf Sh Si Sj Uw Ux Uy Uz Va Vb Vc Vh Vi Vw Vz Wb Wc We Wf Wg Yd Yg Yh Yi Yj Yk Yl Zq Zw Zx Ye Tl Xa Ti Th Yf) mE(Dr Du Eq Fi Gb Gc Gh Gn Hl Ho Lt Op Rt Ru Rv Rx Ry Rz Sf Sh Si Sj Uw Ux Uy Uz Va Vb Vc Vh Vi Vw Vz Wb Wc We Wf Wg Yd Yg Yh Yi Yj Yk Yl Zq Zw Zx Ye Tm Tl Xa Ti Th Yf) Sf(dE Ed eM Fa FB Fi fR Fw kC kE kF kI kK kN kO kP lW lX lY MF mM mS mT mU mW mY nA nB nC ND nF nJ nK nL nM nN nO nR nT nU oF oP oQ Or Ou Pg) kI(Dr Fc Fd Gb Gh Hl Ho Op Ps Rt Ru Rv Rx Ry Rz Sh Si Sj Uw Ux Uy Uz Va Vb Vc Vh Vi Vw Wc Wd We Wf Wg Yd Yg Yh Yi Yj Yk Yl Zq Zw Ye Tl Xa Ti Th Yf) nR(Eq Fc Fi Gb Gh Gn Hl Hp Lt Pc Ps Rt Ru Rv Rx Ry Sh Uw Ux Uy Uz Va Vb Vc Vh Vi Vw Vz Wb Wc Wd We Wf Wg Wh Yg Yh Yi Yj Zq Zx Tl Xa Ti Th Yf) nA(Dr Du Fc Fd Fi Gh Hl Ho Hp Lt Rt Ru Rv Rx Ry Rz Sh Sj Ux Uy Uz Va Vb Vc Vh Vi Vw Vz Wc We Wf Wg Yd Yg Yh Yi Yj Yk Yl Zq Zw Ye Tl Xa Ti Th) kN(Dr Fd Fi Gb Gc Gh Hl Ho Ps Rt Ru Rv Rx Ry Rz Sh Si Sj Uw Ux Uy Uz Va Vb Vc Vh Vi Vw Vz Wb Wc We Wf Wg Yh Yi Yj Yl Zq Zw Zx Xa Ti Th Yf) lW(Dr Eq Fc Gb Gc Gh Gn Hl Hp Lt Op Rt Ru Rv Rx Ry Rz Sh Sj Uw Ux Uy Va Vb Vh Vi Vw Vz We Wf Yd Yg Yh Yi Yj Zq Zw Zx Ye Tl Xa Ti Th Yf) kK(Eq Fc Fd Gn Hl Hp Lt Op Ps Rt Ru Rv Rx Ry Rz Uw Ux Uy Uz Va Vb Vc Vh Vi Vw Wc Wc Wf Wg Wh Yd Yg Yh Yi Yk Yl Zq Zw Zx Ye Tl Ti Th Yf) lX(Eq Fd Gh Hl Ho Lt Ps Rt Ru Rv Rx Ry Si Uw Ux Uy Uz Va Vb Vc Vh Vi Vw Vz Wc We Wf Wg Wh Yd

Figure 40 Continued

Yg Yh Yi Zq Zw Zx Ye Tl Xa Ti Th Yf) mY(Fd Fi Gb Hl Ps Rt Ru Rv Rx Ry Sh Uw Uy Uz Va Vb Vc Vh Vi Vw Vz Wc Wd We Wf Wg Wh
Yd Yg Yh Yi Yj Yk Zq Zw Zx Ti Th Yf) eM(Fd Gh Hl Ps Rt Ru Rv Rx Ry Sh Uw Ux Uy Uz Vb Vc Vh Vi Vw Wd We Wf Wg Wh Yg Yh Yi
Yj Yk Zq Zw Tl Xa Ti Th Yf) nU(Fc Fd Gb Gh Hl Ps Rt Ru Rv Sh Uw Uy Uz Va Vc Vh Vi Vw Vz Wc Wd We Wf Wg Wh Yd Yh Yi Yj Yk
Zq Zw Tl Xa Ti Th) oP(Dr Du Eq Fc Fd Fi Gb Gc Gh Gn Hl Ho Hp Lt Op Rx Ry Rz Sh Si Sj Vz Wb Yd Yg Yh Yi Yj Yk Yl Zw Zx Ye Tm Tl
Xa) mU(Fc Gn Hl Ps Rt Ru Rv Ry Uw Ux Uy Uz Va Vb Vc Vh Vi Vw Wc Wd We Wf Wg Wh Yg Yh Yi Yj Zq Zw Tl Ti Th Yf) kF(Fc Gb Hl
Ps Rt Ru Rv Rx Ry Uw Uy Uz Vb Vc Vh Vi Vw Wc Wd We Wf Wg Yd Yh Yi Zq Zw Zx Tl Ti Th Yf) kP(Fc Fd Fi Gn Ho Ps Rt Ru Ry Si Uw
Uy Va Vb Vh Vi Vw Vz Wc We Wf Wh Yd Yh Yi Yj Zq Zw Xa Ti Th Yf) nT(Fc Gb Gn Hl Op Ps Rt Ru Rv Ry Uw Uy Va Vh Vi Vw Vz Wc
We Wf Wh Yd Yh Yi Yj Zq Zw Xa Ti Th Yf) lY(Eq Fd Fi Gn Hl Ho Ps Ru Rx Ry Rz Si Uw Ux Uy Vh Vi Vz Wf Yd Yg Yh Yj Yk Zq Zw Zx
Ye Ti Th Yf) nH(Fc Fi Gn Hl Op Ps Rt Ru Rv Ry Uw Ux Uy Va Vh Vi Vw Vz We Wf Wh Yh Yi Yj Zq Zw Zx Tl Ti Th) mP(Fc Fi Gb Gn Hl
Ps Rt Ru Rv Ry Uw Uy Va Vb Vh Vi Vz Wc Wd Wf Wh Yh Yi Zq Zx Ti Th Yf) mF(Gh Hl Ho Ps Ru Rx Ry Sh Uw Ux Uy Vi Vw Vz Wd Wf
Wh Yg Yh Yi Zq Zw Tl Ti Th) mZ(Fd Hl Ps Rt Ry Uw Ux Uz Va Vb Vc Vh Vi Vw Wc We Wf Wg Yh Yi Zw Zx Ti Th Yf) kE(Ho Ps Rt Rv
Ry Rz Uw Ux Uy Uz Vc Vh Vi Vw We Wf Wg Yh Yi Yk Zq Tl Xa Ti Th) mM(Eq Fc Fi Gn Hl Ps Ry Rz Sh Uw Uy Vb Vi Vz Wd Wh Yh Yi
Yj Zq Zw Xa Th) nK(Gb Hl Ho Ps Rx Ry Rz Uw Ux Uy Vb Vh Vi Vw Wh Yg Yh Yi Zq Xa Ti Th Yf) nN(Eq Fd Fi Hl Ho Ps Ry Rz Sh Si Uw
Ux Uy Vi Wh Yh Yj Zq Zw Ye Xa Th) nC(Fc Fi Ps Ru Rv Uw Ux Uy Va Vh Vi Vz Wf Yd Yh Yi Yj Zq Zw Ti Th Yf) kO(Eq Hl Ps Ru Ry Uw
Ux Uy Vi Wh Yh Yi Zq Zx Ye Ti Th) nD(Hl Ps Ru Rv Ry Uw Ux Uy Vb Vh Vi Vw Wd Wf Yg Yh Yi Zq Ti Th) nJ(Gh Ho Ru
Rx Ry Sh Uw Ux Uy Vh Vi Vw Wd Yh Yi Yj Zq Zw Th) Gb(Ed Fa Fi Fw Hc Ho Jl Jr Mi Nd Nw On Ou Pe Pg Ps Un Vu Vv) mS(Fc Ps Ru
Ry Uw Ux Uy Vh Vi Vw Wd Wh Yg Yh Yi Yj Zq Zw Th) nL(Fc Fi Hl Ps Ru Rv Ry Uw Uy Vi Vz Wd Wf Wh Yh Zq Zw Ti Th) mT(Eq Hl Ho
Ps Ru Rv Rz Uw Ux Vh Vi We Wh Yh Yi Zq Ti Th) nB(Eq Ps Ru Ry Rz Uw Ux Uy Vh Vi Vz Wd Wh Yd Yh Yj Zq Th) mW(Hl Ps Ru Ry Uw
Uy Vi Wd We Wh Yh Yi Yj Zq Xa Ti Th) kC(Hl Ps Ru Ry Rz Uw Uy Vi Wh Yd Yh Zq Xa Ti Th) Nd(Fc Fi Ps Ru Rx Sh Si Uy Va Vi Vw Tl
Yf) nO(Ps Ry Uw Vi Vw Wd Wh Yh Zq Zw Zx Th) oQ(Fc Fd Fi Hl Hp Ry Vz Yh Yi Yj Zw Tl) nM(Ps Ry Uw Vi Wd Wh Yd Yh Zq Zw Th)
nF(Ps Ry Uw Vi Wd Wh Yd Yh Zq Zw Th) Sh(cU Fa fR Hc Jr Mf Ou Pg tF) Pc(fB gC oV oW pH pK) eP(Fy hG Jr Kx Ky Ld) lN(aM Id Ky Or
Rc Tz) Ed(Rx Si Uy Wh Zq) Fi(aZ hC oE oF Tz) dX(Fy Jr Kx Ky Lv) fB(cM Qa Qd Vv Yh) Yf(aM Bn Hv Ic) Fc(dR hC oF) Si(Jr Ou Tz)
Yl(hC Or Ou) fR(Ps Vb Vi) oV(Al Ny Oa) Fa(Ry Zq) Fb(Ps Wh) Ho(Ko Nm) MejV TzRx HbQd JvoT RytF LdjB} Ma{fB(aF aN Ax Bb bI cD cM Co cQ Cw Dr Du Ez Fa Fb Fr Fy Gb Gc Gd Ha Hb Hp Ij Il Iz Jk Jo Js Jt Ju Jv Ky Kz Li Lj Mm Mw Mz Nm No Ny Oa Of Oz Pb Pc pF Pj Pz Qa Qb Qc Qd Qg Qm Qt Qu Qw Qx Qy Qz Ra Rb Rf Rg Ri Rj Rx Ry Rz Sf Sh Si Tz Ua Ub Uc Ud Ue Ug Uk Um Uo Ur Uv Vp Vs Vt Vu Vv Wb Yd Yi Zw Wm) oV(Ad aF Al Ap Ar Ax Bb Bc Co Cs cT cU Cw Dc Dg Dk Dl Ef Ez Fa Fb Fp Fr Fy Ha Ib Ih Ii Im Io Iz Jg Jj Jk Jm Jo Jq Js Jt Jy Kl Lh Lj Mm Nm No Nv Nw Oa Oe Of Ok Om On Pc Pj Pz Qb Qe Ql Qm Qn Rc Sr Ss St Ue Uf Un Uu Vq Vt Vu) jB(Ad AL Ar Ax Bb Bc bU bZ cD cF cM Cs Ez Fa Fr Fy Ha Ii Ij Im Jj Jk Jm Jo Jq Js Jt Jv Kc Kk Kz Li Mm Mw Nf Nm Ns Nx Ny Oa Of Og Pc Pj Qb Qh Qm Qv Qz Rc Rf Rm Sr St Ug Vo Vq Vt Vu) oT(Al Ar Ax Bb Bc cM Co Cs cU Dg Fa Fb Fp Fr Ha Hb Ib Ij Im Jk Jm Jq Js Jt Ju Jv Kz Lh Li Lj Mb Mm MW nI Nm No Nv Oa Oe Of Pc Pj Qb Qe Qh Qm Qn Qz Rc Rf Rm Sr St To Vt Vv) mE(aA aC Ad Aj Al Ap Ax Bb Bc Cv Cw Dg Dl Ef Eq Fa Fb Gb Gd Gh Hl Hp Iz Jj Jo Jt Kj Kl Nm Of Qv Rc Rt Rv Rx Rz Uc Ue Ug Ux Uy Va Vo Vw Wb Wd Yg Yi Yj Zw Th Yf) kE(Ad Al Ax Bb Dg Dl Dr Du Ef Fa Fd Gc Gd Gn Hp Jo Jt Kl Li Mm Nm Of Pc Pj Ps Rt Rx Ry Rz Sh Si Ue Uw Va Vw Vz Wb Wc Yd Yg Yi Yj Zq Zw Tm Tl Th Yf) mH(Ad Dg Dl Dr Du Eq Gb Gc Gd Gh Gn Hl Hp Jo Jt Op Ru Rv Rx Ry Rz Sh Uz Va Vc Vh Vi Vz Wb Wc We Wf Wg Wh Yd Yg Yj Zq Zw Zx Ye Xa Ti Th Yf) Jt(dU eQ gZ kC kF kI kK kN kO kP lW lX lY mF mI mM mP mS mT mU mW mY mZ nA nB nC nD nF nH nI nJ nK nL nM nN nO nR nT nU oP oQ pI) pK(Al Ar Ax bU Cs Cw Fa Fb Fp Fr Ha Ij Jk Jo Js Ju Li Lj Mm Nm Nn Oa Of Pc Qg Qh Qt Qv Qw Rb Rc Ri Rm Sr St Ue Ur Uv Vq Vt Vu) dU(Al Ar Ax Bb bZ cD Co Cw Fa Fb Fp Fr Fy Ha Jj Jk Jo Js Ju Jv Li Lj Mm Nm Nn Ny Oa Of Pc Pj Qb Qh Qz Rc Rf Rm Sr Ug Vo) nI(Ad aF Al Ap Ax Bb Bc Cv dA Dg Dl Ef Eq Gb Gd Gn Hl Hp Jo Kl Of Rt Rv Rx Rz Sh Ue Ux Uy Va Vw Wb Wd Yg Yi Yj Zw Th Yf) kI(Ad Al Ar Ax Bb Bc Dg Dl Dr Ef Fa Gc Gd Hl Jo Of Op Pc Pj Ps Rt Rx Ry Rz Sf Sh Si Ue Va Vw Vz Wb We Yd Yg Yl Zq Zw Th) Ad(kC kF kK kN kO kP lW lX lY mF mI mM mP mS mT mU mW mY mZ nA nB nC nD nF nH nJ nK nL nM nN nO nR nT nU oP oQ) Dg(kC kF kK kN kP lN lW lX lY mF mI mM mP mS mT mU mW mY mZ nA nB nC nD nF nH nJ nK nL nM nN nO nR nT nU oQ) Gb(aZ Ed kC kF kK kN kO kP lW lX lY mF mI mM mS mT mU mW mY mZ nA nB nC nD nF nH nK nL nM nN nO nR nT nU Tz) Gd(kC kF kK kN kO kP lW lX lY mF mI mM mP mS mT mU mW mY mZ nB nC nD nF nH nJ nK nL nM nN nO nR nT nU oP oQ) Hl(kC kF kK kN kO kP lW lX lY mF mI mM mP mS mT mU mW mY mZ nA nB nC nD nF nH nJ nL nM nN nO nR nT nU oP oQ) Yg(kC kF kK kN kO kP lW lY mF mI mM mP mS mT mU mW mY nA nB nC nD nF nH nJ nK nM nN nO nR nT nU oP oQ) Rz(kF kN kO kP lW lX lY mF mI mM mP mS mT mU mW mY mZ nA nB nC nD nF nH nJ nK nL nM nN nO nR nT nU oP) Vw(kC kF kK kN kO kP lW lX lY mF mI mM mS mT mU mW mY mZ nA nB nC nD nF nH nJ nK nL nM nN nO nR nT nU) gZ(Al Ar Ax Bb Bc Co Cw Fa Fp Fr Ha Ij Im Jj Jk Jo Js Jv Li Lj Mm Nm Nn Ny Om Pj Qe Qh Rc Rf Rm To Vt) Rx(kC kF kK kN kO kP lW lX mF mI mM mS mT mU mW mY mZ nA nB nC nD nH nJ nK nL nN nO nT nU oP oQ) Wb(kC kF kK kN kO kP lW lX lY mF mI mM mP mS mT mU mW mZ nA nB nC nF nJ nK nM nN nO nR nU oQ) eQ(Al Ar Ax Bb Dc Ef Fa Fb Fp Fr Ha Ij Jk Js Jy Li Lj Mm Nn Ny Of Pc Qh Qm Rc Rf Rm St Vt) oQ(aF Al Ap Ar Ax cF Dc Dd Dl Fa Fr Gc Gn Hb Li Nn Of Op Pj Qe Rf Rm Ry Ue Vt Yi Yj Yl Zw) Ux(kC kF kK kN kO lW lY mF mI mM mT mU mW mY nA nB nC nD nF nH nJ nK nL nM nN nR nT nU) Va(kF kK kN kP lX mF mI mM mP mS mT mW mZ nA nB nC nF nH nJ nK nL nM nN nO nR nU) Yi(cU Jr kC kF kK kO kP lW lX mF mI mM mP mS mT mU mY mZ nA nD nJ nK nO nR oP) oD(aF Al Ar Ax bZ Cs Cw Fa Fr Ha Jk Js Li Lj Mm Nm Nn Oa Of Qh Ue Vq Vt Vu) pI(Al Ar Ax Bb bZ Cs Fa Fr Ha Ij Jk Js Li Lj Mm Nn Oa Pc Pj Qe Qh Rc Rf Rm) pH(Al Ar Ax bZ Fa Fr Ha Ij Jk Js Li Lj Mm Nn Ny Oa Qh Qz Rf Rm To Uf Vv) nJ(Al Ap Bb Bc Cw Dl Fb fP Gn Hb Hp Kl Ks Pj Rc Rv Sh Si Uw Uy Yj Zq) oP(Al Ar Ax Du Fa Gc Gh Gn Kz Nn Of Op Pj Rm Ry Sf Sh Uc Yl Zw Zx) oW(aO Ar Ax Bb Co cT Fa Fb Fr Ha Jk Js Li Lj Mm Ny Qb Qh Rf Vq Vt) Uy(kC kF kK kO kP lX mF mI mM mP mT mU mY mZ nA nD nK nN nO nR) Jo(kC kF kP lW lY mM mP mS mT mU mZ nA nF nK nN nO nR nT nU) Rt(kF kN kO lW lX mI mM mS mT mU mY nB nD nF nK nM nO nR) gC(Al Ax Fa Fr Li Lj Mm Nn Ny Oa Qh Qz Rc Rf Rm Sr) nK(Al Ar Ax Bb Bc Dl Ef Eq Fb Gh Hp Kl Rc Yj Zw Th) kP(Al Bb Gn Hp Nm Nn Ny Of Rc Ry Sh Uw We Yj Th) mS(Al Ar Ax Gc Of Ps Sh Ue Uw Vb Vh We Zq Th) Th(kO lW mM mU mW mY nC nH nL nO nU) Of(mI mM mP mT mU mY nB nN nR nT nU) Al(fA lW mP mT mY nA nC nH nO nT) Sh(lX mF mI mM mP mT mW Nd nN) fA(Ar Ax Fa Fr Li Lj Mm Ny Oa) Hp(kC mF mI mU nA nH nT nU) Yj(kF lW mF mI mT nD nN nR) Jj(fR mP mU nN nO nT nU) Uw(kC kK mU mY mZ nA nO) Rv(mI mT nC nD nL nU) Dl(kN lW mW mY nA) mF(Eq Gh Ry Wd Zw) mI(Fd Gh Gn Wd We) mT(Cv Fd Gn Wf Zw) Kl(mZ nA nH nR) We(kC mU nO) dX(Jf oH Uh) eP(cU Ld Uf) nR(Bb Nm Vi) nA(Bc Gh Zq) rZ(eD jF jY) nD(Eq Zw) BbnH YfnU GhlY GnmM NmmY TzSi YhoF PseM RymU aAeD cUfR} Gb{Nw(aA aD aG aH aI aJ aM aN AO aP aR aS aW aX aZ Ba Bb BC bE bH bI bJ BN bO bU bX cA cB cF cI cK Co Ct cU CV cW CX cZ dC Dg Dk Dl Du Ed eM Fi Fp Fw Fy Gc Gh gL Gn Gz Hb Hc Hf Hl Ho Hq Hr Hu Id Im Ir Jd Jf Jg Jh Jm Jp Jq Jr Jt Kc kE kF kK kN kO KP Kz Li Lt lW Mb Md mF Ml Mk Ml mM MP Mr mS mT Mu Mv mW mY Mz NB nC ND Ne nH nJ nK NL NN Nq nR Ns Nt NU oF On oP Ow Oy Oz Pb Pc Pd Pe Pf Pg Qb Qg Qy Rg Rx Ry Rz Ub Uy Vu Vv Vw

Figure 40 Continued

IY(Wc We) hR(cF lN) DukE YfnH GcmS MejV TzlN YjmW YdnN SfmP} Hp{Pg(cU Ed fB g

MfrB} oQ{Sf(Jn Nv Pf Ph) Du(cY Jf) Ju(bQ Ph) NmNt YkbQ RydA RhcL} Gd{nK(dA dF Om Up) De(Oh Yl) Pf(kP nO) MpVz VucF} pI{Fy(Oz Pb) Lj(aR Pe) Ny(bQ oN) NnPd UeiO IocT UrPb} Du{Po(kP lW nK) Mh(De Hv) Oh(Hv nD) bB(mP mU)} Ry{Nv(Ed Nb oF) nD(aQ Mz) HvcT OkoF bQkI dRmU} bO{jG(Iu Je Ky Oi Rj) Wh(mM mY) WdmY PsmF} Mj{Wf(kC nT) mP(Mm Nm) JjfR YlcL cFnO} Si{Ua(Lz Mh) Ji(Um Uo) Vu(Ex Jq) AoEd} dA{nT(Lz Rf Rh Tr Wm) nO(Lz Pf)} gZ{Pb(Qx Ur Wm) MwQu UeiO ToUr LjPe} Sh{mU(Mv My) ComF CtkI NgoF VucF} Sf{kI(cF Ct Mz) Pf(kP mM)} Ky{qV(Ko Li) AnjG LyjF OzlM} Oh{Rf(kP nA nB) HvYl HbVw} Um{jO(Ap Dg) MxlM HbJi TmoF} mP{Ok(Jj Jo Jt) TtJj WboN} Ye{mI(Mg Mv) QtmU VukO} Nv{Yl(Jo Mh Rc) WbnK} kK{ChUr NqOf ToeC YkdR} Nn{nK(Nm Th) WemI} lM{BoMx ThUr LirC} Ns{MbmU fRoF} Ji{ApcF HbWg} Jj{ChnO OknT} Up{EqnB WhnK} AdMzcF DifRoF YfIiJq TicMmU LyaWjP MxLjrY YkaQmF JfKiqW LirCjD

Unconstrained panels with 2 analytes, where 1.0E-8 >= 'AUC p-value' > 0. Contains 45 panels of 142,491 total panels evaluated. : gV(aL aZ bA cT CU) Is(dX Gb Uy Yi Yl) Tn(eP fB oO pK) cU(fR Gd Si Yg) Cu(Gb Ux Yi) kG(Mj Nb Yj) Lx(Yi Yl) Hl(nR nU) Jr(dX eP) hR(cF rZ) lN(Ky Tz) oO(oF oQ) GbNw NsoE JvoT LdeP LpkN YlOu aAeD aFoW Unconstrained panels with 2 analytes, where 1.0E-7 >= 'AUC p-value' > 1.0E-8. Contains 32 panels of 142,491 total panels evaluated. : kG(Gb Hl Tz Yg) Nd(Lp Rx Sh) lN(aM Or rZ) Gb(cU Jr) Tn(dX nI) Yi(Jr On) Ut(eP mE) oO(aJ Nn) AxIs BclL DcgV GdGp NqlY MxrZ TopH HbQd IvaA JndX PcoV cUnI Unconstrained panels with 2 analytes, where 1.0E-6 >= 'AUC p-value' > 1.0E-7. Contains 105 panels of 142,491 total panels evaluated. : kG(aF Fw Gn Gp Hp Is Kq Lx Mp Nd Or Pg Rv Ut Vb) cU(Aa BO cA cF cI dH Jr Lh Mm oE Yi) rZ(jD jF jI jO jP jT jV jY lO rC) oO(aA aP bV Jl Nb nR oE Ut) nR(cF Jj Mh Mm nI Nm) oE(Fa Hc Pc Um Vv) Nd(Hl Sf Va Yf) aA(Lv Mb Nj Nt) lN(Dl Fr hR Mx) Gp(Fi Sf Sh) Tz(Hp Rx Va) kF(Mb Oi Qd) De(Gd Oy) Gb(Pg Vu) Is(eP Iq) Rx(Fy Jr) On(Jt Mb) cD(jO Uv) lL(Id Mx) AaaZ GhoF NeOh TnnU YiPg SfoP JiLi JuoT LpVu YlOr VaVv PcoW aFmP hRjO Unconstrained panels with 2 analytes, where 1.0E-5 >= 'AUC p-value' > 1.0E-6. Contains 409 panels of 142,491 total panels evaluated. : cU(aA aC aD aE aF aG aH aI aJ aK aL aN aO aP aQ aR aS aU aV aW aX aY aZ bA bB BC bE bG bH bI bJ bL bM BN bQ bR bS bU bV bX cB cC cD cE cG cH cJ cK cM cN cO cQ cR cS cT cV cW cX cY cZ dA dB dC dD DE dF dI dK dL dM dN dX Em eP Hp Hr Hw Lt Mb Me Mh Mx Nd Ne Nn Ns oO Oy Rx Ry Sf Sh Uw Zq) oE(Ad Al Ax Bo Dg Ed Ef Ez Fw Gp Hr Id Iu Je Jf Ju Kc Kg Ko Kz Ld Mm Nd Ne Nl Oe Og Ou Oz Pg Pj Qn Tz tF) kG(aA Dd DU Em Fd Gd hC Hr Ic Jl Ke Lh Ma Mv Mx Ne Nq Ou Oz Pb Pc Qa Qd Tn Wb Yd Yi) oO(aF aO Aw bQ bZ cF Cu dF dG eC fA hB Kq Ma Mj Mt Mx) nR(aA Ad aF Dg Gb Gn Hr Ju Lh Mb Mn Nb Pc Rb To Um) rZ(eD hA iC jE jG jM jQ jR jU lL lM qT qW qX rA) Nd(Du Ho Hp Lt Qv Ru Ry Um Yi Tl) On(aA eP Gb Iq Iv Jm Lj Me Nj Ry) aA(Aa Ik Mk Mx Nl Nu Pg Po Qd) Gb(cG Fy Gp Hq Jp Lx Qd Tz) dX(cT Fy Ji Lx Pf Qa Uf Ut) lN(Dg jP Kj Mf Mt Mv Nn Nq) Cu(Ad Dg Hl Hp Jo Va Vw) Nu(Is Jl Lv Mx Mz Nv Oh) eP(Aw Fy Ji Jn Kq Lx Uf) gV(Ao Aw Ba bO Cp Cw dD) kF(Jj Jo Jt Lx Mh Mj Ut) Nw(Ik Me Rx Si Va Yi) Nt(Jj Jo Mg Mh Ng) Tn(eM mE mY oT Rc) Is(Al Hb Jm Lj Rm) Jr(Em Hp Si Yl Zq) Mb(Ji Nv Ok Pg) Me(Ji Mx Nn Nv) Tz(Qv Ry Si Yg) Iv(Jj Jm Lv Ng) Yi(Jl Mt oF Vi) Sh(Hc Hq Ou Vu) Qd(Ax Ik Iu kC) Lp(Hv mU nI oP) Ut(lY mW nI nU) oT(kN Ld Ow Vv) Gp(Rx Wc Yf) Qa(Iq Jm Nx) eD(cF jI jP) oF(fR Hl Yg) Ed(Aa Hp) Nn(Hv Ne) Nq(kN mE) Lv(Hv Mx) Ji(Jt Lj) Rx(aZ cT) Ld(dU Yl) Vi(Ib nH) Pg(Hp Jj) aF(nT oD) aO(nI oV) lL(bO jD) PoLj LxmZ MiaC MjnI MvmE NbkN NeNv ZqdF RyVv RfOh OuVa aPcF Unconstrained panels with 2 analytes, where 1.0E-4 >= 'AUC p-value' > 1.0E-5. Contains 1,350 panels of 142,491 total panels evaluated. : oE(aA aC aD AF aG aH Aj aK aM An AO Ap aR As Aw aX aY aZ Bb BC BG bH BN bO bP bQ bR bS bU bV bZ cA cB cC cD cE cF Ch cI cL cM CO Cp Cq cR CS CT Cu Cv CW CX dA Db Dc Dd De dG dH DI dJ DK Dl dN Dp Fb Fn FP Fy Gh GL gW Ha HB Hf Hv Hw iA Ib Ic Ii IJ Ik Im In Io Is Iv Iz Jd Ji Jj Jk Jm Jo Jr Jt Jv Jy Kd Ke Kf Ki Kj Kk Kl Kn Kp Kq KR Ks Kx Ky Lh Li Lj Lu Lw Lx Ly Ma Mb Md Me Mh Mi Mk Ml Mp Mr Mu Mw Mx My Mz Nb Nc Nf Ng Nh Ni Nk Nm Nn Nq Nr Nt Nu Nv Nw Nx NY Oa Of Oh Oi Ok Om Or Ow Oy Pb Pd Pe pF Ph Pi Pk Po Qd Ql Qm Qt Qu Qv Qw Ra Rb Rc Rg Rj Rm Ss Tn To Ua Ub Ue Uf Uh Ul Uo Up Ur Us Ut Uu Uv Vo Vu Tj) cU(Ad Af Aj Al aM An Ao Ap Ar As Aw Ax Ba Bb bF Bg bP bW bZ Ch cL Co CP Cq Cs Ct Cu Cv Cw Cx Db Dc Dd DG Di dJ Dk Dl Dr eM Fc Fi Fp Fr Gc Gh Gn Ho Hq Hu Hv Hx Id Ih Ii Ij Ik Il Im In Io Ip Iq Ir Is It Iu Iv Jg Jh Ji Jj Jk Jl Jm Jn Jo Jp Js Jt Li Lj lN Lp Lu Lv LW Lx LY Ma Mc mE MF Mi Mj Mk Ml Mn Mp Mq Mr MT Mu Mw MY MZ NA Nb Nc Nf Ng Nh Ni Nj NK Nl Nm NO nR NT NU Nv Nx Ny Oe Of Og Oh Oi Ok Om On Op oT oV Oz Pa Pb Pc Pd Pe Pf Pg Po Qd Rz Sj Um Ux Uy Vb Vz Wb Yj Yk Yl Zw Ye Tm Tl Xa) kG(Al aO Aw Cu Di Dk Dr Et Fc Fi Fn Fr Hq Hu In Jh Ji Jj Jk Jn Jo Jq Jt Kd Ky Lp Lu Lv Ly Lz Mb Mf Mh Ml Mr Mu Nh Nl Nn Nv Nw On Pd Pf Pi pK Po Ps Qe Sh Si Uf Yh Yk Ye Tm Xa Th Yf) aA(bO cF Et FR HR Hu Ih Ij Il Im Ip Ir Is Jh Ji Jj Jl Jp Jq Jr kF kN lN Lx Ma Me Mf Mh Mj Mt Mu Mz Nb Nc Ne Nh Nl Nk Nn Nq Nr nU Nv Nw Nx Ok Pe Qa Qe) Is(aC Ad aO Ap aR Bb bV cC cF Dg dJ fR Ii Ik Iu Iv Jj Jo Jt Ju Jv kF Lh Li Lv Mb Me Mh Ms Nj Nk Nl Nm Ns Nt Nx Ny Of Om Pz Qd Qv Rc Rx Uw Va Vz Yg Yj) Iv(Et Fr Hr Ii In Iu Jh Ji Jk Jl Jo Jp Li Lj Ma Mb Me Mf Mg Mh Mj Mu Mx Mz Nd Nj Nk Nl Nn Nq Nt Nu Nw Nx Oe Of Og Oi Ok Pa Pg Po Qa Qd) Nt(Ii In Ji Jt Li Lv Mb Mc Me Mj Mm Mx Mz Nb Nd Nj Nk Nl Nm Nn Nu Nw Oe Of Og Oi On Pa Pg Po Pz Qa Qb Qd) nR(Al aO Ap Bb cC cM DD Di Dl Io Ip Jr Jv kE kJ kN kO Lz Mj mS Mx nF Nv Ny Of Oh Qv Tr Ug Ur Ut) kF(aF Dl Ii In Jn kJ Lu Lv Lz Ml Mm Mn Nb nI Nm Nq Ny Oe Of oO Ou Oz Pb Pc Pf Qa Qb Tz) Nu(Hv Hx Im Ji Jj Jn Jr Lh Lx Mb Md Me Mf Mh Mj Mp Mu Nb Ne Nk Nl Nn On Pg Po Qa Qd) Nd(Eq Fd Fi Gb Gh Ik Op Ps Ra Rz Si Tn Ue Uf Uw Ux Uy Uz Vb Vi Vj Vu Vv Wb Yl Ye) Qd(Ad Al aO Bb cF dX Iq Jm Jt Jv Ko Lh Li Lj lY Mb Mx nC Nl Nn Ns Nx Pz Si Uy) Ut(eM fB Gb Jo kC kE kK kN lW lX mF mI mT mY mZ nA nD nF nJ nL nT Qv Si Yg) Pg(Ii Ik Iq Ji Jm Jo Lj Lp Lv Mh Mi Mx Ne nI Nj Nl Nn On Pf Sh Uy Va Yj) lN(aD aJ An aP Bo Gp hA hX jD jI jO jT Kl Ko Mj Mu Mw Oh Ph Qb rC) oO(Ax Cs cT dD eF fB fR hC Kx Ld Lx Mv nN Nq On pH Pi Qt Qu Uf Yj) Gb(Ed Ez Fw Hc Im Ji Jl Js mP oF Oh oP Ow Pe Ps Tn Uf Vv Yi) Lx(Cs Du fR Gd Hp kC kO lY Mh nI nO Ns Op Rx Ry Uy Vz Yg) eP(Ba cG Cq Cu Jd Kx Ky Mz Nw Oh Pe Qa Qe Tz Uh Vu) rZ(hV hW hX iB Il It jH jK jL lK Nv Qe qU qV qY rB) Lv(dX Ik Lj Mi Mz Ne Nl Nn Nv Of Oh On Pc Qa Qb) Tn(Ad Bb dU fR Hb Ib Jo kK kP mH nA nJ nT Rx Uu) nI(aF Aw bF bQ bZ cG Cv dF Fw Mv Nb nU oT Pi tF) lL(aD aH aM aW aX Bb bC bI cH dI eD hR jO jP Nq) On(Ad dX Ik Jj Li Mh Nc Nl Nq Of Pf Pz Vh Yg) Me(Aa aU bV cB cF gW Lh Mi Mu Mz Nb Oh Ok) Jr(bO Du eM fR Gd Hl Lp Ry Sf Sh Yg Yj Zw) dX(Aw bA Kq Ky Mn Mz Nw Oh Pe Pi St Tz Uh) Mb(aZ Jk Jl Mi Mj mP mT mU Mx nN nU Nw) Hv(Lw Mi Mj Rx Um Uz Wg Yh Yi Yj Yl Yf) Mx(Jh Jj jO JP Li Mh Mi Ne Nh Nl) Cu(Aa Dl Jt Mm Nm Rx Sh Vb Yg Yj) Tz(Hb Ib Jv Lj Lp mZ Rc Uw Uy Yl) oF(Du Gd Hp Lp Ns Rx Sh Yh Yj Yl) Ji(Ap Bb Hb Ik Iq Ms Mw Nj Nl) eD(aS dI jE Lu Mv Nq Qw qX rB) gV(aU Ax bB bQ cG Cq Cs dB Dd) oT(aF bH dL iO mP mS oN Pc Rj) Po(Jj Mz Nj Nl Ns Nx Of Og) Nn(lY Mh mW Ng Nh Nj Nl pH) Qa(Iu Li Lj lY mZ Nj Ns Yi) Rx(aO bA bF cG dF Oh oP Vv) aZ(aO aP bO cF De fR Lu Uy) Mz(Ik Iq Lj Mh Ne Oz Yi) nU(aF Aw Jj Lp Ns Ur Vi) jO(Ap iC jD Ly Mf Ni Um) Gp(Fc Ne Ps Si Uy Wh) Nv(Ik Mh Nh Of Va Yi) hR(aO hA jH jP Lu Pc) Nl(Et Im Jj Ma Nq) Oh(Jv mZ Oz Uy Yi) Ou(kN nO Sf

Figure 40 Continued

Vz Yi) aF(fA kE nN nO oV) aP(aC aL cB dG dH) tF(Jo Ky Lp Ns Um) lY(Kq Ma Mj Mu Mv) De(aC bO Jo Of) Hl(Ho kN mW Nb) Yg(aO cG dF Mt) Nw(Li Lj Uy Yl) Vi(nC nJ nL Ny) Vu(Gd Hp Jv Rc) cF(aJ bA Ed nO) mZ(Lz Mj Pe Pf) pH(Al Nm Ny Vt) Aw(Gd mE Oy) Nq(jV mW Ne) Jl(Iq Jm Nj) Lp(mW Nb Vv) cB(Jo Mh Ng) jD(jP Mh rC) kE(aO Ma Pi) Ne(Lh Mi) Ik(Jj Ok) Hc(Gd Va) Yi(Jn Js) Ky(Um Yl) Vv(fB Rt) bF(oV Sh) fA(Ax Jv) mE(Kq Qu) jB(Ld Ow) AaPi AloW BojV CthA NmUf MfjU MjOf NbYj IdjI JjNx JtOk JuOr LhLj VhnC aCaX aUgC bAfR bOjG cSdU

Unconstrained panels with 2 analytes, where 1.0E-3 >= 'AUC p-value' > 1.0E-4. Contains 3,985 panels of 142,491 total panels evaluated. : nR(aC aE aL aM aN aR aS Aw Ax aY aZ bC bF bJ bM bN bO bP bQ bR bU bV bW bX bZ cA cD cE cI cJ cO cP cQ cT Cv cW cX dE dG dH dI dJ Dp Ed Ez Fn fP Fw Gd Gh Gp Ha Hb Hc Hp Hq Hv Hw Ij Ik Il In Iq Ir It Iu Jd Je Jf Jg Jk Jl Jm Jo Js Jt Jy kC Kd kF kG kK Kl Ko kP Kr Ks Ld Lp Lu Lv LW LX LY Mc Md ME MF mH MI Mk Ml mM mP Mq Ms MT mU Mv MW MY MZ nA nB NC ND Ne Ng NH Ni nJ nK nL nM NN nO Nq Nr Ns nT nU Nx Oe Og Oi Om On oP oQ Or Ou Ow Oy Oz Pb Pg Pj Po Qc Qh Ql Qn Qt Qu Qw Qx Qz Rc Ri Rj Sh Ss St Tn Tv Ue Uf Un Uo Uu Uw Uy Vb Vi Vo Vp Vs Vu Yi) kG(aM Ap aU Bb bF bQ cF cL cU Cv Cx dA Db Dc dD Dg dI Dl dR eM eQ Ex Ez fB FP GC Gh Gz Ha Hb Hc Ho Hv Hw Hx IH Ii Ij Ik Il Im Io Ip Iq Ir It Iu Iv jB Jg Jm Jp Jr Js Ju Kc Kf Kg Kk Kn kQ Kr Ks Kx Ld Li Lj Lt Lw Mc Md ME Mg Mk MM Mn Mq Ms Mt mU Mw My Mz Na Nc Nf NI Nj Nk Nm No Nr Ns Nt NU Nx Ny OE Of Og OH Oi Ok Om oO OP oQ oV Ow Oy Pa Pc Ph pI Pj Pk Qb Qc Qh Qm Qn Qt Qv Rx Ry Sf Uw Ux Uy Va Vi Vp Vs Vu Vz Wc Wh Yl Zq Zw Zx Tl tF) Is(Aa aF aH aS aU BC bO bU cB cD cL cN CO cQ cR CS cV Cw DE dH Et Fp Fr Gd Hl Hq Hr Hu Hv Hw Hx Id Ih Ij Il Im In Io Ip It Jg Jh Ji Jk Jl Jn Jp Jq Jr Js kC Ko lN Lu Lw Lx LY Lz Ma Mc Md Mf Mg Mi Mj Mk Ml Mm Mn Mp Mq Mr Mt Mu Mv Mw Mx My MZ Na Nb Nc Nd Ne Nf Ng Nh Ni Nn No Nq Nr Nv Nw Oe Og Oh Oi Ok On oT Oy Oz Pa Pb Pc Pd Pe Pf Pg Po Qa Qb Qc Qe Rt Ry Sf Si Ue Um Ux Vb Vh Vi tF) Qd(aC Ap aR aS aU BN bV cB cQ Dg eP Et Fp Fr Gd Hq Hr Hu Hv Hw Hx Ih Ii Ij Il Im In Io Ip Ir It Jg Jh Ji Jj Jk Jl Jn Jo Jp Jq Jr Js Ju Ke lN Lp Lu Lv Lw Lx Ly Lz Ma Mc Md Me Mf Mg Mh Mi Mj Mk Ml Mm Mn Mp Mq Mr Ms Mt Mu Mv Mw My MZ Na Nb Nc Nd Ne Nf Ng NH Ni Nj Nk Nm No Nq Nr nU Nv Nw Ny Of Og Oh Oi Ok Om On Oy Oz Pa Pb Pc Pd Pe Pf Pg Pj Po Qa Qb Qc Qe Qv Rc rZ Ue Va tF) oE(Aa aE aI aJ aL aN aP aQ Ar aS aU aV aW BA bB bE bF bI bJ bL bM bW bX cG cH cJ cK cN cP cQ cV cY cZ dB dC dD dE dF dL dM dR eC eF Et Ex Fr gP Gz hC hF hG Hq Hu Hx IH Il iO IP Iq Ir It iZ Jg Jh Jl Jn Jp Jq Js kQ kS Lv Lz Mc Mf Mg Mj Mn Mq Ms Mt Mv Na nI Nj No nW oF oH oK ON Pa Pf Pz Qa Qb Qc Qe Qg Qh Qx Qy Qz Rf Rh Ri Sr St Tr Tv Uc Ud Ug Uk Un Vp Vq Vs Vt Wm) kF(Ad aO Ap Bb Bc bQ bR cF cU Cv DD Dg Dp eC Et Fa Fb Gb Gd Ha Hr Hv Hw Hx Ih Ik Il Io Iq Ir It Iu Iv Jg Ji Jl Jm Jr Ju Jv kE Kj Kl Ky Lh Li Lj Lp lW Ly Ma Mc Md Me Mf Mk Mp Mq Mr MS Mt Mu Mv Mw Mx MY Mz Na Nc Nd Ne NF Ng Nh Ni Nj Nk Nr Ns Nu Nv Nw Og Om Or oT oV Pa Pe Pg Pj Po Pz Qc Qe Qv Qx Rg Rj Rx Ss Tn To Tv Ug Uh Um Up Ur Uu) Qa(Aa cU Et fB Fp Hq Hr Hu Hw Hx Ih Ii Ij Ik Il Im In Io Ip Ir It Jg Jh Ji Jj Jl Jn Jo Jp Jq Jr Js Jt kP Lh lN Lu Lw Lx Ly Ma Mb Mc Md mE Mf Mg Mh Mi Mk Ml Mm Mn Mp Mr Ms Mt Mu Mv Mw Mx My Mz Na Nb Nc Nd Ne Nf Ng Nh Nl Nk Nl Nm Nn No Nq Nr nU Nv Nw Ny Oe Of Og Oh Oi Ok Om On oO Oy Oz Pa Pb Pc Pd Pe Pf Pg Po Pz Qb Qc Qe) Pg(Et Fp Fr Gh Hl Hq Hr Hu Hv Hw Hx Ij Il Im Io Ip Ir Iu Jg Jh Jl Jn Jp Jq Jr Ju Jv kE kN kO kP Lh Li lN Lu Lw Lx lY Lz Ma Mc ME Mf Mg Mj Mk Mm Mp Mq Mr Ms Mt Mu Mv Mw My MZ Nb NC Nd Nf Ng NH Ni Nk nL Nm No Nq Nr Ns nU Nv Nw Nx Ny Oe Of Og Oh Oi Ok Om oO Oy Oz Pa Pb Pc Pe Po Qv Rt Rx Sf Si Um Ux Vb Yg Yl Zq) aA(aC aK aO aR aU aW aX aZ bC bN bR cB cH cS dD De dH Di Fp Gb Hq Hv Hw Hx Ii In Io Iq It Iu Jg Jk Jm Jn Jo jP Js Jt kE kI kO kP Lh Li Lj lL lM Lu Lw lX Ly Lz Mc Md mE mF Mg Mi Ml Mm Mn MP Mq Mr Ms mU Mv Mw My mZ NA nC Nd NF Ng nH nL Nm nN No Ns nT Ny Oe Of Og Oh Oi Om oV Oy Oz Pa Pb Pc Pd Pf Pz Qb Qc Rx) lN(Ad aF aG aI Aj aK aO Ap Aw aX aY aZ Ba BB BC bE bI Bn bO bX cC cE cF cG cJ cN Cp Cq CT Cv CW Cx cY cZ Dd De dF dG dI dL eD Et Fw Gl Hu Hv hW iB iC In jE Jh Jk JL jU Kd Kg Ki Kk Kn Kp Kr Ks Kx Lh lK lL Lu Lx Ly Mh Mk Mm Mp Mz Nb Nd On Ou Ow Pi Po Qe Qt rB rY Ut Vu) cU(DU eD Eq Et Ex fB Fd fP Fw Gp Gz Hb Hf Hl jB Je Jf Jq Ju Jv kC kE kI kK kN kO kP Ky lX Lz Md Mg mI mM mP MS mU Mv mW nB nC nD nF nH nJ nL nM nN Nq Nr Nw Or Ow pI Pj pK Ps Pz Qb Qc Qe Rt Ru Rv Uo Up Uz Va Vc Vh Vi Vw Wc Wd We Wf Wg Wh Yd Yh Zx tF Yf) Po(aZ bO bV cB eP Et Fp Hq Hr Hv Ii Ik Ip Iq It Iu Jg Jh Jl Jl Jm Jn Jo JP jT Lh Li lL Lu Lv Lw lY Mb Mc Md Me Mg Mh Mi Mk Mp Mt Mu Mw Mx My mZ Nb Nc Nd Ne Nf Ng Nh Nl Nk Nm Nn Nv Nw Ny Oe Oh Oi Ok On oO Oy Pb Pc Pf Pz Qb Qc qT Qv qW rA rZ Um Yi) Nt(aZ dX Et Fp Fr Gb Hq Hr Hu Hv Hw Hx Ih Ij Ik Il Im Io Ip Iq Ir It Iu Jg Jh Jk Jl Jm Jn Jp Jq Jr Js Lh Lj Lu Lw Lx Ly Lz Ma Md mE Mf Mi Mk Ml Mn Mp Mq Mr Ms Mt Mu Mv Mw My Na Nc Ne Nf Nh Ni No Nq Nr Ns Nv Nx Ny Oh Ok Om Oy Oz Pb Pc Pd Pe Pf Qc Qe Rx rZ) Me(aC aJ aK aL aO aP aR aV aZ bA bL BO cC cG cL cY De dF dR Et Hc Hx Ih Io Ip Ir It Iu Jg Jh Jj Jk Jl Jn Jo Jp Jq Jr Js Jt Li Lu Lv Lw Lx Lz Ma Mc Md Mf Mj Ml Mm Mn Mp Mq Mt Mw Nc Nd Ng Nh Nk Nl Nm No Nq Nr Nx Oe OF Og Pb Pc Pf Qc tF) Iv(Aa aU bO cB De Fp Hq Hu Hv Hw Hx Ih Ij Ik Il Im Io Ip Iq Ir It Jg Jn Jq Jr Js Jt Lh Lu Lw Lx Ly Lz Mc Md Mi Mk Ml Mm Mn Mp Mq Mr Ms Mt Mv Mw My Na Nb Nc Ne Nf Nh Ni Nm No Nr Ns Nv Ny Oh Om Oy Oz Pb Pc Pd Pe Pf Pz Qb Qc Qe Yj) lL(aF aG aI aK AN aO Ap aQ aR Ax aY bB bE bJ Bo bP bR bS bV bW cA cB cC cD cE cF cG cI cJ cO CT cW cX cY cZ dA dC dE dG dH dJ DL Dp Fr hA IB jH jI jL jV Kd Kj Kl Ko Ky Ld lK lM Mf Mj Mm Mu Mv Nd Nn Oh Qv Um) Nd(cB ED Fc Fy Gp Gz Je Jf jI jO jP jT Ju Jv Kc Kx Ky Lv Mb Ne Nj Nl Oa oF On Ou Ow Qh Ql Qt Qx Qz Rj Rt Rv Sj St Tv Tz Ub Ug Uh Uo Up Ur Ut Vc Vh Vp Vs Vw Wc Wd We Wf Wg Wh Yd Yg Yh Yj Zq Zw Zx Tm Xa Th tF) On(Ap Bb Co Et FR Gd Hl Hp Hq Hr Hu Hv Hw Ii Ij Il Ip Iu Jg Jl Jo Jp Lh Lx Mc Mg Mm Mn Mp Ms Mu Mx My Na Nc Ng Nh Ni Nk Nm Nn Nr Ns Nx Og Oh Oi Om Oy Oz Pa Pb Qb Qc Si Uw Ux Va Vb Yj Yl) Lv(aZ bV cB cF De eM eP Et Hu Im Iq Ir Jg Jh Ji Jj Jl Jm Jn Jp kC Lh Lx Ly Lz Mb Mc Md mE Mf Mh Mj Mm Mp Mr Mt Mu Mw Nb Nc Nf Ng Nh nI Nj Nk Nm NO Nq Ns Nw Nx Ny Ok Oz Pd Pf Qc Va tF) aP(Aa aD aF aI aK aN aO Ap aQ aS aU aV AW Ax aY bA Bb Bc bE bF bL bN BO bR bS bU cA cC cD cE cG cH cI cK cL cO cR cS cT cX cY cZ dA dD DE dF Dg DI dJ dK DL eD fR gV lM Um) Nu(Bo bV cB De Et Fr Ii Ij Ik Il In Io Ip Ir It Jh Jk Jp Jq Li Lw Ly Lz Mc Mi Mk Ml Mq Mr Mt Mv Mw Na Nc Nf Ng Nh Nj Nm No Nq Nr Ns Nw Nx Ny Oe Of Og Oi Ok Oz Pa Pc Pe Pf Qb Qc Qe) Lx(bO cB cC cD cF Dr Fa Hl Hv Iu Jj kE kK kN kP Lj Lp lW Mc Md mE mF Mi Mp mS Mt mW Mx mY Mz nA Nb nC Ne nF Ng nH nJ NK NL Nm nU Ny Of Oh oT Oz Pc Pf Sf Si Va Wc Yj Zw) Nl(Fr Hr Hv Ih Ik In Ip Jh Jk Jl Jm Jn Jp Jq Jr Lh Li Lj Lu Ly Lz Mb Mf Mh Mi Mj Mk Mm Mp Mq Mr Mt Mu Mv Mz Nb Nc Ng Nh Ni No Nv Nw Nx Og Oh Oi Ok Pc Pd Pe Pf Qb Qc) oO(aL aY bA bF BO bR cE cG cS CV Dc Dd Di Dk Ez Fr gL Gp Gz Hb Hc hG iZ Ju Jv Kd kQ Lp Lz MP Mu Mw Nr nU Nv nY Oh oN oP Or oT Ou oV oW Qv Tz Um Vu Yi Zw Xa) Mx(aZ cB De dX eP hA Hx Ik Im Ip jG JI Jl Jm jT kN Lh Lj lK Lw Ly Md Mf Mp Mt MZ Na Nb Nf Ng Nl Nj Nk Ns Nv Nx Oe Of Og Oh Oi Qc Qv qW qY Rx rY Ue Um tF) Jl(eD Hp Ii Ik Il Iu Jh Ji Jj Jo Lh Lj Lp Lu Md Mg Mh Mi Mm Mp Ms Mw My Mz Nb Ne Ng Nh nI Nk Nn Ns Nv Nw Nx Oe Of Og Oi Om Oy Pe Pf Qv Rc Rx Um Uy Va Yl) Tn(Dg eQ Ez gC Gd Gh Gz Hp Ii jB Jd Jg Jt Jv kE kI Kl lW lY mF mS mU mZ nD nF Ng nL nN nO Ny Ok oQ pH Pj Pz Qu Qv Rt Ry Sh Si Um Ux Va Vb Yg) Mh(aU aZ cF cG cL cS De Et hA Ho Hv Ik Im It Jh Ji jO jT Ky Lh Mi Mj MP MT mU mZ Nb Nc Nh Nj Nk nN Nx Ny Oh Ok Om Yh Xa tF) oT(Aa aO aU bA bC bF bU cF cM cS cT Cv dN eF Ez Fw Hb Hc Kk lW Ma Mb mE Mp Mw mZ Nb nD Ni Nm Ny oK Ou Oz Pa Pb Pi Pj Qn Tz Uc Ut) Rx(aC Ao aS bO bQ bV cF cL De dM Ed Ex Ez Fw Hc Hq Js kK kN Mj Mt Mv Nb No Ns Nv Oa Ok oN Or Ow Pa Pd Pf Pi Qn Vp Yi Yk Xa) Tz(Aa Ax Bb bN cF Dp eD Eq Gn Ho Jm Jo jV Li mF Mm Ng Nm Ns nU Ny Of Og Pc Rt

Figure 40 Continued

Sh Ue Um Uu Vh Vz Wc We Wg Wh Yh Yk Zq tF) Gp(Aa aC Ap cD dE Dr Du eP fR Fw Gc Gh Gn Hl Ho Ju Jv Lp mZ Ng Qv Ru Rv Ry Sj Ux Va Vb Vc Vi Vw Wb Wd Yd Yl Ye Tl tF) Mj(cB dX eD eP Gb Ik Iq Iu Jj Jm jO jV kC kN Li Lj lM mE mH Mi mP MW Ne Ng Nh Ni Nj Nk nO Ns Oe Pf Qv rA Ue Um Yl) De(Af AJ aL aM aO As aU bA bE Bo bV cF cG cI cT Cu Cx cZ dD dF Dg dL gV Jj Jk Jr Mb Mm Nb Ne Ng Oe Og Oi Um Yj) Ut(dU fR Gd Ib Ii Jj Jv kI kO kP mH MM mP mS mU nB nC Ng nH nK nM nN nO oP oQ Pc Rc Ry Sh Ue Um Uu Va Vb Vh) aO(aJ aM aR aX bC bO bV cE cL eD fB Fw Gh Ho Hp Je Jf Ji kN kP lM Lp Mi mP mU nN nT nU oD oW Sf Sh Yi Zq) aZ(aC aJ aM aR Aw bA Bn bV cD cI cT Cu dF Di dL eD Fi Gb Gd Ho Li Lj Lp Mm Ne Ng Ni Nm Pc Sf Si Yh Zq tF) Mb(Aa aU bO bV cB cF cG cL Et Fr Ih Ij Ik Ir Jp Jq Js Jt Lh Lw Mm Mp Mt Mz Nb Nn No nT Oh Pe Qb tF) Hv(cB Dr Du Gb Gn Jh jP Lt Lz Mc Md Mf Mq Mt Mu Mw Ne Ns Nv Oh Ru Ry Sh Uy Vh Vz Wc Wf Yg Yk Tm) Ji(Aa aC Ax bV cF Dg Hu Ii Iu Jj Jm Jp Mk Mm Mu mZ Nc Ne Ng Nh Nk Nm Nn Nv Oe Oi Pa Pf Pz Qb Yi) hR(aJ aM aV bJ bO bQ bW cB cE cI cQ dI dJ dK eD Hr hW jD jE jI jL Lj Ly Mf Qt rC rX rY Um Uv Vq) cF(aM bO bV cG cS cT dF Id jI Jj Ju Jv kE Ky Lp Ly Mi mZ nT Nw oP Or Qv Sf Sh Up Vu Wc Yl tF) oF(Ax Dr Em Fi Gn Ho Jf Jv Lj Ly Nx Ru Ry Rz Sf Si Um Uw Uy Vb Vz Wc Wf Wg Yk Zw Tm Tl tF Yf) Nb(Du eM fB Gd kE kK lY mE mF mU mW MZ Ne nF Nh Nj Nk nT nU Oh Rv Ry Sf Sh Um Vb Yi Tl) Gb(Ao bA bQ bZ dF Dk Et Ho Ij Jd Jt Ke Ld Ma Mi Mp Mt mU nH nU Oa Ok Ou Pf Qe Ua Uh Zq) Oh(eD Hb Hu Ik Iu Jh Ju Lh Md Mz Nh Nj Ns Nv Nx Pc Ps Qv Rc Rm rZ Ue Um Va Vz Yl Wm tF) Vu(Ad Al Bb dI Du dX eD fR Gh Hb Hl Iu Jm Jo Ju Ly mE nI Oa Qv Si Ue Um Uu Ux Va Yg Ye) tF(Ad Aj Bo bV cT Dg hG Je Jf Jj Jm Ju Kj Ko Kx Ly Lz Ml Nw nY Of Or Ou Pc Qv Uo) Jr(Al Bo bR bS cB cK dB dL Dr Fc Gh Gn Gz Ho Ib MU nN nU Sj Vz Zx Ye Tm Tl) Cu(Ap Ax Bb bO dX Gd Ii Jj Lp mE nI Nn Of Rt Ry Uw Uy Uz Vh Vi Wg Wh Yf) bV(Aa aI aJ Aw aY Bb Bc BO bR cB cC cI Dg Di Ed gV Je Jf Mi nU Oe Ou) eD(aJ aM aN aY bI Fr hA jD jH Jp Lj Ly Md Mm Mu Nn Pc Qt rX Ue Um Vs) jP(aM Bb hA Hr iC Id jE jF jG jH jI jL jO jQ jR jT Ko Lj Lu Ly Ok rA) cB(aJ bA gV Ii Im jI Jj Lp Lu Ly Lz Ne Nm Ns Nw Oe Oi Oy Pc Ry Yi) nU(aL bQ cT Cv dD kK lY mE Nm Pc Ps Rt Rv Uh Um Vh Vv Wh Ye Ti) mZ(aF Cv eC Jj Ju Lh Li Ma Mp Mq nI Nn Nq oQ Ou Pc Qx Ri Uf Ur) Ed(aU Ax bO cI Du Gn Ju Ky Lj Lp Qv Sf Si Um Uy Vz Wh Yg Yh) Gd(Ao bA bZ cG cL cS dR Ez Fy gL hG Hq Ma Nw oP Pf Uf Yh Yj) Nn(cG fA Ik Jj Jp kE kN Lh Mm mT Mz nA Nk oW Oz Qb Ue Wm) Ky(aF dJ jF jG Jm Ju Jv Mm Mz Nm nO Ra Rg Sr Ue Uo Vt Vv) eP(Ao bA Cp cT Ex Ij Im Jp Js Ke Mn Ny Om Pf Pi Qb St Vs) Nq(bA jD jO jU Jv kK lM lW mT Ng nI Nj Nk rZ Sh Ue Yl) Yi(dF dJ Ex Fw hC Hq Im Jq Kq Lh mH oN Pe Pf Ps Rc Vv) Qv(Fw Je Jf jG jO Ly Mp Nw Or Ou Qe Um Uo Up Vp Vv Yh) Jj(aU Et fR Ho Ij Im Jk kN mP mU Nh Nj nN nT Nv Qb) Um(aC aR Fw hA Hw Hx Jp Mk Mp Mz nO Or Pi Rh Ue Up) cG(aC Ad Ap Bb Bc Bo cE cI Dg dH Jo Mm Ng Oy Ry Si) gV(Ad aG aK Al aM aQ AR aX bZ cC cS cW cY dF Dk) Ne(Aa Im Jh Jk Ly Md Mf Mp Mq Mt Mu Mv Nm Nr Pc) Lp(bO Hc Ho Hq kO kP lW mE mH mI nC nH nL Ou Vq) dX(Ba Cq Ij Im Jf Jq Ke Kx NY Ok Qb Qe Ua Vs) nI(cS dD Gn hC kC kN Kq Lu MU nT Qu Uf Vi Vp) Ou(aR Gh Ju Jv kC lY Op Oz Pc Si Ue Uy Yd Zw) Mz(Ad Hq Jh Jm Lh Mn Mw Ng Nh Ni Nm Ns Pc) Vv(Bb Gh Hb Hp Ks pK Sf Sh Si Ux Uy Vb Vw) bA(Aa aU AW aX bO cC cI cS dH Em Jf oV) dF(aR bR cC cE cH Dg dH Gh Ng Oe Oy Ry Sh) Or(Aa Ax Hb jU JV Ly Oe Ue Va Vw Vz) hA(dI Hq Ib iC Jt Ld Ly Mr Ni Of Ok rA) Ik(Et Jp Jq Lh Ly Ma Mi Mp Nk Og Qb) Im(aC Ap Bb Cs Dl Jp Lj Nk Pj Si Ue) aF(Fi kK kN kP mH mI mT mU nK oQ pH) bF(kE kI lW mS mU nO nT oP oQ oW Sf) Nw(Bb Hb Hp Iq Ms Nh Nj Ry Uw Vz) lY(Aw Et Fr Mp Mt Mw Pf Pi Qu Uf) jI(An cH jD jE jG jO Ko lM Ly rC) Hq(Fi Ry Sf Si Uy Va Vj Yl Tl) Jp(Hp Lh Mp Nj Qb Sh Si Uw Uy) Nv(Iq Jm Ng Ni Oe Qb Ry Yj Yl) bO(aJ aM Aw Bo Cq cT Ps Vi Yj) Fw(Hl Hp Jo Mm Nm Sf Va Yj) Jv(Bo cH Dk gZ Ho oV pK Uf) mU(dD Hp Lu Mm Nm Ns Of Ye) kN(Al Aw Cv Gn Mp Mu Mv Mw) Ma(Co Dg jB kP Qb Ue Yl) Lj(Et hW Ir Oa Ok oW Pe) Uf(dU fB Jo kE Li pK Ue) Va(cL Jq Mp Nx Ps Vp Yh) Vi(Ad lW mW nN nT Yg Yj) aJ(aC aL bR dG dH Di lM) bQ(kE kI lW mE nO nT oQ) jO(aM Dg Hr jG Ko Lu Ok) Aw(eM fR kE lW nA oV) Mv(kE lW nA Ng Sh Ue) Qe(Aa Al Ax Hb Nx Uy) Lh(Iq Jm Li Nh Nj Yl) Pi(kI kP mE mS nA oQ) cT(Aa aR Bo Jo oD oV) nN(Jt Lu Nm Of Oi Pc) nC(Gn Rv Uw Wb Wh Ti) oP(Gh Ho Hp Lt Rz Sh) Et(Li Nc Nj Nk Nx) Ld(eQ mW oV pI pK) Ok(Bb Iq Li Ms Nj) Uy(cL Fy Js Mp Vp) Mu(kE mE Nh Ue) Hc(eQ Sf Ux Vb) Yl(dA In oN Ow) dD(lW mP nO nT) nJ(bZ eC Kq Uw) hC(Gh Hl Rz Yj) lM(Bo Id jD Ko) pH(Hb Mm Pb Pc) Fr(Ng Nj Ux) Nm(Ho mP oW) Mf(jD qT qW) Nk(Mi Mr Ni) Si(Ow Ua Uh) Sh(Ao cL Mn) Vj(Mm Pa Ue) Vp(Dp Rc Rt) aU(Ar Jm Ns) cS(mT oV pK) nO(Cv dR pK) oN(Ry Wf Zw) Al(fA oV) Gh(dR kR) Gn(Ho mP) Mp(Iu kE) Mt(mT Pf) Qb(Jm Nx) Jf(aC hG) Wc(Mk Pf) Kq(Aa mT) Uh(Hb Ib) aL(aR mP) aM(jG lK) mW(Dd Yj) nH(Hl Hp) jT(jD Ly) AxOa BaDg DrPe EzfB ExYg MdHx MiNj MmoW IqIr YhRc VzOw JehG JupK RvnL NyfA UoaC VbVw PcgC bZmE cCkK eQkC

Constrained panels with 3 analytes, where 1.0E-10 >= 'AUC p-value' > 0. Contains 23,209 panels of 23,517,221 total panels evaluated. :
oO{Cu(AA Ad aF AJ Al Ao Ap aS Aw Ax Bb Bc bI bV cF Co cT Cv Dc Dd Dg Dl dN Dp Ef fB Fr Gc Gd hG Ii Ij Io Iz Jg Jj Jk Jm Jo Jq Js Jt Ju Jv kE Kf KG Kj Kl Kq Ks Lh Li Lu Mb mE Mh Mm My Nb Ng nI Nm Nn nO Ns Nv Nx Ny Oe Of Ok On Pc Pj Pz Qe Qg Qh Qv Rc Rj Rm Rx Sf Sh Tn Ue Ug Um Ur Uu Uv Vo Wb Yd Yj Zw Zx) Kq(AA Ad aF Aj Al Ao Ap aS bA Bb Bc Bg bI Bo bV cF Co cT Cv Dc Dd Dg dI Dl dN Ef Ez fB Fy Gc Gn Hb hC Hl Ii Is It Jg Ji Jj Jk Jq Jt Jv KE Kf kG Kj Kl Ks Lh Li Lp Lu lY Mb mE Mh Mm mT Nb Ng nI Nn Nv Nx Ny Oe oF Oh Oi Ok On Pa Pc Pj Qe Qh Qn Qv Rc Ry Tn Ub Ue Uf Um Ur Uv Vq Wb Yj Zx Ye) Jv(Ad aK aL aO aP aQ As aU Aw Ax BA bF Bg Bo bQ bV bZ cE cF cG Ch cL Cp Cq CS cT cU cY dD dF dG Di Dk dR Ef Eq Ex FR Fw Gl Gn hB Hc iP Jk Jl Kx Ky Ld Mj Mt Mu Mv Mw Nb Nd Ng NN Nq nR nU Nv Oh oN oP oQ Or Ou oW Ph Pi Qu Rz Sh Ua Uf Ut Vu Yd Zw Xa tF) oF(AA Ad aJ Al Ao aR Aw aY bA Bg BO bP bV cE cF Ch cL cN cT Cv cZ Db Dd Di dL dN dU Hb Hq Hr Ii Ij Iz jB Jd Jh Jj Ju Kd kF kG kK kQ Mk Mm Mn mP mU My mZ Nb Nd Ni Nm Nn nO nR Ns Nu Nx oD Of Om Oy Pi Qd Qw Qx Rb Ug Um Ur Vv) Ju(aH aL aO aP aQ aU Aw Ax bA bF bQ bV bZ cE cF cL Cq cS cT cU Dc dD dF Di Dk eC Ex FR Fw Fy gL hB HC Is Kx Ky Ld Lx Ma Mj Mt Mu Mz Nb Nn nR Nv oE Oh ON oQ Or Ou oW Pg PH Pi Qa Qu Tn Tr Uf Ut Vu Yh Yi) nR(aA Ad aJ AP Ar Ax bA Bb Bg bV Co Cs cT cU Dd Dg Dl Dp fR Fy Gd Hb hC Hr lZ Jj kE kG Ko Ks Kx Ld Lx Lz Ma Mb Mh Ml Nb Nm Nn No oE Of Oh oQ Pc Pe Pf Pj Qv Rb Rf Rh Sf Sh Tn Tr Ue Ug Uk Um Ur Yi Wm) aJ(Aa aC aF aL aO aQ Aw bF bQ bR bV bZ cF cS cT cU dA dD dF Dl dK dN eC Fy Gb Gh Gn Ho Hr kE kG kN Kx Ld Lp Lv Lx Lz Ma Mh Ml mW mZ nA Nb nC Ne nH Ni nO Og Oh oV Pa Pc Pe pH Pi Tr Ug Ur Yi Yl) pH(aP aR Ax bA Bb bZ cF cJ cP CS cT cU Cv Dd dL Ez gL HC Ik It Iv iZ Jj kC kE kN Lx Lz Ma Mb mE Mk Ml Mw NB nD Nl Nn Nr nW Ny oE Oh Ow Pc Pe Pf Qa Qt Qx Ra Rh Tn Wm Tj) Nn(aA aF bQ bV bZ cT Dd dF fB Fd Hr Hw Is Jj Jl Jo kE kF kG kK kN Lv Lx lY Mb Mh Mm mZ Nb Nd nK Nm Ns Ny oE Of Og oQ oW Pc Pj Qd Qg Qv Rg Sh Tn Tr Tz Uc Ue Ug Um Ur Vv Yi Yj) Oh(Aa aF aO aP aS aU aV Aw AX aY aZ Bc bF bI bO bQ bV bZ cD cF cS cU Cv Dd dF Di Dl dN Dr fB Gb Gn Hb hG iZ Mj mP Mu Nq nU oD Pj Qg Qu Qv Rf Rg Rm Rx Sf Sh Ug Um Vo Yi Yj) dF(AA aM aP Ax Bb cF Cs Cv Dd dN Dp Hb Ib Ii Io Jj Jk Ld Lh Lz Mb Mh Ml Mm Mn Nb Nc Nl Nm nO Nu Nv Nx Ny Oe Of Og Oi oQ Oy Pc Pe Qh Qv Rf Rh Rj Sf Um Ur Yg Yk Yl) Ma(AA aC Ad Aj Al Ao Ap aS AX aZ Bb Bc bV cF cN Co cT Cv Cw Db Dc Dd Dg dI DL dN Dr Ef Gc Gn Hb hC Iz Kd Kg Kj Kl Ks Kz Mj mP nN oD oQ Pj Sf Yd Yh Zw Zx Ye) aP(aA aC aF aL aO Ap aS aZ bA bO bQ bV cF cT cU cV cX dA DD Du fB Fd fR Gb Hb hC Hr Ii Jl kF kG Lv mT MZ Nd Nm nY Or oT Oy Qa Qg Si Sj Tz Uc Ug Um Yd Yi) bZ(aA Ad aF Al Ao Bb Co Cv Dd Dr Fr gC Gn Hl Hr Ij Jd Jh Jj Jo Jt Kd Mk Mm My nI Nm nO Ns Ny oD Og oV Oy Pc Pj Qv Qw Qx Qz Rb Rf Ue Ug Um Ur Wb Yh Yj Zx) Lx(AA Ad Al Ao Ap aS aU aV Aw AX aY aZ Bo bV cF cN cT cU Cv Db Dd Dl dN Dr fB Gd Gn Hb Hl Hu Ib Iz Kd Ks Lu Mj mP Mu nN Nq nU Op oQ Pj Yd Yj Zx) cT(AA aM Aw Cv Dd Di dN eF FR gC Gn Hr

Figure 40 Continued

Ib Jl Mb Mr Mt Mu Nb Ni Nq NU oD OE oK Pi Qa Qd Qu Qv Rh Rj Rx Sf Tn Ug Um Ut Vv Yj Yk tF) Ld(AA aF aU aV aY aZ Bo bV cB cF Dd dI dU fB gZ hC Hr jB Jl kE kN Mb Me Mh mZ Nb Nd Nl OE oV Pg Qd Qg Qh Qv Tn Uc Ue Ug Um Ut Vv tF) oQ(Aa aC aF cF cU fR Fy Gc Gd Hp Hr Ib Je Jf kE kF kG kK kN Lv Mb Mh Mm mZ Nb Nd Nm Oe Pc Qd Rg Rx Ry Sh Tn Tr Ue Ug Um Ur Ut Vv Yg Yk Zw) cF(aA aO bQ cU cV Dc dG dH Ez Fy hC Is Jl Jr kF Lv Mh Mj MP Mr Mz nO oE Or Pe Pg Qa Qd Qn Rf Rh Rm Tn Tr Tv Tz Uc Vu Vv Zw) Yi(aA aO aQ aU aV aY aZ bO cN cW dG dH dN Fy Gd Gn Hv Ij Iv Jn Js kE Ly Mj mP mU mW mZ NB Nm Ny Or Ow Oy Pb Pg Sh Yj) Jl(Al Ax bA Bb bV cS cU Cv Dc Dd Dp Gc Gh Gn Hb Hl kF kG Lp Qh Qv Rb Rf Rh Rm Tn Tv Ub Ug Um Ur Us Vo Yg Yj Yl Zw Wm) Fy(Ad aF Al aM aQ aU aV aY aZ bC Bo bV cL cN Cq cX cY Dd dG dJ dL dN dU Gb Gc Gd Gn hC Hl Lp mU nO Pj Rx Sh Wb Yj) Tn(Aj aS Ba Bg bX Co Cp Dc dH Fb Hb hC Hu Ib Iz Ji Kf Kn Ko Lu Me Mf Mj mM MP Mt MU Mx Nj nN nO nT nU Ph) bA(Aa aR bR Cv eC Ez fR gC Hr Ib Jy Lp Ni Nu oD oE oV oW Pe Pf Qa Qd Qt Qu Qv Rf Rh Rj Rz Uc Um Ut Vu Vv Yj Zw) Tr(Ad Al Aw Ax BC Bo bP Cv Dc Dd Dg DL dN Hb Hu It Iz Kf Kj Ks Kx Lu mP MU Mx nN nO nU Ph Pi Pj) Rf(Aa aF aL aO aQ aU aV aZ bF bL bQ bR cB cG cL cV Dc dD Dk eF gC Gz hB kQ Mj Mp mU Nd oE Or Ou Pi Ut Vu) Ut(Aa Ao Bb Co Cp Dd Dp Hr Iz Jg Ji Jo Jt KF Kg Kj mF Nx Og Om Pc Pj Qm Qv Qw Rc Rh Ug Uk Um Ur Uu) aA(Aa aQ aU Ax bC bF bQ bV cL cM CS cU cW dD dG eC Ex kG kN Kx mP Mt Nb Ni nU oE oN Or oV Pi Qt Zw) bV(aM Aw Cv dG dN eC eF fP hC Hr Is Iv Kx Lv Mb mF Mh Mp Mr Mz Nb Ni nT NU oE Pe Pi Qa Qd Rh Uc) bQ(Aa aR Ax Bb bR Cs cU Dd dL dN Em Hb Ib Jj Kd kE Kx Mb Mh mP Mw nO Ny Pc Pe Qz Rh Ug Ur Vv Yj) Um(aO Ax bF CS cU dD dG eF hB Hc Kx Ky Mj Mk Nb nO nW oE ON oP Ou Pc Pi Pk Po Qa Qt Vu) Sh(AO Ba cE Co Ct cU Dk Ez Hc Ij Jh Jn Js Jy kN Lv Mj Mv Mz Nv Ok Om On oP Ou Pf Pi Rz) Rh(aF aL aO aQ aU aV aZ bF bR cB cL cN cV cY Dc dD dG Dk Gz hB Mj Mp mU Nd nU Or Ou Pi Vu) oE(Aa Ad Al aO Aw bC cS cU Cv Dd dL dN Hr Iu Jj Jr kF kG kK mP mU mW mZ Nb nO Ns Pc Pi) Qa(Aa Ad Al aU Aw AX bF CS Cv Dc Dd Di dN Ha Oa oD Pj Qb Qg Qh Qv Rm Vq Vt) Ez(Aa aC Ad Ap aU Aw Bb Bo Ct Cv Dd Dl dN dU Gc Gd Gn Hl Iz Kd Kj mU Pj Yj Ye) cU(Aa bR cl cN Cv DD dG dl dU Em fR Gd Gn Hr Lp Lv Nb nl oV Pa Pc Pj Qg Qv) hC(Aa Al aR Aw aX bC cS Cv Cx cZ eC eF fR gC hB Kc kF kG mP Nl nO Ns Nu oD) aO(Aa aR dL dN Dp fA Ib Je kE Lp Mb Mh NB Ni nO nT oW Pc Pi Rz Sf Ur Yl) Mj(Aw Cv fB fR Gn Hl Hr kE kF kG kN Lp Lt Lz Mh Nb Nu Op Qv Ur Wb Yj) aF(Ax Cs Cx eC fR Im kF kN Kx Li Lz Mh Ml mP Ni No Nt Nu oW Pe Pf) kG(Aw Dc dU Fd Gc Gp Hu Ic Jk Kd Mu Mw Mx Nb Nq nW Or Ou Pa Pi Ye) Sf(aH Dk fR Ij Jn Js kN Lv Nb nC Nr Nv Ok Om oP Ow Pf Pi) Pc(Aw cG cS fR gC iA jB kF nU Ou oV oW Qt Rz Uc Ug Vs Vu) Is(Al aX cS Cv Dd dN Gc Hb Hl Op Rx Si Wb Yd Yj Yl Zx) Pi(Dd Dp fB Jj kF Lp Qg Qt Qv Rj Ub Ug Uk Up Ur Wm) Gb(Ba dG Et fR Ij Jn Mz Nq Nw On oP Ow Pd Pe Pf) Dd(cG eC fR Fw kN Lv Nb Pe Pg Qd Qe Uc Uf Vv) kF(Aa Cv eC Gc iH Lt Mp Mt Nb Ne Nq Or pF Vu) Yj(cO Ct Iv Jn Js Mq Nr Oa On Ow Pe Pf Po) Qv(cG cL Dc dD Kx Mp Mx Nd oP Ow Tz Uf Vu) Ur(bF Ch cS Dk EF Hc hG Mu Nq oN oW Ph) fB(Aa aR cL dG dN Ik kN Mf Ni Og ON Zw) Ax(aL cV dD Lv mZ nA Nb Pg Qd Rg Uc Vv) Mh(aU aV Aw cL cV Dc dD fR Hc Or Ou Yd) On(Gc Gd Iz Op Rx Ry Si Wb Yd Yg Zx) nO(bF dD dG dR eF fA hG iP oN oT oV) Nb(aC dD Dr Hl Hr Lp Lv nU Zw Tl) Vv(Aa Cs Cv cW Dc Hb Iz Kf Kj Ks) cS(Cv Fd Lv Mp Mz Pg Qd Tz Ue Ug) eC(aC aL cV cX dJ Gz Kd kK Mf Pj) fR(bF bH bO dL dN Gn Jj mT nW Rg) Zw(aU aV bO dG dH Gn Gp Hq mU) Ow(Aa Dr Gc Gd Gn Hr jB oD Ye) Pf(Al aZ Gc Gd Hl Lp Op Zx Ye) hB(dU Hb Hr Iv kE oW Qw Rb Ug) dD(Cs Cv Hr Lz Ml Pe Rj Wm) dG(Aa aX Lp Lt Oe oT Yl Ye) Kx(mZ nA Qd Qg Rg Uc Ug) Cv(kN Lv Mz oV oW Qd) Jj(Aw Ba Ct Fw Hc oN) Aa(Ba cG kN Pe St) Al(kN Pg Qd Qc Uc) Tt(dN Kf mP Pj Rc) Lp(Ct Im Nr oP Po) Cs(cV Qd Rg Uc) Gd(Dg Ij Kl Rz) Gn(dH Hx Js Po) Ye(Ct Hc Nq Ql) Uf(Jo Rj Ue Uk) Pe(aL aU aV bF) oN(Dp oT Rb Ug) oV(bO mP nW Rj) Em(Qd Rg Uc) Hl(Jn kN nU) Hr(Fa Qt Vu) Zx(Hc Nq Nv) Js(Dr Gc Rx) Rz(cN dH dL) Yl(dH Mz Pg) aL(dN Lz Ni) cG(Bb nl Oi) Ct(Og Ug) Wm(aU bF) Lv(aX gL) Qt(aC mU) Xa(bO kE) Ry(Mz Nv) aQ(Hp Yk) cV(Lz Ml) nW(gC oD) oW(Rg To) ApNt AwkN DraZ DuPo FbNq FdPg NmKl MtUe NinY HcOy YdNv SjcP QdaS QwbF JnRx KynI dLhG mPoT} kG{Vb(aF aG aH al Aj aL Ba bF Bg bN bQ cG Ch cL Co Cq CT cU CX Dc dE dF Di Dk Du Eq Fa Gn Gp Hc Hl Hr Ij Is It Iz Jd Jf Jg Jl Jq Jr Jt Ke Kg Kj Kk kN Kr Lh mH Mn My Nf nR Ns Nw Nx Ny Of Ok On Ou Pd Pe Pf Ph Pi Ps Pz Qm Qn Qu Qz Rc Rm Rt Rv Sh Tv Tz Ua Uc Uf Up Uw Uy Vh Vi Vo Vp Vs Vw Wd Wc Wh Yd Yh Yj Tj) Hp(aI AO aQ aU aX aZ bA bF bZ cL Cp Cq cT cU Cx dF dI dR Ef Et Ex Ez Fd Fn Fw hB HC Hr Hv Ij Im It Jd Ji Jk Jp Jq kI Kk Kr kS Lh Lv Lx Lz Ma Mg mH mI Mj Mp Mq mU Mv Mx Mz Nd Nq nR Oa Ok ON OP Or Ou Ow Pe Pi Qb Qc Qe Qh Ql Qm Qn Rg Rv Tv Ua Uc Uf Uh Un Uw Vp Vs Vu Vv Wh Yd Yi Yk) Yi(aH aI Al aO aQ aU aX aZ bA bF bN cL Co Cq cT cU cV CX dA Dc dF dH dR Ex Fd Fn Fw Gl Hv Ij Im Jd Ji Jl Jn Jp kI KK Kr KS Lv Lx Lz Mp Mq mU Mv Mx Mz Nm Nn Nq nR Nv Ny Oh Ok Om oN OP Or Ou Ow Pe Pi Ps Qa Qb Qc Qd Qh Qm Qn Rg St Tn Uc Uh Un Uw Vi Vp Yd Yg) Yg(aH al aO aQ aU Aw aZ bA bF bN bZ cE cL Cq cT CU cV CX dA Dc dF dH dR eM Ex Ez Fd Fw Hv Ij Im Jd Ji Jl Jn Jp Jq Jr KK Kr kS Lh Lv Lx Ma Mp Mq mU Mv Mx Mz Nq nR Ny Oh Ok ON OP Or Ow Pe Pi Ps Qa Qd Qh Qm Qn Rm St Uc Uh Uw Vi Vp Yd) Hl(aO aS aX aY bF bI bO bW Ch cL cM cV dB DC dF dI Dk Fd Fy Hc Hq Hv Il In Ip Iq Is Jf Jl kN Kq Kr Lh Lv lW Mf mH mI Mj Mp mT mW Mz Nd nI Nq nR NU Nv nW Oa ON Or Pf Pg Pi Ps Qa Qd Qe Qh Qn Qt Rg Rh Rv Tv Uc Up Vp Vv Yd Yh Th) Gb(aH aI Ao aU aX bB cG Cu Dc dE Dk Et Fw Hc Ij Iq Is It Jd Jf Ji Jl Jn Jq Jr Js Ke Kk Kp Kr Lh Lv Lx Mg Mj Mp Mx Mz Nd Nf nI Nv Nw Ny Oh Ok Om ON Op Ou Pd Pf Pg Qm Qn Qt Tz Uc Up Uw Vv Wh Yj Tj) Kq(aF Al Ap aU Bb Bc Bg cR Cv Dg dI Ef Fb fP Fr Hw Ii Iz jB Jg Jj Jk Jm Jt Kf Kl Kn Ks Ky Lh Li lW Ma Mb mE Mm Mn Nd Ng Nh nI nK Nv Ny Oe Of Oi Ok On Oz Pb Pc Rb Rz Si Ss Tr Tv Ue Wb) Uw(aH Ap aQ aU aZ Bb cU dF Fb Fw Gd Gl Ib Ij Ji Jl Jn Jp Jr Kk Kr Ks Lv Lx Mg mI Mm Mn Mp mT mU Mx Mz nJ Nn Nv Ny Oh Om Op Or Ow Pe Pg Ps Qa Qb Qc Qd Qe Qm Rg Rm St Uc Uh Un Ux Vi) Gn(aF aO aZ bO bW bZ cL cN Cx dB Dc dI Ez Fd Fn hC Hv Ip Iq Is Jf Jl Js Lv Lx Ma mI Mj Mp mT Mx Mz Nu nW Oa Oh Or Ow Pg Ps Qb Qd Qn Qt Rg Rh Rm Rv Tv Tz Up Vp Vu Yh Th) Mj(aC aF Al aU Bb cF cR cY dI Ex Fb Fr Gd Gp Ho Hr Ic Ii Jj Jk Jt Ju Ky Lh Li Lp lY Mb Mh Mm Mn nI Nm Nn Ns Nv Ny Oe Of oQ Oz Pb Pc Ry Rz Tn To Ue Vv Vw Tm tF) Nb(aC aF AL aO aU aZ bF cG cL cR dA dE dI dU Fb gC Gp Hr Ic Ii Is iZ Jj Jt Li Lx lY Lz Ma Mh Mm Mv Mx nC nH nI nL Nm Nq nR Oi Or Ou Pb Pc Qd Qn Rv Tn Tz Up) Ut(aC Ad Al Ap aU Bb cR Dg dI dU EQ Fb fP Fr Hw Ib Je Jg Kl Lh Li lW Ma Mb mE Mn Nd nI Nx Oh Oi Om Pb Pc pI Pk Qz Rb Rz Si Ss Tr Tv Ue Ux Vw) Tn(Ad Aj Ap aU Ba Bb Bc Bg bX Cp cR Dg dK Dl Ef Eq Fb fP gC Gd Hw In Iz Jg Jt Kg Kj Kl Ks Lh mE Mn Mp Nd Nh nT nU Oi Oz Pb Pc Qu Ss Tr Tv Vw) aU(Ap Bb fP Fw Gh Gp hC Hv Ic Is Jn Jr kS Lv Lx Lz Ma Mh Mm Mx Nm Nn Ny Oh Oi Or Ou Pc Pe Pf Pg Pi Qd Rv Tr Tz Ul Up Vv Yh) Gp(Aa aK aQ Ax aZ bC bM bO bP cL cR dI Em fB Fd fR Ic Jr Kd lW lY mE Mp mT mW nA Nd nK Nm oV Oz Pb Pc Qd Vv Th) Lp(cE cL Cu dB Dc dI Dk Fd hC Hv Ip Iq Jl Jn Kk Lh lW mI Nd nI Nv Om On Ou Oy Pa Po Ps Qh Rg Rm Tv Vi Vp Yd) Rv(aV aZ bH bW cL cN dA DC dI Fd Fn Hv In Jl lW Lx Mp mT Mx Mz nC Ow Oz Pb Pc Pg Pi Po Ps Qa Qn Ug Um Yj) Tz(Aa Ar Bb cF cI cR fB fP Ic Id Io jB Lh Li Mb Mm Mn Nd Nh Ni Nj Nm nU Oe Oh Om Oz Pa Pb Pc pK Vt tF) Yd(Al Bb Dg dK Fb fP Gd Gl Ib Jj Jp Ks Lh Lz Ma Mh Mm Mn mT nI nJ Nm Nn nU Ny Oh Om Ow Rh Rt Sh Tv Ux) Ou(Ad Al cR cY dI Ef Ex Fb fP Fr Ic jB Jk Ju Jv Lh Li lW mE Mm Mn Nd Nh nI Nm Oe Oz Pb Pc Si To Zq tF) Pb(aZ bB cU Ed Fw Hr Ic Is Ji KE Lv Lx Lz Mf Mh Nq oD Or Pf Qa Qd Qh Rg St Uc Uh Up Vi Vu) Yj(Ap bW dB dI Dl fP Hv Ic Ip Iq Jf Lh Mf mI mT mW Nd Nt Nu Oi Qb Qn Qt Rg Rh To Vp Yh) Is(aF Ax cF cR dA dE Dg Dl Ex Fb Hr Ic jB Jt Lu mE Mm Nm Oz Rm Si Uy Vt Zq tF) Or(aK Al cI cR cY Dl Ex fB Ic Lh Li lW mE Mn Nd Nh nI Oz Pa Pc Si To Uy Tm tF) Pg(aC Al Cq dA Dg Fb fP Gh Hr jB Jj Jt Kl Ks Lh Mm Mn Nm Ow Oz Sh Si Vw Wb Zq Th) Lx(Ar Ax cR dA dE Du Fa Hr Ic jB Jt Ju Lh Li Lj Lu Mm Nd Nm Of Oz Pc Si tF) Ps(Bb Bc dC dK Fb Gl Hu Ib Jp Lh Ma mH Mk Mm Mn Nm Nn Ny Oh Om Ow Tv) Op(Ap Bb dC Gd Gl Ib Jp Ks Lh Ma Mm Mn mT nJ Nm Nn Ny Om Pj

Nn Pf Pg Qa Qd Qy Rh Rj Rx Uf Uo Ut Va) mW(aU aV cO Ex Ij Jj Jl Jn Jo Js Kx Li Oh oQ Ow Pe Pf Po Qa Rh Rt Tv) kF(aH aU aZ bB dD dR In Jq Ky Lh Lv Mj Nm Nq Oh Oi Or Pf Pg Vi) Lx(aO bO cA cF cK De dJ eM Hc Ho kC Lu lY Ml mY nJ Nv Yh tF) Nw(Aa bU cF cI Hb Ib Iv lW mY Mz nC nD nH Ni nU Ow Rc Rf Si) kI(aF aO bF dF Ez Fy Jn Js Mz Ok oN Pb Pi Qb Rf Tn Uf Vv) Pg(aK bO bU cF dJ Ii Ks Ld lW Lz Mh Ml nD nJ nK Ow Qx) mZ(cO Ij Jn Js Kx Ld Li Lz Ml Mz Oh oQ Ow Po Qa Qx Tz) nN(aF aO dF Ex hC Jl Jp Jq Lh Lv Mj Ok Om oN Op Ut) oQ(Ao Ch Co cY dA Gp Hq Ks Mn My Nx Ok Om Ph Yd) nU(aF bF dF Ex Ji Js Ke Ld Lh Oh Ok Tz) kK(bB Co cS dR gL Gp Lv Mk Mt Nn Nq pF) Iv(aO bF dF hC Kq Lh Mz Nv Ok Vi) Js(aO cF dA De dJ iH kO kP lW nA) eM(Ij Jj Nm Ow Pe Po Qa Rh Rt Vb) nH(aF aQ dD dF Ij Ji Jp Lh Lv Oh) kE(aQ Ax bF bQ cL Ez Ld Ma Om Pi) kN(aK aQ aU dR Ji Kc Ld Lh Ow Tn) mP(aF aK dF dR Ex Lh Mj oN Vi) Mz(cC cF lW Mh mS nI Nv Rx) Ut(bH cH mE mF mU mY nA Rc) nC(aQ Et Ij Jp Jq Lh Lv Oh) nL(aF dF Ex Jp Lh Lv Mj oN) Mt(dE dI mI Mj mT Tz Yh) Nv(Ad Ks mF Mh nK Oi Rc) De(Dg Gd Hp Jo Mh Oh) Tz(cS Hb Ni nJ Oh Rf) dF(lW mT mU nD nK) lX(aK aQ aU cY dR) nI(aF cG Lh Ok oN) nJ(bZ Fy Hq Ma Nm) kP(aO Jn Ma Qa Uw) Jl(bS cF Ld lW) Jq(cF Ni nK Rf) mI(gL Ij Nn Pe) mS(bQ bZ Ez Ma) nA(Ez Gp Jn Qa) Lv(cT kC Na) Hb(aZ Or Qd) Kq(Gd Mh Sh) Lh(Ii nK Rf) aF(mT mU nT) dR(kC mM mU) fB(bF Pi Yh) tF(Ld Ow Qa) mF(aQ Jn Qa) Ex(mT Rf) Tn(fR lW) Rx(aZ Iu) Or(Na Rf) Vi(bO dJ) Pe(hC kR) aO(Nb Rc) mM(dD Fw) EdLj FydJ GhkR NnmE LuRh MhOm MihC MjnK HoPf IjlY JnkO OhdA OkmU VvlW bQkC mToN} oV{cT(Ad aG Al Ap Ar As Ax Ba Bb Bc bH Co Cp Cs Cu Cw Dg Ez Fa Fb Fp Fr Fy Ha Hb Hw Ib Id Ii Ij Im Io Iz Jd Jj Jm Jo Jq Js Jt Ju Jv Kf Kl Kq Ks Lh Lj Ma MM Mn Mw Nm Nv Nw Ny Oa Oe Of Oh Om On oQ Pc Pj Pz Qb Qh Ql Qm Qn Rf Ss To Ue Vq Vs Vt Vu) Ma(Ad aF Ap Bb Bc Co CU Dc DG Dk Dl Ef Ez Fb Fr Fy Ib Ih Ii Im Io Iz Jg Ji Jk Jm Jo Jq Js Jt Jy Ke Kl Kq Lh Mm Mw Nm No Nv Nw Oa Oe Of Ok Om On Pj Pz Qe Ql Qm Qn Rc Sr St Uc Ue Uf Un Vq Vt Vu) Pc(aA aC aF Al aO Aw BA bF bH bO bQ cG cS cU Cv dN eF EM Ez Fy Hb HC Hr Ib Ip Iv Jj Jv kC kF Kg kK kN Lu Mh Mm Mv mY Na Nb Nf Nm nO nR nY oK oN Ou Ph Pi Pk Qn Rb Rj Tn To Tz Up Us tF) cU(aF Al Ap Ax bH cF cM Cs dA Ef Em Et Ex Fa Fb FP Fr gC Gl Ha Hb Hw Hx Ib Ii Ij Io Jl Jm Jp Jt kC Kk Lh Li Lj MM Mn Mr nI Nm Nn Ny Oa Oh Om oQ Ow Oz Pb Pj Qh Rf Rm To Un Vq Vt tF) aF(aR aW AX bH bZ cF cS Cx Em Ez fA Fw Fy Hb Hc Hf Ik Im kC kN Kq Kx Ky Ld Lx Lz mE MH Ml mP Nb nD nI nK Nn Nr Nt Nu oF Oh OW Pd Pe Pf Qt Qu Qx Ra Rf Rh Uf Wm) Al(bA bF bH bQ bV bZ cG dF Ex Ez Fa Fw Fy Gl Gp hC Iv Jr Jv Kk Kq Kx Ld Lx Mx nN Oa oN Ou Ow Pd Pg Ph Pl Qe Qn Qt Qu Rf Rh St Tv Tz Uc Vp Vs) aO(aG Bb cF Ex Fa Fb Gz Io Jd Je Ju Jv kC KE Kf Kk Ko Kq Lh Mb Mh Mm My nA Nb nI Nv Ny Oa Om Or Ou Ow Qh Qm Qn Rm To Tz Ua Uh Ul tF) Vv(Ad Ao Ap Bb Cw Dc Dg Fb Ha Hb Iz Jg Jj Jo Jq Jt Ke Kf Kj Kl Ks Lh Li Mm mT Nm Nn Nr Ny Oe Of Oh Ok Om Pj Pz Qd Qe Ss Uu Vt) Ez(Ad Ax Bb Bc Co Dc Dg Ef Fr Hb Ih Ii Ij Im Is Jm Jo Jq Jt Lh Mm Mt Nm Nn Ny Oe Of Oh Om Pj Qe Qh Qm Qn Ue Vq Vt Vu) Ld(Ad Bb Bc bH cR Dk dU Ef Ex Fb Fr Hb Io Iz Jg Jk Jm Jq Ke Kf Ko Kq Li Mb Mh Mm Mq mW Nm Nv Nw Nx Of Ok Om Oz Qn tF) bF(Ad Bb Bg bH cD cF Dd Dp Ib Io Jk Jv Mh Mw My Nd Oa Oe Qh Qw Qz Rc Rj Ua Ue Ur Us Uu Uv Vs) bQ(Ef Fa Fb Fy Ha Hb Ib Ij Iz Jd Jm Jt Kf Li Mm Mw Nm Nn Nv Ny Oa Pj Qm Qn Rc Rf Rm Vq) oN(Ap Cw Fa Fb Fy Ha Hb Jy Kf Kn Li Mm Nm Nn Ny Oa Qh Qm Rf Rm Vq Vt) kF(Ap Fa Fb Hb Ib Jv Jy Kf Kn Mm Nm Oe Pj Qw Sr Ue Uh Un Vt) bA(aC dM Ef Fb Ha Hb Io Jk Jm Li Lj Mm Nn Ny Oa Qh Ue tF) Uf(Ad Ap Fb Fr Ii Iz Jg Jk Ke Kf Lh Nm Nv Oh Pz Uu) bZ(Ad Fr Hb Ih Ij Jk Jm Js Nm Oa Of Qh Sr St Ue Vt) Nm(Cu Em Fw Hc kC kN Na Nt Ok On Pk Qu Ut) Mm(Ba bV cG dK Fw Hc kC kN Na Ok On Pd Pk) Hb(bH bV Fw kC Kq mU Na Nw Ow Pa Pd Qn Tz) Hc(aA Ad Ap Fb Jg Jv mT Nn Of Pj Pz) Ut(Cp Fb Jk Jm Kf Nx Of Om Ue Vq Vt) Ef(Cu kN Lx Nn oF Oh Ow Pe Pf) Jv(Ba Cq Fp Lj Oz Pa Pb Pd tF) kC(Ad Ap Iz mT Mw Qy Rg Ss Ug) Tn(Ad Cp Is Jd Mt Pz Qn Vq) Nn(cG Fw kN Mx Ok On Pk) Pd(Ad Rf Rm Ue Vo Vq Vt) Lj(Fy hC Kx oF Oh Rf) Ny(cG dF hC kN Ok Pk) Oh(Ax Fa Rf Rm Vt) Pi(Ii Jm Rb Ub Uv) kN(Ap Jy Kf Oa Pj) Bb(Ok Pk Qn Tz) Cu(Ad Fb Jt Li) Fy(cR Oz Pb tF) Lx(Fp Iu Rf Vt) Fb(cG Fw Ok) Mx(Ha Li Qh) Ow(Ih Jm Rf) bH(Em pK Rb) Fp(hC Rf) Mh(Di Ns) Tz(Jk Jq) Oa(Gp hC) Ok(Iz Uu) Vt(Jl Nw) AaaA AdOn ApcS CvaC EmmW ExQn UePa IbeM KfbV cFnR mTnD} Tn{nU(aC Ad Aj Ap Ba Cp Dg Dl Dp Ef Ez Fd fR Fy Ii It Iu Iz Jg Jj Jk Jm Jo Jt Kg Kj Kl Lv Mb mE Mm mT My Ng Nm Nn Ns Nt Nv Ny Oe Of Og Oh Oi oT Pz Qu Rb Rg Ry Sh Uf Ug Um Ur Uu Uy Vo Vs Yj Ye) kI(Aa Ad Ap Ax Bc Bg cM Cp Cu eC Ef Fa Fb Fy Gd Hb Ii It Iz Jg Jm Jq Jt Ju Ke Kl Kq Ks Lh Li mF Mm Mn Ng Nh Nm Nn Nv Nw Ny Of Oh Ok On Pc Pj Pz Qc Rm Sj Uw Va Vo Vt Vw We) nT(Ax dA Dp Ez Fy Gd Hl Ii Iu Iz Jg Jj Jk Jm Jo Jt Kj Mm mT Ng nI Nm Nn Nv Ny Of Oh Oi Ou Ph Pz Qu Qv Rc Rm Uf Ug Ur Uu Ux Uy Vo Vw) nN(Ad Ap Ax Ba Bb Bc Ez Fb Fy Ii It Iz Jg Jj Jk Jm Jo Jt Kg Kj Mb Mm mT Ng Nm Nn Nt Nv Ny Of Oh Oi Ok Pz Qu Rm Uf Ug Ur Uu Vo) nI(Ad Al Ao Ap aZ Ba Bb Bc Bg bX Cp Ct dA dC DG Dl dM Ef Fb fP fR Gd Hc Ib It Iz Jg Jt Kj Ko Ks Ky Mp Nh Pk Pz Rc Ux Vw Wh) pK(aF aO bH cE Ct Dd Dk Hq Ir Iu Jd Jh KC Kg kR Mh Ms Mw Nd Nj Ns Nt Nx Ny oD Oe Og Oi Pf Ph Pz Qv Qw Qy Qz Rc Rj Ur Vu Vv) mS(Aa Ad Ao Ap Ax Bc Cu Fa Fb Fy Gd Ii It Iz Jg Jq Jt Ju Jv Kl Kq Ks Mm Nm Nn Nv Ny Of Oh Ok On Pc Pj Pz Rm Ux) mP(Ad Ap Ba Bb Bg Dg Ef Ez Fy Ii Iz Jg Jj Jk Jm Jo Jt Kg Kj Mb Mm mT Nm Of Oh Oi Pz Ss Uf Ug Uu Vo) nR(Bg Dg Ez Fy Ii Jg Jj Jk Jm Jo Jt Kl Ks Lh Mb Mm Mn Ng Nn Nv Of Oh Oi Pz Qu Rc Uf Ur Uu Ux Vs) kP(Ap Bb Fy Hw Ii Jg Jj Jo Jt Kl Lh Li Ma Mm Mn Ng Nm Nn Nv Ny Oh Ok On Pc Pz Rc Ss Uf Uu Uw) fR(Ad Aj Al Bb Gd Hp Ii Iz Jj Jo Jt Kf Ks Lp Mm Nm Nv Of Ok Rc Rt Ug Uu Va Vo) eP(Af aG cU Cx Ha hB Ib Jk Kc Mp Mt Oe oF Ou Qt Qv Qw Rc Rj Ur Uu Vp) oQ(Fr Jj Jk Jm Ld Mm Nm Nn Nv Ny Oe Of Oh Oi On Pz Qe Ss Ug Uu) eM(Ad Bc Gn Hl Hp Im Jt Kj Ou Qv Rc Rx Ug Ur Uu Wb We Yj Ye) mT(Af Al bX cS Cx dA dG dM Gd Jj Jo Kc Kq Mp Mu Nn Nq Qy) mU(Ii Jj Jk Jm Jo Mb Ng Nn Nv Ny Of Oi Pz Qu Ss Ug Ur Uu) Nd(Dr Gn Hl Lp Rx Ry Sh Ux Uz Va Vi We Wf Wg Yg Tl) Rc(Du eQ Gn Hl Ru Ry Um Uw Uz Vb Vh Wf Wg Yj Yl Tl) pH(Bb cJ dC fP Gl Hw Hx Ib Ii Lh Mz Oz Pb Pc To Uh) mM(Ii Jj Jk Jm Jo Mb Mm Nn Nv Of Oi Pz Ss Ug Uu) oT(Bb Cp fP Ii Jh Jy Ke Li Lu Ms mW Nq Oe Qn Uv) oP(Ao Ap Bb Bg Cs Dc Fb Ii Kf Kn Ok Ow Pj Ug) eQ(aF Dc Hw Id Kf Ko Lu Nm Nt Pc Pz Uu Vo) gZ(Bg cM Dk Fp Hx Is Jy Lj Ny Pc Rf To Un) mY(Gd Ii Mm Nk Nm Of Ok Ps Ry Si Uw Vw We) nJ(Eq Fd fP Gd Ks Ok Rx Ry Rz Sh Uw Vw Ye) mF(Ct dU Gd Kl pI Si Sj Ss Uw Va Vo Vw) nA(Al Bb Cp Dg fP Kl Ko Ok Si Sj Uw Va) nO(Ii Jj Jo Oi Pz Ry Ss Tv Ug Uu We) mE(Bc Cv Dp Jj Oe Og Oh Ug Um Ur) dU(aO cM cS Dl hB Kn Lu Ns Vq) fB(Iz Jj Jv Kj Nr On Vo) gC(Ad Dl Ju Jv mW Ph Qz) oD(bF Dp Ez Kn Nf oH) pI(Dl Jj Kc Ns Ph Pz) Gd(kN Mz nK nL Ry) Yg(aY cA cK fP oF) dX(bI dG Kf Of Uu) mH(Al Rt Wd Zw Ye) mW(Dg Hl Kj Rt Vw) nB(Bb Ii Jj Kl Oi) kC(Ps Si Sj Uy Vw) kF(Ad Ba Dg Kl Oi) oW(Dg Kn Li Nx Ok) nL(Eq Ux Vw Wb) kK(Af dM cC Fa) oE(Ad Bb Ez Ry) Gz(Ad Hp Mm) Sj(kN kO nD) lW(Lp Uw Wf) jB(Ii In Kc) Ry(hC oF) lX(Ap Bb) mI(Jo Uu) nK(Ux Vw) kE(Al Fa) EdHp EqnC IvYj WbnH RtmZ VakN} Lp{nI(Al Ao aV bA bB Bg bO bQ bZ cE cF cG Ch cL Co Cp Cq cS cT CU dA Dc dF Di Dk dR Ef eM Eq Fr Fw Fy Gl Gn Gp Hc Hp Hr Il In Is Iz Jl Jp Jq Jr Jy Kk kN Kq Kr Lh Lv Ma Mf Mj Mu Mv mW My MZ nC Nn NR Nv oF OK Om ON oP Or Ou PF Ph Pi Qd Qe Qh Qu Qw Rg Rz Uc Uf Uv Uw Vi Yd Zx) kN(aJ aQ aU aV Aw aZ Ba bO cL cU dR Ez Fn Fw Im Jk Jl Jr Js kC Kq Ld Lv lW Lx Mb Me MF mH ml Mj Mp Mq mU nB Nq Nv Nw oF Oh Om Or Ou Ow Oy Pb Pd Pe Pf Pg Po Ps Qa Qd Qe Qt Qz Rb Rg Rj Rm Tz Ua Vi Vp Vq Vs Vt Wd) Nd(Ax aZ Bo bX Co cS CU Ed Ez Fi Gz Ho Hq Is Iv Jf Jl Jr Kp Lx lY Ma mE mF Mi Ml Mp Nj Nn Nq nR nU Nw Oa oQ Ow Pg Ps Qd Qe Qh Qm Qy Rx Tz Uf Uh Vp Vq Vu Vv Wb Tl Tj tF Yf) mW(aJ aK aP aQ aU bO cT cY dJ Ex Fn Gl Hc Hv Jf Jn Jr Js Kk Kx Ky Lx mE Mf Mh Mk Mp mU Nb Nl Nw Oa oE oF Oh oP Ow Pc Pf Po Ps Qa Qd Qe Qx Qy Rg Tz Ua Uf Un Ut Uv Uw Vi Wd Wh) nU(aF aK aL aQ aU aV Aw aZ bA bO cT cY dE dF dI dJ dM Fw Gl Hv Jf Jn Jq Jr Js Kk mE ml mT nJ Nw Oh Ow Oz Pb Pc Ps Qh Qn Qt Rg Rm Tv Us Uw Vi Vp Vs Vv Wh Xa Th) lW(Ao Aw bZ Ch Co Cu dR Ef Hq Il iO Iz Jd Jh Jl Jp Jy Kq Ma Mf Mu Mv My Nn Nq Nv Om oN Ou Qu Qw Qz Rz Ua Ut Uv Vi Vu Zx) mT(Ao bZ Co cS Cu Ef Eq gL HC iO Iz Jd Kq Ma Mg Mu Mv Mw My Nn Nq

Figure 40 Continued

Om Ou Pf Qd Qh Rz Tz Ua Ut Uv) mE(Bg bZ cE Ch Co Cu Ef gL iH iO Iz Jd Jh Jy Kq Ma Mu Mv My Nn Nq Nv Ou Pf Pg Qd Qu Rz Ua Ut) mI(bC bF cS Ct Eq Ez Gp Hc Hv kF Mg mP Mt Ng nH Ni Nn oF oK Oy Qd Qu Rz Uf Ut) mH(aJ aP Ct Ez Fy Ih Im Js kF Nn oE Oh Ow Pe Ps Qa Rf Rh Rz Uf Ut Uw Vq) nH(cU dI gL In Jn Pz Qa Qb Qc Qd Qe Qh Qt Qz Rg Rv Tz Uw Vi Vq) nR(aQ aU cM Gn Hv Pb Pc Ps Qa Qd Qv Rg Ri Sf Tz Vi Wh Yj Th) oP(An aQ bB bX cD cF cI cM Ct cY De dI Gh Hv Id Nn Ny Oy Pg) mF(bF Bg bZ Ch Co Ef Hq iO Jl Ma My Nq oE Pg Qa Qd Ut Wh) lX(aK aQ aV bO cY dR oF Qd Qt Rg Ri Ua Um Uv Vs) mU(Bg cF cM dI hC Jf Kz Qa Qd Qu Qw Qz Us Ut Vi) kI(bC bF Ct Gl Hv Oy Pa Pc Qa Qd Uf Ut Vq) Cu(Ad Cw Hv Kn Nn Rj Ud Um Uo Up Uz Wg) nJ(Aw bF cE cU Hq Jl Kk Lv Ma Pi Ut Vi) Vu(bH bO cH Hv Ib nL Nn Ow Sh) nD(Hq Jl Lx oF Ps Qa Rm Tz Vp) kE(bC bF Ct cY Ez Oy Pb Pi Vs) Vv(Hv Ib kC kF kP Oi pF Rc) nC(dI Jf Qb Qe Rg Rv Tz Vq) oF(An aY bG Gh hB Hv iA Jf) Is(Ad Fa Hb Nn Qa Uy Yl) Qd(fR kC kO kP mY nA) Tz(cF Hb Hc iH Nj) mZ(bF oN Qa Vq Wh) nA(Fy Qa Uf Ut Vq) Hc(aZ Gz Hv nB) Pg(aH kS nB pF) nN(aF hC Ma Uc) mP(hC Qh Vi) Nb(Uo Yf) Hv(Id Kd) Qa(Fa kP) Yl(Or Ou) Rg(kF mM) On(Ad Nn) fB(cM Hq) nO(In tF) nB(Nx Yd) kO(Ua Uv) EdGp MjmY JfoQ QtmM QhnL JrRx UtfR dBkF kKoN} Nd{Hl(aJ aM aP Ax bB bO Cq Cs CU Dc dG Ed Em Et Fd Fi Fp Fy Ha Ho Hq Hr Hv Hx Ij In Is Iv Jf Ji Jl Jn Jr Js Jt Kd KE kN KQ Kz Li Lj Lx Mi Mj Mk Mq Mr Mt mW Mx Mz Na Nb nD Nj No Nq Nr nU Nw Ny Oa oF Oh Ok On Ou Ow Pe Pf Pg Pi Po Qa Qd Qe Qh Rb Sh Tv Tz Uf Ut Uz Va Vi Vp Vq Vu Vv Wb Xa Tj Th Yf) Ry(aA aJ aM aP Ax bB bQ cG CU dF Ed Et Ex Gp Hq Ij Is Iv Jl Jr Js Ju Kx Kz Ld Lx Mi Mj Mv Mx Na Nb nN No NR Nv Nw Oa oF Oh Ok On Ou Ow Pe Pg Pi Po Ps Qa Qd Qe Sf Tz Uf Uh Ut Va Vp Vv Tj) Sh(aN AO aZ Bc bF Bo bZ cG cI Co cU dA Di Ed Ez Gp Gz Hc Hq Is Jl Jr Lt Lx Ma Mv My Nn Nq nR nU Nw Oh Ou Ow Pg Qd Qh Rz Uf Ul Ut Vu Vv Wg Th Yf) Rx(aP Ax aZ cT CU Ed Ez Fy Gp Hq Is Jl Jp Jr Ju kE kF kN kO Lj Lx Lz Mh Mj mM mP Mv Nj Nq nR Nw Oa Oh Ow Pg Qd Sf Tz Vv Wb Yl Tl Tj Yf) Yf(cU Ez Gp Gz Hp Hq In Jd Ji Ke Kg Kp Kq Kx Ky Kz Ld Li Lv Mp Mq Mt Nq Nw Nx Om Or Ou Ow Pf Qd Sf Ug Ut Va Vj) Va(Cu Ez Fi Hq Is Iv Je Jr kK Kp Mg Mp Nj nR Nw Nx On Ou Ow Pg Po Rz Tz Uf Up Ut Vq Vu Vv Wb Yh Tl) Sf(Ao aZ Bc Bo Ct cU dA Ed Gp Gz Hq Is Jf kE Kp Lx Lz Mh Mp mS Nq Nw Oh Ou Ow Pg Tz Uh Vu Vv Tl) Uy(Ax cU Ed Fi Gz Hq Is Iv Js Kd kE Lx Mi MP nH nN nR nT nU Nw Oa Pg Qd Qe Qh Tz Vv Wb Tj) Du(Ax Cs Is Iv Jr Kx Li Lj Lx Mv Mx No Oa Oh On Ow Pe Pg Po Qa) Hp(aZ CU Ed Is Iv Jl Lx mU nR nU Oa Pg Qd Qe Tz Vu Vv) Si(aZ Ed Et Gp Lx Nq Nw Ow Pe Pg Qd Tz Uf Uh Vj Vq Vu Vv) Ru(Ed Fy Hq Is Iv Li Lx Mh nN No Nr Oa Oh On Ow Pf Qd) Gd(Eq Ez Fi Fy Gp Ho Jd Rz Uf Vq Vu Yh Yj Yl Zq Tl) Lx(Rt Uw Uz Vb Vh Vi Wf Wg Yg Yl Zq Zw Tl Xa) Fi(aZ Gp Jo kE Kp Mh Oi Oy Ue Ug Ul Um Vb) Yg(aO CU dF Ij Kq On Pe Pg Po Qa Ut Vi) Is(Rm Rt Uw Uz Vh Vi Wf Wg Yj Xa) Tl(aM Cu Gp Ju Jv oF Pe Ut Vi Vo) Ye(mP mT mU Nq nR nU Qd Uf Vu) Kp(Fd Ho Ps Uz Vi Wb Yl Xa) Rz(Aj aZ kE Mh Oi Oy Tz Ux) Vb(cU Fy Iv Jr nR Oa Pg Uf) Uz(Iv Jr On Pe Pg Po Qa) Ho(Jo kE Kf Nm Oy Ug) Yj(bB Iv Jf On Pg Po) Wg(Iv Jr Kq Ou Ow Po) Uw(cU Ed Nw On Pg Qd) Gh(nR oE oF Vu) Wf(Fy Ou Pg Ut) Vi(On Pg Um Uo) Ou(nO Yl Zx) eD(Ha Um Tj) nR(Ha Ju Qh) nI(cU Rj Ut) oE(Fa Hc Ns) Eq(Mh Oy) Fc(Gp Ug) Yh(aZ Ne) Wb(Mh Ow) Qd(Hb Um) Ky(jF lN) Rt(On Pg) Ux(Ez Uf) Vh(On Po) mE(Qu Ut) oT(Ju Jv) EdGn FdPg NqZx MbkF IdlL SjVv ZwOw QxmZ QhpH PsUo LdjB YlOr QmVj} oT{Vv(Ad bE Cp Cs Cu Dc Dg dN Et Fb FP Ha Ib Ii iO It Iz Jg Ji Jj Jk Jo Jq Jt Ke Kl Li Lj Lu Ma Mb mF mW Nn Nr nU Nw Oa Oi Ok Om On Pc Pj Pz Qb Qe Qh Rj Ug Ul Uu Vo) Jv(Aj Ao aR Ba bC bJ Ch cL Cs CT cZ Em Ez Fw Hc Hq iO Kc Kf Kg Kj Kk Kp Kq Lj lW Ma Ml Mp mS Mw nI Ns Nw Oa Oh oN Ou Ow Oy Oz Pa Pb Pd Pe Pg Pz Qd Ri To Uc) Ju(aO bA bZ cL CT Cu Dc Dk Ez Fw Hc iO Is Iu Jl Kq Ld Lv lW Lx Ma Mg Mj Mp Mz nI nR Nw Oh oN oP Ou Ow Oz Pa Pc Pd Pf Pg Ph Qa Qd Qn Rm Tv Tz Uc Vp) Ny(BA cL CT cU Dc dF Fy Is Ji Jl Kl kN Kq Kx Lh Lv Lx Mg Mj Mp Mv Mz Nb Nv Nw Oh OK Om ON Ou Ow Pd Pe Pf Pg Pi Po Qn Uc Ut Vs) Ma(Ar Ax Bc cM Cs cU Dk Fr Gl Hb Ib Ij Im Jk Jq Js Jt Lh Li Mm MW nI No Nv Oe Ow Pj Qb Qm Qn Sr St) Ut(Bb Cp Cs dI fP Hb Ib IO Jd Jg Jm Ke Kf Ks Lh Mn mW Nm Nn Nr Oh Ok Om Pa Pj Qm Uv) Ow(Aa Ar Bb bC cR Cs dI Fp Fr Hb Ij Kz lW Ml MW nI No Ns Oe Pa Pj Qm Qz Rf Uv) nI(aF aN aO bF cF cN cT cU Iv kN Lx Mj mP MZ Nb oK oN Pi Qn Rj Rm Tz Um Vp) iO(aF aN aZ bA cT cU Cv cX Hr Iv Mh Nb oN Pc Pg Qd Qg Um Vp) Lx(Ar Ax cM Cs Fp Fr Ij Jk Jm Lh Li mW Nn Oa Oe Qz Rf To) mW(cF Em Ez Fy Hc Kx Ld Mb Nb Oh oN Pc Qx Ra Rf Rh Wm) aF(aR aW bC bJ cV Cx cZ dN Ik mH mP mS Ni oD oH oW) oN(Ar Ax cM Cs Fp Hc Io Kz Lj Mm Mw Nm Nn Pc Qm Rf) Kq(Bb Hb Ib Jg Ji Jk Lh Nm No Oh Ok Om Pj Rc Uf) Mm(Dg dL eF Ez Ji Kl mP mS On Pd Pf Pg Qd Uc) Nn(Ba cL eF Fw Fy Ji mP nR Oh On Pf Pi Po) Ni(aO aZ bA bF bH cU Jf lW Ou Pc Pg Tv Tz) Oh(Aa Al Ax cM Cs Fa Io Lj Oe Rf Rm To) Pc(bC bU dN eF Hf Kd kN Mb Nb oK Ou Uc) Ez(dI Fr Ib Jk Li Oe Pa Pj Qm Rf Rm) bH(aR bC bW cL cS cZ eF mP Nb Qd) cT(Ax bC cM Cq Cs Ib Io Lj Oe) Qd(Al bF Dd Hb Io Lu Nm Pj) Pi(aU cF dI Hr Mb Rj Uv Vp) Cs(bZ cU oE oF Pe Po Qa) Bb(bC cL Cu Fw Ke Nw) Mb(aO bG cL Nv Nw Pb) Ib(bF cU eF Nw Om Pg) Pd(Fb Jj Jy Nm Pj Rc) Ld(cR dI dU Li Pa) bA(aR bC cM Cq Oe) Ax(Nb oF Pe Po) Mw(kF mP NB) To(dN Lv mP pH) Li(CU eF Pf) Lj(Oa Pe Pf Po) Pa(dN Hf Kg Uf) bC(bF Jj kN nU) bZ(Ar cM Fr Pj) Aa(Is Mp Pg) Fy(lW Oe Oz) Hc(Fr Oe Rj) Qa(Fp Oa Pj) Qm(aO mU Uc) cL(Jf Jj Qn) cU(cM fP lW) Ml(kN Kx) Tz(bJ cV) Pg(cS Io) mP(mE Ri) AlQe FbNw FpPe FwPj MpHb HqJk TvbJ RbmS JfcZ JlJm KchC RfcM PbdN} nR{Hl(aM aR aW bG bH bM bO cH cJ cM cP cS cV cW Db dI Gh Gp hC Ib Il Iv Jf Js kN kO Ld LX Lz mE Mf Mh Mj Mx Mz Nl nU nW Oh oN Ow Pa Pc Pe Pf Qa Qx Ry To Yk) Gn(Ad aF Ap aZ Bb bG bO bW cQ Cw cX Dg dH Dl Eq Fb Fn Gd Gh hC Iv Jf Jg Jr Jt Kl Ko Kp Mh Mz nl Nm Nn Ny Oi Pc Qx Rg Rx Sh Ss Tz Up Ux Vb Wf) Vb(aO Ba bC bF bQ cF Co cS cT cU Ez Hc Jr kF Lh Na nL Nv Nw Ok Pc Pd Ph Pi Pk Ri Uf Ut Vi Vw Wd Wh Yh Xa) Hp(aA aQ aZ cT cU Fw Gh gL HC Iv Jn Jp Jr Ld Lx Nb nl Pc Pe Ql Qx Ri Rm St Ut Uv Vu Wd Wh) Al(aZ cU dJ Ed Fw Ih Iv Jn Jr Kx Lx Mh Mx Nb Nq Oh Pe Qa Qb Qg Rb Rm Tz Uf Ut Vu Vv Wh) Jj(bC cF Di Fw Hq Ik Jr kF Kg Ma Nb Nl Ns Nt Ok Oz Pb Pc Pi Qn To Tz Vv We Wh Yh Xa) Nm(aU cF Ez Fw Ji Jr Ke Kx Ld Lx Lz Mg Mh Ml Mq Mx Nb Nl Oh Pf Yh) Tz(Aa cF Em Io Jk Jm Ju Jv Lh Mm Mn Nv Pc Rc Rt Sf Sh Si Uw Uy Va Yg) cF(Ad Ap Dd Dg Dl Gd Jo Jr kl Ko Lz mE Ml Mm Or Pj Qb Rb Sf Sh) Gh(aQ aU bO cM cY Gp Jr Ju Kn Mm Nn Ny Pc Qv Sf Ug Um Ur Yj) Uw(cU Fw Gd Ji Jn Jp Jq Js Kx Lh Nv Oh Pe Pf Qa Ut Vi Xa) Mm(aU aZ cY Di Fw Hr Im Lh Lx Lz Mx Nb Oh On Pf Qa Vi) Ju(aQ aU Is Ji kl Lh Lx Lz mE Mj Ml Nb nl Oh pK Qb) Ut(Bb Cp Dg Gd Jg Jk Jm Kl Ks Lh Ma Mn Nv Rt Tr Yg) Vv(Ad Bb Dg Gd Jo Jt Kj Kl Ks Rc Rt Ss Ug Uu Vo) Pc(Cv Ed Gp Li Lx Lz Mb Pf Qd Rb Sh Uh Um Ur Tj) To(Fy Is Jo Ky Li Lx Lz Ml Oh Pe Pf Qa Ur) Dg(aQ aU cY Di Ez kF Kq nl Rz Uf Wh Yh) Nn(aU fA Fw Is Ji Jt Li Lx Lz Nb Pe Pf) Ld(Dr Gd Of Op Rx Ry Rz Sf Sh Tr Wb Yl) Rt(aO bF cT Hq Jq Na Nv Ok Pi Qn Yh) nl(Ad aF Ap Cv Dl gC Jt Mn pK Ug Um) Yg(aO aZ cU Fw Jp Jr Lh Nv Qx Vi) Zq(cU Gp Js Lh Lx Lz Oh Ow Pe Pf) Yh(Ad Bb Gd Kf Mh Ur Uu Ux Vw) Vi(Fb Ib Kn Ks Lh Ma Mn Ny Om) Jr(Du Rb Ry Um Ur Ux Uy Xa) Jt(cT Ez Is Nb Nt Oh Pf Uf) Uy(bZ Jq mH Mx Nv Nw Th) Ad(cI Ez Hc Mg Nb Wh) Bb(aQ aU Di eM Ke Nw) Gd(Ez Gp Hc Jf Wh Yj) Gp(Rv Ry Sh Ti Th) Jo(Ez kF Ma Nt Uf) Of(Ji Ma Mx Nt Nw) Ux(Ez Hc Mg Pf Rz) Ax(Kx Lz Oh Pe) Hq(Fd Sh Va Ye) Rb(cM Ip mE Ns) Qd(Em Lh lY Mn) Wh(Cv Ib Kf Kl) Jm(cT Lx Nb Qa) aU(Ap Cw Kf kR) Sh(Aw Fw Ri) Qx(Em Nh Sf) aF(Lz Yj Yk) Lx(Ny Sr) Mb(kF Ns) Nb(Ii Ug) Kq(Kl Ks) Lh(cU Si) Oh(Rf Rm) Ur(mE Pb) CvaC EmQb EzRc FwKs LzMn TrdA IsQh SsRz WcbF LiPe RvRi NwVt UmmE cMcU} Cu{Yj(Aa Ad Aj Ap Ba Bb Bc Bg Ch Co Cw Dg Dl Ef Ez FR Fy Gd Gl Ib Iz Jg Jp Jt Jv Kf Kg Kj Kl Kn Ko Kq Ky Li Ma Mh Mm Ng Nm Nn No Nv Ny Of Oh Oi Ok Om Ow Pj Qu Qv Rc Rt Rx Rz Sh Si Sr Ss Tr Uf Uh Un Uu Uw Ux Uy Va Vb Vj Vo Vs Vw Wb Zq) nI(Ad aF Al Ap Ax Ba Bb Bc Dg Dl Ef Fb Fr Fy Gd It Iz Jg Jj Jk Jm Jo Jt Ju Jv Kl Ks Li Mm Ng Nm Nn Nv Ny Of Ok Pj Pz Qn Rc Rx Sf Sh Ss Uc Ue Uf Ug Ur Uu Vo Wb Wd Ye) Ux(Ad An As cF Cq Dc Dd Dr Gn Hl Hr Hx Ib Ii In Ir Jn Jq Jr Kd Kk Kn Kr lW Na Nf nH Ns Ny Pk Ra Rj Rt Ry Sr Tv Um Uo Up Us Uy Uz Vh Vi Vp Wg Yl) Hl(Ad Cw Dg Ef Hr Hv Ib Jg Jo kE Kl Ko Ks Kx Ky Kz Ma Mh mT mW Mz Ng Nn nT nU Ny oF Oh Oi Ok Ow pF Pj Rc Rj Rx Ry Si)

Nq(Co Hq JT Ko Mu Mw Nf Nr Of Om On Oy Qb Rc Vs) rC(aA Hu In jD Jk Lj Lu Mu Mv Mw Nn rZ) Qb(An Ax Bn cF Cs De Id Ko Ld Mu) Dl(An Hv Hw Lv Ly Md Ql Ra Uh) Mj(Ax Ko Mr Mz Nf Nr Ny Pe Ra) Dg(An Fr JP Lv Ma Ou) Mf(jD jO jP Kj Rc rZ Uu) Mx(Bo In It Kr IL IM Mb) Ko(Ji Lh Lv Ml Ou Qd Ql) Ax(Ji Mh Ml Oa Qa Qd) Id(Gp Ly Ml Qd Ql) aM(An Bo cF Kn) rZ(jD Jk Lu Mv) Oy(Bg Dk Ef) An(jI Ly) Ml(Ke Ld) cF(Ct Lz) dl(Ed Rg) IL(aD Bc) GpRc QzcJ KjVs KkcZ KlOu aPdH} Ma{mE(aA aC Ad Aj Al Ap Bb Bc Co Cv Cw Dg Dl Ef Fb Gn Iz Jj Jk Jo Jt Kj Kl Mm Nm Of Qz Rc Rx Ue Ug Wb Yj Zw) jB(aL aO As Ax bU cM Co Ez Ii Jj Jk Jm Jo Jq Js Kc Kk Kz Ld Mw Nf Ns Nx Oa Of Og Qb Qh Qm Qz Vq Vu) nJ(Ad Ap Bb Cw Dg Ef Fb fP Gd Hb Hl Iz Kl Ks Pj Rv Rz Sh Si Uw Ux Vw Wb Yg Zq) kI(Al Ar Ax Bb Du Ef Fa Gd Jt Nm Of Pc Pj Rx Ry Si Ue Va Vt Vw Vz Yg Yl Zq Zw) kE(Al Ax dG Du Fa Gn Kz Li Pc Ry Uw Va Vz We Yg Zq Zw Tm Tl) mH(Dg Dl Gd Gh Gn Rx Sh Va Wb Yd Yg Yj Zw) oQ(Aa Ad aF bI Dc Dd Fr Gd Hb Li Nn Pj Rf) fB(aF bI cQ Il Ny Of Qb Rf Vt) nN(Gd Jj Jk Jo Jt Nn Of Rx Va) nA(DG fR Gh Rx Vw Wb Yg Zq) mS(Ax Gc Ue Uw Va Vw Zq Th) kP(Bb Jj Mm Nm Nn Ny Rc Yg) pK(bU Ju Qt Qv Qw Ri Ue) mF(Gd Gh Ry Rz Wb Yg) mP(Jj Jo Of Sh Wb Yg) mU(Fr Jj Jk Jo Jt Of) nK(Bb Bc Ef Fb Kl Rx) mT(Cv Hl Rv Rx Yj) gZ(Jv Li Nn Rf) pH(Ar To Uf Vv) mM(Jj Jo Of) Rx(lW mI) Uy(lX mY) Va(lX nO) Vo(dU pI) fR(aA Jj) lY(Gh Mj) rZ(jF jY) ArpI BbnL EfeQ YgnT YhoF YjmI SiaZ JfdX QzgC JtnM KlnH PseM KzoP LddU OueP} cU{Yg(aK aM aO aU aV bA bS cB cT cX cY dA Dc dJ Dk Ed Hc Ho Hv Iv Jl Jq Jr Js lX mE mF mH mI Mz Na Nb nC nK nN Nv Nw Ny Oh Ok On Ou Pg Pi Um Vi Vv Xa) Si(Ao aZ bR bS cI cM dH Ed Fw Gc Hc Ho Jf Jl Jr Lx mE mH Mp Nb Nq Nw Oh On Or Ou Ow Pg Pi Ps Qd Uh Um Up Vc Vu Yk) gV(Ad Ar aZ bA bF BO bZ cE cH cL cM cO Cp Cs cT Cw Dc Dd dH Di) eP(Ao Aw De Ef Ex Jg Jk Ko Ld Mv Ns Nv Nw Ok Om On Vs) mE(Aa cI cM fP Gn Ib Ju Lh Mm Mn Nm Nn To Uw Vb Yj Zq) Zq(bA cB dF dI kE lX lY mF mI mU nK nN) pK(aR bC bP bU cM Em Ju mS Mw Ny) Gd(De Gp Hc Jf nH Pi Um Yj) fR(Ji Jj Jr Lx Nw On Pi Qd) lY(cF cI fP Gn Lh Mn Pb Uw) Ow(Ho Ps Sh Vc Vi Yk Yf) Ny(Ps Sh Vc Vi Yk Yf) Uw(Ed Hc mF mH mI Pg) nJ(Hl Lh Lt Vi Wh Xa) Uy(Hq Iv Jr mH Qd) Mm(Gc Ho lX Wc) Sh(Gp Hc Kn Um) Ju(dU fB lX pI) mH(Aa Gn Vb Yj) nK(Al cI Em Lh) Hl(kN nC oP) Ho(Ib Oh Om) Yk(Bb Ib Oh) Pc(eQ fB pI) Aa(dH mI) Gc(dX Pj) Gn(mF nH) Ns(dU oE) Yj(mF mI) Sf(Gp oP) Rx(cT dI) cM(kK pI) eD(bW dI) fB(Hc Oz) nT(bM Pb) GhcB NugC LxdX MejV QdcF JjmZ JvpI VbnC fPnA} kN{Hl(aK aM Ao aQ aU aV aW bC bZ cM CO cS cY Db De dR Ef Ez Fc Fi Gc Hc Ho Hq iO Jd Jh Ji Jn Jr Kc Kd Kg Kr Ld Lh Lv MF Mg mH Mi Mk Mp Mu Mv My Nb Ni Nj Nn Nq Nv Nw Oh Om Ou Ow Pf Pg Qd Qu Qz Rx Uc Uf Vq Vu Wh Tj) aU(Ad Al Ap Bb Bc Cv Dd Dg Dl Gh Ii Jj Jo Jr Jt Kf Kl Mm Nk Nm Nn Ns Oi Ou Ux Vo Wb Yh) Rx(aF aK aO aQ bF cL cT Dc dF Hq Jq Lh mH Mp Nw Oh Om Ou Ow Qn Yh Yk) Ke(Ad Gd Jj Jo Jt Li Mm Nm Nn Pj Uw Zq) pH(Fb Lj Mm Mw Nn Ny Oz Pb Pc Qh Rf Uh) aQ(Fd Gh Rt Ry Rz Uw Ux Vb Wb Yg) Zq(aZ Gp Ji Jq Lh Nw Oh Ou Ow) Wb(Ao Co cY Hq Ld Om Ou) Uf(Ad Dg Jo Jt Nm Rz Vb) Al(Fw Jr Lx Ou Pg) Gd(cL Kg Ld Mp Ow) Nq(lY Mm Nm Nn Pc) Hq(Rt Ry Sh Wf Ye) Uw(Ji Lh Nw Ou Ow) Uy(cL Mg Mp Oh Ow) Ld(Du Nm Ry Yg) Ux(Ao Ji Om Ou) mH(Fc Rz Sh Wd) Gp(Ry Sh Th) Jo(cL Kg Kj) Rt(aK cL cY) Ur(Ou Pi Wh) Vb(Ba Kg Wd) dR(Gh Ry Yg) Ad(bZ Qd) Fw(Jt Nm) Gn(Hv kP) Mp(Jt Ue) Wf(Jd Nb) Jj(dA Kg) Rz(Up Vw) Ow(Du Zw) aF(Cx oD) fA(Mm Nn) EfQd GhcY MgVw ToOu LtoP RfOh VocL} Ld{eP(aA aC Af aP Ax aZ bO cG Cp Cq Cs cT Dc Dd Dk dM Ed Fp Ha Hb Hq Hv Hw Ij Il In Ip Iq Ir It Iv Jf Jk Jl Jp Js Jt Ke Kr Ks Ky Li Lj Me Mj Mn Mp Mt Mv My Mz Nj No Nq Ny Oa oF Oh Ok On Ou Ow Pa Pd Pf Pg Ph Pi Qa Qb Qc Qd Qe Qh Qm Qu Rb Rm Sr St Ua Uc Uf Uh Us Vp Vs Vu Vv Tj) dU(Ad aF Ap Ar aZ Bb Bc bG bI cD Co cQ CS Cw Dg Dl Ef Fa Fb Fn FP Fr Ha Ii Io Ip Jg Jk Jo Jq Jt Ju Jv Kl kS Ky Kz Lh Li Lj lY Mf MM Mw Mz Nm Nn Nv Ny Oe Of Og Oh Oi Om On Pc Pk Tj) jB(aD aO bF bU Cv cY dE Gp Hc Hr Ii Jf Jv mM Mq Mw Of oH Oi) eQ(Al aU Bb Fa Ha Hb Ip Iz Jk Jv Ko Mb Mh Mq Nm Nv Pc tF) pI(aF Bb Fr Ju Jv Li Mm Mw Nn Pc Pk) gZ(aU Jk Jm Jv Jy Mh Nv Oz Pc tF) kE(Du Gn Hl Rx Ry Si Vz Wb Yg) Yl(hC Hv kS Nf Or Ou) Yg(kI kQ mZ oF) Ry(mZ nD oF tF) Rx(aZ lW mS nN) Si(aZ nA) gC(Li Mm) mZ(Mb Yk) oF(fR Gd) pK(aU Jv) DmN DunD GhmH GckK YjRc WbkI QdeM WfpF VitF} On{Yj(Aa Ad Ap Bb Bc Gd Hb Ib Iz Jg Jt Lh Mh Mm Ng nJ Nn Ny Oh Oi Ok Om Ow Pj Rc Rx Sh Si Sr Uu Zq) Ry(Aa Ad bH bO cB cF Hb Hv Ii Jo Ju Jv Ko Ks Lh Mm Nn Oh Om Ow Pj Sf Sh Si Um Vh) eP(Ad Al Ap Aw Ax bO cI Cv Dg Dl Ii Io Iu Jo Jt Mm Nl Nm Nn Ny Of Oh Pz Rm) Yg(aD aK aO aS aV aZ bG bI bO cB cC cF cZ dC dJ dM eM fB Hv kO nL oF Uo) Vh(Hb Ib Ih Ii Jl Ks Lh nJ Ny Oh Ow Rc Si) Hl(Ad Ib Ks Mh mP Mz Nn Ny Ok Rc) Ks(Dr dX Gn Uz Vi Wf Wg Yl Tl) Ad(Gn Ho mP Rx Si Va Yl Zq) Ii(Dr Uz Vi Wg Yl Tl Yf) Vb(mI mP nC nK nL nN nT) Gd(mP mT nH nK nL nN) Rx(Jo lW mE mT nJ Oy) Vw(mP mT nC nK nN nT) Rc(Du Gn Uz Vi Wg) Zq(aZ Jo kI mI mT) Ux(nC nH nL nN nT) Wf(Ib nH Ny Ow) Yl(Jo Jt Mh Sh) Uw(eM kI kO nB) Wb(nC nH nL) Si(aZ Rj Um) Nn(fA pH) Mz(Sh Tl) Sf(kI mH) Wg(Ib Jm) Jt(mP nN) Rt(mZ nJ) Of(mP nN) Va(kC mH) eQ(Hb Qh) fR(Jj Jo) AaZw CxdX DuMh MmoD ShnH JudU NypK OpoP OujV} Jr{Yg(aO aX bC bE cC cF cG cL cS cZ De dH dJ dK Hv kP kR mP mT nK nL nN oF) Va(An As Cq Cv Dc Dr Du Hl Ib Id Kd Kn kP Lw Ry Ud Um Uo Uz Wg Yl Xa) Rx(An Du Gn Gp Ha Hl Id Ii Iu Jo Kd Kn Ko Nm Ns Oy Qg Yj Yl) Uy(bO Cq Gp Gz Hb Ib Ju mP mT nK nL nN nT Si Uo Yj) Du(Aa Hb Ib Ii mP nH nK nL NN nT oF Op Rc) Yj(dJ Hb Ib Iv Jv Lh Nn Oh Ow Qv Rc Sh Sr Zq) Hl(Hb Ib Ii mP Mz Nn nT oF Ow Rc Ry Si) Ry(Hb Ii Ju Jv mP nH nL NN Sf Um) Yl(dL Ib Ii Ju nA Nn oF Rc Sh Ug) Hb(Dr Rt Uz Vh Vi Wf Wg Tl Xa) Si(Cv Gp Ha Qy Rj Uf Vu Wf) Sf(Gp mP mT nJ nK nL nN) Uw(kP mP mT nK nL nN) Ib(Uz Vj Wc Wf Wg) Zq(dF nC nK nO Uo) Ux(mP mT nK nL nN) Gn(mP nH nL nO) Ii(Em Fc Tl Yf) Sh(Gp Hc nL oP) Zw(mP nK Vu) Wg(cV Jm Rc) Wf(nC nH Ow) Vb(mP nK nN) Al(kE mP) Em(Mz Nn) Ny(nN Uz) aU(lX nO) cS(dU mE) nJ(Fc Vh) GdGp NnRz MxlL HoJm IdjI YkmZ WbnL RcUz JjfR YenH PsnN LhdX} pH{To(Al AR Ax bX bZ cF cI cJ cP CS Cv cW Di dN eF Ez Fw gZ Hc iH Ik It Jj Jm Ju Jv kC Kd Kn Kx Lh Lx Lz mE Mg Mh Ml Mr Na nD nJ Nn oE oF Oh oK Om oN Ow Pd Pe Po Qt Qx Ra Rf Rh Ri Uf Ul Ur Wm) Vv(aG Cp Fb fP Gl Hw Ib Jk Jl Jm Jq Ke Kn Ks Lh Mm Mn nJ Nw Om Ow Pc Qh) Pc(Al cM Fa Gp Ha Hf Jm Jv kC Ly Nb Qb Qg Qu Rb Uf Up Us Vs tF) Nn(aR Ba bC cF cS Em Ez Fw Hc kC Mg Na Nb nD Nt oN Pd Qu Uf) Lj(Kx Mh Nb Nr Qt Qu Qx Ra Rf Rh Ri Wm) Ny(bV cF Ct Di Em Hc kC Mx Na Nb Ok Pk) Uf(Bb cM Fb fP Ib Io Kn Lh Mn Om Ow) cF(aF Al Fb Ky Mm Mw Nm Rb Sr Uh Vt) Pb(Jf Jj Qv Qx Ra Rf Rh Ub Ur Wm) Hc(Jq Jv Mm Nm Of Qc Qe Rm Vt) Qu(cM Fb fP Hb Ib Mm Oz) Ax(bZ Mh Qx Ra Wm) Cs(Qx Ra Rf Rh Wm) Fp(Qt Qx Ra Rf Rh) Em(aF Mz Nm) Vt(cA oN Ri) Al(Jn Ri) Mm(Ao Na) Oz(Jf Jv) iO(Uk Up) FbNq MgUh MwkC NbJm HqJk QbKx aFcV} Vv{Va(aZ cI fR Gh Hc Hv kC kI kP Md Mf mH Mk mS Oi Or Ou Qx Rc Um Uy) pI(Ad aO Dc Ii Io Jo Jt Ju mF Mm Oa Oh Ph Pz Qh Uu) Rc(Gh Gn Hl kP mU nN oQ Uy Vi Vj Vz Yj Yl) Si(Ed Ji Ke Li Nq Ou Ow Qa Qd Ql Vj) kI(Al eC Gd Hb Hl Rx Uw Ux Uy Vb Yg) nN(Dl Jj Jo Jt Kj Oi Ss Ug Vb Vo) oE(Ad Ap Ax Dg Dl Jo Jt Ns Ok) Jj(kP mM mP mT mU nT oP oQ) Rx(aZ Jo kE kK kO mY nO Ns) mU(Jo Jt Mm Nm Ss Ug Uu) kP(Bb Jo Mm Nm Rz Wb Yg) oD(bF Iz Kn Nv Ny Of Uu) Rt(Id lW mF mH mZ oF) Vb(kC mF mP mT nL oF) pK(dN Io Jf Ju Kx Ur) Ug(mP nO nT oP oQ) Vj(Hb Ke Ny Oh Ow) fB(bO bQ Gp Qv) mP(Jo Jt Kj Ss) kE(Hl Uw Uy Yg) oP(Ii Jq Mm Nm) Sh(Gp mH Ry) eQ(Dc Uu Vo) mT(Gd Jo Kj) oQ(Ii Mm Nm) oF(Gh Uw Yg) Ry(Nb Um) dU(cS iO) nT(Jo Vo) jB(Fb Ii) HbJi YglW WfmH JpdX OpOu UreP} nH{Vi(aU bX cH Fb fR Hf Hl In Je Lz mE mF nA Nu Oh Oi Or Qu Qw Qx Up Vb Wf Ye) Gn(aF aO aZ dD dH hC Hv Lh Mj oF Oi Or Pg Qd Qe Qh Rg Rv Uc Up Vp Vu) Uw(aU bS Dg Gd Gp Ib Ij In Ji Jp Jq kI Lh mF nA Nw Op Vb Ye) Rt(bB Ez kE kI Lh Lv Lx Lz Mh Mk Ml Om Ow Pf Qx) Hl(aO bF Hc Il In Jf Jl Mj Nr oF oN Pg Rg) Ye(aO Hc Jn Mj Pg Qa Qd Qt Rm Vu Wh) Op(aF Qv Rc Ug Ur Uu Ux Uy Vb Vw) Wh(bB In Ji kI Lv Mh Mk Qx) Rv(Ji kI Ky Mk Po Ur Yh) Vb(aO Co dF Lh Mz Nw Ok) Gh(aQ aU cY dR hC Rg) Wf(Ao Co In Lv Nq Pg) Yh(aZ Qb Qx Rg Uh) aO(Eq Sh We Yg Yj) In(Vh Vw Wd Ti) Uy(Ji Jq Oh Pf) Gd(Jf Pg Ti) Rz(Qb Qx Rg) Ou(Sf Sh Zx) Ao(Sh Ux) Du(bB Lx) Yf(mH Oh) Wb(hC Pg) Lh(Sf Va) Ru(Oh Pf) TiMj ThbB FdPg LvWe LzWd MzUx YgJp ZxQx RxPi NwVa UofB} gV{bA(aE aG aH aL aM Ao Ap AW

Figure 40 Continued aZ Ba bB bI bL cB cC cG cH cI cK Co Cw Dc De dM Em) cT(aK aL aM Ao aS aU Aw aX aZ bB bI BO cB cC cD Cp cV Cw Dc De dX)
Dc(aK aL aM AR aU Ax aZ Ba bB bO bQ cG cH cP Cs cW cY dF) aL(AI AR AW Ax Ba bO bZ Cp cQ Cs CW Cx Dd De dI) Ba(aC Aj Al An
Ar bE BO cH Cp Cs cZ DD Dk dN) dD(Al Ao aU aX aZ bC cG Cp cS CW Dd DE dI) Cs(aK Ao aU aZ bC cB cG Cp Cq Cw cY De) Ar(aK Ao
aU aZ bB bQ cB cG Cw cY dC) Cw(aC Ad Aj Ap aZ Bc bO cM dB Dg) aZ(An aR Ax bO bV bZ cH Cp) bO(Aj Al Ax bB cB dB Dd) Ao(aC Aj
Ax bW dJ) aU(Al cH dB dJ Fr) Cp(Aj aM Ax bZ) aK(dB dI dJ Fr) bQ(Bo cO Dd) Aw(Al dJ) Ax(aX De) aC(aX cW) cG(Aj eP) DdbZ bBcH]
nC{Vh(aU Bb Dg Dl Eq Gd Hf Hl In Jj Jo Jt kI Lv Lz Mh Mk Ml Mp Nq Oi Or Ph Qb Qv Qx Rg Tv Vb) Rv(aQ aU bB Et Gn Jd Ke Mk Mp Nq
Po Ri Uh Un Yh Yj) Uw(aU Dg Ij In Ji Jq kI Lh Nw Op Ou Qv Vb Wb) Wh(Hf In kI Lv Lz Mh Mk Ml Mp Qx Uh Wb) Ti(aU Dd In Jj kE kI Mj
Mp Or Po) Gn(aO Hv Jf Pg Qa Qd Qe Qt Rg Uc) Rt(Ez Lh Li Lz Mk Ml Om Ow Po Qx) Gh(aQ aU bB oF oP Ou Pg Rg Uc) Yh(Qb Qv Qx Rg
Tv Uh Vb Vt) Wb(Ao cl Hq Jf Pg Un Vu Yj) Vb(Ao Co cS Et Ji Nw Op) Uy(lq Ji Jq Lh Mf Mg Pf) Sf(Lh Lx Oh Ou Pf) Ry(Ji Lh Lx Nw Pf)
Rz(Qb Rg Vt) Va(Ji Nw Ou) Ao(Sh Ux) Th(bB Et) Gd(Jf Pg) Mk(Ps Wc) In(Vw Wd) Qx(Eq Yd) Ru(Oh Pf) Op(Ny Rc) YfOh FcUh FdPg GcaF
MfHl MjWf YgJp YkaQ YjaU QaYe JiVw PsNw RxPi VicI} Gp{Gd(An Ar bO cA De Hx iJ In Lh Lv lW Mb mI Mj Mz Nw oF Oh oP Or Qd Qh Qv Qx Rf Sf St Uf Un Vp Vu Wb Zq) Sf(dB dE Ed Fi Fw kC kI mE MF mH mI mM Nb nJ oF Or Ou Pg) Sh(bF Ch Ed Hc Jl kI Mf mI Mv Or Ou Pg tF) mE(Eq Ho Rx Ry Rz Uw Ux Vb Vi Vw We Yh Zq) Ry(kI lW mI mU oP oQ Ou tF) mH(Rz Uw Vw Wd Yh Zw Xa Yf) Wh(Ed eM kK kO nB nK nN) nA(Dr Fd Vi Vw Yh Zw Xa) Yf(aM Bn Hv Ic oF) Fi(aZ dR hC nL oF) Ho(Jo Ko Mh Nm nN) Zq(dF Ed Fa kK) Fc(dR hC oF) Gh(mF mI oF) Yh(Fb mI nN) Wd(kO nD nJ) Rx(aZ lY oP) Yl(hC Or Ou) Vi(kO lW nJ) fB(Pc Qa Qd) Ed(Si Uy) Hl(oP oQ) Zw(mF mM) Ps(lX mI) Rt(Aa nT) Uw(lW nK) mU(Ru Uy) ThkK HbQd YjkP SiOu XakI RznN PcpK ePhG} oP{Sf(aN Ao aQ aW bB Bc bO bU bX cD cF Ch cK cM cY dA dG dJ Gh Hq Hv Id Il Jf kP Ks Lt Lx Mn Mu MY Nr Nx Oe Ok Oy Yh) Rx(An bH Ch Ct CX Ez Fy Gh Hq Jf Jq Js Mj Mx Na Ns Ok Pg Qn Yh) Gh(aF aQ aU bB cM cY dA Fn Hv Jn Ju Jv Nb Nm Nq Pg) Ho(aF Bb bO cW Gd Kp Nm Nn Ny Oe Om Ql Si Ye) Zx(Bg bU Ch cM Co Iz Mu Mv My Ou Pg) Sh(cF cM cY Hv Id Jf Pg Ph Pi) Fi(aF Mz Nm Nn Ny Pc) Gd(cG Ez Jf Kg Kj Pg) Yh(aF cX Nm Nn Ql Qn) Rz(bH Cw Kp Mz Nn Oi) Du(Ez Ow Pe Po) Pg(Op Si Yd Yg) Jf(Gc Hl Op) Eq(bH Kp) Hv(Si Ye) Jv(cF Lt) AlVu FyTo GcMg NmNt MmQd NiaF YddA VzKp JuLt RmPi} nJ{Vi(aI aK aQ As aU aV bB bO cG dA dD Hv Ij In Iq Je Jf Ji Js Ke Lh Li Lv Lx Lz Mj Ml Mp Nw Oh Or Ou Ow Pe Pg Po Qa Qb Qd Qx Rg Uh Uo Wb Yh) Rt(bZ Li Lv Lx Mk Mz Nw Ow Pe Pf Po Qa) Uw(aK aQ aU aZ bZ Ji kP Kx mH Or Rg Uh) Lx(Sj Vh Vw Wc Wd We Yg Zq) Rz(aZ bZ oF Qa Qb Qd Rg Vt) Pg(Fd Gd Gh Gn Hl Sf Yj) Wd(Ji Js Mj Oh Om Or) Wh(bB Et Ji Ky Mj Uh) bZ(Gd Rv Rx Si Ux Wb) Vw(aU Jq Mj Or Ou) Qa(Op Sj Yd Yh) We(Lv Oh Ow Pf) Rv(aO bF Ez Pi) Sh(bF Lh Om) Rx(Lh Nw Pi) Wf(Mj Nv) Ou(Va Zx) Vh(dD Pf) EqaZ GhdR GdUc HliO YgbQ YhRg YdQx VzNw SfLh WcPf JqRu OmVa OwjB UyPi VuPc} fB{Qa(aC aF Al Ax cF Cs Fp Ha Hb Hc Ih Io Jm Ju Lj Lu Oz Pb Pc Qg Rf Rm Uf Uo Vt) Lx(aF Ju Qe Qg Qu Qv Rf Ri Ss Ua Ub Uc Uf Um Uo Vt) Ez(aF bI cQ cX Fa Il Nm Of Qc Rh Rx Up Uu Vq Vu) Rz(bW cM Fb Ib Lh Li Mm Mn Nn Om Ow Qm Yg) Qt(aF aO bA cT CX Mz Nw Pd Qn) Yg(Ba bQ Ch Ct Hc Hq Lh Nv Om) bZ(aF bI cQ Il Ny Of Qb Uo) Yh(Ax cM cQ Gd Ib Nm Ny) aO(Hc Ju Jv Kc Qu Rx Uf) dD(Qx Ra Rf Rh Ri Wm) aF(cS gL Mk Nt Ow) Hq(Gd Gh Zx) Qu(cT Oh Ow) Ju(oF oN Pg) Pc(bQ Uc Vu) cM(Eq Gn Sj) Jv(oF Ua) Pi(Ry Si) GdMg UckC LhOp RimP RfOh NwVt OwUp VuPd} kE{Hl(Ao aU bC bZ cL Co Ef Ez Ho Hq iH iJ iO Mu Nn Nq Om Ow Ph Qu) Rz(aF aK Ap aU bW hC mT Nn Oz Pb Pc Ss Ux) Pi(Al aU Fd Gn Nn Rx Ry Ur Uw Uy Va Zq) Zq(aO cT dF Ez Jq Mz Nw Ok Om Sj) Gn(aQ cL cY Ez Hq Hv Kg Pb Yh) aU(Cv Fy Gh Jv Lu Mm Nm Ns Yh) bF(Fc Ho Ju Sf Sh Wd Wh Yg Yk) Ez(Rx Ry Uw Ux Uy We Yg) Hq(Rx Sf Yg Zx Ye Ti) Uf(Jo Jt Pj Uw Ux Vw) Yh(aK cY Qv Ri Rx) Pb(Fy Ho Uw Wd Ye) aF(bC Fi Ho mP Wd) Rx(bQ cL cT Jq) Om(Uw Ux Uy We) Pc(Eq Mu Nq Wd) aQ(Du Uw Yg) Uy(bC cL) aK(Rv Yl) bQ(Uw Yg) bZ(Du Tl) cY(Fy Gh) lY(Mu Nn) AlVu YfMg WcRi WhQg VicL} Yl{Or(Ao aU bC bF cF cL CO cS De dK dR Ef Ez Hb Hc Ho Hq Jh Ju Kc Kg Kj Li Mg Mi Mp Mq Mt Mu Mv Na Nb Nn Nq Nv Nw Om Ow Pd Qy Rz Sf Uf Va Wd) Ou(Ad aM Ap aZ Bb bG bO cE Dg Gd Hb hC Ii Iv Jj Jo Ju Jv Ks Lh Mh Mm Mz Nb Nm Nn Ny Om Op Ow Sf Sh Si Sr Tr Ue Va Vo) Nw(Aa gP Hb Ib Ii Jt Jv Ke Li Lj Lu Mz Nn oF Oh Oi Ow Pj Rc Rf Rx Si Va) Lx(aF Ax cA cF cK De eM Hb hC Hv Jv Lj Lu Mz Nn No Ow Qn) Nv(Jo Mh Rc) Ow(hC Li Lu) Gd(De Hc) Hv(Mh Oh) aF(mT nL) hC(Mp Nq) kI(bQ Pi) LuOh NhQd ZqdF aUlX} lL{Id(aM aR bC Bo bS bV Ct Dg dI dJ dN Ed Jf Ji Jo Lh lM Lv Ly Lz Me Ml Ni Nw Or Ou Ph Qb Qc Qd Qe Ql Rc Um Un Up Vt Th) Mx(Ax eD Hr Hv Hw Hx Ib Ij In It Je Jf Jh Jn Jo Js lO Me Mr Na Nf Ny Om Pb Pd Pe Qa Ra Rj Um) eD(aE aM bR bW cF cG dH dI Fr hR jD lM Mj Mm Mu Mv Mw Nn Nq Oh Qy) Bc(An aW bS cH dI Jf Ky Me Nf Ni Ra Um) Ez(aI Fr Ky Mf Nq Ou) aW(Je Jf Kd Ly Me Ra) Ky(An Bb Ko Li Ok) Ax(aD bC Ly Me) Je(An bS dI dJ) Bb(Jf Me Um) hR(bC cF cH) An(jK Ni) aX(cB Jf) jV(Bo rZ) CtjK DlcH MeHf MfJv UmdJ} eP{Uf(Ad Aj aO Ap aR Aw Ax bA bI Cv Dg Dl Dp Ed Ha Hq Ii Iz Jj Jp Jt Kf Kj Kl kR Mm Nm Ns Ou Ph Qz Vo) Ex(aU bW cC Ez Kc Kd Kg Kj Mi Qy) Fy(Ji Lh Or Qa Qb Qc Qd Qe) Jf(cG hB Ir Jj Lv oE oF Rm) Om(Iz Kj Kn Qv Qz Ue Ug Uu) bV(dR Ke Mi Mp Mt Ow Uh) Ef(bO Iz Jj oF Ug Uu) cT(cS Mi Mp Mt Ow Pj) Mv(hB oF Qw Ug) Ur(Jk Nt Ok Ua) Lx(Fa nW oN) Kj(aO Jj Jp) Vq(Aw eM Ns) bA(Aw De Jd) cG(Ar cE dH) oF(Di Kg Na) Ao(aA Uh) Dr(dR Fw) Ke(aO bQ) Ky(Um Uo) Oh(dG dH) hB(Kg Pi) AxPe CoUg WmMg FaIr NaKk NgUh NkKx TtOu JdQw JpQm KcOk UnbF} kI{Uf(Aa Em Ii Jt Li Mm Nm Of Pc Pj Pz Si Ue Uw Ux Vb Wb Yg) Yh(bO Ju Nm Qg Qv Ri Rt Ug Um Uu Uw Ux Uy Va Vb) Rz(aF Ap Bb hC Iz Jv Nm Nn Pc Ss Ux) Pi(Ju Jv Nm Nn Qb Rx Ug Ur Uw Uy Va) Sf(bF bZ cF Ct Hc Hq Mz Pc Pg Ph) Zq(aO bA cT dF Ez Fy Js Oh Ok Ow) Uw(bQ Ez Fy Ib Js Mn Mz nL Ok) Ez(Ax Rx Ue Ux Uy Va Yg) bF(Ju Jv Rx Sh Yk) Al(Qa Tr Uc Vu) Pc(Eq Fi Qu Vu) aF(cS mP Ni Wh) Jv(aU Aw tF) bZ(Du Si Yg) nL(Rv Vi Wh) Ct(Sh Vb) Uy(bC Fy) bQ(Ju Ry) EmQu MgUx HohC HqZx HcVa RxcT VbVw ViPb} mH{Sf(bB bZ Ez Fy Ij Js Lx Nn oF oN Ow Pe Pf Qa) Sh(bB bZ cS Ez gL Hc Ij Mg Nn Pf Qa Qt Rz Uf) Uy(cL Ez Hv Ji Mp Pi Po Qa Qd Qe Uf Uw Yh) Rx(cT Ez Fy Js Lx Oh oN Ow Pe Pf) Va(bZ Ij Ji Js Oh Pf Qa Yh) Ez(Gd Rt Wd Yg Yj Zw Ye) Ps(bO cS Ib nK Nn Ow) Rz(hC Jj Oy Rj Uo Ux) Uw(Ib Ij Js Nn Pf Qa) Vb(cS Ij nK Nn Pe Vw) Yg(bZ Ow Pe Pf Qa) Gh(bZ Lx Ow Pe) Zq(bQ Js Lx Oh) Yj(Nn Ow Pe) Rt(bZ Ow Yh) Du(Ow Po) Mg(Ux Ye) Zw(bZ Lx) Zx(Nn Pf) Qa(Hl Ye) Ry(bZ oN) Vi(Ib nT) PoRu GdUf IjUx YhUr WhRj OpPf} pK{Ju(aQ aU bZ dK Et Fw Ji Js Kx Lx nO oF Oh oK oN Ow Pc Ph Qa Uf) Qw(aP bZ cS Ez Li Mg Mv Nn Ow Pe Qt Uf) Jv(aK aQ aU AW cF dK Et nO Pc Pz Uf) Ow(bX cC cD Jm Ny Qh Qz Rf Ri Rm Ue) Pc(bU Kz Qt Qu Uc Uf Vq Vu) bZ(bU cD Qz Rf Ri Rm Ue Uv) Kx(cC Ny Qd Qz Rf Ri To) Uf(Ad bH Ib Jj Mw Ue) Ur(Ao Hc Kg Mg nO) bC(Jf oF Qx Wm) cD(cT Ez Lx oN) Oh(Jm Qh Rf) Pi(Rj Up Vp) nO(Al eC Jj) Ez(Qz Ue) Qa(Ha Jm) Ny(Lx oN) bH(aR mP) cS(aN cX) dA(Qx Wm) dN(cX Hc) kC(Qd Uc) AlRm AxPe BbKe EmcC FbNq JfcZ RfoF} nL{Rv(aO bB bF bZ Co cS Fy Jd Jl Ky Lh Lx Mk Mt Mz Nq Nw Oh Ok Ou Ow Pg Pi Po Vi) Gn(aF aO Mj Oi Or Pg Qa Qd Qe Rg Uc Vp) Mj(Hl Ry Sf Uw Ux Uy Vb Vw We Wf Ti) Vi(Fb Fc Je mE Up Ux Vb) aO(Eq Hl Rt Sj Uy Vb Yg) Hl(Jl nW oE oF oN) Lv(Gh Rt Wh Th) In(Sf Vh Wc Wh) Lh(Ry Sf Uw Va) Uy(Jq Or Ou Pf) Pg(Fd Gd Wb Ye) Sh(Ao Nq Ou) Vb(dF Mz Ok) Pf(Ru Ry Sf) hC(Gh Vz Wb) Yg(dF Jp) Wh(bB Oi) Rt(Mk Ok) Rg(Vh Yh) Uw(Jp Qv) YfOh EtZq FdHq GhoF GcaF GdHc NqSf MzUx YdQx WbgL ZxOu RydR OpUp OiVh} lX{aU(Aa Ad Ao Ap Bb Cv Cw Dd Dg Dl Dp eC Gd Hb hC Ii Io Iz Jj Jo Jt Ju Jv Kf Kl Kn Ks Lu Mb Mm Ng Nk Nm Nn Ns Ny Oc Of Oi Ok Oy Pc Pe Pi Pj Pz Qd Rc Rj Rt Rx Sf Sh Ue Ug Uk Um Uo Ur Uu Vb Vo) aQ(Gd Ju Rt Rx Sf Sh Si Ug Uw Vb Wc Yg Ye) cY(Gd Gh Gn Jj Rt Rx Sf Sh Uy Va Vb Wb Yg) dR(Gh Rx Ry Sf Sh Yg Yj Zx Ye) aK(Rt Rx Sf Uy Va Yj) Ug(Eq Rz Yh) Uy(aV cL Nw) Va(bF cL Ou) bF(Rt Rv) bZ(Gh Ux) AxLx GnHv RxoN VbbQ} eD{Uv(Fp Fy Ha Hr Hw Ih In Ir It jG Ji Jo Js JT Li Lj Mf Mq Mr Mu Mx Nf Nj Nm Nn No Nr Nt Nu Nw Nx Oa Ok Pg Qx Rm Tv Uc Um Up Us Vt) Lj(aA jI jO Md Oa Pc Qe

Figure 40 Continued

Figure 40 Continued nA Oi Oy Ug Vu) Oy(Fd Ho Sf Va Wd) Ed(Sf Si) Gd(De Sf) kK(Of Va) YhRc SiQd YemU PsVo VbmM aUnT} Gn{mU(bO cD Jf Rg Uc Up Vp) Pg(mI nA nD nT) mY(Mj Or Qd) Vu(kK kO) nA(Qd Rg) nD(cL Hv) RcOk JfoQ JvmI VpnT aFkP} Yh{Qv(mU mY Ns nT) Va(kC mI nA) mS(Ri Ug Um) bO(mY nA) IW(Tv Vb) nD(aU Ug) AaaA EdIb HaHv NmoQ RtmI OiaJ UmmY UrnO} Ow{gC(Ny Qe Qh Qw Qz Sr) gZ(Ju Jv Li Nn Sr) Vz(Gd Hv Lu) Ry(hC tF) DeGd DucB GhkR UaSi OrVw} Lx{Ho(Ax Ii Jm Nm) Hb(Dr Em Ru) kC(Nn No Zw) Gh(kR nA) nB(Sf Sh) AlgZ DeGd DumY NsZq LuRy LjfR} mI{bZ(Gd Ps Rz Sh Si Vw Wb We Xa) Nn(Ux Vb Ye) Hq(Gd Sh) Ye(Mg Mv) Rz(Bb Jj) RvRi VbVw} mS{Rz(aF Ap hC Ss) Zq(aO bQ bZ) Va(Ez Jq Pi) bF(Ju Sh Wf) Hq(Sf Zx) Uf(Aa Jt) EzUx HohC VuPc} Qa{Al(gC kO mU nA oQ) Um(Ax Hb Li Lj) Si(kP nA Yk) gC(Ha Oa) FakK NsnT MmkP HbYk LjpI} nT{dA(Lz Mh Oh Pc Rf Rh Wm) aO(Dp Rt Um Ur) Rv(bF Ri) aU(kR Qu) GhcY JjOk VbbF} Ry{Nv(Ed Nb Oa Xa) mU(aO bF dR Mz) Hq(Ex hC) Hv(cT Oh) nD(aQ Mz) GdMv bZkP dAoQ} jV{Bo(aM Dl Ki Ky lM Ly Or) Ly(An Dl Kj Or) Ky(Ko Kr) AxMh LurC MfRi OmOr} Zq{dF(cE dN Ed Gh Mh nD Oy) aO(Ed Oh) mM(aH Mj) kK(bB Pf) JnnA PgnD bQmY} pI{Pc(Aw Gl Ju Kc Qt) aO(Ju Jv Kc Nb) Jv(Aw bF) cT(Io Kc) JuPg LjaR NyaU} nA{Ez(Dg Gd Rt Rz Ux Vw Wb) Gh(bZ dR) BbUf JfXa PsbO NvVa VbVw} kK{Hq(Rt Ru Va) Vb(cS Nn Pf) eC(Qd To) ThbB GhdR MkRt YkaK JqVa UxPf} oQ{bZ(Gd Ju Jv Sf Sh Um) Du(aU cY Jf) bQ(Ju Jv) NmNt SfPf RhcL} Si{Vu(Ex Jq Js Ke Lh) Ua(Lz Mh) Ji(Um Uo) Pg(kP lW) AoEd} gZ{Al(bV Fw Ph) Jv(aW bU) EzLi FrUf MwQu UeiO UrPb PctF aUcB} Oh{Ax(Ho kP tF) Du(Hv nD) Lj(Ra Um) DeGd FiRf GhkR HvVz} gC{Qz(bZ Ez Pd) Qw(cS iO) bF(Ny Pc) FacT MmOk JfcZ JviO} mU{Ye(hC Qt Qz) Ti(aF cM) DubB GdPg NsMb WebF RvRi OkVb} Sh{Pg(Aa iJ kC mM Mz) Hq(mM nD) GhoN NqbH UfiJ} bO{jG(Bc Iu Je Ky Oi Ra Rj) mY(Wd Wh)} nO{Pf(Al Ax dA Gd) AlLv ChJj LzdA RvRi aUkR} nD{Hq(Ps Ye) Pg(Fd Wb) aU(Ps Zw) bF(Rv Wh) BaVb} Mh{Du(De Ef Hv) Ax(jI jT) DeWb EqHv WcbF} Hb{Qd(aO Hr Ns Um) Ji(Um Uz Wg) KyqW} mM{Hq(Rt Vb Ye) CoVb YkdR YeaU} Rz{mY(aF Bb Ux) IzkC JjkP} Li{Or(qV qW) IvJi KyqV rCjD} Gh{dR(kP lW) aMkR aUnW} Ly{AxjT KyjF VqhR aWjP} aA{Aa(Vj Yd) Lv(fR Iv)} lM{Mx(Bo Um) ThUr KyOz} Yf{Ii(Jq Pg) JqVa} Jv{Bo(jI jP) NqYk} Vq{hR(jO Oz Qt)} kO{YeVu RvRi RtNv} kP{Pc(Pf Vu) YkaQ} Gd{DePf MpVz} Mj{WfkC JjfR} Sf{EdbF HqmY} Qd{AxcB LubH} Um{jO(Ap Dg)} lW{LzdA PsOm} nB{AoUx EqUp} jI{BcMd KoaO} AnKyjG DuPohC MxLjrY IbSjJp RcWgOk OraWqW VbVwkC

Constrained panels with 3 analytes, where 1.0E-9 >= 'AUC p-value' > 1.0E-10. Contains 5,926 panels of 23,517,221 total panels evaluated. :

oO{Ju(aF Ar aY aZ Ba cG Ch cW cY Dg dK Et Ez Gp iP mU Mx Nd Nq Ny Ok oP Pc Qt Rz) Qv(aJ aP cS dG Ex Ez Ky mU Nj nN nO Nv oE oF oQ Pc pF Qe) Ld(aP Aw bQ cL CU CV cY Hw Is Kq Mz nA Pa Qa Qu) bV(Aa Ax Bo cU cW Ez kE Lz Mj mP oQ Pf Pg pH Vu) Jv(aF aV Dc Dg Kj Lx Ma mU Nj nO On Op Qa) oQ(aY cT hC Is Jj Jl Kd Kx nN Nu Of Pi Rf) cF(Cv cX DD Lz Ml Nr oP Ow Pf Qt Wm) oE(Bo bP cL dF Di dU Iv kN Mm Nm Ny Rh) Mh(aL aQ aY bF cE cG cU dG mP Mu Rz) Mj(aA aX Bo dN Fy Jj Ml Oc Pe Sf Ug) Nb(aZ CS fR hC Jl Kd Kx mP nN Ug) aJ(Ax aZ Bo Dd Mb Mz No Rf Um Vv Zw) cT(aY bR bZ cS cU dG gL hB Hc hG Lp) oF(aX bC cU hC Ib Iv Je Jo Lj Nh Pc) Ez(aQ aV aY aZ cX Db dI Hb Ib nO) bQ(Cv Dp Jg Lv Lz Mm Nu Oy Qa Um) Nn(aC cV Iu Jt Li Lu Oy Qn Sf) Hr(aO cS Cu dF Hc Kq Lx Mt Yi) aF(cU dN Is iZ mF Mr Mt Um Zw) dG(aL dD fR Gd nI Og Rf Rg Ue) kG(Aa Bo Dd Dk dM Ma Mp Mt Mv) Qa(aC aL aO aQ cL eF mP Vo) aA(Dd eF kF mZ nN On oP Tr) aP(aQ bW Jj Lu Ms Qd Ue Ur) fR(Ap cP kE kK Mm nO Oh Pi) nR(Gb Jo kF My Nd Ni nN Nu) Sf(bB Fw Il Mt Ou Rz Yd) Rf(aH aI bC cN cY Mu nU) Ut(Ad dL Jd mP mU Nc Oy) aU(Ax Kq Lz Mr Pf Rg Yl) cS(Jo Pj Qg Qn Qy Tv Uc) cU(Al eC Is Iv Jj Qd Ug) dF(aR Cp Jo kE Mw Sh Vo) Dd(kF Mz Nq oN Pf Ph) Fy(Ks mP Nj nU Op Qy) Um(Ex Lx Mp Mt Nj Or) bZ(Ch Iz lW Nx Of Om) hC(bJ dK gL Hc hG Pe) Aw(dD Hu Nc Nd Oy) Ax(aO aV bF Is Pe) Cs(aL Jl Lv mZ nA) Kq(Fb hG Hw Mn mU) Kx(bF Jl kF Nm Vv) Rh(bC cX eF kQ Mu) mP(fB Mb Pc Yl Zw) Al(Mz Oh Pi Tt) Lx(dL Ml mU Mx) Lz(aO aZ bF Yj) Hc(Mb nO Qw Ug) Ur(Ad Co hB Ou) pH(dN hG Io No) Tt(Bb dL Iz) Is(Ad Dc hG) Iv(Eq Fd Sj) Jj(Ks Mt Mu) Jl(aX Ks Oh) Vv(aS Lu Mt) Pe(aO aQ aZ) cG(Jo Jr Ue) gL(kK Mp Qn) Aa(Tz Uc) Ba(Ug Ye) Cu(dI Mw) Gb(Dg Ok) Sh(Jr Yd) Qt(mZ Pa) Oa(Di Gn) Oh(cN mU) Or(kN Ml) Pc(eF Ua) Pf(Ad cL) Pi(aQ Hl) bF(dN Ib) dD(dN Nm) nO(Dk Qg) mE(eC oW) kF(dM Mw) oN(Uu Vo) CtHp ExHb NqPj LuMp LviZ ManU MeTr MqhG MraL MzaX NiaS HocW YeaQ KdeF RzkE YlbA RmVu aOlW cXoW} kG{Pb(aC aH cZ dJ hC Jj kI Ky Ly Mb Ml Mr Mx Nd Nw oE Pg Qb) Lx(aC aF Al aV dI dJ Fb Id Ih Kd lY Mn Nn No Ns nU Ny) Mb(aC Cu dE Gp Jl Ke Kg mP mU Mv Nb nN Nq nU Nv Pk) Qd(aC bF cY Hr Hu Lh Mm Mn mU Mv Mx Nm nN Nq Pk Uf) Fw(aF Al aV cL cY dA dI Fb Hw Jt mE mW nA Oi Vb) Pg(Ap bE cF Dd dI Gp Ha Ii Jo Ju Kn Lu nI Ny Pc) Is(Ad Dd fP Gp Ih Lh Li Mn Mx nU Ny Of) Ut(aK aV Cp Cv cY dA dC Ef Ha Jh Kf Nh) Uw(aO Co dA Dc Fn Hv It Mv Qh Vp Vu Yd) Pc(aZ dA Ji kI Mv Nd nR Nw Qh St Uf Vu) Ic(dJ Fn Hr kE kI Kq lW Lz Ml Ne Pf) Nq(aC Ap Bb Dg fP Ma nI Pj Tn Ul) Or(Ar Cv dE fP Fr Kd lY Mm mW Nm) Qa(aU Ha Hr Jt Lh Mn Nm Nn Ns) Kq(aQ cY dA Fa Gp Mt pI Tn Ur) Ou(Bb dE Gp Kd lY mT mW Nj Of) Vv(Aj Bc cZ fP Ks Mp Nb oP Sh) Al(Dk Hq Jl Jq Mz Pi Uc Vi) Ma(aC Bb Bc cR dA mE Mj Oz) Mx(Hr In Ne Nh nI Nn Oi Oz) Ke(cR cY dI Jv Mn Nb Nh) aF(bR dH fP Gp Jr kI Oh) Nw(Bb Fa fP Hb Kd nU) Pi(aQ aV cY eQ kE nI) dA(Hq Lz Mj Ow Pd Pf) Gb(Ex oF Un Vi Vp) Lv(aC Hu Lu Vb tF) Lh(Jl Ju Li Pj Vt) cR(Ez Jy Ky Oh Up) dE(Lz Mj Ml Pe Pf) fP(Jq Mj Nb Op Uh) Ad(Mj Mz Ok On) Ap(dU Et Mn Ps) Fd(cZ Ml Nn Om) Gp(aC eQ Mz Tz) Mm(gC Hq Jl Mp) Tn(aZ Ct Kn Lz) Wh(bB Ib Kf Nm) Jr(aK cG dU tF) Th(cG nU Pf) Ha(Jl Po Yh) Nn(nK oQ Xa) Mp(Nm Ue tF) Mv(Li Ny Oz) Nd(Aw aZ dJ) Tz(Cx Fb Mu) Ji(Hb Pj Vb) Jv(fB oP pK) Oh(dG Di Kd) Uf(Nb nI Ss) dI(Hq Ky Ow) mE(Mu Pf tF) Cu(Fr Oi) Cv(aC aL) Dg(bZ Ok) Gh(cN oF) Ho(Pa Vp) Hp(Qt Qx) Yh(bO Wb) Yd(kI Ml) Si(Jn Un) Jj(aO Ks) Ye(Om Qt) Ps(Kf Ko) Rt(Mh Qn) Up(cY mU) Ux(It Vi) aZ(Hc jB) cL(Fn Kd) dU(bV cO) nR(Mn To) nI(Ky Lu) oP(Ue Vt) AoYg BbaL DdmW DkWb EfRz FbJq GnlX NmcG MjUr HlQb IjZq YjRm JfVi JlJo JmVu XaLi JupI RvcF RgfB OfOn OiaK OwaV VbcE PaoT aUjB cXpK hCoQ} Gb{Vu(Ax bA Cs dF Hc Jn kF Ki Ld Lh Lp Lz Mh Ow Pk Qx Tn Uf Uo Yi Xa) Qd(aZ bO dI Gp Hf Kx Lx Ns Nv Oh Pa Pd Pg Ra Vj Yh Yj Yk Ti) Tz(bN bW Cu cZ Ef Fi Hq iH Im iO Jg Kg oF oK Vq Vv Wm) aZ(aW Ba bZ Ct Iz Jd mT Ps Ql Qy Qz Rx Tn Ut Ux Yh Yi) cU(bR cM Dk Gc Ho Js Li Mv Nb nL Nq Oa oP Ou Po Wb) Nd(Ao Ax Co Fi Fp Jd Jl Jp Mr Mv Mx Nn Qe Rz Tj) On(Cp Dc Ed Is Jo Kn Mp Nb Ny Om Ow Ph Rt Tv Wf) Jr(Fw Kg Lw Pd Pg Ra Rb Rt Ru Sr Vi Vq Vs Vz) Oh(bC cB cF Gp Hq Jp Mp mW Nn nR Pg Ua Uf) Lx(aD cB Hq Jh Jp Ms Ns Nt Pb Pg Wd Yj) Yi(bC cB Co Gp Hc Mq Mt Mu Mv Pd Pg Ql) Ow(Fi Gp Hq Hv Iv Jg Tn Vp Vw Yk Yl) Hc(aA Gz Hq Ji Jl Na nH Oa Pg) Jp(De Ho Im Iv Nq nU Pe Po Rx) oP(Ao aQ cR dJ Et Jn Jt Mw Po) Cu(dL dN Mh oE Qm Qy Uf Ur) Ed(dF Ji Ld Mg Mu Nn Ou Rz) Fy(dA Gp Im Kc Nn Uf Uh Vj) Is(Cq Dg Du Ho It Jg Vi Xa) Pe(Ao cB kF Ml Mp Mu Mv Yj) Gp(Hq Mp oF Po Wb Wc Yf) Mi(Ao cT Dk dM Mj Nv Or) Jl(Ap bC Gh Kg Nn Uf) Vv(Gz kI nL Om Rx Uh) Pg(Jd Jn Lz Mh Ql Uy) nU(cL Gn Mx Nv Nx oF) Nq(bH dM Jt mE Oa) Ao(Ax Mx nH oQ) Co(Fd Js nI Oa) nR(Di Jm Lz nL) mP(Gc Nb Nv Up) mU(Cw Gn Jf Mg) Fd(Jd Ld Nn) Hv(In Mh Wm) Kq(Lw Ud Wg) nH(cI Hb Yd) Fw(mT nL) Hq(cE Sh) Tn(Mk Uh) Ij(mH mW) Qa(Um Uo) Ji(Nf Ul) Js(mW Rz) Pi(kE nA) cG(Iv Jh) nN(Jf Mv) nC(cI Vh) BakI YfNw EzdI NnnJ MhUa MpJt UcnL WbLd JnkF KcOa PsUo OkmT OrUf UwkP bFnK bQnI cSmH} Nd{Ry(aO aV cT dG dL Ez Fa Fd Fi Fw Fy Ho Ji Li Lj MP Mq Mr My Nq Pf Qh Sh Ub Vi Vj Tl Xa) Yi(aF Aj aO BO dJ Dl Ez Fi Hq Jl Jo Ks Mh Mj Mz Ne Og Or Oy Qx) Yf(aM Aw cG cO De Et Ic Jh Ma Mu Mv Nb Nn Rh Ru Vu Tl) Hl(cG cS Ct dL Ez Gz It Ju Jv Ld Mp Nn Oi Ps Rt Rx Tl) Rx(aN aO cG dF Iv Jv Kz Ly Nb Ns Oy Ps Qe Qh Sh Uf) Sh(Bg cF cL cO Gn Lz Mf Nj Ua Ug Um Uy Vq) Tl(AO aP cB cF cG hC Is Iv Nb Pi Qa Vp) Ru(Ax Cs Il Kx Lj Mi Mk Nn Nw oF Pg Po Va) Uy(aZ Cu Fd Fy Jr Mx nC Nj Ps Uf Vq) Lp(AO Hf Hv Jv Mu oF Oi Ou Sf) Du(aP Cu Fy Kz Mi Nr Ou Qe Tj) Hp(Ax Et Nw Oh Ow Qh Tn Uf Wb) Wg(Cu Fy Kz Oa On Pe Pg Qa Vi) Tn(Bb Gd

Figure 40 Continued

Gh Rt Si Um Uw Vh) Si(Cu Is Ji Jr Mi Oa Oh) Vb(Cu Ez Is Kz Ld On Rz) Fi(Aj Kf Kj Tt Uo Vo) Sf(kI Mk mW Nj Pf Qb) Um(Ho Is lL Oh Qa Ue) Va(Gz Ib Lv Ps Uh Uo) nR(cF Kl Qx Ur Ux Vo) Yj(Kz Ld Oi Qv Tj) Gn(Fy Ho Oa Ut) Iv(Rt Vh Wc Wf) Kp(Rt Rz Vw Vz) Uz(Cu Ij Kd Oa) Ho(Hr Ul Uo) Yg(bQ Jr No) Qd(Ju Qv Rm) Xa(Cv Oy Uo) Lt(aM Ct Oy) Ux(Et Pg Vu) eD(Rg Uk Ul) oE(Jf Qn Vv) Bb(IL Rz) Ez(mE Wb) Fd(Cv Is) Gh(aM cG) Gd(Kc Ow) Lx(Rv Wc) Wf(Oa On) Ye(nH Nn) Yl(Nq Vu) Ou(Rt Vh) nI(cG Uf) BclL MhPs TzQv IdVi IsWc WbUg WdOy WhLd JoRz KyiC RfOh UtmW UwPe} nR{Nm(aK Aw aZ dD Di Hr Is Ky Lh Li Mb nF Nn Nt Nw Pk Qa) cF(Al aZ Bb cU Jt Jv Kl Lh Lp Mj Mn nI Oh Oi Pf) Mm(cU Hq Is Jh Ji kF kI kN Ne nI Nn No Rb) Jj(aK aU bV Ez Iv Jq Ke Mx Nw Pg Pk Ri Tt) Lh(Fw Gh Hp Lx Lz Nb nI Nw Ny Of Qa Um) Mn(cU Fw Gh Lx Ml Mx Nb Oh Qa Um Vv) Nn(Dg Jr Mb Ml Mx Ni Nw Po Rb Vi) To(Cv Dp Jr nI Nw Ou Pc Rb Ug Ut) Yi(Ad cL Dg Im Ji Jq Mq Oa Pk) Jt(aU Di Gp kF Mx nN Nw On Yh) Al(Hc Li Lz Pf Qd Rf Rh Um) Nb(Cv Ha Jk Jo nI Of Um Ur) Ad(cA Jn Nt Pk Rz Uf Xa) Bb(aK cY Fw Gh Ld Na Pk) Jo(aK cT Nl Pc Pk Yh) Uw(Ar Im Ke Li Lz Qx Ux) Vb(Ch Ct Fy Kg Kx Nt Tz) Dg(aK Ba eC Gp Ni Oh) Hp(hG Im Js Pz Qt Vv) Yg(aQ cT Gh Jn Ri Sh) Of(Hc Jq kF nI Ok Tz) Lz(cM Jv Pb Sf Sr) Ju(Ke Nw Pc Rb Ut) Lp(aF aK Gl mE Oz) Ur(nI Ns Pk Qn Vv) aU(Dd Kl Ma Pj Tr) Tz(cM Hb Ny Yl) Jr(Ha Ow Si Uv) Uy(In Js Ke Ow) Pc(Hr kI Pe Ug) nI(Hr kF Rb Ux) Fw(Dd Ii Nv) Nh(Kr Um Ut) Rc(Ok Pb Qn) Jm(bA Mb Vu) Ny(Pf Po Tn) Gh(Om oP) Gd(Ba Ow) Wb(Vv Yh) Sh(Di Jf) Qa(Li Si) DlcI EmaZ MzVi NiSs TrRb IpUm SfOh RzUf LdUu OiPk UxVv aFcE} kF{Oi(aL Cu dA dD dJ Is Ke Kf Ld Mb Mj Mx Pb Pc Qd Vi) nI(aF Ap Is Jo Ky Lu Lv Lx Mx Ou Pf Qa tF) Mb(aC aU aV cY Hu kI kP Lu Nb nN Nq Nv) Mj(Al cF cM Jo kO Lh Li Mn Uu Yg) Lz(aU cM dA Mm Nm Of Pc Qg Yi) Lv(Al Gd Hl Oz Pc Va Vb Zq) Is(Ad Dg Gd Jm Js Oz Vt Zw) Ut(aU fP fR Ha Io Kj Pb Vo) Nm(aQ Ke kI Nw Or Ou Qa) oV(bH Cw Fr Ii Iz Ke Rf) Tz(Aa Ii Mm Pb Si Va) In(Gd Lp Lt lY Of Vb) Qa(Cs Fp Lh Of Pc Rm) Qd(Ap cF cM Id lY Ue) Li(Ji kI Or oW Pe Po) Nq(aC Ii Jo Ny Ur) Lx(cM Jj Lj Pc Sr) Rx(cY Mp Oh Om Ou) Or(cF Fa Jm Rm To) Vb(aL Kf kI Mf Mk) Nn(Jt Ky Mv Pf) Mm(aZ Lh Pf Qb) Ny(aU bB Ky Pg) dA(Iv Jj Jr Mh) Bc(dD Fw Jr) Ml(cM Lj Pc) Nb(Dl Gd Wb) Jt(aQ Jq Lh) Dg(aL bR) Mn(aU Vi) Yi(aQ Mt) Jj(Lh Pf) Jo(Mu Yh) Uw(Ux Vu) AlRg ChUr DlbR DubB FaNw FrOu GdMg MhPb IiLh HcUx ShJr QbPc} Cu{Ux(Cp Cv Du Ha Hc Hp Hv Ij It Js Kf Lw Mr Mz Nb Pb Pe Pi Ud Ul Vs Wc Xa) Hl(Aa Ap aZ Bc bO cF Dl Hb Hp Ii Jj Jt Kn Kq Op Pc Rt Rv Uf Vj) Wg(Al Ap Bc Ef Jg Jj Kj Kn Nn Ny Oi Ok Rz Tr Vj) Uz(Ap Bc Dg Ef Jj Kn Nn Oh Oi Ok Rz Sh Sr Tr Vj) Hp(Aj In Ko Qd Ra Rb Rt Ru Rx Ry Tv Uw Vi Vp) Uy(Ad Bb Cq Fb Gd Gn Gp Lh Mm Rc Uu Va) Yj(Ao bO Hb Hv Lh Mg Nb Op Yg) Uw(cU Gl Jt Kn Ko Ks Ma Oy Uo) Yg(Cv Hx Iu Jm Ns Rx Tz) Vb(Ib Kq Ks Lh Nn Ns Oh) nI(aC Co Cv Fa Ii Oh Um) Gn(Hb Ks Mm Ry Sh Uu) Ry(Cv Jo Ma Pj Qn) Rx(aZ Hw Iu Jo Ns) Yl(Ad Jo Kl Rc) Vj(Cq Kq Lw Ud) kI(Al Ax Pj Si) Gd(aZ cU De) Zq(aZ In Jo) Rz(In Rj Ud) Du(Mh Rj) Wf(Ii Ks) Um(Si Vh) Pj(eQ oT) mE(Fb Ug) mU(Fr Kl) AaFd AdYd BbgZ GhKn GlWc MboT MzLp TrRu HbnJ RcmW JrVa JsdU OpUo UrmM UvoQ} Yi{cU(aE aH cM cT dJ Hp Ib Jf Jl Js Ks Lx Mz Nn Nv Nw Or Pg Pi Yg) Ou(Cs It Jl Jn Jo Jv Lz Mt Nb Qx Ra Sf Yl) Hv(Ad Al aO dI Du Hl Lz Mh Mz Ng Ra Uy) oF(cC cT Cx Dk Fi Gh Gz Iv Jf Nl We Wh) Lx(bS dA Ld Mi Mt Mv Na Qn) Mt(aX bO cT Gd Jl kN Pg) Tz(aW Ib iH Ma Nn Rc) Pg(aM bS cT Na Ni Wm) dJ(fP Ij Mj Mz Oh) Ed(aO bF bZ Hp) Jl(bO Hp Iv Nv) Jq(aM aW dG Qv) Rx(bJ Js Ns Yj) nC(bB Ke mM Op) hC(Ke Mp mU Ow) kE(dK Pb Rz Yh) kI(Nm Ow Qa Xa) Mz(aM Lh Or) Is(Qc Rc Va) Ji(Hb mW Si) Ld(cB Nb On) Nw(bX Jv Nb) Vi(bS dL Yh) aO(Pe Qa Yg) cT(Lh Mk nU) dD(kK mP mU) nN(Hq Mv Oi) oP(Mn Nt Po) De(Ad Ks) Iv(Or Vv) Lp(mH mU) Oh(Ho iH) mW(aQ Uw) mZ(Fw Nn) AoRc PomH ExnK GdOm TveM IncF JnmP KqtF PsbO LjcB RtOw OpnH OnVh VvaM PedA aUnD cLkN cSmI} nI{mZ(Ad aF Dl Is Nb Nn nU oE Ou Rj) Pi(aF aU Bb Cv Dd Dl Jj Qv Tz) Kq(aC Aj Jm Jv Ok On Um Un) Pg(cE Cv Lu Nm oT Um Ux tF) Mz(Dd Dg Gn Hb Ib Rj Um) Lp(cY dH Et Jk Ky mP Um) Ut(Ba Em fP Fr Mk Mu nT) cG(Jj Jo Jr Of Rc Va Vb) cU(Ap Dd Jr Nb Nm Ns Vv) Uf(Bb Hp It Pz Uu Ux) aF(aU Fy Ky Nb nU Vu) tF(aZ Jj Jl Mj Qa Ur) bZ(Ad Jo Jt Nm oT) Hp(Fy Nb Ou Vp) Yd(Cv hC Mh Tv) Ju(Ky Lh Lx Ou) bF(Fn Ug Um Wb) cS(Ap dU Is Mj) Al(Jl pH Qh) Fw(It Jt Mm) Ky(jB oT Vv) Cv(Is Jl) Nm(Nn Qa) Ma(Pj Ye) Hl(Il kN) Jv(fA Oh) Vv(Bb Ou) dA(Ez Rh) kC(Jl Lx) AdOn AwOy FyRx GnLv LuaU MjUm MvYe TzIo TnOh ItQa YhUr SfdR JjbQ KchC UgPk VaVp aOkE iPoT kNpH} cU{Yg(aE An aQ Aw aZ bR cM Cq De dI Fd Gp Jf Kq Lx Mv My Or Qn Tv Ut Vc Wc Yk Tj) Hp(aM aV bA cF cY dI Fw Jr Ju Nb Nw Wb Tj) Sh(bS cF Ch dA Hq Lh Mv nB Nf Nq Om Yd) oV(aU Bb Dk Jk Ju Kq Mw Nh Nw oT) Uw(aK aM aU dJ Jr Qn Um) mE(Cv eC Ma nU Qd Rx tF) Si(cT Gp Ji Ld Ri Tn) Gd(Ao Aw Bn cB Vc) Mm(Bo cB kP nK Vc) Lh(aU cB Ho lX nA) Zq(bS Gp Jr Um) Uy(cB Js Mi Qh) oE(Fa fP Oz pF) Em(mH mI nA) Hc(fR Lp Vb) aU(Mb Me Nn) cF(hR Is nT) dH(aJ Mb Me) nK(cM eC Mn) Sf(dA dI) Ow(Vj Wc) Vc(Om Oz) fR(Ok Um) AlnU AxIs BaeP FiGp HvLp HwmW TolY WdnJ JrRx LdjB LtoP YlOr OhVi OycB OzpK cMnN} Tz{Hp(cL Co dL Eq Ez Fc kR Li Ma Mt Nb Ni Nj Nn On Pe Si Wh Wm) Rx(An cL cO cZ Hc Jv Lz Mm Oh Pf Sf Uw Yj) Uy(Fy Hc iH Mt Mu Mv Nq Ny oF oH Uo Vq Wh) Si(cZ Gn Hc iO Ji Lx nL oF Ri Tn Wh) Va(bE cI Ib Kc Mg Nq Qb Vp) Hb(cF Et Fi Gn Kc Ry Tn) Yl(Co kR Ma Nb Nj On Vu) Ry(cB Ho Lu Mt Qv) cF(mP mZ nO nU Zq) oE(Aa Ii Kz Mr Ny) Yg(aK cL cY dF) nU(aX bC Jm Qe) jV(Bo De Ld Lu) Aa(Cx Gc mW) Yf(Gp Ib Ny) Eq(Lh Oh Om) Ho(Ii Om Rj) Rc(Rz Vj Wg) mZ(Fy Ii Nn) Gh(kR oF) Yj(Nj Qv) Uw(cO cS) eD(Ih Oa) AxlL GnnT HvLp IdjO HcSh IolX SfaW ZqoF WdnJ RzOh VwPj PckP} Is{Ax(Cq De Hr In Jo kN Me Um) Hp(Jt Kn Nw Oh Rj Sf Up Us) Hb(Em Fd Hr Mr Ul Vh Vp Xa) Vz(An Cp Cq Dc Dr Jt Mz) Sf(Gp In Mr Ry Vi Vp) Va(Id Kn Lj Mr Pc Qe) cF(Aa Dg Du Jj Jv Nn) Dr(Ad Mh Nn Tr Uy) Hl(Ho Ju kS Ow Rx) Wg(cV Jl Ju Ny Pb) Ry(Ir Ju nD nH Up) Um(Gh Ju Jv Lj Sh) Yj(bO Iv Jg Ma) Rm(Lh Om oT Ru) Uo(Lp Sh Zq Tm) nN(Jm Jt Ny Qh) Yg(cT De Iu) Uy(bN Og Rc) Uz(cV Ju Pb) Vi(Qe Rf Si) kC(Nm Nn Oe) lN(Cs Kn Ph) Aa(aS bV) Gd(nH nL) Gn(Ad nC) Gp(Rx Yf) Yh(Ii Jo) Jv(Vh Xa) Ps(In Kn) Yl(mW Qt) Uw(Iu Jm) cS(lY mE) DuLu EmOh FanO NmmP IhVh SinJ RceM ZwKd QbTl QhmU JjfR KoLp} Jr{Si(Du Gn Ow Oy Rx Ry Ul Um Uo Us Vj Yj Yl) Va(Ad Bn Cp Cw Dd Gn Ha Kp Kq Kr Pi Pk Tl) Rx(Aa Ad bO cL Cq Cv Dd Hp Jt Lw Nf Ud) Ry(Cv De dJ nC Nv oF Pj Sh) Yl(Gp Hb In mF Mz oE Or) Gn(Hb Ib kE Mz Nn) Du(mT Mz Ny Pj) Hl(cF Ny Oh Zq) Hp(bE Lh Nn Rj) Id(oE Sf Sh Uy) Yj(Aa bO Fc Jp) Wb(mP mT nN nU) Tl(cF Ju Mz Nn) Hb(Ru Vj Wc) Yg(bW dF gL) Sf(Um Uo Uy) Zq(Gp Ha Hr) nN(Fa Nm Nn) Em(cF Oh) Ib(Vh Vi) Wg(Ks Ny) Lp(Gz Rj) Ow(Uy Wc) Uz(cV Ks) Vj(Aa Ke) nT(Al aU) GpVh HrOp JupK cGmE} nU{Uy(aZ cL Ji kK mH Ok Qn Th) Vv(Dd Iz Lv Lz Of Ph Wf) mE(aO Cv Ed Ju Ki Pk Rb) Al(Fw Jn St Uf Un Vi) Ur(Eq Kg Ok Pc Qu Yk) Gn(Dd Hx Ps Qn Uc) Ns(aF Jj Lx Qb Qd) Gd(Ke Ok Wh Ti) Tn(Ct Kd kI Tv) Sh(cG Di Kc Lh) Ji(Ju Nn Of Uw) Wh(aZ cG Vb) Jj(Nb Ok Yk) Ye(Jn Qa Wc) Rz(Aj Qb Vt) Vi(bB dI Uo) cT(Cv Jo Qd) Aw(Hp Oy) Gh(dF Nq) Mg(Ux Yf) Yj(bW Lh) Xa(Pz Vb) Ry(Ex Nw) Lp(Fn Mx) Rt(Nv Ug) Oh(Sf Vq) Uh(lY Pc) Ut(Ef Mw) CvTh DdaU DpaO EmQd EqbV FwWb NmYh MaKj NaPs NblY HpVs YdQv VzNw JdWf KeUx YlOr OfOn aAfR} oT{Kq(Ad Bc Fr Jt Ks Nv On Pa Qn) Mm(Ba Et Fw Hc kN Lx) Ow(Bc cS Ib Id Io Ji) iO(bH iP kE Lx Pa) oN(Ij mM No Nv Pb) Aa(bZ cT Jl Ma) Oh(Ar Jq Nm Oa) Pc(Et Ji Lx mS) mW(cT Mh Ni Pf) kN(Hc Mb Nn Ou) Cs(Kx Rf Rh) Ez(Bc lW Mw) Ma(Io Kc Om) Ju(Cq Pb Ri) Ny(mP mU Qa) Nm(aR Ok) Lx(Ml No) Mb(dE Ns) Mj(cM Lj) Mw(bG Iv) Nb(Lj Nn) Ib(Ct Qn) Kc(bA Pa) Qm(cT Pg) Oz(dN Pi) eF(aF Fb) ArKx PoFp FrPf MhbC MloF IlRj HbNw QaLi JjPi JmRm QnbJ bFmS bHoV mPmT} oV{bQ(Ax Cw Fr Jo Ke Kl Ks Lh Oe Of) bA(aG bH Ii Jl Lh Ma Ow Qm) cT(Bg dG Dk dM Ke Mp Ok Ow) Ez(Ap Jv Kl On Ql) kC(aZ Jv Ou Pj Qn) Al(dM Ha mP Po) Hb(bF cG mW On) Hc(Bb bH Iz Kf) Ld(Bg MT On) bV(bH Ib Io Nn) bZ(Fb Im Jt Qe) Fw(Jk Kf Oh) Nm(bF Mx Pi) Ma(Ju Kf Ks) Jj(Ns Pk tF) Jv(Di mW Qn) Lj(Mx Oa oN) Rf(Cs kN Kx) aF(Cs dK nA) Ef(Ct It) Qn(Ib Jk) bH(Cv fA) kN(Ax Fa) AdoN BbNw FpRh FrbF NnPi NaPj IuOw JtOn cSmT} lN{Nq(Cp Dg Jh Jo Kj Kl Ml Mx My Nx Ra Wm) Or(aZ bA Cs cT jG Jl jM Pb Pd Qa Rm Us) Dl(aM BO dI dJ Mg Ml Qt) Kj(Bg cF Ch Fr Ly Ou Qt) aM(Ax Iu Jc jP Kk Ra) Dg(aO cJ Gl Kf Qd) Mj(Dc Ir Om Vp Vs) Qb(dI Fr Mf Nn Qy) Ou(Jt Kk Ok Oy Uf) Ax(Gp Ly Mq Uh) Bo(Ap

Figure 40 Continued

Figure 40 Continued

Nq) HodF QeeM JhcG KqdM UfmU} rZ{Mx(Hv Li Mb Mr Na Nf) iC(Ip jV Po) jT(jD jV Po) FrjY NqjU MjlO NijV IpqY QeLi rCjP}
pH{Ny(Hq Kx Pc) Fp(Ri Wm) Nn(Iz Pk) Lj(Lz Pf) Pc(cY Ii) AxRh DiMm EmPk NtLi IbbV QeKx KocF OzcS} Ma{jB(bM Dc Iq Kn Qn) mS(Li Pc Pj) Nn(mU nT) nK(Ap Iz) BbnA CvmM PckP aUlX bVoQ cSdU} mH{Rz(Bb Iz Wd) Uy(aW Mq Vu) Fy(Sh Uw) Wb(cS Uf) BbUw EtSf ShPe ZxcS YePd UfUx UrbF} mT{Kq(Ap Co Cv Mm Ok Pj To) Rz(Nm Og Rg) Gd(dF Nn) GnMj MgYe MtHl TtJj cSdU} Ry{Nv(bA cB Fy Iv Oi Sh) Nb(Qn Uo) dR(kC kO) AwhC PoeM HqnD ZqdF UmoN PgeC} eP{Ao(Ug Uu) Ex(Aw Nn) aO(Mi Pj) BgUh MgUg MvoH JddF JfOa JhQw QycT KgbA VqbV cGcH} nL{Rv(aF Ao dF Ij Ji Mf) Gn(Fn hC) Rt(Mh Qx) DrhC ThbB FcQa GddF WcPf} Hl{Rc(Fy Mz Ok Vu) Ho(Ib Va) nT(iJ Ok) lX(aQ dR) FbKq NnMt MhHv RgnK} Qa{Hb(Gn Uz Wg) Fa(jB nA) fB(cS cY) kP(Al Fp) CsnA FreM NngZ UymF} Gd{De(Ax bA Fy Gn Mh Mk) nK(Cq Nv Ok) Yl(Ao Ef) TimU} Ju{dU(Aw Ez Nt) pK(aK aW gL) pI(Cq cT) NnoQ MjkP UyPg PimS} lX{aQ(Jj Jt Oe We) aU(Lz Mh Nu) dR(Gn Yd) MpUy JocY VbaK} nT{Ok(Jo Vb) aO(aU Ug) dA(Ax Ra) AlbQ NmaU MjcF WeaK PcPf} Uy{Uo(Cq Dc Jq Mz Nb) Qe(bO Dp) CokK FySh YhnA} jV{Bo(Ap dE Ed Kj Mh) Ly(Bc Dg Ky Qv) NqOy} oD{aF(Jn Mh Pf) Fa(bA hC) Nn(Ok oN) HaPg RmcT bFcF} eM{Ps(Iz Ks) Rm(Rt Uw) Ux(Et Vq) DlUf MmQe HoJj} Zq{dF(Aj bO bW dl Hb Lz Oi) PfmI} nA{AxPe BbEz WmdA FdPi HqZx InWh HbKq YhRt} Sh{Vu(bH cR) CvPg EdMv EzNf NnmI NqYl} Rc{Ok(Rt Uz Vh) AoPs EzkP GnJq UfnK} Jf{dX(bC dD Kg Mg) kK(aU Va) YemU} fR{Jj(bZ Jk Mv Nt Ua) NqbA PfaA} jO{Ly(Bc Um) hR(Ni Vt) MfNg KobW UmdJ} pK{Rh(aU dA) WmaU EzbH IjbZ IzKq RfcM} Id{jI(An Na Uh) lM(Jo Qt) bOjG} Yh{Ed(Mz Si) MhcB IbJp KsPg UrnK} Ji{AxcT NmmU HbUl JocF JtPg YlhC} eQ{Pc(Nt Pi) IhbZ IocT RgkC OabQ} nO{Pf(cF Pc) NqUm LvaU MhdA KeLi} Ye{NnVu HqfB QtmM PcmU aQnD} mF{Sf(Jn Mj) Pg(Rt Si) FihC} kK{Oi(aU Wh) BbaU QtVb UwbB} Gh{Mp(hC nW) PskR VuhC} Gn{mY(Js Qe) NmHo nKhC} aO{HoIb KjfB KohA dXoN} cS{dU(cO cT Pg) WbmI} fA{Ny(Dc dF Jl) MwcM} mU{AxKx EzJo NtJt OfOk} jB{bZ(bM cM Kc) EdiO} kP{BbUf EqJj MjSf KlVb} Mx{AlgC LvaA RmlM} Hq{MhSf WfnD UxmM} Si{Ua(Ed Uh) UhVu} Kq{IzfB QvoQ VqmY} Ky{jF(Bo De) OkjP} Uw{JskO PemI PimS} Vj{Aa(Fy Pi) HbJl} aF{FyfB NimS aPdH} Nn{MmnK NeNg} Ly{AxjI BcjU} Mz{TlNv dDfB} Qu{VbmM cToQ} Ko{jP(Ss Um)} Lh{IcdX VanB} Yl{NqbH JqRj} Oy{DeaC dlhA} aA{LvNj IvLj} lW{AlPf MnPs} AnbOjG ArdRdX EdTrYd YfNbJm EzcDdU NmRzmY MdVthV MhMlXa HvRvUm IbNvVa YkaQnD WhVbmM KkcHlM UfPjmS PedAnK aMcFlO Constrained panels with 3 analytes, where 1.0E-8 >= 'AUC p-value' > 1.0E-9. Contains 9,153 panels of 23,517,221 total panels evaluated. : oO{Dd(Ax aY Ba cL cS dD dG hC Kx Lz Mf MP Mt mU Mx mZ No Nt Ou oW) Mh(aI aX aZ bC cB cS Cv cX dA Di Dk dN eF hB hG Mt Nb Nq Pi Vu) Mj(Al aQ aU Ax Ez Jm Ld Li Mb mP Mq Ni Nm No Nt oD Of Qa) kG(aM bQ cF Cv dG Di Fr Gb Is kR Lx mU nU oP oW Pg pH Qa) Aw(aC Ax aZ Ct fR Hr Ib Is Kd kE kF Lz Ni Og Pe Yi Zw) cU(aL aO Ax bA cL Lz mE Mm MZ Nq Ns Nu Pe Sf Ur Yi) Nn(aJ aL Ap aY aZ cF cS cX hB Ii Jm Kd Kx Mt Or) Ax(aZ cF cL cT cX hG kF Mp Mz Pf Qv Tz Ut Yj) Yi(bA cE cL Dc Gb Ii In kN Lv Ml Mp Mq oP Ou) Ju(aA aK Bo dG Gl Ks Lv Mf Mp Mw nO nU Tt Vp) bZ(Aa Ap bV Dg Ii Jk Ld Mn Mw Nd Nu Qd Rh Uk) dG(aF aS bR cS dN Jj Jo kE Mb Nm Oy Ug Vo) Mt(Ii Jl Lv Mm Nb Nm nR Of Pc Qv Tr Tz) aJ(Cs Cv Is Jl Jr Mr oE Pf Pg Rh Ut Yh) oQ(aL aZ bO cV dD Jr Li Ni Ny Qa Qg Rh) Aa(aF aP bB dH dL fR Is Jn kE Kx Qe) Pc(bF dD gL hB kQ nN Pi Qg Qh St Tr) Pe(aY Bo cV cX cY Gn hG Or Ou Pj Yd) kF(aM bR FR hG Lx mP nN nU On Rj) Nq(aA Bb Hr Kf Ld Nb Rf Sh Tr Um) Kx(aO aU aY cF Hc hG kE Lv mW pH) cT(aX cF Is Lu Lv Mz NO nT Og) nR(Ii kN Mm mP nI nU Ny Oy Qz Zw) oV(bV fB hC kC kE kK Lu nH nL Ub) Cv(aL aU Ex iZ kQ mZ Ni Pg Pi) Hr(aF bF Ez gL hG mP nN nW Qy) Qv(Dk Fw Is Ma mP Pg Pk St Vv) Ld(aO bR cN cX dN Jj lW Nu Or) aA(Fr Fy Is Jl Lv Mg Mu nT Yh) cS(Ad Dc Jj Jt Kd Mb Nm Of Sh) dF(fR iZ Jq Lp Ng Pi Qd Ug Wm) Cs(aO aU aV aZ bF cF cX Pg) Sf(cE Dc Mq nH Nw Or Pa Yj) bQ(Co Ii Jo Ml Ni Nm Nx Qd) fR(aZ dl Iv Jo kN Nm Rf Sh) Lz(aV aY cL cX hG Or Ou) Nb(Al gL Jj kE Ns Uf Vu) Hc(aZ Bo cG cX Iz Mq Qy) Um(cL Fy Mf Nd nU Nv Pd) aO(aM aY Ml mP Nu Pf Uk) aU(hC Is It Jl Lu Ml Nr) cF(aZ gL hB Ky No nT Rg) dN(hC Jl Mq Qt Rh Vu Zw) Jv(cW Hu mM Pd Pg Zx) bV(An aY bL cl Qe Rf) dL(aF eC Gb hB Is Jl) fB(aM cM cZ Hq oW Po) hG(aR Mb Ni oW Pi Qa) Qt(Al dU Mp Pj Qg) Vv(Bb Em mU nN Pj) aP(Is Jo Mk Pj Rg) aQ(Lu Pf Rj Zw Wm) cL(Lu Ml Nr Ub Wm) oE(Cu Jo Kq Pj Qd) oN(Al Kd Nm oD Uk) pH(cZ dl Fy mH Mm) Ez(Al Hw Kg Ks) Yj(Ij Mf nH nI) Sh(Ad Mg mW nU) Lp(Ba Kk Ni Or) Rf(dA iJ Kd Nv) Ut(Ap Jh My Nj) aF(bP cZ Mb oD) eC(aD dH nJ nY) nO(aL Jy nY Ug) mP(aL Lv nI Rh) hC(Io Mb Mq oW) Bo(Is Jl kN) Cu(iZ mU Pa) Fd(cP Nr Pf) Nm(Ba cG Pi) Nu(bF bO Kq) Mr(dU Hl Wb) Nd(Kk Ow Rj) Tz(Cx eF Rj) Tr(mM Mw Qy) Qa(aS Bc nN) Rz(cP mW Or) aZ(Ni Nr oF) cX(Cx Ni Pf) Di(Is nW) Lx(Jl mZ) Mq(aX Ye) Hl(Nr Nw) Iv(dD oT) Qu(Pi Uk) Jr(Yd Yk) Rh(bL Hu) Vu(mE Qx) Pg(aX oD) aY(bA Yl) bF(aM Mb) cG(Gd Kr) eF(Jf Rb) nN(kE Oh) kN(Lt oF) oW(nW Ul) BaJo DpNv WmdU TjoF FrKq FyMp GcIj GpNs LumU MaQm MedD MfPi MlaL IbOn TtKs ImKd SjcW QdbO JdhB JjPh RgcY UfmF PfkQ cVgL dKkE} Gb{Is(As aW Ba Dr Fd Hr Hw Hx Id Ij Jn Jr Kd Kn Kr Lp Lw Mr Nf oF Pj Ql Tz Vs) Nd(aP aU bO cG De Gc Hc Ij Kc Ke Kg Kq Li Ma Mg Mk Mu Nj nK No Pf Qh Uz) Yi(aO Bb Ed Fw Ho Jh Jp Lh Li Mg Mi mT nH nK Qm Rx Rz Uh Un Ut Vj Yj) Vu(Ar Dc Jl Kx Mi Ml Na nI Nr Ns Nt Nv Oa Or Pd Pi Po Ps Qn Ub Vw Tj) Vv(aF aX Co De Gh Im Jh Jp Lx Mg Mm mP Mu Nn Pd Pf Po Qe Qy Uf) On(An bO cB Cv Hc Ii Jj Jm Jq Kd Lh Nm Ns Nx Pd Rb Sh Tz Vs) Fy(cB cU Cv De Ed Fi Fw Gc Jh Mg Mv Nf nR oP Pe Qy Tz Uy) Lx(aZ bO cA Cu dA Dk gL Im Jd Jt Mz Nf Ow Rx Vj Wb) Mi(bA bO dl Ex Fw Gc hC Hf Lv No Nt oF Ok Pf Qm Yd) Qd(bS cI Gc Hp Ji kF Lh Me Mh Mt Ow Pf Ps Qm Wm) Ed(bC bO De Dg Et Iz Kr Mt Nv Ok Ql Uf Ut Wh) aZ(aX bC bU bW Gp Hq iO Jp Mp Na Nv Qa Qu Ua) Jp(Ao bO cH Jf nH nL oE Ou Pf Qy Sh Tl) Pe(Co Jd Jg Kc kI Kr My Nq nR Qg Uf Xa) Hc(Aj Et Ez Fd Hv Jj Js Ld Ou Tn Xa) Jl(aX cS Im Mm mT Mv nN Pj Qy Uh Yj) Ps(bO cG CU Jr Nq Ns Rx Uh Uy Vj) Gp(aM cI dI dM Ji Mj Nv Oa Vi Vq) Tz(aM Ba Il Jd Jr nN Pf Pg Ql Wd) oF(Gc kF Ml mP My nN Ns Qn Uf Uh) Ao(aA cB cT Ow Pi Qe Qh Tj) Fd(bZ cS Kc Li Mg Mv Ow Rz) Tn(Gz Ib Mh Mp Oy Rx Ry Sh) Jr(Mb Ud Ur Uz Vt Vw Wc Wg) Oh(Ef Gc Ho Jg Li My Rx Wd) Ou(Ax Bb cF mT Na Ub Vw Yf) cU(aM Bb Co dH dI Jf Ji nU) mT(bA bF Hq It Jf Pi Yd) nH(aQ Dc Gn Ij Lp mI Ti) kF(hB Hv kC Ko Mk oP Qa) Mp(Ax cF Js Mx Ok Yl) Ow(dE Fw Ok Qy Ua Ub) Pg(Hp iH Ms Ub Um Wd) nU(Kp Kx Qn Uw Vi Yh) nK(mI Nq Ok Uc Vi Yj) nL(aQ aU Ba cT Or Uw) oP(aK bR cC cL Gh Mf) Hq(bO Gz Jh Lz Yl) Li(Js kN Ml nR Yk) Ut(Oy Sh Uf Ul Yf) nN(Jn Nv oN Uy Vp) Gn(Ho Hv Ji Ke) Im(cB cG Ns Yl) Yj(Fw Jq Js Qe) Oa(cG De Ez Mv) Pi(nI Pf Vj Zq) Co(cT kE Mx) Cu(Ma Uw Vp) Nn(Js kI Mx) Hl(Ji Ke Mz) Rj(Jq Ke Mz) Uf(dI Nw Un) nR(aQ cI Hv) mP(bB Et Ok) Ez(Iv Nf) Nq(nT Ok) Ub(Ji Vq) Wb(Pf Zq) Qh(Ld Mt) Yl(Fw Kr) Rm(kG Zq) Vj(Qe Vp) cG(Ax Mh) mW(Jn Po) nC(bB Dk) oQ(Ch Yh) GckG GzNt LwHv MaMx MgkI MuJs JiaD KgkN LdcB NvkP UoVi UhgL} kG{Pg(Ad aV cR dJ Dl Ic Jv Ke Li lY Lz Ml nC nH Ni nL Nv Of To Tr Ue Vt) Is(aC Ap Bb Cv cY dJ Hu Ii Io MU nI NN Nq nR Ns Ue) Mx(Fi Jj Jo Jr Lh Lv Lx Ma Mh Mm Mn Nd nU Ny Of Tn Yf) Fw(aK cR Dl Ic Jv lW Ly Mb Mp mT Ne Nh Oh Or Ou Up) Pc(aC aF aL Ez Fy hC Hq Ly Ma Mf Ml mS Mu nU Uc) dA(Cu hC Jl Jn Ke Mb Mh Ml Mp Pb Po Qa Rf Rh Wm) Lh(aF Bb cU dE Gn Jt Mm Mn Mp Nm nR Nw Ny Of) Lx(cY Ex fP fR Hu Ii MU nN Nq nR Ue) Pb(aF dR eC Jq Lu Ma mU Mv Nn nR nU Pe) aC(dU fP HC Ji Kd Kq Mp Nm Ou Pf Qa) Mb(bF bM Di dJ hC Hu Lu Ma Mp Mw oP) Nd(aL bZ cU cX Lu Lv Lz Ml mU nI Pf) Hr(jB Lz Ml Mp Mv nR nU Oz Pf Qb Wh) Qd(cT iZ Jk Jt Ks lY mE mP nR Ut Ye) Jj(aK bF Ch Hq Hu Jl Nq On Uw Wh) Pi(aK dJ dK Hw Ii kI Lz Ml Oi Tv) Mm(aK cY dU Et Ky mU Mv nR On) Uw(aI Ao aX cL Im Jd Mq Ok Qn) cR(Dk Hc Jr Nq Qa Qh Qn Vt Vu) fP(aL aQ dJ Fn mE Mp Oh Qm Qn) Nm(aK Hq Ky Nn nR Nw On Vh) Jl(Dd fR Gp Jt nI Of Oz Tz) Vv(aZ Fb Iz Nq Oh Ou Ux Yg) Mp(cF dI Ii jB Lu Uf Ut) Ic(cF Hc Ji Jq Lv Nl Nw) mE(aA Cu dR Jy Ky Mv Qa) Dg(cG dF Mz nR

Figure 40 Continued

Pb Pc Uy) Pg(Jk Jm Nm Of) hC(Al Ax Fd Ns) Mj(Jt Nm We) Vb(Mv Nv Qt) Uy(In mH Or) Qa(Li Mm) Up(Sf Wh) Uw(Bb Jq) aF(Ns Wc) AlUv AxPe CvaC PoRv GdJf NmJd MbPc TvYh XaOi RyLh OfPf} nH{Wh(Hf Jj Oi Or Rj Uh) Gn(aL Pf Qg Rm Ub) Gd(Lh Lv Ok Op) Uy(aO Iq Mf Ok) Wf(cS Jp Jy) Ye(hC Qz St) Lh(Ry Sh Zq) Uw(dC Ha Wb) Op(Ny Rj) DuOh EqbF FdMz GcaF HldI InSf YdQb WboN ZqJi QafB RzVt UgVh} Yg{aO(bO Hw Jh Ke Mz Pe Ps Qe) Hv(bF bQ Ok Ra Wm) dF(Jh Mt Na Ow) cT(Ao Kq Vu) Qa(kP mF) Js(cF De) Pi(aJ oN) bA(Gz Kq) dM(Mv Nq) mH(Jn Uf) EdbF PoeM EznT FwmM MtcX QukK UwlW PgaK aQnD bOmY dRmU mToN} pH{Pc(Ax Db Ip Jj Nf Ni Nl) Pb(bH cS Cv Ha Nm Ny) Qu(Lh Nv Om) Lj(Ax cF Cs) Ri(Cs Ha Qe) Oz(kC Qx Ur) Fb(bV Jd) Gz(Ug Um) Mm(bU Pz) Nb(Dd Nm) Vt(bR iO) cF(Cw Hb) cM(bV kC) AxRf GlUf NjTo QhoN NyeM} mP{Nm(aU dD Lh Pf Pg Yh) aF(bP Kd Lv Mj Pf) Mj(Pc Ue Vz) Jq(Of Uw Vb) Ok(Gd Hl Rc) Pg(Jt Mm Vb) Gn(aL Up) CqGd DpaO DuOh MblY MvOf NbJj Hlln TtSs SiUh QaLi WhUp JpUw JtdF RvbW YldA OpUx OrcF PcPf} lY{Nq(Hr Jo Lv Mw My Og Pf Um Ur) cS(Jj Jo Ke Ky Lv Lz Mb Mj Oh) Mu(Jo Lv Mh Ml Nb Pe) Mj(cF Li Oe Zq) Kq(Aj Dd Lh Pc) Ma(Nb Ny Pc) HaQa LzMv OrcF PbPf PedA} Um{Kq(Ad Bb Hb Jv Li Si) Qa(Jv Ny Rm St) Mj(Hb Jv nO) jO(hR jD Ni) Rc(Vu Yh) Jq(Uy Va) Li(Ji Mp) Oh(Ax Rf) nO(Lv Pf) FyfB HxLj IdlM ShcL ZqdF JuOr JvVu KytF NvVa PimS} Uy{Hv(bO Fy In Js Lw Mh Ud Uz Wg) Pg(cA cK Ks Qx Rc Vo) bO(cL Ed Jp Js Qh) Ed(Ao cF Hq) Rg(nC nL) mH(cS Jd) FyGd HqcE IuQe ShJp OacF VubH aOnT aVnC} dU{Ld(Bg Cp Cv Il Im Iq Jf Js Ng No Nx Oz) cS(bO bZ cF dD hC Jj Kn Nm Ow Pb) Uf(Ii Of Rm) Ez(Ns Ue) Mg(Uu Vo) bC(bO Ub) CpJv NsMa QwbZ KqaO} rZ{Mx(Hw iC In Js Lj lO Ny Of Om) jD(Iq Lj Ma Mp Nk) iC(jP Ma Mu Qa) lO(Fr jI Mu Po) jV(jR Ma rA) Pb(Il Nv) jO(Li Nj) LurC LvjY NbjT HrHw JnjP} Gd{De(cA cR cT Iv Li Lz Mb Mj Vz) Yl(Co Kr Mu Mv) Uc(nD nK nL) oP(cC Fi Mu) Ow(Du Kz) Uw(nJ nL) Vu(Gn Ns) nK(Kr Vp) AofB TjOh EzVz MgnC JfgL VjPa} Sh{Hq(bL cF Cv Hf Mh Nf Vz Yl tF) Nq(Oz Pa Yk) mH(Ps Qu Uw) oP(bB Ct Hu) bF(cI Ed) eM(Hv Ps) nB(Nb Pf) LvcF MvbH IbJp IiPg ZqdF JhmF QumT UfnO aOnK} Or{Yl(aM bQ bV CT hC Hv Mz nC) jV(cF Ct Iu Jm Jo Ko) Wh(nC nJ nL) Vw(Hb Lh Ny) cF(Ju Jv Sf) Si(Uf Vu) Js(jO qW) AxjG EzVz IbVj RvnL} Ow{Si(Hv Nf Pg Qy Up Vu) jB(dE In Jj Ml Qa Tj) Ed(Du Rz Yh) Gh(kS Lu) Ho(Nm Rf) Lj(Vz Yl) DuHv FyVj ManJ NfSf YkRf ZweM WcfP QtfB aFeQ} nL{Rv(aV bW cO Et Js Jy Rz Yd) Gn(aC dH Lh Tv) Op(Nm Qv Rc Ug) Uw(Up Vw Wb) Mk(We Wh) Yd(Qb Qv) Rg(Rz Ti) LzWh WbQu WdbB OkUx} Ma{jB(aU Hr Ne Oh Tj) kP(Fr Li Nv Ok) oQ(aU Kg Kj Ks) nK(Cw Fa Ks) aA(Iv Nj) mS(Ap Ij) AaoP DpnO HvYl ZqdF JmmU JotF KjnJ VonT} gV{aM(aC Cs dB) cG(cH cP dH) Cp(bB cW) aF(bQ dF) aK(cH dD) bO(bN Ct) AdaU AlcY AoaW ArcH AwdD AxcC CqbS CsaX CwbW aCbC bBdI bQcV bVcB} nC{Rv(Co cY Hb Uf Ur Wt Vu) Uw(aK dC Mh Oi) Vh(Qg Vt Wb) Gn(aU dH) Qb(Wh Yd) TinA MgUx MvWe HlUc HbWh WbJn SfJq QafB RtNx} Me{jG(aI aK dJ Hf) jU(bA bC dE Pi) jM(bJ dJ Ky) Mf(jD jO) Mx(aA Ji) jP(Bb bZ) jT(An Kz) lM(Hf Pi) ApjO CtiB NstF OkcF aOfP} Yh{Ed(Aa Hb Ks Oh) Rc(aO gL Jp Pf) oP(Hb Ib Kp Mz) Va(mF mY) nD(dR Ss) nJ(Qx Uh) MjHb IbaA IioQ SiQa KofB RycB UrnA} fB{Qt(cV dF kK Oh Ok Pa Pg) Qa(Hx kC Ns Ny Qn) Fy(Ub Uo) Jv(Cq Vu) aU(Rh Wm) FngL MfJu KnRz OpPi OkUu aFaP} nT{aU(Ap Cv Fy Jf Lu Mm nY Pc) dA(aF Cs Fy Ml Pf) Ok(Jt Of) aO(dJ Qv) AldR AxbQ DiaF MjWh HlbF TUj} Si{Vu(Ji Ld Mh Ml Mx Qx) Ed(bZ cS) Nq(bH cT) Hv(Kd Oh) Uo(Kq Qa) Uh(Fy Pi) Vj(Pa Pg) CvPg FwoP JiUl QyOh} Ry{Nv(Ax cT Js Oh Pe) Hv(eC Mh Wm) mU(dD hC Ok) Ed(bF Ok) cF(cT Oa) NqbH NsNb OhdA VuhC PeeM bSoN cBcT} aA{Mb(Iv Lj Lv Mx Nj Nt Nv Pg) Lv(Hr Nk Nl Nt) Nj(Iv Mx Nt Pg) Iv(Hr Li Mx) NtNg IdlM bZfR} mT{Rz(bO Jo Oi Pf Qa) Co(Hl Wd Yf) Kq(Dc Ip Lh) Eq(bF Ur) Qu(aR Rt) DpaO EfYe FnGn NqSf MjVb HlhC OkUx} nJ{Et(Kq Wd Wc) Wh(aI cG Mn) Rz(Hv Qx Uh) Rt(Lz Mq) Op(Ug Ur) EzJt FdPi GnQe MnbZ InVw SjPf QaYe JueC PsbQ} jV{Bo(cM Je jl Jo jP Kl Lv Mx Ra) Ly(Ap cB Ct Ki Kn Ko Mf Ue) rY(Mu Mx) CoNq EddI LzcF} oD{aF(aW bN bR cA Kx Pc Rf) cT(Bc Cv Ha mM oQ To Ur) aU(bH Jf) DpQn NmOk NbbF LdjB LjhC} cF{nO(aF Ky Mp) Aa(Ji Qa) Hv(Uz Wg) In(Ps Wc) Jo(Lv Po) Vu(Dg Sf) DuOa MhJi WdOy YemU JvfA aMiC} Uw{eM(Ih Im Sr Vu) mU(Mg Op) nA(bO Ez) kK(Jp Nq) kP(Kf Nm) DeOh EdbZ JnmF PslW UfmH} eP{Ex(Dc Mt Mu Nq) Mp(aO Ok) Jd(aL aO) Ug(Ba Fw) cG(Aw Nk) AoVo EfUr MvhG KqeM OmbV} Hl{bO(Nb oQ Vu) nK(dR Uc Vp) Ho(Jo Oi) Ib(Jp Vu) NbUo HvhC IjmH looP lvpF cLnD} Id{lM(aJ Ct Db Hv Kj Ky) jT(Bo Qm Rb Uh) jG(aM Ky) jP(aJ Ks) KojI} Ld{jB(bZ iH Jj Md Tj) Yl(cB dI) gZ(Iz Of) CopI NmHo HbdX cHlM dRlW eQkC} Ji{Hb(Hr Rj Ud Vh) Li(Ik Nj Nt Pg) Aa(aS cC) BbNs NtJt IvLj OfmU} Oh{Li(Ra Rz Uf) Zq(dF Jp) Lj(Ho Yl) tF(Jm Ns) jB(bZ Kc) DeVz HvZw RaRf} mH{Rz(Aj Pz Ur) Mg(Ps Wd) Sf(gL nK) FyVa GnPe NiVh HvYl WfcS PscW UgbF} oP{Gh(aK aV bU Ho) Ho(Ap bW Qn) Ns(Mb Ug) Sf(Cq De) FbRz FicQ IbSj} Mh{Ml(Ho Wc Yd) Ps(Ao De Eq) Mx(jD qZ) EqJl HoaO UaYe HqWc dAlW} Va{Nv(Jo Of Ul Uo Wf) Jq(Uo Vu) eM(Jf Uc) YfMz EznA MjmF} lX{aQ(Io Pj Rc Yk) cY(Mm Nm Ug Vo) aU(nY Qa tF) QvPs} hR{jO(jG jR Lj Lu rY) Vq(Pb Pc Po Qn) aO(dI lK) QUv} mU{Ye(aF Qu Wd Wh) Nt(Jj Of) GnOg WbhC WfcS JjOk NyOp} nK{Vb(My Nx) FwJf GhhC GnMj MzVw InRt WbbF WhdA JqUx} Pi{nA(Al Gh Ii Lz) mS(Ug Uo) AacC RvmF eQkC} eM{Vb(Et Im Iv Jn) Ps(fP Lh Tv) FiJj LiUx} Hv{In(Rt Vz Zw) GnhC TrYd VzUo KdRv YlPf} Rc{Nv(Wf Wg) GnMz IuPs KqgC UfkP VjVp aOeQ} Oy{De(bS Mk Ne Nl Pa) Aw(cB Ho) NqjD} Pc{Vj(Pg Vp) kP(Gn Yd) AljB EqmY FypI KxeQ} fA{Ny(cV Cx Dk) Ar(aO dD) cM(aL cT) LjdN} kK{aU(Io kR) CoRt DubB MuUr TvRz WhaK JmVu} Hb{Qa(Dr Hr) Js(Uz Wg) Vj(Fy Ps) YfJq} Zq{dF(Gz In Jj Jo Ks Nl) LjaO} Ko{aO(jT lM) jO(dH Qv) jP(Ky Uv) bXdX} Pg{FdhC NtJo HoJm SfiJ JjfR JtOk JukP} bO{jG(aM cZ Dl Ez Up) GhkR WhkC} nO{Al(eC Mj) EzJo GndR HaMj LvTo QuJj} Ib{Ed(Gn Wd) Rz(hC mI) WfNv dIhA} Kq{Yf(Ii Ks) FbGn KyjP OkoQ VtmY} eQ{bZ(Qe Vq) kC(bA Qw) QhOk cTtF} lM{Ax(cH Po) Mx(It Vs) DlcH KlaO} Nq{Yl(cT Jv) jD(Jd Om) SfbH} Gh{kR(cT Mp) cBnW dRoN} Ho{Jm(Jl Pf) NmMt JoaO} Jj{EqmI MgkP ImfR QumF} Ju{Yk(Mf Pf) pI(Fw Pa)} Jv{CqpI MfqV MpgZ VjPa} Lj{Im(bS cK) LvIv MbOk} hA{Ct(Ly Ra) AnLy DlcG} nA{Ez(Ad Kl) AlFy MjkC} jB{bZ(dD Og) AlUk cSdD} jP{Ti(aW Kc) BbQt KiKk} oQ{EzLi FyTo TrbC YldA} Aa{EdQl QabS RtVj} Yf{DeNm IiLh QaQe} Jf{dX(bF Tt) aUkP} Ky{BojG NstF LyiC} gC{EmaF MmbF QtOa} nD{Ps(aK Gn) DuJs} hC{EqmF FimS RzdN} Ap{jO(Bo Iu)} Ax{TrmS PflW} Lv{Ng(Iv Nt)} Mj{Yl(kP Mp)} Mx{qW(Li Mf)} Hq{EdSf WfkC} kO{NmQa YdUr} AlbZlW AnQzjI ThbBkC NsNbTl MbNvOf NkQmdX UeVjPa YkSfPf WbcSmM YeRvVu RzVwmY NyaQpI Constrained panels with 3 analytes, where 6.7E-8 >= 'AUC p-value' > 1.0E-8. Contains 11,712 panels of 23,517,221 total panels evaluated. :
oO{Kx(aL Aw aZ bM cT cV cX dF hB hC Hr Lu Mj Mm Oe oF Or Ou Pg Pj Qh Qu Ut Yj) Ax(aQ aX bR cE cG Dc dG dN Hr kE mW Nm No Oe Or Ou Pi Qn Ug) Lz(Aa aQ aX bA Bo cE cG cN cT Cv Dc dG dN Hc mP nN Nq Pi Vu) hC(aJ aO bP bQ bW cL CU dL Li Lv Lx Mt Nn Nt Ou Pc Ql Vv) kN(Ad Bc bM cT dG dM Fd Mt Nb nN Nq nY Ou pF Pi Vu Yj) Ju(Ad dR hG Hr In Jp Jy Lh Mv mZ nN Pd Pk Po Uc Zw) Pi(aF Aw aZ cS Ez gL hB Hc Hr Jo Ld Mb Nc Nj Nl) cT(bC Bo cL cW dD dL Io mF Mh Mj Ml mP mZ Nm Nr) Dd(bF Bo Et Hc Im Ml Mq nO Nv Nw Ny oQ Rm Vu) Pf(aA aV Aw aY Bo cN Cv dJ dN Gn Mj mP nN oQ) Ld(aQ Bb bF cS dA Di Dk kF Li Lv Nm oF Pj) Nb(kC Lx mF Mp mU Mx mZ Ne nT Qv Tz Ur) dG(cD Di Dl Ii Kd Ml Mm Nn Ns Of Oi Pc) mP(dD hG Is Jl Jv kG Ne Nr Qg Rf Um Vu) oW(Al Ap Bb bV cD Il Kd kK Mm Nm Qw Ut) aU(Bb gL hB iZ Nm No nW Pc Pg pI Sf) cG(Ad bV Cs Dl Jj Jt Mb Ml Of Pj Sf) Cv(aP aQ Dk nI Nn Nr nW Or Qe Vu) Lv(Al Aw bC dN fR Hb hG kG nN Yj) Hc(cU Hp Ib Kd Me Nc Nd Of Tz Yg) Cs(Aw cL cU Hr Is Mp mW Mz Oe) Mh(aP bZ De Fd kF mU nN nU Yi) Mt(aC Al Jo kE kK Lx mZ Uc Ug) Qv(fR Mg Mu Mv nT Ny Or Qd Qu) Um(Em Fr Jd Jy mM mU Mx Nh Tz) bF(bV Jd kE Ml My Ni Nx Oy Uk) cS(dU Ed nO Ny oQ Or Pa Rf Zx) oN(Aa aJ Hb Iz Jo Mb Mm Nx Og) Fy(Hu mM Mu Mx nN Nq Qg Vu) Mj(bC Di Hb Ii Mm Nn Ny Ub) Is(aO aS bC bI gL Ks nN Nq) Jl(Ad Aw eF gL Hr kQ nC nN) Jv(Hr Jy Mf Mp Mx Pc Qt Tt) Ut(cF Hq Hv Ib Kd Mk Mv Qa) aZ(Cu eF

Figure 40 Continued kG Kq Ml Mr No Zw) Ug(bA Ex Fw gL On Pd Qa) aP(Al Kd My Nn Of Og Qx) bV(bJ cL dl gZ Jf mS nO) bZ(cE cF Hb Hq Ib Kj Mv) fR(bQ
cW Hr nB Pe Pj Ye) hG(kE kK Ml MZ Nn No) kF(aL Gd Mi Mx Pg Qt Qy) Wm(aF aV Aw bR Di Mp) Ez(aA cN dL Hu Mu Mx) Rh(Jk Mx nN
Nq Nv Tz) Rf(bO Hu Jk Mx nN oP) cF(dM Io iZ Lu Ni nW) dD(kE lW Mb Mm mU Ni) dN(bA Nd Nr oQ Pe Vs) nR(Em Jk ml nM Ub Vv)
kG(cL Hq Nd Ne On Po) Gb(Dk Kl Mq mU Po) Hh(Dk Mp Nw Pg Tt) Yi(cP cX dL Ng Of) Pc(cE Gp iZ Or tF) aJ(Ky Li Nm Qd Qg) cU(bM dF
Hl kE Uk) hB(jB Jc mU nB Nm) Aa(dM Ed No Nq) Aw(aL dL Ml Mz) Mb(nN nY oT Tz) Hr(bQ iZ On Ua) Tr(mT Nh nT Pd) Zw(cE Iv kE oP)
Qt(cV Kd Mz Ue) Qn(Bo Di eF oE) Pe(bM cE cL cN) aA(Mp mU Mv Mz) dF(Qa Qm Rx Sj) Al(Jn On St) Ba(Ib Jt Of) Nn(cL Dl Gc) Nq(Ad
Ap Oy) Nu(cV Gp nU) Ml(aY cX Ou) Ni(bO cV Hl) J

OwjB VbeM} nJ{Wh(bQ In Kk Og Pe Po) Uw(aF cY In Jf Ke Mp) Ps(Ao bO Co Pf) Qx(Eq Sj) Ju(bZ Ky) eC(Ra Rb) ApUf GhMz GndH HlPi YeaQ UrbZ} Hc{Va(Gz Ml Nu Ul) Sf(Gz Hv Oi) Ux(cG kP Ow) Ed(Aa Uw) Ps(Jo Uu) eQ(cD Ct) fB(hC Uu) EqlX GzWf HvTl YkbO SiOw ZqdF RtkK bZjB} mH{Ti(bQ cL Ni Po) Sf(aW Mg Rm Sr) Fi(Qx Ra Wm) Ps(Li nD Ni) Uf(Gh Va Ye) FyRt GnaR YkoN XabO RzRh UraO UwPc VacT} Ow{Vz(Hb Ju Or Pj Sf Si Ue) Si(Ed Ml Uh) Gh(Ml nW) hC(Du Zw) jB(dA Kn) EdWh YfLj YkLi RzeM UwaO VjPa VpfB eQkC} aU{kK(Bc Mm Ny Qu To) mF(Cv Dg Dl Mh) Pf(nK nO) fB(Qx Ra) mY(Ns Pc) jB(bZ hB) AwOy WmnK SfoP cToD nOnY kRpl} rZ{jT(lM Mm Mv Oy) Hr(jP Nv Po) iC(jI Mj Qc) jY(Jl Mv Qc) jD(Js Mb) rA(Fr Nq) LuIh NjrC lllO LjjH NvNy PejI} dU{Mg(Qv Rb Rg) Ld(bV Kx Pb) Uf(Kj Kl Uu) cS(Co Dg Ns) Ez(bU Kz) Ju(Di Ic) Kc(bV oN) NsbZ JdJv RabC aXbA} lY{Nq(Iz Jh Mk Ml Of Pe) Mj(Io Mg Mt Ny) Uf(Li Mb Rc Ss) Mu(My Ny Pc) cS(Ml Nb) LuMp MbKg MhMv} mU{Ye(aO dI Lj Up) Gn(Fb Jv Kp) Nm(Nb Nt) Mm(Pf Pg) EzOf FyTo NsMh NtJo LuMb MzRc NbIi YkcY QvPi UwbB} Gh{oP(cG cX De Kp Ny) kR(Jl Ld Lv Mh) Jl(Cv mF) cY(nW oQ) dR(aM Sf) EznA LuMp MlPf bOhC} eP{Ok(cC Li Nq) Bg(Ic Ur) Ex(Co Iu) Mg(Qv Ue) Jd(bF bV) Uf(Lh Nq) NsMp MvUe NlcG KgaO KjUr VqoN} Hv{Wm(Du Ru Uz Vh Wg) Wg(Hf Qx Ra) Rv(In Lw Ud) Uz(Hf Qx Ra) Ye(Aa Kd) RaRu KojP} Nv{Va(An As Cw Nf Oy Vh We Tl) Mb(Hq Ng Og) Rc(Uz Vj) DuMh YfIi NuNg HlOi WfNy} Pg{Sf(Cv Jo Mh Mz) Iv(Jm Pf) Va(Cv Nh) Vj(Hb Om) DeOy NqSi MhZq WfkC Jtml JvkP RzmT RteM} Ed{Yd(Ju Mz Om Sf) Aa(bS Lh Pi) Si(Ef Ez Ld) Ax(cT lK) Ib(Eq Wh) AoSf DeGn DubO} Ez{nA(Al Ap Bc Zq) jB(aD aL Ld) Bb(kP nK) oQ(bA cT) MfjO NfUx UemS JtnO PckP} mT{Gn(cR Jd Nq) Rz(Aj Mj Uk) Uw(dF Jq) AoVa NqNu NsMb HlaO JoOk YebW RgPc bZcM} Id{jI(Db Je Mf Qn Qt) jG(Bo Lh Qt Uh) lM(jO Ml Qb) jP(Ko Ky) OrlO} lX{aQ(Aa Bb Jo Nm Of) cY(Bb Ju Rj) GnaK YdQv WdUg WebQ JudR JvpI dJeC} Zq{dF(An bS cG dG dH Nf Pi Yf) Jp(aO Mh) mM(Fw Lv) IjmI IreM} Vj{Aa(Jq Mz Ny Tv Up Vp) Si(Fy Jp Pi Vp) Pa(Oi Rc) HbVp LjOa} nO{Pf(cM Cs Ju Mm) Al(Dk hC Jl) bZ(cM Jo Jt) Cv(dR Lv) MjUg QzYe} kK{Al(gL Uv) Ar(Pe Pf) Nq(Ny Ur) Oi(Xa tF) AdtF TiNb YkcY WhbB NybZ UseC} De{Oy(bO cB cK Iv Mm Oz Po) Mh(Em Hl) Jo(cB Iv) AxDr MjHl} Ky{jG(Bb Bc Js Li Qv) lM(Ax jF Ko) BojU NmtF LylO UedI HbjP} hR{Qv(jG Ly Uv) jO(Hr jD Ly) Vq(Tt Vo) bO(jG lK) LjjH aMlK aOjG} nA{Pi(Hl Jm Wb Wm) Al(Jl Qu) In(Ps Vw) bO(Wh Xa) QuVb KlUf} jP{Bb(Iu Kf Ld) Ko(Bc Iu Ra) BoLi FrOk IudI SsKl JoLd JsOr} Nt{Ng(Iv Ly Mj Mu Nq) Jo(Iv Nx Po) Jt(Ok oQ) LioQ} Jv{gZ(bE Im Iu Mi Mt) fA(Dd Jn) pI(bA cT) NqVz NsOr} Uw{kP(Bb Hw Jl Pc Si) cM(No Oa) lW(Bb Jl) BoOk dDmM} nK{In(We Wh) Jg(Uf Vb) MjWf SfUp SscS WeVb QwbZ QuUr LhUx} Hl{mI(bF hC Jl) Nb(Fi Tj) Rc(Jq Vp) Qe(eM Hb) MihC} eQ{kC(bO cT Mp) Ld(aR nD) AlbV MgIz MwbQ HboN QnPc} jB{Ld(aQ cL Pf) bZ(Jq Kz Nx) AlUu NidD JfiO bAbW} oP{Du(Kx Li Na Pd) ChOp FdMz GlSi MmJh XaOi LtnD} oD{cT(Ar As dG dM Li) aF(Fy Ri) FbcZ KnUf OghC} cB{bV(Lz Mh Ng) Po(Jo Ns) AxOa DlIm FwJo NsNg} pI{Fy(aF Ju) Ld(bI Cw) Pc(Hb Tv) JfbC QhcT JubA} dX{Jf(dE Nx) MjMt TtdR InPi QzLh aOpF bAkQ} fB{Qt(Dc Jq Mj Tv) WmOm PoQg UaPc QyaO} lM{Ax(Fp Mh Uh) cH(aO Iu Ko) EtKo GlKj} Mz{Yf(Ii Ks) Rc(Uz Wg) WgJm TlOk UoVa} bO{jG(aI Bb Or) AaUh AwOy WdmF RzmI} cM{Qe(Rt Vb) Ux(Im Pd) JlRt JtVb PsUu} Iv{Ok(Jt Mb) DrdF GnhC NuNg JlJm} Ly{Dl(jD jU) MfjU aCaX aWjl} Si{NqbA UaPf UcUh JqRj cYoQ} Or{AaNa MmVw JsjY JtlK LdqW} dI{hA(Ct Je Ra) Uf(Nm Ue)} jO{AnAp MfjD MjiC JoUv LjrY} Lv{kC(Nm Pb) BojU WhnD} Jq{Yf(Ib Ny) Va(In Rj)} Ps{EfMh MkIu HbUh cMnD} Oy{AnhA AwcL UaTm RzhC} Pc{kP(Qu Uc Tj) eFfA} Al{JlmF bFgC bZmM} Mp{Vz(hC Lu) DuhC} fA{MlMw QmdJ cMcX} Aa{Rt(Ld Ql)} Po{DukR NsbS} Fy{AxmS UgfR} Gn{RcVp mIhC} Mf{WcVa LjqW} Mh{EqMl aCaX} Mm{GcaO WcPf} Jl{AdRz WfcV} Ok{DrRc NuJt} gC{QzcS aFbR} tF{JoPd aOgZ} lW{KlVb PfdA} kC{DkUr MjOe} YfKsOm FiNqIb GzcTfP MdNbTl MtUoUx TobVgZ YkaQmM VzcMoQ JeaMqV WhbBnD QvUvhW KjRzmS LjjDrY RvPikP Constrained panels with 2 analytes, where 1.0E-8 >= 'AUC p-value' > 0. Contains 35 panels of 142,491 total panels evaluated. : gV(aL aZ bA cT CU) Is(Gb Uy Yi Yl) kG(Mj Nb Yj) Cu(Gb Yi) Lx(Yi Yl) Hl(nR nU) cU(Gd Yg) hR(cF rZ) lN(Ky Tz) oO(oF oQ) GbNw NsoE JvoT LdeP LpkN YlOu aAeD aFoW Constrained panels with 2 analytes, where 1.0E-7 >= 'AUC p-value' > 1.0E-8. Contains 25 panels of 142,491 total panels evaluated. : Nd(Lp Rx Sh) lN(aM Or rZ) Yi(Jr On) kG(Hl Tz) oO(aJ Nn) AxIs BclL DcgV GbJr GdGp NqlY MxrZ TopH HbQd IvaA UtmE PcoV cUnl Constrained panels with 2 analytes, where 1.0E-6 >= 'AUC p-value' > 1.0E-7. Contains 88 panels of 142,491 total panels evaluated. : kG(aF Fw Gn Gp Hp Is Kq Lx Mp Nd Or Pg Rv Ut Vb) cU(Bo cA cF cI dH Jr Lh Mm oE Yi) nR(cF Jj Mm nI Nm oO) aA(Lv Mb Nj Nt oO) oE(Hc oO Pc Um Vv) Nd(Hl Sf Va Yf) lN(Dl Fr hR Mx) Gp(Fi Sf Sh) Tz(Hp Rx Va) kF(Mb Oi Qd) rZ(jD jP jT) oO(aP bV Nb) De(Gd Oy) Gb(Pg Vu) Rx(Fy Jr) eD(jO Uv) lL(Id Mx) AaaZ GhoF MbOn TnnU IqIs YiPg SfoP JuoT LpVu YlOr VaVv PcoW aFmP hRjO Constrained panels with 2 analytes, where 1.0E-5 >= 'AUC p-value' > 1.0E-6. Contains 211 panels of 142,491 total panels evaluated. : cU(aA aV aZ bQ bR bU cB cC cE cO cT cY dA De Hp Hr Me oO Oy Sf Sh Uw) kG(aA hC Hr Ic Jl Ke Ma Mv Mx Nq Ou Pb Pc Qa Qd Tn Yd) nR(aA Ad aF Dg Gb Gn Hr Ju Lh Mb Mn Nb Pc Rb To Um) oO(aF aO Aw bQ bZ cF Cu dF dG hB Kq Mj Mt) oE(Ad Ax Dg Ed Hr Iu Je Jf Nd Ne Oz Qn Tz) aA(Aa Ik Mk Mx Nl Nu On Pg Po Qd) Gb(cG Fy Gp Hq Jp Lx On Qd Tz) Nu(Is Jl Lv Mx Mz Nv Oh) lN(Dg jP Mf Mt Mv Nn Nq) Yi(Jl Mt Nd Nw oF Vi) Cu(Ad Dg Hl Hp Jo) Nw(Ik Me Rx Si Va) gV(Ba bO Cp Cw dD) Mb(Ji Nv Ok Pg) Is(Hb Jm Lj Rm) Sh(Hc Hq Ou Vu) Jj(Iv kF Nt Pg) Jr(Em Hp Si Yl) Lp(Hv mU nI oP) Me(Mx Nn Nv) Nd(Qv Ry Um) Rx(aZ cT Gp) On(Iv Nj Ry) eD(cF jI jP) kN(Nb Nq oT) Nt(Jo Ng) Lv(Iv Mx) Lx(kF mZ) Mj(kF nI) Hp(Ed Pg) Tz(Qv Si) Qa(Jm Nx) Qd(Ax Iu) Ld(dU Yl) aO(nI oV) lL(bO jD) oF(fR Hl) oT(Ow Vv) YfGp PoLj IbVi TnRc ZqdF RfOh UfeP aPcF Constrained panels with 2 analytes, where 1.0E-4 >= 'AUC p-value' > 1.0E-5. Contains 546 panels of 142,491 total panels evaluated. : Is(aA Ad Bb cF cU Ii Iu Iv Jj Ju Jv kF Lv Mb Me Mh Nj Nk Nl Ns Nt Of Qv Rx Uw Va Yj) Qd(Ad Al Bb cF cU Iv Jm Jv Ko Lh Li Lj lY Mb Mx Nl Nn Ns Nt Nx oE Si Uy) kG(aO Aw Cu Di Hu Jj Jk Jq Kd Lu Lv Lz Mb Mh Ml Mu Nn Nw Pf Pi Po Ps Uf) Gb(Ed Ez Fw Hc Im Ji Jl Js mP Nd Oh oP Ow Pe Ps Tn Uf Ut Vv Yi) kF(aA Dl kI Lu Lv Lz Ml Mm Nb nI Nm Nq Oe Of Ou Pc Pf Qa Qb Tz) Pg(Ii Iv Ji Jm Jo Lp Lv Mi Mx nI Nj Nl Nn Nt Nu Sh Uy Va Yj) aA(bO cF hR Ji Jl lN Ma Mf Mh Mj Mu Nk Nn nU Nw Nx Ok Qa) Nu(Im Iv Ji Jj Lh Mb Mh Mj Mp Mu Nk Nl Nn On Po Qa) cU(As dJ Im Iv Jj Jo Lv LY mE oT oV Pa Um) oO(Ax Cs cT dD eF fR hC Kx Ld Lx nN pH Pi Yj) Mb(aZ Jk Jl Mi Mj mP mT mU Mx nN Nt nU Nw) lN(An Bo Gp jD jI jO jT Ko Mj Mu Mw Oh Qb) Iv(Ji Jl Lj Ma Mu Mx Nd Nn Nq Nt Nw Ok) nI(aF bF bQ bZ cG Cv dF Fw nU oT Pi tF) Me(aU bV cB cF Lh Mi Mu Mz oE Oh Ok) Nl(Et Im Ji Jj Lv Ma Mx Nn Nq On Po) Rx(aO bA bF Cu dF Hv Lx Oh oP Tn Vv) nR(Al Bb cM DD Di Lz Of Oh Ug Ur) Nt(Ji Lv Mx Nd Nk Nn Nw Of On Qa) lL(aD aM aX Bb bC dI eD hR jP Nq) Cu(Aa Dl Jt Mm Nm Sh Vb Yg Yj) Tn(Ad Bb fR Hb Ib Jo Nd nT Uu) Jr(bO Du Hl Lp Ry Sf Sh Yg Yj) Nn(Lv lY Mh mW Ng Nj oE pH) Yi(Hv Jn Js Mz Nv Oh Ou Qa) aZ(aO aP bO cF De Lu oE Uy) Lv(Mi Mz Nv Oh On Qa Qb) Mh(cB jD Lx Mx Mz Nv On) Nd(Ik Ue Uf Vj Vu Yl Ye) Tz(Hb Ib Lp mZ Uw Uy Yl) gV(aU Ax bB bQ cG Cs Dd) jO(Ap jD Ly Mf Mx Ni Um) Ns(Lx nU oF Po Qa tF) Jj(Ik Mx nU Nx On Po) eD(dI jE Lu Mv Nq qX) oE(Gh Jm Jo Mp Nm Uo) Lp(mW Nb nU oF Vv) lY(Kq Ma Mj Mu Mv) oT(bH iO mP mS oN) Lx(Du Hp Ry Uy) Nj(Ji Jl Po Qa) Hl(Ho kN mW Nb) Jo(cB De Ut tF) On(Ad Of Vh Yg) Ou(kN nO Sf Vz) cF(aJ bA Ed nO) Gd(Aw Hc Vu) Hv(Uz Wg Yl) Nv(Of rZ Va) Vi(nJ nU Ny) aF(nN nU

Figure 40 Continued oV) aO(hR kE Yg) aP(cB dG dH) mZ(Lz Pe Pf) oF(Du Hp Sh) De(bO Of) Mx(jP Mi) Qa(Iu Lj) Ji(Bb Hb) Nw(Uy Yl) Ut(Qv Si) Pi(Aa kE) bF(oV Sh) tF(Ky Um) mE(Kq Qu) hR(jH Lu) rZ(Il Qe) AloW AwOy BojV CthA PoOg GpNe NmUf MzIk NbYj NgcB HpVu IdjI HcVa YgdF JIJm JuOr JvOh RtVv NypH OwjB UrnU VhnC aCaX bOjG cGeP cSdU jDjP

Constrained panels with 2 analytes, where 1.0E-3 >= 'AUC p-value' > 1.0E-4. Contains 1,259 panels of 142,491 total panels evaluated. : Me(aK aO aP aR aZ bO cC cL cY De Et Hc Ih Jh Jj Jk Jl Jp Jq Js Jt Lw Lx Lz Mf Mm Mp Mt Nd No Nq Nx oF Pc tF) Mb(aU bO bV cF cG cL De Et Fr Ih Ij Jp Jq Js Jt Lh Lv Lw Mm Mp Mt Mz Nb Nd Nl Nn No nT Oh oT Pe Po Qa Qb) Oh(eD Hb Hu Ik Is Iv Jh Ju kG Lh lL Lx Mh Mx Mz Nb Nj Nl Ns Nt Nv Nx oO Pg Po Qa Qv Rm Um Vz Yl Wm tF) Jl(Hp Ji Jj Jo kF Lh Lp Lv Mh Mi Mx Nb Ng nl Nk Nl Nn Ns Nt Nw Nx Of Og Pg Po Qa Qd Qv Rx Um Uy Yl) Gb(aA Ao aZ bA bQ bZ dF Dk Et Ho Ij Jd Jt Ke kF Ld Ma Mi Mj Mp Mt nH Nt nU Oa Ok Ou Pf Qe Ua Uh) Is(Aa aU bO cB Cw De Gd Hl Id Ji Ko Ma Mi Mx Ng Nn Oe Og Ok On Pg Rt Ry Sf Si Ue Um Ux Vb Vh Vi) cF(aM bO bV cG cS cT dF Ji Jj Jv kF kG Ky lN Lv Lx Ly Mh Mi mZ nT Nw Or Qv Sf Sh Tz Up Vu tF) On(Bb Gd Hl Hp Hq Hr Ii Jg Lh Mm Mx My Ng Nk Nm Nn Og Om Oy Pb Qa Qd Si Uw Ux Va Vb Yj Yl) Tn(Dg Ez Gd Gz Hp Ii Jd Jg Jt Jv kI Kl Ng nN Ny Ok Pj Qu Qv Rt Ry Sh Si Um Ux Va Vb) Lv(aZ cB De Im Ji Jj kC Mh Mj Mt Mu Nb Nd nI Nj Nk Nq nR Ns Nw Ok Po Qd Va tF) Pg(Hl Hq Im Ju Jv kF Lh lY Ng Ns nU Nw Of Ok Oy Pb Qa Rt Rx Sf Si Um Ux Vb Zq) oO(aL aY bA BO bR cE cG cS Cv Dd Di gL Hc hG Ju Jv mP oN oP Or Ou Qv Um Yi) Jj(aU cB Cu De Et Ho Ij Im Jk kN Lx Mj mP mU Nj NN nT Nv Qa Qb Qd Ut tF) Mh(aU aZ cL cS De Et Ho Im Lh MP MT mU Nb Nj Nk Nl nN Nx Ok Yh tF) kF(bR Cv DD Dg eC Gd Ji kE Ky Lh Mp Mu Mv Mx Nw Or Pe Po Rg Rx Ug Um) Nl(Fr Jk Jp Jq Lh Lx Mi Mj Mp Mt Mu Mz Nb Nd Nv Nw Nx Ok Pc Pe Qa Qb) Yi(aO cB dF dJ Ex Fw hC Hq Im Ji Jq Kq Lh mH Nb nR Pe Pf Po Rc Rx Vv) lL(aA An Ap Ax cB Dl Fr jI Kl Ky lN Mf Mj Mm Mu Mv Nd Nn Po Qv Um) Nd(cB Ed Gp Gz jI jO jP jT Kc Ky Ne Nj Ou Ow Tz Uo Ut Yj tF) Um(aC aR eD hR Hx Jp Mj Mp Mx Mz Nb nO nU Or Qv Tz Ue Ut Vu) nR(aL aZ Cv fP Gd Gh Hp Jo Jt kG Lp Lx Ml Ni Ns Sh Uw Uy Vb) Cu(Ax Bb bO De Gd Ii Lp nI Nn Of Rt Ry Uw Uy Uz Vh Vi Wg) aO(aM aR aX bC bO cE Hp Je Jf lM mP nN nU oT oW Sf Sh Zq) Mx(aZ cB Im Ji kN Mp nI Nj Nk Ns Nv Nx Po Qa Qv qW Ue) Qd(aU cB Ji Ju Ke lN Lp Ma Mu Nj Nq nU Ok Pj Qv Ue tF) Rx(bO bQ cL Hc Hq Js kN Mj Nb Ns Nv Oa Or Ow Pf Qn Vp) Vu(dI Gh Hb Hl Iu Jo Ju kG Ly mE nI Qv Si Ue Ux Va Ye) Ut(dU fR Gd Ib Ii Jv Mm Ng Pc Ry Sh Ue Uu Va Vb Vh) kG(aM bF dD dI dR Ez fP mU Mw nI nU Pe Qb Qn Vp tF) Dc(aA aP aU Bo bV cT gV Iv Jr Mm Ne Ng Oe Og Yj) Nu(Bo Et Jq Mi Mt Ng Nj Nq Nw Nx Og Ok Pc Pe Qb) oT(bA bC bU cT dN eF Ez Hc Lx Ma Mp Nb Ni Ny Ou) Ed(aU Ax bO cI Gn Ju Lj Lp Qv Sf Uy Wh Yh) Tz(Aa Ax Bb bN eD Jo jV Li Mm Ns nU Pc tF) Qa(fB Hw Ij In Ma mE Mi Nn nU Nv Nw Pb Pc) cB(aA aJ bV hR Im Iv Jr Lp Lz Nm Ns Nw Oy) Lx(cC Hl Mp Mt Mz Nk nU Pc Sf Si Yj Zw) Nb(Du kE Mz Nj Nk nT nU Ry Sf Sh Vb Tl) Qv(Fw Gp jG jO Ly Mp Or Ou Uo Up Yh tF) Nn(cG eD Ik Ji kE nA Nk oW Po Qb Ue) Jr(Bo bS cK Dr Gn Ib MU nN nU Tl) aZ(aA aJ cT Fi Mm Ne Nt Po Si Yh tF) Gp(Aa aC Ap cU Fw Ho Ju Jv mZ tF) Uy(Fy Hq Hv Jp Js Mp Ou Qe Vp Vv) bO(aJ aM aP Aw bA Bo bV hR Iv Yj) dF(aR cE Dg dH Gh gV Ng Oe Oy Sh) Nj(Et Fr Jp Lh Mi Mj Nq Nw Ok) Nk(Et Ik Im Ji Mi Mj Mr Ni Nq) Ue(Ma Mj Mu Mv Nq Or Ou Uf Vj) eD(aM Fr hR jD Lj Md Mm Mu Pc) nI(cS hC Kq Lu mU mZ nT oE Po) Ik(Et Jp Jq Lh Mi Mp Og Qb) Im(aC Bb Dl Iv Jp Lj Pj Si) Sh(Ao cL Hv Jp Mn Mv Nq Vv) Nw(Bb cU Hb Hp Po Ry Uw Vz) cG(Bo cE Dg dH Jo Mm Ng Oy) nU(aL bV cT Cv dD Pc Vv Ye) Nt(Hq Ly Mi Mt Mu Ok rZ) Yj(Fw Gd hC lv mW Nv Vi) Yl(Hq In Lh Mj Nq Nv Ow) tF(Bo Jf Kx nY Or Pc Uo) hR(aJ Hr jD jE jI Lj Ly) lN(dI Hu jE Jk Lu Po Qt) Nm(Fw Ho Ky mP nN oW) Mm(Fw Ky mU oW pH Vj) Mp(Iv Jp kE kN lY Va) Jv(Bo cH Ky Nq oF Ou) aA(aR dH mE Mi mP nN) bV(Bo cC Je Jf Mi Oe) gV(aK Al aM Ar aX cY) lM(aJ aP Bo Id Ko Nq) Ax(Ji Oa oF Or Qe) Gd(Ez Fy Pf Uf Yh) Ns(aU Iv Mj mU Mz) Ly(hA jP jT oF Or) Ng(Fr Mv Nq Nv Po) Hp(Fw Jp mU nH Vv) Si(Jp Ou Ow Ua Uh) Sf(bF Fw Hc Hq oF) Pc(Iv MZ nN pH) cT(Aa aR Bo Jo oV) cU(fP Je Jf Ju Vc) Dg(aP Ba jO Ma) Gh(dR hC kR Ou) Lu(jO jP mU nN) Hb(Or Qe Uh Vv) bA(Aa cC cS oV) lY(Fr Mt Mw Qu) kN(Al Aw Cv Mv) Gn(Ho Hv mP) Mu(Ji kE mE) Hc(Lp Ux Vb) Qb(Jm Ma Nx) Jf(aC hG oF) Ju(Ky mZ Ou) Va(Ps Vp Yh) Vv(Ux Vb Vw) aP(bL Bo bR) jP(Bb Id Ko) Ad(Mz Vi) Po(jT Li) Mf(jD qW) Mi(Iv Mj) Vz(Or Ow) Jo(Fw Uf) Ry(Nv oN) Lj(oW Pe) Lp(Ho Ou) Of(mU nN) Uw(Jp nJ) Vj(Hq Pa) Pi(kI mE) aL(aR mP) aU(Ar Iv) bF(kI nT) eC(kK mZ) nO(dR pK) mT(cS Kq) mW(Dd Ld) nC(Wh Ti) hC(Hl Rz) jG(jO Ky) jI(An Ko) AaJi AlQe BbOk DrPe ExeP FrUx MvkE YhRc JehG WcPf QxmZ JtnN YemU LiUf RvnL NxoF OrjV UoaC VbVw PbpH aJdH eQkC hArA jDjT

Figure 40 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Aa | mg/dL | 7.1E1 | 1.1E2 | 8.0E1 | 1.2E2 | 5.5E1 | 8.4E1 | 7.0E0 | 1.2E1 | 4.0E2 | 4.8E2 | 186 | 86 | 186 | 86 | 0.68 |
| Ad | ug/mL | 4.2E-2 | 5.9E-2 | 6.6E-2 | 2.5E-1 | 7.9E-2 | 1.1E0 | 6.8E-4 | 9.4E-4 | 3.7E-1 | 8.5E0 | 87 | 54 | 87 | 54 | 0.61 |
| Af | ng/mL | 1.3E0 | 1.1E0 | 1.3E1 | 4.7E0 | 6.0E1 | 6.4E0 | 1.7E-3 | 1.7E-3 | 5.3E2 | 2.3E1 | 87 | 54 | 87 | 54 | 0.49 |
| Aj | ug/mL | 1.6E0 | 2.7E-1 | 2.5E0 | 1.8E0 | 2.4E0 | 2.4E0 | 1.5E-3 | 2.1E-3 | 6.1E0 | 6.1E0 | 87 | 54 | 87 | 54 | 0.39 |
| Al | mg/mL | 7.5E-5 | 1.1E-4 | 2.3E-4 | 3.3E-4 | 4.2E-4 | 4.6E-4 | 4.6E-6 | 7.6E-6 | 1.8E-3 | 1.8E-3 | 87 | 54 | 87 | 54 | 0.60 |
| An | U/mL | 5.3E1 | 8.9E1 | 2.3E2 | 3.8E2 | 6.9E2 | 1.1E3 | 6.1E-1 | 6.4E-1 | 5.5E3 | 7.8E3 | 87 | 54 | 87 | 54 | 0.61 |
| Ao | pg/mL | 9.2E1 | 1.0E2 | 8.6E2 | 1.8E2 | 4.9E3 | 1.9E2 | 2.8E0 | 5.4E0 | 3.9E4 | 8.3E2 | 87 | 54 | 87 | 54 | 0.58 |
| Ap | ng/mL | 3.2E1 | 3.5E1 | 4.1E1 | 4.9E1 | 4.0E1 | 5.1E1 | 2.0E0 | 2.4E0 | 2.8E2 | 2.9E2 | 87 | 54 | 87 | 54 | 0.55 |
| Ar | ng/mL | 4.4E-1 | 1.7E0 | 2.5E0 | 5.2E0 | 6.4E0 | 1.0E1 | 4.1E-2 | 3.4E-2 | 4.7E1 | 5.1E1 | 87 | 54 | 87 | 54 | 0.69 |
| As | ng/mL | 8.7E-3 | 1.1E-2 | 1.2E-2 | 3.7E-2 | 1.5E-2 | 1.7E-1 | 1.7E-3 | 1.7E-3 | 9.8E-2 | 1.2E0 | 87 | 54 | 87 | 54 | 0.52 |
| Aw | pg/mL | 1.6E1 | 1.6E1 | 1.7E1 | 1.7E1 | 6.0E0 | 7.1E0 | 6.8E0 | 2.9E-2 | 4.2E1 | 5.1E1 | 87 | 54 | 87 | 54 | 0.47 |
| Ax | ng/mL | 1.5E0 | 6.4E0 | 1.7E1 | 6.5E1 | 8.4E1 | 1.6E2 | 1.3E-2 | 1.2E-2 | 7.7E2 | 8.5E2 | 87 | 54 | 87 | 54 | 0.66 |
| Ba | ng/mL | 9.0E1 | 9.1E1 | 5.7E2 | 7.4E2 | 1.5E3 | 1.7E3 | 1.1E0 | 3.1E0 | 8.1E3 | 8.1E3 | 87 | 54 | 87 | 54 | 0.54 |
| Bb | ng/mL | 3.7E0 | 6.0E0 | 6.0E0 | 9.4E0 | 7.9E0 | 8.9E0 | 4.1E-3 | 6.8E-1 | 4.9E1 | 3.7E1 | 87 | 54 | 87 | 54 | 0.64 |
| Bc | ng/mL | 3.1E1 | 6.1E1 | 1.1E2 | 1.6E2 | 2.1E2 | 2.7E2 | 4.9E-1 | 4.0E0 | 1.0E3 | 1.2E3 | 87 | 54 | 87 | 54 | 0.61 |
| Bg | ng/mL | 1.1E-1 | 1.2E-1 | 4.7E0 | 1.1E1 | 1.9E1 | 5.6E1 | 5.3E-4 | 1.9E-2 | 1.5E2 | 4.0E2 | 87 | 54 | 87 | 54 | 0.53 |
| Bn | ng/mL | 5.6E-2 | 5.6E-2 | 1.1E0 | 2.1E0 | 2.0E0 | 8.0E0 | 5.6E-2 | 5.6E-2 | 8.5E0 | 5.8E1 | 87 | 54 | 87 | 54 | 0.51 |
| Bo | ng/mL | 1.4E1 | 1.2E1 | 1.5E1 | 1.6E1 | 1.0E1 | 1.3E1 | 1.6E-2 | 1.6E-2 | 3.9E1 | 5.3E1 | 87 | 54 | 87 | 54 | 0.50 |
| Ch | uIU/mL | 1.2E0 | 1.0E0 | 4.2E1 | 4.0E1 | 2.1E2 | 1.8E2 | 3.4E-3 | 3.9E-2 | 1.8E3 | 1.2E3 | 87 | 54 | 87 | 54 | 0.43 |
| Co | pg/mL | 4.4E1 | 5.4E1 | 1.4E2 | 4.4E2 | 4.6E2 | 2.3E3 | 1.5E-1 | 1.5E-1 | 3.7E3 | 1.7E4 | 87 | 54 | 87 | 54 | 0.57 |
| Cp | ng/mL | 2.2E1 | 2.3E1 | 2.7E1 | 5.4E1 | 2.2E1 | 1.7E2 | 6.0E-1 | 1.0E1 | 1.3E2 | 1.3E3 | 87 | 54 | 87 | 54 | 0.56 |
| Cq | ng/mL | 2.8E-2 | 3.8E-2 | 8.9E-2 | 1.1E0 | 2.6E-1 | 6.7E0 | 8.0E-4 | 8.0E-4 | 2.0E0 | 4.9E1 | 87 | 54 | 87 | 54 | 0.59 |
| Cs | ng/mL | 4.6E1 | 2.2E2 | 3.3E2 | 9.8E2 | 1.2E3 | 2.6E3 | 1.0E0 | 8.3E-1 | 1.1E4 | 1.8E4 | 87 | 54 | 87 | 54 | 0.69 |
| Ct | ng/mL | 3.7E-1 | 1.5E-1 | 4.7E1 | 4.3E1 | 1.3E2 | 1.2E2 | 2.2E-2 | 1.1E-4 | 6.2E2 | 6.2E2 | 87 | 54 | 87 | 54 | 0.43 |
| Cu | ng/mL | 2.3E-1 | 3.4E-1 | 3.7E-1 | 2.2E0 | 4.1E-1 | 9.3E0 | 2.8E-2 | 3.5E-2 | 2.4E0 | 6.6E1 | 87 | 54 | 87 | 54 | 0.61 |
| Cv | ng/mL | 3.4E0 | 9.1E0 | 2.2E1 | 3.6E1 | 6.6E1 | 7.7E1 | 2.0E-2 | 5.1E-2 | 5.3E2 | 4.7E2 | 87 | 54 | 87 | 54 | 0.61 |
| Cw | mIU/mL | 2.8E-2 | 4.3E-2 | 4.0E-2 | 1.7E-1 | 3.3E-2 | 9.2E-1 | 8.9E-4 | 4.1E-3 | 1.8E-1 | 6.8E0 | 87 | 54 | 87 | 54 | 0.56 |
| Cx | ng/mL | 8.5E-1 | 3.3E-1 | 5.6E1 | 3.3E1 | 1.0E2 | 7.6E1 | 9.3E-5 | 9.3E-5 | 3.9E2 | 2.8E2 | 87 | 54 | 87 | 54 | 0.48 |
| Db | ug/mL | 7.5E0 | 7.2E0 | 8.5E0 | 8.2E0 | 6.7E0 | 8.8E0 | 4.5E-1 | 8.2E-1 | 4.3E1 | 5.9E1 | 87 | 54 | 87 | 54 | 0.46 |
| Dc | nmol/L | 1.8E-2 | 2.4E-2 | 4.4E-2 | 4.1E-1 | 8.2E-2 | 1.9E0 | 5.2E-6 | 1.3E-3 | 6.3E-1 | 1.4E1 | 87 | 54 | 87 | 54 | 0.62 |
| Dd | ug/mL | 6.3E-2 | 1.6E-1 | 1.4E-1 | 3.2E-1 | 2.3E-1 | 5.5E-1 | 4.8E-4 | 3.4E-3 | 1.6E0 | 3.6E0 | 87 | 54 | 87 | 54 | 0.63 |
| De | ng/mL | 3.4E-3 | 3.4E-3 | 8.0E-2 | 9.7E-2 | 1.5E-1 | 2.0E-1 | 3.4E-3 | 3.4E-3 | 9.2E-1 | 1.1E0 | 87 | 54 | 87 | 54 | 0.50 |
| Dg | ng/mL | 3.2E1 | 3.9E1 | 4.4E1 | 5.4E1 | 3.6E1 | 4.4E1 | 7.8E-1 | 7.1E-1 | 1.2E2 | 1.9E2 | 87 | 54 | 87 | 54 | 0.56 |
| Di | pg/mL | 2.0E0 | 2.7E0 | 2.4E0 | 2.7E0 | 2.4E0 | 1.8E0 | 1.8E-1 | 1.8E-1 | 1.3E1 | 9.0E0 | 87 | 54 | 87 | 54 | 0.57 |
| Dk | uIU/mL | 1.5E-2 | 1.7E-2 | 6.5E-2 | 7.7E-2 | 2.1E-1 | 1.8E-1 | 1.1E-4 | 1.1E-4 | 1.6E0 | 9.8E-1 | 87 | 54 | 87 | 54 | 0.55 |
| Dl | ng/mL | 1.9E2 | 2.5E2 | 2.8E2 | 3.6E2 | 2.7E2 | 3.2E2 | 8.9E0 | 5.5E0 | 1.3E3 | 1.6E3 | 87 | 54 | 87 | 54 | 0.57 |
| Dp | ng/ml | 2.1E0 | 2.1E0 | 5.4E0 | 5.4E0 | 8.4E0 | 1.0E1 | 3.7E-3 | 3.7E-3 | 4.6E1 | 5.6E1 | 70 | 43 | 70 | 43 | 0.48 |
| Dr | pg/ml | 1.2E1 | 3.0E1 | 3.6E1 | 5.5E2 | 5.5E1 | 2.2E3 | 7.5E-1 | 7.5E-1 | 2.5E2 | 1.0E4 | 35 | 23 | 35 | 23 | 0.68 |
| Du | pg/ml | 4.8E1 | 7.9E2 | 5.1E2 | 2.9E3 | 1.1E3 | 6.5E3 | 1.2E0 | 1.2E0 | 5.4E3 | 2.4E4 | 28 | 20 | 28 | 20 | 0.71 |
| Dw | ng/ml | 9.2E-3 | 2.3E-2 | 4.3E-2 | 6.0E-2 | 6.1E-2 | 7.6E-2 | 9.2E-3 | 9.2E-3 | 1.9E-1 | 1.9E-1 | 9 | 8 | 9 | 8 | 0.56 |
| Ef | ng/ml | 9.9E-2 | 1.1E-1 | 7.9E-1 | 9.7E-1 | 1.6E0 | 2.4E0 | 5.7E-4 | 5.7E-4 | 9.5E0 | 9.9E0 | 74 | 49 | 74 | 49 | 0.51 |
| Wm | % | 8.5E-2 | 4.5E-1 | 3.9E0 | 6.6E1 | 2.2E1 | 2.2E2 | 5.4E-2 | 8.5E-2 | 2.0E2 | 1.0E3 | 83 | 47 | 83 | 47 | 0.58 |
| Ed | pg/ml | 5.2E-1 | 2.3E1 | 2.4E1 | 6.3E1 | 3.6E1 | 1.1E2 | 5.2E-1 | 5.2E-1 | 1.3E2 | 5.0E2 | 70 | 43 | 70 | 43 | 0.61 |
| Eo | ng/ml | 6.1E0 | 3.0E0 | 6.9E0 | 7.8E0 | 5.3E0 | 1.3E1 | 3.6E-1 | 3.6E-1 | 1.6E1 | 4.0E1 | 9 | 8 | 9 | 8 | 0.37 |
| Yf | ng/ml | 1.4E1 | 1.7E1 | 3.2E1 | 8.9E1 | 4.9E1 | 1.6E2 | 2.9E-1 | 2.9E-1 | 2.4E2 | 5.9E2 | 30 | 19 | 30 | 19 | 0.54 |
| Tj | pg/mL | 3.7E-1 | 3.7E-1 | 2.4E1 | 7.9E1 | 1.1E2 | 3.4E2 | 3.7E-1 | 3.7E-1 | 8.7E2 | 2.3E3 | 74 | 45 | 74 | 45 | 0.59 |
| Po | pg/ml | 1.3E-1 | 3.5E0 | 7.6E0 | 1.9E1 | 2.5E1 | 4.3E1 | 8.0E-3 | 2.6E-2 | 2.7E2 | 2.2E2 | 180 | 88 | 180 | 88 | 0.62 |
| Ti | ug/mL | 2.3E0 | 6.3E0 | 3.6E0 | 6.7E0 | 3.4E0 | 4.8E0 | 1.2E-1 | 6.0E-1 | 1.4E1 | 1.8E1 | 42 | 27 | 42 | 27 | 0.71 |
| Em | ng/ml | 9.2E-3 | 2.6E-2 | 5.3E-2 | 1.3E-1 | 9.3E-2 | 3.6E-1 | 8.4E-4 | 8.4E-4 | 5.0E-1 | 1.9E0 | 43 | 30 | 43 | 30 | 0.55 |
| Et | ng/ml | 1.3E3 | 2.2E3 | 1.6E3 | 2.4E3 | 1.1E3 | 1.2E3 | 7.9E1 | 3.1E2 | 4.3E3 | 5.0E3 | 179 | 88 | 179 | 88 | 0.69 |
| Eq | pg/ml | 2.6E2 | 4.8E1 | 4.0E2 | 2.9E2 | 4.1E2 | 4.1E2 | 1.0E0 | 1.0E0 | 1.5E3 | 1.4E3 | 28 | 20 | 28 | 20 | 0.37 |
| Ew | U/ml | 2.0E0 | 2.1E0 | 2.8E0 | 2.5E0 | 2.4E0 | 1.3E0 | 1.1E0 | 1.3E0 | 8.8E0 | 5.0E0 | 9 | 8 | 9 | 8 | 0.54 |
| Th | ug/mL | 1.2E0 | 1.6E0 | 1.8E0 | 2.1E0 | 1.3E0 | 2.0E0 | 2.4E-1 | 2.6E-3 | 5.4E0 | 7.5E0 | 42 | 27 | 42 | 27 | 0.50 |
| Fa | ng/ml | 3.5E1 | 8.5E1 | 5.1E1 | 2.6E2 | 5.5E1 | 6.7E2 | 2.6E-1 | 6.0E-1 | 2.6E2 | 3.7E3 | 68 | 42 | 68 | 42 | 0.67 |

Figure 41

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Ez | ng/ml | 4.3E0 | 4.1E0 | 1.6E1 | 1.6E1 | 2.7E1 | 3.5E1 | 1.3E-2 | 1.3E-2 | 1.6E2 | 2.0E2 | 70 | 43 | 70 | 43 | 0.52 |
| Fb | ng/ml | 2.7E1 | 2.7E1 | 2.2E1 | 2.5E1 | 1.3E1 | 8.7E0 | 6.6E-1 | 2.7E0 | 4.3E1 | 4.1E1 | 68 | 43 | 68 | 43 | 0.56 |
| Ex | ng/ml | 7.4E-2 | 1.4E-1 | 1.6E-1 | 2.4E-1 | 2.3E-1 | 3.4E-1 | 3.5E-5 | 1.7E-4 | 1.0E0 | 1.5E0 | 53 | 34 | 53 | 34 | 0.63 |
| Fc | pg/ml | 2.2E-1 | 2.2E-1 | 3.8E0 | 4.0E1 | 9.6E0 | 1.1E2 | 2.2E-1 | 2.2E-1 | 4.4E1 | 3.9E2 | 29 | 20 | 29 | 20 | 0.59 |
| Fd | pg/ml | 2.3E1 | 2.1E2 | 5.8E2 | 2.7E3 | 1.8E3 | 7.2E3 | 4.5E-1 | 9.8E-1 | 9.2E3 | 2.5E4 | 29 | 20 | 29 | 20 | 0.61 |
| Fi | pg/ml | 2.5E-1 | 2.5E-1 | 2.0E1 | 1.6E2 | 5.9E1 | 4.2E2 | 2.5E-1 | 2.5E-1 | 2.5E2 | 1.8E3 | 29 | 20 | 29 | 20 | 0.64 |
| Fn | ng/ml | 2.5E-1 | 2.1E-1 | 4.4E0 | 4.6E0 | 8.0E0 | 6.8E0 | 1.1E-14 | 2.1E-1 | 3.7E1 | 2.7E1 | 70 | 43 | 70 | 43 | 0.52 |
| Fp | ng/ml | 1.0E1 | 2.5E1 | 2.0E1 | 3.7E1 | 2.4E1 | 3.3E1 | 6.0E-3 | 2.8E-1 | 1.3E2 | 1.3E2 | 181 | 90 | 181 | 90 | 0.67 |
| Fr | ng/ml | 3.1E4 | 6.8E4 | 1.2E5 | 1.9E5 | 1.9E5 | 2.3E5 | 1.9E2 | 1.8E3 | 8.4E5 | 8.4E5 | 184 | 91 | 184 | 91 | 0.63 |
| Fw | pg/ml | 8.5E-1 | 7.6E0 | 4.8E1 | 5.8E1 | 3.4E2 | 1.5E2 | 1.2E-1 | 1.2E-1 | 3.0E3 | 9.1E2 | 75 | 48 | 75 | 48 | 0.63 |
| Fy | ng/ml | 3.2E1 | 5.5E1 | 5.3E1 | 1.1E2 | 5.9E1 | 1.5E2 | 1.2E-1 | 1.2E-1 | 2.8E2 | 6.5E2 | 69 | 42 | 69 | 42 | 0.64 |
| Gh | pg/ml | 2.0E0 | 3.7E0 | 2.3E1 | 1.5E1 | 6.6E1 | 3.3E1 | 2.9E-2 | 2.9E-2 | 3.2E2 | 1.4E2 | 29 | 20 | 29 | 20 | 0.54 |
| Gb | % | 4.3E1 | 5.5E1 | 3.9E1 | 7.3E1 | 2.6E1 | 6.8E1 | 2.2E0 | 1.3E1 | 1.0E2 | 3.0E2 | 29 | 20 | 29 | 20 | 0.67 |
| Gc | ng/ml | 6.2E1 | 1.6E2 | 1.0E2 | 3.0E2 | 1.3E2 | 2.8E2 | 6.4E0 | 6.9E0 | 7.3E2 | 1.2E3 | 35 | 23 | 35 | 23 | 0.80 |
| Gd | ng/ml | 3.4E1 | 3.6E1 | 3.5E1 | 3.5E1 | 1.7E1 | 2.0E1 | 3.0E0 | 3.7E0 | 6.9E1 | 8.0E1 | 43 | 24 | 43 | 24 | 0.49 |
| Gn | U/ml | 2.5E-1 | 2.2E-1 | 1.6E0 | 5.6E0 | 5.2E0 | 2.3E1 | 5.6E-3 | 1.2E-2 | 3.0E1 | 1.1E2 | 34 | 23 | 34 | 23 | 0.53 |
| Gl | pg/ml | 8.5E3 | 1.6E4 | 1.1E4 | 1.5E4 | 9.2E3 | 1.0E4 | 9.1E1 | 4.0E2 | 3.1E4 | 3.1E4 | 75 | 48 | 75 | 48 | 0.59 |
| Gp | U/ml | 1.2E0 | 1.0E0 | 2.1E0 | 2.5E0 | 2.6E0 | 3.6E0 | 1.5E-2 | 1.5E-2 | 1.6E1 | 1.8E1 | 75 | 48 | 75 | 48 | 0.48 |
| Gz | ug/ml | 6.4E0 | 9.6E-1 | 6.2E0 | 4.0E0 | 6.0E0 | 5.0E0 | 4.2E-2 | 1.0E-1 | 2.5E1 | 1.5E1 | 48 | 31 | 48 | 31 | 0.43 |
| Ha | ng/ml | 1.6E0 | 4.8E0 | 5.8E0 | 1.5E1 | 1.4E1 | 2.9E1 | 1.7E-2 | 1.7E-2 | 1.0E2 | 1.0E2 | 68 | 43 | 68 | 43 | 0.67 |
| Nm | pg/ml | 1.4E4 | 2.6E4 | 2.8E4 | 6.9E4 | 6.3E4 | 1.5E5 | 1.0E-9 | 1.0E-9 | 7.8E5 | 9.6E5 | 181 | 90 | 181 | 90 | 0.63 |
| Nn | pg/ml | 1.4E2 | 3.3E2 | 2.0E3 | 7.3E3 | 9.0E3 | 3.5E4 | 1.0E-9 | 3.3E0 | 9.5E4 | 3.1E5 | 181 | 90 | 181 | 90 | 0.61 |
| No | pg/ml | 1.4E1 | 2.6E1 | 2.9E1 | 7.7E1 | 5.5E1 | 1.6E2 | 1.0E-9 | 1.0E-9 | 5.6E2 | 9.1E2 | 181 | 90 | 181 | 90 | 0.66 |
| Nq | pg/ml | 2.3E0 | 2.3E0 | 2.7E1 | 3.6E1 | 8.7E1 | 1.0E2 | 1.0E-9 | 1.0E-9 | 6.7E2 | 6.3E2 | 181 | 90 | 181 | 90 | 0.52 |
| Nr | pg/ml | 1.3E0 | 4.7E0 | 2.1E1 | 5.2E1 | 8.7E1 | 1.7E2 | 1.0E-9 | 1.0E-9 | 9.8E2 | 1.4E3 | 181 | 90 | 181 | 90 | 0.61 |
| Ns | pg/ml | 1.0E-9 | 1.0E-9 | 1.3E1 | 2.6E0 | 8.8E1 | 1.5E1 | 1.0E-9 | 1.0E-9 | 1.1E3 | 1.0E2 | 181 | 90 | 181 | 90 | 0.48 |
| Nt | pg/ml | 1.0E2 | 1.4E2 | 1.3E2 | 2.0E2 | 1.0E2 | 2.3E2 | 1.5E1 | 2.3E1 | 8.8E2 | 1.7E3 | 181 | 90 | 181 | 90 | 0.65 |
| Nu | pg/ml | 1.9E1 | 5.0E1 | 5.2E1 | 8.2E1 | 8.2E1 | 1.0E2 | 1.0E-9 | 1.0E-9 | 3.7E2 | 6.3E2 | 181 | 90 | 181 | 90 | 0.63 |
| Lu | pg/ml | 1.0E4 | 1.0E4 | 1.9E4 | 1.2E4 | 5.4E4 | 1.1E4 | 9.4E2 | 5.2E2 | 5.6E5 | 5.9E4 | 181 | 90 | 181 | 90 | 0.49 |
| Lv | pg/ml | 1.0E-9 | 7.0E0 | 1.5E1 | 2.5E1 | 3.2E1 | 4.0E1 | 1.0E-9 | 1.0E-9 | 2.6E2 | 1.9E2 | 181 | 90 | 181 | 90 | 0.58 |
| Lw | pg/ml | 1.0E-9 | 1.0E-9 | 1.8E-1 | 3.9E0 | 2.4E0 | 2.1E1 | 1.0E-9 | 1.0E-9 | 3.2E1 | 1.8E2 | 181 | 90 | 181 | 90 | 0.54 |
| Lx | pg/ml | 1.0E-9 | 6.0E1 | 1.5E2 | 6.4E2 | 5.4E2 | 2.5E3 | 1.0E-9 | 1.0E-9 | 6.2E3 | 2.2E4 | 181 | 90 | 181 | 90 | 0.65 |
| Ly | pg/ml | 1.0E-9 | 1.0E-9 | 9.3E0 | 1.0E1 | 1.8E1 | 1.8E1 | 1.0E-9 | 1.0E-9 | 1.1E2 | 9.6E1 | 181 | 90 | 181 | 90 | 0.51 |
| Lz | pg/ml | 1.0E-9 | 1.0E-9 | 3.1E0 | 4.5E0 | 3.3E1 | 1.7E1 | 1.0E-9 | 1.0E-9 | 4.3E2 | 1.3E2 | 181 | 90 | 181 | 90 | 0.56 |
| Ma | pg/ml | 4.4E2 | 8.2E2 | 2.3E3 | 3.6E3 | 6.2E3 | 7.9E3 | 1.0E-9 | 1.0E-9 | 6.5E4 | 5.2E4 | 181 | 90 | 181 | 90 | 0.60 |
| Mb | pg/ml | 2.5E1 | 2.9E1 | 3.2E1 | 3.5E1 | 1.9E1 | 1.8E1 | 9.2E0 | 4.1E0 | 2.1E2 | 1.1E2 | 181 | 90 | 181 | 90 | 0.55 |
| Mc | pg/ml | 1.0E-9 | 1.0E-9 | 1.1E-1 | 1.0E-9 | 1.0E0 | 0.0E0 | 1.0E-9 | 1.0E-9 | 1.3E1 | 1.0E-9 | 181 | 90 | 181 | 90 | 0.49 |
| Md | pg/ml | 1.0E-9 | 1.0E-9 | 5.0E-1 | 8.6E-1 | 4.9E0 | 3.9E0 | 1.0E-9 | 1.0E-9 | 6.5E1 | 2.9E1 | 181 | 90 | 181 | 90 | 0.52 |
| Me | pg/ml | 3.1E1 | 3.3E1 | 3.0E1 | 3.4E1 | 1.9E1 | 3.9E1 | 1.1E-1 | 1.0E-9 | 1.6E2 | 3.2E2 | 181 | 90 | 181 | 90 | 0.52 |
| Mf | pg/ml | 1.0E-9 | 1.0E-9 | 5.8E-1 | 1.2E0 | 3.2E0 | 6.0E0 | 1.0E-9 | 1.0E-9 | 3.7E1 | 5.6E1 | 181 | 90 | 181 | 90 | 0.54 |
| Mg | pg/ml | 1.1E0 | 1.8E0 | 6.9E0 | 1.0E1 | 1.2E1 | 2.2E1 | 1.0E-9 | 1.0E-9 | 8.8E1 | 1.5E2 | 181 | 90 | 181 | 90 | 0.52 |
| Mh | pg/ml | 1.0E-9 | 1.0E-9 | 1.0E0 | 1.3E0 | 8.3E0 | 5.1E0 | 1.0E-9 | 1.0E-9 | 1.1E2 | 4.2E1 | 181 | 90 | 181 | 90 | 0.58 |
| Mi | pg/ml | 1.0E-9 | 1.0E-9 | 1.1E0 | 1.2E1 | 9.6E0 | 6.5E1 | 1.0E-9 | 1.0E-9 | 1.2E2 | 5.2E2 | 181 | 90 | 181 | 90 | 0.54 |
| Mj | pg/ml | 1.0E-9 | 1.0E-9 | 6.5E0 | 1.0E1 | 3.6E1 | 3.2E1 | 1.0E-9 | 1.0E-9 | 4.6E2 | 2.1E2 | 181 | 90 | 181 | 90 | 0.53 |
| Mk | pg/ml | 2.1E0 | 2.9E0 | 1.6E1 | 2.7E1 | 7.9E1 | 1.5E2 | 1.0E-9 | 1.0E-9 | 1.0E3 | 1.3E3 | 181 | 90 | 181 | 90 | 0.49 |
| Ml | pg/ml | 1.0E-9 | 1.0E-9 | 1.4E1 | 1.4E1 | 1.6E2 | 6.6E1 | 1.0E-9 | 1.0E-9 | 2.1E3 | 5.1E2 | 181 | 90 | 181 | 90 | 0.56 |
| Mm | pg/ml | 4.5E2 | 8.7E2 | 9.7E2 | 1.6E3 | 1.1E3 | 1.9E3 | 1.0E-9 | 1.9E1 | 6.0E3 | 1.0E4 | 181 | 90 | 181 | 90 | 0.61 |
| Mn | pg/ml | 5.4E0 | 1.0E1 | 1.2E1 | 1.3E1 | 3.3E1 | 1.1E1 | 1.0E-9 | 1.0E-9 | 3.5E2 | 6.8E1 | 181 | 90 | 181 | 90 | 0.66 |
| Mp | pg/ml | 1.0E-9 | 1.0E-9 | 1.1E1 | 5.6E1 | 2.6E1 | 2.6E2 | 1.0E-9 | 1.0E-9 | 1.8E2 | 2.4E3 | 181 | 90 | 181 | 90 | 0.54 |
| Mq | pg/ml | 1.0E-9 | 1.0E-9 | 2.1E0 | 5.3E0 | 1.4E1 | 1.8E1 | 1.0E-9 | 1.0E-9 | 1.8E2 | 1.0E2 | 181 | 90 | 181 | 90 | 0.53 |
| Mr | pg/ml | 1.0E-9 | 1.0E-9 | 2.3E1 | 1.2E2 | 1.1E2 | 4.8E2 | 1.0E-9 | 1.0E-9 | 1.4E3 | 3.4E3 | 181 | 90 | 181 | 90 | 0.59 |
| Ms | pg/ml | 3.8E2 | 2.6E2 | 4.9E2 | 3.7E2 | 5.5E2 | 3.8E2 | 1.0E-9 | 1.0E-9 | 3.3E3 | 1.5E3 | 181 | 90 | 181 | 90 | 0.43 |
| Mt | pg/ml | 3.3E-1 | 1.0E0 | 9.4E0 | 5.5E1 | 5.6E1 | 3.4E2 | 1.0E-9 | 1.0E-9 | 7.1E2 | 3.2E3 | 181 | 90 | 181 | 90 | 0.60 |
| Mu | pg/ml | 1.0E-9 | 1.0E-9 | 2.4E0 | 1.7E0 | 1.9E1 | 6.7E0 | 1.0E-9 | 1.0E-9 | 2.3E2 | 4.8E1 | 181 | 90 | 181 | 90 | 0.53 |
| Mv | pg/ml | 1.0E-9 | 1.0E-9 | 9.3E1 | 7.9E1 | 4.5E2 | 2.1E2 | 1.0E-9 | 1.0E-9 | 4.5E3 | 9.2E2 | 181 | 90 | 181 | 90 | 0.54 |
| Mw | pg/ml | 2.9E1 | 7.4E1 | 3.7E2 | 3.6E2 | 1.8E3 | 9.1E2 | 1.0E-9 | 1.0E-9 | 1.8E4 | 5.3E3 | 181 | 90 | 181 | 90 | 0.60 |
| Mx | pg/ml | 1.0E-9 | 1.0E-9 | 4.2E-1 | 7.0E-1 | 2.5E0 | 2.3E0 | 1.0E-9 | 1.0E-9 | 3.2E1 | 2.0E1 | 181 | 90 | 181 | 90 | 0.57 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| My | pg/ml | 1.0E-9 | 1.0E-9 | 5.1E2 | 2.1E2 | 3.3E3 | 8.9E2 | 1.0E-9 | 1.0E-9 | 3.9E4 | 8.0E3 | 181 | 90 | 181 | 90 | 0.51 |
| Mz | pg/ml | 1.0E1 | 2.0E1 | 2.3E1 | 7.5E1 | 5.2E1 | 2.4E2 | 1.0E-9 | 1.0E-9 | 5.5E2 | 1.9E3 | 181 | 90 | 181 | 90 | 0.68 |
| Na | pg/ml | 1.0E-9 | 1.0E-9 | 6.1E-1 | 9.1E-1 | 1.9E0 | 4.6E0 | 1.0E-9 | 1.0E-9 | 9.6E0 | 4.2E1 | 181 | 90 | 181 | 90 | 0.52 |
| Nb | pg/ml | 2.0E0 | 2.5E0 | 4.0E0 | 7.5E0 | 1.3E1 | 2.5E1 | 1.0E-9 | 1.0E-9 | 1.5E2 | 2.1E2 | 181 | 90 | 181 | 90 | 0.57 |
| Nc | pg/ml | 3.6E2 | 2.1E2 | 5.6E2 | 4.0E2 | 8.5E2 | 5.2E2 | 1.0E-9 | 1.0E-9 | 9.2E3 | 3.2E3 | 181 | 90 | 181 | 90 | 0.44 |
| Nd | pg/ml | 2.7E1 | 1.6E1 | 2.3E1 | 6.0E1 | 1.8E1 | 2.5E2 | 1.0E-9 | 1.0E-9 | 7.8E1 | 2.1E3 | 181 | 90 | 181 | 90 | 0.48 |
| Ne | pg/ml | 4.5E2 | 3.6E2 | 5.6E2 | 4.4E2 | 6.4E2 | 4.6E2 | 1.0E-9 | 1.0E-9 | 7.0E3 | 3.6E3 | 181 | 90 | 181 | 90 | 0.44 |
| Nf | pg/ml | 1.0E-9 | 1.0E-9 | 2.5E0 | 4.3E0 | 9.8E0 | 1.9E1 | 1.0E-9 | 1.0E-9 | 8.2E1 | 1.3E2 | 181 | 90 | 181 | 90 | 0.50 |
| Ng | pg/ml | 2.0E1 | 1.7E1 | 1.1E2 | 8.9E1 | 2.2E2 | 1.5E2 | 1.0E-9 | 1.0E-9 | 1.6E3 | 8.5E2 | 181 | 90 | 181 | 90 | 0.51 |
| Nh | pg/ml | 6.1E1 | 5.4E1 | 8.6E1 | 6.5E1 | 8.0E1 | 6.8E1 | 1.0E-9 | 3.6E0 | 5.6E2 | 5.1E2 | 181 | 90 | 181 | 90 | 0.42 |
| Ni | pg/ml | 1.0E-9 | 1.0E-9 | 8.2E1 | 1.0E2 | 1.3E2 | 1.7E2 | 1.0E-9 | 1.0E-9 | 7.1E2 | 1.1E3 | 181 | 90 | 181 | 90 | 0.51 |
| Nj | pg/ml | 7.2E0 | 5.3E0 | 1.1E1 | 7.7E0 | 1.1E1 | 8.6E0 | 1.0E-9 | 1.0E-9 | 6.8E1 | 4.6E1 | 181 | 90 | 181 | 90 | 0.41 |
| Nk | pg/ml | 1.6E1 | 1.6E1 | 3.1E1 | 3.2E1 | 3.8E1 | 4.2E1 | 1.0E-9 | 1.0E-9 | 2.0E2 | 2.0E2 | 181 | 90 | 181 | 90 | 0.51 |
| Nl | pg/ml | 4.4E1 | 3.7E1 | 6.0E1 | 4.4E1 | 9.1E1 | 4.2E1 | 1.0E-9 | 1.0E-9 | 1.1E3 | 2.3E2 | 181 | 90 | 181 | 90 | 0.43 |
| Hl | pg/ml | 4.6E0 | 1.7E1 | 3.7E1 | 2.1E2 | 6.5E1 | 8.0E2 | 1.0E-9 | 1.0E-9 | 3.0E2 | 3.6E3 | 29 | 20 | 29 | 20 | 0.56 |
| Ho | pg/ml | 1.7E1 | 2.0E1 | 2.2E1 | 5.5E1 | 1.9E1 | 9.0E1 | 1.1E0 | 7.6E0 | 8.3E1 | 3.9E2 | 29 | 20 | 29 | 20 | 0.64 |
| Hp | ng/ml | 1.8E0 | 1.6E0 | 1.3E2 | 1.3E2 | 3.1E2 | 3.2E2 | 1.0E-9 | 8.1E-1 | 8.9E2 | 8.9E2 | 29 | 20 | 29 | 20 | 0.50 |
| Tz | pg/ml | 3.5E3 | 7.2E3 | 7.7E3 | 6.4E4 | 2.0E4 | 3.2E5 | 7.4E1 | 1.0E-9 | 1.7E5 | 2.1E6 | 71 | 43 | 71 | 43 | 0.63 |
| Ua | pg/ml | 2.5E3 | 4.3E3 | 1.5E4 | 1.3E4 | 3.0E4 | 2.5E4 | 2.3E2 | 1.0E-9 | 1.4E5 | 1.2E5 | 71 | 43 | 71 | 43 | 0.57 |
| Ub | pg/ml | 5.8E2 | 4.1E2 | 8.8E2 | 6.9E2 | 1.3E3 | 9.0E2 | 5.4E0 | 1.0E-9 | 9.8E3 | 4.4E3 | 71 | 43 | 71 | 43 | 0.44 |
| Ue | pg/ml | 2.8E1 | 2.6E1 | 3.6E1 | 3.8E1 | 3.5E1 | 3.3E1 | 5.2E0 | 9.8E-2 | 2.7E2 | 1.4E2 | 71 | 43 | 71 | 43 | 0.51 |
| Uc | pg/ml | 7.1E2 | 9.5E2 | 1.3E3 | 3.0E3 | 1.6E3 | 8.7E3 | 1.5E1 | 1.0E-9 | 9.4E3 | 5.7E4 | 71 | 43 | 71 | 43 | 0.55 |
| Ud | pg/ml | 1.0E-9 | 1.0E-9 | 5.5E0 | 1.2E0 | 4.6E1 | 8.1E0 | 1.0E-9 | 1.0E-9 | 3.9E2 | 5.3E1 | 71 | 43 | 71 | 43 | 0.50 |
| Hq | pg/ml | 1.2E0 | 1.2E0 | 1.2E2 | 3.7E2 | 1.5E3 | 3.0E3 | 1.0E-9 | 1.0E-9 | 2.0E4 | 2.8E4 | 181 | 88 | 181 | 88 | 0.51 |
| Hr | pg/ml | 8.5E1 | 8.8E1 | 5.5E2 | 5.5E2 | 1.0E3 | 1.4E3 | 1.0E-9 | 1.0E-9 | 8.4E3 | 8.9E3 | 181 | 88 | 181 | 88 | 0.51 |
| Hu | pg/ml | 5.3E0 | 3.2E1 | 8.3E0 | 5.3E2 | 5.4E4 | 1.3E3 | 1.0E-9 | 1.0E-9 | 6.3E5 | 6.5E3 | 181 | 88 | 181 | 88 | 0.55 |
| Hv | pg/ml | 1.5E0 | 1.3E0 | 2.6E0 | 1.5E1 | 6.1E0 | 9.7E1 | 1.0E-9 | 1.0E-9 | 6.9E1 | 8.9E2 | 181 | 88 | 181 | 88 | 0.51 |
| Hw | pg/ml | 5.5E0 | 6.5E0 | 1.7E1 | 1.3E2 | 5.8E1 | 1.0E3 | 1.0E-9 | 5.1E-1 | 6.4E2 | 9.4E3 | 181 | 88 | 181 | 88 | 0.50 |
| Hx | pg/ml | 8.8E0 | 1.1E1 | 7.7E1 | 5.2E1 | 6.9E2 | 1.7E2 | 1.0E-9 | 1.0E-9 | 9.3E3 | 1.3E3 | 181 | 88 | 181 | 88 | 0.53 |
| Ib | ng/ml | 3.3E-2 | 3.6E-2 | 1.6E0 | 1.5E0 | 6.0E0 | 8.6E0 | 1.0E-9 | 1.0E-9 | 3.6E1 | 5.6E1 | 69 | 42 | 69 | 42 | 0.50 |
| Ic | U/ml | 2.2E2 | 2.2E2 | 1.4E3 | 2.2E2 | 7.9E3 | 1.6E2 | 2.4E0 | 1.1E1 | 6.5E4 | 7.9E2 | 69 | 42 | 69 | 42 | 0.52 |
| Id | U/ml | 5.0E-1 | 1.1E0 | 8.8E-1 | 1.2E1 | 1.2E0 | 6.6E1 | 1.0E-9 | 5.1E-2 | 6.4E0 | 4.3E2 | 69 | 42 | 69 | 42 | 0.71 |
| Tt | pg/ml | 1.7E2 | 1.7E2 | 1.7E2 | 1.8E2 | 5.1E1 | 7.0E1 | 4.3E1 | 7.3E1 | 3.0E2 | 4.4E2 | 63 | 40 | 63 | 40 | 0.50 |
| To | pg/ml | 1.8E0 | 1.4E0 | 2.2E0 | 1.9E0 | 2.1E0 | 2.4E0 | 1.0E-9 | 1.0E-9 | 9.9E0 | 1.2E1 | 68 | 41 | 68 | 41 | 0.43 |
| Tr | pg/ml | 3.6E0 | 4.4E0 | 5.6E0 | 1.7E1 | 6.8E0 | 5.0E1 | 1.0E-9 | 2.4E-1 | 3.8E1 | 3.1E2 | 66 | 40 | 66 | 40 | 0.57 |
| Tn | pg/ml | 3.3E1 | 4.3E1 | 8.3E1 | 2.1E2 | 2.1E2 | 5.3E2 | 3.5E0 | 2.4E0 | 1.7E3 | 2.3E3 | 68 | 41 | 68 | 41 | 0.56 |
| Tv | ng/ml | 1.2E1 | 1.2E1 | 2.2E1 | 2.2E2 | 4.3E1 | 1.1E3 | 1.0E-9 | 1.0E-9 | 3.2E2 | 7.1E3 | 68 | 41 | 68 | 41 | 0.52 |
| Ih | ng/ml | 5.6E1 | 1.3E2 | 2.0E2 | 4.0E2 | 3.5E2 | 6.2E2 | 1.0E-9 | 1.0E-9 | 2.1E3 | 3.6E3 | 181 | 89 | 181 | 89 | 0.63 |
| Ii | ng/ml | 7.1E1 | 1.2E2 | 2.1E2 | 3.0E2 | 5.1E2 | 6.4E2 | 7.3E-1 | 2.3E0 | 5.2E3 | 4.5E3 | 181 | 89 | 181 | 89 | 0.61 |
| Ij | ng/ml | 7.3E1 | 1.2E2 | 2.0E2 | 4.7E2 | 7.0E2 | 2.6E3 | 2.8E0 | 2.1E1 | 6.4E3 | 2.4E4 | 180 | 87 | 180 | 87 | 0.66 |
| Ik | ng/ml | 9.4E0 | 1.7E1 | 2.3E3 | 2.6E2 | 1.6E4 | 4.7E2 | 5.9E-1 | 2.3E0 | 1.2E5 | 1.8E3 | 179 | 88 | 179 | 88 | 0.59 |
| Il | ng/ml | 3.4E2 | 4.9E2 | 1.2E3 | 1.7E3 | 2.7E3 | 3.2E3 | 1.0E-9 | 1.0E-9 | 1.2E4 | 1.2E4 | 178 | 87 | 178 | 87 | 0.57 |
| Im | ng/ml | 1.9E2 | 3.5E2 | 3.5E2 | 8.4E2 | 5.6E2 | 1.3E3 | 1.4E1 | 4.7E1 | 6.0E3 | 6.2E3 | 179 | 88 | 179 | 88 | 0.69 |
| In | ng/ml | 3.2E0 | 3.9E0 | 1.8E1 | 7.1E1 | 8.6E1 | 4.8E2 | 1.0E-9 | 1.0E-9 | 1.1E3 | 4.5E3 | 181 | 89 | 181 | 89 | 0.54 |
| Hb | ng/ml | 2.0E1 | 3.7E1 | 3.0E1 | 4.8E1 | 3.4E1 | 4.2E1 | 4.8E-1 | 2.6E0 | 2.0E2 | 1.9E2 | 69 | 46 | 69 | 46 | 0.66 |
| Hc | pg/ml | 7.2E2 | 6.4E2 | 3.8E3 | 2.2E3 | 1.3E4 | 7.5E3 | 1.0E-9 | 1.0E-9 | 1.0E5 | 5.0E4 | 69 | 46 | 69 | 46 | 0.44 |
| Hf | ng/ml | 1.6E2 | 3.1E2 | 3.7E2 | 4.9E2 | 5.3E2 | 6.4E2 | 1.0E-9 | 1.0E-9 | 2.5E3 | 3.2E3 | 69 | 46 | 69 | 46 | 0.58 |
| Io | ng/ml | 1.0E4 | 1.5E4 | 2.1E4 | 2.2E4 | 5.9E4 | 2.3E4 | 1.2E2 | 1.0E-9 | 7.1E5 | 1.1E5 | 180 | 90 | 180 | 90 | 0.59 |
| Ip | ng/ml | 9.3E0 | 2.9E0 | 2.1E1 | 2.7E1 | 2.9E1 | 2.2E1 | 1.0E-9 | 1.0E-9 | 2.3E2 | 7.8E1 | 180 | 90 | 180 | 90 | 0.60 |
| Iq | ug/ml | 1.1E-1 | 1.5E-1 | 6.5E-1 | 4.1E0 | 2.7E0 | 2.3E1 | 1.0E-9 | 1.0E-9 | 3.4E1 | 2.2E2 | 180 | 90 | 180 | 90 | 0.58 |
| Ir | ug/ml | 3.5E-1 | 9.3E-1 | 1.4E0 | 1.2E1 | 3.4E0 | 4.6E1 | 1.0E-9 | 1.0E-9 | 2.6E1 | 3.7E2 | 179 | 90 | 179 | 90 | 0.65 |
| Is | ng/ml | 1.7E0 | 3.8E0 | 6.7E0 | 1.8E1 | 1.4E1 | 3.8E1 | 1.0E-9 | 1.0E-9 | 1.1E2 | 2.6E2 | 180 | 90 | 180 | 90 | 0.61 |
| It | ng/ml | 1.7E0 | 3.0E0 | 1.4E1 | 2.4E1 | 7.0E1 | 9.4E1 | 1.0E-9 | 1.0E-9 | 8.3E2 | 6.8E2 | 180 | 90 | 180 | 90 | 0.60 |
| Iu | ng/ml | 1.7E2 | 1.8E2 | 1.1E3 | 1.7E3 | 3.5E3 | 5.1E3 | 1.0E-9 | 1.0E-9 | 2.9E4 | 2.4E4 | 180 | 90 | 180 | 90 | 0.52 |
| Iv | ng/ml | 1.3E1 | 2.2E1 | 3.6E1 | 1.8E2 | 8.6E1 | 6.8E2 | 1.0E-9 | 1.0E-9 | 7.7E2 | 3.8E3 | 179 | 90 | 179 | 90 | 0.60 |
| Iz | ng/ml | 1.2E2 | 1.3E2 | 4.0E2 | 2.6E2 | 8.5E2 | 3.3E2 | 1.5E0 | 4.9E0 | 6.1E3 | 1.7E3 | 69 | 46 | 69 | 46 | 0.52 |
| Yg | pg/ml | 2.4E2 | 2.8E2 | 2.2E3 | 8.1E2 | 9.2E3 | 1.1E3 | 1.0E-9 | 6.9E1 | 5.0E4 | 3.9E3 | 29 | 19 | 29 | 19 | 0.60 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Yh | pg/ml | 2.1E2 | 2.6E2 | 3.6E2 | 4.5E2 | 4.7E2 | 5.6E2 | 1.0E-9 | 1.0E-9 | 1.8E3 | 2.1E3 | 29 | 19 | 29 | 19 | 0.55 |
| Yi | pg/ml | 2.2E2 | 5.1E2 | 4.8E2 | 2.4E3 | 6.0E2 | 6.2E3 | 1.0E-9 | 5.8E1 | 2.0E3 | 2.6E4 | 29 | 19 | 29 | 19 | 0.69 |
| Yk | U/ml | 1.0E-9 | 1.0E-9 | 2.8E-1 | 9.9E-2 | 7.0E-1 | 3.3E-1 | 1.0E-9 | 1.0E-9 | 3.0E0 | 1.4E0 | 29 | 19 | 29 | 19 | 0.43 |
| Yj | pg/ml | 1.5E2 | 1.1E2 | 3.4E2 | 2.4E2 | 6.2E2 | 3.3E2 | 1.0E-9 | 5.2E1 | 3.2E3 | 1.5E3 | 29 | 19 | 29 | 19 | 0.50 |
| Yd | ng/ml | 1.6E-1 | 2.8E-1 | 4.1E-1 | 3.9E-1 | 5.7E-1 | 5.0E-1 | 6.6E-3 | 1.7E-2 | 1.9E0 | 2.3E0 | 30 | 20 | 30 | 20 | 0.57 |
| Wb | pg/ml | 2.6E4 | 5.0E4 | 3.0E4 | 7.6E4 | 1.8E4 | 1.4E5 | 6.3E3 | 1.4E4 | 8.4E4 | 6.4E5 | 30 | 20 | 30 | 20 | 0.73 |
| Vz | pg/ml | 3.7E0 | 3.9E0 | 4.6E0 | 5.4E0 | 4.0E0 | 5.9E0 | 1.0E-9 | 7.6E-2 | 1.6E1 | 2.2E1 | 30 | 20 | 30 | 20 | 0.54 |
| Si | ng/ml | 1.0E0 | 1.4E0 | 2.0E0 | 2.0E0 | 3.0E0 | 1.7E0 | 8.6E-3 | 3.3E-1 | 1.0E1 | 6.0E0 | 29 | 20 | 29 | 20 | 0.61 |
| Sf | mIU/mL | 2.0E1 | 2.0E1 | 7.0E1 | 2.4E1 | 1.4E2 | 2.0E1 | 7.8E-1 | 1.7E0 | 7.2E2 | 8.3E1 | 29 | 20 | 29 | 20 | 0.49 |
| Sh | mIU/mL | 1.7E1 | 1.2E1 | 6.0E1 | 2.1E1 | 1.2E2 | 1.9E1 | 1.4E-1 | 7.8E-2 | 5.7E2 | 6.1E1 | 29 | 20 | 29 | 20 | 0.48 |
| Sj | ng/ml | 4.4E-1 | 4.4E-1 | 4.3E-1 | 4.3E-1 | 1.1E-1 | 6.0E-2 | 2.5E-1 | 3.2E-1 | 7.2E-1 | 5.1E-1 | 29 | 20 | 29 | 20 | 0.52 |
| Rc | pg/ml | 6.9E3 | 7.1E3 | 8.0E3 | 7.0E3 | 5.6E3 | 4.5E3 | 5.5E2 | 6.7E2 | 2.7E4 | 2.2E4 | 70 | 43 | 70 | 43 | 0.47 |
| Rb | pg/ml | 8.2E-1 | 1.2E0 | 2.5E0 | 4.0E0 | 3.8E0 | 9.1E0 | 1.0E-9 | 1.0E-9 | 1.6E1 | 5.6E1 | 70 | 43 | 70 | 43 | 0.54 |
| Zq | 2.6ng/ml | 1.8E2 | 3.6E2 | 2.3E2 | 3.9E2 | 1.6E2 | 1.8E2 | 1.7E1 | 1.1E2 | 5.2E2 | 9.7E2 | 29 | 19 | 29 | 19 | 0.73 |
| Zw | 2.5ng/ml | 5.3E0 | 6.5E0 | 9.8E0 | 1.3E1 | 1.2E1 | 1.8E1 | 2.4E-1 | 2.4E-1 | 5.9E1 | 6.3E1 | 30 | 20 | 30 | 20 | 0.52 |
| Zx | 2.3mU/ml | 8.8E-2 | 1.6E-1 | 2.8E-1 | 3.8E-1 | 5.3E-1 | 5.8E-1 | 3.2E-2 | 5.0E-2 | 2.9E0 | 2.1E0 | 30 | 20 | 30 | 20 | 0.61 |
| Pz | ng/ml | 3.2E3 | 5.7E3 | 5.8E3 | 6.3E3 | 6.9E3 | 4.4E3 | 1.6E1 | 1.9E2 | 7.0E4 | 2.5E4 | 178 | 88 | 178 | 88 | 0.58 |
| Qa | ng/ml | 3.3E3 | 6.7E3 | 6.3E3 | 1.2E4 | 7.6E3 | 2.5E4 | 1.5E2 | 4.2E2 | 4.2E4 | 2.2E5 | 178 | 88 | 178 | 88 | 0.65 |
| Qb | ng/ml | 1.1E2 | 1.5E2 | 2.1E2 | 3.2E2 | 3.1E2 | 5.0E2 | 7.9E-1 | 6.7E0 | 2.8E3 | 4.1E3 | 178 | 88 | 178 | 88 | 0.61 |
| Qc | ng/ml | 1.8E2 | 4.4E2 | 3.9E2 | 6.3E2 | 5.3E2 | 6.8E2 | 1.0E0 | 1.0E-9 | 3.8E3 | 4.3E3 | 178 | 88 | 178 | 88 | 0.63 |
| Qd | ng/ml | 7.9E3 | 1.4E4 | 2.7E4 | 4.1E4 | 1.5E5 | 6.8E4 | 2.4E2 | 1.7E3 | 2.0E6 | 4.3E5 | 178 | 88 | 178 | 88 | 0.68 |
| Qe | ng/ml | 7.7E2 | 1.9E3 | 2.1E3 | 2.7E3 | 7.5E3 | 2.7E3 | 7.6E0 | 8.8E0 | 9.7E4 | 1.8E4 | 178 | 88 | 178 | 88 | 0.69 |
| Jd | ng/ml | 6.9E-1 | 1.7E0 | 5.0E0 | 3.0E0 | 1.9E1 | 4.3E0 | 1.0E-9 | 1.0E-9 | 1.2E2 | 2.1E1 | 70 | 43 | 70 | 43 | 0.63 |
| Je | ng/ml | 1.0E-9 | 1.0E-9 | 2.2E0 | 1.6E0 | 6.4E0 | 2.4E0 | 1.0E-9 | 1.0E-9 | 4.6E1 | 1.1E1 | 70 | 43 | 70 | 43 | 0.53 |
| Jf | ng/ml | 1.0E-9 | 1.0E-9 | 1.1E0 | 1.6E0 | 2.2E0 | 2.5E0 | 1.0E-9 | 1.0E-9 | 1.2E1 | 9.1E0 | 70 | 43 | 70 | 43 | 0.56 |
| Jg | ng/ml | 4.0E2 | 8.1E2 | 7.6E2 | 1.2E3 | 1.0E3 | 1.2E3 | 5.8E0 | 1.3E1 | 1.0E4 | 7.1E3 | 181 | 88 | 181 | 88 | 0.65 |
| Jh | ng/ml | 2.9E0 | 5.2E0 | 2.8E1 | 2.8E1 | 1.1E2 | 7.0E1 | 1.0E-9 | 1.0E-9 | 1.2E3 | 4.9E2 | 181 | 88 | 181 | 88 | 0.58 |
| Ji | ng/ml | 4.7E1 | 8.8E1 | 7.2E1 | 1.7E2 | 7.4E1 | 1.9E2 | 1.1E0 | 1.5E1 | 5.3E2 | 1.3E3 | 181 | 88 | 181 | 88 | 0.71 |
| Sr | pg/mL | 2.9E2 | 8.5E2 | 7.3E2 | 1.8E3 | 1.2E3 | 3.3E3 | 1.0E-9 | 1.0E-9 | 5.5E3 | 2.1E4 | 70 | 42 | 70 | 42 | 0.71 |
| Ss | pg/mL | 1.1E5 | 6.0E4 | 1.5E5 | 1.5E5 | 1.5E5 | 2.3E5 | 7.6E3 | 2.7E3 | 7.0E5 | 1.3E6 | 70 | 42 | 70 | 42 | 0.45 |
| St | pg/mL | 2.2E7 | 5.3E7 | 4.8E7 | 1.3E8 | 6.9E7 | 3.1E8 | 7.8E5 | 1.0E-9 | 4.1E8 | 1.7E9 | 68 | 43 | 68 | 43 | 0.63 |
| Wc | ng/ml | 1.0E-9 | 1.0E-9 | 4.2E-2 | 1.5E-1 | 7.5E-2 | 4.1E-1 | 1.0E-9 | 1.0E-9 | 3.0E-1 | 1.8E0 | 30 | 20 | 30 | 20 | 0.49 |
| Wd | ng/ml | 9.6E0 | 1.0E1 | 2.6E1 | 5.2E1 | 5.5E1 | 1.2E2 | 1.0E0 | 1.5E0 | 2.9E2 | 4.1E2 | 30 | 20 | 30 | 20 | 0.53 |
| We | ng/ml | 2.8E-1 | 4.9E-1 | 1.0E0 | 1.8E0 | 1.4E0 | 5.0E0 | 1.0E-9 | 1.0E-9 | 5.5E0 | 2.3E1 | 30 | 20 | 30 | 20 | 0.53 |
| Wg | ng/ml | 1.0E-9 | 1.0E-9 | 1.0E-9 | 2.7E-2 | 0.0E0 | 1.2E-1 | 1.0E-9 | 1.0E-9 | 1.0E-9 | 5.3E-1 | 30 | 20 | 30 | 20 | 0.53 |
| Wh | ng/ml | 1.2E-2 | 1.0E-2 | 4.0E-2 | 3.4E-2 | 8.2E-2 | 7.5E-2 | 1.0E-9 | 1.0E-9 | 3.5E-1 | 3.4E-1 | 30 | 20 | 30 | 20 | 0.49 |
| Wf | ng/ml | 1.0E-9 | 1.0E-9 | 1.1E-1 | 1.9E-1 | 2.5E-1 | 5.2E-1 | 1.0E-9 | 1.0E-9 | 1.2E0 | 2.3E0 | 30 | 20 | 30 | 20 | 0.51 |
| Ra | pg/ml | 1.0E-9 | 1.0E-9 | 4.1E-1 | 2.0E0 | 9.8E-1 | 9.8E0 | 1.0E-9 | 1.0E-9 | 3.8E0 | 6.4E1 | 70 | 43 | 70 | 43 | 0.50 |
| Qz | pg/ml | 9.1E0 | 1.2E1 | 5.4E1 | 4.7E1 | 9.5E1 | 7.2E1 | 1.0E-9 | 1.0E-9 | 4.5E2 | 2.8E2 | 70 | 43 | 70 | 43 | 0.54 |
| Qy | pg/ml | 3.7E-1 | 4.7E-1 | 1.2E1 | 1.8E1 | 5.9E1 | 1.1E2 | 1.0E-9 | 1.0E-9 | 4.3E2 | 7.3E2 | 70 | 43 | 70 | 43 | 0.55 |
| Qx | pg/ml | 1.0E-9 | 1.0E-9 | 4.3E0 | 4.2E0 | 2.3E1 | 1.7E1 | 1.0E-9 | 1.0E-9 | 1.9E2 | 1.1E2 | 70 | 43 | 70 | 43 | 0.47 |
| Qw | pg/ml | 9.0E-2 | 1.0E-9 | 3.3E0 | 2.7E0 | 1.0E1 | 1.0E1 | 1.0E-9 | 1.0E-9 | 5.6E1 | 6.6E1 | 70 | 43 | 70 | 43 | 0.47 |
| Qv | pg/ml | 1.8E4 | 1.4E4 | 2.7E4 | 2.9E4 | 4.6E4 | 5.1E4 | 1.4E3 | 1.0E-9 | 3.7E5 | 3.3E5 | 70 | 43 | 70 | 43 | 0.48 |
| Qu | pg/ml | 8.3E0 | 7.8E0 | 9.2E1 | 1.1E2 | 1.8E2 | 2.2E2 | 1.0E-9 | 1.0E-9 | 7.1E2 | 9.8E2 | 70 | 43 | 70 | 43 | 0.48 |
| Qt | pg/ml | 1.8E1 | 1.0E1 | 5.3E1 | 3.9E1 | 1.2E2 | 6.6E1 | 1.0E-9 | 1.0E-9 | 7.1E2 | 2.2E2 | 70 | 43 | 70 | 43 | 0.46 |
| Qh | ng/ml | 1.7E1 | 2.9E1 | 3.8E1 | 8.1E1 | 5.6E1 | 1.4E2 | 4.6E-1 | 4.3E-1 | 3.4E2 | 8.0E2 | 70 | 43 | 70 | 43 | 0.64 |
| Qg | ng/ml | 7.1E0 | 7.8E0 | 1.2E1 | 1.2E1 | 1.4E1 | 1.5E1 | 1.5E-1 | 3.0E-1 | 7.5E1 | 8.1E1 | 70 | 43 | 70 | 43 | 0.51 |
| Jj | ng/ml | 6.1E2 | 3.9E2 | 3.0E3 | 6.2E2 | 2.5E4 | 6.3E2 | 2.0E1 | 1.2E1 | 3.4E5 | 3.4E3 | 181 | 88 | 181 | 88 | 0.41 |
| Jk | ng/ml | 3.0E0 | 3.0E0 | 2.4E1 | 2.6E1 | 5.6E1 | 4.9E1 | 1.0E-9 | 2.4E-1 | 3.9E2 | 2.4E2 | 181 | 88 | 181 | 88 | 0.54 |
| Jl | ng/ml | 5.1E-1 | 6.4E-1 | 1.8E0 | 1.2E2 | 3.7E0 | 1.1E3 | 1.2E-3 | 7.5E-2 | 2.0E1 | 9.9E3 | 181 | 88 | 181 | 88 | 0.58 |
| Jm | ng/ml | 1.8E1 | 3.4E1 | 6.0E1 | 8.4E1 | 1.3E2 | 2.3E2 | 1.0E-9 | 1.9E-1 | 1.0E3 | 2.1E3 | 181 | 88 | 181 | 88 | 0.61 |
| Jn | pg/ml | 3.2E-1 | 5.5E-1 | 1.8E0 | 2.0E1 | 6.1E0 | 1.0E2 | 1.0E-9 | 1.0E-9 | 5.8E1 | 7.3E2 | 181 | 88 | 181 | 88 | 0.62 |
| Jo | pg/ml | 4.1E3 | 4.8E3 | 5.0E3 | 6.9E3 | 3.9E3 | 1.2E4 | 2.6E2 | 2.3E2 | 2.4E4 | 1.0E5 | 181 | 88 | 181 | 88 | 0.54 |
| Jp | pg/ml | 7.1E4 | 8.4E4 | 7.2E4 | 9.3E4 | 3.5E4 | 4.6E4 | 2.1E3 | 2.8E4 | 1.9E5 | 3.8E5 | 181 | 88 | 181 | 88 | 0.64 |
| Jq | pg/ml | 9.2E1 | 1.4E2 | 1.5E2 | 3.6E2 | 1.7E2 | 1.0E3 | 5.6E0 | 5.6E0 | 1.1E3 | 8.7E3 | 181 | 88 | 181 | 88 | 0.60 |
| Jr | pg/ml | 2.6E0 | 8.9E0 | 2.8E1 | 1.9E2 | 1.6E2 | 9.8E2 | 1.0E-9 | 1.0E-9 | 1.9E3 | 7.4E3 | 181 | 88 | 181 | 88 | 0.64 |
| Js | pg/ml | 1.4E1 | 1.9E1 | 4.5E1 | 1.4E2 | 1.5E2 | 5.4E2 | 1.0E-9 | 1.9E0 | 1.6E3 | 3.0E3 | 181 | 88 | 181 | 88 | 0.64 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Jt | pg/ml | 2.3E3 | 3.3E3 | 2.8E3 | 5.0E3 | 1.9E3 | 7.3E3 | 1.5E2 | 3.8E2 | 9.2E3 | 5.2E4 | 181 | 88 | 181 | 88 | 0.63 |
| Xa | pg/ml | 1.0E-9 | 6.9E0 | 9.3E0 | 9.9E1 | 1.9E1 | 2.9E2 | 1.0E-9 | 1.0E-9 | 9.6E1 | 1.2E3 | 30 | 20 | 30 | 20 | 0.64 |
| Ye | pg/ml | 1.0E-9 | 1.0E-9 | 6.8E0 | 1.4E0 | 1.8E1 | 3.5E0 | 1.0E-9 | 1.0E-9 | 6.9E1 | 1.4E1 | 30 | 20 | 30 | 20 | 0.42 |
| Tm | pg/ml | 1.0E-9 | 1.0E-9 | 3.6E0 | 1.7E0 | 5.1E0 | 3.4E0 | 1.0E-9 | 1.0E-9 | 1.8E1 | 8.4E0 | 30 | 20 | 30 | 20 | 0.41 |
| Tl | pg/ml | 1.2E-1 | 1.3E-1 | 3.0E-1 | 1.6E0 | 3.7E-1 | 5.5E0 | 1.0E-9 | 1.0E-9 | 1.2E0 | 2.5E1 | 30 | 20 | 30 | 20 | 0.54 |
| Ju | mIU/ml | 1.2E1 | 1.2E1 | 2.9E1 | 2.2E1 | 4.2E1 | 2.4E1 | 2.5E-1 | 1.7E-1 | 2.3E2 | 1.1E2 | 70 | 43 | 70 | 43 | 0.52 |
| Jv | mIU/ml | 2.4E1 | 1.5E1 | 5.2E1 | 2.6E1 | 7.7E1 | 2.9E1 | 2.4E-2 | 1.7E-2 | 4.4E2 | 1.4E2 | 70 | 43 | 70 | 43 | 0.45 |
| Jy | ng/ml | 1.6E-3 | 1.6E-3 | 1.9E-3 | 4.2E-3 | 1.0E-3 | 8.7E-3 | 2.2E-4 | 1.7E-4 | 4.4E-3 | 4.1E-2 | 70 | 43 | 70 | 43 | 0.54 |
| Kc | pg/ml | 2.2E1 | 2.6E1 | 3.6E1 | 5.3E1 | 4.2E1 | 6.8E1 | 1.0E-9 | 1.0E-9 | 1.9E2 | 3.2E2 | 69 | 46 | 69 | 46 | 0.59 |
| Kd | pg/ml | 1.0E-9 | 1.0E-9 | 1.8E2 | 1.3E3 | 7.0E2 | 5.7E3 | 1.0E-9 | 1.0E-9 | 4.8E3 | 3.8E4 | 69 | 46 | 69 | 46 | 0.57 |
| Ke | pg/ml | 1.1E4 | 1.5E4 | 1.2E4 | 3.0E4 | 7.8E3 | 4.8E4 | 6.7E2 | 4.2E3 | 3.3E4 | 3.2E5 | 69 | 46 | 69 | 46 | 0.69 |
| Kf | pg/mL | 5.9E0 | 7.1E0 | 6.4E0 | 9.6E0 | 5.1E0 | 1.3E1 | 1.0E-9 | 1.0E-9 | 2.2E1 | 7.8E1 | 69 | 46 | 69 | 46 | 0.57 |
| Kg | pg/mL | 8.2E2 | 1.1E3 | 1.5E3 | 2.9E3 | 1.6E3 | 6.5E3 | 7.7E1 | 1.3E2 | 8.1E3 | 3.6E4 | 69 | 46 | 69 | 46 | 0.56 |
| Ki | pg/ml | 5.6E1 | 7.3E1 | 6.3E1 | 8.3E1 | 5.2E1 | 6.1E1 | 1.0E-9 | 1.0E-9 | 2.9E2 | 2.5E2 | 69 | 46 | 69 | 46 | 0.63 |
| Kj | pg/ml | 7.6E2 | 9.0E2 | 1.4E3 | 1.6E3 | 1.6E3 | 2.4E3 | 6.6E1 | 3.3E1 | 8.8E3 | 1.5E4 | 69 | 46 | 69 | 46 | 0.52 |
| Kk | pg/ml | 6.8E0 | 9.4E0 | 1.1E1 | 1.8E1 | 1.5E1 | 1.8E1 | 1.0E-9 | 1.0E-9 | 8.1E1 | 6.1E1 | 69 | 46 | 69 | 46 | 0.63 |
| Kl | pg/ml | 2.1E4 | 1.7E4 | 2.9E4 | 2.7E4 | 2.6E4 | 2.7E4 | 2.4E2 | 2.3E2 | 1.1E5 | 1.3E5 | 69 | 46 | 69 | 46 | 0.47 |
| Kn | pg/ml | 1.5E1 | 5.6E1 | 5.1E1 | 2.0E2 | 7.6E1 | 7.2E2 | 1.0E-9 | 1.0E-9 | 3.4E2 | 4.9E3 | 69 | 46 | 69 | 46 | 0.62 |
| Ko | pg/ml | 3.1E2 | 4.7E2 | 4.2E2 | 7.2E2 | 4.6E2 | 8.5E2 | 1.0E-9 | 1.0E-9 | 2.0E3 | 4.1E3 | 69 | 46 | 69 | 46 | 0.63 |
| Kp | pg/ml | 3.2E2 | 3.9E2 | 3.4E2 | 6.9E2 | 2.5E2 | 1.9E3 | 1.0E-9 | 1.0E-9 | 9.4E2 | 1.3E4 | 69 | 46 | 69 | 46 | 0.58 |
| Kq | pg/ml | 3.1E2 | 4.5E2 | 3.6E2 | 4.6E3 | 3.3E2 | 2.4E4 | 1.6E0 | 6.1E1 | 2.1E3 | 1.6E5 | 66 | 44 | 66 | 44 | 0.68 |
| Kr | pg/ml | 1.0E-9 | 1.6E0 | 1.5E0 | 1.3E1 | 2.7E0 | 6.2E1 | 1.0E-9 | 1.0E-9 | 1.3E1 | 4.2E2 | 66 | 44 | 66 | 44 | 0.63 |
| Ks | pg/ml | 1.3E4 | 2.1E4 | 1.9E4 | 2.4E4 | 1.9E4 | 1.8E4 | 5.1E1 | 9.9E2 | 7.9E4 | 5.1E4 | 66 | 44 | 66 | 44 | 0.59 |
| Ps | ng/ml | 1.5E2 | 2.9E2 | 7.0E2 | 9.2E2 | 2.2E3 | 1.8E3 | 5.5E0 | 1.6E1 | 1.2E4 | 7.6E3 | 29 | 20 | 29 | 20 | 0.64 |
| Kx | ng/ml | 1.0E-9 | 4.7E-3 | 6.7E-3 | 1.3E-2 | 1.6E-2 | 2.0E-2 | 1.0E-9 | 1.0E-9 | 1.0E-1 | 7.9E-2 | 68 | 46 | 68 | 46 | 0.62 |
| Ky | ng/ml | 1.6E-1 | 2.0E-1 | 4.1E-1 | 4.9E-1 | 8.1E-1 | 8.3E-1 | 1.0E-9 | 1.0E-9 | 5.1E0 | 4.4E0 | 68 | 46 | 68 | 46 | 0.54 |
| Kz | ng/ml | 1.0E-9 | 1.0E-9 | 3.4E-3 | 4.6E-3 | 5.4E-3 | 7.0E-3 | 1.0E-9 | 1.0E-9 | 1.4E-2 | 2.5E-2 | 68 | 46 | 68 | 46 | 0.51 |
| Rz | ng/ml | 3.1E-1 | 3.4E-1 | 6.8E-1 | 9.3E-1 | 9.3E-1 | 1.7E0 | 4.6E-3 | 1.7E-2 | 3.4E0 | 7.5E0 | 29 | 20 | 29 | 20 | 0.57 |
| Ry | ng/ml | 1.6E-2 | 2.4E-2 | 1.9E-2 | 4.8E-2 | 1.9E-2 | 7.9E-2 | 1.0E-9 | 1.0E-9 | 6.5E-2 | 3.5E-1 | 29 | 20 | 29 | 20 | 0.62 |
| Rx | ng/ml | 1.0E-9 | 1.8E-5 | 1.6E-3 | 1.5E-3 | 2.6E-3 | 2.4E-3 | 1.0E-9 | 1.0E-9 | 8.6E-3 | 7.6E-3 | 29 | 20 | 29 | 20 | 0.52 |
| Ld | pg/ml | 1.0E-9 | 7.5E-1 | 3.3E0 | 5.5E0 | 9.1E0 | 9.7E0 | 1.0E-9 | 1.0E-9 | 6.9E1 | 5.0E1 | 69 | 47 | 69 | 47 | 0.58 |
| Lh | pg/ml | 1.2E4 | 2.1E4 | 2.1E4 | 4.4E4 | 2.9E4 | 7.9E4 | 1.0E-9 | 1.0E3 | 2.6E5 | 4.8E5 | 181 | 89 | 181 | 89 | 0.64 |
| Li | pg/ml | 3.1E3 | 8.6E3 | 9.4E3 | 4.3E4 | 2.9E4 | 1.1E5 | 1.3E1 | 3.7E1 | 2.9E5 | 9.2E5 | 181 | 89 | 181 | 89 | 0.71 |
| Lj | pg/ml | 2.1E3 | 6.7E3 | 1.2E4 | 3.8E4 | 4.2E4 | 7.2E4 | 1.0E-9 | 1.4E2 | 4.3E5 | 4.1E5 | 181 | 89 | 181 | 89 | 0.68 |
| Lp | pg/ml | 6.4E0 | 1.7E1 | 5.2E1 | 1.8E2 | 1.3E2 | 4.0E2 | 1.0E-9 | 1.0E-9 | 5.8E2 | 1.4E3 | 29 | 20 | 29 | 20 | 0.60 |
| Lt | pg/ml | 1.0E-9 | 1.0E-9 | 1.4E0 | 2.3E0 | 5.3E0 | 7.0E0 | 1.0E-9 | 1.0E-9 | 2.5E1 | 2.5E1 | 29 | 20 | 29 | 20 | 0.52 |
| Rv | ng/ml | 5.0E-4 | 5.4E-4 | 8.4E-4 | 2.4E-3 | 8.5E-4 | 4.5E-3 | 1.0E-9 | 1.0E-9 | 2.6E-3 | 1.6E-2 | 29 | 20 | 29 | 20 | 0.49 |
| Ru | ng/ml | 1.0E-9 | 1.0E-9 | 1.8E-2 | 3.8E-2 | 6.8E-2 | 1.1E-1 | 1.0E-9 | 1.0E-9 | 3.1E-1 | 3.5E-1 | 29 | 20 | 29 | 20 | 0.54 |
| Rt | ng/ml | 7.1E-2 | 7.8E-2 | 9.5E-2 | 5.1E-1 | 9.6E-2 | 1.6E0 | 2.2E-3 | 1.3E-3 | 3.8E-1 | 7.4E0 | 29 | 20 | 29 | 20 | 0.58 |
| Yl | pg/ml | 1.3E1 | 1.2E1 | 1.5E1 | 3.1E1 | 1.3E1 | 4.9E1 | 1.0E-9 | 1.0E-9 | 4.7E1 | 2.2E2 | 30 | 20 | 30 | 20 | 0.56 |
| Rm | pg/ml | 1.6E1 | 2.1E1 | 4.3E1 | 6.6E1 | 7.5E1 | 1.1E2 | 2.2E-1 | 3.9E-1 | 3.4E2 | 6.5E2 | 70 | 42 | 70 | 42 | 0.61 |
| Rh | ng/ml | 1.4E2 | 1.9E2 | 2.8E2 | 6.9E2 | 4.9E2 | 2.6E3 | 7.5E0 | 2.5E1 | 3.8E3 | 1.7E4 | 70 | 42 | 70 | 42 | 0.55 |
| Ri | ng/ml | 4.4E-2 | 1.0E-9 | 3.4E0 | 2.9E0 | 7.3E0 | 5.4E0 | 1.0E-9 | 1.0E-9 | 4.5E1 | 2.5E1 | 70 | 42 | 70 | 42 | 0.47 |
| Rg | ng/ml | 1.0E-9 | 1.0E-9 | 4.7E-2 | 1.7E-1 | 3.6E-1 | 5.9E-1 | 1.0E-9 | 1.0E-9 | 3.0E0 | 3.3E0 | 70 | 42 | 70 | 42 | 0.56 |
| Rj | ng/ml | 1.0E-9 | 1.0E-9 | 7.5E-1 | 7.5E0 | 1.8E0 | 4.2E1 | 1.0E-9 | 1.0E-9 | 1.1E1 | 2.7E2 | 70 | 42 | 70 | 42 | 0.52 |
| Rf | ng/ml | 3.5E-1 | 3.8E-1 | 6.6E-1 | 1.6E0 | 7.7E-1 | 3.5E0 | 2.1E-2 | 3.2E-2 | 3.6E0 | 1.7E1 | 70 | 42 | 70 | 42 | 0.55 |
| Ql | pg/ml | 2.6E0 | 7.3E0 | 1.1E1 | 1.7E1 | 1.9E1 | 3.2E1 | 1.0E-9 | 1.0E-9 | 1.1E2 | 1.8E2 | 70 | 43 | 70 | 43 | 0.56 |
| Qm | pg/ml | 4.7E-1 | 1.4E1 | 1.8E1 | 2.6E1 | 3.5E1 | 3.7E1 | 1.0E-9 | 1.0E-9 | 1.9E2 | 1.8E2 | 70 | 43 | 70 | 43 | 0.61 |
| Qn | pg/ml | 5.8E-1 | 6.1E-1 | 6.7E0 | 3.6E0 | 2.8E1 | 1.0E1 | 1.0E-9 | 1.0E-9 | 2.2E2 | 6.0E1 | 70 | 43 | 70 | 43 | 0.53 |
| Nv | pg/ml | 3.2E3 | 6.8E3 | 9.7E3 | 1.6E4 | 2.0E4 | 2.7E4 | 1.0E-9 | 3.3E2 | 1.5E5 | 1.6E5 | 181 | 90 | 181 | 90 | 0.64 |
| Nw | pg/ml | 9.0E3 | 1.5E4 | 1.2E4 | 2.3E4 | 1.8E4 | 3.2E4 | 1.9E2 | 3.0E2 | 2.1E5 | 2.2E5 | 181 | 90 | 181 | 90 | 0.70 |
| Nx | pg/ml | 2.0E2 | 2.6E2 | 4.0E2 | 6.5E2 | 6.1E2 | 7.8E2 | 1.0E-9 | 1.0E-9 | 3.5E3 | 4.1E3 | 181 | 90 | 181 | 90 | 0.63 |
| Ny | pg/ml | 4.9E0 | 1.4E1 | 1.6E2 | 8.9E1 | 1.8E3 | 3.3E2 | 1.0E-9 | 1.0E-9 | 2.5E4 | 2.8E3 | 181 | 90 | 181 | 90 | 0.66 |
| Oa | pg/ml | 1.2E2 | 3.7E2 | 3.4E2 | 8.3E2 | 5.8E2 | 1.0E3 | 1.0E-9 | 1.0E-9 | 3.0E3 | 4.5E3 | 70 | 43 | 70 | 43 | 0.69 |
| Op | pg/ml | 4.0E5 | 4.5E5 | 4.0E5 | 4.6E5 | 1.5E5 | 1.8E5 | 1.4E5 | 5.2E4 | 7.3E5 | 7.5E5 | 29 | 20 | 29 | 20 | 0.63 |
| Wn | ng/ml | 1.1E1 | 1.8E1 | 1.2E2 | 2.2E1 | 3.9E2 | 1.9E1 | 1.2E0 | 3.8E0 | 1.8E3 | 5.6E1 | 22 | 9 | 22 | 9 | 0.56 |
| Tk | ng/ml | 1.3E2 | 1.3E2 | 3.4E2 | 4.6E2 | 8.5E2 | 7.2E2 | 3.0E0 | 1.4E1 | 4.2E3 | 2.3E3 | 23 | 12 | 23 | 12 | 0.54 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oe | pg/ml | 4.8E1 | 9.4E0 | 2.8E2 | 2.3E2 | 4.1E2 | 3.7E2 | 1.0E-9 | 1.0E-9 | 2.3E3 | 2.0E3 | 180 | 89 | 180 | 89 | 0.47 |
| Of | pg/ml | 2.1E2 | 9.8E1 | 5.8E3 | 7.2E3 | 2.2E4 | 2.5E4 | 1.0E-9 | 1.0E-9 | 1.9E5 | 1.7E5 | 181 | 90 | 181 | 90 | 0.45 |
| Og | pg/ml | 8.0E-2 | 6.2E-2 | 5.0E-1 | 1.3E-1 | 1.9E0 | 3.1E-1 | 1.0E-9 | 1.0E-9 | 1.9E1 | 2.5E0 | 181 | 90 | 181 | 90 | 0.43 |
| Oh | pg/ml | 2.8E0 | 4.1E0 | 1.9E1 | 2.0E2 | 1.2E2 | 1.7E3 | 1.0E-9 | 1.0E-9 | 1.4E3 | 1.6E4 | 181 | 90 | 181 | 90 | 0.56 |
| Oi | pg/ml | 2.5E0 | 2.7E0 | 5.3E0 | 5.4E0 | 7.5E0 | 6.9E0 | 1.0E-9 | 1.0E-9 | 4.2E1 | 3.1E1 | 181 | 90 | 181 | 90 | 0.53 |
| Ok | pg/ml | 3.8E2 | 6.3E2 | 4.6E2 | 9.0E2 | 3.9E2 | 1.1E3 | 1.5E1 | 6.4E1 | 2.2E3 | 7.8E3 | 181 | 90 | 181 | 90 | 0.70 |
| Om | pg/ml | 4.0E2 | 5.4E2 | 9.1E2 | 1.6E3 | 2.7E3 | 5.5E3 | 1.0E-9 | 1.0E-9 | 3.0E4 | 5.1E4 | 181 | 90 | 181 | 90 | 0.61 |
| On | pg/ml | 1.8E2 | 2.8E2 | 2.9E2 | 5.7E2 | 4.7E2 | 1.0E3 | 8.4E-1 | 2.2E1 | 4.5E3 | 8.5E3 | 181 | 90 | 181 | 90 | 0.64 |
| Or | pg/ml | 1.1E1 | 1.9E1 | 2.8E1 | 7.4E1 | 5.1E1 | 1.3E2 | 1.0E-9 | 1.0E-9 | 3.4E2 | 5.1E2 | 69 | 47 | 69 | 47 | 0.58 |
| Ow | pg/ml | 3.5E1 | 4.8E1 | 1.5E2 | 2.4E2 | 4.1E2 | 5.4E2 | 1.0E-9 | 1.0E-9 | 2.7E3 | 3.0E3 | 69 | 47 | 69 | 47 | 0.56 |
| Ou | pg/ml | 4.2E2 | 6.2E2 | 1.0E3 | 1.6E3 | 1.6E3 | 2.6E3 | 2.0E1 | 1.0E-9 | 9.8E3 | 1.1E4 | 69 | 47 | 69 | 47 | 0.56 |
| Ul | ng/ml | 1.0E-9 | 1.0E-9 | 9.9E-1 | 2.3E0 | 4.1E0 | 9.3E0 | 1.0E-9 | 1.0E-9 | 2.3E1 | 5.6E1 | 71 | 43 | 71 | 43 | 0.51 |
| Uo | ng/ml | 1.0E-9 | 1.0E-9 | 7.7E-2 | 7.1E-2 | 2.2E-1 | 1.7E-1 | 1.0E-9 | 1.0E-9 | 1.3E0 | 6.9E-1 | 71 | 43 | 71 | 43 | 0.49 |
| Uk | ng/ml | 1.0E-9 | 1.0E-9 | 8.0E-3 | 4.6E-3 | 4.0E-2 | 2.0E-2 | 1.0E-9 | 1.0E-9 | 3.2E-1 | 1.3E-1 | 71 | 43 | 71 | 43 | 0.44 |
| Um | ng/ml | 1.0E-9 | 1.0E-9 | 2.8E-1 | 1.7E-1 | 7.0E-1 | 4.5E-1 | 1.0E-9 | 1.0E-9 | 3.6E0 | 2.3E0 | 71 | 43 | 71 | 43 | 0.45 |
| Uf | ng/ml | 6.0E-2 | 9.5E-2 | 1.2E-1 | 3.0E-1 | 1.5E-1 | 7.9E-1 | 1.0E-3 | 6.8E-3 | 7.8E-1 | 5.1E0 | 71 | 43 | 71 | 43 | 0.61 |
| Uh | ng/ml | 1.8E0 | 4.5E0 | 2.8E0 | 5.5E0 | 2.6E0 | 4.3E0 | 3.6E-2 | 4.5E-1 | 1.0E1 | 1.8E1 | 71 | 43 | 71 | 43 | 0.70 |
| Un | ng/ml | 1.6E0 | 2.3E0 | 1.7E0 | 3.2E0 | 9.7E-1 | 3.9E0 | 3.4E-1 | 4.6E-1 | 4.4E0 | 2.5E1 | 71 | 43 | 71 | 43 | 0.68 |
| Ug | ng/ml | 1.1E1 | 8.5E0 | 2.2E1 | 2.2E1 | 2.6E1 | 3.2E1 | 1.5E0 | 1.2E0 | 1.4E2 | 1.6E2 | 71 | 43 | 71 | 43 | 0.46 |
| Ur | ng/ml | 1.1E-1 | 5.2E-2 | 3.5E-1 | 4.9E-1 | 6.1E-1 | 1.4E0 | 1.0E-9 | 1.0E-9 | 3.0E0 | 7.3E0 | 71 | 42 | 71 | 42 | 0.41 |
| Up | ng/ml | 1.0E-9 | 1.0E-9 | 2.3E-3 | 6.3E-2 | 7.9E-3 | 3.7E-1 | 1.0E-9 | 1.0E-9 | 5.3E-2 | 2.4E0 | 71 | 42 | 71 | 42 | 0.60 |
| Us | ng/ml | 4.2E-3 | 2.6E-3 | 1.1E-2 | 7.0E-2 | 2.0E-2 | 2.6E-1 | 1.0E-9 | 1.0E-9 | 1.2E-1 | 1.7E0 | 71 | 42 | 71 | 42 | 0.51 |
| Uv | ng/ml | 3.4E-3 | 2.5E-3 | 1.4E-2 | 1.6E-2 | 3.8E-2 | 6.3E-2 | 1.0E-9 | 1.0E-9 | 2.3E-1 | 4.1E-1 | 71 | 42 | 71 | 42 | 0.45 |
| Ut | ng/ml | 6.0E-1 | 1.2E0 | 2.6E0 | 5.1E0 | 6.9E0 | 1.1E1 | 1.0E-9 | 1.0E-9 | 5.2E1 | 6.5E1 | 71 | 42 | 71 | 42 | 0.62 |
| Uu | ng/ml | 7.2E0 | 6.1E0 | 7.9E0 | 6.7E0 | 5.4E0 | 3.9E0 | 8.3E-1 | 5.7E-1 | 2.9E1 | 1.7E1 | 71 | 42 | 71 | 42 | 0.44 |
| Uw | ng/ml | 2.0E0 | 2.8E0 | 2.6E0 | 5.1E0 | 2.3E0 | 8.3E0 | 1.0E-9 | 7.7E-1 | 7.1E0 | 3.9E1 | 30 | 20 | 30 | 20 | 0.66 |
| Vb | ng/ml | 1.2E0 | 1.1E0 | 1.1E0 | 1.2E0 | 4.5E-1 | 1.3E0 | 8.5E-2 | 2.6E-1 | 2.0E0 | 6.4E0 | 30 | 20 | 30 | 20 | 0.40 |
| Vc | ng/ml | 1.0E-9 | 1.0E-9 | 4.6E-3 | 1.0E-9 | 2.0E-2 | 0.0E0 | 1.0E-9 | 1.0E-9 | 1.1E-1 | 1.0E-9 | 30 | 20 | 30 | 20 | 0.45 |
| Uy | ng/ml | 8.6E-1 | 1.6E0 | 2.7E0 | 1.6E1 | 6.6E0 | 2.8E1 | 8.7E-2 | 2.0E-2 | 3.5E1 | 9.9E1 | 30 | 20 | 30 | 20 | 0.65 |
| Uz | ng/ml | 1.0E-9 | 1.0E-9 | 1.5E-2 | 1.7E0 | 7.9E-2 | 7.4E0 | 1.0E-9 | 1.0E-9 | 4.4E-1 | 3.3E1 | 30 | 20 | 30 | 20 | 0.53 |
| Ux | ng/ml | 1.8E2 | 1.9E2 | 1.8E2 | 2.2E2 | 1.3E2 | 1.4E2 | 4.5E0 | 2.0E1 | 4.6E2 | 4.9E2 | 30 | 20 | 30 | 20 | 0.58 |
| Va | ng/ml | 1.3E1 | 6.6E0 | 2.5E1 | 2.2E1 | 3.2E1 | 2.6E1 | 3.1E-1 | 1.2E0 | 1.2E2 | 9.6E1 | 30 | 20 | 30 | 20 | 0.49 |
| Vh | ng/ml | 8.1E-3 | 2.2E-2 | 1.7E-2 | 6.6E-2 | 2.5E-2 | 1.9E-1 | 1.0E-3 | 3.0E-3 | 1.2E-1 | 8.6E-1 | 30 | 20 | 30 | 20 | 0.73 |
| Vi | ng/ml | 4.0E-3 | 1.0E-2 | 7.5E-3 | 1.1E-1 | 7.8E-3 | 4.0E-1 | 1.0E-9 | 1.0E-9 | 2.7E-2 | 1.8E0 | 30 | 20 | 30 | 20 | 0.60 |
| Vj | ng/ml | 3.2E1 | 5.7E1 | 6.1E1 | 9.6E1 | 7.4E1 | 1.5E2 | 1.4E0 | 8.3E0 | 3.4E2 | 6.5E2 | 30 | 19 | 30 | 19 | 0.59 |
| Vp | ng/ml | 1.0E-9 | 1.0E-9 | 1.3E-1 | 1.3E0 | 5.4E-1 | 7.5E0 | 1.0E-9 | 1.0E-9 | 3.9E0 | 4.9E1 | 71 | 43 | 71 | 43 | 0.55 |
| Vt | ng/ml | 5.6E0 | 9.3E0 | 6.5E0 | 1.6E1 | 5.3E0 | 2.4E1 | 5.6E-1 | 1.9E0 | 3.2E1 | 1.6E2 | 71 | 43 | 71 | 43 | 0.72 |
| Vu | ng/ml | 1.0E-9 | 4.5E-1 | 1.4E0 | 2.4E0 | 3.0E0 | 4.5E0 | 1.0E-9 | 1.0E-9 | 1.6E1 | 2.2E1 | 69 | 41 | 69 | 41 | 0.59 |
| Vq | ng/ml | 7.5E1 | 3.5E2 | 5.0E2 | 1.2E3 | 8.9E2 | 2.4E3 | 9.2E-1 | 8.9E0 | 5.0E3 | 1.2E4 | 59 | 31 | 59 | 31 | 0.64 |
| Vo | ng/ml | 2.5E1 | 2.6E1 | 2.4E1 | 2.5E1 | 4.9E0 | 6.7E0 | 9.7E0 | 4.9E0 | 3.5E1 | 4.8E1 | 71 | 43 | 71 | 43 | 0.54 |
| Vs | ng/ml | 1.0E-9 | 1.0E-9 | 4.8E0 | 1.5E1 | 1.3E1 | 7.1E1 | 1.0E-9 | 1.0E-9 | 8.9E1 | 4.5E2 | 70 | 41 | 70 | 41 | 0.47 |
| Vv | ng/ml | 2.8E0 | 3.7E0 | 6.4E0 | 5.7E0 | 1.1E1 | 7.9E0 | 1.0E-9 | 1.0E-9 | 8.4E1 | 4.4E1 | 71 | 42 | 71 | 42 | 0.48 |
| Vw | ng/ml | 3.4E1 | 4.3E1 | 3.1E1 | 4.1E1 | 1.8E1 | 1.9E1 | 2.5E0 | 4.4E0 | 6.7E1 | 6.9E1 | 30 | 20 | 30 | 20 | 0.66 |
| Oy | pg/ml | 5.3E-1 | 4.8E-1 | 8.9E0 | 3.7E0 | 4.1E1 | 1.2E1 | 1.0E-9 | 1.0E-9 | 4.0E2 | 9.9E1 | 181 | 89 | 181 | 89 | 0.45 |
| Oz | pg/ml | 4.9E-2 | 1.0E-9 | 2.8E-1 | 8.0E-1 | 3.9E-1 | 4.2E0 | 1.0E-9 | 1.0E-9 | 2.1E0 | 2.9E1 | 181 | 89 | 181 | 89 | 0.41 |
| Pa | pg/ml | 3.9E-1 | 5.3E-1 | 1.5E0 | 5.5E0 | 7.1E0 | 2.6E1 | 1.0E-9 | 1.0E-9 | 8.6E1 | 2.3E2 | 181 | 89 | 181 | 89 | 0.55 |
| Pb | pg/ml | 1.0E-9 | 1.0E-9 | 2.8E0 | 8.6E-1 | 3.6E1 | 4.5E0 | 1.0E-9 | 1.0E-9 | 4.9E2 | 3.2E1 | 181 | 89 | 181 | 89 | 0.45 |
| Pc | pg/ml | 2.0E-1 | 1.0E-9 | 4.8E-1 | 4.4E0 | 1.1E0 | 3.5E1 | 1.0E-9 | 1.0E-9 | 1.4E1 | 3.3E2 | 181 | 89 | 181 | 89 | 0.43 |
| Pd | pg/ml | 1.7E0 | 2.3E0 | 4.0E0 | 1.6E1 | 8.8E0 | 9.0E1 | 1.0E-9 | 1.0E-9 | 9.4E1 | 8.4E2 | 181 | 89 | 181 | 89 | 0.54 |
| Pe | pg/ml | 2.0E1 | 4.4E1 | 9.4E1 | 5.0E2 | 4.2E2 | 1.9E3 | 1.0E-9 | 1.0E-9 | 4.7E3 | 1.5E4 | 181 | 89 | 181 | 89 | 0.65 |
| Pf | pg/ml | 1.6E0 | 3.4E0 | 8.2E0 | 3.7E1 | 3.2E1 | 1.7E2 | 1.0E-9 | 1.0E-9 | 3.3E2 | 1.5E3 | 181 | 89 | 181 | 89 | 0.62 |
| Pg | pg/ml | 4.0E0 | 8.8E0 | 6.6E1 | 1.9E2 | 4.0E2 | 8.7E2 | 1.0E-9 | 1.0E-9 | 4.2E3 | 7.7E3 | 181 | 89 | 181 | 89 | 0.59 |
| Ph | ng/ml | 1.4E-1 | 1.8E-1 | 3.3E-1 | 4.9E-1 | 4.6E-1 | 9.3E-1 | 1.0E-9 | 1.0E-9 | 2.2E0 | 5.4E0 | 69 | 47 | 69 | 47 | 0.54 |
| Pi | ng/ml | 1.9E-1 | 2.2E-1 | 3.0E-1 | 2.1E0 | 4.5E-1 | 1.2E1 | 1.0E-9 | 1.0E-9 | 3.2E0 | 8.2E1 | 69 | 47 | 69 | 47 | 0.56 |
| Pj | ng/mL | 4.4E0 | 7.3E0 | 4.9E0 | 8.4E0 | 3.3E0 | 5.8E0 | 4.0E-1 | 1.5E0 | 1.6E1 | 3.1E1 | 69 | 47 | 69 | 47 | 0.71 |
| Pk | ng/ml | 7.7E-3 | 1.3E-2 | 1.2E-2 | 5.0E-2 | 3.1E-2 | 2.2E-1 | 1.0E-9 | 1.0E-9 | 2.5E-1 | 1.5E0 | 69 | 47 | 69 | 47 | 0.68 |
| aA | mg/dL | 8.8E-1 | 9.2E-1 | 1.0E0 | 1.2E0 | 4.9E-1 | 7.8E-1 | 3.0E-1 | 4.0E-1 | 4.2E0 | 4.7E0 | 294 | 111 | 294 | 111 | 0.55 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| aC | mg/mL | 2.3E0 | 2.0E0 | 2.7E0 | 2.2E0 | 1.2E0 | 1.0E0 | 1.1E0 | 7.5E-1 | 7.2E0 | 5.5E0 | 86 | 56 | 86 | 56 | 0.37 |
| aD | ug/mL | 2.9E0 | 3.5E0 | 4.3E0 | 5.0E0 | 4.2E0 | 4.1E0 | 8.5E-1 | 7.5E-1 | 3.1E1 | 2.1E1 | 86 | 56 | 86 | 56 | 0.55 |
| aE | mg/mL | 5.6E-1 | 5.9E-1 | 5.9E-1 | 6.0E-1 | 1.6E-1 | 2.0E-1 | 2.8E-1 | 1.8E-1 | 1.1E0 | 1.2E0 | 86 | 56 | 86 | 56 | 0.52 |
| aF | ng/mL | 2.2E0 | 2.2E0 | 6.2E0 | 3.7E0 | 9.7E0 | 3.9E0 | 4.3E-3 | 4.3E-3 | 5.0E1 | 1.9E1 | 86 | 56 | 86 | 56 | 0.46 |
| aG | mg/mL | 1.3E-1 | 1.4E-1 | 1.5E-1 | 1.6E-1 | 7.9E-2 | 8.4E-2 | 5.0E-2 | 5.1E-2 | 4.2E-1 | 4.8E-1 | 86 | 56 | 86 | 56 | 0.50 |
| aH | ug/mL | 6.5E1 | 7.1E1 | 7.3E1 | 7.8E1 | 3.5E1 | 4.3E1 | 1.5E1 | 1.1E1 | 2.0E2 | 1.8E2 | 86 | 56 | 86 | 56 | 0.52 |
| aI | ug/mL | 1.7E2 | 1.6E2 | 1.7E2 | 1.7E2 | 5.7E1 | 6.5E1 | 6.1E1 | 4.7E1 | 3.3E2 | 3.4E2 | 86 | 56 | 86 | 56 | 0.46 |
| aJ | ng/mL | 2.5E0 | 2.5E0 | 3.1E0 | 3.5E0 | 2.3E0 | 2.4E0 | 9.5E-1 | 8.2E-1 | 1.4E1 | 1.1E1 | 86 | 56 | 86 | 56 | 0.56 |
| aK | ng/mL | 1.4E0 | 1.2E0 | 2.0E0 | 1.8E0 | 1.8E0 | 2.0E0 | 6.9E-2 | 2.9E-4 | 7.5E0 | 1.0E1 | 86 | 56 | 86 | 56 | 0.45 |
| aL | mg/mL | 7.3E-1 | 7.2E-1 | 7.5E-1 | 7.5E-1 | 2.2E-1 | 2.6E-1 | 2.2E-1 | 2.7E-1 | 1.3E0 | 1.7E0 | 86 | 56 | 86 | 56 | 0.49 |
| aM | U/mL | 1.4E1 | 2.3E1 | 2.8E1 | 6.1E1 | 4.8E1 | 1.2E2 | 4.2E-2 | 4.2E-2 | 3.5E2 | 8.2E2 | 86 | 56 | 86 | 56 | 0.64 |
| aN | U/mL | 1.2E1 | 2.0E1 | 1.9E1 | 4.0E1 | 2.3E1 | 6.6E1 | 2.5E-3 | 2.5E-3 | 1.3E2 | 3.8E2 | 86 | 56 | 86 | 56 | 0.66 |
| aO | pg/mL | 7.4E1 | 4.8E1 | 5.4E2 | 3.2E2 | 1.2E3 | 6.1E2 | 6.0E-2 | 6.0E-2 | 6.6E3 | 2.4E3 | 86 | 56 | 86 | 56 | 0.47 |
| aP | ng/mL | 1.5E0 | 1.7E0 | 2.0E0 | 2.2E0 | 1.3E0 | 1.4E0 | 5.4E-1 | 6.8E-1 | 6.5E0 | 6.6E0 | 86 | 56 | 86 | 56 | 0.56 |
| aQ | ng/mL | 2.3E-1 | 2.5E-1 | 3.1E-1 | 3.8E-1 | 2.5E-1 | 4.0E-1 | 2.0E-4 | 2.0E-4 | 1.1E0 | 2.0E0 | 86 | 56 | 86 | 56 | 0.53 |
| aR | ng/mL | 1.8E0 | 1.8E0 | 3.4E0 | 2.7E0 | 4.9E0 | 2.7E0 | 2.6E-1 | 5.6E-1 | 3.4E1 | 1.7E1 | 86 | 56 | 86 | 56 | 0.51 |
| aS | ng/mL | 3.7E-1 | 5.1E-1 | 1.2E0 | 1.0E0 | 3.6E0 | 1.2E0 | 4.2E-3 | 4.2E-3 | 3.3E1 | 6.2E0 | 86 | 56 | 86 | 56 | 0.56 |
| aU | pg/mL | 7.2E1 | 6.1E1 | 9.9E1 | 1.0E2 | 9.5E1 | 1.2E2 | 6.5E0 | 7.4E-2 | 5.1E2 | 7.0E2 | 86 | 56 | 86 | 56 | 0.47 |
| aV | ng/mL | 6.2E-1 | 4.6E-1 | 8.0E-1 | 1.4E0 | 7.2E-1 | 4.3E0 | 5.9E-2 | 7.6E-4 | 4.0E0 | 3.3E1 | 86 | 56 | 86 | 56 | 0.48 |
| aW | pg/mL | 2.1E1 | 1.9E1 | 2.2E1 | 2.6E1 | 1.9E1 | 5.4E1 | 7.2E-2 | 7.2E-2 | 1.7E2 | 4.2E2 | 86 | 56 | 86 | 56 | 0.45 |
| aX | ng/mL | 8.1E0 | 6.8E0 | 1.1E1 | 1.2E1 | 9.9E0 | 1.7E1 | 3.0E-1 | 6.2E-1 | 5.4E1 | 1.1E2 | 86 | 56 | 86 | 56 | 0.44 |
| aY | pg/mL | 5.3E1 | 5.2E1 | 7.0E1 | 8.5E1 | 5.8E1 | 1.7E2 | 4.1E-1 | 4.1E-1 | 3.1E2 | 1.2E3 | 86 | 56 | 86 | 56 | 0.48 |
| aZ | pg/mL | 2.2E2 | 2.4E2 | 6.9E2 | 5.5E2 | 1.5E3 | 8.8E2 | 1.7E0 | 1.7E0 | 1.2E4 | 4.7E3 | 86 | 56 | 86 | 56 | 0.50 |
| bA | ng/mL | 1.3E1 | 2.3E1 | 4.3E1 | 1.1E2 | 7.2E1 | 2.1E2 | 3.0E-2 | 3.0E-2 | 4.1E2 | 9.4E2 | 86 | 56 | 86 | 56 | 0.60 |
| bB | ng/mL | 2.8E2 | 2.7E2 | 2.9E2 | 2.8E2 | 1.5E2 | 1.8E2 | 5.7E1 | 1.2E1 | 7.4E2 | 8.1E2 | 86 | 56 | 86 | 56 | 0.47 |
| bC | ng/mL | 3.4E2 | 3.0E2 | 5.3E2 | 7.1E2 | 6.2E2 | 1.0E3 | 2.7E1 | 3.5E1 | 4.0E3 | 4.7E3 | 86 | 56 | 86 | 56 | 0.49 |
| bE | mg/mL | 5.2E0 | 4.5E0 | 5.4E0 | 4.9E0 | 1.8E0 | 2.0E0 | 1.9E0 | 1.3E0 | 1.2E1 | 1.1E1 | 86 | 56 | 86 | 56 | 0.41 |
| bF | pg/mL | 3.6E1 | 3.6E1 | 3.7E2 | 4.5E2 | 1.4E3 | 1.6E3 | 5.0E-2 | 2.5E0 | 1.1E4 | 1.0E4 | 86 | 56 | 86 | 56 | 0.49 |
| bG | ng/mL | 1.7E0 | 2.3E0 | 3.0E0 | 4.0E0 | 4.4E0 | 5.2E0 | 1.1E-1 | 2.4E-1 | 2.6E1 | 3.0E1 | 86 | 56 | 86 | 56 | 0.56 |
| bH | pg/mL | 5.7E-1 | 5.7E-1 | 6.8E0 | 7.2E0 | 3.0E1 | 1.7E1 | 5.7E-1 | 5.7E-1 | 2.8E2 | 1.2E2 | 86 | 56 | 86 | 56 | 0.54 |
| bI | ng/mL | 4.0E-3 | 4.0E-3 | 9.5E-2 | 1.1E-1 | 2.0E-1 | 2.2E-1 | 4.0E-3 | 4.0E-3 | 9.8E-1 | 8.8E-1 | 86 | 56 | 86 | 56 | 0.49 |
| bJ | mg/mL | 1.8E0 | 1.7E0 | 2.1E0 | 2.1E0 | 1.6E0 | 2.1E0 | 2.5E-4 | 2.5E-4 | 6.6E0 | 1.1E1 | 86 | 56 | 86 | 56 | 0.47 |
| bL | pg/mL | 4.3E0 | 3.0E0 | 9.5E0 | 8.2E0 | 1.1E1 | 1.0E1 | 4.6E-2 | 4.6E-2 | 4.9E1 | 3.5E1 | 86 | 56 | 86 | 56 | 0.46 |
| bM | mg/mL | 1.7E0 | 2.2E0 | 1.9E0 | 2.7E0 | 1.3E0 | 1.7E0 | 2.4E-1 | 1.8E-2 | 8.6E0 | 7.9E0 | 86 | 56 | 86 | 56 | 0.65 |
| bN | ng/mL | 3.6E1 | 3.6E1 | 1.2E2 | 1.2E2 | 2.6E2 | 3.0E2 | 1.4E-1 | 5.9E-1 | 1.9E3 | 1.9E3 | 86 | 56 | 86 | 56 | 0.47 |
| bO | ng/mL | 4.0E-2 | 4.0E-2 | 8.2E0 | 8.9E0 | 1.5E1 | 2.3E1 | 4.0E-2 | 4.0E-2 | 6.4E1 | 1.3E2 | 86 | 56 | 86 | 56 | 0.44 |
| bP | mg/mL | 4.7E-1 | 5.2E-1 | 6.7E-1 | 7.5E-1 | 5.3E-1 | 8.3E-1 | 8.2E-2 | 9.2E-2 | 2.5E0 | 4.8E0 | 86 | 56 | 86 | 56 | 0.51 |
| bQ | pg/mL | 2.1E1 | 2.5E1 | 6.9E1 | 2.8E2 | 2.6E2 | 1.8E3 | 3.5E0 | 1.5E-1 | 2.4E3 | 1.3E4 | 86 | 56 | 86 | 56 | 0.54 |
| bR | ng/mL | 1.2E-2 | 1.2E-2 | 1.2E-1 | 2.3E-1 | 3.8E-1 | 1.2E0 | 1.2E-2 | 1.2E-2 | 3.4E0 | 8.7E0 | 86 | 56 | 86 | 56 | 0.52 |
| bS | pg/mL | 9.4E-1 | 9.4E-1 | 9.1E0 | 1.1E1 | 3.9E1 | 5.3E1 | 9.4E-1 | 9.4E-1 | 3.4E2 | 3.9E2 | 86 | 56 | 86 | 56 | 0.48 |
| bU | ng/mL | 6.9E-2 | 5.7E-2 | 1.6E-1 | 2.5E-1 | 2.5E-1 | 8.8E-1 | 1.3E-2 | 1.3E-2 | 1.8E0 | 6.6E0 | 86 | 56 | 86 | 56 | 0.50 |
| bV | pg/mL | 4.3E2 | 5.3E2 | 5.3E2 | 6.3E2 | 2.8E2 | 3.9E2 | 1.8E0 | 3.1E3 | 3.8E3 | 2.2E3 | 86 | 56 | 86 | 56 | 0.59 |
| bW | pg/mL | 3.3E2 | 3.2E2 | 4.3E2 | 5.7E2 | 3.6E2 | 8.5E2 | 8.4E1 | 1.3E2 | 2.2E3 | 4.8E3 | 86 | 56 | 86 | 56 | 0.53 |
| bX | ng/mL | 7.0E-4 | 1.5E-3 | 2.5E-3 | 2.5E-3 | 3.0E-3 | 2.8E-3 | 2.5E-5 | 2.5E-5 | 1.2E-2 | 8.4E-3 | 86 | 56 | 86 | 56 | 0.50 |
| bZ | pg/mL | 2.8E2 | 3.2E2 | 1.8E3 | 2.6E3 | 6.0E3 | 9.5E3 | 1.5E-1 | 3.5E1 | 4.4E4 | 5.8E4 | 86 | 56 | 86 | 56 | 0.52 |
| cA | pg/mL | 6.0E-1 | 6.0E-1 | 1.6E0 | 8.6E0 | 3.1E0 | 5.0E1 | 6.0E-1 | 6.0E-1 | 1.6E1 | 3.7E2 | 86 | 56 | 86 | 56 | 0.51 |
| cB | ng/mL | 3.7E-2 | 5.2E-2 | 5.5E-2 | 8.3E-2 | 6.0E-2 | 1.0E-1 | 1.7E-3 | 1.7E-3 | 3.1E-1 | 4.3E-1 | 86 | 56 | 86 | 56 | 0.54 |
| cC | pg/mL | 4.6E1 | 3.4E1 | 4.9E1 | 4.3E1 | 4.7E1 | 6.2E1 | 1.0E0 | 1.0E0 | 3.7E2 | 4.5E2 | 86 | 56 | 86 | 56 | 0.43 |
| cD | pg/mL | 6.1E0 | 4.1E0 | 1.5E1 | 1.4E1 | 5.5E1 | 4.4E1 | 3.3E-1 | 3.3E-1 | 4.8E2 | 2.9E2 | 86 | 56 | 86 | 56 | 0.41 |
| cE | pg/mL | 6.7E1 | 6.7E1 | 2.9E2 | 2.5E2 | 6.6E2 | 6.0E2 | 1.8E0 | 1.2E-1 | 3.1E3 | 3.8E3 | 86 | 56 | 86 | 56 | 0.53 |
| cF | pg/mL | 5.3E-1 | 5.3E-1 | 1.4E1 | 1.6E1 | 2.7E1 | 3.8E1 | 5.3E-1 | 5.3E-1 | 1.4E2 | 2.7E2 | 86 | 56 | 86 | 56 | 0.52 |
| cG | pg/mL | 5.2E1 | 6.3E1 | 1.1E2 | 3.0E2 | 1.7E2 | 1.4E3 | 1.5E1 | 7.8E0 | 1.1E3 | 1.0E4 | 86 | 56 | 86 | 56 | 0.55 |
| cH | uIU/mL | 3.1E0 | 3.3E0 | 7.3E0 | 9.2E0 | 1.8E1 | 1.8E1 | 8.6E-3 | 8.6E-3 | 1.6E2 | 1.2E2 | 86 | 56 | 86 | 56 | 0.53 |
| cI | ng/mL | 5.0E0 | 6.6E0 | 1.0E1 | 1.9E1 | 1.5E1 | 2.7E1 | 3.2E-2 | 3.1E-1 | 1.0E2 | 1.2E2 | 86 | 56 | 86 | 56 | 0.56 |
| cJ | ug/mL | 6.5E1 | 5.5E1 | 9.3E1 | 9.7E1 | 1.0E2 | 1.1E2 | 6.9E0 | 7.2E0 | 6.4E2 | 6.2E2 | 86 | 56 | 86 | 56 | 0.51 |
| cK | ng/mL | 3.8E-3 | 3.8E-3 | 1.1E-2 | 3.7E-2 | 2.5E-2 | 2.0E-1 | 3.8E-3 | 3.8E-3 | 1.3E-1 | 1.5E0 | 86 | 56 | 86 | 56 | 0.51 |
| cL | pg/mL | 2.2E2 | 1.9E2 | 5.3E2 | 6.6E2 | 1.2E3 | 3.2E3 | 3.6E1 | 3.1E1 | 7.4E3 | 2.4E4 | 86 | 56 | 86 | 56 | 0.47 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cM | pg/mL | 2.7E2 | 2.7E2 | 3.1E2 | 2.6E2 | 1.9E2 | 1.3E2 | 6.0E1 | 4.2E1 | 1.1E3 | 6.7E2 | 86 | 56 | 86 | 56 | 0.45 |
| cN | pg/mL | 1.2E2 | 1.2E2 | 1.3E2 | 1.4E2 | 5.6E1 | 1.3E2 | 3.8E1 | 6.3E1 | 3.2E2 | 1.1E3 | 86 | 56 | 86 | 56 | 0.51 |
| cO | pg/mL | 2.0E2 | 2.1E2 | 3.3E2 | 6.0E2 | 3.8E2 | 2.6E3 | 5.4E1 | 8.2E1 | 2.4E3 | 1.9E4 | 86 | 56 | 86 | 56 | 0.50 |
| cP | ng/mL | 2.5E3 | 2.4E3 | 2.6E3 | 2.6E3 | 1.0E3 | 9.6E2 | 6.2E2 | 1.0E3 | 5.6E3 | 4.7E3 | 86 | 56 | 86 | 56 | 0.50 |
| cQ | ng/mL | 4.9E-2 | 5.5E-2 | 1.2E-1 | 1.4E-1 | 1.9E-1 | 2.5E-1 | 2.0E-3 | 2.0E-3 | 1.2E0 | 1.3E0 | 86 | 56 | 86 | 56 | 0.50 |
| cR | ng/mL | 3.0E2 | 3.0E2 | 5.2E2 | 6.4E2 | 6.6E2 | 1.1E3 | 3.6E1 | 2.0E1 | 4.8E3 | 7.7E3 | 86 | 56 | 86 | 56 | 0.51 |
| cS | ng/mL | 2.4E2 | 2.9E2 | 4.0E2 | 4.0E2 | 4.4E2 | 3.9E2 | 8.0E1 | 9.7E1 | 2.5E3 | 2.4E3 | 86 | 56 | 86 | 56 | 0.54 |
| cT | ng/mL | 5.2E1 | 6.5E1 | 1.3E2 | 2.3E2 | 2.1E2 | 4.2E2 | 5.1E0 | 4.2E0 | 1.3E3 | 2.1E3 | 86 | 56 | 86 | 56 | 0.56 |
| cU | ng/mL | 5.6E1 | 6.6E1 | 8.2E1 | 1.3E2 | 9.4E1 | 2.2E2 | 6.2E0 | 1.4E1 | 7.7E2 | 1.6E3 | 86 | 56 | 86 | 56 | 0.58 |
| cV | ng/mL | 1.9E-1 | 2.2E-1 | 1.0E0 | 5.9E-1 | 5.1E0 | 1.3E0 | 3.4E-2 | 3.6E-2 | 4.7E1 | 8.7E0 | 86 | 56 | 86 | 56 | 0.52 |
| cW | mIU/mL | 4.8E-2 | 4.5E-2 | 1.1E-1 | 6.7E-2 | 4.8E-1 | 6.4E-2 | 4.8E-3 | 4.8E-3 | 4.5E0 | 3.9E-1 | 86 | 56 | 86 | 56 | 0.51 |
| cX | ng/mL | 1.4E-1 | 7.6E-2 | 2.5E0 | 1.7E0 | 6.8E0 | 5.0E0 | 2.3E-4 | 2.3E-4 | 2.8E1 | 2.8E1 | 86 | 56 | 86 | 56 | 0.52 |
| cY | ng/mL | 7.6E0 | 7.1E0 | 1.0E1 | 1.2E1 | 9.0E0 | 1.4E1 | 2.2E-1 | 1.7E-1 | 4.1E1 | 6.1E1 | 86 | 56 | 86 | 56 | 0.49 |
| cZ | ug/mL | 1.2E1 | 1.2E1 | 1.4E1 | 1.4E1 | 5.3E0 | 6.9E0 | 6.0E0 | 2.8E0 | 2.9E1 | 3.0E1 | 86 | 56 | 86 | 56 | 0.46 |
| dA | pg/mL | 2.9E2 | 3.3E2 | 3.2E2 | 4.7E2 | 1.3E2 | 7.5E2 | 1.0E2 | 1.1E2 | 9.4E2 | 5.8E3 | 86 | 56 | 86 | 56 | 0.57 |
| dB | ug/mL | 1.9E1 | 1.7E1 | 2.1E1 | 1.5E1 | 2.7E1 | 9.7E0 | 2.1E0 | 2.1E0 | 2.5E2 | 3.0E1 | 86 | 56 | 86 | 56 | 0.41 |
| dC | nmol/L | 3.5E1 | 3.2E1 | 3.9E1 | 3.6E1 | 1.9E1 | 1.4E1 | 1.0E1 | 7.8E0 | 1.4E2 | 7.0E1 | 86 | 56 | 86 | 56 | 0.48 |
| dD | ug/mL | 3.4E1 | 3.2E1 | 3.5E1 | 3.2E1 | 9.9E0 | 1.1E1 | 1.4E1 | 1.4E1 | 7.4E1 | 6.0E1 | 86 | 56 | 86 | 56 | 0.41 |
| dE | ng/mL | 5.2E-1 | 3.4E-1 | 5.7E-1 | 4.9E-1 | 5.5E-1 | 5.8E-1 | 8.4E-3 | 8.4E-3 | 2.7E0 | 2.4E0 | 86 | 56 | 86 | 56 | 0.44 |
| dF | ng/mL | 2.5E2 | 2.8E2 | 3.3E2 | 3.9E2 | 2.4E2 | 2.9E2 | 7.5E1 | 7.5E1 | 1.2E3 | 1.3E3 | 86 | 56 | 86 | 56 | 0.57 |
| dG | ng/mL | 1.3E1 | 1.2E1 | 1.6E1 | 1.9E1 | 1.3E1 | 2.6E1 | 3.2E0 | 3.0E0 | 9.7E1 | 1.8E2 | 86 | 56 | 86 | 56 | 0.53 |
| dH | pg/mL | 7.3E0 | 8.8E0 | 1.8E1 | 2.3E1 | 4.1E1 | 8.9E1 | 4.0E-2 | 4.0E-2 | 3.1E2 | 6.7E2 | 86 | 56 | 86 | 56 | 0.57 |
| dI | pg/mL | 4.6E-1 | 4.6E-1 | 1.6E0 | 7.5E0 | 4.1E0 | 4.4E1 | 4.6E-1 | 4.6E-1 | 3.4E1 | 3.3E2 | 86 | 56 | 86 | 56 | 0.56 |
| dJ | ng/mL | 1.8E0 | 2.2E0 | 2.1E0 | 2.2E0 | 1.1E0 | 1.2E0 | 3.2E-2 | 3.2E-2 | 5.1E0 | 4.8E0 | 86 | 56 | 86 | 56 | 0.54 |
| dK | uIU/mL | 1.5E0 | 1.0E0 | 2.6E0 | 1.9E0 | 4.7E0 | 2.1E0 | 2.8E-4 | 2.9E-2 | 3.9E1 | 1.1E1 | 86 | 56 | 86 | 56 | 0.43 |
| dL | ng/mL | 8.5E2 | 9.0E2 | 9.7E2 | 1.2E3 | 4.9E2 | 8.0E2 | 3.4E2 | 2.8E2 | 3.4E3 | 4.8E3 | 86 | 56 | 86 | 56 | 0.58 |
| dM | pg/mL | 9.5E2 | 1.0E3 | 1.3E3 | 1.5E3 | 1.7E3 | 1.6E3 | 3.9E2 | 3.7E2 | 1.5E4 | 9.6E3 | 86 | 56 | 86 | 56 | 0.56 |
| dN | ug/mL | 9.8E1 | 1.0E2 | 1.0E2 | 1.1E2 | 3.7E1 | 4.9E1 | 2.5E1 | 2.4E1 | 2.2E2 | 3.3E2 | 86 | 56 | 86 | 56 | 0.54 |
| dR | pg/ml | 1.4E3 | 1.2E3 | 1.9E3 | 2.1E3 | 1.7E3 | 2.5E3 | 1.4E2 | 1.3E2 | 7.8E3 | 9.8E3 | 64 | 48 | 64 | 48 | 0.45 |
| dU | pg/ml | 7.3E3 | 1.9E4 | 8.7E3 | 2.3E4 | 8.1E3 | 2.1E4 | 1.7E3 | 6.9E2 | 3.5E4 | 8.1E4 | 15 | 14 | 15 | 14 | 0.76 |
| dX | ng/ml | 5.2E-2 | 8.2E-2 | 1.6E-1 | 9.5E-2 | 2.6E-1 | 1.1E-1 | 2.6E-3 | 2.6E-3 | 1.2E0 | 4.2E-1 | 27 | 18 | 27 | 18 | 0.47 |
| dW | ng/ml | 1.2E-1 | 1.7E-1 | 2.4E-1 | 2.2E-1 | 2.7E-1 | 1.7E-1 | 6.4E-2 | 6.8E-2 | 8.0E-1 | 5.9E-1 | 9 | 8 | 9 | 8 | 0.60 |
| eF | ng/ml | 4.4E0 | 4.0E0 | 5.1E0 | 4.6E0 | 2.4E0 | 2.2E0 | 2.0E0 | 2.0E0 | 1.2E1 | 1.5E1 | 64 | 48 | 64 | 48 | 0.43 |
| eC | pg/ml | 3.1E2 | 2.8E2 | 3.9E2 | 3.5E2 | 2.9E2 | 3.1E2 | 1.1E2 | 1.9E1 | 1.6E3 | 2.0E3 | 58 | 43 | 58 | 43 | 0.44 |
| eD | pg/ml | 2.2E2 | 1.9E2 | 6.9E2 | 6.5E2 | 1.4E3 | 1.4E3 | 5.2E-1 | 5.2E-1 | 6.8E3 | 7.0E3 | 52 | 30 | 52 | 30 | 0.48 |
| eO | ng/ml | 4.6E1 | 9.4E1 | 2.5E2 | 1.0E2 | 3.5E2 | 4.6E1 | 2.0E1 | 4.3E1 | 9.6E2 | 1.7E2 | 9 | 8 | 9 | 8 | 0.64 |
| eM | ng/ml | 3.2E0 | 2.5E0 | 4.2E0 | 5.0E0 | 3.4E0 | 6.5E0 | 7.6E-1 | 6.9E-1 | 1.7E1 | 2.6E1 | 37 | 25 | 37 | 25 | 0.45 |
| eP | ng/ml | 3.1E-2 | 3.7E-3 | 8.7E-1 | 1.7E0 | 1.8E0 | 6.5E0 | 3.7E-3 | 3.7E-3 | 8.6E0 | 2.8E1 | 27 | 18 | 27 | 18 | 0.37 |
| eT | pg/ml | 2.7E2 | 2.9E2 | 7.2E2 | 7.7E2 | 8.1E2 | 9.6E2 | 1.0E2 | 7.1E1 | 2.9E3 | 2.9E3 | 31 | 18 | 31 | 18 | 0.52 |
| eQ | pg/ml | 1.0E0 | 1.0E0 | 6.8E1 | 3.5E1 | 1.4E2 | 5.6E1 | 1.0E0 | 1.0E0 | 4.7E2 | 1.5E2 | 15 | 14 | 15 | 14 | 0.52 |
| eW | U/ml | 1.1E-2 | 6.7E-3 | 2.3E-1 | 5.2E-2 | 5.1E-1 | 8.4E-2 | 6.7E-3 | 6.7E-3 | 1.6E0 | 1.9E-1 | 9 | 8 | 9 | 8 | 0.36 |
| fA | ng/ml | 2.3E2 | 1.6E2 | 3.5E2 | 5.2E2 | 4.2E2 | 5.4E2 | 3.9E1 | 4.0E1 | 1.5E3 | 1.4E3 | 15 | 12 | 15 | 12 | 0.53 |
| eZ | ng/ml | 4.3E1 | 5.8E1 | 5.5E1 | 6.2E1 | 2.7E1 | 2.4E1 | 1.8E1 | 2.3E1 | 1.2E2 | 1.1E2 | 31 | 18 | 31 | 18 | 0.60 |
| fB | ng/ml | 5.7E2 | 6.6E2 | 6.7E2 | 6.9E2 | 2.6E2 | 2.9E2 | 3.1E2 | 2.6E2 | 1.3E3 | 1.3E3 | 15 | 13 | 15 | 13 | 0.55 |
| fN | ng/ml | 2.1E-1 | 2.1E-1 | 2.1E0 | 3.8E0 | 3.8E0 | 6.4E0 | 2.1E-1 | 2.1E-1 | 1.4E1 | 2.1E1 | 31 | 18 | 31 | 18 | 0.53 |
| fP | ng/ml | 2.8E2 | 2.6E2 | 3.5E2 | 3.1E2 | 2.1E2 | 1.6E2 | 1.8E0 | 3.7E1 | 1.0E3 | 7.7E2 | 63 | 46 | 63 | 46 | 0.46 |
| fR | ng/ml | 1.7E5 | 1.7E5 | 2.1E5 | 2.3E5 | 1.6E5 | 1.8E5 | 3.9E4 | 1.9E2 | 6.3E5 | 6.8E5 | 56 | 35 | 56 | 35 | 0.54 |
| fY | ng/ml | 2.5E2 | 2.5E2 | 2.5E2 | 2.5E2 | 9.5E1 | 1.2E2 | 6.5E1 | 3.6E1 | 4.2E2 | 4.8E2 | 31 | 18 | 31 | 18 | 0.49 |
| gC | ng/ml | 2.2E2 | 2.4E2 | 2.6E2 | 2.5E2 | 1.2E2 | 1.1E2 | 9.7E1 | 8.3E1 | 6.4E2 | 4.8E2 | 21 | 17 | 21 | 17 | 0.50 |
| gL | pg/ml | 6.5E4 | 6.5E4 | 7.4E4 | 7.0E4 | 3.2E4 | 3.3E4 | 2.3E4 | 1.1E4 | 1.6E5 | 1.7E5 | 64 | 48 | 64 | 48 | 0.47 |
| gP | U/ml | 2.7E2 | 2.9E2 | 2.8E2 | 2.9E2 | 1.3E2 | 9.8E1 | 6.5E1 | 1.2E1 | 1.1E3 | 5.2E2 | 64 | 47 | 64 | 47 | 0.58 |
| gW | ng/ml | 5.2E2 | 3.6E2 | 8.9E2 | 7.5E2 | 1.0E3 | 9.4E2 | 2.3E0 | 5.3E1 | 6.1E3 | 4.2E3 | 49 | 33 | 49 | 33 | 0.44 |
| gV | ng/ml | 1.7E1 | 2.2E1 | 1.9E1 | 2.0E1 | 5.6E0 | 8.6E0 | 1.0E1 | 8.1E-2 | 2.7E1 | 3.0E1 | 19 | 10 | 19 | 10 | 0.58 |
| fF | pg/mL | 1.3E3 | 9.0E2 | 1.3E4 | 1.2E4 | 4.2E4 | 4.2E4 | 1.8E1 | 1.2E1 | 2.8E5 | 2.5E5 | 58 | 45 | 58 | 45 | 0.47 |
| gZ | ug/ml | 7.8E-1 | 7.5E-1 | 2.8E1 | 4.4E1 | 1.0E2 | 1.2E2 | 8.7E-2 | 3.6E-1 | 4.1E2 | 4.0E2 | 15 | 14 | 15 | 14 | 0.60 |
| hA | ng/ml | 2.6E0 | 2.9E0 | 1.4E1 | 1.9E1 | 5.3E1 | 5.5E1 | 1.7E-2 | 1.7E-2 | 3.5E2 | 2.9E2 | 52 | 31 | 52 | 31 | 0.54 |
| nM | pg/ml | 1.0E-9 | 1.0E-9 | 1.0E-9 | 5.7E1 | 0.0E0 | 2.9E2 | 1.0E-9 | 1.0E-9 | 1.0E-9 | 1.5E3 | 36 | 27 | 36 | 27 | 0.52 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| nN | pg/ml | 1.1E3 | 2.2E3 | 4.8E3 | 1.1E4 | 1.7E4 | 3.0E4 | 1.1E2 | 3.5E2 | 1.0E5 | 1.5E5 | 36 | 27 | 36 | 27 | 0.66 |
| nO | pg/ml | 2.2E1 | 2.5E1 | 3.7E1 | 3.8E1 | 5.4E1 | 3.8E1 | 6.7E0 | 4.0E0 | 3.1E2 | 2.0E2 | 36 | 27 | 36 | 27 | 0.55 |
| nR | pg/ml | 2.0E1 | 1.8E1 | 7.5E1 | 1.4E2 | 1.5E2 | 3.9E2 | 1.4E0 | 1.0E0 | 8.2E2 | 1.9E3 | 36 | 27 | 36 | 27 | 0.50 |
| nT | pg/ml | 5.9E1 | 1.1E2 | 9.9E1 | 1.4E2 | 1.1E2 | 1.8E2 | 1.0E-9 | 1.0E-9 | 6.4E2 | 9.2E2 | 36 | 27 | 36 | 27 | 0.60 |
| nU | pg/ml | 4.4E1 | 4.4E1 | 9.8E1 | 1.1E2 | 2.5E2 | 2.0E2 | 1.0E-9 | 1.0E-9 | 1.5E3 | 9.2E2 | 36 | 27 | 36 | 27 | 0.51 |
| lW | pg/ml | 1.0E-9 | 1.0E-9 | 9.4E0 | 1.6E1 | 1.8E1 | 4.4E1 | 1.0E-9 | 1.0E-9 | 7.0E1 | 1.7E2 | 36 | 27 | 36 | 27 | 0.48 |
| lX | pg/ml | 9.1E2 | 8.6E2 | 9.4E2 | 9.4E2 | 4.9E2 | 6.3E2 | 3.2E2 | 1.9E2 | 1.9E3 | 2.5E3 | 36 | 27 | 36 | 27 | 0.47 |
| lY | pg/ml | 1.7E1 | 2.2E1 | 1.8E1 | 2.4E1 | 1.3E1 | 2.3E1 | 1.0E-9 | 1.0E-9 | 4.8E1 | 1.2E2 | 36 | 27 | 36 | 27 | 0.56 |
| mE | pg/ml | 1.0E-9 | 1.0E-9 | 1.7E0 | 4.1E0 | 4.7E0 | 1.1E1 | 1.0E-9 | 1.0E-9 | 2.8E1 | 5.7E1 | 36 | 27 | 36 | 27 | 0.59 |
| mF | pg/ml | 1.4E-1 | 2.7E-1 | 8.4E0 | 5.7E0 | 4.1E1 | 2.0E1 | 1.0E-9 | 1.0E-9 | 2.5E2 | 1.1E2 | 36 | 27 | 36 | 27 | 0.51 |
| mH | pg/ml | 3.3E0 | 3.1E0 | 4.7E0 | 6.0E0 | 5.3E0 | 1.0E1 | 4.0E-1 | 4.0E-1 | 3.2E1 | 5.3E1 | 36 | 27 | 36 | 27 | 0.49 |
| mI | pg/ml | 1.0E-9 | 3.4E0 | 9.5E0 | 3.5E1 | 1.8E1 | 9.3E1 | 1.0E-9 | 1.0E-9 | 6.7E1 | 4.6E2 | 36 | 27 | 36 | 27 | 0.58 |
| mM | pg/ml | 4.1E1 | 3.8E1 | 9.6E1 | 9.0E1 | 1.9E2 | 1.2E2 | 1.0E-9 | 1.0E-9 | 1.1E3 | 4.7E2 | 36 | 27 | 36 | 27 | 0.47 |
| mP | pg/ml | 1.4E1 | 1.5E1 | 1.8E1 | 5.0E1 | 2.0E1 | 1.5E2 | 1.0E-9 | 1.0E-9 | 1.2E2 | 8.1E2 | 35 | 27 | 35 | 27 | 0.51 |
| mS | pg/ml | 1.6E3 | 1.4E3 | 1.8E3 | 1.7E3 | 8.2E2 | 1.2E3 | 8.8E1 | 1.0E-9 | 3.7E3 | 5.1E3 | 36 | 27 | 36 | 27 | 0.44 |
| mT | pg/ml | 4.8E1 | 7.0E1 | 1.6E2 | 1.7E2 | 3.0E2 | 3.5E2 | 1.0E1 | 1.2E1 | 1.4E3 | 1.7E3 | 35 | 27 | 35 | 27 | 0.54 |
| mU | pg/ml | 2.5E0 | 1.9E0 | 9.5E0 | 3.8E0 | 3.7E1 | 4.6E0 | 1.0E-9 | 1.0E-9 | 2.2E2 | 2.3E1 | 35 | 27 | 35 | 27 | 0.44 |
| mW | pg/ml | 2.5E3 | 1.9E3 | 2.6E3 | 2.6E3 | 1.2E3 | 2.2E3 | 1.0E-9 | 3.7E2 | 5.5E3 | 1.1E4 | 35 | 27 | 35 | 27 | 0.40 |
| mY | pg/ml | 6.6E2 | 6.2E2 | 8.3E2 | 1.2E3 | 8.6E2 | 1.8E3 | 1.0E-9 | 1.0E-9 | 4.2E3 | 8.0E3 | 36 | 27 | 36 | 27 | 0.52 |
| mZ | pg/ml | 2.5E2 | 1.4E2 | 4.2E2 | 2.9E2 | 5.7E2 | 3.5E2 | 1.6E1 | 1.1E1 | 3.1E3 | 1.2E3 | 35 | 27 | 35 | 27 | 0.39 |
| nA | pg/ml | 1.8E0 | 9.3E-1 | 7.2E0 | 5.2E0 | 1.4E1 | 1.3E1 | 1.0E-9 | 1.0E-9 | 5.4E1 | 6.5E1 | 35 | 27 | 35 | 27 | 0.44 |
| nB | pg/ml | 2.7E2 | 3.0E2 | 3.1E2 | 3.4E2 | 1.7E2 | 2.0E2 | 3.0E1 | 3.8E1 | 8.2E2 | 9.6E2 | 36 | 27 | 36 | 27 | 0.53 |
| nC | pg/ml | 1.0E-9 | 5.8E1 | 1.1E4 | 8.9E3 | 6.4E4 | 4.2E4 | 1.0E-9 | 1.0E-9 | 3.8E5 | 2.2E5 | 36 | 27 | 36 | 27 | 0.50 |
| nD | pg/ml | 7.0E0 | 6.4E0 | 9.3E0 | 1.6E1 | 9.1E0 | 4.9E1 | 1.0E-9 | 1.0E-9 | 3.7E1 | 2.6E2 | 35 | 27 | 35 | 27 | 0.45 |
| nF | pg/ml | 1.0E-9 | 1.0E-9 | 4.0E0 | 1.5E0 | 1.6E1 | 5.8E0 | 1.0E-9 | 1.0E-9 | 9.3E1 | 2.7E1 | 36 | 27 | 36 | 27 | 0.48 |
| nH | pg/ml | 1.2E0 | 1.1E0 | 7.9E1 | 3.8E2 | 4.4E2 | 1.9E3 | 1.0E-9 | 1.0E-9 | 2.6E3 | 1.0E4 | 35 | 27 | 35 | 27 | 0.52 |
| nI | pg/ml | 4.6E1 | 1.0E-9 | 5.2E1 | 5.3E1 | 6.0E1 | 9.2E1 | 1.0E-9 | 1.0E-9 | 2.0E2 | 3.5E2 | 36 | 27 | 36 | 27 | 0.41 |
| nJ | pg/ml | 6.2E-1 | 1.7E-1 | 1.2E0 | 5.5E0 | 1.8E0 | 2.5E1 | 1.0E-9 | 1.0E-9 | 7.0E0 | 1.3E2 | 36 | 27 | 36 | 27 | 0.43 |
| nK | pg/ml | 1.0E-9 | 1.0E-9 | 1.0E1 | 1.5E1 | 2.1E1 | 2.5E1 | 1.0E-9 | 1.0E-9 | 9.6E1 | 1.0E2 | 35 | 27 | 35 | 27 | 0.58 |
| nL | pg/ml | 1.0E-9 | 1.0E-9 | 1.3E2 | 5.5E2 | 7.2E2 | 2.6E3 | 1.0E-9 | 1.0E-9 | 4.3E3 | 1.4E4 | 36 | 27 | 36 | 27 | 0.55 |
| hL | pg/ml | 1.5E4 | 2.7E4 | 1.9E4 | 2.7E4 | 1.4E4 | 1.5E4 | 2.6E3 | 5.1E3 | 7.2E4 | 6.0E4 | 31 | 18 | 31 | 18 | 0.68 |
| hO | pg/ml | 1.6E4 | 1.6E4 | 1.6E4 | 1.6E4 | 2.6E3 | 2.3E3 | 1.3E4 | 1.1E4 | 2.4E4 | 2.1E4 | 31 | 18 | 31 | 18 | 0.49 |
| hP | ng/ml | 4.4E5 | 4.4E5 | 3.8E5 | 6.9E5 | 1.7E5 | 7.5E5 | 4.7E4 | 1.7E4 | 9.0E5 | 2.8E6 | 31 | 18 | 31 | 18 | 0.64 |
| wJ | pg/ml | 1.4E5 | 1.0E5 | 1.6E5 | 1.6E5 | 9.7E4 | 1.5E5 | 1.1E4 | 1.3E4 | 4.0E5 | 5.8E5 | 32 | 19 | 32 | 19 | 0.45 |
| wK | pg/ml | 3.2E4 | 3.5E4 | 5.6E4 | 3.9E4 | 8.7E4 | 3.0E4 | 3.7E3 | 7.5E3 | 5.0E5 | 1.2E5 | 32 | 19 | 32 | 19 | 0.45 |
| wL | pg/ml | 6.7E0 | 3.9E0 | 6.2E1 | 4.0E1 | 1.7E2 | 1.0E2 | 1.0E-9 | 1.0E-9 | 8.4E2 | 3.5E2 | 32 | 19 | 32 | 19 | 0.43 |
| wP | pg/ml | 2.8E4 | 2.8E4 | 4.0E4 | 7.0E4 | 4.0E4 | 8.1E4 | 4.5E3 | 1.3E3 | 1.7E5 | 3.0E5 | 32 | 19 | 32 | 19 | 0.58 |
| wQ | pg/ml | 3.5E1 | 3.9E1 | 6.1E1 | 6.3E1 | 8.4E1 | 1.1E2 | 1.0E-9 | 1.0E-9 | 3.7E2 | 5.1E2 | 32 | 19 | 32 | 19 | 0.52 |
| hR | pg/ml | 2.8E4 | 2.4E4 | 3.1E4 | 2.6E4 | 1.1E4 | 1.1E4 | 1.0E-9 | 4.3E3 | 5.8E4 | 4.9E4 | 46 | 30 | 46 | 30 | 0.39 |
| hV | pg/ml | 4.3E2 | 4.4E2 | 4.3E2 | 4.4E2 | 2.1E2 | 2.4E2 | 1.0E-9 | 8.2E1 | 9.3E2 | 9.6E2 | 46 | 30 | 46 | 30 | 0.50 |
| hW | pg/ml | 1.8E3 | 2.4E3 | 2.0E3 | 3.7E3 | 1.2E3 | 6.9E3 | 1.0E-9 | 1.1E3 | 7.3E3 | 4.0E4 | 46 | 30 | 46 | 30 | 0.64 |
| hX | pg/ml | 1.1E3 | 1.1E3 | 1.2E3 | 1.1E3 | 1.2E3 | 5.7E2 | 2.5E0 | 1.3E2 | 8.6E3 | 2.9E3 | 46 | 30 | 46 | 30 | 0.52 |
| iA | pg/ml | 1.9E2 | 1.7E2 | 2.9E2 | 2.5E2 | 3.0E2 | 2.5E2 | 2.9E1 | 1.5E1 | 1.8E3 | 8.7E2 | 58 | 45 | 58 | 45 | 0.43 |
| iB | ng/ml | 5.0E0 | 6.8E0 | 6.5E0 | 7.7E0 | 5.1E0 | 5.4E0 | 3.3E-2 | 1.6E0 | 2.4E1 | 2.2E1 | 52 | 31 | 52 | 31 | 0.57 |
| iC | U/ml | 3.6E-1 | 3.8E-1 | 1.7E0 | 6.5E-1 | 7.7E0 | 7.6E-1 | 1.0E-9 | 3.7E-2 | 5.5E1 | 3.2E0 | 52 | 31 | 52 | 31 | 0.55 |
| tQ | pg/ml | 1.5E3 | 1.4E3 | 1.5E3 | 1.5E3 | 5.3E2 | 6.9E2 | 3.7E2 | 7.2E2 | 2.5E3 | 3.3E3 | 31 | 16 | 31 | 16 | 0.47 |
| tT | pg/ml | 1.5E1 | 2.4E1 | 1.8E1 | 2.9E1 | 9.6E0 | 2.0E1 | 5.4E0 | 1.1E1 | 4.8E1 | 9.3E1 | 31 | 17 | 31 | 17 | 0.70 |
| tS | pg/ml | 7.7E-1 | 7.7E-1 | 9.8E-1 | 1.6E0 | 9.8E-1 | 2.5E0 | 1.0E-9 | 1.0E-9 | 4.0E0 | 1.0E1 | 31 | 18 | 31 | 18 | 0.56 |
| tX | pg/ml | 7.1E-1 | 1.6E0 | 1.0E0 | 2.9E0 | 8.4E-1 | 2.9E0 | 2.5E-2 | 3.2E-1 | 3.3E0 | 1.0E1 | 31 | 17 | 31 | 17 | 0.74 |
| tO | pg/ml | 4.4E0 | 3.9E0 | 4.5E0 | 5.7E0 | 2.6E0 | 4.5E0 | 1.7E0 | 1.7E0 | 9.9E0 | 1.8E1 | 31 | 18 | 31 | 18 | 0.55 |
| tR | pg/ml | 1.9E-1 | 2.2E-1 | 2.4E-1 | 4.4E-1 | 2.4E-1 | 6.6E-1 | 1.0E-9 | 1.0E-9 | 9.1E-1 | 2.5E0 | 31 | 17 | 31 | 17 | 0.57 |
| tU | pg/ml | 8.9E0 | 1.1E1 | 1.1E1 | 1.6E1 | 1.0E1 | 1.8E1 | 1.5E0 | 2.2E-1 | 5.5E1 | 8.0E1 | 31 | 19 | 31 | 19 | 0.61 |
| tN | pg/ml | 1.9E1 | 2.2E1 | 2.2E1 | 4.5E1 | 1.7E1 | 4.7E1 | 1.0E-9 | 1.0E1 | 7.6E1 | 1.6E2 | 30 | 17 | 30 | 17 | 0.66 |
| tV | ng/ml | 4.8E2 | 1.1E3 | 6.2E2 | 1.1E3 | 4.3E2 | 7.1E2 | 1.9E2 | 5.3E1 | 1.8E3 | 3.1E3 | 32 | 18 | 32 | 18 | 0.71 |
| iH | ng/ml | 1.7E5 | 1.6E5 | 1.6E5 | 1.5E5 | 4.7E4 | 5.5E4 | 7.1E4 | 2.9E3 | 2.6E5 | 2.4E5 | 58 | 45 | 58 | 45 | 0.46 |
| iJ | ng/ml | 5.3E4 | 4.3E4 | 6.0E4 | 5.1E4 | 3.6E4 | 3.8E4 | 2.1E4 | 1.8E3 | 2.5E5 | 2.5E5 | 58 | 45 | 58 | 45 | 0.40 |
| hB | ng/ml | 4.8E-1 | 5.1E-1 | 6.4E-1 | 6.9E-1 | 4.7E-1 | 5.9E-1 | 1.4E-1 | 1.2E-1 | 2.3E0 | 3.2E0 | 58 | 45 | 58 | 45 | 0.51 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| hC | pg/ml | 4.0E3 | 7.7E3 | 6.4E3 | 1.1E4 | 6.3E3 | 1.8E4 | 6.0E1 | 4.1E1 | 3.3E4 | 1.1E5 | 58 | 45 | 58 | 45 | 0.59 |
| hF | ng/ml | 1.0E-9 | 1.0E-9 | 6.9E1 | 1.0E-9 | 5.3E2 | 0.0E0 | 1.0E-9 | 1.0E-9 | 4.0E3 | 1.0E-9 | 58 | 45 | 58 | 45 | 0.49 |
| hG | pg/ml | 7.2E3 | 6.5E3 | 8.1E3 | 7.4E3 | 3.2E3 | 3.9E3 | 1.8E3 | 2.3E3 | 1.8E4 | 2.0E4 | 58 | 45 | 58 | 45 | 0.38 |
| iO | ng/ml | 4.0E5 | 3.9E5 | 4.5E5 | 4.1E5 | 2.1E5 | 1.8E5 | 1.3E5 | 9.8E4 | 1.1E6 | 8.2E5 | 58 | 45 | 58 | 45 | 0.45 |
| iP | ng/ml | 6.0E4 | 4.8E4 | 6.2E4 | 5.3E4 | 5.5E4 | 3.7E4 | 8.3E3 | 7.1E3 | 4.4E5 | 2.2E5 | 58 | 45 | 58 | 45 | 0.42 |
| iZ | ng/ml | 1.5E3 | 1.9E3 | 1.8E3 | 2.1E3 | 8.6E2 | 8.9E2 | 8.2E2 | 7.5E2 | 5.7E3 | 4.6E3 | 58 | 43 | 58 | 43 | 0.62 |
| yH | pg/ml | 9.1E2 | 1.1E3 | 1.8E3 | 3.6E3 | 2.9E3 | 7.6E3 | 1.0E-9 | 1.0E-9 | 1.5E4 | 2.5E4 | 31 | 18 | 31 | 18 | 0.50 |
| yK | U/ml | 1.8E1 | 2.5E1 | 4.7E1 | 3.3E1 | 8.8E1 | 3.5E1 | 1.0E-9 | 1.0E-9 | 3.8E2 | 1.4E2 | 31 | 18 | 31 | 18 | 0.56 |
| yJ | pg/ml | 3.4E4 | 3.6E4 | 4.5E4 | 3.5E4 | 3.0E4 | 2.2E4 | 9.2E3 | 1.9E3 | 1.4E5 | 8.2E4 | 31 | 18 | 31 | 18 | 0.41 |
| yD | ng/ml | 1.3E-2 | 1.3E-2 | 1.3E-2 | 1.3E-2 | 5.7E-3 | 6.5E-3 | 1.0E-9 | 1.0E-9 | 2.8E-2 | 2.4E-2 | 32 | 19 | 32 | 19 | 0.46 |
| jB | ng/ml | 2.5E5 | 2.0E5 | 2.7E5 | 2.0E5 | 7.1E4 | 6.3E4 | 1.5E5 | 9.9E4 | 3.6E5 | 3.3E5 | 15 | 14 | 15 | 14 | 0.25 |
| wB | pg/ml | 8.9E3 | 1.2E4 | 1.0E4 | 1.5E4 | 7.0E3 | 1.1E4 | 1.9E3 | 2.3E3 | 3.3E4 | 4.2E4 | 32 | 19 | 32 | 19 | 0.62 |
| pY | pg/ml | 5.7E0 | 6.8E0 | 1.2E1 | 7.6E0 | 3.5E1 | 4.2E0 | 1.6E0 | 3.0E0 | 2.0E2 | 1.8E1 | 31 | 18 | 31 | 18 | 0.64 |
| sI | ng/ml | 5.4E-2 | 5.2E-2 | 5.6E-2 | 5.9E-2 | 2.2E-2 | 4.2E-2 | 2.1E-2 | 1.0E-2 | 1.1E-1 | 1.5E-1 | 16 | 10 | 16 | 10 | 0.47 |
| sF | mIU/mL | 7.4E0 | 5.0E0 | 1.2E1 | 1.1E1 | 1.8E1 | 1.5E1 | 6.2E-1 | 1.5E0 | 7.5E1 | 5.2E1 | 16 | 10 | 16 | 10 | 0.45 |
| sH | mIU/mL | 4.6E0 | 2.6E0 | 4.9E0 | 4.1E0 | 5.2E0 | 4.5E0 | 1.0E-9 | 3.9E-1 | 2.1E1 | 1.5E1 | 16 | 10 | 16 | 10 | 0.45 |
| sJ | ng/ml | 1.5E-1 | 2.4E-1 | 7.4E-1 | 2.2E-1 | 1.7E0 | 1.9E-1 | 1.0E-9 | 3.0E-2 | 6.4E0 | 6.1E-1 | 16 | 10 | 16 | 10 | 0.52 |
| rC | pg/ml | 1.6E3 | 1.4E3 | 2.3E3 | 2.1E3 | 2.5E3 | 2.3E3 | 1.1E2 | 1.0E-9 | 1.5E4 | 1.1E4 | 44 | 29 | 44 | 29 | 0.47 |
| rB | pg/ml | 3.1E1 | 2.9E1 | 4.9E1 | 6.3E1 | 7.1E1 | 7.9E1 | 1.0E-9 | 1.0E-9 | 3.9E2 | 3.2E2 | 44 | 29 | 44 | 29 | 0.53 |
| zG | 2.5ng/ml | 2.2E-1 | 2.2E-1 | 7.1E-1 | 4.1E-1 | 1.2E0 | 6.4E-1 | 1.0E-9 | 1.0E-9 | 4.8E0 | 2.7E0 | 31 | 18 | 31 | 18 | 0.48 |
| zH | 2.3mU/ml | 8.8E-2 | 8.7E-2 | 9.8E-2 | 9.1E-2 | 5.0E-2 | 4.1E-2 | 1.0E-2 | 2.1E-2 | 3.1E-1 | 1.8E-1 | 31 | 18 | 31 | 18 | 0.45 |
| zI | 2.6ng/ml | 1.9E0 | 2.4E0 | 3.4E0 | 6.5E0 | 3.5E0 | 8.2E0 | 6.1E-1 | 5.4E-1 | 1.5E1 | 2.7E1 | 31 | 18 | 31 | 18 | 0.56 |
| qA | ng/ml | 7.8E6 | 1.3E7 | 1.1E7 | 1.3E7 | 8.0E6 | 5.9E6 | 3.7E6 | 4.3E6 | 3.9E7 | 3.0E7 | 31 | 18 | 31 | 18 | 0.69 |
| qB | ng/ml | 6.6E5 | 6.7E5 | 8.5E5 | 8.8E5 | 6.3E5 | 8.1E5 | 1.9E5 | 2.4E5 | 2.9E6 | 3.8E6 | 31 | 18 | 31 | 18 | 0.50 |
| qC | ng/ml | 3.1E5 | 2.5E5 | 5.9E5 | 6.1E5 | 7.4E5 | 1.1E6 | 2.5E4 | 6.5E4 | 3.1E6 | 4.7E6 | 31 | 18 | 31 | 18 | 0.48 |
| qD | ng/ml | 1.5E7 | 1.5E7 | 1.7E7 | 1.7E7 | 7.5E6 | 7.3E6 | 7.0E6 | 8.7E6 | 3.7E7 | 3.4E7 | 31 | 18 | 31 | 18 | 0.51 |
| jD | ng/ml | 3.8E1 | 3.2E1 | 4.3E1 | 5.3E1 | 4.1E1 | 6.3E1 | 1.0E-9 | 1.0E-9 | 1.9E2 | 2.9E2 | 52 | 31 | 52 | 31 | 0.52 |
| jE | ng/ml | 1.0E-9 | 1.0E-9 | 4.6E0 | 6.1E0 | 1.2E1 | 1.1E1 | 1.0E-9 | 1.0E-9 | 6.2E1 | 3.5E1 | 52 | 31 | 52 | 31 | 0.55 |
| jF | ng/ml | 4.5E1 | 1.6E1 | 4.7E1 | 3.9E1 | 4.9E1 | 5.4E1 | 1.0E-9 | 1.0E-9 | 1.9E2 | 1.9E2 | 52 | 31 | 52 | 31 | 0.43 |
| jG | ng/ml | 4.2E3 | 4.2E3 | 4.4E3 | 4.4E3 | 1.9E3 | 2.0E3 | 6.7E2 | 1.4E3 | 9.5E3 | 9.6E3 | 52 | 31 | 52 | 31 | 0.48 |
| jH | ng/ml | 7.9E1 | 7.5E1 | 8.4E1 | 8.9E1 | 4.7E1 | 7.4E1 | 1.3E1 | 1.5E1 | 2.4E2 | 4.3E2 | 52 | 31 | 52 | 31 | 0.48 |
| jI | ng/ml | 7.4E1 | 8.7E1 | 7.9E1 | 1.0E2 | 3.3E1 | 7.9E1 | 3.8E1 | 3.8E1 | 1.9E2 | 4.4E2 | 52 | 31 | 52 | 31 | 0.56 |
| sK | pg/mL | 4.1E3 | 3.8E3 | 4.0E3 | 5.5E3 | 1.7E3 | 5.1E3 | 1.8E3 | 2.1E3 | 8.8E3 | 2.3E4 | 30 | 17 | 30 | 17 | 0.55 |
| sM | pg/mL | 7.3E4 | 7.9E4 | 7.8E4 | 8.9E4 | 2.7E4 | 4.3E4 | 4.3E4 | 3.9E4 | 1.6E5 | 2.0E5 | 30 | 17 | 30 | 17 | 0.56 |
| sO | pg/mL | 2.3E8 | 2.3E8 | 2.4E8 | 2.3E8 | 8.4E7 | 1.1E8 | 4.9E7 | 6.6E7 | 4.4E8 | 4.2E8 | 30 | 17 | 30 | 17 | 0.45 |
| wC | ng/ml | 1.5E0 | 1.6E0 | 2.0E0 | 1.8E0 | 1.4E0 | 1.1E0 | 3.6E-1 | 6.1E-2 | 6.5E0 | 4.8E0 | 32 | 19 | 32 | 19 | 0.51 |
| wD | ng/ml | 2.2E1 | 2.8E1 | 1.0E2 | 6.0E1 | 3.7E2 | 7.0E1 | 3.8E0 | 2.8E0 | 2.1E3 | 2.9E2 | 32 | 19 | 32 | 19 | 0.63 |
| wE | ng/ml | 4.9E1 | 5.8E1 | 4.9E1 | 5.4E1 | 1.9E1 | 2.0E1 | 8.1E0 | 2.0E1 | 8.9E1 | 8.9E1 | 32 | 19 | 32 | 19 | 0.56 |
| wG | ng/ml | 1.1E-1 | 8.6E-2 | 1.4E-1 | 1.3E-1 | 1.3E-1 | 1.7E-1 | 1.0E-9 | 1.0E-9 | 4.8E-1 | 6.8E-1 | 32 | 19 | 32 | 19 | 0.45 |
| wH | ng/ml | 3.2E-2 | 3.9E-2 | 2.9E-1 | 5.5E-1 | 7.9E-1 | 1.3E0 | 1.0E-9 | 1.0E-9 | 4.2E0 | 5.6E0 | 32 | 19 | 32 | 19 | 0.55 |
| wF | ng/ml | 2.7E-1 | 2.6E-1 | 2.9E0 | 2.0E0 | 1.1E1 | 4.4E0 | 1.0E-9 | 1.0E-9 | 5.7E1 | 1.9E1 | 32 | 19 | 32 | 19 | 0.54 |
| rA | pg/ml | 2.4E1 | 1.9E1 | 2.7E1 | 2.8E1 | 1.7E1 | 2.5E1 | 1.0E-9 | 1.0E-9 | 6.4E1 | 1.1E2 | 50 | 30 | 50 | 30 | 0.47 |
| qZ | pg/ml | 4.7E1 | 5.8E1 | 8.4E2 | 2.5E2 | 2.7E3 | 7.1E2 | 2.8E-4 | 5.9E-4 | 1.0E4 | 3.4E3 | 38 | 22 | 38 | 22 | 0.54 |
| qY | pg/ml | 1.5E1 | 1.3E1 | 4.1E1 | 2.9E1 | 5.0E1 | 6.1E1 | 8.7E-1 | 2.1E0 | 1.8E2 | 3.3E2 | 50 | 30 | 50 | 30 | 0.40 |
| qX | pg/ml | 5.5E1 | 6.4E1 | 6.5E1 | 7.5E1 | 4.5E1 | 4.8E1 | 1.0E-9 | 1.0E-9 | 1.7E2 | 2.1E2 | 50 | 30 | 50 | 30 | 0.55 |
| qW | pg/ml | 7.4E0 | 7.3E0 | 9.6E0 | 8.6E0 | 9.0E0 | 8.7E0 | 1.0E-9 | 1.0E-9 | 3.6E1 | 3.1E1 | 50 | 30 | 50 | 30 | 0.45 |
| qV | pg/ml | 1.5E3 | 1.9E3 | 2.3E3 | 2.4E3 | 2.0E3 | 1.9E3 | 1.7E2 | 1.0E2 | 1.1E4 | 9.6E3 | 50 | 30 | 50 | 30 | 0.53 |
| qU | pg/ml | 4.6E1 | 9.6E1 | 1.4E2 | 2.8E2 | 2.3E2 | 4.4E2 | 1.0E-9 | 1.0E-9 | 1.2E3 | 2.1E3 | 50 | 30 | 50 | 30 | 0.62 |
| qT | pg/ml | 3.9E1 | 4.0E1 | 7.3E1 | 5.3E1 | 8.8E1 | 4.0E1 | 1.0E-9 | 1.0E-9 | 4.9E2 | 1.6E2 | 50 | 30 | 50 | 30 | 0.50 |
| qI | ng/ml | 6.2E4 | 6.3E4 | 6.4E4 | 6.2E4 | 3.3E4 | 2.7E4 | 1.0E4 | 2.5E4 | 1.6E5 | 1.3E5 | 29 | 17 | 29 | 17 | 0.49 |
| qH | ng/ml | 5.4E4 | 6.2E4 | 6.6E4 | 7.9E4 | 4.0E4 | 4.0E4 | 1.5E4 | 3.2E4 | 1.8E5 | 1.8E5 | 29 | 17 | 29 | 17 | 0.62 |
| qG | ng/ml | 1.8E5 | 1.8E5 | 1.9E5 | 1.9E5 | 6.2E4 | 8.3E4 | 3.4E4 | 8.4E4 | 3.0E5 | 4.2E5 | 29 | 17 | 29 | 17 | 0.47 |
| jK | ng/ml | 1.6E3 | 1.3E3 | 1.7E3 | 1.5E3 | 6.4E2 | 6.3E2 | 2.8E2 | 7.5E2 | 4.1E3 | 3.6E3 | 52 | 31 | 52 | 31 | 0.39 |
| jL | ng/ml | 1.7E2 | 2.4E2 | 2.8E2 | 2.7E2 | 2.1E2 | 1.7E2 | 5.9E1 | 6.4E1 | 8.1E2 | 7.6E2 | 52 | 31 | 52 | 31 | 0.55 |
| jM | ng/ml | 6.7E4 | 6.8E4 | 7.0E4 | 7.6E4 | 3.4E4 | 4.8E4 | 2.1E4 | 4.6E3 | 1.7E5 | 1.7E5 | 52 | 31 | 52 | 31 | 0.53 |
| jO | pg/ml | 2.4E5 | 2.5E5 | 2.8E5 | 2.5E5 | 1.5E5 | 1.3E5 | 7.6E4 | 9.6E4 | 7.7E5 | 6.5E5 | 52 | 31 | 52 | 31 | 0.46 |
| jP | pg/ml | 2.6E5 | 3.2E5 | 2.8E5 | 3.4E5 | 1.4E5 | 1.7E5 | 6.1E4 | 1.3E5 | 7.1E5 | 7.0E5 | 52 | 31 | 52 | 31 | 0.59 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| jQ | pg/ml | 2.4E3 | 1.3E3 | 2.9E3 | 3.0E3 | 2.3E3 | 3.3E3 | 2.5E2 | 5.0E0 | 1.0E4 | 1.3E4 | 52 | 31 | 52 | 31 | 0.44 |
| jR | pg/ml | 5.9E3 | 3.8E3 | 8.5E3 | 1.1E4 | 8.0E3 | 1.5E4 | 3.0E1 | 1.0E-9 | 3.5E4 | 5.6E4 | 52 | 31 | 52 | 31 | 0.46 |
| jT | pg/ml | 1.7E5 | 1.6E5 | 1.7E5 | 1.7E5 | 5.8E4 | 6.5E4 | 7.1E4 | 7.5E4 | 3.5E5 | 3.5E5 | 52 | 31 | 52 | 31 | 0.50 |
| xA | pg/ml | 5.7E0 | 6.0E0 | 1.2E1 | 2.1E1 | 1.5E1 | 4.3E1 | 1.0E-9 | 1.0E-9 | 6.1E1 | 1.6E2 | 31 | 18 | 31 | 18 | 0.48 |
| yE | pg/ml | 7.9E1 | 9.1E1 | 7.8E1 | 9.3E1 | 3.2E1 | 4.0E1 | 6.4E0 | 3.5E1 | 1.4E2 | 2.0E2 | 31 | 18 | 31 | 18 | 0.61 |
| tM | pg/ml | 4.3E1 | 4.2E1 | 3.9E1 | 4.3E1 | 1.9E1 | 1.9E1 | 1.0E-9 | 1.6E1 | 8.3E1 | 9.9E1 | 31 | 18 | 31 | 18 | 0.55 |
| tL | pg/ml | 1.0E-9 | 1.0E-9 | 2.4E0 | 4.7E-1 | 1.2E1 | 1.0E0 | 1.0E-9 | 1.0E-9 | 6.7E1 | 3.6E0 | 31 | 18 | 31 | 18 | 0.55 |
| jU | mIU/ml | 5.8E0 | 4.8E0 | 1.4E1 | 1.1E1 | 2.2E1 | 1.4E1 | 8.1E-2 | 7.1E-1 | 1.1E2 | 5.7E1 | 52 | 31 | 52 | 31 | 0.48 |
| jV | mIU/ml | 2.3E0 | 1.8E0 | 4.7E0 | 3.0E0 | 6.4E0 | 3.4E0 | 2.7E-3 | 1.0E-1 | 3.2E1 | 1.5E1 | 52 | 31 | 52 | 31 | 0.44 |
| jY | ng/ml | 5.8E-4 | 2.0E-3 | 1.0E-2 | 6.1E-3 | 4.3E-2 | 1.0E-2 | 1.0E-9 | 1.0E-9 | 3.0E-1 | 5.1E-2 | 52 | 31 | 52 | 31 | 0.60 |
| kC | pg/ml | 1.0E2 | 9.6E1 | 1.5E2 | 2.5E2 | 1.7E2 | 5.3E2 | 2.1E1 | 3.6E1 | 1.1E3 | 2.7E3 | 36 | 27 | 36 | 27 | 0.53 |
| kE | pg/ml | 1.5E5 | 1.4E5 | 1.4E5 | 1.4E5 | 3.6E4 | 4.2E4 | 4.1E4 | 7.5E4 | 2.3E5 | 2.7E5 | 36 | 27 | 36 | 27 | 0.48 |
| kF | pg/mL | 6.9E1 | 5.7E1 | 6.9E1 | 7.4E1 | 1.7E1 | 3.4E1 | 3.5E1 | 4.0E1 | 1.1E2 | 1.5E2 | 36 | 27 | 36 | 27 | 0.44 |
| kG | pg/mL | 8.0E3 | 9.0E3 | 1.2E4 | 1.7E4 | 1.2E4 | 3.1E4 | 1.9E3 | 1.1E3 | 5.8E4 | 1.6E5 | 36 | 27 | 36 | 27 | 0.52 |
| kI | pg/ml | 2.1E2 | 2.1E2 | 2.3E2 | 2.0E2 | 1.2E2 | 9.5E1 | 6.4E1 | 1.0E-9 | 6.7E2 | 3.7E2 | 36 | 27 | 36 | 27 | 0.46 |
| kK | pg/ml | 1.2E2 | 1.2E2 | 1.7E2 | 1.5E2 | 1.7E2 | 1.0E2 | 2.2E1 | 2.1E1 | 9.1E2 | 4.6E2 | 36 | 27 | 36 | 27 | 0.50 |
| kN | pg/ml | 1.0E3 | 1.1E3 | 1.5E3 | 1.9E3 | 1.7E3 | 2.1E3 | 2.1E2 | 3.8E2 | 1.0E4 | 8.7E3 | 36 | 27 | 36 | 27 | 0.53 |
| kO | pg/ml | 7.1E3 | 7.3E3 | 8.1E3 | 1.2E4 | 4.0E3 | 2.7E4 | 4.0E3 | 3.8E3 | 2.5E4 | 1.5E5 | 36 | 27 | 36 | 27 | 0.49 |
| kP | pg/ml | 5.5E3 | 5.2E3 | 6.8E3 | 6.3E3 | 4.6E3 | 3.9E3 | 9.6E2 | 1.6E3 | 2.7E4 | 1.5E4 | 36 | 27 | 36 | 27 | 0.46 |
| kQ | pg/ml | 4.3E3 | 4.7E3 | 5.4E3 | 5.9E3 | 3.9E3 | 4.7E3 | 5.6E2 | 1.1E3 | 2.5E4 | 2.5E4 | 58 | 45 | 58 | 45 | 0.53 |
| kR | pg/ml | 2.2E1 | 2.7E1 | 4.5E1 | 3.2E1 | 1.3E2 | 2.5E1 | 1.0E-9 | 3.4E0 | 1.0E3 | 1.1E2 | 58 | 45 | 58 | 45 | 0.54 |
| kS | pg/ml | 8.3E2 | 9.5E2 | 9.5E2 | 1.0E3 | 5.7E2 | 6.4E2 | 8.2E1 | 2.6E2 | 3.2E3 | 3.0E3 | 58 | 45 | 58 | 45 | 0.56 |
| pS | ng/ml | 1.6E5 | 1.4E5 | 2.0E5 | 1.6E5 | 1.1E5 | 8.3E4 | 7.5E4 | 6.8E4 | 5.7E5 | 3.6E5 | 30 | 17 | 30 | 17 | 0.41 |
| rZ | ng/ml | 1.4E-3 | 3.2E-3 | 5.9E-3 | 1.4E-2 | 1.5E-2 | 2.5E-2 | 1.0E-9 | 1.0E-9 | 9.4E-2 | 1.1E-1 | 45 | 29 | 45 | 29 | 0.62 |
| rY | ng/ml | 6.1E-2 | 7.1E-2 | 2.6E-1 | 7.7E-1 | 9.4E-1 | 3.7E0 | 2.4E-3 | 1.0E-9 | 6.3E0 | 2.0E1 | 45 | 29 | 45 | 29 | 0.56 |
| rX | ng/ml | 1.0E-9 | 1.0E-9 | 1.2E-1 | 1.1E-1 | 5.6E-1 | 5.7E-1 | 1.0E-9 | 1.0E-9 | 3.7E0 | 3.1E0 | 45 | 29 | 45 | 29 | 0.52 |
| lK | pg/ml | 6.5E1 | 6.8E1 | 1.4E2 | 1.3E2 | 1.7E2 | 1.7E2 | 1.0E-9 | 1.0E-9 | 7.0E2 | 6.9E2 | 51 | 31 | 51 | 31 | 0.44 |
| lL | pg/ml | 1.8E3 | 1.7E3 | 3.3E3 | 2.5E3 | 6.3E3 | 2.2E3 | 7.5E1 | 1.2E2 | 4.2E4 | 7.7E3 | 52 | 31 | 52 | 31 | 0.50 |
| lM | pg/ml | 1.6E3 | 1.1E3 | 4.7E3 | 5.8E3 | 7.6E3 | 1.4E4 | 2.2E2 | 9.5E0 | 4.2E4 | 6.7E4 | 52 | 31 | 52 | 31 | 0.44 |
| lN | pg/ml | 1.0E-9 | 1.0E-9 | 2.9E0 | 4.1E0 | 7.2E0 | 7.1E0 | 1.0E-9 | 1.0E-9 | 4.3E1 | 2.4E1 | 52 | 31 | 52 | 31 | 0.56 |
| lO | pg/ml | 1.0E-9 | 1.0E-9 | 6.7E-1 | 8.5E0 | 4.7E0 | 3.3E1 | 1.0E-9 | 1.0E-9 | 3.4E1 | 1.4E2 | 51 | 31 | 51 | 31 | 0.52 |
| zA | ng/ml | 2.1E7 | 2.1E7 | 2.2E7 | 2.0E7 | 6.5E6 | 5.9E6 | 1.0E7 | 1.0E7 | 3.6E7 | 3.1E7 | 31 | 19 | 31 | 19 | 0.45 |
| rW | ng/ml | 1.2E-2 | 1.4E-2 | 2.3E-2 | 4.9E-2 | 3.5E-2 | 8.9E-2 | 1.0E-9 | 1.0E-9 | 1.7E-1 | 3.2E-1 | 31 | 15 | 31 | 15 | 0.58 |
| rV | ng/ml | 1.0E-9 | 1.0E-9 | 1.0E-2 | 1.9E-2 | 5.1E-2 | 4.0E-2 | 1.0E-9 | 1.0E-9 | 2.8E-1 | 1.5E-1 | 31 | 15 | 31 | 15 | 0.67 |
| rU | ng/ml | 4.2E-2 | 9.7E-2 | 1.7E-1 | 1.3E-1 | 4.8E-1 | 1.2E-1 | 1.0E-9 | 1.0E-9 | 2.7E0 | 4.0E-1 | 31 | 15 | 31 | 15 | 0.61 |
| rT | ng/ml | 6.3E0 | 4.2E0 | 6.5E0 | 7.8E0 | 4.1E0 | 6.2E0 | 6.5E-1 | 1.0E0 | 2.1E1 | 2.0E1 | 31 | 15 | 31 | 15 | 0.52 |
| rS | ng/ml | 3.5E0 | 7.4E0 | 5.2E0 | 1.7E1 | 5.3E0 | 2.1E1 | 1.1E0 | 1.0E0 | 2.5E1 | 7.0E1 | 31 | 15 | 31 | 15 | 0.72 |
| sC | pg/mL | 5.3E3 | 8.5E3 | 8.9E3 | 1.4E4 | 1.1E4 | 1.8E4 | 2.3E3 | 1.7E3 | 5.1E4 | 7.4E4 | 30 | 17 | 30 | 17 | 0.59 |
| yL | pg/ml | 3.0E1 | 3.2E1 | 3.5E1 | 1.2E2 | 3.0E1 | 3.3E2 | 5.6E0 | 9.1E0 | 1.8E2 | 1.4E3 | 31 | 18 | 31 | 18 | 0.58 |
| rP | ng/ml | 9.8E1 | 2.1E2 | 1.8E2 | 3.1E2 | 1.8E2 | 2.5E2 | 1.0E-9 | 1.2E1 | 5.0E2 | 8.0E2 | 31 | 15 | 31 | 15 | 0.62 |
| rQ | ng/ml | 1.0E-9 | 1.0E-9 | 1.0E-9 | 2.1E1 | 0.0E0 | 5.1E1 | 1.0E-9 | 1.0E-9 | 1.0E-9 | 1.7E2 | 31 | 15 | 31 | 15 | 0.60 |
| rO | ng/ml | 1.5E-2 | 2.5E-2 | 3.6E-2 | 4.6E-2 | 7.3E-2 | 5.5E-2 | 1.0E-9 | 1.0E-9 | 4.0E-1 | 1.9E-1 | 31 | 15 | 31 | 15 | 0.58 |
| rR | ng/ml | 1.0E-9 | 4.0E0 | 9.9E0 | 1.5E1 | 2.2E1 | 2.2E1 | 1.0E-9 | 1.0E-9 | 9.5E1 | 7.5E1 | 31 | 15 | 31 | 15 | 0.59 |
| rN | ng/ml | 6.4E-1 | 6.3E-1 | 8.3E-1 | 1.8E0 | 5.6E-1 | 3.3E0 | 5.1E-2 | 2.1E-1 | 2.3E0 | 1.3E1 | 31 | 15 | 31 | 15 | 0.52 |
| qO | pg/ml | 7.8E3 | 9.3E3 | 1.1E4 | 1.5E4 | 8.2E3 | 1.3E4 | 7.4E2 | 1.9E3 | 3.7E4 | 4.8E4 | 29 | 18 | 29 | 18 | 0.56 |
| qP | pg/ml | 3.6E2 | 3.3E2 | 3.7E2 | 4.8E2 | 2.2E2 | 3.6E2 | 7.0E1 | 1.2E2 | 1.0E3 | 1.5E3 | 29 | 18 | 29 | 18 | 0.56 |
| qQ | pg/ml | 1.5E1 | 1.5E1 | 2.0E1 | 3.1E1 | 1.5E1 | 6.0E1 | 1.0E-9 | 1.0E-9 | 2.8E2 | 2.6E2 | 29 | 18 | 29 | 18 | 0.61 |
| nW | pg/ml | 1.1E5 | 1.1E5 | 1.1E5 | 1.1E5 | 2.7E4 | 2.9E4 | 5.8E4 | 3.6E4 | 1.8E5 | 1.7E5 | 58 | 45 | 58 | 45 | 0.47 |
| nY | pg/ml | 2.2E3 | 2.8E3 | 2.5E3 | 3.0E3 | 1.6E3 | 1.6E3 | 5.1E2 | 6.3E2 | 1.0E4 | 8.1E3 | 58 | 45 | 58 | 45 | 0.59 |
| oO | pg/ml | 9.3E4 | 9.1E4 | 1.1E5 | 1.1E5 | 5.9E4 | 8.6E4 | 3.2E3 | 3.3E3 | 2.6E5 | 4.0E5 | 30 | 26 | 30 | 26 | 0.44 |
| oP | pg/ml | 1.5E5 | 1.3E5 | 1.6E5 | 1.5E5 | 8.1E4 | 1.2E5 | 4.9E4 | 2.4E4 | 4.1E5 | 5.7E5 | 30 | 26 | 30 | 26 | 0.40 |
| oQ | pg/ml | 3.5E3 | 2.9E3 | 4.3E3 | 4.7E3 | 3.7E3 | 5.9E3 | 1.1E3 | 7.7E2 | 2.1E4 | 3.2E4 | 30 | 26 | 30 | 26 | 0.46 |
| oE | pg/ml | 2.0E2 | 2.6E2 | 4.9E2 | 6.5E2 | 6.2E2 | 7.8E2 | 1.0E-9 | 1.0E-9 | 2.8E3 | 3.4E3 | 58 | 45 | 58 | 45 | 0.56 |
| oF | pg/ml | 1.3E4 | 1.9E4 | 2.5E4 | 3.7E4 | 3.0E4 | 5.0E4 | 4.3E2 | 5.1E2 | 1.5E5 | 2.5E5 | 58 | 45 | 58 | 45 | 0.56 |
| oH | pg/ml | 3.5E1 | 3.5E1 | 8.3E1 | 7.9E1 | 1.4E2 | 1.1E2 | 5.4E0 | 4.4E0 | 8.6E2 | 4.8E2 | 58 | 45 | 58 | 45 | 0.49 |
| oK | pg/ml | 1.0E3 | 8.8E2 | 1.8E3 | 1.4E3 | 2.1E3 | 1.3E3 | 8.8E1 | 1.4E2 | 1.2E4 | 5.9E3 | 58 | 45 | 58 | 45 | 0.48 |
| oN | pg/ml | 5.6E2 | 5.6E2 | 1.2E3 | 7.7E2 | 2.6E3 | 7.9E2 | 1.6E2 | 1.1E2 | 1.8E4 | 5.3E3 | 58 | 45 | 58 | 45 | 0.52 |

Figure 41 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| oW | pg/ml | 2.0E2 | 4.1E2 | 2.7E2 | 1.1E3 | 1.8E2 | 2.0E3 | 7.7E1 | 2.9E1 | 7.3E2 | 7.6E3 | 15 | 14 | 15 | 14 | 0.65 |
| oT | pg/ml | 2.9E2 | 2.9E2 | 3.2E2 | 3.5E2 | 1.5E2 | 2.1E2 | 1.0E2 | 1.3E2 | 7.4E2 | 7.9E2 | 15 | 14 | 15 | 14 | 0.51 |
| oV | pg/ml | 9.8E1 | 8.9E1 | 2.6E2 | 3.1E2 | 3.7E2 | 5.9E2 | 2.1E1 | 1.0E-9 | 1.4E3 | 2.2E3 | 15 | 14 | 15 | 14 | 0.48 |
| oD | pg/ml | 1.7E4 | 1.4E4 | 1.6E4 | 1.5E4 | 5.0E3 | 7.0E3 | 8.7E3 | 6.6E3 | 2.5E4 | 3.2E4 | 15 | 14 | 15 | 14 | 0.40 |
| uL | ng/ml | 3.8E1 | 3.3E1 | 5.2E1 | 3.7E1 | 5.3E1 | 1.8E1 | 1.5E1 | 1.4E1 | 2.9E2 | 8.0E1 | 30 | 17 | 30 | 17 | 0.41 |
| uO | ng/ml | 4.6E-1 | 3.4E-1 | 9.3E-1 | 7.6E-1 | 1.7E0 | 7.9E-1 | 1.0E-9 | 1.0E-9 | 9.3E0 | 2.1E0 | 30 | 17 | 30 | 17 | 0.50 |
| uM | ng/ml | 6.2E-1 | 4.4E-1 | 1.2E0 | 5.3E-1 | 2.3E0 | 6.0E-1 | 1.0E-9 | 1.0E-9 | 1.3E1 | 2.5E0 | 30 | 17 | 30 | 17 | 0.34 |
| uI | ng/ml | 7.4E-2 | 5.4E-2 | 1.2E-1 | 9.0E-2 | 1.2E-1 | 1.0E-1 | 1.6E-2 | 1.5E-2 | 5.8E-1 | 4.3E-1 | 30 | 16 | 30 | 16 | 0.41 |
| uN | ng/ml | 1.4E1 | 1.7E1 | 1.6E1 | 2.0E1 | 5.8E0 | 8.9E0 | 8.0E0 | 1.0E1 | 3.0E1 | 4.1E1 | 30 | 17 | 30 | 17 | 0.63 |
| uG | ng/ml | 1.8E1 | 1.9E1 | 2.2E1 | 2.7E1 | 1.5E1 | 3.0E1 | 6.1E0 | 1.2E0 | 7.9E1 | 1.3E2 | 30 | 17 | 30 | 17 | 0.51 |
| uR | ng/ml | 2.1E0 | 2.0E0 | 2.8E0 | 2.9E0 | 2.4E0 | 2.2E0 | 8.9E-1 | 7.5E-1 | 1.3E1 | 8.3E0 | 31 | 18 | 31 | 18 | 0.51 |
| uP | ng/ml | 2.1E0 | 2.6E0 | 2.3E0 | 2.9E0 | 9.4E-1 | 1.4E0 | 1.2E0 | 9.3E-1 | 6.0E0 | 6.1E0 | 31 | 18 | 31 | 18 | 0.65 |
| uV | ng/ml | 2.3E-4 | 3.2E-3 | 1.8E-2 | 8.4E-3 | 4.0E-2 | 1.2E-2 | 1.0E-9 | 1.0E-9 | 2.0E-1 | 4.3E-2 | 31 | 18 | 31 | 18 | 0.49 |
| uT | ng/ml | 6.3E1 | 1.0E2 | 9.2E1 | 1.2E2 | 9.4E1 | 9.5E1 | 1.3E1 | 2.2E1 | 4.5E2 | 4.1E2 | 31 | 18 | 31 | 18 | 0.68 |
| uU | ng/ml | 1.2E0 | 2.0E0 | 1.7E0 | 2.9E0 | 1.2E0 | 4.3E0 | 6.0E-1 | 5.4E-1 | 6.0E0 | 2.0E1 | 31 | 18 | 31 | 18 | 0.64 |
| uW | ng/ml | 7.4E0 | 8.1E0 | 7.7E0 | 8.7E0 | 2.0E0 | 2.6E0 | 4.4E0 | 5.7E0 | 1.3E1 | 1.6E1 | 30 | 17 | 30 | 17 | 0.61 |
| vB | ng/ml | 2.9E0 | 3.3E0 | 3.4E0 | 3.4E0 | 2.3E0 | 2.2E0 | 5.9E-1 | 8.3E-1 | 1.0E1 | 1.0E1 | 30 | 17 | 30 | 17 | 0.52 |
| vC | ng/ml | 1.0E-9 | 1.0E-9 | 1.0E-9 | 1.0E-9 | 0.0E0 | 0.0E0 | 1.0E-9 | 1.0E-9 | 1.0E-9 | 1.0E-9 | 30 | 17 | 30 | 17 | 0.50 |
| uY | ng/ml | 6.1E-1 | 7.5E-1 | 9.0E-1 | 1.2E0 | 8.4E-1 | 1.2E0 | 6.8E-2 | 3.1E-1 | 3.8E0 | 4.4E0 | 30 | 17 | 30 | 17 | 0.61 |
| uZ | ng/ml | 5.8E-1 | 5.3E-1 | 8.0E-1 | 6.3E-1 | 9.4E-1 | 4.1E-1 | 1.0E-1 | 1.7E-1 | 4.9E0 | 1.9E0 | 30 | 17 | 30 | 17 | 0.48 |
| uX | ng/ml | 8.1E0 | 8.6E0 | 1.1E1 | 1.6E1 | 7.1E0 | 1.8E1 | 3.6E0 | 4.2E0 | 4.0E1 | 6.5E1 | 30 | 17 | 30 | 17 | 0.54 |
| vA | ng/ml | 6.3E-2 | 6.3E-2 | 8.0E-2 | 8.5E-2 | 5.5E-2 | 9.0E-2 | 2.9E-2 | 2.5E-2 | 2.7E-1 | 4.2E-1 | 30 | 17 | 30 | 17 | 0.49 |
| vH | ng/ml | 1.3E-1 | 1.2E-1 | 1.6E-1 | 2.3E-1 | 1.5E-1 | 4.4E-1 | 2.0E-2 | 2.1E-2 | 6.6E-1 | 1.9E0 | 30 | 17 | 30 | 17 | 0.45 |
| vI | ng/ml | 2.2E0 | 2.9E0 | 2.2E0 | 3.5E0 | 1.4E0 | 2.9E0 | 6.3E-3 | 8.7E-2 | 6.4E0 | 1.0E1 | 30 | 17 | 30 | 17 | 0.65 |
| vP | ng/ml | 3.8E2 | 2.6E2 | 4.3E2 | 5.1E2 | 3.0E2 | 5.8E2 | 6.7E1 | 9.2E1 | 1.1E3 | 2.4E3 | 31 | 18 | 31 | 18 | 0.49 |
| vT | ng/ml | 7.2E1 | 7.0E1 | 8.9E1 | 7.8E1 | 4.4E1 | 3.2E1 | 4.1E1 | 4.6E1 | 2.4E2 | 1.6E2 | 31 | 18 | 31 | 18 | 0.42 |
| vU | ng/ml | 1.0E-9 | 1.0E-9 | 2.3E1 | 2.1E1 | 3.5E1 | 3.6E1 | 1.0E-9 | 1.0E-9 | 1.2E2 | 1.1E2 | 31 | 18 | 31 | 18 | 0.46 |
| vQ | ng/ml | 4.0E2 | 4.4E2 | 4.1E2 | 4.1E2 | 1.6E2 | 1.7E2 | 7.2E1 | 1.2E2 | 8.4E2 | 6.7E2 | 31 | 18 | 31 | 18 | 0.51 |
| vO | ng/ml | 1.7E3 | 1.6E3 | 1.8E3 | 1.7E3 | 4.6E2 | 4.9E2 | 1.1E3 | 1.0E3 | 2.9E3 | 3.2E3 | 31 | 18 | 31 | 18 | 0.44 |
| vS | ng/ml | 1.3E3 | 1.3E3 | 1.2E3 | 1.3E3 | 4.2E2 | 5.6E2 | 1.0E-9 | 1.0E-9 | 2.1E3 | 2.0E3 | 31 | 18 | 31 | 18 | 0.52 |
| vV | ng/ml | 9.2E2 | 7.6E2 | 9.3E2 | 1.2E3 | 6.4E2 | 1.3E3 | 1.1E2 | 1.0E2 | 2.4E3 | 4.6E3 | 31 | 18 | 31 | 18 | 0.49 |
| vW | ng/ml | 1.2E2 | 1.1E2 | 1.5E2 | 1.9E2 | 7.6E1 | 1.9E2 | 4.3E1 | 6.0E1 | 2.9E2 | 7.7E2 | 31 | 18 | 31 | 18 | 0.50 |
| pF | pg/ml | 7.7E-1 | 5.2E-1 | 1.1E0 | 2.6E0 | 1.4E0 | 1.3E1 | 1.0E-9 | 1.0E-9 | 9.4E0 | 8.7E1 | 58 | 45 | 58 | 45 | 0.40 |
| pH | ng/ml | 6.9E0 | 8.9E0 | 9.0E0 | 1.0E1 | 5.2E0 | 5.2E0 | 3.0E0 | 1.2E0 | 2.0E1 | 2.3E1 | 15 | 14 | 15 | 14 | 0.60 |
| pI | ng/ml | 7.1E1 | 6.3E1 | 6.9E1 | 7.6E1 | 3.2E1 | 5.7E1 | 2.6E1 | 2.3E1 | 1.5E2 | 2.0E2 | 15 | 14 | 15 | 14 | 0.47 |
| pK | ng/ml | 4.0E-1 | 5.7E-1 | 3.8E-1 | 5.7E-1 | 1.7E-1 | 2.0E-1 | 1.7E-1 | 2.7E-1 | 7.7E-1 | 8.6E-1 | 15 | 14 | 15 | 14 | 0.79 |

Analyte panel data:

Unconstrained panels with 3 analytes, where 1.0E-10 >= 'model p-value' > 0. Contains 822 panels of 37,941,150 total panels evaluated. :
Ji{Ms(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jj(Et Fp Fr Hq Hr Hu Hv Hw Hx Ih Ii Ij Ik Il Im In Io Ip Iq Ir Is It Iu Iv Jg Jh Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Lj(aA Et Fp Fr Hq Hr Hu Hv Hw Hx Ii Ij Ik Il Im In Io Ip Iq Ir Is It Iu Iv Jg Jh Jk Jl Jm Jn Jo Jp Jq Jr Js Jt Lh Li Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Li(aA Et Fp Fr Hq Hr Hu Hv Hx Ii Ik Im Io Ip Ir Iu Iv Jg Jh Jk Jl Jo Jq Js Jt Lu Lw Lz Ma Mc Md Me Mg Mh Mj Mk Ml Mn Mp Mt Mu Mv Mw My Mz Nb Nd Ne Nf Ng Nh Ni Nj Nk Nl Nm Nn No Nq Ns Nt Nu Nv Nx Ny Oe Of Og Oh Oi Ok Om On Oy Oz Pa Pb Pc Pd Pe Pf Pg Po Pz Qa Qb Qc Qd Qe) Oy(Et Fp Fr Hu Hx Il Im Io Iq Ir Is Iv Jh Jl Jp Jq Jt Lu Lw Lx Lz Mc Mh Mk Ml Mp Mr Mv Mw My Mz Nd Ne Nk Nm Nn No Ns Nt Nu Nw Ny Oe Og Ok Oz Pb Pc Pd Pe Pf Po Pz Qa Qb Qc Qd Qe) Fp(Et Hu Hv Hx Ik Im Ir Jh Jk Jo Jq Lu Lw Mc Mh Mj Mk Ml Mp Mv Mw My Nd Ne Nf Ng Nh Nk Nm Nn Nq Ns Nu Ny Oe Of Og Oh Om Oz Pa Pb Pc Pd Pe Pg) Og(Et Hu Ij Il Im Ir Iv Jm Jq Jt Lu Lw Lz Mc Me Mh Mp My Mz Ne Nm Ns Nt Nu Ny Ok Oz Pb Pc Pg Po Pz Qa Qb Qc Qd Qe) Mp(Et Fr Hu Ik Im Ir Iv Jl Jp Jq Jt Lu Lw Lx Lz Mc Mh My Nd Ne Nn No Nu Nw Ok Pc Pf Pz Qa Qb Qc Qd Qe) Pc(Hu Hx Im Ir Jh Jo Jq Lu Lw Lz Mh Mv My Ng Nn Nu Ny Oe Of Qe) Nu(Hu Im Jh Jo Lu Mv Mw My Ne Ng Ns Oe Of Om Pb Pd Pg) Hu(Et Im Ir Jq Lu Lz Mc Mh Mr Nn Nt Ok Pb Qa Qd Qe) Im(Jh Jk Jq Lz Mv Mw My Ng Oe Of Pb Pg) My(Et Jg Lu Mh Nn Nw Ok Pb Po Qe) Pb(Ir Jq Lu Lw Lz Mh Nn Oe Qe) Et(Jh Mv Mw Ng Of Om) Qe(Ng Pg) NnMv YkeF OfOk} Li{Jj(Et Fp Hu Im Ir Jm Jq Jt Lj Lw Mc Mj Mz Nm Nn Nt Nu Nw Nx Ny Og Ok Oy Oz Pb Pc Qe) Hu(aA Et Im Ir Jp Lw Nw Og Ok Oy Pc) Lw(Ng Nq Og Oy Pb) Nw(Mp Ng Og Oy) Ok(Ng Of Og Oy) Im(Og Oy) EtOy NmOg}

Figure 41 Continued

Im{Og(Et Fp Hu Iq Ir Jt Lj Lw Lz Nj Nm Nn Nt Nu Nw Ok) Lj(Et Jj Lw Nw Ok) Ok(Jj Of Oy) Et(Hu Oy) Nw(Hu Oy) FpJj} Lj{Et(Hu Jj Lw Ms Oc Og Oy Pc) Ok(Jj Lw Mp Ms Oe Of Og Oy) Nw(Jj Lw Mp Ms Oy)} Fp{Nw(Hu Mj My) Ok(Jj Og) EtOy}

Unconstrained panels with 3 analytes, where 1.0E-9 >= 'model p-value' > 1.0E-10. Contains 3,417 panels of 37,941,150 total panels evaluated. : Ji{Jq(aA Et Fr Hq Hr Hv Hw Hx Ih Ii Ik Il In Io Ip Iq Ir Is It Iu Iv Jg Jh Jk Jl Jm Jn Jo Jp Jr Js Jt Lh Lu Lv Lw Lx Ly Lz Ma Mb Mc Md Me Mf Mg Mh Mi Mj Mk Ml Mm Mn Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oh Oi Ok Om On Oz Pa Pd Pe Pf Pg Po Pz Qa Qb Qc Qd Qe) Qe(aA Et Fp Fr Hq Hr Hv Hw Hx Ii Ij Ik Il Im In Io Ip Iq Ir Is It Iu Iv Jg Jh Jk Jl Jm Jn Jo Jp Jr Js Jt Lh Lu Lv Lw Lx Ly Lz Ma Mb Mc Md Me Mf Mg Mh Mi Mj Mk Ml Mm Mn Mq Mr Mt Mu Mv Mw Mx Mz Na Nb Nc Nd Ne Nf Nh Ni Nj Nk Nl Nm Nn No Nq Nr Ns Nt Nu Nv Nw Nx Ny Oe Of Oh Oi Ok Om On Oz Pa Pd Pe Pf Po Pz Qa Qb Qc Qd) Pb(aA Et Fr Hq Hr Hv Hw Hx Ih Ii Ij Ik Il In Io Ip Iq Is It Iu Iv Jg Jh Jk Jl Jm Jn Jo Jp Jr Js Jt Lh Lv Lx Ly Ma Mb Mc Md Me Mf Mg Mi Mj Mk Ml Mm Mn Mq Mr Mt Mu Mv Mw Mx Mz Na Nb Nc Nd Ne Nf Ng Nh Ni Nj Nk Nl Nm No Nq Nr Ns Nt Nv Nw Nx Ny Of Oh Oi Ok Om On Oz Pa Pc Pd Pe Pf Pg Po Pz Qa Qb Qc Qd) My(aA Fr Hq Hr Hu Hv Hw Hx Ih Ii Ij Ik Il In Io Ip Iq Ir Is It Iu Iv Jh Jk Jl Jm Jn Jo Jp Jr Js Jt Lh Lv Lw Lx Ly Lz Ma Mb Mc Md Me Mf Mg Mi Mj Mk Ml Mm Mn Mq Mr Mt Mu Mv Mw Mx Mz Na Nb Nc Nd Ne Nf Ng Nh Ni Nj Nk Nl Nm No Nq Nr Ns Nt Nv Nx Ny Oe Of Oh Oi Om On Oz Pa Pd Pe Pf Pg Pz Qa Qb Qc Qd) Im(aA Et Fr Hq Hr Hv Hw Hx Ih Ii Ij Ik Il In Io Ip Iq Ir Is It Iu Iv Jg Jl Jm Jn Jo Jp Jr Js Jt Lh Lu Lv Lw Lx Ly Ma Mb Mc Md Me Mf Mg Mh Mi Mj Mk Ml Mm Mn Mq Mr Mt Mu Mx Mz Na Nb Nc Nd Ne Nf Nh Ni Nj Nk Nl Nm Nn No Nq Nr Ns Nt Nv Nw Nx Ny Oh Oi Ok Om On Oz Pa Pd Pe Pf Po Pz Qa Qb Qc Qd) Hu(aA Fr Hq Hr Hv Hw Hx Ih Ii Ij Ik Il In Io Ip Iq Is It Iu Iv Jg Jh Jk Jl Jm Jn Jo Jp Jr Js Jt Lh Lv Lw Lx Ly Ma Mb Md Me Mf Mg Mi Mj Mk Ml Mm Mn Mq Mt Mu Mv Mw Mx Mz Na Nb Nc Nd Ne Nf Ng Nh Ni Nj Nk Nl Nm No Nq Nr Ns Nv Nw Nx Ny Oe Of Oh Oi Om On Oz Pa Pd Pe Pf Pg Po Pz Qb Qc) Nu(aA Et Fr Hq Hr Hv Hw Hx Ih Ii Ij Ik Il In Io Ip Iq Ir Is It Iu Iv Jg Jk Jl Jm Jn Jp Jr Js Jt Lh Lv Lw Lx Ly Lz Ma Mb Mc Md Me Mf Mg Mh Mi Mj Mk Ml Mm Mn Mq Mr Mt Mu Mx Mz Na Nb Nc Nd Nf Nh Ni Nj Nk Nl Nm Nn No Nq Nr Nt Nv Nw Nx Ny Oh Oi Ok On Oz Pa Pe Pf Po Pz Qa Qb Qc Qd) Pc(aA Et Fr Hq Hr Hv Hw Ih Ii Ij Ik Il In Io Ip Iq Is It Iu Iv Jg Jk Jl Jm Jn Jp Jr Js Jt Lh Lv Lx Ly Ma Mb Mc Md Me Mf Mg Mi Mj Mk Ml Mm Mn Mq Mr Mt Mu Mw Mx Mz Na Nb Nc Nd Ne Nf Nh Ni Nj Nk Nl Nm No Nq Nr Ns Nt Nv Nw Nx Oh Oi Ok Om On Oz Pa Pd Pe Pf Pg Po Pz Qa Qb Qc Qd) Ng(aA Fr Hq Hv Hw Hx Ik Il Io Ip Iq Ir Is It Iu Iv Jg Jh Jl Jm Jn Jo Jp Jr Jt Lh Lu Lv Lw Lx Lz Mb Mc Me Mf Mg Mh Mi Mj Mk Ml Mm Mn Mp Mr Mt Mv Mw Mx Mz Nb Nd Ne Nf Nh Ni Nj Nk Nl Nm Nn No Nr Ns Nt Nw Nx Ny Oe Of Og Oh Ok Om On Oy Oz Pa Pd Pe Pf Pg Po Pz Qa Qb Qc Qd) Lz(Et Fp Hq Hr Hv Hx Ii Ik Il Io Ip Ir Iu Iv Jg Jh Jk Jl Jn Jo Jp Js Jt Lu Lw Lx Mc Md Me Mg Mh Mj Mk Ml Mm Mn Mq Mr Mu Mv Mw Mz Nb Nd Ne Nf Nh Ni Nj Nk Nl Nm Nn Nq Ns Nt Nv Nw Nx Ny Oe Of Oh Ok Om On Oz Pa Pd Pe Pf Pg Po Pz Qa Qb Qc Qd) Mp(aA Hq Hr Hv Hw Hx Ih Ii Ij Il In Io Ip Iq Is It Iu Jg Jh Jk Jm Jn Jo Jr Js Lh Lv Ly Ma Mb Md Me Mf Mg Mi Mj Mk Ml Mm Mn Mq Mr Mt Mu Mv Mw Mx Mz Na Nb Nc Nf Nh Ni Nj Nk Nl Nm Nq Nr Ns Nt Nv Nx Ny Oe Of Oh Oi Om On Oz Pa Pd Pe Pg Po) Og(aA Fr Hq Hr Hv Hw Hx Ih Ii Ik In Io Ip Iq Is It Iu Jg Jh Jk Jl Jn Jo Jp Jr Js Lh Lv Lx Ly Ma Mb Md Mf Mg Mi Mj Mk Ml Mm Mn Mq Mr Mt Mu Mv Mw Mx Na Nb Nc Nd Nf Nh Ni Nj Nk Nl No Nq Nr Nv Nw Nx Oe Of Oh Oi Om On Pa Pd Pe Pf) Mh(aA Et Hq Hv Hx Ii Ik Io Ip Iq Ir Is It Iu Iv Jh Jk Jl Jo Jp Jt Lu Lw Lx Mc Md Me Mg Mj Mk Ml Mm Mn Mr Mu Mv Mw Mz Nb Nd Ne Nf Nh Ni Nj Nk Nm Nn Nq Ns Nt Nw Nx Ny Oe Of Oh Ok Om Oz Pa Pd Pe Pf Pg Po Pz Qa Qb Qc Qd) Lu(aA Et Hq Hv Hx Ii Ik Io Ip Iq Ir Iu Iv Jh Jk Jl Jo Jp Jt Lw Lx Mc Md Me Mg Mj Mk Ml Mm Mr Mu Mv Mw Mz Nb Nd Ne Nh Ni Nj Nk Nm Nn No Nq Ns Nt Nv Nw Nx Ny Oe Of Oh Ok Om Oz Pa Pd Pe Pf Pg Po Pz Qa Qb Qc Qd) Fp(aA Fr Hq Hr Hw Ih Ii Ij Il In Io Ip Iq Is It Iu Iv Jg Jl Jm Jn Jp Jr Js Jt Lh Lv Lx Ly Ma Mb Md Me Mf Mg Mi Mm Mn Mq Mr Mt Mu Mx Mz Na Nb Nc Ni Nj Nl No Nr Nt Nv Nw Nx Oi Ok On Pf Po Pz Qa Qb Qc Qd) Et(Fr Hq Hv Hx Ii Ij Ik Io Ip Iq Ir Iu Iv Jk Jl Jn Jo Jr Jt Lw Mb Mc Md Me Mg Mj Mk Ml Mn Mr Mu Mx Mz Na Nb Nd Ne Nf Nh Ni Nj Nk Nm Nn No Nq Ns Nt Nv Nw Nx Ny Oe Oh Ok On Oz Pa Pd Pe Pf Pg Pz Qc Qd) Mv(Fr Hv Hx Ik Il Io Ip Iq Ir Is Iu Iv Jg Jl Jn Jo Jp Jr Jt Lw Lx Mc Mi Mj Ml Mm Mn Mr Mt Mz Nb Nd Ne Nh Nj Nk Nm No Ns Nt Nw Ny Oe Of Oh Ok On Oz Pa Pd Pe Pf Pg Po Pz Qa Qb Qc Qd) Ir(Hq Hv Hx Ii Ij Ik It Iu Jh Jk Jo Jp Js Lw Mc Me Mj Ml Mm Mn Mu Mw Mx Mz Na Nb Nd Ne Nf Nh Nj Nk Nm Nn Nq Ns Nt Nw Nx Ny Oe Of Oh Ok Om On Oz Pa Pd Pe Pf Pg Po Pz Qa Qb Qc Qd) Oe(aA Hv Hx Ik Il Io Ip Iq Iv Jh Jl Jm Jo Jp Jr Jt Lw Lx Mc Mj Ml Mm Mn Mr Mu Mw Mz Nd Ne Nh Nj Nk Nm Nn No Nq Ns Nt Nw Nx Ny Of Ok Om Oz Pa Pd Pe Pf Pg Po Pz Qa Qb Qc Qd) Oy(aA Hq Hr Hv Hw Ih Ii Ij Ik In Ip It Iu Jg Jk Jm Jn Jo Jr Js Lh Lv Ly Ma Mb Md Me Mf Mg Mi Mj Mm Mn Mq Mt Mu Mx Na Nb Nc Nf Nh Ni Nj Nl Nq Nr Nv Nx Of Oh Oi Om On Pa Pg) Jh(Fr Hv Hx Ik Io Iq Is Iu Iv Jg Jl Jn Jo Jp Jt Lw Lx Mc Me Mj Ml Mm Mn Mr Mz Nd Ne Nh Ni Nj Nk Nm Nn No Ns Nt Nw Ny Of Oh Ok Oz Pa Pd Pe Pf Pg Po Pz Qa Qb Qc Qd) Mc(Hv Hx Ik Io Iq Iu Iv Jk Jl Jo Jp Jt Lw Mb Mj Ml Mn Mr Mu Mw Mz Nd Ne Nh Nj Nk Nm Nn No Nq Ns Nt Nw Nx Ny Of Oh Ok Om Oz Pa Pd Pe Pf Pg Po Pz Qa Qb Qc Qd) Qd(Hq Hv Hx Ii Ik Il Io Ip Iq It Iu Iv Jk Jo Js Lw Me Mg Mj Mk Ml Mn Mu Mw Mz Nd Ne Nh Nj Nk Nm Nn Nq Ns Nt Nx Ny Of Oh Ok Om On Oz Pa Pd Pe Pf Pg Pz Qc) Of(Fr Hv Hx Ik Io Iq Iv Jg Jl Jm Jp Jt Lw Lx Me Mj Ml Mm Mn Mr Mu Mw Mz Nd Ne Nh Ni Nj Nk Nm Nn No Ns Nt Nw Nx Ny Oz Pa Pd Pe Pf Pg Po Pz Qa Qb Qc) Nn(Hq Hv Hx Ii Ik Io Iq Iu Iv Jk Jo Lw Mj Ml Mn Mr Mu Mw Mz Nd Ne Nf Nh Ni Nj Nk Nm Nq Ns Nt Nx Ny Oh Ok Om On Oz Pa Pd Pe Pg Po Pz Qa Qc) Mw(Fr Hx Ik Io Iq Is Iu Iv Jg Jl Jo Jp Jt Lw Lx Mi Ml Mm Mr Mt Mz Nd Ne Nh Nk Nm No Ns Nt Nw Ny Ok On Oz Pa Pd Pe Pf Pg Po Pz Qa Qb Qc) Ne(Hv Hx Ik Io Iq Iv Jl Jo Jp Jr Lw Lx Ml Mn Mr Mu Mz Nd Nj Nl Nm No Nq Ns Nt Nw Nx Ny Ok Om Oz Pa Pd Pe Pf Pg Po Pz Qa Qb Qc) Pg(aA Hv Hx Ik Il Io Iq Iv Jl Jo Jp Jt Lw Lx Ml Mn Mr Mz Nd Nh Nj Nk No Ns Nt Nw Ny Ok Oz Pd Pe Pf Po Pz Qa Qb Qc) Ns(Hv Hx Ik Io Iq Iu Iv Jl Jo Jp Jt Lw Mj Ml Mr Mz Nd Nh Nm No Nt Nw Nx Ny Ok Oz Pa Pd Pe Pf Po Pz Qa Qb Qc) Lw(Hv Hx Ik Io Iq Iv Jk Jo Jp Ml Mn Mr Mu Mz Nd Nh Nk No Nq Nt Nw Nx Ny Ok Om Oz Pa Pd Pe Po Pz Qa Qb Qc) Ok(Hx Ii Io Ip Iu Iv Jk Jo Md Mg Mj Ml Mn Mu Mz Na Nb Nd Nf Nj Nk Nq Nx Ny Oh Om On Oz Pa Pd Po Pz Qc) Hx(Ik Io Iq Iv Jl Jo Jp Lx Mi Ml Mm Mr Mt Mz Nd Nh Nk No Nt Nw Ny Oz Pa Pd Pe Po Pz Qa Qb Qc) Ny(Ik Io Iv Jk Jl Jo Jp Lx Mi Ml Mr Mt Mz Nd Nh Nk No Nt Nw Om Oz Pa Pd Pe Po Pz Qa Qb Qc) Li(Hr Hw Ih Ij Il In Iq Is It Jm Jn Jp Jr Lh Lv Lx Ly Mb Mf Mi Mm Mq Mr Mx Na Nc Nr Nw) Jo(Hv Ik Io Iq Iv Jl Jm Jt Ml Mm Mr Mz Nd Nk Nm No Nt Oz Pa Pd Pe Pf Po Pz Qa Qb Qc) Pd(Ik Io Iq Iv Jl Jp Jt Lx Ml Mr Mz Nd Nk Nm No Nt Nw Oz Pf Po Pz Qa Qb Qc) Oz(Io Iq Iu Iv Jl Jp Ml Mr Mu Mz Nd Nh Nk No Nt Nw Nx Pf Pz Qa Qc) Pz(Hv Io Iq Iv Jk Jp Jt Mj Ml Mn Mz Nd Nh Nm Nt Om Pa Pf) Nt(Ii Ik Io Iu Jk Mj Ml Mz Nh Nk Nq Nx Om Pe Po Qc) Qa(Hv Io Iu Jk Mj Ml Nh Nk Nq Oh Om Pa Pe) Qc(Ik Io Iv Jk Mj Ml Mz Nd Nh Nk Nq Om Pa) Nd(Ik Ml Mn Mz Nj Nk Nq Nx Pa Po) Om(Iv Jg Jp Jt Mm Mz Nw Pe Po Qb) Mj(Iq Iv Jl Mr Mz No Qb) Ik(Hv Io Iq Nj Nx Pf) Ml(Jp Mz Nw Pe Po) Ii(Iv Jl Mr Pe) Nb(Iv Jl Pe) Mz(aA Pa) Nx(Iv Jl) PoPe NhbM NjNk IhLj IlIq YkiA QbJk JjaA} Li{Hu(Fp Fr Hq Hr Hv Hw Hx Ih Ij Ik Il Io Iq Is Iu Iv Jg Jh Jk Jl Jm Jn Jo Jq Jr Js Jt Lh Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Oh Oi Om On Oz Pa Pb Pd Pe Pf Pg Po Pz Qa Qb Qc Qd Qe) Jj(aA Fr Hq Hr Hv Hw Hx Ih Ii Ij Ik Il In Io Ip Iq Is It Iu Iv Jg Jh Jk Jl Jn Jo Jp Jr Js Lh Lu Lv Lx Ly Lz Ma Mb Md Me Mf Mg Mh Mi Mk Ml Mm Mn Mp Mq Mr Ms Mt Mu Mv Mw Mx My Na Nb Nc Nd Ne Nf Ng Nh Ni Nj Nk Nl No Nq Nr Ns Nv Oe Of Oh Oi Om On Pa Pd Pe Pf Pg Po Pz Qa Qb Qc Qd) Lw(cO Et Fp Fr Hq Hx Ik Im Io Ir Iv Jh Jk Jo Jp Lj Lu Lz Mc Me Mg Mh Mj Mk Ml Mp Ms Mu Mv Mw My Mz Ne Nj

Figure 41 Continued

Nk Nn Ns Nt Nu Nw Ny Oe Of Oi Ok Oz Pc Pd Pg Qe) Og(aA Et Fr Hq Ij Ik Il Io Ir Is Iv Jl Jm Jp Jq Jt Lh Lj Lu Lz Mc Me Mh Mj Mp Ms Mv Mz
Nd Ne Ng Nj Nk Nn Nq Ns Nt Nu Nx Ny On Oy Oz Pb Pc Qc Qd Qe) Nw(Fp Hx Ik Im Io Ir Jh Jk Lj Mc Me Mh Mj Ms Mu Mv Mw My Ne Nj
Nq Ns Oe Of Ok Oz Pb Pc) Ok(Fp Hx Im Io Ir Jh Jk Jo Lj Mc Mg Mj Mp Ms Mv Mw My Mz Nq Ns Oe Oz Pb Pc) Oy(aA Ir Jl Jp Jq Jt Lj Mc
Ms Mz Nd Nm Nn Nq Nt Nu Nx Ny On Pg Qd Qe) Im(Et Fp Ir Jk Lj Mc Mp Ms Mv Mw My Mz Ne Ng Nq Oe Of Pb Pc) Et(Jk Lj Mh Mp Ms
Mv My Mz Ng Nq Oe Of Pb Pc) Ng(aA Ir Jg Jp Jt Mz Nm Nt Nu Pc) aA(Lj My Mz Nq Pb) Ir(Ik Mj Pb Pc) Pb(Jp Mz)} Lj{Et(aA Fp Fr Hq Hr
Hv Hw Hx Ij Ik Il Io Ip Iq Ir Is It Iu Iv Jg Jh Jk Jl Jm Jn Jo Jp Jq Jr Js Jt Lh Lu Lv Lx Ly Lz Ma Mb Mc Md Me Mf Mg Mh Mi Mj Mk Ml Mm
Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Of Oh Oi Ok
Om On Oz Pa Pb Pd Pe Pf Pg Po Pz Qa Qb Qc Qd Qe) Ok(aA Fp Fr Hq Hu Hv Hx Ik Il Io Ip Iq Ir Is It Iu Iv Jk Jl Jo Jp Jq Jt Lh Lu Lv Lx Ly Lz
Ma Mb Mc Me Mf Mg Mh Mi Mj Mk Ml Mm Mn Mr Mt Mv Mw Mx My Mz Na Nb Nc Nd Ne Ng Nh Ni Nj Nk Nl Nm Nn No Nq Nr Ns Nt
Nu Nw Nx Ny Oh Oi Om On Oz Pa Pb Pc Pd Pf Pg Pz) Nw(aA Fp Hu Hv Hx Ij Ik Il Io Ip Ir Iv Jt Lu Lv Lx Lz Mc Me Mg Mh Mi Mj Mk Ml
Mm Mv Mw My Mz Nb Nd Ne Ng Nh Ni Nj Nk Nl Nm Nn Nq Ns Nt Nu Nx Ny Oe Of Og Oh Oz Pa Pb Pc Pd Pe Pg) Im(aA Hu Iq Ir Jl Jp Jt
Lu Lv Lz Mc Mi Mj Mp Ms Nd Nj Nm Nn Nq Nt Nu Oe Oy Pb Pc Pf) Lw(Jg Jj Jp Mm Ms Nn Nt Nu Ny Og Oy Pc) Jj(Jg Jp Jt Mm Nn Nt Nu
Ny On) Jp(Mp Ms Nm Nt Oy) Og(Ij Jg Nm On) OnOy} Im{Og(aA Fr Hq Hr Hv Hw Hx Ih Ii Ij Ik In Io Is It Iu Iv Jg Jh Jj Jk Jl Jm Jn Jo Jp Jq Jr
Js Lh Lu Lv Lx Ly Mb Mc Md Me Mf Mg Mh Mi Mj Mk Ml Mm Mn Mp Mq Mr Ms Mt Mu Mv Mx My Mz Na Nb Nc Nd Ne Nf Ng Nh Ni
Nk Nl No Nq Nr Ns Nv Nx Ny Oe Of Oh Oi Om On Oy Oz Pa Pb Pc Pd Pe Pf Pg Po Pz Qa Qc Qd Qe) Nw(Fp Iq Ir Jj Jk Lw Lz Mh Mp Ms Mv
Mw My Ng Nj Nq Ns Nu Oe Of Ok Pb Pc Pg) Hu(Fp Ir Jj Jl Jp Jt Lw Lz Nn Nt Ok On Oy Pe Pf) Jj(Et Iq Jt Lw Lz Mz Nn Nt Nu Oy Pb) Ok(Fp
Jk Lw Lz Mp Ms My Ng Nq Oe Pb) Et(Fp Jk Lz Mh Ms Ng Oe Of) Oy(Fp Jp Jt Lw Lz) Lw(Fp Ng) NgJt} Ok{Oy(Fp Il Io Iq Ir Is It Iv Jj Lw Lz
Mc Mh Mp Ms Mz Nd Nn Nu Nw Of Og Qe) Of(Aa Fp Ir Jj Lw Mc Ms Nd Nn Nq Nu Nw Og Oz Pb Pc) Fp(Hu Lw Mc Mj Mp Ms My Ne Ng
Nq Nw Oe Pb Pc) Og(Ij Il Ir Lw Lz Mc Mh Ms Nn Nu Nw Oz Pc) Jj(Jm Lw Lz Mc Ms Nn Nu Oz Pb Pc Qe) Ms(Lw Lz Mz Nn Nw Pb Pc)
Nw(Mp My) LwNg} Nw{Fp(Ik Ir Jj Lw Mc Mh Ml Mp Ms Mv Mw Nd Ne Ng Nj Nk Nm Nq Ns Nu Ny Oe Of Og Oy Oz Pb Pc Pg) My(Ir Lw
Me Mh Mp Ms Nj Nm Nt Nu Oy Pc) Lw(Hu Mp Ms Mw Ng Og Oy Pb Pc) Oy(Et Hu Ir Ms Nj Nt Nu Qe) Nu(Hu Jj Mp Ms Ng Og) Ms(Ir Nj Pb
Pc) Og(Ij Il Nj Nm) Hu(Nt Pc) NmNg} Et{Fp(Hu Jj Lw Mc Mz Ng Og Oz Pb Pc) Oy(Lw Mz Qe)} Gc{eC(Pa Vs) YkhC} Qe{Aa(Jj Oy) AjNm}
Ij{Og(Lw Nm)} AlSfPj FpJjJt MzdNtX Unconstrained panels with 3 analytes, where 1.0E-8 >= 'model p-value' > 1.0E-9. Contains 8,924 panels of 37,941,150 total panels evaluated. :
Ji{Ih(aA Et Fr Hq Hr Hv Hw Hx Ii Ij Ik Il In Io Ip Iq Ir Is It Iu Iv Jg Jh Jk Jl Jm Jn Jo Jp Jr Js Jt Lh Lu Lv Lw Lx Ly Lz Ma Mb Mc Md Me Mf
Mg Mh Mi Mj Mk Ml Mm Mn Mq Mr Mt Mu Mv Mw Mx Mz Na Nb Nc Nd Ne Nf Ng Nh Ni Nj Nk Nl Nm Nn No Nq Nr Ns Nt Nv Nw Nx
Ny Oe Of Oh Oi Ok Om On Oz Pa Pd Pe Pf Pg Po Pz Qa Qb Qc Qd Qe) In(aA Et Fr Hq Hr Hv Hw Hx Ii Ij Ik Il Io Ip Iq Ir Is It Iu Iv Jg Jh Jk Jl
Jm Jn Jo Jp Jr Js Jt Lh Lu Lv Lw Lx Ly Lz Ma Mb Mc Md Me Mf Mg Mh Mi Mj Mk Ml Mm Mn Mq Mr Mt Mu Mv Mw Mx Mz Na Nb Nc Nd
Ne Nf Ng Nh Ni Nj Nk Nl Nm Nn No Nq Nr Ns Nt Nv Nw Nx Ny Oe Of Oh Oi Ok Om On Oz Pa Pd Pe Pf Pg Po Pz Qa Qb Qc Qd) Oi(aA Et
Fr Hq Hr Hv Hw Hx Ii Ij Ik Il Io Ip Iq Ir Is It Iu Iv Jg Jh Jk Jl Jm Jn Jo Jp Jr Js Jt Lh Lu Lv Lw Lx Ly Lz Ma Mb Mc Md Me Mf Mg Mh Mi Mj
Mk Ml Mm Mn Mq Mr Mt Mu Mv Mw Mx Mz Na Nb Nc Nd Ne Nf Ng Nh Ni Nj Nk Nl Nm Nn No Nq Nr Ns Nt Nv Nw Nx Ny Oe Of Oh Ok
Om On Oz Pa Pd Pe Pf Pg Po Pz Qa Qb Qc Qd) Ly(aA Et Fr Hq Hr Hv Hw Hx Ii Ik Il Io Ip Iq Ir Is It Iu Iv Jg Jh Jk Jl Jm Jn Jo Jp Jr Js Jt Lh Lu
Lv Lw Lx Lz Ma Mb Mc Md Me Mf Mg Mh Mi Mj Mk Ml Mm Mn Mq Mr Mt Mu Mv Mw Mx Mz Na Nb Nc Nd Ne Nf Ng Nh Ni Nj Nk Nl
Nm Nn No Nq Nr Ns Nt Nv Nw Nx Ny Oe Of Oh Ok Om On Oz Pa Pd Pe Pf Pg Po Pz Qa Qb Qc Qd) Ma(aA Et Fr Hq Hr Hv Hw Hx Ii Ik Il Io
Ip Iq Ir Is It Iu Iv Jg Jh Jk Jl Jm Jn Jo Jp Jr Js Jt Lh Lu Lv Lw Lx Lz Mb Mc Md Me Mf Mg Mh Mi Mj Mk Ml Mm Mn Mq Mr Mt Mu Mv Mw
Mx Mz Na Nb Nc Nd Ne Nf Ng Nh Ni Nj Nk Nl Nm Nn No Nq Nr Ns Nt Nv Nw Nx Ny Oe Of Oh Ok Om On Oz Pa Pd Pe Pf Pg Po Pz Qa Qb
Qc Qd) Nc(aA Et Fr Hq Hr Hv Hw Hx Ii Ik Il Io Ip Iq Ir Is It Iu Iv Jg Jh Jk Jl Jm Jn Jo Jp Jr Js Jt Lh Lu Lv Lw Lx Lz Mb Mc Md Me Mf Mg Mh
Mi Mj Mk Ml Mm Mn Mq Mr Mt Mu Mv Mw Mx Mz Na Nb Nd Ne Nf Ng Nh Ni Nj Nk Nl Nm Nn No Nq Nr Ns Nt Nv Nw Nx Ny Oe Of Oh
Ok Om On Oz Pa Pd Pe Pf Pg Po Pz Qa Qb Qc Qd) Hr(aA Et Fr Hq Hv Hw Hx Ii Ij Ik Il Io Ip Iq Ir Is It Iu Iv Jg Jh Jk Jl Jm Jn Jo Jp Jr Js Jt Lh
Lu Lv Lw Lx Mb Mc Md Me Mf Mg Mh Mi Mj Mk Ml Mm Mn Mq Mr Mt Mu Mv Mw Mx Mz Na Nb Nd Ne Nf Ng Nh Ni Nj Nk Nl Nm Nn
No Nq Nr Ns Nt Nv Nw Nx Ny Oe Of Oh Ok Om On Oz Pa Pd Pe Pf Pg Po Pz Qa Qb Qc Qd) Hw(aA Et Fr Hq Hv Hx Ii Ij Ik Il Io Ip Iq Ir Is It
Iu Iv Jg Jh Jk Jl Jm Jn Jo Jp Jr Js Jt Lh Lu Lv Lw Lx Lz Mb Mc Md Me Mf Mg Mh Mi Mj Mk Ml Mm Mn Mq Mr Mt Mu Mv Mw Mx Mz Na
Nb Nd Ne Nf Nh Ni Nj Nk Nl Nm Nn No Nq Nr Ns Nt Nv Nw Nx Ny Oe Of Oh Ok Om On Oz Pa Pd Pe Pf Pg Po Pz Qa Qb Qc Qd) Nr(aA Et
Fr Hq Hv Hx Ii Ik Il Io Ip Iq Ir Is It Iu Iv Jg Jh Jk Jl Jm Jn Jo Jp Jr Js Jt Lh Lu Lv Lw Lx Lz Mb Mc Md Me Mf Mg Mh Mi Mj Mk Ml Mm Mn
Mq Mr Mt Mu Mv Mw Mx Mz Na Nb Nd Ne Nf Nh Ni Nj Nk Nl Nm Nn No Nq Ns Nt Nv Nw Nx Ny Oe Of Oh Ok Om On Oz Pa Pd Pe Pf Pg
Po Pz Qa Qb Qc Qd) Lv(aA Et Fr Hq Hv Hx Ii Ik Il Io Ip Iq Ir Is It Iu Iv Jg Jh Jk Jl Jm Jn Jo Jp Jr Js Jt Lh Lu Lw Lx Lz Mb Mc Md Me Mf Mg
Mh Mi Mj Mk Ml Mm Mn Mq Mr Mt Mu Mv Mw Mx Mz Na Nb Nd Ne Nf Nh Ni Nj Nk Nl Nm Nn No Nq Ns Nt Nv Nw Nx Ny Oe Of Oh Ok
Om On Oz Pa Pd Pe Pf Pg Po Pz Qa Qb Qc Qd) Mf(aA Et Fr Hq Hv Hx Ii Ik Il Io Ip Iq Ir Is It Iu Iv Jg Jh Jk Jl Jm Jn Jo Jp Jr Js Jt Lh Lu Lw Lx
Lz Mb Mc Md Me Mg Mh Mi Mj Mk Ml Mm Mn Mq Mr Mt Mu Mv Mw Mx Mz Na Nb Nd Ne Nf Nh Ni Nj Nk Nl Nm Nn No Nq Ns Nt Nv
Nw Nx Ny Oe Of Oh Ok Om On Oz Pa Pd Pe Pf Pg Po Pz Qa Qb Qc Qd) Mq(aA Et Fr Hq Hv Hx Ii Ik Il Io Ip Iq Ir Is It Iu Iv Jg Jh Jk Jl Jm Jn
Jo Jp Jr Js Jt Lh Lu Lw Lx Mb Mc Md Me Mg Mh Mi Mj Mk Ml Mm Mn Mr Mt Mu Mv Mw Mx Mz Na Nb Nd Ne Nf Ng Nh Ni Nj Nk Nl Nm
Nn No Nq Ns Nt Nv Nw Nx Ny Oe Of Oh Ok Om On Oz Pa Pd Pe Pf Pg Po Pz Qa Qb Qc Qd) Lh(aA Et Fr Hq Hv Hx Ii Ik Il Io Ip Iq Ir Is It Iu
Iv Jg Jh Jk Jl Jm Jn Jo Jp Jr Js Jt Lu Lw Lx Lz Mb Mc Md Me Mg Mh Mi Mj Mk Ml Mm Mn Mr Mt Mu Mv Mw Mx Mz Na Nb Nd Ne Nf Nh
Ni Nj Nk Nl Nm Nn No Nq Ns Nt Nv Nw Nx Ny Oe Of Oh Ok Om On Oz Pa Pd Pe Pf Pg Po Pz Qa Qb Qc Qd) Mb(aA Fr Hq Hv Hx Ii Ij Ik Il
Io Ip Iq Ir Is It Iu Iv Jg Jh Jk Jl Jm Jn Jo Jp Jr Js Jt Lu Lw Lx Lz Md Me Mg Mh Mi Mj Mk Ml Mm Mn Mr Mt Mu Mv Mw Mx Mz Na Nb Nd
Ne Nf Nh Ni Nj Nk Nl Nm Nn No Nq Ns Nt Nv Nw Nx Ny Oe Of Oh Ok Om On Oz Pa Pd Pe Pf Pg Po Pz Qa Qb Qc Qd) Mx(aA Fr Hq Hv Hx
Ii Ij Ik Il Io Ip Iq Is It Iu Iv Jg Jh Jk Jl Jm Jn Jo Jp Jr Js Jt Lu Lw Lx Lz Mc Md Me Mg Mh Mi Mj Mk Ml Mm Mn Mr Mt Mu Mv Mw Mz Na
Nb Nd Ne Nf Nh Ni Nj Nk Nl Nm Nn No Nq Ns Nt Nv Nw Nx Ny Oe Of Oh Ok Om On Oz Pa Pd Pe Pf Pg Po Pz Qa Qb Qc Qd) Nl(aA Et Fr
Hq Hv Hx Ii Ij Ik Il Io Ip Iq Ir Is It Iu Iv Jg Jh Jk Jl Jm Jn Jo Jp Jr Js Jt Lu Lw Lx Mc Md Me Mg Mh Mi Mj Mk Ml Mm Mn Mr Mt Mu Mv Mw
Mz Na Nb Nd Nf Nh Ni Nj Nk Nm Nn No Nq Ns Nt Nv Nw Nx Ny Oe Of Oh Ok Om On Oz Pa Pd Pe Pf Pg Po Pz Qa Qb Qc Qd) Na(aA Fr Hq
Hv Hx Ii Ik Il Io Ip Iq Is It Iu Iv Jg Jh Jk Jl Jm Jn Jo Jp Jr Js Jt Lu Lw Lx Lz Mc Md Me Mg Mh Mi Mj Mk Ml Mm Mn Mr Mt Mu Mv Mw Mz
Nb Nd Ne Nf Ng Nh Ni Nj Nk Nm Nn No Nq Ns Nt Nv Nw Nx Ny Oe Of Oh Om On Oz Pa Pd Pe Pf Pg Po Pz Qa Qb Qc Qd) It(aA Et Fr Hq
Hv Hx Ii Ij Ik Il Io Ip Iq Is It Iu Iv Jg Jh Jk Jl Jm Jn Jo Jp Jr Js Jt Lu Lw Lx Lz Mc Md Me Mg Mi Mj Mk Ml Mm Mn Mr Mt Mu Mv Mw Mz Nb
Nd Ne Nf Nh Ni Nj Nk Nm Nn No Nq Ns Nt Nv Nw Nx Ny Oe Of Oh Ok Om On Oz Pa Pd Pe Pf Pg Po Pz Qa Qb Qc) Jm(aA Et Fr Hq Hv Hx
Ii Ij Ik Il Io Ip Iq Ir Is Iu Iv Jg Jh Jk Jl Jn Jp Jr Js Jt Lu Lw Lx Lz Mc Md Me Mg Mh Mi Mj Mk Ml Mm Mn Mr Mt Mu Mv Mw Mz Nb Nd Ne

Ip Iq Is It Iu Iv Jg Jh Jl Jm Jn Jo Jp Jq Jr Js Jt Lh Lu Lv Lx Ly Lz Ma Mb Md Me Mf Mg Mh Mi Mj Mk Ml Mm Mn Mq Mr Mt Mu Mx Na Nb Nc Nd Nf Nh Ni Nj Nk Nl Nm Nn No Nr Ns Nt Nu Nv Nx Ny Oh Oi Om On Oz Pa Pd Pe Pf Pg Po Pz Qa Qb Qc Qd Qe) Oy(Aa Fp Fr Hq Hr Hv Hw Hx Ih Ii Ij Ik Il In Io Ip Iq Is It Iu Iv Jg Jh Jk Jm Jn Jo Jr Js Lh Lu Lv Lx Ly Lz Ma Mb Md Me Mf Mg Mh Mi Mj Mk Ml Mm Mn Mp Mq Mr Mt Mu Mv Mw Mx My Na Nb Nc Ne Nf Ng Nh Ni Nj Nk Nl No Nr Ns Nv Oe Of Oh Oi Om Oz Pa Pc Pd Pe Pf Po Pz Qa Qb Qc) Ok(aA Fr Hq Hr Hv Hw Ih Ii Ij Ik Il In Ip Iq Is It Iu Iv Jg Jl Jm Jn Jp Jq Jr Js Jt Lh Lu Lv Lx Ly Lz Ma Mb Md Me Mf Mh Mi Mk Ml Mm Mn Mq Mr Mt Mu Mx Na Nb Nc Nd Ne Nf Nh Ni Nj Nk Nl Nm Nn No Nr Nt Nu Nv Nx Ny Oh Oi Om On Pa Pd Pe Pf Pg Po Pz Qa Qb Qc Qd Qe) Ng(Fp Hq Hw Hx Ih Ij Ik Il Io Iq Is Iv Jl Jm Jn Jq Jr Js Lh Lj Lu Lv Lx Lz Mb Mc Md Me Mf Mg Mh Mi Mj Mk Ml Mm Mn Mp Mr Ms Mt Mu Mv Mw Mx My Nb Nc Nd Ne Nf Nh Ni Nj Nk Nl Nn No Nq Nr Ns Nv Nx Ny Oe Of Oh Oi Om On Oz Pa Pd Pe Pf Pg Po Pz Qa Qb Qc Qd Qe) Nw(aA Fr Hq Hr Hv Hw Ih Ii Ij Il In Ip Iq Is It Iu Iv Jg Jl Jm Jn Jo Jp Jq Jr Js Jt Lh Lu Lv Lx Ly Lz Ma Mb Md Mf Mg Mi Mk Ml Mm Mn Mq Mr Mt Mx Mz Na Nb Nc Nd Nf Nh Ni Nk Nl Nm Nn No Nr Nt Nu Nv Nx Ny Oh Oi Om On Pa Pd Pe Pf Pg Po Pz Qa Qb Qc Qd Qe) Mz(Fp Fr Hq Hx Ik Il Io Is Iu Iv Jh Jk Jl Jn Jo Jp Jq Jr Jt Lj Lu Lv Lx Lz Mb Mc Me Mg Mh Mi Mj Mk Ml Mm Mn Mp Mr Ms Mu Mv Mw My Nc Nd Ne Nf Nh Ni Nj Nk Nl Nm Nn No Nq Ns Nt Nu Nx Ny Oe Of Oh Oi Om Oz Pa Pc Pd Pe Pg Po Pz Qc Qd Qe) Pc(aA Fp Hq Hx Ih Ik Il Io Is Iv Jh Jk Jl Jn Jo Jp Jq Jr Jt Lh Lj Lu Lv Lx Lz Mb Mc Me Mg Mh Mi Mj Mk Ml Mp Mr Ms Mu Mv Mw Mx My Nd Ne Nf Nh Ni Nj Nk Nl Nm Nn No Nq Ns Nt Nu Nx Ny Oe Of Oi Oz Pd Pe Pf Qc Qd Qe) Lw(AA bQ Hr Hv Hw Ih Ii Ij Il In Ip Iq Is It Iu Jg Jl Jm Jn Jq Jr Js Jt Lh Lv Lx Ly Ma Mb Md Mf Mi Mm Mn Mq Mr Mt Mx Na Nb Nc Nd Nf Nh Ni Nl Nm No Nr Nv Nx Oh Om On Pa Pe Pf Po Pz Qa Qb Qc Qd) Lj(Fp Hx Ik Io Is Iv Jg Jk Jl Jn Jp Jq Jt Lh Lu Lv Lx Lz Mc Me Mh Mi Mj Mk Ml Mm Mp Mr Ms Mv Mw My Nb Nc Nd Ne Nf Nh Ni Nj Nk Nl Nm Nn No Nq Ns Nt Nu Nx Ny Oe Of Oh Oi On Oz Pa Pd Pe Pf Pg Qd Qe) Og(Fr Hq Hr Hv Hw Hx Ih Ii In Ip Iq It Iu Jg Jh Jk Jn Jo Jr Js Lv Lx Ly Ma Mb Md Mf Mg Mi Mk Ml Mm Mn Mq Mr Mt Mu Mw Mx My Na Nb Nc Nf Nh Ni Nl No Nr Nv Oe Of Oh Oi Om Pa Pd Pe Pf Pg Po Pz Qa Qb) aA(Fp Fr Hq Hx Ih Ik Io Jh Jk Jl Jm Jn Jp Jq Lu Lz Mc Me Mg Mh Mj Ml Mm Mp Ms Mu Mv Mw Nd Ne Nh Ni Nj Nk Nn Ns Nt Nu Nx Ny Oe Of Oi Oz Pd Pe Pf Pg Qd Qe) Ik(Fp Hx Ih Io Iq Iv Jh Jk Jl Jn Jp Jq Jr Jt Lh Lu Lz Mc Me Mh Ml Mp Ms Mv Mw My Nd Ne Nj Nk Nm Nn Nq Ns Nt Nu Ny Oe Of Oz Qc Qd Qe) Mv(Fp Io Is Iv Jg Jl Jp Jq Jt Lh Lu Lx Mc Md Mh Mi Mp Mr Ms Mt Nd Ne Nj Nk Nm Nn No Nq Ns Nt Nu Nx Ny Oe Of On Oz Pe Po Qd Qe) Nq(Fp Ih Is Iv Jl Jp Jq Jt Lh Lu Lx Mc Me Mh Mi Mp Ms Mw My Nd Ne Nk Nm Nn No Ns Nt Nu Nx Ny Oe Of On Oz Qa Qb Qc Qd Qe) Jp(Fp Fr Hx Io Jh Jk Jq Lu Lz Mc Me Mg Mh Mj Mp Ms Mw My Ne Nj Nk Nm Ns Nt Nu Oe Of Oz Pd Pg Pz Qe) My(Fp Is Jg Jl Jq Jt Lh Lx Mc Mh Mi Mp Ms Mt Nd Ne Nj Nk Nm Nn Nt Nu Nx Ny Of On Oz Qd Qe) Mc(Fp Jh Jk Jl Jq Lz Mb Mh Mp Ms Mw Nd Ne Nj Nm Nn Ns Nt Nx Ny Oe Of Oz Pd Qd Qe) Oz(Fp Hx Io Jh Jl Jq Mh Mp Ms Mw Nd Ne Nj Nk Nm Nn Ns Nt Nu Oe Of Pd Qd Qe) Ne(Fp Iv Jl Jn Jq Mh Mp Ms Mw Nd Nj Nl Nm Nn Nt Nu Ny Oe Of Qd Qe) Of(Fp Jl Jq Jt Lh Mm Ms Nd Nj Nk Nm Nn Nt Nu Nx Ny On Qd Qe) Mw(Fp Is Iv Jg Jl Jq Jt Lh Lx Mi Nm Nn Nt Nu Ny On Qe) Mp(Fp Is Iv Jl Jq Jt Nd Nm Nn Nt Nu Nx Ny On Qd Qe) Ms(Fp Jl Jn Jq Jt Nk Nm Nn Ns Nt Nu Nx Ny On Qd Qe) Mj(Fp Ih Iq Is Iv Jl Jq Jt Mh Mx Nt Ny Pe Qd Qe) Jk(Is Jl Jq Jt Nd Nm Nn Nt Nu Ny On Qa Qd Qe) Oe(Fp Jl Jq Jt Nj Nm Nn Nt Nu Nx Ny Qd Qe) Nm(Aj Fp Jh Jo Mg Mh Nj Ns Oi Pd Qe) Nt(Fp Jh Jo Mg Mk Nk Ns Oi Pd Qe) Qe(Hx Jh Jq Nj Nk Ns Nu Pd Pg) Jq(Fp Hx Jh Mh Nu Om Pd) Ns(Fp Nd Nn Nu Ny) Nu(Fp Jh Jl Pd) Nj(Jl Nd Nk Nn) Hu(Ii In Ip It) Jt(Fp Jh Jo Mg) Nk(Fp Nd Nn) Mh(Nn Qd) Jl(Hx Pd) AaJj IlIq QdPd} Nw{Oy(aA Fr Hq Hv Hw Hx Ih Ij Ik Il In Io Ip Iq Is It Iu Iv Jg Jh Jj Jl Jm Jn Jo Jp Jq Jr Jt Lh Lu Lv Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Ng Nh Ni Nk Nl Nm Nn No Nq Nr Ns Nv Nx Ny Oe Of Og Oh Oi Om On Oz Pa Pb Pc Pd Pe Pf Pg Po Qa Qb Qd) Ms(aA Et Fr Hu Hx Ih Ij Ik Il In Io Ip Iq Is It Iu Iv Jj Jm Jn Jq Jr Jt Lh Lu Lv Lx Ly Lz Ma Mb Mc Md Me Mf Mg Mh Mi Mj Mk Ml Mm Mn Mp Mq Mr Mt Mu Mv Mw Mx Mz Na Nb Nc Nd Ne Nf Ng Nh Ni Nk Nl Nn No Nq Nr Ns Nt Nv Nx Ny Oe Of Og Oh Oi Om On Oz Pa Pd Pe Pf Pg Qa Qd Qe) My(aA Et Fr Hu Hx Ih Ij Ik Il In Io Ip Iq Is It Iu Iv Jg Jj Jm Jn Jr Jt Lh Lu Lv Lx Ly Lz Ma Mb Mc Md Mf Mg Mi Mj Mk Ml Mm Mn Mq Mr Mt Mu Mv Mw Mx Mz Na Nb Nc Nd Ne Nf Ng Nh Ni Nk Nl Nn No Nq Nr Ns Nv Nx Ny Oe Of Og Oh Oi Om On Oz Pa Pb Pd Pe Pf Pg Qa Qd Qe) Fp(AA Et Fr Hq Hr Hv Hw Hx Ih Ii Ij Il In Io Ip Iq Is It Iu Iv Jg Jh Jk Jl Jm Jn Jo Jp Jq Jr Js Jt Lh Lu Lv Lx Ly Lz Ma Mb Md Me Mf Mg Mi Mk Mm Mn Mq Mr Mt Mu Mx Mz Na Nb Nc Nf Nh Ni Nl Nn No Nr Nt Nv Nx Oh Oi Om On Pa Pd Pe Pf Po Pz Qa Qb Qc Qd Qe) Im(aA Et Fr Hq Hv Hw Hx Ih Ii Ij Ik Il In Io Ip Is It Iu Iv Jh Jl Jn Jp Jq Jr Js Jt Lh Lu Lv Lx Ly Ma Mb Mc Md Me Mf Mg Mj Mk Ml Mm Mn Mq Mr Mt Mu Mx Mz Na Nb Nc Nd Ne Nf Nh Ni Nk Nl Nm Nn No Nr Nt Nv Nx Ny Oh Oi Om On Oz Pa Pd Pe Pf Pz Qc Qd Qe) Hu(aA Et Fr Hq Hv Hw Hx Ih Ij Ik Il Io Iq Ir Is It Iv Jg Jj Jk Jl Jm Jn Jo Jp Jq Jr Jt Lh Lu Lv Lx Lz Mb Mc Me Mf Mh Mi Mj Ml Mm Mp Mr Mv Mx Mz Nb Nc Nd Ne Nh Nj Nk Nl Nm Nn No Nq Nr Ns Nx Ny Oe Of Og Ok On Oz Pa Pb Pd Pe Pf Pg Po Qa Qb Qc Qd Qe) Og(aA Et Ih Ik Io Iq Ir Is It Iv Jj Jm Jt Lu Lv Lx Lz Mb Mc Me Mf Mh Mi Mj Ml Mm Mp Mr Mu Mv Mw Mx Mz Nb Nc Nd Ne Ng Nh Nk Nl Nn No Nq Nr Ns Nt Nx Ny Oe Of Oh Oz Pb Pc Pd Pg Qd Qe) Lj(Fr Hq Hr Hw Ih Ii In Iq Is It Iu Jg Jh Jk Jl Jm Jn Jo Jp Jq Js Lh Ly Ma Mb Md Mf Mn Mq Mr Mt Mu Mx Na Nc Nf No Nr Nv Oi Om On Pf Po Pz Qa Qb Qc Qd Qe) Jj(Et Hv Hx Ij Il Io Iq Ir Is It Iv Jg Jm Jn Jr Jt Lu Lw Lz Mc Me Mh Ml Mp Mv Mw Mx Mz Nb Nd Ne Nj Nm Nn Nt Nx Ny Ok Oz Pb Pc Pd Pf Pg Po Qa Qd Qe) Lw(Hx Ii Ik Il Io Ip Ir It Iv Jh Lu Lz Mb Mc Md Me Mh Mj Ml Mu Mv Mx Mz Nd Ne Nj Nk Nl Nn Nq Ns Nt Nu Nv Ny Oe Of Oh Ok Om Oz Pa Pd Pe Pg Qe) Mv(Ij Il Io Iq Ir Is It Iv Lu Lx Lz Mc Me Mh Mi Mj Ml Mp Mr Mt Mx Mz Nb Nd Ne Nj Nm Nn No Nq Ns Nt Nu Ny Oe Of Ok On Oz Pb Pc Pd Pe Qe) Nj(Ik Il Io Iq Ir Is Iv Lu Lz Mc Me Mh Mi Mj Mk Ml Mp Mr Mu Mw Mz Nd Ne Ng Nh Ni Nk Nm Nn No Ns Nt Nu Ny Oe Of Ok Oz Pb Pc Pd Pg Qe) Pb(Et Hx Ik Il Io Ir Is Iv Jn Jt Lu Lz Mc Me Mh Ml Mp Mw Mz Nd Ne Ng Nm Nn Nq Ns Nt Nu Ny Oe Of Ok Oz Pc Pd Pe Pf Pg Qe) Mp(aA Et Ij Il Io Iq Ir Is Iv Jt Lu Lx Lz Mc Me Mh Mi Ml Mm Mw Mx Mz Nd Ne Ng Nm Nn No Nq Ns Nt Nx Ny Of Oz Pc Pd Qe) Ir(Hx Ii Ij Ik Il Jh Lu Lz Mc Mh Mj Ml Mw Mz Na Nb Nd Ne Nf Ng Nm Nn Nq Ns Nt Nu Nv Ny Oe Of Ok Om Oz Pc Pd Pg) Pc(Et Hx Il Io Iv Jh Jt Lu Lz Mc Me Mh Ml Mw Mz Nd Ne Ng Nm Nn Nq Ns Nt Nu Ny Oe Of Ok Oz Pd Pf Pg Qe) Nu(Hx Io Iv Jh Lu Lz Mc Me Mh Mj Ml Mu Mw Mz Nd Ne Nm Nn Nq Ns Ny Oe Of Ok Oz Pa Pd Pe Pg) Mh(aA Et Hx Ik Il Iv Lu Lz Mc Me Mj Ml Mw Mz Nd Ne Ng Nm Nn Nq Ns Nt Ny Of Ok Oz Pg) Mw(Ij Il Io Is Iv Jt Lu Lx Lz Mc Me Mi Ml Mr Mz Nd Nm Nn Nt Ny Of Ok On Oz Pe) Ng(aA Et Ij Il Iv Jg Jt Lu Lz Mc Me Mg Mj Ml Mm Mz Nd Nn Nt Nx Ny Ok Oz Pd Qe) Ok(Ii Io Jh Lu Lz Mc Me Mj Ml Mz Nb Nd Nn Nq Ns Ny Oe Om Oz Pg) Me(Lz Mj Ml Nd Nm Ns Nt Ny Of Oz Pg) Nt(Mj Mz Ne Nq Ns Ny Oe Of Pg) Lz(Ik Il Mc Mj Nm Ns Oz Pg) Ny(Ml Nm Ns Oz) Iq(Ik Il Mj) Of(Et Nm Nn) NmLu NnNq NsNd McMl MjMx NbIv HxPe QePg} Ok{Jj(Aa Et Fr Hq Hr Hu Hv Hw Hx Ih Ii Ij Ik Il Io Ip Iq Ir Is It Iu Iv Jg Jh Jk Jl Jn Jo Jp Jq Jr Js Jt Lh Lu Lv Lx Ly Ma Mb Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm No Nq Nr Ns Nt Nv Nx Ny Oe Og Oh Oi Om On Pa Pd Pe Pf Pg Po Pz Qa Qb Qc Qd) Of(aA Et Fr Hu Hv Hw Hx Ih Ii Ij Ik Il In Io Ip Iq Is It Iu Iv Jg Jl Jm Jn Jp Jq Jr Js Jt Lh Lu Lv Lx Ly Lz Ma Mb Md Me Mf Mg Mh Mi Mj Mk Ml Mm Mn Mp Mq Mr Mt Mu Mv Mw Mx My Mz Na Nb Nc Ne Nf Ng Nh Ni Nj Nk Nl Nm No Nr Ns Nt Nv Nx Ny Oe Oh Oi Om On Pa Pd Pe Pf Pg Pz Qa Qb Qc Qd Qe) Ms(Aa Et Fr Hu Hx Ih Ij Ik Il Io Ip Iq Ir Is It Iu Iv Jk Jl Jm Jn Jo Jp Jq Jr Js Jt Lu Lv Lx Ly Ma Mb Mc Md Me Mf Mg Mh Mi Mj Mk Ml Mm Mn Mp Mq Mr Mt Mu Mv Mw Mx My Na Nb Nc Nd Ne Nf Ng Nh Ni Nj Nk Nl Nm No Nq Nr Ns Nt Nu Nv Nx Ny Oe Oh Oi Om On Oz Pa Pd Pe Pf Pg Pz Qa Qb Qc Qd Qe) Oy(AA Et Fr Hq Hr Hu Hv Hw Hx Ih Ii Ij Ik In Ip Iu Jg Jh Jk Jl Jm Jn Jo Jp Jq Jr Js Jt Lh Lu Lv Lx Ly Ma Mb Md Me Mf Mg Mh Mi Mj Mk Ml Mm Mn Mq Mr

Figure 41 Continued

Mt Mu Mv Mw Mx My Na Nb Nc Ne Nf Ng Nh Ni Nj Nk Nl Nm No Nq Nr Ns Nt Nv Nx Ny Oe Oh Oi Om On Oz Pa Pb Pc Pd Pe Pf Pg Po Pz Qa Qb Qc Qd) Fp(AA Et Fr Hq Hr Hv Hx Ih Ii Ij Ik Il In Io Ip Iq Ir Is It Iu Iv Jh Jk Jl Jm Jn Jo Jp Jq Jt Lh Lu Lv Lx Ly Lz Ma Mb Md Me Mf Mg Mh Mi Mk Ml Mm Mn Mq Mr Mt Mu Mv Mw Mx Mz Na Nb Nc Nd Nf Nh Ni Nj Nk Nl Nm Nn No Nr Ns Nt Nu Nv Nx Ny Oh Oi Om On Oz Pa Pd Pe Pf Pg Po Pz Qc Qd Qe) Og(aA Fr Hu Hv Hx Ih Ii Ik In Io Ip Iq Is It Iu Iv Jg Jl Jm Jn Jo Jq Jr Js Jt Lh Lu Lv Lx Ly Ma Mb Md Me Mf Mg Mi Mj Mk Ml Mm Mn Mp Mq Mr Mt Mu Mv Mw Mx My Mz Na Nb Nc Nd Ne Nf Ng Nh Ni Nj Nk Nl Nm No Nq Nr Ns Nt Nv Nx Ny Oe Oh Oi Om On Pa Pb Pd Pe Pf Pg Po Qa Qb Qc Qd Qe) Im(aA Et Fr Hq Hr Hv Hx Ih Ii Ik Il In Io Ip Iq Ir Is It Iu Iv Jh Jl Jn Jo Jq Jr Jt Lu Lv Lx Ly Ma Mb Mc Md Me Mf Mg Mh Mi Mj Mk Ml Mm Mn Mq Mr Mt Mu Mv Mw Mx Mz Na Nb Nc Nd Ne Nf Nh Ni Nj Nk Nl Nm Nn No Nr Ns Nt Nu Nv Nx Ny Oh Oi Om On Oz Pa Pc Pd Pe Pf Pg Pz Qc Qd Qe) Ng(aA Io Ip Iq Ir Is It Iu Iv Jg Lu Lx Lz Mc Mh Mi Ml Mp Mr Mz Nb Nd Ne Nj Nm Nn No Nr Nt Nu Ny Oe Oz Pb Pc Qa Qd Qe) Hu(Hq Io Ir Is Iv Lu Lw Lx Lz Mc Mg Mh Mp Mr Mz Nd Nj Nn Nt Nu Ny Oe Oz Pb Pc Qa Qd Qe) Lw(Aa Io Ir Iv Lu Lz Mc Me Mg Mh Ml Mp Mw My Mz Nj Nn Nq Ns Nu Oe Oz Pb Pc Pd) Lj(Hr Hw Ih Ii Ij In Jg Jh Jm Jn Jr Js Md Mq Mu Nf Nv Pe Po Qa Qb Qc Qd Qe) Lz(Aa Ik Il Io Ir Mc Mg Mj Mp Mv My Mz Ne Nj Nn Nq Ns Nu Oe Oz Pb Pc Pd) Oe(Aa Il Io Ir Is Iv Mc Mg Mh Mp Mz Nj Nn Nu Ny Oz Pb Pc Qe) Pb(Io Ir Is Iv Mc Mg Mh Ml Mp My Mz Nd Nj Nn Nq Nu Ot Pd Pf Qe) Ir(Jo Mc Mg Mh Mj Mp My Mz Na Nj Nn Nq Nu Oz Pc) Pc(Io Mc Mg Mh Ml Mp My Mz Nd Nj Nn Nq Nu) Mh(Mc Mg Mj Mp My Mz Nj Nn Nq Nu Oz) Mc(Mg Ml Mp My Mz Nj Nq Oz) Mp(Is Iv Mz Nd Nn Nq Nu) Mg(Io It Iv Nj Nn Nu) My(Lx Mt Mz Nn Oz) Nq(Mz Nn Nu) Nj(Mz Nd Nn) Aa(Io Lu) AjNm NuPd MjIq IoOz} Lj{Im(Fp Fr Hq Hr Hv Hw Hx Ih Ii Ij Ik Il In Io Ip Is It Iu Iv Jg Jh Jk Jm Jn Jo Jq Jr Js Lh Lx Ly Ma Mb Md Me Mf Mg Mh Mk Ml Mm Mn Mq Mr Mt Mu Mv Mw Mx My Mz Na Nb Nc Ne Nf Ng Nh Ni Nk Nl No Nr Ns Nv Nx Ny Of Oh Oi Om On Oz Pa Pd Pe Pg Po Pz Qa Qb Qc Qd Qe) Jp(aA Fp Hq Hu Hv Hw Hx Ij Ik Il Io Iq Ir Is Iv Jg Jk Jl Jm Jn Jo Jq Jr Jt Jv Kl Lh Lu Lv Lx Ly Lz Ma Mc Me Mf Mg Mh Mi Mj Mk Ml Mm Mr Mt Mx My Mz Nb Nd Ne Ng Nh Ni Nj Nk Nl Nn No Nq Ns Nu Nv Nx Ny Oe Of Og Oh Oi On Oz Pa Pb Pc Pd Pe Pf Pg Po Pz Qd Qe) Lw(aA Fp Fr Hu Hv Hx Ij Ik Il Io Ip Iq Ir Is Iv Jl Jn Jq Jr Js Jt Lh Lu Lv Lx Ly Lz Ma Mb Mc Md Me Mf Mg Mh Mi Mj Mk Ml Mn Mp Mr Mt Mw Mx My Mz Na Nb Nc Nd Ne Ng Nh Ni Nj Nk Nl Nm No Nq Ns Nv Nx Oe Of Oh Oi Om On Oz Pa Pb Pd Pe pF Pg Po Pz Qc Qd Qe) Nt(aA Hu Ik Ir Jg Jl Jq Jt Lh Mc Mi Mj Mm Mp Ms Mz Nd Ne Nh Nk Nm Nn Nx Ny Oe Og On Oy Oz Pb Pc) Jj(aA Ii Ij Ir Is Jl Jm Jn Jo Jq Lh Lx Mc Mg Mi Mp Ms Mz Nd Nm Nv Nx Of Pc Pd Pe Pg Po Pz Qd Qe) Nu(aA Hu Ir Jg Jl Jq Jt Mi Mm Mp Ms Mz Nd Nm Nn Nx Ny Og On Oy Pc) On(aA Hu Ik Ir Mc Mj Mm Mp Ms Mw My Ng Nk Nm Nn Nq Oe Of Pc) Jt(aA Hu Ik Lx Mj Mm Mp Ms Mz Nd Nk Nn Ny Oe Og Oy Pc) Og(aA Il Ir Jl Jq Lh Lx Mg Mi Mm Mp Nn Nv Nx Ny Of) aA(Ij Ik Jg Mi Mm Mp Mz Nd Nm Nn Ny Of Om Oy Pc) Nm(Aj Ir Jl Lx Mi Mm Mp Ms Mz Nd Nn Ny Oy) Jg(Hu Ir Jl Mi Mp Ms My Nd Ng Oe Of Oy Pc) Nn(Hu Ik Ir Mi Mp Ms Nk Nq Ny Oe Oy Pc) Mp(Ir Mm Ms Mz Nk Ny Oy Pc) Mm(Ir Mi Ms Oe Oy) Ny(Ir Mi Ms Oe Oy) Et(Ih Ii In) Oy(Jl Lh Nv) bM(iJ Ke) MiPc IkIq SfPj cMdU} Im{Jj(aA Fr Hq Hv Hw Hx Ih Ii In Io Ip Ir Is It Iu Iv Jg Jh Jk Jl Jm Jn Jo Jp Jq Jr Js Lh Lu Lv Lx Ly Mb Mc Md Me Mf Mh Mi Mj Mk Ml Mm Mn Mp Mq Mr Ms Mt Mu Mv Mw Mx My Na Nb Nc Nd Ne Nf Ng Nh Ni Nj Nk Nl Nm No Nq Nr Ns Nv Nx Ny Oe Of Oh On Oz Pa Pc Pd Pe Pf Pg Po Qa Qc Qd Qe) Hu(aA Fr Hq Hv Hw Hx Ik In Iq Is Iu Iv Jg Jh Jk Jn Jq Jr Js Lh Lu Lv Lx Ly Mc Md Me Mf Mh Mi Mj Mk Ml Mm Mp Mr Ms Mt Mu Mv Mx Mz Nb Nc Nd Ne Ng Nh Nj Nk Nl Nm No Nq Nr Ns Nu Nv Nx Ny Oe Of Oh Om Oz Pa Pb Pc Pd Pg Po Qa Qc Qd Qe) Et(aA Hq Hv Hx Io Iq Ir Iu Iv Jh Jl Jn Jo Jq Jr Jt Lu Lv Lw Mc Me Mg Mi Mj Ml Mp Mr Mu Mv Mw Mx My Mz Nd Ne Nj Nm Nn No Nq Ns Nt Nu Oi Oz Pa Pb Pc Pd Pe Pf Pg Pz Qc Qd Qe) Oy(aA Iq Ir Iv Jg Jl Jn Jq Jr Js Lh Lu Lx Mc Mh Mi Mm Mp Ms Mz Nj Nm Nn No Nt Nu Oe On Oz Pd Pe Pf Pg Po Qc Qd Qe) Fp(aA Hx Ik Iq Ir Jk Jl Jp Jq Jt Lz Mc Mj Mm Mp Ms My Mz Ne Ng Nj Nk Nm Nn Nq Ns Nt Nu Oe Pb Pc Qc Qd) Lz(Hx Ir Jk Jp Jq Jt Lw Mc Mj Ms Mz Ne Ng Nj Nk Nm Nn Nq Ns Nt Nu Oe Oz Pb Pc Pd Pe Pg Qd) Oe(Iq Ir Jl Jp Jt Lw Nj Nn Nt Nu Pb Qd Qe) Ng(Iq Ir Jg Jp Lh Nm Nn Nt Nu Pf) Lw(Ir Jk Jp Ms My Mz Nj Nq Pb) Pb(Ir Jl Jp Jt Mh Nt Pe Pf) Jk(Ir Jl Jp Jt Nn Nt Qd) Og(Il Ip Ma Mw Qb) Ms(Jp Jt) Nj(Mz Nk) NnNq NtNe MhJp MyJt HxPe} Et{Fp(aA Fr Hq Hr Hv Hw Hx Ih Ii Ij Ik Il Io Ip Iq Ir Is It Iu Iv Jg Jh Jk Jl Jm Jn Jo Jp Jq Jr Js Jt Lh Lu Lv Lx Ly Lz Ma Mb Md Me Mf Mg Mh Mi Mj Mk Ml Mm Mn Mp Mq Mr Ms Mt Mu Mv Mw Mx My Na Nb Nc Nd Ne Nf Nh Ni Nj Nk Nl Nm Nn No Nq Nr Ns Nt Nu Nv Nx Ny Oe Of Oh Oi Om On Pa Pd Pe Pf Pg Po Pz Qa Qb Qc Qd Qe) Oy(AA Hu Ih Ij Il Iq Ir Is Iv Jj Jl Jm Jn Jq Jr Js Jt Lh Lx Lz Mc Mh Mi Ml Mp Mr Ms Mx Nd Nj Nm Nn No Nr Ns Nt Nu Nx Ny Of Og Oz Pd Pe Pf Po Qa Qb Qc Qd) Jj(Aa Hu Ir Jm Jn Jq Js Jt Lw Lz Mc Mh Ml Ms Mz Nj Nn No Nt Nu Nx Ny Oz Pb Pc Qa Qd Qe) Hu(Ij Ir Lw Lz Mh Ml Mz Nn Nt Nu Pc Qa Qb Qd Qe) Og(Ij Il Ir Lw Mh Mz Nn Nu Qe) Mh(Lw Ms Mz Nn Pb Pc Qd) Lw(Ml Ms Mz Ng Pc) Qe(Aj Ms Ng Oe Of) Nn(Ms Ng Of) Ng(Nt Nu) LzPc MsMz} Fp{Jj(Aa Jg Jm Jp Lh Lw Mm Nm Nn Nu Ny On Qd) Aa(Jp Lu Lw Mm Nk Nm Nn Nu Og Oy Pc) Jp(Hu Lw Nm Og Oy Oz Pb Pc) Og(Ij Jg Jt Lw Nm Nn) Hu(Jg Jt Nn On) Lw(Mz Nn) Jt(Ng Oy) AjNm GcUy} Aa{Qe(In Iu Jr Lu Lw Ms No Nu Oe Of Og Pc Pg) Jj(Jm Jp Nn Nu Ny Po Qa Qc) Nu(Lu Oy) MzbM JpOy} Aj{Nm(Cs Cu Jp Kq Nn Qd) Kq(bM dB Fw Gp Pj) Qe(Ad Jt Ne) bM(Ad Jt)} jB{aO(aH Al bF cA Js Ly Mj Mx My Mz Ne Nk nR Pg) NkbN OzbU} Nn{Jj(Jt Nt Nu Ny Qd Qe) Og(Ij Lw) cRpK} bU{Oz(dU eQ pH pK) AxdU eFoW} hP{Mz(dA Oe Um) Id(aV cF dA)} Qe{Og(Ij Lw Nm) Jj(Jt Nu)} Gc{hC(Mj Wc) MwSf UueC} Pj{Kq(Ef Kl) aC(Jv Pk)} dU{aW(bB Nj) OzbB mYkP} Uh{KrtO tTrA} cR{oW(bB Nj)} EfIlKe NtJjNy LwJpOy IjOgaA

Unconstrained panels with 3 analytes, where 1.0E-7 >= 'model p-value' > 1.0E-8. Contains 16,720 panels of 37,941,150 total panels evaluated. : Li{Mu(Fp Fr Hq Hr Hv Hw Hx Ih Ik Il In Io Ip Iq Is It Iu Iv Jg Jh Jk Jl Jm Jn Jo Jp Jq Jr Js Jt Lh Lj Lu Lv Lx Ly Lz Ma Mb Mc Md Me Mf Mg Mh Mi Mj Mk Ml Mm Mn Mp Mq Mr Ms Mt Mv Mw Mx My Na Nb Nc Nd Ne Nf Nh Ni Nj Nk Nl Nm Nn No Nq Nr Ns Nt Nu Nv Nx Ny Oe Of Oh Oi Om On Oz Pa Pd Pe Pf Pg Po Pz Qa Qb Qc Qd Qe) Ni(Aa Fp Fr Hq Hr Hv Hw Hx Ih Ik Il Io Ip Iq Is It Iu Iv Jg Jh Jk Jl Jm Jn Jo Jp Jq Jr Js Jt Lh Lu Lv Lx Ly Lz Ma Mb Mc Md Me Mf Mg Mh Mi Mj Mk Ml Mm Mn Mp Mq Mr Ms Mt Mv Mw Mx My Na Nb Nc Nd Ne Nf Nh Nj Nk Nl Nm Nn No Nq Nr Ns Nt Nu Nv Nx Ny Oe Of Oh Oi Om On Oz Pa Pd Pe Pf Pg Po Pz Qa Qb Qc Qd Qe) No(AA Fp Fr Hq Hr Hv Hw Hx Ih Ik Il Io Ip Iq Is It Iu Iv Jg Jh Jk Jl Jm Jn Jo Jp Jq Jr Js Jt Lh Lu Lv Lx Ly Lz Ma Mb Mc Md Me Mf Mg Mh Mi Mj Mk Ml Mm Mn Mp Mq Mr Ms Mt Mw Mx My Na Nb Nc Nd Ne Nf Nh Nj Nk Nl Nm Nn Nr Ns Nt Nu Nv Nx Ny Oe Of Oh Oi Om On Oz Pa Pd Pe Pf Pg Po Pz Qa Qb Qc Qd Qe) Mk(aA Fp Fr Hq Hr Hv Hw Hx Ih Ik Il Io Ip Iq Is It Iu Iv Jg Jh Jk Jl Jm Jn Jo Jp Jq Jr Js Jt Lh Lu Lv Lx Ly Lz Ma Mb Mc Md Me Mf Mg Mh Mi Mj Ml Mm Mn Mp Mq Mr Ms Mt Mv Mw Mx My Na Nb Nc Nd Ne Nf Nh Nj Nk Nl Nm Nn Nq Nr Ns Nu Nv Nx Ny Oe Of Oh Oi Om On Oz Pa Pd Pe Pf Pg Po Pz Qa Qb Qc Qd Qe) Qc(AA Fp Fr Hq Hr Hv Hw Hx Ih Il Io Iq Is It Iu Iv Jg Jh Jk Jl Jm Jn Jo Jp Jq Jr Js Jt Lh Lj Lu Lv Lx Ly Lz Ma Mb Mc Md Me Mf Mg Mh Mi Mj Ml Mm Mn Mp Mq Mr Ms Mt Mv Mw Mx My Na Nb Nc Nd Ne Nf Nh Nj Nk Nl Nm Nn Nr Ns Nt Nu Nv Nx Ny Oe Of Oh Oi Om On Oz Pa Pd Pe Pf Pg Po Pz Qa Qb Qd Qe) Jr(aA Fp Fr Hq Hr Hv Hw Hx Ih Ij Il Io Iq Is Iu Iv Jg Jh Jk Jl Jm Jn Jo Jp Jq Js Jt Lh Lj Lu Lv Lx Ly Lz Ma Mb Mc Md Me Mf Mg Mh Mi Mj Ml Mm Mn Mp Mq Mr Ms Mt Mv Mw Mx My Na Nb Nc Nd Ne Nf Nh Nj Nk Nl Nm Nn Nq Nr Ns Nt Nu Nv Nx Ny Oe Of Oh Oi Om On Oz Pa Pd Pe Pf Pg Po Pz Qa Qb Qd Qe) Oi(Aa Fp Fr Hq Hr Hv Hw Hx Ih Ij Ik Il Io Ip Iq Is It Iu Iv Jg Jh Jk Jl Jm Jn Jo Jp Jq Js Jt Lh Lu Lv Lx Ly Lz Ma Mb Mc Md Me Mf Mg Mh Mi Mj Ml Mm Mn Mp Mq Mr Ms Mt Mv Mw Mx My Na Nb Nc Nd Ne Nf Nh Nj Nk Nl Nn Nq Nr Ns Nu Nv Nx Ny Oe Of Oh Om On Oz Pa Pd Pe Pf Pg Po Pz Qa Qb Qd Qe) Lz(Aa Fp Fr Hq Hr Hv Hw Hx Ih Il In Io Ip Iq Is It Iu Iv Jg Jh Jk Jl Jm Jn Jo Jq Js Jt Lh Lu Lv Lx Ly Ma Mb Md Me

Figure 41 Continued

Pd Qc) Nu(Aa Is Iv Jl Jn Jq Jr Me Mg Nj No Nq Ns Oz Pd Qa Qc) Nj(Ih Is Iv Jl Mp Mr Nd Ne No Ny Oz Qa Qc) Oz(aA Is Iv Jl Jq Mc Me Mp No Pe Pf Qa) Aa(Fp Ji Jr Lu Mb Me Mr Nb Qc) Qa(aA Jk Mp Nq Pd) No(Mp Nq Ns Pd) Mv(Lx Mt Po) bM(Aj Ji Pk) Mw(Lx Po) Hx(Iv Pe) Iq(Ik Il) Jt(Jo Mg) aA(Ih Jm) AjNm FpIn GcNk JhJq} Aa{Qe(aA Fp Fr Hq Hr Hu Hv Hw Hx Ih Ii Ij Ik Il Io Ip Iq Ir Is It Iv Jg Jh Ji Jk Jl Jm Jn Jo Jp Jq Js Jt Lh Lv Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn Nq Nr Ns Nt Nv Nx Ny Oh Oi Om On Oz Pa Pb Pd Pe Pf Po Pz Qa Qb Qc Qd) Fp(Fr Hq Hu Hw Ih Ii Ij Ik Il In Io Ip Iq Ir Is It Iu Iv Jg Ji Jl Jm Jr Jt Lh Lv Lx Ly Lz Ma Mb Mc Md Me Mf Mg Mh Mi Mj Mk Ml Mn Mp Mq Mr Ms Mt Mu Mv Mw Mx My Mz Na Nb Nc Nd Ne Nf Ng Nh Ni Nj Nl No Nq Nr Ns Nt Nv Nx Ny Oc Of Oh Oi Om On Oz Pa Pb Pd Pe Pf Pg Qa Qc Qd) bM(aC Aj aN bA bE cA cB cM dA dD dR eC EF gL gP hG iA Ik Il In Io iP Iq Ir Is Iu Iv Ji Jj Jm Jp Ke Lw Lx Lz Mh Mi Mq Mr Ms Mt Mu Mw Nb Nd Ne Nf Nh Nk Nn Nu Oe Of Og Oi oK Or Oy Pc Pf Pg Pk Qd Uh Vt Vv) Jj(Fr Hu Ii Iq Iv Jg Jl Jr Jt Lh Lu Lw Lx Lz Me Mf Mg Mh Ml Mm Mp Mr Ms Mt Mv Mw Mz Nb Nd Ne Nm Nt Nv Nx On Oy Oz Pc Pd Pf Pz Qb Qd) Lw(Fr In Iv Ji Jp Lh Lu Lx Lz Mb Me Mf Mh Ml Mm Mr Ms Mt Mz Nb Nd Ne Nh Ni Nn Nt Nu Nx Ny Og Oy Pc Po Qa Qc Qd) Nu(Fr In Ji Jp Jr Lx Lz Mb Me Mf Mh Ml Mm Mp Mq Mr Ms Mt Mz Nd Ne Nh Nm Nn Nq Nx Ny Oe Of Og Pc Pd Qc) Lu(Fr In Iv Ji Jp Lx Lz Me Mh Mm Mp Mr Ms Mt Mw Mz Nb Nm Nn Nt Ny Og Oy Pc Qa Qd) Oy(Fr Jg Ji Lx Lz Mm Mp Mr Mt Mz Nm Nn Nt Nv Nx Ny On Pd Po Qa Qb Qc Qd) Nn(In Iv Lx Lz Mb Me Mh Mr Ms Nb Ne Nt Oe Of Og Pc) Lz(Ji Jp Lx Mm Ms Nb Nm Nt Nx Ny Pc) Ms(Ji Jp Lx Mm Mr Mt Nt Nx Ny) Jp(Ji Jr Me Mh Of Pc Qc) In(Ji Lx Nb Nt Ny) Mm(Me Mh Mr Of) Ji(Jq Of Pc Qc) Lx(Oe Pc) FrMe GnNi MrPc NyOg dLiA tXjV} Ji{bM(aA aC aD aE AF aG aH al aJ aK aL aM aN AO AP aQ aR aS aU aV AW AX aY aZ bA bB bC bE bF bG bH bI bJ bL bN bO bP bQ bR bS bU bV bW bX bZ cA cC cD cE cF cG CH cI cJ cK cL cN CO cP cQ cR CS CT cU cV CW CX cY cZ dA dC dD DE dF DG dH dI dJ dK dL dM dN eF FP Fr Gl hG Hq Hr Hu Hv Hw Hx IH Ii Ij Ik Il In Io Ip Iq Ir Is It Iv Jg Jh Jk Jl Jm Jn Jp Jq Jr Js Jt Kl Lh Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Nf Ng Ni Nj Nl Nm Nn No Nq Nr Ns Nt Nu Nv Nx Ny Oe Oh Oi oK Om ON Ou Oz Pa Pb Pc Pd Pe Pf Pk Po Pz Qa Qb Qc Qd Qe Ss Uh Um Uu Vv Wm) Jv(aC aE aF aG aH Aj Al aN AO As Aw Ax aY aZ bH bQ cB cC cH cI cJ Cs Cv dA Dc Dd dE dK eF Fp Fw Gl Gp Hf Hr Hu Hv iA Ib Ic iH Ik Il In Io Ip Iq Ir Is It Iu Iv Jd Jf Jh Jj Jm Jo Jp Ju Ke Kk Kl Kq Kz Lv Lz Mc Mg Mj Mk Ml Mp Mt My Nc Ne Nk Nl Nm Nn No Nr Oa Oe Of Og oK oN Ow Oy Oz Pa Pf Pg Pj Pk Qe Qn Qx Rc Sr Ss Uh Um Uu Vt) Wm(Aj Ef Fp Hu Ik In Io It Iu Jh Jj Jo Ki Kl Mk Mp My Nc Ng Nh Nk Nl Nu Of Og Ou Oz Pe Pg Qe Qx Ss Vt Vv) Yk(fP gP kF kN kO kP kR IW IX mM mP mZ nA nR nT nY oE oK Uu Vp) Ij(Fr Js Lh Lv Ly Ma Mf Mq Mt Na Nc Nr Nv On) aN(aC aF Aj dB Jj Jo Ne Nh Nk Oy Qe) dB(aC Ef Iu Jj Jo Ne Nh Nk Og Oy) Aj(Ad aF Jt Ms Ne Nh Nk Nl Qd) Ef(iJ Jp Kq Ne Nh Nk Nm) Nk(aC cI eF hG iZ Sf) iJ(aF eF iZ My Nh Oy) aC(aF cB Ne Nh) aF(dH Jj Nh) Fw(Ps Vv) jO(sK yJ) CsNh NeiH IuaM SfaW QxjD JjaO OyiZ fPtX tRqZ} Fp{Jp(aA Hv Hx Ih Ij Ik Io Iq Ir Is It Iv Jg Jh Jk Jl Jm Jn Jq Jt Lu Lx Lz Mc Me Mh Mi Mj Mk Ml Mm Mp Ms Mu Mv Mw My Mz Nd Ne Ng Nh Nj Nk Nl Nn No Nq Ns Nt Nu Nx Ny Oe Of Oh Pa Pd Pe Pf Pg Pz Qa Qc Qd Qe) Jt(Aj Ij Ik Jh Jo Lw Lz Mc Mj Mm Mp Ms Mw My Mz Na Nd Ne Nk Nn Nq Nu Ny Oe Of Oi Oz Pb Pc Pd Qd Qe) Lw(Hu Ij Ik Ir Jg Jl Jn Lh Mc Mm Ms My Ne Nk Nm Nt Nu Nv Nx Ny On Oy Oz Pb Pc Pz Qa Qc Qd Qe) Jj(aA Ii Ij Iq Ir Is Jl Jn Jq Js Lz Mc Me Mp Mz Nd No Nt Nv Nx Oz Pb Pc Pz Qa Qc Qe) Nn(aA Ik Ir Jq Mc Mj Mm Ms Mz Ne Nk Nm Nq Nt Nu Oe Oy Oz Pb Pc Qd) Nm(Hu Ir Lh Mc Mm Ms My Mz Ng Ny On Oy Qd Qe) Og(aA Ir Jq Lh Mm Mz Nt Nu Nv Nx Ny On Qd Qe) Mm(aA Hu Ir Jq Mc Ms Mz Ne Oy Pb Pc Qd) Hu(Ij Ir Jq Lh Nt Nu Nv Nx Ny Qd Qe) Jg(Ir Jh Ms Mw My Ng Oy Pb Pc) Vt(cM dB Il Jv Mj Ne Nf Oy Wm) Qd(Ik Mc Mj Nu Oy Oz Pb Pc) On(Mj Ms My Ng Nq Oy) Gc(eC Nk) Mz(aA hP) Pj(bM Jv) NuJq QeOy} Jj{Nn(Hu Ih Ii Ij Iq Ir Is It Iv Jg Jl Jm Jn Jp Jq Jr Js Lh Lu Lv Lw Lx Lz Mc Me Mh Ml Mm Mp Mr Ms Mx Mz Nd Nj Nm No Nx Og On Oy Oz Pb Pc Pe Po Qa Qc) Qe(Aj Dd Gc Hu Ii Ij Ir Jg Jn Jp Jq Lh Lw Lz Mc Mm Mp Ms Mz Nj Nm Nt Nx Ny Og On Oy Oz Pb Pc) Qd(Hu Ik Il Ir Jg Jm Jn Jp Jt Lh Lw Lz Mc Mh Mj Mm Mz Nd Nm Nt Nu Nx Ny Og On Oy Oz Pc) Ny(Ir Jg Jl Jm Jn Jp Jq Js Jt Lh Lw Lz Mm Mp Mz Nm No Nu Nx Og On Qa) Lh(Ih Ij Ir Is Jg Jm Jn Jt Lw Lz Ms Mz Nm Nt Nu Oy Oz Pb Pc Qa) On(Hu Ir Jm Jt Lw Lz Mh Mp Ms Mz Nt Nu Of Oy Oz Pb Pc) Jp(Ir Jm Jt Lw Lz Mh Mz Nm Nt Nu Qa) Jt(Jm Lz Mm Mz Nt Nu Nv Nx Qa Qb) Nt(Iq Ir Jm Mm Mz Qa) Jg(Jm Lw Lz Mz Qa) Nu(Jm Jq Mz Qa) bM(Ke Pj Uh) Mm(Ir Jm) GcUy} Aj{Nm(aC Ad Af Al aN Ar Ax BA Bb Bc bM cB cI Cv dA dB Dc Fa Fr Ii Iq Jk Jl Jm Jt Lh Lx Lz Md Mr Mt Mz Ne Nk Nv Ny Og On Pf Qa Qc) Qe(aN Bb Bg cM cQ Cv dB Dc Dd Dg Di Gc Io Iq Ir Iu Jg Jp Lw Mb Mc Md Mg Mj Mm Mt Nc Ng Nh Nk Nl Nn Nt Nu Nx Pb Pd Pf Pg Pj Qb) Kq(aF Aw Bo cC Cv Dk Ef Hu Hx Ib Id Il Io Ir Iz Jv Kg Ks Lv Mb Mc Mj My Ne Nh Nk Nu Pg Qx Vt Wm) Ad(Cu dA dB Lw Mt Ne Nk Nn Nu) Jt(dB Mt Nk Nn Pf) Pj(bM Fa Fw Il Lw) Ke(bM dB Il) Gc(gP Uy) bM(Bb Dc) CvNt LhdB} Og{Ij(Hu Ih Ii Iq Ir Is Jg Jl Jp Jt Lh Lx Lz Me Mm Mp Ms Mz Nj No Nt Nu Nv Nx Ny On Pb Qd) Nn(aA Hu Il Ir Is Iv Jg Jt Lz Mh Ms Mz Nj Nm Nt Nu Ny Qd Qe) Qd(Ik Il Ir Jg Jt Lw Mz Nm Nt Nu Ny Oy Oz) Qe(aA Il Ir Jg Jp Jq Jt Mm Nt Nu Ny Oy) Ny(Il Ir Jp Jt Lw Mz Nm Nt Nu) Lw(Jg Jp Lh Nt Nu Nx On Qa) Nm(Cs Il Jp Lh On Qa) Mz(hP Jt Nt) Jg(Il Ir Lz) On(Hu Oy) CsVt GcUy NuJp IlJt XaoP} Oy{Qd(aA Ik Il Ir Jg Jl Jp Jt Lh Lw Lx Lz Mh Mm Mp Mz Nd Nm Nn Nt Nu Nx Ny On Pd) Jp(Ih Ir Is Jl Jm Jq Jt Lx Lz Mh Mp Ms Mz Nm Nn No Nt Nu Ny Po Qa Qe) Nn(Hu Ir Is Jg Jl Jt Lw Lx Lz Nt Nu On Po Qe) Qe(aA Ir Jg Jq Jt Lh Lw Mm Nm Nt Nu Ny On) On(Hu Ir Lw Ms Nu) Jg(Ir Lw Lz Qa) Gc(gP iZ Uy) Jt(Mz Ny) CsVt LwLh KebM} hP{Mz(aA aC AF aS aV aX bG bL bQ bU bW cA cD cF cG cK cN cO cU dH dI dK hR hV hW Hx Id Il Io Ip Iq Is It Iu Jl jO Kk IK IL IO Lw Lx Ly Lz Mk Mp Mt Nd Oz Pa Pb Pd Pe Pf Po Ug Uh uV) Id(bQ bR bU cA cK Co dI Jy Lw Lz Mk Nd Oz Pa Pd Pe Pf Rg Tj) MjLh} Gc{hC(bG Dg Dk Dl Du Hc Hx Jt Kr Mh Mq Nk Nl nR Pa Pg Qm Rm Vp) Nk(Ex gL gP iA Mw Po Qa Qd Qe Uk Uy Va) Uy(aCr Cs Du Gd Mg Mw Oz Pa Sf Uc Uu) eC(cD Cs Mg pF Pg) iZ(Dl Du Hc Jt Pa) Sf(Al aW Il Kd) Qe(Nc Nh Ni Of) Du(hB kS Vq) gP(bG Dg Dl) Gd(kR Vq) MwVt UuVq} Jp{Lw(Hu Ir Lz Mh Ms Mz Ng Nt Ny Pb Pc Qe) Hu(Ij Ir Lz Mh Nn Nt Nu Ny Qd Qe) Lz(Ik Ms Nm Nt Ny Oz Pb Pc) Jv(aC Ar Ax Cs dB Ic Id Pj) Nt(Ms Ne Ng Pb) Nk(Eq Sf Si Yd) Kl(Kq Nm Pj Qe) Mh(Pb Pc Qd) Cs(Uu Vt) Nm(Eq Ng) Ms(Ny Qe) bM(Ne Pk) EfKq GnVp NcYd NgJt} Pj{aC(aM aN aQ bM cB dA dB dM Gp iH iJ Mz Nk Vt) Sf(aW Fw Il Jm Kd Ki Nk Nr Uy) Fa(Ic Jo Jt Jv Kl Ou Uu) Kq(Ad Ap Dg Jo Jv Uu) Jv(Cs Id Ki Or) Cs(bM Vt) Pk(bM iJ) WmUu GzrB MzlK NkUy KliJ} Nn{Hu(aA Ij Ir Is Iv Jg Jl Jn Jt Lh Lw Lx Lz Mh Mr Ms Mz No Nt Nu Ny On Pc Pe Po Qd Qe) Ng(Jg Jt Lw Nm Nt Nu) Ms(Ir Jt Qe) Qd(Jk Nq Oe) Ir(Lw Nu) CsVt JvKe PkbM} Ke{Jv(aC Ar Ax bM cB cI Cs dB eF Ic Il tO Wm) bM(aC Aw cM dB dN EF Ib Il Kl Ne Pk) Ef(dB iJ Kq) Wm(Kl Ne Uu) Il(Aw Iz Kl) KlKq} Cs{Vt(bM cM dB Fw Il In Jv Mj Ne Nf Nh Nk Nm Oe Oi Ou Pe Pg Qx Uh Wm) Uh(bM cM dB Jv Nk Vv) TnWn IlJv} Hu{On(Mh Ms Nt Nu Ny Of) Qe(Jg Jt Nt Nu) Qd(Jg Nt Nu) Jg(Lz Qa) NtNy} Id{uM(cQ Qm rC Uh) Jv(Mn No Uh) jV(aC Hf Or) Kd(hR vT) MzhW UhbM yJvT} Ng{Jg(Lh Lw Lz Ny Qd Qe) Nm(On Qe) Jt(Ny Qe) NtNy LwOn aOjB} Uh{bM(aA cM Fw Pk Rj Vv) Wm(Ne Uu) MztO QetR WnUu PeoN} Mz{aQ(jQ uM) cI(hW rB) OfqY UmrB aSlK} Ef{Kq(bM dB Fw Lv Nt Nu)} gV{AdMb LvcM MncW NjaM QedC} Vt{Nr(Ti Th) WmNe NoIb} Du{FwmU aWkI cNmE} Qe{NuLw MjdU MyJg} Oz{bU(fB oW pl)} aO{jB(Kx Kz Nh)} fA{Nk(Nx pK) Axcl} Gz{Kr(qT rC)} Ny{JktX iPyJ} mT{EqNe FyYg} LzIkQd MnYknR MyIjaA OrclrB PkaCbM wBjMul Unconstrained panels with 2 analytes, where 1.0E-8 >= 'model p-value' > 0. Contains 218 panels of 199,653 total panels evaluated. : Ji(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md

Figure 41 Continued

Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr
Ns Nt Nu Nv Nw Nx Ny Oe Of Og Oh Oi Ok Om On Oy Oz Pa Pb Pc Pd Pe Pf Pg Po Pz Qa Qb Qc Qd Qe) Lj(aA Et Fp Hu Ik Im Ir Jj Jl Jp Jq
Lj Lw Mc Mh Mp Ms Mv Mw My Mz Ne Ng Nj Nk Nm Nn Nq Ns Nt Nu Nw Ny Oe Of Og Ok Oy Oz Pb Pc Qd Qe) Nw(Fp Hu Im Ir Jj Lj Lw
Lz Me Mh Mp Ms Mv Mw My Ng Nj Nt Nu Og Ok Oy Pb Pc) Ok(Fp Hu Im Ir Jj Lj Lw Lz Mh Ms Ng Oe Of Og Oy Pb Pc) Im(Et Fp Hu Jj Lj
Og) Lj(Et Jp Lw Nt On) Et(Fp Oy) AaQe

Unconstrained panels with 2 analytes, where 1.0E-7 >= 'model p-value' > 1.0E-8. Contains 339 panels of 199,653 total panels evaluated. :
Ok(AA Et Fr Hx Ih Ii Ik Il Io Ip Iq Is It Iu Iv Jh Jk Jn Jo Jq Jr Lu Lv Lx Ly Ma Mb Mc Md Me Mf Mg Mi Mj Mk Ml Mm Mn Mp Mq Mr Mt
Mu Mv Mw Mx My Mz Na Nb Nc Nd Ne Nf Nh Ni Nj Nk Nl Nm Nn No Nq Nr Ns Nt Nu Nv Nx Ny Oh Oi Om On Oz Pa Pd Pe Pf Pg Pz Qa
Qb Qd Qe) Nw(AA Et Fr Hv Hx Ih Ii Ij Ik Il In Io Ip Iq Is It Iu Iv Jh Jn Jr Jt Lh Lu Lv Lx Ly Ma Mb Mc Md Mf Mg Mi Mj Mk Ml Mm Mn Mq
Mr Mt Mu Mx Mz Na Nb Nc Nd Ne Nf Nh Ni Nk Nl Nm Nn No Nq Nr Ns Nv Nx Ny Oe Of Oh Oi Om On Oz Pa Pd Pe Pf Pg Qa Qd Qe)
Li(Aa Fr Hq Hr Hv Hw Hx Ih Ii Ij Il In Io Ip Iq Is It Iu Iv Jg Jh Jk Jm Jn Jo Jr Js Jt Lh Lu Lv Lx Ly Lz Ma Mb Md Me Mf Mg Mi Mj Mk Ml
Mm Mn Mq Mr Mt Mu Mx Na Nb Nc Nd Nf Nh Ni Nl No Nr Nv Nx Oh Oi Om On Pa Pd Pe Pf Pg Po Pz Qa Qb Qc) Lj(aA Ij Ir Is Jg Jj Jl Jq Jt
Lh Lv Lx Mg Mi Mm Mp Ms Mz Nd Nm Nn Nu Nv Nx Ny Og Pc Pd Pg Qd Qe) Im(aA Iq Ir Jk Jl Jp Jq Jr Jt Lw Lz Mh Ms Mz Ng Nj Nn Nt
Nu Oe Oy Pb Pc Pf Qd Qe) Et(Aa Hu Ir Jj Lw Lz Mh Ml Ms Mz Ng Nn No Nt Nu Of Og Pc Qd Qe) Aa(Fp Ji Jj Lu Lw Nn Nu) Fp(Jp Jt Lw)
Ji(bM Jv Wm) Aj(Kq Qe) Jj(Nn Qe) MzhP IjOg Unconstrained panels with 2 analytes, where 1.0E-6 >= 'model p-value' > 1.0E-7. Contains 440 panels of 199,653 total panels evaluated. : Et(aA
Fr Hq Hr Hv Hw Hx Ih Ij Ik Il In Io Iq Is It Iu Iv Jg Jh Jk Jl Jm Jn Jo Jp Jq Jr Js Jt Lh Lu Lv Lx Ly Ma Mb Mc Md Me Mf Mg Mi Mj Mk Mm
Mn Mp Mq Mr Mt Mu Mv Mw Mx My Na Nb Nc Nd Ne Nf Nh Ni Nj Nk Nl Nm Nq Nr Ns Nv Nx Ny Oe Oh Oi Om On Oz Pa Pb Pd Pe Pf Pg
Po Pz Qa Qb Qc) Im(Aa Fr Hq Hr Hv Hw Hx Ih Ii Ij Ik Il In Io Ip Is It Iu Iv Jg Jh Jm Jn Jo Js Lh Lu Lv Lx Ly Ma Mb Mc Md Me Mf Mg Mi Mj
Mk Ml Mm Mn Mp Mq Mr Mt Mu Mv Mw Mx My Na Nb Nc Nd Ne Nf Nh Ni Nk Nl Nm No Nq Nr Ns Nv Nx Ny Of Oh Oi Om On Oz Pa Pc
Pd Pg Po Pz Qa Qb Qc) Lj(Aa bM Fp Fr Hq Hu Hv Hw Hx Ih Ii iJ Ik Il In Io Ip Iq It Iu Iv Jh Jk Jm Jn Jo Jr Js Jv Ke Lu Ly Lz Ma Mb Mc Md
Me Mf Mh Mj Mk Ml Mn Mq Mr Mt Mu Mv Mw Mx My Na Nb Nc Ne Nf Ng Nh Ni Nj Nk Nl No Nq Nr Ns Oe Of Oh Oi Om Oy Oz Pa Pb Pe
Pf Po Pz Qa Qb Qc Uh Vt) Aa(bM Fr In Iv Jp Jr Lh Lv Lx Lz Ma Mb Me Mf Mh Ml Mm Mp Mq Mr Ms Mt Mv Mw Mz Nb Nd Ne Nh Ni Nj
Nk Nl Nm Nt Nv Nx Ny Oe Og On Oy Pc Pd Pf Po Qa Qb Qc Qd) Fp(Ir Jg Jj Jq Lh Mm Mz Nm Nn Nt Nu Ny Og On Qd Qe Vt) Nw(bM Hq
Hr Hw Jg Jk Jl Jm Jo Jp Jq Js Po Pz Qb Qc) Ok(Aj Hq Hr Hv Hw Ij In Jg Jl Jm Jp Js Jt Lh Po Qc) Qd(Hu Ik Ir Jj Jp Lw Mh Mz Nn Nt Nu Ny
Og Oy Oz) Qe(aA Gc Hu Jp Jt Lw Nm Nn Nt Nu Og Oy) Jp(Hu Ir Jj Lw Lz Mh Nt Ny Oy) Nn(Hu Ir Jt Lw Nt Og Oy) Ji(aC aF Aj aN dB Ef iJ)
Jj(Jg Jt Lh Nt Ny On Qa) On(Hu Ms Og Oy) Aj(Ad Jt Nm) Gc(eC hC Uy) Pj(aC Fa Sf) Cs(Uh Vt) Ke(bM Jv) Og(Jg Ny) EfKq WmVt TiLi
NtMz Unconstrained panels with 2 analytes, where 1.0E-5 >= 'model p-value' > 1.0E-6. Contains 762 panels of 199,653 total panels evaluated. : Qd(aA
Aj Fr Hq Hv Hw Hx Ih Ij Il Io Iq Is It Iu Iv Jg Jh Jk Jl Jm Jn Jo Jq Jr Js Jt Lh Lu Lv Lx Lz Ma Mb Mc Me Mf Mi Mj Mk Ml Mm Mn Mp Mr Ms
Mt Mu Mv Mw Mx My Nb Nc Nd Ne Ng Nh Nj Nk Nl Nm No Nq Nr Ns Nv Nx Oe Of Oh Oi On Pa Pb Pc Pd Pe Pf Pg Po Pz Qa Qc Qe) Ji(aE
Af aG aH aK aM AO Ap aQ AR AW AX Ba Bg bL bP bQ cB cC Ch cI cJ cM Co Cs Ct Cu Cw Cx dA Db dD dE Dg dH Dk dL dR Ed eF Ex Fa
fP Fw GL Gp hC hG iA Ic Id iH iP iZ Ju Ki Kl oN Ou Qu Qx Rc Sf Sr Ss Uh Uu Uv Uy Vt Vv) Qe(aC aN Aw bM cM Cs Ct Cv dB Dd Di Id Ij
Ik Iq Ir Is Iv Jg Jl Jn Jq Jr Js Jv Ke Lh Lx Lz Mc Me Mh Mi Ml Mm Mp Mr Ms My Mz Nd Ne Ng Nh Nj Nk Nl No Nq Ns Nv Ny Oe On Ou Oz
Pa Pb Pc Pd Pe Pf Pg Pj Uh Vt) Jp(aA aC bM Cs Eq Hc Ic Id Ih Ij Iq Is It Iv Iz Jl Jm Jn Jq Jr Js Jt Jv Kl Lh Lu Lx Me Mi Ml Mp Mr Ms Mx My
Mz Ne Ng Nj Nm Nn No Ns Nu Nx Of Og Oz Pb Pc Pe Pf Pj Po Qa Qb Qc Vt) Aa(Hq Hr Hu Hv Hw Hx Ih Ii Ij Ik Il Io Ip Iq Ir Is It Iu Jg Jh Jk
Jl Jm Jn Jo Jq Js Jt Ly Mc Md Mg Mi Mj Mk Mn Mu Mx My Na Nc Nf Ng No Nq Nr Ns Of Oh Oi Om Oz Pa Pb Pe Pg Pz) Nn(aA Aj Ih Ij Ik Iq
Is Iv Jg Jl Jn Jq Jr Js Lh Lu Lv Lx Lz Me Mh Mi Ml Mm Mp Mr Ms Mx My Mz Ng Nj Nk Nm No Nq Ns Nu Nx Ny Oe On Oz Pb Pc Pe Po Qa
Qc Vt) Fp(aA Fr Hu Ih Ii Ij Ik Iq Is Iv Jl Jm Jn Js Ke Lx Lz Ma Mc Me Mh Mi Mp Mr Ms Nd Ne Nh Nj Nk Nl No Nv Nx Oe Oh Oy Oz Pb Pc
Pe Pj Pz Qa Qb Qc Uh Un Wm) Vt(aC Aj Ar Ax bM cM dB Ed Fa Fw Gc Il Jd Jv Ke Kq Kr Li Lz Mz Ne Nf Nm No Nr Nt Nu Og Ou Oy Pf Pg
Pj Uh Um Ti Th) Ke(aC Aj aN Aw Ax cB Ch Cs dB EF Fw Gp Ib Ik Il Iz Jj Kl IM Ne Nk Og Oy Pj Uu Wm) Ny(aA Hu Ir Is Jg Jl Jn Jq Jt Lh
Lw Lz Mp Ms Mz Nm No Nt Nu Oy Qa) Gc(fP gP iA iJ iP iZ kR Ni Nk nY oE Pz Qa Qb Qc Sf Uk Uu Va Vq) Pj(Aj Ax bM Cs Fw hC Id iJ Il
iZ Jj Jv Ki Kq Lj Lw Mz No Or Uy) Nt(aA Hu Ir Is Jq Js Jt Lh Lw Lx Lz Mm Ne Og On Oy Pc Qa Qc) Lh(aA Hu Ih Ir Is Jt Lw Lx Ms Mz Ng
Nm Nu Og Oy Pb Pc Qa) Lj(aC cM Fn hG Hr Id iO Jd Jy Kq Or Un Up Us Ut Wb Wm Ti) Mz(aA iC Ir Jg Jj Jt Lw Lx Lz Mm Nu On Qa qT)
Qa(aA Hu Ir Jg Jt Lw Lz Nm Nu Og Oy Pc) Jj(Ii Ij Jm Jn Js Kq Lx Mm Nu Nv Po Uh) Id(aC bM hP Il jV Kq IK Mn No rC Uh) Jg(Hu Ir Lw Lz
Mh My Ng No Of Oy) Kq(Bg bM Dk Hc Ib Iz Jh Jv Kl Of) Uh(Ax bM cM Fa Fw Gp Jv No Vv Wm) Jt(Hu Lx Lz Mh Ms Ng Nu Og Oy) On(Ir
Lw Lz Mh My Ng Nu Oe Of) Aj(Dc Et Li Nw Un) Lw(Cs Ir Lx Mm Nu) bM(Bb Et Li Ok Pk) Un(aC Cs Oy Wm) Et(Cs Ii Ip) Nu(Ir Jl Jq)
Lx(Hu Ir Oy) Mm(Ir Lz Og) Nv(Hu Og Oy) Nw(aC aN) Ok(Eq Yk) CsJv NoIc Hulj JsjV PkaC aOjB Unconstrained panels with 2 analytes, where 1.0E-4 >= 'model p-value' > 1.0E-5. Contains 3,110 panels of 199,653 total panels evaluated. :
Vt(AA Ad AF aG aK AL aM AN AO AP aR AS aU aV Aw aX aY aZ Ba BB BC bE BG bH bL BN BO bP bQ bR bS bU bV bX bZ cA cB cC
cE cF cG Ch cI cJ cK cL CO Cp CQ Ct CU CV Cw CX cY cZ dA Db DC DD DE Dg dH DI dJ DK DL Dp Du EF Et Fb Fn Fr Fy Gd Gl Gp Ha
Hb Hf hG Hq Hr Hu Hv Hw Hx Ib Ic Id Ih Ii Ij Ik Im In Io Ip Iq Ir Is It Iu Iv Iz Je Jf Jg Jh Jj Jk Jl Jm Jn Jo Jq Jr Js Jt Jy Ki Kn Ko Ks Kx Kz Lh
Lu Lv Lw Lx Ly Ma Mb Mc Md Me Mf Mg Mh Mi Mj Mk Ml Mm Mn Mp Mq Mr Ms Mt Mu Mv Mw Mx My Na Nb Nc Nd Ng Nh Ni Nj Nk
Nl Nq Ns Nv Nw Nx Ny Oa Oe Of Oh Oi Ok Om On Or Ow Oz Pa Pb Pc Pd Pe Pk Po Pz Qa Qb Qc Qd Qg Qh Ql Qm Qn Qt Qu Qv Qw Qx Qy
Qz Ra Rb Rc Rf Rg Rh Ri Rj Rm Sr Ss St Tn To Tr Tt Tv Tz Ua Ub Uc Ud Ue Uf Ug Uk Ul Un Uo Up Ur Us Ut Uu Uv Vh Vi Vo Vp Vv Tj)
Qe(AD aE AF aG aH aI aJ aK AL aM An AO AP aQ AR AS aU aV aW AX aY aZ BA BB BC bE bF BG bH bI bJ bL BN BO bP bQ bR bS bU
bV bW bX bZ cA cB cC cD cE cF cG CH cI cJ cK cL cN CO CP CQ cR cS cT CU cV CW CX cY cZ dA Db DC dD DE dF DG dH dI dJ DK
DL dM dN Du Ed EF Fa Fn Fr Fw Gl Gp Hb hC Hf hG Hq Hr Hv Hw Hx iA Ib Ic Ih Ii iJ Il In Io IP It Iu Iz Jd Jh Jk Jm Jo Kc Ki Kk Kl Kn Kp
Kq Kr Ld Lu Lv Ly Ma Mb Md Mf Mg Mj Mk Mn Mq Mt Mu Mv Mw Mx Na Nb Nc Nf Ni Nr Nv Of Oh Oi Om oN Or Ow Pk Po Ps Pz Qa
Qb Qc Qt Qu Qw Rc Rf Rh Rj Rm Sr Ss St Tn To Tr Tt Tv Ua Uc Un Ur Us Uu Vv Wh Yk Ye Wm Ti Th) Ke(aA Ad AF aH Al aM An AO Ap
Ar As Ba Bc bE bF Bg bH Bo bP bQ cC cF cI cJ cL cM Co Cp Cq Ct Cu Cv Cw Cx dA Db Dc Dd DE Dg Di Dk DL Ed Et Fa fP Fr GL HB HC
Hf hG hP Hu Hv Hw iA Ic Id iH Ii IJ Im In Io iP Iq Ir Is It Iu iZ Jd Jf Jg Jh Ji Jo Jp Jq Ju Jy Kf Ki Kj Kk Ko Kp Kq Kr Kx Ky Kz Ld Lh Li lK
Lu Lv Lw Lx Ly Lz Ma Mb Mc Md Me Mf Mg Mh Mi Mj Mk Ml Mm Mp Mq Mr Ms Mt Mu Mv Mw Mx My Mz Na Nb Nc Nd Nf Ng Nh Ni

Figure 41 Continued

Nj Nl Nm Nn No Nq Nr Ns Nt Nu Nv Nw Nx Ny Oa Oe Of Oh Oi OK Om ON Or Ou Ow Oz Pa Pb Pc Pd Pe Pf Pg Ph Pi Pk Po QA Qd QU Qx Rc Sf Sr Ss tO Uc Uh uM Un Us Uv Vo Vv yJ) Ji(AD al aJ AL An aP AS aU aV aY aZ bA BB BC bE bF bG bH bI bJ BN BO bR bS bU bV bW bX bZ cA cD cE cF cG cH cK cL cN cO CP CQ cR cS cT cU CV cW cX cY cZ DC Dd De dF dG DI dJ dK Dl dM dN Dp Dr eC Ez Fc Fn fR Gb Gc gP Ha hB Hc HF hP Ib iO Iz JD Je Jf Jy Kf Kg Kj Kk KQ KR kS Kx Ky Kz Ld IM nW nY Oa oE oF oH oK Or Ow pF Ph Pi Pj Pk Ps Qg Qh ql Qn Qt Qv Qw Qy Qz Ra Rb Rf Rg Rh Ri Rj Rm Ru Rv rW Sh Si St Tn To TR TT Tv tX Tz Ua Ub Uc Ud Ue Uf Ug Uk Ul Um Un Uo Up Ur Us Ut Uw Ux Va Vb Vc Vh Vi Vj Vo Vp Vs Vu Vw Wb Wc Wd We Wf Wg Wh Yd Yk Tj Ti Th tF) Pj(aA Af aJ aK Al aM aN Ap Ar As Aw aX bA Bc bE bH bP cB cF Ch cI cM Co Cq CU Cv dA dB Dc dD dE DG dH dI dL dM dR eC Ed EF Ex fP Fr Gd gL GP Gz Ha hB hF hG Hv iA Ic iH Ik Im In iO iP Iq Ir Is Iv jD jK Jl Jo Ju Kd Kj Kk Kl Kn kQ KR kS Kx Ld Lh Li lK lO Lx Lz Md Me Mg Mi Ml Mp Mq Mr Ms Mt Mu Mx Na Nd Ne Nk Nm Nn Nr Nu NW NY Oa OE OF Og oH Oi OK oN Ou Oy Oz Pa Pb Pd Pe PF Pk Po Qa Qb Qd Qv Rc Ry Sh Si Tn Tr Uh Uk Un Us Uu Va Vi Vv Wb Wm Tj) Uh(aA aC Ad aF Aj Al aM aN AO Ap Ar As Aw Bn cB cE Ch Cp Cq Cu Cv Cw dA dB Dc Dd dE dL dR Ed Fn fP Fy Gc Ha hC Hu Hv Hw Hx iA Ic iH lJ Ik Il In Io iP Iq Ir It Iv iZ Jd Jl Jn Jp Jq Jr Jt Jy Kd Ki Kl Kn Ko Kp Kq Kr Lh Li Lw Lx Lz Mb Md Me Mi Ml Mq Mr Mt Mx My Mz Na Nb Nc Ne Nf Ng Nh Nk Nl Nm Nn Nr Nt Nu Nw Ny Oa Of Og Ok Om oN Or Ou Oy Pa Pb Pd Pe Pf Pg Pi Pk Po Qa Qd Qh Qu Ra Rb Rc Rf Rg Rh Ri Rj Rm Sr Ss Tn Tr tT Tv Ua Ub Uc Un Up Us Uu Vp Vu) Lj(Ad Aj aK aM aN Ao As aU Aw aX bA BB Bc bE Bg bS bW cC cG Co Cp CQ Cs Cu Cv dA dB Dc DD dE Di Dp eC Ed Ez Fa Fb Fi fP Fy Gb Gc Ha HB HC HF iA Ib Ic iH iP Iz Je Jf Ju Kc Kd Kf Kg Ki Kj Kk Kl Kn Ko Kp kQ KR kS Ld nW nY Oa oE oF oH oK oN Op Ou Ow pF Ph Pi Pk Qg Qh Ql Qm Qn Qt Qu Qv Qw Qx Qy Qz Ra Rb Rc Rf Rg Rh Ri Rj Rm Sr Ss St Tn To Tr Tv Tz Ua Ub Uc Ud Ue Uf Ug Uk Ul Um Uo Ur Uu Uv Ux Vh Vo Vp Vs Vv Vw Zq Tl Wn Th tF) Gc(aC aM cD dR EF eM Et Ex Fp gL hA hB hF hG iB iC iH Ik iO jD jF jG jl Jj jL jP jT JU JV jY Kd kQ kS Li lL lM lN Ml Mr Mw Nc Ne nW Ny oF oH OK oN Oy Oz Pb Pc pF Po Qd Qh Qv Qw Qx Qz Ra Rb Rc Rg Ru Rv Sh Sr Ss St Tn To Tt Tz Ua Ub Uc Ud Ue Ug Ul Um Un Uo Ur Us Ut Uv Uw Vb Vc Vi Vo Vp Vs Vv Wc Wd We Wh Wm Tj Ti Th tF) Mz(aC aN bM Cs eD eF eT eZ Fa fN Fr fY hA hC hG hL hO hR Hu hV hW hX iA iB Id Ih lJ iP Iq Is Iv jD jE jF jG jH jl jK JL jM Jn jO jP JQ JR Js jT jU jV jY lK lL lM lN lO Lv Mh Mi Mp Mr Ms Mt Mx Nh Nj Nl Nm No Nr Nv Nx nY Og oN Oy Oz Pb Pc Pe Pf Po pY qA QB QC qD qH ql qO qP qQ qU qV qW qX qY qZ rA rB rC Un Wm) Id(aF Aj Ar Ax bE cB cM Cq Cs Cu dB dD dK dL Ed Et Fa FN Fp Fw Fy Hb hL hR HV hW hX Ic In JD Jj jK Jl jO jQ jR Jv Jy Ki Kr Ks Lh Li lM lO Lw Lx Lz Mi Mm Mt Na Nd Ne Nk Nm Nn Nr Nt Nw Ny Oa Og Oh Ok Or Ou Oy Oz Pa Pd Pe Pf Pk Po pY Qa qB qC Qd qH qY qZ rB rQ rX rY rZ Sr uG ul uM Un Us uX vT Wm Tj Ti) Lh(aC Aj aN bM dB Fr hG Hv Hx Ii Ij Ik Il In Io Iq It Iv Jg Jk Jl Jm Jn Jo Jq Jr Js Jv Ki lM Lu Lv Lx Mb Mc Me Mf Mg Mh Mi Mj Mk Ml Mm Mp Mr Mt Mu Mv Mw Mx My Na Nb Nc Nd Ne Nf Nh Ni Nj Nk Nl No Nq Nr Ns Nv Nx Oe Of Oh On Ou Oz Pa Pd Pe Pf Pg Po Qb Qc Sf Sh Ss Uu Uy Vc Wb Wh Wm) Jp(Aj aN aO Ax dB dE Ed Ef Fa Fr Hf Hq Hr Hv Hw Hx Ib Ii Il Ik Il In Io Ip Iu Jg Jh Jk Jo Ki Kq Kr Ks Ll Lv Ly Ma Mb Mc Md Mf Mg Mj Mk Mn Mq Mt Mu Mv Mw Na Nb Nc Nd Nf Nh Ni Nk Nl Nq Nr Nv Oa Oe Oh Oi Om On Or Ou Ow Pa Pd Pg Pk Pz Qu Rc Sf Sh Un Uu Vc Vv Wb Yd Yj Yk Wm Ti) Nt(Aj Fr Hq Hr Hv Hw Hx Ih Ii Ij Ik Il In Io Ip Iq It Iu Iv Jg Jh Jk Jl Jm Jn Jo Jr Lu Lv Ly Ma Mb Mc Md Me Mf Mg Mh Mi Mj Mk Ml Mn Mp Mq Mr Ms Mt Mu Mv Mw Mx My Na Nb Nc Nd Nf Ng Nh Ni Nj Nk Nl Nm No Nq Nr Ns Nu Nv Nx Oe Of Oh Oi Om Oz Pa Pb Pd Pe Pf Pg Po Pz Qb Uy) Cs(aC Aj aN Bb bM cM Cv dB Ed Fa Fn Fy Ha Hb Ic iJ Jd Jj Jt Ju Jy Kq Li Ne Nh Nk Nm Nn Nw Og Ok Or Ou Pk Qc Qd Qg Qh Qt Qu Qv Qw Qx Qy Qz Ra Rb Rc Rf Rg Rh Ri Rj Rm Sr Ss St Tn To Tr Tz Ua Ub Uc Ud Ue Uf Uk Ul Um Uo Up Ur Us Ut Uu Uv Vo Vp Vs Vv Wm Ti) Ny(Fr Hq Hr Hv Hw Hx Ih Ij Ik Il Iq It Iv Jh Jk Jm Jo Jr Js Lu Lv Lx Mb Mc Me Mf Mg Mh Mi Ml Mm Mn Mq Mr Mt Mu Mv Mw Mx My Na Nb Nc Nd Ne Ng Nh Ni Nj Nk Nl Nq Nr Ns Nv Nx Oe Of Oh Om On Oz Pa Pb Pc Pd Pe Pf Po Pz Qb Qc tR tT tX yJ) On(aA Aj Eq Hv Hw Hx Ih Ii Ij Ik Io Iq Is It Iv Jg Jh Jk Jl Jm Jn Jq Jr Js Jt Lu Lv Lx Mb Mc Me Mf Mg Mi Mj Mk Ml Mm Mn Mp Mr Mu Mv Mw Mx Nb Nc Nd Ne Nh Ni Nj Nk Nl Nm No Nq Ns Nx Oi Om Oz Pa Pb Pc Pd Pe Pf Pg Po Qa Qb Qc) Qa(Aj bM Fr Hv Hx Ib Ij Ik Iq Is Iu Iv Jh Jk Jl Jn Jq Jr Js Lu Lv Lx Ma Mb Mc Me Mh Mi Mj Mk Ml Mm Mn Mp Mr Ms Mt Mu Mv Mw Mx Na Nb Nc Nd Ne Nj Nm Ns Nv Nx Nr Ns Nv Nx Oe Of Oh Ou Oz Pa Pb Pd Pe Pf Pg Po Qc) Jt(aA aC bM Fr Ih Ij Ik Il In Ir Is Iv Jg Jh Jl Jm Jn Jo Jq Jr Js Lu Lv Lw Mb Mc Me Mg Mi Ml Mm Mp Mr Mt Mv Mw Mx My Na Nb Nc Nd Ne Nh Nj Nk Nl Nm No Nq Nr Ns Nv Nx Oe Of Oz Pb Pc Pd Pe Pf Po Qb Qc) Nn(aC aN bM dB Fa Fr Hq Hr Hv Hw Hx Ii Il In Io Ip It Iu Jh Jk Jm Jo Jv Ki Lv Ma Mb Mc Md Mf Mg Mj Mk Mn Mq Mt Mu Mv Mw Na Nb Nc Nd Ne Nf Nh Ni Nl Nr Nv Of Oh Oi Om Pa Pd Pf Pg Pz Qb Un) Fp(bM Hq Hr Hv Hw Hx Il In Io Ip It Iu Jd Jh Jk Jo Jr Jv Lu Lv Ly Mb Md Mf Mg Mj Mk Ml Mn Mq Mt Mu Mv Mw Mx My Na Nb Nc Nf Ng Ni Nq Nr Ns Of Oi Om Pa Pd Pf Pg Po Rc Sr Up Ur Us Uu) Jg(aA Aj bM Eq Hv Ih Ij Ik Iq Is Iv Jh Jl Jm Jn Jq Jr Js Kq Lu Lv Lx Mc Me Mg Mi Ml Mm Mp Mr Ms Mv Mw Md Ne Nj Nm Ns Nu Nv Nx Oe Oz Pb Pc Pd Pe Pf Po Qb Qc) Un(aN Ar Aw Ax bM dB dK Ed EF Fa Fw Gp hG hP Hu Hv Ib Ic iJ Il In Iz Jh Jj Jv Ki Li Lz Ms My Ne Ng Nh Nk Nm No Of Og Ou Pf Pg Pk Qu Qx Rc Sr Ss To Tr Uu Vv) Fa(aC aF Aj aN Aw bM dB Et Fn Fw Hb Hu Ib Ic Il In Jd Jj Jv Jy Kq Kr Lu Lw Mb Mc Mj Mm Nc Nk Nm Nu Nw Og Ou Oy Oz Pk Qa Sr Ur Wm) Kq(aC aM aN Ao Ar Aw Ba Ch Ct dB Ed Eq Fw Gp Hu Ic Ik Jk Jo Li Mg Mv Mw My Ne Ng Nq Nv Og Oi Om Ou Oy Pg Pk Qu Ss Tn Uc Uu Wm) Mm(aA aC Aj Hu Ih Ij Iq Is Iv Jl Jn Jq Jr Js Lx Me Mh Mi Ml Mp Mr Ms Mx Ng Nj Nm No Nu Nv Oy Oz Pb Pc Pe Pf Po Qb Qc) Lx(aA Eo EW Ij Iq Is Iv Jl Jn Jq Js Lz Mh Mp Ms My Nj Nm No Nu Nv Nx Oe Og Oz Pb Pc Pe Qc Wm Ti) Lw(aC Aj aN Ar Ax bM cI Fr Ih Ij Is Iv Jj Jl Jn Js Lz Mh Mr Mx Nm No Nv Nx Og Oy Pc Pe Po Qb Qc) Nw(aF aM AO Ax bE cB cC cl Cu Cx dA dB Dd dE jD jO Jv lK lM Ou Pk qT qU qV qX qY rA rB Wm) Ok(aC aN cl dB Dr Ef Fc Fi Gb Gd Gn Hp Kl Ps Rv Rx Sf Sh Uy Vb Vc Wb Wc We Wh Yd Zw Ye Tl Wm) Ir(aA Fr Hu Ih Ij Ik Jj Jl Jm Jn Jq Js Lz Mp Mt Nj Nm No Nv Nx Og Oy Oz Pb Pc Po Pz Qb Qc) Nu(aA Fr Hu Ih Ij Is Iv Jn Jr Js Lz Mh Mp Nm No Nv Nx Og Oy oN Oz Pb Pc Pe Qb Qc) Qd(aC aN bM dB hP Hr Ii iJ In Ip Jv Ly Md Mg Mq Na Nf Ni Om Qb rB Wm) Js(aA bM Fr Hu jD Jl jU IM Lz Mh Mp Ms Nj Nm No Og Oy Oz Pb Pc rB) Jj(Al Ax bM Dc Fr Ih Is Jl Jq Ks Lz Nm No Nr Nx Py Qb Qc) Nv(aA Is Iv Jn Lz Mh Ml Ms My Ng Nj Nm No Oe Oz Pb Pc) bM(Ax bA Cu Dc Hb Ij Im Jd Jq Mt Ne Nm Oa Or Pf Qc) No(Hu Ib Ij Jd Jn Jv Nj Nm Nx Og Oy Oz Pc Wm Ti) Et(aC aO Ap Ax dB Dd Dg Dr Du Ef Ic Jv Kl Wm) Li(aC aN dB fP hG Ic Jv Jy lM Qu Uu Wb Wm Th) Lz(aA Fr Ih Ii Ij Is Jn Jq Nm Nx Oz Pc) Sr(aA aC Aw eC jV Rf Rg Rh Ri Rj Rm) Og(Fr Ii Is Jl Jm Jn Jq Nm Po Qb) Nk(Ax Dr gZ Ho pK Vi Wb Zq Xa) Aj(Ax Bb Cu Fr Fy Ii Ij Im) Nm(aA aC Is Jl Jn Qb Sf Sh) Ti(Ar Ax Ed Nb Nr Pe Po) Ij(aA Jl Mp Ms My Oy Pb) Jn(aA Fr Is Jl Mp Ms Wh) aC(Aa Ar Bb Dc Im Vq) Ax(Ic Jd Jv Jy Ur) Zq(aM Eq Kl Mh Ml) Oy(Fr Is Jd Jl Po) aA(Aa Ih Jm Qb Qc) Wm(Fw Hb Mt Po) Hu(Fr Is Jl Po) Jv(Ar Dc Jd) Pk(dB dL iJ) Fw(Hb Jd) Ne(Oa tV) Im(aN dB) Jl(Oz Pc) Jr(jD jV) AatX DltT EwaM FrJq MthP YicD YdjP WbKx KrtO UtUy VchA VhjD OzjB bBdU

Unconstrained panels with 2 analytes, where 1.0E-3 >= 'model p-value' > 1.0E-4. Contains 6,974 panels of 199,653 total panels evaluated. :
Id(aA AD aE Af aG aH al aJ aK AL aM AN AO AP aQ aR AS aU aV AW aX aY aZ BA BB BC bF BG bH bI bJ bL BN BO bP bQ bR bS bU bV bW bX bZ cA cC cD cE cF cG CH cl cJ cK cL cN CO CP cQ cR cS CT cU CV CW CX cY cZ dA Db DC Dd DE dF DG dH DI dJ Dk Dl dM dN Dp eC eD EF eT EZ Fb fP Fr fY Gl Gp gW HA HC Hf hG hO Hq Hr Hu Hw Hx IB iC lH Ii lJ Ik Im Io IP Iq Ir Is It Iu Iv Iz JE JF JG JH jI Jk jL JM Jn Jo jP Jq Jr Js JT JU jY Kc Kd Kf Kg Kj Kk Kl Kn Ko Kp Kx Ky Kz Ld IL lN Lu Lv Ly Ma Mb Mc Md Me Mf Mg Mh Mj Mk

Jr Ju Jy Ki Ko Kr Lu Lv Lz Ma Mb Mc Me Mf Mh Mj Ml Mn Mp Mr Ms Mt Mv Mw Mx My Nb Nc Nd Ne Ng Nh Nk Nl Nr Ns Oa Oe Op Or
Ou Pa Pb Pd Pe Pf Pk Po Pz Qb Qc Qm Qn Qt Qu Qv Qw Qx Qz Rc Rf Rg Rh Rj Rm Sf Sh Sr Ss Tn To Tr Tv Tz Ua Uc Ud Uf Uk Um Up Ur
Us Uu Uv Uy Vh Vv Wb Yk Yl Zq Zw Ye Th) Mz(aF Aj aM aO Ar aW Ax bA BB bE bV cB cC cl cM CU Cv Cx dA dB Dc DD dE dL dR eC
Ed Fw Fy gL gP HB hF Hq Hr Hv Hw Hx Ib Ic iH Ii Ik Il In lO Ip It Iu iZ Jd Jh Jk Jm Jo Jv Ki Kn kQ KR kS Lu Ly Ma Mb Mc Md Me Mf Mg
Mj Mk Ml Mn Mq Mu Mv Mw My Na Nb Nc Nd Ne Nf Ng Ni Nk Nq Ns nW Oa OE OF OH Oi oK Om Or Ou Pa Pd pF Pg Pk Pz qG Rf Rg
Rh Rj rP rQ rS rU rV rW Sr Tn Tr Tv) Ok(Ad aE AF aG aH Al aM An AO Ap aQ AR As aV AW AX BA Bb Bc bE Bg bJ bL BN bP bQ bR bU
bW cA cB cC cE cF cG Ch cL cM Co Cp Cq Ct CU Cv Cw Cx dA Db Dc DD DE Dg Dl DK DL dN Du Ed eF Em Ex Fd fR Fw Gh Gp Gz Hc
Hl Ho Ic Iz Jv Ki Kr Lp Lt Op Or Ou Ow Pk Qu Qx Rc Rt Ru Ry Rz Si Sj Ss Uu Uw Ux Uz Va Vh Vi Vj Vw Vz Wd Wf Wg Yg Yh Yi Yj Yl
Zq Zx Tm Xa Ti Th Yf) Qd(Ad AF aK Al aM An AO Ar AS aU aV AW AX BA BB Bc bE Bg bl bJ bL Bn bS cA cB cC cD cF cG Ch cl cL cM
Co Cp CQ cS Ct CU Cv Cw Cx cZ dA Dc DD dE Dg Dl DK DL Du Ed EfeZ FN Hb HC Hf hG hR hV hW hX iA Ib Ic iH iP Iz JD jV Jy Ki Kl
Kn lK lM Oa Or Ou Pk qA qO qP qQ QT QU Qx qZ RC Rf Rh Rj Sr Ss Tr Ua Ub Uc Ur Us Uu Vv Ti) Js(aC Aj aN eD hA hP Hq HR HV HW
HX iB iC Ih Ii Ij Ik Il In Io Ip Iq Is It Iu Iv jE jF jG JH jI JK jL JM Jn JO jP JQ JR jT Jv jY IK IL IN IO Lu Lv Ly Ma Mb Mc Md Me Mf Mg Mi
Mj Mk Ml Mn Mq Mr Mt Mu Mv Mw Mx My Na Nb Nc Nd Ne Nf Ng Nh Ni Nk Nl Nq Nr Ns Nv Nx Oe Of Oh Oi Om Pa Pd Pe Pf Pg Po Pz
Qb Qc qT qU qV qW qX qY rA rC Wm) Ji(Du EM Eq eT eZ Fb Fd Fi fN FY Gd Gh Gn Gz Hb HL HO Hp iC jO jQ jR jU jV jY Kc Kd Kn Ko
Kp Ks IK IN IO Lp Lt Op pY qA qB qC qD qG qH Ql Qm qO qP qQ qT qU qZ rA rB rO rP rQ rR rS RT rU rV Rx Ry Rz Sj sK sM tN tO tS tU
tV uL uM uN uU Uz vA Vq vT Vz wB wC wD wE wF wG wH wJ wK wL wP wQ yD yH Yi yJ YL zG zl Zq Zw Zx Ye Tm Tl Xa Yf) Vt(aD
aE aH al aJ aQ aW bA bF bl bJ bW cD cH cN cP cR cS cT cW dF dG dM dN DR eC Em Ex Ez Fc Fi fP Gb Gh gL Gn gP gV Gz hB HC Hl Ho
hP iA iH iJ iP iZ Ju jV Kc Kd Kf Kg Kj Kk Kl Kp Ky Ld Lp Lt nW oE oK oN Op pF Ph Pi Ps Rt Ru Rv Rx Rz Sf Sh Si sK tO tR uM Uw Ux
Uy Uz Va Vb Vc vO Vs vT Vu Vw Vz Wb Wc Wd We Wf Wg Wh Yi Yk Yl Zq Ye Tl Xa Yf) Lh(aF aM aO Ax cB cC Ch cl dE Dr Ed EF Eq
Fc Fi fP Gb Gz hA HC hP Hq Hr Hw iA Ib IC iH iJ IP Iu IZ jD Jh jM jO jR jV Kl IK Lp Ly Ma Md Mn Mq Oa Oi oK Om oN Or Ow Pk Ps Pz
QT QU Qx rB Rc Rt Ru Rv Rx Si Sr tO tR TT tX Tz Uc Up Ur Us Uv Uw Ux Uz Va Vb Vh Vi Vj Vv Vw Vz Wc Wd We Wf Wg wQ Yd Yk
Yl Zq Zw Ye Tm Xa Ti Th Yf) bM(aA aC Ad Aj aM aN Ar Bc bE cB cl cM Cp cT Cv dB DD Ed Fb Fr Fw Fy Gl Ha Hv Hw Hx Ic Ih Ii iJ In Io
Iq Ir Is It Iv jB Jh Jk Jl Jm Jn Jo Jr Jv Jy Kd Kf Kn Ko Kp Kr Ks Ld Lv Lx Lz Md Mi Mj Ml Mm Mn Mq Mr Mu Mw Mx Nb Nk Nr Nt Nu Nv
Nx Ny Og Om On Ou Oy Oz Pa Pb Pc Pd Pe Pi Po Qb Qh Rf Rj Rm rS Sr St Tn Tv Tz Uf Up Us Vu Vv Wm) Ax(aC Ad aF aM aN Ar Bb cC
cM Cu Cx dB Dc Dd Dp dU Ed Fn Fy Ha Hb Ib iJ Ir Jf Jq Jt Ju Ki Ko Lx Lz Mc Mm Mt Mu Nb Ne Nh Nl Nm Nn Nt Nu Oa Og Oi Or Ou Pb
Pd Pk Po Qa Qb Qc Qg Qh Ql Qm Qn Qt Qu Qv Qw Qx Qy Qz Ra Rb Rc Rf Rg Rh Ri Rj Rm Sr Ss St Tn Tr Tz Ua Ub Uc Ud Ue Uf Ug Uk Ul
Um Uo Up Us Ut Uu Uv Vo Vp Vs Vv Wb Zq Wn Wm Th) Lx(aC aF Aj aN aO Bb dB Dd DW Ed eO Fr Hb hP Hq Hr Hv Hw Hx Ih Ii Ik Il In
Io Ip It Iu Jd Jh Jk Jm Jo Jr Jv lM Lu Lv Ly Ma Mb Mc Md Me Mf Mg Mi Mj Mk Ml Mn Mq Mr Mt Mu Mv Mw My Nb Nc Nd Ne Ng Nh Ni
Nh Ni Nk Nl Nq Nr Ns Of Oh Oi Om oN Pa Pd Pf Pg Pk Po Ps Pz Qb Qx Sr Wb Zq) Fp(aC Ad Aj aN Bb cM Cv dB Dc Dd Dp Ed Fb Fn fP Fy
Ha Hb Hc Hf hG iA Ib Ic iJ Iz Je Jf Ju Jy Kc Kd Kf Ki Kn Ko Kp Kr Oa oN Or Ou Pk Qg Qh Qm Qn Qt Qu Qv Qw Qx Qy Qz Ra Rb Rf Rg Rh
Ri Rj Rm Ss St Tn To Tr Tv Tz Ua Ub Uc Ud Ue Uf Ug Uk Ul Um Uo Ut Uv Uy Vo Vp Vq Vs Vu Vv Ti) Jn(Dr Eq Gb Hu Hv Ih Ii Ij Ik Il Iq Iv
Jm Jq Jr Lu Lv Ma Mc Me Mh Mi Ml Mn Mr Mt Mw Mx My Nb Nc Nd Ne Nh Nj Nk Nl Nr Ns Nx Oe Oh Oy Oz Pa Pb Pc Pd Pe Pf Po Ps
Pz Qb Qc Rt Ru Rv Sf Sh Uw Ux Uy Uz Va Vb Vc Vh Vi Vw Wb Wc Wd We Wf Wg Yk Yl Zq Ye Yf) Et(Ad AF aG aH Al aM AN Ao aQ
AR As aV Aw aX BA bE Bg Bn cA cB cF Ch cl cM Co Cp Cq Ct CU Cv Cw Cx cY dA Db Dc dD dE Dl Dk Dl Ed Eq Fc Fw Gl Gn Gp Ha Hc
Ib Iz Kd Ki Kn Kr Kx Oa Or Ou Pk Qu Rc Ry Sf Sh Sr Ss Us Uu Uy Vc Vv Wb) Ir(aC Aj aN Hq Hr Hv Hw Hx Ii Il In Io Ip Iq Is It Iu Iv Jd Jh
Jk Jo Jr Lu Lv Ly Ma Mb Mc Md Me Mf Mg Mh Mi Mj Mk Ml Mn Mq Mr Ms Mu Mv Mw Mx My Na Nb Nc Nd Ne Nf Ng Nh Ni Nk Nl Nq
Nr Ns Oe Of Oh Oi Om Pa Pd Pe Pf Pg Sf Uy Wb Wh Yk Zq Wm Ti) Lw(aA Ad aF Al aM aO bA Bb Bc bE bO bS cB cC cL Cp CT CU Cv Cx
dB Dc DD dE Ed eF Fw Hb hP Hu Hv Ii Ik Il Ip Iq It Jh Jm Jq Jr Lu Lv Ma Mb Mc Me Mi Ml Mn Mp Ms Mt Mw My Nb Nc Nd Ne Ng Nh Nj
Nk Nl Nr Ns Oa Oz Pa Pb Pd Pf Pk Pz Wm) Nv(aC Aj Fr Hq Hr Hv Hw Hx Ih Ii Ij Ik Il In Io Ip Iq It Iu Jh Jk Jl Jm Jo Jq Jr Lu Lv Ly Ma Mb
Mc Md Me Mf Mg Mi Mj Mk Mn Mp Mq Mr Mt Mu Mv Mw Mx Na Nb Nc Nd Ne Nf Nh Ni Nk Nl Nq Nr Ns Nx Of Oh Oi Om On Pa Pd Pe
Pf Pg Po Pz Qb Qc Ti) Nm(Af aM aN Ar bA bE cB cl Ct CU dB Dc dD Dr Ed eF Eq Ex Fr Fw Gn Hu Ih Ii Ij Iq Iv Jm Jq Jr Jv Lu Lv Mh Mi Ml
Mp Mr Ms Mt Mx Nd Ng Nh Nj Nl Nr Nx Oa Or Oy Oz Pb Pc Pe Pf Pk Po Pz Qc Rv Sr tT tX Uk Uu Uy Va Vb Vc Vi Wb Wh Ye Wm) Pk(aF
al aJ aK aM aN AR aU aV aW aX aY aZ bA bB bC bE bG bH bL bO bP bQ bR bU bW bX cA cB cC cG cl cK cM cN cO cQ cU cW cY cZ dA
dC dD dE dG dH dl dJ dK dM dR eF Fw gL hC hG iH Il iO Jd Jj Ki Ko Mm Mt Ne Nk Nn oK oN Qa Sr Wm) Lz(aC Ad aN Bb Cv dB Dc Dd
Ed Fb Hu Hv Hw iJ Ik Il In Ip It Iv Jd Jh Jl Jm Jo Jr Jv Ko Lu Lv Ma Mc Me Mh Mi Mn Mp Mr Ms Mt Mw Mx Nb Nc Ne Nh Nj Nk Nl Nr Ns
Oa Og Oy Pb Pd Pe Po Pz Qb Qc qT qU qW qY rB rS Sr Us Wb Zq Wm Ti) Ar(AA Ad aF Aj aN aO Bb bE cM Cu Cv Cx dB Dc Dd Ed Fn Fy
Hb Ic Jd Jj Jt Ju Jy Ki Kr Mt Ne Nk Nn Oa Oy Pd Pe Qa Qc Qh Qu Qx Qy Qz Rb Rc Rf Rh Rj Sr Ss St Tn Tr Tz Uc Uf Uk Up Us Uu Uy Vc Vh
Vi Vu Vv Wb Zq Wm Th) Ij(aC aN dB Dr Eq Fr Hx Ih Ii Ik In Iq Is It Iv Jh Jk Jq Jr Jv Lu Lv Mb Mc Me Mh Mi Ml Mn Mr Mt Mu Mv Mw Mx
Nb Nc Nd Ne Nf Ng Nh Nj Nk Nl Nq Nr Ns Nx Oe Of Oh Oz Pc Pd Pe Pf Pg Po Qb Qc Sf Sh Uy Vc Wb We Wh Yk Ti) Qa(aC aN aO Bb cM
Ct Cv dB Dd Du Ed Hb Hc hG hP Hq Hr Hw iA Ic Ih Ii iJ Il In Io IP It Iz Jd Jm Jo Jv Ki Kl Kn Ly Md Mf Mg Mq Na Nf Ni Oi Om Or Ow Pz
Qb Qt Qu rB Sr Ss Tn To Tv Ur Uu Uy Vv Wb Wh Ye Wm Ti Th) Zq(aC Aj Al aO bO bR bU cD cL cM Cu Cv dD Dg Di Dl Dr Du Ed Ez Fw
Gd Ha Ik Il Io It Jj Ju Jv Kd Ki Kx Mp Mr Nc Ne Nr Ns Ny Oa Oi Or Oy Oz Pb Pc Pe Pg Po Qn Qz Rc Rg Rx Rz Sf Sh Us Uu Uy Vc Vo Vs
Wb Ye) Mm(aN Eq Fr Hq Hr Hv Hw Hx Ii Ik Il In Io Ip It Iu Jh Jk Jm Jo Lu Lv Ly Ma Mb Mc Md Mf Mg Mj Mk Mn Mq Mt Mu Mv Mw My
Na Nb Nc Nd Ne Nf Nh Ni Nk Nl Nq Nr Ns Nx Oe Of Oh Oi Om Pa Pd Pg Pz Sf Sh Wb) Is(aA aN Fr Hx Ih Ii Ik Iq It Iv Jh Jk Jl Jm Jq Jr Lu Lv
Ma Mb Mc Me Mh Mi Ml Mn Mp Mr Ms Mt Mv Mw Mx My Nb Nc Nd Ne Ng Nh Nj Nk Nl Nr Ns Nx Oe Oz Pb Pc Pd Pe Pf Po Pz Qb Qc rB)
aC(Ad Aj Al aM aN Ao Ap bA Bc cB Cp Cu Cv dA Dd Dg Di Dl Ed Fb Fr Fw Fy Gp Hb Ih Ii iJ Iq Jd Jg Jj Jv Jy Kf Kg Kn Ko Mr Mt Mu Mw
Nb Ne Nk Nt Nu Ny Oa On Or Pd Pe Pf Qc Uf Us Wm) Nu(Hq Hr Hv Hw Hx Ii Ik In Ip Iq It Jh Jk Jm Jo Lu Lv Ma Mb Mc Md Me Mf Mi Ml
Mn Mq Mr Ms Mt Mw Mx My Nb Nc Nd Ne Ng Nh Nj Nk Nl Nr Ns Oe Oh Pa Pd Pf Pg Po Pz Uy) Jj(aA Ad Bb Cu Cv Dd Ed Fb Fw Fy Ha Hb
Ip Iq It Iv Jd Jk Jo Jr Kg Kn Kr Lv Ma Mh Mi Mn Mp Mr Mt Mw Mx Nd Nj Oa Oh Or Oz Pc Pd Pe Pf Qh Sr Uf Up Vh Vq Wb Yi Wm Ti)
Jl(aA Fr hP Hx Ih Ii Ik Iq It Iv Jm Jq Jr Lv Ma Mb Mc Me Mh Ml Mn Mp Mr Ms Mt Mw Mx Nb Nc Ne Nh Nj Nk Nl Nr Ns Nx Pb Pd Po
Pz Qb Qc qH qZ rB rS Wm Ti) Nn(aF aM AO Aw bA Bb bE bL cB cC cD Ch cl cM Ct Cu Cv dA Dc DD dE dU Ed Ef Fw Hb HC iA Ic iP Iz
Jd Kd Kk Kl Kn Ko Kr Ld Oa Or Ou Ow Uu Wm Ti) Po(aA Aj aN Fr hG hP Ib Ih Ik Iq Iv Iz Jd Jq Jr Jv Mc Mi Ml Mn Mp Ms Mt Mv Mx My
Ne Ng Nj Nk Ns Nx Oe oN Oz Pb Pc Pd Pe Pz Qb Qc Sr Ur Uy Vh Wb wQ) Jg(Fr Hq Hr Hw Hx Ii Il In Io Ip It Iu Jk Jo Ly Ma Mb Md Mf Mj
Mk Mn Mq Mt Mu Na Nb Nc Nf Nh Ni Nk Nl Nq Nr Oh Oi Om Pa Pg Pz tT tX) Wm(Aj aN Bb Cu Dc Ed Fy Gl Iq Jd Jq Jt Kd Ki Kn Kr Mi Mr
Ne Nt Oa Og On Or Pa Pe Pf Qc Qh rB Rf Sr St Tz Ur Us Uu Ti) Fw(Aj Gz Ib Ic iJ Jf Jv Jy Ki Kk Kn Ko Kr Lu Nk Oa oN Or Ou Qu Qv Rf Sr
St Tr Uf Uk Ur Us Vc Vh vO Vq Vv Wb wE Ti) Jt(aN cl Ct dB Hq Hr Hw Hx Ii Io Ip Iq It Iu Jk Jv Ly Ma Md Mf Mj Mk Mn Mq Mu Nf Ni

Figure 41 Continued

Oh Oi Om Pa Pg Pz Sf Uy Vb) Jq(aA Hu Ih Ii Iq Iv Jm Jr Jv Lv Mc Mh Mi Ml Mp Mr Ms Mt Mw Mx My Nd Nh Nj Nl Nr Nx Oy Oz Pb Pc Pe Pf Pz Qb Qc) On(aN Dr Fr Gb Hq Hr Il Ih Ip Iu Jo Jv Ly Ma Md Mq Mt Na Nf Nr Oh Pz Rv Sf Sh Uy Vc Wb We Wh Yd Yk Zw Ye Ti) Aj(Aa Al Ap bA Bc Cv dB Dd Dg Dl Fb Hb Ih Iq Iz Jd Jm Kg Kn Ko Kr Ks Mt Ne Nx Ny Oa Pd Pe Pf Qc Sr Uf Vq) Nk(aN cl Cu Dc DU Ed EQ fA fB Fd Fi Gb gC Gn jB Lp Oa oD oV oW pH pI Rt Sf Sh Uw Uy Vh Yi Ye Ti Yf) aA(Fr Hu Ii Ik Ip It Iv Jr Lv Ma Mh Mi Ml Mn Mp Mr Mt Mw Mx My Nj Nr Ns Nx Oa Og Oy Oz Pb Pc Pd Pe Pf Pz) Ti(aM Bc cM Cu Dc Dd Du Ha Il iZ Kd Kx Mh Mi Mr Mt Nt Oa Og Or Pf Pg Rg Sf Sr tX Uf Ut Uy Vi Wb Tj) Fr(Eq Hv Ih Iq It Iv Jm Jr Lv Mc Me Mh Mi Ml Mp Mr Ms Mx My Ng Nj Nq Ns Nx Oe Oz Pb Pc Pe Pf Qb Qc) aN(Aa aF bA Bb Cu Dc Dd Ed Jm Mr Mt Ne Nt Nx Ny Oa Pe Pf Qc qT rB rC rQ rW rY rZ sC tV uL wE) Qc(cM Cu dB Dc DD Hu Ih Ii Ik Iv Jr Mh Mi Mp Mr Ms Mt Mx Nd Nj Nx Og Oy Pc Pd Pe Qb) Ny(Du hP Ib Ii In Io Ip Iu Jv Ly Ma Md Mj Mk Nf Oi Pg qA Sf tN tO tS uN Wb wQ Yk Ye Tl) Sr(cM Cu Cv Dc Ed Ha hP Il jD jK jO jQ Jv Ki Kn lK IM Mt Ne Oa Or Oy Pe Pf rB Uy) Ih(Hu Ii Iq Iv Lv Ma Mc Me Mh Mp Mr Ms Ne Nj Nx Og Oy Oz Pb Pc Pd Pe Pf Pz) Wb(aM As bB Cu Du Fy Hf Ii Il Mf Mh Ml Mn Mt Mw Mx Nr Nt Oz Pe Pf Qx Ut Yl) Qb(Hu Iq Iv Jr Lv Mc Me Mh Mi Mp Mr Ms Nh Nj Nx Oe Oy Oz Pb Pc Pd Pe Pf) Il(Du Ed Hb Hc Ic Iq Jd Jv Kn Ko Kr Oa Og Or Qw Rf Sf St Uk Ur Uu Vv) Cu(aF aO Bb cl dB Du Eq Hb hP Ib Jd Jv Ne Oy Ps Sh Uy Vb Vc Vv Wh) Jr(hP iC jE jG jH jK jM jO jQ jR jU jY lK IL IM IN IO Mp qU qW rB) Og(Bb Cv Dc Dd Iq Iv Jd Mi Mp Mr Mt Mw Mx Nr Nx Oa Pe Pz Yi) Mt(aF aO Bb dB Dc Dd Ed Hb Hu Iv Jd Jv Mp Nx Oy Oz rB) Oy(Ad Bb Dc Fy Ii iJ Iq Iv jB Jm Mp Nr Nx Oa Pe Vq) aM(Aa Bb dK Dr DW EO eW Fi Gb Gd Hb Si Vh Yi) Jd(Dc Ed Gp Ha Ic Kd Kl Oa Or Pe Qu Rc Us Uu Vv) Nt(Dr Du Eq Rv Sf Sh Vb Vc Vj Wc Wd Wh Yl Ye) Jv(Al Bb Dd Fy Hb Im Iq Kn Ko Nr Oa Or Qh Uf) Nx(Hu Iq Iv Mh Mi Mp Mr Ms Mx My Pc Pe Pf tX) Aa(cB dA dB dD dL DR eF gL hC hG iA tV) Pe(Hb hP Hu Hx Jm Nj oN Oz Pb Pc Pz Uy Th) Dc(cB cl Ct dB Ed Nb Ne Nh Ou Sf Ur Uu) Mp(Hu li Iv Jm Mh Ml Mr Nj Nr Oz Pc Pz) Mn(Dr dU eM Eq Ex fR Gz Ic Sf Sh Uy) Ii(Hu Iv Mh Ms Ng Nj Oz Pb Sf Sh Uy) Hb(dL Du Ed Ex Fc Gz Oa Or Pf Sf Uy) tX(dB Dl Hx Im iP jM Mf Qm qZ rB zG) Oa(dB iJ In Jy Ml Nl Oi Ou rB Ur) dU(aW bU Lt mE Mw Nj nK Oz Ut Wf) Du(Al Gb iJ kR mE Qh Qy Up Vq) Ed(Cv dB Jy Kn Rf Tr Ur Us Vq) rS(cl dB dE iP Kk Mf qX rQ uM) Sf(Al Dd Dk Fy Im Ng Nr Yi) Sh(Al Dd Dk Fy Ng Nr Ut Yi) Kx(Dr dX Em eP Gb Gd gV Uy) bU(Dr eQ jB nN oW pK Uy Vh) Eq(Ad Ap Dk Fy iJ Ng Ut) Ne(Al Bb Dd Or St Vh Vq) jB(aW bF bN cR mE nK pK) Im(bE dE iJ Ou rB Ye) Kr(qU rX rY rZ tT tV) Uy(bB Dk Mf Ng Nr Vh) qZ(tO tR tS tT uM yJ) Iv(Jm Nj Oz Pc Pz) An(rQ rZ tT tV) Mb(Dw eO eW gV) Pc(Mh Mi Mx Pf) bB(Dr fB Gb oW) cR(oD oT oW pK) dB(bA Bb Fy tV) hP(dA Kn Or Pd) Dl(tO tR uM) Ut(Dr oP Vc) Vh(cM jY Ml) nK(pK Vz Yl) hW(cl Kz Qx) rB(Or St Tz) jM(sH sl sJ) Nr(Hu Th) Mh(Jm Pz) Nj(lq Mr) Yd(hA jY) Qm(tV wF) Vq(cC mS) eW(Bo Lv) gV(aD Ki) nJ(hR IN) tT(iP Mf) qX(uI uM) pK(aW eC) BbNb CwVb DdPf DrMw FyOr GbMl HaOu MsJm IkIq YiYk ZxjD StiJ XacD YemT TljY KkrW KorQ UrUs VcjP VaiC PahA aFbA bSeO dEtV mMlL nIhR

Constrained panels with 3 analytes, where 1.0E-10 >= 'model p-value' > 0. Contains 253 panels of 37,941,150 total panels evaluated. : Ji{Li(Hu Ii Jh Jj Jk Jo Mh Mj Ml Mp Ms Mv Mw My Ng Nq Ny Of Og Om Oy Pb Pc) Nu(Hu Im Jh Jj Jo Lj Lu Mp Ms Mv Mw My Ng Of Og Om Oy Pb Pc Pd Pg) Im(Hu Jh Jj Jk Jq Lz Mp Mv Mw My Ng Oe Of Og Oy Pb Pc Pg) Mp(Fp Hu Jj Lj Lw Lz Ms My Nd Nn Og Ok Oy Pb Pc Qe) Fp(Hu Ik Jj Jq Mc Mj My Ne Og Om Oy Pb Pc) Oy(Et Hu Jj Lj Lw Lz Ms Nn Og Ok Pc Qe) Lj(Et Jj Jp Jq Lw Ms Og Ok Pb Pc) Pc(Hu Jj Jq Lz Mh Ms My Ng Og) My(Et Jg Lu Ms Nn Nw Ok) Pb(Hu Jj Jq Lz Mh Ms Og) Og(Lw Ms Nm Nn Ok) Et(Jh Mv Mw Om) Nn(Hu Jj Mv) Ms(Jj Jo Ne) LuHu McJj YkeF QePg OfOk} Li{Jj(Et Hu Im Ir Jm Lw Mc Mz Nu Nw Ok Oy Pb Pc Qe) Hu(aA Et Im Ir Jp Lw Nw Og Ok Oy Pc) Lw(Ng Nq Og Oy Pb) Nw(Mp Ng Og Oy) Ok(Ng Of Og Oy) Im(Og Oy) EtOy NmOg} Im{Og(Et Fp Hu Iq Ir Jt Lj Lw Lz Nj Nm Nn Nt Nu Nw Ok) Ok(Jj Lj Of Oy) Et(Hu Oy) Jj(Fp Lj) Nw(Hu Oy) LwLj} Lj{Et(Hu Jj Lw Ms Oe Og Oy Pc) Ok(Jj Lw Mp Ms Oe Of Og Oy) Nw(Jj Lw Mp Ms Oy)} Fp{Nw(Hu Mj My) Ok(Jj Og) EtOy}

Constrained panels with 3 analytes, where 1.0E-9 >= 'model p-value' > 1.0E-10. Contains 552 panels of 37,941,150 total panels evaluated. : Li{Im(Et Fp Ir Jk Lj Lw Mc Mp Ms Mv Mw My Mz Ne Ng Nq Oe Of Ok Pb Pc) Ok(Hx Jh Jk Jo Lj Lw Mc Mg Mj Mp Ms Mv Mw My Nq Oe Pb Pc) Oy(aA Ir Jl Jp Jq Jt Mc Mz Nm Nn Nt Nu Og On Pg Qd Qe) Nw(Hx Ir Jh Jk Lw Mj Ms Mv Mw My Nj Nq Of Oz Pb Pc) Et(Jk Mh Mp Ms Mv My Mz Ng Nq Oe Of Og Pb Pc) Lw(cO Ir Jh Jk Lj Mp Mv Mw My Mz Of Pc) Og(Ir Jq Lj Mc Mz Ne Nu Ny Pb Pc Qe) Ng(Ir Jg Jp Jt Mz Nm Nt Nu Pc) Hu(Jl Jq Mc Mz Nn Nt Nu On Pb) Ir(Mj Pb Pc) aA(My Mz Nq) Pb(Jp Mz)} Ji{Ny(Et Hx Im Jh Jp Mv Mw My Mz Nn Nt Nu Nw Ok Om) Ok(Hx Ii Jh Jo Ml Mv Mw Ng Nu Nx Om) Nt(Hx Ii Jo Ml Mv Mw My Ne Ng Om) aA(Hu Jq Mh Mp My Ng Oy Pb Pc) Nn(Hx Jh Ml Mw Ng Of Oh Om) Mv(Jg Jp Lu Mh Mm Mz Nw) Hx(Et Im Jp Mz Nu Nw Pe) Om(Im Jg Jp Mm Mz Nw Qe) Ml(Et Im Jp Mz Nu Nw) Mw(Jg Jp Mm Mz Nw) Ii(Et Jl Mr Pe) Mj(Iq Qd Qe) My(Jp Mm Mz) Ng(Jg Lw Nm) Qe(Jk Pd) Jh(Jp Nw) LzMc NbPc NhbM NjNk IrJq YkiA QdJk PfPg} Im{Nw(Fp Ir Jj Jk Lw Lz Mh Mp Ms Mv Mw My Ng Nj Nq Ns Nu Oe Of Pb Pc Pg) Lj(Hu Iq Ir Jp Jt Lz Mc Mi Mp Ms Nm Nt Oe Oy Pb Pc Pf) Hu(Fp Ir Jj Jl Jp Jt Lw Lz Nn Nt Ok On Oy Pe Pf) Jj(Et Iq Jt Lw Lz Mz Nn Nt Nu Og Oy Pb) Og(Jg Jl Jq Lh Ml Mz Oy Pb Pe Qd Qe) Ok(Fp Jk Lw Lz Mp Ms My Ng Nq Oe Pb) Et(Fp Jk Lz Mh Ms Ng Oe Of) Oy(Fp Jp Jt Lw Lz) Lw(Fp Ng) NgJt} Nw{Fp(Jj Lw Mc Mh Mp Ms Mv Mw Ng Nm Nq Ny Og Oy Oz Pb Pc Pg) My(Ir Lw Me Mh Mp Ms Nj Nm Nt Nu Ok Oy Pc) Lj(Hu Ir Mj Nj Nm Nu Og Ok Pb Pc) Oy(Et Hu Ir Lw Ms Nj Nt Nu Ok Qe) Lw(Hu Mp Ms Mw Ng Og Pb Pc) Nu(Hu Jj Mp Ms Ng Og) Ms(Ir Nj Ok Pb Pc) Og(Ij Nj Nm Ok) Hu(Nt Pc) Ok(Mp Of) NmNg} Ok{Fp(Hu Lw Mc Mj Mp Ms My Ng Nq Of Oy Pb Pc) Jj(Jm Lw Lz Mc Ms Nn Nu Of Oy Oz Pb Pc Qe) Og(Ij Lw Lz Mc Mh Ms Nn Nu Of Oy Oz Pc) Oy(Lw Lz Mc Ms Mz Nd Nn Nu Of Qe) Of(Aa Lw Mc Ms Nn Oz Pb Pc) Ms(Lw Lz Mz Nn Pb Pc) Lj(Hu Mc Mj Pb Pc) LwNg} Lj{Lw(Jg Jj Jp Mm Ms Nn Nt Nu Ny Og Oy Pc) Jj(Jg Jp Jt Mm Nn Nt Nu Ny On) Jp(Mp Ms Nm Nt Oy) Og(Ij Jg Nm On) EtMc OnOy} Et{Fp(Hu Jj Lw Mc Mz Ng Og Oz Pb Pc) Oy(Lw Mz Qe)} Gc{eC(Pa Vs) YkhC} Qe{Aa(Jj Oy) AjNm} Ij{Og(Lw Nm)} AlSfPj FpJjJt MzdNtX Constrained panels with 3 analytes, where 1.0E-8 >= 'model p-value' > 1.0E-9. Contains 1,134 panels of 37,941,150 total panels evaluated. : Nw{Mp(aA Et Hu Ir Jj Jt Lz Me Mh Mv Mw Nd Nj Nm Nn Nq Nt Ny Og Oz Pb Pc Qe) Ir(Hu Hx Ii Jh Jj Lw Mj Mv Mw Nb Ng Nj Nu Ny Og Om Oz Pb Pc Pg) Mh(Et Hu Hx Jj Lw Lz Mj Mv Mw Ng Nj Nu Ny Og Ok Oz Pb Pc Pg) Jj(Et Jm Jt Lw Ms Nj Nm Nn Nt Ny Oy Oz Pb Pc Qe) Mv(Lu Lw Lz Me Nj Nn Nt Nu Ok Oy Oz Pb Pc Qe) Ng(Et Jg Jt Nd Nj Nn Nt Ny Ok Oz Pc Pd Qc) Oy(Hq Ij Jt Mk Mz Nd Nm Nn Pc Pd Pg Qa Qd) Nu(Lw Mw Nj Nq Ns Oe Of Oz Pb Pc Pd Pg) Hu(aA Et Jt Me Ms Nj Nn Ny Ok Oz Pb Qe) Nt(Mw Ne Ns Ny Oe Of Og Pb Pc Pg) Ok(Ii Jh Mc Mj Mw Nj Nq Oz Pb Pc) Mw(Jt Me Nj Nm Nn Oz Pc Pe) Pb(Lz Me My Nj Og Pc Pd Qe) Oz(Lz Me Ms My Nj Ny Og) Lw(Jh Me Nj Ns Pg) Ms(Jt Me Nm Pg Qe) My(Ij Jg Jt Ml Qe) Og(Et Jt Nn Pc Qe) Lz(Mc Mj Pc Pg) Hx(Fp Pc Pe) Ny(Me Ml Pc) Of(Et Nm Nn) Mj(Iq Mx) Nd(Nj Ns) Pg(Me Qe) EtFp NnNq McMl NbIv NjPc IiJi ImJh} Lj{Jj(Ii Ij Ir Is Jl Jm Jn Jo Jq Lh Lx Mc Mg Mi Mp Mz Nd Nm Nv Nx Of Pc Pd Pg Po Pz Qd Qe) Nu(aA Hu Ir Jg Jl Jp Jq Jt Mi Mm Mp Ms Mz Nd Nm Nn Nx Ny Og On Oy Pc) Og(aA Ir Jl Jp Jq Jt Lh Lx Mg Mi Mm Mp Nn Nt Nv Nx Ny Of) Nm(aA Aj Ir Jl Li Lx Mi Mm Mp Ms Mz Nd Nn Ny On Oy) On(Hu Ir Lw Mc Mj Mm Mp Ms Mw My Nq Oe Of Pc) Jg(aA Hu Ir Mi Mp Ms My Nd Ng Oe Of Oy Pc) Mp(Ir Jt Mm Ms Mz Nk Nn Ny Oy Pc) Nt(Hu Li Ne Nk Nn Ny Oe Oy Pc) Jp(Hu Ir Jv Kl Li Mi Nj Pb Pc) Jt(Hu Mj Ms Mz Nd Nn Ny Oy Pc) Oy(aA Jl Lh Mm Nn Nv Ny) aA(Mm Mz Nd Ny Of Pc) Nn(Hu Ir Mi Ms Pc) Lw(Ir Mz Pb pF)

Figure 41 Continued

Figure 41 Continued

Bb Bc bM cB cl Cv dA dB Dc Fa Fr Ii Iq Jk Jl Jm Jt Lh Lx Lz Md Mr Mt Mz Ne Nk Nv Nw Ny Og On Pf Qa Qc) Kq(aF Aw Bo cC Cv Ef Hu
Hx Ib Id Il Jv Kg Ks Lv Mb Ne Nk Nu Pg Qx Vt Wm) Qe(aN Bb cM cQ Cv dB Dd Dg Gc Jg Jp Lw Mg Mm Nh Nk Nl Nn Pb Pd Pj Qb) Ad(Cu
dA dB Li Lw Mt Ne Nk Nn Nu) bM(Bb Dc Ke Li Nw Ok Pj) Jt(dB Li Mt Nk Nn Pf) Pj(Fa Fw Il Lw) dB(Ke Lh Ok) Lw(Li Ok) CvNt GcUy
McLi llKe} Jp{Oy(Ih Ir Is Jl Jm Jq Jt Lx Lz Mh Mp Ms Mz Nm Nn No Nt Nu Ny Po Qa Qd Qe) Lw(Hu Ir Lz Mh Ms Mz Ng Nt Ny Og Pb Pc
Qe) Hu(Ij Ir Lz Mh Nn Nt Nu Ny Qd Qe) Jv(aC Ar Ax Cs dB Ic Id Pj) Lz(Ms Nm Nt Ny Oz Pb Pc) Nt(Ms Ne Ng Og Pb) Nm(Eq Kl Ng Og)
Mh(Pb Pc Qd) Nk(Eq Si Yd) Qe(Kl Ms Og) Cs(Uu Vt) Kl(Kq Pj) Ny(Ms Og) bM(Ne Pk) EfKq GnVp NeYd NgJt IjOg OkPc} Og{Ij(Hu Ir Jg Jl
Jt Lh Lz Me Mm Mp Ms Mz Nj Nt Nu Nv Nx Ny On Pb Qd) Nn(Hu Ir Is Iv Jg Jt Lz Mh Ms Mz Nj Nm Nt Nu Ny Qd Qe) Qd(Ir Jg Jt Lw Mz
Nm Nt Nu Ny Oy Oz) Qe(Ir Jg Jq Jt Mm Nt Nu Ny Oy) Lw(Jg Lh Nt Nu Ny On Qa) Nm(Cs Il Lh Ny On Qa) Ny(Ir Jt Mz Nt Nu) Mz(hP Jt Nt)
Jg(Ir Lz) On(Hu Oy) TiLi GcUy XaoP} Oy{Qd(Ir Jg Jl Jt Lh Lw Lx Lz Mh Mm Mp Mz Nd Nm Nn Nt Nu Nx Ny On Pd) Nn(Hu Ir Is Jg Jl Jt
Lw Lx Lz Nt Nu On Po Qe) Qe(aA Ir Jg Jq Jt Lh Lw Mm Nm Nt Nu Ny On) On(Hu Ir Lw Ms Nu) Jg(Ir Lw Lz Qa) Gc(iZ Uy) Jt(Mz Ny)
bM(Ke Nw) CsVt LwLh} Gc{hC(bG Dg Dk Dl Hc Hx Jt Kr Li Mh Mq Nk Nl nR Pa Pg Qm Rm Vp) Uy(Ar Cs Du Gd Mg Mw Nk Oz Pa Sf Uc
Uu) Nk(iA Mw Ok Po Qe Uk Va) eC(cD Cs Mg pF Pg) Sf(Al aW Il Kd) Qe(Nc Nh Ni Of) iZ(Dl Hc Jt) DuhB GdkR MwVt LifP OkVp bGgP}
Nw{Hx(aA Iv Jt Me Mi Ml Mr Nt Ok Oz) bM(aC aO bE dB Ne Of Pg Pk) Qe(Jk Mj Mw Nq Oz Pd) Qa(Jk Mj Mp Nq Oe) Jh(Iv Jt Me Nm Nt)
Om(Hv Hw In Jn Jq) Pe(Ii Mj Ml Nb Ny) Pg(aA Jt Ns Qd) Ii(Iv Lh Mr) Qd(Mp Nq) Jt(Mv Of) MlaA MwJg} Ok{Qe(Jk Lw Mc Mp My Nq Oz
Pc Pd) Qd(Jk Mc Mj Mp My Nq Oe Oz) Jo(Mp Nd Nj Nn Nt Nu Oz) Qa(Jk Mp My Nq Oe) Lx(Hx Mh Mv Mw) aA(Hu Ml Mp Nq) Nn(Jh Jk
Mc) My(Ij Nd Po) Hx(Mi Pc Pe) Nd(Nq Ns) Ii(Mr Pe) EqVp MjMx MtMv NaPc YkeF QbJk} Pj{aC(aM aN aQ bM cB dA dB dM Gp iH iJ Mz
Nk Vt) Sf(aW Fw Il Jm Kd Ki Nk Nr Uy) Fa(Ic Jo Jt Jv Kl Ou Uu) Kq(Ad Ap Dg Jo Jv Uu) Jv(Cs Id Ki Or) Cs(bM Vt) Pk(bM iJ) WmUu GzrB
MzlK NkUy KliJ} hP{Mz(Af aS aV bG bW cA cF dH hR hV hW Hx Id Il Iq Iu jO Kk lK lL Lw Ly Lz Oz Pb Pd Ug Uh uV) Id(bQ bR bU cA
cK Co dI Jy Lw Lz Mk Nd Oz Pa Pd Pe Pf Rg Tj) MjLh} Nn{Hu(aA Ij Ir Is Iv Jg Jl Jn Jt Lh Lw Lx Lz Mh Mr Ms Mz No Nt Nu Ny On Pc Pe
Po Qd Qe) Ng(Jg Jt Lw Nm Nt Nu) Ms(Ir Jt Qe) Qd(Jk Nq Oe) Ir(Lw Nu) CsVt JvKe PkbM} Ke{Jv(aC Ar Ax bM cB cl Cs dB eF Ic Il tO Wm)
bM(aC Aw cM dB dN EF Ib Il Kl Ne Pk) Ef(dB iJ Kq) Wm(Kl Ne Uu) Il(Aw Iz Kl) KlKq} Cs{Vt(bM cM dB Fw Il Jv Mj Ne Nh Nk Oe Ou Pe
Pg Uh Wm) Uh(bM cM dB Jv Nk Vv) TnWn IlJv} Hu{On(Mh Ms Nt Nu Ny Of) Qe(Jg Jt Nt Nu) Qd(Jg Nt Nu) Jg(Lz Qa) NtNy} Uh{bM(aA
cM Fw Id Pk Rj Vv) Wm(Ne Uu) Id(Jv uM) MztO QetR WnUu PeoN} Ng{Jg(Lh Lw Lz Ny Qd Qe) Nm(On Qe) Jt(Ny Qe) NtNy LwOn aOjB}
Id{jV(aC Hf Or) uM(cQ Qm rC) Jv(Mn No) vT(Kd yJ) MzhW} Li{bM(fP Mc Ne) Ti(Nk Nl) Iq(Lz Qd) LwdH IsJh aApK} Mz{aQ(jQ uM)
cI(hW rB) OfqY UmrB aSIK} Ef{Kq(bM dB Fw Lv Nt Nu)} Qe{NuLw MjdU MyJg dCgV} Du{FwmU aWkI cNmE} aO{jB(Kx Kz Nh)}
fA{Nk(Nx pK) Axcl} Gz{Kr(qT rC)} Mn{YknR cWgV} Ne{WmVt EqmT} Ny{JktX iPyJ} Oz{bU(fB oW)} AdMbgV FyYgmT NolbVt
MyljaA OrcIrB PkaCbM wBjMul Constrained panels with 3 analytes, where 1.0E-6 >= 'model p-value' > 1.0E-7. Contains 7,175 panels of 37,941,150 total panels evaluated. :
Jp{Jv(aF aH Al aN Aw bH bM cB cl cJ Cv Dc Dd eF Fa Fp Fw Gc Gp Hc Ju Ke Ki Kl Li Lz My Mz Ne Nn No Ny Oa Ou Oy Pk Qd Qe Qu Uh
Un Vt Vv Wm) Hu(aA Ic Ih Is Iv Jg Jj Jl Jm Jn Jq Js Jt Kq Lh Lu Lx Ml Mp Mr Ms Mx Mz Nj Nm No Nx Og On Oy Oz Pb Pc Pe Po Qa Qb)
Pj(aC Aj Ap Aw bM Ch Cs dB Dg Ef Eq Fp Gd Gp Ic Id Ik Iz Jg Jj Jo Ki Mg Ne Of Ou Oy Rc Sf Sh Uu Vt Vv Wm) Ms(Ih Ij Ir Is Iv Jj Jm Jn Jq
Jr Js Jt Lh Lx Mh Ml Mp Mz Ne Nj Nm Nn No Nu Nx Og Oz Pb Pc Pe Qa Qb Qd) Og(Ih Ir Is Iv Jl Jm Jn Jq Js Jt Lh Lx Lz Mh Ml Mp Mx Mz
Nj Nn No Nu Nx Oz Pb Pc Pe Po Qa Qb Qc Qd) Pb(Ih Ij Ir Is Iv Jj Jl Jn Jq Jt Lh Lx Ml Mp Mr Mx Mz Nj Nm Nn No Nu Nx Ny Pd Pe Po Qa
Qd Qe) Oy(aA bM dB Fa Ic Id Ij Iq Iv Jg Jj Jn Jr Js Ke Lh Mi Ml Mr Mx Nj Ns Nx On Pd Pe Pg Qb Vt) Iz(Ar Ax bM Cs dB Fa Fp Fw Gp Ic Id
Il Jj Kq Ks Li Mz Ne Nk Nm Nn No Ny Po Qd Qe Vt Wm) Nu(Ih Ir Is Jl Jn Jq Jt Lw Lz Mh Ml Mp Mz Ng Nj Nm Nn No Ns Ny Oe Oz Pc Qa
Qd Qe) Id(aC aF Aw bM dB Fw hP Ib Ic Jh Ki Kl My Ne Nk No Ou Qu Rc Rj Uh uM Uu Vv Wm) Oz(Ir Is Iv Jj Jl Jq Jt Lw Lx Mh Ml Mp Mz
Ng Nj Nm Nn No Nt Ny Pe Qa Qd Qe) Pc(Ih Ir Is Iv Jj Jl Jn Jq Jt Lx Ml Mp Mx Mz Ng Nj Nm Nn No Nt Pe Qa Qd Qe) Kl(Ar Ax bM Cs dB Fp
Fw Ji Ke Kr Ks Li Mz Ne Nn No nT Ny Qd Un Wm Ti) Nj(Ih Ir Is Jj Jl Jt Lw Lz Mh Mp Mr Mz Ne Nk Nm Nn No Ny Qa Qd Qe) Jj(bM Ih Ii Ij
Is It Iv Jg Jl Jn Jq Jr Js Lx Ml Mp No Nx Po Qb) Eq(Ad Ap aS aW aZ Db Dg Dl Nc Ne Ng Qw St To Ug Vc Vh Vp) Mz(aA bM Hc Ir Jn Jq Jr Jt
Lz Mh Ml Mp Ng Nm Nn Nt Ny Qd) Cs(bM Fn Hc Ic Lw Ne Nh Nk Nl Ou Qu Qx Rc Ss Uh Vs Vv) My(Ic Ij Jg Jq Jt Kq Lw Lx Nm Nn Nt Ny
On Po Qd Qe) Ng(Ij Ir Is Jg Jm Jn Jq Lx Lz Mp Nn Ny Po Qa Qd Qe) Ne(aC Aj dB Hc Ic Lz Mh Oa Ou Pk Sf Vt Yd Yk Wm) Ic(aF Ar Ax bM
Ch Fw Hc Jh Li Nm No Qe Vt Wm) Lj(aC Aj aN dB hG iJ Qu Qx Rc Uh Vs Vv Wb Ti) Qe(aN aO Ef Ir Jk Lz Mh Nm Nq Nt Oe Ou Pd) Nn(Ir
Iv Lw Lz Mh Ml Mp Nm Nq Ns Oe Of) bM(aC Aj aO dB Fp Li Nh Nk Ou Uh Vv) Nm(Dg Ef Mh Ml No Ny Of Qd Sh Uu) Gc(Nk Sf Sh Tt Ua
Uc Uu Vb Vs) Ny(aA Ir Mh Ml Mp Ns Nt Oe Of) dB(aC Aj Hc Ji Pk Uh Uu Vv) Wm(Ef Fp Fw Hc Qu Uh Uu Vt) Qd(Aj Ir Jk Lw Lz Nq Oe
Of) Kq(Aw Bg Ch Dk Hc Ib Jh Uu) Ns(Jt Lw Lz Mh Mp Nt Yd) Fw(Hc Ib Ou Qu Uu Vv) Ax(Ou Qu Uu Vt Vv) Lz(Ih Ir Jq Jt Mc) Mh(aA Ir Jq
Jt Nt) Ib(Ke Kr Rj Vt Vv) Hc(Fp Gp Il Nk) Lw(Is Ml Mx) Qa(Jk Nq Oe) Jt(Aj Ml Of) Ke(Aw Ef Gp) aC(Nk Pk Vt) eM(Rg Rv Uu) Ed(Qu Vv)
Nt(Ir Of) AjKs AwFa ChTi DdSh EfUn FpUu GnNk GpUh LxMv MjOa MlMp YjWe JiaO WhnI QuLi OuVt VsnO PkdE} Ji{iJ(aC Aj AO Ap
AW Ba Bg bL cB Ch cl cL Co Cs Ct dB dE dF Dg Dk fP Fw Gp Hc Hu iA Ib Ic Iz Jg Jh Jj Jo Kl Lz Mg Mj Mp Ms Mv Mz Ne Nk Nq Of Og
Om On Ou Pg Pk Qe Qu Qx Rc Ss Uu Vv) Vt(aC aF Aj bM dB Ed Ef Fw Gp Ib Il Jh Jj Ki Lj Mj Mp Ms My Ne Nh Nk Nl Nn Of Ou Ow Oy Pg
Qx Rc Um Uu Vv Yk) aF(aM cB cl dB dD Ef hC iH Ik Iu Jo Ju Lj Lw Mr Ms Nb Ne Nk Nl Of Og Oy Pg Qe Rc Sf Uh Uu Vv Wm) Wm(aC aN
AO Ap Aw Ba Bg Ch cL cM Co Ct Dg Fw Gp Ib Ic Iz Ju Ow Ph Qu Rc Uc Uh Uv Vs) Lj(aC aO bQ cB cC cM dE Ef Fn hB hG Ic iH Ju Ki Kl
oN Ou Qx Rc Rf Rm Sf Uh Uu Vv Wb) aO(aC aM aN cB cl dB dD dH dL hC iH Iu iZ Jo Lw Lx Ms Mt Nb Ne Nh Nk Nl Og Pf Qe) Nk(aM Ao
Ax cB Cs dA dE Ed fP Fw Gl Gp iH Ou Qx Rc Rv Sh Si Ss Uu Uy Yd Yf) iZ(aJ aP aW aY bQ dB dF DK eC fP gL hB Hc hG iA iH Jh Mj Nc
Nh Nl oN Qx) Yk(Ed Ju Jv kE Ny oP Qe Qt Qw Qz Rb Rc Sf Sh Ss Uc Ux Uy Vb Vo Vs Vv Tj) iH(aC Aj aR cM Ef Fw HC Hu Is Iz Jg Jj Jo
Mj Ms Nc Nh Og Ou Oy Pg) Ne(aM cB cl Cs dA Gl Gp hC hP Ju Ou Qt Qu Qx Rc Ss tV tX Uh Uu Vv) Cs(dB Ik Iu Jq Ju Lw Mj Mp Nc Nl Og
Ou Pg Qx Rc Rf Rm Uu Vv) Ef(aC aN bH cM cB cE Fr Rw Il Jd Ki Lw Ms Nl Nn Nt Ok Qe) Rc(aN Ax Ed Fp Fw Id Il In Jd Jj Ki Ms My Nh
Ou Qx Uh Uv) Lw(aC Aj aN bQ cB cC cE Ch cl cL Co dB Dk cF oN Ou pF) Uu(Ax dB Fp Fw Gc Gp Il Jd Jf Ki Ms Nh Nm Pj Qe Qx Uh)
aC(aL aM cZ Gl Gp Jj Jo Jq Nc Nj Nl oN Oy Pg Pk Qe) cB(Aj aN cC Ik Jj Jo Ju Mp Ms Nb Nh Og Oy Pg Qe) dB(Af cl Ed eF Ik Jq Ju Ms Nc
Oe Of oN Pg Uh Vv) Fw(Aj Ic Jj Ju Ki Kl oN Ou Ow Oy Pg Qu Sf Ss) Sf(Al aY cV Dd Gc Il Jm Kd Mj Mp Nm Pj Qn) Ou(Ax Ed Fa Gp Id Ik
Il Jj Ju Oy Qe Uh Vv) Nh(aM cl dA dE dH dL Gl Gp hG Ju Ss Uh) jO(hP Jv qA rQ sC sM tR tX uN vV wK zH) Aj(aM bW cC cM Cv dE Gp Li
Nc Nn Pg) oN(cM cU dL Lx Lz Mz Pa Pe Pf Po Tj) Ju(Ax bM cl Gp Id Il Ki Ms Vv) dE(cl Iu Jj Jo Ms Of Og Oy Pg) Qx(bM Fp hC Jj jV Nl Ss
Vv) Gp(Ed Jj Ki Uh Um Uv Vv) aM(cl dK Ik Mp Og Oy Pg) bM(eC Ed Ic Jf Ki Uv Vs) Vv(aN Ax Ed Il Ki Uh) cl(aN cM Ik Nl Oy Pg) Ax(Jo
Mc Nl Ss) Id(hP Jh jV Ki) Qe(Ch cM Co Kl) Uh(Aw Ki Oy Pg) Uy(bU Db Rm Vp) aN(Ik Nl Of Og) hC(Hc hG Mj Oy) Wb(Mh Ps Vp) eF(cM
Mz Nl) tX(dN jM rA) tR(oE rA rS) Aw(Nb Sr) Co(Mt Pf) Fa(Jv Mj) Nm(Ap Dg) Il(Ss Tn) Kq(Iz Kl) bQ(Mt Pf) cC(Jo Oy) dA(hP Pg) hG(Io
Nc) EdQu McRg YdgC SrRf JvfP cRtO dLiA tTrA wEqI} Pj{Aj(Al aM As Ax Bc bW cM Cq Cs Cu Cv dA dB Dc dG dL Fb Fp Fr Gp Ii iJ Iq Ir

Cs(aF aM aN aO Aw Bo cB cE Fn Fw Gp iJ Il Io It Jj Ki Kl Mc Mj Mk Nc Ne Nh Nl Nq Oi Ou Rc Uu Vs) Jv(aC Ar Ax dB Dc Dd Fp Fw iA iP
Jj Kq Lz No Qd Qe Un Vt Vv) cM(Ax dA dR Fp Fw Gp Ic iH iZ Kl oN Pk Qe Uu Vt) Fw(Aj aN Aw cB cE dB Gp Ic Jj Ki Oy Pg Vv) Kq(Aw
Dk Ef Ib Iz Jh Kl Tn Uc Uu) Fp(dB Gp Jj Ne Rc Uu Vv) Vt(aC cB dB Il Lz Ne Oy) Qe(Aj Gp Jj Ou Uu Vv) Pk(aC aN dB hG iJ oN) Ax(dB Gp
Ou Uu Vv) Jj(dB Dd Gp Hw) Fa(Aw dB Mj) Vv(Aw iJ iP) tT(aW fP jO) oN(Lx Pf Po) Nm(Aj Uu) Mc(Li Rg) iA(dL Yk) tO(cH Dl) BotX
DcUu EddB PoOy GpaC IlaN WncF dAhP} Oy{Jg(aA Hu Ih Ij Iq Is Iv Jj Jl Jm Jn Jq Js Jt Lh Lx Mh Mi Mp Mr Ms Mx My Nd Ng No Nt Nu Nv Ny Og On Pd Pe Pf Pg Po Qb) Jt(bM Fr Ir Jj Jl Jn Lh Lw Lx Lz Mm Mp Ms Ng No Nt Nu Nv Nx Og On Po Qa Qb) Fp(aA Fr Ii Ij Ir Is Jl Jm Jn Jq Js Lh Lx Mp No Nt Nu Nv Nx Ny Po Pz Qa) On(Ij Lh Lx Lz Mh Mk Mm My Ng Nj Nm Nq Ns Nt Ny Oe Of Pc Pd Pe Pg Po Qa) Lh(AA bM Hu Ih Ij Ir Is Jl Jn Lx Lz Mp Ms Nm No Nt Nu Ny Og Qa) Qe(aN cM Cv Dd Hu iJ Jl Jn Lx Lz Mp Ms Nj No Nx Pd Pf Vt) Nt(Fr Ij Iq Ir Is Jl Jq Js Lw Lx Lz Mm Nv Ny Qa Qb Vt) Qa(aA Hu Ir Jj Jq Lw Lx Lz Mm Mp Nm No Nu Nx Ny Og) Vt(Ar Ax bM Et Fw Il Jd Kq Li Mt Ne No Nr Nu Pf Wm) Ny(aA Hu Ir Jl Jn Jq Js Lw Lx Lz No Nu Pe Po) Ij(aA Jj Lw Lx Lz Mk Mm Mp Nd Pd Pf Pg Po) Nu(Ir Is Jl Jq Js Lw Lx No Nv) Mm(Ir Is Jl Lw Lx Lz No Po) Aa(Iv Jl Jm Jr Ms Oz Pf) Nv(Hu Ir Jj Lw Lz Nm Og) bM(Bb Et Jd Kq Li Ok) Un(Fw iJ Il Ou Wm) Lw(Fr Ir Js Lx) Lx(Ir Jl Jq) Fr(Hu Ir) Jj(Ii Jm) Ok(dB Yk) jB(aO bN) CsEt FwJd IdIl JhKq NwaN} Jj{Mm(Hu Ih Ii Ij Is Iv Jg Jl Jn Jq Jr Js Lw Lx Lz Mh Ml Mp Mx Nm No Nu Nv Nx Oz Pc Pe Po Qa Qb Qc) Jg(Hu Ih Ii Ij Ir Is Jl Jn Jq Js Jt Lx Mh Mp Mx My Ng No Nt Nu Nx Og Po Qb Qc) Jm(aA bM Fr Ij Ir Is Jl Jn Jq Js Lv Lw Lx Lz Mp Ms Nm No Nv Nx Og Oz Pc Po) Nu(Fr Ih Ii Ij Iq Ir Is Jl Jn Js Lw Lx Lz Mp Nm No Nv Nx Pc Po Qb Qc) Jt(bM Ih Ii Ij Ir Jl Jn Jq Js Lw Lx Mh Ml Mp Ms Na Ng Nj Og Pc Po) Nt(Hu Ih Ii Ij Is Jl Jn Jq Js Lw Lx Lz Mw Ne Nv Nx Pc Qb Qc) Qa(Hu Ii Ir Jn Jq Lw Lz Mc Ne Nm Nx Og Oz Pb Pc) bM(Bb Cs Dc Et Fp Ij Im Kq Ks Lh Nm Nw Ok Pk Qe) Nv(Hu Ij Ir Jn Lw Lz Mh Ml Nj Nm Oz Pb Pc) Ii(Hu Ir Lw Lz Mh Ms Og Oz Pb Qd) Ij(Hu Jl Jn Lw Lx Lz Mp Ny Og Pb) Js(jU jV Lw Lz Mc Ms Nm Nx Pc) Qe(aF aN aO cM dB Jv Ou) Jn(Lw Lx Lz Nm On Po) Ny(Hu Is Iv Lx Qc) Nm(Cs Lz On Qb) Lw(Cs Ir Lx Lz) Kq(Gp Jh Jv Kl) Lh(aA Hu Mc Nx) Fp(Dd Ih Vt) Nx(Ir Lx Lz) On(Mc Og) CsJv TiLi LxIr LzJq IlVt aOjB} Aj{Ad(aC aF aM aN aQ aV bC bH bR bW cA cB cC cI cU dI Et Fp Ii Im Jm Jt Lh Lx Lz Md Mi Mq Nc Nd Nh Nl Nt Ok Oz Pb Pd Pe Pf Po Qa Qc Qd) Jt(aC aF Al aM aN Ar As Ax bH bW cB Cs CU dA dE Et Fr Im Iq Jm Lw Lx Lz Md Mq Mu Nc Ne Nh Nl Nt Ny Ok Oz Pa Pd Po Qa Qd) Et(aF Al Ax cB Cs Cu Cv dA dB Dc Dd Fp Im Iq Ir Jm Li Lw Md Mi Mt Nb Ne Nt Pd Pe Pf Po Qa Qc Qd) Ok(aF aH aN bH bW cB cC cM Cv dA Dc dK Il Jm Li Mc Mi Mt Ne Nh Nk Nt Pd Pf Qd Yk) Qe(Aa bC bM Fn Id iJ Jd Jv Kg Kq Ou St Un Vt Wm) Nm(cM Fb Fw Gl Ij Jg Jn Ks No Pe Pk Po Un Vt) Ne(Cu Dc Ii Lh Li Nw On Qa Qd Un Vq Vt) bM(Cu Ii Ij Im Jg Ks Lh On Pk Qd Un Vt) Li(Bg Cv dB Dc fP Iq Jy Nk Nt Qd Vt) Vt(dB Fp Fw Il Jd Ks No Nt Wm) dB(Bb Cu Cw Dc Nw On Qd Un) Kq(aH aO aZ bQ Jh To Ug) Cu(aF Bb Cv Nh Nk) Qd(cM Cv iJ Lw Nk) Un(Fw Il Kg Ks Wm) Nt(Bb Dc Iq) Nk(Dc Fa Qa) Id(Fy Il No) Il(Fa Jd) LwNw NhQa} Fp{Hu(aA Fr Ih Ii Iq Is Jl Jm Jn Js Lx Lz Mc Me Mg Mi Mp Nd No Nq Og Oz Pc Pe Pz Qa) Pc(aA Ir Is Jl Jn Jq Js Lh Lz Mc Mp Nm No Nt Nu Nv Nx Og On Pz Qa Qc Qe) Mc(aA Ir Jg Jl Jq Js Lh Lz Mp Nt Nv Nx Ny Og On Pz Qa Qc Qe) Nu(aA Ih Ir Is Jl Lh Lz Mp Ms Nd Ne Nm No Nx Ny Oz Pb Qe) Og(Ih Ii Iq Is Jl Jm Js Me Mg Mp No Oz Pz Qa Qc Vt Wm) Pb(aA Ir Jl Jm Jn Jq Lh Mp Nm Nt Nv Nx Ny On Pz Qa Qe) Mj(Ih Iq Ir Is Jl Jq Lh Mp Nv Nx Ny Qa Qe Un) Ms(Ij Ir Jn Jq Js Lh Mp Nt Nv Nx Ny Qa Qd Qe) Jg(aA Ik Jq Lz Mp Mv Nd Ne Nm Oe Of Oz Qe) Vt(aC aF bL bM dE Ib Nm Ou Pe Pg Qx Ti) Oz(aA Ir Jl Jq Lh Mm Mp No Nv On Qa Qe) Ne(Lh Mp Nt Nv Ny On Qa Qd Qe Wm) On(Ir Jh Jk Mp Mv Mw Nk Oe Of) Nt(Ik Ir Jq Nd Nk Ny Qe) Mp(Jq Lh Nk Nx Ny Qc Qe) My(aA Ij Jq Nv Nx) Nk(Ir Nm Nv Ny Qd) Ir(Nv Ny Qd Qe) aA(Ih Jm Lh Pz) Wm(Et Nw Qd) Lz(Jq Nx Ny) bM(Et Nw Pk) Qe(Jq Mm) Jv(Jd Un) NdJq NgNv IjOe} Qe{Hu(aA Ij Ir Jl Jn Jq Lh Lw Lx Lz Mm Mp Nm No Nv Nx Ny Og On Oz Pc) Ms(Ir Jg Jn Jq Jt Lh Lw Lz Mm Mp Nm Nt Nu Nx Ny On Oz Pb Pc) Lw(aC aN bS dB Ir Jg Lz Mm Ng Nt Ny Ou Oz Pb Pc Pd Pg) Pc(aA Ir Jg Jq Jt Lh Lz Mh Mm Mp Nm Nt Nu Oe Og) Jg(aA Ir Jh Jk Lz Mh Mv Mw Nq Oe Of Pb Pd) Nu(Ir Jq Jt Lz Ng Nm Oe Oz Pb Pd Pg) cM(aC aN bM cI eF Iu My Nb Ne Of oN) Mm(aA Ir Jq Lz Mh Ng Nj Oe Oz Pb) Pb(aA Ir Jq Jt Lh Lz Nm Nt Ny) aN(aC aF Ne Nh Nk Nm Of Og Oi) aA(Mh My Ng Nm Ny Oz Pd Pg) Lz(Jq Jt Mc Nj Nm Ny Oz) Og(Dd Lh Nj Nx On Oz Wm) My(Jq Jt Lx Nm Nx On) Ne(aC bM dB Nt Ou Vt) Jv(Cs Id Ki Ou Vt) Et(Ap Dg Ef Kl) Nt(Ng Oe Pd Pg) Ir(Mj Ny Oz Pd) Jt(Nj Nq Oe Pd) Ng(Lh Ny On) Nk(aC Nj Ye) Id(hP In Ou) Kq(Ef Kl Tn) Vt(Ou Pg Wm) Nm(Mh Pd) Iu(aM dB) Ny(Nj Oe) AwNb CsNh TiRm ImLh OeOn} Id{uM(aV bH bQ bR bS bU cA cC cF cG cK cL Co Cq CU dA dH dI Gl Il Jl Jy Kq Lw Lz Mi Mk Mp Mq Mt Nd Ns Ny Oz Pa Pd Pe Pf Ph Po Qh Rg rQ Tn Tr Ul Un Up Us Ut vT Vu wE Wm Tj) hP(aC As aY bE bH bS bW cC cD cG cL cN cO cP CQ CU cV dD dG dH dK Hq Il iO Jl Js jY Kd Lh lK lO Lx Mi Mp Mt Mu Nu Ny Or Pb pF Pg Po Qd Ql Tr Us Wm) jV(aX bG bH bR bZ cF CU dB fP hG Il Jr Js Jy Kq Kr kS lK Lv Lx Lz No PF Rg) Il(aC aN bM Cs dB Hv Jd Jv Nk Ou Vt) Jv(aC Cs dB Et Jd Kq Lh Nr Nw) rC(bC cI fP iA Kd Mp nW Qd) Kq(Dk Ef Ib Iz Jh Kl Qu) No(Aw bM Ib Ki Ou Qu) bM(Aa aC Jd qY uX) hX(cF Lz Oz Th) Hf(lK lM lO) rB(Or Tn Tr) uX(dH Im Un) cR(oW qY) lK(cV Kd) uI(bJ Im) McLi MwIb NkfA KrTk KzjK QmwF dDhR uYvT} Og{Jg(AA Hu Ih Is Iv Jl Jm Jq Js Jt Lh Lx Mh Mp Mx My Ng Nm No Ns Nt Nu Ny Of Oz Pe Po Qa Qb Qc) Jt(Fr Ir Jm Jn Lh Lw Lx Lz Mh Ml Mm Ms Nj Nt Nu Nv Nx On Oz Pc Po Qa Qb Qc) Ny(aA Hu Ih Iq Is Iv Jl Jq Lh Lx Lz Ml Mm Mp Nj No On Pe Qa Qc) Nm(Aa aC Ir Is Jl Jm Jn Jq Js Lw Lx Lz Mm Nt Nu Nv Nx Po Qb) Nt(aA Ir Is Jm Jq Js Lh Lx Lz Mm Ne Nv On Pc Qa Qb Qc) On(Ir Lz Mh Ml Mp Ms Ne Nj Nq Ns Nu Of Oz Pc Qa) Lh(aA Hu Ih Ir Is Lz Ms Nu Oz Pb Pc Qa Qd Wm) Lw(Fr Il Ir Is Jm Jn Js Lx Mm Nv Po Qb) Nu(Ir Is Jl Jm Jn Jq Js Mm Nv Nx Qa) Qa(Hu Ij Ir Jq Mm Ne Oz Pc) Aa(Fr Mf Mv Pd Po Qc) Mm(Il Ir Is Jq Lz Qd) Qd(Hu Mh Nx Pc Wm) Ij(Jn Jq Jr Qc) Vt(Il Ne Wm) Ir(Lx Nv) bM(Bb Li) nK(Yl Xa) CsJv HuNv JmaA} Hu{Jg(aA Ih Ij Ir Is Iv Jl Jn Jq Js Jt Lh Lw Lx Mh Mm Mp Mr Ms Mx Nd Ng No Nt Nu Nv Nx Ny Of On Pc Pe Po Qb) Ny(aA Fr Ij Ir Is Jl Jn Jq Jt Lh Lv Lw Lx Lz Mi Mm Mp Mr Ms Mt Nm No Nq Nu Nv Nx Pe Po Qa Qd) Nt(aA Fr Ij Iq Ir Is Jl Jq Jt Lh Lw Lx Lz Mm Ne Nv Pc Qa Qb) Qd(aA Hq Ij Ir Jt Lh Lw Lx Lz Mh Mm Mp Nm Nx On Oz Pc) Ij(aA Fr Jl Jt Lh Lw Lx Lz Mm Mp Nu Nv On) Lh(aA Ih Ir Is Jt Lw Lx Lz Ms Nu Pc Qa) Nu(Fr Ir Is Jl Jq Jt Nv Qa) On(Ir Lw Lz Ml Mm Mp Mr Pc) Jt(Fr Lx Lz Nv Qa Qb) Ir(Fr Lx Mm Nv Qa) Lw(Lx Nv Qa) Mm(Is Lx Qa) Kq(bM Kl) LzNv QaaA} Vt{Bc(aC bR cA cG cK dA dI Il Jy Lw Mi Nd Oz Pa Pd Pf Tr Wm Tj) Ne(aC Ar Ax bM dB Ed Fw Il Jv Kq Li Lx Lz No Nr Oa Ou Qv Th) Il(aC aN Ar Ax bM dB Li Mg My Nf Nh Ou Pe Pg Um Ur Wm) aC(aF bM cM Cs dB Jv Li Lz Nk Nm Nt Nu Pk Qx Sr Wm) Kq(Dk Ef Ib Iz Jh Jv Kl My Of Ou Pg Tn Uu) Wm(bM cM Ed Fw Kr Nf Nh Ou Pe Pg Um Ur) Ou(Ax Ed Fa Fw Kr Lh No) bM(Ax cM Fw Li Pk Qg Um) Cs(aP bH dE dK Fn hG) Jv(Ar Ax Jd Kr Li No) Pg(Fw Kr No Nt Pf) dB(Ar Ax Ed Li Pk) Th(Hx Nk Nl Po) Ti(Ed Li Qv) Ok(Ps Yk) bS(Mi Pf) AxcM DdDu FwaN LzQx McLi MnIb} Qd{Ms(Ir Jg Jn Jq Jt Lh Lw Lz Mm Nm Nt Nu Nx Ny On Oz Pc) Lz(Jg Jt Lw Mc Mj Mm Nk Nm Nu Ny Oz Pb Pc) Nu(Lw Mh My Ng Nq Oe Oz Pb Pc Pd Pg) Mh(Aa Jg Lw Mj Mm Nm Ny Oz Pb Pc) Nt(Lw Ne Ng Oe Oz Pb Pc Pd Pg) Jg(Jh Jk Mv Mw My Nq Oe Of) Jt(Mj My Ng Nq Oe Of Pb Pc) Lw(Ng Nq Ny Oz Pb Pc Pd) Lh(Jk Mj Ng Oe Of Pb Pc) Mm(Ir Jk Ng Of Pb Pc) Ny(Jk Ng Nq Oe Pb) On(My Ng Nq Oe Of) Mj(aA Iq Ir Pe) Ir(Oz Pb Pc) Oe(Jn Lx Nx) Aa(Of Pc) Nm(My Ng) WmUu MpPc NjNk PdaA} bM{Pk(aG aK aU Ax Bb cM Cs dB dD dK Fw Hb iJ Il In Jd Kq Kr Ld Lh Li Mm Ne Nk Nm Ny Ok Or Pf) Li(aC aN aX bA bE cB cM Cv dB eF hG iJ In Jv Jy Lw Nh Nk Nl Nw Of Oi oK oN) Aa(Cu Cv Dc dI Fa Ha Hb Ic Jv Ki Kq Qh Qz Ss Uk Un Uu Vu Wm) Nw(aF aN aP cI Cs dN Ef Jv Lw Nh Nk Pc) Kq(Dk Ib Iz Jh Kl Of Ss) Cs(Bb Et Jd Jv Un) Bb(aC Ne Of) Et(Ne Of) DcNe FwJd JoJt OfOk} Aa{Ms(Fr Iq Iv Jl Jr Lh Me Mh Mp Nm On Pc Pd Po Qa Qb Qc) In(Ih Iv Jm Jr Lh Me Mh Mp Mq Nm Nx Pc Pd Po Qa Qb Qc) Pc(Fr Im Jr Mb Mh Mm Mp Mt Nt Oz Pd Pf Po Qa Qc) Mb(Jl Mc Mm Mp Nd Pd Pf) Jr(Fr Im Lu Lw Mm Nm Qc) Of(Fr Jg Lh Nv On Qa) Mc(Nm Pd Qc) Qc(Lu Pd) Pa(Lx Pf) NmMr MfIk MuMw NkNl

Figure 41 Continued

KlKq fPtV} Ng{Jg(aA Ih Ij Ir Is Jl Jm Jn Jq Js Jt Lx Mh Mi Mm Mp Mr Nd Nm No Nt Nu Nv Nx On Pc Pd Pe Pf Po Qa Qb) Jt(Fr Ir Jl Jn Lh Lw Lx Lz Mm Mp Nd Nt Nu Nv Nx On Pc Pe Po Qa Qb) On(Ir Lz Mh Ms Nt Nu Ny Of Pc) Nm(Lh Nt Nv Ny Qa) Nt(Lh Lw Mm Qa) Lw(Lh Nv Ny) Nu(Lh Ny) EqiJ LhNy} Kq{Kl(Aw Cs Dg Dk Et Fw Hc Hf Ib Iz Jd Jh Jv Ko Li Lu Lv Mw My Ne Nm Nu Ok Ou Pg) Ef(aN cC Cs cW Gp hG Ic iJ Jd Jv Kz Na Ne Nm No Nr Pg Qy Sr Un Up Wm) Iz(Ar dB Fw Gp Ic Li Lv Ne Nk Pg) Jh(Ar Cs Fw Lv Ne Nk Pg) Jv(Ar Cs dB Ib Ic) Fw(Dk Qu) Ib(Li No) AwSr WmUu TnLi YdgC} Lw{Ny(Ir Lz Mh Ml Ms My Nj No Nt Nu Pb) Li(aC aN aO Cs dB eF fP iA oN pF) Lh(Ir Lz Ms My Nt Nu Pb Pc) Lz(Jg Mm Nt Nu On Pc) Ir(Jg Lx Mm Nt Nu) Jg(Mh Ms My Of) Cs(Et Ne Nk) Nu(Jn Pc Qa) Nw(aC aN aO) On(Mh Ms My) Nt(Pc Qa) Nofb MhMm QaPc} Et{Cs(Dg Ic Jv Kl Ne Nh Nk Of Uu) Mp(Ij Js Lx Nq Ns Po Qb) My(Jl Js Jt Mi Nm Nx Qc) Mv(Ij Lh Mi Mr On Pe) Mw(Lh Mr Mt On Pe) Hx(Lx Mr Po) Jh(Ij On Po) Nq(Ij Qb) Ii(Mr Pe) aA(Me Nu) AxKl DrNk NmMg NsJr LxNy MjIq aCcB aOjB} Ms{On(Ir Jk Jn Jt Lz Mh Ml My Ne Nk Nm Nq Nt Nu Ny Oe Of Oz Pb Pc) Lh(Ih Ir Is Jn Jt Nm Nt Nu Ny Pb) Jt(Lz Mm Nu Ny Qa Qb) Ny(Ir Jn Jq Lz Nt) NuJq LzJg MmIr} Li{Ti(aM aQ cM Cu dA Db Gp Hx Io Jv Jy Lz Ne Nr Oi Or Pk Rf Rg Ur Uu) Mc(aC aN Cs Jv Qw Rg Un Ur) Qu(fP iJ Il Ne) pK(cM kF Kn Rf) fP(Jv Uu) TjoN JksF RmpH PfcO} dU{bL(Tz Ua Ub Uc Ue Uk Um Uo) Mw(bH hG Ib Jf Nk Vs) Ut(bH bX Gp mE Oi Po) bU(fP Ha nN Qw Ua Vs) Nj(Im nK Nr) bX(Ss Tv Uu) Ha(Gp mE) Qv(aW nK) Kl(Cw Iq) AxmE QcKr QyaW bBoW} Jg{My(aA Ij Ir Jq Js Lh Lx Lz Mh Mr Nt Nu Ny On Pe Po Qa Qb) Lz(Ir Jq Mc Nu Ny Of Oz Pb Pc) Mw(Im Lx Po) Qa(Jk Oe Of) Mv(Im Lx) MhPb ImJh IrOf UofB} Cs{Jv(Bb cM Cv dB Dc Dd Fw Hb In Jd Jy Ki Lh Mu Ne Nh Nk Nm Nw Un) Il(Qu Qw Un Uu Vv) Un(Mj Ne Nk Ou) Nm(Jo Oi Uu) Nk(Tr Wm)} Ny{Nt(aA Ir Lz My Ne Ns Oe Pb) Jt(Lz Mg Mh My Nu Oe Of Pb) Lz(Ir Jq Mc Nj Nm Nu) Jk(sF tN tT) Nu(Ir Jq) Lx(Im My) MmIr MyOn NeyJ YkOk} Ok{Yk(Ar Aw Eq gP Hb iP kP Oi Oz Pa Pc Rg Un Uw Vp Vs) Nk(Eq Ps Rx Sf Yd) Vp(Dr Gn Rv Wb Wh) Eq(Cx Qn Rm) MhWb RvRm OfdB} jB{aO(aI aM bB cF cM Db Ex Hb Hv Ii In Jk Jn Jr mE Mk mU Nc Nl Pc Qm Qn Rg Rm Ur Uv Vp Vs) NkKl UkaW nKpF} Im{Mw(Mi Mr Mt Nb Pa) Lv(Ne Pd Pg) Po(Hx Jh) Nq(Iv On) My(Mr Nx) Lh(Hx Ii) aC(aN dB) NsOz LxMh MjMx MpOn MvPa NcNk dBwE} Nk{Dd(pK Sf Sh) Nt(Eq Uy Wh) Il(Hl Sf Yl) Ti(Nr Pe) Mn(Sf Wb) aC(Nw Pk) gZ(Mw Nx) pK(bN Uu) IjTl WbKx WhJn eQmE} cR{oW(aJ Ic Jf Ql Qy Tv) oD(Jd Kd mI To Ul) pK(Kd nN Qu To) Jf(fA gZ) MnoT TvgZ YenA RumU YlnK UnvA} aC{Nw(aF aN aO cB dB Ne Nm Pk) Pk(bW cC dB Iu Mm Nm) Un(Jv Wm) NmcB} Ir{Mm(Lx Lz Nt Nu Oz Pb Pc) Nu(Oz Pc Qa) Lh(Pb Pc) NtNe} Lh{Jv(cB dB Ki Ou) Wm(Ne Uu) Nt(Ne Pb) DdSh LzPc HciJ} On{My(Ij Mh Nm Nt Nu Of) Mh(Pb Pc) NtOf LzPc} Un{Wm(Ne Ou Ss Uu) AxOu FwaN NevA TvuM JkuX eFiJ} Dl{cF(rW tO tT) qQ(tO tR tX) tT(bU cI)} Lz{Pc(Jt Mm Nt Nu) Nu(Jq Jt) NtNe MjJt} Sr{Th(hR hV hW hX) IbRj dBeC} Jv{Ar(Dc Il Jd) Ax(dB Jd) BbtO} Kr{aN(rX rY rZ) Gz(qW rZ) OfrZ} qU{Ti(jY Lx Or Pg) NwqT dBtX} Qa{Nt(Ne Oe) NuOe tRqZ} Js{Jk(sF sH) rB(tO tR)} Vq{dB(rT wE) iPwE wHqX} pK{DdUp IzUu QukI UtnR} Po{hP(Mj Nq) QwoN} Nm{LxMy MhWb ZxUu} No{Ib(Cq Rj Vv)} Zq{MhcM YkkP KliJ} Kf{cB(tO tT) cFtO} tX{RijM QmjO dBrS} An{KxpI lLrQ} Du{mE(aJ dM)} Fa{eFiJ qHlL} Lx{My(Ij Jt)} Jd{Qu(Fw Il)} Nw{aFaN tRqZ} nK{YhNx VzcZ} rA{TiOr QlrS} CwKlfA ThTzhW NrRmpH LvMthP MftTrS TtlttV IhtRqZ YkUtmU QwbUoW KkjEuI aNjOrQ Constrained panels with 2 analytes, where 1.0E-8 >= 'model p-value' > 0. Contains 91 panels of 199,653 total panels evaluated. : Nw(Fp Hu Im Ir Jj Li Lj Lw Lz Me Mh Mp Ms Mv Mw My Ng Nj Nt Nu Og Ok Oy Pb Pc) Li(aA Et Hu Im Ir Ji Jj Jp Lj Lw Mv Mz Ng Nq Og Ok Oy Oz Pb Pc) Ji(aA Fp Hu Im Jj Jq Lj Mp Ms My Ng Nu Og Oy Pb Pc) Ok(Fp Hu Im Jj Lj Lw Lz Mh Ms Ng Oe Of Og Oy Pb Pc) Im(Et Fp Hu Jj Lj Og) Lj(Et Jp Lw Nt On) Et(Fp Oy) AaQe Constrained panels with 2 analytes, where 1.0E-7 >= 'model p-value' > 1.0E-8. Contains 106 panels of 199,653 total panels evaluated. : Lj(aA Ir Is Jg Jj Jl Jq Jt Lh Lv Lx Mg Mi Mm Mp Ms Mz Nd Nm Nn Nu Nv Nx Ny Og Pc Pd Pg Qd Qe) Im(aA Iq Ir Jk Jl Jp Jt Lw Lz Mh Ms Mz Ng Nj Nn Nt Nu Oe Oy Pb Pe Pf Qd Qe) Et(Aa Hu Ir Jj Lw Lz Mh Ml Ms Mz Ng Nn No Nt Nu Of Og Ok Pc Qd Qe) Aa(Fp Ji Jj Li Lu Lw Nn Nu Nw Ok) Ok(Mc Mg Mp Mz Oz Qd Qe) Fp(Jp Jt Lw) Qe(Aj Jj Nw) Ji(bM Jv Wm) AjKq NnJj MzhP IjOg NwOz Constrained panels with 2 analytes, where 1.0E-6 >= 'model p-value' > 1.0E-7. Contains 141 panels of 199,653 total panels evaluated. : Aa(bM Fr Im Iv Jp Jr Lj Lx Lz Me Mh Mm Mr Ms Mt Nt Ny Oy Pc Pd Po Qa Qc Qd) Fp(Ir Jg Jj Jq Lh Mm Mz Nm Nn Nt Nu Ny Og On Qd Qe Vt) Qd(Hu Ir Jj Jp Lw Mh Mz Nn Nt Nu Ny Og Oy Oz) Qe(aA Gc Hu Jp Jt Lw Nm Nn Nt Nu Og Oy) Et(aA Ih Jn Jq Me Nj Oz Pb Qa Qc) Jp(Hu Ir Jj Lw Lz Mh Nt Ny Oy) Lj(bM iJ Jv Ke No Oy Pe Uh Vt) Nn(Hu Ir Jt Lw Nt Og Oy) Ji(aC aF Aj aN dB Ef iJ) Jj(Jg Jt Lh Nt Ny On Qa) Aj(Ad Jt Nm Ok) On(Hu Ms Og Oy) Gc(eC hC Uy) Pj(aC Fa Sf) Cs(Uh Vt) Ke(bM Jv) Og(Jg Ny) EfKq WmVt TiLi NtMz NwbM Constrained panels with 2 analytes, where 1.0E-5 >= 'model p-value' > 1.0E-6. Contains 465 panels of 199,653 total panels evaluated. : Jp(aA aC bM Cs Eq Hc Ic Id Ih Is Iv Iz Jl Jn Jq Js Jt Jv Kl Lx Me Ml Mp Ms Mx Mz Ng Nj Nm Nn No Ns Nu Og Oz Pb Pc Pe Pj Qa Vt) Vt(aC Aj Ar Ax bM cM dB Ed Fa Fw Gc Il Jd Ji Jv Ke Kq Kr Li Lz Mz Ne Nf Nm Nn No Nr Nt Nu Og Ou Oy Pf Pg Pj Qe Uh Um) Fp(aA Hu Ih Ii Iq Is Jl Jm Jn Js Ke Lx Lz Mc Mp Ms Ne No Nv Nx Oy Oz Pb Pc Pj Pz Qa Qc Uh Un Wm) Nn(aA Aj Ih Is Iv Jg Jl Jn Jq Jr Lh Lx Lz Mh Mr Ms Mx Mz Ng Nj Nm No Nu Ny Oe Oz Pb Pc Pe Qa Qc) Ke(aC Aj aN Aw Ax cB Ch Cs dB EF Fw Gp Ib Ik Il Iz Jj Kl lM Ne Nk Og Oy Pj Qe Uu Wm) Ji(aM aO cB cl Cs dE Ed eF Fa Gl Gp hG Ic Id iH Ju Ki Kl Ou Qx Rc Sf Ss Uh Uu Uy Vv) Qe(aC aN bM cM dB Id Ir Jg Jn Jq Jv Lh Lz Mm Mp Ms Mz Nj No Ny Ou Oz Pb Pc Pj Uh) Lh(aA Hu Ih Ir Is Jt Lw Lz Ms Mz Ng Nm Nt Nu Ny Og Oy Pb Pc Qa Qd) Ny(aA Hu Ir Is Jg Jl Jn Jq Jt Lw Lz Mp Ms Mz Nm No Nt Nu Oy Qa) Pj(Aj Ax bM Cs Fw hC Id iJ Il iZ Jj Jv Ki Kq Lj Lw Mz No Or Uy) Nt(aA Hu Ir Is Jq Js Jt Lw Lx Lz Mm Ne Og On Oy Pc Qa Qc) Mz(aA Ir Jg Jj Jt Lw Lx Lz Mm Nu On Qa qT) Kq(Bg bM Dk Hc Ib Id Iz Jh Jj Jv Kl Lj Of) Jg(Hu Ir Lw Lz Mh My Ng No Of Oy Qa Qd) Lj(aC cM Fn hG Id iO Jd Jy Or Un Wb Ti) Uh(Ax bM cM Fa Fw Gp Id Jj Jv No Vv Wm) Jt(Hu Lx Lz Mh Ms Ng Nu Og Oy Qa Qd) Jj(Ii Ij Jm Jn Js Lx Mm Nu Nv Po) Id(aC bM hP Il jV lK Mn No rC) Qa(Hu Ir Lw Lz Nm Nu Og Oy Pc) On(Ir Lw Lz Mh My Ng Nu Oe Of) Aj(Dc Et Li Nw Qd Un) Gc(Ni Nk Sf Uk Uu Va) Lw(Cs Ir Lx Mm Nu) Qd(Lz Mm Ms Nm Pc) bM(Bb Et Li Ok Pk) Un(aC Cs Oy Wm) Nu(Ir Jl Jq) Lx(Hu Ir Oy) Mm(Ir Lz Og) Nv(Hu Og Oy) Cs(Et Jv) Nw(aC aN) Ok(Eq Yk) AaJl HuIj JsjV PkaC aOjB Constrained panels with 2 analytes, where 1.0E-4 >= 'model p-value' > 1.0E-5. Contains 1,129 panels of 199,653 total panels evaluated. : Pj(aM aN Ar aX bA bE bH cB cF cM Cq CU dA dB Dc dD dH dL Ed fP Gd Gp Gz Ha Hv Ic Ik Ir jD jK Jl Jo Ju Kl Lh Li lK lO Lx Lz Md Mg Mi Mq Mt Ne Nk Nn Nr Nw Oa Of Og Ou Oy Pa Pb Pd Pe Pf Pk Po Qa Qd Qv Rc Ry Sh Si Tr Uh Uk Un Us Uu Vi Vv Wb Wm Tj) Uh(aC aF Aj aM aN aO Ar As Aw cB cE Cq Cu Cv dA dB Dc Dd dE dL Ed Fy hC Hw iA Ic iH iJ Il iP Ir iZ Jp Jq Ke Ki Kl Kn Kq Kr Lh Li Lw Lx Lz Md Me Mi Ml Mt Mz Ne Nm Nn Nr Oa oN Or Ou Oy Pb Pe Pk Po Qa Qd Rc Sr tT Un Up Us Uu) Id(aF Ax bE cB cM Cs Cu dB dD dK dL Et Fa Fp Fw Fy Hb Hv Ic Jd jK jQ Jv Jy Ke Ki Lh Li lM Lx Lz Mz Na Nk Nn Nr Nw Ny Og Oh Ok Or Ou Pa Pf Po Qa Qd qY rQ uG uI uM Un Us uX VT Wm Ti) Mz(aC aN bM Cs Fa Fr Hu Ih Ij Iq Is Iv Jl Jn Jq Jr Js Ke Lv Mh Mi Mp Mr Ms Mt Mx Nh Nj Nl Nm No Nr Nv Nx Og Oy Oz Pb Pc Pe Pf Po Qb Qc qZ rB Wm) Gc(aC aM cD hA iB iC Ik jD jF jG jI Jj jL jP jT JU JV jY Kd Li Lj lL lM lN Ml Mr Mw Nc Ne Ny Oy Oz Pb Pc Rg Sh Tt Un Us Vv) Mm(aA aC Aj Fa Hu Ih Ij Iq Is Iv Jl Jn Jq Jr Js Jt Lx Me Mh Mi Ml Mp Mr Ms Mx Ng Nj Nm No Nu Nv Ny Oy Oz Pb Pc

Figure 41 Continued

Pe Pf Po Qa Qb Qc) Ke(aF aM aO bH bP cM dA dE dL Ed Fa fP hG hP Hu iA Ic iH iJ Jp Ju Ki IK Mg Nc Ng Nn Of oN Ou Pg qA QU Qx Rc Sf Ss tO uM Vv yJ) Kq(aC aM aN Ar Aw Ba Ch Cs Ct dB Ed Eq Fa Fw Gp Hu Ic Jg Jk Li Mg Mv Mw My Ne Ng Nq Nv Og Oi Om Ou Oy Pg Pk Qu Ss Tn Uc Uu Wm) Lw(aC Aj aN Ar Ax bM cI Fa Fr Ih Ij Is Iv Jj Jl Jn Js Jt Lz Mh Mr Mx Nm No Nv Nx Og Oy Pc Pe Po Qb Qc) Lx(aA Eo EW Ij Iq Is Iv Jg Jl Jn Jq Js Lh Lz Mp Ms My Nj Nm No Nu Nx Ny Og Oz Pb Pc Pe Qc Vt Wm Ti) Jg(aA Aj bM Eq Ih Iq Is Iv Jl Jn Jq Js Jt Lh Mg Mp Mr Ms Mw Mx Ns Nt Nu Oe Oz Pb Pc Pe Qb Qc) Cs(aC Aj aN Bb bM cM Cv dB Fn Hb iJ Jd Jj Jt Jy Li Ne Nh Nk Nm Nn Nw Og Ok Pk Qd Vv Ti) Fa(aC aF Aj aN Aw bM dB Et Ib Il In Jd Jj Jp Jv Lj Lu Mj Ne Nk Nm Nn Ou Oy Qe Qx Un Wm) Un(aN Ar Ax bM dB dK Ed eF Fw hG hP Ib iJ Il Jj Jp Jv Ki Li Ne Og Ou Pg Qe Qu Uu Vv) Lh(aC Aj aN bM dB hG Iv Jn Jv Ki IM Mh Mp My No Ou Oz Sf Sh Ss Uu Uy Vc Wb Wh Wm) Nu(aA Fr Hu Ih Ij Is Iv Jn Jr Js Lz Mh Mp Nm No Nv Nx Og Oy Oz Pb Pc Pe Qb Qc) Ir(aA Fr Hu Ih Ij Jj Jm Jn Js Jt Lz Mp Mt Nj Nm No Nv Nx Og Oy Oz Pc Po Qb Qc) Jp(Aj aN aO Ax dB dE Ed Ef Ki Oa Ou Pk Qu Rc Sf Sh Uu Vc Vv Wb Yj Yk Wm Ti) bM(Ax bA Cu Dc Fp Hb Ij Im Jd Jj Jq Js Jt Mt Ne Nm Nn Oa Or Pf Qa Qc Qd) Lj(Aj aK aM aN aU bB cC dB dD Fi Gb Op Pk Qm Tn Tr Ux Vh Vw Zq Wn) Js(aA Fr Hu jD Jl jU lM Lz Mh Mp Ms Nj Nm No Og Oy Oz Pb Pc rB) Nv(aA Is Iv Jn Jt Lz Mh Ml Ms My Ng Nj Nm No Oc Oz Pb Pc) On(Aj Eq Jk Jn Jt Ml Mp Mv Mw Nj Nm Nq Ns Ny Oz Pb Pc Qa) Jj(Al Ax Dc Fr Ih Is Jl Jq Ks Lz Nm No Nr Nx Pz Qb Qc) Ji(Fc hP Ib Iz jD lM rW Sh Si tR tT tX Vs Wb Yd Yk) Et(aC aO Ap Ax dB Dd Dg Dr Du Ef Ic Jv Kl Vt Wm) No(Hu Ij Jd Jn Jt Jv Nj Nm Nx Og Oy Oz Pc Qa Ti) Ny(Ih Iq Iv Mh Ml Ng Nj Oe Pe Pf Qc tR tT tX yJ) Jt(aA aC Jl Jn Ml Mp Mr Mx Nj Oz Pb Pc Qb Qc) Nw(aF aM aO bE cB cI dB jO Jv lM Ou Pk rB Wm) Ok(aC aN cI dB Ef Kl Ps Rx Sf Sh Wb Yd Wm) Lz(aA Fr Ih Ii Ij Is Jn Jq Nm Nx Oz Pc) Li(aC aN dB fP hG Ic Jv Jy lM Qu Uu Wb) Vt(aN aS bH cB dE dK Du eF hG Ic Ur Vh) Nt(Aj Ih Jl Jn Ms Ng Ns Oz Pb Qb Uy) Qe(Fn hG iJ Ki Kl oN Qu Uu Vv Yk Ye) Qa(Aj Ib Jq Ms Ne Nj Oe Ou Oz Pb) Og(Fr Ii Is Jl Jm Jn Jq Nm Po Qb) aC(Aa Ar Bb Dc Im Nm Nn Qd Sr Vq) Nk(Ax Dr gZ Ho pK Vi Wb Zq Xa) Aj(Ax Bb Cu Fr Fy Ii Ij Im) Ti(Ar Ax Ed Nb Nr Pe Po) Nm(aA Is Jl Jn Qb Sf Sh) Ij(aA Jl Mp Ms My Oy Pb) Qd(aN dB hP iJ Jv rB Wm) Jn(aA Fr Is Jl Mp Ms) Jv(Ar Ax Dc Fp Jd Nn) Zq(aM Eq Kl Mh Ml) Oy(Fr Is Jd Jl Po) Wm(Fw Hb Mt Po) Hu(Fr Is Jl Po) aA(Ih Jm Qb Qc) Ax(Jd Jy Ur) Nn(aN dB Ki) Pk(dB dL iJ) Fw(Hb Jd) Ne(Oa tV) Im(aN dB) Sr(Aw jV) Jl(Oz Pc) Jr(jD jV) AatX DltT EwaM FpJd FrJq MthP YicD YdjP WbKx KrtO UtUy VchA VhjD OzjB bBdU

Constrained panels with 2 analytes, where 1.0E-3 >= 'model p-value' > 1.0E-4. Contains 1,935 panels of 199,653 total panels evaluated. : bM(aA aC Ad Aj aM aN Ar Bc bE cI cM cT Cv dB DD Ed Fb Fr Fw Fy Gc Ha iJ Iq Ir Is Iv jB Jl Jm Jn Jr Jv Jy Kd Kn Ko Kp Kr Lx Lz Mi Ml Mm Mr Nb Nk No Nt Nv Nx Ny Og On Oy Pb Pc Pd Pe Pi Po Qb Qh Rf rS Sr St Tz Uf Up Us Vu Wm) aC(Ad aM aN Ax bA Bc cB Cu Cv dA Dd Dg Ed Fb Fp Fr Fw Fy Hb Ih Ii IJ Iq Ir Jd Jg Jj Js Jv Jy Kf Kn Ko Lx Lz Mr Mt Mu Mw Nb Ne Nk No Nt Nu Nv Ny Oa On Or Pd Pe Pf Qa Qc Uf Us Zq Wm) Nm(aM aN Ar Ax bA bE cB cI Ct Cu dB Dc dD Ed eF Eq Fr Fw Hu Ih Ij Iq Iv Jm Jq Jr Jv Mh Mi Ml Mp Mr Ms Mt Mx Ng Nj Nr Nx Oa Or Oy Pc Pe Pf Pk Po Qc Sr tT tX Uk Uu Uy Vb Vi Wb Ye Wm) Jj(aA Ad Ar Bb Cu Cv Dd Ed Fb Fw Fy Ha Hb Ip Iq It Iv Jd Jk Jo Jr Kg Kn Kr Lv Ma Mh Mi Mn Mp Mr Mt Mw Mx Nd Nj Oa Oh Or Oz Pc Pd Pe Pf Pk Qh Sr Uf Up Vh Vq Wb Yi Zq Wm Ti) Zq(Al aO Ar bO bU cD cL cM Cs Cv dD Dg Dl Du Ez Fa Fw Gd Ha Il Ir It Jv Ki Kx Li Mp Nc Ne Nr Ns Oi Oy Oz Pb Pc Pg Po Rc Rg Sf Sh Us Uu Uy Vc Vo Vs Vt Wb) Ti(aM Bc cM Cu Dc Dd Du Fa Fp Fw Ha Ij Il Ir iZ Jl Kd Kq Kx Lz Mh Mi Mr Mt Nk Nn Nt Nv Oa Og On Or Pf Pg Qa Qd Rg Sf Sr tX Uf Uh Ut Uy Vi Wb Wm Tj) Aj(Aa Al Ap Ar bA Bc Cv dB Dd Dg Dl Fb Fp Fw Gc Hb Ih Iq Ir Iz Jd Jm Js Kg Kn Ko Kr Ks Lx Mt Mz Ne Nv Nx Ny Oa Pd Pe Pf Po Qc Sr Uf Vq Wm) aN(Aa aF Ar Ax bA Bb Cu Dc Dd Ed Et Fp Ij Ir Is Jm Js Jt Lx Lz Mm Mr Mt Ne Nk Nt Nx Ny Oa On Pe Pf Pk Po Qa Qc qT rQ rW sC tV uL wE Wm) Lh(aF aM aO cB cC Ch cI dE Dr Ed EF Eq fP Gb hC hP iA Ib Ic iH iJ Iz jD jO Kl Oa oN Ow Qu rB Rc tO tR tT tX Ur Uv Vv wQ Yd Yk) Wm(Ar Ax Bb Cu Dc Ed Fy Gl Iq Ir Jd Jl Jq Js Jt Kd Ki Kn Kr Lw Lz Mi Mr Ne Nn Nt Oa Og On Or Pa Pe Pf Pk Qc rB Sr St Ur Us Uu) Ar(Aa aF aO Bb bE cM Cu Cv dB Dc Dd Ed Et Fn Hb Ic Jd Jp Jt Jy Ki Kr Mt Mz Ne Nk Nn Oy Pd Pk Qc Qd Up Us Uy Vc Vh Vi Wb) Lz(Ad Ax Bb Cv dB Dc Dd Ed Fb Gc Hu iJ Iv Jd Jl Jm Jv Ko Ma Mc Mp Mt Nj No Nr Oa Og Oy Po Pz Qb Qc rB rS Sr Us Wb) Li(aF aM aO AX Bb cB cM Cv dE Dr dU Fb Fn hC hP iA iJ Jd Ki Kl oN Or PK rB rS tO tR tT tV tX Uy Vc Vv Wh yJ) Wb(aM As Ax bB Cs Du Et Fw Fy Gc Hf Ii Ij Il Ir Ke Lx Mf Mh Ml Mm Mn Mt Mw Mx No Nr On Oz Pe Pf Po Qa Qx Ut Yl) Qc(cM Cu dB Dc DD Fr Hu Ih Ii Ij Is Iv Jl Jn Jq Jr Mh Mi Mp Mr Ms Mt Mx Nd Nj No Nv Nx Og Oy Pc Pd Pe Po) Lw(aA aF bA Bb cC cL dB Dc Dd Ed eF Fw Hb hP Hu Ii Iq Jm Jq Jr Ma Mi Ml Mp Ms Mt Nj Nr Oa Oz Pb Pf Pk Pz) Sr(cM Cu Cv Dc Ed Et Fw Ha hP Il Jv Ki Kn Kq lM Lx Mt Mz Ne Oa Or Oy Pe Pf Pj Pk Po Qa Qd rB Uy) Jq(aA Hu Ih Ij Iv Jl Jm Jn Jv Mh Mp Mr Ms Mt Mw Mx Nd Nj No Nr Nv Nx Oy Oz Pb Pc Pe Pf Po Pz Qb) Nn(aF aM aO Ax bA cC Ch cI cM Cu Dc Dd dU Ed Hb hC iA Ic iP Iz Jd Kd Kl Kq Oa Or Ou Ow Pk Uu) Kq(aF aO Ax bF De eF Et Gc Hb hG iP Jd Nf Nw Oa oN oP Qt qU Rc rW Sf Sh Ua Ut Uv Vs Vv Wh) Jv(Al Bb Cu Dd Fw Fy Hb Ij Il Im Iq Js Jt Kn Ko Lx Mt Mz Nr Ny Oa Ok On Or Po Qa Qh Uf) Jd(Cu Dc Ed Gp Ha Ic Il Ir Kd Kl Lx Mt Mz Oa Og Or Pe Pj Pk Po Qa Qd Qu Rc Us Uu Vv) Ax(aF aM Bb cC cM dB dU Fn Hb iJ Mc Mt Mu Mz Nb Ne Og Ok Or Ou Pb Pd Pk Qd Vv Wn) Et(aF aM cB Ch cI dA Dc Ed Eq Gp Ha Iz Ki Oa Or Pk Qu Rc Sf Sh Ss Us Uu Uy Vc Vv) Gc(aS bU cM Cu dD eP Fa Ha Im Jn Jp kP Kx Ky mS nB nK Ns Nt Oa Or Pe Pg Pk Ry Si) aA(Fr Hu Ii Iv Jl Lv Mh Mi Ml Mp Mr Mt Mw Mx Nj Nr Nx Og Oy Oz Pc Pe Pf Po Pz) Uy(bB bU Cs Cu Dk Fp Hb Ii Ij Jt Ke Kx Mf Mn Ng Nk No Nr Nu On Pe Po Un Vh) Mp(Fr Hu Ih Ii Is Iv Jm Jr Mh Ml Mr Mt Nj No Nr Nx Og Oy Oz Pc Po Pz Qb) Mz(aF aM aO bA cI Cu Cv dB Dc Dd Ed Fy Hb Hx Ib Ki Oa Or Ou Pk rQ rS) Sf(Al Dc Dd Dk Fy Hb Ii Ij Il Im Ir Jn Jt Mm Mn Ng Nk No Nr Nt On Yi) Ih(Fr Hu Ij Iq Iv Jl Jn Mh Mr Ms Nj No Nv Nx Og Oy Oz Pc Pe Pf Po) hP(Cu dA Fa Jl Jp Jr Js Kn Lj Lx No Nw Ny Or Pd Pe Po Qa Qe Uh Vt) Qd(aF aO cM DD Du Ed Ef hG iP jD jV Kl Ou Pk qT qU Us Uu Vv) Nx(Fr Hu Iq Is Iv Jl Mh Mi Mr Ms Mt Mx My Og Oy Pc Pe Pf Qb tX) Un(aF aO Du eC iH jO jV oN qU rB rS sK tO tR tT uG uM uX vA Yk) Nk(cI Cu Dc Ed eQ fA Fd Fi Fw Gb Lp Oa Pk Rt Uw Vh Yi Ye Yf) Jn(Dr Hu Ij Iq Iv Mh Mi Mr Mx Oy Oz Pb Pc Pe Pf Po Qb Sh Yk) Ok(aF aH aO cB Ch Ct Ed eF Ic Iz Ki Or Ou Pk Qu Qx Rc Ss Uu) Fr(Eq Is Iv Jl Jr Me Mh Ml Ms Mx Ng Nj No Oz Pb Pc Pe Qb) Il(Du Ed Hb Hc Kn Ko Kr Oa Og Or Pk Qw Rf St Uk Ur Uu Vv) Ke(Eq jD rB rQ rR Sh Si sO tR tT tX uN Vs vU Wh wQ Yk zG) Po(hG Ib Is Iv Iz Jl Ms Mv My Nu oN Oz Pb Pc Ur Vh wQ) No(Hb hG Hp iA iJ Is Jm Ki Ou Pb Pk Pz Qb Ur Vv Yk Ye) Oy(Ad Bb Cu Dc Fy Ii iJ Iq Iv jB Jm Mt Nr Oa Pe Qb Vq) dB(Aa bA Bb Cu Dc Ed Fp Fy Ij Jt Lx Mt Oa Qa rS tV tX) Fw(iJ Jy Ki Lu oN Or Ou Pk Rf Uk Ur Vc Vh vO Vv wE) Jp(aF aM aX cB cC Ch cI Dr hG iA iH iP rB Ss Vs Yi) Og(Bb Cv Dc Dd Iq Iv Mi Mr Mt Mw Mx Nr Oa Pe Pz Yi) Du(Al Cu Gb Hb iJ kR mE Nt Ny Pj Qh Qy Uh Up Vq) Ij(Dr Eq Iq Is Jr Mh Ng Nj Oe Oz Pc Pf Sh Vc Yk) tX(Dl Hx Id iP Jg jM Lj Mf Nw Pj Qm qZ rB Uh zG) Cs(Aa aF aK aM Gb hG iA Mm Mu Nl Oi Pb tV Vh) Sh(Al Cu Dd Dk Fy Ii Mm Mn Ng Nr Nt On Ut Yi) Fp(Ad Bb cM Cv Dc Dd Hb hG iJ Jy oN Pk Vv) Lx(aF aO Bb Dd Ed Hb Hx lM Mv oN Pk Ps Qx) Qa(aO cM Ed Hb hG iJ iP Ki rB Ur Uu Vv Ye) Qb(Hu Is Iv Jl Mh Mi Ms Nj Oz Pb Pc Pe Pf) dU(aW bU Lj Lt mE Mn Mw Nj nK Oz Qe Ut Wf) Cu(aF aO Bb cI Eq Hb Ib Ne Ps Vb Vv Wh) Dr(Aa aM bB bU Kx Lj Mn Mw Nt On Uh Ut) Fa(Aa bH bQ cM eC eF Gb hG iJ oN rB vO) Mt(aF aO Bb Dc Dd Ed Hb Hu Iv Oz Pk rB) Nw(Ed eF hG iA iJ Kl Qx Rc rQ Us Uu Vv) Nu(Ii Iq It Jm Mi Ml Mr Ms Mx Nj Pf) Pe(Hb Hu Hx Ir Jm Nj oN Oz Pb Pc Pz) rS(cI dE iP Ji Jl Kk Lj Mf qX rQ uM) Dc(cB cI Ct Ed Nb Ne Nh Ou Ur Uu) Eq(Ad Ap Dk Fy iJ Mm Mn Ng Nt Ut) Uh(cC jD jI lM qA qU sK tO Yk Wn) Vt(iH iJ jV sK tO tR uM vO vT Yi) Pk(aU cC cM dD dE hG Ki Ko Mm Ne) rB(Im Is Ji Jl Jr Oa Or Qe St Tz) Aa(aM cB dA dD dL hC hG iA tV) Id(eC eF fP iJ tN tO tT wF zG) Ii(Hu Iv Mh Ms Ng Nj Oz

Figure 41 Continued

Pb) Ji(jO IN qZ rQ tN tO tS uM) Oa(Hb iJ Jy Mj Nl Oi Ou Ur) aM(Bb dK Fi Gb Hb Si Vh Yi) Ed(Cv Hb Jy Kn Rf Tr Us) Ne(Al Bb Dd Or St Vh Vq) Is(Ir Mh Ms Nj Oz Pb Pc) Jl(Mh Ml Nj Nr Pb qH qZ) Kr(qU rX rY rZ tT tV) Ny(Ib qA tN tO uN Yk) jB(aW bF bN mE nK pK) qZ(tO tR tS tT uM yJ) lm(bE dE iJ Ou Ye) Iv(Jm Nj Oz Pc Pz) Pj(hW Jy nN qU Rg) pK(aW bU cR eC nK) An(rQ rZ tT tV) Hb(dL Fc Or Pf) Vh(bU cM jY Ml) Pc(Mh Mi Mx Pf) Dl(tO tR uM) Gb(bB Kx Ml) Yk(Ir On Yi) Jt(cl Ct Vb) cR(oD oT oW) hW(cl Kz Qx) tT(iP Jg Mf) Mh(Jm Pz) Mn(Gz Ic) Nj(Iq Mr) Yd(hA jY) Qm(tV wF) Ut(oP Vc) Vq(cC mS) bU(nN oW) nJ(hR IN) nK(Vz Yl) qX(uI uM) BbNb BoeW CwVb DdPf FyOr HaOu NrHu McJs MsJm ZxjD StiJ WeOn XacD YemT TljY KkrW KorQ UrUs VcjP VaiC PahA aFbA bBoW bSeO dEtV mMIL nIhR Unconstrained panels with 3 analytes, where 0.0E0 >= 'AUC p-value' > 0. Contains 50,000 panels of 37,941,150 total panels evaluated. :
Gc{hC(AA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR Du eC Ed EF Em Eq Et Ex Ez Fa Fb Fc Fd Fi Fn FP FR Fw Fy Gb Gd Gh GL Gn GP Gz Ha HB Hc HF hG HI Ho Hp Hq Hr Hu Hv Hw Hx iA Ib Ic Id IH Ii IJ Ik Il Im In IO IP Iq Ir Is It Iu Iv IZ Jd Je Jf Jg Jh Ji Jj Jk Jl Jm Jn Jo Jp Jq Jr Js Jt Ju Jv Jy Kc Kd Ke KF Kg Kl Kj KK Kl Kn Ko KP KQ KR KS Kx Ky Kz Ld Lh Li Lj Lp Lt Lu Lv Lw Lx Ly Lz Ma Mb Mc Md ME Mf Mg Mh Mi Mj Mk Ml MM Mn MP Mq Mr MS Mt Mu Mv Mw Mx My MZ Na NB Nc Nd Ne Nf Ng Nh Ni NJ NK Nl Nm Nn No Nq Nr Ns Nt Nu Nv NW Nx NY Oa OE OF Og OH Oi OK Om ON Op Or Ou Ow Oy Oz Pa Pb Pc Pd Pe PF Pg Ph Pi Pj Pk Po Ps Pz Qa Qb Qc Qd Qe Qg Qh Ql Qm Qn Qt Qu Qv Qw Qx Qy Qz Ra Rb Rc Rf Rg Rh Ri Rj Rm Rt Ru Rv Rx Ry Rz Sf Sh Si Sj Sr Ss St Tn To Tr Tt Tv Tz Ua Ub Uc Ud Ue Uf Ug Uh Uk Ul Um Un Uo Up Ur Us Ut Uu Uv Uw Ux Uy Va Vb Vc Vh Vi Vj Vo Vp Vq Vs Vt Vu Vv Vw Vz Wb Wc Wd We Wf Wg Wh Yd Yg Yh Yi Yj Yl Zq Zw Zx Ye Tm Tl Xa Wm Tj Ti Th tF Yf) eC(AA aC AD aE AF aG aH al AJ aK AL aM AN AO AP aQ AR AS aU aV AW AX aY aZ BA BB BC bE bF BG bH bI bJ bL bM BN BO bP bQ bR bS bU bV bW bX bZ cA cB cC cD cE cF cG CH cI cJ cK cL cM cN CO CP CQ cR CS CT CU CV CW CX cY cZ dA DB DC DD DE dF DG dH DI dJ DK DL dM dN Dp DR Du Ed EF Em Eq Et Ex Ez Fa Fb Fc Fd Fi Fn FP FR Fw Fy Gb Gd Gh GL Gn GP Gz Ha HB Hc HF hG HI Ho Hp Hq Hr Hu Hv Hw Hx iA Ib Ic Id IH IJ Ik Il Im In IO IP Iq Ir Is It Iu Iv IZ Jd Je Jf Jg Jh Ji Jj Jk Jl Jm Jn Jo Jp Jq Jr Js Jt Ju Jv Jy Kc Kd Ke Kf Kg Kl Kj Kk Kl Kn Ko KP KQ KR KS Kx Ky Kz Ld Lh Li Lj Lp Lt Lu Lv LW Lx LY Lz Ma Mb Mc Md ME Mf Mg Mh Mi Mj Mk Ml Mm Mn Mp Mq Mr MS MT MU Mv Mw Mx My Mz Na NB Nc Nd Ne Nf Ng Nh Ni Nj Nk Nl Nm NN No Nq NR Ns NT NU Nv NW Nx NY Oa OE OF Og OH Oi OK Om ON oO OP Or Ou Ow Oy Oz Pb Pc Pd Pe PF Pg Ph Pi Pj Pk Po Ps Pz Qa Qb Qc Qd Qe Qg Qh Ql Qm Qn Qt Qu Qv Qw Qy Qz Rc Rf Rg Rh Ri Rj Rm Rv Rx Ry Rz Sf Sh Si Sj Sr Ss St Tn To Tr Tt Tv Tz Ua Ub Uc Ud Ue Uf Uh Uk Ul Um Un Up Ur Us Ut Uu Uv Uw Ux Uy Va Vb Vh Vj Vo Vp Vq Vu Vv Vw Vz Wb Wc Wd We Wf Wh Yd Yg Yh Yi Yj Yk Yl Zq Zw Zx Ye Tm Tl Xa Wm Tj Ti Th Yf) Uy(AA aC AD aE Af aG al Aj aK Al aM AN aO AP aQ Ar As aU AW Ax aY aZ Ba BB Bc bF BG bH bI bL bM BN BO bQ bR bU bW bX bZ cA cC cD cE cF Ch cI cJ cK cL cM CO Cp Cq cR CS Ct CU CV cW Cx cY cZ DB DC DD De DG dH DI Dk Dl dN DR Du Ed EF EM Eq Et Ex Ez Fc Fi Fn FP Fr Fw Fy Gb Gd Gh GL Gn gP Gz Ha hB Hc HF Hq Hr Hu Hv Hw Hx iA Ib Ic Id IH IJ Ik Il Im In IO IP Iq Ir Is It Iu Iv IZ Je Jg Jh Ji Jj Jl Jm Jn Jo Jp Jr Js Jt Ju Jv Jy Kc Kd Kf Kg Ki Kj Kk Kl Kn Ko KP KQ KR KS Kx Ky Kz Ld Lh Li Lj lO Lp Lt Lu Lv Lw Lx Ly Lz Ma Mb Mc Md Me Mf Mg Mh Mi Mk Ml Mm Mn Mp Mq Mr Ms Mt Mu Mv Mw Mx My Mz Na Nb Nc Nd Ne Nf Ng Nh Ni Nj Nk Nl Nn No Nq Nr Ns Nt Nu Nv NW Nx NY Oa oE OF Og OH Oi OK Om ON Op Or Ou Ow Oy Oz Pa Pb Pc Pd Pe PF Pg Ph Pj Pk Po Ps Pz Qa Qb Qd Qe Qg Qm Qn Qt Qu Qv Qx Qy Qz Ra Rb Rc Rg Rh Rj Rm Rt Ru Rv Rx Ry Rz Sf Sh Si Sj Sr Ss St Tn To Tt Tv Tz Ua Ub Uc Ud Ue Uf Ug Uh Uk Ul Um Un Uo Ur Us Ut Uu Uv Uw Ux Uz Va Vb Vc Vh Vi Vo Vp Vq Vs Vt Vv Vz Wb Wc Wd We Wf Wg Wh Yj Yk Yl Zx Ye Tm Wm Tj Ti Th Yf) iZ(Aa aC AD aE aG al AJ aK AL aM An AO AP aQ Ar AS aU aV aW AX aZ BA BB BC bE bF BG bH bI bJ bL bM BN BO bP bQ bR bS bU bV bW bX bZ cA cB cC cD cE cF Ch cI cJ cK cL cM cN cO CP Cq cR CS CT Cu cV CW Cx cY cZ dA DB dC DD DE DG dH DI dJ Dk DL dM dN DR Du Ed EF Eq Et Ex Ez Fa fB Fc FP Fr Fw Gb Gd GL Gn GP Gz Ha Hc HF hG Ho Hp Hq Hu Hw Hx iA Ib Ic Id iH Ii IJ Ik Il Im IO IP Ir Is It Iu Iv Iz Jd Je Jg Jh Ji Jj Jk Jl Jm Jp Jq Js Jt Jv Jy Kc Kf Ki Kj Kk Kl Ko kP KQ KR kS Kx Ky Kz Lh Li Lj Lt Lv Lw Ly Lz Ma Mb Mc Md Me Mf Mg Mh Mi Mj Mk Ml Mn Mp Mq Mr Ms Mu Mv Mw Mx My Na Nb Nc Nd Ne Nf Ng Nh Ni Nj Nk Nl Nm No Nq NR Ns Nt Nu nW Nx nY Oa OE OF Og oH Oi OK oN Or Ou Oy Oz Pa Pb Pc Pd Pe PF Pg Ph Pi Pj Pk Po Ps Pz Qe Ql Qn Qu Qv Qw Qy Qz Rc Rg Rm Rv Ry Rz Sf Sh Si To Tt Tz Ua Ub Uc Ue Ug Uk Um Ur Us Uu Uw Ux Va Vh Vo Vp Vq Vs Vv Vw Vz Wb Wc Wd We Wf Wh Yd Yg Yk Yl Zw Zx Ye Tm Tl Tj) jV(aA AD aE AF aG aH al Aj AL aM aN AO AR AW aY aZ BA bB bC bF BG bH bM Bn Bo bP bQ bR bU bX bZ cB cC cE cF cG CH cI cK cM cN CO Cp CQ cR CS CT CU CV CW CX cZ dA Db Dc DD DE dF Dg DI dJ DK Dl dM Dr Du Ef Em Eq Et Ex Ez Fd Fn Fp Fr Fw Fy Gb Gh Gl Gn Gp hA Hc Hl Ho Hq Hu Hw Hx iB iC Id Ii Il Im In Iq Is Iv Iz Jd Jg JH Jl JK Jl Jn Jo JP Jq JT JU Jv Jy Kc Kf Kg Ki Kj Kk Kl Kn Ko Kp Kr Ks Ky Kz Ld Lh Li Lj IL IM lO Lt Lu Lv Lw Lx Ly Lz Ma Mc Mf Mg Mh Mi Mj Mm Mn Mq Mt Mu Mv Mw My Mz Na Nb Nc Ne Nf Ni Nj Nk Nl Nn Nq Nr Ns Nt Nv Nw Nx Ny Oa Of Ok On Op Or Ou Oy Pf Pg Pi Pj Po Ps Pz Qa Qd Qe Qh Ql Qt Qu Qv Qy Qz Ra Rb Rc Rh Rj Rm Rt Rv Ry Sf Sh Si Sj Sr Ss St Tn Tr Tt Tv Ua Ub Uc Ud Uf Uk Uw Ux Uz Vh Vi Vo Vp Vq Vs Vt Vv Vz Wc Wd We Wf Wg Wh Yd Yl Zw Zx Tm Tl Wm Tj Ti) iA(Aa aC aD AF aG al AJ Al aM AN aO AP AR As aU aW Ax aY bB BC bF BG bI bJ bL bM BN BO bQ bR bU bW bZ cB cD cE Ch cM cN CO CP cQ cR CS Ct Cv CW Cx dB DD DE dH dI Dk DL dN Dr DU Ed EfeP Eq Et Fa Fb Fc Fp Fw Fy Gd GL Gn gP Gz Ha hB Hc Hf hG Ho Hq Hu Hw Hx Ib iH Ii IJ Ik Il Im Io iP Ir It Iu Iz Jf Jg Jh Ji Jj Jm Jn Jp Jr Js Jt Ju Jv Kc Kf Kg Ki Kj Kk Ko KQ Kr KS Kx Ky Kz Ld Lh Li Lj Lw Lx Lz Ma Mf Mg Mh Mj Ml Mm Mn Mp Mq Mr Ms Mt Mu Mv Mw Mx My Mz Na NB Nc Nd Ne Nf Ng Nh Ni NK Nl Nm Nn No Nq Nr Nt NW Nx Ny Oa oE OF Og OH Ok Om ON Op Ou Ow Oy Oz Pb Pc Pd Pe Pf Pg Ph Pi Pk Po Pz Qa Qb Qd Qe Qv Qz Rc Rg Rm Rx Ry Sf Sh Si St Tr Tt Ua Uc Ud Ue Ug Uk Um Un Us Uu Va Vb Vo Vp Vq Vs Vt Vv Vz Wc Wd We Wf Wh Yd Yk Yl Zx Ye Xa Tj Yf) oE(Aa aC AD AF aG al Aj aK aL aM aO aQ AR As aU AW Ax aZ BA BB Bc bF BG bH bJ bL bM BN BO bQ bR bU bZ cD cE Ch cK cL cM cN Co Cp cQ cR CS CT cW Cx cY dD DE dF DG dH dI Dk Dl dM DR Du Ed EF Eq Et Ez Fa Fp Fr Fw Gd Gn gP Ha Hc Hf Hp Hq Hu Hv Hx Ib IJ Ik Io IP Ir It Iu Iv Iz Jd Jg Jh Jj Jk Jm Jr Jt Jv Kc Kf Kg Ki Kj Kl Ko KR Ks Kx Ky Kz Li Lj Lv Lz ME Mg Mh Mj Mk Ml Mm Mp Ms Mu Mv Mw Mx My Mz Na Nc Nd Nf Ng Nh Ni Nk Nl Nm No Nq nR Ns Nt Nu Ny Oa Of Og oH Oi Op Ou Oy Oz Pa Pb Pc Pd Pe Pf Pg Pj Pk Po Ps Pz Qb Ql Qm Qn Qu Qv Qw Rc Rg Rm Rz Sf Sh Si Sj To Tr Tt Tz Ua Uc Ue Us Uu Uw Va Vb Vj Vo Vp Vq Vs Vu Vv Vz Wb Wc Wd We Wf Wh Yd Yg Yk Yl Zx Ye) jE(AD aE aH AJ AL An Ao Ap aR aU Aw AX BA bB bH bI bJ bM Bo bP bR bS bV bW cA cB cC cD cF cG cI cJ cK cM CP CQ CT Cv CW CX cZ DC DE dF dH DI Dk dL dM Dp Ef Em Eq Et Ex Fc Fd Fn Fr Fy Gb Gh Gl Gn HA Hf Hl Hu Hv Hx IB Id Ij Im Iq Ir Is Iu Iv Iz Je Jf Jg JH Ji JK jM Jn JO JQ jR Js Ju Jv Kc Kd Kg Kj Kl Kn Ko Kp Kr Kz Ld lN lO Lt Lu Lw Ly Lz Mc Md Mf Mi Mm Mp Mq Mr Ms Mu Na Nb Nd Nf Ni Nj Nl Nq Ns Nt Nu Nw Oa Oe Of Oh Om Ow Pa Pe Pz Qa Qc Qd Qe Qg Qh Qm Qu Qw Qx Qy Ra Rf Rh Ri Rm Rt Ru Ry Rz Sf Si Ss St To Tr Tt Tv Tz Ua Ub Uc Ud Uf Ul Um Uo Uw Ux Uz Vc Vo Vq Vs Vt We Wf Wg Yl Zq Zw Tm Tl Xa Tj Ti) hA(aC AD aE aF aG AL aN Ao aP aR aU aV AW aX BB bC BG bH bI bL BO bR bS bV bW bX bZ cB cD cF CH cI cJ cL cM cN Co cP cR cS cU Cv cW CX cY cZ dA Db DC DG dH Di dJ dK dL Dr Ef Eq Fp Fr Gb Gl Gn Gz Hb Hc Hf Hl Hr Hu Hv Hw Hx iB Ic Ih Il Io Iq Ir Iu Iz Je JF JH Ji

Figure 41 Continued

JK Jm Jn JO JP Jq Jr Ju jY Kg Kj Kk Kl Kn Ko Kq Kr Kx Ky Ld Li lO Lt Lv Lw Lz Ma Md Mf Mg Mi Mm Mn Ms Mt Mz Na Nc Nj Nk Nn
No Nr Nu Nv Nw Ny Oa Og Oi Om Ou Ow Oy Pc Pd Pe Pi Pj Pk Ps Qa Qc Qd Qm Qt Qu Qv Qx Qy Qz Ra Rc Rh Rj Rm Ry Rz Sf Sh Sj Ss Tv
Tz Ud Ue Uf Ug Uz Va Vb Vc Vh Vi Vo Vq Vt Vz Wc Wd We Wf Wg Yd Yl Zq Zw Ye Tm Ti Th) Nk(Aj aM Ax cD cM Cq Cs Cu dR dU Ed
EF cM cQ Et Ex fA fB FP Gb gC Gd gL gP gW gZ Ha hB hF hG Hv iB iH lJ ll ln iO iP Iq Ir Iv jB jD jF jG Ji Jj jK jM Jn JP JR Js jT jU jY Kd
kF kG kP kQ kR kS Ky Li Lj lK lM lW LX lY ME Mi mM mP Mr mS MT mU MW Mx mY mZ Na nB nC nH nI Nj nK nL nN nO NR nU nW
NY oD oF oH OK oN oO oP oQ oT oV oW Pb Pe pF Pg pH pI pK Po Ps Pz Qa Qb Qc Qd Qe Qg Qh Qt Qu Qv Qw Qx Qy Qz Ra Rb Rc Rg Rj
Rm Rt Ru Rv Sf Sh Sr Ss St Tn To Tr Tt Tv Tz Ua Ub Uc Ud Ue Uf Ug Uh Uk Ul Um Un Uo Up Ur Us Ut Uu Uv Uw Ux Uz Va Vb Vc Vh Vi
Vo Vp Vq Vs Vt Vv Vw Wc Wd We Wf Wg Wh Wm Tj Ti tF Yf) jM(aC AD aE aG al AJ Al An AR As aU AW AX BA bB bH bI bJ bM bN
Bo bP bR bS bV bW cA cC cF cI cK cM cO CP CQ cR CT Cu Cv CW CX cZ dA dB DC DD dE dF Dg dH dI dJ dL dM dN Dp Ef Em Eq Ex
Fc Fd Fn Gh Gl Gn Ha Hl Hu Hv Hx Ib Id Ii Ij Im Iq Ir Is Iu Iv IzjD Je Jf Jg jH Ji Jj jK Jn Jo JQ jR Js Jv Kd Kg Kj Kl Kn Ko Kp Kr Kz Ld Lh
Li lO Lt Lw Ly Lz Mc Md Mf Mh Mi Mp Mq Mx Na Nb Nd Nf Ng Ns Nv Oa Oe Of Oh Oi Ou Ow Pa Pe Pz Qc Qe Qh Qm Qn Qu Qx Ra Rf
Rg Rh Ri Rm Rt Ru Ry Si Ss St To Tt Tv Tz Ua Ub Uc Ud Uh Uk Ul Um Uz Va Vb Vc Vo Vq Vs Wb We Wg Yd Ye Tl Xa Tj Ti) lO(aA AD
aE aG AJ AL An Ap aQ AR aU Aw AX bA Bb bI bJ bL bM Bo bP bR bS bV cA cB cF cI cJ cK cM cO Cp CQ CT Cv CW CX cY cZ dB dC
dD DE Dg DI dJ DK dL dM dN Dp Dr Em Eq Ex Fc Fd Fr Gh Gl Gp Ha Hf Ho Hu Hv Hw Hx Ib Id Ii Ij Ik Im Iq Ir Is Iu Iv Iz Je Jf Jg jH Jj jK
Jn Jo JQ Js Jv Kd Kf Kg Kj Kl Kn Ko Kz Ld lK Lt Lu Lw Ly Lz Mc Md Mf Mh Mi Mp Mq Ms Mu Na Nc Nd Nf Nh Nj Nl Ns Nt Nw Oa Of
On Ou Ow Pe Pi Pz Qc Qe Qg Qh Qm Qw Qx Qy Ra Rh Ri Rm Rt Ru Ry Rz Ss St To Tt Tv Tz Ua Ub Ud Uf Ul Um Uw Ux Uz Vc Vo Vq Vs
Vt We Wg Xa Tj Ti Th) jD(aA aC aD aH aI AJ aK AL An AP aQ aR aV Aw bA BB bC bE bF BG bH bI bQ bV bX bZ cB cC cE CH cJ cM Co
cP cQ cR cS Ct cV cW Cx cZ dA dC DD Dg dH dJ Dk dL dM Dp Ef Eq Fd Fn Fr Fw Gh Gl Gn Gz Hc Hl Hq lB Ic Ii Ij Ik Il In Ip Ir Is Iu JF jG
jH Ji Jj jK Jm Jq Jr jU JY Kc Kg Ki Kj Kk Ko Ks Lh Li lK IM Lp Lt Lv Lx Ma Md Mf Mg Mk Mm Mn Mp Ms Mt Mv My Mz Nc Ne Ng Ni
Nj Nq Nr Ns Nv Nw Nx Og Oi Ok On Op Or Ou Pc Pf Pg Pj Pk Qc Qg Qh Qm Qw Rb Rg Rh Rx Sh Tn To Tr Ue Uf Uo Ux Vh Vi Vo Vp Vq
Vs Vt Vw Wc We Wf Yd Zw Zx Tm Tl Ti Th) iP(Aa aC Ad Aj Al aM AO Ar aW Ax aY bB BG bI bJ bN BO bQ bR bU cD cF cK cM cQ cR
Cs Ct cW dB dD De Dg dH dI Dk Dl Du Ed Ef Eq Et Fa Fp Fw Gd Gn Ha Hc Hf Hq Hu Hv Hx Ih Ii Ik Im Io Ip Ir Iu Iv Iz Jg Jj Jl Jm Jn Jp Jt Jv
Kc Kj Kk Kl KR Ks Kx Ky Kz Li Lj Lv lW Lz Mg Mh Mj Ml Mr Ms Mv Mw My Mz Na nB Nc Nd Nf Ng Nh Ni Nl No Nq NR Nu nW NY Oa
Of Og Ok ON oP Oy Oz Pa Pb Pc Pd Pe Pf Pg Pi Pk Po Qa Qb Qd Qe Qv Qz Rc Rg Rm Sf Sh Me Mf Mg Mh Mj Ml Mr Mv Mw Mz Na Nc
Vs Vv Vz Wc Wd We Wf Wh Yk Yl Zx Ye Xa) jQ(aC Ad aE aF AJ Al An Ao aR aU aV Aw aX Bb bH bI bJ bP bQ bR bS bV bZ cA cC cE cF
Ch cI cK cM CP Cq cS CT Cv CW CX cZ dA dB DC dE dF dH dI dM Dp Em Eq Ex Fc Fd Fr Fy Gh Gl Gn Gp Ha Hf Hl Hq Hu Hv Hx lB Id Im
Ir lu Iz Je Jf JG jK Jo Js Jt Jv Kc Kd Kg Kj Kl Kn Ko Kp Kr Ks Kz Ld lK Lt Lv Lx Ly Lz Ma Mc Md Mf Mi Mp Mq Ms Mv My Na Nb Nf Nh
Ni Nj Nl Nn Nq Ns Nu Nx Oa Oe Og Oh Ou Ow Pa Pb Pz Qm Qu Ra Rg Ri Rm Ru Ry Sf Si Ss St To Tr Tt Tz Ua Ub Uh Ul Um Vb Vc Vo Vp
Vs We Wf Wh Zw Tm Tl Xa Tj Th) jH(Ad aE aH AJ An aR aU AX bH bI bJ bM bP bQ bR bS bU bV bW cA cD cF Ch cI cK cM cP cR CT cU
Cv CW dA dB dC dE dF dH DI dN Du Eq Et Fc Fd Fn Fy Gl Gn Ha Hf Hl Hu Hv Hw IB Id Ij Il Im Ir Iu Iv Je JF jG Jn Jo Jp Js JU Kd Kg Kj Kl
Kn Kp Kz Ld Li Lt Lu Lv Lw Lx Ly Mb Mc Md Mf Mg Mi Mk Ml Mn Mp Mq Ms Mv Nd Nf Ni Nn Nq Ns Nu Nv Nx Oa Oe Oi Ok Or Ou Oz
Pb Pc Pe Pg Po Ps Qc Qe Ql Qm Qx Ra Rg Rh Ri Rj Rt Ru Ry Si Ss Tz Ub Ud Uh Uk Ul Um Uu Uz Va Vb Vc Vo Vs Vt Wb Tl Xa Tj Ti Th)
gP(Aa aC Ad Af aG AJ aK aM aO Ap Ar aS aU aw aZ Bb bF BG bI bJ bM bN BO bU cA cB cD Ch cL cM cQ cR CS Ct Cx cZ dA dD De DG
dI DK DL dM Du Ed Ef eP Eq Et Ex Fa FP Gd Ha Hc Hf Hq Hu Ih Ik Io Ip Iu Iz Jg Jh Jj Jm Jt Ju Jv Kc Kf Kj KR Ks Kx Ky Kz Li Lj Lu Lv Lz
Me Mf Mg Mj Ml Mm Mr Mv Mw Mx My Mz Na Nc Ne Nf Ng Nh Ni Nj Nl No Nq Ns Oa Of Og Oi Oy Oz Pa Pb Pc Pd Pe Pf Pg Pi Pk Qe Qv
Rg Rm Sf Sh Ua Uc Ue Us Uu Va Vb Vo Vs Vv Vw Vz Wc We Wf Wh Yk Yl Zx Ye) nW(Aa aC Ad Af aG AJ aK aL aM aQ Ar aU AW bB
BG bJ Bn BO bQ bU bV bZ cD cG cL cM cN cP cR Ct Cx cY De DG dH dI Dk DL dM dR Du Ed EF Eq Et FP Gd Ha Hc Hf Hq Hu Ik Ir Is Iu
Iz Jd Jg Jh Jm Jt Jv Kc Kf Ki Kj Kl kP KR Kx Ky Kz Li Lj Lv Lz Mb Me Mf Mg Mh Mj Ml Mr Mv Mw My Mz Na Nc Ne Nf Nh Ni Nl No Nq
nR Nu Oe Of Og Oi Ou Oy Oz Pa Pb Pc Pd Pe Pf Pg Pi Pk Pz Ql Qm Qt Qv Rg Rm Sf Sh Si Ua Uc Ue Uo Us Uu Va Vb Vo Vq Vs Vu Vv Vw
Vz Wc Wd We Wf Wh Yg Yk Yl Zx Ye) Vt(aC aD aF aI aM Ar aW Ax aY aZ BB Bc bJ bM Bn bU bX cA cD Ch cK cL cM cN Cs Cu Cx Db dD
Dr Du Ed Fa Fc Fi Fn Fp Fw Fy Gd Gn Ha Hl Hu Hx iC lj lk Il Is jG jK Jn Jr Jt Jv Kc Ki Kk Kl Kq Kr Kx Ky Kz Li Lj Lx Lz Me Mf Mh Mr
Mw My Na Nc Ne Nf Ng Ni Nn No Nr Ns Nw Ny Og Oh Oi Ok On Or Oz Pa Pb Pc Pe Pf Pg Pk Po Ps Qc Qe Qn Qt Qv Qx Qy Ra Rb Rc Rm
Rv Rz Sf Sh Si Sj Tn To Tt Tv Tz Ua Uc Uh Uk Un Ur Us Ut Uu Ux Va Vb Vi Vp Vs Wc Wd Wh Yk Yl Wm Tj) gW(aA AD aG aH aI aJ aK
aL AN aO AP aQ Ar AS aW AX BA Bb bB bF bG bH bI bJ bL BN BO bP bQ bR bV bX bZ cC cD cE cF cJ cL Co Cp cQ cS cT Cv CW cX cY
dA Db Dc DD dE dF dG dH dJ dK dL dM dN Dr Ef Em Ex Fr GL Gp Hu Hv Hx Ih Ii Ij Ik Il In Iq Ir Is Iu Iv Jg Ji Jj Jk Jl Jo Jp Jq Jr Js Lh Li Lj
Lv Lx Ma Mg Mh Mj Ml Mn Mp Mr Mt Mu Mv Mw Mx My Na Nb Nc Nd Ni Nm Nn No Nq Ns Nt Nv Nw Nx Oh Ok On Oz Pa Pb Pe Pf Pg
Qa Qb Qc Qd Qe) lK(aA aE aF aH AJ Al An Ao Ap aQ Ar aS aV aW aY aZ bB bH bM bS bV cA cC cD cF cG Ch cK cM Cq cT Cu Cv dA Dc dD De dI Dk
DL dM Dp Ef Em Ez Fc Fd Fi Fn Fw Fy Gh Gl Gn Gz Ha Hl Hq Hv Hx IB Ir It Iu JG ji Jo Js Jv Kc Kd Kk Ko Kp Kr Kx Kz Ld Li lM Lt Lw Ly
Lz Mc Mi Mj Mm Mn Mq Mz Na Nc Nf Ng Ni Nl Nn Nu Oe Oh On Ou Ow Oy Pa Qc Qe Qu Qv Qw Qx Ra Rm Ru Ry Sf Si Ss To Tt Tz Ua
Ub Ud Uf Ug Uh Ul Um Ux Uz Vb Vo Vs We Wg Zw Zx Ye Tl Xa Tj Th) iJ(aC aD aG Aj Al aM An Ar aU aW Ax bB bF BG bJ bL bM bN
Bo bQ bR bU bX cD Ch cK cM cR Ct cW Cx dB Dg dI Dk Dl dN Du Ed Ef Eq Fa Fp Fr Fw Gd Ha Hc Hf Hq Hu Ik Il Ir It Iu Iz Jd Ji Jj Jk Jl Jp
Jr Jt Jv Kc Kj Kl KR Kx Ky Kz Lh Li Lj Lv Lz Mf Mg Mh Mj Mk Ml Mn Ms Mt Mv Mw Mx My Na Nc Ng Nh Nl No Oa Of Og Ok Oy Oz Pa
Pb Pc Pe Pf Pg Pk Po Pz Qb Qv Qw Rg Sf Sh Tt Uc Ue Us Uu Va Vb Vo Vs Vv Vz Wc Wd We Wf Yd Yk Zx Ye) jY(aA aD aE aG aH AJ Al
Ao Ap aQ Ar aS aV aW aY aZ bB Bc bE Bg bl bL bN Bo bQ bR bS cA cD Ch cI cL cM Cs CT cU CW cX DC DE Dg dH dI dJ dK Eq Et Fd Fp
Fr Fw Fy Gl Gp Hb Hc Hf Hl Ho Hq Hr Hx IB Jd Je Jf Jg Jm Jp Js JT jU Ke Kg Ki Kj Kk Kl Kp Kr Ks Kz Ld Lh Li Lj lN Lp Lt Lu Lx Ml Mq
Mr Ms Mw My Nf Ng No Nr Ny Oa Of On Ou Pa Pd Ph Pk Pz Qc Qm Qz Rh Ri Rj Rv Ry Rz Ss Ub Ue Ug Ux Vq Vw Wc Yd Zq Tm) fP(Aa
aC A dc Ad aG Aj aM Ap AR bB BG bN BO bQ bR bU cD cL cM cQ cR Cs cW dD De Dg dI Dl dN Dr Du Ed Ef Eq Fa Fp Gd Ha Hc Hf Hu Ij Ik Io
Iu Iz Jg Jj Jp Jt Jv Kc Kf Kg Kj kQ Kr Kx Ky Kz Li Lj Lv Lz Mf Mg Mh Ml Mn Mr Mv Mw Mx My Na Nc Nd Ne Nf Ng Nh Ni Nl No Nu nY
Oa Of Og Ok Oy Oz Pa Pb Pe Pg Ph Pk Po Pz Qe Qv Rc Rg Rm Sf Sh Si Ua Uc Ue Ug Uk Um Us Uu Va Vb Vo Vp Vq Vv Vz Wc Wd We Wf
Wh Yk Yl Zx Ye) kR(Aa aC Ad Af aG Aj aM AO Ar As Ax bB BG bN BO bQ bU cD Ch cM cQ cR Cs Ct cW dB dD De Dg dI dN Du Ed Ef
Eq Fa Fb Fd Fp Gd Gn Gz Ha Hc Hf Io Ip It Iu Jg Ji Jj Jl Jt Ju Jv Kc Kf Kj Kl Kr Kx Ky Kz Lh Li Lj Lv lX lY Mf Mg Mh Ml Mm Mw Mx
nB Nc Nf Ni Nl No Oa Of Og Op Or Oy Oz Pa Pb Pc Pd Pe Pf Pg Pk Po Pz Qa Qe Qv Qy Rc Rg Sf Sh Si Uc Um Us Uu Vb Vo Vs Vv Vz Wc

Figure 41 Continued

We Wh Yk Yl Zx Ye) nY(Aa aC Ad Af aG AJ aM aO Ar aU Ax bB BG bJ bM bN Bo bQ bU cD Ch cM cR Cs Ct cW Cx dE Dg dI Dk Dl dM dN Du Ed Ef Eq Fa Fp Gd Ha Hc Hf Hq Io Ip Iz Jg Ji Jj Jt Jv Kc Kf Ki Kj Kl kP Kr Kx Ky Kz Lh Li Lj Lz Me Mg Mh Ml Mw Mx Nc Ne Nf Nh Ni Nl No nR Oa Of Og Oi Oy Oz Pa Pb Pc Pd Pe Pg Pk Po Pz Qn Qv Rg Sf Sh Tt Tz Ua Uc Uo Uu Va Vb Vo Vp Vs Vv Vz Wc Wh Yk Yl Zx Ye) iC(aD aE al aj AL aN aO aR bF BG bQ bU bX bZ cE cF Ch cl cM Co cS Cu cW Cx cZ Db dD Dk dM Du Ef Eq Et Fi Fn Fr Gl Gn Hc Hq iB Il Io Iq Is It Jd Jh Ji JK Jl Jo Jp Jq Ju Jv Jy Kg Ki Kj Kk Kl Ko Kq Lh lM Lv Ma Mf Mg Mj Mm Mn Mu Mv My Mz Nj Nq Nv Nw Of Ok On Ou Oy Pf Pg Pz Qd Qe Qh Qn Qu Qv Qw Qz Rb Ri Rt Sf Sj Ss St Tn Tr Ua Ub Uc Uf Vi Vq Wb Wf Yd Zw Zx Tm) jG(AD aF aG al aN aO AR Aw aX aZ Ba bG bL bM bN Bo bU bV bX cM cO Cp cQ Cs cT Cv cW Cx cY Db dF dK dM Dr Eq Et Fc Fn Fr Gh Gl Gp Ha Hb Hv Ii Iq Iu Ji Jm jP jT Ju Jv Kc Ke Kl Ko Kr Lh Li Lj lM Lt Lv Me Mf Mh Mj Ml Mn Mt Mu Mv My Nc Nd Ne No Nq Nt Nx Oe Of Om On Ou Pa Pe Ph Ps Qb Qc Qd Qh Qw Qz Rc Rf Rg Rm Sf Sr Ss To Tt Ua Va Vo Vs Wc Wd Wh Zq Tl Tj) jK(aD AJ aL aP aU AX aZ Ba bB bC bF bH bJ bM bN Bo bR bS bV cC cF cl cK cL cM cO Cq cS CT cW dA dB dC Dd Dg Dp Dr Du Eq Et Fc Fn Fr Gl Hf Ib Ih Ij Iq Jh Jt Kd Kg Kp Kr Kz Ld Lt Lw Ly Lz Mc Md Mg Mi Mp Mq Ms Na Nc Nf Ng Ns Oa Oe On Ou Pe Po Ps Ql Qm Qx Ra Rh Rj Ru Rz Sh Si Sj Ss St Ua Ud Uh Ul Um Ux Uz Va Vc Wc We Wg Wh Yl Zw Tm Xa Tj Th) oH(Aa aC Ad al Aj aL aM aO Ar As Ax bB BG bN BO bQ bR bU cD cM Cs cW De Dg Dl Dr Du Ed Ef Eq Fa Fp Gd Ha Hc Hf Hu Ik Io It Iu Iz Jj Jp Jt Jv Kc Kg Ki Kj Kl Kr Kx Ky Kz Li Lj Lv Lz Me Mg Mh Ml Mp Mr Mv Mw nB Nc Ni Nl No Oa Of Oy Oz Pa Pb Pc Pd Pe Pf Pg Pk Po Pz Qe Qv Rg Sf Sh Si Ua Uc Ug Um Us Uu Va Vb Vo Vs Vv Vw Vz Wc Wh Yk Yl Zx Ye Xa) kQ(Aa aC Ad aG Aj aM aO Ar aS aW Ax aZ BB BG bJ bN Bo bR bU cD cL cM cR Cs dD Dg Dk Dl Du Ed EF eP Eq Fa Fp Gd Gn Ha Hc Hf Iu Iz Jd Jj Jt Jv Kc Kf Kj Kl kP Kr Kx Ky Kz Li Lj Mg Mh Mj Mv Mw My Nc Ne Nh nK Nl No Nq NR Of Og Oi Oy Oz Pa Pb Pd Pe Pg Pk Qb Qv Rc Rg Sf Sh To Ua Uc Ur Uu Vb Vo Vp Vq Vs Vv Vw Vz Wc Wd We Wh Yk Yl Zx Ye) hG(Aa aC Ad Aj Al aM Ao Ar As Ax bB bF BG bJ bQ bU cD Ch cL cM Cs cW dD De Dg Dk Dl Du Ef Fp Gd Ha Hc Hf Ip Ir Iu Iz Jg Jj Jt Jv Kf Kj Kl kP Kr Kx Ky Kz Li Lj Lv Lz Mf Mg Mh Mr Mv Mw Mx My Mz Na nB Nc Nf Ng Ni Nl No Nr Ns Oa Of Og Oy Oz Pa Pb Pc Pd Pe Pf Pg Pk Pz Qe Ql Qv Rg Ry Sh Ua Uc Uu Va Vb Vo Vs Vv Vw Wc Wd We Wh Yk Yl Zx Ye) nB(aC Ad al Aj aL aW bB bN bU bX cD Ch cM cN cR Ct Dc dD Dl DU Ed eF eM EQ Et fA gC Gd Hc Ho Hv Ic Ii Ik Il In iO It Iu jB Jj Jp Jt Jv Jy Kf kG kI Kl kP Ky Li Lj lW mE Mg Mn mS Na nK Nl Nr Nx oD Oe Of Og oO oP oQ oT oV oW Oy Oz Pa Pb Pd pH pK Pz Ql Qz Rm Sf Sh Si Uc Ue Ug Ur Uu Va Vb Vq Vs Vw Wc Wh Yk Ye) iH(Aa aC Ad Af Aj aM Ar aW Ax bB BG bJ bL BO bU cD Ch cM Cx Dg Dk Dl Du Ef Eq Et Fa Fp Fw Gd Ha Hc Hf Hu Iz Jg Jj Jt Jv Kf Kj Kl Kr Kx Ky Kz Lh Li Lj Lz Mg Mh Ml Mu Mv Mw My Na Nc Ni Nl No Of Og Oi Oy Oz Pa Pb Pc Pe Pf Pg Pk Qv Qz Rc Rg Rm Sf Sh Si Ua Uc Us Uu Vb Vo Vp Vq Vs Vv Wc We Wh Yk Yl Zx Ye) jT(AD AfaG aH Al aN aR aU aV aX Bg bJ Bn bO bQ bZ cC cD cF cl cJ cL cM Cp cQ cS CT Cv cW cY dA DC dG dH Di DL dM Dr Ed Ef Em Eq Et Fn Fw Fy Gl Ho Ih Im Ip Is Iz jF Jg Jl Jp Jy Kf Ki Kj Kk Ko Kx Ky Li lM Lt Me Mf Mg Mh Ms Nc Ni Nj Nv Ny Og Oh On Ou Pa Ps Qb Ql Qu Rh Rj Rz Tt Ua Ue Ug Vb Zw Tm) oK(Aa aC Ad Aj Ar As Ax BG bJ bO bQ bU cD cM Cs cW Cx Dg dI Dk Dl Du dX Ed Ef Eq Et Fp Gd Ha Hc Hf Hu Iz Ji Jj Jt Jv Kc Kj Kl Kr Kx Ky Kz Li Lj Lv Lz Mg Mh Mj Mw Mx My Na Nc Nh Ni Nl No Nr Oa Of Og Ok On Oy Oz Pa Pb Pc Pe Pf Pg Pk Qe Qv Rg Sf Sh Tt Ua Uc Uu Va Vb Vo Vs Vv Vz Wc We Yk Yl Zx Ye Tj) hB(Aa aC Ad aG Aj aM Ar Ax bB BG Bo bQ bR bU cD cL cM Cs cW dB Dg dI Dk Dl Du Ef Eq Fa Fp Gd Ha Hc Hf Ip It Iu Iz Jd Jg Jj Jt Jv Kc Kf Kj Kl Kr Kx Ky Kz Lh Li Lj Lv Mg Mh Mj Nc Ng Nh Nl No nR Oa Of Og oP Oy Oz Pa Pb Pc Pd Pe Pf Pg Pk Po Pz Qv Rc Rg Sh Uc Uu Vb Vo Vs Vv Vw Wd We Yk Yl Zx Ye) oN(aC Ad Af Aj aM aO Ar Ax bB bF BG bJ bU cD cL cM cR Cs cW Cx Dg dI Dk Dl Du Ef Eq Fa Fp Gd Ha Hc Hf Ik Iz Jd Jg Jj Jt Jv Kc Kf Kj Kl Kr Kx Ky Kz Li Lj Mg Mh Mj Mw Nc Ne Ng Nh Nl No nR Of Og Oy Oz Pa Pb Pc Pd Pe Pf Pg Pk Pz Qv Rc Rg Sf Sh Uc Us Uu Vb Vo Vs Vv Vw Vz Wc Yk Yl Zx Ye) kS(Aa aC Ad aG Aj aM Ar As Ax bB BG bU cD cM Cs cW Dg Dk Dl Du Ed Ef eP Eq Fp Gd Ha Hc Iu Iz Jj Jt Jv Kc Kf Kj Kr Kx Ky Kz Li Lj Lz Me Mg Mh Ml Mw Na Nc Nf Ni Nl No Nq Oa Of Og Oy Oz Pa Pb Pd Pe Pg Pk Po Pz Qv Qy Rg Sf Sh Ua Uc Uu Va Vb Vo Vs Vv Vz Wc Wd We Wh Yk Yl Zx Ye) mS(aC aD aM An aW bB bI bL bN bQ bU cD cM cR dN Du Ed Et Fa Gb Gd Gp Hc Hu Ic Id Ij Il Ir Iu Jj Jp Jv Kc Kf kG Kj Kp Ky Kz Li Lj Lv mF Mg Mm Mn Mr mU Mw mY Na Nb Nc Nl nN No Og Ok On oP Oy Oz Pa Pb Pc Pd Pe Pf Pg Qe Qv Rb Rc Rg Sh Ue Ug Us Uu Va Vb Vo Vs Vz Yk Yl Ye Tj) iB(AD al AP aR aV Ax aZ Bc bF bM bO cD cE cG cl cJ cM Cq cS CU cW dJ dN Du Ed Eq Et Fc Fi Fw Gl Gz Ha Hu Ih Ii Ik Jg Ji jO Jp JU Ke Kr Lh Lx Mb Md Me Mg Mk Mn Mu Nj Nq Nt Nu Of Og Om Op Or Ou Pj Po Pz Qm Qt Rc Rh Rj Rx Si Sr St Uh Uo Vh Vo Ye Xa Wm Tj Th) oF(Aa aC Ad aG Aj Ar As Ax BG bJ bO bQ bU cD cM Cs cW dD Dg Dk Dl Du Ed Ef Eq Fa Fp Gd Ha Hc Hf Iz Jj Jt Jv Kc Kf Kj Kl Kr Kx Ky Kz Lh Li Lj Mg Mh Ml Na Nc Nf Nh Nl No nR Oa Og Oy Oz Pa Pb Pc Pe Pg Pk Po Pz Qv Rg Sf Sh Uc Uu Vb Vo Vs Vv Vz Wc Wf Wh Yk Yl Zx Ye) iO(Aa aC Ad Aj Al aM Ar Ax bB BG bQ bU cD cM Cs Ct cW Dg Dl Du Ed Ef Eq Fp Gd Ha Hc Hf Hq Iz Jj Jt Jv Kc Ki Kj Kl Kr Kx Ky Kz Li Lj Lv Mg Mh Mw Mx My Nc Ng Nh Ni Nl No Oa Of Og Ok Oy Oz Pa Pb Pe Pg Pk Pz Qv Rg Sh Ua Uc Uu Va Vb Vo Vs Vv Wc Wd We Yk Yl Zx Ye) kP(Aa aC Aj aM aP Ax bB bN Bo bQ bU cD cM Cq cR Cs cW dD dN DU Ed Fa fR Gd Gn Gp Hu Ii Jj Jp Ju Jv Kf kG Ki Kj Kk Kx Li Lj Lv lW mE mF mI Mr Mx nA Nb Nc nD Ne Ni nK Nl NN No Nr Oa Of Og Ok Oy Oz Pa Pb Pe Pf Pg Pz Qa Qe Qv Sf Sh Ug Ur Uu Va Vs Yk Yl Ye Xa) jU(aH aI Al Ar Aw aY BA BB BG bM Bn bZ cE cJ cM Cv cW cX cZ DD Di Dk Et Ex Ez Fy Gb Gl It Iu Jh Jl Jk Jv Kk Ky Li Lv Mb Mf Mj Mn Mw My Mz Ng Ni Nj Nl Nu Ny Oa Ou Oz Pc Pd Pk Qd Qe Qh Qm Qv Qy Rb Rf Rg Rj Ry Sf Tr Ug Vb Vq Wb Wf Wh Yl Zx Ti Th) jO(aD Aj aV Ax BA bB bM bN bR bS cA cF cK cL cM cS Ct cW dA Dd De dF dI Em Et Fc Fn Gl Hv Hx Iu Jg jI Jp Jt Jv Kd Kz Lh lN Lt Lx Ly Mc Md Mg Ml Mp Mq Ms Mt Nd Nf Ng Ni Nj Nq Ns Nv Oe Oi Ou Ps Qw Qx Rm Ru Rx Sf Sj Ss Uh Ul Um Uo Vb Vc Wb Wg Tj) lN(aD aG aI aL aM aN aP aW aX bA Bb bG Bo bZ cB CH cM cR Cs cU cV cW dB dD De dF Eq Fy Gb Gl Hx Ic Il Jd Jj Jl Jv Kx Lu Lv Lx Ma Md Mk Ms Mu My Nb Nh Nj Nt Nv Oa Oi Op Or Ou Pd Pe Pg Qa Qd Ql Qm Qn Qy Rg Rx Tn Tr Ug Uk Va Vh Vp Wf Zq Tj) mE(aC Ad Aj aM bB Bg bN cD Ch cM Cp cR Cs Dg Dk Dl dN DU Ef Eq FA fB Gd Hc Jj Jo Jt Ju Jv Kc Kf Ki Kj Kl Kr Kx Li Lj lX lY Mg Mh Ml Nc Nl Of Og oP Oy Oz Pa Pb Pe Pg Qv Rg Sf Sh Si Tt Uc Ug Ur Uu Va Vb Vo Vs Vv Vz Wc We Yk Yl Ye) Lj(dU eF eQ fA gL gZ hF jB kC Kd kE kF kG kI kK kN kO lW lX lY mF mH mI mM mP mT mU mW mY mZ nA NC nF nH NI nJ nK nL nM nN nO nR nT nU oD oO oP oQ oT oV oW pF pH pK Qb Qv Rg Rv Sf To Uk Ul Un Ur Uu Vb Vi Vq Vv Vw Wb Wc tF) jI(aD aE aG aH Al aM aO aQ Ax BC bF bH bI bP bX cA cG Ch cM cO CT Cu Cv cW cZ dA Dd De dK Dp Em Et Fn Gb Gh Gl Ho Hv Ij Is Iz Je Jf Jt Ki Kk Li Lu Mj Mm Ms Mu Mv My Nb Nc Oh Ou Pd Ph Ps Pz Qb Qz Ri St Ub Uk Vo Vs Wd Wf Tm) pF(Aa Ad aG Aj aM Ar Ax bB BG bL Bo bU cD cM Cs cW Dg Dl Du Ef Eq Fp Gd Ha Hc Hf Iu Iz Jj Jt Jv Kj Kr Kx Ky Kz Li Mg Mh Mw Nc Nf Ni Nl No Oa Og Oy Oz Pa Pb Pc Pe Pg Pk Qv Rg Sh Uc Uu Va Vb Vo Vs Vv Wc We Wf Wh Yk Yl Zx Ye) Vq(aC Aj aM Ar Ax bU cD cM Cs Dl Du Ed Eq Fa Fp Gd Ha Hc Ij Ik Ir Jj jL Jv Kl Kz Lh Li Me Mg Mh Mr Mw Na Nb Ne Ng No Nr Oa Oi Ok Oy Oz Pa Pb Pe Pg Po Qa Qe Qv Qz Rc Sf Sh Tt Ue Uk Us Uu Va Vb Vo Wb Wc Ye Tj) jF(aD aH Al aP aR Aw Ax BC bM bN bW cC cG cM Cu cW Cx dA Dd dG dL dN Dp Dr Eq Et Fn Gl Gz It Ju Kc Ko Kr lL Lu Mb Me Mj Ms My Ng Nj Nq Nu Nv Oi Op Or Ou Ps Qd Qm Rm Sh St To Ua Uh Un Uo Vb Vw Wb Wh Ti Th) hF(aC Ad Aj aM Ar bB BG bQ bU cD cM Cs Dg Dl Du Ef Eq Fa Fp Gd Ha Hc Hf Iu Iz Jt Jv Kj Kr Kx Ky Kz Li Mg Mh Ml Mw Nc Nl No Og Oy Oz Pa Pb Pe Pg Pk Qv Rg Sf Sh Uc Uu Va Vb Vo Vv Vz Wc We Wh Yk Yl Zx Ye) jL(aD aE Af aH aI Aj aZ bB bM bP bU bX cM cO Cu Cv cW Db dD dH dK Fi Fn Fr Gl Gn Hc Ho Ih Io Iu Jo Jq Jr Kg Kk Lh Lt Lu Lv Mf Mg Ms Nc Nh Ni Nt Nv Oa On Op Or Ou Pg Pj Qu Qz Rt Ry Ss Ux Vi Vo Wb Zw) Qe(Aj aW Ba cD cM Ct Cx cZ Db DG DL Du Ef Em

Figure 41 Continued

Figure 41 Continued

Va Vb Vc Vh Vo Vp Vs Vv Vw Vz Wb Wc We Wg Yd Yg Yi Yk Yl Zq Zw Ye Tm Tl Xa Wm Ti Th Yf) bU(aF aG aO aR bE bN cC cK cR cS Cv dM eF fP Fy gL Hc Ic Id Ip Ir Iz Je Ji Ju kP Kx Ky Kz Lj mE Mf Ml Mn Mx nA Nj NN No Nr Oa oO oP Pa Pb Ph PK Ps Pz Qa Qb Qc Qd Qe Qg Qh Qt Qu Qv Qx Qy Qz Ra Rb Rc Rg Rj Rv Sr Ss St To Tr Tt Tv Tz Ub Uc Ud Ue Uf Ug Uh Uk Ul Uo Up Ur Us Uu Uv Ux Va Vb Vh Vj Vo Vq Vu Vv Wc Yj Yl Wm Tj) bL(Bb bI Cw Du Fd Fi Gp Hb hG Ic Ir Jf Jg Ji Kd Ko Kq lY mE mI Nj Nk Nm Nn Ok Oz Pk Ps Qc Qe Qg Qh Qt Qu Qv Qw Qx Qy Qz Ra Rb Rc Rf Rg Rh Ri Rj Rm Rt Ru Rv Ry Si Sr Ss St Tn To Tr Tt Tv Ud Uf Ug Uh Ul Un Up Ur Us Uu Uv Uw Ux Uy Uz Va Vb Vc Vh Vj Vo Vp Vq Vs Vt Vu Vv Vw Wc Wd We Wg Wh Yi Wm Th Yf) mE(Aa Af aI Ax bH bI bR cA cI cM Cx dM Dr Du eC Ef Et Fa Fb Fd Fw Fy Gl Ha Hb Id Iu Je Jf Ju Kd Ke Kf Kg Kj Kl Ko kP Kq Ks Kx Ky Ld Lh Lj Lt Lu Mf Ml Mn Mx Mz nC Ne Nk Nl No Nr Oa Ok Or Ow Ph Pj pK Qe Qh Qt Qu Qw Ra Rb Rf Rg Ri Rt Ru Sr Tn Tr Tt Tv Un Us Uv Vs Vt Wc Yg Yh Yi Yj Yk Zq Tj Ti Yf) bX(Ax Fd Fy Ha Hf Id Je Ko Kq Ks Kx Ky Kz Lt Nj Nn Oz Pk Ps Qe Qg Qh Qt Qu Qv Qw Qx Qy Qz Ra Rb Rc Rf Rg Rh Ri Rj Rm Rt Ru Rv Sr St Tn To Tr Tt Tv Tz Ua Ub Uc Ud Ue Uf Ug Uh Uk Ul Um Un Uo Up Ur Us Uv Uw Ux Uy Uz Va Vb Vc Vh Vi Vj Vo Vp Vq Vs Vt Vu Vv Vw Wc Wd We Wg Wh Yi Wm Ti Th Yf) Lj(Bo cI cQ cR cW Dr Du Eq Fc Fd Fi fR Gb Gh Gz Hb Hl Ho Hp Id Jf Kl Ko Lp Lt Mj Nj Nn Op Ps Qg Qm Qz Rt Ru Rv Rx Ry Rz Si Sj Ub Uo Ur Uw Ux Uz Va Vc Vh Vi Vj Vv Vw Vz Wb Wd We Wg Wh Yd Yg Yh Yi Yj Yl Zq Zw Zx Ye Tm Tl Xa Ti Th Yf) Lt(Al aN aO AX bH bI Dc dE Fb Fw Fy Ii Ij Il Im Ip Iq Ir Jg Jm Kd Ke kR Lv Me mH mI Mm Mn Mx mY mZ nA Ne Ng Nk NN No Nr Ny Oa Ok oP Oz Pb Pc Ph Qa Qb Qc Qe Qh Qu Ri Ru Ry Sr To Ul Uy Wd Zq Ti Th) Wc(Al AX bH bI cJ Dc dE dG dJ Et Fy Gp Ha Ih Ii Ik Il Im Io Ip Ir Is Jn Js Ke Kn kR Lh Lp Lv Me Mm Mn NA Ne Ng Nk No Nr Nv Ny Oa Ok On oP Oz Pb Ph Pj Po Qa Qe Qh Rb Rj Rt Rv Si St Tv Wd Yl Zq) Vb(An Ao bH bI bJ cH Dd Fi Fw Fy Ha Hq Hw Hx Id Il Im In It Jg Jt Kq kR Ks Lv lW Mf mH Mm Mn Mx mZ nA Ng Nk Nm Nn Nr Of On Or oW Oz Pb Ph Pj Pz Qb Qc Qh Qu Rt Ru Rz Tv Uk Vh We Yj Ti) Dd(Ax bH Dr eC Eq Fd Fi Gb Gh Gn Hb Hl Ho Hp Jf Kc Kr Kz Lp Nk Qe Qv Qz Rt Ru Rv Rx Ry Rz Sf Sh Si Ux Uy Uz Vc Vh Vv Vz Wb Wd Wg Yd Yg Yh Yj Yl Zq Zw Zx Tm Ti Yf) Kl(Ap Ax bI Dg eC Et Fb Fy Gp Ij Im Ir Is jB Jg Ko Kq mI Mm Mn mZ Ng Nk Nm Nn No Nr Of Oh Ok On OW Oz Pa Pb Pz Qb Qc Qe Qh Qu Ru Rz Sr Tn Uf Uw Uy Yi Zq Xa Ti) Nj(aF aQ Ar Ax aY bG bH bI bJ bN bR bW cA cK cR Cx dK eC Fw hC Hx Im Jn Jr Kd kP Ky Lp Ml Ms Mt mZ NB Nk nL NN No Nr Og Ok On oW Pa Pf Qa Qe Qu To Uy Vs) Ng(Ax Du eC Eq Fc Fd Fi fR Gb Gh Ho Hp Kc Lp mI Ps Qz Ru Rv Rx Ry Rz Sh Sj Uu Uw Uy Va Vh Vi Vs Vz We Wh Yd Yg Yh Yi Yj Yk Zx Ye Tm Tl Xa Ti Th) Ru(aN Bc cD cJ cK cM cR Db dG dM Du eF Em Fy Gn Ha hC Hu iA Ij Ji kP Kx Ky Kz Lu lW Mk Mm Na Nd Nx Ok Pa Pe Pf Pj Qb Qc Qy Rt Tv Up Yl) Tv(Ax dJ eC Eq Fc Gh Hl Hp Lp mI mZ nH nL Qc Qz Ry Sf Si Uw Uy Va Vz Wd We Wh Yg Yk Yl Zx Ye Tm Tl Ti Yf) Mn(cH cM Du eC Eq Fd Ic Jd Kc Kz Lp nI Nk nR Sf Si Us Uy Vj Vz Wb Wd We Yd Yj Yk Yl Zw Zx Ye Xa Th) Nk(Al aO Ax bM bN Ha Id Ih Im Ir Ju Ky mI Ml nL Nn Nr oW Pj pK Qc Qu Qv Rc Ss Uc Ur Uu Uw Ux Vo) Jf(Ax cJ cK cR Fb kP Ky Mt Mz Nn No Pk Qa Qb Qe Qg Qv Rc Ss Uc Ud Ug Um Ur Uu Ux Vo Vs Vv Xa) Nn(Ax Bg bH bW cM cR Cs Ct Du Fp Gn hG Hu Ji kF Kz Mg mI Nd oP Oy Oz Pa Pb pK Qc Wh Yl) Vs(aL cK cM Cq cR dD Fy Ha Id Ij Il jB kP Kq Ky Kz Mv Mx Ok Oz Pb Ph Qh Qu Qz Tn Xa) Gp(aG aO Bc bI bJ cJ cK cM Fd Fp Fy Il Ji Jo kP Ky Mm Mx No nR Pj Ub Uk Uo Yj Ti) cM(Ax Fp Kd Ko Ky Kz mI Ml nN Nr Oz Ph Pj Qc Qe Qu Sr Tr Uh Uk Ul Us Uu Ti) Xa(bM Eq Fy Ha iA Jd Ji kP mW Mx NA Ne Nh Nr oP Oz Pb Uk Uo Ti) Ax(bJ dM Fd Hc Id Ji Jl Js Kz Lv Mj Mv nA nI Pa Pc Qu Rf Ub Vv) Uy(Al aN Bc cJ cK cR eF Ha hC iA Ji kP Kx Kz Mv Mx Na Nx Pj Th) Oz(aL aQ bH Bo cB cF cK cR eC Fr Jg Jp kE kP Me Mj nL Ok Yh Tl) Qu(bF bH cD cR Ef HC Iz Kc kP Kz Mg oP pK Uw Wd Wh Yk Zx) Lp(Bc cR dM Fp Hu Ij Ji Kx Ky Kz Mm Na Nd Nf Nx oP Pf Qb Yl) Fy(Aj eC kP mI mZ nL Ou Rx Uu Uw Ux Vv Wd Wh Yg Yh Yk Zx) Du(aN bN cJ dG Ed Fw Ij Il Im Ir Jm Mx nN No Nr Ph) Uw(bI Ij Im Ir Is Jp Js Kq Ks Mx No Ok Qa Qb Qh Yi) cR(aO cZ Fc Kd Ki KK Ko Ql Ri To Ul Uv Vp Wd Th) kP(Jg Kd Ko Qz Rv Ry To Ua Ul Uv Vp Wd Wh Yg Yl Zq) Ha(Dp Eq Fc Fd Jp Ko Mj mZ nR Po Rv Ry Vp Wh Yl) Rt(Al Ed Fw Il Im Jm Kd Mx nL nN No Nr Ph To Uu) Yi(Bc Ch Ct dM Fr iA Lv lW Mx oP Ql Wh Yg Yk) Qc(Bo cK Hc Jd Kd Ki Mj Nh nR Qm To Up Vp) Kz(Fw Im Jm Jn Jp Kd kK mZ Nr To Ul Tm Tl) Uu(Ao bH bI Fi Iq Jo Lv mZ Nm Of Pj Pz Rz) Id(Ar eC Ir mI mZ Ne nL No Pj Qe Ue Wd) Ij(Eq Hp Kr Ps Ux Va Vw We Wh Yg Yk Ye) Il(Fc Kc Ko Qv Rv Ux Vv Wh Yh Yl Zx Yf) Im(Fc Ko pK Ps Rv Vq Vv Wd Wh Yl Ti) Yl(Al Fw Jm Ju Kd Ks Mx nL Nr Ph) oP(Kc Qv Rz Sf Va Vi We Zq Ti Yf) bH(Ky nN Qg Qv Ud Um Ur Ux Vv) Fd(Aa kR lW Me Ml NA Nr) Mx(Gh Ko Rv Sf Sh Ux Vh Wh) cK(hG Ko Qe Ry Uh Wd Zq Ti) mI(bV Cw Kd Kq Ks Oa Tn Ul) Eq(Ky nA No Ok Ph Qz Tj) Wh(Al Cq Ks Ow Qa Qb Tn) eC(cJ Io Kn Mk mM Rb Tj) Ti(Bc cJ Ed hC Lv Ux) Nr(Ic Kc Rf Rv Vv Vz) Mj(Kq Oa Ow Qe Rb St) Yk(cJ Ji No Ok Ph Qh) Wd(bJ Hq oW Ph Qa Qz) Kd(hC hG Hu Ko Nx pK) nA(Gh Rv Sf Yh Zw Ye) Qb(Aa Qz Rm Rx Ub) mZ(Ji Kx Qv Rb Uh) No(hG Kc Vv Yd) Ir(Aa kO Ky Oe) Qe(Aa cF nR Pg) Al(Hl Ub Ux) Th(Bc nB Ne) To(aL hC Hu) Ye(In Jj Jo) Ko(Ch Jm oW) Kx(An Fc Po) Ok(Jd Oe Vv) Ph(Ps Rv Zx) bI(Ed Ub Yh) Ih(Ux Vv) Yj(cJ Um) Ks(Dp Rv) Pj(nR Oa) dD(nR Uo) lW(Op Ry) pK(Aa nN) BgJg ChCw DkKq EtJd FcNx FwQv MeHf NakF TtOy YdJi ZxUk QaPs QhnL JoUx JsRm UlhC aOjB} gV{Ki(AA aC Ad aE aF aG AJ aK AL aM An AO Ap aR AS aU aV AW AX aY aZ Bb Bc bE Bg bI bJ bM BN BO bR bS bU bV bW bX cA cB cC cE cF cG cH cI cK cL cM cN CO Cp CQ cR Cs CV Cw CX cY cZ dA DC Dd DE dH DI dJ DK DL dM dN Dp dX Ef Em eP Et Ez Fa Fb Fp Fr Fw Fy Gd Gl Gp Hb Hc Hf Hq Hr Hv Ib Ic Id Ii Ij Ik Im In Is Iu Iz Jd Je Jg Jh Ji Jj Jk Jl Jm Jn Jo Jp Jq Js Ju Jv Jy Kc Kd Kg Kj Kk Kl Ko Kr Ks Kx Ky Kz Ld Li Lj Lu Lv Lx Ly Lz Ma Mb Mc Md Me Mf Mg Mh Mi Mj Mk Ml Mm Mn Mq Mr Ms Mt Mu Mv My Mz Na Nb Nc Nd Ne Ng Nh Ni Nj Nk Nl Nm Nn No Nq Nr Ns Nt Nu Nv Nw Ny Oa Oe Of Og Oh Om Or Ou Oy Oz Pa Pb Pc Pd Pe Pf Pg Ph Pi Pj Pk Po Pz Qa Qc Qd Qe Qg Qh Ql Qm Qn Qt Qu Qv Qw Qx Qy Ra Rc Rf Rh Ri Rj Rm Sr Ss St Ua Ub Uc Ue Uf Ug Uh Um Un Ur Ut Uu Uv Vt Vu Vv Wm Tj) Kx(Aa AD aJ aK aM AN AO AP aQ AR AS aU aV AW AX aY Ba bC bF BG bH bI bJ bL bM BN BO bP bQ bR bS bU bV bX bZ cA cC cD cE cG Ch cI cJ cK cL cM cN CO cP CQ cS Ct CU cV CW CX cY cZ DB DC DE dF dG dH DI dJ DK DL dM dN Ed Ef EM Et Ez Fa fP fR Fw Fy Gl Ha Hb Hf Hq Hr Hu Hw Hx Ib Ii Ij Ik Il Im In Io Ip Iq Ir It Iv Iz Jg Jh Jj Jl Jm Jn Jo Jp Jr Js Jv Jy Kc Kd Ke Kf Kg Kk Kl Kp Kr Kz Ld Lh Lj Lu Lx Ly Lz Ma Mb Mc Md Me Mf Mg Mh Mi Mk Ml Mn Mq Ms Mu Mw Mx Na Nd Nf Nh Ni Nk Nn Nq Nr Ns Nu Nv Ny Oa Of Og Oh Ok Om Ou Ow Oy Oz Pb Pc Pe Pf Pg Ph Pk Po Qd Qe Qg Qh Qm Qv Rj Rm Tz Ub Uf Ug Uh Un Up Us Ut Vo Vp Vs Vt Vv Tj) Vt(Aa aC aE AF aG AJ aN AO aP aQ AR aS aV AW AX aY aZ bA bB Bc bF Bg bH bI bJ bL bM BN Bo bP bR bS bV bX cB cD cG CH cK cN CO CP CQ cR Cs cT CU Cv CW CX cY cZ DB Dc dD DE dG dH Di dJ DK dM dX Ed Ef EM eP Et Fn FP fR Fw Fy Gd Gp Hb Hc Hf Hr Hw Ib Ic Id Ih Ik Il Is It Iu Iv Iz Jd Jg Jh Ji Jj Jk Jl Jo Jq Ju Jv Kc Kd Ke Kg Kk Kn Kp Kr Ks Ld Li Lu Lv Lw Lx Lz Ma Mb Mc Md Me Mg Mi Mm Mp Mr Mt Mu Mw My Mz Na Nb Nd Nf Nj Nn No Nq Ns Nu Ny Oa Of Oh Oi Om On Or Ow Oy Oz Pa Pb Pc Pe Pf Po Qa Qe Qv Qx Qy Rc Rh Ri Rj Sr St Tz Ua Ub Uc Ud Ue Uf Uh Ul Um Un Uo Ur Ut Uu Uv Vo Vp Vu Vv Wm Tj) Uu(aC Ad aF Aj Ao aQ aV Ax bH bO cL cP CQ Cs Cv Cw Dc Dd Dg dL Et Fp Fr Ha Hb Hx Io Ip Is Jk Jp Ke Kf Kl Ko Kq Ky Lh Li Lj Mr Mt Mx Nr Nw Oa On Pe Pj Po Pz Qa Rg Rm Uc Uf Uh Um Un Vu) Ug(aF aK aM Ap aQ AR aU aV bH bO cB cD Cv cY dD dI eP Et Fp Gp Hq Hu Hx Ih Iv Jn Jp Jv Ke Ko Kq Lh Li Lj Lu Lx Mb Mn Mq Mr Mx Nf Nm Nq Nt Oa Ow Pd Po Qa Qe Qh Qt Rg Rm St Vu) Mb(aM As cP Dd dR dW Ed EF eO EW Ex Fy GL Gp Io Jr Kd Ke Kf Kj Kn Kq Kr Ks Nk Nw Oa Ok Or Ou Ow Pi Pj Qh Rb Rg Ri Tz Ub Uh Um Un Up Us Ut Vo Vp Vs Tj) Lx(aM Dp dR Ed Ez Fn Fy Gp Ha Hc Hf Ic Jd Je Jv Kd Kf Kl Ky Kz Pi Ql Qt Qu Qw Qz Rb Rc Rf Rg Ss Tz Ua Ub Ud Uh Uk Ul Um Un Uo Ur Us Ut Uv Vo Vp Vs Vu Wm Tj) aC(aD Dp Ed Ez Fn Ha Ib Ic Id Jd Je Jf Jy Lw Pj Qg Ql Qm Qn Qt Qu Qv Qw Qx Qz Ra Rb Rc Rf Rg Rm Sr Ss St Ub Uc Ud Uf Uk Ul Up Ur Us Ut Vo Vp Vs Vu Vv Wm) aD(aF aK aL aM Ax bE Bo cB cP cT Cu

Figure 41 Continued

CX Dc dD Fp Hv Hx Ij Iq Ir Is Ji Jl Jr Li Lj Lv Mh Mi Mj Mk Mn Mr Mx Nr Oh Ok Pe Qb Qd Qe Qh Uf Uh) Lj(aM cW Dp dR Ez Fa Ha Hc Iz Jv Jy Ke Kg Kj Kl Ks Oa Qn Qv Qw Qx Qy Ra Rg Rh Ri Rj Sr St Tz Ub Uc Uf Uk Um Up Ur Us Ut Uv Vo Vs Tj) Vo(Aa Ad AF aK cI Cs Cw Dc dD Et Ex Fp Hx Ij Is Iu Ke Kn Ko Li Lv Ma Mf Mj Mk Mt Mx On Ow Pj Po Qe Qn Qv Qx Rf St Uf Tj) aM(aF Aj bA Bo cH cP CX Dc Dd Dw eO Ew Hc Iq Is Ji Jy Kc Kd Ke Kn Ko Kp Ky Lv Lz Ml Mn Mz Nw Oh Pj Qh Qm Qu) Rg(Ad Aj aU aZ cI cP Fp Gd Is Iu Jp Ke Ko Ky Li Lv Mk Mr Mz Nm No Ok On Ow Qh Sr Ue Uh Un Vu Tj) Fa(Aa Aj Bg bX cF Ch Cp cR cX dG Fb Hc Ik Il Iz Jh Ji Kl Lh Lz Mf Mh Ng Ni Oe Of Oh Or Ph Pj) dR(AF Ax cA cP cV CX Dc eP Hx Ih Iq Ir Ji Lh Li Mf Mj Mk Ml Mw Mz Nw Nx Ok On Po Qb Qe) Aj(Ad Ap bM Bo cW Dp Jf Lw Nw Oa Ok Ow Qn Qt Qu Rb Rm Ub Up Ur Us Uv Vp Vu Tj) Vv(aI aL aQ aU Ax bB bH Cs Cw cY dD Et Fp Hx Is Ji Jp Ko Ky Mk Nt Oa Ok Uh Un) Iq(Dp Fy Id Jd Je Ky Ld Oa Of Qw Qz Ra Rf Ub Ud Uk Ul Un Up Vp Vs Wm) Ss(aK Ap cP Cs Cw dD Et Fp Fr Fy Hx Ko Li Mh Nn Ok On Ow Pc Pj Po Sr) Qx(aF aI aK Cs Cv dA Dc dD Fy Ha Ip Ji Jl Jp Ke Mr Nr Po Qe Uh Vu) Un(Bg bX Ch Cs Cx dD Dk Fw Hc Ib Io Jv Kj Kr My Nd Ph Qv Uc Tj) Li(eF Ez Hc Ib Iz Jd Jv Kf Kg Kj Kl Kn Nj Qv St Tz Uc Uo Uv) Oa(Ch Gd Hu Ib Ih Ii In Jj Jk Kr Mh My Nu Nv Oi Qv Qy Ua Ur) Qh(Bb Bo cA dC Hv Ii Io Jj Jn Jp Js Mf Nh Rm Uk Up Ur Vp) Jp(cX Hc Ic Iz Ju Jv Jy Kj Kz Ld Or Ou Pk Qn Qu Qv Uc) Cs(Gp Je Kf Kg Kj Kl Qc Qw Qy Qz Ra Rm Sr Tz Us Uv) Hx(Hc Ib Iz Jd Jv Kf Kj Kl Kr Ow Qw Rc Ur Us Ut Vp) Mn(cE dC Hc Ib Jd Kf Kj Kr Ky Ow Ph Pi Qw Qy Rc) Bo(aF aO bS CX dC dX eW Jv Mu Ok Or Pk Us) cP(dC Hu Iz Ji Jy Mu Mv Nw Qc Qu Qw Qy Us) cX(Ad bB Dk Dl Et Gp Id Ji Ko Nw Ok Pd Uf) Mh(Kk Ko Kp Qn Qv Ri Sr Ub Uh Uo Ut Uv) Ml(Ad Dd Ed Ez Jt Ju Kd Ok Qc Qg Sr Tz) Qe(eF gL gP Ha Ib Iz Kj Pg Qv Uc Ur Ut) dD(dC Ib Jy Kk Qg Qm Qt Qu Qw Qy Ri Ur) Po(Ez Jv Jy Kj Ql Qu Rm Uo Ur Ut Uv) Fy(cB Ch cZ Ez Gd Hw In Jj Jo Og Or) Kq(Bg Ch Ef Gd Io Jg Jv Kj Nu Of Uc) aF(Ar dC Gp Hb Je Kj Ow Ph Pj Qw Ur) Qw(Ax Jl Jr Ky Mj Mx Nr Qb Vu) Ke(Ch Jv Kf Kj Kr My Nu Nv Oi) Kl(Ap Ax Et Ir Jt Ko No Nw Ok) Iz(Ax Et Hb Ir Nw On Pj Sr) dC(bB Iv Jn Jr Lv Qb St Uh) Jv(Cw Et Ky Lh Nw Uf Vu) Qn(aK aQ aV bM cB cY Et) Ow(Ba bS Ez Hc Jo Nj Nx) Ur(bE Dc Fp Ha Jl Jr No) Nw(eF Lv Nd Of Qv Uc) Ok(Ef Ez gL Kj Lv Qv) Uh(aG Gd Ju Kg My Qv) Ax(Kj Pj Qu Rc Uc) Ko(Bg Ch Jg Oy Rc) cB(Ib Je Ky Rf Rh) Ir(Kj Ph Qy Sr) Jy(aQ cY dI Nn) aK(Qv Qz Uc Uk) Ch(Kf Rf Uf) Et(Or Ph Pk) Gd(Pj Qv Uf) No(Hc Ib Qy) Je(aV bM fP) St(Co Io Kf) Ju(Ji Mp Uf) Cw(Jo Of) Eo(Jn Jr) Fp(Jd Qy) Fr(Hc Qu) Nu(Pj Rf) Hu(Ez Rf) Or(bB Wm) Ph(Kn Mt) bE(Ib Rj) bM(Cx Mu) bS(dW eO) AaKj AdOf AfGp BgSr HaMy LveW lnJr HcdL RcKy QaQy JigP QtbB JjJm KkOy LdcZ LhUv OiVu PegL} jD{Op(aC aD Af aI aK aL aM An aQ As Aw Ax bA Bb Bc bE bJ BN Bo cC cD cH cM cO Cp Ct Cu Cw dA Dd De Di Dk DL dM dN Ef Eq Et Ex Fc Fd Fn Fy Gb Gn Gp Ha Hf Hl Hp Hr Hu Hv Hw iB IC Id Ii Ij Il In Ir Is Iv Jd jE Jg JH JI Jl jM Jn Jo Jp JR Js Jt jY Kc Kd Ke Kg Kj Kk Kn Ko Kp Kx Ky Ld Lh Li lO Lp Lv Lw Lx Mb Me Mf Mg Mi Mj Mk Ml Mm Mn Mr Mv Mw Mx Mz Na Nb Nc Nf Nh Ni Nn Nr Nv Nw Nx Of Ok Om On Or Ou Oy Oz Pa Pc Pe Pf Pg Pi Pj Pk Ps Qc Qe Qg Qh Ql Qm Qx Ra Rb Rj Rm Ru Ry Si Sr Tn To Tr Tv Tz Uc Ud Ue Uf Ug Um Uo Uw Uy Uz Vb Vh Vq Wc Wd We Wf Wg Wh Yl Zq Zw Ye Wm Tj Ti) Yd(aA aD AJ Al An Ar aV BA Bb bC bI Bo bP bQ bV cC cD CP cQ cS CT cU cW dA Dc Dd dE Di Dl dN Du Et Fc Fd Fi Fp Fw Gl Gn Gp hA Hc Ho Hq Hw Hx IB Ih Ii Ij Ik Il Im In Iq Is It Iz Jd jE JH Ji Jj jL Jo JP Js jT Jv Kc Kd Ke Kg Kj Kn Kp Kq Kr Ks Kx Ky Kz Ld Lh Lj lO Lp Lv Lw Md Mf Mi Mj Ml Mn Mp Mq Mr Ms Mv Mw Mx Mz Na Nc Nf Nh Nj Nk Nn No Nr Nt Nu Nx Of Oh Ou Ow Oy Oz Pa Pb Pc Pd Pf Pg Ph Pi Pj Ps Qa Qb Qc Qg Ql Qm Qu Qx Qy Ra Rb Rf Ri Rj Rm Rt Ru Rv Si St Tr Tv Tz Uc Ud Uc Ug Ul Un Uo Ux Uy Uz Va Vh Vp Vs Vt Vw Vz Wd We Wg Wh Yl Zq Zx Ye Tm Tl Xa Wm Tj Ti) Zx(Af aG aJ aM aO aP aQ aS Ba BG bH bJ bM bS bW bZ cA cC cE Ch cJ cK cN CO CP Cq CU Cv cW cZ DB DE Dg DI dL Dr Ed Ef Em Eq Et Ex Fp Fr Gz hA Hb Hf Hp Hu Hv Hx Ib IC Ik Il Io Ir It Iv Iz Jd jF Jh Ji jK jP jR Jt jU Kd Kf Kg Ki Kk Ko Kp Kq Kz Ld Lj lK lM lO Lt Lw Ly Lz Mc Mg Mi Mj Mq Mu Mv Mx My Na Nb Nf Nm Nn No Nu Nx Ny Ou Ow Pb Pd Pf Ph Pi Pj Pk Qg Qh Ql Qn Qx Qy Qz Ra Rb Rc Rg Rh Ru Rv Sj To Tz Ua Ud Ue Uf Ug Uh Uk Ul Um Un Uo Uw Ux Uz Va Vb Vh Vp Vq Wd We Wg Tl Ti) Si(aC aD aE aF aG aH AJ AL aN Ao aP aR As aU aW aY Bb bF bG bI bJ bO bP bR bS bU bZ cB cD cG CH cI Co cS Ct CW Cx dA Db DD dF Di Dk dL dM Ef Et Fd Fi Fr Fw Gl Hl Ho Hp IB Ic Ii Ij Io Ip It Iz Je Jf jH Ji Jj JK Jl Jm JP Jq Jr JT jV Kc Kf Kk Kn Kp Kq Ky Kz Lh lN Lp Mb Mf Mg Mm Mp Mq Mv Mw Mx My Nd Ne Nf Nk Nm Nn Nq Nr Ns Nt Nv Nx Og Oh Oi Om Or Ou Ph Pj Po Qa Qc Qe Qm Qn Qu Qv Rb Rh Ri Rj Rx Sj Sr Ss St Uc Ue Uf Un Ux Vc Vq We Zw Tl Wm Ti) Vh(Af Aj AP AR As Aw Ax bA bJ bP cK Cq CW dB Dc Dd dM dN Ez Fd Gn Hb Hw Hx iC Il Im In Jh JI Jn jO jP Jq Jr Js Ju Lv Mg Mm Mw Nh Nl Nw Oi Pa Pe Pj Pk Ps Qy Qz Ul Vq Vw Vz Wf Wg Wh Zw Xa Ti) Dr(Af Al bB bC bO cH Co cU Dk Ef Et Ez Fn Hc Hf Hp Hu In Is Iz JP Jt Ke Kf Kg Ko Lx Ma Mz Nr Nw Nx Om Or Pd Pf Pj Po Qc Ql Qy Rg Sr Uk Uo Ux Vq Vz Ti) Va(aD aH aI aR aV bB bR cB Co Cu cZ Dc dD Et Hb iC Ij Il Iq Is jK Jp jQ jR Jy Kk Ko Kq Ky Lh Lv Lx Mg Mj Mm Mn Mz Nb Ok Om On Ou Oz Pj Po Qa Qc Qh Un Vi) Pj(Em Eq Fc Fd Fi fR Gb Gh Gn Gz Hl Ho Hp Lp Lt Mz nl Ps Rt Ru Rv Ry Rz Sf Sh Sj Ux Uy Uz Vb Vc Vw Vz Wb Wc Wd We Wf Wg Yl Zq Zw Ye Tm Tl Xa) Vi(aJ aL aQ BC bQ bS cF cH Cv cY Db Dc dG Ed Et Fn Hx Ic Io Iq Iu Iv jM Kg Kk Ko Lt Mf Mg Nf Nm Nx Ok Or Pk Qc Qg Qm Qz To Vq Ti) Tl(aR bO bR dK Et Fw Hb Ih Ii Il Iq Jf Jn Jv Ke Kq Kx Lh Lv Lx Mb Mj Mk Mr Mz Nr Oa Oh Ok On Or Ou Pf Qm Rg St Ub Uh Vc Yl) Et(Du Eq Fc Fd Fi Gb Gh Hp Lp Lt Ps Ru Rv Rx Rz Sf Sh Sj Uw Ux Uy Uz Vb Vc Vw Vz Wc Wd We Wf Wg Wh Zq Zw Ye Tm) Uw(aA aJ aR bS cQ Dc Fn Ha Hb Hp Hu Hx Ib Ic Im Iq jP Kg Mg Mh Mw Nm Nw Oi Ou Qn Qy To Ua Ub Uf Uh Un Ye) Ux(aI Dg Hb Ic Is Ji jK jR Ky Ld Lh Lu Lv Lx Mf Mk Nw Nx Oi Or Ou Ow Oy Oz Pc Pf Qb Qc Qg Qx Rg Rv Ss Tz) Lt(aH aI aV bB bR cB Co Cu cZ Dc iB Il Iq Is Jp Jq Ko Lv Lx Mg Mz Nq Nw Nx Ok Om On Or Ou Pc Pf Vq Ti) Ps(aJ aP aR bP bS cN Cx Dc Hb Hf Hp Hu Je Ji jP Jq Jr Kg Lp Mg Mz Nf Nu Nw Nx Ou Qn Qt Uh Un Vq Ye) Vq(Du Em Eq Fd Gb Gh Gn Hl Ho Lp Rt Ru Rv Ry Rz Sf Sh Uy Uz Vb Vc Vw Vz Wc Wd We Wg Wh Yl Zq Tm) Qc(Fc Fi Gb Ho Hp Rt Ru Rv Rx Ry Rz Sf Sh Sj Uy Uz Vc Vz Wb Wc Wd We Wf Wg Wh Zq Zw Tm Xa) Ye(aE aR bR Cu Dk Ef Hb Hu Ib Ic Ih Ii Is Jh Jn Ke Kg Lh Mf Nm Nt Nx On Qe Qy Un Vc Ti) Zq(aG aJ Al aP cQ Cu Dc Dd Fn Hb Hf Ic Il Io Iq Ir Je jH Ji Kg Mf Ni Nw Ok Uh) We(aR aV bB bR cB Cu Dc Il Ji Jp Jq Jy Lh Lv Mf Mn Mv Nx Ok Or Ou Qh Rb Un Ti) Vc(aY bC bP bZ cE cG CU Dc dF Gl Hb Iq JP Ma Mg Mm Nm Nw Ok Sr Uf Uh Ti) Ti(Du Eq Ex Fc Fd Gh Gn Lp Ru Rv Rx Rz Sf Sj Uz Vz Wc Wd Wf Wg Tm Xa) Hp(cD Dk Ef Ih Is Jh Jl Jn Jt Ke Kg Kj Kn Mf Nx Po Qe Ql Qm Rm Sr Un) Dc(Du Eq Fc Gh Gn Hl Ho Ru Rv Rz Sf Sj Uz Vb Vz Wb Wf Wg Wh Yl) Ji(Eq Qx Ru Sf Sh Sj sK tR Uz Vb Vw Wb Wc wE Wf Wg Wh Yl Tm Xa) Nw(Eq Fc Fi Gb Gh Gn Ho Rt Ru Rv Rx Uz Vb Vz Wc Wg Yl Tm Xa) aR(Du Fc Fd Fi Gb Gh Gn Hl Ho kO Ru Rx Rz Uy Uz Wh Yl Zw Xa) Hb(Fc Fi Ho Lp Rt Rv Ry Rz Sf Vw Vz Wb Wc Wd Wf Yl Tm) Iq(Du Fc Fd Fi Lp Ru Rx Sh Sj Uy Uz Wc Wg Yl Zw Tm) Lp(bR cD Ii Il Jn Ke Kg Kq Mg Mz Nm Qa Qe Rm Un) Mf(Fd Gh Gn Rt Ru Rv Ry Sf Sh Uy Uz Vb Vz Wb) Yl(Ad Al cD cH Dd Fn Hf jM Kz Mg Mz Nf Vw) Uh(Du Fd Gb Gn Rt Ru Sj Uy Uz Wc Wd Wg Wh) Il(Du Fi Gn Ru Rx Ry Uy Uz Vz Wf Wg Tm) Un(Gh Hl Ho Ry Rz Uy Vz Wc Wd Wf Zw Xa) Eq(Aj Dg Fn Gl Jm Jp Ko Ma Mg Mm Qh) Fc(aG Cu Ic Kg Lh Mk Mm Ne Nm Nx Ok) Mz(Em Gh Gn hP Rz Sj Vz Wc Wf Zw Tm) Fd(Ad aG bR Hf Ii Mg Nm Nx Qe) Gb(aP cQ dC dM Ic jH Mk Or Rx) Mm(Em Gn Ho Ru Rv Rz Sh Vb Wf) Zw(aG aJ Ic Je Lh Mg Ou Qn Qz) Vw(dC Ic In Jt Lh Nm Nx Or Ou) Kg(Hl Rt Rx Sf Sh Sj Wb Wc) Ok(Du Fi Ru Sj Uz Vz Wc Tm) Mg(Fi Hl Rv Rz Uy Vb Wf) Rt(aG cQ Cu Ic Ke Ne Qm) Rz(Ad bP Jm Lh Ma Nm) Nx(Du Gn Vz Wb Wf Wh) Cu(Fi Gh Gn Wd Wh) Ry(bR Dd Hf Kq Nm) Ad(Rx Sh Wd Wh) Wb(bR bU Lh Ou) Sj(bR Ou Ql Qm) Tk(Kk Kz To tF) Vb(Dd Kj Nm Qm) Uy(Hf Is Lv Or) Vz(cH Jp Ou) Wd(Hf Lh On) Wf(Jn Jr Ou) Xa(dB Ic Jq) Rv(Fn Kj Nm) Dd(Du Wc) Lv(Rx Sh) Ho(aG Ne) Wh(Ef Jl) Kl(mP mZ) fR(Qh Uc) nN(cH Ko) mW(Bn Ph) AjkF AlGh BcRx DuSr EmkS FiQm GnIi NmHl HxsH IcWc SfJp ShcB KrqH aSnT} Mz{hP(AA aC AD aE AF aG aH aI AJ aK AL aM AN AO AP aQ AR AS aU aV AW AX aY aZ BA BB BC bE bF BG bH bI bJ

Po) Fr(Hx Jn Jp Jr No Po Qa) Ik(aC Iv Jr Mk Mr No Oh) Bb(Ad Dd Gp Ii Jm Jq) Ml(Aa aQ aX dA Dd Lw) Oi(cW dL Iv Ne Nn Qb) bS(cW dL Hx Nn No Oh) Jp(bR dD Jk Mu Oe) Jr(Hu Mv Nb Nh Nv) Lj(As Lw Mm Mp Nx) Af(aW Jn Nj No) Po(Gd Ip Mu Ng) Mk(aF aQ cM dA) Ir(Ao Jg Jo Ly) Oh(An bR Jo Ma) Ok(aX Cs Ef Pz) Nj(Hx Mr Qb) Nx(aC Og Oy) aQ(dN Nd Nl) cP(aX cZ dC) Ef(Is On) Gd(Gp Jn) Mp(aF Cs) Mu(Jn Qa) Hx(De Dk) cW(aX Oy) AxcZ BgJm CwJo CxaC DlPa GpLy NoHu IlbR aFaI cCdC} hA{Yd(aA aC aD AF aG aH Aj AL aM aN aO aQ Ar As aV aW AX aZ BA Bb bC bH bI bJ bL BN BO bU bZ cA cC cF cI cJ cK cM cN CP Cq cR Cs Ct Cu Cv CW Cx cY cZ Db Dc dD DE Dg DI dJ DK Du Ed Em Ex Fc Fd Fi Fn Gb Gh Gl Gn Gp Hc Hl Ho Hp Hq Hr Hv Hx iC Id Ii Ik Il Im Iq Ir Is It Iu Iv Jd JE jF JG Jh JL jM Jn JO Jp JQ jR Js JT Ju Jy Kc Kf Kg Kj Kk Ko Kp Kq Kr Ks Kx Kz Ld Lh Lj lL lO Lp Lt Lw Lx Ly Lz Ma Mb Mc Md Me Mg Mi Ml Mp Mq Ms Mv Mw My Na Ng Nh Nr Ns Nx Ny Oe Of Og Oh Oi Ok Om On Op Ow Oy Pf Pi Pk Po Qa Qb Qd Qg Ql Qm Qt Qu Qv Qw Qx Qy Qz Ra Rb Rf Rg Rh Rj Rm Rt Rx Sf Si Sj Sr Ss St Tn To Tt Tz Uc Ud Ue Ug Uo Ux Uy Uz Va Vb Vh Vi Vp Vq Vs Vt Vw Wb Wc Wd We Wf Zq Zx Tl Wm Tj) Vc(Ad aF aI AL aM Ao aU Aw AX aY aZ Ba Bc bI bJ Bn bR bV bW cB cG cI Co Cu Cw cZ Db dC Dg dH Di dJ Du Ed Em Et Fy Gz Hf Hu Hx Ip Is Iu Iz Jg jH jK JM Jp Jq jR jT Ju Kc Kf Kl Kq Ma Mf Mg Mm Ms Nb Nk Oe Om Op Oy Pg Pi Po Qc Qm Qy Rf Rt Rz Sf Si Sj Sr Tn Ua Ub Uf Ug Uh Un Vo Vp Wc Zw Zx Tm) Si(Ad aE Aj An aO aU aZ bE bR bS bU bV cC cE cI cL CU dB DE dH dK Fn Gl Hc Id Io jE Jl jO jQ jU Kc Kp Kz lL Ml Mp Mx Nc Ne Nf Ng Nh Ni Nj Nk Nl Ns Nu Oh Ou Oz Pd Ph Pi Po Qe Qm Qy Rc Rg Ry Sr Tz Ug Uh Um Ux Vq Vs Vw Yl Zw Th) Dr(aG Aj aM aO Ap Aw AX Ba bE bF Bg bS bX cE cI cM cP cR cS Cx cZ dE dF Dg dK dM Ed Ef Ex Fp Fr Fw Gn Gp Hb Hc Jd jF Jh Jk Jl Jq Ke Kq Lp Mg No Nu Nv Oa Om Oy Pi Qa Qd Qe Qg Ql Qu Rc Sr Ss St Tr Tt Tz Uh Va Vw Zq Zw) Qm(Du Eq Fc Fd Fi Gb Gh Gn Ho Hp Lp Lt Op Ps Rt Ru Rv Rx Ry Rz SF Sh Sj Uw Ux Uy Uz Va Vh Vi Vw Vz Wb Wc Wd We Wf Wg Wh Yl Zq Zw Zx Ye Tm Tl Xa) Va(aD aR bB bR bS cG cL cM cO CU dJ Et Hb iC Jf Jn jO Jp Jq Ke Kk Ky lL Lx Nw Or Ou Pi Po Qa Qd Ql Qy Tz Un Zq Th) Vh(aF aG aO bN bS cE cL dG dH dK Fw Hb Hf Kc Kd Kg lL lM Mr Nh Nu Ok Ou Pi Ps Qy Sh Uh Ul Um Un Vt Vz Wh Zx Xa) aR(Ho Hp kC kE kF kG kI kK kN kP lW lX lY mE mH mI mM mP mT mU mW mY nA nB nI nJ nM nR nU Ps Sf Vi Vw Tl Xa) Ou(Fd Fi Gh Gn Hl Ho Hp Lt Op Ru Rv Rx Ry Rz Sf Sh Sj Uw Ux Uz Vb Vi Vw Vz Wc Wd Wf Wg Yl Zq Zx Ye Tm Tl) Jf(Fc Fd Fi Gh Gn Hl Ho Hp Lt Op Rt Ru Rv Rx Ry Sh Uw Uy Vi Vz Wc Wd We Wf Wh Yl Ye Tm Tl Xa) Op(aE aH BA bN bR bS cG cM cQ Ct CU Fy Gb Ii jO Lh lL Ma Nd Ni Ok Pi Ql Ry Sr Ug) bR(Du Fc Fi Gb Hp Lt Rt Ru Ry Sf Sh Sj Uw Ux Uz Vb Vi Vz Wc Wd We Wf Wg Wh Zw Ye Tm) Lh(Fd fR Gh Gn Gz Hl Hp Ru Rv Rz Sh Uy Vw Vz Wb Wd We Wf Wh Yl Zq Zw Ye Tm Tl Xa) cL(Du Eq Gb Ho Rt Rx Ry Rz Sf Sh Ux Uy Vw Vz Wc Wd Zq Zw Xa) Zq(aE aP cD cG dB Ic Ii Il Io Iq jO lL Ni Qc To Vq Th) Tl(Ar aY bN cG dF dK Hb Nw Po Qa Qc Qd Qg Un Th) Rz(Ad Bc Ct Cu Hb Hf Jg Ke Kf Ng Ql Qu Uy Vq Th) Zw(aO aY bN bS cE cG cO dF dH Hf Ok Pi Ql Uh) Vq(Fc Fi Gh Ho Hp Rt Ru Sf Sj Vb Vi Wb We Zx) Ps(aJ aO aP bS cG Cu dB dG Hf Hp Nf Ok Pi) Zx(Ad aP aY bF Cu Ii jO lL Mg Nq Pa Ug) cG(Fd Fi Hl Ho Rv Sf Uw Vz Wc Wd We Tm) Hf(Du Lt Sf Sh Ux Vw Vz Wb Wc) Yl(aO bS cE cO cX Pi Qc Ql Un) dG(Fd Gn Hl Ho Uw Vi Wc Wd) Gb(aE bS bV lL Oi Or Th) Uh(Rv sF sH sJ Vw We Wf) Cu(Fd Hl Hp Lp Wb Ye) Du(Dc dH Il Oi Pi Ql) Ux(bN Hb jO lL Un Th) cU(Lt mE mW nA nD nN) sH(jE jM rW sC vV yH) Eq(Aj Fn Kl Mg Qu) Wc(bS cE cO Pi Ql) Ye(Fw Hb Ii Jr Sr) Lp(bS Hb Ii Jr Ok) sJ(cC iH jM uM vI) lL(Hl Lt Rx Sf Vw) Gh(aE Dc Ok Uc) Hp(Ii Jn Ok Po) Ry(aE bS dH Un) Ad(Sh Wd Wh) Wb(bN bU Hb) Vz(Iq Qc Ql) Sf(bS Pi Ql) Wf(Jn Jr Sr) Uw(bN dF Th) dB(sF sI Xa) Dc(Sh Wh) Gn(Hb Iq) Ic(Tm Xa) Rv(Fn Nm) Ok(Wd We) Vb(Pa Un) Uy(Qc Ti) Vi(bF Qw) aG(Fc Fi) sF(No Vu) PoSj FdIi MfSh IduM TmcE LtjO QlwF NwsI cHnN} Eo{Mb(Aa aC aE aF aH AJ aK aM AO aQ aR As aV AX Ba bE bF bG bJ bL bM Bo bQ bR bS bU bW bX bZ cC cE cG CH cL cM cN CO CP Cq cR cS CT cU CX cZ dA dB DC dD dF DG dH DI dJ DK dL dM dN dX EM eP Et Ew FP fR Fw Gd Hq Hu Hv Hw Hx Ih Ij Ik Im Ip Iq Jj Jl Jo Jp Jr Js Jt Lh Li Lu Lw Lx Ly Ma Me Mf Mg Mh Ml Mm Mn Mp Ms Mt Mu Mv Mw Mx My Nf Nn No Nq Nr Nu Nv Nw Oc Ok Oy Oz Pa Po Pz Qa Qb Qd Qe) aM(AD aE aF aH aI AJ aN AO AP aQ AR AS aV AW AX aY aZ bA Bb BC bH bI bL bM bN BO bR bU bX cA cB cC cD cF CH cI CO cP CQ Cs CT cW dA DB Dc dE Dg dH DI dJ DK Dl dM dN DW dX Ef EM eP Ew Fp Fr Fw Gp Hu Hv Hx Ih Ij Ik Il In Ip Iq Is It Jh Jj Jl Jt Lv Lx Ly Me Ml Mn Mr Mu Mw Nb Nc Nd Ng Nh Ni Nl Nm Nq Nv Nx Of Og Oi Ok On Oy Pa Pb Pc Pe Pg Pz Qa Qe) Lx(aA aC aD AF aI AL AN AP aR aS aX bA Bg bM BO bP bR bX cB cC cF Ch cJ cM Co cP cQ cR CS Cu CV CW cX cZ dC DD dE DG dI dJ dK Dl Dw Ef eM Ew fR Fw Gp Hq Hr Hu Hw Ih Ik Il Io Ip Iq Is It Iv Jh Jk Jl Jr Js Lh Li Lv Lw Lz Ma Me Mf Mh Mi Mj Mm Mn Mp Mv Mw My Na Nd Ng Nh Nk Nn Nq Nu Nv Nw Of Ok Om On Oy Pb Pe Po Pz Qd Qe) Jr(aC Aj aO aW Ax aZ bA bB bC bE bF bN Bo cA cB cD cE cF cG cP CQ cS CT Cu Cx dA DC Dd dE dW eM Ew Fr Hv Hw Jg Jj Jk Jm Jn Js Lw Ly Mi Mk Mn Mp Mr Mv Mw Na Nc Ne Ng Nh Ni Nl Nr Nv Nx Oe Of Og Oh Ok Oy Pa Pc Qa) Lv(aD aF aG Aj Al AP aS aV Ba bF bI bM bR bW cB cF cM cP cS dA Dc DE dH Ef eP fR Gl In Ip Is Iv Jm Jo Jq Js Lj Me Mg Mi Mn Mx Na Nf Nh Nr Nu Nw Of Ok Oy Pc Po) Mn(aC aD aP AR As aY Bb bM Bo cU cW Db DC dG dJ dL dN Hw Hx Ir Is It Jn Jp Lh Lj Mf Mh Mk Ms Mt Nd Nf Nl Nn Nw Nx Og Po Qb Qe) Qe(Af Aj Ax bA Bn BO bS cH cT CX De Dl eM eP Fr Gd Hu Hv Ik Ip Jj Jk Mk Ml Mu Mw Nf Ng Nj Oe Oi Om) Hx(Aa Af aK aQ aV aY bA bC bE bF Bo cG cR Cu Cw cX cY Dd Dk Dw Fr Ij Im Ir Iv Jn Jt Lh Mf Mi Mk Nl) bM(Aj As aZ bB bE bX Cq Ct Cu cX Dc Gd Hv Ij Il Iq Is Jk Jn Lj Mi Ml Mu Mw Mx Na Nv Oe Oh Oi Pe) cX(Ad aF aO bB BO bR cB cC Ch Co Cu Dd Di Dk Dl Gp Hw Ii Is Jm Nm Nt Nx Ok On Pe Qd) Po(aD Aj As aX bA bJ bS Ct dA DE eM Fr Gd Hu Hv Ip Ly Mp Mq Mu Mw Nf Ng Nj Nv Oy) Aj(Ap bB cB cI cW Dc Et Gl Hw Ih Iq Iu Iv Jn Jq Js Mg Nj Nx Oh On Pd) Of(aI Al bC bO Cv CW Gl Gp Iq Iu Jm Mf Mg Mp Ng Nj Ok On) aD(aC aH aL aY bA bB bE Bn Bo bS cB cT Cu Cx De Hu Mf Mk Oi) Bo(aC Af An Ao Bb bS bX Cx dD Dg dX Jg Jl Jm Lj Mh Mu) Is(aC Ap aR Ba Bb Dl Ew Ik Jn Jp Ml Mp Mv No Og Pd Qb) bB(aC aF aH Ax dC Dl Fw Gd Hv In It Jh Jn Li Lj Ml Nu) Nw(bA Bb bN bV bX cT Jh Li Lj Mk Ml Mu No Oe) No(aI aX bQ cG De Fr Hu Mu Nj Nx Oh Ok) cB(AF An Ax bA Bb bN bS cA Cx Ml Oi) Gd(Cu CW Gp Jm Jn Mf Mg Oh On Pa) Ml(aX cM dA dX Io Nj Nm Nx Ok Qc) Bb(Ad aK cM Dd Gp Iq Jq Mf Nj) Jj(aC Al Gl Hw Iv Jm Mf Qc) Oh(aF As aX bS Hq Jo Ok Qb) Af(Cu Dc Hw Jl Jn Pe Qc) Mu(Et Jl Jn Jp Mt Ny Qa) Nx(aQ Cs cY dD Li Lj Oy) Qb(Ax bA bS Cu Hv Na) Ok(dC Dg Dl Hv Jo Mk) dL(Cq Cu Dc dG Il Js) Bg(cW Gp Mf Nj On) Ir(bA bP Jg Mm Mp) Jp(aY bE dD Mr Oe) bR(aC aI Gl Hw Iv) Nj(Jl Mh Mr Qa) Lj(As cZ eM Mm) Oi(cW Gl Nn Qa) On(Ch Ct Dl Hv) Mp(aF Cs Nr) Jl(Cx Hv Pg) Pa(aC bE Mh) cP(aC aX bE) Ct(cW Il) Et(Ao dD) Mf(bP Ng) Mr(Ik Mm) Jo(Cw Gl) aF(cU dF) CscZ CxJn DccA DgcW EfIi EmNa GpJg MkdA MtaC NkHu HvQa HwOg aOdF bNdC} jM{sI(Aa AD Af aG aH aI Aj aK AL AN AO Ap AR As aU AW aY Ba BB bE bF BG bI bJ bL BN Bo bQ bS bX bZ cB cC cE cF CH Co Cp Cq cR Cs CT Cu CV CW Cx cZ DB Dc DD DE dF DG Di dJ Dk Dl Dp dR eC ED EF Et EZ Fn FP Fr Fy GL GP gW hB HC HF hG hL hP HR Hu HV HW Hx iA IH Ii IJ Il In iO IP Iq Ir Is It IZ Jd Je Jf JG Jh Jj jK Jl Jp JQ JR JT JV Jy Kc Kd Ke Kf Kj Kk Kl Kn Ko Kp kQ kR kS Kx Kz Lh Li Lj Mh Mm Mr Mx Nc Nd Ng Ni Nj Nk Nl Nm Nn No Nt Nu Nv Nx NY Oa Oe OF OH OK ON Or Ou Ow Pc Pd pF Pg Ph Pi Pk qA qB qC qG Qh Ql Qm qQ QT QU Qv QW QX QZ RA Rb Rc Rf Rg Rh Ri Rj Rm rN rP rQ rT rU rV rW rZ sH sO Sr Ss tN TO tQ TR tS Tt tU Tv Tz Ua Ub Uc Ud Uf Ug Uh Ul UM UN UO Us uT UU Uv uX uY uZ vB vC vH vI Vo VP VS VT Vu VV vW wB wC wD wF wG wH wJ wK wL wP wQ yD yH yJ yK yL zG zH zI tL xA Tj tF) sH(Aa aE Af aG aJ aL aP aR As aW aY bA BB bF bI bN Bo bZ cE Cv cZ DD dE dN eD eZ Fn Fw Gl Gp Ha Hb hC hL hO hP Hv hW Iq Jd Jq Js Ju JV Ke Ki Kn Kp Kx Li Ms Ne Nk Nx Ny Ow Pd Pg qB qC qD QG Qm Qt qU QW qY qZ rB rS sO Ss tS tT Tv Uh Uk uL uM uO uP uR uT uU Uv uZ vA vH vI vO vQ vT vU wB wC wE wF wG wK wP yD zG zI xA) sJ(Aa aE AF aG aL aO aP Ar bB bF bI Bn bQ bZ cB cC cE cJ Ct cW Cx dB dE Dg Dk Et eZ Fn Fw Gl Gp Ha Hb HC hG hP Hv HW iJ iP It Jj Jq Jr Js Kd Ke Kk Kn Ko Kp Ky

Figure 41 Continued

Ld Li Lx Ms Nk Nl Ny Or Ou Pd Pg Pk qB qC Qg Qm Qn QW Qx QZ Rc rN rO rS sO St tT tX Uk uL UM uO Up uT uU uZ vI VT vU vW wB wE wK wL wP yD zG zI tL xA) sF(Aa aE Af aG aO As aY bA bB bF bI bZ cE Ct cW Cx dB dD dF dN Dp Et eZ Fn Ha Hb hC hP Hv HW In iP Jq Jr Js Ke Ki Kk Kn Kp Ld Li Lx Mr Nk Nw Nx Ny Or Ou Ow Pd Pg qA qD QG Qm qT QW qY qZ rS sO tS Uh Uk Up uT uZ vI vU wB wE zI tM xA) Yd(Ar cG cM Cu dD Fw Hf iC Id Jq Jr Js Kn Ky Lx Mp No Nu Nw Ok Pe Po Qa Qe Ql Un Zx) Uy(bB Hb In Is Ld Lj Lv Lz Ml On Ow Pe Pg Ph Qa Qb Qg Qx Rx Sr Tz Vb) wB(bQ cK Cu dA dH Jy Lw Lz Mi Mp Mq Mt Pb Pd Pe rQ uI Vq Vu) Rv(aH Ba cM cV cX Fn jG jK Lh Lx Ok On Pe Po Qu Uh Vt) Vh(aI Fw Jj Kd Lh Li Nc Nd Nu Ou Po Ql Ru Ul Vc Vt) tX(Aa An cZ Et Id iO iP Ke Kn Lh Li Nw Ri Uh uI) Vq(Hp Rt Sh tQ Uw Vb Vc Vz Wc We Wh Zq Zx Ye) Lh(Fc Fi Rx Sh Sj Ux Wc Wh Yl Zw Ye Tm Xa) Dr(bO dD Fw Jp Nu Ou Po Qm Rj Sr Vt) Zx(cM CT Db Gl Hx Ii Mg Ok Qw Vt) Po(Hp Lp Op Sf Va Vz Yl Zq Ye Tl) Sh(bB Dc Ii Mg Mr Ok Qa Qh Ry Vi) Li(Op Rt tT Vc Wb Wc Wf Yl Zw Ye) Yc(Db Jl Jr Kq Ok On Qd Qm) Ke(rQ tN tO tT tU uG uI wF) Uw(aI aV Hx Ic jK Rg Vt Wh) Vc(aY bB cE cJ dD dF Jj Jp) Op(Bc cQ Ct Hw Id Ok Pa) Ou(Rx Sf Si Va Vz Zq Tl) aR(kO kP lX lY mM nC nN) Eq(Ba cM cV Dg Fn Ne) Hp(Hf Jn Nb Qa Qe Ql) Yl(aV Ba Hf Jj Ql Qm) On(Lp Va Wd We Wf Tl) Si(dD Fw Nu Ql Sr) Zq(aH Il Io Oi Qc) Rz(cM cV Gl Ok Qu) Rx(cM Ct Ii Ok Vt) Qm(Fi Gh Ho Sj Tl) bB(Gb Ru Ry Vz Wh) Jr(Lp Wf Wh Tl) Uh(Rt tT Vw wF) Ux(Ld Ml Qx Vt) Du(cB Ne Oi) Hf(Vb Wc Wf) Ps(Ih Ok Qa) Vt(Wb Wf Tm) fR(aG Ao Mn) tN(Aa An cZ) wF(Cs Kn Ri) Dc(Sf Wh) Vz(aI Sr) Ry(aV Oi) Vb(cM Of) Va(aI iC) Vi(aG Qw) cU(mE mT) lY(bG Ki) tT(An Ri) FawG FiHb FwTl GnSr IduI WbcM ZwOk JnLp JsTk RgVw aSnT cHnN} cR{oW(AA aJ Ap Ax bH bL bM Bo bU bV Ch cM Cw cZ Dd dG Di dM Dp Du Ed Ef Ez Fa Fb Fc Fd Fi Fn fR Fy Gb Gh Gp Gz Ha Hb Hc Hf hG Hl Ho Hp Ib Io Iz Jd Je Jg Jh Jt Ju Jv Jy Kd Ke Kf Kg Ki Kj Kk Kl Kn Ko Kp Kq Kr Ks Kx Kz Lj Lp Lt Lw ME Mf Mg Mm Mn My Nk Nm Nn Nx Oa oD Op oQ Oz Pb pK Ps Qe Qg Qh Qm Qn Qt Qv Qw Qx Qz Ra Rb Rc Rf Rg Rh Ri Rj Rm Ru Rv Rx Ry Rz Sf Sh Si Sj Sr Ss St Tn To Tr Tt Tz Ua Ub Uc Ud Ue Uf Ug Uh Uk Ul Um Un Uo Up Ur Us Ut Uu Uv Uw Ux Uy Uz Va Vb Vc Vh Vi Vj Vo Vp Vq Vs Vt Vu Vv Vw Vz Wb Wc We Wf Wg Wh Yd Yg Yh Yi Yj Yk Yl Zq Zw Ye Tm Tl Xa Wm Tj Ti Th Yf) oD(aG aJ aO aV aW bB bH bM bU bV bX cN Cx cY cZ dG dH Dk dM dR eC Ez fP fR Fw Fy Ha Hc hG Hq Hx Im iP Ir Je Jf Jl kK Kl Ko KR Kx Li Lj Lv Lz mE Mf mH mI Mj Mn Mw NA Ne Nh NK Nl NN No NR oH Oi oP oT Ou Oz Pb Pc Pg pK Ps Qe Qg Qh Ql Qu Qy Ri Ss Tr Tv Tz Ua Ub Uc Ue Ug Uk Um Uo Ut Uv Uw Uy Vp Vs Vu Vv Wd Yj Yk Ti Th) eQ(bB Ed Ez Fa Fb Fc Fi fR Fy Gp Ha Hb Hc Hf Ib Ic Id Ir Iz Jd Je Jf Ju Jv Jy Kc Ke Kg Ki Kj Kl Ko Kp Kr Ks Ky Lp mE Mn Nj Nn Nr Oz pK Ps Qe Qg Qh Ql Qm Qn Qt Qu Qv Qw Qz Rc Rh Ri Rt Ru Rv Sr St To Tt Tv Tz Ua Ub Uc Ud Ue Uf Ug Uh Uk Ul Un Up Us Ut Uu Uv Uy Vb Vo Vp Vq Vs Vt Vu Vv Wc Wd Wf Wh Yh Yi Yj Tm Xa Tj Th Yf) pK(Aa aK Al aO aW aX aY BB bL Bo bU cF Cv Dd dH Dp Ed Ef Ez Fb Fc Fw Fy Gp Gz Hc Id Ih Im Io Iq Ir Jd Je Jf Jg Jm Ju Jy Kf Ki Kj Kk Ko Kp Kr Li Lj Lw ME Mk Mw MY nI Nj NK nN nO NR Oa Or Ow Oz Pb Pc Pf Ph Qe Ql Qm Qn Qv Qz Ri Sr Tt Ua Ub Uc Ud Uh Uk Ul Um Ut Uu Uv Uy Vp Vs Vu Vz Wf Ye Tl Xa Wm Tj Th) oT(aI aJ aO Ax bB bH bL Bo bU cF cO cZ dG dJ Ed Ez Fa Gp hG Id Io Ir Je Jf Jl Jy Kd Ko Kx Li Lj Lp lX mE Mn Mw Nn Nr Oa oQ Or Ou Oz Qe Ql Qm Qu Qv Rc Ri Ru Rv Sr Ss To Ul Uu Uv Uy Vb Vs Vu Ye) nK(Du Eq Fc Fd Fi Gb Gh Hl Ho Hp Lp Lt Op Ps Rt Ru Rv Rx Ry Rz Sf Sh Si Sj Uw Ux Uy Uz Va Vb Vc Vh Vi Vj Vw Vz Wb Wc Wd We Wf Wg Wh Yd Yg Yh Yi Yj Yk Yl Zq Zw Zx Ye Tm Tl Xa Ti Yf) gZ(bB fR Ha Ic Jd Je Ke Kl Ko Lp ME Nj Nk Nn Oz Pb Qe Ql Qn Qu Rc Rg Ri Ru Rv Rx Sr To Ua Uc Ue Uh Ul Uo Uu Uy Vs Vu Wd We Yj Ti) mW(Du Eq Fc Fd Fi Gh Ho Lp Op Ps Rt Ru Rv Rx Ry Sj Uw Ux Uy Va Vb Vh Vi Vw Vz Wb Wc Wd We Wf Wh Yd Yg Yh Yi Yk Yl Ye Tm Xa) pH(bB Ed Fc Fy Id Ir Jf Jy Kd Ko Kr Lp mE Mn Nj Nn Oa Oz Pb Qe Qh Ql Qu Ru Tv Ul Ut Uv Uy Vp Vs Vu Wd Th) pI(Ax bB cZ Eq Fi Fy Ha Jd Je Jf Kd Ko Lp mE Nn Oz Qe Qg Ql Qu Ri Ru To Tv Ua Ub Uc Ul Uo Ut Uy Vs Wd) oV(bB bU Ed Fa Fb Id Jd Jf Jg Kd Kk Ko Lp mE Nn Ql Qm Qn Qt Qu Ri Rj Ru Sr To Uh Ul Uv Uy Vs Wd) mU(Eq Fc Fi Gh Hp Lp Lt Op Ru Sh Si Uy Wc Wd Wh Yg Yi Yj Ye) oP(Fd Lp Op Ru Rv Ry Rz Sj Ux Uy Vz Yj Zq Tm Tl Xa) Ye(kE mE mF mI mP mS mT mY mZ nA nB nC nD nH nN) fA(bB Lp Nj Nk Ql Qu Ri Ru Tv Uh Ul Uy Vs) Ru(kO mE nA nC nD nH nO oO oQ) nH(Ps Uw Uy Wc Wd Wf Wh Yg) Ti(nB sK tS tX vV wG) Wd(nA nB nC nD nN oO) Wf(mE mH mI mZ nB nC) Ke(tO tR tS tX uM) fB(Ax bB bU Kd) Eq(nA nC nN) Id(qH uM vA) Wh(nB nC nN) Uh(sK tT tX) dW(aM Mb Qe) gC(Kd mE Uy) Dw(aM Mb) Ex(qZ wC) Yg(mE nC) EwNx ThnB ImvO YdjI ZqjK ZxjG WemE LpoQ NyyJ UnvA UynA nTrA tOqZ} Id{uM(AF As aV aY Bb BC bF bG bH bI bJ bL Bn bQ bR bS bU bW bX bZ cA cB cC cD cE cF cG cJ cL cN CO Cq cS cU Cv cW cX dA dE dF dG dH dI dN eD eT Fa Gl gP Ha Hq hR HV hX IB iC Ik Il iO IP Is It Iv jF jG jI JL jO jQ jR jU jV Jy Ko Kr lK lL lN lO Lw Lx Ly Mb Md Mi Mk Mm Mn Mp Mq Mt Mu Mv Mx Nc Nd Ne Nl Nn Ns Nu oE oK Or Ou Ow Oz Pa Pb Pd Pe PF Pg Ph Po pY Qb Qh qP qT QU qV Qw Qx qY qZ rC Rg rO rQ rS rT rU rV rZ Ss To Tr uI Ul Up Us UV Vo VP Vq Vt Vu vV wD wF Tj tF) uI(aA aD Af aM An aP aQ aX aZ BB bC bJ bP bQ cC cF cS Cu Cv cX cY dB dC dH dJ dK dN dR eC Ed Fa Fb fN fP Fw Fy Gl GP hB Hc hP Hq Hr Hu hV hW HX Ik Il Im Io IP Iq Iu Iv jE jF jL jO Ke Kf Kj Ks Ky Kz Lh lK lN Lv Ma Md Mp My No Nq Nr NW Ny Oi oK Or Ou Pc qH Ql Qm Qn Qw QX rA Rh rQ rR rW rX rY rZ sC sK Sr Ss St TO Tv Ua Uh Um Un uO uR uX uY vA Vo vT Vu vV wJ yH yK zG tM tL Wm Tj tF) tO(aN aV aY bF bG bQ bR bS bU bZ cA cD cF cG cK CO Cq CU dA dH dI Hq hR Il Jl Jy Kq lK lO Lw Lx Lz Mh Mi Mk Mp Mq Mt Mu Nd Nr Ns Ow Oz Pa Pb Pd Pe PF Pg Po Qw rC Rg rQ Tn Tr Uh Us Uv wP Wm Tj) hP(aV bH bQ bR bU cA cC cD cF cG cK CO Cq dA dI Gz Hq Jl Jn Jy Ke lK lO Lw Lx Mi Mk Mp Mu Nd Oz Pa Pb Pd Pe PF Pg Po Rg rQ Sr Tr Uh Un Vq wF Tj) vA(aV bG bQ bR bU bZ cA cF cG cK CO Cq cU dA dI Ha Hq Il Jy lO Lw Lx Lz Mk Mq Nd Oz Pa Pb Pd Pe Pf Pg Po Rg Tr Us Vq Tj) vT(aV aX bG bQ bR bS bZ cA cF cG cK cL cN CO Cq dA dH dI Jy Lw Lx Mi Mk Mp Ns Oz Pa Pb Pd Pe Pf Pg Rg tN Tr Vu wF Wm) uR(aV bG bQ bR bU bZ cF cG cK CO Cq cU dA dG dH dI Il Jy lO Lw Mk Mq Nd Oz Pa Pb Pd Pf Pg Po rC Rg rQ Tr wF Tj) sJ(aP Bb Bc bL Dg Dl dN gP hG Hv Hx iH Jr Me Ms Mt Nm Og Oi oN pF Qg qT qY Rh Tr Uk Ur Vo) sF(aP bA bL cT cV dB Dg dJ dN Fn gP Hv Hx iH Jk Jr kR Kz No Oh Oi Qm qZ Rh To Ue Uh Ur) sH(aM aN aZ bP cI cW dB Dp Hv Hx Jh kR Kz Mn Nt Ny oK Pa pF Qm rA Rb Rh St Tr Ub Ue Uh) uX(bA bG bM dH dM Fr Gl Il Im Ip Jl Ny On Po rQ rZ Ss tV tX Uc Uh Un Vq Vu Tj) sI(aP Ax bP cW dK dN fP Hf Hq Hv Hx iH Ik Iu Jh Kz Mf Mn pF qZ Rh Tr Ue Vo) bR(tN tQ tR tS tT tU tV tX uG uO uW wC wD wH wJ wL wP yD yK tM) Yd(iC jF jH jK jQ jR jT jU lL lM lN lO) rQ(aX bQ Hq iA jO Lu nW oK pF Qm vO) tX(bQ dB dN hB lP Qm Ue Uh zG) tN(dB dN iC jO kR Kz Qm rR Ue zG) dH(uO vO wB wD wJ yJ yK zA tM) tT(dM fP iB Il Kz qZ rS Tt Uh) rC(eF gL hB iA lM oK oN Qd qH) wF(bC bP bQ Im Ip Qm Ri rR) Tr(hX rB rZ uN vU wJ zG) Op(iB jF jO jR lK lL lN) jV(aC Gz No Or Pf Rx uG) Th(hR hV hW rX rY rZ) bG(rX rY rZ uO yJ yK) jK(Fd Lt Ry Vi We Yl) Il(tR uW vO yD tM) Ip(tU wC wK wQ yD) Uh(qA uG uO uV vU) Nk(eQ fB gZ pK) cF(rR uL uO wJ) tV(Aa aX dB Kr) rB(Jl Jy pF Vp) qZ(lM tR tS yJ) Tk(KR Mn) zG(cU dA Un) uG(dM jO Ur) vO(hR Ou Tj) No(wB wQ) Lj(Wb Wn) dD(hR lM) wP(cI rR) qB(Ex Gz) qY(bM hG) rZ(Kr lM) ZxlN JshW LipK LplK QmhL WnkR UxjQ VaiC VjnK VuvH VqtM PdqH aXqG dByD} Nk{pK(aA aF Al aO aR aS AW Ax aY aZ bI bN cB cF cH cI cM cN Cq cV cX DD dF dG dH dI dL dN Dr Ed eF Em Ex Ez Fp Fw Gl Gn Gp gZ Ha Hc Hq Hr Hw Hx iA Ib Ih Ii Ij Il Im In IP Ir Is Iv iZ Jd Jk Jm Jn Jr Ju Jv Kd kF Kg Kl KN Ks Ky Ld Li Lj Lp Lt lW Ly mE Mj Ml Mn Ms Mu Mw mZ nC Ng nH nI NJ nK nL NN No NR Nt NU Nx Ny oF Oh oK Om oP Or Ou oW Oz Pa pF Ph Pk Qa Qb Qc Qd Qe Qg Qh Qm Qt Qu Qw Qy Qz Rb Rc Rf Rg Rh Ri Rj Rm Ru Sf Sr Ss Tn To Tr Tv Tz Uc Ue Ug Uh Uk Ul Um Un Uo Ur Us Ut Uv Uw Vh Vo Vp Vs Vu Vv Wc Yi Tm Tl Xa tF Yf) fA(aC Al aO Ax bB bE bM bN cF cJ cK Cq Cs cU Db dJ Dr Du Ed Ef Eq Ex Fa Fc Fi Fp Gh Ha Hb hC Hf hG Hl Hp Hv Ic lH Ip Iq Ir Iv Jf Jn Jr Ju Kc Kd Ke KF Kk Kl Kn Kq kR Kx Ky Lt mE Ml Mn Mw Nb Nj Nn Nr Oh oK Oz Ps Qb Qc Qh Ql Qm Qt Qu Qv Qz Ra Rb Rc Rf Rg Ri Rj Rm Rv Rx Ry Rz Sf Sr St Tn To Tr Tv Tz

Figure 41 Continued

Figure 41 Continued bW dL Nr Ow Ue Uf Vt Wm) uP(cI dN Hx Jk Jn Kl Ma Mn Ms Ne uM) Sr(hR hV hW hX sO tQ uV vW wE tM) aV(hW rX uR uX vI wB wJ yH yL tM) eP(aM Du Fa Iv Ki Kx Lj Mt Po Qe) Wm(sM vT wD wF wJ wK wL zA xA) Gp(uZ vI vO wB wD wE yH yL tM) Tz(hW rB rX tQ uO vT zG yE tM) dX(aM Du Fa Iv Li Lj Po Qe Yd) uV(bX Fn Jv Kn Ne Og Rf Ub Ue) uT(aK aQ aU bE cY Ma Mn tS vP) Kn(rB rX rY rZ uL uO vI) aQ(uO vP vQ vT wB wD wP) bE(tU vQ wF wJ wK wP yD) Af(uG uL uR vB vT zG) Ne(tV uL vB vQ vT yL) Ar(uO vH vT vW wQ) Ue(vO vU yH tL xA) cI(vP wB wC wL xA) wP(cU cY Qx vP) tN(Jv My Qz tQ) tV(Hb Io uM Up) wD(aK bJ cY Hx) wF(aI Co Oh uM) rX(An hG iZ kS) Du(Jp nL Wb) Ha(yH zH tL) Ry(jG jU jV) mS(Em Yl Xa) wQ(Oz Pc Ub) wB(bV cQ Jv) zG(aK rZ vP) uL(aU Cv Cx) Cq(vP wJ) Qy(vP yD) Ky(sM uX) Lj(mT Wb) Vt(qQ tQ) cU(uO yE) dB(uO wC) dM(tU vH) mE(lY Uk) iZ(qT rC) jV(Vz Tl) vI(Bn Nd) AnrY BchW EmiB EqJp FwvH NoqO UchV HbtS YkOk SfkP RcvT JkvW KstU OgnB UofB UyjH VaiC VqqV OzgZ aKvQ bUnN cVtL} Ew{Mb(AA aC Ad aE AF aI AJ An AO aQ Ar As aV AW aX aZ Ba Bb bF bJ bL BN Bo bQ bR bS bU bW bX bZ cB cC cF cG cL cM cO CP CQ CU cW CX cZ dA Db dC Dd dE dG dH DI Dk dN dX Em Et Gd Hq Hu Hv Ij Ik Il Im In Iq Ir Is Iv Jg Jh Jj Jl Jm Jn Jp Jr Js Lv Lw Lx Ly Ma Me Mf Mi Mj Ml Mn Mq Ms Mu Mv Mw My Na Nb Nc Nf Ni Nj Nl Nn No Nq Nu Nv Nw Nx Oe Oi Ok Om On Pa Pb Pc Pg Po Qa Qd Qe) Lx(aA aC aD aE aH aI An Ao aP Aw bA BB BC bE bF Bg bJ BO bQ bR bW bZ cB cD cF Ch cJ cO Cs Cv cW Cx dB dC dD dE dF dG dH Di dJ dK DL dN dX Ef eM fP FR Fw Gd Gl Gp Hq Hr Hu Hv Hw Hx Ih Ii Im In Ip Ir Iu Jh Jj Jk Jl Jo Jp Jr Js Lh Li Lv Mc Mf Ml Mq Ms Mx Nb Ng Nh Nj No Nr Nx Ok On Oz Pb Pd Qd Qe) aM(aA aC aE AF aG aJ aL aN aS AW bB bE bF bI bM BN Bo bS bU bX bZ cA cB cC cD cE cF cK cL cO CP CQ cS Cu cW dF DI dK dN dX EM eP FR Hq Hr Hu Hx Ih Ij Im Ip Iv Jl Jp Lv Ly Lz Mc Md Mh Mi Mj Mk Ml Mn Mt Mu Mv Mw Na Nh Ni Nj Nn Ns Nt Nv Oi Pf Po Pz Qa Qb) Nj(aD aK aQ Ax Bb Bg bS Ch Cs cT cW cX Db DC dD Hv Hx Ir Is Jm Jr Lh Li Lv Lz Me Mn My Na Nn No Nr Of Ok Oy Oz Pb Pd Pe Qa) Lv(aD aG AL AO aS bC bE bI bM bN bR cB cF cM cS Cv dA cP fR Gl Jm Jo Li Lj Ml Mn Nh Nu Nv Of Oy Pb Pc Qb Qe) Mn(aC Al Ao AR As aZ bB bM Bo cL Cp Cs Cw cX DC dN Hr Ir Jh Jm Jp Lh Lj Ms Nd Ni Nl Nw Og Qb) aD(aC Af aI Ax bA bB bE cB Cq Cu CX dD Ij Il Ir Is Jr Js Lj Mi Na Nr) Of(Al Ap bC Cv CW Ii Il Iq Iv Jm Lw Mf Mg Mp Ng Nx) Aj(Ap bB cB Co cW Et Gl Ih Il Jn Mm Nx Ok On Po Qe) Bo(aC AF Ao Bn bS cA CX dX Gd Jm Lj Mh Mu Nx) cX(Ad bB bM bU cB Dc Dd Dk Dl Jm Nx Ok Pa) bB(Af aH bM bN cA cP Cx Dl Gd Hx Nu) Oi(bM cW Gl Is Iv Nn Nw Ok Qe) Ml(aX dA Dc Dd Is Lw Nx Qc) cB(An Ax bA Bb Bn Cx Dc Oc) Qe(Af Cx dC Jj Jk Nv Ny) aC(aR bM bO bS Fw Nc Nx) Mu(dC Et Hx Jp No Nw) Jr(bX FR Hu Nb Nh) aF(aI cG dF Mm Mp Oh) bM(Af bE Cx Il Mk Oe) Ao(Et Gp Ir Jq Nw) Bb(Dd Jm Jq Jt Nw) Nx(aQ Cs cY Lj Mh) Gd(Cw Gp Jm Pd) Po(bS eM Jj) Gp(Bg Jg Jh) Nd(aX Et Ir) Lj(As Aw eM) Mk(cM dA) Ng(Nm Nw) bS(aW Hq) AxMf BgOk CtPd CvJj CwJo FrNo LwMh MpcP HuHx IrJh IvdC JpaY aOdF bRdX} Op{lL(aA AD aM An Ar As Ax BA Bc Bn cG cM Cp Cq Cs Ct Cv Cw dA Dc dF dG dL dM Dr Em Ex Fc Fd Fi Fy Gn Ha Hf Hl Hv Hx Ib iC Ii Ij In Iq Ir Iv Jd JE Jh Jl Jo Jq Js Jt Kd Ke Kn Kp Kq Kr Ld lO Lw Lx Md Me Mi Mj Ml Mp Mq Mr Mt Mw Na Nb Nf Ni Nm No Nr Nt Nu Nv Nx Ny Ok Om Or Ou Pa Pd Pe Pg Pk Po Qa Qx Ra Rb Rj Rt Rv Ry Sr Tn Tv Uc Ud Uz Vi Vs Vt Wc Wf Wg Zq Tl Xa Wm Tj) iB(aE aH aM aN Ap aY Ba bF Bn bR bS cC cH cM cP CT Cu CX Dg Dl Dr Em Ez Fw Fy Hb Hl Ho Hw Is It jF Jg Jp Jq Jr Jt JU Ki Ky Lh Lv Mf Mk Mn Mv Nc Nd Ne Nh Ni Nl Nm Nn Nq Nt Nu Oe Ok Ph Po Ps Qa Qc Qv Qz Rh Rv Ry Sh Sr St Ug Ux Vc Vq Vw Zq) iC(aG Ap Ba Bc bS cM cQ CT Dg Dr Em Gb Hf Hx Jn jO Kl Mk Nc Ne Nh Ni Nj Nl Nn Nu Oz Pa Pc Pd Ph Ql Qw Rx Ry Ug Vo Vq Th) jO(aH aM bA Bn cG cM cQ Ct Cu dA De dG dM Du Hl Hw jI Jq Lh Li Me Nb Ni Nu Of Ou Pa Po Ql Ry Sr To Uc Uw Uy Vq Vt Zq) jU(aD aI aM Ar Bc cM cQ Ct Cu DL Dr Gb Hr Ir jH Jn Jy Kq Ld Lx Mj Ml Mq Mr Ni Nw Ok On Ou Ow Pa Pe Qa Qx Rv Un Vt) jV(aH aM Ar bA Bc cC cM cQ Cs Ct Cu DL Dr Ex Gb Hf Hr Ir Is Jq Jr Js Ke Kq Ld Lh Mq Mr Nw Ok Or Pa Pe Qa Qg Qx Sr) jH(aH Ao Ap Ba BC bS cI Cp Ct DC dJ Fn Fy Gp Ii Io Iq Mr Nc Ng Nh Ni Nl Nu Of On Oz Po Qm Qu Rx Va Vt Xa) lO(aG Ao Ap Ba Bc cM cQ CT dC Hf Ii Jn Mk Mr Nc Nd Ne Nl Nu Pa Pc Ph Po Ql Rx) jL(Bc Bn cM cQ Ct Dl Fd Fy Hf Jn Nt On Pa Po Ql Ry Ug Uw Uy Vq Vs Vt Zq) jI(aC aG BA Bc cM cQ Ct Dl Hf Hw Ii Kl Mk Nd Oz Pa Qw Ry Ug Va Vo) jE(aE aG aH Bc cM cQ CT Fy Hf Ii Mr Nc Ne Ni Nl Pa Po) lM(Ba bB Bc cM cQ Ct Hf Ii Jn Lh Ok Ql Qm Ry Sr Uy Vc) jG(bA Bc cC cM cQ Ct Gb Hf Ii Je Ni Ok Pa Ql Ry Un) jF(Bc cM cQ Ct Dl Hf Jn Nm Pd Po Ry Vq) jK(Bc cM cQ CT Fy Hf Ni Ok Pa Ql) jR(Bc cM cQ Ct Fy Hf Ii Ni Nu Pa Sr) lK(aE cM cQ Ct Dr Fy Ke Nu Ry Vt) jT(aG Bc cQ Ct Du Hf Ni Pa Ry) jQ(cM Ct Fy Ni Ok Po Ry Vt) lN(cM cQ Ct Fy Ok Ou Ry) Du(lW mE nK nL) Lj(iJ mT nL nN) Pg(nH nK nL nN) Jp(dX Nc) nK(Pd Vv) LimU OkVp aMlW aWmT cDnN cNnB} pK{bU(aF Al aO aR aS aW Ax aY aZ Bb Bc bH bl bM bN cC cF cN Cs Cv dB Dd dH dl Dr Em Fb fP Fw Ha Hc Ii Im In Iq Is Jm Jn Jq Ju Ko kR Ks Kx Ky Li Lj mE Mf Mn mS Ng nH nK nL Nm NN No nR Nx Ny Oh oW Oy Pa Pb Pc Ph Pk Ps Pz Qb Qc Qe Qg Qh Qt Qu Qv Qw Qx Qy Qz Ra Rb Rc Rf Rg Rh Ri Rj Rm Ru Rv Sr Ss St Tn To Tr Tt Tv Tz Ua Ub Uc Ud Ue Uf Ug Uh Uk Ul Um Un Uo Up Ur Us Ut Uu Uv Uw Ux Uy Uz Vb Vc Vh Vj Vo Vp Vq Vs Vt Vu Vv Vw Vz Wb Wc Wd We Wf Wg Wh Yi Wm Tj) Li(Aa aE aJ aO aP aS AW aY bN Bo bZ cE Ch cM cN cQ cU Cv Dd dG dL Dp Dr eC Eq Ez Fa FB Fc Fd Fr Fy gC Gz Hc Hf Ib Ic iP Iz Je Ju Jy Kc Ke KF Kg KI Kj Kk Kl Ko Kp Kq Kr Ks Lt Lw ME Mf Mg Mj Mk MY mZ nB Nh nI Nj Nm nN nR Nx Oa oD oF Og oV Oz Pa Pb pF pH pI Qh Ql Qm Qn Qt Qu Qw Qy Rb Rh Ri Rj Rm Rx Si Sr Tn To Tv Tz Ua Ub Uf Uh Uo Up Ur Uu Uv Uw Vi Vp Vs We Wh Yd Yg Yk Zq Zx Tl Xa Wm Tj) nR(aF aW bB bZ cG Co Cw eC Et Fb Fw Ha Ij Im Jg Jh Kc Kd Ko Kq Ld Mg Ml Mp Mq mT Mu Mw mY Ng nH nK nL NN Nq nU OW Oz Pe Pf Ph Pk Qu Qy Ud Uf Vu Zq) Aa(aO Cq DD dK eC Ha Hl Hw Ii Il Im Iq Iz Jk Kg Ks Or Qz Rh To Ut Uy Vi Vq Vt Vw Yi Th) cM(aW Ax Fb Fw Im Kd Lj mE nK nL NN No oW Oz Qu Ru Tv Um Up Us Uu Va Wc Xa) eC(aO Ax Bo cF Dd iZ Je lW mE Mj Mk Mw Ng nL Pa Qv Rf Wc) Dd(Dc Du Fd Gn Hp Ki Kr Og Ou Oy Sf Ul Uu Va Vh We) Ut(aN bF EQ Ki kK Mj mZ Ou Oy Pg Rm Tv Vp Vs Yk) Rm(Fw Ha Im Jp Kq Lj No Nv Oa On Qa Qu Xa) Yk(cJ Ij Im Ks Mn Mw Ng On pI Yi) aW(aA bN bP dD Du kI Oy Pa Uk Tj) Uu(Ao Jg Mh Mm Nm Of Pz Rz Ux) Mj(Ha Im Kq Ks Oa Qe Vt) Lj(aA aE Gb Gz Rf Wb) Im(eQ iP Ki Og Pa) nL(Oz Pb Pc Rg Rj) pI(Du Gn Ki Vh We) Xa(aY dM fB Og) Kq(Bg Dk mZ Ou) Bo(fB Rg To) Gn(aY In Ks) Lv(Qv Tv Ur) Ri(bX mE Um) Rf(Nb No Nr) Pa(Jn Nn Ru) bN(dB dC iJ) dD(aF aO Uo) nK(gC kI Mk) Fb(aY dL) Ha(Dp Vp) Ng(mS We) To(fR Jp) Um(aY iP) Vs(mT Qz) Oz(bB cF) Pk(eQ nI) mZ(Qg Vj) AnKx BgZq FdKs NndL MeHf QuOg JpUs KimT aFaL aObB bRmE} Gz{yE(aA aN Ao As Ax Bc bF Bn Bo bV cC cD cJ cM Cp CQ Cs Cu cV CW dA DC Dd Di DL dM Et Fw Hq Hu Hv Hw Hx Il Ip Iq Is Iv Jg Jo Jr Js Kj Ko Kq Kr Li Lv Lw Ly Me Mi Mj Ml Mn Mq Mt Mx Na Ne Ni Nm No Nr Nx Ny Og Oh Om Or Ou Pb Pd Pe Ph Pk Qa Qd Qe sC uG uI uM uN uP uU uY wD wF wQ yJ yK zA tL) Ok(pS qQ qU rB rC sK sM sO tU uG uI uL uM uO uP uR uT uU uV uW uX uY uZ vA vB vC vH vI vO vT vU vW wB wC wD wE wF wG wH wL wP wQ yD yH yJ yK yL zA zI tL) qZ(aE Al aM aN Ao aQ Ar aU bE bF bG cL Cw cZ dD Di Gl hC Ii iO iP Iq Is Jl Jn Js KQ Kr Lx Mk Nc Nj Nn Nw Nx Oh Or Ow Pe Po Qa Qc qO qP qW) Im(qG rB rC sC sO uL uM uT uU uV uX vA vB vH vI vO vP vS vT vU vV wB wC wE wF wH wJ wK wL wQ yH yK zA zH zI) Kr(rX rY rZ sC sM uG uM uN uR uT uV uX vB vH vI vS vV wE wF wG wH wJ wL wP wQ yD yH yJ yK yL zA tM tL xA) DI(fN fY hL qA qB qG qI uG uI uM uO uV uW uX uZ vB vC vI vS vU vW wB wH wJ wP yL zA zG zH zI tM tL xA) Kn(qH sO tU uG uI uO uR uU uV uZ vB vH vP vS vU vV vW wC wE wF wG wJ wL yH yK xA) Ke(eT pS qT qU qV qX rB rC sO uG uI uU vH vI vQ vS wJ wQ zG zH tM xA) sM(Cv dH Ih In Iq Jn Jp Jt Kf Kk Ko Kq Ks Lj Mn Mt Nw Nx Ny) aN(rX rY rZ sC uN uR uU uX vB vV wD wF wH wL yH zI xA) rB(Aa Fy Ih Is It Jl Js Lh Lx No Nw Po Qd Qe Rm St Vq) qI(Cs dD Fw Ih Iu Jp Kf Ko Lh Lx Mt Nw Nx On Po Qe) uU(cD dE Di Et Hb Jp Jt Kf Mn Nx Ny Og Oi sK uR) qH(Ax bG Cs Fw Jl Ky Lj Lx Mp Mt Nw Po Qd) rC(Fa Fy Is It Js Lh No Nw Po Qd Rm St) qG(Ax Cs Fw Is Jl Jp Kf Lj Mt Nv Nw Nx) Lh(eT jV qT qU qV qW qX qY rA) Qm(eT cZ fN fY hL hP pY qA) vB(Fw

Vb Vc Vz We Wh Ye) jE(Hp Ru Sf Vb Vc Vz Wc We) jK(Rv Sf Sh Vb Vc Vz Wd We) eP(Eq Fd Ps Rv Va Yd Yf) jQ(Eq Gh Rv Sh Vz Wh
Zx) jR(Hp Rz Sf Vc Vz Wd Wh) lO(Hp Ru Sf Vb Vc Vz Tl) dB(qB qI rS rT uW wH) dX(Du eC Eq mS Sh Yf) jO(Rv Rx Sh Si Vc Vz) tX(cW
dN hG sC uR) qX(rS ul uR uX wH) Eq(Jp mT) yJ(Ke Ny) rT(cC vV) EmqU lbmS YemT KrvV NwtR aAuR bUoW dNsK nKoV} jV{Ou(Du
Eq Fc Fd Fi Gb Gn Hl Ho Hp Lp Lt Rt Rv Rx Rz Sf Sh Si Ux Uy Vc Vh Vi Vz Wb Wd We Wf Yd Yl Zw Zx Tm Tl Xa) Sr(Du Eq Fc Fd Fi fR
Gb Gn Hl Ho Hp Lt Ps Rt Ru Rz Sf Sj Uw Uy Uz Va Vc Vi Vw Vz Wc We Wg Wh Zq Tm Xa) Zx(aD Ar aX aZ Bc BO cC Cu Cv cW Dk Gb
Gl Io Iq Ir Jn Js Jy Ke Kn Kx Ni Qw Rm Ry Vt Tj) Qm(Dr Fc Fd Fi Gb Gn Hl Ho Rt Ru Rv Sj tX Uw Uz Vi Wc We Wg Yl Zq Tl Xa) Vt(Eq Fc
Fi Gh Gn Lp Ry Rz Ux Vc Vw Wb We Wh Yd Yl Zq Ye Tm Tl) Lh(Fc Fd Fi fR Sh Si Va Vi Vz We Wf Yd Yl Zq Zw Ye Tm Tl Xa) Rv(aQ bJ
cC Cu DB Dg Fn Hx Iq Jo Mg Qw) Iq(Du Gh Hl Hp Rt Rx Rz Sh Ux Vw Ye) Qg(Fi Gh Ps Rx Sf Va Vw Wc Yl Zw Xa) Nw(Du Hp Lp Ps Sf
Uw Ux Vh Vw Yd Ye) Po(Fd Sf Si Uy Vz Wf Yd Yl Zq Xa) Rz(Et Jd Jn Kn Kq Mg Mm Nu Ql Zq) Cu(Fd fR Hl Hp Lp Vb Vw We) Va(aD Et
Jq Lx Mj Or Pf Ql) Vh(Ar cC Di Jj Nc Ph Tz Wh) Dr(aD dF Jr Js Ql Uo) Eq(Ad Aj Fn Jd Mf Mr) Gb(aI Ar Hb Lv Or Tz) Si(Fw Ni Nu Ql Tz
Tm) Ok(Du Ps Rt Wd Zw Ye) Yd(bR Fw Kn Nu Ql) Zq(Ar cQ Io Ir Vc) Lt(aD aH Is Lx Pe) Un(Fd Uy Wd Zw Tm) Hp(li Jl Jq Ps) Sf(Fw Jj Nu
Ql) Wh(Ad Dc Jn Ke) Yl(cD Qc Ql Tz) Vc(Ar cU dF Mm) mW(Ar As Bn Ph) Mr(Rx Wc Ye) Hb(Fi Ry Vi) Ke(tO yJ Tm) Vb(Il lr Jo) Ux(Lx
Ml Ow) cF(Du Ps Uw) li(Lp Ye) Tl(Js Tz) Kr(tO tT) cC(Ry Wc) sH(dB hG) wE(Cs Fp) Dull FdFw MfSh WbbU VzQl WfJn JkVi JrYe TmOw
KkqH KlmZ RtPh TkcQ OrfR UwaG UydK aRnO aSnT cHnN} IL{bR(kC kE kF kG kI kK kN kO IW IX IY mE mF mH ml mP mT mU mW
mZ nA nB nD nF nJ nM nN nO nR nT nU) bX(kC kE kF kI kK kN kO kP IW IY mF mH ml mM mP mS mT mW mZ nA nC nD nH nI nJ nK
nL nN nO nR nT) Ou(Eq Fc Gh Gn Hl Ho Lt Ps Ru Rx Rz Sh Si Uw Uy Uz Va Vb Vi Vw Vz Wg Yl Zq Zw Tm Tl) Cu(Fc Fi Gb Gh Hl Rt Ru
Rv Rx Sh Sj Ux Uy Uz Vb Vc Vw Vz Wc Wg Wh Yl Zq Tm) Lh(Du Fc Fd Fi Gh Hl Ho Hp Lp mM Ps Rv Sf Si Sj Uw Uz Wc Wf Wg Zq Ye
Tm Tl) As(kC kF kG kK kN kP IW IY mM mP mT mW mZ nA nB nC nD nH nJ nK nL nN nO) Nu(Dr Fc Fi Hp Lt Rt Rx Ry Si Sj Va Vh Yd
Ye) Hp(aP Ex Fw Ii Iq Jn Jr Nt Po Ps Qe Sr Un) Un(Gb Lp Rz Si Ux Uy Vi Yd Zq Ye) Vh(cH Kd Nc Nd Nl Nw Qm Ru Ul Vc) Sr(Lp Ps Rx Sj
Vi Wf Wh Zw Zx) nT(Af aM aS aW aX bG bJ Bn Ki) cU(kO nB nC nl nJ nK nL Vz) Ye(DK Ii Jr Nt Ql Qm) bJ(kO IX mY nC nH nJ nL) Dr(Ct
dF Jp Po Qm Uo) Zx(cC Db jE Nm Qw Rj) Lp(Fw Ii Jn Nw Po Qe) Vc(aY cG Ct dF Hf Jp) kF(Af Aj bE Bn Cx oP) Eq(Aj Dg Fn Jp Ux) Sh(Dc
Jp Mf Mm Uf) Zq(aG Fi Hf Io Or) aR(kO nC nJ nL nO) nN(aP aS bB cH cN) mY(Af Bn cA Cx hR) Fa(qH vO vW yH) Sj(Et Po Ql Qm)
Wh(Ad Cw Dc dF) mM(Jo Js Qb Qc) Fi(Hb Qm Vt) Hx(sH Uw Vi) Yd(Ar Kn Ql) Ok(Du Gh We) Or(Lt Ux Vw) aS(kO nC nL) aZ(mS nC nL)
mW(Bn De Ph) Fw(Wf Tl) Wb(bU Ql) Jp(Ru Vz) Qm(Rt tX) Ux(Hf Jj) Va(Po Ql) dF(Lt We) rQ(AN) AfnO DuOi FnRv MfSf NiSi lzmZ QwVi
UwaW dBmT} Du{Dd(eQ fB gZ iJ iP kC kE kF kG kI kK kN kO kP kR IW IX IY mE mF mH ml mM mP mS mT mU mW mY mZ nA nB nC
nD nF nH nI nJ nK nL nM nN nO nR nT nU) oD oE oH oN oO oP oQ oW pF pH pl Vc Vt) mE(Aa aG aH aJ aN aP aS aW cM Cx dG dM fA fB
Hb iP kI kO kP Me mU nY Og oQ oT Oz Pb pI Qm Qn Rj We Yg) aW(eQ fA fB gC iJ iK IX IY mP mS mT mU mW mY mZ nA nB nC nD nH
nK nL oD oT oV oW pH pl) Aa(eC fP gP hB hC hF hG iA iH iJ iO iP iZ kQ kR kS nY oE oF oH oN oV pF pl tF) fA(aI aJ Ao bN bR bU bX cA Cx
Et Fb Gn Hr Ip It Jn Jp Nr Ny Qd Qe Qn Sr Ut) Me(kI kN mM mS mT mU mW nH nJ nL nU oO pH) lM(aG aJ aP bC bP bS Fp Il Mm Qn Qz
Yd Ye) nK(aJ cN dL dM eF kI mT Og oH oN oO Pd) jH(aE bR bU cD Oi Qc Qm Ug Vc) Jp(eF Gb hG jR kQ IK IW Vs) iJ(aO bF bL bR dG Ed No
Sr) oW(aP aS bU dG dM mT oT Wb) dX(aM Jj Mn Mt Un Vt Zx) iP(aO bU Ih Nm Nt Qc Wb) oT(Fw Im Jm Lj Oz Ru Uy) fB(bU gZ IW Mw
Nn Qu) pl(aN aO cJ Ct Li Zq) Yd(jE jQ jR IK IN) eP(aM Hb Jj Mn Ur) Mx(jK jQ jR jT) Fw(oN oV pF) aG(jE jT jU) aJ(iZ nN nU) aS(gC gZ
oN) iB(cC dB Oi) Qy(Ib Rj) Li(mU oV) Ok(jl Vp) Ou(jO jU) aO(gL hB) kP(oP) dG(hB pH) gZ(aN bI) jE(Ne Oi) jF(Fn Hx) jL(aE Jq)
kR(Cw Nm) lN(Hb Hf) CueF DkjI DrjK MjQe IlVt LhjO PhmU cNnH} Lj{Wn(aA AD aE al Aj aR aU aW aY aZ BA bB BC Bg bI bJ bO bP
bV bW cG cH cI cJ cK cL cM CO cP cQ CT cW cZ dB DC Dd De dG dH dI Dk Dp dR Ef Ez Fa Fb Fn fP Fr gP Ha hC hG Hu Hv Hw Hx Ib Ic
Ih Im In iO IP Ir Is It Iu Je Jg Jh Jk Jl Jn Jr Js Ju Jy Kf Kk Kl kQ kR kS Kz Lx Ma Mh Mk Mn Ms Mw Mx My Nb Nd Ne Ng Ni Nj No Nr Nu
nW NY Oa OE Of Og oH Oi oK Om Or Ow Pd PF Qa Qb Qd Qg Qh Qm Qu Qv Qx Ra Rb Rf Rg Ri Ss Tv Uc Ug Uk Um Un Us Ut Uu Vp Vv
Wm tF) Wb(Aa Af Aj Ao Ap As bO bS Cu Db Dg Dk Dl Et Fn Hx iJ Il Jd Jg Jp Jt Kg Kp Kr Kx Mg mS mU Nf Ng Nm Nt Nu Nx Qm St Ug Ut
Vh Zq Tl) fA(bB bU cl cM cQ Cw Ko Rf Rz Zq Zw) Db(Gb Gh Rz Uw Ux Vi Vw Zq Ye) Ry(eP gZ kl mE mT mW nU oD oT) cM(eQ gZ oD
oT oV oW pH pl) iJ(Dr Fc Fi Lt Vw Zq Ye Tl) Gb(Cu eM mE mW oV oW pl) bU(eQ fB gZ oV oW pH pl) qZ(tN tO tR tS tT tX zA) Vi(Cu mE
mT oV pH pl) dX(Fc Lt Rv Uy Zx) eP(Fc Lt Rv Wc Zx) sF(Dp Pi qX vl Vu) Ex(qH sM yE tM) tT(Dl hP jK rB) tX(hB hP kS rB) sI(Dp Fn lK
Pi) sH(Dp hG Pi qX) Vw(eF iP Wf) mE(We Yg Tl) Zq(mU Ni) Ko(fB oV) tN(hP Jv) tV(dC nY) pl(Dr Sh) CuWh YemT TInK RmoV PisJ bBfB
cQoW nJhR tOrS qXzA} Ke{tO(aJ aM bR bU cB cD cF Ch cM cN dB Dg dH DL dN Ef fN fP Fw fY Gp hB hG iH iO Ip Iz Jh Jk JQ Jr Jv Kj
KR Kz IK IM Mg Mh Mj Ne Of oH Or Pc qA qZ RA rB rO rS rV ul uM Un vB Vt wE zG) uM(aI Ao Aw bU cB cF cK cM cN cT dB fP Gp hB
hG Hu Ib Ic iZ JE jL Ju Jv Kl Kp Kz Ma Mh Mn My Nm No Of Or qU qV qX qY RA rB rQ sH sl sJ sK sO tR tS vH Vt Vv wE wQ yJ Wm)
yJ(aJ aN Bb bM cB cF cP dA dB Dl fN fP iP iZ jO Jv kS Kz Mh nW Ny Or Qe qZ rB rQ rV sF sJ sM Un Vt vU Wm tF) tR(aS Bo cB cF cT dB
dL fP hB hG Im Ip jO Jv Kz IM Mh Or Qd Qe RA rB Un zG) tT(Aw cB Dl dN fP hP jO Jv kR Kz RA rB) sF(Aw Bc Co dB Fn fP hG Ib Jk Jv
Kf Oy Pk) sI(aZ dB eF hG jE Jh Jk Kp Kr Nr Oy Tn) sJ(Aw Bc Co dB eF fP iH Kf Kp Oy Tn) rQ(aZ Co Dk iA Jk JO Kp pF vA) tX(aO dN
fP hB Hu jE Kz rB Tn) sH(Ba Bc dB Ef hG Jk Kf Kl Oy) tS(cF dB fP hG Jv rB zG) lM(aN Hp qU Wh Yd Ye) vU(fP Gp Or rA zG) Ex(eT qG
uG wJ) tN(bl Jh Jv rA) jL(Ux Va Vw Wb) Gp(rR vA wQ) cB(vV wJ zG) cF(vA wJ wQ) Ne(hP tV) Yd(dX jQ) Jv(sO wQ) dB(qU rS) fP(qU tV)
rA(kF nT) ul(jE Of) SfdX ZxIK WeOk OrvA UmqA UxjU aNrR dAhP dHwJ rBrO] iB{Va(al Aw Bb BG bN cC Eq Et Hf Ik In It Jj Ju Jv Lh
Lx Ms Og Oi Oy Ph Po Qm Qn Qt Qz Rc Sh Wd Wh Ye) Ux(Bg bS cC cF Dg Dl Ez Hb Hf Iz Ld Lx Lz Mk Ml Oi Ou Oy Ph Qb Qm Qx Qz Rg
Rx Rz Sh Ss Tz Vw Zx) Hf(Dr Fc Fd Fi Gn Hl Ho Hp Rt Ru Rv Rx Ry Sj Uy Vc Vz Wc Wd We Wf Wh Yd Yl Ye Tl Xa) cC(Dr Fi Gb Gn Hp
Lp Ps Rx Sj Vc Wb Wc Wf Wh Yd Yl Zq Zw Ye Tm) Yd(cH jE Kn Lh Nc Nd Ne Ni Nl Nu Ok Qc Ql Qm Qw Un) Ye(aE aS bR Db Iq Jl Jr Nw
Oe Po Qc Ql Sr Ug) Hp(aE aS bR Ii Iq Ir Jr Nw Po Ps Qc Sr) Vh(aG Ef Mr Nc Ou Ql Qw Ru Sh Ul Wh) Lp(bU cD Ii Iq Jn Nm Oe Qe Qm Sr)
Vc(aY bC bW cG dF Fn Jp Mg Uf Vt) Dr(Gl Nu Ou Po Ql Qm Sf Zq) Ok(Fc Fi Gh Rz Uw Wc Wf) aR(kC kO mM nC nL nO nT) Sh(Dc Dd Hx
Iq Qw Sr) Tl(Ar aS Jr Lh Ou Qm) Vw(Lh Mh Oi Ou Qw Vt) Sr(Ho Ps Rv Vz Wf) Zq(dB Il Ou Qw) Zx(cH Hx Nq Rt) Wf(cD Db Ql Qm) Qz(Fd
Hl Ps Zw) Vt(Fd Fi Uy Xa) fR(Kr Ne Oi qU) Bc(Fc Fi Rx) Eq(Ad Cu Mg) Fn(Ru Rv Vz) Qw(Fc Uw Xa) Lt(Em Ii Lh) Un(Gh Rv Sf) dB(nT sH
sJ) Hc(mZ nH) We(Jq Uc) Wh(Ad Nt) aE(Fc Fi) bR(mT nU) mW(Dc Iz) hG(sH sJ) AjkF AskC NmVb MhUy NiSi HoPh HuUw IlSf HbWc
WbbU VzLh JqPs RtQm aSnT bLnL cWnK] Eq{Jp(Ad aF Ap aS aW aZ cZ Db eM Fi iJ jO Kg ml Mm nA Nc Ne Ng Ni Nl Nm nN Ns Ok Ps
Qc Qe Qh Qv Qw Qy Qz Sr Ss St To Ua Ub Ue Uf Ug Uk Um Uo Up Uv Ux Vc Vh Vp Vw We Wh Yi) Ng(dR eC eF fP gL gP hB hC hF hG
iA iH iJ iO iP iZ jK kG kQ kR kS IW mE mS mT nR nU nW nY oD oE oF oH oK oN oV pF tF) Ok(bU Cu cZ Db dl Gb iJ iO jF kG IK Lv mE
ml mS mT Nc Nj nK Nl pF Ps Qn Qu Qy Rf Rm To Ub Vp Vw Wb Yd Zq) Fn(jE jF jG jH jl jK jL jO jQ jR jT jU IK IM IN IO) dX(Ad aM aW
aX Co Db Dl Fy iH iO Kd Li Ni Pz Ur) mT(Al aW Cv Cw dB Fy Ij Il Ip Iq nB nK oW Ut Tl) eP(Ad aM Ap aW aX Co Fy iH Mn Mt Ni Pz Rz)
Mg(jG jH jl jK jO jQ jT jU IM) Dg(jG jl jK jL jO jQ jR jT IN) Aj(jE jF jH jL jO jT IO) jK(Ad Ap Cu Jd Nu Va Xa) Ux(jF jl jL jO jR Pk) Oz(mE
ml nK oT oV oW) iJ(Et Ha Nm No Ut Tj) Cu(jF IK IM IN) Et(mE mS mZ nK) Qu(jT jU IN IO) Mf(jG jT jU) Mn(iO mE ml) Ut(aM IW mU)

YieQ TloT bCoD} mS{aW(Rv Rx Sf Sh Sj Uw Vb Vh Vz Yh Yi Yl Ye Tm Tl Xa) Il(Dr Vj Vz Wb Yh Yl Xa) Ye(Ao Jo Kg Mm Nm) Mm(Gd Vz Yl) Ij(Ps Vi Yg) Fd(Ok Qe) Uf(Wh Yg) JtYl XacN RzUu nJhR} rB{sK(Im Nw Qd Vt Vu Wm) Un(fY qO rW vV) tN(Fp Js Qd Ql) Kk(qO rU rW) mW(Aa Pa Pe) tS(Fw Js No) Fa(qO rW) Im(uG uX) Lh(hG rO) Vu(uG uM) WmwC FwvT MtzA TrsC QdrW SrtM KnrO OrcI} mZ{Ye(Ao cJ iJ Jo Kg Kj Ko Mn Ng) Mn(Dr Lp Lt Rt Rx We Yl) Wd(bZ Co Kq Nn Nq) Dr(bB cJ Qv) Hc(qW qX qY) Yl(aW bB iJ) Rz(Ct Uu) GdMm NgWe XaOg KxoV RvaW bBeQ} Ok{Vp(Dr Gh Gn Rv Rz Sh Vb Wb Wh Yl Tl) We(Dd Mf Nt Qe Qn) Ps(iP Ki Mf Vt Wb) oP(Gn Rt Yj) Nc(Dr Gn) Sf(Ju Qn) Rx(bF nR) Rv(Mj Rm) MhWb WhKi KlUx OuoV UwVt} pH{Rm(Al Ax Ha Ir Jn Mn No Nr Qa Qe Sr Yi) eC(Fd Or Ou Ow Ps Tn Tr Tz Vp) Wc(Me Rj) Uu(Ao Rz) Vi(No Qn) AnKx AxcM DkYi FdHa MjQe NgWe YhiP RgbX bBnR} fA{Ax(An bl bJ bX cM Cw Hw Lp Ng Pb Pc We) Cw(Bg Uu Yl) Ha(Vp Zw) Ng(We Yg) Qe(bX Mj) Kq(Dk Pg) bI(Qv Yh) AnKx FyUw NmUu MnRf MwYe YgPc RgbX} oV{Ha(Dp Fd Mj Pg Rm Vp) Kx(An aW kK Po) Ax(cM Pc) We(nA Ng) Qu(bF Hq) Ou(bB Fy) AoUu CqVs FwbM NoVi MjQe MlcM MxPs TtOy YgYi KsPg RvaW RgbX UodD} Un{uM(An Mb Tt Tv vO wE) vA(An aV cF Ne zG) Jk(qH sM uG uX) rS(iA Mg Ng) uX(Ib Ne Of) Tv(rW sC) AnwE EmqY cFrW dAhP dNsK} aR{qV(kC kO mM nC nJ nL nO nT) nN(eD qT qW qX qY) qT(kO nD nO nT) qX(kO lX nC) qW(kO lX nO) TkeD fRhR} eQ{Ha(Fd Mj Pg Ps Qh Rm Vp) Mn(Qh Sj Tr Yd) Uu(Ao bX Mm) Kx(An aO) AxcM NoVi MjQe NgWe YiPb KsVa PsPh UodD} Im{wE(AN dB dE hG iH) dB(uX vO wH wQ) Jk(rQ uI uO) Kr(sK wF) aN(vH vT) MjsK NevA IcuI YemU iZvO qXuV} qY{cU(kC kO nH nL nN) nT(aS bJ Ki) Kl(kF kN) fR(Mp Ng) nN(cH Kk) AjkF ApkK EmOr PhmW aMlY bHlW} qW{cU(lW lY mW nB nO nT) nT(aS bH cI Kc Kk) kF(bH Kc) AskN LhhG OrkP PhmW cHnN fRtF} aW{Yl(lY mU mY nA nC nD nH nJ) Vz(mU nA nC nH oD) FclY XaoO LpkI RvkG VbnH} cF{Dl(rS rW sK uR vA vV wE) Kf(rW sK vA vV wJ) Qm(wF wQ) LhwQ TkeD fRhW nTqX} Qe{Mj(gC gZ oD oT pI) Rm(Rx Va Yi Ye) Tv(wE zA) AaPs FdkG TtwE YjoP WfVp tSqZ} Kq{Dk(gC gZ oD oP oT pI) Of(rX rY wJ) AjwJ GnoP IbrQ JvqH PggZ bFgC dBrV iPrS} Kr{Of(rQ rX rY rZ) wJ(dH Nn rS Sr) aN(rX rY rZ) AjrZ aQwD dBrV dHzA fRqT tSiP} No{iJ(Fd Hp Ps Uw Vi Wd Wf Wh Yg Ye) Vi(iO iP nY) Rf(oO pI) TvTk} Ha{Mj(gZ oD oT pI) Vp(gZ oD oT pI) Dp(gZ pI) Fd(mW pI) Rm(gZ oD) NqvT} hR{nI(Hv kC mF Nc Ni) nJ(Aa Jr Lh Qc) mM(Jn Qc) AamU MaoP JskN cMfR} uM{Vt(cX Kk Qm sK Vu wE) Sr(Qx Tn Tv) wE(Dl Kf Oa) WmrS FavO QmVv} We{Ng(gC gZ nD nU oD oP) Mn(nB nR) AaiO IlnB JtoK OnoP nCnL} Xa{Og(kO mU mW nA nB nO nR nU) cN(hC nB) ml(dM Pb) cDiP} An{Kx(gZ oD oT pI) eD(rQ Tk) wE(Ed Fw) qX(tS uV) RbrQ eCwF} dB{rV(Io Iq Ir Is It Iu Iv Ks) rS(Qd tQ) TkeD tSqZ} mU{Ye(Ao Mw Nn) Aa(hW rC) Wc(Ao Cu) NgRx HlQa IjSf RzUu bGeD} mW{Pe(hW hX rY) qV(Kc Ki Ph) Pa(hX rY) AarC PhqX mMrZ} tN{Aa(Ch Ez Jv) Dl(Aj Mg Of) Jk(Cu Ny) IpaN JvRh OazG} mI{Rg(Dr Wb Wf Yg Yc) Pb(Rx Yj Tl) iP(Vz Wc)} hP{Po(Mj Nq Uk) Nq(Jl Lx) WmrS LudA MjLh JlUk VtuI} oP{Gn(Ao Cu On) Tl(Cu hB) TjTt EtVh WcJn KpfR RzUu} tS{qZ(dE eC Ih Mx Nw zG) DlqQ GlNe IphG} qX{kF(Af Bc Or) rS(Lu Mf Qd) aSnT cHnN cUmF} Nm{Uu(oD oT Zx) Gd(iP kR) Vb(Cu iJ) MhWb} Mn{nR(Rt Sf Tm) eM(Sf Yd) RxcM RtgZ VinB} Tk{Sr(Tn Tv) cB(eC eD) NnUu MthG NgeD IrIu} qT{cU(mP nH nN) EmOr LhhG PimP aSnT cHnN} wE{Fw(aN iP) EdaN FaQm QdJv LhhG OazG} Dd{Sf(kP Lh) oO(Og Wc) ShLh RvkG} cM{Ax(gZ oD oT pI) CsgZ fRhX} sK{Ri(iP oH Vt) Vt(Ne Qm) IpJf} Em{hW(Dk Fn) hX(Jq Tn) bRhV} Ql{Of(tQ wC wD) JkrQ wCqI} eD{aS(kF lX nT) nN(cH cU)} rZ{mM(Hu Jh Po) oO(Jj nD)} rS{Wm(aC bC) CsuO KsiP RidA} pI{AoUu FadR FybF RgbX UodD} Wb{Mh(iJ Mm) Vp(Lh On)} Jv{JswL KkqH NwrR NyvP} aN{vT(Ed Fa Fw) NxrR} qV{cU(nH nN) LhhG cHnN} oT{Ao(Uu Wc) NgYd UodD} Aa{AlSf GnNi UykG} Tv{SrvA QmuP NyqA} Vb{CuCv CwkR HwiJ} fR{AdhW SrgW aPhX} uI{Of(Kf Vu) VvrW} Cs{qZ(wQ zA)} Et{YdiJ RxnR} Il{GnlY YhkG} Uu{AooD UxkE} Uy{DbbB NtOy} dN{wF(Ar Ko)} PoKxoD FcHbaM FwnWvU GbcDeC GdHfgW NcKkzG NeLhvA NgShnY HpHwnL IbNyqA IpiZvO SrKztQ QubFgC KfcBvV YlcNnH UodDgZ VibBnB dHwLpF

Unconstrained panels with 2 analytes, where 1.0E-8 >= 'AUC p-value' > 0. Contains 649 panels of 199,653 total panels evaluated. : Ji(aA aC aN bM dB Et Fp Fr hP Hq Hr Hu Hv Hw Hx Ih Ii IJ Ik Il Im In Io Ip Iq Ir Is It Iu Iv Jg Jh Jj Jk Jl Jm Jn Jo Jp Jq Jr Js Jt Jv Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Ps Pz Qa Qb Qc Qd Qe qI Sf Sh Si Uy Vj Wb Wc Wd We Wh Yk) Li(AA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg pK Po Pz Qa Qb Qc Qd Qe Ti) Gc(aC Aj aM Dl dR eC EF FP gL gP gW Ha hB hC hF hG iA iH iJ Ik iO iP iZ jE jH Jj jK jM jO jQ jR jV kP kQ kR kS Lj lK lO mS nB Nc Ne Ni Nk Nl nW nY oE oF oH OK oN Oy Oz Pa Pb pF Pz Qb Qe Qv Qw Qz Rc Rg Sf Uc Ue Uh Uk Un Uu Uy Va Vb Vo Vq Vs Vt Vv Wc Wh tF) Ok(Aa Aj Dr Eq Fp Hu Hx Ii Im Io Is It Iv Jh Jj Lj Lu Lv Lw Lz Mb Mc Me Mf Mg Mh Mj Ml Mp Mr Ms Mv Mw My Mz Nb Ne Ng Nj Nk Nq Ns Nt Nu Nw Ny Oe Of Og Oy Oz Pb Pc Ps Qd Qe Rx Sf Sh Wb Yk) Nw(Et Fp Hu Ij Im Iq Jj Lj Lu Lw Lz Mb Me Mh Ml Mp Mr Ms Mv Mx My Mz Ne Ng Nj Nm Ns Nt Nu Of Og Oy Oz Pb Pc Qe) Lj(aA bM Et IJ Im Jg Jj Jl Jp Jt Jv Lh Lw Mm Nm Nt Nu Nv Nx Ny Og On Pc Pj Qd Qe Uh Vt Wb Zq Wn) Et(Fp Hu Im Jj Mh Ml Ms Mz Ng Nj Nu Oe Of Og Oy Qc Qe) Fp(Aa Im Jg Jj Jp Lw Mz Nm Nx Ny Og Qc Qd Qe Vt) Qe(Aa Aj aN Du Hu Im Jj Ms Nm Og Oy Oz Pb Ti) Im(Aa Hu Jj Ms Ng Nj Nu Og Oy Pb pK) Pj(aC Cs Fa jB Sf Sh Uy Va Vi) dU(bB Gp mE Mw Nj Oz Qc Ut Wf) aM(DW EO EW Zq) Mb(DW EO EW) Id(hR No rC uG uI uM) Kc(bM lM tO tR uM yJ) Vt(aC Cs gV Vh Ti Th) jP(Dr Vc Vh Yl Zw) Kq(Aj Ef Iz Jh) jB(aO aW bN Oz) Aa(bM Jj Nu) Lv(Dw Eo eW) Lx(DW eO) Mz(fN hP qQ) Yd(hA jD jY) Uh(bM Cs tT) cR(oD oT pK) Bo(dW eW) Si(hA jD) Qd(Jj Oy) Kx(dX gV) jY(Vh Tl) pK(bU Nk) AjNm CsJv DltT DuQy EoJr TitX EqJp EwMn ThqA MhZq ZxjD KigV LhUy YlnK VaiC PkbM bSeO tOqZ sIjM Unconstrained panels with 2 analytes, where 1.0E-7 >= 'AUC p-value' > 1.0E-8. Contains 715 panels of 199,653 total panels evaluated. : Qe(aA aC aF Al Ar As Aw bM Bn bS cB cI cM Cs Ct dB Dk dU Hr Hx Id Ij Ik Il Io Ip Iq Ir Is It Iu Iv Jg Jh Jk Jl Jn Jp Jq Jr Jv Ki Lu Lw Lx Ly Lz Ma Mb Mc Md Mf Mh Mi Mj Mk Ml Mm Mn Mt Mu Mv Mw My Mz Nc Nd Ne Ng Nh Nj Nk Nl Nq Ns Nt Nu Nx Ny Oe Of Oi Om Ou Pa Pc Pd Pe Pf Pg Pj Ps Qb Qc Qd Vt Yk Zw Ye Wm) Nw(AA aC bM Eo Fr Hq Hv Hx Ih Ii Ik Il In Io Ip Ir Is It Iu Iv Jg Jh Jk Jm Jn Jr Jt Lh Lv Lx Ly Ma Mc Mf Mg Mi Mj Mk Mm Mn Mq Mt Mu Mw Na Nb Nc Nd Nf Nh Ni Nk Nl Nn No Nq Nr Nv Nx Ny Oe Oh Oi Om On Pa Pd Pe Pf Pg Po Pz Qa Qb Qc Qd) Ok(aA Et Fr Hp Hq Hr Hv Hw Ih Ij Ik Il In Ip Iq Ir Iu Jg Jk Jl Jm Jn Jo Jp Jq Jr Js Lh Lx Ly Ma Md Mi Mk Mm Mn Mq Mt Mu Mx Na Nc Nd Nf Nh Ni Nl Nm Nn No Nr Nv Nx Oh Oi Om On Pa Pd Pe Pf Pg Po Pz Qa Qb Qc Rv Vb Wc We Wh Yd) Lj(Aa dU Fp Fr hG Id Ii Ik iO Iq Ir Is Jd Jn Jq Js Jy Ke Kq Lv Lx Lz Ma Mc Md Mg Mh Mi Mp Ms Mt Mu Mw Mz Nb Nd Nh Ni Nj Nk Nn No Nq Oe Of Oz Pb Pd Pe Pf Pg Po Qa Qc Qm Un Up Vw Ti) Im(Fr Hx Ik Ir Iu Jg Jh Jk Jl Jm Jp Jq Jr Jt Lh Lu Lw Lx Lz Mc Mg Mh Mj Ml Mn Mv Mw Mx My Mz Nd Ne Nh Nk Nm Nn Nq Ns Nt Nv Nx Ny Oe Of Om Oz Pc Pe Pf Pg Po Pz Qc Qd) Gc(bU cM Dg Du eP Gd Kd kE Kx Lz mE Mr Nf Nh nK nL Ns Ny Og Oi oO oP Pd Pg Qa Qc Qd Qh Qt Rb Rv Ry Sh Sr St To Tv Tz Ua Ud Ug Um Ur Us Ux Vc Vi Vp Wd We Wm Th) Et(Aa Aj Cs Hx Ij It Jh Jl Jm Jn Jr Js Lu Lv Lw Lx Lz Mb Mc Me Mg Mr Mv Mx My Nb Ne Nh Nq Ns Nt Ny Oz Pb Pc Pd Pe Pf Qa Qb Qd) Ji(Aa aF Aj Ar cB Ch cI Cs Dr EF Eo Ex Fc hG iH iZ pY qH Qx Rc Rv rW tR tS tX Va Vb Vc Vi Vv Vw Wf Wg Yd Wm Th) Mz(eT eZ hO Hx Ij Ir It Jr

Figure 41 Continued

Lw Mn Ms Nm Nt Nu Ny Of Og Oy Pj pY qC Qd qH qI rW) Aa(Fr In Iv Jp Lu Lx Lz Mb Mf Mh Ml Mq Mr Ms Mt Nb Nn Nt Ny Oy Po Qa Qd tX) Pj(Ax bM Du Fp Gd hC iA iJ iZ Jj Jv lK Or Si Uu Vb Vt Wb) Fp(Hu Ij Ik Jm Jn Jt Lh Mm Nt Nu Nv On Oz Uh) dU(aW Ax bU hG Lt Mn nK Nn Pb pK Ru Xa) Qd(Hu Mh Ms My Nk Nm Nu Og Oz Pb Pc) Id(aC jK Jp jV lK lM Uh wF) Ny(Jj Mh Of Og Oy qA tT yJ) Vt(Aj Ax bM dE Du Kr sK tO) Zq(aC cM Eq jY Ki Kl) Jp(Hc Ic Iz Mh Sh Yd) Uh(aC Ar Ax cM tX Wm) Ke(aC EF Jv qA) jB(bU cM dM mE Oy) Eq(Jg Kq On Qu) No(Ib Qw Uy Wb) Jj(Jg Nt Qa) Lh(Sf Sh Wh) Li(bM Qu Wb) Un(Cs tO vA) jM(sF sH wB) pK(eC nR Oz) Aj(Ad Jt) Dw(cX Mn) Nk(fA gZ) Zx(jY lN) Kx(eP Wb) Va(iB jY) bM(Bb Sr) dB(rV tV) hR(nI nJ) CuVb DrhA DuiJ EoPo TiuW ExqH GzyE NmOf NtUy IjOg YdjE JsjV TljP KlKq KrtV OpiB OnOy PkaC aDeW aNrQ bBfB cRoW

Unconstrained panels with 2 analytes, where 1.0E-6 >= 'AUC p-value' > 1.0E-7. Contains 1,236 panels of 199,653 total panels evaluated. :
Qe(AD aE Af aG al aJ aK aL aM An AO AP aQ aR aS aU aV aW AX aY aZ BA BB BC bE bF Bg bH bI bJ bL bN BO bP bQ bR bU bV bX bZ cA cD cF cG CH cK cL cN CO CP CQ cS cT CU CV CW CX cY cZ dA Db DC DD DE Dg dH DI dJ dK DL dM dN Dr Ef Eo Fa Fd Fn Fr hG Hp Hq Hv Hw Ib Ic Ih Ii iJ In iP Iz Jm Jo Js Jt Kc Kk Kl Ld Lh Lv Me Mg Mp Mr Mx Na Nb Nf Ni Nn No Nr Nv Oh ON Or Ow Ph Pk Po Pz Qa Qt Qu Qw Rm Rv Sf Sj Sr Ss St Tn To Tr Tv Uh Uu Va Vb Vc Vi Vv Wb Wd We Wf Wh Tl Th) Gc(aD aG aJ aO Ar aS Aw Ax Ba bB bE bM bN bR bV cB cD cF cL cQ cR Cs Ct Cu Cv dB dC DD dH Di Dr Ed EM Et Ex Gn Hc Hu Hv Hw Il Io Ip It Iv Ji Jm Jn Jp Jr kI Kz Li Lv IW IX IY Ma Me Mf Mh Mi Ml Mp Mq Mw Mx Mz Nd nH Nj nN nR Of Or Pc Pe Pf Po Ps Qg Qu Qx Qy Ra Rm Rt Ru Si Ss Tn Tt Ub Uf Ul Uo Ut Uv Uw Uz Vh Vw Wf Wg Tj Ti Yf) Lj(aC cM dB eC fP Gb hC Hq Hr Hu Hv Hw Hx Ic IH Il In Io Ip It Iu Iv Jh Jk Jm Jo Jr Ju Lu Ly Mb Me Mf Mj Mk Ml Mn Mq Mr Mv Mx My Na Nc Ne Nf Ng Nl Nr Ns Oh Oi Om oN Or Oy Pa pF Pk Pz Qb Qw Qy Rc Rf Rg Ri Rj Rm Sr Tn Ur Us Ut Vh Wm) Ji(aG aH aM AO AW AX bE cC cD cF cM Co Ct Cv Cw Cx dA dD dE dH DK dL dR DU eT eW Fa Fi fN fP Fw Gb Gl Gn Gp hC iA Ib Ic Id Iz Ju Ki nY Oa oN Ou qO qP Qt Rg rQ rR Rt Ru Ss To Uh uM Uu Uv Uw Ux Uz Vh Vt wE Xa Ti Yf) Qd(aA Aj bM Fr Hv Hx Ik Il Io Ip Iq Ir It Iu Iv Jg Jh Jk Jl Jn Jp Jq Jr Js Jt Lu Lw Lx Ly Lz Ma Mb Mc Md Mf Mj Mk Ml Mm Mn Mp Mq Mu Mv Mx Nb Nd Ne Ng Nj No Nq Ns Nt Nv Nx Ny Oe Of Pa Pd Pe Pf Pg Po Qa Qc) Et(aA aC Ax bM Dr Eq Fr Hq Hr Hv Hw Ih Ii Ik Il In Io Ip Iq Ir Is Iu Iv Jg Jk Jo Jp Jq Jt Lh Ly Ma Md Mf Mi Mj Mk Mm Mn Mp Mq Mt Mu Mw Na Nc Nd Nf Ni Nk Nl Nm Nn No Nr Nv Nx Oh Oi Om On Pa Pg Po Pz) Fp(aA Fr Hr Hv Hx Id Ih Ii Ip Iq Ir Is It Jh Jl Jq Js Lu Lv Lx Lz Ma Mb Mc Me Mf Mg Mh Mi Mj Mk Ml Mn Mp Ms Mt Mv Mw Mx My Nb Nc Nd Nf Ng Nh Ni Nj Nk Nl Nn No Nq Ns Oe Of Oh Oy Pb Pc Pz Qa Qb Un Wm) Aa(Hu Ih Il Io Iq Is Iu Jg Jl Jr Lh Lv Lw Ly Ma Mc Md Me Mg Mi Mk Mm Mp Mu Mv Mw Mx My Mz Na Nd Ne Nh Ni Nj Nk Nl Nm Nq Nr Ns Nv Nx Oe Of Og On Oz Pc Pd Pf Pg Qb Qc tV) Im(aA bM dB Hq Hr Hv Hw Ih Ii Ij Il In Io Ip Iq Is It Iv Jn Jo Js Lv Ly Ma Mb Md Me Mf Mi Mk Mm Mp Mq Mr Mt Mu Na Nb Nc Nf Ni Nl No Nr Oh Oi On Pa Pd Qa Qb) Mz(aN aO Dd fY Hc hG hL Hq Hr Ib Il Io Iv Jg Jj Jn jO Jp Lv Lx Lz Mc Mh Mi Ml Mx My Nb Nj No Ns Pc Pe Pf Pk qA qB qD qG qO qP qY qZ Sr Uh uM Vt) Pj(Aj aM aN cB cF cM dB dD dL Dr Ex fP hG Id iH Ik Il iP jD jK Jp Ki Kl Kq Lz Mr nY Oa Of oK Pa pF Rc Rt Ru Rv Ry tX Un Uz Vc Vv Wc Wh Yl Wm Yf) Cs(bM cM Fn Id Jd Jj Jp Ju Jy Ke Li Nk Nm Ok Pk Qu Qw Qy Rb Rj Rm Sr St Tn tV Uf Uo Up Ur Us Ut Uu Uv) Vt(Ar bL cM dB Ed eF Fw hG Il Jj Jp Jv Ki Kq Ks Ne Nh Nm Og Ou Oy Qc Qx Uh uM vO Wb Zq Wm) Ok(aC bM dB Du Ef Gd Gh Gn Jt Kl Op Rz Uw Uz Vc Vh Vi Vj Wd Wf Yg Yl Ye Tm) Id(Ax bM dD dL hV Il jO jQ Jv Kq lO Mn qY rQ rZ sI sK tN vU yK Ti) Uh(aN dA dL Fa Gp hC iA iP iZ Jj Jv Ki Kq Lz Ne No Oa sH tO Uu Vv) Ny(Hu Hx Ij Ir Jp Jr Lx Ml Mn Ms My Ng Nm No Nt Oe Qa Qc tR) Jp(aC Ar bM Du Jj Jr Jv Kl Ms Nj Nw Oy Oz Pc Sf Uu Wb) Jj(Dc li Ij Ir Jm Js Jt Kq Lh Mn Nm Nu Nv On) dU(Bb Du Jf Jg Kz Li Lp ml mY Nk nN Uu Vb) Ke(Aw Ax Ch dB hP Ne qU Sf Sh sO tT tX) pK(aO aW aY bN cM Dd dK jB Mw nK Nn) On(Hu Mh Ms Ng Nj Of Og Oz Sh Wb) Kq(Ar Aw Bg bM Ch Dk Hc oP Ss) Nw(aN Hr Hw Jl Jo Jq Js lM Md) Ti(Ax Du No Nr Or qA Sr tT) Jg(Hu Mh Ms My Ng Og Oy Qa) bM(Dd Hb Jd Js Kr Oa Qc Qh) Mn(dW Ir Lx Lz My Nh Nu) jB(cN cR kF mZ nK nR oP) No(Hc Ic Jv Sf Vv Yl) Nt(Eq Ne Og Pc Qa Qc) Wb(aM Ij Lh Lx Ml Po) Sr(Ib jV Of oN rB) Js(jD jU Ms Pc rB) Kr(Ar qH rS sI tO) Lh(hP jO Pb Vc Yd) Og(Ih Ir Nu Oa Qa) Un(aC Ax Du uM uX) Vh(bU iB jE lM Nk) Eq(Cu iJ Ng Nm) Li(Aj oD Wf yJ) gV(aD Fa Mb Uu) Eo(aD cX Is) Th(mZ uL vT) Nm(Sf Sh Vb) Lv(dW eO Ew) Nk(eQ oW Zq) Ir(Iu Lx Yk) Qa(Nu Oy Pc) tV(Bb Ql Qm) Ar(aC Jv) Du(fA mE) Zq(Jv Oi) Vq(mS tT) dB(rS tX) gZ(cR Oz) rB(Jr Tz) oW(bB bU) AxUr BoeO DwaD PohP FrHu NuQc LxHx NgJt YicD SijP KnwQ NvOy OpjD PkiJ aNsC cBeW mMIL mWrZ Unconstrained panels with 2 analytes, where 1.0E-5 >= 'AUC p-value' > 1.0E-6. Contains 2,517 panels of 199,653 total panels evaluated. :
Ji(AD aE Af aI aJ aK AL An AP aQ aR AS aU aV aY aZ BA BB BC bF BG bH bI bJ bL BN BO bP bQ bR bS bU bV bW bX bZ cA cE cG cH cJ cK cL cN cO CP CQ cR cS cT CU cV cW cX cY cZ Db DC Dd De dF DG DI dJ Dl dM dN dX Ed Eq eZ Fn fR fY Gh gL gP Gz Ha hB Hc hF hL HO Hp iO iP jB JD Je Kf Kl kQ kR kS Kx Ky Kz Ld Lt nW oE oF oH oK Or Ow pF Ph Pi Pj Pk qA qB qC qD QG qQ Qu Qv Qw Qy Qz Ra Rb Rh Ri Rj Rm rO rS rU rV Rx Ry Sr TN tO TT tU Tv Tz Ua Ub Uc Ud Ue Uf Ug Uk UL Um UN Uo Up Ur Ut Vo Vp Vs vT Vz Yl zG Zw Zx Yc Tm Tl xA Tj tF) Gc(Aa Ad aE AF aH aI aK AL AN Ao AP aQ aR As aU aV aW aX aY aZ bA bC bF BG bH bI bJ bL Bn BO bP bQ bS bW bX bZ cA cC cE cG CH cl cJ cK cN CO CP Cq cS cT cU cV cW CX cY cZ dA Db Dc DE dF dG dI dJ DK dL dM dN dU Eq Fa Fi Fr Fw Gb Gl Gp Hq Hr Hx Ih Ii Ij Im In Iq Ir Is Iu Jg Jh Jk Jl Jo Jq Js Jt Ju Jv kG Ki Kj Ky Lh Lu Lw Lx Ly Mb Mc Md mF Mg ml Mj Mk MM Mn Ms Mt MU Mv MY Na Nb nC Ng nl Nn NO Nq Nr Nt Nu Nv Nw Nx Oa Oe Oh Om On Pj Pk Rf Rh Ri Rj Tr Up Vj Vu Wb Yl Ye Xa) Vt(aA AF Al aM aN AO aR aS aU aX aZ Ba bB BC bE bG bH bS cB cC cI cJ Cu cV Cx cZ Dc DD Dg dJ dK dL Dp Dr eP Et Fa Fn Fr Ha Hf Hr Hu Hv Hx Ib Ic Id Ih In Iq Je Jf Jh Jl Js Jt Jy Ko Ld Lh Li Lu Lw Lx Ly Lz Mg Mh Mi Mj Ml Mn Mt Mx My Na Nb Nf Ng Nk Nl Nn No Nr Nt Nu Nw Ny Oa Oe Of Oi Ok Om Op Oz Pa Pc Pd Pe Pf Pg Pk Po Qa Qb Qd Qg Qh Qm Qt Qu Qv Qw Qy Qz Ra Rb Rc Rg Rt St To Tr tT Ud Um Up Ur Uu Uv Ux Vw Wh Yi Tj) Pj(aA Af Al Ap AR As Aw aX Bc bE bG bH bO Ch cI Co CQ Cu Cv dA Dc Dd Dg dH dI dK dM eC Ed EF Em eP Eq Fc Fi Fr Fw Gb gL GP Gz Ha hB hF Ic li lm iO Iq Ir It Jl Ju Ke Kk Kn kQ kR kS Ld Li lO Lv Lw Lx Md Mg Mi Mq Ms Mt Na Nd Ne Nk Nn No Nr Nu NW Nx Ny oE oF Og oH Oi Ok ON Ou Ow Oz Pb Pe Pf Pk Po Ps Qa Qb Qd Rg Sr Tn tT Uh Uk Us Uw Ux Vh Vj Vz Wd We Wf Wg Yd Tm Tj) Mz(aA aC Aj Ao Ar Aw bF bJ bL bM Bo bQ bS bX cA cI cP Cs cV cW dB dH DK eC Ed gL hC hR Hu HV HW hX iB IC Id IH Ik In Ip Iq Is Iu jD jE jK JL jM jP jQ Js Jt jY Kd Ke Kj Kr Ky lK lM IN Ly Ma Md Mf Mj Mk Mm Mq Mt Mu Na Nc Ne Nf Ng Nh Nl Nq Nr Nv nW Nx nY OE Oh Oi oK Om ON Oz Pa Pb Pg Ph Po Qa Qm qT qU qW Qx rB Rg Rj rQ rR rS Tt Tz Um Ur Wm) Qe(aH bG bW cC cE cJ cR dF dG Dp dR Ed eF Eq Ex Fb Fc Fi fP Fw Fy Gb Gh GL GP Hb HC HF Hl iA iH iO Jd Je Jf Ju Jy Kc Kd Kf Kg Kj Kn Ko Kp KQ KR Ks Kx Ky Kz nW nY Oa oH oK Op pF Pi Qg Qh Qm Qn Qv Qx Qy Qz Ra RB Rc Rf Rg Rh Ri Rj Rt Ru Rx Sh Si Tt Tz Ua Ub Uc Ud Ue Uf Ug Uk Ul Um Un Uo Ur Ut Uv Uw Ux Uy Uz Vh Vo Vp Vs Vw Wc Wg Yd Yg Yj Zx Yf) Lj(Ad Aj aM aN As aX BB Bg bS cC Co Cp cQ Cs Cu dD Di dL Dp Ed Ez Fa Fb Fw Fy Gl Ha HB Hc HF iA Ib iP Iz Je Jf Kc Kd Kf Kg Ki Kj Kk Kn Ko Kp kQ KR kS Ld nW nY Oa oE oF oH oK Op Ou Ow Pi pK Qg Qh Ql Qn Qt Qu Qv Qx Qz Ra Rb Rh Ss St To Tr Tz Ua Ub Uc Ud Ue Uf Ug Uk Ul Um Uo Uu Uv Uw Ux Vo Vp Vv Zx tF) Uh(aD aF Aj Al aM Ap As Aw bF Bn cB cE cF Ch Cv dB Dd dE DR DU Ed eF fP Fw Fy Hw Hx Ic iH iJ Il In Ir JD Jp Js Kl Kn Kr Lh Li Lw Lx Md Me Mh Mk Ml Mq Ms Mt My Na Nh Ni Nk Nm Nr Nt Nu Of Og OK oN Or Oy Pa Pb Pe Pk Po QA Qc Qd Ra Rb Rc Rf Rg Rj sK Sr Ss TN TR Ua Ub Uc Un Vu Yk Wn Ti) Cs(aA aC aM aN Bb dB Dd Dp Ed Ez Fa Fy Ha Hb Hf hG Ib Ic iJ iO Je Jf Jg Jt

Figure 41 Continued

Kd Kg Ki Kk Kn Ko Kp Kq Mj Mm Mt Ne Nh Nl Nw Nx Oa Og Oi Or Ou Po Qc Qd Qg Qh Ql Qm Qn Qt Qv Qx QZ Ra Rc Rf Rg Rh Ri rS Ss
To Tr Tt Tv Tz Ua Ub Uc Ud Ue Ug Uk Ul Um Uy Vo Vp Vq Vs Vu Vv Wb wQ Wn Wm Ti) Id(aF Aj An Ar Aw bE bP bS cB cI cM Cu dB
dE dK Ed Et Fa Fr Fw hA hL Hv Ib IC Im In Ip JD Jj Jl jM Js jU JY Ki Ko Lh Li IL Lw Lx Lz Mi Mt Nd Nk Nn Nr Nt Nu Ny Oa Og Oh Ok Or
Ou Oy Pa Pe Pf Pk Qa Qd Qh Qn qW Rg rV Sr Ss Tr tU Um UN Us Uu uV uY wP wQ Wm) No(Aa Ez Fn Gz Hb hG Hp Hr Hu Hx Ij Ir Iz Je Jn
Jp Js Ju Kd Kf Kg Ki Kk Kl Kn Ko Lw Lx Mj Mn Mv My Na Nk Nm Ns Nu Oa Og Or Ou Oz Pc Pe PF Pi PK Qc Qn Qu Qv Qx Rb Rf Rg Ri
Rj Rm Rt Sr Ss St Tn Tr Tt Tv Tz Uc Ud Ue Ul Um Up Ur Uu Vp Vz Yk Zw Wm) Jp(Aj aN aO Ax Ch Zr Ed Fa Fc Hb Hu Ib Ih Ij Jd Je Jn Js
Ki Kq Kr Kx Ky Kz Lx Lz Ml Mx Ne Ng Nm Ns Nt Nu Oa Of Og Or Ou Ow Pb Ph Pi Pk Po Qa Qb Qc Qz Rx Vc Vv Wh Yg Yi Yj Yk Zx Wm
Ti) Ny(bM Du Hq Hr Hv Ib Ih Il Ip Is It Iu Iv Jg Jh Jk Jm Jn Jq Js Jt Ki Lh Lu Lv Lw Lz Ma Mb Mc Mf Mi Mj Mq Mr Mt Mw Mx Na Nb Nh
Nj Nq Ns Nu Nx On Oz Pb Pc Pe Pf Pk Po Qb tN tX uN) Qd(aC aM Ar Ax Du Eq Fa hP Hq Hr Hw Ih Ii Ij In Is Jm Jo Jv Ki Lh IM Lv Me Mg
Mi Mr Mt Mw Na Nc Nf Nh Ni Nl Nn Nr Oh Oi Om On Pz Qb qQ Wm) Ke(Aj aM aN Ar Bg cB cM dL dU Fa FP Gp hG Ib iJ Il IZ jD Jj Kl IK
Nc Nh Nk Nl Og oN Or Oy Qa qH Rc rQ rW tS uN Uu vU Wh wQ zG Wm Ti) Lh(aA aC aN bM Eq hG Hu Ib Ih Ij Is Jg Jr Jv Ki IM Lx Mh Ml
Ms Nj Nm Nt Nu Og oN Ou Oy Oz Pc Ps Qa Qc Rv Si tR Uu Vb Vh Wc Wd We Wm Ti) Ar(AA bA Bb bM Dd Et Fn Fy Ic Jd Jj Jy Li Nb Ne
Nk Nw Og Ok Pe Pf Qc Qx Rb Rg Rh Ri Rj Rm Sr Ss St Tn Tr Uc Uk Um Up Uy Wb Ti) Ij(Aa bM Fr Hu Ii Ik Ip Ir Is Iv Jg Lu Lv Lw Lx Lz
Mc Mh Mi Ml Mm Mn Mr Ms Mt Mx My Nb Nc Nd Ne Nj Nm Ns Nt Nu Nv On Oy Pb Pe Qc) Lx(hP Hq Hu Ih Ip It Jg Jj Jn Jq Jr Js Jt Mk Ml
Mr Ms My Nj Nm Ns Nt Nu Nx Oe Of Og Om On Oy Oz Pb Pc Pe Qa Qc Qw Sr Ur Ti) Mn(Aa Dr EO eW Hq Hr Hu Hx Ih Ik Io Ip Iq Is Iv Jn
Jr Lw Mb Mc Md Mh Mi Mq Mr Ms Ne Nm Ns Of Og Om Pe Pf Pg Qc Sf Sh) dU(bH bL Bo cM Cw Dd eC Ed Et Fd fR Fy Ha Hb hC Ih Im Ir
Ju Kc Kd Kl Ko Me mM Nr oW Qu Qv Rb Rt Sf Sr Ur Uy Vv Wd Yl Ti) Js(Aa aN hC hV Ib iC Jg jM jO Jv IK IM Mb Mr Nj Nm Nt Nu Oa Of
Og Ou Oy Oz Pb Pk Qc qU qV qX qY rA Sf Ur) Fp(bM Hq Hw Il In Io Iu Iv Jd Jk Jo Jr Jv Ly Md Mq Mr Mu Na Ne Nr Oi Om Pa Pd Pe Pf Pg
Po Sr Up Ur Uu) bM(aC Aj Ax Bc Cv Dc Ed Fa Fb jB Jg Jj Jm Jq Jt Kd Ki Kn Mr Nb Ne Nk Nn Nv Nx Or Qa Qb Rm rS Tv Un) Aa(aA Hq Hr
Hv Hw Hx Ii Ik Ip Ir It Jh Jk Jm Jn Jo Jq Jt Mj Nc Nf Ng Oh Oi Om Pa Pb Pe pK Pz tN) Nt(aA Aj Fr Hu Ih Is Jg Jq Lz Ml Ms Mx My Ng Nk
Nn Ns Nv On Oy Oz Pb Po Qb Rv Sf Sh Vb Vj Wc Wh) Sr(aA aC aM aN Ax Bg bS Ch hB Hc hP Jh Jv Ki IK IM Lz Ml Mw Og Pk Rg Ri Rj
Rm To uM vA Vv Wm) Ok(aN Ax Ch cI Fc Fi fR Gb Hl Ho Lp Lt Rt Ru Si Sj Uu Ux Uy Va Vw Vz Wg Zq Zw Zx Tl Xa Yf) Ax(fA Ic Jd Jj Ju
Jv Jy Li Nw Or PK Qu Qy Rg Rm Uf Up Us Ut Uu Wn) Qa(aA Aj aN Du Hu Ib Jn Jt Jv Mh Ms Nj Nk Nm Oz Pb Qx Vh Wb Wh Ye Ti) Jg(aA
Aj Ih Jn Jr Lw Lz Mg Ml Mr Mx Ns Nu Oe Of Oz Pb Pc Pe Po Qb Qc) Kq(aC Ba Ct eF Hu Ib Jv Mg Mv Mw My Ng Nq Of Oy Qu Sf Sh Tn
Uu Vb Wb) On(Aj Jk Jn Mb Ml Mp Mr Mv Mw My Nk Nm Nq Nu Oe Pb Pc Qc Sf Uy We Wh) Un(Aj aN dB dK Dr Fw hG hP Ib iJ Jj Jv Ne
Oy Ss tR tT Uy wE Yk Ti) Zq(bU cD Ez Gd Ha iJ Jj jP kP Kx Ml mS Ne Or Po Sf Sh Wb) Nw(aM cl dB dE jD jO Jv IK Pk qH qT qU qV qY
rA rB rC rW) Nv(Hu Lz Mh Ml Mr Ms Mx Ng Nj Nu Of Og Oz Pb Pc Qc) Du(Al Et Gb gL Hb Il iP kR Nk Nu oN pF Uy Vq Wb) Ir(Hr Hx Jt
Lw Lz Mc Mj Mx Nm Nu Oz Pc Pe Pf Wb) Jj(Al Dd Fr Fy Ha Jn Ks Mm Nn Nx Po Qb Qc Vh Yi) Pe(Hr Hx Io Lw Mj Nm Ns Oz pF Qc Qw
Uy Wb Ti) aN(Dd Im Li Nx Oa Pk Qc qT rR rY rZ uL wE yJ) pK(bB bI Bo cF dD eQ iP Jn mE Ng nL nN oW Ut) Li(aC aX dB dE fP hG Jv IM
Op Ur Uu Vh) jB(aG bI cF Ct fB Kl Kz Nk Pb Pg Vs Vv) Ti(aM Cu Ed Ha iZ Nb Nk Oa Po Sf Wb) Aj(Bb Bc Cu Dc Dw Fy Im Ks Nn Qc)
Nm(aC Fa Is Jq Jr Mx Ng Og tT Wb) Et(Ap Ef eW Fa Jv Kl Sf Sh Uy) Vh(aM bO cD cM Jn Mw Ne Nu Rg) Kr(Fa Oa qU qW tR wJ yJ zA)
Pk(cM dB dD dE dH dL hG Ki) Qc(Fr Jn Lz Ms Mx Nx Og) Jt(aC Mr Ms Mx Og Oy Vb) Uy(bB bU Cu iJ Nr Qm Ut) Nu(aA Jn Jr Mh Oz Pc)
Hb(aC dL Fi Il Wm Yf) Wb(Hf Mh Nk Oa Oz Ut) rS(cI iP Ql qX rA uN) Sf(Dc Ii Im Mm Ou) Dr(iJ Kx Nk Ut) Eq(Dg Mm Ut Ux) Sh(Fy Ii Mm
Ut) Jn(Mh Og Oy Wh) aC(Bb Im Mm Vq) gV(aM Bo cP cX) tX(Bb Dl jM Qm) rB(Im Oa Rm tT) Fa(Fw Lu Nk) Fr(Ng Og Oy) qZ(Gz tR tS)
An(rQ tT) Cu(Wd Wh) Dl(tO tR) Gb(aM Kx) Ha(Nk oN) Ii(Og Wh) Jd(Ch Jv) Kn(hP rO) Vq(Wc wE) Oy(Nn Po) bU(eQ pH) mE(Wc Yk)
tV(dE Ne) BoDw WmwE EwNj ExyE FnsF FwvT Nrlb YdiB ZwjY ZxjH JlhP JrjO XacD YemT KkrW NxOg OaUr bSdW cBeO cReQ cXcW
dBtT sJjM qXuI kFoW lNoP Unconstrained panels with 2 analytes, where 1.0E-4 >= 'AUC p-value' > 1.0E-5. Contains 5,386 panels of 199,653 total panels evaluated. : Id(aA Ad aE Af aG aI aK AL aM aN AO AP aQ aR As aU aV aW aX aY aZ Ba BB BC bF BG bH bI bL BN BO bQ bR bU bV bW bZ cA cC cD cE cF cG CH cK cL cN CO cP CQ cR Ct cU CV CW Cx cY cZ dA Db DC dF DG dH DI dJ Dk dM dN Dp eD Ef Ez Fb Fn Fy Gc Gl gW Ha Hb HC Hf hG hP Hq Hr Hu Hw HX iB Ih Ii IJ Ik Io Ir Is It Iu Iv Iz JE JF JG JH jI Jk jL Jm Jn Jo jP Jq JR jT Ju Kc Kd Ke Kf Kg Kj Kk Kl Kp Kr Ks Ld lN Lu Lv Ly Ma Mb Mc Md Me Mg Mh Mj Mk Ml Mm Mp Mq Mr Ms Mu Mv Mw Mx My Na Nb Nc Ne Nf Ng Nh Ni Nj Nl Nm Nq Ns Nv Nw Nx Oe Of Oi Om ON Ow Oz Pb Pc Pd Pg Ph Pi Po pS pY Pz Qb Qc Qg Ql Qm Qt QU QV Qw Qx Qy Qz Ra RB Rc Rf Rh Ri Rj Rm sH sJ sM sO St Tn tV tX Tz Ub Uc Ud Ue Uf Ug Uk Ul Uo Up Ur Ut Uv uW uZ vB vC vH vI Vo Vp vQ vT Vu Vv wC wD wH wJ wK wL yD yH zH zI Tj Th) Pj(Aa AD aE aF aG aH aI aJ aK aL An AO aP aQ aS aU aV aW aY aZ BA BB bC bF Bg bI bJ bL BN Bo bP bQ bR bS bU bV bW bX bZ cA cC cD cE cG cH cJ cK cL cN cO CP cR cS CT cU cV CW CX cY cZ Db dC DE dF dG Di dJ Dk Dl dN dR dU dX eM Et Fb Fd Fn Gl Gn hA Hb Hc Hf Hl Ho Hq Hu Hv HW Hx Ib Ih Ij In Io Ip Is Iu Iv Iz Jd Jf jG Jh jI JM Jn JO Jq Jr Js Jt jV JY Kd Kf Kg Kj Ko Kp Kr Ks Kx Ky Kz Lh lM lN Lp Lu lX LY Ma Mb Mc Me Mf Mh Mj Mk Ml MM Mn Mp mS Mu Mv Mw Mx MY Nb Nc Nf Ng Nh Ni Nj NL Nm nN Nq Ns Nt Nv Oe Oh Om Op Oy Pc Pd Pg Ph Pi Pz Qc Qh Qt QU Qv Qx Qy Qz Ra RB Rj Rm rS Rx rZ Sj Ss St tN To Tr TV Tz Uf Ul Um Up Ur Uv Vo Vp Vq Vu Vw wF Yj Yk Zq Zw YE Tl Xa Th tF) Ar(Ad AF Aj aK Al aM AN AO Ap aR AS aU Aw AX Ba bB Bc bE BG bJ bL Bn bS bX cC cD Ch cI cL cM Co Cp Cq Cs cT CU CV Cw Cx cY cZ DB DC dD DE Dg dH DI DK dL Dp Ed Ez Fa Fb Fp Fr Gb Gl Gp Ha Hb Hc Hf Ho Hq Hr Hu Hv Hw Hx Ib Ih Ii IJ Ik Il Im Io Ip Iq Ir Is Iv Iz jB Je Jf Jg Jh Jk Jl Jm Jn Jo Jq Jr Js Jt Ju Kc Kd Kf Kg Ki Kk Kl Kn Ko Kp Ks Lh Lj Lv Lx Lz Mb Mc Me Mf Mg Mi Mj Mk Ml Mm Mn Mq Mr Mt Mu Mx Na Nd Nf Ni Nj Nm No Nq Nr Nt Nu Nv Nx Ny Oa Oe Oi ON Or Oy Oz Pa Pb Pc Pd Pg Pk Po Pz Qa Qb Qg Qh Ql Qm Qn Qt Qu Qv Qw Qy Qz Ra Rc Rf Rt Sf To Tt Tv Tz Ua Ub Ud Ue Uf Ug Ul Un Uo Ur Us Ut Uu Uv Vc Vh Vi Vo Vp Vs Vu Vv Zq Wm Tj Th) Vt(Aa AD aE aG aH aI aJ aK aL An AP aQ As aV AW aY bA Bb bF Bg bI bJ BN BO bP bQ bR bU bV bW bX bZ cA cD cE cF cG CH cK cL cN CO cP CQ cR cS CT cU Cv CW cX cY dA Db dC De dF dG dH DI Dk DI dM dN dX eC Ef Em Eq Ex Ez Fb Fc Fi fP Fy Gb Gd Gh GL Gn Gp Gz hB HC Hl Ho Hq Hw iH Ii IJ Ik Im Io IP Ir Is It Iu Iv Iz Jd Jg Jk Jm Jn Jo Jq Jr Ju Kc Kd Ke Kf Kg Kj Kk Kl Kn Kp Kx Ky Kz lM Lv Mb Mc Md Me Mf Mk Mm Mp Mq Mr Ms Mu Mv Mw Nc Nd Ni Nj Nq Ns Nv nW Nx Oh oK On Or Ow Pb Ph Pi Ps Pz qH Ql Qn Qz Rf Rh Ri Rj Rx Rz Sf Sr Ss Tn tR Tt Tz Ua Ub Uc Ue Uf Ug Uk Ul Un Uo Us Ut Uw vA Vb Vc Vi Vo Vp Vs vT Vu Vv Wd WE Yj Xa Yf) Uh(aA Ad Af aG aH An AO aQ aW BA BB Bc bE Bg bH bL BO bP bQ bV cI cJ cL Co Cp CQ Ct Cu Cw Cx cY Db Dc dD De Dg Di DK Dl dM Dp eC Ef Et Ez Fb Fn Fr GL gP Ha HB Hc Hf hG hL hP Hq Hr Hu Hv Ib Ih Ii Ij Ik Im IO Ip Iq Is It Iu Iv Iz Je Jf Jg Jh jI JK Jl Jm Jn Jo Jq Jr Jt Ju jV Jy Kd Ke Kf Kg Kk Ko Kp kQ kS Kx Ky Kz Ld lM lO Lu Lv Ly Ma Mb Mc Mf Mg Mi Mj Mm Mn Mp Mr Mu Mv Mw Mx Nb Nc Nd Nf Ng Nj Nl Nn Nq Ns Nv NW Nx NY OE oF OH Oi Om On Ou Ow Oz Pc Pd PF Pg Ph Pi pY Pz Qb Qg QH Ql Qm Qn Qt Qu Qv Qw Qx Qy Qz Rh Ri Rm rS sF sI sJ St To Tv Tz Ud Ue Uf Ug Uk Ul Um uN Uo Up Ur Us Ut UV uY Vi Vo Vp Vs Wb wF yJ Tj) Cs(Ad AF Aj aK Al An AO Ap AS aU Aw AX Ba bB Bc bE Bg BN BO bQ bW cB cC cD cG Ch cI Co Cp CQ

Figure 41 Continued mZ Ne NK Nr Ny Oa oP Or Oz Pb Pz Qb Qc Qe Qh Qu Ru Ry To Uk Ul Uy Zq Ti) nK(aK Ax bM Bo bZ Ch cJ cK cS cU Cw Em Fa Fc Ic Id Io Iq Ir Jg Ji Kc Kr Kx Ky Kz Lw Me Mk Mn My Ng Nm nT Nx Ok Oz Pa Pd Pe Pf Pg Qe Qy Rt Ss Tv Us Uw Vz Xa tF) Ax(Aa aJ bJ bM bV bX cI cK Cw Dd dG dM eC fB Fd Fi Hc Id Ir Jf Jg Ji Jl Kz Lv Mj Mk Mm Mn Mv nA Ne Ng nI Nm nN oH Oz Pa Pb Pc Pj Qu To Tv Ub Uo Vp Vv) Qu(aO Ba bF BG bW cD cE Ch Ct cW Du EF eM Eq Fp Gn HC Hu Iz Jk Kc Kz Lv Mg Mk Nd Ng Om oP Ou Oy Oz Pb pK Pz Qw Ua Uw Vv Wd Wh Yg Yl Zx) Xa(aG aO aU aV bG bJ bM Ct dG dM eM Eq FR Hw iA Il In iP Jd Jf Ji Lz mI mW NA Ne Ng Nh NO oH oP Pb Pj pK Ri Ua Uc Ue Uk Uo Wd Wh Ti) Kz(Al aO bH bI bN bR bX cA cF Dd eC Fw Ih Il Im Jg Jm Jn Jp Kd kE kF kK Lp Lu Lw Me Mj Mn My mZ nN NR Nx Or oW Pf Ru To Ul Uy Vz Yh Tm Tl) Id(aO Ar bH bI bX cA cW dK Du eC Fd Hb hG Ij Iq Ir Jp Ko lY mI Mm Mn Ne nL No Nr Ok Ow Oy Pj Pk Qb Qc Qe Sf Si Sr Ua Ue Wd Yi Zq Ti) Fy(Aj aL Bc bF Bg bH bX Ct Dk Dp cF eM Ez Gp In Kc Lv lX Mg mI Mj nH nL Oe oP Ou Po Qz Uc Ue Ur Uu Uw Ux Vo Vv Wd Wh Yd Yg Yh Yk) Mj(bH Du eC Fa Fb Fd Gc Ha hG Ih Ij Iq Ir Jf Ji Js Kq Mf Mn Mz No Nr Oa Oh Ow Oz Pb Ph Pj pK Qa Qb Qc Qe Qh Ru Sr St Uy Yi Ti) Uu(Aa Ao bI cH cI Cw Dd Du eQ Et Fi Hw Hx Ij Im Iq Iu Jf Jo Jp Kf Kg Kj Kq Lv Mm Mn mZ nA Ng Nm Of Ok On Pj Pz Qc Rt Rz Vh Ti) Jf(aO bI bN cJ Cs Dd Fb Fd Ha Ij Ip Jp kP Ky Mt Mz nB Ng nL No Ok Pb Pg Ph Pk Qa Qb Qc Qe Qv Ry Um Ux Uy Vo Vv Yi Yl Tl) Gp(aO Ar aU Bc bJ bM bN cJ cK Du eF Fd FP Hv iP Ji Ju kF kP Kx Ky Lz Mf Mx Nf Ng No nR oP Pj Pk Po Ub Uc Uo Yj) Ha(aL bH Bo bX cF cH cU dJ Dp eC Eq Fd Ii In Jp kE Ko Me mI MZ nR Or Ou Oy Pg pI Po Qv Qz Rv Up Ur Uv Vp Wh Yh) Ir(Aj cI cK cN Ct Dc dG Dk eC Eq hG Hl Hx In Jl Kc kF kO kP Ky mI mS Nk Oe Oy Oz Pb Pg Qv Qz Rm Uc Un Uw Vp Vv Yk) Ng(Af aO bH Bo bR cN dM Dp eC Eq Fc fR Gc hG Kc kF Lp ml Ml Of pK Qc Qz Ra Ru Uw Uy Vv We Wh Yg Yh Zx Ye Tm) Ky(Aa aO aS bH Bo bX cI cW Dd eC Eq Fc Gc Ib Ip Jp kK Lp Lv Me Mm mZ Ne Nk Oz Pb Qc Ru To Uv Uy Yk Ti) Lp(aN Bc cJ cK Cs dM Du eF Fp hC Hu iA In Ji kP Kx lW NA Nd Nf Nx oP Pa Pf Pg Pj Rt Tv Ur Yl Th) Ru(aN Bc cD cJ cK Db dG dM eF Fp hC Hv iA In Ji kP Kx Lv lW NA Nd Nf Nx oK Pa Pf Pg Rt Tv Yl Zx) bX(aF bM Du Fb Fd Hf Ih Je Jg Ji Ko Kq Ks Kx Lw Mf My Nm nN Nx Oh Oz Pk Qa Qb Qe Ry Tv Vo Vz Yi Yl) No(aO aV bH bM cH cK cU Cv Cw Du Eq hG Ic Jl Kc kF Ko Lw Me mI My nR pK Qc Qv Qz Rv Uw Vv Yd Zw) Pb(aK aQ bC bH bN Bo cA cF cK Cq Cw dJ eC Fd Im Ip Jg Ji Jn Jr kP Me Mn My nH nI nL Nr Ok Sf Yi) mI(aO bI bM Ch cJ cK cS Cv Cw Dd Fd Hc Io Iq Jg Ji kF Ks Lw Me Mf Mk My Nm nN Oa oD Ok Rg Tv) Mn(aO bG cH cI cK Cv Cw eC Eq Fd Hc Ic Kc kF kP Lw Mk mZ nI Nk nR oT Oy Oz Pa Pg Rf Vv Yd) Yi(Bc BG Ch cJ Ct dG Dk EF eM Eq Fr Gh iA kR Lv lW Mk nA oP Ou Pa Ql Uw Wh Yd Yg Zx) Qe(Aa aL cF Ch cI cK cU Cv Cw Dd dJ Dk eC Jg Jl kP Lv Lw Me My mZ nI nL Nm nR Pg Qv Ub Vp) Du(Aa aJ aY bN cF cJ dG Ed Fw iA Ij Il Im Jm Ju Kd lW nL nN Nr Ny Or oW Ph Pj Sf To Ul) Qc(bM Bo Ch cK Cw eC Hc iP Ji kF kP Kx Lw Me Mh Mx My Nh Nk Nl Nm nR Pa Pg Tv Up Uw) Uy(aL aN Bc cD cJ cK cX dC dM eF Fp hC Hl iA In Ji kP Kx lW Mv Na Nx Pj Rj Rt Tv Th) Oz(aK aL aQ bH bI Bo bR cA cF cK Cp Cq dD eC Eq Jn Jp kE kF Lw My nH nL NR Ok Tl) Dd(bH bR Cx Dc Dk Dp eC Eq Fp Kc kP Kx Lu Ml Ne Nk Nl Oy pK Qv Qz Rc Rt Vv Yj Zx) Ko(aG Bc bG bN Ch cK Fp hC Il Jd Jm Jr Kd kP kR Kx lW Mh Mx nA nB nN NR oP) Uw(bI Cq Et Ih Ii Ij Im Is Jo Jp Js Kq Ks Lh Mm Nm Ok On Ow Qa Qb Qh Tn Uf Ti) pK(Aa aY bI bN Bo cF cK Cw Ih Ij Im jB Jg Kd Me Mk nN NR Oa oW Ph pI Pk To) bH(aF bN Ch cK Cw Fb Hc Iq Jg Ji Ju kP Lw lX Me My Mz Nm nN Oy Pk Rv Sf Yl) eC(cJ Io Jg Jt Ks Kx Mk MM NA Nm Nr On oP Pc Pf Pg Pj Rj Rv Tv Wh Tj) Wd(bJ Co Hq Hw Ij Im In Is Iv Iz Jr Kq Ks Nq On OW Ph Qa Qh Qz Tn Tv) Fd(Aa cN Dk Gh Je kR lW Mb Me Ml NA Or Ou Pd Pe Pf Pg Qv Rj Rv Vp) Yl(bN Fw Il Im Jo Ju Kd Ks Mx mZ nD nL nN Nr Or Pe Ph Pj Sf Ub Uk Ti) Vv(bI Fw Ih Ij Il Im Ip Is Ji Jm kR Mx NA Nr Ok On oP Qa Qb Tv Ti) kP(Bo Ch Cw Gc Io Jg Ji Jt Kd Lw Me Mm My nA Nm nN Ok To Ul Uv Zq Ti) aO(aI aL Bo Cw dD Et Jg Ji mM Mv Mz nA Nm nN Ok oN Qv Ub Ur Zx Th) Rt(Aj aY Ed Fw Il Im Jm Kd mZ nC nH nL nN Nr Of oW Ph To Va Ye) kF(bZ Cw Et Ij Im Io jB Ji Kq Ma Mf Na nN On OW Pe Qa Tn) cK(Bb Bo Cw Gc hG Ih Ip Iq Jg Ji Kd Me mY Nk nN Ok To Zq) Eq(Ao Cq Cw Et Fb Ij Kq Ks Mz nN Oi Ok On Ow Ph Qz Tj) Nr(Bo cI dM eQ Ic Ji Jl Kc Lw Mk My Nk Nm Nx Oy Rf) Im(bM Ct dM Fc fR Hx Ic Ji Kc Me Nx Oy Ps Qv Vq Wh) Cw(aG Aj Bg Ch dG Dk dM Ef Fp Ml Mx Of Oy Uc Ux) Gc(Bc Bg Ch cJ Ed Hv iA Jr Kr Mk Mx nA oP Ux Zx) Kd(aN Bc cH Fp Hb hC Hu Ji Me Na Nd Nx Oy Pj Th) Ti(aL bA Bc bQ cJ Ed eF hC iZ Lv Mk nB Ph Ux) Wh(Al Cq Ih Ij Il Is Jp Ks mZ On Ow Qa Qh Tn) Ok(Aj Dk dM Jd kK Mg mZ nI Oe Of Ou Oy Pa Yd) oP(Bo Fb Hl jB Kc Kq Qv Qz Rz Sf Ub Ur Vi Zq) Nk(cJ Ih Ij Iq Jg Jm Ju Lw Me Mf My Nm Ux) nN(bI bR Cs Fp fR Hb hG Ji Kc Na nU Oy Pg) Th(Bc Hv Jm Kr Kx Ms Mx mZ nB Ne Pj To) Jg(Aj Bg Ch Cs Ct Dk Mg Ml nR Of Oy Pg) Ye(Hw Il In Jj Jo Kg Ks Nm Or Pj Tv Yj) Bo(bI bM bN bV hG Iq Mf Mx nA nR Pj) Qv(bJ Fw Il Iu kK Lv Mx mZ nA Pj Uk) Me(bR Ch Fw Hc Hf Kx Mx Nd oW To) Ji(cH Dc Fw Ml Mp Ms mZ Ou oW To) Ux(Al Ao bI Ih Ij Il Ip Iq Jo Nm) Tv(dJ Dp Fc In Kc nH nL Qz Tm) Qb(Aa cI Dp Rm Ub Uc Vp Vu Yk) Kx(Aa cU Fc kK Lv mZ nL pI Po) Ow(cN dG Dk Gh Jl Lv nR Ou) nA(aK Dp Gh Qz Rv Yh Zw Tl) hC(cN Ju Or Pj Sf To Uk Ul) Il(Fc Gn Ic Kc Qz Yh Zx) Yj(Aa gC Gn Hl jB Um Ur) mZ(Ke Lw My Rb Rj Uh Us) nL(Fa Je Mf Oa Qh Rx We) Fw(cW Fc Hb Ic Kc Mm) Mx(Dp Kc Rm Rv Ub Vp) To(Bc cD dJ Fp Hu Kc) Ih(Ct Jl Jn Ne Nl Oy) Ij(Ic Ps Rm Up Vw We) Zx(bI bN Jk kQ Uk Ul) Kq(Bg Ef Jd Ml Ou Uc) Pj(Ki Kj nB nR Oa Yd) Qa(Jl Ps Ql Rm Vp) Qh(bF Dk nH Oi Ou) On(Dk Oe Ps Ua Uc) dD(bN dG dH dM nR) oW(dM Na Nx Pf Pg) Al(Hl Ne Ub Ur) Ch(Ap Mm Nm Uf) Mk(bN hG Pe Sr) Ml(cW Et Mv Ub) Sf(bG Hv Mf nB) Je(cH Dr Kc Wb) Ry(Bc eF iA lW) Rv(dB Ks Ph Pi) aL(bM bN dM Uk) nR(aI Hb Mz Ph) Cq(Ic Qz Uv) Nm(Aj Fp Uc) Jd(aI Et Ke) Rz(Bg Ef iA) Ul(cD dJ Kc) Pg(Pe Pf Ph) bI(Ed Ur Yh) hG(mY nB Pk) Ap(Aj Of) Cv(bN Og) Ub(bG Ip) In(Hl Va) Sr(Hv Oe) Ss(Lz Uo) Qz(iA Ks) Ke(lW Ms) Oy(Jt Tt) cF(Mf Uo) AaRc AoVo BcmY BgUf DpKs EdRx FbGh FcNx FiPd FpMm NaYh HxTm YkcJ RbVp ZqlW QwJp JoVa JsRm JubG OabF UkoE PfbA PkkK} Gc{mE(aC Ad aI Aj aM Ar Ax bE BG bL bN BO cD Ch cM Cp cR Cs Ct Dc dD Dg Dk Dl dN Du eC Ef Eq FA fB Fp Gd HC Ik Iz Jj Jo Jt Ju Jv Kc Kf KG Ki Kj Kl kP Kr Kx Kz Li Lj lX lY Mg Mh Ml mU My nB Nc nN Oa oE Of Og Oy Oz Pa Pb Pe Pg Ps Pz Qv Rc Rg Rm Sf Sh Si Tt Ua Uc Ug Uk Ur Us Uu Uy Va Vb Vo Vs Vv Vw Vz Wd We Wh Yd Yl Zx) Nk(aC aM aS Ax bM cD Cq Cu eC Ed Fa Fp Fw Fy Gd Ha hC Ho Hv iA Ij Il In Iq Ir Iv Jj Jn Jp Jr Js Ju Jv Kd kG kP Kx Ky Li Lj Lx Me Mi Ml Mr mS Mt Mw Mx Nj nK Nr Ny Oa Ok On oP Pb Pc Pe Pg Pi Pk Po Qe Qz Rb Rg Ry Sf Sh Si Tt Ub Ue Uk Un Us Uu Uv Uy Va Vb Vi Vo Vs Vt Wb Xa) hC(aF Aj aO aW BG bU cD cN Cx Dg Dk Dl eC Ef Eq Et Gn Hc Ho Hx Io It Iv Jd Jt Kf Ki Kj Kl kP KR Li Lj Lv Ly Mg Mh Mj Mm Mq mS mU mZ Nb Nc Nh nK Nl Of Og On oP Ou Oy Oz Pa Pg Ps Qc Ql Qm Qn Qv Rm Si To Tz Ua Uc Ug Up Uy Va Vi Vp Vq Vs Vu Vv Wc We Yd Yg Ye) Vs(aM Ax bB Bc bO cM Cu cW dD Dk Du Fa Fp Fr Fw Fy Gd Hv Ij iP Ir iZ jB Ji Jl Jn Jp Jr Ju Jv Kd kE kG Kl Kk kP Kq Kx Lh Li lO Mf Mr mS Mt Mw Mz Na NB Ng Ni Nr Nv nW Oa oE Ok On Or oV oW Pe Pi Po Qa Qe Rg Ry Sf Si Tn Tv Uk Un Ut Vi Vt Wb Yi Zq Wm) Vb(aM As aW Ax Bc bN Cu Cv Cw Dr Du Fb Fc Fw Fy Hv Hw Id Ij Ir Iv iZ Jl Jp Jr Ju Jy Kd Kf Kk Ko Kq Kx Lh Li lW Ml Mm Mn Mr mS Mt Mw Mz Na NB Ng Ni Nm Nn No Nr Nv Ny Oi Om On Pe Pi Pj Pk Po Qa Qx Ra Ry Sf Si Tn Un Us Ut Uw Uy Va Vi Vt Wb Yk Yl Zq) Uu(Al aM Ar As bB bM bN cD Co Cu Dk Du Fb Fw Fy gZ Hv Ii Il Im Ir Iz Ji Jl Jm Jn Jp Jy Kd KE kI Ko kP Kq Lh Li Lp Lt Mf mS Mt Mw Mz Nb Ng nH Nm No Nr Nv oH Ok Om On oT Ou Pj Qa Qc Qd Qe Qh Rg Ry Sr Uk Un Ut Uy Vi Vt Wb Zq Zx) mS(aC Aj aW bB bN bU cD cM cR Cs cW dN Du Ed Fa Fy Gb Gd Gp Hc Hu Id Ij Il Jj Jp Jv Kc Kf kG Kp Kz Li Lj Lv Mm Mn Mr Mw mY Na nB nN Oa Og Ok On Oy Oz Pa Pb Pc Pd Pe Pf Pg Qv Rb Rc Rg Sh St Ue Ug Us Uy Va Vo Vv Vz Wd Wh Yl Tj) eC(aA Aj bF bG cC cD cL cM cR Cs Dg Ez Fp Gd Hc Hq Ic Iu Iv iZ Kd Kj Kl Kr Li Lj Lv LW Mg Mi Mj Mp mU Na nR nT nY Og OP Oy Pd Pe PF Pg Pk Pz Qv Qx Ra Rc Rf Rj Rm Si Ua Uc Ur Us Uz Vo Vq Vv Vz Wc Wg Yg Yh Yk Yl Zx) Sf(Al aM Ar aW bN cD Cs Cx Dd Du Fa Fb Fw Fy Gd Ha iA Ij Il Im Ir Ji Jm Jn Jp Kd Ke kP Kq Kx Ky Lh Li Lj lW Mf Mn Mt Mw Mx Mz NB Nd Ne Ng nK nN No Nr Ny Ok On oW Oz Pb Pk Qa Qc Qh

Figure 41 Continued

Ru Ry Uh Ut Uy Va Vt Vv Wc Yi Yl) Vv(Ar As aW Ax bB bR bU bX cF Cs Cu cW Cx Du dX Ed eQ Fp Fw jB Ji Jj Jl Jp Jr Kd Ki Kk Ko Kp
Kq Kx Lh Li Lx Lz mF Mt Na Nb nH nK nL No Nr Nt Nu Oi Ok On Or Pe Pk Qa Qe Qn Qv Si Ue Uk Uv Va Vi Wb Ye) kP(Aj aM An Ax bB
bN Bo bQ bU cR Cs cW dD dN Ed Fa Fp fR Gn Gp iZ Jj Jp Ju Jv KG Ki Kj Kk Li Lj mF nB Nc Nh nK Nl NN No Nr Oa Of Og Oy Pe Pg Qv
Rm Sh Si Ug Up Ur Us Uy Va We Yk Yl Ye Xa) Sh(Al aM Ar aW bB bN cD Ch Co Cs Cu Dk Du Fb Fr Fy Hv iA Ij Ik Il Im Ji Jj Jl Jp Kd Ke
Kq Kx Lh Li Lj lW Mn Mt Mw NB Ng nK Nn No Nt Ny Ok On Pk Qa Qe Qh Qu Rg Ry Ut Uy Va Vi Zx Xa) Uc(Bc Cu Dc Dk Fb Fr Fw Fy gL
Il Im Is iZ Ji Jl Jm Jn Jp Jr Kd kI Kk Kq Lh Li Mr Ms Mt Mz NB Ng Nr Nv Ny Oa Ok On Or oT Qa Qd Qe Qh Qv Rg Ry Si Tn Tr Uh Uk Un
Uy Va Vi Vt Wb Zq) nB(Ad aI Aj aL aW bB bN bU bX cD cJ cM cN cR Ct Dc Dl eQ gC Ho Ic Ii Ik It Iu Jj Jp Jt Jv Jy Kf kG Kl KR Ky Mg Nx
Og oW Oy Oz Pa Pb Pc Qz Rm Si Ue Ug Uk Ur Va Vq We Wh Yk Ye) Tt(Al Ar As aW bB bU Cu Dk Ed Fb Fw Fy Hv Il Im iZ jB Ji Jl Jm Jn
Jp Jr Jy Kd Kk Ko Kq Ky Lh Li Mn Mt Mw Mz Nb Nd Ng No Nr Nt Nv Ok Om On Or Ph Pk Qa Qe Qh Rg Ry Tn Ut Vi Ye) Qe(Aj aW Bg cA
cM cN Ct Cx cZ DG Dl Du Ef Eq gC Gd Io Jj Ju Jv Kd Ki Kl Kr lK Mj Nc Ne Nh Ni Nj Nl nR Of Oi Oy Pa Pg Ps Qd Ql Qn Qv Qz Rm Si St
Ua Uk Va Vp Vq Yk) iZ(AJ aO bB Bg Ch Ct Cx Dg Dk Dl dM Ef Eq gL Hc Hp Io It Jd Jg Jt Kf Ki Kl mU Nc Nh Nl Oi Oy Pb Pd Pe Pf Pg Ql
Qn Qu Qy Rg Rm Tz Ua Ug Ur Us Uy Vp Vw Wd We Yl Ye) nK(aC aI Aj aM An bE cD cM cR Cs Ct dD Dg Dl Fa Gd Gz Hc Ic It Iu Jp Jt Ju
Kl Kk Kl lX lY Mg Mr Og Oy Oz Pa Pb Pc Pd Pe Pf Pg Pz Qv Si Ug Ur Us Va Vo Vz Yh Yl) Kd(aC aM Ar bM bU cD cM Cs Dl Du Ex Fa Fp
Gd Ha Hc Ik Jj Jt Ju Jv Kf Kx Ky Kz Li Lj Mg Mh Mr Ne Ni No Ny Og Or Oy Oz Pa Pb Pg Po Qv Rg Si Uk Ur Us Va Vo Wc Tm) Rg(aF aQ
Ar aW bB bJ bS bU bX cL cM Cs Ed Eq Fp Fw Fy Gd Iv Jj Ki KR Li Lz mF Mh mI Mt Mw Na Nb Ne nH Ni nL No nR Ns Nu Oi On Pk Ry Si
Sr Ue Uv Va Wb) nR(aC Ad aI aL aM aY bB bF bO bQ bZ Ch cW dD Ed Et Gd hB Il In iP jB Ji Jp kE Kj Kk Kq Kr Ky Ma Mn Mr Nr nW oE
oF Og Ok ON Or oW Oz Pf pK Ug Va Ye) Nc(aC Ar Ax bB bM bN bU cD cM Cu cW Et Fp Fr Gd iA Ij Ik Ir Jj Jn kG Ky Lh Li Lj lW Ml Mt
Mw Mx Ng No nT Ny Ok On Oz Pc Pe Qh Uk Un Us Ut Uy Va Vi) Uy(Aj aM Ar bJ bU cD cM cR Cs Dl Du Ed Eq Ex Fa Fp Gd Hc Jj Jv Kr
Kx Li Lj Lz Mg Mw Na Ni nL No Og Oi Oy Oz Pa Pb Si Uk Ul Ut Va Vq Wb Wc Yk) Va(Ar Ax bF bG bN cD cI cL cM Du Eq Fa Fp Gd Ha
Hv iA Ik Ip Ji Jr Jv Ki Kx Lh Lp Lz Mf Mp Mw Mz nA Nd Ne Ni Ns Ok oP Or Pg Pk Ry Un Vt) Ni(aA aC Aj aM BB bN cD cM cQ dD Ed Gd
Ha Ik Il Jj Jn Jp Li Lj Mk Mn Mw Mx Ny Ok Oz Pa Pb Pc Pg Qh Rv Ue Uk Us Ut Uv Vo) Jv(Al Ar aW bB bN bO Du Gd iA Il Im Ji Jm Jp Ke
kO Kq Lh Lj lW Mn Mt Mw nL No Ny Ok On Pb Pk Qa Qh Ru Ry Ut Vi Wc Yi Zq) Vt(Ar aW bB bJ bU bX cD cM Cs Du Fp Gd Jj Jp Ki Kr
Kx Li Lj Lz Mf Mh Mp Mw Na No Nr Pa Pg Pk Ql Qv Si Ut Vq Wc Yk) kI(Ad Aj aW Ax BG bL bM bN Ch cR Cs Dc Du Ed Ef Eq Iz Kf Kj
Kl Kr Li Lj Mh mI Ml Na No Nr Oa Of Rc Rm Wc Yk) Ne(aC aM Ax bB cD cQ Cs dH Et Fp Ik jB Jj Ju kG Kx Ky Li Lj Ml MT Mw No Ny Oz
Pb Pc Si Uk Un Ur Ut) Uk(Al aM Ar aW Ax bG bU cD cM Eq Fp Hv Ip It Ki Kx Lz Mh Ml Mw Mx Mz Nb Nd Nh Ns Pg Pk Qv Ry Wb Yk)
Ok(Aj aM aS bF BG cD Dg Dl Ef Gd Ik Jj Ju Lj Of Oy Oz Pb Pg Ps Rm Si Ua Uf Uv Vp Vq We Yd) Nl(aC Ax bB bU cD Cu Ed Fp iA Ir Iv jB
jE Jn JR Ju Ky Li Lj lK lX Mi Mw Ng nT Ny On oP) Vi(Aj bF BG cD cE cM Dk Du Eq Hq It Ki Lj Mh Ml Nh Oi oP Pa Pe Pg Ql Rm Ua Vo
Vp We) kG(aM aO Ax bI Ct Fp Hc Hf Hv Ic Il Kg Ki Li Lj Mg Mw Mx Nh Oy Pa Pb Pc Ql Rm Uv Yl) Jj(Al aM aS bI bN bU cD cM dD Fw Fy
Il Ip Jm Ky Lj lW Mr Mw Mz Ns Pk Qv Ry Us Ut) Ju(Al Ar aW bN cM Du Fy Gd Hc iA Im Ji Jm Jn Jp Ke Lh Lj Mt Mw Ng No Ny Pk Ry Ue)
cM(aC Aj aM bN eP Fb Fp jB Ko Kx Lj lW Ml Mn nN Oy Pb Qh Ru Si Sr Uh Un Uv) nL(aC aI aM As bB bE cD dD Du Fa Ic Ki Lh Lj Oz Pa
Pb Pc Pd Pe Pf Pg Us Yl) Qa(Aj Ct Dg Ef Eq Hc iP Ki Kl Kr Nh Of Ps Ql Qn Qz Rm Ua Ur Uv Vp Vq Yk) Ry(Aj Eq Gd Kf Kx Ky Lz Ny Og
Oi Oy Oz Pa Pb Pc Rx Si Ua Ub Ue Wc Wh Yk) nN(Bb bU cD cR Ct Dg Dl dM Eq Fi Hc Hv Ic Ii iP Jt Kl Mg Nh Og Pa Ql Wc) Mr(aC Aj aW
bM bU cQ eP Kx Mn Mw mZ Nh Oy Oz Pa Pb Qn Si Ua Ub Ue Ur) Uv(bB bM bU cD cR Fa Ji Jp Jr Kq Kx Lh Nb On Pe Pg Pk Po Us Ut Yk)
Qz(Al bB Fp Fy Jl Jn Jp Jr Kq Kx Mf Mt Mw Mx Nb Ng On Ut Wc Yl) aM(bP bU cD cX cZ dC eF gC iA Ik kR Ky lW mU Mw Ny Pa Pk Ut
Wb) jB(aG bF bG bJ bN cD Ct Dg Dl Fa fB Ha Hc Kl Lv Pd Pe Pf Pg Tl) oP(Bo bQ bZ Cu Fi Fr Gn hB Jl Jp Kq Nb nH Nn Nq Pf Qv Um Ur
Ye) Aj(As bM bU Co Cu dD dH Fr Fw Il kN Lh Li mT Mw Ns Qu Ut) Nh(Ax Cs Et Fp Ij Jn Jp jR kE Li Lj mT Mw NY oE oO Pc) Si(Ha Ik Ji
Jp Ke Lh Li Lj Mn Mw Mx Nd Ns Ny Ua Ue Un Yl) Qv(Ba bM Bo Ed Ha Hb iA kR lK mZ Na nO oT Oz Pb pK Ue Un) Vq(Ed Fa Fi Ha Ij Il Ir
Iv Kz Na Nr nW Oa oE oW Pb Ue Tj) Oy(bM bN bU Cu dD dH Fw gZ Jn Jp Li mM Mt Mw nH nU oW Ut) Us(Ar aW bJ Eq Fc Fp Fw Ki Lz
Mh Mw nH No Nu Oi Wb Yk) Pk(aC aI aV bB bM bO bU cB cC cD cF dD Gd Nm Ny Oz Wc) jK(aZ bC cC Cq CT dC Dp Dr Ij jD jR Kr St Ua
We Zw) Vo(aW bB bN bU Cu eQ Fw Ji Kq Lz mF Mw Ng Oi On Wb) eP(Ar aX Bc bF bG bN Bo bW cB cK dE It Mh Ml Mw Pf) Ua(Dk Fr Im
Jl Jm Jn Jp Kq Mt Mw Nb Nv Oa On Qh) Un(aW bO bU Dl Fw It Kl Kr Li Mh Ml Oi Pg Wc Yk) Ur(bM Ha Hv Ik Ip Ir Lh Lp lW Nb Nd No Nr
Ns Oi) Ut(Bg Ch Ct cW Eq Gd Hc Jf Ki Lt Ml Ng Of Oi We) Vp(Cu Fa Hv Il Jl Jp Jr Lx Mz Nr nY oE On Or Tn) Lj(bN bU cD Db Fc Ik Jy Ky
mW nH Ns oV pK Wb) Rm(Al Ir jF Jl Jn Kq Lx Mw Mz Nb Nr oE On oW) lK(Ao Ch De Dk Ef Mm Mn Mz Nn Qc Qw Uf Ux Zx) eQ(aG Ar
Cs Ed Fp Gd Ha Kx Kz Mg Mw No Wf) oE(bF bG bJ cR Eq Jd Jg Jt Mj Ms mZ Ql Yk) Qh(BG cD cL Db Eq It jD Mh Oi Wh Yk) nH(aO Du
Hc Ic Ki Pa Pc Pd Pe Pf Pg Yl) oW(cR Ct Hc Hv Ic Jt Kf Kl Kr Mj Pz Wc) Dl(bN Cu dH Ij Im mF Nm Nt ON oQ) Jp(Ef Eq Ha Hc iA Kx Qw
Uf Vc Wh Yd) lW(bB cW Du Fa Hf iP Kk Lh Oa Ug Ye) mU(cR Ha Hf Li Mw Mx Nb Nn No Oa Xa) jD(aL CH cJ dJ Hc Jq Mf Nw Tr Zx)
aC(aW bJ bN bU cZ Lz Mw mZ Nj Oz) iA(Bo bQ cR cW dH dN Kj Ug Um Ye) Ny(cD Du Fa Gd iP Ki Kx Qn Yk) Pb(bU cC cQ dD dH Fw Jn
kO Li) lX(aW bG bJ bM cW dR kR Lz oH) lY(aW bN bX cW Il kR nD Nr Ue) jO(De Em Hx Jg Mt Nd Nq Qw) Ik(Al aS bN Fp Kx Mw Pg)
We(Kq Lh Nb Nr On Rb Tn) Oz(aS bU Fw gZ Li mM Wb) Pa(Cu fA Fw gZ Il nC On) mZ(aI bB cJ Mn Og Yl Ye) kE(Dg Jt Kf Kl Kr Mj Wc)
Gd(bU Fy Ko kR Me Sr) Ha(aW Cx Hp Ki Nj Qn) Ue(aW bN Ip Nj Oa Yk) Wh(Jl Lh Mt Mw Mx Nb) iP(Jn Lv No Nr nY Oa) jH(aR Ch jU Mn
Nq Ps) Eq(mT mY Qu Tn Um) Wc(bN Hv Jf Lt nU) Kx(bU kR Mk Pc Wb) Ql(nW nY oO oQ Wm) Pg(Cu Fw Ij Lz Pe) cR(fP jM kC mF mW)
jU(Bg cZ Mn Zx Ti) Dg(dH hB kN oN) Du(fA hB nC pI) Jt(kQ mF mY oN) Kf(Lh lO mY oD) Kr(kN nW Qd Tn) Ps(jF Jl Kq Mz) Li(fP kC
mW Or) iJ(aG bN Ed No) jR(aU cY Nq Tr) Cs(Ex mW Rf) Ef(MT On) Fp(Nj Oi Pd) Mw(cD Ki Oi) Kj(kR mW oT) Rv(Ip Nd Oi) Yl(fA gL mI)
Oa(Og Tz Ub) Ul(aW Il Ru) Ug(Mf nA pK) Pc(bM cQ Db) bG(gC gP mT) Dr(jF lO) Po(Ns Wb) Tn(bF Bg) Hc(gL Jn) Yk(Rb Uh) Sr(It Ki)
Kl(kN oN) Ky(Ki Ns) Of(Ng Nm) Or(Il Lz) Um(dR kR) aW(jM lM) bU(bN oO) AlOg BajE CtlM FakK FbkR GnpK NokO MjnW MlmF
MsmY MyQw TvJr RcKq ZxPz JdmT WdkS XalO TldX RucD UofB PdbB aFjQ aGlN bMdD bXoO cCjF cWoK} Ji{Yk(aC Al aS Ax bJ bU
cC cM Cq Cu Ed Fi Fw gP gZ Ha Ho Ii Ij Ik Il Ir Jj Jm Jn Jp Ju Jv Kd kE Lj lW Mk Mp Mr Mx mZ Ne Nk No NR Ns Nx Ny Oa OK Pc Pg Qe
Qt Qw Qz Rb Rc Ry Sf Sh Si Ss To Tt Uc Up Uu Ux Uy Vb Vj Vo Vp Vq Vs Vt Vv Wb Yd Tj) tX(Aa aI aS Aw bB bI bP bQ bR Ch cK Cp cR
cS cV dJ Dk Dl dN Dp Ef eT fN fP hB Hc hP Hw Hx Id Io Is jE jG Jk jM Jn jO Jp Jv Kz lN Mj Mk Ne Nm Nn Nq nW oE Oh oK Qb Qx qZ rA
rS Tn To tU Uh uM Vt Vv zG) bM(aC aF Aj aN aO cB cI cM dB eC Ed EF Fc fP Gl hG hP Ic iH iJ Ik In Iu Jf Jj JO Ju Jv Ki Kl Lj Ne Nh Nk Nl
Of Og oK oN Ou Oy Pg Pk Qx qZ rR rS rW Ss Uh uL UM Uu Uv VT Vv Wb wE tM Wm) Jv(aC aF aN Ar Ax cB cI cJ Cs Cv dB dK eF Fa fP
Fw Gl Gp hP iA Ic Id iH Il Jd Jj jO Jp jR Ki Lj lM Ms Ne Nh Nk Nn oK oN Ou Pj PS qH rR sF sK tO tR tS tV Uh uL Uy VT Vv Wb wE Yh Tl
Wm) uM(aI aQ cB cK cS CX cZ dA Dl dN eC hP Hx Ih Io Ip Is It Iv jE JF Jk JM JO Kp Mj Na Nk Nv Of oK Or Qb qH qT QX rA rQ rS rW tO
tR tS tT TV Uh Un VT Vv wE wQ Wm) iJ(aC aF Aj Ao AW Bg bL cB Ch cI Co Cs dB dE Dg Dk Du EF fP Gp Hc Hu iA Ic IZ Jg Jh Jj Jo Kl Lj
Mg Ms Mv My mZ Ne Nh Nk Og On Ou Oy Pg Pk Qu Uu Uy Vv Wc We Wh Yd Yg) Ps(Ax Bc bJ bO bU cC cM Cu Cv Di Ed Eq Fc Fw Gn
hC Ik Im Ip Jn Jr Ju Kd Ki Li Lj Lx Mk mM Mx mZ Ne Ni nK nN Nr Nt Nu Oa Ok Pe Qa Qe Qw Sf Sh Si Uu Uy Vt Wb) vT(aI AJ Al aN Ba bI

Figure 41 Continued

Figure 41 Continued kP(Bc bU lr mE Nl pF Vq) Qy(vP vQ wJ wK wP yL) aQ(uM uU uX vB vH vP) eQ(aO Fn Lv Pd Uy Tl) iC(Ex Op Ux Yd Zx Tl) jE(Fr hL iJ Kk Pf Yd) jL(Ex Ho Uw Vh Vw Zq) Nn(hV jR qO tS vP) lc(eZ fY hO hP qD) t Ua Vj Wd) Mj(Fp Ih Iq Pc Qd) We(Ad eM iJ Mf nR) Ye(eM mT mU mZ nH) Vc(Cu iP IK oH Vq) Uy(Dd eM eP Nt Ut) mS(bU Cv Ib Rf Ur)
IM(fR IY qT sK Yd) Aj(dB Jt Ne Nm) Mw(Jg Jl Jq On) Wd(Cu iJ iO Ou) hG(qT sH tS tV) rS(dB qX rA uM) Db(Sf Sh Wf) Gz(qO qP yE)
Ne(Nj Pb tV) Jh(Jq Kq sJ) Wn(Ba Ss Tn) aN(uM vT wJ) cM(lY ml Vh) gZ(Ps Vs Xa) mU(hR Zq Yf) Cu(Ps Vb) Ew(Fr Nj) Gb(aM cD) Mh(Pb Pc) Mp(Ny Qd) Yg(iJ nR) Qw(Vi Zx) Jt(Jo Mg) Kq(Iz Tn) Ry(nC nH) Lt(eF kP) Oe(Ny Qd) Oz(aA Mc) fP(Jv tV) lK(Dr wJ) oH(lX pI) oT(cQ cR) ExyE FceP NmMs NiVh IbsJ HbSi YicD ZqiA JlPb XanK UxeF VajT aFdW hArQ nJhR hPsK qXuM rVvV} Zq{Kl(Al aM bB bO bU cM Cu Cv dD iJ Il iO lP Ir Jm Jp Jv Ki kK Lh lY mE Ml Mp mS Nc Ne Nm Nr Ns Nu Oi Ok oW Rg Sf To Vc) mS(aJ Al aW bL bS cD cN Cx dB dG gP Hu Ib Il iP Je kO kP lW Mf Ml mU nH Ny oP Oy Pd Pe Pf Pg Qn Rc Uu Vp Vs Ye Tl) Mh(aE Aw bB bU cD cL cM Cv dD Dr iA iJ jG jK Jm Jv Ki Mb Mp mU Ne Ns Og Oi oK oN Pc Rg Sf Vc Wb) jK(aE aG aX bP cC CH cR Iz Jj Jk jM Jv Kd Kn lN Mv Mx Nn Nq Qz Ru Sh Sj Ua Ul Vc Vz) aM(aC aJ aW bU cD cK cL cM Dd dG dL Fw Il jI kP lW Mj Mp Ne Ns Oi Qn To Ut Vs Wh) cM(aC Ar bM cD Ez Fw Il iP Ir jI Kx mE Ml Mw Mx nK Nr Oi Oz Pb Qn Rg Rx Vo Vs) kP(aO aQ bU cR Ct Db Io Jn Ju Jv Kf Ki mE Ml Mq Ms nR Pg Ps Sf To) mM(Af Bn cN Cx dM Ml mU nC nH Ny Oi oP Oz Pb Pg Ps Qn Vp Vs Ye) lN(aA aG aS bB bR cL dD Hb Ii Ir Iu Jm Nc Ni Nl Nr Qc Sr Yd Yl) Ne(aC cD Dl iP Ju Jv Ki Kx Ml Oi Ps Qn Rc Rg Rx Sf Sh Uu) hA(aP aY bN cD cG dB Dr Ic Ii jO lL Qc Ri Rz To Ue Ug Va) iJ(aO aW BG cD Ct Dg Dl eF Gd iP Rc Uc Uu Uy Vb Vo) Al(Aj Bg cD Ef Jj jL Ju Og Oi Oy Qz Rg Sf Sh Ua) Ki(aS cD Ha Jv Nc Oz Qw Sf Sh Up Us Ut Vc Vt) aC(aW bJ bU cD cL Cx Jv Mp Nc Ni Oi Pk Qn) jL(aS cD Cv Fw Ii Iq Iu Ni Nm Qg Sr Ug) Ml(bU Ha Jv kG mE Mp nR Pc Sf To Wb) Rg(Cv Ez fA Fw mE mZ Nc nK Nl nR Ns) Oi(Ar Fw Gd Ha jM jQ mE Nl Nm Vo Wb) iP(bJ bR bU cD Gd Ha iA mZ nB nR Vc) mU(bL bU Fp Jn Mx Vb Wc Xa) jH(aX cC cH Ez Hx Nq Qw Ug) Mp(Cs Jj Kx Lx Oa Or Po) Io(eF eP jF lM lW oK Pc) Qn(Ha Jv Oa Po Qe Sh Vt) nB(bE cN Og Ps Rf Rx) jG(aX Db dE jM Kn Sj) lL(aW cE dE Fi Lh Or) Ez(Fa Kx Lx Mf Pg) Gd(aO Il kK mE nY) Sh(Db Dd Mf Ut Tl) nR(aI bB gP Mn nW) jV(Ar cQ Ir Qm Rz) Cv(Aj Oy Vb Vs) Dl(mE mZ nK nO) Fw(cD jI Nl Pg) Qe(Ps Rm Ua Vp) aO(Cu hC kG oF) bU(cD gP Kx oP) Nc(Cu Kd Po) Uu(lW mT Tl) lY(aW kR Ps) jF(aH Qw Va) lM(Ic Mg Yd) oP(cR Qv Tl) Cs(Db To) Ha(Cx Sf) Nl(Ed Tj) Hx(jR lK) Qc(jI lK) Jr(Vp Vs) eC(bF cD) mE(Bg We) jM(aH dD) jO(cE Op) kG(Rj To) CuVs DiKx LxOw NbQw NiPc HvVp IrRm UrlW VtcL VokK aGjT aJiZ aUjQ bLkI gPmZ mHnK} tO{Dl(aF Aj An aO Bb bF bG bR bU cB cE cF cI Co Cq cU cZ dD dF dH Fa Fw Gl Hf hL Ih Ip Jj Jl Js Kk Kn Kp Kr Kz Ld Lh Lx Mg Mr Mt No Nr Nu Nv Nw Nx Ny Oa Og Oi Ou Oz Pk Po qQ qZ Rg Ri sJ Sr Ug uI Un wD) qZ(Aj AN Ar As Ax bM cD cH cQ cR Cs Dg Dp eC Fw Ih Ij iO lP It jE Jh Jl Js Jv Kd Kn Ko Lh Lu Mf Mm Nm Nn No Nr Nv Nw Oa Oy pS QA qB Qd Qe Qm rB Ri rP sC Un Vt zG Wm) Kr(Aj aM AN Ar bU cK cN Cq cR Cu cX dN Ed Gl Im lP jE JU Jv Lh Ly Mh Ms My Ny Of Oi Or Ou Pk Po Qm qQ qU qW Qx rB Ri rQ rS rV Sr tV Un Ur Vt yE) Un(Aa AN Bb bU cR cX cZ Dg dN eC gP Hc hG hP Hw iP Iq Jh Jj Jk jO Jv Kc Kd Kk Kn Ko kR Kz Ld Me Ne NW Pe Qm qU rB Ri rS rT uG uI uM uX zG tM tF) rB(Co Cu Fa Fw Fy Ih Ii Im In Is Jl Js Kn Kp Kq Lh Lx Mp Mq Mt Nm Nn No Nr Nt Nv Nw Ny Oa Oh Om Ou Pb Pd Pe Pf Po Qa Qd Qe St Vt Wm) Vt(aC AN aX bR cF cR cZ Dg dH eZ Gl Ip Iq Js Jv Kd Ld lK Lz Nb Ne Nm Nn No Nv Nw Oz Qm Qy Ri rS tS zG) Vq(aC An aW bP bW cH cM cZ Fa Ii Jg Jj Jn Jq Ko Md Pi Qm qY Ri rS rT rV To vB) Nw(Bc cF cK cR dL fP hL jO Jv Kd lK Or Pk qA qX rA rC rP rQ rS Wm) Lh(AN cF dB dN fP hG hP iH iP jM jO Kz Mj Mk Ne nW rA rS uM) Aa(cK cM cN dL iO Jl Or Oz pF rP rQ sH) Dg(cF hL hW Kd kR Pk qQ qX rN sJ vB Vv) Ip(AN cB cF iP Kk Ko rP rS sF Sr Ur) Bb(cH Ed Fw Jv Mh Ne No Ou rQ sJ yL) rS(Cs Jl Ks Lz Mh Mt No Nr Oa rP Wm) Nm(Aj cF iP qQ qX Ri sI Ur) No(An hG jV nW Pk qU sH Tv) Kf(An bR bU cB cF fP hG iH) Fa(Hw lL Lu nW Qm Ri zG) Gl(An cH Cs Js Mf Ne Qd) Ld(iO iP Mh rP sJ zG) Ny(cH cR dL Jv lK Ne) Kq(bU Ch iP Iz Jv) Ri(dH kR Mt Oa qQ) An(Im kR Mh rQ) Jl(dN iP jO nW) Ou(aN dN iP sI) Cu(aN dN Lu) Et(cR Jv rQ) Mh(aN Kn Ko) Js(eC iP qU) Nv(jO Ne nW) hL(Ql Qm zG) sJ(Ap Hq Pa) rP(Aj Kc Qm) Ar(nW uI) Fw(Lu nW) Nr(eC hG) Mt(dN eC) Jv(Ij Jd) Kn(fP zG) Ko(bU rQ) Oa(hP lL) kR(Nx Ql) ApqQ CsjV PohA MaTr HxsI ImcM QxOk KpzG} tT{Dl(Aj An aY bR bU cB cF cI Ct dB DK dN eC Fa FP Hf hL iB iH iP Iu Jh Jk Js Kk Kp KR Kz Mf Mg Mt My Ng nY Oa Of Ou Oz Pk Pz qH qQ Ss uM vT Vv wG) rB(An Ax Cs dB Fa Fp Fr Fw Gl Hx Ij Ik Im lP Js Kg Kk Kp Kr Lh Lv Lz Md Mf Mh Mt Nm No Nr Nv Nw Ny Oa Oz Pb Pk Qd Qe Rh Ri rP Un) Kr(bU cH Cu cX dN Fa fN Gl Im lP jE JV Kz Lh Mf Mh My Na Nc Ne Nl Ny Of Or Po Qm qU Qz rP rQ Sr Un Vt wJ yE tM) qZ(As Ax cH Ct Dg Dp eC Ef Fp Ih Ij Ik lP jE Jh Jk jM Ko Kz Lh Mf Mh My Nm No Nw Oy QA qB Qd Qe Qm rA Un zG) Un(Aa An aP cQ dN eC hP Hw Hx Iq Jk jO Ko kR Kz Ld My Ne nW Qm Ri rS uX vA vT tF) Ny(aN cF cR dL dN eC fP hP Hx iP Iq Jk JM Jr Jv lK Mf Mj Mk Ne Oy pF rA uN) hP(An Bb Cs Dg Et iP Kn Kp Lh Mf Mh Mm Mt Nw Oa Qd Ql Ri rP Sr Vt) rA(Aa An Ap Bb Dg Et Ip Jg Kc Kn Ld Lh Nw Ok Qm Ri Tr uI) dN(An Ar Cu Et Jl Js Kg Ko Lh Nm No Ok Or Qd Qe Uf Wm) Dg(bU cB cF fP hL iB iH jM kR My Of Pk qH qQ qX Vv) Vt(aC aM aX bR Ip Iq kR Kz My Ne Oz Rh Ri To uM) fP(Aa Ao Ar Et Gl Ij Kf Kg Kn Ko Lh Nw Ri Uf) An(eC fN Ip jE kR Kz Mh My Rh rP rQ rW zG) Mf(Aa aN hG Jg jO Ld Mk qU qY rS rT tF) Ri(jM jO kR Kz My Ne qI Qz rP uV Vq yL) iP(Ax Et gL Ip It jM Lh My Nm Nw Qm uI) Ip(aN cB cF eC hG Ko qI qU rP tF) Kz(Aa Ar Bb Cu Et hW Kn Lh rP Sr) Qm(cB cF Fa hL jK jO My Oz qI Vv) jM(aL Co cZ Et Fp Ij iO Lh Nw Tr) dB(Bb iH Pk qU qV qW qY rP rS) jO(Fb Gl Lh Nv Nw Oa Rh Sr) Mh(Aa aN Bb Ko Ld rS tF) Nm(cF eC hG hL Pk qQ) Vq(bW dM hG Kk uW tM) Aa(dL Fr oH Oz tV) No(eC qU sF sJ tF) Nw(fN hB Jv qI qX) Bb(cH Je Jv yL) Fa(eD Lu My nW) Js(aN eC qU To) Kf(bR cB cF iH) jV(Ax Cs Fp Rh) Ap(bU cB sJ) Lh(hG Mk Ne) eC(Ij Ok Qe) zG(hL Kp Oa) rP(Hq Ld Me) nW(Ar Md Nv) Et(jE qX) My(Kq Sr) Jg(Jk vT) Ko(kR rQ) Rh(cR Jv) Of(Ks Vo) aN(qT uL) tF(Fw Md) sI(Hv Hx) AroK ChIm CsgW LurQ TnKq IjhG IqOk QdrC KcsF KnsJ LdjE} hA{Yd(aC aF aG aL aO aQ As aW BA Bb bI bJ bL bN Bo bZ cA cC cJ cM cN Cq cR Ct cZ Db dK Em Gb Gh Hl Hq Hv Hx Ii Iq Je jL jM Jn jO jQ lL Ma Ms Mv Pi Pk Qm Qv Qw Qy Rx Si Tz Ue Ug Va Zx) Si(Ad aE Aj aZ bE bR bS bU cC cI cU dB dE dH dK Fn Gl Hc Io Jl jQ Kc Nc Ne Ng Nh Ni Nj Nl Ns Oh Oz Ph Pi Po Qy Rc Sr Tz Ug Um Ux Vq Vs Vw Zw) Va(aD aF aR aV bB bR bS bW cE cG cM cO cU dJ Hb iB Ic Jf Jh Jn jO Jp Jq Kk Ky Ld lL Lx Nw Ny Or Pe Pi Qa Qd Ql Qx Qy Rv St Tz Un Vi) Vh(aF aG aO bN bS cD cE cU dG dH dK Hf Ir Jn Kc Kd Kg Kj lL lM Mg Nh Oi Pi Ps Qy Sh Tz Ul Um Un Vz Wh Zx Xa) Op(aE aH BA bN bR bS cC cG cO cU dA dF Fw Gb Ii Jh jO lL Ma Nd Pi Ql Ug) Rz(Ad Ba Bc cM Ct Cw Hb Jd Jg Jh Jk Kf Kl Mg Ne Ng Of Ql Qu Uy Vq Vt Wd) Dr(aO Ap bS cE cS dF dK Ef Ex Fr Gn Hc Jd Jh Lp Mg Oa Pi Ql Sr Tz) Ps(aJ aO aP aR aW aY bN bS cE cG cO cS Cu dB dF dG Fn Hf Lu Nf Oi) Zx(Ad An aO aP aY bF bN bZ cG cU jO lL Mg Nq Nx Pa Ue Ug Vo) Zw(aG aO aY bN bR bS cE cG cO cU dF dH Hf Oi Ph Pi Ql Um) Tl(Ar aY bN dF dK Ez Hb Is Ml Nw Qa Qb Qc Qd) sJ(An cC Dl hG iH Js Nm Nw pS Qv rS tU uM wP) dG(Fd Gb Gn Hl Ho Rv Uw Uz Vi Wc Wd Wg) Yl(aO bS cE cO cU cX Pi Qc Ql Ug) Ux(aO Ar bN bR cS Hb jO lL Oh Pf) Gb(aY bR bV cC cU Mf Oi Or Um) Vi(bF bQ bR bZ Ez Hq Ma Um) Sf(bR cG cO Hf lL Ou Pi) sH(jE Jr rW sC Sr vV yH) Vz(bR cG Hf Iq Qc Ql) Wc(bS cE cG cO Hf Pi) Cu(Fd fR Hp Lp Wb) Sh(bR jO Ma Mf Ou) Xa(aR aY dB Ic Jf) Lt(bR cU Ic jO lL) Rt(aO bQ dF Ph Um) Uy(bV cU lM Mf Ms) Po(HP Sj wH) Ye(Fw Hb Qm Sr) Tm(bR cE Cw Ic) aR(kF kP lX Vw) Ho(bV Fc Um) Wf(bR Jn Sr) Ry(dH Jf Um) Rv(Fn Jt Nm) Uw(bN dF Ue) cU(mE nA nD) sI(Nw pY uO) sF(jE No Vu) rQ(AN Nw) Gh(Dc Uc) Gn(Hb Iq) Hl(bU Jq) Wd(aY cG) Lp(cE Hb) Tk(Pe Pg) Vb(Ad Pa) Vw(Jt lL) AfkF EzWe FcUg FiaG LxhP WbbN SjbR QcmM JfRx WhOm KknN LhcF QlwF} Ok{We(aF Al aO Ar As bJ Cs cT Cu Cv Cw Cx Dd Dr Fn Hb Ho Hv Hw IJ Im Ir Iv jI Jn jO Jt Kc Kd Kg Kq Kx Lh lL mE Mf Mi mT Mw Nb Ng Nm No Nt Om Pc Pi Pk Po Ps Qc Qn Ut Vh Vi Wb Yl Tl) Ps(Aj Ar aS bF BG bJ bO bU cM Cs Cu Db Dr Ed Fw Hb hC Hv iP Jj Jn Jr Ki Kp Kx Lh Lx Lz Mf Mh Ml mS Nc No Oi Or Oy Pa Pe Po Qe Rg Sf Un Uu Vt Wb) Rx(aO aQ aU bF bG bJ cD cM Db dR Hq Jj jO kR mE mU mZ Nc Ne Nh Ni nK Nl nR Oi Oy Pg) Im(Fp Hu Hx Ii Jh Jj Jk Lw Lz Mc Mg Mh Mj Mp Ms My Ng Nj Nq Oe Of Og Oy Pb Pc)

Figure 41 Continued

Sf(aF aJ aO aW bF bJ cT Cx Db Dd dF dG dM dX Ju Ki Mf Mh Ml Nc Ne Oi Qn To Vs) Yd(aJ bU cD cM Db dG dI eQ fA Hb Hv iJ iP Ki Lh
Nc Oi Op Pa To Ut Vt Wb) Oy(Aa bM dB Fp Hu Jj Lw Lz Mc Ms Nd Nn Nu Nw Of Og oW Qa Qd Qe Tl) Wb(aO Ar Cx Hp iP Jl Kx Lz Mh
Ml Nc Oi Oz Pa Pg Qn Qw Ua Vp) Fp(Aa Hu Jj Lw Mc Mj Mp Ms My Ng Nq Of Og Oz Pb Pc) Rv(aW bG bJ cQ Db dG dI Jl jM lN Ly Mj Rm
To Vp Vs) Og(Hu Ij Lw Lz Mc Mh Ms Nu Nw Of Oz Pb Pc Qe) Jj(Aa Jm Lw Lz Mc Mh Ms Nu Of Oz Pb Pc Qe) Sh(aF aO bJ cV Cx Db Dd Ki
Qn To Ut Tl) Lz(Aa Hu Mc Mj Mp Ms Ng Oz Pb Pc Zw) Of(Aa bM Hu Lw Mc Ms Nn Nw Oz Pb Pc) Aj(aF aN bM cB dB dW Ne Nh Nm Nt)
Wh(aF Dd iP Ki Kx Lh mS Mw Qn Vp) Ms(Aa Hu Lw Nw Oz Pb Pc Qe) Ng(Lw Nt Ny Oz Pc Qe) Tl(dX jl Oz Pa Tt Uu) Vb(Db Dd lN Nm Qn
Ux) oP(Dp Gn Ki Qm Rt Yj) Mh(Mp Nw Oz Pb Pc) Zw(bM Kx nK No Po) Dr(Dc Hp iC Vp) Gn(Aa aO Hb Vp) Yg(kG mS nK Pe) Qe(Hu Nq
Oe Oz) Wc(aO Db iJ iP) Nw(Mj Mp Nj Oz) Ux(Kl lN Uu Vs) Pc(Hx Lw Nj Oe) eW(aV aX Fr Pz) Gd(aO iJ mE) Wd(iJ iO jO) Qx(sK tR yJ)
Ye(mE mS mZ) eQ(Ou Sj Tr) Dw(Ba Dl) Ex(wP tM) Fc(Hb Rg) Fd(mS nO) Gz(sM sO) Nu(Oe Pb) Lw(Mp My) Hp(bJ Hw) Yh(mS nK) Jk(rQ sF) Kl(Kq nT) Uw(mZ Vt) Vs(Vi Yi) tR(dN jO) yJ(iP Iq) wE(aQ cY) AaLu NtVj McNj MyOz TnsH HbSi PzdW WfiC RzjM RtkP RmpH OpiB OuoV UuVh VwlK PkbM rBqO sKjO qXuV} Jp{Sh(aF aJ Al aO Ar aS aZ bB bJ bM Cv Db Dd dM Dr hG iJ Ir Iu Jm Kk Kx lL Mf Ml Mw Ne Ng Nl Nm Ns nY Pc Qu Ug Ut Vc Yi Yj) Yd(aF aO aS Ax bB bI Db Di Dr eM Hb hG iJ Ik Ir Iu kS Lh lM mW Nc Ne Ni Nl Nm Ns Op Qw Vc Yi Yj) Vc(aF aO Ar bF BG bM bO cE Ch Cv Db eF Ib iP jM Ki Kl lM lN Mf Nd Oi Sf Uu Yg) Wh(aF aO Cv Dd Fw iJ iO Iu Kx mE mM mS mT mZ Nl nK nY Yi Yj) Uu(Ax Cs dB Dr eM Gn kO mS nC nH nJ nL Nm nO oP Vh Yi Yj Wm) Jv(aF aH Ar Ax cB Cs dB Dr eF Fp Ic Ki Lz My Op Vv Yi Yj) Kl(Ar Ax bM Cs eM Kq ml mP Ne Nm nN nO nT Ny Qe Vh Yi Wm) Dr(aO Ez hG iC jL Ju Kd Kx mS mZ Qu Sf Ua Vp Vs We) eM(Hc Kx Ps Qu Qv Qx Rg Rm Rv St Uc Uw Uy Vi Vo Vv) We(Cv Dd Ho Kq mE mT mZ nA nK Nm nO oP Yi Yj Tl) Wb(Ax Il Je Kx Lz Mh Ml Nl Oi Oz Pa Pb Qw Ua) Ic(Ar Ax Bg bM Ch Cs Hc Iz My Ne nT Wm) Sf(Al aW Dd dX Fw Il Mf Mw Ne Nm Yj) Wd(iJ iO kG kP mE ml mT mZ nI nK nL) Gn(Hp iJ Nc Qu Qv Rm Ua Uv Vp Vs) Iz(Ar Cs Fp Kq Ne Nm Nn nT Ny Qe) Ps(mE mF mW mZ nA nI nK nO pH Qe) Yj(aM Jj Qu Qw Ua Ur Uv Vp Vs) Vi(kP lW nB nI nK nL nN oW) eW(Aj cW cX Fr Hu Jk Oe Of) Ne(bM Hc hP Oa Rx Si Yg) Uw(mE ml mZ nA nK nO nT) Fp(Aa Hu Im Jj Ms Nm) Gz(qU sM uG uU vB yE) Yg(hG iJ mE ml mS nK) Yi(Bg Ch Hq Oi Vp Vs) Yl(Db jM lM lN nK Oy) eP(Fn iJ iP Ki kK To) fR(Ha jF lL lM qV qW) nT(dX Ef Hc Ib Ou Vs) Ax(fB oP Ou Ow Vv) Cs(Qu Ss Vs Vt Vv) bM(Aa aC Aj Oy Pk) mS(dX Ib Ou Rc Zx) rB(aN aQ cB cY dA) Ch(Gb Kq Qz Vh) Fc(Qu Rg Tt Uv) Im(Hu Jj Ms Oy) Wc(iJ mU mW nO) nN(aO Ef hG Vj) Aj(Nm Qe Vt) Gb(aM Mh Ml) Kq(Aw Ef Jh) Vh(Bg Jj lM) Vs(Ho mM nO) Pk(aC dB dX) iJ(Sj Vb Vj) Fi(Oy Qu) Ha(Fd Hp) Mu(DW) Ib(No Rj) Vz(lL nK) Ye(mE mZ) Ru(jK lL) dB(jO qU) dX(kG lX) hP(dA jO) oP(Qv Up) pH(Ou Rm) AaJj ArHc AwSr DbRv EdQu EwaY NmVb HoUa YhnK QeOw RzaW UofB VaiB VjlW VtaC aMdW aNqT aOnO hRoO sIjM rArS kFoW} jM{wB(An aV aY Bc bG bQ bU bZ cA cD cF cG cK cL cN CO Cq CU dA DG dH dI Il Jl Jy lK lO Lw Lx Lz Mi Mk Mp Mq Mt Nd Nr Ns Or Ou Ow Oz Pa Pb Pd Pe PF Pg rC Rg Ri rQ sI Tr uI Us Vu Wm Tj) sI(Af As aY bE Cs Cx dD De Di Ez hL hW Ip Ir It Jd Jh Jr Jv Kc Lh Ng No Nv Nx Oa On Or Ow Pk Qz Rb Tr Un Us uZ Vs wP xA) Uy(bB cZ dC dD Ex Fw Hb In Is Ky Ld Lv Lz Mh Ml Oa On Ow Oz Pe Pg Ph Qa Qb Qd Qg Qx Rx Tv Tz Vb Zx) Yd(aL aM cG cM cR Cs dD Dr Ex Fw Ha Hf iC Ij Ir Jq Ky Ld Lx Ml Mp Nb Nw Ny Pe Pf Qa Qe Qw Qx Uw) Uw(Af aG aI aJ aR aV aX bO cI De dG dM Em Hp Hu Ic Il It JG jK Lp Ni Qt Rg Rj Ua Wh) sJ(AF bB bQ Cx Fn Hw It Or Qg Qn Uk Up uT vU wK wP tL) Sh(bB Dc Ii Jq Kq Lh Mg Mr Qa Qd Qh Ry St Uc Vi Yl) sH(aL aR dN eZ Gp Ha Hv jV qU rB sO Ss uP uU vT yD) Rv(aG aH Ba cM cV cX Gl jG jK Lh Lx Pe Po Qu) wF(An Ar Cs Gl Kn Ko Qm Ri Sr Uk Ur) Vh(aI Ed Fw It jF Jj Oe Uk Vt) vO(Cu dG Fa Jl Lx Mq Mt Pe Po) Dr(aV bH dD Fw jG Rj Sf Sr) Ye(Db Dc Jl Kq On Qd Ql) Ry(aV bB Dl Hb Mk Oi Rg) Yl(aG aV Ba cT Em Hf Jj) tN(Aa Cs cZ Kn Ko Ri Sr) Zx(aH cM CT cV Gl) Lh(Fc Fi Rx uI uX wH) Vc(bB cJ dD dF iC Jj) Vi(aG cC Ct Ez Hb Qz) rS(Fr iP Mt Qd Ri Un) An(rQ tV wD yL zA) Si(Db dD Fw Ou Ql) Wh(bB Dc Ir Mt Qe) lY(aR bG cV Hf Ki) sF(eZ Ha Nx Ou uZ) Hp(Nb Oa Qa Qe) Vz(aI aV bB Po) Sf(aI Ir Po Qa) Wf(Hf Jr On Vt) Js(cV mM tV Tk) Ps(aV Ih Kq Qa) wD(dD Ql Qm Ri) qZ(aN bM tU tV) Kn(rQ uG vT) Rx(cM Ct Ii) Vb(cM Ii Of) aR(kO kP lX) wP(aF Cs Fp) wH(Lx Pe Po) uI(qX Sr Vt) Zw(Jj Qz) We(Nb On) Rz(cV Qu) Lp(Kq On) Op(Bc Hx) Va(aI Ou) Vq(tQ wE) bB(Gb Ru) cU(mE mT) tR(Cu Uc) wG(Fa Mt) rQ(Aa aN) uM(Pe Tr) AofR CstV GnaG MqvT HfWc JrTl XaaV TmVt RisK RgVw UnuX UxaH PkmW aSnT cZtU dDqA} Op{lL(aA AD Af aM An Ar As Ax Ba Bc Bn cG cM Cp Cq Cs Cv Cw dA Dc dF dG dL dM Dr Em Ex Fc Fd Fi Fy Gn Ha Hl Hv Hx Ib iC Ij Il In Iq Ir Iv Jd JE Jh Jl Jo Jq Js Jt Kd Kg Kn Kp Kq Kr Ld lO Lw Lx Md Me Mi Mj Ml Mp Mq Mr Mt Mw Na Nb Nf Nm No Nr Nu Nv Nx Ny Oa Om Or Ou Ow Pa Pd Pe Pg Pk Po Qa Qx Ra Rb Rj Rt Rv Sr Tn Tv Ud Uz Vi Vs Wc Wf Wg Tl Xa Wm Tj) jO(aH aM Ax bA bI Bn cG cP cQ Cu cW dA dD De dG dM Ex Fi iC jE jI Jo Jy Lh Mj Nb Of Ou Pa Pf Po Qe Ql Ry Sr Tn To Tr Uc Uw Uy Vt Tj) iB(aE Ba Bn bR cC cM cP cT cX dI Em Ez It jF Jq JU Ki Ky Lv Mf Mk Nd Ne Nh Nn Nt Oe Qa Qv Rv Ry Sh Sr St Ux Vc Vw) jU(aD aI aM Ar Ax DL Dr Fw Gb Hr Ij Ir Iv Jd jH Jn Jy Kn Kx Ld Lx Mj Ml Mq Mr Mx Ni Nw Ow Pe Ps Qa Qx Rv Un) iC(Ad aG Ao Ap Ba bI bS cA cM Dg Dp Dr Em Fn Jn Kc Kl Mk Nc Ne Nh Ni Nj Nl Nn Nu Oz Pc Pd Ph Rx Ug Vc Vo Zx) jV(aD aH aM Ar Ax cC cH Cs dA Dk DL Dr Ex Hr Ir Is Jd jH Jq Jr Js Ld Mj Mq Mr Mx Or Pe Ps Qx Sr) jH(Ad aI Ba Bc bS Cp dB Dc dJ Gp Ii Io Iq Jg Mr Nc Ng Nh Ni Nl Nu Of Oi Oz Rx Xa) jI(aC aG Ao Ba bS cA cM Db Dl Fn Hx Kl Mk Nd Nj Oz Qw Ug Va Vo) lO(aG Ao Ap Ba cM dC Kl Mk Mr Nc Nd Ne Nl Nu Pc Ph Ql Rx) jE(aG Hb Io jG Kl Mr Nc Nd Ne Ni Nl Rx Ug Vc) nK(cD Pe Pf Pg Vo Vv Vz Yg Yl) jG(bA bI Ii Je Kn Ni Ql Ug) jL(Bc Bn Pa Ql Ug Uw Uy Vs) lM(Ba bB Bc cQ dD Gl Ry Vc) nN(aO bU cD cR Kl Pg Vs) jK(cC dC Io Mr Rx Ug) Pg(mT nH nL Pe Qe) Jj(Ha Qa Us Uy) Cs(Ex Uy Vt) Nu(jQ jR lK) Oz(mM nB nR) iJ(Bg Sh Vo) jF(Ad Pd Ug) Ni(jQ jR) Ky(jR lK) Rg(mE nL) cR(nB oP) DdSh DrlK PoMk FanL MjQe NdlN KqUv UsaW VskG aGjT aMlW cNnB} Nw{cW(Aj AN Ar aW AX Bg bM Ch Co cR Ct cX dC Dk Dl Fp Fw Ii Il Jj Jt Mv Ng Nj Ny Om On Pg Pz Qd) Fp(Et Hu Hx Im Jj Lw Mc Mh Mj Mp Ms Mv Mw My Ng Nm Nq Ny Og Oy Oz Pb Pc Pg sF) tR(Bc cF cK dH DL fN fP jO Jv oH Pk qA qX qZ rA rB rQ rS rW Un Vt) sH(Aw aX Bc cL Fn Gp hG hO Hu iH Jd Jk Jv Kf Or Pa Pi qU qY sK Tn Tt) Mh(Et Hu Hx Im Jj Lw Mj Mp Mv Mw My Ng Nj Nu Ny Og Oz Pb Pc Pg) Nj(Hu Im Ir Jj Lw Mp Ms Mv Mw My Nd Ng Nu Og Oy Oz Pb Pc) Oy(bM Et Hu Ij Im Ir Jj Lw Ms My Nd Nm Nt Nu Pc Qd Qe) Nu(Hu Im Jj Mp Ms My Ng Oe Of Og Oz Pb Pc Pg) sK(cF fN hP Jf jO jV lL qX rA rB rW sF sJ Vt) Ms(Hu Im Ir Jj Lw Me My Nm Oz Pb Pc Pg Qe) Nt(Hu Jj Mp Mv My Ne Ng Ns Of Og Pb Pc) Qe(Hu Jj Jk Mj Mp My Ng Nq Og Oz Pb Pg) Im(Jj Mp Mv My Ng Nq Of Og Pb Pc) bM(aC Aj bE Ne Pk qT qZ rS rW wQ) dW(aF An Ef Fr Ii Jk Mv Mw Pz) Oz(Hu Ir Jj Lz Mp My Ng Og) Pc(Hu Jj Lw Lz Mp My Ng Og) wQ(cF dH Fa Jv qI qX rA Wm) sF(aA Fn Ib Iu Jk pF Qt vT) qU(aX dB dE dK fP Gz iP Kr) sI(aY Hw Kk Kr lK Pa pF) Nm(Aj Mp My Ng Of Og) lK(qH rW Va Vc vV Yd) Pb(Ir Jj Lw Lz Og) jL(Hl mM Ux Va Vw) Dw(Ad Jh Jo Jt) Et(Hu Jj Ml Mp) Gz(sO uU vB zH) Jv(qH qO rR tS) iB(Hp Lp mM Ye) tN(qI qT rA rB) jO(hL qA uN yJ) rQ(aN Kp Ma Of) Ew(Cs Mn Ng) Mp(Lw Lz Nn) Tl(iC jH jU) Pk(aC hG iJ) tV(aQ fP Ne) sJ(aA Iu Qn) rA(rS vU wE) qX(rS uM uV) jV(Ux Vw Wf) rW(Kp Rc yJ) Ml(Mc My) Jj(Jm Ny) aN(aC qT) nK(Fd Ps) rB(cU Or) qH(cN Rc) lL(mM Vh) DdSf GpWn LwMy HuNy YdlN SjjU KqfB VajG Vwjl aMdK cBsM cFwJ cXqA dAhP dBrS dLqT nJhR tSqZ iPyJ rZoO lOvA} tR{qZ(aH Al As Ax Bb dB dE Dg Dl Fw Hx Ih Il Im lP It Jd Jf Jm Kc Ko Kr Lh Lu Mf Mx Nm No Ny Of Oy Pi pS Qa Qd Qe Ql Qm Rb Ri Rm sC Un Vt zG Wm) Dl(Aj An aQ Bb Bo bR bU cB cF cI Cw dB dH dN lP Jd Jj Js Ki Kk Kr Lx Mr Na Ng nW Ny Ou Pi Pk qH qQ qX sI sJ) Ip(Ad AN Bb cB cF cM cR Cs dB Fa hG iP Jd jE Jf Kk Kn Ko Kr Pk qD qU qX rA Ri rP rS rW sI sJ Ur Vt Vv tF) Im(AN Ao Ba Bb Bo cF Ch dB dE Dk Hc hG Iz Jd Je Kc Kg Kr Kz Ld nW Ou Qx Qy rB rC Ri) Ny(aM aN cF CH cR dB dL Ed hP Jk Jv Kr lK Lv Ne Pk qA qX rA rB Ri rS rW uN Vt) Lh(AN Bo cB cF dB dN fP hG hP Hw

Figure 41 Continued iH iP jO Kr Kz Mj Ne nW rA rB rS uM) rB(Cs Cu Fa Ih Ii Ij It Js Kn Kr Mt Mx No Nr Nv Oa Qa Qd Qe Vt Vu) Un(Aa An dN hG hP Hw KR Ld Me nW Ql Qm Ri rS uX zG) Js(AN aS cX dN eC fN Gl hG hP jO jU Kc qU rS Vt) Vt(dB dC dE hP Jd Kr Ql Qm qX Ri Ue uM Vu zG) Kr(bU Cu Ed Gl iP Jd Ly Mh Qm rQ rR rW) rS(Ih Ij Jd Jl Lu Lx Mh No Qd Ri) dN(Cu Jl Mp Mt No Nr Nv Ou Qe) Ri(Bb dM jG Kd kR lO oH rV) Qm(cF dH Fa hL Mt Nu qQ rP) Jd(iP jE Jv kR No oE rW) Ld(iP jE rP rR rW sF sJ) nW(Cu Fa Fw li No Nv Ou) Bb(Ed Fw Pi qX rA sJ) Nm(cF iP qQ qX sl) No(hG hP sH Tv) Lu(Cu Fa Fw hL) Ij(hG Kz Qx rC) Ql(jV kR ql qX) Dg(Pk qQ qX) Gl(An Ne Qd) Kf(bR cB cF) sI(Fw Hv Hx) jO(Ii Nv Vu) rQ(Aa An dB) Ih(hP jK) Kc(sF sJ) Kq(iP rW) aN(Pi Vu) qX(Et Jg) FazG FwsJ NeNv TvQe IliP KndB} sH{hG(Al An Ar Ax bA Cv Dc Dd cD Fa Ha hL hW HX iB iJ Im jE Js jV Kc Kd Kn Ky Lh Lx Lz Mb Mf Mh Mj Mk Ml Mr Mt Nj Nv nY Oa oE oF Oh Or Pb Pe Pk Po Qc Qd Qm qV qW rP rQ rW rX rY sC Sr St uM Un vl Vp Vu wJ wK yH zA) iH(Aa bA bZ cT Ha Im Kc Ko Kp Kr Lx Nv Pb Pk Qg Qm Qn Qt Qw Qx qZ Rc rS Ub vl Vu Tj) dB(hL Im Jr jV Kc Ko Kr Lx Ny Oa Pk Qd Qe Qn Qt Qv Qw Qx Qy Rf Rm Tv Vp Vu) uM(cD cU cV cX dC Di dR Gl hC jL Kf Kg Kn kQ kS Nb Nd Om Or qP uR vT) Bc(Aa Ap Ar Bb Dl Js Ko kQ My Nm Nn No Nv Ny Qc Qm rS wP) Ko(Aw aX bC cC Ch dN EF fP Jh Jk Kz My Oy qU) Ny(cV dE Hq Ib Jd Jk Jv pF Pi Qh Tn yJ) An(Ed Fw Nv Pb Pg Qm qU Vu Tj) Jk(Cs Dl Ij Jg Nv Om On Ua Ut) Pk(aN dC Fn Ha Hf Hq Jh Kq Nt) Aw(Aa Dg Dl Gl Js My zA) Fn(Hx Ii My Nv Qe Ql Qm) Hx(aI Dp Hb hL jV uO) Ib(Dg Dl
Nm Nv qZ Vo) Jh(Ap cC Dg Ez Om Ua) Kr(bC cC dR Jf qU rA) Qm(aD Dp jV Pa pF Qh) cF(Ap Ax Dg Dl Kq Nt) hV(fY jQ lK rT vP zG)
hW(aQ cY jR qO vP vV) yJ(Aa aM Kc No uL vT) zA(Ch Cq Dd Ef Kc Pi) Qt(aN cC Hc Kz pF) Js(Fy Hq Jd Jv Qh) bC(aN Dg Hr Nm Nn)
Ax(qU qX Ss Uv) No(Jd qU Tn Uu) aQ(hL jQ Kq lK) cY(hL Kq Ld rT) cC(Jd Qw Tn) dN(nY uN uP) pS(Nh Nl vT) uR(dE Iu vI) pF(Aa Kn rS)
Nt(iA qU) Tt(Ip Qe) Tv(Hq Qc) Oy(Qu uL) aN(Ar Cs) rT(jR vP) AatS BbTn DbvI DlUu FwHw FyIp GlcV NmcD LxvT NhHr UecL HbrA
QcKk SrlK KsqU NvbW dRuI eCjV zGqX uLuN vBvP} tV{Ne(AN aQ Ax Bb cI cQ Cs cU cY dB dH dK Fp gL Ii Ij iP Jg Jm Js Kr Lh Mx Nh
Nv nW Nx Ny Oa Om Pi Qd QH Ql Qm qQ RB Ri rR rS sM Sr uM Vt Wm tF) Aa(aN Ao aQ Ba cB cF Ch cM cR Cs dA dB dE dH Dk dL dN
Ef fP Gp hB Hf hG Hx Ib Ij IZ Kg Kk Kz Ld lM Mj Nb Ny Oa oK Or rW sF Vt wE wQ) An(aH aQ aU Cp Cs cY dB Dk dN Dp eC eF fP hB Hx
iP Iq jE Jh Kr Lu My Na No oK qH Ql Qm qT rA rQ rW uL uM vT Vu zG Wm) Kr(aA Aj aN aQ bI cQ cR Cs cX cY dB dN hG Hx iP jE Js Kz
Mg My Nb Oa Of Pg qG qX Qz rW sC Tr Tt uM vP vV) Qm(aN aR bR bU cB cF cR Cs dB dH Fa FP Js Jv Kf Kk Kn Mf Ml Mt Oa Of Ou Oz
Pk Qd qX Vv) dB(aF Ax cP cR Cs cV dK Fp jO Kf Kn Lu My Ny qI qT qU qV qW rB rS rT uL) Bb(Ao aZ Ba dE Dk Dp fP Hc Hu Iz Jd Jk Mg
My Oa Qy rA uN wH wQ) Cs(aN cF cR cX dN fP Hx iP Js Jv Kz Mg Mk Of qH qQ rB rS zG) Js(cR cX Dk dN eC EF fP hG Ib jO Jv Ld Mj qI
Qx rB Ut) Ql(aN bI cQ cR dN eF fP Hc Hw Iq Jh Jk Mg My Pg Tt Vv zG) Qd(aQ cR cX dN Dp hG Jv rB) Oa(dN Hx jO Kx qQ uM zG) aN(aQ
Fp Il Ip qT uL Vu) dE(bU My oK rR rS uV tF) dN(Ij It Mt Nm Nv Qe) fP(Fp Kn Ko Lh Ny) Dl(aQ Na qH) It(cR eF hG) Fp(nW rB) Nm(Aj aQ)
No(hG Tn) Mj(Ij Lh) Hx(Kn sI) Ip(cB tF) Ld(aQ jE) Ri(bO jG) LuaX MtbQ ImHc HfrS IrnW QchG QhJk JrrB VucQ aHqZ} oW{bU(aC aO
AR aU bE bF bQ cE cL cN cR CS Cv dH Dr Fp Fr Gn Ha Hc Hq Hr Hu iA Ib iH iP kF kI Kl kQ Kx Kz Mk Ml mS Mv My Nd Nf Nj Nx oK oP
Ou Oy Oz Pa Pf Pz Qu Ua Uf Uu Vo Vs Vv Yg Yj) cR(Aa aJ aO aP bA bH bL bM Bo bV Ch cI cM cN Cw cZ dG Di dM Ef fR hB hG Io iP Je
Jh Kc kF Kl Kr Kx Kz Lt Lw Me Mf Mk Mv Mw My Na Nm Nx oD oQ Pd Rv Ut Wf Yj Yl) bB(aS aU Aw bA bF bZ cE cG cL cM cQ Cs cT
dF Dk dL Hq iP kI kQ Lv Ly Mj Mp mU nR Og Ou Oy Pa Pd PF Pg Rm Uc) cM(aI Ar Ax bF Cs Cw Ex Fp Hc Kf Kn Ko Kx Ky mE Nd Nj Oy
Pb Qn To Ul Ur Wb) nR(aI aL Ax cJ Cs Ha Hb iJ Ko Mn mT oP Qe) kF(bX Cs dR hB Kn kQ Kx mT mY Ng Pd Pf Ut) Nx(bF cL Ct Dk Fp Hq
Nd Og Ou Oy Vs Yg) Cs(bZ cI dM iJ Mj Mk mT Ng Vi Tl) Wb(cD Kl Mj Pa Pd Pe Pf Pg Ql Wd) aO(aI aL bX cJ cX dC dD Kx Mk mT) Ko(Ap
cD Dg Dl Fp Kl mS Pg Vs) Oy(Al Cv Dd Ha mT Tt Ut Tl) Me(Hc Hf Kx Nd Uo Wc) Yg(Dd Ks Mw Ng Tv Yi) Xa(aJ cN dG dM Hq iP) iJ(Hc
Kl Kx Kz Pk Uc) Ax(cE cQ iP Mk Vi) bF(aL Ng Pk Ud Ut) Dr(Mj mS nU Vq) Wc(Ao Dd Hu Rj) Vi(Aa bL Fp No) mT(Ic Kl Ql Rm) Ct(Cv Va
Yi) Yl(cN dM mZ) Ut(cL cT Hq) Pa(aW bI Yi) oP(Fi We Yj) Fa(mZ Rm) Hb(Dk Vq) aL(aW dH) cQ(Ha No) dD(aW bM) dM(kQ Sj) AaGn
AlHq DdPs FpRf FwbZ GbKl MhKx MjVt MkcL YiRm YjUr VzoQ WdmZ WebL RvRj RtVs VbPb PePg cEcJ} Qe{Jj(Aa aF aN aO bM dB
Dd Et Fp Im Jg Jn Jq Jt Jv Lh Lw Lz Mc Nj Nm Nt Nu Nx Ny Og Ou Oy Oz Pb Pc Ps Tl) Aj(Ad aN Bb bC bM cM cQ Cv dB Dd Dg Et iJ Jg Jt
Jv Kg Kq Mg Mm Ne Nh Nl Nm Nn Pb Pd Qb rB rC St Vt) Og(aN Et Fp Hu Im Jg Jq Lw Nj Nm Nt Nu Nx Ny Oy Oz Vz Tl) rB(aN aS cF cI
cU hG Kp nY Or qQ sK tN To tS wC) We(Cu Cv Dd Jt Ko Kq Lh mE Nb Nm Nx Rb Rj Vi) Wh(cQ Cu Cv Cw Dd Jt Kg Kq Kx Ml Mt Nm Nx
Qn) Aa(Hp In Iu Lu Lw Oe Of Oy Pc Ps Sf Sh Ye) Et(Ap Dg Ef Hu Kl Ms Ng Nq Oe Of Oy Oz Pb) Ye(bU cQ Db dC iJ Jn Ly Mb mE mS Ng
Rm) Ps(aG cM Cu Db dC Dr iJ Jn kG Nt Nu Qw) dW(aF bO bS Cq cR Fw Ip Jh Mb Nq Nu Oe) Nm(aA Fp Hp Hu Im Ms My Ng Oy Pb Pc)
Sf(aJ aW bS cN Cx Dd dX Ng Qn Ut Tl) Oy(aN cM Cv iJ Im Jg Nu Vt Tl) wE(An cF hG jO JV Tt Tv) Zw(cQ kG Kx Lz Na nK No) Fd(cM kG
kP Mj mS nK) aN(aC aF Ne Nh Of Oi) Hp(Dr Hw jQ lK Wb) Im(Hu Jk Ms Pb Pg) Lp(iB jL jO lL Ur) rS(cF dB Kd Ou qX) oP(bU Dp Gn Up
Yj) Jv(Cs Ki Ou Vt) sK(dN jO lL qZ) jL(Ux Va Vh Yd) Gz(qI vB yE) Iu(aF aM cM) Tl(Oz Sh Uu) Rm(pH Vi Yi) iJ(Mg Wd Yg) vT(sJ Tt Tv)
Dk(pI Vi) Dr(dG Nh) Gb(Oi Qn) Mb(Dw eW) Hu(Jg Nu) Tn(Kq Wn) Yd(lK lM) Ou(Pk Vt) Pg(cB Vt) cM(gZ Yh) dN(qQ tN) qU(dB Hf)
oV(Mj nR) AfEw CsNh CwVb DcoD DdSh EfKq FnTk GdOr HlmU TrKl TvtN YgkG WbQn WntF UuVh VajG ViVp aZeQ bUmS cTwQ
tSqZ hGwB iPyJ qXuV jOqQ} jV{Zx(aD aE aH Ar aX aZ Bc BO bU bW Cu Cv cW dE Dk Dp Gb Gl Gn Gp Io Iq Ir Jn Js Jy Kn Kq Kx Mr Qa
Rm Ry) Sr(Aj Fd fR Gn Gz Hl Ho HP Hu Jj Jk Kr lM Mg My Of oK Oy Ps Qt Qy rS Rt Rz Sf Vw Wh) Rv(An aQ bJ cC cD cY DB Dg Fn Gb
Hx Ih Io Iq Ir Iu Jo jR Kk lK Lt Mg Ng Nt Qw Uf Vw) Js(Dr Gz HP Ib Io It Jj Jk Jm Ly My Nq Oy Ux wE Tl) Rz(Et Iq Jd Jn Jt Kn Kq Mg Mm
Ng Nu Qa Ql) Dr(aD dF dK Ex Jr Mf Mp Ow Pf Qb Ql Qm) Hb(Fi Gb Lp Ps Ry Uw Uz Vb Vi Wg Tl Xa) Lt(aD aH dD Ij Is Ld Lx Mj Ml Oh
Pe Qx) Gb(aI aM Ar Bb dK Lv Mk Or Qm Tz) Yl(cD dK Kd Ql Qm Ru Tz Ul Vc Vt) Tm(Cw Ex Kn Lh Ny Ow Si Un Vt) Ux(Ar Ij Iq Lx Ml
Oh Ou Ow Po) Vw(Ar cF Cu Ld Lz Ow Qg Qx Tz) Va(aD Ij Jq Lh Lx Mj Or Pf) wE(Cs Fp Fw Kr Qd Rf St Vu) Iq(Gh Hl Hp Rt Rx Sh Wh)
Si(Fw jT Ni Nu Ql Tz) Sf(Fw Jj Nu Po Qg Ql) mW(Af Ar As Bn Ph rZ) rS(cI Cs Kk Qd qX rA) Un(Fd Gz Uy Wd Zw) Vb(Cv Il Ir Jo Pa)
Vh(Ar cF cQ Mx Tz) Ps(cF Jn Qt Ua) Ar(Uw Vc Wb) Cu(fR Hl Lp) Mr(Rx Wc Ye) We(Is Jh Jq) Kk(qA qH rW) Kq(Of qH Wd) Lh(Gz Vi Xa)
sK(Cs Jf Qd) Fd(Fw Po) Mm(Sh Vc) Wh(Dc Jn) Qg(Zw Xa) Ye(Ni Rm) Tl(dK Tz) Ry(cC Vt) Qm(HL) Or(Kr Qx) Uw(aG cF) Vi(Jk Tt) dB(rV
yD) hP(Cs dA) AatN FpwQ MfSh MkRx HpRm IlLp VzQl QdhG WccC WfOu KlmZ RtPh NyqA TkcQ VccU UydK VtuM aSnT cHnN fRhX}
nK{Yl(aI aM An Ao aZ bA bI bN bR cA cD cM cN cR CT CX cZ Db dH dM Et iJ iP Iu Jn kF kI kP Kz mH mM Mn mP mS mT mU nB nJ Nx
Og Oi oN oT oV Pd pI Qn Rj Wb Wf Tl Tj) Vz(aC aI aK aL bB bU cD cJ cN Ct Cx cY cZ dA dD dM eF Et Fd hG iP Iu kG kP Lh mH Mn mP
mU nA nJ nT Nx Og oH Oi oT oV Pd Qn Rj) Yh(Ao bB bI cJ cR Cu dD Dr Fy Hu Ij Il iP Iq Jl Jq Jr Kq Ks Lh Mn Mr Nn Nq Nv Nx Ny On Ou
oV Qh Qu Rb Rg Tn Tz Ut Vu Yi) We(Al Ao Co Em iP Jm kI Kq Ks Mf Mn Nn Nq Nr Nx oK On Oz Pc Rb tF) Ye(Al aZ cR Dd dM iP Jm kF
Ks Mb Me mT mU Ng Nx oK ON Qz Rj) oV(Ax bE Cv Fa Fp kQ Kx Mk Oz Ps Qv Rv Uw Vq Wd Wh) Dr(aC aK aL An bE cJ cY cZ dD kP
mS Og Pa Qv) Yg(cR Iz Kq Lh mE Mn Nn Nq Nx On Qu Ut Vu Yi) Rv(bN cM Dd kG kI kP Ks lW mU Nl Og) Ps(aH cR Cu Et Jn Kq Lh Nq
On Ou) Wb(aC aK bE cZ Ml Mn Oi Pa Vw) Tl(aI cJ Jj Og Oy Oz Pa Pb Vs) Vb(Ao Jm lW mT nH oN Oz Pb Pc) cR(Fd Lp oD Uw Wd Wf Wh
Zw) Xa(cD cN Ct dM mU Og Oi) Nx(Sh Va Wd Wh Yi Zw) Mn(Rt Sf Si Yd) Yi(cM Ct Lh Oi) Vi(hB hC No Nq) cU(jU lL qT qX) Uw(Kq On
Ou) lN(hX My oP) Et(Sf Vh) Fa(Fd pI) Zw(Ks Lh) Wh(Jn nT) Lp(Al oT) Va(Dd Me) lL(aZ bX) CtRt YfkP FdHa YjOg SfaI SjoH RceP KcrA
RxoT UyaH VwmT bZlM cHjU cWiB} Gz{yE(aA aD aN As bA Bc Bn Bo bV cC cD cH cJ cM Cp CQ Cu CW dA DC Dd dG Di dL dM Et Fp

Figure 41 Continued

Fw Hv Hw Hx II Ip Iq Is Iv Jg Jh Jl Jo Jr Js Kg Kj Ko Kq Kr Ky Lh Lv Lw Ly Me Mi Mj Ml Mn Mp Mq Mr Mt Mx Na Nb Nf Ni Nm No Nr Nt
Nx Ny Oh Om Or Ou Pb Pd Pe Ph Pk Qa Qd sC uG uM uN uP uU uY vA vH vW wD wF yJ yK tL) qZ(aA Al aM AN Ao aQ Ar aX bG bW bX
cL cV Cw dD Dg Di Gl hC Ii iO iP Iq Jm Jn KQ Kr Lx Mk Mw Nc Nj Nl Nm Nn Oh Om Or Ow Qa Qc qO qP qW) Kr(pY qT rX rY rZ sM uM
uN uV vI wF wH wJ wL yD yH yK yL tM tL xA) uU(aK bW cD cF dD dE Di Et Hb Im Jr Jt Mn Ms Nx Ny Om uR tM) qU(Et Fa Hb iP Is Jq Jr
Kq Ky Lh Mm Ms On Qd Ql Un Vq Vt) vB(aN Dl Et Gl Hv Hw Ij It Jt Kn Ko Mn Mp Mt Nx pS Qa tM) Dl(hL uG uV uX vI vW wH wP yL zA
zG zI xA) tM(Ad An Bb Bo cM Is Jg Jn Jt sC) sM(cJ dH Ih Jt Kf Kk Kq Nx) cD(uP uX vI vW wD wP yL) Hb(qP rZ sC uN vW wF) aN(rZ sC
uX wF wH wL) yL(Bb Bc Bo Jn Ms Pk) ql(dD Iu Lx Mt Qb) Bo(uX wF wL) Hv(qQ wE yD) Kn(wF yK xA) aW(lY mS oO) zG(Kf Kk Mt)
Nm(eT eZ) Hf(qV xA) Un(qY rA) aJ(uV wH) pY(Dg Tt) qA(Gl Ny) qH(bG bX) qG(Is Nv) uI(Kq Nu) uR(dA Mr) MtuZ UceT IhqB IiqO IlmS
ImyH JlqT JsrB KdvO LhjU QmfY OfuX dCvU rAqX qVrY} Un{uM(Aj An aQ cV CX cY dN eC hG jE Jk jO Kk Mb No nW Of Pe Pg Qc qH
Qm QX rB rS rW sK Tt Tv uR uU uV uX vA vH vO wE tF) vA(Aj AN aQ aV aX Bb bG bO bR bU cF cQ cR cY dA dE dH Hc hG iP Iq Jf Jk
jO Jv Lz Mg Nb Ne Of Qm qQ Qy rS rW zG Tj) rS(Ba cF Ch cI cY dB hG hP Hq Hx iA Ib Iq jE jF Jk JO Kk Kp Mg Ng Of Pz qX rA rW sK Ss
Tt Uc Uk Uu Vv yJ) uX(Aj AN Bn cF dH Ef hP Hq iA Ib Jk Jv Kk Kp Mg Mn Ne No Of Qx rB Tt Uu Vv yJ) sK(Aj An cQ dN Hq Hw Jf jO Kx
lL Lu Mg Ne nW Qm rB) hP(aV cA dA Hc Iq jO lL Mj Ne Ug Uk uV vH) vT(Aj AN Hq Jk Mg Of Pg Tn Tt Tv yJ) uG(Ef Hw iA Is Jk Mg Ne
Nq Of rB) An(qH rR uR uV vH vO wE wJ yJ) iJ(aC eF Oy Uy Vb Wc Wd We) Of(qY rC rT rV uI vO tM) yJ(dN iP Kk nW Ny Qm Qx) rW(aN
cF Iq Jk rB Tt Tv) hG(jO qW rB wE zG tL) qH(Jk Jv lL Ne rB Tv) wE(aN Hq Hx iP Qm) jL(Vz Wd Yl Zw Tl) Mg(uU uV vO tM) Tv(sC uL vP
vV) eP(lW Ps Qv Va) Ne(aC uR vO) iB(Rv Sf Wh) tN(dN My Tn) vV(Iq Kd rB) Dr(bO iC) Nm(Uy Vb) Jk(uU tM) Jv(Cs vP) cY(uI vO) dX(Sf
Yf) jG(Ux Yl) jO(Rz Zx) lL(Vi Yd) AabM DdSh EmqY ExeZ FnsF FwPs GnOz MnuI IssI SjjU QcvW WemE WhQh XaOi TmjT TlbU VwjQ
aNrR cFuV dNsJ iAqZ zGjF} Lh{Wb(aM aW bO bS Hp Hu Jj Jv Mh Mj Mk Ml Nc Nm Oi Oz Pb Pg Ps Qn Qw Rm Sf Sh Ua Ur Uu Uv Uy Vp
Vv Wh Yd) Sf(Aa aF aW bS cE Dd Dr eF Fw Gb Hb Kd Kk Ko Mk Ne Nm Oz Qn) rB(aN Ap aQ cY dA dE hG Ib Jj rO sK tS uL uM vV wQ yJ
Wm) hP(cF cM dA fP Jj jO lL Mj Mt Ne Nf Of oH Oi Qx vH wH) Uy(Aa aF aO bS bU Dr eF Jj Nm Nt Oy Oz Ur Uu Vc) Wh(Aa aF aO bS Dd
Jn Kd mS Nm oN Qn Vc) jO(aN cF dB hG Ib Jv Qy sK tN uN vA yJ) uM(aN hG jE Mj Ne Of qX qZ rS rW Vv wQ) Sh(Aa aF bS Dd iJ Kd Kk
Ko Ng Nm Qn) Yd(Aa bS eF eP Hb iA iJ Il Og) We(aF Dd Jn Jt jU mE mT Nm Qh) aN(qT vA vH vT vV wE wQ yJ) hG(iZ nN qH uL vA vT
wE wQ) lK(cW fR Ib oN Si Sj Vh) Dr(jL jU Qw Uu Uv) Ne(tN vA vO vT yJ) Zw(bU kR mZ oN Vc) Va(eP iB iC jG jU) wQ(An cF cT Hw qX)
iJ(eP Hc Vb Wc Wd) Mj(qH rS vA vT) Im(Jj Og Oy Pb) dX(iA pF Sj Uv) dW(aF bS bW Fr) mE(Bg Rx Yg Ye) hR(nJ oO oP oQ) qX(sF uI uV
wH) Vb(Cu Dd Nm) Vc(bO Fw Uu) dB(Jv qU rS) nN(aO aW cL) mM(jG lL rZ) Ex(sM vS) Gb(Uu Uv) Wf(jT lL) Jj(Aa Fp) Jk(rQ sF) Xa(Oi
Vs) Rv(Oz Qw) fR(jR jU) sI(Hx Pa) rA(rS vO) qU(dE fP) oP(Gn Yj) AjNm EwMn YgnI SiiC WcnO YemT TmlL JvqH KlnT KrwJ PsnL
KzhW LpUr VhjK VijU VvzG cFvA mPlM iPyJ iZvO} eW{Et(Ad Af Aj aN aW AX bA Bb Bc Bg bI Bn bO bR bS bX Ch Co cP Cq cR Cs cT
CX De dN eM eP fR Gd Hw Ii Io Ip Ir Is It Iu Jg Jh Jk Jo Jq Ly Mj Mk Ms Mv Mw Nj Nq Nu Nv Oe Of Og Oi Om Oy) cB(aD Aj Ax BG bM
Bo bR Ch cJ cP Cs cT Cv dC Jj Na Of Oh Oi Oy Pc) Mb(aE aF aR bE Bg bQ bR bW cC cF cL cP cS cV dI Jo Ma Ni Ns Qb) Ik(aC aM Ar bA
bB bM Cs cW Fp Gp Ij Iv Jr Lv Nd No Oh Po) Bo(aD aH aM aO aP Ba cD cM cS Ct dC DG Hr Nm Pd Pf) Jj(aK aN aW Ax bB Cs cW cY DC
Gl Ir Jq Nm Nn Oh Po) bB(aD aH Aj aN bG bM cG cL Cs Ct Fw It Jo Mg Nv Of) Oh(An aQ aX bS cL cO dX Hq Jo Ma Mg Of) Lv(aD Aj aV
Bc bS dM fP Gp Of Pf Pg) bM(Af aR cR Cx Hu Il Im Mv Mw Nu Nv) Ly(aK aQ aU Cs cY Gp Il Ir Mh) aD(aG Aj aU cY Dw Gp Nv Oe Oi)
aM(aR aS aX cF cR Dd Mv Nj Nu) bS(cW dG dL Hw Hx Jl Nn No Qa) aQ(dN Iv Jr Nd Nj Nl Oz Pb) dC(bH bU cC cP Mt Nt Of) Ct(Cu Dw Gp
Ij) Hu(cP Mt No Pa) aX(cP cW Ni Po) Hx(Bn De Dk) Af(Ir No) Aj(Mt Nn) Ch(Jq Pa) Po(Ip Mq) Gp(eM Og) Mn(cV Jh) Mv(cC Mt) Nj(Mr Qb)
Qa(cX Fr) Jo(aU Cw) Nx(aC Of) Oz(Ax bA) BaMu DlPa EfIs GdNn MkaF NeOi QbbO OfcI aKbP aRcW cPcZ} Vt{sK(aX bC bR cF cI dB dE
dN Ed hP Ip Jf jO Js Kd Ld Lu My Ne Ni nW Qm qX rB Ri rT uM vB Vu zG) uM(Af An aQ cQ cV CX dB dC dH hP jU Jv Kk Mb qH Ql Qm
QX qZ rB Ri rT uV vO Vu wE) Cs(aC aP bH bM cM dB dE Fn Fw hG Il Jv Mj Ne Nh Nn Oe Ou Oy Pe Pg Wm) aC(aF Ar Bc bM cM dB Ed
Fp Fw Il Jv Ne Nh Nm Nt Nu Oy Pk Sr Ur Wm) Fp(Aj bM cM dB dE dX hG Il Jj Jv Mj Ne Nf Og Ou Oy Pg Qx vO) vO(aA aQ aX cF dE Fa
Fw hP Ip Md Ne rQ rX rY rZ) vA(cF cR dH Ip lK lO Nv Po Qy rQ zG Tj) yJ(dK iP Kk Kr Ld Ne Ny Ql Qm qZ vT) bM(Aa Aj aR Ax eF Kr Ne
Oy Pk Qg) Ps(bB Cu Dc Fy Jn Jr No On Ut) Aj(Et Il Kq Ks Ne Nm Nn Nt) vT(Jk Jv Mg Ne Nq rB Ur uY) Vb(Ad Ao Cu Cw Dg iJ Nm) Vh(aW
bU cM lN Mw Pg Qv) lN(Dr Ry Wf Yd Yl Zw) Ax(cM dB eM Mj Ou) Kq(Dk Ef Jh Jv Ne) Wb(Kx Mn Nm Oz) hP(rQ uG uX wF) qX(rS rV uI
uV) Wm(eF Kr Ne) Gn(Ii Nm Qc) Jv(Dc Kr qH) Qm(uN wF zG) dB(rS rT zG) dX(Ar aX Sf) eP(eM lW Tr) iJ(Pk Wd Wf) jL(Hl Rt Zw) lK(qH
Vc Yd) Dr(Cw jU) Fi(iB lL) No(Hp Ib) Vw(Oz Pb) rB(rW uG) wE(aX Ne) lM(Va Yd) CuFd DdSh FwPg NmSf NtOy NhsI YicD SijT JkrQ
JoVc XaiB YemT KkzG KrwJ RtjU PkhG aNrR aQuI aWmS bCwP cFrW dErT fAmE} sF{Jk(AA An Ao Ap dE Dl Et Ez Hr Ij Jt Ko Kq Kr Nd
Nm Nn No Nv Nx Om Pa qZ Sr Ua) Fn(bZ cC cL dH dR Fw Hx iH Kc Ki Ko Ky My Nb Nm Nn No Ow qG Ql Qm Qz Ra Ug Wm) Ko(Aw BC
Ch Co Cp Ef Hu Ib Iz Jd Jh Jv Mg Mv Mw Nc Ne Nl Nq Oy pF Ua uM) Kr(Ad aV bE bJ cL Cx cY Fy Gp gW Io Jg Kl Mn No Of Pz qU Ss)
hG(aF Ar bA DK Ip Kc Ny Pf Qn qT Qw Qx Qy vI) Aa(Ad Bc Ch Cp Ef Fy Jd Kj Kl pF Rc Tn Tr yJ) Hr(aX BC Cp dE eF Hu Jd Jv Nc Nh Nq
Qt) An(dH Ed Ez Jh Mg Oy Pb Pf Qh wF Tj) Ib(bV Di Dl Et Ez iH Ij Iz Tr Uc Uf) No(hV sK vA vO vT vV vW wE wG yJ) Qt(aN bV cC cO Ly
Mk My Pa pF qZ) iH(bA cT hW Jv Qg Qm Qw Qx Rc Vu) Oy(bA cC Dg Ez Qm Qu qZ Tr Ua) Vu(aE dG dN fP hB Mk Nh tF) Jh(Ap cC dE
Dg Nd Sr) vT(dR jE Js Lx Nt vV) Hx(Ct Dp Kq pS wJ) uM(dC Iv Nb Nd Pi) Nm(Ct Jo Ss Uu) Js(Hq Jv Qh yE) aQ(hL hW jQ jR) dB(jU Qn Qw
Qx) Aw(hW My Nn) Cs(aN Iu Je) Ju(Co jE Ss) cL(Qv Rj Ue) dN(nY Oa Tv) hP(qQ rW vP) rS(aY Bc pF) vI(oK rR uR) Ap(Bc Of) Bo(hW Qn)
Dl(Ss Uu) Ez(Mg Pf) Nn(EF) Hw(Fw qC) Tn(Dg Et) Qm(aY Pa) Pk(dE tU) hL(cY jR) jE(qZ vO) AxSr BbQh CqrW CtUg DeNh DieF GlcV
MgcC QwPa KsqU NyqX fYhV} Dw{Ct(aC aF Al Ap aW aY BC Bg bM bN bO bX cA Ch Co CW Dc Dl Ef eM Gl Ih Ii Iq Iu Jh Jm Mb Me
Mg Mp Mu My Ng Nj Nm Nq Nx Om Oy Pa Qc) Mb(aD Af aS aV Ba bL bP bR cC cD CP cR cX Ew Fp Hx Jg Jl Jo Ly Ma Mf Mg Mx My Nb
No Nr Oi Pa Po Qa Qb) Lx(aE aH aI Aj aL Aw aY bA bH bP bS cC CP cX cZ DB dD Dk Hr Il Jk Jn My Nt Nu Nv Of Pz) aD(aI AJ aK aL AS
Ba bB bE bN Bo bR cA cJ cP cV dD Ip Ml Mp Of Qb) Aj(Ad Ap BC Bg bO Ch cM Co Ef eM Gl Io Jh Lv Lw Me Mp My Ng Oy) cX(BC Bo
cC Cw Ef fR Io Lu Me Mg Nj Nx Om Oy Qc) Nj(Af aS bI bO bR cA cP cT Ew Iu Mr Ni Nq Og) aM(aY bO dC dI eM Fw In Jl Js Nh No Po Pz
Qa) Of(Bg bO cD Ch Co Dd eM Hv Io Lv Lw My Ng) Bo(aG Ao Ap Ba Dg Dl Ef Gd Nu) Gd(BC Cq Jh Mn Nq Nx) Mn(aE aH bH Em Jh Jt)
Jg(Ad Co Iq Jm Jq) Nx(Ba Bg Ch Dl Og) Bb(aK Al cB cM) Ml(bB bM bN bU) bR(bX Cp Ni Nu) fR(Af bN dL Jj) Bg(Ch Jq My) Jo(Al bC Ii)
aG(aH Cx Mp) bB(dC It Nu) bM(Dg Dl Il) Ba(cW Pa) Lv(bQ cL) Mf(Af Jj) Oh(aF bW) bN(dC In) cB(cT Mk) CscZ CxaW DgcW DlQc EfGp
FrQa MuJn IkaY QbbO OyeM aHdC aOdL bXcP} Im{wE(Aj AN aQ aX aZ cF cQ cR Cs Cw DB dE dN dR EF Ex fP Hf hG iA Ib iC iH iP jO
Jv Kr qX rA) Jj(Aa bM Et Fp Hu Iq Ir Jt Lw Lz Mc Mh Ms Nj Nn Nt Nu Oe Og Oy Pb Pf Qd) Og(Aa Et Fp Hu Iq Ir Jg Jl Jq Jt Lw Lz Ml Nj Nm
Nn Nt Nu Oy Pb Pe Qd) Et(Fp Hu Jk Lz Mh Ml Mp Ms My Ng Nj Nq Oe Of Oy Pb Pc) vO(aM An cB cF Ch cR dB dE Ef fP Hc iZ Jv Kj rA rB
Vv) sK(Aj aN cF Ch cM dN Ef Hc Jf jO Kg Kr Mj Ne nW rB) Fp(Hu Jk Jt Lw Mc Mj Ms Ne Ng Nm Nq Oe Oy Pb Pc) Hu(Jg Jl Jt Lw Lz Ms Nj
Nn Nt Nu On Oy Pf Qd) Oy(Aa Iq Jl Jt Lw Lz Nj Nn Nt Nu Pf Qd) rB(aN aS cI uG uM uV uX vH vT vV) tN(Ch Dk dN Ef Hc Iz Jk Mj) Aj(bM
dB Nm rC uL uX vT) aN(aC uL vA vH vT wH wQ) Pb(Jl Lz Mh Ms Nt Nu) cF(rS uM uX vA wH wQ) yJ(An cM iP Kr nW Ou) Ng(Jg Jt Nm

Figure 41 Continued

Nt Nu) ul(aQ cY Ic Kk qX) vA(An cR dH Jf Nc) Ye(iB iJ mS mU) uM(nW qX qZ Tv) An(vH vT wQ) dB(rS uV uX) sI(cV Hx pF) oD(cR Dk
Ps) Ch(uX vT) Ef(uG wF) Ex(uX zA) Nj(Ms Ne) Sf(bS Qn) Jk(rQ vB) wQ(Hf Ou) hG(uL vT) uV(dE qX) EwaM MhPc MjqQ HlmU HpjH
WdiJ TloP KrvV PsiC UofB VcjI bSdW bUeQ dHwH rArS nWuN} iB{Ux(aM Bg bS bV cC cF Dg Dl Ez Hb Hf Hp Hq Hu Ij It Iz Jq Ld Lx Lz
Mk Ml Mp Oi Ou Oy Ph Qb Qg Qm Qx Qz Rg Rx Rz Sh Ss Tn Tz Ua Vw Wd Wh Zx Ye) Va(aI Aw Bb BG bN cC Ch Em Hf Ik In It Jj Ju Jv
Ms Mv Og Oi Oy Ph Po Qm Qn Qt Qz Rc Rj Sh Tt Wd Wh Ye) Ye(aS bM bR Db dK Ih Iq Ir Jl Oe Pe Qc Ql Sr Ug Vc) Hp(aS bM bR Ih Ii Ir
Jm Ps Qc Sr St Vc) Yd(cC CH dI Ez Hx Mn Qc Ru Sh Ul Vc) Lp(bR bU cD Dr Ii Iq Jn Nm Oe Qm Sr) Zx(cH Em Ez Gp Hx Il Mb Rc Rt)
Dr(bC bM bW cD cX Ju Qz Sf) Uw(Aw Ez Hu Jh Mu Mw Qy Ua) Vc(bC bW dH Fn Hu jE lK Uf) Wh(Ad cP Dd Fd Ic Nt Vh) Vw(aX bV cF
Mh Ml Oi Tv) Ho(Aw Bc cF Jj Ph We) Sh(Dc Dd Il Iq Kg) Wf(cD Db Nt Qm Sr) Qz(Fd Hl Ps Wd Zw) As(kC kF lY mH) Bc(Fc Fi Rt Rx)
We(cP Dc Jq Nm) Lt(cI dJ Em Ii) Vh(Ef Ru Ua Ul) aR(kC mM nD nJ) aS(kC nT Tm Tl) mW(bG De Iz rZ) Fc(aE Ir Pk) Fi(aE aG Ir) Hl(In Oy
Rc) Hc(mZ nD nH) Ps(Jq Mj Oe) Tk(Aj Ng Qu) Uy(Cp Il Mh) Vq(Rv Sf Zw) bR(mT nT nU) Fn(Ru Vz) Sj(cC Et) Rx(Ap Dg) dB(nT nU)
nL(bL dG) AjkF ArTl BgkC DcWd EzRz NmVb IlSf HbWc WbbU VzSr SiRc QcmM KrfR bBnN cBmT sIrS} iC{Va(aD aG aH Aj As aX aZ
BA bB Bn Bo Ct cW cZ dA dC Dl dM dN Ed Hl Ho Ic Is Jg jH jK Jt Ju Jv Ki Ky Ld lK Lv Mb Me Mf Mk Mm Mn Mp Ms Ng Nr Nt Nu Nv Oi
Or Ou Ow Pa Pb Pc Pf Qc Qx Rx Ry Si Ss Tv Vb Vq Vw Wd We Wf Zx) Dr(Al Ap aQ Ar aY bC bE bP bR bS cO cP Dd Dg dN Ex Ez Hc Ik Iz
Jd Jh Kc Kg Nd Ng Nr Oy Pd Qc Qw Sj Sr Uc Um Ux Vq) Si(aE Al cC Cv Db dF DK Fn Hf Io Iq Mf Nc Nd Ne Nj Nl Ns Or Sj Ux Vo) Yd(cH
dK Hx Kd lK Mn Nc Nd Ne Ni Nl Nn Ph Ru Sj Ul Vc Wh) Ux(aG aR aX bN bS bV dB dG Ez Hb Ic Ki Lu Mf Ph Tt Tv Ue) aR(Gb kO kP lX
nC nD nL nO nR nT nU Sj Vc Zx Xa) Vc(bS bW Cw Dd Dg Fn Jo Kg Mf Vq) Ps(aE aG Cx Hu Mw On Qn Qy Ug) Fn(Hl Rt Ru Wd Wh Zx)
Mf(Gb Lt Rx Uy Vw) Hb(Fc Hl Ho Rt Wc) Lp(aE bU Db Dk On) Zx(Em Hx Mg Vo) Wh(Iq Jt On Pa) Tl(dK Jq Js Nl) aG(Fd Fi Ho Rt) Cu(Gh
Rt Vb) Dc(Vz Wd We) Gb(bS Cw Lv) Ne(Ho Rt Vh) Hp(Dl Ih On) Wf(Iq Jn Qm) Ad(Wd Zw) Sf(Hf Nd) Ye(dB Dl) Qm(Vb Vi) cU(kO nN)
wE(Js Oa) DgRz EmLt FdIi NmHl NuVi NhVh IcXa IqWb VzQc ShOn ZwUg RuVq cSnN mWrZ} Ye{mT(Al aO aS aW bG bI bJ bU bV cE
cM cN Cv dB Dd dG Fy Hv Hw iA Ih Ii Il IP Iq Iu Iv Jm Kg kR Ks Lp Lu Me Mf Mx mZ Ne Ng Nm nR Nx Of Qg To Ut Uy Vq Vs Tl) mZ(Ao
Ap aW bB bZ cJ Co cR Dd Et iJ Jo KG Kj Ko Kq Ks mE Mg Mm Mn Mr Mu Mw Na Ng Nn Nq Nr Oz Qt Qu Qz Rb Rt Uf Ut Vu) mS(Ad Ao
bJ bU Dd Hw Ij Il Ir Is Iu Jo Jt Kg mE mI Mm Mn Ng Nm Qc) mE(aF aM Ax bI cR Cs Et iP Jn Js Ks Kx Mf Ml Mn Nm Nx Rg) mU(Ao aW Co
Hw Ij Jo Kg Mg Mm Mw Nn Nq Om Qu Qz Ut) jO(Al aP cP DK Fr Fw Jd Jg Jl Nt Nu Ux) iJ(aF aO bF Ha Ii Jn Mf Mw Ng No Qa Ut) lM(Aj
Fw Gl Ib Jr Nm Nv Oy Po Qa Sr Uc) Qm(jE jH jK jL jQ jR) bR(jF jQ jR lK Ut) cR(mI mW nA nB nC) jT(cM Hf Ii Ug Va) Ao(kO lW nB nR)
eP(Mt Mw Ni Nu) mI(iP Mn Mw Rg) kG(Il Ng Pz Rj) lL(dK Ex Nt Nu) cM(Nm Nt Ut) nR(Kq Mg Mn) mM(Et Mm Oz) jl(Db Ug Va) kP(Dd
Nm Vq) Ne(jE jH) Qc(jQ jR) dX(Mw Wm) nN(Al Nx) jU(Fw Rm) lK(Jq Vc) oP(Iz Ng) DljF NoiO HwpI JhjQ QzpH KgkI QljG UtlW VajK
nAiP nCnL} rB{tS(Cs Cu Fa Fp Ih In Jl Js Kn Kr Lv Mq Mt Nm No Nr Nt Ou Pd Pe Po St Tt Vu) Tz(Af Aj aN bU cF cI Ct cU kR nY Or qU rQ
rR rS sK vU wC tM) Js(aN bG bM cV hR iZ Jj lM nY Or rO sK sM tN Um wC yJ) Fa(aN cI cY Dp eF Of qH qO rW uR vO vP vS vV yJ)
sK(Cs Fp Ha Kk Lx Oa Qd Qh Ql Qm Ri Sr St Vu Wm) tN(Cs Ed Fp Ih Ij It Kk Kr Mf No Pk Qd Qm Qz) Kk(qA qD qO qP rQ rS rU rW sC vU
vV yJ) Qd(aN hG hR Or Rc rP rQ vV wC yJ Wm) Sr(aN bM cI Jj Kz lM rQ Ug wC tM) Jl(cI cY qH qO qP rR uM vP vV) Wm(cI nY rP rR rV
vT wC tM) Mt(hP rW vP vV wJ yJ zA tM) Jr(aN bG bM cJ rO rS uM vU) sC(Lx Lz Mp Nu Rg Tr Us Tj) Vu(aN rO uG uM vT vV wC) Cs(rQ
uO wC wF yJ yK) Ql(rQ rS vU wC wD wF) Fw(uG uM uV vO vT) Or(Aa aN cI uM uR) Fp(uO wC yJ yK) Oa(cI Og rW tM) rQ(aN Kn Pk Rb)
Cu(Jj Of Ss) Kr(rO sI wJ) Ny(qA vU yJ) cI(bG iZ Qa) dA(Rh St Vp) vV(Fy Kq Lx) Po(rO vP) Ha(zA tM) Is(uM yJ) Pe(mW vP) wC(In No)
vT(Ed Ou) ExqZ FyrW IhcU QanY KnrO UurP PamW dBrV qXuV} jL{Hl(aG aM aR bR bS bV dK Hr Ic In Is Ld Lx Lz Mf Ml Nf Or Po Qb
Qc Qx Rv Rz Vc Yd Zx) Dr(Af Ap aR Cw DK Ex Fr Hc Hu Ik Jd Jh Jr Jt Mf Nf Nr Nt Pd Pf Pg Qy Tz Um) Vc(Ad Ar aY cP Cw Dc Dd dG Dk
Ex Fw Jd Jh Jt Kp Mm Pd Uc) Zx(Ad Aj Cu Dd Dl Ic Is Jt Kf Mf Mg On Ug Zw Wm) Ux(aM Is Jq Ky Ld Lv Lx Ml Or Pe Po Qa Qx Rz) Ps(aR
bS cC Cw Dc Fn Hu jE jF Kc Mf Mg Vh) Va(Dk jI Jn Kk Kq Lx Mj Ny Om Pe Ql Uw) Vw(aM Ld Lz Ml Nt Or Qx Rg Rv Rz Tz) Rz(cP Dg Jd
Ng Nt Pd Ql Sr Uc) aR(Gn kO lX nC nL nN nT nU Ry) Ho(aG dK Hr Ne Pz Qg Tt Tz) Yd(aP cP dA dG dL Ex Fw) Uw(Cv DB Io Mf Nm Ug)
Vh(cC Dk Iq Nh Oe Rh Tz) Si(bU Cv Dk Fi Fw Tj) Qc(Gh Gn Vz Wd Yl Zw) Gb(Dc Lv Mf Or Yl) Vi(aS bF bN Ko Ug) Gn(cO Et Qm Qy)
Rv(Jt Ng Nh Ug) Yl(bR cB Nt Ug) Hp(Dk Po Qm) Hb(Fc Fd Wc) Vb(Ad Jt Nm) aE(Lp Rx Wf) Tz(Rt Uy) Tl(dK Rm) AwfR DcGh FdNe IqSf
IrWe WbbU VzcB ZwSr WcaG WdcC WfJn JqLp JskF KnhP LtOn UydK PhmW sIuM} jE{Yd(aG bR CH cM Ct DD Em Ez Gb Hb jF Jj Jn Kd
Ky Nc Nd Ne Ni Nl Nn Ph Qc Qm Ru Sh Ua Uf Uk Ul Vc Wh Zx Xa) uI(Ar cJ Cv dH Fb Fn hF hP Jd Kk Kn Ko KR Ld Nx Ou qX Rf sJ Vv tL)
sI(Ap Ax Bb Dg Hr Ip Or Qg Qm Qn Qv Qz Rj Ue Ug Ur) Vc(aG aI Ao aV bH bQ bZ cI cM dD Fn Hb Pf Zx) Yl(aG Ao aV Ba bL cB cM Ct
Em Gp Ky Uk Vz) rS(cI Cs Kk Kq Kr Ks Ld Nx Ny Qd Ql Ri) An(rQ tQ uR wD wE wF yL zI) Zx(bJ Ic Io Kx lL Mg Ni Ri) Kr(rV sK tN tQ uY
wB wD yJ) Hp(Ih Ne Nl Po Qc Ql Qm) Wh(bB Ef Jh Mg Qa Uc Zw) Lp(bR Dr In Po Ps Qa Qm) Rv(cM Ct cV Dg jG Qu) Vh(aG bR dD jF Mr
Uk) uM(Jl Kk Ld Nx qZ Vu) Dr(Ao bB bH dD Qm) Fc(aG aH Nc Ni Nl) Ne(Gh Gn Hl Sh Vb) aH(Fi Rx Uy Tl) bB(Ru Rx Va Xa) jG(Ps Vb
Tm Xa) rT(Fa Mt sJ Vq) Gn(Nc Ni Nl) wE(Cs Fa Vq) vO(Fa Jl Lz) Wc(cM Dc) Kk(rV vU) Ps(cN Qa) Rz(dD Dg) Ld(tN uY) Ou(Fi rV) Vi(Ic
lL) aG(Ry Zw) aN(qZ rC) sJ(hL Me) GbaI HbTm HcmZ JdsK WfJr TlQl KxmT RxjK NyyJ VadD PhmW bMqZ} lK{Vc(aC aD aH aI aL aO Ar
aU aV bB bE bJ bQ bZ cE cI cJ cM cU cZ Dc dD Hb Is Jj jK JQ Jr Kq Kx Ky Ld Mj Ml Mn Mp Mt Nq Oh On Ow Oz Pg Qh Qx Rv Vi) Dr(aD
aP aV BB Et Fr Hb In jI jK Ky Lp Lv Lz Mh Mj Mk Ml Mp Nv Ny Or Ow Pe Pg Ph Qb Qd Qg Qm Qx Rg Rt Rx Tv Tz Uk Uw Vb Yd Yl)
Yd(aD aH Ar cC cH cI cM Cs cZ dD dJ Ed Fw Hf Is Jy Kr Ky Ld Mp Mq No Ny On Or Ou Ow Pg Ps Ql Rv Sr Uw Vi) Vh(aH aM bR cB dI dJ
In Is jF Jq Ky Oi Or St) Qc(Fc Fd Gb Gn Rt Ru Rv Uz Vb Wc Wg Xa) Zx(aZ bB cL cM dB dJ Hf Ii Oi Ry) Vi(aO bV cL dB Hf lL Nf Ph Rz)
Sr(bS Hf iA Kz nW Qy) Rz(aI bB cV dD On Qu) Yl(bS bV cB cD Hf Oi) Ps(cN Hp Ih Oi Qa) qH(Ar Dl Kn Ql) Hx(Uw Ux Vw) Si(aI On Or)
Jq(Hp Lp Tl) Rv(aP cM Jf) Oi(Ry Wd Zw) Va(Ky Or Ou) aS(lX nN nT) cU(mT mU nD) Dc(Vb Wd) Mf(Uw Uy) Hb(Fi Gn) Hf(Lp Zw) Tl(Lx
Nu) nN(aP dG) DemW MkRx HoIn UaUx UcOf HvsI QyQm KnhP QlrS NyqA OrUy UwaR VbcM aGfR cHmT} Nm{Vb(Ad Al aM Ao As Ax
bU cD cM Cp CQ Cs Cu Cw Dc Dd Dr Em Fw Gd gL Hv Ii IJ iO iP Iv Jm Jr Js Ju Jv Jy Kd Ki Kn Kq Kr Lu Mi Ml Mr Mt Nb Ng Ni Nr Nu Oi
Om On Pe Pi Pk Qn Rb Rj Sf Us Vi Vp Wb Tl) Aj(aC Ad Af Al Ar Ax BA Bb Bc bM cB cI cM Cs Cu Cv dA dB Dc Et Fa Fp Fr Fw Ii Iq Jg Jk
Jm Kq Md Mr Mt Ne Nn No Ny Og On Pf Pk Qa Qc Qd Sf Si Vi Wb) Sf(Al aM cM Cs Cx eF Hb Hv Il Jj Jn Ju Ki Lx Lz Mh Ml Mn Mw Nb Ne
No Og Oi Qn) Sh(aM bB Dd Gd Hv iP jH Jj jK Jr Ki lM Lx Mn Mt Mw Nb) Wb(aM Cs Hp Kx Lz Mh Ml Oi Po Rg Uu) We(eC iZ Jr Kq kR
mE Nb oK On Vi) Fp(Hu Jg Jj Ms My Ng Ny Og Qd) Wh(Cs jH jK Jl lM Nb) Vi(Bg Jj Uu Vs) sI(cY Pk vV yJ) lM(Hp Lp Va Yd) Gd(iP kR
mE) Og(hP Ir Qd) Uy(Jr No Rg) qX(rS uM uV) Dr(Of Rg) Ps(Jr Lx) Rv(cM eC) Uu(mS Zx) EfKq ExeZ MgrQ HpJl QdJj QvfA XaiP TmjK
RyOi YlmS UofB VacM VvsJ PkaC bOoP dNtN mWhR qHuM qQvA} dW{Bo(aC aD aG Ao Ap aY bA bB bC bE Bg bN Ct dC dD Dg Di Dl
Fr Gd Hu Ih Jh Mh Mu Mw Nd Ng Nu Of Oi Oy Pe Pf Pg Pz Qa) bS(aD aL Ar aS bB bI bZ cC cF cO Db dC dF Et Gl Hx Is Jn Jr Lz Mf Mj Mk
Mq Mt Nd No Nr Nx Oe Oh Om Pe Pf Po Qa Qb) bB(aD aE aH aN Ap aW Ax Bg Ch Ct Dl dN Ef EM eP Fp Ih It Iu Mb Ms Nd Ny) Mb(AF bR
bU bZ cG cL cO cP cS dB dI eP Hq Hu Jl Lv Ma) aM(aR AX bA bR bW cO cP cR Db Di Ew Jj Ma Mn Nj Pa) aF(Aa cC cU Gp Ij Is Iv Jr Mf
Mx Nq Pf Qc) Lx(bN bQ cH CV Jj Mw) Mu(aO bF cE cL dH dL Lu) cB(Bg dK dN Io Mk Of) cX(aN bF bG cC dH Nx) Lv(aC aV bN Mt Nh)

Figure 41 Continued

We(Ad Qc) Yl(bJ Jt) Rf(No Sr) On(Ps Vi) Uu(Rz Yi) DdYf NqWd MnLt mWrZ nJhR} oP{Gn(Ao Dg Ij Jn Ks Mm Mn On Ph) We(Co hB On Ph Qu Rz) On(hR Ki Up Uu Yj) bO(Cw Fy Mm Uf) hR(Ma Mm nl Nn) Yj(Jn Mn Ph) hB(Ur Uu Tl) Dp(Al Ha) Tj(Tr Tt) Sr(iZ Og) Wc(Dg Jn) Rz(Ct Uu) Up(Ha Nq) AxcS DdQv FbOg NoTl KpfR aMdC} tS{qZ(Aj As Ax Bo Cs dB dE Dl Dp eC Fw Gp hG Hq Hx Ih IP Jh Js Ko Lu Mf Ms Mx Ne No Of Oy pS QA Ql Qm Qy Ri Uk zG) nW(Fa Fw Jl) Ne(Gl Ny) Kn(dB Kz) zG(Kp Ld) BoRi DlqQ IpiP OudN} Fp{Jj(Ii Ij Jg Jm Jn Jt Lw Mm Nt Nu Nv Nx Ny On Oz Qc Qd) Og(Ij Jg Jt Lw Me Mm Nt Nu Nx Ny Qd Wm) Jg(Hu Jh Lw Mw My Ng Oy Pb) Jt(Lw Ms Ng) Hu(Nv On) Nx(Ms My) cM(fA gZ) LwNy QdOz blgZ wQqZ} eQ{Ha(cA Mf ml Pg Pi Ps Qh Rv Vp Vs Yd) Mn(Dr kQ Ps Qh Rt Si Sj Tr Vs Vz Yd) Kx(aF aO bF Lv) Ks(Ps Va Yd) Oz(Fa Gh Ho) Nn(Dk Nd) Ij(Yd Tl) Ps(Jn Ph) Pb(Ho Yi) AoVo AxMj CqQh DcIr DrNr NoVi MwIb OnaO PhbF bBmZ} qW{kF(Af bE bH bJ Bn Cx Kc Ki Kk Or Ph) nT(aS bH bJ cl cU Dl Kc Kk) Kc(kC kN lW mF) Or(kC kN kP mF) cU(lW mW nB nO) nN(cH cQ Kk) lY(aM bG Ki) aR(kO lX) bH(kC kP) kK(bG Dl) kN(As cY) HcmZ aGkO aSlX bJml fRtF} pH{eC(aF aO cL dH Fd Fn Jl Or Ou Ow Ps Qn Tn Tr Tv Tz Vp Vs) Rm(Al Ax bl bJ Ha Ir Iu Jn Mn No Nr Qa Sr Yi) Dk(Hb Ko Yi) Yh(iP Lz) Yi(Pg Vs) Wc(Me Rj) cM(Tv Vs) nR(bB Mn) MjHb TlOy KsPg QnVi} tN{Dl(Aj Ba bC cl Dk dN iP Jh Jk Mg My Ng Of qQ Ss) Ip(Aj aR Ct eT Uk) dN(Fw Js Ko No Ou) Ne(iO Ny Qm Ri) Ny(Jk Mj Oy) nW(Ax Pk Tj) Qm(aR ql) zG(hL Oa) qZ(Jh Oy) kR(Cs Ko) AxOf NoTn Luql MyKn TteT} fA{Ax(Ao bG bl cH cM Cw gZ Hw Hx iO Lp Ng Pb Rz Ss We) Cw(cD Cs Ic Mg Rc Vv Yl) aO(Ko Mk On Yl) cM(al bE Cs Ml) bl(Qv Yh Yl) Yg(Ng Pc) Ko(Pf Pg) AlDp DkOn FacH FbcD FdRj FyUw YlaZ RgbX alnR} We{Oz(kG mF ml mM nD nJ nL nU) Ij(kG Mf oF oK oN pF) kG(Al Hw Il Ng Qc) Jt(Jr Mf oK Or) On(aO Dd Fw Kd) Ng(kl nR nU) Dd(Jl Jr) Jo(iZ kl) mZ(bZ Mn) iP(nN Yi) AdlO CwkR MwnR QunH KoaM Pbml} Wh{lO(Dk Ef Fn Jh Qy Ua Zw) Jn(aM Dc Dd iP nY Qh) On(aF aO Dd Ki Qn Vp) Kx(Dc kR Pz Qy) aM(Ef Kg Ng Nt) mZ(bZ Nn Nq Uf) Dd(Jl Po) No(iO Kg) AonB BcbB CsIz CwkR DcPo NtcM IhkG QaiP JlKg} Qm{Vv(pS rW uN vW wD wF zA zG) wQ(dH Fa hL Lx Lz Mt Oz qQ) wE(Cs Fa iZ Mh Mt qQ) Ne(qA vU yE) cB(wD wF Tk) Of(wD wF) aW(lY mM) qA(Kk qZ) lO(Wf Yd) TvuP JfsK dAuR dHsM dNwF} mZ{Wd(bZ Co Ef Nn Nq) Yl(aW bZ cN cS Og) Dr(al bB cJ Qv) Mm(Gd Gn Vb) Mn(Hp Lp Rt) Rz(Ct Pb Uu) Vj(iP Rg) GhOz HaaW HcqY YgbZ YdQv WfbX RtUr UfOy UuVh cCeD mWrZ} No{Hp(Aw cM Cv iO iP Mb mU oF oN) Vi(iO iP kl kO kP mW nY) Ib(Cq Rj Tv Vv) mU(Rx Rz Wc Zw) wQ(eC Iz Pk Ur) Ps(Dc iO) DkhG YgiO VzRf JkrQ TlPc} gZ{Oz(bC bl bR cM dH Fa iO Ip Ld Md Mq Mt Ns Nv Nx On) cM(aM aR Ax Cs Ih Tr) Pb(bC Fa Mq Vj) bl(Ar Cs kQ) Mn(Rt Wc) bG(Ko Kx) KsVa OnaO} hR{nJ(hW Jr kC kF kO nD nH nL Pa Pc Qc qY) nl(Hv kC kF kN mF mW My Nc Ni) mW(Iu Nn Pc Pe Pf rZ) Js(kN mM nD) fR(aR cM) HvkE QcoO JtoQ} wE{Fa(cY Hx Rb Ur vS) Dl(cU Mg Ng qQ) Fw(Bb iP Kn zG) iP(dL iZ qZ) Ri(iH Ne) aZ(dH Ou) hG(Po Qd) BbEd GldE MtbQ HrVu HxqZ RbrQ StdL QlyE OazG PkdH} Qd{rQ(Aj cX hG Hw Jk Ou pF Tt Tv) Jj(Jn Nt Nx Oz Pc) sK(cK dN iO Ri) qQ(dB dN Ml) NuOy TvpY JurW cNvT cXqA dNwP hGrU qZvV} dH{vO(Ch fP iA Ne pF) wJ(iO iP Ko Pk) zA(Ax Dl iA Ko) pF(uL wF wH wL) Fw(wH wQ) Lu(sK sM) Pk(vA wH) qH(bX Dl) NevT NiuR wQiP iAuI} mI{Mn(Si Vz Yd Yg) Tl(bB Oy Oz Pb) Rg(Dr Wf Yg Zw) Vz(bB iP oD) Vb(kl Oz Pb) Dd(Ki Oy) Rx(Pb Pc) iP(Rv Wc) DrcZ IlYh YgbB YlOg bXqY} cD{Yi(Fw Hb iP Jj Mx Oz Pb Pc Qn Rx Uv Vp Zw) Gb(bB eC iP Kx) Dr(bB Kx) Fw(Vc Vi) Rv(Dd eC) DcRt IjYl HbVi PsiP RukI} aW{Yl(lY mU mY nC nJ nO) Vz(nC nJ oD) Rv(kG kl nC) Fc(kl lY) Lp(kl lY) Ri(nN sK) CsVh DrKx GbhC HonC YdoD OgnN VbnH VikE} qY{kK(Af Ao Ap bG Ct Cw Kk Ow) Kl(fR kF kN lW) nT(aS bJ cN) lY(aM Ap bX) cU(kC kO) lW(bH bX) kF(Ad Aj) KknN PhmW} Ne{Nv(tU vA vT zG) Wm(uR vT vU) Ny(qA uN vU) vO(Fa Fw Oa) uR(Fa Ha) AdAj PovA GlvU HplO TzTk SruO JluZ KkrW RisK NxrR} lO{Lp(DK In Iq Ps) Yd(Db Ph Qw) Wd(Ad Dc Dk) Fn(Vb Vc) Hp(dK Dr) Ux(Ph Tt) Vh(Kd Ph) FiaG GnNi MgVb InVa ItPs} Jl{qH(Hr Kk Nn Nq) dN(sK wH wQ) iP(sK uR wQ) rW(Jk uR vO) zG(oN Ow) rR(Aj Jk) qQ(Nn vA) vO(cQ fP) mMrZ wQnW} Of{Ql(wD wF wH wP zA) uI(Kf Ou Vu Tj) Cs(uO wP yK) Uc(rC rX rZ) Dl(qH rQ) Ks(wD wF) Ri(rP rV) KorQ NyqA} Ny{qA(aY bC cM cV dD iA Ib Kp Mg Mn Tv) Jk(uN uP wP) uN(cM nW) DkrQ EfvU NtJj RczG dLvA} Uu{Ux(kE kG lW On) Vh(cM Dk Iz On) Kf(Vb Vc Yi) Rz(kG kl lW) Ko(Gd Yi) Uw(kP lW) GbOn MmnH JtYl} oD{Vs(Iz Ld Om Qz Rz) bF(dK Ld Qu) Ha(Mj Vp) Rz(Oz Pb) DkOn NnNd MwHq TtOy QaPs TlJy LdOz PbbC PePg} Ri{sK(Bb cB dA fN iP Jf oH qQ) aQ(rV wD) CvzG IcrP WckG KkrW cAnN dAvB dNwF fPvl iZuV} Cs{wF(dN eC hG) Kd(rN rQ) cM(oN Pk) wD(dN hB) DbVh GbmW IlQw JdQu JjKg KzqZ OgnN tUhG rTuO} Vb{Jt(Cx Ki Mf Ni) Cw(Db iA kR) Ao(Ii mU) Ng(Dr Oi) On(bF Dd) DcdC HwHb KgaM UxlW nCnL} kG{Yg(Il Ng Qh Rj Tn Uf) Ih(Ps Vi Wd) Wd(Ao Iz) Kl(Uf Ux) Rv(bX Dd) Rj(Fc Wc) IlYh} rZ{mW(Jj kK mM mY Na nD nO) mM(Hu Jh mU Po Qc) oO(Jj mU nD nH nO)} Dl{Aj(rQ sK vT) Mg(qH rQ vT) qQ(sK vA wQ) cU(vA vO) qH(Kk Ug) aQvU dDvV dNwF} Dr{On(Kd Ps Uv Vp) bO(Kd Kx Ru Sr) Ng(iP Ju) DdUk FwRg MnaS IlKx JnVp aMdC} Gb{aM(Fc Fw Hf Jn) hC(aO Cx Oi Qn) On(Mh Vp) nB(bB Og) AlJj NiKx JrVp QnOa} Vh{Jj(Al Hv Jn) Mm(nO oO) Qa(Mj Rm) aM(bP dC) cM(Ar Ml) FwPg NuVv MwHu bBnR cCeC} pI{Fa(dR mF nA) Fy(bF Dk Yd) bX(Ks Qn Vv) Ha(Fd Vp) Kx(bF dR) AxdR DdeC OznI} Kk{zG(cN Nc Nl Pk) rW(cN Nc Nl yK) qA(cX Ql) AjrP NcrQ TzTk bGqH dMsC} qT{mP(bH cU Hf Kf Ld Pi) cU(kC nD nH) Aj(kF kN) nT(aS aZ) OrkF aRnD} vO{Fa(aM Ch dL fN Hc Jo zG) Wm(iP nY uN) Ip(iZ nY) BbFw PoMj HaNq} Ps{Hb(Fw hC Lx Nt On) Jn(iP mW Pe) On(Fw mM) DcJj NtLx JtOr bBnB} Ql{wF(dN Jk pF Tt) aC(pY rW) wD(Tt vU) qI(wC yD) rV(Ch Ph) rQ(Jk Mg)} Tk{eD(aR cB Ng Vv) Mn(cX Pk) Mt(hG Lu) cB(bV eC) TzTv IrIu QutF aRgP} mU{Wc(aM Ao cG Jn Uf) Nn(Vz Yg) Qa(Hl Rm) FwVz MnRt NgRx YlPe bGeD} Sr{Tv(uI vU wG) Kz(hV hW) KiPk LdwQ RflY NxvA dBeC iPsK rVuO nWuN} dB{rV(Af aY dK Il Na nY Uk zG) Aj(Ad Jt) TvvT PkwD} cM{Nt(Rv Wd) Mn(Si Yd) dR(Vj Yi) DdRv EmKx NrLt KcqH UrgC} qV{aR(kC mM nD nJ) cU(kC kO) mW(Kc Ph) JskN bHkC bJlY} dN{wF(Ap Ar Dg Kl Ko) Mt(wH wQ) ArwD WmsK FawG} Vi{nB(bB Mn On) Nr(iZ kl) Qa(gP iP) MnbF IrRm} rQ{Ko(Ef Ma vA) Kn(Dk Jo) Uv(Ij Js) JkNx VviP} uR{Ar(dA Or wF) Wm(bS vT) oN(Lx Po) OriP UvPe} Fw{Tl(Oz Pb) nW(vU wQ) BbvA MjvT SiaM JdQu} Og{Dd(nN oO) Ir(Lw Vz) nB(Fi Yi) NtVj NuIj} Vc{bB(Bc dR kR) ArIl DcbO MnbG KxkR gLiP} Ip{Ur(sK wQ) hG(uU yE) TvuP JfsK iZuV} Wc{Ao(nA oT) Jn(iP oO) DdoO HwoT OniP} Oz{Bc(Fc Fi) NtVj YipF TlnL RynJ LtkP} Fd{Mn(mF nA) HamW IjnO OnVp bBnB} hW{Js(Ib wQ) Kz(cI rW) uI(aQ vV)} Aj{Ad(dA Lz Nc Nh) CvNt} Wm{qH(Qw rT) BbsK iAuI xAvU} Yi{iZ(aJ Dk Oi) ToJj cNhC} Tl{Jj(Ij Qa) AxUr NcQh PbnL} Kf{cB(sK vA vV zG) VvzG} Uw{hC(aO cN) YgkP UrlW aJiZ} qZ{HaNq LzpF MmiA OazG eCwQ} Hb{aM(Fc Fi) YdOn ZwKx} Rv{DdJj MjeC nNkR nCnL} Vs{nO(gL Is Mw oE)} hX{Em(Jq Tn) PemW aJfR} Bb{Qx(sK uN) dLvA} Gd{Jt(iP kR) MmnI} Nt{Vj(Oy Pa Pc)} Mn{Rt(mW nR) TmnR} Zw{NaQa IiUr KxkR} Kc{qH(bG rW) JfsK} Lp{Ur(aM iP) DbbB} Ux{Kl(Jn nN) cNhC} eD{nN(aR cH) GlfR} wD{sC(Kz To) VuaZ} kP{CtRz YgUf LtbB} oT{bX(Tv Vu) FyYd} vT{Fa(Mj Nq) HaNq} Dd{HpoO OynI} Gn{IllY cNnB} Mm{YdgC PkaC} Tt{PowH PewQ} Tr{Uv(sC uN)} Yj{HakR IqlW} Si{JsQn aOhC} Vv{NvzG rWuI} Pc{BcFc MhVw} nH{NnYg YlcN} rY{QcnT JsoO} ArTjoN DgcIpY EmbRhV FiPzJj HpHwnL JdiPsK KpcBzG LtbBnR OraQuI Constrained panels with 2 analytes, where 1.0E-8 >= 'AUC p-value' > 0. Contains 307 panels of 199,653 total panels evaluated. : Lj(aA bM Et Gc iJ Im Jg Ji Jj Jl Jp Jt Jv Lh Li Lw Mm Nm Nt Nu Nv Nw Nx Ny Og Ok On Pc Pj Qd Qe Uh Vt Wb Zq Wn) Ok(Aa Aj Eq Fp Hu Im Jj Li Lw Lz Mc Mg Mh Mp Ms Mz Ng Nw Oe Of Og Oy Oz Pb Pc Ps Qd Qe Rx Sf Sh Wb Yk) Gc(aC Aj aM eC Ha hC Ik Jj jV kP mS nB Nc Ne Ni Nk Oy Oz Pb Qe Rg Sf Uk Un Uu Uy Va Vt Vv) Ji(aA aC aN bM dB Fp hP Hu iJ Im Jj Jq Jv Li Mp Ms My Ng Nu Og Oy Pb Pc Sf Sh Si Uy Wb Yk) Nw(Fp Hu Im Jj Li Lw Lz Me Mh Mp Ms Mv My Ng Nj Nt Nu Og Oy Oz Pb Pc Qe) Li(AA Et Hu Im Ir Jj Jp Lw Mv Mz Ng Nq Og Oy Oz

Figure 41 Continued

Pb Pc pK Ti) Et(Fp Hu Im Jj Mh Ml Ms Mz Ng Nj Nu Of Og Oy Qc Qe) Fp(Aa Im Jg Jj Jp Lw Mz Nm Nx Ny Og Qc Qd Qe Vt) Im(Aa Hu Jj Ms Ng Nj Nu Og Oy Pb pK Qe) Qe(Aa Aj aN Hu Jj Ms Nm Og Oy Oz Pb) dU(bB Gp mE Mw Nj Oz Qc Ut Wf) Pj(aC Cs Fa jB Sf Sh Uy Vi) Ke(bM lM tO tR uM yJ) Id(No rC uG uI uM) Kq(Aj Ef Iz Jh) jB(aO aW bN Oz) jP(Dr Vc Vh Zw) Aa(bM Jj Nu) Cs(Jv Uh Vt) Yd(hA jD jY) cR(oD oT pK) Bo(dW cW) Si(hA jD) Zq(aM Mh) Qd(Jj Oy) Uh(bM tT) Vh(jY Vt) pK(bU Nk) AjNm DltT DuQy EoJr TitX EqJp EwaM MzhP ZxjD TljY LhUy YlnK VaiC VtaC PkbM bSeO tOqZ

Constrained panels with 2 analytes, where 1.0E-7 >= 'AUC p-value' > 1.0E-8. Contains 306 panels of 199,653 total panels evaluated. : Lj(Aa dU hG ld iO lr ls Jd Jq Jy Ke Kq Lv Lx Mg Mi Mp Ms Mz Nd Nn No Pd Pe Pg Qm Un Vw Ti) Qe(aA aC bM cM dB dU Id Ir Jg Jn Jp Jq Jv Ki Lw Lz Mm Mz Nj Nt Nu Ny Ou Pc Pj Vt Yk Ye) Aa(Et Fr Iv Ji Jp Lu Lx Lz Mh Mr Ms Mt Nn Nt Nw Ny Oy Po Qa Qd tX) Ji(aF Aj cB cl Cs EF Fc hG iH Qx Rc rW tR tS tX Vv Yd Wm) Pj(Ax bM Du Fp Gd hC iJ iZ Jj Jv lK Mz Or Si Uu Vt Wb) lm(Ir Jk Jl Jp Jt Lw Lz Mh Mz Nn Nt Oe Pe Pf Qd) Gc(bU cM eP Kd Kx Lz Mr nK Ns Ny Pg Ry Sh Us) Et(Aj Cs Jn Lw Lz Me Nt Ok Oz Pb Pc Qa Qd) Mz(Hx Ij Ir Jr Lw Ms Nm Nt Nu Ny Og Oy Qd) Fp(Hu Jm Jn Jt Lh Mm Nt Nu Nv On Oz Uh) dU(aW Ax bU Lt Mn nK Nn Pb pK Ru) Id(aC jK Jp jV lK lM Uh wF) Qd(Hu Mh Ms Nm Nu Og Oz Pc) Vt(Aj Ax bM dE Du Kr sK tO) Ny(Jj Mh Og Oy qA tT yJ) Zq(aC cM Eq jY Ki Kl) Uh(aC Ar Ax cM tX Wm) Jp(Hc Ic Iz Mh Sh) Ke(aC EF Jv qA) Eq(Jg Kq On Qu) Nw(aC bM Ir Mw) jB(cM dM mE Oy) Wb(Kx Li No) Jj(Jg Nt Qa) Lh(Sf Sh Wh) Un(Cs tO vA) bM(Bb Li Sr) Aj(Ad Jt) Nk(fA gZ) Yd(jE Ok) Zx(jY IN) Uy(No Nt) Va(iB jY) dB(rV tV) hR(nI nJ) pK(eC nR) CuVb DrhA DuiJ EoPo TiuW ExqH ljOg QuLi JsjV KlKq KrtV OpiB OnOy PkaC aNrQ cRoW wBjM Constrained panels with 2 analytes, where 1.0E-6 >= 'AUC p-value' > 1.0E-7. Contains 467 panels of 199,653 total panels evaluated. : Pj(Aj aM aN cB cF cM dB dD dL fP ld Ik Il jD jK Jp Ki Kl Kq Lz Oa Of Pa Rc Ry tX Un Vv Wm) Mz(aN aO Dd Jb Iv Jg Jj Jn Jp Lv Lx Lz Mh Mi Mx Nj No Pc Pe Pf Pk qZ Sr Uh uM Vt) Fp(aA Id Ih Ii Iq Ir Is Jl Jq Js Lx Lz Mc Mp Ms Nn No Oy Pb Pc Pz Qa Un Wm) Uh(aN dA dL Fa Gp hC iA iP iZ Ji Jj Jv Ki Kq Lz Ne No Oa Qe tO Uu Vt Vv) Vt(Ar cM dB Ed eF Fw hG Il Ji Jp Jv Kq Ne Nm Og Ou Oy uM vO Zq Wm) Ji(aM aO dE dU Fa Gl Gp Ib Ic Id Iz Ju Ki Ou rQ Ss uM Uu) Jp(aC Ar bM Cs Gc Jj Jv Kl Ms Nj Ny Oy Oz Pc Qd Sf Uu Wb) bM(Cs Dd Et Gc Hb Id lm Jd Js Kq Kr Oa Ok Qc Qd Qh) Qe(Fa Fn hG iJ Jt Ke Kl Lh Mp Nn No oN Qu Uu Vv) Jj(Cs Dc li Ij Ir Jm Js Jt Kq Lh Mn Nm Nu Nv On) Ny(Hu Ir Lx Ml Ms Ng Nm No Nt Oe Qa Qc Qd tR) Gc(aS cD Cu dD Jn Li Ml Mw Or Pc Pe Si Tt) Id(Ax Cs dD dL Il jQ Jv Kq Mn qY rQ tN Ti) Ke(Aw Ax Ch Cs dB hP Ne qU Sf Sh sO tT tX) pK(aO aW aY bN cM Dd dK jB Mw nK Nn) Cs(cM Fn Jd Jy Li Nk Nm Ok Pk tV) Et(aA aC Ax Dr Eq Ih Ir Jq Nn No) Jg(dU Hu Mh Ms My Ng Og Oy Qa Qd) On(Hu Mh Ms Ng Nj Of Og Oz Sh Wb) Aa(Jl Jr Lw Me Mm Pc Pd Qc tV) Lj(aC cM dB Gb Or Oy Pk Tn Vh) Kq(Ar Aw Bg Ch Dk Hc oP Ss) dU(Du Jf Kz Li Lp ml nN Vb) Ti(Ax Du No Nr Or Sr iT) Nt(Eq Ne Og Pc Qa Qc Qd) Wb(aM Ij Lh Lx Ml Po) Qd(Aj Ir Jt Lw Lz Mm) jB(cN kF mZ nK nR oP) Js(jD jU Ms Pc rB) Lh(hP jO Pb Vc Yd) Og(Ih lr Nu Oa Qa) Un(aC Ax Du uM uX) Eq(Cu iJ Ng Nm) Kr(Ar qH rS tO) Ok(aC dB Ef Kl) Th(mZ uL vT) Nm(Sf Sh Vh) No(Jv Sf Vv) Nk(eQ Vh Zq) Im(aA dB Iq) Qa(Nu Oy Pc) Sr(Ib jV rB) Ar(aC Jv) Du(fA mE) Lx(Hx Ir) Zq(Jv Oi) Li(Aj yJ) Nw(aN IM) bU(oW Vh) dB(rS tX) tV(Bb Qm) rB(Jr Tz) AxUr EoIs PohP FagV FrHu NuQc MnNh NgJt IrYk YicD SijP NvOy OpjD VqmS PkiJ aNsC bBoW mMIL mWrZ Constrained panels with 2 analytes, where 1.0E-5 >= 'AUC p-value' > 1.0E-6. Contains 965 panels of 199,653 total panels evaluated. : Uh(aF Aj aM As Aw cB cE Cv dB Dd dE Dr Du Ed Fw Fy Hw Ic iH iJ Il Ir jD Jp Kl Kn Kr Lh Li Lw Lx Md Me Ml Mt Nm Nr oN Or Oy Pb Pe Pj Pk Po QA Qd Rc sK Sr tN tR Un Yk Wn Ti) Pj(Ar aX bE bH Cq Cu dA Dc dH Ed Fw Gp Gz Ha Ic Ir Jl Ju Ke Li IO Lw Lx Md Mg Mi Mq Mt Ne Nk Nn No Nr Nw Og Ou Pb Pe Pf Pk Po Qa Qd Rg Sr tT Uk Us Tj) Id(aF bE cB cM Cu dB dK Et Fa Fw Hv Ic Jd Jy Ki Lh Li Lx Lz Mz Nk Nn Nr Ny Og Oh Ok Or Ou Pa Pf Qa Qd Un Us Vt Wm) Jp(Aj aN aO Ax Ch Dr Ed Fa Hu Ih Jn Js Ki Lx Lz Ml Mx Ng Nm No Ns Nt Nu Oa Og Ou Pb Pk Qa Vc Vv Yi Yj Yk Wm Ti) Mz(aA aC Aj Ar bM cl Cs dB Ed Hu Ih Iq Is Jl Js Jt Ke Mm Mt Nh Nl Nr Nv Nx On Oz Pb Po Qa Qc qT rB rQ rS Wm) bM(aC Aj Ar Ax Bc Cv Dc Ed Fa Fb Fp Ij jB Jg Jj Jm Jq Jt Kd Kn Lh Mr Nb Ne Nk Nn Nv Nx Ny Or Qa Qb rS Un) Ke(Aj aM aN cB cM dL Fa FP Gp hG Ib iJ Il Iz jD Jj Kl lK Nc Nk Og oN Oy Rc rQ uN Uu vU Wh wQ zG Wm) Lh(aA aC aN Eq hG Hu Ib Ih Is Jg Jv Ki lM Lx Mh Ms Nm Nt Nu Ny Og oN Ou Oy Oz Pc Qa Qd tR Uu Wm) Lx(hP Hu Ij Jg Jj Jn Jq Js Jt Ms My Nj Nm No Nt Nu Nx Og Oy Oz Pb Pc Pe Qc Sr Vt Ti) Cs(aC aM aN Bb dB Hb hG iJ Jt Kq Mm Ne Nh Nl Nw Og Oi Qd rS Uy Vv Wb Wn Ti) No(Hb hG Hp Hu Ij Ir Jn Js Ki Lw Nm Nu Og Ou Oz Pc PK Qc Ur Vt Yk) Nt(aA Aj Gc Hu Ih Is Jg Jq Js Lz Ms Ng Nn Ns On Oy Oz Pb Qb Sf Sh Vt) Jg(aA Aj lh Jn Js Lw Lz Mg Mr Mx Ns Nu Ny Oe Of Oz Pb Pc Pe Qb Qc) Ar(Aa bA Bb Dd Et Fn Ic Jd Jj Jy Nb Ne Nk Og Qc Qd Up Uy Wb Ti) Kq(aC Ba Ct eF Hu Ib Jv Mg Mv Mw My Ng Nq Of Oy Qu Sf Sh Tn Uu) Ny(Du Ib Ih Is Iv Jn Jq Jt Ki Lw Lz Nj Nu On Pe Pf Pk tN tX uN) Vt(aN aS bH cB dK Et Fa Ic Li Lz Nf Nn Nr Nu Pf Pg tT Um Ur Yi) Jj(Al Ax Dd Fr Fy Ha Jn Ks Mm Nn Nx Po Qb Qc Un Vh Yi Zq) On(Aj Jk Jn Ml Mp Mv Mw My Nm Nq Nu Oe Pb Pc Sf Uy We) Un(Aj aN dB dK Fw hG hP Ib iJ Jv Ne Oy Qe tR tT Uy Yk) Nm(aC Fa Ij Ir Is Jq Jr Js Mx Ng Og Pe Qa tT Wb) Zq(bU cD Ez Gd Ha iJ kP Kx Ml mS Ne Po Sf Sh Wb) aN(Dd lm Js Li Lj Nx Oa Ok Pk Qa Qc qT Sr uL wE) Du(Al Et Gb Hb Il iP kR Nu oN pF Qd Uy Vq Wb) Ij(Hu Ir Is Lw Lz Mh Mm Ms My Nj Nu Oy Pb Qc) dU(bH bL Bo cM Cw eC Fd lm Ir Kd Kl Me Nr oW) Ti(aM Cu Ed Ha iZ Nb Nk Oa Pe Po Qa Sf Wb) Nv(Hu Lz Mh Ml Ms Ng Nj Nu Og Oz Pb Pc) Js(Jv lM Nj Nu Og Ou Oy Oz Pb Pk Sf Ur) pK(bl dD eQ iP Jn Lj mE Ng nL nN oW Ut) Aj(Bb Bc Cu Dc Fy Im Ks Lj Nn Qa Qc) Pk(Ax cM dB dD dE dL Gc hG Ki Nw Sr) Mn(Dr Hu Iq Jr Mh Mr Ms Og Sf Sh) Wb(Gc Hf Ir Mh Nk Oa Oz Pe Qa Ut) Jv(Ax Et Fp Gc Jd Li Nw Qa Qd Sr) Ji(Ed jB jD Kl rS tN tO tT Vs) Jt(aC lr Mr Ms Mx Og Oy Qa Vb) Li(aC AX dB dE fP hG lM Uu) Uy(bB bU Cu Et iJ Nr Pe Qm Ut) Qc(Fr Jn Lz Ms Mx Nx Og Pe) Sr(aC hP Ki lM Lz Og uM Wm) Lj(aM bB cC dD Fa Op Tr Ux) jB(aG bI cF Ct Pb Pg Vs Vv) Et(Ap Ef eW Fa Kl Sf Sh) Nu(aA Ir Jn Jr Mh Oz Pc) Qa(Hu Ib Ms Nj Oz Pb Ye) Vh(aM bO cD cM Mw Ne Rg) Ax(Jd Jy Ok Or Qd Wn) Nw(aM cl dB jO rB rW) aC(Bb Hb lm Mm Qd Vq) Eq(Dg Mm Qd Ut Ux) Gc(Fa Im Ju Ky Oa) Ir(Lw Lz Oz Pc Pe) Sf(Dc Ii Im Mm Ou) rB(Im Oa Qe Rm tT) rS(cI iP Ql qX rA) Hb(dL Fi Il Wm) Sh(Fy Ii Mm Ut) Og(Fr Ii Jn Nx) Oy(Fr Jn Nn Po) tX(Bb Dl jM Qm) Dr(Kx Nk Ut) Qd(hP Nn Wm) Ok(Ch cl Uu) Pe(Hx Lw Oz) qZ(Gz tR tS) An(rQ tT) Dl(tO tR) Fa(Lu Nk) Fp(Jd Ne) Gb(aM Kx) Ha(Nk oN) Kr(qU yJ) mE(We Yk) hP(Jl Kn) tV(dE Ne) AatN ChJd CuWh EwNj FnsF FrNg FwvT MhJn XacD YemT KkrW OaUr VqwE bSdW dBtT qXuI kFoW Constrained panels with 2 analytes, where 1.0E-4 >= 'AUC p-value' > 1.0E-5. Contains 1,484 panels of 199,653 total panels evaluated. : bM(aA Ad aM aN bA bE cI dB dD dU Fr Fw Fy Ha Iq Ir Is Iv Jl Jn Jr Jv Jy Ko Kp Lx Mi Mm Mt No Nt On Oy Pb Pc Pe Pf Pi Po Rf St Tz Uf Up Vu Wb Yi Xa Ti) Ti(aC Al cM Dc Dd Dr Fa Fp Fw hC Ii Il Iq Ir Jl Js Kq Mi Mr mS Mt Nt Nv Og Oi On Pg Pk Qb Qd Qh qU Uf uP Ut Uy Vi Vq Xa Wm Tj) Lh(aF Aj aM aO dB dE Dr eF fP Gb hC iA iH iJ lr lv Iz jD Jn Jt Kl Lw Lz Mp My Mz Ng No Oa Ow Pj Qu rB Ss tO tT uM Uv wQ Yk) aN(Aa aC aF aM Ar Ax Bb cl Ed Et Fa Fp Ha Hb lj Ir Is Jn Jt Kq Lx Lz Mr Mt Ne Nk No Nu Nv Ny On Or Pe Pf Qd qZ rW tT tV tX) Wb(Aa As Ax bB bO cD Dk Et Fp Fy li Il Jj Js Ke Lz Mf Mn Mt Mw Mx Nr Nu Or Pc Pf Qb Qx Rg Rv Sr Uh Us Vh Yl) Zq(Al aO Ar bO cL Cs Cv dD Dg Dl Du Fw iP Ir It Mp mU Nc Nr Ns Oy Oz Pb Pc Pe Rc Rg Us Uu Vc Vo Vs) Qc(aA aC aM dB dD Ih li Ir Is Iv Jl Jm Jq Jr Jt Lv

Lw Ms Oa oN Op tR uM) Jd(Il Iz jK Kn Kr Lx Mg Pe Qa qH Rc Up) Vv(Aa Cu Et Ii Js Ke Nr Nt Nw Qa Qd Un) Cs(Aa jK jV Lw nN pY rQ tN uO Vh yJ) Sf(Ad Ap Ax Ih Jg Jt Ks Mw Qh Uh Vh) Qb(aA Ad Ir Is Jq Kr Lw No Pb Pe Pf) Ok(eF iA Ic jO oP Ou qH Qx Rc tR yJ) tV(Ax cI cR fP Hf Hx iP Kk qQ Rb uM) rW(Et Ii Jl Kc Kp Lx No Ny Qd Qe Un) Dc(Aa cI Ct Et Fp Mz Nh Nl Qc Uk) Mt(aA aO eP hG Ir Jq Ms Pb Pe Pf) Wb(aW bS Fw Kd Ld Na Nb Ng Ou oW) Jn(Iq Is Iv Jq Lw Mi Mp Mr Mx Pf) Nv(aO cI iA Iv Iz oP Ou qT Ss tR) Oa(Il Jy Lw mS Nl Oi oN Op Vh vT) cM(Ed hL nN Qa Qc Qd Qh Uw Vj Vq) qZ(An aQ Ex iA iP nY Pj Qe uM vV) rQ(Aa dE Kk Kn Ko Lj Pj Qd Ql Rb) Ar(fP hG jO Lw qH uO vU wQ yJ) Cu(Aa Ct Ef Ib Ic Of Ps Qc Qu) Ha(cC dL iH In mS My Na Op Yk) Mw(aA Jr Ml Mr Ms Pe Pf Uw Vw) Yi(aW cC iP Ju Oi Uv Wh Zq Zw) Jl(Ih Iz Jq Jt qT uM vA Yk Ye) Jp(aX cB cC dE eF eP fP hG iA) Kr(Ed Hv hW iZ jV Ny pY sC wF) Qm(iZ jK mM sK uM vU wD wF yJ) Vc(Ax cG dF Fp Fw gL Ij Kx Li) jB(aD bR eC Hc No Rm Tr Uo Vp) Et(dA Ed iZ oP Rc Ss tR Up) Ma(Iv Jr Lv Ml Ms Mx Nh Pb) Ny(hC hG Iz Ko qU uM UP) jD(Gc Qc Qd Qe Uw Vh Vi Tl) Ax(Aa aF cC Mc Mu Pb Pd) Lx(aF cC cI lM Mp oN Qx) Ii(aA Iz Ml Ng Nu Ss Yk) Ij(cI Cv hG Ib Iz tR Yk) Jq(Ih Mr Ms Mx No Pe Pf) yJ(Gl Kk Kp Nw Ql rP Vt) qU(dE Ex Gz nA Ql Tz Uh) jV(bA Ed Jr Rv Tz Un Vt) Fw(Lu Pg pK Uk uV wE) Fy(dL eF mS Mz Of Yk) Gc(hA iC jL jP jT lN) Nr(Lw Ms Mx Pe Qu Vh) Mn(Gz Ic Me mZ Nl oP) Id(dU eC eF fP uX zG) Il(eO hW Kk Ko Yl Zq) Qc(bE hC iP mM Nd Pd) Kn(dL eF hG qH vT wE) Op(jI Kd lO nB nN Us) On(aF Ef Hc Iz Ou Ss) Uf(Ch Kl Ng oP qH Ss) Vq(bF bL cC In lX pF) rZ(Gz mM mU nD nO oO) oW(aI aO bF cL dD Pa) vU(Dl Gl Kk Ko Ql Uh) Aa(aD aF cA dD hC) Cv(Cx Ed Mz Nb Vj) Lw(aA Is Iv Jt Pf) Mr(aA aF aO Ko Nu) Pz(aA Jr Lv Ms Mx) Nw(Ed eF hG Qx wQ) Uw(bO cD Ed Mf Qn) hW(cI hR Kz nW Qx) tN(Ch Dl iP jM Lj) vT(Ed Kf Ou Tv Vu) Ad(cI Ct Fp Wh) No(dE iA lM wQ) Ih(Iv Ms Pe Pf) Js(cI dD sJ tR) Ke(dE eP Pg Vs) Li(iA uM uN Zq) Uh(cC Ho rR Ry) Vi(bF bU Kx Qw) Pb(Ho Is Jt Pf) Pj(eQ hL sK wD) dU(cK dD Kx Mx) wE(dL Rm St Tz) oP(Ji Pe Qu Zq) Fp(aF aK Wn) Nt(eF Gz Ss) Ml(aA nN Vw) Mp(eP Jr Jt) Ir(Eo Ko nJ) Qd(Ed qT Yk) Xa(kR Oi pK) Ye(Is ml mZ) Kk(pY rV sC) Ks(hC In iZ) Ut(Hc Ib mZ) aQ(hL jQ wD) mS(aW Qe St) hG(bA iZ sH) An(pY wF) Dl(uN vV) Ex(Lu Yk) Fi(cD kR) Gl(lK tR) Nu(Mi Mx) Tr(qH Ss) Iv(Jr Pf) Kz(hL wD) Rv(kG nK) Yl(Jt Vw) Ou(qH vO) Un(oN Pg) Vb(Jo Kf) Vh(Kd Us) Pe(My oN) bU(nN Ry) cU(jO jQ) dL(Fb iA) gV(dR Vo) mM(aW Zq) wP(jM rA) hC(Lu Si) zG(Kp Vt) lL(fN hL) uM(Mq Vu) CqIb DguN MiJr MsIs MxaA IcnK HfpY QaaO QeqT JfsK WcpK WeKo WhKg PsjP RmpH QljK OmtR UpdK VajI PalM aKdA bBeO bEnL dFjO dHvO dMuR eFnN mYhR iZuI rArV

Figure 41 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Wm | % | 8.5E-2 | 2.4E0 | 2.1E1 | 4.3E1 | 1.3E2 | 7.4E1 | 5.4E-2 | 8.5E-2 | 1.0E3 | 1.9E2 | 151 | 7 | 151 | 7 | 0.64 |
| Po | pg/ml | 3.0E-1 | 3.0E1 | 8.3E0 | 7.1E1 | 2.6E1 | 7.6E1 | 8.0E-3 | 2.6E-2 | 2.7E2 | 2.2E2 | 341 | 12 | 341 | 12 | 0.83 |
| Et | ng/ml | 1.4E3 | 4.0E3 | 1.7E3 | 3.4E3 | 1.1E3 | 1.5E3 | 7.5E1 | 5.9E2 | 4.8E3 | 5.0E3 | 340 | 12 | 340 | 12 | 0.81 |
| Fp | ng/ml | 1.3E1 | 4.6E1 | 2.3E1 | 4.4E1 | 2.7E1 | 3.4E1 | 6.0E-3 | 2.3E0 | 1.3E2 | 1.3E2 | 343 | 12 | 343 | 12 | 0.72 |
| Fr | ng/ml | 3.5E4 | 6.0E5 | 1.2E5 | 5.2E5 | 1.8E5 | 3.0E5 | 1.9E2 | 7.0E3 | 8.4E5 | 8.4E5 | 348 | 14 | 348 | 14 | 0.84 |
| Nm | pg/ml | 1.3E4 | 5.3E4 | 3.3E4 | 1.5E5 | 8.2E4 | 2.4E5 | 1.0E-9 | 1.0E-9 | 9.6E5 | 8.2E5 | 344 | 12 | 344 | 12 | 0.74 |
| Nn | pg/ml | 1.6E2 | 8.3E3 | 1.4E3 | 4.9E4 | 6.6E3 | 8.9E4 | 1.0E-9 | 1.0E-9 | 9.5E4 | 3.1E5 | 344 | 12 | 344 | 12 | 0.85 |
| No | pg/ml | 1.5E1 | 1.6E2 | 3.2E1 | 3.1E2 | 5.7E1 | 3.4E2 | 1.0E-9 | 1.6E0 | 5.6E2 | 9.1E2 | 344 | 12 | 344 | 12 | 0.77 |
| Nq | pg/ml | 1.9E0 | 7.7E1 | 1.9E1 | 1.7E2 | 6.6E1 | 2.2E2 | 1.0E-9 | 1.0E-9 | 6.7E2 | 6.3E2 | 344 | 12 | 344 | 12 | 0.80 |
| Nr | pg/ml | 1.5E0 | 3.8E1 | 2.1E1 | 2.2E2 | 7.4E1 | 4.1E2 | 1.0E-9 | 1.0E-9 | 9.8E2 | 1.4E3 | 344 | 12 | 344 | 12 | 0.77 |
| Ns | pg/ml | 1.0E-9 | 1.0E-9 | 7.8E0 | 3.0E-1 | 6.4E1 | 1.0E0 | 1.0E-9 | 1.0E-9 | 1.1E3 | 3.6E0 | 344 | 12 | 344 | 12 | 0.51 |
| Nt | pg/ml | 1.0E2 | 3.0E2 | 1.3E2 | 4.8E2 | 9.9E1 | 5.2E2 | 9.8E-1 | 7.5E1 | 8.8E2 | 1.7E3 | 344 | 12 | 344 | 12 | 0.77 |
| Nu | pg/ml | 1.7E1 | 1.2E2 | 5.5E1 | 1.3E2 | 9.1E1 | 1.1E2 | 1.0E-9 | 1.0E-9 | 6.3E2 | 3.7E2 | 344 | 12 | 344 | 12 | 0.74 |
| Lu | pg/ml | 1.0E4 | 5.9E3 | 1.6E4 | 6.9E3 | 4.0E4 | 4.7E3 | 7.7E2 | 5.2E2 | 5.6E5 | 1.7E4 | 344 | 12 | 344 | 12 | 0.34 |
| Lv | pg/ml | 1.0E-9 | 5.9E1 | 1.5E1 | 6.0E1 | 3.1E1 | 4.8E1 | 1.0E-9 | 1.0E-9 | 2.6E2 | 1.6E2 | 344 | 12 | 344 | 12 | 0.78 |
| Lw | pg/ml | 1.0E-9 | 1.0E-9 | 4.7E-1 | 2.2E1 | 5.0E0 | 5.1E1 | 1.0E-9 | 1.0E-9 | 8.0E1 | 1.8E2 | 344 | 12 | 344 | 12 | 0.66 |
| Lx | pg/ml | 1.0E-9 | 1.3E3 | 1.7E2 | 3.0E3 | 5.5E2 | 6.2E3 | 1.0E-9 | 1.0E-9 | 6.2E3 | 2.2E4 | 344 | 12 | 344 | 12 | 0.84 |
| Ly | pg/ml | 1.0E-9 | 1.0E-9 | 9.1E0 | 9.1E0 | 1.8E1 | 1.8E1 | 1.0E-9 | 1.0E-9 | 1.1E2 | 6.0E1 | 344 | 12 | 344 | 12 | 0.53 |
| Lz | pg/ml | 1.0E-9 | 1.0E-9 | 3.2E0 | 1.1E1 | 2.6E1 | 2.1E1 | 1.0E-9 | 1.0E-9 | 4.3E2 | 6.2E1 | 344 | 12 | 344 | 12 | 0.63 |
| Ma | pg/ml | 3.9E2 | 4.9E3 | 2.2E3 | 8.2E3 | 6.0E3 | 1.1E4 | 1.0E-9 | 2.4E1 | 6.5E4 | 3.6E4 | 344 | 12 | 344 | 12 | 0.78 |
| Mb | pg/ml | 2.5E1 | 2.2E1 | 3.2E1 | 2.7E1 | 1.8E1 | 1.6E1 | 9.2E0 | 4.1E0 | 2.1E2 | 5.3E1 | 344 | 12 | 344 | 12 | 0.39 |
| Mc | pg/ml | 1.0E-9 | 1.0E-9 | 5.5E-2 | 1.0E-9 | 7.4E-1 | 0.0E0 | 1.0E-9 | 1.0E-9 | 1.3E1 | 1.0E-9 | 344 | 12 | 344 | 12 | 0.49 |
| Md | pg/ml | 1.0E-9 | 1.0E-9 | 5.7E-1 | 3.4E0 | 5.2E0 | 8.4E0 | 1.0E-9 | 1.0E-9 | 6.8E1 | 2.9E1 | 344 | 12 | 344 | 12 | 0.68 |
| Me | pg/ml | 3.2E1 | 2.9E1 | 3.1E1 | 3.7E1 | 2.4E1 | 4.8E1 | 1.0E-9 | 1.0E-9 | 3.2E2 | 1.8E2 | 344 | 12 | 344 | 12 | 0.45 |
| Mf | pg/ml | 1.0E-9 | 1.0E-9 | 6.4E-1 | 5.0E-1 | 3.9E0 | 1.3E0 | 1.0E-9 | 1.0E-9 | 5.6E1 | 4.5E0 | 344 | 12 | 344 | 12 | 0.58 |
| Mg | pg/ml | 1.0E0 | 8.0E0 | 6.2E0 | 2.9E1 | 1.2E1 | 4.7E1 | 1.0E-9 | 1.0E-9 | 9.2E1 | 1.5E2 | 344 | 12 | 344 | 12 | 0.59 |
| Mh | pg/ml | 1.0E-9 | 1.4E-1 | 1.1E0 | 3.1E0 | 7.6E0 | 6.0E0 | 1.0E-9 | 1.0E-9 | 1.1E2 | 1.8E1 | 344 | 12 | 344 | 12 | 0.70 |
| Mi | pg/ml | 1.0E-9 | 4.7E1 | 1.0E0 | 8.4E1 | 8.3E0 | 1.7E2 | 1.0E-9 | 1.0E-9 | 1.2E2 | 5.2E2 | 344 | 12 | 344 | 12 | 0.74 |
| Mj | pg/ml | 1.0E-9 | 1.3E1 | 5.7E0 | 5.1E1 | 3.1E1 | 7.4E1 | 1.0E-9 | 1.0E-9 | 4.6E2 | 2.1E2 | 344 | 12 | 344 | 12 | 0.69 |
| Mk | pg/ml | 1.8E0 | 6.3E0 | 1.5E1 | 6.0E1 | 9.2E1 | 1.4E2 | 1.0E-9 | 1.0E-9 | 1.3E3 | 5.0E2 | 344 | 12 | 344 | 12 | 0.65 |
| Ml | pg/ml | 1.0E-9 | 1.0E-9 | 9.9E0 | 4.4E1 | 1.2E2 | 1.5E2 | 1.0E-9 | 1.0E-9 | 2.1E3 | 5.1E2 | 344 | 12 | 344 | 12 | 0.53 |
| Mm | pg/ml | 5.5E2 | 3.0E3 | 1.0E3 | 3.3E3 | 1.3E3 | 3.0E3 | 1.0E-9 | 1.0E-9 | 1.0E4 | 1.0E4 | 344 | 12 | 344 | 12 | 0.73 |
| Mn | pg/ml | 5.7E0 | 1.3E1 | 1.1E1 | 1.7E1 | 2.5E1 | 1.3E1 | 1.0E-9 | 1.1E0 | 3.5E2 | 5.1E1 | 344 | 12 | 344 | 12 | 0.74 |
| Mp | pg/ml | 1.0E-9 | 6.9E1 | 1.2E1 | 3.0E2 | 4.3E1 | 6.7E2 | 1.0E-9 | 1.0E-9 | 6.3E2 | 2.4E3 | 344 | 12 | 344 | 12 | 0.88 |
| Mq | pg/ml | 1.0E-9 | 1.0E-9 | 2.1E0 | 2.2E1 | 1.3E1 | 3.6E1 | 1.0E-9 | 1.0E-9 | 1.8E2 | 1.0E2 | 344 | 12 | 344 | 12 | 0.64 |
| Mr | pg/ml | 1.0E-9 | 1.7E1 | 2.3E1 | 6.4E2 | 1.2E2 | 1.1E3 | 1.0E-9 | 1.0E-9 | 1.5E3 | 3.4E3 | 344 | 12 | 344 | 12 | 0.73 |
| Ms | pg/ml | 3.3E2 | 2.2E2 | 4.8E2 | 2.9E2 | 5.7E2 | 3.3E2 | 1.0E-9 | 1.0E-9 | 4.7E3 | 9.8E2 | 344 | 12 | 344 | 12 | 0.39 |
| Mt | pg/ml | 2.4E-1 | 7.8E1 | 8.0E0 | 3.5E2 | 4.3E1 | 9.2E2 | 1.0E-9 | 1.0E-9 | 7.1E2 | 3.2E3 | 344 | 12 | 344 | 12 | 0.87 |
| Mu | pg/ml | 1.0E-9 | 4.5E0 | 1.4E0 | 1.1E1 | 1.4E1 | 1.6E1 | 1.0E-9 | 1.0E-9 | 2.3E2 | 4.8E1 | 344 | 12 | 344 | 12 | 0.84 |
| Mv | pg/ml | 1.0E-9 | 2.0E2 | 6.1E1 | 3.6E2 | 3.3E2 | 4.0E2 | 1.0E-9 | 1.0E-9 | 4.5E3 | 9.2E2 | 344 | 12 | 344 | 12 | 0.72 |
| Mw | pg/ml | 3.6E1 | 1.2E3 | 2.5E2 | 1.8E3 | 1.3E3 | 1.9E3 | 1.0E-9 | 1.0E-9 | 1.8E4 | 5.3E3 | 344 | 12 | 344 | 12 | 0.87 |
| Mx | pg/ml | 1.0E-9 | 3.9E-1 | 3.5E-1 | 2.6E0 | 1.9E0 | 5.6E0 | 1.0E-9 | 1.0E-9 | 3.2E1 | 2.0E1 | 344 | 12 | 344 | 12 | 0.72 |
| My | pg/ml | 1.0E-9 | 2.1E2 | 3.2E2 | 4.9E2 | 2.4E3 | 6.9E2 | 1.0E-9 | 1.0E-9 | 3.9E4 | 1.9E3 | 344 | 12 | 344 | 12 | 0.72 |
| Mz | pg/ml | 1.1E1 | 1.1E2 | 2.6E1 | 3.4E2 | 5.0E1 | 6.1E2 | 1.0E-9 | 1.0E-9 | 5.5E2 | 1.9E3 | 344 | 12 | 344 | 12 | 0.80 |
| Na | pg/ml | 1.0E-9 | 1.6E-1 | 6.4E-1 | 5.0E0 | 1.9E0 | 1.2E1 | 1.0E-9 | 1.0E-9 | 9.6E0 | 4.2E1 | 344 | 12 | 344 | 12 | 0.66 |
| Nb | pg/ml | 2.2E0 | 1.1E1 | 3.6E0 | 3.8E1 | 9.9E0 | 6.2E1 | 1.0E-9 | 1.0E-9 | 1.5E2 | 2.1E2 | 344 | 12 | 344 | 12 | 0.75 |
| Nc | pg/ml | 3.3E2 | 6.5E0 | 5.2E2 | 1.8E2 | 7.4E2 | 3.1E2 | 1.0E-9 | 1.0E-9 | 9.2E3 | 7.9E2 | 344 | 12 | 344 | 12 | 0.31 |
| Nd | pg/ml | 2.7E1 | 4.1E1 | 2.7E1 | 2.2E2 | 6.8E1 | 6.0E2 | 1.0E-9 | 7.2E-1 | 1.2E3 | 2.1E3 | 344 | 12 | 344 | 12 | 0.69 |
| Ne | pg/ml | 4.2E2 | 2.7E2 | 5.2E2 | 5.2E2 | 5.4E2 | 9.8E2 | 1.0E-9 | 1.0E-9 | 7.0E3 | 3.6E3 | 344 | 12 | 344 | 12 | 0.38 |
| Nf | pg/ml | 1.0E-9 | 1.0E-9 | 2.3E0 | 2.4E1 | 8.6E0 | 4.7E1 | 1.0E-9 | 1.0E-9 | 8.2E1 | 1.3E2 | 344 | 12 | 344 | 12 | 0.63 |
| Ng | pg/ml | 1.2E1 | 2.7E1 | 9.0E1 | 9.7E1 | 1.8E2 | 1.3E2 | 1.0E-9 | 1.0E-9 | 1.6E3 | 4.2E2 | 344 | 12 | 344 | 12 | 0.52 |
| Nh | pg/ml | 6.2E1 | 3.1E1 | 8.0E1 | 7.4E1 | 7.3E1 | 1.4E2 | 1.0E-9 | 4.1E0 | 5.6E2 | 5.1E2 | 344 | 12 | 344 | 12 | 0.33 |
| Ni | pg/ml | 1.0E-9 | 1.0E-9 | 8.3E1 | 1.6E2 | 1.3E2 | 3.2E2 | 1.0E-9 | 1.0E-9 | 7.1E2 | 1.1E3 | 344 | 12 | 344 | 12 | 0.47 |
| Nj | pg/ml | 7.2E0 | 4.0E0 | 1.1E1 | 6.9E0 | 1.2E1 | 7.6E0 | 1.0E-9 | 1.0E-9 | 6.9E1 | 2.2E1 | 344 | 12 | 344 | 12 | 0.39 |

Figure 42

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nk | pg/ml | 1.8E1 | 3.5E-1 | 3.3E1 | 1.3E1 | 3.9E1 | 2.2E1 | 1.0E-9 | 1.0E-9 | 2.0E2 | 6.6E1 | 344 | 12 | 344 | 12 | 0.33 |
| Nl | pg/ml | 4.3E1 | 1.0E1 | 5.7E1 | 3.2E1 | 7.5E1 | 5.2E1 | 1.0E-9 | 1.0E-9 | 1.1E3 | 1.8E2 | 344 | 12 | 344 | 12 | 0.31 |
| Hq | pg/ml | 1.2E0 | 1.2E1 | 1.5E2 | 2.6E2 | 1.9E3 | 8.0E2 | 1.0E-9 | 1.0E-9 | 2.8E4 | 2.8E3 | 342 | 12 | 342 | 12 | 0.73 |
| Hr | pg/ml | 8.9E1 | 2.7E2 | 6.3E2 | 1.3E3 | 1.3E3 | 2.6E3 | 1.0E-9 | 1.0E-9 | 1.2E4 | 8.9E3 | 342 | 12 | 342 | 12 | 0.59 |
| Hu | pg/ml | 7.9E0 | 6.5E2 | 4.6E3 | 1.6E3 | 4.0E4 | 2.3E3 | 1.0E-9 | 1.0E-9 | 6.3E5 | 6.5E3 | 342 | 12 | 342 | 12 | 0.71 |
| Hv | pg/ml | 1.4E0 | 3.6E0 | 2.9E0 | 8.3E1 | 1.0E1 | 2.6E2 | 1.0E-9 | 1.0E-9 | 1.6E2 | 8.9E2 | 342 | 12 | 342 | 12 | 0.75 |
| Hw | pg/ml | 6.2E0 | 3.5E1 | 1.5E1 | 8.7E2 | 4.5E1 | 2.7E3 | 1.0E-9 | 4.6E-1 | 6.4E2 | 9.4E3 | 342 | 12 | 342 | 12 | 0.64 |
| Hx | pg/ml | 8.8E0 | 4.4E1 | 5.2E1 | 2.2E2 | 5.0E2 | 4.1E2 | 1.0E-9 | 3.9E0 | 9.3E3 | 1.3E3 | 342 | 12 | 342 | 12 | 0.77 |
| Ih | ng/ml | 6.3E1 | 6.6E2 | 2.5E2 | 8.3E2 | 4.4E2 | 8.3E2 | 1.0E-9 | 2.4E0 | 3.6E3 | 2.8E3 | 343 | 12 | 343 | 12 | 0.73 |
| Ii | ng/ml | 7.9E1 | 4.7E2 | 2.0E2 | 1.1E3 | 4.6E2 | 1.5E3 | 7.3E-1 | 7.5E-1 | 5.2E3 | 4.5E3 | 343 | 12 | 343 | 12 | 0.73 |
| Ij | ng/ml | 7.9E1 | 2.3E2 | 1.8E2 | 2.4E3 | 5.7E2 | 6.9E3 | 2.8E0 | 9.5E0 | 6.4E3 | 2.4E4 | 339 | 12 | 339 | 12 | 0.74 |
| Ik | ng/ml | 1.1E1 | 1.8E1 | 1.3E3 | 2.1E3 | 1.2E4 | 4.3E2 | 5.9E-1 | 6.2E-1 | 1.2E5 | 1.5E3 | 339 | 12 | 339 | 12 | 0.57 |
| Il | ng/ml | 3.6E2 | 7.0E2 | 1.3E3 | 3.6E3 | 2.8E3 | 5.1E3 | 1.0E-9 | 1.9E-1 | 1.2E4 | 1.2E4 | 337 | 12 | 337 | 12 | 0.64 |
| Im | ng/ml | 2.1E2 | 7.0E2 | 4.6E2 | 1.8E3 | 1.0E3 | 2.2E3 | 1.4E1 | 2.2E1 | 1.5E4 | 6.2E3 | 339 | 12 | 339 | 12 | 0.78 |
| In | ng/ml | 3.4E0 | 2.8E0 | 2.0E1 | 4.5E2 | 8.9E1 | 1.3E3 | 1.0E-9 | 1.0E-9 | 1.1E3 | 4.5E3 | 343 | 12 | 343 | 12 | 0.55 |
| Io | ng/ml | 9.6E3 | 9.4E3 | 2.0E4 | 1.3E4 | 4.6E4 | 1.2E4 | 1.0E-9 | 1.0E3 | 7.1E5 | 3.3E4 | 343 | 12 | 343 | 12 | 0.47 |
| Ip | ng/ml | 1.0E1 | 4.2E1 | 2.1E1 | 4.2E1 | 2.6E1 | 1.9E1 | 1.0E-9 | 9.8E0 | 2.3E2 | 7.1E1 | 343 | 12 | 343 | 12 | 0.79 |
| Iq | ug/ml | 1.0E-1 | 2.5E0 | 4.0E1 | 2.4E1 | 7.3E2 | 6.2E1 | 1.0E-9 | 1.0E-9 | 1.4E4 | 2.2E2 | 343 | 12 | 343 | 12 | 0.75 |
| Ir | ug/ml | 3.7E-1 | 6.0E0 | 4.5E0 | 5.8E1 | 3.2E1 | 1.1E2 | 1.0E-9 | 3.5E-2 | 5.1E2 | 3.7E2 | 342 | 12 | 342 | 12 | 0.78 |
| Is | ng/ml | 2.0E0 | 4.0E1 | 9.1E0 | 6.4E1 | 3.4E1 | 7.5E1 | 1.0E-9 | 4.3E-1 | 5.5E2 | 2.6E2 | 343 | 12 | 343 | 12 | 0.87 |
| It | ng/ml | 2.1E0 | 8.1E0 | 2.2E1 | 6.8E1 | 1.0E2 | 1.9E2 | 1.0E-9 | 1.0E-9 | 1.1E3 | 6.8E2 | 343 | 12 | 343 | 12 | 0.68 |
| Iu | ng/ml | 1.6E2 | 1.2E3 | 1.2E3 | 7.4E3 | 3.9E3 | 1.1E4 | 1.0E-9 | 1.0E-9 | 2.9E4 | 2.4E4 | 343 | 12 | 343 | 12 | 0.68 |
| Iv | ng/ml | 1.3E1 | 1.1E2 | 9.4E1 | 7.8E2 | 8.8E2 | 1.4E3 | 1.0E-9 | 1.0E0 | 1.6E4 | 3.8E3 | 342 | 12 | 342 | 12 | 0.74 |
| Pz | ng/ml | 3.6E3 | 4.0E3 | 5.6E3 | 5.8E3 | 6.0E3 | 4.4E3 | 1.6E1 | 4.0E1 | 7.0E4 | 1.3E4 | 339 | 12 | 339 | 12 | 0.56 |
| Qa | ng/ml | 3.6E3 | 2.3E4 | 6.9E3 | 3.5E4 | 7.9E3 | 6.0E4 | 1.5E2 | 9.4E2 | 4.2E4 | 2.2E5 | 339 | 12 | 339 | 12 | 0.82 |
| Qb | ng/ml | 1.1E2 | 3.8E2 | 2.3E2 | 4.5E2 | 4.4E2 | 4.1E2 | 7.9E-1 | 3.2E1 | 5.3E3 | 1.6E3 | 339 | 12 | 339 | 12 | 0.74 |
| Qc | ng/ml | 2.1E2 | 5.4E2 | 4.5E2 | 6.8E2 | 5.9E2 | 8.3E2 | 1.0E-9 | 1.3E1 | 4.3E3 | 2.8E3 | 339 | 12 | 339 | 12 | 0.57 |
| Qd | ng/ml | 8.9E3 | 1.0E5 | 2.5E4 | 1.0E5 | 1.2E5 | 8.7E4 | 1.5E2 | 1.9E3 | 2.0E6 | 2.3E5 | 339 | 12 | 339 | 12 | 0.77 |
| Qe | ng/ml | 8.8E2 | 4.4E3 | 2.0E3 | 5.2E3 | 5.6E3 | 4.9E3 | 1.0E-9 | 1.2E2 | 9.7E4 | 1.8E4 | 339 | 12 | 339 | 12 | 0.77 |
| Jg | ng/ml | 4.6E2 | 2.2E3 | 7.7E2 | 2.2E3 | 9.4E2 | 1.9E3 | 5.8E0 | 8.4E1 | 1.0E4 | 7.1E3 | 342 | 12 | 342 | 12 | 0.77 |
| Jh | ng/ml | 2.9E0 | 7.8E1 | 2.0E1 | 1.2E2 | 8.1E1 | 1.4E2 | 1.0E-9 | 1.0E-9 | 1.2E3 | 4.9E2 | 342 | 12 | 342 | 12 | 0.82 |
| Ji | ng/ml | 5.6E1 | 3.4E2 | 8.6E1 | 4.1E2 | 9.6E1 | 3.4E2 | 1.1E0 | 2.3E1 | 1.8E3 | 1.3E3 | 342 | 12 | 342 | 12 | 0.85 |
| Jj | ng/ml | 5.4E2 | 1.0E2 | 1.9E3 | 2.8E2 | 1.8E4 | 3.6E2 | 2.3E0 | 8.7E0 | 3.4E5 | 1.0E3 | 342 | 12 | 342 | 12 | 0.23 |
| Jk | ng/ml | 2.6E0 | 6.5E1 | 2.0E1 | 8.9E1 | 4.6E1 | 8.4E1 | 1.0E-9 | 1.2E-1 | 3.9E2 | 2.4E2 | 342 | 12 | 342 | 12 | 0.77 |
| Jl | ng/ml | 4.8E-1 | 1.5E1 | 1.9E0 | 8.4E2 | 4.7E0 | 2.9E3 | 1.2E-3 | 2.5E-1 | 4.0E1 | 9.9E3 | 342 | 12 | 342 | 12 | 0.87 |
| Jm | ng/ml | 2.0E1 | 3.1E1 | 6.7E1 | 7.5E1 | 1.7E2 | 1.1E2 | 1.0E-9 | 4.0E-1 | 2.1E3 | 3.6E2 | 342 | 12 | 342 | 12 | 0.57 |
| Jn | pg/ml | 3.4E-1 | 1.9E0 | 4.0E0 | 1.2E2 | 3.6E1 | 2.6E2 | 1.0E-9 | 2.4E-1 | 6.2E2 | 7.3E2 | 342 | 12 | 342 | 12 | 0.81 |
| Jo | pg/ml | 3.8E3 | 4.1E3 | 4.8E3 | 1.7E4 | 3.9E3 | 2.9E4 | 2.0E1 | 2.4E1 | 2.4E4 | 1.0E5 | 342 | 12 | 342 | 12 | 0.58 |
| Jp | pg/ml | 7.1E4 | 1.1E5 | 7.4E4 | 1.1E5 | 3.9E4 | 4.1E4 | 5.8E2 | 6.5E4 | 3.8E5 | 2.1E5 | 342 | 12 | 342 | 12 | 0.79 |
| Jq | pg/ml | 9.6E1 | 4.0E2 | 1.6E2 | 1.5E3 | 2.0E2 | 2.5E3 | 1.0E0 | 1.3E1 | 2.0E3 | 8.7E3 | 342 | 12 | 342 | 12 | 0.76 |
| Jr | pg/ml | 4.2E0 | 3.4E1 | 5.9E1 | 1.1E3 | 6.0E2 | 2.5E3 | 1.0E-9 | 6.7E0 | 1.1E4 | 7.4E3 | 342 | 12 | 342 | 12 | 0.86 |
| Js | pg/ml | 1.5E1 | 3.4E1 | 7.4E1 | 5.7E2 | 5.7E2 | 1.1E3 | 1.0E-9 | 2.7E0 | 1.0E4 | 3.0E3 | 342 | 12 | 342 | 12 | 0.74 |
| Jt | pg/ml | 2.4E3 | 4.8E3 | 3.0E3 | 1.3E4 | 2.4E3 | 1.7E4 | 2.2E1 | 1.5E2 | 2.2E4 | 5.2E4 | 342 | 12 | 342 | 12 | 0.68 |
| Lh | pg/ml | 1.3E4 | 3.7E4 | 2.1E4 | 1.5E5 | 2.7E4 | 1.8E5 | 1.0E-9 | 1.8E3 | 2.6E5 | 4.8E5 | 343 | 12 | 343 | 12 | 0.77 |
| Li | pg/ml | 3.5E3 | 9.3E4 | 1.9E4 | 1.2E5 | 8.9E4 | 1.4E5 | 1.2E1 | 8.4E1 | 1.3E6 | 4.1E5 | 343 | 12 | 343 | 12 | 0.75 |
| Lj | pg/ml | 2.9E3 | 9.2E3 | 2.0E4 | 4.8E4 | 5.6E4 | 1.1E5 | 1.0E-9 | 8.9E1 | 4.3E5 | 3.9E5 | 343 | 12 | 343 | 12 | 0.65 |
| Nv | pg/ml | 3.9E3 | 2.8E4 | 9.2E3 | 4.5E4 | 1.8E4 | 4.5E4 | 1.0E-9 | 1.6E2 | 1.6E5 | 1.2E5 | 344 | 12 | 344 | 12 | 0.78 |
| Nw | pg/ml | 9.6E3 | 2.7E4 | 1.3E4 | 6.1E4 | 1.6E4 | 7.5E4 | 1.9E2 | 4.5E3 | 2.1E5 | 2.2E5 | 344 | 12 | 344 | 12 | 0.82 |
| Nx | pg/ml | 2.2E2 | 1.1E3 | 4.3E2 | 1.1E3 | 6.1E2 | 1.2E3 | 1.0E-9 | 1.0E-9 | 3.5E3 | 4.1E3 | 344 | 12 | 344 | 12 | 0.69 |
| Ny | pg/ml | 6.5E0 | 1.5E2 | 9.7E1 | 4.0E2 | 1.3E3 | 7.7E2 | 1.0E-9 | 1.0E-9 | 2.5E4 | 2.8E3 | 344 | 12 | 344 | 12 | 0.80 |
| Oe | pg/ml | 3.5E1 | 1.0E-9 | 2.5E2 | 1.6E2 | 3.8E2 | 3.6E2 | 1.0E-9 | 1.0E-9 | 2.3E3 | 1.1E3 | 342 | 12 | 342 | 12 | 0.39 |
| Of | pg/ml | 1.3E2 | 1.2E2 | 4.9E3 | 8.9E3 | 2.0E4 | 1.9E4 | 1.0E-9 | 1.0E-9 | 1.9E5 | 6.6E4 | 344 | 12 | 344 | 12 | 0.55 |
| Og | pg/ml | 7.0E-2 | 9.2E-3 | 3.6E-1 | 5.8E-2 | 1.5E0 | 9.3E-2 | 1.0E-9 | 1.0E-9 | 1.9E1 | 3.2E-1 | 344 | 12 | 344 | 12 | 0.36 |
| Oh | pg/ml | 2.5E0 | 3.8E1 | 1.4E1 | 1.4E3 | 8.8E1 | 4.5E3 | 1.0E-9 | 1.0E-9 | 1.4E3 | 1.6E4 | 344 | 12 | 344 | 12 | 0.79 |
| Oi | pg/ml | 2.0E0 | 1.0E-9 | 5.0E0 | 6.1E0 | 7.8E0 | 9.6E0 | 1.0E-9 | 1.0E-9 | 6.7E1 | 3.1E1 | 344 | 12 | 344 | 12 | 0.46 |
| Ok | pg/ml | 3.9E2 | 1.3E3 | 5.4E2 | 2.1E3 | 6.2E2 | 2.3E3 | 1.5E1 | 5.3E1 | 7.0E3 | 7.8E3 | 344 | 12 | 344 | 12 | 0.78 |
| Om | pg/ml | 4.2E2 | 2.9E3 | 7.9E2 | 6.8E3 | 2.0E3 | 1.4E4 | 1.0E-9 | 7.0E1 | 3.0E4 | 5.1E4 | 344 | 12 | 344 | 12 | 0.81 |

Figure 42 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| On | pg/ml | 1.8E2 | 1.3E3 | 2.9E2 | 2.0E3 | 4.1E2 | 2.3E3 | 1.0E-9 | 1.6E1 | 4.5E3 | 8.5E3 | 344 | 12 | 344 | 12 | 0.87 |
| Oy | pg/ml | 4.7E-1 | 3.5E0 | 6.0E0 | 8.2E0 | 3.1E1 | 1.0E1 | 1.0E-9 | 1.0E-9 | 4.0E2 | 3.3E1 | 343 | 12 | 343 | 12 | 0.68 |
| Oz | pg/ml | 4.5E-3 | 1.0E-9 | 3.2E-1 | 2.4E0 | 1.6E0 | 8.1E0 | 1.0E-9 | 1.0E-9 | 2.9E1 | 2.8E1 | 343 | 12 | 343 | 12 | 0.43 |
| Pa | pg/ml | 3.9E-1 | 4.7E0 | 1.3E0 | 3.3E1 | 5.6E0 | 6.7E1 | 1.0E-9 | 1.0E-9 | 8.6E1 | 2.3E2 | 343 | 12 | 343 | 12 | 0.74 |
| Pb | pg/ml | 1.0E-9 | 1.0E-9 | 1.6E0 | 2.8E0 | 2.6E1 | 9.1E0 | 1.0E-9 | 1.0E-9 | 4.9E2 | 3.2E1 | 343 | 12 | 343 | 12 | 0.46 |
| Pc | pg/ml | 4.4E-2 | 1.0E-9 | 3.7E-1 | 3.1E1 | 8.8E-1 | 9.4E1 | 1.0E-9 | 1.0E-9 | 1.4E1 | 3.3E2 | 343 | 12 | 343 | 12 | 0.53 |
| Pd | pg/ml | 1.6E0 | 1.4E1 | 6.2E0 | 2.6E1 | 4.6E1 | 3.5E1 | 1.0E-9 | 7.3E-2 | 8.4E2 | 1.2E2 | 343 | 12 | 343 | 12 | 0.68 |
| Pe | pg/ml | 2.2E1 | 4.4E2 | 1.1E2 | 2.5E3 | 4.4E2 | 4.5E3 | 1.0E-9 | 3.3E0 | 4.7E3 | 1.5E4 | 343 | 12 | 343 | 12 | 0.81 |
| Pf | pg/ml | 1.6E0 | 2.6E1 | 1.5E1 | 7.2E1 | 9.0E1 | 1.2E2 | 1.0E-9 | 1.0E-9 | 1.5E3 | 4.3E2 | 343 | 12 | 343 | 12 | 0.85 |
| Pg | pg/ml | 3.9E0 | 2.1E2 | 6.8E1 | 5.3E2 | 5.1E2 | 7.0E2 | 1.0E-9 | 4.6E-1 | 7.7E3 | 2.2E3 | 343 | 12 | 343 | 12 | 0.81 |
| aA | mg/dL | 9.0E-1 | 2.8E0 | 1.0E0 | 2.4E0 | 5.0E-1 | 1.3E0 | 3.0E-1 | 5.5E-1 | 4.2E0 | 4.7E0 | 521 | 16 | 521 | 16 | 0.82 |
| aC | mg/mL | 2.2E0 | 2.4E0 | 2.6E0 | 3.0E0 | 1.3E0 | 1.9E0 | 7.5E-1 | 1.1E0 | 7.4E0 | 5.5E0 | 169 | 7 | 169 | 7 | 0.53 |
| aD | ug/mL | 2.9E0 | 3.7E0 | 4.6E0 | 6.3E0 | 4.7E0 | 5.9E0 | 7.5E-1 | 1.8E0 | 3.5E1 | 1.8E1 | 169 | 7 | 169 | 7 | 0.59 |
| aE | mg/mL | 5.7E-1 | 5.5E-1 | 5.9E-1 | 5.6E-1 | 1.7E-1 | 1.4E-1 | 1.8E-1 | 3.9E-1 | 1.2E0 | 7.2E-1 | 169 | 7 | 169 | 7 | 0.46 |
| aF | ng/mL | 2.2E0 | 9.1E0 | 4.9E0 | 8.7E0 | 7.7E0 | 5.2E0 | 4.3E-3 | 4.3E-3 | 5.0E1 | 1.5E1 | 169 | 7 | 169 | 7 | 0.74 |
| aG | mg/mL | 1.4E-1 | 9.5E-2 | 1.6E-1 | 1.2E-1 | 8.7E-2 | 4.2E-2 | 3.2E-2 | 6.9E-2 | 4.8E-1 | 1.7E-1 | 169 | 7 | 169 | 7 | 0.37 |
| aH | ug/mL | 7.1E1 | 5.6E1 | 7.8E1 | 6.0E1 | 4.1E1 | 2.8E1 | 8.9E0 | 1.1E1 | 2.0E2 | 1.0E2 | 169 | 7 | 169 | 7 | 0.41 |
| aI | ug/mL | 1.7E2 | 1.4E2 | 1.8E2 | 1.2E2 | 6.1E1 | 2.8E1 | 3.2E1 | 7.6E1 | 3.4E2 | 1.6E2 | 169 | 7 | 169 | 7 | 0.23 |
| aJ | ug/mL | 2.4E0 | 7.0E0 | 3.1E0 | 9.1E0 | 2.2E0 | 6.7E0 | 8.2E-1 | 2.2E0 | 1.4E1 | 2.3E1 | 169 | 7 | 169 | 7 | 0.87 |
| aK | ng/mL | 1.3E0 | 1.6E0 | 2.0E0 | 2.0E0 | 1.9E0 | 2.3E0 | 2.9E-4 | 1.3E-1 | 1.0E1 | 6.5E0 | 169 | 7 | 169 | 7 | 0.48 |
| aL | mg/mL | 7.4E-1 | 7.3E-1 | 7.7E-1 | 6.5E-1 | 2.6E-1 | 2.5E-1 | 2.2E-1 | 2.7E-1 | 1.7E0 | 9.2E-1 | 169 | 7 | 169 | 7 | 0.40 |
| aM | U/mL | 1.9E1 | 4.7E1 | 3.9E1 | 1.9E2 | 6.9E1 | 3.1E2 | 4.2E-2 | 4.2E-2 | 6.8E2 | 8.2E2 | 169 | 7 | 169 | 7 | 0.70 |
| aN | U/mL | 1.5E1 | 2.6E1 | 2.5E1 | 3.5E1 | 4.3E1 | 2.9E1 | 2.5E-3 | 7.4E0 | 3.8E2 | 8.8E1 | 169 | 7 | 169 | 7 | 0.68 |
| aO | pg/mL | 4.9E1 | 1.3E3 | 4.1E2 | 1.1E3 | 9.8E2 | 9.6E2 | 6.0E-2 | 7.2E1 | 6.6E3 | 2.4E3 | 169 | 7 | 169 | 7 | 0.82 |
| aP | ng/mL | 1.6E0 | 5.0E0 | 2.2E0 | 7.7E0 | 2.4E0 | 9.1E0 | 4.5E-1 | 1.6E0 | 2.8E1 | 2.8E1 | 169 | 7 | 169 | 7 | 0.88 |
| aQ | ng/mL | 2.4E-1 | 4.1E-1 | 3.5E-1 | 3.9E-1 | 3.2E-1 | 2.9E-1 | 2.0E-4 | 5.1E-2 | 2.0E0 | 9.0E-1 | 169 | 7 | 169 | 7 | 0.55 |
| aR | ng/mL | 1.7E0 | 4.6E0 | 3.0E0 | 3.9E0 | 4.1E0 | 1.7E0 | 2.6E-1 | 6.5E-1 | 3.4E1 | 5.5E0 | 169 | 7 | 169 | 7 | 0.71 |
| aS | ng/mL | 3.7E-1 | 5.4E-1 | 9.9E-1 | 1.1E0 | 2.7E0 | 1.2E0 | 4.2E-3 | 8.0E-2 | 3.3E1 | 2.8E0 | 169 | 7 | 169 | 7 | 0.56 |
| aU | pg/mL | 6.6E1 | 7.8E1 | 9.9E1 | 1.2E2 | 1.0E2 | 1.8E2 | 7.4E-2 | 7.4E-2 | 7.0E2 | 5.1E2 | 169 | 7 | 169 | 7 | 0.47 |
| aV | ng/mL | 5.8E-1 | 5.8E-1 | 1.1E0 | 7.8E-1 | 2.6E0 | 8.3E-1 | 7.6E-4 | 1.0E-1 | 3.3E1 | 2.4E0 | 169 | 7 | 169 | 7 | 0.46 |
| aW | pg/mL | 1.9E1 | 3.1E1 | 2.2E1 | 2.6E1 | 3.4E1 | 1.5E1 | 7.2E-2 | 7.2E-2 | 4.2E2 | 4.7E1 | 169 | 7 | 169 | 7 | 0.68 |
| aX | ng/mL | 8.0E0 | 1.8E1 | 1.5E1 | 4.5E1 | 3.1E1 | 5.3E1 | 3.0E-1 | 2.6E0 | 3.1E2 | 1.3E2 | 169 | 7 | 169 | 7 | 0.67 |
| aY | pg/mL | 5.3E1 | 4.7E1 | 7.6E1 | 7.1E1 | 1.1E2 | 6.1E1 | 4.1E-1 | 2.7E1 | 1.2E3 | 2.0E2 | 169 | 7 | 169 | 7 | 0.50 |
| aZ | pg/mL | 2.3E2 | 2.9E2 | 6.8E2 | 5.2E2 | 1.4E3 | 7.0E2 | 1.7E0 | 7.5E1 | 1.2E4 | 2.1E3 | 169 | 7 | 169 | 7 | 0.56 |
| bA | ng/mL | 1.3E1 | 1.5E2 | 6.0E1 | 4.2E2 | 1.3E2 | 5.6E2 | 3.0E-2 | 4.7E0 | 9.4E2 | 1.5E3 | 169 | 7 | 169 | 7 | 0.82 |
| bB | ng/mL | 2.8E2 | 1.9E2 | 3.1E2 | 2.0E2 | 1.8E2 | 1.1E2 | 2.1E0 | 3.3E1 | 9.5E2 | 3.8E2 | 169 | 7 | 169 | 7 | 0.34 |
| bC | ng/mL | 3.2E2 | 1.6E3 | 6.0E2 | 1.8E3 | 8.1E2 | 1.7E3 | 1.4E1 | 1.4E2 | 4.7E3 | 4.0E3 | 169 | 7 | 169 | 7 | 0.75 |
| bE | mg/mL | 5.1E0 | 5.5E0 | 5.4E0 | 6.6E0 | 2.1E0 | 3.8E0 | 1.8E0 | 1.3E0 | 1.2E1 | 1.1E1 | 169 | 7 | 169 | 7 | 0.58 |
| bF | pg/mL | 3.5E1 | 6.8E1 | 3.5E2 | 3.3E2 | 1.4E3 | 6.8E2 | 5.0E-2 | 2.0E1 | 1.1E4 | 1.9E3 | 169 | 7 | 169 | 7 | 0.71 |
| bG | ng/mL | 1.7E0 | 2.6E0 | 3.1E0 | 5.4E0 | 4.3E0 | 5.8E0 | 1.1E-1 | 2.4E-1 | 3.0E1 | 1.5E1 | 169 | 7 | 169 | 7 | 0.63 |
| bH | pg/mL | 5.7E-1 | 1.3E1 | 6.1E0 | 9.7E0 | 2.4E1 | 9.0E0 | 5.7E-1 | 5.7E-1 | 2.8E2 | 2.3E1 | 169 | 7 | 169 | 7 | 0.68 |
| bI | ng/mL | 4.0E-3 | 4.0E-3 | 9.0E-2 | 1.6E-1 | 2.0E-1 | 2.1E-1 | 4.0E-3 | 4.0E-3 | 9.8E-1 | 5.1E-1 | 169 | 7 | 169 | 7 | 0.61 |
| bJ | mg/mL | 1.9E0 | 2.3E0 | 2.4E0 | 2.7E0 | 2.0E0 | 2.9E0 | 2.5E-4 | 2.5E-4 | 1.1E1 | 8.9E0 | 169 | 7 | 169 | 7 | 0.52 |
| bL | pg/mL | 3.7E0 | 1.1E1 | 9.1E0 | 1.3E1 | 1.2E1 | 8.0E0 | 4.6E-2 | 3.0E0 | 6.0E1 | 2.4E1 | 169 | 7 | 169 | 7 | 0.71 |
| bM | mg/mL | 1.8E0 | 1.8E0 | 2.2E0 | 1.9E0 | 1.5E0 | 1.1E0 | 1.6E-2 | 5.5E-1 | 8.6E0 | 3.8E0 | 169 | 7 | 169 | 7 | 0.47 |
| bN | ng/mL | 3.3E1 | 6.0E1 | 1.2E2 | 9.5E1 | 2.9E2 | 9.0E1 | 1.4E-1 | 6.7E0 | 1.9E3 | 2.5E2 | 169 | 7 | 169 | 7 | 0.60 |
| bO | ng/mL | 4.0E-2 | 4.0E-2 | 9.4E0 | 4.0E-2 | 2.0E1 | 0.0E0 | 4.0E-2 | 4.0E-2 | 1.3E2 | 4.0E-2 | 169 | 7 | 169 | 7 | 0.33 |
| bP | mg/mL | 5.3E-1 | 4.9E-1 | 7.5E-1 | 7.1E-1 | 7.1E-1 | 5.4E-1 | 4.9E-2 | 9.2E-2 | 4.8E0 | 1.6E0 | 169 | 7 | 169 | 7 | 0.50 |
| bQ | pg/mL | 2.1E1 | 9.3E1 | 1.4E2 | 1.1E2 | 1.0E3 | 6.2E1 | 1.5E-1 | 2.2E1 | 1.3E4 | 2.2E2 | 169 | 7 | 169 | 7 | 0.85 |
| bR | ng/mL | 1.2E-2 | 1.2E-2 | 1.6E-1 | 1.0E-1 | 7.2E-1 | 1.6E-1 | 1.2E-2 | 1.2E-2 | 8.7E0 | 3.8E-1 | 169 | 7 | 169 | 7 | 0.50 |
| bS | pg/mL | 9.4E-1 | 9.4E-1 | 8.9E0 | 2.4E1 | 4.1E1 | 3.2E1 | 9.4E-1 | 9.4E-1 | 3.9E2 | 7.2E1 | 169 | 7 | 169 | 7 | 0.66 |
| bU | pg/mL | 7.0E-2 | 1.6E-1 | 1.9E-1 | 1.6E-1 | 5.4E-1 | 1.1E-1 | 1.3E-2 | 1.3E-2 | 6.6E0 | 4.1E-1 | 169 | 7 | 169 | 7 | 0.55 |
| bV | pg/mL | 4.9E2 | 1.0E3 | 6.1E2 | 1.2E3 | 8.9E2 | 7.0E2 | 1.6E2 | 5.3E2 | 1.2E4 | 2.2E3 | 169 | 7 | 169 | 7 | 0.83 |
| bW | pg/mL | 3.1E2 | 6.1E2 | 4.9E2 | 1.5E3 | 5.4E2 | 1.7E3 | 8.4E1 | 3.1E2 | 4.8E3 | 3.9E3 | 169 | 7 | 169 | 7 | 0.78 |
| bX | ng/mL | 2.5E-5 | 3.1E-3 | 2.6E-3 | 3.1E-3 | 3.2E-3 | 3.1E-3 | 2.5E-5 | 2.5E-5 | 1.3E-2 | 7.2E-3 | 169 | 7 | 169 | 7 | 0.56 |
| bZ | pg/mL | 2.7E2 | 1.8E3 | 2.0E3 | 2.6E3 | 7.2E3 | 2.7E3 | 1.5E-1 | 1.8E2 | 5.8E4 | 7.4E3 | 169 | 7 | 169 | 7 | 0.73 |
| cA | pg/mL | 6.0E-1 | 6.0E-1 | 4.1E0 | 3.5E0 | 2.9E1 | 7.7E0 | 6.0E-1 | 6.0E-1 | 3.7E2 | 2.1E1 | 169 | 7 | 169 | 7 | 0.52 |

Figure 42 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| cB | ng/mL | 4.9E-2 | 4.6E-2 | 7.4E-2 | 8.6E-2 | 8.7E-2 | 1.1E-1 | 1.7E-3 | 1.7E-3 | 4.3E-1 | 2.6E-1 | 169 | 7 | 169 | 7 | 0.49 |
| cC | pg/mL | 4.1E1 | 3.5E1 | 4.6E1 | 2.8E1 | 5.0E1 | 2.6E1 | 1.0E0 | 1.0E0 | 4.5E2 | 5.9E1 | 169 | 7 | 169 | 7 | 0.36 |
| cD | pg/mL | 4.9E0 | 2.9E0 | 1.3E1 | 4.7E0 | 4.6E1 | 4.3E0 | 3.3E-1 | 3.3E-1 | 4.8E2 | 9.6E0 | 169 | 7 | 169 | 7 | 0.45 |
| cE | pg/mL | 5.9E1 | 2.6E2 | 2.7E2 | 2.3E2 | 6.0E2 | 1.4E2 | 1.2E-1 | 3.5E1 | 3.8E3 | 4.5E2 | 169 | 7 | 169 | 7 | 0.73 |
| cF | pg/mL | 4.5E0 | 5.3E-1 | 1.6E1 | 5.8E0 | 3.0E1 | 1.4E1 | 5.3E-1 | 5.3E-1 | 2.7E2 | 3.8E1 | 169 | 7 | 169 | 7 | 0.34 |
| cG | pg/mL | 5.4E1 | 3.3E2 | 1.7E2 | 2.7E2 | 8.1E2 | 1.8E2 | 7.8E0 | 4.0E1 | 1.0E4 | 4.9E2 | 169 | 7 | 169 | 7 | 0.80 |
| cH | uIU/mL | 3.2E0 | 2.5E0 | 7.6E0 | 7.8E0 | 1.7E1 | 1.2E1 | 8.6E-3 | 8.6E-3 | 1.6E2 | 3.4E1 | 169 | 7 | 169 | 7 | 0.45 |
| cI | ng/mL | 6.1E0 | 3.0E0 | 1.4E1 | 9.7E0 | 2.1E1 | 1.4E1 | 3.2E-2 | 1.1E0 | 1.2E2 | 4.1E1 | 169 | 7 | 169 | 7 | 0.43 |
| cJ | ug/mL | 6.6E1 | 3.6E1 | 1.0E2 | 5.0E1 | 1.0E2 | 5.8E1 | 6.9E0 | 5.6E0 | 6.4E2 | 1.7E2 | 169 | 7 | 169 | 7 | 0.31 |
| cK | ng/mL | 3.8E-3 | 3.8E-3 | 2.2E-2 | 4.9E-2 | 1.2E-1 | 7.5E-2 | 3.8E-3 | 3.8E-3 | 1.5E0 | 2.1E-1 | 169 | 7 | 169 | 7 | 0.66 |
| cL | pg/mL | 2.1E2 | 2.3E2 | 5.4E2 | 4.0E2 | 2.0E3 | 4.4E2 | 3.1E1 | 6.7E1 | 2.4E4 | 1.3E3 | 169 | 7 | 169 | 7 | 0.57 |
| cM | pg/mL | 2.7E2 | 2.1E2 | 2.9E2 | 2.1E2 | 1.7E2 | 8.3E1 | 2.5E1 | 5.7E1 | 1.1E3 | 3.1E2 | 169 | 7 | 169 | 7 | 0.34 |
| cN | pg/mL | 1.2E2 | 1.3E2 | 1.3E2 | 1.4E2 | 8.6E1 | 4.3E1 | 3.8E1 | 8.6E1 | 1.1E3 | 2.0E2 | 169 | 7 | 169 | 7 | 0.59 |
| cO | pg/mL | 2.1E2 | 4.4E2 | 4.0E2 | 5.4E2 | 1.5E3 | 4.9E2 | 5.4E1 | 9.6E1 | 1.9E4 | 1.5E3 | 169 | 7 | 169 | 7 | 0.66 |
| cP | ng/mL | 2.4E3 | 3.1E3 | 2.5E3 | 3.0E3 | 9.3E2 | 1.4E3 | 6.2E2 | 1.4E3 | 5.6E3 | 4.7E3 | 169 | 7 | 169 | 7 | 0.60 |
| cQ | ng/mL | 4.9E-2 | 1.6E-1 | 1.2E-1 | 2.8E-1 | 2.0E-1 | 3.0E-1 | 2.0E-3 | 2.0E-3 | 1.3E0 | 8.7E-1 | 169 | 7 | 169 | 7 | 0.72 |
| cR | ng/mL | 3.2E2 | 5.7E2 | 5.9E2 | 8.4E2 | 8.3E2 | 6.9E2 | 2.0E1 | 3.2E2 | 7.7E3 | 2.2E3 | 169 | 7 | 169 | 7 | 0.70 |
| cS | ng/mL | 2.8E2 | 6.6E2 | 4.2E2 | 1.8E3 | 4.7E2 | 2.5E3 | 4.1E1 | 1.4E2 | 3.3E3 | 7.1E3 | 169 | 7 | 169 | 7 | 0.77 |
| cT | ng/mL | 4.9E1 | 1.5E2 | 1.5E2 | 5.0E2 | 2.8E2 | 6.5E2 | 3.6E0 | 1.9E1 | 2.1E3 | 1.5E3 | 169 | 7 | 169 | 7 | 0.74 |
| cU | ng/mL | 5.8E1 | 1.3E2 | 9.6E1 | 1.6E2 | 1.5E2 | 9.0E1 | 6.2E0 | 8.0E1 | 1.6E3 | 3.3E2 | 169 | 7 | 169 | 7 | 0.81 |
| cV | ng/mL | 1.9E-1 | 3.5E-1 | 7.4E-1 | 3.7E-1 | 3.8E0 | 3.0E-1 | 2.5E-2 | 7.6E-2 | 4.7E1 | 9.3E-1 | 169 | 7 | 169 | 7 | 0.59 |
| cW | mIU/mL | 4.8E-2 | 9.4E-2 | 8.7E-2 | 1.3E-1 | 3.4E-1 | 1.3E-1 | 4.8E-3 | 3.3E-2 | 4.5E0 | 3.9E-1 | 169 | 7 | 169 | 7 | 0.71 |
| cX | ng/mL | 1.2E-1 | 4.4E-2 | 1.9E0 | 4.6E-1 | 5.7E0 | 9.1E-1 | 2.3E-4 | 1.1E-2 | 2.8E1 | 2.5E0 | 169 | 7 | 169 | 7 | 0.47 |
| cY | ng/mL | 7.4E0 | 8.9E0 | 1.1E1 | 1.2E1 | 1.1E1 | 1.3E1 | 1.7E-1 | 6.0E-1 | 6.1E1 | 3.6E1 | 169 | 7 | 169 | 7 | 0.47 |
| cZ | ug/mL | 1.3E1 | 1.1E1 | 1.5E1 | 1.4E1 | 6.7E0 | 8.3E0 | 2.3E0 | 3.3E0 | 4.6E1 | 3.0E1 | 169 | 7 | 169 | 7 | 0.44 |
| dA | pg/mL | 3.1E2 | 6.3E2 | 3.8E2 | 5.6E2 | 4.6E2 | 2.7E2 | 1.0E2 | 1.7E2 | 5.8E3 | 8.8E2 | 169 | 7 | 169 | 7 | 0.72 |
| dB | ug/mL | 1.8E1 | 1.9E1 | 1.8E1 | 1.9E1 | 2.0E1 | 8.5E0 | 2.1E0 | 4.5E0 | 2.5E2 | 2.8E1 | 169 | 7 | 169 | 7 | 0.57 |
| dC | nmol/L | 3.4E1 | 2.7E1 | 3.8E1 | 3.0E1 | 1.7E1 | 5.7E0 | 7.8E0 | 2.5E1 | 1.4E2 | 4.0E1 | 169 | 7 | 169 | 7 | 0.35 |
| dD | ug/mL | 3.4E1 | 2.8E1 | 3.5E1 | 2.8E1 | 1.1E1 | 6.8E0 | 1.4E1 | 2.1E1 | 7.4E1 | 4.3E1 | 169 | 7 | 169 | 7 | 0.27 |
| dE | ng/mL | 4.1E-1 | 1.0E0 | 5.5E-1 | 1.2E0 | 5.8E-1 | 9.5E-1 | 8.4E-3 | 8.4E-3 | 2.9E0 | 2.4E0 | 169 | 7 | 169 | 7 | 0.71 |
| dF | ng/mL | 2.5E2 | 7.8E2 | 3.3E2 | 6.7E2 | 2.4E2 | 3.6E2 | 7.5E1 | 2.8E2 | 1.3E3 | 1.2E3 | 169 | 7 | 169 | 7 | 0.81 |
| dG | ng/mL | 1.2E1 | 2.6E1 | 1.6E1 | 3.7E1 | 1.8E1 | 2.9E1 | 3.0E0 | 6.7E0 | 1.8E2 | 8.7E1 | 169 | 7 | 169 | 7 | 0.79 |
| dH | pg/mL | 8.0E0 | 1.4E1 | 2.1E1 | 2.2E1 | 6.3E1 | 2.5E1 | 4.0E-2 | 8.3E-1 | 6.7E2 | 7.6E1 | 169 | 7 | 169 | 7 | 0.69 |
| dI | pg/mL | 4.6E-1 | 2.9E0 | 3.7E0 | 5.5E0 | 2.6E1 | 6.7E0 | 4.6E-1 | 4.6E-1 | 3.3E2 | 1.9E1 | 169 | 7 | 169 | 7 | 0.70 |
| dJ | ng/mL | 2.0E0 | 2.2E0 | 2.1E0 | 2.1E0 | 1.1E0 | 1.2E0 | 3.2E-2 | 4.9E-1 | 5.6E0 | 4.0E0 | 169 | 7 | 169 | 7 | 0.50 |
| dK | uIU/mL | 1.3E0 | 3.2E-1 | 2.2E0 | 1.2E0 | 3.6E0 | 2.2E0 | 2.8E-4 | 1.4E-2 | 3.9E1 | 6.1E0 | 169 | 7 | 169 | 7 | 0.25 |
| dL | ng/mL | 8.7E2 | 1.3E3 | 1.0E3 | 1.8E3 | 5.5E2 | 1.4E3 | 2.8E2 | 6.3E2 | 3.8E3 | 4.8E3 | 169 | 7 | 169 | 7 | 0.69 |
| dM | pg/mL | 9.7E2 | 4.0E3 | 1.3E3 | 3.4E3 | 1.4E3 | 2.1E3 | 3.7E2 | 7.1E2 | 1.5E4 | 5.8E3 | 169 | 7 | 169 | 7 | 0.77 |
| dN | ug/mL | 9.8E1 | 1.6E2 | 1.0E2 | 1.8E2 | 4.0E1 | 6.7E1 | 2.4E1 | 1.4E2 | 2.8E2 | 3.3E2 | 169 | 7 | 169 | 7 | 0.91 |
| fR | ng/ml | 1.5E5 | 4.4E5 | 2.1E5 | 4.1E5 | 1.6E5 | 3.1E5 | 3.6E4 | 1.9E2 | 6.9E5 | 8.7E5 | 108 | 7 | 108 | 7 | 0.70 |

Analyte panel data:

Unconstrained panels with 3 analytes, where 1.0E-8 >= 'model p-value' > 0. Contains 10,463 panels of 397,580 total panels evaluated. :
aA{Fr(Et Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nn(Et Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Lw(Et Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Mg(Et Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Mp(Et Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lx Ly Lz Ma Mb Mc Md Me Mf Mh Mi Mj Mk Ml Mm Mn Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Mu(Et Fp Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lx Ly Lz Ma Mb Mc Md Me Mf Mh Mi Mj Mk Ml Mm Mn Mq Mr Ms Mt Mv Mw Mx My Mz Na Nb Nc Nd Ne Nf Ng Nh Ni Nj Nk Nl Nm No Nq Nr Ns Nt Nu Nv Nw Nx Ny Oe

Po Qa) Qc(Et Ij In Io Jg Jh Jj Jk Jn Lh Lv Lx Ma Me Mh Mi Mm Ms Mt No Nq Nt Nw Og Oi Pa Po Qa) Pb(Et Ij In Io Is Jg Jh Jj Jk Jn Jq Lv Lx Ma Me Mh Mi Mm Ms No Nq Nt Nw Og Oi Pa Po Qa) Ml(Et Ij Io Is Jg Jh Jj Jk Jn Lx Ma Me Mh Mi Mm Ms Ne No Nq Nt Nw Og Oi On Pa Po Qa) Oy(Et Ij In Io Is Jj Jk Jn Jq Lh Lv Lx Ma Me Mh Mi Mm Ms No Nq Nt Nw Og Oi Pa Po Qa) Hu(Et Ij In Io Is Jj Jn Lh Lx Ma Me Mh Mi Ms Mt Ne Ng No Ns Nt Nw Og Oi Pa Po Qa) Ns(Et Hr Ij In Io Is Jj Jk Jn Lh Me Mh Mi Mm Ms Mt Ne Nq Nw Og Oi Pa Qa) Ne(Et Hr Ij In Io Jh Jj Jk Me Mh Mi Ms Mt Nq Nw Og Oi Pa Pz Qa) Ng(Et Ij In Io Is Jh Jj Jn Jq Me Mh Mi Mm Ms Mt Nw Og Oi Pa Qa) Hr(Et Ij In Io Jh Jj Jk Ma Me Mh Mi Ms Mt Nq Nw Og Oi Pa Qa) Of(Et Ij In Io Jh Jj Jn Jq Me Mh Mi Mm Ms Nq Nw Og Oi Pa Qa) Pz(In Io Jh Jj Me Mh Mi Ms Nq Og Oi Pa) Jh(Et Ij In Io Jg Jk Mt Nq Nw On Qa) Jj(Io Me Mm Ms Nw Og Oi) Mh(Ij In Mi Ms Qa) Pa(In Jk Lh Lx Mi) Ms(Et Io Og Oi) Ij(In Mt Qa) Nq(Jk Me) Qa(In Jn) Nw(Et Mt) Oi(Io Og) MeJk} Ji{Il(Et Fp Hq Hr Hu Hv Hw Hx Ih Ii Ij Ik Im In Io Ip Iq Ir Is It Iu Iv Jg Jh Jk Jm Jn Jo Jp Jq Jr Js Jt Lh Li Lj Lu Lv Lw Lx Ly Lz Ma Mb Mc Md Me Mf Mg Mh Mi Mj Mk Ml Mn Mq Mr Mt Mv Mw Mx My Mz Na Nb Nc Nd Ne Nf Ng Nh Ni Nj Nk Nl Nm Nq Nr Ns Nu Nv Nw Nx Ny Oe Of Oh Oi Ok Om On Oy Oz Pa Pb Pd Pe Pf Pg Po Qa Qb Qc Qd Qe) Nv(Et Fp Hq Hr Hu Hv Hw Hx Ih Ii Ij Ik Im In Ip Iq Ir Is It Iu Iv Jg Jh Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Mt Mv Mw Mx My Mz Na Nb Nc Nd Ne Nf Ng Nh Ni Nj Nk Nl Nm Nq Nr Ns Nu Nw Ny Oe Of Oh Oi Ok Om On Oy Oz Pa Pb Pd Pe Pf Pg Po Pz Qa Qb Qc Qd Qe) Nr(Et Fp Hq Hr Hu Hv Hw Hx Ih Ii Ij Ik Im In Ip Iq Ir Is It Iu Iv Jg Jh Jk Jm Jn Jo Jp Jq Jr Js Jt Lh Li Lj Lu Lv Ly Lz Ma Mb Mc Md Me Mf Mg Mh Mi Mj Mk Mn Mq Mr Mt Mv Mw Mx My Mz Na Nb Nc Ne Nf Ng Nh Ni Nj Nk Nl Nm Ns Nu Nw Nx Ny Oe Of Oh Oi Ok Om On Oy Oz Pa Pb Pd Pe Pf Pg Po Pz Qa Qb Qd Qe) Ma(Et Fp Hq Hr Hu Hv Hx Ih Ii Ij Ik Im In Ip Iq Ir Is It Iv Jg Jh Jm Jn Jo Jp Jq Js Jt Li Lj Lu Lv Lw Ly Lz Mb Mc Md Me Mf Mg Mh Mj Mk Ml Mm Mn Mq Mr Mt Mv Mw Mx My Mz Na Nb Nc Nd Ne Nf Ng Nh Ni Nj Nk Nl Nm Nq Ns Nu Nw Nx Ny Oe Of Og Oh Oi Ok Om On Oy Oz Pb Pd Pe Pf Pg Po Qa Qb Qc Qd Qe) Et(Fp Hq Hr Hu Hv Hx Ih Ii Ij Ik Im In Ip Iq Ir Is It Iv Jg Jh Jj Jm Jn Jo Jp Jq Jr Js Jt Li Lj Lu Lv Lw Ly Lz Mb Mc Md Me Mf Mg Mh Mj Mk Ml Mn Mq Mr Mt Mv Mw Mx My Mz Na Nb Nc Ne Nf Ng Nh Ni Nj Nl Nm Ns Nu Nw Nx Ny Oe Of Oh Oi Ok Om On Oy Oz Pb Pd Pe Pf Pg Po Qa Qb Qc Qd Qe) Jo(Fp Hq Hr Hu Hv Hx Ih Ii Ij Ik Im In Ip Iq Ir Is It Iv Jg Jh Jm Jn Jp Jq Jr Js Jt Li Lj Lu Lv Lw Ly Lz Mb Mc Md Me Mf Mg Mh Mj Mk Ml Mm Mn Mq Mt Mv Mw Mx My Mz Na Nb Nc Nd Ne Nf Ng Nh Ni Nj Nk Nl Nm Ns Nu Nw Nx Ny Oe Of Oh Oi Ok Om On Oy Oz Pb Pd Pe Pf Po Qa Qb Qc Qd Qe) Na(Fp Hq Hr Hu Hv Hw Hx Ih Ii Ij Ik Im In Iq Ir Is It Iv Jg Jh Jm Jn Jp Jq Jr Js Jt Li Lj Lu Lv Lw Ly Lz Mb Mc Md Me Mf Mg Mh Mj Mk Ml Mn Mq Mr Mt Mv Mw Mx My Mz Nb Nc Ne Nf Ng Nh Ni Nj Nk Nl Nm Ns Nu Nw Nx Ny Oe Of Oh Oi Ok Om On Oy Oz Pb Pd Pe Pf Po Qa Qb Qc Qd Qe) Is(Fp Hq Hr Hu Hv Hx Ih Ii Ij Ik Im In Ip Iq Ir It Iv Jg Jh Jm Jn Jp Jq Jr Js Jt Li Lj Lv Lw Ly Lz Mb Mc Md Me Mf Mg Mh Mj Mk Ml Mn Mq Mr Mt Mv Mw Mx My Mz Nb Nc Ne Nf Ng Nh Ni Nj Nk Nl Nm Ns Nu Nw Ny Oe Of Oh Oi Ok Om On Oy Oz Pb Pd Pe Pf Pg Po Qa Qb Qd Qe) Po(Fp Hq Hr Hu Hv Hw Ih Ii Ij Ik Im In Ip Iq Ir It Iv Jg Jh Jk Jm Jn Jp Jq Jr Js Jt Lh Li Lj Lu Lv Lw Lx Ly Lz Mb Mc Me Mf Mg Mj Mk Ml Mv Mw Mx My Mz Nb Nc Nd Ne Nf Ng Nh Ni Nj Nk Nl Nm Nq Ns Nu Nw Oe Oh Oi Ok Om On Oz Pd Pe Pf Pg Qa Qb Qd Qe) Mg(Fp Hr Hu Hv Hx Ih Ii Ij Ik In Io Ip Ir It Iv Jg Jh Jn Jp Jq Jt Li Lj Lu Lv Lw Ly Lz Mb Mc Md Me Mf Mh Mj Mk Ml Mm Mq Mr Mt Mv Mw Mx My Mz Nb Nc Nd Ne Nf Ng Nh Ni Nj Nk Nl Nm Ns Nu Nw Nx Ny Oe Of Oh Oi Om On Oy Oz Pb Pd Pe Pf Pg Pz Qa Qb Qc Qd Qe) Nc(Fp Hr Hu Hv Hw Hx Ii Ik Im In Ip Ir It Iu Iv Jg Jh Jn Jp Jq Jr Jt Lh Li Lu Lv Lw Ly Lz Mb Mc Md Me Mf Mh Mj Mk Ml Mq Mr Mt Mv Mw Mx My Mz Nb Nd Nf Ng Nh Ni Nj Nk Nl Nm Ns Nu Nw Nx Ny Oe Of Og Oh Oi Ok Om Oy Oz Pb Pd Pe Pf Pg Pz Qa Qb Qc Qd Qe) Qc(Fp Hq Hr Hu Hv Hx Ih Ii Ij Ik Im In Io Ip Iq Ir It Iv Jg Jh Jj Jm Jn Jp Jq Js Jt Li Lj Lv Lw Ly Lz Mb Mc Md Me Mf Mh Mk Ml Mm Mn Mq Mv Mw Mx My Mz Nb Nd Ne Nf Ng Nh Ni Nj Nl Nm Ns Nu Nw Nx Ny Oe Of Oi Ok Om On Oy Oz Pb Pd Pf Pz Qa Qb Qd Qe) Mt(Fp Hq Hr Hu Hv Hx Ih Ii Ij Ik Im In Ip Iq Ir It Iv Jg Jh Jm Jn Jp Jq Jr Js Jt Lh Li Lj Lu Lv Lw Ly Lz Mb Mc Me Mf Mh Mj Mk Mn Mq Mr Mv Mw Mx Mz Nb Nd Ne Nf Ng Nh Ni Nj Nk Nl Nm Ns Nu Nw Nx Oe Oh Oi Ok Om On Oy Oz Pd Pe Pf Pg Qa Qb Qd Qe) Ml(Fp Hq Hr Hu Hv Hx Ih Ij Ik Im Ip Iq Ir It Iv Jg Jh Jj Jm Jn Jp Jq Js Jt Li Lj Lv Lw Ly Lz Mb Mc Md Me Mf Mh Mj Mk Mm Mn Mq Mv Mw Mx My Mz Nb Ne Nf Ng Nh Ni Nj Nk Nl Nm Ns Nu Nw Nx Ny Oe Of Og Oh Oi Ok Om Oy Oz Pb Pd Pf Pz Qa Qb Qd Qe) Lu(Fp Hq Hr Hu Hv Hx Ih Ii Ij Ik Im In Io Iq Ir It Iv Jg Jh Jm Jn Jp Jq Js Jt Lh Li Lj Lv Ly Lz Mb Mc Md Mf Mh Mj Mk Mn Mq Mr Mv Mw Mx My Mz Nb Ne Nf Ng Nh Ni Nl Nm Ns Nu Nw Ny Oe Of Oh Oi Ok Om On Oy Oz Pb Pd Pe Pf Pg Pz Qa Qb Qd Qe) Hu(Fp Hr Hv Hw Hx Ii Ij Ik Im In Io Ip Ir It Iv Jg Jh Jn Jp Jq Jr Jt Lh Li Lv Lw Lx Ly Lz Mb Md Me Mf Mh Mj Mk Mq Mr Mv Mw Mx My Nb Nd Ne Ng Nh Ni Nj Nk Nl Nm Ns Nu Nw Nx Ny Oe Of Og Oh Oi Om On Oy Oz Pb Pd Pe Pg Pz Qa Qb Qd Qe) Pz(Fp Hq Hr Hv Hx Ih Ii Ij Ik Im In Io Iq Ir It Iv Jh Jj Jm Jn Jp Jq Js Jt Li Lj Lv Lw Ly Lz Mb Mc Md Me Mf Mh Mj Mk Mn Mq Mv Mw Mx My Mz Nb Ne Nf Ng Nh Ni Nj Nl Nm Ns Nu Nw Nx Ny Oe Of Og Oh Oi Ok Om Oy Oz Pb Pd Pf Qb Qd) Nk(Fp Hq Hr Hv Hx Ih Ii Ij Ik Im In Iq Ir It Iv Jg Jh Jm Jn Jp Jq Js Jt Li Lj Lv Lw Ly Lz Mb Mc Md Me Mf Mh Mj Mk Mn Mq Mv Mw Mx My Mz Nb Nf Ng Nh Ni Nj Nl Nm Ns Nu Nw Nx Ny Oe Of Oh Oi Ok Om Oy Oz Pb Pd Pf Qa Qb Qd Qe) Jr(Fp Hq Hr Hv Hx Ih Ii Ij Ik Im In Iq Ir It Iv Jg Jh Jm Jn Jp Jq Js Jt Li Lj Lv Lw Ly Lz Mb Mc Md Me Mf Mh Mj Mk Mn Mq Mv Mw Mx My Mz Nb Ne Nf Ng Nh Ni Nj Nl Nm Ns Nu Nw Ny Oe Of Oh Oi Ok Om Oy Oz Pb Pd Pf Qa Qb Qd Qe) On(Fp Hq Hr Hv Hw Hx Ih Ii Ij Ik Im In Iq Ir It Iv Jg Jh Jk Jm Jn Jp Jq Js Jt Lh Li Lj Lv Lw Ly Lz Mb Mc Md Me Mf Mh Mj Mk Mn Mq Mr Mv Mw Mx Mz Nb Ne Nf Nh Ni Nl Nm Ns Nu Nw Ny Oh Ok Om Oz Pa Pb Pd Pe Pf Pg Qa Qb Qd Qe) Nd(Fp Hr Hv Hx Ih Ii Ij Ik Im In Iq Ir It Iv Jg Jh Jm Jn Jp Js Jt Lh Lj Lv Lw Lx Ly Lz Mb Mc Md Mc Mf Mh Mi Mj Mk Mn Mq Mr Mv Mw Mx My Mz Nb Ne Nf Ng Ni Nl Nm Nu Nw Ny Oe Of Oh Oi Ok Om Oy Oz Pb Pd Pf Pg Qa Qb Qd Qe) Ip(Fp Hq Hr Hv Hx Ih Ii Ij Ik Im In Iq Ir It Iv Jg Jh Jm Jn Jp Jq Js Jt Li Lj Lv Lw Ly Lz Mb Mc Md Me Mf Mh Mj Mk Mn Mq Mv Mw Mx My Mz Nb Ne Nf Ng Nh Ni Nj Nl Ns Nu Nw Ny Oe Of Oh Ok Om Oy Oz Pb Pd Pf Qa Qb Qd Qe) Mm(Fp Hq Hr Hv Hx Ih Ii Ij Ik Im In Iq Ir It Iv Jg Jh Jm Jp Jq Js Jt Li Lj Lv Lw Lz Mb Mc Md Me Mf Mj Mk Mn Mq Mv Mw Mx My Mz Nb Nc Nf Ng Nh Ni Nj Nl Ns Nu Nw Nx Ny Oe Of Oh Ok Om Oy Oz Pb Pd Pf Qa Qb Qd Qe) Hw(Fp Hq Hr Hv Hx Ih Ii Ij Ik Im In Iq Ir It Iv Jg Jh Jm Jn Jp Js Jt Lh Li Lj Lv Lw Ly Lz Mb Mc Md Me Mf Mh Mj Mk Mn Mq Mr Mv Mw Mx My Mz Nb Nf Ng Ni Nl Nm Nu Nw Ny Oe Oh Ok Om Oy Oz Pb Pd Pe Pf Qa Qb Qd Qe) Nx(Fp Hr Hv Hx Ih Ii Ik Im In Io Ir Iv Jg Jh Jj Jn Jp Jq Js Jt Li Lv Lw Ly Lz Mb Md Mf Mh Mj Mk Mn Mq Mv Mw Mx My Mz Nb Ne Nf Ng Nh Ni Nj Nl Nm Ns Nu Nw Ny Oe Of Og Oh Oi Ok Om Oy Oz Pb Pd Pf Qa Qb Qd Qe) Mr(Fp Hq Hr Hv Ih Ii Ij Ik Im In Iq Ir It Iv Jg Jh Jm Jn Jp Js Jt Lh Li Lj Lv Lw Lx Ly Lz Mb Mc Me Mf Mi Mj Mk Mn Mq Mv Mw Mx Mz Nb Ne Nf Ng Ni Nj Nl Nm Ns Nu Nw Ok Om Oy Oz Pa Pd Pe Pf Pg Qa Qb Qd Qe) Io(Fp Hq Hr Hv Hx Ih Ii Ij Ik Im In Iq Ir It Iv Jg Jh Jm Jn Jp Jq Js Li Lj Ly Lz Mb Mc Md Mc Mf Mh Mj Mk Mn Mq Mv Mw Mx My Mz Nb Ne Nf Ng Nh Ni Nm Ns Nu Nw Ny Oe Of Oh Oi Ok Om Oy Oz Pb Pd Pf Qb Qd) Pg(Fp Hq Hr Hv Hx Ih Ij Ik Im In Iq Ir It Iv Jg Jh Jm Jn Jp Jq Js Jt Lh Li Lj Lv Lw Ly Lz Mb Mc Me Mf Mh Mj Mk Mn Mq Mv Mw Mx Mz Nb Nc Nf Nh Ni Nj Nl Nm Ns Nu Nw Oe Oh Ok Om Oz Pd Pe Pf Qa Qb Qd Qe) Og(Fp Hq Hr Hv Ih Ij Ik Im Iq Ir It Iv Jm Jn Jp Jq Js Jt Li Lj Lv Lw Ly Lz Mb Mc Md Me Mf Mh Mj Mk Mn Mq Mx My Mz Ne Nf Ng Nh Ni Nj Nl Nm Ns Nu Nw Ny Oe Of Oh Oi Ok Oy Oz Pb Pd Pf Qa Qb Qd Qe) Jj(Fp Hq Hr Hv Hx Ih Ij Ik Im In Iq Ir It Iv Jm Jp Js Lj Lv Lw Ly Lz Mb Mc Me Mf Mh Mj Mk Mn Mq Mv Mw Mx My Mz Nb Ne Nf Ng Ni Nj Nl Nm Ns Nu Nw Ny Oe Of Oi Ok Om Oy Oz Pb Pf Qa Qb Qd Qe) Pe(Fp Hq Hv Ih Ii Ij Ik Im In Iq Ir It Iv Jg Jh Jm Jn Jp Js Jt Lh Li Lj Lv Lw Ly Lz Mb Mc Me Mf Mj Mk Mn Mq Mv Mw Mx Mz Nb Nc Nf Ng Nh Ni Nj Nl Nm Ns Nu Nw Ok Om Oz Pa Pd Pf Qa Qb Qd Qe) Iu(Fp Hq Hv Hx Ih Ii Ij Ik Im In Iq Ir It Iv Jh Jm Jn Jp Js Li Lj Lv Lw Ly Lz Mb Mc Md Me Mf Mh Mj Mk Mn Mq Mv

Figure 42 Continued

Mw Mx My Mz Nb Nf Ni Nl Nm Ns Nu Ny Oe Ok Om Oy Oz Pb Pd Pf Qa Qb Qd Qe) Mi(Fp Hq Hr Hv Ih Ii Ij Ik Im In Iq Ir It Iv Jg Jh Jm Js Jt Lh Lj Lv Lw Lx Ly Lz Mb Mc Me Mf Mj Mk Mn Mq Mv Mw Mx Mz Nb Ne Nf Ni Nl Nm Ns Nu Nw Oe Oh Ok Om Oz Pd Pf Qa Qb Qd Qe) Pc(Fp Hq Hr Hv Ih Ii Ij Ik Im In Iq It Jg Jh Jm Jp Js Jt Li Lj Lv Lw Mb Mc Md Me Mf Mh Mj Mk Mn Mq Mv Mw Mx Mz Nb Ne Nf Ng Ni Nj Nl Nm Nu Nw Ny Oe Of Oh Ok Om Oy Pb Pd Pf Qb Qe) Oz(Fp Hq Hr Hx Ik Im In Ir It Iv Jg Jh Jk Jn Jp Jq Jt Lh Li Lv Lw Ly Lz Md Me Mh Mj Mk Mq Mv Mw My Mz Ne Nf Ng Nh Nj Nl Nm Ns Nw Ny Oe Of Oh Oi Om Oy Pa Pb Pd Qa Qb Qd Qe) Jg(Fp Hx Ii Ik In Ir Iv Jk Jn Jp Jq Jt Lh Li Lv Lw Ly Lz Mb Md Mf Mh Mj Mq Mv Mw Mx My Mz Nb Ne Ng Nh Ni Nj Nl Nm Nq Ns Nu Nw Ny Oe Of Oh Oi Om Oy Pa Pb Pd Qa Qd Qe) Lh(Fp Hq Hv Ih Ij Ik Im In Iq Ir It Iv Jh Jm Jn Jp Js Jt Li Lj Lv Lx Ly Lz Mb Mc Me Mf Mj Mk Mn Mq Mv Mw Mx Mz Nb Nf Ni Nl Nm Ns Nu Nw Ok Om Pa Pd Pf Qa Qb Qd Qe) Oi(Fp Hr Hv Hx Ih Ii In Ir Iv Jh Jn Jp Jq Jt Li Lv Lw Ly Lz Mb Md Me Mh Mj Mk Mn Mq Mv Mw Mx My Mz Nb Ne Nf Nh Ni Nj Nl Ns Nu Nw Ny Oh Om Oy Pb Pd Qa Qb Qd Qe) Pd(Fp Hr Hx Ii Ik In Ir It Iv Jh Jk Jn Jp Jq Jt Li Lv Lw Lx Ly Lz Mb Md Me Mf Mh Mj Mq Mw My Nb Ne Ng Nh Nj Nl Nm Nq Ns Nu Ny Oe Of Oh Om Oy Pa Pb Qa Qd Qe) Lx(Fp Hv Ih Ii Ij Ik Im In Iq Ir It Iv Jh Jm Jp Js Lj Lv Ly Lz Mb Mc Me Mf Mj Mk Mn Mv Mw Mx Mz Nb Nf Ni Nl Nm Ns Nu Nw Oe Ok Om Pf Qa Qb Qd Qe) Nq(Fp Hq Hr Hv Ih Ii Ij Im In Iq Ir It Jh Jm Jp Js Jt Lv Lw Ly Lz Mb Mc Me Mf Mj Mk Mn Mq Mx Mz Nb Nf Ni Nl Nm Nu Nw Ok Om Pf Qa Qb Qd Qe) Li(Hr Hx Ii Ik Ir Iv Jh Jn Jp Jq Jt Lj Lv Lw Ly Lz Mb Md Mh Mj Mk Mq Mv Mw Mx My Nb Ne Ng Nh Nj Nl Nm Ns Nu Nw Ny Oe Of Oh Om Pb Qa Qd Qe) Mh(Hr Hx Ii Ik In It Iv Jh Jn Jp Jq Jt Lv Lw Ly Mb Md Me Mj Mq Mw My Nb Ne Ng Nh Nj Nl Ns Nu Nw Ny Oe Of Oh Om Pb Qa Qb Qd Qe) Iv(Hr Hx Ii Ik It Jh Jn Jp Jq Jt Lv Lw Ly Lz Mb Md Me Mj Mq Mv Mw My Nb Ne Ng Nh Nj Nm Nu Nw Ny Oe Of Oh Om Pb Qa Qb Qe) Oh(Fp Hr Hx Ii Im In Ir Jh Jn Jp Jq Jt Lv Ly Lz Md Mj Mk Mq Mv Mw My Nb Ne Nh Nj Nl Nm Nu Nw Ny Oe Of Om Pb Qa Qd Qe) Ly(Hr Hx Ik Ir It Jh Jk Jn Jp Jq Jt Lv Lw Lz Mb Md Mj Mq Mv Mw My Nb Ne Nh Nj Nl Nu Ny Oe Of Om Pa Pb Qa Qd Qe) Pa(Fp Hq Hv Ih Im Iq Ir It Jh Jm Jp Js Lj Lz Mb Mc Me Mf Mn Mq Mx Mz Nf Ni Nl Nm Ns Nu Nw Ok Pf Qa Qb Qd Qe) Nh(Fp Hr Hx Ii Ir Jh Jn Jp Jq Jt Lv Lw Lz Md Mj Mk Mq Mv Mw Mx My Nb Nj Nl Nu Nw Ny Oe Of Om Pb Qa Qd Qe) Jk(Fp Hq Hv Ih Im In Iq Ir It Jh Jm Jp Js Mb Mc Me Mj Mk Mn Mx Mz Nb Nf Ni Nl Nu Nw Ok Pf Qa Qb Qd Qe) Jn(Hr Hx Ii It Jh Jp Jq Js Jt Lv Lw Lz Mb Md Mj Mq Mv Mw My Nb Ne Nj Nl Nm Nu Nw Ny Oe Of Om Pb Qa Qe) Jq(Fp Hv Hx Ii Jh Jp Jt Lv Lz Mb Md Mj Mk Mq Mv Mw Mx My Nb Ne Nj Nl Nm Nu Ny Oe Of Om Pb Qa Qe) Nj(Fp Hx Ii Ir Jh Jp Jt Lv Lz Mb Md Mj Mq Mv Mw Mx My Nb Ne Ng Nu Nw Of Om Pb Qa Qd Qe) Md(Hx Ii In Ir Jp Jt Lv Lz Mj Mq Mv Mw My Nb Ne Nl Nu Nw Ny Oe Of Om Pb Qa Qd Qe) Hx(Hr Ii In Jp Jt Lv Lw Lz Mj Mq Mw My Nb Ne Nu Nw Ny Oe Of Om Oy Pb Qa) Om(Ir Jt Lv Lw Lz Mj Mq My Ne Ng Nl Nm Nu Ny Oe Of Oy Pb Qa Qe) Ms(Hq Ij Ik Im In Jm Js Lj Mc Mf Mz Nf Ng Nw Ok Oy Pf Qb) Nb(Hr Jp Lv Lw Lz Mw My Ne Ng Nu Ny Oe Oy Pb Qa Qd Qe) Pb(Ii In Jh Jp Lz Mj Mq Mv Mw My Ne Nf Nu Nw Ny Qe) Lz(Hr Ii Jh Jp Lv Lw Mb Mq Mw My Ne Nw Qb Qe) Of(Ii In Jh Jp Jt Mj Mk Mq Mv Mw Nu Nw Qa Qe) Jp(Jt Lv Lw Mj Mq My Ne Nm Nu Ny Oe Qa) Nu(Ik Lv Mj Mq Mw Ne Nw Ny Qa Qe) Lv(Ii Jt Mb Mj Mq Mw Ne Oe Qb) Mw(Jt Mj Mq Ne Nl Nm Ny Oe) Qa(Ii Lw Mq Ne Nm Nw Oe Qb) Qe(Hr Jt Mq Ne Ng Nm Oe Qb) Ny(Ii In Mj Mv Nf Nw) Ne(Ir Jt Mj Mq Mv) Nw(Jt Mq My Oe) Mj(Ik Im Oe) Ng(Jh Jt Mv) Ii(My Oe Oy) Nm(Jt Lw) Ns(Jh Mq) Me(Hv Mf) In(Ij My) Qd(Ik Im) MqOe Irlt} No{Lv(Et Fp Hq Hr Hu Hv Hw Hx Ih Ii Ij Ik Il Im In Io Iq Ir It Iu Iv Jg Jh Jk Jl Jm Jn Jo Jp Js Jt Lh Li Lj Lu Lx Ly Lz Ma Mb Mc Md Me Mf Mh Mi Mj Mk Ml Mn Mq Mr Ms Mt Mv Mw Mx My Mz Na Nb Nc Nd Ne Nf Ng Nh Ni Nj Nk Nl Nm Nq Nr Ns Nt Nu Nv Nw Nx Ny Oe Of Og Oi Ok Om Oy Oz Pa Pb Pd Pe Pf Pg Po Pz Qa Qb Qc Qd Qe) Et(Fp Fr Hq Hr Hu Hv Hw Hx Ih Ii Ij Ik Il Im In Io Ip Iq Ir It Iu Iv Jg Jh Jk Jl Jm Jo Jp Js Jt Lh Li Lj Lu Lx Ly Lz Ma Mb Mc Md Me Mf Mh Mi Mj Mk Ml Mn Mq Mr Ms Mt Mv Mw Mx My Mz Na Nb Nc Ne Nf Ng Nh Ni Nk Nl Nm Nq Nr Ns Nt Nu Nv Nw Nx Ny Oe Of Og Oi Ok Om Oy Oz Pa Pb Pd Pe Pf Pg Po Pz Qa Qb Qc Qd Qe) Mz(Fp Hq Hr Hu Hv Hw Hx Ih Ii Ij Ik Il Im In Io Iq Ir It Iu Iv Jg Jh Jk Jl Jm Jn Jo Jp Jq Js Jt Lh Li Lj Lu Lx Ly Lz Ma Mb Mc Md Me Mf Mh Mj Mk Ml Mn Mq Mr Ms Mt Mv Mw Mx My Na Nb Nc Nd Ne Nf Ng Nh Ni Nk Nl Nm Nr Ns Nt Nu Nv Nw Nx Ny Oe Of Og Oi Ok Om Oy Oz Pa Pb Pd Pe Pf Pg Po Pz Qa Qb Qc Qd Qe) Jn(Fp Hq Hr Hu Hv Hw Hx Ih Ii Ij Ik Il Im In Io Iq Ir It Iu Iv Jh Jk Jl Jm Jo Jp Jr Js Jt Lh Li Lj Lu Lx Ly Lz Ma Mb Mc Md Me Mf Mh Mj Mk Ml Mn Mq Mr Ms Mt Mv Mw Mx My Na Nb Nc Nd Ne Nf Ng Nh Ni Nk Nl Nm Nr Ns Nt Nu Nv Nw Nx Ny Oe Of Og Oi Ok Om Oy Oz Pa Pb Pd Pe Pf Pg Po Pz Qa Qb Qc Qd Qe) Mi(Fp Hq Hr Hu Hv Hw Hx Ih Ii Ij Ik Il Im In Iq Ir It Iu Iv Jh Jk Jm Jo Jp Js Jt Lh Li Lj Lu Lx Ly Lz Ma Mb Mc Md Me Mf Mh Mj Mk Ml Mn Mq Mr Ms Mt Mv Mw Mx My Na Nb Nc Nd Ne Nf Ng Nh Ni Nk Nl Nm Nq Nr Ns Nt Nu Nv Nw Nx Ny Oe Of Og Oh Oi Ok Oy Oz Pa Pb Pd Pe Pf Pg Po Pz Qb Qc Qd Qe) Qa(Fp Hq Hr Hu Hv Hw Hx Ih Ii Ij Ik Il Im In Io Iq Ir It Iu Iv Jh Jk Jl Jm Jp Js Jt Lh Li Lj Lu Lx Ly Lz Ma Mb Mc Md Me Mf Mh Mj Mk Ml Mn Mq Mr Ms Mt Mv Mw Mx My Na Nb Nc Nd Ne Nf Ng Nh Ni Nk Nl Nm Nr Ns Nt Nu Nv Nw Nx Ny Oe Of Og Oi Ok Om Oy Oz Pa Pb Pd Pe Pf Pg Po Pz Qb Qc Qd Qe) Jg(Fp Fr Hq Hr Hu Hv Hw Hx Ih Ii Ij Ik Il Im In Io Iq Ir It Iu Iv Jh Jk Jm Jo Jp Js Lh Li Lj Lu Lx Ly Lz Ma Mb Mc Md Me Mf Mh Mj Mk Ml Mn Mq Mr Ms Mt Mv Mw Mx Na Nb Nc Nd Ne Nf Nh Ni Nj Nk Nl Nm Nq Nr Nt Nu Nv Nw Nx Ny Oe Of Ok Om On Oy Oz Pa Pb Pd Pe Pf Pg Po Pz Qb Qc Qd Qe) Oh(Fp Hq Hr Hu Hv Hw Hx Ih Ii Ij Ik Il Im Io Iq Ir It Iu Iv Jh Jk Jm Jo Jp Js Jt Lh Li Lj Lu Lx Ly Lz Ma Mb Mc Md Me Mf Mh Mj Mk Ml Mn Mq Mr Ms Mt Mv Mw Mx My Na Nb Nc Nd Ne Nf Ng Nh Ni Nk Nl Nm Nq Nr Ns Nt Nu Nv Nw Nx Ny Oe Of Og Ok Oy Oz Pa Pb Pd Pe Pf Pg Po Pz Qb Qc Qd Qe) Ip(Fp Hq Hr Hu Hv Hw Hx Ih Ii Ij Ik Il Im In Io Iq Ir It Iu Iv Jh Jk Jl Jm Jp Js Lh Li Lj Lu Lx Ly Lz Ma Mb Mc Md Me Mf Mh Mj Mk Ml Mn Mq Mr Ms Mt Mv Mw Mx My Na Nb Nc Nd Ne Nf Ng Nh Ni Nk Nl Nm Nr Ns Nt Nu Nv Nw Nx Ny Oe Of Og Oi Ok Oy Pa Pb Pd Pe Pf Pg Po Qb Qc Qd Qe) Nq(Fp Fr Hq Hr Hv Hw Hx Ih Ii Ij Ik Il Im Io Iq Ir It Iu Iv Jh Jk Jm Jo Jp Js Lh Li Lj Lu Lx Ly Lz Ma Mb Mc Md Me Mf Mg Mh Mj Mk Ml Mn Mq Mr Ms Mt Mv Mw Mx Nb Nc Nd Ne Nf Nh Ni Nk Nl Nm Nr Ns Nt Nu Nv Nw Nx Ny Oe Of Om On Oy Oz Pa Pb Pd Pe Pf Pg Po Pz Qb Qc Qd Qe) Nj(Fp Hq Hr Hv Hw Hx Ih Ii Ij Ik Il Im In Io Iq Ir It Iu Iv Jh Jk Jl Jm Jo Jp Js Lh Li Lj Lu Lx Ly Lz Ma Mb Mc Md Me Mf Mh Mj Mk Ml Mn Mq Mr Ms Mt Mv Mw Mx My Na Nb Nc Nd Ne Nf Ng Nh Ni Nk Nl Nm Nr Ns Nt Nu Nv Nw Nx Ny Oe Of Og Oi Ok Oz Pa Pb Pd Pe Pg Po Pz Qb Qd Qe) Om(Fp Hq Hr Hu Hv Hw Hx Ih Ij Ik Il Im In Io Iq Ir It Iu Iv Jh Jk Jl Jm Jp Js Lh Li Lj Lu Lx Ly Lz Ma Mb Mc Md Me Mf Mh Mj Mk Ml Mn Mq Mr Ms Mt Mv Mw Mx Na Nb Nc Nd Ne Nf Nh Ni Nk Nl Nm Nr Ns Nt Nu Nv Nw Nx Ny Oe Oi Ok On Oy Oz Pa Pb Pd Pe Pf Pg Po Qb Qc Qd Qe) Jt(Fp Hq Hr Hu Hv Hw Hx Ih Ij Ik Il Im Iq Ir It Iu Iv Jh Jk Jm Jp Js Lh Li Lj Lu Lx Ly Lz Ma Mb Mc Md Me Mf Mh Mj Mk Ml Mn Mq Mr Ms Mt Mv Mw Mx My Na Nb Nc Nd Ne Nf Nh Ni Nk Nl Nm Nr Ns Nt Nu Nv Nw Nx Ny Oe Of Oi Ok Oy Oz Pa Pb Pd Pe Pf Pg Po Pz Qb Qc Qd Qe) Jl(Fp Hq Hu Hv Hw Hx Ih Ij Ik Il Im In Iq Ir It Iu Iv Jh Jk Jm Jp Js Lh Li Lj Lu Lx Ly Lz Ma Mb Mc Md Me Mf Mh Mj Mk Ml Mn Mq Mr Ms Mt Mv Mw Mx My Na Nb Nc Nd Ne Nf Ng Nh Ni Nk Nl Nr Ns Nt Nu Nv Nw Nx Ny Of Ok Oy Oz Pa Pb Pd Pe Pf Pg Po Qb Qc Qd Qe) Fr(Fp Hq Hr Hu Hx Ih Ii Ik Il Im Iq It Iu Iv Jh Jk Jm Jp Js Lh Li Lj Lu Lx Ly Lz Ma Mb Mc Md Me Mf Mh Mj Mk Ml Mn Mr Ms Mt Mv Mw Mx My Nb Nc Nd Ne Nf Nh Ni Nk Nl Nr Ns Nu Nv Nw Nx Ny Of Oy Pa Pb Pd Pe Pf Pg Po Qb Qc Qd Qe) Ok(Hr Hv Hx Ii Ik Im In Io Ir Iu Iv Jh Jk Jo Jp Jq Lh Li Lu Lw Ma Mb Md Me Mf Mh Mk Ml Mn Mq Ms Mt Mv Mw Mx Na Nb Nc Nd Ne Nf Ng Nh Ni Nk Nm Ns Nt Nv Nw Nx Oe Of Og Oi On Oz Pa Pb Pe Pg Po Pz Qb Qd Qe) Nm(Fp Hr Hv Hx Ii Im In Io Ir Iu Iv Jh Jk Jm Jo Jp Jq Js Lh Li Lu Lw Lx Ma Mb Md Mf Mg Mh Mk Mn Mq Ms Mt Mv Mw Mx Na Nb Nc Nd Ne Nf Ng Nh Ni Nk Ns Nt Nv Nw Oe Of Og Oi Oz Pa Pb Pe Pg Po Pz Qb Qd) Jr(Fp Hq Hu Hv Hw Hx Ih Ij Ik Il In Iq Ir It Iu Iv Jm Jp Js Li Lu Lx Ly Lz Mc Md Mk Mn Mr Ms Mv Mw Mx My Na Nb Nc Nf Ng Ni Nk Nl Nr Nu Nv Nw Nx Ny Of Oy Oz Pa Pb Pd Pe Pf Pg Po Qb Qd Qe) Mt(Hr Hv Hw Hx Ii Ij Ik Im In Io Ir Iu Iv Jh Jk Jm Jo Jp Lh Li Lj Ly

Lw Mj Ms Mt Mx My Nf Ng Ns Oy) Lv(Hv Ih Ij Im Iu Jp Ms Mt Nd Nf Ng Og Pc) Im(Hv Ij Iu Md Mj Mq Ms Nc Nf Og Oz Pz) Hv(Iu Jp Ma Mm Ms Mt Nd Nv Og Oz) Ms(Ij Iu Jh Jp Lw Mt Nf) Og(Il Jg Lw Nf Nm Nv Qe) Mt(Ij Mm Nf Oy Pb Pz) Iu(Ij Jp Lw Nf Ni) Jp(Ij Io Nf Pz) Jq(Hr Ij Ik Lw) Lw(Lu Me) Nf(Nj Oz) WmJr NsMq MrIl NdIj NgJg NiNk NvOe NyPb} Fr{Ir(Et Fp Hq Hr Hu Hv Hw Hx Ih Ii Ij Ik Il Im In Io
Ip Iq Is It Iu Iv Jg Jh Jk Jl Jm Jn Jo Jp Js Jt Lh Li Lj Lu Lv Lw Lx Ly Lz Ma Mb Mc Md Me Mf Mg Mh Mi Mj Mk Ml Mm Mn Mq Mr Ms Mt
Mu Mv Mw Mx My Mz Na Nb Nc Nd Ne Nf Ng Nh Ni Nj Nk Nl Nm Nq Nr Ns Nt Nu Nv Nw Nx Ny Oe Of Og Oh Oi Ok Om On Oy Oz Pa Pb
Pc Pd Pe Pf Pg Po Qa Qc) Qa(Et Fp Hq Hr Hu Hv Hw Hx Ih Ii Ij Ik Il Im In Io Ip Iq It Iu Iv Jg Jh Jk Jl Jm Jn Jo Jp Js Jt Lh Li Lj Lu Lv Lw Lx
Ly Lz Ma Mb Mc Md Me Mf Mh Mi Mj Mk Ml Mm Mn Mq Mr Ms Mt Mu Mv Mw Mx My Mz Na Nb Nc Nd Ne Nf Nh Ni Nj Nk Nl Nm Nq
Nr Ns Nt Nu Nv Nw Nx Ny Oe Of Og Oh Oi Ok Om On Oy Oz Pa Pb Pc Pd Pe Pf Pg Po Qb Qc Qd Qe) Jt(Et Fp Hq Hr Hu Hv Hw Hx Ih Ii Ij Ik
Il Im In Ip Iq It Iu Iv Jg Jh Jk Jl Jm Jn Jp Js Lh Li Lj Lu Lv Lw Lx Ly Lz Ma Mb Mc Md Me Mf Mh Mi Mj Mk Ml Mm Mn Mp Mq Mr Mt Mu
Mv Mw Mx My Mz Na Nb Nc Nd Ne Nf Nh Ni Nj Nk Nl Nm Nq Nr Ns Nt Nu Nv Nw Nx Ny Oe Of Oh Oi Ok Om On Oy Oz Pa Pb Pc Pd Pe
Pf Pg Po Qb Qc Qd Qe) Jn(Et Fp Hq Hr Hu Hv Hw Hx Ih Ii Ij Il Im In Io Ip Iq It Iu Iv Jg Jh Jk Jl Jm Jo Jp Js Lh Li Lj Lu Lv Lx Ly Lz Ma Mb
Mc Md Me Mf Mh Mj Mk Ml Mm Mn Mq Mr Mt Mv Mw Mx My Mz Nb Nc Nd Ne Nf Nh Ni Nj Nk Nl Nm Nq Nr Ns Nu Nv Nw Nx Ny Oe
Of Oh Oi Ok Om On Oy Oz Pa Pb Pd Pe Pf Pg Po Qb Qc Qd Qe) Nt(Et Fp Hq Hr Hu Hv Hw Hx Ih Ii Ij Il Im In Ip Iq It Iu Iv Jg Jh Jk Jl Jm Jp
Js Lh Li Lj Lu Lv Lx Ly Lz Ma Mb Mc Md Me Mf Mh Mi Mj Mk Ml Mm Mn Mq Mr Ms Mt Mu Mv Mw Mx My Na Nb Nc Nd Ne Nf Nh Ni
Nk Nl Nm Nq Nr Ns Nu Nv Nw Nx Ny Of Oi Ok Om On Oy Oz Pa Pb Pc Pd Pe Pf Pg Po Qb Qc Qd Qe) Na(Et Fp Hq Hr Hu Hv Hw Hx Ih Ii Ij
Ik Il Im In Io Ip It Iu Iv Jl Jo Jp Js Lh Li Lj Lv Lw Lx Ly Lz Ma Md Mf Mg Mh Mi Ml Mm Mq Mr Ms Mt Mu Mw Mx My Nc Nd Ne Nf Nh Ni
Nj Nk Nl Nm Nq Nr Ns Nu Nv Nw Nx Ny Oe Of Og Oh Oi Ok Om On Oy Oz Pa Pb Pc Pd Pe Pg Po Pz Qb Qd) Hw(Et Fp Hq Hr Hu Hv Hx Ih
Ii Ik Il Im In Io Ip It Iu Iv Jg Jh Jl Jm Jp Js Lh Li Lj Lv Lw Lx Ly Lz Ma Md Mf Mg Mh Mi Mk Ml Mm Mq Mr Ms Mt Mu Mv Mw Mx My Mz
Nc Nd Ne Nf Nh Ni Nj Nk Nl Nm Nq Ns Nv Nw Nx Ny Oe Og Oi Ok Om On Oy Oz Pa Pb Pc Pd Pe Pg Pz Qb Qd Qe) Mz(Et Fp Hr Hu Hv Hx
Ih Ik Il Im In Io Ip Iu Iv Jl Jo Jq Lh Li Lj Lv Lw Lx Ly Lz Ma Mb Md Mf Mg Mh Mi Ml Mm Mn Mq Mr Ms Mt Mu Mv Mw Mx My Nb Nc Nd
Ne Nf Ng Nh Ni Nj Nk Nl Nm Nq Nr Ns Nu Nv Nw Nx Ny Oe Of Oh Oi Ok Om On Oy Oz Pa Pb Pc Pe Pg Pz Qb Qc Qd) Jj(Et Fp Hq Hr Hu Ik
Il Io Iq It Jg Jm Jp Li Lj Lu Ly Lz Ma Mb Mc Me Mf Mh Mj Mk Ml Mm Mn Ms Mv Mw My Nb Nd Ne Ng Nh Ni Nj Nl Nm Ns Nu Nv Nw Nx
Ny Oe Of Og Oi Ok Oy Oz Pa Pb Pc Pf Po Qc Qd Qe) Lh(Et Hq Hr Hu Hv Hx Ih Ii Ik Il Im In Io Ip Iu Iv Jl Jm Js Lj Lv Ly Md Mh Mi Mk Ml
Mm Mp Mq Ms Mt Mu Mv Mw Mx My Nc Nd Ne Nh Ni Nj Nk Nm Ns Nw Nx Ny Oe Oh Oi Ok Om On Oy Oz Pb Pc Pe Pg Pz Qd) Lw(Et Fp
Hu Hv Hx Ih Ij Im In Io Ip Iu Iv Jo Js Lj Lu Lv Lx Lz Md Me Mf Mg Mh Mi Mm Mp Mq Mr Ms Mt Mu Mx My Nb Nc Nd Nf Ng Nk Nr Ns
Nw Oe Of Og Oh Oi Ok Om On Oy Pa Pe Pg Po Pz Qb Qd Qe) Jl(Et Hq Hr Hu Hv Ih Ii Ij Ik Im In Io Ip Is Iu Iv Jm Jo Js Lx Md Me Mf Mg Mh
Mi Mm Mp Mq Mr Ms Mt Mu Mx My Nc Ne Nf Ni Nj Nk Nm Ns Nw Nx Oe Of Oh Oi Ok Om On Oy Oz Pb Pc Pe Qd) Is(Et Fp Hr Hx Ih Im
Iq It Iv Jh Jk Jp Js Li Lj Lu Lv Ly Lz Ma Mc Md Me Mf Mj Mk Ml Mn Mv Mw Mx Nb Nd Ni Nl Nq Nr Nu Nv Nw Ny Ok Om On Oz Pa Pb
Pd Pf Pg Po Qb Qd Qe) Pe(Et Hq Hr Hu Hv Hx Ih Ij Ik Il Im In Io Ip Iu Iv Jo Lv Lz Mb Mg Mh Mi Mk Ml Mm Mp Mq Ms Mt Mu My Nc Ng
Nj Nk Nm Ns Nw Ny Oe Of Og Oh Oi Ok On Oy Oz Pb Pc Pf Pz Qd) Mu(Et Hu Hv Ih Ij Ik Im In Ip Iu Iv Jo Js Lj Lv Lx Lz Me Mf Mg Mh Mi
Mm Mp Mq Mr Ms Mt Mv Mx My Nc Nf Nj Nk Nm Nr Ns Nw Oe Of Og Oh Oi Ok On Oy Pa Pb Pc Pz Qd) Mp(Et Fp Hq Hu Hv Hx Ih Ij Im
In Io Ip It Iv Jo Js Lj Me Mg Mh Mi Mk Mq Mr Ms Mt Mx Nb Nc Nf Ni Nj Nk Nm Nr Ns Nw Oe Of Og Oh Oi Ok Om On Oy Pd Pf Pg Qd)
Ng(Et Hv Hx Ih Ii Ij Im In Ip Iu Iv Jg Jh Jk Js Lv Lx Md Me Mg Mi Mq Mr Mt Mw Mx Nb Nc Nf Nm Nr Nv Oh Ok Om Pa Pc Pg Po Qd)
Mi(Et Hq Hv Ih Ij Ik Im In Io Ip Iv Jo Lv Me Mg Mm Mq Ms My Nc Nf Ni Nj Nk Nm Nw Og Oh Oi Ok Om On Oy Pc Pz Qd) Hv(Hu Ih Im Ip
Iu Iv Jo Lx Mg Mh Mm Mq Mr Ms Mt Mx My Nc Nj Nk Nl Nw Oe Of Og Oh On Oy Pa Pb Pc Pz Qd) In(Hu Hx Ih Im Ip Iu Iv Jo Jq Md Mg
Mh Ml Mm Ms Mt My Nc Nj Nk Nw Ny Oh On Oy Pb Pc Pz Qd) Mq(Hu Ih Im Io Ip Iu Iv Jo Lx Mg Mm Mr Ms Mt Nc Nf Nj Nk Ns Nw Oe
Og Oh On Oy Pb Pz Qd) Pz(Hu Hx Ih Ij Im It Iu Iv Jo Js Li Mm Mr Mt Mx Nf Nj Nm Nr Nw Oh Ok Om Pc Pg Qb Qe) On(Hu Ih Ij Ik Im Io Ip
Iv Jo Lj Mg Mm Mv Mw Mx Nc Nf Nj Nk Nm Ns Of Oh Oi Pb Qd) Jq(Iq It Jg Jh Jm Jp Js Lu Ly Ma Mb Mc Mj Mk Mn Mw Nb Nf Nv Nw Ok
Pd Pf Qe) Og(Ih Ii Ip Iu Iv Jg Jh Jo Lx Mg Mr Mx Nf Nm Nr Nw Oh Ok Pa Pc Pg Po Qe) Oh(Hx Ij Im Io Ip Iv Jo Lv Lx Me Mg Mr Ms Nc Nf
Nj Nm Nr Oi Ok Om Pa) Iv(Hu Ij Ik Im Io Ip Jo Lv Mg Mm Ms Mt My Nj Nm Oe Oi Ok Oy Pc) Ip(Ih Ij Io Jo Mg Mm Mr Ms Mt Nc Nf Nk Nr
Of Oi Ok Pa Pc) Mr(Jo Lv Mg Mh Mm Ms My Nc Nm Oe Of Oy Pb Pc Qd) Oy(Hx Ii Ij Jo Lx Md Mt Mw Nf Nw Om Pa Pg Po) Mg(Et Hx Ij Iu
Mx Nc Nf Nm Nr Ok Om Pc Pg) Jo(Hu Ih Im Ms Mt Nk Nw Oe Of Pb Pc Qd) Pc(Ih Ij Ms Mx Nf Nr Oi Ok Pa Qd) Mt(Hx Mh Mv Nm Ny Of
Oi Ok Pb) Ms(Hx Ij Jh Nb Nm Nw Ok Om) My(Hx Ii Ij Jh Lx Md Nf Nw) Nf(Iu Mm Nc Nj Nk Of Qd) Nk(Et Ij Im Ni Nm Ok) Ih(Ij Lv Nm Oi
Ok) Qd(Ik Il Im Mm Qc) Nc(Ij Im Nm Ok) Jr(Iq It Qb Qe) Oe(Hx Nb Nr Pa) Lx(Hq Nm Ok) Mx(Io Nm Ok) Hu(Jh Jk Om) Ij(Iu Of Pb) Mm(Et
Nw) Iu(Io Ok) NrPb MjIm MkPa NdHq NeNl HxOf} On{Jl(Et Fp Hq Hr Hu Hv Hw Hx Ih Ii Ij Ik Il Im In Io Ip Ir Is It Iu Iv Jg Jh Jk Jm Jn Jp Jr
Js Jt Lh Li Lj Lu Lv Lw Lx Ly Lz Ma Mb Mc Md Me Mf Mg Mh Mi Mj Mk Ml Mn Mp Mq Mr Mt Mu Mv Mw Mx Mz Na Nb Nc Nd Ne Nf
Nh Ni Nj Nk Nl Nm Nq Nr Ns Nt Nu Nv Nw Nx Ny Oh Ok Om Oz Pa Pb Pc Pd Pe Pf Pg Qa Qc Qd) Mm(Et Fp Hq Hr Hu Hv Hw Hx Ih Ii Ij Ik
Il Im In Iq Ir It Iu Iv Jg Jh Jk Jm Jn Jo Jp Js Jt Lh Li Lj Lu Lv Lw Lx Ly Lz Ma Mb Mc Md Me Mf Mg Mh Mi Mj Mk Ml Mn Mq Mr Mt Mv
Mw Mx Mz Na Nb Nc Nd Ne Nf Nh Ni Nj Nk Nl Nm Nq Nr Ns Nu Nv Nw Nx Ny Oh Ok Om Oz Pa Pb Pc Pd Pe Pf Pg Po Qa Qb Qc Qd Qe)
Ns(Et Fp Hq Hr Hu Hv Hw Ih Ii Ij Ik Il Im In Iq Ir It Iu Iv Jg Jh Jk Jm Jn Jo Jp Js Jt Lh Li Lj Lu Lv Lw Lx Ly Lz Ma Mb Mc Md Me Mf Mg Mi
Mj Mk Ml Mn Mq Mr Mt Mv Mw Mx Mz Na Nb Nc Nd Ne Nf Ng Nh Ni Nj Nk Nl Nm Nq Nr Nt Nu Nv Nw Nx Oh Ok Om Oz Pa Pd Pe Pf Pg
Po Qa Qb Qc Qd Qe) Jr(Et Fp Hq Hr Hv Hw Hx Ih Ii Ij Ik Il Im In Iq Ir Is It Iu Iv Jg Jh Jk Jm Jn Jo Jp Js Jt Lh Li Lj Lu Lv Lx Ly Lz Ma Mb Mc
Md Me Mf Mg Mh Mi Mj Mk Ml Mn Mq Mr Mt Mv Mw Mx Mz Na Nb Nc Nd Ne Nf Nh Ni Nj Nk Nl Nm Nq Nr Nu Nv Nw Nx Ny Oh Ok
Om Oz Pa Pb Pd Pe Pf Pg Po Qa Qb Qd Qe) Hu(Et Fp Hq Hr Hv Hw Ih Ii Ij Ik Il Im In Iq Ir It Iu Iv Jg Jh Jk Jm Jn Jo Jp Jq Js Jt Lh Li Lj Lu Lv
Lw Lx Ly Lz Ma Mb Mc Md Me Mf Mg Mi Mj Mk Ml Mn Mp Mq Mr Mt Mv Mw Mx Mz Na Nb Nc Nd Ne Nf Nh Ni Nj Nk Nl Nm Nr Nt Nu
Nv Nw Nx Oh Ok Om Oz Pa Pd Pe Pf Pg Po Qa Qb Qd Qe) Of(Et Fp Hq Hr Hx Ih Ii Ik Il Im Iq Ir Is It Iu Iv Jg Jh Jk Jm Jn Jp Js Jt Li Lj Lu Lv
Lw Lx Ly Lz Ma Mb Mc Md Me Mf Mg Mh Mi Mj Mk Ml Mn Mq Mr Mt Mv Mw Mx Nb Nc Nd Ne Ng Nh Ni Nj Nk Nl Nm Nq Nr Nu Nv
Nw Nx Ny Oh Ok Oz Pa Pb Pc Pd Pf Pg Po Qb Qc Qd Qe) Jq(Et Fp Hq Hr Hv Hw Hx Ih Ii Ij Ik Il Im In Iq Ir Is It Iu Iv Jg Jh Jk Jm Jn Jp Js Jt Li
Lj Lu Lv Lw Ly Lz Ma Mb Mc Md Me Mf Mh Mj Mk Mn Mq Mr Mt Mv Mw Mx Mz Na Nb Nc Ne Nf Nh Ni Nk Nl Nm Nr Nu Nv Nw Ny Oh
Ok Om Oz Pb Pd Pe Pf Pg Po Qa Qb Qd Qe) Mu(Et Fp Hq Hr Hv Hw Hx Ih Ii Ij Ik Im In Io Ip Ir It Iu Iv Jg Jh Jk Jm Jn Jo Js Jt Lh Li Lj Lv Lw
Lx Lz Ma Md Me Mf Mh Mi Mj Mk Ml Mn Mp Mq Mr Mt Mx Mz Na Nb Nc Nd Ne Nf Nh Ni Nk Nm Nq Nr Nt Nv Nw Nx Ny Oh Ok Oz Pa
Pb Pc Pe Pg Qa Qb Qc Qd Qe) Oi(Et Fp Hq Hr Hv Hw Hx Ih Ik Im In Io Iq Ir It Iu Iv Jh Jk Jo Jp Js Jt Lh Li Lj Lv Lw Lx Lz Ma Me Mf Mg Mh
Mi Mj Mk Mp Mq Mr Mt Mv Mw Mx Mz Na Nc Nd Nf Ni Nj Nk Nl Nm Nq Nr Nt Nv Nw Nx Ny Oh Ok Om Pa Pb Pd Pe Pg Po Qa Qb Qd
Qe) Ip(Et Fp Hr Hv Hw Hx Ii Ij Ik Im In Io Ir Is Iu Iv Jm Jn Jo Js Jt Lh Li Lj Lu Lv Lw Lx Lz Ma Md Me Mf Mg Mh Mi Mk Ml Mp Mr Mt Mv
Mw Mx Mz Na Nc Nd Ne Nf Nh Ni Nj Nk Nr Nt Nv Nw Nx Ny Oh Ok Om Oz Pa Pb Pc Pe Pg Qa Qc Qd) Is(Et Hr Hv Hw Hx Ii Ij Ik Il Im In
Iu Iv Jh Jm Jn Jo Jt Lh Li Lj Lu Lv Lw Lx Ma Md Me Mf Mg Mh Mi Mj Mk Ml Mn Mp Mq Mr Mt Mv Mw Mz Na Nc Nd Ne Nf Nh Ni Nj Nk

Figure 42 Continued

Nm Nq Nr Nt Nu Nv Nw Nx Ny Oh Ok Om Pa Pb Pc Pe Pg Qa Qc) Pz(Fp Hq Hr Hv Hw Hx Ih Ii Ij Ik Il Im In Io Iq It Jg Jh Jk Jm Jo Jp Js Lh
Lj Lu Lv Lx Ly Lz Ma Mb Mc Md Me Mf Mh Mj Mk Ml Mn Mq Mr Mv Mw Mx Nb Nd Ne Nf Nh Ni Nl Nm Nq Nr Nu Nv Nw Ny Ok Om Oz
Pa Pd Pf Pg Po Qb Qc Qe) Ng(Et Fp Hq Hv Hx Ih Ii Ij Ik Il Im Iq Ir It Iv Jh Jm Jo Jp Js Jt Li Lj Lu Lv Ly Lz Mb Mc Md Mf Mh Mj Mk Mn Mq
Mv Mw Mx Mz Nb Nc Nd Nf Nh Ni Nl Nm Nr Nu Nv Nw Ny Oh Ok Oz Pb Pd Pf Qa Qb Qd Qe) Io(Et Hr Hv Hw Ih Ik Im In Ir Iv Jh Jn Jo Js Jt Lh
Li Lj Lv Lx Lz Mb Me Mg Mh Mj Mn Mq Mr Mt Mv Mw Mx Mz Na Nc Nd Nf Nh Ni Nj Nl Nm Nr Nu Nw Nx Ny Oh Ok Pa Pb Pc Pe Pg Qd)
Nt(Et Hq Hr Hv Hw Hx Ii Ik Il Im In Ir Iv Jm Jn Jp Jt Li Lj Lv Lw Ly Ma Me Mg Mh Mi Mk Mp Mt Mv Mw Mz Na Nc Nd Ne Nf Nh Ni Nj Nk
Nm Nv Nw Nx Ny Oh Ok Pb Pc Pe Qa Qd) Oe(Fp Hv Hx Ih Ii Ij Ik Il Iq It Jg Jh Jm Jp Js Jt Li Lu Ly Lz Ma Mb Mc Md Mf Mh Mi Mj Mk Mn
Mq Mr Mv Mw Nb Nd Nf Nh Ni Nl Nm Nr Nu Nv Nx Ny Oh Ok Oz Pd Pf Qb) Mp(Et Hq Hv Hw Ij Ik Im In Ir Iv Jn Jo Jt Lh Li Lj Lv Lw Lx
Mg Mh Mi Mn Mr Mt Mv Mw Na Nc Nd Nf Ni Nj Nk Nm Nw Nx Oh Ok Om Oz Pb Pc Pd Pe Pf Pg Qa Qd) Lw(Et Fp Hw Im Ir Iu Iv Jn Jo Jt
Lh Li Lj Lu Lx Ma Mg Mh Mi Mr Mt Mw Mx Mz Na Nc Nd Nf Nj Nk Nm Nq Nx Oh Pa Pb Pe Pg Qa Qd) Qa(Et Hr Hx Ii Ik Im In Iu Jn Jo Jt
Lh Li Lx Ma Me Mg Mi Ml Mt Mv Mw Nb Nc Nd Nj Nk Nm Nq Nw Nx Ny Oh Pa Pb Pc Pe Pg Qc) Pc(Et Hv Hw Ij Im In Ir Iu Iv Jg Jn Jo Jt
Lh Lx Mg Mi Mn Mr Mv Mw Mz Na Nd Nf Ni Nm Nr Nx Ok Pa Pe Qd) Mg(Et Hv Hw In Ir Iu Jn Jo Jt Lh Lx Ma Mh Mi Mj Mq Mr Mt Mv
Mw Mz Na Nj Nq Oh Pa Pe) Mz(Et Hx Im Iu Jo Lh Lx Md Mh Mi Ml Mv Mw Na Nb Nc Nd Nj Nk Nm Nq Nx Ny Oh Pb Qc) Jn(Et Hr Hw Ik
Im Iu Jo Jt Lh Lx Mi Ml Mv Mw Nc Nd Nj Nk Nm Nq Nx Pa Pb Pe Qc) Jo(Et Hv Hw In Ir Iu Iv Jt Lx Mh Mi Mq Mr Na Nc Nj Nk Nr Nx Pe
Pg) Nj(Et Hv Hw Im In Ir Lh Lx Mi Mt Mv Mw Na Nd Nf Ni Pe Qd) Pe(Et Hr Hx Ii Ik Mh Mk Ml Mv Mw Nc Nk Nm Nx Ny Oh Pb) Mw(Hr
Hv Hw In Jk Lh Lx Mr Mt Na Nk Nq Om Pa Qc) Mi(Et Hq Hv Hw In Ir Mk Mv Na Nc Ni Nm Nx Qd) Hw(Et Hr Ii Jt Lx Mt Nb Nk Nm Nw Nx
Oh Qd) Lh(Hr Hx Ii Ik Mh Mk Mv Nk Nm Nx Oh Pb Qd) Lx(Et Hq Jt Mh Mk Mv Na Oh Qd) In(Mh Ml Mv Nb Nk Nx Ny Oh Pb) Nk(Et Hv
Im Mv Na Ni Ok) Jj(Hq Ik Lz Mb Mc Oz) Mt(Ik Mh Mv Ny Pb) Nc(Et Im Ne Ni) Qd(Ik Im Nd Qc) Nx(Hv Ij Iu Na) Pb(Hv Ij Na Pa) Mr(Mk
Mv Oh) Mv(Nq Pa) Nd(Hq Mk) Ir(Jt Qc) Oh(Hv Na) NmJt MhPa NeNl IkIv QcLj} Jl{Pc(Et Fp Hq Hr Hu Hv Hw Hx Ih Ii Ij Ik Il In Ip Iq Ir Is It Iu Iv Jg Jh Jk Jm Jn Jp Js Jt Li Lj Lu Lv Lw Lx Ly Lz Ma Mb Mc Md Me Mf Mh Mj Mk Ml Mn Mp Mq Mr Mt Mv Mw Mx My Na Nb Nc Nd Ne Nh Ni Nj Nk Nl Nm Nq Nr Ns Nu Nv Nw Nx Ny Oe Of Oh Ok Om Oy Oz Pa Pb Pd Pe Pf Pg Po Qb Qc Qd Qe) Mu(Et Fp Hq Hr Hu Hv Hw Hx Ih Ii Ij Il Im In Io Ip Iq Ir It Iu Iv Jg Jh Jk Jm Jn Jp Js Jt Lh Li Lj Lu Lv Lx Ly Lz Ma Mb Mc Md Me Mf Mh Mj Mk Ml Mn Mq Mr Ms Mt Mv Mw Mx My Na Nb Nc Nd Ne Nf Nh Ni Nj Nk Nl Nm Nq Nr Ns Nu Nv Nw Nx Ny Ok Om Oz Pa Pd Pe Pf Pg Po Qa Qb Qc Qd Qe) Lw(Et Fp Hq Hr Hu Hv Hw Hx Ih Ii Ij Ik Il In Ip Iq Ir Is It Iu Iv Jg Jh Jk Jm Jn Jp Js Jt Li Lj Lv Ly Lz Ma Mb Mc Md Me Mf Mh Mj Mk Ml Mn Mp Mq Mr Mv Mw Mx My Na Nb Nc Nd Ne Nh Ni Nj Nk Nl Nm Nq Nr Ns Nu Nv Nw Nx Ny Of Ok Om Oy Oz Pa Pb Pd Pe Pf Pg Po Qa Qb Qc Qd Qe) Nt(Et Hq Hr Hu Hv Hw Hx Ih Ii Ij Ik Il Im In Ip Ir Is It Iu Iv Jg Jh Jm Jn Jp Jr Js Jt Lh Li Lu Lv Ly Ma Mb Md Me Mf Mg Mh Mi Mj Mk Ml Mm Mp Mq Mr Ms Mt Mw Mx My Mz Na Nc Nd Ne Nf Nh Ni Nj Nk Nl Nm Nq Nr Ns Nv Nw Nx Ny Oe Of Oh Oi Ok Om Oy Oz Pb Pd Pe Pg Qa Qc Qd) Mp(Et Fp Hr Hu Hv Hw Hx Ih Ii Ij Ik Im In Ip Ir Is Iu Iv Jg Jh Jk Jm Jp Js Jt Lh Li Lj Lu Lv Lx Ly Lz Ma Md Me Mf Mg Mh Mi Mj Mn Mr Ms Mt Mw Mx My Na Nb Nc Ne Nh Ni Nj Nk Nm Nq Nv Nw Nx Oe Of Oh Oi Ok Om Oy Pa Pb Pd Pe Pf Pg Qa Qd) Mg(Et Hq Hr Hu Hv Hw Hx Ih Ii Ij Ik Im In Io Ip Ir Is Iu Iv Jg Jh Jm Jn Jp Js Jt Lh Li Lj Lu Lv Lx Ma Mb Md Me Mh Mi Mj Mk Ml Mr Mt Mv Mx My Na Nc Nd Ne Nf Nh Ni Nj Nk Nm Nq Ns Nv Nw Nx Ny Oh Ok Om Oy Oz Pa Pb Pe Pg Qa Qc Qd) Mm(Fp Hq Hr Hu Hv Hw Hx Ih Ii Ij Ik Im In Ip Ir Is Iv Jg Jh Jm Jo Jp Js Jt Lh Li Lu Lv Lx Ma Md Me Mf Mh Mi Mk Mr Ms Mw Mx My Na Nb Nc Nd Ne Ng Nh Ni Nj Nk Nm Nq Nr Ns Nw Nx Oe Of Oh Oi Ok Om Oy Oz Pa Pb Pd Pe Pg Po Qd) Jq(Fp Hq Hu Hv Hw Hx Ih Ij Ik Il In Iq Ir Is Iu Iv Jh Jk Jm Jn Jp Li Lj Lu Lv Ly Lz Ma Mb Mc Md Mf Mj Mk Mn Mq Mr Mt Mv Mw Mx My Mz Na Nb Nc Nf Ni Nk Nl Nm Nr Ns Nu Nv Nw Ny Ok Om Oy Pb Pd Pe Pf Pg Po Qa Qb Qd Qe) Og(Fp Hq Hr Hu Ih Ik Il Iq Ir It Jk Jm Jp Js Li Lj Lu Lv Lx Ly Lz Ma Mb Mc Me Mf Mh Mj Mk Ml Mn Mq Mr Ms Mx My Nc Nd Ne Ng Nh Ni Nj Nk Nl Nr Nu Nv Nx Oe Of Oi Oy Oz Pb Pd Pe Pf Pg Po Qb Qc Qd Qe) Mz(Et Hr Hw Hx Ii Ik Im Io Ip Is Iu Iv Jg Jh Jk Jm Jn Jr Jt Lh Li Lj Lu Lv Lx Ma Md Me Mh Mj Ml Ms Mt Mw My Na Nc Nd Ne Ng Nh Nj Nk Nm Nq Ns Nw Nx Ny Oe Of Oh Oi Ok Om Oy Oz Pa Pb Pe Pg Pz Qc) Mi(Et Hq Hr Hv Hw Hx Ii Ij Ik Im In Ip Ir Is Iu Iv Jg Jh Jm Jn Jp Jt Lh Li Lu Lv Lx Ly Ma Md Me Mh Mj Mk Ms Mt My Na Nc Ne Nf Ng Nh Ni Nj Nm Nq Ns Nw Nx Oe Of Oh Oi Ok Om Oy Oz Pb Pe Qa Qd) Oh(Et Hr Hu Hv Hw Ij Ik Im In Ip Ir Is Iu Iv Jg Jh Jk Jm Jn Jo Jp Jr Jt Lh Lu Lv Lx Ma Md Mh Mj Mr Ms Mt Mw Na Nb Nd Ne Nf Ng Nh Ni Nj Nm Nq Ns Nw Nx Oe Of Ok Om Oz Pa Pe Pg Po Qa Qc) Jr(Et Hr Hv Hw Ii Ij Ik Im In Io Ip Is Iu Jg Jh Jk Jm Jo Jt Lh Lu Lx Ma Md Me Mh Mj Ml Mr Ms Mt Mw Na Nd Ne Nf Ng Nh Ni Nj Nm Ns Nw Nx Oe Of Oi Ok Om Oz Pa Pb Pe Pg Qa Qc) Oe(Et Hr Hv Hw Hx Ih Ij Ik Im In Io Ip Ir Is Iu Iv Jg Jk Jm Jn Jo Jt Lh Li Lu Lx Ma Mb Md Mh Mr Ms Mt Mv Mw Na Nb Ne Nf Ng Nm Nq Ns Nv Nw Of Ok Om Oz Pa Pe Pg Po Pz Qa) Pz(Hr Hv Hw Ih Ij In Io Ip Ir Iu Iv Jh Jk Jo Jp Js Jt Lh Li Lu Lx Ma Md Mr Ms Mt Mv Mw Na Nb Nc Ne Nf Nj Nk Nm Nq Ns Nu Nw Oi Ok Oz Pa Pb Pe Pg Po Qa Qd) Lh(Et Hr Hx Ii Ik Im Io Ip Is Jg Jm Jn Jt Ly Ma Md Mh Mj Mk Ml Ms Mt My Ne Nj Nm Nq Nw Nx Ny Of Oi Om Oy Pb Qa Qd) Nq(Et Hu Hv Hw Ij Im In Io Ip Ir Is Jm Jn Jo Jt Md Mf Ms Mt My Na Nf Ni Nj Nm Nw Of Oi Ok Om Oy Pe Qa Qd) Md(Et Hq Hr Hw Ii Ik Im Io Ip Is Jn Jt Mh Mk Ms Mt My Na Ne Nf Ng Nj Nm Ns Nv Nx Of Oi Ok Oy Oz Pb Qa) Ng(Et Hv Hw Ij Im In Io Ip Is Iu Jg Jh Jn Jo Jt Li Lx Ma Mr Mt Mv Mw Na Nf Nm Oi Ok Om Pa Pe Pg Qa) Io(Et Hr Hw Ih Ik Im Ip Ir Iu Iv Jg Jn Jo Jp Li Lx Ma Ms Mt Na Nf Nm Nw Ok Om Pa Pc Pg Qa Qd) Jo(Et Hv Ij In Ip Ir Is Iu Iv Jg Jh Jn Li Lx Ma Mr Ms Mt Na Nb Nd Nf Nw Oi Ok Pa Pe Pg Po) Is(Et Hr Hw Ii Ik Im Ip Iu Jm Jt Lu Lx Mh Mj Ms Mt Ne Nf Nm Nw Nx Of Oi Ok Om Oz Pa) Et(Hr Hw Im In Ip Jn Jt Lu Lx Ms Mt Na Nd Ne Nf Nk Nm Nw Of Oi Om Pa Pe Qa) Oi(Hr Ih Im Ip Ir Iv Jg Jh Jn Jt Li Ma Ms Mt Nf Nm Nw Ok Om Pe Qa) Ms(Hv Hw Im In Ip Jg Jn Jt Mt Mw Na Nb Nf Nm Nw Ok Om Qa) Mt(Hr Hv Hw Im In Ip Jt Lx Ml Na Ni Nj Nm Ok Om Qa Qc) Im(Hv Hw Ij In Jn Jt Na Nc Nf Nm Nw Of Om Qa Qd) Lx(Hq Hv Hw Jn Jt Ly Mh Na Nf Nm Of Ok Om Qa) Jt(Hr Ii Ik Ip It Jg Nd Ne Nf Nw Of Om Pa) Nf(Hr Ii Ip Ma Mh Ml Na Nj Nm Of Pb) Om(Ii Ik Ip Mh My Na Nm Ns Nx Oy Pb) Of(Hw Jg Jh Ma Na Nb Nm Ok Qa) Nm(Hr Ii Ip Lu Nw Pa Pb) Hr(Hw In Jn Ok Pe Qa) Nw(Hv Hw Mh Na Ok Qa) Pb(Hw Nb Ok Pe Qa) Nb(Mh My Oy) Ip(Hw Ok) Jg(My Oy) Pe(Ik Oz) MkPa NdHq NeNl HuJh} Mu{Et(Fp Hq Hr Hu Hv Hw Hx Ih Ii Ij Ik Il Im In Io Ip Iq Ir It Iu Iv Jg Jh Jk Jm Jn Jo Jp Js Jt Lh Li Lj Lu Lv Lw Lx Ly Lz Ma Mb Mc Md Me Mf Mh Mj Mk Ml Mn Mp Mq Mr Ms Mt Mv Mw Mx My Mz Na Nb Nc Nd Ne Nf Nh Ni Nj Nk Nl Nm Nq Nr Ns Nu Nv Nw Nx Ny Oe Oh Oi Ok Om Oy Oz Pa Pb Pc Pd Pe Pf Pg Po Qa Qb Qc Qd Qe) Jq(Fp Hq Hr Hu Hv Hw Hx Ih Ii Ij Ik Il Im In Io Iq Ir It Iv Jg Jh Jk Jm Jn Jo Jp Js Jt Li Lj Lu Lv Lw Ly Lz Ma Mb Mc Md Me Mf Mg Mh Mj Mk Ml Mn Mq Ms Mt Mv Mw Mx My Mz Na Nb Nc Ne Nf Ng Nh Ni Nk Nl Nm Nq Nr Ns Nu Nv Nw Nx Ny Oe Of Oh Oi Ok Om Oy Oz Pb Pd Pf Pg Po Pz Qa Qb Qc Qd Qe) Lh(Fp Hq Hr Hu Hv Hw Hx Ih Ii Ij Ik Il Im In Io Ip Iq Ir It Iu Iv Jg Jh Jk Jm Jn Jp Js Jt Li Lj Lu Lv Lx Ly Lz Ma Mb Mc Md Me Mf Mh Mi Mj Mk Ml Mn Mp Mq Mr Mt Mv Mw Mx Mz Na Nb Nc Nd Ne Nf Nh Ni Nk Nl Nm Nq Nr Ns Nt Nu Nv Nw Nx Ny Oh Oi Ok Om Oz Pa Pd Pe Pf Pg Po Pz Qa Qb Qc Qd Qe) Jr(Fp Hq Hr Hu Hv Hw Hx Ih Ii Ij Ik Il Im In Io Iq Ir It Iu Iv Jg Jh Jk Jm Jn Jo Jp Js Jt Li Lj Lu Lv Ly Lz Ma Mb Mc Md Me Mf Mg Mh Mj Mk Ml Mn Mq Ms Mt Mv Mw Mx My Mz Na Nb Nc Nd Ne Nf Ng Nh Ni Nk Nl Nm Nr Ns Nu Nv Nw Nx Ny Oe Of Oi Om Oy Oz Pb Pd Pf Pg Po Pz Qa Qb Qc Qd Qe) Pe(Fp Hq Hr Hu Hv Hw Hx Ih Ii Ij Il Im In Io Ip Iq Ir Iu Iv Jg Jk Jm Jn Jp Js Jt Li Lj Lu Lv Lx Ly Lz Ma Mb Mc Md Me Mf Mh Mi Mj Mk Ml Mn Mp Mq Mr Ms Mt Mv Mw Mx My Mz Na Nb Nc Nd Ne Nf Nh Ni Nj Nk Nl Nm Nq Nr Ns Nt Nv Nw Nx Ny Oe Oi Ok Om Oz Pa Pd Pf Pg Po Qa Qc Qd) Is(Fp Hq Hr Hu Hv Hw Hx Ih Ii Ij Il Im In Ip Iq Ir It Iu Iv Jg Jh Jk

Figure 42 Continued

Li Lj Lu Lv Lw Ly Lz Mb Mc Md Mf Mh Mi Mj Mk Ml Mn Mq Mr Ms Mx My Mz Na Nc Nd Ne Nf Ng Nh Ni Nk Nl Nm Nr Ns Nu Nv Nx Ny Oe Of Oh Oi Ok Oy Oz Pa Pb Pd Pf Pz Qa Qb Qc Qd Qe) Om(Fp Hq Hu Ih Ii Ij Ik Il Im In Io Iq Jh Jo Jp Js Li Lj Lu Lv Lz Ma Mg Mh Mj Ml Mq Ms Mv Mx My Mz Na Nc Nd Ne Nf Ng Ni Nj Nk Nl Nm Ns Nv Nw Nx Oi Ok Oy Oz Pb Pg Po Pz Qb Qd) Mw(Hr Ii Ik Io Iq It Jh Jk Jm Lu Ly Ma Mb Mc Md Me Mf Mj Mk Ml Mn Mv Nc Nd Ne Nh Ni Nj Nl Nq Ns Nu Nx Ny Oe Of Oi Oz Pb Pd Pf Pz Qb Qc) Lh(Et Hr Hx Ih Ij Im In Io Ir Iv Jk Jo Jp Jt Lv Ma Md Me Mh Mi Mz Ne Ng Nj Nk Nm Nq Nt Nv Oh Ok Pa Pb Pe Pg Po Qa Qd) Mt(Hv Hw Ij Il Im In Io Ip Ir Iu Iv Jn Jo Jt Lv Lw Mg Mh Mi Mm My Mz Na Nj Nm Nq Nv Nw Ny Ok Pb Pg Po Qa Qd Qe) Jg(Hw Ii Ij Ip Ir Iv Jh Jk Jn Jt Lx Mr Mx Nf Nq Nr Nv Nw Pg Qa Qd) Jh(Hx Ip Ir Iu Jk Jn Jt Lw Mm Mx Mz Nr Nv Oh Ok Pg Po Qa Qe) Nt(Et Io Ip Jn Jt Mg Mi Mm Mz Ne Nf Nj Nq Oh Ok Pe Po Qa) Nw(Hw Hx Ii In Jt Lw Mg Mi Mr Na Nq Nr Pa Pe Qa) Mi(Et Ii Ij In Ip Jk Jn Lw Mz Pe Qa) Pe(Et Ip Jn Jt Mg Mv Mz Nm Nq Oh) Pa(Et Ip Jn Jt Mg Mv Mz Nm Ok) Mz(Jk Lx Mg Mm Nq Pg) Nq(Jn Jt Mr Ok) Mm(Hx Jn Mr Qa) Po(Et Ip Lw) Lx(Jn Jt Lw) Mv(Jt Mr Nr) Jk(Et Ok) MgMr} Mm{Pe(Et Fp Hq Hr Hu Hv Hw Hx Ih Ii Ij Il Im In Ip Iq Ir It Iu Iv Jg Jh Jk Jm Jn Jp Js Jt Lh Li Lj Lu Lv Lw Lx Ly Lz Ma Mb Mc Md Me Mf Mh Mi Mj Mk Ml Mn Mq Mr Ms Mt Mv Mw Mx My Na Nb Nc Nd Ne Nf Nh Ni Nj Nk Nl Nm Nq Nr Ns Nt Nu Nv Nw Nx Ny Oe Of Oh Oi Ok Om Oz Pa Pb Pd Pf Pg Po Qa Qb Qc Qd Qe) Lh(Et Fp Hq Hr Hu Hv Hw Hx Ih Ii Ij Ik Im In Ip Iq Ir Iv Jg Jh Jk Jm Jp Js Jt Li Lj Lu Lv Lw Lx Ly Ma Mc Md Me Mf Mh Mi Mj Mk Ml Mn Mq Mr Ms Mt Mv Mw Mx My Na Nc Nd Ne Nf Nh Ni Nj Nk Nl Nm Nq Ns Nt Nu Nw Nx Ny Oe Of Oh Oi Ok Om Oy Pa Pb Pd Pf Pg Po Qa Qb Qd Qe) Mz(Et Fp Hw Hx Il Im Io Ip Ir Iu Iv Jk Jn Li Lu Lv Lx Ly Mh Mi Ml Mr Ms Mt Na Nb Nc Nd Nk Nq Nr Nv Nw Ny Of Oi Om Pb Pd Po Pz Qa Qb Qd) Nt(Et Hv Hw Ij Ik In Ip Ir Jo Jp Jt Lv Lw Md Mg Na Ne Nf Ng Nj Oe Oh Oi Ok Om Pg Pz Qa Qd) Qa(Io Ip Jk Jn Jo Lu Lx Md Mg Mi Mr Ms Mt Nb Nd Nf Ng Nh Nq Nr Nv Oi Om Pa Pg Po) Mr(Hv Io Ip Ir Lv Lw Mg Mh Mt Na Nf Ng Ni Nw Oe Om Pg Pz Qd) Jn(Hw Io Ip Jk Lu Lv Lx Mi Ms Nb Nq Nr Nw Oi Om Pa Pg Po) Om(Hw Ir Mi Ms Mt Ng Of Oy Pz Wm) Nw(Et Hv In Ir Jo Jt Na Nr Pz) Pg(Hw Io Ir Mg Na Nf Ng Ok Pz) Pa(Hv Hw In Ir Jt Mk Na Nf) Lx(Et Hq Hv Hw Ir Jt Na) Mt(Et Hw My) Mi(Et Hw) My(Mw Nb) Ir(Io Pz) PoOy NbOf HwIp PzQd} Nt{Nw(Et Hq Hr Hv Hw Hx Ii Ij Ik Il Im In Ip Ir Jm Jn Jo Jp Jt Li Lv Lw Ly Ma Mb Mf Mg Mh Mi Ml Mq Ms Mt My Mz Na Nc Nd Ne Nf Ng Nh Ni Nj Nk Nm Nq Ns Nv Nx Ny Oe Of Oh Oi Ok Om Oy Pb Pg Pz Qa Qd) Mz(Et Hr Hx Ik Im In Io Ip It Iu Jg Jh Jm Jn Jp Jt Li Lv Ly Ma Me Mf Mg Mh Mi Ml Mq Ms Mt Mv Mx My Nd Ne Nf Ng Nh Nk Nm Nq Ny Oe Of Oh Oi Om Pb Pe Pg Po Pz Qa Qc Qd) Mt(Et Hw Hx Ik Im In Io Ip Jg Jn Jo Jp Jt Lv Ly Ma Mg Ml Mq Ms Mv Mw Na Nd Ne Ng Nj Nm Nq Ny Oe Of Oh Oi Om Oy Pg Pz Qa Qc Qd) Lw(Et Ip Ir Jm Jn Jo Jp Lh Li Lj Lu Ma Mg Mi Ms Mx Ne Nf Ng Nh Nj Nq Oe Of Oh Oi Om Pe Po Qa Qd) Ip(Et Ik Io Jm Jn Jo Mg Mi Ne Nf Ng Nj Oe Oh Oi Om Pz Qa) Jn(Et Ik Io It Jm Jo Ma Mg Ne Ng Nj Nq Oe Oh Oi Om Pz) Io(Et Ih Ik Jo Jp Jt Me Mg Mi Nd Nj Oh Om Qa Qd) Jo(Et Jg Jt Lh Ma Mi Ne Nf Oe Oh Pe Pg Po Qa) Om(Ii Ik Mg Ms My Ng Nj Oe Oh Oi Oy Pb Pz Qa) Ng(Et Jp Jt Lh Li Ma Mg Mi Mw Nj Nq Qa) Et(Mg Nd Nf Oe Of Oh Oi Pz Qa) Oh(Jg Jp Lv Nj Oe Oi Qa) Qa(It Ne Oe Pz) Nj(Mi Ne Nf) Oe(Jg Jk Jp) My(Jh Mv) Ik(Pe Qd) LxHq MaMg MsJg MwOy PzQd} Lh{Lw(Et Fp Hq Hr Hu Hv Hx Ih Ii Ik Im In Ip Ir Iu Iv Jg Jh Jk Jm Jn Jp Js Jt Li Lj Lu Lv Lx Ly Ma Md Mf Mh Mi Mk Ml Mr Mt Mw Mx My Mz Na Nc Nd Ne Nf Ng Nh Ni Nj Nk Nm Nq Ns Nw Nx Ny Oe Of Oh Oi Om Oy Pb Pe Pg Po Pz Qa Qb Qd) Jo(Hx Im Ir Iv Jg Jh Jk Jp Js Jt Lv Mg Mh Mi Ml Ms Mt Mw Mz Nq Nw Ny Of Oh Ok Om Pb Pe Pg Po Qa Qd) Nw(Et Hx Ii Io Ip Jn Jt Md Mg Ml Ms My Ng Ny Oe Of Oh Oi Oy Pb Pz Qa) Jn(Et Hr Hx Ii Io Ip Ma Mg Mh Ml Ms Ng Nj Nq Oe Of Oh Oi Pb Pz) Ip(Et Ii Io Mg Mi Ms Mt Mz Ng Of Oh Oi Pb Pz Qa Qd) Mt(Et Hx Mg Mh Ml Ms Ng Ny Oe Of Oh Oi Oy Pb) Ng(Et Jh Jk Jp Jt Mw Nq Oh Om Pg Qa Qd) Of(Et Jg Jk Ma Mg Mi Mv Mw Mz Nb Nq Pg) Oh(Et Im Io Lv Mg Ms Nj Oe Oi Om Qa) Et(Io Mg Mz Oe Of Oh Oi Pb Pz) Mg(Jt My Nq Om Pg Qd) Qd(Ik Il Im Io Pz) Nq(Hu Ms My Oy) Jg(Ms My Oe Oy) Om(Ms Oe Oy Pb) Io(Jt Mi Qa) Mh(Lx Mz) Jh(Hu Ms) Pb(Ma Pg) MlMz PzQa} Mt{My(Fp Hq Hr Hu Hv Ih Ij Ik Il Im In Io Ip Ir Iu Iv Jn Jo Jp Jt Li Lj Lu Lv Lw Lx Lz Ma Mb Me Mg Mh Mi Mj Mq Ms Mv Mx Mz Na Nc Nd Ne Nf Ng Nh Ni Nj Nk Nm Nr Ns Nv Nw Ny Of Oi Ok Oy Oz Pb Pd Pf Pg Po Pz Qa Qb Qd Qe) Pb(Et Hu Hv Hx Ii Ij Im In Ip Ir Iv Jn Jo Lv Lw Mi Mr Ms Na Ng Nj Nr Nw Ny Oi Ok Om Pa Pe Pg Qd) Ny(Et Hw Ii In Jn Mr Mz Ng Ns Ok Om Oy Pa Pe Qa) Of(Hv Ij Jt Mz Na Nb Ok Pe Pg) Oy(Jh Mh Mr Nb Om Pa Pe Pg Po) Hw(Et Hx Ip Lw Md Mh Ml) Et(Lw Mh Mi Oi Pz) Ml(In Mz Na Pe Qa) Mh(li Nr Ns Qa) Lw(Mr Pa Pe) Md(In Mz Qa) Mi(Io Mz Qa) Hx(Mr Pa Pe) NqNg LxJt OhPe} Mi{Mz(Et Hx Im Ip Jg Jn Jo Lv Lw Ma Md Mh Ml Ms My Nf Ng Nj Nw Ny Of Oi Om Oy Pb Pe Pg Qa Qd) Om(Et Hq Hx Io Ip Ir Jn Jo Lj Md Mh Ml Ms Mv Nj Ny Oe Oh Oi Pb Pz Qa Qd) Qa(Et Hr Ip Jg Jn Jo Jp Lw Ma Mg Ml Ms Ng Nj Nw Of Oh Oi Pb Pz) Nw(Et Hv Hw Hx Io Jn Jo Jt Mh Ms My Na Ny Pb Pz) Jn(Et Io Ip Jm Jo Js Lw Mh Ms Ng Nj Oi Pz) Et(Hw Io Lw Mg Nf Ng Oi Pe) Io(Ip Jp Lv Lw Nj Qd) Ng(Jk Mg Mw) Ms(Jg Jh) Hq(Lx Pg) MwOy MyJg HuJh PzQd JoJt} Nw{Hw(Et Io Ip Iu Lw Lx Mg Mh Ml Ms Nd Nj Nq Ns Ny Oe Of Oh Oi Pb Pz) Qa(Et Io Iu Lx Mg Ml Nd Nq Pz) Jo(Io Mg Mh Ml My Ng Of Pb Pz) Nq(Hu Jt Ms My Na Ng Oy) Jt(Io Ip Lx Nd Oi Pz) Pe(Hx Lw Mh Ny Oh Pb) Lw(Io Lu Mr Pa) Mh(li Mr Nr Pa) Na(Et Lx Nd Pz) Jk(Ms My Ng Oy) My(Jh Nb) Of(Nb Om) Oy(Jh Mw) EtPz MlIn IoIu} Nq{Mz(Et Hu Hw Ip Iu Lw Md Ml Ms Mv My Ng Nj Ny Of Oi Ok Oy Pa Pb Pe Qa Qd) Pe(Hu Ik Jn Lw Mg Mk Ms My Ng Oe Of Oy) Jn(Et Hu Lw Ms My Ng Oi Ok Oy Pz) Hu(Hw Ir Jh Jt Na Ok Om Qa) Ng(Jg Jt Nb Om Po Qa) Oy(Jh Mw Nb Om) My(Hx Mr Pa) Mg(Jt Ok) LwMr MkPa MsOm JoJt} Lw{Pa(Et Ip Ir Jn Lu Mk Ms My Mz Nf Ng Oh Oy Qa Qd) Mr(Et Io Ip Jn Jo Jp Lu Ma Mg Ms Mz Oh Qa Qd) Pe(Et Ik Io Ip Jn Jo Lu Mg Mz Ng Of Oh) Lx(Et Hq Io Jn Mz Ng Qa) Et(Io Lu Mz Po) Io(Jp Pg Qa) Po(Of Oy) Mz(Iu Pg) MwMy} Lx{Jt(Et Hq Io Ip Jn Mg Mh Mz Ng Of Oy) Mz(Et Hq Mh Ml Ny Of Pb) Hq(Jn Mg Mh Om Pd Qa) Qa(Et Ml Of Oh Pb) Om(My Ng Oh Oy Pb) Of(Ij In Na Nb) Mh(Jn Nd Pg) My(Jg Jh Nb) Et(Jn Pz) Ng(Jh Mw) Oy(Jg Nb) HwPb} Mw{My(Fp Hx Ih Im Iu Iv Jp Js Jt Lu Lv Lz Ma Md Mg Mh Mr Ms Mv Mx Nf Ng Nv Oe Ok Om Oy Po Qa Qd Qe) Oy(Et Hx Ip Ir Jk Jn Nd Nv Oh Pa Pb Pg) Hu(Hx Pb) MzOf} Et{Pz(Hw Ir Jk Jn Jt Mr Mz Nk Om Pa Pe Pg Po Qd Qe) Pe(Ik Io Jo Mg Ng Of Oh Oi) Mz(Hw Iu Oi Pa Pg) Of(Jk Nb Om Pg) Io(Jn Nk Qa) Pg(Jo Mg Ng) Jk(Ng Oe) Pa(Mk Oe) MrOh HwJo} Om{Of(Hw Hx Ir Iu Iv Jk Jn Jo Jt Mk Mx Nv Oh Qa Wm) Oh(Hw Mr Ms My Oi Pa Pe) Pa(Mk Ms My Ng Oy Pb) Oy(Pe Pg Po Wm) Iu(Mg Ms Ng) My(Mr Nb) Pz(Qa Qd) Jt(Jo Mg) NdHq} Pe{Oh(Im Ip Jn Jo Lv Nj Oi) Jg(Ms My Ng Oy) Mg(Ik Ma Ng) My(Jh Jt) Of(Jh Nb) MaNg MlMz} Pa{Mz(Ip Mh Ml Of Pb) Jt(Io Jo Mg Mk) Ng(Jg Mg) MkJh NbOf QaOh} Pg{Mz(Iu Jo Of Pb) My(Jh Mv Nb) Jt(Io Jo Ng) Jg(Ng Oy) NbOf JoOk} Jh{Oy(Hx Ir Jk Lz Mh Mr Nk Nv Oh) My(Mr Po)} Mg{Ng(Jk Mr) PoOy MaJt MlMz} Jg{Po(Ng Oy) MyNb NgJk PzQd} Mr{IpOh JoJt} PoJoJt

Unconstrained panels with 3 analytes, where 2.4E-7 >= 'model p-value' > 1.0E-7. Contains 15,033 panels of 397,580 total panels evaluated. :
No{Nf(Fp Hq Hu Hv Hw Hx Ih Ii Ij Ik In Io Iq Ir Jh Jm Js Lh Li Lj Lu Lx Ly Lz Mb Mc Md Mh Mj Mk Ml Mn Mr Ms Mv Mw Mx My Na Nb Nc Nd Ne Ng Nh Ni Nk Nl Nr Nu Nv Nx Ny Oe Of Oy Oz Pa Pd Pe Po Pz Qb Qe) Md(Fp Hr Hu Hv Hw Hx Ih Ii Ij Ik In Io Ir Iu Jh Jk Jo Js Lh Li Lu Lx Ly Ma Mb Me Mh Mj Mk Ml Mn Mr Ms Mv Mw Mx My Na Nc Nd Ne Ng Nh Ni Nk Nu Nv Nx Ny Of Oi Oz Pa Pb Pe Pg Po Pz Qb Qd Qe) Ij(Fp Hu Hv Hw Hx Ih Ik Il In Io Iq Ir It Iv Jh Jm Js Lh Lu Lx Ly Lz Mb Mc Mh Mj Mk Ml Mn Ms Mv Mw Mx My Na Nb Nc Ne Ng Nh Ni Nk Nl Nm Nt Nu Nv Nx Ny Of Ok Oy Oz Pa Pd Pe Po Pz Qb Qe) Jp(Fp Hq Hr Hu Hx Ih Ii Ik Il Iq Ir It Iv Jm Js Li Lj Lu Lx Ly Lz Ma Mc Me Mh Mj Mk Ml Mn Mr Ms Mv Mw Mx My Nc Ne Nh Ni Nk Nl Nr Nu Nv Nw Nx Ny Of Og Oy Pa Pb Pd Pf Po Qb Qc Qd Qe) Pg(Fp Hq Hu Hx Ih Ik Il Iq It Iu Iv Jh Jk Jm Js Li Lj Lu Lx Ly Lz Ma Mc Me Mh Mj Mk Ml Mn Mr Ms Mv Mw Mx My Nb Nc Ne Nh Ni Nk Nl Nr Nt Nu Nv Nx Ny Oy Pa Pd Pe Pf Po Qb Qc Qd Qe) Na(Fp Hq Hu Hv Hw Hx Ih Ii Ik Il In Io Iq Ir It Jm Js Lh Lj Lu Lx Ly Lz Mb Mc Mh Mj

Na Nd Nf Nh Nw Nx Ok Om Pa Pb) Ip(Hq Ih Il Iq It Jg Jh Jk Jp Ly Mb Mc Mj Mn Mq Nb Nl Nq Nu Pd Pf Po Qb Qe) Is(Fp Hq Ih Iq Ir It Jg Jk Jp Js Ly Lz Mb Mc Mx Nb Nl Oz Pd Pf Po Qb Qe) Im(Hr Hv Ij Ik In Ir Iu Iv Jo Jt Lv Mh Mj Mq Mr Mt Na Nd Nf Ni Pb Pg) Iu(Hr Hv Ii Ij Ik In Ir Iv Jm Jt Lj Lv Mh Mq Mt Na Nf Ni Nw Ok Om) Jo(Ii Ij Ik Js Li Lv Ma Me Mj Mt Nd Nf Ni Nq Nu Nw Om Pa Pb Pd Po) Na(Hr Ii Ik Ir Iv Jt Li Lv Lz Ma Mh Mr Mt Nb Nd Nf Nq Nw Pa) Oi(Ii Ij Il Jg Jm Lu Ly Mb Mc Md Ml Mn Nb Ne Nh Nu Oz Pf Qc) Ir(Hr Ii Ik In Jm Li Lv Ma Mh Ml Mt Nd Ni Nq Nx Pa Pb Pg) Jt(Hr Hv Ii Ik Li Lu Mh Mr Mt Nd Nq Nw Nx Pa Pb) Nx(Iv Li Lv Mh Mq Mr Mt Nd Nf Ni Om Pa Pd Pg) Pb(Iv Li Lv Ma Mh Mq Mr Mx Nf Ni Nr Om Pg Po) Mu(Il Iq Jp Lu Ly Mb Mc Nl Nu Om Pd Pf Po) Hv(Hr Ii Ik Jh Li Ma Mh Mt Nb Nd Nq Nw Pa) Ik(In Li Ma Mh Mj Mr Ni Nu Pa Pg Po) In(Hr Hx Ii Iv Li Ma Md Mt Nd Om) Mt(Hx Lv Ml Mr Nd Nf Ni Qc) Mr(Hr Hx Ii Lv Mh Ny) Nd(Iv Jm Lj Mh Ni Ok) Pa(Hx Ii Ml Ni Ny) Nf(Ii Lv Ml Ny) Iv(Hr Lv Ma Qc) Mh(Ii Li Ni) Lj(Lv Ma Nq) Mk(Pd Pg) NbIj} Fr{Iv(Et Fp Hq Hr Hx Ih Ii Il Iq It Iu Jg Jh Jk Jm Jp Js Li Lj Lu Lx Ly Lz Ma Mb Mc Md Me Mf Mh Mj Mk Ml Mn Mr Mv Mw Mx Nb Nc Nd Ne Nf Nh Ni Nk Nl Nq Nr Ns Nu Nv Nw Nx Ny Of Om Oz Pa Pb Pd Pf Pg Po Qc Qd) Hv(Et Fp Hq Hr Hx Ii Ij Ik Il In Io Iq It Jg Jh Jk Jm Jp Js Li Lj Lu Lv Ly Lz Ma Mb Md Me Mf Ml Mn Mv Mw Nb Nd Ne Nf Nh Ni Nm Nq Nr Ns Nu Nv Nx Ny Oi Ok Om Oz Pd Pg Po Qb Qc Qe) Mi(Fp Hr Hu Hx Ii Il It Iu Jg Jh Jk Jm Jp Js Li Lj Lu Lx Lz Mb Md Mf Mh Mk Ml Mn Mr Mt Mv Mw Mx Nb Nd Ne Nh Nl Nr Ns Nu Nx Ny Oe Of Oz Pa Pb Pd Pf Pg Qb Qc Qe) Pe(Fp Ii Iq It Jg Jh Jk Jm Jp Js Li Lj Lu Lx Ly Ma Mc Md Me Mf Mj Mn Mr Mv Mw Mx Nb Nd Ne Nf Nh Ni Nl Nq Nr Nu Nv Nx Om Pa Pd Pg Po Qb Qc Qe) Ok(Et Hu Hx Ij Ik Im In Io Jo Js Lv Lz Md Mh Mm Mq Mr My Nd Ne Nf Nh Ni Nj Nl Nm Nq Nr Ns Nv Nw Oe Of Oi Om Oy Pa Pb Pd Pg Qb Qd Qe) Mp(Hr Ii Ik Il Iq Iu Jg Jh Jk Jm Jp Li Lu Lv Lx Ly Lz Mb Md Mf Mj Ml Mn Mv Mw My Nd Ne Nh Nl Nq Nu Nv Nx Ny Oz Pa Pb Pc Po Qb Qe) Lw(Hq Hr Ii Ik Il Iq It Jg Jh Jk Jm Jp Li Ly Ma Mb Mc Mj Mk Ml Mn Mv Mw Ne Nh Ni Nj Nl Nm Nq Nu Nv Nx Ny Oz Pb Pc Pd Pf Qc) Mu(Fp Hq Hr Hx Ii Il Io Iq It Jk Jm Jp Li Lu Ly Mb Md Mj Mk Ml Mn Mw Nb Nd Ne Nh Ni Nl Nq Nu Nx Ny Om Oz Pd Pf Pg Po Qb Qe) Ip(Et Fp Hu Hx Ii Ik Im It Iu Jm Js Li Lu Lv Lx Lz Mb Md Me Mf Mh Mx My Nb Nd Ni Nj Nl Nm Nu Nw Nx Oe Om Oy Oz Pb Pg Po Qd) Mq(Et Fp Hq Hx Ij Ik In It Js Li Lj Lv Lz Md Me Mf Mh Mw Mx My Nb Nd Nc Nl Nm Nr Nx Of Oi Om Oz Pa Pc Pg Po Qb) Qd(Et Hu Hx Ih Ij Io Ir Iu Lv Lx Lz Mb Md Mg Mh Ms Mt Mx Nb Nc Nd Nj Nk Nm Nr Oe Of Og Oh Oi Om Oz Pa Pg Po) Nn(Hr Ik Il Iq Jh Jp Li Lj Lu Ly Lz Ma Mb Md Mj Mm Mn Mv Mw Nd Nh Nl Nq Ns Nu Nv Nx Of Oh Oz Pb Pd Qb Qe) Lh(Fp Ij Iq It Jg Jh Jk Jp Li Lu Lx Lz Ma Mb Mc Me Mf Mj Mn Mr Nb Nf Nl Nq Nr Nu Nv Pa Pd Pf Po Qb Qc Qe) Ih(Et Hu Hx Im Io Iu Lx Mb Md Me Mg Mh Mj Mm Mr Ms Mx My Nb Nc Nf Ni Nj Nk Nr Nu Nw Oe Oh Om Oy Pa Pg) Jo(Et Hr Hx Ij Ik Io Iu Js Lj Lv Lx Lz Md Mh Mm Mx My Nc Nd Nf Nh Ni Nj Nl Nm Nr Ns Oi Oz Pa Pg Qb) Nm(Fp Hu Hx Im In Io Iu Lv Lz Md Mf Mh Mm My Nd Nf Nj Nl Nr Nw Oe Of Oi Oy Pa Pb Pc Pg Po Qb) Oh(Et Fp Hu Ii It Iu Js Lj Mb Md Mf Mh Mm Mt Mx My Nb Nd Ni Nk Nl Ns Nu Nw Oe Oy Pc Pg Po Qb) Mr(Et Hq Hu Hx Ij Ik Im In Io Iu Js Ly Md Me Mk Ml Mt Mx Nf Ni Nj Nk Nw Ny Oi Om Oz) Mg(Ii Im Jk Js Li Lv Lx Mb Md Me Mh Ms Mt My Nb Nj Nk Nl Nu Nw Oe Oi Pa Pd Po Pz) Mx(Et Hu Ij Ik Im In Iu Lv Md Mf Mm Ms My Nc Nf Nj Nk Nw Oe Of Oi Om Oy Oz Pb) Nw(Et Hu Ij Im Io Iu Lv Mb Me Mh Nc Nd Nf Ng Ni Nj Nk Nr Nu Oe Of Oi Pb Pc) Pz(Jg Jk Jp Lj Lv Lx Lz Mb Me Mh Ms Mw Nb Nc Ng Nk Nl Nu Og Oy Oz Pa Po) Pc(Et Fp Hu Hx Ii Im Io Iu Js Lv Lx Mc Mt My Nb Nc Ni Nk Ns Om Oy Pg Po) In(Et Ij Ik Io Li Lj Lv Lx Lz Mf Mv Nd Ni Nl Nr Ns Oe Oi Om Pa Pg Qb) Im(Et Hu Ij Iu Js Lv Md Mh Mm Ms Mt Nb Nf Nj Nr Oe Og Oi Om Oy Pa) Mz(Hq Ii Ij Iq It Jg Jh Jk Jm Jp Js Lu Mc Me Mj Mk Pd Pf Po Qe) Ng(Fp Hu Iq It Li Mb Mh Nd Ni Nj Nk Nl Nq Nu Nx Oe Og Pd Qb Qe) Et(Fp Hu Hx Ij Io Iu Lx Md Mh Ms Mt Nc Nf Nr Oe Of Og Oi Pa) Nc(Hu Hx Io Iu Js Lv Lx Md Me Mt Nb Ne Ni Nr Og Oi Om Pa) Na(Iq Jg Jh Jk Jm Lu Mb Mc Me Mj Mk Mn Mv Nb Pf Qc Qe) Ij(Hu Hw Ik Lx Lz Mh Ml Mm Mt Nd Nj Nl Ny Oe Oi Pa) Og(Fp Hu It Jk Js Lv Mb Md Me Mh Mv Nk Nu Nv Nx Qb) Nr(Hu Hw Io Lv Md Mm Ms Mt My Nf Nj Nk Oi Oy Oz) Hw(Iq Jk Lu Mb Mc Me Mj Mn Nb Nu Pf Po Qc) Ms(Ii Iu Jg Js Lx Mb Md Mt Nf Pa Pg Qb) Nf(Hu Lv Mh Ml Nl Ny Oe Oi Pa Pb Pg) Iu(Fp Hu Lv Me Mm Mt Ni Nj Oe Oi Om) Om(Ik Lx Mh Ml Mm Nk Ns Oe Oi Pb) Mt(Hu Lv Me Ml Mm Nj Nk Oe Pg) Nb(Hu Hx Mh Ml Nj Nk Ny Oi Pb) Hx(Hu Io Mh Mm Nk Ny Oi Pb) Lx(Lv Me Mh Nj Of Pb) My(Jg Mv Nv Pa Pg Po) Of(Ii Md Pa Pg Po) Nk(Io Lv Me Oi) Hu(Md Nq Pg Qb) Js(Io Mm Nj Oi) Oy(Jg Nv Qb) Md(Lj Nj) Mh(Mb Oi) Ir(Qb Qe) Pa(Lv Nj) NsNd MjIk MmPg NyPb} Is{Et(Fp Hq Hr Hu Hv Hx Ih Ii Ij Il Im In It Iu Iv Jg Jh Jk Jm Jn Jo Jp Js Jt Li Lv Ly Lz Ma Mb Mc Me Mf Mh Mj Mk Ml Mq Mv Mw Mx My Na Nb Nc Ni Ns Nu Nv Nx Ny Ok Om Oy Oz Pb Pd Pf Qa Qb Qc) Lx(Hu Hv Hx Ih Ii Ij Il Im In It Iu Iv Jg Jh Jn Jp Li Lu Lv Ma Mb Md Me Mf Mj Mk Ml Mr Mw Mx Nb Nc Nd Nf Nh Nj Nk Nl Nq Nr Ns Nu Nv Nx Ny Oz Pa Pb Pe Pg Qb Qc) Nt(Fp Hq Hu Hv Hx Ih Ij Im Iq Ir Iv Jh Jk Js Lj Lz Mb Mc Me Mf Mh Mk Ml Mn Mr Mv Mw Mx My Na Nb Nc Ni Nk Nr Ns Nu Nv Ny Oy Oz Pa Pb Pd Pf Po Qa Qb Qc Qd Qe) Jq(Fp Hr Hu Hv Hx Ih Ii Ij Ik Im In Jh Jm Jn Jo Jp Lv Ly Lz Mb Md Me Mj Mk Mq Mv Mw Mx My Mz Na Nb Nc Ne Nf Ng Ni Nk Nm Ns Nw Nx Of Ok Om Oz Pb Pd Pf Qa) Lw(Fp Hr Hu Hv Hx Ii Ij Ik Im In It Iu Iv Jg Jh Jm Jn Jo Jp Lv Ly Lz Ma Mb Mf Mq Mv Mw Mx My Na Nc Ne Ng Ni Nj Nk Nm Ns Nu Nv Oe Of Ok Pd Qa Qc) Io(Hu Hv Hx Ii Ij Il Im In Iq Ir Iv Jh Jn Js Ly Lz Mb Mc Mf Mj Mk Ml Mn Mv Mw Mx My Na Ne Ng Ni Nl Ns Nx Ny Of Oy Oz Pb Pd Pf Qb Qc Qd Qe) Pa(Hr Hv Hw Hx Ii Ij Ik In It Iu Jn Jo Jp Li Lu Lv Ly Ma Md Mj Ml Mq Mt Na Nc Ne Nf Ni Nm Nq Nw Nx Ny Of Ok Om Oy Oz Pb Pe Pg Qa) Pe(Hw Hx Ii Il Im In It Iu Iv Jg Jm Jp Jt Lu Lv Ma Mb Md Me Mk Ml Mq Mz Nd Ne Nf Nh Nj Nk Nm Nx Ok Om Oy Oz Pf Pg Qb Qc) Mg(Hr Hv Ii Ij Im In Ip It Iu Jn Jp Jt Li Lv Ma Mb Mf Mh Mq My Na Nb Nc Nd Ne Nh Ni Nj Nk Nm Ns Nu Nv Nx Oy Po Qa Qc) Mm(Hq Ih Il Im Iq It Iu Iv Jg Jh Js Lj Ly Lz Mc Mj Mk Ml Mn Mv Mw Mx Nl Nx Ny Oy Oz Pb Pf Qb Qc Qd Qe) Mt(Hr Ik Im Ip Iu Jm Jo Jr Jt Lj Lu Lv Ma Mq Mr Mv Na Nc Nd Ng Ni Nj Nm Nr Nu Oe Oh Ok Om Qa) Nq(Hr Hv Ij In Ip Iu Jn Jo Jp Jt Li Lu Md Mh Mq Na Nc Nh Ni Nk Nm Nu Nx Oh Om Pg Po Qa) Mz(Hr Hw Ip Iu Jg Jk Jr Js Li Lj Lu Lv Ma Md Mh Ml Mq Mr Mx Nj Nr Nv Nw Oe Om Po) Og(Hr Hv Ij Im In It Iu Jm Jp Li Ma Mb Me Mh My Na Nd Nj Nk Nu Ny Oe Oi Oz Pd Qa) Mi(Fp Hu Ih Iq Ir Iv Jk Js Lj Lz Mc Mf Mk Ml Mn Mv Nb Nd Nv Oz Pd Pf Qb Qd Qe) Ms(Hr Hv Hx Ij Ik In Ip It Iu Jk Jm Jo Jp Li Lu Mh Mv Na Ni Nr Nu Nv Of Oz Qa) Oh(Hv Ij In Ip Jg Jk Jo Jp Jr Lu Lv Md Mq Na Nb Nd Nf Ni Nj Nr Nw Oe Ok Qa Qc) Pz(Hr Hu Hx Ij Im It Iu Jh Jo Mq Mw Nc Nd Nh Nj Nk Nm Oe Oz Pd Qa Qd) Nw(Hv Ik In Ip Iu Jr Lu Mb Mh Mr My Na Nf Ni Nj Nm Nr Nu Nx Ok Pg Qa) Pg(Hr Hw Ii Im Ip It Iu Jr Jt Lu Mq Mr Nf Ni Nm Ns Nx Ok Om Oy Oz) Hw(Hr Ii Ik Ip Iv Jg Jp Jr Lu Ma Md Ml Nf Ng Nj Oe Of Om) Mr(Hr Ii Ik In Ip It Jm Jr Lu Ma Md Mh Mq Nf Ng Of Om) Pc(Hq Ih Il Iq Jg Js Lj Mc Mj Mk Ml Mv Nl Ny Pb Qb Qe) Mp(Ih Il Iq Js Lj Mc Mf Ml Mv Nd Nu Ny Pb Qb Qd Qe) Om(Hu Ip Iu Jm Jo Jr Lu Nd Ng Nk Nm Ns Nx Pb) Nf(Hr Ip It Iu Jo Jr Lu Ma Ml Nd Nj Qc) Oi(Ip It Jk Jo Jr Jt Li Ma Mh Nb Nr Pd) Po(Hr Ii Ip Jm Jo Jr My Ng Nj Of Pb) Md(Ik Ip Jr Li Ng Nj Nr Ns Nx Oe Ok) Lu(Ik Ip Jr Nj Nm Oe) It(Hv Ij Jn Jo Jt Qa) Nd(Hq Jm Jr Jt Ok) Jg(Hu Ns Oe Oy) Ng(Jo Ma Mw) Jr(Ip Ma) NrOe NuIk MvMy NbOf HuJh IrLh JoJt} Mu{Ir(Fp Hu Hv Hw Hx Ih Ii Ij In It Iu Iv Jg Jm Jn Jp Js Jt Li Lu Lz Mb Md Me Mf Mj Ml Mn Mq Mw My Na Nb Nc Nd Ne Nf Ni Nk Nm Nr Ns Nu Nv Nx Om Oy Oz Pd Po Qa Qc Qd) Ok(Fp Hq Hv Hx Ii Ij Il Im In Iq It Jg Jh Jk Jm Jp Js Lu Ly Ma Mb Mc Me Mf Mj Mk Ml Mn Mq Mv Mw Mx Na Nb Ni Nl Nm Nr Nu Nv Nx Ny Om Pd Pf Qc) Jn(Hr Hu Hv Hx Ih In It Iv Jg Jm Jp Js Li Lu Lz Ma Mb Md Me Mh Ml Mq Mt Mw My Na Nb Nc Ne Nf Nh Nk Nm Ns Nu Nv Nx Of Om Oy Oz Pb Po Qc Qd) Nw(Fp Hq Hr Ii Il Iq It Jg Jh Jk Jm Jp Js Li Lj Lu Ly Ma Mc Md Mf Mj Mk Ml Mn Mt Mw Mx Nb Ne Ni Nl Nq Nv Nx Om Oz Pd Pf Pg Po Qb Qc Qe) Qa(Hr Hu Hw Hx Ih Ii In Iv Jg Jm Jp Li Lu Md Me Mf Mh Ml Mn Mq Mv My Na Nb Nc Ne Nf Nh Ni Nk Nl Nm Nr Ns Nu Nv Om Oy Oz Po Qc Qd) Qd(Hr Hu Hv Hx Ih Ij In Io Iu Iv Jg Jm Jo Li Lu Lz Ma Mb Mg Mh Mq Na Nb Nc Nh Ni Nk Nm Nq Ns Nv Of Om Oz Pb Qc) Jt(Fp Hr Hu Hw Hx Ih Ii In It Iu Iv Jp Li Lj Lu Lz Ma Md Mh My Nc Ne Nf Nh Nk Nq Nr Ns Nv Nx Om Oy Oz Po Qb

Md Mr Ms My Na Nc Ni Nj Nk Nr Oe Of Oh Ok Pg Qd) Nw(Hq Ij In Ip Ir Iv Lv Lw Ml Mm Ng Ni Nj Oi Ok Oy Pe) Mt(Hq Hv Hw Ip Jt Lv Lw Mh Ms Na Ng Ny Ok Pe Pz) Og(Hv Hw Hx Im Ir Iv Jt Mr Nf Nv Ok Pg Po Qd) Pe(Hq Hr Ik Io Ip Jg Jo Lw Mg Ng Nj Ok Oy) Mm(Hv In Io Ip Ir Jt Mr Na Nf Pg Pz Qd) Ip(Hq Hv Hw Jt Lw Ms Na Ok Pz Qd) Io(Hw Ir Iu Jg Jk Jt Nc Pg) Lw(Ir Jp Lu Mr Ms Ng Qd) Qd(Hw Im Jg Nf Nj Ok) Nj(Hw Na Nf Ok) Of(Ij In Jh Nb) Oy(Jg Jk Pg Po) Pz(Jg Jk Jp) Pg(Jo Ng Ok) Jt(Mg Ms) MvMy HwJp NyPb} Mm{Mz(Hq Hr Hu Hv Ih Ii Ij In Iq It Jg Jh Jm Jo Jp Js Jt Lj Lw Lz Ma Mb Mc Md Me Mf Mg Mj Mk Mn Mq Mv Mw Mx My Ne Nf Ng Nh Ni Nj Nl Nm Ns Nu Nx Oe Oh Ok Oy Oz Pf Qc Qe) Qa(Et Fp Hr Hu Hw Hx Ih Ii Ij Ik Il Im In Ir It Iu Iv Jg Jh Jp Jt Li Lv Lw Ly Lz Ma Mf Mh Ml Mn Mq Mv Mw Mx Na Nc Ne Nj Nk Nm Ns Oe Of Oh Ok Pb Pd Qb Qc Qd) Mr(Et Fp Hw Ih Ij Im In Iv Jh Jk Jo Jp Js Jt Lu Ly Ma Md Mk Mq Ms Mx My Nc Nq Of Oh Oi Ok Oy Pa Pb Pd Po Qb) Jn(Et Fp Hv Hx Ii Ij Im In Jo Lw Ly Md Mg Mh Mt Na Nd Nf Ng Ni Nv Oe Ok Pd) Nw(Fp Ij Io Ip Iu Iv Lv Lx Mt Nf Og Ok Pa Pg Wm) Ir(Hw Ip Jk Lu Lv Md Mt Nf Nq Og Oi Po) Pg(Et Hq Hv Ij In Iv Jo Jt Mt Ns Og Oy) Pa(Et Ij Ip Lv Lw Ng Ni Og Ok Om Qd) Om(Et Ih Ip Iu Iv Lx Mg My Qd) Po(Et Hw Ip Ng Ns Og Pz Qd) Mt(Jo Jt Lv Ma Na Nr Pb) Hw(Et Ih Io Lv Nf Nq Qd) Et(Ip Jk Lw Md) Lx(In Ng Ok Qd) Nb(Ip Ms Oe Pz) Nf(Ip Lv Nr Qd) IiOg IoJt IvPz JhOy NyPb} Et{Pe(Hr Hw Im Ip Iu Jk Jn Jt Lx Mb Md Ml Mt Mz Na Nc Nd Ne Nf Nh Nj Nk Nm Nq Nw Oe Oz Pb Pf) Hw(Io Ip Jn Lw Lx Md Mg Nf Ng Nq Oe Of Og Oh Oi Pa Pg) Pz(Hx Ih Ip Iu Iv Li Lw Md Nb Nc Nf Nq Nr Nv Oh Qb) Lx(Hq Hv Io Ip Ir Mg Mh Mt Na Nc Ng Of Og Oh Oi) Mz(Io Ip Jk Mg Ml Mr Ms Na Nd Nk Nv Of Og Oh) Mr(Io Ip Jn Jo Mg Mt Ng Nw Oe Of Og Qa) Mt(Hx Ip Iu Ml Na Nc Nk Of Oy Pg Qa) Jn(Ip Jk Lu Lw Ms Nd Oe Og Oi Pa Pg) Nw(Iu Jo Jt Lw Nd Nk Nr Oe Og Oi) Pa(Io Ip Jt Mg Na Ng Of Oh Qa) Lw(Iu Jk Mh Nf Og Pg Qa) Mg(Iu Jk Jt Nq Om Po) Qa(Ip Md Nq Oh Oi Pg) Og(Hx Jh Mv Nr Pg) Po(Ng Of Oh Oy) My(Mv Nb Om) Io(Iu Jt Pg) Nq(Hu Ng) Ms(Nb Om) Nf(Iu Nk) Jt(Jo Ng) Oh(Oi Om) NbOe HuJk JhOy} Mt{Og(Fp Hq Hr Hu Ih It Jp Js Li Lj Lu Lx Ma Mb Me Mf Mj Ml Mn Mq Ms Mv Mx Nc Ne Nf Ni Nk Ns Nx Of Oi Oy Pd Pf Qb) Ny(Hu Hv Hx Ij Im Ip Ir Iv Jo Jt Lv Lw Ms Na Nb Nr Nw Oi Pg Qd) My(Iq It Jm Js Ly Mc Md Mf Mk Ml Mn Nl Nu Nx Oe Oh Qc) Mh(Hu Im Ip Ir Iu Iv Jn Lx Mz Nb Ng Nj Nw Ok Pg Qd) Pb(Io Iu Jt Lx Ma Mj Mv Mx Nb Nc Nf Ni Nk Nm Oe Po) Ml(Hv Ii Ij Jn Jo Jt Ns Ok Om Oy) Nq(Hw Lw Mv Mz Ok Oy Pe Qa) Lw(Io Iu Lx Nr Pg Qa) Md(Hv Ij Jo Na Om) Hx(Ii Mz Nb Nr Qa) Jt(Io Jo Nw Pa Pg) Of(Jk Mr Nr Pa) Hw(Lv Nw Pg) Qa(Ip Lx Pg) Oy(Jg Nr Oz) Pe(Ip Lv) WmMw MrOh MsNb MzIu NdHq NgJk QcQd OkPg} Nw{Hw(Hr Hx Ii Ik Im Iv Jk Jn Jo Jt Lu Lv Ma Md My Mz Na Nc Ne Ng Nh Nk Nm Nx Oy Pa Pe Pg Qa Qc) Jo(Hx Ii Ik Im Ip Iu Jt Lw Lx Md Ms Na Nd Nk Nm Nq Ns Nx Ny Oe Oh Oi Oy Qa) Jt(Im Iu Jk Lu Mg Mh Ml Mr Ms My Ng Nj Nm Ny Of Pa Pb Pe Pg Qa Qc) Qa(Ip Jk Lw Ma Md Mh Mr Ms Na Ny Oe Of Oh Oi Pa Pb Pg Qc) Na(Io Ip Iu Lw Mg Ms Oh Oi Pa Pe) Og(Hv Ij Ip Iu Mb Nm Pg Po) Pe(Ip Mg Ml Ms My Nq Oe Of) Nq(Hv Jn Mv Mz Ok) My(Jg Mg Om Pg) Iu(Hv Mz Oi Ok) Jk(Hu Oe Pz) Lx(Lw Mh) Nb(Ms Oy) In(Mh Pb) MgNg MrOh NdHq} Lw{Mr(Fp Ih Im In Ir Iu Iv Jg Jh Jk Js Li Lv Lx Ly Md Mf Mh Mk Mw Mx My Nc Nf Ng Nj Nk Ns Nv Oe Of Oi Om Oy Pb Pe Pg Po) Pe(Hq Hr Hw Im Ir Iu Jg Jk Jp Lx Ma Mf Mk Ms My Nf Ns Oi Om Oy Oz Pa Pb Pd Pf Pz Qa Qd) Pa(Fp Hv Hw Im Iv Jp Js Jt Li Lv Ma Mf Mg Mx Na Nc Nj Nq Oe Of Om Pb Pg Po) Lx(Ir Iv Jm Jt Lu My Oh Om Oy Qd) Po(Io Ip Jn My Ng Ns Qa) Og(Hx Jg Jk Mv Pg) Om(Ms My Ng Qa) Lu(Im Jn Qa) Nq(Ir Qa) Mz(Hw Jk) MsNb IoJn} Nq{Mz(Hx Im Ir Iv Jn Jo Jt Lj Lv Ma Mg Mh Mq Mr Na Nc Nf Nk Nr Oe Oz Pg) Qa(Io Ip Jn Jo Lx Mg Mr Ms Nj Oe Og Oh Oi Ok Pa Pe Pz) Jn(Hw Ik Io Ip Jm Jo Mg Mr Nj Nr Ns Oe Pa) Ok(Ih Ip Ir Ms My Nc Ng Nj Nk Oh Oy Pe Qd) Pe(Hr Hw Ip Jm Jo Jt Na Nj Oh Pb Pz Qd) Og(Hx Ir Jh Nr Pa Po) Ng(Ir Lx Mr Pa Pg) Hu(Hv Mr Mx Nf Qd) Oy(Lx Mr Pa) Ms(Jt Nb) Hw(Ip Qd) MyJh NbOf IrOi PzQd} Om{Og(Hr Hv It Jm Ly Mb Mc Md Me Mf Mk Mn Nh Nu Ny Oe Pd Pf Qc) Oh(Ip Iu Jo Mg Nd Ng Oe Oy Pz Qa) My(Ir Iu Jk Jn Jt Nv Pe Pg Qa) Of(Ii Ip Lu Lz Mg Mh Mw Mz Nr) Ms(Hw Jt Lx Mr Nb Pe Qa) Ng(Hw Jk Jt Mr Nd Pe Pg) Ik(Iv Pe Qa Qd) Jo(Hw Iu Mr Pe) Oy(Jk Mr Nb Nv) Oe(Hw Iu Pa) Lx(Jt Qa) Ml(Mz Qa) Pa(Hx Ny) Pe(Mg Pb) WmLj NsNd MzIu HwIp IrPz} Lx{Jt(Hr Hx Ii Ik Im In Jg Jm Jp Lv Ly Ma Md Ml Ms My Nj Nx Ny Oh Oi Pb Pe Pg Pz Qa Qd) Hq(Hv Hw Ij In Ip Jo Mb Na Nb Nd Pg) Qa(Io Ip Lz Ma Mg Mh Ng Og Pz) Mz(Hx Ip Iu Md My Oh) Jn(Ip Ng Of Oh Ok Pb) Mh(Ir Nb Pd Pf) Hw(Ip Of Oh) Jk(Ng Oy) Of(Hv Jo) Oh(Na Ok) Pb(In Ny) HuJh IjOg IpOk} Mz{Pg(Im Io Ip Jt Md Mg Mh Ml Ms My Ng Nj Ny Oh Oi Ok Oy Pa Pz) Mg(Ip Iu Mr My Ny Of Pa Pb Pe) Iu(Im Ip Jg Lv Ma Ms Og Pe) Ip(Hw Jk Mr Og Pe) Pa(Hx Lv Nj Ny Oh) Og(Jo Mr Po) Jg(My Of) Oh(Mr Pe) Oy(Jh Mw) MlNb NdHq JkOf LiLj} Pe{Oh(Hr Hw Ik Io Jg Jh Jp Ma Mg Mh Ms Ng Oe Pb Pf Pg Pz Qa) Mg(Ip Jg Jn Jo Jt Of Oy Pb) Jg(Ik Oe Of Pb Pz) Jt(Hr Ik Io Ng Pz) Ip(Ik Pb Pz) Jo(Hw Jn Ma) Og(Im Iu Jk) MaIk MyNb JkOy} Og{Jg(In Io Iu Jo Lu Md Mq Na Oh Ok Qe) Po(Jn Jt Lz Mg Ns) Mv(Hx Ip Ir Jo Ok) Jh(Ii Iv Lz Mh Qd) Mg(Hx Jn Nr Qa) Mr(Ip Jn Jt Oh) Pa(Ij Im Oh Qa) Jt(Ip Jk Pg) HwIp JkJn OkPg} Pa{Oh(Hv Hw Ip Jn Lv Ok) Qa(Ip Mg Mk Ml Oe) Jt(Ip Ms Ng Nj Of) Jn(Ip Mk Oe) My(Jg Nb) Jh(Ms Ng) Ok(Ip Mk)} Mw{My(Hu Hw Ii Ij Il In Jg Jh Jo Li Mj Na Nd Nj Nk Pb Qb) Oy(Ny Qa Qd) HuNy} Pg{Ok(Mg Ng Pb Pz) Qa(Io Jo Pz) Jt(Im Mg Pz) Jo(Hw Jn) MgNg MyJg NbOy} Mr{Oh(Im Jn Lv Oi Qa) Mg(Jn Ma Qa) Ng(Jg Ma) MvMy} Qa{Mg(Jo Ng Pz) Ma(Ng Pz) Nv(Io Oe) PzJg JhOy} Nb{Of(Im Ip Ma Mg Po) Ms(Ip Jg) MyIp} Jt{Jo(Ip Jk Nd) MaNg IoJp JhOy} Po{NsMh MgNg MyJg IpOy PzQd} Jh{Oy(Iu Jn Mx Nd)} Ng{Jg(Mg Nv)} HuNyPb HwIpOh

Unconstrained panels with 2 analytes, where 1.0E-7 >= 'model p-value' > 0. Contains 576 panels of 11,037 total panels evaluated. : Ji(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) aA(Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) No(Et Fr Hr Hv Hw Hx Ij Im In Io Ip Ir Is Iu Iv Jg Jh Jj Jk Jl Jn Jo Jp Jq Jr Js Jt Lh Li Lv Lw Ma Mb Md Me Mf Mg Mi Mm Mn Mp Mq Mt Mu Mw Mx Mz Na Nb Nd Nf Nj Nm Nn Nq Ns Nt Nv Nw Nx Oe Og Oh Oi Ok Om On Oz Pc Pe Pg Po Qa Qb Qd) On(Et Fr Hu Hw Im Io Ip Ir Is Jj Jl Jn Jq Jr Jt Lh Lw Mg Mi Mm Mp Ms Mu Mv Mw My Mz Ng Nj Nk Nm Nn Ns Nt Oe Of Og Oh Oi Oy Pc Pe Pz Qa Qd) Nn(Et Fr Hu Hw Hx Ii In Ir Is Iv Jj Jl Jn Jo Jq Jr Jt Lh Lx Mi Mp Mr Mu Mz Na Nb Nr Nt Nw Oi Ok Om Pa Pe Pg Po Qa Qd) Jl(Et Fr Im Io Is Jj Jn Jo Jq Jr Jt Lh Lw Lx Md Mg Mi Mm Mp Mt Mu Mz Nf Ng Nm Nq Nt Nw Oe Og Oh Oi Ok Om Pc Pz Qa) Fr(Hv Hw Ih In Ip Ir Is Iv Jj Jn Jo Jq Jr Jt Lh Lw Mi Mp Mq Mr Mu Mz Na Nt Oh Ok Pe Qa) Mu(Et Ir Is Jj Jn Jq Jr Jt Lh Mi Mp Mr Mz Nt Nw Ok Pe Qa Qd) Jq(Et Ip Is Jj Lh Lx Mg Mi Mm Mp Mr Nd Nq Nt Pa Pc Pe Pg) Is(Et Io Jj Lh Lw Lx Mg Mi Mm Mp Ms Nt Og Pa Pc Pe) Lh(Et Ip Jj Jn Jo Jr Lw Mm Mp Nw Og Oh Pc) Jr(Et Jj Lx Mg Mi Mm Mp Nq Nt Pc) Nt(Jj Lw Mm Mp Mt Mz Nw Pc) Jj(Jk Jn Nq Om Pe Pg Po) Mi(Jn Mz Om Pc Qa) Mm(Mr Mz Pe Qa) Mp(Jn Mz Nw Om) Og(Mt Mw Nb Om) Pc(Mr Mz Pe) LwMr MtMy HwNw Unconstrained panels with 2 analytes, where 1.0E-6 >= 'model p-value' > 1.0E-7. Contains 746 panels of 11,037 total panels evaluated. : Fr(Et Fp Hq Hr Hu Hx Ii Ij Ik Il In Io Iq It Iu Jg Jh Jk Jp Js Li Lj Lu Lv Lx Ly Lz Ma Mb Md Me Mf Mg Mh Mj Mm Ms Mt Mw Mx My Nb Nc Nd Ne Nf Ng Nh Ni Nj Nk Nl Nm Nq Nr Ns Nu Nv Nw Nx Ny Oe Of Og Oi Om Oy Oz Pa Pb Pc Pd Pg Po Pz Qb Qd Qe) Jl(Fp Hq Hr Hu Hv Hw Hx Ih Ii Ij Ik Il In Ip Iq Ir It Iu Iv Jg Jh Jk Jm Jp Js Li Lj Lu Lv Ly Lz Ma Mb Mc Me Mf Mh Mj Mk Ml Mn Mq Mr Ms Mv Mw Mx My Na Nb

Figure 42 Continued

Nc Nd Ne Nh Ni Nj Nk Nl Nr Ns Nu Nv Nx Ny Of Oy Oz Pa Pb Pd Pe Pf Pg Po Qb Qc Qd Qe) On(Fp Hq Hr Hv Hx Ih Ii Ij Ik Il In Iq It Iu Iv Jg
Jh Jk Jm Jo Jp Js Li Lj Lu Lv Lx Ly Lz Ma Mb Mc Md Me Mf Mh Mj Mk Ml Mn Mq Mr Mt Mx Na Nb Nc Nd Ne Nf Nh Ni Nl Nq Nr Nu Nv
Nw Nx Ny Ok Om Oz Pa Pb Pd Pf Pg Po Qb Qc Qe) Is(Hr Hv Hw Hx Ij Ik Im In Ip It Iu Jg Jk Jm Jo Jp Jr Jt Li Lu Lv Ma Mb Md Mh Mq Mr
Mt Mv Mz Na Nb Nd Nf Ng Nh Ni Nj Nk Nm Nq Nr Nu Nv Nw Oe Of Oh Oi Ok Om Pd Pg Po Pz Qa) Lh(Hq Hr Hx Ih Im In Io Ir Iu Iv Jg Jh
Jk Jp Jt Li Lv Lx Ly Ma Md Me Mg Mh Mi Ml Ms Mt Mw Mx My Mz Nc Nd Ne Ng Nj Nk Nm Nq Nt Ny Oe Of Oi Ok Om Oy Pb Pe Pg Po
Qa Qb Qd Qe) Jq(Fp Hv Hw Hx Im Ir It Iu Iv Jg Jh Jk Jn Jo Jp Jr Jt Li Lu Lv Lw Lz Ma Mh Ml Mq Ms Mt Mv Mw Mx Na Nb Nj Nk Nr Nu Nv
Nw Og Oh Ok Om Oz Po Qa Qd Qe) No(Fp Hq Hu Ih Ii Ik Il Iq It Jm Lj Lu Lx Ly Lz Mc Mh Mj Mk Ml Mr Ms Mv My Nc Ne Ng Nh Ni Nk
Nl Nr Nu Ny Of Oy Pa Pb Pd Pf Pz Qc Qe) Mu(Hv Hw Hx Ih Im In Ip Iu Iv Jo Jp Js Li Lv Lw Lx Lz Ma Md Mh Mj Mm Ms Mt Na Nb Nf Ng
Nj Nm Nr Oe Og Oh Oi Om Pa Pc Pg Po Qb Qe) Nt(Et Ik Im Io Ip Ir Jg Jn Jo Jp Jt Li Lv Ma Md Mg Mi Mw Nd Ne Nf Ng Nj Nq Oe Og Oh Oi
Ok Om Pe Pg Po Qa Qd) Nn(Fp Hv Ih Ij Il Im Ip Iu Jp Js Li Lv Lw Ma Md Me Mf Mh Mj Mq Ms Mt Mx Nd Nf Ni Nm Nv Nx Og Oz Pc Qb
Qe) Et(Hw Hx Ir Jj Jk Jn Jt Lw Lx Md Mi Mp Mr Mt Mz Nf Nr Nw Om Pa Pc Pe Pg Po Pz Qa) Pe(Hr Hw Ik Im Ip Iu Jg Jn Jr Jt Lv Lw Mg Mi
Mp Mt Mz Nq Nw Og Oh Ok Om Pb Qa) Jr(Hw Im Ip Iu Jg Jk Jo Jt Lw Ma Mr Mt Mz Nb Nd Nv Nw Oh Ok Om Pa Pg Po) Mi(Hv Hw Im Io
Ip Ir Jg Jj Jk Jp Jt Lw Mm Mp Ms Mt Nq Nw Ok Pg Po Qd) Jj(Ii Ij Ip Ir Iv Jh Jo Jt Lx Mp Mr Mt Mz Nv Nw Pa Qa) Lx(Hq Ir Jn Jt Lw Mp Mz
Ok Om Pc Qa Qd) Nw(Hv Iu Jo Jt Lw Mm Mr Mz Na Nq Pc Qa) Mp(Hw In Ir Jt Mr Nb Nf Ok Po Qa Qd) Pc(Hw Ir Jn Ok Om Pa Pg Po Qa
Qd) Mm(Hw Ir Jn Nf Om Pa Pg Po) Qa(Mg Mt Nq Oh Om Pa Pg) Mz(Ip Iu Lw Nq Pa Pg) Om(Ir Iu Jt Ms Of Oh) Pg(Jn Jt Lw Mt Ok) Nq(Ir Jn
Jt Ok) Mt(Mh Ny Pb) Pa(Jn Jt Lw) Mr(Jn Oh) PoLw MwMy

Unconstrained panels with 2 analytes, where 1.0E-5 >= 'model p-value' > 1.0E-6. Contains 1,192 panels of 11,037 total panels evaluated. : Pe(Fp
Hq Hu Hv Hx Ih Ii Ij Il In Io Iq Ir It Iv Jh Jk Jm Jo Jp Js Li Lj Lu Lv Lz Ma Mb Mc Md Me Mf Mh Mj Mk Ml Mn Mq Mr Ms Mv Mw Mx
My Na Nb Nc Nd Ne Nf Ng Nh Ni Nj Nk Nl Nm Nr Ns Nu Nv Nx Ny Oe Of Oi Oy Oz Pa Pd Pf Pg Po Pz Qb Qc Qd Qe) Mi(Fp Hq Hr Hu Hx
Ih Ii Ij Ik Il In Iq It Iu Iv Jh Jm Jo Js Li Lj Lu Lv Lx Ly Lz Ma Mb Mc Md Me Mf Mg Mh Mj Mk Ml Mn Mq Mr Mv Mw Mx My Na Nb Nc Nd
Ne Nf Ng Nh Ni Nj Nk Nl Nm Nr Ns Nu Nv Nx Ny Oe Of Og Oh Oi Oy Oz Pa Pb Pd Pf Pz Qb Qc Qe) Nw(Fp Hu Hx Ih Ii Ij Il Im In Io Ip Iq Ir
Iv Jg Jh Jk Jn Jp Js Li Lu Lv Lx Lz Ma Mb Md Me Mf Mg Mh Mj Mk Mq Ms Mt Mv Mw Mx My Nb Nc Nd Nf Ni Nj Nk Nl Nm Nr Ns Nu Nv
Ny Oe Og Oh Oi Ok Om Oy Oz Pa Pb Pd Pg Po Pz Qb Qc Qd Qe Wm) Jr(Fp Hr Hu Hv Hx Ih Ij Ik Il In Io Iq Ir It Iv Jh Jm Jn Jp Js Li Lj Lu
Lv Ly Lz Mb Mc Md Me Mf Mh Mk Ml Mn Mq Ms Mv Mw Mx My Na Nc Ne Nf Ng Nh Ni Nj Nk Nl Nm Nr Ns Nu Nx Ny Oe Og Oi Oy Oz
Pb Pd Pf Pz Qa Qb Qc Qd Qe) Pg(Hq Hr Hu Hv Hw Hx Ih Ij Ik Im In Io Ip Ir Iu Iv Jg Jh Jk Jm Jo Jp Js Li Lj Lu Lv Lx Lz Ma Mb Md Mg Mh
Mj Mp Mq Mr Ms Mw Mx My Na Nb Nc Nd Nf Ng Ni Nj Nm Nq Nr Ns Oe Of Og Oh Oi Om Oy Oz Pa Pb Po Pz Qd Qe) Nt(Fp Hq Hr Hu Hv
Hw Hx Ih Ii Ij Il In Iq It Iu Iv Jh Jk Jm Js Lj Lu Lx Ly Lz Mb Mc Me Mf Mh Mj Mk Ml Mn Mq Mr Ms Mv Mx My Na Nb Nc Nh Ni Nk Nl Nm
Nr Ns Nu Nv Nx Ny Of Oy Oz Pa Pb Pd Pf Pz Qb Qc Qe) Et(Fp Hr Hu Hv Ih Ii Ij Il Im In Io Ip Iq Iu Iv Jg Jh Jo Js Li Lj Lu Lv Ly Lz Ma Mb
Mg Mh Mj Mk Mm Mq Ms Mv Mw Mx Na Nb Nc Nd Ng Nj Nk Nl Nm Nq Ns Nu Nv Oe Of Og Oh Oi Ok Oz Pd Pf Qb Qd Qe) Mu(Fp Hq Hr
Hu Ii Ij Ik Il Io Iq It Jg Jh Jk Jm Lj Lu Ly Mb Mc Me Mf Mg Mk Ml Mn Mq Mv Mw Mx My Nc Nd Ne Nh Ni Nk Nl Nq Ns Nu Nv Nx Ny Of
Oy Oz Pb Pd Pf Pz Qc) Jq(Hq Hr Hu Ih Ii Ij Ik Il In Io Iq Jm Js Lj Ly Mb Mc Md Me Mf Mj Mk Mn My Mz Nc Ne Nf Ng Nh Ni Nl Nm Ns Nx
Ny Oe Of Oi Oy Pb Pd Pf Pz Qb Qc Wm) Om(Hu Hw Hx Ih Ik Im Ip Iv Jn Jo Jp Li Lj Lu Lv Lw Lz Mg Mh Mq Mr Mt Mx My Mz Na Nc Nd
Ng Nj Nk Nl Nq Nr Ns Nv Oe Oi Ok Oy Pa Pb Po Pz Qd Qe) Nn(Hq Hr Ik Io Iq It Jg Jh Jk Jm Lj Lu Ly Lz Mb Mc Mg Mk Ml Mm Mn Mv Mw
My Nc Ne Ng Nh Nj Nk Nl Nq Ns Nu Ny Oe Of Oh Oy Pb Pd Pf Pz Qc) Mp(Fp Hq Hv Hx Ih Ii Ij Im Ip Iv Jg Jh Jk Jo Jp Js Li Lu Lv Lw Ma
Md Mh Mj Mm Ms Mt Mw Mx Na Ni Nj Nm Nq Nr Ns Nv Oh Pa Pc Pd Qb Qe) Lh(Fp Hu Hv Hw Hx Ii Ij Ik Il Iq It Jm Js Lj Lu Lz Mb Mc Mf Mj
Mk Mn Mq Mr Mv Na Nb Nf Nh Ni Nl Nr Ns Nu Nv Nx Oz Pa Pd Pf Pz Qc) Is(Fp Hq Hu Ih Ii Il Iq Ir Iv Jh Jn Js Lj Ly Lz Mc Me Mf Mj Mk
Ml Mn Mw Mx My Nc Ne Nl Ns Nx Ny Oy Oz Pb Pf Qb Qc Qd Qe) Mz(Hw Im Ir Iv Jg Jk Jn Jo Jp Jt Li Lv Ma Mg Ml Mq Mr Ms Mt Mw Na
Nb Nc Nd Nj Nk Nr Nv Og Oh Ok Pb Po Qa Qd) Jt(Hx Im Io Ip Ir Iv Jg Jk Jn Jo Jp Li Lu Lv Ma Md Mg Mm Mr Ms Mt Mw Nd Nf Ng Nv Og
Oh Ok Pc Po Qa Qb Qd) Qa(Hw Hx Ii Im Io Ip Iu Jg Jk Jn Jo Jp Li Lu Lw Ma Md Ml Mq Mr Nb Nd Nf Nj Nr Nv Oe Og Oi Ok Po Pz) Jj(Hw
Hx Ih Il Im Iu Jg Js Li Lv Lw Ma Md Mg Mv Mw Mx Nb Nf Nr Nx Ny Ok Pc Pd Qb Qd Qe) Lx(Hv Hw Ih Im In Ip Iv Jo Jp Li Lv Ly Ma Mg
Mh Mm Mq Mt Na Ng Nm Of Og Oh Oy Pb Po) Mt(Hw Hx Im Ip Ir Iu Iv Jn Jo Lv Lw Ml Mm Mr Nb Nf Nq Nr Of Oh Ok Oy Pa Pc Po Qd)
Mm(Fp Hv Hx Ih Ii Ij In Ip Iv Jk Jo Js Lv Md Mx Na Nb Nr Nv Ok Qb Qd) Ok(Hw Hx Ip Ir Iu Iv Jk Jn Jp Md Mg Mr Nc Nd Nk Nv Oh Pa Po
Qd Qe) Po(Hw Im Ip Ir Iv Jn Jo Lv Ma Mr Na Nb Nf Nq Og Oh Oy Pa Qd) Mr(Ih Im Ip Ir Iv Jg Jk Jp Li Lv Ma Md Mg Mw Nq Og Qd) Lw(Hw
Hx Ir Iv Jk Jn Jp Li Lu Mx Nb Nf Nq Nr Nv Qd) Pc(Hv Hx Ii Im In Ip Iv Jo Jp Js Mx Na Nb Nf Nr) Jn(Hw Ip Jg Jk Jo Ma Md Mg Nb Nd Nr Nv
Oh) Pa(Hv Hw Im Ip Ir Li Lv Ma Na Og Oh Qd) Nq(Hu Hv Hw Ih Ip Iv Jo Na Nf Nr Qd) Nb(Im Ip Ir Li Ms My Of Oh Qd) Hw(Im Ip Jg Jp Li
Ma Mg Oh Qd) Fr(Jm Mc Mk Ml Mn Mv Pf Qc) Ir(Ip Jg Jk Ma Md Mg Nv Oh) Qd(Jg Jk Jo Md Nf Nr Nv) Og(Hx Jg Jh Jk) Wm(Ji No) Ip(Md
Nv) Oy(Jh Mw) NfIu ImOh aJdN Unconstrained panels with 2 analytes, where 1.0E-4 >= 'model p-value' > 1.0E-5. Contains 1,439 panels of 11,037 total panels evaluated. : Po(Fp
Hq Hr Hu Hv Hx Ih Ii Ij Ik Il In Io Iq It Iu Jg Jh Jk Jm Jp Js Li Lj Lu Ly Lz Mb Mc Md Me Mf Mg Mh Mj Mk Ml Mn Mq Ms Mv Mw Mx My
Nc Nd Ne Ng Nh Ni Nj Nk Nl Nm Nr Ns Nu Nv Nx Ny Oe Of Oi Oz Pb Pd Pf Pz Qb Qc Qe) Mr(Fp Hq Hr Hu Hv Hw Hx Ii Ij Ik Il In Io Iq It Iu
Jh Jm Jo Js Lj Lu Lx Ly Lz Mb Mc Me Mf Mh Mj Mk Ml Mn Mq Ms Mv Mx My Na Nb Nc Nd Ne Nf Ng Nh Ni Nj Nk Nl Nm Nr Ns Nu Nv
Nx Ny Oc Of Oi Oy Oz Pa Pb Pd Pf Pz Qb Qc Qe) Ok(Fp Hq Hr Hu Hv Ih Ii Ij Ik Il Im In Io Iq It Jg Jh Jm Jo Js Li Lj Lu Lv Ly Lz Ma Mb
Mc Me Mf Mh Mj Mk Mn Mq Ms Mv Mw Mx My Na Nb Ne Nf Ng Nh Ni Nj Nl Nr Ns Nu Nx Ny Oe Of Og Oi Oz Pb Pd Pf Pz Qb) Ir(Fp Hr
Hu Hv Hw Hx Ih Ii Ij Ik Im In Io Iq It Iu Iv Jh Jm Jn Jo Jp Li Lu Lv Ly Lz Mb Me Mh Mk Ml Mn Mq Ms Mv Mw Mx My Na Nc Nd Ne Nf Ng
Nh Ni Nj Nk Nm Nr Ns Nu Nv Ny Oe Og Oi Oz Pd Pf Pz Qa Qc Qd) Jn(Fp Hr Hu Hv Hx Ih Ii Ij Ik Il Im In Io It Iu Iv Jh Jm Jp Js Li Lu Lv Ly
Lz Mb Me Mf Mh Mj Mk Ml Mn Mq Ms Mv Mw Mx My Na Nc Ne Nf Ng Nh Ni Nj Nk Nm Ns Nu Nx Ny Oe Og Oi Oz Pd Pf Pz Qc Qd Qe)
Lx(Fp Hr Hu Hx Ii Ij Ik Il Io Iq It Iu Jg Jh Jk Jm Js Lj Lu Lz Mb Mc Md Me Mf Mj Mk Ml Mn Ms Mv Mw Mx My Nb Nc Nd Ne Nf Nh Ni Nj
Nk Nl Nq Nr Ns Nu Nv Nx Ny Oe Oi Oz Pa Pd Pf Pz Qb Qc Qe) Jt(Fp Hq Hr Hu Hv Hw Ih Ii Ij Ik Il Im In Io Iq It Iu Jh Jm Js Lj Lw Ly Lz Mb Mc
Me Mf Mh Mj Mk Ml Mn Mq Mv Mx My Na Nb Nc Ne Nh Ni Nj Nk Nl Nm Nr Ns Nu Nx Ny Oe Of Oi Oy Oz Pb Pd Pf Pz Qc Qe) aA(aC aH
aI aJ aM aN aO aP aR aU aW aX aY aZ bA bB bC bE bF bH bI bL bM bN bO bQ bS bV bW bZ cC cD cE cF cG cH cI cK cM cO cP cR cS cT
cU cV cW cX dB dC dD dE dF dG dH dI dK dL dM dN) Mz(Fp Hq Hr Hu Hv Hx Ih Ii Ij Ik Il In Io Iq It Jh Jm Js Lj Lu Ly Lz Mb Mc Md Me
Mf Mh Mj Mk Mn Mv Mx My Nc Nf Ng Nh Ni Nl Nm Ns Nu Nx Ny Oe Of Oi Oy Oz Pd Pf Pz Qb Qc Qe Wm) Qa(Fp Hq Hr Hu Hv Ih Ij Ik Il
In Iq It Iv Jh Jm Js Lj Lv Ly Lz Mb Mc Me Mf Mh Mj Mk Mn Ms Mv Mw Mx My Na Nc Ne Ng Nh Ni Nk Nl Nm Ns Nu Nx Ny Of Oy Oz Pb
Pd Pf Qb Qc Qd Qe) Mt(Fp Hr Hv Hx Ih Ii Ij Ik Il In Io Iq Jg Jh Jk Jp Js Li Lu Lz Ma Mb Md Me Mg Mj Mn Mq Ms Mv Mw Mx Na Nc Nd Ne Ng
Ni Nj Nk Nm Ns Nu Nv Nx Oe Oi Oz Pz Qb Qe Wm) Qd(Hr Hv Hx Ih Ii Ij Ik Il Im In Io Ip Iu Iv Jh Jp Li Lu Lv Ma Mb Mg Mh Mq Ms Mv

Figure 42 Continued

Mw Mx Na Nc Nd Nj Nk Nm Nu Nx Oe Og Oh Oi Oz Pd Pz Qc) Om(Fp Hq Hr Hv Ii Ij Il In Io Iq It Jg Jh Jk Jm Js Ly Ma Mb Mc Md Me Mf
Mj Mk Ml Mn Mv Mw Nb Nc Nf Nh Ni Nm Nu Nx Ny Oz Pd Pf Qb Qc Wm) Nq(Fp Hx Ii Ij Im In Iu Jg Jk Jp Js Li Lj Lv Lz Ma Md Mh Mj
Mm Mq Ms Mw Mx My Nb Nc Ng Ni Nj Nk Nm Nu Nv Oe Og Oh Oi Oy Pa Pc Qb Qe) Mp(Hr Hu Ik Il Io Iq It Iu Jm Lj Ly Lz Mb Mc Me Mf
Mg Mk Ml Mn Mq Mv My Nc Nd Ne Ng Nh Nk Nl Nu Nx Ny Oe Of Og Oi Oy Oz Pb Pf Pz Qc) Pa(Fp Hx Ih Ij In Iu Iv Jg Jh Jk Jo Jp Js Md
Me Mf Mg Mh Mk Mq Ms Mv Mw Mx My Nc Nf Ng Ni Nj Nk Nm Nr Nv Nx Ny Oe Oy Pb Qb Qe) Lw(Fp Hu Hv Ih Ii Ij Il Im In Io Ip Iu Jg
Jh Jo Js Lv Lz Ma Md Mg Mh Mj Mm Mq Ms Mv Mw Na Nc Nd Nk Ny Og Oh Pc Qb Qe Wm) Nv(Fp Hv Hw Ih Ij Im In Io Iu Iv Jo Jp Js Li Lj
Lv Lz Ma Mg Mh Mq Mw Mx Na Nb Nf Ng Nj Nm Nr Oe Og Oh Oi Pc Pg Qe) Mm(Hr Hu Il Im Io Iq Iu Jg Jh Jj Jp Li Lj Lu Lz Ma Me Mh Mj
Mq Mv Mw Nc Nd Ni Nk Nu Nx Og Oh Pc Pd Pf Pz Qe) Nb(Fp Hw Hx Ih Iu Iv Jg Jh Jk Jp Js Lv Lz Ma Md Mg Mh Ml Mw Mx Nc Nd Nf Nj
Nk Nm Ny Oe Oi Oy Pb Qb Qe) Pc(Fp Hu Ih Ij Il Iu Jg Jh Jk Li Lu Lv Lz Ma Md Mg Mh Mj Mq Ms Mw Nd Ni Nm Nx Ny Og Oh Oi Pd Qb
Qe) Ip(Hv Hx Ih Ii Ij Im In Iu Iv Jg Jk Jo Jp Js Li Lu Lv Lz Ma Mg Mv Mw Mx Na Nf Nr Og Oh) Li(Hv Hx Ii Ij Im In Iu Iv Jh Jk Jo Jp Lu Lv
Ma Md Mg Mq Mx Na Nd Nf Nm Nr Oh Oi) Pg(Fp Ii Il Iq It Ly Mc Me Mf Mk Ml Mn Mv Ne Nh Nk Nl Nu Nx Ny Pd Pf Qb Qc) Jo(Hx Ih Im
Iu Iv Jg Jk Jp Lv Lz Ma Md Mg Mw Mx Nd Nf Ng Og Oh Qb Qe) Hw(Hx Ih Iu Iv Jh Jk Js Lv Lz Md Mn Mw Mx Nd Nf Nj Ns Ny Qb Qe)
Et(Hq Ik It Jm Jp Mc Me Mf Ml Mn My Ne Nh Ni Nx Ny Oy Pb Qc) Ma(Hv Hx Ih Ii Ij In Iu Iv Jk Js Md Mq Mx Na Nf Nr Oh Qb Qe) Im(Hv
Hx Ii In Iu Iv Jg Jk Jp Lu Lv Md Mg Mh Mj Mq Na Nf Nr) aJ(aI aM aO bA bC bM bO bP bQ bW bX cC cF cM cQ cU dD dF dH) Oh(Hv Hx Ii
Ij In Iv Jg Jh Jj Jk Jp Lv Mw Mx Na Nf Nr Qe) dN(aO aP aY bA bH bO bS bW cC cJ cS cT dC dE dH dK dM) Nw(Hq Hr Ik It Jm Lj Ly Mc Ml
Mn Ne Ng Nh Nx Of Pf) Mg(Hv Hx Ih Iv Jp Js Lv Md Mx Na Nf Nr Og Qb Qe) Jg(Hx Ih Iu Iv Js Lv Mq Ms Mx My Na Nf Ng Nr Ns) Jj(Fp Hv
In Iq Jm Jp Mj Mn Mq My Na Nc Nd Nm Nu) Jk(Hu Hv Ih Iv Jp Js Lv Md Mh Mq Na Nf Ng Nr Oe) Iv(Hx Iu Jh Jp Lv Md Mq Mw Nd Nf Nr
Og) Jp(Hx Ii In Iu Lv Md Mx Na Nf Nr Wm) Lv(Hx Ih Ii Iu Md Mw Nf Nr) Md(Hx Iu Mx Nr Qe) Wm(Fr Jr Mw On) Nr(Js Nf Og) Iu(Hv Hx
Ij) Jr(Hq Mj Of) Nf(Mx Qe) Og(Ii Mv) aP(cF dH) MqMw NyPb cSdM

Unconstrained panels with 2 analytes, where 1.0E-3 >= 'model p-value' > 1.0E-4. Contains 1,598 panels of 11,037 total panels evaluated. : aP(aC aD aE aF aG aH aI aJ aK aL aM aN aO aQ aR aS aU aV aW aX aY aZ bA bB bC bE bF bG bH bI bJ bL bM bN bO bP bQ bR bS bU bV bW bX bZ cA cB cC cD cE cG cH cI cJ cK cL cM cN cO cP cQ cR cS cT cU cV cW cX cY cZ dA dB dC dD dE dF dG dI dJ dK dL dM) dN(aC aD aE aF aG aH aI aK aL aM aN aQ aR aS aU aV aW aX aZ bB bC bE bF bG bI bJ bL bM bN bP bQ bR bU bV bX bZ cA cB cD cE cF cG cH cI cK cL cM cN cO cP cQ cR cU cV cW cX cY cZ dA dB dD dF dG dI dJ dL) aJ(aC aD aE aF aG aH aK aL aN aQ aR aS aU aV aW aX aY aZ bB bE bF bG bH bI bJ bL bN bR bS bU bV bZ cA cB cD cE cG cH cI cJ cK cL cN cO cP cR cS cT cV cW cX cY cZ dA dB dC dE dG dI dJ dK dL dM) Iv(Fp Hq Hr Hu Hv Ih Ii Ij Ik Il In Io Iq It Jm Js Lj Lu Ly Lz Mb Mc Me Mf Mh Mj Mk Ml Mn Ms Mv Mx My Na Nc Ne Ng Nh Ni Nj Nk Nl Nm Ns Nu Nx Ny Oe Of Oi Oy Oz Pb Pd Pf Pz Qb Qc Qe) Jo(Fp Hq Hr Hu Hv Hw Ii Ij Ik Il In Io Iq It Jh Jm Js Lj Lu Ly Mb Mc Me Mf Mh Mj Mk Ml Mn Mq Ms Mv My Na Nb Nc Ne Nh Ni Nj Nk Nl Nm Nr Ns Nu Nx Ny Oe Of Oi Oy Oz Pb Pd Pf Pz Qc) Hx(Fp Hr Hu Hv Ih Ii Ij In Io Iq Jh Jk Jm Js Lj Lu Lz Mb Me Mf Mh Mj Ml Mn Mq Ms Mv Mw Mx My Na Nc Nd Nf Ng Ni Nj Nk Nl Nm Nr Ns Nu Nv Nx Ny Oe Of Oi Oy Oz Pb Pd Pf Qb Qe) Li(Fp Hq Hr Hu Ih Ik Il Io Iq It Jg Jm Js Lj Ly Lz Mb Mc Me Mf Mh Mj Mk Ml Mn Ms Mv Mw My Nc Ne Ng Nh Ni Nj Nk Nl Ns Nu Nx Ny Oe Of Og Oy Oz Pb Pd Pf Pz Qb Qc Qe) Hw(Fp Hq Hr Hu Hv Ii Ij Ik Il In Io Iq It Jm Lj Lu Ly Mb Mc Me Mf Mh Mj Mk Ml Mq Ms Mv My Na Nc Ne Ng Nh Ni Nk Nl Nm Nr Nu Nx Oe Of Og Oi Oy Oz Pb Pd Pf Pz Qc) Ip(Fp Hq Hr Hu Ik Il Io Iq It Jh Jm Lj Mb Mc Me Mf Mh Mj Mk Ml Mn Mq Ms My Nc Nd Ne Ng Ni Nj Nk Nl Nm Ns Nu Nx Ny Oe Of Oi Oy Oz Pb Pd Pf Pz Qb Qc Qe) Jk(Fp Hr Ii Ij Ik In Io Iq Iu Jg Jh Jm Lj Lu Ly Lz Mb Me Mf Mg Mj Mn Ms Mv Mw Mx My Nc Nd Ni Nj Nk Nl Nm Ns Nu Nv Nx Ny Of Oi Oy Oz Pb Pd Pf Pz Qb Qe) Nv(Hq Hr Hu Ii Ik Il Iq It Jg Jh Jm Lu Ly Mb Mc Md Me Mf Mj Mk Ml Mn Ms Mv My Nc Nd Ne Nh Ni Nk Nl Ns Nu Nx Ny Of Oy Oz Pb Pd Pf Pz Qb Qc) Ma(Fp Hr Ik Il Im Io Iq Jg Jh Jp Lj Lu Lv Ly Lz Mb Me Mg Mh Mj Mk Ms Mv Mw Nc Nd Ng Ni Nj Nk Nl Nm Ns Nu Nx Ny Oe Of Og Oi Oz Pd Pz) Nb(Hq Hr Hu Hv Ii Ij Ik Il In Io Iq It Jm Lj Lu Ly Mb Mc Me Mf Mj Mk Mn Mq Mv Na Ne Ng Nh Ni Nl Nr Ns Nu Nx Oz Pa Pd Pf Pz Qc Wm) Jp(Fp Hr Hv Ih Ij Il Io Iq Jg Jh Js Lu Ly Lz Mb Me Mf Mh Mj Mq Ms Mv Mw Nc Nd Ng Ni Nj Nk Nl Nm Nu Nx Ny Oe Og Oi Oz Pd Pz Qb Qe) Im(Fp Hr Hu Ih Ij Io Iq Jh Js Ly Lz Mb Me Mf Mk Mn Ms Mv Mw Mx My Nc Nd Ng Ni Nj Nk Nl Nm Nu Nx Ny Oe Og Oi Oz Pd Pf Pz Qb Qe) Nf(Fp Hu Hv Ih Ii Ij Il Iq Jh Js Lu Lz Md Mf Mh Mj Mk Mn Mq Ms Mv Mw My Na Nc Nd Nj Nk Nl Nm Nu Nx Ny Og Oi Oz Pb Pd Qb Wm) Nr(Fp Hv Ih Ii Ij In Iq Iu Jh Lu Lz Mf Mh Mj Mk Mn Mq Ms Mv Mw Mx My Na Nc Nd Nj Nk Nm Nx Ny Oe Oi Oz Pb Pd Qb Qe) Oh(Fp Hr Hu Ih Il Iq Iu Js Lj Lu Lz Md Me Mg Mh Mj Mk Mn Mq Ms Mv My Nc Nd Ni Nj Nk Nm Nu Nx Ny Oe Og Oi Oz Pd Qb) Lw(Hq Hr Ik Iq It Jm Lj Ly Mb Mc Me Mf Mk Ml Mn My Ne Ng Nh Ni Nj Nl Nm Ns Nu Nx Oe Of Oi Oy Oz Pb Pd Pf Pz Qc) Pc(Hq Hr Ik Io Iq It Jm Lj Ly Mb Mc Me Mf Mk Ml Mn Mv My Nc Ne Ng Nh Nj Nk Nl Ns Nu Oe Of Oy Oz Pb Pf Pz Qc Wm) Nq(Hq Hr Ik Il Io Iq It Jh Jm Lu Ly Mb Mc Me Mf Mg Mk Ml Mn Mv Nd Ne Nh Nl Ns Nx Ny Of Oz Pb Pd Pf Pz Qc) Ii(Fp Hv Ih Iu Jg Jh Js Lu Lz Md Mg Mh Mn Mq Ms Mv Mw Mx My Na Nc Nd Nj Nk Nm Nu Ny Oe Oi Pa Pb Pd Qb Qe) Md(Fp Hv Ih Ij Il In Iq Jg Jh Js Lj Lz Mb Mh Mj Mn Mq Mv Mw My Na Nc Nd Nj Nm Ns Nu Nx Ny Og Pd Qb) Qd(Fp Hq Hu Iq It Jm Js Lj Ly Lz Mc Me Mf Mj Mk Ml Mn My Ne Ng Nh Ni Nl Ns Ny Of Oy Pb Pf Qb Qe Wm) Lv(Fp Hv Ij Il In Iq Jh Js Lu Lz Mb Mh Mj Mq Mv Mx My Na Nc Nd Nj Nk Nm Nu Nx Ny Oe Og Pd Qb Qe) Mg(Fp Ij Il In Iq Iu Jg Jh Lj Lu Lz Mb Me Mh Mj Mm Mn Mq Ms Mw Nc Nd Ng Nk Nl Nu Nx Ny Oe Oi Oz) Pa(Hq Hr Hu Ik Il Io Iq It Jm Lj Lu Ly Lz Mb Mc Mj Ml Mn Nd Ne Nh Nl Ns Nu Of Oi Oz Pd Pf Pz Qc) Jg(Fp Hu Hv Ij In Io Iq Jh Lj Lu Lz Mh Mj Mw Nc Nd Ni Nk Nl Nm Nu Oe Oi Oy Pd Pz Qb Qe Wm) Mm(Hq Ik It Jm Ly Mb Mc Mf Mk Ml Mn Ms My Ne Ng Nh Nj Nl Nm Ns Ny Oe Of Oi Oy Oz Pb Qc) aA(aD aE aF aG aK aL aQ aS aV bG bJ bP bR bU bX cA cB cI cL cN cQ cY cZ dA dJ fR Wm) Js(Hv Ij Io Ir Iu Jh Lu Lz Mh Mq Ms Mv Mw Mx Na Nc Nd Nj Nm Nu Oe Og Oi Oz Pd Qe) Jj(Hq Hr Hu Ik It Lj Lu Lz Mb Me Mf Mh Mk Ng Nj Nk Nl Of Oy Oz Pf Qc Wm) bA(aI aM aO aS bC bE bH bJ bL bO bS bW cC cF cK cR cS cT cU dE dF dK dM) Mx(Hv Ih Ij In Iu Jh Lu Mb Mh Mn Mq Mv Mw Na Nd Nm Nx Ny Og Oi Pd Qe) Iu(Fp Ih In Jh Lu Mh Mj Mn Mq Mv Mw Na Ni Nm Nu Nx Ny Og Pd Qb Qe) Qe(Hv Ij In Ir Jh Lu Mh Mq Mv Mw Na Nd Nm Nu Nx Oe Og Oi Pd) Ih(Hv Ij In Jh Lu Mh Mj Mq Mv Mw Na Nd Nm Nu Nx Oi Pd Wm) dM(aI aM aO aU bC bO bQ bW cF cG cM cN dE dF dK) Wm(Et Iq Ir Is Jl Jn Jt Lh Mi Mu Nn Ny Po Qa) Mw(Hv Ij In Lu Lz Mh Mj Ms Na Nd Ng Nm Nu Nx) Mt(Hq Hu It Jm Lj Ly Mc Mf Mk Nh Nl Pf Qc) Na(Fp Jh Lz Mh Mn Mv Nd Nj Nk Ny Pd Qb) Ir(Hq Il Lj Mc Mf Mj Nl Of Oy Pb Qb) Jh(Hu Hv Ij In Lz Mh Mq Ms My Qb) Jn(Hq Iq Lj Mc Nl Of Oy Pb Qb) Nm(Fp Lu Lz Mh Nd Og Ok Qb) Ij(Lu Lz Mh Mq Ms Nd Oe Og) Mq(Lz Mv Nd Nk Ns Qb) In(Lz Mh Mv Nd Og Qb) cS(aM aO bO cF dD dF) Nd(Fp Hq Hv Nx) Nx(Lz Mh Og) Ok(Ml Oy Qc) Mj(Ik Il) Hv(Lz Qb) aM(aO bW) NsPd MvMy aObC bWcT Unconstrained panels with 2 analytes, where 1.0E-2 >= 'model p-value' > 1.0E-3. Contains 1,592 panels of 11,037 total panels evaluated. : cS(aC aD aE aF aG aH aI aK aL aN aQ aR aS aU aV aW aX aY aZ bB bC bE bF bG bH bI bJ bL bM bN bP bQ bR bS bU bV bW bX bZ cA cB cC cD cE cG cH cI cJ cK cL cM cN cO cP cQ cR cT cU cV cW cX cY cZ dA dB dC dE dG dH dI dJ dK dL) dF(aC aD aF aG aH aI aK aM aN aO aQ aR aU aV aX aY aZ bC bE bF bH bI bJ bL bM bN bO bP bQ bR bS bU bV bW bX bZ cA cB cC cD cE cF cG cH cI cJ cK cL cM cN cO cP cQ cR cT cU cV cW cX cY cZ dA dB dC dD dE dG dH dI dK dL) aO(aC aD aF aG aI aK aL aN aQ aR aU aV aW aX aY aZ bB bE bF bG bH bI bJ

Figure 42 Continued

Figure 42 Continued

Ji(Iu Lh Mm Mp Nd No Nx Qc) Mg(Et Ii Is Jo Jt Lh Om) Ok(Ip Iu Mf Mp Mu Nd Pg) Oy(Jh Lh Mw Nb Om Pg Po) Nr(Et Im Is Mu Pc Qd)
Ng(Is Jo Lh Om Pg Po) Mp(In Ir Jt Mm Na) Et(In Mm Mu Na) Is(Io Lh Mf No) Jo(Im Jt Lh Mf) Mu(Ii Ir Nb) Fr(Ir Na) No(Ln Io) Nb(Oe Of)
Jt(Nd Pg) MfIr MtMv NaPg IoLh} Og{Mw(aA Et Fp Fr Hq Hu Hx Ih Ij Im In Ip Ir Is Iu Iv Jg Ji Jl Jn Jq Jr Js Jt Lh Lj Lv Lx Mg Mh Mi Mp Mq
Mr Mt Mu Mx My Mz Na Nb Nf No Nr Nt Nw Oh Ok Om On Oy Pa Pc Pe Pg Po Qa Qd Qe) Om(aA Et Fr Hw Hx Ip Ir Is Iu Iv Jg Ji Jk Jl Jn Jr
Jt Lh Lw Lx Mi Mm Mp Mr Mt Mu Nb No Nq Nr Nt Of Oh On Pa Pc Pe Qa Qe) Ji(aA Fr Hw Hx Ii Il In Io Ip Is Iu Jg Jh Jk Jl Jo Jr Lh Lx Mg
Mi Mm Mr Mt Mu Mv Nb Nq Nr Nt Nv Pa Pc Pe Pg Po) Nb(aA Et Fr Im Io Ip Is Jg Jh Jl Jn Jq Jr Lx Ma Me Mg Mm Mp Mt Mu Mv Nj No Nq
Nt Nw Pc Pe Pg Po) Jl(aA Ij In Io Is Jg Jh Jn Jq Jr Jt Lh Lw Mg Mi Mm Mp Mt Mu Mv Mz Nf Nm No Nq Nt Oh Ok Pc Pz) Mu(aA Et Hx Ij Ir
Is Jg Jn Jq Jr Jt Lh Lw Mi Mp Mr Mt Mz No Nt Nw Ok On Pa Pe) aA(Hx Ii Ij In Ip Is Jg Jh Jk Jo Jq Jt Lh Lv Mf Mg Mt Mv Nt Nv Pa Pc)
Mt(Et Fr Hx Ii Is Jg Jh Jk Jr Lh Mp Mr No Nr Nt On Pa Pc Pe) Lh(Fr Ip Is Jg Jh Jn Jq Jr Lw Mg Mm Mp Mv Nw Pc) Jq(Fr Jg Jk Lx Mg Mi Mr
Nq Nt Pa Pc Pe Po) Is(Fr Io Jg Jh Mg Mi Nq Nt Pa Pc Pe Po) Jh(Jr Lx Mi Mr No Nt Nw On Pa Pc Pe) Jg(Hx Jr Mi Mz No Nt On Pa Pe Po) Fr(Hx Ij In Jn Jr Jt Mz Nt) Jr(Jk Mg Mi Nq Nt On Pc) On(In Io Ip Mg Mv Pc) Lw(Mr No Nt Pa Pe) Nt(Mv Nw Pc) No(Mg Mv) Nw(Jk Jo) Pc(Mr Pe) MmPe} aA{Io(Hx Ii Ij In Ip Is Iu Jg Ji Jk Jl Jn Jo Jr Jt Lh Li Lv Lw Ma Me Mg Mh Mi Mk Mm Mn Mp Mt Mu Nc Nj Nk Nq Nr Nt Nv Nw On Pa Pc Pe Pg Qa Qd Qe) Nj(Fr In Ip Jg Ji Jk Jl Jq Jr Lh Lv Lw Ma Mg Mp Mt Mu Mw Nd No Nq Nt Om On Pa Pc Pe Pg) Mm(Ij In Ip Is Ji Jl Jn Jq Jr Lh Lv Ma Mh Mp Mu Mz No Nt Nw Om On Pd Pe Pg Po Pz Qa) Pc(In Ip Is Ji Jl Jn Jq Jr Lh Lv Lx Mg Mp Ms Mu No Nt Oi Pa Pe Pg) Me(Ii Ij In Jh Ji Jn Jq Jr Lv Ma Mg Mh Mz No Nt Oi Pe) Lw(Fr Ip Jl Jr Lx Mg Mp Ms Mu Nq Pa Pe Pg Po) Mp(Hq In Ip Jg Ji Jn Jq Jr Mu No Ns Nt Om) Oi(Jg Jk Jn Lh Li Ma Mg Mt Mu Nq On Qa) Pz(Et Ip Is Ji Jk Jl Li Ma On Qa Qd) Jg(Ip Jq Lv Ms My No Ns Nt Oe) Nq(Hu In Ji Jn Jq Jr Mz Qa) Mg(Ip Jl Jq Jr Lv Ng No) Mu(Hu Ip Ji Jr Lv Mi Oe) Jq(Fr Lh Lx Mi Nt Pa) Oe(Jh Jk Jl Mw Nv On) Ms(Jh Ji Jn Mv Mw) Mt(Hx Mh My Ny Pb) Jr(Fr Hr Ip Jk Ma) My(Jh Mv Mw Om) Ji(Fr Jk Jl Nh) Ma(In Jk) Mw(Ng Oy) Ne(Nc Nl) FrJn NtIp HuJk JhOy JoNw OfOm} Ji{Ms(Fr Hw Ii Is Iu Jg Jh Jk Jl Jr Lh Mi Mm Mp Mr Mu Mw Na Nb Nd Nq Nt On Pa Pc Pe Po Qc) Io(Hw Ip Is Iu Jk Jl Jo Jr Jt Lh Lv Lw Mi Mm Mp Mr Mt Na Nc Nd Nk Nr Nt On Pa Pc Pe Pg) Mm(Et Fr Hw Ip Is Iu Jk Jl Jr Lh Lu Lx Mp Mr Mt Mu No Nq On Pa Pc Pe Pg Pz Wm) Pz(Et Fr Il Ip Is Iu Jg Jk Jl Jo Ma Mp Mt Mu Nq Nt On Pe Pg Po Qa Qe) Pc(Hu Hw Is Iu Jr Lh Lu Lx Mi Mp Mr Na Nd No Nt Nx Oi Pa Pe) Nx(Fr Hw Iu Jk Jl Jr Lh Lu Mi Mu Nq Nv On Pa Pe Pg Po) Ml(Ii In Jk Lh Lu Lx Mr Mt Nr Pa Pe Po) Qc(Is Jl Jr Lu Mj Mt Mu Nr Oh On Pe Po) Of(Jk Lx Mt Mu Nb Nq On Pa Pe Po) Pa(Hx Md Mh Mk My Ny Oe Oy Pb) Po(Hx Md Mh My Ny Oy Pb) My(Jh Jk Mt Mv Mw Nq) Nq(Hu Jr Ng Oy) Nk(Fr Ip Lu Ne) Jk(Ng Oe Oy Pb) Mh(Lx Mr Pe) Mp(Fr Jl No) Mt(Md Ny Pb) Jo(Hw Jl Nt) Jr(Fr Mi Nd) Oi(Jl Mu On) Lu(Me Nj) Ne(Nc Nl) Oy(Jh Mw) Pb(Lx Pe) NoMu NdHq HwIp IiLh} Jq{Mm(Fp Hw Ip Is Jk Jl Jr Lh Lx Mh Mi Mp Mr Mu Nd No Nq Nr Nt On Pa Pc Pe Pg Po Pz Qa) Pc(Et Hw Im Ip Is Iu Jl Jr Lh Lx Mi Mp Mr Mu Nd No Nq Nr Nt On Pa Pe Pg Po Qa) Pa(Hr Hx Ii Ip Jo Md Mg Mh Mk Ml Mp Ms Mu My Nb Nj Nq Ny Oe Of Oy Pb) Mp(Fr Hq Jg Jl Jo Lh Mi Mr Mu Nj No Ns Nt Of On Pd Pe Pg) Lx(Et Hq Ip Is Jl Md Mh Ml Mu Nj Ny Of On Pb) Mu(Et Ip Iu Jl Lh Mi Mr Nd Nj No Nt On Pe) Nq(Hu Hw Ip Jl Jr Mr My Nj No Nr Oy Pe) Mi(Fr Ip Jl Jr Md Mh Ml Nj Ny Of Pb) On(Io Ip Nd Nj Nx Of Oi Pz Qc) Fr(Is Jr Na Nj Nk No Nt Pz) Mr(Et Hr Ip Jo Lw Mg Mh Ml) Pe(Hr Ip Mg Mh Ml Nj Of Pb) Jl(Ii Io Jo Mg Ms Nd Pz) Lh(Ii Jo Mh Ml Nj Of) Nt(Ii Io Ip Jo Nj) No(Ip Jo Mg Nj) Mt(Md Of Pb) MwMy NdHq IsIt} On{Of(Hu Hv Hw Ij In Io Ip Jl Jo Jr Lh Mm Mp Mu Mz Na Nf No Ns Nt Oi Om Pe Pz Qa) Pz(Et Fr Hu Ip Is Jl Jn Jr Mi Mm Mp Ms Mu My Ng No Nt Oy Pc Qa Qd) Ng(Fr Io Ip Jk Lx Mg Mp Ms Mu Nd No Nq Nt Oi Pa Pc Qc) Io(Hu Is Iu Jr Lw Mi Mm Mp Ms My Nk No Ns Nt Oy Qa) Mu(Hu Jr Mg Mm Ms Mv Mw My Nj Ns Oe Oi Oy) Jr(Hu Ip Lw Mm Mp No Ns Nt Oe Oi Pc Qc) Hu(Hx Ip Is Mh Nq Ny Oi Pb Pc Qc) Ns(Hx Ip Is Mh Mp Ny Oi Pb Pc) My(Jh Jk Mg Mt Mv Mw Nq Om Qc) Mm(Ip Is Jl Mp No Nt Oe Oi) Oy(Jh Jk Mg Mp Mw Nq Oi Qc) Oe(Ip Is Jl Jn Mp No Qa) Oi(Ip Is Jl Jn No Pc) Ms(Ip Mg Mp Pc) Jo(Jl Lh Nt) No(Ip Nj) Mk(Mp Pa) NmIp MpMz HwPb} Mu{Nt(Et Ik Io Ip Is Jl Jn Jo Jr Lw Mg Mm Mp Ms Mt Mz Ng Nj Nw Oe Of Oh Oi Pc Pz) Mi(Hq Ik Is Jo Jr Mg Ms Mz Ng Nj No Of Oy Pb Pc Pz Qa) Is(Ik Io Lh Lw Mg Mm Mp Ms Ng Nj No Oe Of Oi Pc Pz) Jl(Ik Jo Jr Lw Mg Mm Mp Ng Oe Of Oh Oi Pb Pc Pz) Lh(Jo Jr Lw Mg Mm Ms My Ng Nj Oe Of Oy Pb Pc) Pe(Ik Jo Jr Lw Mg Mm Ng Of Oh Oy Pb Pc Pz) Jr(Et Ip Lw Lx Mm Mp Nj No Nq Pa Pc) Mp(Hq Jn Mm Mz Ng No Ns Nw Ok) Ng(Et Fr Jt Lx Pa Pg) No(Hu Ip Lw Mm Nj) Et(Mg Mm Of Pz) Oy(Mw Pa Pg) Mm(Jn Mz) Mr(Lw Pc) Pz(Qa Qd) Of(Nb Om) FrJn MkPa MtMy IkQd JoJt} No{Mp(Hq In Io Is Jg Jn Jr Lw Mg Mm Mz Nj Ns Om Pc Pg Qa) Mm(Hv Ij In Io Ip Is Jn Jr Lv Mz Om Pz Qa) Mg(Is Jl Jn Jo Jr Lw Ng Nj Oi Pc Qa) Oh(In Ip Jg Jl Jn Jr Lv Nj Oi Om Qa) Pc(In Io Is Jn Jr Mi Mz Oi Qa) Fr(Is Jn Jr Jt Lw Nj Pz Qa) Nq(Hu Ip Jn Jr Mz Nj Oi Qa) Mi(Io Jn Jr Mz Nj Om Qa) Lw(Io Is Jl Jo Jr Om) My(Jg Jh Mt Mv Mw Om) Nj(Jr Jt Mz Qa) Jg(Ng Ns Oi Qa) Jo(Jl Jt Om Qa) Mt(Mh Ny Pb) Pz(Et Is Jl) Mw(Ng Oy) Io(Is Jt) Jr(Hr Ip) NdHq JhOy OfOm} Jl{Lw(Im Io Jo Jr Lh Lu Lx Mg Mm Ms Mt Mz Nf Ng Nt Oe Oh Oi Pz) Pc(Im Io Jo Jr Lh Mg Mi Mm Ms Mz Nf Ng Nt Oi Pz Qa) Pz(Et Fr Im Is Jg Jn Jr Mg Mi Mm Mp Nt Oh Om) Mp(Hq Io Jn Jo Jr Mk Mm Mz Nf Ng Ns Oz) Jo(Hw Jt Lh Md Mg Mi Mz Nm Nt Om Qa) Mm(Et Io Jn Jr Mg Mt Mz Nf Qa) Mg(Jr Ms Mz Ng Oe Of Oi) Mt(Hx Mh My Ny Of Oy Pb) Io(Is Jt Mi Nt Oh) Ng(Fr Lh Nq Nt) Jh(Ms My Oe Oy) Mi(Jr Mz) Mw(My Oy) NqJr MvMy OfOm OhOi} Fr{Nt(Ik Jn Jo Jr Lw Mg Mz Ng Nj Oe Oh Pz) Mp(Hw Ir Jn Jr Mm Mz Na Ng Pz Qa) Is(Io Mg Mm Ms Ng Oe Of Oi Pz) Pz(Et Ip Ir Jn Jr Jt Qa Qd) Ng(Hw Jn Jo Jt Lh Na Qa) Mg(Jo Jr Jt Lh Qa) Of(Hw In Lh Nb Om) My(Mt Mw Nb Om) Lw(Jn Jr Lh) Jo(Hw Jt Lh) Ms(Jn Jt) Na(Jn Mz) Oy(Jh Nb) MmJr HwOh IoJt} Pc{Is(Hw Io Lh Lx Mi Mr Ms Mz Nf Nt Oi Pa Pe Pz) Lh(Io Jn Jo Jr Mg Mp Ms Mz Ng Nw Oi Qa Qd) Pe(Io Jn Jo Jr Mg Mp Mz Ng Nw Oi Pf Pz) Nt(Io Jn Jr Mp Mt Mz Nf Ng Nw Oi Qa) Mi(Io Jn Jr Ms Mz Qa) Jr(Et Lx Mp Mr Pa) Mz(Lx Mp Mr Pa) Qa(Lx Nw Pa) Jn(Lx Mr Pa) My(Jh Mt) HwNw JhOy} Mp{Jr(Et Hq Io Lh Mi Mr Mz Ns Nt Nw Om) Mz(Et Hq Is Nj Ns Nt Of Pd Pf) Nw(Hv Hw Is Jo Jt Na Ok Qa) Nt(Io Jo Mm Mt Ng Oe) Lh(Hq Jo Mg Mm Ng) Om(Mm Ng Ns Of Oy) Is(Io Ms Pz) Mk(Pa Pe) Mw(My Ng) Nb(Ms Of) EtMm MtMy NgJg IoJn JhOy} Mm{Jr(Hw Io Lh Lu Lx Mi Mr Ms Mz Nt Oi Pa Pe Pz) Is(Io Lh Mr Ms Mz Nf Nt Pe Pz) Pe(Ik Io Jo Mg Mz Ng Oy Pz) Lh(Io Jn Jo Mg Mz Ng Pz) Nt(Io Jn Mt Mz Nw) Mz(Pa Pg) Pz(Jn Qa) Nw(Hw Qa) MrJn} My{Mw(Et Ip Ir Is Jn Jr Lh Lx Mi Mt Mz Nb Nq Nt Nw Oh Pa Pe Pg) Mt(Et Hw Hx Ii Is Jg Jh Jk Jr Lh Mr Nb Nq Nt Om Pa Pe) Jh(Lh Mi Nb Pa) Nq(Jr Nb Om) Mv(Lh Nb) Om(Lh Mi)} Lh{Jo(Et Ip Is Jn Jr Lw Ma) Lw(Io Is Jr Mg Ms) Ng(Is Jg Ma Mg) Is(Io Mg Pz) Jh(Of Oy) MaMg MhNw MwOy HrJr OfOm} Nt{Is(Io Jm Jo Ne Oe Pz) Jr(Io Jo Lw Ne Oe) Lw(Io Mt Mz) Mt(Mh Pb) Mz(Jo Nj) Om(Jo Of) NgJg IoNw JhOy} Oy{Jh(Lx Mi Nb Pa Pe Pg Po) Mw(Jr Lx Mt Pe Po) Nq(Jr Po) Mt(Jk Pb) MiOm} Of{Om(Is Lx Mi Mr Mt Nb Nd Nq Pa Pe Pg Po) Mt(Hw In Jo Qa)} Mi{Jr(Et Io Lw Nj) Ng(Jg Jh Om) Io(Is Qa) Pz(Et Is) MgOm} Is{Io(Et Lw Oh Pa) Mg(Ms Oi Pz) Lw(Lu Pa) EtPz} Mt{Pb(Hw Mz Ns Qa) Mh(Mr Pa Pe)} Jr{Nq(Hu Lw Ms Ng Ns) Lw(Mr Pa)} Lx{Ng(Jg Mg) NsMh JoJt} EtPzQa LwIoPa

Constrained panels with 3 analytes, where 1.0E-7 >= 'model p-value' > 1.0E-8. Contains 4,478 panels of 397,580 total panels evaluated. : Jj{Mi(Fp Hu Hv Hw Hx Ih Ii Im In Iu Iv Jg Jo Jp Js Li Lj Lv Lw Lx Ma Md Mg Mn Mq Mr Mv Mw Mx Na Nc Nf Nj Nk Nr Nv Nw Ny Oh Ok Pc Pd Qb Qd Qe) Nv(Et Fp Hv Hw Ih Im Io Ir Iu Iv Jg Jh Jo Jp Jq Jt Li Lv Lw Lx Ma Mg Mp Mr Mt Mw Mz Na Nd Nf Nr Nw Oe Om Pa Pc Po Pz Qa Qb Qd Qe) Lx(Et Hq Hv Hx Ih Ii In Iu Iv Jg Jp Js Li Lv Ma Mg Mh Mm Mq Mr Mw My Mz Na Nc Nj Nm Nq Nr Nw Ny Og Oh Ok Pb Pd Po Qb Qd Qe) Mp(Fp Hq Hu Hv Ih Il Im Iu Jp Js Li Lv Lw Ma Md Mg Mh Mm Ms Mv Mw Na Nc Nd Nk Nm Nr Ns Nu Nx Ny Oh Ok Pc Pd Qb Qd Qe) Mt(Et Hv Hx Ii Ij In Ip Ir Iv Jg Jh Jn Jt Lv Lw Md Mg Mh Ml Mm Mq Ms Mz Na Nb Nc Nd Nf Nk Nr Og Oh Om Pc Pd Po Qa)

Figure 42 Continued

Figure 42 Continued

Lx Mr Nt Om Pa Pe Po) Nw(Hw Jo Jt Nt Pc Qc) Pg(Ik Jm Jo Mz Ng Of) Et(Jq Lx Mi Pa Pc) Po(Ik Mh Oy Pc) Nt(Ik It Mz Ng) Pa(Jm Mh Mk Mz) Mi(Jm Mz Ng) My(Jg Jh Om) It(Hw In Na) Jo(Hw Mr Pe) Oy(Jh Mw Om) Lx(Jm Mh) Ik(Om Pe) Jq(Js Nd) Pc(Jr Lu) MzQc NgJg IiLh NxOn} Nt{Ip(Et Ik Io Jn Jo Jr Lw Mg Mm Mt Mz Ne Nf Ng Nj Nw Oe Oh Oi Om On Pc Pz Qa) Jo(Et Io Jg Jn Jt Lh Lw Ma Mi Mm Mt Ne Nf No Oe Oh Pc Pe Pg Po Qa) Ng(Et Jn Jp Jt Lh Li Lw Ma Mg Mi Mm Mt Mw Nj Nq Nw Om Qa) Io(Et Ih Ik Jn Jp Jt Me Mg Mi Mt Mz Nd Nj Oh Qa Qd) Et(Jn Jr Lw Mg Mm Mt Mz Nw Oe Of Oh Oi Pc Pz) Nw(Hx Jr Jt Lw Mh My Nj Ny Oe Oi Pb Pz Qa) Jn(Ik It Jm Lw Ma Mg Ne Nj Nq Oe Oh Oi) Om(Ik Lw Mg Mm Ms My Oe Oh Oy Pb Pc Pz) Mt(Hx Lv Ml Ne Nj Ny Oe Of Oi Oy Qa) Oh(Jg Jp Jr Lv Lw Nj Oe Oi Qa) Pc(Ir Jp Mg Mi Ms Oe Ok On Qd) Mm(Hv In Ir Mg Nf Oi Pz Qa) On(Ik Lw Mg Mk Mz Nj Oi) Mz(Ml Ne Nq Oe Oi) Nj(Jr Mi Ne Nf) Qa(It Ne Oe Pz) Lw(Jp Lu Nf) Jr(It Mg Nq) Oe(Jg Jk Jp) My(Jh Mv) Ik(Pe Qd) NoNd LxHq MaMg MsJg MwOy PzQd} Pc{Pa(Et Hv Hw Ij Im In Ip Ir Jo Jt Lv Lw Mk Ms Mt Na Nf Ni Nw Oi Ok Om Qd) Mr(Et Im Io Ip Ir Jo Jp Lv Lw Mg Mi Ms Mt Ng Nw Oi Om On Qa Qd) Mz(Et Hw Im Ip Iu Jr Ml Mm Ms Mt Nd Nq Nr Nw Oi On Pg Qa Qd) Jr(Hw Im Io Ip Jk Lu Mg Ms Nd Nr Ns Nw Oi Ok Om Pg Po) Et(Hw Ir Jn Lu Lx Mi Mt Nf Nr Nw Oi Po Pz Qa) Lx(Hv Hw In Ir Iv Jo Jt Na Ng Nw Ok Om Qd) Qa(Io Ip Ms Mt Nd Oi Om On Pg Po Pz) Jn(Hw Io Lu Ms Nd Nw Oi Ok On Pg Po) Hw(Im Ip Jp Mi Mt Om On Pg Qd) Nw(Hv In Ir Jo Jt Na Nr Oi Ok) Jq(Jo Lu Mg Ms Mt Oi Oz) On(Io Jg Mg Mi Mm Mv Mw) Om(Ir Mg Ms My Ng Oy) Mi(Hu Oi Ok Pz Qd) Qd(Nf Pe Po Pz) Ms(Nb Pe Po) Ip(Lh Pe) Ok(Nd Pg) PoOy MtPe MwMy IrOi} Mt{Pb(Et Hu Hv Hx Ii Ij Im In Ip Ir Iv Jn Jo Jr Lh Lv Lw Mi Mr Ms Na Ng Nj Nr Nw Ny Oi Ok Om On Pa Pe Pg Qd) Ny(Et Hw Ii In Jn Jq Jr Lh Mr Mz Ng Ns Ok Om On Oy Pa Pe Qa) Lh(Hx Ip Jo Lw Mg Mh Ml Ms Ng Oe Of Oi Oy) Mh(Et Hw Ii Ji Jr Nr Ns On Oy Qa) Of(Hv Ij Jt Mz Na Nb Ok On Pe Pg) Ml(Hw In Jq Jr Mz Na No Pe Qa) Oy(Jh Mr Nb Om Pa Pe Pg Po) My(Ip Jn Jq Nr Nw Pg Qa) Hw(Et Hx Ip Jq Lw Md Mm) Hx(Ji Jr Mr No Pa Pe) Mm(Et Mr Om On Qa) Lw(Et Mr Pa Pe) Md(In Mz Qa) Mi(Io Mz Qa) Jq(Iu Nd Nr) Et(Oi Pz) No(Lv Nj) On(Io Oi) NqNg OhPe}
On{Jo(Hv Hw In Ip Ir Iu Jt Mg Mh Mi Mr Na Nr Nx Pe Pg Qa) Io(Et Hw Im Ip Ir Jn Jt Lh Mv Mw Na Nc Nj Oh Oi Qd) Mg(Ip Iu Jt Lh Lw Ma Mi Mr Mv Mw Nj Oi Pe) Mz(Iu Mi Ml Mm Nb Nj Nx Oi Pb Qc) Nx(Hv Hw Ij In Ip Jr Lw Na Qa) Oi(Et Ir Iv Lj Nj Nk Oh Qa Qd) Lx(Hq Jt Lw Mh Mk Mv Nj) In(Mh Ml Mv Mw Nb Ny Pb) Nj(Hw Ip Jr Mi Na Qa) Lw(Jn Jt Lu Mm Pa) Mk(Lh Mi Mr Nd Pe) Nk(Et Hw Im Ip Ni) Of(Ii Nb Pa Pg Po) Pb(Hv Ij Na Pa Pe) Qc(Jn Lj Qd) Mi(Jn Jr) Mv(Lh Pa) Nc(Im Ne) Ik(Iv Pe) Qa(Ip Mm) MhPa MwPz NdHq NeNl IiLh OhPe}
Nw{Hw(Et Io Ip Iu Jr Mg Mh Mi Ml Nj Nq Ns Ny Of Oh Oi Pb) Lh(Hx Io Ip Jo Md Ml Mm Ms My Ng Ny Of Oi Oy Pb Qa) Mi(Et Hv Hx Io Jn Jo Jt Mh Ms My Na Ny Pb Pz Qa) Mm(Et Hv In Ir Jn Jo Jt Mr Na Nr Pz) Jo(Io Jr Mg Mh Ml My Ng Of Pb Pz) Qa(Et Io Iu Lx Mg Ml Nd Nq Pz) Jt(Io Ip Jr Lx Nd Nq Oi Pz) Nq(Hu Ms My Na Ng Oy) Lw(Io Jr Lu Mr Pa Pe) Mh(Ii Mr Nr Pa Pe) Na(Et Lx Nd No Pz) Jk(Ms My Ng Oy) Pe(Hx Ny Oh Pb) My(Jh Nb) Iu(Io Jq) Of(Nb Om) Oy(Jh Mw) EtPz MlIn} Lh{Jo(Ir Iv Jg Jk Jt Mg Mh Mi Ml No Of Oh Om Pg Po Qa Qd) Ng(Et Ip Jh Jk Jn Jp Jt Lw Mw Nq Om Pg Qa Qd) Of(Et Jg Jk Jn Ma Mg Mi Mv Mw Mz Nb Nq Pg) Mg(Et Ip Jn Jr Jt My Nq Oh Om Pg Qd) Io(Et Jn Jt Mi Oh Qa Qd) Ip(Jn Jr Mm Mz Oh Pb) Ms(Jg Jh Jn Nq Om) Jn(Et Ii Lw Oe) Oh(Lw Nj Oi Om) Nq(Hu My Oy) Mz(Lw Mh Ml) Pz(Et Qa Qd) Jg(My Oe Oy) Om(Oe Oy Pb) Pb(Ma Pg) LxMh MmQa HuJh} Jq{Hw(Et Im Ip It Jg Jp Jr Li Ma Mg Ml Nd Nj) Po(Hx Im Ip Md Mh Ml My Nj Ny Of Oy Pb) Mg(Ip Jo Jr Ms Nd Nk Nr Oi Oz Qa) Nd(Et Ip Jg Jr Li Nj Nr Ns Qa) Ip(Iu Jg Jk Jr Li Nk Nr Pg) Jg(Iu Ms My Ng Ns Oy Qa) Jk(Et Hu Im Jr Li Ml Nj) Et(Jr Mm Nk Pe Pz) Iu(Im It Jr Js Pg) Qa(Io It Ma Ml Pz) Nq(Mi Ms Ng Of) Nr(Im Ma Ml Nj) Ml(Hx Nb) Mw(Of Oy) Jr(It Ma) MhNb MvMy JhOy JoPg} Mm{Jn(Hw Io Ip Jk Lu Lx Mi Ms Nb Nq Nr Oi Om Pa Pe Pg Po) Mr(Io Ip Ir Lv Lw Mg Mz Om Pg Pz Qa Qd) Mz(Hw Ip Iu Jk Lv Lx Mi Nq Pz Qa) Pg(Hw Io Ir Mg Na Nf Ng Ok Pz Qa) Pa(Hv Hw In Ir Jt Mk Na Nf Qa) Lx(Et Hq Hv Hw Ir Jt Na Qa) Om(Hw Ir Ms Ng Of Oy Pz Qa) Qa(Io Ip Mi Pe Po) Pe(Hq Ip Ns Qd) Ji(Ma Mw Oh) Mi(Et Hw) My(Mw Nb) Ir(Io Pz) PoOy NbOf HwIp PzQd} Jr{Lw(Et Hw Io Jk Lu Lx Ma Mg Ms Nb Om Pe Pg Po) Et(Hw Io Ip Jk Lx Mg Mr Oe Oi Pa Pe Pz) Ip(Hw Jk Lx Ma Mg Mi Mr Nq Om Pa Pe) Mg(Hw Jo Lx Mr Ms Oi Pa Pe) Pa(Hr Jt Ma Mk Nj Oe Oh) Nq(Hw Mv Mz Ok Pe) Lx(Hq Hr Jt Mh Oh) Om(Mi Ms My Of Oh) Jg(Ms My Ng Ns) Pe(Hr Ma Ml Oh) Mr(Hr Ma Oh) Jk(Ng Oe Oh) MiHr JhOy} Nq{Mz(Et Hu Hw Ip Iu Lw Md Ml Ms Mv My Ng Nj Ny Of Oi Ok Oy Pa Pb Pe Qa Qd) Pe(Hu Ik Jn Lw Mg Mk Ms My Ng Oe Of Oy) Jn(Et Hu Lw Ms My Ng Oi Ok Oy Pz) Hu(Hw Ir Jh Jt Na Ok Om Qa) Ng(Jg Jt Nb Om Po Qa) Oy(Jh Mw Nb Om) My(Hx Mr Pa) Mg(Jt Ok) LwMr MkPa MsOm JoJt} Mi{Mz(Et Hx Im Ip Lv Lw Mh Ml My Nj Ny Of Om Pb Qd) Om(Hx Io Ip Jn Jo Ml Ms Nj Ny Pb Qa) Jn(Et Io Ip Jo Js Lw Ms Nj Oi) Et(Io Lw Mg Ng Oi Pe Qa) Io(Ip Jp Lv Lw Nj Qd) Qa(Ip Jo Ng Nj Of Pz) Ng(Jk Mg Mw) Ms(Jg Jh) Hq(Lx Pg) MwOy MyJg HuJh PzQd JoJt} Lx{Hq(Jn Jt Lw Mg Mh Mz Om Pd Qa) Mz(Et Lw Mh Ml Ny Of Pb) Jt(Et Io Ip Mg Mh Ng Of) Qa(Et Lw Ml Of Oh Pb) Om(My Ng Oh Oy Pb) Lw(Et Io Jn Ng) Mh(Jn Nd No Pg) Of(Ij In Na Nb) My(Jg Jh Nb) Et(Jn Pz) Ng(Jh Mw) Oy(Jg Nb) HwPb} My{Mw(Fp Hx Ih Im Iu Iv Jp Js Jt Lu Lv Lw Lz Ma Md Mg Mh Mr Ms Mv Mx Nf Ng Nv Oe Ok Om Oy Po Qa Qd Qe) Nb(Jg Ji No Om Pg) Jh(Mr Pe Pg Po) Om(Ji Mr Oh Pa) Mv(Pe Pg) Jg(Ji Pe) LwPa IiJi} Et{Pz(Hw Ir Jk Jn Jt Mr Mz Nk Om Pa Pe Pg Po Qd Qe) Lw(Io Lu Mr Mz Pa Pe Po) Mz(Hw Iu Oi Pa Pg) Pe(Io Jo Mg Ng Oh) Of(Jk Nb Om Pg) Io(Jn Nk Qa) Pg(Jo Mg Ng) Jk(Ng Oe) Pa(Mk Oe) MrOh MwOy HwJo} Lw{Pa(Ip Ir Jn Lu Mk Ms Mz Nf Ng Oh Oy Qa Qd) Pe(Io Ip Jn Jo Lu Mg Mz Ng Of Oh) Mr(Io Ip Jn Jo Lu Ms Mz Oh Qa) Io(Jp Pg Qa) Po(Of Oy) Mz(Iu Pg)} Om{Of(Hw Hx Ir Iu Iv Ji Jk Jn Jo Jt Mk Mx Nv Oh Qa) Oh(Hw Mr Ms Oi Pa Pe) Pa(Mk Ms Ng Oy Pb) Iu(Mg Ms Ng) Oy(Pe Pg Po) Pz(Qa Qd) Jt(Jo Mg) NdHq} Ji{Ii(Hx Mh Nx Ny Of Pb) Pz(Hu Li Lu Nx Oh Qd) Ml(Il Mh Nb Nv) Nb(Hx Ny Pb) In(Mh Ny Pb) Of(Mv Mw Nv) Io(Nx Oh) Qc(Il Iv) Oi(Oh Pd) JgNx NyPb} No{Nj(In Lv Mb Mq Na Nb Nf) Ns(Jh Mq Nd) Pz(Jg Qa Qd) Jo(In Nm Pg) Oe(Jg Jk Mw) Ne(Nc Nl) Jh(Hu Ng) MeIo NbOf JgOy NyPb} Oy{Mw(Hx Ip Ir Jk Jn Nd Nv Oh Pa Pb Pg) Jh(Hx Ir Jk Lz Mh Mr Nk Nv Oh) Jg(Pe Pg Po) PoMg} Pe{Oh(Im Ip Jn Jo Lv Nj Oi) Mg(Ik Ma Ng) Ng(Jg Ma) Jo(Ip Jt) Of(Jh Nb) MlMz MsJg} Pa{Mz(Ip Mh Ml Of Pb) Jt(Io Jo Mg Mk) Ng(Jg Mg) MkJh NbOf QaOh} Pg{Mz(Iu Jo Of Pb) Jt(Io Jo Ng) NbOf NgJg JoOk} Mg{Ng(Jk Mr) MaJt MlMz} Mw{Hu(Hx Pb) MzOf} Jg{Ng(Jk Po) PzQd} Mr{IpOh JoJt} PoJoJt NyPbaA

Constrained panels with 3 analytes, where 1.0E-6 >= 'model p-value' > 1.0E-7. Contains 6,251 panels of 397,580 total panels evaluated. :
Jj{Jg(Et Fp Hv Hx Ii Ij Il Im In Io Iq Jh Jm Li Lu Lv Lw Lz Ma Md Mg Mh Mj Mq Ms Mw My Na Nb Nc Nd Nf Nk Nr Nu Nw Ny Og Oh Oi Ok Pa Pc Pd Qb Qe) Mg(Fp Hv Hx Ij Il Im In Iq Iu Jh Jm Jp Li Lj Lw Lz Ma Md Mh Mj Mn Mq Mv Mw Na Nb Nc Nd Nf Nk Nu Nx Ny Og Oh Pc Pd) Mw(Hx Ih Ij Il In Iq Ir Iv Jh Jm Js Li Lv Lw Md Mh Ml Mq Mx Mz Na Nb Nc Nd Nf Nr Nu Nx Ny Oh Ok Oy Pc Pd Qd) Nr(Hw Hx Ih Ij Il Im In Iu Iv Jh Jp Js Jt Li Lv Lw Md Mm Mn Mx Mz Nb Nd Nf Nx Ny Oh Ok Pa Pc Qb Qd Qe) Nb(Hx Ih Im Ir Iu Iv Jm Jp Js Li Lv Lw Md Mh Ml Mm Mv Mx My Nc Nd Nw Ny Of Oh Ok Pb Pc Pd Qb Qd Qe) Iu(Hv Ih Im In Iv Jp Js Lw Md Mj Mm Mn Mq Mv Mx Na Nc Nm Nu Nx Ny Oh Ok Pa Pc Pd Pf Qb Qd Qe) Jh(Hx Ii Il Im Iq Iv Jm Jp Js Li Lj Lv Lw Lz Ma Ms Mx Mz Nc Nk Nl Nw Of Og Ok Oy Pd Qb Qd Qe) Mz(Hx Ih Ii Ij Il Im Ir Iv Jm Li Lv Lw Ml Mn Mq Mv Nc Nk Nl Nu Nw Ny Oh Ok Pd Qb Qd Qe) Pa(Fp Hv Hx Ii In Jm Jp Js Mk Mn Mq Mv Mx Na Nc Nf Nj Nm Nu Nx Ny Og Ok Pd Qb Qd Qe) Ma(Hv Ij In Ip Jm Js Lv Lw Md Mh Mq Mx Na Nc Nd Nk Nu Nw Nx Oh Ok Pc Pd Qb Qd Qe) Hw(Fp Hx Ii Ij Il Iq Iv Jm Jp Js Lv Lw Mn Mv Mx Nc Nd Nf Nm Nx Ny Ok Pd Qb Qe) Lv(Et Hx Ih Ii Ij Il Im Ir Iv Js Jt Li Md Mm Nd Nf Nw Oh Ok Pc Pd Qd Qe) Hx(Ih Im Ir Iv Jp Js Jt Li Lw Md Mm Mv Nc Nd Nw Ny Og Oh Ok Pd Qd Qe) Ih(Ii Il In Jp Jt Li Lw Md Mj Mm Mq Mv My Nd Nf Nu Oh Ok Pc Pd Qd) Li(Ii Ij Il In Iv Jt Lw Md Mq Na Nc Nd Nf Nu Nw Nx Oh Ok Pc Pd) Nw(Et Hv Ii Ij In Ir Iv Lw Mb Md Mq Mv Nc Nf Nk Nu Oh Pd) Pc(Fp Hu Hv Im In Iq Jp Md Mj Mv Na Nd Nx Ny Ok Pd Qb) Lw(Et Fp Ij Im Ir Iv Jp Js Lu Mv Mx Nd

Figure 42 Continued

Nf Qb Qd Qe) Mm(Hv Ii Il In Ip Iv Js Md Mi Mx Na Nf Nv Qb Qd Qe) Ok(Il Ip Jm Js Md Mv Nc Nd Nf Nk Nv Oh Pd Qd Qe) Md(Ii Ij Il Im Jm Jp Js Mv Mx My Qb Qd Qe) Et(Ij In Iv Jm Js Lu Mh Mv Na Oh Pz Qe) Im(Ii Mh Mj Mq Mv Nc Nf Nk Oh Pd Qd) Il(Jp Js Mq Mv Mx Nf Nm Ny Oh Pd) Ip(Hu Hv Lu Lz Mn Mq My Qd Qe) Nd(Iv Js Nx Ny Oh Qb Qd Qe) Nv(Ii Ij Js Mq Mx Nc Nm Og) Mp(Iq Jm Lj Lu Ly Mq Mx) Iv(Ii Ij Jt Mv Nf Oh Pd) Qe(In Nf Nm Nu Nx Oh Pd) Qd(In Mq Mt Nf Nx Oh) Po(Jp Ml Ny Of Qb) Ij(Jp Nc Nk Og) Jt(Fp Io Ir Pd) Nf(Ir Jm Qb) Oh(In Pd Qb) Mi(Io Ms) Js(Mq Nu) Ny(Pb Pd) WmJr MlQa MxIi JpPd} Mt{Mp(Hv Hx Ii Ij Im In Io Ip Ir Iu Iv Jg Jo Jp Lv Lw Lx Mg Mh Mi Mk Ml Mr Ms Mv Nb Nc Nf Ni Nj Nm Nq Nr Ny Of Oi Pa Pc Pd Pf Pg Po Qd) Lw(Hx Ii Im Io Ip Ir Iu Iv Jk Jn Jo Jr Li Lu Lv Lx Mh Mi Ml Mm Ms Mx Mz Na Nb Nf Nn Nq Nr Nv Nw Ny Of Om Pg Po Qa Qd) Hx(Et Hu Ii Im In Ip Ir Iu Iv Jn Jo Jq Jt Lv Mh Mi Ml Mm Mu Mz Na Nb Ng Nr Ns Nw Ny Of Oi Ok Om Oy Pc Pg Qa Qd) Ml(Et Fr Hu Hv Ii Ij Im Ip Ir Iv Jn Jo Jt Lv Mi Mr Ms Mu Nb Nf Ng Ni Nr Ns Nw Oi Ok Om Oy Pa Pg Qd) Mm(Fp Fr Hv Ii Ij Im In Io Ip Ir Iu Iv Jo Jt Lv Lx Ma Mh Na Nb Nf Ni Nr Nw Of Ok Oy Pa Pc Pg Pz Qd) Pc(Hv Ii Ij Im In Io Ip Ir Iu Iv Jo Jt Lv Lx Mh Ms Mu Mv Na Nb Nf Nn Nr Nw Of Oi Ok Oy Pg Po Qd) Mh(Hu Im In Ip Ir Iu Iv Jn Jo Jq Jt Lv Lx Mi Ms Mx Mz Na Nb Ng Nj Nw Of Oi Ok Om Pg Po Qd) Ip(Et Iu Jo Jr Jt Lv Lx Mi Mr Mz Na Nb Nq Nr Ny Of Oi Ok Om Oy Pa Pe Pg Qa) Hw(Ij Im Iu Jr Lv Lx Ma Mg Mi Mz Nj Nq Ns Nw Oe Oh Oi Om Oy Pa Pe Pg Qd) Jt(Im Io Jk Jo Jr Lv Md Mg Mi Mr Ms Mz Nd Ng Nj Nq Ny Oi Pa Pb Pg Po Pz) Ny(Hu Hv Ij Im Ir Iv Jo Lv Mi Ms Na Nb Nj Nn Nr Nw Oi Pg Qd) Pe(Ik Im Iu Jo Lj Lv Ma Md Mg Ms Mz Ng Oe Oi Pf Pg Pz Qd) Mi(Hq Hv Im Jn Jo Lv Mg Ms Na Ng Nj Nw Oi Ok Oy Pg Pz) Jr(Im Io Iu Jo Lv Ms Nj Of Oh Oi Ok Oy Pz Qa Qc) Ok(Iu Jk Lv Lx Md Mg Nc Nd Nk Nq Oh Pa Pg Pz) Of(Et Ii Im Jg Jk Jn Lv Mr Nf Nn Nr Pa Po) Qa(Et Io Iu Ma Mg Nq Oi Oy Pa Pg Pz Qc) Jo(Im Lv Lx Md Mg Mu Ng Nq Oi Oy Pg Qd) Lv(Fr Im Iu Lh Lx Mr Na Nq Nr Pa) Mz(Iu Lx Mg Mr Ms Nd Oh Oi Pa) Et(Iu Na Nc Nk Nr Oy Pa Pg) Om(Ik Iu Md Mg Ms Mv Ng Pz) Mr(Mg Ms Ng Oe Oh Oi Qd) Mu(Ik Im Ms Na Nr Oe Pz) Pa(Hv Jn Mk Ms Na Oe Oh) Nq(Hu Mv Na Nr Oy Qd) Oi(Ir Nb Nw Oh Pg Qd) Lx(Hq Ly Na Ng Oh) Oy(Ii Jg Mk Nr Oz) Pg(Im Iu Na Ng Nm) Mv(Jg Jh Jk Mw) Md(Hv Ij Na) Nb(Ms Oe Pb) Iu(Fr Nn Nw) Ng(Jg Jk) Im(Nc Nr) Pz(Nw Qd) Qc(On Qd) Lh(Io Nj) FrMs NdHq} Mp{Mm(Fp Hv Hx Ii Ij Im In Iu Iv Jh Jk Js Li Lu Lv Lw Lx Ma Md Mg Mh Mj Ms Na Nc Ni Nl Nm Nq Nr Nu Nv Ny Oh Pc Pg Qd) Pc(Fp Hq Hu Hv Hx Ih Ii Ij Im In Io Ip Iv Jo Jp Lu Lv Md Mg Mx Na Nb Nf Ng Ni Nr Og Oi Pg Qd) Ip(Hq Hv Hx Ii Ij In Iv Jg Jk Jo Jp Jt Lu Lx Md Mi Ms Na Nb Nf Nr Ns Og Oh Pa Pg Po) Pa(Hv Hw Ij Im In Io Iv Jo Jp Lv Md Mg Na Nf Ng Ni Nj Nm Ns Oe Oh Oy Oz Pd Pg Qd) Hq(Fp Hu Hx Ii Ij Ir Iv Jg Jk Jo Lv Lw Md Mi Mj Nd Ni Nj Nm Nv Oi Oz Pd Pf Qd) Lx(Hv Hw Ir Iv Jo Lw Ly Mh Ms Na Nd Ng Ni Nm Ns Of Og Oh Ok Oy Pd Pg Qd) Qd(Hv Hw Hx Ii Ij In Io Jg Jh Jk Jo Mi Mr Na Nb Nf Nq Nr Ns Pe Po Pz) Ns(Hr Hu Hx Ii Ij Ir Iv Jk Jo Lv Lw Md Mi Mj Mw Nj Nu Nv Oz Pd) Pg(Hv Hx Ii In Io Jo Lw Mg Mk Mr Na Nb Ng Nr Of Og Oy Pd Po Pz) Nq(Hu Hv Hw In Ir Iv Jo Jt Lw Mg Ms Na Nf Ng Nr Og Ok Pe Qa) Po(Hv Ij In Jt Lw Mg Mh Mk Ms My Na Ng Oe Of Oh Pb Pd Pf) Jo(Hv Ii Ij Im In Jg Jp Mg Mr Ms Nb Ng Nj Of Og Oh Pd) Jp(Hv Hx Ii Ij In Io Iv Mr Na Nb Nf Ni Nr Pd Pe) Mi(Hv In Ir Iv Jt Lw Mg Na Nf Ni Nj Nw Pe Pz) Jg(Hu Hv Hw Ij In Ir Iv Mg My Na Nf Nr Oy Pz) Ms(Hv Hw Ii In Iv Jh Jk Lw Mw Na Nf Nr Oh) Mr(Im Io Ir Jt Ly Mg Nf Ng Oe Oy Oz Pd) Og(Hw Hx Ii Ij Iv Jk Jt Lw Mv Nm Nr Nv) Im(Hv Hw Ii Ij In Mj Na Nb Nf Nr Pe) Pd(Hv Hx Ii Ij In Lw Na Nb Nf Nr Nt) Lw(Hw Hx Io Iv Lu Mh Mx Nb Nr) Nj(Hv Hx Ii Ij In Na Nb Nr Pe) Ii(Io Li Mg Mk Ng Of Oy) Pe(Io Ir Nf Oe Pb Pf Pz) Nb(Io Mg Ml Nf Oe Oh) Iv(In Io Md Na Nf Ng) Jk(Hu Hv Mg Na Oe Oy) Nr(Mk Nf Oy Pf) Hw(Md Mg Nf Oh) In(Li Of Oh Pb) Hx(Io Ng Oy) Ij(Io Of Oy) Jt(Lu Mk Nd) Na(Li Of) Hv(Of Pb) Oe(Et Nv) NmNn MkOz NfIr NiNk HuJh JnPf} Og{Mi(Fp Hq Hu Hv Hw Hx Im Io Ir Iv Jo Jp Js Jt Li Lv Lx Ma Md Mg Mr Mv Na Nf Ni Nj Nm Nq Nr Nv Ok Pa Pg Po Qb Qd Qe) Jg(Et Fp Hr Hv Ih Il In Io Iu Jo Js Lu Lv Lw Lz Md Mg Mh Mj Mq Mv Na Ng Nx Oh Ok Pc Pd Qb Qe) Po(Hx Ij Im Ir Jk Jn Jr Jt Lv Lz Ma Mg Mm Mr Mv Mz Nm Nq Ns Nv Nw Oh Ok Pa Pe Pg Qa Qd) Nw(Et Hv Ij Il Im Io Ip Ir Iu Iv Jn Jq Lv Lx Mb Mm Mq Mv Mx Mz Nd Nf Nm Nu Nv Ok Pg) Lx(Et Hv Hw Hx Ii Ij In Ip Ir Iv Jk Jo Ly Mg Mm Na Nf Nm Nq Ns Nt Oh Ok Qa) Pa(Hv Hw Hx Ij Im In Ir Iv Jk Jo Lv Ma Md Mm Na Nf Nq Nt Nv Nx Oh Pg Qa Qd) Jh(Et Hw Ih Ii Il Im Iv Jo Jp Js Li Lj Lv Lz Mg Mh Mv Nd Nf Nk Nq Qb Qd) Pg(Et Hq Hw Hx Ii Ip Ir Iu Iv Jn Jt Lw Mg Mm Mr Mv Nf Nm Nq Ok Pe) Et(Hw Hx Ii Ij Il In Ip Ir Iu Iv Jt Lw Mr Mv Mz Nq Nr Nv Qe) Mr(Hx Ij Im Ip Ir Jk Jn Jt Lv Ma Md Mz Nm Nt Nv Oh Qa Qd) Nn(Fp Ih Iu Jk Js Li Ma Md Me Mg Ml Mq Mx Ni Nx Oz Qb) Lw(Hx Ii Im Ip Ir Iv Jk Jn Jo Jq Mv Mz Nq Nr Nv Qa) Pc(Hu Hv Im In Ip Iv Jk Jt Mx Na Nf Nr Nv Qd Qe) Mz(Hw Hx Ii Im Ip Iu Jo Jr Jt Ma Mv Nr Nv Qa) Nq(Hw Hx Ii Ij In Ip Ir Iv Jo Nf Nr Qa Qd) Jk(Hx Ip Ir Iv Jn Jt Mm Nf Nm Nr Nt Pe Qa) Jr(Hw Hx Ii Im Ip Iu Jo Jq Jt Nm Nr Nv Ok) Pe(Ih Ij Im Ir Iu Iv Ma Nv Oi Ok Qa Qd) Mv(Hw Hx Ii Ij Ip Ir Iv Jn Jo Ok Qa) Mg(Hw Hx Ii Ir Jn Jt Nf Nr Ok Qa) Ip(Hw Hx Ii Jt Nr Nv Ok Qa) Jq(Ii Il Iv Lv Me Mq Ok Qe) Nt(Im Ir Jp Li Lv Nm Qd) Mm(Ii Ij In Ir Iv Jt Nr) Nv(Fr Jn Jt Ok Qa) Hx(Jt Ma Oh Ok) Fr(Js Md) Nr(Im Jn) Jt(Im Io) IiOh IuOk JnJo} Nw{Ip(Et Hv In Io Ir Iu Jk Jn Jo Jr Lw Lx Mb Mg Mi Mm Mr Mz Nd Nk Nm Nq Nr Nu Oh Oi Ok Pa Pc Pe Pz Qa) Lw(Et Fp Hv Im Ir Iu Iv Jk Jn Li Lx Mh Mi Mm Ms Mx My Mz Na Nd Nq Nr Oi Ok Pg Po Pz Qa) Mg(Hv In Io Ir Iv Jn Mb Mh Mm Mr Ms My Mz Na Nc Nd Ng Nr Ny Oi Ok Oy Pa Pb Pe Pz) Iu(Et Hv Ij Im In Jo Jr Lv Mh Mm Mq Ms Mz Na Nf Ni Oi Ok Om Pc Pe Pg Pz) Na(Hx Im Io Jq Jr Li Md Mh Ml Ms My Mz Ny Of Oh Oi Ok Pa Pb Pe Qa) Mm(Fp Ij Io Iv Lv Lx Me Mi Mq Mx My Nf Ni Nq Ok Pa Pc Pg Qd Wm) Pa(Hv Hx In Io Jn Lv Mk Ms My Mz Nm Ny Oe Oh Oi Ok Oy Pb Qa) Nd(Et Hq Hv Ij In Io Ir Jn Jr Mb Mq Mz Nr Ns Oh Ok Om Pc) Nq(Hv Ij In Ir Iv Mq Mv Nc Nk Nr Ns Oe Oi Ok Pe Pz Qd) Io(Et Ir Iv Jk Jn Lv Mb Mq Mr Nc Nk Nm Oh Pc Pg) Ms(Ii Ij In Jg Jh Jo Jt Mb Mr Nb Nr Om Pc Pe) Lx(Hv Ij In Ir Mb Mh Mq My Mz Nm Oh Ok Pb) Oi(Et Ir Iv Jk Jn Jo Mi Mr Nb Nr Nu Oh) Pb(Hv Ii Ij In Mr Mz Nb Nr Ny Om Pg Qa) My(Hw Ii In Jg Mr Mv Om Pc Pe Pg Po) Pz(Ir Iv Jk Jn Jr Nu Ok Om Pc Pg Qd) Im(Hw Jo Jt Mj Mq Mr Nr Pc Pe) Ny(Hv Ii Ij In Jo Mr Nb Pg) Pc(Ij Iv Lu Lv Nf Ni Pg Qd) Mi(In Ml Ng Ni Nj Ok Oy) Jk(Hu Mq Mz Oe Of Oh Ok) Pe(Et Jr Md Ml Oe Of Oy) Nk(Et In Jq Mq Ni Ok) Oh(Hv Ij In Mr Mz Qa) Mh(In Ir Nb Pg Po) Ml(Hv Ij Mz Nb Om) Oe(Et Mr Nb Nr Pg) Oy(Jo Nb Om Pg Po) Md(Hw Ij In Jo) Hx(Hw Jo Mr Nb) Qc(Iv Jn Jr Qa) Of(Hv Ij In Pg) Et(Jo Mr Nr) Jr(Jq Mr Ok) Nm(Lu Pg) Nc(Ne Ok) Ng(Jg Om) NsMq NeNl} Et{Mm(Hx Im In Ip Ir Iu Iv Jk Jn Jt Li Lw Md Mh Mw Nc Nd Nf Nk Nq Nr Nv Oh Om Pa Pc Pg Po Pz Qd Qe) Ip(Hw Hx Io Jk Jn Jt Lu Lw Lz Md Mg Mh Mr Mz Nb Nc Nd Nf Nk Nm Nq Nr Nv Oh Oi Pa Po Pz Qa) Pz(Hx Ih Ij Il Im In Iu Iv Js Li Lu Lw Lz Md Mg Mh Mv Mw Nb Nc Nd Nf Nq Nr Nv Oh Ok Qb) Nq(Hu Hv Hw In Ir Iv Jt Lj Lw Mg Mh Ms My Na Nf Ng Nk Nr Of Oi Oy Qa Qd) Io(Hw Hx Ih Ir Iu Iv Jk Jt Mh Mr Mx Nb Nc Nd Nr Nv Oh Pa Pc Pg Qb Qd) Lw(Hw Hx Il Ir Iu Jk Jn Mf Mg Mh Mx Nb Nf Nk Nr Nv Oh Om Pg Qa) Mg(Hw Hx Ii Iu Jk Jo Jt Lx Mh Mr Mv Nb Ng Nr Nv Om Pa Pc Po) Oi(Hw Ih Ir Iu Iv Jk Jn Jt Mh Nb Nk Nr Nv Oh Om Po Qa Qd) Nd(Hq Iv Jn Jt Lu Mh Na Nc Nk Nr Ns Oh Ok Om Pc Qd) Pc(Hu Hv Hx In Iu Iv Md Ms Mx Na Ng Ok Om Pg Qd) Jk(Hu Ir Jn Jo Mh Ms My Mz Nk Nm Oh Ok Oy Qd) Ng(Hw Iu Jo Jt Lx Mr Mw Nb Nr Nv Om Pa Po) Oh(Hw Hx In Lu Lx Na Nb Nr Om Pa Po Qa) Nk(Im In Lu Mz Na Nb Nf Ni Ok Om) Of(Hw Hx Iu Lx Md Mr Nr Nv Pa Po) Oe(Hw Hx Mr Nb Nr Nv Om Po) Jn(Hw Lu Mr Ms Pa Pe Pg) Lu(Ir Iu Jt Na Qd) Jo(Jt Mr Nb Nr Po) Md(Hw Iu Nr Qa) Ms(Mi Mw Nb Om) Nc(Fr Im Ne Ok) Oy(Jh Nb Om Po) Lx(Hq Hw Na) My(Mv Nb Om) Pa(Jt Na Qa) Iu(Nf Om) Pg(Hw Qa) MlIn NeNl} Om{Of(Fp Hv Ih Ii Il Im Ip Iq Jp Jq Li Lu Lw Lz Ma Mg Mh Mj Mv Mw Mz Na Nk Nl Nr Ok Oz Pc Qb Qd Qe) Oy(Hw Hx Ip Ir Iu Iv Jh Jk Jn Jr Jt Lu Lw Lz Mh Ml Mr Mw Mx Nb Nd Nr Nv Oh Pb) My(Hw Hx Ip Ir Iu Iv Jg Jk Jn Jt Lu Lw Mg Mh Mm Mv Mz Nv Pe Pg Po Qa Qd) Ms(Hw Hx Ih Ip Ir Iv Jg Jn Jq Jt Lw Lx Mr Na Nb Nd Nr Nv Pe Pg Qa) Ng(Hw Ip Ir Iv Jg Jk Jn Jt Li Lu Lw Mg Mr Nd Nk Nv Oh Pc Pg Po Qa) Ip(Hw Iu Jn Jo Jt Lw Lx Lz Mg Mm Mr Mz Nk Nm Oh Pa Pb Pc Pz) Lw(Hw Io Iu Iv Jn Jo Lu Lx Mg Mr Mz Nd Oi Pa Pz Qa Qd) Iu(Fr Io Jo Jr Mm Mu Mz Oe Oh Oi Pc Pe Pz) Lx(Hx Ir Jo Ly Md Mg Mh Ml Mm Na Ny Qd) Oe(Fr Hw Ir Mr Mu Nb Nq Nr Nv Pa Pe Qa) Pc(Hu Ih Iv Jn Jo Mx Nd Nr Ns Oi Pz Qd)

Figure 42 Continued

Mg(Hw Ir Iv Mm Mr Nd Nq Oh Pa Pe Pg) Pz(Ir Iv Jn Jr Jt Mu Oh Pe Qe) Mr(Hx Jo Jt Mh Ml Ny Pb Qd) Hw(Jo Jr Mz Nq Ns Oi Pb Qd) Pa(Hx Jo Lv Mh Ml Mm Ny Qd) Ik(Ir Iv Mu Pe Pg Qa Qd) Nd(Iv Jn Jt Ns Oh Qd) Pb(Fr Mu Mz Nr Pe Pg) Ml(Jl Lh Mz Pe Qa) Jo(Ir Iv Oh Pe Pg) Nq(Ih Ir Lj Qd) Lh(Hx Ii Mh Ny) Oi(Ir Iv Jt Mu) Mm(Ih Iv Qd) Mu(Hu Lj) Mz(Md Ny) Nk(Fr Jq) Io(Jt Qa) On(In Nx) QaOh} Mi{Nj(Hq Hv Hw Ij Im In Ip Iv Jk Jo Jp Jt Lh Lv Md Ms Na Nf Ni Nq Nv Oh Ok Qd) Nf(Hq Hx Im Ip Iu Iv Jg Jp Lv Lw Ma Mh Ml Mm My Ng Ny Of Oy Pb Pg Qd) Hq(Hv Io Ip Iv Jg Jh Jk Jp Lv Lw Ma Mm Ms Na Nd Nt Pc Pd Pe Po) Ng(Hu Ij Im In Ip Jo Jp Jt Lh Li Lv Lw Lx Ma Mm Nq Pe Pg Po) Io(Hw Ih Ir Iu Iv Jg Jk Jt Li Ma Mm Nc Nk Ok Pe Pg Po Qe) Ip(Hv Hw In Ir Jg Jk Jo Jp Jt Lv Lw Mg Mm Ms Na Ok Pz Qd) Lw(Hw Ir Iv Jk Jp Li Lj Lu Lx Ms My Nq Oh Pg Po Qd) Na(Im Jo Jp Li Lx Ma Mm Ms Nq Of Oh Pg Po) Hw(Im Jg Jo Jp Ma Ms Nq Of Oh Pb Pg Po Qd) Mg(Jg Jk Jo Jp Jt Lh Li Ma Nq Nt Pe Pg) In(Hx Im Jp Mh Ml Mm My Ny Of Oy Pb) Ms(Ii Jk Jp Jt Lh Mm Mw Nb Oh Pg) Hv(Im Jg Jo Jp Ma Mm Of Pb Pg Po) Pz(Im Jg Jh Jk Jp Ma Mm Ok Qe) Nb(Hx Mh Ml My Ny Of Oy Pb) Oy(Ij Jg Jk Lx Pe Pg Po) Lv(Im Jp Li Mm Mr Oh) Jo(Im Jk Jp Pe Pg Po) Of(Ii Ij Jh Jk Lx Po) Mm(Ir Jt Ni Pg Qd) Jn(Im Pe Pg Qd) Jp(Ij Jt Ni Ok) Nc(Jg Jh Ne) Ir(Im Nq Oi) Pb(Ij Lx Ny) My(Ij Mv) Jk(Oe Oh) Lj(Jg Jh) Oi(Iv Li) NqJt LxMh MkPa MrIm NeNl NiNk OkPg} Pc{Nf(Hu Hw Hx Im Ip Ir Iu Iv Jk Jo Jp Jt Lu Lv Lx Ma Mm Ms Mx Na Nb Nd Nr Oi Ok Oz Pg Po Qe) Qd(Hu Hv Hx Ii Ij In Io Ip Jk Jo Jt Lu Md Ms Na Nb Nd Nq Nr Nv Oi Ok Pg) Im(Hv Ii Ij In Iv Jo Jt Lu Lx Md Mj Ms Mu Na Nb Nr Oi Pg Po) Hw(Hu Ih Ir Iv Lv Ma Md Mg Mm Ms Mx Nd Nq Ns Oh Oi Ok Po) Lx(Fr Hq Ih Ij Ip Jp Lv Mg Mh Ms My Ni Nm Nr Ns Oi Oy) Iv(Hx Io Ip Jo Jp Lu Ma Md Mm Nb Nd Nr Oi Ok Pa Pg Po) Ok(Hu Hx Ip Ir Iu Jk Jp Lu Md Mg Ms Mx Nq Oi Po Pz) Pg(Hv In Io Ip Ir Jo Jt Mg Ms My Na Ng Ns Oi Oy Pa) Po(Hv Ip Ir Jp Jt Lv Mg My Na Ng Ns Of Oi Pa) Nn(Fp Ih Jp Md Me Mf Mh Mq Ms Mx Nu Nv Oz Qb) Jo(Hu Ih Ip Jn Jp Jt Lu Mg Ms Mx Nd Ng Oi) Jt(Io Ip Jp Lu Ma Mg Ms Mx Nd Ng Nv Oi) Ip(Hv Hx Ii In Ir Jn Lu Na Nb Nr) Pa(Hu Io Jp Mg My Ng Nm Oe Oy) Nr(Jn Jp Lu Lv Md Ms Mx Oi) Mu(Hu In Iu Mg Na Nj Ns Oy) Ir(Io Lu Md Mg Mm Ms Nd Nq) Nb(Jn My Nd Oe Of Oi Oy) Jp(Hv In Io Mx Na Oi) Oi(Hx Ii Js Mx) Ms(Hx Ii Jh) Nd(Hv In Na) Nq(Hu Jn) NsPd MmIn MwOy HuJh PzJn NyPb} Mm{Qd(Hv Hw Hx Ii Ij In Io Ip Jk Jo Jt Lu Lv Lx Md Na Nb Nf Nq Nr Nv Ok Pa Pg Po) Nb(Fp Hv Hx Ih Im Io Ip Iv Lv Lw Lx Ms Nc Nf Ng Ny Oe Oi Oy Pb Pz) Ip(Hv Hx Ii Ij In Ir Iv Jk Jo Jt Lu Lx Md Na Nf Nr Nv Ok Pa Po) Jt(Fp Hx Im Io Jk Jo Lu Lv Md Mg Nd Nf Ng Nq Nv Pg Po Pz Qb) Iv(Hw Hx In Io Lv Lx Md Na Nf Nq Nr Nv Oi Ok Pa Pg Po Pz) Nf(Fp Hw Hx Im Ir Iu Jk Lu Lv Lx Nc Nk Nq Nr Nv Po) Pa(Fp Ih Ij Im Io Jo Js Lv Me Ms Ng Ni Oe Ok Oy Pz) Po(Hv Hw In Ir Lv Mg Mu Na Ng Ni Ns Of Ok Pz) Lx(Ih Ij In Jo Lv Ly Ng Ni Nr Ns Of Ok Oy) Pz(Hv Hw Hx Ii Ij In Jk Lv Nn Nr Ok Qe) Hw(Ih Im Io Ir Jp Lv Md Nq Qb) Ok(Hx Jk Lv Md Mh Nc Nk Nv Qe) In(Fp Ih Im Lv Nq Nr Nv Pg) Pg(Hq Hv Ij Jo Ni Ns Oy) Ir(Jk Lu Lv Md Nq Oi) Nr(Im Js Lv Md Nq) Hv(Hx Ih Jk Nq Nv) Mu(Fp Mh Oi Qb) Na(Ih Jk Nq Nv) Lv(Hx Ih Ii) Jo(Ih Mg Ng) Hx(Io Oe) Jk(Mg Ng) Oy(Jh Mw) LuLw IoJs NyPb} Mz{Mg(Hw Hx Im Ip Ir Iu Jk Lh Lv Lw Lx Md Mh Mr Ms My Nc Nd Ng Nk Nr Ny Of Oi Ok Pa Pb Pe Po Qa Qd) Ip(Hw Iu Jg Jk Jr Jt Lw Lx Ma Ml Mr Ms Nb Nd Nk Nr Nv Oh Pe Pg Po Qa) Jk(Hu Im Jr Jt Lv Lw Ma Ml My Ng Nj Ny Oe Of Oh Ok Oy Pb Qd) Lw(Hw Im Io Iv Jo Li Lu Ma Ms Mx Nb Nd Nr Nv Oi Po Qa) Pa(Hx Im Jn Jt Lv Ma Md Mk Ms My Nj Ny Oe Oh Oy Qa Qd) Ma(Hw Iu Jt Lx Ml Mr Ms Na Nk Of Oi Pb Pe Qa) Im(Hw Iu Jo Jr Jt Lv Mr Nb Nr Nv Oh Pe Pg) Ml(Hw Ii Iu Jg Jq Jr Mr Nb Nr Pg Po Qa) Lx(Hx Iu Lv Md My Nf Ng Nj Oh Oy Qd) Jg(Hw Iu Ms My Ng Ny Of Oi Oy Pb Qd) Mr(Hx Jt Lv Mh Nj Of Oh Pb Qd) Iu(Io Jo Jr Lv Ms Oi Pe) Nb(Hx Mh My Ny Of Pb) Nd(Hq Jr Jt Lv Oh Qd) Pb(Lh Nv Ny Pe Po) Jr(Jo Ms Oh Pg) Jt(Io Jo Ms Oi) Po(Mh Of Oh) Nj(Hw Lh Nv) Qa(Io Pe Pz) Oy(Jh Mw Pg) Hw(Lv Oh) Qd(Pe Qc) Nv(Oe Of) NqJn MhIi MvOf MyJh HrPe LiLj} Mu{Ik(Fp Ij Ip Iu Jo Js Li Lz Ma Md Mg Mj Mx Nb Nj Nr Nu Nv Pa Po Qb Qe) Ms(Hv Hx Ii Ij Iv Jg Jh Jo Js Lx Mb Md Mj Mw Na Nf Nm Nq Qb Qe) Mg(Ii Ij Iv Li Lj Lx Mj Nb Nj Nm Nq Nr Nv Nx Oi Oy Po) Ng(Hv Ii Ij Im In Jh Jk Jp Js Lz Mh Mj Mv Na Nf Qb Qe) Im(Hv Jo Md Mh Mj Nb Nc Nf Nj Nk Nr Oe Oi Pz Qe) Oi(Fp Hw Hx Js Lj Lz Mh Nb Nm Nr Po Qb Qe) Of(Hw Hx Ii Ij In Jo Ma Md Nf Nv) Nj(Hv In Jo Js Lz Mj Oy Po Qe) Oe(Hx Iu Jo Li Nv Pg Po Qb Qe) My(Hx Ii Jg Jh Md Mv Nq Nv) Hu(Jg Jh Jk Md Nv Pb Po Qb) Pz(Ih Iv Jg Jp Js Ma Po Qb) Oy(Hx Ii Ij Jg Jo Nq Nv Qb) Pb(Hx Ij Jo Nb Nv Ny Qb) Ns(Jg Mq Nu Pd Po) Lx(Hv Ih Iv Nm) Iu(Hv Hw Io Jo) Na(Ma Nq Pa) Nb(Hx Ip Ny) Lj(Md Nq Nv) Po(Ip Mh) Nn(Jk Lu) Ne(Nc Nl) Nk(Mq Ni) Pa(Hw Ih) NrJo LzHv IoIv} Nq{Hu(Fr Hv Hx Ih Ij Im In Ip Iv Jg Jk Jo Jp Li Lj Lw Mr Mx Nb Nf Nr Nt Pg Po Qd Qe) Qd(Hv Hw In Ip Jo Jt Lw Mb Mg Mr Na Nf Ng Nr Oi Ok Pa Pe Po Pz) Hw(Ih Im Ip Iv Jn Jo Jp Lw Ms My Ng Nj Ns Of Oh Oy) Lw(Ip Ir Iv Jp Lj Ms Mx Nb Nf Ng Nr Oh Qa) Ng(Hx Ii Ir Iv Jo Lx Mr Mw Nf Ok Pa Pg) My(Ii Jg Jh Jt Lx Nf Nr Nt Ok Pg Po) Ip(Jn Jt Mr Na Nf Nr Ok Pa Pe Qa) Oy(Hx Ii Jg Jt Lx Mr Nf Ok Pa Pg) Nt(Ik Ir Jo Mg Ms Nj Oe Oi Qa) Ms(Ir Jg Jt Mr Nb Nr Ok Pa) Jn(Io Jm Jo Mg Mr Nr Oe Pa) Pe(Ih Ir Jo Jt Ok Pb Pz Qa) Qa(Jo Mg Nj Ok Pa Pz) Ir(Jm Jo Mg Oi Ok) Oe(Lh Mr Nb Nr Pa) Jt(Im Io Of Oi) Mg(Iv Jo Mr) Na(Nj Pa) Ok(Nc Nk) LvMr NbOf HvPa IvOi} Lx{Mh(Hv Hw Hx Ii Ij In Ip Ir Iv Jo Js Lw Ly Lz Mg Mk Mr Na Nb Nf Nm Nt Oh Ok Oy Pd Pe Pf Qa Qd) Lw(Hw Ip Ir Iv Jm Jp Li Lu Ly Mf Mg My Na Nb Nr Ns Of Oh Ok Oy Pg Qd) Hq(Hv Hw Ii Ij In Ip Jk Jo Lh Lj Mb Mq Na Nb Nd Nm Ok Pa Pg) Oh(Hv Hw Ij Im In Ip Ir Iv Jn Jo Jp Lv Na Ni Nj Nm Ok Qd) Ip(Hv Hw Ir Jn Jo Ly Na Nb Ng Ok Oy Qa Qd) Of(Fr Hv Hw Jg Jh Jn Jo Mg Nf Nm Nt) Na(Jp Ly Ma Mg Ml Ng Nj Oy Pb Qd) Hw(Jo Jp Ly Ma Mg Ml Ng Oy Qd) Ng(Jk Jn Ma Nb Nm Nt Pg) Oy(Jk Jo Mb Mg Nm Nt Pg) Pb(Hv Ij In Jn Jo Nb Ny) Ly(Iv Jo Nj Nt Pe) Mg(Fr Ir My Ok Qa) Qd(Jo Mb Ok Pz) Nb(Hx Ml Ny) NsMq NtIk MlIn MsJg MvMy HuJh PzQa JnOk} Pg{Ng(Hw Im Ip Ir Iu Iv Jh Jk Jo Li Lw Ma Mg Mr Mw Na Nb Nf Nm Nt Oh Ok Pa Pe Qa) Jo(Fr Hv Hw In Ip Ir Iu Iv Jn Lw Mg Mr Na Nf Nm Of Oh Pe Qa) Lw(Hq Hw Im Ir Iu Iv Jn Lu Mg Nf Ns Oy Qa) Mg(Hw Ip Ir Iu Jn Jt Nm Ok On Oy Pe Qa) Io(Ih Ir Iu Iv Jn Nm Nt Oh Qa Qd) Pz(Im Ip Ir Jg Jn Jt Ok Qa Qd) Nf(Ip Iu My Of Oy Pb Qd) Oh(Hw Im Ip Na Oi Pa Qa) Oy(Jk Lh Nb Pa Pe Po) Pb(Hw Mr Nb Ok On Pe) Im(Hw Jn Jt Mj Na) Ip(Hw Jn Jr Mr Pa) Ns(Hw Jg Mq) My(Fr Jg Lh) Of(Hw In Pe) Nt(Ik Jm) Mk(Pa Pe) Ms(Jg Nb) Oe(Nb Pe) FrHu NdHq IiLh IkIv JnPa} Nt{Ng(Hw Im Io Ir Jh Jk Lv Mb Md Mv Nd Ne Nf Nm Oe Oh Ok Pe Po Qd) Jo(Hv Hw In Ir Jh Jk Jp Js Li Lv Mb Md Mg Mq Mr Mw Nj Nm Ok Qd) Ik(Im Ir Iv Jg Jh Jk Jt Lh Li Ma Mg Mj Nj Po) Mg(Jg Jk Jt Lh Li Ne Nm Oe Oi Qa) Pz(Im Ir Jg Jk Jp Jt Li Ma Ok) Oi(Ih Im Ir Jg Lh Li Ma Ne) Nj(Jt Lv Md Nd Oe Qa Qd) Oe(Ir Jh Mx Nd Nf Qd) Ne(Ih Jp Nd Nl Qd) Io(Ir Jg Jk Lv Pb) Ms(Jh Mw Nb) It(Hv Ir Na) Jg(My Oy Qd) Jm(Jk Qa Qb) Of(Jh Nb Po) Nd(Hq Ns) Nf(Lv Qd) Oh(Im Pe) Oy(Mv Po) MkPa MyNb HuJh NyPb} Ip{Hw(Jg Jk Jn Jo Jp Lw Ma Md Mg Nf Nj Ns Nv Oh Ok Pa Pb Po Qa Qd) Jt(Io Jk Jo Jr Lu Md Mg Mr Ms Nd Nf Ng Nv Oh Pa Po Pz) Qa(Io Jg Jk Lw Ma Md Mg Mr Nb Nv Oh Ok Pa Po Pz) Po(Jn Jo Jr Lw Mg Mh Ng Of Oh Ok Oy Pb Qd) Pa(Hv Ir Jn Lv Md Mk Ms Na Nf Oe Oh Ok Qd) Nb(Jn Jr Lw Ms My Oe Of Oh Oy Pb) Ok(Jk Jn Jr Lu Md Mg Nc Nk Nv Oh) Jr(Jg Lu Lw Md Ms Nv Oh Qc) Mr(Jn Jo Lv Ma Md Mg Qd) Pe(Ik Jn Md Mg Oz Pb Pz) Jk(Hu Jn Oh) Lw(Jn Lu) MgJn MvMy JhOy} Nn{Ms(Fp Ih Il Jg Jk Js Ma Mb Md Me Mj Mq Mw Mx Nd Ni Nm Nv Nx Oz Qb Qe) Ni(Ih Il Jk Jp Mf Nc Nd Nj Nl Nv Oz Qb Qe) Mf(Fp Jk Jp Lu Mh Mq Nd Nj Nm Nv Qe) Lw(Fp Il Io Jp Mh Mx Nd Nv) Me(Iu Mb Mj My Nd Nj Nm Ns) Mq(Ih Il Iu Mw Nd Nj Nk) Pz(Ij Jg Jk Li Ma Nv Qe) Nm(Il Lu Mh Mx Nd Nv) Ns(Jg Jh Md Nx Pd) Mg(Iu Jg Jk Ma Nx) Ng(Jh Jk Ma Mw Nv) Fp(Iu Jp Nd Nv) Im(Jp Js Nk Qe) Md(Iu Mx Nj) My(Jg Nv Nx) Nd(Hq Jp Nj) Ih(Ma Mj) Ij(Oe Oz) Jg(Io Oy) MbMh MvJh HxPb JkOe NvOy} Nb{Of(Hx Im Is Iv Jg Jh Jk Jn Jp Jq Jr Li Lw Ma Md Mg Mr Mv Mw Nd Nf Nj Nv Po Qa) Ms(Im Jg Jh Jn Jq Jr Lw Ma Mg Ml Mw Oh Pe Po Qa Qd) My(Im Is Jk Jp Jr Lh Lw Ma Md Mg Nj Pa Pe Po Qa) Oe(Im Jk Jn Jr Oh Pe Po Qa Qd) Fr(Hx Mg Mh Ml Ny Oi Pb) Lw(Im Jn Li Oh Po Qa Qd) Jr(Hr Im Mh Ml Nd Nj Oh) Oy(Jg Jk Mv Mw Pa Pe Po) Pe(Hx Mh Ml Ny Pb) Jl(Hx Ml Ny) Jq(Im Nj Pb) Pa(Hx Ny Pb) Ma(Mg Ng) Pz(Qa Qd) NdHq NgJg IjOn ImOh IsOi} Pa{Oh(Hv Hw Ij Im In Ir Jn Jo Jp Lv Mk Ms Na Ni Nj Nm Oi Ok Po Qd) Mk(Hv Hw Ir Jg Jn Jo Lh Ma Mg Na Ok Pd Pe Po Qa) Jn(Im Io Lv Ma Mg Mh Ml Ms Nj Oe Ok) Ok(Lv Mg Ms Nc Nj Nk Oe Of Pb Qd) Qa(Io Jo Ma Mg Ml Nj Oe

Constrained panels with 2 analytes, where 1.0E-7 >= 'model p-value' > 0. Contains 354 panels of 11,037 total panels evaluated. : On(aA Et Fr Hu Im Io Ip Ir Is Ji Jj Jl Jn Jq Jr Lh Lw Mi Mm Mp Ms Mu Mv Mw My Mz Ng Nj Nk Nn No Ns Nt Oe Of Og Oi Oy Pc Pe Pz Qa Qd) Nn(aA Et Fr Hu Hw Hx Ii In Ir Is Iv Ji Jj Jl Jn Jo Jq Jr Jt Lh Lx Mi Mp Mr Mu Mz Na Nb No Nr Nt Nw Oi Ok Om Pa Pe Pg Po Qa Qd) Jl(aA Et Fr Im Io Is Ji Jj Jn Jq Jr Jt Lh Lw Md Mg Mi Mm Mp Mt Mu Mz Nf Ng Nm No Nq Nt Nw Oe Og Oh Oi Ok Om Pc Pz Qa) aA(Et Fr In Ip Is Jg Ji Jk Jn Jq Jr Lh Lv Lw Lx Ma Mg Mi Mm Mp Mt Mu Nj No Nq Nt Nw Om Pa Pc Pe Pg Po Qa) Fr(Hv Hw Ih In Ip Ir Is Iv Ji Jj Jn Jo Jq Jr Jt Lh Lw Mi Mp Mq Mr Mu Mz Na No Nt Oh Ok Pe Qa) Ji(Hw Io Ip Is Iu Jj Jk Jr Lh Lu Lx Mi Mm Mp Mr Ms Mu Nd Nk No Nq Nt Nx Og Pa Pc Pe Pg) No(Et Ip Is Jg Jj Jn Jq Jr Jt Lv Lw Mg Mi Mm Mp Mt Mu Mz Nj Nm Nq Oh Ok Om Pc Qa) Mu(Et Ir Is Jj Jn Jq Jr Jt Lh Mi Mp Mr Mz Nt Nw Ok Pe Qa Qd) Jq(Et Ip Is Jj Lh Lx Mg Mi Mm Mp Mr Nd Nq Nt Pa Pc Pe Pg) Is(Et Io Jj Lh Lw Lx Mg Mi Mm Mp Ms Nt Og Pa Pc Pe) Lh(Et Ip Jj Jn Jo Jr Lw Mm Mp Nw Og Oh Pc) Jr(Et Jj Lx Mg Mi Mm Mp Nq Nt Pc) Nt(Jj Lw Mm Mp Mt Mz Nw Pc) Jj(Jk Jn Nq Om Pe Pg Po) Mi(Jn Mz Om Pc Qa) Mm(Mr Mz Pe Qa) Mp(Jn Mz Nw Om) Og(Mt Mw Nb Om) Pc(Mr Mz Pe) LwMr MtMy HwNw Constrained panels with 2 analytes, where 1.0E-6 >= 'model p-value' > 1.0E-7. Contains 357 panels of 11,037 total panels evaluated. : Mu(Hv Hw Ih Im Ip Iu Iv Jo Js Li Lv Lw Lx Lz Md Mh Mm Ms Mt Na Nb Nf Ng Nj Nm Nr Oe Og Oh Oi Om Pa Pc Pg Po Qb Qe) Nn(Fp Hv Ih Ij Il Im Ip Iu Jp Js Lv Lw Ma Md Me Mf Mh Mq Ms Mt Mx Nd Nf Ni Nm Nv Og Pc Qb Qe) Nt(Et Im Io Ip Ir Jg Jn Jo Jp Jt Li Lv Ma Md Mi Ne Nf Ng Nj Nq Oe Og Oh Ok Om Pe Pg Po Qa Qd) Et(Fr Hw Hx Ir Jj Jk Jn Jt Lw Lx Md Mi Mp Mr Mt Mz Nf Nr Nw Om Pa Pc Pe Pg Po Pz Qa) Jr(Hw Im Ip Is Iu Jg Jk Jo Jq Jt Lw Ma Mr Mt Mz Nb Nd Nv Nw Oh Ok Om Pa Pe Pg Po) Jq(Hw Hx Im Iu Jg Jk Jo Jp Li Ma Mt Mv Mw Nb Nj Nr Nv Nw Og Ok Om Oz Po Qa) Mi(Hv Hw Io Ip Ir Jg Jj Jk Jp Jt Lh Lw Mm Mp Ms Mt Nq Nw Ok Pe Pg Po Qd) Jj(Ii Ij Ip Ir Iv Jh Jo Jt Lx Mp Mr Mt Mz Nv Nw Pa Qa) Is(Hw Lu Md Mr Mt Mz Nf Nq Nw Oh Oi Ok Om Pg Po Pz) Nw(Fr Hv Iu Jo Jt Lw Mm Mr Mz Na Nq Pc Pe Qa) Mp(Hw In Ir Jt Lx Mr Nb Nf Ok Pc Po Qa Qd) Om(Ir Iu Jt Lh Lx Mm Ms Of Oh Pc Pe Qa) Fr(Ij Iu Mx Nc Nf Ng Nm Nr Pc Pz Qd) Pc(Ip Jg Jn Jt Lw Mg Mt Mz Nq Og Oh) Lx(Hq Ir Jn Jt Lw Mz Ok Pc Qa Qd) Lh(Ma Mg Mt Mz Ng Of Pb Qa Qd) Pc(Hw Ir Jn Ok Pa Pg Po Qa Qd) Pg(Jn Jt Lw Mm Mt Mz Ok Qa) Nq(Jr Jn Jt Mz Ok Qa) Mm(Hw Ir Jn Nf Pa Po) Pa(Jn Jt Lw Mz Qa) Mt(Mh Ny Pb Qa) Mz(Ip Iu Lw) Mr(Jn Oh) Qa(Mg Oh) PoLw MwMy Constrained panels with 2 analytes, where 1.0E-5 >= 'model p-value' > 1.0E-6. Contains 491 panels of 11,037 total panels evaluated. : Mp(Fp Hq Hv Hx Ih Ii Ij Im Ip Iv Jg Jh Jk Jo Jp Js Li Lu Lv Lw Ma Md Mh Mj Mm Ms Mt Mw Mx Na Ni Nj Nm Nq Nr Ns Nv Oh Pa Pc Pd Pg Qb Qe) Mz(Hw Im Ir Iv Jg Jk Jn Jo Jp Jt Li Lv Ma Mg Ml Mq Mr Ms Mt Mw Na Nb Nd Nj Nk Nr Nv Og Oh Ok Om Pb Po Qa Qd) Mt(Hw Hx Im Ip Ir Iu Iv Jn Jo Jt Lv Lw Lx Ml Mm Mr Nb Nf Nq Nr Of Oh Ok Om Oy Pa Pc Po Qd) Jj(Hw Hx Ih Il Im Iu Jg Js Li Lv Lw Ma Md Mg Mv Mw Mx Nb Nf Nr Nx Ny Ok Pc Pd Qb Qd Qe) Lx(Hv Hw Ih Im In Ip Iv Jo Jp Li Lv Ly Ma Mg Mh Mm Mq Na Ng Nm Nw Of Og Oh Oy Pb Po) Ok(Et Hw Hx Ip Ir Iu Iv Jk Jn Jp Md Mg Mm Mr Nc Nd Nk Nv Nw Oh Om Pa Po Qa Qd Qe) Jt(Hx Im Io Ip Jg Jk Jn Jo Jp Li Lu Ma Md Mm Mr Ms Nd Nf Nv Og Pc Po Qa Qd) Om(Hw Ih Ip Iv Jn Lw Lz Mg Mh Mr Mx My Nd Ng Nk Nq Nw Oe Oy Pa Pg Po Qd) Mm(Et Fp Hv Hx Ih Ii Ij In Ip Iv Jk Jo Js Lv Md Mx Na Nb Nr Nv Qb Qd) Po(Hw Im Ip Ir Iv Jn Jo Lv Ma Mr Na Nb Nf Nq Og Oh Oy Pa Pc Qa Qd) Nw(Ij In Ip Ir Iv Jk Jn Li Mb Mg Mq Nd Nr Nu Og Oh Oi Pa Pg Wm) Mr(Ih Im Ip Ir Iv Jg Jk Jp Li Lv Ma Md Mg Mw Nq Og Pg Qa Qd) Et(In Io Ip Iu Iv Lu Mh Na Nb Nc Nd Nk Nq Nv Oe Oh Oi Qd) Lw(Hw Hx Ir Iv Jk Jn Jp Li Lu Mx Nb Nf Nq Nr Nv Qa Qd) Pg(Hw Ih Im Ip Ir Iu Iv Jo Na Nf Ng Nm Og Oh Oy Pe Qd) Pc(Hv Hx Ii Im In Ip Iv Jo Jp Js Mx Na Nb Nf Nr) Qa(Hw Io Ip Iu Jg Jk Jr Ma Md Nb Nd Nf Nv Pz) Jn(Hw Ip Jg Jk Jo Ma Md Mg Nb Nd Nr Nv Oh) Qd(Hw Jg Jk Jo Md Nb Nf Nq Nr Nv Pa Pe) Pa(Hv Hw Im Ip Ir Li Lv Ma Na Og Oh) Nq(Hu Hv Hw Ih Ip Iv Jo Na Nf Nr) Ir(Ip Jg Jk Ma Md Mg Nb Nv Oh) Hw(Im Ip Jg Jp Li Ma Mg Oh) Nb(Im Ip Li Ms My Of Oh) Mi(Hq Li Lj Lv Nf) Jr(Jp Lu Md Mw Nr) Og(Hx Jg Jh Jk) Ip(Md Nv) Oy(Jh Mw) WmJq NfIu ImOh aJdN Constrained panels with 2 analytes, where 1.0E-4 >= 'model p-value' > 1.0E-5. Contains 579 panels of 11,037 total panels evaluated. : Lw(Fp Hv Ih Ii Ij Il Im In Io Ip Iu Jg Jh Jo Js Lv Lz Ma Md Mg Mh Mj Mm Mq Ms Mv Mw Na Nc Nd Nk Ny Og Oh Ok Pc Qb Qe) Nq(Fp Hx Ii Ij Im In Iu Jp Js Li Lj Lv Lz Ma Md Mh Mj Mm Mq Ms Mx My Nb Nc Ng Nj Nk Nm Nv Og Oh Oy Pa Pc Qb Qe) Nv(Fp Hv Hw Ih Im In Io Iu Iv Jo Jp Li Lv Lz Ma Mg Mh Mq Mt Mx Na Nb Nf Ng Nj Nm Nr Oe Og Oh Oi Pa Pc Qe) Pc(Fp Hu Ih Ij Il Iu Jg Jh Jk Li Lu Lv Lz Ma Md Mg Mh Mj Mm Mq Ms Mw Nd Ni Nm Nx Ny Og Oh Oi Pd Qb Qe) Ip(Hv Hx Ih Ii Ij Im In Iu Iv Jg Jk Jo Jp Js Li Lu Lv Lz Ma Mg Mv Mw Mx Na Nf Nr Og Oh Qd) Nb(Hw Hx Ih Iu Iv Jk Jp Js Lv Lx Ma Md Mg Mh Ml Mw Mx Nc Nd Nf Nj Nk Ny Oe Ok Oy Pb Qe) Li(Hv Hx Ii Ij Im In Ir Iu Iv Jk Jn Jo Jp Lu Lv Ma Md Mg Mm Mq Mt Na Nd Nf Nr Oh Oi Ok) Pa(Ih Ij In Iv Jg Jh Jk Jo Jp Js Lx Md Mg Mk Mq Ms Mw Mx Nc Nf Ni Nj Nm Oe Pb Qe) Ma(Hv Hx Ih Ii Ij In Iu Iv Jk Jo Js Md Mm Mq Mt Mx Na Nf Nr Oh Ok Qb Qd Qe) Im(Hv Hx Ii In Iu Iv Jg Jk Jo Jp Lu Lv Md Mg Mh Mj Mm Mq Na Nf Nr Qd) Hw(Hx Ih Ir Iu Iv Jh Jk Js Lv Lz Md Mn Mw Mx Nd Nf Nj Ns Ny Qb Qe) Jo(Hx Ih Ir Iu Iv Jg Jk Jp Lv Lz Md Mg Mw Mx Nd Nf Ng Og Oh Qb Qe) Mt(Hv Ii In Jh Jk Md Mg Mq Mv Mw Na Nc Nd Nj Nm Oe Oi Qb Qe) Jp(Hx Ii In Ir Iu Iv Jj Jk Jn Lv Md Mg Mm Mx Na Nf Nr Oh Po) Jg(Hx Ih Iu Iv Js Lv Lx Mq Ms Mv Mx My Na Nf Ng Nr Ns Oh Ok) Jk(Hu Hv Ih Iv Js Lv Lx Md Mh Mq Na Nf Ng Nr Oe Oh Po) Mg(Hv Hx Ih Iv Js Lv Md Mp Mx Na Nf Nr Og Qb Qd Qe) Jj(Fp Hv In Iq Jm Mj Mm Mn Mq My Na Nc Nd Nm Nu Oh) Oh(Hv Hx Ii Ij In Iv Jh Lv Mw Mx Na Nf Nr Qd Qe) Lv(Hx Ih Ii Ir Iu Iv Jn Md Mw Nf Nr Ok Qd) Mm(Il Iq Iu Lu Me Mh Mj Mq Ni Nx Pd Pz Qe) Qd(Hx Ii In Iu Jh Lu Mb Mq Mw Na Nd Pz) Iv(Hx Iu Jh Md Mq Mw Nd Nf Nr Og) Lx(Ij Iu Mr My Nc Nf Nr Qe) Ir(Hx Jh Lu Mw Nd Nf Nr Og) Po(Iu Jh Mh My Ns Of Pb) Ok(Ih Mh Mw Mx Nf Og Pz) Mp(Iu Lj Lz Nc Nu Og) Md(Hx Iu Mx Nr Qe) Iu(Hv Hx Ij Jn) Og(Ii Jn Mv Nr) aA(bC bW cJ dN) Nf(Mx Nr Qe) aJ(aM bC cF) Jn(Lu Ms) aP(cF dH) dN(aY dC) NmMr NrJs MqMw NyPb cSdM Constrained panels with 2 analytes, where 1.0E-3 >= 'model p-value' > 1.0E-4. Contains 408 panels of 11,037 total panels evaluated. : Mw(Hv Hx Ih Ii Ij In Iu Jg Js Lu Lz Md Mg Mh Mj Ms Mx Na Nd Nf Ng Nm Nr Nu Nx Qe) Nd(Fp Hq Hv Hx Ih Ii Ij In Ip Jg Jp Js Lv Ma Md Mg Mq Mx Na Nf Nm Nr Nx Oh Qe) Iu(Fp Ih Ii In Jh Jk Js Lu Mg Mh Mn Mq Mv Mx Na Nm Nr Nu Nx Ny Og Oh Pd Qb Qe) Jg(Fp Hu Hv Ji Ij In Io Jp Lu Lz Ma Md Mg Mh Mj Nc Nk Nu Oe Oi Oy Pz Qb Qe) Ih(Hv Hx Ii Ij In Jh Jp Lu Md Mh Mj Mq Mv Na Nf Nm Nr Nu Nx Oh Oi Pd) Qe(Hv Ii Ij Im In Ip Jh Jk Jp Lu Lv Mq Mx Na Nm Nr Nx Oe Og Oi Pd) Oh(Fp Hu Il Js Lu Md Mg Mh Mj Mn Mq Mv Nc Nj Nm Nx Ny Oi Oz Pd Qb) Jh(Hu Hv Hx Ii Ij In Ip Js Lv Lz Md Mh Mq Ms Mx My Na Nf Nr Qb) Lv(Hv Ij In Js Lu Lz Ma Mb Mh Mj Mq Mv Mx Na Nc Nm Pd) Mg(Fp Ii Ij In Jk Lj Lu Lz Ma Mb Mh Mj Mq Nc Ng Nk Oi) Md(Fp Hv Ii Ij In Js Lz Mh Mj Mq Mv Na Nf Nj Nm Qb) Jp(Fp Hv Ij Io Js Lu Lz Ma Mh Mq Nm Nu Pd Qb) Nf(Hx Ii Lz Mh Mv Na Nc Nj Nk Nl Og Oz Qb) Mx(Hv Hx Ii Ij Im In Jk Na Nm Nr Nx Og) Ma(Im Mb Mh Nc Ng Nk Nm Nu Nx Og Oi) Lz(Hv Ij Im In Jj Jk Mq Na Nm Nx) Na(Fp Mh Mn Mv Nj Nk Ny Pd Qb) dM(aI aO aU bA bC bO bW dE dF) Nm(Fp Hx Jk Lu Mh Nr Og Qb) Mq(Ii Ij Ip Js Mv Nk Ns Qb) Im(Ij Js Mv Nc Nu Nx Og Pd) Ip(Mh Mj Mn Nc Nk Nu Nx) Jj(Hq Hu Mh Nk Nl Oz Pf) Jk(Fp Hx In Mj Oi Pz Qb) bA(aO bC bE bW cF cS cU) Nr(Hx Ij Lu Nj Oe Qb) Ii(Fp Mh Ms Mv Nc Nj) cS(aM aO bO cF dD dF) Ij(Lu Mh Ms Oe Og) In(Mh Mv Og Qb) Hx(Js Ms Oe) Js(Lu Og) Nx(Mh Og) aM(aO bW) WmQd NsPd LwMf MvMy HvQb IvOi aObC bWcT

Ny Oe Og Oh Oi Om Oy Oz Pb Pc Pd Pf Pz Qc Wm) Mw(aA Et Fp Hq Hr Hu Hv Hw Ik In Io Iq It Iu Iv Jg Jm Jo Jp Jq Js Jt Li Lu Lw Lx Ly Lz Mc Md Mf Mg Mi Mj Mk Ml Mm Mn Mq Mr Ms Mv Mx My Mz Na Nb Nc Nd Ne Nf Nj Nk Nl Nm No Nr Ns Nu Nw Nx Ny Oe Og Oh Ok Om Oz Pb Pc Pd Wm) Nw(aA Fp Hq Hr Hu Hv Hw Ik In Io Iq It Iu Iv Jg Jm Jo Js Li Lj Lu Lw Lx Ly Lz Mc Md Mf Mg Mh Mi Mj Mk Mm Mn Mq Mr Ms Mv Mx My Mz Na Nb Nc Nd Ne Nf Nh Nj Nk Nm No Nr Ns Nu Oe Og Oi Ok Om Oy Pd Pf Pz Qc Wm) Lx(aA Et Fp Hq Hu Hv Hw Ik In Io Iq Iu Iv Jg Jh Jm Jo Jp Jq Js Jt Li Lj Lu Lw Lz Mc Me Mf Mg Mi Mj Mk Ml Mm Mn Mq Mr Ms Mv Mz Nb Nd Ne Nf Ni Nj Nk Nm Nr Ns Nu Nx Ny Oe Og Oh Ok Om Oz Pd Pf Pz Wm) Iu(aA Et Fp Hq Hu Hv Hw Ik In Io Iq It Iv Jg Jh Jm Jo Jp Jq Js Jt Li Lj Lw Mb Md Mf Mg Mi Mj Mk Mn Mq Mr Ms Mv Mx My Mz Nb Nc Nd Ne Nf Nj Nk Nm No Nr Nx Ny Oe Og Oh Oi Ok Om Pd Pf Pz Wm) Nr(aA Et Fp Hq Hu Hv Hw Ik In Io Iq It Iv Jh Jo Js Jt Li Lj Ly Lz Mb Mc Me Mg Mh Mi Mk Ml Mm Mn Mq Mr Ms Mz Na Nb Nd Ne Nf Ng Nh Nl Nm No Ns Nu Nx Ny Of Oi Ok Om Oy Pd Pz Qc Wm) Hw(aA Et Fp Hq Hu Hv Ik In Io Iq It Iv Jg Jh Jm Jo Jp Jq Js Li Lj Lw Mc Mf Mg Mi Mj Mk Ml Mm Mn Ms Mv My Mz Na Nb Nd Ne Nf Nj Nk Nm Ns Nx Ny Oe Of Og Oh Ok Om Oy Oz Pd Pf Pz) Li(aA Fp Hr Hu Hv Ik In Io Iv Jm Jo Jp Jq Js Lu Lw Ly Mc Md Mf Mg Mh Mi Mj Mk Ml Mn Mq Mr Ms Mx My Mz Nb Nc Nd Ne Nf Nh Nj Nk Nl Nm No Nx Ny Oe Og Oh Oi Ok Oz Pd Pz Qc Wm) Om(aA Fp Hu Ik In Io Iq It Iv Jm Jo Jp Jq Js Lu Ly Lz Md Mg Mh Mi Mj Mk Mn Mr Ms Mv Mx Mz Nb Nc Nd Ne Nf Nh Ni Nj Nk Nl No Ns Nu Oe Og Oi Oz Pd Pz Qc Wm) Js(aA Et Fp Hq Hu In Io Iq Jg Jh Jm Jo Lj Lw Ly Mc Mf Mg Mi Ml Mm Mn Mq Mr Ms Mv Mx My Na Nb Nd Ne Ng Nh Ni Nk Nm No Ny Oe Og Oi Oy Pd Pf Qc Wm) Fp(aA Et Hu In Iq It Iv Jg Jm Jo Jp Jq Jt Lw Lz Md Mg Mi Mj Mk Mm Mn Mq Mr Ms Mv My Mz Nb Nc Nd Nf Nj Nk Nm No Nx Ny Og Oi Pd) Jo(aA Et Hq Hu In Iq It Iv Jh Jm Jp Jq Lj Lw Mi Mj Mk Mm Mn Mx Mz Nb Nc Nd Ne Nh Nj Nk Nm No Nx Ny Oe Og Oi Ok Pd Pf Wm) In(aA Et Hq Hu Iq It Iv Jg Jm Jp Lw Lz Mf Mg Mi Mk Ml Mm Mn Mq Mv My Na Nc Nd Nk Nm No Nu Nx Ny Of Oh Ok Pb Pd Pf) Mi(Et Hu Hv Ik Io Iq Jh Jm Jp Jq Lj Lu Ly Md Mf Mg Mk Mm Mn Mq Ms Nd Nj Nk Ny Oe Og Ok Pc Pd Pf Pz Wm) Mg(aA Hq Hu Iq Iv Jm Jp Jq Lj Md Mh Mj Mk Mn Mr Ms Mx Mz Nb Nc Nd Nf Nk No Nx Ny Og Oi Ok Pf Wm) Et(aA Hu Io Iv Jm Ly Mh Mj Mk Mn Mr Ms Mx My Mz Nb Nc Nd Ne Nh Ni Nj Nk No Oe Og Oi Pz Wm) Ny(aA Hu Io Iv Jm Lu Ly Md Mh Mj Mk Mr Ms Mx My Mz Nc Nd Nf Nj Nk No Nu Oe Og Oi Pd Wm) Wm(Hu Hv Iv Jg Jh Jp Jq Jt Md Mm Mq Mr Mv My Mz Nb Nc Nd Nf Nh Nm No Oy Pd Qc) Nd(Hu Ik Iq Iv Jg Jh Jm Jp Jq Jt Lj Mk Mm Mn Mq My Mz Nb Nj Nm No Nu Pd Pf) Hu(aA Hq Iq It Jg Jm Jt Lw Mj Mk Mm Mn Mx My Mz Nb Nm No Ok Pc) No(Hv Ik Iq Iv Jh Jp Mf Mk Mm Mn Mq My Ne Nh Nj Oe Oz) Mn(aA Io Iv Mj Mk Mm Mr Ms Mx Mz Nb Nf Nk Og Oi Pd) aA(Hq Iq Jh Jm Jp Lw Mf Mk Mm Mv My Nj Nk Nm Pc) Jm(Io Iq Iv Jh Mk Mm Mq Mr Mv My Mz Nf Pd) Iq(Iv Jp Mr Ms Mv Mz Nb Nk Nu Og Pd) Mm(Jq Mj Mr Mz Nb Nc Nk Og Oi) Mr(Jh My Ne Nj Nx Oe) Nb(Mk Ml Nk Of Og Pb) Jg(Mj Mx Nk Og Oi) Jh(Lz Mh Mx Nc Nk) Iv(Nh Nj Nk Og) Mk(Jp Jq Ms) Mv(Ms Oi Pb) Og(Jt Ok Pd) Mx(Lw Pd) MlMz NkHq} Jl{Ms(aA Et Fp Fr Hq Hr Hu Hv Hw Hx Ih Ii Ij Ik Il Im In Io Ip Iq Ir Is It Iu Iv Jg Jh Ji Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nj(aA Et Fp Fr Hq Hr Hu Hv Hw Hx Ih Ii Ij Ik Il Im In Io Ip Iq Ir Is It Iu Iv Jg Jh Ji Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Io(aA Et Fp Fr Hq Hr Hu Hv Hw Hx Ih Ii Ij Ik Il Im In Ip Iq Ir Is It Iu Iv Jg Jh Ji Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ip(aA Et Fp Fr Hq Hr Hu Hv Hw Hx Ih Ii Ij Ik Il Im In Iq Ir Is It Iu Iv Jg Jh Ji Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Pz(aA Et Fp Fr Hq Hr Hu Hv Hw Hx Ih Ii Ij Ik Il Im In Iq Ir Is It Iu Iv Jg Jh Ji Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om On Oy Oz Pa Pb Pc Pd Pe Pf Pg Po Qa Qb Qc Qd Qe) Ji(aA Et Fp Fr Hq Hr Hu Hv Hw Hx Ih Ii Ij Ik Il Im In Iq Ir Is It Iu Iv Jg Jh Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om On Oy Oz Pa Pb Pc Pd Pe Pf Pg Po Qa Qb Qc Qd Qe) Jm(aA Et Fp Fr Hq Hr Hu Hv Hw Hx Ih Ii Ij Ik Il Im In Iq Ir Is It Iu Iv Jg Jh Jk Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nn No Nq Nr Ns Nu Nv Nw Nx Ny Oe Of Og Oh Oi Ok Om On Oy Oz Pa Pb Pc Pd Pe Pf Pg Po Qa Qb Qc Qd Qe Wm) Of(aA Et Fp Fr Hq Hr Hu Hv Hw Hx Ih Ii Ij Ik Il Im In Iq Ir Is It Iu Iv Jg Jh Jk Jn Jo Jp Jq Js Jt Lh Li Lj Lu Lv Lw Lx Ly Lz Ma Mb Mc Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nn No Nq Nr Ns Nt Nu Nv Nw Nx Ny Oe Og Oh Oi Ok Om On Oy Oz Pa Pb Pc Pd Pe Pf Pg Po Qa Qb Qc Qd Qe Wm) Og(aA Et Fp Fr Hq Hr Hu Hv Hw Hx Ih Ii Ij Ik Il Im In Iq Ir Is It Iu Iv Jg Jh Jk Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nn No Nq Nr Ns Nt Nu Nv Nw Nx Ny Oe Oh Oi Ok Om On Oy Oz Pa Pb Pc Pd Pe Pf Pg Po Qa Qb Qc Qd Qe) Oi(aA Et Fp Fr Hq Hr Hu Hv Hw Hx Ih Ii Ij Ik Il Im In Iq Ir Is It Iu Iv Jg Jh Jk Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nn No Nq Nr Ns Nt Nu Nv Nw Nx Ny Oe Oh Ok Om On Oy Oz Pa Pb Pc Pd Pe Pf Pg Po Qa Qb Qc Qd Qe) Nn(aA Et Fp Fr Hq Hr Hu Hv Hw Hx Ih Ii Ij Ik Il Im In Iq Ir Is It Iu Iv Jg Jh Jk Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm No Nq Nr Ns Nt Nu Nv Nw Nx Ny Oe Oh Ok Om On Oy Oz Pa Pb Pc Pd Pe Pf Pg Po Qa Qb Qc Qe) Is(aA Et Fp Fr Hq Hr Hu Hv Hw Hx Ih Ii Ij Ik Il Im In Iq Ir It Iu Iv Jg Jh Jk Jn Jo Jp Jq Js Jt Lh Li Lj Lu Lv Lw Lx Ly Lz Ma Mb Mc Md Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm Nq Nr Ns Nt Nu Nv Nw Nx Ny Oe Oh Ok Om On Oy Oz Pa Pb Pc Pd Pe Pf Pg Po Qa Qb Qc Qd Qe) Lu(aA Et Fp Fr Hq Hr Hu Hv Hw Hx Ih Ii Ij Ik Il Im In Iq It Iu Iv Jg Jh Jk Jn Jo Jp Jq Js Jt Lh Lj Lv Lw Lx Ly Lz Ma Mb Mc Me Mf Mg Mh Mi Mj Mk Ml Mm Mn Mp Mq Mr Mt Mu Mv Mw Mx My Mz Na Nb Nc Nd Ne Nf Ng Nh Ni Nk Nl Nm No Nq Nr Ns Nt Nu Nv Nw Nx Ny Oe Oh Ok Om On Oy Oz Pa Pb Pc Pd Pe Pf Pg Po Qa Qb Qc Qd Qe) Mp(aA Fp Fr Hq Hr Hu Hv Hw Hx Ih Ii Ij Ik Il Im In Iq Ir It Iu Iv Jg Jh Jk Jn Jo Jp Jq Js Jt Lh Li Lj Lv Lw Lx Ly Lz Ma Mb Mc Md Me Mf Mg Mh Mi Mj Mk Ml Mm Mn Mq Mr Mt Mu Mv Mw Mx My Mz Na Nb Nc Nd Ne Nf Ng Nh Ni Nk Nl Nm No Nq Nr Ns Nt Nu Nv Nw Nx Ny Oe Oh Ok Om On Oy Pa Pb Pc Pd Pe Pf Pg Po Qa Qb Qc Qe) Jo(aA Et Fp Fr Hq Hu Hv Hw Hx Ih Ii Ij Ik Il Im In Iq Ir It Iu Iv Jg Jh Jk Jn Jp Jq Js Jt Lh Li Lj Lv Lw Lx Ly Lz Ma Mb Mc Md Me Mf Mg Mh Mi Mj Mk Ml Mm Mn Mq Mr Mt Mu Mv Mw Mx My Mz Na Nb Nc Nd Ne Nf Ng Nh Ni Nk Nl Nm No Nq Nr Ns Nt Nu Nv Nx Ny Oe Oh Ok Om On Oy Oz Pa Pc Pd Pe Pf Pg Po Qa Qb Qc Qd Qe) Mu(aA Et Fp Fr Hq Hr Hu Hv Hw Hx Ih Ii Ij Ik Il Im In Iq It Iu Iv Jg Jh Jk Jn Jp Jq Js Jt Lh Li Lj Lv Lw Lx Ly Lz Ma Mb Mc Md Me Mf Mg Mh Mi Mj Mk Ml Mm Mn Mq Mr Mt Mv Mw Mx My Mz Na Nb Nc Nd Ne Nf Ng Nh Ni Nk Nl Nm

Hv Hw Hx Ii Ij Ik Im In It Iv Jh Jm Jn Jo Jq Js Jt Lj Lu Lw Lx Lz Mb Mc Md Me Mh Mi Mj Mk Ml Mm Mp Mr Mv Mw Mx My Mz Nb Nl Nn Ns Nu Nw Ny Oh Om Oy Pb Pc Pf Po) Oe(aA Et Fp Fr Hu Hv Hx Ii Ij Ik Im In Ir It Iv Jg Jh Jn Js Li Lj Lu Lw Lx Mb Mc Me Mf Mi Mj Mk Ml Mm Mp Mu Mw Mx Mz Na Nd Nf Ni No Ns Nu Nw Ny Oh Ok Pb Pc Pf Qb Qd) Lu(aA Fp Fr Hu Hw Ii Ik Im In Ir It Iu Iv Jg Jm Jn Jq Lh Lj Lw Lx Mb Mc Md Me Mi Mj Ml Mm Mp Mr Mu Mw Mx My Na Nd Ni Nn Nq Nr Ns Nu Nv Nw Oh Oz Pb Pg Po Qd Qe) aA(Fr Hr Hu Hw Hx Ij In Iu Iv Jg Jn Jt Lh Li Lw Lx Ma Me Mf Mg Mh Mk Ml Mm Mn Mp Mr Mu Mv Mw Mx My Na Nc Nd Ni Nl Nn No Nq Ns Nt Nu Oh Ok Oz Pc Pg Po Qe) Ns(Fp Hq Hr Hv Hx Ih Ii Ik Im In Iq Ir Iu Iv Jm Jq Js Lh Lj Lw Lz Mc Me Mf Mi Mj Ml Mp Mr Mx Mz Nd Nf Ni Nr Nt Ny Oh Ok Pb Qd Qe Wm) Hx(Fp Hq Hr Hu Hv Ij Ik Im In Ir It Iv Jh Jm Jn Jq Js Lw Lx Mb Mc Md Me Mf Mh Ml Mp Mw Mx My Mz Nd Nn Nu Ny Oh Ok Oy Pc Pf Po Qd) Po(Fp Hq Hu Hv Hw Ii Ij Ik It Jm Jn Jo Js Jt Lj Lx Mb Md Me Mf Mh Mi Ml Mp Mr Mw Mx My Nb Nd Ni Nr Nu Nw Ny Ok Oz Pb Pf) Mx(Fp Hr Hu Hv Ii Ij Ik In It Iv Jg Jh Jm Jn Js Lj Lw Mb Mc Me Mf Mg Mh Mk Ml Mw Mz Nb Nf Ni Nl Nu Nw Ny Oh Ok Pb Pc) Mp(Hq Hu Hw Ii Ik It Iv Jm Jn Jo Js Jt Lz Mg Mh Mi Mj Mk Mm Mn Mw Mz Nb Nc Nd Nr Nt Nw Oh Ok Pd Pf Pg Qd Qe) Jn(Fp Fr Hu Hv Hw Ii Ik Im Ir It Iu Jh Js Lx Mb Me Mh Mi Ml Mm Mu Mw Nd Ni Nn Nq Nr Nu Pg Qd Qe) Jt(Et Fr Hw Ir Iu Jg Jo Lh Ma Mg Mi Mj Ml Mm Mr Mu Mv Na Nb Nl Nn No Nq Nr Nt Nv Oh Oz Pc Pg Qe) In(Fp Hr Ij Ik Im It Jh Js Li Lw Mc Md Me Mh Ml Mm Mq My Ni Nn Ny Oy Pb Pc Pf Pg) Lx(Hq Hu Hw Ii Ik It Jo Md Mh Ml Mv Mw My Nd Nf Nu Ny Ok Pb Pf Pg Qd) Ii(Fr Hw Ik It Iu Lh Mh Mi Mr Mu Mw Nb No Nq Nr Nt Nu Nv Pg) Mm(Et Fr Hu Hw Iu Ma Mg Mu Mw Ni Nn Nq Oh Ok Pc Pg Wm) Jo(Fr Hw Iu Lh Ma Mg Mi Mr Mu Na No Nq Nr Nt Nv Pg Wm) It(Hw Iu Mh Mi Mj Mr Nd Ni No Nr Nt Nu Qd Qe Wm) Ik(Hu Hw Iv Mj Mr Mu Nd Nq Nt Nu Pg Qd Wm) Mg(Fr Iu Jg Lh Ma Mi Mu Mv Nn Nq Nt Pg) Ml(Hw Ij Iu Mh Mj Mr Mz No Nr) Mu(Hq Ij Jg Ni Oh Ok Pf Pg) Qd(Hv Im Mb Mh Mw Nd Nn) Pg(Et Fr Hq Ij Na Nv Pf) Wm(Ij Im Iu Oh Ok Pf) Fr(Hq Jg Ni Ok Pf) Nu(Hv Hw Me Nd No) Nn(Mf Ni Oh Pc) Mw(Hw Ir My Nd) Mb(Fp Hu Ir) Nd(Hq Iv Mh) Hw(Hq Iv Me) Ij(Nq Ny Pb) Im(Hu Mh Ni) Et(Hu Ok) No(Hq Pf) NtIu MiOk NcNl NiHv} dN{aA(aC aD aE aF aG aH aI aJ aK aL aM aN aO aP aQ aR aS aU aV aW aX aY aZ bA bB bC bE bF bG bH bI bJ bL bM bN bO bP bQ bR bS bU bV bW bX bZ cA cB cC cD cE cF cG cH cI cJ cK cL cM cN cO cP cQ cR cS cT cU cV cW cX cY cZ dA dB dC dD dE dF dG dH dI dJ dK dL dM) aJ(aC aD aE aF aG aH aI aK aL aM aN aO aP aQ aR aS aU aV aW aX aY aZ bA bB bC bE bF bG bH bI bJ bL bM bN bO bP bQ bR bS bU bV bW bX bZ cA cB cC cD cE cF cG cH cI cJ cK cL cM cN cO cP cQ cR cS cT cU cV cW cX cY cZ dA dB dC dD dE dF dG dH dI dJ dK dL dM) aY(aC aD aE aF aG aH aI aK aL aM aN aO aP aQ aR aS aU aV aW aX aZ bA bB bC bE bF bG bH bI bJ bL bM bN bO bP bQ bR bS bU bV bW bX bZ cA cB cC cD cE cF cG cH cI cJ cK cL cM cN cO cP cQ cR cS cT cU cV cW cX cY cZ dA dB dC dD dE dF dG dH dI dJ dK dL dM) dC(aC aD aE aF aG aH aI aK aL aM aN aO aP aQ aR aS aU aV aW aX aZ bA bB bC bE bF bG bH bI bJ bL bM bN bO bP bQ bR bS bU bV bW bX bZ cA cB cC cD cE cF cG cH cI cJ cK cL cM cN cO cP cQ cR cS cT cU cV cW cX cY cZ dA dB dD dE dF dG dH dI dJ dK dL dM) aL(aC aD aE aF aG aH aI aK aM aN aO aP aQ aR aS aU aV aW aX aZ bA bB bC bE bF bG bH bI bJ bL bM bN bO bP bR bS bU bV bW bX bZ cA cB cC cD cE cF cG cH cI cJ cK cL cM cN cO cP cQ cR cS cT cU cV cW cX cY cZ dA dB dD dE dF dG dH dI dJ dK dL dM) aO(aC aD aE aF aG aH aI aK aM aN aP aQ aR aS aU aV aW aX aZ bA bB bC bE bF bG bH bI bJ bL bM bN bO bP bQ bR bS bU bV bW bX cA cB cC cD cE cF cG cH cI cJ cK cL cM cN cO cP cQ cR cS cT cU cV cW cX cY cZ dA dB dD dE dF dG dH dI dJ dK dL dM) bH(aC aD aE aF aG aH aI aK aN aP aQ aR aS aU aV aW aX aZ bA bB bC bE bF bG bI bJ bL bM bN bO bP bQ bR bS bU bV bW bX bZ cA cB cC cD cE cF cG cH cI cJ cK cL cM cN cO cP cQ cR cS cT cU cV cW cX cY cZ dA dB dD dE dF dG dH dI dJ dK dL dM) bS(aC aD aE aF aG aH aI aK aM aN aP aQ aR aS aU aV aW aX aZ bA bB bC bE bF bG bI bJ bL bM bN bO bP bQ bR bU bV bX bZ cA cB cC cD cE cF cG cH cI cJ cK cL cM cN cO cP cQ cR cS cT cU cV cW cX cY cZ dA dB dD dE dF dG dH dI dJ dK dL dM) bX(aC aD aE aF aG aH aI aK aM aN aP aQ aR aS aU aV aW aX bA bB bC bE bF bG bI bJ bL bM bN bO bP bQ bR bU bV bW bZ cA cB cC cD cE cF cG cH cI cJ cK cL cM cN cO cP cQ cR cS cT cU cV cW cX cY cZ dA dB dD dE dF dG dH dI dJ dK dL dM) bC(aC aD aE aF aG aH aI aK aM aN aP aQ aR aS aU aV aW aX aZ bA bB bE bF bG bI bJ bL bM bN bO bP bQ bR bU bV bW bZ cA cB cC cD cE cF cG cH cI cJ cL cM cN cO cP cQ cR cS cT cU cV cW cX cY cZ dA dB dD dE dF dG dH dJ dK dL dM) cF(aC aD aE aF aG aH aI aK aM aN aP aQ aR aS aU aV aW aX aZ bA bB bE bF bG bI bJ bL bM bN bO bP bQ bU bV bW bZ cA cB cC cD cE cG cH cI cJ cK cL cM cN cO cP cQ cR cS cT cU cW cX cY cZ dA dB dD dE dF dG dH dI dJ dK dL dM) cU(aC aD aE aF aG aH aI aK aM aN aP aQ aR aS aU aV aW aX aZ bA bB bE bF bG bI bJ bL bM bN bO bP bQ bR bU bV bZ cA cB cC cD cE cG cH cI cJ cK cL cM cN cO cP cQ cR cS cT cV cW cX cY cZ dA dB dD dE dG dH dI dJ dK dL dM) aG(aC aD aE aF aH aI aK aM aN aP aQ aR aS aU aV aW aX aZ bA bB bE bF bG bJ bL bM bN bO bP bQ bR bU bW bZ cA cB cC cD cE cG cH cI cJ cK cL cM cN cO cP cQ cR cS cT cW cX cY cZ dA dB dD dE dF dG dH dI dJ dK dL dM) aP(aC aD aE aF aH aI aK aM aN aQ aR aS aU aV aW aX bA bB bE bF bG bI bJ bL bM bN bO bP bQ bR bU bV bW bZ cA cB cC cD cE cG cH cI cJ cL cM cN cO cP cQ cS cT cV cW cX cY cZ dA dB dD dE dF dG dH dI dJ dK dL dM) bA(aC aD aE aF aH aI aK aM aN aQ aR aS aU aV aW aX aZ bB bE bF bG bI bJ bM bN bO bP bQ bU bV bW bZ cA cC cD cE cG cH cI cJ cK cL cM cN cO cP cQ cR cS cT cV cW cX cY cZ dA dB dD dE dF dG dH dI dJ dK dL dM) cS(aC aD aE aF aH aI aK aM aN aQ aR aS aU aV aW aX bB bE bF bG bI bJ bL bM bN bO bP bQ bU bV bW bZ cA cB cC cD cE cG cH cI cK cL cM cN cO cP cQ cR cT cV cW cX cY cZ dA dB dD dE dF dG dH dI dJ dK dL dM) aX(aC aD aE aF aH aI aK aM aN aQ aR aS aU aV aW bB bE bF bG bI bJ bL bM bN bO bP bQ bR bU bV bW bZ cB cC cD cE cG cH cI cL cM cN cO cP cQ cT cV cW cX cY cZ dA dB dD dE dF dG dH dI dJ dK dL dM) bG(aC aD aE aH aI aM aN aQ aR aS aU aV aW bB bE bF bI bJ bL bM bO bP bQ bR bU bV bW bZ cA cB cC cD cE cG cH cI cJ cK cL cM cN cO cQ cR cT cV cW cX cY cZ dA dB dD dE dF dG dH dI dJ dK dL dM) dE(aC aD aE aF aH aI aK aM aN aQ aS aU aV aW aZ bB bE bF bI bJ bL bM bN bO bP bQ bR bU bV bW bZ cA cB cC cD cE cG cH cI cJ cK cL cM cN cO cQ cR cT cV cW cX cY cZ dA dB dD dF dH dI dJ dK) dM(aD aE aF aH aI aK aM aN aQ aS aU aV aW aZ bB bE bF bI bJ bL bM bO bP bQ bR bU bV bW bZ cA cB cC cD cE cG cH cJ cK cL cM cN cO cP cQ cR cT cV cW cX cY cZ dA dB dD dG dH dI dJ dK dL) bL(aC aD aE aF aH aI aK aM aN aQ aR aS aU aV aW bB bE bF bI bJ bM bN bO bP bQ bU bZ cA cB cC cE cG cH cI cJ cK cL cM cN cO cQ cR cT cV cW cX cY cZ dA dB dD dF dG dH dI dJ dK dL) aI(aC aD aE aH aK aM aN aQ aR aU aV bB bE bF bJ bM bN bO bP bR bU bW bZ cA cB cC cD cE cG cI cJ cK cL cM cN cO cP cQ cR cT cW cX cY cZ dA dB dF dG dH dI dK dL) bO(aC aD aF aH aK aM aN aQ aS aU aV aW bB bE bF bI bJ bM bN bP bQ bU bW bZ cA cB cC cD cE cG cH cJ cK cL cM cN cO cQ cW cY cZ dA dB dD dF dG dH dI dJ dK dL) dD(aC aD aE aF aH aK aM aQ aS aU aV bE bF bI bJ bM bN bP bU bW bZ cA cB cC cD cE cH cI cJ cK cL cM cN cO cP cQ cR cT cW cX cY cZ dA dB dF dG dH dI dK dL) cM(aC aD aE aF aH aK aM aN aQ aS aU aV aW bF bJ bM bN bP bR bU bW bZ cB cC cD cE cG cH cI cJ cL cN cO cP cQ cR cT cW cX cZ dA dB dF dG dH dJ dK dL) dB(aC aD aE aF aH aM aN aQ aR aS aV aW bF bI bJ bM bN bP bQ bU bW bZ cA cB cC cE cG cH cI cJ cK cL cN cO cP cQ cT cW cX cZ dA dF dG dH dI dK dL) dK(aD aE aH aK aM aN aQ aU aV aW bF bI bJ bM bN bP bQ bU bW bZ cA cB cD cE cG cI cJ cK cL cO cP cQ cT cV cW cX cY cZ dA dF dG dH dI dJ dL) cN(aD aE aH aK aN aU bF bJ bM bN bP bQ bU bW cA cB cC cG cI cJ cK cL cO cP cQ cR cT cX cZ dA dF dG dI) cE(aC aD aF aH aM aN aR aS aU bB bF bI bM bN bP bQ bW bZ cA cG cJ cK cL cO cQ cR cT dA dF dG dH dI) cR(aD aF aH aM aN aS aV aW bF bI bN bO bU bW bZ cB cG cH cI cJ cL cO cO cX cY cZ dA dF dG dH dJ) dH(aC aD aF aM aN aS aU aZ bB bF bI bM bN bP bQ bV bW bZ cB cG cJ cK cO cQ cT dA dF dG dI) bW(aE aF aH aK aM aN aQ aS aU aW bI bJ bM bN bP bZ cG cJ cL cQ cT cV cX cY cZ dF dL) bP(aC aD aE aM aN aS aU bB bE bZ cB cC cG cJ cK cL cO cQ cT cV cY dA dF dG dI) bM(aC aD aE

Pz Qa Qb Qc Qe) aA(Fp Fr Hq Hr Hu Hv Hw Hx Ih Ii Ik Il In Io Ip Ir It Iu Iv Jg Jh Jk Jm Jo Jp Jq Js Jt Lh Li Lj Lu Lv Lw Lx Ly Lz Ma Mb Mc Md Me Mf Mg Mh Mi Mj Mk Ml Mn Mq Mr Mt Mu Mv Mw Mx My Mz Na Nb Nc Nd Ne Nf Ng Nh Nj Nk Nl Nm Nn No Nq Nr Ns Nt Nu Nv Nw Nx Ny Oe Of Og Oh Oi Ok Oy Oz Pa Pb Pc Pd Pe Pf Pg Pz Qa Qb Qc) Nj(Et Fp Fr Hq Hr Hu Hv Hw Hx Ih Ii Ij Ik Il Im In Ip Iq Ir It Iu Iv Jg Jh Jk Jm Jo Jp Jq Js Jt Lh Lj Lu Lv Lw Lx Ly Lz Ma Mc Md Me Mf Mg Mh Mi Mj Ml Mn Mq Mr Mt Mu Mv Mw Mx My Mz Na Nb Nc Nd Ne Nf Ng Nh Nk Nl Nm Nn No Nq Nr Ns Nt Nu Nv Nw Nx Ny Oe Og Oh Oi Ok Om Pa Pb Pc Pe Pg Po Pz Qa Qb Qc Qd Qe) Og(Fp Fr Hq Hr Hu Hv Hw Hx Ih Ii Ij Ik Il In Io Ip Ir It Iu Iv Jg Jh Jk Jm Jo Jp Jq Js Jt Lh Lu Lv Lw Lx Ly Lz Mc Md Me Mf Mg Mh Mi Mj Mk Ml Mn Mq Mr Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Oh Oi Ok Om Oz Pa Pb Pc Pe Pg Po Pz Qa Qb Qc) Ng(Fr Hq Hr Hu Hv Hw Hx Ih Ii Ij Il In Io Ip Iq It Iu Iv Jg Jh Jk Jo Jp Jq Js Jt Lh Lu Lv Lw Lx Lz Mc Md Me Mf Mg Mh Mi Mj Mk Ml Mn Mq Mr Mt Mu Mv Mw Mx My Mz Na Nb Nc Nd Nf Nh Nk Nl Nm Nn No Nq Nr Ns Nt Nu Nv Nw Nx Oe Of Oh Oi Ok Oz Pa Pc Pd Pe Pg Po Pz Qa Qb Qc) Jq(Fp Hq Hr Hu Hv Hw Hx Ih Ii Ij Ik Il Io Ip Iq Ir It Iu Iv Jh Jk Jm Jo Jp Js Jt Lh Lj Lu Lv Lw Lx Ly Lz Mb Mc Md Me Mh Mi Mj Ml Mn Mq Mr Mt Mw Mx My Mz Nb Nc Nd Ne Nf Nh Ni Nk Nl Nm Nn Nr Ns Nu Nv Nw Nx Ny Oe Of Oh Oi Oz Pa Pb Pc Pd Pe Pf Po Pz Qa Qb Qc Qd Qe) Oi(Et Fr Hq Hu Hv Hw Hx Ih Ii Ik In Ip Ir It Iu Iv Jg Jh Jm Jp Js Jt Lh Lj Lu Lv Lw Lx Lz Mc Md Me Mf Mh Mi Mj Mn Mq Mr Mt Mu Mv Mw Mx My Mz Na Nb Nc Nf Nh Nk Nl Nm Nn No Nq Nr Ns Nt Nu Nv Nw Nx Oe Of Oh Ok Om Oz Pa Pb Pc Pd Pe Pg Po Qa Qb Qc) Lv(Hq Hv Hw Ih Ii Ik Il In Io Ip It Iu Jg Jk Jm Jp Lh Lu Lw Lx Ly Lz Mc Md Me Mf Mh Mi Mj Ml Mq Mr Mt Mu Mv Mx Na Nb Nc Nd Ne Nf Nk Nl Nm Nn No Nq Nr Ns Nt Nu Nv Nw Nx Oe Of Oh Ok Oy Oz Pa Pb Pc Pd Pe Po Pz) Pz(Et Fr Hq Hv Hw Ih Ii Ij Ik In Io Ip Iq Ir It Iu Iv Jh Jk Jm Jp Js Lh Lu Lw Lx Lz Mc Md Me Mh Mi Mj Ml Mq Mr Mt Mu Mw Mx Mz Nb Nd Nf Nn No Nq Nr Nt Nu Nv Nw Ny Oe Oh Ok Om Oz Pa Pc Pe Pg Po Qa Qb Qd Qe) Ip(Hq Hu Hv Hw Hx Ih Ii Ij Ik In Io Iq Iu Jh Jk Jm Jp Lh Lu Lw Lx Ly Lz Md Mg Mh Mi Mj Mq Mr Mt Mu Mw Mx Mz Nb Nc Nd Nf Nk Nl Nm Nn No Nq Nr Ns Nt Nu Nv Nw Ny Oe Of Oh Ok Pa Pc Pe Pg Po Qa Qb) Mh(Fp Fr Hq Hr Hu Hv Hw Ih Il Im In Io Iq It Iu Jh Jk Jm Jp Lj Lu Lw Lx Ly Lz Mc Md Me Mf Mi Mj Ml Mn Mq Mu Mx Ne Ni Nm Nn Nq Nr Ns Nt Nu Nv Ny Oe Of Oh Oy Pa Pc Pg Qa Qc) Lx(Fp Hq Hv Hx Ik Il In Io Iv Jh Jm Jp Lu Lw Lz Mc Md Me Mg Mi Mj Mk Ml Mn Mq Mt Mu Mw Mx My Nb Nc Ne Nf Nh Nk Nl Nr Nt Nu Nx Ny Oe Of Oy Oz Pa Pb Pc Po Qb) Jp(Hq Hu Hv Hw Hx Ii Ij Ik Il In Io Jh Jk Lh Lu Lw Ly Mc Md Me Mg Mi Mj Mq Mt Mu Mx My Mz Nb Nc Nd Ne Nh Nk Nn Nr Ns Nt Nv Nw Nx Oe Of Pa Pe Po Qa Qb Wm) Io(Hq Hv Hw Hx Ih Ii Il Iq Ir Iu Iv Lh Lu Lw Lz Md Mi Mj Mq Mt Mx Mz Nc Nh Nk Nl Nn No Nq Nr Ns Nt Nu Nv Nw Nx Oe Of Oh Ok Pa Pb Pc Pe Pg Po Qa Qb) Mg(Et Fr Hq Hv Hx Ii Ij In Ir Iu Jg Jh Jo Js Jt Lh Lw Md Mi Mj Mr Mt Mu Mv Mw Mz Na Nb Nf Nm Nn Nq Ns Nt Nu Nv Nw Nx Ny Ok Om Pa Pc Pe Pg Po Qa) Lw(Hq Hu Hv Ik Iq Jm Lu Ly Lz Mc Md Me Mf Mi Mj Mn Mq Mr Mt Mu Mv Mx Nb Nd Nk Nl Nm Nr Ns Nu Nx Oe Of Oz Pa Pb Pe Pd Pe Po Qc) Nu(Fr Hu Hv Ih Il In Jh Jk Jm Lu Mc Md Me Mi Mk Mn Mr Mt Mu Mw Nc Nd Ni Nk Nn Nq Nr Nv Nx Oe Of Oh Oy Pa Pb Pc Pg Po Qb) Hq(Hu Hv Ik In Jh Jm Lh Lu Lz Mc Md Mi Mj Mk Ml Mq Mr Mt Mu Mw Mx Mz Na Nb Nc Ne Nf Nk Nq Nr Nw Ny Oe Oz Pa Pb Pc Pe Po) Of(Fr Hv Hw Ih Ii Il It Iu Jh Js Lh Lz Md Me Mi Mj Mq Mr Mu Mx Mz Na Nb Nd Nf Nn No Nq Nr Nt Oe Oh Om Oz Pc Pe Pg Po) Pa(Hr Hv Ii Ik Il It Jm Li Lu Lz Mc Md Me Mi Mj Mk Mn Mq Mt Mu Mw My Nc Ne Nh Nl Nn Nq Nr Ns Nt Oe Oh Oz Pc Qc) Mi(Hu Hv Ik Lu Lz Mc Md Me Mj Mk Ml Mn Mq Mt Mu Mw Mx My Mz Nb Nc Ne Nk Nl Nw Nx Ny Oe Oy Pb Pc Pf Po Qc) Lu(Hu Hv Hw Ii Il In Jh Lh Mf Mq Mr Mt Mu Mw Mx My Mz Nb Nc Nd Nf Nk Nn Nq Ns Nt Nv Oe Pc Pg Po Qa) Mz(Hr Hu Ii Ik In It Jm Jo Lh Lz Mb Me Mk Mn Mt Mw Mx Nc Nf Nk Nl Nt Nx Oe Oh Oy Oz Pd Pf Qc) Oe(Et Fr Ik Iv Jk Jm Lh Lz Mc Md Mj Mq Mr Mt Mu Mx Na Nb Nc Nf Nh Nk No Nr Nt Oz Pc Pg Po) Pc(Hu Ij Ik It Jh Jk Jm Mc Md Me Mf Mj Mn Mq Mt Mu Mw Mx Nn Nq Nr Ny Oh Pb Pe Pf Po Qc) Ik(Hw Ii Ij In Jm Lh Mc Mj Mt Mw Na Nb Nd Nf Nn Nq Nr Ns Nt Ny Oh Pc Pg Po Qa) Mu(Hv Lh Lz Mc Md Mf Mj Mk Mn Mq Mv Mw Mx My Nc Nd Nk Nl Nq Nt Pb Pd Pf Po) Nk(Fr Ii Jh Lh Md Mj Mq Mr Mt Mx Na Nb Ni No Ns Nt Ok Pe Pg Po Qa) Mt(Hu Hv Hx Jm Mc Mj Mw My Nc Nd Nl Ns Nt Ny Oh Pb Pe Pf Qc) Nn(Jm Ly Me Mf Mn My Nc Nd Nl Nq Nt Oh Oy Pe Pf Pg Qb Qc) Po(Hr Il Jh Jm Jo Mc Me Mk Ml Mn My Nl Nx Ny Pd Pf Qc) Nc(Fr Hv Hw Ij Il Im In Jk Jm Mq Mx Nq Ns Pe Pg Qa) Jo(Hv Hw Ii Ij Ir Lh Mr Nb No Nr Nt Ok Om Pe Pg Qa) Mw(Hu Hv In Jm Mc Md Mj Mr Mv My Nb Nd Ny Pb Pe) Nl(Hw Ii Ij In Jm Mc Md Ml Mx Nd Ne Oh Pg Qc) Pd(Hv Ij In It Jh Lh Md Mj Mq Mr Nb Nf Nr Pe) Nt(Hv Hx Ii Iu Jm Nm Nv Nw Nx Oh Pb Qa Qc) Pb(Hv Hw Ij In Lh Mj Ml Mq Mr Ny Pe Pg) Md(Jm Mc Ml Mn Mq My Nd Nh Nx Pf Qc) Nb(Hr Ii Mk Ml Mn My Nd Nq Nx Oh Oz) Nw(Hv Hw In Jk Lh Mj Mk Ne Nh Pe Pf) Pe(Ii Mj Mk Nm Ns Nx Oh Oz Qc) Jm(In Lz Mj Mx Nd Nq Oh Pg) Qc(Lh Lz Mj Mx Nv Oh Pg) Mk(Ii Lh Mj Mq Mr Nr) Hv(Hr Mb Mc Ml Ni Oh) Oy(Ii Ij Jk Lz Mj Oh) ln(Hr Hw Ly Mb Nx) Pg(Im Na Nx Ok Oz) Ns(Hu Lh Ne Ny) Nq(Hx Ly Mn) Mr(My Oz Pf) Hr(Hw Ii Nr) Hu(Na No Ok) Nm(Lh Qa) Mc(Mj Mq) Mn(Jh Lh) Mx(Mf Ml) Nd(Jh Ny) Nx(Ii Nv) NrOz MbHw MeOh Mjll NfPf lrIu} aA{Nj(Et Fp Fr Hq Hr Hu Hv Hw Hx Ih Ii Ij Ik Il Im In Io Ip Iq Ir It Iu Iv Jg Jh Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Ip(Et Fp Fr Hq Hr Hu Hv Hw Hx Ih Ii Ij Ik Il Im In Io Iq Ir It Iu Iv Jg Jh Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Nn(Fp Fr Hq Hr Hu Hv Hw Hx Ih Ii Ij Ik Il Im In Io Iq Ir It Iu Iv Jg Jh Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nk Nl Nm No Nq Nr Ns Nt Nu Nv Nw Nx Ny Oe Of Og Oh Oi Ok Oy Oz Pa Pb Pc Pd Pe Pf Pg Po Pz Qa Qb Qc Qe Wm) Pg(Et Fp Fr Hq Hr Hu Hv Hw Hx Ih Ii Ij Ik Il Im In Io Ir It Iu Iv Jg Jh Jk Jm Jn Jo Jp Jq Js Jt Lh Li Lj Lu Lv Lw Lx Ly Lz Ma Mc Md Me Mf Mg Mh Mi Mj Mk Ml Mm Mn Mq Mr Ms Mt Mu Mv Mw Mx My Mz Na Nb Nc Nd Nf Ng Ni Nk Nl Nm No Nq Nr Ns Nt Nu Nv Nw Nx Ny Oe Of Og Oh Oi Ok Oy Oz Pa Pb Pc Pd Pe Pf Pz Qa Qb Qc Qd Qe) Mu(Hq Hr Hu Hv Hw Hx Ih Ii Ij Il In Io It Iu Jh Jk Jm Jn Jp Jq Js Lh Li Lu Lv Lw Lx Ly Lz Ma Mb Mc Md Me Mh Mi Mj Mk Ml Mq Mr Ms Mt Mv Mw Mx My Mz Na Nb Nc Nd Ne Nf Ng Nh Ni Nk Nl Nm No Nq Nr Ns Nt Nu Nv Nx Ny Oe Of Og Oh Oi Ok Ov Oz Pa Pb Pc Pe Pf Pz Qa Qc) bC(aC aD aE aF aG aH aI aJ aK aL aM aN aO aP aQ aR aS aU aV aW aX aY aZ bA bB bE bF bG bH bI bJ bL bM bN bO bP bQ bR bS bU bV bW bX bZ cA cB cC cD cE cF cG cH cI cJ cK cL cM cN cO cP cQ cR cS cT cU cV cW cX cY cZ dA dB dC dD dE dF dG dH dI dJ dK dL dM) cU(aC aD aE aF aG aH aI aJ aK aL aM aN aO aP aQ aR aS aU aV aW aX aY aZ bA bB bE bF bG bH bI bJ bL bM bN bO bP bQ bR bS bU bV bW bX bZ cA cB cC cD cE cF cG cH cI cJ cK cL cM cN cO cQ cR cS cT cV cW cX cY cZ dA dB dC dD dE dF dG dH dI dJ dK dL dM) bW(aC aD aE aF aG aH aI aJ aK aL aM aN aO aP aQ aS aU aV aW aX aY aZ bA bB bE bF bG bH bI bJ bL bM bN bO bP bQ bR bS bU bV bX bZ cA cC cD cE cF cG cH cI cJ cK cL cM cN cO cQ cR cS cT cV cW cX cY cZ dA dB dC dD dE dF dG dH dI dJ dK dL dM) cJ(aC aD aE aF aG aH aI aJ aK aL aM aN aO aP aQ aR aS aU aV aW aX aY aZ bB bE bF bG bH bI bJ bL bM bN bO bP bQ bR bS bU bV bX bZ cA cB cC cD cE cF cG cH cI cK cL cM cN cO cQ cR cS cV cW cX cY cZ dA dB dC dD dE dF dG dH dI dJ dK dL) Nq(Fr Hq Hr Hu Hv Hw Hx Ii Ik In Io It Iu Jg Jh Jm Jn Jp Jq Lh Li Lu Lv Lw Lx Ly Lz Mb Mc Me Mf Mh Mi Mj Mk Ml Mq Mr Mt Mv Mw Mx My Mz Nb Nc Nd Ne Nf Ng Nk Nl Nm Nr Ns Nu Nx Oe Of Og Oh Oi Ok Oy Oz Pa Pb Pc Pf Pz Qa Qb Qc) Lv(Et Fp Fr Hq Hr Hu Hv Hw Hx Ih Ij Io Iu Iv Jg Jh Jk Jn Jp Jq Js Lh Li Lj Lw Lx Ma Mc Me Mf Mg Mh Mi Mk Ml Mm Mq Mr Mt Mv Mw Nc Nd Ni Nk Nl Nm Nr Ns Nt Nu Nw Ny Oe Og Oh Ok Oz Pa Pb Pc Pf Po

Om(Et Fp Hq Hu Hv Hw Hx Ih Ii Ij Il Im In Io Ip Iq Ir Iu Iv Jg Jh Jk Jn Jo Jp Jq Js Jt Lh Li Lj Lu Lv Lw Ly Lz Ma Mb Mg Mh Mi Mj Mk Ml Mm Mq Mr Ms Mt Mv Mx My Mz Na Nb Nc Nd Ne Ng Nh Ni Nk Nl Nm Nn No Nq Nr Ns Nt Nu Nv Nw Ny Of Oh Oi Ok Pa Pb Pc Pe Pg Po Pz Qa Qb Qc Qd Qe Wm) Po(Et Fp Hq Hr Hu Hv Hw Hx Ih Ii Ik Il In Io Ip Iq Iu Jg Jh Jm Jn Jp Jq Lh Li Lj Lu Lv Lw Ly Lz Ma Mc Md Me Mf Mg Mh Mi Mj Mk Ml Mm Mn Mq Mr Ms Mt Mv Mx My Mz Na Nb Nc Ne Ng Nh Ni Nk Nl Nm Nn Nq Nr Ns Nt Nu Nv Nw Nx Ny Oe Of Oh Oi Ok Oy Pa Pc Pd Pe Pf Pg Pz Qa Qb Qc Wm) Nt(Et Fp Hq Hu Hv Hw Hx Ii Ij Ik Im In Io Ip Ir It Jg Jh Jk Jn Jo Jp Jq Lh Lj Lv Lw Ly Lz Ma Mb Mc Me Mf Mg Mh Mi Mj Mk Ml Mm Mn Mr Ms Mt Mv Mx Mz Na Nb Nc Nd Ne Ng Nk Nl Nm Nn No Nq Nr Ns Nu Nw Nx Ny Of Oh Oi Ok Oy Oz Pa Pb Pc Pe Pg Pz Qa Qb Qe) Jg(Hu Hv Hx Ii Ij Il In Io Ip Ir Iu Jh Jk Jn Jo Jp Jq Lh Li Lu Lv Lw Ly Md Mh Mi Mj Ml Mq Mr Ms Mt Mv Mx Mz Nb Nc Nd Ne Ng Nh Nk Nm Nn No Nq Nr Nu Nv Nw Ny Of Oi Ok Oz Pa Pe Pg Pz Qa Qb Qe) Nn(Et Hr Hu Hv Hw Hx Ii Ij Il In Ip Ir It Iu Iv Jh Jn Jp Jq Jt Lh Lu Lv Lw Lz Md Mf Mi Mj Mk Ml Mq Mr Mt Mx Mz Na Nb Nf Nl No Nr Ns Nu Nv Nw Nx Ny Of Oi Ok Oz Pa Pb Pe Pg Qa Qd Qe) Jh(Et Hw Hx Ih Ii Il Ip Ir Iu Iv Jk Jn Jo Jp Jt Lh Lv Lw Lz Mh Mi Mj Mq Mr Mt Mv Mx Mz Nb Nd Ni Nk Nl No Nq Nr Nu Nv Nw Nx Oh Ok Oz Pa Pc Pe Pg Qa Qb Qe) Mt(Et Hw Hx Ii Il Ip Ir Iu Iv Jk Jn Jo Jp Jt Lh Li Lv Lw Me Mi Mj Ml Mm Mq Mr My Nb Nc Nk No Nq Nr Nv Nw Ny Ok Oz Pa Pb Pc Pe Pg Qa Qb Qe) Nq(Hr Hu Hv Hw Hx Ih Ii Il In Ip Iq Ir Iu Jn Jp Jq Lh Lu Lv Mi Mj Mq Mr Mx Mz Na Nb No Nr Nu Nv Nw Nx Ny Ok Oz Pa Pe Qa Qb) Ip(Et Hw Hx Ii Il Ir Iu Iv Jk Jn Jp Jq Jt Lh Lv Lz Ma Mh Mi Mj Mr Mv Mx Mz Nb No Nr Nv Nw Ok Oz Pa Pc Pe Pg Qa Qd Qe) Qa(Et Ih Ii Il It Iu Jk Jn Jp Jq Lh Ma Me Mg Mi Ml Mm Mr Nb Nc Nd Ni Nk No Nu Nv Nw Oh Ok Oz Pa Pc Pe Pz Qe) Et(Hu Hw Hx Ii Ij Il In Jk Jn Jq Lh Lv Lw Ly Mh Mi Mm Mr Ms Mv Mz Nb Ng Nk Nr Pa Pe Pg Pz Qb Qe) Nw(Fp Hv Hw Hx Ii Ij Il In Io Iu Jk Jn Lh Lv Lw Mf Mg Mi Mj Mq Mv Nm Nu Nv Ok Pe Pg Pz Qb Qe) Jk(Hu Hx Ih Ir Iv Jn Jp Jq Jt Lh Lv Lw Ma Mf Mg Mi Mz Nb Nm No Oh Ok Pe Pz Qe) Jn(Hw Hx Ii Il Iu Jp Lh Lv Ma Mg Mi Mm Mr Mv Mz Nb Nm No Nv Ok Pa Pc Pe Pg) Nm(Hw Hx Ii Il Iu Lh Lz Mi Mr Mx Mz No Nr Nv Ok Oz Pa Pe) Mm(Hu Hw Hx Ii Ij In Ir Jq Lh Lv Mr Mz Nb Nr Nv Pa Pe Pg) Mv(Hw Hx Ii Iu Jq Lh Mi Mr Nb No Nr Nv Ok Oz Pa Pe Qe) Lw(Hw Hx Ii Il Iu Lh Mi Mr Mz Nb No Nr Nv Ok Pa Pe) Lv(Hw Ii Iu Jp Jq Lh Ma Mi Mj Mx No Nv Oh Ok Pa) Ok(Hu Hx Il In Iu Mf Mg Ms Nk Nu Oe Pe Pg) Mi(Ii Io Jp Jq Ma Mf Mk Mn Nk No Oh Pa) Ma(Hw Hx Ii Ir Lh Mr Nb Nr Pa Pe) Pe(Im Io Jp Me Mg Pb Pc Pf Pz) Mf(Ii Lh Mr Mz No Nr Nv Pa) Mg(Ii Lh Mz Nb No Nv Pa) Jp(Hw Hx Ii Lh Pa Pg Wm) Io(Hw Lh Nb No Nv Pg) Im(Ii Lh Nb Pa Pg) Pc(Hx Lh Nb Nr) Jq(Hw Hx Pg) NoHu NuNv MeNb PzPg) Mu{Oi(Fp Fr Hq Hr Hu Hv Hw Hx Ih Ii Ij Ik Il In Io Ip Iq Ir It Iu Iv Jg Jh Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mq Mr Ms Mt Mv Mw Mx My Mz Na Nb Nc Nd Ne Nf Ng Nh Ni Nk Nl Nm Nn No Nq Nr Ns Nt Nu Nv Nw Nx Ny Oe Of Oh Ok Om Oy Oz Pa Pb Pc Pd Pe Pf Pg Po Pz Qa Qb Qc Qd Qe) Jn(Fp Fr Hq Hr Hu Hv Hw Hx Ih Ii Ij Ik Il Im In Io Ip Iq It Iu Iv Jg Jh Jk Jm Jo Jp Jq Js Lh Li Lj Lu Lv Lw Lx Ly Lz Mb Mc Md Me Mf Mg Mh Mi Mj Mk Ml Mn Mq Mr Ms Mt Mv Mw Mx My Mz Na Nb Nc Nd Ne Nf Ng Nh Ni Nk Nl Nm Nn No Nq Nr Ns Nt Nu Nv Nw Nx Ny Oe Of Oh Oy Oz Pa Pb Pc Pd Pe Pf Pg Po Pz Qa Qb Qc Qe) Nk(Fr Hq Hr Hu Hv Hw Hx Ih Ii Ij Ik Il Im In Io Ip It Iu Jh Jk Jm Jo Jp Jq Js Lh Lu Lv Lw Lx Lz Mb Mc Md Me Mf Mg Mh Mi Mj Mk Ml Mn Mq Mr Ms Mt Mv Mw Mx My Mz Na Nb Nc Nd Ne Nf Ng Nh Ni Nl Nm Nn Nq Nr Ns Nt Nu Nv Nw Nx Ny Oe Of Oh Ok Oy Oz Pa Pb Pc Pe Pf Pg Po Pz Qa Qb Wm) Pz(Et Fp Fr Hq Hu Hv Hw Hx Ih Ii Ij Il Im In Ip Ir It Iu Iv Jh Jk Jp Jq Js Jt Lh Li Lj Lv Lw Lx Lz Ma Mb Mh Mi Mj Mk Mn Mq Mr Mt Mw Mx My Mz Nb Nc Nd Ne Nf Ng Nh Ni Nm Nn No Nq Nr Ns Nt Nv Nw Nx Ny Oh Ok Om Oy Pa Pc Pe Pf Pg Po Qa Qb Qd Qe Wm) Lv(Fr Hq Hr Hu Hv Hw Hx Ii Ij Ik Il Im In Io Ip Iu Jg Jh Jk Jm Jo Jp Jq Js Lh Lu Lw Lx Ly Lz Ma Mc Md Me Mf Mg Mh Mi Mj Mk Ml Mn Mq Mr Ms Mt Mv Mx My Na Nc Nd Ne Nf Ng Nh Ni Nl Nm Nn Nr Ns Nv Nw Ny Oe Of Oh Ok Oy Oz Pa Pb Pc Pg Po Qc Wm) Mg(Et Fp Fr Hq Hv Hw Hx Ii Ij Il In Ip Ir It Iu Iv Jg Jk Jo Jp Js Jt Lh Lu Lw Lx Lz Ma Mb Mc Md Me Mf Mh Mi Mj Mk Ml Mn Mq Mr Mt Mv Mw Mx My Mz Na Nb Nc Nd Ne Nf Ng Nh Ni Nl Nm Nn Nq Nr Ns Nt Nu Nv Nw Nx Ny Oe Oh Ok Om Oz Pa Pc Pe Pf Pg Po Qa Qb Wm) Ng(Fr Hr Hv Hw Hx Ih Ii Il In Io Ip It Iu Iv Jh Jk Jm Jo Jp Jq Js Lh Lu Lw Lx Lz Ma Mc Md Me Mf Mh Mi Mj Mk Mq Mr Ms Mt Mv Mw Mx Mz Na Nb Nc Nd Nh Ni Nl Nn No Nq Nr Ns Nt Nu Nv Ny Oe Of Oh Ok Oy Oz Pa Pb Pe Pf Pg Po Qa Qb Wm) Pg(Hq Hr Hu Hv Hw Hx Ii Ij Ik Il Im In Io Ip Jk Jm Jo Jp Jq Lh Lu Lw Lx Ly Mc Md Mf Mh Mj Mk Ml Mn Mq Mr Ms Mt Mv Mw Mx My Mz Na Nb Nc Nd Nf Nl Nq Nr Ns Nu Nv Nx Ny Oe Of Oh Oy Oz Pa Pb Pc Pd Pf Qc) Ip(Hw Hx Ii Ij Ik Il In Io Ir Jk Jm Jp Jq Lh Lu Lx Mb Mh Mj Ms Mt Mw Mx Mz Nb Nc Nd Ne Ni Nm Nn Nr Nw Nx Oe Of Oz Pa Pb Pe Po Qa Qb) Oe(Hv Hw Hx Ii In Io It Jp Js Lh Lu Lx Mf Mh Mi Mj Mk Ms Mt Mw Mx Mz Nb Nc Nd Ne Nh Ni Nr Nt Nu Nv Nx Ny Of Pa Pe Po Qa Qb) Mh(Fp Hv Hw Hx Ij Il Im In Io Iq It Iu Jk Jp Jq Js Lj Lu Mb Me Mj Mn Ms Mw Mx Nc Nd Ne Nh Nn Nr Nu Nv Nx Qa Qb Qc) Nd(Hq Hu Hv Hw Ii Ij Io Jh Lu Lw Lz Mc Md Mi Mk Mq Mr Mt Mv My Nc Nl Nn Nq Ns Ny Of Oh Oy Pa Pc) Ms(Hv Hw Hx Ik Io Ir Jp Jq Js Lh Lj Lw Lx Mb Mj Mr Mt Mw Nb Ni Nn Nq Nr Nu Nw Ok Oy Pa Po Qa) Io(Hw Hx Ii Ij Il In Ir Jp Lh Lx Mj Mt Mx Mz Nc Ni Nw Pa Pe Qa Qb) Lu(Hw Hx Ii Ij Il In Jp Jq Lh Lx Mj Mt Mw Mx Mz Nc Nr Pa) Ni(Hv Hw Ij Im In Jm Jq Lw Me Mq Mz Nf Nr Nu Oy Qa) Pa(Hr Ii Il Jk Jm Jo Jp Jq Mk My Nc Nl Nu Oy Oz Pf) Qc(Ii Iu Jq Lh Lz Mi Mj Mr Mt Mz Nb Nf Nn Nr Oh) Jp(Hw Hx Ij Il In Jq Mx Mz Nc Ne Nh Qa Wm) Of(Hv Ii Ir Js Lh Ma Mj Mw Nr Ny Qa Wm) Nc(Hw Ij Il In Mx Ne Nh Pe Qa Qb Wm) Nl(Hw Ii Ij Il In Jk Mj Mx Mz Ne Nr) Hr(Hw Ii Ij Il In Lx Mj Mx Mz Nr Po) Jo(Hw Ir Jq Js Lh Mi Pe Po Qa Wm) Jm(Hw Ii Ij Il In Mx Mz Qa Wm) Nr(Hq Il Jk Mk Ml Mv My Ny) Ik(Jq Lh Mt Ne Pe Qa Qb Wm) Pb(Mt Mx Ne Nh Ny Pe Qa) Nu(Hw Ii Ij Jq Oh Wm) Mj(Hq It Mf Ml Mv My) Hv(Jq Mf Ml Mv My) Pf(Jq Lh Pe Qa Wm) Mw(Hq Mc Mv My) In(Hw It Me Oy) Oz(Ne Nh Pe Qa) Pd(Lw Lx Lz Mi) Mm(Et Fr Wm) Mt(Hq My Ny) Mx(Hq My Oy) Ij(It Me Pc) Nn(Ly Pc) Lx(Hq Mn) Nh(Jq Nw) Nx(Pe Wm) NmLw LyOh NeNw HwIt HxJq IiPe JkOy LhNv} Nn{Oi(Et Fp Fr Hq Hr Hu Hv Hw Hx Ih Ii Ij Ik Il Im In Io Ip Iq Ir It Iu Iv Jg Jh Jk Jm Jn Jo Jp Jq Js Jt Lh Li Lj Lu Lv Lw Lx Ly Lz Ma Mb Mc Md Me Mf Mg Mh Mi Mj Mk Ml Mm Mn Mq Mr Ms Mt Mv Mw Mx My Mz Na Nb Nc Nd Ne Nf Ng Nh Ni Nk Nl Nm No Nq Nr Ns Nt Nu Nv Nw Nx Ny Oe Of Oh Ok Om Oy Oz Pa Pb Pc Pd Pe Pf Pg Po Pz Qa Qb Qc Qd Qe) Jn(Fp Fr Hq Hr Hu Hv Hw Hx Ih Ii Ij Ik Il Im In Io Ip Iq It Iu Jg Jh Jk Jm Jp Jq Js Lh Li Lj Lu Lv Lw Lx Ly Lz Ma Mb Mc Md Me Mf Mg Mh Mi Mj Mk Ml Mm Mn Mq Mr Ms Mt Mv Mw Mx My Mz Na Nb Nc Nd Ne Nf Ng Nh Nk Nl Nm No Nq Nr Ns Nu Nv Nw Nx Ny Oe Of Oh Ok Oy Oz Pa Pb Pc Pe Pf Pg Po Pz Qa Qb Qc Qe) Lv(Fr Hu Hv Hw Ii Ij Ik Il In Io Ip It Iu Jm Jp Jq Lh Lu Lw Lx Ly Lz Ma Mb Mc Md Mf Mg Mh Mi Mj Mk Ml Mm Mn Mq Mr Mt Mv Mw Mx My Na Nc Nd Ne Nf Ng Nh Nk Nl Nm No Nq Nr Ns Nv Nw Nx Of Oh Ok Oy Oz Pa Pb Pe Pf Po Pz Qc Wm) Ng(Fr Hr Hu Hv Hw Ii Il In Ip It Iu Jp Jq Js Lh Lu Lw Lx Md Mf Mi Mj Mk Ml Mr Mv Mw Mx Mz Na Nb Nd No Nq Nr Nt Nu Nv Of Ok Pa Pe Pg Po Qa) Pz(Et Fr Hu Hw Hx Ii Ij Il Im Ip Ir Iu Jg Jk Jp Jq Lh Lx Ma Mj Mk Mq Mt Mw Mx Mz Nb Nl No Nr Nt Nv Nw Ok Om Pa Pe Pg Po Qa Qb Qd Qe) Jp(Hw Ii Ij Il In Io Ip Jq Lu Lx Ly Mf Mg Mh Mj Mm Mn Ms Mt Mx My Mz Nb Nc Nd Ne Nh Nk Nr Ns Oh Pa Pc Pe Pg Po Qa Qb Qc Wm) Jq(Fp Hv Hw Hx Ii Ij Il In Io Ip Ir Jk Lu Lx Ly Mf Mh Ms Mt Mw Mz Nd Ne Nh Ni Nk Nm Nr Nu Nx Oe Of Oh Pa Pe Po Qa Qb Qe) Io(Hu Hv Hw Hx Ih Ii Il In Ip Ir Iu Lh Lx Mf Mi Mj Mk Mq Mr Mt Mx Mz Nb Nl No Nr Nt Nv Nw Ok Oz Pa Pc Pg Po Qa Qb) Mg(Et Fr Hu Hv Hw Hx Ii In Ip Ir Iu Jo Js Lh Lw Lx Mf Mi Mq Mr Mt Mv Mz Nb Nt Nv Nw Nx Ok Om Pa Pe Pg Po Qa) Ms(Fp Fr Hv Hw Hx Ij Ip Ir Lx Ma Mb Mh Mi Mj Mq Mr Mt Mw Mx Mz Na Nb Nd No Nr Nw Oh Ok Pa Pb Pe Pf Po Qa) Ip(Hu Hw Hx Ii Ij Il In Lu Lx Ly Me Mf Mh Mm Mt Mw Mx Mz Na Nb Nc Nd No Nr Nw Of Pa Pc Pe Pg Po Qa Qb) Pe(Hr Ik Il It Jg Jm Jo Jt Lu Ly Mb Mf Mj Mk Ml Mm Mn Mv Mx My Nb Nc Nq Nu Nv Nw Of Oz Pc Pf Po Qc) Qc(Hu Hv Ii Ij In It Lh Lw Lx Lz Md Mf Ml Mq Mr Mt Mw Mx Mz Nb Nr Nv Nw Ny Oh Pa Po Qa) Nd(Hu Ij Ik Jh Lu Lw Lx Mc Mf Mv Mw My Nl Ny Of Oh Oy Pa Pb Pf) Pc(Hw Ii Il Iu Lh Lx Lz Mi Mj Mq Mr Mx Mz

Figure 42 Continued

Qa) Pg(Ik Jm Jp Jq Lu Mh Ms Nc Ng Nm Nx Of Oz Pb) Pe(Ik Iu Lu Ms Nc Ng Nk Nm Of Oh Pb Pc Pf) Ms(In Jq Mi Mz Nb Ok Qa) Hu(In Jq Ng Qa) Nk(In Jq Mz) Qa(Jt Mh Of) Lh(Jt Ng Of) Nw(Lw Mi Pc) In(Lu Nc) NtNg MhJk} bA{bW(aC aE aI aK aM aQ aU aX aY aZ bB bC bE bG bH bJ bM bN bO bP bQ bV bX cA cC cD cE cF cG cL cO cQ cR cT cW cY cZ dB dC dD dE dG dH dI dK) cF(aM aX bC bE bF bH bJ bL bO bQ bV bZ cB cD cE cG cK cL cM cR cS cT cU dB dD dE dI dK) bC(aZ bE dE dK) cU(aZ bE dD dE) cC(cS dE dI) aI(bE bJ) aZcS} Qa{Ik(Iu Jg Jk Jp Jq Lu Ma Mg Mh Mi Mv Nc No Nv Nw Ok Pa Pb Po) Jp(It Jq Lu Lw Mh Mi Ms Nc Of Pb Pc Qc) Jq(Hv Lu Ml Ms Ng Ni Nk Nu Of Qc) Mh(Im It Jh Lw Ml Ng Ok Pb) Pb(Jt Jh Ml Ms Nc Of) Et(Ms Ng Nk Of) Ma(Mg Ng Nm Of) Nw(Lu Ms Nm Qc) Ii(No Pg) Im(Nc Nk) Jt(Mi Pc) Of(Ml Ok) NtNg MsOk} Pg{Ii(Et Hw Jg Jq Jt Lh Mr Mz Na Nb Nf No Nt Nw Ok Om Pe) Et(Ik Lu Mg Mh Ms Ng Nk Nm Nv Nx Oe Of Pb Pf) Im(Jp Jq Lh Mh Mr Nc No Nw Pc Pe Po) Mg(Jg Jp Ma Mi Nt Ok Om) Nx(Jp Jq Nw Ok Om) Ng(Jg Jp Ma) Of(Ma Ok Om) Ik(Mi Qd) Jh(My Oy) NvNw} Mg{Nt(Et Jg Jh Jp Lh Lw Ma Mi Mn Mv Nm Nw Oh Om Pc) Et(Il In Lh Mh Nk Oe Pa Pe Po) Om(Hw Iu Lh Mh Mi Nk Nv Pa Pe) Ma(Hw Hx Ii Jk Lh Nb Pe Po) Po(Lw Mf Ng Pc) Mi(Jg Jh Me Mn) Iu(Jg Lw) Jq(Ms Nk) Pe(Jg Ng)} Jq{Jk(Fp Hq Hv Ii Ik Jm Jp Lu Ma Mh Ms Nu Nw Nx Of Oy Qc) Po(Hr Hv Il Jm Jp Ml Of Pb Pc) Ms(Hv Ma Nt Nw Ok Pc) Nt(Jt Nd Of Qc) Nk(Hv Iu Nw) Pa(Jg Jp Ma) Pe(Jp Ml Pc) Hw(Of Pc) NuHv NdOe IuOf} Of{Po(Hr Ik Jh Jm Jp Lj Lz Ml Ms Nd Om) Et(Ij Il In Jk Nk Pa Pe) Om(Ii Jk Lh Nd Nk Pa Pe) Jh(Ii Lh Nr Pe) Pe(Jp Nw Oh) Ma(Lh Mi) InNw} bV{dK(aM aQ aU bL bM bQ bS cK cY dD dE) bW(aK cF cR cY) cK(aI cS cU dD) aM(aY bE cS) cC(aI bF dE) cM(cR cU) aZcU bEdD bLcR cScY} Ng{Jh(Ii Iu Jk Lh Lz Md Mi No Nt Nv) Ma(Hw Ii Jk Lh Nt Pe Po) Nt(Jp Lw Me Pc) Et(Mh Nk Pa) Mi(Hr Jk) Om(Mh Pa) PoNm LwIu} Pe{Oh(Il In Ly Ml Nl Nr Oy) Pf(Et Jg Lw Ma Nw Om Pc) Et(Ik Nk Nm) Ma(Ik Mb) Jp(Lw Pc) Nw(Mh My) Om(Ik Nd) IiJg JhOy} cF{cS(aI aM bG bM bQ cK cQ cT cU dA dD dF dM) dK(cU dA dF dG dM) bW(aF cT dM)} Et{Nk(Im In Jk Ms Nd Ne Nh Oe Pa) Ms(Jk Mi Nd) Ne(Mh Nc Nl) Nh(Mh Nc) Jk(Hu Oe) OePa} Po{Hr(Lw Mh Ml My Ny Oh) My(Jm Lj Ml Pd) Oy(In Lz Ml) Jm(Ml Oh) MkLj IkQd QcOh JpOe} Pa{Jh(Hr Ik Jm Jp Ly) Jp(Lw Mq Nm Pc) Nm(Ik Jm) Mi(Hr Il) LuJg LwJm OmPb} dM{dK(aI aX bX cD cM cU dB dD) aI(aX bE bW cS) dD(aX bE cS) bOcS} Lw{Hv(Mf Ml Nd Nm) MiPd MsOk MxHu NdJh IkQd IlJp} Jp{Jk(Mi Mq Ms Oe) Mi(Ms Nh) Qd(Ik Im) NtNh} Nd{Jh(Hu Mi My Ns) Om(Fp Hq Ns)} Ms{Ok(Hr Mf Ml) Ma(Mi Mz) JkNw} Qd{Ik(Jk Nm No Ok) Im(Nc Nk)} Nw{In(Ml Nm Pb) MiQc MlHw} aM{aIdI aLbE aXbF cSdD cUdE} dK{dD(bS dA) bGcU bQcE} Im{Nk(Lh No) NcJk} aI{bQcE cCdI cKcU} cS{cK(aL dD) bQcL} Jh{NsNi MiQc} Oh{MlHv NlIj} aYcUdG

Unconstrained panels with 3 analytes, where 3.3E-8 >= 'AUC p-value' > 1.0E-8. Contains 12,486 panels of 397,580 total panels evaluated. : Is{Ne(Fp Hq Hu Hv Hw Hx Ih Ii Ij Il In Iq Ir It Iu Iv Jk Jn Jq Js Lj Ly Mc Md Mf Mj Mk Mn Mq Mr Mv Mz Na Nb Nf Ng Nh Ni Nm No Nr Ns Nu Nv Ny Oh Ok Oy Pd Pe Pf Pg Po Qb Qc Qe) Mw(Et Fp Hq Hv Hw Hx Ih Ii Ij Il Im In Iq Ir It Iu Iv Jh Jn Js Lh Lj Ly Mc Me Mf Mg Mi Mn Mq Mz Na Nb Nd Nh Ni Nl Nm No Nt Nu Nw Ny Oh Ok Om On Oz Pd Pe Pg Po Qa Qb Qe) Hu(aA Fp Hq Hv Hw Hx Ih Ii Ij Il In Iq Ir It Iu Iv Jg Jn Jq Lh Li Lj Ly Mc Mf Mi Mk Mn Mr Mx My Mz Nb Nc Nd Nh Nl Nm No Ns Nt Nu Nv Nw Ny Oh Ok Oy Oz Pe Qa Qb Qc Qd Qe) Qb(Hq Hv Hw Hx Ih Ii Ij Il Im In It Iu Iv Jm Jq Lj Lu Ly Ma Mc Me Mf Mg Mi Mj Mk Ml Mn Mt My Mz Nb Nc Nd Ng Nh Nl Nm Ns Nt Nu Nv Nw Ny Oh Oy Pe Pf Po Qa Qc Qe) Lh(Hv Hw Hx Ih Ij Ik Il In Iq Ir Iv Jh Jk Jq Js Lj Lu Lx Ly Lz Mc Mf Mi Mk Mm Mq Mr Mt Mv Mx My Mz Na Nb Nc Nr Ns Nt Nv Ny Oh Ok Oy Pa Pb Pe Pf Pg Po Qa Qc Qe) Nd(Et Fp Hq Hv Hw Hx Ih Ij Im In Iq Ir It Iv Jk Jn Js Lj Mc Md Me Mf Mi Mk Ml Mn Mq Mr Mx My Mz Nb Nc Ng Ni Nl Nm No Nv Ny Oh Ok Oy Oz Pb Pd Pf Qa Qc Qe) Ns(Fp Hq Hv Hw Hx Ih Ii Ij Il In Iq Ir Iv Jn Js Lj Ly Mc Md Mf Mi Mk Mn Mq Mr My Mz Na Nb Ng Nh Ni Nl Nm No Nr Nv Nw Ny Oh Ok Pd Pe Pf Qa Qc Qd Qe) Oy(Hv Hw Hx Ih Ii Ij Il Im In Iq It Iu Iv Jg Jm Jn Jq Js Lj Lu Ly Mc Mf Mk Mn Mq Mr Mz Na Nh Nl Nm No Nr Nt Nu Nv Nw Nx Ny Oh Ok Oz Pe Pf Qa Qc Qe) Mg(aA Et Fp Hv Ih Ij Il Im In Iq Ir Iv Jh Jn Js Li Lj Ly Mb Mc Md Me Mf Mk Ml Mn Mr Mv Mx Na Nb Nf Ni Nl No Nu Nv Ny Oh Ok Oz Pd Pe Pf Qa Qd Qe) Nt(aA Fp Hv Hw Ih Ij Im In Iq Ir Iv Jh Jq Js Li Ma Mc Mf Mh Mi Mk Mm Mn Mq Mr Mt Mu Mx Mz Na Nb Nc Nr Nu Nw Ny Oh Ok Om Pd Pe Pf Po Qa Qe) Il(Fp Hq Hv Hw Hx Ih Ii Ij Im In Iq It Iu Iv Jh Jn Jq Js Lj Lu Ly Mc Mf Mi Mk Mn My Mz Nb Nc Ng Nh Nl Nm Nu Nw Ny Oh Ok Om Pf Po Qa Qc Qe) My(Fp Hq Hv Hw Hx Ih Ii Ij Im In Iq Iv Jg Jn Jq Js Lj Lu Ly Mc Mf Mk Mn Mq Mr Mz Na Nc Ng Nh Nl Nm No Nu Nv Nw Ny Oh Ok Pe Qa Qc Qe) Jh(aA Fp Hq Hv Hx Ih Ij Iq Ir Iu Iv Jn Js Lj Lu Ly Mc Mf Mk Mn Mq Mr Mv Mx Mz Na Nb Nf Nh Ni Nl Nm No Nu Nw Ny Ok Om Pd Pf Qa Qe) Im(Fp Hq Hv Hw Hx Ih Ii Ij Iq Ir Iu Iv Jn Js Jt Lj Ly Mb Mc Md Mi Mj Mk Mn Mq Mr Mx Mz Na Nf Nh Ni Nl Nm No Nr Nv Ny Pf Qa Qe) Mi(Hv Hw Hx Ih Ij In Iq Ir Iv Jk Jm Jn Js Lz Mc Mf Mk Ml Mn Mr Mt Mv Mz Nb Nm Nv Nw Ny Oh Ok Oz Pa Pb Pd Pe Pf Po Qa Qe) Nl(Hq Hw Hx Ih Ii In Iq It Iu Jn Jq Lu Ly Ma Mc Me Mf Mk Ml Mr Mt Nb Nh Nm No Nr Nu Nv Nx Ny Oh Ok Om Oz Pe Pf Qa Qc Qe) Mj(Fp Hq Hv Ih Ij Iq Ir It Jn Jt Ly Lz Mc Md Me Mf Mn Mq Mv Mx Mz Na Nf Ng Ni Nu Nv Nw Nx Ny Ok Om Oz Pb Pd Pf Qa Qc) Ng(aA Fp Hq Hv Hx Ii Ij In Iq It Jg Jo Js Jt Li Lj Ly Lz Mc Mk Mn Mr Mz Nb Nf No Nr Nv Nw Ny Oh Ok Pd Pe Pf Qa Qe) Hw(Fp Hq Hv Hx Ih Ij Iq Ir Iv Jk Jq Mb Mc Me Mf Mh Mk Mm Mn Mt Mv Mz Nc Nh Ni Nm Ny Oh Oz Pa Pd Pe Pf Pg Po Qc Qe) Qc(Et Fp Hq Hv Hx Ij In Iq It Iu Js Lj Ly Lz Mc Md Mf Mk Ml Mn Mq Mr Mv Na Nh Ni Nm Nu Nv Ny Ok Pd Pf Qa Qd Qe) Jq(Fp Hq Ij Iq Ir Iu Iv Jn Jr Js Lj Lu Ly Mc Mf Mh Mn Mq Mr Mt Mv Mx Mz Nb Nc Nf Ni Ny Oh Ok Om Pb Pd Pf Qd Qe) Me(Fp Hq Hv Hx Ih Iq Ir Iv Jn Js Jt Lj Ly Mc Md Mk Mn Mr Mv Mx Mz Na Nf Nh Nm Nr Nv Ny Oh Ok Pd Pf Qa Qd Qe) Oz(Et Fp Hq Hv Ih Iq Ir Iu Jn Js Jt Lj Ly Mb Mc Mk Mq Mt Mx Na Nb Ni Nm Nr Nv Ny Ok Om Pb Pd Pf Qa Qd Qe) No(Hx Ik In Iq It Jg Jk Jl Jm Jn Jp Js Li Lj Lu Lw Lx Ly Lz Ma Mh Mm Mr Mt Mv Nk Nv Om On Pa Pb Pg Qe) Nw(Fp Hq Hv Hx Iq Ir Iu Js Lj Ly Mc Mf Mk Mn Mq Mr Mv Mx Nb Nf Nh Ni Nr Nv Ny Oh Ok Pb Pd Pf Po Qd Qe) Pe(Et Hv Hx Ih In Iq Ir Iv Jk Js Lj Ly Lz Mb Mc Mf Mn Mq Mr Mv Mz Na Nb Ni Nr Nu Ny Oh Ok Pa Pd Qa Qd) Lu(aA Et Fp Hv Ih Iq Ir Iu Lj Mb Mc Md Mk Mq Mr Mv Mx Mz Na Nb Nf Nh Ni Nr Nv Ny Oh Ok Pd Pf Qd Qe) Po(Fp Hv Ih Ij In Ir Iv Js Lx Mb Mc Mf Mm Mq Mt Mv Mx Mz Na Nb Nf Nh Ni Nu Nv Oh Ok Pa Pd Qa Qe) Ij(Et Fp Hq Hv Hx Ih Iq Ir Iu Iv Jk Js Lj Ly Mc Mf Mn Mr Mv Mz Nb Nh Nm Nr Ny Oh Ok Pd Qa Qe) Mt(Fp Hq Hv In Ir Iu Js Jt Ly Lz Mc Mf Mk Mn Mq Mr Mz Na Nb Nf Nh Ni Nr Nu Oh Ok Pd Qd Qe) Om(aA Hv Hx Ih Ii Ik In Iq Iu Lj Lz Md Mk Mn Mq Mr Mv Mx Na Ni Nr Nv Ny Oh Ok Pb Pd Qd Qe) Pa(Fp Hv In Ir Jn Jt Lj Mb Md Mk Mn Mq Mr Mv Mx Mz Na Nf Nh Ni Nr Nu Nv Ny Ok Pd Pf Qa Qd) Nm(aA Fp Hq Hv Hx Ih In Iq Ir Iv Js Lj Ly Mc Mf Mn Mr Mz Nb Nh Ni Ny Oh Pd Pf Pg Qa Qe) Nc(Et Hq Hv Ih Iq Ir Iv Jn Js Jt Lj Lz Mf Mk Mn Mq Mr Mx Mz Nf Ni Nr Nv Ny Ok Pf Qd Qe) Pb(aA Hq Ih Iq Ir Iv Jn Jo Js Jt Lj Lz Mc Mk Mn Mv Mx Mz Na Nf Nv Ny Oh Ok Pd Pf Qd Qe) It(aA Et Fp Hq Ih Iq Iu Jo Js Jt Lj Ly Mb Mc Md Mf Mk Ml Mn Mv Nh Nv Ny Oh Pd Pf Qe) Jm(Fp Hq Hv Iq Ir Jo Js Jt Lj Lz Mb Md Mk Mq Mv Mx Mz Na Nf Ni Nr Ny Ok Pd Pf Qd) Pg(Fp Hv Hx Iq Ir Jk Jn Lj Lz Md Mf Mk Mn Mq Mr Mv Mx Mz Nb Nf Ni Nr Nu Pd Qa Qd) Ml(Et Hq Hx Ih Iq Ir Jo Js Lj Lz Mb Mc Md Mn Mv Mx Nh Ni Nv Ny Pd Pf Qa Qd Qe) In(Et Fp Hq Ih Iq Ir Iu Iv Js Lj Ly Mc Mf Mk Mn Mq Mv Nh Nu Nv Ny Oh Pf Qa Qe) Nx(aA Et Fp Hq Hx Iq Ir Iv Js Jt Lj Lz Mk Mn Mx Na Nf Nh Ni Ny Ok Pd Pf Qd Qe) Nu(aA Fp Hq Ih Iv Jk Ly Mc Mf Mh Mk Mn Mz Nb Nv Ny Oh Ok Pd Pf Qa Qe) Ii(Fp Hq Ih Iq Ir Iv Jo Ly Mc Mf Mh Mk Mn Mv Na Ni Ny Oh Pd Qe) Jk(Et Fp Ih Iq Ir Js Jt Lj Lz Mb Mr Mx Mz Nb Nf Nh Nr Pd Pf Qa) Nk(Iq Ir Iv Js Jt Lj Lz Mb Md Mk Mx Nf Nr Ny Pd Pf Qd Qe) Hx(Fp Hq Hv Ih Iq Iv Js Ly Mq Mz Na Nb Ni Nv Oh Ok Qa Qe) Oh(Hv Iq Iv Js Lj Ly Mc Mf Mn Mz Nb Nh Ni Ny Qa Qd Qe) Jn(Hv Ih Iu Js Jt Lj Lz Mb Md Mf Mh Mr Mz Na Ni Nr) Et(Fr Hr Ik Iv Ji Js Lv Lw Lx Mp Nq On Pc Qa) Mm(Fp Hr Hv Jo Jt Mr Mu Mv Na Nf Ni Nr Qd) Nh(Fp Hv Ih Iq Iu Iv Jt Ly Mf Mn Ok Pd Qa) Lx(aA Ir Jt Mb Md Mr Na Nf Nr Nv Ok Qd) Hr(Fp Ir Jo Jt

Figure 42 Continued

Lz Mb Md Mv Mx Nv Ok Pd) Ih(aA Ir Iu Ly Mc Mf Mk Mn Mq Mr Nf Qe) Li(Jt Md Mq Mv Nf Ni Nr Nv Oe Pd Qa Qd) Nb(Fp Hq Ik Iv Ly
Mc Mf Mk Ms Ny Qe) Jp(Jo Jt Mb Md Mv Mx Mz Nf Nv Ok Pd) Ma(Jo Jt Md Mv Mx Na Ni Nr Nv Ok) Mh(Ir Iu Lz Mr Mv Mz Nf Nr Pd Pf)
Ik(Jo Jt Lz Mb Md Mr Mx Nr Nv Pd) Jg(Ir Jt Lz Mb Md Mv Mx Ok On Qd) Qe(Iu Ly Mc Mk Mn Mq Mr Nr Qa) Lv(Ir Jo Md Ni Nv Pd Qa Qd)
Mz(Iq Iv Js Lj Mc Mf Mn) Iv(aA Fp Iu Js Mn Nr) Qa(aA Fp Mf Mv Na Ni) Mc(Iu Ly Mf Mn Ok) Mn(Iu Mf Ni) Mr(Lj Ly Mk) Mv(aA Ok On)
Js(Hv Jr Nf) Fr(Jt Na) Nq(Jo Qd) Mb(Pc Pd) Iu(Mf Ok) MuQd N

Ne Oe Pe) Po(Hq Lu Nx Pf) Lw(Hr Mc Md Mi) Nd(Hq Mi Mn Ni) Hv(Hu In It Ly) Of(Mb Mi Na Nt) Og(Hu Ma Mv Nm) Wm(Lu Oe Oz)
Lz(Hq Lj Pf) Nj(Jh Mv Om) Nl(In Mc Oh) Nu(Nr Oh) My(Jh Nq) Ne(Ma Om) Jg(In Lu) Jo(Nt Pe) Pb(Ly Mb) Pg(Mm Oy) MdHq NaIt NcIm
NfLj NgQa NhOm OePe} Mu{Ms(Hq Ih Ii In Iu Jh Jk Lu Ly Lz Mc Mi Mm Mq Mv Mx My Mz Nc Nt Nv Nx Of Oh Oz Pc Pf Pz) Nc(Hq Hv
Hx Ii Ik Im Jh Jm Mi Mq Mw My Nl Nn Nr Ns Nu Of Oh Oy Oz Pc) Nd(Il In It Jp Jq Js Lh Lx Me Mf Mj Ml Mw Nf Nr Nv Nx Pe Pf) Oe(Hq Ij
Iu Jm Lw Lz Mb Mc Me Mr Nn Nq Nw Ok Oy Oz Pb Pf Pz) Jp(Ii Iu Jk Lh Lx Ly Mj Mk Nb Nr Oz Pb Pe Po Qb Qc) Io(Iq Js Lu Lz Mi Mk Nb
Ne Nh Nn Nr Nt Nu Nv Pz) Pz(Hr Iq Jg Jm Jo Lu Ly Mc Md Ml Na Nl Nu Of) Lv(Ih It Mm Mw Mz No Nq Nt Nu Nx Pe Pf Qa) Pg(Iu Jg Jh Lz
Ma Mb Me Ne Nh Nm Nw Ok Qa) Mh(Ih Jh Mf Mv Ns Nt Of Pb Qd Qe Wm) Ng(Fp Hu Ik Iq Ir Ml My Ne Nf Nm Nx) Mw(Hv Lw Lz Mj Mq Nl Ns Ny Pa Pc) Pe(Hr Jm Jq Ly Mj Nv Of Oy Qc) Nu(Il In Lh My Nn Nr Nx Pd) Nk(Et Fp Iq Jg Jt Ly Ma No) Lu(Iu Nb Ne Nh Nv Pf Qa) Nr(Jo Lw Mc Me Mi Pf) Mg(Hr Iq Jh Mm Pd Qc) Jn(Ir Jt Ma Mm Ok Om) Of(Hx It Iu Jk Qd Qe) Jm(Hx Mj Ne Nh Qb) Jo(In Iu Mz Nb Nt) Jq(Hw Il Jk Po Qb) Pa(Ik Lh Nx Oh Pc) Mf(Ij Nn Wm) Mv(Hw Ny Pf) Ni(Na Ns Nx) Nj(Hu Oy Oz) Ii(Hu Oy Qa) Im(Nl Og Oi) Et(Nh Oi) My(Lh Ny) Hv(It Mc) Hw(Mb Me) Ik(Nx Qd) Qb(Oz Pb) Og(Li Qd) PoMn NnNq LyIj MiOy MjMk NlNv HqNy HrIu IlPb QaNw} Jn{Mm(Fr Hq Hw Ih Im Iq Ir Iu Iv Jh Lh Li Lj Lz Ma Mb Mc Md Mj Mk Mn Mq Mr Mx My Nb No Nr Nu Nx Ny Oy Oz Pb Pc Pf Qd Qe) Nq(Fp Hr Hu Hv Iq It Jg Li Ly Ma Mc Me Mi Mk Ml Mn Mr Nb Nc No Nr Ny Oh Om Oz Pb Pc Pf Qb Qe) Lv(Fp Hq Hr Hv Ij Il It Iu Jk Jq Lj Lw Lz Mc Mj Mq Ms Mz Nd Nk Nl Nm Nr Nu Oe Om Oz Pf Qa Qb) Fr(Hv Ih Ir Iv Li Lw Md Me Mj Mq Mz Nf Nl No Nu Ok Om Qd) Po(Hr Hx Jg Js Lx Lz Ma Me Mh Mw Nw Oe Oh Ok Pc Pz Qc) Lx(Hu Ik Li Ma Mi Mr Nb Ng Nr Nv Nw Ok Om Oz Pa Pe) Ma(Hx Ik Im In Mb Mw Nh Nj Oe Of Pe) Nw(Hw Il Im In Jh Lj Ml Nd Ns Nx Pe) Oi(Hw Iv Jt Lh Mh Mq Mw Nb Nm Nu Nv) Lw(Hw Io Jp Lu Mi Mx Ng Og Pe Pz) Nj(Hx In Iv Jq Md Mg Mj Ms Mw Oh) Om(Io Mg Ms Mx Nd Ne Nn Pe Pg Qa) Og(Im Jt Mh Mq Na Nr Nu Oz Qe) Mw(Jq Mz Ns Ok Oy Qc Wm) Im(Jg Jp Ms Nc No Pg Qa) Pc(Jp Lu Ng Pa Pe Pz Qc) Ml(Jg Jk No Ok Pe Qa) Jh(Li Mh Mz Ns Pa Pe) Et(Ne Ng Nn Pa Qc) Nt(Ii Ms Nd Oe Of) Nn(Ir Ni Pd Qd) Io(Mh Mv Nr Pe) Jk(In Jg Oy Pb) Hr(Ms Pa Pe) Qa(Mh Ng Qc) No(Jo Oe) Lh(Ng Oe) Of(Ok Wm) MgPz MsJq IiPa} Nj{Pe(Hq Hr Hu Il Iv Js Jt Lz Me Mg Mk Mn Nk Nl Nm Ns Ny Oe Oy Qb Qe) Et(Fr Hu Hx Ii Io Lu Ms Nd Nk Nn Nq Nv Nw Of Qb) Nw(Fp Jp Jt Md Mg Mj Nr Nu Nx Of Oh Pb Qb) Mx(Hu Hx Io Jp Jt Lw Ma Mq Mv Mw Nf Oh) Mz(Ih Ij Il Lh Ma Md Nb Ne Nh Nk Po Qc) Ok(Hq It Jg Jp Jt Mc Mf Mw My Oh Oz Pf) Nq(Hr Io It Jg Jp Lj Lx Lz Mc Me Nu) Lh(Ij Iv Jk Lv Ma Mn Ne Nt Of Pg) Nv(Ij In Lj Lv Ma Mi Ni Ny Oe Qe) Hw(Fp Hx Jh Mn Ng Om Pg Po Qb) Nt(Jg Jh Lv Mb Mi Mw Na Ny) Nb(Iq Iv Jk Lj Na Pg Wm) Hx(Io Jt Lw Mq Na Pg) Ir(Ii In Jp Jt Ng Oi) Qd(In Jh Jk Md Nd Wm) Jq(Hu Ij Mv Mw Nk Om) Mr(Ij Im Jp Nn Po) Qa(Jm Jo Nk Pd Pg) Jk(Fp Iv Mn Nm Og) Oh(Hq Im Lw Nm Qe) Pa(Hv Jt Lv Nu Pg) No(Jm Mb Nc Nx) Lx(Im Nl Om Qb) Mw(Lz Md Mj Nd) Nn(Jt Ma Mm) Lv(Lj Qb Qe) Mi(Il In Mb) Ih(Jg Og Wm) Jh(Iq Lw Mj) Pg(Jm Mq Nx) Nr(Ms Og) Md(Im Qb) Na(Js Qe) Iv(Fr Ii) Jg(Iu Lu) Jp(Il Mg) PoNd LwHv MjIm NfQe NgOm} Og{Nt(Hr Ih Iq Iu Iv Lu Md Mq My Nf Nh Ni Oe Pf Qc) Jg(Ih Ik It Iv Jm Jt Mc Me Mg Mk Nl Nx Oh Pb Qd) Et(Fr Io Iu Jt Mx Nc Ne Nh Ni Nq Nv Oe Oi Pc) Om(Hr Ik It Jm Mc Md Me Mf Mn Nf Oe Oz Pd Pf) Nw(Im It Jp Jq Lj Mh Mr Mx Na Nd Nk Nr Oi) Nn(Im Jk Me Mh Mv Nd Ni Nm Oy Pc Qb) Lh(Hr Hx Jo Li Mi Ml Mn Ok Pe Pg Qb) Pg(Hx Ma Mh Mi Mr Mv Nm No Nq Pe) Po(Im Js Jt Nd Nf No Oz Pb Qe) Ok(Hr Ij Im Jq Ma Mm Nd Nv Qb) Lv(Fp Ih Jt Lz Mq Mr Nu Pe) Qa(Hx Ly Lz Md Mh Mv Nh Nr) Jp(Iu Jq Mg Mv Mz Nb Nm Nv) Fr(Iq Iv Jk Js Mm Mn Pd) Nq(Ij Jt Mf Mh Nm Of Oi) Mi(Hx Im Mm Nr Nv Pc Qb) No(Ij Iu Mq Nk Nu Pe) Im(Jk Jq Lx Mj Qd) Jh(Mf Mg Nc Nm Qd) Nu(Jq Mz Nm Oh) Ma(Il Mz Nv) Jk(Lx Nx Qb) Jq(Iv Li Nv) Pe(Hr Li Oz) Nm(Ih Nl) Mv(Ir Jt) Hw(Hr Oh) NrMg LxIv MmMx MqPa NbLi IiPc} Nn{Jp(Hu Hv Hx Ik Im Jm Lh Lw Mc Me Mi Mk Mr Mv Nq Nv Nx Oe Of Oy Oz Pb Pf) Mf(Ik Jm Lu Lw Mc Mi Ml Mx Mz Nl Ny Oh Pc Pf) Pe(Hu Hx Lz Ma Mh Mw Nd Nx Oh Ok Om Pb Pd Wm) Mw(Hv Ij Io Mc Ne Nh Nl Ns Ny Oh) Jq(Ik Iu Mb Me Mj Ml Mx Nb Nl Qc) Ms(Ii In Js Lw Mn Nl Nt Oz Qb) Ly(In Lw Mi Mj Ml Nd Nr) Pg(Et Na Nv Oh Ok Pb Pc) Lv(Hq Jh Mz Nb Nu Qb) Mh(Fr Il Lw Ng Nv Pc) Lx(Hx Mb My Nx Qb) Mg(Il Jt Nd Nf Qe) Mm(Lh Ma Ny Ok Wm) Ij(Hu Ml Mv Ns Nx) Ik(Lh Nb Nr Nv Wm) Pz(In Mi Mr Nx Ny) Lu(Il Lh Nw Qb) Ir(Iu Ng Pc Qc) Of(Hv Ii Il Mx) Pa(Hu Jh Lz Nu) Po(Hr My Nu) Mz(Jm Nl Nx) Io(Lz Nu Nx) Qa(Nc Oh Pc) Qc(Mi Mj No) Nw(Il Mx Oh) Et(In Nk) Nb(Jm Mn) Ii(Hu Ns) Om(In Jo) NoNk MdNd MiPd MjNe MxHv NcIm NfNg HrHw HxPc OeOk} Lx{Pz(Et Md Mj Mz Na Nr Nt Om Pe Pf Pg Qe Wm) Mw(In Jh Lw Mq Ms Nb Nd Ne Ns Ny Pb Pc) Hq(Ij In Iu Jh Jq Md My Nf Nq Nt Ny Pa) Oi(Jh Lz Mc Mk Nd Nr Ns Nx Om Pd Pf Pg) Lv(Fr Js Mf Mm Mr Mz Nw Ny Pf Qb Qc) Oz(Fp Hv Hx Jm Jp Mc Ne Nu Ny Pb Qb) My(Hv Jq Lh Lw Mc Mq Nr Pd Pf) Jp(Jh Jq Mi Mq Ms Ne Nh Nq Pg) Nk(Et Fp Jh Mf Mi Ng Ny Qa) Hr(It Lu Mk Nf Nq Nr Nu Oh) Of(Et Hv Ij Lw Mq Nx Qa) Oy(Hv Hw Ij Jk Mf Oh Pf) Ms(Hu Hw Lw Lz Nu Pd) Io(Fp Jm Js Lh Lw Qb) Jq(Iv Jk Md Mh Pg Qa) Pb(Hw Ij Lu Lz Mi Om) Nu(In Lz Mi Nr) Hv(Me Ml Nd Ni) Mg(Et Lw Nq) Ng(Ma Mv Qa) Lu(Hx In) Mk(Nh Nr) Nd(Hw Jh) Hu(Mm Ok) Qc(Mj Oh) Jm(Ij Mx) Jo(Lh Om) Oe(Na Nm) MhLh NhNl HwIt} Fr{Lv(Hq Hu Ii Il In Jk Jm Mc Mi Mj Mk Mn Mr Mx My Nc Nq Nr Nx Ny Of Oh Oy Pf Po Qc) Ms(Hu Ii In Jh Jm Lw Mi Mj Mx My Mz Na Nm Ns Oe Of Oh Oy Pa Pe Pf Pg) Ng(Ij Il It Iv Lz Ma Mb Md Me Ml Mn My Na Ne No Ns Nv Ny Of Oh Ok Oy) Nk(Hq Lw Ly Ma Mc Mk Ml Mr Mv Nr Ns Nu Nw Ny Of Oh Oy Pa Pb Pe Po Qa) Pz(Hq Hu Ik Jg Mc Md Me Mf Mg Ml Mr My Na Nq Nu Oh Oy Pc) Io(Ir Js Ly Mi Mw Ne Nh Nr Nw Oe) Mh(Hw Ij Jp Lu Mf My Oe Qc) Mm(Jk Li Lw Mi Mq Oh Qd Qe) Pg(Hu Jp Jq Lu Mn My Qc) Mg(Ih Iq Li Qe) Jq(Hq Ne Nh Pf) Oi(Et Im Iq It) Mx(Nc Oe Oz) Of(Ma Mb Mw) Mz(Jo Qc) Nc(Qa Wm) Nh(Jp Nl) Ni(Hw Qa) NdOe HqHx IiPe InJp LhPf} Qa{Pz(Fp Hv Hx Ih Il In Ir Js Mb Mc Mk Ms Mx Na Nc Nd Nf Nh Ni Nk Nl Nr Ns Nu Ny Of Oi Oz Pd Qb Qc Wm) Io(Hu Ih Il In Iv Jh Js Jt Lj Lu Ly Lz Mf Mg Mj Mk Mx Ng Nh Ns Ok Om Oz Pf) Ik(Et Iv Lj Lw Md Mk Mm Mq Ms Mw Nl Nr Nu Nx Of Oh Om Oz Pc Pf) Jp(Im Iu Jh Li Lj Ml Nd Ng Ni Nk Ns Nt Nw Oh Pa) Mh(Jg Lu Lv Ma Me Nq Oh Oi Pc Qc) Jq(Hu Im It Lv Ly Ma Me Mw Nq Nw) Pb(Hr Hu Lu Ma Mr Mw Ng Nt Pa Pc) Nw(Il Jm Lj Ng Ni Ns Nx Pa) Mm(Lu Nc Ng Nk Nm) Of(It Lw No Nx) Oi(Il Nf Nt Pg) Mg(Lh Mi Om) Ma(Lu Ms) Jo(Jt Nr) WmIu EtLy MsIt} Et{Oi(Hw Hx Ih Il Io Jg Jk Jq Lu Lw Mi Ms Mx Nb No Nt Nw Of Pz Qb) Pz(Hu Hx Jg Jp Jq Lh Li Lw Mm Mn My Nd Nq Nw Oe Po) Pg(Hx Im Jm My Nd Ne Nh Ns Oy Oz Pa Qc) Mg(Hu Hw Hx Ii Io Iu Jk Mi Mv Nb Pc) Mm(Ir Jg Jh Lh Mh Ms Mx Nt Nv Ny Qe) Io(Hx Lh Mh Mi Mj Mx Ne Nh Qb) Of(Hu Hx Lv Nd Ne Nh Qb) Nk(Hu Il Jh Jq Lv Nm) Ms(Jq Lv Mh Mz Pc) Ng(Hu In Lh Pe) Jk(Lv Mh My Oy) Jo(Hx Ii Nt Po) Oe(Hx Il Nb Nh) Pa(Lv Mh Mk My) Nd(Hq Ns Pe) Ml(In Pe) Pc(Hu Pe) WmIk} Lv{Jp(Fp Jq Lj Lu Lw Lz Ma Mf Ml Ms Mv Mw My Nc Ng Ni Nk Nr Nv Oe Ok Qb) Oh(Iu Jh Lh Lz Ma Mh Mw Mx Na Nl Nm No Pc) Nw(Jk Lh Mi Mm Mr Ms Mw Nk Nq Oe Qc) Po(Hr Ii Jg Jm Ma Mb Mm My Nx Pd) No(Hr Ii Ik It Jh Jm Lh Nx Qc) Mi(Hv Jg Jm Ma Mb Nd Pb Pf) Ok(Jh Ly Lz Mh Ne Ng Nl Pb) Ma(Lu Mh Ms Nd Pe) Mm(Lz Mf Mr Oe Pg) Io(Hv Jt Lz Mx Nc) Jg(Jq Mf Ms Nd Pa) Lh(Oe Oi Pz Qc) Nt(Jo Ng) Mr(In Jm) Nd(Jh Om) Hv(Jq Ng) Pz(Mz Pe) HxJq IkJh ImPg NyPb OzPa} aP{dD(aC aD aQ aS aZ bA bF bI bJ bM bQ bR bS bU cC cD cG cI cQ cW cY dB dC dE) aI(aE bE bM bN bP bR bU bZ cA cC cD cG cI cK cL cO cW cX cZ dA dB dC dE) dH(aC aF aM aS aW bH bJ bP bS cA cH cT cV cW dE dG dJ) dK(aC aK bG bN bQ bS bZ cE cQ cS cX cY cZ dC dJ) bO(aO bM bP bR cD cE cN cU dG) aY(aC aE aZ cC cT cU) aO(aX bF cJ cM cU) cU(aJ bP cC cD) aU(aK bA cL) bX(aL cE cN) bC(aZ bA) bM(bR cD) bW(cQ cT) cMcN} Jq{Jk(Hr Hx It Iv Jg Jh Mi Ml Mw My Nq Ns Nt Om Oz Pc) Po(Fp Iv Jh Lj Lw Md Me Mh My Ni Nk Nq Ns Oi Pz) Mw(Fp Hw Ii Iv Mi Nb Nd Nq Pe) Pe(Hv Io Jg Lw Nk Nw Of Pf) Nq(Fp Hw Ii Mh Nf Pg Qe) Pa(Hv Iv Jh Li Lw Mm Pc) Nk(Hw Io Jg Jp Ma Nd) Nu(Il Io Iu Oe Oi) Mm(Jt Ly Mh Nh Ni) Jp(Il Ms Oe Pg) Nw(Il Nm Oi Pz) Lw(Hv Hw Ms) Oi(Iv Li Mv) Me(Hw Iu) Hr(Hw Iu) Pz(Li Qd) Oe(Hv Ok) Of(Mi Wm) NtNg MhQd NcIm IlJg QcPg} aJ{aI(aC aF aH aK aM aS aZ bB bF bL bP bQ bS bV cH cI cK cL cO cX cY

Figure 42 Continued dB dE) dD(aC aD aE aF aH aK aM aR aS aV aW bA bB bQ cA cG cH cL cO cW dC dL) dH(aC aK aM aN aV aX aZ bR bS bU cB cE cP cT cX cY dJ dL) cU(aS aW bG bI bJ bV cB cO cY cZ) aO(aU aX aY bF bV cC cN cS cX) bX(aE aM aU bA bB bC bI dC dF) bC(aZ bM cN dK) bO(bR cN) bV(bU cC) cJ(aY dG) dK(bM cR) bAcS bIcM bPbW} Nw{Io(Hq Hr Hu Ih Ik Im Iq It Jm Jo Js Li Lj Mb Mc Md Mg Mm Mn My Na Nf Ns Nx Ok Oy Pb Pd Pf Qc) Oi(Hr Ih Ij Ik Im Ir Jh Jt Ly Mj My Nc Ne Nf Nh Nm No Ns Nv Oz Pd Qb Qc Qd Qe) Pz(Ih It Jh Lu Mh Mn Mw Na Nf Ns Nv Oh Ok Pd) Jk(Fp In Mi My Ng Ns Oy Oz) Pe(Hx Ii Md Ml Ng Ny Pb) Pa(In Lw Mh Mw) Nq(Ms Ng) Hw(Nm Of) Oe(Lu Wm) NtOf MlIj MsHx MyHv NkIm InNy} Pg{Im(Hv Ii Ij Io Ir Jg Jh Lw Ma Mj Ms Mw Mx Mz Na Nb Nd Nf Nk Nq Nr Of Om Oz) Mm(Hu Hv Ij In Mf Mn My Mz Nd Nk Ns Oh Ok Oy Pa Qc Wm) Io(Hw Ik Iu Lu Nk Nm Nq Nr Nu Nx Pz) Ii(Hv In Lw Mi Mq Nm Nr Pa) Pz(Jh Nq Oz Po Qd) Jp(Mh Mi Ms Na) Jo(Iq Mb Mh) Ma(Ik Nx) Ng(Jh Om) Oi(Oh Pc) Ok(Nq Pf) MgIk MiPb NdOm} Mw{Oh(Ij Lw Mc Me Mi Ml Nb Ne Nh Ny Pc Pe) Mi(Hr Hv Io Jm Md Mj Mx Ns Oy Pa) Jm(Lz Md Nb Ne Nh Ny Of Pf) Pf(Hu Ik Io Mc Ne Nh Po) My(Lh Ma Mk Ml No Nv) Pa(Hu Ik Mc Ne Ng Oe) Pz(Ik Md Nd Ne Of) Hv(Lw Mc Nd Ns) Ik(Ne Nh Of) Pb(Mj Ny Oy) Po(Hq Mk) Lw(Mf Nd) Io(Ih No) Of(Mj Nd) WmHx LzHq MdMl MzQc OiOk} Pe{Jo(Fp Hq Hu Ih Ik II Jm Lj Ly Mc Mh Mj Mk Mx My Ny Pd Qb) Mm(Hu Ii Jm Jp Ly Mb Mk My Nd Ns Oe Oy Oz) Pf(Hr Im Jp Nq Ok Pb) Ma(Im Io Ml Nd Of) Pz(Jk Ml No Oh Pb) Oh(Hx It My Oi) Om(Hu Ng Ns Pb) Mg(Ik Lw Oi) Ng(Jg Pc) Ii(Lw Pc) Oi(Me Nt) Pb(Jh Jp) NqMs NcIm IkJg IoOk} Jp{Io(Hx Ii Ij Jg Jt Mh My Mx Nd Sk Qb) Jk(Hv Hw Iu Lw Mh Nf Nm Oh Oy Oz Pc) Nq(II Ly Mf Mh Mx My Mz Ns Qb) Oi(Hw Li Mf Mq Nb No Om) Po(Lw Lz Mh Ms My Ns) Wm(Iq Mb Nx Ok) Mi(Il Nk Pa Qc) Pz(Ij Ma Mg Nt) In(Lw Mm Pc) Pa(Jg Mf Oe) NtMs MgLh NbOf IlQd] Oi{Jg(Fp Ij Mg Mk Mv My Ns Pa) Om(Hw Iu Iv Jt Lw Mg Mx Pz) Ma(Ih Nb Nk Nt Nv Qd Qe) Mm(Iv Jh Jt Mj Ms Ok Pc) Nq(Fp Hq Iv Lj Nf) Lh(Hr Li Me Mf Mg) Nt(Mh Mv Nf Qb) Po(My Of Oh) No(Jh Jk Lw) Mz(Li Mv Pc) LwMr MfOk MiNd LiPc} Po{Lw(Hu Il In Ms My Nm Of) Oy(Mc Mh Mj Ms Nd Of) My(Hq Lz Me Ms Nl) Mm(Io Ng Nk) Jo(Jk Jt Qd) Lj(Hx Ml Ny) Pc(Hu Nx Qc) Mh(Jm Ms) Im(Nc Pz) Io(Hr Lh) Of(Nl Pf) Wmlu NqMs NuOh MfNg JmNy} Nq{Nd(Hv Io Lw Me Mf Mi Mj Mq Mr My Ny Oh) Ng(Hq Ir Lz Md Me Mk Mn Na Nf No Ok) Io(Il Mf Ny Qb) Mg(Ir Js Nm) Lu(In Pa) Ms(Mr Mz) Mx(Ik Jm) Hr(Ij In) MnPz IlJm} bA{bW(aD aG aL aS aW bI bR bU cH cM cS cU cX dF) aO(aF bJ cF cU) bC(aY cC cD cY) cS(aM aU cK cY) cC(aX bE bZ) cF(aV cH cV) bO(bE bJ)} cU(aY bL)} Om{Pz(Il Iu Jt Ni Ok Pc) Nd(Jo Lu Nk Oe Pa) Of(Hw Iu Mi Mx Nv) Mg(Hx Ir Jo Lu) Io(Lh Mi Pa) Wm(Ik Nm) Ng(Jk Nk) Jo(Ii Ir) Pa(Mk Ml) NkIm} bV{dK(aE aK aY bG bX cF cR cU) bL(bO bR cC cU) aU(cK cS cY) aO(bJ bO) cK(bU cD) cR(bC cS) cU(cA cX) aYbQ bWdD cCdB cFcS} Io{Mm(Ir Mj Nk Qb) Ok(Hu Nk Nt Nv) Mz(Nk Nx Wm) No(Ni Qb) Nt(Nd Ni) Lw(Mr Mx) Ma(Ir Lh) Mi(Me Mn) Pc(Ir Pa) MnNb ImLh} Ma{Ng(Hx Mh Mr Nb No) Pz(Ih Il Iv Jt Nv) Mg(Ir Iv Mr) Of(Hw In Mr) Jo(In Ir) Pa(Lw My) NoNh MsOk} Ms{Ok(Hv In It Iu Lj Mc Me Mq Ne Ns Oe Oh Pc) Mi(Hr Mb Nd) Jg(Hx Nb Pa) Mm(Hu Hv)} Jh{Pa(Hq Mc Nd Nh Oh Pf) Nc(Mx Wm) Nd(Pf Pz) Of(Mi Nb) NsNk NhPf HwIk JkOy OeOk} Jo{Nt(Hx Mk My Ne Nk Pf) Lh(Iu Mn Of Qb Qe) Hw(Mn Nv) Jk(Jt Mq) NoLi IjOk} Mm{Hu(Ik Lu Mz Oe Pa) Pz(Hx Mx Mz) Mg(Jt Nv) Nc(Jk Pa) Ng(Hw Pa) NbNk IkQd} cS{cF(aQ aW cR cY dG) dM(aY bR dH) aO(cQ dA) aMbF aWbO bGdK bQdH cQcU} aO{aX(aD dM) bC(bJ dB) bW(bO cT) cU(dH dK) aMdJ bHcF bQcE} Pz{No(Jk Li) Mi(Im Jg) Qd(Mh Ok) QbJg JkLh} bW{cF(aW bO cQ) bQ(cL dH) aWbO cTcY dDdM} Wm{Mz(Iu Nm) Of(Nv Pd) NtIk NgJg IuQd} dM{dK(aY bR cR) al(bC cZ) aX(cD cF)} Mg{Nt(It Mf Nx) Nmlu LwMi JgLh} Ok{Jk(Mh Oz) IlOe OzPa} cU{bE(aM cZ) dE(aI cQ)} Lw{Hu(Hv Oh) NrJm} aX{aI(aM cK) bQcF} Hr{NtNg HwOh} Ik{Qd(Jg Nx)} dK{aMdJ bOdA} MiliIn cFcJcK Unconstrained panels with 2 analytes, where 1.0E-7 >= 'AUC p-value' > 0. Contains 811 panels of 11,037 total panels evaluated. : Is(aA Et Fp Fr Hq Hr Hu Hv Hw Hx Ih Ii Ij Ik Il Im In Io Ip Iq Ir It Iu Iv Jg Jh Ji Jj Jk Jl Jm Jn Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jl(aA Et Fp Fr Hq Hr Hv Hw Hx Ih Ii Ij Ik Il Im In Io Ip Iq It Iu Iv Jg Jh Ji Jj Jk Jm Jn Jo Jp Jq Jr Js Jt Lh Li Lj Lu Lv Lw Lx Ly Lz Ma Mc Me Mf Mg Mh Mi Mj Mk Ml Mm Mn Mp Mq Mr Ms Mt Mu Mv Mw Mx My Mz Na Nb Nc Nd Ne Nf Ng Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) On(aA Fp Hq Hr Hu Hv Hw Hx Ih Ii Ij Il Im Io Ip Iq It Iu Jg Ji Jj Jk Jm Jn Jo Jp Jq Jr Js Lh Li Lu Lv Lw Lx Ly Lz Ma Mb Mc Md Me Mf Mg Mh Mi Mj Mk Ml Mm Mn Mp Mq Mr Ms Mt Mu My Mz Na Nb Nd Ne Nf Nh Ni Nj Nl Nm Nn Nq Nr Ns Nu Nv Nw Nx Ny Oe Of Og Oh Oi Ok Om Oy Oz Pa Pb Pc Pd Pf Pg Po Pz Qa Qb Qc Qd Qe) Jr(aA Et Fp Fr Hr Hv Hw Hx Ii Il Im In Io Ip It Iu Jg Jh Ji Jj Jk Jn Jp Jq Lh Li Lj Lv Lw Lx Ma Mc Me Mf Mg Mh Mi Mj Ml Mm Mn Mp Mq Mr Ms Mt Mu Mv Mw Mx Mz Na Nb Nd Ng Nj Nk Nm Nn No Nq Nr Ns Nt Nu Nv Nw Oe Of Og Oh Oi Ok Om Pa Pc Pe Pf Pg Po Pz Qa Qb Qc) dN(aA aC aD aF aG aH al aJ aL aM aN aO aP aQ aS aU aV aX aY bA bB bC bF bG bH bI bL bM bN bO bP bQ bS bW bX bZ cB cC cE cF cG cJ cK cL cM cN cO cQ cR cS cT cU cW cY dA dB dC dD dE dF dH dI dK dM) Mp(aA Hq Hv Ik In Io Ip Jh Ji Jj Jm Jn Jp Jq Lu Lv Lw Lx Lz Mc Md Me Mh Mi Mj Mm Mq Mr Ms Mt Mu Mw Mx Mz Nb Nc Nd Ng Nj Nk Nl Nn Nq Nr Ns Nt Nu Ny Oe Og Oh Oi Pa Pc Pg Po Pz) Ji(aA Hv Hw Hx Il In Io Ip Ir It Jj Jk Jn Jp Lu Lv Lx Ly Ms Mt Mw Mx Nd Ne Ng Nh Ni Nj Nk Nm Ns Nu Nx Oe Of Og Oi Pa Pe Po Pz Qa Qc Qd Qe) Jj(Et Fr Hw Hx Ih Ii Ij Il Im Ip Ir Iu Jk Jn Jo Js Lh Li Lv Lx Ma Mi Mt Mu Mw Nn Nq Nr Nt Nv Nw Om Pa Pe Pg Po Qa Qb Qd Qe) Mt(Hv Hx Ik In Io Ip Jm Jn Lv Lw Lx Mc Me Mi Mj Ms Mu Mw Nb Nj Nk Nl Ny Oi Oz Pa Pb Pc Pz Qc) aA(al aX aY bC bW cF cJ cS cU dK Fr Ip Jk Lv Lw Mf Mm Mu Mw Nj Nn Nq Pc Pg Qa) Mu(Hv Ip Jn Jp Lv Mg Mh Mj Ms Mw Nc Nd Ng Nj Nk Nr Oe Og Pz) Mw(Hv Ik Jm Lx Mc Md Mi Mr My Nd Nh Nn Ny Of Og Oh Pa Pf Po Pz) Lx(Hq Hr Hu Io Ip Jn Lv Ms My Nj Nu Oe Og Oi Oz Pb Pz) Nn(Ip Jn Jp Lv Mf Ms Nd Ng Nj Oi Pa Pe) Fr(Ip Jn Lv Mg Mh Ng Nj Nk Og Oi Pz) Nj(Mz No Nq Ok Pe Po Qa) Lv(Jg Jn Jp No Oh Ok) Qa(Ik Io Ip Jp Nw Pz) aJ(al cF cU dD dH) aP(al cF dD dH dK) Po(Ip Jq Og Oy) Nq(Io Jn Nd Ng) Nw(Io Ip Oi Pz) Og(Jg Nt Om) Mm(Jn Pe) Ip(Jn Jq) Pg(Et Im) WmJp MsOk JhPa JkJq JoPe aObC bAbW Unconstrained panels with 2 analytes, where 1.0E-6 >= 'AUC p-value' > 1.0E-7. Contains 434 panels of 11,037 total panels evaluated. : Mt(Fp Hq Hr Hu Ii Ij Iq It Jg Jh Jp Jq Lu Ly Lz Mb Md Mf Mk Mn Mq Mr Mz Na Nd Ne Nf Ng Nh Nn Nq Nr Ns Nu Nw Nx Oe Og Oh Pf Po) Ji(Et Fp Fr Hu Ii Ik Im Iu Iv Jh Jm Mb Mc Me Mf Mh Mi Mj Ml Mr Mu Mz Nb Nn Nq Nr Nt Nv Nw Ny Pb Pg) Jr(Hq Hu Ih Ij Ik Ir Iv Jm Js Jt Lu Ly Lz Mb Md Mk My Nc Ne Nf Nh Ni Nl Nx Ny Oy Oz Pb Qd Qe) Mw(Ij In Ip Iq Jh Jn Jq Lw Lz Me Mj Mq Mx Mz Nb Ne Nf Nj Nq Nr Ns Nw On Oy Oz Pb Pc Wm) aA(aF aU aW bH bL bO bQ bZ cM cO cX dB dD Hr Jg Jh Jj Jn Me Mg Mh Mv Nk Nt Oe Og) Mu(Hq Hw Hx Ii Ij Ik In Io Iq Jq Js Lh Lu Lx Mx Nn Nu Ny Of Oy Pa Pb Pe Pf Qb) Nn(Hv Ii Ij Ik In Jq Lu Lw Lx Ly Mc Mh Mi Mj My Mz Nr Ns Nw Ny Og Pe Pf) dN(aE aK aR aW aZ bE bJ bR bU bV cA cD cH cI cP cV cX cZ dG dJ dL) Ip(Et Hx Jg Jh Jk Jp Lh Ma Mi Mz Nb No Og Ok Om Pa Pe Pg) Po(Hq Hr Io Jh Jn Jp Lj Lv My Nd Nl Of Oi On Pz) Lx(Fp Hv Hx Jh Jp Jq Lu Mc Mi Mk Mq Nr Oh Oy Pf) Et(Jn Mg Mm Nj Nk Oe Og Oi On Pa Pe Pz Qa) Mp(Hw Ii Ij Il Iq Ir It Lh Na Nf Nv Nw Qb) Jj(Fp In Iv Jh Jm Mg Mn Mr Mv No Ny Pd Wm) Nj(Hx Ir Jn Lh Mi Nb Nt Nv Nw Pg Qd) Qa(Jn Iq Ma Mh Ms Of Oi Om On Pb) Jn(Im Jg Jh Jk Jp Ma Nw Oi Om) On(Ik Im Jt Lj Mx Nt Pe Pg Qb) Pf(Io Jh Lw Mc Nd Ne Ns Oh Pz) Nw(In Jk Lv Oe Og Pa Pe Pg) Og(Jh Lh Mi No Ok Pe Pg) Fr(Io Ms Oe Of Pe Pg) aP(aO bO bR bX cN cU) Jp(Nq Nt Pa Pe Pg) aJ(aO bC bO bX cM) Lv(Hv Mi Mm Mr) Jh(In Mj Nd Ny) Jl(Ir Mb Md Nh) Om(Oi Pa Pe Pg) Nq(Jq Oi Pz) Pe(Ma Oh Pz) Pg(Io Mm Pz) Hv(Lw Oh) bA(cF cU) bV(cU dK) NuJq MaIr MmOi IsJo aObW

Figure 42 Continued

Unconstrained panels with 2 analytes, where 1.0E-5 >= 'AUC p-value' > 1.0E-6. Contains 833 panels of 11,037 total panels evaluated. : Nw(aA
Fp Fr Hv Hx Ii Ij Il Im Iq Ir Iu Iv Jg Jh Jq Lh Lj Lu Lw Lx Ma Mf Mg Mh Mi Mj Mk Mm Mq Mr Ms Mu Mx Mz Na Nb Nd Ne Nf Nh Nk
Nm Nq Nr Ns Nt Nu Of Ok Om Po Qb Qc Qd Qe) aA(aE aG aJ aK aL aO aP aQ aR bE bF bJ bM bU bX cB cC cD cE cG cN cV dC dE dG dH
dI Et Fp fR Hu Io Iu Iv Jp Li Lx Ma Mi Mk Mn Mq Mt Nc Nm Nr Nu Oi Om Oz Pe Po Qb) Lx(Et Hw Ii Ij Il Im In Iq Iu Jg Jm Jo Js Li Lj Lw
Lz Ma Me Mf Mh Mj Ml Mn Mx Nb Nd Ne Nf Ng Nh Nk Nm Nq Ns Nt Nx Ny Om Pa Pc Pe Po Qa Qb Qe) Po(Et Hv Hx Ij Ik Iq Jg Jm Lu Lw
Ly Ma Mc Me Mi Mj Mk Ml Mn Mq Ms Mu Ng Nk Nn Nr Ns Nu Nx Ny Oe Oh Ok Om Oz Pa Pc Pe Pf Pg Qc) Ji(Hq Hr Ih Ij Iq Jg Jq Js Jt Lh
Li Lj Lw Lz Ma Md Mg Mk Mm Mn Mq Mv My Na Nc Nf Nl No Oh Ok Om Oy Oz Pc Pf) aP(aC aE aG aL aU aV aW aY aZ bA bB bC bE bF
bI bM bP bQ bU bW cD cE cI cJ cL cM cQ cR cS cT cX dA dB dC dG) Mu(Et Fp Ih Il Im Ir It Iu Jh Jk Jm Lj Lw Lz Mb Mc Md Me Mi Mk Mn
Mq My Mz Nb Ne Nh Nl Nt Nv Nx Oz Qa Qe) Ip(Fp Hv Hw Ih Ii Im Iq Ir Iv Js Jt Li Lu Lv Mh Mj Mm Mn Mr Mx Na Nc Nd Nj Nq Nr Nt Nv
Ny Oh Pf Qb Qd Qe) Fr(Hx Ii Ij Ik In Ir Jh Jp Jq Js Lh Lu Ly Mb Mf Mk Mn Mp Mw Mx Nc Nl Nr Nu On Oz Pa Qa Qb Qc) Nn(Et Hw Hx Il Io
Iq Ir It Jh Jm Lh Lz Md Mk Ml Mq Mx Nb Nc Nl Nu Nv Of Oh Oz Pb Pg Pz Qa Qb) Pf(Hv Hw Ik In It Jm Ly Lz Md Me Mj Ml Mq Mr Ng Nh
Nj Nm Nq Nr Ny Of Og Oy Oz Pa Pe Pg) Om(Fp Hw Hx Il Im Iq Ir Jk Lh Lv Mg Mh Mp Ms Mt Mw Mx Nd Ne Nh Nj Nk Oe Pz Qb Qd Qe)
Qa(Hr Hu It Jg Jh Lh Lu Lv Lw Mi Ml Mm Mp Mt Mw Mz Nc Ng Ni Nl Nq Nu Og Ok Pc Pe) Jn(Fp Hr Hw Hx Io Iu Lw Me Mg Mh Mi Ml
Mn Ms Mz Nd No Nt Nv Oe Og Ok Pa Pc Pe Pz) Et(Hu Hx Il In Io Jh Jk Jp Lu Lv Ly Mh Mp Ms Mw Mx Mz Nc Nd Ne Ng Nh Nm Of Qb)
aJ(aE aL aU aX aY bA bB bF bI bM bQ bR bW cC cD cG cJ cN cR cS cT cX dC dJ dK) Mw(Hq Hr Hw Ii Io Ir It Jg Lh Lv Mh Ml Mv Na Nl
Nm No Nu Nv Ok Pe Pg) Mp(Hu Hx Ih Iu Js Ly Mf Ml Mn Mv My Ne Nm No Nx Of Ok Oz Pb Pe Qe) Pe(Hr Ik Im Io Jg Jh Jq Lw Mb Me Ml
Nc Nd No Nq Oi Ok Oz Pb Pc) Jp(Hw Hx Ii Il In Io Iu Jj Jk Lh Lw Mg Mi Mz Nb Nv Oi Qb) Jq(Fp Hv Hw Hx Im Iu Li Lv Ma Mi Ms Nd Nj
Nk Nt Pa Pg Qb) Jh(Hv Hw Hx Ii Ik Iq Lh Lv Mi Mz Nb Ne Nr Pg Pz Qe) Jj(Hq Hu Iq It Jg Md Mj Mk Mm Mx My Mz Nb Nd Nf Ok) Ma(Hx
Ii In Jk Lh Lv Mt Mx Mz Pa Pg Qb Qd Qe) Mt(Ih Il Js Lh Lj Mg Mx My Ni No Nv Pd Qb) Nq(Hx Ii Ij Ik Iq Lu Lv Nr Ny Og Pa Qb) Pg(Ik Jm
Lu Mh Nc Ng Nx Oe Oi Ok Oz Pb) Og(Hw Hx Ii Ir Jk Mq Mz Nb Nm Nu Nv) Lv(Fp Lh Mx Mz Ng Nv Pa) Nj(Im Jg Mx Nr Oh Pa Qe) Oi(Jg
Lh Li Mi No Nt Ok) On(Ir Iv Ng Nk No Pb Qd) Io(Lh Mz Nb Nr Nt Nv) Ok(Hu Ij In Jk Oe Pa) Mm(Hu Hx Ij Ir Qb) Jr(Iq Jo Pd Wm) bA(bC bE
bJ cS) bV(aO bL bQ cR) Qd(Im Mh Pz) Jg(Ms Pa Pz) Lh(Im Jo Oe) cS(aO cF dM) cU(al aO cM) Nt(Jo Ng) Mz(Mh Nk) Hu(Lw Pc) Oh(In Nr)
bQ(bO cE) dK(dF dM) NbOe NyPb aMaX bWcF Unconstrained panels with 2 analytes, where 1.0E-4 >= 'AUC p-value' > 1.0E-5. Contains 1,477 panels of 11,037 total panels evaluated. : aA(aC
aD aH aM aN aS aV aZ bA bB bG bI bN bP bR bS bV cA cI cK cL cQ cT cW cY cZ dA dF dJ dL dM Hq Hv Hw Hx Ih Ii Ij Il Im In Ir It Jo Jq
Js Jt Lh Lj Lu Ly Mc Mj Ml Mr Ms My Mz Na Nb Nd Ne Nf Ng Ni Nl No Ns Nv Nx Ny Of Oh Pa Pb Pd Pf Pz Qc Qd Qe) Pg(Fp Hq Hr Hu Hv
Hw Hx Ih Ii Ij Il In Iq Ir It Iu Iv Jg Jk Jn Jo Js Jt Lh Li Lj Lv Lw Lx Ly Lz Mc Md Me Mf Mg Mi Mj Mk Ml Mn Mq Mr Ms Mt Mv Mx My Mz
Na Nb Nd Ne Nf Nh Ni Nk Nl Nm No Nq Nr Ns Nt Nu Nv Ny Of Oh Oy Pa Pc Pd Pe Qa Qb Qc Qd Qe) Et(Fp Fr Hq Hr Hv Hw Ih Ii Ij Ik Im Iq
Ir It Iu Iv Jg Jm Jo Jq Js Jt Lh Li Lj Lw Lz Ma Mb Mc Md Me Mf Mi Mj Mk Ml Mn Mq Mr Mt Mv My Na Nb Nf Ni Nl No Nq Nr Ns Nt Nu
Nv Nw Nx Ny Oh Ok Om Oy Oz Pb Pc Pd Pf Qc Qd Qe) Pe(Fp Hq Hu Hv Hw Hx Ih Ii Ij Il In Iq Ir It Iu Iv Jk Jm Js Jt Lh Li Lj Lu Lv Ly Lz Mc
Md Mf Mg Mh Mi Mj Mk Mn Mq Mr Ms Mt Mv Mx My Mz Na Nb Ne Nf Ng Nh Ni Nk Nl Nm Nr Ns Nt Nu Nv Nx Ny Oe Of Oy Pa Pd Qb
Qc Qe) Om(Fr Hq Hr Hu Hv Ih Ii Ij Ik Io It Iu Iv Jg Jh Jo Jp Jq Js Li Lj Lu Lw Lz Ma Mb Mc Md Me Mf Mi Mj Mk Ml Mm Mn Mq Mr Mu My
Mz Na Nb Nc Nf Ng Ni Nl Nm Nn No Nq Nr Ns Nt Nu Nv Ny Of Oh Ok Oy Oz Pb Pc Pd Pf Qc) Fr(Fp Hq Hr Hu Hv Hw Ih Il Im Iq It Iu Iv Jg
Jk Jm Jo Li Lj Lw Lx Lz Ma Mc Md Me Mi Mj Ml Mq Mr Mt Mu Mv My Mz Na Nb Nd Ne Nf Nh Nm Nn No Nq Ns Nt Nv Nx Ny Oh Ok Oy
Pb Pc Pf Po Qd Qe) Qa(Fp Hq Hv Hw Hx Ih Ii Ij Il Im In Iq Ir Iu Iv Jk Jm Js Jt Li Lj Ly Lz Mb Mc Md Me Mf Mg Mj Mk Mn Mq Mr Mv Mx
Na Nb Nd Ne Nf Nh Nk Nm No Nr Ns Nt Nv Nx Ny Oe Oh Oz Pa Pf Po Qb Qc Qe) Jn(Hq Hu Hv Ih Ii Ij Ik Il In Iq Ir It Iv Jq Js Lh Li Lj Lu Ly
Lz Mb Mc Md Mf Mj Mk Mq Mr Mv Mx My Na Nb Nc Ne Nf Ng Nh Ni Nk Nl Nm Nr Ns Nu Nx Ny Of Oh Oy Oz Pb Pf Qb Qc Qd Qe)
Ma(Fp Hr Hv Hw Ih Ij Il Im Io Iq Iv Jh Jp Js Li Lj Lu Lw Md Mg Mh Mi Mj Mk Mn Mp Mq Mr Ms Mu Mw Nb Nc Nf Ng Nj Nk Nn No Nq Nr
Nt Nu Nv Ny Oe Og Oi Ok Pz) aJ(aC aD aF aG aH aK aM aN aP aQ aR aS aV aW aZ bE bG bH bJ bL bN bP bS bU bV bZ cA cB cE cH cI cK
cL cO cP cQ cV cW cY cZ dA dB dE dF dG dI dL) Jh(Fp Hq Ij Il Ir Iu Iv Jg Jk Jm Jp Jq Js Lw Ly Lz Mc Md Me Mh Ml Mn Mq Mr Mx Na Nc
Nf Nh Nj Nk Nl Nm Nq Ns Nu Nv Of Oh Oi Ok On Oz Pb Pc Qb) Jp(Fp Hv Ih Ij Im Ir Iv Jg Jq Js Lu Lz Md Mf Mh Mj Mk Mm Mq Mr Ms Mv
Mw Mx Nc Nd Ne Nf Nj Nk Nm No Nr Ns Nu Nw Nx Oe Og Oh Ok Pc Qd Qe) Im(Fp Hx Ih Ii Iq Ir Iv Jg Jk Js Jt Li Lu Lv Lw Mh Mi Mj Mp
Mr Mt Mw Mz Nb Nc Nk Nn No Nq Nr Nt Nv Nx Og Oh Oa Pc Pe Pf Po Qe) Po(Fp Hu Hw Ih Ii Il In It Iu Jo Lh Lz Mb Md Mf Mg Mh Mm
Mr Mv Mx Mz Na Nb Ne Nf Nh Ni Nm No Nq Nt Nv Pb Pd Qb Qe) Nw(Hq Hr Hu Ih Ik It Jm Jo Js Jt Li Ly Lz Mb Mc Md Me Ml Mn Mv My
Nc Ng Ni Nl No Nv Nx Ny Oh Oy Oz Pb Pc Pd Pf) aP(aD aF aH aK aM aN aQ aR aS aX bG bH bJ bL bN bS bV bZ cA cB cC cG cH cK cO
cV cW cY cZ dE dF dI dJ dL dM) Lv(Hx Ih Io Iq Ir Iv Jk Li Lj Lz Md Mh Mj Mn Nb Nc Nd Nf Nh Ni Nj Nm Nr Nt Nu Nx Ny Og Pb Pc Pf Qb
Qe) Mz(Fp Hr Hv It Jg Jq Li Lw Lx Mi Ml Mm Mn Nd Ni Nl Nm Nq Nt Nu Oe Of Oh Oi Ok Oy Pb Pf Pz Wm) Ok(Fp Hx Ii Il Io Iq Ir Iu Lh Lx
Mh Mt Mu Nc Nd Ne Nh Nk Nn Nq Nr Nt Nu Nv Ny Of Qb Qd Qe) Mw(Fp Hu Hx Ih Il Iu Iv Jk Js Lj Lu Ly Mf Mk Mm Mn Ms Nc Ng Ni Nk
Nl Nx Oe Oi Qb Qc Qe) Ip(Hq Hu Ij Il In Io Iu Lj Lw Lz Mb Md Mk Mq Ms Mv My Na Nf Ni Nl Nv Oi Oy Oz Pc Pd Pz) Nn(Fp Hq Hu Ih Iu
Jk Js Mb Me Mn Mr Mv Na Ne Nf Nh No Nq Nt Nx Oy Qd Qe) Mm(Fp Ii In Io Iv Jk Jq Js Lh Lu Lx Mh Ms Mx Nc Nj Nk Nt Og Pa Pz Qd Qe)
Nq(Fp Hv Hw Il In Ir Jm Lh Mf Mh Mi Mj Mn Mu Nb Nc Ne Nk Nu Oh Qd Qe) Jq(Hu Ii Il Ir Iv Jg Jj Lh Mg Mh Mn Mr Mv Mx Nb Nl No Nr
Nv Og Qd Qe) bV(aC aG al aM aX aY bC bE bF bJ bO bW bZ cC cG cK cM cO cS dC dD dE) Lx(Ih Ik Ir It Iv Jk Lh Ly Mb Md Mg Mr Mv
Na Nc Nl Nv Pd Qc Qd) bQ(aI aQ aY aZ bA bL bU bW bX cC cD cL cM cS cV cX dB dD dH dK) Oh(Hu Hw Ii It Iu Lh Mi Mj Ms Mu Mx Nb
Nt Nu Nv Ny Oi Pa Pz) No(Fp Hx Ij In Io Jk Lh Li Mn Ms Nd Nt Nu Oe Of Qb Qe) Jj(Hv Ik Jt Lj Lu Lz Mh Mq Nc Nk Nl Nm Nu Nx Of Oy
Pf) Mu(Hr Iv Jg Jo Li Ly Mf Ml Mr Mv Na Nf Ns Pc Qd Wm) Pf(Hr Il Iq Iu Mn Mp Mv Mx Na Nf Ni Nl Nv Oi Pb Pc) Jg(Hx Ii Ij In Iq It Lh
Lu Ly Mp Mx Ny Qb Qd Qe) aO(aM aR aX bA bH bJ bO cE cJ cM dG dI dK dL dM) Nj(Hw Ih Ii Iq Iv Jk Js Jt Mj Mr Nu Ny Qb) Mi(Hr Io Lw
Mn Ms Nd Ng Nk Ny Pa Pb Qb) Mt(Hw Ir Iu Jk Jt Ml Nc Nm Nt Of Qe Wm) Mp(Fp Hr Iv Jk Lj Mg Mk Nh Pd Qc Qd) Ny(Hv Ik Jm Lw Mq
Na Nd Nm Nu Og) Nt(Hx Ik Mh Ms Nd Nk Oe Pa Qb) Og(Ih Iu Iv Jt Li Mv Nr Qd Qe) bA(aI aX bO bZ cG cR cT dB dD) Lw(Fp Hx Iq Ir Mx
Nd Nu Qe) Lh(Fp In Mg Ng Nk Of Pz Qb) Nv(Fp Mh Mx Nd Nu Oe Oi Qb) Ir(Hr Io Jk Li Mn Oi Pc) cS(aF aM bG cQ cU dD dF) Jk(Fp Io Mh
Of Oi Pz) Pa(Hv Nc Nm Nu Oe Oz) cU(cG cH cK cW dK dM) bW(cQ cT dD dF dM) Ji(Jo Pd Qb Wm) Oi(Ih Iv Jt Qd) al(cK dE dI dM) bC(aF
dF dM) Md(Hv Nu) Mx(Nc Nl) Nd(Hv Nm) Qd(Li Mb) On(Mv Nc) dF(cC cF) dM(aU aX) MhHx NbNk NgLi lolq PzQe dAdK Unconstrained panels with 2 analytes, where 1.0E-3 >= 'AUC p-value' > 1.0E-4. Contains 1,796 panels of 11,037 total panels evaluated. : Qd(Fp
Hq Hu Hv Hw Hx Ih Ii Ij Ik Il In Io Iq Ir It Iu Iv Jh Jk Jm Js Jt Lh Lj Lu Lv Lw Ly Lz Mc Md Me Mg Mi Mj Mk Ml Mn Mq Mr Ms Mt Mv Mw
Mx My Mz Na Nb Nc Nd Ne Nf Ng Nh Nk Nl Nm No Nr Ns Nt Nu Nv Nx Ny Oe Of Oh Oy Oz Pa Pb Pc Pe Pf Po Qa Qb Qc Qe Wm) Ir(Fp Hq
Hu Hv Hw Hx Ih Ii Ij Ik Il In Iq It Iu Iv Jm Js Jt Lh Lj Lu Lz Mb Mc Md Me Mf Mg Mh Mi Mj Mk Ml Mq Mr Ms Mv Mx My Mz Na Nb Nc

Figure 42 Continued

Nd Ne Nf Ng Nh Ni Nk Nl Nm No Nr Ns Nt Nu Nv Nx Ny Oe Of Oh Oy Oz Pa Pb Pd Pf Po Pz Qb Qc Qe) Jk(Hq Hv Hw Hx Ii Ij Ik Il In Iq It Iu Iv Jg Jm Js Lh Li Lj Lu Lw Ly Lz Mb Mc Md Me Mf Mg Mi Mj Mk Ml Mn Mq Mr Ms Mv Mx My Mz Na Nb Nc Nd Ne Nf Ng Nh Ni Nk Nl Nm Nq Nr Ns Nt Nu Nv Nx Ny Oe Oh Oy Oz Pa Pb Pc Pd Pf Po Qb Qc Qe) Qe(Fp Hq Hr Hv Hw Hx Ih Ii Ij Ik Il In Io Iq It Iu Iv Jm Js Lh Li Lj Lu Mb Mc Md Mf Mg Mh Mi Mj Mk Ml Mn Mq Mr Ms Mv Mx Mz Na Nb Nc Nd Ne Nf Ng Nk Nm Nr Ns Nt Nu Nv Nx Ny Oe Oh Oi Oy Pa Pb Pc Pf Qb Qc) Nt(Fp Hq Hr Hu Hv Hw Ih Ii Ij In Iq It Iu Iv Jg Jh Jm Js Lh Li Lj Lu Lw Lz Mb Mc Md Me Mi Mj Mk Ml Mn Mq Mr Mv Mx Na Nb Nc Ne Nf Nh Nl Nm Nq Nr Ns Nu Nv Nx Ny Of Oy Oz Pb Pc Pf Pz) Hx(Fp Hr Hu Hv Hw Ih Ii Ij Ik In Io Iq Iu Iv Jm Lh Li Lj Lu Ly Mc Md Me Mf Mg Mi Mj Ml Mn Mq Mr Ms Mv Mx My Mz Na Nc Nd Ng Ni Nk Nm Ns Nu Nv Nx Ny Oe Of Oh Oi Oy Pb Pc Pf Pz Qb) Ny(Fp Hq Hu Hw Ih Ii Ij Il Im In Io Iq It Iu Iv Jp Jq Js Lh Li Lj Lz Mc Md Me Mf Mh Mj Mk Ml Mm Mn Mr Mv Mx My Mz Nc Ne Nf Nh Nk Nl No Nr Ns Nv Oe Of Oi Oy Oz Pa Pc Pz Qb) No(Hq Hr Hv Hw Ih Ii Iq Iu Iv Jg Jh Js Lu Lw Lx Ly Mc Mf Mh Mi Mj Mk Ml Mm Mq Mu Mv Mx My Mz Nb Nc Ne Ng Nh Nk Nl Nm Nq Nr Ns Nv Nx Oh Ok Oy Oz Pa Pb Pf Pz Qc Wm) Im(Hq Hr Hu Hv Hw Ij Ik Il In Io It Iu Jh Jm Lj Ly Lz Mb Mc Md Me Mf Mg Mk Ml Mm Mn Mq Ms Mv Mx My Na Nd Ne Nf Ng Nh Nl Nm Ns Nu Oe Of Oi Oy Oz Pb Pd Pz Qb Qc) Nv(Hq Hr Hu Hv Hw Ii Ij Ik Il In Iq It Jg Jm Lh Li Lj Lu Lw Ly Mb Mc Md Mf Mi Mj Mk Ml Mm Mn Mq Mr Ms Mv My Mz Na Nb Ne Ng Nh Nk Nm Nq Nr Ns Of Oy Oz Pa Pz) bQ(aD aE aF aG aH aK aL aM aN aO aR aS aV aW aX bB bC bE bF bG bH bI bJ bM bN bP bR bS bZ cA cB cF cG cI cJ cK cN cO cQ cR cT cW cY cZ dA dC dE dI dL) Ok(aA Hq Hr Hv Hw Ih Ik It Iv Jg Jm Jq Js Li Lj Lu Lw Ly Mc Md Me Mf Mg Mi Mj Mk Ml Mm Mn Mq Mr Mv Mx My Nb Nf Ng Ni Nl Nm Ns Nx Oh Oz Pb Pc Pf Pz) Lh(Hq Hr Hu Hv Hw Ij Iq It Iv Li Lj Lu Lw Mb Mc Md Me Mh Mi Mk Ml Mn Mq Mr Ms Mx My Mz Na Nb Nc Nd Ne Ni Nm Nr Ns Nu Nx Oy Pb Pc Pd Pf Qc) Mz(Hq Hu Hw Ii Ij Ik Il In Iq Iu Iv Js Lj Lz Mb Mc Md Me Mf Mg Mj Mk Mq Mr Ms Mv Mx My Na Nb Nc Nf Ng Nr Ns Nx Oz Pa Pc Qb Qc) Jg(Fp Hq Hv Hw Ih Ik Il Io Iu Iv Js Lj Lw Ma Mc Md Mh Mi Mj Mk Mn Mq Mr My Nb Nc Nd Nk Nm Nn Nq Nr Ns Nu Nx Oe Of Oh Pb Pc Pf) aO(aC aD aF aG aI aL aN aU aY aZ bF bG bI bL bP bS bX bZ cB cC cD cF cG cI cK cL cP cQ cR cT cV cW cX cZ dA dB dC dD dE dF dH) Ma(Hq Hu Ik It Iu Jm Jo Jt Ly Lz Mb Mc Me Mf Ml Mm Mv My Na Nd Ne Nh Ni Nl Nm Ns Nx Of Oh Oy Oz Pb Pc Pd Pf Qc) Li(Fp Ih Ii Il In Io Iq Iv Jh Jp Lu Lw Mb Md Mm Mn Mp Ms Mt Mw Mx Nb Nc Ne Nh Nj Nk Nn Nq Ns Nx Pa Pb Po Pz Qb) bA(aC aD aE aM aN aQ aR aS aU aW aY aZ bB bH bL bS bV bX cC cD cE cJ cK cM cO cQ cV cX cY dC dE dF dG dH dI dK) bV(aE aF aK aQ aS aU aV aW aZ bB bG bH bM bP bR bS bU cA cB cD cE cF cI cL cN cT cV cX cY dB dF dG dH dI dJ) Qb(Fp Hv Hw Ih Ii Io Iq Iu Iv Jm Js Jt Lu Lw Md Mg Mh Mj Mn Mq Mr Mv Mx Na Nb Nm Nr Nu Nx Og Oh Pa Pc Pf) Jq(Hq Ih Ij Iq Jm Jo Jt Lj Lu Lw Ly Lz Md Me Mf Mj Mk Ml Mq My Na Nc Nf Ni Nm Ns Oe Of Oh Oi Oy Pc Pd Pf) Mn(Fp Hv Hw Ih Ii Ij In Io Iq Iu Iv Jp Js Lu Lw Md Mh Mj Mm Mq Mr Ms Mx Nb Nd Nj Nm Nr Og Oh Oi Pa) dF(aC aG aI aM aX aY aZ bB bE bF bH bJ bL bO bS bX cD cE cK cM cN cR cU cV cX dB dC dD dE dH dM) Lv(Hr Hu Hw Ii Ik Il Iu Js Jt Lu Lw Mc Me Mf Mk Ml Mq Ms Mv My Na Nk Nl Ns Oe Of Oi Oz Pz Qc) Jp(Hq Hr Hu Ik Iq It Jm Jo Jt Lj Ly Mb Mc Me Ml My Na Ng Nh Ni Nl Of Oy Oz Pb Pd Pf Pz Qc) Nq(Hq Ih It Iu Iv Js Lj Lw Ly Lz Mc Md Me Mk Mq Mr Ms Mx My Na Nf Nh Nl Ns Nx Oy Oz Pc) Mm(Fr Hv Hw Ih Il Iq Lj Lw Ly Mb Md Mi Mj Mk Mr Mt Mu Nb Nd Ng Nl Nr Nu Nx Oe Pf) Jj(Hr Io Lw Ly Mb Mc Me Mf Ml Ms Na Ne Ng Nh Ni Nj Ns Oe Og Oh Oz Pb Pc Pz Qc) cU(aF aL aM aR aU aZ bB bG bI bL bN bO bS bW cF cJ cQ cR cT cX dA dD dE dG dL) Oh(Fp Hq Ih Ij Il Iq Lw Ly Lz Mc Md Ml Mq Mr My Nd Ne Nh Nm Ns Oy Oz Pb) Nm(Fp Hu Hv Ii In Iq Mh Mi Mj Mu Mx Nb Ng Nj Nn Nr Nu Of Oi Pb Pz) Ip(Hr Ik It Jm Jo Ly Mc Me Mf Mg Ml Ne Ng Nh Ni Nl Ns Oe Of Pb Qc) Nr(Hr Hv Lw Mc Md Mh Mi Mq Mr Ms Mx Na Nb Ng Nk Ns Nu Oe Of Pb) Ij(Fp Ii Iq Js Lz Md Mh Mi Mr Mv Mx Nb Nc Nd Nf Nj Nk Og Pb Pc) cG(aI aK aM aQ aU bO bS bX cE cF cK cL cQ cR cT cY dC dD dK dM) Mx(aA Hq Hu Ih Ii Io Iv Js Mh Mi Mv Nb Nk Nu Nx Oe Og Pd) Fp(Hw Ih Ii Iq Iu Js Md Mh Mi Mj Mq Nb Nd Nj Nx Pa Pc) Nb(Hr Hu Hv Lj Lw Ly Ms Nc Nd Nu Of Oi Pf Pz Wm) Mi(Hu Ii Iq Mb Mh Mk Ml Nc Nl Nu Oe Of Pz Qc) Iv(Ik Io Iq Lw Mh Ms Mt Nd Ng Nk Nn Oe Pa Po) Pf(Hq Ih Js Lj Mb Mf Mh Mk Ms My Nu Nx Oe Qc) Jh(Hr Ih Io It Jt Lu Mf Mk Mv Ng Nx Oe Qc) Pa(Hr Ik Il Io Jm Ly Mf Mq Mv Na Ng Og Pz) dM(aJ bB bE bL bO bZ cD cF cJ cM cR dC dD) Wm(aA Et Fr Jl Lx Mp Nw Om On Pd Pg Po) aI(aM aR aX bC bH bS bW bZ cS dA dG dK) Hv(Hu Ii Ik Me Mh Ml Mr Nj Nk Nl Of) aA(cH cP cR Ik Iq Jm Lz Mb Md Nh Oy) dK(aN bC bG bO bS bW bZ cF cW dD dG) Lw(Hw Js Lu Mh Mj Mr Mv My Og) Nu(Ih Ii Io Iq Iu Mr Ms Ng) Jt(Fr Jn Lx Mp Ms Mu Mw Om) Nj(Iu Md Mv My Nf Oy Pd) bC(bO cK cQ cR cT cY dE) cS(bM bO cK cR cT cY dA) Nk(Ii Js Md Mj Nn Nx) Iq(Ii Mf Mv Nx Og Pc) dG(aX aY bO cF cR dD) Mr(Oe Of Og Oi Pb) Na(Ih Ii Js Oe Og) Om(In Jm Ly Mv Nx) Pd(Fr Jn Mu Mw Qa) Nd(Md Mf Mq Nh) Ni(Fr Lx Mp Mu) Hu(Md Mh Mq Mu) Ih(Io Oe Pb Pz) Js(Io Ms Oi Po) bW(aL bG bO cK) dD(bS cK dE dI) Nn(Hr Lj Qc) Mb(Mp Mw Pg) Mv(Ms Ng Oi) My(Md Nc Qa) Ii(Ik Ly Nc) Jo(Jn Mp Qa) Nx(Io Ms Og) aM(bZ dE dI) Nl(Hw In) aL(bE dE) dI(cC cF) PoNc LxOf MgMw MjNh MuQc IlOg QaOy JmJn aPcP bBbS bOdA bZcT

Unconstrained panels with 2 analytes, where 1.0E-2 >= 'AUC p-value' > 1.0E-3. Contains 1,990 panels of 11,037 total panels evaluated. : dG(aC aD aE aF aG aH aK aL aM aN aQ aR aS aV aW aZ bB bC bE bF bG bH bI bJ bL bM bN bP bQ bR bS bU bW bX bZ cA cB cC cD cE cG cH cI cJ cK cL cM cN cO cQ cS cT cV cW cX cY cZ dA dB dC dE dF dH dI dJ dL dM) Js(Hq Hr Hu Hv Hw Hx Ih Ii Il In Iq It Iu Iv Jm Jq Jt Lh Li Lj Lu Ly Lz Mb Mc Md Me Mf Mg Mh Mi Mj Mk Ml Mq Mr Mv My Nb Nc Nd Ne Nf Ng Nh Ni Nm Nr Ns Nu Nv Nx Oe Of Og Oh Oy Oz Pa Pb Pc Pd Pz Qc) Iv(Fp Hq Hr Hu Hv Hw Ih Ii Ij Il In It Iu Jm Jt Lj Lu Ly Lz Mb Mc Md Me Mf Mg Mi Mj Mk Ml Mq Mr Mv My Na Nb Nc Ne Nf Nh Ni Nl Nm Nr Ns Nu Nv Nx Of Oh Oy Oz Pb Pc Pd Pf Pz Qc Wm) Iq(Hq Hu Hv Hw Ih Ik Il In It Iu Jm Jt Lj Lu Ly Lz Mb Mc Md Me Mg Mh Mj Mk Ml Mq Mr Ms Mx My Na Nb Nc Nd Ne Nf Ng Nh Ni Nk Nl Nr Ns Oe Of Oi Oy Oz Pa Pb Pd Pz Qc) cG(aC aD aE aF aG aH aL aN aR aS aV aW aX aY aZ bB bC bF bG bH bI bJ bL bM bN bP bR bU bZ cA cB cC cD cI cJ cM cN cO cP cS cV cW cX cZ dA dB dE dF dH dI dL) Fp(Hq Hr Hu Hv Ik Il In Io It Jm Jo Jt Lj Lu Ly Lz Mb Mc Me Mf Mg Mk Ml Mr Ms Mv Mx My Na Nc Ne Nf Ng Nh Nk Nl Nr Ns Nu Oe Of Og Oi Oy Oz Pb Pd Pf Pz Qc) Ih(Hq Hu Hv Hw Ii Ij Ik In It Iu Jk Jm Lh Lj Lu Lw Ly Mb Mc Md Mf Mg Mh Mi Mj Mk Ml Mq Mr Ms Mv My Mz Nb Nc Nd Ne Nf Ng Nh Nk Nl Nm Nr Ns Nv Nx Pa Pc Wm) Ij(Hq Hr Hu Hv Hw Ik In Io It Jm Jt Li Lj Lu Lv Lw Ly Mb Mc Me Mf Mj Mk Ml Mq Ms My Na Ne Ng Nh Ni Nl Nm Nr Ns Nu Nx Oe Of Oi Oy Oz Pa Pd Pf Pz Qb Qc) aI(aC aD aE aF aG aH aK aN aQ aU aV aW aY aZ bE bF bG bJ bL bN bO bR bU bX cA cB cC cD cE cF cJ cL cM cN cO cP cQ cR cT cV cW cX cY cZ dB dC dH dJ dL) Ii(Hq Hr Hu Hw Il In Io It Iu Jm Jt Lh Lj Lu Lw Lz Mc Md Me Mf Mk Ml Mq Mr Ms Mv My Nb Nd Nf Ng Nh Ni Nl Nr Ns Oe Of Oi Oy Oz Pa Pb Pc Pd Pf Pz Qc) Li(Hq Hr Hu Hv Hw Ik It Iu Jg Jm Jo Jt Lj Ly Lz Mc Me Mf Mg Mh Mi Mj Mk Ml Mq Mr Mv My Na Nd Nf Ni Nl Nm Nr Nu Oe Of Oh Oy Oz Pc Pd Pf Qc) Mh(Hq Hr Hw Il In Io It Iu Jt Lj Lu Mb Md Mf Mg Mj Mk Ml Mq Ms Mt Mv My Na Nb Nc Nd Nf Nh Ni Nj Nk Nu Nx Oe Og Oh Oi Oy Oz Pa Pb Pd) cU(aC aD aE aG aH aK aN aQ aS aV aW aX aY bC bE bF bH bJ bM bP bQ bR bU bX bZ cA cB cC cD cE cI cL cN cO cP cV cY cZ dB dC dH dI dJ) bW(aC aF aK aM aN aQ aR aS aU aW aZ bB bC bI bJ bL bM bN bR bS bX cA cB cH cI cJ cL cM cO cR cV cW cX cY cZ dA dB dC dE dH dI dJ) cS(aC aD aE aG aH aK aL aN aQ aS aU aV aW aX aZ bB bF bI bJ bL bP bR bS bU bZ cB cC cD cE cH cJ cL cM cN cW cX cZ dC dE dH dJ dK) dM(aE aF aG aH aK aL aM aN aQ aR aV aW aY aZ bA bF bH bI bM bQ bR bU bV bX cA cB cC cE cN cO cP cQ cT cV cX cY dB dE dH dI dJ dL) Mn(Hq Hr Hu Ik Il It Jm Jt Lj Ly Lz Mb Mc Me Mf Mg Mk Ml Mv My Na Nc Ne Nf Ng Nh Ni Nk Nl Ns Nu Nx Oe Of Oy Oz Pb Pc Pd Pz Qc) dF(aD aE aF aH aK aL aN aQ aR aS aU aV aW bG bI bM bN bP bQ bR bU bZ cA

Figure 42 Continued cB cH cI cJ cL cO cP cQ cT cW cY cZ dA dI dJ dL) Nu(Hq Hu Hv Hw Il In It Jm Lj Lu Lz Mc Me Mj Mk Ml Mq Mv My Na Nc Nd Ne Nf Nh Ni Nk Nl Ns Nx Oe Of Oi Oz Pb Pc Pz Qc) Qb(Hq Hr Hu Ik Il In It Jo Lj Ly Lz Mb Mc Me Mf Mk Ml Ms My Nc Nd Ne Nf Ng Nh Ni Nk Nl Ns Oe Of Oi Oy Oz Pb Pd Pz Qc) Nb(Hq Hw Hx Ik Il In It Iu Jm Lu Lz Mb Mc Md Me Mf Mi Mk Ml Mq Mr Mv My Na Ne Nf Nh Ni Nl Ns Nx Ny Oz Pa Pb Pc Qc) Mm(Hq Hr Ik It Iu Jg Jh Jm Jo Jt Lz Mc Me Mf Mg Ml Mq Mv My Na Ne Nf Nh Ni Nm Nn Nq Ns Of Oh Oy Oz Pb Pc Pd Qc) Nc(Hq Hu Hv Hw Il In It Iu Jt Lu Lw Md Mg Mj Mq Mr Mv Na Nd Ne Nf Nh Nl Nm Nr Nv Nx Oe Of Og Oh Pd Pf) Pa(Hq Hu Hw In Iu Jt Lh Lj Lu Lw Lz Mb Mc Md Mg Mr Ms Mx Nd Ne Nf Nh Ni Nk Nl Nr Ns Nx Oi Pc Pd Qc Wm) Nm(Hq Hw Ik Il It Iu Lj Lu Lw Ly Lz Mc Md Mf Mk Mr Ms Mv My Ne Nf Nh Ni Nk Nl Nq Ns Nx Oe Oy Oz) Mx(Hv Ik Il It Iu Jm Jt Lj Lu Ly Lz Mc Md Mg Mk Ml Mq Mr Ms My Na Nd Nf Ng Ni Oi Oy Pb Pc Pz Qc) Mv(Hq Hv Io Iu Jg Jm Lh Lu Ly Mc Md Me Mi Mj Mq Mr Mt Na Nd Nk Nl Nq Nr Oe Of Oh Oy Oz Pb Pz) Hq(Hv Hx Ik In It Lj Lv Lw Lz Mc Md Mi Mj Mk Ml Mq Mr Na Nj Nr Ns Nx Of Og Oy Pz) Hu(Hw Iu Jg Jh Jt Lu Lz Mb Mg Mj Mr My Na Nd Nj Nk Nl No Nq Nr Ns Nx Oe Og Pf Qe) bA(aF aG aH aK aL aV bF bG bl bM bN bP bR bU cA cB cH cl cL cN cP cW cZ dA dJ dL) Hv(Hr In Io It Iu Jm Lu Ly Lz Mc Mf Ml Mj Mq Ms My Na Ng Ni Ns Nx Oe Og Pb Pc) Jt(Hx Io Jg Jk Jo Lh Lj Ly Ml Mz Nd Ng Nk Nn No Nq Nt Nv Ny Ok Pb Po Pz Qe Wm) Nr(Hx Ik In It Iu Lj Lu Ly Lz Me Mf Mj Ml My Nd Nf Ni Nl Oi Oy Oz Pc Pz) bC(aD aK aM aN aQ aU aW aZ bB bE bG bL bN bR bS bZ cC cF cW dA dB dC dD) Mi(Ik It Jm Lj Lu Ly Lz Mc Md Me Mf Mj Mq Mr My Na Ne Nh Nx Oy Oz Wm) Jg(Hr It Jm Jo Lz Mb Me Mf Mg Ml Na Ne Nf Ng Nh Ni Nl Oy Oz Pd Qc Wm) dK(aD aL aM aR aU aW bB bL bM bP cE cK cN cO cP cQ cR cT cY cZ dE dI) bO(aF aM aN aR aW aX bF bH bL bZ cE cJ cK cQ cT cW dD dE dH dI dL) Mr(Hr Ik In Io Lj Mc Md Mf Mj Ml Mq Ms My Nd Ne Ng Nk Nl No Ns) aO(aE aH aK aQ aS aV aW bB bE bM bN bR bU cA cH cN cO cY dJ) cT(aG aR aX bE bH bJ bL bS cC cF cK cO cQ cR cX dA dD dE dI) Wm(Ip Is Jh Jk Jn Jq Lh Ma Md Nn Nq Nv Ny Og Pe Qa Qc Qe) Iu(Ik Io Lh Lj Lu Lw Ms Nd Ng Nh Nk Nl Nv Nx Oe Oi Pc Pz) Pd(Hx Il In Jh Lv Ms Mz Nd Nk No Nt Ny Oe Og Oi Ok Qd Qe) bZ(aL aN aS bB bI bN cC cD cF cJ cM cQ cR cW cZ dA dD dL) My(Ik Lu Mc Mj Ms Nd Ne Ng Nh Nk Nl Nt Oe Of Og Oi Qe) Jo(Im Ir Jh Jk Lv Mw Mz Ng Nj Nk No Nq Nv Og Ok Qd Qe) Nx(Hw Il In Jq Lj Lu Mj Na Nd Ng Nj Nv Ny Oe Of Oh Oi) bV(aD aH aL aN aR bl bN bX cH cJ cP cQ cW cZ dA dL) Lw(Hr Il In It Lj Lz Mk Mq Ms Na Nf Ni Nk Nl Oy) Mj(Ik Io Lh Lj Md Mf Ml Mq Ms Nd Nl Og Pb Pz) Jq(Hr Ik In Io It Mb Mc Ne Ng Nh Oz Pb Pz Qc) Oh(Hr Ik Jm Lj Lu Me Mf Mk Na Nf Nl Oe Of Og) No(Il It Jm Lj Lz Mb Md Me Mg Na Nf Ni Pc) bL(aL aM aN bl cC cF cJ cM cQ cW dA dD dL) dE(aH bB bl cC cD cF cJ cM cQ cR cW dL) Lz(Hx Io Lh Lj Ms Nj Nv Og Oi Ok Qe) Mg(Jh Lj Lv Nk Nn Nq Nt Nv Ny Og Oi) Nl(Hx Il Lh Ly Mq Na Ne Nj Nv Og Qe) dI(aE aF aL aS bB bl cM cQ cR cV cW) Lu(Hw Mf Mq Mz Na Nd Nj Ny Pc Pf) Ni(Im Jh Nk Nn Nq Nt Nv Ny Qd Qe) aX(aH aL cC cF cK cQ cW cZ dA dD) Nk(Hw In It Mq Na Nd Nf Og Pf) Hx(Il It Mb Mk Ne Nf Nh Oz Qc) dD(aC aR bE bH cF cR cW dA dL) Hw(Hr Io Me Ms Ng Oe Of Pc) Lh(Ik Il Jm Ly Mf Nf Nh Oz) Nq(Hr Mb Ml Oe Of Pb Qc) Lv(In It Jm Ly Mb Ne Oy) Md(Io Lj Mb Mk Mq Na Og) Nd(Il It Ml Ms Na Nf Nj) aF(aK aM aV aW cV cX dL) cR(aL aN bS cJ cW dA dL) Nj(Il In Lj Mk Mq Na) Ny(Hr Ly Mb Ms Ng Qc) cW(aG aY bF cE cO dC) Qe(Ly Me Nh Of Oz) Nv(Me Nf Pb Pc Qc) bQ(aC aU cH cP dJ) bS(bF cD cE cF cM) cK(aL cJ cM cQ dL) dA(aU bB cE cF cM) Nt(Il Ly Mf Qc) Mq(Lj Ms Oe Pb) Mz(Jm Ly Ne Nh) Jh(Lj Mb Ms Oy) Ok(Mb Na Oy Qc) Oi(Jj Lj Pc) aM(bE bF cJ) Mf(Og Qd) Hr(Jk Qd) Pc(Il Og) bF(cQ dL) bH(bl cM) cE(cF cM) cJ(cF cQ) dC(aD aR) NnOe LyIr MsNa MtOy blcO Constrained panels with 3 analytes, where 1.0E-8 >= 'AUC p-value' > 0. Contains 7,778 panels of 397,580 total panels evaluated. : Jj{Mp(aA Et Fp Fr Hq Hu Hv Hw Hx Ih Ii Ij Il Im In Ip Iq Ir Is Iu Iv Jg Jh Ji Jk Jl Jm Jn Jo Jp Jq Jr Js Jt Lh Li Lj Lu Lv Lw Lx Ly Ma Md Mg Mh Mi Mm Mq Mr Ms Mt Mu Mv Mw Mx Mz Na Nb Nc Nd Nf Nk Nm Nn No Nq Nr Ns Nt Nu Nv Nw Nx Ny Oh Ok Om On Pa Pc Pd Pe Pg Po Qa Qb Qd Qe) Nq(aA Et Fp Hu Hv Hw Hx Ih Ii Ij Il Im In Ip Iq Ir Is Iu Iv Jg Jh Ji Jk Jl Jn Jo Jp Jq Jr Js Jt Lh Li Lj Lv Lw Lx Ma Md Mi Mn Mq Mr Mt Mu Mw Mx Mz Na Nb Nc Nf Nj Nm No Nr Nt Nu Nv Nw Nx Ny Oh Ok Om On Pa Pc Pd Pe Pg Po Qa Qb Qd Qe) Nn(aA Et Fp Fr Hu Hv Hw Hx Ih Ii Ij Il Im In Ip Ir Is Iu Iv Jg Ji Jk Jl Jn Jo Jp Jq Jr Js Jt Lh Li Lv Lw Lx Ma Md Me Mf Mg Mi Mq Mr Mt Mu Mw Mx Mz Na Nb Nd Nf Nm No Nr Nt Nu Nv Nw Nx Ny Oi Ok Om On Oz Pa Pd Pe Pg Po Qa Qb Qd Qe) Ip(Et Fr Hu Hv Hw Hx Ih Ii Ij Il In Ir Is Iu Iv Jg Jh Ji Jk Jn Jo Jq Jr Js Jt Lh Li Lu Lv Lw Lx Lz Ma Md Mg Mi Mm Mn Mq Mr Mt Mu Mw Mx My Mz Na Nb Nc Nd Nf Nk No Nr Nt Nu Nv Nw Oh Ok Om On Pa Pc Pd Pe Pg Po Qa Qb Qd Qe) Iu(Et Fp Fr Hv Hw Hx Ih Ii Ij Im In Is Iv Jg Jh Ji Jk Jl Jm Jn Jo Jp Jq Jr Js Lh Li Lv Lw Lx Ma Md Mg Mi Mj Mn Mq Mr Mt Mu Mv Mw Mx Mz Nb Nc Nd Nf Nm Nr Nv Nw Nx Ny Oh Ok Om On Pa Pd Pe Pf Pg Po Qa Qb Qd Qe) Mg(aA Fp Fr Hw Hx Ih Ii Ij Il Im In Iq Ir Is Iv Ji Jk Jl Jm Jn Jp Jq Jr Js Lh Li Lj Lv Lx Ma Md Mh Mi Mj Mn Mr Mt Mu Mw Mx Mz Nb Nc Nd Nf Nk No Nr Nt Nv Nw Nx Ny Og Ok Om On Pa Pe Pg Po Qa Qb Qd Qe) Lv(Et Fp Fr Hu Hw Hx Ih Ii Ij Il Im In Iq Ir Iv Jg Jm Jn Jo Jp Js Jt Li Lw Lx Ma Md Mi Mm Mn Mq Mr Mt Mu Mv Mw Mx My Mz Na Nb Nc Nd Nf Nm No Nr Nu Nv Nw Nx Ny Oh Ok On Pa Pc Pd Po Qb Qd Qe) Pa(aA Et Fp Hv Hw Hx Ih Ii Ij Im In Ir Is Iv Jg Jh Ji Jk Jm Jn Jo Jp Jr Js Jt Li Lw Ma Md Mi Mm Mn Mq Mr Mt Mu Mv Mw Mx Mz Na Nc Nf Nj Nm Nr Nu Nv Nw Nx Ny Og Oh Ok Om Pc Pd Po Qa Qb Qd Qe) Mw(aA Hv Hw Hx Ih Ii Ij Il Im In Iq Ir Iv Jg Jm Jn Jo Jq Jr Js Jt Lh Li Lu Lw Lx Md Mi Ml Mq Mr Mv Mx My Mz Na Nb Nc Nd Nf Nk Nl Nr Nt Nu Nv Nx Ny Og Oh Ok Pb Pc Pd Po Qd Qe) Mt(Fr Hv Hw Hx Ii Ij Il In Ir Is Iv Jg Jh Ji Jk Jn Jo Jq Jr Jt Lh Lw Lx Md Mh Mi Ml Mm Mq Mr Ms Mu My Mz Na Nb Nc Nd Nf Nk No Nr Nt Nv Ny Og Oh Om On Pb Pc Pd Pe Po Qa Qd) Nd(Et Fp Hw Hx Ih Ii Ij Im In Iq Ir Is Iv Jg Jh Ji Jk Jl Jm Jn Jo Jp Jq Jr Js Jt Lh Li Lj Ma Mm Mn Mq Mu My Mz Nb Nj Nm Nr Nt Nu Nv Nw Ny Om On Pd Pf Po Qa Qb Qd Qe) Mi(Et Fp Fr Hu Hv Hw Hx Ih Ii Ij Im In Io Ir Is Jh Ji Jk Jl Jn Jo Jq Jr Js Jt Lh Li Lw Md Mr Nj No Nr Nt Nv Nw Oh Ok Om Mn Mq Ms Mu Nj Nk Nr Nv Nw Ny Ok Om On Pc Pd Pe Po Qa Qb Qd Qe) Hw(aA Et Fp Fr Hx Ih Ii Ij Il Im Iq Ir Is Iv Jg Jh Ji Jk Jm Jn Jp Jq Jr Js Li Lw Lx Ma Mm Mn Mu Mv Mz Nf Nm Nr Nv Nw Nx Ny Oh Ok Om On Pd Pe Pg Po Qa Qb Qd Qe) Lx(aA Et Fr Hq Hv Ih Ii Ij In Ir Is Iv Jg Jh Ji Jk Jl Jn Jo Jp Jq Jr Js Jt Lh Li Lw Ma Mm Mq Mr Mu Mz Nj Nm Nr Nv Nw Ny Og Oh Ok Om On Pd Po Qa Qb Qd Qe) Il(aA Et Fp Hv Ih Im In Iq Jg Jh Ji Jm Jn Jo Jp Jq Jr Js Jt Li Lw Ma Md Mf Mm Mn Mq Mu Mv Mx My Mz Na Nc Nf Nj Nm Nr Nu Nw Nx Ny Oh Ok Pc Pd Pf Qa Qb Qd) Ma(Hv Hx Ih Ii Ij In Ir Iv Jh Ji Jm Jn Jo Jq Jr Js Jt Lh Lw Md Mh Mq Mr Mu Mx Mz Na Nb Nc Nf Nk Nr Nt Nu Nv Nw Nx Oh Ok Pd Po Qa Qb Qd Qe) Mu(aA Et Fr Ih Ii Ij Im Ir Is Iv Ji Jk Jl Jn Jo Jq Jr Js Jt Lh Li Lw Md Mr Nj No Nr Nt Nv Nw Oh Ok Om On Pd Pe Pg Po Qa Qb Qd Qe) Nr(aA Et Fp Fr Hv Hx Ih Ij Im In Iq Iv Jh Ji Jn Jo Jr Js Jt Li Mm Mn Mq Mr Mz Na Nb Nf Nm Nu Nv Nw Nx Ny Ok Pd Qa Qb Qd Qe) Fr(Hv Hx Ih Ii Ij In Ir Is Iv Jh Ji Jk Jn Jo Jq Jr Js Jt Lh Lw Md Mq Mr Mx Mz Nc Nf Nk No Nt Om Pd Pe Pg Pz Qa Qb) Nv(Et Fp Hv Ih Ii Ij Im Io Ir Is Jh Ji Jn Jo Jp Jq Jr Js Li Mm Mq Mr Na Nf Nw Oe Og Om Pc Po Pz Qa Qb Qd Qe) Po(Et Im Ir Is Iv Jg Ji Jn Jo Jp Jq Jr Jt Lw Md Mh Ml Mm Mr Mz Na Nt Nw Ny Of Og Oy Pb Pc Qa Qb Qd Qe) On(aA Hx Io Is Ji Jk Jn Jo Jq Jr Lh Mh Ml Mm Mr Ms My Nc Nj Nk No Nt Ny Oe Of Og Oi Pb Pd Pe Pg Pz Qc) Ih(Et Hv Hx Ii In Jg Jh Jk Jo Jp Js Jt Li Lw Md Mj Mm Mq Mr Mv My Mz Nb Nf Nu Oh Oi Ok Om Pc Pd Qd) Im(Hu Hv Hx Ii In Jg Jo Jp Jq Jt Lu Lw Md Mh Mj Mk Mq Mr Mv Mx My Mz Na Nb Nc Nf Nk Nu Nx Oh Pc Qd) Jr(aA Et Hx Ii Ij Is Jg Jh Ji Jk Jl Jo Jq Jt Lh Lw Md Mm Mr Nb No Nt Nu Oh Om Pc Pd Pe Pg Wm) In(aA Et Fp Iq Jg Jm Jp Li Lw Lz Ml Mm Mn Mq Mv My Nc Nk Nm Nu Nw Nx Ny Oh Pf Qb Qd Qe) Jo(aA Et Fp Hx Ir Is Iv Jl Jk Jl Jn Jp Jq Js Li Lw Mm Mz No Nw Ny Og Om Pc Qa Qb Qd Qe) Hx(aA Et Ir Iv Jg Jn Jp Jq Js Jt Li Lw Md Mm Mv Mz Nc Nw Ny Og Oh Ok Pc Pd Qd Qe) Qb(Hu Hv Jg Jh Jp Jt Lu Lw Md Mm Mq Mr Mv My Mz Na Nb Nf Nm Nu Nx Oh Ok Pc Pd) Nw(Hv Ii Ij Ir Iv Jg Lh Li Lw Md Mq Mr Mv Mz Na Nb Nc Nf Nk Nt Nu Pd Qa Wm)

Jq Lh Lu Lx Mi Mr Ms Mu Mz No Nt Oi On Pa Pe) Io(aA Et Hr Iu Jg Ji Jk Jl Jp Jt Lv Me Mi Mt Nm Nt Nv On Qa Qd) Nq(aA Hu Hw Ji Jl Jq
Ms Mu Mv My Mz Ng No Ns Nt Ok Oy Pe) Mg(aA Et Fr Hw Is Jl Jo Jq Lh Lx Ma Mr Ms No Nt Oi Pa Pe) Mt(Hw Hx Im Iu Lv Mh Ml Ms My
Nj Ny Of Oh Oi Ok Pb Qa Qc) Hr(aA Hw Hx Jo Lh Lu Lx Mi Mr Ms Nb No Pa Pe Po) Oh(Hw Im Jg Jk Jl Lx Nb Nd No Nt Om Pa Pe Po Qa)
Nj(aA Jk Lu Mi Mu Nb Nd Nf No Nt Nv On Pa) Et(Hw Jk Jq Lx Mi Mr Mu Nt Oe Oi Pa Pe) Jg(Hu Hw Iu Jq Ms My Nd Ng Ns Oe Oi Oy)
On(Hu Mi Mu No Ns Nt Nx Oe Of Oi Qc) Nw(Hw Iu Jq Mr Na Nd Nt Ok Pe Qc) Ms(Iu Jh Ji Jk Jp Mw Nd Nm Om) Mu(aA Jl Lh Lx Mi No Nt
Pa Pe) Jk(aA Ik Jq Ma Mz Ng Oe Ok) Jq(Fr Hw Im Iu Ma Mi Nd) Nt(Fr It Jl Jo Ne Oe) Mh(Ii Iu Lx Nb Pa Po) Ma(aA Hw Mr Pa Pe) Nb(Im Ml
Nd Oc Of) Ji(Fr Mi Nd Nx Qc) Hw(Im Jp Ml Om) Jh(Hu My Ns Oy) Mi(Jl No Om) Mw(My Ns Oy) Oe(Jl Nv Pa) Fr(aA No) Nr(Im Jp) Lu(Iu
Me) Lx(Hq Jt) Ml(Mz Pe) Jo(Jl Lh) Om(Iu Of) WmMj NsMq MeaA MkPa MvMy NdOk InIt QcQd NyPb} Oi{Nn(aA Et Fp Fr Hu Hv Hw Hx Ih Ii Ij Il Im In Ip Ir Is Iu Iv Jg Jh Ji Jk Jl Jn Jo Jp Jq Js Jt Lh Li Lv Lw Lx Ma Md Me Mf Mg Mi Mq Mr Mt Mu Mw Mx Mz Na Nb Nf Nm No Nr Nt Nu Nv Nw Nx Ny Ok Om On Pa Pe Pg Po Qa Qb Qd Qe) Mu(aA Fp Hw Hx Ih Ip Ir Is Iu Iv Ji Jl Jn Js Jt Lh Li Lj Lw Lz Mg Mh Mm Mr Mt Mz Nb Nj Nm Nr Nt Nw Oh Om On Pa Pc Po Qa Qb Qd Qe) Mt(Et Fr Hx Ip Is Jg Jl Jn Jp Lh Li Lv Ma Mg Mi Ml Mm Mq Mr Mz Na Nb Nq Nt Nw Ny Oh Om On Pa Pb Pc Pg Qa) Jg(aA Ih Ip Ir Is Iu Iv Jl Jn Jp Jq Js Jt Lu Lv Mm Mq Ms Mz Nk No Nt Nu Nv Oh Pe Pg Qa Qd) Is(Et Fr Hw Jl Lh Lu Lw Md Mg Mi Mm Mr Ms Mz Nb Nf Nq Nt Nv Nw Oh Om On Pa Pc Pg Po) On(Et Hu Io Ip Ir Iv Ji Jl Jn Jq Lj Mg Mm Mz Ng Nj Nk No Ns Nt Of Oh Oy Pc Qa Qd) Pc(aA Et Fr Hu Ip Ir Iv Ji Jl Jn Jp Lh Lx Ma Mi No Nt Nw Ok Om Pe Po Qa Qd) Nw(Hw Ip Iu Iv Jk Jl Jn Lh Li Lw Mg Mi Mq Mr Nb Nq Nr Nt Nu Oh Pa) Nq(aA Et Hx Ih Ip Ir Jl Jn Js Jt Mr Mz No Nr Nt Om Pa Qb) Jl(Et Fr Im Ji Jn Jt Li Lw Mg Mi Mm Mz Nf Nm Oh) Ip(Et Ih Jk Jt Li Ma Mm Mv Nb Nt Nv Oh) Jn(aA Et Iu Jk Jp Li Ma Mg Mi Mm Nt Om) Ma(aA Hx Ir Jk Lh Mh Mz Pa Qb) Oh(Et Fr Ji Lx Mm Mv Nt Om Qa) Et(Mh Mz Nk Po Qa) Mm(Ih Ir Js Nb Nt) Mg(aA Jp No Qa) Jp(Iu Lw Nv) Fr(Ih Nb) Nt(Lh Mz) aA(Li Me) IrOm QaNv JiPd} Io{On(aA Et Hu Hw Im Ip Ir Is Iu Ji Jl Jn Jq Jt Lh Lw Mi Mm Ms Mt Mv Mw My Na Nc Ng Nj Nk Nn No Ns Nt Of Oh Oy Pc Qa Qd) Qa(aA Et Hw Ip Iu Jg Jk Jl Jn Jp Jq Lh Lv Lw Ma Md Mi Ml Mm Mr Mt Mu Mz Nb Nd Nm Nn Nt Nv Nw Oh Pa Pc Pg) Is(aA Et Fr Hw Iu Ji Jl Jq Jt Lh Lw Lx Mg Mi Mm Mr Mt Mu Mz Nm Nn No Nq Nt Nv Nw Oh Pa Pc Pe Pg Po) Nw(aA Hw Hx Ip Ir Iu Jk Jl Jn Jt Lh Lv Lw Mi Mq Mr Mt Mx Nb Nc Nd Nk Nm Nn Nt Oh Pa Pc Pg Qd) Ji(aA Hw Ip Iu Jk Jl Jt Lh Lv Lw Mi Mm Mr Mt Na Nc Nd Nk Nr Nt Nx Oh Pa Pc Pe Pg) Jn(aA Et Hw Ip Iu Jg Jk Jl Jp Lh Lv Ma Mg Mi Mm Mt Mw Nb Nn Nq Nt Nv Pa Pc Pg) Jp(Hw Ip Ir Iu Jk Js Lh Lv Lw Lx Ma Mg Mi Mm Nb Nk Nm Nn Nt Nv Pa Pc Pe Pg) Jl(aA Et Fr Im Ip Ir Iu Jq Jt Lh Lw Md Mg Mi Mm Mt Nm Nn Nq Nt Oh Pc Pe) aA(Ip Jg Jk Lv Lw Ma Me Mm Mn Mt Mu Nj Nk Nn Nq Nr Pc Pg) Pg(Et Jt Lw Mi Mm Na Nn Nt Oh Pa Pb Pc) Mt(Hx Ih Ip Iu Lh Mi Nd Nm Nv Pa Pc) Nn(Ii Ir Lh Mi Mr No Nt Pa Pe) Mm(Hu Hx Ii Lh Lv Mx Nc Pa Pe) Lw(Ir Lh Mi No Pa Pe Po) Et(Ip Nc Ni Nk Pa Pe) Ip(Mi Mx Nt Nv) Lv(Lh Mi Nv) Nj(Mi Nt Nv) Pc(Lh No Pe) Fr(Mx Nc) Pa(Ma Nm) NtMg MuIr NkOm} Mu{Nj(aA Fr Hv Hw Ih Ik Im In Ip Ir Is Iu Iv Jn Jo Jq Js Jt Lh Lv Lw Lx Lz Md Mg Mi Mj Mr Ms Mt Mz Na Nb Nd Nf Ng Nn No Nr Nt Nw Oh Ok On Pa Pc Pe Pg Po Qa Qd Qe) Ng(Fr Hv Hw Hx Ii In Ip Is Iu Iv Jh Jk Jl Jn Jo Jp Js Lh Lv Lw Lx Lz Ma Md Mh Mi Mj Mr Mt Mv Mw Mz Na Nb Nd Nn Nq Nr Nt Nv Ok On Pa Pe Pg Po Qa Qb) Mg(Et Fr Ii Ij Ip Is Iu Iv Jl Jo Jt Lh Lv Lw Lx Ma Mi Mj Mr Nb Nm Nn Nq Nr Nt Nv Nx Ok Om On Pa Pc Pe Pg Po) Ms(Hv Hx Ip Is Ji Jn Jq Js Lh Lw Lx Mb Mj Mr Mt Mw Nb Nn Nq Nr Nw Ok On Pa Pg Po) Ip(aA Hw Ik Jn Jq Lh Lv Lx Mt Mz Nb Nn Nr On Pa Pb Pe Pg Po Qa) Oe(aA Hw Hx Is Jl Lh Mt Nb Nr Nt Nv On Pa Pe Pg Po Qa Qb) Lv(aA Hw Im Iu Lw Lx Mr Mt Nf Nn Nr Oh Pa Pc) Pg(Hu Ik Im Jo Lw My Mz Ns Of Oh Oy Pb Pc) Jn(Fr Ik Lh Lw Lx Mr Nn Nt On Pa Pc Pe) Jl(Ik Jo Jq Lw Mm Nn Nt Of Oh Pb Pc) On(Ik Jo Mm My Nn Ns Of Oy) Is(Ik Lh Lw Mi No Of Pc) Jo(Hw Ir Lh Mi Pe Qa) aA(Hu Ji Lw Mi Nn Pc) Mt(Ik My Ny Pb) Pa(Jq Mk My Oy) Mm(Et Ji Wm) Nk(Im Mq Ni) Ik(Lh Pe Qb) Of(Ii Lh Ma) Pb(Ny Pe Qa) Nd(Hq Ns) Ne(Nc Nl) Ji(Nx Qc) NnPc LxHq MhIm MwMy} Jl{Jo(Et Fr Hv Hw Ij In Ip Is Jg Jh Ji Jn Jq Jt Lh Lw Lx Md Mg Mi Mr Mz Na Nf Ng Nm Nn No Nq Nt Oh Ok Om On Pc Pe Pg Qa) Mm(aA Et Fr Hv Hw Ij In Ip Is Jg Ji Jn Jq Lh Lw Md Mg Mi Mt Mz Nf Ng Nm Nn Nq Oe Oh On Pc Qa) Mg(aA Et Fr Ik Is Jg Jn Jq Jt Lh Lw Ma Mi Ms Mz Ng Nm Nn Nq Nt Oe Of Oh Om On Oy Pc) Ms(Is Jg Jh Ji Jn Jq Jt Lw Mi Mt Mw Mz Na Nb Nf Nm Nn Nq Oe Oh Om Pc) Ng(Fr Hw Jg Jh Jt Lh Lw Lx Ma Md Mi Na Nf Nm Nn Nq Nt Ok Om Pc Pe Qa) Oe(aA Et Fr Im Is Jg Jh Lw Md Mi Mt Mz Nf Nn Nq Nt Nw Oh Om On Pc) Nn(Hu Hw Im In Ji Jn Jq Lw Mf Mi Mz Na Nt Pc Qa) Of(Et Fr Jg Jh Lh Ma Mt Mv Nb Nm Nq Nt Om On) Nq(Hu Hw Jn Jq My Mz Na Nf Ok Oy Qa) Mt(Hx Im Lw Mh Ml My Nm Nt Ny Oy Pb) Pc(aA Hw Im In Is Jq Lx Mi Pe) Lx(Hq Jn Jq Lw Mh Na Qa) Im(Jt Lw Md Mz Nf Oh) Oy(Jh Mv Mw Nb Pa Po) My(Jh Mv Mw Nb Om) Mh(Nb Nw Pa Po) Mi(Hq Jn Jq Qa) Nt(Ii Ik Oh) Ji(aA Nx Qc) Lw(aA Lu) Ml(Mz Om) Hr(Hw In) Ii(Jq Lh) Jh(Hu Ns) NdJq NiNk NjaA HwNw IkPe} Nn{Ms(aA Fp Fr Hv Hw Hx Ij Ip Ir Is Ji Jn Jp Jq Ma Mb Mi Mj Mq Mr Mt Mw Mx Mz Na Nb Nd Nr Nw Ok On Pa Pe Po Qa) Ip(aA Hu Hw Hx Ii Ij In Jp Jq Lv Lx Mf Mt Mz Na Nb Nr On Pa Pc Po) Mf(aA Hv Ii Ij In Is Jp Jq Lv Mh Mj My Nd Ng Nj Nr Ns Pa Pe) Mg(aA Et Fr Ii Is Iu Jo Lh Lx Mr Nb Nt Nx Om On Pa Pe Pg Po) Jn(aA Fr Hu Hw Lh Lx Mi Mr Mz Nd No Nr Ok On Pa Pe Pg Po Qc) Lv(aA Hu Hv Hw Ii Ij Iu Lx Mi Mr Mt Na Nf Nr On Pa Po) Ng(Fr Hw Ii Is Lh Lx Mi Mr Mw Nb Nt Nv On Pa Pe Pg Po) On(Hu Hw In Jq Lw Mm Mv Mw My Na Ns Of Oy Pc) Is(Hu Hw Jq Lh Lx Mi Mr Mz No Nr Nt Pa Pe) aA(Hu In Ji Jq Lw Mx Nj No Nt Oe Pe Pg) Pc(Jp Mq Mr Mx Nb Nr Nv Oz Pa Pe Po) Nj(Hw Lx Md Me Na Nb Nd Nf Nt Pa) Jq(Hw Lx Nd Nr Pa Pe Po) Ji(Mm Nx Pa Pe Qc) Jo(Hw Lh Mr Nt Pe) Jp(Hw Ij In Nd Nr) My(Ii Mt Mw Pe) Mm(Et Mt Nw) Nd(Ij Lw) Oy(Ii Pa) LxHq MkPa MtMv ImPg InNw NyPb PePf} Nj{Mt(aA Hv Hw Hx Ip Jk Jt Lh Lv Mh Mi Mj Ml Mq Ms Mw Mx Na Nb Nd Nf Ni No Nr Nt Nv Ny Pa Pb) Oh(Hu Hv Hw Hx Ii Ij Il In Ip Jk Lh Lv Mi Mj Mr Mw Mz Nb Nd No Nq Nr Nt Nv Pa Pe Po Qa) Nq(aA Hv Hw Ih Ii Ij Im In Ip Iu Jq Lv Mi Mj Mr Mx Mz Na Nb Ng No Nr Nv Pa Po Qa) aA(Fr In Ip Jg Ji Jk Jq Lh Lv Lw Ma Mg Mw Nd No Nt Om On Pa Pc Pe Pg) Mi(Fr Ij Im Ip Jk Jp Jq Lv Ms Mz Na No Nw Ok Om On Qa Qd) Jq(Fr Hw Jk Lh Lx Nb Nd No Nr Nt Nv On Pa Pe Po) Pa(Im Ip Iv Jp Lx Ma Mq Mw Mz Na Ni Ok Qa Qd) No(Fr In Jt Lv Mg Mq Mz Na Nb Nf On Qa) Nt(Fr Ip Jn Jo Mz Nd Ne Ng Nw On Qa Qd) Mz(Hw Jk Lx Mq Mr Na Nd Nr Nv On) Na(Fr Ih Jk Lx Nv On Po) Nb(Im Ip Lx Mw Oe Of) Hw(Im Ip Mx Nw On) Lx(Mq Nf Ni On) Qa(Nd Nf Nv On) Jk(Hx Im Ms Mx) Lu(Im Ip Ji) Po(Mh Mq) Md(Fr Hx) Ip(Nv On) MbPe MgOn MxNv NdOm NyPb} Ip{Jq(Hw Iu Jg Jk Lx Mi Mm Mr Nd Nk No Nq Nr Nt On Pa Pc Pe Pg Po) Jn(Et Hw Jg Jk Lu Lw Lx Ma Mm Ms Mt Nd Nq Nw Ok Om Pc Pe Po) Mg(aA Et Fr Jg Jk Jt Lh Ma Mi Mv Nb Nq Nt Om On Pe Pg Po) Lx(Hq Hv Hw Lw Mh Mt Mz Na Nb Ng Nw Oh Oy Pc Qa) Mt(Jk Lv Ml My Mz Nk Nw Ny Oh Pa Pb Pe Pg Qa) On(Hu Jo Mm Ms Ng Nk Nm No Ns Nt Nx Oe Of Qa) Pe(Fr Ik Jo Lw Mm Nq Nw Oh Oz Pb Pc) Mm(aA Et Fr In Ji Jk Lu Pa Qa) Jo(Hw Lh Mi Mr Nb Nt Om Pg Po) Jp(Hw Hx In Jk Lu Lv Mi Nq Nu) Nw(In Jk Lv Nk Nm Nq Nu Pa Qa) Ng(Fr Lh Ma Nq Nt Om Pg Po) Pa(Et Na Nq Oe Oh Ok Om) Ms(Jg Jk Mi Mw Mz Nb) Nk(Et Fr Jh Ji Mz Om) Ma(In Jk Lu Mz Qa) Et(Jk Nd Nm Qa) Jg(aA In Lu Qa) Po(Mh Of Pb) Fr(Hw In Mz) Jk(Jm Oh Ok) aA(Lw Nt Pc) Nq(Mz Qa) Mw(Lu My) Nb(Oe Of) NmOm NtIk LvOh MhJh NcIm HuPc HwJi QaOk} Is{Ms(Et Fr Hw Jg Jh Ji Jk Jq Jt Lh Lw Mg Mi Mm Mt Mw Mz Nf Nq Nw Oh Om Pa Pc Po) Oe(Et Fr Jg Jk Lh Mr Nb Nq Nr Nt Nv Nw Om On Pa Pe Po) Pc(aA Hw Ji Jq Lh Lu Lx Mi Mr Mz Nf No Nt Nw Pa Pe Po) Lw(Hw Lh Lu Lx Mi Mr Mt Mz Nf Nq Nt Om On Pa Pe Po) Mm(aA Et Fr Ji Jq Lu Lx Mz Nw On Pa Pe Pg Qa) Ng(Fr Jh Jk Lh Ma Mg Mi Mv Mw Nq Nt Pg) Nq(Hu Hw Jm Jq Mg My Mz Ok Oy Pe) It(Hv Hw Ij In Ir Jn Jq Na Nt Qa) Mg(Fr Ik Jo Jq Lh Ma Mi Mz Om) Mt(Hx Mh Ml My Ny Of Oy Pb Qc) Jo(Hw Jt Lh Mr Nt Pe Pg) Ik(Jk Nt Nu Pe Pg Po) My(Jh Mv Mw Nb Om) Lx(Jm Jq Mh Oh) Of(Fr Nb Om Pg) Pa(Et Jm Mh Oh) Ns(Jg Jh On) Ne(Nc Nl Nt) Hu(Jh Jk On) Qc(Ji Mz Nw) Oy(Jh Mw Po) Fr(Jq No) Nd(Jm Jq) Hw(Ml Nw) PoMh NmLu NiNk IiLh JmPg NxOn} Mg{Fr(Et Hv Hw Hx Ij In

Figure 42 Continued

Iu Iv Jo Js Jt Lh Lv Lw Lx Mi Mq Mr Mx Na Nb Nc Nf Nm Nr Nt Om On Pa Pc Pe Pg Qa) Nq(Et Hv Ii Ij In Jn Jp Mq Nb Nt Nx Ok Om Pe Pg Qa) Ma(Hw Hx Ii Jk Jn Lh Lv Nb Nt On Pe Pg Po Qa) Om(Hw Iu Lh Lv Lx Mh Mi Nk Nt Pa Pe Pg) On(Ik Iu Jo Lw Mi Ms My Ng Nt Oy Pc Pg) Et(Il In Lh Mh Nk Nt Oe Pa Pe Pg Po) Mm(Ii Jo Lh Mr Nt Nw Pe Pg Po) Jg(Iu Jo Mi Mt Nt Pe Pg) Jo(Ir Jn Lh Pe Qa) Nt(Lh Mi Nm Pc) Ng(Jn Lx Pe Po) aA(Lv Lw Me Pc) Ms(Jn Jq Lx) Po(Lw Pc) Pg(Mi Ok) LvJp MtLh NkJq} Ji{Ms(aA Fr Hw Ii Iu Jg Jh Jk Lh Mi Mm Mr Mw Na Nb Nd Nq Nt On Pa Pc Pe Po Qc) Mm(aA Et Fr Hw Iu Jk Lu Ma Mt Mw Nq Oh On Pa Pc Pe Pg Wm) Nx(Fr Hw Ii Iu Jk Lh Lu Mi Nq Nv On Pa Pc Pe Pg Po) Ml(Il In Jk Lu Lx Mh Mr Mt Nr Pa Pe Po) Pa(Hx Md Mh Mk My Ny Oe Of Oy Pb Pc) Qc(Il Iv Lu Mj Mt Nr Oh On Pe Po) Of(Ii Jk Lx Mt Mw Nb On Pe Po) Po(Hx Md Mh My Ny Pb) aA(Fr Jk Me Nh Nq Pc) Mh(Ii In Lx Mt Pe) Pb(In Jk Lx Mt Pe) Mt(Md My Ny) Jk(My Ng Oy) Wm(Nm Oh) Lu(Me Nk) Jo(Hw Nt) FrNk NqNg MwMy NdHq IiLh InNy PcPe} Jo{Pg(Et Fr Hv Hw Ij In Ir Iu Iv Jn Jq Jt Lh Li Lw Mi Mm Mq Mr Mz Na Nb Nf Nm No Nr Nt Oh Ok Om On Pe Qa) Pe(Et Fr Hw Iu Jg Jt Li Lw Ma Mi Mm Na Nm Nq Nt Om On Qa) Lh(Et Fr Jk Jn Ma Mi Mm Mt Nt Nw Om On Po Qa Qd) On(Hv Hw In Ir Iu Jt Mh Mi Mr Na Nr Nt Of Qa) Nt(Ir Jk Jp Jq Js Li Ma Mw Om Po Qa Qd) Qa(Fr Iu Ma Mi Mr No Nq Pa) Hw(Et Fr Ma Mt Nq Om Po) Om(Iu Mh Mi Nk No Pa) Ma(Ii Mr Nb Nr) Jk(Et Mi Nb Ok) Nq(Ir Jn) Mi(Ij Jn) PoNb FrNg} Ng{Nq(Hv Hw Hx Ii Ij In Iu Jh Jn Jp Jq Lh Lv Lx Mf Mi Mq Mr Mt Mw Mz Nb Nm Nr Nt Nu Nv Ny On Pa Pe Po Qa Qb) Fr(Hv Hw Hx Ii In Iu Jh Jn Js Lh Lv Lw Lx Mi Mq Mr Mt Mw Mx Nb Nc Nd Nm Nr Nt On Pa Pc Pe Pg Po Qa) Ma(Hw Ii Jk Jn Lh Lv Nt Pe Pg Po Qa) Jh(Ii Iu Jk Lh Lx Lz Md Mi No Nt Nv) Nt(Jn Jp Lw Lx Mm On Pc Qa) Mw(aA Lx Mi My Nd) Mt(Lh Ml Pb Po) Pg(Et Jg Jp Mm) Mm(Lh Pe) Om(Mh Pa) On(Ms Qc) PoNm EtPa MiJk} Mt{Lv(Fr Hw Hx Iu Jn Lh Lw Lx Mh Mi Ml Mm Mr Mw Nf No Nq Nr Ny Of Oh Ok Pa Pb Pc Pe) Pb(Hu Hv Hw Ij In Jn Jq Lw Mi Ny On Oy Pg) Of(Hv Jn Jq Lh Lw Mq Mr Nr Om Pe Qa) Mm(Et Fr Hx Jp Ma Nw Om On Pc) Jn(Hx Lw Mh Ml My Ny Oe) Pc(Hu Ij In Lx Ms My Pa) Ms(Mi Mw Nd Nq Po) Lw(Hx Mf Ml Ny) My(Ii Mw On Pg) Mi(Hq Hx Ml) Ny(On Oy Pg) Mh(On Pg) Ml(Hv Jq) Qc(On Qa) Jk(Ik Oy) Oe(Nb Pa) LxHq MdJq MwHv HxPe ImPg IrIt} aA{Pc(In Jn Jq Lh Lv Lx Ms Nt Pa Pe Pg) Mm(In Jn Lv Ma Mh Nw On Pg Qa) dH(aJ aP bC bQ bW cS cU dD dN) Lw(Fr Lx Ms Nq Pa Pe Pg Po) aY(aI aM cG cJ cU dD dN) Nq(Hu In Jn Jq Mz Qa) Me(Jh Jn Lv Ma Nt Pe) bC(aO aZ bB bV cJ dI) Oe(Jg Jh Jk Mw On) My(Jh Mv Mw Om) cF(bW cJ cS dK) cJ(bH bO dN) Fr(Jn Jq) Ms(Jn Mw) dD(bE bH) dN(bV dC) LvJg MaJk MwOy OfOm aFaO aZcU} Lv{Oh(Hv Ii In Jg Jn Jp Lw Lx Mi Mm Mr Nq Nr Ok Pa Pc Po) Jp(Hw Hx Ii Iu Jk Lx Mi Mr Nd Nf Nm Nq Pa Pc) Nw(Iu Lu Lw Mq Nm Pa Pc) Ok(Hw Iu Mz Nb Nf Pa Po) Lx(Iu Nm Of Oy Pc) Jh(Hu My Ns Oy) Jn(Hw Mr Pa Po) Mm(Lu Mi Pa) PoOy LuJg MaPa MeHv MiHq NcIm} On{Of(Hu Hv Hw Ii Ij In Jq Lh Mm Mz Na Nb Nf No Ns Nt Om Pa Pe Po Qa) My(Jh Jk Mv Mw Nq Om Qc) Mm(Lw No Nt Oe Pc) Ns(Hx Mh Ny Pb) Jn(Lw Oe Pc Qc) Oy(Jh Jk Nq Qc) Mk(Mi Nt Pd) In(Ml Nb Pb) Nk(Et Im) Pb(Hw Pe) LwJt MlMz MsPc NbIj IiLh} Jn{Mm(Et Jk Lu Lx Mi Ms Nq Nw Pa Pe Pg Po) Ms(Et Fr Jg Jp Lw Ma Mw Nq Ok Pc Qa) Nq(Hw Jm Lw My Mz Ok Oy Pa Pe) Lx(Hq Lw Mh Of Oh Pb Pc) Jk(Et Ik Ma Oe Ok) Po(Lw Of Oy) Oe(Nb Pa Pe) EtPg LwPa MwMy ItQa QcNw} Mw{My(Jp Jq Lu Lx Lz Md Mh Mi Mr Ms Mv Mx Mz Nf Nq Nw Oh Ok Om Oy Pa Pc Po) Ms(Jp Jq Mi Mm Nw Ok) Of(Mi Mr Nf Pe) Oy(Jk Nd Pa Wm) Oh(Hv Nd Ns) Pb(Hu Hw Mi) EtMm NdHu} dN{dH(aJ aO aP bA bC bQ bS bV bW cG cS cU dE) aY(aJ aL aP bA bC bS bW cJ cS dC dM) cE(aO bF bQ cG dF) cC(bA bH bS dE) bA(cF cV) bH(cJ dC) dM(bO cN) aJcF aLbE bRbS} aO{bC(aM aY bA bF bQ bR bU bZ cA cC cD cE cF cG cL cN cR dH dI dM) bW(aM cE cF cL dH) cE(aP cG cU) aM(aX cS) cC(bV dI) dH(aJ aP) aFdM cFcS} Et{Mm(Fr Hx Im Jk Lw Lx Ma Nd Nk Nq Nw Om Pa Pc Pg Po Qb Qd) Of(Ij Il In Jk Pa Pg) Nk(Im In Jk Nd) Jk(Hu Ms Oe) Ne(Nc Nl) MiMs OePa} cF{bA(aJ bE bL bW cS cU dE dK) dK(aJ cU dA dF dG dM) aP(aY bV cC cJ dH) cS(aI cK dD dF dM) aJ(aI bC) bW(cT dM)} Of{Om(Ii Jk Lh Lx Nd Nk Pa Pe Pg Po) Po(Jh Jp Jq Lj Lz) Jh(Ii Lh Nr Pe) Lx(Jq Mi) Nw(In Pe) WmQd MaLh} Jq{Ml(Lx Pe Po Qa) Pc(Hw Ms Pe Po) Nq(Ms Pa Pe) Mm(Pg Wm) Nk(Fr Nw) Pb(Lx Po) QaQc} dH{aJ(aI bB bC bQ bV bW cG cM cO cU) aP(aI bF bQ cO dD) bAbW} Jp{Nq(Hw Ij In Ms Pa) Jk(Mq Ms Oe) Lx(In Mh) Pa(Nm Pc) LwPe MiMs} Nw{Mm(Fr Lw Mi Nq Pc Wm) Ml(Hw In) Pe(Mh My) WmOh MsJk InPb QaQc} bA{bW(aY bQ cA cC cD cE cG cL dI) cC(dE dI) aIbE aZbC} Lx{Hq(Hv Lh Lj Lw Mi Mq Pg) Oy(In Pa) NqMs HvPb} Pe{Nq(Ik Mk My Pb) Ik(Ma Mm Om) Fr(Pb Pf) JhOy PcPf} Nd{Jh(Hu Lw My Ns) Fr(Hq Ns) Om(Hq Ns) LwHv} Ms{Fr(Hx Nb) Mm(Mi Nb) LwOk MaMz} aJ{bX(cC cD cJ) aMaY cCcU} Qd{Wm(Ik Mm) NcIm IkJk} Pg{Jh(My Oy) IiLh ImPc} aI{dM(bE cS) bQcE cCdI} Fr{Nk(Na Ok) NeNl} aY{aM(aP bV) cUdG} dD{bE(bV dM) bSdK} Mm{LuIn MhJk} cE{aPbF bQdK} NcImJk OmPaPb bVcCdE

Constrained panels with 3 analytes, where 1.0E-7 >= 'AUC p-value' > 1.0E-8. Contains 2,744 panels of 397,580 total panels evaluated. :
Ip{Mt(Et Hv Hw Hx Im Ir Iu Lw Md Mh Mi Mr Ms Na Nb Nc Nf Nq Nr Nt Ok Om Pc Qd) Oh(Et Fr Hw Hx Ii In Jh Jn Jp Ma Mu Mw Mz Nb No Nt Nw Og Om Pg Po Qa) Og(Hv Ih Ij Im In Iq Jo Li Lw Mm Mq Na Nc Nd Nf Nk Nm Nu Nx) Mz(Et Hw Jg Jk Lw Mi Ml Mm Nd Nt Nw Om Pa Pc Pe Pg Po Qa) Mm(Hw Hx Ii Io Ir Iv Jp Lh Lv Lx Mg Mh Mx No Po Qd) Ma(Hv Hw Hx Ii Ij Io Ir Lz Mr Mx Nc Nf Nk Nr) Jk(Hu Hv Iv Md Mh Mi Na Nf Ng Oe Of Oy Pc Qa) Jp(Hv Ii Ij Iu Iv Lw Md Mg Mx Na Nf Nr Nv Pc) Ok(Fr Hw Iu Lu Lx Mi Mu Nc Nd Nk Nn Nq Nw Po) Lv(Hx Iv Jg Lu Mi Mr Mw Nc Nd Pa Pc) Qa(Hw Lw Md Mi Mr Nb Nt Nv Pa Pc Po) Jg(Hw Hx Ir Mi Mp Mx Nd Nk Nm Qd) Nw(Et Hv Hw Lw Mb Mg Mi Mr Nd Nt) Et(Hw Hx Lu Mh Nb Nc Nq Po) Lw(Hx Lu Mh Mu Mx Nn Pa Po) Lx(Ir Iv Jo Jt Ly Of Om Qd) Jn(Lh Md Mg Mr Nb Nr Pa Pg) Mu(Fr Iu Mr Nf No Nt Pc) Jh(Ih Lu Mj Mx Nc Nd Oi) Om(Hw Mi Mr Ms Nn Pb Pc) Po(Hw Nf Oy Pc Qd) Fr(Ih Mr Na Nf Nn) Nq(Hx In Mr Nb No) Lu(Hx Im Mn Nd Pc) Pa(Hv Ms Pc Pg Qd) Nn(Hv Iu Mr Nv) Mw(Hv Mh Mx Oi) Nj(Md Mq Nd Nf) Pg(Hw Mr Nf Pc) Mp(Iv Jt Na) Nb(Im My Nk) Io(Jt Mn Qd) Mg(Iu Jq) Mv(Ng Pz) Nd(Iv Mq) Im(Mh Mj) Oi(Ir Iu) Pb(Lh Ny) MsLi HxPc JoJt JqLi} Jj{Mv(Et Iv Jp Jq Md Mg Mi Mn Mr Mx Mz Nb Nc Nd Nx Og Pd) Jg(aA Et Io Iq Iv Jm Jo Li Lu Ma Mg Mi Mr No Nv Ny) Mx(Hw In Jm Jp Mi Mm My Nb Nd Nm Nv Nx Ok) Pd(aA Et Im Iv Jp Mg Mm Mz Nb Nc Nf Ns Nx) Mn(Hv Jm Lu Md Mh Mq My Nc Nl Nm Nu Ok) Jh(Et Hx Iv Jp Lv Mg Mw Nl Nn Nw Og Qd) Pc(Et Fp Hw In Iu Jo Js Li Lx Ma Nw Om) My(Hq Iq Jp Lx Md Mm Nb Nc Nk Nr Nx) Lw(Et Iv Mi Mj Mr Nd No Nv Ny Om) Jm(Hv Jp Jq Md Nb Nm Nr Nu Oh Ok) Mm(Hv Iu Iv Jp Lu Md Mh Nf Nx) Iq(Hv Md Mh Mq Nc Nf Nj Nm Nx) Et(Jq Lu Md Mg Mt Nf Nw Oh) Nk(Jq Mq Mz Nr Nu Ok Pf) Jt(Li Mi Mr No Nv Nw Om) Oh(Fp Hu Jo Mg Nw Ny Om) Nb(Hx Iv Md Mh Nj Ny) Nd(Hq Hv Il Mj Ns Ok) Nv(aA Iv Mz Nc Nm Ok) Lx(Hx Mh Na Nc Pb) Mr(Iv Jo Jp Jq Ok) Nu(Fp Iu Js Li) Md(Hw Jo Jp Js) Mi(aA Iv Mz Nc) Ny(Hv Mq Nx Pb) Mg(Hv Jo Lz) Na(Fr Iu Li) Nl(In Ne Wm) Mh(Hu Nw) Nf(Jo Jp) Iv(Jq Mz) FpHv NnNj NoJq NrJp MjIn MkPa MwOy NcHw HuPf JsOk} Og{Jg(Et Fp Hr Hw Ih Iv Js Jt Lz Mg Na Nf Nx Oh Pc Qd) Pg(Hw Hx Ii Jk Jt Lw Mi Mr Mv Na Nb Nm Nq Nr Pa Pe) Im(Jk Jq Lv Lx Mh Mi Mj Mr Mu Nn Nr Nv Nw Po Qd) Mi(Hu Hv Hx Lh Mg Mr Nr Nv Ok Pc Pe Qb) Jk(Ii Io Lx Mh Mm Mr Nn Nr Nx Pa Po Qb) Nw(Et Ir Jo Jq Jt Mm Mr Mx Mz Na Nd Nr) Jq(Ii Il Iv Jh Lh Nv Ok Pa Pc Pe) Jt(Et Io Jn Mm Mv Nq Nt Pe Po Qa) Ok(Et Ih Ii Ij Ma Mm Mz Nv Pa) Jh(Iq Js Li Md Mg Nc Nm Qd) Jp(Ij Il Iu Mg Mv Nm Nr Nv) Nq(Et Ij Jo Lw Mf Mh Nm) Ma(Ij Il In Mx Mz Nv Qb) Mm(Il Jo Mj Mx Nx Qb Qe) Qa(Hw Hx Io Lw Mv Nm Nr) Lv(Hx Il Mq Mr Mz Pc) Li(Ii Jn Mp Mu Nt Pa) Et(Ir Iu Iv Nv Pc) Nn(Jo Me Ni Nm Qb) Mq(Ii Jn Nm Ny Pa) Po(Ir Iv Jo Nf) Mg(Hx Mr Nr Qe) aA(Hx Ij Jo Lh) Lx(Ir Iv Nb) Mt(Ij Na Qd) Jn(Jo Lw Nr) Fr(Iv Js) No(Hx Ij) Mv(Ir Mz) Ii(Me Pc) Nv(Hv Oh) NmIh NtNf NuNy LwIr MuQd MzIu HuPc HxIv JoLh OhPe} Mp{Ns(Hv Hw Ii Ij In Ir Jh Lx Md Mi Mj Mq Mr Mu Mw Mz Nb Nf Nn Nr Nv Nw Oz Pg Po) Nn(Hq Hu Hv Ii Ij Im In Iv Ji Lx Mu Mz Nr Po) Mt(Ii Ij In Lh Mh Ml Mr Mu Nb Nf Nq Nr Pd) Pc(Fp Hw Ii Im In Ji Jp Mr Nf Ni Nt Nw Pg) Lx(Hw Ir Jo Ly Na Ni Nm Oh Ok Pg Qd) Nq(Hv Hw Ij In Ir Lw Nr Oy Pe Qa) Mu(In Jq Mr Mz Na Nb Nf Nr Oh On)

Figure 42 Continued

Io(Et Fr Ij Jk Jt Mr Ny Qd Qe) Pa(Hw Ij In Iv Jh Mz Nf Ni Nm) Oh(Hw Ij In Jh Lu Lw Nr Po) Nw(Ij Ir Mr My Mz Nr Qa) Lu(Ih Im Iu Mg Nm Nr) Lw(Fp Hw Im Iv Nt Pg) Mi(Et In Na Nf Pe Qa) Hq(Ii Ij Ir Nv Pf Pg) Mg(Hu Jk Lv Mh Oi) Pd(Hu Hw Ii Na Pg) Jp(Mr Na Nf Ni) Oe(Jg Jh Mw Nv) On(Ir Na Nf Qa) Et(In Is Jn) Nu(Iu Jg Qd) Jq(No Nt Pg) Pb(Hx Om Po) Md(Na Nr) Mk(Jk Oz) Mm(Jo Pz) Ni(Nc Nj) Ji(Fr No) PoMh NmNk NtNe LvMw MjJh MsMz NgOm IiLh IjOf ImNv PzJg JoJt} Mt{Hx(Hu Hv Ii Ij Ji Lh Lx Mr Mu Ng Nr Ns Oe Pa Pc Pg) Ml(Hw Ii Ij In Lh Mr Mu Na Nr Om Pe Pg Qa) Oi(Ih Ii Iu Iv Jk Js Lj Mw Nf Nr Nv Pe Po) Pc(Hv Hw Ii Jq Mr Mz Nb Nd Nf Nn Nr Pe Po) Mg(Ik Iu Jo Ma Mi Mm Mr Nd Ng Nq Om Pz) Ny(Hv Ii Ij Jq Lh Mi Na Ng Nn Nr Ns Pe) Ms(Fr Ii Jg Lh Mb Mr Nb Om Pa Pe) Of(Hw In Mb Mu Mz Na Nb Nt Pg) Pb(Ii Lh Mr Na Nn Nr Ns Pe Qa) Lw(Io Lu Mi Mu Mz Nr Nw Pe) Nd(Hq Jn Jp Jq Mj Mq Ns) Io(Ir Jp Js Jt Mm Nt Oh) My(Jh Jk Lh Nq Nw Qa) Pz(Et Ir Jg Jp Jt Ok) Hv(Lx Mi Nk Nn Pa) Jn(Md Mi Nb Oh Pa) Oe(Iv Lh Mr Nw Pe) Lv(Jk Na Nb Nc) Mz(Lx Mi Pa Pe) Mw(Hu Mq Oy) Ng(Hw Jo Lx) Pc(Ik Jo Pf) Pg(Et Mm Oy) Nn(In Mf) Nt(Is Jo) Mh(Ii Lh) Mu(Mv Nr) Hw(Is Jq) Oh(Nb Pa) NqNj LuMm NcIm NfPa IkOm IuJq QaOy JrJt} Et{Pz(Hw Hx Im Jq Js Lh Li Lw Lx Mi Mm Mv Mz Nd No Nq Nt Nv Nw Oh Po) Oi(Hw Ih Ir Iu Iv Jk Jt Mg Mi Nb Nc Nr Nt Nv Nw) Mm(Ih Ir Iv Jq Js Li Md Mh Mi Nc Nt Nv Qe) Mg(Hw Hx Ii Iu Jk Lw Lx Mi Mv Nb Nd Pc) Io(Hw Hx Jk Lh Lw Mh Mi Mx Nd Nn Qb) Of(Hw Hx Ii Lh Lx Mu Nq Nt Po) Nk(Fr Jq Lw Mu Mz Nb Nq Nw) Jn(Lu Lx Mu Nn Nq Pa Pc) Oe(Hw Hx Il Nb Nc Nr Po) Ng(Il Lh Nn Nq Pe Po) Is(Jq Lw Lx Mi Pc) Jk(Jq Mh My Nm Oy) Pg(Lw Mz Nn Pc Qa) Pa(Lw Mk Nn Pc) In(Ml Nn Pc) Ms(Mw Nn) Nd(Hq Ns) Jo(Nt Po) LwPe MwMy HuPc} Mu{Ms(Fr Ii Iu Iv Jh Md Mi Mz Na Nf Nm Nt Oh Pc Qb) Of(Hw Hx In Ji Lx Mi Nb Pa Pe Po) Ng(Ij Ir Jt Nf Nm Nw Pc) Mm(Is Jn Lv Mg Pg Pz) Oy(Hx Ii Mi Nj Pe Qb) Nr(Jo Lw Oh Pb Pc) Jq(Lx Nd Nn On Pe) Oe(Iu Jo Mr Nw Ok) Lw(Io Mh On Pe) My(Hx Ii Lh Lx) Ik(Ij Mi Pa Qd) Oh(Hv In Pa Pe) Pc(In Lh Pa Pe) Nt(Io Is Jo) On(Hu Mv Mw) Pb(Hx Mi Qb) Lv(Ih Mz) Im(Nc Oi) Iu(Io Jo) NnMf NsNu LzHv MgLi MiHq MrJo HuQb IhPg PzJg QaNw} Oi{Ma(Ih Ii Iv Jg Jt Li Mr Mx Nb Nk Nq Nt Nu Nv Oh Qd Qe) Jg(Fp Hw Ij Li Lz Mg Mx My Nc Nr Ns Oy Pa Pd Po Qe) Li(Ir Jh Jp Lv Mz Nb Nq Nt Nv Om Pc) Nq(Fp Iu Iv Jk Lj Mw Nb Oh Qd) Om(Hw Ih Iu Iv Jt Lw Mx Qe) Mm(Ij Iq Iv Lj Pc Qe) Jn(Hw Jh Jt Mw Nb Nv) Oh(Jp Lh Mw Pe Pg Po) Nw(Ir Jo Jt Mx Na) Jp(Ir Iv Jk Nb) Pc(Ih Im Mz Pg) Mg(Ir Lh Pe) Qa(aA Jt Nb) Nt(Ih Ir) aA(Jk On) PoHr} Jn{Lw(Fr Hw Io Lu Ma Mi Mr Nd Nw Pe) Oe(Jg Lh Mr Mw Nq Nt Nv Om) Mm(Hw Lh Mr Nb No Nr Nt) Pc(Jl Lu Nq Pa Pe Po Pz) Lv(Iu Lu Md Mg Ms Nr) Ma(Hw Mr Nb Nd Nr Pe) Ms(Iu Jk Jq Mq Om) Io(Im Jh Mr Nd Nm) Nq(Hu Mr No Nr) Nt(Ik Jo Nn) Mg(Lh Om Pz) Nd(Jg Nw Om) Ng(Jk Lh Lx) Jp(Hw Iu Pz) Pe(Hr Ik Ml) Po(Mh Oh) Fr(Na No) Mi(Om On) Mw(Mq Oy) Is(Jr Js) Ok(Lx Pa) NsJh LuMe MhNw NjNv HwJg ImPg JkOh} Jp{Io(Hx Ih Ii Ij Jg Jo Jt Li Lz Md Mx Nr Nx Oh Qb Qd) Jk(Hv In Iu Lw Mh Na Nf Nm Oh Oy Pc) Nq(Hv Lw Mh Mr Mx My Nb Nr Ns Oy) Lv(Ih Iv Lu Lz Md Na Nr) Pz(Ij Im Ir Li Ma Mg Nt) Po(Lw Mh Ms My Ng Pc) Nn(Hu Hv Im Iu Lw Nf) Lx(Hv Hw Lw Mq Ng) Lw(Hw Iu Mx) Mg(Lh Mi Pa) In(Iu Oh Pc) Mw(Ns Oy) Nj(Md Na) Jq(Hw Iu) Oe(Pa Pe) LuMm NbOf NgLh NkJh OhPa} Lx{Hq(Ii Ij In Jk Jq Na Nt On Pa Pc) Of(Hv Ii Ij In Jh Jo Lw Mq Nt Qa) Mh(Ij Jq Lh Nw On Oy Pe) Oy(Hv Hw Ij Jk Pg Po) Pb(Hw Ij In Mi Ny Om) My(Jh Lw Mv Nn Pf) Ng(Ma Mi Mm Mv Om) Lv(Ih Mg Mm Mz) Jq(Md Ny On Pc) Lw(Io Mg On) Ms(Jg Jh Pc) Nj(Mb Nq Oh) Ma(In Mg) Jg(Oe Pz) Ji(Nn Pc) MkOn MlHv MqMw JlJt JoOm} Om{Ng(Iu Jk Lh Mi Nk Nq Nt Pe Pg Po) Pz(Ih Iu Iv Jt Lw Lz Ma Nl Ok Pc) Of(Hw Hx Il Iu Mi Mr Mx Nt Nv) Nd(Iv Jo Mg Ms My Nk Oe) Pa(Hx Lw Mh Mk Ml Ny Pc) Jo(Ir Mg Nl Nr Po) Jl(Mi Oh Oy Pb) Mg(Ir Iv Jk) Ik(Is Pg Qa) Oy(Is Jr Pc) Nk(Im Jq) Io(Mi Qa) Pb(Pe Pg) MlIn MsPg MxOe NcNe HuJk IsOh NxOn} Nn{Ms(Ii In Jo Js Lh Lv Lw Me Nm Nt Nv Oz Pc Qb) Mf(Hw Ir Lu Lw Mq Mx Mz Nb Nv Pc Qa) Jq(Im Iu Lh Mi Mr Oz) Hu(Ii Ij In Pa Pe) Nd(In Ji Mq Nb) Lv(Hx Nb Pc) Lw(Lu Mh Pa) Ok(Mm Pa Pg) Mg(Jk Jt) Mh(Ii Pc) Mi(Nj Pz) My(Nb Po) Ng(Hx Jo) Hw(Ji Nw) On(Mz Oe) Pg(Na Pc) MlIn MrPz NcIm IjNw IoQd IuJi} Mm{Pg(Hq Hv Hw Ij In Ir Mi Mz Na Nf Ns Nw Ok Oy Qa) Lv(In Jk Md Mr Mz Nb Nf No Nr Nw Po) Io(Ij Ir Mi Mj Nk Nw Qb) Is(Hw Lh Mr Nf No Nt) Jq(aA Jk Mh Pa Qa) Pz(Fr Hx Mr Mz) Pe(aA Hq Ns Oy) aA(Ij Lh Po) Mg(Ij Jt) Ms(Ii Pa) Ng(Pa Po) Nk(Jh Ok) Hu(Lw Mj) Jl(Na Nt) LuQb MhIn} Io{aA(Hx Iu Lh Li Mg Mh Mi Mk Nc Nt Pa Pe) Ma(Hx Ir Lh Mi Mx Nb Nk Qb) Mi(Fr Jg Nk Pc Pe Po) Lv(Ih Jt Mx Nc Pa) Lw(Fr Hx Jk Mr Mx) Nt(Jg Jq Mz Nd) Qa(Jt Mg Mn Ok) Nw(Jo Mb Mg Na) Ir(Jg Mw Pc) Pg(Im Iu Nm) Nv(My Nm) FrIu QbJt JiJo PaPc} Ng{Nq(Ih Ir Jg Jt Md Mg Na Nf Nw Nx Ok Pg) Ma(Hx Ir Mh Mi Mr Nb Nk Nr Nu Pa) Fr(Ij Iv Jt Md Mg Na Nv) Nt(Lv Mv Nd Pg) Mg(aA Jk Pa Qa) Jh(Mx Pe Pg Po) Mw(Iu Jr Pa) Jg(Is Jk Pe) Po(Lv Mf) Pc(Lh Pe) LvMv IsJo JkNw OkPg} Nj{Nb(Hw Jk Ml Ms My Mz Na Pb) Nv(Hv Hw Ij In Lv Mi Ni Oe) Nf(Hx Im Mw Mx Nq Nt Ok) Pa(Hv Hw Jk Jt Lv Oe) Nt(Lv Md Mi Nq Oe) Mx(Mi Mq Na Oh) Md(Mw Na Qb) Mb(No Qd) Mq(Hx Oh) Jk(Oe Pz) MiIn MwNd MzLh NaHx IkOn IqJh} Nw{Ms(Fr Hx In Jg Jh Lh Nq Pa Pe Po) In(Md Mh My Nq Ny Pa) Jk(Lw Mq My Oh Ok Oy) Pe(Hx Md Ml Ny Pb Pc) Hw(Mh Of Pb) Is(Jo Jt Nt) Pz(Na Nc Ok) Jl(Na Nm Qa) Pa(Lw Mh Qa) Ij(Ml Pb) Jr(Jo Jt) PoPb LvOe MyHv} On{Pc(Hu Hw Jq Mi Mr Mz Ns Nt) Hu(Hx Mh Nq Ny Pb Qc) Mg(Jt Lh Mr Mv Pe) In(Hx Md Mh Nx Ny) Mz(Iu Mi Nb Qc) Pa(Hx Lw Mh Pb) Nx(Hv Hw Lw) Pe(Ik Oh) Pg(Of Pb) FrNk LuLw MhMr MkLh NcIm NdJq QcLj} Ma{Mg(In Ir Iv Jo Mr Nr Nu Ok Pa Qe) Lv(Lu Mr Mw Nd Oh) Pz(Ih Iv Jg Jt) Qa(Jq Lw Ml Pa) Jk(Hu Mh Ms Mz) Of(Hw Mr Nb Pe) In(aA Jo Pa) My(Mw Pa) Nk(Mz Ok) FpNd IjPa JoJt} Oh{Lv(Hw Iu Jh Md Mw Na Nb Nd Nf No Nv Pc) Jl(Fr Hw In Lh Lw No Qa) Is(Hw Mr Nt Pe Po) Jr(Mr Ms Mz Ok) Lw(Hu Hv Pe) Mw(Ij In Oy) Jh(In Nd Pa) FrPz NtJo MsOk} Jg{Ms(aA Hx Jk Lv Nb Pa Pe Pg Po) Pz(Hx Ir Jq Lh Mi Po Qb) Lv(Mh Mz Nd Nf Nr) Is(Hu My Oy) Pe(Ik Oy Pb) Mg(Lh Po) Jl(My Oy) Jq(aA Qa) JiNx} Jo{Nt(Fr In Lv Mb Mr Mz Ne Ok Pc) Jk(Hw Iv Jt Mq Pc Po) Po(Jt Mi Pe) Im(Jr Jt) Qa(Jt Pz) Lh(Mh Of) Nv(Hw Nb) Pe(Jr Qd) Pg(Mb Pa) IsIt} Jl{Pc(Lh Md Mz Nf Nt Qa) Lw(Lh Mz Nf No Nt) Nb(Hx Ml Ny Pb) Mz(Fr Mi Nt) Pb(Ij Ny Po) Mg(No Qa) Nd(Hq Ns) Ne(Nc Nl) FrNa HuJk LhOe} Mw{My(Fp Fr Hx Ir Lh Lv Nb No Nv Pe) Oe(Mr Pa Pe) Oy(Mi Pb Pe) Ns(Pb Pf) Lw(Mf Nd) Of(Mz Nb) WmHu MqPa MsQa NdHv NkJh} Jq{Po(Hx Md Mh My Ny) Of(Mi Nq Pa Pe) Im(Jk Nc Nk) Qa(It Nd Pc) Pa(Hr Mg Pc) Nq(Hw Nr) Jr(It Js) MgaA MlJk IsJs IuPc PbPe} Fr{Ms(Ii Jh Lh Mi Mr Na Pa) Pz(Hu Mr Na Pc) Pg(Hu My Oy) Nc(Im In) Nk(Im In) MgIh MkPa LhOf OyPe} Nq{Ms(Hw Mr Mz Na Nr Ok Pe Po) Mg(Ir Iv Jt Lh Mi Mr Nm) Lv(Hu Oy) My(Ii Nr) Of(Ji Pe) NyPb} Is{Mg(Hw Mr No Pe) Mz(Mi Nt Pa Pg) Nd(Hq Jt) Jm(Mi Nt) NoLw NsPd MdHw MhIi MkPa MsNb IrIv ItJt JrJs NyPb} Jr{Mz(Im Iu Nd Pg) Md(Hw Im Iu) Jt(Im Ms Po) Ns(Nd Pd) NmLu NaIt NdHq NeNl NfIu HxPb PzOk LiLj} Jh{Nd(Lv Mh Mj Pc) Oy(aA Jk Mj Mx) Nk(Hu Ns Pa) Mh(Ns Pa) Hu(Pe Pg) Of(Mi Nb) MyLh PbPe} Ji{Ii(Hx Ml My Ny Pb) Pc(Hu Hw Lu Nd) Nb(Ml My Pb) Ne(Nc Nk Nl) Of(Mv Nv) JkOe NyPb} Pz{Qd(Nx Ok Pe Pg) Im(Jt Mi Po) Jk(Nt Pe) MiNv NfQa IvPg QePc JtPe} cF{aI(bA bW dM) aO(bA cJ dK) bW(cQ dD) cS(cZ dG) bSdK cJcK cTcU} Po{Lw(Ms My Of Pd) Pb(Hv Hw Lz) Of(Lv Mi) LzMy NcIm} Mg{Lh(Lw Mi Pc Qa) Pe(Ik Lw Pb) Pg(Ik Nm) NtOe} dH{aJ(bA bM cE) aO(bV cU) bQ(bW cS) aFaP cUdG} Im{Pg(Hw Ir Lw Mj Mz Na Nf) MjNc} cC{bA(bC bE bL) bV(bL cK) dE(aI cT)} aA{Me(Ij In) NeNl HuJk NvOe aYdF} bW{aO(bF bP) bA(bR bU) aWbO bQcL} Ms{Qa(Lw Pc) Ok(Jk Pc)} cE{aO(aR bQ) bAcG bFdG} cU{aIdE aLbE aObZ aYcW} Mi{Ne(Nc Nl) LwHq} dK{aIbV bQcL bRdA} Lv{MzNd HqPf} Ok{Pb(Pe Pg)} aM{aIaX aYdI} aZ{aPbC aXdM} cS{aUdD aWbO} WmIuQd NtIkPe LuLwQa MvJkOy

Constrained panels with 3 analytes, where 1.0E-6 >= 'AUC p-value' > 1.0E-7. Contains 3,323 panels of 397,580 total panels evaluated. : Ip{Mm(Fp Hv Ih Ij Js Jt Md Mi Mr Mt Mu Nb Nf Nr Nt Nv Nw Oh Ok Om) Jg(Hu Hv Ih Ii Io Iu Iv Js Lz Mh Mq Na Nc Nf Ng Nr Ns Oe Oh Oy) Pc(Hv Hw Ii Ij Im In Ir Iv Lh Ms Mx Na Nb Nd Nt Nv Nw Ok Qd) Qd(Hw Hx Ii Jk Lu Lw Mb Mg Mi Mr Nb Nd Nf Nq Nr Nv Oh) Nq(Hu Hv Hw Ih Ii Ij Iv Lv Lw Ms Na Nf Nk Nr Oh) Im(Hv Ii Ij In Iu Lv Lw Lz Md Mq Nf Nr Nu Oh Qe) Nd(Fp Hq Hv Ir Mh Ms Mx Na Nc Nk Ns

Figure 42 Continued

Nu Nx Oh) Nv(Et Hv Hw Iv Jn Li Lw Mt Mz Na Nf Oe Oh Ok) Lu(Hv Ij In Ir Iu Li Mv Mx Na Nc Nk Nm Oh) Md(Et Hw Hx Li Lv Ma Mx Na Nn Og Ok Pa Pe) Lw(Et Hw Ir Iv Jk Ma Mi Mr Nb Oh Oi Om) Mg(Hx Ir Jo Mx Mz Ng Og Oi Ok Pa Qa) Nk(Hv Ij In Mj Mq Mv Na Nf Ni Nm Nx) Iu(Hx Io Jh Ma Mw Mx Mz Ng Nw Oh Om) Jt(Et Jk Ms Mt Mu Ng Nn Om Pa Po) Lz(Et Hx Jh Jk Jp Lv Mw Na Om) Mi(Hq Hv Hw In Ir Jn Na Ng) Nb(Hx Mh Ml Mz Nc Ny Oy Pb) Li(Hx In Jk Lv Mp Mt Nw Pa) Oh(Hv Ij Ir Lh Mr Na Nr Ok) Jh(Hu Ms My Na Ng Ns Oy) Nr(Et Jk Lv Mz Nw Pb) Nt(Et Jn Ne Nf Oe Om) Mw(Hu In Mq Na Ns Oy) Nf(Et Hw Lv Nn Pa) Ma(Ih Iv Js Na) Jk(Hw Ih Ir Lv) Pa(Hw In Ir Mk) Mt(Iv Lh Of) Nw(Ir Lh Pb) Oi(Iq Ny Qe) Lv(Ih Na) Mh(Na Nm) Mn(Mq Ms) Mr(Et Mz) Iv(Hx Nn) Og(Js Pd) Om(Of Oy) NsPf MpPd MsMv MzLh HvIt HwPb IhIn JoJp} Og{Iu(Hv Hw Hx Ij Im In Jk Jq Na Nr Nu Nv Nx Ny Pe Pg Qb) Iv(Ii Im Jp Lv Lw Ma Mm Mv Nd Nq Nw Ok Pa Pc Pe Pg) Hx(Ii Im Ir Jt Li Mn Mr Mz Nr Nv Oh Pa Pd) Jk(Hv Hw Jo Js Li Md Mq Mv Na Nq Nv Pc Qd) Nm(In Ir Lv Mj Mm Mv Nd Ny Oh Pc Qb Qe) Qe(Jp Jq Li Lw Lx Ma Mi Nq Nv Ok Pc) Mz(Hw Im Lh Li Mi Mq Mt Pc Pg Qa) Nv(aA Fp Hw Ij Jt Li Mh Mq Na Pe) Ma(Fp Jh Jo Jt Mq Nk Nn Nq Nw) Im(Hw Jt Mq Mt Nc Nk Nq Nx Pc) Lw(Hu Jo Jp Mj Mv Mx Oz Qd) Mg(Et Hw Ir Jq Mt Mx Pg Qb) Ok(Ir Jo Jt Li Mh Nc Nr Pc) Lv(Hv Iq Ir Mv Na Nr Nx) Oh(Hv Ii Il Jn Lh Mv Nq) Mi(Fp Hq Ij Ir Md Na) Mr(Jp Jq Li Lx Pc Qd) Pg(Hq In Ir Jo Nf Pc) aA(Ii In Jq Jt Nb Pa) Nq(Fp Js Md Nf Nj) Mq(Jp Jq Mn Nk Qb) Qd(Ii Nt Pc Pe Po) Nw(Li Nb Nf Pa Pc) Mm(Hr Ih Iq Jh) Mv(Mx Na Nj Ny) Jo(Et Jp Nb Qa) Nr(Jq Li Mn) Hw(Mn Ny Qb) Pa(Ij Nj Nx) Nn(Fp Js) Me(Jh Lh) Nb(Jq Pe) Ii(Ir Oi) Jp(In Nx) PoIj NuIh MtJq NaJh IrPc QbJt JgPd NyPb OmOy} Mt{Hx(aA Hw Jq Mh Ml My Na Nb Nt Nw Ny Oh Pb Po Qa) Ng(Ii Iu Mi Mm Mr Mv Mw Nt Nv Pa Pe Pg) Oh(Hv Hw Ii Ij Im In Lw Lx Mz Nd Pe Po) Pa(Et Hw In Lw Ma Mk Na Nm Ny Ok Pb) Lw(Hw Ii Lx Mr Mx Na Nf Nn Po) Nw(Hw Iu Mh Mi Mq Nm Ny Pb Pc) Oe(Hw Ii Ir Jg Jk Md Nr Nv Om) Mz(Hw Iu Mg Ml Mr Ms Nd Pb) Na(Jn Lx Mi Mp Mw Nk Nn Pg) Ny(aA Hu In Mr Ms Nt Qa) Oi(Im Jh Jt Nc Qb Qd Qe) Nn(Hu Ij Iu Mp Nf Nr) Lv(Iv Mb Mg Nt Om Oy) Mh(aA Nr Nt Pc Pe Qa) Nm(Jp Lu Lx Nd Of) Ma(In Ir Nf Pe Qa) Md(Hv Ij Om Pe Qa) Mp(Hw Ir Iu Po Qa) Ms(Jh Jn Jp Mg Pb) My(aA Fr Jq Nt Om) Pz(Im Jo Mm Qd Qe) Ns(Hw Jh Mq Pd) Ml(Nb Nf Nt Po) Nk(Et Mq Ok Om) Jo(Ik Jr Jt Of) Nr(Jn Jp Jq) Mu(Hw Oy Pc) Hv(Jp Js Nd) Iu(Jn Jp Pc) Of(Ij Mw Ok) Et(Nc Qa) Nq(Ii Nf) Lx(Hw Ly) Mg(In Jt) Pb(aA Nt) MmNc MqPc NdIn NeNl IjIk IoIv JrOy LiLj OkPg} Jj{Jg(Hv Jq Lz Md Mh Mq Ms Mz Na Nb Nc Nf Nr Nu Ok Pd Pz) Nf(Iv Jt Mi Mq Mv Mx Nc Nd Nj Nk Nm Nu Ok) Oh(Iq Iv Jh Mi Mn Mr Mv Mx My Nd No Pd) Nu(Jp Jq Md Mg Mj Mm Mv Mx My Mz Pf) Mq(Jp Lz Md Mg Mm Mv My Mz Nc Ok Pd) Na(Et Fp Jm Jp Mg Mi Mn Nd Nk Ny Pd) Lw(Iq Jh Jm Jp Mg Mn Mv Nk Nr Ok) Nc(Hq Jm Mj Mr Mx Mz Nd Ne Ok Pf) Md(Hv Iv Jt Mr Mx Nr Ok Pd) Pc(Iv Mg Mj Mr Mx Nd No Ny) Jh(Im Ms Mv Mz Of Pd Qe) Ok(Jp Mh Mm Mv Mz Nb Pd) Nm(Jp Lz Mj My Nk Pd) Hv(Lz Mc Mj Mv My Nk) Nx(Jm Jp Mn Nd Nk) Mh(Hu In Jp My) Mm(Im Iq Mv Pz) Nj(Hq Jm My Pd) Jt(Et Iv Mg Pd) Nr(Jq Mv Mx) Mr(aA Mi Mz) Nl(Hq My Pd) Mb(Fp Lv) Nb(Jp Oe) Iq(Lu Mn) Oz(In Pd) LzMy NiNk} Ms{Jg(Et Fr Hw Ii In Iu Iv Jq Lh Lu Mi Mj Mq Mr Mu Mw Mx Mz Nd Nn Nq Nr Nt Nv Qa Qb) Mw(Hv Hw Ih Ir Iu Iv Jt Ma Mj Mq Mx Na Nf Nm Nq Nr Nt Nu Nx Oy Po Qd) Nn(Hu Ih Il Im Iu Iv Jt Mf Nf Nx Om Pg Qd Qe) Jh(aA Hw Hx Iu Jn Lh Mi Nb Nt Ok Pe Pg Po Qa) Nw(Ii Ij Iu Lw Mb Mg Mi Mr Na Nm Nr Om Pc) Nq(Et Hx Ii Lh Lv Mh Mq Mx Nb Nj Nt) Jn(Jt Lh Mb Mi Mz Nb Nd Nr Nv Oh Pa) Om(Hx Ir Iv Jq Lh Mi Mp Nb Pa Pe Qa) Jp(Hx Ii Jt Lw Mb Mg Mv Na Pa Pc) Ma(Hx Ii Jt Mb Nd Pa) Fr(Ij Jt Pc Qb) Mi(Jk Lw Oh Pg) Mv(aA Et Jq Ok) Et(Nb Pc) Mu(Jo Jt) Jk(Na Oh) Jr(Mz Nb) PoPc NdOk QaOh} Ma{Ng(Et Hv Ij Il In Iv Jo Jp Js Jt Li Lu Mb Mj Mp Mq Mx Nc Nn Nq Nv Nx Ok Om Qb Qe) Mg(Et Hv Jt Li Mb Mh Mi Mj Mp Mq Nk Nn Nv Om) In(Jk Lw Mi Ml Nc Nk Nq Nv Oh Pc Qb) Pa(Hv Hw Ir Jn Mk Mq Mz Na Nm Oe Oh) Lv(Ii Iu Jk Mb Md Nb Nc Nf Nr Pc) Qb(Lw Mb Mq Na Nm Nq Oe Oh Pc) Jk(Hv Io Ir Js Oe Of Oh Oy Pc) Io(Jt Mp Mr Nc Nd Nv Qe) Po(Ir Mh My Ns Of Pb) Mz(Lx Ml Nd Of Pe Qa) Nk(Hv Ij Im Jh Na Nb) Oi(Fp Hw Ij Js Nc Nr) Nd(Hv Iv Nj Ns) Hx(Lw Oe Of Pc) Hw(Ir Jq Lx) Qa(Mr Oh Pe) Lw(Ir Lu) Mb(Qd Qe) Nc(Im Ok) Ik(Mu Nt) Jo(Hv Iv) Pe(Oe Pb) LxIj NfNj IiOf ImPz} Nw{Nn(Hu Hv Ir Iu Mp Mu My Mz Na Nd Nr Oy Qa) Pa(Hv Jn Mg My Mz Na Nm Oe Oh Ok Pc) Nq(Hv Hw Ij Ir Na Nk Nr Ns Pe Qa) Ij(Iu Lx Md Mm My Nd Nk Ny Of) In(Iu Lx Mg Mi Mm Nd Nk Oh Pc) Hw(Hx Md Mu My Ns Ny Oh Pc) Qa(Et Lh Lx Mi Ml Mm Nd Pb) Oe(Et Jk Mb Nr Om Pe Pg Po) Po(Lw Mh My Ny Of Oy) Lw(Iu Lu Mx Pe Pg) Mb(Im Lv Mg Nj Pz) Mp(Jn Mu Na Nm Ok) Lx(Hv Mq My Pb) Mh(Ii Mi Mj Nr) Mu(Iu My Oy Pe) Nk(Mq Ni Nm Om) Mg(Jo Ng Pe) Ns(Jh Nd) Lu(Nm Pc) Ml(Hv Om) Nc(Im Ne) Ng(Jo Nt) Qc(Iv Mj) Jk(Hu Mz) Jn(Pb Pc) Of(Hv Lh) Pe(Oh Oy) EtIo MqNd MyHx NeNl IuJq JlJt OmPb} Mp{Oh(Fp Ii Im Iv Jk Lh Mr Nf Ni Nv) Nq(Hu Ih Iv Lj Na Nf Oc Ok Qd) Lw(Hx Ii Iu Jh Jk Js Li No Nv) Hq(Hw Hx Jk Nm No Nt Ok Pd Qa) Nn(Hw Hx Ir Nb Nf Ni Om Qa) Ns(Hx Jk Na No Ok Om Pd Qa) Pc(Hv Ih Ir Iv Lh Mz Nb No) Pd(Hx Jp Nj Nm Nt Nv Ok) Mi(Hw Ir Iv Ni Ok Qd) In(Fr Iv Jg Jo No Po) Oy(Hx Mr Mw Pa Pe Pg) Ir(Mr Mu Nf Om Pe) Md(Hw Im Iv Li) Mg(Fp Li Mx Nc) Lz(Ij Na Ni) Mk(Hu Nt Pg) My(Jh Mv Om) Nf(Mr Nb Pe) Qa(Et Mu Om) Lu(Jt Li) Hu(Jk Mx) Hv(Jk Po) Io(Js Nb) Jg(Jq Pa) Jp(Iv Jo) FpIu FrJq NuIm LxJt MuHw NaPa QeOe OmaA PePf} Jp{Lw(Fp Hx Ii Im Lu Mh Mi Na Nb Nd Nr Nt) Io(Im In Iv Mb Mq Mr Na Nc Nd Nu Qe) Oe(Hx Iu Jg Mr Nb Nq Nr Nt Nv Qb) Pa(Hv Hw Ij In Iv Jo Md Na Nf Ni) Pc(Hw Hx Ii Iu Lu Lx Mx Nd Nt Pz) Mg(Hx Ij In Jk Jo Mh Mx Ng Qb) Nq(Hu Ih Iu Mq Na Nf Nm Oh) Po(Hw Iu Na Oh Oy Pb) Lx(Jo Na Nm Of Oh Oy) Oi(Fp Hx Ih Js Mx Qe) Iu(Hw Hx Ij Nb Ng) Jk(Hu Ih Iv Jt Of) Mm(Hw Ij Mh Mx) Nn(Fp Na Ni) Mi(Hq Ij In) Nd(In Mq Nb) Ng(Jo Mv Nv) Pz(Ih Jg Qe) Jn(Lu Nr Oh) Nt(Ne Oh) Mh(Im Nv) Mw(Hu Mq) NsJh LvMx MlIn NcIm NfNj IiOh} Et{Io(Ih Ii Ir Iu Iv Jt Mr Nb Nl Nr Nt Nv Oh Pc Qd Qe) Ng(Fr Hw Ii Ij Iu Jk Lx Mi Mu Mw Nb Nr Nt Nv Pc) Pz(aA Iu Jt Lu Lz Md Mg Mr Nb Nf Nr Ok) Qa(Lw Lx Md Mi Mu Nn Nq Oh Pa Pc) Mg(Jo Jt Li Mr Nr Nv Om Pd) Jn(Hw Lh Lw Mi Mr Nd Nt Pe) Of(Iu Jo Md Mr Nb Nr Nv) Mm(In Iu Jt Lv Oh Ok) Nk(Lu Na Nf Ni Ok Om) Lw(Il Jk Lu Mh Mx) Nd(Iv Lu Mh Nc Om) Oe(Mr Mu Nt Nv Qb) Oi(Js Li Om Qd Qe) Jk(Ir Mz Oh Ok) Jo(Mr Nb Nr) Nq(In Mh) Nc(Fr Im) Oh(In Pa) Pe(Mi Mu) NnHx LxHq MzPa HwPg} Nn{Hu(Hw Hx Il Ir Ji Jk Jq Lh Lu Lx Mj Mx Mz Nc Nr Pg Po Qa) Lx(Hv Hw Ij In Ir Lw Mq Mu Mz Nr Qa) Pa(Hv Hw Ij In Ir My Mz Qa) Lw(Fp Hx Ii Mi Mu Mx Nr) Mf(Iu Jk Na Nt Oy Pg) Mi(Hv Ij In Ji Mz Oy) Mu(Hv Ij Ir Mz Nr) Im(Hx Ii Js Nk On) Ji(Jq Lh Mr No Nt) Md(Mx Nr Ns Pc) Nd(Hv Mz Na Nm) My(Hx Lh Nv) Jq(Fr No Nt) Oy(Mw Pe Pg) Pc(Ih Nu Qb) Po(Hv Ns) Mg(Jg Ng) Nb(Mv Of) Hx(Fr Pb) Pz(Iv Jt) On(Ir Qa) NrIn MlMz MqMw NeNl NgJh NiNj IjOz} Mw{Oy(Hx Ji Li Lu Lw Lx Lz Md Ml Mr Mu Mx Mz Nf Nk Nq Nr Pc Pd Pf Pg Po) Lv(Io Iv Lu Md Mh Mx Mz Nf Pa Pc) Mq(Lw Mz Nd Nf Nj Nq Oh Pc Po) Oi(Ih Ir Iv Jg Nb Pc Qd) My(Ih Im Js Mm Oe Qa) Ng(Im Lh Mg No Nt Pe) Oh(Hw Iu Md Na Nf Nr) Nj(Hw Ii In Lu Na) Pc(Lu Lw Md Nd On) Ns(Hx Jh Lz Ml) Of(Ii Lh Ok Qa) Lz(Hu Hv In) Nd(Ij In Mj) Lu(Jg Lw) Mz(Ml Pb) Hu(Hx Mx) LwMh MdMj MgOn NbOe NcIm IoQd JoPe} Lx{Mh(Hx Ii Jo Js Mk Nd Nt Oh Ok Om Pc Qa) Hq(Fr Hw Jo Mg Mz Nb Nd Nm Ok Om Qa) Hx(Ii Ij In My Ny Of Oy Pb Pf) Lw(Jm Mf Mi Mu Nr Oh Qa) Of(Hw Mz Na Nb Nf Nm Pg) My(Ii Ij In Nf Nq Ns) Pc(Hv Hw Ij In Mu Nr) Ml(Hw Ii Ij In Qa) Pb(Ii Na Nf Pf Qa) Ny(Hv Ij Js Pf) Oh(Hv Ij In Mu) Ly(Nj Pe Pg) Ng(Lv On Pg) Md(Ij Om) Mg(Jk Nm) Mu(Hv Qa) Jh(Mv Ns) Oy(Ii Mz) MmJi IrOm JmPg JtOn} Pz{Jg(Hw Ih Ij Im Iu Iv Js Jt Lv Mh Mm Mq Mz Nb No Nq Nt Nv Oh Ok Pa) Qd(aA Hw Hx Ii Ir Iv Jh Lh Mb Mg Mi Mr Nb Nm No Nt Nv Oh Pa Po) Jk(Im Ir Iv Jt Li Lv Mh Mx Mz Nb Oh Pc Po Qe) Mm(Hv Ii Il Im Jq Lu Mj Nb Nr Nv Ok) Im(Ir Mj Nb Nt Om Pc) Qe(Jh Mi Nt Ok Pg Po) Ir(Li Mg Nt Pg) Mi(Jh Lv Ok) Li(Nt Nv Om) Pg(Ih Jt Mg) Ok(Mg Nt) FrJt} Io{Mm(Hw Iq Iv Jk Js Mr Nb No Nr Nt Nv Ny Qd Qe) Nt(Ih Ir Jk Jo Lv Me Ng Oh Pb Pc) Lv(Hx Iq Ir Iv Jg Js Li Ny Qb) Nv(aA Im Lw Nb Oh Pa Pc Qb) aA(Ii Ij In Jo Jt Qd Qe) Ir(Jh Jk Li Mi Mn Pg) Iu(Mn Mz Om Pe Qb) Jg(Nb Nk Pa Qb) Jt(Im Jk Jn Pe) Pc(Ii Mr Mx Qd) Pg(Ih Iv Of Oy) Lw(Ii Iv Mj) Mi(Jk Li Nc) Im(Mj Nk) Qd(Jn Nc) Lh(Mh Oh) NoMe MuIv NjJk HxJn QaJo} Oi{Jg(Hu Hx Ii Im In Iq Jk Jo Lj Lw Mh Mj Mr Na Nb Nf Ng Nq Pc Qb) Li(Hw Hx Ih Ii Ij Iu Iv Jk Jt Lu Md Mi Mm Nr Oh Qd) Oh(Hu Hw Iu Iv Jh Jk Jn Lv Mq Nb No Nu Nv Qd) Pc(Fp Hx Jh Jk Jq Js Jt

Nr Qe) Qa(Lh Lx Mi Mr Mt Mu Mz No Nt Po) Qb(Hv Hw Ij Jo Jt Md Mt Na Ni Ok) Lv(Ij Im Iv Jo Jt Li Na) Jp(Fp Iu Md Na Nq Nr Pd) Jq(Lh Lx Mi Nq Nr Nt Po) Nw(Fp Hw Lh Me Mu Mx Nf) Mh(Ih Im Jh Md Mu Ok) Ms(Ij Iq Jh Nq Om) Nc(Im Ma Nf Ni Oh) Ng(Ij Jt Mu Nb Nq) Hx(Hv Iv Oe Ok) Io(Ih Jh Nx Pf) Ip(Jo Li Na Nq) Mt(Mr Nb Nf) Nk(Im Nf Ni) Ij(Et Lx Qe) Jj(Jh Na Oh) Po(Ns Of) Mg(Oi Pd) Ji(Mr No) aA(Om Pd) FpMd LxHq MzOn NbOf HuIq} Ma{Mg(Hr Ij Iu Jh Jp Js Md Na Nc Nf Ng Nm Nq Nx Oi Pd Qb) Nb(Hx Iv Lx Mh Ml Ms Mt My Nc Ny Oe Oh Pb) Ih(Hw Ii Ij In Io Jk Lu Lv Lx Mb Mp Pa Pe) Qd(Hv Hw Hx Ii In Lu Mr Na Nf Ng Nr) Mt(Hv Hw Lx Mq Mr Ms Nc Ng Nr) Nd(Hq Ij Lu Me Mh Nc Ng Nk Nu) Iv(Hw Hx Ik Io Jk Mb Na Pa Po) Nm(Fp Jk Lu Mx Ng Nk Oi Pz) Oh(Fp Hw Hx Ii Ij Mx Nr Qe) Na(Hx Jk Jo Lx Mh Ng Po) Nf(Hw Ir Lx Ng Nk Oi Pa) Iu(In Io Jk Jq Mz Ng Oi) Mq(Im Jk Lv Lx Mw Nk) Hv(Lx Me Mi Nn Nq Nv) Jo(Ip Jk Nk Of Pa Qb) Mb(Fp Im Io Mx Nk) Md(Hw Mh Mx Ng Qe) Nr(Jq Lx Oe Pb) Mr(Ir Mh Mz Oe) Nc(Ii Ij Jk Pa) Im(Ij Lu Mh Qe) Ns(Hw Jh Pd) Mi(Hq Hw Ij) Pb(Lh Mz Ny) Nl(Io Ne) Ii(Mh My) Pz(Li Nx) Qe(Nv Oe) Oy(Mw Po) NqIj MzHw NgPd NiNk HxOk InLi JhLj JnJt} Jh{Ms(Et Ih Ii Ir Iv Jp Jt Lv Lz Mh Mw Mx Mz Nc Nn Nq Nr Nv Pa) Hu(Hw Hx Il Iq Ir Jk Jp Js Mh Mt Mx Nl Nw Po Qa Qb Qe) Oe(Hx Ir Jn Jp Mi Mw Mx Nb Nk Ny Oz Pa Pe Qa Qb) Ng(Et Hx Ir Jo Jp Js Li Mw Nk Nl Nw Oh Pa Qa) Ns(Ir Iu Js Mx Nb Nn Nv Oh Pf Qa Qe) Nd(Hv Lu Mx Na Nc Nk Nm Nu Oy Qb) Nk(Ij Iq Lz Mt Mz Na Nf Nu Qe) My(Hx Ir Js Mi Mx Mz Nw Qa) Oh(Fp Hv Hx Iu Nb Nr Nv Qe) Qb(Hv Lu Md Mq Na Nm Oy) Oi(Ih Iq Iu Js Mn Ny Qe) Lv(Hw Hx Ih Iu Lu Na) Lz(Hv Hw Hx Ii Ij Nb) Oy(Ir Ji Lh Mw Nl Nw) Mh(Ih Ij Im In Qe) Mp(Ih Lj Mx Qd) Na(Mt Mx Po Qe) Nc(Ij Im Mi Pa) Nf(Hw Hx Mx Nj) Iu(Hv Hx Ij In) Jj(Iq Jt Li Ok) Mg(Jo Nq) Ik(Iv Nt) Of(Mz Pg) LxLj MdNj MiHq MxIo IrPz} Om{Pb(Fr Hw Lh Lu Mh Mi Mq Mr Mt Mu Mx Mz Nb Nq Nr Nt Nv Ny Po) Ms(Et Fr Hw Ih Iu Jt Lx Mr Mu Na Nq Nr Nt Nv Oh) Oe(Et Iu Iv Jk Lh Mr Na Nb Nr Nv Pa Pe Po) Nn(Hu Im Iu Lx Mi Mu Nd Ng Nr Ns Oy) My(Hw Ip Ir Iu Lx Mh Mx Mz Nv Nw Qa) Of(Et Fr Im Jp Jq Lu Mw No Nq Nw Qb) Ng(Et Jt Li Lz Mu Na Nl Nr Nw Oh) Mz(Hw Hx Iu Md Mh Mi Ml Nd Ny) Ik(Fp Ir Iv Mg Mu Mx Nq Nt Qd) Oy(Hw Hx Ir Iv Jn Lh Mh Mx Nw) Mt(Hw Hx Iu Mh Nc Nr Ny) Nq(Hw Lj Nc Nk Ns Qd) Lx(Hx Ly Ml Ny Oh Qd) Mp(Hq Hw Mk Mr No Pd) Ml(Hx Lh Mi Nb Po) Nb(Hx Md Mh Ny) Nd(Nw Oh Ok Qd) Lh(Hx Mh Ny Oh) Po(Hx Mh Ny) Qd(Hw Mr Pa) Mu(Iu Lj) Na(Jo Mg) Io(Jt Nl) Nw(Iu Md) NrIm NcOk HwOh HxNy IhPg JoJt LjNv} Nw{Pb(Hv Ii Lh Mi Mr Mx Mz Nb Nf Nr Ny Pa Pg) Mg(Hv Hw Ir Jn Mr Mz Na Nc Nd Nr Oy Qa) Iu(Hv Hw Mh Mq Mz Na Nf Ni Nm Ok Pe Qa) My(Fr Ii Lh Mi Mq Mr Mv Nb Nq Nv Pg) Im(Hw Jt Lv Mj Mq Mr Nb Nn Nr Nu Pe) Mh(Hx Ir Lh Mb Mq Mr Mx Nb Nt Pg) Na(Jq Lx Mi Mu Mz Nd Oh Pe Qa) Nd(Et Hv Ir Mb Mz Nr Oh Ok) Ny(Hv Ii Lh Mi Mr Mx Nb Nr) Nq(Hu Iv Mq Mv Nc Oe Oy) Mp(Et Fr Iv Jo Jt Ni Pg) Mi(Hv Hw Hx Jn Jo Ng) Oh(Hv Ij Lx Mr Mz Qa) Ml(Ii Lh Mt Mz Nb) Hx(Ii Lh Mr Nb Nr) Oy(Fr Ii Mw Pa Pg) Nt(Et Mu Oe Qa) Lx(Ir Mb Mz Nm) Nn(Iv Ni Ok) Ms(Jo Jt Nb) Oe(Mr Nb Nv) Of(Ii Jk Nb) Et(Hw Pe) Ns(Mq Pd) Mb(Li Nk) Md(Hv Lh) Mu(Jo Jt) Ip(Jo Jt) WmLy LvLi MkPa IoIv IrJs} Mt{Mh(Et Fr Hw Ir Iu Iv Jq Lx Mi Mr Mu Mz Nb Ok Po) Ok(Hx Jk Lx Mi Ml Mp Ms Nc Nd Ny Oh Pb) Ir(Hx Lv Ml Ny Of Oh Oi Pa Pb Qc) Nq(Hu Hv Hw Ij Nc Nr Oe Oh Qa) Im(Iv Lv Mp Mu Ng Ny Pa Pb Pe) Et(Hw Hx Ml Mp My Ny Of Pb) Ms(Iu Ml Mn Mq Na Nf Nr Qb) Na(Jp Md Mu Nc Nd Oh Po) Iu(Hx Md Ml Mu Nf Oe Qa) Fr(Hx Ml Mv Ny Of Pb) Nm(Md Ml Mp Ng Nk Oi) My(Mr No Nr Pa Pe) Jo(Ip Lv Ml Oi Pa) Jt(Lv Mz Ng Of Pa) Oh(Iv Jk Mr Nf Nr) Oy(Ii Ip Lx Mp Po) Hw(Md Mi Ny Oi) Qa(Mi Nt Pa Pg) Of(Jp Mp Nc On) Mg(Hv Nf Oe) Mz(Hx Md Ny) Nb(Ng Ny Pb) Jk(Hv Nc Ng) Nr(Md Nf) Nt(Mu Oe) Mp(Mv Qd) Lj(Mj Pe) PoPa LvLi LxMl MbNj MiPg MvIp MwNc NdIv NgJp NiNk HvNv QcQe OiaA} Im{Nn(Hu Hv Hw Ij In Lv Mf Mj Mq Mu Mz Nb Nr Oz Pa Po Qe) Jp(Hw Ih Ij In Iu Jk Js Jt Lu Mj Mq Nr Nu Oh Qe) Lv(Io Iv Lu Lx Mi Mr Mz Nb Oh Pa Po Qe) Mp(Hv Ii Ij In Io Mj Mr Nb Pa Pe Qe) Oh(Ii Ir Jk Lx Mu Oi Pa Pe Po Pz Qd) Mh(Ij In Md Mq Nm Nq Nv Pa) Nk(Hv Ij In Mq Mw Na Ni Nm) Mz(Jk Mi Ms Mu Nv Pa Pe) Nb(Hx My Ng Nq Oe Of Oi) Ng(Jk Lh Mi Nt Pa) Mu(Hv Mj Nr Qe) Nc(Hx Io Js Mg) Iv(Jk Nv Oi Pz) Nq(Mj Pa Qe) Mw(Hu Mq Ms) Pz(Li Mv Qe) Oi(Ih Nt Nv) Po(Oy Pb) Nr(Lx Qd) Io(Iu Js) Ip(Na Pd) Jk(Hu Oe) Jn(Jo Pd) Jt(Mg Ms) FpNd NmPa NtIk LxMq MbNj MjQd NeNl JoJq NvOe NyPb} Mw{Ms(Fp Hx Ii In Iq Js Li Lj Lv Lz Mn Mr Mz Nb Nc Nd Ny Oh Pa Pb Pd Qb Qe) Oy(Et Fr Ih Il Iu Jq Lh Lv Mj Mq Nb Nc No Nv Ny Ok On Qa Qb) Mh(Hv In Jj Lu Md Mq Na Nb Nm Oh) Lv(Hw Hx Ih Ii Ir Mq Na Nb Nr) Oi(Hx Iq Iu Js Mx Nv Pd Qe) My(Iu Iv Jt Nt Pg Qd Qe) Na(Ih Lz Md Mx Mz Nd Nf) Ns(Et Hw Iq Mq Pd Qe) Ng(Ip Jn Jo Mv Po Qa) Hu(Et Iq Ml Mv Of) Nm(Io Lu Lz Nd) Lu(In Jp Mq) Md(Hw Iu Mz) Mx(Nc Nf Oh) Io(Iu Iv Jt) Oe(Hx Jk Nr) Mp(Ni Of) Mq(Jk Nv) Mz(Hx Ny) Pz(Ir On) Pa(Mk Ni) FpOh NuIh LzIj NeNl NfHw HvIu IkIv InOn JoJt JqOf} Oh{Oi(Fp Hx Ih Ii Il Ir Jt Mg Mj Mn My Mz Nm Nr Oz Pa Qb Qe) Jp(Fp Hw Hx Ij Iu Iv Jj Mg Mr Mx Mz Nb Nd Nf Nr Nu Nv) Qa(Fr Jk Lx Mr Nd No Nt Pa Pg Po) Jj(Md Mz Nb Nc Nf Nr Nu Nx Ok) Jn(Hw Io Lu Mr Nb Nd Nr Nt Ok) Po(Et Hw In Mz Ok Oy Pa) Lv(Hu Hx Iv Jo Mb Nc Qb) Nq(Hv Hw Hx In Ms Nb) Lx(Et Hw Jo Mz Nb Nm) Jk(Hv Ij Io Mh Mi Ok) Ip(Iv Jt Li Md Mg) Ij(Fr Hu Iu Pa) Et(Hx Lu Pe) Nd(Hu Hv Mq) Oe(Nb Nt Nv) Pa(Hw Nm Ok) Fr(In Pe) Ml(In Mz) Nj(Nf Oz) Hv(Hu Ms) Lh(Jo Mg) Pg(Na Ng) NtMu MpLi} Nn{Et(Hu Hv Hw Ii Ir Jq Lx Mf Mi Mp Mu Mz Nr Po) Pg(Hv Hw In Ir Iv Mu My Mz Nr Ns Qa) Qd(Hu Hx Lx Mf Mp Mu Na On Qc) Fr(Hw Ij In Ir Mf Mz Nr Qa) Mu(Ih Iu Jp Mi Na Nv Qa) Nm(Lu Lx Mf Mh Mp Pa) Iu(Hu Hv Ij In Md Mz) Oe(Hx Nb Nt Nv Pa Pe) Lx(Iv Jo Na Ok Oy) Qa(Mi Mr Nd Nt Po) Mf(Fp Nf Ok Qe) Na(Hx Mp Pa Po) Jo(Ip Jn Jq Mp) Mi(Hw Ir My) Ni(Ms Nk Qb) Nv(Fp Hu Hv) Nt(Hu Mz) Me(Nd Pa) Mq(Il Ns) Ng(Jk Jt) In(No Oz) Io(Iv Jt) Ok(Mp Nd) Oy(Hx Po) LvIv MbNj MlPb MrMy MzHw PzLi} Jk{Oi(Fp Ih Ir Iu Iv Js Jt Mg Mq Mx Mz Nb Ng Nv Pa Qe) Ng(Iv Jp Lh Li Lx Mh Nm Nt Ok On Oz Pe Pz) Mg(Iu Jo Mh Mq Ms Nb Nc Nm Nx Po Pz) Io(Hx Ih Iu Iv Js Lv Mx Nm Nv Pa Qd) Pz(Fp Hx Ih Iu Js Lz Mj Na Nm Nr) Oe(Hx Iv Lv Mh Nt Nx Pe Pg) Ms(Hx Iu Mq Mz Nm Oz) Jo(Hv Ij In Ip Nf Nj) Mp(Fp Ih Na Nm Pd) Oy(Md Mq Nu Pe) Lx(Jm Ly My) Ik(Iv Nt Po) Ok(Mz Nk Qa) Lv(Mh Na) Mq(Nk Pb) Nd(Fp Nj) Hu(Fr Nj) Of(Mz Nm) PoPb EtQd MhNa JnJt} Nq{Ms(Fp Hv Ih Ir Iu Iv Nx Pa Pg Qb Qe) Mz(Et Md Ml Mv My Pa Pb Pe Qa) Oy(Hx Ij Ji Mr Pa Pe Pg Qb) Hu(Hx Ir Ji Jq Mg Pg Qa) Et(Hw Ir My Nr Qd) Lv(Hx Ih Mq Na Nb) Hv(Lx Mh Of Pa Pg) Qa(No Nt Ok Pa Pe) Oe(Hx Ii Nb Pa Pe) My(Hx In Nv Pg) Nc(Hx In Lx Pa) Jo(Jp Mp Ng Nj) Ir(Mi Ok Pe) Jt(Io Ip Mp) Lj(Jp Lx Mu) Nm(Oi Qb) Ns(Hw Pf) Mg(Iu Pd) Ng(Li Qd) Nk(Mq Nf) Ik(Iv Nt) Of(Hx Nb) Pb(Mr Po) NoJq MbQd MhNa MpNi NdNj NeNl IjPa IpLi IvJp} Lx{Mh(Hq Hv Hw In Iu Iv Mi Mr Mu Mz Nb Nm Ns Pd Pf Pg Qd) Ng(Hv Hw In Iu Mb Mq My Nm Nv Po) Mg(In Ir Jo Jt My Nc Pb Qa) Mu(Hw Ih Iv Mz Na Nm Oy Qd) Mz(Et Hx Md Ml My Pb) Nb(Hx Md Ml My Oe Pb) Oy(Mi Mq Na Nt) Ns(Hx Mq Pb) Ml(Hx Na Nf) My(Fr Nm Nv) In(Iu Md Ny) Et(Hw Jq) Ly(Iv Nc) Mb(Mf Qd) Ne(Nc Nl) Nf(Hx Ny) Ni(Nk Of) Ij(Iu Ms) FrOf NmPb NtIk LvLi HqPd HvIu HwJo IiNy IoJt JqaA} Jp{Mg(Fp Hv Hw Ih Iu Jt Lu Md Mr Nb Nd Nf Nr) Iu(Fp Hv Lu Md Mx Na Nf Ni Nu Nv Ok) Nb(Hx Iv Mh Ml Ms My Ny Pb) Nd(Hq Hv Ih Ij Ir Na Nm Ok) Nv(Hv Hw Na Nf Nm Nr Pz) Mh(Hv Ii Ij Md Na Nm) Mi(Hv Hw Na Nf Ng Ni) Pz(Iv Jt Mv Ny Ok) Md(Hw Hx Mx Ns) Ms(Ij Mz Nx Qb) Nm(Fp Lu Mx) Lz(Ij In Mj) Mq(Lu Nk Ns) Ni(Nj Nk) Ih(Ij Nu) Pa(Mk Ng) LuQb MvMy NeNl HvJj IoPd IqOi QcQd NyPb} Ip{Mg(Ih Ii Iv Lu Lv Mh Mr Nc Nd Nk) Nf(Ir Iu Iv Jt Li Lu Mi Na Nc Nr) Md(Ih Ir Iu Iv Jt Lz Mr Nr Qd) Ih(Hv Ij Lu Mj Mq Mv Nu) Nc(Ij Mj Mq Mv Ni Nm) Jt(Lu Mi Mr Mz Nd Nv) Iu(Hv Ij In Lv Na) Lu(Js Lz Mj Nr) Mb(Fp Mh Ms Nj) Nd(Ij In Mj Nm) Jo(Mp Ng Pa Qd) Lz(Hv Ij In) Li(Ii Na Nb) Nr(Nv Oz) Ns(Hw Pd) Ms(Js My) LvIi NeNl IrNv} Mp{Fr(Hq Hv Hw Ij Ir Mr Mu Mz Na Nf Ns Pe Qa) Et(Hv Hw Ir Lh Mr Mu Mz Nb Nf Ns Ok Pe) Qd(Hq Hv Hx Ij In Mu Na Ns) Ns(Hr Iv Jo Jt Nt Nu) Mu(Ih Iv Lj No Ok Oy) Po(Ij Jt Na Oy) Hq(Fp Iv Jo Ni) No(Mg Mz Qa) Jt(Nd Of Pa) Nm(Io Lz) Nr(Nf Oy) Ni(Iu Qb) Ih(Mg Mj) Qa(Mr Pa) Lj(Nv Pf) NfHw NgLi InOf JoPa LhOy} Po{Ng(Hw Iu Jo Jt Lz Mi Mr Mv Pe Pg) Of(Fr Ij Mz Na Nb Nm Ns Nt Nv Pg) Ns(Hw Hx Mh Ml Mu My Nd Pb) Pb(Fr Mu Mz Nr Pe Qa) My(Fr Md Nm Nv Pg) Mg(Ik Jo Lv Ms) Ml(Ij In Mz Qa) Oy(Et Mu Mz Pg) Oe(Mr Nv Pe) Oi(Ih Nb Nv) Hv(Mi Pa) Iv(Ik Nd) NmLu LzNy MsNb NeNl IoJt} Lv{Nd(Fp Io Iv Li Lu Mh Mq Nb Nc Nf Nm) Mz(Hw Iu Ml Mr Na

Figure 42 Continued

Nb Nr Nv Pa) Nc(Hv Lu Mj Mq Mv Nf Nm) Nm(Io Lz Mx Nk Pa) Na(Ih Mh Nf Nj) Io(Iu Nk Qd Qe) Hx(Iv Lu Md) Li(Mu Ng Ok) Nv(Mh Oe Oi) Mx(Md Mg) Nf(Mi Nt) Nj(Hw Lu) LzHv MqNk NbOy NgLh IhOi} Mg{Oi(Hx Iv Js Li Lj Mx Nt Nv Pa Qd Qe) Ng(Et Ii Ir Iv Mj Mr Mz) Jn(Hw Jt Lu Mr Nd No Nr) Jo(Iv Mr Nr Nt Pg) Ok(Nc Nk Pa Qa) Pe(Hr Jt Mi Oy) Li(Ii Iu Mi) Io(Ir Nv) Pz(Qb Qe) Jq(Hw Nr) Lh(Pg Qd) MhQb MkPa MuIk NaPg NbNj} Jj{Nc(Hv Mh Na Nb Ni Nm Nr Nu Nx) Nm(Hv Lu Md Mh NI Nu Pf) Mh(Hv Md Mq Nd Nu Of) NI(Hv Mq Mz Nd Nf Pf) Md(Na Nd Nf Nx) Mq(Nj Ns Pf) Na(Hu Mj My) Mb(Mk Nk) Nb(Jq Ms) Nf(Nx Oz) Nj(Nr Pf) Hv(Nu Pf) Jt(Io Mz) LzNx MvMy OyOz} Io{Nv(Ir Iu Li Lj Mx Na Ng Nk Nr Qd Qe) Mi(Iv Lh Lj No Nt Ok Qd Qe) Jt(Fr Hx Ir Li Mu Nj Nk Pa) Qd(Lh Mb Nt Nx Pg) Nm(Ih Iq Mn Qb) Iv(Fr Hx Ir Nd) Hx(Ir Ok) Js(Et Pa) Ny(Ih Iu) NtIk MnMx MyNb NdIr JnJo} Mz{MI(Hw Iu Lh Lz Mi Mj Mr Mv Nd Nr Pa Qa) Mu(Et Fr Iu Mi Nt Ny Pa) Of(Fr Lh Mi Nd Pg) Et(Hw Iu Mi Nt) Oi(Hw Iv Jt) Fr(Mi Nt) Ms(Mq Ok) Qa(Pa Pe) Jn(Nd Pa) Oe(Nb Nt) Pb(Mi Mv) MeaA HrPe PzQd JoJr OyPg} Jq{Pa(aA Md Mh My Nb Ny Oy) Mi(aA Fr Md Mh Ny Pb) MI(Hx Ii II Lh Mh Nb) It(Hv Hw II Ir Iu Qe) Nd(Et Hq Hw Nr Ns) Et(Hw Mu Pe) Fr(No Nt) Mh(Ii Nb) Nj(Mq Oz) Iu(Js Pg) Pb(Hx Nb) NoMu LuMe LhaA} Pg{Pb(Hq Hv Ij In Jo Lh Mr Nf Nr Pa) Ng(Hw Ir Iu Jo Jt Lh Mr Nf Pe) Of(Hv Hw Ij In Lh Nb Nf Pe) Oy(Lh Mi Mr Mv Nb Nf Pa Pe) Hq(Mi Oe Oi) Na(Mi Pa) Jm(Iu Nt) MvMy NeNI NiNk} Nj{Md(Hv Ii Iq Iu Mb Mj My Nr) Nf(Hw Iv Mi Mj Nb Nr) Mq(Ih Iq Mj Nr Ny) Na(Ii Ij Mv Ny Pd) Nd(Hx Ih Ir Nr Pd) Pa(In Jo My) Lu(Nm Qb) Ih(In Mb) NtIk NuMj LzNi MiJt MvNg HvIq JoNv} Oe{Nb(Hx Iv Mh Mi MI Nc Ny Pb Pe Qa Qb) Pa(Fr Hv Hx Iv Js Mq Nm Nv Nx Ok Qa) Nt(Fr Jo Nd Ng Qa) Qa(MI Mr Pe) Nv(Hw Ok Pe) Fr(Mr Pe) EtQe NrJn MuLi} Oi{Mv(Hx Ih Mn Mx Nr Qb Qe) Nv(Iv Jt Lj Mq Qd Qe) Nb(Fp Iv Lj Qb Qd) Mi(Ir Lj Qe) Ih(Fp Mq Nu) Iu(Iv Mn Qb) Nm(Li Mn) Ir(Iv Jt) NtNe LuQd MxLi IqIv LhaA} cU{cM(aY bQ bR cA cC cE cF cL dH) al(bE bZ cC cE dK) dG(bQ bU cA cE cL) aY(aM cG dL) cC(cK cT dl) cL(bW cW dK) bS(bR cD) cG(bZ dH) cK(bU cD) bEcT cWdH} Ng{Nt(Ir Jt Md Nf Ok Qd) Mv(Et Hx Mi Mr Ny Ok) Li(Et Hw Mi Nv Nx Pe) Et(Jo Jt Mr) Qa(Iu Jo Jt) Pe(Iu Jt Mi) On(Nd No) MiHu MqNv JnJo LhPb} Mu{Pa(Hw Ih Na Nm Qd) Pb(Jo Nb Nv Ok) Md(Ik Lj My) Iu(Hv Hw Nf) Lh(Et Oy Qd) Fr(Ir My) Ms(Ij Qe) Ik(Jt Qe) Of(Jo Nf) EtNt MrOy NbNy QdOn LjNv} Jn{Nb(Hx Mh Ml Nd Ny Pb) Nd(Hq Hw Lu Nr Ns) Ns(Mq Pd) Lu(Iu Nm) Mh(Ii Pa) Ne(Nc Nl) It(Hv Na) NtJm MdOk MkPa MsJo MvMy IiLh LiLj NyPb} Fr{My(Md Mi Mr Nb Nv Pe) Pb(Hw Ij Jo Nr Ny) In(Iu Mh Mi Ny) Of(Hv Jo Mr Nb) Nc(Nf Ni Nm) Mi(Hq Qa) NoQa NiNk IiOy IjIu} Qa{Ml(Ii Lz Nb Nf Ny Pa) It(Hv Ii Ir Iv Nv) Nd(Hq Ns Ok) Nt(Jm Ne) Ms(Jt Nb) NmLu MdOk MvMy NbOf NeNl} bW{aY(aO bQ cQ dF dM) dH(bV cQ dF dM) aO(bR cN cO) cD(bQ cQ dM) bZ(bQ dF) dE(aI dD) bRdM bVcC cLcQ} Pz{Qd(Iu Jo Jt Lu Md Mq Na Nd Nf Nr) Qe(Jt Li Mv Nv) Nt(Hx Ih Iq) Li(Ij Mi) QbJt} cF{cK(aI bQ dK dL) cT(bH bL dI) dG(bE cN dH) cC(dF dI) cG(dK dM) bAdM bCbQ cJdA dEdL} Jo{Jt(Et Jr Nt Qb Qd) Pe(Ir Js Qe) Nt(Mq Nm) Nb(Ir Js) MrIj NaNv HwOk IvLh NxOn} Nd{Ns(No Nt Pd) Et(Nr Qd) Md(Fp Mq) Ms(Mq Mv) Hq(Pd Pe) Iv(Ok Qd) NoNt NkOk} bQ{bC(aY bR bZ cA cD cL dH) dH(bS cK dE) dK(bF bZ) aYdL bAcO cCcS} bS{cD(aI aO bB cG dD dF) bR(aO cG cS dD dF) cE(aO cG) aLbE} Pa{Mk(Mi On Pd) Ok(Nc Nk Pb) Et(Jt Na) Hv(Ml Of) NmMy NuLy} Pb{Ny(Et Hq Hw Mh Mx) On(Hv Ij Nf) Mi(Hv Ij) LhPe} bV{dH(bE cG cK cS dE) cC(cS dF) aYcG aZdE bBdK bEcZ} cC{dF(aX dE dI) bO(dE dI) aMdI aOdA aXdM bCcK} Of{Pe(Md Nb Nv) Mi(Hv Ij) Mv(Nb Nr) HvNv} Pf{Ns(Hv In Md Mq Ny) MdHq} dK{bG(aX bO cR) aWbO cRdA dDdE} bE{aI(aM cQ dA) aL(aN bH)} dF{cE(aP bC) aMdE aYcK cSdH} Et{Lu(Iu Qd) MyNb NcOk} Nt{Ik(Ir Iv Qd) QbJm} Ne{Nc(Ok On) Nl(Lh Ok)} dH{cK(bC cS) aJcQ aOdI} Mv{My(Ji Nr) OyPe} On{MkMr NkHw IkIv} Wm{LyNl QdJm} Me{NoaA MdHv} Mh{MbQd NaNv} Mi{Pe(Hq Oy)} aO{bFdI bRdA} aY{aMdE cGcQ} bC{aZdM cKdI} LuJrJt MnMqMs IuQbJm aIdEdM bRcSdA

Constrained panels with 2 analytes, where 1.0E-7 >= 'AUC p-value' > 0. Contains 367 panels of 11,037 total panels evaluated. : Mp(aA Hq Hv In Ip Is Jh Ji Jj Jl Jn Jp Jq Jr Lu Lv Lw Lx Lz Md Mh Mi Mj Mm Mr Ms Mt Mu Mw Mx Mz Nb Nc Nj Nn Nq Nr Ns Nt Nu Og Oh On Pa Pc Pg Po) Jr(aA Et Fr Hw Im Ip Is Iu Jg Ji Jj Jk Jl Jp Jq Lh Lw Lx Ma Mg Mi Mm Mr Mt Mu Mw Mz Nb Nd Nn No Nq Nr Nt Nv Nw Oh Ok Om On Pa Pc Pe Pg Po Qa) Jj(Et Fr Hw Hx Ih Ii Ij Il Im Ip Ir Is Iu Ji Jk Jl Jn Jo Js Lh Li Lv Lx Ma Mi Mt Mu Mw Nn Nq Nr Nt Nv Nw Om On Pa Pe Pg Po Qa Qb Qd Qe) Is(aA Et Fr Hw Io Ji Jl Jq Lh Lu Lw Lx Md Mg Mi Mm Mr Ms Mt Mu Mz Nf Nn No Nq Nt Nw Og Oh Oi Ok Om On Pa Pc Pe Pg Po Pz) Jl(aA Et Fr Im Io Ji Jn Jq Jt Lh Lw Mg Mi Mm Mt Mu Mz Nf Ng Nm Nn No Nq Nt Nw Oe Og Oh Oi Ok Om On Pc Pz Qa) On(aA Hu Io Ip Ji Jn Jq Lh Lw Mi Mm Ms Mu My Mz Nj Nn Ns Oe Of Og Oi Oy Pc Pz) Mt(Hv Hx In Ip Jn Lv Lw Lx Mi Mu Mw Nb Nj Ny Oi Pa Pb Pc) aA(bC bW cJ dN Fr Ip Ji Jk Lv Lw Mm Mu Nj Nn Nq Pc Pg Qa) Mu(Hv Ip Jn Lv Mh Ms Ng Nj Nr Oe Og Oi Pg) Ji(Hw Io Ip Jk Lu Lx Ms Nd Nk Nx Og Pa Pe) Nn(Ip Jn Jp Lv Mf Ms Nd Oi Pa Pe) Mw(Hv Md Mr My Nd Og Oh Pa) Lv(Jg Jn Jp Lx No Oh Ok) Ip(Fr Jn Jq Lx Nw Po Qa) Lx(Hq Jn My Og Pb) Og(Jg Nt Om Po) Fr(Jn Ng Pz) Nq(Jn Ng Nj) Qa(Io Nw Pz) dN(aJ aY dC) Po(Jq Oy) Mm(Jn Pe) Nj(Mz No) Pg(Et Im) aP(cF dH) JhPa JkJq NwOi aJcF aObC bAbW Constrained panels with 2 analytes, where 1.0E-6 >= 'AUC p-value' > 1.0E-7. Contains 189 panels of 11,037 total panels evaluated. : Ip(Et Hx Jg Jh Jk Jp Lh Ma Mi Mw Mz Nb No Og Ok Om Pa Pe Pg) Nn(Hv Ii Ij In Ji Jq Lw Lx Mh Mi Mt Mu Mz Nr Nw Og Pc) Mt(Ii Jh Jq Md Mq Mr Mz Na Nd Nf Nq Nr Oe Og Oh Po) Mw(Ij In Jq Lw Lz Mj Mq Mx Mz Nb Nf Nr On Oy Pc) Jj(Fp In Iv Jh Jm Mg Mn Mr Mv No Ny Pd) Et(Jn Mm Nk Oe Oi On Pa Pe Pz Qa) Mp(Hw Ii Ij Ir Lh Na Nf Nv Nw Qb) Mu(Hw Ji Jq Js Lh Lx Pa Pe Qb) Jn(aA Jg Jk Jp Ma Nw Om Po) Lx(Hv Jp Jq Mq Nr Oh Oy) Ji(Fr Iu Mi Mr Nq Nt Pg) Nw(In Jk Og Pa Pe Pg) Po(Jh Jp Lv My Of) Og(Jh Lh Ok Pe Pg) Nt(aA Jp Nj On) Lv(Hv Mi Mm Mr) Qa(Jq Ma Om On) Pe(Fr Oh Om On) Jh(In Mj Nd) Jr(Jt Lu Md) Nq(Jp Jq) Nj(Nb Nv) Hv(Lw Oh) Om(Pa Pg) aA(Jg Mg) bA(cF cU) NsPf MaIr MdJl MmPg ImOn JpPa aJbC aObW bVdK Constrained panels with 2 analytes, where 1.0E-5 >= 'AUC p-value' > 1.0E-6. Contains 350 panels of 11,037 total panels evaluated. : Ip(Hv Hw Ih Ii Im Ir Iv Js Jt Li Lu Lv Mh Mj Mm Mn Mr Mx Na Nc Nd Nq Nr Nt Nv Oh Qd Qe) Nw(aA Fr Hv Hw Ij Ir Iu Iv Jq Lh Lw Lx Mg Mi Mm Mq Mr Mu Mz Na Nd Nq Nr Nt Nu Ok Om) Lx(aA Et Hw Ij Im In Iu Jg Jo Li Lw Ma Mh Nb Nf Ng Nm Om Pa Pc Po Qa Qe) Ma(aA Hx Ii In Jk Jq Lh Lv Mt Mx Mz Pa Po Qb Qd Qe) Jn(Hw Iu Lw Mg Mi Ms Mz Nd No Nt Nv Og Ok Pa Pc Pe) Nn(Et Hw Hx Il Ir Lh Md Mq Mx Nb Nv Pg Po Qa Qb) Mu(Et Ih Im Ir Iu Lw Lz Md Mi Mz Nb Nt Po Qa Qe) Jj(Hq Hu Iq Jg Jp Md Mj Mm Mx My Mz Nb Nd Nf Ok) Om(aA Hw Ir Lh Mg Mh Mp Ms Mt Mx Nd Nk Oe Po Qd) Jp(Hw Hx Ii In Io Iu Jk Lw Mg Mi Mz Nb Nv Qb) Jq(Fr Hw Hx Im Iu Li Mi Nd Nj Nt Pa Pe Pg) Et(aA Hx In Io Jk Lu Mh Mp Mz Nc Nd Po) Qa(Fr Jg Lh Lw Mi Mm Mp Mt Mz Nq Ok Pc) Mp(Fr Hx Ih Iu Js Nm No Ok Pe Qe) Mw(Hw Ii Ir Jg Lv Mh Na Nm Nu Ok) Og(Hx Ii Ir Jk Mq Mz Nb Nm Nq Nv) Po(aA Lw Mi Ns Oh Ok Pa Pc Pe) Fr(Ij In Ir Lh Mx Nc Nr On) Nq(Hx Ii Ij Lv Nr Pa Pe Qb) Jh(Hv Hw Hx Ii Iq Lv Nr Qe) Mt(aA Lh Mg My No Nv Qb) Mm(Hx Ij Ir Ji Qb) Jg(Ms Oi Pa Pe Pz) On(Ir Ng Nk No Qd) Lv(Mx Mz Nv Pa) cS(aO bA cF dM) Nt(Io Jo Ng) Nj(Nr Oh Pa) Ji(Lh No Pc) Ok(Jk Pa Pg) Pe(aA Lw Pc) Qd(Im Pz) Jo(Jr Lh) Oh(In Nr) bA(bC bE) bQ(bO cE) MiaA MzNk NbOe NgPg HuPc IoNv LiOi NyPb aObV bWcF dFdK Constrained panels with 2 analytes, where 1.0E-4 >= 'AUC p-value' > 1.0E-5. Contains 538 panels of 11,037 total panels evaluated. : Im(Hx Ii Iv Jg Jk Jp Js Jt Li Lu Lv Lw Ma Mh Mj Mp Mr Mt Mz Nb Nc Nn Nq Nr Nt Nv Nx Og Oh Pa Pc Po Qe) Ma(Hv Hw Ih Ij Iv Jp Js Li Lw Md Mg

Figure 42 Continued

Mh Mp Mq Mr Nb Nc Nf Ng Nk Nn Nq Nr Nt Nu Nv Og Oi Ok) Et(Fr Hw Ir Iu Iv Jq Jt Lh Lw Md Mi Mr Mt Na Nb Nf No Nq Nr Nt Nv Nw Oh Ok Om Pc Qd) Jp(Fp Hv Ih Ij Ir Iv Jg Jq Js Lu Lz Md Mh Mm Mq Mr Mx Nd Nf Nm Nr Nu Oh Ok Pc Qe) Oh(Fr Hu Hw Ii Iu Jh Jn Lh Mj Mu Mx Mz Nb Nq Nt Nv Nw Ny Oi Om Pa Pg Qa) Pg(Hw Ih Ir Iu Iv Jn Jo Jt Lw Mi Mr Mt Mz Na Nf Nm Nt Oy Pc Pe Qa Qd) Fr(Hv Hw Ih Iu Iv Jo Lw Mi Mq Mr Mu Mz Na Nf Nm Nn No Nt Ok Pc Qd) Om(Ih Iu Iv Jq Lw Lz Mi Mm Mr Mu My Mz Ng Nn No Nq Nt Of Ok Oy Pc) Jh(Fp Ij Ir Iu Iv Js Lw Lz Md Mh Mq Mx Na Nc Nf Nk Nm Ns Pc Qb) Lv(Hx Ih Ir Iv Jk Li Lz Md Mh Mj Nb Nc Nd Nf Nm Nr Nt Pc Qe) Mm(Fp Ii In Iv Jk Jq Js Lh Lu Lx Mh Mx Mz Nt Pa Po Pz Qd Qe) Ok(Hx Ir Iu Lx Mh Mt Mu Mz Nc Nd Nk Nn Nq Nt Nv Qd Qe) Nq(Fp Hv Hw In Ir Mh Mi Mj Mz Nb Nc Nk Po Qd Qe) Qa(Hw Iu Jk Jt Md Mg Mr Nb Nd Nf No Nt Nv Pa Po) Nn(Fp Hu Ih Iu Js Me Mr Na Nf No Nt Qd Qe) Ip(Ij In Iu Lw Lz Md Mq Mv Nf Nk Nu Nx Pc) Jg(Hx Ii Ij In Ir Jq Lu Mp Mx Mz Qb Qd Qe) Jj(Hv Jq Jt Lz Mh Mq Nc Nk Nl Nm Nu Nx Pf) Mt(Hw Ir Iu Jk Jt Ml Nc Nm Nt Of Pe Qe) Po(Hw Iu Jo Mh Mr Mz Na Nb Nf Nt Pb) Lx(Ih Ir Iv Jk Ly Mg Mr Mz Na Nc Qd) Mw(Fp Hx Ih Iu Iv Js Lu Ms Ng Nx Qe) Jq(aA Lh Mg Mr Mv Nb No Nr Nv Og) Lw(Fp Hx Ir Mi Mx Mz Nd Ny Qe) Mu(Iv Jo Li Mr Na Nf Pc Qd) Og(Ih Iu Iv Jt Mv Nr Ny Qe) Mp(Fp Iv Jk Lj Mg Pd Qd) Mz(Li Mi Ml Nd Nt Pb Pe) Jn(Lh Li Lu Md Mr Nb Nr) Ny(Hv Mq Na Nd Nm Nu) Jk(Fp Ir Mh Oi Pz) Nv(Fp Mh Mx Oe Oi) Nw(Jo Jt Li Mb Pc) Pa(aA Hv Nc Nm Oe) dM(aI aO aU bC bW) Nj(Hw Ii Iq Mj) Lh(aA Mg Ng Of) Pe(Jt Mg Mi Nt) aM(aJ aO bV cS) bQ(cC dH dK) bV(bO bW cC) dF(bC bW cS) Mi(Io Ms) Nd(Hv Nm) Ir(Li Pc) Oi(Ih Iv) aA(In No) aI(dE dI) aO(aX bA) NtOe MbQd MdHv MvOn NbNk bWcT cSdD cUdK

Constrained panels with 2 analytes, where 1.0E-3 >= 'AUC p-value' > 1.0E-4. Contains 489 panels of 11,037 total panels evaluated. : Qd(Hw Hx Ii In Iu Jh Jk Jt Lh Lu Lv Lw Md Mg Mi Mq Mr Mt Mw Mz Na Nb Nd Nf Nr Nt Nv Oh Pa Pc Pe Po Wm) Jk(Hv Hw Hx In Iu Iv Js Li Lw Lz Md Mg Mi Mj Mq Mr Mx Mz Na Nb Nf Ng Nm Nr Oe Oh Pa Pc Po Qb Qe) Jg(Fp Hv Hw Ih Io Iu Iv Js Lw Ma Md Mh Mi Mj Mq Mr My Nc Nd Nk No Nr Ns Nt Nu Oe Oh Ok Pc) Qe(Hv Hw Ii Ij In Iu Lu Md Mg Mq Mx Na Nb Nd Nf Nm Nr Nv Nx Oe Oh Oi Pa Pc) Lw(Hw Iv Jj Js Lh Li Lu Lv Mh Mj Mm Mr Mv Nb No Nq Nr Nt Nv Og Oh Ok Qb) Nq(Ih Iu Iv Js Li Lj Lz Md Mq Mr Ms Mx My Na Nf No Nt Nv Oy Pc) Mm(Hv Hw Ih Il Im Iq Li Ma Md Mi Mj Mr Mt Mu Nb No Nr Nv Nx Ok) Qb(Hv Hw Iu Lu Md Mg Mh Mj Mq Mv Na Nm Nr Nu Nx Og Oh Pc) Ir(Hw Hx Lu Md Mg Mi Mr Mz Nb Nd Nf Nr Nt Nv Oh Pa Po) Oh(Fp Hx Ih Ij Il Jj Ma Md Mn Mq Mr Nd Nm No Ok Oz) Mz(Hw Iu Iv Lh Mg Mq Mr Ms Na Nb No Nr Nv Pa Pc) Im(Hv Hw Ij In Iu Lz Md Mg Mq Mv Mx Na Nf Nu Pd) Ok(Hw Ih Iv Jq Li Md Mg Mi Mr Mx Nb Nf No Pc Pz) Hx(Hw Ih Iu Iv Li Md Mg Ms Mx Nd Nm Oe Pc) Li(Ii In Iv Jp Lu Md Mp Mt Nb Nt Nv Pa) Fp(Ih Ii Iq Iu Md Mj Mq Nd Nm Ny Pc) Nv(Hv Hw In Lj Mq Na Nb Ng Nm Nr Pa) Mn(Hv Hw In Iu Lu Mh Mj Mq Ms Nm) Ma(Iu Jo Jt Mb Na Nd Nm Nx Pc) Ij(Lz Md Mh Mv Mx Nd Ny Og Pc) Lv(Hw Ii Iu Js Lu Mq Mv Na) Jt(Fr Jn Jp Lx Mp Ms Mu Om) Nm(Mh Mj Mu Mx Nn No Nr) Ny(Hw In Iu Lz Mh Mj Pc) Og(Il Iq Mr Mx Nx Pa) dK(aI bG bO bS cF cG) Nt(Md Mi Ne Nf Pc) Nb(Ms Mx Nc Nd Of) Iv(Mt Nd Nn Pa Po) Jo(Ip Jn Jp Jq Mp) dE(aO bQ cU dD dF) Na(Ih Jj Jp Pa) Nx(Jh Ms Mx Nk) aM(bZ cU dF dI) bO(bC bW cS dM) cF(cG cU dG dI) Nr(Md Mx Oe) Nu(Ih Iq Iu) Nd(Md Mf Mq) Nj(Md My Nf) Hv(Me Mh Nk) Lh(Mi Pb Pc) aI(aX bC cS) cT(bC cS cU) No(Mi Mu) Mg(Ip Mw) Nc(Ii My) Ng(Jh Mv) Jj(Oz Pc) Pd(Jp Mw) bQ(bF bZ) cE(cG dF) WmNw LxOf MpNi MqPa MxIi IhJh JqPc aLbE cCdI cGcL dFdM Constrained panels with 2 analytes, where 1.0E-2 >= 'AUC p-value' > 1.0E-3. Contains 365 panels of 11,037 total panels evaluated. : Ih(Hv Hw Ii Ij In Iu Jk Lu Lw Md Mg Mh Mj Mq Mr Mv Nb Nd Nf Nm Nr Nv Nx Pa Pc) Nd(Hu Ii Iq Js Jt Li Lu Mh Mj Ms Mv Mx Na Nc Nf Nj Nk Nr Nu Nx Qb) Pc(Hv Hw Ii Il Iu Iv Js Li Lu Mm Mx Nb No Nr Nv Og Oi Pa) Mh(In Iq Iu Mb Md Mg Mq Mt Mv My Na Nb Nc Nf Nx Oh Pd) Jo(Im Ir Jg Jk Jt Li Lv Mm Mw Mz Ng Nq Nv Og Qb Qd Qe) Nf(Hx Ii Iv Jg Li Lw Mm Mx Nb Nc Nk Nr Nv Oh Pa Qb) Lu(Hv Ij Iq Iu Js Mq My Nc Nj Nm Nr Nu Nx Ny Oh) Mg(Fp Iv Jg Js Li Lj Lv Mx Nc Nk No Nv Og Oi Pa) Mq(Hv Ii Ij Iv Js Li Lw Md Mj Mm Mv Nc Nj Nk) Iu(Hv Ii Iv Js Li Lw Mm Mv Mx Nb Nm Nr Nv Nx) Jt(Hx Io Jg Jk Li Mm Mz Nn No Nq Nt Nv Pa Po) Na(Fp Jg Li Lw Md Mm Mn Mv Mx Nc Nj Nk Oh) Md(Ii Iv Js Mj Mr Mv Mx Nb Nm Pa) Nc(Hv In Iq Lw Mj Mn Mv Nm Nu Oh) cT(aI bE bL bO bS cK cR dE dK) Lw(Ii Ij Il In Lz Ms Nk Pa) Nb(Hw Hx Iv Js Ml My Ny Pb) Ij(Li Lv Ms Nr Oe Pa Qb) In(Fp Lv Nj Nk Pa Pd Qb) dE(bO bW cC cG dG dL dM) Nm(Il Lz Mr Mv Nk Nq) Js(Hw Hx Nr Og Oh Pa) Li(Hv Hw Mi Mr Nr Oh) Pd(Jh Lv Mm Og Qb Qe) Ms(Ii Iq Jh My Pa) Mv(Hv Ii Mj Mt Oh) Hu(Jg Jh Mb Nq Og) Iv(Hw Mr Nr Nv Oh) aM(bC bL bO bW dG) Lz(Hv Jg Mn Nv) Ni(Mm Nk Nn Pa) Nu(Mj Mn My) Mi(Hq Hv Lj) Nk(Iq My Og) Oy(Jg Jh Mt) Mb(Fp Lv) Mm(Me Nq) Mx(Hv Pa) Jq(Oz Wm) Og(Mj My) bE(aI dD) bL(cC cF) cG(aY cC) cJ(bV cK) dK(bB cQ) NrHx NeNl NgJg HwPa QbOe JhLj NxOh bAdM bOdL cFdA dGdH

Figure 42 Continued

Descriptive statistics for the assays used to form the panels presented in this figure.

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Po | pg/ml | 3.4E-1 | 8.2E1 | 8.9E0 | 9.3E1 | 2.6E1 | 8.6E1 | 8.0E-3 | 2.6E-2 | 2.7E2 | 2.2E2 | 260 | 8 | 260 | 8 | 0.86 |
| Et | ng/ml | 1.5E3 | 4.0E3 | 1.8E3 | 3.9E3 | 1.2E3 | 1.0E3 | 7.9E1 | 1.8E3 | 4.7E3 | 5.0E3 | 259 | 8 | 259 | 8 | 0.91 |
| Fp | ng/ml | 1.4E1 | 5.0E1 | 2.5E1 | 5.0E1 | 2.8E1 | 3.6E1 | 6.0E-3 | 1.1E1 | 1.3E2 | 1.3E2 | 263 | 8 | 263 | 8 | 0.77 |
| Fr | ng/ml | 3.9E4 | 6.8E5 | 1.3E5 | 5.8E5 | 1.9E5 | 2.7E5 | 1.9E2 | 2.2E4 | 8.4E5 | 8.4E5 | 266 | 9 | 266 | 9 | 0.89 |
| Nm | pg/ml | 1.4E4 | 5.3E4 | 3.8E4 | 1.6E5 | 9.1E4 | 2.7E5 | 1.0E-9 | 1.0E4 | 9.6E5 | 8.2E5 | 263 | 8 | 263 | 8 | 0.80 |
| Nn | pg/ml | 1.9E2 | 8.3E3 | 3.0E3 | 3.0E4 | 2.0E4 | 4.2E4 | 1.0E-9 | 2.8E2 | 3.1E5 | 1.1E5 | 263 | 8 | 263 | 8 | 0.91 |
| No | pg/ml | 1.7E1 | 4.6E2 | 3.4E1 | 4.3E2 | 5.8E1 | 3.5E2 | 1.0E-9 | 4.4E0 | 5.6E2 | 9.1E2 | 263 | 8 | 263 | 8 | 0.87 |
| Nq | pg/ml | 2.0E0 | 7.7E1 | 2.6E1 | 1.5E2 | 8.5E1 | 2.1E2 | 1.0E-9 | 1.0E-9 | 6.7E2 | 6.3E2 | 263 | 8 | 263 | 8 | 0.84 |
| Nr | pg/ml | 2.0E0 | 5.0E1 | 2.3E1 | 3.0E2 | 8.0E1 | 4.9E2 | 1.0E-9 | 1.0E-9 | 9.8E2 | 1.4E3 | 263 | 8 | 263 | 8 | 0.78 |
| Ns | pg/ml | 1.0E-9 | 1.0E-9 | 9.6E0 | 1.0E-9 | 7.3E1 | 0.0E0 | 1.0E-9 | 1.0E-9 | 1.1E3 | 1.0E-9 | 263 | 8 | 263 | 8 | 0.47 |
| Nt | pg/ml | 1.2E2 | 3.0E2 | 1.4E2 | 5.7E2 | 1.0E2 | 6.1E2 | 1.5E1 | 7.5E1 | 8.8E2 | 1.7E3 | 263 | 8 | 263 | 8 | 0.76 |
| Nu | pg/ml | 2.4E1 | 9.9E1 | 6.0E1 | 1.3E2 | 8.8E1 | 1.4E2 | 1.0E-9 | 1.0E-9 | 6.3E2 | 3.7E2 | 263 | 8 | 263 | 8 | 0.67 |
| Lu | pg/ml | 1.0E4 | 4.9E3 | 1.7E4 | 6.6E3 | 4.5E4 | 5.4E3 | 9.4E2 | 5.2E2 | 5.6E5 | 1.7E4 | 263 | 8 | 263 | 8 | 0.33 |
| Lv | pg/ml | 1.0E-9 | 5.9E1 | 1.7E1 | 5.6E1 | 3.4E1 | 5.7E1 | 1.0E-9 | 1.0E-9 | 2.6E2 | 1.6E2 | 263 | 8 | 263 | 8 | 0.70 |
| Lw | pg/ml | 1.0E-9 | 1.0E-9 | 1.1E0 | 1.0E1 | 1.2E1 | 1.5E1 | 1.0E-9 | 1.0E-9 | 1.8E2 | 4.0E1 | 263 | 8 | 263 | 8 | 0.68 |
| Lx | pg/ml | 1.0E-9 | 1.7E3 | 2.0E2 | 4.1E3 | 6.2E2 | 7.5E3 | 1.0E-9 | 1.0E-9 | 6.2E3 | 2.2E4 | 263 | 8 | 263 | 8 | 0.88 |
| Ly | pg/ml | 1.0E-9 | 1.0E-9 | 9.5E0 | 9.4E0 | 1.8E1 | 2.1E1 | 1.0E-9 | 1.0E-9 | 1.1E2 | 6.0E1 | 263 | 8 | 263 | 8 | 0.51 |
| Lz | pg/ml | 1.0E-9 | 1.0E-9 | 3.2E0 | 1.6E1 | 2.9E1 | 2.5E1 | 1.0E-9 | 1.0E-9 | 4.3E2 | 6.2E1 | 263 | 8 | 263 | 8 | 0.67 |
| Ma | pg/ml | 5.2E2 | 4.9E3 | 2.7E3 | 4.7E3 | 6.9E3 | 2.1E3 | 1.0E-9 | 2.0E3 | 6.5E4 | 7.5E3 | 263 | 8 | 263 | 8 | 0.86 |
| Mb | pg/ml | 2.6E1 | 2.1E1 | 3.3E1 | 2.3E1 | 1.9E1 | 1.3E1 | 9.2E0 | 4.1E0 | 2.1E2 | 4.7E1 | 263 | 8 | 263 | 8 | 0.31 |
| Mc | pg/ml | 1.0E-9 | 1.0E-9 | 7.2E-2 | 1.0E-9 | 8.5E-1 | 0.0E0 | 1.0E-9 | 1.0E-9 | 1.3E1 | 1.0E-9 | 263 | 8 | 263 | 8 | 0.49 |
| Md | pg/ml | 1.0E-9 | 1.8E-1 | 5.0E-1 | 4.6E0 | 4.3E0 | 1.0E1 | 1.0E-9 | 1.0E-9 | 6.5E1 | 2.9E1 | 263 | 8 | 263 | 8 | 0.71 |
| Me | pg/ml | 3.1E1 | 3.1E1 | 3.1E1 | 4.3E1 | 2.6E1 | 5.9E1 | 1.0E-9 | 1.0E-9 | 3.2E2 | 1.8E2 | 263 | 8 | 263 | 8 | 0.48 |
| Mf | pg/ml | 1.0E-9 | 1.0E-9 | 7.8E-1 | 6.0E0 | 4.4E0 | 1.6E0 | 1.0E-9 | 1.0E-9 | 5.6E1 | 4.5E0 | 263 | 8 | 263 | 8 | 0.53 |
| Mg | pg/ml | 1.6E0 | 8.0E0 | 7.8E0 | 1.2E1 | 1.6E1 | 1.4E1 | 1.0E-9 | 1.0E-9 | 1.5E2 | 3.7E1 | 263 | 8 | 263 | 8 | 0.55 |
| Mh | pg/ml | 1.0E-9 | 4.2E-1 | 1.0E0 | 4.3E0 | 7.4E0 | 7.2E0 | 1.0E-9 | 1.0E-9 | 1.1E2 | 1.8E1 | 263 | 8 | 263 | 8 | 0.74 |
| Mi | pg/ml | 1.0E-9 | 1.1E1 | 3.1E0 | 5.9E1 | 3.3E1 | 1.1E2 | 1.0E-9 | 1.0E-9 | 5.2E2 | 3.2E2 | 263 | 8 | 263 | 8 | 0.73 |
| Mj | pg/ml | 1.0E-9 | 1.9E1 | 6.2E0 | 5.7E1 | 3.1E1 | 8.3E1 | 1.0E-9 | 1.0E-9 | 4.6E2 | 2.1E2 | 263 | 8 | 263 | 8 | 0.69 |
| Mk | pg/ml | 2.1E0 | 5.5E0 | 1.8E1 | 8.3E1 | 1.0E2 | 1.8E2 | 1.0E-9 | 1.0E-9 | 1.3E3 | 5.0E2 | 263 | 8 | 263 | 8 | 0.63 |
| Ml | pg/ml | 1.0E-9 | 1.0E-9 | 1.2E1 | 6.6E1 | 1.3E2 | 1.8E2 | 1.0E-9 | 1.0E-9 | 2.1E3 | 5.1E2 | 263 | 8 | 263 | 8 | 0.60 |
| Mm | pg/ml | 6.3E2 | 3.0E3 | 1.1E3 | 3.1E3 | 1.4E3 | 2.1E3 | 1.0E-9 | 3.6E2 | 1.0E4 | 6.5E3 | 263 | 8 | 263 | 8 | 0.82 |
| Mn | pg/ml | 6.5E0 | 1.8E1 | 1.2E1 | 2.0E1 | 2.8E1 | 1.4E1 | 1.0E-9 | 6.5E0 | 3.5E2 | 5.1E1 | 263 | 8 | 263 | 8 | 0.79 |
| Mp | pg/ml | 1.0E-9 | 6.9E1 | 2.3E1 | 1.2E2 | 1.5E2 | 1.6E2 | 1.0E-9 | 6.8E0 | 2.4E3 | 5.0E2 | 263 | 8 | 263 | 8 | 0.91 |
| Mq | pg/ml | 1.0E-9 | 1.0E-9 | 2.7E0 | 1.9E1 | 1.4E1 | 3.8E1 | 1.0E-9 | 1.0E-9 | 1.8E2 | 1.0E2 | 263 | 8 | 263 | 8 | 0.59 |
| Mr | pg/ml | 1.0E-9 | 3.2E2 | 2.8E1 | 9.5E2 | 1.4E2 | 1.3E3 | 1.0E-9 | 1.0E-9 | 1.5E3 | 3.4E3 | 263 | 8 | 263 | 8 | 0.77 |
| Ms | pg/ml | 3.3E2 | 2.2E2 | 4.5E2 | 3.5E2 | 5.1E2 | 3.8E2 | 1.0E-9 | 1.0E-9 | 3.3E3 | 9.8E2 | 263 | 8 | 263 | 8 | 0.44 |
| Mt | pg/ml | 4.8E-1 | 8.7E1 | 1.1E1 | 4.7E2 | 5.2E1 | 1.1E3 | 1.0E-9 | 2.8E-1 | 7.1E2 | 3.2E3 | 263 | 8 | 263 | 8 | 0.90 |
| Mu | pg/ml | 1.0E-9 | 4.5E0 | 2.0E0 | 9.7E0 | 1.6E1 | 1.2E1 | 1.0E-9 | 1.0E-9 | 2.3E2 | 3.5E1 | 263 | 8 | 263 | 8 | 0.90 |
| Mv | pg/ml | 1.0E-9 | 2.0E2 | 8.0E1 | 3.4E2 | 3.8E2 | 3.9E2 | 1.0E-9 | 1.0E-9 | 4.5E3 | 9.2E2 | 263 | 8 | 263 | 8 | 0.73 |
| Mw | pg/ml | 3.7E1 | 1.4E3 | 3.1E2 | 2.2E3 | 1.5E3 | 2.2E3 | 1.0E-9 | 1.0E2 | 1.8E4 | 5.3E3 | 263 | 8 | 263 | 8 | 0.91 |
| Mx | pg/ml | 1.0E-9 | 7.3E-1 | 4.2E-1 | 3.7E0 | 2.1E0 | 6.7E0 | 1.0E-9 | 1.0E-9 | 3.2E1 | 2.0E1 | 263 | 8 | 263 | 8 | 0.74 |
| My | pg/ml | 1.0E-9 | 2.5E2 | 4.0E2 | 4.7E2 | 2.8E3 | 6.8E2 | 1.0E-9 | 1.0E-9 | 3.9E4 | 1.9E3 | 263 | 8 | 263 | 8 | 0.69 |
| Mz | pg/ml | 1.2E1 | 1.7E2 | 2.7E1 | 4.8E2 | 5.1E1 | 7.2E2 | 1.0E-9 | 1.0E-9 | 5.5E2 | 1.9E3 | 263 | 8 | 263 | 8 | 0.82 |
| Na | pg/ml | 1.0E-9 | 1.6E-1 | 5.2E-1 | 6.8E0 | 1.7E0 | 1.4E1 | 1.0E-9 | 1.0E-9 | 9.6E0 | 4.2E1 | 263 | 8 | 263 | 8 | 0.67 |
| Nb | pg/ml | 2.2E0 | 1.6E1 | 3.9E0 | 4.8E1 | 1.1E1 | 7.4E1 | 1.0E-9 | 1.0E-9 | 1.5E2 | 2.1E2 | 263 | 8 | 263 | 8 | 0.74 |
| Nc | pg/ml | 3.4E2 | 1.0E-9 | 5.2E2 | 1.1E2 | 7.7E2 | 2.8E2 | 1.0E-9 | 1.0E-9 | 9.2E3 | 7.9E2 | 263 | 8 | 263 | 8 | 0.24 |
| Nd | pg/ml | 2.5E1 | 4.1E1 | 2.8E1 | 3.0E2 | 7.7E1 | 7.4E2 | 1.0E-9 | 4.8E0 | 1.2E3 | 2.1E3 | 263 | 8 | 263 | 8 | 0.76 |
| Ne | pg/ml | 4.2E2 | 2.0E2 | 5.3E2 | 2.3E2 | 6.0E2 | 2.0E2 | 1.0E-9 | 1.0E-9 | 7.0E3 | 4.7E2 | 263 | 8 | 263 | 8 | 0.30 |
| Nf | pg/ml | 1.0E-9 | 1.0E-9 | 2.1E0 | 3.6E1 | 8.8E0 | 5.5E1 | 1.0E-9 | 1.0E-9 | 8.2E1 | 1.3E2 | 263 | 8 | 263 | 8 | 0.62 |
| Ng | pg/ml | 1.7E1 | 2.7E1 | 1.0E2 | 9.6E1 | 2.0E2 | 1.5E2 | 1.0E-9 | 1.0E-9 | 1.6E3 | 4.2E2 | 263 | 8 | 263 | 8 | 0.50 |
| Nh | pg/ml | 6.0E1 | 3.1E1 | 8.0E1 | 3.6E1 | 7.8E1 | 2.5E1 | 1.0E-9 | 4.1E0 | 5.6E2 | 7.5E1 | 263 | 8 | 263 | 8 | 0.29 |
| Ni | pg/ml | 1.0E-9 | 1.0E-9 | 8.5E1 | 1.9E2 | 1.3E2 | 3.8E2 | 1.0E-9 | 1.0E-9 | 7.1E2 | 1.1E3 | 263 | 8 | 263 | 8 | 0.50 |
| Nj | pg/ml | 6.2E0 | 3.4E0 | 9.9E0 | 7.8E0 | 1.1E1 | 9.0E0 | 1.0E-9 | 1.0E-9 | 6.8E1 | 2.2E1 | 263 | 8 | 263 | 8 | 0.43 |
| Nk | pg/ml | 1.7E1 | 2.6E0 | 3.2E1 | 1.5E1 | 4.0E1 | 2.4E1 | 1.0E-9 | 1.0E-9 | 2.0E2 | 6.6E1 | 263 | 8 | 263 | 8 | 0.38 |

Figure 43

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Nl | pg/ml | 4.2E1 | 1.0E1 | 5.6E1 | 2.0E1 | 7.9E1 | 2.8E1 | 1.0E-9 | 1.0E-9 | 1.1E3 | 8.2E1 | 263 | 8 | 263 | 8 | 0.27 |
| Hq | pg/ml | 1.2E0 | 1.2E1 | 2.0E2 | 3.8E2 | 2.1E3 | 9.7E2 | 1.0E-9 | 6.2E-2 | 2.8E4 | 2.8E3 | 261 | 8 | 261 | 8 | 0.73 |
| Hr | pg/ml | 8.5E1 | 4.9E2 | 5.1E2 | 1.8E3 | 1.0E3 | 3.1E3 | 1.0E-9 | 1.0E-9 | 8.4E3 | 8.9E3 | 261 | 8 | 261 | 8 | 0.61 |
| Hu | pg/ml | 1.4E1 | 6.5E2 | 5.9E3 | 1.3E3 | 4.5E4 | 2.2E3 | 1.0E-9 | 1.0E-9 | 6.3E5 | 6.5E3 | 261 | 8 | 261 | 8 | 0.70 |
| Hv | pg/ml | 1.4E0 | 8.1E0 | 3.1E0 | 1.2E2 | 1.1E1 | 3.1E2 | 1.0E-9 | 1.0E-9 | 1.6E2 | 8.9E2 | 261 | 8 | 261 | 8 | 0.74 |
| Hw | pg/ml | 5.5E0 | 1.1E1 | 1.6E1 | 1.3E3 | 5.0E1 | 3.3E3 | 1.0E-9 | 5.1E-1 | 6.4E2 | 9.4E3 | 261 | 8 | 261 | 8 | 0.59 |
| Hx | pg/ml | 8.9E0 | 4.2E1 | 6.1E1 | 3.1E2 | 5.7E2 | 4.8E2 | 1.0E-9 | 3.9E0 | 9.3E3 | 1.3E3 | 261 | 8 | 261 | 8 | 0.75 |
| Ih | ng/ml | 7.3E1 | 9.9E2 | 2.5E2 | 9.7E2 | 4.3E2 | 9.1E2 | 1.0E-9 | 5.7E0 | 3.6E3 | 2.8E3 | 262 | 8 | 262 | 8 | 0.76 |
| Ii | ng/ml | 9.2E1 | 4.7E2 | 2.0E2 | 1.4E3 | 4.4E2 | 1.7E3 | 7.3E-1 | 2.3E0 | 5.2E3 | 4.5E3 | 262 | 8 | 262 | 8 | 0.79 |
| Ij | ng/ml | 8.7E1 | 1.5E2 | 2.0E2 | 3.2E3 | 6.1E2 | 8.5E3 | 2.8E0 | 4.6E1 | 6.4E3 | 2.4E4 | 259 | 8 | 259 | 8 | 0.73 |
| Ik | ng/ml | 1.2E1 | 1.6E1 | 1.6E3 | 7.5E1 | 1.3E4 | 1.6E2 | 5.9E-1 | 5.5E0 | 1.2E5 | 4.6E2 | 259 | 8 | 259 | 8 | 0.53 |
| Il | ng/ml | 3.8E2 | 7.0E2 | 1.3E3 | 3.6E3 | 2.8E3 | 5.3E3 | 1.0E-9 | 7.1E1 | 1.2E4 | 1.2E4 | 257 | 8 | 257 | 8 | 0.64 |
| Im | ng/ml | 2.3E2 | 7.0E2 | 4.7E2 | 2.0E3 | 7.5E2 | 2.5E3 | 1.4E1 | 1.5E2 | 6.0E3 | 6.2E3 | 259 | 8 | 259 | 8 | 0.82 |
| In | ng/ml | 3.3E0 | 2.8E0 | 1.9E1 | 6.0E2 | 8.2E1 | 1.6E3 | 1.0E-9 | 1.0E-9 | 1.1E3 | 4.5E3 | 262 | 8 | 262 | 8 | 0.52 |
| Io | ng/ml | 1.1E4 | 1.2E4 | 2.2E4 | 1.3E4 | 5.1E4 | 1.1E4 | 1.0E-9 | 1.5E3 | 7.1E5 | 3.3E4 | 262 | 8 | 262 | 8 | 0.47 |
| Ip | ng/ml | 1.4E1 | 4.2E1 | 2.2E1 | 4.2E1 | 2.7E1 | 1.5E1 | 1.0E-9 | 2.1E1 | 2.3E2 | 5.8E1 | 262 | 8 | 262 | 8 | 0.78 |
| Iq | ug/ml | 1.2E-1 | 3.5E0 | 8.2E-1 | 3.4E1 | 2.8E0 | 7.6E1 | 1.0E-9 | 7.4E-2 | 3.4E1 | 2.2E2 | 262 | 8 | 262 | 8 | 0.77 |
| Ir | ug/ml | 4.1E-1 | 1.4E1 | 2.7E0 | 8.1E1 | 1.2E1 | 1.3E2 | 1.0E-9 | 3.4E-1 | 1.6E2 | 3.7E2 | 261 | 8 | 261 | 8 | 0.82 |
| Is | ng/ml | 2.2E0 | 5.1E1 | 8.3E0 | 8.2E1 | 1.8E1 | 8.5E1 | 1.0E-9 | 8.9E0 | 1.5E2 | 2.6E2 | 262 | 8 | 262 | 8 | 0.93 |
| It | ng/ml | 2.1E0 | 1.4E1 | 1.5E1 | 9.9E1 | 6.8E1 | 2.4E2 | 1.0E-9 | 1.0E-9 | 8.3E2 | 6.8E2 | 262 | 8 | 262 | 8 | 0.70 |
| Iu | ng/ml | 1.8E2 | 6.6E2 | 1.2E3 | 6.4E3 | 3.7E3 | 1.1E4 | 1.0E-9 | 8.5E0 | 2.9E4 | 2.4E4 | 262 | 8 | 262 | 8 | 0.64 |
| Iv | ng/ml | 1.4E1 | 3.7E2 | 5.3E1 | 1.1E3 | 2.5E2 | 1.6E3 | 1.0E-9 | 1.0E0 | 3.8E3 | 3.8E3 | 261 | 8 | 261 | 8 | 0.75 |
| Pz | ng/ml | 4.3E3 | 3.5E3 | 5.9E3 | 5.7E3 | 6.2E3 | 4.5E3 | 1.6E1 | 1.1E3 | 7.0E4 | 1.3E4 | 258 | 8 | 258 | 8 | 0.54 |
| Qa | ng/ml | 3.9E3 | 2.0E4 | 7.2E3 | 4.3E4 | 8.2E3 | 7.3E4 | 1.5E2 | 2.9E3 | 4.2E4 | 2.2E5 | 258 | 8 | 258 | 8 | 0.85 |
| Qb | ng/ml | 1.2E2 | 5.3E2 | 2.4E2 | 4.3E2 | 3.9E2 | 2.0E2 | 7.9E-1 | 1.3E2 | 4.1E3 | 6.0E2 | 258 | 8 | 258 | 8 | 0.80 |
| Qc | ng/ml | 2.5E2 | 5.4E2 | 4.6E2 | 7.8E2 | 5.8E2 | 9.5E2 | 1.0E-9 | 1.3E1 | 4.3E3 | 2.8E3 | 258 | 8 | 258 | 8 | 0.59 |
| Qd | ng/ml | 1.0E4 | 7.9E4 | 3.0E4 | 9.4E4 | 1.3E5 | 8.8E4 | 2.4E2 | 3.5E3 | 2.0E6 | 2.3E5 | 258 | 8 | 258 | 8 | 0.77 |
| Qe | ng/ml | 1.1E3 | 4.3E3 | 2.2E3 | 5.8E3 | 6.3E3 | 5.8E3 | 7.6E0 | 5.7E2 | 9.7E4 | 1.8E4 | 258 | 8 | 258 | 8 | 0.79 |
| Jg | ng/ml | 5.5E2 | 2.4E3 | 8.5E2 | 2.7E3 | 9.9E2 | 2.0E3 | 5.8E0 | 2.8E2 | 1.0E4 | 7.1E3 | 261 | 8 | 261 | 8 | 0.86 |
| Jh | ng/ml | 3.0E0 | 1.1E2 | 2.4E1 | 1.4E2 | 9.4E1 | 1.5E2 | 1.0E-9 | 4.3E0 | 1.2E3 | 4.9E2 | 261 | 8 | 261 | 8 | 0.90 |
| Ji | ng/ml | 6.3E1 | 3.8E2 | 9.2E1 | 4.8E2 | 1.0E2 | 3.5E2 | 1.1E0 | 1.2E2 | 6.7E2 | 1.3E3 | 261 | 8 | 261 | 8 | 0.95 |
| Jj | ng/ml | 5.5E2 | 1.0E2 | 2.3E3 | 2.2E2 | 2.1E4 | 3.2E2 | 2.0E1 | 1.2E1 | 3.4E5 | 1.0E3 | 261 | 8 | 261 | 8 | 0.18 |
| Jk | ng/ml | 3.0E0 | 7.8E1 | 2.2E1 | 9.8E1 | 5.1E1 | 9.0E1 | 1.0E-9 | 1.3E0 | 3.9E2 | 2.4E2 | 261 | 8 | 261 | 8 | 0.80 |
| Jl | ng/ml | 5.1E-1 | 2.0E1 | 2.2E0 | 1.3E3 | 5.1E0 | 3.5E3 | 1.2E-3 | 1.2E0 | 4.0E1 | 9.9E3 | 261 | 8 | 261 | 8 | 0.92 |
| Jm | ng/ml | 2.3E1 | 3.1E1 | 6.8E1 | 7.4E1 | 1.7E2 | 1.2E2 | 1.0E-9 | 2.1E0 | 2.1E3 | 3.6E2 | 261 | 8 | 261 | 8 | 0.57 |
| Jn | pg/ml | 4.0E-1 | 2.8E0 | 2.7E0 | 1.7E2 | 1.6E1 | 3.1E2 | 1.0E-9 | 4.2E-1 | 2.4E2 | 7.3E2 | 261 | 8 | 261 | 8 | 0.83 |
| Jo | pg/ml | 4.3E3 | 4.1E3 | 5.2E3 | 2.1E4 | 4.1E3 | 3.5E4 | 2.6E2 | 2.3E2 | 2.4E4 | 1.0E5 | 261 | 8 | 261 | 8 | 0.55 |
| Jp | pg/ml | 7.4E4 | 1.2E5 | 7.8E4 | 1.3E5 | 3.9E4 | 4.6E4 | 2.1E3 | 6.5E4 | 3.8E5 | 2.1E5 | 261 | 8 | 261 | 8 | 0.83 |
| Jq | pg/ml | 9.9E1 | 4.6E2 | 1.6E2 | 2.0E3 | 2.0E2 | 3.0E3 | 5.6E0 | 7.1E1 | 1.7E3 | 8.7E3 | 261 | 8 | 261 | 8 | 0.85 |
| Jr | pg/ml | 4.1E0 | 7.2E1 | 3.5E1 | 1.6E3 | 2.0E2 | 2.9E3 | 1.0E-9 | 6.7E0 | 2.4E3 | 7.4E3 | 261 | 8 | 261 | 8 | 0.88 |
| Js | pg/ml | 1.6E1 | 5.4E1 | 5.5E1 | 7.9E2 | 2.3E2 | 1.3E3 | 1.0E-9 | 6.1E0 | 3.0E3 | 3.0E3 | 261 | 8 | 261 | 8 | 0.78 |
| Jt | pg/ml | 2.6E3 | 4.8E3 | 3.3E3 | 1.3E4 | 3.3E3 | 1.8E4 | 1.5E2 | 1.0E3 | 4.1E4 | 5.2E4 | 261 | 8 | 261 | 8 | 0.71 |
| Lh | pg/ml | 1.5E4 | 8.2E4 | 2.4E4 | 1.9E5 | 3.1E4 | 2.0E5 | 1.0E-9 | 1.8E3 | 2.6E5 | 4.8E5 | 262 | 8 | 262 | 8 | 0.80 |
| Li | pg/ml | 4.0E3 | 9.3E4 | 1.8E4 | 1.0E5 | 6.9E4 | 1.1E5 | 1.3E1 | 2.5E3 | 9.2E5 | 3.1E5 | 262 | 8 | 262 | 8 | 0.79 |
| Lj | pg/ml | 3.1E3 | 1.8E4 | 1.9E4 | 6.9E4 | 5.1E4 | 1.3E5 | 1.0E-9 | 2.6E3 | 4.3E5 | 3.9E5 | 262 | 8 | 262 | 8 | 0.72 |
| Nv | pg/ml | 4.1E3 | 4.5E4 | 1.1E4 | 4.9E4 | 2.1E4 | 4.1E4 | 1.0E-9 | 2.6E3 | 1.6E5 | 1.1E5 | 263 | 8 | 263 | 8 | 0.82 |
| Nw | pg/ml | 1.0E4 | 3.1E4 | 1.4E4 | 7.9E4 | 1.7E4 | 8.6E4 | 1.9E2 | 1.5E4 | 2.1E5 | 2.2E5 | 263 | 8 | 263 | 8 | 0.92 |
| Nx | pg/ml | 2.2E2 | 1.2E3 | 4.5E2 | 1.4E3 | 6.4E2 | 1.2E3 | 1.0E-9 | 1.0E-9 | 3.5E3 | 4.1E3 | 263 | 8 | 263 | 8 | 0.79 |
| Ny | pg/ml | 7.8E0 | 2.8E2 | 1.2E2 | 5.6E2 | 1.5E3 | 9.2E2 | 1.0E-9 | 9.8E0 | 2.5E4 | 2.8E3 | 263 | 8 | 263 | 8 | 0.85 |
| Oe | pg/ml | 3.1E1 | 4.7E0 | 2.6E2 | 2.3E2 | 4.0E2 | 4.3E2 | 1.0E-9 | 1.0E-9 | 2.3E3 | 1.1E3 | 261 | 8 | 261 | 8 | 0.46 |
| Of | pg/ml | 1.9E2 | 3.3E2 | 6.1E3 | 1.3E4 | 2.3E4 | 2.3E4 | 1.0E-9 | 1.1E1 | 1.9E5 | 6.6E4 | 263 | 8 | 263 | 8 | 0.59 |
| Og | pg/ml | 7.6E-2 | 9.2E-3 | 3.9E-1 | 6.9E-2 | 1.6E0 | 1.1E-1 | 1.0E-9 | 1.0E-9 | 1.9E1 | 3.2E-1 | 263 | 8 | 263 | 8 | 0.37 |
| Oh | pg/ml | 2.9E0 | 5.5E1 | 7.7E1 | 1.9E2 | 9.8E2 | 3.8E2 | 1.0E-9 | 8.3E0 | 1.6E4 | 1.1E3 | 263 | 8 | 263 | 8 | 0.93 |
| Oi | pg/ml | 2.6E0 | 1.0E-9 | 5.3E0 | 6.5E0 | 7.2E0 | 1.1E1 | 1.0E-9 | 1.0E-9 | 4.2E1 | 3.1E1 | 263 | 8 | 263 | 8 | 0.43 |
| Ok | pg/ml | 4.2E2 | 1.9E3 | 5.4E2 | 2.7E3 | 4.7E2 | 2.5E3 | 1.5E1 | 5.2E2 | 3.2E3 | 7.8E3 | 263 | 8 | 263 | 8 | 0.92 |
| Om | pg/ml | 4.3E2 | 4.7E3 | 8.7E2 | 9.5E3 | 2.3E3 | 1.7E4 | 1.0E-9 | 5.4E2 | 3.0E4 | 5.1E4 | 263 | 8 | 263 | 8 | 0.92 |
| On | pg/ml | 2.0E2 | 1.7E3 | 3.3E2 | 2.4E3 | 4.8E2 | 2.6E3 | 8.4E-1 | 3.3E2 | 4.5E3 | 8.5E3 | 263 | 8 | 263 | 8 | 0.94 |

Figure 43 Continued

| Code | Units | Median | | Average | | Standard Deviation | | Minimum | | Maximum | | Number of Samples | | Number of Patients | | AUC |
|---|---|---|---|---|---|---|---|---|---|---|---|---|---|---|---|---|
| | | NonDis | Dis | NonDis | Dis | NonDis | Dis | NonDis | Dis | NonDis | Dis | NonDis | Dis | NonDis | Dis | |
| Oy | pg/ml | 4.9E-1 | 2.1E0 | 7.2E0 | 7.9E0 | 3.5E1 | 1.2E1 | 1.0E-9 | 1.0E-9 | 4.0E2 | 3.3E1 | 262 | 8 | 262 | 8 | 0.65 |
| Oz | pg/ml | 8.5E-3 | 1.0E-9 | 3.6E-1 | 3.6E0 | 1.8E0 | 9.9E0 | 1.0E-9 | 1.0E-9 | 2.9E1 | 2.8E1 | 262 | 8 | 262 | 8 | 0.44 |
| Pa | pg/ml | 4.3E-1 | 4.7E0 | 1.5E0 | 4.4E1 | 6.4E1 | 8.1E1 | 1.0E-9 | 1.7E-1 | 8.6E1 | 2.3E2 | 262 | 8 | 262 | 8 | 0.79 |
| Pb | pg/ml | 1.0E-9 | 1.0E-9 | 2.1E0 | 4.2E0 | 3.0E1 | 1.1E1 | 1.0E-9 | 1.0E-9 | 4.9E2 | 3.2E1 | 262 | 8 | 262 | 8 | 0.45 |
| Pc | pg/ml | 9.9E-2 | 1.0E-9 | 1.7E0 | 5.6E0 | 2.0E1 | 1.3E1 | 1.0E-9 | 1.0E-9 | 3.3E2 | 3.8E1 | 262 | 8 | 262 | 8 | 0.52 |
| Pd | pg/ml | 1.7E0 | 2.4E1 | 7.3E0 | 3.1E1 | 5.3E1 | 4.0E1 | 1.0E-9 | 7.3E-2 | 8.4E2 | 1.2E2 | 262 | 8 | 262 | 8 | 0.74 |
| Pe | pg/ml | 2.4E1 | 8.2E2 | 1.3E2 | 3.6E3 | 5.0E2 | 5.3E3 | 1.0E-9 | 2.6E1 | 4.7E3 | 1.5E4 | 262 | 8 | 262 | 8 | 0.83 |
| Pf | pg/ml | 1.9E0 | 4.3E1 | 1.5E1 | 9.5E1 | 9.7E1 | 1.4E2 | 1.0E-9 | 3.7E0 | 1.5E3 | 4.3E2 | 262 | 8 | 262 | 8 | 0.91 |
| Pg | pg/ml | 4.6E0 | 2.1E2 | 9.2E1 | 5.8E2 | 5.9E2 | 7.8E2 | 1.0E-9 | 4.6E-1 | 7.7E3 | 2.2E3 | 262 | 8 | 262 | 8 | 0.81 |
| aA | mg/dL | 9.0E-1 | 2.9E0 | 1.0E0 | 2.6E0 | 4.9E-1 | 1.4E0 | 3.0E-1 | 5.5E-1 | 4.2E0 | 4.7E0 | 394 | 11 | 394 | 11 | 0.84 |

Analyte panel data:

Unconstrained panels with 3 analytes, where 1.0E-8 >= 'model p-value' > 0. Contains 2,423 panels of 287,980 total panels evaluated. : No{Jh(aA Et Fp Fr Hq Hr Hu Hv Hw Hx Ih Ii Ij Ik Il Im In Io Ip Iq Ir Is It Iu Iv Jg Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ji(aA Et Fp Fr Hq Hr Hu Hv Hw Hx Ih Ii Ij Ik Il Im In Io Ip Iq Ir Is It Iu Iv Jg Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jj(aA Et Fp Fr Hq Hr Hu Hv Hw Hx Ih Ii Ij Ik Il Im In Io Ip Iq Ir Is It Iu Iv Jg Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Om(aA Et Fp Fr Hq Hr Hu Hv Hw Hx Ih Ii Ij Ik Il Im In Io Ip Iq Ir Is It Iu Iv Jg Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok On Oy Oz Pa Pb Pc Pd Pe Pf Pg Po Pz Qa Qb Qc Qd Qe) Jq(aA Et Fr Hu Hw Ih Ii Ij Ik Il Im In Io Ip Is It Jg Jl Jm Jo Jp Jr Js Jt Lh Lv Lw Ly Ma Mb Md Me Mg Mh Mi Mj Mm Mn Mp Mq Mr Ms Mt Mu Mw My Mz Nb Nc Nd Nf Ng Nj Nl Nn Nr Ns Nv Nx Og Oh Oi Ok On Oy Pb Pc Pf Pg Pz Qc Qd) Is(Et Fr Hr Hu Hw Ih Ii Ij Ik Il Im In Io It Iu Jg Jm Jn Jo Jr Js Jt Lv Lw Lx Ly Lz Ma Mb Me Mg Mh Mj Mm Mp Mq Mr Ms Mt Mu Mw Mz Na Nb Nc Nd Nf Ng Nj Nl Nn Nq Nr Nt Nu Nv Nx Og Oi Ok On Oz Pb Pg Pz Qb Qc Qd Qe) Ok(aA Et Fr Hr Hu Ii Ik Im In Io Iu Jg Jm Jo Jr Jt Lh Li Lj Lv Lw Ly Lz Ma Mb Me Mg Mh Mj Mm Mp Mq Mr Ms Mt Mu Mw Mz Nb Nc Nd Ne Nf Ng Nj Nl Nn Nt Nu Nv Nx Og Oi On Pb Pz Qc Qd) Et(aA Hr Hu Hv Hw Ik Im In Io Ir Iu Jg Jm Jn Jo Jr Jt Lv Lw Ly Mb Me Mg Mj Mp Ms Mt Mu Mw Mz Na Nb Nc Nd Nf Ng Nj Nl Nn Nu Nv Oh Oi On Oz Pb Pz Qd) Jg(aA Hr Hu Hv Hw Ik Il Im In Io Ip Ir Jk Jm Jn Jo Jr Js Lw Mb Mg Mj Mp Ms Mu Mv Mw My Mz Na Nf Ng Ni Nj Nn Nq Ns Nv Oe Og Oh Oi Oy Pb Pg Pz Qa) Nn(Hr Hu Hv Hw Ij Ik Il Im In Io Ip Ir Iu Iv Jm Jn Jo Jr Lw Lz Mb Mg Mh Mi Mj Mp Ms Mw My Mz Na Nf Ng Ni Nj Nl Nq Ns Nv Oh Oi Pc Pz Qa) Mw(aA Hr Hu Ii Ik Il Im Io Ip Iq Ir Jk Jm Jn Jo Jr Lw Ly Mb Mg Mj Mp Ms My Mz Nb Ng Nj Ns Nv Og Oi Oy Pb Pg) On(Hr Hu Ii Ik Il Im Io Jm Jo Mb Me Mj My Mz Nb Ng Nj Ns Nv Oi Oy Pb Pz) Mp(aA Hr Hv Ik Im In Io Ir Jm Jn Jr Lw Mb Mj Ms Mu Mz Na Nf Nj Ns Oi) Mu(aA Hr Hu Ik Ir Jn Jr Mb Mj Ms Ng Nj Ns Oi Pb) Hr(aA Im Ip Ir Jl Jn Jr Lw Mb Ms Mt Mz Nf Oi) Nj(aA Fr Ik Im Jn Lw Ly Mb Ms Mz Nf Nl) Im(Fr Hu Ir Jn Jr Lw Mb Me Ms Mz) Mj(Ir Jn Jr Js Lw Ms Mz Nf Oh) Mb(Fr Il Ip Me Mt Ns Nw Pb) Lw(Io Jo Ms Nv Pb) Mm(Io Iu Jn Jr Mz) Me(aA Io Jm Ms) Oi(aA Mt Oh) Nm(Jo Mg) Io(aA Ms) Pb(Ir Na) FrJn} aA{Om(Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok On Oy Oz Pa Pb Pc Pd Pe Pf Pg Po Pz Qa Qb Qc Qd Qe) Ji(Et Fr Hu Hv Hw Ih Ij Ik Im In Io Ip Ir Is It Iu Jg Jh Jj Jk Jl Jm Jn Jo Jq Jr Js Jt Lh Li Lu Lv Lw Lx Lz Ma Mb Me Mf Mg Mh Mi Mj Ml Mm Mn Mp Mq Mr Ms Mt Mu Mw Mx My Mz Na Nb Nc Nd Ne Nf Nh Ni Nj Nl Nm Nn Nq Nr Ns Nt Nu Nv Nw Nx Ny Oe Of Og Oh Oi Ok On Oy Oz Pa Pb Pc Pe Pf Po Pz Qa Qb Qc Qd Qe) Nj(Et Fr Hr Hw Ii Ij Ik Im In Io Ip Iq Is Jg Jh Jj Jk Jl Jq Jr Jt Lh Lv Lw Lx Ma Mb Md Me Mg Mj Mm Mn Mp Mq Mr Mt Mu Mv Mw Mz Na Nd Nf Ng Ni Nk Nl Nm Nn Ns Nt Nu Nw Nx Ny Og Oh Oi Ok On Pa Pc Pe Pf Po Pz Qd Qe) Jg(Hr Hu Ik Io Ip Jj Jl Jq Lj Lw Me Mg Mp Mq Ms Mu Mv Mw My Ng Ns Nu Oe Og Oh Oi Ok Oy Pb Pc Pf Pz) Jh(Hr Hu Ik Im Io Ip Jj Jl Jr Lw Lx Me Mg Mh Mp My Nd Ng Nu Nw Oe Og Oi Ok Oy Pb Pz) Io(Et Fr Hr Ip Is Jl Ma Me Mm Mn Mp Mt Mu Mw Nc Nm Nn Nw Ok On Pf) Me(Hu Is Ij Jn Jq Jr Lh Mf Mu My Mz Nf Nw Oi Ok On Pc Pe Pf) Oi(Et Fr Hr Jl Ma Mn Mp Mt Mu Mw Nn Nw Ok On Pf) Hr(Et Fr Ip Jl Jr Mt Mu Mw Ok On Pf Po) On(Ik Jj Jt Mg Mj Mp My Oh Pc Pz) Mu(Et Ik Is Jj Jq Jr Mp Ok) Mw(Hu Ik Jj Mg My Og Ok Oy) Oh(Fr Lw Mm Mp Nn Ok Pc) Fr(Ik Jj My Pz) Nn(Mp My Pc) Jj(Jl Lx Mr) Ok(Jt Mq Pz) Jq(Lx Nd) NmJt LwPc IkJl} Jj{On(Fr Hu Hv Hw Ik Im Io Iv Jh Ji Jk Jl Jn Jq Jr Lh Lw Lx Ma Mg Mj Mp Mr Mu Mw My Mz Nc Nd Ne Nf Nj Nn Nt Oe Og Oh Oi Om Oy Pa Pb Pc Pe Pz Qc Qd) Nt(Fr Ii Ip Iq Is Jg Jh Ji Jk Jl Jn Jq Jr Js Lh Mn Mp Mt Mu Mw Mz Nf Nj Nn Nw Ny Ok Om Pf) Mu(Et Hw Ii Il Iq Ir Is Iv Ji Jl Jn Jr Lh Lx Mp Mr Mw Nc Nd Nj Og Ok On Pb Qb) Mr(Et Fr Ik Ip Is Jg Jh Ji Jk Jl Jq Jr Lw Ma Mm Mp Mt Mw Nc Nm Nn Nw Oh Ok Om Pb) Lh(Et Fr Is Jg Jh Ji Jk Jl Jq Jr Ma Me Mm Mn Mp Mt Mw Nj Nm Nn Nw Ok Om Pb) Lx(Et Fr Ii Ir Is Iv Jh Ji Jk Jl Jn Jq Jr Ly Mh Mw My Nm Nn Ok Om) Ji(Fr Hu Ik Im Io Jg Jh Ji Jq Mp Mw Nc Nd Nf Nj Nn Og Oi Om Qc) Fr(Hw Il Im Ir Is Iv Ji Jn Jq Jr Nd Ok Pe) Nd(Ii Is Jh Ji Jk Jq Mw Nn Ok Om) Mw(Iq Ir Ji Jn Jr Mz Ne Ok) Jh(Hw Iq Is Ji Jr Nc Pe) Jk(Is Ji Jr Og Oi Ok) Om(Hw Im Is Nc Nl Og) Ji(Hw Nn Pa Pe) Po(Ik Oy) Pe(Ik Nn) Iilm JqPa} Ji{Mu(Et Hr Hu Hw Hx Ii Ij Ik Im In Io Iq Ir Is Iv Jl Jm Jo Js Jt Lj Lv Lw Lx Ma Mb Md Mf Mg Mh Mj Ml Mp Mq Mr Ms Mv Mw My Mz Nb Nc Nd Ne Nf Ng Nj Nn Nq Nr Ns Nt Nu Nv Nx Ny Of Og Oh Oi Ok Oy Pa Pb Pc Pe Pz Qc Qd) Fr(Ik Im Io Jo Jt Lv Ma Mg Mv My Mz Ne Ng Nr Nu Nx Og Oh Oi Oy Pb Pc Pz Qc) Ik(Hw Io Iv Jh Jk Jl Lz Mk Mr Mt Mw Nn Nr Nt Ok Om On Oz Pa Pe Pf Po) Jl(Hr Ii Im Io Jh Lv Mj Mq Mz Nx Og Oi Pb Pz Qc Qd Qe) Jh(Ij Im Mg My Nc Nd Ng Of Og Oi Oy Pb Pz) Io(Et Hw Iq Lx Mb Mr Nc Nd Nt Ok Pa Pe) Mr(Hr Ii Ij Mj Nx Og Pb Pz) Mw(Ij Mg My Ng Og Oi Oy Qc) Pz(Et Jg Nd Nn Ok On Pf) Oi(Et Jg Mt Nn Ok On Pa) Nt(Ii Jo Lv Mg Mj Nx) Qc(Iq Jn Jr Mp Mt Mz) Jk(My Ng Nx Og Oy Pb) Om(Ij My Of Og Oy Pb) Pa(My Ng Nx Og Oy Pb) Ok(Ij Im Jt Mq) Mg(Ma Mm Nn) Pe(Ij Og Pb) Lx(Ly Nx) Nd(In Nx) Jg(My Og) NnOh HwIj} Ik{On(Fp Hu Hv Hw Ij Im In Io Ir Is

Figure 43 Continued

It Iv Jh Jn Jq Jr Lw Lz Mg Mk Mp Mr Mt Mu Mw My Mz Na Nc Nh Ni Nj Nr Nt Og Oh Oi Ok Om Pa Pc Pe Pf Pz Qc) Jh(Fr Hw Iq Ir Is Iv Jl Jr Lh Lz Mh Mi Mj Mk Mr Mx Nb Nc Nr Nt Ok Oz Pa Pe Pf Po Qa) Om(Et Fr Hw Iq Ir Is Iv Jl Lh Lz Mk Mp Mr Mt Mu Mw Nb Nr Nt Og Ok Oz Pa Pe Pf Po) Pe(Et Fr Is Jg Jk Jl Jq Lw Lx Ma Me Mm Mp Mt Mu Mw Nj Nn Nw Ok Pf) Mr(Fr Is Jg Jl Jq Lw Lx Ma Mp Mt Mu Mw Nn Nw Ok) Mw(Iq Ir Is Iv Jl Jn Jq Jr Lz Mz Ok Pa Pf) Iv(Fr Jg Jq Lw Lx Ma Mt Mu Nn Nw Ok) Ok(Fr Jk Jl Lx Mu Nn Nw Pa Pf Po) Mu(Ir Is Jl Lh Pa) Is(Fr Lx Pf Po) Fr(Ir Jr) Jl(Jg Mt) Jq(Mk Pa) LxIr} Om{Og(Et Hq Hw Im Iq Ir Is Iv Jg Jl Lh Lx Mr Nb Nt Nw Oh Ok On Oy Pa Pb Pe) Oy(Et Fr Ii Is Jl Lh Lx Mp Mr Mt Mw Nd Nt Oh Ok On Pa Pe Po) Of(Is Jl Lh Lx Mr Nd Nt Ok On Pa Pe Po) Pb(Et Hw Is Jl Lh Mr Nr Nt Ok On Pa Pe) My(Fr Is Lh Lx Mr Nt Nw Ok On Pa) Mg(Lh Lx Mi Mp Nt Ok) Ng(Lh Lx Nd Nt Pa) Lx(Hu Ly) Ij(Is Ok) PzOk} On{Pz(Hr Hu Iq Ir Is Lj Mg My Ng Nn Nv Og Ok Oy Pb) Oy(Ii Im Io Jg Jh Mj Mu Mw Oh Oi Qc Qd) My(Fr Im Io Jg Jh Mu Mw Mz Nq Oi Qc) Oi(Hr Hu Lj Lv Mg Ng Of Pb) Ng(Im Io Jh Lx Mu Nd) Og(Io Jg Jh) Jq(Ij Im) HuIo PbPe} Jh{Ng(Jl Lh Lx Mr Nd Nt Pa Pe Po) Og(Is Jl Lh Mh Mr Nw Ok Pa Pe) My(Jl Lh Lx Mh Mr Nw Pa Po) Oy(Jl Lh Lx Mh Mr Pa Pe Po) Mg(Iq Jl Lh Lx Mr Ok Pe) Hu(Jl Lh Lx Mr Nt Pa) Pb(Jl Lh Mr Pe) Pz(Jl Ok) LhOf} Ok{Mg(Fr Jk Lx Mu Mw Nd Nn) Mw(My Ng Og Oy Pb Pz) Pz(Fr Mu Nd Nn) Lx(Jo Ly Pb) Mq(Mp Mu Nn) Nw(Im Oi Pb) Fr(Jo Ng) Jq(Im Nd) NnOi MuPb} Jq{Pa(Im Md My Nb Og Oy Pb) Mr(Hr Im Mj Mp Og Pb) Im(Fr Jl Nc Pe) NdJl JgOg PbPe} Is{Mu(Hr Mg My Ng Nj Og Oi Oy Pb Pz) Fr(Mg My Ng Oi Pz) Mw(My Og) NnOi JgOg} Mw{Ng(Lx Mr Po) Oy(Lx Mt Po) My(Iq Nw) Og(Jr Mz)} Jg{Ng(Lh Lx Nd Nt) Jl(Og Pz)} Nn{Jl(Oi Pz) MgPe IiOy} Pb{Mu(Ir Pe) NfJl HwNw} Fr{Mg(Iv Nm) IrJo} Lx{Ly(Mr Pe)} MuNgPa

Unconstrained panels with 3 analytes, where 1.0E-7 >= 'model p-value' > 1.0E-8. Contains 14,716 panels of 287,980 total panels evaluated. : No{Nm(aA Et Fp Fr Hq Hr Hu Hv Hw Hx Ih Ii Ij Ik Il Im In Io Ip Iq Ir Is It Iu Iv Jg Jk Jl Jm Jn Jp Jq Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nn Nq Nr Ns Nt Nu Nv Nw Nx Ny Oe Of Og Oh Oi Ok On Oy Oz Pa Pb Pc Pd Pe Pf Pg Po Pz Qa Qb Qc Qd Qe) Jl(aA Et Fp Fr Hq Hu Hv Hw Hx Ih Ii Ij Ik Il Im In Io Ip Iq Ir Is It Iu Iv Jg Jk Jm Jn Jo Jp Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nn Nq Nr Ns Nt Nu Nv Nw Nx Ny Oe Of Og Oh Oi Ok On Oy Oz Pa Pb Pc Pd Pe Pf Pg Po Pz Qa Qb Qc Qd Qe) Oh(aA Fp Fr Hq Hr Hu Hv Hw Hx Ih Ii Ij Ik Il Im In Io Ip Iq Ir Is It Iu Iv Jk Jm Jn Jo Jp Jr Js Jt Lh Li Lj Lu Lv Lw Lx Ly Lz Ma Mb Mc Md Me Mf Mg Mh Mi Mk Ml Mm Mn Mp Mq Mr Ms Mt Mu Mv Mw Mx My Mz Na Nb Nc Nd Ne Nf Ng Nh Ni Nj Nk Nl Nq Nr Ns Nt Nu Nv Nw Nx Ny Oe Of Og Ok On Oy Oz Pa Pb Pc Pd Pe Pf Pg Po Pz Qa Qb Qc Qd Qe) Fr(aA Et Fp Hq Hr Hu Hv Hw Hx Ih Ii Ij Ik Il In Io Ip Iq Ir It Iu Iv Jg Jk Jm Jo Jp Jr Js Jt Lh Li Lj Lu Lv Lw Lx Ly Lz Ma Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nk Nl Nn Nq Nr Ns Nt Nu Nv Nw Nx Ny Oe Of Og Oi On Oy Oz Pa Pb Pc Pd Pe Pf Pg Po Pz Qa Qb Qc Qd Qe) Mt(aA Fp Hq Hu Hv Hw Hx Ih Ii Ij Ik Il Im In Io Ip Iq Ir It Iu Iv Jg Jk Jm Jn Jo Jp Jr Js Jt Lh Li Lj Lu Lv Lw Lx Ly Lz Ma Mc Md Me Mf Mg Mh Mi Mj Mk Ml Mm Mn Mp Mq Mr Ms Mu Mv Mw Mx My Mz Na Nb Nc Nd Ne Nf Ng Nh Ni Nj Nk Nl Nn Nq Nr Ns Nt Nu Nv Nw Nx Ny Oe Of Og On Oy Oz Pa Pb Pc Pd Pe Pf Pg Po Pz Qa Qb Qc Qd Qe) Ip(aA Et Fp Hq Hu Hv Hw Hx Ih Ii Ij Ik Il Im In Io Iq Ir Is It Iu Iv Jk Jm Jn Jo Jp Jr Js Jt Lh Li Lj Lu Lv Lw Lx Ly Lz Ma Mc Md Me Mf Mg Mh Mi Mj Mk Ml Mm Mn Mp Mq Mr Ms Mu Mv Mx My Mz Na Nb Nc Nd Ne Nf Ng Nh Ni Nj Nk Nl Nq Nr Ns Nt Nu Nv Nw Nx Ny Oe Of Og Oi Ok On Oy Oz Pa Pb Pc Pd Pe Pf Pg Po Pz Qa Qb Qc Qd) Ns(aA Et Fp Hq Hr Hu Hv Hw Hx Ih Ii Ij Ik Il Im In Io Iq Ir Is It Iu Iv Jk Jm Jn Jo Jp Jr Js Jt Lh Li Lj Lu Lv Lw Lx Ly Lz Ma Mc Md Me Mf Mg Mh Mi Mj Mk Ml Mm Mn Mq Mr Ms Mv Mx My Mz Na Nb Nc Nd Ne Nf Ng Nh Ni Nj Nk Nl Nq Nr Nt Nu Nv Nw Nx Ny Oe Of Og Oi Ok Oy Oz Pa Pb Pc Pd Pe Pf Pg Po Pz Qa Qb Qc Qd Qe) Mm(aA Et Fp Hq Hr Hu Hv Hw Hx Ih Ii Ij Ik Il Im In Iq Ir It Iv Jg Jk Jm Jo Jp Js Jt Lh Li Lj Lu Lv Lw Lx Ly Lz Ma Mb Mc Md Me Mf Mg Mh Mi Mj Mk Ml Mn Mp Mq Mr Ms Mu Mv Mw Mx My Na Nb Nc Nd Ne Nf Ng Nh Ni Nj Nk Nl Nn Nq Nr Nt Nu Nv Nw Nx Ny Oe Of Og Oi On Oy Oz Pa Pb Pc Pd Pe Pf Pg Po Pz Qa Qb Qc Qd) Nf(aA Fp Hq Hu Hv Hw Hx Ih Ii Ij Ik Il Im In Io Iq Ir It Iu Iv Jk Jm Jn Jo Jp Jr Js Jt Lh Li Lj Lu Lv Lw Lx Ly Lz Ma Mb Mc Md Me Mf Mg Mh Mi Mk Ml Mn Mq Mr Ms Mu Mv Mw Mx My Mz Na Nb Nc Nd Ne Ng Nh Ni Nk Nl Nq Nr Nt Nu Nv Nw Nx Ny Oe Of Og Oi Ok On Oy Oz Pa Pb Pc Pd Pe Pf Pg Po Pz Qa Qb Qc Qd) Ir(aA Fp Hq Hu Hv Hw Hx Ih Ii Ij Ik Il In Io Iq Is It Iu Iv Jk Jm Jn Jo Jp Jq Jr Js Jt Lh Li Lj Lu Lv Lw Lx Ly Lz Ma Mb Mc Md Me Mf Mg Mh Mi Mk Ml Mn Mq Mr Ms Mv Mx My Mz Na Nb Nc Nd Ne Ng Nh Ni Nj Nk Nl Nq Nr Nt Nu Nv Nw Nx Ny Oe Of Og Oi Ok On Oy Oz Pa Pc Pd Pe Pf Pg Po Pz Qa Qb Qc Qd Qe) Jn(aA Fp Hq Hu Hv Hw Hx Ih Ii Ij Ik Il In Io Iq It Iu Iv Jk Jm Jo Jp Jq Jr Js Jt Lh Li Lj Lu Lv Lw Lx Ly Lz Ma Mb Mc Md Me Mf Mg Mh Mi Mk Ml Mn Mq Mr Ms Mv Mx My Mz Na Nb Nc Nd Ne Ng Nh Ni Nk Nl Nq Nr Nt Nu Nv Nw Nx Ny Oe Of Og Oi Ok On Oy Oz Pa Pb Pc Pd Pe Pf Pg Po Pz Qa Qb Qc Qd Qe) Jr(aA Fp Hq Hu Hv Hw Hx Ih Ii Ij Ik Il In Io Iq It Iu Iv Jk Jm Jo Jp Js Jt Lh Li Lj Lu Lv Lw Lx Ly Lz Ma Mb Mc Md Me Mf Mg Mh Mi Mk Ml Mn Mq Mr Ms Mv Mx My Mz Na Nb Nc Nd Ne Ng Nh Ni Nj Nk Nl Nq Nr Nt Nu Nv Nw Nx Ny Oe Of Og Oi On Oy Oz Pa Pb Pc Pd Pe Pf Pg Po Pz Qa Qb Qc Qd Qe) aA(Fp Hq Hu Hv Hw Hx Ih Ii Ij Ik Il Im In Iq Is It Iu Iv Jk Jm Jo Jp Js Jt Lh Li Lj Lu Lv Lw Lx Ly Lz Ma Mb Mc Md Mf Mg Mh Mi Mj Mk Ml Mn Mq Mr Ms Mv Mx My Mz Na Nb Nc Nd Ne Ng Nh Ni Nk Nl Nn Nq Nr Nt Nu Nv Nw Nx Ny Oe Of Og On Oy Oz Pa Pb Pc Pd Pe Pf Pg Po Pz Qa Qb Qc Qd Qe) Mn(Et Fp Hq Hr Hu Hv Hw Ii Ij Ik Il Im In Io Iq Is It Iu Iv Jg Jk Jm Jo Jp Js Jt Lh Li Lj Lu Lv Lw Ly Lz Ma Mb Md Me Mf Mg Mh Mi Mj Mk Ml Mp Mq Mr Ms Mu Mv Mw Mx My Mz Na Nb Nc Nd Ne Ng Nh Ni Nj Nk Nl Nn Nq Nr Nt Nv Nw Nx Ny Og Oi Ok On Oy Oz Pa Pb Pc Pe Pf Pg Pz Qa Qb) Mz(Fp Hq Hu Hv Hw Hx Ih Ii Ij Ik Il In Io Iq It Iu Iv Jk Jm Jo Jp Js Jt Lh Li Lj Lu Lv Lw Lx Ly Lz Ma Mb Mc Md Me Mf Mg Mh Mi Mk Ml Mq Mr Ms Mu Mv Mx My Na Nb Nc Nd Ne Ng Nh Ni Nk Nl Nq Nr Nt Nu Nv Nw Nx Ny Oe Of Og Oi Oy Oz Pa Pb Pc Pd Pe Pf Pg Po Pz Qa Qb Qc Qd Qe) Hr(Fp Hq Hu Hv Hw Hx Ih Ii Ij Ik Il In Io Iq It Iu Iv Jk Jm Jo Jp Js Jt Lh Li Lj Lu Lv Lx Ly Lz Ma Mc Md Me Mf Mg Mh Mi Mj Mk Ml Mq Mr Mv Mx My Na Nb Nc Nd Ne Ng Nh Ni Nj Nk Nl Nq Nr Nt Nu Nv Nw Nx Ny Oe Of Og Oy Oz Pa Pb Pc Pd Pe Pf Pg Po Pz Qa Qb Qc Qd Qe) Ms(Fp Hq Hu Hv Hw Hx Ih Ii Ij Ik Il In Iq It Iu Iv Jk Jm Jo Jp Js Jt Lh Li Lj Lu Lv Lx Ly Lz Ma Mb Mc Md Mf Mg Mh Mi Mk Ml Mq Mr Mv Mx My Na Nb Nc Nd Ne Ng Nh Ni Nk Nl Nq Nr Nt Nu Nv Nw Nx Ny Oe Of Og Oi On Oy Oz Pa Pb Pc Pd Pe Pf Pg Po Pz Qa Qb Qc Qd Qe) Mu(Fp Hq Hv Hw Hx Ih Ii Ij Il Im In Io Iq It Iu Iv Jk Jm Jo Jp Js Jt Lh Li Lj Lu Lv Lw Lx Ly Lz Ma Mc Md Me Mf Mg Mh Mi Mk Ml Mq Mr Mv Mw Mx My Na Nb Nc Nd Ne Nh Ni Nk Nl Nn Nq Nr Nt Nu Nv Nw Nx Ny Oe Of Og On Oy Oz Pa Pc Pd Pe Pf Pg Po Pz Qa Qb Qc Qd Qe) Im(Fp Hq Hv Hw Hx Ih Ii Ij Ik Il In Io Iq It Iu Iv Jk Jm Jo Jp Js Jt Lh Li Lj Lu Lv Lx Ly Lz Ma Mc Md Mf Mg Mh Mi Mj Mk Ml Mq Mr Mv Mx My Na Nb Nc Nd Ne Ng Nh Ni Nk Nl Nq Nr Nt Nu Nv Nw Nx Ny Oe Of Og Oi Oy Oz Pa Pb Pc Pd Pe Pf Pg Po Pz Qa Qb Qc Qd Qe) Lw(Fp Hq Hu Hv Hw Hx Ih Ii Ij Ik Il In Iq It Iu Iv Jk Jm Jp Js Jt Lh Li Lj Lu Lv Lx Ly Lz Ma Mb Mc Md Me Mf Mg Mh Mi Mk Ml Mq Mr Mv Mx My Na Nb Nc Nd Ne Ng Nh Ni Nk Nl Nq Nr Nt Nu Nw Nx Ny Oe Of Og Oi On Oy Oz Pa Pc Pd Pe Pf Pg Po Pz Qa Qb Qc Qd Qe) Nj(Fp Hq Hu Hv Hw Hx Ih Ii Ij Il In Io Iq It Iu Iv Jk Jm Jo Jp Js Jt Lh Li Lj Lu Lv Lx Lz Ma Mc Md Me Mf Mg Mh Mi Mj Mk Ml Mq Mr Mv Mx My Na Nb Nc Nd Ne Ng Nh Ni Nk Nq Nr Nt Nu Nv Nw Nx Ny Oe Of Og Oi Oy Oz Pa Pb Pc Pd Pe Pf Pg Po Pz Qa Qb Qc Qd Qe) Mb(Fp Hq Hu Hv Hw Hx Ih Ii Ij Ik In Io Iq It Iu Iv Jk Jm Jo Jp Js Jt Lh Li Lj Lu Lv Lx Ly Lz Ma Mc Md Mf Mg Mh Mi Mj Mk Ml Mq Mr Mv Mx My Na Nb Nc Nd Ne Ng Nh Ni Nk Nl Nq Nr Nt Nu Nv Nx Ny Oe Of Og Oi Oy Oz Pa Pc Pd Pe Pf Pg Po Pz Qa Qb Qc Qd Qe) Mp(Fp Hq Hu Hw Hx Ih Ii Ij Il Iq It Iu Iv Jk Jo Jp Js Jt Lh Li Lj Lu Lv Lx Ly Lz Ma Mc Md

On(Et Hr Hu Hv Hx Ih Ii Ij In Ip Iq Ir Is Iv Jg Jm Jn Jo Jq Jr Js Jt Lh Lj Lu Lv Lw Ma Mb Md Me Mf Mg Mh Mi Mj Mk Ml Mm Mp Mq Ms Mt Mu Mv Mw My Mz Na Nb Nc Ne Nf Ng Nh Ni Nj Nl Nr Ns Nu Nv Ny Oe Of Og Oh Om Oy Pb Pc Qb Qc Qd Qe) Mw(Et Hr Hu Hx Ii In Ip Iq Ir Is Iu Iv Jg Jk Jm Jn Jo Jp Jq Jr Js Jt Lh Lj Lu Lv Lw Lz Ma Mb Md Mf Mh Mj Mk Ml Mm Mp Mq Ms Mt Mv Mx Mz Na Nb Nc Ne Nf Nh Ni Nj Nk Nl Nm Nq Nr Ns Nu Nw Ny Oe Of Oh Om Oz Pb Pc Pz Qb) Iq(Et Fp Hr Ih Ii Ij Ik In Ip Is It Iv Jg Jk Jm Jo Jq Jr Js Jt Lh Li Lj Lu Lv Lw Ma Mb Me Mf Mg Mh Mi Mj Mk Ml Mm Mp Mq Ms Mt Mx My Mz Na Nb Nc Ne Nf Ng Ni Nj Nr Nu Nw Ny Og Oh Oi Om Oy Oz Pb Pc Po Pz Qb Qd Qe) Lh(Et Fp Hr Hu Hx Ii Ij Ik In Ip Ir Is Jg Jm Jn Jo Jq Jr Js Jt Lv Lw Ma Mb Md Me Mf Mg Mh Mi Mj Mk Ml Mm Mp Mq Ms Mt Mu Mv My Mz Na Nb Nc Ne Nf Ng Nj Nr Nu Nw Ny Of Og Oh Oi Om Oy Pb Pc Pz Qb Qc Qd Qe) Mt(Et Fp Hr Hu Hx Ij In Ir Is Iv Jk Jo Jq Jr Js Jt Lu Lv Lw Ma Mb Md Me Mf Mg Mh Mj Ml Mm Mp Mq Ms Mu Mv My Mz Na Nb Nc Ne Nf Ng Nj Nl Nr Ns Nu Ny Of Og Oh Om Oy Oz Pb Pc Pz Qb Qd Qe) Et(Hr Hu Ij Ik In Ir Is Iv Jg Jk Jn Jo Jq Jr Js Jt Lu Lv Lw Ly Ma Mb Md Mf Mg Mh Mj Ml Mp Mq Ms My Mz Na Nc Ne Nf Ng Nj Nl Nm Nr Ns Nu Nw Og Oh Om Oy Oz Pb Pc Po Qb Qc Qd) Lu(Hr Hx Ij Ik In Ir Is Iv Jg Jk Jo Jq Jr Js Lv Lw Ma Mb Md Me Mg Mh Mj Ml Mm Mp Ms Mu Mv My Mz Na Nb Nc Ne Nf Ng Nj Nl Nr Ny Of Og Oh Oi Om Oy Oz Pb Pz Qb Qc) Jk(Hr Hu Hx Ii Ij In Ir Is Jm Jn Jo Jq Jr Js Jt Lj Lv Ma Mb Md Mg Mh Mj Mk Ml Mm Mp Mq Ms Mu Mv Mz Na Nb Nc Ne Nf Nl Nr Ns Nu Ny Oe Of Oh Oi Pc Pz Qb Qc Qe) Is(Fp Hr Ih Ij Ik In It Jg Jq Js Jt Lv Lw Ma Mb Me Mf Mg Mj Ml Mm Mp Mq Ms Mx My Mz Nc Nf Nm Nr Nw Og Oh Oi Om Pb Pc Po Pz Qa Qb Qc Qd Qe) Oi(Hr Ii Ij Ik Ip Ir Iu Iv Jn Jo Jp Jr Li Ma Mb Me Mh Ml Mm Mp Ms Mx Mz Na Nb Nc Ne Nf Nk Nm Nq Nr Nv Nw Og Oh Om Oy Oz Pd Po Pz Qb Qc) Mu(Fp Hq Hv Ih Il Ip It Iu Jg Jn Jp Jq Jr Li Ly Lz Mc Me Mi Mk Mm Mn Mx Na Nh Ni Nk Nl Nm Nw Oe Om Oz Pd Pg Po Qa Qb Qe) Qc(Hr Ij Ik In Ir Iu Iv Jg Jp Jq Js Lw Ma Mb Mf Mg Ml Mm Ms Mx My Na Nc Ne Nf Nl Nm Nr Nw Og Oh Om Oz Pb Pc Po Pz Qb) Pz(Hq Hr Ii Ij Ik Ir Iu Iv Jn Jo Jp Jr Ma Mb Mf Mi Ml Mm Mp Ms Mz Na Nb Nc Nm Nr Nv Nw Og Oh Om Oz Pb Po Qb) Mb(Hr Hu Ij Ik In Ir Iv Jg Jn Jo Jq Jr Lw Lz Ma Mg Mh Ml Mm Mp Ms My Nc Ne Nl Nr Nw Og Oh Om Pb Pc Po) Ma(Hr Ij Ik In Ir Iv Jn Jo Jr Lv Lw Mf Ml Mp Ms Mv My Mz Na Nc Ne Ng Nr Ny Og Oh Oy Oz Pb Pc) Mp(Hr Ik Ir Iu Iv Jg Jn Jq Jr Lv Lw Mf Mg Mj Mm Ms Mz Na Nc Ne Nr Og Oh Om Pb Pc Po Qb Qd) Ik(Hq Hr Hu Ii Il Ir Iu Jg Jo Jr Li Mh Mj Mm Ms Mv Na Nb Nc Ne Nu Nv Nw Of Og Oh Pd) Om(Hr Hu Hx In Ir Iu Iv Jo Jr Lj Lv Md Mg Mh Ml Ms Mv Mz Na Nc Ne Ng Nl Nr Ny Oh) Nr(Hr Ii Ij In Jg Jo Jq Jt Lv Mg Mj Ml Mm Mq Ms My Nc Ng Og Oy Pb Qe) Jg(Ij In Ir Jo Jr Jt Lv Mf Mg Ml Ms Mv Mz Nc Ne Ng Ny Of Oh Oy Pb) Po(Hr Hx Ij In Js Md Mg Mh Mj Ml Ms Mv My Nc Ng Ny Of Og Oy Pb) Ij(Hr Hv Ii In Ir Iv Jn Jo Jq Jr Mz Na Nb Nf Ny Qa) Og(Hr Ii Ir Iv Jr Js Me Mm Na Nb Nf Nw Ny Of Oz) Mm(Ir Iv Jr Lw Mf Ms My Nc Ne Ng Oh Pc) Ms(Hr Ii Ir Iv Jr Na Nb Nc Oz Qd) Ii(Hx Md Mh Ml My Ny Of Oy Pb) Ir(Hr In Js Jt Me Mj Pb Qd) Oh(Iu Lw Mg Mi Mj Nc Pc) Hr(Iv Jr Mf Na Ne Oz) Nc(Jq Jr Ni Nw Pc) Mg(Iu Nm Nq Nv) Pb(Iv Nb Ny Oz) Me(Iv Mf) MlNf MyNb IuPc IvQd JrJs} Jj{Om(Et Fp Fr Hq Hr Hu Hv Hx Ih Ii Ij Ik Il In Io Ip Iq Ir It Iu Iv Jg Jh Jk Jm Jn Jo Jp Jq Jr Js Jt Li Lj Lu Lv Lw Ly Lz Ma Mb Mc Md Me Mf Mg Mh Mi Mj Mk Ml Mm Mn Mp Mq Ms Mt Mv Mw Mx My Mz Na Nb Ne Nf Ng Nh Ni Nj Nk Nm Nn Nq Nr Ns Nu Nv Nw Nx Ny Oe Of Oh Oi Ok Oy Oz Pa Pb Pc Pd Pe Pf Pg Po Pz Qa Qb Qc Qd Qe) Mw(Et Fp Fr Hq Hr Hu Hv Hw Hx Ih Ii Ij Ik Il Im In Io Ip Is It Iu Iv Jg Jh Jk Jm Jo Jp Jq Js Jt Li Lj Lu Lv Lw Ly Lz Ma Mb Mc Md Me Mf Mg Mh Mi Mj Mk Ml Mm Mn Mp Mq Ms Mt Mv Mx My Na Nb Nc Nf Ng Nh Ni Nj Nk Nl Nm Nn Nq Nr Ns Nu Nv Nw Nx Ny Oe Of Og Oh Oi Oy Oz Pa Pb Pc Pd Pe Pf Pg Po Pz Qa Qb Qc Qe) Jk(Et Fp Fr Hq Hr Hu Hv Hw Hx Ih Ii Ij Ik Il Im In Io Ip Iq Ir It Iu Iv Jg Jh Jl Jn Jo Jp Jq Js Li Lj Lu Lv Lw Ly Lz Ma Mb Mc Md Me Mf Mg Mh Mi Mk Ml Mm Mn Mp Ms Mt Mu Mv Mx My Mz Na Nb Nc Ne Nf Ng Nh Ni Nj Nk Nl Nm Nn Nq Nr Ns Nu Nv Nw Nx Ny Oe Of Oh Oy Oz Pa Pb Pc Pd Pe Pf Pg Po Pz Qa Qb Qc Qd) Jl(Et Fp Hq Hr Hv Hw Hx Ih Ii Ij Il In Ip Iq Ir Is It Iu Iv Jm Jn Jo Jp Jr Js Jt Li Lj Lu Lv Lw Ly Lz Ma Mb Mc Md Me Mf Mg Mh Mi Mj Mk Ml Mm Mn Mq Ms Mt Mv Mx My Mz Na Nb Ne Ng Nh Ni Nk Nl Nm Nq Nr Ns Nu Nv Nw Nx Ny Oe Of Oh Ok Oy Oz Pa Pb Pc Pd Pe Pf Pg Po Pz Qa Qb Qd Qe) Lh(Fp Hq Hr Hu Hv Hw Hx Ih Ii Ij Ik Il Im In Io Ip Iq Ir It Iu Iv Jm Jn Jo Jp Js Jt Li Lj Lu Lv Lw Lx Ly Lz Mb Mc Md Mf Mg Mh Mi Mj Mk Ml Mq Mr Ms Mv Mx My Mz Na Nb Nc Nd Ne Nf Ng Nh Ni Nk Nl Nq Nr Ns Nu Nv Nx Ny Oe Of Og Oh Oi Oy Oz Pa Pc Pd Pe Pf Pg Po Pz Qa Qb Qc Qd Qe) Mr(Fp Hq Hr Hu Hv Hw Hx Ih Ii Ij Il Im In Io Iq Ir It Iu Iv Jm Jn Jo Jp Js Jt Li Lj Lu Lv Lx Ly Lz Mb Mc Md Me Mf Mg Mh Mi Mj Mk Ml Mn Mq Ms Mv Mx My Mz Na Nb Nd Ne Nf Ng Nh Ni Nj Nk Nl Nq Nr Ns Nt Nu Nv Nx Ny Oe Of Og Oi Oy Oz Pa Pc Pd Pe Pf Pg Po Pz Qa Qb Qc Qd Qe) Nt(Et Fp Hq Hr Hu Hv Hw Hx Ih Ij Ik Il Im In Io Ir It Iu Iv Jm Jo Jp Jt Li Lj Lu Lv Lw Lx Ly Lz Ma Mb Mc Md Me Mf Mg Mh Mi Mj Mk Ml Mm Mq Ms Mv Mx My Na Nb Nc Nd Ne Ng Nh Ni Nk Nl Nm Nq Nr Ns Nu Nv Nx Oe Of Og Oh Oi Oy Oz Pa Pb Pc Pd Pe Pg Po Pz Qa Qb Qc Qd Qe) Mu(Fp Fr Hq Hr Hu Hv Hx Ih Ij Ik Im In Io Ip It Iu Jg Jh Jm Jo Jp Jq Js Jt Li Lj Lu Lv Lw Ly Lz Ma Mb Mc Md Me Mf Mg Mh Mi Mj Mk Ml Mm Mn Mq Ms Mt Mv Mx My Mz Na Nb Ne Nf Ng Nh Ni Nk Nl Nm Nn Nq Ns Nu Nv Nw Nx Ny Oe Of Oh Oi Oy Oz Pb Pc Pd Pf Pg Pz Qa Qc Qd Qe) Fr(Et Fp Hq Hr Hu Hv Hx Ih Ii Ij Ik In Io Ip Iq It Iu Jg Jh Jm Jo Js Jt Lj Lu Lv Lw Ly Lz Ma Mb Md Me Mf Mg Mh Mm Mn Mp Mq Ms Mt Mx My Mz Na Nb Nc Ne Nf Nh Ni Nj Nk Nl Nm Nn Nq Nr Nu Nv Nw Nx Ny Of Og Oh Oi Oy Oz Pa Pb Pc Pd Pf Pg Po Pz Qa Qb Qc Qd Qe) Jh(Et Fp Hq Hr Hu Hv Hx Ih Ii Ik Il Im Ip Ir It Iu Iv Jg Jm Jn Jo Jq Js Li Lj Lu Lv Lw Ly Lz Ma Mb Md Mg Mh Mi Mk Mn Mp Ms Mt Mx My Mz Na Nb Ne Nf Nh Ni Nj Nk Nl Nn Nq Nr Nu Nv Nw Nx Ny Oe Og Oh Oi Ok Oy Oz Pa Pb Pd Pf Pg Po Pz Qa Qb Qe) On(Et Fp Hq Hr Hx Ih Ii Ij Il In Ip Iq Ir Is It Iu Jg Jm Jo Jp Js Jt Li Lj Lu Lv Ly Lz Mb Mc Md Me Mf Mh Mi Mk Ml Mm Mn Mq Ms Mt Mv Mx Na Nb Ng Nh Ni Nk Nl Nm Nq Nr Ns Nu Nv Nw Nx Ny Of Ok Oz Pd Pf Pg Po Qa Qb Qe) Lx(Hq Hr Hu Hv Hw Hx Ih Ij Ik Il Im In Ip Iq It Jg Jo Jp Js Jt Li Lj Lw Ma Mb Me Mg Ml Mm Mn Mp Mq Mt Mv Mx Mz Na Nc Ne Nf Ng Nh Ni Nj Nl Nr Nu Nv Nw Nx Ny Of Og Oh Oy Pb Pd Pe Pf Pg Po Qa) Nn(Et Hq Hr Hu Hv Hw Hx Ii Ij Il Im In Io Ip Ir Is It Iv Jn Jo Jq Jr Js Lu Lw Ly Ma Mb Md Me Mf Mg Mm Mp Ms Mt Mz Na Nb Nc Ne Nf Nj Nl Nr Nv Nw Nx Ny Of Oh Oi Ok Pa Pc Pg Po Pz Qa) Ok(Hq Hr Hu Hw Ii Ik Il Im Io Ip Iq Is Jg Jm Jq Jr Lu Lw Ma Mb Md Mg Mn Mp Mq Mt Mz Nc Ne Nf Nj Nk Nl Nq Nv Nw Ny Og Oh Oi Pa Pb Pc Pe Pf Pg Po Pz) Is(Et Hq Hw Ii Ik Io Iq Jg Jo Jq Lu Lw Ma Md Mm Mn Mp Ms Mt Mz Nc Nf Nm Nv Nw Ny Of Og Oi Pa Pe Pf Pg Po) Po(Et Hx Im Ip Jg Jq Jr Lw Mh Ml Mm Mp Mt Mv My Nc Nd Nl Nm Ny Of Og Oh Pb) Pe(Et Ih Ii Im Ip Jg Jq Jr Lw Ma Mm Mn Mp Mt Nc Nd Nm Nv Nw Oh Pb) Nd(Et Ij Il Ir Iv Jg Jn Jr Mp Mt Mz Nm Nr Nv Nw Ny Oh Pf Pg) Ii(Et Io Iq Jg Jn Jr Mp Mt My Nc Of Og Oy Pa Pb Pf) Mt(Hw Il Im Ir Iv Jo Jq Mb Nc Nr Oi Pa) Mp(Hw Il Ir Iv Jn Jq Jr Mz Nf Pa) Il(Et Iq Jg Jq Jr Pf) Nw(Hw Ir Iv Jo Mb Na) Im(Iq Jq Nv Pf Pg) Et(Hw Jq Nc Nf) Jg(Hw Ir Jq Jr) Hw(Jq Ny) Ik(Iv Pf) Pa(Jn Lw) NcNy JqPf JrOf} On{Oi(Et Fp Fr Hq Hv Hw Hx Ih Ii Ij Il Im In Io Ip Iq Ir Is It Iu Iv Jg Jh Jk Jl Jm Jn Jo Jp Jq Jr Js Jt Lh Li Lu Lw Lx Ly Lz Ma Mb Mc Md Me Mf Mh Mi Mj Mk Ml Mm Mn Mp Mq Mr Ms Mt Mu Mv Mw Mx Mz Na Nb Nc Nd Ne Nf Nh Ni Nj Nk Nl Nm Nn Nq Nr Ns Nt Nu Nv Nw Nx Ny Oe Og Oh Ok Om Oz Pa Pc Pd Pe Pf Pg Po Pz Qa Qb Qc Qd Qe) My(Et Fp Hq Hr Hu Hv Hw Hx Ih Ii Ij Il In Ip Iq Ir Is It Iu Iv Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mv Mx Na Nb Nc Nd Ne Nf Ng Nh Ni Nj Nk Nl Nm Nn Nr Ns Nt Nu Nv Nw Nx Ny Oe Of Og Oh Ok Oy Oz Pa Pb Pc Pd Pe Pf Pg Po Qa Qb Qd Qe) Oy(Et Fp Fr Hq Hr Hu Hv Hw Hx Ih Ij Ik Il In Ip Iq Ir Is It Iu Iv Jk Jl Jm Jn Jo Jp Jq Jr Js Jt Lh Li Lj Lu Lv Lw Lx Ly Lz Ma Mb Mc Md Me Mf Mg Mh Mi Mk Ml Mm Mn Mp Mq Mr Ms Mt Mv Mx Mz Na Nb Nc Nd Ne Nf Ng Nh Ni Nj Nk Nl Nm Nn Nq Nr Ns Nt Nu Nv Nw Nx Ny Oe Of Og Ok Oz Pa Pb Pc Pd Pe Pf Pg Po Qa Qb Qe) Pz(Et Fp Fr Hq Hv Hw Hx Ih Ii Ij Il Im In Io Ip It Iu Iv Jg Jh Jk Jl Jm Jn Jo Jp Jq Jr Js Jt Lh Li Lu Lv Lw Lx Ly Lz Ma Mb Mc Md Me Mf Mh Mi Mj Mk Ml Mm Mn Mp Mq Mr Ms Mt Mu Mv Mw Mx Mz Na Nb Nc Nd Ne Nf Nh Ni Nj Nk Nl Nm Nq Nr Ns Nt Nu Nw Nx Ny Oe Of Oh Om Oz Pa Pc Pd Pe Pf

Hv Hw Hx Ih Ik Il Im Ip Iq Ir Iu Iv Jg Jh Jk Jn Jp Jr Lu Lz Mb Mg Mh Mi Mj Mk Mm Mn Mu Mx Mz Na Nb Nc Ne Nf Ng Nl Nn Nq Nr Nv Nw Ny Oi Oz Pb Pf Pg Qa Qb Qe) Of(Et Fp Fr Hq Hw Hx Ih Ii Ik Im Iq Ir Iu Iv Jn Jr Lu Lz Mb Mh Mi Mp Mt Mu Mw Mx Mz Nb Nc Nf Nl Nn Nr Nv Nw Ny Oh Pf Pg Qb) Ik(Fp Hq Ih Ii Im Iu Jh Jn Jo Jr Li Lj Lu Lx Mh Mi Mj Mm Mx My Na Nc Nd Ne Ng Nh Nl Nn Nu Nw Oh Pb Qa Qb Qd Qe) Pb(Fp Fr Ii Im Ip Iq Ir Iu Iv Jn Jr Lx Lz Mh Mi Mp Mt Mu Mw Na Nb Nd Ne Nn Nw Oh Oz Pf Po Qa) My(Et Hw Ii Im Iq Ir Iv Jg Jl Jn Jr Lu Mh Mi Mp Mt Mu Mw Mz Nb Nd Nf Nn Nv Ny Oh Pc Po) Ng(Et Fr Im Iq Ir Iu Jg Jk Jl Jr Mm Mp Mr Mt Mu Mw Nn Nw Oh Pe Pf Po) Jl(Et Hr Hu Hx Ij Im Iq Jo Lx Mg Mh Ml Mp Ms Mv Nc Ny Oe Oh Oi Pz) Mg(Et Fr Im Iq Ir Iu Mm Mr Mt Mu Nd Nn Oh Pa Pe Pf) Oh(Im Lx Mr Ms Mv Nc Nt Oi Pc Pz) Et(Hu Iq Jh Lj Lx Ms Nc Nd Pz) Nt(Hu Il Iq Jn Jo Jr Lj) Lx(Hq Ir Jm Lj Mv Pg) Iq(Il Im Mp Oi Pz Qc) Hu(Fr Im Lh Mr Nn) Ir(Ij Im Mp Oi Pz) Mv(Lh Mt Nn Nw) Mr(Hx Jo) Ij(Hw Lh) Im(Jr Nc) Pa(Il Mk) NnOi MeIv MpMs NdHq JoLh} Ik{Pe(Fp Hr Hw Hx Il Im In Io Ip Ir Iv Jn Jo Jp Jr Li Lv Md Mf Mi Mj Mk Ml Mn Mr Mv Mz Nc Ne Nh Nl Nm Nq Nt Nv Nx Ny Of Og Oh Oi Oz Pa Pb Pg Po Pz Qa Qb) Jh(Et Fp Hx Ih Ii Il Ip Iu Jn Jo Js Li Lj Lu Lx Mp Mt Mu Mw Mz Na Nd Ne Nf Nk Nl Nn Nu Nv Nw Ny Og Oh Pg Qb Qd Qe) Jl(Et Fp Fr Im Io Ir Iv Jn Jr Js Lh Li Lw Lx Md Mp Mz Nb Nf Nm Nn Nt Nw Ny Og Oi Pf Po) Mu(Et Iq Jn Jr Lx Lz Mi Mk Mp Mt Mw Mz Nb Nj Nr Nt Nw Ny Oz Pf Po Qb) Mr(Et Im Ip Jk Jn Jr Li Me Mm Nj Nm Ny Oh Pb Pf Pg Po Qd) Mw(Et Js Lh Lj Mg Mk Mt Mx Nb Ne Ng Nr Nt Nw Oz Po Qd) Iv(Et Ip Jk Me Mm Mp Nj Nm Ny Oh Pf Pg Po) Nw(Hw Ir Jo Lh Mk Na Nb Nr Nt Pa Pf Po) Lx(Et Hq Mh Mk My Ng Nt Ny Oz Pa Pb) Mt(Ir Lh Mk Nb Nr Nt Oz Pa Po) Pf(Et Ii Ir Lh Nb Nt Ny Po) Fr(Hv Jn Lh Mz Nb Nt Po) Po(Et Jg Lw Mp Nn) Ir(Im Jg Ma Mp Nn) Lh(Jg Jo Nn) Pa(Mz Nn Ny) Nt(Jr Mz) MkNy} Jh{Jl(Et Hr Hw Hx Ih Ii Ij Il Im Io Ip Iq Ir Jk Jm Jn Jo Jr Lh Lj Lw Lx Ma Mb Mh Mj Mk Mp Mq Ms Mt Mv Mw Mz Na Nc Nd Ne Nf Nj Nl Nq Nr Ns Nt Nu Nv Nw Nx Ny Oe Of Oh Oi Oz) Ng(Et Fr Hw Ii Iq Ir Jr Lz Mh Mp Mt Mu Mz Nc Nf Nw Oh Pf) Oy(Et Fr Ii Iq Ir Jr Lz Mt Mz Nb Nc Nd Nf Nt Nw Ny Oh Pf) Og(Et Hw Hx Iq Ir Iv Jr Lx Lz Mt Mz Nb Nc Nr Nt Oh Po) Mg(Et Fr Ir Iv Jr Lz Mh Mi Mp Nd Nt Oh Pa Pf Po) Hu(Fr Iq Jr Lu Lz Mh Mp Mt Nd Nn Nw Oh Pe Pf Po) Jr(Fr Im Lh Lx Mp Mr My Nc Nd Nt Pz) My(Fr Ii Iq Mz Nb Nf Nt Oh Pe) Ir(Fr Jt Lx Mp Nd Oi Pb Pz) Lx(Hq Jm Lj Ly Mv Of) Iq(Im Mp Mv Nt Oi Pz) Mz(Ml Mp Nt Of Pb) Oh(Mr Oi Pc Pe Pz) Of(Mh Mr Pe Po) Lj(Lh Nd Nt) Pb(Hw Nr Po) Mr(Jo Lw) Jn(Mp Nt) Nw(Mv Nc) Pa(Il Mk) MhMs JoLh} Mu{Et(Hr Hu Hw Ih Iq Ir Iv Jl Jn Jr Js Lh Lj Lx Mg Mh Mp Mr My Mz Nc Nd Nf Ng Nj Nk Ns Nt Nw Og Oh Oi Oy Pa Pb Pe Pz) Jr(Fr Hr Im Iq Ir Iv Jl Lh Lx Me Mp Mr Mw Nc Nd Nj Ns Nt Og Oh Oi Pa Pb Pe Qc) Ir(Fr Hr Im Jl Jo Jt Lx Mg Mp Mt Mw Nd Ng Nj Nt Nw Og Oi Oy Pz) Ng(Fr Iq Iv Jg Jl Lh Lx Mp Mr Mt Mw Mz Nd Nt Nw Pe Po) Jl(Hu Im Iq Jn Mg My Mz Nf Og Oi Oy Pb Pz) Nw(Hw Iv Mb Mv My Na Nc Nt Og Oi Oy Pb) Oy(Ii Lh Mp Mr Mw Nb Pa Pe Po) Mg(Iq Iv Lh Mp Mr Nm Nt Pe) Pb(Hw Iv Lh Mr Mz Nr Po) Og(Iv Lh Mr Mz Nb Pe) Oi(Ih Iq Lj Oh) Mp(Iv Jn Mz) Mr(Hu Lw Ly) Lh(Hu Jo My) Nt(Jn Mz) Iq(Nj Pz) Iv(Me Oh) LxLy MzOf JnPa OhPc} Fr{Jr(Et Hr Hu Hw Il Im Ir Iv Jl Jn Lw Ma Mb Mg Mp Mr Mv My Na Nc Ng Nj Nt Nu Og Oi Oy Pb Pz Qc) Ir(Hr Im Io Jt Lw Lx Mg Mj Mp Ms Mt Mv Mw My Nc Nd Ng Nj Nu Nw Of Og Oi Oy Pb Pz) Ng(Hv Hw Ii Im Iv Jn Jo Lh Lx Mb Mr Mw Na Nf Nm Nt Pe Po Qa) Mg(Et Hv Hw In Jn Jo Js Lh Mb Mp Mr Mz Na Nt Pe Qa) My(Hv Hw Ii Iv Jn Js Lh Mr Mw Mz Na Nb Nw Ny Pe) Jn(Im Jl Lx Mp Nc Nt Nw Oi Pb Pz) Pb(Hv Hw Iv Lh Mr Mz Na Pe) Oy(Ii Lh Mr Mw Nb Pe Po) Mz(Im Mp Nt Oi Pz) Iv(Im Jo Nw Og Pz) Na(Im Jo Nc Nw) Mr(Hu Lw) Pz(Et Jl) LxJm ImJs JoLh LjOi} Nw{Mb(Im Lx Mv My Nc Nd Ne Nj Nl Nt Ny Of Og Oi Oy Pb Pf) Hw(Et Hr Ij Im Ml Mp My Nc Nd Nn Nt Of Og Oi Oy) Ir(Hr Ij Im Lx Mp Nc Nd Nn Nt Og Oi Pb Pz Qc) Nt(Et Io Jm Jn Jr My Na Ng Nv Og Oi Pg) Im(Et Hv Iv Jl Jn Jo Jr Lw Na Nr Pe Qa) Oi(Et Jl Jo Lh Mp Mr Na Nn Nr Oh Pe) Na(Hr Ij Lx Mp Nc Nd Nn Og Pb) Lh(Hx Mh My Ng Og Oy Pb) Og(Ii Jg Mr Mw Nb Pe) My(Ii Jg Jk Nn Pe) Mr(Et Lw Mh Pb) Nd(Hv Iv Jn Jr) Oy(Ii Jk Mw Pe) Pz(Et Jl Nn) Qc(Iq Jn Jr) Pb(Jo Nr Pe) Mw(Mv Ng) Iv(Mp Nn) MhPe NcNi} Jl{Im(Et Hr Io Iq Ir Jg Jn Jr Lw Md Mp Mt Mz Nf Nm Nn Og Oi Pb Pz) Mz(Et Hr Io Jo Lw Lx Mj Mp Mw Nn Og Oi Pb Pz Qc) Jn(Et Hr Io Jo Lw Lx Mp Mw Nn Og Oi Pb Pz) Pb(Hv Hw Ij In Ir Jr Mt Mw Na Pe Pz Qa) Pz(Et Hr Iq Mp Mt Mw Nm Oh Pf) Oi(Et Hr Iq Jg Mp Mt Mw Nf Oh) Nn(Io Jr Mg My Ng Og Oy Pc) Io(Et Hr Lw Mp Mt Nc Oh) Mg(Et Jg Lh Mp Mw Nm) Nf(Et Hr Jo Lw Mj Og) Jr(Hr Lw Lx Mp Mw Og) Mw(My Ng Og Oy) Jg(My Ng Oy) Jo(Ir Lh Nm) Et(Hr Og) Mt(Hr Oy) Lwlq LxLy IrOg} Mw{My(Et Ir Jn Jr Lh Lx Mr Mt Mz Nb Nf Oh Pa Pe Po) Oy(Et Ii Iq Ir Jn Jr Lh Mr Mz Nb Nf Ny Pa Pe Pf) Ng(Et Iq Ir Jn Jr Lh Mt Mz Nd Nf Nt Pa Pe Pf) Mg(Et Iq Ir Jr Lh Lx Mr Nm Nt Oh Pe Pf) Og(Et Hu Iq Ir Jn Lh Mr Mt Nb Nf Pe) Mz(Et Hu Ml Mv Nt Ny Of Oi Pb) Hu(Im Iq Jn Jr Lx Mr Mx Oi) Jr(Et Im Mv Nt Of Pb Pz) Ir(Ij Im Jo Jt Pb Pz) Pb(Hw Jn Lh Mr Pe) Iq(Et Mv Oi Pz) Et(Jn Pz) Lx(Jm Ly) NtJn MtMv} Nn{Oi(Et Hw Ih Ir Iv Jn Jr Lh Lj Mr Mt Mz Nb Nc Nr Nt Pa Pe) Mr(Et Hu In Jo Jr Lw Mg My Ng Og Oy Pb Pz) Pe(Et Jo My Ng Nu Og Oy Pb Pz) Mg(Et Ii Ir Iv Lh Mz) Ir(Im Jo Lx Pz) Lh(Jo My Ng Oy) Iv(Jo Og Pz) Nb(Og Oy) Ii(My Ng) Pz(Et Jr) PoOy} Lx{Ly(Et Hq Hr Hv Hw Ii Ij In Ir Iv Jm Jn Jo Jr Lh Lw Ma Mb Mg Mp Mt Mv My Mz Na Nb Nc Ne Ng Nj Nm Nq Nr Nt Og Oz Pa Pg Qa) Et(Ir Jn Jr Mg Mz Ng) Jg(Jm My Og Oy) Ir(Jo Mp Pb) NmMg NbOy HwPb} Jg{Og(Ir Jr Lh Mr Mt Mz Nb Ny Pa Pe Po) My(Jr Lh Mr Mt Mz Po) Ng(Mp Mr Mt Pa Pe Po) Oy(Lh Mr Mt Pe Po) Mg(Lh Mp Mr Pe) Oi(Iq Oh) IrPz PbPe} Et{Pz(Iq Ir Mr Mt Mz Nc Pf Po) Mg(Lh Mr Nt Pe Po) Mr(Io Jo Lw Pb) Mz(Im Mp Nt Oi) Po(Oy Pb) Lh(Jo Ng) NtJn MtHr NcIo OhOi PbPe} Mp{Ir(Hw Im In Io Jo Jt Mg Mj Mq Oi Pb Pz) Mr(Jn Jr Mg Mz Pb) Nt(Jn Jr Mz) Mg(Lh Pe) Mz(Im Oi) Pa(Jn Jr) NgLh PbPe} Lw{Mr(Im Iq Jn Jo Jr Mg Mt Mz Og Oy Pb) Im(Iq Ir Mz) Lh(Jo Mg) Pa(Jn Jr) PoOy NtMz PbPe} Pb{Mt(Hw Ir Iv Lh Mr Nr Pe) Pe(Il Im Mz Oh) Po(Hw Na) Mz(Mr Pa)} Mg{Lh(Ma Mm Mt Nm Pf) Ma(Iv Mr Pe) Mm(Mr Pe) NmMr} Mt{Ir(Hr Im Oi) Oi(Hr Mr) IiOy} Oh{Mj(Mr Pe) Oi(Mr Pe) IiOy} Lh{Jr(Hr Mj) NmJo MaNg} PoMjOy Unconstrained panels with 3 analytes, where 6.5E-7 >= 'model p-value' > 1.0E-7. Contains 32,861 panels of 287,980 total panels evaluated. : Ji{Il(Et Fp Hq Hr Hu Hv Hw Hx Ih Ii Ij Im In Ip Iq Ir Is It Iu Iv Jg Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Ms Mt Mv Mw Mx My Mz Na Nb Nc Ne Nf Ng Nh Ni Nj Nk Nl Nm Nn Nq Nr Ns Nu Nv Nw Ny Of Og Oh Oi Om On Oy Oz Pb Pc Pd Pf Pg Po Pz Qa Qb Qc Qd Qe) Nk(Et Fp Hq Hr Hu Hv Hw Hx Ih Ii Ij Ik In Ip Iq Ir Is It Iu Iv Jg Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Ms Mt Mv Mx My Mz Na Nb Nc Ne Nf Ng Nh Ni Nj Nl Nm Nq Nr Ns Nu Nv Nw Ny Oe Of Og Oh Om On Oy Oz Pb Pc Pd Pe Pf Pg Po Pz Qa Qb Qc Qd Qe) Hq(Et Fp Hr Hu Hv Hw Hx Ih Ii Ij In Ip Iq Ir Is It Iu Iv Jg Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Ms Mt Mv Mw Mx My Mz Na Nb Nc Ne Nf Ng Nh Ni Nj Nl Nm Nq Nr Ns Nu Nv Nw Ny Oe Of Og Oh Oi Om On Oy Oz Pb Pc Pd Pe Pf Pg Po Qa Qb Qc Qd Qe) Pg(Et Fp Hr Hu Hv Hw Hx Ih Ii Ij Ik In Ip Iq Ir Is It Iu Iv Jg Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Ms Mt Mv Mw Mx My Mz Na Nb Nc Ne Nf Ng Nh Ni Nj Nl Nm Nq Nr Ns Nu Nv Nw Ny Of Og Oh Oi Om On Oy Oz Pb Pc Pd Pf Po Pz Qa Qb Qc Qd Qe) Nq(Et Fp Hr Hu Hv Hw Hx Ih Ii Ij Ik Im In Ip Iq Ir Is It Iu Iv Jg Jk Jm Jn Jo Jp Jq Jr Js Jt Lh Li Lj Lu Lv Lw Ly Lz Ma Mb Mc Md Me Mf Mh Mi Mj Mk Ml Mm Mn Mp Mq Ms Mt Mv Mx My Mz Na Nb Nc Ne Nf Ng Nh Ni Nj Nl Nm Nr Ns Nu Nv Nw Ny Of Og Oh Om On Oy Oz Pb Pc Pd Pe Pf Po Pz Qa Qb Qc Qd Qe) Ly(Fp Hr Hu Hv Hw Hx Ih Ii Ij Ik Im In Ip Iq Ir Is It Iu Iv Jg Jk Jm Jn Jo Jp Jq Jr Js Lh Li Lj Lu Lv Lw Lz Ma Mb Mc Md Me Mf Mg Mh Mi Mj Mk Ml Mm Mn Mp Mq Ms Mt Mv Mw Mx My Mz Na Nb Nc Ne Nf Ng Nh Ni Nj Nl Nm Nr Ns Nu Nv Nw Ny Of Og Oh Oi Om On Oy Oz Pb Pc Pd Pf Po Pz Qa Qb Qc Qd Qe) Lz(Et Fp Hr Hu Hv Hw Hx Ih Ii Ij In Ip Iq Ir Is It Iu Iv Jg Jk Jm Jn Jo Jp Jq Jr Js Jt Lh Li Lj Lu Lv Lw Ma Mc Md Me Mf Mg Mh Mi Mj

Figure 43 Continued

Qa Qb Qd Qe) Hr(Et Fp Fr Hq Hv Hx Ih Ii Ij Il In Ip It Iu Iv Jg Jh Jk Jm Jo Jp Js Jt Lh Li Lu Lv Lx Ly Lz Ma Mb Mc Md Me Mf Mh Mi Mj Mk Ml Mm Mn Mp Mq Mt Mw Mx Na Nb Nd Ne Nf Nh Ni Nj Nk Nl Nm Nn Nq Nr Nt Nu Nv Nw Nx Ny Of Oh Om Oz Pa Pb Pd Pe Pf Pg Po Qa Qb Qc Qd Qe) Hu(Et Fp Fr Hq Hv Hw Hx Ih Ii Ij Il In Ip Ir It Iu Iv Jg Jk Jm Jn Jo Jp Jr Js Jt Lh Li Lu Lv Ly Lz Ma Mb Mc Md Me Mf Mh Mi Mk Ml Mm Mn Mp Mq Mt Mx Na Nb Nd Ne Nf Ng Nh Ni Nj Nk Nl Nm Nn Nq Nr Nt Nu Nv Nw Nx Ny Of Ok Oz Pa Pb Pd Pe Pf Pg Po Qa Qb Qd Qe) Ir(Et Fp Fr Hq Hv Hw Hx Ih Ii Il Ip It Iu Iv Jg Jh Jk Jm Jn Jp Jq Jr Js Lh Li Lu Lv Ly Lz Ma Mb Mc Md Me Mf Mh Mi Mk Ml Mm Mn Mp Mr Mt Mw Mx Na Nb Nd Ne Nf Nh Ni Nj Nk Nl Nm Nn Nq Nr Nt Nu Nv Nw Ny Oh Ok Om Oz Pa Pc Pd Pe Pf Pg Po Qa Qb Qc Qd Qe) Jn(Et Fp Fr Hq Hv Hw Hx Ih Ii Il Ip It Iu Iv Jg Jh Jk Jm Jp Jq Jr Js Lh Li Lu Lv Ly Lz Ma Mb Mc Md Me Mf Mh Mi Mk Ml Mm Mn Mp Mq Mr Mt Mw Mx Na Nb Nd Ne Nf Nh Ni Nj Nk Nl Nm Nn Nq Nr Nt Nu Nv Nw Ny Oh Ok Om Oz Pa Pc Pd Pe Pf Pg Po Qa Qb Qd Qe) Jr(Et Fp Fr Hq Hv Hw Hx Ih Ii Il Ip It Iu Iv Jg Jh Jk Jm Jp Js Lh Li Lu Lv Ly Lz Ma Mb Mc Md Me Mf Mh Mi Mk Ml Mm Mn Mp Mq Mr Mt Mw Mx Na Nb Nd Ne Nf Nh Ni Nj Nk Nl Nm Nn Nq Nr Nt Nu Nv Nw Nx Ny Oh Ok Om Oz Pa Pc Pd Pe Pf Pg Po Qa Qb Qd Qe) Of(Et Fp Fr Hq Hx Ih Ii Il Ip It Iu Iv Jg Jk Jm Jo Jp Js Jt Lh Li Lu Lv Lx Ly Lz Ma Mb Mc Md Me Mf Mg Mh Mi Mj Mk Ml Mm Mn Mp Mq Mt Mw Mx Nb Nd Ne Ng Nh Ni Nj Nk Nl Nm Nn Nq Nr Nt Nu Nv Nw Nx Ny Oz Pa Pb Pc Pd Pf Pg Po Qa Qb Qc Qd Qe) Ok(Et Fp Fr Hq Hv Hw Hx Ih Ii Il In Ip It Iu Iv Jg Jh Jk Jm Jp Js Lh Li Lu Lv Ly Lz Ma Mb Mc Md Me Mf Mh Mi Mk Ml Mm Mn Mp Mr Mt Mw Mx Na Nb Ne Nf Nh Ni Nj Nk Nl Nm Nn Nq Nr Nt Nv Nw Ny Oh Om Oz Pa Pc Pd Pe Pf Pg Po Qa Qb Qd Qe) Io(Fp Fr Hq Hv Hw Hx Ih Ii Ij Il In It Iu Jg Jk Jm Jo Jp Js Jt Lh Li Lu Lv Lx Ly Lz Ma Mb Mc Md Mf Mh Mi Mj Mk Ml Mm Mn Mq Mt Mx Nb Ne Nf Nh Ni Nj Nk Nl Nm Nn Nq Nr Nu Nv Nw Nx Ny Oh Om Oz Pa Pc Pd Pe Pf Pg Po Qa Qb Qc Qd Qe) Mr(Et Fr Hq Hv Hw Hx Ih Ii Ij Il In Ip It Iu Iv Jg Jh Jk Jm Js Jt Lh Lu Lv Lx Ly Ma Mb Mc Md Me Mh Mi Mj Mk Ml Mm Mn Mp Mq Mt Mw Mx Na Nb Nd Ne Nf Nh Ni Nj Nk Nl Nm Nn Nq Nr Nt Nu Nv Nw Nx Ny Oh Om Oz Pa Pc Pf Pg Po Qa Qc) Hw(Et Fr Hq Hv Hx Ih Ii Il In Ip It Iv Jg Jh Jk Jm Jp Jq Js Lh Lv Lx Ly Lz Ma Mb Mc Md Me Mf Mh Mj Mk Ml Mm Mn Mp Mt Mw Mx Na Nb Nd Ne Nf Nh Ni Nj Nk Nl Nm Nn Nq Nr Nt Nu Nv Nw Oh Om Pa Pc Pd Pe Pf Pg Qa Qc) Jo(Et Fp Fr Hq Hx Ii Ij Il Ip It Iu Jg Jh Jk Jm Jp Js Jt Li Lu Lv Lx Ly Lz Ma Mb Mc Md Me Mf Mh Mi Mj Mk Ml Mm Mn Mp Mq Mt Mw Mx Nb Nd Ne Nf Nh Nj Nk Nl Nm Nn Nq Nu Nv Nw Nx Ny Oh Om Oz Pa Pb Pc Pd Pf Pg Po Qb Qc) Et(Fp Fr Hq Hv Hx Ih Ii Ij In Ip It Iv Jh Jm Js Jt Lh Lu Lv Lx Lz Ma Mb Md Me Mh Mj Mk Mn Mp Mq Mt Mw Mx Na Nb Nd Ne Nf Nh Ni Nj Nk Nl Nn Nq Nr Nt Nu Nv Nw Nx Ny Oh Om Pa Pb Pc Pe Pf Po Qa Qc) Iv(Fr Hq Hv Hx Ii Ij Il In Ip It Jh Jk Jm Jq Js Lh Lv Lx Lz Ma Mb Md Me Mh Mj Mk Ml Mm Mn Mp Mq Mt Mw Mx Na Nb Nd Ne Nf Nh Ni Nj Nk Nl Nn Nq Nr Nt Nu Nv Nw Nx Ny Oh Om Pa Pc Pe Pf Pg Qc Qe) Pe(Fr Hq Hv Hx Ii Ij Il In Ip Jh Jk Jm Js Jt Lh Lv Lx Ly Ma Mb Md Me Mh Mj Mk Ml Mm Mn Mp Mq Mt Mw Mx Na Nb Nd Ne Nf Nh Ni Nj Nl Nn Nq Nr Nt Nu Nv Nw Nx Ny Oh Om Oz Pc Pf Pg Po Qa Qc) Pb(Fp Fr Hq Hx Ih Ii Il Ip It Iu Jg Jk Jm Jp Jt Li Lu Lv Lx Ly Lz Ma Mc Md Me Mf Mh Mi Mj Mk Ml Mm Mn Mq Mw Mx Nb Nd Ne Nh Nj Nk Nl Nm Nn Nq Nt Nv Nw Nx Ny Oz Pa Pd Pg Po Qb Qd Qe) Nu(Fp Fr Hv Hx Ij Il In Ip It Jh Jm Jq Js Lh Lv Lx Ly Ma Mb Mc Me Mg Mh Mi Mj Mk Mm Mp Mq Mt Mw Mx Na Nb Nd Ne Nf Nh Ni Nj Nk Nl Nm Nn Nq Nr Nt Nv Nx Ny Oh Om Pa Pc Pf Pg Qa Qc) Hv(Fr Hq Hx Ih Ii Il In Ip Jh Jk Jm Jq Js Jt Lh Lv Lx Lz Ma Md Me Mf Mh Mj Mk Ml Mm Mn Mp Mq Mt Mw Mx Na Nb Nd Ne Nf Nh Nj Nk Nl Nm Nn Nq Nr Nt Nv Nw Ny Oh Om Pa Pc Pf Pg Qc) Lx(Fr Hq Hx Ih Ii Ij Il In Ip It Jh Jk Js Jt Lh Lu Lv Ma Mb Md Me Mh Mi Mj Mk Ml Mn Mp Mq Mt Mw Mx Na Nb Nd Ne Nf Nh Ni Nj Nl Nm Nn Nr Nw Nx Ny Oh Om Pc Pf Pg Po Qa Qc) Na(Fr Hq Hx Ih Ii Il In Ip It Jh Jk Jm Jq Js Lh Lv Lz Ma Mc Md Me Mf Mh Mj Mk Ml Mm Mp Mt Mw Mx Nb Nd Ne Nf Nh Nj Nk Nl Nm Nn Nq Nr Nt Nv Nw Ny Oh Om Pa Pc Pf Pg Qc) Nt(Fr Hq Hx Ii Ij Il Im In Ip Iu Jh Jk Js Jt Lh Lv Ly Ma Mb Mc Mh Mi Mj Mk Ml Mp Mq Mt Mw Mx Nb Nd Ne Nf Nh Ni Nj Nk Nl Nn Nq Nr Nw Nx Ny Oh Om Pc Pf Pg Qa Qc) Mp(Fr Hq Hx Ii Ij Il In Ip It Jh Jm Js Jt Lh Lv Ma Mb Me Mh Mi Mj Mk Mm Mn Mq Mt Mw Mx Nb Nd Ne Nf Nh Ni Nj Nl Nn Nq Nr Nv Nw Nx Ny Oh Om Pa Pc Pf Pg Qa Qc) Lh(Fr Hx Ii Ij Il Im In Ip Jh Jk Jm Js Jt Lv Ly Ma Mb Md Me Mh Mi Mj Mk Ml Mq Mt Mw Mx Nb Nd Ne Nf Nh Ni Nj Nl Nn Nq Nr Nv Nw Nx Ny Oh Om Pc Pf Pg Qa Qc) Mg(Fp Hq Hx Ih Ii Ij Il Ip It Iu Jk Jm Jp Js Jt Li Lu Lv Ly Lz Mc Md Mf Mh Mj Ml Mn Mq Mt Mw Mx Nb Nd Ne Nf Nh Ni Nj Nl Nm Nn Nq Nr Nv Nw Ny Oh Om Pa Pc Pd Pg Po Qb Qd Qe) In(Fp Fr Hx Ih Ii Il Ip It Jh Jm Js Jt Li Lv Ma Mb Md Me Mh Mi Mj Ml Mq Mt Mw Nb Nd Ne Nf Nh Ni Nj Nk Nl Nm Nn Nq Nr Nv Nw Ny Oh Om Pa Pc Pf Qa Qc) Nf(Fr Hx Ii Ij Il Ip Jh Jm Js Jt Lv Ma Mb Md Me Mh Mj Mk Ml Mm Mq Mt Mw Nb Nd Ne Nh Ni Nj Nk Nl Nn Nq Nr Nv Nw Nx Ny Oh Pa Pc Pf Pg Qc) Js(Fr Hx Ii Ij Il Ip Jh Jm Jq Jt Lv Ma Mb Md Me Mh Mj Mk Ml Mm Mq Mt Mw Nb Nd Ne Ng Ni Nj Nl Nn Nq Nr Nv Nw Nx Ny Oh Om Pa Pc Pf Qc) Jq(Fp Hq Hx Ih Il It Iu Jg Jh Jk Jm Jp Li Lu Ly Lz Mc Mf Mi Mk Mn Mt Mw Mx Nh Ni Nk Nl Nm Nq Nr Nw Oz Pd Pg Po Qa Qb Qd Qe) Nv(Fr Ij Ip It Iu Jh Jm Lv Ma Mb Md Me Mh Mj Mk Mm Mn Mq Mt Mw Nb Nd Ne Nh Ni Nj Nl Nm Nn Nr Nw Nx Oh Om Pa Pc Pf Qa Qc) Nd(Hq Ii Ij Il Im Ip Jh Jk Lv Ly Ma Mb Me Mh Mj Mk Mn Mq Mt Mw Nb Ne Nh Ni Nj Nl Nn Nq Nw Nx Oh Om Pc Pf Pg Qa Qc) Ip(Fr Hq Ii Ij Jh Jm Lv Ma Mb Me Mh Mj Mq Mt Mw Nb Ne Nh Ni Nj Nk Nl Nn Nq Nr Nw Nx Ny Oh Om Pa Pc Pf Pg Qa Qc) Ng(Fp Hq Hx Ih Ij Il It Iu Jm Jp Li Lu Ly Lz Mc Mf Mh Mi Mk Ml Mn Mx Ne Nh Nk Nl Nq Nr Ny Oz Pd Pg Qa Qb Qe) Qc(Hq Ij Il Im Jh Jk Jm Lv Ma Mb Me Mh Mj Mk Mn Mq Mt Mw Mx Nb Ne Nh Ni Nj Nl Nn Nq Nw Nx Oh Om Pc Pf Pg Qa) Pf(Hq Ij Il It Jh Jm Lv Lz Ma Mb Me Mh Mj Mk Mn Mq Mt Mw Nb Ne Ni Nj Nn Nq Nr Nw Nx Oh Om Pc Pd Pg Qa) Im(Fp Hq Hx Ih Ii It Iu Jg Jk Jp Jt Li Lu Lz Mc Md Mf Mk Ml Mm Nh Nm Nx Ny Oz Pa Pd Po Qb Qd Qe) Pc(Fr Hx Ii Il Jh Jm Lv Lz Mb Me Mh Mj Ml Mm Mt Mw Mx Nb Ne Nh Ni Nj Nl Nm Nn Nw Nx Ny Oh Pg Qa) Qa(Fr Hx Ii Il Jh Jm Jt Lv Ma Md Me Mh Mj Mk Ml Mm Mq Mt Mw Nb Ne Nj Nk Nl Nn Nw Ny Oh Pa) Nx(Fr Hx Il It Jh Jm Ma Mb Me Mh Mk Mq Mt Mw Nb Ne Nh Ni Nj Nk Nl Nn Nq Nr Nw Ny Oh Om Pa) Jh(Hx Ih Ij Il Jk Jm Lv Lz Ma Mb Mh Mk Mq Mt Mw Nb Ne Ni Nj Nk Nl Nq Nr Nw Ny Oh Om Pg) Ne(Fr Hq Ii Il Jm Lv Ly Ma Mb Me Mj Mk Mq Mw Nb Ni Nj Nm Nn Nr Nw Oh Om Pg) Mw(Fr Hq Ij Jg Jm Jt Lv Ma Mb Me Mj Mk Mq Nb Ni Nj Nn Nq Nw Oh Om Pa) Ni(Fr Ii Ij Jm Jt Lv Ma Me Mh Mj Mm Mq Nb Nj Nk Nl Nn Nw Ny Oh Pa) Om(Hx Ih Ii Ij Il Jm Lv Ma Md Mh Mk Ml Mn Mq Nb Nj Nk Nl Nn Ny Oh) Nj(Fr Ii Ij Jm Lv Ma Mb Mh Mj Mk Mm Mx Nb Nl Nn Nr Nw Oh Pa) Nl(Fr Hq Ii Ij Jm Jt Lv Ma Mb Me Mj Mk Mq Nb Nn Nr Nw Oh) Og(Fp Ih Il It Iu Jk Jp Li Lu Mm Mn Mx Nh Qb Qd Qe) Jm(Fr Lv Ma Mb Me Mh Mj Mq Nb Nm Nn Nw Oh Pa) Oh(Il Lv Ma Mb Me Mh Mj Mk Mm Mq Nb Nm Nn) Nn(Ij Lv Ma Mb Me Mj Mq Nb Nq Nr Nw) Mb(Fr Jt Lv Me Mh Mq Nb Nh Nw) Ij(Fr Ii It Jt Lv Mc Mj Mq Ny) Mh(Lv Ma Mj Mk Mq Nb Nw Pa) Me(Fr Jt Lv Mf Mj Mq Nb) Fr(It Lv Ma Nb Nq) Nr(Ii Mj Mk Mq Nw) Pa(Hx Il Mk Ny Pg) Mq(Jt Nh Nm Ny) Mj(Fp Mx) Nw(Hx Ny) NmJt M

Jt Lh Li Lj Lu Lv Lx Ly Lz Ma Md Me Mf Mg Mh Mi Mj Mk Ml Mn Mq Mr Mv Mx My Na Nb Nc Nd Ne Ng Nh Ni Nk Nl Nq Nr Nt Nu Nv Nw Nx Ny Og Oi Oy Oz Pa Pb Pc Pe Pf Pg Po Pz Qa Qb Qc Qd) Mk(Fp Hq Hu Hv Hw Hx Ih Ii Ij Ik Il In Io Iq It Iu Iv Jk Jm Jo Jp Js Jt Lh Li Lj Lu Lv Lx Ly Lz Ma Md Me Mf Mg Mh Mi Mj Ml Mq Mr Mv Mx My Na Nb Nc Nd Ne Ng Nh Ni Nk Nl Nq Nr Nt Nu Nv Nw Nx Ny Og Oi Oy Oz Pa Pb Pc Pe Pf Pg Po Pz Qa Qb Qc Qd) Qc(Fp Hq Hu Hv Hw Hx Ih Ii Ij Ik Il In Io Iq It Iu Iv Jk Jm Jo Jp Js Jt Lh Li Lj Lu Lv Lx Ly Lz Ma Md Me Mf Mg Mh Mi Mj Ml Mn Mq Mr Mv Mx My Na Nb Nc Nd Ne Ng Nh Ni Nk Nl Nq Nr Nt Nu Nv Nx Ny Og Oi Oy Oz Pa Pb Pc Pe Pf Pg Po Pz Qa Qb Qd) Po(Fp Hq Hu Hv Hw Hx Ih Ii Ij Il In Io Iq It Iu Iv Jk Jm Jo Jp Js Jt Lh Li Lj Lu Lv Lx Ly Lz Ma Md Me Mf Mg Mh Mi Mj Ml Mn Mq Mr Mv Mx My Na Nb Nc Nd Ne Ng Nh Ni Nk Nl Nq Nr Nt Nu Nv Nw Nx Ny Og Oi Oy Oz Pa Pc Pe Pf Pg Pz Qa Qb Qd) Nq(Fp Hq Hu Hv Hw Hx Ih Ii Ij Ik Il In Io Iq It Iu Iv Jk Jo Jp Js Jt Lh Li Lj Lu Lv Lx Ly Lz Ma Md Me Mf Mg Mh Mi Mj Ml Mq Mr Mv Mx My Na Nb Nc Nd Ne Ng Nh Ni Nk Nl Nr Nt Nu Nv Nw Nx Ny Og Oi Oy Oz Pa Pb Pc Pe Pf Pg Pz Qa Qb Qd) Ml(Fp Hq Hu Hv Hw Hx Ih Ii Ij Ik Il In Io Iq It Iu Iv Jk Jm Jo Jp Js Jt Lh Li Lj Lu Lv Lx Ly Lz Ma Md Mf Mg Mh Mi Mj Mq Mr Mv Mx My Na Nb Nc Nd Ne Ng Nh Ni Nk Nl Nr Nt Nu Nv Nw Nx Ny Og Oi Oy Oz Pa Pb Pc Pe Pf Pg Pz Qa Qb Qd) Hq(Fp Hu Hv Hw Hx Ih Ii Ij Ik Il In Io Iq It Iu Iv Jk Jm Jo Jp Js Jt Lh Li Lj Lu Lv Lx Ly Lz Ma Md Me Mf Mg Mh Mi Mj Mq Mr Mv Mx My Na Nb Nc Ne Ng Nh Ni Nk Nl Nr Nt Nu Nv Nw Nx Ny Og Oi Oy Oz Pa Pb Pc Pe Pf Pg Pz Qa Qb Qd) Hx(Fp Hu Hv Hw Ih Ii Ij Ik In Io Iq It Iu Iv Jk Jm Jo Jp Js Jt Lh Li Lj Lu Lv Lx Ly Lz Ma Md Me Mf Mg Mh Mi Mj Mn Mq Mr Mv Mx My Na Nb Nc Nd Ne Ng Nh Ni Nk Nl Nr Nt Nu Nv Nx Ny Og Oi Oy Oz Pa Pb Pc Pe Pf Pg Pz Qa Qb Qd) Ih(Fp Hu Hv Hw Ii Ij Ik Il In Io Iq It Iu Iv Jk Jm Jo Jp Js Jt Lh Li Lj Lu Lv Lx Ly Lz Ma Md Me Mf Mg Mh Mi Mj Mn Mq Mr Mv Mx My Nb Nc Nd Ne Ng Nh Ni Nk Nl Nr Nt Nu Nv Nw Nx Ny Og Oy Oz Pa Pb Pc Pe Pf Pg Pz Qa Qb Qd) Pg(Fp Hu Hv Hw Ii Ij Ik Il In Io Iq It Iu Iv Jk Jm Jo Jp Js Jt Lh Li Lj Lu Lv Lx Ly Lz Ma Md Me Mf Mg Mh Mi Mj Mq Mr Mv Mx My Na Nb Nc Nd Ne Ng Nh Ni Nk Nl Nr Nt Nu Nv Nx Ny Og Oi Oy Oz Pa Pb Pc Pe Pf Pz Qa Qb Qd) Lu(Fp Hu Hv Hw Ii Ij Ik Il In Io Iq It Iu Iv Jk Jm Jo Jp Js Jt Lh Li Lj Lv Lx Ly Lz Ma Md Mf Mg Mh Mi Mj Mq Mr Mv Mx My Nb Nc Nd Ne Ng Nh Ni Nk Nl Nr Nt Nu Nv Nw Nx Ny Og Oi Oy Oz Pa Pb Pc Pe Pf Pz Qa Qb Qd) Lz(Fp Hu Hv Hw Ii Ij Ik Il In Io Iq It Iu Iv Jk Jm Jo Jp Js Jt Lh Li Lj Lv Lx Ly Ma Md Me Mf Mg Mh Mi Mj Mq Mr Mv Mx My Na Nb Nc Nd Ne Ng Nh Ni Nk Nl Nr Nt Nu Nv Nx Ny Og Oi Oy Oz Pa Pb Pc Pe Pz Qa Qb Qd) Qd(Fp Hu Hv Hw Ii Ij Ik Il In Io Iq It Iu Iv Jk Jm Jo Jp Jt Lh Li Lj Lv Lx Ly Ma Md Me Mf Mg Mh Mi Mj Mn Mq Mr Mv Mx My Na Nb Nc Nd Ne Ng Nh Ni Nk Nl Nr Nt Nu Nv Nx Ny Og Oi Oy Oz Pa Pb Pc Pe Pf Pz Qb) Pc(Fp Hu Hv Hw Ii Ij Ik Il In Io Iq It Iu Iv Jk Jm Jo Jp Js Jt Lh Li Lj Lv Lx Ly Ma Md Me Mf Mg Mh Mi Mj Mq Mr Mv Mx My Na Nb Nc Nd Ne Ng Nh Ni Nk Nl Nr Nt Nu Nv Nx Ny Og Oi Oy Oz Pa Pb Pe Pz Qa Qb) Lx(Fp Hv Hw Ii Ij Il In Io Iq It Iu Iv Jk Jm Jo Jp Js Jt Lh Li Lj Lv Ma Md Me Mf Mg Mh Mi Mj Mn Mq Mr Mv Mx My Nb Nc Nd Ne Ng Nh Ni Nk Nl Nr Nt Nu Nv Nw Nx Ny Og Oi Oy Oz Pa Pb Pe Pf Pz Qa Qb) Ne(Fp Hu Hv Hw Ii Ij Ik Il In Io Iq It Iu Iv Jk Jm Jo Jp Js Jt Lh Li Lj Lv Ly Ma Md Mf Mg Mh Mi Mj Mq Mr Mv Mx My Nb Nc Nd Ng Nh Ni Nk Nl Nr Nt Nu Nv Nw Nx Ny Og Oy Oz Pa Pb Pe Pf Pz Qa Qb) Nh(Fp Hu Hv Hw Ii Ij Ik Il In Io Iq It Iu Iv Jk Jm Jo Jp Jt Lh Li Lj Lv Ly Ma Md Mf Mg Mh Mi Mj Mq Mr Mv Mx My Nb Nc Nd Ng Ni Nk Nl Nr Nt Nu Nv Nw Nx Ny Og Oi Oy Oz Pa Pb Pe Pf Pz Qa Qb) Oy(Fp Hu Hv Hw Ii Ij Ik Il In Io Iq It Iu Iv Jk Jm Jo Jp Js Jt Lh Li Lj Lv Ly Ma Md Mf Mg Mh Mi Mj Mq Mr Mv Mx My Na Nc Nd Ng Ni Nk Nl Nr Nt Nu Nv Nx Ny Og Oi Oz Pa Pb Pe Pf Pz Qa Qb) My(Fp Hu Hv Hw Ii Ij Ik Il In Io Iq It Iu Iv Jk Jm Jo Jp Js Jt Lh Li Lj Lv Ly Ma Md Mf Mg Mh Mi Mj Mq Mr Mv Na Nc Nd Ng Ni Nk Nl Nr Nt Nu Nv Nx Ny Og Oi Oz Pa Pb Pe Pf Pz Qa Qb) Nr(Fp Hu Hv Hw Ii Ij Ik In Io Iq It Iu Iv Jk Jm Jo Jp Js Jt Lh Li Lj Lv Ly Ma Md Mf Mg Mh Mi Mj Mq Mr Mv Mx Na Nb Nc Nd Ng Ni Nk Nl Nt Nu Nv Nx Ny Og Oi Oz Pa Pe Pz Qa Qb) Mi(Fp Hu Hv Hw Ii Ij Il In Iq It Iu Iv Jk Jm Jo Jp Js Jt Lh Li Lj Lv Ly Ma Md Mf Mg Mh Mq Mr Mv Mx Na Nb Nc Nd Ng Ni Nk Nl Nt Nu Nv Nw Nx Ny Og Oz Pa Pb Pe Pf Pz Qa Qb) Mq(Fp Hu Hv Hw Ii Ij Ik Il In Io Iq It Iu Iv Jk Jm Jo Jp Js Jt Lh Li Lj Lv Ly Ma Md Mf Mg Mh Mr Mv Mx Nb Nc Nd Ng Ni Nk Nl Nt Nu Nv Nx Ny Og Oi Oz Pa Pe Pf Pz Qa Qb) Mv(Fp Hv Hw Ii Ij Ik In Io Iq It Iu Iv Jk Jm Jo Jp Js Jt Lh Li Lj Lv Ly Ma Md Me Mf Mg Mh Mj Mr Mx Nb Nc Nd Ng Ni Nk Nl Nt Nu Nv Nx Ny Og Oz Pa Pb Pe Pf Pz Qa Qb) Nk(Fp Hu Hv Hw Ii Ij Ik Il In Io Iq It Iu Iv Jk Jm Jo Jp Js Jt Lh Li Lj Lv Ly Ma Md Mf Mg Mh Mj Mr Mx Nb Nd Ng Ni Nl Nt Nu Nv Nx Ny Og Oz Pa Pb Pe Pf Pz Qa Qb) Lj(Fp Hu Hv Hw Ii Ij Ik In Io Iq It Iu Iv Jk Jm Jo Jp Jt Lh Li Lv Ly Ma Md Me Mf Mg Mh Mj Mr Mx Na Nb Nc Nd Ng Ni Nl Nt Nu Nv Nx Ny Og Oz Pa Pb Pe Pz Qa Qb) Nu(Fp Hu Ii Ik Il Io Iq It Iu Iv Jk Jm Jo Jp Js Jt Lh Li Lv Ly Ma Md Me Mf Mg Mh Mj Mn Mr Mx Nb Nc Nd Ng Ni Nl Nt Nv Nx Ny Og Oi Oz Pa Pb Pe Pf Pz Qb) Nv(Fp Hu Hv Hw Ij Ik Il Io Iq It Iu Iv Jk Jm Jo Jp Js Jt Lh Li Lv Ly Ma Md Me Mf Mg Mh Mj Mr Mx Nc Nd Ng Ni Nl Nt Nx Og Oi Oz Pa Pb Pe Pf Pz Qa Qb) Oz(Fp Hu Hv Hw Ii Ij Ik In Io Iq It Iu Iv Jk Jm Jo Jp Js Jt Lh Li Lv Ly Md Mf Mg Mh Mj Mr Mx Na Nb Nc Nd Ng Ni Nl Nt Nx Ny Og Pa Pb Pe Pz Qa Qb) Md(Fp Hv Hw Ii Ij In Io Iq It Iu Iv Jk Jm Jo Jp Js Jt Lh Li Lv Ly Ma Mf Mg Mh Mr Mx Na Nb Nc Nd Ng Ni Nl Nt Nw Nx Ny Og Pa Pe Pf Pz Qa Qb) Iu(Fp Hu Hv Hw Ii Ij Ik Il In Io Iq It Jk Jm Jo Jp Js Jt Li Lv Ly Mf Mg Mh Mj Mr Mx Nb Nc Nd Ng Ni Nl Nt Nx Ny Og Oi Pa Pb Pf Pz Qa Qb) Pz(Fp Hu Hv Hw Ii Ij Ik In Io Iq It Iv Jk Jm Jo Jt Lh Li Lv Ly Mf Mg Mh Mj Mr Mx Na Nb Nc Nd Ng Ni Nl Nt Nx Ny Og Oi Pa Pb Pe Qa Qb) Jk(Fp Hv Hw Ii Ij In Io Iq It Iv Jo Jp Jt Lh Li Lv Ly Ma Me Mf Mg Mh Mj Mr Mx Na Nb Nc Nd Ng Ni Nl Nt Nw Nx Ny Og Pa Pe Pf Qa Qb) Lv(Fp Hu Hv Hw Ii Ij In Io Iq It Iv Jm Jo Jp Jt Lh Li Ly Ma Mf Mg Mh Mr Mx Na Nb Nc Nd Ng Ni Nl Nt Nx Ny Og Pa Pe Pf Qa Qb) Nt(Fp Hv Hw Ii Ij In Io Iq It Iv Jo Jp Js Jt Lh Li Ma Mf Mg Mh Mr Mx Na Nb Nc Nd Ng Ni Nl Nx Ny Og Pa Pe Pf Qa Qb) Mg(Fp Hu Hw Ii Ik Il Io Iq It Jm Jo Jp Js Jt Lh Li Ly Mf Mh Mj Mr Mx Nb Nc Nd Ng Ni Nl Nx Ny Og Oi Pa Pb Pe Qb) Fp(Hu Hv Hw Ii Ij In Io Iq It Jm Jo Jp Js Jt Lh Li Mf Mh Mr Mx Nb Nc Ng Ni Nl Nx Ny Og Pa Pe Pf Qa Qb) Mx(Hu Ii Il Io Iq It Iv Jm Jo Jp Js Jt Lh Li Ly Mf Mh Mj Mr Nb Nc Nd Ng Ni Nl Nx Ny Og Pa Pb Pe Pf Qa Qb) Nl(Hu Hv Hw Ii Ij Ik In Io Iq It Jm Jo Jp Jt Li Ly Mf Mh Mj Mr Nb Nc Nd Ng Ni Nl Nx Ny Og Pa Pb Qb) Qb(Hu Hw Ii Ij Io Iq It Iv Jo Jp Js Jt Lh Li Ly Mf Mh Mr Nb Nc Nd Ng Ni Nx Ny Og Pa Pb Pe Pf Qa) Li(Hu Hw Ii Ij Io Iq It Iv Jm Jo Jp Js Jt Lh Ly Ma Mf Mr Nb Nc Nd Ng Ni Nx Ny Og Pa Pb Pe Pf Qa) Pa(Hu Ii Ij Ik Io Iq It Iv Jm Jo Jp Jt Lh Ly Ma Mf Mh Mj Mr Nb Nc Nd Ng Ni Nx Ny Og Pe Pf) Mf(Hu Hv Hw Ii Ij In Io Iq It Iv Jo Jt Lh Ly Ma Mh Mr Nb Nc Ng Ni Nx Ny Og Pe Pf Qa) Ng(Hu Ii Ik Il Io Iq It Jm Jo Jp Js Jt Lh Ly Mh Mj Mr Nc Nd Ni Nx Og Oi Pb Pe Pf) It(Hu Hw Ii Ij In Io Iq Iv Jo Jp Js Jt Lh Ly Mh Mr Na Nb Nc Ni Nx Ny Og Pe Qa) Lh(Hv Hw Ii Ij In Io Iq Iv Jp Js Jt Mh Mr Na Nb Nc Nd Ni Nx Ny Og Pe Pf Qa) Og(Hu Hw Ii Ik Il Io Iq Jm Jo Jp Jt Ly Ma Mh Mj Mr Nc Nd Ni Nx Pb Pe Pf) Ni(Hu Hv Hw Ii Ij In Io Iq Iv Jm Jo Js Jt Ly Mh Mr Na Nb Nx Pe Qa) Jt(Hu Hv Hw Ii Ij In Iq Iv Jm Js Ly Mh Mr Na Nb Nc Nx Ny Pe Qa) Mh(Hu Hv Hw Ii Ij In Iq Iv Jo Jp Ly Mj Nb Nc Nd Nx Pb Qa) Pe(Hv Hw Ii Ij In Io Iq Iv Jm Jp Mr Na Nb Nd Nx Ny Pf Qa) Mr(Hw Ii Ij Il In Io Iq Iv Jm Jo Jp Nb Nc Nd Nx Ny) Ii(Hw Ij Io Iq Iv Jo Jp Js Nb Nc Nd Nx Pf) Nb(Hw Ij Iq Iv Jo Jp Nc Nd Nx Ny Qa) Nx(Hv Hw Ij Io Iv Jp Na Ny Pf Qa) Iq(Hu Jm Jp Js Ly Nc Nd Pb Pf) Nc(Hu Ik Jp Ly Mj Nd Pb) Ij(Hv Hw Ii Jv Js Na Qa) Qa(Hv Hw Ii Jv Js Na) Jm(Hu Il Io Jp Ly) Jp(Ly Nd Ny Pf) Iv(Hv Hw Js) Ly(Hu Ik) MaPf MjIo NaHv} Ok{Jk(Et Fp Fr Hq Hu Hv Hw Hx Ih Ii Ij Il In Io Ip Iq Ir Is It Iu Iv Jg Jh Jl Jm Jn Jp Jr Js Jt Lh Li Lj Lu Lv Lw Lx Ly Lz Ma Mb Mc Md Me Mf Mh Mi Mj Mk Ml Mm Mn Mp Mr Ms Mt Mv Mw Mx Mz Na Nb Nc Nd Ne Nf Nh Ni Nj Nk Nl Nm Nn Nq Nr Ns Nt Nu Nv Nw Nx Ny Oc Of Oh Om Oz Pa Pc Pd Pe Pf Pg Po Qb Qc Qe) Jl(Et Fp Fr Hq Hu Hv Hw Hx Ih Ii Ij Il In Io Ip Iq Ir Is It Iu Iv Jg Jm Jn Jp Jr Js Jt Lh Li Lj Lu Lv Lw Lx Ly Lz Ma Mb Mc Md Me Mf Mh Mi Mk Ml Mm Mn Mp Mr Ms Mt Mv Mw Mx My Mz Na Nb Nc Ne Nf Nh Ni Nj Nk Nl Nm Nq Nr Ns Nt Nu Nv Nw Nx Ny Oe Of Oh Oy Oz Pa Pc Pd Pe Pf Pg Po Qa Qb Qc Qd Qe) Pa(Et Fp Fr Hq Hu Hv Hw Hx Ih Ii Ij Il In Ip Iq Ir It Iu Iv Jg Jm Jn Jp Jr Js Jt Lh Li Lj Lu Lv Lw Lx Ly Lz Ma Mb Mc Md Me Mf Mh Mi Ml Mm Mn Mp Mr Ms Mt Mv Mw Mx My Mz Na Nb Nc Nd Ne Nf Nh Ni

Oy Oz Pa Pc Pd Pe Pf Pg Po Pz Qa Qb Qc Qd Qe) Ir(Fp Hq Hu Hv Hw Hx Ih Ii Il In Io Ip Iq It Iu Iv Jg Jh Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mq Mr Ms Mt Mv Mw Mx My Mz Nb Ne Nf Ng Nh Ni Nj Nk Nl Nm Nq Nr Ns Nu Nv Nx Ny Oe Of Oh Om Oy Oz Pa Pc Pd Pe Pf Pg Po Qa Qb Qd Qe) Mb(Fp Fr Hq Hr Hu Hv Hw Hx Ih Ii Ij Ik Il In Io Ip Iq It Iu Iv Jg Jh Jk Jm Jn Jo Jp Jq Jr Js Jt Lh Li Lj Lu Lv Lw Ly Lz Ma Mc Md Me Mf Mg Mh Mi Mj Mk Ml Mm Mn Mp Mq Mr Ms Mt Mw Mx Mz Nb Nf Ng Nh Ni Nk Nm Nn Nq Nr Ns Nu Nv Nx Oe Oh Om Oz Pa Pc Pd Pe Pg Po Pz Qa Qb Qc Qd Qe) Hw(Fp Hq Hu Hv Hx Ih Ii Il In Io Ip Iq It Iu Iv Jg Jh Jk Jm Jn Jo Jp Jq Jr Js Jt Lh Li Lj Lu Lv Lw Lx Ly Lz Ma Mc Md Me Mf Mg Mh Mi Mj Mk Mm Mn Mq Mr Ms Mt Mv Mw Mx Mz Nb Ne Nf Ng Nh Ni Nj Nk Nl Nm Nq Nr Ns Nu Nv Nx Ny Oe Oh Om Oz Pa Pc Pd Pe Pf Pg Po Pz Qa Qb Qc Qd Qe) Nt(Fp Fr Hq Hr Hu Hv Hx Ii Ij Il Im In Ip Iq It Iu Iv Jg Jh Jk Jo Jp Js Jt Lh Li Lj Lv Lw Ly Ma Md Me Mg Mh Mi Mj Mk Ml Mm Mp Mq Ms Mt Mv Mw Mx Mz Nb Nc Nd Ne Nf Nh Ni Nj Nl Nm Nn Nq Nr Ns Nu Nx Ny Oe Of Oh Om Oy Pa Pb Pc Pe Pf Pz Qa Qc) Mu(Fp Fr Hr Hu Hv Hx Ih Ij Im In Io Ip Iq It Iu Jh Jm Jn Jo Jq Jr Js Jt Lh Li Lj Lv Lw Lx Lz Ma Md Me Mg Mh Mi Mj Ml Mm Mp Mr Ms Mt Mw Mx Mz Nb Nd Ne Nf Nh Ni Nj Nk Nl Nm Nn Nr Ns Nu Nv Ny Oe Of Oh Om Oz Pa Pc Pe Pf Pg Pz Qa Qb Qc) Lh(Fr Hr Hu Hv Ii Il Im In Io Ip Iq Iv Jh Jm Jn Jo Jq Jr Js Lj Lv Lw Ly Md Me Mg Mj Ml Mm Mp Ms Mt Mv Mw Mx Mz Nc Nd Ne Nh Ni Nj Nl Nm Nn Ns Nu Nv Ny Oe Of Oh Om Pf Pg Po Pz Qa Qc) Jo(Fr Hr Hu Hx Ij In Io Ip Iq Iv Jh Jq Jr Jt Lv Lw Lx Md Me Mg Mh Mj Ml Mm Mp Mq Mr Ms Mt Mv Mw My Mz Nc Nd Ne Ng Nj Nk Nl Nn Ns Nx Ny Of Og Oh Oy Pa Pf Pz Qc) Im(Fr Hr Hu Ii Ij Ik In Io Iq It Jg Jh Jj Js Jt Me Mh Mi Mj Mm Mp Mq Mr Mt Mv Mw My Mz Nb Nc Nd Ne Nf Ng Ni Nj Nl Nm Nn Nu Ny Og Oh Oi Om Oy Oz Pa Pb Pf) Oi(Fr Hr Hv Ih Ij Ik In Ip Iq Iu Iv Jg Jh Jj Jk Jn Jq Jr Jt Li Lw Lx Me Mh Mi Mm Mn Mt Mw My Mz Nb Nc Nd Ne Nf Nl Nm Nu Og Om Oy Oz Pa Pb Pf Po Qa) Nn(Hr Hu Hv Ij Ik In Io It Jh Jn Jq Jr Js Lj Lx Ma Me Mg Mh Mp Mr Ms Mv Mz Nc Nd Ne Nf Ng Ni Nl Nq Nr Ns Og Oh Om Oy Pa Pb Pc Pe Qa Qc) Iv(Hr Hx Ij Io Ip Iq Jh Jq Jr Jt Lw Lx Ma Me Mg Mh Mj Ml Mm Mr Ms Mt Mw My Mz Nc Nm Ny Og Oh Om Oy Pb Pe Pf Pz Qc Qd Qc) Pe(Fr Hr Hu Hv Hx Io Ip Jh Jn Jq Jr Lw Ly Md Me Mg Mj Mk Ml Mm Mp Ms Mt Mv Mw Mz Nc Nd Ne Ng Nl Ny Oe Of Oh Om Pz Qa) Mr(Fr Hr Hu Hv Hx Il In Io Jh Jn Jr Ly Mg Mj Ml Mm Mp Mt Mv Mw My Mz Nc Ng Ni Nm Ny Of Oh Om Oy Pg Po Pz Qa) Fr(Hr Hu Hv Ij Ik In It Jr Js Lj Lw Ma Me Mg Mh Mp Ms Mv Mz Nc Nd Ne Nf Ng Ni Nl Nm Nr Og Oy Pb Pz Qa) Jq(Hr Ij Ik Iq Iu Jg Jh Jj Jr Md Mh Ml Mm Mp Mt Mw My Ne Nj Nk Nl Nr Ny Of Og Oh Oy Oz Pb Pf Qc) Nd(Hq Hr Ij In Io It Jh Jm Js Jt Lw Ly Me Mh Mv My Mz Nc Ne Ng Nh Ni Nj Nl Nr Og Om Oy Pz Qa) Hv(Hr Hx Ij Ik Iq Iu Jh Jj Lx Md Me Mh Ml Mm Mp Mt Mv Mw My Nc Ny Of Og Oh Oy Pa Pb Pf Qc) Mp(Hr Ij Ik In Io Iq It Jh Jj Jn Jr Js Mg My Mz Nc Ne Nf Ni Nr Og Oh Om Pz Qa Qc) Jh(Iq Jn Jr Lj Lw Lx Lz Mg Mh Ms Mw Mz Ne Nl Nr Ns Ny Oe Of Oh Pa Pb Pf Pz Qa) Jj(Hq Hr Ii Ij Il In It Iu Jg Jn Jr Lw Mt Mz Nc Nf Nm Nr Nu Of Pa Pf Pg Po Qa) Jn(Hr Ij Ik Iu Js Lw Lx Md Ml Mm Mt Mw My Nc Nr Ny Og Oh Oz Pa Pb Pf) Mw(Hu Iq Jr Lj Mg Mh Ms Mz Nc Ne Nl Ny Of Om Pb Pf Pz Qa Qc) Qa(Hr Ij Ik Iq Iu Lx Md Ml Mm My Nc Ny Og Oh Pa Pb Pf Qc) Om(Hu Hx Iq Jr Lj Lx Md Mg Mh Ml Ms Nc Ne Nl Ny Oh Pf) Jr(Hr Ik Iu Lw Lx Mm My Nc Nr Og Oh Pa Pb Pf) In(Hx Ij Ik Lx Md Ml My Nc Ny Of Og Oy Pb) Og(Hr Ij Jk Lw Lx Mt Mz Nf Nm Nr Pa Po) My(Hr Ij Lx Mt Mz Nb Nf Nr Pa Po) Ik(Hr Ii Iq Jk Lz Mj Mt Nu Oz) Mz(Lx Md Ml Mm Nc Ny Pb Qc) Oy(Jg Mt Nb Nf Nr Pa Po) Lx(Hu Jt Lw Ly Mh Ng) Nc(Hr Ij Io Mt Nf Nr) Ii(Hx Mh Ny Of Pb) Lw(Iq Ne Nr Pa) Nf(Ml Ny Of Pb) Ng(Jg Jk Pa Po) Mh(Nr Pa Po) Ij(Md Ml Pb) Pz(Nm Pf) Qc(Js Mt) Pb(Hr Pa) PoMv HuJk} Fr{Mz(Fp Hq Hr Hu Hv Hw Hx Ih Ii Ij Il In Io Ip Iq Ir It Iu Iv Jg Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mw Mx Na Nb Nc Nd Ne Nf Ng Nh Ni Nj Nk Nl Nm Nn Nq Nr Ns Nu Nv Nx Ny Oe Of Og Oh Om Oy Oz Pa Pc Pd Pe Pf Pg Po Qa Qb Qc Qe) Iv(Fp Hq Hr Hu Hv Hw Hx Ih Ii Ij Il In Io Ip Iq Ir It Iu Jg Jh Jk Jm Jn Jp Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx Na Nb Nc Nd Ne Nf Nh Ni Nj Nk Nl Nm Nn Nq Nr Ns Nt Nu Nv Nx Ny Oe Of Oh Oi Om Oy Oz Pa Pc Pd Pe Pf Pg Po Qa Qb Qc Qd Qe) Jn(Fp Hq Hr Hu Hv Hw Hx Ih Ii Ij Il In Io Ip Iq Ir It Iu Jg Jh Jk Jm Jo Jp Js Jt Lh Li Lj Lu Lv Lw Ly Lz Ma Mb Mc Md Me Mf Mh Mi Mj Mk Ml Mm Mn Mq Mr Ms Mt Mu Mv Mw Mx Na Nb Nd Ne Nf Nh Ni Nj Nk Nl Nm Nn Nq Nr Ns Nu Nv Nx Ny Oe Of Og Oh Om Oy Oz Pa Pc Pd Pe Pf Pg Po Qa Qb Qc Qd Qe) Jr(Fp Hq Hv Hx Ih Ii Ij In Io Ip Iq It Iu Jg Jk Jm Jo Jp Js Jt Lh Li Lj Lu Lv Lx Ly Lz Mc Md Me Mf Mh Mi Mj Mk Ml Mm Mn Mq Ms Mt Mw Mx Nb Nd Ne Nf Nh Ni Nk Nl Nm Nn Nq Nr Ns Nv Nx Ny Oe Of Oh Om Oz Pa Pc Pd Pe Pf Pg Po Qa Qb Qd Qe) Ir(Fp Hq Hu Hv Hw Hx Ih Ii Ij Il In Ip Iq It Iu Jg Jk Jm Jp Js Lh Li Lj Lu Lv Ly Lz Ma Mb Mc Md Me Mf Mh Mi Mk Ml Mm Mn Mq Mr Mx Na Nb Ne Nf Nh Ni Nk Nl Nm Nn Nq Nr Ns Nt Nv Nx Ny Oe Oh Om Oz Pa Pc Pd Pe Pf Pg Po Qa Qb Qc Qd Qe) Na(Fp Hr Hu Ih Ij Ik Io Ip Iq It Jg Jh Jm Js Lh Li Lj Lv Lw Lx Lz Ma Md Mf Mh Mj Mk Ml Mm Mp Mq Mr Ms Mt Mu Mv Mw Mx Nb Nd Ne Nf Nh Ni Nj Nk Nl Nm Nn Nq Ns Nt Nu Nx Ny Oe Of Og Oh Oi Om Oy Pa Pc Pe Pf Po Pz Qb) Hw(Hr Hu Ih Ij Ik Io Ip Iq Jg Jh Js Lh Lj Lv Lw Lx Lz Ma Mf Mh Mj Mm Mp Mr Ms Mt Mu Mv Mw Nc Nd Ne Nf Nh Nj Nk Nl Nn Ns Nt Nu Of Og Oh Oi Om Oy Pa Pe Pf Pz) Jq(Hq Hv Hx Ih Ii Il In Io Ip It Iu Jg Jk Jm Jp Js Jt Li Lu Ly Mc Mi Mj Mk Mn Mq Ms Mx Nb Nf Nh Ni Nm Nq Ns Nu Nv Oe Om Pd Pg Po Qa Qb Qc Qd Qe) Hv(Hu Ih Ij Im Io Iq Jh Jo Lh Lj Lv Lw Lx Lz Ma Me Mf Mh Mm Mp Mr Ms Mt Mu Mv Nc Nd Ne Nj Nk Nl Nn Nt Nu Of Og Oh Oi Om Oy Pa Pe Pf Pz) Js(Hr Hu Ik Io Ip Jh Jo Lh Lj Lw Lx Ma Mb Mm Mp Mr Ms Mt Mu Mv Mw Nc Nd Ne Ng Nh Nj Nl Nm Nn Nr Nt Nu Of Og Oh Oi Om Oy Pa Pb Pe Pz) Mr(Hr Hx Ih Il Im Io Ip Iq Jh Jm Jo Lj Ly Mb Mh Mj Mk Mp Ms Mt Mu Mv Nc Ne Nf Nh Nj Nl Nm Nn Nq Nu Ny Of Og Oh Oi Om Pg Pz Qa) Im(Hr Hu Ih Ij Ik In Iq It Jo Jt Lh Lj Lw Ma Mb Me Mg Mh Mj Mp Mt My Nc Ne Nf Nj Nl Nm Nq Nr Nt Oh Oi Om Pa Pb Pe Pf Pz Qa) Pe(Hr Hu Hx Ih Il Io Ip Iq Jh Jo Lj Lv Lw Ly Mh Mk Ml Mp Ms Mt Mu Mv Nc Ne Nf Nh Nj Nl Nn Nu Ny Of Og Oh Oi Om Pz) Mg(Hr Hx Ii Ij Ip Iq It Jg Jt Lw Lx Me Mi Mm Mq Mt Mu Mw Nb Nc Nd Ne Nf Nh Nj Nl Nn Nr Nx Ny Oh Oi Pa Pf Po) Nf(Hu Hx Ih Ik Jh Jo Lj Lw Mb Md Mh Ml Mp Mu Mv My Nc Ne Nh Nj Nl Nr Nt Nu Ny Of Og Oh Oi Oy Pb Pz) Mp(Hr Hu Ij Ik In Io Iq It Jh Jo Lh Lj Ma Me Mu My Nc Ne Ng Nh Ni Nl Nr Nt Oh Oi Om Oy Pz Qa) Lh(Hr Hu Ih Il Io Iq Jh Jm Lj Lw Ly Mt Mu Mv Nc Ne Nh Nj Nn Nq Nu Of Og Oh Oi Om Pz) Ik(Fp Hr Ii Ij In Iq It Jo Lx Lz Me Mj Mk Mt Mu Mw Ne Nh Nl Nm Nr Ny Pa Pf Qa Qb) Om(Hx Ih Iq Jh Jo Lj Lx Lz Ma Mb Ml Ms Mu Mv Mw Nc Nd Ne Nl Ns Nt Ny Oh Oi Pz) Ng(Hr Hx Ih Ij In Iq It Jg Jj Jt Lw Md Me Mt Nb Nc Nd Ne Nn Nr Ny Oh Pa Qb) Qa(Hu Ih Iq Jh Jo Lj Lx Mt Mu Mv My Nc Nd Ne Nj Nl Nt Of Og Oh Oi Oy Pb Pz) Nt(Hu Io Iq Jh Jm Jo Lj Lw Ly Mb Mt Mu My Nj Nq Og Oh Oi Oy Pb Pz) My(Hr Hx Ij In Iq It Jg Jo Lx Mb Md Mt Mu Ne Nn Nr Oh Pa Po) Pz(Ih Iq It Jg Jh Jo Jt Lj Lw Mb Mt Mu Mw Nc Nm Nn Nr Oh Pf) Mb(Ih Io Iq Lj Mt Mu Nc Ne Nh Nl Oh Oi Pb) Oy(Hr Hx Ij In Jg Jo Lx Md Mt Mu Ne Nr Ny) In(Ih Iq Jo Lj Nc Ne Nl Of Og Oh Pb) Iq(Ij It Jh Jo Lw Me Mu Mw Nr Oi) Jj(Jp Li Mc Mi Mj Mk Ml Mv Ns Oe) Oh(Ij Io Jh Jo Ma Me Ne Nn Oi Pc) Mt(Hu Lw Ma Mv Nc Nj Og Oi Pb) Nc(Ij Io Jh Jo Me Ni Ny Oi) Hu(Lx Mu Mw Mx Ne Nn Ny) Jh(Ih Lj Mh Ms Og Oi Pb) Ij(Ih Lj Ne Nl Of Pb) Og(Jg Mu Nb Nr Ny Po) Lw(Ih Lj Ma Ne Pa) Pb(Hr Jo Nb Nr Po) Oi(Ih Ma Nn) Lx(Hq Ly) Mu(Ih Lj) PoOf MaPf MdLj} Jq{Nn(Fp Hq Hr Hu Hv Hx Ih Ii Ij Ik Il In Io Ip Iq Ir It Iu Jg Jh Jk Jm Jn Jo Jp Jr Js Jt Li Lj Lu Lv Ly Lz Ma Mb Mc Md Me Mf Mh Mi Mj Mk Ml Mm Mn Mp Mq Ms Mt Mu Mv Mw Mx My Mz Na Nb Ne Nf Ng Nh Ni Nj Nk Nl Nm Nq Nr Ns Nu Nv Nx Ny Oe Of Og Om Oy Oz Pb Pd Pf Pg Po Qa Qb Qc Qd Qe) Mu(Fp Hq Hr Hu Hv Hw Hx Ih Ii Ij Il In Io Ip It Iu Jg Jh Jk Jm Jn Jo Jp Js Jt Li Lu Lv Lw Ly Lz Ma Mb Mc Md Me Mf Mg Mi Mj Mk Ml Mm Mn Mq Ms Mt Mv Mw Mx My Mz Na Nb Ne Nf Nh Ni Nk Nl Nm Nq Ns Nu Nv Nx Ny Oe Of Oh Oi Om Oz Pc Pd Pf Pg Po Pz Qa Qb Qc Qd Qe) Mw(Fp Hq Hr Hv Hw Hx Ih Ii Il In Io Ip Ir It Iu Iv Jg Jh Jk Jm Jn Jo Jp Jr Js Jt Li Lu Lv Lw Ly Lz Ma Mb Mc Me Mf Mh Mi Mj Mk Ml Mm Mn Mq Ms Mt Mv Mx Mz Na Nb Ne Nf Nh Ni Nj Nk Nl Nm Nq Nr Ns Nu Nv Nx Ny Oe Oh Oi Om Oz Pc Pd Pf Pg Po Pz Qa Qb Qc Qd Qe) Pf(Fp Hq Hr

Unconstrained panels with 2 analytes, where 1.0E-6 >= 'model p-value' > 0. Contains 1,045 panels of 7,260 total panels evaluated. : No(aA Et Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ji(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ok(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Om On Oy Oz Pa Pb Pc Pd Pe Pf Pg Po Pz Qa Qb Qc Qd Qe) On(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Om Oy Oz Pa Pb Pc Pd Pe Pf Pg Po Pz Qa Qb Qc Qd Qe) aA(Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn Nq Nr Ns Nt Nu Nv Nw Nx Ny Oe Of Og Oh Oi Om Oy Oz Pa Pb Pc Pd Pe Pf Pg Po Pz Qa Qb Qc Qd Qe) Is(Et Fr Hr Hv Hw Ii Ij Ik Im In Io Ip Iq Ir Jg Jh Jj Jk Jl Jm Jn Jo Jp Jq Jr Lh Li Lu Lw Lx Lz Ma Mb Md Me Mg Mh Mi Mj Mm Mn Mp Mr Ms Mt Mu Mw Mz Na Nb Nc Nd Ne Nf Ng Ni Nj Nl Nm Nn Nq Nr Ns Nt Nv Nw Ny Oe Og Oh Oi Om Pa Pb Pe Pf Po Pz Qb Qc) Jl(Et Fr Hr Hv Hw Ih Ij Ik Im In Io Iq Ir Iv Jg Jh Jj Jn Jo Jq Jr Js Lh Li Lw Lx Ma Mb Md Me Mg Mm Mp Mr Mt Mu Mw Mz Na Nc Nd Nf Ng Ni Nm Nn Nt Nw Oe Og Oh Oi Om Pa Pb Pe Pf Pz Qa) Et(Fr Hw Iq Ir Iv Jh Jj Jn Jq Jr Js Lh Lu Lx Md Mh Mp Mr Mt Mu Mw Mz Nc Nd Ne Nf Nl Nn Nr Nt Nw Ny Oh Om Pa Pe Pf Po Pz) Fr(Hv Hw Ih Ij Im In Iq Ir Iv Jj Jn Jo Jq Jr Js Lh Lw Mb Mg Mp Mr Mt Mu Mz Na Nc Ne Nf Ng Nr Nt Nw Oh Om Pe Qa) Om(Hu Ih Ik Im Iq Ir Jj Jq Jr Lh Lj Lx Lz Mg Mp Mr Ms Mt My Nc Nd Ng Nn Nt Nw Of Og Oh Oy Pb Pf) Jq(Hw Im Iq Jg Jh Jj Jk Lh Li Lx Ma Mm Mp Mr Mt Mu Mw Nc Nd Nn Nr Nt Nw Oh Oz Pa Pe Pf Po) Nw(Hv Hw Im Ir Iv Jh Jj Jn Jo Jr Lh Mb Mp Mr Mt Mu Mw Mz Na Nd Nn Nr Nt Oi Pe Pf Qa) Mt(Hw Ik Im Iq Ir Iv Jh Jj Jn Jr Lh Lw Mb Mp Mr Mu Mz Na Nr Nt Oi Pa Pb Pe) Mu(Ih Ik Iq Ir Iv Jj Jn Jr Js Lh Lj Mp Mr Mz Nr Nt Oh Pa Pe Pf) Jh(Hu Ik Iq Ir Jj Jr Lh Lj Lx Lz Mh Mp Mr Mz Ng Nt Og Oh Pe Pf) Jj(Ii Jg Jk Jr Lh Lx Mp Mr Mw Nn Nt Nv Ny Pe Pf Pg Po) Nn(Hw Ir Iv Jn Jr Lh Mr Mz Na Nt Oi Pa Pe) Mw(Hu Ik Iq Ir Jn Jr Lh Mr My Mz Ng Og Oy) Mp(Hw Iq Ir Iv Jn Jr Lh Mr Mz Nf Nt Pe) Lh(Ik Iq Jn Jr Lw Mg Mz Oh Pb Pf) Ik(Ir Iv Mr Pe Pf Po) Jr(Im Jg Lx Mm Mr Nt) Lx(Ir Jn Ly) Mr(Lw Mz Oh) Nt(Jn Mz) Pe(Oh Pb) PoOy MzIm JnPa Unconstrained panels with 2 analytes, where 1.0E-5 >= 'model p-value' > 1.0E-6. Contains 1,122 panels of 7,260 total panels evaluated. : Mt(Fp Hq Hr Hu Hv Hx Ih Ii Ij Il In Io Ip It Iu Jg Jk Jm Jo Jp Js Jt Li Lj Lu Lv Lx Ly Lz Ma Mc Md Me Mf Mg Mh Mi Mj Mk Ml Mm Mn Mq Ms Mv Mw Mx My Nb Nc Nd Ne Nf Ng Nh Ni Nj Nk Nl Nm Nn Nq Ns Nu Nv Nx Ny Oe Of Og Oh Oy Oz Pc Pd Pf Pg Po Pz Qa Qb Qc Qd Qe) Jq(Fp Hq Hr Hu Hv Hx Ih Ii Ij Ik Il In Io Ip Ir It Iu Iv Jm Jn Jo Jp Jr Js Jt Lj Lu Lv Lw Ly Lz Mb Mc Md Me Mf Mg Mh Mi Mj Mk Ml Mn Mq Ms Mv Mx My Mz Na Nb Ne Nf Nh Ni Nj Nk Nl Nm Nq Ns Nu Nv Nx Ny Oe Of Og Oi Oy Pb Pc Pd Pg Pz Qa Qb Qc Qd Qe) Nw(Fp Hq Hr Hu Hx Ih Ii Ij Ik Il In Io Ip Iq It Iu Jg Jk Jm Jp Js Jt Li Lj Lu Lv Lw Lx Lz Ma Md Me Mg Mh Mi Mj Mk Ml Mm Mn Mq Ms Mv Mx My Nb Nc Ne Nf Ng Nh Ni Nj Nk Nl Nm Nq Ns Nu Nv Nx Ny Oe Of Og Oh Oy Oz Pa Pb Pc Pd Pg Po Pz Qb Qc Qe) Fr(Fp Hq Hr Hu Hx Ii Ik Il Io Ip It Iu Jg Jh Jk Jm Jp Jt Li Lj Lu Lv Lx Ly Lz Ma Mc Md Me Mf Mh Mi Mj Mk Ml Mm Mn Mq Ms Mv Mw Mx My Nb Nd Nh Ni Nj Nk Nl Nm Nn Nq Ns Nu Nv Nx Ny Oe Of Og Oi Oy Oz Pb Pc Pd Pf Pg Po Pz Qb Qc Qd Qe) Et(Fp Hq Hr Hu Hv Hx Ih Ii Ij Ik Il Im In Io Ip It Iu Jg Jk Jm Jo Jp Jt Li Lj Lv Lw Ly Lz Ma Mb Mc Me Mf Mg Mi Mj Mk Ml Mm Mn Mq Ms Mv Mx My Na Nb Ng Nh Ni Nj Nk Nm Nq Ns Nu Nv Nx Oe Of Og Oi Oy Oz Pb Pc Pd Pg Qa Qb Qc Qd Qe) Lh(Fp Hq Hr Hu Hv Hw Hx Ih Ii Il Im In Io Ip Ir Iu Iv Jg Jk Jm Jo Jp Js Li Lj Lv Lx Ly Ma Mb Md Me Mh Mi Mj Ml Mm Mn Mq Ms Mx My Na Nc Nd Ne Nf Ng Nh Ni Nj Nk Nl Nm Nq Ns Nt Nu Nv Ny Oe Of Og Oi Oy Pa Pe Pg Po Pz Qa Qb Qd Qe) Om(Fp Hq Hr Hv Hw Hx Ii Ij In Io Ip It Iu Iv Jg Jh Jm Jn Jo Jp Js Jt Li Lu Lv Lw Ly Ma Mb Md Me Mf Mh Mi Mj Mk Ml Mm Mn Mq Mu Mv Mw Mx Mz Na Nb Ne Nf Nh Ni Nj Nk Nl Nm Nr Ns Nu Nv Nx Ny Oe Oi Oz Pa Pe Pg Po Pz Qa Qb Qc Qd Qe) Nn(Fp Hr Hu Hv Hx Ih Ii Ij Ik Im In Io Ip It Jg Jh Jo Jp Js Jt Lj Lu Lv Lw Lx Mb Md Me Mf Mg Mh Mi Mj Mp Ms Mu Mw Mx My Nb Nc Nd Ne Nf Ng Nh Ni Nj Nl Nm Nr Ns Nx Ny Og Oh Oy Oz Pc Pf Pg Po Pz Qb Qd) Mu(Fp Hr Hu Hv Hw Ii Ij Im In Ip It Iu Jg Jh Jo Jp Jt Li Lv Lw Lx Lz Ma Mb Md Me Mg Mh Mi Mj Ml Mm Mn Mw Mx My Na Nb Nc Nd Ne Nf Ng Nh Nj Nl Nm Ns Nv Nx Ny Oe Og Oi Oy Pb Pg Po Pz Qa Qb Qd Qe) Jl(Fp Hq Hu Hx Ii Il Ip It Iu Jk Jm Jp Jt Lj Lu Lv Ly Lz Mc Mf Mh Mi Mj Mk Ml Mn Mq Ms Mv Mx My Nb Ne Nh Nj Nk Nl Nq Nr Ns Nu Nv Ny Of Oy Oz Pc Pd Pg Po Qb Qc Qd Qe) Jh(Hw Ih Im Ip Iu Iv Jn Js Li Lw Mb Mg Mi Mj Ms Mv Na Nb Nc Nd Ne Nf Nl Nr Ny Oe Oi Oy Pa Pb Pg Po Pz Qa Qb Qd Qe) Is(Fp Hq Hu Hx Ih Il It Iu Iv Js Jt Lj Lv Ly Mc Mf Mk Ml Mq Mv Mx My Nh Nk Nu Nx Of Oy Oz Pc Pd Pg Qa Qd Qe) Mw(Hv Hw Ih Im Ip Iv Js Lj Lw Lx Lz Mg Mh Mi Mp Ms Mx Na Nc Ne Nf Nl Nr Nt Oh Oi Pa Pb Pe Pf Po Qa) Mz(Hw Ip Iq Ir Iu Iv Jg Jj Jk Jr Li Lw Lx Ma Ml Mm Nc Nd Nm Nq Nr Nv Ny Og Oh Pa Pb Pe Pf Pg Po) Mp(Fp Hr Hv Ii Ij Im In Ip Jg Jo Jp Js Lx Mb Md Mg Mh Na Nb Nc Ne Ni Nl Nr Ny Oi Pa Pf Po Qa) Mr(Hr Ih Im In Ip Iq Ir Jg Jn Jp Js Ly Ma Md Mg Mh Mm Mx Nc Nf Nm Ny Og Oi Pb Pf Po Qa) Jj(Hq Hw Hx Il Im Iq Ir Iv Jn Jo Js Li Ma Mm Nb Nd Nf Nm Nr Nx Of Oh Pa Pd Qa) Jr(Hr Hw Ii Ip Ir Iu Jk Jo Lu Lw Ma Mb Nb Nd Nf Nm Nq Nr Nv Ny Oh Pa Pe Pf Po) Pe(Hr Ih Im Ip Iq Ir Jg Jn Jo Jp Js Lw Ma Mb Mg Mm Nc Nf Nt Ny Og Pf Qa) Oh(Hv Hw Ii Iq Ir Iv Jg Jn Jo Jp Lx Na Nb Nf Nt Ny Oi Pa Po Qa) Pf(Hv Hw Ii Im In Ir Iv Jg Jn Lw Lx Mb Na Nb Nf Nt Ny Pa Qa) Ir(Hr Im Jg Jk Lw Ma Mm Nd Nf Nt Nv Ny Oi Pa Pg Po) Nt(Ik Im Io Ip Iq Jg Jp Js Lw Ma Mm Nf Ny Qa) Lx(Hq Hv Hw Ik Iq Iv Jg Js Jt Lw Na Ng Qa) Iq(Hw Ii Ik Im Jg Jo Lw Mb Na Ny) Po(Im Jn Lw My Nc Ng Of Og Pb) Jg(Hw Jn Nf Ng Og Oi Pa Qa) Ny(Ik Im Lw My Nc Of Og Oy) Jn(Im Ma Mm Nd) Pa(Js Lw Nf Qa) Nb(Ik Og) Im(Mj Nf) Iv(Ma Mm)

Unconstrained panels with 2 analytes, where 1.0E-4 >= 'model p-value' > 1.0E-5. Contains 1,312 panels of 7,260 total panels evaluated. : Nt(Fp Hq Hr Hu Hv Hw Hx Ih Ii Ij Il In It Iu Iv Jk Jm Jo Jt Li Lj Lu Lv Lx Ly Lz Mb Mc Md Me Mf Mg Mh Mi Mj Mk Ml Mn Mq Mr Ms Mv Mx My Na Nb Nc Nd Ne Ng Nh Ni Nj Nk Nl Nm Nq Nr Ns Nu Nv Nx Oe Of Og Oi Oy Oz Pa Pb Pc Pd Pg Po Pz Qb Qc Qd Qe) Ir(Fp Hq Hu Hv Hw Hx Ih Ii Ij Il In Io Ip Iq It Iu Iv Jm Jn Jo Jp Js Jt Li Lj Lu Lv Ly Lz Mb Mc Md Me Mf Mg Mh Mi Mj Mk Ml Mm Mq Ms Mv Mx My Na Nb Nc Ne Ng Nh Ni Nj Nk Nl Nm Nq Nr Ns Nu Nx Oe Of Og Oy Oz Pb Pc Pd Pz Qa Qb Qc Qd Qe) Pf(Fp Hq Hr Hu Hx Ih Ij Il Io Ip Iq It Iu Jk Jm Jo Jp Js Jt Li Lj Lu Lv Ly Lz Ma Mc Md Me Mf Mg Mh Mi Mj Mk Ml Mm Mn Mq Ms Mv Mx My Nc Nd Ne Ng Nh Ni Nj Nk Nl Nm Nq Nr Ns Nu Nv Nx Oe Of Og Oh Oi Oy Oz Pb Pc Pd Pg Po Pz Qb Qc Qd Qe) Pe(Fp Hq Hu Hv Hw Hx Ii Ij Il In Io It Iu Iv Jk Jm Jt Li Lj Lu Lv Lx Ly Lz Mc Md Me Mf Mh Mi Mj Mk Ml Mn Mq Mr Ms Mv Mx My Na Nb Nd Ne Ng Nh Ni Nj Nk Nl Nm Nq Nr Ns Nu Nv Nx Oe Of Oi Oy Oz Pa Pc Pd Pg Po Pz Qb Qc Qd Qe) Po(Fp Hq Hr Hu Hv Hw Hx Ih Ii Ij Il In Io Ip Iq It Iu Iv Jg Jk Jm Jo Jp Js Jt Li Lj Lv Lx Ly Ma Mb Md

Figure 43 Continued

Me Mg Mh Mi Mk Ml Mm Mn Ms Mv Mx Na Nb Nd Ne Nf Nh Ni Nj Nk Nl Nm Nr Ns Nv Ny Oe Oi Pa Pd Pg Pz Qa Qb Qd Qe) Jr(Fp Hq Hu Hv Hx Ih Ij Ik Il In Io Iq It Iv Jm Jn Jp Js Jt Li Lj Lv Ly Lz Mc Md Me Mf Mg Mh Mi Mj Mk Ml Mn Mq Ms Mv Mx My Na Nc Ne Ng Nh Ni Nj Nk Nl Ns Nu Nx Oe Of Og Oi Oy Oz Pb Pc Pd Pg Pz Qa Qb Qc Qd Qe) Ny(Fp Hr Hu Hv Hw Hx Ih Ii In Io Ip Iu Iv Jg Jm Jn Jo Jp Js Jt Li Lj Lu Lv Lx Lz Ma Mb Md Me Mg Mh Mi Mj Ml Mm Mn Mq Ms Mv Mw Mx Na Nb Nd Ne Nf Ng Nh Ni Nj Nk Nl Nm Nr Ns Nu Oe Oi Oz Pa Pb Pd Pg Pz Qa Qd Qe) Mz(Fp Hq Hr Hu Hv Hx Ih Ii Ij Ik Il In Io It Jm Jn Jo Jp Js Jt Lj Lu Lv Ly Lz Mb Mc Md Me Mf Mg Mh Mi Mj Mk Mn Mq Ms Mv Mx My Na Nb Ne Nf Ng Nh Ni Nj Nk Nl Ns Nu Nx Oe Of Oi Oy Oz Pc Pd Pz Qa Qb Qc Qd Qe) Mr(Fp Hq Hu Hv Hw Hx Ii Ij Il Io It Iu Iv Jk Jm Jo Jt Lh Li Lj Lu Lv Lx Lz Mb Mc Me Mf Mi Mj Mk Ml Mn Mq Ms Mv My Na Nb Nd Ne Ng Nh Ni Nj Nk Nl Nq Nr Ns Nu Nv Nx Oe Of Oy Oz Pa Pc Pd Pg Pz Qb Qc Qd Qe) Mp(Hq Hu Hx Ih Ik Il Io It Iu Jk Jm Jt Li Lj Lu Lv Lw Ly Lz Ma Mc Me Mf Mi Mj Mk Ml Mm Mn Mq Ms Mv Mx My Nd Ng Nh Nj Nk Nm Nq Ns Nu Nv Nx Oe Of Og Oh Oy Oz Pb Pc Pd Pg Pz Qb Qc Qd Qe) Mw(Fp Hq Hr Hx Ii Ij Il In Io It Iu Jg Jh Jk Jm Jo Jp Jt Li Lu Lv Ly Ma Mb Mc Md Me Mf Mj Mk Ml Mm Mn Mq Mv Nb Nd Nh Ni Nj Nk Nm Nq Ns Nu Nv Nx Oe Of Oz Pc Pd Pg Pz Qb Qc Qd Qe) Oh(Fp Hq Hr Hu Hx Ih Ij Ik Im In Io Ip It Jk Js Jt Li Lu Lv Lw Ma Mb Md Me Mh Mi Mj Mm Mn Ms Mx Nc Nd Ne Nh Ni Nj Nl Nm Nr Nv Nx Oe Og Oz Pc Pg Qb Qd Qe) Lx(Hr Hu Hx Ih Ij Im In Ip It Jk Jm Jo Jp Li Lj Lv Ma Mb Me Mg Mh Mi Mm Mq Mx My Nb Nc Ne Nf Nh Ni Nl Nm Nr Nv Nx Of Og Oy Pa Pb Pg Qb Qd Qe) Jh(Fp Hq Hr Hv Hx Ii Ij Il In Io It Jg Jk Jm Jo Jp Jt Lu Lv Ly Ma Mc Md Me Mf Mk Ml Mm Mn Mq Mv Nh Ni Nj Nk Nm Nq Ns Nu Nv Nx Of Oz Pc Pd Qc) Pa(Fp Hr Hv Hw Ih Ij Ik Il Im In Io Ip Iq It Iv Jk Jo Jp Jt Li Lv Ma Mb Md Me Mi Mm Mx Na Nc Ne Ng Nh Ni Nj Nl Nm Nr Nv Nx Og Oi Oy Oz Pb) Jg(Fp Hr Hv Hx Ih Ii Ij Ik Im In Io Ip Iv Jo Js Jt Li Lj Lu Lw Lz Mb Md Mg Mh Mi Mx My Na Nb Nc Nd Ne Ni Nl Nr Nv Oy Pg Pz Qb Qd Qe) Iq(Fp Hr Hv Hx Ih Ij Il In Ip Iv Jk Jn Jp Jt Li Lj Lv Lz Ma Md Mi Mm Mn Nb Nc Nd Nf Ni Nj Nm Nr Nv Nx Oi Pg Qa Qc) Jn(Hq Hr Hw Ii Ik Ip Iu Iv Jk Jo Jp Li Lu Lw Lz Mb Md Mh Mi Na Nb Nc Nf Nm Nq Nr Nv Oi Oz Pg Qa) Nn(Hq Il Io Iu Jk Jm Li Ly Lz Ma Mc Mk Ml Mm Mn Mq Mv Nk Nq Nu Nv Oe Of Pb Pd Qc Qe) Qa(Hr Hw Ii Ik Im Io Ip Iv Jk Jp Lu Lw Ma Mb Md Mi Mm Mn Nb Nc Nd Nf Nm Nr Nv Oi Pg) Mu(Hq Hx Il Io Jk Jm Lu Ly Mc Mf Mk Mq Ms Mv Ni Nk Nq Nu Of Oz Pc Pd Qc) Jj(Fp Hv Ih Ij In Ip Iu Jm Jp Jt Lw Md Mi Mn Mv Mx Na Nc Nl Nq Qb Qe) Nf(Hw Ip Iu Iv Jk Jp Li Lw Lz Ma Mi Mm Nc Nd Nl Nm Nr Nv Oz Pg Qd) Im(Hw Ii Iv Jo Jp Js Jt Lw Mb Md Mi Na Nb Nr Nv Pg) Lh(Ij It Jt Lu Lz Mc Mf Mk Mv Nb Nr Nx Oz Pc Pd Qc) Iv(Ih Ip Jk Jp Li Lw Lz Mb Md Me Nd Nq Nv Pg) Hw(Ih Ip Jp Li Lw Lz Ma Md Mi Mm Nd Nv Pg) Ii(Ih Ik Li Lj Lw Ma Mm My Nc Of Og Oy Pb) Nb(Ip Js Li Lw Ma Mm My Nc Oy Pb) Nv(Hv Ik Jo Js Lw Mi Na Nm Nr Oi) Mm(Hv Ij In Jo Js Mi Na Nr) Li(Ik Lw Mb Na Nd Oi) Om(Il Jk Mc Nq Pc Pd) Ma(Hv Ih Js Na Nr) Lw(Jp Js Mi Nr) Nw(Ly Mc Mf Qd) Ik(Mi Mj Pg) Nr(Jp Md) Nd(Hv Js) NmLu MiJp NgJq

Unconstrained panels with 2 analytes, where 1.0E-3 >= 'model p-value' > 1.0E-4. Contains 1,281 panels of 7,260 total panels evaluated. : Mi(Fp Hq Hr Hu Hv Hx Ih Ii Ij Il In Io Ip It Iu Iv Jk Jm Jo Js Jt Li Lj Lu Lv Ly Lz Ma Mb Mc Md Me Mf Mg Mh Mj Mk Ml Mn Mq Ms Mv Mx My Na Nb Nc Nd Ne Ng Nh Ni Nj Nk Nl Nm Nq Nr Ns Nu Nx Oe Of Og Oi Oy Oz Pb Pc Pd Pg Pz Qb Qc Qd Qe) Nv(Fp Hq Hr Hu Hx Ih Ii Ij Il In Io Ip It Iu Jk Jm Jp Jt Li Lj Lu Lv Ly Lz Ma Mc Md Me Mf Mg Mh Mj Mk Ml Mm Mq Ms Mv Mx My Nb Nc Nd Ne Ng Nh Ni Nj Nk Nl Nq Ns Nu Nx Ny Oe Of Og Oy Oz Pb Pc Pd Pg Pz Qb Qc Qd Qe) Iv(Fp Hq Hr Hu Hv Hw Hx Ii Ij Il In Io It Iu Jm Jo Js Jt Lj Lu Lv Ly Mc Mf Mg Mh Mj Mk Ml Mn Mq Ms Mv Mx My Na Nb Nc Ne Ng Nh Ni Nj Nk Nl Nm Nr Ns Nu Nx Oe Of Og Oi Oy Oz Pb Pc Pd Pz Qb Qc Qd Qe) Pg(Fp Hq Hr Hu Hv Hx Ih Ii Ij In Io Ip Iu Jk Jm Jo Jp Js Jt Li Lj Lu Lw Ly Lz Ma Mb Md Me Mg Mh Mj Ml Mm Mn Mq Mx My Na Nb Nc Nd Ne Ng Nh Ni Nj Nl Nm Nr Ns Nx Of Og Oi Oy Oz Pa Pb Pz Qb Qd Qe) Nf(Fp Hq Hr Hu Hv Hx Ih Ii Ij Il In Io It Jm Jo Js Jt Lj Lu Lv Ly Mb Mc Md Me Mf Mg Mh Mj Mk Ml Mn Mq Ms Mv Mx My Na Nb Nc Ng Nh Ni Nj Nk Nq Ns Nu Nx Oe Of Og Oi Oy Pb Pc Pd Pz Qb Qe) Qa(Fp Hq Hu Hv Hx Ih Ij Il In It Iu Jm Jo Js Jt Li Lj Lv Lz Mc Me Mf Mg Mh Mj Mk Ml Mq Ms Mv Mx My Na Ne Ng Nh Ni Nj Nk Nl Nq Ns Nu Nx Oe Of Og Oy Oz Pb Pc Pd Pz Qb Qc Qd Qe) Jn(Fp Hu Hv Hx Ih Ij Il In Io It Jm Js Jt Lj Lv Ly Mc Me Mf Mg Mj Mk Ml Mn Mq Ms Mv Mx My Ne Ng Nh Ni Nj Nk Nl Ns Nu Nx Oe Of Og Oy Pb Pc Pd Pz Qb Qc Qd Qe) Nb(Fp Hq Hr Hv Hw Hx Ih Ii In Iu Jk Jo Jp Jt Lj Lu Lv Lz Mb Md Me Mg Mh Ml Mn Ms Mv Mx Na Nd Ne Ng Nh Nj Nk Nl Nm Nq Nr Nx Oe Of Oi Pa Pd Qb Qd Qe) Li(Hq Hr Hv Hx Ih Ij Il Im In Io Ip It Iu Jk Jo Jp Js Jt Li Lu Lv Me Mh Mn Mv Mx Nc Ne Ng Nh Ni Nk Nl Nq Nr Ns Nx Oe Of Oi Oz Pb Pd Pz Qb Qe) Im(Fp Hq Hr Hv Hx Ih Ij Ik In Io Ip It Iu Jk Lj Lu Lv Lz Ma Me Mh Mk Mm Mn Mq Mv Mx Nc Nd Ne Nh Ni Nj Nl Nm Nq Nu Nx Og Oi Oz Pd Qb Qd Qe) Iq(Hq Hu Io It Iu Jm Js Lu Ly Mc Me Mf Mg Mh Mj Mk Ml Mq Ms Mv Mx My Nc Ng Nh Nk Nl Nq Ns Nu Oe Of Og Oy Oz Pb Pc Pd Pz Qb Qd Qe) Hw(Fp Hq Hr Hx Ii Ik In Iu Jk Jo Js Jt Lj Lu Lv Me Mh Mn Mv Mx Nc Ne Ng Nh Nj Nk Nl Nm Nq Nr Ns Nx Og Oi Oz Pb Pd Qb Qc Qd Qe) Ii(Fp Hr Hv Hx In Ip Iu Jk Jo Jp Js Jt Lv Lx Lz Mb Md Mg Mh Ml Mn Ms Mx Na Nd Ne Ng Nh Nj Nk Nl Nm Nq Nr Oe Oi Pa Qb Qd Qe) Lw(Fp Hq Hr Hv Hx Ih Ij Il In Ip Iu Jk Jo Lj Lu Lz Ma Mb Md Mh Mj Mm Mn Mv Mx Na Nc Nd Ne Nh Nl Nq Nx Og Oi Qb Qd Qe) Nr(Fp Hq Hr Hv Hx Ih Ij Ik In Ip Jk Jo Js Jt Lu Lv Mb Mh Mn Mx Na Nc Nd Ne Nh Nj Nl Nm Nq Nx Og Oi Oz Pb Qb Qd Qe) Jg(Hq Hu Il It Iu Jk Jm Jp Lv Ly Ma Mc Me Mf Mj Mk Ml Mm Mn Mq Ms Mv Nh Nj Nk Nl Nm Nx Oe Of Oz Pb Pc Pd Qc) Jp(Fp Hr Hv Hx Ih Ij In Ip Iu Jk Jo Js Jt Lu Lz Ma Mb Md Mh Mm Mx Na Nc Nd Ne Nh Nl Nm Nq Nu Nx Oi Pd Qb Qd Qe) Pa(Hq Hu Hx Iu Jm Lj Lu Ly Lz Mc Mf Mg Mh Mj Mk Ml Mn Mq Ms Mv My Nd Nk Nq Ns Nu Oe Of Pc Pd Pz Qb Qc Qd Qe) Mm(Fp Hr Hx Ih Io Ip It Jk Jt Lj Lu Lv Lz Ma Mb Md Me Mg Mh Mj Ml Mx Nc Nd Ne Ng Nh Ni Nl Nx Oi Qb Qd Qe) Jk(Fp Hu Hv Ih Ij Ik In Ip Jo Js Jt Lj Lz Ma Mb Md Mg Mh Mj Mx Na Nc Nd Ng Ni Nm Nx Ny Og Oi Qd Qe) Lx(Fp Il Io Iu Lu Lz Mc Md Mf Mj Mk Ml Mn Ms Mv Nd Nj Nk Nq Ns Nu Oe Oi Oz Pc Pd Pz Qc) Ma(Fp Hr Hx Ij Ik In Ip It Jo Jt Lj Lz Mb Md Mg Mh Mx Nc Nd Ne Ng Nl Nm Nx Oi Qb Qd Qe) Jj(Hr Hu It Lj Lu Lv Lz Mb Me Mg Mh Mj Mk Mq My Ne Ng Nh Ni Nj Nk Nu Oi Oy Oz Pz Qc Qd) Jo(Fp Hr Hx Ih Ik Ip Js Lj Lu Lz Md Mg Mh Mn Mx Nc Nd Ng Nl Nq Og Pb Qb Qd Qe) Oh(Il Iu Jm Lj Ly Lz Mc Mf Mg Mk Ml Mq Mv My Ng Nk Nq Ns Nu Of Oy Pb Pd Pz Qc) Js(Hq Hr Hx Ih Ik Ip Iu Jt Lu Lv Lz Mb Md Mh Mn Na Nc Nm Nq Nx Oi Oz Qb Qe) Nm(Fp Hv Hx Ih Ip Lz Md Mg Mh Mx Na Nc Nd Ne Ng Nl Og Oi Qb Qd Qe) Nd(Fp Hx Ih Ij In Ip Jt Lj Md Me Mh Mx Na Nc Ne Nh Nl Nx Qd Qe) Na(Fp Hq Hx Ih Ip Iu Lz Md Mh Mn Mx Nc Nl Nq Qb Qd Qe) Ih(Hq Hr Hv Hx Ij In Ip Jt Lu Mb Md Mh Mj Nx Oi) Jt(Fp Hq Hx Ip Lj Lu Lz Md Mg Mh Mn Nc Qb Qe) Ny(Hq Ij Il It Ly Mc Mf Mk Nq Nx Pc Qb Qc) Po(Lu Lz Mc Mf Mj Mq Nq Nu Nx Oz Pc Qc) Md(Fp Hv Hx Ip Lj Lz Mb Mh Mx Qb Qd Qe) Ip(Hv Hx Ij In Lz Mb Mn Nc Nl Nx) Lz(Hv Hx Ij Ik In Mb Nx) Mb(Fp Mh Mx Qb Qd Qe) Nc(Hv Hx Ij In Ni Nx) Qd(Hx Ik Lu Nx) Hv(Iu Me Nq) NqLj NsPd MhNx MjIl HxOg QeOi Unconstrained panels with 2 analytes, where 1.0E-2 >= 'model p-value' > 1.0E-3. Contains 1,269 panels of 7,260 total panels evaluated. : Qd(Fp Hq Hr Hu Hv Ih Ij Il In Io Ip It Iu Js Jt Li Lj Lv Ly Lz Mc Me Mf Mg Mh Mj Mk Ml Mn Mq Ms Mv Mx My Nc Ne Ng Nh Ni Nj Nk Nl Nq Ns Nu Oe Of Og Oi Oy Oz Pb Pd Pz Qb Qc Qe) Hx(Fp Hq Hr Hu Hv Ij Ik Il In Io It Iu Jk Jm Lj Lu Lv Ly Mb Mc Me Mf Mg Mh Mj Mk Ml Mn Mq Ms Mv Mx My Ne Ng Nh Ni Nj Nk Nl Nq Ns Nu Nx Oe Of Oi Oy Oz Pb Pc Pd Pz Qb Qc Qe) Nx(Fp Hq Hr Hu Hv Ii Ij Ik Il In Io It Iu Jo Jt Lj Lu Lv Mb Md Me Mf Mg Mj Mk Mn Ms Mv Mx My Na Ne Ng Nh Ni Nj Nk Nl Nm Nq Ns Nu Oe Og Oi Oy Oz Pb Pc Pd Pz Qb Qc Qe) Qc(Fp Hq Hr Hu Hv Ih Ij Ik Il In Io Ip It Iu Jm Lj Lu Lv Lz Me Mg Mh Mj Mk Ml Mn Mq Ms Mv Mx My Nc Ne Ng Nh Ni Nj Nk Nl Nq Ns Nu Oe Of Og Oz Pb Pd Pz Qb Qc) Jt(Hr Hu Hv Ij Ik Il In Io It Iu Jm Jo Lv Lw Ly Mb Mc Me Mf Mj Mk Ml Mq Ms Mv Mx My Na Ne Ng Nh

Figure 43 Continued

Ni Nj Nk Nl Nm Nq Ns Nu Oc Of Og Oi Oy Oz Pb Pc Pd Pz Qc) Md(Hq Hr Hu Ij Ik Il In Io It Iu Jm Lu Lv Ly Mc Me Mf Mg Mj Mk Ml Mn Mq Ms Mv My Nc Ne Ng Nh Ni Nj Nk Nl Nq Ns Nu Oe Of Og Oi Oy Oz Pb Pc Pd Pz Qc) Na(Hr Hu Hv Hw Ij Ik Il In Io It Jm Jo Lj Lu Lv Ly Mb Mc Me Mf Mg Mj Mk Ml Mq Ms Mv My Ne Ng Nh Ni Nj Nk Ns Nu Oe Of Og Oi Oy Oz Pb Pc Pd Pz Qc) Nm(Hq Hr Hu Ij Ik Il In Io It Iu Jm Jo Lj Lv Lw Ly Mb Mc Me Mf Mj Mk Ml Mm Mn Mq Ms Mv My Nh Ni Nj Nk Nq Ns Nu Oe Of Oy Oz Pb Pc Pd Pz Qc) Ip(Fp Hq Hr Hu Ik Il Io It Iu Jm Lj Lu Lv Me Mg Mh Mj Mk Ml Mq Ms Mv Mx My Ne Ng Nh Ni Nj Nk Nq Ns Nu Of Og Oi Oy Oz Pb Pc Pd Pz Qb Qc) Hv(Fp Hq Hr Hu Hw Ij Ik Il In It Jo Js Lj Lu Lv Mb Mg Mh Mj Mk Mn Mv Mx My Ne Nh Ni Nj Nk Nl Ns Nu Of Og Oi Oy Oz Pb Pd Qb Qc) Ih(Fp Hu Ik Il Io It Iu Lj Lv Lz Me Mf Mg Mk Ml Mn Mq Ms Mv Mx My Nc Ne Nh Ni Nj Nk Nl Nq Ns Nu Of Og Oy Oz Pb Pc Pd Pz Qb) Js(Fp Hu Ij Il In Io It Jm Lj Ly Mc Me Mf Mg Mj Mk Ml Mq Ms Mv Mx My Ne Ng Nh Ni Nj Nk Nl Ns Nu Oe Of Og Oy Pb Pc Pd Pz Qc) Jk(Hq Hr Il Io It Iu Jm Lu Lv Ly Mc Me Mf Mk Ml Mn Mq Ms Mv My Ne Nh Nj Nk Nl Nq Ns Nu Oe Of Oy Oz Pb Pc Pd Pz Qb Qc) Ma(Hq Hu Il Io Iu Jm Lu Lv Ly Mc Me Mf Mj Mk Ml Mn Mq Ms Mv My Nh Ni Nj Nk Nq Ns Nu Oe Of Og Oy Oz Pb Pc Pd Pz Qc) Jo(Hq Hu Ij Il Io It Iu Jm Lv Ly Mb Mc Me Mf Mj Mk Ml Mq Ms Mv My Ne Nh Ni Nj Nk Ns Nu Oe Of Oi Oy Oz Pc Pd Pz Qc) Jp(Hq Hu Ik Il Io It Jm Lj Lv Ly Mc Me Mf Mg Mj Mk Ml Mn Mq Ms Mv My Ng Ni Nj Nk Ns Oe Of Og Oy Oz Pb Pc Pz Qc) Mx(Fp Hq Hr Hu Ij Ik Il In Io Iu Lj Lu Lv Lz Me Mf Mh Mj Mn Mq Mv My Nc Ne Nh Ni Nj Nl Nq Of Og Oi Oz Pd Qb) Nr(Hu Il Io It Iu Jm Lj Ly Lz Mc Me Mf Mg Mj Mk Ml Mq Ms Mv My Ng Ni Nk Ns Nu Oe Of Oy Pc Pd Pz Qc) Lw(Hu Ik Io It Jm Lv Ly Mc Me Mf Mg Mk Ml Mq Ms My Ng Ni Nj Nk Ns Nu Oe Of Oy Oz Pb Pc Pd Pz Qc) Qb(Fp Hq Hr Ij Ik In Io It Iu Lu Lv Lz Me Mh Mj Mn Mq Mv Nc Nd Ne Nh Ni Nj Nl Nq Nu Og Oi Oz Pd) Mm(Hq Hu Ik Il Iu Jm Ly Mc Mf Mk Mn Mq Ms Mv My Nj Nk Nq Ns Nu Oe Of Og Oy Oz Pb Pc Pd Pz Qc) Lz(Fp Hq Hr Il It Iu Li Lu Lv Me Mh Mj Mn Mq Mv My Nc Nd Ne Nh Ni Nj Nl Nq Of Oi Pd) Hw(Hu Ij Il Io It Jm Ly Mb Mc Mf Mg Mj Mk Ml Mq Ms My Ni Nu Oe Of Oy Pc Pz) Ii(Hq Hu Ij Il Io It Jm Lu Ly Mc Me Mf Mj Mk Mq Mv Ni Ns Nu Oz Pc Pd Pz Qc) Fp(Hq Hr Ij Ik In Iu Li Lu Lv Me Mh Mj Mn Mv My Nc Ne Nh Nl Nq Oi Oz Pd) Nd(Hq Hr Hu It Iu Lu Lv Mb Mf Mj Ml Mn Mq Mv Ni Nj Nk Nq Ns Nu Oi Pd Qc) Mh(Hq Hr Ij Ik In It Iu Lu Lv Mj Mn Mv My Nc Ne Nh Ni Nl Nq Of Oz Pd) Nq(Hr Hu Ij In It Iu Lv Mb Me Mj Mn Mq Nc Ne Nh Ni Nl Oi Oz Pg) Im(Hu Il Jm Ly Mc Mf Mg Ml Ms My Ng Nk Ns Oe Of Oy Pb Pc Pz Qc) Li(Hu Jm Lj Ly Mc Mf Mj Mk Ml Ms Mv My Nj Ns Nu Oe Of Oy Pc Qc) Pd(Hr Ij Ik In Iu Lj Lu Lv Mb Mg Mj Mn Nc Ne Nh Nl Og Oi Pb Pg) Nb(Hu Ij Il Io It Jm Ly Mc Mf Mj Mk Mq Ni Ns Nu Oz Pc Pz Qc) Mb(Hq Ij Il Iu Lj Lu Lv Mj Mk Ml Mn Mv Nc Ne Nh Nj Nl Oz) Mn(Hq Hr Ij In Iu Lj Lu Lv Mj Mq Mv Nc Ne Nh Ni Nl Oi) In(Hq Il Iu Lj Lu Lv Mj Mv Ne Nh Nj Nk Nl Og Oz Pb) Ij(Hq Ik Iu Lj Lu Mj Mv Ne Nh Nj Nl Og Oi Oz Pb) Hq(Hr Ik Iu Lj Lv Mj Nc Ne Nh Ni Nl Og Pb) Pg(Il It Lv Mc Mf Mk Ms Mv Nk Nu Oe Pc Qc) Jj(Ik Io Ly Mc Mf Ml Ms Ns Oe Og Pb Pc) Lj(Hr Iu Lu Lv Mv Nc Nl Oi Oz) Lv(Hr Iu Lu Nc Ne Nh Nl) Mv(Ik Iu Nc Ne Nl Og Oi) Lu(Hr Iu Mj Nc Nl) Nc(Hr Iu Mj Mq) Nl(Hr Mj Ni) Iu(Hr Ni Oi) Ik(Mk Oz) NsMq NeHr NfQc

Unconstrained panels with 2 analytes, where 5.0E-2 >= 'model p-value' > 1.0E-2. Contains 641 panels of 7,260 total panels evaluated. : Mv(Hq Hr Hu Il Io It Lu Lv Mc Me Mf Mg Mj Mk Ml Mq Ms My Ng Nh Ni Nj Nk Nq Ns Nu Oe Of Oy Oz Pb Pd Pz Qc) Nc(Hu Ik Il Io It Jm Ly Mc Me Mf Mg Mk Ml Ms My Nc Ng Nh Nj Nk Nl Ns Nu Oe Of Og Oi Oy Oz Pb Pc Pz Qc) Hq(Hu Il Io It Jm Lu Ly Mc Me Mf Mg Mk Ml Mq Ms My Ng Nj Nk Nq Ns Nu Oe Of Oi Oy Oz Pc Pd Pz Qc) Mb(Hr Hu Ik In Io It Jm Ly Mc Me Mf Mg Mq Ms My Ng Ni Nk Ns Nu Oe Of Og Oi Oy Pb Pc Pz Qc) Mn(Hu Ik Il Io It Jm Ly Mc Me Mf Mg Mk Ml Ms My Ng Nj Nk Ns Nu Oe Of Og Oy Oz Pb Pc Pz Qc) Ij(Hr Hu Il In Io It Jm Lv Ly Mc Me Mf Mg Mk Ml Mq Ms My Ng Ni Nk Ns Nu Oe Of Oy Pc Pz Qc) Iu(Hu Ik Il Io It Jm Me Mg Mj Mk Ml Mq Ms My Ne Ng Nh Nj Nk Nl Ns Nu Oe Of Og Oz Pb Pc Qc) Fp(Hu Il Io It Jm Lj Ly Mc Mf Mg Mk Ml Mq Ms Ng Ni Nj Nk Ns Nu Oe Of Og Oy Pb Pc Pz Qc) Nq(Ik Il Io Jm Lu Ly Mc Mf Mg Mk Ml Ms My Ng Nj Nk Ns Nu Oe Of Og Oy Pb Pc Pd Pz Qc) Mh(Hu Il Io Jm Lj Ly Mc Me Mf Mg Mk Ml Mq Ms Ng Nj Nk Ns Nu Oe Og Oi Oy Pb Pc Pz Qc) In(Hr Hu Ik Io It Jm Ly Mc Me Mf Mg Mk Ml Mq Ms My Ng Ni Ns Nu Oe Of Oi Oy Pc Pz Qc) Pd(Hu Il Io It Jm Ly Mc Me Mf Mk Ml Mq Ms My Ng Ni Nj Nk Nu Oe Of Oy Oz Pc Pz Qc) Lj(Hu Ik Il Io It Lz Me Mg Mj Mk Ml Mq My Ne Nh Ni Nj Nk Ns Nu Of Og Oy Pb Qb) Lv(Hu Ik Il Io It Me Mj Mk Ml Mq My Ni Nj Nk Ns Nu Of Og Oi Oz Pb Qc) Lz(Hu Io Jm Ly Mc Mf Mg Mk Ml Ms Ng Nk Ns Nu Oe Og Oy Oz Pb Pc Pz Qc) Nh(Hr Ik Il Io It Lu Me Mj Mk Ml Mq My Ni Nj Nl Ns Nu Of Og Oi Oz Qc) Nl(Hu Ik Il Io It Ly Me Mk Ml Mq My Nj Ns Nu Of Og Oi Oy Oz Pb Qc) Qb(Hu Il Jm Ly Mc Mf Mg Mk Ml Ms My Ng Nk Ns Oe Of Oy Pb Pc Pz Qc) Hr(Hu Ik Il It Me Mj Mk Ml Mq My Ni Nj Nk Ns Nu Og Oi Oz Pb Qc) Nd(Ik Il Io Jm Ly Mc Mg Mk Ms My Ng Oe Of Og Oy Oz Pb Pc Pz) Mx(It Jm Ly Mc Mg Mk Ml Ms Ng Nk Ns Nu Oe Oy Pb Pc Pz Qc) Lu(Ik Il It Me Ml Mq My Ne Ni Nj Nk Nu Of Og Oi Oz Qc) Ne(Ik Il It Me Mj Mq My Ni Nj Ns Nu Of Og Oi Oz Qc) Mj(Hu It Me Mk Mq My Ni Nj Nk Nu Of Og Oi Oz) Hv(Io Jm Ly Mc Mf Ml Mq Ms Ng Oe Pc Pz) Oz(It Me Mq Ni Nj Ns Og Oi Pb) Ih(Jm Ly Mc Ng Oe Qc) Nx(Jm Ly Mc Ml Mq Of) Qe(Ly Mc Mf Oy Pc) Il(Mq Ni Og Oi) Ip(Ly Mc Mf Oe) Nu(Ik It) Mq(Nj Nk) Ni(Nj Nk) Qd(Jm Pc) IkIt Constrained panels with 3 analytes, where 1.0E-8 >= 'model p-value' > 0. Contains 1,085 panels of 287,980 total panels evaluated. : Jj{Nt(Fr Ii Ip Iq Is Jg Jh Ji Jk Jl Jn Jq Jr Js Lh Mn Mp Mt Mu Mw Mz Nf Nj Nn Nw Ny Ok Om On Pf) Mr(aA Et Fr Ik Ip Is Jg Jh Ji Jk Jl Jq Jr Lw Ma Mm Mp Mt Mu Mw Nc Nm Nn Nw Oh Ok Om On Pb) Mu(Et Hw Ii Il Iq Ir Is Iv Ji Jl Jn Jr Lh Lx Mp Mw Nc Nd Nj No Nr Og Ok Om Pa Pe Po Qb) Lx(aA Et Fr Ii Ir Is Iv Jh Ji Jk Jl Jn Jq Jr Ly Mh Mw My Nm Nn Ok Om On) Lh(Fr Is Jg Jh Ji Jk Jl Jq Jr Mp Mt Mw Nn Ok Om Pb) Fr(aA Hw Im Ir Is Iv Ji Jn Jq Jr Nd Ok Pe) Mw(aA Iq Ir Ji Jl Jn Jr Mz Nd Ne No Ok) Nd(Ii Is Jh Ji Jk Jl Jq Nn Ok Om On) Jh(Hw Iq Is Ji Jl Jr Nc No Pe) Ji(Hw Jk Jl Nn No Pa Pe) Om(Hw Is Jl Nc Nl No Og) Jk(Is Jr Og Oi Ok) No(Jg Mj Nj Nn) Jl(aA Io Oi) On(Io Oi Pz) Po(Ik Oy) Pe(Ik Nn) aA(Jg Me) IiIm JqPa} Ik{Jh(aA Fr Hw Iq Ir Is Iv Ji Jl Jr Lh Lz Mh Mi Mj Mk Mr Mx Nb Nc No Nr Nt Ok On Oz Pa Pe Pf Po Qa) Om(aA Et Fr Hw Iq Ir Is Iv Ji Jl Lh Lz Mk Mp Mr Mt Mu Mw Nb No Nr Nt Og Ok On Oz Pa Pe Pf Po) Pe(Et Fr Is Jg Ji Jk Jl Jq Lw Lx Ma Me Mm Mp Mt Mu Mw Nj Nn Nw Ok On Pf) Ji(Fr Hw Io Iv Jk Jl Lz Mk Mr Mt Mu Mw Nn No Nr Nt Ok Oz Pa Pf Po) Mw(aA Iq Ir Is Iv Jl Jn Jq Jr Lz Mr Mz No Ok On Pa Pf) Mr(Fr Is Jg Jl Jq Lw Lx Ma Mp Mt Mu Nn Nw Ok On) Iv(Fr Jg Jq Lw Lx Ma Mt Mu Nn Nw Ok On) Ok(Fr Jk Jl Lx Mu Nn No Nw Pa Pf Po) Mu(aA Ir Is Jl Lh No On Pa) On(Io Mp No Oh Oi Pc Pz) Is(Fr Lx No Pf Po) Jg(aA Jl No) Fr(Ir Jr) Nj(aA No) Jq(Mk Pa) LxIr MtJl} Ji{Io(aA Et Hw Iq Jl Lx Mb Mr Nc Nd Nt Ok Pa Pe) Jh(aA Ij Im Mg My Nc Nd Ng Og Oi Oy Pb Pz) Oi(aA Et Fr Jg Jl Mt Mu Mw Nn Ok On Pa) Pz(Et Fr Jg Jl Mr Mu Nd Nn Ok On Pf) Og(Fr Jg Jk Jl Mr Mu Mw Om Pa Pe) Nx(Fr Jk Jl Lx Mr Nd No Nt Pa) Mg(Fr Ma Mm Mu Mw Nn Nt) My(Fr Jg Jk Mu Mw Om Pa) Ij(Hw Mr Mu Mw Ok Om Pe) Qc(Iq Jn Jr Mp Mt Mw Mz) aA(Hr Ih Me Mj Mu Oh Qd) Pb(Jk Mr Mu Om Pa Pe) No(Hr Ii Mj Qd) Ng(Jk Mu Mw Pa) Oy(Jk Mw Om Pa) Nt(Ii Jo Lv) Mr(Hr Ii Mj) Im(Fr Jl Ok) Ma(Fr Mu) Jl(Lv Mj) Ok(Jt Mq) NnOh LxLy NdIn OfOm} No{Hr(aA Et Im Ip Ir Is Jh Jl Jn Jq Jr Ms Mt Mu Mw Mz Nf Oi Ok Om On) Mj(Et Ir Is Jn Jq Jr Js Lw Mp Ms Mz Nf Nn Oh Ok Om On) Jg(aA Hu Il Im Jm Mv My Ng Ns Nv Og Oi Oy Pz) Nj(aA Fr Jn Ly Mb Ms Mu Mw Mz Nf Nl) Om(Hu Jo Mg My Ng Nv Of Og Oy Pb Po) Mb(Et Il Im Is Me Mt Ns Nw Pb) Mw(Hu Il Jm My Ng Nv Og Oy Pb) Jh(Hu Mg My Ng Og Oy Pb) Mm(Io Iu Jn Jr Mz) Im(Jn Lw Mp Ms Mz) Ok(Jo Mg Mq Pb Pz) Oi(Mt Nn Oh On) Me(aA Io Jm) Nm(Jo Mg) Pz(Et On) Pb(Ir Na) FrJn MpIo MuHu IsQd NvOn} aA{Io(Et Fr Hr Ip Is Jg Jl Ma Me Mm Mn Mp Mt Mw Nc Nj Nm Nn Nw Ok On Pf) Me(Hu Is Jh Jn Jq Jr Lx Mf My Mz Nf Nj Nw Oi Ok Om On Pc Pe Pf) Oi(Et Fr Hr Jg Jl Ma Mp Mt Mu Mw Nj Nn Nw Ok Om On) Hr(Et Ip Jl Jr Mt Mu Mw Nj Ok Om On Pf Po) Nj(Fr Jg Jh Ma Mb Mp Mu Mw Nd

Figure 43 Continued

Nn Om) Jg(Hu Ms Mv My Ng Ns Og Oy) Oh(Lw Mm Mp Nn Ok On Pc) My(Fr Mw Nn Om On) Om(Og Oy Pb) Nn(Mp Pc) Mw(Og Oy) Jq(Lx Nd) Jt(Nm Ok) LwPc MqOk PzOn} Om{Og(Et Hq Hw Im Iq Ir Is Iv Jg Jl Lh Lx Mr Nb Nt Nw Oh Ok On Oy Pa Pb Pe) Oy(Et Fr Ii Is Jl Lh Lx Mp Mr Mt Mw Nd Nt Oh Ok On Pa Pe Po) Of(Is Jl Lh Lx Mr Nd Nt Ok On Pa Pe Po) Pb(Et Hw Is Jl Lh Mr Nr Nt Ok On Pa Pe) My(Fr Is Lh Lx Mr Nt Nw Ok On Pa) Mg(Lh Lx Mi Mp Nt Ok) Ng(Lh Lx Nd Nt Pa) Lx(Hu Ly) Ij(Is Ok) PzOk} Jh{Ng(Jl Lh Lx Mr Nd Nt On Pa Pe Po) Og(Is Jl Lh Mh Mr Nw Ok On Pa Pe) My(Jl Lh Lx Mh Mr Nw On Pa Po) Oy(Jl Lh Lx Mh Mr On Pa Pe Po) Mg(Iq Jl Lh Lx Mr Ok Pe) Hu(Jl Lh Lx Mr Nt Pa) Pb(Jl Lh Mr Pe) Pz(Jl Ok) LhOf} On{Oy(Ii Im Io Jg Mj Mu Mw Oh Oi Pz Qc Qd) Oi(Hr Hu Lj Lv Mg My Ng Of Pb) Pz(Hr Hu Mg My Ng Nv Og Pb) My(Im Io Jg Mu Mw Nq) Ng(Im Io Lx Mu Nd) Io(Hu Og) Jq(Ij Im) JgOg PbPe} Ok{Mg(Fr Jk Lx Mu Mw Nd Nn) Mw(My Ng Og Oy Pb Pz) Pz(Fr Mu Nd Nn) Lx(Jo Ly Pb) Mq(Mp Mu Nn) Nw(Im Oi Pb) Fr(Jo Ng) Jq(Im Nd) NnOi MuPb} Jq{Pa(Im Md My Nb Og Oy Pb) Mr(Hr Im Mj Mp Og Pb) Im(Fr Jl Nc Pe) NdJl JgOg PbPe} Is{Mu(Hr Mg My Ng Nj Og Oi Oy Pb Pz) Fr(Mg My Ng Oi Pz) Mw(My Og) NnOi JgOg} Mw{Ng(Lx Mr Po) Oy(Lx Mt Po) My(Iq Nw) Og(Jr Mz)} Jg{Ng(Lh Lx Nd Nt) Jl(Og Pz)} Nn{Jl(Oi Pz) MgPe IiOy} Pb{Mu(Ir Pe) NfJl HwNw} Fr{Mg(Iv Nm) IrJo} Lx{Ly(Mr Pe)} MuNgPa

Constrained panels with 3 analytes, where 1.0E-7 >= 'model p-value' > 1.0E-8. Contains 2,610 panels of 287,980 total panels evaluated. : Ik{Jh(Et Fp Hx Ih Ii Il Ip Iu Jn Jo Jq Js Li Lj Lu Lx Mp Mt Mu Mw Mz Na Nd Ne Nf Nk Nl Nn Nu Nv Nw Ny Og Oh Om Pg Qb Qd Qe) Jl(Fr Im Io Ir Is Iv Jn Jr Js Lh Li Lw Lx Md Mp Mz Nb Nf Nm Nn No Nt Nw Ny Og Oi Pf Po) Om(Fp Im Iu Jn Jo Jr Li Lj Lx Mh Mi Mj Mm Mx My Na Nc Nd Ne Nl Nn Nu Nw Oh Qa Qe) Mu(Et Iq Jn Jq Jr Lx Lz Mi Mk Mp Mt Mw Mz Nb Nj Nr Nt Nw Ny Oz Pf Po Qb) Is(Et Hw Ii Io Ir Iv Jg Ji Jk Lh Lz Mk Mp Mt Nb Nn Nr Nt Nw Oi Ok Pa Pb) Mr(aA Et Im Ip Jk Jn Jr Me Mm Nj No Ny Oh Pb Pf Pg Po Qd) Ok(Im Io Jg Jt Lz Mk Mp Mq Mt Nd Nj Nt Ny Oh Oi Oz Pc Pz) Mw(Et Js Lh Lj Mg Mk Mt Mx Nb Ne Ng Nr Nt Nw Oz Po Qd) Iv(Et Ip Jj Jk Me Mm Mp Nj Nm No Ny Oh Pf Pg Po) Nw(Hw Ir Jo Lh Mk Na Nb Nr Nt Pa Pf Po) Lx(Et Hq Mh Mk My Ng Nt Ny Oz Pa Pb) Pf(Et Ii Ir Jj Jq Lh Nb No Nt Ny Po) Mt(Ir Jq Lh Mk Nb Nr Nt Oz Pa Po) Po(aA Et Fr Jg Jq Lw Mp Nn) Pe(aA Im Jr Mj No Ny Oh Pb) Ir(Im Jg Ji Ma Mp Nn) Lh(Fr Jg Ji Jo Jq Nn) Fr(Hv Jn Nb Nt) Ji(Jg Ma Na Nb) Nt(Jq Jr Mz) Pa(Mz Nn Ny) NoNs MkNy} Jj{Lx(Hq Hv Hw Hx Ih Ip It Jg Jo Js Jt Lh Lw Mb Ml Mm Mp Mt Mv Mz Na Nc Ng Nj Nr Nt Nv Nw Nx Ny Og Oh Oy Pb Pf Pg Qa) Po(aA Et Hx Im Ip Is Jg Jh Jq Jr Lw Mh Ml Mm Mp Mt Mv My Nc Nd Nl Nm Nn Ny Of Og Oh Pb) Nn(aA Hu Hw Ii Il Ir Is Iv Jo Jq Jr Ma Mp Mz Nc Ne Nf Ny Of Oh Oi Ok Om Pa Pc Pg) Nd(aA Et Ij Il Ir Iv Jg Jn Jr Lh Mp Mr Mt Mz Nm Nr Nt Nv Nw Ny Oh Pe Pf Pg) Pe(aA Et Ih Im Ip Is Jg Jk Jq Jr Lw Ma Mm Mn Mp Mt Mw Nc Nm Nv Nw Oh Pb) Mr(Hx Ih Ii Jn Lh Ml Mn My Nv Ny Of Og Pf) Jh(Fr Ir Lu Lz Mh Ne Nk Nl Og Ok Pa Pf Pg) Fr(Hv It Jo Mu Mz Na Nc Ne Nf Nr Om) Mp(Hw Ii Il Ir Iv Jn Jq Jr Mz Nf Pa) Mt(Hw Ii Ir Iv Jo Jq Mb Nc Nr Oi Pa) Is(Hq Hw Ii Io Jg Jq Lu Mw Nf Pa) Ii(aA Iq Jr My Of Oy Pb Pf) Jq(Hw Il Im Jg Jk Mu Mw Pf) Om(Ji Ml My Ne Of Ok Pb) aA(Hq Il Jk Nf Of Pa Pg) Et(Hw Il Jk Nc Nf Nt) Mw(Hw Lu Nc Nf Nl Og) Nw(Hw Ir Iv Jo Mb Na) Im(Iq Jk Nv Pg) Jg(Hw Il Ir Jr) Pa(Jn Lw Ok) Mu(Pf Pg) Il(Iq Jr) Ji(Io Lu) Jk(Jn Nm) Ny(Hw Nc) JrOf OiOk} Om{Pb(Fp Fr Ii Im Ip Iq Ir Iu Iv Jn Jr Lx Lz Mh Mi Mp Mt Mu Mw Na Nb Nd Ne Nn Nw Oh Oz Pf Po Qa) My(Et Hw Ii Im Iq Ir Iv Jg Jl Jn Jr Lu Mh Mi Mp Mt Mu Mw Mz Nb Nd Nf Nn Nv Ny Oh Pe Po) Ng(Et Fr Im Iq Ir Is Iu Jg Ji Jk Jl Jr Mm Mp Mr Mt Mu Mw Nn Nw Oh Ok On Pe Pf Po) Of(Et Fr Hw Ii Im Iq Ir Iv Jn Jr Lu Lz Mh Mp Mt Mu Mw Mx Mz Nb Nr Nw Oh Pf) Oy(Hq Hw Hx Im Iq Ir Iv Jk Jn Jr Lu Lz Mh Mi Mu Mx Nb Nn Nr Nv Nw Pf) Mg(Et Fr Im Iq Ir Is Iu Ji Jl Mm Mr Mt Mu Nd Nn Og Oh On Pa Pe Pf) Et(Hu Iq Jh Lj Lx Ms Nc Nd Pz) Mv(Is Ji Lh Lx Mt Nn Nw Oh On) Im(Hu Iq Ir Jl Jq Jr Nc Oh Ok) Nt(Hu Il Iq Jn Jo Jr Lj Oh) Oi(Iq Ir Is Ji Jl Nn Oh Ok) Lx(Hq Ir Jm Lj Oh Pg) Hu(Fr Is Lh Mr Nn On) Pz(Iq Ir Is Ji Jl Oh) Ms(Is Ji Mp Oh On) Jo(Jl Lh Mr Ok) Nd(Hq Og Ok) Ij(Hw Ir Lh) Mp(Iq Ir) Mr(Hx Oh) Ji(Md Ml) Ok(Hr Mq) Pa(Il Mk) MeIv IqQc} Ok{Jo(Hq Hw Ii Jg Jh Ji Jk Jl Lh Ma Mp Mr Mw Nc Nd Nn Nt Nv On Pa Pe Pg Po) Pb(Fr Hr Ii Im Jg Jh Ji Jk Jl Jt Lh Mp Mr Mt Nd Nn On Pa Pe Pf Po Pz) Mq(Fr Hr Im Is Jg Jk Jl Jq Lw Lx Mt Mw Nd Nq Nt Nw Oh On Pa Pf) Mg(Hq Hr Im Jg Jl Lh Ma Mp Mr Mt Nq Nt On Pa Pf) Hr(Im Io Is Jh Jl Jq Lx Mt Nd Nw Oi On Pa Pz) Pz(Is Jg Jk Jl Jq Lx Mb Mp Mt Nc Nw Pa Pf) Oi(Et Fr Jg Jh Jl Mp Mt Mw Mz Nc Nd Oh Pa) Ng(Jg Jh Jk Lh Lx Mu Nd Nn Nt On Pa) Jt(Fr Jg Jh Jq Lw Mp Mw Nc Nn On) Lx(Jh Jq Mh Mj Nl Nu Nw) Io(Is Mp Nc Nd Nt Pa) Jh(Ij My Nd Nu Of Oy) Mj(Is Jl On Pa Pf) Nu(Fr Mw Nd Nn) Mp(Hw Im Nw Oh) Og(Jg Jk Jl Pa) Mw(Hw Ij Of) My(Fr Jg Jk) Im(Fr Jl Lw) Qc(Iq Ji Mz) Nn(Oh Pc) Nx(Ji On) Oy(Jk Mu) NmLw MkPa NdNw} Jq{Im(aA Et Hw Iq Ir Is Iv Jg Jh Jk Jo Lh Mb Mh Mj Mm Mp Mt Mu Mw Nb Nd Nj Nn Nr Nt Nw Oz Pf Po) Lx(Et Hu Is Jh Jl Ly Md Mg Ml Mp Mu Mw My Nc Nf Ng Nj Nn Ny Og On Oy Pb Pe Pg) Nd(Et Fr Hr In Io Ir Is Iv Jg Jh Mr Mu Mw Ne Nj Nw On Pa Pe) Pa(Et Hr Hx Ii Ij Il Is Mh Ml Mp Nc Ng Nj Nn Ny Of) Mw(Hu Ij Iq Lj Md Mg My Nc Ng Of Og Oy Pb) Mu(Et Iq Iv Mp Nc Ng Nj Og Oy Pb Pe) Nn(Iv Lw Mg Mr Oh Oi Pc Pe Pz) Po(Md Ml My Ny Of Og Oy Pb) Nc(Et Fr Jg Jh Mp Nw Pe) Lh(Hr Ii Io Md Mj Nj Og) Pe(Et Hr Mh Mp Og Oy) Nt(Io Jo Mp Nj) Hr(aA Is Jl On) Jg(My Ng Oy Pf) Fr(My Oy Pz) Mp(Lw Oh Pc) Is(Ij Mm Qd) On(Jt Nx Pb) Et(Hw Mr) Iq(Jh Qc) LwMm MeIv IiOy IoaA JhOg JlPb} Jh{Ng(Et Fr Hw Ii Iq Ir Is Jr Lz Mh Mp Mt Mu Mz Nc Nf Nw Oh Pf) Oy(Et Fr Ii Iq Ir Is Jr Lz Mt Mz Nb Nc Nd Nf Nt Nw Ny Oh Pf) Mg(Et Fr Ir Is Iv Jr Lz Mh Mi Mp Nd Nt Oh On Pa Pf Po) Hu(Fr Iq Is Jr Lu Lz Mh Mp Mt Nd Nn Nw Oh On Pe Pf Po) Og(Et Hw Hx Iq Ir Iv Jr Lx Lz Mt Mz Nb Nc Nr Nt Oh Po) My(Fr Ii Iq Is Jr Mz Nb Nf Nt Oh Pe) Jr(Im Lh Lx Mp Mr Nc Nd Nt Pz) Of(Jl Lx Mh Mr Mz On Pe Po) Ir(Jt Lx Mp Nd Oi Pb Pz) Lx(Hq Jm Lj Ly Mv) Iq(Mp Mv Nt Oi Pz) Oh(Mr Oi Pc Pe Pz) Pb(Hw Is Mz Nr Po) Lj(Lh Nd Nt On) Ms(Is Mh On) Mz(Ml Mp Nt) Mr(Jo Lw) Mv(Nw On) Is(Oi Pz) Jl(Oe Oi) Jn(Mp Nt) Pa(Il Mk) NcNw JoLh} Nw{Mb(Im Is Lx Mu Mv My Nc Nd Ne Nj Nl Nt Ny Of Og Oi Oy Pb Pf) Oi(Et Hw Ir Is Jl Jo Lh Mp Mr Mu Na Nn No Nr Nt Oh Pe) Im(Et Hv Hw Ir Is Iv Jl Jn Jo Jr Lw Na Nr Pe Qa) Nt(Et Io Ir Jm Jn Jr Mu My Na Ng Nv Og Pg) Na(Fr Ij Lx Mp Mu Nc Nd Nn No Og Pb) Hw(Et Hr Ij Is Ml Mp Nc Nd Nn Og) Mu(Ir Iv Mv My Nc Ng Og Oy Pb) Og(Ii Is Jg Lh Mr Mw Nb Pe) My(Fr Ii Jg Jk Lh Nn Pe) Ir(Ij Lx Mp Nd Nn Pb Qc) Nd(Hv Is Iv Jn Jr) Lh(Hx Mh Ng Oy Pb) Mr(Et Lw Mh Pb) Oy(Ii Jk Mw Pe) Iv(Fr Mp Nn) Pz(Et Jl Nn) Qc(Iq Jn Jr) Pb(Jo Nr Pe) Mw(Mv Ng) MhPe NcNi HrIs} Mw{Ng(Et Fr Iq Ir Is Jl Jn Jr Lh Mt Mu Mz Nd Nf Nt On Pa Pe Pf) Oy(Et Fr Ii Iq Ir Is Jl Jn Jr Lh Mr Mu Mz Nb Nf Ny Pa Pe Pf) My(Et Fr Ir Jl Jn Jr Lh Lx Mr Mt Mz Nb Nf Oh Pa Pe Po) Mg(Et Iq Ir Is Jl Jr Lh Lx Mr Nm Nt Oh Pe Pf) Og(Et Hu Iq Ir Jl Jn Lh Mr Mt Nb Nf Pe) Pb(Hw Ir Is Ji Jl Jn Jr Lh Mr Mz Pe) Hu(Im Iq Is Jn Jr Lx Mr Mx Mz Oi) Mz(Et Is Ml Mv Nt Ny Of Oi) Pz(Et Iq Ir Is Ji Jl Jr) Jr(Et Im Jl Mv Nt Of) Iq(Et Is Mv Oi) Ir(Ij Im Jo Jt) Ji(Ms Nx Of) Jn(Et Jl Nt) Lx(Jm Ly) Is(Ms Oi) MtMv JlOi} On{Pb(Hv Hw Ij In Io Ir Jn Jo Jr Mr Mu Mz Na Nf Ni Nr Qa) Jo(Hv Hw In Ir Iv Jn Jr Lh Mr Na Ni Nr Nt Pe Qa) Io(Hr Iq Ir Is Ji Lj Me Mg Ms Mv Nc Ns Of) Ij(Hv Hw In Ir Ji Jn Jr Mz Na Nx Of Qa) Mg(Fr Im Ji Lh Lw Lx Mr Mu Nm Nn Pe) Im(Hr Hu Ir Ji Jn Jr Lw Mz Og Oi) Of(Hv Hw In Jn Mu Mz Nf Pe) Jt(Hw Ir Iv Ji Jn Jr Na) Nx(Hv Hw In Ji Mz Na Qa) Lx(Hu Jm Ly My Nq Nv) Hr(Ir Is Jn Jr Mz) Qc(Iq Ji Jn Jr Mz) Mj(Ng Ns Og) Mq(Hw Ir Na) Mu(Hu Lj Mv) Oi(Hq Iq Pg) Nt(Jm Nv) Mp(My Oy) Ng(Jg Pa) MyOh NdJm JiOg OyPc} Jl{Im(Et Hr Io Iq Ir Jn Jr Lw Md Mp Mt Mz Nf Og Oi Pz) Pz(Et Fr Hr Iq Is Jn Mp Mt Mu Mz Nm Oh Pb Pf) Pb(Hv Hw Ij In Ir Jn Jr Mt Mu Mz Na Pe Qa) Oi(Et Hr Iq Is Jg Jn Mp Mt Mu Mz Nf Oh) Nn(Io Jn Jr Mg My Ng Og Oy Pc) Io(Et Hr Is Lw Mp Mt Nc Oh) Og(Et Ir Is Jn Jr Mu Mz Nf) Mu(Jn Mg My Mz Ng Oy) Hr(Is Jn Jr Mt Mz Nf) Jo(Ir Jn Lh Nf Nm) Lw(Iq Jn Jr Nf) Mg(Jg Lh Mp Nm) Lx(Jn Jr Ly) Mj(Is Nf No) Mp(Jn Jr Mz) Jg(My Ng Oy) EtNf MtOy MzQc} Ji{Oi(Hw Iq Is Jk Ma Mb Mm Mp Mr Oh Pe Pf) Po(Hx Ij Mh Ml My Ny Of Og Oy Pb) Pz(Hw Iq Ir Jk Mb Mm Mt Nr Pa Pe) Mg(Iu Jg Jk Lh Lx Mt Nm Nq Pa) Ii(Hx Ij Ml My Ny Of Og Oy Pb) Ij(Ir Is Iv Jk Na Nb Nr Pa) Lh(Hr Io Mj Nx Pb) Oh(Iu Lw Mm Mp Pc) Pa(Hx Mh Mj Mk

Figure 43 Continued

Nb) Lu(Hr Me Mj Nx) Im(Ir Jg Pe Pf) Qc(Ir Jp Mx Pf) Nr(Io Og Pb) Me(Io Iv Mf) Ms(Jg Jk Mb) Nx(Hw Nc Pe) Mm(Lw Pc) Nb(Og Pb) Nf(Lx Ml) Is(Io Mj) Jg(Ng Oy) Jk(Mv Of) NnPc HrPe HwPb JrJs} Fr{Ng(Hv Hw Ii Im Ir Iv Jn Jo Lh Lx Mb Mr Mu Na Nf Nm Nt Pe Po Qa) Mg(Et Hv Hw In Ir Jn Jo Jr Js Lh Mb Mp Mr Mz Na Nt Pe Qa) My(Hv Hw Ii Ir Iv Jn Js Lh Mr Na Nb Ny Pe) Pb(Hv Hw Ir Is Iv Jn Lh Mr Mz Na Pe) Im(Hw Ir Iv Jn Jr Js Mz Na) Oy(Ii Is Lh Mr Nb Pe Po) Pz(Et Ir Iv Jn Jr Mz) Jo(Hw Is Iv Lh Na) Jn(Mp Nc Nt Oi) Mz(Mp Nt Oi) Mr(Hu Lw) Oi(Ir Lj) NtJr LxJm NaNc IvOg} Is{Io(Et Hr Lh Lw Lx Me Mm Mp Mr Nc Nd Nn Nt Pa Pe) Oi(Et Hr Iq Jg Lh Lw Mm Mp Mt Mz Nf Oh) Hr(Et Lh Lx Mr Mt Mz Nf Pe Pf Po) Mj(Lh Lx Mr Mz Nf Pe Pf) Jg(Hu Ms My Ng Ns Oy Pz) Og(Ii Lw Me Nb Nn Pe Po) Mg(Lh Mr Nm Nn Pe Pf) Lw(Lh Lx Mr Nf Pa) Pz(Et Mm Mt Nn Pf) Pb(Lh Mt Pe Po) Lx(Il Jm Ly) Mz(Mm Mp Qc) Nd(Jm Nj) PoOy NtJm MmOh IlPa} Mu{Ng(Et Iq Iv Jg Lh Lx Mp Mr Mt Mz Nd Nt Pe Po) Mg(Et Iq Ir Iv Lh Mp Mr Nm Nt Pe) Ir(Et Hr Im Lx Mp Nj Og Oi Pz) Oy(Et Ii Lh Mp Mr Nb Pa Pe Po) Pb(Hw Iv Jr Lh Mr Mz Nr Po) Og(Iv Lh Mr Mz Nb Pe) Mp(Iv Jn Jr Mz) Oi(Ih Iq Lj Oh) Nt(Jn Jr Mz) Mr(Hu Lw Ly) Lh(Hu Jo My) Et(Lj Mz) Nj(Iq Jr) Iv(Me Oh) NsJr LxLy MzOf HuaA IqPz JnPa OhPc} Nn{Oi(Et Hw Ih Ir Iv Jn Jr Lh Lj Mr Mt Mz Nb Nc Nr Nt Pa Pe) Mr(Et Hu In Jo Jr Lw Mg My Ng Og Oy Pb Pz) Pe(Et Jo My Ng Nu Og Oy Pb Pz) Mg(aA Et Ii Ir Iv Lh Mz) Pz(aA Et Ir Iv Jr) Lh(Jo My Ng Oy) Ir(Im Jo Lx) Nb(Og Oy) Ii(My Ng) Iv(Jo Og) PoOy} Lx{Ly(aA Et Hr Hv Hw Ii Ir Iv Jm Jn Jo Jr Lh Mb Mg My Mz Na Nc Ne Ng Nj Oz Pa) Et(Ir Jn Jr Mg Mz Ng) Jg(Jm My Og Oy) Ir(Jo Mp Pb) NmMg NbOy HraA HwPb} Mr{Lw(Et Im Iq Jn Jo Jr Mg Mt Mz Og Oy Pb) Mg(Et Jg Ma Mm Mp Nm) Et(Io Jo Pb Pz) Mp(Jn Jr Mz Pb) Jg(My Ng Og Oy) Mt(Oi Pb) Oh(Mj Oi) MzPb HraA} Jg{Og(Ir Jr Lh Mt Mz Nb Ny Pa Pe Po) My(Jr Lh Mt Mz Po) Ng(Mp Mt Pa Pe Po) Oy(Lh Mt Pe Po) Mg(Lh Mp Pe) Oi(Iq Oh) IrPz PbPe} Pb{No(Hv Hw Ii Ij In Jo Lh Nf Nx Pe Qa) Pe(Et Il Lw Mp Mt Mz Oh) Mt(Hw Ir Iv Lh Nr) Po(Et Hw Na) MpIr MzPa} Et{Pz(Iq Ir Mt Mz Nc Pf Po) Mg(Lh Nt Pe Po) Mz(Im Mp Nt Oi) Lh(Jo Ng) PoOy NtJn MeaA MtHr NcIo OhOi} Mp{Ir(Hw Im Io Jo Jt Mg Oi Pz) Nt(Jn Jr Mz) Mg(Lh Pe) Mz(Im Oi) Pa(Jn Jr) aA(Lw Mm) NgLh} No{Mj(Hv Ij In It Iv Jt Lh Qa) Me(Ng Oi) Mm(Nf Oi) Nj(Ir Mh) HuJk} aA{Hr(Ii Mn Mz Nf Ny Pe) Io(Lw Ny) Jk(Hu Oy) Oh(Ma Nm) MmPc} Lh{Mg(Lw Ma Mm Mt Nm Pf) Jo(Lw Nm) Jr(Hr Mj) MaNg} Lw{Im(Iq Ir Mz) Pa(Jn Jr) PoOy NtMz} Mt{Ir(Hr Im Oi) HrOi IiOy} Pe{Mg(Ma Mm) Oh(Mj Oi)} Oy{PoMj IiOh} MaMgIv

Constrained panels with 3 analytes, where 1.0E-6 >= 'model p-value' > 1.0E-7. Contains 4,335 panels of 287,980 total panels evaluated. :
Jh{Mg(Hu Hw Ii Ik Ip Iu Jn Jo Js Jt Li Lj Lw Mb Mj Mt Mu Mw Mx My Mz Na Nb Nc Nf Nl Nm Nn Nr Nw Og Oy Qa) Ng(Hu Hx Ih Ik Ip Iu Iv Jg Jk Jn Jo Jq Lj Lu Md Mi My Na Nb Nn Nr Nv Ny Om Oy Pg Qa Qb Qe) Nc(Et Fr Hu Hw Im Ip Jn Lh Lj Lx Mh Mi Mp Mr Mt My Mz Na Nd Nf Nn Oh Oi Pa Pe Po Qa) Oy(Hw Hx Ih Iv Jk Jn Jq Js Lu Md Mi Mj Mk Mp Mu Mw Mx Nk Nl Nn Nr Nv Nx Oz Pg Qa Qb) Oi(Et Fr Hu Hw Ih Ip Iv Jn Jr Lh Lj Lz Mh Mi Mp Mr Mz Nf Nn Nr Nt Nw Pa Pe Po Qa) My(Et Hw Hx Ih Ir Iv Jg Jn Jq Lu Lz Mi Mp Mt Mw Mx Nd Nn Nr Nv Nx Ny Pf Pg Qb) Og(Fr Hu Ih Ii Ip Jg Jn Lj Mi Mp Mu Mw Mx Na Nd Nf Nn Ny Pf Qa Qb Qe) Pz(Et Fr Ih Iv Jn Lj Lz Mh Mi Mp Mr Mt Mz Nn Nt Nw Pa Pe Pf Qa Qe) Pa(Et Hx Ih Im Ip Jn Js Lj Lw Mp Ms Mv Mz Na Nf Oe Of Oh Pb Qa) Nd(Et Hv Hw Ih Iv Jn Js Mh Ms Mz Na Nf Nj Nl Ns Nw Qa Qd) Hu(Et Hw Im Ir Jq Li Mi Mu Mw Mx Mz Nf Nv Ny Om Pg Qa Qb) Lx(Hw Ih Iv Jn Js Lw Mh Ms Mz Na Nq Nw Ny Oh Pb Pg Qa) Lj(Et Fr Lu Mb Mh Mp Mr Mt Mu Nn Nv Nw Oh Pe Po) Pb(Fr Ii Iv Mh Mi Mt Na Nb Nf Nt Nw Ny Pf Qa) Mp(Et Hw Iv Js Lh Ma Mh Mr Ms Nf Nt Nw Pe) Mz(Hw Hx Ij Im Iu Lz Md Mr Mv Ny Pe) Of(Hw Ii Ir Mi Nb Nf Nr Nt Nw Ny Pf) Et(Hw Iq Ir Jn Mh Mr Nt Pe Pf) Ms(Fr Ih Lh Lz Mr Nr Nw Pe Po) Mv(Fr Lh Lz Mh Mt Nf Nn Pf Po) Hw(Ih Ij Ip Jn Jo Jq Oe Oh) Im(Ik Ir Iv Jn Mh Mj Nr Nw) Jn(Iu Lh Lz Mr Nr Pe) Jq(Jg Lz Mb Mh Nr Oh) Nw(Mh Mw Ne Nl Pe Pf) Ir(Hr Ij Jo Nt Oh) Pe(Hr Jo Mk Oe) Nt(Jo Mt Oh) Lh(Hr Il Oh) Lz(Ip Na) Mr(Il Oe) Mw(On Po) Iq(Lw Mb) NnOh NrOe NuPf MeIv HrJr HvIk} Jj{Nd(Fp Hq Hr Hu Hv Hw Hx Ih Im In Ip Iq It Jo Jp Js Jt Li Lw Ma Mb Md Mm Mn Mx Na Nb Nc Ne Nf Nh Nl Nx Of Pa Pd Qa Qb Qe) Jg(Et Hq Hu Hv Ih Im Io Ip Iq Iu Iv Jn Jo Js Lu Md Mi Mp Mx Mz Nc Ne Nf Nh Nl Nm Nr Nv Nw Og Oh Oi Pa Pf Pg Qa Qe) Pa(Et Hv Hw Ih Ik Ip Iq Ir It Iv Jo Jr Js Li Ma Md Mm Mn Mz Na Nc Nf Nj Nm Nw Nx Oh Pf Qa) Hq(Et Hv Hw Ih Il Im Ip Iq Ir Iv Jn Jo Jq Jr Js Mb Mm Mn Mp Mz Na Nc Nf Nm Oh Qa) Mp(Et Hr Hu Hv Im In Iq Jo Js Lu Md Na Nb Nc Ne Nl Nr Nw Ny Of Oi Pf Pg Qa) Mz(Et Hw Il Im Ip Iu Iv Jm Jo Lw Ma Ml Mm Mn Nc Nm Nq Nr Nw Of Oh Pf Pg) Nf(Hw Il Im Ip Iq Ir Iu Iv Jm Jo Lw Ma Mm Mn Nc Nm Nq Nr Nv Nw Oh Pf Pg) Hw(Ih Il Im Ip Iq Jm Jn Jp Jr Li Ma Md Mm Mn Nc Nm Nq Nv Oh Pf Pg) Nm(Hx Ih Il Im Iq Ir Iv Jn Jr Lu Md Mn Nc Ne Nr Nw Oh Pf) Jq(Ip Iq Iu Iv Jo Jr Li Lu Ma Mm Mn Nc Nj Nr Nw Of Oh Oz) Ir(Et Ik Im Ip Jm Lw Ma Md Mm Mn Nc Nq Nv Of Oh Pf Pg) Jn(Et Il Iu Jm Jo Lw Ma Mm Nc Nq Nr Nv Nw Of Oh Pg) Iv(Et Im Ip Lw Ma Md Me Mm Mn Nq Nv Oh Pf) Il(Ip Jp Li Lw Ma Md Mm Mn Nw Og Oh Qa) Et(Io Jo Lu Md Ne Nj Nl Nr Ny Pf Pg) Jr(Ip Iu Jo Lu Ma Mm Nc Nq Nr Nw Pg) Iq(Ih Jo Lw Lz Md Mn Nc Nx Of Pg) Oh(Hr Hv In Jo Nb Nr Of Oi Pc) Pf(Ih Jo Lz Mb Na Nc Nx Of Pe) Nr(Im Ip Ma Md Mm Mn Nw) Im(Jo Jt Mi Mj Nb Pd) Nw(Hr Hv In Nc Nu Of) Pe(Mb Mj Ml Ny Pg Qc) Mm(Hv Jo Js Lu) Ii(Hx Ik Ml) Jo(Ma Mn Pb) Md(Ip Po) Nc(Ma Of) Ny(Og Pb) NbOg IoNv} Mu{Ng(Hq Hv Hw Hx Ih Ii Im Iu Jo Js Li Lz Ma Mb Md Mh Mi Mm Nb Nc Nf Nm Nn Nr Nv Ny Oh Pf Pg Qa Qb Qe) Ik(Fp Fr Hr Hv Hw Ih Ii Ij Im It Jg Jo Js Li Lj Md Mh Mj Ml Na Nc Nf Nm Nn Nv Nx Og Oh Pg Qa Qd Qc) Og(Fr Hr Hv Hw Hx Ih Ii In Jg Jn Js Lx Mb Mh Mi Mp Mt Mw Na Nf Nm Nn Nr Nt Ny Pa Po Qa Qb Qe) Mg(Fr Hv Hw Ii Jg Jo Jt Li Lx Ma Mb Mh Mi Mj Mm Mt Mw Nb Nd Nn Nr Ny Oh Pa Pf Po Qa) Pb(Fr Hv Ii Ij In Ip Jn Jo Js Lx Mb Mh Mi Mp Mt Mw Na Nb Nf Nt Nx Ny Pa Pf Qa Qb Qe) Oi(Hw Jg Jn Js Li Mh Mi Mp Mr Mz Nb Nc Nf Nj Nr Ny Om Pa Pe Qa Qb Qe) Oy(Fr Iv Jg Lx Md Mi Mt Mz Nd Nf Nn Nr Nt Ny Pf Pg Qb) Lj(Fr Lh Lx Mb Md Mi Mp Mw Nd Nf Nt Nw Ny Om Pa Pz) Hu(Fr Lx Mp Mt Mw Nf Nn Nt Nw Ny Om Pa Pe Po Qb) Pa(Hv Hw Il Js Lw Mk My Mz Na Nf Nj Oe Of Qa) Mp(Hv Hw Ih Iq Js Ma Mr Nf Nt Oh Pe Pz Qa) My(Fr Ii Jg Lx Mr Mt Mw Mz Nb Nf Ny Po) Mz(Im Lx Md Ml Mr Mv Nc Nj Ny Oh Pe) Lx(Hq Hv Hw Jm Jn Js Na Of Qa) Pz(Fr Li Nn Nw Oh Om Pf Qa Qe) Nj(Hw Ih Jn Mi Na Nd Nf Nt) Im(Jn Js Lw Mh Mj Nc Nr Nw) Of(Ii Lh Nb Nf Ny Pe Po) Jn(Hr Lh Mr Nd Nw Pe) Oh(Hw Mr Nn Nt Pe) Om(Ih Iq Ms Mv Nc) Na(Lz Nc Nd Pf) Hv(Lz Nd Nw) Ns(Hw Pf) Nt(Js Mt) Nc(Nf Ny) Iq(Iv Lw) Jo(Iv Pe) Nw(Pe Qa) NdJs HrLh HwPf} Nw{Nc(Et Fr Hr Hv Ii Ij Im In Io Jn Jo Jr Lw Lx Mt Mw Mz Nd Nf Nn Nr Oi Om Pa Pe Qa) Ik(Fr Hr Hv Ii Ij In Iq It Jg Jk Jr Js Li Lx Lz Me Mj Ne Nm Nn Nu Oi Oz) Og(Fr Hr Hv Ij In Iv Jk Jl Jo Lw Lx Mp Mt Mz Nd Nf Nm Nn Nr Ny Of Pa Po) Nd(Et Hr Ij In Jo Js Jt Lw Ly Me Mv My Mz Ne Ng Ni Nr Oi Om Oy Qa) In(Fr Hx Ij Im Iq Lx Md Mh Ml Mm Mp My Ny Of Oh Oy Pb) My(Hr Ij Jo Lx Mp Mr Mt Mz Nb Nf Nm Nr Ny Pa Po) Im(Fr Hr Ij Iq Jt Lh Mj Mp Mr Mz Nm Nn Oi Om Pf) Oi(Fr Hv Iv Jg Jn Jq Jt Lw Mt Mw Mz Nm Om Qa) Pb(Hr Hv Ii Ij Is Jl Jn Mw Mz Nf Pa Po Qa) Lx(Hu Hv Ij Jn Jr Jt Lw Mh Mz Ng Ni Qa) Mp(Hv Is Jn Jo Jr Lh Mr Ne Ni Nt Pe Qa) Oy(Fr Hr Ij Jg Jo Mr Mt Nb Nf Nn Pa Po) Om(Hu Hx Md Mg Mh Ml Ms Mw Ne Nl Ny) Lh(Et Hr Hu Lw Mg Ml Mv Ny Of Pg) Mw(Hu Lj Mg Ms Ne Nl Of Pz Qc) Nn(Hv Jn Jr Mg Mv Ne Ng Qa) Nf(Hx Md Mh Ml Mv Ny Of Qc) Ij(Hv Iq Ji Jo Md Ml Ny Of) Pz(Fr Iq Iv Jg Mr Nm Pe Pf) Mm(Hv It Iv Jn Jr Me Mz) Ng(Fr Ii Jg Jk Mr Pa Po) Lw(Iq Ne Nr Nt Pa Pe) Ny(Ii Mr Mz Pa Pe Po) Hx(Ii Mr Pa Pe Po) Et(Iv Mb Na Pe) Fr(Hv It Mv Qa) Mh(Ii Nr Pa Po) Ml(Ii Mz Pe) Mr(Hu Jn Ly) Qc(Js Mt Mz) Of(Ii Pe Po) Nm(Mg Ne) Mv(Jk Po) Hv(Jl Nt) Pa(Jn Jr) MdMz HuJk IoJl} Fr{Ik(Fp Hr Hw Hx Ii Ij Im In It Jo Js Jt Lx Lz Me Mh Mj Mk Mt Mw Mx Na Ne Nf Nh Nl Nm Nn Nr Ny Oz Pa Pf Qa Qb Qd) Pz(Hu Hv Ih Ip Iq It Jg Jo Js Jt Lh Li Lj Lw Mb Mp Mr Mt Mw Mx Na Nc Nm Nn Nr Nt Oh Om Pe Pf Po Qa) Mg(Hr Ij Im Iq It Jg Jl Jt Lw Lx Me Mq Mt Mw Nb Nc Nf Nn Nr Nx Oh Oi Pf Po) Ng(Et Hr Hx Ij In It Jg Jl Js Jt Lw Md Me Mp Mt Nb Nc Nd Ne Nn Nr Ny Pa Qb) My(Hr Hx Ij In It Jg Jl Jo Lx Mb Md Mt Nd Ne Nf Nm Nn Nr Nt Pa Po Qa) Im(Hr Hu Hv Ij In Iq Jo Jt Lh Lj Lw Mb Mp Nc Nf Nr Om Pe Qa) Nc(Hr

Figure 43 Continued

Figure 43 Continued

Io(Jp Lw Oh) Is(Hr Il Mj) Ma(Mg Ng) Ir(Jo Oh) Ok(Mj Nl) NmMg LwJp IlOn OhOi} Is{Og(Hr Hw Ma Mb Mr Nm Nr) Ij(Hv Hw In Lr Na) Iq(Hr Mb Mj Pz Qc) Me(Hv Ir Lu Mf) Nd(Ir Jn Jr Mz) Nm(Jt Ng Pz) Hr(Hw Lu Md) Ma(Mb Mg) Mj(Mh Oe) Pz(Ir Po) NsPd MbNj Nalt IiOy} P

Figure 43 Continued

Jn Jr Lh Mr Mz Na No Nt Oi Pa Pe) Mw(aA Hu Ik Iq Ir Jn Jr Lh Mr My Mz Ng No Og Oy) Mp(aA Hw Iq Ir Iv Jn Jr Lh Mr Mz Nf No Nt Pe) aA(Io Ip Jg Lw Lx Ma Me Nj No Oi Pf) Lh(Ik Iq Jn Jr Lw Mg Mz Oh Pb Pf) No(Hr Im Jg Jn Jr Lw Mb Ms Mz) Ik(Ir Iv Mr Pc Pf Po) Jr(Im Jg Lx Mm Mr Nt) Lx(Ir Jn Ly) Mr(Lw Mz Oh) Nt(Jn Mz) Pe(Oh Pb) PoOy MzIm JnPa

Constrained panels with 2 analytes, where 1.0E-5 >= 'model p-value' > 1.0E-6. Contains 407 panels of 7,260 total panels evaluated. : Mz(Hw Ip Iq Ir Iu Iv Jg Jj Jk Jr Li Lw Lx Ma Ml Mm Nc Nd Nm Nq Nr Nv Ny Og Oh Om Pa Pb Pe Pf Pg Po) Jh(Fr Hw Ih Im Ip Iv Jn Js Li Lw Mg Mi Ms Mx My Na Nc Nd Nf Nl Nn Nr Ny Oi Oy Pa Po Qa Qb Qd Qe) Mw(Hw Ih Im Ip Iv Js Lj Lw Lx Lz Mg Mh Mi Mp Ms Na Nc Ne Nf Nl Nr Nt Oh Oi Pa Pb Pe Pf Qa) Jj(Hq Hw Hx Il Im Iq Ir Iv Jn Jo Js Li Ma Mm Nb Nd Nf Nm Nr Nx Of Oh Pa Pd Qa) Mp(Hr Hv Ii Ij Im In Jg Jo Jp Js Lx Mg Mh Na Nb Nc Ni Nr Ny Oi Pa Pf Po Qa) Mu(Hv Hw Im Jo Li Lw Lx Lz Mh Mi Na Nd Nf Ng Nm Nn Ny Og Oi Om Po Qa Qb Qe) Pf(Hv Hw Ii Im In Ir Iv Jg Jn Jr Lw Lx Mb Mr Na Nb Nf Nn Nt Ny Pa Pe Qa) Oh(Hv Hw Ii Iq Ir Iv Jg Jn Jo Jp Jr Lx Na Nb Nf Nt Nw Ny Oi Pa Po Qa) Ir(Hr Im Jg Jk Jq Jr Lw Ma Mm Mr Nd Nf Nt Nv Ny Oi Pa Pe Pg Po) Nn(Hv Ii Im In Iq Jo Js Lx Mb Nb Nc Ne Nf Nr Ny Po Qa) Jr(Hw Ii Iu Jk Jq Lw Ma Mb Nb Nd Nm Nr Ny Pa Pe Po) Mr(Im Ip Iq Jg Jn Jp Js Ly Ma Mm Nf Ny Og Pb Qa) Pe(Hr Ih Im Ip Iq Jg Jn Lw Ma Mg Mm Nf Ny Og Om) Nt(Ik Im Io Ip Iq Jg Jp Js Lw Ma Mm Nf Ny Qa) Lx(Hq Hv Hw Ik Iq Iv Jg Js Jt Lw Na Ng Nw Qa) Iq(Hw Ii Im Jg Jo Lw Mb Na Nw Ny) Po(Im Jn Lw My Nc Ng Of Og Pb) Jg(Hw Jn Lh Nf Ng Og Oi Pa Qa) Jq(Ii Iu Iv Jo Lu Lz Mb Mh Nb) Ny(Ik Im Lw My Nc Of Og Oy) Om(Hw Iv Jn Mv Ne Nl Pa Qa) Lh(Hr Im Jo Ma Mm Og) Nw(Ij In Jt Lw Nc Og) Fr(It Lj Me Nl Pz) Jn(Im Ma Mm Nd) Pa(Js Lw Nf Qa) Et(Io Lw) Nb(Ik Og) Im(Mj Nf) Iv(Ma Mm)

Constrained panels with 2 analytes, where 1.0E-4 >= 'model p-value' > 1.0E-5. Contains 348 panels of 7,260 total panels evaluated. : Jg(Fp Hv Ih Ii Ik Im In Ip Iv Jo Js Lj Lu Lw Lz Mb Md Mg Mh Mi Mx My Na Nc Nd Ne Nl Nr Nv Oy Pg Po Pz Qb Qd) Iq(Hr Hv Hx Ih Ij In Ip Ir Iv Jk Jn Jt Lv Lz Ma Md Mm Mn Nb Nc Nf Nm Nr Nv Nx Oi Pa Pg Po Qa) Lx(Hu Ih Ij Im In Ip Jm Jo Jp Li Lj Mb Mh Mm Nc Nf Ni Nm Nr Ny Og Oy Po Qd) Nf(Hw Ip Iu Iv Jk Jp Li Lw Lz Ma Mi Mm Nc Nd Nl Nm Nr Nv Oz Pg Po Qa Qd) Jj(Fp Hv Ih Ij In Ip Iu Jm Jp Jt Lw Md Mi Mn Mv Mx Na Nc Nl Nq Qb Qe) Pa(Hv Hw Ik Im Ip Iv Jo Li Ma Md Mm Na Nc Nh Ni Nj Nm Nv Ny Po) Jn(Hq Hw Ii Ip Ir Iu Jk Li Lu Lw Mb Nb Nm Nq Nr Nv Ny Pg Qa) Oh(Hr Hx Ij Im In Ip Jk Js Lu Lw Mb Md Nc Ne Nm Nr Nv Pc Pf) Iv(Ih Im Ip Ir Jk Jp Li Lw Lz Mb Md Me Nd Nq Nv Ny Pg Po) Hw(Ih Im Ip Jp Li Lw Lz Ma Md Mi Mm Nd Nv Ny Pg) Ii(Ih Ik Im Li Lj Lw Ma Mm My Nc Of Og Oy Pb Qa) Im(Jo Jp Js Jt Lw Mb Md Mi Na Nb Nr Nv Pg) Po(Hx Ih Ip Js Mb Mh Mm Na Nm Nt Ny Qa) Mm(Hv Ij In Jo Js Mi Na Nb Nr Ny Qa) Ir(Hx Ip Jp Li Lz Mn Nc Nq Og Pb Qa) Nv(Hv Ik Jo Js Lw Mi Na Nm Nr Oi Qa) Nb(Ip Js Li Lw Ma My Nc Oy Pb Qa) Qa(Lw Ma Md Mz Nc Nd Pg) Li(Ik Lw Mb Na Nd Nt Oi) Ny(Nd Ng Nl Nr Oi Pb) Ma(Hv Ih Js Na Nr) Lw(Jp Js Mi Nr) Nr(Jp Md) Nd(Hv Js) Pf(Jo Js) NmLu NtMd MiJp MzOi IkPg Constrained panels with 2 analytes, where 1.0E-3 >= 'model p-value' > 1.0E-4. Contains 418 panels of 7,260 total panels evaluated. : Jp(Fp Hr Hv Hx Ih Ii Ij In Ip Iu Jk Jo Js Jt Li Lu Lz Ma Mb Md Mh Mm Mx Na Nb Nd Nh Nl Nm Nx Pg Qb Qe) Nm(Fp Hv Hw Hx Ih Ii Im Ip Iv Jk Js Lz Ma Md Mg Mh Mx Na Nb Nc Nd Ne Ng Nl Nr Og Oi Pg Qb Qd Qe) Mm(Fp Hr Hx Ih Im Io Ip It Jk Jt Lj Lu Lw Lz Mb Md Me Mh Ml Mx Nc Nd Ni Nx Oi Pg Qb Qd Qe) Jk(Fp Hu Hv Hw Ih Ik Im In Ip Jo Js Jt Li Lj Lw Lz Ma Mb Md Mh Mi Mj Na Ng Nr Og Oi Qd) Nd(Fp Hx Ih Ii Ij Im In Ip Jo Jt Lj Lw Ma Md Me Mh Mx Na Nb Nc Ne Nh Nl Nr Nx Qd Qe) Ma(Hr Hv Ij Ik Im In Ip It Jo Jt Lw Mb Md Mg Mh Mx Nc Ne Ng Nl Nx Oi Qb Qd Qe) Ih(Hq Hr Hv Hx Ij In Ip Jo Jt Li Lu Lw Mb Md Mh Mj Na Nb Nr Nx Oi Pg) Ip(Hv Hx Ii Ij Im In Jo Js Jt Li Lw Lz Mb Md Mn Na Nc Nl Nr Nx Pg) Lw(Fp Hv Hx Jo Lj Lu Lz Md Mh Mx Nc Ne Nl Pg Qb Qd Qe) Na(Fp Hq Hx Iu Lz Md Mh Mi Mn Mx Nc Nl Nq Pg Qb Qd Qe) Js(Hq Hw Hx Ii Iu Jo Li Lz Mb Md Mn Nq Nr Nx Oz Pg) Im(Hr Hv Hx Ij In Li Lz Mh Nc Nl Nx Oi Oz Qd Qe) Jj(Hr Hu It Lj Lu Lv Lz Mb Mh My Ne Nh Nu Oz Qd) Md(Fp Hv Hx Jo Li Lj Lz Mb Mh Mx Nb Qb Qd Qe) Nb(Hx Iv Lj Lz Ms Ne Nf Nh Nl Of Oi Pg Qd) Nc(Hv Hw Hx Ij In Jo Jt Li Ni Nr Nx) Lz(Hv Hx Ii Ij Ik In Jo Jt Mb Nx) Nr(Li Mn Mx Nq Og Oi Pb Pg Qd) Jo(Li Mg Mh Nf Pb Pg Qb Qd Qe) Mb(Fp Mh Mx Pg Qb Qd Qe) Hw(Iv Mn Nq Pb Qb Qd Qe) Ii(Hx Iv Ml Ng Nh Nl Qd) Hv(Iu Li Me Nq Pg) Jt(Fp Lu Mg Mh Qb) Hx(Jn Li Og Qd) Nf(Nh Nj Qe) Li(In Lu Pg) Ns(Jg Pd) Mh(Nv Nx) Iv(Mi Og) Qd(Lu Nx) Qe(Jn Oi) Lj(Nq Pa) HuJg QbJn PaPg Constrained panels with 2 analytes, where 1.0E-2 >= 'model p-value' > 1.0E-3. Contains 194 panels of 7,260 total panels evaluated. : Mn(Fp Hr Hv Ij In Iu Lj Lu Lz Mb Md Mh Mj Mv Mx Nc Ne Nh Ni Nl Oi Qd) Nc(Fp Hq Hr Iu Lj Lu Lv Lz Mb Md Mh Mj Mq Mv Mx Nq Pd Qd Qe) Nl(Hq Hr Hx Ij In Lj Lu Lv Mb Mh Mj Mv Ni Nq Nx Qe) Ij(Hq Ik Iu Lj Lu Mh Mx Ne Nq Og Oz Qb Qd Qe) Mb(Hq Iu Lj Lu Lv Mj Mv Nd Ne Nh Nm Nq Pd) Mh(Hq Hr Hv In Ip Iu Mv Nq Pd Qb Qd) Hr(Ip Lu Lj Lu Lv Lz Nd Ne Nq Qd) In(Fp Hq Iu Lj Mx Nq Oz Qb Qd Qe) Ip(Fp Lu Mv Mx Ne Nh Qb Qd Qe) Nd(It Lv Lz Mj Ml Ni Nj Qb) Nq(Fp Ih Iu Mq Ne Nh Oi) Mx(Hq Hu Hv Ik Iu Mf Nx) Lj(Hq Hx Iu Lu Lv Na Oi) Hv(Hq Lu Oz Qb Qd Qe) Ih(Fp Lv Lz Mv Ni Pd) Ik(Fp Hq Mk Mv Oz Pd) Lv(Iu Lu Ne Nh) Mj(Lu Lz Md Qd) Iu(Fp Nx Oi) Qe(Nc Nx Og) Mv(Na Nc) Qb(Lu Pd) Jt(Ng Oi) FpOi NsMq LzIt Constrained panels with 2 analytes, where 5.0E-2 >= 'model p-value' > 1.0E-2. Contains 6 panels of 7,260 total panels evaluated. : Mj(Lv Ne) Ni(Nj Nk) NuIk MvMy Unconstrained panels with 3 analytes, where 2.0E-12 >= 'AUC p-value' > 0. Contains 50,000 panels of 287,980 total panels evaluated. : Ji[Po(aA Et Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Et(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Fp(aA Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Fr(aA Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Nm(aA Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nn No Nq Nr Ns Nt Nu Nv Nw Nx Ny Oe Of Og Oh Oi Ok Om On Oy Oz Pa Pb Pc Pd Pe Pf Pg Pz Qa Qb Qc Qd Qe) Nn(aA Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf

Jp Jq Jr Js Jt Lh Li Lj Nv Nw Nx Ny Oe Of Og Oh Oi Ok Om On Oy Oz Pa Pb Pc Pd Pe Pf Pg Qe) Qe(aA Jg Jh Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jg(aA Jh Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jh(aA Jj Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jj(aA Jk Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jk(aA Jl Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jl(aA Jm Jn Jo Jp Jq Jr Js Jt Lh Li Lj Nv Nw Nx Ny Oe Of Og Oh Oi Ok Om On Oy Oz Pa Pb Pc Pd Pe Pf Pg) Jm(aA Jn Jo Jp Jq Jr Js Jt Lh Li Lj Nv Nw Nx Ny Oe Of Og Oh Oi Ok Om On Oy Oz Pa Pb Pc Pd Pe Pf Pg) Jn(aA Jo Jp Jq Jr Js Jt Lh Li Lj Nv Nw Nx Ny Oe Of Og Oh Oi Ok Om On Oy Oz Pa Pb Pc Pd Pe Pf Pg) Jo(aA Jp Jq Jr Js Jt Lh Li Lj Nv Nw Nx Ny Oe Of Og Oh Oi Ok Om On Oy Oz Pa Pb Pc Pd Pe Pf Pg) Jp(aA Jq Jr Js Jt Lh Li Lj Nv Nw Nx Ny Oe Of Og Oh Oi Ok Om On Oy Oz Pa Pb Pc Pd Pe Pf Pg) Jq(aA Jr Js Jt Lh Li Lj Nv Nw Nx Ny Oe Of Og Oh Oi Ok Om On Oy Oz Pa Pb Pc Pd Pe Pf Pg) Jr(aA Js Jt Lh Li Lj Nv Nw Nx Ny Oe Of Og Oh Oi Ok Om On Oy Oz Pa Pb Pc Pd Pe Pf Pg) Js(aA Jt Lh Li Lj Nv Nw Nx Ny Oe Of Og Oh Oi Ok Om On Oy Oz Pa Pb Pc Pd Pe Pf Pg) Jt(aA Lh Li Lj Nv Nw Nx Ny Oe Of Og Oh Oi Ok Om On Oy Oz Pa Pb Pc Pd Pe Pf Pg) Lh(aA Li Lj Nv Nw Nx Ny Oe Of Og Oh Oi Ok Om On Oy Oz Pa Pb Pc Pd Pe Pf Pg) Li(aA Lj Nv Nw Nx Ny Oe Of Og Oh Oi Ok Om On Oy Oz Pa Pb Pc Pd Pe Pf Pg) Lj(aA Nv Nw Nx Ny Oe Of Og Oh Oi Ok Om On Oy Oz Pa Pb Pc Pd Pe Pf Pg) Nv(aA Nw Nx Ny Oe Of Og Oh Oi Ok Om On Oy Oz Pa Pb Pc Pd Pe Pf Pg) Nw(aA Nx Ny Oe Of Og Oh Oi Ok Om On Oy Oz Pa Pb Pc Pd Pe Pf Pg) Nx(aA Ny Oe Of Og Oh Oi Ok Om On Oy Oz Pa Pb Pc Pd Pe Pf Pg) Ny(aA Oe Of Og Oh Oi Ok Om On Oy Oz Pa Pb Pc Pd Pe Pf Pg) Oe(aA Of Og Oh Oi Ok Om On Oy Oz Pa Pb Pc Pd Pe Pf Pg) Of(aA Og Oh Oi Ok Om On Oy Oz Pa Pb Pc Pd Pe Pf Pg) Og(aA Oh Oi Ok Om On Oy Oz Pa Pb Pc Pd Pe Pf Pg) Oh(aA Oi Ok Om On Oy Oz Pa Pb Pc Pd Pe Pf Pg) Oi(aA Ok Om On Oy Oz Pa Pb Pc Pd Pe Pf Pg) Ok(aA Om On Oy Oz Pa Pb Pc Pd Pe Pf Pg) Om(aA On Oy Oz Pa Pb Pc Pd Pe Pf Pg) On(aA Oy Oz Pa Pb Pc Pd Pe Pf Pg) Oy(aA Oz Pa Pb Pc Pd Pe Pf Pg) Oz(aA Pa Pb Pc Pd Pe Pf Pg) Pa(aA Pb Pc Pd Pe Pf Pg) Pb(aA Pc Pd Pe Pf Pg) Pc(aA Pd Pe Pf Pg) Pd(aA Pe Pf Pg) Pe(aA Pf Pg) Pf(aA Pg) PgaA} On{Et(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Ns(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nu Nv Nw Nx Ny Oe Of Og Oh Oi Ok Om Oy Oz Pa Pb Pc Pd Pe Pf Pg Po Pz Qa Qb Qc Qd Qe) Nu(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Lv(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Lw(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Lx(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Ly(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Lz(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Ma(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Mb(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Mf(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mc Md Me Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Mg(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mc Md Me Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Mh(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mc Md Me Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Mj(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mc Md Me Mi Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Ml(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mc Md Me Mi Mk Mm Mn Mp Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Mp(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mc Md Me Mi Mk Mm Mn Mq Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Mq(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mc Md Me Mi Mk Mm Mn Mr Ms Mt Mu Mv Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Mv(aA Fp Fr Hq Hr Hu Hv Hw Hx Ih Ii Ij Ik Il Im In Io Ip Iq Ir Is It Iu Iv Jg Jh Jj Jk Jl Jm Jn Jo Jp Jq Jr Js Jt Lh Li Lj Lu Mc Md Me Mi Mk Mm Mn Mr Ms Mt Mu Mw Mx My Mz Na Nb Nc Nd Ne Nf Ng Nh Ni Nj Nk Nl Nm Nn No Nq Nr Nt Nv Nw Nx Ny Oe Of Og Oh Oi Ok Om Oy Oz Pa Pb Pc Pd Pe Pf Pg Po Pz Qa Qb Qc Qd Qe) Mw(aA Fp Fr Hq Hr Hu Hv Hw Hx Ih Ii Ij Ik Il Im In Io Ip

Pc Pd Pe Pf Pg Po Qa Qb Qd Qe) Pc(aA Fp Fr Hv Hw Ih Ij In Iq Ir It Iv Jg Jl Jn Jo Jp Jr Js Jt Lh Li Lj Lu Mc Md Me Mi Mk Mm Mn Mr Ms Mt Mu Mx Mz Nc Ne Nf Nh Ni Nk Nl Nm Nn No Nq Nr Nt Nw Nx Oh Ok Om Oz Pa Pe Po Qa Qb Qd Qe) Pd(aA Fp Fr Hv Hw Ih Ij In Iq Ir It Iv Jg Jl Jn Jo Jp Jr Js Jt Lh Li Lj Lu Mc Md Me Mi Mk Mm Mn Mr Ms Mt Mu Mx Mz Nc Ne Nf Nh Ni Nk Nl Nm Nn No Nq Nr Nt Nw Nx Oh Ok Om Oz Pa Pe Pf Pg Po Qa Qb Qd Qe) Pf(aA Fp Fr Hv Hw Ih Ij In Iq Ir It Iv Jg Jl Jn Jo Jp Jr Js Jt Lh Li Lj Lu Mc Md Me Mi Mk Mm Mn Mr Ms Mt Mu Mx Mz Nc Ne Nf Nh Ni Nk Nl Nm Nn No Nq Nr Nt Nw Nx Oh Ok Om Oz Pa Pe Pg Po Qa Qb Qd Qe) Pg(aA Fp Fr Hv Hw Ih Ij In Iq Ir It Iv Jg Jl Jn Jo Jp Jr Js Jt Lh Li Lj Lu Mc Md Me Mi Mk Mm Mn Mr Ms Mt Mu Mx Mz Nc Ne Nf Nh Ni Nk Nl Nm Nn No Nq Nr Nt Nw Nx Oh Ok Om Oz Pa Pe Po Qa Qb Qd Qe) Lu(aA Fp Fr Hv Hw Ih Ij In Iq Ir It Iv Jg Jl Jn Jo Jp Jr Js Jt Lh Li Lj Mc Md Me Mi Mk Mm Mn Mr Ms Mt Mu Mx Mz Nc Ne Nf Nh Ni Nk Nl Nn No Nq Nr Nt Nw Nx Oh Ok Om Oz Pa Pe Po Qa Qb Qd Qe) Mc(aA Fp Fr Hv Hw Ih Ij In Iq Ir It Iv Jg Jl Jn Jo Jp Jr Js Jt Lh Li Lj Md Me Mi Mk Mm Mn Mr Ms Mt Mu Mx Mz Nc Ne Nf Nh Ni Nk Nl Nm Nn No Nq Nr Nt Nw Nx Oh Ok Om Oz Pa Pe Po Qa Qb Qe) Md(aA Fp Fr Hv Hw Ih Ij In Iq Ir It Iv Jg Jl Jn Jo Jp Jr Js Jt Lh Li Me Mi Mk Mm Mn Mr Ms Mt Mu Mx Mz Nc Ne Nf Nh Ni Nk Nl Nm Nn No Nq Nr Nt Nw Nx Oh Ok Om Oz Pa Pe Po Qa Qb Qd Qe) Mi(aA Fp Fr Hv Hw Ih Ij In Iq Ir It Iv Jl Jn Jo Jp Jr Js Jt Lh Li Lj Me Mk Mm Mn Mr Ms Mt Mu Mx Mz Nc Ne Nf Nh Ni Nk Nl Nm Nn No Nq Nr Nt Nw Nx Oh Ok Om Oz Pa Pe Po Qa Qb Qd Qe) Mn(aA Fp Fr Hv Hw Ih Ij In Iq Ir It Iv Jg Jl Jn Jo Jp Jr Js Jt Lh Li Lj Me Mk Mm Mr Ms Mt Mu Mx Mz Nc Ne Nf Nh Ni Nk Nl Nm Nn Nq Nr Nt Nw Nx Oh Ok Om Oz Pa Pe Po Qa Qb Qd Qe) Mt(aA Fp Fr Hv Hw Ih Ij In Iq Ir It Iv Jg Jl Jn Jo Jp Jr Js Jt Lh Li Lj Me Mm Mr Ms Mu Mx Mz Nc Ne Nf Nh Ni Nk Nl Nm Nn No Nq Nr Nt Nw Nx Oh Ok Om Oz Pa Pe Po Qa Qb Qd Qe) Mu(aA Fp Fr Hv Hw Ih Ij In Iq Ir It Iv Jg Jl Jn Jo Jp Jr Js Jt Lh Li Lj Me Mk Mm Mr Ms Mx Mz Nc Ne Nf Nh Ni Nk Nl Nm Nn No Nq Nr Nt Nw Nx Oh Ok Om Oz Pa Pe Po Qa Qb Qe) Nh(aA Fp Hv Hw Ih Ij In Iq Ir It Iv Jg Jl Jn Jo Jp Jr Js Jt Lh Li Lj Me Mk Mm Mr Ms Mx Mz Nc Ne Nf Ni Nk Nl Nm Nn No Nq Nr Nt Nw Nx Oh Ok Om Oz Pa Pe Po Qa Qb Qd Qe) Hw(aA Fp Fr Hv Ih Ij In Iq Ir It Iv Jg Jl Jn Jo Jp Jr Js Jt Lh Li Lj Me Mk Mr Ms Mx Mz Nc Ne Nf Ni Nk Nl Nm Nn No Nq Nr Nt Nw Nx Oh Ok Om Oz Pa Pe Po Qa Qb Qd Qe) Ij(aA Fp Fr Hv Ih In Iq Ir It Iv Jg Jl Jn Jo Jp Jr Js Jt Lh Li Lj Me Mk Mm Mr Ms Mx Mz Nc Ne Nf Ni Nk Nl Nm Nn No Nq Nr Nt Nw Oh Ok Om Oz Pa Pe Po Qa Qb Qd Qe) In(aA Fp Fr Hv Ih Iq Ir It Iv Jg Jl Jn Jo Jp Jr Js Jt Lh Li Lj Me Mk Mm Mr Ms Mx Mz Nc Ne Nf Ni Nk Nl Nm Nn No Nq Nr Nt Nw Oh Ok Om Oz Pa Pe Po Qa Qb Qd Qe) Qe(aA Fp Fr Hv Ih Iq Ir It Iv Jg Jl Jn Jo Jp Jr Js Jt Lh Li Lj Me Mk Mm Mr Ms Mx Mz Nc Ne Nf Ni Nk Nl Nm Nn No Nq Nr Nt Nw Nx Oh Ok Om Oz Pa Pe Po Qa Qb) Jl(aA Fp Fr Hv Ih Iq Ir It Iv Jn Jo Jp Jr Js Jt Lh Li Lj Me Mk Mm Mr Ms Mx Mz Nc Ne Nf Ni Nk Nl Nm Nn No Nq Nr Nt Nw Nx Oh Ok Om Oz Pa Pe Po Qa Qb Qd) Jo(aA Fp Fr Hv Ih Iq Ir It Iv Jg Jn Jp Jr Js Jt Lh Li Lj Me Mk Mm Mr Ms Mx Mz Nc Ne Nf Ni Nk Nl Nm Nn No Nq Nr Nt Nw Oh Ok Om Oz Pa Pe Po Qa Qb Qd) Jt(aA Fp Hv Ih Iq Ir It Iv Jg Jn Jp Jr Js Lh Li Lj Me Mk Mm Mr Ms Mx Mz Nc Ne Nf Ni Nk Nl Nm Nn No Nq Nr Nt Nw Nx Oh Ok Om Oz Pa Pe Po Qa Qb Qd) Oh(aA Fp Fr Hv Ih Iq Ir It Iv Jg Jn Jp Jr Js Lh Li Lj Me Mk Mm Mr Ms Mx Mz Nc Ne Nf Ni Nk Nl Nm Nn No Nq Nr Nt Nw Nx Ok Om Pa Pe Po Qa Qb) Oz(aA Fp Fr Hv Ih Iq Ir It Iv Jg Jn Jp Jr Js Lh Li Lj Me Mk Mm Mr Ms Mx Mz Ne Nf Ni Nk Nl Nm Nn No Nq Nr Nt Nw Nx Ok Om Pa Pe Po Qa Qb Qd) Nn(Fp Fr Hv Ih Iq Ir It Iv Jg Jn Jp Jr Js Lh Li Lj Me Mk Mm Mr Ms Mx Mz Nc Ne Nf Ni Nk Nl Nm No Nq Nr Nt Nw Nx Ok Om Pa Pe Po Qa Qb) Me(aA Fp Hv Ih Iq Ir It Iv Jg Jn Jp Jr Js Lh Li Lj Mk Mr Ms Mx Mz Nc Ne Nf Ni Nk Nl Nm No Nq Nr Nt Nw Nx Ok Om Pa Pe Po Qa Qb Qd) Mx(aA Fp Hv Ih Iq Ir It Iv Jn Jp Jr Js Lh Li Lj Mk Mm Mr Ms Mz Nc Ne Nf Ni Nk Nl Nm No Nq Nr Nt Nw Nx Ok Om Pa Pe Po Qa Qb Qd) It(aA Fp Hv Ih Iq Ir Iv Jg Jn Jp Jr Js Lh Li Lj Mk Mr Ms Mz Nc Ne Nf Ni Nk Nl Nm No Nq Nr Nt Nw Nx Ok Om Pa Pe Po Qa Qb Qd) Iv(aA Fp Hv Ih Iq Ir Jg Jn Jp Jr Js Lh Li Lj Mk Mr Ms Mz Nc Ne Nf Ni Nk Nl Nm No Nq Nr Nt Nw Nx Ok Om Pa Pe Po Qa Qb Qd) Jn(aA Fp Hv Ih Iq Ir Jg Jp Jr Js Lh Li Lj Mk Mr Ms Mz Nc Ne Nf Ni Nk Nl Nm No Nq Nr Nt Nw Nx Ok Om Pa Pe Po Qa Qb Qd) Jr(aA Fp Hv Ih Iq Ir Jg Jp Js Lh Li Lj Mk Mr Ms Mz Nc Ne Nf Ni Nk Nl Nm No Nq Nr Nt Nw Nx Ok Om Pa Pe Po Qa Qb Qd) Nw(aA Fp Fr Hv Ih Iq Ir Jg Jp Js Lh Li Lj Mk Mm Mr Ms Mz Nf Ni Nk Nl Nm No Nq Nr Nt Nx Ok Om Pa Pe Po Qa Qb Qd) aA(Fp Fr Hv Ih Iq Ir Jp Js Lh Li Lj Mk Mm Mr Ms Mz Nc Ne Nf Ni Nk Nl Nm No Nq Nr Nt Nx Ok Pa Pe Po Qa Qb Qd) Po(Fp Fr Hv Ih Iq Ir Jg Jp Js Lh Li Lj Mk Mm Mr Ms Mz Ne Nf Ni Nk Nm No Nq Nr Nt Nx Ok Om Pa Pe Qa Qb) Nq(Fp Fr Hv Ih Iq Ir Jp Js Lh Li Lj Mk Mr Ms Mz Nc Ne Nf Ni Nk Nl No Nr Nt Nx Ok Om Pa Pe Qa Qb Qd) Mr(Fp Fr Hv Ih Iq Ir Jg Jp Js Lh Li Lj Mk Mz Nc Nf Ni Nk Nl Nm No Nr Nt Nx Ok Om Pa Pe Qa Qb Qd) Ir(Fp Ih Iq Jp Js Lh Li Lj Mk Mm Ms Mz Nc Ne Nf Ni Nk Nl Nm No Nr Nt Nx Ok Om Pa Pe Qa Qb Qd) Hv(Fp Ih Iq Jg Jp Js Lh Li Lj Mk Ms Mz Nc Ne Nf Ni Nk Nl Nm No Nr Nt Nx Ok Om Pa Pe Qb Qd) Js(Fp Ih Iq Jg Jp Lh Li Lj Ms Mz Nc Ne Nf Ni Nk Nl Nm No Nr Nt Nx Ok Om Pa Pe Qa Qb Qd) Li(Fp Fr Ih Iq Jg Jp Lh Lj Mm Ms Mz Nc Ne Nf Ni Nk Nl No Nr Nx Ok Om Pa Pe Qa Qb Qd) Ok(Fp Ih Iq Jg Jp Lh Lj Ms Mz Nc Ne Nf Ni Nk Nl Nm No Nr Nt Nx Om Pa Pe Qa Qb Qd) Mk(Fr Ih Jg Jp Lh Lj Mm Ms Mz Nc Ne Nf Ni Nk Nl Nm No Nr Nt Nx Om Pa Pe Qb Qd) Om(Fp Fr Ih Iq Jg Jp Lh Lj Mm Ms Mz Nc Ne Nf Ni Nk Nm No Nr Nt Pa Pe Qa Qb) Fp(Iq Jg Jp Lh Lj Ms Mz Nc Ne Nf Ni Nk Nl No Nr Nt Pa Pe Qa Qb Qd) Mz(Ih Iq Jg Jp Lh Lj Mm Ms Nc Nf Ni Nk Nl Nm No Nr Pa Pe Qa Qb Qd) Nk(Fr Ih Iq Jp Lh Lj Mm Ms Nc Ne Nl No Nr Nt Nx Pa Pe Qa Qb Qd) Iq(Fr Ih Jp Lh Lj Mm Ms Nc Ne Nf Nl No Nt Nx Pa Pe Qa Qb Qd) Lj(Ih Jp Lh Mm Ms Nc Ne Nf Ni Nl No Nr Nx Pa Pe Qa Qb Qd) Nr(Lh Ms Nc Ne Nf Ni Nl Nm Nt Nx Pa Pe Qa Qb Qd) No(Fr Ih Lh Mm Ms Nc Ne Ni Nl Nt Pa Pe Qa Qb Qd) Jp(Fr Ih Jg Lh Mm Ms Nc Nf Ni Nx Pa Pe Qa Qb Qd) Ne(Ih Lh Ms Nc Nf Nl Nt Pa Pe Qa Qb Qd) Ni(Lh Nc Nf Nl Nm Nt Nx Pa Pe Qa Qb Qd) Nf(Fr Ih Jg Lh Nm Nt Pa Pe Qa Qb Qd) Nc(Fr Ih Mm Ms Nl Nt Nx Qa Qb Qd) Lh(Fr Jg Mm Nm Nt Pa Pe Qa Qb Qd) Nl(Ih Mm Ms Ni Nx Pa Pe Qa Qb Qd) Pa(Fr Ih Jg Mm Nt Nx Pe Qa Qb) Ms(Ih Mm Nt Nx Qa Qb Qd) Pe(Ih Jg Nm Nt Qa Qb Qd) Nx(Ih Jg Mm Nm Qb) Qa(Ih Nm Qb Qd) Mm(Fr Jg Nm) Nt(Qb Qd) Ih(Qb Qd) FrJg} Is{Et(aA Fp Fr Hq Hr Hu Hv Hw Hx Ih Ii Ij Ik Il Im In Io Ip Iq Ir It Iu Iv Jg Jh Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Lw(aA Fp Fr Hq Hr Hu Hv Hw Hx Ih Ii Ij Ik Il Im In Io Ip Iq Ir It Iu Iv Jg Jh Jj Jk Jl Jm Jn Jo Jp Jq Jr Js Jt Lh Li Lj Lu Lv Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Ma(aA Fp Fr Hq Hr Hu Hv Hw Hx Ih Ii Ij Ik Il Im In Io Ip Iq Ir It Iu Iv Jg Jh Jj Jk Jl Jm Jn Jo Jp Jq Jr Js Jt Lh Li Lj Lu Lv Lx Ly Lz Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Me(aA Fp Fr Hq Hr Hu Hv Hw Hx Ih Ii Ij Ik Il Im In Io Ip Iq Ir It Iu Iv Jg Jh Jj Jk Jl Jm Jn Jo Jp Jq Jr Js Jt Lh Li Lj Lu Lv Lx Ly Lz Mb Mc Md Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Mh(aA Fp Fr Hq Hr Hu Hv Hw Hx Ih Ii Ij Ik Il Im In Io Ip Iq Ir It Iu Iv Jg Jh Jj Jk Jl Jm Jn Jo Jp Jq Jr Js Jt Lh Li Lj Lu Lv Lx Ly Lz Mb Mc Md Mf Mg Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd Pe Pf Pg Po Pz Qa Qb Qc Qd Qe) Mj(aA Fp Fr Hq Hr Hu Hv Hw Hx Ih Ii Ij Ik Il Im In Io Ip Iq Ir It Iu Iv Jg Jh Jj Jk Jl Jm Jn Jo Jp Jq Jr Js Jt Lh Li Lj Lu Lv Lx Ly Lz Mb Mc Md Mf Mg Mi Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om Oy Oz Pa Pb Pc Pd

Lj Mi Nn Oz Qa) Pc(aA Li Lv Mn Mv Nh Nn) My(Iq Jk Jt Mi Nm Nq) Nl(Im Jt Ly Mk Ng Oz) Mf(Lv Mi Ng Nm Nq) Ni(Jt Ml Nq Of) Mk(Lv Mi Ms) Nh(Jt Ly Oz) Jt(Nm Nq) aA(Hr Nn) LvIu MiMx MlNg HuJk ImPg IqLj} Jl{Mg(aA Et Fp Fr Hq Hr Hu Hv Hw Hx Ih Ii Ij Ik Il Im In Io Ip Iq Ir It Iu Iv Jg Jh Jj Jk Jm Jn Jo Jp Jq Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Om Oy Oz Pa Pb Pc Pd Pe Pf Pg Po Pz Qa Qb Qc Qd Qe) Io(aA Et Fp Fr Hq Hr Hu Hv Hw Hx Ih Ii Ij Ik Il Im In Ip Iq Ir It Iu Iv Jg Jh Jj Jk Jm Jn Jo Jp Jq Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Om Oy Oz Pa Pb Pc Pd Pe Pf Pg Po Pz Qa Qb Qc Qd Qe) Pz(aA Et Fp Fr Hq Hr Hu Hv Hw Hx Ih Ii Ij Ik Il Im In Ip Iq Ir It Iu Iv Jg Jh Jj Jk Jm Jn Jo Jp Jq Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Om Oy Oz Pa Pb Pc Pd Pe Pf Pg Po Qa Qb Qc Qd Qe) Jj(aA Et Fp Fr Hq Hr Hu Hv Hw Hx Ih Ii Ij Ik Il Im In Ip Iq Ir It Iu Iv Jg Jh Jk Jm Jn Jo Jp Jq Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Om Oy Oz Pa Pb Pc Pd Pe Pf Pg Po Qa Qb Qc Qd Qe) Jq(aA Et Fp Fr Hq Hr Hu Hv Hw Hx Ih Ii Ij Ik Il Im In Ip Iq Ir It Iu Iv Jg Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Om Oy Oz Pa Pb Pc Pd Pe Pf Pg Po Qa Qb Qc Qd Qe) Og(aA Et Fp Fr Hq Hr Hu Hv Hw Hx Ih Ii Ij Ik Il Im In Ip Iq Ir It Iu Iv Jg Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Oi Ok Om Oy Oz Pa Pb Pc Pd Pe Pf Pg Po Qa Qb Qc Qd Qe) Oi(aA Et Fp Fr Hq Hr Hu Hv Hw Hx Ih Ii Ij Ik Il Im In Ip Iq Ir It Iu Iv Jg Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Ok Om Oy Oz Pa Pb Pc Pd Pe Pf Pg Po Qa Qb Qc Qd Qe) Pb(aA Et Fp Fr Hq Hr Hu Hv Hw Hx Ih Ii Ij Ik Il Im In Ip Iq Ir It Iu Iv Jg Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Ok Om Oy Oz Pa Pc Pd Pe Pf Pg Po Qa Qb Qc Qd Qe) Nn(aA Et Fp Fr Hq Hr Hu Hv Hw Hx Ih Ii Ij Ik Il Im In Ip Iq Ir It Iu Iv Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Ok Om Oy Oz Pa Pc Pd Pe Pf Pg Po Qa Qb Qc Qd Qe) Mp(aA Et Fp Fr Hq Hr Hu Hv Hw Hx Ih Ii Ij Ik Il Im In Ip Iq Ir It Iu Iv Jg Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Ok Om Oy Pa Pc Pd Pe Pf Pg Po Qa Qb Qc Qd Qe) Jh(aA Et Fp Fr Hq Hr Hu Hv Hw Hx Ih Ii Ij Il Im In Ip Iq Ir It Iu Iv Jg Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Ok Om Oy Oz Pa Pc Pd Pe Pf Pg Po Qa Qb Qc Qd Qe) Ok(aA Et Fp Fr Hq Hr Hu Hv Hw Hx Ih Ii Ij Il Im In Ip Iq Ir It Iu Iv Jg Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Om Oy Oz Pa Pc Pd Pe Pf Pg Po Qa Qb Qc Qd Qe) Om(aA Et Fp Fr Hq Hr Hu Hv Hw Hx Ih Ii Ij Ik Il Im In Ip Iq Ir It Iu Iv Jg Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mw Mx My Mz Na Nb Nc Nd Ne Nf Ng Nh Ni Nj Nk Nl Nm No Nq Nr Ns Nt Nu Nv Nw Ny Oe Of Oy Oz Pa Pc Pd Pe Pf Pg Po Qa Qb Qc Qd Qe) Mw(aA Et Fp Fr Hq Hr Hu Hv Hw Hx Ih Ii Ij Il Im In Ip Iq Ir It Iu Iv Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mx My Mz Na Nb Nc Nd Ne Nf Ng Nh Ni Nj Nk Nl Nm No Nq Nr Ns Nt Nu Nv Nw Nx Ny Oe Of Oy Oz Pa Pc Pd Pe Pf Pg Po Qa Qb Qc Qd Qe) Im(aA Et Fp Fr Hq Hr Hu Hv Hw Hx Ih Ii Ij Ik Il In Ip Iq Ir It Iu Iv Jg Jk Jm Jn Jo Jr Js Jt Lh Li Lj Lu Lv Lw Lx Ly Lz Ma Mb Mc Md Me Mf Mh Mi Mj Mk Ml Mn Mq Mr Ms Mt Mu Mv Mx My Mz Na Nb Nc Nd Ne Nf Ng Nh Ni Nj Nk Nl Nm No Nq Nr Ns Nt Nu Nv Nw Nx Ny Oe Of Oy Oz Pa Pc Pd Pe Pf Pg Po Qa Qb Qc Qd Qe) Et(aA Fp Fr Hq Hr Hu Hv Hw Hx Ih Ii Ij Ik Il In Ip Iq Ir It Iu Iv Jk Jm Jn Jo Jp Jr Js Jt Lh Li Lj Lv Lw Lx Ly Lz Ma Mb Mc Md Me Mf Mh Mi Mj Mk Ml Mm Mn Mq Mr Ms Mt Mu Mv Mx My Mz Na Nb Nc Nd Ne Nf Ng Nh Ni Nj Nk Nl Nm Nq Nr Ns Nt Nu Nv Nw Nx Ny Oe Of Oy Oz Pa Pc Pd Pe Pf Pg Po Qa Qb Qc Qd Qe) Ik(aA Fp Fr Hq Hr Hu Hv Hw Hx Ih Ii Ij Il In Ip Iq Ir It Iu Iv Jg Jk Jm Jn Jo Jp Jr Js Jt Lh Li Lj Lu Lv Ly Lz Ma Mb Mc Md Me Mf Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nw Nx Oe Of Oy Oz Pa Pc Pd Pe Pf Pg Po Qa Qb Qc Qd Qe) Ma(aA Fp Hq Hr Hu Hv Hw Hx Ih Ii Ij Il In Ip Iq Ir It Iu Iv Jk Jm Jn Jo Jp Jr Js Jt Lh Li Lj Lu Lv Lx Ly Lz Mb Mc Me Mf Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nw Nx Ny Oe Of Oy Oz Pa Pc Pd Pe Pf Pg Po Qa Qb Qc Qd Qe) Nw(aA Fp Fr Hq Hr Hu Hv Hw Hx Ii Ij Il In Ip Iq Ir It Iu Iv Jk Jm Jn Jo Jp Jr Js Jt Lh Li Lj Lu Lv Lw Lx Ly Lz Mb Mc Me Mf Mh Mi Mj Mk Ml Mm Mn Mq Mr Mt Mu Mv Mx My Mz Na Nb Nc Nd Nf Ng Ni Nj Nk Nl Nm No Nq Nr Ns Nt Nu Nv Nx Ny Oe Of Oy Oz Pa Pc Pd Pe Pf Pg Po Qa Qb Qc Qd Qe) Nj(aA Fp Fr Hq Hu Hv Hw Hx Ih Ii Ij Il In Ip Iq Ir It Iu Iv Jk Jm Jn Jo Jp Jr Js Jt Lh Lj Lu Lv Lw Lx Ly Lz Mb Mc Md Mf Mh Mi Mj Mk Ml Mm Mn Mq Mr Ms Mt Mu Mv Mx My Mz Na Nb Nd Ne Nf Ng Nh Ni Nk Nm No Nq Nr Ns Nt Nu Nv Nx Ny Of Oy Oz Pa Pc Pd Pe Pf Pg Po Qa Qb Qc Qd Qe) Mu(aA Fp Hq Hr Hu Hv Hw Hx Ii Ij Il In Ip Iq Ir It Iu Iv Jk Jm Jn Jo Jp Jr Js Jt Lh Li Lj Lu Lv Lw Lx Ly Lz Mb Mc Md Me Mf Mh Mi Mj Mk Ml Mn Mq Mr Ms Mt Mv Mx My Mz Na Nb Nc Nd Ne Nf Ng Nh Nk Nl No Nq Ns Nt Nu Nv Ny Oe Of Oy Oz Pa Pc Pd Pe Pf Pg Po Qa Qb Qc Qd Qe) Pf(aA Fp Hq Hr Hu Hv Hw Hx Ii Ij Il In Ip Ir It Iu Iv Jk Jm Jn Jo Jp Jr Js Jt Lh Li Lj Lu Lv Lw Lx Ly Lz Mb Mc Me Mf Mh Mi Mj Mk Mm Mn Mq Mr Ms Mv Mx My Mz Na Nb Nc Nd Ne Nf Ng Nh Ni Nk Nl No Nq Nr Ns Nu Nv Nx Ny Oe Of Oy Pa Pc Pd Pe Pg Po Qb Qc Qd Qe) Mj(aA Fp Fr Hq Hr Hv Hw Ii Ij Il In Ip Iq Ir It Iv Jk Jm Jn Jo Jr Js Jt Lh Li Lj Lu Lw Lx Ly Lz Mb Md Me Mh Mi Mk Mm Mn Mr Mt Mx My Mz Na Nb Nc Nd Nf Nh No Nq Nr Ns Nt Nx Ny Oe Of Oy Oz Pa Pc Pd Pe Po Qa Qc) aA(Fp Fr Hr Hu Hw Hx Ih Ii Il In Ip Iq Iu Jg Jk Jm Jn Jo Jr Js Jt Lh Li Lj Lu Lv Lz Mb Mc Me Mf Mh Mi Mk Mn Mq Mx My Na Nb Nc Nd Nh Nl Nq Ns Nu Nv Ny Oe Of Oy Oz Pa Pd Pg Qc Qd Qe) Jm(Fr Hq Hr Hu Hw Hx Ii Il In Ip Iq Ir Iu Jk Jn Lh Li Lu Lv Lw Lx Lz Mb Mc Me Mh Mi Mk Mm Mn Mq Mr Ms Mt My Mz Nb Nc Nd Nf Nk Nl Nm No Nq Ns Nt Nv Nx Ny Oe Of Oy Oz Pa Pc Pe Po Qc) Nd(Fp Fr Hq Hv Hw Hx Ii Ij Il In Ip Ir It Iv Jn Jr Js Lh Li Lj Lu Lw Lx Ly Mb Me Mf Mh Mn Mr Ms Mt My Na Nc Ne Ng Nh Ni Nl Nm No Nr Ns Ny Oe Of Oy Pc Pe Po Qa Qc) Oy(Fp Fr Hr Hu Hv Hw Ii Ij In Ip Iq Ir Jg Jk Jn Jr Jt Lh Li Lu Lw Lx Mb Md Me Mh Mi Mk Ml Mn Mq Mr Mt Mv Mz Na Nb Nc Nf No Nq Nr Ns Nx Oz Pa Pc Pd Pe Pg Po Qc) Lx(Fp Hq Hr Hu Hv Hw Hx Ij Il In Ir Iu Iv Jk Jn Jr Js Lu Lv Lw Ly Mb Me Mh Mi Mk Mq Mv Mx My Na Nc Ng Nk Nl No Nq Ns Nu Nv Ny Of Pa Pc Pd Pg Qb Qc) Mb(Fr Hu Ii In Ip Iq Ir Jn Jo Jr Js Lh Lv Lw Lz Me Mf Mh Mm Mn Mq Mr Mt My Mz Nc Ne Nf Ng Nh Nk Nl Nm No Nq Ns Nu Ny Oe Of Oz Pa Pc Pe Po Qc) Pc(Fp Fr Hr Hu Il Ip Iq Ir Jn Jo Jr Js Lh Li Lu Lv Lw Ly Me Mh Mk Mn Mr Mt Mx My Mz Nb Nc Nf Ng Nl Nm Nq Ns Nu Ny Pa Pe Qc) Nc(Fp Hq Hv Hw Ij Il In Ip Ir It Iv Jn Jo Jr Jt Lh

Figure 43 Continued

Lw Mk Ms My Mz Na Ne Ng Nh Ni Nk Nl No Nr Ns Nu Nx Of Pe Pg Qa Qc) Jo(Fp Hv Hw Ii Ij In Ir It Iv Jn Jr Js Jt Lh Lw Md Mh Mr Mt Mz Na Nb Nf Nh Nm No Nr Nx Ny Oe Oz Pe Qa) Lw(Fp Hv Hw Ii Il Ip Iq Jn Jr Jt Lv Ly Lz Me Mf Mh Mi Mm Mq Mt Mv My Na Nf Nk Ns Nv Of Oz Qc) Qc(Fp Hr Hv Ip Iq Ir Jn Jr Js Lh Lj Lv Me Mh Mr Mt Mx My Mz Nf Nh No Ns Ny Oe Oz Pe Po) Lv(Fr Hr Hv Hw Ii In Ip Ir Lh Lu Mh Mn Mr Mt Na Nb Nf Nm No Nq Ns Nx Ny Oz Pe Po) Hr(Hv Hw Ii In Iq Ir Iv Jn Jr Js Lu Mf Mq Mr Mt Mz Na Nb Nf Nk No Ny Oz Pe Po) Mq(Hv Hw Ij Il In Ir It Jn Jr Js Jt Lh Mh Mr Mt Mz Na Nb Nf Nh No Pe Qa) My(Fr In Ip Iq Ir Jk Jn Jr Js Lh Lu Me Mh Mr Mt Mv Nf No Nq Ns Pa Pe Po) Ns(Fp Hv Ip Ir It Jg Jn Jp Jr Lu Mh Mr Mt Na Nb Nf No Nq Oz Pe Po) Nu(Fr Iq Ir Jn Jr Js Lh Li Mh Mi Mm Mr Mt Mz Na Nf Nm No Pe Po) Mh(Fr Hv Hw Hx Il Iq Ly Me Mk Mm Mt Na Nf Ng No Of Po Qe) No(Hu Il Iu Jk Ly Me Mk Mm Mr Ne Nl Nq Nt Nv Po Qd) Mt(Hu Il Ip Jk Me Mk Mx Nb Ng Nq Nv Oe Of Pg Po) Nf(Hu Ij Il In Jr Js Jt Me Mm Mz Of Qb Qe) Of(Hv Hw Ij In Ir Jn Jr Mr Mz Na Nb Pe) Me(Hv Ir Jn Jr Js Mf Mr Na Ny Pe) Jt(Hv Hw Ir Jn Jr Js Mz Na Nm Qa) Ly(Fr Lh Md Mr Nt Pa Pe Po) Hu(Fr Jg Lh Mr Nq Pa Pe Po) Il(Iq Lh Mi Mr Nt Pa Pe Po) Jn(Ij Jr Lj Ml Mx Mz Qb Qe) Jr(Iq Ir Lj Ml Mz Na Qe) Ng(Ip Jg Md Oz Pa Po) Na(Ip Mr Ne Oe Oz) Qe(Ir Iv Js Mz Pe) Mk(Mr Pa Pe Po) In(Ir Lh Pe) Ip(Lj Mm Oe) Fr(Mv Nq) Mz(Lj Ml) Oz(Nx Pa) IiLh IjIr IqLj NvNy} Jj{Nn(aA Et Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oi Ok Om Oy Oz Pa Pb Pc Pd Pe Pf Pg Po Pz Qa Qb Qc Qd Qe) No(aA Et Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nt Nu Nv Nw Nx Ny Oe Of Og Oi Ok Om Oy Oz Pa Pb Pc Pd Pe Pf Pg Po Pz Qa Qb Qc Qd Qe) Nt(aA Et Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nq Nr Ns Nu Nv Nw Nx Ny Oe Of Og Oi Ok Om Oy Oz Pa Pb Pc Pd Pe Pf Pg Po Pz Qa Qb Qc Qd Qe) Lx(aA Et Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Mn Nq Nr Ns Nu Nv Nw Nx Ny Oe Of Og Oi Ok Om Oy Oz Pa Pb Pc Pd Pe Pf Pg Po Pz Qa Qb Qc Qd Qe) Mp(aA Et Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm Nq Nr Ns Nu Nv Nw Nx Ny Oe Of Og Oi Ok Om Oy Oz Pa Pb Pc Pd Pe Pf Pg Po Pz Qa Qb Qc Qd Qe) Mr(aA Et Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mq Ms Mt Mu Mv Mw Mx My Mz Na Nb Nc Nd Ne Nf Ng Nh Ni Nj Nk Nl Nm Nq Nr Ns Nu Nv Nw Nx Ny Oe Of Og Oi Ok Om Oy Oz Pa Pb Pc Pd Pe Pf Pg Po Pz Qa Qb Qc Qd Qe) Mw(aA Et Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mq Ms Mt Mu Mv Mx My Mz Na Nb Nc Nd Ne Nf Ng Nh Ni Nj Nk Nl Nm Nq Nr Ns Nu Nv Nw Nx Ny Oe Of Og Oi Ok Om Oy Oz Pa Pb Pc Pd Pe Pf Pg Po Pz Qa Qb Qc Qd Qe) Ii(aA Et Fp Fr Hq Hr Hu Hv Hw Hx Ih Ij Ik Il Im In Io Ip Iq Ir It Iu Iv Jg Jh Jk Jm Jn Jo Jp Jq Jr Js Jt Lh Li Lj Lu Lv Lw Ly Lz Ma Mb Mc Md Me Mf Mg Mh Mi Mj Mk Ml Mm Mn Mq Ms Mt Mu Mv Mx My Mz Na Nb Nc Nd Ne Nf Ng Nh Ni Nj Nk Nl Nm Nq Nr Ns Nu Nv Nw Nx Ny Oe Of Og Oi Ok Om Oy Oz Pa Pb Pc Pd Pe Pf Pg Po Pz Qa Qb Qc Qd Qe) Lh(aA Et Fp Fr Hq Hr Hu Hv Hw Hx Ih Ij Ik Il Im In Io Ip Iq Ir It Iu Iv Jg Jh Jk Jm Jn Jo Jp Jq Jr Js Jt Li Lj Lu Lv Lw Ly Lz Ma Mb Mc Md Me Mf Mg Mh Mi Mj Mk Ml Mm Mn Mq Ms Mt Mu Mv Mx My Mz Na Nb Nc Nd Ne Nf Ng Nh Ni Nj Nk Nl Nm Nq Nr Ns Nu Nv Nw Nx Ny Oe Of Og Oi Ok Om Oy Oz Pa Pb Pc Pd Pe Pf Pg Po Pz Qa Qb Qc Qd Qe) Nv(aA Et Fp Fr Hq Hr Hu Hv Hw Hx Ih Ij Ik Il Im In Io Ip Iq Ir It Iu Iv Jg Jh Jk Jm Jn Jo Jp Jq Jr Js Jt Li Lj Lu Lv Lw Ly Lz Ma Mb Mc Md Me Mf Mg Mh Mi Mj Mk Ml Mm Mn Mq Ms Mt Mu Mv Mx My Mz Na Nb Nc Nd Ne Nf Ng Nh Ni Nj Nk Nl Nm Nq Nr Ns Nu Nw Nx Ny Oe Of Og Oi Ok Om Oy Oz Pa Pb Pc Pd Pe Pf Pg Po Pz Qa Qb Qc Qd Qe) Ok(aA Et Fp Fr Hq Hr Hu Hv Hw Hx Ih Ij Ik Il Im In Io Ip Iq Ir It Iu Iv Jg Jh Jk Jm Jn Jo Jp Jq Jr Js Jt Li Lj Lu Lv Lw Ly Lz Ma Mb Mc Md Me Mf Mg Mh Mi Mj Mk Ml Mm Mn Mq Ms Mt Mu Mv Mx My Mz Na Nb Nc Nd Ne Nf Ng Nh Ni Nj Nk Nl Nm Nq Nr Ns Nu Nw Nx Ny Oe Of Og Oi Om Oy Oz Pa Pb Pc Pd Pe Pf Pg Po Pz Qa Qb Qc Qd Qe) Pf(aA Et Fp Fr Hq Hr Hu Hv Hw Hx Ih Ij Ik Il Im In Io Ip Iq Ir It Iu Iv Jg Jh Jk Jm Jn Jo Jp Jq Jr Js Jt Li Lj Lu Lv Ly Lz Ma Mb Mc Md Me Mf Mg Mh Mi Mj Mk Ml Mm Mn Mq Ms Mt Mu Mv Mx My Mz Na Nb Nc Nd Ne Nf Ng Nh Ni Nj Nk Nl Nm Nq Nr Ns Nu Nw Nx Ny Oe Of Og Oi Om Oy Oz Pa Pb Pc Pd Pe Pg Po Pz Qa Qb Qc Qd Qe) Pg(aA Et Fp Fr Hq Hr Hu Hv Hw Hx Ih Ij Ik Il Im In Io Ip Iq Ir It Iu Iv Jg Jh Jk Jm Jn Jo Jp Jq Jr Js Jt Li Lj Lu Lv Lw Ly Lz Ma Mb Mc Me Mf Mg Mh Mi Mj Mk Ml Mm Mn Mq Ms Mt Mu Mv Mx My Mz Na Nb Nc Nd Ne Nf Ng Nh Ni Nj Nk Nl Nm Nq Nr Ns Nu Nw Nx Ny Oe Of Og Oi Om Oy Oz Pa Pb Pc Pd Pe Po Pz Qa Qb Qc Qd Qe) Po(aA Et Fp Fr Hq Hr Hu Hv Hw Hx Ih Ij Ik Il Im In Io Ip Iq Ir It Iu Iv Jg Jh Jk Jm Jn Jo Jp Jq Jr Js Jt Li Lj Lu Lv Lw Ly Lz Ma Mb Mc Md Me Mf Mg Mh Mi Mj Mk Ml Mm Mn Mq Mt Mu Mv Mx My Mz Na Nb Nc Nd Ne Nf Ng Nh Ni Nj Nk Nl Nm Nq Nr Ns Nu Nw Nx Ny Oe Of Og Oi Om Oy Oz Pa Pb Pc Pd Pz Qa Qb Qc Qd Qe) Ny(aA Et Fp Fr Hq Hr Hu Hv Hw Hx Ih Ij Ik Il Im In Io Ip Iq Ir It Iu Iv Jg Jh Jk Jm Jn Jo Jp Jq Jr Js Jt Li Lj Lu Lv Lw Ly Lz Ma Mb Mc Md Me Mf Mh Mi Mj Mk Ml Mm Mn Mq Ms Mt Mu Mv Mx My Mz Na Nb Nc Nd Ne Nf Ng Nh Ni Nj Nk Nl Nm Nq Nr Ns Nu Nw Nx Oe Of Og Oi Om Oy Oz Pa Pb Pc Pd Pe Pz Qa Qb Qc Qd Qe) Fr(aA Et Fp Hq Hr Hu Hv Hw Hx Ih Ij Ik Il Im In Io Ip Iq Ir It Iu Iv Jg Jh Jk Jm Jn Jo Jp Jq Jr Js Jt Li Lj Lu Lv Lw Ly Lz Ma Mb Mc Md Me Mf Mg Mh Mi Mj Mk Ml Mm Mn Mq Mt Mu Mv Mx My Mz Na Nb Nc Nd Ne Nf Nh Ni Nj Nk Nl Nm Nq Nr Ns Nu Nw Nx Oe Of Og Oi Om Oy Oz Pa Pb Pc Pd Pe Pz Qa Qb Qc Qd) Mu(aA Et Fp Hq Hr Hu Hv Hw Hx Ih Ij Ik Il Im In Io Ip Iq Ir It Iu Iv Jg Jh Jk Jm Jn Jo Jp Jq Jr Js Li Lj Lu Lv Lw Ly Lz Ma Mb Mc Md Me Mf Mg Mh Mi Mj Mk Ml Mm Mn Mq Ms Mt Mv Mx My Mz Na Nb Nc Nd Ne Nf Ng Nh Ni Nj Nk Nl Nm Nq Nr Ns Nu Nw Nx Oe Of Og Oi Om Oy Oz Pa Pb Pc Pe Pz Qa Qb Qc Qd) Pe(Et Fp Hq Hr Hu Hv Hw Hx Ih Ij Ik Il Im In Io Ip Iq Ir It Iu Iv Jg Jh Jk Jm Jn Jo Jp Jq Jr Js Jt Li Lj Lv Lw Ly Lz Ma Mb Mc Md Me Mg Mh Mi Mj Mk Ml Mm Mn Mq Ms Mt Mv Mx Mz Na Nc Nd Ne Nf Ng Nh Ni Nj Nk Nl Nm Nq Nr Ns Nu Nw Nx Oe Of Og Oi Om Oy Oz Pa Pb Pc Pd Pz Qa Qb Qc Qd Qe) Nw(aA Et Fp Hq Hr Hu Hv Hw Hx Ih Ij Ik Il Im In Io Ip Iq Ir It Iu Iv Jh Jk Jm Jn Jo Jq Jr Js Jt Li Lj Lu Lv Lw Ly Ma Mb Mc Md Me Mh Mi Mj Mk Mn Ms Mt Mv Mx My Mz Na Nb Nc Nd Ne Nf Ng Nh Nj Nk Nl Nm Nq Nr Ns Nu Nx Oe Of Og Oi Om Pa Pb Pc Pd Pz Qa Qb Qc) Mt(aA Et Hq Hr Hu Hv Hw Hx Ih Ij Ik Il Im In Io Ip Iq Ir Iu Iv Jg Jh Jk Jm Jn Jo Jq Jr Jt Li Lj Lu Lw Lz Mb Mc Md Mf Mh Mi Mk Ml Mm Mn Mq Ms Mx Mz Na Nb Nc Nd Ne Nf Nj Nk Nl Nq Nr Ns Nu Nx Oe Of Og Oi Om Oz Pa Pb Pc Pd Pz Qa Qc Qd Qe) Nd(aA Et Hq Hr Hu Hv Hw Hx Ih Ij Ik Il Im Ip Iq Ir It Iv Jg Jh Jk Jm Jn Jo Jp Jq Jr Js Jt Li Lj Lv Lw Ma Mb Md Mh Mi Mj Mm Mn Mq Mv Mx Mz Na Nb Nc Ne Nf Nh Nj Nl Nm Nq Nr Nu Nx Of Om Pa Pd Pz Qa Qb Qc Qd Qe) Il(Et Fp Hq Hr Hu Hw Hx Ih Ik Im Ip Iq Ir It Iu Iv Jg Jh Jk Jm Jn Jo Jp Jq Jr Li Lu Lv Lw Lz Ma Mb Mc Md Me Mh Mi Mj Mk Mm Mn Mv Mx My Mz Nc Ne Nf Ng Nh Nj Nk Nl Nm Nq Nr Nx Oe Of Og Oi Om Oz Pa Pb Pz Qa Qb) Jh(aA Et Fp Hq Hw Hx Ih Ik Im In Io Ip Iq Ir It Iu Iv Jk Jm Jn Jo Jr Js Li Lj Lu Lv Ly Lz Mb Md Mg Mh Mi Mk Mn Ms Mx Na Nc Ne Nf Nh Ni Nj Nk Nl Nm Nq Nr Ns Nx Oe Og Oi Om Oy Pa Pb Pz Qa Qb) Nq(aA Et Hq Hr Hu Hv Hw Hx Ih Ij In Ip Iq Ir It Iu Iv Jk Jm Jn Jo Jp Jq Jr Js Li Lv Lw Ma Mb Md Mh Mi Mm Mn Mq Mz Na Nb Nc Ne Nf Nh Nj Nk Nl Nm Nr Nu Nx Of Oi Om Pa Qa Qb Qd Qe) Jr(aA Et Hq Hr Hu Hw Hx Ih Ik Im Ip Iq Iu Jg Jk Jo

Figure 43 Continued

Jp Li Lu Lv Ly Ma Mb Md Me Mg Mh Mi Ml Mm Mn Ms Mv My Nb Nc Ne Nf Ng Ni Nj Nk Nl Nm Nr Nu Nx Of Og Oi Om Pa Pd Pz Qa Qc) Om(aA Et Fp Hq Hu Hw Ih Ik Im Io Ip Iq Ir It Iu Iv Jk Jm Jo Li Lu Lv Ly Lz Mb Mh Mi Mk Ml Mm My Na Nc Ne Nf Nh Ni Nj Nk Nl Nm Nr Ns Oe Of Og Oi Oy Pa Pb Pz Qa Qb Qc Qe) Pa(Et Fp Hq Hv Hw Ih Ij Ik In Ip Iq Ir It Iv Jk Jm Jn Jo Jp Jq Js Li Lj Lv Lw Ma Mb Md Mk Mn Mq Mv Mx Mz Na Nc Ne Nf Nh Nj Nk Nl Nm Nx Oe Of Og Oi Oz Pb Qa Qb Qe) Ma(aA Et Hq Hr Hu Hv Hw Hx Ih Ik Im In Ip Iq Ir Iu Iv Jk Jm Jn Jo Jq Js Li Lu Ly Lz Mb Md Mh Mi Mz Nb Nc Ne Nf Nh Nk Nl Nr Nu Nx Of Oi Qa Qb Qe) Hq(Et Hu Hv Hw Ih Ik Im Ip Iq Iu Iv Jk Jm Jn Jo Jp Jq Js Li Lw Mb Md Mh Mi Mm Mn Mz Nb Nc Nf Nh Nj Nk Nl Nm Nr Nx Of Og Oi Oz Pb Pc Qa Qb) Et(aA Hu Hw Ih Ik Im In Io Ip Iq It Iu Iv Jk Jm Jo Jq Lw Lz Mb Mc Md Mg Mh Mi Mn Mz Nc Nf Nh Nj Nk Nl Nr Ns Nx Oe Of Og Oi Pb Pz Qb) Jk(aA Hu Hw Ih Ik Im Io Ip Iq Iu Iv Jn Jo Jq Lu Md Mh Mi Mk Mn Nc Ne Nf Nh Nj Nk Nl Nm Nr Ns Nx Oe Of Og Oi Oz Pb Pc Pz Qc) Nc(aA Hw Hx Ih Im In Ip Iq Ir Iu Jg Jm Jn Jo Jq Js Li Lu Lv Lw Lz Md Mh Mi Mm Mx Mz Nb Nf Ni Nm Nr Nx Of Pd Qa Qb) Iq(aA Hw Ih Ik Im In Io Ip Iu Iv Jg Jm Jq Li Lv Lw Lz Md Mh Mi Mm Mn Mz Nb Nf Nj Nk Nl Nr Nx Of Og Oi Pb Pz Qb) Ip(aA Hu Hw Hx Im Ir Iu Iv Jg Jo Li Lu Lz Md Mh Mi Mk Mn Mv Mz Nb Ne Nf Nk Nl Nr Nx Of Qa) Mi(Ih Ik Im Io Jg Jm Jn Lw Mb Me Mh Mn Nj Nk Nl Nm Nx Of Og Oi Oz Pb Qb) aA(Hr Jg Jm Jn Jq Li Lw Me Mh Mk Mm Mn Nj Nk Nm Nx Of Oz Pb Qa Qb) Im(Hu Ih Ij Ir Iv Jg Jn Jq Js Mb Mh Mn Nj Nk Nl Nm Nx Of Og Qb) Of(Ih Ir It Jn Js Li Lz Md Mh Mz Nf Nk Nl Og Pb) Hw(Ih Jm Jn Jq Js Md Mm Mn Nf Nj Nm Pb Qb) Iu(Ih Ij Jg Jq Lw Mn Mz Nf Nm Nx) Jo(Ih Ik Jm Jn Jq Md Nk Nl Pb Qb) Nx(Li Lu Lz Md Mh Mm Nl Pb Qa) Nm(Jn Lu Lz Md Mh Nf Nk Oi) Oi(Ih Ir Jg Js Li Mm Qa) Md(Jm Jn Li Mh Nj Qb) Nf(Ih Ir Jm Jn Nj Nl) Ik(Ir Iv Js Li Nb) Lu(Jn Jq Mn Nj) Mh(Jm Js Mm Qa) Ir(Mb Ni Qc) Jn(Mm Mn Nl) Jq(Li Ne) Js(Mb Nk) Pb(Nb Nr) Melv MmHu MnNl QaOg] Mp[Et(aA Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Om Oy Oz Pa Pb Pc Pd Pe Pf Pg Po Pz Qa Qb Qc Qd Qe) Jh(aA Fp Fr Hq Hr Hu Hv Hw Hx Ih Ii Ij Ik Il Im In Io Ip Iq Ir It Iu Iv Jg Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Om Oy Oz Pa Pb Pc Pd Pe Pf Pg Po Pz Qa Qb Qc Qd Qe) Jq(aA Fp Fr Hq Hr Hu Hv Hw Hx Ih Ii Ij Ik Il Im In Io Ip Iq Ir It Iu Iv Jg Jk Jm Jn Jo Jp Jr Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Om Oy Oz Pa Pb Pc Pd Pe Pf Pg Po Pz Qa Qb Qc Qd Qe) Om(aA Fp Fr Hq Hr Hu Hv Hw Hx Ih Ii Ij Ik Il Im In Io Ip Iq Ir It Iu Iv Jg Jk Jm Jn Jo Jp Jr Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oi Ok Oy Oz Pa Pb Pc Pd Pe Pf Pg Po Pz Qa Qb Qc Qd Qe) Nw(aA Fp Fr Hq Hr Hu Hv Hw Hx Ih Ii Ij Ik Il Im In Io Ip Iq Ir It Iu Iv Jg Jk Jm Jn Jo Jp Jr Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Oe Of Og Oi Ok Oy Oz Pa Pb Pc Pd Pe Pf Pg Po Pz Qa Qb Qc Qd Qe) Mg(aA Fp Fr Hq Hr Hu Hv Hw Hx Ih Ii Ij Ik Il Im In Io Ip Iq Ir It Iu Iv Jg Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nx Ny Oe Of Og Oi Ok Oy Oz Pa Pc Pd Pe Pf Pg Po Pz Qa Qb Qc Qd Qe) Mu(aA Fp Fr Hq Hr Hu Hv Hw Ih Ii Ij Ik Il Im In Io Ip Iq Ir It Iu Iv Jg Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mv Mw Mx My Mz Na Nb Nc Nd Ne Nf Ng Nh Ni Nj Nk Nl Nm Nn No Nq Nr Ns Nt Nu Nv Nx Ny Oe Of Og Oi Ok Oy Oz Pa Pb Pc Pd Pe Pf Pg Po Pz Qa Qb Qd Qe) Oi(aA Fp Fr Hq Hr Hu Hv Hw Hx Ih Ii Ij Ik Il Im In Ip Iq Ir It Iu Iv Jg Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mv Mw Mx My Mz Na Nb Nc Nd Ne Nf Ng Nh Ni Nj Nk Nl Nm Nn No Nq Nr Ns Nt Nu Nv Ny Oe Of Og Ok Oy Oz Pa Pb Pc Pd Pe Pf Pg Po Pz Qa Qb Qc Qd Qe) Ok(Fp Fr Hq Hr Hu Hv Hw Hx Ih Ii Ij Ik Il Im In Io Ip Iq Ir It Iu Iv Jg Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mv Mw Mx My Mz Na Nb Nc Nd Ne Nf Ng Nh Ni Nj Nk Nl Nm Nn No Nq Nr Ns Nt Nu Nv Ny Oe Of Og Oy Oz Pa Pb Pc Pd Pe Pf Pg Po Pz Qa Qb Qc Qd Qe) Mt(aA Fp Fr Hq Hr Hu Hv Hx Ih Ii Ij Ik Il Im In Io Ip Iq Ir It Iu Iv Jg Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mv Mw Mx My Mz Na Nb Nc Nd Ne Nf Ng Nh Ni Nj Nk Nl Nm Nn No Nq Nr Ns Nu Nv Nx Ny Oe Of Og Oy Oz Pa Pb Pc Pd Pf Pg Po Pz Qa Qb Qc Qd Qe) No(Fp Fr Hq Hr Hu Hv Hw Hx Ih Ii Ij Ik Il Im In Io Ip Iq Ir It Iu Iv Jg Jk Jm Jn Jo Jp Jr Js Jt Lh Li Lj Lu Lv Lw Lx Ly Lz Ma Mb Mc Md Me Mf Mh Mi Mj Mk Ml Mn Mq Mr Ms Mv Mw Mx My Mz Na Nb Nc Nd Ne Nf Ng Nh Ni Nj Nl Nm Nq Ns Nt Nu Nv Nx Ny Oe Of Og Oy Oz Pa Pb Pc Pd Pe Pf Pg Po Pz Qa Qb Qc Qd Qe) Pf(Fr Hq Hu Hv Hw Ih Ii Ij Ik Il Im In Io Ip Iq Ir It Iu Iv Jg Jk Jm Jn Jo Jp Jr Js Jt Lh Lu Lv Lw Lx Ly Lz Ma Mb Mc Md Me Mf Mh Mi Mj Mk Mm Mn Mq Mr Ms Mv Mw Mx My Mz Na Nb Nc Nd Ne Nf Ng Nh Ni Nj Nk Nl Nm Nn Nq Nr Ns Nt Nu Nv Nx Ny Oe Of Og Oy Oz Pa Pb Pc Pd Pe Pg Po Pz Qa Qb Qc Qd) aA(Fp Hq Hr Hu Hv Hw Hx Ih Ii Ij Ik Il Im In Io Ip Iq Ir It Iu Iv Jg Jk Jm Jn Jp Jr Js Jt Lh Li Lj Lu Lv Lx Ly Lz Mb Mc Md Me Mf Mh Mi Mj Mk Ml Mn Mq Mr Ms Mv Mw Mx My Mz Na Nb Nc Nd Ne Nf Ng Nh Nj Nl Nm Nn Nq Nr Ns Nu Nv Nx Ny Oe Og Oy Oz Pa Pb Pc Pd Pe Pg Po Pz Qa Qb Qc Qd Qe) Nj(Fr Hq Hr Hu Hv Hw Ih Ii Ij Ik Im In Io Ip Iq Ir It Iu Iv Jg Jk Jm Jn Jo Jp Jr Js Jt Lh Lu Lv Lw Lx Ly Lz Mc Md Me Mf Mh Mi Mj Ml Mm Mn Mq Mr Ms Mv Mw Mx My Mz Na Nb Nc Ne Nf Ng Nh Ni Nk Nl Nm Nn Nr Ns Nt Nv Nx Ny Oe Og Oy Oz Pa Pc Pe Pg Po Qa Qd Qe) Io(Fp Fr Hq Hr Hu Hv Hw Hx Ih Ii Ij Ik In Ip Iq Ir It Iu Iv Jg Jk Jn Jo Jp Jr Js Jt Lh Li Lj Lu Lx Lz Ma Mb Md Me Mh Mi Mj Mk Ml Mm Mn Mq Mr Mv Mw Mz Na Nb Nc Nd Ne Nf Nh Ni Nk Nl Nm Nn Nr Ns Nt Nu Nv Nx Ny Oe Og Oz Pa Pe Pg Po Qa Qb Qc Qd Qe) Ik(Fp Fr Hq Hr Hu Hv Hw Hx Ih Ii Ij Il In Ip Iq Ir It Iu Iv Jg Jk Jm Jn Jo Jp Jr Js Jt Lh Lj Lu Lv Lw Lx Lz Ma Mc Me Mf Mh Mi Mj Ml Mq Mr Mw Mx My Mz Na Nb Nc Ne Nf Nh Ni Nk Nl Nm Nn Nq Nr Ns Nt Nv Nx Ny Oe Oz Pa Pc Pe Po Pz Qa Qb Qd Qe) Ny(Fp Fr Hq Hr Hu Hv Hw Ij Il Im In Ip Iq Ir Iv Jg Jk Jm Jn Jp Jr Js Jt Lj Lu Lv Lw Lx Ly Ma Mb Mc Me Mf Mh Mi Mj Mk Mm Mn Mq Mr Mv Mw Mx My Mz Na Nb Nc Nd Ne Nf Ng Nh Ni Nm Nn Nq Ns Nu Nv Nx Oe Of Og Oy Oz Pa Pb Pc Pd Pe Pg Pz Qc) Nn(Fr Hq Hr Hu Hv Hw Ii Ij Im In Ip Iq Ir It Iv Jm Jn Jr Js Lu Lv Lz Mc Md Me Mf Mh Mj Mk Mm Mn Mq Mr Ms Mv Mw My Mz Na Nb Nc Nd Ne Nf Ng Nh Ni Nk Nl Nm Nq Nr Ns Nu Nx Oe Of Og Oy Oz Pa Pb Pc Pd Pe Pg Po Pz Qa Qc) Mz(Fp Fr Hq Hr Hu Hv Hx Ii Ij Im In Ip Jg Jm Jn Jo Jr Js Jt Lh Lj Lv Lw Lx Lz Mb Mc Md Me Mf Mh Mj Ml Mm Mn Mq Mv Mw Mx My Na Nc Nd Ne Nf Ng Nh Nk Nl Nm Nq Ns Nu Nx Oe Of Og Oy Pa Pb Pc Pd Pe Pg Pz Qa Qb Qc Qd) Jr(Fr Hr Hu Hv Ih Ij In Ip Iq Ir It Jg Jk Jm Jn Jo Jp Js Jt Li Lu Lv Lw Lx Ma Mb Mc Md Me Mf Mh Mi Mj Mk Ml Mm Mn Mv Mw Mx My Na Nc Nd Ne Nf Ng Nh Ni Nk Nl Nm Nq Ns Nu Oe Of Og Oy Pb Pc Pz Qa Qb Qc Qd Qe) Mh(Fr Hq Hu Hv Hw Ih Ij Im In Ip Iq Ir It Iu Iv Jg Jm Jn Jp Js Jt Lw Ly Lz Mc Md Me Mf Mi Mj Mk Mm Ms Mw Mx My Na Nb Ne Nf Ng Nh Ni Nk Nl Nm Nq Nr Ns Nt Nu Nx Oe Og Oy Pa Pb Pc Pd Pz Qa Qd) Lx(Hq Hu Hv Hw Hx Ij Il In Ip Iq Ir Iu Iv Jg Jm Jn Jo Jp Js Jt Lu Lw Ly Lz Ma Mb Mc Md Mf Mi Mj Mk Mn Mq Ms Mv Mw Mx My Nb Nc Nd Ne Nf Ng Nh Nk Nl Nm Nq Ns Nu Nx Oe Og Oy Oz Pc Pe Pg Pz) Nh(Fr Hq Hu Hv Hw Ih Ii Ij Im In Ip Iq Ir Iu Iv Jg Jm Jn Jp Js Jt Lv Lw Ly Ma Mb Mc Md Me Mf Mj Mk Mm Mr Mv Mw Mx My Na Nb Nc Nd Nf Ng Ni Nm Nq Nr Ns Nu Nx Oe Of Og Oy Oz Pb Pc Pe Pz) Ip(Fr Hq Hu Hv Hw Ih Ii Ij Im In Iq Ir Iv Jg Jm Jn Jp Js Jt Lh Lu Lw Ly Lz Ma Md Me Mf Mi Mj Ml Mr Ms Mw Mx My Na Nb Nc Ne Nf Ng Ni Nk Nl Nm Ns Nu Oe Og Pa Pe Po Pz Qa Qd) Mw(Fp Fr Hq Hv Ih Ij

Nq Nr Ns Nt Nu Nv Nx Ny Oe Of Og Oy Oz Pa Pb Pc Pd Pe Pf Pg Po Pz Qa Qb Qc Qd Qe) Ik(aA Et Fp Fr Hr Hu Hv Hw Hx Ih Ii Ij Il Im In Ip Iq Ir It Iu Iv Jg Jh Jk Jm Jn Jo Jp Jq Jr Js Jt Lh Li Lj Lu Lv Lw Lx Ly Lz Ma Mc Md Me Mf Mh Mi Mj Mk Mm Mn Mq Mr Mt Mu Mv Mx My Mz Na Nb Nc Nd Ne Nf Ng Nh Ni Nj Nk Nl Nm Nn No Nq Nr Ns Nt Nu Nv Nx Ny Oe Of Og Oy Oz Pa Pb Pc Pd Pe Pf Pg Po Pz Qa Qb Qc Qd Qe) Jh(aA Et Fp Fr Hq Hr Hv Hw Hx Ii Ij Il Im In Ip Iq Ir It Iu Iv Jg Jk Jm Jn Jo Jp Jq Jr Js Jt Lh Li Lj Lu Lv Lw Lx Ly Lz Ma Mc Md Me Mf Mg Mh Mi Mj Mk Ml Mm Mn Mq Mr Ms Mt Mu Mv Mx My Mz Na Nb Nc Nd Ne Nf Ng Nh Ni Nj Nk Nl Nm Nn Nr Ns Nt Nu Nv Nx Ny Oe Of Og Oy Oz Pa Pb Pc Pd Pe Pf Pg Po Pz Qa Qb Qc Qe) Nn(aA Et Fp Hq Hr Hu Hv Hw Hx Ii Ij Il Im In Ip Iq Ir Iv Jg Jk Jm Jn Jo Jp Jq Jr Js Jt Lh Li Lj Lu Lv Lw Lx Ly Lz Ma Mc Me Mf Mg Mh Mi Mj Mk Ml Mm Mn Mq Mr Ms Mt Mu Mv Mx My Mz Na Nb Nc Nd Nf Ng Nh Ni Nj Nk Nl No Nq Nr Ns Nt Nu Nv Nx Ny Oe Of Og Oy Oz Pa Pb Pc Pd Pe Pf Pg Po Pz Qa Qb Qc Qd Qe) Pz(Et Fp Fr Hq Hr Hu Hv Hw Hx Ih Ii Ij Il Im In Ip Iq Ir It Iu Iv Jg Jk Jm Jn Jo Jq Jr Js Jt Lh Li Lj Lu Lv Lw Lx Ly Lz Ma Mc Me Mf Mg Mh Mi Mj Mk Mm Mn Mq Mr Mt Mu Mv Mx My Mz Na Nb Nc Nd Nf Ng Nh Nj Nk Nl Nm No Nr Ns Nt Nu Nv Nx Ny Oe Of Og Oy Oz Pa Pc Pd Pe Pf Pg Po Qa Qb Qc) Nj(aA Et Fp Fr Hq Hr Hu Hv Hw Hx Ih Ii Ij Il Im In Ip Iq Ir It Iu Iv Jg Jk Jm Jn Jo Jp Jq Jr Js Jt Lh Li Lj Lu Lv Lw Lx Ly Lz Ma Mc Md Me Mf Mh Mi Mj Mk Mn Mq Mr Ms Mt Mu Mx My Mz Na Nb Nd Nf Ng Ni Nm No Nq Nr Ns Nt Nu Nx Oe Og Oy Oz Pa Pc Pd Pe Pf Pg Po Qa Qb Qc Qd Qe) Mu(aA Et Fp Hq Hr Hu Hv Hw Hx Ii Ij Il Im In Ip Iq Ir It Iu Iv Jk Jm Jn Jo Jp Jq Jr Js Lh Lu Lv Lw Lx Ly Lz Ma Mc Me Mf Mg Mh Mi Mj Mk Ml Mn Mq Mr Mt Mv My Mz Na Nb Nc Nd Nf Ng Nh Nk Nl Nq Nr Ns Nv Ny Oe Of Og Oy Oz Pa Pb Pc Pd Pe Pf Pg Po Qa Qb Qc) Jq(Et Fp Fr Hq Hr Hu Hv Hw Hx Ih Ii Ij Il Im In Ip Iq Ir It Iu Iv Jk Jm Jn Jr Jt Lh Li Lu Lv Lx Ly Lz Ma Mc Md Me Mf Mh Mi Mj Mk Ml Mn Mq Mt Mx My Mz Nb Nc Nd Ng Nh Ni No Nq Nr Ns Nt Nv Ny Oe Of Og Oy Oz Pb Pc Pd Pe Pf Pg Po Qa Qb Qc Qd Qe) Nd(aA Fp Hq Hr Hv Hw Ih Ii Ij Il Im In Ip Iq Ir It Iv Jk Jm Jn Jo Jr Js Lh Li Lj Lu Lv Lw Lx Ly Lz Mc Me Mf Mh Mi Mk Mn Mr Ms Mt Mx My Mz Na Ne Ne Nf Ng Nh Ni Nl No Ns Nt Nu Nv Nx Oe Og Oy Pa Pc Pd Pe Pf Po Qa Qb Qc Qd Qe) Qc(aA Et Fp Fr Hr Hu Hv Hw Ih Ii Ij Il In Ip Iq Ir It Iv Jm Jn Jo Jr Js Jt Lh Li Lj Lu Lv Lw Lx Ly Lz Ma Mc Me Mf Mh Mi Mj Mk Mn Mq Mr Mt Mx My Mz Na Nb Nc Nf Ng No Nr Ns Nx Oe Og Oy Oz Pa Pd Pe Pf Pg Po Qa Qb) Pf(aA Et Fp Hu Hv Hw Hx Ii Ij Il Im In Ip Iq Ir It Iv Jm Jn Jr Js Lh Lj Lu Lw Lx Ly Lz Ma Mb Me Mf Mg Mh Mi Mj Mr Mt Mv Mx My Mz Na Nb Nc Nf Ng Nk Nr Ns Nu Nx Ny Oe Of Og Oy Oz Pa Pb Pc Pd Pe Pg Po Qa Qb Qd) Hw(Hq Hr Hu Hx Ii Ij Il Im In Ip It Jk Jm Jo Jr Jt Lh Lv Lw Lx Ly Ma Mc Md Mc Mg Mh Mj Ml Mq Mr Mt My Mz Nb Nc Nf Ng Nq Ns Nu Nv Ny Of Og Oy Pa Pb Pc Pe Pg Qb Qd Qe) Og(Et Fp Fr Hr Hv Hx Ii Ij Im In Ip Iq Ir It Iv Jg Jk Jn Jo Jr Js Jt Li Lv Lw Lx Ma Md Me Mh Mi Mj Mq Mr Mt Mx Mz Na Nb Nc Nf Nm No Nq Nr Nt Nx Pc Pd Pe Po Qa Qb) Ma(aA Fp Hr Hu Hv Ii Ij Il Im In Ip Iq Ir It Iv Jm Jn Jo Jr Js Lh Lx Me Mg Mi Mj Mq Mr Mx My Mz Na Nb Nf Ng No Nr Ns Nx Pa Pc Pd Pe Po Qa Qb) Na(Fr Hq Hr Hu Hx Im Ip Iq Jk Jr Jt Lh Lw Lx Md Me Mh Ml Mq Mr Mt My Mz Nb Nc Ni Nk Nl No Nq Ns Nt Nu Ny Oe Of Oy Pa Pb Pe Po Qb Qd Qe) Mr(Fp Hq Hr Hu Hv Hx Ii Il Im In Ip Jm Jn Jo Jr Lh Lu Lw Lx Ly Lz Mc Me Mg Mh Mj Mm My Ng Ns Nu Nv Ny Of Oy Pa Pb Pc Pg Qb Qd) Pe(Fp Hq Hr Hu Hv Ii Ij Il Im Ip Jm Jn Jo Jr Lh Lu Lw Lx Ly Me Mh Mj Mk Mm Mq My Nb Ng Ns Nu Nv Of Oy Pa Pb Pc Pg Qb Qd) Jr(Et Hr Hu Hv Im In Ip Ir Iv Jg Jn Jo Jt Lj Lw Lx Me Mg Mi My Mz Nc Nf Ni Nm Nq Ns Of Oy Pa Pb Pc Po Qa) Hv(Hr Hu Il Im Ip Jn Jt Lh Lw Lx Md Me Mg Mi Mj Ml My Mz Nb Nc Ng Nq Ns Ny Of Oy Pa Pb Pc Po Qb Qd) Im(Ii Ij In Ip Ir Iv Jm Jn Jo Js Lh Li Lw Ly Me Mh Mi Mq My Nc Nf Ng Nh Nk Nl Nr Ns Nx Oe Oy Qa) Iv(Hr Hu Hx Ip Jm Jt Lv Lw Lx Ly Me Mg Mh Mj My Mz Nb Nc Ng Ns Of Oy Pb Pc Qb Qd Qe) Lx(Hq Ii Ij Il In Ip Ir Jm Jn Js Lh Lw Ly Mh Mj Mq My Mz Nb Nf Ng Ns Pc Qa) Pb(aA Et Fr Hr Ij In Ir Jn Jo Jt Lh Me Mh Mq Mt Mz Nb Nf Ni Nm No Nr Nx Qa) Nc(aA Et Fp Hr Ij In Ip Ir It Jm Jn Jo Jt Lw Me Mq My Mz Ni Nm No Nx Qa) In(Et Hr Hu Hx Ip Jm Lh Md Me Mj Ml My Mz Nb Ns Ny Oy Pa Pc Po Qd) Jn(Hr Hu Ii Ip Ir Lj Lv Me Mg Mi Mj Ml My Mz Nq Ns Oy Pa Pc Po) Po(Hr Hu Ij Il Jm Lw Ly Mh Mj My Nb Ng Ns Nv Of Oy Pc Pg) Lh(Fp Hr Il Jm Jo Lw Ly Me Mg Mj Nb Ns Nv Pa Pc Qb Qe) No(Hr Hu Il Ly Me Mg Mh Mj Ms My Nb Ng Nu Nv Oy Qd) Nf(Hr Hu Hx Ip Jm Lw Me Ml Mm My Ng Ns Ny Of Oy Pc) Mh(aA Et Ih Ip Lv Lw Ly Mg Mj Mm Mv My Ng Ni Oy) Ir(Hr Hu Ij Ip Jo Jt Me Mj Ml Mz Nb Nu Qb Qd) Et(Hr Hu Ij Ip Lw Mg Ng Nk Ns Oe Oy Pa) Lw(aA Hu Ip Iq Jm Lv Mi My Ns Oy Pa) Qa(Ip Jt Mg Mj My Mz Ng Oy Pc Qb Qd) Mj(aA Ij Jo Js Mi Mt Mz Nr Nt) Ng(Fr Iq Jk Js Mi Nq Nr Nt Pa) Ii(Hr Ip Jm Ly My Nb Ns Oy Pc) Ij(Hr Hu Ip Jm Me Nb Pa Pc) Pc(Fr Ip It Js Mn Nq Nx) aA(Hr Ip Me Oz Qd) Nr(Hr Ly Mg Nu) Js(Hr Lj Me Ns) My(Nb Nq Nx) Nt(Ly Nb) Ip(Jm Mt) Jo(Jt Mz) FrNb NmMg LyPa Hrlt HuNx} Mw{Et(aA Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mx My Mz Na Nb Nc Nd Ne Nf Ng Nh Ni Nj Nk Nl Nm Nn No Nq Nr Ns Nt Nu Nv Nx Ny Oe Of Og Oi Oy Oz Pa Pb Pc Pd Pe Pf Pg Po Pz Qa Qb Qc Qd Qe) Mg(aA Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mx My Mz Na Nb Nc Nd Ne Nf Ng Nh Ni Nj Nk Nl Nm Nn No Nq Nr Ns Nt Nu Nv Nx Ny Oe Of Og Oi Oy Oz Pa Pb Pc Pd Pe Pf Pg Po Pz Qa Qb Qc Qd Qe) Ng(aA Fp Fr Hq Hr Hu Hv Hw Hx Ih Ii Ij Ik Il Im In Io Ip Iq Ir It Iu Iv Jg Jh Jk Jm Jn Jo Jp Jq Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mx My Mz Na Nb Nc Nd Ne Nf Nh Ni Nj Nk Nl Nm Nn No Nq Nr Ns Nt Nu Nv Nx Ny Oe Of Og Oi Oy Oz Pa Pb Pc Pd Pe Pf Pg Po Pz Qa Qb Qc Qd Qe) Jq(aA Fp Fr Hq Hr Hu Hv Hw Hx Ih Ii Ij Ik Il Im In Io Ip Iq Ir It Iu Iv Jg Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mx My Mz Na Nb Nc Nd Ne Nf Nh Ni Nj Nk Nl Nm Nn No Nq Nr Ns Nt Nu Nv Nx Ny Oe Of Oi Oy Oz Pa Pb Pc Pd Pe Pf Pg Po Pz Qa Qb Qc Qd Qe) Og(aA Fp Fr Hq Hr Hu Hv Hw Hx Ih Ii Ij Ik Il Im In Io Ip Iq Ir It Iu Iv Jg Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mx My Mz Na Nb Nc Nd Ne Nf Nh Ni Nj Nk Nl Nm Nn No Nq Nr Ns Nt Nu Nv Nx Ny Oe Of Oi Oy Oz Pa Pb Pc Pd Pe Pf Pg Po Pz Qa Qb Qc Qe) aA(Fp Fr Hq Hr Hu Hv Hw Hx Ih Ii Ij Ik Il Im In Io Ip Iq Ir It Iu Iv Jh Jk Jm Jn Jo Jp Jr Js Jt Lh Li Lj Lu Lv Lw Lx Ly Lz Ma Mb Mc Md Me Mf Mh Mi Mj Mk Ml Mm Mn Mq Mr Ms Mt Mu Mv Mx My Mz Na Nb Nc Nd Ne Nf Nh Ni Nj Nk Nl Nm Nn No Nq Nr Ns Nt Nu Nv Nx Ny Oe Of Oi Oy Oz Pa Pb Pc Pd Pe Pf Pg Po Pz Qa Qb Qc Qd Qe) Jr(Fp Fr Hq Hr Hu Hv Hw Hx Ih Ii Ij Ik Il Im In Io Ip Iq Ir It Iv Jg Jh Jk Jm Jn Jo Jp Js Jt Lh Li Lj Lu Lv Lw Lx Ly Lz Ma Mb Mc Md Me Mf Mh Mi Mj Mk Ml Mm Mn Mq Mr Ms Mt Mu Mv Mx My Mz Na Nb Nc Nd Ne Nf Nh Ni Nj Nk Nl Nm Nn No Nq Ns Nu Nv Nx Ny Oe Of Oi Oy Oz Pa Pb Pc Pd Pe Pf Pg Po Pz Qa Qb Qc Qd Qe) Ik(Fp Fr Hq Hr Hu Hv Hw Hx Ih Ii Il Im Io Ip Iq Ir Iu Iv Jg Jh Jm Jn Jp Js Jt Lh Li Lj Lu Lx Lz Ma Md Mf Mh Mi Mj Mk Ml Mm Mn Mq Mr Ms Mt Mu Mx My Mz Na Nb Nc Ne Nf Nh Nj Nk Nl Nm Nn No Nq Nr Ns Nt Nu Nv Nx Ny Oe Of Oi Oy Oz Pa Pb Pc Pd Pe Pf Pg Po Pz Qa Qb Qc Qd Qe) Pf(Fr Hq Hr Hu Hv Hw Hx Ii Ij Il Im In Io Ip Iq Ir It Iu Iv Jh Jk Jm Jn Jo Jp Js Jt Lh Lu Lv Lw Lx Ly Lz Ma Mb Mc Md Mf Mh Mi Mj Ml Mm Mq Mr Ms Mt Mu Mx My Mz Na Nb Nc Nd Ne Nf Nh Ni Nj Nl Nm Nn No Nq Ns Nu Nv Nx Ny Oe Of Oi Oy Oz Pa Pb Pc Pd Pe Pg Po Pz Qc) Pb(Fp Fr Hr Hu Hv Hw Hx Ih Ii Ij Il Im In Io Ip Iq Ir It Iv Jh Jm Jn Jo Jp Js Jt Lh Li Lj Lu Lv Lw Lx Ly Lz Ma Mb Md Me Mf Mh Mi Mj Ml Mm Mq Mr Ms Mt Mu Mx My Mz Na Nb Nc Nd Ne Nf Nh Ni Nj Nl Nm Nn No Nq Nr Ns Nt Nu Nx Ny Oe Oi Oy Pa Pc Pe Po Pz Qa) No(Fp Hq Hr Hu Hv Hw Hx Ii Il Im In Io Ip Iq Iu Jh Jk Jm Jn Jo Jt Lv Lx Ly Ma Mb Mc Md Me Mh Mi Mj Mk Ml Mm Mq Ms Mt Mu Mv My Na Nb Nc Nd Ne Nh Nj Nk Nl Nn Nq Nr Ns Nt Nu Nv Nx Ny Oe Of Oi Oy Oz Pa Pd Pg Po Pz Qc Qd Qe) Oy(Fp Fr Hu Hv Hw Ih Ii Ij Il Im In Io Iq Iu Iv Jg Jh Jk Jm Jn Jp Js Lh Li Lj Lu Lv Lx Lz Ma Mb Md Mf Mh Mi Mj Mk Ml Mr Mt Mu Mx Mz Na Nb Nd Ne Nf Nh Nj Nk Nl Nn Nq Nr Ns Nt Nu Nx Oi Oz Pd Pe Pg Po Pz Qa Qb Qc) Hu(Fp Fr Hv Hw Hx Ih Il Im Io Ip Iq Ir Iv Jh Jk Jm Jn

NmNc} Im{Nc(Iv Jm Nb) MhNy IkLh IrNx} Nq{Ng(Ii Js Pe) HwOg OyPe} Jo{Lh(Hr Ip Me Nc) IqNx} Ik{Ip(Ir Pe) MePe JkJn} Nd{Ng(Nt Ny)} In{MeLh NcPe} MbNyOg

Unconstrained panels with 2 analytes, where 1.0E-6 >= 'AUC p-value' > 0. Contains 2,273 panels of 7,260 total panels evaluated. : Et(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm Nn No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nn(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mp Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Mp(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mt Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Mt(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mw Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Mw(aA Fp Fr Hq Hr Hu Hv Hw Hx Ih Ii Ij Ik Il Im In Io Ip Iq Ir Is It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Is(aA Fp Fr Hq Hr Hu Hv Hw Hx Ih Ii Ij Ik Il Im In Io Ip Iq Ir It Iu Iv Jg Jh Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jh(aA Fp Fr Hq Hr Hu Hv Hw Hx Ih Ii Ij Ik Il Im In Io Ip Iq Ir It Iu Iv Jg Ji Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Ji(aA Fp Fr Hq Hr Hu Hv Hw Hx Ih Ii Ij Ik Il Im In Io Ip Iq Ir It Iu Iv Jg Jj Jk Jl Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Jl(aA Fp Fr Hq Hr Hu Hv Hw Hx Ih Ii Ij Ik Il Im In Io Ip Iq Ir It Iu Iv Jg Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nw Nx Ny Oe Of Og Oh Oi Ok Om On Oy Oz Pa Pb Pc Pd Pe Pf Pg Po Pz Qa Qb Qc Qd Qe) Nw(aA Fp Fr Hq Hr Hu Hv Hw Hx Ih Ii Ij Ik Il Im In Io Ip Iq Ir It Iu Iv Jg Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nx Ny Oe Of Og Oh Oi Ok Om On Oy Oz Pa Pb Pc Pd Pe Pf Pg Po Pz Qa Qb Qc Qd Qc) Oh(aA Fp Fr Hq Hr Hu Hv Hw Hx Ih Ii Ij Ik Il Im In Io Ip Iq Ir It Iu Iv Jg Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nx Ny Oe Of Og Oi Ok Om On Oy Oz Pa Pb Pc Pd Pe Pf Pg Po Pz Qa Qb Qc Qd Qe) Ok(aA Fp Fr Hq Hr Hu Hv Hw Hx Ih Ii Ij Ik Il Im In Io Ip Iq Ir It Iu Iv Jg Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nx Ny Oe Of Og Oi Om On Oy Oz Pa Pb Pc Pd Pe Pf Pg Po Pz Qa Qb Qc Qd Qe) Om(aA Fp Fr Hq Hr Hu Hv Hw Hx Ih Ii Ij Ik Il Im In Io Ip Iq Ir It Iu Iv Jg Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Nc Nf Ng Nh Ni Nj Nk Nl Nm No Nq Nr Ns Nt Nu Nv Nx Ny Oe Of Og Oi On Oy Oz Pa Pb Pc Pd Pe Pf Pg Po Pz Qa Qb Qc Qd Qe) On(aA Fp Fr Hq Hr Hu Hv Hw Hx Ih Ii Ij Ik Il Im In Io Ip Iq Ir It Iu Iv Jg Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nx Ny Oe Of Og Oi Oy Oz Pa Pb Pc Pd Pe Pf Pg Po Pz Qa Qb Qc Qd Qe) Pf(aA Fp Fr Hq Hr Hu Hv Hw Hx Ih Ii Ij Ik Il Im In Io Ip Iq Ir It Iu Iv Jg Jj Jk Jm Jn Jo Jp Jq Jr Js Jt Lh Li Lj Lu Lv Lw Lx Ly Lz Ma Mb Mc Md Me Mf Mg Mh Mi Mj Mk Ml Mm Mn Mq Mr Ms Mu Mv Mx My Mz Na Nb Nc Nd Ne Nf Ng Nh Ni Nj Nk Nl Nm No Nq Nr Ns Nt Nu Nv Nx Ny Oe Of Og Oi Oy Oz Pa Pb Pc Pd Pe Pg Po Pz Qa Qb Qc Qd Qe) Mu(aA Fp Fr Hv Hw Ih Ii Ij Ik Il Im In Io Ip Iq Ir It Iu Jg Jj Jm Jn Jo Jp Jq Jr Js Lh Li Lj Lu Lw Lx Ly Lz Ma Mb Mc Md Mf Mg Mh Mi Mj Mk Ml Mm Mn Mq Mr Mv Mx My Na Nc Nd Ne Nf Ng Nh Nj Nk Nl Nm No Nr Ns Nv Nx Ny Oe Og Oi Oy Pa Pb Pc Pe Pg Pz Qa Qb Qe) Fr(aA Fp Hq Hu Hv Hw Ii Ij Ik Il Im In Io Ip Iq Ir It Iv Jg Jj Jn Jo Jq Jr Js Lh Li Lj Lw Lx Ly Mb Mc Md Mf Mg Mh Mi Mj Mq Mr Mv Mx My Mz Na Nc Nd Ne Nf Ng Nh Nj Nk Nm No Nq Nr Ns Nu Nv Nx Ny Oe Of Og Oi Oy Oz Pa Pb Pc Pe Pg Po Pz Qa Qb Qc) Ma(aA Fp Hr Hv Hw Hx Ih Ii Ij Ik Im In Io Ip Iq Ir Iv Jj Jn Jp Jq Jr Js Jt Lh Lj Lu Lv Lw Lx Lz Mb Md Mh Mi Mj Ml Mq Mr Mx Mz Na Nb Nc Ne Nf Nh No Nr Nt Nu Nv Nx Ny Oi Pa Pe Po Qa Qb Qe) Lx(Fp Hq Hv Hw Hx Ii Ij Ik Il In Io Ip Iq Ir Iu Jg Jj Jn Jo Jp Jq Jr Js Li Lj Lu Lw Ly Mb Mc Mm Mn Mv My Nc Nd Ne Ng Nj Nk Nm Nr Ns Nu Nx Ny Oe Og Oi Oy Pb Pc Pe Pz Qa Qb) Jq(aA Fp Hv Hw Hx Ih Ii Il Im Ip Iq Ir Iu Iv Jg Jj Jk Jr Lh Li Lu Lv Lw Lz Mb Mh Mi Mj Mk Mm Mn Mr Mv Mx Nb Nc Nd Nf Nk Nl Nm No Nq Nr Nt Nu Nv Nx Ny Pa Pd Pe Po Qa Qb) Jj(aA Hq Hw Hx Ih Ii Il Im Ip Iq Ir Iu Iv Jg Jk Jm Jn Jo Jr Js Lh Li Lu Lz Md Mh Mi Mm Mn Mr Mv Mz Nc Nd Nf Nl Nm No Nq Nr Nt Nv Nx Ny Of Pa Pe Pg Po Qa Qb Qe) Jr(aA Hr Ii Ik Im In Io Ip Iv Jg Jk Jp Lh Li Lv Lw Mb Me Mg Mh Mi Mj Ml Mm Mn Mr Mv Mz Na Nc Nd Nh Nj Nm No Nq Nr Ns Nv Nx Ny Og Oi Pb Pe Pg Po Pz Qa Qb Qc) No(Fp Hr Ik Il Ip Jg Lh Li Lj Ly Mb Me Mj Mk Mm Mn Ms Nc Nd Nj Nm Nu Nx Ny Og Oi Oy Pb Qb) Po(Hr Ik Il In Ip Jg Jm Jn Js Ly Me Mm Nd Nj Nx Og Oi Oy Pb) Jg(aA Ik Io Ip Lu Md Mg Mz Ny Og Oi Pa Pz Qa Qb) Mm(aA Ir Iv Jn Lh Mh Mr Mz Nb Nx Ny Pa Pe Qa) aA(Hr Ip Li Lw Me Mh Mn Nc Nd Nj Nm Nx Pg) Ny(Im Io Ip Mb Mg Mh Nd Nj Og Oi Pb) Nd(Jn Lv Lw Md Nh Nt) Im(Lh Nj Nv Nx Pg) Pb(Ii Ir Lh Nr Pe) Oi(Li Nv Pe Qa) Nq(Jn Js Ng) Lw(Hv Iq Jn) Mz(Mb Me Nj) Jp(Ip Mh Nj) Ik(Nt Qa) In(Lh Mr) NmMg MbPe NjPa JoLh Unconstrained panels with 2 analytes, where 1.0E-5 >= 'AUC p-value' > 1.0E-6. Contains 411 panels of 7,260 total panels evaluated. : Jg(Fp Hq Hv Hw Hx Ih Ii Il Im In Iq Ir Iv Jn Jp Js Lh Lv Lw Lz Ma Mf Mh Mi Mj Mm Mn Mr Ms Mx My Nb Nc Nd Ne Nf Nh Ni Nl Nm Nr Ns Nt Nv Nx Oy Pc Pd Pe Pg Qd Qe) Jr(Fp Hu Hv Hw Hx Ih Ij Il Iq Ir It Iu Jm Jn Js Jt Lj Lu Lz Mc Md Mf Mk Mq Ms Mx My Nb Ne Nf Ng Ni Nk Nl Nu Oe Of Oy Oz Pc Qd Qe) No(Hq Hu Hw Ii Ij Im Iu Jn Jp Js Lu Lw Lx Lz Mc Mg Mh Mv My Ne Ng Nh Nl Nq Nr Ns Oe Oz Pa Pe Pg Qa Qc Qd Qe) Lx(aA Hu Ih Im It Iv Jt Lv Lz Md Me Mf Mh Mi Mj Mk Ml Mq Ms Mx Na Nf Nh Nl Nq Nv Oz Pd Po Qc Qe) Mm(Fp Fr Hv Hw Hx Ih Ii In Ip Js Jt Lv Lw Md Mi Mj Na Nc Nf Nr Nt Nv Oi Pg Qd Qe) Ma(Hq Hu Il It Iu Jk Jo Li Me Mk Mn Mv Nd Nj Nl Nm Nq Ns Og Oz Pg Pz Qc Qd) Po(Hq Hw Hx Ii Ij Im Io Jp Lw Mb Ml Mn Mu My Nm Nr Ns Pd Pe Qa Qb) Fr(Hr Hx Ih Iu Jk Jm Jp Jt Lu Lv Lz Mc Ml Mn Ms Nb Ni

Figure 43 Continued

Nl Nt Qd Qe) Ny(aA Fp Hr Ik In Jp Li Lj Lw Me Mn Na Nc Ng Nm Oy Pz Qa) Jj(Fp Hu Ij It Jp Lv Mj Mk Mx My Nb Ne Nh Nk Pd Qd) Mu(Hu Hx Iv Jk Lv Me Mz Ni Nq Nt Nu Of Oz Qc Qd) Qa(aA Im In Io Ip Jp Lw Nc Nd Nj Nm Og Pb) Jn(aA Hr Ik Jk Jp Me Mn Na Nj Nm Oi Pb) Jq(Hq Jm Jp Js Ly Me Ms My Mz Pg Qd Qe) Ip(Im Ir Iv Lh Li Mn Mr Mz Nc Nv Pe) aA(Ik Jk Lj Lv Mb Nv Og Oz Pb Qb) Pe(Hr Im In Io Jp Lw Ly Mj Of) Jp(Ii Lh Nq Nt Nx Oi Qb) Mz(Hr Mn Nc Nd Nx) Ii(Ik In Mg Na Og) Im(Lw Mh Nc Nl Pa) Ir(Hr Lw Mb Nj Oi) Nq(Ij Jm Ly Nr) Nv(Ik Io Mg Og) Lh(Ik Na Oi) Lw(Mr Mx) MbMd MrPb JkOi

Unconstrained panels with 2 analytes, where 1.0E-4 >= 'AUC p-value' > 1.0E-5. Contains 666 panels of 7,260 total panels evaluated. : Qa(Fp Hr Hu Hv Hw Hx Ih Ii Ij Il Iq Ir It Iu Iv Jk Jm Jn Js Jt Lh Li Lj Lu Lv Lz Mb Mc Md Me Mf Mg Mh Mi Mj Mk Ml Mn Mq Mr Ms Mv Mx My Mz Na Nb Ne Nf Ng Nh Ni Nk Nl Nq Nr Ns Nt Nu Nv Nx Oe Of Oz Pa Pc Pe Pz Qb Qc Qd Qe) Ny(Hq Hu Hv Hw Hx Ih Ii Ij Il Iq Ir Iv Jk Jm Jn Js Lh Lu Lv Ly Lz Mc Md Mf Mi Mj Mk Ml Mq Mr Ms Mx My Mz Nb Ne Nf Nh Nk Nl Nq Ns Nt Nu Nv Nx Oe Of Oz Pa Pc Pe Pg Qb Qc Qe) Jp(aA Fp Hq Hv Hw Ik Im In Io Iq Ir Iv Jk Js Li Lv Lw Md Mi Mj Mm Mn Mr Ms Mz Nb Nc Nd Ne Nf Nh Nk Nm Nr Ns Nv Og Pa Pb Pc Pg Pz) Im(Fp Hq Hx Ih Ii Ik Io Iq Ir Iv Jk Jn Js Jt Lj Lv Lz Md Mg Mi Mj Mm Mn Mr Mv Mx Mz Nb Nd Ne Nh Nk Nm Nr Nt Pd Qb Qe) Po(aA Fp Hu Hv Iq It Iu Lh Lj Lu Lz Mc Md Mh Mi Mj Mk Mq Mr Mv Mx Mz Na Nc Nf Ng No Nq Nt Nu Nv Of Oz Pa Pc Pz Qc) No(Hv Hx Ih In Io Iq Ir It Iv Jk Jo Jt Lv Md Mf Mi Mq Mr Mx Mz Na Nb Nf Nt Nv Of Pc Pd Pz) Mm(Hq Hr Hu Ij Ik Io Iq It Jk Jo Li Lj Lu Ma Me Ml Mn Mq Mx Nd Ne Nh Ni Nl Nm Nu Og Pd Qb) Jg(Hr Hu Ij It Iu Jk Jm Jo Jt Li Lj Ly Mb Mc Me Mk Ml Mq Mv Na Nj Nk Nq Nu Oe Of Oz Pb Qc) Jn(Fp Hw In Io Iq Ir Iv Jq Lv Lz Mb Mh Mi Mv Mx Mz Nc Ne Nl Nr Nx Og Pe Pz Qc) Ip(Fp Hx Ih Iq Jk Jt Lz Mh Mi Mx Na Nb Nd Nh Nl Nm Nt Nx Pa Pg Qb Qd Qe) Pe(Hu Hx Ik Il Jm Jo Me Ml Mn Mq Mx Na Nd Nj Nm Nq Ns Og Oz Pz Qb Qc) Nm(Fp Ik Io Iq Ir Iv Lh Mh Mi Mr Mz Nb Nc Nd Ng Nv Og Oi Pa Qb) aA(Fp Hq Ih Io Iq Lh Mf Mk Mv Ne Nh Nk Nl Ns Nu Oe Of Oi Pa Pc) Ma(Fr Jm Ly Mc Mf Mg Ms My Ng Ni Nk Oe Of Oy Pb Pc Pd) Jq(Hr Ij Ik Io Jo Jt Lj Mc Ml Mq Na Ne Ng Nh Nj Ns Of) Nv(Fp Li Lj Lw Mb Mh Mx Na Nc Nd Ng Nj Pb Pz Qb) Nq(Hu Hv Hw Io Iq Ir Lw Mf Mi My Nj Ns Oy) Lx(Hr Jk Jm Lh Mg Mr Mz Nb Ni Nt Pa Pg Qd) Jj(Hr Hv In Jt Lj Lw Ly Mb Mg Ng Nj Nu Og) Nx(Fp Io Iq Ir Mn Mr Mx Na Ng Og Pb Qb) Lw(Fp Js Lh Li Lz Mh Mi Mn Mz Qb Qe) Nd(Fp Hv Ir Iv Mi Ne Nl Nu Pg Qd Qe) Mn(Ih Io Ir Iv Lh Mr Nb Nh Oi) Og(Ir Iv Jk Lh Mr Mz Nb Nr Nt) Pg(Fp Ik Io Mb Mg Na Nc Pb) Mz(Fp Ik Li Lj Mg Oi Qb) Lh(Hr Il Io Ly Mg Mj Qb) Mu(Hq Hr Jt Ms Nb Pd) Nc(Hv Ii Mx Na Nb Pa) Li(Ik Io Md Mg Ng Pz) Oi(Ih Iq Lj Pa Qb Qe) Nj(Hx Mr Mx Qd Qe) Pb(Iq Iv Nb Nt Pa) Ik(Ir Jk Pa Qe) Jr(Hq Jo Ly Pd) Ii(Mx Oy Qb) Ir(In Io Mh) Fr(Mk Pd) Nt(Ly Mg) Mb(Pa Qd) Na(Ih Js) Jk(Fp Mg) LvQb MhQd MrJo InJs Unconstrained panels with 2 analytes, where 1.0E-3 >= 'AUC p-value' > 1.0E-4. Contains 1,025 panels of 7,260 total panels evaluated. : Pg(Hq Hu Hv Hw Hx Ih Ii Ij Il In Iq Ir It Iv Jm Jn Js Lh Li Lj Lu Lw Ly Lz Mc Md Me Mf Mh Mi Mj Mk Mn Mq Mr Ms Mx My Mz Nb Ne Nf Ng Nh Nj Nk Nl Nm Nr Ns Nu Nv Nx Oe Of Og Oi Oy Oz Pa Pc Pd Pe Pz Qa Qb Qc Qe) Nv(Hq Hr Hu Hv Hw Hx Ih Ii Ij Il In Iq Ir It Iu Iv Jk Jm Jn Jo Js Jt Lh Lu Lv Ly Lz Mc Md Me Mf Mi Mj Mk Mn Mq Mr Ms Mv My Mz Nb Ne Nf Nh Ni Nk Nl Nq Nr Ns Nt Nu Nx Oe Of Oy Oz Pa Pc Pe Qc Qd Qe) Ir(aA Hu Hv Hw Ii Ij Il It Iu Jk Jm Js Jt Lv Ly Lz Mc Md Mf Mg Mi Mj Mk Ml Mq Mr Ms Mv Mx My Mz Na Nb Nc Ne Nf Ng Nh Ni Nk Nl Nr Ns Nu Oe Of Oy Oz Pc Pd Pe Po Pz Qb Qc Qe) Qb(Fp Hv Hw Hx Ih Ij Ik In Io Iq Iu Iv Jk Jm Jn Js Jt Li Lu Lz Mb Md Mh Mi Mj Mk Mn Mr Ms Mx Na Nb Nc Nd Ne Nf Nh Nj Nl Nq Nr Nt Nu Og Pa Pb Qd) aA(Hu Hv Hw Hx Ii Ij Il Im In It Iu Iv Jm Jo Js Jt Lu Ly Lz Mc Md Mg Mi Mj Ml Mq Mr Ms Mx My Mz Na Nb Nf Ng Ni No Nq Nr Nt Oy Pd Pe Pz Qc Qd Qe) Mn(Fp Hv Hw Hx Ii Ij Ik In Iq It Jk Js Jt Li Lu Lv Lz Md Mg Mh Mi Mj Mx Na Nc Nd Ne Nf Ng Nj Nl Nm Nq Nr Ns Nu Oe Of Pc Pz Qd Qe) Im(Hr Hu Hv Hw Ij Il In It Iu Jm Li Lu Ly Mb Mc Me Mf Mk Ml Mq Ms My Na Nf Ng Ni Nq Ns Nu Oe Of Og Oi Oy Oz Pb Pc Pz Qc Qd) Pe(Fp Hq Hv Hw Ii Ij Iq It Iu Jk Js Jt Lh Li Lj Lu Lv Lz Mc Md Mf Mg Mh Mi Mk Mr Mv Mz Nb Nc Ng Ni Nk Nr Nt Nu Nx Oy Pd Qe) Jn(Hu Hv Ii Ij Il Ip It Jm Js Jt Lj Lu Ly Mc Md Mf Mg Mj Mk Ml Mq Mr Ms My Nf Ng Nh Ni Nk Ns Nu Oe Of Oy Oz Pa Pc Pd) Jp(Hr Hu Hx Ih Ij Il It Iu Jm Jo Jt Lj Lu Ly Lz Mb Mc Me Mf Mg Mk Mq Mv Mx My Na Ng Ni Nl Nu Oe Of Oy Oz Pd Qc Qd Qe) Lh(Fp Hq Hu Hv Hx Iu Jk Li Lj Lv Mb Md Me Mk Mq Mr Mx My Mz Nc Nd Ng Nh Ni Nj Nk Nl Nq Ns Nt Nx Oe Of Oy Pa Pc Pz Qe) Jk(Hv Ih Io Iq Iv Js Li Lj Lw Mb Md Mh Mi Mr Ms Mx Mz Na Nb Nc Nd Ne Nf Ng Nh Nj Nl Nm Ns Nx Oy Pa Pb Po Pz Qe) Nq(Fp Ih Ii In Ip It Iv Lj Lz Mc Md Me Mg Mh Mj Mm Mq Mr Mx Mz Na Nb Nc Nf Nh Nl Nm Nx Of Oi Oz Pa Pz Qd Qe) Nm(Hq Hv Hw Hx Ih Ii Iu Js Li Lj Lu Lw Lz Md Mj Ms Mx Na Ne Nf Nh Nj Nk Nl Nr Ns Nt Nx Pb Pz Qd Qe) Mz(Hv Hx Ii Ij In Io Js Lz Mc Md Mf Mh Mi Mk Ml Mx My Na Nf Ng Ni Nk Nr Ns Oe Of Oy Pb Pc Pz Qc Qe) Nx(Hq Hv Hx Ih Ik Iv Js Li Lj Lw Ly Lz Md Mi Ms Nb Nc Nd Nf Nh Ni Nk Nl Ns Nt Oy Pa Pc Pz Qd Qe) Ip(Hq Hr Hv Hw Ii Ik Iu Js Lj Lu Lv Lw Mb Md Mj Mk Mq Mv My Ne Nf Nj Nk Nr Nu Og Oi Oz Pd) Mm(Il Iu Jm Ly Lz Mb Mc Mf Mg Mk Ms Mv My Ng Nj Nk Ns Oe Of Oy Oz Pb Pc Pz Qc) Nd(Hw Hx Ih Ii Ij In Iq It Js Jt Li Lj Mf Mh Mj Mq Mr Mx Na Nb Nc Nf Nr Pa) Nc(Fp Hq Hv Ij Iq It Iv Js Li Lv Lw Mb Md Mh Mi Mj Mr Ni Nr Nt Qd Qe) Li(Fp Ih Lu Lv Mb Mh Mx Na Ne Nh Ni Nj Nl Nt Og Pa Pb Pc Po Qd Qe) Pa(Fp Hu Il Io Jr Lw Ly Mg Mh Na Ne Ng Nh Nl Og Oy Oz Pc Qe) Jj(Ik Io Mc Me Mf Ml Mq Ms Na Ni Ns Oe Oy Oz Pb Pc Pz Qc) Po(Ih Iv Jo Jt Lv Mf Mg Nb Ne Nh Ni Nk Nl Ny Qd Qe) Fp(Ih Ii Ik Lv Mb Md Mh Nh Nj Nl Nt Oi Qd) Ii(Hu Hv Iq Jm Lj Me Ng Nj Nk Oe Of Oi) Qe(Io Lv Mb Mg Mh Mx Na Nh Og Pb Pz) Jq(Hu It Ni Oe Og Oi Oy Oz Pb Pz Qc) Nr(Hr Ik Io Lw Mg Mx Na Nj Ny Oy) Mr(Hr Io Lv Mb Mf Mg Mj Mk Ng Oi) Lw(Hu Hw Hx Iv Lu Mj Mv Nl Qd) Mb(Ih Iq Js Lz Mh Mi Nh Nl) Nj(Hq Ih Iq Js Mi Mj Nb Nt) Ny(It Iu Jo Jt Mv Ni Pd Qd) Og(Hw Hx Ih Iq Jt Ml Mj Mv) Mh(Hx Iq Iv Md Nh Nt) Mx(Hq Ih Ij Js Lv Nl) Nb(Hr Ik In Io Me Nk) Pb(Hx Ih Js Jt Mi Mj) Qa(Hq Jo Ly Oy Pd) No(Jm Ml Ni Nk) Nt(In Lj Ng Oi) Js(Hr Me Nl Oi) Hv(Lv Md Me) Ik(Hx Ih Qd) Iq(Io Lv Mg) Mi(Io Ov) Ng(Iv Jg) In(Hw Iv) MdLj NaHq QdOi Unconstrained panels with 2 analytes, where 1.0E-2 >= 'AUC p-value' > 1.0E-3. Contains 1,190 panels of 7,260 total panels evaluated. : Qd(Hq Hv Hw Hx Ih Ii Ij Il In Io Ir It Iu Iv Jk Jm Jn Js Jt Lh Li Lj Lv Lz Mc Md Me Mg Mi Mk Ml Mq Mr Ms Mv Mx My Mz Na Nb Ne Nf Ng Nh Nk Nl Nr Ns Nt Nu Oe Of Og Oy Oz Pa Pb Pc Pe Pg Pz Qc Qe) Nt(Hq Hr Hu Hv Hw Hx Ih Ii Ij Il Io Iq Ir It Iu Iv Jk Jm Jn Jr Js Jt Lw Lz Mb Mc Md Me Mf Mi Mj Mk Ml Mr Ms Mv Mx My Mz Na Nb Ne Nf Nh Nl Nq Nr Ns Oe Of Oy Oz Pa Pc Pg Pz Qc Qe) Fp(Hq Hr Hu Hv Hw Hx Ij Il In Io Iq Ir It Iu Iv Jm Js Jt Lj Lu Ly Lz Mc Me Mf Mg Mi Mj Mk Ml Mq Mr Ms Mv Mx My Na Nb Ne Nf Ng Ni Nk Nr Ns Nu Oe Of Og Oy Oz Pb Pc Pd Pz Qc Qe) Qe(Hq Hr Hu Hv Hw Hx Ih Ii Ij Il In Iq It Iu Iv Jm Jn Js Jt Lj Lu Ly Lz Mc Md Me Mf Mi Mj Mk Ml Mq Mr Ms Mv My Nb Ne Nf Ng Ni Nk Nl Nr Ns Nu Oe Of Oy Oz Pc Pd Qb Qc) Hx(Hq Hr Hu Hv Ih Ii Il Io Iq Ir Iv Jk Jm Jn Js Li Lj Lv Ly Mb Mc Md Me Mf Mg Mi Mr Ms Mv Mx My Na Nb Ne Ng Nh Ni Nk Nl Nq Ns Oe Of Oi Oy Pa Pc Pz) Js(Hv Hw Ih Ii Ij Ik Io Iq It Iv Jm Jt Lh Li Lj Lv Ly Lz Mc Md Mg Mh Mi Mj Mk Ml Mq Mr Ms Mv My Ne Nf Ng Nh Ni Nk Nr Ns Nu Oe Of Og Pa Pc Pz Qc) Li(Hq Hr Hu Hv Hw Ii Ij Il In Iq Ir It Iu Iv Jm Jn Jo Jt Lj Ly Lz Mc Me Mf Mi Mj Mk Ml Mq Mr Ms Mv My Nb Nf Nk Nq Nr Ns Nu Oe Of Oy Oz Pd Qc) Pa(Hq Hr Hv Hw Ih Ii Ij In Iq Ir It Iu Iv Jm Jo Jt Lj Lu Lv Lz Mc Md Me Mf Mi Mj Ml Mq Mr Ms Mv Mx My Mz Nb Ni Nk Nr Ns Nu Oe Of Pd Pc Pz Qc) Nc(Hr Hu Hw Ih Ik Il In Io Iu Jm Jt Lj Lu Lv Lz Mc Me Mf Mg Mk Ml Mq Ms Mv Ne Nf Nh Nk Nl Ns Nu Of Og Oi Oy Pb Pd Qc) Ii(Hq Hw Ih Ij Il Io It Iu Iv Jk Jt Lh Lw Ly Lz Mb Mc Md Mf Mi Mj Mk Ml Mq Mr Mv My Nb Nf Nh Nl Nr Ns Nu Nx Oz Pc Qc) Jk(Hq Hr Hu Hw Ij Il In It Iu Jm Jo Jt Lu Lv Ly Lz Mc Me Mf Mj Mk Ml Mq Mv My Ni Nk Nq Nr Nu Oe Of Oz Pc Pd Pg Qc) Mh(Hq Hr Hu Hv Ih Ij Ik Io It Jt Lh Lj Lu Lv Mi Mj

Figure 43 Continued

Mq Ms Mx Na Ne Nf Ng Ni Nj Nk Nl Nr Nu Nx Og Oi Oz Pb Pc Pd) Ih(Hv Hw Ij In Io Ir It Iv Jm Jn Lh Lj Lv Lw Mc Md Mf Mi Mj Mk Mq Mr Mz Ne Nh Nk Nl Nr Ns Nu Oe Pc Pe Pz) Nx(Hr Hu Hw Ij Il In It Iu Jm Jt Lu Lv Mb Mc Me Mf Mg Mj Mk Ml Mq Mv My Ne Nj Nr Nu Oe Of Oi Oz Pd Qc) Nl(Hq Hr Hv Hw Ij Ik In Iq It Iv Jt Lj Lv Md Mi Mj Mk Ml Mr Mv My Mz Na Nb Nf Nr Ns Of Og Oi Pd Pe) Mn(Hq Hr Hu Il Iu Jm Jo Lj Ly Mb Mc Me Mf Mk Ml Mq Ms Mv My Ni Nk Nu Oe Of Oy Oz Pb Pd Qc) Iv(Hr Ik Io Ir Jm Jt Lh Lj Lv Mb Md Me Mf Mg Mv Mx Mz Na Nb Nh Nj Nk Ns Oe Oi Oz Pc Pe Pz) Nm(Hr Hu Ij Il In It Jm Jt Lv Ly Mb Mc Me Mf Mk Ml Mq Mv My Ni Nu Oe Of Oy Oz Pc Pd Qc) Mr(Hv Ij Ik Il Iu Lj Ly Lz Mc Md Me Mi Ml Mv Mx My Mz Na Nh Nk Nr Ns Nu Oe Of Oy Pc Pz) Qb(Hq Hr Hu Il It Jo Lj Ly Mc Me Mf Mg Ml Mq Mv My Ng Ni Nk Ns Oe Of Oy Oz Pc Pd Pz Qc) Ip(Hu Ij Il In Io It Jm Jo Ly Mc Me Mf Mg Ml Ms Ng Ni Ns Oe Of Oy Pb Pc Pz Qc) Lj(Hq Hw Ik Il In Io Ir Iu Lu Lv Lw Lz Mb Mi Mj Mx Na Nb Ne Nf Nh Nj Nr Og Pc) Lh(Hw Ij Iq Ir It Jm Jn Jt Lu Lz Mc Mf Mi Ml Ms Mv Nb Ne Nf Nr Nu Oz Pd Qc) Nr(Hv Ij Iq Lv Lz Mc Md Me Mi Mj Ml Mq Mv Ng Nh Nk Ns Nu Oe Oi Oz Pz) Mx(Ik Il Io Iq It Jt Mb Md Me Mv Nb Ne Ng Nh Nk Oe Og Oi Pb Pd Qc) Nd(Hq Hr Hu Jm Lu Lz Mc Me Mk Ml Mv Ng Ni Nj Nk Nq Ns Og Oi Pd) Nh(Hq Hv Hw Ik Iq Jt Lv Lw Lz Mi Mj Mv Mz Na Nb Nj Oi Pd Pe) Ij(Hv Hw Ik In Io Iq Lv Lw Lz Md Mi Mj Mv Na Ne Nf Og Oi Pb) Nq(Hr Ik Il Iu Jt Lu Lv Mb Mk Ml Mv Ne Nu Og Pc Pg Qc) Lw(Hq Hr Il Iu Mb Md Mk My Na Nb Ne Nf Nk Nu Og Pd) Mz(Hq Hw Il Iq It Iu Jm Jt Lv Mj Mq Ms Nb Ne Nu Oz) Mv(Ik Io Iq Mb Md Mg Na Ne Ng Nj Oi Oy Pb Pc Pg) Mi(Ik Iq Lv Ly Md Me Mg Mk Ml Ng Nk Oy Pc Pz) Hq(Ik Io Ir Jn Ne Ng Nk Oe Og Oi Pb Pd) Hv(Hr Hu In Io Mb Nb Nj Nk Ns Oe Pb Pc) Iq(Ik Ir It Lz Mc Md Mj Na Ng Ns Pc) Nb(Hu Jn Mb Mg Na Ne Ns Oe Of Oi) Md(Jq Lv Lz Me My Na Nj Nk Nu) Lv(Lz Mb Mg Ne Nf Ng Pg) Nj(Jt Lu Lz Ne Nf Nu Pd) Og(Hr Il Iu Mq Na Nu Pd) Jt(Ik In Io Nk Oi Pg) Na(Hu It Ne Nk Pd) Pe(My Ne Nf Oe Pc) Pg(Hr Iu Jo Ml Ni) Jq(In Mf Mg Pc) Oi(Jj Lz Ne Nu) Pb(Hr Hw Mq Nu) Mb(Lu Ne Nf) Ir(Jo Lu Me) Pd(Ik Nk Nv) Po(Ms Oe) Mg(Hw Nu) Ml(Jp Nv) Jo(Im Jn) LxOf MjIo NeIk

Unconstrained panels with 2 analytes, where 5.0E-2 >= 'AUC p-value' > 1.0E-2. Contains 815 panels of 7,260 total panels evaluated. : Pd(Hr Hu Hv Hw Hx Ih Ii Ij Il In Io Iq It Iu Iv Jm Js Jt Lj Lu Lv Ly Lz Mb Mc Md Me Mf Mg Mi Mj Mk Ml Mq Mr Ms Mv My Mz Nb Ne Nf Ng Ni Nq Nr Ns Nt Nu Oe Of Oi Oy Oz Pb Pz Qc Qd) Hq(Hr Hu Hv Hw Ih Ij Il In Iq It Iu Iv Jm Js Jt Lu Lv Ly Lz Mb Mc Md Me Mf Mg Mi Mj Mk Ml Mq Mr Ms Mv My Nb Nf Ni Nq Nr Ns Nu Of Oy Oz Pc Pz Qc) Ne(Hr Hu Hv Hw Ii In Io Iq It Iv Jm Jt Lu Ly Lz Mc Md Mf Mg Mi Mj Mk Ml Mq Mr Ms My Nf Ng Nk Nl Nr Ns Nu Of Og Oy Pb Pc Qc) Jt(Hr Hu Hv Hw Hx Ih Ij Iq It Iu Jm Lj Lu Lv Lw Lz Mb Mc Md Me Mg Mi Mj Mk Mq Mr Ms Mv Na Nb Nf Ng Ni Nr Ns Oe Of Oy Pz) Nh(Hu Ij Il In Io It Iu Jm Jo Lu Ly Mc Md Mf Mg Mk Ml Mq Ms My Nf Ng Nk Nl Ns Nu Oe Of Og Oy Oz Pb Pc Pz Qc) Nb(Hw Ih Ij Il Iq It Jm Js Lv Ly Lz Mc Md Mf Mh Mi Mj Mk Ml Mq Mr Ms Mv My Nf Ni Nr Nu Oy Oz Pc Pz Qc) Lj(Hr Hu Hv Ij Iq It Jm Jo Ly Mc Me Mf Mg Mk Ml Mq Ms Mv My Ng Ni Nk Ns Nu Oe Of Oy Oz Pb Pz Qc) Mv(Hr Hv Ih Il It Iu Jm Lu Lv Ly Lz Mc Me Mf Mh Mi Mj Ml Mq Ms Mz Nf Ni Nk Ns Nu Of Oz Pz) Lv(Hr Hu Hw Ii Io Lu Lw Mc Me Mf Mj Mk Ml Ms My Na Nj Nk Ns Nt Nu Og Oi Pb Pc Pz Qc) Nl(Hu Il Io Iu Jm Jo Lu Ly Lz Mc Me Mf Mg Mq Ms Ng Ni Nj Nk Nu Oe Oy Oz Pb Pc Pz Qc) Mb(Hu Hw Ij Il In Io It Iu Mg Mj Mk Ml Ms My Nd Nj Nk Nr Ns Nu Of Og Oi Pb Qc) Mx(Hv Iu Lu Ly Lz Mc Mf Mg Mi Mj Mk Ml Mq Ms My Na Nf Ni Ns Nu Of Oy Oz Pc Pz) Iq(Hu Hv Ih Il In Iu Iv Jm Lu Mf Mk Ml Mq Mr Ms My Nf Ni Nk Nu Oe Oy Oz Pz Qc) Md(Hu Hw Ik Il Io It Jm Jo Lu Ly Mc Mf Mj Mk Ml Mq Ns Of Og Oi Oz Pb Pz Qc) Iv(Hu Hv Hw Ij It Iu Jo Lz Mc Mi Mj Mk Ml Mq Mr Ms My Nf Ni Nr Nu Of Oy Qc) Mh(Hw Il In Iu Jm Ly Lz Mc Me Mf Mg Mk Ml Mr My Ns Oe Of Oy Pz Qc) Hv(Ik Il It Iu Jm Lu Ly Lz Mc Mi Mj Mk Mq Ms My Ng Ni Ng Ni Og Oi Oz) Ih(Hr Hu Il Iu Jo Lu Ly Lz Me Mg Ml Ms My Nf Ng Ni Of Oy Oz Qc) Ij(Hr Hu Hx Lu Mc Mg Mk Mq Ms My Ng Ni Nk Ns Nu Oe Oy Pc Pz) Na(Ik Il Jm Lu Lz Me Mi Mj Ms My Nf Ni Nj Oe Oy Pb Pc Qc) Nr(Hu Hw Hx In It Iu Jm Lu Ly Mf Mk Ms My Nf Ni Pc) Mi(Hu It Jm Lu Lz Mc Mf Mq Ms My Ni Ns Nu Oe Oz Qc) Nd(Ik Il Io Iu Jo Mg Ms My Oe Of Oy Oz Pb Pc Pz Qc) Hx(Hw In It Iu Lu Lz Mj Mk Ml Mq Nf Nu Oz Qc) Jo(Fp In Lw Mg Mz Nc Nm Nq Nt Nx Og Pb Qd Qe) Hu(Ik Js Lz Mj Mr My Mz Nj Ns Og Oi Pc Qd) Lu(Ii Ik Io Js Mr Mz Nt Og Oi Pc Qd) Nk(Hw Il In It Mj My Nf Nq Nt Nu Oi) Lz(Io It Ly Mq Ng Ni Og Pb Pc) Mr(Hw Il Jm Mq Ms Nf Ni Oz Qc) Nj(Hr Hw Il In It Iu My Nc Oy) Lw(In It Mf Ml Mq Of Oi Pb) Mj(Ik Jm Mg Ng Ns Oi Pc Pz) Iu(Ik Jm Jn Js Ly Mg Ng) My(Ik Mg Ng Ns Og Oi) Hr(Ii Ik Io Me Oi Qd) Il(Ik Js Ly Oe Oi Pb) Nu(Ik Io Ms Ng Nt) Nc(Ng Oe Oz Pc Pz) It(Ns Og Pb Pc Pz) Nq(Ms Ni Oe Pb) Nf(In Oe Og Pa) Hw(Ik Io Me Ng) Mk(Og Oi Pa) Ni(Li Nt Qd) Js(Mf Oy Oz) Ly(Mz Qd) Ms(Ii Pe) Og(In Oz) PoPg NtMq MfQd IiPz QcOi Constrained panels with 3 analytes, where 1.0E-8 >= 'AUC p-value' > 0. Contains 10,122 panels of 287,980 total panels evaluated. : Jj{Nd(aA Et Fp Fr Hq Hr Hu Hv Hw Hx Ih Ii Ij Il Im In Ip Iq Ir Is It Iu Iv Jg Jh Ji Jk Jl Jm Jn Jo Jp Jq Jr Js Jt Lh Li Lj Lv Lw Ma Mb Md Mi Mm Mn Mp Mq Mr Mt Mu Mv Mw Mx Mz Na Nb Nc Ne Nf Nh Nj Nl Nm Nn Nr Nt Nu Nv Nw Nx Ny Of Oh Ok Om On Pa Pd Pe Pf Pg Po Qa Qb Qe) Nc(Et Fp Fr Hq Hr Hu Hv Hw Hx Ij Im In Ip Iq Ir It Iu Iv Jg Jh Jm Jn Jo Jp Jq Jr Jt Li Lu Lv Lx Ma Mb Mh Mi Mm Mp Mr Mt Mu Mv Mw Mx My Mz Na Nb Nf Ni Nm Nn Nq Nr Nw Nx Ny Of Om Pa Pd Pe Pf Po Qa Qb Qd Qe) Lx(aA Et Fr Hq Hv Hw Hx Ih Ii Ip Ir Is It Iv Jg Jh Ji Jk Jl Jn Jo Jq Jr Js Jt Lh Lw Ly Mb Mh Ml Mm Mp Mt Mu Mv Mw My Mz Na Ng Nj Nm Nn Nr Nt Nv Nw Nx Ny Og Oh Ok Om On Oy Pb Pf Pg Qa) Hw(Et Fr Hq Ih Il Im Ip Iq Is Iv Jg Jh Ji Jm Jn Jp Jq Jr Js Li Lu Lw Ma Md Mm Mn Mp Mt Mu Mw Mz Nf Nj Nm Nn Nq Nv Nw Nx Ny Oh Om Pa Pb Pd Pf Pg Qa Qb) Im(Fr Hq Hr Hu Hv Ii Ij In Iq Ir Iu Iv Jg Jk Jo Jp Jq Js Jt Lu Lw Ma Mb Md Mh Mi Mj Mm Mn Mp Mv Mz Na Nb Nf Nl Nm Nq Nr Nv Nx Of Pd Pc Pg Po Qd) Ip(Hq Hr Hu Hv Hx Ih Ij Il In Iq Ir Iu Iv Jg Jn Jo Jq Jr Js Li Lu Lw Lz Md Mi Mm Mn Mr Mv Mz Na Nb Ne Nf Nk Nl Nq Nr Nt Nu Nx Of Pa Pd Pe Po) Of(aA Ih Ii Iq Ir It Iv Jm Jn Jp Jq Jr Js Li Lu Lw Lz Ma Md Mh Mi Mm Mn Mp Mr Mz Nf Nk Nl Nn Nq Nr Nw Nx Og Oh Oi Om Pb Pd Pf Po Qa Qb Qe) Pa(aA Et Hv Ih Ij Ik In Iq Ir Is It Iv Jg Jh Ji Jn Jo Jq Jr Js Jt Li Lv Lw Ma Md Mk Mm Mn Mp Mt Mu Mz Na Nf Nh Nj Nm Nn Nw Nx Oh Ok Pf Qa) Jg(aA Et Hq Hu Ih Il Io Iq Ir Is Iu Iv Jn Jo Jq Jr Js Lh Lu Md Mi Mp Mr Mx Mz Ne Nf Nh Nl No Nr Nt Nv Nw Og Oh Oi Pe Pf Pg Po Qa Qe) Mm(Fp Hq Hr Hu Hv Hx Ih Ij Il In Iq Ir It Iv Jn Jo Jq Jr Js Lu Md Mh Mi Mn Mr Mz Na Nb Ne Nf Nl Nr Nx Pd Pe Po Qa Qe) Mp(Et Hq Hr Hu Hv Ii Il In Iq Ir Iv Jn Jo Jq Jr Js Lh Lu Md Mr Mu Mz Na Nb Ne Nf Nl Nn Nr Nt Nw Ny Oi Pe Pf Pg Po Qa) Ma(Hr Hv Hx Ih Ij Il In Iq Ir It Iv Jn Jo Jq Jr Js Lu Lw Mb Md Mi Mn Mr Mz Na Nb Ne Nf Nk Nl Nn Nr Nx Pd Pe Qa Qb) Mr(aA Et Fr Hx Ih Ii Ik Is Jh Ji Jk Jl Jn Jq Jr Lh Lw Ml Mn Mt Mu Mw My Nm Nn Nv Nw Ny Og Oh Ok Om On Pb Pf) Nf(aA Et Fr Hq Ih Il Iq Ir Is Iu Iv Jm Jo Jp Li Lw Mn Mw Nj Nl Nm Nn Nq Nr Nt Nv Nw Oh Oz Pf Pg Qa Qb Qe) Iq(Hq Hu Hx Ih Ii Ij Il Iv Jh Jm Jo Jq Lj Lu Lw Lz Mb Md Mn Mu Mw Na Nb Nj Nm Nr Nt Nx Oi Pg Qa Qc Qd) Nq(Fp Hr Hu Hv Ih Ij In Ir It Iv Jm Jn Jo Jp Jr Js Lj Mb Mn Mz Na Ne Nh Nl Nr Pc Qa Qb Qe) Pe(aA Et Fr Ih Ik Is Jh Ji Jk Jq Jr Lw Mb Mj Ml Mn Mt Mu Mw Nm Nn Nv Nw Ny Oh Pb Pf Pg Qc) Nm(Fp Hq Hx Ih Il Ir Iv Jk Jn Jr Lu Md Mh Mn Mz Nb Ne Nk Nl Nr Nw Oh Pf Po Qa Qb) Nt(Et Fr Ii Is Jh Ji Jk Jl Jn Jq Jr Js Lh Mn Mt Mu Mw Mz Nj Nn Nw Ny Ok Om On Pf) Mu(Et Fr Ii Il Ir Is Iv Ji Jl Jn Jq Jr Lh Mw Nj No Nr Og Ok Om Pf Pg Po Qb) Jm(Hr Hu Hv Ij In Ir Iv Jn Jo Jp Jr Js Jt Lu Mb Md Mv Mz Na Nb Ne Nl Nr Qa) Nn(aA Hu Ii Il Ir Is Iv Ji Jo Jq Jr Lh Mz Ne No Ny Oh Oi Ok Om Pc Pg Po) Mn(Hq Hv Hx Il In Ir Iu Iv Jo Jq Li Lu Md Mi Mv Mz Nb Ne Nh Nl Nr Nx Pd) Oh(Hq Hr Hu Hv Ij Il In Ir Iv Jn Jo Jq Lu Mz Na Nb Nr Nx Oi Pc Po Qa) Iu(Fp Hr Hu Hv Ij In It Jn Jp Jq Jr Js Lj Lv Lw Md Mv Mx Mz Na Qb) Po(aA Et Hx Ik Is Jh Jq Jr Lw Md Mh Ml Mt Mv My Nl Ny Og Oy Pb) Fr(aA Hv Ir Is It Iv Jh Ji Jn Jo Jq Jr Lh Mz Na Ne Nr Ok Om) Et(Hq Il Io Ir Iv Jk Jn Jo Lu Md Mz Ne Nj Nl Nr Ny Pf Pg) Nr(Ih Jn Jp Jq Jr Js Li Mb Md Mt Mz Nl Nw Nx Pb Qa Qb) Lu(Ih Is It Jh Ji Jn Jp Jq Jr Li Lw Mv Mw Nh Qa Qb Qe) Hq(aA Hv Ih Il Ir Is Iv Jn Jo Jq Jr Js Mb Mz Na

Figure 43 Continued

Pb Qa) Jh(Ir Is Ji Jl Jr Lh Lz Mh Ne Nk Nl No Og Ok Pf Pg) Md(Fp Ih Il Ir Iv Jo Jp Li Mi Mv Nb Oz Qa Qb Qe) Mw(aA Ir Is Ji Jl Jn Jq Jr Lh
Mz Ne Nl No Og Ok) Nw(Hr Hv Il In Ir Iv Jn Jo Jq Jr Mb Mz Na Nu) Nb(Hx Ih Ik Jn Li Ml My Nj Nl Og Pb Qa Qb) Om(Is Ji Jl Lh Ml My Ne
Nl No Og Ok Pb) Pf(Ih Ii Ik Ir Iv Jo Jq Lz Mb Mz Na Nx) Lw(Hu Hx Il Jn Js Li Lz Mh Mi Mx Qb) Nl(Fp Hv In Jp Mb Mi Mv Mx Qb Qe) Ii(aA
Hx Ik Is Jr Ml Mt My Oy Pb) Iv(Ih Ik Li Me Mt Mz Nv Nx Qa Qb) Jk(aA Is Ji Jn Jq Jr Lh Og Oi Ok) Jo(Ih Jn Jp Jq Jr Mt Mz Pb Qa Qb) Il(aA
Jn Jp Jq Jr Li Mz Og Qa) Lh(Is Ji Jl Jq Jr Mt Ok Pb) Lz(Hu Hv Ik In It Mb Na) Mb(Hu Li Mh Mt Ne Qb) Ih(Hv In Li Mi Mj Mv) Io(Is Ji Jl Nv
On) Pg(aA Ir Jn Jr Mz) Mh(Hu In Jp Nh) Jq(Is Jr Li Mt) Oi(Jl Mt Ok On) No(Ji Mj Nj) Ir(Ik Mt Nv) Qb(Hv In Js) Mi(Hu Nj) Hx(Li Pb) Jl(aA
Ji) Nx(Jp Li) Ny(Og Pb) NsPd MeaA MlMz MyHu PzOn JnNv} Ik{Jh(aA Et Fp Fr Hv Hw Hx Ih Ii Il Im Ip Iq Ir Is Iu Iv Ji Jn Jo Jq Jr Js Lh Li
Lj Lu Lx Lz Mg Mh Mi Mj Mk Mp Mr Mt Mu Mw Mx Mz Na Nb Nc Nd Ne Nf Ng Nk Nl Nn No Nr Nt Nu Nv Nw Ny Og Oh Ok Om On Oz
Pa Pe Pf Pg Po Qa Qb Qd Qe) Mu(aA Et Fp Fr Hr Hv Hw Ih Ii Ij Im Iq Ir Is It Iv Jg Ji Jl Jn Jo Jq Jr Js Lh Li Lj Lx Lz Md Mh Mi Mj Mk Ml Mp
Mr Mt Mw Mz Na Nb Nc Nf Nj Nm Nn No Nr Nt Nv Nw Nx Ny Og Oh Ok Om On Oz Pa Pe Pf Pg Po Qa Qb Qd Qe) Lx(Et Fp Fr Hq Hu Hv
Hw Hx Im Iq Ir Is Iv Jg Jn Jo Jr Js Jt Lh Li Lj Lw Lz Mb Mh Mj Mk Mm Mp Mr Mv Mw My Na Nb Nc Ne Ng Nh Nj Nl Nm Nn Nr Nt Nw Ny
Og Oh Ok Om Oy Oz Pa Pb Pe Pf Pg Qa Qd) Mw(aA Et Fp Fr Hu Hv Hw Ii Im Ip Iq Ir Is Iv Ji Jn Jo Jq Jr Js Lh Li Lj Lz Mg Mh Mi Mj Mk Mr
Mt Mx My Mz Na Nb Nc Ne Nf Ng Nh Nl No Nr Nt Nw Ny Og Oh Ok Om On Oy Oz Pa Pe Pf Po Qa Qd) Fr(Fp Hr Hv Hw Hx Ii Ij Im In Ir Is
It Iv Jg Ji Jl Jn Jo Jr Js Jt Lh Li Lz Me Mh Mj Mk Mr Mt Mx Na Nb Ne Nf Nh Nl Nm Nn Nr Nt Nw Ny Ok Om Oz Pa Pe Pf Po Qa Qb Qd)
Om(aA Et Fp Hw Im Iq Ir Is Iu Iv Ji Jl Jn Jo Jr Lh Li Lj Lz Mh Mi Mj Mk Mm Mp Mr Mt Mx My Na Nb Nc Nd Ne Nl Nn No Nr Nt Nu Nw Og
Oh Ok On Oz Pa Pe Pf Po Qa Qe) Ma(Fp Hr Hv Hw Hx Ih Ii Ij In Ip Iq Ir It Iv Ji Jk Jn Jo Jr Js Lh Li Lj Lw Lz Me Mh Mi Mj Mk Mr Mx Nb Nc
Ne Nf Nh Nl Nr Nt Nu Nx Oz Pa Pe Po Qa Qb Qd Qe) Jg(aA Hw Hx Ii Io Ip Iq Ir Is Iv Ji Jk Jl Jn Jr Js Lh Lu Lz Mh Mi Mj Mk Mp Mr Mx Nb
Ne Nh Nn No Nr Nt Nv Nw Ok Oz Pa Pe Pf Pg Po Pz Qa Qb Qd) Nn(Et Fp Hv Hw Hx Ii Ij Im In Ip Ir Is Iv Ji Jl Jn Jo Jq Lh Lu Me Mi Mj Mk
Mr Mt Nb Ne Nh Ni Nl Nr Nt Nw Ny Oh Ok Oz Pa Pe Pf Po Qa Qd) Pf(Et Hr Hw Ii Im Io Iq Ir Is Iv Ji Jk Jl Jn Jo Jq Jr Lh Lw Mb Mj Mk Mp
Mr Mt Mz Na Nb Nc Ne Nf Nh Nj Nl No Nt Nw Ny Ok Pa Pe Po Qa) Po(aA Et Hu Hx Im Ip Ir Is Iv Ji Jl Jq Jr Li Lw Mh Mk Ml Mm Mp Mr
Mt My Nc Ng Nj Nm Nt Nw Ny Of Og Oh Ok Oy Oz Pa Pb) Nw(Hr Hv Hw Ii Ij In Iq Ir Is It Iv Jk Jl Jo Jr Js Lh Li Lz Me Mj Mk Mr Na Nb Ne
Nm Nr Nt Nu Oi Ok Oz Pa Pe) Mp(Fp Hu Ii Io Ir Is Iv Jk Jl Lh Li Lz Md Mh Mk Mr Mt Nb Nc Ne Nh Nl Nr Nt Nu Ny Ok On Oz Pa Pe)
Mt(Hw Ii Iq Ir Is Iv Ji Jn Jo Jq Jr Lh Lz Mj Mk Mr Na Nb Nr Nt Oi Ok Oz Pa Pe Qa) Is(Et Hw Ii Io Ir Iv Ji Jk Jl Lh Lz Mk Mr Nb Nm No Nr Nt
Ny Oi Ok Pa Pb Pe) Jl(Im Io Ir Iv Ji Jn Jr Js Lh Li Lw Md Mr Mz Nb Nf Nm No Nt Ny Og Oi Pe) Ok(Im Io Iv Ji Jk Jt Lz Mk Mq Mr Nd Nj No
Nt Ny Oh Oi Oz Pa Pc Pe Pz) Et(Fp Ii Io Ir Iv Jk Lh Lz Mk Mr Nb Ne Nh Nl Nr Nt Ny Pa Pe) Jr(Ii Ir Iv Jk Lh Li Lz Mj Mk Mr Nb Nj Nr Nt Ny
Oz Pa Pe Pg) Ji(Hw Io Ir Iv Jk Lh Lz Mk Mr Na Nb No Nr Nt Oz Pa Pe) Ny(Im Ir Iv Li Lw Lz Mk Mr Nb Nr Nt Og Oh Oz Pa Pe) Jq(Ii Ir Iv Jk
Lh Lz Mk Mr Nb Nr Nt Pa Pe) Jn(Ii Im Jk Lh Lz Mk Mr Nb Nm Nq Pa) Mm(Ii Ir Iv Mh Mi Mr Nb Nr Pe Qd) Oh(Fp Ii Iv Li Mk Mr On Oz Pa
Pe) Nt(Fp Im Io Ip Ir Jp Nj Qa) On(Io Iv Mr No Oi Pc Pe Pz) Ii(Fp Jp Li Mx Og Pb Qa) Nj(aA Ir Nb No Pa Pe) Ip(Ir Iv Lz Mr Nb) Nm(Iv Lz
Mh Pa) Lw(Ir Mr Mx Pe) Im(Ir Lh Nv Pg) Qa(Lz Mk Nb Oz) Fp(Nb Nv Pa) Io(Lh Nv) Nx(Mx Pa) Pe(Me Pb) NoNs NqNr NbQb JoLh LiOi}
Jh{Oy(Et Fr Hw Hx Ih Ii Iq Ir Is Iv Ji Jk Jl Jn Jq Jr Js Lh Lu Lx Lz Md Mg Mh Mi Mj Mk Mp Mr Mt Mu Mw Mx Mz Nb Nc Nd Nf Ng Nk Nl
Nn No Nr Nt Nv Nw Nx Ny Oh Ok On Oz Pa Pe Pf Pg Po Qa Qb) My(Et Fr Hw Hx Ih Ii Ip Iq Ir Is Iv Jg Ji Jl Jn Jq Jr Js Lh Lu Lx Lz Mg Mh
Mi Mj Mp Mr Mt Mu Mw Mx Mz Nb Nc Nd Nf Ng Nj Nn No Nr Nt Nv Nw Nx Ny Og Oh Ok On Pa Pe Pf Pg Po Qa Qb Qe) Mg(Et Fr Hu Hw
Ii Ip Iq Ir Is Iu Iv Ji Jl Jn Jo Jr Js Jt Lh Li Lj Lw Lx Lz Mb Mh Mi Mj Mp Mr Mt Mu Mw Mx Mz Na Nb Nc Nd Nf Nl Nm Nn No Nr Nt Nw Og
Oh Ok On Pa Pe Pf Po Qa) Ng(Et Fr Hw Hx Ih Ii Ip Iq Ir Is Iu Iv Jg Ji Jk Jl Jn Jo Jq Jr Lh Lj Lu Lx Lz Md Mh Mi Mp Mr Mt Mu Mz Nb Nc Nd
Nf Nn No Nr Nt Nv Nw Ny Oh Ok Om On Pa Pe Pf Pg Po Qa Qb Qe) Og(Et Fr Hu Hw Hx Ih Ii Ip Iq Ir Is Iv Jg Ji Jl Jn Jq Jr Lh Lj Lx Lz Mh
Mi Mp Mr Mt Mu Mw Mx Mz Na Nb Nc Nd Nf Nn No Nr Nt Nw Ny Oh Ok On Pa Pe Pf Po Qa Qb Qe) Pb(Fp Fr Hv Hw Hx Ii In Ip Ir Is Iv Ji
Jl Jo Lh Li Lu Lx Mb Mh Mi Mj Mr Mt Mu Mx Mz Na Nb Nc Nd Nf Nn No Nr Nt Nv Nw Ny Ok Oz Pa Pe Pf Pg Po Qa Qb Qd Qe) Hu(Et Fr Hw Im Iq Ir Is Jl
Jq Jr Lh Li Lu Lz Mh Mi Mp Mr Mt Mu Mw Mx Mz Nc Nd Nf Nn No Nr Nt Nv Nw Ny Oh Oi On Pa Pe Pf Pg Po Qa Qb) Oi(Et Fr Hw Ih Ip Iq Ir
Is Iu Iv Ji Jl Jn Jr Js Lh Li Lj Lz Mh Mi Mp Mr Mx Mz Nb Nc Nf Nn Nr Nt Nw Ny Oh Ok Pa Pe Po Qa Qb Qe) Of(Hr Hv Hw Hx Ii In Ir Jl Jo
Js Lh Lu Lx Mb Mh Mi Mj Mr Mx Mz Na Nb Nc Nf Nr Nt Nv Nw Nx Ny Ok On Pa Pe Pf Pg Po Qb) Nc(Et Fr Hw Im Ip Ji Jn Jq Jr Lh Lj Lw
Lx Mh Mi Mp Mr Ms Mt Mx Mz Na Nd Nf Ni Nn Nr Nw Ny Oh Pa Pe Po Qa Qd) Nd(Et Hq Hv Hw Ih Ir Iv Ji Jn Jq Jr Js Lj Mh Ms Mx Mz Na
Ne Nf Nj Nl Nr Ns Nw Ok Qa Qd) Lx(Hq Hw Ih Ir Iv Jm Jn Jq Jr Js Lj Lw Ly Mh Ms Mv Mz Na Nq Nw Ny Oh Ok Pg Qa) Ms(Fr Ih Ii Is Jg Js
Lh Lz Mh Mn Mp Mr Mx Nb Nn Nr Nv Ny On Pa Pe Po Qb Qe) Mp(Et Hw Iq Ir Iv Jn Jr Js Lh Lj Ma Mh Mr Mz Nf Nt Nw Pa Pe) Im(Ir Iv Ji
Jn Jq Jr Js Lw Mb Mh Mj My Nb Nf Nl Nr Nw Pa Po) Lj(Et Fr Lh Lu Mb Mh Mr Mt Mu Nn Nt Nv Nw Oh On Pa Pe Po) Pa(Et Hx Ih Il Ip Jn Js
Lw Mk Mv Mz Na Nf Oe Oh Qa) Mv(Fr Iq Lh Lz Mh Mt Mz Nf Nn Nw Ny On Pf Po) Oe(Hw Iu Jl Mr Mx Nb Nr Ny Pe Po Qb Qe) Mz(Hw Hx
Ij Iu Lz Md Ml Mr Nt Ny Pe) Et(Hw Iq Ir Jn Mh Mr Nt Om Pe Pf) Oh(Hw Ir Jq Lh Mr Nn Nt Pc Pe) Lw(Fp Iq Iv Lu Mr Mx Nf Po) Jn(Hw Iu
Lh Lz Mr Nr Nt Pc) Jo(Hw Ir Lh Mr Nt Ok Pe) Jq(Hw Iq Jg Lz Mb Mh Nr) Nl(Ip Nf Nw Ny Po Qe) Hr(Ir Jr Lh No Ok Pe) Ij(Hw In Ir Ji Ok)
Nw(Mh Mw Ne Pe Pf) Po(Hx Mh Mw Ny) Nt(Iq Ir Jr Mt) Me(aA Hv Iv) Mm(Hv Iv Js) Nf(Iu Iv Na) Ip(Hw Lz Ne) Nn(Ne Nr) Nu(Ok Pf)
Mb(Iq Qd) Mr(Il Jr) Mw(Om On) Jt(Ir Ok) Lh(Il Jr) aA(Ji Nj) LzNa MkPe HwIh IuJs} Om{Pb(aA Et Fp Fr Hw Ih Ii Im Ip Iq Ir Is Iu Iv Ji Jl Jn
Jr Lh Lx Lz Mh Mi Mp Mr Mt Mu Mw Mz Na Nb Nd Ne Nn No Nr Nt Nw Og Oh Ok On Oz Pa Pe Pf Po Qa) Mg(Et Fr Hw Im Ip Iq Ir Is Iu Iv
Ji Jl Jn Jr Lh Li Lj Lx Lz Mh Mi Mm Mp Mr Mt Mu Mw Nc Nd Nl Nm Nn No Nr Nt Nw Og Oh Ok On Pa Pe Pf Po Qa) Oy(aA Et Fr Hq Hw
Hx Ii Im Iq Ir Is Iv Ji Jk Jl Jn Jr Lh Lu Lx Lz Mh Mi Mp Mr Mt Mu Mw Mx Nb Nd Nn No Nr Nt Nv Nw Og Oh Ok On Pa Pe Pf Po) My(aA Et
Fr Hw Ii Im Iq Ir Is Iv Jg Ji Jl Jn Jr Lh Lu Lx Mh Mi Mp Mr Mt Mu Mw Mz Nb Nd Nf Nn No Nr Nt Nv Nw Ny Oh Ok On Pa Pe Po) Of(Et Fr Hw
Ii Im Iq Ir Is Iv Ji Jl Jn Jr Lh Lu Lx Lz Mh Mp Mr Mt Mu Mw Mx Mz Nb Nd No Nr Nt Nw Oh Ok On Pa Pe Pf Po) Ng(Et Fr Hw Im Iq Ir Is Iu
Iv Ji Jk Jl Jn Jr Lh Lx Mm Mp Mr Mt Mu Mw Nd Nn No Nt Nw Oh Ok On Pa Pe Pf Po) Ij(Et Hv Hw Ih In Iq Ir Is Iu Ji Jn Jq Jr Js Lh Mh Mr
Mw Mx Mz Na Nr Ns Nt Ok On Pe Qa Qe) Pz(Et Fr Iq Ir Is Iv Jg Ji Jl Jn Jp Li Lj Lz Mi Mm Mp Mr Mu Mw Nn Oh Ok Pa Pe Pf Qa Qd Qe)
Oi(aA Et Hw Ih Ip Iq Ir Is Iu Iv Ji Jl Jn Lh Li Lj Mh Mp Mr Mu Mz Nn Nr Nw Oh Ok Pa Pe Qa) Im(Fr Hu Hw Iq Ir Iv Jl Jn Jq Jr Lj Lw Lz Mh
Mp Mr Mt Mv Mz Nc Nd Nl Nw Og Oh Ok Pe Pf) Mv(Fr Is Ji Jn Jr Lh Lx Mh Mi Mp Mr Mt Mu Mw Mz Nd Nf Nn Nt Nw Oh On Pa Pe Po
Qa) Ms(Et Fr Hw Ih Is Iu Ji Jn Jr Lh Lx Mp Mr Mt Mu Mw Na Nd Nn Nt Nw Oh On Pa Pe) Og(aA Et Hq Hw Iq Ir Is Iv Jg Ji Jl Lh Lx Mr Nb
Nd No Nt Nw Oh Ok On Pa Pe) Lx(Et Hq Hu Hx Il Ir Jm Jn Jr Lj Ly Md Mh Ml Na Nc Nq Ny Oh Pg) Nd(Et Hq Hu Ih Ir Iv Jm Jn Jo Jr Lj Ly
Na Nc Nl Ns Nw Ok Pg) Hu(Et Fr Hw Is Jr Lh Mp Mr Mt Mu Mw Nn No Nt Nw On Pa Pf) Nc(Et Fr In Io Ip Jq Jr Lh Lj Mp Mr Mt Mu Nn Nw
Pe) Jo(Hw Iu Jl Jr Lh Mi Mr Ne Nl No Nr Nt Ok Pa Pe) Ml(Ji Lh Mh Mi Mr Mx Mz Nf Ns Nw Pa Pe Po) Md(Ji Jq Lh Mh Mi Mr Mz Nf Nw Pa
Pe Po) Mr(Hx Ii Il In Jr Mh Mp Mw Nb Ny Oh) Ny(Lh Mh Mi Mx Mz Nf Nw Pa Pe Po) Nt(Il In Iq Jn Jr Lj Ly Mz Oh) Pa(Hx Il Jn Lw Mh Mk
Mw Mz Oe) Mp(Iq Jr Jn Jr Lj Ma Ns) Mh(Hx Lh Mz Nw Pe Po) Mw(Fr Jg Lh Nw On Po) Hr(aA Ir No Ok Pe) Hw(In Jn Jq Mz Oe) Hx(Lh Mz
Nw Pe Po) Lj(Et Fr Lh Mu Nn) No(Mj Nv Po) Iq(Et Mu Qc) Iu(In Jn Mz) Me(aA Iv) Mm(Iv Jn) Ih(Fr Mu) Lh(Il In) Nw(Ne Nl) Pc(Jn Mk)

Ii Nb Ny On Po) Ns(Md Ne Pd Pf Po) Mr(Jn Jr Lw Ly Mz) Jo(Hw Ir Lh Ok Pe) Et(Jn Jr Mz Nf) Nn(aA Jt Lw Mi) Ni(Jp Mh Nk Nl) Mb(Fp Lj Mh) Mt(Hw Na Pc) Jl(Jn Jr Mz) Jt(Ir Ok Pc) aA(Lw Mm Nj) Hu(Jk Mx) Hw(Ir Ok) Is(Mm Mz) Jn(Lh Pe) Jr(Lh Pe) Lj(Ii Md) Of(Ny Po) NoMj MqOk MsNb NaPf Nflv HrJp QcJi} Nn{Ng(Fr Hw Hx Ii Iv Jl Jo Lh Lu Md Mr Mt Nb Nd Ne Nm Nt Ny Ok Pa Pe Po) Pa(Hv Hw In Jn Jr Js Lw Mk My Mz Na Nf Ni Oy Pc Qa) My(aA Fr Hx Ii Jl Lh Md Mr Mz Nb Ny Pe Po) Oy(Fr Hx Ii Jl Lh Md Mr Nb Ny Oz Pe Po) Pc(aA Ji Jl Jt Lw Mh Nc Nr Ok Pf) Jo(Hw Iq Ir Iv Lh Mr Nt Ok Pe) Hu(Fr Ii Jk Mr Mt Nb Ny Po) Nc(Ii Ij In Nb Nf Ni Ny) Nt(Jm Jn Jr Mz Nf) Et(Hw Mr Mz Pe) Mv(Ii Mz Ny Po) Iq(Hv In Na Qa) Mr(In Jr Lw) Of(Ii Ny Po) Ok(Jt Mq Nu) Nq(Fr Lh) Ms(Ii Nb) Nd(Jm Ni) Jl(Jn Jr) NoMj NsPd NuPe MbPf MdLj MfNi MlMz NeIp NjaA IrJt JrLh} Hr{Jr(aA Hw Ii Ip Ir Iu Jk Jl Jo Lh Lu Mr Mt Mz Nb Nd Nf No Nq Nr Nt Ny On Pa Pe Po) Mt(aA Et Hv Hw Ir Is Iv Jl Jn Jo Lh Mr Mz Na No Nr Nt Ok Pa Pe Qa) Is(Et Hw Iq Jl Lh Lu Md Mr Mz Nf No Nt Ok On Pa Pe Pf Po) aA(Et Ii Ip Ji Jl Mn Mr Mz Nf Nj No Ny Ok On Pe Pf Po) Jl(Hv Hw Iq Ir Jn Js Lh Md Mz Na Nf No Ok) No(Et Ip Ir Ji Jn Ms Nf Ok On) Jn(Et Mr Nd On Pe Po) Ny(Et Ip Na Nd Pf) Ji(Lh Lu Mr Pe) Ok(Mq Nd On Pa) Po(Ng Oy) Et(Ir Pe) Lh(Ng Pf) On(Ir Mz) FrNc} Fr{My(aA Hv Hw Ii Ij Ir Is It Iv Ji Jl Jn Jo Js Lh Mb Mr Mt Na Nd Nm Nr Nx Ny Ok Pe Qa Qb) Ng(Hv Hw Ii Ij Ir Is Iv Jl Lh Mb Md Mr Mt Nb Nc Nd Ne Nf Nt Ny Ok Pa Pe Po Qb) Oy(Ii Ij Is Lh Mr Mt Nb Nr Ny Pe Po Qb) Nc(Hv Hw Ij In It Jn Jo Me Na Ni Qa) Mb(Ih Iq Lj Mt Ne Nl) Ok(Jo Jt Mq Nu) Et(Js Mz Nf) Hu(Lh Ny Qb) Nj(aA No) Jm(Nd Nt) Jo(Is Lh) Of(Ii Ny) LwLh LyMr JiNx} Ji{Ij(Hw Ii Il Ir Is Iv Jk Mr Na Nb Nr Ok On Pa Pe Po) Nx(Hw Jk Jl Lh Lu Mr Nc Nd No Nt Ok On Pa Pe) Qc(Iq Ir Jn Jp Jr Mt Mx Mz Ok On Pf) Ii(Hx Ml Mr My No Nt Ny Of Oy) Mj(aA Is Jl Lh Lu Mr No Pa) Po(Hx Mh Ml My Ny Of Oy) Pa(Hx Mh Mk My Nb Ng Oy) Jk(Ms Mv My Ng Of Oy) Me(aA Iv Lu Mf) Ok(Jo Jt Mq) Nt(Jo Lv) Mm(Lw Pc) Qd(aA No) LvJl MbMs MlNf NdIn IhaA JrJs JtOn} On{Jo(Hv Hw In Ir Iv Jn Jr Lh Mr Na Ni Nr Nt Nx Ok Pe Qa) Ij(Hv Hw In Ir Jn Jr Mz Na Nx Of Qa) Jt(Hv Hw Ir Iv Jn Jr Na Nm Ok) Nx(Hv Hw In Mz Na Ok Qa) Of(Hv Hw In Jn Mz Nf Pe) Qc(Iq Jn Jr Mt Mz Oy) Mj(Ng No Ns Ok Oy) Mq(Hw Ir Na Ok) Nt(Il Jm Nv) Nd(Hq Jm Ng) Oy(Ii Pc Qd) Pa(Il Mk Ng) My(aA Nq) Nv(Lh No) MeaA MrIn NcNi NgOk} Pf{Mm(Hv Ij In Ir It Iv Jn Js Ng Ns Qa) Oy(Hx Ii Jk Mb Md Nb Nv Ny) Nc(Hv Ij In Nf Ni Ns Qa) Ng(Ii Jk Lh Nd Nm Nt) Ns(Lw Mb Md Nd Po) Iq(Ij In Lj Lz Qc) Pa(Hv In Js Mk Qa) Mb(Hq Jn Jr Pd) Mj(Ir Is Lh Ok) Jo(Hw Lh Nt Pe) My(Ii Nb Ny) Hq(Lw Md Nd) Ly(Mr Nt) Me(aA Iv) Of(Ii Nb) LwPd LzJr MhMr MlMz MqOk} Nd{Lw(Et Fp Hq Iv Jn Jr Js Ml Ne Nh Ns Ny) Et(Hv Ir Iv Jn Js Mz Ne Ng Nh Nl) Ng(Jk Jl Mt Nm Nt Nv Ny Ok) Ny(My Na Nc Ne Nh Of Oy) Nj(aA Is Jn Jr Mt Qd) Mz(Is Jr Ml Nh Of) Is(Ir Jm Jn Jr) Nh(Ip Mn Na) Ok(Jo Mq Nu) Po(Hq Ly) Mt(Jn Oy) In(Ir Iv) Ip(Ne Nl) NsMd NtIl LvMx NcNi} Ok{Jo(Hw Ii Jk Jl Lh Mr Nc No Nq Nt Nv Ny Pe Pg Po) Mq(Is Jk Jl Lw Mt No Nq Nt Pa) Mj(Is Jl Jr No Nt Pa Pe Po) Me(aA Iv Lu Mf Nm) Jt(aA Lw Mm Nc Nq) Ng(Jk Lh Nt Pa) Lw(Mr Nm Pc) My(Jk Mv Nq) Oy(Jk Pa Pg) Qc(Iq Mz) Pa(Mk Nr) PoMh NtNl NuMb MmPc} Mt{Oy(Ii Jk Jl Lh Mb Mr Nb Ny Pa Pe Po) Ng(Ii Jk Lh Mb Mr Nb Nt Pa Po) My(Ii Lh Mz Nb Ny Pa Po) Ii(Hx Mh Ml Ny Of) Of(Mz Nb Ny Po) Lw(Iq Jl Pa) Mb(Iq Nj No) Nt(Et Jm) Mh(Mr Po) Qc(Iq Is) LyMr MlMz NcNi HuJk JoLh} Et{Lw(Fp Iq Lj Lu Mr Nc Pa) Ng(Hw Jk Lh Nr Pa Po) Nc(Hw Ip Jn Nf Ni) Jo(Hw Lh Mr Nr Pe) Oy(Ii Jk Nb Ny Po) Nt(Iq Jn Jr Mz) My(Jk Mv Ny Po) Me(aA Hv Iv) Pa(Jn Jr Js) No(Mb Mj) Hw(Iq Jn) Jk(Hu Lj) MdLj NfJl JrLh} Is{Mj(Iq Jl Lh Mh Mr Mz Nf No Nt Oe Pa Pe) Me(aA Hv Ir Lu Mf) Ij(Hv Hw In Ir Na) Lw(Lh Mr Nf Pa) Mb(Iq Nj No) Nm(Jt Ng) Nt(Il Jm) Mm(Mz Pc) Qc(Iq Mz) Oy(Ii Po) Pa(Il Jm) NoQd NsPd NaIt} Jl{Jo(Hv Hw Ij In Ir Jn Jt Lh Mr Na Nf Nm Nt Pe Qa) Oy(Ii Md Mv Nb Pa Po) Ng(Lh Nm Nt Pa Po) Lw(Iq Jn Jr Nf) Mj(Lh Nf No) My(Mv Nb Nq) Nc(Ni Nk) Qc(Jr Mz) NtJm MeIv MkPa} Mm{Ny(Hw Jn Js Lj My Na Ng Of Oy Qa) Jr(Ir Iv Lh Mr Pc Pe) Ng(Ii Mr Nt Po) Nc(Ip Na Ni) Iv(Jn Nu Pa) Oy(Nb Pe Po) Lu(Ip Jn) Lw(Fp Mh) Lh(Jo Mi) Pc(aA Jn) NoIu LyMr MdMh NbOf} No{Mj(Ij In Ir Jn Jr Js Lh Lw Ms Qa) Nj(aA Ir Jn Ly Mb Mh Ms Mz Nf Nl) Me(aA Jm Mb Ng) Mb(Il Ns)} Jr{Mj(Lh Mr Nt Pa Pe) Me(aA Iv Lu Mf) Jk(In Lw Ng Oy) Jo(Lh Mr Pc) Po(Lw Of) Ip(Hw Mn) NqIr LuLw MbNj MrIn IiOy} Ng{Jk(Jn Lw Mf Mi Nm Ny Po) Po(Ip Lw Me Nm Nq) Nq(Ii Nb Ny Pe) Nm(Mh Nc) Lw(Mr Pa) Me(Nt Ny)} Lw{Mr(Jn Jo Ly Oy) Oy(Pa Pe Po) Nc(Na Ny) Iq(Mb Qc) Jo(Lh Pe) PoJn MeHv MhJp PcaA} Jo{Lh(Ip Jn Ly Nm) Pe(Ip Mb Nc Ny) Mr(Ip Ny) NmNy NtNx IrPg} aA{Me(Hu Jn Mf My Mz Nf Nj Pc Pe) Jk(Hu Oy) NmJt MbNj} Nj{Na(Iq Mz Nq Pa) Mb(Md Pa Pe) NqMz NiIq} Ip{Nc(Jp Mz Na) PoOf NtJm MbMd IvJp} Oy{Pe(Jk Mv Nq) Po(Mh Mj) NqIi} Jn{In(Lh Mr) PoMy LuMe MjLh} Ny{Mb(Mh Of) IlPa} My{PoMe NqPe} In{MrNc JsLh} IlNxPa Constrained panels with 3 analytes, where 1.0E-7 >= 'AUC p-value' > 1.0E-8. Contains 1,036 panels of 287,980 total panels evaluated. : Jg{Lx(Hq Hv Hw Iq Iv Jn Js Lj Lw Mb Mh My Mz Na Nc Nf Ni Nq Ns Pb Qa) My(Fr Ii Ip Ir Js Md Mh Mr Mu Nv Pa Pg Po) Oy(Fr Ir Js Lu Md Mh Mr Mu Nb Nc Nv Pa Pg) Ik(Fp Hv Im Iu Jo Li Md Nl Ny Qe) Nd(Ir Jn Mh Nc Ne Ni Nl Ns Qd) Mg(Hr Ij Jn Lw Lz Mq Mx Qe) Ns(Ip Lh Md Mu Nc No) Ng(Jn Js Lz Mh Nf Og) Pz(Iu Jo Js Na Nt Oz) Pa(Hv Hw Iv Mk Na Nc) Mv(Lh No Ny Po) Hu(Ip Lh No Ny) Ms(Jn Nn Ny) Io(Jt Lj Lw) Ip(Lz Ne Nl) Of(Nb Pe Po) Im(No Pg) In(Ir Iv) Jj(Hv Nm) Jo(Mr Pe) FpLw NtJm MwNy NcNi HxPb IlPe JqLj} Im{Nc(Hr Hx Ij In Li Mq Na Nf Ni Pd Qd) Fr(Hu Hv Ij Ir Jn Jo Js Lw Nr Qa) Nv(Hv Ir Iv Jn Js Jt Mb Nf Nm Qa) Ma(Hx Ij Ik In Jk Jo Md Oi Qe) Ik(Ii Jk Lz Mj Nb Nr Pa Qa) Pg(Hv Hw Jp Jt Mb Mm Na Qa) Lw(Iq Ir Jp Li Mu Pe) Mm(Ir Mh Nx Pa Qa) Po(Hr Ly Ng Oy) Nr(Et Mt Mu Og) Mb(Lx Nl Pe Qd) Ir(Lh Mt Mu Ny) Oi(Iq Jk Nl Pa) Nm(Nl Ny Pa) Mz(Hr Lh Mt) Jn(Lh Mt Ny) Mg(Lh Mr) Ip(Jp Lz) Jk(Mh Ng) MnNl MpJo MuHu HwPb IvNy JpNx OgPa} Mm{Mg(Hr Hx Ij In It Jk Lx Mj Na Nb Nw Pa) Ng(Hw Ir Iv Jk Lh Md Mh Nb Nx Pa Pe Pg) Lx(Hq It Jo Me Na Nf Nr Oy Qa) Io(Ih Ip Jk Jp Mb Nd Ne Nl Qb) Jn(Ii No Nt Pa Pe Po) Mz(Iv Lh Nt Pa Pe) Jo(Ir Iv Mr Pb Pe) Mh(Hv Ih Na Ni) Oi(Hx Lw Nt Qe) Nc(Ij In Nf) Ni(Nd Pa Po) Og(Hr Hx Qe) Ns(Pd Po) Nt(Ir Jm) Me(Jj Pa) Nb(My Pz) Ii(Oy Pz) Jr(No Pa) FpOh LuNf LwOk MdIp NaIh NdIr NhIk IqPe} Pb{Nr(Hv Ir Jn Mn Mx Mz Na Nc Nm Nv Nx Og Pa) Nb(Fp Ik Jk Li Nd Nv Og Pa Pg Po) Ii(Hv Iq Ir Jn Lj Nm Nv Of) Pa(Fr Hw Ij Ir Iv Jo Mz Ny) Hw(Lw Mn Nv Qb) Ny(Jo Jr Of Oz) Lx(In Md Ni) Mr(Ij Jn Mb) Pg(Ir Mb Na) Ma(In Nf) Md(Nd Pe) Mz(Ip Pe) Hx(Ip Mt) Jk(Jn Na) Nv(Io Ir) Oz(Hv Jn) PoNi JoJp} Ik{Nt(Iq Iv Jn Js Li Lj Lz Nb) Qa(Jk Li Mj Nm Nr Nv Pa) Jn(Iq Li Mh Mj Nr Oz) Ip(Ii Li Mx Nr Pa) Lw(Iv Lz Mi Pa) Nv(Iv Jp Mh Nb) Lx(Me Ml Ni) Nj(Iq Mi Mx) Ir(Ii Jk Nd) Li(Io Nb Pa) Fp(Jk Pg) Ma(Md Nd) Qd(Lh Po) Ny(Hr Iq) NmMi NoMr NrQb MkJj MnNh MzIi NbJp JkPe JoJr} Lx{Lw(Hw Iq Ir Jp Lj Ns Qa) Mg(Hv Hw Ir Jo Jt Qa) Hq(Fr Iv Li Nf Nt) Mu(Hv Hw Ir Qa) My(Fr In Md Nf) Hx(In Ns Ny Og) Jp(Hu Mb Nm Oy) Lj(Ij In Mb) Ny(Jm Ml Of) Oy(Hr Mz Nt) Hu(Jh Jo) FrNq LyMz MhPe NbOg HrQa IhOi IjIq InIr JmNv JnJs} Ma{Nc(Hr Hx Ii Jo Mh Mi Qe) Ng(In Js Lw Ne Nm Pa Qe) Ne(Ii Jp Jt Mx Nx) Jo(Ih Iq Nd Pa Qb) Mg(Ij Iu Md Nd) Nl(Hr Hx Jp Nf) Lj(Hr Lw Md Nd) Hx(Iq My Oy) Jp(Fp Hr Mb) Ih(Hr Jk) Qe(In Lw) NmQb MbMx NdNi NfOg IjIu IqQc} Jj{Lw(Fp Ih Iv Jm Mn Mv Mz Nr Qe) Lu(Fp Hu Hv Iu Jt Lj Lv Mb) Na(Ih Li Mh Mn Nk Nl Nr Qb) Hr(Ih Lz Mh Mn Nl Qb) Mb(Fp It Mv Nh) Jp(In Iv Nb Nu) Mn(Ij Js Jt) Hu(Lv Mx) Jn(Li Qb) MiPc MyNe NbOy IhJs IvJq} Fr{Ng(Et Hx In It Jn Jo Js Lw Na Nm Nr Qa) My(Hx In Md Ml Ne Nf Pa Po) Jo(Hv Hw Ir Iv Mr Nm Pe) Oy(In Md Ne Nf Nt Pa) Hu(Md Mu Mx Ne Pe) Ij(Iq Lj Of) In(Lj Ne) Of(Nf Pe) LwLj MdMl MfMx MkPe NaIq} Ip{Nc(Ir Jn Jt Lw Mb Md Nb Nd Nm Pe Po Qa) Jp(Hv Hw Ii In Js Lz Mb Md Na Nr) Mb(Ih Jn Nh Nl) Mn(Ir Na Ne Nh) Og(Hx Jk Nm Nx) Oi(Jk Lj Nb) Po(Hr Mh) NmMg LyMr NdNx HrJn JkJm} Ny{Og(Ir Lh Mr Mz Nb Nr Nt Pa Pe) Oi(Ih Lz Mr Nt Pa Pe) Nd(Hw Jm Jn Lj Nl) Hr(Mr Nc Pe Po Qa) Po(Hu Ng Oy) Me(Mf My) Mg(Mr Pe) Io(Iu Nt) NmNg LzMb MrIn MwIi NcNi HwJo} Nm{Mg(Fp Ih Ir Jp Md Mx Nl Nx) Og(Hw Hx Jk Mh Mz Nr Nx Qb) Jo(Mr No Nv Pa Pe Po) Io(aA Ih Iv Nv Qb) Oi(Fp Jp Nf Qb) LuJr NdNh PzPe} Oi{Jk(Jp Mh Nf Pa) Nv(Jn Mr Mz Qa) Lw(Ih Mz Qe) Fp(Jp Nc) Mb(Ih Li) Mn(Ne Qb) Ii(Iq Mx) Qa(Nb Nf) Lj(Hw Jt) PoOf LuLi MeIr} Og{Jk(Hu Iv Nb Nr Pa) Ii(Jn Li Lj Qa)

Figure 43 Continued

Nq(Hr Nr Nx) Jn(Mr Nb Pe) Me(Mr Nt) PoNb NrMn LwIl MbNv MvIv HxJq} Mu{Pa(Hv Il My Oe Oy Qa) Lj(Md Mi Nf Nt) Oy(Hr Mz Qe) Lz(In Na) Hx(My Ng) MbQd MfMx NbOe IvJo OfPe} Mg{Jk(Ii Mb Mr Nx Pe) Jp(Ii Lh Mr Nt Pe) Li(Ii Lw Nb Nx) NqIr MePe MrQa MtNb JrLh JtOh} Nd{Nh(Fp Ii Jp Nb Ng Ns Nx) Md(Lj Mh Ml Nj) Mz(Nc Nj) Jr(Ir Iv) LwNc NaNl HqPd} Io{Nv(Iv Mi Mx Pa Qa) Jp(Mi Mr Pa Qb) Nt(Ly Qa) Me(Jn Mi) Nc(Li Qd) LwJn JqaA} Lw{Mr(In Jr Mt) Jt(Mp Nn Oh) Ng(Ii Lh) Jn(Jk Lu) PoPd FpJp MfMx IlPa JrPe} Pa{Mt(Jn Jr Mz) Nj(Ir Ni Qa) Mw(Mv Oe) Nc(Nw Om) PoIl JoOk} Ng{Jk(Hu Lh Md) Me(Lh Pe) EtNt NqNx MnIi HuJh OfOh} Jn{Hr(Hw Jk Lh Lu Nb) Po(Hx Mh) NtMt PzJp JkOy} Mb{Mh(Md Qd) Iq(Nn Pf) FpOh MzNh JpPg OyPe} Jo{Nv(Hw Ir Iv Mr Pe) Ir(Nq Om) HwPg} No{Mj(Hv It Iv Mz Nf) MzHr} Nw{Nc(Ii Nf) Jk(Ms Of) MlLh NeNf} Jp{Pz(Jk Li Pg Qa) MhNa} Om{Iv(Ij In Ms) HuJh LhNx} Mv{Mt(Ii Nb) MyJq NbJh} Mw{NrOe NfNl HxIi NvOy} Na{Nj(Jk Md) PoHr} Jq{Fp(Hr Iu) IiLh} Nq{NbOy HuIi} Nt{MtJr NfPf} Me{MfPe MpHv} In{LyMr MnIr} Iq{Qc(Jr Qa)} PoHrJs MqIlPe OhOkaA

Constrained panels with 3 analytes, where 1.0E-6 >= 'AUC p-value' > 1.0E-7. Contains 1,288 panels of 287,980 total panels evaluated. : Jg{Ns(Ih Ir Iv Jn Lu Mi Mz Ne Nh Nr Nt Nv Pa Pd Pg Po Qa Qb) Oy(Hw Ih Im Iq Iv Jk Mi Mz Nd Ne Nf Nh Nq Nr Nt Qa Qb) My(Ih Iq Lu Mi Mz Nb Nd Ne Nh Nl Nq Nt Qa Qb) Ng(Hq Hv Hw Ih Ip Ir Iu Iv Jo Mb Mj Nr Om Qa) Hu(Ir Lu Lx Md Mg Mu Nc Ne Nt Nv Pa Pg Po Qa) Nd(Hr Hv Hw Ij Ik In Iv Js Lj Me Na Nf Qa) Im(Ih Ir Iv Jn Js Lw Md Mh Mz Ne Nf Nr Pe) Nc(Hv Ij In Mb Na Pe Po Qb) Mv(Jq Js Lx Mr Mu Pa Pe) Jo(Hw Ip Iv Nr Nt Ok Pb) Ih(Hv Hw Lx Mb Na Ni) Lw(Iq Lu Ne Pz Qb) Ms(aA Io Ip Pa Qb) Ik(In Nf Ni Nu Pd) Po(Hx Mh Na Ny) Mb(Ip Mh Nl Qd) Mz(Hw Ny Of Pe) Lj(Lu Md Nv Ny) Ni(Iq Lz Mg) Pb(Ij In Nf) Lx(Nr Pg) Jn(Pa Pe) Of(Hx Nf) NoNv NtIr MaNl MhNa MrIl MwLh IqQc JrPa} Mm{Lu(Hv Ij Im In It Js Lw Mb Me Mg Na Ng Qb) Iq(Hv Hw Ii Ij In It Iv Me Mr Na Nb Ni Qa) Js(Hw Ii Im Lh Mr Nb Nd Nr Nt Pa Pe Po) Ih(Fp Hv Hw Ii Ij In It Mb Me Nb Ni) Ng(Hq Hv Hx In Jo Mi Na Nr Nv Qa) Io(Hr It Lj Lv Lw Md Ml Mx Nk Qe) Pa(Hv Hw Ij Ik In Ir It Na Nf Qa) Im(Hv Iv Md Nb Nl Pe Qd) Mh(Ij In It Jo Mb Mr) Nf(Hw Iv No Nr Nt Pe) Ik(Fp Jk Md Mx Ne Nu) Pz(Jk Jp Mj Nt Qd Qe) Po(Hv Hw Lj Na Qa) Nc(Hr Ii Me Mj Nb) Mg(Hq Li Ma Pd) Nd(Hv Ij Me Ne) Ip(Hr Mb Me Ne) Jn(Lh Mr Nb Nr) Lj(In Lx Md Nv) Oi(Hr Ml Mx Qd) Nt(Hv Jr Qa) Ni(Lx Lz Nv) Md(Nr Qb) Mr(Ir Mz) Ii(My Of) Jk(Hu Og) FpNb NoMz NsHw LwNc LxPg LzHv MbQd MeNv MuIt NaQb InOg} Im{Lw(Ii Iv Jn Js Lx Mi Mj Mr Mx No Nr Pa Po Qa) Fr(Hr Hw In Iq Iv Jt Mz Na Nf Pe) Mh(Hv Ij In Lx Mb Mn Nd) Og(Ir Iv Jk Mr Nm Pe) Ii(Iq Jn Js Ng Nl) Ik(Ij Mi Nh Oz Pe) Jo(Lx Nc Nv Pb Pg) Po(Il My Nm Of) Jp(Nl Nm Nv Pa) Lx(Hu Ir Jm) Mb(Ma Md Nc) Mn(Ip Ir Nh) Hr(Iq Mr Pe) Hw(Ip Nv Ny) Oi(Ih Lz Mj) Nm(Pg Qd) Nr(Nv Ny) Nt(Io Jm) Md(Ip Li) Mu(Mj Mz) Nd(Ma Ne) MeIr MgPe NaNv NbNl NgPa HuJk IqLh} Pb{Ii(Hw Hx Iv Js Li Lw My Nf Nh Nl Nr) Mz(Hw Ir Iu Iv Jk Mr Mu Nv Oz Pg) Jk(Hv Hw Ip Ma Mb Mi Nm Nr Nx) Hw(Li Nc Nd Nm Nx Pg Qe) Ir(Li Mb Md Me Mr Nt Oz) Nv(Hv Ij Iv Jo Qa) Nx(Fp Hx Li Lz Oz) Pa(Hr Ip Jt Lx Me) Nb(Lj Na Nh Nl) Ny(Hr Hu Mh Nc) Nr(Ij Md Pg) Lx(Ij Ml Nf) Fr(Md Ml) Na(Ip Li) Qa(Jo Pg) PoNs NtIo MaMl MrHv NdIv NfPe HxJr} Ik{Nv(Ii Ir Li Lj Lz Mj Mk Na Nm Nr Oz Pa) Jk(Ip Iv Jp Li Mr Mx Nb Nm Og Oi Pa) Pg(Ii Jp Lz Mk Na Nb Oz Pa Qa) Nm(Fp Mk Mx Ne Nh Nl Nr Qd) Ii(Iq Js Lz Mi Nh Qd Qe) Fp(Ip Lw Lz Nc Oz) Nr(Jp Mn Nj) Nt(Mz Nf Qd) Lz(Ij Nx Qb) Nb(Ir Lj Me) Lx(Jm Mg) Md(Li Qa) Mr(aA Nj) Mx(Ij Nc) Ir(Lh Oi) Pa(Ij Qb) Pe(aA No) MaPd MhQd MkNx MnNe NjIv IpOz} Lx{Hu(Fr Hv Hw Hx Ii Ij In Jk Jn Js Mr Mu Mz Na Nb Nf Pe) Iq(Hv Hw In Jo Mh Nm Qa) Of(Hv Hw In Ir Na Nb Nf) Mh(Hq Ih Mk Ns Pd) Jp(Hv Hw Jm Jo Na) Mg(Iv Mq Na Ny) Nf(Hx Ml Mz Nr) In(Iv Md Ml Nc) Jo(Hw Ir Nm) Pg(Jm Nt Pa) Mb(Jm Qd) Mx(Lw Nm) Nc(Ij Ny) Hq(Mz Nb) Ii(Mv Ng) Oy(Jt Pa) NsMq NtIl MdMl MkOz MuNa NiLj QeOg} Jp{Lw(Hw Ii Io Ir Iv Jj Jk Li Lu Mi Mx Nb Nf Nr Nt Qa) Ip(Iu Jk Jo Jt Nl Nm Qa) Mb(Io Jj Jn Md Nl Pa) Nc(Hv Ij In Lv Ni Nx) Io(Hw Ih Nl Nm Nr) Oi(Ih Iq Iu Nb Nf) Mh(In Iu Nd Nm) Pz(Ir Nt Pe Po) Jj(Hr Hv Js Jt) Nd(Ne Nl Nx) Ii(Ng Of Oy) Jk(Mg Og Oy) Ma(Mg Ng) NmQb NqHu NtIl NaPg} Nm{Ng(Hq Ii Lh Lz Mi Mr Nq Nt Nv Pa Pe Pg Qa Qb) Jo(Hw Ii Lu Mg Mi Nt Pg Qa) Og(Fp Hr Ih Nc Ne Nt Nv Qe) Oi(Hx Ip Iv Jk Mn Qd Qe) Nc(Fp Md Na Nd Ni) Io(Hx Mn Mx Nk) Pz(Ir Lz Ma Pa) Mg(Hv Nh Qe) Nd(Fp Ne Nl) Po(In Of) Ma(Mx Ne) MdMh MrIn IlPa OhaA} Ip{Nc(Hr Hv Hw Hx Ii Ij In Iq Jk Li Mh Mj Nf Ni Nr Nx Pa) Mn(Ih Iq Lu Md Mh Nl Qd) Na(Iq Lz Md Mh Nd Pa) Mb(Iq Lz Mh Ne Qd) Po(Iq Jn Mz) Nd(Hv Js Mh) Jk(Mz Ng Oy) Oi(Ih Mv Nr) Md(Li Mh) Nb(Of Oy) NqJn LzNx MrHr MzPa NgIi QeOg} Oi{Mn(Fp Hr Hw Hx Ii Mh Mv Mx Nb Nf Nl Nr) Jk(Ih Js Jt Lw Lz Mi Na Nb Nr) Nv(Ih Nb Nf Nr Pa) Lj(Iu Lv Lw Mv) Nr(Jn Ny Qa) Po(Ih Ir) Nt(Iq Mz) Nb(Jn Qb) Hw(Jn Ny) FpIh NqMh MaIu MrHr MzLh NcHx IiQa IqNx} Ny{Hr(Hw Iq Ir Iv Jn Lz Mz Ne Nl Nr Pa) Nd(Hq Hu Ir Iv Js Ly) Ng(Lh Mr Nt Pa Pe) Iq(Lw Mb Og Pz Qc) Mg(Iu Jo Lw) Po(Jn Of) Nt(In Jm) Me(Hv Iv) Mh(Hx Ml) Hu(Jk Pa) FrMd NcPe IhIo IrJo JkOy} Fr{Nt(Hu Jn Jr Js My Nq) Iq(Hw In It Jo Lw) Hr(Hu My Ng Oy) Po(Hu Mv Of) Mr(Hu Lw Mh) Nf(Hu Mv Nc) Jo(Jt Na Qa) My(Jt Nb) Ng(Jt Me) In(Ih Of) Pa(Lw Mk) NoJn MdLj NcPe HxOy} Nd{Nh(Hv Hw Ij In Jt Lj Nr Qd Qe) Po(Hv Jn Js Na) Lw(Mz Nl Qd) Nc(Lv Md Na) Ne(Md Mn Nx) Nt(Io Jm) Ng(Ma Pg) Ni(Nk Nl) Qd(Mh Nx) LvIh MzNl} Po{Hr(Hw Ir Mz Pe) In(Hv Hw Ir Iv) Of(Mb Mh Mu Qa) My(Hq Lw Ns) Mg(Mr Pe) Mu(Hu Mv) Og(Ir Mz) NtLy MbNj MhIl MvJq NcNi} Jj{Lu(Hr Lz Mx Na Nu Qd) Mb(Lv Mk Mx Qd) Lw(Ir Nb) Mv(Hv Na) Nk(Hr Ni) In(Lj Qd) LvMx NaNx NbJs QeJn} Pa{Mu(Hu Hw Lw Nf Of) Nj(Hv Hw Iq Mz Nt) Il(Ma Mz Qa) Mk(Lw Nx) Ng(Jk Mn) Hr(Ir Mz) Og(Nv Nx) MgJk} Ma{Ng(Ij It Iu Md Me) Nl(Ii Ij In Nb Nx) Ns(Nu Oz) Mj(Ih Lz) Lj(Jk Nq) FpMb MfMx MgMn MhIi} Mg{Jk(Ir Iv Li Mh Mi Mn Nb) Nv(Ii Mr Nb Pe) Jn(Lh Mr Pe) Lw(Ii Iu) NqIv MnNx LiOf} Og{Nr(Jn Me Nv) Mv(Hw Iu Nb) Jk(Mb Na Nx) Lw(Hx Ih) Me(Jn Jq) Nv(Ir Iv) MiNx NcIi HxJn} Nt{Mu(Hu Jn Js Mt) Jm(Jr Nj Qa Qb) Nj(Iq Mz) Io(Nv Qb) MvNg JoLi} Jo{Ir(Ii Lh Nx) Pe(Hw Jk Qa) Mr(Jk Ly) Lh(Js Mz) HqOk IqPf} Lw{Pe(Jn Mq Nu) Nc(Hv Io) FpHw LzHv MeIv MhMx MrMu LhOy} Mb{Md(Lj Nc Qb) Mh(Jn Nv) Ih(Lv Nj) Iq(Jr Oh) MnNh} Me{Mf(Ir Jn) Io(Iv Pe) Oy(Nb Pe) LuIr MyMz NgIi} Mu{Hu(Md Mr Nf No Pe) Nb(My Of) HxOy} Io{Nv(Hr Jt Lj) Jn(Hr Iu) MiQb MxNc} Ng{Jk(Mz Nv Nx) Jh(Jt Na) LyLh} Nq{NrJn MyIi NaNc HuNx} Mr{Hr(Ir Mz) MjJn InJs} Na{MdNc MnNh NfNj} Ir{Jk(Oy Pz) HrPe} Lh{MjMz IhIn JkOy} Nb{MsNw MwJh} Iq{Pf(Ih Qd)} Jr{NsPd MiOh} NoMjJt NrHrJn MkOmOz MqOkaA MvMyPe MxIiOy NfNlNw Constrained panels with 3 analytes, where 1.0E-5 >= 'AUC p-value' > 1.0E-6. Contains 1,466 panels of 287,980 total panels evaluated. : Jg{Ms(Fp Fr Hw Hx Ii Ir Iv Js Lh Lu Lx Mr Mu Mz Nb Nc Ne Nv Nx Pe Po Qa Qe) Hu(Fp Hv Hw Ih Im In Iq Iv Jk Jn Js Mi Mr Mz Nd Nf Nh Nl Nr Qe) My(Fp Hv Hw Hx Ij Im In Iv Jk Jo Lz Mx Na Nf Ng Nr Qd Qe) Ns(Fp Hv Hw Im In Iq Jo Js Jt Lz Mq Mx Na Nf Nl Qd Qe) Oy(Fp Hq Hr Hv Hx Ij In Jo Jt Lz Mb Mx Na Nl Qd Qe) Im(Hr Hv Hw Ii In Iq Jo Jt Mj Mx Na) Nf(Hw Iv Lz Mv Nc Ne Nl Nr Nt Pa) Iq(Hv Hw In Mb Mr Na Nr Nt Pe Qa) Ng(Hx Jt Mx Mz Na Nx Pz Qb Qe) Nc(Hr Ii Jo Lu Mi Mz Nb) Mw(Ii Lx Mr Pa Pe Po) Lz(Hv Ij In Mb Na) Ii(Hx Lj Ml Nl Ny) Jn(Hw Iu Mr Nr Nt) Mz(Md Ml Mv Pb) Nd(Fp Jm Jo Jt) Nt(Il Jr Js) Nl(Lu Nb Po) Lj(Hx Pg Po) Oe(Hx Jk Nb) Ni(Iu Nk) Js(Iu Pa) LxOf MbQb MeIv MhHv MiMv IrJo QaPa} Im{Mm(Hr Hw Hx Ii Ij In It Jk Jt Lj Lv Mb Me Mj Ml Na Nf Nr Qb Qe) Jp(Hv Hw Ii Ij In Iv Jk Js Jt Li Md Mi Mj Nb Nf Nr Qa) Nm(Hx Ih Iq Jk Jn Js Lu Lz Md Mx Ne Nf Ng Oi Qa Qb) Ik(Fp Hq Hx Li Lu Mk Mr Mv Mx Pd) Po(Hu Iq Ir Iv Jn Js Mh Nf) Lw(Hw Hx Jk Lj Mz Nb Nf Oi) Nl(Hr Ij In Lv Mx Na Qe) Jn(Jk Mr Nd No Nr Pa Pe) Oi(Hx Ip Mx Nb Nr Nt Pd) Pa(Il Jm Jr Js Mb Md) Nd(Fp Ir Iv Qa Qe) Ii(Lj My Of Oy Qa) Og(Hr Hx Mj Nb Qe) Md(Ir Iv Mr Nr) Iq(Lv Lx Nt Pe) Jk(In Js Lj Lz) Hr(Ip Nb Nr) Jt(Lx Mg Mu) Mn(Hv Ne) Mz(No Nt) Na(Ip Mh) NsPd MbQa MeHv MgJo MuNb NiNk IjIp JqaA JsPe} Ik{Jk(Hu Ii Iq Js Lj Lz Mb Mf Mh Mi Mj Mk Mz Na Ng Nh Nr Nx Oz Qd) Fp(Iq Jt Mh Mi Mj Mk Mn Nh Nl Nr Nx Qd Qe) Pg(Hw Iq Ir Jn Li Lj Mj Mz Nf Nm Nr) Ii(Ih Lj Lw Nc Ne Nj Nl Pa) Lz(Jp Lv Mm Mn Mz Nh Qe) Nr(Ij Mz Nc Nh Nx Qe) Oz(Jq Mm Nm Nx Qb Qe) Mk(Ij Ip Mm Mz Qb) Nh(Ip Mh Nx Pa Qe) Mj(Li Nc Nj Pe)

Figure 43 Continued

Mn(Hx Mh Mx Nl) Hq(Jn Mm Mx Nc) Nv(Hv Jo Js Mi) Pa(Jp Lj Lv Qe) Ip(Mv Nu Qd) Io(Iq Mi) Qd(Qb Qe) Li(Na Ne) Nolv NuJp MmPd MrPb NlNx JnJo} Ip{Jk(Hu Hv Ih Jn Js Mb Na Ne Nf Nh Nl Nm) Iq(Hv Ii Ir Md Nb Nt Pa Pe Qa) Mb(Fp Iv Js Lj Lu Mx Pa Qb) Mn(Hr Hv Hw Ij In Js Lz Mj) Nd(Ij In Jt Me Nb Nf Ni Nj) Pa(Hv Jn Jr Js Li Md Nf) Nq(Hv Js Na Ne Nl Oi) Nb(Jn Js Ms My Nf Nl) Lw(Lu Ne Nl Og) Md(Ir Iv Lj Nj) Ii(Jn Js Nl Oy) Jo(Mg Nc Og Pb) Mz(Hw Nr Pe) Nf(Mr Nj Pb) Hr(Mh Og Pe) Nm(Ne Nl) Me(Hv Iv) Mv(Nc Og) Jn(Hw Pe) Oi(Fp Qe) Pb(Hv Oz) NsPd NtIo LuNc MhIn MwMy} Nd{Nc(Hv Ii Ij In Jk Mj Nb Nr Nx Qd Qe) Nl(Ii Ij In Jn Nb Nr Nx Qd Qe) Nm(Ii Jp Lj Mh Mx Nf Pz Qd) Ni(Ih Jp Mn Ne Nv Qb Qd Qe) Nh(Hr Hx Iq Mh Mi Mx Nf) Na(Jk Jp Mm Ne Qb Qd) Nb(Fp Hq Il Jp Ne Oy) Mm(Fp Hr Ml Ng) Ne(Jk Lj Ns Qd) Jp(Hv Ij In Mb) Ng(Ii Lw Nx) Nj(Ir Lv Qa) Qd(Hw Ij In) Jn(Iv Jm Qa) Lj(Nv Nx) Og(Ij Qe) NsNx LxHu HqIi HvNv IoIv IrJo JkJm} Mm{Lj(Hr Hx Ii Jk Jp Lu Lw Nb Ni Nx Pg) Ng(Ij It Jt Li Lv Ma Me) Ih(Hr Jk Jo Lu Md Mj Pg) Ni(Jk Jp Mg Nk Nl Qb) Fp(Ii Ij In Mb Na) Lz(Hr Ij In It Na) Mb(Iq Jk Qb Qe) Qd(Hr Jk Lu Nc) Nt(Hw Jo Na) Me(Iv Jk Qb) Iq(Jo Nf Nr) Jt(Lu Pc Qb) Md(Og Qe) Mx(Hu Mf) NsMq LuJo LvPz LwMl MgMn MkPa MrNf MsNb JkOy} Nm{Ng(Fp Hw Hx Il Ir Iv Jp Js Li Lu Mn Mv Mx Nb Ne Nh Nl Nr) Nc(Hv Hw In Jn Js Lu Mx Nf Nr Qb Qd) Jp(Fp Ih Lu Md Mx Ne Nl Nv Pg) Jo(Hx Iv Jk Js Nr) Og(Hq Il Mv Na Nf) Oi(Hw Ii Nb Nr Nt) Io(Hq Lj Ne Nl) Lu(Jn Qa Qb) Ih(Fp Lx Mh) Md(Fp Qb) MgQd MhJs MkPa InIv IqQc PzJk} Lx{Hu(Hr It Jm Mx Ni Ns Pf Pg Po Qa) Mz(Lw Ml Mu My Nc Ng Of Pb) Mh(In Mp Mr Nb Nf Pf Pg) Nb(Hx Lw Ml Nc Pb) Nf(Lw Md Nc Ng Ny) Iq(Iv Jm Jt Mb Na) Ih(Hv Hw Ij In) Jm(Ij Pe Po Qe) Of(Hr Mu Ni) Pb(Hv Hx Nr) Pg(Ij Lw Mb) Ns(Ml Pd) In(Jo Ny) Jp(Ni Nr) Jt(Jo Mi) LwIv MbLi MvNy MyPf HqPd} Pb{Nr(Hw Ih In Js Li Lv Mi Qd) Nb(Hv Jn Lw Mx Mz Ne Nt Oi) Hq(Hw Ir Iv Mb Mz Na Nx Ny) Nf(Jk Nt Nv Oz Pa Pg) Ii(Ih Jo Mb Ni Nt Qd) Pg(Hr Hv Ij In Jo) Jk(Ij In Iv Mq) Mr(Ly Md Na) Hw(Fp Ih Qd) Nx(Hv Lu Mh) Pa(In Md Ni) Nv(Hr In) MaPd MzOi HxJp IhPe IjOz} Og{Ii(Hq Hu Ih Iq Ir Js Mi My Mz Nf Oy Pe) Jk(Hr Hv Hw Hx In Jt Li Lj Lw Mh Mi Nf) Hx(Jp Li Me Mn Mv) Nx(Iu Iv Nf Nr Qe) Nv(Hr In Mz Nf) Pa(Jp Mv Na Qa) Nt(Io Nc) Mz(Lh Pe) Hr(Mn Qb) Qe(Lw Mb) NqIj LyMr MvJt} Oi{Ih(Ii Ir Lh Mh Mv Na Nq Nx Pg) Lj(Hq Hr Hx Mb Md Mx Nc Of Oz) Mz(Iq Ir Ml Nq Nr Pe Po) Fp(Jt Nb Nq Nx) Mn(Iu Iv Lw Nc) Qe(Iq Jp Mb Nx) Nq(Nc Nr Nx) Nb(Hr Lw Po) Hx(Hr Jp) Iv(Jk Jp) Qb(Mv Nr) NtLy NfIr HwJk IqLh} Po{Of(Hv Hw Ij In Ir Jn Lw Na) Hr(Iq Iv Jo Mr Nf Pa Qa) Ns(Hw Hx Lw Mh Ml Nc) Jo(Hw Ir Iv Jt Mg Pe) Ny(Hx Mg Mh Ml My) Lw(Hq Iq Ir Lj) Mg(Iv Jt) My(Nu Pf) NtIl MbIq MdIj MeIv MhMk MlHv IhIn} Jp{Pz(Iq Iu Mi Mr Mv Nb Nr Pa Qe) Mb(Jk Mh Qb Qd) Io(Iu Iv Jt Ne) Nc(Hr Lu Nq) Ng(Jk Lh Pa) Ii(Hx My Ny) Nt(Ir Jm) Na(Jj Jk) Nb(Of Oy) Lj(Nq Nv) Pa(Hv Mk) NsPd LzNx MgJo MhIh MnNe HuJk HwJn} Nt{Jo(Ir Jn Jr Js Mz Nf Qa) Mg(Io Ir Jt Nx) In(Ir Jn Jr Js) Ng(Jk Li Mn) Nj(Io Md Nf) Fr(Iq Mz) Nc(Nk Nl) Ir(Hr Io) Jm(Jn Me) Ny(Il Oy) MbIq MuMz} Ii{Mg(Hx Me Ml My Nq Of Oy) Oy(Jk Mn Mv Mz Ny Qa) Of(Mn Mz Ny Qa) Nc(Jn Mz Nf) Ng(Jk Li Nv) Jo(Hw Iv Na) In(Ih Ir) MeIo MxHu HrIr JqPa} Lw{Pa(Io Jn Jr Lj Mx) Lu(Li Mh Nc Qb) Qa(Jn Nb Nf Nr) Ny(Ir Iv Jn Lj) Fp(Ih Iu Jk) Iq(Mr Nr Pe) Pe(Js Of) NrJn MgJo MzLh JkOy} Na{Jj(Fp Hu Nh Pd Qd Qe) Md(Lj Mh Mn Qb) Mn(Mh Ne Nl) Ng(Jk Nv Ny) Nq(Ih Qb) Lz(Jn Nc) Iq(Nv Pg) Pa(Mu Ny) LuNj NcJk ItJn JoPe} Nc{Ni(Fp Ih Jk Li Mx Nv Pa Qb Qd Qe) Io(Ih Iq Iv Jt Mi Pa Pg) Nq(Hv Ij) LvMb LyPa MdMh MgPe MrNk MzNy} Mb{Md(Fp Ih Ne Nl) Lz(Jn Nv Qa) Iq(Nj Pe Pg) Lj(Jj Nv Pg) Nq(Ih Nh) Mh(Pg Qa) Mn(Ne Nl) NgJk NhQb QdPa JnLi} Hr{Ir(Jk Lh Lu Mz Nf) Pe(Iq Js Mz Qa) Jj(Hu Nj Qd) Mz(Hw Lh) Qa(Mr Pa) Jn(Oz Pa) MuOf IhNy IoJq IqPz} Jk{Mg(Hv Ij In Jo Jt Mj) Ng(Js Mh Mr) Oy(Mi Nx Qb) Hu(No Qa) Pz(Iq Li) MaQd MzNj IhIo IrJo} Ny{Of(Lh Mr Mz Nf Pa Pe) Oy(Lh Mk Mr Nb Pa Pe) Pa(Mk My Oe) Mz(Ml Mu) NgHw IjIr} Nq{My(Hx Nb Nx) Hw(Jn Js Nj) Hu(Ij Qb) Jn(Iv Oz) Js(Nr Oz) Nx(Mg Oy) MzOy NfNj} Mu{Mz(Md Ml Mr Mv My Of Pa Pe) Nb(Hu Ms) Of(In Nf) NsPd MxHu IqIv} Me{Hv(Ir Jj Md) Mf(Jq Qa) Nb(Io My) MrNg MzIv IoJq LhOy} Nb{Fr(Ms Mv Of) Oy(Nj Qa Qb) MaMs MzNj NgNv} Jo{Mg(Li Mn Nv) Mr(Lv Qa) Jn(In Pe) QaPa JtOm} Iq{Qc(Jn Lv Nx Qb) Jr(Lj Qd) NjLj} In{Mr(Md Mz Nf) Nf(Pa Pe) FrNl} Mg{Jt(Li Mn) Nx(Mv Pa) MiJq} Ma{FrHu MjQd NiNk JtPc} Nj{Pa(Jn Jr) NiIh JjJq} Ng{Li(Nv Of) NvPa} Jj{Mx(Nh Nu) JqOz} Oy{Mv(Mr Nr) NxPa} Fr{NlIj HxOf} NsQaPd MdHxJq MzQcQe IhIoNv Constrained panels with 2 analytes, where 1.0E-6 >= 'AUC p-value' > 0. Contains 845 panels of 7,260 total panels evaluated. : Jj(Et Fr Hq Hw Hx Ih Ii Il Im Ip Iq Ir Is Iu Iv Jg Jh Ji Jk Jl Jm Jn Jo Jq Jr Js Lh Li Lu Lx Lz Ma Md Mh Mi Mm Mn Mp Mr Mt Mu Mv Mw Mz Nc Nd Nf Nl Nm Nn No Nq Nr Nt Nv Nw Nx Ny Of Oh Ok Om On Pa Pe Pf Pg Po Qa Qb Qe) Jh(aA Et Fr Hu Hw Ih Ik Im Ip Iq Ir Is Iv Ji Jl Jn Jq Jr Js Lh Li Lj Lw Lx Lz Mg Mh Mi Mp Mr Ms Mx My Mz Na Nc Nd Nf Ng Nl Nn No Nr Nt Nw Ny Og Oh Oi Ok Oy Pa Pe Pf Po Qa Qb Qd Qe) Mw(aA Et Hu Hw Ih Ik Im Ip Iq Ir Is Iv Ji Jl Jn Jq Jr Js Lh Lj Lw Lx Lz Mg Mh Mi Mp Mr Ms My Mz Na Nc Ne Nf Ng Nl No Nr Nt Nw Og Oh Oi Ok Oy Pa Pb Pe Pf Qa) Mu(aA Et Fr Hv Hw Ih Ik Im Iq Ir Is Ji Jl Jn Jo Jq Jr Js Lh Li Lj Lw Lx Lz Mh Mi Mp Mr Mt Na Nd Nf Ng Nm Nn No Nr Nw Ny Og Oh Oi Ok Om Pa Pe Pf Qa Qb Qe) Oh(Et Fr Hr Hv Hw Hx Ii Ij Im In Ip Iq Ir Iv Jg Jk Jn Jo Jp Jq Jr Js Lh Lu Lw Lx Mb Md Mr Mz Na Nb Nc Ne Nf Nm Nr Nt Nv Nw Ny Oi Om Pa Pc Pe Pf Po Qa) Mp(aA Et Fr Hr Hv Hw Ii Ij Im In Iq Ir Is Iv Jg Jl Jn Jo Jp Jq Jr Js Lh Lx Mg Mh Mr Mt Mz Na Nb Nc Nf Ni No Nr Nt Nw Ny Oi Ok Om Pa Pe Pf Po Qa) Om(aA Et Fr Hu Hw Ih Ik Im Iq Ir Is Iv Jl Jn Jq Jr Lh Lj Lx Lz Mg Mr Ms Mt Mv My Mz Nc Nd Ne Ng Nl Nn No Nt Nw Of Og Ok Oy Pa Pb Pe Pf Qa) Ma(aA Hr Hv Hw Hx Ih Ii Ij Ik Im In Ip Iq Ir Iv Jn Jp Jq Jr Js Jt Lh Lw Mb Md Mh Mr Mx Mz Na Nb Nc Ne Nf Nr Nt Nx Oi Pa Pe Qa Qb Qe) Nn(aA Et Hv Hw Ii Im In Iq Ir Is Iv Ji Jl Jn Jo Jq Jr Js Lh Lx Mb Mr Mz Na Nb Nc Ne Nf No Nr Nt Nw Ny Oi Ok Pa Pe Pf Po Qa) Fr(aA Et Hv Hw Ij Im In Iq Ir Is It Iv Ji Jn Jo Jq Jr Js Lh Lj Lw Mb Mg Mr Mt Mz Na Nc Ne Nf Ng No Nr Nw Ok Pe Pz Qa) Jq(aA Et Hw Ii Im Iq Ir Is Iu Iv Jg Jk Jl Jr Lh Li Lu Lx Lz Mb Mh Mm Mr Mt Nb Nc Nd No Nr Nt Nw Ok On Pa Pe Pf Po) Et(aA Hw Io Iq Ir Is Iv Jl Jn Jr Js Lh Lu Lw Lx Md Mh Mr Mt Mz Nc Nd Ne Nf Nl No Nr Nt Nw Ny Pa Pe Pf Po Pz) Lx(Hq Hv Hw Ij Ik In Ip Iq Ir Is Jg Ji Jn Jo Jp Jr Js Li Lj Lw Ly Mb Mm Nc Ng Nm Nr Nw Ny Og Ok Oy Pf Qa) Nw(aA Hv Hw Ij Im In Iq Ir Is Iv Jl Jn Jo Jr Jt Lh Lw Mb Mr Mz Na Nc Nd Nr Nt Og Oi Ok Pe Pf Qa) Pf(aA Hv Hw Ii Ik Im In Ir Is Iv Jg Ji Jn Jo Jr Js Lh Lw Mb Mr Mz Na Nb Nf Nt Ny Pa Pe Qa) Jl(aA Ik Im Io Iq Ir Is Jg Ji Jn Jr Lw Md Mt Mz Nf Og Oi Ok Pz) On(aA Hu Ik Im Io Is Ji Jn Mg Ms My Ng No Og Oi Ok Oy Pb Pz) Jr(Ii Im Jg Jk Lh Lw Mb Mm Mr Mt Mz Nd Nm No Nr Ny Pe Po) Mt(aA Hw Ik Ir Is Iv Lh Lw Mb Mr Na No Nt Oi Ok Pe) Mm(Ir Is Iv Jn Lh Mh Mr Mz Nb Nx Ny Pa Pe Po Qa) Jg(aA Ik Ip Lu Md Mg Mz No Og Oi Pa Po Pz Qa Qb) Ok(aA Hr Ik Im Is Ji Mg Mq Nd No Oi Pa Pb Pz) Ji(aA Hw Im Io Iq Mr Nd No Nt Nx Pa Pe) Is(aA Ik Io Lh Lw Mr Mz Nf No Oi Pe) Po(Ik Ip Jn Js Og Oy Pb) Nd(Jn Lv Lw Md Nh Ny) Pb(Ii Ir Lh Nr Ny Pe) Im(Lh Nv Nx Ny Pg) Lw(aA Hv Iq Jn) No(Hr Mb Ms) Oi(Li Nv Ny) aA(Ip Me Nj) Nq(Jn Js) Jp(Ip Mh) NmMg NtIk NjPa JoLh NyOg Constrained panels with 2 analytes, where 1.0E-5 >= 'AUC p-value' > 1.0E-6. Contains 154 panels of 7,260 total panels evaluated. : Jg(Fp Hv Hw Ih Ii Im In Iq Ir Iv Jn Js Lh Lw Lz Mh Mi Mr Mx My Nc Nd Ne Nf Nl Nr Ns Nt Nv Oy Pe Pg Qd) Mm(Fp Hv Hw Hx Ih Ii In Ip Js Jt Lw Md Mi Na Nc Nf Nr Nt Oi Pg Qd Qe) Jj(Fp Hu Ij It Jp Lv Mx My Nb Ne Nh Pd Qd) Lx(aA Hu Ih Im Iv Jt Mh Na Nf Po) Lw(Im Ir Mr Mx No Ny Pe Po Qa) Ip(Im Ir Iv Li Mn Mr Mz Nc Pe) Po(Hx Im Mb Mu My Nm Qa) Ma(It Jk Jo Nd Nl Nm Qd) Im(Mh Nc Nl No Pa Pe) Fr(Ih Me Nl Nt) Ik(Ii Lh Nv Ny) Jp(Ii Nt Nx Qb) Jr(Hw Ir Iu Nb) Mu(Iv Mz Nt) Nc(Mz Ny Qa) Jn(Jk Nm No) Nq(Ij Nr) Nd(Mz Qa) Hr(Ir Pe) Ny(Ng Oy) Oi(Ir Jk) MbMd MrPb IiOg

Figure 43 Continued

Constrained panels with 2 analytes, where 1.0E-4 >= 'AUC p-value' > 1.0E-5. Contains 226 panels of 7,260 total panels evaluated. : Im(Hx Ii Iq Ir Iv Jk Jn Jp Js Jt Lz Md Mi Mj Mm Mr Mz Nb Nd Nm Nr Nt Qe) Ip(Fp Hx Ih Iq Jk Jt Lz Mh Mx Na Nb Nd Nh Nl Nm Nt Nx Pa Pg Qb Qd Qe) Jp(Fp Hv Hw In Ir Iv Jk Js Li Lw Md Mi Mm Mr Nb Nd Nf Nh Nm Nr Pg) Mm(Hr Ij Io Iq It Jk Jo Lj Lu Me Ml Mx Nd Ni Qb) Nm(Fp Iq Iv Mh Mz Nb Nc Nd Ng Nv Og Oi Pa Qb) Ny(Hw Iq Ir Iv Jn Mr My Mz Nl Nt Of Pa Pe) Lw(Fp Jj Js Lh Li Lz Mh Mi Mz Nv Qb Qe) Qa(Ii Iq Ir Jn Md Mr Mz Nb Nf Nt Nv Pa) Po(Iq Mh Mz Na Nc Nf Ng Nt Of Pa) Og(Ir Iv Jk Lh Mr Mz Nb Nr Pe) Nd(Fp Hv Ir Iv Ne Nl Qd Qe) Jj(Hr Hv In Jt Lj Mb Nu) Oi(aA Ih Iq Lj Mn Mz Qe) Nc(Hv Ii Mx Na Nb Pa) Ik(Ir Jk Li Pa Pe Pg) Jn(Hw Iq Ir Mb Nr Pe) Jg(Hu Jo Lj Mb Na) Lx(Jm Mz Ni Qd) Nq(Hv Hw Ir) Na(Ih Nv Pg) Ma(Mg Ng) Mb(Pg Qd) Mh(Nv Qd) Mn(Ir Nh) Mz(Li No) Lh(Hr Mg) Nx(Iq Mx) FpJk MdLi NbPb IiOy IoaA JoJq Constrained panels with 2 analytes, where 1.0E-3 >= 'AUC p-value' > 1.0E-4. Contains 268 panels of 7,260 total panels evaluated. : Nc(Fp Hq Hx Ij Iq Ir Li Lv Lw Mb Md Mh Mj Mn Nd Ni Nq Nr Nx Qd Qe) Nd(Hw Hx Ih Ii Ij In It Js Jt Li Lj Mh Mj Mx Na Nb Nf Nr Nx Qb) Nm(Hv Hw Hx Ih Ii Jk Js Lu Lz Md Mx Na Ne Nf Nl Nr Pg Qd Qe) Mn(Fp Hv Hw Ij In Iq Js Lu Lz Md Mh Mj Mx Na Ne Nl Nr Qd) Jk(Hv Ih Iq Ir Iv Js Li Lj Lw Mb Md Mh Mi Mz Na Nf Ng) Pg(Hv Hw Ih Ir Iv Jn Js Li Lw Mz Nb Nf Nr Pa Qa) Mb(Fp Ih Im Ip Iq Jp Js Li Lz Mh Mm Nh Nl Qb Qe) Ip(Hr Hv Hw Ii Jn Js Lu Lw Md Mv Ne Nf Nr) Jp(Hr Hx Ih Ij Iu Jo Jt Lu Lz Mx Na Nl Qe) Nv(Hv Hw Iq Ir Iv Jn Jo Js Mi Mz Nf Nr Pa) Nq(Fp Ih In Iv Lj Mh Mq Mz Na Nh Nl Oi) Im(Hr Hv Hw Ij In Li Na Nf Oi Oz Qd) Qb(Hv Ij In Jn Jt Lu Md Mh Na) Lw(Hw Hx Iv Lu Nl Nr Pa Qd) Mz(Ir Lh Ml Nr Pb Pe) Nx(Ih Js Lz Nl Qd Qe) Na(Hq Jj Li Pa Qe) Ii(Iq Jn Lj Ng Of) Ir(Lz Mr Nf Pe Po) Fp(Ih Ik Md Oi) Li(Ih Lu Nt Pa) Po(Ih Iv Ny) Md(Hv Lj Mh) Mx(Hq Ij Nr) Jn(Lu Mr Pa) Iq(Lv Pe) Og(Hx Qe) Oz(Ij Jq) Pa(Jr Nh) NoaA NrNy LzMm MeHv MgPe NbIk NgJg Constrained panels with 2 analytes, where 1.0E-2 >= 'AUC p-value' > 1.0E-3. Contains 227 panels of 7,260 total panels evaluated. : Nl(Hq Hr Hx Ii Ij In Lj Lv Mh Mj Mv Na Nb Nf Qe) Md(Hx Ih Iq Iv Js Lw Lz Mx Na Nr Nt Pa Qd Qe) Ih(Hv Hw Hx Ii Ij In Iv Lv Lw Mh Mj Nr Pe) Li(Hv Hw Hx Ii In Ir Iv Jn Jo Js Nb Nf Nr) Lj(Hq Hx In Iu Lu Lv Lw Mb Mn Na Nb Nc Pa) Nc(Hr Hw In Iu Jt Lu Lz Mq Mv Nf Pd) Qd(Hv Hw Hx Ii Ij In Jk Na Nb Nf Nr) Iq(Hx Ij Ir Lh Lz Mz Na Nr Nt Pa) Mb(Iv Lu Lv Mn Mv Mx Ne Nm Nq) Nt(Io Ir Jn Jr Js Lw Mz Nf) Mh(Hq Hr Hv Ij Jt Na Nx Pd) Nh(Hx Iv Jn Lw Ne Nh Of Oi) Ii(Hx Iv Js Lw Lz Ml My Nh) Jk(Hu Hw In Jo Jt Lz Mj Nr) Pa(Hv Hw Ir Iv Jo Js Mz Ni) Ik(Hq Ij Iv Mr Mv Mx Pd) Qe(Hv Hw Ij In Jn Ne Nf) Nd(Hr Lz Me Ml Ni Nj) Ne(Ij Lv Lw Mv Nq) Iu(Fp Mn Mz Nq Nx) Js(Hw Hx Lz Mr Nr) Jo(Im Ip Pg Qb) Fp(In Jt Na) Mn(Hr Mv Ni) Mz(Hw Iv Mr) Nf(Lw Nj Pe) Hx(Ir Jn Na) Ij(Ip Lz Og) Iv(Ir Me) Jn(Hq Lh) Oi(Jt Nr) NqHr LvNh LyMr MvNa HwPb InIp QbPd Constrained panels with 2 analytes, where 5.0E-2 >= 'AUC p-value' > 1.0E-2. Contains 88 panels of 7,260 total panels evaluated. : Ih(Hq Hr Iq Jo Jt Lu Lz Mv Nb Ni Pd) Nb(Iq Js Lz Md Ms My Nf Oy) Jo(Lw Md Mg Nc Nd Pb Qd Qe) Hv(Hq Iq Iu Lu Lz Mx Oz) Nf(Iq Iv Mr Nh Nr Pa) Lu(Ij Jt Lv Nl Qd) Lz(Hx It Iv Jt Na) Mb(Hq Iu Mj Nd Pd) Hr(Lj Lv Ne Qd) Iq(In Iv Jt Mr) Iu(Jn Js Mh Mx) Mj(Lv Md Ne) Hq(Ij In Js) Mh(In Mv) Mi(Iv Na) Mx(Mf Na) Hw(Iv Md) Jt(Mg Ng) NsPd NuIk NiNl IjLj JsOz

Figure 43 Continued

METHODS AND COMPOSITIONS FOR DIAGNOSIS AND PROGNOSIS OF RENAL INJURY AND RENAL FAILURE

The present invention is filed under 35 U.S.C. §371 as the U.S. national phase of International Application No. PCT/US2011/026384, filed Sep. 26, 2011, which designated the U.S. and claims the benefit of priority to U.S. Provisional Patent Application No. 61/308,861 filed Feb. 26, 2010, which is hereby incorporated in its entirety including all tables, figures, and claims.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety.

TABLE 1

| Type | Risk Factors |
|---|---|
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |

TABLE 1-continued

| Type | Risk Factors |
| --- | --- |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, Curr Opin Nephrol Hypertens 14:265-270, 2005 and Chertow et al, J Am Soc Nephrol 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., Crit Care. 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, Crit. Care Med. 36: S141-45, 2008 and Ricci et al., Kidney Int. 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of a plurality of assays, wherein one or more of the assays is configured to detect one or more of the biomarkers listed in Table 2 herein (collectively referred to herein as "kidney injury markers, and each individually as a "kidney injury marker") The plurality of assays are combined to provide a "biomarker panel approach" which can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury). Preferred biomarker panels comprise two, three, four, five, or more assays configured to detect two, three, four, five, or more of the biomarkers listed in Table 2 herein.

These kidney injury markers may be used in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more kidney injury markers of the present invention in a body fluid sample obtained from the subject. A plurality of assay results, for example comprising a measured concentration of one or more markers selected from the group consisting of the markers listed in Table 2 herein are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay results, for example comprising a measured concentration of one or more markers selected from the group consisting of the biomarkers listed in Table 2 herein are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result (s0 is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay results, for example a measured concentration of one or more markers selected from the group consisting of the biomarkers listed in Table 2 herein are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay results, for example a measured concentration of one or more markers selected from the group consisting of the biomarkers listed in Table 2 herein are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test or combination of tests to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1−specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

As previously noted, preferred biomarker panels comprise two, three, four, five, or more assays configured to detect two, three, four, five, or more of the biomarkers listed in Table 2 herein. That said, the foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

BRIEF DESCRIPTION OF THE FIGURES

FIGS. 1-43 provide a detailed summary of the ability of panels of biomarkers to evaluate acute kidney injury in an ICU patient population. Patients in the population are divided based on the RIFLE classification of renal status. The following analyses are provided:

FIG. 1. No or R RIFLE stage versus RIFLE I or F. RIFLE stage adjudicated by sCr and Urine Output. Diseased group sample is obtained 24 hours prior to RIFLE I diagnosis.

FIG. 2. No or R RIFLE stage versus RIFLE I or F. RIFLE stage adjudicated by sCr. Diseased group sample is obtained 24 hours prior to RIFLE I diagnosis.

FIG. 3. No or R RIFLE stage versus RIFLE I or F. RIFLE stage adjudicated by Urine Output. Diseased group sample is obtained 24 hours prior to RIFLE I diagnosis.

FIG. 4. No RIFLE stage versus RIFLE R, I, or F. RIFLE stage adjudicated by sCr and Urine Output. Diseased group sample is obtained 24 hours prior to RIFLE R diagnosis.

FIG. 5. No RIFLE stage versus RIFLE R, I, or F. RIFLE stage adjudicated by sCr. Diseased group sample is obtained 24 hours prior to RIFLE R diagnosis.

FIG. 6. No RIFLE stage versus RIFLE R, I, or F. RIFLE stage adjudicated by Urine Output. Diseased group sample is obtained 24 hours prior to RIFLE R diagnosis.

FIG. 7. No, R, or I RIFLE stage versus RIFLE F. RIFLE stage adjudicated by sCr and Urine Output. Diseased group sample is obtained 24 hours prior to RIFLE I diagnosis.

FIG. 8. No, R, or I RIFLE stage versus RIFLE F. RIFLE stage adjudicated by Urine Output. Diseased group sample is obtained 24 hours prior to RIFLE I diagnosis.

FIG. 9. No or R RIFLE stage versus RIFLE I or F. RIFLE stage adjudicated by sCr and Urine Output. Diseased group sample is obtained at RIFLE I diagnosis.

FIG. 10. No or R RIFLE stage versus RIFLE I or F. RIFLE stage adjudicated by sCr. Diseased group sample is obtained at RIFLE I diagnosis.

FIG. 11. No or R RIFLE stage versus RIFLE I or F. RIFLE stage adjudicated by Urine Output. Diseased group sample is obtained at RIFLE I diagnosis.

FIG. 12. No RIFLE stage versus RIFLE R, I, or F. RIFLE stage adjudicated by sCr and Urine Output. Diseased group sample is obtained at RIFLE R diagnosis.

FIG. 13. No RIFLE stage versus RIFLE R, I, or F. RIFLE stage adjudicated by sCr. Diseased group sample is obtained at RIFLE R diagnosis.

FIG. 14. No RIFLE stage versus RIFLE R, I, or F. RIFLE stage adjudicated by Urine Output. Diseased group sample is obtained at RIFLE R diagnosis.

FIG. 15. No, R, or I RIFLE stage versus RIFLE F. RIFLE stage adjudicated by sCr and Urine Output. Diseased group sample is obtained at RIFLE I diagnosis.

FIG. 16. No, R, or I RIFLE stage versus RIFLE F. RIFLE stage adjudicated by sCr. Diseased group sample is obtained at RIFLE I diagnosis.

FIG. 17. No, R, or I RIFLE stage versus RIFLE F. RIFLE stage adjudicated by Urine Output. Diseased group sample is obtained at RIFLE I diagnosis.

FIG. 18. No or R RIFLE stage versus RIFLE I or F. RIFLE stage adjudicated by sCr and Urine Output. Diseased group sample is obtained 48 hours prior to RIFLE I diagnosis.

FIG. 19. No or R RIFLE stage versus RIFLE I or F. RIFLE stage adjudicated by sCr. Diseased group sample is obtained 48 hours prior to RIFLE I diagnosis.

FIG. 20. No or R RIFLE stage versus RIFLE I or F. RIFLE stage adjudicated by Urine Output. Diseased group sample is obtained 48 hours prior to RIFLE I diagnosis.

FIG. 21. No RIFLE stage versus RIFLE R, I, or F. RIFLE stage adjudicated by sCr and Urine Output. Diseased group sample is obtained 48 hours prior to RIFLE R diagnosis.

FIG. 22. No RIFLE stage versus RIFLE R, I, or F. RIFLE stage adjudicated by sCr. Diseased group sample is obtained 48 hours prior to RIFLE R diagnosis.

FIG. 23. No RIFLE stage versus RIFLE R, I, or F. RIFLE stage adjudicated by Urine Output. Diseased group sample is obtained 48 hours prior to RIFLE R diagnosis.

FIG. 24. No, R, or I RIFLE stage versus RIFLE F. RIFLE stage adjudicated by sCr and Urine Output. Diseased group sample is obtained 48 hours prior to RIFLE I diagnosis.

FIG. 25. Progression of RIFLE R to RIFLE I or F. RIFLE stage adjudicated by sCr and Urine Output. Sample is obtained at R diagnosis.

FIG. 26. Progression of RIFLE R to RIFLE I or F. RIFLE stage adjudicated by sCr. Sample is obtained at R diagnosis.

FIG. 27. Progression of RIFLE R to RIFLE I or F. RIFLE stage adjudicated by Urine Output. Sample is obtained at R diagnosis.

FIG. 28. No or R RIFLE stage versus RIFLE I or F. RIFLE stage adjudicated by sCr and Urine Output, within 48 hrs of enrollment. Sample is obtained at enrollment.

FIG. 29. No or R RIFLE stage versus RIFLE I or F. RIFLE stage adjudicated by sCr, within 48 hrs of enrollment. Sample is obtained at enrollment.

FIG. 30. No or R RIFLE stage versus RIFLE I or F. RIFLE stage adjudicated by Urine Output, within 48 hrs of enrollment. Sample is obtained at enrollment.

FIG. 31. No RIFLE stage versus RIFLE R, I, or F. RIFLE stage adjudicated by sCr and Urine Output, within 48 hrs of enrollment. Sample is obtained at enrollment.

FIG. 32. No RIFLE stage versus RIFLE R, I, or F. RIFLE stage adjudicated by sCr, within 48 hrs of enrollment. Sample is obtained at enrollment.

FIG. 33. No RIFLE stage versus RIFLE R, I, or F. RIFLE stage adjudicated by Urine Output, within 48 hrs of enrollment. Sample is obtained at enrollment.

FIG. 34. No, R, or I RIFLE stage versus RIFLE F. RIFLE stage adjudicated by sCr and Urine Output, within 48 hrs of enrollment. Sample is obtained at enrollment.

FIG. 35. No, R, or I RIFLE stage versus RIFLE F. RIFLE stage adjudicated by Urine Output, within 48 hrs of enrollment. Sample is obtained at enrollment.

FIG. 36. No or R RIFLE stage versus RIFLE I or F. RIFLE stage adjudicated by sCr and Urine Output, within 24 hrs of enrollment. Sample is obtained at enrollment.

FIG. 37. No or R RIFLE stage versus RIFLE I or F. RIFLE stage adjudicated by sCr, within 24 hrs of enrollment. Sample is obtained at enrollment.

FIG. 38. No or R RIFLE stage versus RIFLE I or F. RIFLE stage adjudicated by Urine Output, within 24 hrs of enrollment. Sample is obtained at enrollment.

FIG. 39. No RIFLE stage versus RIFLE R, I, or F. RIFLE stage adjudicated by sCr and Urine Output, within 24 hrs of enrollment. Sample is obtained at enrollment.

FIG. 40. No RIFLE stage versus RIFLE R, I, or F. RIFLE stage adjudicated by sCr, within 24 hrs of enrollment. Sample is obtained at enrollment.

FIG. 41. No RIFLE stage versus RIFLE R, I, or F. RIFLE stage adjudicated by Urine Output, within 24 hrs of enrollment. Sample is obtained at enrollment.

FIG. 42. No, R, or I RIFLE stage versus RIFLE F. RIFLE stage adjudicated by sCr and Urine Output, within 24 hrs of enrollment. Sample is obtained at enrollment.

FIG. 43. No, R, or I RIFLE stage versus RIFLE F. RIFLE stage adjudicated by Urine Output, within 24 hrs of enrollment. Sample is obtained at enrollment.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers.

In various embodiments, a biomarker recited in Table 2 herein, or one or more markers related thereto, is combined with one or more additional biomarkers listed in Table 2 herein and/or with one or more other biomarkers or clinical indicia, and the combination correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL ($\geq 8.8$ μmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl ($\geq 26.4$ μmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

In the case of polypeptide biomarkers used herein, a "marker" or "biomarker" refers to polypeptides present in a biological sample that are derived from a particular biosynthetic precursor. In the case of biomarkers that are not polypeptides (e.g., Hyaluronic acid), a "marker" or "biomarker" refers to the particular molecular entity recited.

The following Table 2 provides a list of preferred biomarkers finding use in the present invention. In the table, the "recommended name" for the biomarker precursor from the Swiss-Prot "UniProtKB" database, and for most polypeptide biomarkers the Swiss-Prot entry number for the human precursor. In the event that the assay detects a complex, the Swiss Prot entry is listed for each member of the complex.

TABLE 2

| Preferred Name | Swiss-Prot: | Preferred Name | Swiss-Prot: |
| --- | --- | --- | --- |
| 60 kDa heat shock protein, mitochondrial | P10809 | 72 kDa type IV collagenase | P08253 |
| 72 kDa type IV collagenase:Metalloproteinase inhibitor 1 complex | P08253 P01033 | 72 kDa type IV collagenase:Metalloproteinase inhibitor 2 complex | P08253 P16035 |
| 72 kDa type IV collagenase:Metalloproteinase inhibitor 4 complex | P08253 Q99727 | Adiponectin | Q15848 |
| Advanced glycosylation end product-specific receptor | Q15109 | Agouti-related protein | O00253 |
| Alkaline phosphatase, tissue-nonspecific isozyme | P05186 | Alpha-1-antitrypsin | P01009 |

TABLE 2-continued

| Preferred Name | Swiss-Prot: | Preferred Name | Swiss-Prot: |
|---|---|---|---|
| Alpha-1-antitrypsin:Neutrophil elastase complex | P01009 P08246 | Alpha-1-antitrypsin:Plasminogen complex | P01009 P00747 |
| Alpha-2 macroglobulin | P01023 | Alpha-2-HS-glycoprotein | P02765 |
| Alpha-fetoprotein | P02771 | Amphiregulin | P15514 |
| Amyloid Beta 40 | P05067 (aa672-711) | Amyloid Beta 42 | P05067 (aa672-713) |
| Angiogenin | P03950 | Angiopoietin-1 | Q15389 |
| Angiopoietin-1 receptor | Q02763 | Angiopoietin-2 | O15123 |
| Angiopoietin-related protein 3 | Q9Y5C1 | Angiopoietin-related protein 4 | Q9BY76 |
| Angiopoietin-related protein 6 | Q8NI99 | Anti-Cathepsin-G (ANCA) | NA |
| Antileukoproteinase | P03973 | Apolipoprotein A-I | P02647 |
| Apolipoprotein A-II | P02652 | Apolipoprotein B-100 | P04114 |
| Apolipoprotein C-III | P02656 | Apolipoprotein E | P02649 |
| Apolipoprotein(a) | P08519 | Appetite-regulating hormone | Q9UBU3 |
| Aspartate aminotransferase, cytoplasmic | P17174 | Bactericidal permeability-increasing protein | P17213 |
| Bcl2 antagonist of cell death | Q92934 | Beta-2-glycoprotein 1 | P02749 |
| Beta-2-microglobulin | P61769 | Beta-nerve growth factor | P01138 |
| Betacellulin | P35070 | Bone morphogenetic protein 7 | P18075 |
| Brain-derived neurotrophic factor | P23560 | C—C motif chemokine 1 | P22362 |
| C—C motif chemokine 13 | Q99616 | C—C motif chemokine 15 | Q16663 |
| C—C motif chemokine 17 | Q92583 | C—C motif chemokine 18 | P55774 |
| C—C motif chemokine 19 | Q99731 | C—C motif chemokine 2 | P13500 |
| C—C motif chemokine 20 | P78556 | C—C motif chemokine 21 | O00585 |
| C—C motif chemokine 22 | O00626 | C—C motif chemokine 23 | P55773 |
| C—C motif chemokine 24 | O00175 | C—C motif chemokine 26 | Q9Y258 |
| C—C motif chemokine 27 | Q9Y4X3 | C—C motif chemokine 3 | P10147 |
| C—C motif chemokine 4 | P13236 | C—C motif chemokine 5 | P13501 |
| C—C motif chemokine 7 | P80098 | C—C motif chemokine 8 | P80075 |
| C-Peptide | P01308(aa 57-87) | C-reactive protein | P02741 |
| C—X—C motif chemokine 10 | P02778 | C—X—C motif chemokine 11 | O14625 |
| C—X—C motif chemokine 13 | O43927 | C—X—C motif chemokine 16 | Q9H2A7 |
| C—X—C motif chemokine 2 | P19875 | C—X—C motif chemokine 5 | P42830 |
| C—X—C motif chemokine 6 | P80162 | C—X—C motif chemokine 9 | Q07325 |
| Cadherin-1 | P12830 | Cadherin-16 | O75309 |
| Cadherin-3 | P22223 | Cadherin-5 | P33151 |
| Calbindin | P05937 | Calcitonin | P01258 |
| Calcitonin (Procalcitonin) | P01258-Pro | Cancer Antigen 15-3 | NA |
| Cancer Antigen 19-9 | NA | Carbonic anhydrase 9 | Q16790 |
| Carcinoembryonic antigen-related cell adhesion molecule 1 | P13688 | Carcinoembryonic antigen-related cell adhesion molecule 5 | P06731 |
| Caspase-1 | P29466 | Caspase-3, active | P42574 |
| Caspase-8 | Q14790 | Caspase-9 | P55211 |
| Cathepsin B | P07858 | Cathepsin D | P07339 |
| Cathepsin S | P25774 | CD40 ligand | P29965 |
| CD44 antigen | P16070 | Cellular tumor antigen p53 | P04637 |
| Choriogonadotropin subunit beta | P01233 | Ciliary neurotrophic factor | P26441 |
| Clusterin | P10909 | Coagulation factor VII | P08709 |
| Collagenase 3 | P45452 | Complement C3 | P01024 |
| Complement C4-B | P0C0L5 | Complement C5 | P01031 |
| Complement factor H | P08603 | Corticotropin | P01189(aa 138-176) |
| Cortisol | NA | Creatine Kinase-MB | P12277 P06732 |
| Creatinine | NA | Cyclin-dependent kinase inhibitor 1 | P38936 |
| Cystatin-C | P01034 | Cytochrome c | P99999 |
| DDRGK domain-containing protein 1 | Q96HY6 | Dipeptidyl peptidase 4 | P27487 |
| E-selectin | P16581 | Endoglin | P17813 |
| Endostatin | P39060(aa 1572-1754) | Endothelial protein C receptor | Q9UNN8 |
| Endothelin-1 | P05305 | Eotaxin | P51671 |
| Epidermal growth factor receptor | P00533 | Epiregulin | O14944 |
| Epithelial cell adhesion molecule | P16422 | Erythropoietin | P01588 |
| Erythropoietin receptor | P19235 | Fatty acid-binding protein, heart | P05413 |
| Fatty acid-binding protein, intestinal | P12104 | Fatty acid-binding protein, liver | P07148 |
| Ferritin | P02792 P02794 | Fibrinogen | P02671 P02675 P02679 |
| Fibroblast growth factor 19 | O95750 | Fibroblast growth factor 21 | Q9NSA1 |
| Fibroblast growth factor 23 | Q9GZV9 | Fibronectin | P02751 |
| Follistatin | P19883 | Follitropin | P01215 P01225 |
| Follitropin subunit beta | P01225 | Fractalkine | P78423 |
| Galectin-3 | P17931 | Gastric inhibitory polypeptide | P09681 |
| Glial cell line-derived neurotrophic factor | P39905 | Glial fibrillary acidic protein | P14136 |

TABLE 2-continued

| Preferred Name | Swiss-Prot: | Preferred Name | Swiss-Prot: |
|---|---|---|---|
| Glucagon | P01275 | Glucagon-like peptide 1 | P01275(aa 98-127 aa98-128) |
| Glutathione S-transferase A1 | P08263 | Glutathione S-transferase P | P09211 |
| Granulocyte colony-stimulating factor | P09919 | Granulocyte-macrophage colony-stimulating factor | P04141 |
| Granzyme B | P10144 | Granzyme M | P51124 |
| Growth-regulated alpha protein | P09341 | Haptoglobin | P00738 |
| Heat shock 70 kDa protein 1 | P08107 | Heat shock protein beta-1 | P04792 |
| Heat shock protein beta-1 (phospho SER78/ phospho SER82) | P04792 (pS78/pS82) | Heat shock protein HSP 90-alpha | P07900 |
| Heme oxygenase 1 | P09601 | Heparan Sulfate | NA |
| Heparin-binding EGF-like growth factor | Q99075 | Heparin-binding growth factor 1 | P05230 |
| Heparin-binding growth factor 2 | P09038 | Hepatitis A virus cellular receptor 1 | O43656 |
| Hepatocyte growth factor | P14210 | Hepatocyte growth factor receptor | P08581 |
| Hyaluronic acid | NA | Hypoxia-inducible factor 1 alpha | Q16665 |
| Immunoglobulin A | NA | Immunoglobulin E | NA |
| Immunoglobulin M | NA | Immunoglulin G1 | NA |
| Immunoglulin G2 | NA | Immunoglulin G3 | NA |
| Immunoglulin G4 | NA | Insulin | P01308 |
| Insulin receptor substrate 1 | P35568 | Insulin-like growth factor 1 receptor | P08069 |
| Insulin-like growth factor IA | P01343 | Insulin-like growth factor-binding protein 1 | P08833 |
| Insulin-like growth factor-binding protein 2 | P18065 | Insulin-like growth factor-binding protein 3 | P17936 |
| Insulin-like growth factor-binding protein 4 | P22692 | Insulin-like growth factor-binding protein 5 | P24593 |
| Insulin-like growth factor-binding protein 6 | P24592 | Insulin-like growth factor-binding protein 7 | Q16270 |
| Intercellular adhesion molecule 1 | P05362 | Intercellular adhesion molecule 2 | P13598 |
| Intercellular adhesion molecule 3 | P32942 | Interferon alpha-2 | P01563 |
| Interferon gamma | P01579 | Interleukin-1 alpha | P01583 |
| Interleukin-1 beta | P01584 | Interleukin-1 receptor antagonist protein | P18510 |
| Interleukin-1 receptor type I | P14778 | Interleukin-1 receptor type II | P27930 |
| Interleukin-10 | P22301 | Interleukin-11 | P20809 |
| Interleukin-12 | P29459 P29460 | Interleukin-12 subunit beta | P29460 |
| Interleukin-13 | P35225 | Interleukin-15 | P40933 |
| Interleukin-17A | Q16552 | Interleukin-18 | Q14116 |
| Interleukin-2 | P60568 | Interleukin-2 receptor alpha chain | P01589 |
| Interleukin-20 | Q9NYY1 | Interleukin-21 | Q9HBE4 |
| Interleukin-23 | Q9NPF7 P29460 | Interleukin-28A | Q8IZJ0 |
| Interleukin-29 | Q8IU54 | Interleukin-3 | P08700 |
| Interleukin-33 | O95760 | Interleukin-4 | P05112 |
| Interleukin-4 receptor alpha chain | P24394 | Interleukin-5 | P05113 |
| Interleukin-6 | P05231 | Interleukin-6 receptor subunit alpha | P08887 |
| Interleukin-6 receptor subunit beta | P40189 | Interleukin-7 | P13232 |
| Interleukin-8 | P10145 | Interleukin-9 | P15248 |
| Interstitial collagenase | P03956 | Interstitial collagenase:Metalloproteinase inhibitor 2 complex | P03956 P16035 |
| Involucrin | P07476 | Islet amyloid polypeptide | P10997 |
| Keratin, type I cytoskeletal 19 (aa311-367) | P08727 | Keratin, type II cytoskeletal 1; type1 cytoskeletal 10 (Keratin-1,-10 mix) | P04264 P13645 |
| Keratin, type II cytoskeletal 6 (6A, -6B, -6C mix) | P02538 P04259 P48668 | Kit ligand | P21583 |
| Lactotransferrin | P02788 | Leptin | P41159 |
| Leukemia inhibitory factor | P15018 | Lipopolysaccharide (serotypes-K,-O) | NA |
| Lutropin | P01215 P01229 | Lutropin subunit beta | P01229 |
| Lymphatic vessel endothelial hyaluronic acid receptor 1 | Q9Y5Y7 | Lymphotactin | P47992 |
| Lymphotoxin-alpha | P01374 | Lysozyme C | P61626 |
| Macrophage colony-stimulating factor 1 | P09603 | Macrophage metalloelastase | P39900 |
| Macrophage migration inhibitory factor | P14174 | Malondialdehyde-modified low-density lipoprotein | NA |
| Matrilysin | P09237 | Matrix metalloproteinase-9 | P14780 |
| Matrix metalloproteinase-9:Metalloproteinase inhibitor 2 complex | P14780 P16035 | Matrix metalloproteinase-9:Metalloproteinase inhibitor 3 complex | P14780 P35625 |
| Metalloproteinase inhibitor 1 | P01033 | Metalloproteinase inhibitor 2 | P16035 |
| Metalloproteinase inhibitor 3 | P35625 | Metalloproteinase inhibitor 4 | Q99727 |
| Midkine | P21741 | Mix of Growth-regulated alpha, beta, and gamma proteins | P09341 P19875 P19876 |
| Monocyte differentiation antigen CD14 | P08571 | Mucin-16 | Q8WXI7 |
| Myeloid differentiation primary response protein MyD88 | Q99836 | Myeloperoxidase | P05164 |
| Myoglobin | P02144 | Neprilysin | P08473 |
| Netrin-1 | O95631 | Neural cell adhesion molecule 1 | P13591 |
| Neuronal cell adhesion molecule | Q92823 | Neutrophil collagenase | P22894 |

TABLE 2-continued

| Preferred Name | Swiss-Prot: | Preferred Name | Swiss-Prot: |
|---|---|---|---|
| Neutrophil elastase | P08246 | Neutrophil gelatinase-associated lipocalin | P80188 |
| NF-kappa-B inhibitor alpha | P25963 | Nidogen-1 | P14543 |
| Nitric oxide synthase, inducible | P35228 | NT-pro-BNP | P16860 |
| Osteocalcin | P02818 | Osteopontin | P10451 |
| Oxidized low-density lipoprotein receptor 1 | P78380 | P-selectin | P16109 |
| P-selectin glycoprotein ligand 1 | Q14242 | Pancreatic prohormone | P01298 |
| Pappalysin-1 | Q13219 | Parathyroid hormone | P01270 |
| Peptide YY | P10082 | Pigment epithelium-derived factor | P36955 |
| Placenta growth factor | P49763 | Plasminogen activator inhibitor 1 | P05121 |
| Platelet basic protein | P02775 | Platelet endothelial cell adhesion molecule | P16284 |
| Platelet factor 4 | P02776 | Platelet-derived growth factor A | P04085 P01127 |
| Platelet-derived growth factor subunit A (dimer) | P04085 | Platelet-derived growth factor subunit B (dimer) | P01127 |
| Poly [ADP-ribose] polymerase 1 (cleaved) | P09874 | Pro-epidermal growth factor | P01133 |
| Pro-Interleukin-1 beta | P01584-Pro | Pro-interleukin-16 | Q14005 |
| Prolactin | P01236 | Prostate-specific antigen | P07288 |
| Prostatic acid phosphatase | P15309 | Protein NOV homolog | P48745 |
| Protein S100-A12 | P80511 | Protein S100-B | P04271 |
| Protransforming growth factor alpha | P01135 | Renin | P00797 |
| Resistin | Q9HD89 | Serum albumin | P02768 |
| Serum amyloid A protein | P02735 | Serum amyloid P-component | P02743 |
| Sex hormone-binding globulin | P04278 | SL cytokine | P49771 |
| Somatotropin | P01241 | Stromal cell-derived factor 1 | P48061 |
| Stromelysin-1 | P08254 | Stromelysin-1:Metalloproteinase inhibitor 2 complex | P08254 P16035 |
| Stromelysin-2 | P09238 | Tenascin | P24821 |
| Thrombomodulin | P07204 | Thrombopoietin | P40225 |
| Thrombospondin-1 | P07996 | Thrombospondin-2 | P35442 |
| Thymic stromal lymphopoietin | Q969D9 | Thyrotropin | P01215 P01222 |
| Thyroxine-binding globulin | P05543 | Tissue factor | P13726 |
| Tissue-type plasminogen activator | P00750 | Transforming growth factor beta-1 | P01137 |
| Transforming growth factor beta-2 | P61812 | Transforming growth factor beta-3 | P10600 |
| Transmembrane glycoprotein NMB | Q14956 | Transthyretin | P02766 |
| Trefoil factor 3 | Q07654 | Tubulointerstitial nephritis antigen | Q9UJW2 |
| Tumor necrosis factor | P01375 | Tumor necrosis factor ligand superfamily member 10 | P50591 |
| Tumor necrosis factor ligand superfamily member 11 | O14788 | Tumor necrosis factor ligand superfamily member 6 | P48023 |
| Tumor necrosis factor receptor superfamily member 10B | O14763 | Tumor necrosis factor receptor superfamily member 11B | O00300 |
| Tumor necrosis factor receptor superfamily member 1A | P19438 | Tumor necrosis factor receptor superfamily member 1B | P20333 |
| Tumor necrosis factor receptor superfamily member 5 | P25942 | Tumor necrosis factor receptor superfamily member 6 | P25445 |
| Tumor necrosis factor receptor superfamily member 8 | P28908 | Urokinase plasminogen activator surface receptor | Q03405 |
| Urokinase-type plasminogen activator | P00749 | Vascular cell adhesion protein 1 | P19320 |
| Vascular endothelial growth factor A | P15692 | Vascular endothelial growth factor D | O43915 |
| Vascular endothelial growth factor receptor 1 | P17948 | Vascular endothelial growth factor receptor 2 | P35968 |
| Vascular endothelial growth factor receptor 3 | P35916 | Versican core protein | P13611 |
| Vitamin D-binding protein | P02774 | Vitamin K-dependent protein C | P04070 |
| von Willebrand Factor | P04275 | WAP four-disulfide core domain protein 2 | Q14508 |

Included in this list are a number of proteins which exist in one form as type-I, type-II, or GPI-anchored membrane proteins. Typically, such membrane proteins comprise a substantial extracellular domain, some or all of which can be detected as soluble forms present in aqueous samples such as blood, serum, plasma, urine, etc., either as cleavage products or as splice variants which delete an effective membrane spanning domain. These membrane proteins include Swiss-Prot entry numbers O14788, O14944, O75309, P00797, P05186, P08473, P13688, P15514, P22223, P27487, P35070, Q03405, Q14956, Q16790, Q99075, Q9Y5Y7Q15109, Q02763, P17213, P12830, P33151, P06731, P29965, P16070, Q9H2A7, P17813, Q9UNN8, P00533, P16422, P19235, P16581, P78423, O43656, P08581, P08069, P05362, P13598, P32942, P14778, P27930, P01589, P24394, P08887, P40189, P21583, P09603, P08571, Q8WXI7, P13591, Q92823, P78380, P16284, P01133, P15309, P01135, P16109, Q14242, P49771, P07204, P13726, P01375, P50591, P48023, O14763, P19438, P20333, P25942, P25445, P28908, P19320, P17948, and P35968. Preferred assays detect soluble forms of these biomarkers.

In this regard, the skilled artisan will understand that the signals obtained from an immunoassay are a direct result of complexes formed between one or more antibodies and the corresponding target biomolecule (i.e., the analyte) containing the necessary epitope(s) to which the antibodies bind. While such assays may detect the full length biomarker and the assay result be expressed as a concentration of a biomarker of interest, the signal from the assay is actually a result of all such "immunoreactive" molecules present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

As used herein, a "plurality" as used herein refers to at least two. Preferably, a plurality refers to at least 3, more preferably at least 4, even more preferably at least 5, even more preferably at least 10, and most preferably at least 20.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGel™ resins (Rapp Polymere GmbH), AgroGel™ resins (I.L.S.A. Industria Lavorazione Sottoprodotti Animali S.P.A.), polyethylene glycol and acrylamide (PEGA) gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ M$^{-1}$, and preferably between about $10^8$ M-1 to about $10^9$ M$^{-1}$, about $10^9$ M$^{-1}$ to about $10^{10}$ M$^{-1}$, or about $10^{10}$ M$^{-1}$ to about $10^{12}$ M$^{-1}$.

Affinity is calculated as Kd=koff/kon (koff is the dissociation rate constant, Kon is the association rate constant and Kd is the equilibrium constant). Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., J. Immunoassay 12: 425-43, 1991; Nelson and Griswold, Comput. Methods Programs Biomed. 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g., Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities. Assay Correlations Assay Correlations The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the $97.5^{th}$ percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1−specificity, the ROC graph is sometimes called the sensitivity vs (1−specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1−specificity)) of greater than 1, at least 2, more preferably at least 3, still more preferably at least 5, and most preferably at least 10; and or a negative likelihood ratio (calculated as (1−sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Cathepsin B (P07858); Ceruloplasmin (P00450); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr-corrected} = \frac{C_{cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:
Inclusion Criteria
males and females 18 years of age or older;
undergoing a radiographic/angiographic procedure (such as a CT scan or coronary intervention) involving the intravascular administration of contrast media;
expected to be hospitalized for at least 48 hours after contrast administration.
able and willing to provide written informed consent for study participation and to comply with all study procedures.
Exclusion Criteria
renal transplant recipients;
acutely worsening renal function prior to the contrast procedure;
already receiving dialysis (either acute or chronic) or in imminent need of dialysis at enrollment;
expected to undergo a major surgical procedure (such as involving cardiopulmonary bypass) or an additional imaging procedure with contrast media with significant risk for further renal insult within the 48 hrs following contrast administration;
participation in an interventional clinical study with an experimental therapy within the previous 30 days;
known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age >75 yrs=4 points; hematocrit level <39% for men, <35% for women=3 points; diabetes=3 points; contrast media volume=1 point for each 100 mL; serum creatinine level >1.5 g/dL=4 points OR estimated GFR 40-60 mL/min/1.73 m$^2$=2 points, 20-40 mL/min/1.73 m$^2$=4 points, <20 mL/min/1.73 m$^2$=6 points. The risks assigned are as follows: risk for CIN and dialysis: 5 or less total points=risk of CIN—7.5%, risk of dialysis—0.04%; 6-10 total points=risk of CIN—14%, risk of dialysis—0.12%; 11-16 total points=risk of CIN—26.1%, risk of dialysis—1.09%; >16 total points=risk of CIN—57.3%, risk of dialysis—12.8%.

Example 2

Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:
Inclusion Criteria
males and females 18 years of age or older;
undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.
Exclusion Criteria
known pregnancy;
previous renal transplantation;
acutely worsening renal function prior to enrollment (e.g., any category of RIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3

Acutely Ill Subject Sample Collection

The objective of this study is to collect samples from acutely ill patients. Approximately 900 adults expected to be in the ICU for at least 48 hours will be enrolled. To be enrolled in the study, each patient must meet all of the following inclusion criteria and none of the following exclusion criteria:
Inclusion Criteria
males and females 18 years of age or older;
Study population 1: approximately 300 patients that have at least one of:
shock (SBP <90 mmHg and/or need for vasopressor support to maintain MAP >60 mmHg and/or documented drop in SBP of at least 40 mmHg); and
sepsis;
Study population 2: approximately 300 patients that have at least one of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study population 3: approximately 300 patients
expected to be hospitalized through acute care setting (ICU or ED) with a known risk factor for acute renal injury (e.g. sepsis, hypotension/shock (Shock=systolic BP <90 mmHg and/or the need for vasopressor support to maintain a MAP >60 mmHg and/or a documented drop in SBP >40 mmHg), major trauma, hemorrhage, or major surgery); and/or expected to be hospitalized to the ICU for at least 24 hours after enrollment.
Exclusion Criteria
known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HIV) or a hepatitis virus;
meets only the SBP <90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4

Immunoassay Format

Analytes are is measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

Example 5

Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6

Biomarker Panels

The following exemplary method was used to segregate a patient population into two groups, which will be referred to for convenience as "non-diseased" (NonDis) and "diseased" (Dis). The combined NonDis/Dis population formed a data set, and the following analysis was performed. Multiple analytes were measured from either blood or urine or both, for the subjects in the data set. Blood and urine measurements were treated as separate biomarkers in calculating panel results. Panels were formed by algorithmically combing two or more analytes in one of two ways: (i) a very simple product and division of analyte values; and (ii) logistic regression.

Logistic regression is a method widely used for models which have a binary outcome, such as the "diseased" "non-diseased" dichotomy presented here. The method will be briefly described below, full treatments can be found in the literature. The model used is:

$$\prod_i (y_i = 1 \mid x_i) = \frac{e^{\alpha + \beta x_i}}{1 + e^{\alpha + \beta x_i}}$$

In this model, x and $\beta$ are vectors, x representing the different observables or analyte values, $y_i = 1$ indicates a diseased state, and $\Pi_i$ is the model probability of this state for the $i^{th}$ case given $x_i$. The panel value for each sample is $\Pi_i$. The log odds or logit is:

$$logit = \ln\left[\frac{\prod_i (y_i = 1 \mid x_i)}{1 - \prod_i (y_i = 1 \mid x_i)}\right] = \alpha + \beta x_i$$

Define $p_i$ as probability of observing the true outcome:

$$p_i = \begin{cases} \prod_i (y_i = 1 \mid x_i) & \text{if deseased} \\ 1 - \prod_i (y_i = 1 \mid x_i) & \text{if non-diseased} \end{cases}$$

The likelihood function is the product of the probabilities of observing the true outcomes, so the log likelihood (LL) is:

LL=ln($L(\alpha,\beta)$)=$\Sigma$ ln($p_i$)

To find the parameters, $\alpha$ and $\beta$, that best fit the model, the negative log likelihood (–LL) is minimized. This minimization was performed using the Levenberg-Marquardt method (Numerical Recipes The Art of Scientific Computing, Third Edition, Cambridge University Press, 2007). The initial point for each parameter is 0.

A commonly used statistic to compare the fit of two nested models is the likelihood ratio test. This statistic, or the deviance, is the difference in twice the negative log likelihood (–2LL) for the two model, and is asymptotically a $\chi^2$ with DF equal to the change in the number of degrees of freedom (number of analytes) between the models. The p-value is calculated from this statistic. The null hypothesis is that the logistic model is not different than a constant model ($\beta$ set to 0), is tested for each model using the likelihood ratio test. The 'model p-value' is defined as the probability that the null hypothesis is true. For the constant model, a closed form solution for $\alpha$ and –2LL can be found. It is a function of the number of diseased (#D) and the number of non-diseased (#ND) samples in the data set.

$$\alpha = \ln\left(\frac{\#D}{\#ND}\right) - 2LL = -2 * [\#ND\ln(1 - \Pi) + \#D\ln(\Pi)]$$

Where: $\Pi = \frac{\#D}{(\#ND + \#D)}$

Each analyte can be tested for significance by holding its $\beta$ at zero and comparing the model found without the analyte to the full model. The likelihood ratio test is used with 1 degree of freedom. The 'analyte p-value' is defined as the probability that the models are not different when that analyte is removed.

The analyte concentrations used in the panel can either be log transformed or untransformed. For each analyte in the panel, all the permutations of the analytes being log transformed/not transformed are calculated. The permutation with the lowest model p-value is used for that panel. For two marker panels there are 4 permutations, for six marker panels there are 8.

Table 3 contains a list of assays that were measured on urine ("U") and EDTA plasmas ("E") samples. Also listed, are the two letter codes that will be used throughout this document to refer to these assays according to the following convention: if the first character of the code is capitalized, this means the assay was measured in urine. If the second character of the code is capitalized, this means the assay was measured in EDTA plasma. If both characters of the code are capitalized, then the assay was measured in both urine and EDTA plasma. In the table some assays have a single code in capitals, indicating that the same assay format (e.g., microtiter dish, automated analyzer, etc.) was used for both urine and plasma. Other assays have separate U and E codes. This indicates that different assay formats were used for urine and EDTA plasma. A code of "**" indicates that an insufficient number of samples were measured on that assay and it will not appear in the panel results presented hereinafter.

TABLE 3

| Preferred Name | Swiss-Prot: | Code U, E | Preferred Name | Swiss-Prot: | Code U, E |
|---|---|---|---|---|---|
| 60 kDa heat shock protein, mitochondrial | P10809 | YH | 72 kDa type IV collagenase | P08253 | CP |
| 72 kDa type IV collagenase:Metalloproteinase inhibitor 1 complex | P08253 P01033 | FE | 72 kDa type IV collagenase:Metalloproteinase inhibitor 2 complex | P08253 P16035 | FD |
| 72 kDa type IV collagenase:Metalloproteinase inhibitor 4 complex | P08253 Q99727 | FF | Adiponectin | Q15848 | AD |
| Advanced glycosylation end product-specific receptor | Q15109 | KK | Agouti-related protein | O00253 | SI |
| Alkaline phosphatase, tissue-nonspecific isozyme | P05186 | UL | Alpha-1-antitrypsin | P01009 | Jj, aC |
| Alpha-1-antitrypsin Neutrophil elastase complex | P01009 P08246 | WN | Alpha-1-antitrypsin Plasminogen complex | P01009 P00747 | TK |
| Alpha-2 macroglobulin | P01023 | Ir, aE | Alpha-2-HS-glycoprotein | P02765 | IO |
| Alpha-fetoprotein | P02771 | AF | Amphiregulin | P15514 | TN |
| Amyloid Beta 40 | P05067 (aa672-711) | YE | Amyloid Beta 42 | P05067 (aa672-713) | TM |
| Angiogenin | P03950 | Tz, wJ | Angiopoietin-1 | Q15389 | DR |
| Angiopoietin-1 receptor | Q02763 | Us, gV | Angiopoietin-2 | O15123 | HW |

TABLE 3-continued

| Preferred Name | Swiss-Prot: | Code U, E | Preferred Name | Swiss-Prot: | Code U, E |
|---|---|---|---|---|---|
| Angiopoietin-related protein 3 | Q9Y5C1 | WC | Angiopoietin-related protein 4 | Q9BY76 | WD |
| Angiopoietin-related protein 6 | Q8NI99 | WE | Anti-Cathepsin-G (ANCA) | NA | DS |
| Antileukoproteinase | P03973 | GL | Apolipoprotein A-I | P02647 | Il, aG |
| Apolipoprotein A-II | P02652 | IJ | Apolipoprotein B-100 | P04114 | IH |
| Apolipoprotein C-III | P02656 | Ik, aH | Apolipoprotein E | P02649 | In, qI |
| Apolipoprotein(a) | P08519 | It, cJ | Appetite-regulating hormone | Q9UBU3 | RA |
| Aspartate aminotransferase, cytoplasmic | P17174 | DB | Bactericidal permeability-increasing protein | P17213 | DU |
| Bcl2 antagonist of cell death | Q92934 | DQ | Beta-2-glycoprotein 1 | P02749 | Im, aI |
| Beta-2-microglobulin | P61769 | AJ | Beta-nerve growth factor | P01138 | Vz, pY |
| Betacellulin | P35070 | TO | Bone morphogenetic protein 7 | P18075 | UO |
| Brain-derived neurotrophic factor | P23560 | Jn, aK | C—C motif chemokine 1 | P22362 | MU |
| C—C motif chemokine 13 | Q99616 | Mq, oT | C—C motif chemokine 15 | Q16663 | MW |
| C—C motif chemokine 17 | Q92583 | Mx, oV | C—C motif chemokine 18 | P55774 | JL |
| C—C motif chemokine 19 | Q99731 | Nq, iA | C—C motif chemokine 2 | P13500 | Ou, cL |
| C—C motif chemokine 20 | P78556 | NR | C—C motif chemokine 21 | O00585 | MY |
| C—C motif chemokine 22 | O00626 | Mj, cM | C—C motif chemokine 23 | P55773 | VI |
| C—C motif chemokine 24 | O00175 | MZ | C—C motif chemokine 26 | Q9Y258 | NA |
| C—C motif chemokine 27 | Q9Y4X3 | NB | C—C motif chemokine 3 | P10147 | Mk, cN |
| C—C motif chemokine 4 | P13236 | CO | C—C motif chemokine 5 | P13501 | Js, cY |
| C—C motif chemokine 7 | P80098 | MI | C—C motif chemokine 8 | P80075 | MP |
| C-Peptide | P01308(aa 57-87) | QV | C-reactive protein | P02741 | IP |
| C—X—C motif chemokine 10 | P02778 | OW | C—X—C motif chemokine 11 | O14625 | OH |
| C—X—C motif chemokine 13 | O43927 | MT | C—X—C motif chemokine 16 | Q9H2A7 | EF |
| C—X—C motif chemokine 2 | P19875 | PO | C—X—C motif chemokine 5 | P42830 | Mr, aV |
| C—X—C motif chemokine 6 | P80162 | NO | C—X—C motif chemokine 9 | Q07325 | NN |
| Cadherin-1 | P12830 | Gd, oO | Cadherin-16 | O75309 | TH |
| Cadherin-3 | P22223 | UG | Cadherin-5 | P33151 | GT |
| Calbindin | P05937 | YD | Calcitonin | P01258 | AO |
| Calcitonin (Procalcitonin) | P01258-Pro | HO | Cancer Antigen 15-3 | NA | IC |
| Cancer Antigen 19-9 | NA | AN | Carbonic anhydrase 9 | Q16790 | VH |
| Carcinoembryonic antigen-related cell adhesion molecule 1 | P13688 | VT | Carcinoembryonic antigen-related cell adhesion molecule 5 | P06731 | AR |
| Caspase-1 | P29466 | DV | Caspase-3, active | P42574 | Kx, dX |
| Caspase-8 | Q14790 | DW | Caspase-9 | P55211 | DO |
| Cathepsin B | P07858 | UT | Cathepsin D | P07339 | JP |
| Cathepsin S | P25774 | UW | CD40 ligand | P29965 | Ml, aQ |
| CD44 antigen | P16070 | GC | Cellular tumor antigen p53 | P04637 | RX |
| Choriogonadotropin subunit beta | P01233 | Zx, zH | Ciliary neurotrophic factor | P26441 | SJ |
| Clusterin | P10909 | Ii, sO | Coagulation factor VII | P08709 | BB |
| Collagenase 3 | P45452 | Lt, lO | Complement C3 | P01024 | AL |
| Complement C4-B | P0C0L5 | JM | Complement C5 | P01031 | VU |
| Complement factor H | P08603 | QG | Corticotropin | P01189(aa 138-176) | JY |
| Cortisol | NA | Rh, rP | Creatine Kinase-MB | P12277 P06732 | AS |
| Creatinine | NA | AA | Cyclin-dependent kinase inhibitor 1 | P38936 | Fw, rW |
| Cystatin-C | P01034 | IZ | Cytochrome c | P99999 | KY |
| DDRGK domain-containing protein 1 | Q96HY6 | WM | Dipeptidyl peptidase 4 | P27487 | VQ |
| E-selectin | P16581 | PH | Endoglin | P17813 | UP |
| Endostatin | P39060(aa 1572-1754) | Ua, wK | Endothelial protein C receptor | Q9UNN8 | Vj, eC |
| Endothelin-1 | P05305 | AW | Eotaxin | P51671 | Or, aY |
| Epidermal growth factor receptor | P00533 | Kd, tQ | Epiregulin | O14944 | TR |
| Epithelial cell adhesion molecule | P16422 | UV | Erythropoietin | P01588 | Uk, aZ |
| Erythropoietin receptor | P19235 | ED | Fatty acid-binding protein, heart | P05413 | BA |
| Fatty acid-binding protein, intestinal | P12104 | EQ | Fatty acid-binding protein, liver | P07148 | EZ |
| Ferritin | P02792 P02794 | BC | Fibrinogen | P02671 P02675 P02679 | Iq, bE |
| Fibroblast growth factor 19 | O95750 | WG | Fibroblast growth factor 21 | Q9NSA1 | WH |
| Fibroblast growth factor 23 | Q9GZV9 | WF | Fibronectin | P02751 | Rm, jB |
| Follistatin | P19883 | HX | Follitropin | P01215 P01225 | JU |
| Follitropin subunit beta | P01225 | SF | Fractalkine | P78423 | UM |
| Galectin-3 | P17931 | VB | Gastric inhibitory polypeptide | P09681 | QY |
| Glial cell line-derived neurotrophic factor | P39905 | TL | Glial fibrillary acidic protein | P14136 | EH |
| Glucagon | P01275 | QZ | Glucagon-like peptide 1 | P01275(aa 98-127 aa98-128) | QX |
| Glutathione S-transferase A1 | P08263 | Dp, bI | Glutathione S-transferase P | P09211 | FY |
| Granulocyte colony-stimulating factor | P09919 | Hq, bF | Granulocyte-macrophage colony-stimulating factor | P04141 | Pd, bH |
| Granzyme B | P10144 | EO | Granzyme M | P51124 | YF |
| Growth-regulated alpha protein | P09341 | Tj, uI | Haptoglobin | P00738 | Iu, bJ |
| Heat shock 70 kDa protein 1 | P08107 | Yi, eP | Heat shock protein beta-1 | P04792 | Yg, rS |

TABLE 3-continued

| Preferred Name | Swiss-Prot: | Code U, E | Preferred Name | Swiss-Prot: | Code U, E |
|---|---|---|---|---|---|
| Heat shock protein beta-1 (phospho SER78/ phospho SER82) | P04792 (pS78/pS82) | YK | Heat shock protein HSP 90-alpha | P07900 | YJ |
| Heme oxygenase 1 | P09601 | EM | Heparan Sulfate | NA | TI |
| Heparin-binding EGF-like growth factor | Q99075 | TT | Heparin-binding growth factor 1 | P05230 | Ub, wL |
| Heparin-binding growth factor 2 | P09038 | Lv, tS | Hepatitis A virus cellular receptor 1 | O43656 | Uh, tF |
| Hepatocyte growth factor | P14210 | OK | Hepatocyte growth factor receptor | P08581 | RT |
| Hyaluronic acid | NA | ET | Hypoxia-inducible factor 1 alpha | Q16665 | OE |
| Immunoglobulin A | NA | Qe, bM | Immunoglobulin E | NA | BN |
| Immunoglobulin M | NA | Pz, bP | Immunoglogulin G1 | NA | QA |
| Immunoglogulin G2 | NA | QD | Immunoglogulin G3 | NA | QB |
| Immunoglogulin G4 | NA | QC | Insulin | P01308 | CH |
| Insulin receptor substrate 1 | P35568 | RU | Insulin-like growth factor 1 receptor | P08069 | RY |
| Insulin-like growth factor IA | P01343 | BO | Insulin-like growth factor-binding protein 1 | P08833 | OF |
| Insulin-like growth factor-binding protein 2 | P18065 | JD | Insulin-like growth factor-binding protein 3 | P17936 | JG |
| Insulin-like growth factor-binding protein 4 | P22692 | JE | Insulin-like growth factor-binding protein 5 | P24593 | JF |
| Insulin-like growth factor-binding protein 6 | P24592 | JH | Insulin-like growth factor-binding protein 7 | Q16270 | JI |
| Intercellular adhesion molecule 1 | P05362 | JO | Intercellular adhesion molecule 2 | P13598 | GN |
| Intercellular adhesion molecule 3 | P32942 | PK | Interferon alpha-2 | P01563 | LY |
| Interferon gamma | P01579 | Pc, bL | Interleukin-1 alpha | P01583 | Lz, bX |
| Interleukin-1 beta | P01584 | PF | Interleukin-1 receptor antagonist protein | P18510 | Ma, bZ |
| Interleukin-1 receptor type I | P14778 | KF | Interleukin-1 receptor type II | P27930 | KG |
| Interleukin-10 | P22301 | Pb, bQ | Interleukin-11 | P20809 | NT |
| Interleukin-12 | P29459 P29460 | Oz, bS | Interleukin-12 subunit beta | P29460 | Oi, bR |
| Interleukin-13 | P35225 | MF | Interleukin-15 | P40933 | Mg, bU |
| Interleukin-17A | Q16552 | MH | Interleukin-18 | Q14116 | Uf, bW |
| Interleukin-2 | P60568 | Pa, cA | Interleukin-2 receptor alpha chain | P01589 | MM |
| Interleukin-20 | Q9NYY1 | NI | Interleukin-21 | Q9HBE4 | NJ |
| Interleukin-23 | Q9NPF7 P29460 | NC | Interleukin-28A | Q8IZJ0 | NK |
| Interleukin-29 | Q8IU54 | NU | Interleukin-3 | P08700 | Mb, cB |
| Interleukin-33 | O95760 | NL | Interleukin-4 | P05112 | Mc, cC |
| Interleukin-4 receptor alpha chain | P24394 | KI | Interleukin-5 | P05113 | Og, cD |
| Interleukin-6 | P05231 | Pg, cE | Interleukin-6 receptor subunit alpha | P08887 | Kj, oD |
| Interleukin-6 receptor subunit beta | P40189 | KE | Interleukin-7 | P13232 | Md, cF |
| Interleukin-8 | P10145 | Pe, cG | Interleukin-9 | P15248 | ME |
| Interstitial collagenase | P03956 | Lp, lK | Interstitial collagenase:Metalloproteinase inhibitor 2 complex | P03956 P16035 | FC |
| Involucrin | P07476 | Rf, rN | Islet amyloid polypeptide | P10997 | QW |
| Keratin, type I cytoskeletal 19 (aa311-367) | P08727 | Zw, zG | Keratin, type II cytoskeletal 1; type1 cytoskeletal 10 (Keratin-1,-10 mix) | P04264 P13645 | Rj, rR |
| Keratin, type II cytoskeletal 6 (6A, -6B, -6C mix) | P02538 P04259 P48668 | Ri, rQ | Kit ligand | P21583 | Ng, dA |
| Lactotransferrin | P02788 | FA | Leptin | P41159 | Hu, cI |
| Leukemia inhibitory factor | P15018 | ND | Lipopolysaccharide (serotypes-K,-O) | NA | Rg, rO |
| Lutropin | P01215 P01229 | JV | Lutropin subunit beta | P01229 | SH |
| Lymphatic vessel endothelial hyaluronic acid receptor 1 | Q9Y5Y7 | VW | Lymphotactin | P47992 | Ns, cK |
| Lymphotoxin-alpha | P01374 | DI | Lysozyme C | P61626 | FB |
| Macrophage colony-stimulating factor 1 | P09603 | NM | Macrophage metalloelastase | P39900 | Ld, lN |
| Macrophage migration inhibitory factor | P14174 | KS | Malondialdehyde-modified low-density lipoprotein | NA | HF |
| Matrilysin | P09237 | Lh, lL | Matrix metalloproteinase-9 | P14780 | Lj, cR |
| Matrix metalloproteinase-9:Metalloproteinase inhibitor 2 complex | P14780 P16035 | Oa, ** | Matrix metalloproteinase-9:Metalloproteinase inhibitor 3 complex | P14780 P35625 | OB |
| Metalloproteinase inhibitor 1 | P01033 | Nv, dF | Metalloproteinase inhibitor 2 | P16035 | NW |
| Metalloproteinase inhibitor 3 | P35625 | Nx, sC | Metalloproteinase inhibitor 4 | Q99727 | NY |
| Midkine | P21741 | EX | Mix of Growth-regulated alpha, beta, and gamma proteins | P09341 P19875 P19876 | LX |
| Monocyte differentiation antigen CD14 | P08571 | VO | Mucin-16 | Q8WXI7 | Id, aM |
| Myeloid differentiation primary response protein MyD88 | Q99836 | VC | Myeloperoxidase | P05164 | CS |
| Myoglobin | P02144 | CT | Neprilysin | P08473 | UY |
| Netrin-1 | O95631 | FN | Neural cell adhesion molecule 1 | P13591 | JT |
| Neuronal cell adhesion molecule | Q92823 | UZ | Neutrophil collagenase | P22894 | Li, lM |
| Neutrophil elastase | P08246 | FP | Neutrophil gelatinase-associated lipocalin | P80188 | FR |
| NF-kappa-B inhibitor alpha | P25963 | RV | Nidogen-1 | P14543 | VS |
| Nitric oxide synthase, inducible | P35228 | EW | NT-pro-BNP | P16860 | HC |
| Osteocalcin | P02818 | RC | Osteopontin | P10451 | OP |
| Oxidized low-density lipoprotein receptor 1 | P78380 | HB | P-selectin | P16109 | PI |
| P-selectin glycoprotein ligand 1 | Q14242 | GP | Pancreatic prohormone | P01298 | QU |
| Pappalysin-1 | Q13219 | CW | Parathyroid hormone | P01270 | RB |
| Peptide YY | P10082 | QT | Pigment epithelium-derived factor | P36955 | JK |
| Placenta growth factor | P49763 | Ue, tU | Plasminogen activator inhibitor 1 | P05121 | CU |

TABLE 3-continued

| Preferred Name | Swiss-Prot: | Code U, E | Preferred Name | Swiss-Prot: | Code U, E |
|---|---|---|---|---|---|
| Platelet basic protein | P02775 | VP | Platelet endothelial cell adhesion molecule | P16284 | HR |
| Platelet factor 4 | P02776 | VV | Platelet-derived growth factor A | P04085 P01127 | JR |
| Platelet-derived growth factor subunit A (dimer) | P04085 | JQ | Platelet-derived growth factor subunit B (dimer) | P01127 | HV |
| Poly [ADP-ribose] polymerase 1 (cleaved) | P09874 | Kz, ** | Pro-epidermal growth factor | P01133 | Lu, aU |
| Pro-Interleukin-1 beta | P01584-Pro | GH | Pro-interleukin-16 | Q14005 | Mv, bV |
| Prolactin | P01236 | IB | Prostate-specific antigen | P07288 | CX |
| Prostatic acid phosphatase | P15309 | CV | Protein NOV homolog | P48745 | UU |
| Protein S100-A12 | P80511 | AX | Protein S100-B | P04271 | XA |
| Protransforming growth factor alpha | P01135 | Mn, tX | Renin | P00797 | Sr, sK |
| Resistin | Q9HD89 | WB | Serum albumin | P02768 | St, zA |
| Serum amyloid A protein | P02735 | HP | Serum amyloid P-component | P02743 | Is, cZ |
| Sex hormone-binding globulin | P04278 | DC | SL cytokine | P49771 | LW |
| Somatotropin | P01241 | BG | Stromal cell-derived factor 1 | P48061 | MS |
| Stromelysin-1 | P08254 | CQ | Stromelysin-1:Metalloproteinase inhibitor 2 complex | P08254 P16035 | FI |
| Stromelysin-2 | P09238 | UR | Tenascin | P24821 | TV |
| Thrombomodulin | P07204 | Pj, hG | Thrombopoietin | P40225 | Ne, dJ |
| Thrombospondin-1 | P07996 | GW | Thrombospondin-2 | P35442 | Uc, wP |
| Thymic stromal lymphopoietin | Q969D9 | NH | Thyrotropin | P01215 P01222 | DK |
| Thyroxine-binding globulin | P05543 | DD | Tissue factor | P13726 | DE |
| Tissue-type plasminogen activator | P00750 | HL | Transforming growth factor beta-1 | P01137 | Ql, qO |
| Transforming growth factor beta-2 | P61812 | Qm, qP | Transforming growth factor beta-3 | P10600 | Qn, qQ |
| Transmembrane glycoprotein NMB | Q14956 | UN | Transthyretin | P02766 | QH |
| Trefoil factor 3 | Q07654 | Ss, sM | Tubulointerstitial nephritis antigen | Q9UJW2 | GZ |
| Tumor necrosis factor | P01375 | Oy, dH | Tumor necrosis factor ligand superfamily member 10 | P50591 | NF |
| Tumor necrosis factor ligand superfamily member 11 | O14788 | YL | Tumor necrosis factor ligand superfamily member 6 | P48023 | KR |
| Tumor necrosis factor receptor superfamily member 10B | O14763 | RZ | Tumor necrosis factor receptor superfamily member 11B | O00300 | ON |
| Tumor necrosis factor receptor superfamily member 1A | P19438 | Kl, oQ | Tumor necrosis factor receptor superfamily member 1B | P20333 | DG |
| Tumor necrosis factor receptor superfamily member 5 | P25942 | AP | Tumor necrosis factor receptor superfamily member 6 | P25445 | KQ |
| Tumor necrosis factor receptor superfamily member 8 | P28908 | KC | Urokinase plasminogen activator surface receptor | Q03405 | UX |
| Urokinase-type plasminogen activator | P00749 | VA | Vascular cell adhesion protein 1 | P19320 | DL |
| Vascular endothelial growth factor A | P15692 | Om, dM | Vascular endothelial growth factor D | O43915 | Ud, wQ |
| Vascular endothelial growth factor receptor 1 | P17948 | KN | Vascular endothelial growth factor receptor 2 | P35968 | KO |
| Vascular endothelial growth factor receptor 3 | P35916 | KP | Versican core protein | P13611 | HA |
| Vitamin D-binding protein | P02774 | PS | Vitamin K-dependent protein C | P04070 | GB |
| von Willebrand Factor | P04275 | Iv, dN | WAP four-disulfide core domain protein 2 | Q14508 | Zq, zI |

The results of each analysis presented in the following examples are presented in FIGS. 1-43.

Each figure contains an initial table presenting the univariate statistics for the analytes that appear in the biomarker panels that follows in the same figure. The data set was segregated into two groups, non-diseased (NonDis) and diseased (Dis) patients as indicated in the figure heading. The analyte code and units of measurement are shown, followed by the median, average, standard deviation, maximum and minimum of the analyte values calculated for each group. Also shown are the number of samples that make up each group, and the number of patients that the samples were drawn from. Values below the detectable limit of a particular assay are indicated with the value $1 \times 10^{-9}$ (written as "1.0E–9"). The univariate AUC for each analyte is also shown. Standard errors were calculated as described in Hanley, J. A., and McNeil, B. J., "The meaning and use of the area under a receiver operating characteristic (ROC) curve," Radiology (1982) 143: 29-36; p values were calculated with a two-tailed Z-test. In the column specifying the units of measurement, certain analytes are listed as '2.6 ng/ml', '2.5 ng/ml', and '2.3 mU/ml'. For these markers, the values in the tables should be scaled by 2.6, 2.5, and 2.3 respectively. By way of example, a value of 1 in the 'median' column converts to a value of 2.6 ng/ml, 2.5 ng/ml, or 2.3 mU/ml, respectively. Note that applying such a scaling factor to the data does not impact the AUC of a marker or the AUC of a panel of which it is a part.

Following the univariate statistics, each figure provides panel tables which list the biomarker panels having model p-value in the ranges specified in the particular figures. When a panel is formed by combining multiple analytes from this set, the number of samples used was the intersection of the samples measured by all analytes on the particular panel. Panels that have an intersection of less than 7 samples in either the non-diseased or diseased groups were not considered in the analysis. For compactness panels are encoded as follows: aBCdEE represents the two panels aBCdEe and aBCdeE, in this case representing biomarker "ab" measured in plasma, biomarker "cd" measured in urine, and biomarker ee measured in urine for the first panel and ee measured in plasma for the second panel. Codes in ( ) or { } and separated by a space represent a list of analytes that join with the analyte(s) outside the brackets to form panels with a common analyte. For example, Ab{cD(eF gH) Km(EfQR)} represents 5 panels which all have biomarker Ab in common. They are AbcDeF, AbcDgH, AbKmEf, AbKmQr, and AbKmqR.

Those results labeled 'Unconstrained Panels' refer to panels which were not required to have each analyte univariate p-value ≤0.05. Those results labeled 'Constrained Panels' require that each analyte use in the panel to have a univariate p-value ≤0.05.

Example 7

Use of Biomarker Panels

Patients from the intensive care unit (ICU) were classified by kidney status as non-injury (O), risk of injury (R), injury (I), and failure (F) according to the maximum RIFLE stage reached as determined by the RIFLE criteria. Two cohorts were defined as (Cohort 1—"Non-diseased") patients that did not progress beyond a particular RIFLE stage, and (Cohort 2—"Diseased") patients that reached a later RIFLE stage within 10 days. Marker concentrations were measured in samples collected from a subject at 0, 24 hours, and 48 hours prior to reaching the "Diseased" stage.

Each biomarker was measured by standard immunoassay methods using commercially available assay reagents. In the case of those biomarkers which are membrane-associated, assays which recognize soluble forms were used. As noted above, the membrane-associated biomarkers include Swiss-Prot entries O14788, O14944, O75309, P00797, P05186, P08473, P13688, P15514, P22223, P27487, P35070, Q03405, Q14956, Q16790, Q99075, Q9Y5Y7Q15109, Q02763, P17213, P12830, P33151, P06731, P29965, P16070, Q9H2A7, P17813, Q9UNN8, P00533, P16422, P19235, P16581, P78423, O43656, P08581, P08069, P05362, P13598, P32942, P14778, P27930, P01589, P24394, P08887, P40189, P21583, P09603, P08571, Q8WXI7, P13591, Q92823, P78380, P16284, P01133, P15309, P01135, P16109, Q14242, P49771, P07204, P13726, P01375, P50591, P48023, O14763, P19438, P20333, P25942, P25445, P28908, P19320, P17948, and P35968.

The ability of a biomarker panel to distinguish "Diseased" from "Non-Diseased" was determined as described above in Example 6. Patients in Cohort 2 were also separated according to the reason for adjudication to the "Diseased" stage as being based on serum creatinine measurements (sCr), being based on urine output (UO), or being based on either serum creatinine measurements or urine output. As an example, for those patients adjudicated to stage F on the basis of serum creatinine measurements alone, the stage 0 cohort may have included patients adjudicated to stage F on the basis of urine output; for those patients adjudicated to stage F on the basis of urine output alone, the stage 0 cohort may have included patients adjudicated to stage F on the basis of serum creatinine measurements; and for those patients adjudicated to stage F on the basis of serum creatinine measurements or urine output, the stage 0 cohort contains only patients in stage 0 for both serum creatinine measurements and urine output. Also, for those patients adjudicated to stage F on the basis of serum creatinine measurements or urine output, the adjudication method which yielded the most severe RIFLE stage was used.

The following data are presented in the figures:

FIG. 1. No or R RIFLE stage versus RIFLE I or F. RIFLE stage adjudicated by sCr and Urine Output. Diseased group sample is 24 hours prior to RIFLE I diagnosis.

FIG. 2. No or R RIFLE stage versus RIFLE I or F. RIFLE stage adjudicated by sCr. Diseased group sample is 24 hours prior to RIFLE I diagnosis.

FIG. 3. No or R RIFLE stage versus RIFLE I or F. RIFLE stage adjudicated by Urine Output. Diseased group sample is 24 hours prior to RIFLE I diagnosis.

FIG. 4. No RIFLE stage versus RIFLE R, I, or F. RIFLE stage adjudicated by sCr and Urine Output. Diseased group sample is 24 hours prior to RIFLE R diagnosis.

FIG. 5. No RIFLE stage versus RIFLE R, I, or F. RIFLE stage adjudicated by sCr. Diseased group sample is 24 hours prior to RIFLE R diagnosis.

FIG. 6. No RIFLE stage versus RIFLE R, I, or F. RIFLE stage adjudicated by Urine Output. Diseased group sample is 24 hours prior to RIFLE R diagnosis.

FIG. 7. No, R, or I RIFLE stage versus RIFLE F. RIFLE stage adjudicated by sCr and Urine Output. Diseased group sample is 24 hours prior to RIFLE I diagnosis.

FIG. 8. No, R, or I RIFLE stage versus RIFLE F. RIFLE stage adjudicated by Urine Output. Diseased group sample is 24 hours prior to RIFLE I diagnosis.

FIG. 9. No or R RIFLE stage versus RIFLE I or F. RIFLE stage adjudicated by sCr and Urine Output. Diseased group sample is at RIFLE I diagnosis.

FIG. 10. No or R RIFLE stage versus RIFLE I or F. RIFLE stage adjudicated by sCr. Diseased group sample is at RIFLE I diagnosis.

FIG. 11. No or R RIFLE stage versus RIFLE I or F. RIFLE stage adjudicated by Urine Output. Diseased group sample is at RIFLE I diagnosis.

FIG. 12. No RIFLE stage versus RIFLE R, I, or F. RIFLE stage adjudicated by sCr and Urine Output. Diseased group sample is at RIFLE R diagnosis.

FIG. 13. No RIFLE stage versus RIFLE R, I, or F. RIFLE stage adjudicated by sCr. Diseased group sample is at RIFLE R diagnosis.

FIG. 14. No RIFLE stage versus RIFLE R, I, or F. RIFLE stage adjudicated by Urine Output. Diseased group sample is at RIFLE R diagnosis.

FIG. 15. No, R, or I RIFLE stage versus RIFLE F. RIFLE stage adjudicated by sCr and Urine Output. Diseased group sample is at RIFLE I diagnosis.

FIG. 16. No, R, or I RIFLE stage versus RIFLE F. RIFLE stage adjudicated by sCr. Diseased group sample is at RIFLE I diagnosis.

FIG. 17. No, R, or I RIFLE stage versus RIFLE F. RIFLE stage adjudicated by Urine Output. Diseased group sample is at RIFLE I diagnosis.

FIG. 18. No or R RIFLE stage versus RIFLE I or F. RIFLE stage adjudicated by sCr and Urine Output. Diseased group sample is 48 hours prior to RIFLE I diagnosis.

FIG. 19. No or R RIFLE stage versus RIFLE I or F. RIFLE stage adjudicated by sCr. Diseased group sample is 48 hours prior to RIFLE I diagnosis.

FIG. 20. No or R RIFLE stage versus RIFLE I or F. RIFLE stage adjudicated by Urine Output. Diseased group sample is 48 hours prior to RIFLE I diagnosis.

FIG. 21. No RIFLE stage versus RIFLE R, I, or F. RIFLE stage adjudicated by sCr and Urine Output. Diseased group sample is 48 hours prior to RIFLE R diagnosis.

FIG. 22. No RIFLE stage versus RIFLE R, I, or F. RIFLE stage adjudicated by sCr. Diseased group sample is 48 hours prior to RIFLE R diagnosis.

FIG. 23. No RIFLE stage versus RIFLE R, I, or F. RIFLE stage adjudicated by Urine Output. Diseased group sample is 48 hours prior to RIFLE R diagnosis.

FIG. 24. No, R, or I RIFLE stage versus RIFLE F. RIFLE stage adjudicated by sCr and Urine Output. Diseased group sample is 48 hours prior to RIFLE I diagnosis.

FIG. 25. Progression of RIFLE R to RIFLE I or F. RIFLE stage adjudicated by sCr and Urine Output. Sample is at R diagnosis.

FIG. 26. Progression of RIFLE R to RIFLE I or F. RIFLE stage adjudicated by sCr. Sample is at R diagnosis.

FIG. 27. Progression of RIFLE R to RIFLE I or F. RIFLE stage adjudicated by Urine Output. Sample is at R diagnosis.

FIG. 28. No or R RIFLE stage versus RIFLE I or F. RIFLE stage adjudicated by sCr and Urine Output, within 48 hrs of enrollment. Sample is at enrollment.

FIG. 29. No or R RIFLE stage versus RIFLE I or F. RIFLE stage adjudicated by sCr, within 48 hrs of enrollment. Sample is at enrollment.

FIG. 30. No or R RIFLE stage versus RIFLE I or F. RIFLE stage adjudicated by Urine Output, within 48 hrs of enrollment. Sample is at enrollment.

FIG. 31. No RIFLE stage versus RIFLE R, I, or F. RIFLE stage adjudicated by sCr and Urine Output, within 48 hrs of enrollment. Sample is at enrollment.

FIG. 32. No RIFLE stage versus RIFLE R, I, or F. RIFLE stage adjudicated by sCr, within 48 hrs of enrollment. Sample is at enrollment.

FIG. 33. No RIFLE stage versus RIFLE R, I, or F. RIFLE stage adjudicated by Urine Output, within 48 hrs of enrollment. Sample is at enrollment.

FIG. 34. No, R, or I RIFLE stage versus RIFLE F. RIFLE stage adjudicated by sCr and Urine Output, within 48 hrs of enrollment. Sample is at enrollment.

FIG. 35. No, R, or I RIFLE stage versus RIFLE F. RIFLE stage adjudicated by Urine Output, within 48 hrs of enrollment. Sample is at enrollment.

FIG. 36. No or R RIFLE stage versus RIFLE I or F. RIFLE stage adjudicated by sCr and Urine Output, within 24 hrs of enrollment. Sample is at enrollment.

FIG. 37. No or R RIFLE stage versus RIFLE I or F. RIFLE stage adjudicated by sCr, within 24 hrs of enrollment. Sample is at enrollment.

FIG. 38. No or R RIFLE stage versus RIFLE I or F. RIFLE stage adjudicated by Urine Output, within 24 hrs of enrollment. Sample is at enrollment.

FIG. 39. No RIFLE stage versus RIFLE R, I, or F. RIFLE stage adjudicated by sCr and Urine Output, within 24 hrs of enrollment. Sample is at enrollment.

FIG. 40. No RIFLE stage versus RIFLE R, I, or F. RIFLE stage adjudicated by sCr, within 24 hrs of enrollment. Sample is at enrollment.

FIG. 41. No RIFLE stage versus RIFLE R, I, or F. RIFLE stage adjudicated by Urine Output, within 24 hrs of enrollment. Sample is at enrollment.

FIG. 42. No, R, or I RIFLE stage versus RIFLE F. RIFLE stage adjudicated by sCr and Urine Output, within 24 hrs of enrollment. Sample is at enrollment.

FIG. 43. No, R, or I RIFLE stage versus RIFLE F. RIFLE stage adjudicated by Urine Output, within 24 hrs of enrollment. Sample is at enrollment.

Example 8

Use of Biomarker Panels

The foregoing examples rely on logistic regression for identification and use of biomarker panels. As noted, this is but one type of analysis which may be used to generate such panels of markers. Any classification method can be used, including, but not limited to, Bayesian classifiers, discriminant analysis, decision trees, neural networks, support-vector machines, nonparametric kernel density estimation methods, nearest neighbor rules, sums, differences, products and ratios of marker concentrations.

As an example, the following exemplary biomarker panels of 2, 3, 4 and 5 markers were generated using products (indicated by "*" in the table) and ratios (indicated by "/" in the table) of marker concentrations. The product of the maker concentrations was used unless the panel consisted of markers that increased and markers that decreased with kidney injury as determined by the univariate performance for the measured patient population. In this case, a ratio was formed in which markers that increased were divided by markers that decreased.

In this example, Cohort 1 consisted of patients that did not progress beyond RIFLE stage R and Cohort 2 consisted of patients that reached stage I or F within 10 days. Panel values were determined for samples from patients in Cohort 1 and samples drawn 24 (+/−12) hours prior to stage I (or F if no sample at stage I) in Cohort 2. Patients were adjudicated to RIFLE stage R, I, or F based on either serum creatinine or urine output, whichever method yielded the most severe RIFLE stage. A receiver operating characteristic (ROC) curve was generated for each panel and the area under each ROC curve (AUC) was determined. Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test.

Examples of 2-, 3-, 4- and 5-marker panels are shown in the following table. The results for the 4 and 5 marker panels demonstrate that larger panels can be formed with the kidney injury markers of Table 2, and that these panels can have improved p-values relative to 2 and 3-marker panels.

TABLE 4

2-Marker Panels (AUC p-value <1e−3)

| | | | | | | |
|---|---|---|---|---|---|---|
| No/(dR) | Nw * iO | Fp/(Jj) | No/(Ch) | Lx * Nw | Et * oZ | Lx/(cM) |
| No * aA | No * iO | Bc/(Jj) | No/(Ck) | No * Nw | Lx * oZ | Nw * cN |
| Et * aA | No/(iQ) | Jl(Jj) | Gx * No | Ok/(Jj) | Nw * oZ | No * cN |
| No * eF | Nw/(iQ) | Kq/(Jj) | nN/(mX) | Ar * oF | No * oZ | Lx/(cW) |
| Lx * eF | Lj/(iT) | No/(kR) | Im * Lx | Et/(oI) | Nw * pA | No/(cW) |
| Nw * eF | Is/(Bk) | Nw/(kR) | Kq * Lx | No/(oI) | Lj * pA | Nw * cV |
| Ar * eF | Nw * iV | Lh/(Jj) | Ky * Lx | Lx/(oI) | Mz * pA | No * cV |
| Ar/(eC) | Nw/(iL) | Lj/(Jj) | Et * Lx | Nw/(oI) | No * pA | Lx * cV |
| Nw/(eC) | Lx/(iL) | Et * Lj | Lx/(Kj) | Nw/(oH) | Ar * pA | No * dC |
| No/(eC) | No/(iL) | Mz/(Jj) | Lx/(oH) | No/(oH) | Ar * oY | No/(dD) |
| Mz/(eC) | Lj/(iL) | Lx * Mz | Lx/(Ct) | Lx/(oH) | Mz * oY | Lx/(dD) |
| Et/(Bk) | Ar/(iL) | Lx/(Ng) | Lx/(Ch) | Lj/(oH) | Et * oY | Nw * gL |
| Mz * iA | No/(iH) | Nr/(Jj) | Lx/(Gp) | Ar/(oH) | Nw * oY | No * gL |
| Lj * iA | Nw/(iH) | No/(Jj) | Bc * Lx | Oh/(Jj) | No * oY | Mz/(gP) |
| No * iA | No * iK | Jy * No | Lx/(Aj) | Nw * oL | Et * Fp | Et/(gP) |

TABLE 4-continued

| | | | | | |
|---|---|---|---|---|---|
| No * hB | Et * iK | Im * No | Fp * Lx | No/(pC) | bA * fR | Ji/(gP) |
| Nw * hB | Nw * iK | Et * No | Lx/(Az) | Lx * pF | cT * fR | Nw/(gP) |
| Mz * hB | Et * Im | No/(Kj) | Lx/(Bk) | Oa * pF | cV * fR | Lx/(gP) |
| Lj * hB | No/(iI) | Mz * No | Et * Mi | Et * pF | No * aJ | No/(gP) |
| Ar * hB | Nw/(iI) | Lj * No | No/(hH) | Lj * pF | Lx * aZ | Ar/(gP) |
| Et * hF | Ar/(iI) | Mi * No | No * Oa | Mz * pF | Lx * bA | |
| Nw * hF | Et * iZ | Lw * No | No/(nW) | No * pF | Lj * bA | |
| No * hF | Nw * iX | Lx * No | Lx/(nW) | Nw * pF | By * bA | |
| Nw * hG | Et * jA | No/(Bk) | Nw/(nW) | Ar * pF | Bm * bA | |
| Nw/(iR) | Nw * jA | Aw * No | Et/(nW) | Ar * pF | Ar * bA | |
| No/(iR) | Is/(Jj) | Ay * No | Ar/(nW) | Ar * oZ | Bb * bA | |
| Ar/(iR) | Ij(Jj) | Fb * No | Fp * Nw | By * oZ | Ba/(Aj) | |
| Ar * iP | Im/(Jj) | Fp * No | Et * Nw | Nr * oZ | Lj * bZ | |
| No * iP | Ji/(Jj) | No/(Aj) | Nw/(Jj) | Mz * oZ | No * bZ | |
| Nw * iP | Et/(Jj) | By * No | Im * Nw | Lj * oZ | No/(cK) | |

3-Marker Panels (AUC p-value <1e−7)

| | | | | |
|---|---|---|---|---|
| Et * Im/(Jj) | No/(iI)/(Bk) | Bc/(Jj)/(iR) | No * Nw/(eC) | Et * Lj/(iL) |
| Et * No/(Bk) | Et * No/(eC) | No/(Bk)/(iJ) | Ar * Nw/(iL) | Et * oZ/(Ck) |
| Lu * Im/(Jj) | Ar * Nw * oZ | Mz * Nw * pF | Jy * Nw * iK | No * oZ/(Jj) |
| Et * Nw/(Bk) | No/(gP)/(Kj) | Is/(Bk)/(oH) | No/(dR)/(Ch) | oZ * Nw * pA |
| No * eF/(Bk) | No/(eC)/(cW) | No/(nW)/(Ck) | Lj/(Jj)/(iR) | Fp * Nw * oZ |
| Im * Nw/(Jj) | Nw/(gP)/(Jj) | No/(oH)/(Ch) | Lj * Nw * pF | Ar * Nw/(gP) |
| No * cV/(Bk) | Nw/(gP)/(Ck) | oZ * No * pF | No/(iR)/(eC) | iK * No/(iL) |
| Et * Nw/(gP) | No/(oH)/(Ck) | Nw * iK/(gP) | Nw * iK/(Ck) | Et * No/(iR) |
| Et * No/(Jj) | Mz * pF/(Jj) | Mz * pF/(Bk) | Nw * iK/(Jj) | Ar * pA/(Ch) |
| Et * Is/(Bk) | Nw/(nW)/(Ck) | Bc/(Jj)/(nW) | Ar * Nw/(oH) | Bc/(Jj)/(iQ) |
| Lj * bZ/(Jj) | No/(gP)/(Ck) | No/(nW)/(Bk) | Lu * Mz * pF | Nw/(iQ)/(Ck) |
| No/(gP)/(Bk) | Lj * oZ/(Jj) | Lj/(oH)/(Jj) | No * gL/(Bk) | No * oZ/(Bk) |
| Et * Im/(Bk) | Et * Ar/(eC) | Et/(gP)/(Jj) | No * pF/(Bk) | Ar * Et * oZ |
| Im * No/(Jj) | Et * No/(nW) | No/(eC)/(Ch) | Lj/(iL)/(Jj) | No/(nW)/(gP) |
| Et * No/(gP) | oZ * Bc/(Jj) | Jy * Nw/(gP) | Et * iK/(Jj) | Ar * oZ/(Jj) |
| Et * Fp/(Jj) | eF * Lj/(Jj) | dC * Nw/(gP) | No/(nW)/(Jj) | No/(Bk)/(iS) |
| No/(cW)/(Bk) | No * pF/(Ch) | No/(pC)/(eC) | Lj/(iT)/(Jj) | Ar * Et/(nW) |
| No/(gP)/(Jj) | No/(gP)/(cK) | No/(iL)/(Bk) | No/(gP)/(Ch) | No/(nW)/(Ch) |
| Pj * Im/(Jj) | No * eF/(Jj) | Et * Nw * hF | Nw/(iR)/(eC) | Et/(nW)/(Ck) |
| Im * Ok/(Jj) | aA * Nw/(eC) | No/(iQ)/(Bk) | Nw * pF/(Ch) | No/(iI)/(Ch) |
| No/(iR)/(Bk) | Nw/(gP)/(aW) | No/(eC)/(Jj) | Et * Lj * oZ | No/(gP)/(eC) |
| No * Nw/(Bk) | No * iK/(Jj) | Lj * Nw * oZ | Lu * No/(nW) | Nw * pA/(Ch) |
| Nw * oZ/(Ck) | Lj/(Jj)/(gP) | iK * Nw/(iL) | Et * Lj * pF | Ar * Nw/(iR) |
| Et * Nw * iK | Et * Nw * iO | Im/(Jj)/(gP) | Lj/(Jj)/(nW) | Ar * Nw/(nW) |
| Ij * Et/(Bk) | aJ * Nw/(gP) | No * oZ/(nW) | Mz * pF/(Ch) | No * pA/(Bk) |
| No/(oH)/(Bk) | No/(nW)/(eC) | Ar * Nw/(eC) | Nw/(oH)/(Ck) | No/(iR)/(Ck) |
| No * eF/(Ch) | No * hB/(Bk) | Mz * No/(gP) | No * Nw/(nW) | Ar/(oH)/(Jj) |
| No * Nw/(gP) | Lx/(gP)/(Ch) | Mz * No * pF | No * oZ/(Ck) | Nw/(gP)/(eC) |
| Bc/(Jj)/(oH) | Nw/(gP)/(dD) | Lw * Nw/(gP) | No/(iR)/(Jj) | iZ * Nw/(eC) |
| Fy * Et/(Bk) | fS * Lx/(Ch) | Et * No * iK | Et * Nw * pF | |

4-Marker Panels (AUC p-value <1e−8)

| | | | | |
|---|---|---|---|---|
| Nw * Im/Jj/Kg | Oa * Et * Im/Jj | Ar * Et * Im/Jj | Mb * Nw * Im/Jj | Et * Nw * Ji * Fp |
| Nw * Im/Jj/Kj | Fb * Nw * Im/Jj | Pj * Et * Im/Jj | Nt * Et * Im/Jj | Fp * Nw * Im/Jj |
| Ap * Nw * Im/Jj | Hb * Et * Im/Jj | Ke * Et * Im/Jj | Is * Et * Im/Jj | Ji * Et * Im/Jj |
| Bc * Nw * Im/Jj | Bb * Et * Im/Jj | Jy * Et * Im/Jj | Nw * Ji * Fp/Hw | Mb * Ji * Im/Jj |
| Kp * Et * Im/Jj | Cu * Et * Im/Jj | Fb * Et * Im/Jj | Mb * Et * Im/Jj | Ji * Im/Jj/Mc |
| Jy * Nw * Im/Jj | Bc * Et * Im/Jj | Aw * Et * Im/Jj | Et * Im/Jj/Mc | Fp * Et * Im/Jj |
| Cp * Nw * Im/Jj | Et * Im/Jj/Kg | Nt * Nw * Im/Jj | Ok * Et * Im/Jj | Et * Ji * Fp/Jj |
| Fy * Et * Im/Jj | Ar * Ji * Im/Jj | Nw * Im/Jj/Me | Et * Nw * Im/Jj | Fp * Ji * Im/Jj |
| Pj * Nw * Im/Jj | Aw * Nw * Im/Jj | Is * Nw * Im/Jj | Nw * Ji * Fp/Mc | Et * Ji * Fp/Lu |
| Kq * Nw * Im/Jj | Et * Im/Jj/Kj | Qe * Nw * Im/Jj | Ji * Im/Jj/Lu | Et * Ji * Fp/Mc |
| Ke * Nw * Im/Jj | Aw * Ji * Im/Jj | Nw * Im/Jj/Mc | Ji * Nw * Im/Jj | Nw * Ji * Fp/Jj |
| Ar * Nw * Im/Jj | Kq * Et * Im/Jj | Ok * Nw * Im/Jj | Ok * Ji * Im/Jj | Nw * Ji * Fp/Lu |
| Kk * Et * Im/Jj | Cp * Et * Im/Jj | Et * Aw * Qe/Jj | Pj * Is/Jj/Kg | Et * Ke * Is/Jj |
| Et * Is * Ji/Jj | Et * Ji * Nw/Lu | Et * Aw * Is/Jj | Nt * Is * Mt/Ct | Ny * Nm * Mt/Ct |
| Et * Is * Fp/Jj | Et * Jp * Fp/Jj | Et * Is/Kj/Jj | Nm * Pf * Mt/Ct | Nm * Mt/Ct/Jj |
| Et * Ji * Qe/Jj | Et * Qe * Fp/Jj | Im * Nm * Mt/Ct | Or * Cp * Et/Jj | Nw * Et * Is/Kg |
| Mb * Is * Ji/Jj | Et * Fp/Mc/Jj | Mm * Is/Jj/Kg | Jy * Et * Qa/Jj | Ji * Is/Jj/Kg |
| Is * Ji * Fp/Jj | Im * Ok * Fp/Jj | Ar * Et * Is/Jj | Is * Nm * Mt/Ct | Nm * Mt/Ct/Ch |
| Et * Nw * Fp/Jj | Et * Jp * Fp/Jj | Qa * Et * Aw/Jj | Nt * Pf * Mt/Ct | Is * Ok/Jj/Kg |
| Et * Ok * Fp/Jj | Ji * Qe * Fp/Jj | Jy * Et * Qe/Jj | Nb * Pf * Mt/Ct | Mz * Nm * Mt/Ct |
| Et * On * Fp/Jj | Ji * On * Fp/Jj | Is * Im * Mt/Ct | Is * Pf * Mt/Ct | Ke * Is/Jj/Kg |
| Ji * Ok * Fp/Jj | Et * Nw * Fp/Mc | Nb * Is * Mt/Ct | Ji * Et * Aw/Jj | Ke * Et * Fp/Jj |
| Et * Nw * Fp/Lu | Ok * Fp/Jj/Mc | Et * Is * Mt/Ct | Im * Pf * Mt/Ct | Im * Is/Jj/Kg |
| Nw * Ok * Fp/Jj | Et * Is/Jj/Kg | Et * Im * Ji/Aj | Nt * Im * Mt/Ct | Is * Nw/Jj/Kg |

5-Marker Panels (AUC p-value <1e−9)

| | | | |
|---|---|---|---|
| Mz * Nw * Im/Jj/Kg | Lh * Et * Im/Jj/Kg | Nt * Fp * Nw * Im/Jj | Jp * Fp * Nw * Im/Jj |
| Kq * Nw * Im/Jj/Kg | Ip * Nw * Im/Jj/Kg | Mb * Ok * Nw * Ji * Fp | Mz * Fp * Nw * Im/Jj |

TABLE 4-continued

| | | | |
|---|---|---|---|
| Qa * Nw * Im/Jj/Kg | Dg * Ji * Im/Jj/Kj | Et * Is * Nw * Ji * Fp | Nt * Nw * Ji * Fp/Jj |
| Ma * Nw * Ji * Fp/Aj | Et * Cp * Ji * Im/Jj | On * Nw * Ji * Fp/Hw | Jt * Nw * Ji * Fp/Jj |
| Ok * Nw * Im/Jj/Kg | Nm * Et * Im/Jj/Aj | Et * Mi * Nw * Ji * Fp | Mi * Nw * Ji * Fp/Jj |
| Ji * Nw * Im/Jj/Kg | Et * Cp * Nw * Im/Jj | Qe * Fp * Nw * Im/Jj | Pz * Nw * Ji * Fp/Jj |
| Ke * Aw * Nw * Im/Jj | Et * Jy * Ji * Im/Jj | Fp * Nw * Im/Jj/Hw | Jp * Nw * Ji * Fp/Lu |
| Ip * Nw * Im/Jj/Kj | Ad * Nw * Im/Jj/Kj | Is * Fp * Nw * Im/Jj | Mb * Nw * Ji * Fp/Lu |
| Bc * Nw * Im/Jj/Kj | Et * Ar * Nw * Im/Jj | Im * Nw * Ji * Fp/Mc | Mz * Et * Ji * Fp/Hw |
| Ef * Nw * Im/Jj/Aj | Kl * Ji * Im/Jj/Aj | Lw * Nw * Ji * Fp/Jj | Is * Et * Ji * Fp/Hw |
| Ok * Nw * Im/Jj/Kj | Jo * Et * Im/Jj/Kg | Jo * Nw * Ji * Fp/Jj | Ok * Et * Ji * Fp/Hw |
| Ap * Et * Ji * Fp/Jj | Ad * Nw * Im/Jj/Aj | Js * Nw * Ji * Fp/Jj | Et * Is * Ji * Im/Jj |
| Qe * Nw * Im/Jj/Kj | Kq * Et * Im/Jj/Kj | Jp * Nw * Ji * Fp/Mc | Is * Ji * Im/Jj/Hw |
| Nt * Aw * Nw * Im/Jj | Dl * Et * Im/Jj/Aj | Qe * Nw * Ji * Fp/Lu | Is * Et * Ji * Fp/Jj |
| Fb * Aw * Nw * Im/Jj | Bc * Et * Im/Jj/Kj | Lw * Nw * Ji * Fp/Lu | Et * Fp * Nw * Im/Jj |
| Pj * Nw * Im/Jj/Kj | Ok * Et * Im/Jj/Kg | Mb * Nw * Ji * Fp/Mc | Et * Ji * Nw * Im/Jj |
| Ip * Nw * Im/Jj/Aj | Qe * Et * Im/Jj/Kj | Et * Nt * Nw * Im/Jj | Et * Nw * Im/Jj/Lu |
| Qe * Nw * Im/Jj/Kg | Ke * Et * Im/Jj/Ob | Et * Ok * Nw * Ji * Fp | Et * Nw * Im/Jj/Mc |
| Jg * Nw * Im/Jj/Aj | Kq * Aw * Et * Im/Jj | Jp * Nw * Ji * Fp/Hw | Et * Mb * Nw * Im/Jj |
| Kq * Aw * Nw * Im/Jj | Ke * Aw * Et * Im/Jj | Et * Jp * Nw * Ji * Fp | Ji * Et * Im/Jj/Lu |
| Et * Nw * Im/Jj/Aj | Mm * Et * Im/Jj/Kj | Nw * Ji * Fp/Nh/Jj | Ji * Fp * Et * Im/Jj |
| Ad * Et * Ji * Fp/Aj | Mm * Et * Im/Jj/Kg | Ma * Nw * Ji * Fp/Jj | Ji * Et * Im/Jj/Mc |
| Ad * Et * Ji * Fp/Jj | Ke * Et * Im/Jj/Kg | Lh * Nw * Ji * Fp/Jj | Ji * Mb * Et * Im/Jj |
| Jg * Et * Ji * Fp/Aj | Kq * Et * Im/Jj/Aj | Mz * Nt * Nw * Ji * Fp | Ok * Fp * Et * Im/Jj |
| Et * Kk * Ji * Im/Jj | Ad * Ji * Im/Jj/Aj | Ik * Ji * Nw * Im/Jj | Fp * Et * Im/Jj/Mc |
| Pj * Ji * Im/Jj/Kg | Jp * Aw * Et * Im/Jj | Nt * Et * Ji * Fp/Lu | Et * Nt * Ji * Im/Jj |
| Is * Ji * Im/Jj/Kg | Ik * Ji * Im/Jj/Aj | Nt * Nw * Et * Ji * Fp | Fp * Ji * Im/Jj/Hw |
| Ok * Aw * Nw * Im/Jj | Kq * Et * Im/Jj/Ch | Mi * Nw * Ji * Fp/Hw | Et * Ok * Ji * Im/Jj |
| Pf * Nw * Im/Jj/Ct | Dg * Ji * Im/Jj/Aj | Nw * Ji * Fp/Me/Hw | Et * Jp * Ji * Im/Jj |
| Mb * Aw * Nw * Im/Jj | Ef * Et * Im/Jj/Aj | Nw * Ji * Fp/Mc/Hw | Et * Qe * Ji * Im/Jj |
| Dg * Et * Ji * Fp/Aj | Ar * Et * Im/Jj/Mc | Qe * Nw * Ji * Fp/Hw | Et * Mi * Ji * Im/Jj |
| Aw * Nw * Im/Jj/Ob | Nt * Aw * Et * Im/Jj | Qa * Nw * Ji * Fp/Hw | Im * Et * Ji * Fp/Lu |
| Jp * Aw * Nw * Im/Jj | Et * Nw * Im/Jj/Kj | Mb * Fp * Nw * Im/Jj | Jg * Et * Ji * Fp/Jj |
| Et * Cu * Nw * Im/Jj | Qa * Et * Im/Jj/Kg | Nw * Ji * Fp/Me/Jj | Ji * Fp * Nw * Im/Jj |
| Et * Oa * Nw * Im/Jj | Pr * Et * Im/Jj/Kg | Om * Nw * Ji * Fp/Jj | Ji * Nw * Im/Jj/Lu |
| Bb * Et * Ji * Fp/Jj | Pj * Et * Im/Jj/Mc | Mi * Nw * Ji * Fp/Lu | Ji * Mb * Nw * Im/Jj |
| Pj * Nw * Im/Jj/Kg | Ke * Et * Im/Jj/Mc | Ok * Nw * Ji * Fp/Mc | Ji * Nw * Im/Jj/Mc |
| Mt * Nw * Im/Jj/Ct | Lw * Fb * Et * Im/Jj | Qe * Et * Ji * Fp/Hw | Fp * Ji * Im/Jj/Mc |
| Nw * Im/Jj/Ob/Mc | Pj * Et * Im/Jj/Kj | Qa * Et * Ji * Fp/Hw | Ok * Fp * Ji * Im/Jj |
| Et * Kk * Nw * Im/Jj | Ik * Nw * Ji * Im/Jj | Et * Is * Nw * Im/Jj | Fp * Ji * Im/Jj/Lu |
| Nm * Ji * Im/Jj/Aj | Ji * Et * Im/Jj/Kj | Ik * Et * Ji * Fp/Jj | Ok * Ji * Im/Jj/Lu |
| Ji * Ar * Nw * Im/Jj | Pj * Aw * Et * Im/Jj | Ik * Nw * Ji * Fp/Jj | Mb * Ji * Im/Jj/Mc |
| Fb * Aw * Ji * Im/Jj | Mi * Aw * Et * Im/Jj | Ji * Qe * Nw * Im/Jj | Jp * Fp * Ji * Im/Jj |
| Pf * Et * Ji * Fp/Ct | Et * Nw * Im/Jj/Kg | Jg * Nw * Ji * Fp/Jj | Mb * Ok * Ji * Im/Jj |
| Nt * Aw * Ji * Im/Jj | Jy * Et * Im/Jj/Mc | Mb * Ok * Nw * Im/Jj | Ok * Ji * Im/Jj/Mc |
| Ip * Ji * Im/Jj/Aj | Mi * Et * Im/Jj/Ob | Qd * Nw * Ji * Fp/Jj | Mb * Ji * Im/Jj/Lu |
| Et * Ji * Im/Jj/Ch | Qe * Et * Im/Jj/Kg | Mz * Nw * Ji * Fp/Jj | Mz * Fp * Ji * Im/Jj |
| Jg * Ji * Im/Jj/Aj | Fb * Pj * Et * Im/Jj | Mz * Nw * Ji * Fp/Lu | Ji * Im/Jj/Mc/Lu |
| Mt * Ji * Im/Jj/Ct | Ji * Ar * Et * Im/Jj | Nw * Et * Ji * Fp/Hw | On * Fp * Ji * Im/Jj |
| Et * Cu * Ji * Im/Jj | Mb * Et * Im/Jj/Ob | Et * Ji * Fp/Lu/Hw | Mb * Fp * Ji * Im/Jj |
| Et * Bb * Nw * Im/Jj | Et * Fb * Nw * Im/Jj | Nt * Et * Ji * Fp/Hw | Et * Ji * Fp/Mc/Jj |
| Et * Bc * Nw * Im/Jj | Jg * Et * Im/Jj/Aj | Et * Ji * Fp/Jj/Hw | Et * Ji * Fp/Lu/Jj |
| Qe * Aw * Ji * Im/Jj | Ji * Et * Im/Jj/Kg | Mi * Et * Ji * Fp/Hw | Ok * Et * Ji * Fp/Jj |
| Mm * Ji * Im/Jj/Kg | Qe * Aw * Et * Im/Jj | Im * Et * Ji * Fp/Hw | Nw * Et * Ji * Fp/Jj |
| Bc * Ji * Im/Jj/Aj | Ip * Ji * Im/Jj/Kg | Is * Nw * Im/Jj/Hw | Nw * Et * Ji * Fp/Lu |
| Mm * Nw * Im/Jj/Kj | Ji * Fb * Et * Im/Jj | Is * Nw * Ji * Fp/Hw | Et * Ji * Fp/Mc/Lu |
| Ma * Et * Ji * Fp/Aj | Bc * Et * Im/Jj/Aj | Ik * Mz * Nw * Im/Jj | Jp * Et * Ji * Fp/Jj |
| Qe * Aw * Nw * Im/Jj | Ji * Et * Im/Jj/Ob | Ik * Mz * Ji * Im/Jj | Mb * Et * Ji * Fp/Jj |
| Dg * Nw * Im/Jj/Kj | Is * Et * Im/Jj/Kj | Et * Ji * Im/Jj/Me | Qe * Et * Ji * Fp/Jj |
| Aw * Nw * Im/Jj/Mc | Lw * Aw * Et * Im/Jj | Im * Nw * Ji * Fp/Hw | Nt * Et * Ji * Fp/Jj |
| Ar * Ji * Im/Jj/Mc | Dg * Et * Im/Jj/Aj | Ji * Nt * Nw * Im/Jj | Qa * Et * Ji * Fp/Jj |
| Et * Ke * Nw * Im/Jj | Nm * Et * Im/Jj/Kj | Ji * Ok * Nw * Im/Jj | Ok * Et * Ji * Fp/Lu |
| Is * Nw * Im/Jj/Ct | Fb * Aw * Et * Im/Jj | Ji * Nw * Im/Jj/Me | Jt * Et * Ji * Fp/Jj |
| Et * Pj * Nw * Im/Jj | Is * Et * Im/Jj/Kg | Nt * Fp * Ji * Im/Jj | On * Et * Ji * Fp/Jj |
| Ji * Aw * Nw * Im/Jj | Et * Nw * Im/Jj/Ob | Mz * Nt * Ji * Im/Jj | Mi * Et * Ji * Fp/Jj |
| Dg * Nw * Im/Jj/Aj | Mb * Aw * Et * Im/Jj | Nt * Ji * Im/Jj/Mc | Jp * Et * Ji * Fp/Lu |
| Mm * Nw * Im/Jj/Kg | Et * Aw * Nw * Im/Jj | Nt * Ji * Im/Jj/Lu | Qd * Et * Ji * Fp/Jj |
| Mb * Aw * Ji * Im/Jj | Fb * Et * Im/Jj/Ob | Nt * Ok * Ji * Im/Jj | Mz * Et * Ji * Fp/Jj |
| Et * Ke * Ji * Im/Jj | Lw * Et * Im/Jj/Ob | Qe * Fp * Ji * Im/Jj | Nw * Et * Ji * Fp/Mc |
| Kl * Nw * Im/Jj/Aj | Kl * Et * Im/Jj/Aj | Mi * Fp * Ji * Im/Jj | Mz * Et * Ji * Fp/Lu |
| Is * Ji * Im/Jj/Ct | Ji * Aw * Et * Im/Jj | Jp * Mb * Ji * Im/Jj | Mb * Et * Ji * Fp/Lu |
| Et * Pj * Ji * Im/Jj | Fb * Et * Im/Jj/Mc | Qe * Ji * Im/Jj/Mc | Lw * Et * Ji * Fp/Jj |
| Et * Kq * Ji * Im/Jj | Ip * Et * Im/Jj/Kg | Ok * Ji * Im/Jj/Me | Js * Et * Ji * Fp/Jj |
| Is * Nw * Im/Jj/Kj | Ad * Et * Im/Jj/Kj | Et * Ji * Fp/Nh/Jj | Is * Nw * Ji * Fp/Jj |
| Aw * Et * Ji * Fp/Jj | Aw * Et * Im/Jj/Ob | Mz * Nt * Et * Ji * Fp | Nw * Ji * Fp/Lu/Hw |
| Nm * Ji * Im/Jj/Kj | Aw * Et * Im/Jj/Mc | Pz * Et * Ji * Fp/Jj | Ok * Nw * Ji * Fp/Hw |
| Et * Bb * Ji * Im/Jj | Ad * Et * Im/Jj/Aj | Mi * Et * Ji * Fp/Lu | Mz * Nw * Ji * Fp/Hw |
| Et * Kq * Nw * Im/Jj | Ik * Et * Im/Jj/Aj | Om * Et * Ji * Fp/Jj | Ok * Fp * Nw * Im/Jj |
| Ad * Ji * Im/Jj/Kj | Et * Im/Jj/Ob/Mc | Mb * Et * Ji * Fp/Mc | Fp * Nw * Im/Jj/Mc |
| Is * Nw * Im/Jj/Kg | No * Nw * Ji * Fp/Hw | Lh * Et * Ji * Fp/Jj | Ok * Nw * Ji * Fp/Jj |
| Aw * Ji * Im/Jj/Mc | Et * Nw * Ji * Fp/Nh | Mb * Nw * Et * Ji * Fp | Nw * Ji * Fp/Lu/Jj |
| Nm * Nw * Im/Jj/Kj | Nw * Ji * Fp/Nh/Hw | Lw * Et * Ji * Fp/Lu | Nw * Ji * Fp/Mc/Jj |

TABLE 4-continued

| | | | |
|---|---|---|---|
| Et * Ji * Im/Jj/Aj | Nt * Nw * Ji * Fp/Mc | Jp * Et * Ji * Fp/Mc | Qe * Nw * Ji * Fp/Jj |
| Ke * Nt * Et * Im/Jj | Nt * Ok * Nw * Ji * Fp | Jo * Et * Ji * Fp/Jj | Jp * Nw * Ji * Fp/Jj |
| Kk * Pj * Et * Im/Jj | Et * Qe * Nw * Ji * Fp | Nt * Nw * Ji * Fp/Hw | Mb * Nw * Ji * Fp/Jj |
| Pf * Et * Im/Jj/Kg | Jm * Nw * Ji * Fp/Jj | Im * Nw * Ji * Fp/Lu | On * Nw * Ji * Fp/Jj |
| Qd * Et * Im/Jj/Kg | Nt * Nw * Ji * Fp/Lu | Nw * Ji * Fp/Jj/Hw | Qa * Nw * Ji * Fp/Jj |
| Dg * Et * Im/Jj/Kj | Om * Nw * Ji * Fp/Hw | Fp * Nw * Im/Jj/Lu | Nw * Ji * Fp/Mc/Lu |
| Et * Jy * Nw * Im/Jj | Is * Nw * Ji * Fp/Lu | On * Fp * Nw * Im/Jj | Ok * Nw * Ji * Fp/Lu |
| Kl * Et * Im * Ji/Aj | Et * Ke * Is/Jj/Kg | Pf * Nm * Mt/Ct/Ch | Mz * Nm * Pf * Mt/Ct |
| Et * Pj * Is/Jj/Kg | Et * Ji * Is/Jj/Kg | Im * Nm * Pf * Mt/Ct | Mz * Nt * Is * Mt/Ct |
| Dg * Et * Im * Ji/Aj | Mz * Nm * Mt/Ct/Jj | Ji * Im * Nm * Mt/Ct | Et * Mm * Is/Jj/Kg |
| Ad * Et * Im * Ji/Aj | Pj * Et * Is/Kj/Jj | Et * Is * Ok/Jj/Kg | Nm * Pf * Mt/Ct/Aj |
| Jg * Et * Im * Ji/Aj | Dg * Et * Is/Kj/Jj | Nb * Im * Nm * Mt/Ct | Is * Nm * Mt/Ct/Ch |
| Im * Nm * Mt/Ct/Jj | Nb * Nm * Mt/Ct/Ch | Et * Nt * Im * Mt/Ct | Is * Mz * Nm * Mt/Ct |
| Im * Mz * Nm * Mt/Ct | Ny * Nm * Mt/Ct/Hw | Hu * Nm * Mt/Ct/Ch | Di * Im * Nm * Mt/Ct |
| Et * Im * Nm * Mt/Ct | Kq * Et * Is/Jj/Kg | Is * Nm * Mt/Ct/Aj | Et * Is * Nm * Mt/Ct |
| Im * Nm * Mt/Ct/Ch | Kq * Et * Im * Ji/Aj | Ad * Et * Is/Kj/Jj | Pf * Et * Is/Jj/Kg |
| Nm * Pf * Mt/Ct/Oy | Et * Nt * Is * Mt/Ct | Im * Nm * Mt/Ct/Aj | Ip * Et * Is/Jj/Kg |
| Et * Is/Jj/Kg/Mc | Is * Nm * Mt/Ct/Jj | Mz * Nt * Im * Mt/Ct | Jp * Et * Is/Jj/Kg |
| Is * Nt * Im * Mt/Ct | Nb * Nt * Is * Mt/Ct | Nw * Im * Nm * Mt/Ct | Et * Aw * Is/Jj/Kj |
| Is * Im * Nm * Mt/Ct | Et * Is * Nw/Jj/Kg | Ba * Nm * Mt/Ct/Ch | Jy * Et * Is/Jj/Kg |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for evaluating the likelihood of future nonoccurrence of acute renal failure renal in a critically ill subject diagnosed with acute renal injury, comprising:
    obtaining a plasma or urine sample from the subject,
    introducing the plasma or urine sample obtained from the subject into an assay instrument for performing a first immunoassay to determine the concentration of antileukoproteinase and a second immunoassay to determine the concentration of thrombomodulin wherein the first immunoassay comprises: contacting the plasma or urine sample with a first antibody specifically binding antileukoproteinase to obtain a first assay result value indicative of the concentration value of Antileukoproteinase,
    wherein the second immunoassay comprises: contacting the plasma or urine sample with a second antibody specifically binding thrombomodulin to generate a second assay result value indicative of the concentration value of Thrombomodulin,
    obtaining a composite value comprising the ratio of concentration of Antileukoproteinase to the concentration value of thrombomodulin,
    correlating the composite value to a likelihood of occurrence or nonoccurrence of continuing acute renal failure within 72 hours of the time at which the plasma or urine sample is obtained from the subject,
    wherein the composite value that is lower as compared to a threshold is indicative of a likelihood of nonoccurrence of continuing acute renal failure within 72 hours of the time at which the plasma or urine sample is obtained from the subject; and
    wherein the composite value that is higher as compared to the threshold is indicative of a likelihood of occurrence of continuing acute renal failure within 72 hours of the time at which the plasma or urine sample is obtained from the subject; and
    wherein the threshold is a composite result value obtained by performing the first and second immunoassays in plasma or urine sample from a predetermined subpopulation of individuals comprising critically ill subjects with a known occurrence of continuing acute renal failure within 72 hours of the time at which the plasma or urine sample is obtained.

2. A method according to claim 1, wherein the correlating step comprises correlating the composite value to a likelihood of occurrence or nonoccurrence of continuing acute renal failure within 48 hours of the time at which the plasma or urine sample is obtained from the subject,
    wherein the composite value that is lower as compared to a threshold is indicative of a likelihood of nonoccurrence of continuing acute renal failure within 48 hours of the time at which the plasma or urine sample is obtained from the subject; and wherein the composite value that is higher as compared to the threshold is indicative of a likelihood of occurrence of continuing acute renal failure within 48 hours of the time at which the plasma or urine sample is obtained from the subject; and wherein the threshold is a composite result obtained by performing the first and second immunoassays in plasma or urine sample from a predetermined subpopulation of individuals comprising critically ill subjects with a known occurrence of continuing acute renal failure within 48 hours of the time at which the plasma or urine sample is obtained.

3. A method according to claim 1, wherein the correlating step comprises correlating the composite value to a likelihood of occurrence or nonoccurrence of continuing acute renal failure within 24 hours of the time at which the plasma or urine sample is obtained from the subject, wherein the composite value that is lower as compared to a threshold is indicative of a likelihood of nonoccurrence of continuing acute renal failure within 24 hours of the time at which the plasma or urine sample is obtained from the subject; and wherein the composite value that is higher as compared to the threshold is indicative of a likelihood of occurrence of continuing acute renal failure within 24 hours of the time at which the plasma or urine sample is obtained from the subject; and wherein the threshold is a composite result obtained by performing the first and second immunoassays in plasma or urine sample from a predetermined subpopulation of individuals comprising critically ill subjects with a known occurrence of continuing acute renal failure within 24 hours of the time at which the plasma or urine sample is obtained.

4. A method according to claim 1, wherein the subject is in RIFLE stage I or F.

* * * * *